US009213030B2

(12) United States Patent
Wenk et al.

(10) Patent No.: US 9,213,030 B2
(45) Date of Patent: Dec. 15, 2015

(54) LIPID TUMOUR PROFILE

(75) Inventors: Markus R. Wenk, Singapore (SG); Gek Huey Chua, Singapore (SG); Aaron Zefrin Fernandis, Singapore (SG); Xueli Guan, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 1269 days.

(21) Appl. No.: 12/864,876

(22) PCT Filed: Jan. 28, 2009

(86) PCT No.: PCT/SG2009/000035
§ 371 (c)(1), (2), (4) Date: Oct. 6, 2010

(87) PCT Pub. No.: WO2009/096903
PCT Pub. Date: Aug. 6, 2009

(65) Prior Publication Data

US 2011/0021451 A1 Jan. 27, 2011

(30) Foreign Application Priority Data

Jan. 28, 2008 (SG) ................................ 200800773-4

(51) Int. Cl.

| | |
|---|---|
| ***G06G 7/48*** | (2006.01) |
| ***G01N 33/574*** | (2006.01) |
| ***G01N 33/92*** | (2006.01) |
| ***G06F 19/24*** | (2011.01) |
| *G06F 19/18* | (2011.01) |

(52) U.S. Cl.
CPC .......... *G01N 33/57449* (2013.01); *G01N 33/92* (2013.01); *G06F 19/24* (2013.01); *G01N 2800/60* (2013.01); *G06F 19/18* (2013.01)

(58) Field of Classification Search
CPC ........................................................ G06F 19/24
USPC ............................................................. 703/12
See application file for complete search history.

(56) References Cited

U.S. PATENT DOCUMENTS

2007/0111316 A1 5/2007 Shi et al.

FOREIGN PATENT DOCUMENTS

EP 0 531 933 A2 3/1993
EP 1 645 877 A1 4/2006

OTHER PUBLICATIONS

Baker et al., JAMA, 287:3081-3082 (2002). “Plasma lysophosphatidic acid concentration and ovarian cancer.”
Ding and Dubchak, Bioinformatics, 17(4):349-358 (2001). “Multi-class protein fold recognition using support vector machines and neural networks.”
Einhorn et al., Obstet. Gynecol., 80:14-18 (1992). “Prospective evaluation of serum CA 125 levels for early detection of ovarian cancer.”
Glunde and Serkova, Pharmacogenomics, 7:1109-1123 (2006). “Therapeutic targets and biomarkers identified in cancer choline phospholipid metabolism.”
Han and Gross, Proc. Natl. Acad. Sci. USA, 91:10635-10639 (1994). “Electrospray ionization mass spectroscopic analysis of human erythrocyte plasma membrane phospholipids.”
Iorio et al., Cancer Res, 65:9369-9376 (2005). “Alterations of choline phospholipid metabolism in ovarian tumor progression.”
Ivanciuc et al., Reviews in Computational Chemistry, 23:291-400 (2007). “Applications of support vector machines in chemistry.”
Jacobs et al., BMJ, 306:1030-1034 (1993). “Prevalence screening for ovarian cancer in postmenopausal women by CA 125 measurement and ultrasonography.”
Jacobs and Menon, Mol. Cell Proteomics, 3:355-366 (2004). “Progress and challenges in screening for early detection of ovarian cancer.”
Joachims, T., Making large-Scale SVM Learning Practical. Advances in Kernel Methods—Support Vector Learning, B. 1999. MIT Press. Ref Type: Generic.
Kozak et al., Proc. Natl. Acad. Sci. USA, 100:12343-12348 (2003). “Identification of biomarkers for ovarian cancer using strong anion-exchange ProteinChips: potential use in diagnosis and prognosis.”
Lin et al., Journal of Lipid Research, 47:824-831 (2006). “Prediction of the functional class of lipid binding proteins from sequence-derived properties irrespective of sequence similarity.”
Menon and Jacobs, Best. Pract. Res. Clin. Obstet. Gynaecol, 16:469-482 (2002). “Screening for ovarian cancer.”
Merrill et al., Methods, 36:207-224 (2005). Sphingolipidomics: high-throughput, structure-specific, and quantitative analysis of sphingolipids by liquid chromatography tandem mass spectrometry.
Noble, W.S., Nat. Biotechnol, 24:1565-1567 (2006). “What is a support vector machine?”.
Okita et al., Int. J. Cancer, 71:31-34 (1997). “Elevated levels and altered fatty acid composition of plasma lysophosphatidylcholine(lysoPC) in ovarian cancer patients.”
Petricoin et al., Lancet, 359:572-577 (2002). “Use of proteomic patterns in serum to identify ovarian cancer.”
Guan XL, et al. Biochemical membrane lipidomics during Drosophila development Dev Cell (2013) 24(1):90-111.
Lam SM, et al. Meibum Lipid Composition in Asians with Dry Eye Disease PLoS One (2011) 6(10):e24339.

(Continued)

*Primary Examiner* — Jerry Lin
(74) *Attorney, Agent, or Firm* — Nixon Peabody LLP; Mark J. FitzGerald

(57) ABSTRACT

We describe a method of generating a classification model capable of distinguishing between two biological states, the method comprising the steps of: (a) providing a training dataset, X, comprising concentrations of a plurality of lipids in a biological sample in a first state and a biological sample in a second state; (b) subjecting the training dataset X to Principal Components Analysis (PCA), in which the PCA analysis generates a transformation matrix, C, and a transformed dataset, $Y_l$; (c) subjecting the transformed dataset $Y_l$ to Support Vector Machines (SVM) analysis, in which the SVM analysis generates a SVM model, S; (d) forming a classification model comprising (i) the transformation matrix C, and (ii) the corresponding SVM model S.

9 Claims, 16 Drawing Sheets

(56) References Cited

OTHER PUBLICATIONS

Shui G, et al. Comparative Plasma Lipidome between Human and Cynomolgus Monkey: Are Plasma Polar Lipids Good Biomarkers for Diabetic Monkeys? PLoS One (2011) 6(5):e19731.

Shui G, et al. Mycolic acids as diagnostic markers for tuberculosis case detection in humans and drug efficacy in mice EMBO Mol Med (2012) 4(1):27-37.

Wenk MR et al. Lipidomics: new tools and applications Cell (2010) 143(6):888-95.

Dutkowski and Gambin, BMC Bioinformatics, 8:S5 (2007). "On consensus biomarker selection."

Wei et al., Biomarkers, 10:153-172 (2005). "Data-driven analysis approach for biomarker discovery using molecular-profiling technologies."

Lee et al. "Lipidomic Profing of Peripheral Blood in Schizophrenia." Schizophrenia Research 102.1 (2008): 208.

Mutch et al., "Putting the 'Ome' in lipid metabolism", Biotechnol Annu Rev. 12:67-84 (2006).

Fernandis et al., "Lipid-based biomarkers for cancer", Journal of Chromatography B: Biomedical Sciences & Applications, 877(26):2830-2835 (2009).

D. Control + Benign Vs Malignant

E. Benign Vs Early

LIPID TUMOUR PROFILE

CROSS REFERENCE TO RELATED APPLICATIONS

This application is a 35 U.S.C. §371 National Phase Entry application of International Application No. PCT/SG2009/000035, filed Jan. 28, 2009, which designates the United States, and which claims the benefit of priority to Singapore Patent Application No. 200800773-4, filed Jan. 28, 2008, the contents of each of which are incorporated by reference herein in their entirety.

FIELD

The present invention relates to the fields of medicine, cell biology, molecular biology and genetics.

BACKGROUND

Ovarian tumor is the fifth leading cause of cancer-related death and is difficult to diagnose and monitor. Although ovarian cancer accounts for about 4 percent of all cancers in women, it has the highest mortality of all gynecologic cancers, being a silent killer because it is often diagnosed at an advanced stage.

Ovarian cancer may be diagnosed, in part, by collecting a routine medical history from a patient and by performing physical examination, x-ray examination, and chemical and hematological studies on the patient. Hematological tests which may be indicative of ovarian cancer in a patient include analyses of serum levels of proteins designated CA125 and DF3 and plasma levels of lysophosphatidic acid (LPA). Palpation of the ovaries and ultrasound techniques (particularly including endovaginal ultrasound and color Doppler flow ultrasound techniques) can aid detection of ovarian tumors and differentiation of ovarian cancer from benign ovarian cysts. However, a definitive diagnosis of ovarian cancer typically requires performing exploratory laparotomy of the patient.

Thus, while abnormal growth corresponding to ovaries can be monitored by ultrasonography or by the serum marker, CA125, determining whether the growth is benign or malignant is not possible without biopsies. Biopsies are typically done after surgery and the tissue growth is taken for various pathological examinations. This is a tedious and time consuming procedure. The patient is usually out of the surgery room by the time the information is acquired.

Detection and proper measures for the control of the disease by surgery at the early stages can prevent the patient from undergoing agonizing radio and chemotherapy. Such procedures also often, in the most advanced cases, have no substantial curative effects.

Current diagnostic methods include serological diagnostics, which determine the level of CA-125, a protein produced by ovarian cancer cells. While CA-125 is an important test, it unfortunately is not always accurate. For example, some ovarian cancers may not produce enough CA-125 levels to cause a positive test result. Although the level of this antigen is elevated in nearly 80% of the patients with advanced stages of the cancer, expression may be low in early stages of ovarian cancer. Serum CA125 levels may also be falsely elevated in patients having other gynecological conditions like serosa of the peritoneum or pericardium, uterine fibroids, renal disorders or even pregnancy and normal menses.

Other current diagnostic methods include trans-vaginal ultrasound (TVU), which may be conducted alone or in combination with CA-125 testing. These methods can detect ovarian cancer but can also produce many false-positive test results. Use of ultrasound in conjunction with the CA125 has a positive predictive value of only 20%. It is estimated that three out of every four surgeries carried out are for non-malignant conditions, and these could possibly have been avoided saving the patients from the surgical trauma.

The diagnostic and prognostic tools presently available are therefore not adequate to predict the onset of the disease.

Genomic and proteomic techniques for the discovery of novel biomarkers for ovarian cancer from body fluids are known. The blueprints derived from these methods have recently shown assurance for early ovarian cancer detection, but further studies regarding their reproducibility and reliability for early detection and screening are needed.

Some of these proteins which are predicted to have a role as biomarker for ovarian cancer include M-CSF, mesothelin, α-folate receptor, OVX1, CA72-4, Prostasin, Osteopontin, Inhibin and Kallikrien.

Recently there has been an interest in using lysophosphatidic acid (LPA) as a biomarker for ovarian cancer. LPA has been shown to stimulate the proliferation of ovarian cancer cells and has been found in blood of ovarian cancer patients. LPA as a biomarker has been shown to have a sensitivity of 100% in advanced stage and almost 90% in the early stages.

However, the use of LPA as a biomarker for ovarian cancer has been highly controversial. In some studies no significant change in LPA levels in the ovarian cancer patients have been observed, raising questions about the utility of LPA as a biomarker. Some of the discrepancies were attributed to differences in the isolation protocol of plasma as activated platelets could also generate LPA. This lipid is also elevated in patients with other gynecological manifestations.

There is therefore a need for a method of detecting and diagnosing cancers such as ovarian cancers.

SUMMARY

According to a $1^{st}$ aspect of the present invention, we provide a method of generating a classification model capable of distinguishing between two biological states, the method comprising the steps of: (a) providing a training dataset, X, comprising concentrations of a plurality of lipids in a biological sample in a first state and a biological sample in a second state; (b) subjecting the training dataset X to Principal Components Analysis (PCA), in which the PCA analysis generates a transformation matrix, C, and a transformed dataset, $Y_l$; (c) subjecting the transformed dataset $Y_l$ to Support Vector Machines (SVM) analysis, in which the SVM analysis generates a SVM model, S; (d) forming a classification model comprising (i) the transformation matrix C, and (ii) the corresponding SVM model S.

The plurality of lipids may include a plurality of choline lipids, such as phosphatidylcholine (GPCho) or sphingomyelin (SM) or both. It may further optionally comprise one or more of phosphatidic acid (GPA), phosphatidylglycerol (GPGro), phosphatidylserine acid (GPSer), sulfatides, cardiolipin, phosphatidylethanolamine (GPEtn), phosphatidylinositol (GPIns), phosphatidylinositol phosphates (GPInsPs), ceramide (Cer), mono hexosyl ceramide (MonoHexCer) and di hexosyl ceramide (DiHexCer). It may comprise all the aforementioned lipids.

The plurality of lipids may comprise the lipids set out in Table D1. It may comprise the lipids set out in Table D2. It may comprise the lipids set out in Table D3. It may comprise the lipids set out in Table E4. It may comprise the lipids set out in Table E6.

The two biological states may comprise a normal state and a diseased state. The diseased state may comprise a cancerous or tumour state, for example ovarian cancer.

The classification model may be capable of achieving a sensitivity of 98.99% or more. It may be capable of achieving specificity of 92.31% or more. It may be capable of achieving a PPV of 97.03% or more. It may be capable of achieving a NPV of 97.30%. It may be capable of achieving more or an accuracy of 97.10% or more. It may be capable of achieving one or more, such as all, of the above.

The two biological states may comprise a benign state and a malignant state, such as of ovarian cancer.

The classification model may be capable of achieving a sensitivity of 94.92% or more. It may be capable of achieving a specificity of 82.50% or more. It may be capable of achieving a PPV of 88.89% or more. It may be capable of achieving a NPV of 91.67% or more. It may be capable of achieving an accuracy of 89.90% or more. It may be capable of achieving one or more, such as all, of the above.

The two biological states may comprise an early tumour stage and a late tumour stage, such as of ovarian cancer.

The classification model may be capable of achieving a sensitivity of 100%. It may be capable of achieving a specificity of 81.82% or more. It may be capable of achieving a PPV of 90.24% or more. It may be capable of achieving a NPV of 100%. It may be capable of achieving an accuracy of 93.22% or more. It may be capable of achieving one or more, such as all, of the above.

The method may further comprise a step (c1) between step (c) and step (d). The additional step may comprise repeating steps (b) and (c) and selecting principal components which enable optimal classification in step (c).

The method may be such that optimal classification in step (c1) is determined by assessing the output of the SVM for sensitivity, specificity and accuracy at each iteration The classification model may further comprise (iii) the number of selected principal components enabling optimal classification in step (c).

Step (c1) may comprise retaining principal components that perform at least 55%, 65%, 75%, 85%, 90%, 95%, 96%, 97%, 98%, 99%, 99.5%, 99.6%, 99.7%, 99.8%, 99.9% or 100% as well as the full dataset, after step (e), as assessed by any combination of sensitivity, specificity, PPV, NPV, accuracy, true negatives (TN), false negatives (FN), false positives (FP) and true positives (TP). It may comprise removing factors which do not significantly affect the performance of the SVM model. It may comprise retaining principal components whose eigenvalues are greater than or equal to 1. It may comprise retaining principal components that explain at least 55%, 65%, 75%, 85%, 90%, 95%, 96%, 97%, 98%, 99%, 99.5%, 99.6%, 99.7%, 99.8% or 99.9% of the variance in the dataset. It may comprise retaining principal components that in a scree plot of eigenvalues show a smooth decrease of eigenvalues or which are to the left of a levelling off or significant decrease in gradient or elbow in the plot (scree test). Step (c1) may comprise one or more of the above. It may comprise all of the above.

The method may comprise implementing SVM using a default linear kernel. $SVM_{light}$ may be used.

The biological sample may comprise a serum sample of or from an individual.

The lipids may be identified by mass spectroscopy. The mass spectroscopy may comprise electrospray ionization mass spectrometry (ESI-MS). The lipids may be quantified by multiple reaction monitoring (MRM). The lipids may be identified and quantified as set out above.

The concentration of each lipid may be normalized by obtaining $$\text{Lipid}_i = \frac{x_i}{[Std]\cdot\sum_{i=1}^{n} x_i},$$

where $x_i$ is the intensity of a $\text{lipid}_i$ and Std is the ratio of the intensity to the amount in pmoles of a lipid standard.

There is provided, according to a $2^{nd}$ aspect of the present invention, a classification model obtained by a method according to the $1^{st}$ aspect of the invention.

We provide, according to a $3^{rd}$ aspect of the present invention, a classification model capable of distinguishing between a normal sample and an ovarian cancer sample. The classification model may comprise: (a) a 340×340 transformation matrix as shown in Appendix B1 and an SVM model as shown in Appendix C1; (b) a 340×85 transformation matrix comprising the first 85 columns of the matrix as shown in Appendix B1 and an SVM model as shown in Appendix C4; (c) a 340×10 transformation matrix comprising the first 10 columns of the matrix as shown in Appendix B1 and an SVM model as shown in Appendix C7; (d) a 82×82 transformation matrix as shown in Appendix B4 and an SVM model as shown in Appendix C10; or (e) a 77×77 transformation matrix as shown in Appendix B7 and an SVM model as shown in Appendix C13.

As a $4^{th}$ aspect of the present invention, there is provided a classification model capable of distinguishing between a benign cancer sample and an malignant cancer sample. The classification model may comprise: (a) a 340×340 transformation matrix as shown in Appendix B2 and an SVM model as shown in Appendix C2; (b) a 340×87 transformation matrix comprising the first 87 columns of the matrix as shown in Appendix B2 and an SVM model as shown in Appendix C5; (c) a 340×29 transformation matrix comprising the first 29 columns of the matrix as shown in Appendix B2 and an SVM model as shown in Appendix C8; (d) a 82×82 transformation matrix as shown in Appendix B5 and an SVM model as shown in Appendix C11; or (e) a 77×77 transformation matrix as shown in Appendix B8 and an SVM model as shown in Appendix C14.

We provide, according to a $5^{th}$ aspect of the present invention, a classification model capable of distinguishing between an early stage cancer sample and a late stage cancer sample. The classification model comprise (a) a 340×340 transformation matrix as shown in Appendix B3 and an SVM model as shown in Appendix C3; (b) a 340×44 transformation matrix comprising the first 44 columns of the matrix as shown in Appendix B3 and an SVM model as shown in Appendix C6; (c) a 340×82 transformation matrix comprising the first 82 columns of the matrix as shown in Appendix B3 and an SVM model as shown in Appendix C9; (d) a 82×82 transformation matrix as shown in Appendix B6 and an SVM model as shown in Appendix C12; or (e) a 77×77 transformation matrix as shown in Appendix B9 and an SVM model as shown in Appendix C15.

The present invention, in a $6^{th}$ aspect, provides a computer readable medium comprising a classification model as set out above.

In a $7^{th}$ aspect of the present invention, there is provided a method of determining the status of a sample, the method comprising (i) providing a dataset comprising concentrations of a plurality of lipids in the sample and (ii) applying a classification model as set out above.

The plurality of lipids may include a plurality of choline lipids, such as phosphatidylcholine (GPCho) or sphingomyelin (SM) or both. It may further optionally comprises phosphatidic acid (GPA), phosphatidylglycerol (GPGro), phosphatidylserine acid (GPSer), sulfatides, cardiolipin, phosphatidylethanolamine (GPEtn), phosphatidylinositol (GPIns), phosphatidylinositol phosphates (GPInsPs), ceramide (Cer), mono hexosyl ceramide (MonoHexCer) and di hexosyl ceramide (DiHexCer).

The plurality of lipids may comprise the lipids set out in Table D1. It may comprise the lipids set out in Table D2. It may comprise the lipids set out in Table D3. It may comprise the lipids set out in Table E4. It may comprise the lipids set out in Table E6.

The method may be used for determining whether a sample is a normal sample or an ovarian cancer sample. Such a method may comprise (i) transforming the dataset with a transformation matrix of a classification model according to the $3^{rd}$ aspect of the invention to generate a transformed dataset, and (ii) subjecting the transformed dataset to Support Vector Machines (SVM) analysis with an SVM model of the classification model, in which an output of >0 indicates a normal sample and an output of <0 indicates an ovarian cancer sample.

According to an $8^{th}$ aspect of the present invention, we provide a method of obtaining an indication useful in the diagnosis of ovarian cancer in an individual, the method comprising conducting such a method on a sample of or from a patient, in which an output of <0 indicates that the individual is suffering from ovarian cancer.

The method may be used for determining whether a sample is a benign or malignant ovarian cancer sample, the method comprising (i) transforming the dataset with a transformation matrix of a classification model according to the $4^{th}$ aspect of the invention to generate a transformed dataset, and (ii) subjecting the transformed dataset to Support Vector Machines (SVM) analysis with an SVM model of the classification model, in which an output of >0 indicates a benign sample and an output of <0 indicates a malignant sample.

We provide, according to a $9^{th}$ aspect of the invention, a method of obtaining an indication useful in the diagnosis of an individual suffering from a malignant ovarian cancer, the method comprising conducting such a method on a sample of or from a patient, in which an output of >0 indicates that the individual is suffering from a benign ovarian cancer and an output of <0 indicates that the individual is suffering from a malignant ovarian cancer.

The method may be used for determining whether a sample is an early stage cancer or a late stage ovarian cancer sample, the method comprising (i) transforming the dataset with a transformation matrix of a classification model according to the $5^{th}$ aspect of the invention to generate a transformed dataset, and (ii) subjecting the transformed dataset to Support Vector Machines (SVM) analysis with an SVM model of the classification model, in which an output of >0 indicates an early stage cancer sample and an output of <0 indicates a late stage cancer sample.

There is provided, in accordance with a $10^{th}$ aspect of the present invention, a method of obtaining an indication useful in the diagnosis of an individual suffering from a late stage ovarian cancer, the method comprising conducting such a method on a sample of or from a patient, in which an output of >0 indicates that the individual is suffering from an early stage ovarian cancer and an output of <0 indicates that the individual is suffering from a late stage ovarian cancer.

As an $11^{th}$ aspect of the invention, we provide a method of detecting, and optionally classing, ovarian cancer in an individual, the method comprising: (a) providing a dataset comprising concentrations of the lipids set out in Table D1, Table D2, Table D3, Table E4 or Table E6 in a sample from or of the individual; (b) transforming the dataset with a transformation matrix of a classification model according to the $3^{rd}$ aspect of the invention to generate a transformed dataset, and subjecting the transformed dataset to Support Vector Machines (SVM) analysis with an SVM model of the classification model, in which an output of >0 indicates a normal sample and an output of <0 indicates an ovarian cancer sample; and (c) in the case of the latter, further transforming the dataset with a transformation matrix of a classification model according to the $4^{th}$ aspect of the invention to generate a transformed dataset and subjecting the transformed dataset to Support Vector Machines (SVM) analysis with an SVM model of the classification model; in which an output of <0 indicates a benign sample and an output of <0 indicates a malignant sample; (d) in the case of the latter, further transforming the dataset with a transformation matrix of a classification model according to the $5^{th}$ aspect of the invention to generate a transformed dataset and subjecting the transformed dataset to Support Vector Machines (SVM) analysis with an SVM model of the classification model; in which an output of >0 indicates an early stage sample and an output of <0 indicates a late stage sample.

The methods described above may be implemented as computer implemented methods.

We provide, according to a $12^{th}$ aspect of the invention, there is provided a method of treatment or prevention of cancer, such as ovarian cancer, in an individual, the method comprising any one or more of detecting or diagnosing the cancer and optionally classing the cancer, in an individual by a method as set out above, and administering a suitable treatment or prophylactic, such as a drug known or suspected to be useful for treating cancer, to the individual.

According to a $13^{th}$ aspect of the present invention, we provide a method of generating a classification model capable of distinguishing between two biological states, the method comprising the steps of: (a) providing a training dataset, X, comprising concentrations of a plurality of lipids in a biological sample in a first state and a biological sample in a second state; (b) subjecting the training dataset X to Principal Components Analysis (PCA) to generate a transformation matrix, C, comprising principal component coefficients; and a representation, Y, of the dataset X in the principal component space; (c) forming an input vector, $Y_l$, comprising the l most significant row vectors of Y; (d) subjecting the input vector $Y_l$ to Support Vector Machines (SVM) analysis; (e) repeating steps (c) and (d) with varying l to determine a minimum dimension, $l_{min}$, of the principal component space sufficient to obtain optimal classification; (f) forming a classification model comprising (i) the transformation matrix C, (ii) the minimum dimension $l_{min}$, and (ii) the SVM model comprising SVM weights corresponding to the minimum dimension $l_{min}$.

There is provided, according to a $14^{th}$ aspect of the present invention, a combination of lipids selected from the group consisting of: (a) lipids shown in Table D1; (b) lipids shown in Table D2; (c) lipids shown in Table D3; (d) lipids shown in Table E4; and (e) lipids shown in Table E6.

We provide, according to a $15^{th}$ aspect of the present invention, a combination of lipids comprising two or more, such as at least 5, lipids selected from Table D1, Table D2, Table D3, Table E4 or Table E6.

We provide, according to a $16^{th}$ aspect of the present invention, a classification model selected from the group consisting of: (a) a classification model capable of distinguishing between a normal sample and a diseased (ovarian cancer)

sample comprising: (i) an n×m transformation matrix, where n<340 and 1≤m≤n, comprising the first m columns of the matrix shown in Appendix B1; and (ii) an SVM model generated from applying SVM analysis on a transformed dataset, the transformed dataset being generated by transforming a dataset comprising concentrations of the first n lipids shown in Table D3 in a normal sample and a diseased (ovarian cancer) sample with an n×m transformation of (a)(i); (b) a classification model capable of distinguishing between a benign sample and a malignant sample comprising: (i) an n×m transformation matrix, where n<340 and 1≤m≤n, comprising the first m columns of the matrix shown in Appendix B2; and (ii) an SVM model generated from applying SVM analysis on a transformed dataset, the transformed dataset being generated by transforming a dataset comprising concentrations of the first n lipids shown in Table D3 in a benign sample and a malignant sample with an n×m transformation matrix of (b)(i); (c) a classification model capable of distinguishing between an early stage sample and a late stage sample comprising: (i) an n×m transformation matrix, where n<340 and 1≤m≤n, comprising the first m columns of the matrix shown in Appendix B3; and (ii) an SVM model generated from applying SVM analysis on a transformed dataset, the transformed dataset being generated by transforming a dataset comprising concentrations of the first n lipids shown in Table D3 in an early stage sample and a late stage sample with an n×m transformation matrix of (c)(i).

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

APPENDICES

Figure 1:
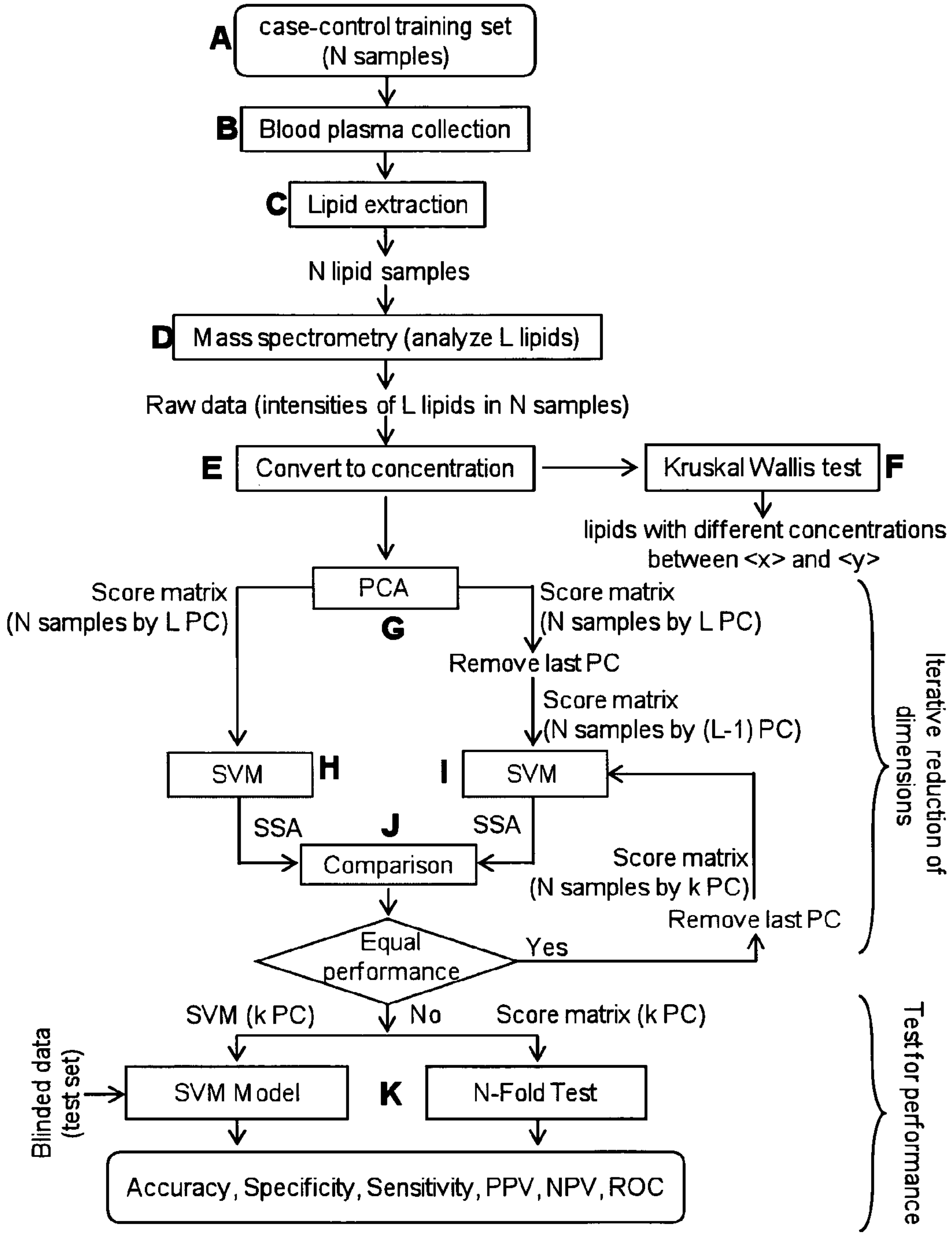
FIG. 1 is a chart illustrating the work flow for development of binary classifiers for ovarian cancers based on multiparameter analysis of plasma lipids and supervised learning. The flow diagram summarises the methodology for building the prediction model and diagnosis of unknown samples.

Appendix A: MRM Conditions for Lipids
Appendix B1: PCA Transformation Matrix (340×340; Normal/Diseased); Appendix B2: PCA Transformation Matrix (340×340; Benign/Malignant); Appendix B3: PCA Transformation Matrix (340×340; Early/Late); Appendix B4: PCA Transformation Matrix (82×82; Normal/Diseased); Appendix B5: PCA Transformation Matrix (82×82; Benign/Malignant); Appendix B6: PCA Transformation Matrix (82×82; Early/Late); Appendix B7: PCA Transformation Matrix (77×77; Normal/Diseased); Appendix B8: PCA Transformation Matrix (77×77; Benign/Malignant); Appendix B9: PCA Transformation Matrix (77×77; Early/Late).

Appendix C1: SVM Model Weights (340; Normal/Diseased); Appendix C2: SVM Model Weights (340; Benign/Malignant); Appendix C3: SVM Model Weights (340; Early/Late); Appendix C4: SVM Model Weights (85; Normal/Diseased); Appendix C5: SVM Model Weights (87; Benign/Malignant); Appendix C6: SVM Model Weights (44; Early/Late); Appendix C7: SVM Model Weights (10; Normal/Diseased); Appendix C8: SVM Model Weights (29; Benign/Malignant); Appendix C9: SVM Model Weights (9; Early/Late); Appendix C10: SVM Model Weights (82; Normal/Diseased); Appendix C11: SVM Model Weights (82; Benign/Malignant); Appendix C12: SVM Model Weights (82; Early/Late); Appendix C13: SVM Model Weights (77; Normal/Diseased); Appendix C14: SVM Model Weights (77; Benign/Malignant); Appendix C15: SVM Model Weights (77; Early/Late).

Appendix D: Ovarian Cancer Training Dataset.
Appendix E1: Cumulative Performance of Model versus Number of Principal Components Selected (Normal vs Diseased; 340 Lipids). Appendix E2: Cumulative Performance of Model versus Number of Principal Components Selected (Benign vs Malignant; 340 Lipids). Appendix E3: Cumulative Performance of Model versus Number of Principal Components Selected (Early vs Late; 340 Lipids)

DETAILED DESCRIPTION

We disclose combinations of lipids which are predictive of a biological state of a sample. We describe various methods of determining the status of a sample, by determining the concentration of one or more, such as a plurality, of lipids in the sample.

We disclose the use of such combinations to predict the biological state of a sample. The methods include both biochemical and bioinformatic methods.

We disclose methods comprising assaying the concentration of particular lipids and combinations of lipids in biological samples as well as rules for determining from such lipid concentrations a biological state of the sample. The lipid concentrations of the combinations of the lipids may therefore be used in a "biochemical" method, as described below, to provide an indication of the state, condition or status of sample, such as a biological state.

The combinations of lipids, and concentrations thereof, may also be used in a "bioinformatics" method.

The bioinformatics methods involve applying classification models disclosed in this document to lipid concentration data obtained from unknown samples. The classification models may be generated using lipid concentration data from biological samples in known states, as described in detail below. The bioinformatics predictive methods may involve biochemical steps, and vice versa. The bioinformatics methods may comprise simply applying already generated classification models onto obtained data, or they may actually include model generation steps.

We therefore disclose classification models, methods of generating such classification models and methods of applying such classification models, which may be used bioinformatically for such predictions.

The biological state may comprise a cancerous state. It may comprise a neoplasmic state or a tumour state. The cancer may comprise ovarian cancer. The biological state may comprise a malignancy state of a cancer. The malignancy state may comprise a benign state or it may comprise a malignant state. The biological state may comprise a stage of a cancer. The stage may comprise an early stage or a late stage.

The term "ovarian cancer" as used in this document may comprise ovarian tumors, carcinomas, (e.g., carcinoma in situ, invasive carcinoma, metastatic carcinoma) and premalignant conditions. It further includes both benign and malignant tumors, such as ovarian germ cell tumors, e.g. teratomas, dysgerminoma, endodermal sinus tumor and embryonal carcinoma, and ovarian stromal tumors, e.g. granulosa, theca, Sertoli, Leydig, and collagen-producing stromal cells. Ovarian cancers also include recognized histological tumor types, such as, for example, serous, mucinous, endometrioid, and clear cell tumors.

The ovarian cancer stage may be established using for example the FIGO staging system, as described in L. Sobin and Ch Wittekind (eds.), *TNM Classification of malignant tumours*. UICC Internation Union against Cancer, Geneva, Switzerland, p155-157; 6th ed. 2002. "Early" stage may correspond to Stage I and Stage II. "Late" stage may correspond to Stage III and Stage IV.

The biological state may comprise one of at least two binary states. It may comprise one two biological states. The biological states may comprise or example, a diseased state (such as a cancer state) and a normal state, a benign state and a malignant state and an early stage state and a late stage state. The biological states may comprise a normal/benign state and a malignant state. The biological states may comprise a benign state and an early state.

Thus, the Examples below show that a combination of 340 lipids, as shown in Table D3, may be analysed in a sample in order to determine the status of a sample. The Examples show that the is capable of revealing whether the sample is normal or diseased (ovarian cancer). These lipids may also be used to further determine whether such a sample is a benign sample or a malignant sample. Further analysis with these lipids may be done to determine whether such a sample is an early stage sample or a late stage sample.

The methods and compositions described here involve determining lipid concentrations in a sample. The concentrations may be those of the lipids in a lipid combination disclosed herein and means of obtaining the concentrations are described in detail below.

Lipid Combinations

Our methods may involve determining lipid concentrations of a number of lipids.

The combination of lipids may comprise any two or more choline lipids, such as phosphatidylcholine (GPCho) or sphingomyelin (SM) or both. The combinations may comprise any two or more lipids selected from the group consisting of: phosphatidic acid (GPA). They may comprise phosphatidylglycerol (GPGro), phosphatidylserine acid (GPSer), sulfatides, cardiolipin, phosphatidylethanolamine (GPEtn), phosphatidylinositol (GPIns), phosphatidylinositol phosphates (GPInsPs), ceramide (Cer), mono hexosyl ceramide (MonoHexCer) and di hexosyl ceramide (DiHexCer). The combinations may comprise lipids from more than one class.

We therefore disclose combinations of lipids comprising, such as consisting of, all or substantially all of the (a) lipids shown in Table D1; (b) lipids shown in Table D2; (c) lipids shown in Table D3; (d) lipids shown in Table E4; and (e) lipids shown in Table E6. We further disclose combinations of such combinations.

We further disclose combinations of any two or more lipids from each of these tables. The two or more lipids may be contiguous or non-contiguous. For example, we disclose a combination of 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 331, 332, 333, 334, 335, 336, 337, 338, 339 or 440 lipids from any of these tables, for example, Table D3.

Any number of lipids within the 340 lipids shown in Table D3 may be employed for the purposes described in this document. For example, all or substantially all of these lipids may be used. As another example, combinations comprising subsets from the 340 lipids may also be employed. Thus, a combination of any n lipids of the list of 340 lipids, where n≤340, may be used for such analysis.

Such combinations may comprise contiguous subsets or non-contiguous subsets. For example, combinations may be formed primarily from the top half of the list of Table D3. They may be formed primarily from the top third of the list, the top quarter, the top fifth, the top sixth, the top seventh, the top eighth, the top ninth or the top tenth of the list. Thus, subsets may be formed from the first 170, the first 114, the first 85, the first 68, the first 57, the first 49, the first 43 or the first 38 members of the list.

In general terms, subsets of the list of Table D3 lipids may, for example, include a certain number of lipids from top of the list of lipids shown in Table D3. Such lipid combinations may comprise the first n lipids from the list of lipids shown in Table D3. For example, n could be 82. Such a combination of lipids is shown in Table D2. A further combination of lipids could comprise the first n lipids from the list of lipids shown in Table D3, where n=44. Such a combination of lipids is shown in Table E6. Yet another combination of lipids may comprise the first 30 lipids from the list of lipids shown in Table D3 (i.e., n=30). Such a combination of lipids is shown in Table E4.

Other combinations comprising subsets of the list of 340 lipids may comprise a selection of lipids from Table D3, based on any suitable criteria, such as lipid class, molecular weight, side group, etc. For example, subsets may be formed comprising all lipids in particular lipid class from the lipids set out in Table D3. A subset may comprise choline lipids, for example. Such an example subset is shown in Table D1 (below), and comprises a list of 77 choline lipids.

Lipid nomenclature is as described in Fahy, et al (2005). A comprehensive classification system for lipids. Journal of Lipid Research, Vol. 46, 839-862.

TABLE D1

List of 77 Choline Lipids

| | Lipid | | |
|---|---|---|---|
| 1 | 494.4/184.1>GPCho:Lyso 16:1 | 40 | 810.6/184.1>GPCho:38:4a |
| 2 | 496.4/184.1>GPCho:Lyso 16:0 | 41 | 812.6/184.1>GPCho:38:3a |
| 3 | 520.4/184.1>GPCho:Lyso 18:2 | 42 | 814.6/184.1>GPCho:38:2a |
| 4 | 522.4/184.1>GPCho:Lyso 18:1 | 43 | 816.6/184.1>GPCho:38:1a |
| 5 | 524.4/184.1>GPCho:Lyso 18:0 | 44 | 820.6/184.1>GPCho:40:5p, 40:6e |
| 6 | 544.4/184.1>GPCho:Lyso 20:4 | 45 | 822.6/184.1>GPCho:40:4p, 40:5e |
| 7 | 568.4/184.1>GPCho:Lyso 22:6 | 46 | 824.6/184.1>GPCho:40:3p, 40:4e |
| 8 | 570.4/184.1>GPCho:Lyso 22:5 | 47 | 826.6/184.1>GPCho:40:2p, 40:3e |
| 9 | 678.5/184.1>GPCho:28:0 | 48 | 828.6/184.1>GPCho:40:1p, 40:2e |
| 10 | 678.5/184.1>GPCho:28:0a | 49 | 834.6/184.1>GPCho:40:6a |
| 11 | 704.6/184.1>GPCho:30:1a | 50 | 836.6/184.1>GPCho:40:5a |
| 12 | 706.6/184.1>GPCho:30:0a | 51 | 838.6/184.1>GPCho:40:4a |
| 13 | 718.6/184.1>GPCho:32:0p, 32:1e | 52 | 701.5/184.1>SM:18/16:1 |
| 14 | 730.8/184.1>GPCho:32:2 | 53 | 703.5/184.1>SM:18/16:0 |
| 15 | 732.6/184.1>GPCho:32:1a | 54 | 703.8/184.4>SM:d18:1/16:0 |
| 16 | 734.6/184.1>GPCho:32:0a | 55 | 705.8/184.4>SM:d18:0/16:0 |
| 17 | 742.6/184.1>GPCho:34:2p, 34:3e | 56 | 727.6/184.1>SM:18/18:2 |
| 18 | 744.6/184.1>GPCho:34:1p, 34:2e | 57 | 729.6/184.1>SM:18/18:1 |
| 19 | 746.6/184.1>GPCho:34:0p, 34:1e | 58 | 731.6/184.1>SM:18/18:0 |
| 20 | 748.6/184.1>GPCho:34:0e | 59 | 731.8/184.4>SM:d18:1/18:0 |
| 21 | 756.6/184.1>GPCho:34:3a | 60 | 733.8/184.4>SM:d18:0/18:0 |
| 22 | 758.7/184.1>GPCho:34:2a | 61 | 757.6/184.1>SM:18/20:1 |
| 23 | 760.6/184.1>GPCho:34:1a | 62 | 759.6/184.1>SM:18/20:0 |
| 24 | 762.6/184.1>GPCho:34:0a | 63 | 759.8/184.4>SM:d18:1/20:0 |
| 25 | 768.6/184.1>GPCho:36:3p, 36:4e | 64 | 761.8/184.4>SM:d18:0/20:0 |
| 26 | 770.6/184.1>GPCho:36:2p, 36:3e | 65 | 773.6/184.1>SM:18/21:0 |
| 27 | 772.6/184.1>GPCho:36:1p, 36:2e | 66 | 787.6/184.1>SM:18/22:0 |
| 28 | 774.6/184.1>GPCho:36:0p, 36:1e | 67 | 787.9/184.4>SM:d18:1/22:0 |
| 29 | 782.6/184.1>GPCho:36:4a | 68 | 789.9/184.4>SM:d18:0/22:0 |
| 30 | 784.6/184.1>GPCho:36:3a | 69 | 813.6/184.1>SM:18/24:1 |
| 31 | 786.6/184.1>GPCho:36:2a | 70 | 813.9/184.4>SM:d18:1/24:1 |

TABLE D1-continued

| List of 77 Choline Lipids | | | |
|---|---|---|---|
| | Lipid | | |
| 32 | 788.6/184.1>GPCho:36:1a | 71 | 815.6/184.1>SM:18/24:0 |
| 33 | 790.8/184.1>GPCho:36:0 | 72 | 815.9/184.4>SM:d18:0/24:1 |
| 34 | 792.6/184.1>GPCho:38:5p, 38:6e | 73 | 817.9/184.4>SM:d18:0/24:0 |
| 35 | 794.6/184.1>GPCho:38:4p, 38:5e | 74 | 841.9/184.4>SM:d18:1/26:1 |
| 36 | 796.6/184.1>GPCho:38:3p, 38:4e | 75 | 843.9/184.4>SM:d18:0/26:1 |
| 37 | 798.6/184.1>GPCho:38:2p, 38:3e | 76 | 843.9/184.4>SM:d18:1/26:0 |
| 38 | 800.6/184.1>GPCho:38:1p, 38:2e | 77 | 845.9/184.4>SM:d18:0/26:0 |
| 39 | 808.6/184.1>GPCho:38:5a | | |

TABLE D2

| List of 82 lipids<br>List of 82 Lipids | | | | | |
|---|---|---|---|---|---|
| | Lipid | m/z | Benign | Malignant | p-value |
| 1 | GPA:36:0 | 703.8 | 29.71 | 80.76 | <1.0E−06 |
| 2 | GPA:16:0/22:5 | 721.8 | 65.75 | 187.84 | <1.0E−06 |
| 3 | GPA:38:0 | 731.8 | 44.66 | 109.80 | <1.0E−06 |
| 4 | GPGro:Lyso 16:0 | 483.4 | 89.99 | 175.45 | <1.0E−06 |
| 5 | GPGro:Lyso 18:0 | 511.4 | 89.22 | 186.02 | <1.0E−06 |
| 6 | GPGro:18:2/18:2 | 769.8 | 101.89 | 68.33 | <1.0E−06 |
| 7 | GPGro:18:0/18:0 | 777.8 | 57.67 | 175.25 | <1.0E−06 |
| 8 | GPEtn:Lyso18:2a | 476.6 | 55.96 | 46.37 | <1.0E−06 |
| 9 | GPEtn:Lyso 18:1 | 478.4 | 61.14 | 53.12 | <1.0E−06 |
| 10 | GPEtn:Lyso 20:4 | 500.4 | 77.46 | 40.49 | <1.0E−06 |
| 11 | GPEtn:Lyso 22:6 | 524.4 | 96.20 | 51.64 | <1.0E−06 |
| 12 | GPCho:32:0a | 734.6 | 106.21 | 125.10 | <1.0E−06 |
| 13 | GPCho:34:2e | 744.6 | 81.22 | 65.69 | <1.0E−06 |
| 14 | GPCho:36:2a | 786.6 | 90.83 | 81.70 | <1.0E−06 |
| 15 | GPCho:38:2a | 814.6 | 103.44 | 127.24 | <1.0E−06 |
| 16 | Cer: d18:1/18:0 | 566.7 | 118.28 | 232.24 | <1.0E−06 |
| 17 | Cer: d18:1/20:0 | 594.7 | 96.63 | 172.62 | <1.0E−06 |
| 18 | Cer: d18:1/22:0 | 622.8 | 74.18 | 122.63 | <1.0E−06 |
| 19 | Cer: d18:1/24:1 | 648.9 | 84.79 | 167.95 | <1.0E−06 |
| 20 | SM: d18:1/18:0 | 731.8 | 120.26 | 154.36 | <1.0E−06 |
| 21 | SM: d18:1/22:0 | 787.9 | 89.88 | 88.01 | <1.0E−06 |
| 22 | SM: d18:1/24:1 | 813.9 | 106.69 | 132.41 | <1.0E−06 |
| 23 | GPA:36:1 | 701.8 | 15.82 | 47.90 | 1.0E−06 |
| 24 | GPCho:36:3a | 784.6 | 93.47 | 79.88 | 1.0E−06 |
| 25 | GPCho:40:5p, 40:6e | 820.6 | 126.80 | 91.35 | 1.0E−06 |
| 26 | GPCho:40:6a | 834.6 | 137.30 | 94.11 | 1.0E−06 |
| 27 | SM: d18:1/26:0 | 843.9 | 135.42 | 92.25 | 1.0E−06 |
| 28 | GPCho:Lyso 18:2 | 520.4 | 78.55 | 75.98 | 2.0E−06 |
| 29 | GPCho:38:5a | 808.6 | 117.55 | 86.87 | 3.0E−06 |
| 30 | GPA:18:1/16:0 | 673.8 | 34.06 | 71.35 | 4.0E−06 |
| 31 | Cer: d18:1/24:0 | 650.9 | 58.15 | 91.39 | 5.0E−06 |
| 32 | GPCho:38:5p, 38:6e | 792.6 | 113.63 | 89.05 | 6.0E−06 |
| 33 | DiHexCer: d18:1/18:0 | 890.7 | 93.33 | 143.80 | 7.0E−06 |
| 34 | GPGro:18:2/18:1 | 771.8 | 75.18 | 77.63 | 1.0E−05 |
| 35 | GPCho:36:2p, 36:3e | 770.6 | 93.96 | 80.83 | 1.0E−05 |
| 36 | GPA:36:2 | 699.8 | 41.77 | 76.41 | 1.1E−05 |
| 37 | GPCho:28:0a | 678.5 | 62.22 | 69.74 | 1.2E−05 |
| 38 | MonoHexCer: d18:1/18:0 | 728.7 | 78.23 | 130.92 | 1.3E−05 |
| 39 | MonoHexCer: d18:1/24:1 | 810.9 | 96.74 | 147.14 | 1.9E−05 |
| 40 | Cer: d18:1/16:0 | 538.7 | 109.71 | 152.16 | 2.6E−05 |
| 41 | GPCho:32:1a | 732.6 | 106.83 | 121.94 | 3.3E−05 |
| 42 | GPGro:18:2/18:0 | 773.8 | 78.31 | 91.50 | 3.5E−05 |
| 43 | GPCho:36:3p, 36:4e | 768.6 | 107.07 | 84.53 | 5.0E−05 |
| 44 | GPGro:18:1/18:0 | 775.8 | 97.92 | 131.80 | 8.4E−05 |
| 45 | SM:d18:1/16:0 | 703.8 | 106.53 | 119.97 | 1.1E−04 |
| 46 | GPA:Lyso 18:0 | 437.4 | 58.55 | 92.21 | 1.4E−04 |
| 47 | GPCho:38:4p, 38:5e | 794.6 | 119.84 | 95.63 | 1.8E−04 |
| 48 | MonoHexCer: d18:1/16:0 | 700.7 | 100.99 | 133.15 | 1.9E−04 |
| 49 | GPCho:Lyso 22:6 | 568.4 | 125.53 | 89.80 | 1.9E−04 |
| 50 | GPCho:40:1p, 40:2e | 828.6 | 96.59 | 128.57 | 2.1E−04 |
| 51 | DiHexCer: d18:1/24:1 | 972.9 | 94.84 | 141.35 | 6.6E−04 |
| 52 | SM: d18:1/26:1 | 841.9 | 92.64 | 128.68 | 7.0E−04 |
| 53 | GPGro:Lyso 18:2 | 507.4 | 81.41 | 123.68 | 9.7E−04 |
| 54 | GPCho:30:1a | 704.6 | 102.55 | 116.54 | 1.1E−03 |
| 55 | GPCho:38:3p, 38:4e | 796.6 | 114.76 | 96.77 | 1.3E−03 |
| 56 | GPCho:Lyso 22:5 | 570.4 | 111.54 | 87.89 | 1.4E−03 |
| 57 | GPCho:36:4a | 782.6 | 109.60 | 91.61 | 1.5E−03 |
| 58 | GPA:40:0 | 759.8 | 61.30 | 93.59 | 2.0E−03 |
| 59 | GPCho:38:4a | 810.6 | 114.05 | 94.41 | 2.4E−03 |
| 60 | GPCho:40:2p, 40:3e | 826.6 | 87.13 | 122.72 | 2.4E−03 |
| 61 | GPA:40:1 | 757.8 | 82.86 | 102.69 | 2.4E−03 |
| 62 | GPA:18:0/20:4 | 723.8 | 64.99 | 86.23 | 2.6E−03 |
| 63 | GPCho:34:3a | 756.6 | 78.28 | 107.87 | 3.0E−03 |
| 64 | DiHexCer: d18:1/24:0 | 974.9 | 90.17 | 119.47 | 3.5E−03 |
| 65 | GPGro:Lyso 18:1 | 509.4 | 126.58 | 136.56 | 3.7E−03 |
| 66 | GPCho:34:2a | 758.7 | 102.25 | 93.80 | 3.7E−03 |
| 67 | GPCho:36:1a | 788.6 | 88.10 | 93.30 | 3.9E−03 |
| 68 | GPCho:34:0e | 748.6 | 100.65 | 109.00 | 4.8E−03 |
| 69 | GPGro:18:2/16:1 | 743.8 | 98.53 | 88.80 | 5.1E−03 |
| 70 | GPCho:38:1a | 816.6 | 89.63 | 102.87 | 8.0E−03 |
| 71 | DiHexCer: d18:1/22:0 | 946.8 | 92.28 | 122.15 | 8.7E−03 |
| 72 | MonoHexCer: d18:1/22:0 | 784.8 | 89.45 | 107.59 | 9.7E−03 |
| 73 | GPCho:36:1p, 36:2e | 772.6 | 87.79 | 88.82 | 1.2E−02 |
| 74 | MonoHexCer: d18:1/24:0 | 812.9 | 90.45 | 102.49 | 1.2E−02 |
| 75 | DiHexCer: d18:1/16:0 | 862.7 | 91.93 | 115.85 | 1.4E−02 |
| 76 | GPEtn:Lyso 18:0 | 480.4 | 89.30 | 104.93 | 1.5E−02 |
| 77 | GPA:16:0/16:0 | 647.8 | 76.90 | 108.70 | 1.6E−02 |
| 78 | GPCho:34:2p, 34:3e | 742.6 | 79.46 | 82.38 | 1.6E−02 |
| 79 | GPCho:34:0a | 762.6 | 101.35 | 109.61 | 3.2E−02 |
| 80 | GPCho:Lyso 20:4 | 544.4 | 102.40 | 89.08 | 3.3E−02 |
| 81 | GPCho:40:5a | 836.6 | 111.74 | 97.42 | 4.1E−02 |
| 82 | GPA:Lyso 16:0 | 409.4 | 93.86 | 115.94 | 4.7E−02 |

TABLE D3

| List of 340 choline lipids<br>List of 340 Lipids | |
|---|---|
| No. | Lipid |
| 1 | GPA:Lyso 16:0 |
| 2 | GPA:Lyso 18:2 |
| 3 | GPA:Lyso 18:1 |
| 4 | GPA:Lyso 18:0 |
| 5 | GPA:Lyso 18:0 |
| 6 | GPA:Lyso 20:3 |
| 7 | GPA:Lyso 20:2 |
| 8 | GPA:Lyso 20:1 |
| 9 | GPA:Lyso 20:0 |
| 10 | GPA:Lyso 22:6 |
| 11 | GPA:Lyso 22:5 |
| 12 | GPA:16:1/16:2 |
| 13 | GPA:16:1/16:1 |
| 14 | GPA:16:1/16:0 |
| 15 | GPA:16:0/16:0 |
| 16 | GPA:34:4 |
| 17 | GPA:34:3 |
| 18 | GPA:34:4 |
| 19 | GPA:18:2/16:0 |
| 20 | GPA:18:1/16:0 |
| 21 | GPA:36:4 |
| 22 | GPA:36:4 |

TABLE D3-continued

| List of 340 choline lipids<br>List of 340 Lipids | |
|---|---|
| No. | Lipid |
| 23 | GPA:20:3/16:0 |
| 24 | GPA:18:1/18:2 |
| 25 | GPA:36:2 |
| 26 | GPA:36:2 |
| 27 | GPA:36:1 |
| 28 | GPA:36:0 |
| 29 | GPA:18:1/20:4 |
| 30 | GPA:16:0/22:5 |
| 31 | GPA:18:0/20:4 |
| 32 | GPA:20:3/18:0 |
| 33 | GPA:38:1 |
| 34 | GPA:38:0 |
| 35 | GPA:40:4 |
| 36 | GPA:40:1 |
| 37 | GPA:40:0 |
| 38 | GPA:42:5 |
| 39 | GPGro:Lyso 16:1 |
| 40 | GPGro:Lyso 16:0 |
| 41 | GPGro:Lyso 18:2 |
| 42 | GPGro:Lyso 18:1 |
| 43 | GPGro:Lyso 18:0 |
| 44 | GPGro:Lyso 20:4 |
| 45 | GPGro:Lyso 22:6 |
| 46 | GPGro:Lyso 22:5 |
| 47 | GPGro:16:1/16:1 |
| 48 | GPGro:16:1/16:0 |
| 49 | GPGro:16:0/16:0 |
| 50 | GPGro:18:2/16:1 |
| 51 | GPGro:18:1/16:2 |
| 52 | GPGro:18:2/16:0 |
| 53 | GPGro:18:1/16:1 |
| 54 | GPGro:16:0/18:1 |
| 55 | GPGro:16:0/18:1 |
| 56 | GPGro:18:0/16:0 |
| 57 | GPGro:20:4/16:1 |
| 58 | GPGro:18:2/18:2 |
| 59 | GPGro:20:4/16:0 |
| 60 | GPGro:18:2/18:1 |
| 61 | GPGro:18:2/18:0 |
| 62 | GPGro:18:1/18:1 |
| 63 | GPGro:18:1/18:0 |
| 64 | GPGro:18:0/18:0 |
| 65 | GPGro:20:4/18:1 |
| 66 | GPGro:20:4/18:0 |
| 67 | GPGro:22:6/18:0 |
| 68 | GPGro:22:5/18:0 |
| 69 | GPSer:Lyso 16:1 |
| 70 | GPSer:Lyso 16:0 |
| 71 | GPSer:Lyso 18:1 |
| 72 | GPSer:Lyso 18:0 |
| 73 | GPSer:Lyso 20:4 |
| 74 | GPSer:Lyso 22:5 |
| 75 | GPSer:32:1 |
| 76 | GPSer:32:0 |
| 77 | GPSer:34:2 |
| 78 | GPSer:34:1 |
| 79 | GPSer:34:0 |
| 80 | GPSer:36:4 |
| 81 | GPSer:36:3 |
| 82 | GPSer:36:2 |
| 83 | GPSer:36:1 |
| 84 | GPSer:36:0 |
| 85 | GPSer:38:6 |
| 86 | GPSer:38:5 |
| 87 | GPSer:38:4 |
| 88 | GPSer:38:3 |
| 89 | GPSer:38:2 |
| 90 | GPSer:38:1 |
| 91 | GPSer:40:6 |
| 92 | GPSer:40:5 |
| 93 | GPSer:40:4 |
| 94 | GPSer:40:3 |
| 95 | Sulfatide:16:0 |
| 96 | Sulfatide:18:0 |
| 97 | Sulfatide:18:0 (OH) |

TABLE D3-continued

| List of 340 choline lipids<br>List of 340 Lipids | |
|---|---|
| No. | Lipid |
| 98 | Sulfatide:20:0 |
| 99 | Sulfatide:20:0 (OH) |
| 100 | Sulfatide:22:1 |
| 101 | Sulfatide:22:1 (OH) |
| 102 | Sulfatide:24:1 |
| 103 | Sulfatide:24:0 |
| 104 | Sulfatide:24:0 (OH) |
| 105 | Cardiolipin:52:3 |
| 106 | Cardiolipin:66:2 |
| 107 | Cardiolipin:68:4 |
| 108 | Cardiolipin:68:3 |
| 109 | Cardiolipin:68:2 |
| 110 | Cardiolipin:68:1 |
| 111 | Cardiolipin:70:5 |
| 112 | Cardiolipin:70:4 |
| 113 | Cardiolipin:70:3 |
| 114 | Cardiolipin:70:2 |
| 115 | Cardiolipin:70:l |
| 116 | Cardiolipin:70:0 |
| 117 | GPEtn:Lyso16:1e/16:0p |
| 118 | GPEtn:Lyso 16:1 |
| 119 | GPEtn:Lyso 16:0 |
| 120 | GPEtn:Lyso18:2e/18:1p |
| 121 | GPEtn:Lyso18:1e/18:0p |
| 122 | GPEtn:Lyso18:2a |
| 123 | GPEtn:Lyso 18:1 |
| 124 | GPEtn:Lyso 18:0 |
| 125 | GPEtn:Lyso20:1e/20:0p |
| 126 | GPEtn:Lyso 20:4 |
| 127 | GPEtn:Lyso 22:6 |
| 128 | GPEtn:16:0/16:1 |
| 129 | GPEtn:16:0/16:0 |
| 130 | GPEtn:34:2p, 34:3e |
| 131 | GPEtn:34:1p, 34:2e |
| 132 | GPEtn:34:0p, 34:1e |
| 133 | GPEtn:18:1/16:1 |
| 134 | GPEtn:18:2/16:1 |
| 135 | GPEtn:18:1/16:1 |
| 136 | GPEtn:18:1/16:0 |
| 137 | GPEtn:18:0/16:0 |
| 138 | GPEtn:36:4p |
| 139 | GPEtn:36:3p, 36:4e |
| 140 | GPEtn:36:2p, 36:3e |
| 141 | GPEtn:36:1p, 36:2e |
| 142 | GPEtn:20:4/16:0 |
| 143 | GPEtn:18:2/18:1 |
| 144 | GPEtn:18:1/18:1 |
| 145 | GPEtn:18:0/18:1 |
| 146 | GPEtn:18:0/18:0 |
| 147 | GPEtn:38:5p, 38:6e |
| 148 | GPEtn:38:4p, 38:5e |
| 149 | GPEtn:38:3p, 38:4e |
| 150 | GPEtn:38:2p, 38:3e |
| 151 | GPEtn:38:1p, 38:2e |
| 152 | GPEtn:20:4/18:2 |
| 153 | GPEtn:20:4/18:1 |
| 154 | GPEtn:20:4/18:0 |
| 155 | GPEtn:20:3/18:0 |
| 156 | GPEtn:20:2/18:0 |
| 157 | GPEtn:20:1/18:0 |
| 158 | GPEtn:40:5p, 40:6e |
| 159 | GPEtn:40:4p, 40:5e |
| 160 | GPEtn:40:3p, 40:4e |
| 161 | GPEtn:40:1p, 40:2e |
| 162 | GPEtn:22:4/18:3 |
| 163 | GPEtn:22:4/18:2 |
| 164 | GPEtn:40:5a |
| 165 | GPEtn:40:4a |
| 166 | GPEtn:40:3a |
| 167 | GPEtn:40:2a |
| 168 | GPIns:Lyso 16:1 |
| 169 | GPIns:Lyso 16:0 |
| 170 | GPIns:Lyso 18:2 |
| 171 | GPIns:Lyso 18:1 |
| 172 | GPIns:Lyso 18:0 |

TABLE D3-continued

List of 340 choline lipids
List of 340 Lipids

| No. | Lipid |
|---|---|
| 173 | GPIns:Lyso 20:4 |
| 174 | GPIns:Lyso 20:3 |
| 175 | GPIns:Lyso 20:2 |
| 176 | GPIns:Lyso 20:1 |
| 177 | GPIns:Lyso 20:0 |
| 178 | GPIns:Lyso 24:2 |
| 179 | GPIns:34:1 |
| 180 | GPIns:34:1 |
| 181 | GPIns:34:1 |
| 182 | GPIns:36:4 |
| 183 | GPIns:36:3 |
| 184 | GPIns:36:2 |
| 185 | GPIns:18:0/18:1 |
| 186 | GPIns:36:0 |
| 187 | GPIns:37:3 |
| 188 | GPIns:38:5 |
| 189 | GPIns:38:4 |
| 190 | GPIns:38:3 |
| 191 | GPIns:38:2 |
| 192 | GPIns:38:1 |
| 193 | GPIns:38:0 |
| 194 | GPIns:40:6 |
| 195 | GPIns:40:5 |
| 196 | GPIns:40:4 |
| 197 | GPIns:40:3 |
| 198 | GPIns:40:2 |
| 199 | GPIns:40:1 |
| 200 | GPInsP:38:5 |
| 201 | GPInsP:38:5 |
| 202 | GPInsP:38:4 |
| 203 | GPInsP:38:4 |
| 204 | GPInsP:38:3 |
| 205 | GPInsP:38:3 |
| 206 | GPInsP2:38:4 |
| 207 | GPInsP2:38:4 |
| 208 | GPInsP2:38:4 |
| 209 | GPInsP2:38:3 |
| 210 | GPInsP2:38:3 |
| 211 | GPInsP2:38:3 |
| 212 | GPInsP3:38:4 |
| 213 | GPInsP3:38:4 |
| 214 | GPInsP3:38:4 |
| 215 | GPInsP3:38:4 |
| 216 | GPCho:Lyso 16:1 |
| 217 | GPCho:Lyso 16:0 |
| 218 | GPCho:Lyso 18:2 |
| 219 | GPCho:Lyso 18:1 |
| 220 | GPCho:Lyso 18:0 |
| 221 | GPCho:Lyso 20:4 |
| 222 | GPCho:Lyso 22:6 |
| 223 | GPCho:Lyso 22:5 |
| 224 | GPCho:28:0 |
| 225 | GPCho:28:0a |
| 226 | GPCho:30:1a |
| 227 | GPCho:30:0a |
| 228 | GPCho:32:0p, 32:1e |
| 229 | GPCho:32:2 |
| 230 | GPCho:32:1a |
| 231 | GPCho:32:0a |
| 232 | GPCho:34:2p, 34:3e |
| 233 | GPCho:34:1p, 34:2e |
| 234 | GPCho:34:0p, 34:1e |
| 235 | GPCho:34:0e |
| 236 | GPCho:34:3a |
| 237 | GPCho:34:2a |
| 238 | GPCho:34:1a |
| 239 | GPCho:34:0a |
| 240 | GPCho:36:3p, 36:4e |
| 241 | GPCho:36:2p, 36:3e |
| 242 | GPCho:36:1p, 36:2e |
| 243 | GPCho:36:0p, 36:1e |
| 244 | GPCho:36:4a |
| 245 | GPCho:36:3a |
| 246 | GPCho:36:2a |
| 247 | GPCho:36:1a |

TABLE D3-continued

List of 340 choline lipids
List of 340 Lipids

| No. | Lipid |
|---|---|
| 248 | GPCho:36:0 |
| 249 | GPCho:38:5p, 38:6e |
| 250 | GPCho:38:4p, 38:5e |
| 251 | GPCho:38:3p, 38:4e |
| 252 | GPCho:38:2p, 38:3e |
| 253 | GPCho:38:1p, 38:2e |
| 254 | GPCho:38:5a |
| 255 | GPCho:38:4a |
| 256 | GPCho:38:3a |
| 257 | GPCho:38:2a |
| 258 | GPCho:38:1a |
| 259 | GPCho:40:5p, 40:6e |
| 260 | GPCho:40:4p, 40:5e |
| 261 | GPCho:40:3p, 40:4e |
| 262 | GPCho:40:2p, 40:3e |
| 263 | GPCho:40:1p, 40:2e |
| 264 | GPCho:40:6a |
| 265 | GPCho:40:5a |
| 266 | GPCho:40:4a |
| 267 | SM:18/16:1 |
| 268 | SM:18/16:0 |
| 269 | SM:d18:1/16:0 |
| 270 | SM:d18:0/16:0 |
| 271 | SM:18/18:2 |
| 272 | SM:18/18:1 |
| 273 | SM:18/18:0 |
| 274 | SM:d18:1/18:0 |
| 275 | SM:d18:0/18:0 |
| 276 | SM:18/20:1 |
| 277 | SM:18/20:0 |
| 278 | SM:d18:1/20:0 |
| 279 | SM:d18:0/20:0 |
| 280 | SM:18/21:0 |
| 281 | SM:18/22:0 |
| 282 | SM:d18:1/22:0 |
| 283 | SM:d18:0/22:0 |
| 284 | SM:18/24:1 |
| 285 | SM:d18:1/24:1 |
| 286 | SM:18/24:0 |
| 287 | SM:d18:0/24:1 |
| 288 | SM:d18:0/24:0 |
| 289 | SM:d18:1/26:1 |
| 290 | SM:d18:0/26:1 |
| 291 | SM:d18:1/26:0 |
| 292 | SM:d18:0/26:0 |
| 293 | Cer:d18:1/16:0 |
| 294 | Cer:d18:0/16:0 |
| 295 | Cer:d18:1/18:0 |
| 296 | Cer:d18:0/18:0 |
| 297 | Cer:d18:1/20:0 |
| 298 | Cer:d18:0/20:0 |
| 299 | Cer:d18:1/22:0 |
| 300 | Cer:d18:0/22:0 |
| 301 | Cer:d18:1/24:1 |
| 302 | Cer:d18:1/24:0 |
| 303 | Cer:d18:0/24:1 |
| 304 | Cer:d18:0/24:0 |
| 305 | Cer:d18:1/26:1 |
| 306 | Cer:d18:1/26:0 |
| 307 | Cer:d18:0/26:1 |
| 308 | Cer:d18:0/26:0 |
| 309 | MonoHexCer:d18:1/16:0 |
| 310 | MonoHexCer:d18:0/16:0 |
| 311 | MonoHexCer:d18:1/18:0 |
| 312 | MonoHexCer:d18:0/18:0 |
| 313 | MonoHexCer:d18:1/20:0 |
| 314 | MonoHexCer:d18:0/20:0 |
| 315 | MonoHexCer:d18:1/22:0 |
| 316 | MonoHexCer:d18:0/22:0 |
| 317 | MonoHexCer:d18:1/24:1 |
| 318 | MonoHexCer:d18:0/24:1 |
| 319 | MonoHexCer:d18:1/24:0 |
| 320 | MonoHexCer:d18:0/24:0 |
| 321 | MonoHexCer:d18:1/26:1 |
| 322 | MonoHexCer:d18:0/26:1 |

TABLE D3-continued

| List of 340 choline lipids<br>List of 340 Lipids | |
|---|---|
| No. | Lipid |
| 323 | MonoHexCer:d18:1/26:0 |
| 324 | MonoHexCer:d18:0/26:0 |
| 325 | DiHexCer:d18:1/16:0 |
| 326 | DiHexCer:d18:0/16:0 |
| 327 | DiHexCer:d18:1/18:0 |
| 328 | DiHexCer:d18:0/18:0 |
| 329 | DiHexCer:d18:1/20:0 |
| 330 | DiHexCer:d18:0/20:0 |
| 331 | DiHexCer:d18:1/22:0 |
| 332 | DiHexCer:d18:0/22:0 |
| 333 | DiHexCer:d18:1/24:1 |
| 334 | DiHexCer:d18:0/24:1 |
| 335 | DiHexCer:d18:1/24:0 |
| 336 | DiHexCer:d18:0/24:0 |
| 337 | DiHexCer:d18:1/26:1 |
| 338 | DiHexCer:d18:0/26:1 |
| 339 | DiHexCer:d18:1/26:0 |
| 340 | DiHexCer:d18:0/26:0 |

Lipid Concentration Determination

Any suitable method of determining the concentration of a lipid in a sample may be carried out as known in the art.

The samples may comprise, for example, bodily fluids, such as blood, blood serum, synoival fluid, tissue lysates, and extracts prepared from tissues.

For example, any of a number of known methods for lipid concentration determination such as involving colorimetric or fluorimetric methods, may be used.

Such methods are described for example in European Patent EP0531933 and at http://www-unix.oit.umass.edu/~mcclemen/581Lipids.html, in Holman et al. (1964) Am J Clin Nutr, 14 (4): 193, Nogueira et al (2007), Critical Care, 11(Suppl 3):P19, etc. Antonis et al (1967). *Automated techniques in serum lipid analysis*. Journal of the American Oil Chemists' Society, 44, 6, 333-340 describes in detail methods of determining lipid concentrations in serum samples. A number of kits for determination of lipid concentrations are also commercially available.

For choline lipids, a number of assays as described in detail in the section "Assays for Choline Lipids" may be employed. Lipid concentration determination methods may involve high performance liquid chromatography (HPLC), as described in Patton et al (1982).

The lipid concentration determination may be conducted using mass spectrometry. For example, electrospray ionization-mass spectrometry (ESI-MS) may be used. ESI-MS is described in detail in Kerwin et al (1994), Kim et al (1994), Han et al (1994), Myher et al (1995), Han et al (1996), Brügger et al (1997), Ramanadham et al (1998) Schneiter et al (1999), Hsu et al (2000), Koivusaloa et al (2001).

Assays for Choline Lipids

Assays for choline lipids, phosphatidylcholine and sphingomyelin are known in the art and may be applied to determine the concentrations of for example the 77 choline lipids shown in Table D1.

An assay for phosphatidylcholine is described in detail in Hojjati, M. R., Jiang, X. *Rapid, specific, and sensitive measurements of plaSphingomyelina sphingomyelin and phosphatidylcholine*. J Lipid Res 47(3) 673-676 (2006). In this assay, PC-specific PLD is first used to hydrolyze PC to choline and phosphatidic acid. The newly formed choline is then used to generate hydrogen peroxide in a reaction catalyzed by choline oxidase. Finally, with peroxidase as a catalyst, hydrogen peroxide reacts with DAOS and 4-aminoantipyrine to generate a blue dye with an optimal absorption at 595 nm. A kit for performing such an assay is commercially available from Cayman (Catalogue Number: 10009926) and Echelon (Catalogue Number: K-31PC).

An assay for sphingomyelin is described in detail in Hojjati, M. R., Jiang, X. *Rapid, specific, and sensitive measurements of plaSphingomyelina sphingomyelin and phosphatidylcholine*. J Lipid Res 47(3) 673-676 (2006). In this assay, sphingomyelinase is first used to hydrolyze SM to phosphorylcholine and ceramide. Alkaline phosphatase then generates choline from the phosphorylcholine and the newly formed choline is used to generate hydrogen peroxide in a reaction catalyzed by choline oxidase. Finally, with peroxidase as a catalyst, hydrogen peroxide reacts with DAOS and 4-aminoantipyrine to generate a blue color with an optimal absorption at 595 nm. A kit for performing such an assay is commercially available from Cayman (Catalogue Number: 10009928) and Echelon (Catalogue Number: K-31SM).

A assay kit capable of assaying both Phosphatidylcholine and Sphingomyelin is commercially available from Echelon (Catalogue Number: K-3100).

Choline lipids may be assayed by means of a immunoassays. A kit for performing such an assay is commercially available from ARUP Laboratory (Catalogue Number: 51590).

Enzyme assays for Phosphatidylcholine and Sphingomyelin are described in detail in Blaton V, de Buyzer M, Spincemaille J and Declercq B (1983). *Enzymic assay for Phosphatidylcholine and Sphingomyelin in serum*. Clinical Chemistry. 29: 806-809. An enzyme assay for quantifying Sphingomyelin is described in detail in He et al. (2001). *An enzymatic assay for quantifying Sphingomyelin in tissues and plaSphingomyelina from humans and mice with Niemann-Pick Disease*. Analytical Biochemistry. 2(15). 204-211.

Choline lipids may be assayed by means of thin layer chromatography. A TLC based assay is described in detail in Tsai et al. (1987). *Assay of disaturated phosphatidylcholine in amniotic fluid as a test of fetal lung maturity: experience with* 2000 *analyses*. Clinical chemistry. 33(9). 1648-1651. In this assay, crude lipid extract is separated by thin layer chromatography and PC is identified by mobility. Another TLC based assay is described in detail in Shimojo T, Abe M, Ohta M (1974). *A method for determination of saturated phosphatidylcholine*. Journal of Lipid Research. 15.525-527.

Choline lipids may be assayed by means of thin layer chromatography followed by GC-MS for fatty acid analysis. This is described in detail in Kahn et al. (1995). *Phosphatidylcholine molecular species of calf lung surfactant*. Am J Physol Lung Cell Mol Physiol. 269. 567-573. Crude lipid extract is separated by thin layer chromatography and PC is identified by mobility. Further characterization of molecular species is performed by gas chromatography mass spectrometry.

Choline lipids may be assayed by means of gas chromatography mass spectrometry. This is described in detail in Miller et al. (1991). *Differences in red blood cell choline and lipid-bound choline between patients with Alzheimer disease and control subjects*. Neurobiology of Aging. 12(1). 61-64.

Choline lipids may be assayed by means of MALDI-MS. This is described in detail in Shelley et al. (2005). *Direct profiling of lipid distribution in brain tissue using MALDI-TOFMS*. Analytical Chemistry. 77(14). 4523-4527. MS characterisation and separation of PC, ionization source is distinct from what we used (which is electrospray ionization).

Prediction Using Lipid Concentrations

The concentrations of the disclosed combinations of lipids in biological samples may be used in predictive processes to determine the state of a sample. The predictive method may provide an indication of the state, condition or status of sample. It may provide an indication of the biological state, as described above.

Various methods for achieving this, including bioinformatic and non-bioinformatic methods, are disclosed in detail below.

The Examples show that ovarian cancer samples display a reduction in levels of choline lipids, phosphatidylcholine (GPCho) and sphingomyelins (SM) compared to normal, undiseased, samples. Reduced levels of such choline lipids are also found in malignant samples compared to benign samples, and also late stage samples compared to early stage samples.

Accordingly, we disclose a method of identifying a cancerous sample, such as an ovarian cancer sample, the method comprising detecting a reduced level of a phosphatidylcholine (GPCho) or a sphingomyelin (SM), or both, in or of the sample. We further disclose methods to identify malignant samples from benign samples, and early stage samples from late stage samples, by detecting a reduced level of a phosphatidylcholine (GPCho) or a sphingomyelin (SM), or both, in or of the sample; in which a reduced level indicates that the sample is a malignant sample or a late stage sample, as the case may be. The reduced level or concentration may comprise a significantly reduced level or concentration.

Such a method may also be used for diagnosis of a cancer such as ovarian cancer, or the diagnosis of a malignant cancer, or the diagnosis of a late stage cancer, in an individual, the method comprising detecting a reduced level of a phosphatidylcholine (GPCho) or a sphingomyelin (SM), or both, in or of the sample of or from an individual.

The phosphatidylcholine (GPCho) or a sphingomyelin (SM) detected in such methods may be chosen from any one or more of the choline lipids shown in Table D1. For example, the concentrations of more than one choline lipid, for example several choline lipids such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76 or 77 lipids of Table D1 may be generated. The first such number of lipids from the top of the table may be used for this purpose.

The Examples also show that ovarian cancer samples display an increase in levels of ceramides (Cer) and glycosylated ceramides (HexCer). Increased levels of ceramides (Cer) and glycosylated ceramides (HexCer) are also found in malignant samples compared to benign samples, and also late stage samples compared to early stage samples.

Accordingly, we disclose a method of identifying a cancerous sample, such as an ovarian cancer sample, the method comprising detecting an increased level of a ceramide (Cer) or a glycosylated ceramide (HexCer), or both, in or of the sample. We further disclose methods to identify malignant samples from benign samples, and early stage samples from late stage samples, by detecting an increased level of a ceramide (Cer) or a glycosylated ceramide (HexCer), or both, in or of the sample; in which a reduced level indicates that the sample is a malignant sample or a late stage sample, as the case may be.

Such a method may also be used for diagnosis of a cancer such as ovarian cancer, or the diagnosis of a malignant cancer, or the diagnosis of a late stage cancer, in an individual, the method comprising detecting an increased level of a ceramide (Cer) or a glycosylated ceramide (HexCer), or both, in or of the sample of or from an individual. The increased level or concentration may comprise a significantly increased level or concentration.

The concentration or level of a lipid in a patient or a sample therefrom or thereof may be considered higher or lower than the normal concentration or level of a lipid if the concentration or level of a lipid is greater or less, respectively, than the normal level by an amount greater than the standard error of the assay employed to assess concentration or level of the lipid, such as at least twice, three, four, five or ten times that amount. Alternately, concentration or level of a lipid in the patient or a sample therefrom or thereof may be considered higher or lower than the normal level if the concentration or level of a lipid is at least about two, such as at least about three, four, or five times, higher or lower, respectively, than the normal concentration or level of a lipid.

The phosphatidylcholine (GPCho) or a sphingomyelin (SM) detected in such methods may be chosen from any one or more of the lipids shown in the relevant section of Table D3.

Generation of Classification Models

The predictive method may comprise applying a classification model generated from bioinformatic analysis of samples in known states. The classification model may be generated by the methods described in this section and below.

As described above, the concentrations of combinations of lipids may be generated from samples which are in "known" states. Such samples are therefore known to be in particular biological states, e.g., diseased, cancerous, tumorous, neoplastic, benign, malignant, early stage, late stage, etc. For classing such samples, known methods may be applied, including as histological means or biochemical means. For example, ovarian cancers may be classed by Trans-vaginal Ultrasonography (TVU), by assaying serum CA125 levels or examination of biopsies. The samples may be staged by methods known in the art.

A classification model capable of distinguishing two biological states may then be built by a model building process or model generation process, using the data from the known samples corresponding to biological states such as described above. Such a dataset may be referred to as a "training dataset".

A training dataset may comprise data from samples from two biological stages, for example, normal and diseased, benign and malignant, and early stage and late stage.

The classification model building process may comprise a number of steps. A dataset may be generated. The dataset may optionally be normalized. Thus, the concentrations of combinations of lipids from the known samples may be formed into a dataset. Other steps may be carried out on the concentrations, prior or subsequent to forming the dataset, for example, normalisation of the intensities or concentrations. Appendix D shows a dataset of normalised lipid concentrations from the lipids shown in Table D3, of normal and diseased (ovarian cancer), benign and malignant and early stage and late stage ovarian cancer samples used in the Examples.

The dataset may go through a first, analysis, step. The first analysis step may comprise Principal Components Analysis (PCA). The resulting dataset may go through a second, classification, step. The second classification step may comprise Support Vectors Machines (SVM) analysis. The classification model may be tested for performance. An iterative process may optionally be conducted to reduce the dimensions of the dataset. These are described in detail in the sections below.

Analysis Step

The first step in the classification model generation process may comprise a step we term an analysis step. This step may comprise an analysis of the dataset using a number of methods which result in a transformation of the dataset.

Methods suitable for use as a first analysis step include factor analysis and principal components analysis (PCA).

The analysis step may reduce the dimensions of the dataset. The analysis step may identify the principal components of the dataset. The analysis step may reduce the noise in the dataset. The analysis step may improve the signal-to-noise ratio. The analysis step may compress the data in the dataset.

The analysis step may result in a transformed dataset. The transformed dataset may have reduced dimensions as compared with the input dataset or it may result in a dataset with full dimensions (unreduced). Accordingly, although this first step may comprise a "dimension reduction" step, although it should be understood that the dimensions of the transformed dataset may not necessarily be reduced.

An output of the first step, for example, principal components analysis, may comprise a transformation matrix. Such a transformation matrix may be saved and form part of a classification model to be used for predictive analysis (described below).

Normalisation Step

Prior to the first analysis step of the classification model building process, an optional step of normalization may be performed.

Consider there are n samples in a training dataset and for each sample, m lipid intensities are measured. It is assumed that the total lipid intensity of each sample should be the same across all samples. Thus, the total lipid intensities of each sample are normalized to 1, as shown from Equation 1 below.

Let $I_{ij}$ represent the intensity of $i^{th}$ sample of lipid j and $\vec{x}_i$ represent a vector containing m normalized intensities of sample i.

$$\vec{x}_i = \begin{pmatrix} x_{i1} \\ x_{i2} \\ \vdots \\ x_{im} \end{pmatrix} = \frac{1}{\sum_{j=1}^{m} I_{ij}} \begin{pmatrix} I_{i1} \\ I_{i2} \\ \vdots \\ I_{im} \end{pmatrix}, \text{ where } i = 1, \ldots n \quad (1)$$

The first analysis step, for example, Principal Components Analysis, may then be performed on the normalized dataset $X=(\vec{x}_1, \vec{x}_2, \ldots, \vec{x}_n)$.

The data is normalized by the total intensities in that mode and the concentrations calculated using the respective spiked standards.

The normalization could be given as:

$$\text{Lipid}_i = \frac{x_i}{[Std] \cdot \sum_{i=1}^{n} x_i}$$

where $x_i$ indicates the intensity of a particular type of lipid, $\text{lipid}_i$. Std indicates the constant obtained from the standard graph or from a spiked lipid standard. In the case of the spiked standard, the Std is obtained as a ratio of the intensity to the amount (pmoles) of the standard spiked. Another way of obtaining Std is to plot a standard graph with varying amount of the standards and then obtaining a standard graph. This graph may then give the ratio of the intensity over concentration and can be substituted in the above equation.

Suitable lipids for spiking and determining concentrations are known in the art and are described in the Examples.

Principal Components Analysis (PCA)

The analysis step of the classification model generation process may comprise a step of Principal Components Analysis (PCA).

Principal Components Analysis is a technique to reduce multidimensional dataset $C=(\vec{c}_1, \vec{c}_2, \ldots, \vec{c}_m)$ to a lower dimension.

Principal Components Analysis linearly transforms the original dataset into a new dimension space. This can be achieved using functions from a number of mathematical packages. For example, principal components analysis may be performed by Pirouette (Infometrix, Inc.), Statistica (StatSoft, Inc.), SPSS (SPSS Inc.), Unscrambler (CAMO Software AS.), PCA/X 5.0 (Windale Technologies Pty Ltd), XLSTAT (Addinsoft), StatistiXL (StatistiXL), NMath Stats (CenterSpace Software), R (Freeware) (http://rss.acs.unt.edu/Rdoc/library/pcaMethods/html/00Index.html), SAS/INSIGHT (SAS Institute Inc.). As a further example, the princomp function in Matlab may be used.

princomp in Matlab returns the principal component coefficients and the representation of X in the principal component space $Y=(\vec{y}_1, \vec{y}_2, \ldots, \vec{y}_n)$. Each vector, $\vec{c}_i$, represents the $i^{th}$ principal component axis with dimension m. The relationship between C and Y is shown in Equation 2.

$$Y = C \cdot (X - rep(\overline{X})), \quad (2)$$

where $$\overline{X} = (\overline{x}_1 \ \overline{x}_2 \ \ldots \ \overline{x}_n), \quad rep(\overline{X}) = \begin{pmatrix} \overline{x}_1 & \overline{x}_2 & \ldots & \overline{x}_n \\ \overline{x}_n & \overline{x}_2 & \ldots & \overline{x}_n \\ \vdots & \vdots & \ddots & \vdots \\ \overline{x}_n & \overline{x}_2 & \ldots & \overline{x}_n \end{pmatrix}$$

$$\overline{x}_i = \frac{1}{m} \sum_{j=1}^{m} x_{ij},$$

Principal components analysis involves a mathematical procedure that transforms a number of (possibly) correlated variables into a (smaller) number of uncorrelated variables called principal components. The first principal component accounts for as much of the variability in the data as possible, and each succeeding component accounts for as much of the remaining variability as possible. This helps in data compression. The outcome of these analysis is a score matrix.

Classification Step

The transformed dataset resulting from the first step may be go through a second step. The second step in the classification model building process may therefore comprise a classification step.

This step may comprise an analysis of the transformed dataset using a number of methods, such as support vector machines (SVM) analysis. The classification step may enable adequate classification of the samples, or it may be subject to further training steps (described below).

The classification analysis may result in an indicator of the class of the sample. The indicator of class may correspond to one of the biological states used for building the classification model. The correspondence between the biological states and the output of the second step may depend on the labels applied to the samples used as basis for the model generation. For example, in an SVM analysis, the labels may be either −1 or +1. Thus, −1 may represent a diseased state and +1 may represent a control state (i.e., a normal sample). As another example, −1 may represent a malignant state and +1 may represent a benign state. As a further example, −1 may represent a late stage state and +1 may represent an early stage state.

In such a case, where SVM analysis is applied, the outputs from the second step may be negative or positive. A negative output would indicate a "worse" condition, that is to say, a diseased (cancerous) sample, a malignant sample, or a late stage sample, as the case may be. A positive output, on the other hand, would in the situation above, indicate a "better" condition. That is to say, a positive output would indicate a normal sample, a benign sample or an early stage sample.

An output of the classification step may comprise a model, such as an SVM model where support vector machines (SVM) analysis is carried out as the second step. Such an SVM model may be saved and form part of a classification model to be used for predictive analysis (described below).

The outcome of the second classification step may be represented in the form of diagnostic utility matrix. The performance of the second classification step may be assessed using a number of factors, such as sensitivity, specificity and accuracy.

Support Vector Machines (SVM)

Support Vector Machines (SVM) is a supervised machine learning method used for classification and regression. SVM is described in detail in Review: Applications of Support Vector Machines in Chemistry, Rev. Comput. Chem. 2007, 23, 291-400.

SVM performs binary classification by constructing an l-dimensional hyperspace that optimally separates the dataset into two categories. The output value from the SVM is a real number which signifies its distance from the hyperplane. The SVM model may be saved (examples are shown in the Appendices).

SVM may be implemented using a number of packages, including SVMlight (svmlight.joachims.org/); SVMstruct (svmlight.joachims.org/svm_struct.html); mySVM (www-ai.cs.uni-dortmund.de/SOFTWARE/MYSVM/index.html); JmySVM (www-ai.cs.uni-dortmund.de/SOFTWARE/YALE/index.html); mySVM/db (www-ai.cs.uni-dortmund.de/SOFTWARE/MYSVMDB/index.html); LIBSVM (www.csie.ntu.edu.tw/~cjlin/libsvm/); looms (www.csie.ntu.edu.tw/~cjlin/looms/); BSVM (www.csie.ntu.edu.tw/~cjlin/bsvm/); SVMTorch (www.idiap.ch/learning/SVMTorch.html); Weka (www.cs.waikato.ac.nz/ml/weka/); SVM in R (cran.r-project.org/src/contrib/Descriptions/e1071.html); M-SVM (www.loria.fr/~guermeur/); Gist (microarray.cpmc.columbia.edu/gist/); MATLAB SVM Toolbox (www.isis.ecs.soton.ac.uk/resources/svminfo/); TinySVM (chasen.org/~taku/software/TinySVM/); SmartLab (www.smartlab.dibe.unige.it/); Gini-SVM (bach.ece.jhu.edu/svm/ginisvm/); GPDT (dm.unife.it/gpdt/); HeroSvm (www.cenparmi.concordia.ca/~people/jdong/HeroSvm.html); Spider (www.kyb.tuebingen.mpg.de/bs/people/spider/); Java applets (svm.dcs.rhbnc.ac.uk/); LEARNSC (www.support-vector.ws/html/downloads.html); Tree Kernels (ai-nlp.info.uniroma2.it/moschitti/Tree-Kernel.htm); LS-SVMlab (www.esat.kuleuven.ac.be/sista/lssvmlab/); MATLAB SVM Toolbox (www.igi.tugraz.at/aschwaig/software.html); SVM/LOO (bach.ece.jhu.edu/pub/gert/svm/incremental/); SVMsequel (www.isi.edu/~hdaume/SVMsequel/); LSVM (www.cs.wisc.edu/dmi/lsvm/); ASVM (www.cs.wisc.edu/dmi/asvm/); PSVM (www.cs.wisc.edu/dmi/svm/psvm/); OSU SVM Classifier Matlab Toolbox (www.ece.osu.edu/~maj/osu_svm/); SimpleSVM Toolbox (asi.insa-rouen.fr/~gloosli/simpleSVM.html); SVM Toolbox (asi.insa-rouen.fr/%7Earakotom/toolbox/index); MATLAB SVM Toolbox (theoval.sys.uea.ac.uk/~gcc/svm/toolbox/); R-SVM (www.biostat.harvard.edu/~xzhang/R-SVM/R-SVM.html); jSVM (www-cad.eecs.berkeley.edu/~hwawen/research/projects/jsvm/doc/manual/index.html); SvmFu (five-percent-nation.mit.edu/SvmFu/); PyML (pyml.sourceforge.net/) and BioJava (www.biojava.org/).

$SVM_{light}$ is a an open source implementation of SVM which may be obtained from http://svmlight.joachims.org/. It is one of the most widely used SVM classification and regression packages. It has a fast optimization algorithm, can be applied to very large datasets, and has a very efficient implementation of the leave-one-out cross-validation. It is distributed as C++ source and binaries for Linux, Windows, Cygwin, and Solaris. Kernels: polynomial, radial basis function, and neural (tanh).

SVM allows users to build in their own mathematical functions, which are known as kernel functions. In $SVM_{light}$, the default kernel function is linear and it has also built in polynomial function, radial basis function (RBF), and sigmoid function (refer to Equation 3 below).

$$\phi = \begin{cases} x_i * x_i & \text{Linear} \\ (\gamma x_i x_j + \text{coefficient})^{degree} & \text{Polynomial} \\ \exp(-\gamma|x_i - x_j|^2) & RBF \\ \tanh(\gamma x_i x_j + \text{coefficient}) & \text{Sigmoid} \end{cases} \quad (3)$$

Any of the kernel functions of SVM may be used for the SVM analysis described here. For example, the default kernel function of $SVM_{light}$ may be implemented.

The SVM analysis may be conducted on a transformed dataset, that is to say, a dataset transformed by applying a transformation matrix to a dataset comprising the concentrations of a plurality of lipids.

Classification Model

A classification model is generated from the classification model generation process described above. The classification model may comprise a number of components.

The classification model may comprise a transformation matrix, also referred to as C, which is the obtained from the PCA analysis. The classification model may further comprise an SVM model, also referred to as S, which is the SVM model obtained from $Y_l$. The classification model may yet further comprise other components, as described below.

The transformation matrix may comprise a full, un-reduced transformation matrix. Such a matrix may comprise an n×m transformation matrix, where n=number of lipids and m=number of principal components. In such a transformation matrix, n may be equal to m. Such a transformation matrix may comprise the total number of principal components.

The transformation matrix may comprise a reduced transformation matrix, in other words, a transformation matrix corresponding to a reduced number of principal components. For example, a reduced transformation matrix may comprise a n×m transformation matrix, where n=number of lipids and m=number of principal components retained (m<number of lipids). Such a reduced transformation matrix may be easily generated by forming a matrix comprising the rows of the full transformation matrix and the first m columns of the full transformation matrix.

The classification model generated may be evaluated by a number of factors such as receiver operating curve, sensitivity, specificity, positive predictive value (PPV) and negative predictive value (NPV) and accuracy. The performance of the model model may therefore be shown in terms of a number of factors, including for example the sensitivity, specificity, positive predictive value (PPV), negative predictive value (NPV), accuracy, true negatives (TN), false negatives (FN), false positives (FP) and true positives (TP).

The model may further be evaluated using the N-fold cross validation and predicting the blinded samples.

Classification Model Training

As an optional step of the model generating process, a training process may take place as part of the model generation process.

The classification model may for example be adjusted and processed with an aim of establishing a model which achieve a certain predetermined level of performance.

The classification model may for example be adjusted and processed with an aim of establishing the minimum number of principal components which allow the model to achieve a certain predetermined level of performance.

The training may be conducted by assessing the output of the analysis step and selecting a number of factors to interpret.

Thus, the training process may comprise retaining principal components whose eigenvalues are greater than or equal to 1. This is also known as the Kaiser stopping rule (Kaiser, 1960).

The training process may comprise retaining principal components that explain a predetermined level of the variance in the dataset. The predetermined level of variance may comprise at least 55%, 65%, 75%, 85%, 90%, 95%, 96%, 97%, 98%, 99%, 99.5%, 99.6%, 99.7%, 99.8% or 99.9%.

The training process alternatively, or in addition, comprise a scree test, as described by Cattell (1966). The magnitude of the eigenvalues on the vertical axis may be plotted against their number (e.g., first factor, second factor, third factor, etc). The training process may comprise retaining all factors in the sharp descent before the first eigenvector where the graph levels off, as described in Stevens, 1966.

A scree plot which shows principal components and eigenvalues may be used. The training process may comprise retaining principal components that in a scree plot of eigenvalues show a smooth decrease of eigenvalues. It may comprise retaining principal components that in a scree plot of eigenvalues are to the left of a levelling off in gradient in the plot. It may comprise retaining principal components that in a scree plot of eigenvalues are to the left of significant decrease in gradient in the plot. It may comprise retaining principal components that in a scree plot of eigenvalues are to the left of an elbow in the plot.

The training process may be conducted by assessing the output of the classification step.

Thus, the training process may comprise retaining principal components that perform to a predetermined level compared to the full dataset, as assessed by the performance of the classification model generated. For example, principal components may be retained to achieve at least 55%, 65%, 75%, 85%, 90%, 95%, 96%, 97%, 98%, 99%, 99.5%, 99.6%, 99.7%, 99.8%, 99.9% or 100% of the performance of the classification model built using the full dataset. The performance of the classification model may be assessed by any combination of sensitivity, specificity, PPV, NPV, accuracy, true negatives (TN), false negatives (FN), false positives (FP) and true positives (TP).

The training process may comprise removing factors which do not significantly affect the performance of the SVM model, as assessed by any of the factors set out above.

The training process may take the form of an iterative process. Thus, the last (least significant) principal component determined by principal components analysis may be removed and the classification model built again. The new classification model may be compared to the original model for its classification performance. The performance may be assessed using a number of factors, such as sensitivity, specificity and accuracy. This process is then repeated until the predetermined level of performance is reached. For example, the process may be repeated until the model loses its performance.

In more detail, the first/row vectors of the transformed dataset Y may be selected to form an input vector, $Y_l$. The input vector $Y_l$ may then be subject to Support Vectors Machines (SVM) analysis. $Y_l$ is equivalent to the input dataset in the principal component space, with reduced dimension of l. The value of l is the minimum dimension of the principal component space needed to obtain optimal classification in the SVM model. This may be established by iterative reduction of dimensions and testing the performance of the resulting model.

The level of performance may be any suitable level which meets the needs of the situation in question.

For example, an iterative reduction in dimensions may be carried out to train the classification model to achieve a performance which is at least as good as, or better than, a known biomarker. The biomarker may comprise, for example, CA-125. The sensitivity of a CA-125 is about 50%, the specificity about 97.15%, the PPV about 17.24% and the NPV about 99.39%.

Thus, the training may comprise determining the number of principal components needed to allow the classification model to achieve any one or more of a sensitivity of about 50% or more, a specificity about 97.15% or more, a PPV about 17.24% or more and an NPV about 99.39% or more.

Where classification model training takes place, the classification model may optionally further comprise a dimension, l. The dimension l may be a reduced dimension. The dimension l may comprise the dimension of principal component space, l, needed for optimal SVM classification.

The dimension l may be derived from principal components analysis of the dataset. This may be achieved by iterative reduction in dimensions and assessing performance of the resulting model (described above).

Classification Models Generated from 340 Lipids

Dataset of 340 Lipids

A dataset comprising concentrations of the 340 lipids shown in Table D3 may be obtained. The dataset may optionally be normalised.

Transformation Matrices (340 Lipids, Unreduced)

Principal Components Analysis may be conducted on the above dataset without dimension reduction.

We disclose in Appendix B1 a 340×340 transformation matrix of a classification model for classifying normal and diseased samples. We disclose in Appendix B2 a 340×340 transformation matrix of a classification model for classifying benign and malignant samples. We disclose in Appendix B3 a 340×340 transformation matrix of a classification model for classifying early and late stage samples.

SVM Models (340 Lipids, Unreduced)

The transformation matrices are used to transform the datasets of the respective sample pairs. SVM analysis is carried out on the transformed datasets.

As an example, SVM analysis may be conducted on a dataset of the concentrations the 340 lipids shown in Table D3 of normal and diseased (ovarian cancer) samples, transformed with a transformation matrix shown in Appendix B1. We disclose in Appendix C1 a resulting SVM model, which is also referred to in this document as "SVM-1". Such an SVM model may be used, together with a 340×340 transformation matrix shown in Appendix B1, as part of a classification model for classifying normal and diseased (ovarian cancer) samples.

As another example, the SVM analysis may be conducted on a transformed dataset of the concentrations of the 340 lipids shown in Table D3 of benign ovarian cancer and malignant ovarian cancer samples, transformed with a transformation matrix shown in Appendix B2. We disclose in Appendix C2 a resulting SVM model, which is also referred to in this document as "SVM-2". Such an SVM model may be used, together with a 340×340 transformation matrix shown in Appendix B2, as a classification model for classifying benign and malignant ovarian cancer samples.

As a further example, the SVM analysis may be conducted on a transformed dataset of the concentrations of the 340 lipids shown in Table D3 of early stage ovarian cancer and late stage ovarian cancer samples, transformed with a transformation matrix shown in Appendix B3. We disclose Appendix C3 a resulting SVM model, which is also referred to in this document as "SVM-3". Such an SVM model may be used, together with a 340×340 transformation matrix shown in Appendix B3, as a classification model for classifying early and late ovarian stage cancer samples.

Classification Models (340 Lipids, Unreduced)

We disclose a classification model comprising a 340×340 transformation matrix shown in Appendix B1 and an SVM model shown in Appendix C1. Such a model may be used to distinguish between normal and diseased, for example, ovarian cancer, samples.

We disclose a further classification model which comprises a 340×340 transformation matrix shown in Appendix B2 and an SVM model shown in Appendix C2. Such a model may be used to distinguishing between benign and malignant samples.

We disclose yet another classification model which comprises a 340×340 transformation matrix shown in Appendix B3 and an SVM model shown in Appendix C3. Such a model may be used to distinguish between early and late stage samples.

Classification Models Generated from 340 Lipids (R1)

The training process may be conducted on a dataset comprising the concentrations of the 340 lipids shown in Table D3.

A further optional step of training the model by iterative reduction of dimensions may be carried out to determine the principal components needed for maximal classifying performance.

The cumulative performance of each of the classification models, as assessed by sensitivity, specificity, PPV and NPV, is shown in Appendices E1, E2 and E3.

We disclose in Appendix E1 the cumulative performance of a classification model (340 lipids) for normal versus diseased, by the number of principal components. We disclose in Appendix E2 the cumulative performance of a classification model (340 lipids) for benign versus malignant, by the number of principal components. We disclose in Appendix E3 the cumulative performance of a classification model (340 lipids) for early versus late, by the number of principal components.

The model with reduced dimensions may be tested for performance, such as by determining sensitivity, specificity, PPV, NPV, etc.

In these Appendices, rows in italics show the number of principal components required for a classification model which has identical performance compared to SVM analysis using the all the principal components.

In the case of the classification model for normal and diseased, maximal classifying performance (i.e., identical to a model with all the principal components) may be obtained using 85 principal components. In the case of the classification model for benign and malignant, maximal classifying performance may be obtained using 87 principal components. In the case of the classification model for early and late, maximal classifying performance may be obtained using 44 principal components.

Transformation Matrices (340 Lipids, Reduced)

We disclose a 340×85 transformation matrix comprising the first 85 columns of a matrix shown in Appendix B1, which may be used in a classification model for classifying normal and diseased, such as ovarian cancer, samples.

We disclose a 340×87 transformation matrix comprising the first 87 columns of a matrix shown in Appendix B2, which may be used in a classification model for classifying benign and malignant samples.

We disclose a 340×44 transformation matrix comprising the first 44 columns of a matrix shown in Appendix B3, which may be used in a classification model for classifying early and late stage samples.

SVM Models (340 Lipids, Reduced)

We disclose at Appendix C4 an SVM model which may be used with a 340×85 transformation matrix comprising the first 85 columns of a matrix shown in Appendix B1 as a classification model for classifying normal and diseased, such as ovarian cancer, samples.

We disclose at Appendix C5 an SVM model which may be used with a 340×87 transformation matrix comprising the first 87 columns of a matrix shown in Appendix B2 as a classification model for classifying benign and malignant samples.

We disclose at Appendix C6 an SVM model which may be used with a 340×44 transformation matrix comprising the first 44 columns of a matrix shown in Appendix B3 as a classification model for classifying early and late stage samples.

Classification Models (340 Lipids, Reduced)

We disclose a classification model which comprises a 340×85 transformation matrix comprising the first 85 columns of a matrix shown in Appendix B1 and an SVM model shown in Appendix C4. Such a model may be used to distinguish between normal and diseased, for example, ovarian cancer, samples.

We disclose a further classification model which comprises a 340×87 transformation matrix comprising the first 87 columns of a matrix shown in Appendix B2 and an SVM model shown in Appendix C5. Such a model may be used to distinguishing between benign and malignant samples.

We disclose yet another classification model which comprises a 340×44 transformation matrix comprising the first 44 columns of a matrix shown in Appendix B3 and an SVM model shown in Appendix C6. Such a model may be used to distinguish between early and late stage samples.

Classification Models Generated from 340 Lipids (R2)

The training process may be conducted on a dataset comprising the concentrations of the 340 lipids shown in Table D3.

A further optional step of training the model by iterative reduction of dimensions may be carried out to identify the number of principal components required for a classification model which provides performance which is as good as or better than CA-125.

The cumulative performance of each of the classification models, as assessed by sensitivity, specificity, PPV and NPV, is shown in Appendices E1, E2 and E3.

We disclose in Appendix E1 the cumulative performance of a classification model (340 lipids) for normal versus diseased, by the number of principal components. We disclose in Appendix E2 the cumulative performance of a classification model (340 lipids) for benign versus malignant, by the number of principal components. We disclose in Appendix E3 the cumulative performance of a classification model (340 lipids) for early versus late, by the number of principal components.

The model with reduced dimensions may be tested for performance, such as by determining sensitivity, specificity, PPV, NPV, etc.

In these Appendices, rows in bold show the number of principal components required for a classification model which provides performance which is as good as or better compared to CA-125 (Sensitivity=50%; Specificity=97.15%; PPV=17.24%; NPV=99.39%).

In the case of the classification model for normal and diseased, a classification model employing 10 principal components performs as well as or better than CA-125. In the case of the classification model for benign and malignant, a classification model employing 29 principal components performs as well as or better than CA-125. In the case of the classification model for early and late, a classification model employing 9 principal components performs as well as or better than CA-125.

Transformation Matrices (340 Lipids, Reduced)

We disclose a 340×10 transformation matrix comprising the first 10 columns of a matrix shown in Appendix B1, which may be used in a classification model for classifying normal and diseased, such as ovarian cancer, samples.

We disclose a 340×29 transformation matrix comprising the first 29 columns of a matrix shown in Appendix B2, which may be used in a classification model for classifying benign and malignant samples.

We disclose a 340×9 transformation matrix comprising the first 9 columns of a matrix shown in Appendix B3, which may be used in a classification model for classifying early and late stage samples.

SVM Models (340 Lipids, Reduced)

We disclose at Appendix C7 an SVM model which may be used with a 340×10 transformation matrix comprising the first 10 columns of a matrix shown in Appendix B1 as a classification model for classifying normal and diseased samples.

We disclose at Appendix C8 an SVM model which may be used with a 340×29 transformation matrix comprising the first 29 columns of a matrix shown in Appendix B2 as a classification model for classifying benign and malignant samples.

We disclose at Appendix C9 an SVM model which may be used with a 340×9 transformation matrix comprising the first 9 columns of a matrix shown in Appendix B3 as a classification model for classifying early and late samples.

Classification Models (340 Lipids, Reduced)

We disclose a classification model which comprises a 340×10 transformation matrix comprising the first 10 columns of a matrix shown in Appendix B1 and an SVM model shown in Appendix C7. Such a model may be used to distinguish between normal and diseased, for example, ovarian cancer, samples.

We disclose a further classification model which comprises a 340×29 transformation matrix comprising the first 29 columns of a matrix shown in Appendix B2 and an SVM model shown in Appendix C8. Such a model may be used to distinguish between benign and malignant samples.

We disclose yet another classification model which comprises a 340×9 transformation matrix comprising the first 9 columns of a matrix shown in Appendix B3 and an SVM model shown in Appendix C9. Such a model may be used to distinguish between early and late stage samples.

Classification Models Generated from N Lipids (N<340)

Classification may be carried out by generating classification models from subsets of the 340 lipids shown in Table D3 and application such classification models to unknown samples.

Datasets

Datasets comprising concentrations of any number of the 340 lipids shown in Table D3 may be derived. Such datasets may comprise concentrations of the first n lipids, where n<340, of Table D3.

Thus, for example, datasets comprising the concentrations of the first 2, 3, 4, 5, 6, 7, 8, 9, 10 lipids of Table D3 may be generated.

As another example, datasets comprising the concentrations of the first 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 lipids of Table D3 may be generated.

As another example, datasets comprising the concentrations of the first 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150 lipids of Table D3 may be generated.

As a further example, datasets comprising the concentrations of the first 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 lipids of Table D3 may be generated.

As a yet further example, datasets comprising the concentrations of the first 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338 or 339 lipids of Table D3 may be generated.

Such datasets may be generated by, for example, selecting appropriate data from the Ovarian Cancer Training Dataset shown in Appendix D. The dataset may optionally be normalised.

Transformation Matrices (n Lipids)

Principal Components Analysis may be conducted on the above datasets with or without dimension reduction.

“Unreduced” n×n transformation matrices of respective classification models for classifying normal and diseased samples, benign and malignant samples and early and late stage samples may be generated by the methods described in this document, such as PCA.

“Reduced” n×m, where m<n, transformation matrices, representing a reduced number of principal components, may also be generated by, for example, iterative reduction of dimensions and testing for the performance of the resulting models, as described elsewhere in this document.

SVM Models (n Lipids)

The transformation matrices may be used to transform the datasets of the respective sample pairs. SVM analysis may be carried out on the transformed datasets.

As an example, SVM analysis may be conducted on a dataset of the concentrations of the n lipids of known normal and diseased (ovarian cancer) samples, transformed with a respective n×n "unreduced" transformation matrix described above. The resulting SVM model may be used, together with the n×n transformation matrix, as part of a classification model for classifying normal and diseased (ovarian cancer) samples.

As another example, the SVM analysis may be conducted on a dataset of the concentrations of the n lipids of known benign ovarian cancer and malignant ovarian cancer samples, transformed with a respective n×n "unreduced" transformation matrix described above. The resulting SVM model may be used, together with the n×n transformation matrix, as a classification model for classifying benign and malignant ovarian cancer samples.

As a further example, the SVM analysis may be conducted on a dataset of the concentrations of the n lipids of known early stage ovarian cancer and late stage ovarian cancer samples, transformed with a respective n×n "unreduced" transformation matrix described above. The resulting SVM model may be used, together with the n×n transformation matrix, as a classification model for classifying early and late ovarian stage cancer samples.

Corresponding SVM models generated on datasets transformed with n×m, where m<n, "reduced" transformation matrices may also be generated by the methods described in this document. Such SVM models together with respective "reduced" transformation matrices, as classification models for classifying normal and diseased samples, benign and malignant samples and early and late stage samples.

Classification Models (n Lipids)

We disclose a classification model comprising a n×n "unreduced" transformation matrix generated from a dataset of known normal and diseased (ovarian cancer) samples described above and a corresponding SVM model as described above. Such a model may be used to distinguish between normal and diseased, for example, ovarian cancer, samples.

We disclose a further classification model which comprises a n×n "unreduced" transformation matrix generated from a dataset of known benign and malignant samples described above and a corresponding SVM model as described above. Such a model may be used to distinguishing between benign and malignant samples.

We disclose yet another classification model which comprises a n×n "unreduced" transformation matrix generated from a dataset of known early stage and late stage samples described above and a corresponding SVM model as described above. Such a model may be used to distinguish between early and late stage samples.

We also disclose corresponding classification models comprising n×m, where m<n, "reduced" transformation matrices generated from datasets of known normal and diseased (ovarian cancer) samples, benign and malignant samples or early stage and late stage (ovarian cancer) samples and their corresponding SVM models, capable of classifying normal and diseased samples, benign and malignant samples and early and late stage samples respectively.

Classification Models Generated from 82 Lipids

Dataset of 82 Lipids

A dataset comprising concentrations of the 82 lipids shown in Table D2 may be obtained. The dataset may optionally be normalised.

Transformation Matrices (82 Lipids, Unreduced)

Principal Components Analysis may be conducted on the above dataset without dimension reduction.

We disclose in Appendix B4 a 82×82 transformation matrix of a classification model for classifying normal and diseased samples. We disclose in Appendix B5 a 82×82 transformation matrix of a classification model for classifying benign and malignant samples. We disclose in Appendix B6 a 82×82 transformation matrix of a classification model for classifying early and late stage samples.

SVM Models (82 Lipids, Unreduced)

The transformation matrices are used to transform the datasets of the respective sample pairs. SVM analysis is carried out on the transformed datasets.

As an example, SVM analysis may be conducted on a dataset of the concentrations the 82 lipids shown in Table D2 of normal and diseased (ovarian cancer) samples, transformed with a transformation matrix shown in Appendix B4. We disclose in Appendix C10 a resulting SVM model. Such an SVM model may be used, together with a 82×82 transformation matrix shown in Appendix B4, as part of a classification model for classifying normal and diseased (ovarian cancer) samples.

As another example, the SVM analysis may be conducted on a transformed dataset of the concentrations of the 82 lipids shown in Table D2 of benign ovarian cancer and malignant ovarian cancer samples, transformed with a transformation matrix shown in Appendix B5. We disclose in Appendix C11 a resulting SVM model. Such an SVM model may be used, together with a 82×82 transformation matrix shown in Appendix B5, as a classification model for classifying benign and malignant ovarian cancer samples.

As a further example, the SVM analysis may be conducted on a transformed dataset of the concentrations of the 82 lipids shown in Table D2 of early stage ovarian cancer and late stage ovarian cancer samples, transformed with a transformation matrix shown in Appendix B6. We disclose Appendix C12 a resulting SVM model. Such an SVM model may be used, together with a 82×82 transformation matrix shown in Appendix B6, as a classification model for classifying early and late ovarian stage cancer samples.

Classification Models (82 Lipids, Unreduced)

We disclose a classification model comprising a 82×82 transformation matrix shown in Appendix B4 and an SVM model shown in Appendix C10. Such a model may be used to distinguish between normal and diseased, for example, ovarian cancer, samples.

We disclose a further classification model which comprises a 82×82 transformation matrix shown in Appendix B5 and an SVM model shown in Appendix C11. Such a model may be used to distinguishing between benign and malignant samples.

We disclose yet another classification model which comprises a 82×82 transformation matrix shown in Appendix B6 and an SVM model shown in Appendix C12. Such a model may be used to distinguish between early and late stage samples.

Classification Models Generated from 44 Lipids

Dataset of 44 Lipids

A dataset comprising concentrations of the first 44 of the 340 lipids shown in Table D3 (i.e., as shown in Table E6) may be derived by, for example, selecting appropriate data from the Ovarian Cancer Training Dataset shown in Appendix D. The dataset may optionally be normalised.

Transformation Matrices (44 Lipids)

Principal Components Analysis may be conducted on the above dataset with or without dimension reduction.

"Unreduced" 44×44 transformation matrices of respective classification models for classifying normal and diseased samples, benign and malignant samples and early and late stage samples may be generated by the methods described in this document, such as PCA.

Respective 44×m, where m<44, "reduced" transformation matrices, representing a reduced number of principal components, may also be generated by, for example, iterative reduction of dimensions and testing for the performance of the resulting models, as described elsewhere in this document.

SVM Models (44 Lipids)

The transformation matrices may be used to transform the datasets of the respective sample pairs. SVM analysis may be carried out on the transformed datasets.

As an example, SVM analysis may be conducted on a dataset of the concentrations of the 44 lipids shown in Table E6 of normal and diseased (ovarian cancer) samples, transformed with a respective 44×44 transformation matrix described above. The resulting SVM model may be used, together with the 44×44 transformation matrix, as part of a classification model for classifying normal and diseased (ovarian cancer) samples.

As another example, the SVM analysis may be conducted on a dataset of the concentrations of the 44 lipids shown in Table E6 of benign ovarian cancer and malignant ovarian cancer samples, transformed with a respective 44×44 transformation matrix described above. The resulting SVM model may be used, together with the 44×44 transformation matrix, as a classification model for classifying benign and malignant ovarian cancer samples.

As a further example, the SVM analysis may be conducted on a dataset of the concentrations of the 44 lipids shown in Table E6 of early stage ovarian cancer and late stage ovarian cancer samples, transformed with a respective 44×44 transformation matrix described above. The resulting SVM model may be used, together with the 44×44 transformation matrix, as a classification model for classifying early and late ovarian stage cancer samples.

Corresponding SVM models generated on datasets transformed with 44×m, where m<44, "reduced" transformation matrices may also be generated by the methods described in this document. Such SVM models together with respective "reduced" transformation matrices, as classification models for classifying normal and diseased samples, benign and malignant samples and early and late stage samples.

Classification Models (44 Lipids)

We disclose a classification model comprising a 44×44 transformation matrix described above and an SVM model as described above. Such a model may be used to distinguish between normal and diseased, for example, ovarian cancer, samples.

We disclose a further classification model which comprises a 44×44 transformation matrix described above and an SVM model as described above. Such a model may be used to distinguishing between benign and malignant samples.

We disclose yet another classification model which comprises a 44×44 transformation matrix described above and an SVM model as described above. Such a model may be used to distinguish between early and late stage samples.

We also disclose corresponding classification models comprising 44×m, where m<44, "reduced" transformation matrices and their corresponding SVM models, capable of classifying normal and diseased samples, benign and malignant samples and early and late stage samples.

Classifications Model Generated from 77 Choline Lipids

Dataset of 77 Choline Lipids

A dataset comprising concentrations of the 77 choline lipids shown in Table D1 may be obtained. The dataset may optionally be normalised.

Transformation Matrices (77 Choline Lipids, Unreduced)

Principal Components Analysis may be conducted on the above dataset without dimension reduction.

We disclose in Appendix B7 a 77×77 transformation matrix of a classification model for classifying normal and diseased samples. We disclose in Appendix B8 a 77×77 transformation matrix of a classification model for classifying benign and malignant samples. We disclose in Appendix B9 a 77×77 transformation matrix of a classification model for classifying early and late stage samples.

SVM Models (77 Choline Lipids, Unreduced)

The transformation matrices are used to transform the datasets of the respective sample pairs. SVM analysis is carried out on the transformed datasets.

As an example, SVM analysis may be conducted on a dataset of the concentrations the 77 choline lipids shown in Table D1 of normal and diseased (ovarian cancer) samples, transformed with a transformation matrix shown in Appendix B7. We disclose in Appendix C13 a resulting SVM model. Such an SVM model may be used, together with a 77×77 transformation matrix shown in Appendix B7, as part of a classification model for classifying normal and diseased (ovarian cancer) samples.

As another example, the SVM analysis may be conducted on a transformed dataset of the concentrations of the 77 choline lipids shown in Table D1 of benign ovarian cancer and malignant ovarian cancer samples, transformed with a transformation matrix shown in Appendix B8. We disclose in Appendix C14 a resulting SVM model. Such an SVM model may be used, together with a 77×77 transformation matrix shown in Appendix B8, as a classification model for classifying benign and malignant ovarian cancer samples.

As a further example, the SVM analysis may be conducted on a transformed dataset of the concentrations of the 77 choline lipids shown in Table D1 of early stage ovarian cancer and late stage ovarian cancer samples, transformed with a transformation matrix shown in Appendix B9. We disclose Appendix C15 a resulting SVM model. Such an SVM model may be used, together with a 77×77 transformation matrix shown in Appendix B9, as a classification model for classifying early and late ovarian stage cancer samples.

Classification Models (77 Choline Lipids, Unreduced)

We disclose a classification model comprising a 77×77 transformation matrix shown in Appendix B7 and an SVM model shown in Appendix C13. Such a model may be used to distinguish between normal and diseased, for example, ovarian cancer, samples.

We disclose a further classification model which comprises a 77×77 transformation matrix shown in Appendix B8 and an SVM model shown in Appendix C14. Such a model may be used to distinguishing between benign and malignant samples.

We disclose yet another classification model which comprises a 77×77 transformation matrix shown in Appendix B9 and an SVM model shown in Appendix C15. Such a model may be used to distinguish between early and late stage samples.

Prediction Using Classification Model

The prediction process may be implemented in a similar manner to that of the model generation process. The prediction process classifies an unknown sample (i.e., a sample whose state is unknown) into one of two states.

The prediction process generally involves obtaining the concentrations of a plurality of lipids from an unknown sample. The lipid concentrations may be formed into a dataset. The dataset may optionally be normalized. These steps may essentially be performed as described above for model generation.

An appropriate classification model is then applied to the dataset of lipid concentrations.

An appropriate classification model suitable for classifying normal and diseased samples, benign and malignant samples and early stage and late stage samples, as set out in the sections "Classification Models Generated from 340 Lipids", "Classification Models Generated from 340 Lipids (R1)", "Classification Models Generated from 340 Lipids (R2)", "Classification Models Generated from n Lipids (n<340)", "Classification Models Generated from 82 Choline Lipids", "Classification Model Generated from 44 Choline Lipids" and "Classification Model Generated from 77 Choline Lipids" may be applied to the data.

As described above, each classification model may comprise a transformation matrix and an SVM model. The dataset may go through a first, transformation, step. In this step, the dataset of lipid concentrations is transformed by a transformation matrix of the classification model. The resulting dataset may go through a second, classification, step. In this step, the resulting dataset is analysed by Support Vectors Machines (SVM), using an SVM model of the classification model.

A positive output of the SVM analysis indicates a normal, benign or early stage sample, as the case may be. A negative output of the SVM analysis indicates a diseased (ovarian cancer), malignant or late stage sample, as the case may be.

Figure 13:
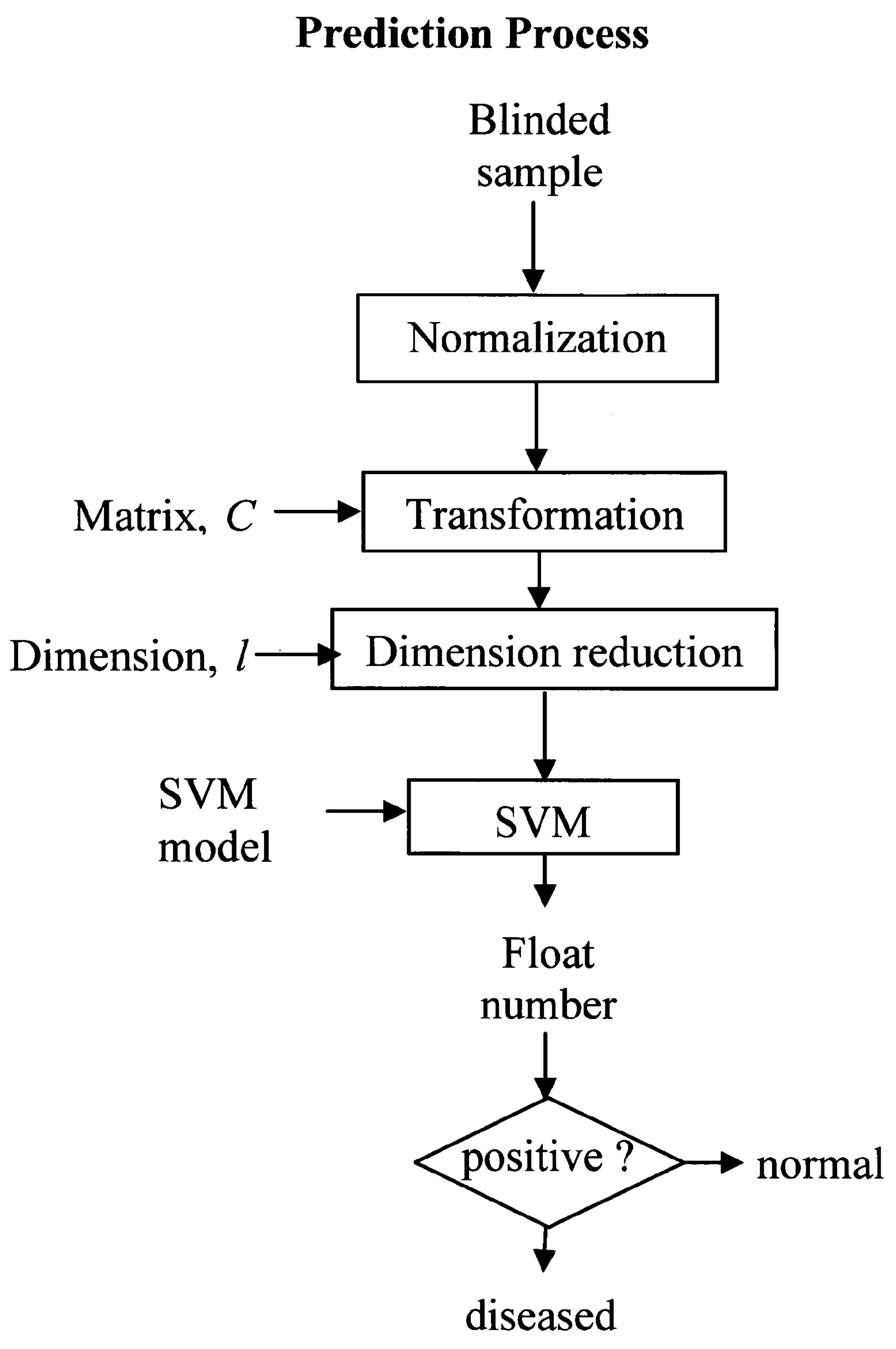
FIG. 13 is a flowchart showing the prediction process.

A schematic of the prediction process is shown in FIG. 13, which shows the optional normalization and dimension reduction steps. The prediction process is similar in some respects to the model generation process, but differs for example in that the PCA process may be replaced by transformation using matrix C defined in the classification model.

A single prediction process may be applied, or a number of prediction processes may be applied. Where this is the case, the classification models may be applied sequentially. Thus, a predictive process may be applied using a classification model for classifying normal and diseased samples, to indicate whether a sample is a normal sample or a diseased (i.e., ovarian cancer) sample. Where the sample is shown to be a diseased, ovarian cancer, sample, a further predictive process applying a classification model for classifying benign and malignant samples, to indicate whether a sample is a benign sample or a malignant ovarian cancer sample. Finally, where the sample is shown to be a malignant sample, a classification model for classifying early stage and late stage samples may be applied to the data, to indicate whether a sample is an early stage sample or a late stage ovarian cancer sample.

It will be clear that the bioinformatics methods of applying the classification models may be mixed and matched with other methods of classification, for example, histological staging and CA-125 serum levels.

Accordingly, an ovarian cancer sample diagnosed or determined by other means, e.g., histologically or biochemically, may be used as the subject of classification using the classification models described above. For example, an known ovarian cancer sample may be classed as a benign or malignant sample using a classification model capable of distinguishing benign and malignant samples.

Such an ovarian cancer sample, where it is classed as a malignant sample, may be subject to further analysis using a classification model capable of distinguishing between an early stage and a late stage sample, as described above, to class the sample as an early stage sample or a late stage sample. Similarly, such a classification model may be applied to lipid concentration data obtained form an ovarian cancer sample known to be a malignant sample (e.g., by histology) to establish whether the malignant sample is an early stage cancer sample or a late stage cancer sample.

In more detail, in the prediction process, the input sample with m lipids measured may be normalized such that the total lipid content is 1. The normalized data may then be transformed into the principal component space defined in the classification model, which is characterized by the matrix C. Upon obtaining the output vector, the transformed vector may be fed into the SVM model, which is stored in the classification model. Optionally, the first l rows, where l is a parameter stored in the classification model, of the transformed vector are selected and fed into SVM. The SVM model then outputs a float value whereby a negative value represents a label of −1 (diseased; benign; early stage) and a positive value represents a label of +1 (normal; malignant; late stage).

Example

The following describes an example of prediction using the methods and compositions described here. A blinded sample from the data obtained in the Examples, sample Id is 270, is used in this example.

The lipid concentrations from the sample are obtained. This data is passed through the prediction models based on the SVM obtained from the training set. When the data is passed through SVM-1 (Appendix C1, predicts if the subject is normal or has ovarian growth). A positive value should indicate that the subject is a control (i.e., undiseased) and a negative value should indicate that the subject has growth in the ovary.

The value obtained from the subject sample 270 using the above analysis −1.702055. Since this value is negative it indicates that the sample is a cancerous sample (i.e., the subject has an ovarian cyst/growth).

Accordingly, this data is then passed through SVM-2 (Appendix C2) which predicts if the growth is benign or malignant. Here the positive value should indicate a benign condition and a negative value should indicate malignancy.

The value obtained for the sample 270 is +1.104463. Since this is a positive value it is predicted as benign growth.

The sample is unblinded. The records show that the actual sample ID is 14757 (this ID is the actual ID used by a collaborator) and is a benign condition. The details of this blinded samples are as follows: Age 46 yrs, Ethnicity Chinese, Type of Cyst Benign, Subtype: Serous, CA125 test: 7.5 (the CA-125 test is a clinically used test and the value of 7.5 indicates that the sample is normal).

It will be appreciated that although the status of this blinded sample has been determined by other means, but is hidden, the exact same steps described below may be implemented on a sample of completely unknown status.

Treatment

Where samples and patients have been determined to have ovarian cancer, or are staged, etc, appropriate treatments may be given to them. For example, where appropriate, surgery to remove the cancerous tissue may be carried out. Radiotherapy or chemotherapy may also be applied.

Chemotherapy for localised ovarian cancer may comprise Carboplatin or a combination of Paclitaxel (Taxol) and carboplatin. The chemotherapy may for example be given intravenously. For recurrent ovarian cancer, carboplatin and paclitaxel (Taxol) treatment may be applied. Other treatments may include Paclitaxel (Taxol) alone, Topotecan or Liposomal doxorubicin (also called Caelyx or Doxil)—a type of a chemotherapy drug, doxorubicin. Other drugs may also be used, either alone or in combination.

If cancer comes recurs than 6 months after initial chemotherapy, Paclitaxel (Taxol) alone, Liposomal doxorubicin, Topotecan (Hycamtin), Gemcitabine or Cisplatin may be applied.

EXAMPLES

Using computational technologies, we have generated a diagnostic model to determine if a biological sample exhibits or is predictive or suggestive of a particular biological state. Such states may be associated with one or more diseases or physiological status.

To produce such a model, a number of samples having a known biological state are analyzed and compared with samples known to have been taken from patients who do not have that biological state. These data are then input into a modeling program, as described below, to find discriminatory patterns that are specific to a particular biological state. Such patterns are based upon various combinations of features or markers found in the data derived from the samples, such as lipid concentrations.

Figure 2:
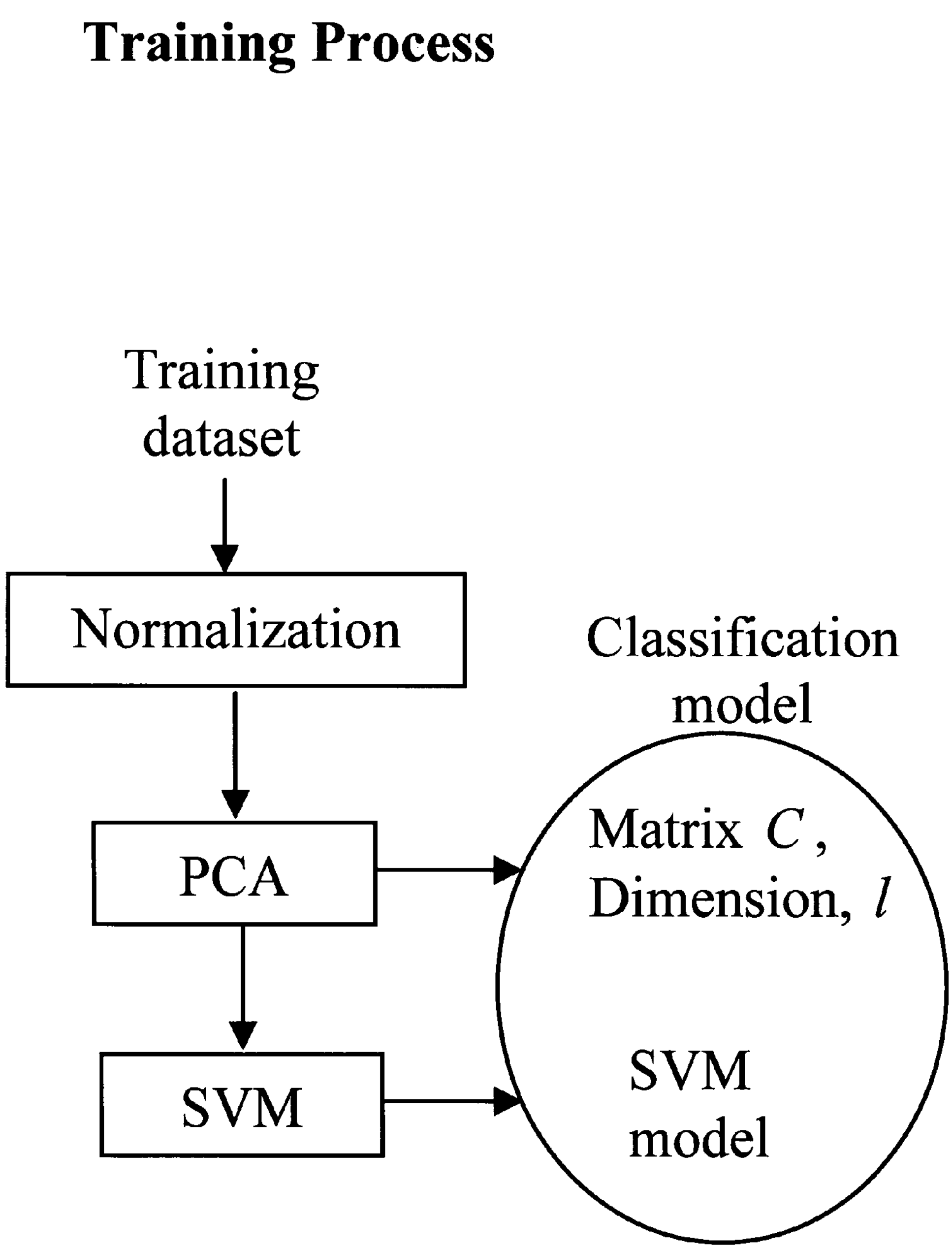
FIG. 2 is a flowchart showing the training process.

FIG. 1 is a chart illustrating the work flow for development of binary classifiers for ovarian cancers based on multiparameter analysis of plasma lipids and supervised learning. The flow diagram summarises the methodology for building the prediction model and diagnosis of unknown samples. FIG. 2 is a flowchart showing the training process.

Example 1

Sample Preparation and Analysis: Lipid Extraction

Lipids are extracted from 50 μl of blood samples using the modified Bligh Dyers extraction method.

Briefly, 600 μl of ice cold chloroform-methanol, 1:2 (v/v) is added to 50 μl of blood plasma along with the internal standards (Table E1) and vortexed vigorously for 1 min.

Table E1

| Standards | | |
|---|---|---|
| | Lipid Species | ug spiked |
| 1 | 17:0 Lyso GPA | 2.5 |
| 2 | 14:0 Lyso GPEtn | 2.5 |
| 3 | 19:0 Cer | 1 |
| 4 | 8:0 Glu Cer | 0.5 |
| 5 | 12:0 SM | 2.5 |
| 6 | di 14:0 GPGro | 0.5 |
| 7 | di 20:4 GPA | 2.5 |
| 8 | di 8:0 GPIns | 0.5 |
| 9 | di 22:6 GPSer | 2.5 |

The samples are incubated in ice for 10 min. followed by the addition of 300 μl chloroform. The phase is broken with the addition of 200 μl of 0.1M HCl or water and vortexed vigorously for 2 min. The phases are separated by centrifugation and the lower organic phase containing the lipids is transferred to fresh tube.

The lipids are re-extracted from the aqueous phase with 300 μl of chloroform pooled with the first organic extract and dried under vacuum. The extracted lipids are stored at −80° C. before analysis. Great care and precaution needs to be taken to ensure the generation of consistent and matched extract libraries.

The lipids are suspended in 200 μl of chloroform: methanol 1:1 (v/v) and used for mass spectrometry analysis.

Example 2

Sample Preparation and Analysis: Lipid Analysis

The lipids are initially separated on Waters XTerra C18 reverse phase column (1 mm×150 mm) column before entering into the mass spectrometer.

Typically, 5 μl of sample is injected for analysis. The inlet system consisted of a Waters CapLC autosampler, and a Waters CapLC pump. Chloroform-methanol 1:1 (v/v) with 15 mM piperidine is used as the mobile phase for isocratic elution at a flow rate of 15 μl/min. The column elutes are measured using Electrospray ionization mass spectrometry (ESI-MS) through a Waters Micromass Q-T of micro mass spectrometer operated in the negative ion mode. The capillary voltage and sample cone voltage are maintained at 3.0 kV and 50 V, respectively. The source temperature is 80° C. and the nanoflow gas pressure is maintained at 0.7 bars.

Figure 3:
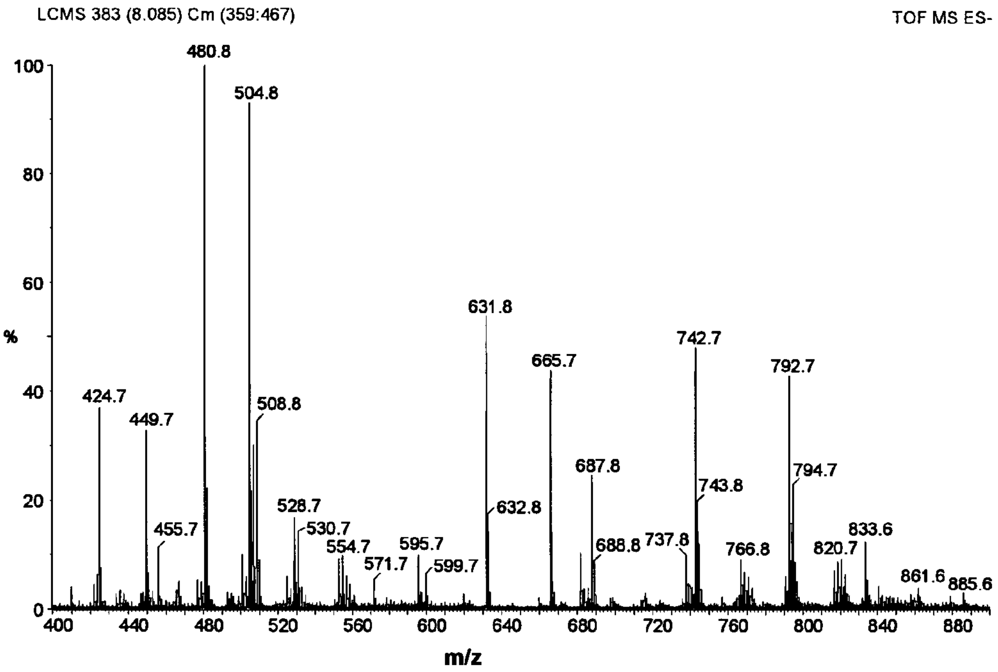
FIG. 3 illustrates the ESI profile of a representative plasma sample.

The mass spectrum is acquired from m/z 400 to 1600 in the negative or positive ion mode with an acquisition time of 20 min; the scan duration is 1.2 s. A representative spectra obtained in negative mode for one of the embodiment is depicted in FIG. 3. Individual molecular species are identified using tandem mass spectrometry and the collision energy used ranged from 25 to 80 eV.

Further identification and characterization of the lipid species is carried out using a 4000 Q-Trap mass spectrometer. The presence of a particular class of lipid is identified by product ion, precursor ion and neutral loss scans.

For GPEtn, GPIns and GPCho, the precursor ion scan for m/z 196 (negative mode), 241 (negative mode) and 184 (positive mode) respectively is carried out. For GPSer, neutral loss of 87 is monitored. For sphingolipids, precursor scans of 264, 266 and 184 are used. Presence of 153 is used for detection of GPA, GPGro as well as other phospholipids. The lipid molecules are further characterized and confirmed by tandem mass spec (MSMS) scans along with the other species like GPA, GPGro, Cardiolipin, Sulfatides, Ceramides and Spingomyelins. The characteristics daughter ion for each lipid molecule is noted.

Example 3

Sample Preparation and Analysis: Lipid Quantification

Quantification of individual lipid molecular species is performed using MRM with an Applied Biosystems 4000 Q-Trap mass spectrometer.

Samples are directly introduced into the mass spectrometry using an Agilent autosampler. In these experiments, the first quadrupole, Q1, are set to pass the precursor lipid ion of interest to the collision cell, Q2, where it underwent collision-induced dissociation. The third quadruple, Q3, is set to pass the structure specific product ion characteristic of the precursor lipid of interest.

Each individual ion dissociation pathway for the lipid species is optimized with regard to collision energy (CE), collision cell exit potential (CXP) and declustering potential (DP) with a dwell time of 25 msec. This is to minimize variations in relative ion abundance due to differences in rates of dissociation. The ion source gas GS1 and GS2 is maintained at 20 and 50 p.s.i. respectively and the curtain gas at 20 p.s.i. The entrance potential (EP) is set at 10.

In order to prevent the loss of the sensitivity of the method, the list is divided into 3 independent analysis sets. The first set consisted of the lipid classes belonging to GPA (Table E2A, Appendix A), GPGro (Table E2B, Appendix A), GPSer (Table E2C, Appendix A), Sulfatides (Table E2D, Appendix A) and Cardiolipins (Table E2E, Appendix A) monitored in the negative mode.

The second set consisted of the GPEtn (Table E2F, Appendix A), GPIns (Table E2G, Appendix A) and phosphoinositide phosphates (Table E2H, Appendix A) in negative mode.

The third set monitored the ions in the positive mode consisting of GPCho (Table E21, Appendix A), Spingomyelins (Table E2J, Appendix A), Ceramides (Table E2K, Appendix A) and their glycosylated derivative (Table E2L and Table E2M, Appendix A).

An optimized 15 μl of samples is injected per run per set with chloroform-methanol 1:1 (v/v) as the mobile phase at the flow rate of 200 μl/min. The run is carried out for 2 min.

Example 4

Data Analysis and Bioinformatics: Concentration Determination—Protocol for Determining Absolute Concentrations of Lipids using Spiked Standards and Standard Curve The data is normalized by the total intensities in that mode and the concentrations calculated using the respective spiked standards.

The normalization could be given as:

$$\text{Lipid}_i = \frac{x_i}{[Std] \cdot \sum_{i=1}^{n} x_i}$$

$x_i$ indicates the intensity of a particular type of lipid, $\text{lipid}_i$. Std indicates the constant obtained from the standard graph or from the spiked lipid standard. In the case of the spiked standard the Std is obtained as a ratio of the intensity to the amount (pmoles) of the standard spiked. The other way is to plot a standard graph with varying amount of the standards and then obtaining a standard graph. This graph then could give the ratio of the intensity over concentration and can be substituted in the above equation.

Depending upon the type of the lipid for which the concentration is to be calculated the respective standard is taken. A list of spiked standards and the lipids the spiked standards can be used to quantify is given in the table below.

| | Lipid Spiked | Can be used for quantification of |
|---|---|---|
| 1 | 17:0 Lyso GPA | Lyso GPA |
| 2 | 14:0 Lyso GPEtn | Lyso GPEtn, GPEtn |
| 3 | 19:0 Cer | Cer |
| 4 | 8:0 Glu Cer | MonoHexCer and DiHexCer |
| 5 | 12:0 SM | SM and Lyso GPCho, GPCho |
| 6 | Di 14:0 GPGro | Lyso GPGro, GPGro, Cardiolipin |
| 7 | Di 20:0 GPA | GPA |
| 8 | Di 8:0 GPIns | GPIns, GPInsP, GPInsP2, Sulfatide |
| 9 | Di 22:6 GPSer | Lyso GPSer, GPSer |

Example 5

Data Analysis and Bioinformatics: Principal Components Analysis (PCA) and Support Vector Machines (SVM)

The data is then processed using multivariate analysis (Principal Components Analysis).

Principal components analysis may be performed by a number of packages, for example Pirouette (Infometrix, Inc.), Statistica (StatSoft, Inc.), SPSS (SPSS Inc.), Unscrambler (CAMO Software AS.), PCA/X 5.0 (Windale Technologies Pty Ltd), XLSTAT (Addinsoft), StatistiXL. (StatistiXL), NMath Stats (CenterSpace Software), R (Freeware) (http://rss.acs.unt.edu/Rdoc/library/pcaMethods/html/00Index.html), SAS/INSIGHT (SAS Institute Inc.).

The outcome of the Principal Components Analysis is a score matrix. The score matrices are used as inputs into supervised learning methods like Support Vector Machine (SVM) for classification based on their diseased conditions.

SVMs are supervised learning methods which can perform binary classification (Noble, 2006). They map input feature vectors to a higher dimensional feature space where a maximal separation hyperplane is constructed.

SVM is implemented using SVMLight, which is executed in C. SVM models are built using default linear kernel functions. The output value from the SVM is a real number which signifies its distance from the hyperplane.

The outcome of the SVM is represented in the form of diagnostic utility matrix and the performance of the model is based on sensitivity, specificity and accuracy.

The model may then go to an iterative reduction in the dimension. The last PC is removed and the model built again. The new model is compared to the original model for its performance. This is repeated till the model loses its performance.

The final model generated is then evaluated by receiver operating curve, sensitivity, specificity, positive predictive value (PPV) and negative predictive value (NPV) and accuracy.

The model is then evaluated using the N-fold cross validation and predicting the blinded samples.

Example 6

Data Analysis and Bioinformatics: Statistical Considerations

The model is evaluated using receiver operating characteristics (ROC) curve, sensitivity, specificity, positive predictive value (PPV) and negative predictive value (NPV).

Sensitivity is the probability that a person who is positive are tested positive. Specificity is the probability that a person who is negative are tested negative. Sensitivity and specificity are also known as true positive and true negative rate respectively. Positive predictive value (PPV) gives the probability that a person tested positive is positive. Negative predictive value (NPV) gives the probability that a person tested negative is negative.

Other statistical tests like the student's t-test in case of normality in distribution or Mann Whitney U Test in case of non-normality in distribution, Kolmogorov-Smirnov goodness-of-fit hypothesis test are used to test for normality.

Example 7

Diagnostic Test for Ovarian Tumours

In this study, the MRM data is obtained to build a prediction model for predicting malignancy of ovarian cancer.

138 samples are used as a training set for model building. 383 lipids measurements are obtained for each and every sample. PCA is used to reduce the dimension of the training set and the reduced set is used as input feature vectors for SVM. Two SVM models are built using linear and quadratic kernel functions.

Example 8

Diagnostic Test for Ovarian Tumours: Patients and Procedures

All patient-derived biological specimens are collected under protocols approved by the National Health Group Institutional Review Board, Singapore and all participants provided written informed consent.

Whole blood samples are obtained preoperatively in EDTA tubes by routine venipuncture of women undergoing surgery for suspected ovarian cancer in National University Hospital (NUH), Singapore. All women ages 16 to 81 years undergoing surgery for suspected ovarian cancer are regarded as eligible for entry into the study. All of the samples are collected before the day of surgery or treatment. The plasma is immediately isolated and stored at −70° C. Just before the lipid extraction, the plasma is thawed. Of the preoperative samples obtained, 99 are from women who are later confirmed to have ovarian cancer.

Whole blood samples from control subjects are collected concurrently from healthy women from the same counties who reported no history of cancer, gynecologic disease, oophorectomy or family history of breast/ovarian cancer. The controls are either volunteers or are on routine checkup at the family care centers. All subjects recruited in this study are non-smokers. Whole blood specimens are obtained from a total of 99 ovarian cancer patients, including 40 patients with benign tumor, 22 patients at the early malignant stage (Stage I and II) and 37 at the late malignant stage (Stage III and IV).

Cancer diagnosis is confirmed for all cases by review of pathology records by a single ovarian cancer expert. Clinical stage is determined according to International Federation of Gynecologists and Obstetricians criteria, and the histological subtype is evaluated according to the WHO classification.

Using this methodology, 211 plasma samples are obtained which include the controls and patients are diagnosed as benign or with the malignant stages. The diagnosis is done using the Trans-vaginal Ultrasonography (TVU), Serum CA125 level and then confirmed by biopsies. The stage 1 and 2 of malignancy is classified as early malignant and the stage 3 and 4 as late malignant. The control samples are collected after careful examination of the donors.

Figure 4:
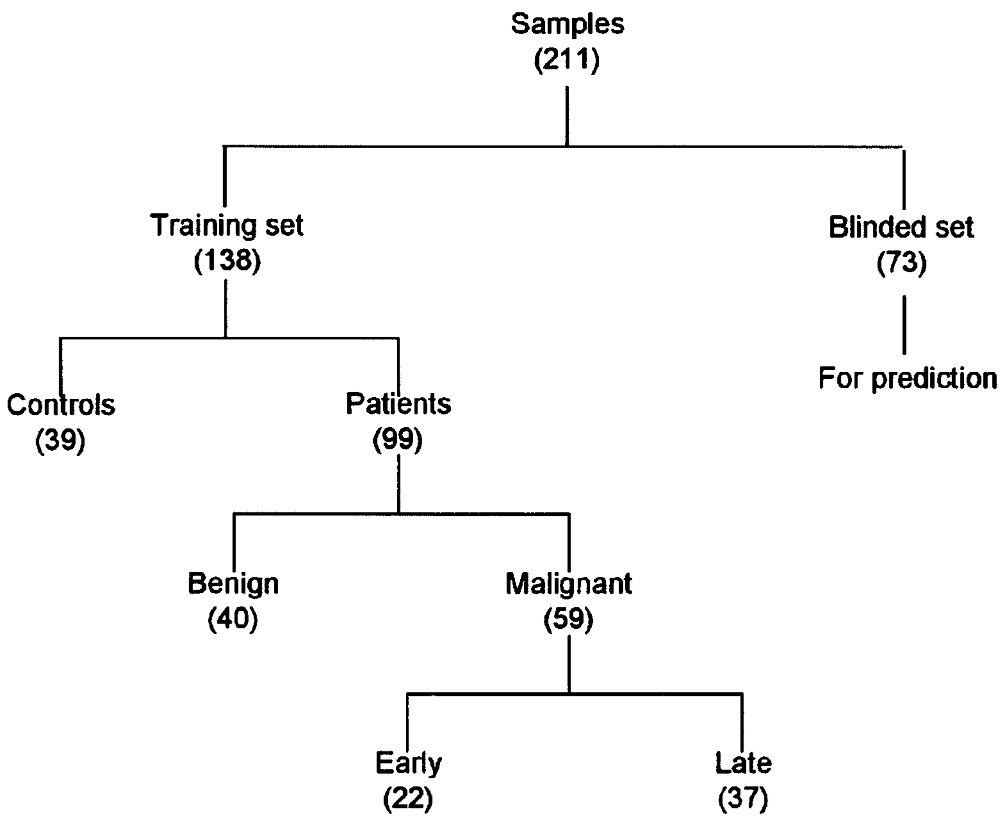
FIG. 4 illustrates the flow diagram of the samples. Case-control study setup. A total of 211 samples are randomly separated into a training set and a test set. The training set comprises 39 controls and 99 patients with 40 benign and 59 malignant forms of cancers, respectively. The model is built based on this training set and evaluated on the remaining 73 test samples.

Of these 211 samples, 138 samples are randomly selected irrespective of their pathological conditions. This formed a training set and the remaining 73 samples are blinded by the hospital staff and disclosed only after the complete analysis is done. The split up of the samples and their subsets is depicted in FIG. 4.

The training set included 39 plasma samples from control individuals and 99 from women with various forms of ovarian cancers. Out of the 99 patients samples 40 of the patients had tumors of benign characteristics and the remaining 59 are malignant tumors (22 of which are in the early stages and 37 in their late stages). The demographic profiling of these samples is represented in Table E3.

TABLE E3

Demographic Profiling of Plasma Samples in Training Set

| | Control | Patient | Benign | Malignant | Early | Late | Total |
|---|---|---|---|---|---|---|---|
| Age | | | | | | | |
| Ave Age | NA | 47 | 41 | 52 | 43 | 53 | |
| Max | NA | 81 | 74 | 81 | 74 | 81 | |
| Min | NA | 16 | 18 | 16 | 20 | 16 | |
| Median | NA | 48 | 41 | 53 | 48 | 56 | |
| Ethnicity | | | | | | | |
| Chinese | 23 | 67 | 26 | 41 | 17 | 24 | 90 |
| Malay | 7 | 20 | 9 | 11 | 2 | 9 | 27 |
| Indian | 6 | 6 | 3 | 3 | 2 | 1 | 12 |
| Other | 3 | 6 | 2 | 4 | 1 | 3 | 9 |
| Sum | 39 | 99 | 40 | 59 | 22 | 37 | 138 |
| Tumor type | | | | | | | |
| Endometroid | | 26 | 11 | 15 | 6 | 9 | 26 |
| Mucinous | | 22 | 13 | 9 | 8 | 1 | 22 |
| Ser/Pap | | 27 | 5 | 22 | 3 | 19 | 27 |
| Dermoid | | 6 | 6 | 0 | 0 | 0 | 6 |
| Physiol/foll | | 3 | 3 | 0 | 0 | 0 | 3 |
| Clear Cell | | 8 | 0 | 8 | 5 | 3 | 8 |
| Mixed Germ | | 1 | 0 | 1 | 0 | 1 | 1 |
| other | | 6 | 2 | 4 | 0 | 4 | 6 |

For the ovarian cancer patients various types of tumors are taken into account. The type of tumor is classified by various pathological test conducted on the tumor tissue. Control and patient samples are arranged randomly before lipid extraction.

Example 9

Diagnostic Test for Ovarian Tumours: Sample Analysis

Samples are extracted as described in Example 1 above and analyzed on an Applied Biosystems 4000 Q-TRAP mass spectrometer with the MRM method described.

Data peaks are integrated and normalized with respect total lipid content and ion response of internal standards.

Figure 5:
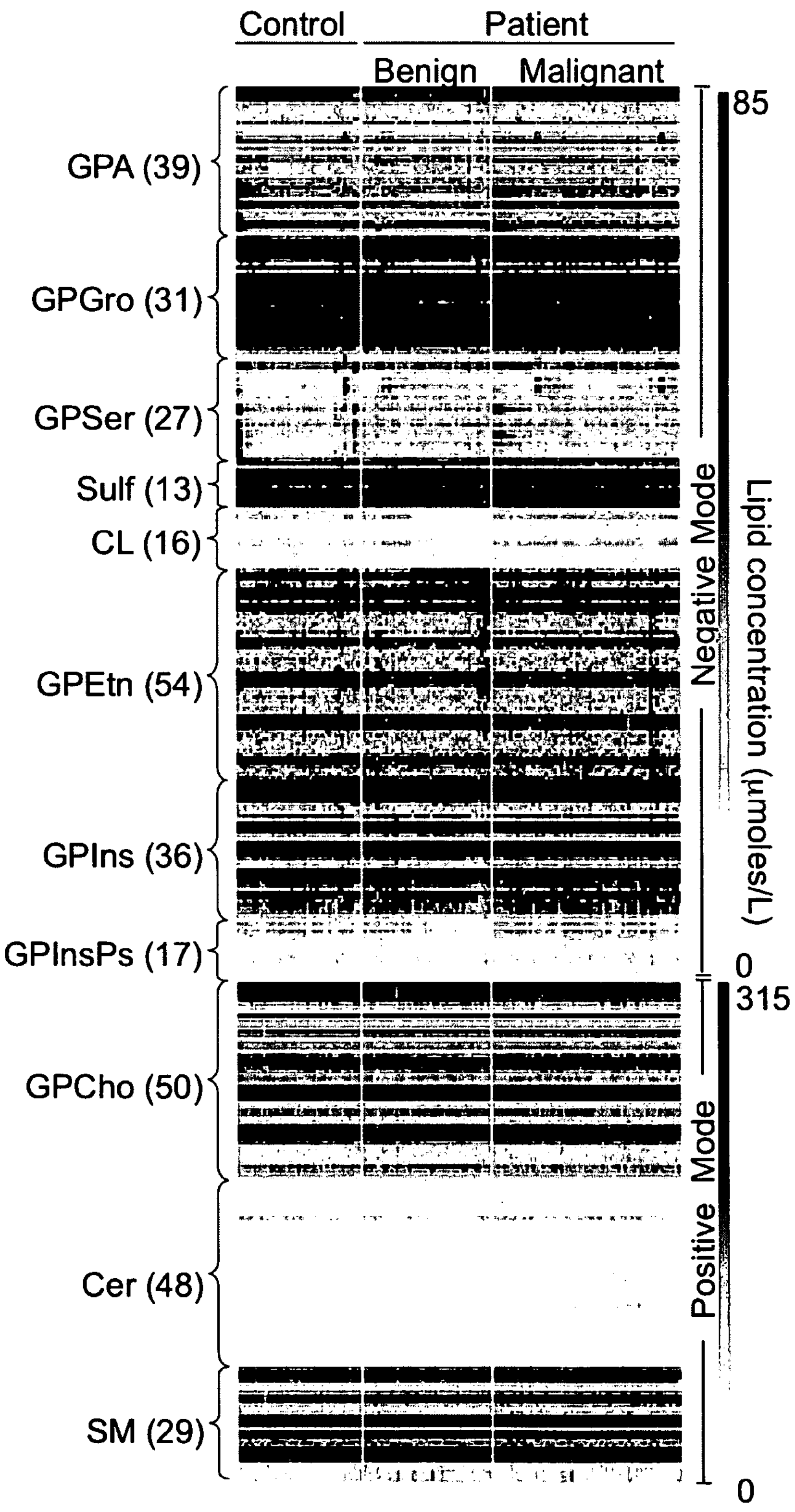
FIG. 5 shows comparative sample lipid levels. Raw data of multiparameter lipid analysis. The levels of individual lipids in plasma samples are quantified by electrospray ionization mass spectrometry and the intensity of each pixel indicates the concentration (from 0-85 μmoles/L and 0-315 μmoles/L for lipids measured in negative and positive ionization mode, respectively). Lipid species from eleven different classes are included in this study. Phosphatidic acid (GPA), phosphatidylglycerol (GPGro), phosphatidylserine (GPSer), sulfatides (Sulf), cardiolipins (CL), phosphatidylethanolamine (GPEtn), phosphatidylinositol (PtdIns) and its singly and doubly phosphorylated derivatives (GPInsPs), phosphatidylcholine (GPCho), ceramides and their glycosyl derivatives (Cer) and sphingomyelins (SM).

The lipid species are graphically represented as heat plot (FIG. 5).

Example 10

Diagnostic Test for Ovarian Tumours: Data Analysis and Bioinformatics

A broad look of the lipid profile doesn't suggest drastic differences in the lipid profile between the samples. Plasma levels within the eleven classes of lipids covered here were very comparable between the various cases and control populations with no apparent differences that would be obvious without thorough statistical evaluation.

Principal Components Analysis (PCA)

Principal Components Analysis is conducted on a dataset comprising the concentrations of the 340 lipids shown in Table D3.

The resulting score matrices (transformation matrices) are set out in the Appendices and are described below and in the detailed description above. The transformation matrices resulting from the PCA analysis may be used to form a classification model.

The principal components analysis (PCA) generated through orthogonal linear transformation of the dataset shows that the controls patients are indeed separated from the patient population (FIG. 6A) on a three dimensional projection ($1^{st}$, $2^{nd}$ and $3^{rd}$ principal components).

Figure 6:
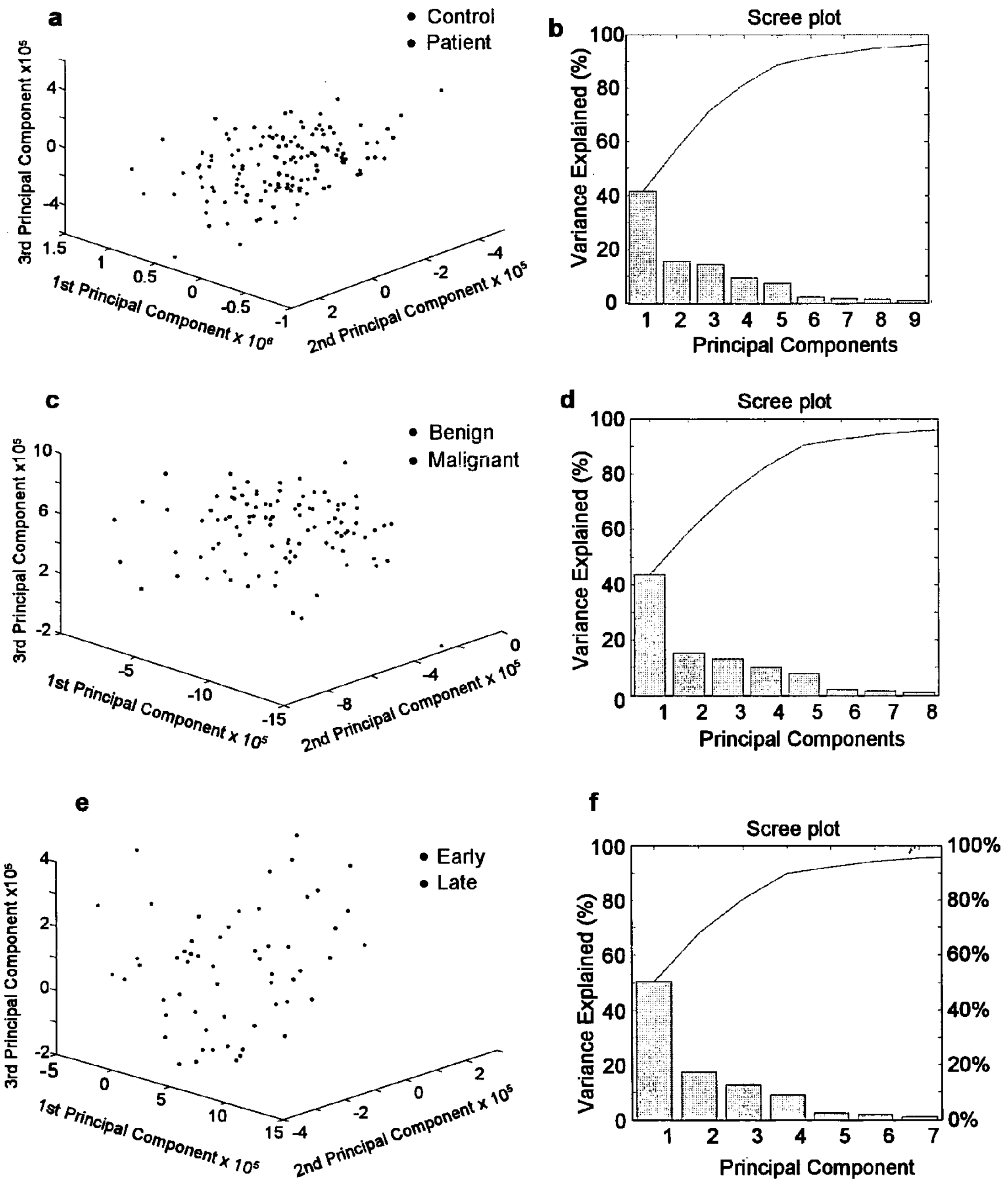
FIG. 6 shows principal component analysis between different sample sets. Multivariate statistical analysis and diagnostic performance in patients with different stages of ovarian cancer. Principal components analysis between (A) and (B) control and patients, (C) and (D) benign and malignant cases, (E) and (F) early and late cases and (G) and (H) control and benign and malignant cases.
Figure 6:
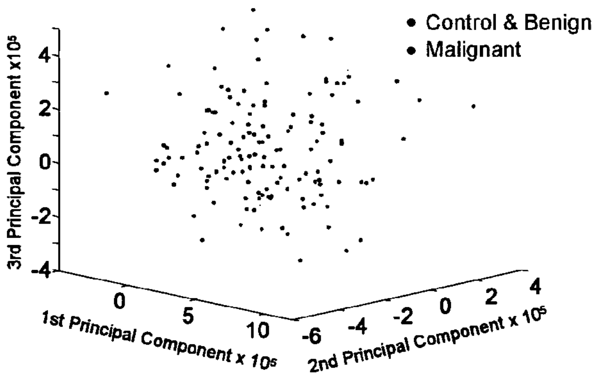
Figure 6:
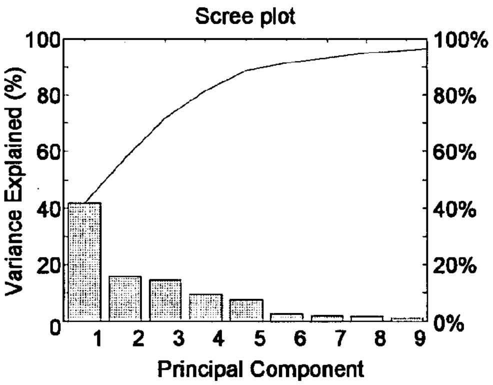

The first 3 principal components are able to define ~70% of the variance based on the Scree plot (FIG. 6B). The classifiers based on the PCA analysis are compiled and the list of these probable biomarker lipids are listed (Table E4).

TABLE E4

Lipid Classifiers for Principal Components Analysis

| No | Q1 mass | Q3 mass | Lipid Species |
|---|---|---|---|
| 1 | 758.7 | 184.1 | GPCho:34:2a |
| 2 | 703.8 | 184.4 | Sphingomyelin:d18:1/16:0 |
| 3 | 786.6 | 184.1 | GPCho:36:2a |
| 4 | 784.6 | 184.1 | GPCho:36:3a |
| 5 | 813.9 | 184.4 | Sphingomyelin:d18:1/24:1 |
| 6 | 782.6 | 184.1 | GPCho:36:4a |
| 7 | 759.8 | 184.4 | Sphingomyelin:d18:1/20:0 |
| 8 | 760.6 | 184.1 | GPCho:34:1a |
| 9 | 810.6 | 184.1 | GPCho:38:4a |
| 10 | 704.6 | 184.1 | GPCho:30:1a |
| 11 | 731.8 | 184.4 | Sphingomyelin:d18:1/18:0 |
| 12 | 814.6 | 184.1 | GPCho:38:2a |
| 13 | 496.4 | 184.1 | GPCho:Lyso 16:0 |
| 14 | 808.6 | 184.1 | GPCho:38:5a |
| 15 | 815.6 | 184.1 | Sphingomyelin:18/24:0 |
| 16 | 520.4 | 184.1 | GPCho:Lyso 18:2 |
| 17 | 761.8 | 184.4 | Sphingomyelin:d18:0/20:0 |
| 18 | 787.9 | 184.4 | Sphingomyelin:d18:1/22:0 |
| 19 | 743.8 | 279.3 | GPGro:18:2/16:1 |
| 20 | 812.6 | 184.1 | GPCho:38:3a |
| 21 | 524.4 | 184.1 | GPCho:Lyso 18:0 |
| 22 | 732.6 | 184.1 | GPCho:32:1a |
| 23 | 762.6 | 184.1 | GPCho:34:0a |
| 24 | 788.6 | 184.1 | GPCho:36:1a |
| 25 | 756.6 | 184.1 | GPCho:34:3a |
| 26 | 544.4 | 184.1 | GPCho:Lyso 20:4 |
| 27 | 834.6 | 184.1 | GPCho:40:6a |
| 28 | 568.4 | 184.1 | GPCho:Lyso 22:6 |
| 29 | 745.8 | 281.3 | GPGro:18:1/16:1 |
| 30 | 522.4 | 184.1 | GPCho:Lyso 18:1 |

Analysis of these lipids showed that mostly the GPCho and the sphingomyelins showed high ability to discriminate between the controls and the patient samples.

Appendix B1 shows a 340×340 transformation matrix of a classification model for classifying normal and diseased samples.

Similar analysis is carried out to differentiate between benign/malignant (FIG. 6C and FIG. 6D) and early/late forms of cancer (FIG. 6E and FIG. 6F).

Appendix B2 shows a 340×340 transformation matrix of a classification model for classifying benign and malignant samples. Appendix B3 shows a 340×340 transformation matrix of a classification model for classifying early and late samples.

Interestingly, PCA is able to separate the benign from the malignant samples, but the late from early are not well clustered. The Scree plot showed that the first 3 components are able to define nearly 70% of the variance for the benign vs. malignant dataset.

The data is also analyzed to check whether it is able to differentiate the malignant samples from a combination of benign and controls (FIG. 6G and FIG. 6F).

Support Vector Machines (SVM) Analysis

To evaluate the robustness of the profiling of lipids, a SVM based approach for classification of the samples is used.

Support Vector Machines analysis is conducted on a transformed dataset of the concentrations the 340 lipids shown in Table D3. The resulting SVM models are set out in the Appendices and are described below and in the detailed description above. The SVM models resulting from the SVM analysis may be used to form a classification model.

SVM is implemented using SVMLight. The PCA score matrix (N=138 samples by L=360 PC in case of the full training set) is used as the input feature vector for a support vector machine.

Figure 7:
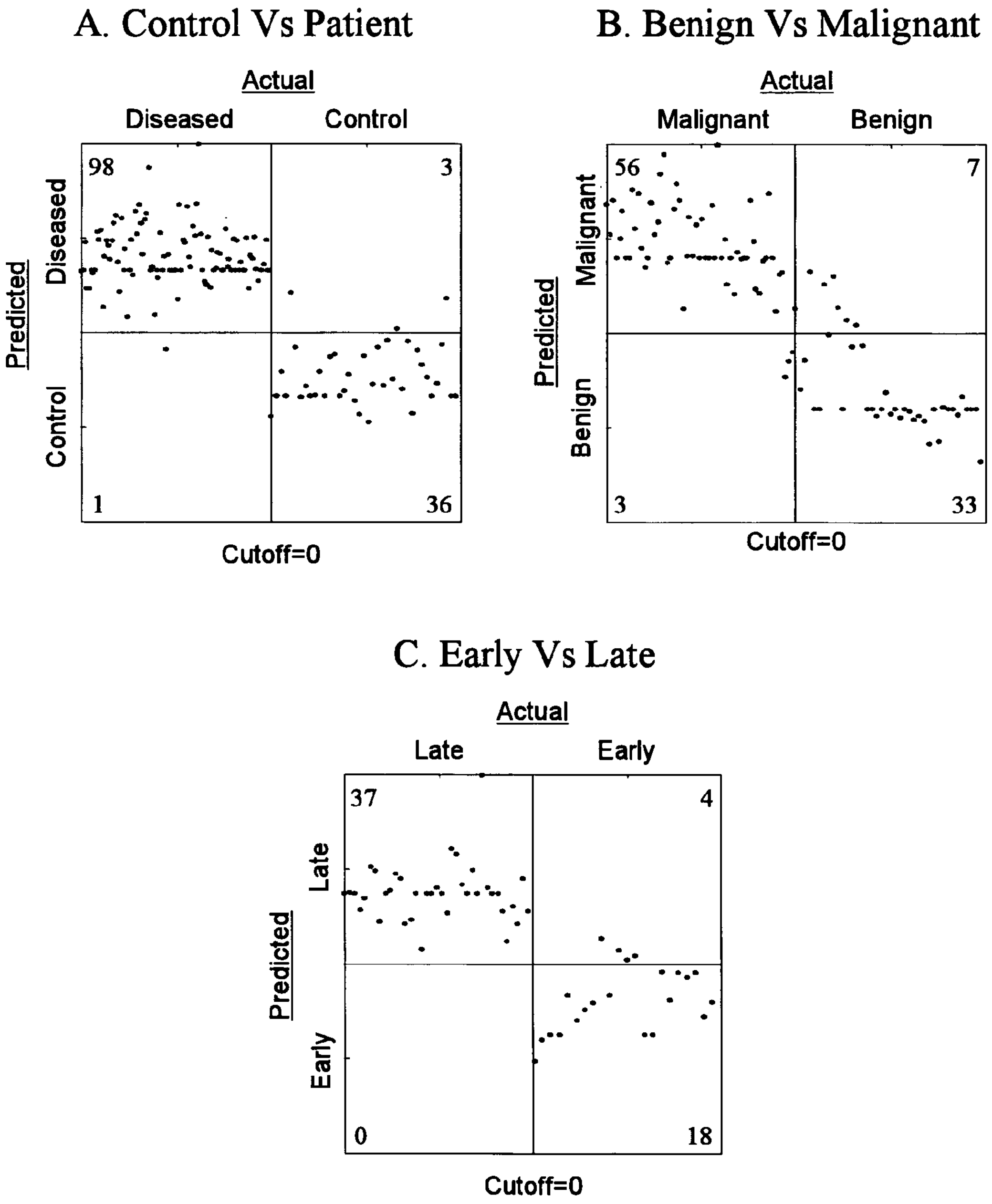
FIG. 7 shows diagnostic utility plot between different sets of sample of conditions. SVM output is represented as diagnostic utility matrixes for comparison between (A) control and patient, (B) benign and malignant forms of tumor differentiation, (C) early and late forms of tumour differentiation, (D) control/benign and malignant and (E) benign and early. The numbers represent true positive (TP), true negative (TN), false positive (FP) and false negative (FN) events in each category.
Figure 7:
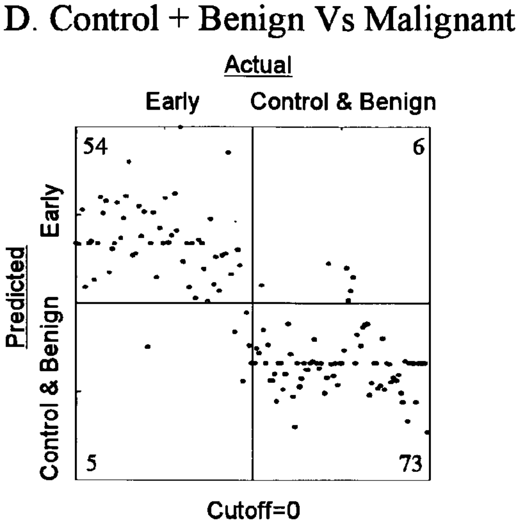
Figure 7:
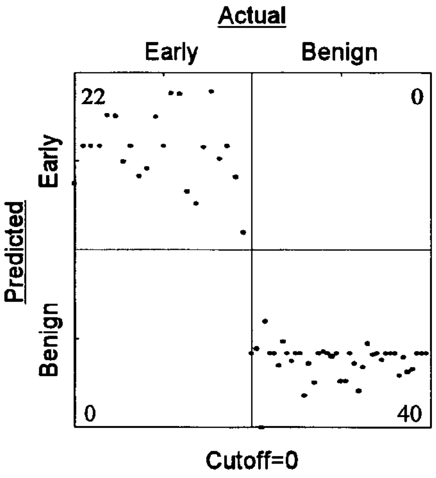

The output from the SVM model is assessed in the form of sensitivity, specificity and accuracy and used to describe the diagnostic utility (FIG. 7). The output of each SVM step can be visualized in a 2×2 matrix displaying true and false positives and negatives.

Appendix C1 shows an SVM model of a classification model for classifying normal and diseased samples. Such an SVM model may be used with a 340×340 transformation matrix shown in Appendix B1 and described above in the PCA section of this Example.

Appendix C2 shows an SVM model of a classification model for classifying benign and malignant samples. Such an SVM model may be used with a 340×340 transformation matrix shown in Appendix B2 and described above in the PCA section of this Example.

Appendix C3 shows an SVM model of a classification model for classifying early and late samples. Such an SVM model may be used with a 340×340 transformation matrix shown in Appendix B3 and described above in the PCA section of this Example.

Training

We next trained the SVM by iterative reduction of dimensions until a minimal set of PCs was found that resulted in maximal classifying performance (SVM model). This step is optional and is not strictly required.

The maximal classifying performance could comprise identical or similar performance compared to SVM analysis using the all or substantially all of the principal components (i.e., un-reduced). Performance may be assessed by any one or more, preferably all, of sensitivity, specificity, PPV, NPV, accuracy, true negatives (TN), false negatives (FN), false positives (FP) and true positives (TP).

The training process was done using the dataset comprising the concentrations of the 340 lipids shown in Table D3. The SVM models resulting from the SVM analysis conducted above using the training sets are set out in the Appendices and are described below and in the detailed description above.

Note that SVMs are binary classifiers. Thus, the above process was repeated to build SVM models for classification of patient vs. control (Patient/Control), i.e., diseased vs Normal, malignant vs. benign (Malignant/Benign) forms of cancers. A sequential arrangement of such binary classifiers can then be used for classification of samples from selected populations.

The cumulative performance of each of the classification models, as assessed by sensitivity, specificity, PPV and NPV, is shown in Appendices E1, E2 and E3. Appendix E1 shows the cumulative performance of a classification model (340 lipids) for normal versus diseased, by the number of principal components. Appendix E2 shows the cumulative performance of a classification model (340 lipids) for benign versus malignant, by the number of principal components. Appendix E3 shows the cumulative performance of a classification model (340 lipids) for early versus late, by the number of principal components. Rows in italics show the number of principal components required for a classification model which has identical performance compared to SVM analysis using the all the principal components.

In the case of the classification model for normal and diseased, maximal classifying performance may be obtained using 85 principal components. Appendix C4 shows the resulting SVM model. Such an SVM model may be used with a 340×85 transformation matrix comprising the first 85 columns of a matrix shown in Appendix B1 for classifying normal and diseased samples.

In the case of the classification model for benign and malignant, maximal classifying performance may be obtained using 87 principal components. Appendix C5 shows the resulting SVM model. Such an SVM model may be used with a 340×87 transformation matrix comprising the first 87 columns of a matrix shown in Appendix B2 for classifying benign and malignant samples.

In the case of the classification model for early and late, maximal classifying performance may be obtained using 44 principal components. Appendix C6 shows the resulting SVM model. Such an SVM model may be used with a 340×44 transformation matrix comprising the first 44 columns of a matrix shown in Appendix B3 for classifying early and late samples.

Example 11

Diagnostic Test for Ovarian Tumours: Model Results

The model showed the ability to discriminate the following conditions.

Normal vs Diseased 98 of the 99 diseased samples are predicted as samples from cancer patients and 36 out of the 39 controls are diagnosed as normal (FIG. 7A).

Benign vs Malignant

The power of the diagnostic tool can be appreciated from its ability to distinguish the benign from the malignant samples.

Of the 59 malignant, only 3 of the samples showed a false negative (FIG. 7B). The sensitivity, specificity and accuracy of this model are 95% (56 of 59), 83% (33 of 40) and 90% (89 of 99) (Table E5).

Early vs Late

Interestingly, the model is also able to show a good degree of classification between the early and the late stages of malignancy with 100% sensitivity (37 of 37), 82% specificity (18 of 22) and 93% accuracy (55 of 59) (FIG. 7C).

Normal or Benign vs Malignant

In a clinical scenario the benign growth is not considered life threatening and hence the lipid profiling is checked if it could also classify between the normal and the benign patients against the more drastic malignant cases.

The model shows that it is able to distinguish the malignancy from the rest of the samples with just 5 of the malignant samples falling in the false positive region (FIG. 7D). Malignancy could be distinguished from the rest of the samples with a specificity and sensitivity of 88% and 92%, respectively.

Benign vs Early

Moreover, the lipid profiling is also able to differentiate between benign and the early stages of cancer (FIG. 7E).

TABLE E5

Diagnostic Utility Matrix Analysis

| | Lipidomic | | | | |
|---|---|---|---|---|---|
| | Control Vs Patient | Benign Vs Malignant | Early Vs Late | Cont + Benign Vs Malignant | CA125 Benign Vs Malignant |
| True Positive (TP) | 98 | 56 | 37 | 52 | 43 |
| True Negative (TN) | 36 | 33 | 18 | 73 | 31 |
| False Positive (FP) | 3 | 7 | 4 | 6 | 9 |
| False Negative (FN) | 1 | 3 | 0 | 7 | 15 |
| Total | 138 | 99 | 59 | 138 | 98 |
| Sensitivity | 98.99 | 94.92 | 100.00 | 88.14 | 74.14 |
| Specificity | 92.31 | 82.50 | 81.82 | 92.41 | 77.50 |
| PPV | 97.03 | 88.89 | 90.24 | 89.66 | 82.69 |
| NPV | 97.30 | 91.67 | 100.00 | 91.25 | 67.39 |
| Accuracy | 97.10 | 89.90 | 93.22 | 90.58 | 75.51 |
| Prevalance | 71.74 | 59.60 | 62.71 | 42.75 | 59.18 |
| False positive rate | 7.69 | 17.50 | 18.18 | 7.59 | 22.50 |
| False Negative rate | 1.01 | 5.08 | 0.00 | 11.86 | 25.86 |
| Odds Ratio | 1176.00 | 88.00 | | 90.38 | 9.87 |
| Cohens Kappa | 0.93 | 0.79 | 0.85 | 0.84 | 0.50 |

Example 12

Diagnostic Test for Ovarian Tumours: Comparison of Model with CA125 Test

To determine whether lipidomic based approach offers a diagnostic advantage over the traditional CA125 test, the accuracy of these tests are compared.

The CA125 test which is gathered from the patients samples are analysed for their diagnostic ability. The same sets of samples are tested for the levels of CA125. The clinically approved level of 35 units/ml is taken as a cut-off to separate the benign from the malignant.

The CA125 test for discriminating between benign and malignancy showed a sensitivity of 74% (43 of 58), specificity of 78% (31 of 40) and accuracy of 76% (74 of 98). The positive predictive value for both the models are comparable but the negative predictive values showed superior performance of 92% when lipidomic based SVM is used as compared to just 59% for CA125. These values for CA125 are better than some of the reported diagnostic utility values for CA125.

Comparison between the models for various statistical diagnostic utility parameters based on SVM is summarized in Table E5. The lipid profiling based model showed superior prediction to differentiate between benign and malignant in comparison to the CA125 test. The model for the CA125 is moderate as the Cohen's Kappa value is only 0.5 as compared to 0.79 for the lipid profile based model which is considered substantial.

Figure 8:
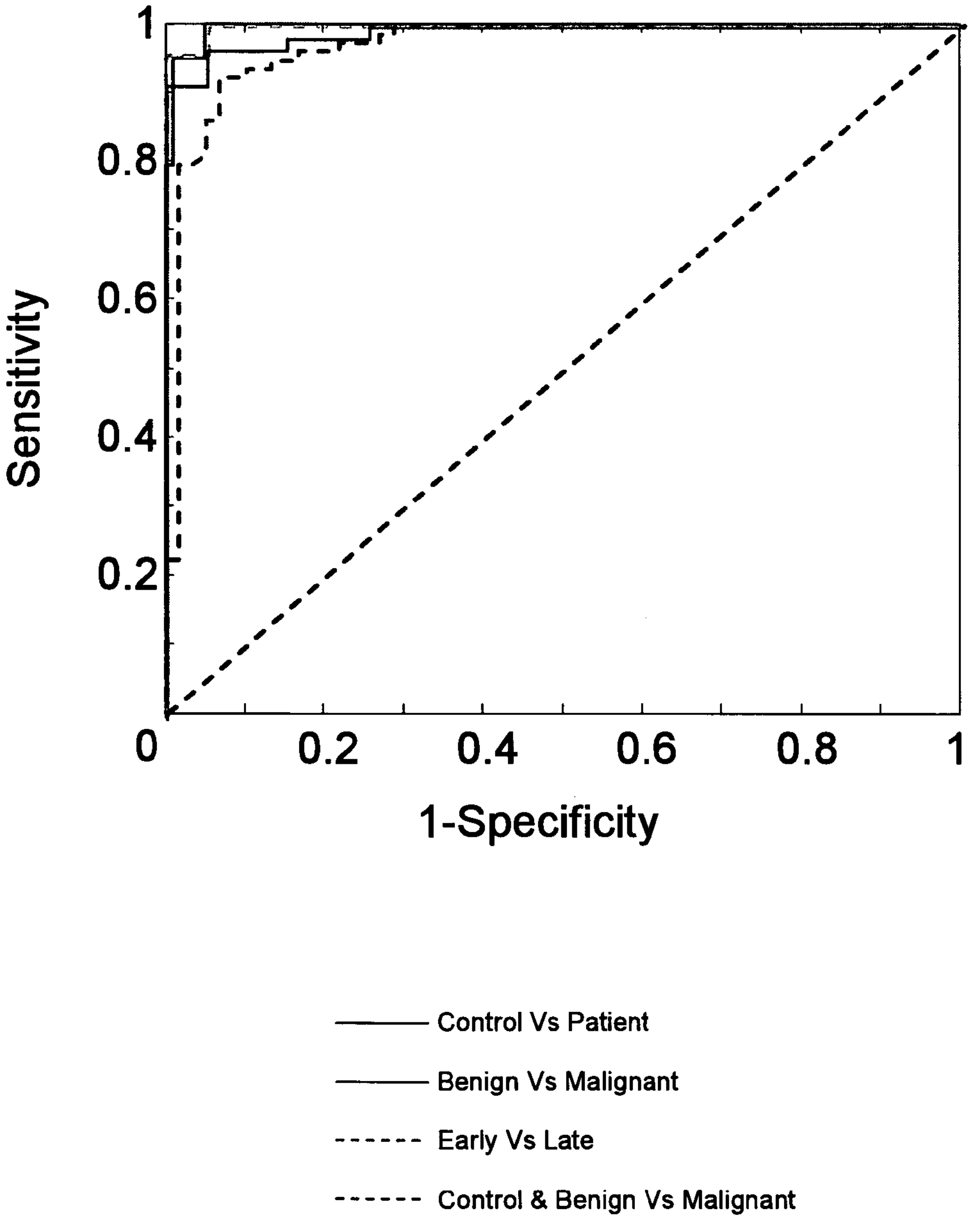
FIG. 8 shows a receiver operating characteristics (ROC) curve comparison for differences between the different diagnostic utilities.
Figure 9:
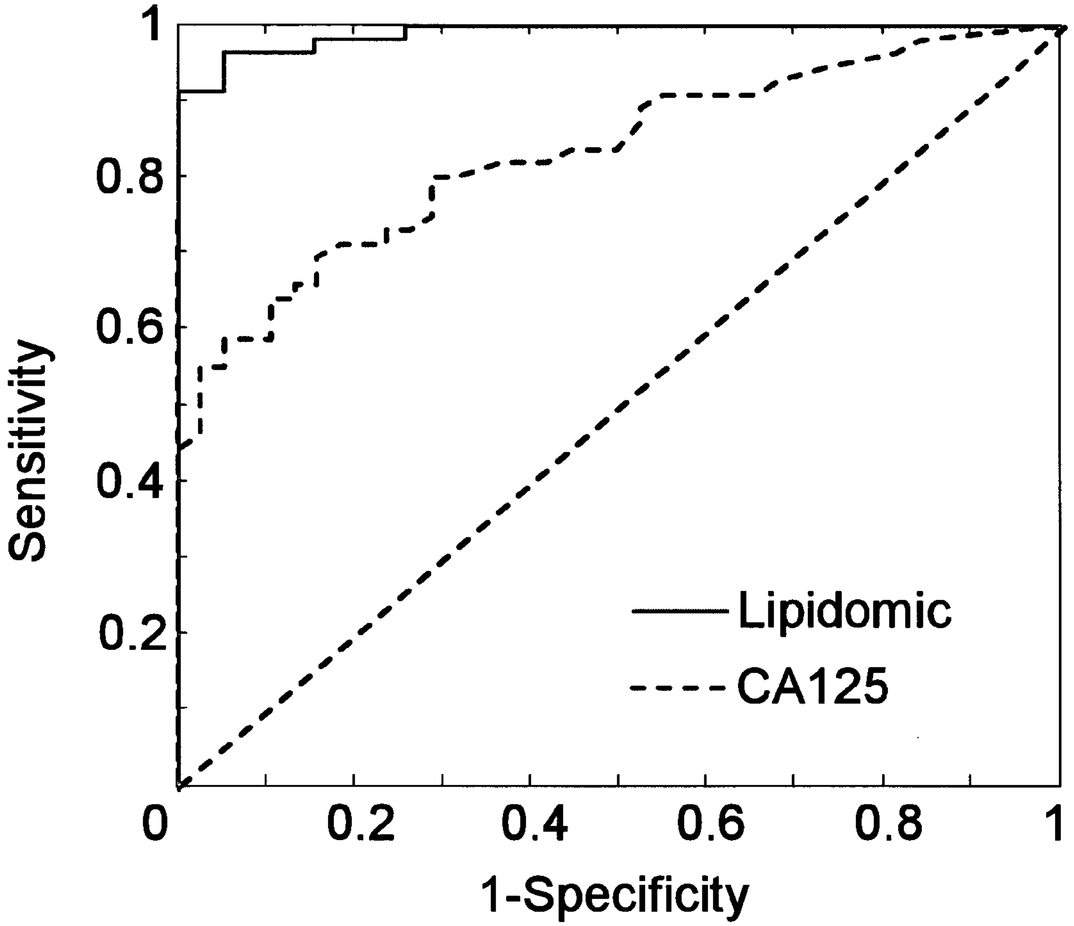
FIG. 9 shows a receiver operating characteristics (ROC) curve comparison between the lipidomic based biomarker and the clinical biomarker CA125 for differentiation of benign samples from malignant. The dashed line and dotted lines are the individual diagnostic performances of CA-125 and lysoGPA, respectively. Note the dramatic increase in predictive performance by multiparameter lipid markers.

The receiver operating characteristics (ROC) curves for the models are plotted and all the models performed better (FIG. 8). The method for diagnosing the difference between benign and malignant also confirmed the superiority of the model over the CA125 test (FIG. 9).

Example 13

Diagnostic Test for Ovarian Tumours: Training and Deriving Minimal Principal Components We further trained the SVM by iterative reduction of dimensions to determine the minimal number of principal components that would provide performance which is as good as or better compared to a CA-125 (Sensitivity=50%; Specificity=97.15%; PPV=17.24%; NPV=99.39%). For example, the number of principal components is chosen such that the model has a sensitivity and specificity which is higher than CA-125.

As described above in Example 10 (under Training), the cumulative performance of each of the classification models is set out in Appendices E1, E2 and E3. Rows in bold show the number of principal components required for a classification model which performs better than CA-125.

In the case of the classification model for normal and diseased, a classification model employing 10 principal components performs as well as or better than CA-125. Appendix C7 shows the resulting SVM model. Such an SVM model may be used with a 340×10 transformation matrix comprising the first 10 columns of a matrix shown in Appendix B1 for classifying normal and diseased samples.

In the case of the classification model for benign and malignant, maximal classifying performance may be obtained using 29 principal components. Appendix C8 shows the resulting SVM model. Such an SVM model may be used with a 340×29 transformation matrix comprising the first 29 columns of a matrix shown in Appendix B2 for classifying benign and malignant samples.

In the case of the classification model for early and late, maximal classifying performance may be obtained using 9 principal components. Appendix C9 shows the resulting SVM model. Such an SVM model may be used with a 340×9 transformation matrix comprising the first 9 columns of a matrix shown in Appendix B3 for classifying early and late samples.

Example 14

Diagnostic Test for Ovarian Tumours: Key Lipids

A major advantage of the targeted approach described here is its inherent foundation on a set of characterized lipid species. This is in complete contrast to previous proteomic studies which were based on pattern analysis of ions from largely unidentified and uncharacterized peptides.

Detailed comparison, using the Kruskal Wallis test (a non-parametric equivalence of ANOVA, FIG. 1), revealed a subset of ~80 lipid (82) species which are sufficient to describe >99.9% of the variance between the different sets of cases and controls.

A further striking result which provides new information on potential association with ovarian cancer is the observation of mis-regulated choline lipids.

Based on the principal components and also by individual calculations of the differences, lipids responsible for the separation of controls from patients are identified.

Figure 10:
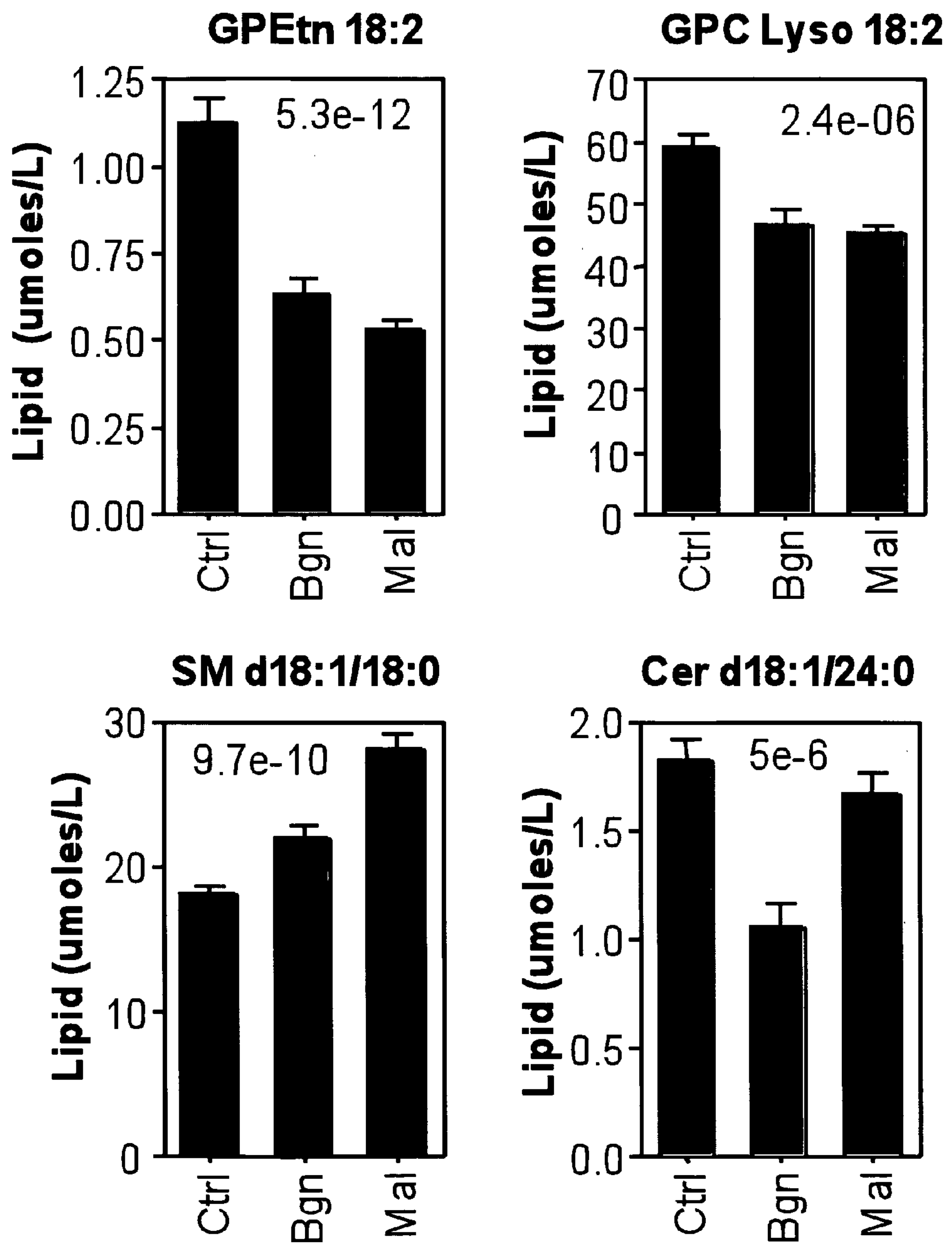
FIG. 10 shows a layout of the predictor model with extent of changes in the concentration of some lipids between cases and controls. Representative panel illustrating the extent of changes in the concentration of individual lipids between cases and controls. Data is represented as mean±s.e.m. and p-values obtained using the Kruskal-Wallis test.
Figure 11:
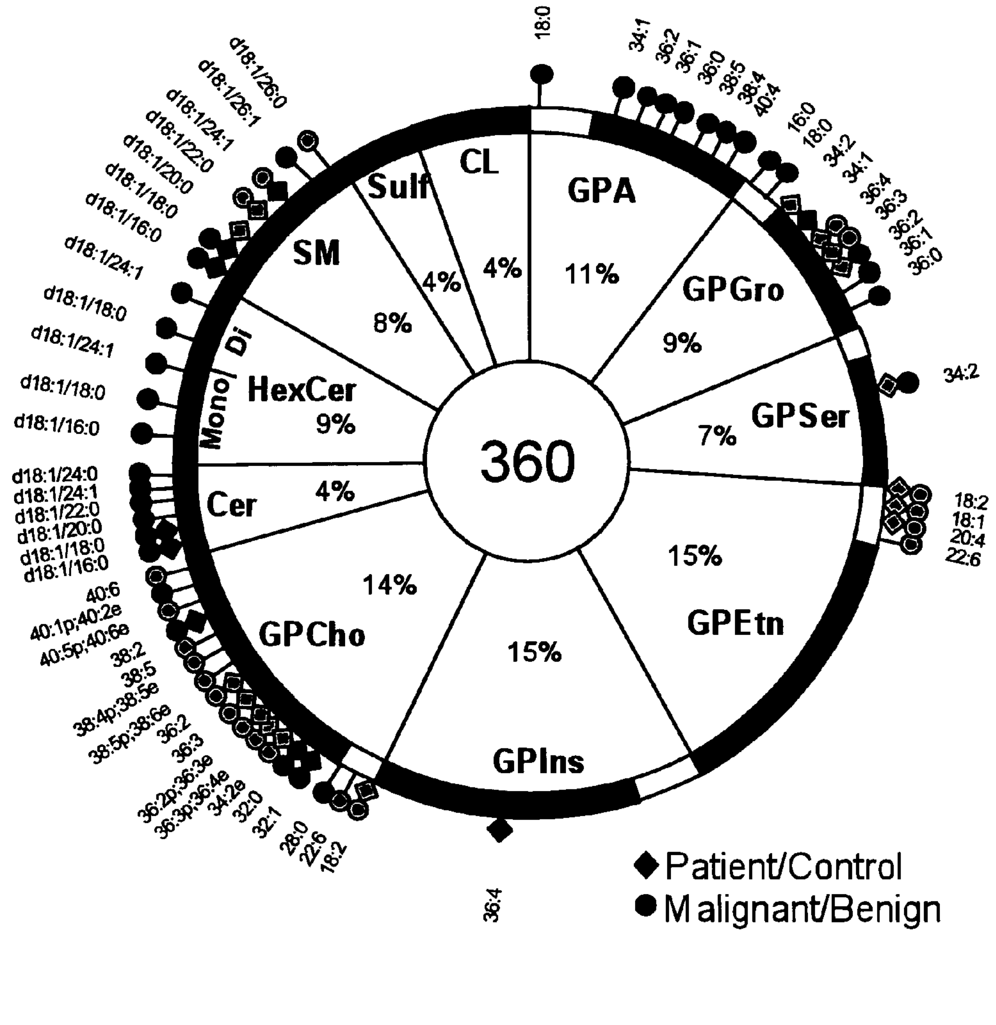
FIG. 11 shows the contribution of individual plasma lipids in diagnosis of patients with different stages of ovarian cancer. The lipid species covered in this study are represented as a pie chart. Percentages indicate the relative distribution among the 11 classes of lipids. The outer boundary of the chart depicts lyso (open) and non-lyso forms of lipids (filled). Only lipids with a difference and $p<0.001$ are shown. A blue circle indicates a increase in a particular lipid in malignant over benign forms of tumor while a red diamond reflects a decrease in the respective lipid in patient over control. Note the dramatic alterations of choline lipids (GPCho and SM) in plasma from patients with ovarian cancer. Some of the lipid species are represented as chemical structures.

Some of the few representative lipids are shown in FIG. 10. Contribution of the major lipid players in the diagnosis is depicted as a pie chart in FIG. 11. The lipids after removal of the standards and the backgrounds are narrowed down to 360 and is covered as a pie chart.

Percentages indicate the relative distribution among the 11 classes of lipids. The outer boundary of the chart depicts lyso (open) and non-lyso forms of lipids (filled). Only lipids with a difference and p<0.001 are shown. A blue circle indicates and increase in a particular lipid in malignant over benign forms of tumor while a red diamond reflects a decrease in the respective lipid in patient over control. Note the dramatic alterations of choline lipids (GPCho and SM) in plasma from patients with ovarian cancer. Some of the lipid species are represented as chemical structures. A list of the altered lipids between the cases and the controls is shown in Table E6.

TABLE E6

Lipids Responsible for Classification of Ovarian Cancers

| | Lipid | m/z | Benign | Malignant | p-value |
|---|---|---|---|---|---|
| 1 | GPA:36:0 | 703.8 | 29.71 | 80.76 | <1.0E−06 |
| 2 | GPA:16:0/22:5 | 721.8 | 65.75 | 187.84 | <1.0E−06 |
| 3 | GPA:38:0 | 731.8 | 44.66 | 109.80 | <1.0E−06 |
| 4 | GPGro:Lyso 16:0 | 483.4 | 89.99 | 175.45 | <1.0E−06 |
| 5 | GPGro:Lyso 18:0 | 511.4 | 89.22 | 186.02 | <1.0E−06 |
| 6 | GPGro:18:2/18:2 | 769.8 | 101.89 | 68.33 | <1.0E−06 |
| 7 | GPGro:18:0/18:0 | 777.8 | 57.67 | 175.25 | <1.0E−06 |
| 8 | GPEin:Lyso 18:2a | 476.6 | 55.96 | 46.37 | <1.0E−06 |
| 9 | GPEtn:Lyso 18:1 | 478.4 | 61.14 | 53.12 | <1.0E−06 |
| 10 | GPEtn:Lyso 20:4 | 500.4 | 77.46 | 40.49 | <1.0E−06 |
| 11 | GPEtn:Lyso 22:6 | 524.4 | 96.20 | 51.64 | <1.0E−06 |
| 12 | GPCho:32:0a | 734.6 | 106.21 | 125.10 | <1.0E−06 |
| 13 | GPCho:34:2e | 744.6 | 81.22 | 65.69 | <1.0E−06 |
| 14 | GPCho:36:2a | 786.6 | 90.83 | 81.70 | <1.0E−06 |
| 15 | GPCho:38:2a | 814.6 | 103.44 | 127.24 | <1.0E−06 |
| 16 | Cer:d18:1/18:0 | 566.7 | 118.28 | 232.24 | <1.0E−06 |
| 17 | Cer:d18:1/20:0 | 594.7 | 96.63 | 172.62 | <1.0E−06 |
| 18 | Cer:d18:1/22:0 | 622.8 | 74.18 | 122.63 | <1.0E−06 |
| 19 | Cer:d18:1/24:1 | 648.9 | 84.79 | 167.95 | <1.0E−06 |
| 20 | SM:d18:1/18:0 | 731.8 | 120.26 | 154.36 | <1.0E−06 |
| 21 | SM:d18:1/22:0 | 787.9 | 89.88 | 88.01 | <1.0E−06 |
| 22 | SM:d18:1/24:1 | 813.9 | 106.69 | 132.41 | <1.0E−06 |
| 23 | GPA:36:1 | 701.8 | 15.82 | 47.90 | 1.0E−06 |
| 24 | GPCho:36:3a | 784.6 | 93.47 | 79.88 | 1.0E−06 |
| 25 | GPCho:40:5p, 40:6e | 820.6 | 126.80 | 91.35 | 1.0E−06 |
| 26 | GPCho:40:6a | 834.6 | 137.30 | 94.11 | 1.0E−06 |
| 27 | SM:d18:1/26:0 | 843.9 | 135.42 | 92.25 | 1.0E−06 |
| 28 | GPCho:Lyso 18:2 | 520.4 | 78.55 | 75.98 | 2.0E−06 |
| 29 | GPCho:38:5a | 808.6 | 117.55 | 86.87 | 3.0E−06 |
| 30 | GPA:18:1/16:0 | 673.8 | 34.06 | 71.35 | 4.0E−06 |
| 31 | Cer:d18:1/24:0 | 650.9 | 58.15 | 91.39 | 513E−06 |
| 32 | GPCho:38:5p, 38:6e | 792.6 | 113.63 | 89.05 | 6.0E−06 |
| 33 | DiHexCer:d18:1/18:0 | 890.7 | 93.33 | 143.80 | 7.0E−06 |
| 34 | GPGro:18:2/18:1 | 771.8 | 75.18 | 77.63 | 1.0E−05 |
| 35 | GPCho:36:2p, 36:3e | 770.6 | 93.96 | 80.83 | 1.0E−05 |
| 36 | GPA:36:2 | 699.8 | 41.77 | 76.41 | 1.1E−05 |
| 37 | GPCho:28:0a | 678.5 | 62.22 | 69.74 | 1.2E−05 |
| 38 | MonoHexCer: d18:1/18:0 | 728.7 | 78.23 | 130.92 | 1.3E−05 |
| 39 | MonoHexCer: d18:1/ 24:1 | 810.9 | 96.74 | 147.14 | 1.9E−05 |
| 40 | Cer:d18:1/16:0 | 538.7 | 109.71 | 152.16 | 2.6E−05 |

Interestingly some of the GPEtn are also shown to be altered. The ovarian cancers have been shown to have an altered phosphatidylcholine metabolism. These three lipids are tightly interlinked both in their biochemical, synthetic and regulatory pathways.

There are reports of increased levels of choline phospholipids in the cancer cells. This is due to the increased activities of choline kinase, phospholipase C and phospholipase D in these cancer tissues. The exact role of these enzymes in carcinogenesis is not studied exclusively and remains inconclusive till date.

The overall reduction of choline lipids is mirrored by an increase in ceramides (Cer) and glycosylated ceramides (HexCer) pointing to activation of hydrolases with are specific for choline headgroups such as phospholipase (PLD) and sphingomyelinases (SMases). Thus it could be predictive that the levels of the lipids in the blood of the individuals could be a representative profile of these lipids in comparison to that in the ovarian tissues.

There could be a leakage or intake of these lipids through the ovarian cancer cells to or from blood, thereby altering their levels. Or else it could be a secondary effect upon the vascular system coming in contact with these abnormally growing cells. Further investigation needs to be carried out to answer the origin of this choline containing species.

Example 15

Diagnostic Test for Ovarian Tumours: Analysis Using Lipid Subset

Example 14 demonstrates that a subset of ~80 lipid (82) species is sufficient to describe >99.9% of the variance between the different sets of cases and controls.

These 82 lipids are set out in Table D2 above.

Corresponding classification models may be formed by applying PCA and SVM on a training dataset comprising concentrations of the 82 lipids shown in Table D2, using the methods described above.

The classification models are described in detail below. They may be used to classify normal vs diseased, benign vs malignant and early vs late, etc as described above. Accordingly, classification can be conducted by simply determining the concentrations of these 82 lipids in a biological sample from an individual and applying the classification methods described in this document.

Appendix B4 shows an 82×82 transformation matrix derived from PCA analysis of a dataset comprising lipid concentrations of the 82 lipids shown in Table D2 in normal and diseased samples. Appendix C10 shows a corresponding SVM model. The transformation matrix of Appendix B4 and the SVM model of Appendix C10 may be used as a classification model for classifying normal and diseased samples.

Appendix B5 shows an 82×82 transformation matrix derived from PCA analysis of a dataset comprising lipid concentrations of the 82 lipids shown in Table D2 in benign and malignant samples. Appendix C11 shows a corresponding SVM model. The transformation matrix of Appendix B5 and the SVM model of Appendix C11 may be used as a classification model for classifying benign and malignant samples.

Appendix B6 shows an 82×82 transformation matrix derived from PCA analysis of a dataset comprising lipid concentrations of the 82 lipids shown in Table D2 in early and late samples. Appendix C12 shows a corresponding SVM model. The transformation matrix of Appendix B6 and the SVM model of Appendix C12 may be used as a classification model for classifying benign and malignant samples.

Example 16

Diagnostic Test for Ovarian Tumours: Analysis Using Choline Lipids

Example 14 demonstrates that levels of choline lipids are associated with ovarian cancer.

Table D1 is a list of 77 choline lipid species, comprising phosphatidylcholines (GPCho) and sphingomyelins (SM).

Corresponding classification models may be formed by applying PCA and SVM on a training dataset comprising concentrations the 77 choline lipids shown in Table D1.

Figure 12:
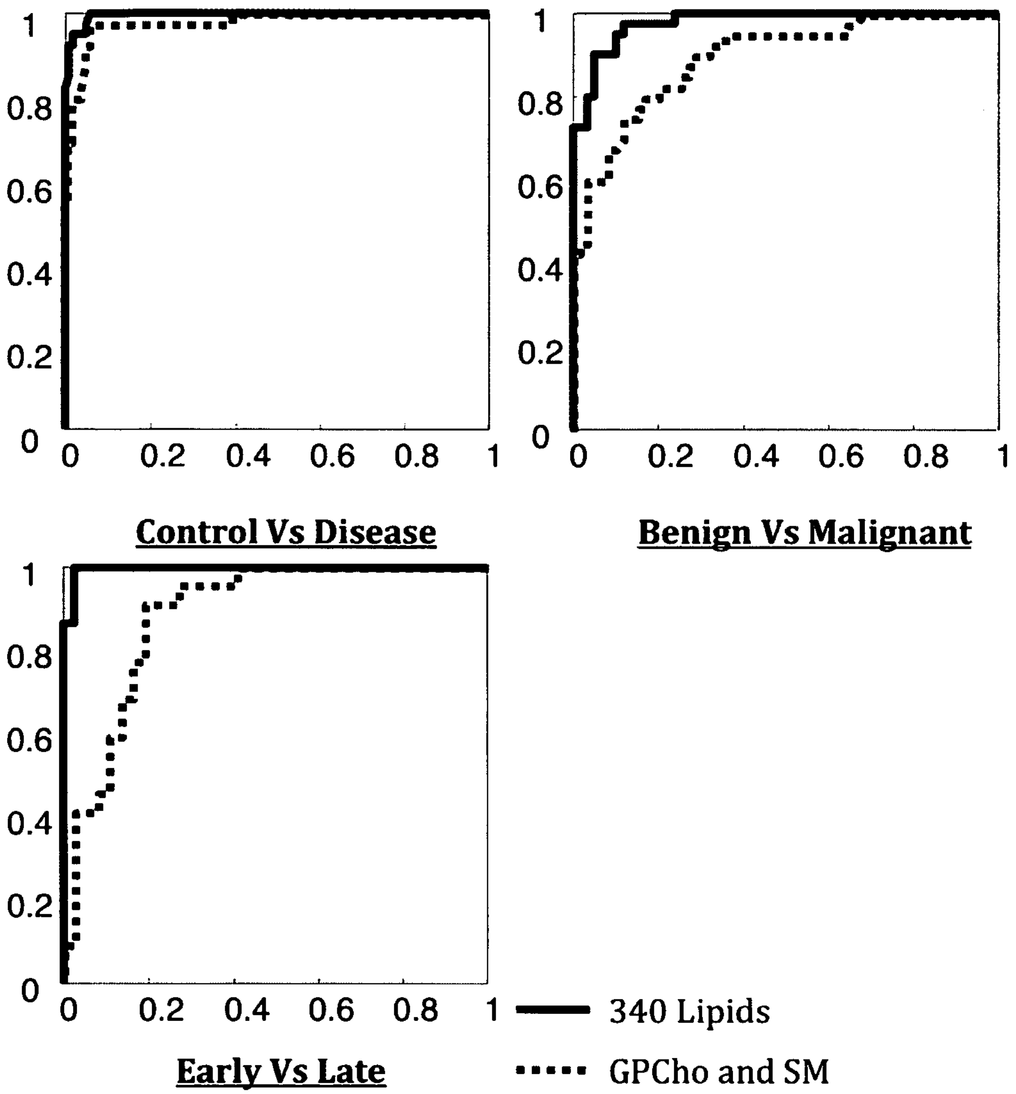
FIG. 12 shows a receiver operating characteristics (ROC) curve comparison between a classification model derived from analysis of the 77 choline lipids (GPCho and SM) in Table D1 (dashed line) and a classification model derived from analysis of the 340 lipids in Table D3 (solid line).

FIG. 12 shows a receiver operating characteristics (ROC) curve. The ROC curve compares the performance of a classification model derived from analysis of the 77 choline lipids (GPCho and SM) in Table D1 (dashed line) and a classification model derived from analysis of the 340 lipids in Table D3 (solid line).

The classification models are described in detail below. They may be used to classify normal vs diseased, benign vs malignant and early vs late, etc as described above. Accordingly, classification can be conducted by simply determining the concentrations of these 77 choline lipids in a biological sample from an individual and applying the classification methods described in this document.

Appendix B7 shows an 77×77 transformation matrix derived from PCA analysis of a dataset comprising lipid concentrations of the 77 choline lipids shown in Table D1 in normal and diseased samples. Appendix C13 shows a corresponding SVM model. The transformation matrix of Appendix B7 and the SVM model of Appendix C13 may be used as a classification model for classifying normal and diseased samples.

Appendix B8 shows an 77×77 transformation matrix derived from PCA analysis of a dataset comprising lipid concentrations of the 77 choline lipids shown in Table D1 in benign and malignant samples. Appendix C14 shows a corresponding SVM model. The transformation matrix of Appendix B8 and the SVM model of Appendix C14 may be used as a classification model for classifying benign and malignant samples.

Appendix B9 shows an 77×77 transformation matrix derived from PCA analysis of a dataset comprising lipid concentrations of the 77 choline lipids shown in Table D1 in early and late samples. Appendix C15 shows a corresponding SVM model. The transformation matrix of Appendix B9 and the SVM model of Appendix C15 may be used as a classification model for classifying benign and malignant samples.

Example 17

Diagnostic Test for Ovarian Tumours: Blinded Tests

To confirm our findings, we subsequently challenged our models to another set of independent 73 test samples which had been blinded before the prediction.

The analysis is done in a pseudo clinical setup in collaboration with the affiliated hospital. The samples are obtained in a set of 5 and the lipid extracts are carried out immediately after obtaining the samples. The lipids are analyzed on the mass spectrometry in a set of 10. This is to introduce day-to-day disparity in the extraction methods and also the mass spectrometry settings.

The prediction process is depicted in the flowchart shown in FIG. 13.

The demographic profiles of these 73 samples are depicted in Table E7.

TABLE E7

| Demographic Profiling of Plasma Samples in Blinded Set | | | | | | | | |
|---|---|---|---|---|---|---|---|---|
| BLIND SAMPLES | Ave Age | Max | Min | Chinese | Malay | Indian | Other/NA | Sum |
| Control | NA | NA | NA | 3 | 3 | 3 | 5 | 14 |
| Patient | 48 | 81 | 16 | 27 | 21 | 5 | 6 | 59 |
| Benign | 46 | 81 | 16 | 20 | 18 | 3 | 6 | 47 |
| Malignant | 49 | 74 | 16 | 7 | 3 | 2 | 0 | 12 |
| Early | 53 | 71 | 23 | 1 | 1 | 0 | 0 | 2 |
| Late | 47 | 74 | 16 | 6 | 2 | 2 | 0 | 10 |
| | | | | | | | | 73 |

| BLIND SAMPLES | Benign | Malignant | Early | Late |
|---|---|---|---|---|
| Endometroid | 11 | 2 | 1 | 1 |
| Mucinous | 8 | 5 | 1 | 4 |
| Ser/Pap | 8 | 3 | 0 | 3 |
| Dermoid | 11 | 0 | 0 | 0 |
| Physiol/foll | 1 | 0 | 0 | 0 |
| other | 8 | 2 | 0 | 2 |
| Clear Cell | 0 | 0 | 0 | 0 |
| Mixed Germ | 0 | 0 | 0 | 0 |
| | 47 | 12 | 2 | 10 |

Figure 14:
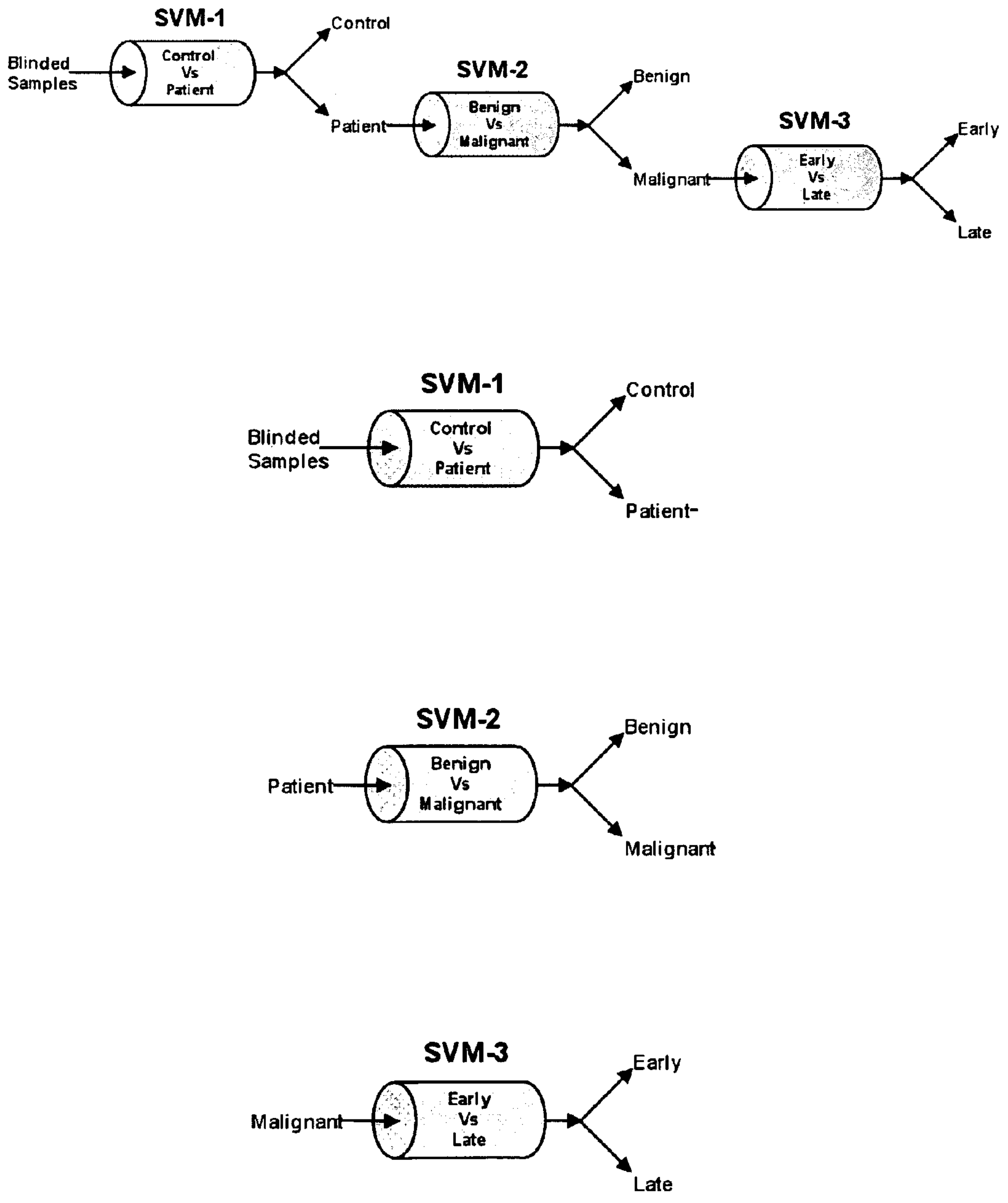
FIG. 14 shows the layout of the predictor model. Arrangement of individual SVMs for classification of blinded samples. SVM-1 is based on the 138 training set (patient/control). SVM-2 is based on 99 patient samples (malignant/benign). SVM-3 is based on 59 samples (early/late malignancy).

The blinded samples are passed through the SVM models which separated the samples into control, benign or malignant (FIG. 14).

In this scenario, a blinded sample passes through a maximum of 3 SVM models for full prediction. Each step makes a binary decision.

The first model (also known as "SVM-1") predicts whether the sample shows 'patient' or 'control' characteristic.

If classified as 'patient' it will continue through a second model (also known as "SVM-2") which predicts whether it is 'benign' or 'malignant'.

The third SVM (also known as "SVM-3") discriminates early vs. late stages.

Each of the blinded samples is passed through the predictors.

The predictions for all the 73 test samples are obtained and then the samples are un-blinded.

Example 18

Diagnostic Test for Ovarian Tumours: Blinded Tests Results

The lipidomic based biomarker is able to correctly diagnose 8 of the 11 malignant patients, 45 out of 48 benign patients and 10 out of 14 samples as normals. So in all 63 out of the 73 samples are predicted accurately. This rate of prediction seems to be quite reasonable.

The SVM also predicted the late from the early malignant samples but the number of malignant samples is observed to be very low and hence is not taken for statistical considerations. This is unavoidable as these sets of blinded samples are randomly separated from the original set of 211.

The prediction summary is depicted in Table E8.

TABLE E8

| Prediction Summary for the Blinded Samples Based on the SVM Models | | | | |
|---|---|---|---|---|
| | Control Vs Patient | Benign Vs Malignant | Early Vs Late | Cont + Benign Vs Malignant |
| True Positive (TP) | 55 | 8 | 1 | 8 |
| True Negative (TN) | 10 | 45 | 3 | 58 |
| False Positive (FP) | 4 | 3 | 5 | 4 |
| False Negative (FN) | 4 | 3 | 0 | 3 |
| Total | 73 | 59 | 9 | 73 |
| Sensitivity | 93.22 | 72.73 | 100.00 | 72.73 |
| Specificity | 71.43 | 93.75 | 37.50 | 93.55 |
| PPV | 93.22 | 72.73 | 16.67 | 66.67 |
| NPV | 71.43 | 93.75 | 100.00 | 95.08 |
| Accuracy | 89.04 | 89.83 | 44.44 | 90.41 |

The model is able to differentiate between the controls and the patients with a PPV and NPV of 93% (55 of 59) and 71% (10 of 14) with 89% accuracy (65 of 73), 93% sensitivity (55 of 59) and 71% specificity (10 of 14).

The predicted patients samples (59) are passed through the second predictor (SVM-2) to distinguish the benign from the malignant, the PPV and NPV obtained is 72% and 93% respectively with an accuracy of 89% (sensitivity 73%, specificity 94%).

The blinded samples are observed to have less number of malignant samples (11) and hence with this low number the third model (SVM-3) even though it is supposed to be a good predictor would not give a statistically significant data and hence is not used for prediction. Another model for the separation of the malignant from the controls and benign is able to give a PPV and NPV of 67% and 95% respectively with an accuracy of 90%.

Even though upon comparison between the model and the blinded samples, the blinded samples did not perform to the expectations, they still seem to justify the use of lipids as biomarker tools. This is so because the markers are able to differentiate between the benign against malignant cancer harboring patients which itself seems quite novel.

Example 19

Discussion

The goal of our study is not only to detect the patients from the normal but also to separate the benign from the malignant. This is because based on the present clinical scenario there are no available tools to identify the benign from the malignant unless the growth is surgically removed and goes to various pathological testing. We are able to do so and also extrapolate our model to separate the late from the early stages of malignancy. Our model worked very well in comparison to the CA125 test. Even though the CA125 showed slightly better performance than the previously reported work, it still could not match the performance of the lipid based biomarkers.

The strength of this method relies not only on using one set or class of biomarkers but a complete profile and then use it as a diagnostic tool. This reduces the room for error as the lipids which are screened as very high. Also the level of the sample that is needs for this type of analysis is very low.

As low as 50 μl of plasma sample which could be easily obtained from the patient is able to diagnose not only whether there is a formation of cyst but also whether this growth is benign or malignant. This will reduce the burden of the patients from going into unwanted surgical procedures and trauma. It could be emphasized that the CA125 in conjunction with the lipid based biomarker and the TVU could also increase then have a very good predictive rate.

This methodology of using MRM for the analysis is novel and there have been no reports to our knowledge to date which uses this robust way of quantification of lipids. This methodology seems superior to the semi-quantitative analysis using the lipid spectra as the spectra could be a mix of more than one species. And also one would need to do further studies to confirm the presence of the regulated species. This makes it less clinically significant.

In conclusion, the lipidomic based biomarker profiling can not only be used for the ovarian cancer but can be extrapolated to other pathological conditions.

References

Baker, D. L. et al. Plasma lysophosphatidic acid concentration and ovarian cancer. *JAMA* 287, 3081-3082 (2002).

Brügger, B., Erben, G., Sandhoff, R., Wieland, F. T., Lehmann, W. D. 1997. Quantitative analysis of biological membrane lipids at the low picomole level by nano-electrospray ionization tandem mass spectrometry [published erratum appears in Proc. Natl. Acad. Sci. USA. 1999. 96:10943]. Proc. Natl. Acad. Sci. USA. 94:2339-2344.

Cattell, R B (1966). The meaning and strategic use of factor analysis. In R. B. Cattell (Ed.), Handbook of multivariate experimental psychology (pp. 174-243). Chicago: Rand McNally.

Einhorn, N. et al. Prospective evaluation of serum CA 125 levels for early detection of ovarian cancer. *Obstet. Gynecol.* 80, 14-18 (1992).

Fernandis, A. Z. & Wenk, M. R. Membrane lipids as signaling molecules. *Curr. Opin. Lipidol.* 18, 121-128 (2007).

Glunde, K. & Serkova, N. J. Therapeutic targets and biomarkers identified in cancer choline phospholipid metabolism. *Pharmacogenomics*. 7, 1109-1123 (2006).

Guan, X. L. & Wenk, M. R. Mass spectrometry-based profiling of phospholipids and sphingolipids in extracts from Saccharomyces cerevisiae. *Yeast* 23, 465-477 (2006)

Han, X., Gross, R. W. 1994. Electrospray ionization mass spectroscopic analysis of human erythrocyte plasma membrane phospholipids. Proc. Natl. Acad. Sci. USA. 91:10635-10639.

Han, X., Gubitosi-Klug, R. A., Collins, B. J., Gross, R. W. 1996. Alterations in individual molecular species of human platelet phospholipids during thrombin stimulation: electrospray ionization mass spectrometry-facilitated identification of the boundary conditions for the magnitude and selectivity of thrombin-induced platelet phospholipid hydrolysis. Biochemistry. 35:5822-5832.

Hsu, F. F., Ma, Z., Wohltmann, M., Bohrer, A., Nowatzke, W., Ramanadham, S., Turk, J. 2000. Electrospray ionization/mass spectrometric analyses of human promonocytic U937 cell glycerophospholipids and evidence that differentiation is associated with membrane lipid composition that facilitate phospholipase A2 activation. J. Biol. Chem. 275:16579-16589.

Iorio, E. et al. Alterations of choline phospholipid metabolism in ovarian tumor progression. *Cancer Res.* 65, 9369-9376 (2005).

Jacobs, I. et al. Prevalence screening for ovarian cancer in postmenopausal women by CA 125 measurement and ultrasonography. *BMJ* 306, 1030-1034 (1993).

Jacobs, I. J. & Menon, U. Progress and challenges in screening for early detection of ovarian cancer. *Mol. Cell Proteomics*. 3, 355-366 (2004).

Joachims T. *Making large-Scale SVM Learning Practical*. Advances in Kernel Methods—Support Vector Learning, B. 1999. MIT Press. Ref Type: Generic Kaddurah-Daouk, R. et al. Metabolomic mapping of atypical antipsychotic effects in schizophrenia. *Mol. Psychiatry* (2007).

Kaiser, H F (1960). The application of electronic computers to factor analysis. Educational and Psychological Measurement, 20, 141-151.

Kerwin, J. L., Tuininga, A. R., Ericsson, L. H.1994. Identification of molecular species of glycerophospholipids and sphingomyelin using electrospray mass spectrometry. J. Lipid Res. 35:1102-1114.

Kim, H. Y., Wang, T. C., Ma, Y. C. 1994. Liquid chromatography/mass spectrometry of phospholipids using electrospray ionization. Anal. Chem. 66:3977-3982.

Koivusaloa et al, 2001. Journal of Lipid Research, Vol. 42, 663-672, April 2001.

Kozak, K. R. et al. Identification of biomarkers for ovarian cancer using strong anion-exchange ProteinChips: potential use in diagnosis and prognosis. *Proc. Natl. Acad. Sci. U. S. A.* 100, 12343-12348 (2003).

Laaksonen, R. et al. A systems biology strategy reveals biological pathways and plasma biomarker candidates for potentially toxic statin-induced changes in muscle. *PLoS. ONE*. 1, e97 (2006).

Menon, U. & Jacobs, I. Screening for ovarian cancer. *Best. Pract. Res. Clin. Obstet. Gynaecol.* 16, 469-482 (2002)

Merrill, A. H., Jr., Sullards, M. C., Allegood, J. C., Kelly, S., & Wang, E. Sphingolipidomics: high-throughput, structure-specific, and quantitative analysis of sphingolipids by liquid chromatography tandem mass spectrometry. *Methods* 36, 207-224 (2005).

Myher, J. J., Kuksis, A. 1995. Electrospray MS for lipid identification. INFORM. 6:1068-1072.

Noble, W. S. 2006. What is a support vector machine? *Nat. Biotechnol.* 24:1565-1567.

Okita, M., Gaudette, D. C., Mills, G. B., & Holub, B. J. Elevated levels and altered fatty acid composition of plasma lysophosphatidylcholine(lysoPC) in ovarian cancer patients! *Int. J. Cancer* 71, 31-34 (1997).

Patton, G. M., Fasulo, J. M., Robins, S. J. 1982. Separation of phospholipids and individual molecular species of phospholipids by high-performance liquid chromatography. *J. Lipid Res.* 23:190-196.

Petricoin, E. F. et al. Use of proteomic patterns in serum to identify ovarian cancer. *Lancet* 359, 572-577 (2002).

Ramanadham, S., Hsu, F. F., Bohrer, A., Nowatzke, W., Ma, Z., Turk, J. 1998. Electrospray ionization mass spectrometric analyses of phospholipids from rat and human pancreatic islets and subcellular membranes: comparison to other tissues and implications for membrane fusion in insulin exocytosis. Biochemistry. 37:4553-4567.

Schneiter, R., Brugger, B., Sandhoff, R., Zellnig, G., Leber, A., Lampl, M., Athenstaedt, K., Hrastnik, C., Eder, S., Daum, G., Paltauf, F., Wieland, F. T., Kohlwein, S. D. 1999. Electrospray ionization tandem mass spectrometry (ESI-MS/MS) analysis of the lipid molecular species composition of yeast subcellular membranes reveals acyl chain-based sorting/remodeling of distinct molecular species en route to the plasma membrane. J. Cell. Biol. 146:741-754.

Sjovall, K., Nilsson, B., & Einhorn, N. The significance of serum CA 125 elevation in malignant and nonmalignant diseases. *Gynecol. Oncol.* 85, 175-178 (2002).

Stevens, J (1966). Applied multivariate statistics for the social sciences ($3^{rd}$ ed. Pp 362-422). Mahwah, N.J., USA: Lawrence Erlbaum Associates.

Sutphen, R. et al. Lysophospholipids are potential biomarkers of ovarian cancer. *Cancer Epidemiol. Biomarkers Prev.* 13, 1185-1191 (2004).

Wenk, M. R. The emerging field of lipidomics. *Nat. Rev. Drug Discov.* 4, 594-610 (2005).

Xu, Y. et al. Lysophosphatidic acid as a potential biomarker for ovarian and other gynecologic cancers. *JAMA* 280, 719-723 (1998).

Yetukuri, L. et al. Bioinformatics strategies for lipidomics analysis: characterization of obesity related hepatic steatosis. *BMC. Syst. Biol.* 1, 12 (2007).

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

APPENDIX A

MRM Conditions for Lipids

| | A | B | C | D | E | F | G | H | I |
|---|---|---|---|---|---|---|---|---|---|
| 1 | Number | Parent Ion | Daughter Ion | Lipid Identification | Dwell (mSec) | DP | EP | CE | CXP |
| 2 | 1 | 409.4 | 255.3 | 409.4/255.3>GPA:Lyso 16:0 | 25 | −110 | −10 | −40 | −10 |
| 3 | 2 | 433.4 | 279.3 | 433.4/279.3>GPA:Lyso 18:2 | 25 | −60 | −10 | −30 | −6 |
| 4 | 3 | 435.4 | 281.3 | 435.4/281.3>GPA:Lyso 18:1 | 25 | −120 | −10 | −30 | −4 |
| 5 | 4 | 437.4 | 283.3 | 437.4/283.3>GPA:Lyso 18:0 | 25 | −110 | −10 | −40 | −5 |
| 6 | 5 | 451.4 | 297.3 | 451.4/283.3>GPA:Lyso 18:0 | 25 | −70 | −10 | −30 | −5 |
| 7 | 6 | 459.6 | 305.5 | 459.6/305.5>GPA:Lyso 20:3 | 25 | −90 | −10 | −20 | −24 |
| 8 | 7 | 461.6 | 307.5 | 461.6/307.5>GPA:Lyso 20:2 | 25 | −80 | −10 | −40 | −20 |
| 9 | 8 | 463.7 | 309.5 | 463.7/309.5>GPA:Lyso 20:1 | 25 | −80 | −10 | −35 | −8 |
| 10 | 9 | 465.7 | 311.5 | 465.7/311.5>GPA:Lyso 20:0 | 25 | −80 | −10 | −30 | −12 |
| 11 | 10 | 481.4 | 327.3 | 481.4/327.3>GPA:Lyso 22:6 | 25 | −110 | −10 | −30 | −4 |
| 12 | 11 | 483.4 | 329.3 | 483.4/329.3>GPA:Lyso 22:5 | 25 | −60 | −10 | −20 | −6 |
| 13 | 12 | 641.8 | 251.3 | 641.8/251.3>GPA:16:1/16:2 | 25 | −140 | −10 | −40 | −8 |
| 14 | 13 | 643.8 | 253.3 | 643.8/253.3>GPA:16:1/16:1 | 25 | −60 | −10 | −70 | −16 |
| 15 | 14 | 645.8 | 255.3 | 645.8/255.3>GPA:16:1/16:0 | 25 | −120 | −10 | −40 | −10 |
| 16 | 15 | 647.8 | 255.3 | 647.8/255.3>GPA:16:0/16:0 | 25 | −120 | −10 | −50 | −4 |
| 17 | 16 | 667.8 | 279.3 | 667.8/279.3>GPA:34:4 | 25 | −160 | −10 | −70 | −4 |
| 18 | 17 | 669.8 | 279.3 | 669.8/279.3>GPA:34:3 | 25 | −100 | −10 | −50 | −14 |
| 19 | 18 | 669.8 | 281.3 | 669.8/281.3>GPA:34:4 | 25 | −140 | −10 | −40 | −4 |
| 20 | 19 | 671.8 | 279.3 | 671.8/279.3>GPA:18:2/16:0 | 25 | −80 | −10 | −40 | −10 |
| 21 | 20 | 673.8 | 281.3 | 673.8/281.3>GPA:18:1/16:0 | 25 | −140 | −10 | −50 | −14 |
| 22 | 21 | 695.8 | 279.3 | 695.8/279.3>GPA:36:4 | 25 | −140 | −10 | −40 | −10 |
| 23 | 22 | 695.8 | 303.3 | 695.8/303.3>GPA:36:4 | 25 | −60 | −10 | −40 | −16 |
| 24 | 23 | 697.8 | 305.3 | 697.8/281.3>GPA:20:3/16:0 | 25 | −100 | −10 | −50 | −5 |
| 25 | 24 | 697.8 | 281.3 | 697.8/305.3>GPA:18:1/18:2 | 25 | −160 | −10 | −50 | −5 |
| 26 | 25 | 699.8 | 279.3 | 699.8/279.3>GPA:36:2 | 25 | −140 | −10 | −40 | −8 |
| 27 | 26 | 699.8 | 281.3 | 699.8/281.3>GPA:36:2 | 25 | −160 | −10 | −50 | −8 |
| 28 | 27 | 701.8 | 283.3 | 701.8/283.3>GPA:36:1 | 25 | −200 | −10 | −50 | −4 |
| 29 | 28 | 703.8 | 283.3 | 703.8/283.3>GPA:36:0 | 25 | −180 | −10 | −50 | −18 |
| 30 | 29 | 721.8 | 281.3 | 721.8/255.3>GPA:18:1/20:4 | 25 | −200 | −10 | −50 | −5 |
| 31 | 30 | 721.8 | 255.3 | 721.8/281.3>GPA:16:0/22:5 | 25 | −140 | −10 | −50 | −14 |
| 32 | 31 | 723.8 | 283.3 | 723.8/283.3>GPA:18:0/20:4 | 25 | −200 | −10 | −50 | −5 |
| 33 | 32 | 725.8 | 305.3 | 725.8/305.3>GPA:20:3/18:0 | 25 | −200 | −10 | −40 | −5 |
| 34 | 33 | 729.8 | 281.3 | 729.8/281.3>GPA:38:1 | 25 | −100 | −10 | −70 | −6 |
| 35 | 34 | 731.8 | 283.3 | 731.8/283.3>GPA:38:0 | 25 | −140 | −10 | −50 | −12 |
| 36 | 35 | 751.8 | 303.3 | 751.8/303.3>GPA:40:4 | 25 | −160 | −10 | −40 | −12 |

APPENDIX A-continued

MRM Conditions for Lipids

| | A | B | C | D | E | F | G | H | I |
|---|---|---|---|---|---|---|---|---|---|
| 37 | 36 | 757.8 | 281.3 | 757.8/281.3>GPA:40:1 | 25 | −180 | −10 | −50 | −20 |
| 38 | 37 | 759.8 | 283.3 | 759.8/283.3>GPA:40:0 | 25 | −60 | −10 | −60 | −16 |
| 39 | 38 | 777.8 | 339.3 | 777.8/329.3>GPA:42:5 | 25 | −160 | −10 | −40 | −14 |
| 40 | 39 | 481.4 | 253.3 | 481.4/253.3>GPGro:Lyso 16:1 | 25 | −80 | −10 | −30 | −7 |
| 41 | 40 | 483.4 | 255.3 | 483.4/255.3>GPGro:Lyso 16:0 | 25 | −70 | −10 | −40 | −5 |
| 42 | 41 | 507.4 | 279.3 | 507.4/279.3>GPGro:Lyso 18:2 | 25 | −60 | −10 | −40 | −7 |
| 43 | 42 | 509.4 | 281.3 | 509.4/281.3>GPGro:Lyso 18:1 | 25 | −60 | −10 | −40 | −5 |
| 44 | 43 | 511.4 | 283.3 | 511.4/283.3>GPGro:Lyso 18:0 | 25 | −70 | −10 | −40 | −5 |
| 45 | 44 | 531.4 | 303.3 | 531.4/303.3>GPGro:Lyso 20:4 | 25 | −60 | −10 | −30 | −5 |
| 46 | 45 | 555.4 | 327.3 | 555.4/327.3>GPGro:Lyso 22:6 | 25 | −100 | −10 | −30 | −5 |
| 47 | 46 | 557.4 | 329.3 | 557.4/329.3>GPGro:Lyso 22:5 | 25 | −80 | −10 | −30 | −5 |
| 48 | 47 | 717.8 | 253.3 | 717.8/253.3>GPGro:16:1/16:1 | 25 | −180 | −10 | −50 | −8 |
| 49 | 48 | 719.8 | 253.3 | 719.8/253.3>GPGro:16:1/16:0 | 25 | −70 | −10 | −50 | −10 |
| 50 | 49 | 721.8 | 255.3 | 721.8/255.3>GPGro:16:0/16:0 | 25 | −180 | −10 | −50 | −4 |
| 51 | 50 | 743.8 | 279.3 | 743.8/279.3>GPGro:18:2/16:1 | 25 | −180 | −10 | −50 | −4 |
| 52 | 51 | 743.8 | 281.3 | 743.8/281.3>GPGro:18:1/16:2 | 25 | −180 | −10 | −40 | −14 |
| 53 | 52 | 745.8 | 279.3 | 745.8/279.3>GPGro:18:2/16:0 | 25 | −160 | −10 | −40 | −7 |
| 54 | 53 | 745.8 | 281.3 | 745.8/281.3>GPGro:18:1/16:1 | 25 | −160 | −10 | −50 | −10 |
| 55 | 54 | 747.8 | 281.3 | 747.8/255.2>GPGro:16:0/18:1 | 25 | −60 | −10 | −50 | −4 |
| 56 | 55 | 747.8 | 283.3 | 747.8/281.1>GPGro:16:0/18:1 | 25 | −200 | −10 | −50 | −5 |
| 57 | 56 | 749.8 | 283.3 | 749.8/283.3>GPGro:18:0/16:0 | 25 | −200 | −10 | −40 | −5 |
| 58 | 57 | 767.8 | 303.3 | 767.8/303.3>GPGro:20:4/16:1 | 25 | −180 | −10 | −40 | −14 |
| 59 | 58 | 769.8 | 279.3 | 769.8/279.3>GPGro:18:2/18:2 | 25 | −110 | −10 | −50 | −5 |
| 60 | 59 | 769.8 | 303.3 | 769.8/303.3>GPGro:20:4/16:0 | 25 | −110 | −10 | −40 | −5 |
| 61 | 60 | 771.8 | 279.3 | 771.8/279.3>GPGro:18:2/18:1 | 25 | −180 | −10 | −50 | −7 |
| 62 | 61 | 773.8 | 279.3 | 773.8/279.3>GPGro:18:2/18:0 | 25 | −160 | −10 | −50 | −5 |
| 63 | 62 | 773.8 | 281.3 | 773.8/281.3>GPGro:18:1/18:1 | 25 | −180 | −10 | −50 | −10 |
| 64 | 63 | 775.8 | 281.3 | 775.8/281.3>GPGro:18:1/18:0 | 25 | −140 | −10 | −50 | −10 |
| 65 | 64 | 777.8 | 283.3 | 777.8/283.3>GPGro:18:0/18:0 | 25 | −140 | −10 | −50 | −7 |
| 66 | 65 | 795.8 | 303.3 | 795.8/303.3>GPGro:20:4/18:1 | 25 | −160 | −10 | −40 | −6 |
| 67 | 66 | 797.8 | 303.3 | 797.8/303.3>GPGro:20:4/18:0 | 25 | −140 | −10 | −50 | −18 |
| 68 | 67 | 821.8 | 327.3 | 821.8/327.3>GPGro:22:6/18:0 | 25 | −140 | −10 | −40 | −7 |
| 69 | 68 | 823.8 | 329.3 | 823.8/329.3>GPGro:22:5/18:0 | 25 | −140 | −10 | −50 | −18 |
| 70 | 69 | 494.4 | 407.4 | 494.4/407.4>Lyso GPSer:16:1 | 25 | −160 | −10 | −30 | −4 |
| 71 | 70 | 490.4 | 409.4 | 490.4/409.4>Lyso GPSer:16:0 | 25 | −110 | −10 | −20 | −14 |
| 72 | 71 | 522.4 | 435.4 | 522.4/435.4>Lyso GPSer:18:1 | 25 | −110 | −10 | −30 | −10 |
| 73 | 72 | 524.4 | 437.4 | 524.4/437.4>Lyso GPSer:18:0 | 25 | −110 | −10 | −30 | −14 |
| 74 | 73 | 544.4 | 457.4 | 544.4/457.4>Lyso GPSer:20:4 | 25 | −180 | −10 | −20 | −7 |
| 75 | 74 | 570.4 | 483.4 | 570.4/483.4>Lyso GPSer:22:5 | 25 | −140 | −10 | −50 | −10 |
| 76 | 75 | 732.6 | 645.6 | 732.6/645.6>GPSer:32:1 | 25 | −120 | −10 | −31 | −15 |
| 77 | 76 | 734.6 | 647.6 | 734.6/647.6>GPSer:32:0 | 25 | −120 | −10 | −31 | −21 |
| 78 | 77 | 758.6 | 671.6 | 758.6/671.6>GPSer:34:2 | 25 | −120 | −10 | −31 | −18 |
| 79 | 78 | 760.8 | 673.8 | 760.8/673.8>GPSer:34:1 | 25 | −80 | −10 | −30 | −10 |
| 80 | 79 | 762.8 | 675.7 | 762.8/675.7>GPSer:34:0 | 25 | −130 | −10 | −35 | −15 |
| 81 | 80 | 782.6 | 695.7 | 782.6/695.7>GPSer:36:4 | 25 | −120 | −10 | −35 | −15 |
| 82 | 81 | 784.8 | 697.8 | 784.8/697.8>GPSer:36:3 | 25 | −100 | −10 | −30 | −14 |
| 83 | 82 | 780.8 | 699.8 | 780.8/699.8>GPSer:36:2 | 25 | −60 | −10 | −30 | −8 |
| 84 | 83 | 788.8 | 701.8 | 788.8/701.8>GPSer:36:1 | 25 | −100 | −10 | −30 | −8 |
| 85 | 84 | 790.8 | 703.8 | 790.8/703.8>GPSer:36:0 | 25 | −80 | −10 | −30 | −10 |
| 86 | 85 | 808.6 | 721.6 | 808.6/721.6>GPSer:38:6 | 25 | −110 | −10 | −31 | −15 |
| 87 | 86 | 810.8 | 723.8 | 810.8/723.8>GPSer:38:5 | 25 | −70 | −10 | −30 | −14 |
| 88 | 87 | 812.8 | 725.8 | 812.8/725.8>GPSer:38:4 | 25 | −180 | −10 | −30 | −10 |
| 89 | 88 | 814.6 | 727.6 | 814.6/727.6>GPSer:38:3 | 25 | −110 | −10 | −35 | −15 |
| 90 | 89 | 810.8 | 729.8 | 810.8/729.8>GPSer:38:2 | 25 | −120 | −10 | −35 | −15 |
| 91 | 90 | 818.8 | 731.8 | 818.8/731.8>GPSer:38:1 | 25 | −120 | −10 | −33 | −12 |
| 92 | 91 | 834.8 | 747.8 | 834.8/747.8>GPSer:40:6 | 25 | −110 | −10 | −40 | −8 |
| 93 | 92 | 830.8 | 749.8 | 830.8/749.8>GPSer:40:5 | 25 | −110 | −10 | −30 | −10 |
| 94 | 93 | 838.8 | 751.8 | 838.8/751.8>GPSer:40:4 | 25 | −70 | −10 | −30 | −6 |
| 95 | 94 | 840.6 | 753.7 | 840.6/753.7>GPSer:40:3 | 25 | −110 | −10 | −35 | −15 |
| 96 | 95 | 778.9 | 97 | 778.9/97>Sulfatide:16:0 | 25 | −160 | −10 | −100 | −5 |
| 97 | 96 | 800.9 | 97 | 800.9/97>Sulfatide:18:0 | 25 | −170 | −10 | −120 | −9 |
| 98 | 97 | 822.9 | 97 | 822.9/97>Sulfatide:18:0 (OH) | 25 | −100 | −10 | −120 | −8 |
| 99 | 98 | 834.9 | 97 | 834.9/97>Sulfatide:20:0 | 25 | −90 | −10 | −100 | −20 |
| 100 | 99 | 850.9 | 97 | 850.9/97>Sulfatide:20:0 (OH) | 25 | −110 | −10 | −110 | −8 |
| 101 | 100 | 862.9 | 97 | 862.9/97>Sulfatide:22:1 | 25 | −90 | −10 | −120 | −20 |
| 102 | 101 | 878.9 | 97 | 878.9/97>Sulfatide: 22:1 (OH) | 25 | −90 | −10 | −120 | −8 |
| 103 | 102 | 888.9 | 97 | 888.9/97>Sulfatide:24:1 | 25 | −90 | −10 | −120 | −16 |
| 104 | 103 | 890.9 | 97 | 890.9/97>Sulfatide:24:0 | 25 | −90 | −10 | −120 | −16 |
| 105 | 104 | 900.7 | 97 | 900.7/97>Sulfatide:24:0 (OH) | 25 | −90 | −10 | −120 | −20 |
| 106 | 105 | 1147 | 281.3 | 1147/281.3>CardioliGPInsn:52:3 | 25 | −140 | −10 | −90 | −6 |
| 107 | 106 | 1376 | 281.3 | 1376/281.3>CardioliGPInsn:66:2 | 25 | −120 | −10 | −90 | −5 |
| 108 | 107 | 1400 | 281.3 | 1400/281.3>CardioliGPInsn:68:4 | 25 | −70 | −10 | −90 | −13 |
| 109 | 108 | 1402 | 281.3 | 1402/281.3>CardioliGPInsn:68:3 | 25 | −70 | −10 | −90 | −10 |
| 110 | 109 | 1404 | 281.3 | 1404/281.3>CardioliGPInsn:68:2 | 25 | −90 | −10 | −70 | −12 |
| 111 | 110 | 1406 | 281.3 | 1406/281.3>CardioliGPInsn:68:1 | 25 | −70 | −10 | −70 | −12 |
| 112 | 111 | 1426 | 281.3 | 1426/281.3>CardioliGPInsn:70:5 | 25 | −110 | −10 | −90 | −12 |

APPENDIX A-continued

MRM Conditions for Lipids

| | A | B | C | D | E | F | G | H | I |
|---|---|---|---|---|---|---|---|---|---|
| 113 | 112 | 1428 | 281.3 | 1428/281.3>CardioliGPInsn:70:4 | 25 | −120 | −10 | −80 | −10 |
| 114 | 113 | 1430 | 281.3 | 1430/281.3>CardioliGPInsn:70:3 | 25 | −70 | −10 | −90 | −11 |
| 115 | 114 | 1432 | 281.3 | 1432/281.3>CardioliGPInsn:70:2 | 25 | −90 | −10 | −70 | −12 |
| 116 | 115 | 1434 | 281.3 | 1434/281.3>CardioliGPInsn:70:1 | 25 | −150 | −10 | −80 | −13 |
| 117 | 116 | 1436 | 281.3 | 1436/281.3>CardioliGPInsn:70:0 | 25 | −90 | −10 | −90 | −8 |
| 118 | 117 | 430.6 | 190.1 | 430.6/190.1>Lyso GPEtn:Lyso16:1e/16:0p | 25 | −110 | −10 | −30 | −10 |
| 119 | 118 | 450.4 | 190.1 | 450.4/190.1>Lyso GPEtn:Lyso 16:1 | 25 | −100 | −10 | −30 | −10 |
| 120 | 119 | 452.4 | 190.1 | 452.4/190.1>Lyso GPEtn:Lyso 16:0 | 25 | −110 | −10 | −30 | −8 |
| 121 | 120 | 462.4 | 190.1 | 462.4/190.1>Lyso GPEtn:Lyso18:2e/18:1p | 25 | −160 | −10 | −35 | −8 |
| 122 | 121 | 464.5 | 190.1 | 464.5/190.1>Lyso GPEtn:Lyso18:1e/18:0p | 25 | −160 | −10 | −35 | −8 |
| 123 | 122 | 470.6 | 190.1 | 470.6/190.1>Lyso GPEtn:Lyso18:2a | 25 | −140 | −10 | −25 | −16 |
| 124 | 123 | 478.4 | 190.1 | 478.4/190.1>Lyso GPEtn:Lyso 18:1 | 25 | −100 | −10 | −30 | −7 |
| 125 | 124 | 480.4 | 190.1 | 480.4/190.1>Lyso GPEtn:Lyso 18:0 | 25 | −100 | −10 | −40 | −7 |
| 126 | 125 | 492.5 | 190.1 | 492.5/190.1>Lyso GPEtn:Lyso20:1e/20:0p | 25 | −70 | −10 | −40 | −12 |
| 127 | 126 | 500.4 | 190.1 | 500.4/190.1>Lyso GPEtn:Lyso 20:4 | 25 | −110 | −10 | −30 | −10 |
| 128 | 127 | 524.4 | 190.1 | 524.4/190.1>Lyso GPEtn:Lyso 22:6 | 25 | −100 | −10 | −30 | −18 |
| 129 | 128 | 688.6 | 190.1 | 688.6/190.1>GPEtn:16:0/16:1 | 25 | −145 | −10 | −63 | −6 |
| 130 | 129 | 690.7 | 190.1 | 690.7/190.1>GPEtn 16:0/16:0 | 25 | −145 | −10 | −63 | −6 |
| 131 | 130 | 698.6 | 190.1 | 698.6/190.1>GPEtn:34:2p, 34:3e | 25 | −145 | −10 | −63 | −6 |
| 132 | 131 | 700.6 | 190.1 | 700.6/190.1>GPEtn:34:1p, 34:2e | 25 | −145 | −10 | −63 | −9 |
| 133 | 132 | 702.6 | 190.1 | 702.6/190.1>GPEtn:34:0p, 34:1e | 25 | −145 | −10 | −63 | −6 |
| 134 | 133 | 710.8 | 190.1 | 710.8/190.1>GPEtn:18:1/16:1 | 25 | −70 | −10 | −50 | −6 |
| 135 | 134 | 712.8 | 190.1 | 712.8/190.1>GPEtn:18:2/16:1 | 25 | −110 | −10 | −40 | −14 |
| 136 | 135 | 714.8 | 190.1 | 714.7/190.1>GPEtn:18:1/16:1 | 25 | −60 | −10 | −50 | −10 |
| 137 | 136 | 710.8 | 190.1 | 710.7/190.1>GPEtn:18:1/16:0 | 25 | −140 | −10 | −60 | −14 |
| 138 | 137 | 718.6 | 190.1 | 718.6/190.1>GPEtn:18:0/16:0 | 25 | −145 | −10 | −60 | −30 |
| 139 | 138 | 722.6 | 190.1 | 722.6/190.1>GPEtn:36:4p | 25 | −175 | −10 | −63 | −6 |
| 140 | 139 | 724.6 | 190.1 | 724.6/190.1>GPEtn:36:3p, 36:4e | 25 | −145 | −10 | −63 | −6 |
| 141 | 140 | 720.6 | 190.1 | 720.6/190.1>GPEtn:36:2p, 36:3e | 25 | −145 | −10 | −63 | −6 |
| 142 | 141 | 728.6 | 190.1 | 728.6/190.1>GPEtn:36:1p, 36:2e | 25 | −170 | −10 | −63 | −21 |
| 143 | 142 | 738.8 | 190.1 | 738.8/190.1>GPEtn:20:4/16:0 | 25 | −100 | −10 | −50 | −5 |
| 144 | 143 | 740.8 | 190.1 | 740.8/190.1>GPEtn:18:2/18:1 | 25 | −80 | −10 | −50 | −14 |
| 145 | 144 | 742.8 | 190.1 | 742.8/190.1>GPEtn:18:1/18:1 | 25 | −120 | −10 | −50 | −10 |
| 146 | 145 | 744.6 | 190.1 | 744.6/190.1>GPEtn:18:0/18:1 | 25 | −185 | −10 | −50 | −9 |
| 147 | 146 | 740.8 | 190.1 | 740.8/190.1>GPEtn:18:0/18:0 | 25 | −60 | −10 | −40 | −10 |
| 148 | 147 | 748.6 | 190.1 | 748.6/190.1>GPEtn:38:5p, 38:6e | 25 | −170 | −10 | −63 | −6 |
| 149 | 148 | 750.6 | 190.1 | 750.6/190.1>GPEtn:38:4p, 38:5e | 25 | −175 | −10 | −63 | −6 |
| 150 | 149 | 752.6 | 190.1 | 752.6/190.1>GPEtn:38:3p, 38:4e | 25 | −175 | −10 | −63 | −6 |
| 151 | 150 | 754.6 | 190.1 | 754.6/190.1>GPEtn:38:2p, 38:3e | 25 | −170 | −10 | −60 | −6 |
| 152 | 151 | 750.6 | 190.1 | 750.6/190.1>GPEtn:38:1p, 38:2e | 25 | −145 | −10 | −63 | −18 |
| 153 | 152 | 762.8 | 190.1 | 762.8/190.1>GPEtn:20:4/18:2 | 25 | −100 | −10 | −50 | −10 |
| 154 | 153 | 764.8 | 190.1 | 764.8/190.1>GPEtn:20:4/18:1 | 25 | −110 | −10 | −50 | −8 |
| 155 | 154 | 760.8 | 190.1 | 760.8/190.1>GPEtn:20:4/18:0 | 25 | −140 | −10 | −60 | −6 |
| 156 | 155 | 768.8 | 190.1 | 768.8/190.1>GPEtn:20:3/18:0 | 25 | −120 | −10 | −60 | −10 |
| 157 | 156 | 770.6 | 190.1 | 770.6/190.1>GPEtn:20:2/18:0 | 25 | −175 | −10 | −63 | −6 |
| 158 | 157 | 772.6 | 190.1 | 772.6/190.1>GPEtn:20:1/18:0 | 25 | −145 | −10 | −60 | −6 |
| 159 | 158 | 770.6 | 190.1 | 770.6/190.1>GPEtn:40:5p, 40:6e | 25 | −170 | −10 | −63 | −21 |
| 160 | 159 | 778.6 | 190.1 | 778.6/190.1>GPEtn:40:4p, 40:5e | 25 | −170 | −10 | −63 | −18 |
| 161 | 160 | 780.6 | 190.1 | 780.6/190.1>GPEtn:40:3p, 40:4e | 25 | −170 | −10 | −66 | −6 |
| 162 | 161 | 784.6 | 190.1 | 784.6/190.1>GPEtn:40:1p, 40:2e | 25 | −170 | −10 | −60 | −21 |
| 163 | 162 | 788.8 | 190.1 | 788.8/190.1>GPEtn:22:4/18:3 | 25 | −70 | −10 | −50 | −6 |
| 164 | 163 | 790.8 | 190.1 | 790.8/190.1>GPEtn:22:4/18:2 | 25 | −110 | −10 | −50 | −10 |
| 165 | 164 | 792.6 | 190.1 | 792.6/190.1>GPEtn:40:5a | 25 | −145 | −10 | −63 | −21 |
| 166 | 165 | 794.6 | 190.1 | 794.6/190.1>GPEtn:40:4a | 25 | −175 | −10 | −60 | −21 |
| 167 | 166 | 790.8 | 190.1 | 790.8/190.1>GPEtn:40:3a | 25 | −145 | −10 | −63 | −6 |
| 168 | 167 | 798.6 | 190.1 | 798.6/190.1>GPEtn:40:2a | 25 | −170 | −10 | −63 | −18 |
| 169 | 168 | 569.4 | 241.1 | 569.4/241.1>GPIns:Llyso 16:1 | 25 | −120 | −10 | −47.5 | −5 |
| 170 | 169 | 571.3 | 241.1 | 571.3/241.1>GPIns:Lyso 16:0 | 25 | −120 | −10 | −47.5 | −5 |
| 171 | 170 | 595.4 | 241.1 | 595.4/241.1>GPIns:Lyso 18:2 | 25 | −140 | −10 | −47.5 | −5 |
| 172 | 171 | 597.4 | 241.1 | 597.4/241.1>GPIns:Lyso 18:1 | 25 | −140 | −10 | −47.5 | −5 |
| 173 | 172 | 599.4 | 241.1 | 599.4/241.1>GPIns:Lyso 18:0 | 25 | −140 | −10 | −47.5 | −5 |
| 174 | 173 | 619.5 | 241.1 | 619.5/241.1>GPIns:Lyso 20:4 | 25 | −140 | −10 | −47.5 | −5 |
| 175 | 174 | 621.5 | 241.1 | 621.5/241.1>GPIns:Lyso 20:3 | 25 | −140 | −10 | −47.5 | −5 |
| 176 | 175 | 623.5 | 241.1 | 623.5/241.1>GPIns:Lyso 20:2 | 25 | −140 | −10 | −47.5 | −5 |
| 177 | 176 | 625.5 | 241.1 | 625.5/241.1>GPIns:Lyso 20:1 | 25 | −140 | −10 | −47.5 | −5 |
| 178 | 177 | 627.5 | 241.1 | 627.5/241.1>GPIns:Lyso 20:0 | 25 | −140 | −10 | −47 | −5 |
| 179 | 178 | 679.5 | 241.1 | 679.5/241.1>GPIns:Lyso 24:2 | 25 | −120 | −10 | −50 | −5 |
| 180 | 179 | 835.7 | 241.1 | 835.7/241.1>GPIns:34:1 | 25 | −175 | −10 | −60 | −5 |
| 181 | 180 | 857.7 | 241.1 | 857.7/241.1>GPIns:36:4 | 25 | −180 | −10 | −60 | −5 |
| 182 | 181 | 859.8 | 241.1 | 859.8/241.1>GPIns:36:3 | 25 | −180 | −10 | −60 | −5 |
| 183 | 182 | 861.8 | 241.1 | 861.8/241.1>GPIns:36:2 | 25 | −180 | −10 | −60 | −5 |
| 184 | 183 | 863.8 | 241.1 | 863.7/241.1>GPIns:36:1 | 25 | −180 | −10 | −60 | −5 |
| 185 | 184 | 865.8 | 241.1 | 865.8/241.1>GPIns:36:0 | 25 | −100 | −10 | −65 | −9 |
| 186 | 185 | 873.8 | 241.1 | 873.8/241.1>GPIns:37:3 | 25 | −180 | −10 | −60 | −5 |
| 187 | 186 | 883.8 | 241.1 | 883.8/241.1>GPIns:38:5 | 25 | −180 | −10 | −60 | −5 |
| 188 | 187 | 885.8 | 241.1 | 885.8/241.1>GPIns:38:4 | 25 | −180 | −10 | −60 | −5 |

APPENDIX A-continued

MRM Conditions for Lipids

| | A | B | C | D | E | F | G | H | I |
|---|---|---|---|---|---|---|---|---|---|
| 189 | 188 | 887.8 | 241.1 | 887.8/241.1>GPIns:38:3 | 25 | −180 | −10 | −60 | −5 |
| 190 | 189 | 889.8 | 241.1 | 889.8/241.1>GPIns:38:2 | 25 | −100 | −10 | −70 | −6 |
| 191 | 190 | 891.8 | 241.1 | 891.8/241.1>GPIns:38:1 | 25 | −100 | −10 | −75 | −9 |
| 192 | 191 | 893.8 | 241.1 | 893.8/241.1>GPIns:38:0 | 25 | −100 | −10 | −75 | −9 |
| 193 | 192 | 909.8 | 241.1 | 909.8/241.1>GPIns:40:6 | 25 | −180 | −10 | −62.5 | −5 |
| 194 | 193 | 911.8 | 241.1 | 911.8/241.1>GPIns:40:5 | 25 | −180 | −10 | −62.5 | −5 |
| 195 | 194 | 913.8 | 241.1 | 913.8/241.1>GPIns:40:4 | 25 | −180 | −10 | −62.5 | −5 |
| 196 | 195 | 915.8 | 241.1 | 915.8/241.1>GPIns:40:3 | 25 | −180 | −10 | −62.5 | −5 |
| 197 | 196 | 917.8 | 241.1 | 917.8/241.1>GPIns:40:2 | 25 | −145 | −10 | −65 | −6 |
| 198 | 197 | 919.8 | 241.1 | 919.8/241.1>GPIns:40:1 | 25 | −100 | −10 | −75 | −9 |
| 199 | 198 | 963.9 | 241.1 | 963.9/241.1>GPInsP: 38:5 | 25 | −165 | −10 | −62.5 | −5 |
| 200 | 199 | 963.9 | 321.1 | 963.9/321.1>GPInsP: 38:5 | 25 | −150 | −10 | −55 | −5 |
| 201 | 200 | 965.9 | 241.1 | 965.9/241.1>GPInsP: 38:4 | 25 | −165 | −10 | −62.5 | −5 |
| 202 | 201 | 965.9 | 321.1 | 965.9/321.1>GPInsP: 38:4 | 25 | −150 | −10 | −55 | −5 |
| 203 | 202 | 967.9 | 241.1 | 967.9/241.1>GPInsP: 38:3 | 25 | −195 | −10 | −62.5 | −5 |
| 204 | 203 | 967.9 | 321.1 | 967.9/321.1>GPInsP: 38:3 | 25 | −150 | −10 | −55 | −5 |
| 205 | 204 | 1045.9 | 241.1 | 1045.9/241.1>GPInsP2: 38:4 | 25 | −150 | −10 | −75 | −5 |
| 206 | 205 | 1045.9 | 321.1 | 1045.9/321.1>GPInsP2: 38:4 | 25 | −175 | −10 | −63 | −5 |
| 207 | 206 | 1045.9 | 401.1 | 1045.9/401.1>GPInsP2: 38:4 | 25 | −175 | −10 | −50 | −5 |
| 208 | 207 | 1047.9 | 321.1 | 1047.9/321.1>GPInsP2: 38:3 | 25 | −175 | −10 | −63 | −5 |
| 209 | 208 | 1047.9 | 401.1 | 1047.9/401.1>GPInsP2: 38:3 | 25 | −175 | −10 | −52.5 | −5 |
| 210 | 209 | 1047.9 | 241.1 | 1047.9/241.1>GPInsP2: 38:3 | 25 | −175 | −10 | −75 | −5 |
| 211 | 210 | 1125.9 | 241.1 | 1125.9/241.1>GPInsP3: 38:4 | 25 | −150 | −10 | −75 | −5 |
| 212 | 211 | 1125.9 | 321.1 | 1125.9/321.1>GPInsP3: 38:4 | 25 | −150 | −10 | −75 | −5 |
| 213 | 212 | 1125.9 | 401.1 | 1125.9/401.1>GPInsP3: 38:4 | 25 | −150 | −10 | −75 | −5 |
| 214 | 213 | 1125.9 | 481.1 | 1125.9/481.1>GPInsP3: 38:4 | 25 | −150 | −10 | −75 | −5 |
| 215 | 214 | 835.8 | 281.1 | 835.7/281.1>GPIns:34:1 | 25 | −130 | −10 | −60 | −5 |
| 216 | 215 | 821.8 | 241.1 | 821.8/241.1>GPIns: 34:1 | 25 | −175 | −10 | −65 | −5 |
| 217 | 216 | 494.4 | 184.1 | 494.4/184.1>GPCho:Lyso 16:1 | 25 | 110 | 10 | 30 | 10 |
| 218 | 217 | 490.4 | 184.1 | 490.4/184.1>GPCho:Lyso 16:0 | 25 | 110 | 10 | 40 | 35 |
| 219 | 218 | 520.4 | 184.1 | 520.4/184.1>GPCho:Lyso 18:2 | 25 | 110 | 10 | 30 | 15 |
| 220 | 219 | 522.4 | 184.1 | 522.4/184.1>GPCho:Lyso 18:1 | 25 | 110 | 10 | 40 | 10 |
| 221 | 220 | 524.4 | 184.1 | 524.4/184.1>GPCho:Lyso 18:0 | 25 | 110 | 10 | 40 | 35 |
| 222 | 221 | 544.4 | 184.1 | 544.4/184.1>GPCho:Lyso 20:4 | 25 | 100 | 10 | 30 | 10 |
| 223 | 222 | 568.4 | 184.1 | 568.4/184.1>GPCho:Lyso 22:6 | 25 | 110 | 10 | 30 | 35 |
| 224 | 223 | 570.4 | 184.1 | 570.4/184.1>GPCho:Lyso 22:5 | 25 | 110 | 10 | 40 | 30 |
| 225 | 224 | 678.5 | 184.1 | 678.5/184.1>GPCho:28:0 | 25 | 130 | 10 | 38 | 32 |
| 226 | 225 | 678.5 | 184.1 | 678.5/184.1>GPCho:28:0a | 25 | 100 | 10 | 46 | 30 |
| 227 | 226 | 704.6 | 184.1 | 704.6/184.1>GPCho:30:1a | 25 | 100 | 10 | 48 | 20 |
| 228 | 227 | 700.6 | 184.1 | 700.6/184.1>GPCho:30:0a | 25 | 110 | 10 | 46 | 30 |
| 229 | 228 | 718.6 | 184.1 | 718.6/184.1>GPCho:32:0p, 32:1e | 25 | 130 | 10 | 38 | 32 |
| 230 | 229 | 730.8 | 184.1 | 730.8/184.1>GPCho:32:2 | 25 | 110 | 10 | 40 | 35 |
| 231 | 230 | 732.6 | 184.1 | 732.6/184.1>GPCho:32:1a | 25 | 120 | 10 | 48 | 15 |
| 232 | 231 | 734.6 | 184.1 | 734.6/184.1>GPCho:32:0a | 25 | 120 | 10 | 46 | 15 |
| 233 | 232 | 742.6 | 184.1 | 742.6/184.1>GPCho:34:2p, 34:3e | 25 | 140 | 10 | 46 | 32 |
| 234 | 233 | 744.6 | 184.1 | 744.6/184.1>GPCho:34:1p, 34:2e | 25 | 130 | 10 | 38 | 32 |
| 235 | 234 | 740.6 | 184.1 | 740.6/184.1>GPCho:34:0p, 34:1e | 25 | 120 | 10 | 46 | 32 |
| 236 | 235 | 748.6 | 184.1 | 748.6/184.1>GPCho:34:0e | 25 | 120 | 10 | 46 | 32 |
| 237 | 236 | 750.6 | 184.1 | 750.6/184.1>GPCho:34:3a | 25 | 120 | 10 | 46 | 20 |
| 238 | 237 | 758.7 | 184.1 | 758.7/184.1>GPCho:34:2a | 25 | 120 | 10 | 46 | 15 |
| 239 | 238 | 760.6 | 184.1 | 760.6/184.1>GPCho:34:1a | 25 | 120 | 10 | 46 | 15 |
| 240 | 239 | 762.6 | 184.1 | 762.6/184.1>GPCho:34:0a | 25 | 100 | 10 | 46 | 15 |
| 241 | 240 | 768.6 | 184.1 | 768.6/184.1>GPCho:36:3p, 36:4e | 25 | 120 | 10 | 46 | 30 |
| 242 | 241 | 770.6 | 184.1 | 770.6/184.1>GPCho:36:2p, 36:3e | 25 | 120 | 10 | 46 | 30 |
| 243 | 242 | 772.6 | 184.1 | 772.6/184.1>GPCho:36:1p, 36:2e | 25 | 120 | 10 | 46 | 30 |
| 244 | 243 | 774.6 | 184.1 | 774.6/184.1>GPCho:36:0p, 36:1e | 25 | 120 | 10 | 46 | 30 |
| 245 | 244 | 782.6 | 184.1 | 782.6/184.1>GPCho:36:4a | 25 | 90 | 10 | 46 | 15 |
| 246 | 245 | 784.6 | 184.1 | 784.6/184.1>GPCho:36:3a | 25 | 90 | 10 | 46 | 15 |
| 247 | 246 | 780.6 | 184.1 | 780.6/184.1>GPCho:36:2a | 25 | 90 | 10 | 46 | 15 |
| 248 | 247 | 788.6 | 184.1 | 788.6/184.1>GPCho:36:1a | 25 | 100 | 10 | 46 | 15 |
| 249 | 248 | 790.8 | 184.1 | 790.8/184.1>GPCho:36:0 | 25 | 100 | 10 | 40 | 35 |
| 250 | 249 | 792.6 | 184.1 | 792.6/184.1>GPCho:38:5p, 38:6e | 25 | 120 | 10 | 46 | 30 |
| 251 | 250 | 794.6 | 184.1 | 794.6/184.1>GPCho:38:4p, 38:5e | 25 | 120 | 10 | 46 | 30 |
| 252 | 251 | 790.6 | 184.1 | 790.6/184.1>GPCho:38:3p, 38:4e | 25 | 120 | 10 | 46 | 30 |
| 253 | 252 | 798.6 | 184.1 | 798.6/184.1>GPCho:38:2p, 38:3e | 25 | 120 | 10 | 46 | 30 |
| 254 | 253 | 800.6 | 184.1 | 800.6/184.1>GPCho:38:1p, 38:2e | 25 | 120 | 10 | 46 | 30 |
| 255 | 254 | 808.6 | 184.1 | 808.6/184.1>GPCho:38:5a | 25 | 100 | 10 | 46 | 15 |
| 256 | 255 | 810.6 | 184.1 | 810.6/184.1>GPCho:38:4a | 25 | 100 | 10 | 46 | 15 |
| 257 | 256 | 812.6 | 184.1 | 812.6/184.1>GPCho:38:3a | 25 | 110 | 10 | 46 | 15 |
| 258 | 257 | 814.6 | 184.1 | 814.6/184.1>GPCho:38:2a | 25 | 110 | 10 | 46 | 15 |
| 259 | 258 | 810.6 | 184.1 | 810.6/184.1>GPCho:38:1a | 25 | 110 | 10 | 46 | 15 |
| 260 | 259 | 820.6 | 184.1 | 820.6/184.1>GPCho:40:5p, 40:6e | 25 | 120 | 10 | 46 | 30 |
| 261 | 260 | 822.6 | 184.1 | 822.6/184.1>GPCho:40:4p, 40:5e | 25 | 120 | 10 | 46 | 30 |
| 262 | 261 | 824.6 | 184.1 | 824.6/184.1>GPCho:40:3p, 40:4e | 25 | 130 | 10 | 46 | 30 |
| 263 | 262 | 820.6 | 184.1 | 820.6/184.1>GPCho:40:2p, 40:3e | 25 | 130 | 10 | 46 | 30 |
| 264 | 263 | 828.6 | 184.1 | 828.6/184.1>GPCho:40:1p, 40:2e | 25 | 130 | 10 | 50 | 30 |

APPENDIX A-continued

MRM Conditions for Lipids

| | A | B | C | D | E | F | G | H | I |
|---|---|---|---|---|---|---|---|---|---|
| 265 | 264 | 834.8 | 184.1 | 834.6/184.1>GPCho:40:6a | 25 | 110 | 10 | 50 | 10 |
| 266 | 265 | 830.6 | 184.1 | 830.6/184.1>GPCho:40:5a | 25 | 110 | 10 | 44 | 15 |
| 267 | 266 | 838.6 | 184.1 | 838.6/184.1>GPCho:40:4a | 25 | 110 | 10 | 46 | 15 |
| 268 | 267 | 701.5 | 184.1 | 701.5/184.1>SM:18/16:1 | 25 | 110 | 10 | 44 | 15 |
| 269 | 268 | 703.5 | 184.1 | 703.5/184.1>SM:18/16:0 | 25 | 120 | 10 | 44 | 15 |
| 270 | 269 | 703.8 | 184.1 | 703.8/184.4>SM:d18:1/16:0 | 25 | 110 | 10 | 40 | 35 |
| 271 | 270 | 705.8 | 184.1 | 705.8/184.4>SM: d18:0/16:0 | 25 | 90 | 10 | 40 | 15 |
| 272 | 271 | 727.6 | 184.1 | 727.6/184.1>SM:18/18:2 | 25 | 120 | 10 | 40 | 32 |
| 273 | 272 | 729.6 | 184.1 | 729.6/184.1>SM:18/18:1 | 25 | 120 | 10 | 44 | 10 |
| 274 | 273 | 731.6 | 184.1 | 731.6/184.1>SM:18/18:0 | 25 | 110 | 10 | 46 | 15 |
| 275 | 274 | 731.8 | 184.1 | 731.8/184.4>SM: d18:1/18:0 | 25 | 110 | 10 | 40 | 35 |
| 276 | 275 | 733.8 | 184.1 | 733.8/184.4>SM: d18:0/ 18:0 | 25 | 110 | 10 | 40 | 35 |
| 277 | 276 | 757.6 | 184.1 | 757.6/184.1>SM:18/20:1 | 25 | 110 | 10 | 46 | 46 |
| 278 | 277 | 759.6 | 184.1 | 759.6/184.1>SM:18/20:0 | 25 | 110 | 10 | 42 | 34 |
| 279 | 278 | 759.8 | 184.1 | 759.8/184.4>SM: d18:1/20:0 | 25 | 90 | 10 | 40 | 30 |
| 280 | 279 | 761.8 | 184.1 | 761.8/184.4>SM: d18:0/20:0 | 25 | 90 | 10 | 40 | 10 |
| 281 | 280 | 773.6 | 184.1 | 773.6/184.1>SM:18/21:0 | 25 | 110 | 10 | 44 | 34 |
| 282 | 281 | 787.6 | 184.1 | 787.6/184.1>SM:18/22:0 | 25 | 110 | 10 | 42 | 10 |
| 283 | 282 | 787.9 | 184.1 | 787.9/184.4>SM: d18:1/22:0 | 25 | 90 | 10 | 40 | 15 |
| 284 | 283 | 789.9 | 184.1 | 789.9/184.4>SM: d18:0/22:0 | 25 | 90 | 10 | 40 | 20 |
| 285 | 284 | 813.6 | 184.1 | 813.6/184.1>SM:18/24:1 | 25 | 110 | 10 | 42 | 10 |
| 286 | 285 | 813.9 | 184.1 | 813.9/184.4>SM: d18:1/24:1 | 25 | 100 | 10 | 40 | 15 |
| 287 | 286 | 815.6 | 184.1 | 815.6/184.1>SM:18/24:0 | 25 | 150 | 10 | 44 | 34 |
| 288 | 287 | 815.9 | 184.1 | 815.9/184.4>SM: d18:0/24:1 | 25 | 50 | 10 | 40 | 35 |
| 289 | 288 | 817.9 | 184.1 | 817.9/184.4>SM: d18:0/24:0 | 25 | 30 | 10 | 50 | 10 |
| 290 | 289 | 841.9 | 184.1 | 841.9/184.4>SM: d18:1/26:1 | 25 | 50 | 10 | 50 | 15 |
| 291 | 290 | 843.9 | 184.1 | 843.9/184.4>SM: d18:0/26:1 | 25 | 50 | 10 | 50 | 15 |
| 292 | 291 | 843.9 | 184.1 | 843.9/184.4>SM: d18:1/26:0 | 25 | 50 | 10 | 50 | 15 |
| 293 | 292 | 845.9 | 184.1 | 845.9/184.4>SM: d18:0/26:0 | 25 | 30 | 10 | 50 | 30 |
| 294 | 293 | 538.7 | 264.4 | 538.7/264.4>Cer: d18:1/16:0 | 25 | 100 | 10 | 40 | 25 |
| 295 | 294 | 540.7 | 260.4 | 540.7/260.4>Cer: d18:0/ 16:0 | 25 | 40 | 10 | 40 | 15 |
| 296 | 295 | 560.7 | 264.4 | 560.7/264.4>Cer: d18:1/18:0 | 25 | 90 | 10 | 40 | 20 |
| 297 | 296 | 568.7 | 260.4 | 568.7/260.4>Cer: d18:0/18:0 | 25 | 70 | 10 | 50 | 25 |
| 298 | 297 | 594.7 | 264.4 | 594.7/264.4>Cer: d18:1/20:0 | 25 | 100 | 10 | 40 | 15 |
| 299 | 298 | 590.7 | 260.4 | 590.7/260.4>Cer: d18:0/20:0 | 25 | 50 | 10 | 20 | 15 |
| 300 | 299 | 622.8 | 264.4 | 622.8/264.4>Cer: d18:1/22:0 | 25 | 110 | 10 | 30 | 10 |
| 301 | 300 | 624.8 | 260.4 | 624.8/260.4>Cer: d18:0/22:0 | 25 | 90 | 10 | 20 | 15 |
| 302 | 301 | 648.9 | 264.4 | 648.9/264.4>Cer: d18:1/24:1 | 25 | 110 | 10 | 50 | 15 |
| 303 | 302 | 650.9 | 260.4 | 650.9/260.4>Cer: d18:0/24:1 | 25 | 70 | 10 | 40 | 10 |
| 304 | 303 | 650.9 | 264.4 | 650.9/264.4>Cer: d18:1/24:0 | 25 | 60 | 10 | 40 | 10 |
| 305 | 304 | 652.9 | 260.4 | 652.9/260.4>Cer: d18:0/24:0 | 25 | 40 | 10 | 50 | 30 |
| 306 | 305 | 670.9 | 264.4 | 670.9/264.4>Cer: d18:1/26:1 | 25 | 110 | 10 | 30 | 35 |
| 307 | 306 | 678.9 | 260.4 | 678.9/260.4>Cer: d18:0/26:1 | 25 | 110 | 10 | 60 | 10 |
| 308 | 307 | 678.9 | 264.4 | 678.9/264.4>Cer: d18:1/26:0 | 25 | 20 | 10 | 20 | 25 |
| 309 | 308 | 680.9 | 260.4 | 680.9/260.4>Cer: d18:0/26:0 | 25 | 60 | 10 | 20 | 15 |
| 310 | 309 | 862.7 | 264.4 | 700.7/264.4>MonoHexCer: d18:1/16:0 | 25 | 110 | 10 | 70 | 15 |
| 311 | 310 | 864.7 | 260.4 | 702.7/260.4>MonoHexCer: d18:0/16:0 | 25 | 80 | 10 | 40 | 15 |
| 312 | 311 | 890.7 | 264.4 | 728.7/264.4>MonoHexCer: d18:1/18:0 | 25 | 100 | 10 | 50 | 15 |
| 313 | 312 | 892.7 | 260.4 | 730.7/260.4>MonoHexCer: d18:0/18:0 | 25 | 20 | 10 | 30 | 15 |
| 314 | 313 | 918.7 | 264.4 | 750.7/264.4>MonoHexCer: d18:1/20:0 | 25 | 100 | 10 | 60 | 25 |
| 315 | 314 | 920.7 | 260.4 | 758.7/260.4>MonoHexCer: d18:0/20:0 | 25 | 40 | 10 | 20 | 10 |
| 316 | 315 | 940.8 | 264.4 | 784.8/264.4>MonoHexCer: d18:1/22:0 | 25 | 70 | 10 | 80 | 25 |
| 317 | 316 | 948.8 | 260.4 | 780.8/260.4>MonoHexCer: d18:0/22:0 | 25 | 60 | 10 | 50 | 10 |
| 318 | 317 | 972.9 | 264.4 | 810.9/264.4>MonoHexCer: d18:1/24:1 | 25 | 40 | 10 | 80 | 20 |
| 319 | 318 | 974.9 | 260.4 | 812.9/260.4>MonoHexCer: d18:0/24:1 | 25 | 40 | 10 | 50 | 30 |
| 320 | 319 | 974.9 | 264.4 | 812.9/264.4>MonoHexCer: d18:1/24:0 | 25 | 110 | 10 | 60 | 30 |
| 321 | 320 | 970.9 | 260.4 | 814.9/260.4>MonoHexCer: d18:0/24:0 | 25 | 60 | 10 | 70 | 15 |
| 322 | 321 | 1000.9 | 264.4 | 838.9/264.4>MonoHexCer: d18:1/26:1 | 25 | 80 | 10 | 100 | 15 |
| 323 | 322 | 1002.9 | 260.4 | 840.9/260.4>MonoHexCer: d18:0/26:1 | 25 | 30 | 10 | 80 | 20 |
| 324 | 323 | 1002.9 | 264.4 | 840.9/264.4>MonoHexCer: d18:1/26:0 | 25 | 20 | 10 | 70 | 15 |
| 325 | 324 | 1004.9 | 260.4 | 842.9/260.4>MonoHexCer: d18:0/26:0 | 25 | 20 | 10 | 40 | 25 |
| 326 | 325 | 700.7 | 264.4 | 862.7/264.4>DiHexCer: d18:1/16:0 | 25 | 90 | 10 | 70 | 10 |
| 327 | 326 | 702.7 | 260.4 | 864.7/260.4>DiHexCer: d18:0/16:0 | 25 | 60 | 10 | 40 | 40 |
| 328 | 327 | 728.7 | 264.4 | 890.7/264.4>DiHexCer: d18:1/18:0 | 25 | 110 | 10 | 50 | 15 |
| 329 | 328 | 730.7 | 260.4 | 892.7/260.4>DiHexCer: d18:0/18:0 | 25 | 110 | 10 | 60 | 15 |
| 330 | 329 | 750.7 | 264.4 | 918.7/264.4>DiHexCer: d18:1/20:0 | 25 | 110 | 10 | 50 | 25 |
| 331 | 330 | 758.7 | 260.4 | 920.7/260.4>DiHexCer: d18:0/20:0 | 25 | 60 | 10 | 60 | 20 |
| 332 | 331 | 784.8 | 264.4 | 940.8/264.4>DiHexCer: d18:1/22:0 | 25 | 110 | 10 | 50 | 15 |
| 333 | 332 | 780.8 | 260.4 | 948.8/260.4>DiHexCer: d18:0/22:0 | 25 | 110 | 10 | 30 | 25 |
| 334 | 333 | 810.9 | 264.4 | 972.9/264.4>DiHexCer: d18:1/24:1 | 25 | 110 | 10 | 50 | 10 |
| 335 | 334 | 812.9 | 260.4 | 974.9/260.4>DiHexCer: d18:0/24:1 | 25 | 110 | 10 | 50 | 15 |

APPENDIX A-continued

MRM Conditions for Lipids

| | A | B | C | D | E | F | G | H | I |
|---|---|---|---|---|---|---|---|---|---|
| 336 | 335 | 812.9 | 264.4 | 974.9/264.4>DiHexCer: d18:1/24:0 | 25 | 100 | 10 | 70 | 15 |
| 337 | 336 | 814.9 | 260.4 | 970.9/260.4>DiHexCer: d18:0/24:0 | 25 | 110 | 10 | 50 | 20 |
| 338 | 337 | 838.9 | 264.4 | 1000.9/264.4>DiHexCer: d18:1/26:1 | 25 | 110 | 10 | 70 | 10 |
| 339 | 338 | 840.9 | 260.4 | 1002.9/260.4>DiHexCer: d18:0/26:1 | 25 | 80 | 10 | 50 | 40 |
| 340 | 339 | 840.9 | 264.4 | 1002.9/264.4>DiHexCer: d18:1/26:0 | 25 | 90 | 10 | 60 | 10 |
| 341 | 340 | 842.9 | 260.4 | 1004.9/260.4>DiHexCer: d18:0/26:0 | 25 | 100 | 10 | 50 | 15 |

APPENDIX B1

PCA Transformation Matrix(340 × 340; Normal/Diseased)

| | A | B | C | D | E | F | G | H | I | J | K |
|---|---|---|---|---|---|---|---|---|---|---|---|
| 1 | 409.4/255.3>GPA:Lyso 16:0 | −0.072048 | −0.00426 | −0.042817 | 0.032854 | 0.11006 | −0.10195 | 0.076834 | 0.028175 | −0.019868 | −0.017638 |
| 2 | 433.4/279.3>GPA:Lyso 18:2 | −0.035066 | −0.063365 | −0.017437 | 0.044861 | 0.064352 | −0.167764 | 0.013261 | −0.000074 | 0.010433 | −0.013335 |
| 3 | 435.4/281.3>GPA:Lyso 18:1 | −0.056634 | −0.044772 | −0.039474 | 0.045356 | 0.080659 | −0.117163 | 0.056561 | 0.001126 | −0.008704 | −0.022679 |
| 4 | 437.4/283.3>GPA:Lyso 18:0 | −0.007636 | 0.039643 | 0.042319 | −0.00977 | 0.108663 | −0.037898 | 0.086333 | 0.075763 | −0.08075 | 0.036092 |
| 5 | 451.4/283.3>GPA:Lyso 18:0 | −0.014777 | −0.031643 | 0.0065 | −0.019739 | 0.044187 | −0.010991 | 0.051433 | 0.106384 | 0.031394 | −0.007591 |
| 6 | 459.6/305.5>GPA:Lyso 20:3 | −0.040964 | −0.039208 | −0.028496 | 0.04662 | 0.040847 | −0.114979 | 0.057059 | −0.071661 | 0.002444 | −0.111178 |
| 7 | 461.6/307.5>GPA:Lyso 20:2 | −0.028006 | −0.075177 | −0.025667 | 0.039713 | 0.049349 | −0.103468 | 0.051128 | 0.042746 | 0.029812 | −0.01215 |
| 8 | 463.7/309.5>GPA:Lyso 20:1 | −0.031997 | 0.009277 | 0.026591 | 0.013594 | 0.040224 | −0.090638 | 0.071173 | 0.017222 | −0.037193 | 0.06109 |
| 9 | 465.7/311.5>GPA:Lyso 20:0 | −0.016862 | 0.047787 | 0.051026 | −0.050398 | 0.07988 | −0.010457 | 0.06937 | 0.053529 | −0.076138 | 0.022603 |
| 10 | 481.4/327.3>GPA:Lyso 22:6 | −0.032556 | −0.042662 | −0.061918 | 0.046493 | 0.100567 | −0.088525 | −0.01486 | −0.057974 | 0.035431 | −0.033435 |
| 11 | 483.4/329.3>GPA:Lyso 22:5 | −0.030836 | −0.018643 | 0.004653 | −0.001132 | 0.063362 | −0.043828 | 0.04747 | −0.053662 | 0.049149 | −0.102141 |
| 12 | 641.8/251.3>GPA:16:1/16:2 | −0.018894 | −0.018285 | 0.027543 | −0.008563 | 0.00197 | 0.016319 | −0.028362 | 0.131618 | 0.026615 | 0.059507 |
| 13 | 643.8/253.3>GPA:16:1/16:1 | −0.006985 | 0.015067 | 0.03653 | 0.030993 | 0.005512 | 0.031601 | −0.1831 | 0.102 | −0.133189 | −0.125881 |
| 14 | 645.8/255.3>GPA:16:1/16:0 | −0.013851 | 0.015549 | 0.042855 | 0.022986 | 0.006604 | 0.023559 | −0.170191 | 0.09903 | −0.143931 | −0.128949 |
| 15 | 647.8/255.3>GPA:16:0/16:0 | −0.078796 | −0.026833 | 0.076326 | 0.087226 | 0.0783 | 0.008389 | −0.009498 | 0.000587 | −0.020026 | −0.061646 |
| 16 | 667.8/279.3>GPA:34:4 | 0.020465 | −0.040376 | 0.031941 | −0.032974 | 0.030055 | −0.032117 | 0.021582 | 0.003465 | −0.042322 | 0.089702 |
| 17 | 669.8/279.3>GPA:34:3 | −0.045384 | −0.042213 | 0.040502 | −0.01318 | 0.018932 | −0.107806 | −0.043028 | 0.140045 | −0.002021 | −0.070259 |
| 18 | 669.8/281.3>GPA:34:4 | −0.04093 | 0.019534 | 0.005895 | −0.056502 | 0.063352 | −0.037127 | −0.034122 | 0.004551 | −0.072166 | −0.061272 |
| 19 | 671.8/279.3>GPA:18:2/16:0 | −0.030903 | −0.048813 | 0.035857 | 0.006967 | 0.106489 | −0.099477 | −0.027117 | 0.032328 | 0.028677 | 0.005248 |
| 20 | 673.8/281.3>GPA:18:1/16:0 | −0.042018 | −0.014759 | 0.141125 | 0.094768 | 0.016068 | 0.068523 | −0.02725 | −0.028771 | −0.002549 | −0.04011 |
| 21 | 695.8/279.3>GPA:36:4 | −0.029587 | −0.05738 | 0.011446 | 0.05299 | 0.055959 | −0.145795 | −0.009879 | 0.030282 | 0.031484 | 0.005711 |
| 22 | 695.8/303.3>GPA:36:4 | −0.044102 | −0.032315 | 0.058107 | 0.061533 | 0.130896 | −0.002599 | 0.012977 | −0.057517 | 0.036618 | −0.016201 |
| 23 | 697.8/281.3>GPA:20:3/16:0 | −0.046553 | −0.047398 | 0.06244 | 0.062472 | 0.075453 | 0.00999 | 0.05207 | −0.012027 | 0.019326 | 0.002573 |
| 24 | 697.8/305.3>GPA:18:1/18:2 | −0.051341 | −0.035914 | 0.066744 | 0.088874 | 0.034627 | −0.079357 | −0.008776 | 0.030632 | 0.013063 | −0.043943 |
| 25 | 699.8/279.3>GPA:36:2 | −0.046837 | −0.043293 | 0.080797 | 0.094328 | 0.020705 | −0.102537 | −0.037823 | 0.010853 | 0.023238 | −0.035109 |
| 26 | 699.8/281.3>GPA:36:2 | −0.041674 | −0.013144 | 0.137412 | 0.100488 | 0.008 | 0.074817 | −0.004032 | −0.0381 | 0.014054 | −0.02506 |
| 27 | 701.8/283.3>GPA:36:1 | −0.035301 | −0.018798 | 0.145537 | 0.090519 | 0.013822 | 0.070913 | 0.010423 | −0.055618 | 0.028019 | −0.001949 |
| 28 | 703.8/283.3>GPA:36:0 | −0.058367 | 0.006176 | 0.133949 | 0.078737 | 0.046965 | 0.030314 | 0.046898 | −0.010892 | −0.000127 | −0.004419 |
| 29 | 721.8/255.3>GPA:18:1/20:4 | −0.031432 | −0.013205 | 0.117323 | 0.095899 | 0.048707 | 0.049778 | −0.003407 | −0.051558 | 0.047363 | 0.012026 |
| 30 | 721.8/281.3>GPA:16:0/22:5 | −0.083459 | 0.077787 | −0.008305 | 0.015057 | 0.068843 | −0.022017 | 0.052255 | 0.074823 | −0.016714 | −0.006306 |
| 31 | 723.8/283.3>GPA:18:0/20:4 | −0.034992 | −0.022993 | 0.134417 | 0.097264 | 0.027253 | 0.079735 | 0.030017 | −0.057089 | 0.011353 | 0.002234 |
| 32 | 725.8/305.3>GPA:20:3/18:0 | −0.024214 | −0.016708 | 0.109811 | 0.104044 | 0.01268 | 0.0471 | 0.042216 | −0.077556 | 0.006282 | −0.034525 |
| 33 | 729.8/281.3>GPA:38:1 | −0.044266 | −0.038759 | 0.144747 | 0.064692 | 0.024636 | 0.048153 | 0.002724 | −0.037949 | 0.043655 | −0.005229 |
| 34 | 731.8/283.3>GPA:38:0 | −0.072558 | 0.021902 | 0.111198 | 0.070193 | 0.057878 | 0.013149 | 0.042976 | 0.012444 | 0.012906 | −0.013929 |
| 35 | 751.8/303.3>GPA:40:4 | 0.029108 | −0.100203 | −0.018158 | 0.066195 | 0.015395 | −0.03893 | −0.044088 | −0.034808 | 0.059295 | −0.030363 |
| 36 | 757.8/281.3>GPA:40:1 | −0.067035 | −0.005102 | 0.092001 | 0.104874 | −0.017357 | 0.06364 | −0.004605 | −0.041369 | 0.058509 | 0.035826 |
| 37 | 759.8/283.3>GPA:40:0 | −0.056072 | −0.014748 | 0.145774 | 0.054636 | 0.023937 | 0.058516 | 0.021256 | −0.057024 | 0.024774 | −0.015399 |
| 38 | 777.8/329.3>GPA:42:5 | −0.017068 | −0.031383 | 0.01114 | −0.06618 | 0.050245 | 0.01312 | 0.008846 | 0.12386 | 0.04076 | 0.06802 |
| 39 | 481.4/253.3>GPGro:Lyso 16:1 | −0.006328 | 0.031149 | 0.010807 | −0.006771 | 0.099684 | 0.025747 | 0.073188 | 0.140166 | 0.046495 | −0.030191 |
| 40 | 483.4/255.3>GPGro:Lyso 16:0 | −0.062602 | 0.056927 | −0.008244 | −0.006527 | 0.12617 | −0.024633 | 0.016792 | 0.091883 | −0.00645 | −0.036505 |
| 41 | 507.4/279.3>GPGro:Lyso 18:2 | −0.045115 | 0.023544 | 0.017782 | 0.004673 | 0.13152 | −0.071835 | −0.004508 | 0.112547 | −0.006728 | −0.034255 |
| 42 | 509.4/281.3>GPGro:Lyso 18:1 | −0.005933 | 0.027512 | 0.009493 | −0.019978 | 0.142959 | 0.02059 | 0.060694 | 0.113534 | −0.010712 | −0.001268 |
| 43 | 511.4/283.3>GPGro:Lyso 18:0 | −0.050559 | 0.073625 | 0.005206 | −0.001329 | 0.12234 | −0.028941 | −0.001017 | 0.101562 | −0.015504 | −0.021383 |
| 44 | 531.4/303.3>GPGro:Lyso 20:4 | −0.047362 | 0.016571 | −0.018802 | 0.018383 | 0.148728 | −0.03682 | 0.005132 | 0.082104 | −0.010457 | −0.071225 |
| 45 | 555.4/327.3>GPGro:Lyso 22:6 | −0.040023 | 0.0395121 | −0.023899 | 0.016492 | 0.149232 | −0.025101 | −0.018469 | 0.080289 | 0.015222 | −0.045335 |
| 46 | 557.4/329.3>GPGro:Lyso 22:5 | −0.025829 | −0.020292 | 0.000241 | −0.031275 | 0.141847 | −0.026567 | 0.001778 | 0.092404 | 0.02818 | −0.061269 |
| 47 | 717.8/253.3>GPGro:16:1/16:1 | −0.000654 | 0.014484 | −0.032278 | −0.004807 | −0.070578 | 0.070598 | 0.128263 | 0.052209 | −0.034951 | −0.059516 |

APPENDIX B1-continued

PCA Transformation Matrix(340 × 340; Normal/Diseased)

| | | | | | | | | | | | |
|---|---|---|---|---|---|---|---|---|---|---|---|
| 48 | 719.8/253.3>GPGro:16:1/16:0 | 0.014846 | 0.003175 | 0.029676 | −0.055977 | 0.03487 | 0.026441 | 0.046469 | 0.092587 | 0.003845 | −0.029125 |
| 49 | 721.8/255.3>GPGro:16:0/16:0 | −0.080404 | 0.083246 | −0.002502 | 0.011387 | 0.068352 | −0.015719 | 0.041856 | 0.069736 | −0.021758 | 0.005238 |
| 50 | 743.8/279.3>GPGro:18:2/16:1 | 0.0135 | −0.062557 | −0.01304 | 0.003635 | −0.141312 | 0.006201 | −0.127467 | 0.002668 | 0.041183 | 0.086041 |
| 51 | 743.8/281.3>GPGro:18:1/16:2 | −0.017369 | 0.003937 | −0.070473 | 0.01125 | −0.103353 | 0.122419 | 0.045984 | 0.022047 | −0.002012 | 0.007082 |
| 52 | 745.8/279.3>GPGro:18:2/16:0 | 0.012958 | −0.075541 | 0.006287 | −0.041602 | −0.105064 | −0.020611 | −0.096897 | 0.043658 | 0.012639 | 0.105664 |
| 53 | 745.8/281.3>GPGro:18:1/16:1 | −0.039102 | 0.005956 | −0.063638 | −0.018985 | −0.1008 | 0.131175 | 0.050665 | −0.004927 | −0.024995 | 0.004489 |
| 54 | 747.8/255.2>GPGro:16:0/18:1 | 0.033447 | −0.000271 | 0.03495 | −0.092079 | 0.080812 | 0.070351 | 0.034117 | 0.098083 | −0.020404 | 0.014955 |
| 55 | 747.8/281.1>GPGro:16:0/18:1 | −0.069905 | 0.012017 | 0.015325 | 0.120809 | −0.063035 | 0.09377 | 0.048 | −0.037284 | 0.019033 | −0.006716 |
| 56 | 749.8/283.3>GPGro:18:0/16:0 | −0.079133 | 0.081272 | 0.00082 | 0.02911 | 0.062013 | −0.021802 | 0.027031 | 0.078356 | −0.011267 | −0.006412 |
| 57 | 767.8/303.3>GPGro:20:4/16:1 | 0.039919 | −0.068997 | −0.095523 | 0.025044 | 0.00639 | 0.114072 | −0.006409 | −0.036782 | 0.030542 | −0.046847 |
| 58 | 769.8/279.3>GPGro:18:2/18:2 | 0.034698 | −0.089669 | 0.079869 | −0.091858 | −0.02705 | −0.058792 | −0.034443 | 0.0069 | 0.019054 | 0.039114 |
| 59 | 769.8/303.3>GPGro:20:4/16:0 | 0.006939 | −0.007337 | −0.041069 | 0.001942 | 0.080456 | 0.061192 | −0.020512 | 0.052507 | −0.015516 | −0.082748 |
| 60 | 771.8/279.3>GPGro:18:2/18:1 | 0.002321 | −0.000637 | −0.022628 | 0.090368 | −0.154851 | −0.093067 | −0.029226 | 0.007314 | 0.068513 | 0.001382 |
| 61 | 773.8/279.3>GPGro:18:2/18:0 | 0.000927 | 0.064628 | 0.016967 | 0.052291 | −0.028682 | −0.096806 | −0.043261 | 0.115162 | 0.021763 | −0.023944 |
| 62 | 773.8/281.3>GPGro:18:1/18:1 | −0.002697 | 0.031536 | −0.020133 | 0.060371 | −0.14239 | −0.015576 | 0.090716 | 0.013327 | 0.034414 | −0.088125 |
| 63 | 775.8/281.3>GPGro:18:1/18:0 | −0.001489 | 0.092452 | 0.004829 | 0.012319 | 0.073068 | 0.013265 | 0.051684 | 0.137948 | −0.017206 | −0.051696 |
| 64 | 777.8/283.3>GPGro:18:0/18:0 | −0.076657 | 0.081993 | 0.001231 | 0.007741 | 0.061194 | −0.052025 | 0.036218 | 0.074135 | −0.005007 | −0.021732 |
| 65 | 795.8/303.3>GPGro:20:4/18:1 | 0.02702 | −0.030317 | −0.106782 | 0.080204 | −0.028822 | 0.045545 | 0.012571 | −0.052531 | 0.059074 | −0.095318 |
| 66 | 797.8/303.3>GPGro:20:4/18:0 | −0.009555 | 0.075174 | −0.048702 | 0.030159 | 0.076649 | 0.020224 | −0.023096 | 0.049547 | 0.016446 | −0.080781 |
| 67 | 821.8/327.3>GPGro:22:6/18:0 | −0.028807 | 0.055138 | −0.047943 | 0.051074 | 0.090474 | 0.011932 | −0.047748 | 0.070696 | 0.023616 | −0.055811 |
| 68 | 823.8/329.3>GPGro:22:5/18:0 | 0.009526 | 0.006435 | −0.053366 | 0.028832 | 0.043851 | 0.007737 | 0.02513 | 0.120132 | 0.067802 | −0.041528 |
| 69 | 494.4/407.4>Lyso GPSer:16:1 | 0.000049 | 0.014817 | 0.037152 | 0.031196 | 0.000903 | 0.023157 | −0.183694 | 0.090526 | −0.127064 | −0.132684 |
| 70 | 490.4/409.4>Lyso GPSer:16:0 | −0.004814 | 0.00543 | 0.028388 | 0.021037 | 0.00804 | 0.016076 | −0.179286 | 0.096006 | −0.138443 | −0.131057 |
| 71 | 522.4/435.4>Lyso GPSer:18:1 | −0.01304 | −0.043484 | 0.10159 | 0.043191 | 0.047226 | 0.012822 | −0.042011 | 0.035479 | −0.119045 | −0.016916 |
| 72 | 524.4/437.4>Lyso GPSer:18:0 | −0.01777 | −0.042641 | 0.083159 | 0.009577 | 0.06069 | 0.034225 | 0.056377 | −0.006427 | −0.104166 | 0.085869 |
| 73 | 544.4/457.4>Lyso GPSer:20:4 | 0.008568 | −0.061429 | 0.032031 | 0.005129 | 0.066669 | 0.013468 | 0.053281 | 0.011068 | −0.105376 | 0.084058 |
| 74 | 570.4/483.4>Lyso GPSer:22:5 | −0.005001 | −0.004352 | 0.020324 | −0.0978 | 0.009534 | −0.02483 | −0.025859 | −0.0738 | 0.028667 | −0.040622 |
| 75 | 732.6/645.6>GPSer:32:1 | −0.000439 | 0.009614 | 0.024004 | 0.020919 | −0.005737 | 0.014723 | −0.180819 | 0.09509 | −0.142745 | −0.137964 |
| 76 | 734.6/647.6>GPSer:32:0 | −0.00608 | 0.010809 | 0.034288 | 0.007887 | −0.005112 | 0.015209 | −0.180693 | 0.073524 | −0.140271 | −0.146728 |
| 77 | 758.6/671.6>GPSer:34:2 | 0.000058 | 0.009638 | 0.024682 | 0.018762 | −0.004496 | 0.01207 | −0.180449 | 0.094075 | −0.140151 | −0.140682 |
| 78 | 760.8/673.8>GPSer:34:1 | −0.002675 | 0.00556 | 0.036222 | 0.02747 | −0.00346 | 0.017938 | −0.176431 | 0.090776 | −0.141822 | −0.135727 |
| 79 | 762.8/675.7>GPSer:34:0 | −0.008781 | 0.003733 | 0.050263 | 0.037335 | −0.004251 | 0.024468 | −0.174471 | 0.08142 | −0.131958 | −0.131867 |
| 80 | 782.6/695.7>GPSer:36:4 | −0.004251 | 0.071616 | 0.04252 | −0.029177 | 0.088303 | 0.033698 | −0.078262 | 0.007625 | 0.037573 | 0.019662 |
| 81 | 784.8/697.8>GPSer:36:3 | −0.019557 | 0.021253 | 0.057839 | −0.046898 | 0.023293 | 0.040394 | −0.154778 | 0.005337 | −0.124088 | −0.084616 |
| 82 | 780.8/699.8>GPSer:36:2 | −0.029408 | −0.025441 | 0.156417 | 0.077729 | 0.0199 | 0.077282 | −0.022644 | −0.037844 | −0.016949 | −0.010934 |
| 83 | 788.8/701.8>GPSer:36:1 | −0.030415 | −0.025361 | 0.150756 | 0.084855 | 0.018391 | 0.075114 | 0.013387 | −0.055445 | 0.014724 | 0.010498 |
| 84 | 790.8/703.8>GPSer:36:0 | −0.030812 | −0.023955 | 0.151004 | 0.083767 | 0.016616 | 0.073743 | 0.013593 | −0.054289 | 0.018944 | 0.008232 |
| 85 | 808.6/721.6>GPSer:38:6 | −0.006996 | −0.031401 | 0.11142 | 0.03233 | 0.055308 | 0.067292 | 0.017047 | −0.025176 | −0.067823 | 0.108184 |
| 86 | 810.8/723.8>GPSer:38:5 | 0.006949 | −0.055014 | 0.085629 | 0.012147 | 0.044979 | 0.060737 | 0.040245 | −0.001881 | −0.08929 | 0.074801 |
| 87 | 812.8/725.8>GPSer:38:4 | −0.011925 | −0.043198 | 0.128979 | 0.062148 | 0.041145 | 0.075043 | 0.035252 | −0.033593 | −0.069918 | 0.043247 |
| 88 | 814.6/727.6>GPSer:38:3 | −0.030825 | −0.021601 | 0.14978 | 0.085769 | 0.017812 | 0.075953 | 0.009236 | −0.052936 | 0.023835 | 0.0114 |
| 89 | 810.8/729.8>GPSer:38:2 | −0.032739 | −0.020884 | 0.14663 | 0.087955 | 0.013918 | 0.070745 | 0.010691 | −0.058008 | 0.03013 | 0.002499 |
| 90 | 818.8/731.8>GPSer:38:1 | −0.032027 | −0.021361 | 0.148534 | 0.087334 | 0.014522 | 0.073663 | 0.011111 | −0.05422 | 0.022039 | 0.00655 |
| 91 | 834.8/747.8>GPSer:40:6 | −0.030983 | −0.022803 | 0.147046 | 0.087386 | 0.021459 | 0.079891 | 0.005607 | −0.052271 | 0.02514 | 0.00202 |
| 92 | 830.8/749.8>GPSer:40:5 | −0.020804 | −0.03098 | 0.1455 | 0.073666 | 0.024054 | 0.083049 | −0.014721 | −0.042746 | −0.028188 | 0.007707 |
| 93 | 838.8/751.8>GPSer:40:4 | −0.022716 | −0.029096 | 0.149962 | 0.081871 | 0.027795 | 0.082107 | 0.019323 | −0.046832 | −0.008881 | 0.030267 |
| 94 | 840.6/753.7>GPSer:40:3 | −0.029738 | −0.005052 | 0.152755 | 0.062969 | 0.033917 | 0.076322 | −0.012849 | −0.073268 | 0.010407 | 0.023027 |
| 95 | 778.9/97>Sulfatide:16:0 | 0.045471 | −0.033572 | 0.037003 | −0.043285 | 0.086475 | −0.055079 | −0.004432 | −0.024079 | −0.024299 | 0.105555 |
| 96 | 800.9/97>Sulfatide:18:0 | −0.000752 | 0.057317 | 0.000734 | −0.002558 | 0.117618 | 0.014159 | 0.025864 | 0.05506 | 0.067229 | 0.035917 |
| 97 | 822.9/97>Sulfatide:18:0 (OH) | −0.083177 | −0.023484 | −0.036274 | −0.05474 | 0.033575 | −0.039833 | −0.041297 | −0.086612 | 0.025132 | 0.030753 |
| 98 | 834.9/97>Sulfatide:20:0 | 0.025634 | 0.100402 | 0.018493 | −0.064878 | 0.106188 | 0.010556 | −0.058657 | −0.037293 | 0.044779 | 0.027923 |

APPENDIX B1-continued

PCA Transformation Matrix(340 × 340; Normal/Diseased)

| | | | | | | | | | | | |
|---|---|---|---|---|---|---|---|---|---|---|---|
| 99 | 850.9/97>Sulfatide:20:0 (OH) | −0.095375 | −0.030341 | −0.066581 | −0.017317 | 0.049369 | 0.007355 | −0.0346 | −0.057925 | 0.019875 | 0.047774 |
| 100 | 862.9/97>Sulfatide:22:1 | 0.048338 | 0.074112 | 0.026382 | −0.087686 | 0.109649 | 0.005879 | −0.042005 | −0.008523 | 0.06073 | 0.018528 |
| 101 | 878.9/97>Sulfatide:22:1 (OH) | 0.002955 | 0.100778 | 0.001099 | −0.064019 | 0.089612 | 0.010975 | −0.081649 | −0.04771 | 0.04401 | 0.019172 |
| 102 | 888.9/97>Sulfatide:24:1 | 0.06178 | −0.023216 | 0.001251 | −0.028247 | 0.090078 | 0.012398 | 0.018263 | 0.021812 | 0.05716 | 0.001865 |
| 103 | 890.9/97>Sulfatide:24:0 | −0.001134 | 0.039156 | 0.0401 | −0.073788 | 0.096307 | −0.03656 | −0.033818 | −0.029525 | 0.064036 | −0.003292 |
| 104 | 900.7/97>Sulfatide:24:0 (OH) | −0.014205 | −0.023615 | −0.014951 | −0.073913 | 0.040283 | −0.058827 | −0.012054 | −0.105587 | 0.091155 | −0.098472 |
| 105 | 1147/281.3>CardioliGPInsn:52:3 | −0.029334 | 0.068436 | −0.003355 | 0.034644 | 0.019276 | −0.000831 | 0.050523 | 0.069929 | 0.035568 | 0.045702 |
| 106 | 1376/281.3>CardioliGPInsn:66:2 | −0.076882 | 0.017512 | −0.034171 | 0.082927 | −0.096053 | −0.032497 | 0.069791 | 0.005418 | 0.006231 | −0.030976 |
| 107 | 1400/281.3>CardioliGPInsn:68:4 | −0.074567 | 0.027803 | −0.031109 | 0.085649 | −0.098903 | −0.037283 | 0.037784 | 0.012112 | −0.007241 | −0.018101 |
| 108 | 1402/281.3>CardioliGPInsn:68:3 | −0.061761 | 0.025756 | −0.037895 | 0.076784 | −0.064267 | −0.029432 | 0.084913 | 0.016946 | −0.000611 | −0.003701 |
| 109 | 1404/281.3>CardioliGPInsn:68:2 | −0.058221 | 0.034444 | −0.030577 | 0.072839 | −0.03602 | 0.001432 | 0.031539 | 0.022322 | −0.005628 | −0.023443 |
| 110 | 1406/281.3>CardioliGPInsn:68:1 | −0.037789 | 0.072698 | −0.040688 | 0.063732 | −0.029739 | 0.020063 | −0.021302 | 0.025604 | 0.011547 | 0.018832 |
| 111 | 1426/281.3>CardioliGPInsn:70:5 | −0.07776 | 0.037283 | −0.03989 | 0.060588 | −0.039831 | −0.017401 | 0.06773 | 0.046131 | −0.000453 | −0.054328 |
| 112 | 1428/281.3>CardioliGPInsn:70:4 | −0.069191 | 0.033542 | −0.037856 | 0.061411 | −0.023848 | −0.023374 | 0.049252 | 0.03872 | 0.020942 | −0.013421 |
| 113 | 1430/281.3>CardioliGPInsn:70:3 | −0.08108 | 0.021824 | −0.04011 | 0.079181 | −0.027842 | −0.015171 | 0.033064 | 0.041396 | 0.012451 | −0.023458 |
| 114 | 1432/281.3>CardioliGPInsn:70:2 | −0.060819 | 0.063724 | −0.003586 | 0.069428 | −0.002404 | −0.012051 | 0.014126 | 0.082187 | −0.057419 | −0.038153 |
| 115 | 1434/281.3>CardioliGPInsn:70:1 | −0.083792 | 0.038425 | 0.023405 | 0.063987 | −0.018616 | 0.009863 | 0.052634 | 0.019258 | 0.023195 | −0.065075 |
| 116 | 1436/281.3>CardioliGPInsn:70:0 | −0.066614 | 0.053208 | −0.008323 | 0.080427 | −0.040529 | 0.010286 | 0.040764 | 0.051444 | −0.002256 | −0.029313 |
| 117 | 430.6/190.1>Lyso GPEtn:Lyso16:1e/16:0p | 0.0362 | −0.062838 | 0.049836 | −0.061108 | 0.009776 | 0.027269 | −0.0017 | 0.058124 | 0.092863 | 0.040738 |
| 118 | 450.4/190.1>Lyso GPEtn:Lyso 16:1 | 0.026052 | −0.044978 | 0.074063 | −0.088943 | −0.014055 | −0.019264 | 0.118215 | 0.0487 | −0.060785 | −0.007038 |
| 119 | 452.4/190.1>Lyso GPEtn:Lyso 16:0 | −0.043781 | −0.029001 | 0.040912 | −0.101775 | 0.016305 | 0.004454 | 0.104145 | 0.004859 | −0.079682 | 0.01465 |
| 120 | 462.4/190.1>Lyso GPEtn:Lyso18:2e/18:1p | 0.012105 | −0.052164 | 0.052236 | −0.095078 | −0.008931 | 0.040637 | −0.003006 | 0.087452 | 0.115408 | 0.01206 |
| 121 | 464.5/190.1>Lyso GPEtn:Lyso18:1e/18:0p | 0.021988 | −0.06136 | 0.035979 | −0.057638 | 0.015829 | 0.024886 | −0.035456 | 0.108708 | 0.115596 | 0.048147 |
| 122 | 470.6/190.1>Lyso GPEtn:Lyso18:2a | 0.027817 | −0.060143 | 0.077894 | 0.023522 | −0.047482 | −0.128917 | 0.057209 | 0.037167 | −0.032312 | 0.004759 |
| 123 | 478.4/190.1>Lyso GPEtn:Lyso 18:1 | 0.020925 | −0.06558 | 0.093202 | −0.028182 | −0.016784 | −0.063959 | 0.086001 | 0.027869 | −0.085825 | 0.025927 |
| 124 | 480.4/190.1>Lyso GPEtn:Lyso 18:0 | −0.046385 | −0.045807 | 0.043919 | −0.103407 | 0.003273 | −0.025072 | 0.096174 | 0.000439 | −0.103904 | −0.010296 |
| 125 | 492.5/190.1>Lyso GPEtn:Lyso20:1e/20:0p | −0.01564 | −0.0615 | 0.057988 | −0.101428 | −0.001306 | 0.045657 | 0.002574 | 0.049621 | 0.071727 | −0.040329 |
| 126 | 500.4/190.1>Lyso GPEtn:Lyso 20:4 | 0.044023 | −0.093147 | 0.038534 | −0.036508 | 0.023962 | −0.000904 | 0.052094 | 0.014343 | −0.067895 | 0.037999 |
| 127 | 524.4/190.1>Lyso GPEtn:Lyso 22:6 | 0.048079 | −0.105776 | 0.021777 | −0.034385 | 0.034896 | 0.005497 | 0.049605 | −0.00063 | −0.039218 | 0.024486 |
| 128 | 688.6/190.1>GPEtn:16:0/16:1 | −0.00783 | 0.032593 | 0.042461 | −0.12784 | −0.016768 | 0.00793 | −0.001173 | −0.034051 | 0.067449 | −0.092917 |
| 129 | 690.7/190.1>GPEtn 16:0/16:0 | −0.023304 | −0.01346 | 0.038898 | −0.082187 | −0.002063 | 0.009512 | 0.020138 | −0.020085 | −0.011948 | 0.001265 |
| 130 | 698.6/190.1>GPEtn:34:2p, 34:3e | −0.004763 | −0.020302 | 0.028992 | −0.120817 | 0.019479 | 0.013632 | −0.031464 | 0.011759 | 0.044841 | −0.026628 |
| 131 | 700.6/190.1>GPEtn:34:1p, 34:2e | −0.011015 | −0.012137 | 0.019999 | −0.033718 | 0.009273 | 0.004084 | 0.01289 | 0.029892 | 0.028907 | 0.06952 |
| 132 | 702.6/190.1>GPEtn:34:0p, 34:1e | −0.015565 | 0.001325 | 0.04284 | −0.124224 | −0.032904 | −0.00019 | −0.025788 | −0.040653 | 0.088318 | −0.095088 |
| 133 | 710.8/190.1>GPEtn:18:1/16:1 | −0.03124 | −0.013521 | 0.056938 | −0.106859 | −0.003051 | 0.027437 | −0.043197 | 0.034726 | 0.056105 | 0.037406 |
| 134 | 712.8/190.1>GPEtn:18:2/16:1 | −0.010473 | −0.035468 | 0.086815 | −0.066121 | −0.030666 | 0.035647 | 0.012272 | 0.041578 | 0.009519 | −0.006447 |
| 135 | 714.7/190.1>GPEtn:18:1/16:1 | −0.020023 | −0.068717 | 0.092995 | −0.125083 | −0.034649 | 0.004462 | −0.005459 | −0.029324 | 0.006234 | −0.08407 |
| 136 | 710.7/190.1>GPEtn:18:1/16:0 | −0.021139 | −0.052545 | 0.060193 | −0.101399 | −0.059418 | 0.05285 | 0.05699 | 0.047045 | −0.010758 | −0.063233 |
| 137 | 718.6/190.1>GPEtn:18:0/16:0 | 0.009552 | −0.00646 | 0.062871 | −0.110355 | 0.035665 | 0.015765 | −0.012278 | −0.068054 | 0.073433 | −0.074194 |
| 138 | 722.6/190.1>GPEtn:36:4p | −0.023059 | −0.018546 | 0.03853 | −0.03202 | 0.02752 | 0.040476 | 0.060639 | 0.083984 | 0.022608 | 0.044132 |
| 139 | 724.6/190.1>GPEtn:36:3p, 36:4e | −0.010315 | −0.008859 | 0.015087 | −0.069699 | −0.001101 | −0.011295 | −0.019802 | 0.10943 | 0.104366 | 0.020964 |
| 140 | 720.6/190.1>GPEtn:36:2p, 36:3e | −0.005385 | −0.011621 | 0.040595 | −0.062009 | −0.045945 | −0.035242 | 0.00583 | −0.048721 | 0.013542 | −0.018764 |
| 141 | 728.6/190.1>GPEtn:36:1p, 36:2e | −0.023592 | −0.026737 | 0.060457 | −0.119054 | −0.036288 | −0.025198 | −0.006571 | −0.049083 | 0.023455 | −0.097558 |
| 142 | 738.8/190.1>GPEtn:20:4/16:0 | 0.02663 | −0.109465 | 0.001241 | −0.065608 | 0.007207 | 0.085337 | 0.027972 | 0.03945 | −0.034676 | 0.005578 |
| 143 | 740.8/190.1>GPEtn:18:2/18:1 | −0.007564 | −0.061536 | 0.106338 | −0.079364 | −0.027424 | −0.050076 | 0.007799 | −0.016899 | −0.011897 | −0.063579 |
| 144 | 742.8/190.1>GPEtn:18:1/18:1 | 0.002414 | −0.065735 | 0.084408 | −0.060832 | −0.070867 | −0.04696 | 0.055636 | 0.049766 | −0.035714 | −0.031636 |
| 145 | 744.6/190.1>GPEtn:18:0/18:1 | −0.017446 | −0.0644 | 0.064632 | −0.100087 | −0.043787 | −0.020663 | 0.028789 | 0.049475 | 0.041781 | −0.070474 |
| 146 | 740.8/190.1>GPEtn:18:0/18:0 | −0.024925 | −0.06844 | 0.105885 | −0.08327 | −0.009299 | 0.060284 | −0.033205 | 0.045633 | 0.080783 | −0.022211 |
| 147 | 748.6/190.1>GPEtn:38:5p, 38:6e | −0.005325 | −0.071261 | 0.044612 | −0.058896 | −0.001271 | 0.055045 | −0.011417 | 0.131419 | 0.081656 | 0.023319 |
| 148 | 750.6/190.1>GPEtn:38:4p, 38:5e | 0.001844 | −0.037154 | 0.030953 | −0.057551 | −0.008687 | −0.078713 | −0.007765 | −0.00604 | 0.072741 | −0.006564 |
| 149 | 752.6/190.1>GPEtn:38:3p, 38:4e | −0.013166 | −0.020915 | 0.053253 | −0.121376 | −0.019478 | −0.049327 | −0.013236 | −0.1092 | 0.019264 | −0.112345 |

APPENDIX B1-continued

PCA Transformation Matrix(340 × 340; Normal/Diseased)

| | | | | | | | | | | | |
|---|---|---|---|---|---|---|---|---|---|---|---|
| 150 | 754.6/190.1>GPEtn:38:2p, 38:3e | −0.022812 | −0.007787 | 0.073568 | −0.101968 | −0.001287 | 0.007269 | 0.012213 | −0.077572 | 0.024634 | −0.10135 |
| 151 | 750.6/190.1>GPEtn:38:1p, 38:2e | −0.004221 | −0.014118 | 0.024214 | −0.019493 | 0.004144 | 0.037335 | 0.016083 | 0.018706 | 0.018845 | 0.012616 |
| 152 | 762.8/190.1>GPEtn:20:4/18:2 | 0.036104 | −0.112645 | −0.022772 | −0.051374 | 0.023874 | 0.08206 | 0.029546 | 0.042141 | 0.018574 | −0.009666 |
| 153 | 764.8/190.1>GPEtn:20:4/18:1 | 0.03089 | −0.103968 | 0.016736 | −0.064039 | 0.006151 | 0.048211 | 0.052274 | 0.051943 | −0.011125 | 0.002259 |
| 154 | 760.8/190.1>GPEtn:20:4/18:0 | 0.03926 | −0.100108 | −0.005985 | −0.061224 | −0.002054 | 0.076527 | 0.041501 | 0.008717 | −0.061355 | −0.019718 |
| 155 | 768.8/190.1>GPEtn:20:3/18:0 | 0.02422 | −0.089093 | 0.046911 | −0.071263 | −0.023158 | 0.052272 | 0.068643 | 0.038074 | 0.006633 | −0.08155 |
| 156 | 770.6/190.1>GPEtn:20:2/18:0 | 0.000083 | −0.02827 | 0.064449 | −0.089016 | −0.040853 | −0.011272 | 0.000823 | −0.013653 | 0.059649 | −0.104055 |
| 157 | 772.6/190.1>GPEtn:20:1/18:0 | −0.026039 | 0.014821 | 0.066929 | −0.129553 | −0.03127 | −0.024394 | 0.019665 | −0.072402 | −0.026535 | −0.056969 |
| 158 | 770.6/190.1>GPEtn:40:5p, 40:6e | −0.006718 | 0.001678 | 0.037603 | −0.028384 | −0.021154 | −0.013743 | 0.048264 | −0.047366 | 0.060737 | −0.067309 |
| 159 | 778.6/190.1>GPEtn:40:4p, 40:5e | −0.030284 | 0.037443 | −0.027856 | −0.015058 | 0.009165 | 0.012056 | 0.039424 | −0.013024 | 0.054217 | −0.061476 |
| 160 | 780.6/190.1>GPEtn:40:3p, 40:4e | −0.008664 | 0.022385 | 0.00337 | −0.030252 | 0.009359 | 0.002008 | 0.000775 | −0.01225 | 0.045231 | −0.001256 |
| 161 | 784.6/190.1>GPEtn:40:1p, 40:2e | −0.024599 | 0.006677 | 0.023335 | −0.067156 | −0.004711 | −0.006494 | 0.003196 | −0.042444 | 0.072606 | −0.102262 |
| 162 | 788.8/190.1>GPEtn:22:4/18:3 | −0.004232 | −0.061655 | 0.075118 | −0.056273 | 0.019669 | 0.032304 | 0.022675 | −0.043176 | −0.006405 | −0.09019 |
| 163 | 790.8/190.1>GPEtn:22:4/18:2 | 0.026265 | −0.080197 | −0.015209 | −0.07173 | 0.012416 | 0.059898 | 0.029514 | −0.088571 | −0.003094 | −0.130057 |
| 164 | 792.6/190.1>GPEtn:40:5a | 0.029626 | −0.062785 | −0.016804 | −0.061867 | −0.01726 | 0.091861 | 0.065935 | 0.033463 | −0.008621 | −0.040099 |
| 165 | 794.6/190.1>GPEtn:40:4a | 0.027241 | −0.036207 | −0.010697 | −0.092714 | −0.027612 | 0.049437 | 0.041325 | −0.035386 | 0.0329 | −0.070926 |
| 166 | 790.8/190.1>GPEtn:40:3a | −0.02203 | 0.0482 | −0.003991 | −0.024547 | −0.024275 | 0.036054 | 0.023546 | 0.00385 | −0.085743 | 0.063955 |
| 167 | 798.6/190.1>GPEtn:40:2a | −0.038308 | 0.028048 | 0.056192 | −0.098884 | −0.049881 | −0.018799 | 0.006721 | −0.058677 | 0.041173 | −0.082599 |
| 168 | 569.4/241.1>GPIns:Lyso 16:1 | 0.024694 | −0.008646 | 0.007463 | −0.028355 | 0.075407 | −0.044688 | 0.133659 | −0.000725 | −0.0843 | −0.052996 |
| 169 | 571.3/241.1>GPIns:Lyso 16:0 | −0.028995 | 0.043925 | 0.033958 | −0.088039 | 0.088149 | −0.092073 | 0.018401 | −0.05571 | −0.05921 | 0.029477 |
| 170 | 595.4/241.1>GPIns:Lyso 18:2 | −0.026605 | 0.049467 | 0.011099 | −0.057553 | 0.097752 | −0.096354 | −0.018612 | −0.054915 | −0.036565 | 0.039831 |
| 171 | 597.4/241.1>GPIns:Lyso 18:1 | −0.006997 | 0.007485 | 0.065465 | −0.064414 | 0.081954 | −0.136702 | 0.03739 | −0.051306 | −0.068554 | 0.029754 |
| 172 | 599.4/241.1>GPIns:Lyso 18:0 | −0.040622 | 0.016975 | 0.033038 | −0.098811 | 0.071984 | −0.090527 | 0.077792 | −0.046308 | −0.099952 | 0.037047 |
| 173 | 619.5/241.1>GPIns:Lyso 20:4 | 0.022192 | −0.090065 | −0.01106 | −0.024939 | 0.116291 | −0.075351 | 0.076299 | −0.025363 | −0.086258 | −0.018081 |
| 174 | 621.5/241.1>GPIns:Lyso 20:3 | 0.038817 | −0.068337 | 0.012475 | −0.009529 | 0.06247 | −0.098366 | 0.110484 | −0.02135 | −0.079676 | −0.071548 |
| 175 | 623.5/241.1>GPIns:Lyso 20:2 | 0.021232 | −0.046425 | 0.040642 | −0.049245 | 0.047777 | −0.111615 | 0.071853 | −0.046158 | −0.066651 | −0.03989 |
| 176 | 625.5/241.1>GPIns:Lyso 20:1 | −0.023271 | 0.042654 | 0.069063 | −0.107497 | 0.013742 | −0.079926 | 0.036724 | −0.056154 | −0.059042 | 0.031418 |
| 177 | 627.5/241.1>GPIns:Lyso 20:0 | 0.006165 | 0.041146 | 0.024821 | 0.000077 | 0.071007 | −0.023043 | 0.048404 | 0.037884 | 0.00509k | 0.089029 |
| 178 | 679.5/241.1>GPIns:Lyso 24:2 | 0.030445 | 0.093314 | 0.02535 | −0.072989 | 0.099334 | −0.006017 | −0.020473 | −0.035298 | 0.043959 | −0.006372 |
| 179 | 835.7/241.1>GPIns:34:1 | 0.047136 | 0.117145 | 0.016675 | −0.026798 | 0.07247 | 0.012677 | −0.026728 | −0.013432 | 0.043715 | −0.012099 |
| 180 | 857.7/241.1>GPIns:36:4 | 0.047898 | 0.112232 | 0.00155 | −0.022801 | 0.087698 | 0.020677 | −0.03105 | −0.009777 | 0.047914 | −0.019112 |
| 181 | 859.8/241.1>GPIns:36:3 | 0.037336 | 0.121473 | 0.012315 | −0.019202 | 0.073428 | 0.005356 | −0.042069 | −0.006609 | 0.050652 | −0.004354 |
| 182 | 861.8/241.1>GPIns:36:2 | 0.05237 | 0.114905 | 0.001845 | −0.013522 | 0.060496 | 0.004423 | −0.044442 | −0.020278 | 0.046725 | 0.002162 |
| 183 | 863.7/241.1>GPIns:36:1 | 0.064912 | 0.101152 | 0.037496 | 0.004344 | 0.016306 | −0.025573 | −0.016423 | −0.014741 | 0.055518 | −0.026293 |
| 184 | 865.8/241.1>GPIns:36:0 | 0.059982 | 0.073228 | 0.065152 | −0.050466 | 0.042642 | −0.023331 | 0.00753 | −0.01836 | 0.028629 | −0.041147 |
| 185 | 873.8/241.1>GPIns:37:3 | 0.066088 | 0.057464 | 0.036025 | −0.006 | 0.042128 | 0.02067 | 0.059951 | 0.018325 | 0.054076 | −0.061287 |
| 186 | 883.8/241.1>GPIns:38:5 | 0.053225 | 0.072512 | 0.012006 | 0.026813 | 0.00738 | −0.02688 | 0.05497 | 0.026189 | 0.044314 | −0.049848 |
| 187 | 885.8/241.1>GPIns:38:4 | 0.092627 | −0.009489 | −0.042495 | 0.020767 | 0.048796 | 0.043159 | 0.024194 | −0.022393 | 0.032324 | −0.080875 |
| 188 | 887.8/241.1>GPIns:38:3 | 0.092179 | 0.004043 | −0.025295 | 0.032706 | 0.018399 | 0.017033 | 0.050659 | −0.006824 | 0.029839 | −0.107957 |
| 189 | 889.8/241.1>GPIns:38:2 | 0.08255 | 0.035637 | 0.031264 | −0.036226 | 0.05051 | −0.009866 | 0.027443 | −0.004773 | 0.013527 | −0.060301 |
| 190 | 891.8/241.1>GPIns:38:1 | −0.031784 | 0.10573 | 0.034051 | −0.108592 | −0.009461 | −0.005749 | −0.028517 | −0.075174 | 0.005489 | −0.008076 |
| 191 | 893.8/241.1>GPIns:38:0 | −0.033686 | 0.081484 | 0.028383 | −0.118149 | −0.004701 | −0.009264 | −0.035888 | −0.10229 | 0.00656 | −0.057571 |
| 192 | 909.8/241.1>GPIns:40:6 | 0.084284 | −0.028354 | −0.032856 | 0.029658 | 0.054342 | 0.029788 | 0.035409 | −0.041744 | 0.064852 | −0.06794 |
| 193 | 911.8/241.1>GPIns:40:5 | 0.083919 | 0.008816 | −0.039538 | 0.058926 | 0.037198 | 0.019125 | 0.040977 | −0.036864 | 0.061635 | −0.091301 |
| 194 | 913.8/241.1>GPIns:40:4 | 0.057061 | 0.080119 | −0.011014 | 0.025131 | −0.003808 | 0.007862 | 0.055747 | 0.001086 | 0.051564 | −0.112443 |
| 195 | 915.8/241.1>GPIns:40:3 | −0.016271 | 0.123658 | 0.004473 | −0.023227 | −0.057049 | 0.036838 | −0.004575 | 0.02264 | 0.004691 | −0.004135 |
| 193 | 917.8/241.1>GPIns:40:2 | −0.009858 | 0.143731 | 0.024526 | −0.036061 | 0.008753 | 0.008757 | −0.022412 | 0.008174 | 0.028327 | 0.004874 |
| 197 | 919.8/241.1>GPIns:40:1 | −0.04028 | 0.104291 | 0.01622 | −0.098204 | −0.017349 | −0.013709 | −0.017571 | −0.06582 | 0.010293 | −0.037461 |
| 198 | 963.9/241.1>GPInsP: 38:5 | −0.054633 | 0.079019 | 0.022424 | −0.043429 | −0.069886 | 0.007296 | 0.035163 | −0.000987 | −0.001847 | 0.013068 |
| 199 | 963.9/321.1>GPInsP: 38:5 | −0.023563 | 0.006282 | 0.030393 | −0.055506 | 0.029819 | −0.007008 | −0.001076 | −0.061874 | −0.028105 | −0.049418 |
| 200 | 965.9/241.1>GPInsP: 38:4 | −0.062202 | 0.085371 | 0.040908 | 0.019071 | −0.036685 | 0.010172 | 0.047302 | −0.004463 | 0.000683 | 0.040968 |

APPENDIX B1-continued

PCA Transformation Matrix(340 × 340; Normal/Diseased)

| | | | | | | | | | | | |
|---|---|---|---|---|---|---|---|---|---|---|---|
| 201 | 965.9/321.1>GPInsP: 38:4 | −0.044461 | −0.005052 | 0.073832 | −0.00295 | −0.030603 | 0.006493 | 0.0376 | −0.056886 | 0.056031 | −0.055706 |
| 202 | 967.9/241.1>GPInsP: 38:3 | −0.052515 | 0.091059 | −0.001016 | −0.006152 | −0.057309 | −0.007944 | 0.035995 | 0.019571 | −0.028666 | 0.043429 |
| 203 | 967.9/321.1>GPInsP: 38:3 | −0.063827 | 0.053574 | 0.01205 | −0.016594 | −0.010818 | −0.025706 | 0.090665 | −0.005536 | 0.00963 | −0.026836 |
| 204 | 1045.9/241.1>GPInsP2: 38:4 | −0.042098 | 0.075571 | −0.004199 | −0.035684 | −0.004479 | −0.00549 | −0.0088 | −0.050291 | 0.052674 | −0.045028 |
| 205 | 1045.9/321.1>GPInsP2: 38:4 | −0.008846 | −0.002681 | −0.016822 | 0.022818 | 0.021529 | 0.009931 | 0.009995 | 0.017213 | −0.00106 | 0.016609 |
| 206 | 1045.9/401.1>GPInsP2: 38:4 | −0.018694 | −0.002087 | −0.022492 | −0.013444 | 0.039441 | −0.01549 | 0.008899 | −0.035909 | −0.033505 | 0.048633 |
| 207 | 1047.9/321.1>GPInsP2: 38:3 | −0.010429 | 0.029762 | −0.01688 | −0.016204 | 0.027898 | −0.000644 | 0.036314 | −0.005312 | −0.013019 | 0.017717 |
| 208 | 1047.9/401.1>GPInsP2: 38:3 | −0.051318 | 0.028272 | 0.014625 | −0.007886 | −0.025941 | −0.007579 | 0.056564 | −0.006241 | −0.010083 | 0.035479 |
| 209 | 1047.9/241.1>GPInsP2: 38:3 | −0.012971 | 0.066843 | 0.033962 | 0.022543 | 0.006299 | −0.039744 | 0.035084 | 0.03293 | −0.026648 | −0.00684 |
| 210 | 1125.9/241.1>GPInsP3: 38:4 | −0.029984 | 0.022336 | 0.009533 | −0.041555 | −0.004964 | 0.004978 | 0.029538 | −0.031664 | −0.012937 | −0.076692 |
| 211 | 1125.9/321.1>GPInsP3: 38:4 | −0.016222 | 0.005081 | 0.037337 | −0.088062 | 0.033587 | −0.039649 | −0.011707 | −0.086866 | −0.066699 | 0.005795 |
| 212 | 1125.9/401.1>GPInsP3: 38:4 | 0.002503 | −0.006292 | 0.015156 | −0.033318 | 0.020684 | 0.008745 | 0.026705 | 0.049713 | −0.047974 | 0.120103 |
| 313 | 1125.9/481.1>GPInsP3: 38:4 | 0.001688 | 0.034477 | 0.009375 | 0.036789 | 0.019359 | 0.025614 | −0.017599 | −0.010838 | −0.003297 | −0.037414 |
| 214 | 835.7/281.1>GPIns:34:1 | 0.055555 | 0.093827 | 0.040725 | −0.058094 | 0.090749 | 0.011097 | −0.028752 | −0.017544 | 0.020652 | −0.001589 |
| 215 | 821.8/241.1>GPIns:34:1 | 0.042299 | 0.09628 | 0.029048 | −0.027608 | 0.053283 | 0.000755 | −0.001673 | −0.011709 | 0.04332 | −0.028917 |
| 216 | 494.4/184.1>GPCho:Lyso 16:1 | −0.005425 | 0.018504 | 0.009556 | 0.033844 | −0.0302 | −0.06527 | 0.170462 | 0.053986 | −0.039506 | −0.083631 |
| 217 | 490.4/184.1>GPCho:Lyso 16:0 | −0.066126 | 0.012355 | −0.004211 | 0.006934 | −0.014294 | −0.057034 | 0.082672 | 0.040368 | 0.008565 | −0.006249 |
| 218 | 520.4/184.1>GPCho:Lyso 18:2 | −0.031768 | −0.081888 | 0.047774 | 0.022534 | −0.018942 | −0.171281 | 0.005934 | 0.018953 | −0.008523 | 0.02214 |
| 219 | 522.4/184.1>GPCho:Lyso 18:1 | −0.067633 | −0.033223 | 0.01147 | 0.028339 | −0.013025 | −0.083018 | 0.104993 | 0.041152 | −0.044027 | −0.021797 |
| 220 | 524.4/184.1>GPCho:Lyso 18:0 | −0.053824 | 0.004731 | 0.02349 | 0.011861 | −0.047669 | −0.132787 | 0.078538 | 0.020155 | 0.014851 | −0.059778 |
| 221 | 544.4/184.1>GPCho:Lyso 20:4 | 0.009079 | −0.113672 | −0.061953 | 0.029582 | 0.071692 | −0.023508 | 0.045904 | −0.028469 | 0.005183 | −0.071705 |
| 222 | 568.4/184.1>GPCho:Lyso 22:6 | 0.00969 | −0.10272 | −0.06014 | 0.039531 | 0.078663 | −0.042984 | 0.019162 | −0.031702 | 0.048719 | −0.053214 |
| 223 | 570.4/184.1>GPCho:Lyso 22:5 | 0.018146 | −0.099415 | −0.051319 | 0.054599 | 0.063676 | −0.064047 | 0.0507 | −0.020122 | 0.033002 | −0.083974 |
| 224 | 678.5/184.1>GPCho:28:0 | −0.032149 | 0.043386 | 0.057997 | 0.015684 | −0.096127 | −0.057057 | 0.063407 | 0.037367 | 0.050428 | −0.013138 |
| 225 | 678.5/184.1>GPCho:28:0a | −0.034025 | 0.036836 | 0.062729 | 0.014871 | −0.094784 | −0.060085 | 0.06687 | 0.036623 | 0.04972 | −0.019595 |
| 226 | 704.6/184.1>GPCho:30:1a | −0.100886 | −0.029821 | −0.052553 | −0.006016 | 0.041317 | 0.019222 | −0.06476 | −0.054353 | −0.033444 | 0.077863 |
| 227 | 700.6/184.1>GPCho:30:0a | −0.074351 | −0.013336 | −0.017934 | 0.03468 | −0.01786 | −0.015687 | −0.000051 | −0.038735 | 0.008269 | −0.010994 |
| 228 | 718.6/184.1>GPCho:32:0p, 32:1e | −0.068625 | 0.042173 | 0.014533 | 0.00974 | −0.002198 | −0.04024 | −0.017299 | −0.076711 | 0.069236 | 0.053207 |
| 229 | 730.8/184.1>GPCho:32:2 | −0.064165 | 0.007089 | −0.040926 | −0.006294 | 0.010464 | −0.023482 | −0.004832 | −0.069965 | −0.014066 | −0.005494 |
| 230 | 732.6/184.1>GPCho:32:1a | −0.043001 | 0.059522 | −0.049222 | −0.026547 | −0.009465 | 0.088029 | 0.116685 | −0.003355 | −0.067338 | −0.059277 |
| 231 | 734.6/184.1>GPCho:32:0a | −0.039067 | 0.064453 | −0.043912 | −0.003799 | 0.000326 | 0.138467 | 0.031229 | −0.0177 | −0.037294 | 0.050407 |
| 232 | 742.6/184.1>GPCho:34:2p, 34:3e | −0.02934 | 0.057911 | 0.078321 | 0.065671 | −0.040247 | −0.086549 | −0.016453 | −0.007451 | 0.050122 | 0.033263 |
| 233 | 744.6/184.1>GPCho:34:1p, 34:2e | 0.041768 | −0.022143 | 0.079397 | 0.071254 | −0.029675 | −0.127978 | −0.059236 | 0.021223 | 0.057587 | 0.028872 |
| 234 | 740.6/184.1>GPCho:34:0p, 34:1e | −0.008644 | 0.06009 | 0.036587 | 0.042602 | 0.030452 | 0.009806 | −0.006687 | 0.002754 | 0.047842 | 0.094738 |
| 235 | 748.6/184.1>GPCho:34:0e | −0.026847 | 0.086912 | 0.026179 | 0.017943 | 0.012284 | 0.022227 | −0.022316 | −0.036871 | 0.08368 | 0.061008 |
| 236 | 750.6/184.1>GPCho:34:3a | −0.032985 | 0.115475 | 0.06783 | −0.023817 | −0.060651 | −0.032716 | 0.014694 | 0.045216 | −0.024 | 0.049365 |
| 237 | 758.7/184.1>GPCho:34:2a | 0.0658 | 0.019386 | 0.083651 | −0.028971 | −0.022078 | 0.025235 | −0.071214 | 0.063685 | −0.001275 | 0.070721 |
| 238 | 760.6/184.1>GPCho:34:1a | 0.02728 | 0.086348 | 0.000073 | −0.012183 | −0.016882 | 0.13059 | 0.082015 | 0.068107 | −0.035036 | 0.00189 |
| 239 | 762.6/184.1>GPCho:34:0a | 0.015714 | 0.086084 | −0.015634 | 0.002646 | −0.040603 | 0.117025 | 0.110244 | 0.052622 | −0.048323 | −0.00776 |
| 240 | 768.6/184.1>GPCho:36:3p, 36:4e | 0.069271 | −0.065922 | −0.015791 | 0.068294 | 0.079555 | −0.016412 | −0.013905 | −0.02915 | 0.051361 | −0.02005 |
| 241 | 770.6/184.1>GPCho:36:2p, 36:3e | 0.057877 | −0.017785 | 0.0518851 | 0.090876 | 0.023 | −0.111677 | −0.037816 | 0.009724 | 0.063845 | −0.005859 |
| 242 | 772.6/184.1>GPCho:36:1p, 36:2e | 0.018568 | 0.076198 | 0.087798 | 0.021536 | −0.037685 | −0.090421 | −0.043206 | 0.011165 | 0.07717 | 0.052019 |
| 243 | 774.6/184.1>GPCho:36:0p, 36:1e | 0.009612 | 0.092968 | 0.045466 | 0.020997 | −0.011564 | −0.039424 | −0.002493 | −0.007776 | 0.122596 | −0.015816 |
| 244 | 782.6/184.1>GPCho:36:4a | −0.08743 | −0.041915 | −0.043373 | 0.02195 | 0.037735 | 0.090976 | 0.013272 | −0.010563 | 0.01911 | −0.067666 |
| 245 | 784.6/184.1>GPCho:36:3a | 0.096564 | −0.005334 | 0.039337 | 0.037215 | −0.033421 | −0.014958 | 0.051395 | 0.039818 | 0.028246 | −0.09081 |
| 246 | 780.6/184.1>GPCho:36:2a | 0.073235 | −0.000703 | 0.087411 | −0.004394 | −0.073539 | −0.10067 | −0.004126 | 0.062138 | 0.027759 | −0.01655 |
| 247 | 788.6/184.1>GPCho:36:1a | 0.000188 | 0.098328 | 0.06633 | −0.027947 | −0.110892 | −0.060577 | 0.059775 | 0.040771 | −0.006497 | −0.041208 |
| 248 | 790.8/184.1>GPCho:36:0 | −0.015147 | 0.117778 | 0.042917 | 0.001595 | −0.090689 | −0.038865 | 0.058102 | 0.016096 | 0.005392 | −0.052266 |
| 249 | 792.6/184.1>GPCho:38:5p, 38:6e | 0.047858 | −0.038225 | −0.017877 | 0.076692 | 0.059437 | −0.027078 | −0.014994 | −0.029446 | 0.101371 | −0.017185 |
| 250 | 794.6/184.1>GPCho:38:4p, 38:5e | 0.065899 | −0.057774 | −0.032489 | 0.066911 | 0.102539 | 0.002753 | −0.022983 | −0.025122 | 0.069695 | −0.01382 |
| 251 | 790.6/184.1>GPCho:38:3p, 38:4e | 0.067508 | −0.032644 | −0.026721 | 0.072074 | 0.101053 | 0.013807 | −0.033088 | −0.021678 | 0.101181 | −0.021095 |

APPENDIX B1-continued

PCA Transformation Matrix(340 × 340; Normal/Diseased)

| | | | | | | | | | | | |
|---|---|---|---|---|---|---|---|---|---|---|---|
| 252 | 798.6/184.1>GPCho:38:2p, 38:3e | 0.042036 | 0.096672 | 0.033529 | 0.033599 | 0.036091 | 0.011236 | −0.019769 | 0.016556 | 0.112756 | −0.011409 |
| 253 | 800.6/184.1>GPCho:38:1p, 38:2e | −0.048269 | 0.076214 | 0.032415 | 0.023994 | 0.000213 | −0.075519 | −0.054029 | −0.027932 | 0.082212 | 0.054523 |
| 254 | 808.6/184.1>GPCho:38:5a | 0.093019 | −0.042904 | −0.043013 | 0.045803 | 0.038016 | 0.030162 | 0.031484 | −0.007155 | 0.073945 | −0.093814 |
| 255 | 810.6/184.1>GPCho:38:4a | 0.092056 | −0.028924 | −0.047293 | 0.02646 | 0.035962 | 0.057324 | 0.027818 | −0.018411 | 0.039242 | −0.106964 |
| 256 | 812.6/184.1>GPCho:38:3a | 0.046431 | 0.037731 | −0.03753 | 0.03411 | −0.006515 | 0.033854 | 0.068401 | −0.027461 | 0.033436 | −0.151343 |
| 257 | 814.6/184.1>GPCho:38:2a | −0.10408 | 0.039064 | −0.061731 | −0.009572 | 0.029254 | 0.035466 | −0.031758 | −0.074536 | −0.011788 | 0.020576 |
| 258 | 810.6/184.1>GPCho:38:1a | −0.079995 | 0.068931 | 0.005327 | −0.030111 | −0.051175 | −0.070191 | −0.055383 | −0.050242 | 0.009759 | 0.013383 |
| 259 | 820.6/184.1>GPCho:40:5p, 40:6e | 0.069602 | −0.038792 | −0.030395 | 0.065025 | 0.080062 | −0.011209 | −0.033233 | −0.037884 | 0.124248 | −0.026102 |
| 260 | 822.6/184.1>GPCho:40:4p, 40:5e | 0.050379 | 0.064562 | −0.0016 | 0.036248 | 0.062756 | 0.030632 | −0.039454 | −0.011857 | 0.118812 | 0.009951 |
| 261 | 824.6/184.1>GPCho:40:3p, 40:4e | 0.037121 | 0.095346 | 0.006101 | 0.027438 | 0.046484 | 0.042958 | −0.036249 | 0.019973 | 0.116617 | 0.019611 |
| 262 | 820.6/184.1>GPCho:40:2p, 40:3e | −0.040032 | 0.129441 | 0.046588 | −0.038574 | −0.023193 | 0.017828 | −0.004408 | 0.03428 | 0.030228 | 0.052262 |
| 263 | 828.6/184.1>GPCho:40:1p, 40:2e | −0.059383 | 0.102388 | 0.044606 | −0.050425 | −0.017013 | 0.033243 | −0.015059 | 0.055953 | 0.082553 | 0.050472 |
| 264 | 834.6/184.1>GPCho:40:6a | 0.077024 | −0.04092 | −0.053904 | 0.047446 | 0.038371 | 0.020502 | 0.027505 | −0.025487 | 0.076004 | −0.092977 |
| 265 | 830.6/184.1>GPCho:40:5a | 0.067107 | 0.045003 | −0.034569 | 0.024566 | −0.021159 | 0.042641 | 0.043151 | −0.00924 | 0.082723 | −0.097389 |
| 266 | 838.6/184.1>GPCho:40:4a | 0.040493 | 0.100277 | 0.001486 | 0.00364 | −0.050233 | 0.042736 | 0.053219 | 0.025669 | 0.052523 | −0.081128 |
| 267 | 701.5/184.1>SM:18/16:1 | −0.088989 | −0.031524 | −0.049358 | −0.0099 | 0.029035 | −0.027226 | −0.04622 | −0.029625 | −0.025892 | 0.065231 |
| 268 | 703.5/184.1>SM:18/16:0 | −0.10443 | −0.041731 | −0.047221 | −0.02837 | 0.040971 | 0.015614 | −0.056839 | −0.034623 | −0.018974 | 0.070243 |
| 269 | 703.8/184.4>SM:d18:1/16:0 | −0.100397 | −0.028907 | −0.058229 | −0.003809 | 0.05473 | 0.01777 | −0.073645 | −0.055485 | −0.019812 | 0.070677 |
| 270 | 705.8/184.4>SM: d18:0/16:0 | −0.100699 | −0.030848 | −0.061691 | 0.000094 | 0.035648 | 0.017317 | −0.058534 | −0.068927 | −0.029149 | 0.041989 |
| 271 | 727.6/184.1>SM:18/18:2 | −0.062192 | 0.034176 | 0.003376 | −0.03124 | 0.01259 | −0.036731 | −0.062214 | −0.092878 | 0.002414 | 0.008374 |
| 272 | 729.6/184.1>SM:18/18:1 | −0.081835 | 0.001602 | −0.059986 | −0.042653 | 0.04558 | 0.040591 | −0.023858 | −0.075154 | −0.036489 | 0.028975 |
| 273 | 731.6/184.1>SM:18/18:0 | −0.093006 | 0.006391 | −0.068758 | −0.047277 | 0.027371 | 0.067163 | −0.01609 | −0.084166 | −0.043131 | 0.010486 |
| 274 | 731.8/184.4>SM: d18:1/18:0 | −0.091697 | 0.00865 | −0.072936 | −0.038578 | 0.031316 | 0.068903 | −0.018929 | −0.085678 | −0.0446 | 0.012519 |
| 275 | 733.8/184.4>SM: d18:0/18:0 | −0.059697 | 0.046748 | −0.065795 | −0.036937 | 0.000413 | 0.099457 | 0.074973 | −0.038589 | −0.062148 | −0.065012 |
| 276 | 757.6/184.1>SM:18/20:1 | −0.056148 | 0.100633 | 0.048969 | −0.026461 | −0.04066 | −0.046547 | −0.008988 | 0.015101 | −0.029897 | 0.059379 |
| 277 | 759.6/184.1>SM:18/20:0 | 0.073739 | 0.007867 | 0.056849 | −0.003726 | −0.0721 | −0.027392 | −0.083835 | 0.06182 | 0.013909 | 0.072093 |
| 278 | 759.8/184.4>SM: d18:1/20:0 | 0.071244 | −0.000971 | 0.063051 | 0.002417 | −0.072799 | −0.037462 | −0.07709 | 0.048824 | −0.007195 | 0.07859 |
| 279 | 761.8/184.4>SM: d18:0/20:0 | 0.018167 | 0.081613 | −0.012334 | 0.010554 | −0.033404 | 0.113157 | 0.100773 | 0.062522 | −0.04772 | −0.002493 |
| 280 | 773.6/184.1>SM:18/21:0 | −0.008113 | 0.016043 | 0.035811 | 0.033425 | −0.047877 | −0.120388 | −0.0612 | −0.043273 | 0.102708 | 0.016918 |
| 281 | 787.6/184.1>SM:18/22:0 | 0.027966 | −0.005049 | 0.058573 | 0.020927 | −0.100824 | −0.15353 | −0.037391 | 0.019534 | 0.039764 | −0.038134 |
| 282 | 787.9/184.4>SM: d18:1/22:0 | 0.010578 | −0.007658 | 0.04586 | 0.024856 | −0.081556 | −0.177509 | −0.048732 | −0.025605 | 0.002132 | −0.033832 |
| 283 | 789.9/184.4>SM: d18:0/22:0 | −0.005775 | 0.096029 | 0.052668 | −0.015747 | −0.095214 | −0.045496 | 0.069952 | 0.028424 | −0.022178 | −0.051108 |
| 284 | 813.6/184.1>SM:18/24:1 | −0.101972 | 0.010778 | −0.074285 | −0.004394 | 0.047097 | 0.045343 | −0.034132 | −0.087407 | −0.010595 | 0.013045 |
| 285 | 813.9/184.4>SM: d18:1/24:1 | −0.100891 | 0.008393 | −0.071288 | 0.001744 | 0.048245 | 0.040035 | −0.037076 | −0.092325 | −0.020349 | 0.020523 |
| 286 | 815.6/184.1>SM:18/24:0 | −0.083879 | −0.001737 | −0.066435 | 0.02672 | 0.014752 | −0.051644 | −0.08079 | −0.087197 | 0.011866 | −0.006135 |
| 287 | 815.9/184.4>SM: d18:0/24:1 | −0.079455 | −0.035952 | −0.042576 | −0.025342 | 0.022042 | −0.047273 | −0.087196 | −0.087255 | −0.001396 | 0.013903 |
| 288 | 817.9/184.4>SM: d18:0/24:0 | −0.027589 | 0.080378 | 0.032588 | −0.06016 | −0.018573 | −0.058138 | −0.058037 | −0.055367 | 0.005254 | 0.037188 |
| 289 | 841.9/184.4>SM: d18:1/26:1 | −0.050894 | 0.1127 | 0.03242 | −0.063669 | −0.047203 | 0.018373 | 0.001122 | −0.021974 | −0.008654 | 0.03723 |
| 290 | 843.9/184.4>SM: d18:0/26:1 | 0.069477 | 0.034935 | 0.030595 | −0.041014 | 0.042206 | 0.038507 | 0.013522 | 0.024098 | 0.029343 | 0.053701 |
| 291 | 843.9/184.4>SM: d18:1/26:0 | 0.069864 | 0.037421 | 0.029489 | −0.038501 | 0.042405 | 0.035168 | 0.014293 | 0.019642 | 0.025249 | 0.052345 |
| 292 | 845.9/184.4>SM: d18:0/26:0 | 0.067518 | 0.039665 | 0.015161 | −0.026493 | 0.058778 | 0.06045 | 0.035718 | 0.032173 | 0.035383 | 0.032965 |
| 293 | 538.7/264.4>Cer: d18:1/16:0 | −0.081671 | −0.028482 | −0.022803 | −0.028836 | 0.10822 | −0.003116 | 0.030613 | 0.04176 | 0.012135 | 0.02178 |
| 294 | 540.7/260.4>Cer: d18:0/16:0 | −0.112976 | −0.040381 | −0.011263 | −0.031203 | 0.032786 | 0.008232 | 0.017742 | 0.002939 | 0.005903 | −0.012814 |
| 295 | 560.7/264.4>Cer: d18:1/18:0 | −0.096464 | 0.004918 | −0.041724 | −0.056698 | 0.045891 | 0.050414 | 0.033671 | −0.033381 | −0.041593 | −0.020064 |
| 296 | 568.7/260.4>Cer: d18:0/18:0 | −0.095406 | −0.032162 | −0.039353 | −0.05126 | 0.003848 | 0.066614 | 0.009127 | 0.033216 | 0.027079 | −0.004445 |
| 297 | 594.7/264.4>Cer: d18:1/20:0 | −0.106277 | −0.015611 | −0.025823 | −0.051478 | 0.024807 | 0.041877 | 0.035279 | 0.014256 | −0.008418 | −0.001582 |
| 298 | 590.7/260.4>Cer: d18:0/20:0 | −0.072024 | 0.043845 | −0.024288 | 0.016228 | 0.084222 | 0.005741 | 0.011443 | 0.028823 | 0.048047 | −0.053485 |
| 299 | 622.8/264.4>Cer: d18:1/22:0 | −0.108979 | −0.031914 | −0.014411 | −0.022147 | −0.002941 | −0.003694 | 0.026732 | 0.04752 | 0.022397 | −0.035514 |
| 300 | 624.8/260.4>Cer: d18:0/22:0 | −0.001949 | 0.071665 | 0.014275 | −0.02713 | 0.103132 | 0.027549 | −0.034951 | 0.001603 | 0.047801 | −0.013576 |
| 301 | 648.9/264.4>Cer: d18:1/24:1 | −0.114834 | −0.003176 | −0.033233 | −0.021612 | 0.0354 | 0.038193 | 0.030352 | 0.003672 | −0.011987 | −0.013092 |
| 302 | 650.9/260.4>Cer: d18:0/24:1 | −0.110893 | −0.027429 | −0.033317 | −0.028988 | −0.011621 | 0.045933 | 0.029423 | 0.025443 | 0.028852 | −0.022536 |

APPENDIX B1-continued

PCA Transformation Matrix(340 × 340; Normal/Diseased)

| | | | | | | | | | | | |
|---|---|---|---|---|---|---|---|---|---|---|---|
| 303 | 650.9/264.4>Cer: d18:1/24:0 | −0.097066 | −0.045965 | −0.005997 | 0.020459 | −0.056436 | −0.027201 | 0.00482 | 0.019454 | 0.032105 | −0.034434 |
| 304 | 652.9/260.4>Cer: d18:0/24:0 | −0.090799 | −0.058164 | −0.013807 | −0.002016 | −0.050461 | −0.013956 | 0.003233 | 0.056739 | 0.064907 | −0.016165 |
| 305 | 670.9/264.4>Cer: d18:1/26:1 | −0.102139 | 0.017725 | −0.041193 | 0.005218 | 0.005478 | 0.034015 | 0.030693 | −0.033251 | −0.023365 | 0.003372 |
| 306 | 678.9/260.4>Cer: d18:0/26:1 | −0.035018 | −0.055373 | 0.032694 | −0.059622 | −0.003467 | 0.039188 | 0.017831 | 0.153842 | 0.099266 | 0.029568 |
| 307 | 678.9/264.4>Cer: d18:1/26:0 | −0.051031 | 0.028146 | 0.040513 | 0.034284 | 0.00785 | −0.038371 | 0.033338 | 0.026951 | 0.021693 | −0.007997 |
| 308 | 680.9/260.4>Cer: d18:0/26:0 | −0.013942 | −0.05412 | 0.014181 | −0.061772 | −0.005409 | 0.025647 | −0.02215 | 0.143509 | 0.109343 | 0.053177 |
| 309 | 700.7/264.4>MonoHexCer:d18:1/16:0 | −0.093441 | −0.066556 | −0.0099 | −0.037818 | −0.005274 | 0.038883 | −0.037747 | 0.086455 | 0.08371 | 0.031229 |
| 310 | 702.7/260.4>MonoHexCer:d18:0/16:0 | −0.066004 | −0.04965 | 0.013454 | −0.036922 | −0.027328 | 0.027982 | 0.000522 | 0.129142 | 0.109671 | 0.034565 |
| 311 | 728.7/264.4>MonoHexCer:d18:1/18:0 | −0.116366 | −0.035275 | −0.019247 | 0.005247 | 0.012577 | 0.016304 | −0.020917 | −0.002818 | 0.013837 | −0.013146 |
| 312 | 730.7/260.4>MonoHexCer:d18:0/18:0 | −0.06663 | −0.001819 | 0.0521 | −0.034233 | −0.037685 | 0.022729 | 0.012984 | −0.054482 | 0.032966 | −0.079693 |
| 313 | 750.7/264.4>MonoHexCer:d18:1/20:0 | −0.104458 | −0.062298 | 0.000774 | −0.004368 | −0.003991 | 0.024321 | −0.014401 | 0.052083 | 0.060607 | 0.00501 |
| 314 | 758.7/260.4>MonoHexCer:d18:0/20:0 | −0.059226 | −0.016067 | 0.006201 | −0.037667 | −0.037038 | 0.025751 | 0.029413 | 0.04022 | 0.016112 | −0.030405 |
| 315 | 784.8/264.4>MonoHexCer:d18:1/22:0 | −0.09291 | −0.07521 | −0.006279 | −0.022238 | −0.017439 | 0.00262 | −0.054086 | 0.069156 | 0.088232 | 0.005784 |
| 316 | 780.8/260.4>MonoHexCer:d18:0/22:0 | −0.070802 | 0.010144 | −0.004934 | −0.013803 | −0.030498 | −0.011344 | −0.058772 | −0.004389 | 0.018578 | −0.024384 |
| 317 | 810.9/264.4>MonoHexCer:d18:1/24:1 | −0.104884 | −0.052794 | −0.024156 | −0.01741 | 0.009774 | 0.045081 | −0.034109 | 0.040499 | 0.070154 | 0.010709 |
| 318 | 812.9/260.4>MonoHexCer:d18:0/24:1 | −0.083584 | −0.065761 | −0.023889 | −0.0221 | −0.001599 | 0.037633 | −0.029203 | 0.084983 | 0.105726 | 0.04407 |
| 319 | 812.9/264.4>MonoHexCer:d18:1/24:0 | −0.083744 | −0.077156 | −0.005128 | −0.029543 | −0.018526 | 0.011794 | −0.048559 | 0.083988 | 0.107765 | 0.015524 |
| 320 | 814.9/260.4>MonoHexCer:d18:0/24:0 | −0.089033 | −0.062703 | 0.003806 | −0.026279 | −0.027456 | 0.017615 | −0.030768 | 0.059948 | 0.110364 | −0.012725 |
| 321 | 838.9/264.4>MonoHexCer:d18:1/26:1 | −0.097906 | −0.051344 | 0.018165 | −0.013912 | 0.008298 | 0.027266 | −0.013752 | 0.046764 | 0.074897 | −0.048319 |
| 322 | 840.9/260.4>MonoHexCer:d18:0/26:1 | −0.061726 | 0.021541 | 0.007593 | −0.004864 | −0.048812 | −0.000355 | 0.001227 | 0.018958 | 0.004339 | −0.087311 |
| 323 | 840.9/264.4>MonoHexCer:d18:1/26:0 | −0.103153 | 0.003172 | −0.012607 | 0.057014 | 0.007811 | 0.00978 | 0.024032 | −0.011555 | −0.018183 | −0.049661 |
| 324 | 842.9/260.4>MonoHexCer:d18:0/26:0 | −0.06271 | 0.025738 | 0.010485 | −0.035959 | −0.063465 | −0.002517 | 0.0199 | −0.068131 | 0.020455 | −0.111476 |
| 325 | 862.7/264.4>DiHexCer:d18:1/16:0 | −0.101736 | −0.05852 | −0.033158 | −0.029651 | −0.005936 | 0.018433 | −0.051189 | 0.032394 | 0.056333 | 0.021313 |
| 326 | 864.7/260.4>DiHexCer:d18:0/16:0 | −0.088768 | −0.015747 | −0.031405 | 0.005121 | −0.024481 | 0.028898 | −0.021278 | −0.012291 | 0.047473 | −0.049436 |
| 327 | 890.7/264.4>DiHexCer:d18:1/18:0 | −0.102763 | −0.054407 | −0.026554 | −0.035736 | −0.007663 | 0.023402 | −0.032187 | 0.068605 | 0.077849 | −0.008707 |
| 328 | 892.7/260.4>DiHexCer:d18:0/18:0 | −0.06167 | 0.042893 | −0.025252 | 0.0011 | −0.00131 | 0.015598 | 0.009456 | −0.001863 | 0.030215 | −0.032798 |
| 329 | 918.7/264.4>DiHexCer:d18:1/20:0 | −0.113315 | −0.038747 | −0.033367 | 0.017344 | −0.004234 | 0.020059 | −0.007585 | 0.012033 | 0.035765 | −0.051171 |
| 330 | 920.7/260.4>DiHexCer:d18:0/20:0 | −0.013096 | 0.019547 | 0.049981 | −0.065262 | 0.005234 | 0.048947 | −0.034386 | −0.049951 | 0.046823 | −0.086375 |
| 331 | 940.8/264.4>DiHexCer:d18:1/22:0 | −0.105047 | −0.060979 | −0.022974 | −0.016706 | −0.007717 | −0.000642 | −0.040223 | 0.039133 | 0.07594 | −0.022739 |
| 332 | 948.8/260.4>DiHexCer:d18:0/22:0 | −0.042865 | 0.033274 | 0.021012 | −0.001276 | 0.020951 | 0.045777 | −0.046834 | 0.002815 | 0.038018 | −0.049072 |
| 333 | 972.9/264.4>DiHexCer:d18:1/24:1 | −0.109255 | −0.041861 | −0.040408 | −0.010967 | 0.007223 | 0.020902 | −0.034676 | 0.002652 | 0.042947 | −0.003286 |
| 334 | 974.9/260.4>DiHexCer:d18:0/24:1 | −0.090433 | −0.008168 | −0.032103 | 0.004996 | −0.007113 | −0.006235 | −0.017842 | −0.051043 | −0.013542 | −0.021985 |
| 335 | 974.9/264.4>DiHexCer:d18:1/24:0 | −0.098299 | −0.061791 | −0.026712 | −0.011876 | −0.011475 | −0.004054 | −0.051455 | 0.068558 | 0.089058 | −0.002765 |
| 336 | 970.9/260.4>DiHexCer:d18:0/24:0 | −0.088834 | −0.006502 | 0.016948 | −0.018238 | −0.039775 | −0.001028 | 0.018336 | −0.051213 | 0.011626 | −0.09637 |
| 337 | 1000.9/264.4>DiHexCer:d18:1/26:1 | −0.098684 | 0.023241 | 0.030815 | 0.006703 | 0.013586 | 0.011914 | 0.031442 | −0.022844 | 0.017705 | −0.0714 |
| 338 | 1002.9/260.4>DiHexCer:d18:0/26:1 | −0.048033 | 0.003694 | 0.005691 | 0.043714 | −0.027531 | 0.002626 | 0.030177 | 0.017318 | −0.046262 | −0.002826 |
| 339 | 1002.9/264.4>DiHexCer:d18:1/26:0 | −0.097594 | 0.041068 | −0.015018 | 0.032414 | 0.032641 | −0.004476 | 0.06076 | 0.045574 | −0.007573 | −0.016444 |
| 340 | 1004.9/260.4>DiHexCer:d18:0/26:0 | −0.022339 | 0.050051 | −0.003707 | 0.020905 | 0.002626 | 0.027829 | 0.040192 | 0.02106 | 0.005104 | 0.00651 |

| | L | M | N | O | P | Q | R | S | T | U | V | W | X | Y |
|---|---|---|---|---|---|---|---|---|---|---|---|---|---|---|
| 1 | −0.017531 | −0.027408 | 0.024407 | −0.003534 | 0.021833 | −0.071983 | 0.040261 | −0.009362 | 0.021492 | 0.01451 | −0.023507 | 0.011981 | 0.022413 | 0.062705 |
| 2 | −0.0383 | 0.003989 | −0.017257 | 0.061125 | 0.015009 | −0.030927 | 0.076012 | −0.051392 | 0.057452 | −0.042072 | −0.013649 | −0.013306 | 0.047099 | 0.084724 |
| 3 | −0.118209 | −0.01969 | −0.035472 | 0.043304 | −0.022766 | −0.040468 | 0.052501 | −0.050744 | 0.060586 | −0.004656 | 0.021257 | −0.031133 | 0.016434 | 0.034548 |
| 4 | 0.143481 | −0.01189 | 0.052912 | −0.126158 | −0.018294 | −0.002289 | −0.009909 | 0.055012 | 0.025936 | −0.007713 | −0.015995 | −0.036036 | 0.042803 | −0.009327 |
| 5 | 0.036199 | −0.118098 | 0.079282 | 0.104575 | 0.011152 | 0.040431 | 0.024923 | −0.029905 | 0.030164 | −0.033235 | −0.040509 | 0.008506 | 0.026611 | 0.040146 |
| 6 | −0.032861 | 0.027774 | −0.050904 | 0.00208 | 0.031447 | −0.016202 | 0.024074 | −0.012797 | 0.060531 | −0.002349 | 0.108874 | −0.001905 | 0.024056 | 0.05387 |
| 7 | −0.099361 | 0.01622 | −0.011191 | 0.055015 | 0.018592 | 0.050615 | −0.015016 | −0.08026 | 0.066189 | 0.038563 | 0.076994 | −0.022193 | 0.064489 | 0.062386 |
| 8 | −0.040113 | −0.047926 | 0.023417 | 0.088066 | 0.015794 | 0.01862 | −0.057569 | −0.086436 | 0.027663 | 0.047508 | −0.092981 | −0.112844 | −0.003344 | 0.06087 |
| 9 | 0.14888 | −0.031032 | 0.069736 | −0.084577 | −0.009724 | 0.018668 | 0.029356 | 0.046729 | −0.017904 | −0.026582 | −0.016974 | −0.05466 | 0.077047 | −0.024373 |
| 10 | −0.058609 | 0.026759 | −0.03972 | 0.040293 | −0.038974 | 0.056632 | 0.033396 | −0.092089 | 0.006004 | 0.088098 | 0.051392 | −0.062129 | 0.014951 | 0.109793 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 11 | −0.0298 | −0.087762 | 0.006976 | 0.047218 | 0.043973 | 0.019863 | 0.098348 | −0.094384 | 0.040403 | 0.043781 | −0.073442 | −0.036435 | −0.079163 | 0.107193 |
| 12 | −0.006404 | 0.052416 | 0.009645 | −0.051274 | 0.054522 | 0.003476 | −0.03365 | −0.009443 | −0.003317 | 0.114518 | −0.017206 | 0.137295 | 0.054467 | 0.031019 |
| 13 | −0.066666 | −0.015096 | 0.042396 | −0.014024 | 0.004309 | 0.017609 | −0.006016 | 0.00826 | 0.010112 | 0.005658 | 0.00954 | −0.029475 | 0.009308 | −0.004329 |
| 14 | −0.071837 | −0.048868 | 0.046524 | −0.006085 | 0.014357 | 0.010371 | 0.000337 | 0.004681 | 0.003591 | 0.02383 | 0.002497 | −0.035597 | −0.00195 | −0.005085 |
| 15 | −0.072593 | 0.00168 | 0.012728 | 0.055135 | 0.014088 | −0.06692 | 0.011379 | 0.027143 | 0.017595 | −0.01723 | −0.050127 | −0.004586 | −0.03018 | 0.007194 |
| 16 | 0.009892 | −0.013078 | 0.092684 | 0.045359 | −0.005536 | −0.071019 | −0.027349 | −0.163244 | −0.118841 | 0.012767 | 0.011765 | 0.089795 | 0.023296 | 0.110142 |
| 17 | −0.018793 | 0.011054 | −0.013677 | −0.075198 | 0.011443 | −0.031833 | 0.022616 | 0.074165 | 0.008416 | −0.080927 | 0.050637 | 0.050966 | 0.064166 | −0.026258 |
| 18 | −0.058107 | −0.054881 | 0.079642 | 0.107442 | 0.034917 | −0.060554 | −0.050821 | −0.09222 | −0.105151 | −0.076685 | −0.071659 | 0.086648 | 0.062895 | −0.140573 |
| 19 | −0.100825 | −0.011928 | −0.039908 | 0.061947 | 0.098455 | −0.079101 | 0.079232 | −0.079697 | −0.014643 | −0.078325 | 0.023776 | −0.046205 | 0.046291 | 0.048347 |
| 20 | −0.042207 | 0.022788 | −0.013308 | 0.041543 | 0.023489 | 0.003387 | −0.00584 | 0.036307 | 0.001553 | 0.003151 | −0.00725 | −0.004522 | −0.017738 | −0.006341 |
| 21 | −0.032216 | 0.030376 | −0.0064 | 0.015974 | 0.03899 | −0.04636 | 0.08762 | −0.058439 | 0.071747 | −0.034651 | 0.033737 | −0.023215 | 0.080723 | 0.059506 |
| 22 | −0.066653 | 0.024556 | −0.000952 | 0.095534 | 0.012886 | 0.02485 | 0.011314 | 0.013172 | 0.029861 | −0.066821 | −0.001186 | 0.010619 | 0.016171 | 0.033551 |
| 23 | −0.078606 | 0.03617 | 0.00402 | 0.022361 | 0.04323 | −0.144385 | 0.007544 | −0.107877 | 0.072972 | 0.017086 | −0.068539 | −0.006464 | 0.028036 | 0.001022 |
| 24 | −0.080271 | −0.021289 | −0.000268 | 0.05211 | 0.037459 | −0.086409 | 0.063737 | −0.05637 | 0.060019 | −0.066308 | −0.025174 | −0.003263 | 0.092703 | 0.009135 |
| 25 | −0.014287 | −0.027619 | −0.029747 | 0.031326 | 0.04099 | −0.043816 | 0.007167 | −0.051967 | 0.008138 | −0.021806 | −0.021336 | −0.04791 | 0.036139 | 0.059261 |
| 26 | −0.037943 | 0.025372 | −0.022785 | 0.039965 | 0.020789 | 0.003362 | −0.003205 | 0.033018 | 0.000345 | 0.002537 | −0.013696 | −0.007391 | −0.021522 | −0.008441 |
| 27 | −0.020004 | 0.039523 | −0.022895 | 0.039313 | 0.018308 | 0.005156 | −0.009477 | 0.03937 | −0.00552 | 0.006861 | −0.013286 | 0.004265 | −0.024961 | −0.000473 |
| 28 | 0.062319 | 0.019768 | 0.004471 | −0.002618 | 0.025945 | 0.001353 | 0.001096 | 0.066231 | 0.0123 | −0.020157 | −0.014685 | −0.038884 | 0.024143 | 0.010472 |
| 29 | −0.042938 | 0.034913 | −0.027542 | 0.037291 | −0.001995 | −0.022141 | 0.002903 | −0.001354 | 0.06247 | 0.006242 | 0.016015 | 0.01782 | 0.036093 | 0.036541 |
| 30 | 0.065249 | 0.011733 | −0.021494 | 0.003716 | 0.014195 | 0.035271 | −0.01289 | 0.047002 | 0.038143 | 0.041415 | 0.066481 | 0.011999 | −0.028298 | −0.021703 |
| 31 | 0.017868 | 0.026596 | −0.01584 | −0.004625 | 0.021525 | 0.006635 | −0.013485 | −0.006483 | 0.009311 | 0.048376 | −0.003157 | 0.015662 | 0.037082 | 0.023634 |
| 32 | −0.027506 | 0.046655 | −0.018283 | 0.015011 | 0.02833 | −0.030826 | −0.035561 | 0.012945 | −0.070955 | −0.034847 | 0.043952 | 0.025914 | 0.03902 | 0.021825 |
| 33 | −0.034412 | −0.00735 | −0.024067 | 0.038265 | 0.014562 | −0.00253 | −0.031117 | 0.039291 | −0.009211 | −0.018703 | −0.035978 | 0.024135 | −0.050325 | −0.003862 |
| 34 | 0.030282 | 0.034979 | −0.035734 | 0.060847 | 0.047833 | 0.028789 | −0.00742 | 0.050005 | −0.01253 | −0.012129 | −0.017897 | −0.023357 | −0.01239 | −0.047027 |
| 35 | 0.020901 | −0.112867 | 0.042094 | −0.008309 | −0.017263 | 0.065853 | −0.038456 | −0.023578 | 0.001917 | 0.020574 | −0.032973 | −0.002793 | −0.045524 | −0.071939 |
| 36 | −0.044662 | −0.026491 | 0.002115 | 0.00774 | 0.006389 | 0.017311 | 0.03676 | −0.002142 | 0.039004 | −0.015187 | 0.001076 | 0.005776 | −0.035899 | −0.080081 |
| 37 | −0.018651 | 0.019036 | −0.02327 | 0.032202 | 0.028289 | 0.001996 | −0.027444 | 0.043353 | 0.008064 | −0.014861 | 0.001186 | −0.009164 | −0.004346 | −0.041302 |
| 38 | −0.144271 | 0.048819 | 0.030722 | 0.034539 | 0.08098 | −0.016753 | −0.031989 | 0.067019 | 0.075935 | −0.003995 | −0.031199 | −0.012989 | −0.01036 | 0.003023 |
| 39 | −0.013736 | −0.144917 | −0.13641 | 0.003327 | 0.026885 | −0.059409 | −0.003552 | −0.011001 | −0.005712 | 0.039841 | 0.016092 | 0.056329 | 0.049052 | 0.02897 |
| 40 | 0.079111 | −0.010532 | −0.075581 | 0.027116 | 0.050522 | −0.00407 | −0.020729 | 0.060513 | −0.034529 | −0.002773 | −0.012567 | 0.069162 | −0.086052 | −0.042226 |
| 41 | 0.111772 | −0.012577 | −0.100012 | 0.038234 | 0.072135 | −0.006648 | 0.017985 | 0.033867 | −0.025019 | −0.017371 | −0.007411 | 0.029417 | −0.034361 | −0.047393 |
| 42 | 0.032339 | −0.130265 | −0.103103 | 0.001202 | 0.104601 | −0.028856 | 0.028352 | −0.021053 | −0.090022 | −0.030182 | 0.022014 | 0.036463 | −0.012977 | −0.021354 |
| 43 | 0.094103 | 0.006144 | −0.093511 | 0.022346 | 0.052131 | 0.033847 | −0.024917 | 0.05078 | −0.013617 | 0.023615 | 0.011352 | 0.024857 | −0.09256 | −0.04519 |
| 44 | 0.100485 | 0.007415 | −0.075138 | 0.033337 | 0.0453 | 0.005947 | −0.056386 | 0.065278 | 0.016568 | −0.051695 | −0.091584 | 0.03036 | −0.083251 | −0.039193 |
| 45 | 0.076369 | 0.006012 | −0.104424 | 0.022217 | 0.001168 | 0.07385 | −0.03827 | 0.027906 | −0.076571 | 0.030913 | −0.004906 | 0.01934 | −0.074218 | 0.003296 |
| 46 | 0.064096 | −0.033778 | −0.118099 | −0.015875 | −0.020772 | 0.049259 | −0.037585 | 0.03941 | −0.057471 | −0.038121 | −0.111572 | 0.01734 | −0.02944 | −0.018921 |
| 47 | −0.106139 | −0.100197 | −0.13339 | −0.010424 | −0.111613 | −0.062815 | −0.024402 | 0.03952 | 0.045076 | −0.017732 | 0.058691 | −0.026372 | 0.036366 | 0.018275 |
| 48 | −0.040265 | −0.166433 | −0.154341 | 0.03876 | −0.059379 | −0.060791 | −0.095868 | 0.042847 | 0.004529 | −0.002939 | −0.006084 | −0.066664 | 0.202688 | 0.055892 |
| 49 | 0.06324 | 0.010018 | −0.027028 | 0.008028 | 0.009868 | 0.038821 | −0.02886 | 0.050284 | 0.053228 | 0.039368 | 0.079582 | 0.002509 | −0.017661 | −0.03622 |
| 50 | 0.002795 | −0.038366 | −0.053829 | 0.03776 | 0.062617 | −0.06757 | 0.06247 | 0.014719 | −0.051643 | −0.011338 | −0.006116 | −0.009682 | 0.006648 | 0.047465 |
| 51 | −0.124982 | −0.077569 | −0.101455 | −0.051217 | −0.046668 | −0.018892 | 0.021504 | −0.030372 | 0.020444 | −0.044509 | 0.014242 | 0.034073 | −0.05542 | −0.002629 |
| 52 | 0.051037 | −0.021399 | −0.067154 | 0.076257 | 0.045017 | −0.073784 | −0.031357 | 0.048418 | −0.027681 | −0.057573 | −0.008822 | 0.018789 | 0.054101 | 0.068178 |
| 53 | −0.11134 | −0.07816 | −0.065353 | −0.042152 | −0.036319 | −0.004427 | −0.020446 | 0.006931 | −0.003484 | −0.066269 | 0.005417 | 0.024696 | −0.055163 | 0.009435 |
| 54 | −0.018596 | −0.108229 | −0.114521 | 0.021742 | 0.039975 | −0.063303 | −0.093913 | −0.024892 | 0.02516 | −0.012239 | −0.041865 | −0.055502 | 0.060129 | 0.027619 |
| 55 | −0.054001 | −0.014341 | −0.013305 | −0.00513 | −0.001043 | −0.000014 | 0.004768 | 0.018838 | −0.012848 | −0.026046 | −0.021445 | 0.016531 | −0.000811 | 0.026 |
| 56 | 0.080065 | 0.023892 | −0.025317 | 0.008534 | 0.01689 | 0.042596 | −0.032129 | 0.035299 | 0.054266 | 0.088567 | 0.058311 | −0.022679 | −0.05032 | −0.046314 |
| 57 | 0.026034 | −0.007567 | 0.01408 | 0.022851 | 0.124889 | −0.026063 | −0.049982 | 0.024085 | 0.054408 | −0.05064 | 0.013859 | −0.012845 | 0.074414 | 0.04705 |
| 58 | 0.000955 | −0.032732 | −0.014075 | 0.008362 | −0.016106 | −0.056747 | −0.037832 | 0.01124 | 0.003588 | −0.037352 | −0.012915 | 0.006252 | −0.058898 | −0.103045 |
| 59 | 0.14435 | 0.019441 | −0.077073 | 0.014022 | 0.11791 | 0.019847 | −0.107753 | 0.006735 | 0.173175 | −0.103034 | −0.072405 | 0.012656 | −0.002312 | 0.039914 |
| 60 | 0.063392 | 0.014826 | 0.011472 | 0.015509 | 0.015831 | −0.012073 | 0.038641 | −0.045482 | −0.027439 | 0.017419 | −0.004124 | −0.013419 | 0.076923 | −0.007904 |
| 61 | 0.15055 | 0.057837 | −0.100033 | 0.027566 | 0.06439 | −0.006662 | −0.029733 | 0.002986 | 0.053697 | 0.017685 | −0.040076 | −0.012829 | 0.000105 | −0.014939 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 62 | −0.074245 | −0.027587 | −0.05007 | −0.079412 | −0.062351 | −0.012222 | −0.025516 | −0.059241 | 0.003703 | −0.004512 | 0.015763 | −0.016503 | −0.001933 | −0.115097 |
| 63 | 0.045067 | −0.000977 | −0.130488 | 0.026658 | 0.052682 | −0.005765 | −0.072946 | 0.004573 | 0.030721 | 0.042653 | −0.017361 | −0.015317 | 0.008475 | 0.017073 |
| 64 | 0.088908 | 0.028774 | −0.032506 | 0.004223 | 0.018271 | 0.041388 | −0.026431 | 0.006308 | 0.04363 | 0.056881 | 0.088898 | −0.0125 | −0.038107 | −0.053667 |
| 65 | 0.038461 | 0.046128 | 0.035436 | 0.00766 | 0.124875 | 0.015164 | −0.070504 | −0.019421 | 0.043584 | 0.016818 | 0.00598 | −0.032139 | 0.099347 | −0.023812 |
| 66 | 0.139272 | 0.093349 | −0.037859 | 0.019331 | 0.055579 | 0.034077 | −0.11641 | 0.033975 | 0.112647 | −0.056891 | −0.060656 | −0.02499 | −0.017421 | −0.017212 |
| 67 | 0.09211 | 0.044011 | −0.077219 | 0.022094 | −0.036152 | 0.088403 | −0.111134 | 0.013389 | −0.038037 | 0.07586 | −0.079656 | −0.010467 | −0.070072 | 0.059378 |
| 68 | −0.022375 | −0.006685 | −0.016239 | 0.03309 | 0.056027 | 0.006755 | −0.062242 | 0.103771 | −0.050799 | 0.059021 | −0.178028 | −0.063636 | −0.057956 | 0.000342 |
| 69 | −0.07407 | −0.044843 | 0.068113 | −0.016359 | 0.00217 | 0.017926 | −0.00944 | −0.001708 | −0.008773 | 0.005126 | −0.001461 | −0.016383 | −0.002219 | 0.010161 |
| 70 | −0.07531 | −0.045308 | 0.084397 | −0.015985 | −0.005695 | 0.024805 | 0.009484 | −0.010609 | 0.00812 | 0.02373 | 0.017567 | −0.019296 | −0.001215 | 0.019428 |
| 71 | 0.057324 | −0.019525 | 0.022348 | −0.116918 | −0.007648 | 0.02446 | −0.00174 | −0.066749 | −0.013977 | 0.001732 | 0.020354 | 0.043618 | 0.061757 | 0.015484 |
| 72 | 0.079291 | −0.040268 | 0.02147 | −0.173077 | −0.030238 | −0.006055 | −0.038808 | −0.103987 | −0.004046 | 0.064455 | 0.070677 | 0.052921 | 0.064122 | 0.074049 |
| 73 | 0.087052 | −0.067157 | 0.034684 | −0.178817 | −0.067592 | −0.023901 | −0.049556 | −0.085067 | −0.001932 | 0.025777 | 0.063486 | 0.04648 | 0.004167 | 0.122913 |
| 74 | −0.024105 | 0.042524 | −0.056747 | −0.091345 | 0.124434 | −0.047666 | 0.084518 | −0.092345 | 0.018914 | −0.024717 | −0.030031 | 0.056118 | −0.018221 | 0.009307 |
| 75 | −0.071744 | −0.047993 | 0.073899 | −0.02475 | −0.001506 | 0.018876 | 0.009339 | 0.000528 | −0.015451 | 0.00836 | 0.009904 | −0.0269 | 0.011692 | 0.012342 |
| 76 | −0.07492 | −0.051734 | 0.069961 | −0.033643 | −0.002758 | 0.026037 | 0.010146 | 0.008801 | −0.027959 | −0.001083 | 0.018251 | −0.03591 | 0.01007 | 0.013628 |
| 77 | −0.071966 | −0.049561 | 0.075554 | −0.027936 | −0.000372 | 0.020175 | 0.008681 | 0.00163 | −0.021357 | 0.007987 | 0.014695 | −0.025221 | 0.014086 | 0.01571 |
| 78 | −0.071092 | −0.048916 | 0.077378 | −0.027086 | −0.000299 | 0.020499 | 0.003651 | 0.003027 | −0.023276 | 0.010512 | 0.014285 | −0.023839 | 0.015469 | 0.01714 |
| 79 | −0.073738 | −0.041368 | 0.08058 | −0.020733 | 0.002873 | 0.018232 | 0.011896 | 0.001593 | −0.029009 | 0.010729 | 0.009844 | −0.02453 | 0.009865 | 0.016045 |
| 80 | −0.048778 | 0.072186 | −0.021572 | 0.036611 | −0.102746 | 0.032766 | 0.000578 | −0.147958 | 0.043286 | 0.069116 | 0.031372 | −0.024213 | 0.006928 | 0.013446 |
| 81 | −0.036837 | −0.020349 | 0.004669 | −0.074441 | −0.0181 | −0.019571 | −0.030033 | 0.006909 | −0.043571 | −0.078022 | 0.076571 | 0.052894 | 0.043037 | −0.001946 |
| 82 | −0.005909 | 0.018066 | −0.011661 | −0.009771 | 0.008105 | −0.003992 | −0.013714 | 0.017942 | −0.020527 | 0.014794 | −0.007892 | 0.015704 | −0.012377 | 0.004807 |
| 83 | −0.004016 | 0.032106 | −0.018437 | 0.013993 | 0.009459 | 0.001332 | −0.018143 | 0.033074 | −0.014305 | 0.011063 | −0.011058 | 0.01578 | −0.015196 | 0.006818 |
| 84 | −0.012587 | 0.034985 | −0.019777 | 0.022282 | 0.015233 | 0.005807 | −0.012615 | 0.035398 | −0.010915 | 0.009929 | −0.011628 | 0.010831 | −0.018362 | 0.010938 |
| 85 | 0.072448 | −0.026504 | −0.000635 | −0.111719 | −0.058966 | −0.040162 | −0.081452 | −0.089803 | 0.022237 | 0.050382 | 0.055129 | 0.058409 | 0.060325 | 0.057834 |
| 86 | 0.107145 | −0.046521 | 0.009843 | −0.173082 | −0.046728 | −0.034747 | −0.058047 | −0.074119 | −0.025951 | 0.078884 | 0.033298 | 0.053936 | 0.063974 | 0.055772 |
| 87 | 0.04685 | 0.006649 | 0.003582 | −0.09004 | −0.030569 | −0.019264 | −0.042978 | −0.041187 | −0.01276 | 0.053189 | 0.03413 | 0.05566 | 0.073062 | 0.022964 |
| 88 | −0.010393 | 0.038727 | −0.020167 | 0.026092 | 0.008659 | −0.000387 | −0.015301 | 0.025372 | −0.011638 | 0.013112 | −0.013538 | 0.013702 | −0.018733 | 0.007535 |
| 89 | −0.018511 | 0.041114 | −0.024541 | 0.044312 | 0.015226 | 0.004105 | −0.011481 | 0.04152 | −0.010174 | −0.000111 | −0.019831 | 0.006306 | −0.024649 | −0.001444 |
| 90 | −0.01325 | 0.0363 | −0.018422 | 0.037057 | 0.01412 | 0.004063 | −0.01271 | 0.039495 | −0.008304 | 0.008333 | −0.015058 | 0.0011 | −0.021321 | −0.003186 |
| 91 | −0.01553 | 0.027037 | −0.028787 | 0.017101 | 0.015125 | 0.003212 | −0.008914 | 0.022144 | −0.005157 | 0.009428 | 0.001847 | 0.002819 | −0.009263 | 0.001539 |
| 92 | 0.00578 | −0.002018 | −0.003107 | −0.055996 | −0.004251 | −0.005462 | −0.004107 | −0.03027 | −0.024417 | 0.065909 | 0.010482 | 0.029129 | 0.056573 | 0.042163 |
| 93 | 0.023523 | 0.021172 | −0.009781 | −0.008437 | −0.009397 | −0.006919 | −0.033091 | 0.003828 | −0.022598 | 0.023813 | −0.000092 | 0.025432 | −0.001228 | 0.015632 |
| 94 | −0.014135 | 0.031657 | −0.029983 | 0.02833 | −0.004417 | 0.003464 | −0.047698 | 0.00318 | 0.000969 | −0.020074 | −0.008371 | −0.033087 | 0.013609 | −0.003432 |
| 95 | 0.023484 | −0.121448 | 0.056133 | −0.052041 | −0.046971 | −0.037435 | −0.06075 | 0.069521 | −0.01818 | 0.001851 | −0.105615 | 0.012709 | 0.023536 | 0.052092 |
| 96 | −0.086146 | −0.071334 | 0.002667 | 0.06497 | 0.016087 | −0.071591 | 0.06476 | 0.068409 | 0.02614 | 0.07254 | 0.048016 | −0.066057 | 0.021341 | 0.106854 |
| 97 | −0.030622 | −0.037811 | 0.007833 | −0.001471 | 0.035221 | −0.132839 | −0.129507 | −0.000113 | −0.007039 | 0.001928 | 0.016809 | 0.001202 | 0.015105 | −0.017551 |
| 98 | −0.041426 | 0.077235 | −0.015605 | −0.007892 | −0.09865 | −0.013874 | −0.016224 | −0.027098 | 0.037995 | −0.035467 | 0.02189 | −0.053052 | 0.047374 | 0.035282 |
| 99 | −0.020588 | −0.059317 | 0.054435 | 0.052734 | 0.011406 | −0.105141 | −0.048036 | −0.001956 | −0.005405 | −0.001416 | −0.033715 | −0.021197 | −0.065381 | −0.012822 |
| 100 | −0.025794 | 0.003407 | −0.01065 | −0.024157 | −0.056038 | −0.089601 | 0.019021 | −0.031649 | 0.01837 | −0.012649 | 0.005613 | −0.017354 | 0.094794 | 0.041764 |
| 101 | −0.018127 | 0.114483 | −0.040846 | −0.012694 | −0.099371 | 0.00743 | −0.0269 | −0.054427 | 0.051583 | −0.017988 | 0.036497 | −0.05237 | −0.003426 | 0.036374 |
| 102 | −0.009754 | −0.122965 | 0.028363 | −0.008789 | −0.041878 | −0.211737 | 0.045997 | 0.065344 | 0.037859 | 0.062902 | −0.040159 | 0.065464 | 0.105719 | −0.012328 |
| 103 | −0.004803 | −0.051981 | 0.039726 | −0.011352 | −0.063944 | −0.112969 | 0.005292 | 0.115639 | 0.023275 | −0.092947 | −0.030273 | 0.058715 | 0.123191 | 0.024847 |
| 104 | 0.044108 | −0.047505 | 0.01021 | −0.031883 | 0.038316 | −0.073639 | −0.054518 | 0.03048 | 0.027698 | −0.048612 | 0.005906 | 0.134213 | −0.039546 | 0.084676 |
| 105 | −0.028913 | 0.003656 | 0.042971 | 0.031908 | 0.113162 | 0.083473 | 0.047178 | −0.042596 | −0.038503 | −0.090756 | 0.059242 | 0.004495 | 0.086499 | −0.065428 |
| 106 | 0.016072 | 0.013436 | 0.036654 | −0.008427 | −0.052682 | 0.003701 | 0.037684 | −0.019685 | 0.021179 | −0.040442 | −0.018565 | 0.021923 | 0.018603 | 0.024766 |
| 107 | −0.007889 | −0.004597 | 0.020829 | −0.013825 | −0.037834 | −0.056782 | 0.041778 | −0.047233 | 0.075772 | −0.011135 | −0.024085 | 0.059783 | −0.025809 | 0.025255 |
| 108 | −0.042671 | −0.012502 | 0.044577 | −0.005671 | −0.005851 | −0.024411 | 0.043687 | −0.040975 | 0.060529 | −0.02585 | 0.013918 | 0.057664 | −0.075938 | 0.048096 |
| 109 | −0.017564 | −0.010376 | 0.062069 | −0.008722 | −0.017722 | 0.022438 | −0.003734 | −0.049374 | 0.013882 | −0.089422 | −0.062607 | 0.035973 | 0.019321 | −0.035508 |
| 110 | 0.015221 | 0.02114 | 0.027842 | 0.034055 | −0.049396 | 0.065947 | −0.027001 | −0.047703 | 0.008537 | −0.037248 | −0.015774 | 0.033556 | 0.07688 | 0.067438 |
| 111 | −0.000267 | −0.030824 | 0.057211 | 0.010229 | −0.005834 | −0.016899 | −0.022723 | −0.025212 | −0.019879 | −0.07857 | 0.037248 | 0.08728 | −0.015796 | −0.032536 |
| 112 | 0.032163 | −0.037476 | 0.066594 | 0.018327 | 0.015414 | 0.005844 | 0.069371 | −0.012562 | 0.069937 | −0.050752 | −0.021005 | 0.055972 | 0.08033 | 0.02205 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 113 | −0.012319 | −0.028445 | 0.065295 | 0.012922 | −0.009766 | −0.014765 | 0.037598 | 0.014662 | 0.085905 | −0.01007 | 0.022568 | 0.071656 | −0.009744 | −0.001038 |
| 114 | −0.008229 | −0.007827 | 0.032183 | 0.013628 | 0.061321 | 0.056334 | 0.086206 | −0.013652 | 0.005354 | 0.040468 | 0.049518 | 0.041958 | 0.038395 | 0.025555 |
| 115 | 0.037905 | −0.018409 | 0.06296 | 0.007933 | 0.009627 | −0.003597 | 0.051631 | 0.000364 | 0.023813 | −0.001638 | 0.008235 | 0.055625 | −0.053641 | 0.021368 |
| 116 | −0.001631 | 0.039949 | −0.004394 | −0.040138 | −0.031014 | 0.070109 | 0.050223 | −0.046521 | 0.064062 | 0.011676 | 0.01964 | 0.009085 | −0.02708 | −0.035142 |
| 117 | −0.090303 | −0.112003 | 0.02204 | 0.085743 | −0.022259 | 0.039958 | 0.022891 | 0.018254 | −0.023032 | 0.152011 | 0.010487 | 0.024942 | 0.049517 | −0.076538 |
| 118 | −0.012228 | −0.063416 | 0.054034 | −0.002702 | −0.075405 | 0.0088 | −0.028713 | 0.037139 | 0.027027 | 0.040259 | −0.051266 | −0.056025 | −0.028081 | −0.10881 |
| 119 | −0.038124 | −0.030048 | 0.090168 | −0.065845 | 0.098502 | 0.053534 | 0.001989 | −0.079658 | 0.026044 | −0.033984 | −0.041075 | −0.103079 | −0.004323 | 0.034631 |
| 120 | −0.05951 | −0.13192 | −0.029916 | 0.051657 | −0.010713 | 0.013396 | 0.021441 | 0.042531 | 0.000659 | 0.09499 | 0.010419 | −0.007058 | 0.08934 | −0.019209 |
| 121 | −0.077616 | −0.113532 | 0.002305 | 0:062018 | −0.048969 | 0.000877 | −0.042443 | −0.025176 | −0.000286 | 0.094577 | −0.011782 | 0.031284 | 0.117592 | −0.056618 |
| 122 | 0.08246 | −0.031376 | 0.081743 | −0.013749 | −0.053467 | 0.012084 | 0.007116 | 0.037603 | 0.050122 | −0.055153 | −0.080088 | −0.015479 | −0.019676 | −0.001081 |
| 123 | 0.082964 | −0.06562 | 0.093337 | −0.053434 | −0.052344 | 0.020897 | −0.038638 | −0.016928 | 0.039891 | −0.072315 | −0.055995 | −0.049735 | −0.065441 | −0.036833 |
| 124 | −0.021113 | 0.017462 | 0.060375 | 0.007101 | 0.07926 | −0.00943 | −0.026806 | −0.112757 | 0.059511 | −0.031656 | −0.067099 | −0.125335 | 0.0128571 | −0.035495 |
| 125 | 0.004178 | −0.074885 | 0.042606 | 0.127138 | −0.017593 | 0.029996 | 0.001027 | 0.051817 | 0.035946 | 0.067063 | 0.090331 | 0.055495 | −0.07615 | −0.049473 |
| 126 | 0.113561 | −0.077394 | 0.112618 | −0.046202 | −0.055434 | 0.059634 | −0.054999 | 0.02163 | 0.021905 | 0.014433 | 0.021108 | 0.019375 | −0.10591 | −0.05531 |
| 127 | 0.078064 | −0.092802 | 0.094871 | −0.049582 | −0.058772 | 0.080687 | −0.043561 | 0.027149 | −0.02475 | 0.024195 | 0.026817 | 0.004746 | −0.116707 | −0.013754 |
| 128 | 0.029831 | −0.015462 | −0.039798 | −0.057525 | 0.071205 | 0.13066 | 0.094737 | 0.07605 | 0.026261 | 0.010132 | −0.056399 | 0.081171 | 0.028038 | 0.068399 |
| 129 | −0.014781 | −0.051755 | 0.038802 | 0.135256 | −0.027242 | 0.057124 | −0.08033 | 0.098017 | −0.024587 | −0.028921 | 0.06785 | −0.189078 | 0.051396 | 0.057031 |
| 130 | 0.043096 | −0.078862 | −0.027245 | 0.075434 | −0.039534 | 0.093451 | −0.001982 | −0.028545 | 0.074932 | 0.080931 | 0.044924 | 0.08085 | 0.032817 | 0.049772 |
| 131 | −0.011609 | −0.057374 | 0.064527 | 0.189734 | −0.050883 | 0.131787 | −0.095712 | −0.046501 | −0.028367 | 0.043548 | 0.11002 | 0.117386 | 0.17314 | −0.084932 |
| 132 | −0.002671 | −0.045073 | −0.05656 | −0.064922 | 0.020825 | 0.043716 | 0.058311 | 0.020247 | 0.080445 | 0.046781 | 0.035001 | 0.048321 | 0.020651 | 0.056405 |
| 133 | −0.087606 | 0.129194 | 0.023306 | −0.000052 | 0.03705 | 0.105681 | −0.041706 | 0.004998 | 0.013977 | −0.042313 | −0.121541 | 0.059928 | −0.001816 | −0.029611 |
| 134 | −0.027809 | 0.004432 | 0.068577 | 0.130805 | −0.076292 | 0.042562 | 0.005858 | 0.024255 | 0.001971 | 0.029825 | −0.043455 | 0.055562 | −0.044757 | −0.038958 |
| 135 | 0.004362 | 0.032604 | −0.033832 | −0.05573 | 0.035955 | −0.003196 | 0.015737 | 0.007097 | 0.010668 | −0.042221 | −0.000397 | −0.006262 | −0.019883 | 0.005634 |
| 136 | −0.011078 | 0.046541 | 0.016275 | 0.024482 | 0.005091 | 0.030028 | 0.04401 | −0.082651 | 0.090499 | −0.009862 | −0.055218 | −0.073049 | −0.023367 | 0.046629 |
| 137 | −0.001793 | −0.057837 | 0.009321 | 0.066546 | −0.056645 | 0.053618 | 0.070599 | −0.006269 | 0.08127 | −0.053856 | 0.028669 | 0.013206 | 0.008849 | 0.040797 |
| 138 | −0.015138 | 0.040473 | 0.11852 | 0.017168 | −0.02111 | 0.049049 | −0.032441 | 0.04785 | −0.059424 | −0.028852 | 0.068591 | 0.076897 | 0.039771 | −0.037779 |
| 139 | −0.055516 | 0.090988 | 0.03123 | −0.150124 | 0.039068 | 0.042928 | −0.004673 | 0.057398 | −0.045258 | 0.039567 | −0.033672 | −0.116411 | −0.027869 | 0.031823 |
| 140 | 0.043023 | −0.080067 | −0.013953 | 0.09804 | −0.048051 | 0.053752 | −0.016075 | −0.102155 | −0.003543 | −0.029875 | −0.203493 | 0.081733 | −0.025462 | −0.056611 |
| 141 | 0.058539 | −0.013036 | −0.059686 | −0.034178 | −0.00855 | 0.04865 | 0.072099 | 0.045264 | −0.027842 | −0.032803 | −0.058607 | 0.081542 | 0.017738 | −0.052269 |
| 142 | 0.014542 | 0.035606 | 0.051179 | −0.021609 | 0.051569 | 0.002898 | 0.034165 | −0.020933 | 0.115048 | 0.006171 | 0.007912 | −0.106254 | −0.023833 | −0.012201 |
| 143 | 0.003521 | 0.064633 | −0.027415 | −0.030718 | 0.02144 | −0.0664 | 0.002328 | −0.024058 | 0.052992 | −0.11078 | −0.0749 | −0.060019 | 0.041685 | −0.021025 |
| 144 | 0.024178 | 0.072825 | 0.024031 | 0.052034 | 0.025485 | −0.050877 | 0.01882 | −0.087969 | 0.061638 | −0.059536 | −0.082811 | −0.127521 | −0.053867 | −0.050313 |
| 145 | 0.002047 | 0.089699 | 0.029237 | −0.029477 | −0.017056 | 0.031009 | 0.0065 | −0.05343 | 0.077758 | −0.108615 | −0.001431 | −0.006463 | −0.036397 | −0.0073 |
| 146 | −0.049862 | 0.07256 | 0.008398 | −0.016225 | 0.018233 | 0.046764 | 0.008509 | 0.072958 | 0.023436 | 0.034173 | 0.037811 | 0.042551 | −0.066676 | −0.026732 |
| 147 | −0.037479 | 0.027473 | 0.088243 | 0.056325 | −0.046834 | 0.05021 | −0.011905 | 0.031933 | 0.019537 | 0.093487 | −0.014953 | 0.01932 | −0.083721 | 0.021195 |
| 148 | 0.012546 | −0.02141 | 0.00284 | 0.004289 | −0.004137 | 0.135171 | −0.043258 | 0.03134 | 0.039293 | −0.072691 | −0.123364 | 0.110085 | −0.001337 | 0.174885 |
| 149 | 0.030889 | −0.032797 | −0.081633 | −0.046781 | 0.033173 | 0.03351 | 0.010638 | 0.000837 | −0.006522 | −0.038124 | −0.018258 | 0.079538 | 0.042502 | 0.015513 |
| 150 | 0.016092 | −0.096092 | −0.049137 | 0.031588 | 0.043015 | 0.016588 | 0.046588 | 0.047533 | 0.000273 | 0.031678 | 0.003881 | 0.030592 | 0.038083 | −0.004342 |
| 151 | 0.045001 | −0.122539 | 0.078546 | 0.178685 | −0.045429 | −0.025602 | 0.025092 | −0.103246 | 0.073323 | −0.02477 | 0.028 | 0.083916 | −0.160948 | 0.167146 |
| 152 | −0.000949 | 0.006519 | 0.03573 | −0.061992 | 0.05144 | 0.040377 | 0.018983 | −0.03429 | 0.016963 | 0.030634 | 0.074916 | −0.055136 | −0.01913 | 0.070352 |
| 153 | 0.028758 | 0.056311 | 0.027222 | −0.121023 | 0.036316 | −0.003214 | −0.013346 | −0.038095 | 0.06209 | −0.011051 | 0.017761 | −0.076221 | −0.007242 | 0.038054 |
| 154 | 0.081149 | 0.0536511 | 0.0589271 | −0.02882 | 0.054048 | −0.010637 | −0.022105 | −0.033414 | 0.083629 | −0.00401 | 0.095172 | −0.078671 | −0.023897 | −0.026786 |
| 155 | 0.041239 | 0.039392 | 0.075292 | 0.017198 | 0.034439 | 0.047813 | −0.024786 | 0.008501 | 0.100016 | 0.036792 | 0.116009 | −0.027587 | −0.033714 | −0.046428 |
| 156 | 0.075227 | −0.094229 | 0.015551 | 0.010473 | 0.02943 | 0.053836 | 0.021389 | 0.000362 | 0.10062 | 0.058006 | 0.068795 | 0.02695 | −0.081748 | 0.012984 |
| 157 | 0.014737 | −0.038645 | −0.032187 | 0.00026 | 0.018779 | −0.038836 | −0.016586 | 0.048865 | −0.015398 | −0.043543 | −0.007436 | −0.105185 | −0.069296 | −0.021751 |
| 158 | 0.012541 | −0.042363 | 0.142897 | 0.136398 | −0.039576 | 0.081054 | −0.012678 | −0.04948 | −0.0367 | −0.002008 | 0.040992 | −0.057201 | −0.142972 | −0.035641 |
| 159 | 0.030915 | −0.064262 | 0.043385 | 0.003628 | 0.071268 | 0.083379 | 0.089365 | −0.002767 | −0.039514 | −0.067186 | −0.107845 | −0.167889 | 0.107997 | 0.0566 |
| 160 | 0.024343 | −0.06163 | 0.017706 | −0.097916 | 0.085409 | 0.022564 | 0.030671 | −0.07677 | −0.074848 | 0.052153 | −0.120002 | −0.129284 | 0.067167 | −0.107388 |
| 161 | −0.013192 | −0.039282 | −0.043692 | −0.063179 | 0.100947 | 0.122706 | 0.159689 | 0.035896 | −0.030291 | 0.091948 | 0.02142 | 0.118334 | −0.008819 | 0.028385 |
| 162 | −0.007942 | −0.016125 | −0.044144 | −0.064 | 0.00276 | −0.031655 | 0.034673 | −0.057949 | 0.048835 | 0.004206 | −0.07228 | −0.100933 | 0.00512 | 0.074956 |
| 163 | 0.029902 | −0.011851 | −0.036337 | −0.071937 | 0.070126 | 0.013863 | 0.026581 | 0.009159 | 0.010498 | 0.029021 | 0.063738 | −0.040676 | −0.010477 | 0.095341 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 164 | −0.025705 | −0.004168 | 0.100198 | 0.108173 | 0.038409 | 0.034226 | −0.078588 | −0.06538 | 0.007124 | −0.037385 | 0.131934 | −0.094584 | −0.040705 | 0.029174 |
| 165 | 0.005339 | 0.021558 | 0.066279 | 0.046599 | 0.099246 | 0.030834 | −0.043351 | 0.013064 | 0.013853 | −0.063747 | 0.039429 | 0.02626 | 0.024816 | 0.021046 |
| 166 | −0.0026 | −0.012626 | 0.061117 | 0.083996 | 0.092995 | −0.006928 | −0.062634 | −0.254353 | 0.023546 | 0.035519 | −0.082449 | −0.051191 | 0.067406 | −0.084109 |
| 167 | 0.037573 | −0.005011 | −0.067861 | −0.050134 | 0.097555 | −0.034133 | 0.019625 | −0.080337 | 0.007615 | 0.038969 | −0.004999 | 0.015349 | 0.008197 | −0.03557 |
| 168 | −0.140602 | 0.010978 | −0.013049 | 0.011292 | −0.056148 | −0.027124 | 0.027705 | 0.090856 | −0.060363 | 0.036211 | 0.079237 | −0.063911 | −0.060377 | 0.048593 |
| 169 | −0.105699 | 0.079553 | −0.057701 | 0.037513 | −0.050545 | 0.109472 | −0.042999 | −0.002422 | −0.024045 | 0.015785 | 0.042607 | −0.064898 | 0.02927 | −0.009039 |
| 170 | −0.076544 | 0.115036 | −0.073938 | 0.044572 | −0.051275 | 0.149613 | −0.00084 | −0.050006 | −0.001342 | 0.070243 | 0.059109 | −0.034945 | 0.024925 | 0.002075 |
| 171 | −0.092484 | 0.062807 | −0.031576 | 0.008429 | −0.060755 | 0.088011 | −0.006402 | −0.016096 | −0.022787 | −0.004355 | −0.018772 | −0.046758 | −0.000778 | −0.007793 |
| 172 | −0.075608 | 0.015243 | 0.058232 | 0.01383 | 0.041825 | 0.00125 | −0.066338 | 0.012789 | −0.038222 | 0.010966 | −0.052743 | 0.00299 | 0.048645 | 0.001182 |
| 173 | −0.019223 | 0.030094 | 0.058918 | −0.065957 | −0.005406 | 0.004617 | −0.020185 | 0.031301 | −0.03882 | 0.020454 | −0.055695 | 0.077287 | 0.012629 | 0.003719 |
| 174 | −0.066145 | 0.048498 | 0.023124 | −0.006538 | −0.02625 | −0.062675 | −0.030164 | 0.051054 | −0.000202 | 0.062665 | 0.014388 | 0.064751 | 0.00664 | −0.009229 |
| 175 | −0.065589 | 0.010145 | 0.028744 | −0.040403 | −0.016413 | −0.026557 | 0.011321 | 0.010179 | −0.034562 | 0.107551 | −0.020152 | 0.113099 | 0.022463 | −0.04175 |
| 176 | −0.093132 | −0.008161 | 0.007178 | 0.040011 | 0.05823 | −0.032952 | −0.047367 | −0.015738 | −0.008239 | −0.000035 | −0.100678 | −0.050476 | 0.018571 | −0.047846 |
| 177 | −0.055319 | −0.025853 | 0.032616 | 0.012247 | 0.090567 | 0.000756 | 0.056883 | 0.073888 | −0.161499 | −0.031123 | 0.0692 | −0.148083 | −0.1823 | −0.003863 |
| 178 | −0.033541 | 0.071613 | 0.049431 | 0.007921 | −0.079903 | −0.016135 | −0.025344 | −0.010664 | 0.035105 | −0.123794 | −0.019156 | −0.037003 | 0.072451 | 0.062951 |
| 179 | −0.029038 | 0.089368 | 0.033548 | 0.005895 | −0.119402 | 0.015688 | 0.03625 | −0.026069 | 0.014168 | 0.007444 | −0.006561 | −0.022072 | −0.010484 | 0.036865 |
| 180 | −0.006904 | 0.103929 | 0.028348 | 0.005982 | −0.103527 | 0.018804 | 0.021874 | −0.036962 | 0.053443 | 0.014319 | −0.00158 | −0.005294 | 0.010589 | 0.021934 |
| 181 | −0.002408 | 0.111887 | 0.02281 | 0.006564 | −0.101335 | 0.023467 | 0.031635 | −0.049758 | 0.056419 | 0.016698 | 0.000095 | −0.009633 | 0.008141 | 0.026279 |
| 182 | 0.006058 | 0.114086 | 0.044267 | 0.003081 | −0.069648 | 0.014756 | 0.07036 | −0.052503 | 0.009055 | 0.043011 | −0.014564 | 0.013503 | 0.017188 | 0.038127 |
| 183 | −0.008922 | 0.054718 | 0.09171 | 0.004923 | −0.09993 | 0.002446 | 0.088889 | 0.008342 | −0.026764 | 0.001052 | −0.036888 | 0.006586 | −0.01573 | 0.014329 |
| 184 | −0.020105 | −0.01651 | 0.088422 | 0.016129 | −0.079249 | −0.066314 | 0.042041 | 0.07654 | −0.0174 | −0.054492 | −0.037046 | −0.025367 | −0.065327 | −0.003389 |
| 185 | 0.016335 | 0.003088 | 0.147444 | 0.018325 | −0.06256 | −0.091469 | 0.000897 | −0.003205 | 0.089187 | −0.020832 | 0.026524 | −0.001064 | −0.007381 | −0.042145 |
| 186 | −0.012043 | 0.02513 | 0.170225 | −0.005897 | −0.015262 | −0.102108 | 0.039972 | 0.016527 | 0.027467 | 0.070809 | −0.056743 | 0.066517 | 0.065977 | −0.047355 |
| 187 | 0.036642 | 0.032725 | 0.116632 | 0.014928 | 0.027069 | −0.070412 | 0.049406 | 0.055385 | −0.011062 | 0.074391 | −0.058797 | 0.080729 | 0.02718 | −0.02189 |
| 188 | 0.008564 | 0.051057 | 0.094596 | 0.026655 | 0.006388 | −0.132561 | 0.024356 | 0.062 | 0.002907 | 0.074784 | −0.002663 | 0.088654 | 0.029786 | −0.033935 |
| 189 | −0.024168 | 0.036857 | 0.079278 | 0.007136 | −0.066188 | −0.141846 | −0.022859 | 0.076439 | −0.025992 | 0.072591 | 0.021073 | 0.056722 | 0.010662 | −0.060297 |
| 190 | −0.008697 | 0.049833 | −0.011989 | −0.010798 | −0.007832 | 0.005712 | −0.028897 | −0.079881 | −0.067053 | −0.010886 | 0.029151 | 0.011384 | 0.008027 | −0.0245 |
| 191 | 0.026859 | 0.039877 | −0.046891 | 0.003163 | −0.030554 | 0.022266 | 0.002211 | −0.039449 | −0.06182 | 0.014588 | 0.024203 | 0.000417 | −0.007868 | −0.030064 |
| 192 | −0.014842 | −0.03234 | 0.077331 | −0.00838 | −0.028185 | −0.003922 | 0.086043 | 0.03343 | −0.129491 | 0.096553 | 0.003218 | −0.005673 | −0.037143 | −0.001422 |
| 193 | −0.0228 | 0.026837 | 0.097283 | −0.02096 | −0.012816 | −0.040284 | 0.059457 | 0.035689 | −0.108756 | 0.060386 | −0.051599 | 0.044433 | 0.019447 | 0.010289 |
| 194 | −0.037471 | 0.01984 | 0.12476 | −0.027921 | 0.004191 | −0.105129 | 0.013478 | 0.009877 | −0.043318 | 0.089132 | −0.10368 | 0.088832 | 0.012612 | −0.012754 |
| 195 | −0.004161 | 0.019322 | 0.080181 | −0.000946 | 0.080163 | −0.006929 | −0.076023 | −0.046444 | 0.003627 | 0.048078 | −0.10089 | 0.066417 | −0.024311 | 0.057409 |
| 196 | −0.01282 | 0.046453 | 0.034008 | −0.007766 | 0.003937 | −0.01045 | −0.077825 | −0.047035 | 0.007081 | 0.044188 | −0.041159 | 0.049792 | −0.047788 | 0.030757 |
| 197 | 0.040029 | 0.056239 | −0.014186 | 0.003621 | −0.004817 | 0.03959 | −0.004413 | −0.034258 | −0.050214 | 0.029734 | 0.044445 | 0.063839 | 0.018888 | −0.031214 |
| 198 | −0.004891 | −0.008252 | 0.146508 | 0.031597 | 0.068383 | −0.006712 | −0.038054 | 0.011841 | 0.026364 | 0.094596 | −0.052607 | 0.047738 | 0.034128 | 0.112481 |
| 199 | 0.004346 | −0.082614 | 0.008125 | −0.09732 | 0.03029 | −0.031826 | 0.003943 | −0.04044 | 0.006871 | −0.094304 | −0.040253 | 0.117257 | −0.14798 | 0.108182 |
| 200 | 0.005193 | −0.003453 | 0.121906 | 0.011853 | 0.102541 | 0.009338 | −0.038564 | −0.02639 | 0.050994 | 0.055171 | −0.057296 | 0.0202 | 0.031162 | 0.091519 |
| 201 | −0.015323 | 0.05213 | −0.039029 | −0.059007 | 0.034087 | −0.014846 | 0.023202 | 0.058613 | −0.109152 | −0.017014 | −0.073148 | −0.126884 | 0.005973 | −0.087926 |
| 202 | 0.001226 | −0.001272 | 0.128089 | 0.04074 | 0.087611 | 0.038768 | −0.059222 | 0.03242 | 0.003282 | 0.051029 | −0.03048 | 0.032877 | 0.0668 | 0.151501 |
| 203 | 0.051459 | 0.006902 | 0.057215 | 0.006931 | 0.056094 | 0.145141 | 0.056889 | 0.025062 | −0.090819 | −0.00358 | 0.063014 | −0.011378 | 0.071558 | 0.033669 |
| 204 | 0.006125 | 0.029134 | 0.006425 | −0.057792 | 0.040267 | 0.037067 | 0.012625 | 0.021193 | −0.060701 | −0.100754 | 0.140149 | 0.080718 | 0.142885 | 0.000162 |
| 205 | −0.024745 | −0.066347 | −0.005574 | 0.013112 | 0.084191 | −0.010747 | 0.05596 | −0.020513 | 0.021658 | −0.127356 | 0.009958 | 0.065893 | −0.220603 | 0.160952 |
| 206 | −0.0139 | −0.021613 | 0.010577 | 0.080046 | −0.00595 | 0.028899 | −0.134881 | 0.074626 | −0.123183 | −0.278725 | 0.238506 | −0.000013 | 0.074737 | −0.007498 |
| 207 | −0.016971 | −0.009982 | 0.065019 | 0.065537 | −0.040165 | 0.110107 | −0.083338 | 0.044554 | −0.118986 | −0.113114 | 0.037999 | 0.11397 | 0.099377 | −0.028496 |
| 208 | 0.039868 | 0.012651 | 0.103923 | 0.134084 | 0.031329 | 0.097984 | −0.047582 | 0.036537 | −0.065114 | −0.004254 | 0.127256 | −0.13559 | 0.091751 | −0.030349 |
| 209 | −0.027653 | 0.019079 | 0.10099 | 0.051839 | 0.059545 | 0.020631 | 0.072812 | −0.095552 | −0.012981 | 0.030911 | −0.100793 | 0.105466 | −0.057074 | 0.100785 |
| 210 | 0.030587 | −0.026283 | 0.086561 | 0.080963 | −0.035715 | 0.112727 | −0.006595 | −0.029923 | 0.052486 | −0.118828 | 0.123396 | 0.19164 | −0.07585 | 0.128788 |
| 211 | −0.031093 | −0.00778 | −0.044203 | 0.014485 | 0.016881 | 0.029072 | −0.093956 | −0.084219 | −0.080417 | −0.118206 | 0.023386 | 0.155914 | 0.058105 | −0.057904 |
| 212 | 0.003174 | 0.060676 | 0.018781 | −0.08852 | 0.022828 | −0.062469 | −0.057391 | −0.095857 | 0.012046 | 0.162946 | −0.00283 | 0.054828 | 0.024383 | −0.065406 |
| 213 | −0.059935 | 0.011403 | 0.031844 | 0.045029 | −0.018803 | 0.008429 | −0.052085 | −0.002008 | −0.053601 | −0.226312 | −0.010816 | 0.12009 | 0.091678 | −0.028899 |
| 214 | −0.055489 | 0.049046 | 0.041108 | 0.005497 | −0.117839 | −0.00671 | −0.002265 | 0.019559 | 0.009363 | −0.03005 | −0.010775 | −0.064814 | −0.019624 | 0.01944 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 215 | −0.049357 | 0.009916 | 0.11693 | 0.022859 | −0.150154 | −0.052602 | −0.016649 | −0.01064 | 0.043674 | −0.031392 | 0.033873 | −0.080757 | −0.018553 | −0.017358 |
| 216 | −0.136985 | −0.02392 | −0.083129 | −0.037916 | −0.085242 | −0.024864 | 0.017201 | 0.021194 | 0.069363 | 0.03122 | 0.041073 | 0.027829 | −0.033007 | −0.010709 |
| 217 | −0.172105 | 0.033833 | −0.008929 | −0.005152 | 0.108506 | 0.006329 | −0.028789 | −0.06416 | −0.049197 | 0.048606 | 0.017672 | 0.032583 | −0.035458 | 0.084284 |
| 218 | −0.014014 | 0.074706 | −0.01715 | −0.03426 | −0.020718 | 0.009616 | 0.060293 | −0.014464 | −0.002029 | −0.050896 | −0.006885 | 0.018959 | 0.015141 | 0.026498 |
| 219 | −0.15145 | 0.029098 | −0.064514 | −0.074987 | −0.085492 | 0.038689 | 0.032371 | −0.02929 | 0.049146 | −0.038782 | 0.003057 | 0.013863 | −0.046624 | −0.013619 |
| 220 | −0.090846 | 0.05379 | −0.00966 | −0.034078 | 0.065069 | 0.028628 | −0.07426 | −0.096539 | 0.000595 | 0.059673 | 0.069038 | −0.034367 | 0.023609 | −0.044692 |
| 221 | −0.002422 | 0.04883 | 0.043063 | −0.058678 | 0.035072 | 0.027291 | −0.064894 | 0.015079 | 0.049375 | −0.066637 | −0.004011 | 0.04402 | 0.033662 | 0.012525 |
| 222 | −0.065898 | 0.005842 | −0.000434 | −0.073406 | −0.038407 | 0.067122 | −0.034244 | −0.020281 | −0.098777 | 0.06089 | 0.000308 | 0.02037 | −0.044591 | 0.08421 |
| 223 | −0.067895 | 0.01266 | −0.014552 | −0.065204 | −0.058316 | 0.04954 | −0.055156 | −0.022833 | −0.059142 | 0.044896 | −0.010888 | 0.029032 | −0.024451 | 0.044893 |
| 224 | 0.006501 | −0.060659 | 0.02677 | −0.017174 | −0.03243 | −0.005179 | −0.091985 | 0.123243 | −0.080608 | −0.043958 | −0.065163 | −0.073019 | 0.063888 | 0.115782 |
| 225 | 0.011938 | −0.062913 | 0.036019 | −0.01662 | −0.041135 | −0.001962 | −0.087297 | 0.126848 | −0.089072 | −0.041101 | −0.059586 | −0.08301 | 0.058197 | 0.116992 |
| 226 | −0.021379 | −0.037664 | 0.039357 | −0.015779 | −0.015622 | 0.028039 | 0.006701 | 0.035041 | 0.048403 | 0.005831 | −0.05152 | −0.020258 | −0.014488 | −0.015759 |
| 227 | −0.004039 | −0.10404 | 0.027391 | −0.012629 | −0.098347 | 0.017085 | −0.043156 | 0.137442 | 0.016243 | −0.035663 | −0.09017 | −0.105835 | 0.07104 | 0.069794 |
| 228 | −0.010433 | −0.130355 | 0.037136 | −0.111111 | −0.009384 | 0.104458 | −0.048244 | 0.081758 | 0.013953 | 0.005966 | 0.021062 | −0.055933 | 0.016137 | −0.001169 |
| 229 | −0.040988 | −0.03714 | 0.031164 | 0.031058 | 0.028245 | −0.014158 | 0.023647 | 0.219749 | 0.064126 | 0.100976 | −0.083377 | −0.034979 | 0.034459 | −0.032592 |
| 230 | −0.076643 | −0.041116 | −0.063857 | −0.01295 | −0.095687 | −0.0333 | 0.039734 | 0.085813 | 0.046464 | 0.017293 | −0.014074 | −0.028496 | 0.004945 | −0.006612 |
| 231 | −0.015647 | −0.037858 | −0.015581 | −0.046433 | −0.013882 | 0.112921 | 0.087432 | −0.027298 | 0.050084 | −0.051739 | −0.032957 | 0.001732 | 0.052623 | 0.020823 |
| 232 | −0.02834 | −0.075982 | 0.034065 | −0.057652 | 0.035944 | 0.053978 | −0.071141 | 0.048872 | −0.010271 | 0.070227 | 0.019674 | −0.0166 | −0.044288 | −0.0194 |
| 233 | 0.029403 | −0.065873 | 0.036367 | −0.026974 | −0.053511 | 0.039902 | 0.036914 | 0.055007 | 0.025048 | −0.042406 | −0.045824 | 0.012531 | −0.015152 | −0.074735 |
| 234 | −0.059274 | −0.135153 | −0.011923 | −0.112332 | −0.064037 | 0.084582 | 0.120031 | −0.024065 | 0.132896 | −0.112907 | 0.013806 | 0.014336 | 0.021545 | −0.160675 |
| 235 | −0.033921 | −0.10484 | 0.027343 | −0.161752 | −0.025778 | 0.057504 | 0.069775 | 0.011201 | 0.124546 | −0.065967 | 0.040765 | −0.015632 | 0.062828 | −0.103672 |
| 236 | −0.008178 | −0.010096 | −0.019213 | 0.021036 | 0.054521 | −0.032751 | −0.001162 | −0.018735 | 0.040838 | 0.036862 | 0.043915 | 0.059678 | −0.039183 | −0.051232 |
| 237 | 0.064949 | 0.00589 | −0.056739 | 0.116893 | −0.008292 | −0.043788 | 0.105439 | −0.058047 | −0.098378 | 0.030962 | 0.059123 | −0.036601 | −0.05555 | 0.057951 |
| 238 | −0.073593 | −0.04755 | −0.090457 | −0.001212 | −0.085312 | 0.023476 | 0.054962 | −0.018375 | −0.010412 | −0.049547 | 0.02047 | 0.015348 | −0.048154 | 0.029747 |
| 239 | −0.068665 | −0.037153 | −0.062093 | −0.037378 | −0.092109 | 0.063389 | 0.024184 | 0.023997 | 0.028598 | −0.051045 | −0.032846 | 0.06161 | −0.000958 | 0.040878 |
| 240 | 0.010502 | −0.067658 | 0.021279 | −0.030065 | 0.021739 | 0.112597 | −0.046475 | −0.059624 | 0.001747 | −0.081233 | −0.019493 | 0.022419 | −0.01727 | −0.111118 |
| 241 | −0.000575 | −0.071738 | 0.013621 | −0.02056 | −0.02449 | 0.041795 | 0.02112 | −0.043649 | 0.042685 | −0.038413 | 0.007352 | 0.022165 | −0.030617 | −0.169517 |
| 242 | 0.037899 | −0.064205 | 0.062626 | −0.068499 | 0.006417 | −0.005733 | 0.081854 | 0.003157 | 0.078644 | 0.001284 | 0.032479 | −0.006111 | 0.028061 | −0.060913 |
| 243 | 0.000247 | −0.089181 | 0.060907 | −0.144067 | −0.018666 | −0.01036 | −0.016676 | 0.043903 | 0.085821 | −0.017639 | 0.077179 | −0.085796 | −0.010204 | 0.051007 |
| 244 | 0.069937 | 0.031009 | 0.037404 | 0:035801 | 0.072343 | −0.000915 | −0.048999 | 0.043342 | 0.083612 | −0.078562 | 0.011709 | −0.008909 | 0.074931 | 0.038036 |
| 245 | 0.016536 | 0.049035 | 0.003408 | 0.046488 | 0.004649 | −0.113407 | −0.040344 | 0.017749 | 0.06228 | −0.032215 | 0.051562 | 0.014032 | 0.06705 | −0.041732 |
| 246 | 0.074915 | 0.022705 | −0.000848 | 0.020096 | −0.043449 | −0.008554 | 0.027234 | −0.047387 | −0.038409 | 0.025094 | −0.002181 | 0.003819 | 0.017949 | −0.066959 |
| 247 | −0.030646 | −0.01095 | −0.034127 | −0.034258 | −0.038142 | −0.017167 | −0.055531 | −0.030962 | −0.028584 | −0.006764 | −0.012112 | 0.019607 | −0.033831 | −0.059708 |
| 248 | −0.054486 | −0.02796 | −0.031094 | −0.0653 | −0.021992 | 0.013513 | −0.083845 | −0.016256 | −0.024139 | 0.018576 | −0.009014 | 0.010905 | −0.068813 | −0.061605 |
| 249 | −0.055972 | −0.097878 | 0.003037 | −0.05188 | −0.002561 | 0.157765 | −0.047548 | −0.095168 | −0.136257 | 0.053805 | 0.011916 | −0.026259 | −0.06297 | −0.029662 |
| 250 | −0.003647 | −0.063832 | −0.002315 | −0.029031 | 0.012069 | 0.084532 | 0.02308 | −0.095446 | −0.008223 | −0.05512 | −0.027855 | 0.016464 | −0.006207 | −0.135091 |
| 251 | −0.010221 | −0.039728 | 0.049307 | −0.056989 | 0.036786 | 0.051562 | 0.003609 | −0.062866 | 0.056869 | −0.077003 | 0.010671 | −0.030342 | 0.021636 | −0.133688 |
| 252 | −0.025219 | −0.060109 | 0.084571 | −0.064289 | 0.074219 | −0.009003 | −0.054443 | −0.055395 | 0.09709 | −0.074859 | −0.009937 | −0.051803 | 0.003127 | −0.022305 |
| 253 | −0.01355 | −0.098658 | 0.073131 | −0.074613 | 0.036169 | 0.01038 | −0.0415 | 0.057226 | 0.087858 | 0.048719 | 0.114689 | −0.070604 | −0.041104 | 0.064998 |
| 254 | 0.003708 | −0.008152 | 0.004229 | −0.022389 | −0.00196 | 0.020768 | −0.094142 | 0.001476 | −0.031599 | 0.028671 | 0.014859 | 0.006003 | 0.050362 | 0.015062 |
| 255 | 0.055957 | 0.045765 | 0.037643 | 0.002942 | 0.070696 | −0.001025 | −0.089772 | −0.002863 | 0.06756 | −0.017318 | 0.038605 | −0.00942 | 0.087922 | −0.042345 |
| 256 | −0.025779 | 0.066955 | 0.039698 | 0.01519 | 0.084303 | −0.102981 | −0.146342 | 0.000343 | 0.066007 | 0.026548 | 0.104167 | 0.015474 | 0.055528 | −0.06244 |
| 257 | −0.02569 | −0.018226 | 0.037076 | −0.008596 | 0.024302 | −0.025377 | 0.001177 | −0.024715 | 0.000842 | 0.027235 | −0.002168 | 0.019085 | −0.060722 | −0.035703 |
| 258 | −0.016918 | −0.02407 | 0.004067 | −0.019564 | 0.041937 | −0.054786 | −0.138311 | −0.011225 | −0.036572 | 0.039827 | 0.036645 | 0.018953 | −0.108259 | 0.030063 |
| 259 | −0.042429 | −0.080674 | 0.015888 | −0.062144 | −0.016929 | 0.083019 | −0.002932 | −0.066333 | −0.085238 | 0.046554 | −0.017665 | −0.039793 | −0.00853 | −0.01441 |
| 260 | −0.031566 | −0.093494 | 0.038242 | −0.058 | 0.059069 | 0.08041 | −0.059308 | −0.107801 | −0.044937 | −0.062222 | −0.120914 | −0.051231 | −0.019971 | 0.024083 |
| 261 | −0.029326 | −0.082663 | 0.041326 | −0.067574 | 0.084437 | 0.060035 | −0.077831 | −0.112031 | 0.006619 | −0.083287 | −0.079718 | −0.028385 | −0.027714 | −0.008959 |
| 262 | −0.01134 | −0.032427 | 0.02978 | −0.026032 | 0.093618 | 0.009282 | −0.033335 | −0.045903 | 0.03327 | 0.010732 | −0.006353 | 0.024584 | 0.001394 | 0.036026 |
| 263 | −0.014737 | −0.034029 | 0.022039 | −0.07202 | 0.07039 | −0.002586 | −0.01387 | −0.023441 | 0.048782 | 0.041416 | 0.048184 | 0.01172 | 0.037706 | 0.033217 |
| 264 | −0.039658 | −0.025345 | −0.039849 | −0.032349 | −0.015901 | 0.072246 | −0.062917 | −0.030293 | −0.121349 | 0.110028 | −0.006626 | −0.036153 | 0.048322 | 0.044486 |
| 265 | −0.052591 | −0.016111 | −0.002892 | −0.038091 | 0.042831 | 0.033683 | −0.187005 | −0.042586 | −0.140258 | 0.072886 | −0.064011 | −0.009418 | 0.012635 | 0.0695 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 266 | −0.036968 | 0.003408 | 0.019573 | −0.030823 | 0.073382 | −0.037901 | −0.195508 | −0.041466 | −0.037846 | −0.004237 | −0.062321 | 0.006286 | −0.007396 | 0.023038 |
| 267 | −0.044502 | −0.011907 | 0.029851 | 0.010432 | 0.02315 | 0.057618 | −0.011213 | 0.115934 | 0.091174 | 0.023263 | 0.015952 | 0.005426 | 0.062374 | 0.031916 |
| 268 | −0.016049 | −0.03091 | 0.036807 | −0.012361 | −0.006629 | 0.032729 | 0.003114 | 0.033398 | 0.036963 | −0.013287 | −0.047144 | 0.006697 | 0.030312 | 0.004772 |
| 269 | −0.030618 | −0.020674 | 0.031479 | −0.006422 | −0.005237 | 0.019297 | 0.007257 | 0.026807 | 0.030238 | 0.004404 | −0.042622 | −0.012188 | −0.012271 | −0.02758 |
| 270 | 0.000083 | −0.025567 | 0.037412 | −0.010579 | −0.007133 | 0.019824 | 0.003337 | 0.040076 | 0.02943 | −0.005063 | −0.074685 | −0.037565 | 0.015941 | 0.008966 |
| 271 | 0.015922 | −0.023582 | 0.032067 | −0.004324 | 0.092544 | −0.033541 | 0.05772 | 0.094872 | 0.112113 | 0.072076 | 0.037805 | 0.036376 | 0.031396 | −0.064563 |
| 272 | −0.039215 | −0.000214 | 0.017944 | 0.002797 | 0.065145 | 0.031784 | 0.031363 | 0.105887 | 0.061931 | 0.078099 | −0.040411 | −0.011353 | 0.022325 | −0.063934 |
| 273 | 0.000348 | 0.008471 | 0.025986 | −0.003935 | 0.036512 | −0.007979 | 0.051177 | 0.03467 | 0.00065 | 0.03255 | −0.068933 | −0.031824 | 0.018296 | −0.021786 |
| 274 | −0.001662 | 0.011087 | 0.028145 | −0.001219 | 0.034403 | −0.011991 | 0.053923 | 0.031006 | 0.001659 | 0.039474 | −0.061652 | −0.039619 | 0.008539 | −0.032309 |
| 275 | −0.02925 | −0.00318 | −0.055611 | −0.021692 | −0.030785 | −0.033111 | 0.029851 | 0.076854 | −0.004053 | 0.019911 | −0.0399 | −0.052532 | 0.037595 | −0.001333 |
| 276 | −0.022146 | −0.026155 | −0.018116 | 0.016558 | 0.067045 | −0.024263 | 0.006792 | 0.039768 | 0.089276 | 0.066279 | 0.049904 | 0.071737 | −0.034695 | −0.065963 |
| 277 | 0.068206 | 0.050129 | −0.061674 | 0.076609 | 0.019064 | −0.030841 | 0.104399 | 0.032616 | −0.060638 | −0.029193 | −0.060382 | 0.014599 | 0.039662 | 0.120964 |
| 278 | 0.081804 | 0.046651 | −0.048685 | 0.078128 | −0.005144 | −0.014557 | 0.08624 | 0.058317 | −0.050096 | −0.014975 | −0.059496 | 0.026085 | 0.046827 | 0.122943 |
| 279 | −0.085263 | −0.016304 | −0.0865 | −0.047659 | −0.083608 | 0.055291 | 0.016573 | 0.033714 | 0.015484 | −0.065182 | −0.059008 | 0.036286 | 0.005978 | 0.02853 |
| 280 | 0.019939 | −0.057575 | 0.069 | −0.098067 | −0.012782 | −0.036404 | −0.050758 | 0.098819 | 0.094536 | 0.02726 | 0.096377 | −0.103652 | 0.008122 | 0.109253 |
| 281 | 0.089506 | 0.016734 | −0.009189 | −0.007292 | −0.01909 | −0.017534 | −0.001207 | −0.00323 | −0.061218 | 0.025934 | −0.015355 | −0.014481 | 0.041799 | −0.032751 |
| 282 | 0.075787 | 0.033181 | −0.015834 | −0.047291 | −0.015913 | −0.032444 | −0.059028 | 0.013105 | −0.045778 | 0.022095 | −0.009142 | −0.00228 | 0.044576 | −0.03611 |
| 283 | −0.062449 | −0.012545 | −0.054029 | −0.068151 | −0.032532 | −0.010754 | −0.09924 | 0.007581 | 0.01542 | −0.010683 | −0.022203 | 0.004468 | −0.042092 | −0.105219 |
| 284 | −0.010075 | −0.017973 | 0.02342 | −0.007193 | 0.021444 | −0.019679 | 0.006484 | −0.012066 | 0.009948 | 0.034751 | −0.000821 | 0.000879 | −0.026104 | −0.051882 |
| 285 | −0.003832 | −0.019083 | 0.02436 | −0.009266 | 0.01986 | −0.008746 | 0.005345 | −0.003578 | 0.023956 | 0.032954 | 0.00834 | 0.005034 | −0.034901 | −0.036434 |
| 286 | −0.004825 | −0.009444 | 0.009121 | −0.013215 | 0.005205 | −0.059094 | −0.101978 | 0.015892 | −0.016018 | 0.075965 | 0.069689 | −0.00859 | −0.09106 | 0.031161 |
| 287 | −0.011631 | −0.02373 | 0.002989 | −0.025329 | −0.006991 | −0.054864 | −0.160539 | 0.049157 | 0.00137 | 0.049753 | 0.069688 | 0.002387 | −0.105049 | 0.023245 |
| 288 | −0.072351 | −0.057601 | −0.039709 | −0.032753 | 0.093175 | −0.123388 | −0.108653 | 0.010282 | −0.066916 | 0.036337 | 0.062451 | 0.01493 | −0.114738 | −0.019689 |
| 289 | −0.02701 | −0.013676 | 0.024611 | −0.011301 | 0.136912 | −0.047671 | −0.073303 | −0.032596 | −0.001136 | 0.008756 | −0.012091 | 0.012327 | 0.015768 | −0.005262 |
| 290 | −0.026675 | −0.075558 | 0.014377 | −0.016064 | 0.140601 | −0.139362 | 0.094334 | −0.025468 | −0.133794 | −0.089102 | 0.088242 | −0.036894 | −0.061319 | −0.020085 |
| 291 | −0.027056 | −0.076819 | 0.009274 | −0.018003 | 0.140954 | −0.145819 | 0.093809 | −0.029371 | −0.14003 | −0.088831 | 0.075885 | −0.033195 | −0.053364 | −0.015051 |
| 292 | −0.051317 | −0.085324 | 0.009395 | −0.034313 | 0.109863 | −0.123824 | 0.107256 | −0.017258 | −0.114217 | −0.090942 | 0.096058 | −0.025801 | −0.058461 | −0.02595 |
| 293 | 0.005168 | 0.004523 | 0.055104 | −0.039802 | −0.030004 | −0.013807 | 0.080186 | 0.038567 | −0.077948 | 0.002764 | −0.032667 | 0.118634 | −0.007081 | −0.053186 |
| 294 | 0.029522 | 0.026378 | 0.032181 | −0.008367 | −0.036021 | −0.046593 | 0.024724 | 0.02885 | −0.055627 | −0.0426 | −0.07793 | 0.00307 | 0.027513 | −0.008862 |
| 295 | 0.02602 | 0.015871 | 0.03559 | −0.007813 | −0.005039 | −0.023243 | 0.098743 | −0.001868 | −0.058302 | 0.01859 | −0.058074 | 0.025301 | 0.024902 | −0.055181 |
| 296 | 0.008822 | 0.06629 | 0.046405 | −0.059374 | −0.008866 | −0.034213 | 0.014135 | 0.008173 | −0.079558 | 0.014221 | −0.041081 | −0.02647 | 0.055791 | −0.029441 |
| 297 | 0.008562 | 0.044783 | 0.041217 | −0.043469 | −0.022465 | −0.017272 | 0.076032 | −0.001075 | −0.045316 | 0.012526 | −0.036555 | 0.040287 | 0.032086 | −0.058531 |
| 298 | 0.087717 | 0.025511 | 0.061544 | −0.008612 | −0.082168 | −0.142589 | 0.018356 | −0.022344 | −0.030458 | −0.062661 | 0.063066 | −0.016625 | −0.083959 | −0.0398 |
| 299 | 0.026864 | 0.076884 | 0.042574 | −0.05151 | −0.033361 | 0.007027 | 0.02223 | 0.025587 | −0.06281 | −0.017773 | 0.028246 | 0.018443 | 0.012084 | −0.008478 |
| 300 | 0.092461 | 0.050126 | 0.039117 | −0.058823 | −0.128722 | −0.098204 | −0.022613 | 0.002884 | 0.061055 | −0.07937 | 0.012518 | −0.051915 | −0.055675 | 0.061003 |
| 301 | 0.03187 | 0.008567 | 0.034752 | −0.010299 | −0.030155 | −0.000122 | 0.048457 | −0.005387 | −0.059381 | −0.014975 | −0.018794 | 0.040946 | 0.011151 | −0.035845 |
| 302 | 0.013628 | 0.07046 | 0.050281 | −0.033166 | −0.023798 | −0.007468 | 0.004396 | 0.011256 | −0.067223 | −0.030743 | −0.010398 | −0.003185 | 0.018405 | 0.027988 |
| 303 | 0.039186 | 0.035004 | 0.04378 | −0.004599 | −0.063736 | −0.032274 | −0.09326 | 0.030482 | −0.045327 | −0.044593 | 0.029912 | −0.022123 | −0.016409 | 0.080555 |
| 304 | 0.007906 | 0.073184 | 0.031929 | −0.036868 | −0.041659 | −0.022649 | −0.097926 | 0.042276 | −0.054632 | −0.06121 | 0.035111 | −0.032852 | 0.002476 | 0.074156 |
| 305 | 0.049886 | −0.033148 | 0.073785 | 0.033607 | −0.012681 | −0.055257 | 0.047425 | 0.016711 | −0.040565 | 0.007214 | −0.048018 | −0.031903 | 0.076187 | −0.000645 |
| 306 | −0.020672 | 0.09275 | 0.055608 | −0.062261 | 0.013574 | 0.034873 | 0.074261 | 0.026134 | −0.092284 | −0.029137 | 0.043653 | 0.022228 | −0.015336 | 0.010551 |
| 307 | 0.07109 | −0.03334 | 0.035861 | −0.03222 | 0.037708 | −0.017531 | 0.080883 | −0.006106 | −0.096723 | −0.011481 | 0.136902 | −0.033118 | −0.018979 | 0.068378 |
| 308 | −0.096906 | 0.15729 | 0.029045 | −0.106494 | 0.048298 | 0.023745 | 0.009432 | 0.041814 | −0.007207 | −0.024913 | 0.013084 | 0.018671 | −0.001518 | −0.001844 |
| 309 | −0.042679 | 0.057796 | 0.00542 | −0.050441 | −0.034494 | −0.007257 | −0.008254 | −0.012555 | 0.002598 | −0.005798 | −0.001307 | 0.010905 | 0.02766 | −0.010727 |
| 310 | −0.06847 | 0.102112 | 0.047454 | −0.053069 | −0.015666 | 0.012893 | −0.001099 | −0.005936 | −0.062305 | −0.027584 | −0.014285 | −0.023401 | 0.024856 | 0.02058 |
| 311 | 0.022982 | −0.039312 | 0.016428 | 0.025668 | −0.054005 | −0.035537 | 0.007343 | −0.018698 | −0.015454 | −0.026278 | −0.064009 | −0.010386 | 0.007697 | −0.024694 |
| 312 | 0.04245 | −0.041463 | −0.006193 | 0.085672 | −0.049792 | 0.021016 | 0.003375 | −0.043345 | −0.028447 | 0.103134 | 0.002034 | −0.023441 | 0.068358 | −0.073066 |
| 313 | 0.004505 | −0.012736 | −0.014445 | 0.025095 | −0.066893 | −0.022733 | −0.047102 | −0.03053 | 0.007963 | −0.000705 | −0.034307 | 0.007968 | 0.040152 | −0.027047 |
| 314 | 0.082618 | −0.143458 | −0.023337 | 0.102677 | −0.101642 | −0.015477 | −0.023358 | −0.093613 | 0.036011 | 0.079799 | 0.050426 | −0.001868 | 0.090181 | −0.013938 |
| 315 | −0.010438 | 0.009782 | −0.001099 | −0.009634 | −0.050374 | −0.037644 | −0.055033 | −0.022945 | 0.003757 | −0.001468 | 0.024839 | 0.032854 | −0.006957 | −0.018255 |
| 316 | 0.041025 | −0.09732 | −0.062639 | 0.007668 | −0.029903 | −0.030692 | 0.061777 | −0.046507 | −0.028155 | 0.086239 | 0.021165 | 0.023124 | 0.141326 | 0.091588 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 317 | −0.012605 | 0.00083 | −0.01385 | −0.02251 | −0.046905 | −0.048907 | −0.008768 | −0.040163 | −0.000601 | −0.001394 | −0.041731 | 0.036083 | 0.011761 | −0.043972 |
| 318 | −0.019791 | 0.034668 | 0.028269 | 0.005717 | −0.055853 | −0.035263 | −0.000921 | −0.029281 | −0.026709 | −0.011452 | −0.036836 | −0.00987 | −0.033375 | −0.031987 |
| 319 | −0.023932 | 0.006126 | −0.023444 | −0.029928 | −0.054688 | −0.045134 | −0.07846 | −0.018003 | −0.002803 | −0.010168 | 0.008279 | 0.036739 | 0.020862 | 0.008202 |
| 320 | −0.040697 | 0.045927 | −0.005156 | −0.047144 | −0.029348 | −0.0261 | −0.039367 | −0.011312 | −0.037357 | −0.072073 | 0.013931 | 0.022807 | −0.009491 | 0.006243 |
| 321 | 0.032219 | 0.066023 | 0.034512 | −0.013106 | 0.02943 | −0.001639 | 0.091192 | −0.030197 | −0.060696 | 0.033362 | 0.07086 | −0.03224 | 0.009985 | −0.03236 |
| 322 | 0.070296 | −0.037254 | −0.083246 | 0.014397 | −0.050698 | −0.01489 | 0.019174 | −0.114484 | −0.06635 | 0.004481 | −0.015537 | −0.089278 | 0.065651 | 0.002613 |
| 323 | 0.043625 | −0.005814 | 0.009361 | 0.026818 | 0.007357 | 0.025073 | 0.077398 | −0.07882 | −0.006063 | 0.015523 | 0.086482 | −0.102783 | 0.036412 | −0.058253 |
| 324 | 0.055346 | −0.027894 | −0.036104 | −0.090412 | −0.036356 | 0.012784 | 0.046201 | −0.038316 | −0.090863 | −0.015606 | 0.031543 | −0.033441 | 0.118673 | 0.066786 |
| 325 | −0.010286 | −0.01281 | 0.008223 | −0.020993 | −0.062605 | −0.041859 | −0.063413 | −0.023997 | 0.019678 | −0.012737 | −0.026354 | 0.021266 | −0.044124 | −0.0052 |
| 326 | 0.074659 | −0.102276 | 0.006741 | 0.070313 | −0.090818 | −0.053226 | −0.051677 | −0.083091 | 0.027445 | 0.029207 | 0.000259 | −0.038109 | −0.068972 | 0.020828 |
| 327 | −0.016063 | 0.064328 | 0.024175 | −0.056546 | 0.005678 | −0.019044 | 0.010175 | −0.006537 | −0.006137 | −0.00682 | 0.034004 | −0.008839 | 0.020064 | −0.020976 |
| 328 | 0.11554 | 0.024514 | 0.055805 | 0.044 | −0.040812 | −0.096777 | 0.036965 | −0.043975 | −0.068887 | 0.023045 | 0.135413 | −0.102672 | −0.010567 | −0.067254 |
| 329 | 0.023241 | 0.002084 | −0.014999 | −0.00652 | −0.012701 | −0.04605 | −0.000009 | −0.069632 | 0.010567 | 0.033219 | 0.011059 | −0.050729 | 0.066423 | −0.015121 |
| 330 | 0.08502 | 0.001199 | −0.07601 | 0.044151 | −0.056962 | −0.036905 | 0.002069 | −0.087867 | −0.012272 | 0.049411 | −0.024023 | −0.066119 | −0.036996 | −0.03772 |
| 331 | 0.006196 | −0.010072 | −0.006133 | −0.027899 | −0.037067 | −0.064259 | −0.037535 | −0.041964 | 0.001876 | 0.014245 | 0.039421 | 0.025167 | −0.023182 | −0.017163 |
| 332 | 0.086667 | 0.001733 | −0.062126 | 0.015138 | −0.162153 | −0.107558 | −0.051319 | −0.126428 | 0.004747 | −0.005499 | −0.04398 | −0.078378 | −0.007398 | 0.012521 |
| 333 | −0.00099 | −0.041726 | −0.008331 | −0.008988 | −0.056744 | −0.061612 | −0.024648 | −0.05105 | 0.003246 | −0.015797 | −0.030532 | 0.026159 | −0.064469 | −0.044635 |
| 334 | −0.001233 | −0.030816 | 0.031182 | 0.028882 | −0.06296 | −0.049349 | −0.064927 | −0.018737 | −0.060837 | −0.114237 | −0.041921 | 0.052332 | −0.026311 | −0.033685 |
| 335 | −0.029448 | 0.038341 | 0.003854 | −0.061046 | −0.022796 | −0.041108 | −0.035724 | −0.030981 | 0.014596 | −0.000298 | 0.013896 | 0.006717 | −0.035716 | −0.00748 |
| 336 | 0.049306 | −0.031012 | 0.033318 | 0.081894 | −0.093556 | −0.037983 | 0.050155 | −0.000471 | −0.059173 | 0.011729 | 0.01293 | −0.025087 | −0.110591 | 0.005315 |
| 337 | 0.093779 | −0.032432 | −0.007411 | −0.024346 | 0.028073 | 0.010532 | 0.090061 | −0.041919 | −0.110663 | 0.014826 | 0.072518 | −0.004431 | 0.026722 | 0.007829 |
| 338 | 0.054651 | −0.019013 | 0.087813 | 0.010487 | 0.008712 | 0.046267 | 0.025841 | 0.048237 | −0.126634 | −0.024036 | −0.089014 | −0.048222 | 0.005127 | −0.056629 |
| 339 | 0.069951 | −0.048422 | 0.038688 | 0.01619 | −0.010307 | 0.020245 | 0.054541 | −0.017361 | −0.063833 | 0.002785 | 0.021777 | −0.048614 | 0.046229 | −0.031261 |
| 340 | 0.073915 | 0.025478 | 0.049035 | −0.063771 | −0.088331 | 0.031372 | 0.048606 | −0.081984 | −0.119329 | −0.011248 | −0.084096 | −0.066441 | −0.060021 | 0.168944 |

| | Z | AA | AB | AC | AD | AE | AF | AG | AH | AI | AJ | AK | AL | AM |
|---|---|---|---|---|---|---|---|---|---|---|---|---|---|---|
| 1 | −0.001908 | 0.025584 | −0.032718 | −0.10464 | −0.017291 | 0.007786 | −0.032158 | −0.057265 | −0.025048 | 0.06869 | −0.026073 | 0.03931 | 0.061824 | −0.039108 |
| 2 | −0.027523 | 0.020722 | 0.013821 | −0.014263 | −0.000752 | 0.015885 | −0.029472 | −0.011812 | 0.00119 | −0.038261 | 0.060458 | −0.031074 | 0.004588 | −0.048791 |
| 3 | −0.042022 | −0.016442 | −0.025467 | −0.02136 | −0.053166 | −0.044625 | −0.023263 | −0.002387 | 0.033507 | 0.091289 | 0.041175 | −0.038299 | 0.062848 | −0.017452 |
| 4 | −0.043332 | 0.024898 | 0.004957 | −0.11248 | 0.030894 | 0.001544 | −0.02366 | −0.007916 | −0.083587 | −0.036462 | −0.055011 | 0.08644 | 0.028892 | −0.010553 |
| 5 | −0.074948 | 0.104351 | 0.000752 | −0.049718 | −0.152903 | −0.010858 | −0.180294 | −0.094478 | 0.014569 | −0.163368 | −0.070551 | 0.184977 | 0.022653 | −0.068852 |
| 6 | −0.088985 | −0.054001 | −0.046301 | −0.041959 | −0.008598 | 0.0079 | −0.011307 | −0.003009 | 0.046466 | −0.133111 | 0.045836 | 0.03695 | 0.092079 | −0.034648 |
| 7 | −0.036735 | −0.102665 | 0.085203 | 0.034036 | 0.001331 | 0.005453 | −0.00784 | −0.006862 | −0.007548 | −0.107062 | −0.010154 | −0.145334 | 0.027008 | −0.023274 |
| 8 | −0.003184 | −0.003512 | 0.143789 | −0.039922 | 0.009002 | −0.004233 | −0.039271 | 0.012348 | −0.208067 | −0.028325 | −0.197083 | −0.260789 | 0.007949 | −0.056429 |
| 9 | −0.066662 | 0.011585 | 0.012605 | −0.13456 | −0.011276 | 0.001726 | −0.063194 | −0.008773 | −0.110391 | −0.007603 | −0.090085 | 0.064004 | 0.000609 | −0.088039 |
| 10 | −0.057256 | 0.006684 | −0.066734 | −0.048034 | −0.021778 | −0.046663 | −0.089125 | −0.056103 | −0.010536 | 0.041427 | 0.021193 | −0.04492 | 0.013569 | −0.086602 |
| 11 | −0.108182 | −0.029556 | 0.116912 | −0.040063 | 0.076803 | 0.030685 | 0.006941 | 0.016364 | −0.012885 | −0.009229 | −0.041842 | 0.067118 | −0.085502 | −0.010309 |
| 12 | 0.06989 | −0.073948 | −0.032785 | 0.217772 | −0.091263 | −0.10238 | 0.100193 | −0.048807 | −0.015498 | −0.185002 | 0.025703 | 0.034534 | 0.053588 | −0.178811 |
| 13 | 0.004776 | −0.012882 | 0.01038 | −0.005742 | 0.000717 | 0.022422 | 0.006103 | 0.009967 | 0.000295 | −0.002943 | −0.000641 | −0.019637 | 0.019634 | −0.002281 |
| 14 | 0.006799 | −0.010607 | −0.011142 | −0.010602 | 0.020878 | 0.015171 | 0.008697 | −0.024853 | −0.009699 | −0.020512 | −0.004333 | −0.010969 | 0.006615 | 0.008036 |
| 15 | 0.001864 | −0.010957 | −0.041766 | −0.042414 | −0.011086 | 0.003596 | −0.017579 | −0.036265 | −0.014374 | 0.04458 | −0.006489 | −0.017401 | 0.027162 | −0.001082 |
| 16 | 0.029508 | −0.126894 | 0.029747 | −0.14785 | 0.080716 | 0.060261 | 0.048604 | 0.027663 | 0.157455 | 0.105448 | 0.073759 | 0.017426 | −0.126526 | 0.13189 |
| 17 | −0.062863 | 0.032858 | −0.049598 | −0.03388 | −0.122913 | 0.031563 | −0.012072 | −0.052007 | 0.029973 | −0.025406 | −0.061464 | 0.001691 | −0.02259 | −0.043971 |
| 18 | 0.066915 | −0.01526 | 0.082138 | −0.079355 | 0.026434 | −0.026369 | −0.086934 | −0.044188 | 0.125143 | 0.041445 | 0.039762 | 0.097236 | −0.0797 | 0.077905 |
| 19 | −0.028229 | −0.00092 | −0.009566 | −0.065614 | 0.012782 | −0.06566 | −0.067825 | −0.019047 | 0.028511 | 0.051453 | 0.007801 | −0.014064 | 0.057933 | −0.064431 |
| 20 | −0.001495 | 0.007431 | 0.01634 | −0.008118 | 0.016069 | 0.001962 | 0.017045 | 0.015981 | −0.024014 | 0.001626 | −0.007926 | −0.005642 | 0.0105 | −0.014856 |
| 21 | −0.064758 | −0.00693 | −0.003068 | −0.027423 | −0.033663 | −0.020232 | −0.100461 | 0.015874 | −0.00267 | 0.0213 | 0.074494 | −0.118951 | 0.054646 | −0.076853 |
| 22 | 0.006238 | −0.075936 | −0.081407 | 0.01277 | −0.051256 | −0.104196 | 0.021724 | −0.046338 | 0.038158 | −0.043901 | −0.063711 | 0.003148 | 0.043078 | 0.046515 |
| 23 | 0.045199 | −0.008921 | 0.057705 | −0.017351 | 0.03802 | 0.003804 | −0.006071 | −0.061217 | 0.023185 | −0.017841 | 0.082817 | 0.012636 | 0.130231 | 0.055334 |
| 24 | 0.001865 | −0.014332 | −0.051351 | −0.06331 | −0.057045 | −0.072366 | −0.048063 | −0.03012 | −0.054212 | −0.013765 | −0.0005 | −0.067236 | −0.060716 | 0.043876 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 25 | −0.006012 | 0.003972 | −0.016022 | −0.037566 | 0.039699 | −0.023896 | −0.057813 | 0.082263 | −0.005724 | 0.021195 | 0.126268 | −0.0233 | −0.000385 | −0.013521 |
| 26 | −0.002503 | 0.003335 | 0.01655 | −0.005411 | 0.014514 | −0.001318 | 0.018549 | 0.015091 | −0.01818 | 0.002646 | −0.00429 | −0.005699 | 0.004923 | −0.014845 |
| 27 | −0.00595 | 0.010207 | 0.007467 | −0.000738 | 0.005806 | 0.001839 | 0.013158 | 0.019795 | −0.022052 | 0.007591 | −0.002103 | 0.019215 | −0.001443 | −0.001515 |
| 28 | −0.034871 | 0.008135 | 0.001121 | −0.059458 | 0.028272 | 0.00296 | −0.008782 | −0.006418 | −0.017159 | −0.037827 | −0.028872 | 0.017095 | 0.001115 | −0.016542 |
| 29 | 0.042404 | −0.086275 | −0.007022 | −0.006804 | −0.023189 | −0.056342 | 0.062792 | 0.014514 | −0.019915 | −0.048991 | −0.000714 | −0.013351 | −0.045112 | 0.020698 |
| 30 | −0.01708 | 0.011069 | 0.048506 | −0.017567 | 0.105571 | −0.015385 | −0.039154 | 0.03927 | −0.006574 | 0.035297 | −0.029835 | −0.016628 | −0.03188 | 0.008716 |
| 31 | −0.01931 | 0.000363 | −0.023305 | −0.013458 | −0.003105 | 0.017717 | −0.028007 | −0.001123 | 0.037681 | −0.004334 | 0.029287 | −0.000361 | −0.011621 | 0.021147 |
| 32 | −0.040306 | 0.03016 | 0.005582 | −0.000316 | 0.01062 | −0.003727 | 0.030001 | −0.007979 | 0.02644 | −0.040277 | 0.076002 | −0.047173 | 0.052377 | 0.084545 |
| 33 | −0.006298 | 0.026961 | 0.040846 | 0.027566 | 0.008931 | 0.011392 | 0.013219 | 0.033602 | −0.06379 | 0.053372 | 0.013019 | 0.018961 | −0.018318 | 0.003851 |
| 34 | 0.004244 | −0.029681 | 0.025203 | 0.003722 | 0.077957 | −0.021801 | 0.002106 | −0.003557 | −0.01184 | −0.01956 | 0.058635 | −0.037243 | −0.053459 | 0.029813 |
| 35 | −0.010805 | −0.036242 | 0.004838 | 0.050603 | 0.01393 | −0.09667 | −0.002088 | 0.003723 | −0.054964 | 0.040167 | 0.041561 | 0.019179 | −0.000093 | −0.040643 |
| 36 | 0.006091 | 0.070732 | −0.006151 | 0.02568 | 0.033305 | 0.044134 | 0.014932 | 0.004347 | −0.005414 | −0.016288 | 0.004904 | 0.00029 | −0.031197 | −0.007479 |
| 37 | −0.004654 | −0.029736 | 0.005937 | −0.021153 | 0.008837 | −0.010651 | −0.004361 | 0.006315 | 0.009101 | −0.01363 | −0.046262 | −0.037775 | −0.01305 | −0.020129 |
| 38 | 0.035401 | 0.037632 | −0.068202 | −0.025903 | 0.062719 | 0.0602 | 0.013453 | 0.044602 | −0.01032 | 0.048247 | 0.103728 | −0.000479 | −0.069704 | −0.101065 |
| 39 | 0.055251 | −0.029895 | 0.02167 | 0?031297 | −0.013957 | 0.110813 | 0.01933 | 0.052987 | 0.021168 | −0.031215 | 0.063856 | −0.020765 | −0.052205 | −0.037404 |
| 40 | 0.070194 | −0.012552 | −0.018616 | 0.009591 | −0.000481 | −0.012941 | 0.0245 | −0.078491 | 0.019299 | 0.02817 | 0.061614 | 0.01344 | −0.02917 | −0.002018 |
| 41 | 0.031167 | −0.002416 | 0.024062 | 0.036088 | −0.025187 | −0.054558 | 0.040793 | 0.022957 | 0.035502 | −0.001428 | 0.06774 | −0.055186 | −0.017221 | −0.04007 |
| 42 | 0.016333 | −0.046621 | 0.001376 | 0.00805 | −0.061661 | −0.01186 | 0.056466 | 0.027552 | −0.019863 | −0.02448 | 0.020137 | −0.013383 | −0.029972 | 0.000211 |
| 43 | 0.053069 | −0.025885 | 0.031769 | 0.00763 | −0.004214 | 0.003037 | 0.014013 | −0.025516 | 0.029074 | 0.023727 | 0.067874 | −0.009562 | −0.024063 | 0.005257 |
| 44 | 0.00749 | −0.03491 | −0.00906 | 0.01247 | −0.038157 | −0.053645 | 0.027863 | −0.012556 | 0.004905 | −0.009913 | 0.067644 | −0.025016 | 0.01066 | 0.056086 |
| 45 | 0.098681 | 0.015114 | 0.031201 | −0.00067 | −0.047113 | −0.071505 | 0.000786 | −0.016776 | 0.066497 | 0.004127 | 0.070119 | −0.002414 | −0.026058 | 0.011319 |
| 46 | −0.058967 | −0.007543 | −0.063005 | 0.022692 | −0.017944 | −0.085122 | 0.000838 | −0.066432 | 0.078397 | −0.025007 | −0.069875 | −0.0587251 | −0.053939 | 0.066278 |
| 47 | 0.049528 | 0.008611 | 0.029918 | 0.017715 | −0.021536 | 0.080062 | 0.00516 | 0.038754 | 0.01074 | −0.053102 | 0.062746 | 0.020517 | −0.011953 | 0.024109 |
| 48 | −0.015343 | 0.114819 | −0.02892 | 0.044857 | 0.031735 | 0.026628 | 0.031141 | 0.092951 | −0.087527 | −0.062268 | 0.058093 | 0.049969 | −0.013124 | 0.012637 |
| 49 | −0.005655 | 0.026476 | 0.077392 | −0.030698 | 0.093194 | −0.016269 | −0.022465 | 0.055211 | −0.004422 | 0.060672 | −0.049101 | −0.045031 | −0.020879 | 0.012228 |
| 50 | 0.032486 | 0.024255 | 0.01072 | −0.036519 | 0.021514 | −0.046412 | −0.032464 | 0.007848 | 0.049761 | 0.048247 | −0.010528 | −0.037326 | 0.064558 | 0.043513 |
| 51 | −0.046011 | 0.016037 | −0.00418 | 0.068177 | −0.000033 | −0.006911 | −0.069858 | −0.00909 | −0.006876 | 0.038204 | 0.024195 | 0.015332 | −0.038248 | −0.026501 |
| 52 | 0.013706 | 0.042153 | 0.029981 | 0.021316 | 0.085431 | −0.012563 | −0.030299 | −0.010141 | 0.054637 | −0.021934 | −0.124722 | −0.044188 | −0.0684 | 0.020111 |
| 53 | −0.0582 | −0.018934 | 0.049145 | 0.034789 | 0.019956 | −0.077697 | −0.047242 | −0.033625 | 0.003426 | 0.039887 | 0.028307 | −0.097168 | 0.01055 | 0.008159 |
| 54 | 0.013676 | 0.01289 | 0.023375 | −0.020752 | 0.042902 | −0.061751 | 0.017471 | 0.082917 | −0.047967 | 0.036787 | −0.050204 | −0.047958 | 0.006998 | 0.019539 |
| 55 | −0.002091 | −0.001725 | 0.025552 | −0.024564 | 0.059005 | −0.019421 | −0.034414 | −0.023954 | 0.00265 | −0.007699 | −0.006991 | −0.038005 | −0.037876 | −0.003342 |
| 56 | −0.00659 | 0.021234 | 0.052334 | −0.007465 | 0.099799 | 0.013525 | −0.033444 | 0.047033 | 0.029118 | 0.062367 | −0.020303 | −0.023309 | 0.017752 | 0.011214 |
| 57 | 0.014237 | −0.058533 | 0.003898 | −0.004329 | −0.012177 | 0.029652 | 0.007199 | −0.048238 | −0.050826 | 0.011327 | 0.009814 | 0.087837 | −0.016052 | −0.007559 |
| 58 | 0.007128 | −0.039393 | −0.016566 | 0.068612 | 0.020906 | 0.007278 | −0.014428 | 0.046256 | 0.008089 | −0.005222 | −0.035602 | 0.024103 | −0.068539 | −0.010592 |
| 59 | 0.033239 | −0.020067 | 0.066221 | −0.051753 | 0.063293 | 0.000239 | 0.040097 | 0.047116 | −0.054826 | 0.027941 | 0.008575 | 0.069326 | 0.050511 | 0.013693 |
| 60 | −0.002053 | 0.019632 | −0.065655 | −0.026986 | 0.016872 | 0.108763 | −0.02692 | 0.016264 | −0.008385 | −0.046635 | 0.010546 | 0.006574 | −0.034281 | 0.021036 |
| 61 | 0.017676 | 0.032373 | −0.012111 | −0.055314 | −0.001537 | 0.083489 | 0.035133 | 0.119783 | 0.008509 | 0.036288 | −0.018457 | 0.006574 | 0.001201 | 0.019479 |
| 62 | −0.059878 | −0.045599 | −0.091016 | 0.017762 | −0.016327 | 0.084471 | −0.028302 | 0.084582 | 0.021756 | −0.002636 | 0.059852 | −0.042801 | 0.010669 | 0.035063 |
| 63 | 0.025722 | 0.022665 | 0.005196 | −0.049541 | 0.003219 | 0.002733 | 0.063945 | 0.149438 | 0.042409 | 0.052512 | −0.012919 | −0.035881 | −0.001406 | 0.026126 |
| 64 | −0.035435 | 0.001407 | 0.046021 | −0.021086 | 0.0684 | 0.035845 | −0.032556 | 0.065374 | −0.016566 | 0.014223 | −0.029895 | −0.003425 | −0.037261 | 0.012846 |
| 65 | −0.003813 | −0.049764 | −0.04238 | −0.002802 | 0.010609 | 0.09272 | −0.027723 | −0.006463 | −0.070086 | −0.049489 | 0.008979 | 0.111674 | −0.040386 | 0.007815 |
| 66 | −0.04321 | −0.032811 | 0.037229 | −0.023459 | −0.002074 | 0.102857 | 0.006222 | 0.005987 | −0.038949 | 0.043548 | 0.035581 | 0.018219 | 0.009461 | 0.05175 |
| 67 | 0.096181 | 0.084563 | −0.035441 | 0.001055 | −0.025833 | 0.104883 | −0.063802 | −0.076905 | 0.068099 | 0.007131 | −0.014174 | −0.000258 | −0.032198 | 0.022715 |
| 68 | −0.087079 | −0.002628 | −0.0199 | 0.040094 | −0.019819 | 0.160958 | −0.126018 | −0.061106 | 0.155422 | 0.067896 | −0.247186 | −0.044425 | 0.109793 | 0.016298 |
| 69 | −0.008334 | 0.00132 | −0.008855 | 0.01259 | 0.032479 | 0.022875 | 0.018934 | −0.009373 | −0.002657 | −0.017854 | −0.031791 | −0.026727 | 0.005169 | 0.002704 |
| 70 | −0.00424 | −0.026623 | 0.006816 | 0.017456 | 0.055848 | 0.02619 | 0.003669 | −0.01673 | −0.010602 | −0.004495 | 0.01168 | −0.008322 | 0.005659 | 0.015739 |
| 71 | −0.081277 | −0.002511 | −0.042748 | 0.004996 | −0.027005 | −0.027468 | −0.006962 | 0.018454 | 0.063414 | −0.024324 | 0.131277 | −0.074445 | −0.051681 | −0.054139 |
| 72 | −0.052329 | −0.013279 | −0.057735 | −0.025494 | −0.047562 | 0.017935 | −0.065288 | −0.025381 | 0.124984 | 0.005703 | 0.031378 | −0.057214 | −0.013347 | 0.016735 |
| 73 | −0.060566 | 0.004473 | −0.07275 | 0.052095 | 0.023195 | 0.03661 | −0.036827 | 0.011581 | 0.158971 | −0.064847 | 0.009071 | −0.006706 | 0.055591 | 0.003655 |
| 74 | 0.045976 | −0.018983 | 0.027544 | −0.028771 | 0.141356 | 0.00667 | −0.06149 | 0.166278 | 0.107262 | 0.071234 | −0.027271 | 0.193675 | 0.059414 | 0.036972 |
| 75 | −0.000883 | −0.012118 | 0.00509 | 0.005576 | 0.037956 | 0.03018 | 0.001093 | −0.019703 | −0.02052 | −0.015537 | −0.006279 | 0.00603 | −0.01041 | 0.020393 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 76 | −0.009036 | 0.00318 | −0.018134 | 0.022375 | 0.020268 | 0.008713 | 0.000306 | −0.028413 | −0.022394 | −0.019889 | −0.000491 | 0.033115 | −0.000708 | 0.026101 |
| 77 | −0.001607 | −0.009051 | 0.008261 | 0.005557 | 0.041404 | 0.025873 | 0.000793 | −0.02347 | −0.023649 | −0.013213 | −0.005397 | 0.00467 | −0.016042 | 0.018772 |
| 78 | 0.001269 | −0.010715 | 0.009585 | 0.005679 | 0.042783 | 0.027208 | −0.002374 | −0.02508 | −0.018153 | −0.014413 | −0.008415 | 0.005741 | −0.019584 | 0.018533 |
| 79 | 0.001866 | −0.008451 | 0.00719 | 0.001823 | 0.046381 | 0.03372 | −0.001046 | −0.022907 | −0.029026 | −0.012488 | −0.009562 | 0.011401 | −0.020498 | 0.023855 |
| 80 | −0.025331 | −0.005369 | −0.009564 | 0:024228 | 0.012808 | 0.049958 | −0.032315 | 0.040229 | 0.089567 | 0.083053 | 0.092687 | 0.074952 | −0.020998 | −0.045296 |
| 81 | 0.024668 | −0.002649 | −0.014227 | −0.026181 | −0.054694 | −0.035393 | −0.062916 | 0.031982 | −0.031645 | 0.015704 | −0.043813 | 0.009124 | −0.040858 | −0.023045 |
| 82 | −0.006528 | 0.011398 | −0.005635 | 0.003026 | 0.004409 | 0.016813 | 0.004368 | −0.008005 | −0.012345 | 0.0029961 | −0.005338 | 0.031688 | 0.003697 | −0.01183 |
| 83 | −0.0126721 | 0.017806 | −0.005885 | 0.00364 | −0.003481 | 0.006227 | 0.010025 | 0.006634 | −0.007661 | 0.008222 | −0.002582 | 0.025524 | 0.000871 | −0.005385 |
| 84 | −0.012405 | 0.017836 | −0.008258 | 0.007823 | 0.000714 | 0.006909 | 0.011607 | 0.016564 | −0.016412 | 0.006042 | 0.004442 | 0.029923 | 0.001894 | 0.002897 |
| 85 | 0.019094 | −0.025454 | −0.06727 | 0.017532 | −0.040076 | 0.049636 | 0.011373 | 0.002737 | −0.00346 | 0.020642 | −0.042966 | −0.051964 | −0.033155 | −0.009239 |
| 86 | −0.041839 | 0.014462 | −0.074986 | 0.00982 | −0.058132 | 0.04369 | −0.033129 | −0.044023 | 0.087337 | 0.030931 | 0.012881 | −0.036326 | −0.012109 | 0.00067 |
| 87 | 0.009632 | 0.008685 | −0.025203 | −0.023076 | −0.03582 | 0.020195 | −0.047693 | −0.022042 | 0.060031 | 0.049127 | 0.007843 | −0.036308 | −0.016109 | −0.002442 |
| 88 | −0.010242 | 0.012159 | 0.000806 | −0.003212 | −0.0033 | 0.009642 | 0.005871 | 0.009472 | −0.013074 | 0.008224 | 0.000921 | 0.031882 | 0.001492 | −0.000238 |
| 89 | −0.00262 | 0.014236 | 0.009435 | 0.000873 | 0.004516 | 0.001519 | 0.014754 | 0.013175 | −0.024231 | 0.00544 | −0.00366 | 0.026599 | 0.00524 | −0.015568 |
| 90 | −0.008594 | 0.016822 | −0.004588 | −0.001775 | 0.004869 | 0.009954 | 0.008935 | 0.014136 | −0.014756 | 0.005751 | −0.00539 | 0.024593 | 0.010353 | −0.004834 |
| 91 | 0.002524 | 0.020649 | −0.001555 | −0.011935 | −0.000228 | 0.012932 | 0.015983 | 0.016007 | −0.030065 | 0.013159 | −0.002396 | 0.030467 | 0.002125 | −0.017786 |
| 92 | −0.020535 | 0.016417 | −0.024894 | −0.012159 | −0.048014 | 0.031656 | −0.028368 | −0.032302 | −0.003789 | 0.055022 | −0.000112 | −0.004494 | 0.010657 | 0.049162 |
| 93 | −0.006851 | 0.013568 | −0.012941 | 0.006541 | −0.006863 | 0.029464 | 0.014065 | 0.013226 | 0.019876 | 0.013419 | −0.005548 | 0.006503 | 0.007608 | −0.012785 |
| 94 | 0.004005 | 0.029535 | −0.021724 | 0.007868 | 0.006863 | −0.019558 | −0.000394 | 0.017611 | 0.006541 | −0.032181 | −0.021348 | 0.030844 | 0.034638 | −0.021767 |
| 95 | −0.082687 | −0.005048 | −0.056572 | 0.061422 | 0.039138 | 0.07689 | −0.08226 | −0.042355 | 0.077666 | 0.091025 | 0.043399 | −0.016834 | −0.047436 | 0.012366 |
| 96 | −0.070105 | 0.028302 | −0.166834 | 0.009352 | −0.002916 | 0.146014 | 0.066506 | −0.012977 | −0.093102 | 0.060755 | −0.007824 | −0.051782 | 0.019567 | −0.05158 |
| 97 | −0.041356 | −0.039808 | −0.00021 | −0.005738 | −0.02429 | 0.090543 | −0.035971 | 0.015313 | −0.068050 | 0.036643 | 0.012912 | −0.077381 | 0.001912 | 0.009756 |
| 98 | 0.027008 | −0.039146 | −0.032211 | −0.012345 | −0.006087 | −0.031655 | −0.016638 | −0.018892 | 0.013702 | −0.046919 | −0.009709 | 0.012201 | 0.022172 | 0.035658 |
| 99 | −0.041364 | 0.014397 | −0.014696 | −0.051195 | 0.016996 | 0.029272 | 0.004075 | −0.008591 | −0.001707 | 0.014599 | −0.022884 | 0.002838 | 0.036284 | 0.010565 |
| 100 | −0.009611 | −0.006194 | −0.042751 | −0.037677 | 0.050211 | −0.039602 | 0.032619 | 0.046646 | 0.02512 | 0.00237 | −0.076633 | −0.004714 | −0.027353 | −0.016901 |
| 101 | 0.002448 | −0.039151 | −0.021192 | 0.007271 | −0.027013 | −0.027992 | −0.040578 | 0.000595 | −0.002177 | −0.014969 | −0.026388 | 0.018754 | 0.010397 | 0.02085 |
| 102 | −0.050531 | 0.055232 | −0.005907 | 0.045793 | 0.133815 | −0.027869 | 0.014906 | −0.000953 | 0.006671 | 0.030753 | −0.008826 | 0.004501 | 0.002753 | −0.067613 |
| 103 | −0.08192 | 0.016182 | −0.033562 | 0.125722 | 0.142043 | −0.002327 | −0.007636 | −0.027829 | −0.011097 | 0.039064 | −0.077328 | −0.065884 | 0.036292 | −0.015683 |
| 104 | −0.147163 | −0.045647 | −0.109771 | 0.081904 | 0.116473 | 0.066018 | 0.05164 | −0.085788 | −0.006499 | 0.057201 | 0.044856 | −0.030107 | −0.048452 | 0.066604 |
| 105 | −0.037471 | −0.010537 | 0.054848 | 0.106348 | −0.057113 | 0.052361 | 0.119188 | −0.001988 | 0.11915 | −0.117044 | −0.034768 | 0.087751 | −0.053661 | −0.120883 |
| 106 | 0.012802 | 0.016171 | 0.026511 | 0.005929 | 0.0535 | −0.02406 | −0.026781 | −0.131944 | −0.03538 | −0.011286 | 0.007469 | 0.058485 | −0.02038 | 0.017546 |
| 107 | −0.030563 | −0.007864 | −0.0241 | −0.0182 | 0.030974 | 0.011751 | −0.019042 | −0.064086 | −0.026981 | 0.005594 | −0.053044 | 0.036223 | −0.096547 | 0.044123 |
| 108 | 0.057411 | −0.01211 | −0.089713 | 0.015509 | −0.074468 | −0.028142 | 0.083438 | −0.043907 | −0.025965 | 0.205012 | −0.038518 | 0.043064 | 0.024635 | 0.145479 |
| 109 | −0.064452 | 0.085969 | −0.041475 | −0.017399 | 0.006395 | 0.037935 | −0.005071 | 0.014272 | 0.134303 | 0.158255 | −0.152038 | −0.000072 | 0.062319 | 0.020237 |
| 110 | −0.097713 | 0.0846 | 0.020338 | −0.05832 | −0.062789 | 0.050977 | −0.093273 | 0.013536 | −0.000146 | 0.134048 | 0.018108 | 0.054374 | −0.091879 | 0.005228 |
| 111 | 0.053273 | −0.061193 | −0.030328 | −0.031749 | −0.067825 | −0.08774 | 0.016264 | −0.015988 | −0.007143 | 0.052929 | 0.007793 | 0.069674 | −0.060076 | 0.009131 |
| 112 | 0.070771 | 0.098106 | −0.048377 | 0.009385 | 0.011095 | −0.053958 | 0.161475 | −0.121101 | 0.069828 | 0.012326 | 0.065322 | 0.069783 | 0.043116 | 0.053632 |
| 113 | 0.022318 | 0.061463 | −0.034648 | −0.021423 | 0.019826 | −0.042362 | −0.039138 | −0.026859 | 0.045373 | 0.151063 | −0.034736 | 0.027873 | 0.164244 | −0.066907 |
| 114 | −0.038664 | 0.022733 | 0.086222 | 0.079464 | −0.038469 | −0.080356 | −0.012276 | 0.009109 | 0.057966 | 0.00286 | 0.10071 | −0.038497 | 0.033185 | −0.098516 |
| 115 | −0.011313 | −0.015051 | 0.016709 | −0.020637 | −0.074057 | −0.010167 | 0.001192 | 0.012933 | 0.044411 | 0.047268 | −0.039213 | 0.020666 | −0.08256 | 0.147256 |
| 116 | −0.060554 | −0.004005 | 0.057071 | −0.003443 | −0.018649 | 0.00208 | −0.037118 | 0.080685 | 0.033542 | −0.084174 | −0.069276 | 0.060029 | 0.019749 | 0.17462 |
| 117 | −0.01064 | −0.114274 | −0.093295 | 0.005658 | −0.006786 | −0.074552 | 0.07105 | 0.008807 | 0.030059 | 0.006067 | 0.030367 | 0.036918 | 0.025425 | 0.011052 |
| 118 | 0.010827 | 0.036523 | 0.057661 | −0.038597 | −0.066515 | 0.037923 | −0.092299 | −0.079831 | −0.052523 | 0.018168 | 0.012038 | 0.035495 | 0.039511 | 0.00531 |
| 119 | 0.030622 | 0.089563 | 0.013805 | −0.032127 | −0.038717 | 0.011065 | 0.047634 | 0.073037 | 0.019257 | 0.075141 | −0.054601 | −0.075261 | −0.01957 | −0.020983 |
| 120 | −0.050799 | 0.006068 | −0.059985 | −0.003172 | 0.01781 | −0.106905 | 0.043251 | 0.048703 | 0.005982 | −0.026517 | 0.037176 | 0.069626 | −0.013644 | 0.03553 |
| 121 | −0.040999 | −0.071638 | −0.04737 | −0.026028 | 0.031202 | −0.064031 | 0.057278 | 0.082992 | 0.029991 | 0.016429 | 0.058009 | 0.07083 | −0.031367 | 0.008192 |
| 122 | −0.020182 | 0.045775 | −0.004221 | −0.007041 | −0.074037 | 0.016483 | −0.000644 | 0.015129 | 0.016239 | 0.018891 | 0.09927 | −0.047311 | −0.025709 | −0.005867 |
| 123 | −0.040144 | 0.00322 | −0.009052 | −0.011799 | −0.089772 | −0.06511 | 0.034195 | −0.003782 | −0.017724 | 0.002386 | −0.013625 | −0.011556 | −0.044772 | −0.022306 |
| 124 | 0.065309 | 0.008666 | 0.032764 | −0.026908 | 0.052379 | −0.020176 | 0.019124 | 0.069972 | 0.010027 | 0.029868 | 0.017014 | −0.041767 | −0.041145 | 0.02839 |
| 125 | −0.03932 | −0.018515 | 0.010942 | −0.111202 | 0.008992 | −0.039418 | −0.083044 | −0.031917 | 0.070484 | −0.001927 | 0.057386 | 0.041757 | 0.018435 | −0.051311 |
| 126 | −0.023569 | −0.055832 | 0.000862 | 0.021062 | −0.029422 | −0.079147 | 0.016316 | −0.001602 | −0.018078 | −0.029798 | −0.032347 | 0.005494 | 0.028399 | −0.049471 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 127 | 0.013223 | −0.020902 | −0.019117 | 0.006276 | 0.004272 | −0.079548 | 0.013139 | −0.001226 | −0.004213 | −0.055439 | −0.036432 | −0.00674 | 0.018372 | −0.037757 |
| 128 | −0.106516 | −0.000746 | −0.01755 | −0.063048 | −0.014638 | 0.039685 | −0.004465 | −0.048704 | 0.036453 | 0.062072 | −0.005176 | −0.00598 | −0.017007 | 0.013907 |
| 129 | −0.065825 | 0.079772 | −0.088939 | 0.110671 | −0.036531 | 0.069202 | 0.013728 | 0.011664 | 0.091006 | 0.070008 | −0.041274 | 0.034332 | 0.025223 | 0.130672 |
| 130 | −0.077973 | 0.027012 | −0.009699 | −0.01588 | 0.032815 | 0.060383 | 0.025746 | −0.025529 | 0.075085 | −0.011224 | −0.052468 | 0.033912 | 0.064484 | 0.034811 |
| 131 | 0.001369 | −0.054448 | 0.069902 | −0.008389 | −0.093817 | 0.059774 | −0.00687 | −0.008149 | −0.041211 | 0.05126 | −0.0399 | 0.042263 | 0.082655 | −0.039937 |
| 132 | −0.10037 | 0.037391 | 0.036118 | −0.044917 | 0.004022 | 0.050954 | −0.011228 | −0.090166 | −0.006744 | 0.125075 | 0.049039 | −0.070385 | −0.049124 | −0.070604 |
| 133 | −0.044819 | −0.045971 | 0.001126 | −0.031486 | 0.071085 | 0.028815 | 0.035787 | −0.056917 | 0.019892 | −0.051768 | −0.022339 | −0.032175 | 0.020553 | 0.050228 |
| 134 | 0.053855 | −0.213169 | 0.027271 | 0.016194 | −0.069188 | 0.060237 | −0.036138 | 0.03285 | −0.094265 | 0.087005 | −0.030609 | −0.04109 | −0.016525 | 0.108448 |
| 135 | −0.002918 | 0.045416 | 0.048569 | 0.021573 | −0.008722 | 0.000533 | 0.015178 | −0.007185 | 0.077555 | −0.03241 | 0.029237 | 0.00105 | −0.005178 | −0.00917 |
| 136 | −0.003606 | 0.098419 | 0.060777 | −0.039838 | 0.013764 | 0.022294 | −0.020152 | −0.023522 | 0.077411 | −0.0003 | 0.015938 | −0.062399 | 0.021534 | 0.031487 |
| 137 | −0.015753 | −0.112932 | −0.028352 | 0.012105 | 0.032448 | −0.04819 | −0.08538 | −0.013365 | 0.144384 | −0.149417 | −0.118262 | −0.035543 | 0.162048 | 0.022426 |
| 138 | −0.000444 | 0.173945 | −0.167311 | −0.008771 | −0.021411 | 0.060115 | −0.108518 | 0.095931 | −0.166097 | 0.109879 | −0.033669 | 0.095397 | 0.152522 | 0.024963 |
| 139 | −0.038192 | 0.069985 | −0.008312 | 0.039093 | −0.085114 | 0.04778 | −0.113198 | −0.036264 | 0.028652 | 0.060621 | 0.133046 | −0.031675 | −0.035715 | 0.036053 |
| 140 | 0.100082 | −0.104617 | 0.030371 | −0.062066 | −0.009949 | 0.215306 | 0.021517 | −0.104054 | 0.051283 | −0.081741 | 0.085474 | −0.085419 | 0.127491 | 0.032486 |
| 141 | 0.035776 | 0.031774 | 0.088753 | −0.030915 | −0.042019 | −0.007364 | −0.021431 | −0.011295 | −0.04362 | −0.014679 | −0.010421 | −0.046902 | −0.04 | −0.083397 |
| 142 | 0.055308 | −0.022226 | −0.033823 | −0.0129 | −0.068642 | 0.051452 | 0.088067 | −0.037488 | 0.015778 | 0.062279 | 0.033219 | −0.05392 | 0.018698 | −0.007842 |
| 143 | 0.047116 | 0.060751 | 0.012389 | 0.055574 | −0.028084 | 0.036808 | 0.02577 | −0.046654 | −0.050835 | 0.04073 | 0.007442 | 0.009811 | −0.12245 | 0.093841 |
| 144 | 0.076132 | 0.053228 | 0.005267 | 0.02404 | −0.003984 | −0.023627 | 0.066563 | 0.02683 | 0.057169 | −0.038926 | −0.010461 | −0.033597 | −0.086969 | 0.061886 |
| 145 | 0.028267 | −0.027951 | 0.015814 | 0.009868 | −0.02563 | −0.051197 | 0.029227 | 0.056664 | 0.114271 | 0.044594 | 0.084798 | −0.070653 | −0.036818 | 0.011929 |
| 146 | −0.027863 | −0.056249 | 0.008588 | −0.017913 | −0.005276 | −0.010006 | −0.024396 | −0.012475 | 0.034962 | 0.01939 | −0.020036 | 0.052462 | 0.005179 | −0.001845 |
| 147 | 0.015186 | −0.111065 | 0.064244 | −0.010112 | −0.050986 | 0.071502 | −0.027211 | −0.063744 | −0.104297 | 0.08447 | 0.05418 | 0.053955 | 0.09336 | 0.055981 |
| 148 | −0.002339 | −0.032015 | −0.022869 | 0.085409 | 0.053073 | 0.024194 | 0.104025 | 0.031229 | −0.051573 | −0.013105 | 0.134487 | −0.155336 | 0.124702 | 0.248397 |
| 149 | −0.004026 | 0.032039 | 0.0361 | 0.054688 | −0.059966 | 0.01011 | −0.036414 | 0.005972 | −0.017523 | 0.000452 | 0.018087 | −0.011917 | −0.059812 | −0.018696 |
| 150 | 0.000026 | 0.109651 | −0.080354 | −0.071996 | −0.081147 | −0.026905 | −0.062651 | −0.05674 | 0.016595 | 0.04107 | 0.024555 | 0.089806 | −0.022198 | −0.005764 |
| 151 | 0.018026 | −0.066313 | 0.016596 | 0.002666 | −0.028756 | 0.120269 | −0.041144 | 0.124879 | −0.144439 | −0.069762 | 0.185611 | −0.008515 | −0.183369 | 0.04511 |
| 152 | 0.124939 | 0.05853 | 0.029939 | −0.032167 | 0.038717 | 0.025342 | 0.080607 | 0.04273 | 0.026436 | −0.000732 | 0.00864 | −0.019116 | 0.003323 | −0.040975 |
| 153 | 0.081911 | 0.03629 | 0.018897 | 0.01867 | −0.005868 | 0.082603 | 0.096641 | 0.020839 | −0.036689 | 0.044916 | 0.024123 | −0.084195 | −0.073408 | 0.050924 |
| 154 | 0.10263 | 0.020931 | −0.008339 | −0.002192 | −0.001075 | 0.005413 | 0.057268 | 0.036792 | 0.04211 | 0.013052 | −0.003483 | −0.000606 | 0.038753 | −0.017979 |
| 155 | −0.046821 | 0.07123 | −0.045259 | −0.033065 | −0.011814 | −0.026056 | 0.002845 | −0.066636 | 0.055392 | −0.012852 | −0.033795 | −0.064845 | 0.011334 | −0.018536 |
| 156 | −0.017353 | −0.073959 | −0.021648 | −0.188097 | 0.04175 | −0.034286 | −0.03793 | −0.05071 | 0.013648 | 0.049741 | 0.003585 | 0.026315 | 0.070086 | −0.025755 |
| 157 | −0.030906 | 0.149824 | −0.07608 | −0.057544 | 0.043231 | −0.097151 | −0.01466 | −0.026203 | −0.032264 | −0.007362 | 0.076084 | 0.001427 | 0.007664 | −0.016909 |
| 158 | 0.016685 | 0.134654 | −0.068046 | −0.09247 | −0.075921 | −0.062486 | −0.043143 | 0.051866 | 0.015307 | 0.030418 | 0.052421 | −0.013134 | 0.072727 | 0.066737 |
| 159 | 0.003447 | 0.069976 | −0.212606 | 0.094508 | −0.13143 | 0.021959 | 0.012735 | 0.026602 | 0.165282 | −0.037649 | 0.021858 | 0.092526 | 0.079238 | 0.084996 |
| 160 | −0.139196 | 0.120758 | 0.070872 | 0.026178 | −0.045953 | −0.139456 | 0.03815 | −0.002749 | −0.213162 | 0.056565 | 0.17654 | 0.13527 | 0.099176 | −0.015932 |
| 161 | −0.056048 | 0.050318 | 0.030726 | 0.044169 | −0.015542 | 0.127595 | 0.006811 | 0.154712 | −0.056735 | 0.056921 | −0.155054 | −0.013044 | 0.092007 | 0.070993 |
| 162 | 0.181513 | 0.04761 | −0.017779 | 0.075163 | −0.155573 | −0.063714 | 0.005337 | 0.07412 | −0.140482 | 0.069447 | −0.129033 | 0.101379 | 0.074553 | 0.030773 |
| 163 | 0.122474 | 0.017287 | −0.037694 | −0.01659 | −0.01603 | −0.012908 | 0.130077 | −0.011645 | 0.01125 | −0.013524 | −0.001587 | −0.010428 | 0.037957 | −0.056389 |
| 164 | 0.061978 | 0.088476 | −0.051121 | −0.022347 | 0.018955 | −0.029013 | −0.011201 | 0.00502 | 0.036512 | −0.014758 | −0.014938 | −0.078235 | 0.072949 | −0.084996 |
| 165 | −0.016135 | −0.085152 | 0.03172 | 0.024385 | −0.023239 | 0.132241 | 0.062982 | −0.074468 | 0.121455 | 0.096862 | −0.013543 | −0.104088 | −0.035256 | −0.169984 |
| 166 | 0.049935 | −0.001795 | −0.061214 | 0.020833 | 0.086239 | 0.002808 | −0.111141 | 0.135141 | 0.003183 | 0.004959 | 0.063061 | −0.012103 | 0.141095 | −0.012239 |
| 167 | 0.000765 | 0.030498 | −0.055892 | −0.00684 | −0.039456 | 0.035063 | 0.067579 | −0.146117 | 0.035554 | 0.034108 | −0.031767 | −0.078684 | −0.025328 | 0.035547 |
| 168 | 0.021753 | 0.062107 | −0.020004 | −0.041267 | 0.01738 | 0.106294 | 0.102215 | −0.011596 | 0.051574 | −0.023643 | −0.01208 | −0.013901 | −0.02155 | 0.004933 |
| 169 | −0.000311 | −0.007583 | 0.020587 | 0.048623 | 0.003055 | 0.00472 | 0.030144 | −0.021875 | −0.007441 | −0.011521 | −0.010374 | 0.050876 | −0.014839 | −0.000549 |
| 170 | 0.026653 | −0.000876 | 0.029507 | 0.056457 | −0.017292 | 0.028247 | 0.03615 | −0.007419 | −0.001683 | 0.004068 | 0.002133 | 0.025546 | 0.002245 | −0.023209 |
| 171 | −0.007108 | −0.039212 | 0.028448 | 0.063734 | −0.008285 | 0.030838 | 0.100125 | −0.019304 | 0.000453 | −0.009523 | −0.020949 | 0.043812 | −0.047886 | 0.008786 |
| 172 | 0.02077 | 0.019632 | 0.053166 | 0.052837 | 0.031344 | −0.038542 | 0.017479 | 0.010944 | −0.051753 | −0.012028 | −0.039291 | 0.055185 | −0.09232 | 0.011572 |
| 173 | 0.009775 | −0.004267 | −0.009249 | 0.052906 | −0.019052 | −0.003852 | 0.053917 | 0.038958 | −0.033003 | −0.031238 | −0.0641 | 0.034839 | 0.001929 | −0.007425 |
| 174 | −0.01414 | 0.032986 | 0.099098 | 0.051219 | −0.021436 | 0.034639 | 0.032104 | −0.007669 | −0.055066 | −0.035611 | −0.025453 | −0.037158 | 0.045216 | 0.042214 |
| 175 | 0.040339 | 0.081125 | 0.155705 | 0.07782 | 0.009445 | −0.000333 | 0.004699 | −0.02219 | −0.026015 | −0.018194 | −0.008208 | 0.032574 | 0.127629 | −0.067798 |
| 176 | 0.003393 | −0.01113 | 0.013416 | 0.011708 | 0.114697 | −0.008731 | 0.007351 | −0.103547 | −0.045512 | 0.001665 | −0.078594 | 0.023911 | −0.077503 | 0.021868 |
| 177 | −0.08359 | −0.079762 | −0.086822 | 0.149581 | −0.031739 | 0.096788 | 0.023724 | −0.012468 | −0.063778 | −0.1109 | 0.084788 | 0.133272 | −0.021873 | 0.004441 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 178 | 0.03568 | −0.011411 | 0.019536 | 0.01755 | −0.018719 | −0.014791 | −0.034194 | −0.028889 | −0.021846 | −0.082367 | 0.014025 | 0.006944 | 0.011139 | 0.060293 |
| 179 | 0.01679 | −0.007823 | −0.021728 | −0.029199 | −0.060195 | 0.022459 | 0.049829 | −0.022253 | 0.009495 | −0.045369 | 0.02175 | 0.000231 | 0.027282 | −0.007171 |
| 180 | 0.02249 | 0.002805 | −0.020112 | −0.003012 | −0.051153 | 0.01707 | 0.011177 | 0.012654 | −0.002023 | −0.051429 | 0.014638 | −0.003078 | 0.061778 | −0.001153 |
| 181 | 0.02075 | 0.006876 | −0.033667 | −0.0093 | −0.045199 | 0.01495 | 0.013518 | −0.001071 | 0.005917 | −0.062439 | 0.029787 | 0.001311 | 0.032488 | −0.002536 |
| 182 | 0.03031 | 0.05598 | −0.036831 | −0.029582 | −0.035059 | 0.014203 | 0.07036 | 0.017956 | 0.012899 | −0.048602 | −0.001961 | −0.000219 | −0.000832 | −0.033485 |
| 183 | −0.003398 | 0.022051 | −0.03386 | −0.064085 | −0.011261 | 0.017126 | 0.098823 | 0.011123 | 0.068024 | 0.003829 | 0.026252 | 0.021718 | −0.052082 | −0.018364 |
| 184 | −0.053219 | −0.00503 | −0.022543 | −0.07632 | 0.012944 | −0.071679 | 0.082273 | 0.044898 | 0.036478 | 0.035827 | 0.052633 | −0.009651 | −0.040465 | −0.004063 |
| 185 | −0.006702 | −0.049054 | 0.03964 | 0.029665 | 0.0155 | −0.033842 | −0.008764 | 0.035901 | 0.037674 | −0.022171 | −0.024016 | −0.066485 | −0.074692 | 0.011672 |
| 186 | 0.027501 | 0.01451 | −0.017925 | 0.129224 | −0.005023 | 0.08812 | 0.043651 | 0.063768 | 0.020949 | 0.042064 | −0.040818 | −0.049369 | −0.050334 | −0.070728 |
| 187 | −0.006031 | 0.029721 | 0.052996 | 0.011392 | 0.001194 | −0.024903 | 0.010811 | 0.079877 | 0.04929 | 0.063128 | −0.015184 | −0.00383 | −0.020329 | −0.037847 |
| 188 | −0.007647 | 0.078228 | 0.113562 | 0.016994 | −0.010341 | 0.000816 | −0.000219 | 0.043928 | 0.055318 | 0.017696 | −0.00362 | −0.034746 | 0.033211 | 0.013884 |
| 189 | −0.003097 | 0.118933 | 0.087457 | 0.016005 | −0.044438 | −0.07505 | 0.046525 | 0.021737 | 0.031334 | 0.049577 | 0.010193 | −0.022904 | 0.084261 | 0.015646 |
| 190 | −0.019582 | 0.020873 | −0.050531 | 0.004493 | 0.007089 | −0.014435 | 0.018125 | −0.011049 | −0.088426 | −0.01833 | −0.039499 | −0.035463 | −0.036257 | −0.023065 |
| 191 | −0.055331 | −0.017573 | −0.016543 | −0.016125 | −0.001161 | 0.001074 | 0.008383 | −0.060774 | −0.098677 | 0.016643 | −0.008227 | −0.045833 | −0.056162 | −0.041547 |
| 192 | 0.052041 | 0.042794 | 0.050308 | −0.088557 | 0.043064 | −0.012534 | 0.05544 | 0.024467 | 0.052975 | 0.011089 | 0.015427 | −0.047718 | −0.1066 | −0.015863 |
| 193 | 0.06776 | 0.059564 | 0.08905 | −0.028922 | 0.052135 | −0.038106 | 0.02596 | 0.055595 | 0.041927 | 0.046137 | −0.027 | −0.034857 | −0.073325 | −0.006136 |
| 194 | 0.010016 | 0.047981 | 0.098663 | 0.019558 | −0.007391 | 0.009032 | 0.064516 | 0.038969 | −0.004101 | −0.002569 | −0.010918 | −0.109719 | −0.004788 | 0.002467 |
| 195 | −0.089268 | 0.033382 | −0.018248 | 0.035167 | −0.111921 | −0.056105 | 0.000494 | 0.019354 | 0.006612 | −0.051784 | 0.023872 | −0.043561 | −0.005247 | −0.053174 |
| 196 | −0.024694 | 0.022832 | 0.000204 | 0.010924 | −0.099596 | −0.038957 | 0.025005 | 0.004629 | −0.027032 | −0.025682 | 0.015992 | −0.049029 | 0.017844 | 0.008923 |
| 197 | −0.017305 | 0.041415 | −0.028782 | −0.006185 | 0.002033 | 0.003216 | 0.078179 | −0.035277 | −0.086986 | −0.023123 | −0.062506 | −0.078292 | −0.046861 | −0.058737 |
| 198 | −0.03713 | 0.005121 | 0.052461 | 0.094627 | −0.02402 | −0.077096 | 0.025789 | −0.032811 | 0.013868 | 0.002862 | 0.058906 | 0.027155 | −0.071165 | −0.082185 |
| 199 | 0.086939 | 0.034223 | 0.086433 | 0.244543 | 0.16509 | 0.038415 | −0.039861 | 0.105656 | 0.104003 | −0.061369 | 0.053249 | 0.13923 | 0.238139 | −0.048117 |
| 200 | −0.011234 | 0.06553 | 0.067952 | 0.078914 | −0.039046 | 0.043006 | 0.02764 | 0.0013 | 0.039471 | −0.091232 | 0.025701 | −0.035452 | −0.038093 | 0.01166 |
| 201 | −0.03554 | 0.031641 | 0.151428 | 0.025278 | 0.038904 | 0.080907 | −0.12167 | −0.024396 | 0.031844 | −0.071415 | −0.012528 | −0.005509 | 0.026875 | −0.144049 |
| 202 | 0.005063 | 0.031413 | 0.040102 | 0.109297 | −0.077724 | −0.05081 | 0.104556 | −0.01952 | 0.00945 | −0.020326 | 0.028531 | 0.023771 | −0.086706 | −0.098857 |
| 203 | −0.072497 | 0.045399 | 0.006661 | 0.057414 | 0.145962 | −0.047396 | −0.031507 | 0.013722 | −0.054556 | −0.143071 | 0.086114 | 0.000551 | −0.046682 | 0.113488 |
| 204 | 0.038594 | 0.047221 | 0.040807 | −0.054295 | −0.133406 | 0.007406 | −0.034474 | 0.087196 | 0.103949 | 0.053817 | 0.002956 | −0.027423 | −0.054374 | −0.040637 |
| 205 | 0.137008 | 0.069638 | −0.183573 | 0.003292 | 0.062987 | 0.274887 | −0.021892 | −0.140612 | −0.097438 | −0.112216 | −0.050769 | −0.011509 | −0.035833 | −0.164843 |
| 206 | 0.045539 | 0.078759 | −0.021479 | 0.087944 | 0.09509 | 0.038909 | 0.053859 | 0.113694 | 0.076451 | 0.056787 | 0.002726 | −0.050547 | 0.016471 | 0.060833 |
| 207 | 0.181612 | 0.123798 | 0.1198 | −0.065289 | −0.166976 | 0.127344 | −0.160779 | −0.013009 | −0.045079 | 0.127487 | 0.155179 | −0.022975 | 0.042868 | 0.005948 |
| 208 | −0.057035 | 0.103309 | −0.020503 | 0.075862 | 0.256366 | 0.047161 | 0.00197 | −0.153614 | 0.023679 | −0.014506 | −0.003441 | −0.056266 | −0.031772 | 0.013376 |
| 209 | 0.053246 | 0.086063 | 0.04795 | 0.035815 | 0.055623 | 0.128405 | −0.033144 | 0.110527 | −0.064893 | −0.076539 | −0.014603 | 0.085252 | 0.077412 | 0.043285 |
| 210 | −0.063717 | −0.007891 | −0.068935 | 0.058624 | 0.165435 | −0.085906 | 0.045159 | 0.22336 | −0.067539 | 0.006967 | 0.028577 | 0.017317 | −0.00654 | −0.108972 |
| 211 | 0.157114 | −0.050744 | 0.078964 | −0.006837 | 0.023973 | 0.029338 | −0.183546 | 0.025177 | 0.085392 | 0.011548 | −0.048176 | 0.083599 | −0.037314 | 0.061154 |
| 212 | 0.03195 | −0.010303 | 0.007068 | −0.069404 | 0.139663 | 0.174281 | −0.039505 | −0.258158 | 0.02358 | −0.045589 | 0.107813 | 0.061239 | 0.117652 | 0.016268 |
| 213 | 0.095219 | 0.038827 | −0.108554 | −0.166321 | −0.063838 | 0.016911 | 0.087851 | −0.013336 | −0.045159 | 0.01016 | 0.017914 | −0.142644 | 0.075856 | −0.279059 |
| 214 | −0.006264 | −0.019377 | −0.033874 | −0.025842 | −0.048796 | −0.04582 | 0.050103 | −0.014244 | 0.030956 | −0.01161 | 0.011952 | −0.024902 | 0.041894 | 0.041096 |
| 215 | 0.017934 | 0.003856 | 0.009226 | −0.065875 | 0.039778 | 0.065673 | −0.023095 | −0.029066 | 0.006319 | 0.025295 | 0.087187 | 0.004526 | −0.03918 | 0.030837 |
| 216 | 0.075985 | 0.009232 | 0.035003 | 0.030447 | −0.029293 | 0.051423 | 0.029901 | −0.016155 | 0.05111 | 0.01715 | −0.005866 | 0.11183 | −0.069339 | −0.017191 |
| 217 | −0.013304 | −0.054793 | −0.013529 | 0.00196 | 0.014475 | −0.062026 | −0.02584 | −0.055211 | 0.034617 | 0.18427 | −0.128402 | 0.066859 | −0.054925 | −0.102467 |
| 218 | 0.024545 | 0.01292 | 0.004646 | 0.027648 | 0.011471 | −0.007401 | 0.002342 | −0.035698 | −0.003483 | 0.007469 | −0.008743 | 0.031064 | −0.02923 | 0.000715 |
| 219 | −0.012371 | −0.032488 | 0.000847 | 0.051653 | 0.002373 | −0.044947 | 0.00642 | −0.031857 | 0.006183 | 0.091552 | 0.010499 | 0.030133 | −0.032112 | 0.007737 |
| 220 | −0.052368 | −0.115867 | −0.078096 | 0.000389 | 0.014139 | 0.027015 | −0.036843 | 0.075999 | −0.004872 | 0.052817 | −0.086632 | 0.080738 | −0.076324 | −0.044549 |
| 221 | 0.027469 | −0.076102 | −0.079788 | −0.020872 | −0.028588 | −0.024222 | 0.03534 | −0.0498 | −0.071179 | −0.010394 | 0.001408 | 0.109452 | −0.023193 | −0.005736 |
| 222 | 0.105215 | 0.049367 | −0.080786 | −0.053113 | 0.043842 | −0.027784 | −0.001318 | −0.018819 | −0.018315 | −0.024062 | −0.010576 | 0.002921 | −0.033284 | 0.024946 |
| 223 | 0.067451 | 0.0282121 | −0.038775 | −0.021057 | 0.049347 | −0.026227 | −0.027613 | −0.03473 | −0.028485 | −0.00893 | −0.077392 | −0.009781 | −0.04885 | 0.050507 |
| 224 | 0.046067 | −0.185835 | 0.030874 | −0.065896 | 0.017684 | 0.043848 | 0.078749 | −0.025669 | 0.066869 | −0.00731 | 0.008073 | 0.037637 | 0.078033 | −0.100253 |
| 225 | 0.036501 | −0.185385 | 0.043864 | −0.051832 | 0.019236 | 0.044246 | 0.05762 | −0.038524 | 0.07228 | −0.008953 | −0.005901 | 0.047933 | 0.050303 | −0.102373 |
| 226 | −0.061806 | 0.014123 | 0.060152 | −0.04244 | −0.012305 | −0.004186 | 0.040617 | 0.071474 | 0.036148 | 0.011608 | −0.009411 | 0.004652 | −0.039247 | 0.021246 |
| 227 | −0.026496 | −0.07416 | 0.117319 | −0.160108 | 0.009849 | 0.098643 | 0.11724 | 0.07693 | 0.117383 | −0.027265 | −0.039478 | 0.149387 | −0.004116 | −0.086871 |
| 228 | 0.133047 | 0.037941 | 0.089362 | −0.007399 | 0.064046 | −0.019002 | −0.031501 | −0.048176 | 0.019978 | 0.00989 | 0.042555 | −0.068926 | −0.057444 | 0.041164 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 229 | 0.16015 | −0.070109 | −0.116769 | 0.093089 | −0.046844 | 0.018753 | −0.217473 | 0.039138 | 0.058383 | 0.001186 | 0.107672 | −0.087577 | −0.040255 | −0.068119 |
| 230 | 0.089583 | −0.034347 | −0.015552 | −0.020574 | −0.013576 | 0.080401 | −0.041155 | 0.046341 | 0.027287 | −0.080273 | 0.074353 | −0.010597 | −0.004231 | −0.037749 |
| 231 | −0.040718 | −0.009069 | 0.058408 | −0.116745 | 0.018332 | 0.027933 | 0.056107 | 0.030553 | 0.008283 | −0.019131 | −0.091021 | 0.0861861 | −0.079149 | −0.051341 |
| 232 | 0.114599 | 0.017396 | −0.036427 | −0.006454 | 0.024767 | −0.065052 | 0.033692 | 0.006028 | 0.031706 | 0.05895 | 0.084216 | −0.001887 | 0.040931 | 0.000594 |
| 233 | 0.003114 | 0.074303 | 0.006737 | 0.037563 | 0.019038 | 0.015784 | −0.04148 | 0.030943 | 0.000651 | 0.020141 | 0.090717 | 0.01596 | 0.000704 | −0.035648 |
| 234 | −0.011775 | 0.082536 | 0.067209 | 0.018673 | 0.047583 | 0.128197 | 0.028702 | −0.055747 | 0.007681 | −0.035002 | −0.027927 | −0.044706 | −0.012745 | 0.018713 |
| 235 | 0.048074 | −0.006784 | 0.054942 | −0.000883 | 0.062289 | 0.086125 | 0.058251 | −0.008431 | −0.030864 | −0.005245 | −0.092137 | −0.022641 | 0.006115 | 0.0099 |
| 236 | 0.098447 | 0.006481 | −0.074814 | −0.008698 | 0.056246 | −0.010927 | 0.051664 | −0.044409 | −0.022257 | 0.023535 | −0.058308 | 0.013902 | 0.037336 | −0.014169 |
| 237 | 0.047921 | 0.030482 | 0.053217 | 0.031776 | −0.046216 | −0.012807 | −0.041592 | −0.037926 | 0.024368 | 0.055832 | −0.093052 | −0.023564 | 0.043021 | −0.030905 |
| 238 | −0.035176 | 0.011314 | 0.038027 | 0.046875 | 0.001478 | −0.05706 | −0.039567 | −0.058079 | −0.022874 | 0.017089 | 0.030046 | −0.059561 | 0.02589 | −0.005945 |
| 239 | −0.038825 | 0.017911 | 0.040769 | 0.008757 | 0.063952 | −0.073045 | −0.026127 | −0.066618 | −0.007332 | −0.018602 | 0.032742 | −0.052575 | −0.01363 | 0.005365 |
| 240 | −0.056473 | −0.055822 | 0.026447 | 0.069871 | −0.024578 | 0.024993 | 0.054602 | 0.000226 | −0.04357 | 0.028291 | 0.046945 | −0.008118 | 0.031936 | −0.030752 |
| 241 | −0.040136 | 0.05711 | 0.054113 | 0.050815 | 0.003914 | 0.049053 | 0.008297 | −0.019334 | 0.001128 | −0.009131 | 0.072854 | −0.052333 | 0.046698 | −0.040329 |
| 242 | 0.121264 | 0.022765 | −0.030395 | −0.025211 | 0.06918 | −0.014379 | −0.017726 | 0.015273 | −0.047381 | −0.019912 | −0.066481 | 0.040954 | −0.023802 | 0.018086 |
| 243 | 0.134271 | −0.067923 | 0.044567 | −0.017975 | 0.014457 | −0.048646 | −0.084439 | 0.029898 | −0.063443 | −0.020432 | −0.04112 | 0.004812 | 0.025873 | 0.029285 |
| 244 | 0.006571 | −0.067599 | 0.010564 | −0.003286 | 0.01136 | −0.017527 | −0.0139 | −0.043713 | −0.039629 | 0.004431 | 0.003657 | 0.069389 | −0.019065 | −0.007515 |
| 245 | −0.015936 | 0.030102 | 0.00701 | 0.019703 | 0.051736 | −0.007699 | −0.008779 | −0.074057 | 0.01673 | −0.057797 | 0.03012 | 0.005848 | −0.043004 | 0.03964 |
| 246 | −0.014853 | 0.010614 | −0.087522 | −0.016408 | 0.008596 | 0.058611 | −0.022721 | 0.062359 | 0.009543 | −0.045494 | −0.021051 | 0.031877 | −0.066138 | 0.013885 |
| 247 | −0.049494 | −0.019632 | −0.118609 | −0.020025 | −0.005636 | 0.015477 | −0.00337 | 0.048896 | −0.008323 | −0.060865 | 0.032507 | 0.010927 | −0.009083 | −0.011241 |
| 248 | 0.008935 | −0.039549 | −0.095236 | −0.027052 | −0.015258 | 0.01943 | 0.024301 | 0.042984 | 0.000204 | 0.000174 | 0.018926 | −0.008879 | 0.020761 | −0.028844 |
| 249 | 0.085944 | 0.01157 | −0.014517 | 0.009839 | 0.049227 | 0.022043 | 0.053302 | 0.02308 | −0.025371 | 0.051687 | 0.022985 | −0.020573 | −0.010693 | −0.007125 |
| 250 | −0.021622 | −0.009745 | −0.004023 | 0.046556 | −0.007885 | 0.05349 | 0.038957 | −0.017968 | −0.022238 | 0.014188 | 0.01234 | −0.010588 | 0.005113 | −0.047731 |
| 251 | −0.028418 | −0.063565 | 0.051757 | 0.037857 | 0.002999 | 0.030712 | 0.032774 | −0.01997 | −0.008758 | 0.043845 | −0.008015 | −0.05018 | 0.058701 | −0.053215 |
| 252 | 0.029949 | −0.039216 | 0.035787 | −0.013749 | −0.003477 | −0.081456 | −0.010823 | −0.045748 | 0.054889 | −0.04695 | 0.000338 | −0.027339 | −0.004026 | 0.007448 |
| 253 | 0.083203 | −0.008547 | 0.011973 | −0.00846 | −0.032772 | −0.018627 | −0.058052 | −0.034157 | −0.042071 | −0.007999 | −0.019231 | 0.034596 | −0.024769 | 0.102395 |
| 254 | 0.06979 | 0.022483 | −0.018268 | 0.022453 | 0.077377 | −0.00847 | −0.053778 | −0.024285 | −0.02473 | 0.003753 | −0.042984 | 0.023279 | −0.044873 | 0.04629 |
| 255 | −0.014636 | −0.068419 | −0.035003 | 0.020471 | 0.006741 | 0.036755 | −0.023186 | 0.018375 | −0.046366 | −0.01697 | −0.027072 | 0.063971 | −0.006267 | 0.022076 |
| 256 | −0.10649 | 0.0167 | −0.019166 | 0.051777 | −0.028224 | 0.069716 | −0.05632 | −0.056487 | 0.004223 | −0.115819 | 0.044513 | −0.012159 | 0.001769 | 0.115778 |
| 257 | −0.069045 | 0.050894 | 0.001794 | −0.024553 | −0.014911 | 0.027222 | 0.052107 | −0.036938 | 0.008474 | −0.028194 | 0.021345 | −0.006574 | 0.000179 | 0.034149 |
| 758 | −0.048975 | 0.018322 | 0.021315 | −0.077086 | −0.046704 | 0.011874 | 0.061341 | −0.025262 | 0.002495 | −0.026924 | −0.015321 | 0.032507 | 0.042336 | −0.026877 |
| 259 | 0.099806 | 0.027253 | −0.001703 | −0.006592 | 0.060751 | −0.020606 | −0.018225 | 0.005247 | −0.016677 | 0.00521 | −0.025802 | −0.041194 | −0.029285 | −0.030798 |
| 260 | 0.071974 | 0.023308 | −0.014632 | −0.007792 | 0.018223 | −0.101587 | −0.042098 | −0.083694 | 0.074961 | −0.019304 | 0.020991 | −0.017584 | −0.065091 | −0.031218 |
| 261 | −0.031179 | −0.00256 | −0.004138 | −0.021643 | −0.016638 | −0.037682 | −0.004505 | −0.051757 | 0.021483 | 0.016117 | 0.000222 | −0.03527 | −0.01976 | −0.048218 |
| 262 | 0.037734 | −0.010733 | −0.021386 | −0.026478 | 0.011425 | −0.050422 | 0.012949 | −0.032142 | 0.01104 | −0.007794 | −0.011934 | 0.027336 | 0.00337 | 0.004452 |
| 263 | 0.06492 | −0.025358 | 0.000768 | −0.025288 | 0.035257 | −0.041161 | 0.035882 | −0.001856 | −0.006885 | −0.006246 | −0.011108 | 0.027653 | −0.014928 | 0.003994 |
| 264 | 0.103377 | 0.042192 | −0.035707 | −0.051727 | 0.070407 | 0.01572 | −0.009628 | 0.047005 | −0.003497 | −0.023175 | −0.020695 | −0.022409 | −0.035911 | 0.050999 |
| 265 | 0.021493 | 0.072229 | −0.021974 | −0.010695 | −0.000958 | −0.051806 | −0.074436 | −0.008353 | 0.006765 | −0.030383 | −0.049485 | −0.053666 | −0.040821 | 0.079297 |
| 266 | −0.063771 | 0.023445 | −0.037811 | 0.021381 | −0.03457 | −0.049269 | −0.064543 | −0.019451 | 0.015194 | −0.02814 | −0.054044 | −0.040487 | −0.0042 | 0.035102 |
| 267 | −0.03959 | 0.000972 | 0.038358 | 0.112616 | −0.086492 | −0.014245 | −0.053488 | −0.001114 | 0.023895 | 0.043953 | 0.087128 | 0.018679 | −0.071949 | 0.099952 |
| 268 | −0.063447 | 0.00758 | 0.05392 | 0.009619 | −0.013023 | 0.011611 | 0.049968 | 0.057813 | 0.01598 | −0.003662 | 0.00682 | 0.018612 | −0.041372 | 0.035678 |
| 269 | −0.04563 | −0.005978 | 0.043726 | −0.00577 | −0.061614 | 0.04243 | 0.05914 | 0.053355 | 0.017708 | 0.029618 | −0.002501 | −0.013465 | −0.020651 | 0.017259 |
| 270 | −0.05244 | −0.001156 | 0.070715 | −0.05905 | −0.042818 | 0.047759 | 0.09524 | 0.070465 | 0.052249 | 0.012322 | 0.00585 | 0.032854 | −0.008757 | 0.004076 |
| 271 | 0.125803 | −0.032351 | −0.088658 | 0.117929 | −0.073485 | −0.013286 | −0.098227 | 0.034342 | 0.066514 | 0.061318 | −0.035028 | −0.037371 | −0.129631 | −0.022354 |
| 272 | 0.066367 | −0.048819 | −0.056274 | 0.10824 | −0.020955 | −0.051374 | −0.179854 | 0.038843 | 0.003565 | 0.019203 | 0.071515 | −0.117425 | −0.042374 | 0.009784 |
| 273 | 0.053374 | −0.064845 | −0.052128 | −0.003311 | −0.002328 | 0.007673 | −0.079103 | 0.084394 | −0.002951 | −0.029343 | 0.060533 | −0.050862 | 0.010186 | −0.050979 |
| 274 | 0.05342 | −0.069979 | −0.055558 | −0.018874 | −0.015701 | 0.013272 | −0.075721 | 0.08018 | −0.001308 | −0.015008 | 0.060033 | −0.061072 | 0.02851 | −0.051581 |
| 275 | 0.071147 | −0.047849 | −0.005536 | −0.090215 | −0.032062 | 0.068102 | 0.033799 | 0.101666 | 0.039598 | −0.025779 | 0.072735 | 0.024258 | 0.053281 | −0.045344 |
| 276 | 0.113848 | 0.009386 | −0.098993 | 0.067413 | 0.044889 | 0.002616 | −0.020169 | −0.046315 | −0.030171 | 0.022939 | −0.038964 | −0.036187 | 0.028883 | −0.024874 |
| 277 | 0.086078 | 0.099524 | 0.027762 | −0.013532 | 0.033509 | −0.019415 | 0.001325 | −0.035646 | −0.005666 | 0.023894 | 0.013486 | −0.00656 | 0.0513 | −0.012843 |
| 278 | 0.088893 | 0.054048 | 0.01589 | −0.034715 | 0.027446 | −0.042797 | 0.010295 | −0.066798 | 0.048531 | 0.023738 | −0.015087 | −0.059936 | 0.082496 | −0.000899 |
| 279 | 0.002899 | 0.005486 | 0.03798 | 0.018324 | 0.039865 | −0.083891 | −0.004611 | −0.052102 | −0.016236 | 0.01794 | 0.076602 | −0.098997 | 0.085046 | 0.018151 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 280 | 0.147185 | −0.050603 | 0.023458 | 0.001055 | 0.003084 | −0.002413 | −0.06087 | 0.054591 | −0.080633 | −0.01123 | −0.020155 | 0.038152 | 0.037644 | 0.030637 |
| 281 | −0.026929 | −0.006358 | −0.088121 | −0.045407 | 0.030002 | 0.065482 | 0.000843 | 0.139117 | −0.018836 | −0.052242 | 0.069762 | −0.001582 | 0.014457 | −0.0238 |
| 282 | −0.017232 | −0.017527 | −0.076826 | −0.039108 | −0.010521 | 0.073638 | 0.034582 | 0.105544 | −0.026712 | −0.07193 | 0.064473 | −0.026403 | 0.048129 | −0.015411 |
| 283 | −0.03234 | −0.045024 | −0.101334 | −0.081757 | 0.017982 | −0.006533 | 0.00968 | 0.088001 | 0.002313 | −0.032847 | 0.069456 | −0.052816 | 0.070764 | −0.000612 |
| 284 | −0.040351 | 0.047682 | 0.014583 | −0.011707 | −0.003914 | 0.02868 | 0.051768 | −0.009008 | 0.012234 | −0.021605 | 0.040843 | −0.030134 | 0.02291 | 0.036058 |
| 285 | −0.036067 | 0.054726 | 0.024242 | −0.032632 | 0.006085 | 0.039701 | 0.061205 | −0.019428 | 0.021175 | −0.015805 | 0.054564 | −0.02833 | 0.02484 | 0.038503 |
| 286 | −0.06476 | 0.063744 | 0.090545 | −0.04263 | −0.056631 | 0.056436 | 0.067163 | 0.007429 | 0.022729 | −0.009254 | 0.035393 | 0.013106 | 0.076765 | −0.04022 |
| 287 | −0.064925 | 0.023594 | 0.103657 | −0.052459 | −0.041145 | 0.007784 | 0.0736 | 0.017765 | 0.033417 | −0.015912 | 0.027626 | −0.001501 | 0.084685 | −0.030176 |
| 288 | −0.005203 | −0.03391 | 0.021164 | −0.145914 | −0.035094 | −0.031839 | 0.095409 | 0.048221 | 0.014863 | 0.016641 | −0.021826 | −0.015317 | 0.11648 | −0.000989 |
| 289 | 0.005277 | −0.025462 | −0.014657 | −0.007591 | −0.003914 | −0.045328 | 0.011261 | −0.022139 | 0.009812 | −0.002515 | −0.012017 | 0.024326 | 0.023052 | −0.002934 |
| 290 | −0.055722 | −0.075089 | 0.057451 | −0.0127 | −0.072005 | 0.035157 | −0.034743 | 0.011884 | −0.020051 | −0.044463 | 0.013144 | −0.008769 | 0.022781 | 0.081624 |
| 291 | −0.05314 | −0.075557 | 0.061249 | −0.002867 | −0.068296 | 0.038424 | −0.034028 | 0.021673 | −0.021829 | −0.049314 | 0.01132 | −0.005003 | 0.019587 | 0.083019 |
| 292 | −0.062544 | −0.068303 | 0.069196 | 0.000205 | −0.05986 | 0.04472 | −0.039804 | 0.025772 | −0.033158 | −0.026806 | 0.029706 | −0.037183 | 0.01954 | 0.071214 |
| 293 | 0.020308 | −0.01261 | −0.095175 | −0.091273 | 0.042481 | −0.012567 | 0.035006 | −0.04384 | −0.082912 | −0.05073 | −0.030884 | 0.057027 | −0.029104 | 0.105577 |
| 294 | 0.035454 | −0.034654 | 0.002803 | −0.043043 | 0.016832 | −0.019968 | 0.011527 | −0.012684 | −0.051589 | −0.047287 | −0.007418 | 0.029649 | −0.016856 | −0.011118 |
| 295 | 0.04567 | −0.058975 | −0.122578 | −0.060162 | 0.055761 | −0.043107 | −0.057067 | 0.004012 | −0.086799 | −0.059549 | 0.014776 | −0.008052 | 0.00821 | 0.021501 |
| 296 | 0.028796 | −0.073903 | −0.06197 | −0.047562 | 0.029581 | −0.001674 | 0.003729 | 0.04639 | −0.050965 | −0.0452 | 0.040872 | 0.028819 | 0.060638 | −0.014319 |
| 297 | 0.030743 | −0.041102 | −0.108786 | −0.028446 | 0.078439 | −0.032701 | −0.06472 | −0.001877 | −0.079458 | −0.080015 | 0.00975 | −0.034519 | 0.00688 | 0.013147 |
| 298 | 0.014305 | −0.016048 | −0.012165 | 0.103375 | 0.022712 | −0.038087 | −0.043997 | −0.052625 | −0.009132 | 0.076851 | −0.047553 | −0.019063 | 0.086117 | 0.04835 |
| 299 | −0.01966 | −0.030992 | −0.021315 | −0.026674 | 0.102598 | −0.081119 | −0.047362 | −0.015676 | −0.072973 | −0.05861 | 0.037769 | −0.03437 | 0.030358 | −0.006902 |
| 300 | 0.006064 | −0.025813 | 0.060911 | 0.113636 | 0.006255 | 0.030219 | −0.106391 | −0.018537 | −0.036401 | 0.077418 | −0.034752 | 0.017448 | 0.066924 | 0.003857 |
| 301 | 0.032577 | −0.006532 | −0.05648 | −0.038533 | 0.082262 | −0.068683 | 0.015191 | −0.061285 | −0.05027 | −0.038032 | 0.014786 | −0.011372 | 0.003981 | 0.059072 |
| 302 | 0.017615 | −0.021135 | 0.004782 | −0.029704 | 0.046813 | −0.030197 | 0.007353 | −0.008613 | −0.032854 | 0.010843 | 0.039241 | 0.045677 | 0.022944 | −0.005421 |
| 303 | −0.012108 | −0.002103 | 0.081782 | 0.023375 | 0.059808 | −0.098749 | −0.065092 | −0.065847 | −0.041586 | −0.042076 | 0.038558 | −0.028683 | 0.048338 | −0.038926 |
| 304 | −0.022764 | −0.012629 | 0.104186 | 0.000318 | 0.046835 | −0.069089 | −0.051042 | −0.010562 | −0.033378 | 0.009369 | 0.047269 | 0.005799 | 0.035276 | −0.041942 |
| 305 | 0.037244 | 0.023256 | −0.017147 | −0.063555 | 0.126034 | 0.022088 | 0.059456 | −0.04556 | −0.011067 | 0.014666 | 0.065678 | 0.007401 | −0.054024 | 0.047716 |
| 306 | −0.020165 | −0.129783 | 0.022714 | −0.007822 | −0.038118 | 0.062091 | −0.049936 | −0.01264 | −0.003645 | −0.038154 | −0.011256 | 0.004102 | −0.023964 | 0.007614 |
| 307 | 0.111518 | −0.069442 | 0.108101 | 0.018755 | −0.140207 | 0.021794 | −0.00816 | −0.035038 | 0.02493 | −0.062688 | −0.03633 | −0.081485 | −0.141437 | 0.038684 |
| 308 | 0.012104 | −0.029006 | 0.043792 | −0.011884 | 0.027613 | 0.009637 | 0.010144 | 0.025369 | 0.00873 | 0.028891 | 0.08834 | 0.025107 | −0.010242 | −0.000022 |
| 309 | −0.003851 | 0.029011 | 0.020941 | 0.013194 | −0.004975 | 0.023299 | 0.036162 | 0.036638 | 0.000636 | −0.007333 | −0.01868 | 0.000222 | −0.012999 | 0.002172 |
| 310 | −0.007321 | −0.041253 | 0.081038 | 0.018979 | 0.008631 | 0.092143 | −0.01047 | 0.025488 | −0.048281 | 0.056668 | 0.054613 | 0.029512 | 0.054101 | 0.029382 |
| 311 | 0.062478 | 0.035921 | −0.013533 | 0.039233 | −0.027209 | −0.004145 | 0.002251 | 0.045522 | 0.040702 | −0.081889 | −0.052575 | −0.058108 | −0.017006 | −0.026922 |
| 312 | 0.053806 | −0.092249 | 0.069344 | 0.089696 | −0.059193 | 0.080376 | −0.037073 | 0.010708 | 0.054161 | −0.154132 | −0.115115 | 0.005695 | 0.022063 | 0.029839 |
| 313 | 0.011637 | 0.051255 | −0.012828 | 0.012798 | 0.030014 | 0.01547 | 0.001523 | 0.049094 | 0.032602 | −0.096383 | −0.060773 | −0.076331 | −0.03226 | 0.011305 |
| 314 | 0.033887 | 0.047348 | 0.086389 | 0.031714 | 0.019806 | −0.011066 | −0.008032 | −0.014097 | −0.104917 | 0.005081 | −0.054175 | −0.092212 | 0.014382 | −0.007181 |
| 315 | −0.004769 | 0.068408 | 0.012826 | 0.009032 | 0.011641 | −0.004478 | 0.017505 | 0.043524 | 0.00403 | −0.062585 | −0.067258 | −0.045687 | −0.03613 | −0.006053 |
| 316 | 0.029617 | 0.070839 | 0.01963 | −0.001095 | −0.048663 | 0.012743 | 0.138434 | −0.032071 | −0.160874 | 0.039108 | 0.046262 | −0.028392 | 0.063728 | 0.15797 |
| 317 | 0.019973 | 0.093627 | −0.045116 | −0.005104 | −0.010699 | 0.020874 | 0.047982 | −0.021367 | 0.007083 | −0.050134 | −0.05052 | −0.026757 | −0.036841 | 0.027896 |
| 318 | 0.0604 | 0.060421 | −0.027198 | −0.007283 | 0.037818 | 0.015415 | 0.004755 | 0.017198 | 0.01108 | −0.004023 | −0.052752 | −0.013387 | −0.070552 | −0.048376 |
| 319 | −0.014589 | 0.074017 | 0.029102 | −0.002594 | 0.008348 | 0.002312 | 0.029613 | 0.018256 | −0.008683 | −0.027175 | −0.049568 | 0.008393 | −0.034246 | 0.004988 |
| 320 | −0.029834 | 0.06508 | 0.021627 | −0.006204 | −0.01452 | 0.008486 | 0.012428 | 0.034129 | −0.024945 | −0.017697 | −0.025672 | 0.036549 | −0.019195 | 0.022676 |
| 321 | −0.003329 | −0.020496 | 0.001563 | −0.009459 | 0.036227 | −0.025585 | −0.032375 | 0.006641 | 0.07737 | −0.026592 | −0.002741 | −0.069982 | 0.029391 | −0.027802 |
| 322 | 0.079735 | −0.088057 | 0.046288 | 0.216624 | 0.00126 | −0.083489 | 0.089835 | −0.124513 | −0.006153 | 0.145483 | 0.017912 | 0.152156 | 0.101507 | 0.000787 |
| 323 | 0.022637 | 0.00482 | 0.018704 | 0.022929 | 0.017766 | 0.012683 | 0.038184 | 0.033947 | 0.063696 | 0.004033 | −0.006943 | −0.0869 | 0.108719 | −0.006824 |
| 324 | −0.050947 | −0.09451 | 0.045914 | 0.008339 | −0.053012 | 0.077241 | −0.012357 | −0.116771 | −0.04924 | 0.092258 | 0.05078 | −0.095253 | 0.082293 | 0.023245 |
| 325 | −0.004133 | 0.044762 | 0.001156 | 0.018131 | −0.041417 | −0.003651 | 0.014863 | 0.005025 | −0.006268 | −0.060266 | −0.046827 | −0.006017 | −0.025999 | −0.005838 |
| 326 | −0.015464 | 0.008079 | −0.014624 | −0.015368 | −0.074296 | −0.043788 | 0.025009 | −0.032491 | 0.04406 | −0.075948 | 0.0219 | 0.013603 | −0.072682 | −0.025568 |
| 327 | 0.024366 | 0.037996 | −0.01476 | 0.018052 | 0.01045 | 0.029398 | 0.009128 | 0.034454 | 0.021511 | 0.014311 | 0.022513 | −0.045205 | 0.019515 | −0.025597 |
| 328 | 0.071052 | −0.095461 | 0.007755 | 0.056792 | 0.053667 | 0.048118 | 0.101001 | −0.14971 | 0.045286 | 0.110363 | 0.060143 | 0.060696 | −0.010835 | −0.020691 |
| 329 | 0.029215 | 0.029254 | −0.021104 | 0.031157 | 0.01423 | 0.009963 | 0.007141 | 0.033364 | 0.029149 | −0.034937 | 0.011859 | −0.032947 | 0.044088 | −0.02249 |
| 330 | −0.025214 | 0.036775 | 0.008858 | 0.096852 | 0.166411 | 0.06404 | −0.039647 | −0.034252 | 0.075916 | 0.136122 | 0.124681 | 0.088114 | −0.160071 | −0.232681 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 331 | 0.006942 | 0.043049 | 0.002181 | 0.031917 | −0.047973 | −0.012653 | −0.001267 | 0.033814 | 0.023666 | −0.037505 | −0.012674 | −0.013713 | 0.007007 | −0.00163 |
| 332 | −0.009627 | −0.037637 | −0.011904 | 0.116283 | −0.065165 | 0.057121 | 0.005982 | 0.055207 | −0.147772 | 0.119633 | 0.015608 | 0.10353 | −0.076931 | −0.095864 |
| 333 | 0.019949 | 0.077658 | −0.042257 | 0.026022 | −0.039295 | 0.011631 | 0.05434 | −0.006124 | 0.015981 | −0.038205 | −0.040978 | −0.013126 | −0.039714 | 0.00068 |
| 334 | 0.031925 | 0.055512 | −0.041455 | 0.0784 | −0.119132 | 0.051672 | 0.007496 | −0.006806 | −0.012698 | −0.004528 | −0.068573 | 0.067564 | 0.006648 | −0.051517 |
| 335 | −0.000654 | 0.066051 | 0.026965 | 0.016561 | −0.037395 | −0.0027 | 0.029039 | 0.029882 | 0.038024 | −0.019787 | −0.012197 | −0.005503 | −0.004039 | −0.013503 |
| 336 | 0.00013 | −0.01995 | 0.013758 | 0.088209 | −0.036327 | −0.027536 | −0.022974 | −0.018753 | 0.068808 | −0.053292 | −0.04846 | 0.015322 | −0.035478 | −0.017724 |
| 337 | −0.036783 | −0.044022 | 0.027222 | 0.006459 | −0.046919 | 0.012797 | −0.002093 | 0.011026 | −0.085423 | 0.004583 | 0.008971 | −0.020738 | −0.035184 | 0.044321 |
| 338 | −0.063598 | −0.188603 | −0.161478 | 0.155552 | 0.025145 | 0.022915 | 0.160793 | 0.044266 | 0.025723 | 0.182972 | −0.097441 | −0.159111 | 0.07312 | 0.024826 |
| 339 | 0.042651 | −0.00694 | 0.031814 | −0.044317 | −0.008777 | −0.027158 | 0.088851 | 0.038438 | 0.029683 | −0.015984 | −0.041559 | 0.002421 | 0.081021 | −0.018597 |
| 340 | −0.127092 | −0.090523 | −0.011467 | 0.04805 | 0.062171 | −0.008453 | −0.174582 | 0.168402 | −0.012025 | 0.056296 | −0.044372 | −0.043307 | −0.007871 | −0.100801 |

| | AN | AO | AP | AQ | AR | AS | AT | AU | AV | AW | AX | AY | AZ | BA |
|---|---|---|---|---|---|---|---|---|---|---|---|---|---|---|
| 1 | 0.004679 | 0.003379 | −0.021793 | 0.004162 | 0.024658 | 0.004743 | −0.027757 | 0.028369 | 0.054758 | −0.014105 | −0.018636 | 0.024726 | −0.013987 | −0.001211 |
| 2 | −0.076035 | 0.019857 | 0.037339 | 0.008095 | 0.042914 | 0.03221 | −0.042727 | 0.00822 | −0.004492 | 0.021129 | 0.027486 | 0.027643 | −0.051439 | 0.046906 |
| 3 | −0.028644 | −0.011921 | 0.046397 | 0.013439 | 0.017877 | 0.023913 | −0.004573 | 0.006351 | 0.041128 | −0.016982 | −0.002519 | 0.039108 | −0.001658 | −0.054432 |
| 4 | 0.057557 | 0.000469 | −0.063349 | −0.051533 | −0.002024 | 0.002313 | −0.061319 | 0.040597 | 0.041518 | −0.025484 | −0.049419 | 0.013391 | 0.010608 | −0.002184 |
| 5 | −0.018513 | −0.080459 | −0.107376 | 0.027465 | −0.015881 | 0.154302 | 0.003594 | 0.027988 | 0.026093 | −0.053233 | 0.033378 | 0.032397 | −0.015661 | 0.183396 |
| 6 | 0.047515 | 0.078679 | 0.020187 | 0.039024 | −0.030085 | 0.004052 | 0.112325 | −0.013117 | −0.061844 | 0.104373 | −0.089609 | 0.111822 | 0.088346 | 0.000878 |
| 7 | 0.055221 | 0.052287 | 0.044452 | −0.058632 | 0.030351 | 0.025275 | 0.064312 | −0.006071 | −0.00188 | −0.014834 | −0.07957 | 0.048681 | −0.019348 | −0.072386 |
| 8 | −0.016121 | 0.00059 | 0.05576 | 0.147233 | −0.041526 | −0.010232 | 0.053579 | 0.064702 | −0.20904 | −0.092989 | −0.005671 | 0.050425 | −0.004089 | 0.134387 |
| 9 | 0.047687 | 0.017344 | −0.053171 | −0.120137 | 0.006372 | 0.032964 | −0.028825 | −0.005685 | 0.04079 | −0.102973 | −0.103582 | −0.057459 | 0.06695 | 0.03458 |
| 10 | 0.008293 | −0.004937 | −0.00115 | −0.028811 | −0.014844 | 0.044273 | −0.063023 | −0.015142 | 0.031529 | 0.047923 | −0.017836 | 0.111717 | 0.011332 | 0.000602 |
| 11 | −0.012495 | 0.118661 | −0.049041 | 0.002113 | 0.059685 | −0.234094 | −0.033933 | −0.131962 | 0.027143 | 0.015095 | 0.086662 | −0.090737 | 0.053902 | 0.018108 |
| 12 | 0.005834 | −0.117366 | 0.058789 | 0.129 | 0.01154 | 0.083161 | 0.08575 | 0.188144 | −0.021562 | −0.115045 | −0.187393 | −0.123941 | −0.102077 | 0.074037 |
| 13 | 0.018458 | 0.01057 | −0.009032 | 0.020899 | −0.002186 | −0.011027 | −0.017766 | −0.022024 | 0.006936 | −0.000198 | −0.023686 | 0.01947 | 0.017638 | −0.000033 |
| 14 | 0.016417 | −0.01214 | 0.012993 | 0.027102 | −0.024147 | −0.008351 | −0.005435 | −0.031354 | −0.00911 | 0.000472 | −0.040709 | 0.007239 | 0.037851 | 0.010449 |
| 15 | 0.022675 | 0.006721 | 0.003396 | 0.010622 | 0.000572 | 0.027939 | 0.011816 | −0.030323 | 0.035231 | 0.000514 | 0.004333 | −0.011308 | −0.009229 | −0.025846 |
| 16 | 0.035173 | −0.116114 | 0.005363 | 0.051463 | 0.024452 | 0.032349 | 0.028413 | −0.109817 | 0.078146 | −0.085501 | −0.208213 | −0.007001 | 0.081753 | 0.124828 |
| 17 | −0.025523 | 0.006672 | −0.023292 | −0.020791 | 0.01533 | 0.017709 | 0.03077 | −0.049538 | −0.047994 | −0.020885 | −0.059214 | −0.011469 | −0.102956 | 0.023249 |
| 18 | −0.025131 | −0.053649 | 0.049683 | −0.057534 | −0.022561 | 0.028322 | 0.10405 | 0.016342 | −0.021297 | −0.107868 | 0.01494 | 0.031245 | 0.047513 | 0.01351 |
| 19 | −0.050059 | −0.004658 | −0.016501 | −0.021276 | −0.063979 | −0.044324 | −0.033291 | −0.016513 | 0.118566 | −0.004034 | 0.033589 | 0.018042 | −0.040485 | −0.045925 |
| 20 | 0.008414 | −0.011335 | −0.017234 | 0.006597 | −0.008666 | 0.000142 | 0.008087 | −0.004307 | −0.007874 | 0.005496 | −0.002555 | −0.005169 | −0.006383 | −0.011839 |
| 21 | −0.116054 | −0.002348 | 0.053389 | 0.033385 | 0.043917 | 0.017155 | −0.065494 | 0.02757 | −0.034795 | −0.047254 | 0.017535 | 0.001458 | −0.061371 | 0.038881 |
| 22 | −0.001078 | 0.094778 | −0.005129 | 0.007607 | −0.080255 | 0.034113 | 0.020134 | −0.024212 | −0.003456 | 0.152452 | −0.012331 | −0.020105 | −0.016098 | 0.006775 |
| 23 | 0.102078 | 0.025111 | 0.005391 | 0.000082 | −0.112697 | −0.026974 | 0.070814 | −0.068007 | 0.045704 | 0.070536 | −0.130566 | −0.018944 | 0.024889 | 0.083667 |
| 24 | −0.008036 | 0.005115 | −0.0393 | 0.0141 | 0.072927 | 0.015244 | −0.012937 | 0.056703 | 0.007266 | −0.051396 | 0.006038 | −0.098589 | −0.025171 | −0.016647 |
| 25 | −0.035326 | 0.021051 | 0.085185 | −0.072453 | 0.062989 | 0.048153 | −0.024273 | −0.047874 | −0.021472 | −0.056283 | −0.018844 | −0.038048 | −0.031982 | 0.055882 |
| 26 | 0.00551 | −0.011961 | −0.026635 | −0.000608 | −0.001545 | 0.003485 | 0.012351 | −0.000504 | −0.003503 | 0.005515 | 0.001086 | −0.005613 | −0.003621 | −0.017596 |
| 27 | −0.007238 | −0.007502 | −0.019638 | −0.001513 | −0.004505 | 0.022043 | −0.002194 | 0.002915 | −0.003835 | 0.000873 | −0.004157 | 0.00917 | 0.003574 | −0.005159 |
| 28 | 0.015258 | 0.015409 | −0.020968 | −0.015112 | 0.01677 | 0.021842 | 0.013118 | 0.044771 | 0.001314 | −0.049184 | −0.012256 | 0.00787 | −0.007086 | 0.000805 |
| 29 | 0.003165 | 0.053075 | 0.022617 | 0.030731 | −0.078638 | 0.042179 | 0.044604 | −0.021754 | −0.007827 | −0.036923 | 0.105107 | 0.047007 | −0.006306 | −0.099919 |
| 30 | 0.04426 | −0.032218 | −0.061515 | 0.034331 | 0.004973 | 0.064726 | −0.01487 | 0.057122 | −0.050162 | 0.067175 | 0.032014 | 0.024925 | 0.00227 | −0.025465 |
| 31 | −0.015035 | 0.00829 | −0.015165 | 0.018163 | 0.04475 | −0.016341 | 0.022571 | −0.003849 | −0.007226 | −0.022142 | 0.039387 | −0.011507 | −0.017486 | −0.002145 |
| 32 | 0.016071 | 0.001599 | 0.063342 | −0.026881 | −0.128715 | −0.011919 | 0.020769 | −0.13765 | 0.036991 | 0.021263 | −0.008755 | 0.003539 | 0.096823 | 0.021656 |
| 33 | −0.026321 | 0.014989 | −0.009775 | 0.028333 | −0.01284 | −0.051366 | −0.007418 | −0.024405 | −0.059849 | 0.044442 | −0.006969 | 0.007662 | −0.000362 | 0.01628 |
| 34 | 0.010658 | −0.012317 | 0.01136 | −0.025279 | 0.01129 | 0.023706 | −0.04081 | −0.023149 | −0.002258 | −0.019097 | 0.01992 | −0.036322 | −0.015777 | −0.033615 |
| 35 | 0.097727 | −0.018421 | −0.124897 | 0.076666 | −0.035149 | −0.012788 | −0.062995 | −0.073836 | −0.03973 | −0.106889 | 0.028314 | −0.07075 | 0.087306 | −0.004843 |
| 36 | 0.024744 | −0.028497 | 0.04276 | 0.001364 | −0.004822 | 0.032526 | −0.048354 | 0.052541 | −0.01719 | 0.039157 | −0.035709 | −0.032017 | −0.040704 | −0.025928 |
| 37 | 0.026123 | −0.028814 | −0.011648 | 0.005528 | 0.012461 | −0.018325 | 0.032822 | −0.012618 | −0.015817 | 0.004012 | 0.007881 | −0.02706 | −0.034309 | −0.050692 |
| 38 | 0.027976 | −0.146547 | 0.032191 | 0.007643 | −0.088557 | −0.068384 | −0.102133 | 0.033431 | 0.081576 | 0.089756 | 0.032086 | 0.174385 | −0.014392 | 0.190438 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 39 | 0.038368 | −0.070255 | −0.088202 | −0.037865 | −0.019937 | −0.030964 | −0.02221 | −0.007798 | 0.023074 | 0.054052 | −0.00364 | −0.015256 | −0.018684 | 0.036774 |
| 40 | −0.036567 | −0.019776 | 0.066363 | −0.00544 | −0.018267 | −0.014908 | −0.017663 | −0.063927 | −0.042318 | 0.016583 | 0.056348 | −0.049984 | 0.002378 | 0.01176 |
| 41 | −0.088968 | −0.026964 | 0.086427 | −0.045554 | 0.010156 | −0.010235 | −0.029632 | −0.027861 | 0.00785 | −0.017857 | 0.000579 | −0.03383 | 0.001414 | 0.013273 |
| 42 | −0.005338 | −0.037613 | 0.030631 | −0.026528 | −0.091746 | −0.048817 | −0.020054 | −0.007781 | 0.052192 | 0.031258 | 0.008543 | −0.063171 | 0.044314 | 0.008663 |
| 43 | −0.055041 | −0.010201 | 0.080264 | −0.042869 | −0.003336 | 0.020383 | 0.006168 | −0.03612 | −0.033923 | 0.005124 | 0.030015 | −0.008961 | 0.014378 | −0.011315 |
| 44 | −0.033122 | −0.014879 | 0.075526 | 0.029666 | 0.025313 | −0.014947 | 0.042963 | −0.074575 | 0.022017 | 0.000246 | 0.052985 | −0.024754 | −0.061245 | −0.063287 |
| 45 | −0.048074 | −0.041395 | 0.104614 | −0.045362 | −0.019782 | −0.010855 | 0.083653 | −0.034486 | −0.056713 | −0.035638 | −0.017598 | −0.008685 | 0.030231 | −0.041157 |
| 46 | 0.028026 | 0.044189 | −0.003134 | −0.017339 | 0.091736 | 0.025912 | 0.102574 | 0.015129 | −0.042641 | 0.008529 | −0.121791 | −0.085464 | −0.001741 | −0.015432 |
| 47 | 0.046473 | 0.026307 | −0.058861 | −0.010055 | 0.033081 | −0.026307 | 0.065292 | −0.042605 | −0.015076 | −0.070933 | −0.004403 | −0.01367 | −0.077518 | 0.043392 |
| 48 | −0.015632 | −0.040072 | −0.074649 | 0.012909 | −0.051625 | −0.095299 | 0.034074 | −0.011518 | −0.029649 | 0.011934 | −0.062225 | 0.033918 | 0.037575 | −0.048785 |
| 49 | 0.042406 | −0.024475 | −0.06902 | 0.025881 | 0.003843 | 0.077235 | −0.004173 | 0.051625 | −0.033785 | 0.045082 | 0.035507 | 0.033743 | 0.022188 | −0.03303 |
| 50 | 0.075215 | 0.052918 | −0.025653 | −0.023239 | 0.029036 | −0.003838 | 0.015526 | 0.000786 | 0.000912 | −0.022517 | −0.034935 | 0.030692 | 0.026901 | −0.015329 |
| 51 | 0.012383 | −0.000252 | 0.051369 | −0.038839 | 0.005784 | 0.049983 | −0.014623 | 0.01198 | −0.045553 | 0.013424 | −0.01805 | −0.012684 | 0.040602 | 0.004091 |
| 52 | 0.058229 | 0.083166 | −0.028914 | 0.058613 | −0.053019 | −0.038815 | −0.003395 | 0.034647 | −0.016141 | 0.005368 | −0.037307 | 0.039249 | −0.021473 | 0.033601 |
| 53 | 0.002804 | −0.004505 | 0.046929 | 0.010988 | 0.033104 | 0.01684 | 0.034818 | −0.016295 | 0.03104 | −0.00444 | −0.031463 | −0.018102 | −0.01755 | −0.021484 |
| 54 | 0.035892 | −0.066623 | 0.024907 | 0.043584 | −0.076863 | 0.012445 | −0.046583 | 0.009513 | 0.036588 | 0.017162 | −0.02241 | −0.047697 | 0.045917 | 0.039983 |
| 55 | 0.017848 | 0.015332 | −0.005262 | 0.035308 | 0.030883 | −0.013533 | 0.05104 | 0.038171 | −0.01616 | 0.022236 | 0.002138 | 0.024946 | 0.002503 | −0.001647 |
| 56 | 0.015679 | −0.000851 | −0.061679 | 0.015921 | 0.020939 | 0.095338 | 0.016053 | 0.033304 | −0.021765 | 0.0314 | 0.059917 | 0.044002 | 0.025438 | 0.008894 |
| 57 | −0.01485 | −0.005726 | 0.003069 | −0.011683 | 0.036016 | −0.072231 | 0.001102 | 0.029113 | −0.048693 | 0.011735 | 0.006292 | 0.03883 | −0.030741 | 0.000797 |
| 58 | 0.05186 | 0.021911 | 0.083034 | 0.000107 | −0.01834 | 0.052865 | −0.013979 | −0.019695 | 0.033179 | −0.007622 | −0.028779 | −0.027807 | −0.003238 | −0.066081 |
| 59 | 0.053609 | −0.03476 | 0.057679 | 0.02071 | −0.027467 | −0.095218 | 0.035331 | −0.053196 | 0.07874 | 0.083745 | 0.053994 | 0.081225 | −0.069687 | −0.109032 |
| 60 | −0.019459 | −0.005963 | −0.017342 | 0.040066 | −0.033205 | 0.026233 | −0.000985 | −0.010404 | −0.010976 | 0.008071 | −0.016633 | −0.028413 | 0.022186 | 0.046686 |
| 61 | −0.012657 | 0.041087 | −0.011335 | 0.006171 | −0.01367 | 0.068981 | −0.021894 | 0.005469 | 0.004551 | 0.032745 | 0.002696 | −0.009188 | 0.077729 | 0.001698 |
| 62 | 0.010221 | −0.072126 | 0.056383 | 0.002948 | −0.036617 | 0.023927 | 0.07924 | −0.001393 | 0.02685 | 0.046986 | 0.017413 | −0.039521 | 0.016447 | −0.032533 |
| 63 | 0.035933 | −0.001813 | −0.072375 | 0.015153 | −0.011961 | 0.037416 | −0.007841 | 0.070109 | 0.062292 | 0.054881 | −0.003914 | −0.036808 | 0.050784 | 0.015572 |
| 64 | 0.01547 | −0.003045 | −0.029186 | 0.01785 | 0.017559 | 0.092201 | −0.003181 | 0.057696 | −0.049964 | 0.031312 | 0.029782 | 0.015312 | 0.042975 | 0.010379 |
| 65 | −0.04635 | −0.023167 | 0.016694 | −0.003174 | 0.063149 | −0.050958 | −0.014518 | 0.050132 | −0.017945 | 0.019437 | 0.012374 | 0.037396 | −0.012626 | 0.026489 |
| 66 | 0.020168 | −0.01303 | 0.003504 | 0.057453 | 0.064626 | −0.073549 | −0.040365 | 0.052857 | 0.099285 | −0.002341 | 0.03914 | 0.040881 | −0.044281 | 0.004524 |
| 67 | 0.026875 | 0.032872 | 0.060672 | 0.04582 | 0.047738 | 0.097469 | 0.010626 | 0.043408 | 0.014892 | 0.061454 | 0.029341 | 0.067166 | −0.088287 | 0.05014 |
| 68 | −0.09366 | 0.092231 | 0.087472 | 0.000526 | 0.142765 | −0.090551 | 0.005843 | 0.039049 | 0.016298 | −0.010598 | −0.107728 | −0.026164 | 0.035198 | −0.034482 |
| 69 | 0.028799 | 0.016742 | −0.040948 | 0.010439 | −0.019349 | 0.028138 | 0.001484 | −0.003205 | −0.00126 | 0.030946 | −0.003226 | −0.003452 | 0.014788 | 0.003409 |
| 70 | 0.015403 | 0.028938 | −0.027894 | −0.004529 | −0.010037 | −0.001853 | 0.005977 | 0.006967 | 0.00493 | 0.017354 | 0.03223 | −0.00518 | 0.003361 | 0.012635 |
| 71 | −0.052687 | −0.024496 | 0.071718 | 0.086906 | 0.147311 | 0.035719 | −0.054103 | 0.00164 | 0.000481 | 0.039504 | −0.004021 | −0.041064 | −0.0187 | −0.046916 |
| 72 | 0.013038 | 0.023068 | −0.00609 | 0.044232 | 0.037917 | −0.04502 | −0.050807 | 0.007909 | −0.003888 | 0.015489 | 0.039368 | −0.024417 | −0.037256 | −0.0213 |
| 73 | −0.003038 | 0.050572 | 0.002566 | −0.008601 | −0.002194 | −0.087635 | −0.066177 | −0.026867 | 0.007928 | 0.035112 | 0.007803 | 0.026506 | −0.030956 | 0.059094 |
| 74 | −0.046033 | 0.031388 | −0.062051 | 0.111388 | 0.041715 | −0.045837 | −0.048476 | 0.027282 | 0.058625 | −0.184601 | 0.071876 | −0.125095 | −0.078043 | −0.068813 |
| 75 | 0.012579 | 0.000907 | −0.006764 | 0.010065 | −0.01315 | −0.006327 | −0.003855 | −0.008689 | −0.017529 | −0.000288 | 0.012847 | −0.002572 | 0.016485 | 0.010664 |
| 76 | −0.005913 | −0.000752 | 0.002052 | 0.009123 | −0.003131 | −0.010247 | 0.010033 | 0.007375 | −0.031186 | −0.029671 | 0.01933 | −0.004862 | −0.0017 | 0.001418 |
| 77 | 0.01534 | −0.001708 | −0.01319 | 0.006669 | −0.013407 | −0.008187 | −0.002303 | −0.006173 | −0.021286 | 0.000008 | 0.020569 | −0.006553 | 0.011868 | 0.006232 |
| 78 | 0.015463 | −0.002269 | −0.010781 | 0.002697 | −0.014449 | −0.006196 | −0.000075 | −0.006705 | −0.023516 | −0.002152 | 0.016573 | −0.002358 | 0.009183 | 0.010177 |
| 79 | 0.009764 | −0.002064 | −0.010364 | 0.013177 | −0.019382 | −0.004679 | −0.002677 | −0.00098 | −0.025786 | −0.004913 | 0.021438 | 0.002045 | 0.01406 | 0.003211 |
| 80 | 0.052016 | −0.017833 | −0.062947 | −0.070847 | −0.032781 | −0.039777 | 0.026726 | −0.07987 | −0.028553 | 0.127608 | 0.052545 | −0.132237 | 0.12026 | 0.123264 |
| 81 | −0.032645 | 0.02987 | 0.00519 | −0.051329 | 0.060583 | −0.038663 | 0.048826 | 0.061083 | 0.052966 | 0.080324 | 0.074202 | 0.067688 | −0.055905 | −0.027688 |
| 82 | −0.010153 | −0.018528 | −0.021618 | −0.023512 | −0.005563 | 0.00647 | −0.016668 | 0.015696 | −0.001569 | 0.010054 | 0.006559 | 0.011451 | 0.016866 | −0.011756 |
| 83 | −0.011014 | −0.008896 | −0.01251 | −0.006976 | 0.002691 | 0.016817 | −0.013213 | 0.009461 | −0.003762 | −0.003016 | −0.00104 | 0.018588 | 0.014291 | 0.005732 |
| 84 | −0.014977 | −0.011817 | −0.014431 | −0.002109 | 0.000567 | 0.019988 | −0.010432 | 0.010413 | −0.005885 | 0.000343 | 0.000203 | 0.018306 | 0.014238 | 0.014832 |
| 85 | 0.021806 | 0.053455 | 0.030149 | 0.021156 | −0.019641 | 0.016823 | 0.009332 | −0.003727 | 0.006345 | −0.011342 | 0.092056 | −0.003442 | −0.044547 | 0.027767 |
| 86 | −0.021622 | −0.013502 | 0.017271 | −0.009528 | 0.036952 | −0.051849 | −0.045018 | −0.00637 | 0.006391 | 0.003653 | 0.025386 | 0.042735 | −0.021886 | 0.027963 |
| 87 | 0.004494 | −0.036427 | 0.006902 | 0.013972 | 0.056808 | 0.00001 | −0.017346 | −0.015351 | −0.063784 | −0.030323 | 0.047247 | 0.002232 | −0.026978 | 0.041973 |
| 88 | −0.01016 | −0.010972 | −0.017964 | −0.004483 | 0.009355 | 0.019067 | −0.008981 | 0.007742 | −0.011009 | −0.00261 | −0.001364 | 0.021602 | 0.022613 | 0.00612 |
| 89 | −0.004942 | −0.004718 | −0.014218 | −0.005187 | −0.000721 | 0.020466 | −0.005454 | 0.009913 | −0.005229 | −0.007897 | −0.00149 | 0.013 | 0.017714 | 0.001832 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 90 | −0.010009 | −0.005749 | −0.011342 | 0.002199 | 0.005207 | 0.025968 | −0.009121 | 0.005262 | −0.005813 | −0.013013 | 0.010078 | 0.020646 | 0.00938 | 0.016714 |
| 91 | −0.020408 | −0.000067 | −0.018921 | −0.011149 | −0.020496 | 0.017903 | 0.004196 | 0.03267 | 0.008468 | 0.010842 | −0.006121 | 0.021187 | 0.01375 | −0.00178 |
| 92 | −0.02245 | 0.01674 | 0.02587 | 0.011548 | 0.031241 | 0.031757 | −0.009379 | 0.034048 | 0.013066 | 0.019052 | 0.02314/ | 0.055086 | −0.016281 | 0.043968 |
| 93 | −0.001316 | 0.027594 | −0.012031 | 0.003752 | −0.006446 | −0.012016 | −0.025792 | 0.012667 | 0.005326 | −0.001155 | 0.031147 | −0.002273 | 0.02009 | −0.016225 |
| 94 | −0.008352 | −0.003564 | −0.03448 | −0.012558 | −0.003104 | −0.02225 | 0.04207 | 0.043081 | 0.007455 | 0.007844 | −0.027172 | −0.020124 | 0.026158 | −0.027886 |
| 95 | −0.004619 | −0.101229 | −0.037001 | −0.033975 | 0.068461 | −0.036004 | −0.022304 | −0.005255 | 0.004662 | −0.001227 | 0.045829 | 0.095665 | −0.013089 | −0.043902 |
| 96 | 0.022717 | 0.037778 | −0.000597 | 0.046532 | 0.04126 | 0.010795 | −0.025768 | 0.062469 | −0.103393 | −0.038256 | 0.012071 | −0.09947 | −0.075144 | −0.052058 |
| 97 | 0.075891 | −0.020404 | 0.061624 | −0.084256 | 0.000011 | 0.064912 | −0.023548 | −0.006568 | −0.059771 | −0.036201 | −0.005247 | −0.088707 | 0.017537 | 0.017499 |
| 98 | −0.006275 | −0.073331 | 0.000624 | −0.002455 | −0.020855 | 0.023528 | −0.007644 | −0.027791 | −0.000349 | −0.036656 | −0.026831 | −0.02676 | 0.01355 | 0.037102 |
| 99 | 0.04668 | −0.028675 | −0.014018 | 0.025844 | −0.004859 | 0.008682 | 0.002208 | 0.015864 | −0.014611 | −0.003805 | −0.046647 | −0.023959 | −0.099611 | 0.018329 |
| 100 | 0.016711 | −0.046147 | −0.011443 | 0.023662 | −0.075959 | 0.005395 | 0.003206 | −0.004225 | 0.000542 | −0.028255 | −0.040152 | −0.059102 | −0.014639 | −0.041591 |
| 101 | 0.012839 | −0.056529 | 0.012814 | 0.008989 | −0.00853 | 0.022319 | −0.020671 | −0.040246 | −0.022525 | −0.047435 | 0.006943 | −0.025867 | 0.040482 | 0.073021 |
| 102 | −0.001654 | 0.016331 | −0.070951 | −0.03002 | 0.044629 | 0.072546 | −0.036846 | −0.04729 | −0.039106 | 0.079585 | 0.001065 | −0.002839 | 0.066289 | −0.020907 |
| 103 | −0.02718 | −0.103336 | −0.051022 | −0.058069 | 0.101101 | 0.154627 | 0.000745 | −0.002355 | −0.09736 | −0.030465 | −0.065636 | −0.038791 | 0.115547 | −0.0709 |
| 104 | −0.02075 | −0.05337 | −0.030682 | 0.082471 | 0.034938 | 0.055883 | 0.067972 | −0.054682 | −0.046611 | −0.015174 | 0.01915 | −0.011841 | −0.025518 | 0.047143 |
| 105 | 0.07211 | −0.03824 | 0.116901 | −0.08826 | −0.027266 | −0.020588 | −0.039904 | −0.049565 | −0.293338 | −0.075264 | 0.047341 | −0.020581 | 0.108177 | 0.037128 |
| 106 | 0.023599 | −0.050661 | −0.028445 | 0.037916 | 0.046025 | 0.029917 | 0.007502 | 0.091601 | 0.080282 | 0.052468 | 0.055429 | 0.02927 | 0.040503 | 0.063491 |
| 107 | 0.093386 | −0.068535 | −0.023228 | 0.017999 | 0.030624 | −0.061847 | 0.023242 | 0.09312 | −0.051703 | −0.020915 | 0.058051 | −0.042688 | 0.012291 | 0.070997 |
| 108 | 0.062345 | −0.030406 | 0.026335 | −0.023785 | −0.022688 | −0.096649 | 0.003785 | −0.024826 | −0.079063 | −0.093446 | −0.014029 | −0.040402 | 0.150731 | −0.05538 |
| 109 | −0.068972 | −0.081042 | −0.058552 | −0.040026 | −0.117939 | 0.010581 | 0.240931 | −0.278895 | 0.084436 | 0.019724 | 0.039289 | −0.044626 | −0.053098 | 0.077707 |
| 110 | 0.039049 | −0.017558 | −0.157399 | −0.195911 | −0.188119 | 0.107135 | −0.199646 | 0.079713 | −0.091606 | 0.04577 | −0.118361 | −0.190068 | −0.089949 | 0.02326 |
| 111 | 0.03385 | −0.019273 | −0.064888 | 0.085133 | 0.044937 | −0.148096 | −0.004792 | −0.022214 | −0.088031 | 0.048676 | 0.111276 | −0.046765 | −0.026095 | 0.035911 |
| 112 | 0.155117 | −0.040763 | −0.008895 | 0.031112 | 0.076911 | 0.048762 | 0.012094 | −0.010592 | −0.124693 | 0.083812 | 0.103009 | −0.032146 | 0.115304 | 0.001287 |
| 113 | 0.103495 | −0.00154 | 0.027501 | −0.039277 | −0.057382 | −0.010057 | 0.018215 | 0.094522 | −0.06104 | 0.004079 | −0.009433 | 0.069927 | 0.062345 | −0.029386 |
| 114 | −0.048951 | −0.005125 | 0.013909 | −0.00131 | −0.006919 | 0.112295 | 0.127987 | 0.033037 | −0.014718 | −0.162526 | 0.038013 | 0.048038 | −0.072032 | −0.073962 |
| 115 | −0.130939 | −0.06065 | −0.066322 | 0.03283 | −0.129843 | 0.061837 | 0.063678 | 0.082518 | 0.138198 | −0.112352 | −0.018327 | −0.023969 | −0.046715 | 0.070356 |
| 116 | 0.014934 | 0.015905 | 0.014789 | 0.0072 | −0.073545 | −0.085883 | −0.063071 | −0.036692 | −0.09251 | −0.121184 | −0.021735 | −0.004828 | −0.000728 | 0.105735 |
| 117 | −0.098006 | −0.022252 | −0.079499 | 0.032155 | 0.070448 | −0.069763 | 0.023023 | 0.047797 | −0.085439 | 0.080373 | −0.000999 | 0.009427 | 0.014704 | −0.097396 |
| 118 | −0.022258 | −0.011112 | −0.049242 | 0.038342 | −0.009007 | −0.00517 | −0.007568 | 0.007346 | 0.016578 | 0.004428 | −0.000089 | 0.014335 | −0.149328 | −0.086813 |
| 119 | 0.03322 | 0.022594 | −0.128185 | 0.023401 | 0.016855 | 0.018509 | 0.066515 | 0.035516 | 0.011772 | −0.002337 | 0.029171 | −0.074039 | −0.033334 | −0.029112 |
| 120 | −0.058774 | −0.068676 | −0.033776 | 0.03338 | 0.019471 | −0.124018 | 0.079862 | 0.034913 | −0.034661 | 0.044222 | 0.010478 | 0.063794 | 0.035664 | 0.005818 |
| 121 | −0.046705 | −0.018726 | −0.069071 | 0.032749 | −0.017505 | −0.057132 | 0.11842 | −0.040917 | −0.048401 | 0.053493 | 0.006837 | 0.000272 | 0.019465 | −0.09382 |
| 122 | 0.016127 | −0.035467 | −0.014304 | 0.009677 | 0.026593 | −0.042051 | −0.02462 | 0.046723 | −0.052103 | 0.00818 | 0.013155 | 0.048927 | 0.029279 | 0.011126 |
| 123 | 0.031926 | −0.03556 | 0.001474 | 0.008187 | −0.053665 | −0.048406 | −0.0116 | 0.034843 | −0.024105 | 0.050626 | 0.017714 | 0.006442 | −0.011269 | −0.022589 |
| 124 | 0.027851 | −0.010585 | −0.018689 | −0.003209 | 0.034253 | 0.033444 | 0.025965 | −0.02759 | −0.004262 | 0.003468 | −0.018145 | −0.022501 | −0.022821 | 0.03957 |
| 125 | 0.010516 | −0.020207 | 0.105562 | 0.021684 | −0.033904 | 0.031605 | −0.062586 | −0.105847 | 0.079236 | −0.012753 | −0.071722 | 0.003513 | −0.069922 | 0.024211 |
| 126 | 0.034338 | 0.01713 | −0.027945 | 0.015926 | −0.104322 | −0.039587 | −0.037063 | −0.035711 | 0.004566 | 0.000455 | 0.002088 | −0.023185 | −0.036831 | −0.00622 |
| 127 | 0.043363 | 0.00835 | −0.063065 | 0.001224 | −0.066015 | −0.022094 | −0.023733 | −0.016848 | 0.000138 | 0.025639 | −0.02093 | −0.047821 | −0.042013 | 0.010608 |
| 128 | 0.021855 | 0.030004 | −0.091941 | −0.04514 | −0.074456 | 0.004005 | 0.050058 | 0.078164 | −0.004781 | 0.024554 | −0.000173 | −0.070449 | −0.041317 | 0.014649 |
| 129 | 0.109171 | 0.067453 | 0.075699 | 0.137888 | 0.141366 | 0.084413 | −0.042461 | 0.056525 | 0.200782 | −0.078757 | 0.105936 | −0.195713 | 0.114808 | −0.100963 |
| 173 | 0.084505 | −0.027461 | 0.02735 | −0.089584 | −0.014874 | 0.056864 | 0.251762 | −0.007001 | 0.173859 | −0.100447 | 0.158291 | 0.219784 | 0.013975 | 0.039959 |
| 131 | 0.106476 | 0.022378 | −0.03734 | −0.096087 | −0.051935 | 0.063332 | −0.03608 | −0.0667 | −0.152428 | −0.029725 | 0.058346 | 0.021526 | 0.176667 | −0.044234 |
| 132 | −0.045599 | −0.018077 | 0.010093 | 0.029607 | −0.053127 | −0.131017 | −0.02619 | 0.0011 | −0.030726 | 0.054323 | −0.06186 | −0.048531 | 0.119242 | −0.001464 |
| 133 | 0.073924 | 0.017615 | −0.10951 | −0.068985 | 0.016783 | 0.043076 | 0.047063 | 0.00192 | 0.054893 | 0.095586 | −0.055573 | −0.13206 | −0.018429 | −0.030048 |
| 134 | −0.021878 | 0.086684 | −0.014377 | 0.022939 | 0.183441 | 0.080638 | −0.041487 | −0.07709 | −0.058467 | −0.017653 | −0.128712 | 0.02526 | −0.052348 | −0.035464 |
| 135 | −0.028535 | −0.042998 | 0.010805 | −0.010829 | 0.00908 | 0.001201 | −0.01053 | 0.001654 | −0.029784 | 0.035322 | −0.018347 | 0.035909 | −0.001125 | 0.023477 |
| 136 | −0.040516 | 0.014082 | 0.109233 | 0.01945 | −0.061278 | −0.009708 | −0.056654 | 0.09444 | −0.098628 | −0.03644 | −0.005866 | −0.031819 | −0.048342 | 0.105878 |
| 137 | 0.045815 | −0.011794 | −0.057744 | 0.010875 | 0.010588 | 0.141112 | 0.038589 | 0.054298 | 0.040767 | 0.014913 | 0.025568 | −0.076828 | −0.058011 | 0.004938 |
| 138 | 0.093435 | −0.037337 | 0.105557 | −0.017651 | 0.107261 | −0.147693 | 0.105784 | 0.03506 | −0.012565 | −0.168673 | −0.096054 | 0.079989 | −0.123778 | 0.020188 |
| 139 | −0.001693 | 0.154684 | −0.036529 | 0.052556 | 0.02467 | −0.056559 | −0.097224 | −0.172996 | −0.089794 | 0.009333 | 0.089772 | 0.049265 | 0.084232 | −0.072216 |
| 140 | −0.031707 | 0.068761 | −0.028464 | −0.164366 | 0.000746 | −0.097904 | −0.04525 | 0.131992 | −0.015515 | 0.052307 | 0.02082 | −0.01175 | −0.072294 | −0.102107 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 141 | 0.042163 | −0.044216 | −0.066839 | −0.081279 | −0.13449 | −0.07103 | 0.040692 | 0.024595 | −0.051443 | 0.089584 | −0.070389 | 0.027841 | −0.023749 | −0.1049 |
| 142 | −0.034756 | −0.006709 | 0.054105 | 0.004891 | −0.005294 | 0.046114 | 0.021432 | −0.037722 | −0.057263 | −0.063879 | 0.024745 | 0.036354 | 0.050008 | −0.026693 |
| 143 | 0.093302 | −0.069318 | 0.102007 | −0.011741 | −0.006101 | 0.034505 | −0.019492 | 0.061435 | −0.036519 | 0.01541 | −0.040953 | 0.101189 | 0.058926 | −0.040713 |
| 144 | 0.087127 | −0.051625 | −0.059563 | 0.033414 | 0.00173 | 0.061484 | 0.037624 | 0.081165 | 0.006886 | −0.016954 | 0.00363 | 0.029365 | 0.050166 | −0.007217 |
| 145 | −0.000557 | 0.003553 | −0.058316 | −0.058496 | 0.042716 | 0.085723 | 0.002486 | 0.135941 | −0.083652 | 0.130744 | 0.017413 | −0.030987 | 0.006299 | 0.00149 |
| 146 | 0.008108 | 0.014807 | 0.008105 | −0.015333 | 0.013543 | 0.05664 | −0.000682 | 0.011264 | 0.009164 | 0.009187 | −0.031873 | 0.028353 | −0.027021 | 0.023618 |
| 147 | 0.003883 | −0.027683 | 0.095417 | 0.069283 | 0.03772 | −0.025678 | −0.013812 | −0.053306 | 0.082437 | −0.021023 | −0.01389 | 0.003765 | 0.058304 | −0.011846 |
| 148 | 0.134527 | 0.091726 | −0.085208 | −0.085524 | −0.016041 | 0.001921 | −0.096263 | −0.050069 | −0.047021 | −0.176059 | 0.091096 | 0.164865 | −0.076994 | 0.040048 |
| 149 | 0.032349 | −0.017692 | −0.06451 | 0.027231 | 0.073382 | −0.002396 | 0.058751 | −0.029842 | −0.075768 | 0.032397 | −0.021307 | 0.027999 | −0.080251 | 0.065416 |
| 150 | −0.078482 | −0.019849 | 0.183147 | 0.019321 | −0.078805 | 0.082412 | −0.024833 | 0.006762 | −0.0545 | −0.060124 | −0.041062 | 0.152794 | 0.048433 | 0.045447 |
| 151 | −0.057825 | 0.041469 | −0.026495 | 0.046274 | 0.110985 | 0.103113 | 0.046376 | −0.021642 | 0.010037 | 0.004675 | −0.033185 | 0.008034 | 0.011705 | −0.042989 |
| 152 | 0.016802 | −0.011179 | 0.000511 | −0.004999 | −0.046957 | 0.019358 | −0.006737 | −0.035357 | −0.001301 | 0.047633 | −0.030649 | −0.040682 | −0.003657 | 0.036608 |
| 153 | −0.045087 | −0.038502 | 0.016563 | −0.039623 | 0.005092 | 0.028267 | 0.010273 | −0.010708 | −0.056587 | −0.029979 | 0.038483 | −0.028894 | 0.091065 | 0.089734 |
| 154 | −0.029972 | −0.00165 | 0.035282 | −0.051473 | −0.021889 | 0.01078 | −0.007068 | −0.056045 | −0.053253 | −0.057119 | −0.00077 | 0.02649 | 0.022055 | 0.026782 |
| 155 | 0.020462 | −0.006116 | 0.012404 | 0.028206 | −0.069673 | −0.00386 | 0.039023 | −0.029119 | −0.01631 | 0.062413 | −0.023376 | −0.014596 | 0.06555 | 0.069469 |
| 156 | −0.015719 | 0.056947 | −0.008837 | −0.017622 | 0.015157 | −0.004888 | −0.017573 | −0.007741 | −0.058975 | −0.122691 | −0.036921 | 0.020224 | 0.03063 | −0.066614 |
| 157 | −0.080995 | −0.10956 | −0.027868 | 0.020386 | −0.036894 | −0.056806 | −0.05965 | 0.119859 | 0.012653 | 0.028627 | 0.019068 | 0.044851 | 0.025701 | −0.008396 |
| 158 | −0.203054 | −0.168924 | 0.041766 | −0.113569 | 0.138618 | −0.151038 | 0.049338 | 0.043701 | −0.002838 | 0.157851 | 0.011452 | −0.077142 | 0.055944 | 0.085529 |
| 159 | 0.049016 | 0.124195 | 0.034914 | −0.016129 | 0.070694 | 0.008383 | −0.083475 | −0.060104 | −0.105884 | 0.13579 | −0.062977 | 0.058983 | −0.070772 | −0.046494 |
| 160 | 0.259293 | 0.083051 | 0.100158 | −0.081364 | 0.031727 | 0.226976 | 0.081266 | −0.124994 | −0.002493 | 0.05187 | 0.167402 | −0.046281 | −0.217177 | −0.024488 |
| 161 | 0.106061 | −0.022671 | 0.049972 | −0.001823 | 0.042596 | −0.117898 | −0.01349 | −0.053611 | −0.005551 | 0.00558 | 0.038271 | −0.094518 | 0.006851 | 0.136621 |
| 162 | −0.041602 | −0.078988 | −0.138139 | −0.044968 | −0.010582 | 0.042997 | −0.073018 | 0.019164 | 0.019011 | −0.045619 | −0.023289 | 0.004119 | 0.11206 | −0.078989 |
| 163 | 0.004158 | 0.004573 | −0.040667 | −0.001915 | −0.006209 | 0.082209 | 0.058838 | 0.012823 | −0.083147 | 0.03408 | −0.079572 | −0.085019 | −0.001971 | −0.005112 |
| 164 | −0.103209 | 0.073356 | −0.030328 | −0.034284 | 0.027105 | 0.062169 | 0.047059 | 0.020788 | −0.064414 | 0.008837 | −0.031649 | −0.091271 | −0.004691 | −0.078506 |
| 165 | −0.04189 | −0.067643 | 0.121422 | 0.111537 | −0.005886 | 0.042882 | 0.120828 | −0.046859 | 0.029897 | −0.073668 | 0.062662 | −0.221802 | 0.133049 | 0.054003 |
| 166 | −0.00918 | −0.062701 | 0.036613 | −0.172656 | 0.017614 | −0.005776 | 0.090704 | −0.026428 | 0.022935 | −0.052806 | 0.05527 | 0.050087 | −0.010091 | −0.028225 |
| 167 | 0.092427 | 0.058519 | −0.059558 | 0.031306 | 0.05287 | 0.074203 | 0.112155 | 0.041529 | 0.03956 | −0.069967 | −0.009344 | 0.081114 | 0.021751 | 0.146616 |
| 168 | 0.085607 | 0.053036 | 0.030948 | 0.044846 | −0.046219 | −0.098948 | 0.02744 | 0.068776 | 0.041542 | −0.125689 | −0.035556 | −0.02358 | −0.128312 | −0.07773 |
| 169 | −0.021359 | 0.000041 | −0.01452 | −0.011097 | 0.024419 | −0.029886 | 0.01558 | 0.0125 | −0.025535 | −0.004824 | 0.042968 | 0.041389 | 0.015072 | −0.004339 |
| 170 | −0.026747 | 0.005401 | −0.003232 | −0.008251 | −0.00272 | −0.014178 | 0.037694 | −0.006134 | −0.005279 | 0.003607 | 0.067436 | 0.022502 | 0.028117 | 0.011534 |
| 171 | 0.014408 | 0.033839 | 0.048586 | 0.026537 | −0.037269 | −0.064246 | 0.023622 | 0.01464 | −0.0194 | −0.003235 | 0.027764 | −0.005599 | −0.032858 | −0.068524 |
| 172 | −0.044071 | 0.052991 | 0.016237 | −0.016454 | 0.039906 | 0.001845 | 0.041318 | −0.001985 | 0.015192 | −0.014145 | −0.009375 | 0.017723 | 0.032111 | −0.000474 |
| 173 | −0.038386 | 0.081316 | −0.020441 | 0.010366 | 0.002146 | −0.017562 | 0.004216 | −0.044271 | 0.05266 | 0.056265 | 0.011126 | −0.034485 | −0.001963 | 0.003964 |
| 174 | −0.025572 | 0.177795 | 0.004607 | −0.010002 | −0.040673 | −0.05019 | 0.01774 | −0.034366 | 0.081846 | 0.045954 | −0.035635 | −0.044533 | 0.064719 | 0.048614 |
| 175 | −0.075745 | 0.155487 | 0.088534 | −0.006651 | −0.053551 | 0.045949 | −0.045152 | −0.014172 | 0.094007 | 0.086291 | 0.000655 | 0.064222 | 0.090406 | 0.093406 |
| 176 | 0.007607 | −0.004209 | 0.094161 | 0.024108 | 0.027371 | −0.053071 | −0.024396 | 0.033676 | −0.03064 | −0.025651 | −0.007707 | 0.044107 | 0.00184 | 0.061671 |
| 177 | −0.118552 | 0.007675 | −0.054834 | −0.04841 | 0.098928 | −0.008946 | 0.077625 | 0.093871 | 0.059055 | −0.003203 | −0.071362 | 0.064173 | 0.064963 | 0.127827 |
| 178 | 0.002442 | 0.090509 | −0.051765 | 0.019876 | 0.038384 | −0.003478 | −0.038611 | −0.005193 | 0.042892 | −0.000193 | 0.016155 | −0.015006 | −0.002194 | 0.090309 |
| 179 | 0.0149 | −0.047163 | −0.02404 | 0.01138 | −0.040228 | −0.03718 | −0.003872 | 0.01941 | −0.027193 | −0.029918 | 0.022452 | 0.008744 | −0.018037 | −0.023984 |
| 180 | −0.001876 | −0.060965 | −0.039008 | 0.00222 | −0.007545 | −0.013364 | −0.040361 | −0.020727 | 0.007575 | −0.017528 | 0.036073 | 0.013859 | −0.010393 | 0.044002 |
| 181 | −0.009043 | −0.045318 | −0.030752 | 0.014492 | −0.020482 | −0.026478 | −0.026624 | −0.021325 | 0.013449 | −0.006822 | 0.009548 | 0.002971 | 0.006005 | 0.042511 |
| 182 | −0.016674 | −0.01485 | −0.007983 | 0.026902 | −0.021704 | −0.01928 | 0.018164 | 0.006151 | 0.021698 | −0.022346 | −0.002137 | 0.005852 | −0.006022 | −0.010611 |
| 183 | 0.007531 | −0.010521 | 0.029983 | 0.058569 | −0.070199 | −0.053857 | 0.035688 | 0.043566 | −0.060142 | −0.038582 | 0.017221 | −0.018807 | −0.036261 | −0.139881 |
| 184 | 0.095376 | 0.016324 | 0.13403 | 0.0374 | −0.051188 | 0.000011 | 0.004356 | 0.040634 | −0.019482 | −0.039943 | 0.001427 | −0.065236 | −0.056095 | −0.110329 |
| 185 | 0.020086 | 0.104893 | −0.061568 | −0.010215 | −0.012787 | −0.021906 | −0.00851 | 0.057213 | −0.056159 | 0.041157 | −0.077482 | 0.11107 | −0.057057 | −0.008474 |
| 186 | −0.005809 | −0.07566 | 0.00356 | −0.046993 | −0.040818 | 0.012002 | 0.006846 | 0.015896 | 0.116435 | −0.056329 | 0.124959 | 0.059959 | −0.10374 | −0.045048 |
| 187 | −0.097177 | −0.012637 | −0.022877 | −0.022483 | 0.08194 | 0.055102 | −0.039569 | 0.017623 | 0.015328 | 0.010653 | 0.040331 | −0.005364 | −0.009997 | −0.022117 |
| 188 | −0.061652 | 0.080731 | −0.039839 | −0.071815 | 0.032006 | 0.048663 | −0.022229 | 0.028373 | 0.013279 | 0.004352 | −0.001879 | −0.006749 | 0.047067 | 0.003185 |
| 189 | −0.037915 | 0.118749 | 0.037355 | −0.095227 | 0.003177 | 0.023794 | −0.056216 | −0.026185 | 0.007563 | −0.044709 | −0.019978 | −0.007991 | 0.111953 | −0.017486 |
| 190 | 0.020345 | 0.01883 | −0.014934 | −0.006832 | 0.036409 | −0.007189 | −0.016433 | −0.043974 | 0.012594 | −0.023777 | 0.007768 | 0.055502 | −0.003131 | −0.009889 |
| 191 | 0.012652 | −0.038895 | −0.019314 | −0.021656 | 0.091519 | −0.018475 | −0.008879 | −0.051637 | −0.006575 | −0.052537 | 0.065763 | 0.0373 | −0.020404 | −0.027137 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 192 | 0.104112 | −0.066118 | 0.058528 | −0.017383 | −0.056539 | 0.019305 | 0.028495 | 0.045986 | −0.024491 | −0.01823 | 0.002754 | 0.058426 | −0.086933 | −0.028848 |
| 193 | 0.019189 | 0.0010461 | 0.008975 | −0.051926 | 0.041982 | 0.043217 | 0.016779 | 0.030116 | −0.090774 | 0.053906 | 0.058196 | 0.046505 | −0.025721 | −0.010027 |
| 194 | −0.067159 | −0.027816 | −0.001969 | −0.056437 | 0.041383 | 0.035449 | −0.075114 | 0.035591 | −0.064816 | 0.039262 | 0.053381 | 0.100111 | 0.034263 | −0.025188 |
| 195 | −0.05825 | 0.065143 | −0.019468 | −0.07228 | −0.061321 | −0.02599 | −0.045391 | −0.081682 | 0.030785 | 0.036688 | 0.028912 | 0.023671 | −0.002333 | −0.017289 |
| 196 | −0.000019 | 0.049382 | −0.035544 | −0.00999 | −0.01608 | 0.013631 | −0.00417 | −0.047222 | 0.020538 | 0.003471 | −0.039265 | 0.058439 | 0.057763 | 0.025254 |
| 197 | −0.005418 | −0.013091 | −0.082524 | 0.008581 | 0.051632 | −0.027648 | 0.027219 | 0.011359 | 0.008089 | 0.045582 | 0.008824 | 0.044488 | −0.031131 | −0.026818 |
| 198 | −0.031286 | −0.049688 | 0.030297 | 0.019539 | −0.030116 | −0.042166 | 0.027362 | −0.072812 | 0.084879 | −0.048582 | 0.010766 | 0.021768 | −0.055681 | −0.006239 |
| 199 | −0.010865 | −0.01674 | 0.003621 | 0.069849 | −0.042966 | −0.010847 | −0.030676 | 0.137369 | 0.030431 | −0.049165 | 0.020605 | −0.048504 | 0.154296 | −0.036562 |
| 200 | −0.021769 | −0.001268 | −0.003974 | −0.017736 | −0.00594 | −0.000821 | 0.067254 | −0.075048 | 0.042005 | 0.014974 | 0.013441 | −0.157372 | 0.022396 | −0.04899 |
| 201 | 0.081377 | −0.145045 | −0.002407 | 0.114289 | 0.061242 | −0.147384 | −0.051246 | −0.285383 | −0.151115 | −0.104647 | −0.022264 | −0.068783 | −0.125543 | 0.031864 |
| 202 | −0.037962 | −0.024448 | −0.022463 | 0.03383 | 0.054801 | −0.006049 | 0.061321 | −0.079845 | 0.062723 | 0.032415 | −0.009507 | −0.014456 | −0.018318 | −0.019649 |
| 203 | −0.051311 | 0.005698 | −0.098031 | 0.021374 | 0.056019 | −0.089768 | −0.080469 | 0.103357 | −0.001993 | −0.038091 | 0.081186 | 0.011796 | 0.139159 | −0.122483 |
| 204 | 0.125753 | 0.026323 | 0.034415 | 0.252451 | 0.006016 | 0.027194 | −0.017828 | −0.118665 | 0.038847 | 0.013118 | −0.15105 | 0.177802 | 0.042012 | −0.140981 |
| 205 | −0.056306 | −0.031206 | −0.059495 | −0.143134 | −0.166569 | 0.127964 | −0.007403 | −0.179565 | −0.031725 | 0.028833 | 0.025651 | 0.025579 | 0.016878 | −0.241319 |
| 206 | −0.088579 | 0.059428 | 0.01989 | −0.114517 | −0.110955 | −0.044763 | −0.062325 | −0.049036 | 0.019604 | −0.079087 | −0.088294 | 0.028623 | −0.068324 | −0.040505 |
| 207 | −0.085948 | 0.140735 | −0.108681 | 0.270228 | −0.126833 | 0.031823 | 0.150144 | 0.109486 | −0.083748 | 0.058026 | 0.011941 | −0.025021 | −0.019289 | −0.009861 |
| 208 | −0.028372 | −0.023055 | −0.081882 | 0.059036 | −0.046912 | 0.036105 | −0.020285 | −0.041085 | 0.094 | 0.063683 | 0.037141 | 0.060077 | −0.02838 | 0.01416 |
| 209 | 0.178119 | −0.172378 | 0.098874 | 0.132493 | 0.071684 | 0.015094 | −0.074193 | −0.029217 | 0.000515 | 0.136769 | −0.318629 | 0.080608 | −0.021364 | −0.104442 |
| 210 | −0.00845 | 0.113993 | 0.146485 | −0.006152 | 0.061926 | 0.007759 | −0.153466 | 0.01492 | −0.093706 | 0.031884 | 0.037928 | −0.021819 | −0.147658 | 0.14277 |
| 211 | −0.049867 | 0.004951 | 0.005037 | −0.020017 | 0.08246 | 0.032069 | −0.005528 | 0.040307 | −0.14772 | 0.016652 | 0.095583 | −0.020155 | −0.113014 | −0.016463 |
| 212 | −0.010212 | −0.023748 | 0.071623 | −0.035237 | 0.022202 | −0.074688 | 0.049225 | 0.11404 | −0.154643 | 0.021324 | 0.049282 | −0.068456 | 0.022719 | −0.190714 |
| 213 | 0.236919 | 0.044696 | 0.084286 | −0.145334 | 0.221917 | −0.15669 | −0.013269 | 0.122013 | 0.220387 | 0.071869 | 0.042244 | −0.122668 | 0.042438 | 0.086728 |
| 214 | 0.018799 | −0.065453 | 0.009736 | 0.006578 | −0.050993 | −0.005639 | −0.012766 | −0.001342 | −0.026127 | −0.06092 | 0.00393 | −0.023774 | −0.025574 | −0.018822 |
| 215 | −0.02928 | −0.094224 | 0.034618 | −0.002546 | 0.002445 | −0.054171 | −0.061 | 0.00015 | −0.026299 | 0.029985 | 0.04615 | 0.025668 | −0.036995 | 0.010687 |
| 216 | 0.05976 | 0.018215 | −0.084218 | −0.001012 | 0.044168 | −0.034768 | 0.010952 | −0.018297 | 0.056857 | −0.012471 | 0.058933 | −0.008607 | −0.106554 | 0.005749 |
| 217 | −0.047084 | 0.027863 | −0.122371 | 0.024513 | 0.047185 | 0.0281 | −0.073907 | 0.041902 | 0.018715 | 0.031237 | 0.054995 | −0.008249 | −0.038593 | −0.110423 |
| 218 | −0.019782 | 0.005443 | −0.019593 | −0.008793 | −0.029019 | 0.013994 | −0.020487 | −0.011114 | −0.028398 | 0.020721 | 0.018774 | 0.043308 | 0.006879 | 0.042238 |
| 219 | −0.002117 | −0.03854 | 0.029418 | 0.006812 | 0.000975 | 0.006524 | 0.00035 | −0.015084 | 0.028671 | 0.034446 | 0.04823 | 0.026963 | 0.019799 | −0.013639 |
| 220 | −0.064837 | −0.011135 | −0.018508 | −0.007344 | 0.015322 | 0.085588 | −0.009132 | 0.011894 | 0.022332 | 0.057155 | −0.005545 | −0.034352 | −0.038553 | −0.072789 |
| 221 | −0.013499 | 0.019846 | −0.020165 | 0.014517 | −0.03886 | −0.080263 | 0.019058 | −0.04961 | −0.021164 | 0.043393 | 0.031652 | 0.045738 | −0.021365 | −0.003161 |
| 222 | 0.062644 | −0.011493 | 0.009657 | −0.02571 | −0.008562 | 0.022473 | −0.009884 | −0.010725 | −0.015085 | 0.051406 | −0.01593 | 0.02116 | −0.018026 | 0.0273 |
| 223 | 0.010013 | −0.012741 | 0.042442 | −0.0259 | 0.018748 | −0.001501 | 0.019656 | −0.029711 | −0.017408 | 0.095393 | 0.002898 | −0.010567 | 0.044546 | 0.049514 |
| 224 | −0.00008 | −0.034001 | 0.049973 | 0.004084 | −0.113111 | 0.010569 | 0.009737 | 0.04507 | −0.016586 | −0.03325 | 0.099447 | 0.002294 | −0.003697 | 0.104164 |
| 225 | −0.002584 | −0.036471 | 0.050421 | −0.027405 | −0.120284 | 0.013638 | −0.005388 | 0.055975 | −0.010082 | −0.051946 | 0.105033 | −0.014781 | −0.014703 | 0.065914 |
| 226 | 0.028768 | −0.005955 | 0.055954 | −0.067555 | 0.003503 | 0.016453 | −0.011028 | 0.005915 | 0.002624 | 0.018014 | −0.036191 | 0.011137 | 0.061686 | −0.025907 |
| 227 | −0.04459 | 0.035349 | 0.055894 | −0.023526 | 0.054071 | 0.06094 | −0.063868 | 0.007157 | −0.094305 | −0.05603 | 0.00849 | 0.066122 | 0.07255 | 0.028335 |
| 228 | 0.004153 | 0.058666 | 0.036229 | 0.005963 | 0.007379 | 0.075546 | 0.061788 | −0.036445 | 0.082405 | 0.047 | −0.006317 | −0.045039 | −0.00589 | −0.009743 |
| 229 | 0.085045 | 0.006952 | −0.08699 | −0.055285 | −0.040733 | −0.035235 | −0.057115 | −0.019437 | −0.016387 | −0.054179 | 0.033773 | −0.029043 | 0.054281 | 0.068229 |
| 230 | 0.023284 | 0.054425 | −0.101615 | 0.007718 | 0.043637 | 0.036477 | −0.025024 | −0.066021 | −0.013531 | −0.09085 | −0.000048 | 0.011295 | −0.01673 | 0.073666 |
| 231 | −0.066924 | 0.051481 | 0.08658 | −0.043298 | 0.110757 | 0.025593 | −0.012749 | 0.024328 | −0.011091 | 0.035423 | −0.078815 | 0.03495 | 0.052561 | 0.034083 |
| 232 | 0.057161 | 0.021767 | −0.044608 | −0.042125 | 0.037184 | 0.022956 | 0.044474 | −0.035092 | 0.039029 | −0.016776 | 0.001413 | −0.059316 | 0.026197 | 0.047118 |
| 233 | −0.029916 | 0.027846 | −0.027461 | −0.006577 | 0.06416 | 0.043423 | 0.043396 | −0.04408 | 0.005378 | −0.052093 | −0.024263 | −0.05147 | 0.013331 | 0.037445 |
| 234 | −0.082375 | 0.011252 | 0.090972 | −0.029642 | −0.007302 | 0.060215 | 0.024337 | 0.020549 | 0.065979 | 0.049017 | −0.068008 | −0.030493 | −0.025533 | 0.04874 |
| 235 | −0.132477 | 0.004272 | 0.088749 | −0.014022 | 0.052237 | 0.034235 | 0.05078 | 0.022278 | 0.045814 | 0.069785 | −0.024224 | 0.031958 | 0.004191 | 0.00186 |
| 236 | 0.02697 | 0.084504 | −0.013486 | −0.004559 | 0.019096 | 0.007387 | −0.071327 | −0.021834 | −0.013251 | −0.063982 | −0.000602 | 0.096061 | 0.017929 | 0.03806 |
| 237 | 0.021978 | 0.048356 | 0.01841 | −0.028851 | 0.01167 | −0.008836 | −0.067835 | −0.022778 | 0.011438 | −0.009116 | 0.085489 | 0.009934 | 0.002089 | 0.021953 |
| 238 | −0.020762 | −0.023494 | 0.029864 | −0.024141 | 0.056763 | 0.036382 | −0.00716 | −0.032321 | −0.013648 | −0.026415 | 0.007969 | −0.004526 | 0.013012 | −0.004461 |
| 239 | −0.018084 | −0.01787 | 0.021258 | 0.013131 | 0.067733 | 0.018196 | 0.003833 | −0.029836 | −0.000608 | −0.005324 | −0.024165 | −0.019551 | 0.007812 | 0.012525 |
| 240 | 0.016703 | −0.011118 | −0.121306 | 0.062696 | −0.019275 | 0.002822 | −0.043522 | 0.037197 | 0.047557 | −0.092195 | −0.004899 | 0.025202 | 0.02076 | 0.002906 |
| 241 | 0.029907 | 0.040643 | −0.079978 | 0.030753 | 0.001234 | −0.031438 | −0.028836 | 0.034413 | 0.059438 | −0.112923 | −0.03725 | −0.014947 | 0.023438 | 0.041759 |
| 242 | −0.043212 | 0.078486 | 0.073075 | −0.022158 | 0.0671 | −0.019287 | 0.045928 | −0.068702 | 0.035074 | 0.02445 | 0.015092 | 0.023624 | 0.003361 | −0.065599 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 243 | −0.063583 | 0.006095 | 0.089101 | −0.014226 | 0.032031 | 0.010495 | 0.086232 | −0.058979 | 0.001044 | 0.052608 | 0.006984 | 0.032098 | −0.017199 | −0.01413 |
| 244 | −0.004155 | −0.045969 | −0.006144 | −0.006739 | 0.046976 | −0.047546 | −0.011249 | 0.002902 | −0.008606 | −0.016326r | 0.042415 | 0.046177 | −0.037479 | −0.025991 |
| 245 | 0.06111 | 0.042544 | −0.022148 | 0.011484 | −0.01065 | −0.039898 | 0.022406 | 0.030074 | 0.011565 | −0.075865 | −0.071752 | 0.012915 | 0.031541 | −0.036131 |
| 246 | −0.012715 | 0.051738 | 0.044513 | 0.003533 | −0.06794 | 0.070019 | −0.011518 | −0.041845 | 0.01208 | −0.015175 | −0.030379 | −0.067777 | 0.006792 | −0.026613 |
| 247 | −0.01942 | 0.015991 | 0.054947 | 0.026437 | −0.040626 | 0.038895 | −0.043656 | −0.001791 | 0.006981 | 0.02005 | 0.004504 | −0.008306 | 0.048559 | 0.019748 |
| 248 | −0.020144 | 0.010295 | 0.028256 | 0.012685 | −0.016144 | 0.037044 | −0.037068 | −0.004829 | 0.007337 | 0.019063 | −0.009131 | 0.019959 | 0.036509 | 0.013999 |
| 249 | 0.075847 | −0.019194 | −0.063012 | 0.023064 | −0.005288 | 0.053588 | −0.060665 | 0.040354 | 0.027032 | −0.091209 | −0.045968 | −0.011029 | 0.057096 | 0.07032 |
| 250 | −0.017307 | −0.026455 | −0.035274 | 0.07608 | −0.022583 | −0.003361 | −0.078443 | 0.053602 | 0.058771 | −0.066146 | 0.00227 | 0.00625 | 0.002708 | 0.02112 |
| 251 | −0.038251 | −0.023109 | −0.067097 | 0.070287 | −0.010082 | −0.033187 | −0.028993 | 0.023355 | 0.069617 | −0.061441 | 0.01023 | 0.061412 | −0.005187 | −0.017551 |
| 252 | −0.020227 | 0.110348 | −0.054307 | 0.026843 | −0.03375 | −0.118086 | 0.003884 | 0.004792 | 0.016909 | −0.02217 | −0.120649 | 0.07986 | 0.012399 | −0.00429 |
| 253 | 0.07062 | 0.019531 | 0.022121 | −0.064041 | −0.027499 | −0.056277 | 0.036871 | 0.047488 | −0.047459 | 0.039253 | −0.054793 | −0.020984 | −0.057609 | −0.007941 |
| 254 | 0.02765 | −0.050906 | 0.057575 | −0.010003 | 0.032022 | 0.01369 | −0.011533 | 0.013261 | 0.000908 | 0.010126 | 0.051607 | −0.022101 | 0.020587 | 0.043759 |
| 255 | −0.035275 | −0.017139 | 0.037284 | −0.015745 | 0.012646 | −0.002279 | 0.000608 | 0.013479 | 0.015774 | −0.011113 | 0.029218 | 0.021997 | −0.012626 | 0.007235 |
| 256 | 0.055794 | 0.079452 | −0.012781 | −0.062834 | −0.0977 | −0.055381 | 0.034565 | 0.02791 | 0.002224 | −0.04349 | −0.081838 | −0.018064 | 0.002538 | 0.00876 |
| 257 | 0.00237 | 0.003009 | −0.025913 | 0.00182 | −0.030881 | 0.026057 | −0.003577 | 0.025108 | −0.021626 | −0.019248 | −0.02632 | −0.005984 | −0.070734 | −0.030029 |
| 258 | 0.00836 | 0.001696 | −0.052694 | −0.008171 | −0.005737 | 0.007952 | −0.071405 | 0.033627 | −0.021979 | −0.0092 | −0.002542 | 0.029244 | 0.004389 | 0.041596 |
| 259 | 0.011133 | −0.020734 | 0.000333 | 0.015277 | 0.01804 | 0.041876 | −0.013996 | 0.019859 | 0.016071 | −0.014144 | −0.000117 | 0.021592 | 0.024415 | 0.023824 |
| 260 | −0.04456 | 0.073571 | 0.017566 | 0.066783 | −0.039979 | −0.031671 | −0.027838 | 0.024001 | 0.031264 | −0.041212 | −0.065181 | 0.032199 | 0.029433 | 0.021865 |
| 261 | −0.045754 | 0.116203 | −0.035694 | 0.045887 | −0.018216 | −0.038835 | −0.058286 | 0.008155 | 0.007418 | −0.033004 | −0.035998 | 0.015142 | 0.026321 | 0.003741 |
| 262 | −0.010859 | 0.077018 | −0.008855 | 0.034751 | −0.001839 | −0.01513 | −0.049805 | −0.029647 | −0.010959 | 0.008811 | −0.048465 | −0.016633 | −0.001919 | 0.029503 |
| 263 | −0.023955 | 0.03956 | −0.012021 | 0.024569 | 0.013313 | −0.001281 | −0.020102 | 0.00052 | 0.00156 | 0.015475 | −0.037435 | −0.002596 | −0.04075 | 0.001881 |
| 264 | 0.066252 | −0.072115 | 0.048937 | −0.022176 | −0.004694 | 0.07435 | 0.00304 | 0.076816 | −0.013074 | −0.024268 | −0.037558 | 0.016549 | −0.051625 | 0.032329 |
| 265 | −0.000719 | −0.001469 | 0.10338 | −0.045387 | −0.010516 | 0.073371 | −0.021355 | 0.031371 | −0.024378 | −0.04249 | −0.011947 | −0.049215 | −0.01886 | −0.002431 |
| 266 | −0.04217 | 0.042194 | 0.065714 | −0.018867 | −0.023002 | −0.012727 | −0.057436 | −0.01717 | −0.015095 | −0.023091 | 0.020886 | −0.065643 | 0.003108 | −0.040439 |
| 267 | 0.103601 | 0.017246 | 0.083304 | −0.072722 | −0.064555 | −0.05145 | −0.016034 | 0.081208 | 0.0119481 | 0.058218 | −0.079407 | −0.071561 | 0.030922 | 0.038122 |
| 268 | 0.015401 | −0.007128 | 0.061235 | −0.030113 | −0.018012 | −0.011534 | 0.02609 | 0.032777 | −0.000513 | 0.041904 | −0.033975 | −0.009146 | 0.042803 | 0.010141 |
| 269 | −0.013972 | −0.006314 | 0.065455 | −0.028501 | 0.000812 | −0.019255 | 0.043824 | 0.024629 | −0.000275 | 0.047293 | −0.029236 | 0.002177 | 0.045252 | −0.021654 |
| 270 | −0.044351 | 0.005857 | 0.047321 | −0.003444 | 0.037608 | 0.018634 | −0.010586 | 0.030781 | 0.007038 | 0.015481 | −0.047484 | 0.029824 | 0.028857 | −0.020062 |
| 271 | 0.050384 | −0.076336 | 0.13658 | 0.024505 | −0.10746 | −0.098147 | −0.080305 | 0.130651 | 0.076835 | −0.022913 | 0.029056 | −0.071207 | −0.066398 | −0.014965 |
| 272 | 0.066493 | −0.033576 | −0.037944 | −0.030051 | −0.068247 | −0.049124 | −0.00507 | 0.052282 | 0.011914 | 0.034719 | −0.005319 | −0.042471 | 0.070477 | 0.024838 |
| 273 | −0.027682 | 0.013257 | −0.041715 | 0.031261 | −0.008504 | 0.017146 | 0.00959 | −0.023321 | 0.003785 | −0.016378 | −0.00502 | 0.030886 | 0.043225 | 0.044904 |
| 274 | −0.033562 | 0.005578 | −0.037498 | 0.027038 | −0.002578 | 0.018548 | 0.004534 | −0.033254 | 0.013009 | −0.026812 | −0.00451 | 0.035979 | 0.043837 | 0.035789 |
| 275 | −0.049849 | 0.042206 | −0.117968 | 0.037405 | 0.050024 | 0.050993 | −0.031667 | −0.033305 | 0.01497 | −0.075961 | −0.020157 | 0.058154 | 0.011193 | 0.041079 |
| 276 | 0.048329 | 0.036747 | −0.024097 | −0.018052 | −0.015704 | −0.035803 | −0.050782 | 0.040618 | −0.027235 | −0.041903 | 0.004392 | 0.079436 | 0.025273 | 0.055652 |
| 277 | 0.001665 | 0.0196 | −0.011359 | 0.042255 | 0.000349 | −0.069649 | 0.042814 | 0.007508 | −0.019993 | 0.021644 | 0.05595 | −0.006741 | 0.014529 | 0.041521 |
| 278 | −0.003914 | 0.019549 | −0.038013 | 0.090393 | 0.058016 | −0.059881 | 0.06121 | −0.03999 | 0.007639 | 0.021215 | 0.009789 | −0.015978 | −0.001834 | 0.031725 |
| 279 | −0.022037 | −0.055142 | −0.004168 | 0.028722 | 0.057014 | −0.022967 | 0.043411 | −0.009773 | 0.022424 | 0.004827 | −0.031121 | 0.003709 | −0.011573 | 0.008358 |
| 280 | −0.049895 | 0.00899 | 0.059684 | −0.058186 | 0.004029 | 0.009305 | 0.144893 | −0.040016 | −0.029169 | 0.054899 | 0.059001 | −0.04212 | −0.063632 | 0.01093 |
| 281 | −0.022283 | −0.052458 | −0.003017 | 0.016342 | −0.041033 | 0.033347 | 0.04045 | −0.017987 | 0.024888 | 0.023911 | −0.018474 | −0.086593 | 0.029002 | 0.001501 |
| 282 | −0.048773 | −0.046171 | −0.041033 | 0.057682 | 0.041239 | 0.016247 | 0.076027 | −0.034544 | −0.008468 | 0.05984 | −0.076595 | −0.073963 | 0.004908 | −0.030039 |
| 283 | −0.003476 | −0.018433 | 0.030466 | 0.0433 | 0.014728 | 0.002218 | −0.000031 | −0.050535 | 0.019069 | 0.033041 | −0.024606 | 0.021015 | 0.04326 | 0.001629 |
| 284 | 0.015803 | −0.032287 | −0.039175 | −0.001407 | −0.032537 | 0.009827 | 0.055988 | 0.032177 | −0.022656 | −0.022672 | −0.024904 | −0.002974 | −0.074137 | −0.041534 |
| 285 | −0.006762 | −0.04134 | −0.025707 | 0:033539 | −0.009554 | −0.003121 | 0.042049 | 0.001759 | −0.016737 | −0.005422 | −0.032605 | 0.000323 | −0.097312 | −0.034262 |
| 286 | 0.012635 | −0.094375 | −0.094552 | −0.003551 | 0.034615 | −0.019751 | 0.016382 | 0.064576 | −0.048314 | 0.005201 | −0.008154 | −0.025919 | −0.040361 | 0.008941 |
| 287 | 0.0193 | −0.08138 | −0.078458 | 0.006482 | 0.046344 | −0.014259 | 0.019468 | 0.015274 | −0.027668 | −0.001738 | −0.040236 | −0.017834 | −0.064043 | −0.000437 |
| 288 | 0.018345 | −0.01311 | −0.05791 | 0.019765 | 0.01812 | 0.000965 | −0.04476 | 0.017191 | −0.025032 | 0.020797 | −0.001968 | 0.047441 | −0.005125 | 0.022804 |
| 289 | −0.040947 | 0.012389 | 0.011829 | 0.012273 | 0.00848 | 0.008307 | −0.063019 | −0.029039 | 0.015116 | 0.002076 | −0.031294 | −0.000487 | −0.011956 | −0.005599 |
| 290 | 0.061516 | 0.006154 | −0.004175 | 0.012727 | −0.017324 | 0.023677 | 0.035731 | 0.044642 | −0.035333 | 0.105173 | 0.115719 | 0.028398 | −0.001472 | 0.060413 |
| 291 | 0.063305 | 0.008505 | −0.007939 | 0.010709 | −0.024377 | 0.019069 | 0.035645 | 0.052503 | −0.028926 | 0.10365 | 0.116396 | 0.028093 | −0.004268 | 0.053389 |
| 292 | 0.063003 | −0.008248 | 0.013581 | −0.005284 | −0.011498 | 0.043434 | 0.018639 | 0.07085 | −0.052003 | 0.083197 | 0.11202 | 0.032919 | −0.017165 | 0.05722 |
| 293 | 0.017497 | 0.04163 | 0.046656 | −0.004836 | −0.045192 | 0.001823 | 0.00926 | −0.001321 | −0.031529 | −0.02073 | 0.013117 | −0.05206 | 0.084498 | 0.069956 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 294 | −0.03586 | 0.038433 | 0.08295 | −0.015577 | −0.023969 | 0.044549 | −0.042566 | −0.036413 | −0.007146 | 0.01093 | −0.023452 | −0.035133 | 0.031116 | 0.033086 |
| 295 | −0.025141 | 0.065852 | −0.009962 | 0.01421 | −0.030877 | 0.019129 | 0.028908 | −0.042494 | −0.000782 | −0.046769 | −0.002543 | −0.022136 | 0.052947 | 0.023145 |
| 296 | −0.012033 | 0.06831 | −0.02591 | 0.025995 | −0.000965 | 0.04109 | −0.014736 | 0.009697 | 0.060176 | 0.04404 | 0.007609 | 0.051118 | 0.057328 | 0.047543 |
| 297 | −0.004562 | 0.042903 | −0.029573 | 0.018737 | −0.021409 | −0.004089 | 0.007335 | 0.001366 | −0.013598 | −0.015258 | 0.004637 | −0.048882 | 0.032483 | 0.028505 |
| 298 | −0.035344 | −0.038389 | −0.012279 | 0.084166 | −0.007027 | −0.017588 | 0.065864 | −0.045576 | −0.067656 | 0.038767 | −0.031129 | −0.044814 | 0.006217 | 0.067016 |
| 200 | −0.010713 | −0.003899 | −0.00165 | −0.036629 | 0.021534 | −0.021599 | 0.011074 | 0.011609 | −0.006798 | −0.052388 | −0.001596 | −0.005379 | 0.067647 | 0.010628 |
| 300 | 0.02962 | −0.043992 | −0.032206 | 0.033147 | 0.035421 | 0.042862 | 0.046481 | −0.075779 | −0.087824 | 0.031548 | 0.021076 | −0.058091 | −0.003789 | 0.033608 |
| 301 | −0.024497 | 0.029549 | 0.018204 | −0.003942 | −0.043877 | −0.013794 | 0.037471 | −0.025673 | −0.017495 | −0.038299 | −0.023362 | −0.030838 | −0.009835 | −0.029317 |
| 302 | −0.036135 | 0.016708 | −0.026183 | −0.001744 | −0.005463 | 0.040951 | 0.019211 | −0.035091 | 0.041978 | −0.00329 | −0.014079 | 0.000496 | −0.057441 | −0.045999 |
| 303 | 0.006767 | −0.043999 | 0.002194 | −0.052184 | 0.043918 | −0.067859 | 0.021072 | 0.028123 | 0.010831 | 0.019667 | −0.052399 | 0.011341 | 0.04168 | 0.000669 |
| 304 | 0.005189 | −0.029573 | −0.026464 | −0.062146 | 0.025831 | −0.017931 | −0.002664 | 0.003435 | 0.016253 | 0.020219 | −0.057038 | 0.015281 | 0.027201 | −0.006763 |
| 305 | −0.010932 | 0.066657 | −0.063278 | 0.059467 | −0.038129 | 0.022067 | −0.018717 | −0.016517 | 0.089423 | 0.049572 | −0.001772 | −0.05748 | −0.041687 | 0.013323 |
| 306 | 0.046595 | 0.026723 | 0.001683 | −0.010209 | −0.013843 | 0.019106 | −0.029202 | 0.019581 | 0.090473 | 0.023225 | −0.034142 | 0.019475 | −0.013937 | −0.043782 |
| 307 | 0.067454 | −0.095112 | −0.137347 | −0.282705 | 0.214758 | −0.112276 | 0.080189 | −0.067768 | 0.108842 | −0.102627 | −0.100036 | 0.045223 | 0.04912 | −0.051617 |
| 308 | 0.013154 | 0.01785 | −0.010939 | −0.027457 | −0.002579 | 0.013496 | −0.012956 | 0.024117 | 0.045738 | −0.005613 | 0.000748 | 0.002776 | −0.050816 | 0.029726 |
| 309 | −0.03402 | 0.007234 | 0.008892 | −0.003271 | −0.005783 | 0.032821 | −0.016393 | 0.032731 | 0.022047 | −0.006441 | 0.024934 | 0.021334 | −0.031761 | −0.019307 |
| 310 | −0.057763 | 0.001699 | 0.01973 | −0.020261 | −0.057745 | 0.017237 | −0.078357 | 0.050716 | 0.068181 | 0.039613 | 0.013165 | 0.008435 | −0.067234 | −0.030826 |
| 311 | 0.010405 | 0.078222 | 0.003953 | 0.016691 | 0.009806 | −0.049809 | −0.017869 | −0.028639 | −0.019914 | −0.025512 | 0.077857 | 0.022192 | 0.022335 | −0.002845 |
| 312 | 0.023688 | −0.039233 | 0.02986 | 0.026168 | −0.000649 | −0.058395 | −0.035325 | −0.008974 | 0.099118 | 0.185362 | 0.08077 | −0.034612 | −0.013321 | 0.074661 |
| 313 | −0.03117 | 0.004348 | 0.003242 | −0.011621 | 0.012542 | 0.003107 | −0.028214 | 0.022619 | −0.041342 | −0.01722 | 0.061247 | −0.029289 | −0.040512 | −0.025767 |
| 314 | 0.075208 | −0.059573 | 0.003108 | 0.078395 | −0.07067 | −0.055047 | −0.187989 | −0.122205 | 0.081212 | 0.152667 | −0.05053 | 0.011741 | −0.078714 | −0.067312 |
| 315 | −0.037381 | 0.000896 | −0.001555 | 0.008365 | 0.030428 | −0.041069 | −0.026271 | 0.018849 | −0.011968 | −0.025479 | 0.095449 | 0.008073 | −0.004278 | −0.016397 |
| 316 | −0.243733 | 0.074321 | 0.054133 | −0.00782 | −0.083214 | −0.089716 | 0.008697 | 0.05583 | 0.003738 | −0.042598 | −0.00993 | −0.105472 | −0.128187 | 0.097146 |
| 317 | −0.030888 | 0.025152 | 0.015743 | 0.033682 | −0.00266 | −0.02004 | 0.00243 | 0.00307 | −0.010642 | −0.020494 | 0.060358 | 0.009414 | −0.04603 | −0.029682 |
| 318 | −0.001433 | −0.01031 | −0.00542 | 0.008368 | −0.055744 | −0.06322 | −0.066973 | −0.080654 | 0.016298 | −0.051277 | 0.050896 | −0.0197 | −0.01666 | 0.012865 |
| 319 | −0.012035 | −0.012183 | −0.022971 | −0.006508 | 0.003506 | −0.056136 | 0.026721 | 0.015278 | −0.014916 | −0.033763 | 0.067286 | 0.031918 | 0.003301 | 0.0055 |
| 320 | −0.020973 | 0.058207 | −0.099744 | −0.030168 | −0.057495 | −0.014039 | −0.002935 | 0.016988 | 0.015632 | −0.012726 | 0.053116 | −0.007098 | 0.003319 | 0.04948 |
| 321 | 0.005307 | 0.013323 | −0.033753 | −0.025553 | 0.0219 | −0.047324 | −0.01559 | 0.069028 | −0.042967 | −0.03587 | −0.062025 | −0.027736 | −0.033768 | −0.016653 |
| 322 | −0.044055 | −0.103775 | −0.032292 | −0.115822 | 0.009874 | 0.019758 | −0.074122 | 0.034147 | 0.014603 | 0.021669 | −0.146329 | 0.016578 | −0.101559 | −0.02676 |
| 323 | −0.028338 | −0.000188 | 0.036501 | −0.000239 | 0.022262 | −0.065726 | −0.012317 | −0.019258 | −0.058724 | −0.039978 | 0.000568 | −0.005372 | −0.047332 | −0.020387 |
| 324 | −0.059147 | −0.096807 | 0.079297 | −0.023994 | −0.037868 | 0.104197 | −0.161765 | 0.052021 | 0.116696 | −0.022696 | 0.020654 | 0.039427 | 0.132024 | −0.094313 |
| 325 | 0.004556 | 0.019572 | 0.040904 | 0.0092 | −0.003324 | 0.06248 | −0.008136 | −0.010273 | 0.03881 | −0.040027 | −0.004831 | 0.061282 | 0.031415 | −0.027679 |
| 326 | 0.089411 | 0.07783 | 0.049611 | 0.069631 | 0.050839 | 0.011588 | −0.020146 | 0.074686 | 0.034198 | −0.067847 | 0.106939 | 0.073592 | 0.084795 | −0.021105 |
| 327 | 0.001012 | 0.0233 | −0.026885 | 0.008716 | −0.002563 | 0.021591 | 0.026352 | −0.012745 | 0.005224 | −0.017174 | 0.041413 | 0.042563 | 0.002413 | 0.013335 |
| 328 | 0.087149 | 0.158537 | 0.025323 | 0.153579 | 0.08818 | 0.034671 | −0.099587 | 0.012955 | 0.022619 | 0.094374 | −0.055382 | −0.043339 | −0.033432 | 0.091703 |
| 329 | 0.006942 | −0.022525 | −0.008126 | 0.050201 | 0.052089 | −0.026884 | 0.001815 | −0.0093 | −0.035005 | −0.027018 | 0.034643 | 0.021095 | −0.014374 | −0.071782 |
| 330 | 0.019705 | 0.154441 | −0.000722 | −0.102495 | −0.023218 | −0.096109 | 0.154771 | 0.012032 | −0.01349 | −0.031649 | −0.124012 | 0.073792 | −0.023636 | 0.108262 |
| 331 | 0.038381 | −0.042917 | 0.036797 | −0.008472 | 0.063603 | −0.018388 | −0.038942 | −0.005111 | 0.003217 | 0.022506 | 0.045383 | 0.022742 | 0.033036 | −0.024277 |
| 732 | 0.017829 | 0.269543 | 0.003904 | −0.078174 | −0.019958 | −0.054386 | 0.129453 | 0.112459 | −0.032717 | −0.028156 | −0.094636 | −0.013261 | 0.020519 | 0.018112 |
| 333 | −0.009355 | −0.010708 | 0.029282 | 0.045005 | 0.030134 | 0.023733 | −0.008079 | −0.033341 | 0.027511 | −0.037071 | 0.027771 | 0.026944 | 0.029421 | −0.030925 |
| 334 | −0.045291 | −0.056575 | −0.044337 | 0.169637 | −0.004691 | 0.02258 | 0.010134 | −0.030668 | −0.028782 | 0.078249 | 0.01284 | 0.072963 | 0.104198 | −0.012202 |
| 335 | 0.005109 | −0.011772 | 0.004135 | −0.038421 | 0.031962 | 0.014242 | 0.016062 | 0.009286 | 0.03688 | −0.032305 | 0.02621 | 0.033154 | 0.043621 | −0.043258 |
| 336 | 0.027072 | 0.043888 | 0.072867 | −0.096065 | −0.092029 | 0.048554 | −0.096134 | −0.016714 | 0.098571 | −0.021799 | 0.031335 | −0.020546 | −0.118141 | −0.000668 |
| 337 | −0.036258 | −0.089193 | 0.052619 | −0.003241 | −0.112099 | −0.076496 | −0.044193 | 0.023232 | 0.053683 | −0.078561 | −0.031504 | 0.028568 | 0.06179 | −0.090627 |
| 338 | −0.061459 | −0.048406 | −0.06936 | −0.045078 | −0.037674 | −0.008281 | 0.048546 | −0.012076 | −0.102084 | 0.098061 | −0.071073 | 0.197391 | −0.117388 | 0.139826 |
| 339 | 0.030241 | 0.018599 | −0.021658 | 0.025309 | −0.031448 | −0.083764 | 0.022558 | 0.0129 | 0.015253 | 0.008487 | 0.015917 | −0.056476 | 0.020562 | −0.073311 |
| 340 | 0.118262 | 0.032672 | 0.081866 | 0.063156 | −0.167229 | −0.091375 | 0.249066 | 0.156968 | 0.002469 | 0.048768 | 0.027373 | 0.062053 | 0.102506 | −0.136259 |

APPENDIX B1-continued

PCA Transformation Matrix(340 × 340; Normal/Diseased)

| | BB | BC | BD | BE | BF | BG | BH | BI | BJ | BK | BL | BM | BN | BO |
|---|---|---|---|---|---|---|---|---|---|---|---|---|---|---|
| 1 | 0.015933 | −0.009547 | −0.002537 | −0.043609 | −0.036965 | 0.037974 | −0.05038 | −0.000574 | 0.003915 | 0.04122 | −0.028286 | 0.058834 | −0.00953 | −0.028842 |
| 2 | 0.013519 | 0.010605 | 0.050864 | −0.05766 | −0.033397 | −0.017173 | 0.028582 | 0.020918 | −0.010711 | 0.050524 | −0.016697 | 0.046774 | −0.048734 | 0.033301 |
| 3 | 0.085515 | 0.057291 | 0.010897 | −0.041679 | −0.033844 | −0.002441 | −0.074173 | 0.024112 | −0.008888 | 0.042212 | 0.002514 | −0.009026 | −0.009572 | −0.010345 |
| 4 | 0.024117 | 0.006615 | −0.004547 | −0.072313 | −0.031858 | 0.050245 | −0.082099 | 0.038283 | −0.000784 | 0.00277 | −0.046298 | 0.047355 | 0.057574 | −0.06854 |
| 5 | −0.186551 | −0.157621 | −0.135197 | 0.003645 | 0.1373 | 0.018334 | 0.103258 | −0.039779 | 0.053298 | −0.169619 | 0.085879 | 0.074447 | −0.022949 | 0.057992 |
| 6 | 0.021862 | −0.118745 | −0.031194 | 0.036433 | 0.094392 | 0.043537 | −0.001009 | 0.184208 | 0.024762 | −0.027457 | 0.030812 | −0.00837 | −0.057495 | −0.001561 |
| 7 | −0.025037 | −0.077596 | −0.092615 | 0.017496 | 0.11102 | −0.001278 | 0.041518 | 0.07308 | 0.018682 | −0.013064 | 0.104274 | −0.052685 | −0.030917 | 0.03613 |
| 8 | 0.09586 | −0.002077 | −0.022203 | 0.026568 | 0.044091 | 0.113055 | −0.004226 | −0.048349 | −0.041704 | −0.071957 | 0.017079 | 0.036346 | 0.058214 | 0.105409 |
| 9 | 0.004014 | 0.031631 | −0.063047 | −0.084465 | 0.014775 | 0.086336 | −0.011342 | −0.006172 | −0.082013 | −0.056262 | −0.010572 | 0.013406 | 0.060478 | 0.009087 |
| 10 | 0.005008 | 0.07145 | 0.121089 | −0.113415 | −0.067701 | 0.020625 | −0.027078 | 0.096683 | 0.031148 | 0.080068 | 0.054727 | −0.089547 | −0.007156 | 0.004932 |
| 11 | −0.256678 | 0.106304 | 0.008963 | −0.267865 | 0.051753 | −0.14801 | 0.059775 | −0.088207 | −0.165213 | 0.052628 | 0.035626 | 0.009192 | −0.01703 | 0.07806 |
| 12 | 0.10448 | −0.001999 | −0.075012 | −0.172654 | −0.027873 | 0.02005 | 0.074492 | 0.125396 | −0.046383 | 0.185874 | 0.009069 | −0.000609 | 0.062504 | 0.035566 |
| 13 | 0.049329 | −0.004757 | 0.006451 | −0.018087 | 0.027055 | 0.006449 | −0.033812 | 0.029716 | −0.051486 | −0.030133 | −0.000235 | −0.016967 | −0.040793 | 0.016677 |
| 14 | 0.019083 | 0.017432 | 0.025335 | −0.033566 | 0.00269 | −0.008943 | −0.030027 | 0.022145 | −0.03574 | −0.028773 | −0.02966 | 0.01133 | −0.034347 | 0.00311 |
| 15 | 0.004859 | 0.001123 | −0.003197 | −0.025369 | 0.004328 | 0.002642 | −0.017604 | −0.047675 | 0.002624 | 0.01734 | −0.041643 | 0.061823 | 0.007629 | −0.027273 |
| 16 | −0.063107 | 0.09162 | −0.06324 | −0.119668 | 0.147578 | 0.140249 | −0.06821 | −0.061581 | −0.022151 | 0.048378 | −0.02548 | −0.018788 | 0.03495 | 0.007576 |
| 17 | 0.038802 | −0.029069 | −0.024236 | −0.078188 | 0.052998 | 0.07622 | −0.030288 | −0.032499 | −0.012347 | −0.105841 | −0.044882 | −0.02358 | 0.065994 | 0.001528 |
| 18 | −0.023362 | 0.004186 | −0.001601 | 0.020729 | −0.191732 | 0.045923 | −0.001069 | −0.138271 | 0.013413 | 0.039139 | 0.0776 | 0.136855 | 0.063104 | 0.058277 |
| 19 | 0.050623 | 0.05878 | 0.027334 | −0.023404 | −0.133809 | 0.003564 | −0.052995 | 0.053214 | −0.026848 | −0.031479 | 0.034015 | −0.004491 | −0.057534 | 0.068947 |
| 20 | −0.002433 | −0.007594 | −0.04166 | −0.018842 | 0.006389 | 0.000467 | −0.011663 | −0.00254 | −0.001639 | −0.022563 | 0.025061 | −0.000037 | 0.007259 | −0.004241 |
| 21 | −0.046136 | 0.080066 | 0.088291 | 0.028282 | −0.077284 | −0.020448 | 0.02887 | 0.065045 | −0.034199 | 0.058455 | −0.149677 | −0.067754 | 0.02361 | 0.00718 |
| 22 | 0.046721 | −0.024141 | 0.045832 | −0.058212 | −0.024606 | 0.01783 | 0.035055 | 0.060214 | −0.019446 | 0.013893 | 0.021908 | −0.111293 | 0.057049 | 0.055295 |
| 23 | 0.03719 | −0.061896 | 0.028883 | 0.028899 | −0.017764 | −0.062442 | −0.006589 | 0.092809 | −0.052728 | −0.03184 | −0.09545 | −0.133453 | −0.026425 | −0.091202 |
| 24 | −0.039497 | 0.061612 | 0.050107 | 0.084461 | −0.059188 | −0.024888 | −0.087239 | 0.048534 | 0.033379 | 0.014244 | −0.00336 | −0.04541 | −0.006351 | −0.012647 |
| 25 | −0.065918 | −0.073836 | −0.020097 | 0.012035 | 0.011461 | −0.051043 | 0.012539 | −0.020408 | −0.09131 | −0.090437 | −0.033849 | 0.026373 | −0.073605 | 0.057796 |
| 26 | −0.004945 | −0.013753 | −0.047101 | −0.017503 | −0.000304 | −0.019673 | −0.00727 | −0.017209 | 0.004313 | −0.023742 | 0.028756 | 0.004894 | 0.006336 | −0.009107 |
| 27 | −0.025323 | 0.015227 | −0.029273 | −0.0028 | −0.000184 | 0.004176 | −0.009436 | 0.004715 | −0.00239 | −0.01013 | 0.004918 | 0.008726 | 0.005882 | 0.009637 |
| 28 | 0.015239 | −0.044911 | −0.015559 | −0.038577 | 0.01029 | 0.025769 | −0.015701 | 0.032172 | 0.007368 | 0.010374 | −0.016993 | 0.043611 | 0.058811 | −0.004715 |
| 29 | 0.030271 | −0.030646 | −0.015531 | 0.003577 | 0.039647 | 0.080023 | −0.162519 | 0.011399 | 0.019738 | 0.069544 | −0.000741 | 0.102706 | 0.069313 | −0.069692 |
| 30 | −0.009401 | −0.056973 | 0.051516 | 0.022571 | 0.014136 | −0.057339 | 0.103363 | −0.074184 | 0.011605 | 0.006453 | −0.024416 | −0.015816 | 0.052585 | 0.027003 |
| 31 | 0.026003 | 0.007576 | −0.015417 | −0.022442 | −0.006941 | −0.000753 | 0.015765 | 0.013202 | 0.005818 | 0.010304 | 0.024017 | −0.002401 | 0.039542 | −0.006626 |
| 32 | 0.003011 | −0.014738 | 0.072495 | −0.036795 | 0.013556 | −0.132832 | 0.003403 | −0.106861 | 0.050794 | 0.042819 | 0.030243 | −0.079664 | −0.015211 | −0.015229 |
| 33 | −0.036104 | −0.005803 | 0.026468 | 0.025914 | −0.004828 | 0.086856 | −0.017925 | 0.013423 | −0.033885 | −0.058765 | 0.023886 | 0.053726 | −0.012043 | −0.08643 |
| 34 | 0.027009 | −0.054555 | 0.015942 | 0.005987 | 0.01902 | 0.026365 | −0.031166 | −0.014235 | −0.045448 | 0.003116 | 0.05567 | 0.007385 | −0.045214 | 0.054389 |
| 35 | 0.006029 | 0.030733 | 0.130172 | −0.107278 | −0.029678 | −0.056552 | −0.018829 | −0.009505 | −0.055851 | −0.086698 | 0.081149 | 0.061791 | 0.016859 | 0.042336 |
| 36 | −0.049659 | 0.030768 | 0.009431 | −0.019461 | 0.081473 | −0.027314 | 0.048556 | −0.037139 | 0.008854 | −0.048974 | 0.035126 | −0.01627 | −0.010644 | −0.02589 |
| 37 | 0.037396 | −0.030057 | −0.028867 | −0.058214 | 0.043108 | −0.001054 | 0.024027 | −0.055056 | 0.036788 | −0.018767 | 0.01753 | 0.013772 | 0.05196 | 0.014992 |
| 38 | 0.006626 | 0.193106 | −0.066408 | −0.010243 | −0.055985 | 0.016432 | −0.050546 | 0.006372 | 0.083168 | 0.051986 | 0.007664 | −0.041671 | 0.132639 | 0.007146 |
| 39 | −0.020126 | −0.002646 | −0.079463 | 0.006561 | 0.053914 | 0.055716 | −0.01325 | 0.029655 | 0.076549 | −0.044961 | −0.013192 | −0.056499 | 0.058645 | 0.046548 |
| 40 | 0.011655 | −0.001405 | 0.035234 | 0.0007 | −0.001565 | 0.020486 | 0.016941 | −0.008001 | −0.00423 | 0.092319 | 0.018611 | 0.034859 | −0.070548 | 0.006787 |
| 41 | −0.054225 | −0.028232 | 0.01326 | 0.020616 | 0.032906 | 0.059795 | 0.003723 | 0.002362 | −0.017265 | 0.052666 | −0.003389 | 0.010861 | −0.031693 | 0.01879 |
| 42 | −0.028622 | −0.052277 | −0.046892 | 0.075244 | 0.04688 | 0.064753 | −0.037578 | 0.044222 | 0.038009 | −0.006651 | 0.000675 | −0.021079 | 0.054992 | −0.018744 |
| 43 | −0.002165 | −0.018042 | 0.001302 | −0.010025 | −0.001479 | −0.012681 | 0.00189 | 0.016948 | −0.008078 | 0.02745 | 0.052495 | −0.016932 | −0.007759 | 0.025681 |
| 44 | −0.053799 | −0.009304 | 0.047755 | −0.005257 | 0.033798 | 0.037064 | 0.033276 | 0.006947 | 0.020156 | 0.043653 | −0.024936 | −0.017624 | 0.001424 | −0.095031 |
| 45 | −0.063821 | −0.050151 | 0.050373 | 0.03831 | 0.050464 | 0.032414 | −0.045537 | 0.041218 | −0.024413 | 0.027464 | 0.117542 | 0.009054 | −0.007725 | −0.016169 |
| 46 | −0.000173 | 0.024033 | 0.060044 | 0.07525 | 0.012709 | −0.047172 | 0.039854 | 0.017521 | 0.045365 | −0.141503 | −0.048134 | 0.112247 | −0.061072 | 0.038092 |
| 47 | −0.024334 | 0.018421 | 0.128748 | 0.023363 | 0.058544 | −0.027348 | −0.038181 | −0.005618 | 0.003127 | 0.071336 | −0.040378 | −0.003064 | 0.037584 | 0.076956 |
| 48 | 0.013363 | 0.027272 | −0.022117 | 0.022028 | −0.040629 | 0.00991 | 0.044949 | 0.01538 | 0.07004 | 0.014074 | −0.021704 | 0.025151 | −0.007385 | −0.02227 |
| 49 | −0.023751 | −0.028799 | 0.012707 | 0.032395 | −0.009118 | −0.086384 | 0.066136 | −0.066364 | −0.001379 | −0.028021 | −0.025286 | −0.012066 | 0.02904 | 0.055965 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 50 | −0.020532 | −0.048248 | −0.023782 | −0.007945 | 0.050701 | −0.010546 | 0.021454 | −0.006018 | 0.006019 | −0.032858 | −0.082495 | 0.021966 | 0.020752 | 0.108415 |
| 51 | −0.07624 | −0.013665 | 0.054095 | 0.023513 | −0.063963 | 0.072139 | 0.046422 | 0.03455 | 0.007026 | 0.019543 | 0.030863 | −0.026992 | 0.033476 | −0.083086 |
| 52 | 0.019662 | 0.00883 | 0.04217 | −0.037967 | −0.039439 | 0.07158 | 0.041393 | 0.052045 | 0.00281 | −0.005498 | −0.018022 | 0.008662 | −0.052731 | −0.025732 |
| 53 | −0.01046 | 0.023939 | −0.026255 | 0.01176 | −0.052241 | 0.008719 | 0.043159 | 0.000471 | −0.015904 | 0.006408 | −0.006863 | 0.003095 | 0.024015 | −0.023121 |
| 54 | 0.021951 | −0.002089 | −0.066487 | 0.139143 | −0.042464 | 0.047005 | 0.001347 | −0.046418 | −0.01257 | −0.001824 | −0.033864 | −0.030564 | −0.059814 | −0.006024 |
| 55 | −0.043046 | 0.03156 | −0.01325 | 0.015366 | −0.01255 | 0.00328 | 0.004377 | 0.005467 | 0.007429 | 0.050785 | −0.056593 | −0.033313 | −0.002989 | −0.035026 |
| 56 | 0.013075 | −0.024472 | 0.013843 | 0.013507 | −0.028588 | −0.099926 | 0.068024 | −0.024803 | −0.000165 | −0.02102 | −0.046249 | −0.007879 | 0.009069 | 0.031634 |
| 57 | 0.042165 | 0.036037 | 0.057596 | −0.002408 | −0.05028 | 0.035006 | 0.065557 | −0.025328 | 0.022198 | −0.02784 | −0.052089 | 0.015188 | −0.051894 | 0.000677 |
| 58 | 0.023779 | 0.027291 | −0.02817 | 0.012146 | 0.051389 | 0.006542 | 0.058413 | −0.012377 | 0.01223 | −0.004283 | 0.067788 | −0.089143 | −0.071707 | −0.021231 |
| 59 | −0.068965 | 0.094647 | −0.029585 | −0.072573 | −0.028543 | −0.016186 | 0.063234 | 0.105484 | 0.043036 | −0.024437 | −0.085674 | −0.027665 | −0.027786 | −0.049366 |
| 60 | −0.034634 | −0.020086 | 0.027965 | −0.013913 | 0.033262 | 0.018331 | −0.066537 | 0.063741 | 0.008455 | 0.010893 | 0.031519 | 0.025054 | 0.032325 | −0.02442 |
| 61 | −0.017807 | 0.025657 | −0.038933 | −0.06143 | 0.005726 | 0.03755 | −0.039133 | −0.013169 | 0.01971 | 0.076439 | 0.048015 | −0.021949 | 0.013637 | −0.042673 |
| 62 | −0.01011 | 0.018126 | −0.04738 | −0.001728 | 0.030512 | −0.019281 | −0.095713 | −0.018267 | 0.008962 | −0.084903 | −0.021135 | −0.060458 | −0.075714 | −0.010629 |
| 63 | 0.065393 | 0.069669 | −0.027876 | 0.019874 | −0.007789 | 0.033276 | −0.009877 | −0.060183 | −0.008165 | 0.041955 | 0.048558 | −0.03128 | −0.011844 | −0.033566 |
| 64 | −0.002445 | −0.010409 | 0.048315 | 0.001128 | 0.005533 | −0.060142 | 0.070283 | −0.052087 | −0.003917 | −0.048194 | 0.021454 | −0.030925 | 0.015271 | 0.037293 |
| 65 | 0.054604 | 0.001401 | 0.031984 | −0.044095 | −0.032589 | 0.016263 | −0.041584 | −0.022645 | 0.019895 | −0.006386 | −0.009409 | 0.006366 | −0.011835 | 0.054584 |
| 66 | 0.049508 | 0.036497 | 0.07105 | −0.026163 | 0.030405 | 0.037451 | 0.014058 | 0.011946 | 0.012134 | −0.004065 | −0.047905 | −0.054059 | 0.028463 | −0.113242 |
| 67 | 0.043398 | 0.000153 | −0.020967 | −0.066981 | 0.002938 | −0.011464 | −0.058137 | 0.000867 | 0.011332 | −0.041183 | 0.016045 | −0.025515 | −0.024954 | −0.011551 |
| 68 | −0.14807 | 0.081631 | −0.002645 | −0.025045 | −0.037365 | 0.050801 | −0.056646 | −0.000892 | 0.086018 | 0.068074 | 0.037315 | 0.027306 | −0.090657 | −0.044966 |
| 69 | −0.000969 | −0.002432 | −0.043995 | 0.012324 | −0.015061 | 0.005153 | −0.000944 | −0.006995 | 0.026769 | 0.003628 | 0.006917 | −0.013917 | −0.015195 | −0.004121 |
| 70 | 0.015182 | −0.002032 | 0.009461 | 0.017493 | −0.003854 | 0.013834 | −0.00313 | 0.011994 | 0.001122 | −0.004169 | −0.005502 | −0.027254 | −0.011426 | −0.021924 |
| 71 | −0.078324 | −0.094088 | 0.071859 | 0.047435 | −0.015075 | 0.019469 | 0.1767 | −0.067999 | 0.039928 | 0.049671 | −0.100423 | 0.093236 | 0.01965 | 0.043883 |
| 72 | 0.072941 | 0.018669 | 0.083774 | 0.023109 | −0.047625 | 0.020338 | 0.025645 | −0.011438 | 0.035015 | 0.030486 | 0.037499 | 0.004864 | −0.012567 | 0.034188 |
| 73 | 0.053571 | 0.005174 | 0.078297 | 0.022788 | −0.0399 | 0.009251 | 0.027081 | −0.001005 | 0.033363 | 0.001195 | 0.048836 | −0.017151 | −0.056171 | −0.003295 |
| 74 | −0.04466 | −0.050155 | −0.003024 | 0.082586 | 0.084312 | 0.047744 | 0.088083 | 0.065969 | 0.013033 | −0.127902 | 0.143582 | −0.076956 | 0.071532 | −0.182682 |
| 75 | 0.011437 | 0.003965 | 0.0032 | 0.003617 | 0.010496 | 0.006146 | −0.0105 | 0.014102 | −0.005627 | 0.002988 | 0.00138 | −0.013384 | −0.006226 | −0.02094 |
| 76 | 0.021398 | −0.006373 | 0.006927 | −0.010022 | −0.00488 | 0.00815 | 0.02112 | 0.002765 | 0.014348 | −0.001088 | 0.025175 | −0.015112 | 0.00489 | −0.006068 |
| 77 | 0.008431 | 0.00341 | −0.00533 | 0.007593 | 0.011247 | 0.0051 | −0.011532 | 0.008772 | 0.005117 | 0.004423 | 0.008347 | −0.010536 | 0.005995 | −0.030526 |
| 78 | 0.00653 | 0.003573 | −0.003498 | 0.014838 | 0.016165 | 0.004983 | −0.007522 | 0.007136 | 0.000359 | −0.004443 | 0.009095 | −0.007362 | 0.004936 | −0.032588 |
| 79 | 0.000084 | 0.006175 | 0.011629 | 0.010315 | 0.020418 | 0.004339 | −0.003328 | 0.000078 | 0.013622 | −0.015104 | 0.004254 | −0.009986 | −0.012139 | −0.032438 |
| 80 | −0.020627 | −0.089828 | 0.037822 | −0.000379 | −0.038922 | −0.043761 | 0.06385 | −0.058471 | 0.034726 | 0.101562 | −0.106752 | 0.031864 | 0.005228 | −0.198985 |
| 81 | −0.070417 | −0.126417 | −0.023619 | −0.037678 | −0.025928 | −0.096347 | −0.071553 | 0.021987 | 0.070189 | 0.140646 | 0.002924 | −0.069174 | 0.1252 | 0.087572 |
| 82 | −0.015684 | 0.000021 | −0.011866 | 0.027944 | 0.012918 | −0.002479 | −0.01405 | 0.002371 | −0.00066 | −0.031757 | −0.012141 | 0.012101 | −0.004984 | −0.000968 |
| 83 | −0.030674 | 0.018722 | −0.012728 | 0.013896 | 0.008156 | 0.009201 | −0.006295 | 0.003037 | :0.008816 | −0.016421 | −0.000587 | 0.017619 | −0.00913 | 0.016467 |
| 84 | −0.025113 | 0.02715 | −0.017518 | 0.006945 | −0.005846 | 0.019271 | 0.005331 | 0.01337 | −0.001736 | −0.014591 | −0.000487 | 0.018998 | −0.015611 | 0.014634 |
| 85 | 0.036446 | 0.030289 | 0.054534 | 0.069536 | −0.005405 | −0.016288 | 0.05291 | −0.022402 | 0.011835 | −0.040923 | 0.039696 | 0.006993 | −0.027912 | 0.089881 |
| 86 | −0.004185 | −0.001191 | 0.049306 | 0.060047 | 0.024223 | 0.019038 | 0.014234 | 0.010171 | 0.014062 | −0.004836 | 0.022334 | 0.00132 | 0.004442 | 0.039264 |
| 87 | 0.000958 | −0.029721 | 0.032691 | 0.003674 | 0.003785 | 0.051958 | −0.018249 | −0.01084 | 0.049451 | 0.017026 | 0.005015 | 0.037072 | 0.046115 | 0.0172 |
| 88 | −0.031293 | 0.02257 | −0.018493 | 0.007505 | 0.004648 | 0.005975 | −0.017438 | 0.010647 | −0.008577 | −0.018952 | −0.002573 | 0.023722 | −0.002114 | 0.0107 |
| 89 | −0.02528 | 0.023055 | −0.025219 | −0.000572 | 0.00755 | 0.00471 | −0.010028 | 0.002793 | −0.007841 | −0.021102 | 0.005184 | 0.008816 | −0.00923 | 0.01486 |
| 90 | −0.03803 | 0.020062 | −0.027327 | −0.008804 | 0.008242 | 0.010051 | −0.014033 | 0.006699 | −0.004172 | −0.0207 | −0.000566 | 0.007612 | 0.007142 | 0.016602 |
| 91 | −0.0165 | 0.020096 | −0.003493 | 0.000546 | −0.020301 | 0.004892 | −0.018014 | 0.030394 | −0.010549 | −0.027703 | −0.008798 | 0.001615 | −0.021285 | −0.001393 |
| 92 | −0.000344 | 0.063007 | 0.044654 | 0.018451 | −0.007838 | 0.030036 | −0.003248 | 0.026273 | −0.005968 | 0.025653 | −0.013224 | −0.03588 | −0.039415 | −0.021544 |
| 93 | −0.012746 | 0.002168 | −0.013303 | 0.012476 | 0.011518 | −0.0057 | −0.006073 | −0.025934 | −0.016782 | −0.03157 | 0.01806 | 0.006875 | −0.027945 | 0.027676 |
| 94 | 0.023604 | 0.002594 | 0.032066 | −0.012367 | 0.004416 | −0.043588 | −0.018156 | 0.016272 | 0.007995 | −0.031433 | 0.003358 | −0.036033 | −0.009362 | 0.005071 |
| 95 | 0.123353 | −0.059288 | −0.031808 | −0.08915 | 0.151396 | 0.020255 | −0.000951 | −0.050293 | 0.045961 | 0.053295 | 0.093811 | 0.000382 | −0.065532 | −0.058989 |
| 96 | −0.019422 | −0.083578 | 0.022778 | 0.03034 | 0.086295 | 0.015149 | 0.112022 | 0.002494 | −0.0663 | 0.054216 | −0.079751 | 0.052162 | 0.01948 | 0.018499 |
| 97 | −0.078066 | −0.043551 | 0.076863 | 0.057835 | 0.038798 | 0.03062 | 0.033683 | −0.049012 | 0.000569 | 0.040487 | −0.046087 | 0.007825 | −0.002608 | −0.020327 |
| 98 | −0.013996 | −0.00353 | 0.008255 | −0.036898 | 0.010261 | −0.014753 | 0.021279 | −0.033922 | 0.041409 | 0.024174 | −0.022482 | 0.004595 | 0.036222 | 0.00583 |
| 99 | 0.04969 | 0.017175 | 0.044969 | 0.009687 | −0.02664 | −0.014832 | 0.007993 | −0.063939 | 0.081727 | 0.070193 | −0.043146 | −0.001412 | −0.040286 | −0.010522 |
| 100 | −0.021854 | 0.004981 | −0.036763 | 0.074919 | −0.029557 | −0.012461 | 0.001012 | −0.038481 | 0.028064 | −0.056283 | −0.026451 | −0.030999 | 0.035941 | 0.011369 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 101 | −0.023903 | −0.026301 | −0.001799 | −0.011052 | −0.020115 | −0.019361 | 0.024425 | −0.015763 | 0.019772 | −0.016015 | 0.040723 | −0.045073 | 0.017616 | −0.003024 |
| 102 | 0.061544 | −0.008549 | 0.044376 | 0.002173 | −0.074375 | −0.017507 | −0.003215 | 0.057338 | 0.0678 | 0.062398 | 0.140565 | 0.0034061 | 0.051011 | −0.019757 |
| 103 | −0.023682 | 0.035811 | −0.021506 | −0.072113 | 0.015128 | −0.003353 | −0.11624 | 0.11957 | 0.038854 | 0.006087 | 0.041213 | 0.049676 | −0.089267 | 0.036567 |
| 104 | 0.154071 | −0.019257 | −0.137802 | 0.056117 | 0.058035 | 0.053022 | −0.103638 | 0.019724 | −0.071 | 0.015455 | 0.054479 | −0.117375 | −0.021823 | −0.010345 |
| 105 | 0.014213 | 0.107905 | 0.120769 | −0.059661 | −0.1065 | 0.087263 | −0.099602 | −0.072274 | 0.047008 | −0.19204 | 0.021903 | −0.117723 | 0.111937 | 0.014822 |
| 106 | −0.002183 | 0.099588 | 0.005983 | 0.093761 | 0.051955 | −0.028248 | 0.015397 | 0.04109 | 0.009303 | −0.01886 | −0.025617 | 0.069347 | 0.064883 | −0.025727 |
| 107 | −0.05042 | −0.026081 | 0.014124 | 0.025716 | −0.005681 | −0.029924 | −0.01303 | 0.024174 | 0.113778 | −0.020585 | 0.013255 | −0.047627 | −0.004688 | −0.0822 |
| 108 | 0.042451 | −0.106645 | −0.085436 | −0.062546 | 0.085354 | 0.041601 | 0.012089 | 0.072232 | 0.096712 | −0.017547 | −0.037121 | 0.105978 | −0.002348 | −0.055392 |
| 109 | 0.011832 | −0.075475 | −0.076735 | 0.237556 | −0.074244 | 0.123184 | 0.025793 | 0.08124 | −0.114208 | 0.155296 | 0.04392 | 0.129907 | 0.084897 | 0.164673 |
| 110 | 0.162684 | 0.153549 | −0.01834 | −0.035546 | −0.069044 | 0.018929 | 0.083997 | 0.0743 | −0.058489 | 0.018218 | 0.029193 | −0.010718 | −0.103402 | 0.030248 |
| 111 | 0.13959 | −0.15701 | −0.018965 | −0.092908 | 0.080323 | 0.058244 | 0.121928 | 0.117744 | 0.053568 | 0.072563 | −0.011058 | 0.050476 | −0.037537 | −0.032729 |
| 112 | −0.015629 | −0.044711 | −0.146125 | −0.095285 | −0.025256 | −0.038565 | 0.017025 | −0.117179 | 0.081031 | −0.003005 | 0.108605 | 0.024619 | −0.11785 | 0.12486 |
| 113 | 0.095063 | 0.000812 | 0.013191 | 0.040701 | 0.046868 | −0.085168 | 0.060049 | −0.091039 | 0.057536 | −0.036993 | −0.133132 | −0.109585 | 0.041829 | −0.020663 |
| 114 | 0.016754 | 0.037037 | −0.045624 | −0.038138 | 0.09166 | 0.037242 | −0.065412 | −0.108571 | 0.081341 | −0.019039 | 0.06938 | −0.043091 | 0.024002 | −0.149929 |
| 115 | 0.047054 | 0.130304 | 0.01976 | −0.033097 | −0.059414 | 0.116266 | −0.017556 | 0.109445 | 0.053493 | −0.06646 | −0.030502 | −0.137773 | 0.038586 | 0.068003 |
| 116 | 0.100372 | −0.019586 | −0.087285 | 0.075991 | −0.200105 | −0.168636 | 0.034152 | 0.059787 | 0.146849 | 0.056333 | 0.069284 | −0.050702 | 0.099148 | 0.160921 |
| 117 | 0.037353 | 0.014129 | 0.015008 | 0.006215 | 0.012399 | −0.004451 | −0.025454 | −0.0051 | 0.052565 | 0.010245 | −0.085591 | −0.050349 | −0.020506 | 0.111192 |
| 118 | −0.038035 | 0.034656 | −0.029823 | −0.061391 | 0.05234 | −0.041858 | −0.05654 | −0.083786 | 0.04198 | 0.010866 | −0.060125 | −0.125831 | −0.040268 | −0.010939 |
| 119 | −0.020087 | −0.053854 | 0.011663 | 0.007477 | −0.011954 | −0.025072 | 0.031573 | −0.014565 | 0.006513 | 0.003386 | 0.061149 | −0.073527 | −0.066035 | −0.047363 |
| 120 | −0.009416 | 0.037024 | 0.014942 | 0.021626 | −0.036426 | −0.035965 | −0.022249 | 0.083972 | 0.023652 | −0.034833 | −0.042271 | −0.005497 | 0.006509 | 0.01625 |
| 121 | 0.028815 | 0.109492 | 0.022767 | 0.076845 | −0.047106 | −0.034684 | 0.045599 | 0.023727 | 0.031905 | −0.033995 | −0.003265 | −0.031713 | −0.000477 | 0.005651 |
| 122 | −0.055107 | −0.009072 | 0.001741 | −0.008909 | −0.017084 | −0.077909 | −0.03119 | 0.061905 | 0.041462 | 0.042804 | −0.023843 | −0.130103 | 0.00668 | 0.059126 |
| 123 | −0.060311 | −0.008361 | 0.004242 | 0.012244 | −0.074335 | −0.05352 | −0.076134 | 0.08859 | 0.012113 | −0.022078 | 0.003242 | −0.087219 | 0.010866 | −0.001755 |
| 124 | −0.019398 | −0.04014 | −0.046237 | 0.005215 | −0.006164 | −0.035646 | −0.005878 | −0.00382 | 0.067402 | −0.031218 | 0.014014 | −0.062236 | −0.001551 | −0.011903 |
| 125 | −0.027802 | 0.043922 | 0.004952 | −0.025445 | −0.077695 | −0.03928 | 0.020393 | −0.067904 | −0.013708 | 0.018182 | 0.013066 | 0.052159 | −0.032462 | −0.029343 |
| 126 | −0.017097 | −0.00727 | 0.003547 | 0.001722 | 0.03318 | −0.066123 | −0.081153 | 0.015594 | −0.025278 | −0.030975 | 0.026745 | −0.047691 | −0.00638 | −0.008346 |
| 127 | −0.027576 | −0.00433 | −0.01687 | −0.019033 | 0.041497 | −0.069463 | −0.058501 | 0.022178 | −0.010943 | −0.028603 | 0.017966 | −0.054857 | −0.011897 | 0.00064 |
| 128 | 0.033182 | −0.061748 | 0.097981 | −0.034474 | −0.050644 | 0.000379 | −0.076205 | 0.002603 | −0.088366 | −0.01383 | −0.090733 | 0.009448 | 0.078675 | −0.03684 |
| 129 | 0.041143 | 0.040566 | −0.010134 | −0.132366 | −0.049992 | −0.029695 | 0.017255 | 0.13574 | 0.093557 | 0.083844 | −0.035477 | −0.001381 | 0.200015 | 0.006893 |
| 130 | 0.081796 | −0.015311 | 0.108975 | −0.054508 | −0.005703 | −0.041242 | 0.014987 | −0.041806 | −0.081345 | −0.104656 | −0.027013 | 0.052199 | −0.058275 | 0.070041 |
| 131 | −0.221894 | 0.093175 | 0.097239 | 0.105765 | −0.007777 | 0.136367 | −0.050295 | 0.082269 | 0.052841 | 0.014773 | −0.111629 | −0.09968 | −0.045123 | −0.199567 |
| 132 | −0.038619 | −0.12666 | 0.024213 | −0.080763 | 0.026519 | 0.083116 | 0.004989 | 0.069494 | 0.056173 | −0.035862 | 0.053462 | 0.061053 | −0.052087 | −0.030736 |
| 133 | 0.064322 | 0.010003 | 0.129758 | 0.035732 | 0.116011 | −0.011478 | −0.042401 | 0.051623 | 0.061137 | −0.023454 | 0.034183 | −0.024691 | 0.061435 | 0.024545 |
| 134 | 0.085928 | 0.086846 | −0.058524 | −0.020908 | 0.013991 | 0.011297 | 0.059784 | 0.137646 | −0.012046 | 0.042503 | 0.206993 | −0.130598 | −0.100018 | 0.045235 |
| 135 | −0.002599 | −0.02321 | 0.007713 | −0.01461 | 0.083016 | 0.000314 | 0.057793 | −0.03765 | −0.057159 | 0.003938 | 0.029643 | 0.087836 | −0.027882 | 0.024613 |
| 136 | −0.016395 | 0.066672 | 0.067093 | 0.0103 | −0.087819 | 0.015338 | −0.015361 | 0.107125 | −0.073956 | −0.021122 | 0.115417 | 0.013885 | −0.048456 | −0.083228 |
| 137 | 0.055113 | 0.053542 | 0.008803 | −0.061871 | −0.022125 | −0.012726 | 0.09894 | −0.096969 | 0.088525 | −0.059011 | −0.067285 | 0.056324 | 0.023578 | −0.005726 |
| 138 | −0.193242 | −0.133202 | 0.13528 | −0.057473 | −0.083335 | 0.011633 | 0.013133 | 0.003733 | −0.112607 | 0.134543 | 0.052425 | −0.056875 | 0.028165 | −0.016614 |
| 139 | 0.078536 | −0.045082 | 0.041832 | 0.072891 | −0.015143 | 0.033404 | −0.038116 | 0.111241 | 0.067155 | −0.069699 | 0.020438 | 0.128176 | −0.014899 | −0.019684 |
| 140 | 0.010636 | −0.140845 | −0.015202 | 0.031054 | −0.179519 | 0.139129 | −0.061896 | 0.01669 | 0.143603 | −0.053762 | 0.071517 | 0.046106 | 0.090619 | 0.034245 |
| 141 | −0.033027 | −0.058975 | 0.033888 | −0.04183 | −0.069332 | −0.036428 | −0.139789 | −0.045076 | −0.05519 | 0.138205 | 0.068423 | −0.022129 | 0.00929 | 0.047706 |
| 142 | 0.024273 | 0.026029 | 0.035974 | −0.028409 | −0.003119 | 0.048624 | −0.001062 | 0.028835 | −0.037294 | 0.030949 | −0.009165 | −0.039132 | −0.001392 | 0.081728 |
| 143 | −0.027193 | 0.007834 | 0.016179 | 0.049398 | −0.027015 | 0.002219 | 0.085885 | 0.032022 | −0.017131 | 0.064375 | −0.080459 | −0.004901 | −0.031779 | 0.0793 |
| 144 | −0.040194 | −0.033901 | 0.047371 | −0.048407 | −0.098106 | −0.027682 | −0.002902 | 0.08093 | 0.018588 | 0.142638 | −0.006306 | −0.012337 | −0.056631 | −0.003135 |
| 145 | −0.071261 | −0.051407 | 0.077666 | −0.010518 | 0.087574 | −0.038193 | −0.080687 | 0.027124 | −0.079356 | 0.038338 | −0.030538 | −0.009325 | 0.045582 | 0.058943 |
| 146 | −0.037681 | 0.005434 | −0.005183 | −0.029638 | −0.012343 | −0.008223 | 0.008029 | 0.034491 | −0.003168 | −0.062188 | −0.00276 | 0.032081 | −0.031349 | −0.011328 |
| 147 | 0.015639 | −0.022407 | −0.032861 | 0.024205 | 0.055342 | 0.049497 | −0.009242 | 0.001911 | −0.023653 | −0.004233 | −0.066989 | −0.063514 | 0.047813 | 0.077896 |
| 148 | 0.011662 | −0.084562 | −0.070091 | −0.018916 | −0.098692 | 0.084056 | −0.028654 | −0.156167 | 0.049631 | 0.040404 | −0.083539 | 0.010488 | 0.068609 | −0.076847 |
| 149 | −0.088205 | 0.013236 | 0.029081 | 0.059925 | −0.047049 | 0.03328 | −0.012603 | −0.127593 | 0.061426 | 0.049317 | −0.075857 | −0.051543 | −0.028819 | −0.008427 |
| 150 | −0.008379 | 0.038577 | −0.142079 | 0.053924 | −0.068067 | −0.108941 | 0.018384 | 0.023704 | 0.052151 | −0.047771 | 0.047419 | 0.085942 | 0.02461 | −0.061104 |
| 151 | 0.082744 | −0.155786 | 0.018988 | 0.069586 | −0.197104 | −0.023594 | −0.046429 | −0.033079 | −0.006834 | −0.063609 | −0.016568 | −0.05064 | 0.071786 | 0.049911 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 152 | −0.003304 | −0.011858 | −0.009989 | 0.025915 | −0.047143 | 0.03547 | 0.019455 | −0.028191 | 0.053078 | 0.019979 | 0.060682 | −0.02269 | −0.043914 | −0.076776 |
| 153 | 0.020389 | 0.049842 | −0.075043 | 0.078456 | 0.036922 | 0.0434 | 0.12613 | 0.02567 | −0.059218 | −0.073616 | −0.065884 | 0.041782 | −0.066618 | 0.041458 |
| 154 | 0.068506 | 0.04793 | 0.002914 | −0.042199 | −0.05355 | 0.05775 | 0.016059 | −0.031311 | −0.036897 | −0.027916 | 0.041361 | 0.005805 | 0.03824 | −0.001776 |
| 155 | −0.032167 | 0.052462 | −0.047555 | −0.023628 | −0.076101 | 0.066916 | −0.038637 | 0.070736 | 0.034225 | 0.02495 | 0.056956 | 0.069481 | −0.023062 | −0.102332 |
| 156 | −0.007509 | 0.051485 | −0.034626 | 0.213248 | 0.104305 | −0.097249 | 0.164062 | 0.088441 | −0.113576 | 0.113163 | 0.08685 | −0.088589 | 0.072799 | −0.050238 |
| 157 | 0.086602 | −0.038861 | 0.015306 | −0.12358 | −0.046874 | 0.021636 | −0.060249 | −0.010206 | 0.004695 | −0.078617 | 0.037585 | 0.060171 | −0.02292 | 0.049533 |
| 158 | 0.195299 | −0.089379 | 0.086257 | −0.02876 | 0.075921 | 0.073374 | 0.127472 | −0.000216 | 0.021082 | −0.083181 | −0.038992 | −0.083972 | 0.025404 | −0.021316 |
| 159 | 0.092193 | 0.125737 | −0.070384 | 0.182869 | 0.08812 | −0.107324 | −0.148002 | −0.169004 | −0.166551 | −0.002161 | −0.000647 | −0.02588 | 0.100657 | −0.040395 |
| 160 | 0.063618 | 0.13173 | 0.063395 | 0.012551 | 0.028323 | 0.073625 | 0.092396 | 0.158613 | 0.051612 | 0.026196 | 0.02072 | 0.046035 | −0.034841 | 0.079482 |
| 161 | 0.086172 | 0.056218 | −0.133129 | −0.018762 | 0.000156 | −0.027208 | −0.06487 | 0.039665 | 0.030046 | 0.022391 | −0.078543 | 0.019008 | −0.006479 | 0.197424 |
| 162 | 0.042286 | −0.009644 | −0.067087 | 0:.011744 | 0.042771 | 0.053129 | −0.039442 | −0.097601 | 0.007948 | 0.101069 | −0.048369 | 0.014309 | 0.015163 | −0.106022 |
| 163 | −0.056455 | 0.026747 | −0.082235 | −0.008813 | 0.015679 | 0.063783 | 0.094643 | −0.073765 | 0.058956 | 0.102062 | 0.008569 | 0.012931 | −0.003604 | 0.039195 |
| 164 | 0.005425 | −0.021805 | 0.047312 | −0.060201 | −0.019929 | 0.054074 | −0.104989 | −0.096462 | 0.099047 | 0.048484 | −0.022042 | 0.071312 | 0.091371 | −0.010074 |
| 165 | 0.052313 | 0.125256 | 0.134126 | 0.010841 | 0.021605 | −0.174111 | −0.065027 | −0.11025 | 0.059799 | 0.004604 | 0.0095 | 0.181735 | −0.099942 | 0.064208 |
| 166 | 0.032409 | −0.034153 | 0.04968 | −0.08073 | 0.240869 | −0.026762 | −0.047765 | 0.071118 | −0.017331 | −0.032366 | 0.058896 | 0.116896 | 0.048619 | 0.070893 |
| 167 | −0.027575 | 0.002462 | 0.045313 | −0.023479 | 0.084564 | −0.086479 | 0.041869 | 0.050868 | −0.033707 | 0.024098 | 0.003414 | −0.170641 | −0.059414 | −0.166291 |
| 168 | −0.051183 | 0.026182 | 0.096481 | 0.045017 | −0.009785 | 0.068115 | 0.033264 | 0.008902 | −0.107573 | −0.152982 | −0.090709 | 0.071073 | 0.081549 | 0.069743 |
| 169 | 0.055407 | 0.012874 | −0.038306 | 0.025587 | −0.007503 | 0.003208 | 0.044651 | −0.015433 | 0.011443 | 0.057265 | 0.034363 | 0.010906 | −0.022233 | 0.01304 |
| 170 | 0.028657 | −0.005949 | −0.035387 | 0.079542 | −0.031084 | −0.029002 | 0.013001 | −0.027906 | −0.025418 | 0.057309 | 0.06067 | −0.019083 | −0.014317 | 0.016677 |
| 171 | 0.00901 | 0.037651 | −0.027358 | 0.073125 | −0.012824 | 0.006713 | 0.044211 | 0.036524 | 0.00451 | −0.005656 | 0.036176 | −0.004132 | −0.095802 | −0.03802 |
| 172 | 0.061748 | −0.008324 | −0.019139 | −0.017061 | −0.032427 | −0.00159 | 0.0136 | −0.004685 | 0.018879 | −0.011051 | −0.03498 | 0.032911 | 0.026032 | −0.039489 |
| 173 | 0.045845 | 0.046611 | −0.003403 | −0.022831 | −0.012108 | 0.004243 | −0.023135 | 0.001662 | 0.00942 | −0.013909 | −0.010087 | 0.016761 | 0.025423 | −0.047244 |
| 174 | 0.074795 | −0.028273 | 0.019325 | 0.02087 | 0.017049 | −0.017675 | 0.000544 | 0.018424 | −0.00033 | −0.012007 | 0.013179 | −0.001082 | 0.00724 | −0.018194 |
| 175 | 0.020239 | −0.034639 | 0.019182 | −0.009212 | 0.031427 | −0.054621 | 0.046841 | 0.017868 | 0.089025 | −0.069983 | −0.078197 | 0.029972 | 0.079924 | 0.042765 |
| 176 | 0.086141 | −0.038571 | 0.038713 | 0.039458 | 0.025329 | −0.014202 | 0.048769 | 0.000026 | 0.059133 | −0.042154 | −0.074554 | −0.022101 | 0.070125 | −0.047177 |
| 177 | 0.079362 | −0.076723 | −0.058457 | 0.076848 | −0.06548 | −0.044199 | −0.070826 | −0.000374 | 0.01214 | 0.063496 | −0.043537 | −0.02287 | −0.168586 | −0.144725 |
| 178 | −0.041292 | 0.02488 | −0.009924 | −0.044756 | 0.066026 | −0.007453 | −0.039341 | −0.006722 | 0.033606 | 0.010275 | 0.001577 | 0.058767 | 0.026047 | −0.026969 |
| 179 | −0.034624 | 0.028648 | 0.017566 | 0.012848 | 0.038709 | 0.022749 | 0.025034 | −0.004528 | −0.018442 | −0.006652 | −0.000475 | 0.016805 | −0.02332 | 0.005093 |
| 180 | −0.029188 | 0.032947 | 0.008519 | −0.014285 | 0.01458 | −0.011275 | 0.002318 | −0.02228 | −0.001481 | 0.033733 | 0.03121 | −0.009553 | −0.033439 | 0.0009 |
| 181 | −0.021388 | 0.012791 | 0.00133 | 0.001538 | 0.013138 | −0.018501 | 0.020546 | −0.016893 | 0.006916 | 0.018265 | 0.038605 | −0.012768 | −0.041331 | −0.006142 |
| 182 | 0.018474 | 0.003718 | −0.002454 | 0.057759 | 0.005042 | −0.004808 | 0.010276 | −0.058522 | 0.025119 | 0.002649 | 0.007524 | −0.024731 | −0.005036 | −0.023759 |
| 183 | −0.007305 | −0.004544 | −0.028049 | 0.042467 | −0.021846 | 0.040951 | 0.087803 | 0.003147 | 0.015156 | −0.0619 | −0.020114 | 0.009761 | −0.008868 | −0.044926 |
| 184 | −0.016401 | −0.088028 | −0.055086 | −0.003892 | −0.056381 | 0.034744 | 0.120112 | 0.024993 | −0.048765 | −0.127214 | −0.027981 | 0.082437 | 0.008697 | −0.040918 |
| 185 | −0.055554 | 0.087059 | −0.107683 | −0.090368 | 0.036404 | −0.033788 | 0.040497 | −0.091668 | −0.018952 | 0.1161 | −0.069191 | 0.00931 | −0.135267 | 0.087077 |
| 186 | 0.057252 | −0.005267 | −0.13734 | 0.046523 | −0.042433 | 0.046207 | −0.013558 | 0.063061 | −0.038658 | −0.076291 | −0.064251 | 0.075015 | −0.198692 | 0.00859 |
| 187 | 0.049378 | 0.043809 | −0.022549 | −0.016421 | −0.034516 | 0.017295 | −0.012906 | −0.037911 | −0.010075 | 0.009055 | 0.055399 | −0.023559 | 0.045702 | −0.069049 |
| 188 | 0.046654 | −0.021394 | 0.003168 | −0.005368 | −0.029088 | −0.006697 | 0.0521 | −0.020719 | −0.009902 | 0.044431 | 0.058584 | −0.010646 | 0.068288 | −0.028012 |
| 189 | 0.055584 | −0.059003 | 0.018156 | −0.013048 | −0.035737 | −0.016195 | 0.052018 | −0.016661 | 0.043155 | −0.002565 | 0.040135 | −0.089989 | 0.16509 | 0.055732 |
| 190 | 0.002594 | 0.00888 | 0.017667 | 0.025307 | −0.041099 | 0.002329 | 0.029116 | 0.012341 | −0.039975 | −0.07669 | −0.043771 | −0.108167 | 0.011005 | −0.017498 |
| 191 | −0.050975 | 0.007494 | −0.010682 | 0.038315 | −0.028325 | 0.109337 | −0.000436 | 0.047507 | −0.048107 | −0.043508 | 0.069555 | −0.072195 | −0.026694 | 0.021678 |
| 192 | 0.004123 | −0.0211 | 0.032736 | 0.044498 | 0.073913 | −0.052321 | 0.029537 | 0.059684 | 0.043075 | 0.028492 | −0.025002 | 0.032166 | 0.009759 | −0.077856 |
| 193 | −0.023411 | −0.02356 | 0.059177 | −0.002477 | 0.011038 | 0.018399 | −0.006307 | 0.102387 | −0.024422 | −0.01637 | −0.048421 | 0.003677 | 0.008643 | −0.017665 |
| 194 | −0.065279 | −0.021268 | 0.103053 | −0.033476 | 0.011494 | 0.019283 | 0.088958 | 0.037229 | 0.001148 | 0.025846 | 0.03933 | −0.015551 | 0.074159 | 0.029528 |
| 195 | −0.022928 | 0.033568 | −0.071824 | −0.069426 | 0.036087 | 0.036037 | 0.063514 | 0.031147 | −0.014663 | 0.004411 | −0.010677 | −0.067643 | −0.012169 | −0.040909 |
| 196 | −0.00364 | 0.042105 | −0.064432 | −0.026524 | 0.020064 | 0.009988 | 0.041617 | 0.051268 | 0.023504 | −0.068787 | 0.006026 | −0.018845 | −0.009051 | 0.026839 |
| 197 | −0.002331 | 0.006043 | −0.014183 | 0.035044 | 0.004161 | 0.054705 | −0.037822 | 0.015153 | −0.061748 | −0.042151 | −0.060558 | −0.069869 | −0.005319 | 0.007047 |
| 198 | −0.098915 | −0.033091 | −0.022705 | 0.021164 | 0.013045 | −0.109703 | −0.048136 | −0.004463 | 0.012615 | −0.0098 | −0.094521 | −0.032494 | 0.007357 | −0.011389 |
| 199 | −0.123192 | 0.068677 | 0.073645 | 0.094219 | −0.034887 | 0.100305 | −0.050206 | 0.04415 | −0.031202 | −0.036397 | −0.028717 | −0.064942 | −0.098875 | 0.090194 |
| 200 | −0.034237 | −0.021124 | 0.019688 | −0.027424 | 0.018192 | −0.050054 | −0.065581 | 0.003371 | 0.028571 | 0.010512 | −0.028205 | 0.059046 | −0.040148 | −0.075664 |
| 201 | 0.092789 | −0.040592 | −0.07837 | −0.046818 | −0.030201 | 0.007884 | 0.102108 | −0.052644 | 0.224348 | 0.098441 | 0.003535 | −0.114068 | 0.03309 | −0.031586 |
| 202 | −0.028618 | −0.036137 | 0.021866 | −0.009812 | −0.021839 | −0.080616 | −0.061372 | 0.017406 | −0.042192 | −0.054076 | −0.005503 | −0.080054 | 0.049721 | −0.069712 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 203 | −0.084637 | 0.105262 | 0.034783 | 0.050904 | 0.116879 | 0.096057 | −0.035189 | 0.036938 | 0.025993 | 0.035552 | 0.067675 | 0.039208 | 0.00666 | 0.170094 |
| 204 | 0.014941 | −0.119861 | −0.033112 | −0.131549 | −0.159767 | 0.032953 | −0.068463 | −0.005257 | −0.113847 | −0.024546 | −0.045856 | 0.011335 | −0.039346 | 0.027845 |
| 205 | 0.03543 | 0.039093 | 0.015666 | −0.048159 | −0.003417 | −0.053775 | 0.179003 | 0.07135 | 0.02709 | −0.022086 | −0.06963 | −0.034879 | 0.134573 | 0.057427 |
| 206 | −0.033617 | −0.009073 | −0.069109 | −0.157986 | 0.04312 | −0.130954 | 0.155045 | 0.107856 | 0.079596 | −0.060505 | 0.052578 | −0.060835 | −0.104793 | −0.005305 |
| 207 | 0.037872 | 0.070582 | −0.033636 | 0.072174 | 0.093469 | −0.08989 | 0.038783 | 0.045016 | 0.085305 | −0.007781 | −0.02552 | 0.031621 | −0.140172 | 0.028107 |
| 208 | −0.0774 | −0.037681 | −0.018743 | 0.098027 | −0.071769 | 0.061707 | 0.025359 | 0.036793 | −0.082488 | 0.116626 | 0.11314 | −0.007708 | 0.040328 | −0.020184 |
| 209 | 0.084921 | 0.055477 | 0.196815 | 0.095349 | −0.001515 | −0.10346 | 0.044041 | −0.084667 | −0.017408 | −0.042678 | 0.153717 | 0.102687 | −0.024581 | −0.016492 |
| 210 | 0.017067 | 0.059573 | −0.099577 | 0.048738 | 0.026475 | 0.029461 | −0.078825 | 0.079856 | −0.052762 | 0.068948 | 0.004313 | 0.11017 | −0.016989 | −0.098265 |
| 211 | 0.10504 | 0.133418 | −0.017214 | −0.093803 | 0.041231 | −0.078553 | −0.026751 | 0.06924 | −0.060515 | 0.012812 | −0.118729 | 0.098226 | 0.049662 | −0.091588 |
| 212 | −0.077903 | 0.080203 | −0.346561 | −0.039841 | −0.119499 | −0.106689 | −0.035851 | 0.034555 | −0.199251 | 0.016938 | −0.056046 | −0.010093 | −0.00955 | 0.011849 |
| 213 | −0.043461 | 0.013203 | −0.118417 | 0.120243 | −0.005038 | 0.020479 | −0.015245 | −0.041582 | 0.063455 | −0.053557 | 0.168593 | −0.119643 | −0.075524 | 0.084848 |
| 214 | −0.026175 | 0.017911 | −0.042691 | 0.003139 | 0.016855 | 0.000564 | 0.015338 | 0.019392 | −0.037157 | −0.067584 | 0.00248 | 0.025023 | 0.027903 | 0.004679 |
| 215 | −0.043851 | 0.057934 | 0.060588 | −0.050097 | 0.105811 | 0.059201 | −0.038343 | 0.010192 | −0.019349 | 0.067458 | −0.041441 | 0.061656 | −0.016336 | 0.076414 |
| 216 | −0.060542 | 0.045369 | 0.051283 | −0.005916 | 0.055424 | 0.022745 | −0.05355 | −0.064898 | 0.029672 | 0.010784 | 0.025781 | −0.021375 | 0.026049 | 0.0394 |
| 217 | −0.064457 | −0.053573 | −0.042949 | 0.049849 | −0.095312 | 0.023237 | 0.044386 | −0.134632 | −0.024238 | 0.014615 | 0.016728 | −0.002832 | −0.019127 | −0.009071 |
| 218 | −0.061225 | 0.00932 | −0.03241 | 0.014765 | 0.012475 | 0.031489 | 0.021812 | 0.002194 | −0.032371 | −0.028698 | −0.008959 | 0.062729 | 0.027776 | 0.032581 |
| 219 | −0.012231 | 0.058042 | −0.06502 | −0.01342 | 0.017116 | 0.004994 | −0.019231 | −0.060893 | 0.008777 | −0.020026 | 0.076262 | 0.036465 | 0.016867 | −0.046927 |
| 220 | −0.021221 | −0.088434 | −0.062347 | 0.01419 | −0.071241 | −0.039723 | 0.007673 | −0.066525 | 0.011564 | −0.093797 | 0.03065 | −0.030434 | −0.036082 | −0.013298 |
| 221 | 0.001661 | 0.027572 | 0.018938 | −0.019348 | 0.018208 | 0.035294 | 0.034898 | −0.046796 | 0.033987 | −0.043902 | 0.015044 | 0.086913 | 0.042282 | −0.026124 |
| 222 | −0.045521 | 0.045825 | 0.004325 | −0.071201 | 0.016498 | 0.018662 | 0.021021 | 0.042247 | 0.00802 | 0.01742 | 0.059961 | 0.030622 | 0.059174 | −0.02611 |
| 223 | −0.028426 | 0.039754 | 0.007465 | −0.060424 | −0.000838 | −0.010842 | −0.008836 | 0.099696 | −0.00777 | −0.098772 | 0.013086 | −0.040191 | 0.026692 | 0.011264 |
| 224 | 0.043286 | −0.080168 | 0.096036 | −0.002292 | −0.032306 | −0.100919 | −0.004842 | 0.019565 | −0.122203 | 0.030334 | 0.052038 | −0.019295 | 0.028553 | −0.087294 |
| 225 | 0.080676 | −0.075774 | 0.074542 | −0.005792 | 0.001862 | −0.08271 | 0.012352 | 0.032811 | −0.065731 | 0.042255 | 0.019138 | −0.031281 | 0.009968 | −0.045683 |
| 226 | −0.008467 | −0.019955 | −0.062954 | −0.00579 | 0.024141 | −0.003062 | 0.015012 | 0.008536 | −0.032041 | 0.027043 | −0.068739 | −0.016997 | 0.034783 | 0.050262 |
| 227 | 0.075951 | −0.09696 | 0.024593 | 0.032826 | 0.086505 | −0.011346 | −0.05538 | 0.054089 | −0.029293 | 0.017547 | 0.037266 | −0.072592 | −0.143195 | 0.014204 |
| 228 | 0.007119 | 0.035709 | 0.037354 | −0.001052 | −0.016579 | 0.09506 | −0.031794 | −0.005729 | −0.05604 | −0.003709 | 0.016454 | −0.014267 | 0.043406 | 0.007473 |
| 229 | 0.029322 | −0.004618 | 0.012229 | 0.014655 | 0.004106 | 0.03148 | 0.039096 | −0.119599 | −0.167141 | −0.070161 | 0.12407 | −0.052065 | −0.025776 | −0.013112 |
| 230 | −0.008511 | 0.037687 | 0.086463 | −0.022627 | 0.056506 | 0.027268 | −0.013646 | 0.046256 | −0.02808 | 0.013787 | −0.028299 | 0.01969 | −0.027443 | 0.071441 |
| 231 | 0.055424 | −0.144378 | 0.027724 | 0.040171 | −0.023643 | 0.008885 | 0.041094 | 0.012645 | 0.01298 | 0.049266 | −0.069871 | −0.005656 | −0.033073 | −0.012385 |
| 232 | 0.074096 | 0.006057 | 0.020834 | −0.111219 | −0.150209 | 0.063307 | 0.033676 | −0.072416 | −0.094547 | −0.037984 | −0.110511 | 0.023877 | −0.145052 | 0.048367 |
| 233 | −0.026272 | 0.07906 | −0.030371 | 0.007946 | −0.057114 | 0.064999 | 0.087232 | −0.071143 | −0.025021 | −0.01615 | −0.040354 | −0.027273 | −0.044269 | −0.052253 |
| 234 | −0.017681 | 0.019486 | 0.001643 | −0.017632 | 0.057419 | 0.058214 | −0.003519 | −0.013306 | −0.044206 | −0.021757 | 0.022803 | −0.014446 | 0.040922 | −0.14568 |
| 235 | 0.011912 | −0.046659 | 0.062956 | −0.019996 | 0.00859 | 0.001397 | −0.054679 | 0.000102 | −0.034008 | 0.077322 | −0.004734 | 0.06409 | 0.002722 | −0.011624 |
| 236 | 0.037603 | −0.036501 | 0.037604 | −0.016871 | 0.038231 | 0.00087 | −0.036435 | 0.025912 | 0.062062 | 0.035044 | −0.018353 | 0.041128 | −0.040121 | 0.034939 |
| 237 | 0.068342 | −0.013393 | 0.016528 | 0.073859 | 0.06273 | −0.007832 | −0.064789 | −0.056614 | −0.012013 | 0.038543 | −0.015735 | −0.049295 | −0.080578 | 0.063663 |
| 238 | 0.039768 | 0.006336 | 0.000145 | −0.008478 | −0.043818 | 0.02522 | 0.005508 | −0.003598 | −0.038747 | 0.020709 | 0.039224 | −0.015056 | 0.007227 | −0.035121 |
| 239 | 0.034522 | 0.050518 | −0.016412 | −0.012585 | −0.030408 | 0.030103 | 0.033191 | 0.027369 | −0.020948 | 0.022766 | 0.000097 | 0.000575 | 0.018934 | −0.029629 |
| 240 | 0.016528 | −0.043834 | 0.008317 | 0.015466 | −0.037962 | −0.009395 | 0.03387 | −0.002683 | −0.025183 | 0.069719 | −0.028756 | 0.032761 | 0.095952 | −0.034038 |
| 241 | 0.029678 | 0.012326 | −0.013607 | 0.012466 | −0.026615 | −0.011754 | 0.074473 | −0.03212 | −0.041971 | 0.007516 | −0.043014 | 0.026385 | 0.016815 | −0.028366 |
| 242 | 0.014441 | 0.074699 | 0.063617 | −0.042289 | 0.019083 | 0.041347 | 0.044014 | −0.024332 | 0.090102 | 0.003122 | −0.019786 | −0.053988 | −0.039006 | −0.035615 |
| 243 | −0.009165 | 0.07141 | −0.041464 | 0.005613 | −0.022073 | 0.073534 | −0.03449 | −0.042035 | 0.042238 | 0.035673 | 0.040457 | −0.03264 | −0.009142 | −0.031411 |
| 244 | 0.020546 | 0.021976 | 0.035768 | 0:028388 | −0.037576 | 0.008104 | 0.0684 | −0.001563 | 0.022223 | −0.057617 | −0.065944 | −0.017318 | −0.053031 | −0.010244 |
| 245 | 0.002382 | −0.025522 | 0.046974 | 0.073626 | 0.061868 | 0.02355 | 0.10961 | 0.027687 | 0.027328 | 0.067574 | 0.035972 | 0.037197 | −0.061702 | −0.046349 |
| 246 | 0.017191 | 0.005056 | 0.007932 | −0.014547 | 0.066595 | 0.031018 | −0.041724 | −0.037233 | 0.025105 | 0.025699 | 0.014251 | −0.034159 | 0.017882 | −0.033899 |
| 247 | −0.031867 | 0.044477 | 0.031559 | −0.051217 | −0.007649 | 0.01337 | 0.007273 | 0.005251 | 0.049731 | 0.022134 | −0.056609 | 0.022422 | 0.016187 | −0.004942 |
| 248 | −0.004406 | 0.014253 | −0.002392 | −0.094568 | −0.056736 | 0.001736 | 0.017651 | 0.002829 | −0.003043 | 0.00842 | −0.052171 | 0.073827 | −0.024436 | 0.009098 |
| 249 | −0.014799 | −0.123348 | −0.061252 | −0.050115 | −0.040009 | −0.046706 | −0.005303 | 0.016397 | −0.029596 | 0.089306 | −0.060621 | 0.014134 | −0.005954 | −0.00354 |
| 250 | 0.018247 | −0.054965 | 0.004297 | −0.00732 | 0.005412 | −0.025281 | −0.014108 | 0.054888 | −0.005043 | −0.0079 | −0.0402 | −0.000617 | 0.046891 | −0.052706 |
| 251 | 0.039216 | −0.014898 | 0.012294 | 0.009741 | −0.018523 | 0.008795 | −0.028366 | 0.016627 | −0.014372 | −0.005863 | 0.021506 | 0.015067 | 0.036884 | 0.013573 |
| 252 | −0.010224 | 0.018558 | −0.000005 | 0.065975 | 0.02291 | 0.033998 | 0.036454 | −0.040633 | 0.014652 | 0.055706 | −0.019279 | 0.045744 | −0.026992 | 0.060345 |
| 253 | −0.022162 | 0.037517 | −0.01633 | −0.021217 | −0.04227 | 0.077731 | −0.021529 | −0.034171 | 0.00884 | −0.020644 | 0.113205 | 0.01877 | 0.00765 | 0.009326 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 254 | 0.037599 | −0.005938 | −0.030016 | −0.01648 | −0.022965 | −0.063178 | −0.01571 | 0.048426 | −0.015051 | −0.091682 | −0.056917 | −0.029786 | −0.060437 | 0.035671 |
| 255 | 0.037726 | −0.003263 | 0.04786 | 0.016542 | −0.040321 | −0.006959 | −0.023775 | −0.06726 | −0.010104 | −0.050818 | −0.005526 | −0.017052 | 0.004249 | 0.022236 |
| 256 | 0.025569 | −0.060078 | 0.064863 | 0.024338 | 0.020495 | 0.037007 | −0.003152 | −0.095711 | −0.078418 | 0.082223 | 0.069148 | 0.032266 | −0.044168 | 0.012684 |
| 257 | −0.022501 | 0.007396 | 0.029556 | −0.048695 | 0.006933 | 0.00962 | −0.012181 | 0.032178 | 0.075916 | 0.034469 | 0.0303 | 0.015224 | −0.022101 | 0.000097 |
| 258 | −0.024669 | 0.053462 | 0.031853 | 0.013209 | 0.01039 | 0.045903 | −0.004597 | 0.036401 | 0.078207 | 0.058979 | −0.041163 | 0.091188 | 0.018599 | −0.002539 |
| 259 | −0.033914 | −0.029018 | −0.013948 | −0.028661 | 0.005747 | −0.041342 | −0.025614 | 0.032843 | 0.040696 | 0.029786 | 0.003057 | −0.036114 | 0.0047 | −0.01134 |
| 260 | −0.019032 | 0.028106 | −0.001172 | 0.107626 | 0.039263 | −0.079746 | 0.006666 | 0.022045 | 0.056187 | 0.002639 | −0.038878 | 0.034889 | −0.012292 | 0.050731 |
| 261 | −0.002353 | 0.005736 | −0.017066 | 0.032691 | 0.007221 | 0.000305 | 0.047344 | −0.003222 | −0.014426 | 0.038112 | −0.006724 | 0.000659 | 0.012597 | 0.055742 |
| 262 | −0.010003 | −0.009154 | 0.057546 | −0.01886 | −0.004348 | −0.052315 | 0.01195 | 0.030156 | 0.002022 | 0.018184 | −0.01873 | −0.017529 | −0.007229 | 0.033721 |
| 263 | −0.013334 | −0.045632 | 0.039874 | −0.018953 | 0.007578 | −0.034114 | −0.002438 | 0.048529 | 0.041484 | 0.003211 | 0.037596 | 0.020313 | −0.010169 | 0.016613 |
| 264 | −0.03049 | −0.026575 | −0.038022 | 0.007402 | 0.00311 | −0.049406 | −0.044149 | 0.005066 | 0.013173 | 0.02071 | −0.002085 | −0.036186 | 0.042058 | −0.018579 |
| 265 | −0.071703 | −0.063718 | −0.018301 | 0.007312 | 0.019068 | 0.022074 | −0.045524 | 0.041594 | −0.029421 | −0.038426 | −0.05113 | −0.08377 | 0.031912 | 0.022668 |
| 266 | −0.009716 | −0.017991 | −0.015001 | −0.004938 | −0.010462 | 0.017291 | 0.012972 | 0.040598 | −0.098394 | −0.010077 | −0.057078 | −0.047644 | −0.000336 | 0.04538 |
| 267 | −0.088236 | −0.035346 | −0.027978 | 0.007735 | 0.055259 | 0.041277 | 0.091284 | −0.015779 | −0.041393 | −0.03363 | −0.059107 | 0.019176 | 0.074133 | 0.012158 |
| 268 | −0.023757 | −0.008853 | −0.037329 | −0.025212 | 0.025899 | −0.002643 | 0.006678 | 0.022498 | −0.011227 | 0.015139 | −0.038091 | −0.017966 | 0.04995 | 0.018495 |
| 269 | 0.008629 | −0.02244 | −0.037456 | −0.041473 | −0.005288 | −0.016034 | −0.008411 | −0.006726 | −0.03053 | 0.012704 | −0.019848 | −0.032598 | 0.011345 | 0.021265 |
| 270 | −0.017864 | −0.011302 | −0.042673 | −0.005462 | −0.001629 | 0.002071 | −0.008992 | 0.034172 | 0.024272 | −0.018448 | −0.005913 | −0.014082 | 0.000827 | 0.022287 |
| 271 | 0.005475 | 0.004151 | 0.035255 | 0.126057 | 0.07965 | −0.098476 | −0.018944 | 0.070589 | 0.025468 | 0.058711 | 0.03979 | 0.016361 | 0.077578 | 0.069891 |
| 272 | −0.035767 | 0.007995 | −0.003779 | −0.011592 | 0.012976 | 0.016933 | 0.031187 | 0.003474 | −0.037924 | −0.030562 | 0.023817 | −0.000193 | 0.069496 | −0.02682 |
| 273 | −0.047823 | −0.02842 | −0.029727 | −0.011725 | −0.032657 | 0.008133 | 0.017988 | 0.079611 | 0.027598 | −0.051597 | −0.0114 | 0.035409 | −0.027538 | −0.008964 |
| 274 | −0.035345 | −0.030843 | −0.031862 | −0.012133 | −0.040657 | −0.002977 | 0.011167 | 0.060271 | 0.022553 | −0.049407 | −0.005964 | 0.030324 | −0.036237 | −0.010688 |
| 275 | −0.077978 | 0.005233 | 0.004659 | −0.005564 | 0.01182 | 0.002696 | −0.005725 | 0.097503 | 0.028031 | −0.023422 | −0.011519 | 0.047329 | −0.017376 | 0.058785 |
| 276 | 0.032572 | −0.044149 | 0.026206 | −0.056196 | 0.030851 | 0.021778 | −0.014349 | 0.065032 | 0.050605 | −0.007172 | 0.01571 | 0.054931 | 0.008938 | −0.014262 |
| 277 | −0.036948 | 0.009958 | 0.008031 | −0.01579 | −0.005834 | 0.004768 | 0.003414 | 0.051102 | 0.011757 | 0.017234 | −0.021681 | 0.037214 | 0.040012 | −0.010802 |
| 278 | 0.036707 | 0.039904 | 0.018342 | −0.029093 | 0.004431 | −0.001899 | 0.033526 | 0.023757 | −0.038606 | −0.01351 | 0.012065 | 0.01994 | 0.037 | −0.006781 |
| 279 | 0.043936 | 0.063482 | −0.009002 | −0.047039 | −0.05781 | −0.024438 | 0.020745 | 0.027104 | −0.073405 | −0.036286 | 0.037211 | 0.030211 | 0.074187 | −0.038868 |
| 280 | −0.059719 | −0.005234 | 0.008616 | 0.052835 | −0.037747 | 0.08978 | 0.019403 | 0.003068 | 0.099995 | 0.049089 | 0.053848 | −0.030794 | 0.029668 | 0.010126 |
| 281 | −0.075279 | 0.018825 | −0.020701 | 0.002169 | −0.033237 | −0.017572 | 0.028333 | 0.050396 | 0.0295 | 0.03029 | −0.021539 | 0.036602 | 0.104056 | 0.02813 |
| 282 | −0.008128 | 0.022068 | 0.007954 | 0.030455 | −0.005117 | −0.028889 | 0.02198 | −0.004868 | −0.031331 | −0.012052 | 0.016201 | 0.03866 | 0.073598 | 0.002957 |
| 283 | −0.007624 | 0.075433 | −0.025949 | −0.034155 | −0.002854 | −0.067677 | −0.029011 | 0.010591 | −0.008753 | −0.07001 | −0.015537 | 0.029088 | −0.001888 | 0.00162 |
| 284 | −0.016878 | 0.006119 | 0.017335 | −0.030601 | 0.007168 | −0.013701 | −0.034328 | 0.042462 | 0.070888 | −0.005042 | 0.023742 | 0.021982 | −0.01634 | −0.000953 |
| 285 | 0.0154031 | 0.010243 | 0.010652 | −0.040981 | −0.024467 | −0.02547 | −0.061899 | 0.015531 | 0.03283 | −0.029099 | 0.072197 | 0.004221 | −0.01606 | −0.004012 |
| 286 | −0.038336 | 0.057014 | 0.01465 | 0.074525 | −0.022498 | 0.021213 | −0.0166 | 0.040784 | 0.065362 | 0.025493 | 0.000613 | 0.022604 | −0.023641 | −0.005892 |
| 287 | 0.012331 | 0.06655 | 0.008575 | 0.060532 | −0.038064 | −0.011123 | −0.005056 | 0.001546 | 0.025727 | −0.002509 | 0.021117 | 0.024184 | −0.009658 | −0.011881 |
| 288 | 0.050414 | 0.089931 | 0.032364 | 0.016003 | 0.003788 | 0.0053 | −0.024568 | −0.037519 | −0.028799 | 0.001478 | −0.001342 | 0.063194 | 0.017565 | −0.001329 |
| 289 | −0.034697 | −0.028587 | 0.047059 | −0.016203 | 0.010628 | −0.038608 | −0.031972 | 0.023227 | 0.008304 | −0.001743 | −0.027136 | −0.016075 | 0.005675 | 0.008081 |
| 290 | −0.020639 | −0.004847 | −0.031975 | −0.043757 | 0.019742 | −0.013335 | 0.011617 | −0.016506 | −0.055238 | 0.019978 | 0.060933 | −0.005984 | 0.022604 | −0.033419 |
| 291 | −0.011633 | −0.006595 | −0.033088 | −0.042403 | 0.01955 | −0.011357 | 0.021857 | −0.019098 | −0.047363 | 0.030445 | 0.046228 | −0.001033 | 0.018841 | −0.036149 |
| 292 | 0.002149 | −0.007773 | −0.032314 | −0.06782 | −0.013873 | −0.014014 | 0.007109 | 0.010809 | −0.097605 | 0.001948 | 0.032232 | −0.028308 | 0.046928 | −0.029579 |
| 293 | 0.02236 | 0.028497 | 0.099194 | −0.00823 | −0.003722 | −0.006224 | −0.029356 | −0.082519 | −0.002814 | 0.117645 | −0.044551 | −0.021031 | −0.082399 | −0.012301 |
| 294 | −0.008383 | 0.0207 | −0.019514 | 0.056743 | −0.03069 | 0.009318 | −0.0048 | 0.016211 | 0.000824 | 0.067186 | −0.07068 | 0.045624 | 0.015853 | −0.011344 |
| 295 | −0.004214 | 0.007221 | 0.016545 | 0.023065 | −0.044439 | −0.004362 | 0.005049 | 0.003959 | 0.006811 | 0.020827 | −0.034034 | 0.000787 | −0.088047 | −0.046726 |
| 296 | −0.094822 | 0.020413 | −0.021854 | 0.02602 | −0.086915 | 0.059504 | 0.063452 | 0.047329 | 0.044617 | −0.060626 | 0.005835 | 0.016816 | 0.008506 | 0.018674 |
| 297 | 0.037971 | −0.030988 | 0.026531 | 0.02625 | −0.035476 | −0.007663 | 0.040054 | −0.00862 | 0.000292 | 0.010803 | −0.020635 | −0.017857 | −0.071714 | −0.045779 |
| 298 | −0.054407 | −0.014363 | −0.008013 | 0.072423 | −0.007489 | −0.046305 | −0.130385 | 0.039086 | 0.044843 | −0.120219 | −0.024117 | −0.01979 | 0.026623 | −0.013121 |
| 299 | 0.057355 | −0.027178 | −0.013765 | 0.068508 | −0.016282 | −0.02452 | 0.010085 | −0.061644 | −0.049917 | 0.05498 | −0.056321 | −0.036085 | −0.009625 | 0.006146 |
| 300 | −0.119947 | −0.104892 | −0.026384 | 0.001979 | −0.104051 | −0.180244 | −0.118054 | 0.124395 | −0.029454 | −0.063655 | −0.044513 | −0.0578 | 0.034399 | 0.082712 |
| 301 | 0.032325 | 0.010359 | 0.025993 | −0.028608 | 0.012467 | −0.017316 | −0.029492 | −0.075289 | 0.001733 | 0.036854 | 0.014787 | −0.036522 | −0.039169 | −0.000268 |
| 302 | −0.039024 | −0.035093 | −0.038625 | −0.009754 | 0.037097 | −0.019355 | −0.045017 | −0.036485 | 0.004553 | 0.042825 | 0.042739 | −0.001117 | 0.069546 | 0.000395 |
| 303 | 0.073611 | 0.062207 | −0.065708 | 0.07564 | 0.038392 | 0.017859 | 0.021062 | −0.070789 | −0.048089 | −0.003487 | −0.043796 | −0.011659 | 0.084691 | −0.05311 |
| 304 | 0.021228 | 0.021308 | −0.082972 | 0.031898 | 0.04372 | 0.047924 | 0.018359 | −0.061245 | 0.022704 | −0.021467 | −0.005656 | 0.046034 | 0.057411 | −0.004473 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 305 | 0.01542 | −0.003091 | −0.021555 | 0.001809 | −0.009525 | 0.022143 | 0.042065 | −0.030282 | −0.030193 | −0.033024 | −0.072393 | −0.14214 | −0.030292 | −0.002678 |
| 306 | −0.02304 | 0.002894 | −0.003682 | −0.047697 | 0.086948 | −0.018415 | 0.056456 | −0.025719 | 0.123294 | 0.00896 | 0.016011 | 0.019545 | −0.111613 | 0.066 |
| 307 | 0.03778 | 0.150826 | 0.019189 | 0.074523 | −0.104989 | −0.150131 | 0.044421 | 0.162683 | −0.015331 | −0.081526 | −0.035416 | 0.132662 | 0.031287 | −0.131579 |
| 308 | 0.006603 | −0.051031 | 0.01676 | −0.034398 | 0.023242 | 0.019783 | −0.022786 | −0.001357 | −0.005787 | −0.053842 | 0.088915 | 0.006777 | −0.005542 | −0.007855 |
| 309 | 0.005319 | −0.051874 | 0.0175 | −0.013532 | 0.011417 | −0.002003 | 0.004956 | −0.019921 | −0.017681 | 0.00032 | 0.051522 | 0.005382 | 0.032953 | 0.01925 |
| 310 | 0.019171 | −0.038077 | −0.011843 | 0.068287 | 0.025685 | −0.018687 | 0.007141 | −0.038401 | 0.023351 | 0.043377 | −0.007433 | 0.048506 | 0.026825 | 0.028128 |
| 311 | 0.040566 | 0.043465 | 0.000749 | −0.037859 | −0.033425 | −0.067177 | 0.039507 | −0.008361 | −0.001284 | −0.020128 | −0.023818 | −0.018106 | −0.03071 | −0.019315 |
| 312 | 0.022029 | −0.03751 | −0.062214 | −0.07059 | −0.11824 | 0.135672 | 0.218846 | 0.056882 | −0.118406 | 0.074629 | 0.008778 | 0.093481 | −0.044919 | −0.053175 |
| 313 | 0.002253 | −0.080035 | −0.023005 | −0.04656 | −0.014393 | −0.0385 | 0.051736 | −0.036795 | −0.001904 | −0.066394 | −0.058958 | −0.018862 | −0.004806 | −0.044595 |
| 314 | 0.014244 | −0.113123 | −0.05464 | 0.020941 | 0.093237 | −0.024014 | −0.144765 | 0.014017 | −0.036246 | −0.090404 | −0.022975 | 0.148084 | 0.007869 | −0.1333 |
| 315 | 0.025187 | −0.012537 | 0.046432 | 0.006365 | −0.014627 | −0.022129 | 0.031677 | −0.023316 | −0.070911 | −0.021099 | −0.054478 | −0.027218 | −0.008527 | 0.006412 |
| 316 | −0.110059 | 0.062919 | −0.016991 | −0.108416 | −0.021074 | −0.054286 | 0.076799 | −0.118247 | 0.034224 | −0.110476 | 0.09802 | −0.068657 | −0.007622 | −0.042526 |
| 317 | 0.006852 | −0.019341 | 0.058917 | −0.032747 | 0.018209 | −0.050953 | −0.037495 | −0.013233 | 0.004965 | −0.013418 | 0.0845731 | −0.019576 | 0.019693 | 0.009973 |
| 318 | 0.036331 | −0.028698 | 0.060787 | −0.025783 | −0.018796 | −0.054476 | −0.044595 | 0.048728 | −0.042754 | 0.003727 | 0.080476 | −0.018403 | −0.041362 | −0.020419 |
| 319 | 0.020799 | 0.007161 | 0.051548 | 0.01569 | 0.021085 | −0.025675 | −0.011094 | −0.006148 | −0.061019 | −0.031074 | 0.037056 | −0.008216 | −0.012594 | −0.009775 |
| 320 | 0.038755 | 0.03203 | −0.001122 | −0.007552 | 0.078538 | −0.030358 | −0.071082 | 0.013332 | 0.009652 | 0.022322 | 0.043174 | 0.064446 | −0.074215 | 0.067407 |
| 321 | 0.052888 | 0.022114 | 0.009997 | 0.006749 | 0.0156 | 0.046041 | −0.063 | 0.04941 | −0.041272 | −0.054923 | −0.093278 | 0.091251 | 0.012642 | −0.102824 |
| 322 | −0.020161 | −0.115205 | 0.12947 | −0.044241 | −0.030102 | 0.067697 | 0.065576 | 0.024654 | −0.065423 | −0.032419 | 0.027081 | −0.02648 | −0.132787 | 0.132116 |
| 323 | 0.021907 | −0.013675 | −0.060379 | −0.043781 | 0.089419 | 0.05593 | −0.055565 | 0.032591 | −0.041419 | 0.003796 | −0.185547 | −0.042175 | −0.050076 | −0.015828 |
| 324 | 0.037304 | 0.023773 | 0.005831 | −0.03409 | 0.03938 | −0.133053 | 0.077153 | −0.056913 | 0.092403 | 0.002896 | 0.040763 | −0.027457 | 0.002787 | −0.059504 |
| 325 | −0.030961 | 0.024746 | −0.005507 | 0.017002 | 0.029522 | 0.052094 | 0.073176 | −0.066369 | 0.006156 | −0.02891 | 0.025106 | −0.011599 | 0.025383 | 0.011302 |
| 326 | −0.014793 | 0.064243 | −0.109713 | 0.029544 | −0.0121 | −0.043735 | 0.036607 | 0.04025 | 0.034992 | 0.057977 | 0.133111 | 0.089871 | 0.071919 | −0.020385 |
| 327 | 0.003017 | −0.012309 | −0.028708 | −0.005024 | −0.011205 | −0.010791 | 0.016534 | −0.003442 | −0.020609 | −0.047615 | 0.018768 | −0.015472 | −0.01738 | −0.029954 |
| 328 | −0.024691 | 0.007003 | 0.033451 | 0.000814 | −0.067971 | 0.137724 | −0.055353 | −0.03803 | 0.055125 | −0.192264 | 0.041873 | −0.012619 | 0.115971 | 0.063892 |
| 329 | 0.021663 | 0.031222 | −0.090482 | −0.040368 | −0.008671 | 0.040294 | −0.002057 | 0.011421 | 0.015543 | 0.022143 | −0.035779 | −0.028392 | 0.057215 | −0.054239 |
| 330 | 0.107134 | 0.060185 | −0.080381 | −0.03963 | 0.098348 | 0.02228 | −0.009748 | −0.00048 | 0.085068 | 0.019622 | −0.090826 | −0.094063 | 0.154601 | 0.110465 |
| 331 | 0.006732 | 0.042504 | 0.021828 | 0.000344 | −0.007951 | −0.01421 | 0.032175 | −0.05042 | −0.06005 | 0.015513 | −0.069344 | −0.004102 | −0.019035 | −0.033019 |
| 332 | 0.031012 | 0.009369 | −0.01303 | −0.056344 | −0.027937 | −0.108642 | −0.021848 | −0.022062 | −0.07676 | 0.003466 | 0.096373 | 0.181613 | 0.094404 | −0.082743 |
| 333 | −0.007664 | 0.040557 | 0.050171 | −0.000396 | 0.004994 | 0.034893 | 0.021457 | −0.053544 | −0.009657 | 0.007593 | 0.021755 | −0.032781 | −0.014468 | −0.030839 |
| 334 | 0.005176 | 0.088612 | 0.048825 | −0.017615 | 0.111672 | 0.15252 | 0.102138 | 0.016397 | −0.251697 | 0.046476 | −0.006404 | −0.123892 | 0.154549 | 0.031177 |
| 335 | 0.036054 | 0.038644 | −0.019847 | −0.018881 | −0.021118 | −0.023127 | 0.006281 | −0.029374 | −0.034069 | −0.006955 | 0.019003 | 0.027401 | −0.055458 | −0.007964 |
| 336 | −0.0614 | 0.028222 | 0.010615 | 0.090908 | 0.010286 | 0.072848 | −0.098028 | −0.009488 | 0.11923 | 0.118075 | −0.166458 | 0.013293 | −0.143032 | 0.042471 |
| 337 | 0.083578 | 0.042027 | 0.011459 | 0.052171 | 0.025526 | 0.039519 | −0.008906 | −0.037301 | −0.004359 | 0.005565 | 0.05208 | −0.045188 | 0.017006 | 0.110001 |
| 338 | −0.185423 | 0.107452 | 0.03766 | 0.021585 | −0.02067 | −0.110889 | 0.141493 | −0.034056 | 0.090577 | −0.039023 | 0.043263 | 0.121635 | 0.07998 | −0.048353 |
| 339 | 0.032433 | 0.062673 | −0.01468 | 0.028696 | 0.026992 | −0.078344 | 0.029265 | 0.037502 | −0.093609 | 0.109686 | 0.027079 | 0.010381 | 0.038355 | −0.013439 |
| 340 | 0.039106 | 0.041108 | 0.046172 | −0.118126 | −0.039655 | 0.163514 | 0.043088 | −0.061984 | 0.113311 | −0.002885 | 0.039431 | −0.048929 | −0.099578 | −0.043438 |

| | BP | BQ | BR | BS | BT | BU | BV | BW | BX | BY | BZ | CA | tc CB | CC |
|---|---|---|---|---|---|---|---|---|---|---|---|---|---|---|
| 1 | −0.028277 | 0.000772 | −0.069196 | 0.057976 | 0.053361 | −0.027805 | 0.003244 | −0.000529 | −0.030384 | 0.009018 | −0.063018 | 0.010903 | −0.016984 | 0.019786 |
| 2 | −0.020629 | 0.023968 | −0.044289 | 0.061056 | 0.044788 | −0.052316 | −0.011239 | −0.024265 | 0.019925 | −0.015659 | −0.033255 | 0.013526 | −0.015262 | 0.030359 |
| 3 | −0.000198 | 0.005996 | 0.017159 | 0.026893 | 0.021321 | −0.031105 | −0.008361 | 0.010201 | −0.039792 | −0.031829 | −0.052053 | 0.015957 | 0.038777 | −0.017379 |
| 4 | 0.016134 | 0.095849 | −0.066349 | −0.011882 | 0.030787 | −0.007795 | 0.076188 | 0.036762 | −0.008154 | 0.06042 | 0.006928 | 0.024649 | −0.076775 | −0.003867 |
| 5 | −0.078591 | 0.025253 | −0.087609 | −0.005676 | 0.138902 | −0.077427 | 0.054318 | 0.144224 | −0.090124 | −0.019261 | −0.083232 | −0.039795 | −0.01455 | −0.011081 |
| 6 | 0.009353 | 0.031432 | 0.010353 | 0.034585 | −0.061221 | −0.032416 | −0.079612 | −0.005088 | 0.044726 | −0.04906 | 0.088919 | −0.088429 | −0.029604 | 0.018675 |
| 7 | 0.019346 | 0.021303 | −0.012155 | −0.040471 | −0.06772 | 0.003323 | 0.039145 | −0.15277 | −0.08898 | −0.023014 | 0.047908 | −0.011109 | 0.150232 | 0.005008 |
| 8 | 0.066688 | 0.058689 | 0.053997 | −0.008745 | −0.083995 | −0.073657 | 0.034781 | −0.083953 | −0.101449 | 0.041287 | −0.020381 | 0.084357 | 0.021296 | 0.075958 |
| 9 | −0.010898 | 0.057733 | −0.046543 | −0.001585 | −0.034566 | −0.007621 | 0.102279 | 0.039871 | −0.00755 | 0.095255 | 0.026133 | −0.02161 | −0.017073 | −0.049679 |
| 10 | 0.05731 | 0.111985 | −0.014228 | 0.026448 | 0.097219 | −0.048287 | 0.031027 | −0.006522 | 0.051168 | −0.055754 | 0.063048 | −0.004573 | −0.035512 | −0.053185 |
| 11 | 0.024194 | −0.214293 | 0.11043 | 0.029691 | −0.107571 | 0.008251 | 0.072996 | 0.064988 | −0.093266 | 0.044675 | −0.080991 | 0.069186 | 0.029255 | 0.049663 |
| 12 | 0.093728 | −0.122906 | −0.039842 | 0.02194 | −0.121733 | 0.004541 | −0.089288 | −0.039681 | −0.102945 | 0.094617 | −0.027733 | −0.004999 | −0.080121 | 0.050185 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 13 | 0.010021 | −0.04065 | −0.008209 | −0.023267 | 0.015525 | 0.054298 | 0.046762 | −0.033543 | 0.013678 | −0.039143 | −0.017754 | 0.063809 | 0.017381 | 0.019054 |
| 14 | −0.007081 | −0.034734 | −0.017035 | −0.021965 | 0.038624 | 0.05802 | 0.013816 | −0.019087 | 0.024289 | −0.029429 | 0.007615 | 0.04388 | −0.005124 | −0.004383 |
| 15 | −0.027841 | −0.042408 | −0.009319 | −0.01777 | 0.019821 | −0.007935 | 0.007083 | −0.010278 | 0.007861 | 0.020976 | −0.04447 | −0.005895 | −0.017419 | −0.024872 |
| 16 | −0.057073 | 0.012855 | −0.039469 | −0.205293 | −0.068586 | −0.035596 | −0.046637 | −0.101957 | 0.031976 | −0.145974 | −0.13875 | −0.144943 | 0.06414 | −0.050874 |
| 17 | −0.074276 | −0.152385 | 0.117014 | 0.041467 | 0.042543 | −0.010366 | −0.070191 | −0.041841 | 0.043626 | −0.003474 | −0.06036 | −0.113651 | 0.067601 | −0.105699 |
| 18 | 0.099705 | −0.046012 | −0.005528 | −0.009836 | 0.014306 | −0.052449 | 0.008203 | −0.031939 | −0.0265 | −0.04597 | 0.111405 | −0.03174 | 0.035876 | −0.024047 |
| 19 | −0.058857 | 0.072945 | −0.091714 | 0.028612 | 0.032455 | 0.018585 | 0.006688 | 0.051599 | 0.03028 | 0.027022 | −0.000181 | 0.009066 | −0.003621 | 0.034956 |
| 20 | 0.000633 | −0.012841 | −0.006145 | −0.009338 | 0.031173 | 0.022548 | 0.021915 | −0.019132 | 0.002368 | −0.002372 | −0.018125 | −0.006541 | −0.004038 | 0.003728 |
| 21 | 0.04019 | 0.016937 | −0.078714 | 0.055658 | 0.01965 | 0.01961 | −0.071337 | 0.026296 | −0.001601 | −0.031898 | −0.007358 | 0.038487 | −0.110598 | −0.02632 |
| 22 | −0.083634 | 0.074932 | −0.027896 | −0.028409 | −0.027438 | 0.01357 | 0.085229 | 0.034753 | −0.030066 | 0.006378 | −0.006184 | 0.060565 | 0.081662 | 0.018488 |
| 23 | 0.002278 | −0.053634 | −0.067661 | −0.131524 | −0.003048 | −0.007358 | −0.049664 | 0.149133 | −0.059529 | −0.007461 | 0.066319 | 0.075032 | −0.054355 | 0.013607 |
| 24 | 0.089825 | −0.003377 | 0.028146 | 0.019948 | −0.022004 | 0.065329 | 0.017061 | −0.040358 | −0.058811 | −0.013874 | 0.113971 | 0.015085 | −0.003627 | −0.145722 |
| 25 | 0.033625 | 0.111325 | −0.011876 | 0.006927 | −0.005917 | −0.016572 | 0.05166 | −0.052052 | −0.007688 | 0.029656 | 0.016595 | 0.034839 | 0.006408 | 0.023368 |
| 26 | −0.003069 | −0.023199 | −0.011203 | −0.010576 | 0.034024 | 0.016833 | 0.008674 | −0.020002 | 0.004135 | −0.003549 | −0.010498 | −0.012796 | −0.019756 | 0.009719 |
| 27 | −0.003776 | −0.010184 | −0.000594 | 0.008778 | 0.011955 | 0.00826 | 0.002456 | 0.001349 | 0.004452 | −0.024999 | −0.008129 | −0.005862 | 0.005222 | −0.013996 |
| 28 | −0.022819 | 0.018044 | −0.009998 | 0.006032 | −0.008491 | 0.03535 | 0.062626 | −0.017193 | −0.020308 | 0.01605 | 0.007124 | −0.01162 | −0.049157 | 0.056988 |
| 29 | 0.021332 | −0.013621 | −0.035541 | 0.038086 | 0.000872 | 0.018674 | −0.036578 | 0.02615 | −0.044647 | 0.10786 | −0.020944 | 0.023057 | −0.006195 | 0.014325 |
| 30 | 0.06913 | −0.050583 | 0.027984 | −0.065604 | −0.02458 | 0.015384 | −0.011099 | 0.013634 | −0.034155 | 0.04155 | 0.018939 | −0.009128 | −0.045612 | −0.038092 |
| 31 | −0.024297 | −0.032944 | −0.003283 | 0.012082 | 0.015507 | −0.008063 | −0.01436 | −0.010237 | −0.039754 | 0.00303 | 0.029789 | −0.00565 | 0.006636 | −0.028232 |
| 32 | 0.004579 | −0.001762 | 0.055681 | 0.078024 | −0.037551 | −0.04665 | −0.006939 | −0.078037 | −0.037975 | 0.057605 | −0.051283 | −0.027474 | −0.085285 | 0.000545 |
| 33 | 0.03809 | −0.037574 | −0.003026 | −0.058758 | 0.057767 | 0.048913 | 0.032582 | 0.004015 | −0.010942 | 0.015002 | −0.001434 | 0.005653 | −0.036506 | −0.008745 |
| 34 | −0.084098 | −0.041549 | −0.006309 | −0.033452 | 0.000047 | 0.005329 | 0.079767 | −0.03244 | −0.025273 | 0.062442 | −0.018721 | −0.017778 | −0.026859 | −0.029872 |
| 35 | 0.032894 | 0.107776 | 0.093753 | −0.120554 | −0.059033 | 0.087282 | −0.044935 | −0.028454 | −0.030461 | −0.013906 | 0.01781 | 0.048395 | −0.143131 | 0.044519 |
| 36 | −0.049507 | −0.001312 | 0.004107 | −0.006943 | −0.000034 | 0.030785 | 0.0216 | 0.012549 | 0.011515 | −0.038731 | −0.026174 | 0.02654 | −0.015944 | −0.053986 |
| 37 | 0.021638 | −0.024227 | −0.027461 | −0.00964 | 0.072523 | −0.003545 | 0.033661 | −0.001815 | 0.01979 | −0.000724 | 0.036191 | 0.014206 | 0.008486 | −0.034803 |
| 38 | −0.032214 | 0.040497 | 0.138496 | −0.110901 | −0.090991 | −0.009306 | 0.063987 | −0.035036 | −0.018374 | 0.077924 | −0.028251 | 0.067898 | −0.005224 | −0.137158 |
| 39 | 0.016154 | −0.005235 | −0.008436 | 0.040881 | 0.029388 | −0.029175 | 0.026497 | −0.026645 | 0.029629 | 0.040677 | −0.046113 | 0.033542 | −0.0505 | −0.013249 |
| 40 | −0.060804 | −0.06247 | −0.001214 | 0.028473 | 0.010772 | 0.020153 | 0.002846 | 0.02211 | 0.029305 | 0.013412 | 0.011311 | −0.079309 | 0.070683 | −0.007077 |
| 41 | −0.050937 | −0.007605 | −0.089147 | 0.024989 | −0.013245 | 0.003078 | 0.002951 | 0.050399 | 0.077624 | −0.006847 | 0.020379 | −0.005513 | 0.043444 | 0.034036 |
| 42 | −0.004548 | −0.030565 | 0.012758 | 0.056273 | −0.048307 | −0.007679 | −0.060224 | 0.055822 | 0.043392 | 0.007662 | −0.027427 | −0.007465 | 0.05536 | −0.000402 |
| 43 | −0.073069 | −0.038059 | 0.0331 | −0.004495 | −0.007234 | 0.026784 | 0.025042 | −0.002174 | 0.01182 | −0.004155 | 0.032943 | −0.032357 | 0.044225 | −0.012753 |
| 44 | 0.019878 | −0.004003 | −0.007439 | −0.022659 | −0.037117 | −0.003342 | 0.029334 | −0.050451 | 0.030235 | −0.037342 | 0.066348 | −0.029884 | 0.004204 | 0.000379 |
| 45 | −0.017533 | −0.018122 | −0.012073 | −0.006173 | −0.048957 | −0.015161 | 0.030411 | −0.022766 | 0.012203 | −0.029853 | 0.030382 | 0.026279 | −0.041065 | −0.059849 |
| 46 | −0.058846 | 0.0204 | 0.045062 | −0.069505 | −0.013623 | −0.041599 | 0.021982 | −0.005771 | 0.051335 | −0.001215 | 0.089924 | 0.103245 | 0.002576 | −0.100721 |
| 47 | −0.03599 | 0.071196 | −0.125855 | −0.094735 | −0.028909 | 0.08352 | 0.036154 | −0.058517 | −0.045137 | −0.013195 | 0.067255 | 0.062122 | 0.016908 | −0.027504 |
| 48 | 0.031198 | 0.004735 | 0.033272 | 0.00617 | 0.038789 | −0.096272 | 0.049058 | 0.007627 | −0.055115 | 0.035679 | −0.019577 | −0.007108 | −0.043975 | 0.025327 |
| 49 | 0.055751 | −0.066002 | 0.060182 | −0.077653 | −0.025714 | −0.007274 | −0.016916 | 0.008822 | −0.01642 | 0.021415 | 0.004813 | −0.009777 | −0.067133 | −0.011917 |
| 50 | 0.052649 | −0.050988 | 0.009665 | −0.034376 | −0.056334 | −0.028847 | −0.000436 | 0.016728 | −0.013232 | 0.022613 | 0.037638 | −0.012345 | −0.058662 | −0.02986 |
| 51 | 0.013052 | 0.085702 | 0.041917 | −0.030042 | 0.097959 | 0.03596 | −0.006355 | 0.018638 | 0.048306 | 0.074562 | −0.00555 | 0.029865 | −0.013489 | −0.061979 |
| 52 | 0.024338 | 0.076847 | −0.100511 | 0.008288 | 0.069222 | −0.13149 | 0.03042 | −0.017411 | −0.003479 | −0.033009 | 0.0245 | 0.005077 | −0.019818 | 0.019705 |
| 53 | −0.030154 | 0.014013 | 0.027967 | −0.048726 | 0.029489 | −0.044228 | 0.007088 | 0.028771 | 0.072617 | 0.043131 | 0.004867 | 0.011218 | −0.011489 | −0.002394 |
| 54 | 0.077133 | 0.013069 | 0.041653 | 0.029932 | −0.010224 | −0.029472 | −0.051596 | −0.022602 | −0.004765 | 0.046355 | 0.078479 | −0.01109 | −0.013976 | 0.036567 |
| 55 | −0.073791 | −0.025355 | 0.015855 | −0.028064 | 0.001842 | −0.012174 | 0.050058 | 0.032667 | 0.043459 | 0.018524 | 0.030666 | 0.040874 | −0.086824 | −0.031637 |
| 56 | 0.01111 | 0.003541 | 0.047014 | −0.045191 | 0.001964 | −0.004686 | 0.024146 | −0.017675 | 0.036765 | 0.029848 | 0.009896 | −0.067355 | 0.00626 | −0.019556 |
| 57 | 0.026659 | −0.01287 | −0.038977 | −0.007211 | −0.030513 | 0.044427 | −0.061033 | 0.03599 | −0.015649 | −0.012653 | −0.020853 | −0.077507 | −0.028945 | 0.014387 |
| 58 | 0.08865 | 0.015847 | 0.004226 | −0.048565 | 0.067839 | −0.033974 | 0.04928 | −0.035103 | −0.003159 | 0.05724 | −0.031216 | 0.084141 | −0.034159 | −0.06068 |
| 59 | 0.067504 | 0.104861 | −0.010009 | 0.043301 | −0.018062 | −0.02407 | −0.044272 | −0.126865 | −0.02339 | −0.056503 | −0.111544 | −0.054511 | 0.076773 | 0.003243 |
| 60 | −0.067468 | 0.028295 | 0.012501 | 0.051559 | 0.026874 | −0.039148 | 0.031496 | −0.071683 | −0.039337 | −0.060792 | 0.00172 | 0.023325 | 0.012098 | −0.005938 |
| 61 | −0.018639 | 0.03569 | −0.01335 | 0.060887 | 0.06178 | −0.073406 | 0.020643 | −0.070022 | −0.013269 | −0.01827 | 0.053189 | 0.070432 | 0.012578 | 0.096652 |
| 62 | 0.019733 | −0.004206 | −0.000659 | 0.066385 | −0.075174 | −0.038053 | 0.009774 | 0.01918 | −0.093876 | −0.06329 | 0.03983 | 0.008192 | −0.019235 | 0.017873 |
| 63 | 0.043007 | 0.038967 | 0.043506 | 0.024652 | 0.060716 | −0.059071 | −0.021854 | 0.012772 | −0.046915 | −0.084409 | 0.01049 | 0.042086 | −0.001484 | 0.116506 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 64 | 0.049659 | −0.019563 | 0.054706 | −0.026948 | −0.041858 | 0.033061 | −0.047683 | −0.043821 | 0.014916 | 0.055331 | 0.009006 | −0.046262 | −0.009354 | −0.019408 |
| 65 | −0.026674 | −0.040595 | 0.003765 | 0.037195 | −0.03587 | 0.047873 | −0.018928 | −0.020183 | −0.052257 | −0.042301 | −0.071048 | −0.058006 | −0.042556 | 0.014193 |
| 66 | 0.034432 | 0.024224 | 0.026498 | 0.029609 | 0.066235 | −0.020155 | −0.039747 | −0.026836 | 0.085511 | −0.072734 | 0.03223 | 0.084219 | 0.02439 | 0.078399 |
| 67 | −0.039246 | 0.055186 | −0.051989 | −0.058852 | 0.026982 | 0.037193 | −0.054086 | 0.028843 | −0.056836 | −0.012576 | −0.039071 | 0.073577 | −0.066928 | 0.009723 |
| 68 | 0.059486 | 0.018533 | −0.086131 | −0.085675 | −0.031106 | 0.066833 | −0.084983 | −0.055468 | 0.041794 | −0.06224 | −0.104959 | −0.117996 | −0.170489 | 0.094517 |
| 69 | −0.003765 | −0.010217 | −0.01256 | 0.019937 | −0.01859 | −0.015266 | −0.024234 | 0.010195 | 0.007985 | −0.015664 | −0.027 | −0.002523 | −0.004061 | 0.018523 |
| 70 | −0.022581 | 0.029595 | −0.013729 | 0.014067 | 0.001415 | 0.000736 | −0.040099 | −0.014546 | −0.047214 | −0.014347 | −0.023945 | −0.003486 | −0.006098 | −0.033397 |
| 71 | −0.044828 | 0.046302 | 0.006501 | −0.101048 | −0.026476 | 0.158515 | 0.041783 | 0.041894 | 0.02855 | 0.102979 | −0.036179 | 0.011833 | 0.008755 | 0.187796 |
| 72 | 0.021617 | −0.001321 | 0.042611 | −0.010003 | −0.049637 | −0.038459 | −0.033743 | −0.010649 | −0.032902 | −0.051571 | 0.03611 | −0.002093 | −0.005607 | 0.039295 |
| 73 | 0.037284 | 0.001069 | 0.037662 | 0.052193 | 0.02953 | −0.03806 | 0.006203 | 0.070686 | −0.011356 | −0.076313 | −0.00944 | 0.031288 | 0.046283 | −0.023478 |
| 74 | 0.005527 | 0.059838 | 0.034113 | −0.085213 | 0.0099 | −0.12315 | −0.081293 | 0.084909 | 0.010944 | −0.110051 | 0.123042 | 0.073617 | −0.044459 | 0.009991 |
| 75 | 0.011053 | 0.004776 | −0.001231 | 0.010842 | 0.005549 | 0.005073 | −0.021967 | −0.011407 | −0.023523 | 0.026846 | −0.006761 | 0.008585 | 0.009247 | 0.007182 |
| 76 | 0.009287 | 0.014577 | 0.028377 | 0.017507 | −0.028401 | −0.019141 | −0.013064 | −0.001451 | −0.020747 | −0.010114 | 0.007513 | −0.009283 | 0.008762 | −0.008627 |
| 77 | 0.007998 | 0.013515 | −0.001985 | 0.023212 | −0.0022 | −0.003222 | −0.029053 | −0.005894 | −0.016692 | 0.027673 | −0.000152 | −0.000222 | 0.016561 | 0.003046 |
| 78 | 0.013773 | 0.014048 | 0.00278 | 0.022044 | −0.002636 | −0.000753 | −0.027391 | −0.002318 | −0.026542 | 0.04148 | −0.00256 | −0.005521 | 0.012979 | 0.000225 |
| 79 | 0.007409 | 0.018451 | −0.004552 | 0.040977 | −0.025982 | −0.004158 | −0.030466 | −0.000445 | −0.018863 | 0.033448 | −0.005825 | −0.031945 | 0.028983 | −0.021503 |
| 80 | 0.068786 | −0.07728 | −0.157945 | 0.043907 | 0.113998 | −0.007453 | −0.107802 | −0.135762 | −0.038984 | 0.035787 | −0.054814 | −0.003794 | −0.043702 | −0.054783 |
| 81 | −0.041398 | 0.065252 | −0.027224 | −0.092966 | −0.012912 | −0.11018 | 0.103448 | 0.000312 | 0.038526 | −0.127943 | 0.006863 | 0.073511 | −0.072156 | 0.058785 |
| 82 | −0.002888 | 0.015263 | 0.012255 | 0.011997 | −0.006621 | 0.009088 | −0.014567 | −0.01842 | 0.002235 | −0.008864 | −0.025739 | −0.018581 | 0.007649 | −0.004057 |
| 83 | 0.003316 | 0.000838 | 0.009387 | 0.003222 | −0.000357 | −0.000679 | −0.012731 | −0.014635 | 0.007421 | −0.016768 | −0.014248 | −0.002257 | 0.004213 | −0.00996 |
| 84 | −0.009168 | 0.009931 | 0.014929 | −0.001293 | −0.001505 | −0.004204 | −0.011364 | −0.006397 | −0.002587 | −0.021464 | −0.007783 | −0.0085 | 0.018295 | −0.01787 |
| 85 | 0.029027 | −0.030068 | −0.03543 | 0.008179 | −0.06331 | −0.11644 | −0.029534 | −0.028568 | −0.004551 | 0.003305 | 0.051369 | −0.008273 | 0.027784 | 0.005687 |
| 86 | 0.000745 | 0.002356 | 0.02319 | 0.022245 | 0.000236 | −0.025479 | −0.03929 | 0.008617 | −0.000809 | −0.009233 | 0.003341 | 0.001835 | 0.040907 | −0.025399 |
| 87 | 0.005926 | −0.027616 | −0.027664 | 0.044458 | −0.002013 | −0.011111 | −0.029194 | −0.030055 | −0.038305 | −0.062874 | 0.073234 | −0.018534 | 0.014369 | −0.011396 |
| 88 | 0.007525 | 0.002894 | 0.010919 | −0.000841 | 0.010044 | 0.003309 | −0.008143 | 0.003398 | 0.000479 | −0.024358 | −0.024446 | 0.000765 | 0.004133 | −0.015511 |
| 89 | 0.000613 | 0.007629 | 0.009066 | −0.004206 | 0.007297 | 0.00611 | −0.005156 | −0.016395 | 0.018453 | −0.010103 | −0.007844 | 0.000824 | 0.001188 | 0.001349 |
| 90 | −0.007009 | −0.004181 | 0.017489 | 0.013661 | 0.003215 | −0.002257 | −0.003282 | −0.007887 | 0.017269 | −0.00641 | −0.005469 | −0.005796 | 0.01841 | 0.005249 |
| 91 | −0.006784 | 0.017643 | 0.00008 | 0.000981 | −0.004462 | −0.020119 | −0.017136 | 0.013832 | 0.022087 | −0.020377 | −0.007116 | 0.004735 | 0.011249 | −0.024315 |
| 92 | −0.005224 | −0.000818 | 0.053024 | −0.00206 | −0.030266 | 0.002082 | −0.023243 | 0.066825 | −0.017518 | −0.019774 | −0.013857 | 0.006134 | −0.016707 | 0.022375 |
| 93 | 0.021362 | 0.023035 | −0.001573 | −0.00567 | 0.020675 | −0.018438 | −0.023463 | −0.038944 | 0.022395 | 0.009912 | −0.033034 | 0.042006 | −0.001202 | 0.00809 |
| 94 | 0.013011 | 0.004901 | −0.008916 | −0.013794 | −0.018248 | −0.018816 | −0.001992 | −0.026877 | −0.016966 | −0.00765 | −0.059065 | 0.002448 | 0.024291 | −0.002702 |
| 95 | −0.108925 | 0.039116 | 0.006163 | 0.084438 | −0.118029 | 0.05587 | 0.091764 | −0.118295 | 0.095885 | −0.116748 | −0.059889 | 0.027622 | −0.158497 | −0.014498 |
| 96 | 0.008894 | 0.042877 | 0.122715 | −0.035308 | 0.101071 | 0.035316 | −0.186225 | −0.007012 | 0.006716 | −0.104267 | −0.038244 | 0.011409 | 0.118096 | −0.148118 |
| 97 | 0.025031 | 0.004114 | −0.000412 | 0.08377 | −0.025412 | 0.009327 | −0.027019 | 0.004547 | 0.019138 | 0.013273 | 0.079884 | −0.020001 | 0.052062 | 0.071629 |
| 98 | 0.002706 | 0.00214 | 0.004088 | −0.012044 | 0.000678 | −0.024034 | 0.020588 | 0.018653 | −0.031221 | 0.004577 | 0.02847 | −0.046756 | −0.024607 | 0.029002 |
| 99 | −0.03073 | −0.075975 | 0.026235 | 0.015456 | 0.009196 | 0.016089 | 0.023605 | 0.035372 | −0.040862 | 0.022825 | 0.020682 | 0.015845 | 0.006326 | 0.050766 |
| 100 | −0.023808 | 0.029552 | −0.027858 | 0.024972 | −0.00132 | 0.020826 | 0.022556 | 0.019791 | −0.019766 | −0.011493 | 0.025339 | −0.021941 | −0.082241 | −0.003629 |
| 101 | 0.020696 | 0.036917 | −0.009152 | −0.043193 | −0.02791 | 0.025082 | 0.008809 | 0.021356 | −0.032203 | 0.013463 | 0.025557 | −0.037335 | 0.011349 | 0.028744 |
| 102 | −0.077224 | 0.039327 | −0.016841 | 0.051404 | −0.046948 | 0.051463 | 0.042319 | 0.041407 | −0.076299 | 0.017764 | −0.009635 | 0.015358 | −0.012399 | −0.073888 |
| 103 | 0.009201 | −0.039614 | 0.009682 | −0.021526 | −0.001795 | 0.171833 | 0.015338 | 0.049179 | 0.067691 | −0.131802 | −0.074674 | 0.084823 | −0.070271 | 0.103101 |
| 104 | 0.084749 | −0.036943 | 0.008705 | −0.017953 | 0.100365 | 0.023979 | 0.023439 | −0.086055 | −0.0627 | 0.041692 | −0.016881 | 0.06849 | −0.03388 | −0.022763 |
| 105 | 0.125553 | 0.036939 | 0.027945 | −0.089181 | 0.212824 | 0.029955 | −0.032609 | −0.013531 | −0.045297 | −0.014311 | −0.050546 | 0.01301 | −0.139688 | −0.03742 |
| 106 | 0.006875 | −0.012883 | −0.01407 | −0.03949 | −0.021288 | 0.047551 | 0.03184 | −0.08271 | 0.143293 | −0.045794 | 0.015893 | −0.006587 | 0.058522 | −0.08216 |
| 107 | −0.006309 | 0.014381 | 0.009456 | −0.01102 | 0.065307 | −0.123004 | 0.02449 | −0.069188 | 0.071334 | −0.059289 | −0.032923 | −0.070264 | 0.088194 | 0.097917 |
| 108 | 0.193366 | 0.074665 | −0.059076 | −0.03202 | −0.028532 | 0.152855 | −0.099972 | 0.063394 | −0.099454 | 0.024242 | −0.045191 | −0.003766 | 0.030284 | 0.096663 |
| 109 | 0.080607 | 0.036434 | 0.054456 | 0.171191 | 0.096199 | 0.063039 | 0.090974 | −0.070091 | 0.033375 | 0.09191 | −0.054265 | −0.037166 | −0.110285 | 0.010468 |
| 110 | 0.015469 | −0.023043 | 0.054066 | −0.06422 | −0.064913 | 0.07483 | −0.071786 | 0.022399 | 0.173907 | 0.100099 | −0.079094 | 0.061525 | 0.105024 | 0.00972 |
| 111 | −0.093408 | 0.054189 | 0.101338 | 0.087643 | −0.040854 | 0.00366 | 0.009765 | 0.044147 | −0.081682 | 0.078052 | 0.028866 | −0.070081 | −0.099355 | −0.035839 |
| 112 | 0.042179 | −0.046048 | −0.093609 | 0.034435 | −0.056479 | −0.027927 | −0.154857 | 0.025021 | 0.087563 | −0.04732 | 0.061571 | 0.221525 | 0.084761 | 0.010807 |
| 113 | −0.018583 | −0.024111 | 0.032289 | −0.010758 | −0.031398 | 0.066059 | 0.093706 | −0.106997 | 0.085355 | 0.07252 | −0.093356 | −0.169221 | 0.124554 | 0.133764 |
| 114 | 0.193096 | 0.075691 | 0.043648 | 0.114352 | −0.065741 | −0.097193 | 0.053102 | 0.154627 | 0.122818 | 0.074191 | −0.042903 | −0.002845 | 0.116423 | −0.136833 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 115 | −0.066151 | 0.042793 | 0.069904 | −0.065498 | 0.071206 | 0.063488 | −0.02975 | 0.190789 | −0.123293 | −0.086886 | 0.076518 | −0.047539 | 0.109019 | 0.063572 |
| 116 | 0.011242 | −0.045868 | −0.080809 | 0.02962 | −0.032666 | 0.106877 | 0.018149 | −0.124925 | 0.206756 | −0.164328 | 0.08726 | 0.022958 | −0.118355 | 0.009779 |
| 117 | −0.018849 | −0.080536 | −0.030156 | −0.023548 | 0.020205 | −0.016307 | 0.060063 | 0.006489 | 0.06866 | −0.016341 | −0.005987 | −0.042561 | 0.101092 | −0.012431 |
| 118 | 0.020604 | −0.037855 | −0.045871 | 0.128697 | 0.042649 | 0.039701 | −0.048642 | 0.01216 | −0.073208 | 0.012024 | 0.066118 | −0.003177 | −0.044376 | −0.032572 |
| 119 | −0.087337 | −0.074907 | 0.064966 | 0.018966 | 0.015132 | 0.058462 | −0.007734 | 0.005675 | 0.05795 | −0.02507 | −0.031395 | −0.070096 | −0.029307 | 0.011822 |
| 120 | −0.024072 | −0.017031 | −0.006492 | −0.01994 | −0.01756 | −0.019878 | 0.00592 | −0.010381 | 0.050775 | 0.005786 | −0.031531 | −0.052687 | 0.048621 | 0.060481 |
| 121 | −0.057446 | 0.067476 | −0.0449 | −0.031723 | −0.028179 | −0.029646 | 0.053064 | −0.048627 | −0.010651 | 0.03196 | 0.003036 | −0.068818 | 0.002433 | 0.022507 |
| 122 | 0.041912 | −0.077968 | 0.020282 | −0.030453 | −0.03326 | −0.033427 | −0.083873 | −0.017021 | −0.022096 | 0.036758 | −0.035001 | −0.036767 | −0.030723 | −0.052523 |
| 123 | 0.047638 | −0.006191 | −0.037828 | 0.035417 | −0.036447 | −0.031531 | −0.09636 | 0.045536 | −0.038189 | 0.026795 | −0.050601 | −0.114244 | −0.0216 | −0.037215 |
| 124 | −0.080965 | −0.068536 | 0.016385 | −0.009733 | −0.010924 | 0.048792 | −0.000236 | −0.010402 | −0.015685 | −0.010482 | 0.00708 | −0.036081 | −0.063422 | −0.000844 |
| 125 | 0.064828 | −0.012821 | −0.076178 | 0.018683 | −0.02914 | −0.042888 | 0.0319 | −0.051731 | −0.011172 | −0.06479 | 0.0402971 | 0.030369 | 0.007525 | −0.001926 |
| 126 | 0.036742 | 0.021313 | −0.04181 | 0.016034 | 0.061452 | 0.046291 | −0.015885 | −0.028635 | 0.044558 | −0.008459 | 0.014744 | −0.014162 | 0.02591 | −0.018494 |
| 127 | 0.045184 | 0.010743 | −0.03508 | 0.023941 | 0.038773 | 0.037676 | −0.006957 | −0.005237 | 0.058956 | 0.010372 | 0.015229 | 0.019392 | 0.037524 | 0.012274 |
| 128 | 0.032305 | −0.034467 | 0.020338 | −0.047862 | 0.015852 | 0.007689 | −0.006887 | −0.052181 | −0.037324 | −0.021692 | 0.07714 | 0.045042 | 0.029756 | 0.015334 |
| 129 | 0.01896 | −0.110153 | 0.065875 | −0.049238 | 0.011342 | −0.053035 | −0.041887 | 0.024694 | 0.019846 | 0.055928 | 0.091594 | 0.026875 | 0.090707 | −0.120305 |
| 130 | −0.050821 | −0.111201 | 0.122623 | 0.016054 | 0.012596 | 0.052361 | −0.122202 | 0.099818 | −0.060041 | 0.106836 | −0.014532 | 0.147333 | −0.16817 | 0.080015 |
| 131 | −0.150917 | −0.082387 | −0.005557 | 0.180621 | −0.144482 | −0.039743 | 0.025859 | 0.026939 | 0.086188 | −0.070665 | 0.005619 | 0.07732 | −0.028894 | 0.078806 |
| 132 | 0.099871 | −0.048978 | 0.023708 | −0.024736 | −0.054215 | −0.034289 | −0.023493 | 0.019778 | 0.006023 | −0.001358 | 0.156996 | −0.035218 | 0.016823 | −0.07188 |
| 133 | 0.102895 | 0.020604 | −0.100739 | 0.052645 | −0.044621 | 0.039856 | 0.093359 | 0.046105 | −0.000503 | −0.052078 | 0.05524 | −0.028676 | 0.089134 | 0.031487 |
| 134 | −0.080827 | 0.036555 | 0.059985 | 0.058684 | 0.11419 | −0.049917 | −0.163771 | 0.010177 | 0.034682 | 0.085436 | 0.002802 | −0.04006 | −0.093273 | 0.150357 |
| 135 | 0.013371 | −0.002525 | −0.028359 | 0.010868 | 0.045226 | −0.005701 | −0.051204 | −0.036486 | −0.012643 | −0.052059 | 0.001146 | −0.012438 | 0.039562 | 0.056157 |
| 136 | −0.107279 | −0.149675 | −0.022262 | 0.073919 | −0.025423 | 0.045355 | 0.047923 | −0.063798 | −0.055311 | −0.090713 | 0.023851 | −0.134164 | −0.012697 | −0.025055 |
| 137 | 0.078917 | 0.011898 | −0.024895 | −0.033954 | −0.037896 | −0.001019 | −0.005607 | −0.061584 | 0.033986 | 0.021628 | −0.076526 | −0.092295 | −0.021839 | −0.004046 |
| 138 | 0.09904 | 0.04751 | 0.086501 | 0.0425 | −0.123004 | −0.019235 | −0.013978 | −0.052267 | 0.081953 | 0.089145 | 0.0511581 | 0.07063 | −0.003063 | −0.004861 |
| 139 | 0.198776 | 0.002664 | 0.000114 | −0.134364 | −0.044988 | −0.041994 | 0.149435 | 0.149878 | −0.08773 | −0.007882 | −0.029075 | −0.04432 | 0.017866 | 0.004017 |
| 140 | −0.058236 | −0.088538 | 0.038161 | −0.152942 | −0.07348 | −0.144624 | −0.117073 | 0.00605 | 0.024565 | 0.179368 | −0.008036 | 0.068694 | −0.002273 | 0.023811 |
| 141 | 0.079351 | 0.108366 | −0.141813 | −0.079799 | 0.06086 | 0.078996 | −0.106094 | 0.083156 | 0.08286 | 0.001567 | −0.050966 | −0.003091 | −0.074896 | −0.05084 |
| 142 | 0.034905 | −0.027698 | 0.029034 | −0.021689 | −0.006358 | 0.044211 | 0.039014 | 0.076612 | 0.0777 | 0.01882 | 0.019006 | 0.114294 | −0.014302 | −0.018207 |
| 143 | 0.080267 | 0.057857 | −0.020445 | −0.022661 | −0.076187 | −0.0732 | 0.062828 | 0.066375 | −0.037297 | 0.029871 | −0.067499 | 0.035245 | 0.045422. | 0.023722 |
| 144 | −0.095198 | 0.028655 | −0.040137 | −0.026497 | 0.019227 | 0.026181 | −0.006144 | −0.038585 | 0.008996 | 0.055147 | −0.100815 | −0.026229 | 0.023729 | −0.002758 |
| 145 | 0.014374 | −0.032489 | −0.013629 | 0.216362 | −0.047812 | −0.010131 | −0.051886 | 0.047129 | −0.066756 | −0.029621 | −0.003589 | −0.085221 | 0.013644 | 0.014352 |
| 146 | 0.024155 | 0.019002 | −0.063388 | 0.008987 | −0.038848 | 0.033385 | −0.007241 | −0.002381 | 0.055709 | −0.041434 | 0.01891 | 0.004489 | 0.107708 | −0.015982 |
| 147 | 0.015523 | −0.079139 | 0.03967 | 0.051978 | 0.095321 | 0.010536 | 0.123614 | 0.025336 | −0.032948 | 0.041811 | 0.091338 | −0.057199 | −0.022417 | 0.017963 |
| 148 | −0.079431 | 0.047195 | −0.031196 | 0.111246 | 0.07061 | 0.112187 | 0.153922 | −0.000962 | −0.014361 | −0.027653 | −0.0081571 | −0.0362291 | 0.147875 | −0.095007 |
| 149 | −0.007358 | −0.037817 | 0.043122 | −0.035992 | −0.049556 | −0.021929 | 0.041099 | −0.037481 | −0.098388 | −0.109128 | −0.123649 | 0.086831 | 0.022139 | −0.04616 |
| 150 | 0.079693 | −0.083808 | 0.014781 | 0.0542 | −0.030568 | 0.020859 | −0.0384 | −0.004541 | −0.06093 | −0.003894 | 0.138567 | −0.041348 | 0.114571 | 0.190357 |
| 151 | 0.159743 | −0.080417 | −0.046552 | −0.000733 | 0.028064 | 0.00897 | 0.030625 | 0.116965 | 0.112305 | −0.100767 | −0.106984 | −0.081944 | −0.078129 | −0.018331 |
| 152 | −0.061776 | 0.000704 | 0.04013 | −0.014229 | 0.054141 | −0.024151 | 0.007302 | 0.033619 | 0.07752 | −0.035577 | 0.009629 | −0.020042 | −0.04436 | 0.016603 |
| 153 | −0.000436 | −0.04157 | −0.010087 | 0.00351 | 0.06052 | 0.073615 | −0.020949 | 0.068046 | 0.057445 | 0.040253 | 0.0554971 | 0.0090461 | −0.011858 | 0.002132 |
| 154 | −0.097049 | −0.061603 | 0.02856 | −0.014299 | −0.002327 | 0.002306 | 0.049274 | −0.026029 | −0.031485 | −0.020926 | −0.003767 | 0.093236 | −0.065487 | 0.021247 |
| 155 | −0.144114 | 0.05695 | 0.009095 | −0.022904 | 0.017704 | 0.033171 | 0.0199 | −0.031756 | −0.070146 | 0.063718 | −0.033779 | 0.076685 | 0.060844 | −0.053779 |
| 156 | −0.072919 | 0.130879 | −0.044747 | −0.056717 | −0.069654 | −0.024884 | −0.034812 | 0.075265 | −0.053204 | −0.024756 | −0.156226 | 0.038412 | 0.008208 | −0.00508 |
| 157 | 0.016124 | −0.041704 | 0.018235 | −0.065199 | 0.04638 | −0.117943 | 0.004323 | −0.061639 | 0.038518 | 0.023017 | 0.046581 | −0.081805 | 0.033323 | 0.014513 |
| 158 | 0.045455 | 0.199637 | −0.033445 | 0.062452 | 0.032501 | −0.032098 | 0.051678 | −0.144534 | −0.028003 | 0.095946 | −0.116361 | 0.186086 | 0.047831 | 0.016824 |
| 159 | −0.027367 | 0.079388 | 0.082172 | −0.054618 | −0.014266 | −0.012039 | −0.076766 | −0.079862 | −0.098189 | 0.027849 | 0.059806 | −0.045348 | 0.00708 | 0.096145 |
| 160 | 0.045796 | −0.091464 | −0.086847 | −0.086797 | 0.028192 | −0.075556 | 0.054581 | −0.114112 | 0.016466 | −0.122296 | −0.040309 | −0.048123 | −0.02197 | 0.043285 |
| 161 | −0.06071 | −0.019099 | −0.118943 | 0.027684 | −0.047171 | −0.188164 | 0.002719 | 0.064278 | 0.0661 | 0.034123 | −0.036266 | −0.004386 | 0.02247 | −0.049092 |
| 162 | −0.002941 | −0.018235 | −0.007373 | 0.027089 | −0.121217 | −0.024998 | −0.034911 | −0.127604 | 0.134375 | −0.040882 | 0.032945 | −0.041656 | −0.061857 | −0.081018 |
| 163 | −0.024659 | 0.001189 | 0.023725 | −0.048558 | 0.047768 | −0.053187 | 0.040877 | 0.013463 | 0.036651 | −0.103941 | 0.047908 | 0.03203 | −0.013487 | 0.107081 |
| 164 | 0.043001 | 0.019149 | −0.052461 | −0.05161 | 0.015662 | 0.043791 | 0.179546 | 0.094242 | 0.02412 | −0.141754 | −0.019169 | 0.071618 | 0.006221 | 0.143683 |
| 165 | −0.133506 | 0.176115 | −0.004986 | 0.066586 | 0.033597 | −0.110121 | −0.006004 | −0.043396 | −0.015334 | −0.058837 | −0.009339 | −0.054752 | 0.043623 | −0.147312 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 166 | −0.029643 | −0.023505 | −0.060623 | −0.117233 | 0.009633 | 0.140346 | −0.068194 | 0.083656 | 0.103036 | −0.056843 | 0.046452 | 0.010739 | 0.115496 | −0.177149 |
| 167 | 0.113746 | −0.03275 | 0.010588 | 0.019012 | 0.024439 | 0.077807 | 0.181847 | 0.017955 | 0.037524 | 0.14442 | −0.040622 | 0.041074 | −0.080677 | −0.037198 |
| 168 | 0.02737 | −0.010086 | −0.121447 | 0.070455 | 0.05782 | 0.02188 | −0.109482 | −0.093366 | 0.103504 | −0.073204 | −0.106389 | 0.042263 | 0.026329 | 0.029097 |
| 169 | 0.002239 | 0.007044 | 0.059172 | −0.043451 | −0.021837 | 0.012244 | −0.012219 | 0.005535 | −0.001955 | 0.005508 | −0.020225 | 0.042638 | 0.034459 | 0.035117 |
| 170 | −0.0431 | −0.009805 | 0.049337 | −0.052958 | −0.006658 | 0.037926 | −0.01852 | 0.006344 | 0.01951 | −0.020071 | −0.05084 | 0.046032 | 0.067317 | 0.042464 |
| 171 | −0.030522 | 0.040831 | 0.006561 | −0.028622 | 0.030663 | 0.028005 | 0.006258 | 0.03432 | 0.065941 | 0.006244 | −0.067457 | 0.052342 | −0.016261 | 0.059339 |
| 172 | 0.034043 | 0.030632 | 0.038744 | −0.039177 | −0.046453 | 0.039593 | 0.002544 | −0.006874 | 0.015226 | −0.002086 | 0.033849 | 0.000552 | 0.024237 | 0.082034 |
| 173 | 0.044672 | 0.009306 | −0.043349 | 0.013342 | −0.014009 | 0.00997 | 0.009426 | 0.027651 | 0.018685 | 0.02597 | −0.019149 | 0.029703 | 0.046828 | 0.000244 |
| 174 | −0.006377 | 0.008673 | −0.049254 | 0.004727 | 0.026287 | −0.004596 | −0.022645 | −0.005704 | 0.052917 | 0.065441 | 0.026874 | −0.009811 | 0.00146 | 0.03692 |
| 175 | −0.043928 | −0.02583 | 0.084511 | −0.028869 | 0.137616 | −0.01385 | −0.067883 | −0.070384 | 0.046699 | −0.027808 | −0.099173 | −0.058621 | −0.037501 | 0.000106 |
| 176 | −0.058034 | 0.071981 | 0.070278 | 0.032931 | −0.036754 | 0.059954 | 0.026764 | 0.046056 | 0.011228 | −0.102975 | 0.024105 | −0.043573 | −0.050483 | 0.043681 |
| 177 | −0.106207 | −0.045686 | −0.066044 | −0.060027 | −0.061208 | 0.081017 | 0.025505 | 0.007961 | 0.033235 | −0.03167 | 0.065797 | −0.029682 | 0.003365 | −0.093517 |
| 178 | 0.025087 | 0.053144 | 0.055221 | 0.071695 | 0.015736 | −0.009566 | 0.041895 | 0.023523 | 0.031232 | 0.021239 | 0.070216 | 0.005766 | −0.058721 | 0.066311 |
| 179 | −0.012705 | 0.016292 | −0.01335 | 0.05059 | 0.029775 | −0.000891 | 0.004754 | 0.028359 | 0.034315 | 0.01129 | −0.017067 | −0.026645 | −0.018986 | 0.006654 |
| 180 | 0.024695 | −0.013125 | 0.00442 | 0.034663 | 0.024277 | −0.004226 | −0.008702 | 0.037007 | −0.01007 | 0.02763 | 0.020275 | −0.012919 | −0.001362 | −0.009533 |
| 181 | −0.000282 | −0.02441 | 0.009188 | 0.007666 | 0.029115 | −0.000689 | 0.032086 | 0.034797 | 0.005406 | 0.028962 | −0.017555 | −0.013799 | −0.036063 | −0.025977 |
| 182 | −0.039289 | −0.034294 | 0.009229 | 0.038969 | 0.004402 | 0.011995 | 0.009976 | 0.0395 | −0.05439 | −0.013513 | 0.012374 | 0.020316 | 0.005659 | 0.013797 |
| 183 | −0.075734 | 0.025276 | −0.001597 | 0.067175 | 0.011891 | 0.026126 | 0.033547 | −0.015536 | 0.008859 | −0.076905 | −0.032031 | 0.042731 | −0.086077 | −0.007069 |
| 184 | −0.042649 | 0.079631 | −0.003892 | 0.043362 | −0.025936 | 0.039502 | 0.027645 | −0.006338 | −0.000149 | −0.034583 | −0.073106 | 0.061537 | −0.122228 | −0.075428 |
| 185 | 0.153195 | 0.081178 | 0.125939 | 0.011366 | 0.055815 | −0.042065 | −0.04815 | 0.019637 | 0.070479 | −0.048809 | 0.181639 | 0.131907 | 0.084904 | −0.10952 |
| 186 | −0.035776 | −0.121976 | −0.08489 | −0.063652 | −0.118948 | −0.082042 | 0.061435 | 0.009185 | −0.007671 | −0.016856 | −0.021219 | 0.020188 | −0.006048 | 0.035418 |
| 187 | 0.043409 | 0.004811 | −0.01562 | 0.052314 | −0.045588 | 0.032912 | 0.011926 | −0.01597 | −0.11707 | −0.026188 | 0.033358 | 0.035646 | 0.055222 | −0.057864 |
| 188 | −0.044959 | 0.044581 | −0.008459 | 0.022566 | −0.022076 | 0.011513 | 0.004908 | −0.040564 | −0.081513 | 0.002125 | 0.047341 | 0.024873 | 0.032326 | −0.048323 |
| 189 | 0.018875 | −0.021274 | 0.044863 | −0.048496 | −0.00466 | 0.010817 | −0.02003 | −0.041693 | −0.101279 | −0.006599 | 0.029542 | −0.071192 | −0.011444 | −0.104103 |
| 190 | 0.044247 | 0.0072 | −0.058766 | −0.002066 | −0.060388 | 0.018647 | 0.024367 | −0.033119 | −0.024855 | −0.075919 | −0.016507 | −0.037626 | −0.000775 | −0.049349 |
| 191 | −0.0183 | 0.022554 | −0.059693 | −0.06265 | −0.017322 | 0.003803 | −0.041686 | −0.038969 | 0.009204 | 0.030337 | 0.047011 | −0.029508 | 0.004412 | −0.095716 |
| 192 | 0.022445 | −0.047247 | −0.004787 | −0.036337 | 0.004889 | −0.023538 | −0.053055 | −0.091386 | 0.043632 | 0.004096 | 0.055044 | −0.023864 | −0.04457 | 0.067753 |
| 193 | −0.027457 | −0.024483 | −0.009422 | 0.022571 | 0.000095 | −0.070168 | 0.033176 | 0.015459 | 0.008467 | −0.035626 | 0.006423 | −0.026737 | 0.011942 | 0.090647 |
| 194 | −0.052669 | 0.050759 | 0.008368 | −0.008086 | −0.030242 | 0.028957 | 0.003359 | −0.003853 | −0.038616 | −0.041951 | 0.051438 | 0.011463 | 0.062324 | 0.053741 |
| 195 | −0.028519 | −0.012267 | −0.050214 | −0.089802 | −0.031763 | −0.071821 | −0.026739 | −0.018726 | 0.083652 | −0.046885 | −0.102868 | 0.024872 | 0.011582 | −0.026793 |
| 196 | −0.014596 | 0.014933 | 0.011158 | −0.072657 | −0.05269 | −0.04126 | −0.059656 | 0.005015 | 0.002358 | −0.01259 | −0.007978 | −0.02998 | 0.001832 | −0.098049 |
| 197 | 0.01642 | 0.043206 | −0.049775 | −0.025586 | −0.053513 | −0.021748 | −0.056806 | −0.032146 | −0.118179 | 0.001696 | −0.029452 | −0.028849 | −0.019175 | −0.035971 |
| 198 | −0.068019 | 0.132206 | 0.11713 | 0.012354 | 0.02096 | 0.021595 | −0.079396 | −0.070074 | 0.055473 | −0.033767 | 0.126093 | 0.074613 | −0.00803 | 0.104484 |
| 199 | −0.004944 | 0.076674 | 0.111318 | 0.015045 | −0.000408 | −0.050362 | 0.078715 | −0.001675 | −0.029764 | 0.096353 | −0.078471 | 0.004207 | 0.023763 | −0.020616 |
| 200 | 0.133219 | 0.049715 | −0.068159 | −0.033803 | −0.000185 | 0.006975 | 0.033739 | −0.022158 | −0.012834 | 0.102111 | 0.002936 | −0.035704 | −0.085646 | 0.157473 |
| 201 | −0.070192 | −0.010761 | −0.045164 | 0.094073 | 0.055508 | 0.007459 | −0.053923 | 0.099036 | −0.05202 | 0.053003 | 0.008625 | 0.001817 | 0.117007 | 0.002697 |
| 202 | −0.006876 | 0.043928 | −0.045278 | −0.017636 | 0.058148 | −0.058509 | −0.038647 | −0.052635 | 0.063399 | 0.052238 | 0.008986 | 0.046221 | 0.101538 | 0.060236 |
| 203 | −0.021161 | 0.039783 | −0.04415 | 0.109958 | 0.082625 | 0.047361 | −0.064085 | 0.000009 | −0.038473 | 0.035321 | 0.061294 | −0.110141 | −0.083822 | −0.004985 |
| 204 | −0.148055 | 0.038526 | 0.049042 | −0.11764 | 0.001247 | 0.135068 | 0.046494 | 0.043975 | 0.08519 | 0.039986 | −0.0698 | −0.056642 | 0.091579 | −0.001402 |
| 205 | −0.095969 | −0.02446 | −0.001631 | 0.015511 | −0.127127 | −0.041861 | 0.027351 | −0.051551 | −0.026656 | 0.012824 | 0.1712 | −0.000425 | −0.055451 | −0.029821 |
| 206 | 0.14587 | −0.111404 | −0.059296 | 0.071549 | 0.012776 | −0.074735 | −0.003763 | −0.023516 | −0.123236 | −0.024822 | −0.11422 | −0.050104 | 0.073804 | 0.013941 |
| 207 | 0.042174 | 0.002077 | 0.039637 | −0.061043 | 0.02653 | 0.031281 | 0.033322 | −0.054704 | −0.058554 | −0.109311 | −0.02266 | 0.060345 | −0.132086 | −0.146128 |
| 208 | 0.017311 | 0.013808 | −0.113809 | 0.044814 | −0.083973 | 0.002409 | −0.141754 | 0.09175 | 0.008044 | −0.011195 | 0.013524 | 0.054977 | 0.071344 | 0.043465 |
| 209 | −0.004161 | 0.036347 | −0.035655 | 0.04268 | −0.071873 | −0.003777 | −0.017504 | 0.12763 | −0.03354 | 0.034816 | 0.016528 | −0.004881 | 0.040171 | −0.067468 |
| 210 | −0.003078 | −0.08204 | −0.005552 | −0.079252 | 0.038908 | 0.063589 | 0.082032 | −0.080588 | 0.004646 | 0.036458 | 0.091965 | −0.092015 | −0.139692 | −0.004481 |
| 211 | −0.110833 | 0.028032 | −0.094516 | 0.011992 | −0.002426 | 0.021544 | −0.032894 | 0.016956 | −0.016585 | 0.192719 | 0.063935 | 0.076184 | 0.053129 | −0.011245 |
| 212 | 0.089811 | 0.139756 | 0.021995 | −0.004484 | 0.138295 | 0.055752 | 0.134349 | −0.089778 | −0.078573 | −0.021956 | 0.001092 | −0.037349 | 0.056597 | −0.032897 |
| 213 | 0.021149 | 0.005831 | 0.066947 | −0.068454 | 0.062984 | 0.110196 | 0.016578 | 0.05668 | −0.036212 | −0.025699 | 0.102882 | −0.107696 | −0.002351 | 0.062481 |
| 214 | −0.017349 | −0.002603 | −0.020703 | 0.005926 | −0.027223 | −0.028179 | −0.021324 | −0.000301 | 0.004824 | 0.007328 | 0.002145 | −0.051574 | −0.010087 | −0.00862 |
| 215 | 0.017404 | −0.078958 | 0.011126 | −0.099306 | 0.059505 | −0.182225 | −0.0402 | 0.016264 | 0.074098 | 0.103318 | −0.032495 | −0.120732 | −0.044964 | 0.095015 |
| 216 | 0.002863 | −0.040552 | −0.06012 | −0.029603 | 0.010475 | 0.084041 | 0.032264 | −0.054109 | −0.032403 | −0.030964 | −0.008902 | 0.062285 | −0.003167 | −0.069057 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 217 | −0.014343 | −0.069443 | −0.021573 | −0.013654 | 0.044385 | −0.04092 | −0.005511 | −0.029482 | −0.008259 | 0.055325 | 0.034574 | −0.019207 | −0.027706 | 0.019371 |
| 218 | 0.007155 | 0.011276 | −0.025131 | −0.007644 | −0.024695 | −0.046502 | −0.011984 | 0.017877 | 0.066532 | 0.036596 | 0.009524 | −0.037578 | 0.032011 | 0.013445 |
| 219 | 0.024775 | 0.009519 | 0.011665 | 0.002522 | −0.06307 | −0.007783 | 0.026881 | 0.043717 | 0.043127 | 0.017408 | −0.026212 | −0.007456 | 0.018749 | −0.024506 |
| 220 | −0.021031 | −0.024287 | 0.020543 | 0.015568 | −0.027852 | −0.002631 | −0.018144 | −0.038234 | −0.015119 | 0.014421 | 0.032847 | −0.019462 | −0.02487 | −0.002967 |
| 221 | 0.004628 | −0.001388 | −0.017521 | −0.01756 | −0.110066 | 0.053317 | −0.044641 | −0.00538 | −0.006332 | 0.000401 | −0.044679 | −0.03039 | −0.028542 | −0.02786 |
| 222 | 0.06476 | 0.035608 | −0.005407 | 0.003834 | 0.017203 | −0.015333 | 0.019189 | −0.00782 | 0.059218 | 0.017843 | 0.010751 | −0.001199 | −0.065693 | −0.017618 |
| 223 | 0.014805 | −0.012576 | 0.043805 | 0.010561 | 0.071368 | −0.00098 | 0.035814 | 0.06118 | 0.062379 | −0.043013 | 0.005884 | 0.046747 | 0.007503 | 0.012409 |
| 224 | 0.035383 | 0.010634 | 0.053188 | −0.067624 | −0.015506 | −0.027418 | 0.030421 | 0.04766 | 0.072009 | −0.055769 | 0.032735 | −0.006606 | −0.00059 | −0.02772 |
| 225 | 0.037794 | 0.00759 | 0.065553 | −0.060417 | −0.054921 | −0.013538 | 0.053254 | 0.006051 | 0.040451 | −0.037678 | 0.017664 | −0.011232 | 0.030226 | 0.003496 |
| 226 | −0.048078 | 0.016113 | −0.028472 | 0.014849 | −0.026265 | −0.027263 | 0.017827 | −0.017663 | −0.023333 | −0.0147 | 0.046341 | 0.049117 | −0.071958 | −0.099341 |
| 227 | 0.041518 | −0.010723 | −0.075117 | 0.008822 | −0.015831 | −0.035037 | 0.034704 | −0.008199 | 0.029066 | 0.087192 | 0.030588 | 0.038415 | 0.044481 | −0.072062 |
| 228 | −0.02801 | 0.067187 | 0.013115 | 0.009673 | −0.056877 | 0.099752 | −0.138503 | −0.078736 | −0.092069 | 0.052152 | −0.021017 | −0.174553 | −0.042995 | −0.04124 |
| 229 | 0.025693 | −0.0789 | −0.020637 | 0.011898 | −0.045373 | −0.045348 | 0.043706 | −0.001971 | 0.025615 | −0.071009 | −0.049277 | −0.039919 | −0.001647 | 0.067227 |
| 230 | 0.010566 | 0.050315 | −0.083257 | −0.047917 | −0.022345 | 0.043162 | 0.017882 | −0.086214 | −0.009933 | 0.018055 | 0.008584 | 0.018271 | 0.039291 | 0.063872 |
| 231 | −0.000007 | −0.034612 | −0.066246 | 0.008024 | −0.02133 | −0.035642 | −0.002563 | 0.008213 | −0.171174 | −0.07645 | −0.056606 | 0.079366 | 0.086843 | −0.073371 |
| 232 | −0.049525 | 0.195505 | −0.120089 | 0.041071 | −0.035099 | −0.115562 | −0.133926 | 0.077593 | −0.032104 | −0.037257 | 0.155745 | −0.064543 | −0.060317 | 0.046641 |
| 233 | −0.044103 | 0.048149 | 0.013192 | −0.012302 | 0.026835 | 0.003717 | 0.017295 | 0.008059 | 0.071675 | −0.012021 | 0.076222 | 0.026242 | 0.068286 | 0.031416 |
| 234 | 0.060272 | 0.003804 | 0.020004 | −0.020508 | −0.069829 | −0.006809 | −0.024111 | −0.047719 | −0.014674 | −0.088283 | −0.023484 | 0.013069 | 0.106434 | 0.089252 |
| 235 | 0.014497 | −0.072363 | −0.019745 | −0.014364 | −0.034388 | −0.04097 | 0.037485 | −0.021029 | 0.053826 | 0.017819 | −0.067408 | −0.08905 | 0.015312 | 0.015736 |
| 236 | −0.016725 | 0.009487 | −0.068182 | −0.001192 | 0.038596 | 0.001522 | −0.005095 | 0.01635 | −0.059981 | −0.090982 | −0.007342 | 0.022404 | −0.029888 | −0.011557 |
| 237 | 0.047211 | −0.00215 | −0.048295 | −0.039584 | −0.05425 | 0.014433 | 0.017427 | −0.030648 | −0.075954 | −0.003327 | 0.003029 | −0.002354 | 0.021843 | 0.011373 |
| 238 | −0.016212 | 0.041571 | 0.006522 | −0.028884 | −0.030403 | −0.026988 | −0.004037 | 0.01672 | −0.031372 | 0.011294 | −0.037883 | 0.008489 | 0.020345 | 0.048045 |
| 239 | −0.078733 | 0.017799 | 0.015461 | 0.01067 | −0.002143 | −0.045494 | 0.005216 | 0.03659 | −0.007902 | 0.012241 | −0.026707 | 0.012656 | 0.002558 | 0.009387 |
| 240 | −0.001468 | 0.034395 | −0.008963 | −0.019824 | 0.049148 | −0.029035 | −0.066491 | −0.042294 | −0.03611 | −0.071785 | −0.015277 | 0.004823 | 0.035984 | 0.022362 |
| 241 | −0.072398 | 0.002673 | −0.026653 | −0.067363 | 0.058193 | −0.01283 | 0.019117 | −0.025165 | 0.030523 | −0.002661 | 0.045585 | 0.005581 | 0.056544 | 0.040303 |
| 242 | 0.019971 | −0.026819 | 0.058355 | −0.017667 | 0.104724 | 0.025073 | 0.015589 | 0.042716 | 0.026874 | 0.014485 | 0.030337 | 0.016393 | 0.016745 | 0.045271 |
| 243 | −0.0019 | −0.067963 | 0.014519 | −0.055136 | 0.020007 | 0.003841 | −0.016743 | 0.03026 | 0.027517 | 0.00855 | −0.013659 | 0.009919 | 0.050942 | −0.031357 |
| 244 | 0.033411 | 0.009695 | −0.08088 | 0.01019 | −0.038379 | 0.042934 | −0.062393 | 0.029526 | 0.003006 | 0.00356 | 0.009976 | −0.049432 | 0.001783 | 0.000075 |
| 245 | −0.016612 | −0.004728 | −0.047707 | −0.109153 | 0.043457 | −0.030295 | 0.048071 | −0.038895 | 0.061788 | 0.155508 | −0.003872 | 0.017795 | −0.01988 | −0.010333 |
| 246 | 0.00539 | 0.02622 | 0.051251 | −0.02774 | −0.010771 | 0.004898 | 0.053051 | −0.045933 | −0.046743 | 0.035929 | −0.025187 | 0.013362 | −0.004956 | 0.016196 |
| 247 | 0.002166 | 0.013685 | 0.040566 | 0.0055 | −0.032537 | 0.01821 | 0.034186 | 0.012246 | −0.038917 | −0.068909 | 0.015292 | 0.037186 | −0.01507 | 0.070116 |
| 248 | 0.011073 | 0.003187 | 0.009098 | 0.045451 | −0.04 | −0.016649 | −0.009434 | 0.025773 | −0.058438 | −0.049443 | 0.040545 | 0.025874 | −0.018935 | 0.058498 |
| 249 | −0.010914 | 0.036414 | −0.082282 | 0.01088 | 0.028764 | −0.08651 | 0.005565 | −0.056626 | −0.012221 | −0.003835 | 0.042621 | 0.008647 | 0.034926 | 0.071099 |
| 250 | 0.003891 | 0.012021 | −0.016038 | −0.02267 | −0.014515 | −0.044991 | −0.041675 | −0.007981 | −0.104355 | −0.071807 | −0.031413 | 0.067167 | 0.036855 | 0.006161 |
| 251 | 0.034867 | −0.037629 | −0.008764 | −0.048057 | −0.020641 | −0.004309 | −0.027891 | −0.006438 | −0.004412 | −0.013938 | −0.047131 | 0.023984 | 0.017507 | 0.036869 |
| 252 | −0.002229 | −0.06687 | −0.002875 | 0.025068 | 0.089091 | −0.04934 | 0.036505 | −0.003946 | 0.090447 | 0.019358 | 0.114938 | 0.034471 | −0.017635 | −0.063391 |
| 253 | −0.094008 | −0.006341 | −0.018938 | 0.064941 | 0.049074 | −0.029162 | 0.034629 | 0.002763 | −0.060998 | −0.047292 | −0.028562 | 0.086301 | −0.022212 | −0.016667 |
| 254 | −0.016168 | −0.027007 | −0.028834 | 0.027145 | 0.042136 | 0.057852 | 0.027213 | 0.121143 | 0.051111 | −0.012207 | 0.011213 | −0.01695 | 0.071551 | 0.002123 |
| 255 | 0.019828 | −0.007042 | −0.012501 | −0.006517 | 0.00749 | 0.063979 | −0.016328 | 0.016163 | −0.016897 | −0.009424 | 0.000932 | −0.02347 | 0.002739 | −0.000681 |
| 256 | −0.089835 | −0.012967 | 0.014722 | −0.061306 | 0.020251 | −0.113584 | −0.001728 | −0.034674 | 0.031091 | 0.037267 | 0.047112 | −0.091912 | −0.017119 | −0.029563 |
| 257 | −0.003368 | 0.007058 | 0.091579 | −0.014688 | −0.034133 | −0.062129 | 0.054826 | −0.007413 | 0.002335 | −0.023368 | 0.01896 | −0.026802 | −0.023331 | 0.040827 |
| 258 | 0.000926 | −0.001789 | 0.013678 | −0.034815 | −0.021932 | 0.044486 | 0.044233 | 0.026906 | −0.029441 | −0.026294 | 0.000692 | 0.008217 | 0.036271 | 0.030142 |
| 259 | 0.032726 | −0.04633 | 0.01067 | −0.003436 | −0.003491 | 0.024669 | 0.010513 | 0.008926 | −0.016334 | 0.067435 | −0.018977 | 0.015551 | −0.018039 | 0.003454 |
| 260 | 0.01287 | −0.094057 | 0.011462 | 0.151096 | −0.079744 | 0.078649 | 0.00937 | −0.002884 | 0.036372 | 0.052518 | 0.060944 | 0.056691 | −0.009038 | −0.045979 |
| 261 | 0.006407 | −0.07295 | −0.00652 | 0.047227 | −0.045073 | 0.094184 | −0.030446 | −0.053385 | −0.00316 | 0.017078 | −0.10459 | 0.029949 | 0.011604 | −0.016602 |
| 262 | 0.006595 | 0.048757 | −0.010755 | 0.02915 | 0.064034 | −0.018474 | −0.007771 | −0.074683 | 0.031019 | 0.023818 | −0.041297 | 0.023443 | −0.018779 | −0.012391 |
| 263 | 0.006749 | 0.035939 | −0.004366 | 0.047434 | 0.078666 | −0.045336 | 0.023267 | −0.044434 | 0.002705 | 0.064306 | −0.033164 | 0.007583 | −0.019711 | −0.017145 |
| 264 | 0.054058 | 0.036912 | 0.021029 | 0.056761 | 0.023117 | 0.002506 | 0.009344 | 0.02527 | −0.015485 | 0.031929 | −0.043541 | −0.055785 | −0.023348 | −0.041702 |
| 265 | −0.015393 | −0.008755 | 0.025666 | 0.026444 | 0.037185 | −0.024854 | 0.025039 | 0.086611 | 0.063662 | 0.022644 | −0.092551 | −0.011347 | 0.043169 | −0.086519 |
| 266 | −0.047277 | −0.06832 | −0.033187 | −0.009801 | 0.0309 | −0.000609 | −0.009054 | 0.057117 | 0.045958 | −0.00457 | −0.092875 | 0.095024 | 0.036968 | −0.043801 |
| 267 | −0.146401 | −0.009759 | −0.001955 | 0.011969 | −0.009331 | 0.014305 | −0.029132 | 0.052909 | −0.115596 | −0.014283 | 0.035476 | 0.042661 | −0.066088 | 0.045682 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 268 | −0.042923 | 0.036735 | 0.00788 | 0.00549 | 0.055024 | −0.042087 | 0.005431 | −0.006534 | 0.001731 | −0.024256 | 0.079652 | 0.032279 | −0.053556 | −0.068986 |
| 269 | −0.029154 | 0.015266 | −0.01255 | 0.028008 | 0.033692 | −0.036039 | 0.003141 | 0.00413 | 0.011383 | −0.036032 | 0.076385 | 0.026878 | −0.059137 | −0.079535 |
| 270 | −0.012047 | 0.022006 | −0.00762 | 0.065615 | 0.040785 | 0.030442 | −0.026539 | −0.02452 | 0.017725 | 0.001838 | 0.039884 | 0.105686 | −0.02321 | −0.081568 |
| 271 | −0.01341 | −0.052653 | −0.183397 | 0.008429 | 0.091296 | 0.022536 | 0.127292 | 0.015183 | 0.00618 | 0.0442 | −0.099103 | 0.151352 | 0.021479 | 0.018819 |
| 272 | 0.008355 | −0.004207 | 0.019514 | 0.041805 | −0.030486 | 0.026455 | 0.004757 | 0.016461 | −0.048888 | −0.025515 | −0.095754 | −0.044344 | 0.008812 | 0.025301 |
| 273 | 0.03494 | 0.048967 | 0.0393 | 0.015923 | 0.017745 | −0.022137 | −0.003768 | −0.057753 | 0.04052 | 0.031108 | 0.002273 | −0.024935 | 0.052006 | 0.009091 |
| 274 | 0.036641 | 0.021237 | 0.031764 | 0.034599 | 0.011647 | −0.013447 | 0.006176 | −0.05166 | 0.036955 | 0.024295 | −0.0057 | −0.033212 | 0.05001 | 0.012787 |
| 275 | 0.052039 | 0.033945 | −0.095038 | 0.016764 | 0.027686 | 0.136371 | −0.038721 | −0.070443 | −0.037754 | 0.067465 | −0.012522 | 0.071355 | 0.057643 | 0.058142 |
| 276 | −0.022555 | 0.003315 | −0.033395 | 0.04023 | 0.069038 | 0.029395 | −0.033502 | 0.033885 | −0.040138 | −0.122168 | −0.03159 | −0.021777 | −0.078631 | −0.044211 |
| 277 | 0.029495 | −0.035205 | 0.073216 | 0.01611 | 0.006989 | 0.018125 | −0.07601 | −0.010141 | 0.034435 | −0.045218 | −0.042765 | −0.008898 | 0.017608 | 0.006219 |
| 278 | 0.005233 | −0.08047 | 0.01904 | 0.051989 | 0.018393 | 0.035966 | −0.017983 | −0.016711 | 0.051741 | −0.071412 | −0.03252 | −0.00339 | 0.035131 | 0.001418 |
| 279 | −0.056998 | −0.010842 | −0.004065 | 0.05355 | 0.002907 | −0.050148 | −0.036277 | 0.047909 | −0.006892 | −0.03165 | −0.03727 | 0.018341 | −0.019525 | 0.000225 |
| 280 | −0.024955 | 0.000388 | 0.033277 | −0.107302 | 0.040716 | 0.039742 | −0.139979 | 0.025559 | 0.002995 | 0.001751 | −0.058546 | −0.008634 | 0.090343 | −0.045285 |
| 281 | −0.016742 | −0.033913 | 0.097137 | −0.003567 | −0.005379 | 0.085113 | −0.040996 | 0.004966 | −0.041204 | −0.00118 | −0.057191 | 0.037733 | −0.01158 | −0.029664 |
| 282 | −0.030288 | −0.074079 | 0.003256 | 0.0447 | 0.034434 | 0.06114 | 0.042749 | 0.052272 | 0.051857 | 0.023672 | −0.026351 | 0.060797 | 0.012024 | 0.005153 |
| 283 | −0.001239 | −0.091534 | −0.052392 | 0.119722 | −0.052795 | 0.008868 | −0.041049 | 0.031732 | −0.005074 | −0.067394 | −0.011911 | 0.063282 | −0.035515 | 0.017664 |
| 284 | 0.009128 | 0.010173 | 0.090934 | 0.012706 | −0.040045 | −0.029193 | 0.010498 | 0.007315 | −0.006568 | −0.025816 | −0.016902 | −0.028537 | −0.022285 | 0.016481 |
| 285 | 0.00394 | −0.038762 | 0.038437 | −0:06407 | −0.00184 | −0.065419 | 0.053927 | 0.009575 | 0.035334 | −0.019953 | 0.009835 | −0.020917 | −0.032535 | 0.048378 |
| 286 | −0.005747 | −0.028896 | 0.053206 | −0.008964 | 0.013558 | 0.078789 | 0.033444 | 0.086166 | −0.00224 | 0.038008 | −0.020651 | −0.020882 | 0.060645 | 0.046782 |
| 287 | 0.012684 | −0.036403 | 0.002433 | 0.004058 | 0.030319 | 0.085334 | 0.047573 | 0.068633 | 0.028656 | 0.047626 | 0.007604 | −0.017064 | 0.069744 | 0.039603 |
| 288 | 0.048562 | −0.074529 | −0.026584 | 0.084012 | 0.003083 | 0.066493 | −0.025549 | 0.018642 | −0.051588 | 0.003002 | −0.030911 | 0.007381 | 0.015207 | −0.038462 |
| 289 | −0.024967 | −0.004725 | −0.00939 | 0.031788 | 0.047872 | −0.018546 | −0.020278 | −0.062211 | 0.070098 | −0.007298 | −0.039158 | 0.010628 | −0.004298 | −0.010415 |
| 290 | −0.020172 | 0.039428 | 0.001501 | 0.043813 | 0.015868 | 0.07735 | −0.056227 | −0.007454 | 0.057875 | 0.008327 | −0.000886 | 0.024619 | −0.005995 | 0.055433 |
| 291 | −0.018493 | 0.038176 | 0.010637 | 0.028826 | 0.0075 | 0.079145 | −0.064003 | −0.0055 | 0.047536 | 0.019867 | −0.008975 | 0.031809 | −0.002276 | 0.067138 |
| 292 | −0.008739 | 0.045293 | 0.016494 | 0.025048 | −0.000764 | 0.031144 | −0.065169 | 0.001888 | 0.007351 | 0.000993 | −0.019666 | 0.029569 | −0.007341 | 0.053369 |
| 293 | 0.011429 | −0.032462 | −0.014756 | −0.027889 | 0.125935 | 0.035509 | 0.016021 | 0.043957 | −0.05374 | −0.006841 | −0.049889 | −0.035194 | 0.080235 | −0.014015 |
| 294 | 0.051001 | −0.052252 | 0.035566 | −0.032368 | −0.022593 | 0.017266 | −0.077782 | 0.065648 | −0.000205 | 0.05098 | −0.011377 | 0.044782 | 0.017321 | −0.012149 |
| 295 | −0.012575 | −0.016574 | 0.073355 | −0.011663 | 0.04735 | −0.0449 | −0.011489 | −0.015528 | −0.014659 | 0.033693 | −0.056204 | 0.034812 | 0.104862 | 0.025838 |
| 296 | −0.00334 | −0.022399 | −0.002742 | 0.058648 | 0.026108 | 0.032316 | −0.059031 | −0.118559 | −0.012241 | 0.07196 | −0.034188 | 0.130963 | 0.026494 | −0.039749 |
| 297 | −0.001312 | −0.043979 | 0.080509 | 0.017669 | 0.054734 | −0.02454 | −0.050964 | −0.029502 | 0.051691 | −0.021263 | −0.029702 | 0.023673 | 0.038964 | 0.001879 |
| 298 | −0.006352 | 0.011388 | −0.053934 | −0.048822 | −0.133762 | 0.011366 | −0.080344 | 0.006949 | 0.051516 | −0.012846 | 0.015727 | 0.037747 | −0.027648 | −0.006032 |
| 299 | −0.039334 | −0.093995 | −0.058407 | −0.042104 | −0.011335 | −0.041021 | −0.056729 | 0.050839 | 0.01565 | −0.067503 | −0.030034 | 0.096922 | −0.009165 | 0.005349 |
| 300 | −0.115732 | 0.040896 | −0.048696 | −0.050851 | −0.012982 | −0.044876 | 0.022958 | −0.103952 | −0.071433 | −0.037198 | 0.044702 | −0.039796 | 0.120663 | 0.033603 |
| 301 | 0.022485 | −0.027531 | 0.046284 | −0.01915 | 0.025103 | −0.084487 | −0.034657 | −0.006484 | 0.018172 | −0.080835 | −0.064895 | 0.052252 | −0.027513 | 0.029848 |
| 302 | −0.003337 | −0.041024 | 0.042044 | −0.027736 | 0.028998 | −0.038076 | −0.042779 | −0.028062 | −0.004417 | 0.000607 | −0.072312 | 0.095544 | −0.038716 | −0.017147 |
| 303 | 0.006146 | −0.103518 | −0.023133 | −0.033914 | −0.036744 | −0.061564 | −0.05516 | −0.002311 | −0.020773 | −0.127962 | −0.029724 | 0.092591 | −0.063019 | 0.039041 |
| 304 | 0.000924 | −0.044871 | −0.028893 | −0.013492 | −0.025416 | 0.011826 | −0.07388 | −0.006934 | −0.075549 | −0.087686 | −0.069104 | 0.147504 | −0.062815 | 0.008486 |
| 305 | 0.041775 | −0.022462 | −0.07946 | 0.019624 | −0.003375 | −0.028051 | 0.067989 | 0.070368 | −0.078073 | −0.014051 | −0.064904 | −0.048734 | −0.046748 | 0.008991 |
| 306 | −0.027749 | 0.060961 | 0.082921 | −0.041473 | −0.055939 | 0.039332 | 0.089264 | −0.003497 | −0.00434 | −0.025083 | 0.024274 | 0.000467 | −0.031898 | 0.109922 |
| 307 | 0.06006 | −0.07037 | 0.071474 | 0.052608 | 0.059979 | −0.047751 | 0.063118 | −0.106559 | −0.090661 | −0.010326 | 0.021681 | 0.031817 | 0.010317 | 0.001554 |
| 308 | 0.021299 | 0.024183 | −0.054431 | 0.034298 | −0.002875 | 0.007866 | 0.012174 | −0.014268 | 0.008188 | −0.00714 | 0.034967 | −0.012385 | −0.033719 | 0.008431 |
| 309 | −0.018371 | 0.035113 | −0.04885 | 0.031457 | 0.049974 | −0.008111 | −0.033098 | 0.006585 | −0.004399 | −0.007906 | 0.002581 | −0.00371 | 0.042832 | 0.027113 |
| 310 | 0.013893 | 0.030527 | −0.002436 | 0.055064 | 0.079454 | −0.016558 | 0.013351 | 0.051513 | −0.062488 | −0.039125 | 0.006273 | −0.004492 | −0.020643 | 0.054332 |
| 311 | −0.000799 | 0.039988 | 0.052532 | 0.048668 | 0.052008 | −0.004697 | −0.000011 | 0.000891 | 0.053884 | −0.015507 | −0.035024 | −0.051291 | −0.008535 | 0.002983 |
| 312 | 0.198241 | 0.105925 | 0.085393 | 0.036959 | −0.100848 | 0.123124 | 0.093203 | 0.025968 | 0.098375 | −0.193867 | 0.018729 | −0.037606 | −0.019919 | −0.149509 |
| 313 | −0.048363 | 0.067769 | 0.042328 | 0.01207 | −0.003229 | 0.059269 | 0.025611 | 0.015248 | 0.067116 | −0.007026 | −0.012995 | −0.082245 | 0.009524 | 0.066404 |
| 314 | −0.013006 | −0.041993 | 0.058995 | −0.025526 | 0.135024 | 0.093243 | −0.028967 | 0.000945 | −0.006961 | −0.00931 | 0.076359 | 0.04698 | 0.06929 | 0.019372 |
| 315 | −0.03402 | −0.009786 | −0.069983 | 0.012656 | −0.028317 | 0.025684 | −0.010345 | 0.024811 | 0.029339 | −0.013974 | 0.013223 | −0.021408 | 0.035677 | −0.050504 |
| 316 | −0.034473 | 0.030984 | −0.186557 | −0.107616 | −0.143028 | 0.176453 | 0.053407 | −0.033586 | 0.01369 | 0.103396 | 0.119519 | −0.023425 | −0.061456 | 0.00583 |
| 317 | −0.012269 | 0.000954 | 0.040242 | 0.029559 | −0.001936 | −0.033754 | −0.046017 | −0.014797 | 0.04068 | −0.021743 | −0.01407 | 0.002993 | 0.062168 | 0.007378 |
| 318 | −0.041349 | −0.029362 | 0.096497 | −0.081513 | −0.01834 | 0.109459 | −0.060037 | −0.041556 | −0.080876 | −0.02881 | 0.054938 | 0.070295 | 0.03543 | 0.037599 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 319 | −0.008591 | 0.045699 | −0.026886 | 0.000877 | −0.050897 | −0.013771 | −0.035301 | −0.001804 | 0.034139 | −0.021744 | 0.002918 | 0.003251 | 0.051732 | −0.005536 |
| 320 | −0.042724 | 0.128851 | 0.092035 | −0.037467 | −0.13026 | −0.037293 | 0.029647 | −0.053536 | 0.007299 | 0.056361 | −0.003785 | 0.039087 | 0.033283 | 0.054452 |
| 321 | −0.018058 | −0.075704 | 0.047104 | 0.016893 | 0.046572 | −0.036535 | −0.072697 | −0.111163 | 0.051339 | 0.040804 | 0.062047 | −0.012025 | −0.030038 | −0.044384 |
| 322 | −0.050133 | −0.051244 | 0.154371 | 0.040829 | 0.131993 | 0.064729 | 0.104399 | −0.105432 | −0.128942 | −0.079666 | −0.001101 | −0.010434 | 0.018101 | −0.044778 |
| 323 | −0.053613 | 0.013276 | 0.045371 | −0.10963 | −0.010051 | −0.040747 | 0.067531 | 0.110453 | 0.040888 | 0.000061 | 0.017888 | 0.027993 | −0.142056 | −0.010195 |
| 324 | −0.043706 | −0.004318 | −0.106349 | 0.036446 | 0.116358 | 0.019152 | −0.034818 | 0.009301 | 0.095285 | 0.069024 | 0.012445 | 0.000943 | −0.121847 | −0.02994 |
| 325 | −0.010061 | 0.024328 | −0.069228 | 0.063754 | 0.023634 | 0.078818 | −0.091337 | −0.103522 | 0.008443 | 0.017409 | −0.030516 | −0.098415 | 0.019998 | −0.021123 |
| 326 | −0.073913 | 0.020458 | −0.061839 | −0.078031 | 0.043511 | 0.005753 | 0.004037 | −0.040486 | −0.061035 | −0.01663 | −0.05412 | −0.022678 | 0.019224 | 0.028726 |
| 327 | 0.018225 | 0.021394 | −0.042147 | 0.003271 | −0.010849 | −0.013421 | −0.017588 | −0.000887 | −0.048976 | 0.039717 | −0.024595 | −0.012136 | −0.048507 | −0.002434 |
| 328 | 0.000296 | 0.014524 | −0.046681 | 0.156592 | −0.207226 | −0.074615 | 0.129646 | −0.068016 | 0.110651 | 0.121507 | −0.05511 | 0.090013 | 0.009625 | −0.027637 |
| 329 | −0.034288 | 0.018836 | 0.008915 | −0.028453 | −0.026651 | −0.064867 | 0.013716 | 0.039525 | −0.023177 | 0.023249 | −0.013914 | −0.039941 | −0.076605 | −0.048334 |
| 330 | 0.002407 | 0.106695 | 0.00137 | 0.122552 | −0.012914 | 0.127132 | −0.102161 | 0.103743 | 0.108364 | 0.005859 | 0.043031 | −0.084548 | 0.008258 | 0.064251 |
| 331 | −0.010595 | 0.026004 | −0.080944 | −0.007074 | −0.008779 | −0.028117 | 0.00208 | 0.060732 | −0.020302 | 0.033743 | −0.030606 | −0.025783 | −0.028237 | −0.050938 |
| 332 | −0.044324 | 0.008812 | 0.029928 | 0.137163 | 0.046615 | −0.093754 | 0.032067 | 0.160169 | 0.019451 | −0.035998 | −0.10202 | −0.036926 | 0.03293 | 0.039585 |
| 333 | 0.001548 | 0.033517 | −0.029822 | 0.023598 | 0.059294 | 0.005315 | −0.068071 | −0.023257 | 0.026442 | 0.013553 | −0.022049 | −0.018615 | −0.015587 | −0.054999 |
| 334 | 0.077546 | −0.142575 | −0.135804 | −0.037506 | 0.11383 | −0.058304 | 0.081301 | −0.008636 | 0.023382 | −0.040564 | 0.217922 | −0.03232 | 0.013799 | 0.095251 |
| 335 | 0.018843 | 0.042778 | −0.061968 | −0.022667 | −0.012547 | −0.00738 | −0.029759 | 0.023876 | 0.014026 | 0.007675 | −0.051069 | −0.019052 | −0.047432 | 0.005637 |
| 336 | 0.078542 | 0.093358 | 0.071639 | 0.024123 | −0.056001 | 0.027445 | −0.101264 | 0.034576 | −0.11366 | −0.011674 | 0.008757 | 0.007308 | −0.009934 | −0.039693 |
| 337 | 0.042594 | 0.058803 | 0.023968 | −0.037779 | −0.011637 | 0.02112 | 0.047845 | −0.055637 | 0.055713 | −0.075654 | −0.09096 | 0.051021 | 0.049799 | 0.103847 |
| 338 | 0.015096 | 0.049099 | −0.10376 | −0.141731 | 0.113341 | −0.088643 | 0.01953 | 0.118989 | −0.06094 | 0.048577 | 0.034756 | −0.031675 | −0.004234 | −0.072876 |
| 339 | −0.069046 | 0.042375 | −0.032087 | −0.013129 | −0.081677 | −0.000551 | 0.083974 | 0.149855 | −0.062909 | −0.061574 | −0.005581 | −0.177257 | 0.015259 | −0.084626 |
| 340 | −0.073144 | −0.129336 | −0.167682 | 0.007637 | 0.054671 | 0.116036 | 0.046329 | −0.119594 | −0.115875 | 0.053993 | 0.132239 | 0.044976 | 0.127797 | 0.002663 |

| | CD | CE | CF | CG | CH | CI | CJ | CK | CL | CM | CN | CO | CP | CQ |
|---|---|---|---|---|---|---|---|---|---|---|---|---|---|---|
| 1 | −0.030787 | 0.021226 | 0.057227 | 0.026446 | 0.020007 | −0.057597 | −0.027153 | 0.011878 | −0.041059 | 0.036329 | −0.022085 | −0.061568 | −0.005806 | −0.0199 |
| 2 | 0.012896 | 0.015959 | 0.024 | 0.036468 | 0.015331 | −0.036137 | 0.023485 | 0.000253 | 0.01609 | −0.02331 | −0.03007 | 0.096143 | −0.024246 | −0.013844 |
| 3 | −0.030331 | 0.021348 | −0.021968 | 0.026155 | −0.009106 | 0.021233 | 0.019243 | 0.049722 | −0.041833 | 0.026777 | −0.026205 | −0.062479 | −0.015042 | 0.032657 |
| 4 | −0.045346 | −0.042564 | 0.012343 | −0.032466 | 0.033391 | −0.030962 | −0.004663 | 0.034839 | 0.106209 | −0.074882 | 0.032615 | −0.027625 | −0.009487 | 0.001703 |
| 5 | −0.069563 | −0.045737 | 0.004696 | −0.054652 | 0.054622 | −0.067109 | −0.052625 | 0.051895 | −0.012128 | 0.074315 | 0.006433 | −0.038101 | 0.098416 | −0.005415 |
| 6 | −0.075238 | 0.007863 | 0.038 | 0.029845 | 0.07621 | 0.022211 | 0.134965 | 0.020385 | −0.047942 | −0.021612 | −0.080936 | 0.124462 | −0.067208 | 0.028486 |
| 7 | −0.07269 | −0.014602 | −0.029105 | −0.105394 | −0.149205 | 0.027066 | 0.073697 | −0.038393 | −0.114393 | −0.071423 | 0.020854 | −0.055453 | 0.064301 | −0.082297 |
| 8 | 0.004779 | 0.047765 | 0.063567 | 0.029582 | 0.038479 | 0.06678 | −0.033101 | 0.003849 | −0.059681 | 0.05694 | −0.097816 | −0.03829 | −0.141497 | 0.070485 |
| 9 | −0.023533 | −0.035485 | 0.058704 | 0.07716 | −0.003851 | −0.048168 | 0.109659 | 0.032362 | −0.020648 | −0.101493 | −0.104399 | 0.048977 | −0.008495 | −0.135748 |
| 10 | 0.081381 | −0.005153 | 0.059809 | −0.000251 | 0.013802 | 0.065771 | −0.096304 | −0.018517 | 0.02778 | 0.082881 | −0.053125 | 0.008381 | −0.050906 | −0.01854 |
| 11 | −0.101342 | −0.101247 | 0.119068 | −0.06268 | 0.029072 | 0.087396 | −0.093195 | −0.024344 | −0.111722 | 0.052612 | 0.040771 | 0.056946 | 0.05941 | −0.02081 |
| 12 | 0.124041 | 0.096952 | 0.053752 | −0.008002 | 0.025331 | −0.094447 | −0.072163 | 0.029329 | −0.115935 | 0.011921 | −0.046677 | −0.061001 | −0.048191 | −0.088435 |
| 13 | 0.005237 | −0.030521 | 0.030695 | −0.00316 | 0.003576 | 0.065959 | 0.006089 | 0.004807 | −0.053531 | −0.012552 | 0.061418 | 0.012536 | −0.013048 | 0.035666 |
| 14 | 0.026733 | −0.062039 | 0.015224 | 0.004603 | 0.007182 | 0.056481 | −0.045244 | −0.000093 | −0.020427 | −0.008472 | 0.014583 | 0.003574 | −0.041372 | −0.015046 |
| 15 | 0.016772 | 0.014561 | 0.029109 | 0.013685 | −0.036831 | −0.008345 | −0.038253 | −0.04478 | 0.012683 | 0.078029 | 0.001019 | 0.005554 | −0.064779 | −0.046284 |
| 16 | 0.135991 | 0.020003 | −0.032711 | −0.079543 | 0.094671 | −0.004416 | 0.061534 | −0.016177 | 0.062775 | 0.02456 | −0.122673 | 0.100386 | −0.007008 | −0.006259 |
| 17 | −0.058957 | −0.031005 | 0.018434 | −0.033306 | 0.113072 | 0.116441 | −0.100337 | −0.10604 | 0.137814 | −0.048612 | 0.089098 | −0.040499 | −0.007605 | 0.10992 |
| 18 | 0.008516 | 0.047551 | −0.076619 | −0.015571 | 0.045602 | 0.007331 | −0.048237 | 0.05566 | −0.062056 | 0.014503 | 0.063726 | −0.034852 | −0.093713 | −0.065688 |
| 19 | −0.011526 | 0.045757 | −0.134369 | −0.018541 | 0.051424 | 0.043954 | 0.039106 | −0.051513 | 0.067552 | 0.155492 | 0.002106 | 0.050045 | −0.003327 | 0.095993 |
| 20 | 0.004224 | 0.013017 | −0.006215 | 0.037504 | −0.020978 | 0.008016 | 0.010503 | −0.020991 | −0.004006 | 0.005737 | −0.012192 | −0.019629 | −0.012991 | −0.003101 |
| 21 | 0.027447 | 0.001946 | −0.103702 | −0.1142 | 0.041733 | 0.013767 | −0.182123 | −0.126559 | −0.011349 | −0.092076 | 0.099917 | 0.081998 | −0.029646 | −0.028849 |
| 22 | −0.032049 | 0.035591 | 0.075107 | 0.018172 | −0.04991 | −0.17136 | 0.084349 | −0.020524 | 0.149439 | 0.018966 | 0.103519 | 0.003194 | 0.09219 | 0.049149 |
| 23 | 0.041863 | 0.11089 | 0.096708 | 0.036386 | 0.040531 | −0.037876 | −0.007962 | −0.097613 | −0.077892 | 0.133659 | 0.057587 | −0.076176 | 0.02849 | −0.006982 |
| 24 | 0.033099 | −0.120798 | −0.016806 | −0.059851 | −0.077493 | −0.002126 | 0.082751 | 0.058757 | −0.013794 | 0.047845 | 0.095885 | 0.003405 | 0.194541 | −0.03503 |
| 25 | 0.016053 | 0.030536 | −0.008542 | −0.092807 | −0.016627 | −0.112979 | 0.018134 | 0.004411 | 0.06112 | −0.098969 | 0.034576 | 0.019104 | −0.015509 | −0.034722 |
| 26 | 0.001373 | 0.012867 | −0.025708 | 0.02199 | −0.01497 | 0.015335 | −0.001408 | −0.011957 | −0.001726 | −0.01705 | −0.014469 | −0.000898 | −0.007311 | 0.000394 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 27 | −0.001134 | 0.003714 | −0.012344 | 0.018451 | −0.019224 | 0.026211 | −0.016183 | −0.014633 | −0.009104 | 0.006788 | −0.00748 | 0.002906 | −0.020428 | 0.008592 |
| 28 | −0.021916 | −0.020661 | 0.033287 | −0.095122 | 0.039941 | 0.019719 | −0.022454 | 0.049755 | 0.061868 | −0.06533 | −0.002551 | −0.042865 | 0.041594 | 0.003308 |
| 29 | −0.017894 | 0.022352 | −0.031784 | −0.098161 | 0.041623 | 0.068505 | −0.038007 | 0.124216 | 0.00966 | −0.13408 | 0.023408 | −0.056275 | −0.050025 | 0.019017 |
| 30 | 0.074399 | −0.013233 | 0.026198 | −0.010522 | −0.009506 | −0.032196 | −0.041911 | −0.003537 | −0.06607 | 0.048919 | 0.045095 | 0.019366 | −0.018042 | −0.069823 |
| 31 | 0.005927 | −0.032414 | −0.040235 | 0.031167 | 0.033379 | −0.007534 | −0.007811 | −0.044253 | 0.00547 | 0.023533 | 0.011058 | −0.022925 | −0.008866 | −0.033039 |
| 32 | 0.010295 | −0.156829 | 0.043165 | 0.131873 | 0.09532 | −0.141694 | 0.034995 | 0.08334 | 0.033312 | −0.017249 | −0.016469 | −0.039168 | −0.011192 | 0.04484 |
| 33 | −0.000527 | −0.014205 | 0.005737 | 0.032411 | −0.010427 | −0.022493 | −0.065471 | −0.018647 | −0.060117 | 0.031348 | −0.03446 | 0.06034 | 0.023048 | −0.038156 |
| 34 | −0.003892 | 0.026168 | −0.068339 | −0.067288 | 0.038046 | −0.029971 | 0.015192 | −0.021456 | 0.03286 | −0.028067 | −0.086701 | 0.035062 | 0.079341 | −0.018801 |
| 35 | 0.045708 | −0.013028 | 0.03706 | −0.081334 | −0.003623 | −0.064537 | 0.052812 | −0.054922 | −0.081312 | −0.120213 | 0.000811 | 0.041228 | −0.008853 | −0.099157 |
| 36 | 0.019862 | 0.065541 | 0.066875 | −0.025646 | 0.00296 | 0.043968 | −0.002873 | −0.031757 | −0.042032 | −0.033588 | 0.031847 | 0.012611 | 0.067084 | 0.002746 |
| 37 | 0.021333 | −0.03417 | −0.004774 | 0.005865 | 0.008072 | 0.009314 | 0.007637 | −0.023875 | −0.02209 | 0.039323 | −0.038721 | −0.069641 | 0.044073 | −0.012837 |
| 38 | −0.074736 | 0.087323 | 0.074099 | 0.019408 | 0.024195 | −0.086379 | 0.0078 | −0.041398 | 0.009378 | 0.000424 | 0.125113 | −0.007364 | −0.006027 | 0.017661 |
| 39 | 0.092425 | −0.030629 | −0.003695 | 0.064409 | −0.095729 | 0.121972 | 0.10042 | 0.010654 | −0.072041 | −0.0148 | 0.031428 | 0.019224 | −0.038305 | −0.016138 |
| 40 | 0.053758 | 0.018986 | 0.076048 | 0.018051 | −0.022319 | 0.016756 | −0.022075 | −0.014812 | −0.047828 | −0.071064 | −0.069841 | −0.038965 | 0.059401 | −0.007366 |
| 41 | 0.017266 | 0.036554 | −0.009623 | −0.047417 | 0.013663 | 0.040157 | 0.048939 | −0.01962 | −0.046951 | 0.010925 | −0.026468 | 0.001041 | −0.011038 | 0.051785 |
| 42 | 0.041792 | 0.039598 | 0.052771 | −0.066436 | −0.048027 | −0.008085 | 0.017724 | 0.041173 | 0.007052 | −0.028888 | −0.005503 | −0.022364 | 0.003735 | 0.010041 |
| 43 | 0.003187 | 0.01477 | −0.011503 | −0.003328 | 0.005613 | −0.022892 | 0.0033 | −0.018154 | −0.055845 | −0.042684 | −0.061271 | −0.022538 | 0.051469 | 0.038212 |
| 44 | 0.022645 | −0.04132 | 0.043699 | −0.045183 | 0.013242 | 0.048666 | 0.071317 | −0.026653 | −0.020636 | 0.023732 | −0.019365 | 0.053781 | −0.022663 | −0.030809 |
| 45 | −0.023671 | −0.036665 | −0.032881 | −0.021518 | −0.077966 | 0.050756 | −0.028262 | −0.026488 | 0.025392 | 0.100943 | −0.030416 | −0.053834 | 0.056038 | 0.046634 |
| 46 | 0.006569 | −0.056902 | −0.043779 | −0.007875 | −0.069155 | −0.102353 | 0.007186 | 0.054884 | 0.0082171 | 0.007999 | 0.107591 | 0.044048 | −0.204811 | 0.0053 |
| 47 | 0.034005 | 0.062664 | −0.01718 | −0.040822 | 0.000035 | 0.077645 | −0.019275 | −0.085764 | 0.017186 | 0.051773 | −0.047589 | −0.036027 | −0.076186 | 0.053992 |
| 48 | −0.018587 | −0.076539 | −0.069971 | 0.022482 | −0.021767 | −0.005779 | 0.086195 | −0.069882 | −0.080045 | 0.062159 | −0.049029 | 0.045634 | 0.001358 | −0.002172 |
| 49 | 0.049085 | 0.036374 | 0.008218 | −0.022797 | −0.010866 | −0.028809 | −0.053547 | −0.005691 | −0.020272 | 0.069093 | 0.053562 | −0.002924 | −0.042745 | −0.067466 |
| 50 | −0.044694 | −0.051332 | 0.031841 | −0.02914 | −0.069625 | 0.007276 | −0.035966 | 0.026772 | −0.03067 | −0.017356 | 0.003556 | 0.071171 | −0.059427 | 0.000192 |
| 51 | 0.020287 | −0.040743 | 0.025826 | −0.039422 | 0.024928 | −0.0224 | 0.07675 | −0.085406 | 0.026508 | −0.064171 | 0.0749681 | −0.033764 | −0.027817 | −0.01536 |
| 52 | 0.081549 | −0.005397 | −0.056537 | 0.001327 | −0.029224 | −0.018609 | 0.056154 | −0.030499 | −0.021887 | 0.0487891 | −0.047825 | −0.016445 | 0.026334 | −0.068518 |
| 53 | −0.056523 | −0.03777 | −0.047297 | −0.014279 | 0.071415 | 0.029979 | 0.067326 | 0.01082 | −0.018809 | −0.009839 | −0.0118441 | 0.000135 | 0.027564 | −0.014481 |
| 54 | −0.032641 | 0.021831 | 0.001611 | −0.016338 | −0.005955 | 0.079283 | 0.00806 | 0.005977 | 0.046331 | −0.019116 | −0.023782 | 0.060338 | 0.025666 | 0.018956 |
| 55 | −0.078385 | 0.009053 | −0.009242 | −0.039708 | 0.045933 | 0.011884 | 0.022785 | −0.000321 | −0.000174 | 0.004039 | −0.011009 | −0.073194 | 0.022702 | −0.042206 |
| 56 | −0.016692 | 0.011927 | −0.007255 | −0.040669 | −0.02532 | −0.018078 | −0.027062 | −0.016733 | −0.05241 | 0.052891 | 0.0250921 | 0.012202 | −0.048022 | 0.02432 |
| 57 | 0.025018 | −0.016834 | 0.017645 | 0.016317 | 0.02996 | −0.031743 | 0.027654 | −0.018404 | −0.027781 | −0.064208 | −0.007473 | −0.062284 | 0.009685 | 0.01635 |
| 58 | 0.064597 | 0.014357 | −0.021174 | −0.035933 | −0.020544 | 0.041775 | 0.031305 | 0.066923 | 0.101621 | −0.076601 | 0.054644 | 0.01046 | −0.031761 | 0.011744 |
| 59 | −0.005679 | −0.040821 | 0.033273 | −0.07371 | 0.0399 | 0.091036 | −0.069894 | 0.01753 | 0.080449 | 0.024354 | −0.022624 | −0.082449 | −0.12716 | −0.173067 |
| 60 | 0.008839 | 0.068862 | 0.024413 | 0.021912 | −0.042895 | −0.028519 | 0.021505 | 0.021583 | 0.016545 | 0.04639 | 0.01934 | −0.016493 | 0.001455 | −0.000053 |
| 61 | −0.043397 | 0.034336 | 0.043557 | 0.032628 | 0.076151 | 0.046588 | 0.054939 | 0.021293 | 0.025986 | −0.069751 | −0.0109411 | −0.009959 | −0.030516 | −0.091328 |
| 62 | −0.069971 | −0.011422 | −0.092058 | 0.005604 | −0.00296 | −0.015152 | −0.064953 | 0.09026 | −0.032341 | 0.086155 | −0.070624 | 0.049969 | −0.019866 | 0.013101 |
| 63 | −0.066527 | 0.000312 | 0.017864 | −0.042873 | 0.071479 | −0.03901 | −0.060294 | 0.109833 | 0.022197 | −0.010482 | −0.0096651 | 0.061034 | 0.112458 | 0.099195 |
| 64 | 0.086171 | 0.015835 | −0.005406 | −0.059083 | −0.003612 | 0.007401 | −0.047437 | −0.019012 | −0.043061 | 0.032571 | 0.038223 | 0.019298 | −0.050114 | −0.022637 |
| 65 | 0.015063 | 0.004919 | −0.01034 | −0.037573 | 0.0293 | −0.055591 | 0.054288 | −0.00437 | 0.080102 | −0.036401 | −0.044726 | −0.032036 | 0.015425 | 0.004964 |
| 66 | 0.035735 | −0.085728 | −0.071448 | 0.104252 | 0.057131 | −0.018862 | 0.073197 | 0.023027 | −0.064942 | −0.009352 | 0.0516681 | 0.021787 | 0.014272 | −0.037896 |
| 67 | 0.029609 | −0.049783 | −0.098823 | 0.014534 | 0.069764 | −0.06674 | −0.107592 | 0.097953 | 0.072492 | −0.040545 | 0.1092051 | 0.031798 | 0.036357 | 0.029018 |
| 68 | −0.153513 | 0.052797 | −0.064944 | 0.024913 | −0.160348 | −0.059177 | 0.023853 | 0.04513 | −0.021484 | −0.032697 | 0.0100151 | −0.005491 | 0.153189 | 0.076637 |
| 69 | 0.015195 | −0.005246 | 0.011603 | 0.008359 | 0.008444 | −0.047429 | −0.027443 | −0.004033 | −0.011695 | 0.047292 | 0.017931 | −0.050888 | −0.040587 | −0.013357 |
| 70 | −0.003721 | 0.01843 | −0.010646 | −0.006141 | −0.011835 | −0.014215 | 0.054574 | 0.047628 | 0.000709 | −0.009503 | −0.022113 | 0.003815 | 0.008942 | −0.013567 |
| 71 | −0.027639 | 0.075389 | 0.010894 | 0.125165 | 0.043737 | 0.136451 | 0.163065 | −0.080085 | 0.0094171 | −0.008057 | −0.01642 | −0.06027 | −0.03358 | 0.133621 |
| 72 | −0.044927 | 0.000843 | −0.031094 | 0.041206 | 0.073901 | −0.003362 | 0.021295 | −0.002534 | 0.044359 | 0.008244 | 0.043047 | −0.055888 | −0.011637 | −0.034139 |
| 73 | −0.008613 | −0.016419 | 0.021741 | 0.022609 | −0.040823 | −0.044014 | −0.121471 | 0.081426 | −0.054659 | −0.048529 | 0.01227 | 0.057786 | −0.02313 | 0.027666 |
| 74 | −0.015047 | −0.078072 | −0.03609 | 0.070118 | −0.139948 | −0.034305 | 0.033042 | −0.060236 | −0.00287 | 0.013093 | −0.102753 | −0.024003 | 0.000102 | 0.035332 |
| 75 | −0.007531 | 0.009686 | −0.004523 | −0.009005 | 0.008174 | −0.004397 | −0.003616 | 0.015385 | −0.00857 | 0.001623 | 0.001597 | 0.000482 | 0.011124 | 0.012881 |
| 76 | 0.004812 | −0.00245 | −0.029964 | −0.038052 | 0.02484 | −0.000995 | 0.023144 | −0.002435 | −0.016592 | −0.021476 | −0.029405 | 0.000171 | 0.039143 | 0.006361 |
| 77 | −0.013496 | 0.016859 | −0.010543 | −0.013603 | 0.008912 | −0.01824 | 0.004083 | 0.020312 | −0.000317 | 0.014382 | −0.008535 | −0.007251 | 0.014821 | 0.006293 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 78 | −0.013244 | 0.029422 | −0.014648 | −0.006774 | 0.008587 | −0.020192 | 0.005173 | 0.02279 | 0.000345 | 0.009518 | −0.011413 | −0.013848 | 0.020054 | 0.00232 |
| 79 | −0.003348 | 0.053582 | −0.023531 | 0.002572 | 0.0121 | −0.030904 | −0.002981 | 0.013687 | −0.009272 | −0.00885 | −0.012154 | 0.015257 | 0.021806 | −0.006503 |
| 80 | 0.029425 | −0.003569 | 0.054041 | −0.002208 | −0.067415 | 0.094595 | −0.025762 | −0.008981 | 0.0864 | −0.077644 | −0.092485 | −0.024246 | −0.007422 | 0.039498 |
| 81 | 0.020694 | −0.068247 | 0.048511 | −0.02253 | −0.140061 | −0.082513 | −0.103042 | −0.09538 | −0.010026 | −0.001545 | −0.047059 | 0.065819 | 0.025421 | −0.034083 |
| 82 | −0.015386 | 0.002921 | −0.031153 | −0.028101 | −0.021162 | 0.021938 | −0.002553 | −0.004446 | −0.003736 | −0.011427 | −0.007353 | 0.022174 | −0.010668 | −0.012454 |
| 83 | −0.012098 | 0.004287 | −0.017168 | −0.010031 | −0.026001 | 0.02663 | −0.008722 | −0.003404 | −0.001871 | −0.007051 | −0.000043 | 0.007175 | −0.011098 | 0.001301 |
| 84 | −0.005156 | 0.00162 | −0.00343 | −0.002474 | −0.020737 | 0.029637 | −0.013176 | 0.013428 | −0.010563 | −0.003695 | −0.019739 | 0.015764 | −0.039717 | 0.015076 |
| 85 | −0.080126 | −0.023337 | −0.012381 | −0.021298 | 0.058147 | −0.049621 | −0.004229 | −0.06012 | −0.073561 | −0.004705 | 0.054273 | −0.017885 | 0.021798 | −0.124249 |
| 86 | −0.012493 | −0.040827 | 0.007329 | −0.016095 | −0.018183 | 0.015153 | −0.068061 | 0.028119 | −0.016196 | 0.067076 | 0.03462 | −0.038735 | 0.007627 | −0.00284 |
| 87 | 0.022207 | −0.028269 | −0.074876 | −0.007962 | −0.009245 | 0.027827 | −0.001317 | −0.00515 | −0.00281 | 0.027821 | 0.084516 | −0.086882 | 0.011712 | −0.058403 |
| 88 | 0.003409 | 0.009076 | −0.004821 | −0.002169 | −0.01751 | 0.031062 | −0.021476 | −0.003862 | −0.014165 | 0.003581 | 0.001776 | 0.01205 | −0.018844 | 0.009427 |
| 89 | −0.006813 | 0.025892 | −0.020669 | 0.000852 | −0.021041 | 0.016733 | −0.001253 | −0.008602 | 0.001984 | −0.004485 | −0.006987 | −0.000762 | −0.027721 | 0.001557 |
| 90 | −0.011371 | 0.023598 | −0.022844 | −0.007276 | −0.030106 | 0.02136 | −0.007697 | −0.004462 | 0.015689 | −0.00943 | −0.010167 | −0.006314 | −0.02709 | 0.016575 |
| 91 | −0.001382 | 0.013593 | −0.0245 | −0.018931 | −0.026859 | 0.034226 | −0.002527 | 0.003996 | −0.001284 | 0.00553 | −0.044045 | 0.023816 | −0.04704 | 0.004159 |
| 92 | 0.055695 | −0.004345 | 0.005572 | 0.031265 | −0.062472 | −0.029944 | −0.001344 | 0.017048 | 0.00708 | 0.012983 | −0.086071 | 0.043844 | 0.023891 | −0.018341 |
| 93 | −0.00504 | 0.015529 | −0.009847 | −0.012297 | −0.01857 | −0.021151 | 0.000274 | 0.011913 | 0.035409 | −0.021992 | −0.018079 | 0.018167 | −0.029769 | 0.00135 |
| 94 | −0.018652 | 0.008496 | −0.014482 | −0.023617 | 0.013458 | 0.02532 | 0.029323 | −0.014685 | −0.040048 | −0.00677 | −0.022295 | 0.04426 | −0.030674 | 0.019445 |
| 95 | 0.007959 | 0.075664 | 0.018036 | 0.079087 | 0.00226 | −0.009592 | 0.031101 | −0.070948 | −0.092744 | 0.04257 | −0.020272 | 0.075393 | 0.038812 | −0.02862 |
| 96 | −0.187795 | −0.04201 | −0.040747 | 0.046147 | −0.024477 | −0.01437 | 0.033588 | 0.032574 | −0.006635 | −0.015035 | −0.070041 | 0.051245 | 0.045429 | 0.073109 |
| 97 | 0.061584 | −0.086666 | 0.012223 | −0.114769 | 0.001208 | −0.044184 | 0.036379 | −0.059123 | 0.008784 | −0.034243 | 0.02786 | −0.08598 | 0.070077 | −0.025319 |
| 98 | −0.011303 | −0.05605 | −0.055243 | −0.01306 | −0.026072 | 0.049072 | −0.023216 | −0.026859 | 0.00057 | 0.005185 | −0.006407 | 0.032092 | 0.061196 | −0.008562 |
| 99 | −0.030539 | −0.04619 | 0.056158 | −0.009407 | −0.024103 | 0.026025 | 0.026532 | −0.063427 | 0.021421 | −0.015084 | −0.026013 | 0.001718 | −0.053506 | −0.060664 |
| 100 | −0.04187 | 0.015823 | −0.01207 | −0.082816 | −0.007418 | 0.056643 | −0.068141 | −0.038486 | −0.105365 | −0.029264 | 0.019744 | −0.022422 | 0.034606 | 0.005036 |
| 101 | 0.036429 | −0.019849 | 0.039461 | −0.020069 | −0.041272 | 0.038427 | 0.02673 | 0.004998 | 0.033166 | 0.046164 | 0.019325 | 0.025224 | 0.044779 | 0.023475 |
| 102 | 0.01845 | −0.048245 | 0.010938 | −0.045861 | 0.005022 | −0.028701 | −0.036171 | −0.05667 | −0.012082 | −0.062999 | −0.081788 | 0.053682 | −0.023224 | 0.08088 |
| 103 | 0.065346 | −0.058423 | 0.00365 | −0.025115 | 0.034505 | 0.082782 | −0.012151 | −0.026678 | 0.059873 | 0.00191 | −0.065859 | −0.05243 | −0.080744 | −0.016294 |
| 104 | 0.124263 | −0.019296 | −0.019405 | −0.026409 | 0.029031 | −0.047418 | −0.148647 | −0.038179 | 0.010379 | 0.06094 | 0.026086 | 0.051413 | 0.079984 | 0.097066 |
| 105 | −0.027805 | −0.101006 | −0.012971 | 0.0864 | 0.008614 | −0.059408 | 0.017043 | −0.010981 | −0.095022 | 0.042577 | −0.124861 | 0.073983 | −0.099654 | 0.014684 |
| 106 | 0.002267 | 0.03326 | −0.087868 | 0.037712 | 0.012572 | 0.11633 | −0.147756 | −0.001851 | −0.017281 | −0.01094 | −0.091982 | −0.043279 | 0.068405 | −0.04245 |
| 107 | −0.028059 | 0.001321 | 0.18312 | −0.005641 | 0.034897 | −0.00632 | −0.039933 | −0.001846 | −0.018012 | −0.057107 | 0.108133 | −0.04537 | 0.083767 | −0.024574 |
| 108 | 0.029825 | −0.021436 | −0.010834 | −0.000916 | −0.048868 | 0.114737 | −0.056324 | −0.023076 | −0.054429 | −0.051825 | 0.10659 | 0.016075 | 0.02477 | 0.035014 |
| 109 | 0.027432 | −0.174598 | 0.109659 | 0.097753 | −0.039674 | −0.03905 | 0.010625 | −0.027428 | −0.025188 | −0.064823 | −0.002767 | 0.022889 | −0.085137 | −0.043349 |
| 110 | 0.012476 | 0.04863 | −0.002659 | −0.024807 | −0.105053 | 0.078981 | −0.053777 | 0.028722 | 0.010586 | 0.001855 | −0.029892 | −0.10019 | 0.165297 | 0.031981 |
| 111 | −0.000816 | 0.152216 | −0.114544 | −0.044112 | −0.111382 | 0.076602 | −0.059518 | 0.09028 | −0.099675 | 0.020549 | 0.006199 | 0.165684 | −0.030561 | −0.033033 |
| 112 | −0.012017 | −0.068664 | −0.026263 | −0.020144 | 0.208808 | −0.034542 | 0.110888 | −0.009814 | 0.162856 | 0.08967 | 0.093024 | −0.010996 | −0.004138 | 0.065991 |
| 113 | −0.010098 | −0.013623 | −0.122577 | 0.024443 | 0.023194 | −0.074694 | −0.023309 | 0.064613 | 0.013834 | 0.223064 | −0.20008 | 0.16908 | −0.027812 | −0.054385 |
| 114 | −0.116422 | 0.02386 | 0.081107 | 0.102146 | −0.110715 | −0.004178 | −0.004451 | −0.238185 | 0.171853 | −0.106414 | −0.094126 | −0.01676 | 0.075652 | −0.1005 |
| 115 | −0.02811 | −0.073197 | 0.058123 | −0.052356 | 0.029066 | 0.145879 | 0.087614 | 0.125825 | −0.067361 | 0.081184 | 0.004672 | 0.05119 | −0.038991 | −0.020284 |
| 116 | −0.073654 | −0.024397 | 0.068984 | −0.0711 | −0.04509 | 0.045135 | 0.033763 | −0.053728 | 0.065198 | −0.077941 | 0.027746 | 0.130144 | −0.013244 | 0.003998 |
| 117 | −0.004392 | −0.053753 | 0.04313 | 0.017577 | −0.0204 | 0.040121 | −0.00624 | 0.194814 | 0.041134 | −0.10681 | 0.036899 | −0.006291 | 0.016879 | −0.064356 |
| 118 | 0.117937 | −0.10796 | 0.040515 | −0.065195 | −0.039673 | 0.005491 | 0.007015 | 0.020132 | −0.051374 | 0.028107 | 0.069692 | −0.009413 | 0.057251 | −0.017581 |
| 119 | 0.065474 | 0.012725 | −0.037349 | 0.004277 | 0.078078 | 0.036964 | 0.010898 | 0.014817 | 0.001018 | 0.014616 | −0.000663 | −0.067101 | −0.058347 | 0.08346 |
| 120 | 0.006303 | 0.029286 | −0.000126 | 0.098831 | 0.017834 | 0.006752 | −0.041929 | 0.04111 | 0.033463 | −0.038376 | 0.002854 | −0.048734 | 0.002311 | 0.018015 |
| 121 | −0.13557 | −0.028957 | −0.005927 | 0.068535 | −0.012634 | −0.019507 | −0.034508 | 0.058619 | 0.0771 | 0.017756 | 0.038787 | −0.054397 | 0.043866 | −0.097041 |
| 122 | −0.03515 | −0.122192 | 0.014334 | 0.041368 | 0.027991 | 0.025758 | −0.023341 | 0.047052 | −0.030729 | −0.02671 | −0.105938 | 0.046252 | 0.066838 | 0.096301 |
| 123 | −0.007327 | −0.049959 | −0.047212 | 0.002999 | −0.00505 | 0.023421 | −0.009924 | −0.023036 | −0.004114 | −0.039387 | 0.010993 | −0.022146 | 0.023818 | 0.045426 |
| 124 | 0.035351 | 0.012562 | −0.027084 | −0.00069 | 0.006958 | 0.026788 | −0.046287 | −0.007679 | 0.007882 | −0.017303 | 0.028773 | −0.047062 | −0.033444 | 0.060985 |
| 125 | 0.008018 | 0.078605 | −0.000238 | 0.127959 | −0.006725 | 0.064004 | 0.023085 | −0.017776 | 0.017905 | −0.006709 | −0.009577 | −0.011654 | −0.031341 | 0.009171 |
| 126 | 0.022903 | 0.008007 | 0.003622 | −0.028705 | −0.001871 | 0.000385 | −0.026823 | −0.047842 | 0.017856 | 0.069478 | −0.035957 | −0.052726 | −0.041306 | −0.013379 |
| 127 | 0.017202 | −0.013896 | 0.001328 | 0.002447 | −0.010162 | 0.052121 | −0.016159 | −0.001967 | −0.003885 | 0.005047 | −0.018 | −0.045327 | −0.028367 | 0.036916 |
| 128 | 0.016082 | −0.00858 | 0.030953 | −0.058866 | −0.047325 | −0.019637 | 0.10294 | 0.021504 | −0.0479 | 0.005795 | −0.054807 | −0.002076 | 0.049776 | 0.093836 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 129 | −0.000719 | −0.011655 | 0.075489 | 0.094979 | 0.076156 | −0.102743 | 0.042617 | −0.058312 | −0.124896 | −0.04541 | 0.000148 | −0.022979 | −0.076219 | −0.068899 |
| 130 | −0.118016 | 0.071035 | −0.013289 | −0.053008 | 0.005208 | 0.088539 | 0.064658 | −0.126163 | 0.000145 | −0.09038 | −0.04185 | 0.015915 | 0.045825 | 0.099677 |
| 131 | 0.040015 | 0.0509 | −0.031458 | −0.123867 | 0.049263 | −0.071714 | 0.008302 | −0.006504 | −0.121005 | −0.020301 | 0.054763 | −0.011554 | 0.017327 | −0.00263 |
| 132 | −0.021403 | 0.144726 | 0.028971 | 0.036982 | 0.027061 | −0.066568 | −0.102223 | −0.039033 | 0.139079 | −0.080739 | 0.056789 | −0.005994 | −0.067466 | −0.195435 |
| 133 | 0.006639 | −0.003383 | 0.011452 | 0.08274 | 0.061941 | −0.00786 | −0.077936 | 0.002785 | −0.066597 | −0.135102 | 0.006522 | 0.059889 | −0.058668 | 0.157523 |
| 134 | −0.027075 | −0.047317 | 0.077658 | 0.027294 | 0.003962 | 0.02928 | 0.002407 | −0.073822 | 0.094239 | 0.142131 | 0.018449 | 0.068989 | −0.063077 | −0.078968 |
| 135 | 0.018203 | −0.046592 | −0.032676 | 0.018198 | −0.019677 | 0.072009 | 0.015765 | −0.009898 | −0.008655 | −0.011837 | −0.045609 | 0.030153 | 0.017711 | 0.002776 |
| 136 | −0.117536 | 0.024563 | −0.090227 | 0.024417 | 0.077412 | −0.002813 | 0.036954 | 0.018779 | 0.00547 | −0.071679 | −0.041287 | −0.000776 | −0.027066 | −0.128471 |
| 137 | −0.0003 | 0.068095 | −0.106344 | −0.059296 | −0.040757 | 0.033639 | 0.050625 | −0.005063 | −0.031458 | 0.017145 | 0.114556 | 0.092542 | −0.037766 | −0.010923 |
| 138 | 0.062573 | 0.029323 | −0.064043 | 0.010954 | 0.01513 | 0.097939 | 0.053661 | 0.146532 | 0.124211 | −0.010868 | 0.032896 | 0.107566 | 0.057969 | 0.007449 |
| 139 | −0.03931 | 0.119944 | −0.129827 | −0.147018 | 0.072235 | −0.013639 | 0.108247 | 0.122587 | −0.027349 | 0.157892 | −0.034896 | −0.038809 | −0.036776 | 0.049803 |
| 140 | −0.049252 | −0.069392 | −0.028845 | −0.054462 | −0.060391 | −0.002469 | −0.176726 | −0.00479 | 0.087709 | −0.060169 | −0.067731 | 0.037236 | −0.043877 | 0.013315 |
| 141 | −0.083718 | 0.093165 | −0.043503 | 0.082356 | 0.135968 | −0.008487 | 0.012111 | −0.094619 | −0.175914 | 0.112209 | 0.062215 | −0.042783 | 0.031587 | −0.054392 |
| 142 | 0.069076 | 0.021037 | 0.028281 | −0.012115 | −0.088218 | −0.052115 | −0.023601 | −0.084669 | −0.081694 | 0.062368 | −0.047732 | 0.054884 | 0.127866 | −0.001928 |
| 143 | 0.068611 | −0.105684 | 0.054282 | 0.028822 | −0.095713 | −0.003879 | 0.015481 | −0.001021 | −0.014006 | −0.070275 | −0.04082 | −0.040907 | 0.076746 | 0.104044 |
| 144 | −0.003263 | −0.007255 | −0.084874 | 0.043579 | −0.057851 | −0.061235 | 0.093745 | −0.038888 | −0.055006 | −0.029677 | −0.006728 | −0.025696 | 0.02091 | 0.038007 |
| 145 | 0.0599 | −0.097022 | −0.071946 | 0.005021 | −0.086361 | −0.057237 | 0.087158 | −0.089871 | 0.106244 | −0.028528 | −0.078313 | 0.07649 | −0.053004 | −0.025279 |
| 146 | 0.025295 | −0.026254 | −0.033086 | −0.034301 | 0.043471 | 0.040059 | −0.007375 | 0.001631 | −0.052599 | 0.014691 | 0.000105 | 0.076304 | −0.000637 | 0.009594 |
| 147 | −0.028144 | −0.009986 | 0.011253 | −0.012705 | 0.032202 | −0.061484 | 0.023152 | −0.174348 | 0.070362 | 0.082806 | −0.047899 | −0.014061 | 0.060622 | −0.027585 |
| 148 | −0.030744 | 0.046773 | 0.022152 | 0.043468 | 0.028073 | 0.038253 | −0.07775 | 0.093287 | −0.124588 | −0.044388 | −0.05556 | −0.089152 | −0.002446 | 0.005797 |
| 149 | −0.10937 | −0.008406 | 0.13417 | −0.005697 | −0.012928 | 0.059541 | 0.119696 | 0.095401 | −0.028745 | 0.137459 | 0.012673 | 0.037274 | 0.084126 | −0.108588 |
| 150 | 0.166378 | 0.026875 | 0.108925 | 0.085135 | −0.062953 | −0.108398 | 0.074928 | 0.027647 | −0.072774 | −0.022012 | 0.04234 | 0.045754 | 0.028153 | 0.101841 |
| 151 | 0.005413 | 0.023839 | 0.081125 | −0.021748 | −0.02938 | −0.033374 | 0.036792 | 0.084335 | 0.035567 | 0.020804 | 0.038113 | −0.046408 | 0.052827 | 0.020379 |
| 152 | −0.087382 | −0.014041 | −0.030769 | −0.057086 | −0.110593 | −0.002355 | −0.025786 | 0.019153 | 0.027164 | 0.05438 | 0.005405 | 0.028218 | −0.039708 | −0.048334 |
| 153 | −0.022787 | 0.035952 | 0.046822 | −0.051978 | −0.123345 | −0.068276 | 0.030908 | −0.005169 | 0.075033 | 0.064465 | −0.025326 | 0.025154 | 0.053372 | −0.080288 |
| 154 | −0.063117 | 0.036355 | −0.063074 | −0.05495 | −0.085632 | −0.048356 | −0.052506 | −0.016578 | −0.051957 | −0.058974 | −0.037348 | −0.004332 | 0.020153 | −0.04104 |
| 155 | 0.039824 | 0.0402 | −0.041291 | 0.060591 | −0.125177 | 0.102487 | −0.024223 | 0.004308 | −0.06443 | −0.026237 | 0.025602 | −0.036554 | 0.084799 | 0.016877 |
| 156 | 0.019333 | 0.036634 | 0.077057 | −0.069872 | 0.166933 | −0.135684 | −0.109027 | 0.068093 | −0.039939 | −0.16099 | −0.087333 | −0.030346 | −0.097299 | 0.177196 |
| 157 | 0.07169 | −0.021594 | 0.019229 | −0.038378 | 0.050278 | 0.009737 | 0.014995 | −0.055138 | 0.035648 | −0.036451 | −0.046768 | 0.103307 | 0.052614 | 0.059856 |
| 158 | −0.072238 | 0.001681 | −0.048742 | −0.061528 | −0.063773 | −0.01329 | 0.048938 | −0.108754 | −0.143328 | 0.031131 | 0.067294 | −0.162576 | −0.053785 | −0.043185 |
| 159 | 0.151019 | 0.016239 | 0.104433 | −0.1044 | −0.009945 | 0.16035 | −0.009718 | −0.098351 | −0.008955 | −0.082977 | −0.086753 | −0.036731 | 0.027827 | −0.211013 |
| 160 | −0.038664 | 0.010276 | 0.061566 | 0.017355 | −0.114441 | 0.009913 | −0.147027 | 0.045269 | −0.011013 | 0.048807 | −0.004631 | −0.001898 | −0.006721 | 0.053711 |
| 161 | 0.130917 | 0.104257 | −0.162979 | −0.096119 | −0.029004 | −0.056183 | 0.074515 | −0.05015 | 0.11652 | 0.05505 | −0.057053 | −0.209002 | 0.028712 | −0.040395 |
| 162 | −0.102189 | 0.030419 | 0.096933 | −0.079938 | 0.014429 | −0.094053 | 0.049667 | −0.065824 | 0.021701 | 0.09815 | 0.180699 | 0.104473 | −0.133925 | 0.144629 |
| 163 | −0.093106 | 0.003796 | −0.022038 | 0.048301 | 0.036501 | −0.049041 | −0.132718 | 0.048094 | 0.006513 | −0.002443 | 0.018701 | −0.022084 | −0.004221 | −0.018645 |
| 164 | 0.046927 | 0.05867 | 0.094102 | 0.061575 | 0.025838 | 0.115376 | −0.037054 | 0.026733 | 0.088486 | −0.014801 | −0.003337 | 0.107734 | 0.029268 | −0.127991 |
| 165 | −0.000278 | −0.144142 | 0.021288 | −0.023222 | −0.067487 | 0.094365 | −0.083601 | 0.078601 | −0.025364 | −0.022316 | 0.059718 | −0.002141 | −0.009717 | 0.090244 |
| 166 | 0.006354 | −0.015112 | 0.032783 | 0.063335 | 0.025977 | −0.103615 | −0.003835 | 0.108397 | −0.078556 | 0.073984 | 0.06629 | 0.056185 | 0.055264 | −0.032136 |
| 167 | 0.009011 | −0.082709 | −0.100709 | 0.06742 | −0.013583 | −0.012932 | −0.033453 | 0.10341 | 0.082017 | 0.012854 | 0.029323 | −0.022135 | −0.089629 | −0.130084 |
| 168 | 0.02684 | 0.046221 | 0.02176 | −0.083821 | 0.060204 | −0.1447 | −0.005004 | −0.025597 | 0.002239 | −0.037566 | −0.012714 | −0.025739 | −0.009813 | −0.057091 |
| 169 | −0.013098 | 0.001971 | −0.079979 | 0.106557 | 0.044646 | −0.025864 | −0.062425 | −0.008796 | 0.027955 | −0.030628 | 0.026097 | 0.048553 | 0.075022 | −0.03742 |
| 170 | −0.037157 | 0.039506 | −0.044135 | 0.085021 | −0.022615 | −0.007475 | −0.050094 | −0.030576 | 0.020925 | −0.021762 | 0.027967 | 0.04241 | 0.048811 | −0.013065 |
| 171 | −0.02001 | −0.024613 | 0.015411 | 0.064989 | 0.033256 | −0.022703 | −0.022527 | 0.011167 | 0.034771 | 0.018382 | 0.020876 | 0.001501 | 0.048106 | −0.068366 |
| 172 | −0.028399 | 0.006298 | −0.066632 | −0.011682 | 0.027068 | 0.02631 | −0.034795 | −0.053866 | 0.017539 | −0.00723 | 0.009866 | −0.005869 | 0.017868 | −0.042276 |
| 173 | −0.014057 | −0.0152 | 0.011235 | −0.020122 | −0.021444 | 0.034898 | 0.01241 | 0.017916 | 0.002403 | 0.068252 | 0.048637 | 0.02313 | −0.015373 | −0.002495 |
| 174 | 0.012924 | −0.03457 | 0.048249 | 0.025303 | 0.004249 | −0.006268 | 0.017326 | 0.023669 | 0.000494 | 0.07375 | −0.012752 | −0.036258 | 0.138769 | −0.053682 |
| 175 | 0.102498 | −0.024206 | 0.066451 | −0.049382 | −0.081 | 0.009246 | 0.160794 | 0.146188 | 0.014957 | −0.09116 | 0.059074 | −0.034762 | 0.020396 | 0.040102 |
| 176 | −0.014039 | 0.031073 | −0.028581 | −0.031643 | 0.083665 | 0.043852 | −0.051105 | −0.02261 | 0.121711 | −0.048041 | 0.085641 | −0.012513 | 0.044198 | −0.009659 |
| 177 | −0.046353 | −0.104203 | 0.074621 | −0.132515 | 0.038973 | −0.045771 | −0.092284 | −0.011332 | −0.085752 | −0.002153 | −0.09467 | −0.031893 | −0.140226 | −0.040829 |
| 178 | 0.004827 | 0.031165 | −0.059949 | −0.020403 | −0.052985 | −0.068005 | −0.019346 | 0.023362 | 0.007584 | 0.018716 | −0.002748 | −0.050118 | 0.083644 | 0.019793 |
| 179 | 0.062965 | −0.034019 | 0.02405 | −0.017413 | 0.005879 | −0.042861 | −0.011156 | 0.029472 | 0.001592 | 0.00837 | 0.000457 | −0.007549 | 0.007216 | −0.026541 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 180 | 0.01303 | 0.015196 | −0.005913 | 0.029023 | −0.021383 | −0.023298 | −0.000259 | −0.002066 | 0.003266 | 0.036802 | −0.000292 | 0.029218 | −0.013294 | 0.010325 |
| 181 | 0.026428 | −0.012008 | 0.026076 | −0.001088 | −0.026012 | −0.027565 | 0.003615 | 0.026937 | 0.023562 | 0.011564 | −0.003022 | 0.024252 | −0.007653 | −0.001665 |
| 182 | 0.050247 | 0.035227 | 0.023669 | −0.032549 | −0.024013 | −0.017044 | 0.020374 | −0.018179 | −0.075047 | −0.019431 | 0.044673 | 0.012478 | 0.010518 | 0.022427 |
| 183 | 0.050905 | −0.030865 | 0.10021 | −0.016349 | 0.011623 | −0.032363 | 0.031973 | 0.000282 | −0.031517 | 0.019381 | −0.02004 | −0.029352 | −0.000239 | −0.096548 |
| 184 | −0.035449 | 0.000709 | 0.068939 | −0.034064 | −0.025654 | −0.00646 | −0.067184 | 0.035272 | 0.13249 | 0.132003 | 0.002617 | −0.058002 | 0.001427 | −0.065948 |
| 185 | −0.130069 | 0.140274 | 0.049352 | 0.04256 | −0.076553 | −0.065947 | 0.040542 | 0.131843 | −0.03344 | −0.045197 | −0.100759 | 0.008211 | −0.089692 | 0.045408 |
| 186 | −0.059686 | −0.059369 | −0.030375 | 0.085837 | 0.012588 | 0.08664 | 0.084114 | −0.083184 | −0.069023 | −0.058444 | −0.048463 | 0.038675 | −0.03704 | −0.058206 |
| 187 | 0.023916 | −0.022802 | −0.07182 | 0.021936 | 0.060136 | 0.019312 | −0.009424 | −0.049297 | 0.019313 | 0.067246 | 0.040099 | −0.005646 | −0.036276 | 0.044159 |
| 188 | −0.015761 | −0.018056 | −0.01359 | 0.032631 | 0.060877 | 0.01378 | −0.052913 | −0.023125 | 0.012778 | 0.030006 | −0.031306 | −0.026775 | 0.044543 | 0.024311 |
| 189 | 0.008937 | 0.053606 | −0.022508 | −0.059402 | 0.033986 | 0.107906 | −0.004887 | 0.038745 | 0.046632 | −0.019024 | −0.057756 | −0.024544 | 0.089096 | −0.01292 |
| 190 | 0.032657 | 0.013305 | 0.000691 | 0.047761 | 0.036514 | 0.026835 | 0.078004 | −0.008801 | 0.044206 | 0.041805 | 0.030779 | 0.002719 | 0.009914 | −0.045983 |
| 191 | 0.026708 | 0.009293 | 0.01191 | 0.045697 | 0.069683 | 0.02509 | 0.048537 | −0.016717 | 0.020493 | 0.005312 | −0.072178 | −0.031691 | −0.048406 | −0.04451 |
| 192 | 0.00083 | −0.060924 | 0.003305 | −0.063969 | 0.050386 | 0.029261 | 0.04347 | −0.026753 | −0.091172 | 0.056885 | 0.027133 | 0.02264 | 0.1594 | 0.054657 |
| 193 | −0.015456 | 0.020515 | −0.044677 | 0.053543 | −0.02107 | −0.005346 | −0.020321 | −0.028001 | −0.068224 | −0.048811 | 0.091494 | 0.078477 | −0.028899 | 0.032997 |
| 194 | 0.045688 | −0.053413 | 0.042116 | −0.027921 | −0.004204 | −0.061688 | −0.021305 | 0.013903 | 0.078238 | 0.012182 | 0.029883 | −0.017499 | −0.080348 | −0.088925 |
| 195 | 0.035557 | −0.045133 | 0.015113 | −0.05835 | 0.008353 | 0.068307 | 0.070659 | −0.086083 | −0.023726 | −0.074178 | 0.095601 | 0.086515 | −0.073605 | −0.03627 |
| 196 | 0.002402 | −0.046607 | 0.012813 | −0.001452 | −0.003606 | 0.03627 | 0.06731 | −0.01562 | 0.00883 | −0.065838 | 0.084241 | 0.031592 | −0.073202 | −0.041004 |
| 197 | −0.044907 | 0.003855 | 0.001558 | 0.021352 | 0.010788 | 0.105899 | 0.074522 | −0.046671 | −0.038285 | −0.027915 | 0.054255 | 0.059079 | 0.019085 | 0.021409 |
| 198 | 0.050472 | 0.040171 | −0.118498 | −0.160996 | −0.094211 | −0.072962 | −0.060433 | −0.000807 | 0.09342 | −0.011099 | −0.088615 | 0.008046 | −0.022528 | 0.093938 |
| 199 | 0.047347 | 0.07933 | 0.106946 | 0.048528 | 0.064388 | 0.127827 | −0.079874 | 0.02473 | 0.028234 | 0.030427 | 0.060118 | 0.099239 | 0.046002 | −0.019044 |
| 200 | −0.046002 | 0.028962 | −0.043475 | −0.058537 | 0.13832 | −0.126039 | 0.023274 | 0.083913 | 0.078517 | 0.006628 | −0.008935 | −0.024095 | 0.012565 | −0.08021 |
| 201 | 0.00488 | 0.078535 | 0.04097 | 0.004426 | 0.005989 | −0.013632 | 0.002727 | 0.052544 | 0.017381 | −0.040262 | 0.042086 | 0.168355 | −0.012565 | 0.047562 |
| 202 | −0.087887 | −0.037286 | −0.064029 | −0.008351 | −0.040905 | −0.054223 | −0.024225 | 0.055033 | 0.003295 | 0.052022 | −0.043174 | 0.123255 | 0.030054 | 0.068212 |
| 203 | 0.084652 | 0.061725 | 0.006245 | 0:027243 | −0.111505 | −0.000943 | −0.073454 | −0.041425 | 0.019647 | 0.059692 | 0.020433 | 0.003465 | 0.077764 | −0.008332 |
| 204 | −0.000814 | −0.110543 | −0.010529 | −0.042941 | −0.162417 | −0.084785 | −0.141642 | 0.030354 | −0.071141 | −0.016442 | 0.067713 | −0.049063 | −0.051024 | −0.005782 |
| 205 | 0.114561 | −0.007199 | −0.125195 | 0.074295 | −0.000821 | −0.005619 | 0.052512 | 0.083927 | 0.04042 | 0.05563 | −0.007148 | 0.0495481 | 0.074678 | −0.071242 |
| 206 | −0.055953 | −0.049927 | −0.050577 | −0.071465 | 0.032324 | 0.000609 | −0.091732 | −0.077659 | −0.053222 | 0.003407 | 0.031506 | −0.083931 | 0.020145 | 0.023789 |
| 207 | 0.041221 | 0.051157 | 0.036645 | −0.005216 | 0.091137 | 0.016607 | 0.022194 | −0.073639 | 0.104975 | −0.123979 | −0.049005 | 0.04636 | 0.015373 | 0.02161 |
| 208 | −0.007145 | 0.003931 | 0.092639 | −0.156865 | −0.128931 | 0.116493 | 0.095183 | 0.12589 | 0.085419 | 0.119054 | 0.033542 | 0.00924 | −0.199243 | −0.033317 |
| 209 | −0.06066 | −0.095532 | −0.068818 | 0.013108 | −0.079886 | 0.066939 | −0.022543 | −0.021572 | −0.03875 | −0.109414 | 0.01363 | −0.062387 | −0.023899 | −0.015988 |
| 210 | −0.080071 | −0.04591 | −0.041102 | 0.047998 | 0.029718 | −0.094567 | 0.126908 | 0.040579 | −0.054061 | −0.00473 | 0.205577 | −0.000688 | −0.011486 | 0.078288 |
| 211 | −0.106935 | −0.042253 | 0.205577 | −0.051247 | −0.016559 | −0.062247 | 0.083347 | 0.032 | 0.019646 | 0.092999 | −0.169387 | −0.026826 | −0.03451 | 0.04817 |
| 212 | −0.050132 | −0.043167 | −0.01214 | −0.072095 | −0.045652 | 0.011676 | 0.097976 | −0.08122 | −0.045645 | 0.040206 | 0.139056 | 0.031789 | −0.063903 | 0.091884 |
| 213 | 0.028213 | 0.106213 | 0.082599 | −0.05924 | −0.022439 | −0.00578 | 0.004351 | 0.026839 | −0.057705 | 0.019401 | −0.083851 | −0.010991 | −0.05045 | 0.012406 |
| 214 | −0.014419 | −0.024462 | 0.02261 | −0.022203 | 0.033681 | 0.00212 | −0.033008 | 0.044683 | 0.002317 | 0.001557 | −0.014326 | 0.01553 | 0.043402 | −0.032265 |
| 215 | 0.063904 | −0.00927 | 0.008924 | 0.097712 | −0.028259 | −0.050904 | 0.002416 | 0.111258 | 0.001755 | −0.034386 | 0.010522 | −0.047826 | −0.15693 | 0.023202 |
| 216 | 0.068178 | 0.063794 | −0.070068 | 0.01003 | −0.034417 | −0.007742 | 0.072648 | −0.032893 | 0.006288 | −0.04541 | 0.004149 | −0.045521 | −0.072467 | 0.01573 |
| 217 | 0.122876 | −0.007672 | −0.0001 | 0.130364 | 0.037219 | −0.075588 | −0.009869 | 0.024336 | −0.090941 | −0.035306 | −0.068126 | −0.114154 | 0.004719 | −0.030776 |
| 218 | −0.025517 | 0.013004 | −0.016008 | −0.015365 | −0.05704 | 0.051323 | 0.001379 | −0.000115 | 0.013253 | −0.064773 | 0.007827 | 0.076792 | −0.047393 | −0.024501 |
| 219 | −0.02266 | 0.027503 | −0.027328 | −0.03623 | −0.014387 | −0.010999 | 0.01691 | 0.021697 | 0.002702 | −0.065972 | −0.028033 | 0.005811 | 0.02596 | −0.064174 |
| 220 | 0.054841 | 0.045553 | −0.016566 | 0.02382 | 0.026049 | 0.011003 | −0.062879 | 0.057388 | −0.054973 | −0.009175 | −0.020528 | −0.03702 | 0.002396 | −0.00523 |
| 221 | −0.05575 | 0.036841 | 0.080182 | −0.024775 | −0.015488 | −0.038252 | 0.003964 | −0.02282 | 0.045973 | −0.005225 | −0.075503 | 0.059837 | −0.076096 | 0.012895 |
| 222 | −0.042775 | −0.069676 | 0.065892 | −0.067003 | 0.038785 | 0.095235 | 0.001374 | 0.00007 | −0.022162 | −0.011564 | −0.071018 | −0.029881 | −0.031583 | 0.020564 |
| 223 | 0.016092 | −0.036669 | 0.06636 | −0.006446 | −0.00629 | 0.002 | −0.016941 | 0.009385 | 0.004669 | −0.059386 | −0.040379 | 0.00081 | −0.077099 | −0.047342 |
| 224 | 0.016426 | 0.030518 | −0.003934 | 0.011316 | −0.05567 | 0.093584 | 0.055939 | −0.010928 | 0.042679 | 0.040272 | 0.076178 | −0.042931 | −0.020785 | −0.008041 |
| 225 | −0.004658 | −0.032302 | 0.012334 | 0.015675 | −0.082935 | 0.095882 | 0.050258 | −0.011026 | 0.037295 | 0.051341 | 0.052735 | −0.050329 | −0.017717 | 0.020872 |
| 226 | −0.044644 | 0.031257 | −0.050486 | 0.02465 | −0.008783 | −0.016622 | −0.001925 | 0.062262 | −0.010175 | 0.00132 | −0.045894 | 0.028481 | −0.011662 | 0.044963 |
| 227 | 0.063902 | 0.032071 | 0.02124 | 0.052569 | −0.065941 | 0.021703 | −0.010846 | 0.059811 | −0.025698 | 0.042376 | 0.112344 | 0.026651 | 0.025076 | −0.085519 |
| 228 | −0.08845 | 0.062338 | 0.094738 | 0.045437 | −0.046214 | −0.066042 | 0.00818 | 0.0205 | −0.014955 | 0.046351 | 0.044097 | 0.139225 | 0.142613 | −0.018355 |
| 229 | −0.020938 | −0.065 | 0.055039 | 0.0322 | −0.081498 | −0.01869 | −0.038983 | −0.012199 | 0.049064 | 0.004358 | 0.122063 | −0.10976 | −0.093027 | 0.044054 |
| 230 | 0.03338 | −0.020512 | −0.016886 | 0.011489 | 0.013379 | 0.01163 | 0.030991 | −0.048146 | −0.008758 | 0.001271 | −0.013638 | −0.010809 | −0.020171 | 0.044578 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 231 | −0.03239 | −0.06536 | 0.052668 | −0.00189 | 0.051997 | 0.019383 | −0.023056 | −0.08301 | 0.036291 | 0.108413 | 0.030947 | 0.072708 | 0.00692 | −0.070791 |
| 232 | −0.050281 | −0.038813 | 0.09226 | 0.038284 | 0.057157 | 0.026006 | −0.004306 | −0.015996 | −0.099661 | −0.091085 | 0.078917 | 0.047327 | 0.147163 | −0.065891 |
| 233 | 0.007453 | 0.028929 | −0.076178 | −0.033724 | 0.03962 | −0.017069 | −0.047497 | −0.065518 | −0.036237 | 0.040901 | 0.012152 | 0.029665 | −0.048718 | −0.031282 |
| 234 | 0.028267 | 0.061548 | 0.024741 | 0.027992 | −0.036565 | −0.0792 | −0.030198 | −0.025027 | −0.006273 | 0.035138 | 0.047771 | 0.002412 | 0.017229 | 0.078861 |
| 235 | 0.000718 | 0.009872 | 0.09071 | −0.0849 | 0.0135 | −0.01768 | −0.074921 | −0.006218 | 0.045002 | 0.05869 | 0.005591 | −0.010933 | 0.039815 | −0.01123 |
| 236 | −0.048746 | −0.009769 | 0.046445 | 0.049419 | −0.074775 | 0.012555 | −0.021679 | −0.061508 | 0.002352 | −0.005917 | −0.0171 | −0.082181 | −0.003782 | 0.025286 |
| 237 | −0.00218 | −0.080909 | −0.03249 | −0.040222 | 0.009784 | −0.004604 | 0.001006 | 0.03833 | 0.014179 | −0.062773 | 0.026343 | 0.048583 | −0.018775 | −0.018539 |
| 238 | 0.011944 | −0.062834 | 0.00762 | −0.056049 | 0.039323 | −0.012018 | 0.017563 | 0.0243 | 0.032354 | −0.017334 | 0.009792 | 0.030801 | −0.000837 | 0.014471 |
| 239 | 0.011192 | −0.048942 | −0.024799 | −0.060506 | 0.02643 | −0.028038 | 0.00361 | 0.019247 | −0.015326 | 0.001927 | −0.001229 | 0.018692 | 0.042605 | 0.006299 |
| 240 | 0.028206 | −0.003872 | −0.078556 | 0.046021 | −0.040615 | −0.07029 | −0.009299 | −0.002887 | 0.039065 | 0.071916 | 0.003846 | 0.032285 | −0.015297 | −0.047328 |
| 241 | 0.049695 | −0.073439 | −0.049204 | −0.017969 | 0.012891 | −0.028107 | −0.009633 | 0.008719 | 0.026326 | −0.018823 | 0.018054 | 0.051023 | 0.00549 | −0.046182 |
| 242 | −0.010437 | 0.015085 | −0.023081 | −0.040126 | 0.040354 | 0.059393 | 0.012014 | −0.00832 | −0.002974 | 0.013425 | −0.050488 | −0.090227 | −0.038706 | 0.05924 |
| 243 | 0.085159 | −0.03127 | −0.056522 | −0.056045 | 0.011071 | −0.06356 | 0.039633 | 0.001462 | −0.083398 | −0.056925 | −0.027752 | −0.056236 | −0.017879 | −0.008147 |
| 244 | −0.0066 | 0.004681 | 0.01479 | 0:017886 | 0.000619 | 0.002186 | −0.014656 | −0.054332 | −0.005973 | 0.000283 | −0.010613 | −0.021453 | 0.031646 | 0.022243 |
| 245 | −0.020874 | −0.015384 | 0.065128 | 0.031531 | −0.01887 | −0.008298 | −0.050431 | 0.031906 | 0.015868 | 0.04221 | 0.025736 | 0.017042 | 0.091845 | −0.026414 |
| 246 | −0.036239 | 0.072651 | −0.012263 | −0.011787 | 0.025668 | 0.017789 | −0.018609 | 0.058949 | 0.017281 | 0.035715 | 0.041788 | −0.015661 | 0.008943 | 0.021134 |
| 247 | −0.016763 | −0.055968 | −0.009848 | −0.002793 | 0.022602 | −0.010828 | 0.006159 | −0.027025 | 0.014361 | 0.054933 | −0.035418 | −0.034 | 0.016558 | −0.010711 |
| 248 | −0.014416 | −0.031321 | 0.063745 | −0.02895 | −0.046824 | 0.007322 | −0.062016 | 0.027569 | 0.004836 | −0.016004 | −0.023099 | −0.01213 | 0.00847 | −0.006699 |
| 249 | −0.049059 | 0.00518 | 0.018922 | 0.023569 | 0.027431 | 0.085483 | −0.001861 | −0.066674 | 0.054759 | −0.011864 | −0.067385 | 0.058035 | 0.030933 | 0.044501 |
| 250 | 0.068501 | 0.022869 | −0.036367 | 0.06121 | −0.082293 | −0.031861 | 0.054069 | −0.000991 | 0.006376 | −0.063113 | 0.08339 | −0.033722 | −0.046524 | −0.04273 |
| 251 | −0.003126 | −0.09987 | −0.058001 | −0.029522 | −0.060955 | −0.022328 | 0.035608 | 0.093721 | 0.047059 | 0.008925 | 0.021611 | −0.020689 | 0.029329 | 0.008839 |
| 252 | −0.001539 | −0.062434 | −0.015915 | −0.069532 | 0.098526 | 0.010301 | 0.035176 | −0.045531 | −0.029117 | −0.020568 | −0.027545 | −0.06912 | 0.021256 | 0.01695 |
| 253 | 0.088926 | −0.019287 | −0.104137 | 0.11581 | 0.01107 | 0.00939 | 0.030939 | 0.045067 | 0.027275 | −0.019124 | 0.007587 | 0.053249 | 0.007392 | 0.03104 |
| 254 | 0.008268 | 0.055569 | 0.070426 | 0.077627 | −0.029403 | 0.057139 | −0.007539 | −0.033403 | 0.106091 | −0.047305 | −0.014136 | 0.025317 | 0.003549 | −0.019799 |
| 255 | −0.003258 | 0.082011 | −0.009446 | −0.019018 | −0.004176 | −0.007638 | 0.01121 | −0.031473 | 0.06896 | 0.010292 | 0.021881 | −0.006167 | 0.017359 | 0.009588 |
| 256 | −0.000933 | 0.037026 | 0.030076 | 0.006074 | −0.008714 | 0.017047 | −0.054028 | −0.081723 | −0.011889 | 0.080432 | 0.055892 | 0.07062 | −0.030787 | 0.032683 |
| 257 | 0.016026 | 0.031286 | 0.004538 | −0.052105 | −0.015418 | 0.050974 | 0.070231 | −0.015867 | −0.033843 | −0.040677 | 0.024375 | −0.053024 | −0.001464 | 0.032193 |
| 258 | −0.0438 | −0.050778 | 0.025033 | −0.012985 | −0.03084 | −0.003922 | 0.038009 | −0.04916 | 0.029687 | 0.022778 | 0.000317 | −0.03698 | 0.033996 | −0.032684 |
| 259 | −0.028156 | −0.046872 | −0.068631 | 0.011522 | −0.038879 | 0.06744 | 0.045482 | −0.001718 | 0.016255 | 0.0047 | −0.056041 | −0.059153 | 0.022967 | 0.025919 |
| 260 | 0.005893 | 0.035042 | −0.043391 | 0.04769 | 0.004332 | 0.009124 | 0.007786 | −0.020357 | −0.002761 | 0.061516 | 0.000015 | −0.083067 | −0.013801 | 0.035049 |
| 261 | −0.031136 | −0.018513 | −0.018308 | 0.082165 | 0.015681 | 0.019726 | 0.09219 | −0.032603 | 0.032838 | 0.01408 | −0.003241 | 0.017201 | 0.002648 | 0.003348 |
| 262 | −0.017944 | 0.000872 | 0.019212 | 0.029535 | −0.012952 | 0.008652 | 0.001228 | −0.034395 | −0.002295 | 0.041935 | −0.090749 | −0.041572 | 0.005817 | 0.039687 |
| 263 | 0.013264 | −0.015754 | 0.024298 | −0.021957 | −0.000312 | 0.003067 | −0.013995 | −0.048168 | −0.011445 | 0.00784 | −0.075753 | −0.022811 | −0.00411 | 0.050621 |
| 264 | −0.064935 | −0.052004 | −0.061967 | −0.016826 | 0.065508 | 0.005415 | −0.025724 | −0.026934 | 0.005899 | 0.043781 | −0.010622 | 0.034104 | −0.04563 | −0.012781 |
| 265 | −0.000889 | 0.039958 | −0.023924 | 0.049793 | 0.02849 | −0.051375 | −0.026238 | −0.050763 | −0.050801 | −0.036175 | 0.045101 | 0.035838 | −0.016224 | −0.00773 |
| 266 | 0.059786 | 0.06722 | 0.040716 | 0.023918 | −0.043362 | 0.004508 | −0.005602 | −0.068693 | 0.00926 | −0.032389 | 0.029065 | 0.107788 | −0.004065 | 0.005924 |
| 267 | 0.002541 | 0.017152 | −0.04149 | 0.087238 | 0.008616 | 0.083261 | −0.024603 | 0.017848 | 0.052068 | 0.128977 | 0.031575 | −0.060908 | −0.158675 | 0.021526 |
| 268 | 0.022412 | 0.012112 | −0.029456 | 0.014841 | 0.008712 | 0.028961 | 0.013869 | −0.011013 | 0.000738 | 0.003611 | −0.02105 | 0.020991 | 0.008806 | 0.010299 |
| 269 | 0.047809 | −0.01105 | 0.003976 | 0.01944 | 0.010401 | 0.023432 | −0.021915 | 0.062891 | −0.027097 | −0.005155 | −0.054238 | 0.022156 | −0.006829 | 0.01272 |
| 270 | 0.034508 | 0.051521 | −0.023515 | 0.035391 | −0.050235 | 0.029545 | −0.030474 | 0.081828 | −0.028944 | −0.031462 | 0.012108 | 0.014593 | 0.028554 | −0.006845 |
| 271 | −0.080252 | −0.00544 | 0.020486 | −0.126029 | 0.12529 | 0.065156 | 0.022045 | 0.14194 | −0.030512 | −0.051314 | −0.032159 | 0.219365 | 0.030286 | −0.133349 |
| 272 | −0.067759 | −0.083788 | 0.002696 | −0.003607 | −0.047539 | −0.034264 | −0.019989 | 0.000346 | 0.055118 | −0.004549 | 0.008822 | −0.008251 | −0.046554 | 0.010596 |
| 273 | −0.01048 | −0.05115 | 0.007739 | 0.026338 | 0.032125 | 0.002934 | 0.023748 | −0.005013 | −0.029351 | −0.020049 | −0.011339 | −0.031172 | 0.059746 | −0.011902 |
| 274 | 0.00554 | −0.043094 | 0.012487 | 0.032968 | 0.042483 | 0.005213 | 0.01519 | 0.011517 | −0.031424 | −0.020758 | −0.002446 | −0.025595 | 0.048435 | −0.00779 |
| 275 | 0.049472 | 0.029959 | −0.030729 | 0.025875 | 0.002289 | −0.015965 | −0.040233 | 0.044795 | 0.010277 | −0.044965 | 0.023174 | −0.011292 | −0.003209 | −0.001642 |
| 276 | −0.060977 | −0.056093 | 0.045234 | 0.070757 | −0.090038 | −0.008688 | 0.013028 | −0.061823 | 0.059193 | −0.000584 | −0.023923 | −0.108893 | −0.00725 | 0.032924 |
| 277 | −0.008114 | −0.025551 | 0.033375 | −0.021054 | −0.027291 | −0.052611 | −0.018752 | −0.054151 | −0.050596 | 0.02993 | 0.027029 | −0.020094 | −0.022143 | −0.00391 |
| 278 | 0.051428 | 0.021927 | 0.040802 | 0.000094 | −0.049686 | −0.014447 | −0.009283 | 0.038429 | −0.086179 | 0.065495 | 0.059867 | −0.001623 | 0.009572 | −0.054097 |
| 279 | 0.019473 | 0.013377 | −0.029309 | −0.066127 | 0.010249 | −0.05443 | 0.003178 | 0.0366 | −0.016694 | 0.009808 | 0.018184 | 0.041681 | 0.003685 | −0.01171 |
| 280 | 0.067342 | −0.077893 | −0.116144 | 0.012421 | 0.061003 | 0.004421 | 0.052197 | −0.088262 | −0.053466 | −0.065309 | 0.037379 | 0.054864 | −0.041593 | −0.03693 |
| 281 | −0.107821 | 0.076547 | 0.034214 | −0.003468 | −0.006316 | −0.035514 | −0.007939 | −0.067302 | 0.057918 | 0.047444 | −0.001185 | −0.009178 | −0.011074 | 0.022938 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 282 | −0.009747 | 0.076225 | 0.003823 | 0.007024 | 0.027242 | −0.016752 | 0.055868 | −0.022303 | −0.009107 | 0.042857 | 0.023462 | −0.04464 | 0.044374 | −0.017682 |
| 283 | −0.043464 | 0.000548 | −0.034588 | 0.013114 | −0.047546 | −0.075753 | −0.046677 | −0.014352 | 0.004354 | 0.051142 | −0.069594 | 0.03654 | −0.009121 | −0.034616 |
| 284 | −0.025811 | 0.02897 | 0.006151 | −0.02097 | −0.013159 | 0.005357 | 0.028742 | −0.021222 | −0.03026 | −0.001954 | −0.003679 | 0.01134 | −0.034891 | 0.014827 |
| 285 | 0.00233 | 0.06009 | −0.009105 | 0.008576 | −0.001563 | 0.017282 | 0.066361 | 0.005396 | −0.037962 | −0.030095 | 0.01329 | −0.046252 | 0.010912 | 0.022299 |
| 286 | −0.011051 | −0.080327 | 0.004441 | −0.065465 | −0.009056 | −0.0609 | 0.063128 | −0.053917 | 0.029207 | −0.007026 | −0.019447 | 0.034306 | −0.031291 | −0.012458 |
| 287 | 0.012087 | −0.044579 | −0.019787 | −0.043015 | −0.013667 | −0.030044 | 0.073465 | −0.021716 | 0.02209 | −0.01477 | −0.009979 | 0.001631 | 0.000206 | 0.009042 |
| 288 | −0.048635 | 0.044284 | −0.047375 | −0.056529 | −0.09242 | −0.025117 | −0.043868 | 0.044713 | 0.089025 | 0.065411 | 0.0244371 | 0.075038 | 0.044603 | −0.068589 |
| 289 | 0.036285 | 0.088611 | −0.015558 | −0.027545 | −0.032906 | 0.051718 | −0.037992 | −0.02421 | −0.011165 | 0.033887 | 0.015851 | −0.004562 | 0.023928 | 0.050364 |
| 290 | −0.010644 | 0.040833 | −0.021856 | 0.064149 | 0.009675 | 0.024673 | −0.000727 | 0.026045 | −0.001138 | −0.042087 | 0.041013 | −0.000651 | 0.02644 | −0.061197 |
| 291 | −0.02138 | 0.018914 | −0.016934 | 0.052559 | 0.002707 | 0.019679 | 0.006779 | 0.025313 | −0.001814 | −0.043109 | 0.053118 | 0.002612 | 0.01135 | −0.055788 |
| 292 | −0.012102 | 0.009547 | −0.034904 | 0.041443 | 0.042951 | −0.016408 | −0.021819 | 0.055078 | 0.052659 | −0.076721 | −0.000236 | −0.006187 | −0.006653 | −0.028448 |
| 293 | −0.037849 | 0.001765 | −0.108752 | −0.037044 | −0.139776 | −0.105087 | 0.073236 | −0.078716 | −0.001953 | −0.043025 | 0.0253 | 0.065643 | −0.086275 | −0.083035 |
| 294 | −0.071188 | −0.001313 | −0.107787 | 0.03065 | 0.080216 | 0.026843 | −0.083515 | −0.044484 | 0.024649 | −0.035487 | 0.006975 | 0.044059 | 0.006504 | −0.058644 |
| 295 | 0.007688 | −0.001184 | −0.068757 | 0.023636 | 0.038209 | 0.043595 | −0.002389 | −0.004915 | −0.010878 | 0.008916 | −0.028531 | 0.021904 | 0.009954 | −0.054193 |
| 296 | 0.045306 | −0.052943 | −0.03042 | 0.082924 | 0.088763 | 0.027001 | −0.076395 | 0.001508 | −0.06022 | 0.005496 | 0.028285 | 0.016614 | 0.037408 | 0.004964 |
| 297 | 0.011656 | −0.053661 | −0.057094 | −0.016647 | −0.003044 | 0.027621 | −0.022256 | −0.017079 | −0.005578 | 0.043118 | −0.041231 | 0.033465 | 0.013417 | −0.018168 |
| 298 | −0.040662 | 0.093935 | 0.059296 | 0.043 | 0.011409 | 0.000692 | −0.045739 | 0.009454 | −0.108452 | −0.002761 | −0.033238 | −0.069035 | 0.004493 | −0.037081 |
| 299 | −0.006223 | −0.086387 | −0.04068 | 0.016308 | −0.051548 | 0.01948 | 0.007148 | −0.004746 | −0.026387 | −0.028377 | −0.01336 | 0.037586 | 0.074205 | −0.022945 |
| 300 | −0.134037 | 0.129526 | −0.02714 | 0.133293 | −0.020583 | 0.003735 | −0.003435 | 0.009067 | 0.002494 | −0.038663 | −0.074758 | −0.106312 | 0.03441 | −0.074008 |
| 301 | −0.006038 | 0.060303 | −0.038015 | −0.021819 | −0.051287 | 0.002452 | 0.025722 | 0.029315 | −0.02371 | −0.032821 | 0.009482 | −0.025467 | 0.051004 | −0.021628 |
| 302 | −0.02681 | 0.057551 | −0.052343 | −0.067984 | −0.040503 | 0.02447 | 0.030766 | 0.080368 | −0.016514 | −0.01442 | 0.064199 | −0.08834 | 0.032504 | −0.019544 |
| 303 | 0.031181 | −0.03874 | −0.025522 | 0.08713 | −0.051436 | −0.02422 | 0.045792 | 0.058379 | −0.00306 | −0.027414 | −0.06868 | −0.055269 | 0.026442 | −0.027425 |
| 304 | 0.007859 | −0.089908 | −0.011821 | 0.073462 | −0.049342 | −0.010809 | 0.065649 | 0.092305 | 0.066834 | −0.040901 | −0.038217 | −0.022317 | 0.058849 | −0.002832 |
| 305 | −0.028814 | 0.177585 | −0.02863 | −0.009329 | −0.12955 | −0.126537 | 0.03814 | −0.067627 | −0.017892 | −0.207543 | −0.049291 | 0.122161 | −0.05906 | −0.00093 |
| 306 | −0.020219 | −0.068751 | 0.023827 | 0.058662 | −0.028282 | 0.054804 | −0.011425 | −0.082068 | −0.01531 | −0.004972 | 0.040223 | 0.034748 | −0.012669 | −0.04342 |
| 307 | 0.017212 | 0.150934 | 0.079501 | 0.078895 | −0.003007 | 0.002926 | −0.086489 | 0.005494 | 0.096358 | −0.032119 | 0.074418 | 0.078628 | −0.010913 | 0.091742 |
| 308 | −0.027862 | −0.082729 | 0.015419 | −0.029553 | 0.037848 | 0.00397 | 0.012923 | −0.014532 | −0.025698 | 0.009397 | 0.015355 | 0.054437 | 0.035767 | 0.039784 |
| 309 | −0.011745 | 0.008019 | 0.060439 | −0.057041 | 0.021245 | 0.010734 | 0.008554 | 0.029523 | −0.001702 | 0.031781 | −0.028869 | −0.017615 | −0.025568 | 0.005855 |
| 310 | 0.035848 | 0.027036 | 0.094426 | 0.022795 | 0.067794 | 0.042002 | −0.084616 | −0.063001 | −0.101281 | 0.024727 | 0.06895 | 0.005072 | −0.087384 | 0.010017 |
| 311 | 0.086109 | 0.05547 | −0.056846 | −0.009386 | −0.025367 | −0.019522 | 0.007687 | −0.024379 | 0.020206 | −0.025786 | −0.015581 | −0.030847 | −0.014609 | 0.026435 |
| 312 | 0.123128 | −0.053627 | −0.043715 | −0.087674 | 0.093439 | −0.028996 | −0.041124 | 0.025688 | −0.032255 | 0.000772 | −0.20915 | −0.012615 | 0.103551 | 0.045041 |
| 313 | 0.02772 | −0.025631 | 0.024664 | 0.008985 | 0.003901 | −0.022831 | −0.024321 | −0.018509 | −0.00363 | −0.017169 | −0.001244 | −0.027131 | −0.013075 | 0.084705 |
| 314 | 0.014494 | −0.074871 | −0.035984 | 0.054551 | 0.035012 | −0.057976 | −0.048997 | −0.094828 | 0.036843 | −0.03074 | −0.00366 | 0.150276 | 0.03751 | −0.053094 |
| 315 | 0.031659 | −0.003065 | 0.076026 | 0.020584 | 0.013118 | −0.05278 | −0.033782 | 0.051158 | −0.022567 | 0.003787 | 0.01583 | 0.025067 | 0.030046 | 0.046218 |
| 316 | 0.029307 | −0.116009 | −0.028067 | 0.133322 | −0.114315 | 0.025379 | −0.078778 | 0.061046 | 0.025079 | 0.005071 | −0.041408 | 0.030106 | −0.104361 | 0.036013 |
| 317 | 0.015875 | 0.09025 | 0.05869 | −0.000644 | 0.026873 | −0.040907 | 0.022293 | −0.020333 | −0.021932 | 0.015088 | 0.002455 | 0.006102 | −0.021623 | −0.047166 |
| 318 | −0.062782 | −0.022322 | 0.074375 | −0.017846 | 0.080944 | −0.050071 | 0.035837 | 0.006194 | 0.070991 | −0.031911 | −0.106772 | −0.046176 | 0.014915 | −0.036787 |
| 319 | 0.010245 | 0.010793 | 0.075306 | 0.015072 | 0.02136 | −0.064524 | 0.011268 | 0.024672 | −0.004756 | 0.025522 | −0.003822 | −0.008908 | −0.013734 | 0.036448 |
| 320 | 0.010799 | −0.054882 | −0.058643 | −0.071203 | 0.082523 | −0.111774 | −0.042407 | −0.037678 | −0.042638 | −0.056662 | 0.065921 | −0.028481 | 0.019437 | −0.054558 |
| 321 | 0.002576 | −0.078366 | 0.049435 | 0.030903 | 0.019276 | 0.026639 | 0.027292 | 0.020476 | 0.027286 | 0.092244 | 0.018284 | −0.018284 | −0.006838 | −0.022955 |
| 322 | −0.050251 | 0.059497 | 0.000255 | −0.088259 | 0.064539 | −0.092421 | 0.101227 | 0.064274 | 0.055498 | −0.062531 | 0.049492 | −0.046104 | 0.009242 | −0.050323 |
| 323 | 0.103177 | −0.015702 | 0.04273 | 0.067955 | 0.079916 | 0.077336 | −0.044086 | 0.058092 | 0.076797 | −0.021164 | 0.067684 | −0.016351 | 0.036314 | 0.091809 |
| 324 | −0.166275 | 0.046158 | 0.010477 | −0.088467 | 0.025558 | 0.028931 | 0.091898 | 0.052667 | −0.118798 | −0.042831 | −0.032461 | −0.022446 | −0.091661 | −0.04759 |
| 325 | −0.067093 | 0.071897 | 0.025136 | 0.072568 | 0.030885 | 0.016307 | 0.023336 | 0.036688 | 0.026593 | −0.010894 | −0.034689 | −0.005382 | 0.025456 | −0.02269 |
| 326 | 0.032936 | −0.02409 | −0.057294 | −0.031371 | −0.053794 | 0.021839 | −0.037655 | −0.14621 | 0.036777 | 0.069907 | 0.033648 | 0.010043 | 0.041168 | −0.068469 |
| 327 | 0.008752 | −0.019073 | 0.080123 | −0.051259 | 0.023091 | 0.01667 | 0.012934 | 0.025977 | 0.00866 | 0.021085 | −0.012075 | −0.014532 | 0.019797 | −0.027701 |
| 328 | −0.044966 | −0.072459 | 0.017983 | −0.014732 | 0.024175 | 0.001027 | 0.041158 | −0.067739 | −0.043741 | 0.033936 | 0.00936 | 0.081775 | 0.040326 | 0.166556 |
| 329 | −0.020507 | −0.069188 | 0.064715 | −0.109041 | −0.075274 | 0.006054 | −0.015827 | 0.062174 | 0.036033 | 0.002604 | 0.00461 | −0.081084 | 0.073307 | 0.033866 |
| 330 | −0.059587 | −0.068828 | −0.072621 | −0.040123 | 0.023986 | −0.011163 | −0.045694 | 0.037226 | −0.02877 | −0.035505 | 0.108991 | −0.099007 | 0.03022 | −0.094553 |
| 331 | 0.071329 | 0.024441 | 0.006984 | 0.009359 | −0.010179 | 0.002881 | −0.021806 | 0.036907 | 0.018016 | −0.014342 | 0.010342 | −0.016233 | −0.014312 | −0.009666 |
| 332 | 0.09551 | 0.045513 | −0.07431 | −0.011957 | −0.013788 | 0.065054 | 0.066036 | 0.000004 | −0.074904 | 0.07067 | −0.028939 | 0.097541 | −0.041386 | 0.039698 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 333 | −0.015548 | 0.126379 | 0.04978 | 0.017609 | −0.022526 | 0.079741 | 0.02534 | 0.060226 | 0.026157 | 0.027785 | 0.015244 | −0.042959 | −0.015967 | 0.029521 |
| 334 | −0.255719 | −0.002833 | −0.127272 | −0.044988 | −0.027102 | 0.063688 | −0.104833 | −0.017006 | 0.016314 | −0.092258 | 0.032525 | −0.051699 | 0.014614 | 0.116402 |
| 335 | 0.063263 | 0.018704 | 0.005173 | 0.021952 | −0.004026 | 0.003322 | 0.006214 | 0.004234 | 0.060693 | 0.010836 | 0.03323 | 0.037168 | −0.008632 | −0.000376 |
| 336 | −0.055269 | −0.056011 | −0.012673 | 0.075819 | −0.028841 | −0.111022 | −0.082303 | −0.037209 | 0.050978 | 0.107641 | −0.034793 | −0.021925 | −0.077088 | 0.043556 |
| 337 | −0.038135 | −0.000683 | 0.020321 | 0.089606 | 0.01816 | −0.112198 | −0.031713 | −0.01865 | −0.034546 | 0.064173 | 0.017365 | −0.047682 | −0.004054 | 0.054732 |
| 338 | 0.076241 | 0.079746 | 0.03647 | −0.065012 | 0.071491 | −0.07603 | 0.028774 | −0.087821 | 0.033264 | 0.02816 | 0.013348 | 0.064007 | −0.135503 | 0.040435 |
| 339 | 0.016619 | −0.085787 | −0.064269 | 0.140285 | 0.07832 | −0.002828 | 0.090522 | −0.038724 | 0.117683 | −0.025115 | 0.088505 | −0.080696 | 0.002236 | 0.061885 |
| 340 | 0.092038 | 0.01205 | 0.090237 | −0.108494 | −0.052312 | −0.084074 | 0.001538 | −0.050454 | 0.127896 | −0.052928 | 0.024473 | 0.009591 | −0.003687 | 0.123708 |

| | CR | CS | CT | CU | CV | CW | CX | CY | CZ | DA | DB | DC | DD | DE |
|---|---|---|---|---|---|---|---|---|---|---|---|---|---|---|
| 1 | −0.058705 | 0.002912 | −0.010599 | 0.024311 | −0.061477 | −0.038691 | 0.013496 | −0.033351 | −0.016599 | 0.032375 | −0.056014 | 0.008826 | −0.02636 | 0.035219 |
| 2 | 0.008078 | −0.029672 | −0.024798 | 0.025512 | 0.03558 | −0.001054 | 0.041845 | 0.021657 | 0.029592 | −0.041596 | −0.016534 | −0.011978 | −0.05979 | 0.049222 |
| 3 | −0.030661 | 0.008178 | 0.034968 | −0.000242 | −0.022347 | −0.020377 | 0.054138 | −0.014918 | 0.010128 | 0.060331 | 0.012926 | 0.033722 | 0.06146 | 0.002855 |
| 4 | −0.041805 | −0.027859 | −0.016789 | 0.038174 | −0.092709 | 0.042122 | −0.080697 | 0.022488 | 0.042487 | 0.055478 | −0.004112 | −0.010448 | −0.048942 | −0.047675 |
| 5 | 0.015967 | −0.00097 | −0.005319 | −0.063768 | −0.02613 | 0.035454 | 0.107275 | 0.010086 | −0.130606 | −0.000524 | 0.02204 | 0.003841 | −0.051472 | −0.040015 |
| 6 | 0.137162 | 0.034696 | −0.027957 | −0.003513 | −0.120444 | 0.02671 | −0.028384 | 0.086533 | −0.035064 | −0.031324 | −0.006743 | −0.075411 | 0.051966 | 0.069429 |
| 7 | −0.083011 | 0.068919 | 0.090509 | 0.132134 | 0.035424 | 0.012213 | 0.006688 | −0.053155 | −0.084418 | −0.036856 | 0.11992 | 0.040783 | −0.055662 | 0.095552 |
| 8 | −0.049769 | 0.153903 | −0.012194 | −0.098547 | −0.063739 | −0.082964 | 0.155759 | −0.029035 | −0.034867 | 0.090695 | 0.041452 | −0.023252 | 0.093351 | −0.080721 |
| 9 | 0.001125 | −0.050145 | −0.033439 | 0.015955 | 0.014884 | 0.027442 | −0.035325 | −0.04544 | 0.066366 | 0.027011 | −0.097699 | −0.143653 | 0.075593 | 0.134553 |
| 10 | −0.011551 | −0.072543 | −0.021889 | 0.011458 | 0.115445 | −0.020615 | −0.036127 | −0.061262 | 0.051971 | 01 09813 | 0.046694 | 0.01542Y | 0.027802 | −0.062142 |
| 11 | 0.104051 | −0.008825 | −0.080827 | −0.088472 | −0.062967 | −0.01893 | −0.076542 | 0.014661 | 0.03333 | 0.000176 | 0.003576 | −0.003164 | 0.076104 | −0.018322 |
| 12 | 0.012685 | −0.106061 | −0.013033 | −0.042001 | −0.048943 | 0.09129 | −0.036506 | 0.000192 | 0.095835 | 0.072905 | 0.072388 | 0.066405 | 0.087828 | 0.03391 |
| 13 | −0.004126 | −0.010036 | −0.025597 | 0.024535 | −0.081844 | 0.008495 | 0.076911 | 0.017378 | −0.01804 | −0.032694 | −0.096657 | 0.078423 | −0.075732 | −0.024608 |
| 14 | −0.052411 | −0.006792 | −0.03999 | −0.001245 | −0.074881 | 0.016981 | 0.00051 | 0.013575 | −0.019719 | 0.036891 | −0.050746 | 0.055926 | −0.03806 | 0.077836 |
| 15 | 0.032465 | 0.064674 | −0.011255 | 0.090825 | −0.038459 | −0.059938 | 0.062943 | 0.032312 | −0.001704 | −0.013305 | −0.025225 | 0.023711 | −0.027547 | 0.013852 |
| 16 | −0.050191 | −0.051509 | 0.127572 | 0.051381 | −0.013267 | −0.112526 | 0.032893 | 0.098717 | −0.009089 | −0.098763 | −0.071886 | 0.000796 | 0.010159 | −0.110006 |
| 17 | 0.065182 | 0.078491 | −0.004894 | −0.019488 | 0.051723 | −0.020941 | −0.028907 | 0.07572 | 0.051136 | −0.052906 | −0.024134 | 0.046755 | 0.022337 | 0.22337 |
| 18 | 0.014469 | −0.016927 | −0.144284 | 0.100658 | 0.052672 | 0.181942 | −0.019665 | −0.015338 | −0.113615 | 0.09347 | 0.044386 | −0.006877 | −0.006437 | −0.033119 |
| 19 | −0.010132 | −0.01036 | −0.008165 | 0.037853 | −0.053164 | −0.142213 | −0.021254 | 0.097128 | 0.007682 | 0.097904 | 0.039109 | 0.015849 | 0.003935 | −0.074852 |
| 20 | 0.014298 | 0.008079 | 0.000243 | 0.006267 | −0.028583 | 0.030137 | −0.015599 | −0.027547 | −0.026101 | 0.001149 | −0.011269 | 0.007492 | −0.034538 | −0.012162 |
| 21 | 0.031365 | −0.011781 | 0.023858 | −0.04532 | 0.126875 | 0.007252 | −0.130564 | 0.025325 | 0.041633 | −0.053159 | 0.022828 | −0.056407 | −0.020465 | −0.125747 |
| 22 | 0.107813 | −0.075779 | 0.120907 | −0.061945 | −0.048448 | 0.044471 | 0.054057 | 0.116173 | 0.045657 | 0.084736 | −0.065697 | −0.047497 | −0.034766 | 0.002554 |
| 23 | 0.005824 | −0.069097 | 0.093659 | −0.021503 | −0.114765 | −0.007969 | 0.072042 | −0.081934 | −0.087035 | −0.124697 | 0.0649 | −0.119394 | 0.013748 | 0.115165 |
| 24 | −0.023076 | 0.013401 | 0.045419 | −0.057742 | −0.10722 | 0.037164 | −0.080309 | −0.103165 | −0.032724 | −0.003534 | −0.056082 | 0.070543 | −0.098865 | −0.059056 |
| 25 | 0.021832 | −0.004854 | −0.045319 | 0.02521 | −0.013894 | 0.02293 | −0.118226 | 0.095048 | −0.079845 | −0.067452 | −0.061461 | 0.060169 | 0.002477 | 0.08757 |
| 26 | 0.009056 | −0.008637 | −0.016333 | 0.01504 | −0.010793 | 0.026995 | −0.005663 | −0.01767 | −0.037129 | 0.006595 | −0.019146 | −0.004491 | −0.030548 | −0.007602 |
| 27 | −0.0041 | 0.00346 | −0.005634 | 0.004945 | −0.001314 | −0.005611 | −0.005483 | −0.021776 | −0.008631 | −0.00472 | 0.002007 | −0.004763 | 0.02025 | −0.01152 |
| 28 | −0.009027 | 0.010855 | −0.015812 | 0.083782 | 0.005391 | −0.03246 | −0.0514 | −0.001303 | 0.089905 | 0.011365 | 0.032202 | 0.023094 | −0.049939 | 0.061785 |
| 29 | 0.100333 | 0.088317 | −0.110504 | 0.003831 | 0.076162 | 0.184505 | 0.057937 | −0.085358 | 0.045499 | −0.012687 | −0.091024 | −0.085405 | −0.049314 | −0.035746 |
| 30 | 0.037919 | −0.054413 | −0.014621 | −0.00828 | −0.018871 | −0.030217 | −0.038196 | 0.043639 | −0.005712 | −0.014157 | −0.05498 | −0.021631 | −0.020377 | 0.001025 |
| 31 | 0.015398 | 0.013563 | 0.010756 | 0.022537 | 0.021949 | 0.002368 | 0.0325 | 0.014203 | −0.020668 | 0.035884 | −0.027318 | 0.012689 | −0.015077 | −0.021958 |
| 32 | −0.075796 | −0.182489 | −0.088161 | −0.055227 | −0.042812 | −0.057513 | −0.058325 | 0.080994 | 0.038505 | 0.165579 | 0.016282 | 0.169351 | 0.010663 | 0.062082 |
| 33 | 0.056239 | 0.025199 | −0.029912 | 0.084672 | −0.004794 | 0.052 | −0.034477 | 0.03723 | −0.000953 | 0.007214 | 0.056911 | −0.010366 | −0.039739 | 0.008469 |
| 34 | 0.089674 | 0.046245 | −0.004876 | 0.02547 | −0.026563 | 0.022154 | 0.062646 | −0.016129 | 0.068353 | −0.063522 | −0.013394 | −0.000067 | 0.007532 | −0.045861 |
| 35 | 0.048172 | 0.02972 | 0.018962 | −0.128977 | 0.142173 | 0.022696 | 0.07733 | 0.08634 | −0.048402 | 0.017301 | 0.163574 | 0.064833 | −0.005824 | 0.070185 |
| 36 | −0.012758 | −0.045731 | 0.01298 | −0.131146 | 0.00367 | 0.057802 | −0.025779 | 0.013961 | −0.086572 | −0.031502 | −0.003916 | −0.062089 | −0.082608 | 0.031919 |
| 37 | 0.025561 | −0.027681 | 0.007443 | −0.062715 | 0.009578 | 0.014367 | −0.051982 | −0.039693 | −0.095119 | −0.002928 | −0.023605 | 0.003159 | −0.139073 | −0.015645 |
| 38 | 0.039343 | −0.057261 | −0.079999 | −0.068136 | −0.007416 | 0.001607 | 0.141746 | −0.0989 | 0.016158 | −0.109203 | 0.049288 | −0.133255 | 0.02714 | 0.027716 |
| 39 | −0.144612 | 0.073642 | −0.048414 | 0:005463 | −0.011021 | −0.050977 | −0.062265 | 0.040011 | 0.029519 | −0.098183 | −0.043177 | 0.015142 | 0.040703 | −0.21129 |
| 40 | 0.006695 | 0.081079 | −0.069571 | 0.00578 | 0.043874 | −0.018587 | −0.015156 | −0.008352 | −0.04651 | 0.020346 | 0.062956 | −0.014579 | −0.063801 | 0.014665 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 41 | −0.043362 | 0.036491 | 0.000917 | −0.044767 | 0.060406 | 0.016155 | −0.015064 | 0.015003 | 0.073778 | 0.013915 | 0.029797 | −0.012144 | 0.051538 | −0.024715 |
| 42 | −0.072416 | −0.014282 | −0.026566 | 0.027038 | −0.032882 | −0.020365 | 0.022021 | −0.026378 | −0.029962 | 0.020053 | 0.015008 | 0.032106 | −0.027398 | −0.093429 |
| 43 | −0.006367 | 0.033806 | 0.012763 | −0.044056 | −0.013406 | 0.013533 | 0.037216 | 0.006494 | 0.017846 | −0.013933 | 0.012802 | −0.032552 | 0.00079 | 0.000156 |
| 44 | 0.018738 | 0.030792 | 0.070918 | 0.009922 | 0.002266 | 0.057288 | 0.045277 | −0.041882 | 0.020018 | 0.107412 | −0.094027 | −0.029325 | −0.024009 | 0.026963 |
| 45 | −0.011557 | −0.014603 | 0.05257 | −0.052725 | −0.031045 | 0.029324 | 0.035918 | −0.015713 | 0.035661 | −0.043112 | −0.009031 | −0.063068 | 0.009965 | 0.044844 |
| 46 | 0.013505 | −0.063814 | −0.076417 | 0.012676 | −0.059515 | −0.110183 | 0.039851 | −0.107966 | 0.169492 | −0.001919 | 0.067358 | 0.008858 | −0.000374 | 0.067772 |
| 47 | 0.032684 | −0.06102 | 0.028202 | 0.021882 | 0.025034 | 0.05299 | −0.017474 | 0.007248 | 0.076309 | −0.033354 | −0.086056 | −0.033032 | −0.092294 | 0.036528 |
| 48 | −0.00977 | 0.036373 | 0.037458 | −0.079639 | 0.049474 | 0.037917 | −0.019548 | 0.038519 | 0.012341 | −0.00414 | 0.122414 | −0.007892 | 0.004441 | −0.043024 |
| 49 | 0.037319 | −0.04495 | −0.003001 | 0.052399 | −0.012776 | −0.027633 | 0.003387 | 0.034577 | 0.013503 | 0.032013 | −0.005385 | 0.006788 | 0.013895 | −0.008496 |
| 50 | 0.043553 | 0.019586 | 0.052647 | −0.0666 | 0.027215 | −0.041647 | −0.003082 | −0.094868 | 0.01944 | 0.066625 | −0.037092 | 0.07995 | 0.047677 | −0.003441 |
| 51 | −0.010549 | −0.07213 | −0.037913 | −0.047537 | −0.02846 | 0.025052 | 0.018406 | 0.10882 | −0.002538 | −0.009535 | 0.057375 | 0.065049 | −0.010214 | 0.045817 |
| 52 | −0.001076 | −0.076544 | −0.016022 | 0.032323 | −0.037486 | 0.043768 | −0.061087 | 0.072367 | −0.028463 | −0.01135 | 0.013735 | 0.048245 | 0.043608 | 0.051758 |
| 53 | 0.037568 | 0.033261 | 0.028854 | −0.03593 | −0.006785 | −0.018659 | −0.036704 | −0.024692 | 0.006438 | 0.02183 | −0.016008 | −0.03908 | 0.00179 | 0.025067 |
| 54 | 0.028744 | 0.00222 | −0.036083 | −0.019596 | −0.034178 | 0.028496 | −0.009488 | −0.019324 | 0.009582 | 0.031929 | 0.020969 | −0.015293 | 0.008942 | 0.086805 |
| 55 | −0.025396 | 0.033073 | −0.060028 | 0.069553 | 0.035869 | 0.038738 | 0.126771 | −0.033034 | 0.01632 | −0.034849 | 0.013085 | 0.038396 | 0.029496 | −0.047933 |
| 56 | 0.031118 | −0.012403 | 0.009826 | −0.071764 | 0.002927 | −0.068157 | 0.013329 | 0.092012 | −0.035454 | 0.043513 | 0.021786 | 0.036626 | −0.007703 | −0.034433 |
| 57 | 0.012739 | 0.014144 | −0.043512 | 0.012962 | −0.053715 | −0.056381 | 0.047378 | 0.048844 | −0.041047 | −0.080934 | −0.028659 | −0.052545 | 0.036457 | −0.037496 |
| 58 | −0.054355 | −0.046478 | 0.037493 | −0.088369 | 0.020903 | 0.012117 | −0.029982 | 0.023789 | −0.035438 | 0.0515 | 0.053825 | −0.015742 | −0.013635 | −0.000625 |
| 59 | −0.06739 | −0.076399 | 0.12146 | −0.041432 | 0.02576 | −0.017084 | −0.108365 | −0.070257 | 0.118918 | 0.048943 | −0.024779 | −0.044148 | −0.050242 | 0.169724 |
| 60 | −0.001489 | 0.00912 | −0.014396 | 0.009945 | −0.027378 | 0.075858 | 0.018708 | −0.038097 | −0.005812 | 0.028595 | 0.011281 | −0.037424 | −0.012395 | −0.012486 |
| 61 | 0.049317 | −0.008761 | −0.020066 | −0.027729 | 0.077794 | 0.011443 | 0.04412 | −0.043067 | −0.066204 | −0.054717 | 0.008849 | −0.01274 | −0.024521 | −0.045624 |
| 62 | −0.023729 | 0.035772 | 0.01453 | 0.020501 | 0.03011 | −0.071591 | 0.030231 | −0.001906 | 0.006182 | 0.028081 | 0.000269 | −0.028279 | 0.029949 | 0.049203 |
| 63 | 0.056661 | −0.082995 | 0.043152 | 0.06782 | 0.024036 | 0.013361 | 0.011288 | 0.004516 | −0.029841 | −0.120052 | 0.004197 | 0.057333 | 0.078285 | 0.027345 |
| 64 | 0.020414 | −0.049634 | 0.056854 | −0.006106 | −0.008033 | −0.04219 | −0.050214 | 0.125677 | −0.011306 | −0.067392 | −0.039485 | 0.039406 | −0.006013 | −0.017231 |
| 65 | 0.024861 | 0.052808 | −0.063417 | 0.029757 | 0.023238 | 0.032121 | 0.030088 | 0.095627 | 0.008758 | −0.033305 | 0.038813 | −0.102069 | 0.067844 | −0.053856 |
| 66 | 0.091045 | −0.004701 | 0.03106 | 0.045663 | −0.028181 | 0.022562 | 0.033312 | −0.044146 | −0.113322 | 0.102351 | 0.070002 | 0.040336 | −0.00961 | −0.006007 |
| 67 | −0.046162 | −0.044818 | −0.092278 | 0.02321 | 0.032217 | 0.004376 | −0.023584 | −0.039525 | −0.152497 | −0.01578 | 0.043913 | −0.014084 | 0.025657 | 0.0068 |
| 68 | −0.017642 | −0.04734 | −0.018804 | −0.078952 | −0.065013 | 0.092561 | 0.004683 | −0.028025 | 0.00605 | −0.068613 | −0.010779 | 0.055384 | 0.045793 | −0.067646 |
| 69 | 0.035438 | 0.018312 | 0.019966 | 0.020753 | 0.012918 | −0.036032 | −0.017868 | 0.008697 | 0.090968 | −0.013268 | 0.007029 | 0.002076 | 0.050137 | 0.052946 |
| 70 | −0.023353 | −0.017648 | −0.0077 | 0.01776 | 0.031434 | −0.04531 | 0.02785 | 0.012799 | 0.048713 | −0.029219 | 0.031339 | −0.022012 | 0.02859 | −0.04079 |
| 71 | 0.177655 | −0.046286 | 0.152015 | −0.046843 | 0.065985 | 0.086587 | 0.104141 | −0.029025 | −0.00827 | 0.034646 | −0.135749 | −0.005949 | 0.076817 | −0.043981 |
| 72 | 0.03234 | −0.033631 | 0.008177 | −0.063173 | 0.024037 | −0.021238 | −0.04604 | −0.037651 | 0.001728 | 0.002095 | −0.036282 | −0.010772 | 0.010748 | −0.040123 |
| 73 | 0.034049 | −0.051953 | −0.012471 | −0.08428 | −0.041579 | 0.016742 | 0.0617 | 0.032552 | −0.033558 | −0.084667 | 0.076561 | −0.069172 | 0.005768 | 0.031103 |
| 74 | 0.027569 | 0.01039 | −0.13741 | −0.004122 | 0.147277 | −0.003191 | 0.182793 | −0.008781 | 0.221922 | 0.05536 | −0.090756 | 0.059329 | 0.017114 | −0.006037 |
| 75 | 0.0024 | −0.009342 | −0.007749 | −0.018909 | −0.012693 | −0.014458 | 0.002401 | 0.009186 | 0.02824 | −0.001635 | 0.002281 | −0.018316 | 0.002233 | −0.034431 |
| 76 | 0.005179 | −0.051765 | 0.03422 | −0.008313 | 0.004074 | 0.022446 | 0.007032 | 0.00573 | 0.024077 | −0.006649 | 0.039066 | 0.014944 | 0.032151 | 0.046262 |
| 77 | −0.00062 | −0.010003 | −0.003741 | −0.032757 | 0.004498 | −0.011087 | −0.010345 | 0.009639 | 0.027374 | −0.001869 | 0.011668 | −0.029163 | 0.014093 | −0.032124 |
| 78 | 0.00754 | −0.012841 | −0.002034 | −0.04244 | −0.003291 | −0.008233 | −0.011992 | −0.00263 | 0.02616 | 0.001417 | 0.013358 | −0.047517 | 0.001143 | −0.045828 |
| 79 | −0.015821 | −0.023907 | −0.027085 | −0.04736 | −0.005108 | −0.028058 | 0.008877 | −0.003904 | 0.024882 | 0.054605 | −0.024839 | −0.029532 | −0.001752 | −0.02713 |
| 80 | 0.009651 | 0.180277 | −0.052306 | 0.101011 | −0.057474 | 0.117465 | 0.077061 | 0.057708 | −0.019378 | 0.052731 | 0.212517 | −0.00213 | 0.091678 | −0.004579 |
| 81 | −0.110508 | 0.107957 | 0.07962 | 0.072278 | 0.074705 | −0.068215 | −0.032697 | −0.078145 | −0.103035 | −0.038407 | 0.05406 | −0.003397 | −0.106945 | −0.001109 |
| 82 | −0.03976 | −0.009971 | −0.0197 | 0.007938 | 0.004394 | −0.005463 | −0.024647 | −0.005826 | 0.001239 | 0.000234 | 0.017705 | 0.007762 | 0.025998 | 0.031571 |
| 83 | −0.021145 | −0.010575 | −0.009721 | 0.019441 | −0.008739 | −0.005769 | −0.015849 | −0.0135 | 0.012232 | 0.000662 | 0.016577 | 0.004523 | 0.031004 | 0.000845 |
| 84 | −0.023423 | 0.003599 | −0.001147 | −0.014993 | 0.018605 | 0.002075 | −0.0111 | −0.021785 | 0.026583 | −0.020668 | 0.016423 | −0.021613 | 0.048039 | −0.000679 |
| 85 | −0.073091 | 0.019812 | −0.065061 | 0.033444 | 0.016486 | −0.036749 | 0.153918 | 0.032876 | 0.046733 | 0.013855 | 0.015098 | −0.003533 | 0.029819 | −0.010617 |
| 86 | 0.045525 | 0.054005 | −0.019195 | −0.096134 | −0.018104 | 0.003712 | −0.064261 | 0.032073 | −0.021801 | 0.004612 | 0.025653 | 0.00755 | 0.002395 | 0.028135 |
| 87 | 0.047313 | 0.123834 | 0.005526 | −0.025184 | −0.062809 | −0.036746 | −0.083313 | −0.026164 | −0.086238 | 0.104602 | −0.028749 | 0.010141 | 0.039569 | 0.019319 |
| 88 | −0.041637 | 0.008348 | −0.014388 | −0.004271 | −0.002755 | −0.011723 | −0.019064 | −0.024062 | 0.009397 | −0.009922 | 0.035084 | 0.003421 | 0.043638 | −0.005017 |
| 89 | −0.026095 | −0.01965 | −0.005765 | 0.023786 | 0.009152 | −0.011071 | −0.007048 | −0.001567 | 0.00332 | −0.000738 | 0.014113 | 0.003909 | 0.017206 | −0.004095 |
| 90 | −0.021128 | −0.016637 | 0.010888 | 0.003843 | 0.002338 | −0.014753 | −0.012371 | −0.006549 | 0.007191 | 0.023557 | 0.019303 | 0.011072 | 0.016016 | 0.002608 |
| 91 | −0.055036 | −0.02161 | −0.012639 | 0.034732 | 0.027029 | −0.033354 | 0.027649 | 0.02148 | 0.009912 | −0.024369 | 0.023294 | −0.015128 | 0.049102 | −0.012074 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 92 | −0.038898 | 0.023111 | 0.008217 | −0.029809 | −0.047263 | −0.04026 | −0.060479 | −0.058437 | 0.04433 | −0.090416 | 0.039521 | −0.077695 | 0.086856 | −0.015813 |
| 93 | −0.033947 | −0.05053 | −0.007813 | 0.006382 | 0.004249 | 0.004274 | −0.000798 | 0.010494 | −0.006537 | −0.030363 | 0.010346 | 0.02403 | 0.000875 | 0.002236 |
| 94 | −0.01931 | −0.074616 | 0.027658 | 0.097415 | 0.064913 | −0.022271 | 0.023456 | −0.021852 | 0.027159 | 0.036605 | −0.025983 | −0.016347 | −0.024886 | −0.036598 |
| 95 | 0.061466 | 0.036383 | −0.008491 | −0.017402 | 0.058249 | 0.022038 | −0.11309 | 0.03776 | −0.009912 | 0.142783 | 0.060795 | 0.037685 | −0.020821 | 0.061325 |
| 96 | −0.06257 | −0.00995 | 0.023885 | 0.01717 | 0.077948 | −0.000181 | 0.088865 | −0.088004 | −0.130766 | −0.061972 | −0.087375 | 0.025338 | 0.067927 | 0.097334 |
| 97 | −0.062178 | −0.053293 | −0.055508 | 0.121878 | −0.044651 | −0.018274 | 0.116683 | 0.054715 | 0.00618 | −0.032458 | 0.047629 | −0.000048 | −0.178952 | 0.053513 |
| 98 | −0.06291 | 0.03709 | −0.019204 | −0.012772 | −0.02147 | −0.00188 | −0.017861 | 0.004134 | 0.048358 | −0.013913 | 0.003266 | 0.031189 | −0.014601 | 0.068859 |
| 99 | −0.013129 | −0.057361 | 0.013291 | 0.050862 | 0.039367 | 0.033493 | 0.024152 | 0.028646 | −0.051226 | −0.036662 | 0.032732 | 0.04521 | 0.038676 | 0.043996 |
| 100 | −0.075239 | −0.040663 | −0.096881 | −0.058536 | 0.030257 | −0.017808 | −0.036965 | 0.012482 | 0.035881 | 0.034382 | 0.044425 | −0.005841 | −0.00457 | 0.079164 |
| 101 | 0.016958 | −0.029658 | −0.037001 | −0.007181 | 0.056399 | 0.045917 | −0.028615 | −0.039154 | 0.049107 | 0.028923 | 0.006176 | 0.012969 | −0.038075 | 0.009463 |
| 102 | 0.032319 | 0.022399 | 0.041597 | 0.027455 | 0.09161 | −0.042272 | 0.01381 | −0.005423 | −0.020761 | 0.03857 | −0.024607 | 0.015208 | 0.05486 | 0.008684 |
| 103 | 0.024588 | −0.056658 | −0.12208 | 0.059388 | −0.134035 | 0.031826 | 0.082796 | 0.051181 | 0.047964 | −0.056529 | 0.022698 | 0.009802 | −0.014352 | −0.047361 |
| 104 | 0.072601 | −0.022011 | −0.043463 | −0.023196 | 0.011645 | 0.125664 | 0.024851 | −0.045642 | −0.020801 | −0.098628 | −0.008399 | 0.020164 | −0.027191 | 0.046574 |
| 105 | 0.087837 | 0.037805 | 0.146391 | −0.022522 | −0.018071 | −0.050903 | −0.095325 | −0.101329 | −0.023074 | −0.012015 | −0.099991 | 0.007565 | −0.046069 | 0.022615 |
| 106 | −0.004008 | −0.038117 | −0.071235 | −0.053494 | −0.033147 | −0.029654 | 0.020053 | 0.051807 | 0.042493 | −0.094461 | 0.00216 | 0.078021 | 0.05136 | −0.032756 |
| 107 | 0.050323 | −0.108494 | 0.173141 | −0.01025 | −0.015362 | 0.005284 | 0.05792 | −0.179766 | 0.033735 | −0.003754 | 0.125676 | −0.083803 | 0.013788 | −0.046926 |
| 108 | −0.038438 | −0.030479 | −0.062918 | −0.029183 | 0.134585 | −0.038967 | −0.0325 | 0.006704 | 0.057597 | −0.074033 | −0.032792 | −0.057765 | 0.000185 | 0.032687 |
| 109 | 0.014494 | −0.0373 | 0.069916 | −0.017401 | 0.056847 | −0.037482 | 0.074412 | −0.047281 | 0.016924 | −0.015968 | 0.048739 | −0.077739 | −0.010081 | 0.021098 |
| 110 | −0.016349 | 0.101997 | 0.026703 | 0.017772 | −0.006748 | −0.014762 | −0.003512 | −0.035325 | −0.002856 | 0.161487 | −0.073472 | −0.034036 | −0.004917 | 0.070015 |
| 111 | −0.066965 | −0.052493 | 0.004655 | 0.038409 | −0.047619 | −0.002983 | 0.064922 | 0.071297 | −0.164099 | 0.034253 | −0.130354 | −0.025838 | −0.022614 | 0.035335 |
| 112 | −0.134851 | 0.06822 | −0.052876 | −0.122854 | 0.056678 | −0.041258 | 0.005011 | −0.034715 | 0.089417 | −0.072053 | 0.063081 | −0.005127 | −0.044579 | −0.084156 |
| 113 | −0.045605 | 0.061399 | −0.054807 | −0.040499 | 0.088222 | 0.197956 | 0.014645 | 0.047526 | 0.019027 | 0.023145 | 0.051642 | −0.00611 | −0.087616 | −0.000733 |
| 114 | 0.102368 | −0.091358 | −0.089449 | −0.031881 | 0.074577 | −0.018306 | −0.004903 | 0.044117 | −0.07454 | −0.078753 | −0.000805 | 0.049824 | 0.098813 | −0.072186 |
| 115 | 0.072875 | 0.026463 | −0.015697 | −0.06431 | 0.066355 | 0.003429 | −0.023328 | 0.168405 | 0.010446 | 0.05924 | 0.063668 | 0.030131 | −0.087544 | −0.002384 |
| 116 | 0.026633 | −0.044353 | −0.044492 | 0.054748 | −0.071956 | −0.023734 | 0.056965 | 0.011819 | −0.092507 | 0.010318 | −0.036321 | −0.003977 | 0.104502 | 0.066834 |
| 117 | 0.078261 | −0.064869 | −0.022177 | −0.065572 | 0.034644 | −0.046687 | 0.005173 | −0.015194 | −0.019346 | −0.020157 | −0.016709 | 0.010224 | 0.000621 | 0.030734 |
| 118 | 0.083043 | −0.024022 | 0.004076 | 0.158913 | 0.087251 | 0.010545 | 0.09085 | −0.097843 | 0.034928 | −0.022988 | −0.119485 | −0.070236 | 0.056312 | 0.074693 |
| 119 | 0.091929 | −0.026373 | −0.041476 | 0.010175 | 0.00073 | −0.004719 | −0.012187 | −0.118131 | −0.03555 | −0.077741 | 0.023547 | −0.002641 | −0.010464 | 0.005604 |
| 120 | −0.012871 | −0.049156 | −0.049402 | 0.022775 | 0.048181 | −0.00217 | 0.069701 | −0.022535 | 0.027917 | 0.039414 | −0.048451 | −0.010771 | −0.087408 | 0.159785 |
| 121 | 0.017145 | 0.034244 | −0.007267 | −0.01332 | −0.08306 | 0.024987 | −0.037219 | 0.036828 | 0.005342 | −0.043724 | −0.012337 | 0.102585 | −0.102674 | −0.027355 |
| 122 | 0.002488 | 0.12076 | 0.006397 | 0.12844 | 0.006666 | 0.083846 | 0.024462 | −0.054252 | 0.090839 | 0.037783 | 0.062292 | 0.050407 | 0.020207 | 0.05939 |
| 123 | 0.025534 | 0.007822 | 0.046119 | 0.014614 | 0.00342 | 0.054901 | 0.0674 | −0.011874 | 0.018941 | −0.005092 | 0.044676 | 0.166673 | −0.044264 | −0.077169 |
| 124 | 0.067782 | 0.023686 | −0.021085 | −0.053333 | 0.008463 | −0.007642 | −0.064553 | −0.076164 | 0.022129 | −0.050574 | 0.084113 | −0.067357 | −0.064222 | −0.066123 |
| 125 | −0.055708 | 0.126671 | 0.139637 | −0.086478 | 0.104676 | −0.034767 | 0.073378 | 0.035696 | −0.071209 | −0.00816 | −0.02639 | 0.023735 | 0.004802 | 0.021164 |
| 126 | 0.007043 | −0.013056 | −0.0162 | 0.040907 | 0.01659 | 0.018325 | 0.049353 | 0.034364 | −0.00805 | −0.040825 | 0.038224 | 0.002269 | −0.023221 | −0.046006 |
| 127 | −0.033027 | −0.050831 | −0.000849 | 0.07013 | 0.001365 | 0.036768 | 0.010876 | 0.006534 | −0.01112 | −0.032245 | 0.025748 | −0.010932 | −0.024985 | −0.072393 |
| 128 | 0.079611 | −0.058757 | −0.035027 | 0.030175 | −0.032721 | −0.07597 | −0.044222 | −0.007368 | −0.027805 | −0.026423 | 0.08248 | 0.012126 | 0.092191 | 0.014417 |
| 129 | 0.000708 | 0.159488 | 0.039156 | 0.05572 | −0.013123 | 0.031591 | −0.123767 | 0.113789 | −0.058971 | 0.006939 | −0.061149 | −0.059825 | −0.056499 | −0.029346 |
| 130 | −0.098125 | −0.127353 | 0.130752 | 0.080893 | 0.053326 | 0.080284 | −0.037685 | −0.023514 | −0.018563 | 0.014108 | −0.031493 | −0.055407 | −0.105641 | −0.036759 |
| 131 | 0.109775 | −0.088186 | 0.012559 | −0.033161 | 0.015638 | −0.006542 | 0.061199 | 0.018041 | 0.023065 | 0.026248 | −0.038258 | 0.011351 | 0.071737 | 0.002813 |
| 132 | −0.040921 | −0.088421 | 0.06322 | 0.087503 | −0.031378 | −0.009942 | −0.04315 | 0.009553 | −0.01267 | 0.051699 | 0.036395 | −0.128654 | −0.062165 | −0.112362 |
| 133 | −0.019183 | −0.017992 | −0.004727 | −0.013114 | −0.098012 | −0.12888 | −0.008695 | 0.054336 | −0.075875 | −0.004223 | −0.099454 | −0.091249 | 0.093102 | −0.060971 |
| 134 | −0.040246 | 0.006938 | −0.087051 | −0.042539 | 0.084603 | 0.001063 | −0.005431 | −0.104481 | −0.008173 | 0.05727 | 0.012917 | −0.231652 | −0.001601 | −0.041811 |
| 135 | 0.051992 | −0.071936 | −0.008885 | −0.08354 | −0.045107 | −0.025213 | 0.031003 | −0.012314 | 0.027098 | 0.022222 | 0.039382 | 0.051249 | 0.020146 | 0.075692 |
| 136 | −0.119447 | −0.115153 | −0.120754 | 0.014001 | 0.105263 | 0.129933 | −0.035643 | 0.0509 | −0.017353 | −0.105074 | −0.098434 | 0.058174 | −0.048966 | 0.12254 |
| 137 | 0.083096 | 0.09624 | 0.016841 | 0.112933 | 0.03407 | −0.014818 | −0.055224 | −0.128189 | 0.05478 | −0.108547 | 0.079695 | −0.006265 | 0.022477 | −0.070637 |
| 138 | −0.005049 | −0.024177 | −0.013574 | −0.01656 | −0.100912 | −0.121375 | −0.006968 | −0.019968 | 0.026706 | −0.094091 | 0.052511 | −0.000183 | −0.020678 | −0.031364 |
| 139 | −0.013816 | −0.073387 | 0.034992 | 0.084176 | 0.097888 | 0.034045 | 0.038947 | −0.018653 | −0.020698 | 0.029239 | 0.094787 | −0.032782 | −0.004345 | 0.027669 |
| 140 | −0.039474 | 0.030751 | 0.069799 | −0.098622 | −0.062041 | −0.064885 | −0.011134 | 0.1503 | 0.036202 | −0.026262 | −0.065624 | −0.01724 | 0.025245 | 0.052215 |
| 141 | −0.007129 | 0.104207 | 0.022172 | −0.004055 | 0.049328 | 0.02154 | 0.046651 | −0.044229 | 0.030138 | 0.041899 | −0.05062 | 0.076787 | 0.026794 | 0.043827 |
| 142 | 0.060327 | −0.045845 | −0.018281 | 0.041827 | −0.000327 | −0.108403 | 0.079614 | 0.003514 | −0.069256 | 0.057213 | 0.015272 | 0.041016 | −0.120932 | −0.067871 |

APPENDIX B1-continued

PCA Transformation Matrix(340 × 340; Normal/Diseased)

| | | | | | | | | | | | | | |
|---|---|---|---|---|---|---|---|---|---|---|---|---|---|
| 143 | 0.047948 | 0.051514 | −0.015132 | −0.134611 | 0.089321 | −0.005478 | −0.087005 | 0.095543 | −0.0142 | −0.148565 | 0.044812 | −0.05605 | 0.029574 | 0.095362 |
| 144 | −0.045691 | −0.140393 | −0.026171 | −0.027317 | −0.006194 | −0.030787 | 0.008223 | 0.069842 | 0.007702 | 0.082607 | −0.006088 | 0.013509 | 0.055646 | −0.110458 |
| 145 | −0.000668 | 0.00573 | 0.05959 | 0.034107 | −0.009832 | 0.075485 | 0.072398 | −0.040145 | 0.008176 | 0.001907 | −0.05229 | −0.003347 | 0.05026 | −0.073383 |
| 146 | −0.081471 | 0.02577 | 0.041883 | −0.057479 | 0.001891 | −0.052981 | 0.037941 | −0.055899 | −0.037506 | 0.039237 | 0.08504 | 0.011308 | 0.092011 | 0.048906 |
| 147 | −0.052526 | 0.106952 | −0.062125 | −0.070166 | −0.084158 | 0.027669 | −0.032721 | 0.10561 | 0.120054 | −0.022097 | 0.07225 | 0.15552 | 0.028028 | 0.021954 |
| 148 | 0.033296 | −0.0404 | 0.028524 | −0.025078 | −0.014871 | −0.075411 | −0.009798 | −0.026657 | 0.098442 | 0.063559 | 0.058804 | −0.014196 | −0.012369 | −0.070879 |
| 149 | −0.040027 | 0.080419 | −0.143146 | 0.028243 | 0.022873 | −0.081405 | 0.04333 | 0.081415 | −0.0116 | 0.114775 | −0.071363 | −0.000888 | −0.005007 | −0.04946 |
| 150 | −0.025746 | 0.06589 | 0.002329 | 0.033838 | −0.056925 | −0.038076 | −0.001354 | 0.038252 | 0.054023 | 0.042298 | −0.0847 | −0.054583 | 0.028674 | −0.106779 |
| 151 | −0.05575 | −0.104769 | 0.014086 | 0.032243 | 0.015918 | 0.064927 | −0.045397 | 0.007708 | −0.036734 | 0.078162 | −0.045754 | 0.045476 | 0.079837 | 0.0665 |
| 152 | 0.024688 | 0.0693 | −0.023334 | 0.023692 | −0.072643 | 0.049527 | −0.085454 | 0.083317 | 0.022133 | −0.042196 | −0.054697 | −0.043559 | 0.04291 | −0.057272 |
| 153 | −0.061789 | 0.030769 | 0.036728 | −0.029347 | −0.052959 | −0.000034 | −0.08276 | −0.076398 | 0.051552 | 0.043275 | 0.061654 | 0.13831 | 0.031261 | 0.073674 |
| 154 | −0.032443 | −0.046705 | −0.046929 | −0.001524 | −0.066673 | −0.019247 | 0.006955 | −0.013186 | −0.047232 | 0.009634 | −0.053152 | 0.005552 | −0.076333 | −0.062022 |
| 155 | 0.021119 | 0.024147 | 0.015877 | 0.130903 | 0.125298 | −0.054513 | −0.06873 | 0.02322 | −0.03177 | −0.029025 | 0.049111 | −0.042964 | 0.066197 | 0.067346 |
| 156 | −0.064842 | 0.064139 | −0.079149 | 0.019687 | −0.066302 | 0.025288 | −0.14535 | −0.059946 | −0.098897 | 0.08105 | 0.023699 | 0.148778 | −0.058686 | −0.018121 |
| 157 | −0.043397 | −0.053154 | 0.048748 | 0.013173 | −0.097549 | 0.014138 | 0.150886 | 0.004778 | −0.014377 | 0.046197 | 0.054647 | 0.001896 | 0.040286 | 0.03066 |
| 158 | 0.047691 | 0.021249 | −0.134449 | −0.021897 | −0.049445 | 0.008386 | −0.066766 | 0.007398 | 0.10324 | −0.079158 | −0.072716 | 0.045219 | 0.041491 | −0.037249 |
| 159 | −0.054457 | −0.073539 | 0.017327 | −0.043078 | −0.107068 | 0.07245 | 0.00078 | −0.029735 | −0.077849 | 0.114294 | −0.01407 | 0.039209 | 0.036775 | −0.074134 |
| 160 | −0.052438 | −0.017749 | −0.078169 | −0.008349 | −0.017083 | 0.019479 | 0.029841 | 0.046677 | 0.014962 | −0.092032 | −0.085908 | 0.032554 | 0.002793 | −0.115855 |
| 161 | 0.21898 | −0.069347 | 0.040581 | −0.020241 | 0.085881 | 0.039173 | −0.039434 | −0.028396 | −0.042318 | 0.020047 | −0.006076 | 0.051229 | −0.039825 | −0.000308 |
| 162 | −0.042904 | −0.028195 | 0.088149 | −0.091626 | 0.11776 | 0.045104 | −0.008271 | 0.064429 | −0.139945 | 0.047153 | −0.076373 | −0.019208 | 0.043224 | 0.059984 |
| 163 | 0.141915 | 0.049572 | 0.004353 | 0.023212 | −0.009347 | −0.007126 | 0.094328 | 0.078441 | −0.002724 | 0.013061 | −0.004252 | −0.048989 | −0.148748 | 0.030673 |
| 164 | −0.032536 | −0.001685 | −0.069558 | −0.076599 | −0.019389 | −0.043478 | 0.013966 | −0.038717 | 0.057961 | −0.015534 | 0.092336 | −0.067667 | −0.090953 | 0.145739 |
| 165 | −0.071126 | −0.100592 | 0.091127 | −0.005676 | 0.024018 | 0.08861 | −0.007391 | 0.017024 | 0.005022 | 0.088865 | −0.045775 | −0.047416 | 0.11954 | −0.014414 |
| 166 | 0.051908 | −0.058809 | 0.034521 | −0.005228 | −0.075617 | 0.138602 | −0.053651 | −0.013388 | 0.082239 | 0.099493 | 0.041496 | −0.035717 | 0.104095 | 0.083659 |
| 167 | −0.089591 | 0.118002 | 0.146059 | −0.008258 | −0.024134 | −0.024182 | 0.118581 | 0.122686 | 0.008889 | 0.015106 | −0.055032 | −0.008604 | 0.097775 | 0.06152 |
| 168 | −0.098835 | 0.049839 | 0.04948 | −0.064494 | 0.064008 | 0.0187 | 0.032165 | 0.015058 | 0.046043 | 0.075431 | 0.030492 | −0.037177 | 0.054192 | 0.015452 |
| 169 | −0.043358 | 0.010855 | 0.028398 | 0.008667 | 0.024614 | 0.030017 | 0.010818 | 0.05379 | −0.005657 | 0.056823 | 0.002756 | −0.00156 | 0.051396 | −0.002762 |
| 170 | −0.037794 | −0.031126 | −0.014266 | 0.033774 | −0.005022 | 0.017358 | −0.026484 | 0.008338 | 0.012366 | 0.032238 | 0.031841 | −0.014125 | 0.027582 | 0.006275 |
| 171 | 0.03102 | −0.012868 | 0.036673 | 0.044512 | 0.015259 | 0.017685 | 0.041917 | 0.023865 | −0.015512 | −0.015699 | −0.021178 | 0.034304 | 0.04683 | 0.009172 |
| 172 | −0.012935 | −0.018252 | −0.058292 | 0.050552 | 0.051768 | 0.012787 | −0.087253 | 0.037287 | 0.001509 | −0.037947 | −0.000987 | 0.028943 | 0.036074 | 0.01805 |
| 173 | −0.054462 | −0.047544 | −0.016055 | 0.036439 | −0.000274 | 0.009941 | −0.005187 | 0.062872 | −0.051689 | −0.080565 | −0.007916 | 0.05886 | −0.035166 | 0.016052 |
| 174 | 0.003099 | −0.021536 | −0.0374 | 0.014597 | −0.025089 | −0.001808 | 0.013613 | 0.035863 | −0.047117 | 0.008003 | −0.108436 | 0.058025 | −0.049609 | −0.034635 |
| 175 | 0.011871 | 0.030127 | −0.087523 | −0.016321 | 0.080343 | 0.04044 | −0.018001 | −0.037059 | 0.011735 | −0.024607 | 0.012519 | −0.119174 | 0.075886 | 0.031995 |
| 176 | 0.06597 | 0.089831 | 0.032673 | 0.03047 | −0.006797 | 0.042617 | −0.027964 | −0.072044 | 0.066009 | 0.053353 | −0.065744 | 0.091724 | 0.048854 | −0.051005 |
| 177 | 0.070484 | −0.034374 | 0.070485 | −0.082605 | 0.121402 | −0.094426 | 0.021492 | −0.043574 | 0.053999 | 0.006647 | 0.003755 | −0.010977 | −0.088813 | −0.108199 |
| 178 | 0.056351 | 0.076168 | 0.027661 | −0.04073 | −0.010258 | 0.008159 | −0.038752 | −0.04817 | −0.02004 | 0.020052 | −0.044674 | −0.012616 | −0.017268 | 0.017805 |
| 179 | 0.004692 | 0.026176 | 0.0549 | 0.004534 | 0.014155 | −0.003452 | 0.017693 | 0.021969 | −0.039897 | −0.052441 | −0.009215 | 0.019444 | −0.011525 | 0.02628 |
| 180 | −0.01603 | 0.035323 | 0.031909 | −0.000567 | −0.021613 | 0.001817 | 0.009748 | −0.004696 | 0.028809 | −0.058571 | −0.039888 | 0.064107 | −0.018294 | 0.050922 |
| 181 | −0.007349 | 0.009583 | 0.020795 | 0.019792 | 0.011245 | −0.003879 | −0.011088 | −0.009075 | 0.059696 | −0.026075 | −0.075785 | 0.04668 | −0.029241 | 0.020855 |
| 182 | −0.019565 | −0.030003 | −0.057922 | 0.012627 | 0.009589 | −0.087741 | −0.033677 | 0.023316 | 0.123001 | 0.016959 | −0.023268 | −0.017358 | 0.014553 | −0.007025 |
| 183 | −0.025858 | −0.009785 | 0.071738 | 0.001777 | 0.017602 | −0.04281 | 0.011951 | 0.015084 | −0.062389 | −0.028402 | 0.077391 | −0.027275 | 0.074965 | −0.027515 |
| 184 | 0.092596 | −0.080083 | 0.055532 | 0.06013 | −0.096219 | 0.057283 | 0.000372 | 0.087052 | −0.044989 | −0.004168 | 0.122744 | −0.062027 | 0.127732 | −0.149908 |
| 185 | −0.000115 | −0.054438 | −0.014848 | 0.135144 | −0.011523 | 0.049378 | −0.00858 | 0.051066 | 0.070732 | −0.005778 | −0.014961 | 0.050962 | −0.02895 | −0.035684 |
| 186 | 0.002075 | 0.019993 | 0.062301 | 0.064476 | −0.099371 | −0.034392 | −0.070895 | −0.024448 | −0.040061 | 0.081676 | 0.007419 | 0.031574 | −0.041792 | 0.028746 |
| 187 | −0.08124 | −0.042017 | 0.07629 | −0.045869 | −0.036561 | −0.013415 | 0.025145 | 0.044156 | −0.01316 | −0.047613 | 0.006616 | 0.013808 | −0.013067 | 0.125662 |
| 188 | −0.050813 | −0.072097 | 0.054028 | −0.041681 | −0.019869 | −0.043682 | 0.036378 | −0.015944 | −0.03606 | −0.009295 | −0.080101 | 0.031386 | 0.024174 | 0.001277 |
| 189 | −0.043553 | −0.050997 | 0.059197 | −0.031653 | −0.029326 | −0.08235 | 0.108027 | −0.110819 | 0.049967 | −0.016887 | −0.018674 | 0.025308 | 0.046406 | −0.022894 |
| 190 | 0.07175 | −0.032045 | −0.032739 | −0.059165 | 0.023956 | 0.038891 | −0.021767 | 0.033388 | −0.133729 | −0.087776 | −0.011462 | 0.011745 | 0.018912 | 0.018182 |
| 191 | 0.036254 | 0.000258 | −0.02822 | −0.0602 | −0.042061 | −0.000992 | −0.013697 | −0.042716 | −0.154497 | −0.042146 | −0.072643 | −0.103567 | −0.021495 | 0.07632 |
| 192 | 0.014312 | −0.04695 | −0.023675 | 0.01994 | 0.002249 | −0.055476 | −0.081558 | 0.034873 | 0.021996 | 0.074728 | 0.027887 | −0.142239 | −0.056165 | 0.009406 |
| 193 | 0.090173 | −0.041758 | 0.012834 | −0.087471 | −0.053836 | −0.068946 | −0.11665 | −0.088183 | −0.009838 | 0.053695 | 0.068219 | 0.065906 | −0.008484 | 0.03589 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 194 | −0.015026 | 0.077039 | 0.072692 | 0.025718 | 0.016043 | 0.169197 | −0.020847 | −0.003434 | 0.017226 | −0.084039 | 0.055889 | −0.0287 | −0.057317 | −0.033509 |
| 195 | 0.034105 | 0.002487 | 0.0403 | 0.097712 | −0.023873 | 0.041662 | 0.03622 | 0.081824 | 0.014587 | −0.054966 | −0.010936 | 0.069536 | −0.049222 | 0.077021 |
| 196 | 0.016541 | −0.054094 | −0.115725 | −0.015314 | 0.090835 | 0.025499 | −0.004268 | 0.00233 | −0.004643 | 0.046221 | 0.073646 | 0.00882 | −0.01249 | −0.091436 |
| 197 | −0.016487 | −0.052601 | −0.155926 | −0.130082 | −0.050264 | 0.021233 | 0.017594 | 0.053467 | −0.037259 | 0.022893 | 0.069088 | 0.00484 | −0.084143 | 0.017835 |
| 198 | 0.11026 | 0.067376 | −0.014547 | 0.000232 | −0.058881 | −0.047978 | 0.08139 | 0.051269 | 0.00393 | 0.113118 | −0.043513 | −0.054669 | 0.019969 | 0.050632 |
| 199 | −0.0703 | 0.091484 | 0.040263 | 0.050304 | −0.074109 | 0.074699 | −0.045683 | −0.12496 | −0.117175 | 0.008207 | −0.085996 | 0.015368 | −0.001034 | −0.033067 |
| 200 | −0.070782 | 0.095236 | −0.021811 | 0.016122 | 0.110019 | −0.213809 | −0.013678 | −0.043848 | −0.036303 | 0.016595 | −0.034035 | 0.024552 | 0.00184 | 0.056828 |
| 201 | −0.082765 | −0.091511 | 0.106817 | 0.055661 | −0.041434 | −0.001547 | −0.048973 | 0.028318 | 0.062031 | −0.026192 | 0.019072 | 0.096825 | −0.065124 | −0.023721 |
| 202 | −0.07651 | 0.003188 | −0.026032 | −0.017126 | −0.033011 | −0.023131 | −0.045969 | −0.086233 | −0.059199 | 0.010292 | 0.052575 | −0.073044 | −0.035927 | 0.022321 |
| 203 | −0.154754 | −0.015529 | −0.0009 | 0:080477 | 0.014904 | −0.09 | 0.062048 | 0.095418 | 0.008086 | 0.00131 | 0.058508 | −0.086863 | 0.020169 | 0.125083 |
| 204 | −0.079608 | 0.035897 | −0.092023 | −0.033537 | −0.005905 | 0.080826 | −0.008155 | −0.06542 | 0.046276 | −0.096549 | −0.061474 | 0.039753 | 0.08021 | −0.021896 |
| 205 | 0.047763 | −0.030445 | −0.064322 | 0.003731 | 0.042891 | 0.025151 | 0.008747 | −0.067799 | 0.02551 | −0.040285 | −0.010981 | 0.078053 | 0.102375 | −0.045697 |
| 206 | 0.061196 | −0.018618 | −0.061204 | −0.046342 | −0.048865 | 0.00541 | 0.113303 | −0.044846 | :0.056645 | 0.06315 | −0.038893 | −0.104791 | 0.043426 | −0.035342 |
| 207 | 0.076242 | 0.009774 | 0.075221 | −0.033885 | −0.100817 | −0.056449 | −0.064983 | −0.026443 | 0.117852 | 0.038135 | −0.013222 | 0.048595 | −0.088836 | 0.00368 |
| 208 | 0.035784 | 0.075377 | 0.073933 | −0.072216 | −0.048697 | 0.068776 | 0.022906 | −0.006578 | −0.023901 | −0.045412 | −0.044193 | 0.166809 | 0.032308 | 0.051166 |
| 209 | 0.092536 | 0.069814 | 0.01128 | 0.125418 | 0.055471 | −0.064546 | 0.104094 | 0.085147 | −0.014978 | 0.058131 | 0.076694 | −0.05461 | −0.197767 | 0.020983 |
| 210 | −0.074111 | 0.06725 | 0.092917 | −0.032454 | −0.009934 | −0.07109 | 0.049296 | 0.00736 | 0.085611 | −0.009999 | −0.006955 | 0.053646 | −0.027759 | 0.006241 |
| 211 | −0.063747 | −0.10551 | 0.022583 | 0.00776 | 0.07191 | −0.058601 | 0.043887 | −0.040428 | −0.064227 | −0.159617 | 0.148425 | 0.085377 | 0.036044 | 0.051401 |
| 212 | 0.105487 | −0.037305 | −0.01768 | 0.043666 | 0.0319 | −0.005898 | 0.017002 | 0.089506 | 0.000951 | 0.060176 | −0.077543 | −0.065229 | −0.046636 | −0.052501 |
| 213 | 0.048522 | −0.080253 | −0.015845 | 0.0268 | 0.132205 | 0.035173 | −0.021328 | 0.079045 | −0.002405 | 0.062169 | 0.0585 | 0.07695 | 0.057641 | 0.005894 |
| 214 | −0.005896 | 0.005691 | 0.019798 | −0.021421 | 0.024643 | −0.011105 | 0.034539 | −0.009373 | −0.027764 | −0.077373 | −0.004743 | 0.054137 | −0.065699 | −0.026531 |
| 215 | 0.084897 | −0.074549 | −0.054068 | −0.059 | 0.033707 | −0.04614 | 0.005244 | −0.072344 | −0.052575 | 0.025417 | −0.118256 | 0.059288 | −0.067391 | −0.017127 |
| 216 | −0.082598 | 0.01794 | −0.029258 | −0.054969 | −0.117209 | 0.091056 | 0.04171 | 0.060908 | 0.023122 | 0.087294 | 0.028021 | −0.064114 | 0.000458 | 0.048305 |
| 217 | −0.021364 | −0.059591 | −0.0145 | 0.030391 | −0.051403 | 0.01126 | −0.026219 | −0.022997 | 0.036432 | −0.06728 | 0.030658 | −0.007625 | −0.030802 | 0.030856 |
| 218 | 0.010907 | −0.079039 | 0.023174 | −0.030295 | −0.009501 | −0.054005 | −0.026869 | −0.053107 | 0.017352 | −0.000475 | 0.011812 | 0.031761 | −0.069014 | −0.005252 |
| 219 | 0.005939 | −0.071028 | 0.030202 | −0.053084 | −0.05828 | −0.022022 | 0.026594 | −0.049124 | −0.04709 | 0.090227 | −0.002884 | 0.03175 | −0.021361 | −0.01581 |
| 220 | −0.011291 | 0.004763 | 0.093387 | −0.027251 | −0.065128 | −0.017188 | −0.055353 | 0.034329 | 0.121881 | −0.019058 | −0.022513 | 0.013314 | −0.060019 | 0.024203 |
| 221 | −0.01785 | 0.02579 | −0.047979 | 0.01123 | −0.033313 | −0.020155 | −0.014113 | 0.001174 | −0.009408 | −0.025364 | 0.019801 | −0.018829 | −0.004877 | −0.037703 |
| 222 | −0.017646 | 0.026355 | 0.002426 | 0.00036 | 0.029984 | −0.017762 | 0.013691 | 0.003812 | −0.033447 | 0.051866 | −0.067605 | −0.008215 | 0.019191 | −0.029984 |
| 223 | −0.030687 | 0.104184 | 0.054514 | −0.02028 | 0.074572 | 0.036464 | −0.032573 | 0.014012 | 0.047931 | 0.083513 | −0.091723 | 0.069482 | −0.015355 | −0.001395 |
| 224 | 0.007049 | −0.060552 | −0.114558 | −0.026606 | 0.075575 | −0.071059 | −0.004761 | −0.007759 | 0.013864 | −0.025781 | −0.062292 | 0.035284 | −0.070851 | 0.001549 |
| 225 | −0.008545 | −0.003859 | −0.0617 | 0.043485 | 0.015218 | −0.064308 | −0.032609 | −0.006075 | −0.008724 | −0.031448 | −0.044964 | −0.044128 | −0.020467 | −0.013563 |
| 226 | −0.034991 | 0.079104 | −0.001935 | −0.033824 | 0.0435 | −0.043997 | −0.009354 | −0.022877 | −0.01625 | −0.004795 | 0.022723 | 0.009254 | 0.010669 | −0.02628 |
| 227 | 0.052006 | 0.00614 | 0.047791 | −0.039731 | 0.050748 | 0.06535 | 0.024602 | 0.040662 | 0.056753 | 0.007678 | 0.043525 | −0.014786 | 0.090021 | 0.009911 |
| 228 | 0.11483 | 0.016077 | 0.009165 | −0.01181 | 0.060659 | −0.065121 | 0.001628 | 0.075329 | 0.098504 | −0.084201 | 0.075268 | −0.011519 | −0.075428 | 0.00126 |
| 229 | −0.073191 | −0.01977 | 0.038692 | 0.029862 | −0.018389 | −0.055678 | −0.033105 | 0.061504 | 0.033899 | −0.010922 | −0.011498 | −0.110696 | 0.020714 | 0.021349 |
| 230 | −0.015507 | 0.016668 | −0.015705 | 0.009947 | 0.042079 | −0.006824 | −0.051784 | −0.013446 | 0.011629 | −0.064211 | 0.0013 | −0.011502 | −0.027916 | −0.039975 |
| 231 | −0.060151 | −0.012093 | −0.019928 | 0.096718 | −0.02938 | 0.02728 | −0.008701 | −0.03594 | 0.128809 | 0.064482 | −0.058865 | −0.01133 | 0.060108 | −0.06108 |
| 232 | −0.052796 | 0.019913 | 0.047359 | −0.052617 | −0.059319 | 0.111079 | 0.119797 | −0.0344 | 0.049636 | −0.037703 | −0.090263 | 0.079197 | 0.016448 | −0.039931 |
| 233 | −0.029471 | 0.098187 | 0.011862 | −0.015018 | −0.008548 | 0.043365 | −0.010381 | −0.024065 | −0.002611 | 0.003769 | 0.019393 | −0.092734 | 0.109182 | 0.088109 |
| 234 | −0.040604 | 0.012461 | −0.019542 | −0.019982 | 0.048655 | −0.050282 | −0.045591 | 0.034897 | −0.035625 | 0.081867 | −0.003224 | 0.069998 | −0.098767 | 0.009395 |
| 235 | 0.024043 | −0.047016 | 0.050203 | 0.036026 | 0.058316 | 0.006224 | 0.106176 | 0.028939 | −0.033811 | 0.051301 | 0.023943 | 0.038734 | −0.022416 | 0.008123 |
| 236 | 0.043589 | 0.082869 | 0.012699 | −0.021228 | −0.032512 | −0.01531 | −0.048434 | 0.008092 | −0.008266 | 0.021744 | −0.015806 | 0.026873 | 0.011321 | 0.053066 |
| 237 | 0.057623 | −0.035218 | 0.062893 | 0.008124 | 0.021205 | 0.025271 | 0.014655 | 0.061038 | 0.095932 | −0.005961 | −0.002265 | −0.068732 | −0.03653 | 0.041347 |
| 238 | 0.021469 | −0.014646 | −0.010813 | 0.062175 | −0.012949 | 0.036779 | −0.020584 | 0.010781 | 0.013811 | 0.020594 | −0.040208 | −0.080829 | 0.013633 | 0.000723 |
| 239 | 0.010045 | 0.028201 | −0.013124 | 0.03231 | −0.065192 | 0.022636 | −0.046357 | 0.046158 | −0.018952 | 0.050278 | 0.031164 | −0.043832 | 0.035526 | −0.002377 |
| 240 | 0.02504 | −0.03797 | −0.049571 | 0.00302 | −0.060769 | 0.009954 | 0.026374 | 0.037408 | −0.008694 | −0.021854 | −0.028279 | −0.0032 | 0.030835 | 0.042467 |
| 241 | 0.024847 | 0.004014 | −0.04563 | −0.029646 | 0.015454 | −0.03701 | −0.013609 | 0.018804 | 0.000235 | −0.015279 | −0.013642 | −0.136087 | −0.000494 | 0.055913 |
| 242 | −0.047683 | −0.051941 | 0.016213 | −0.012871 | −0.056172 | −0.03854 | 0.036317 | 0.003526 | −0.012029 | 0.021623 | −0.02876 | −0.055644 | 0.077496 | 0.031618 |
| 243 | 0.01211 | −0.077583 | 0.054975 | 0.056808 | −0.114807 | −0.033344 | 0.013248 | −0.025164 | −0.062839 | 0.029502 | 0.021869 | 0.00461 | 0.119234 | 0.014402 |
| 244 | 0.008715 | 0.03942 | 0.048176 | 0.;001499 | −0.029929 | −0.048365 | 0.007732 | 0.00379 | −0.033093 | −0.045025 | 0.007038 | −0.002298 | 0.063611 | −0.026134 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 245 | 0.038199 | −0.003353 | −0.001615 | −0.05284 | 0.068252 | −0.025621 | −0.036213 | −0.067452 | −0.074473 | 0.041703 | −0.025086 | 0.063998 | 0.0383 | −0.086858 |
| 246 | −0.041925 | 0.005559 | 0.016477 | −0.004668 | 0.000027 | 0.018405 | −0.008588 | −0.017482 | 0.003865 | 0.023381 | 0.038612 | 0.000505 | −0.027478 | −0.017852 |
| 247 | −0.008183 | −0.001734 | −0.026804 | 0.061032 | 0.052573 | −0.026498 | −0.00792 | 0.021365 | −0.023771 | −0.011416 | 0.006143 | 0.018711 | 0.020015 | −0.018851 |
| 248 | 0.050513 | −0.043477 | 0.021035 | −0.023223 | 0.000671 | −0.033908 | −0.021766 | 0.053527 | −0.014061 | −0.025031 | 0.018791 | 0.016713 | −0.000299 | 0.05904 |
| 249 | 0.076073 | −0.043891 | −0.032856 | 0.115322 | −0.057486 | 0.000646 | −0.127371 | −0.057368 | −0.034871 | −0.011877 | −0.016603 | 0.009303 | 0.024668 | 0.069736 |
| 250 | −0.033259 | −0.004431 | 0.018403 | 0.00228 | 0.001326 | −0.01641 | 0.017069 | −0.059292 | 0.020493 | −0.019191 | 0.026339 | 0.001537 | −0.100293 | 0.001905 |
| 251 | −0.015926 | 0.029504 | −0.025712 | −0.054086 | 0.021555 | −0.037122 | 0.07688 | 0.008436 | −0.025757 | 0.036314 | −0.026808 | 0.017039 | −0.027254 | −0.01825 |
| 252 | −0.007483 | 0.024864 | −0.075094 | −0.037771 | −0.001377 | 0.054997 | −0.054421 | 0.053915 | −0.046772 | −0.030728 | −0.034274 | −0.057399 | 0.079641 | 0.005176 |
| 253 | −0.017879 | −0.032714 | 0.080097 | −0.014249 | 0.051113 | 0.067812 | 0.005625 | 0.052858 | 0.053379 | −0.031814 | 0.019728 | 0.046562 | 0.061022 | −0.036735 |
| 254 | −0.0158 | 0.063185 | 0.027664 | 0.03198 | 0.062649 | 0.007922 | −0.050085 | −0.016054 | −0.014728 | 0.070023 | 0.051559 | 0.04542 | −0.026436 | 0.00594 |
| 255 | −0.002018 | 0.021342 | −0.013401 | −0.047719 | 0.016027 | −0.027209 | 0.044932 | 0.005755 | 0.017699 | 0.013333 | 0.046205 | 0.017092 | 0.053079 | −0.040846 |
| 256 | 0.073999 | 0.024142 | −0.062239 | −0.044748 | 0.109714 | −0.014956 | −0.050041 | −0.067935 | 0.085322 | −0.047067 | 0.030731 | −0.064293 | −0.022937 | −0.023994 |
| 257 | −0.092144 | 0.038081 | 0.024298 | −0.061437 | 0.02942 | 0.085414 | −0.032238 | −0.018724 | 0.037841 | −0.037324 | 0.028669 | 0.043936 | 0.06015 | −0.018198 |
| 258 | −0.047391 | −0.007915 | 0.06066 | 0.022173 | −0.03328 | 0.001098 | −0.059804 | −0.037003 | −0.037516 | 0.006461 | −0.025966 | −0.025609 | 0.013522 | −0.045223 |
| 259 | −0.015299 | −0.063059 | 0.006305 | 0.005789 | −0.002408 | −0.063573 | 0.000268 | −0.008071 | −0.009252 | 0.006562 | −0.035964 | 0.008309 | 0.024712 | 0.021916 |
| 260 | −0.06497 | 0.006674 | 0.07105 | 0.004276 | 0.019088 | 0.060293 | −0.084878 | −0.02983 | −0.010191 | −0.094657 | −0.06987 | −0.080973 | −0.060975 | 0.066668 |
| 261 | −0.072766 | −0.086652 | 0.009011 | 0.025026 | 0.064758 | −0.000754 | 0.024074 | 0.02944 | −0.00205 | 0.074905 | 0.00677 | −0.037799 | −0.043274 | −0.040778 |
| 262 | −0.011497 | −0.052245 | −0.004912 | −0.02486 | 0.068263 | 0.0069 | −0.04198 | 0.016041 | 0.042017 | 0.010188 | −0.011041 | −0.048692 | −0.062735 | −0.007999 |
| 263 | −0.001243 | −0.028058 | 0.033085 | −0.06074 | 0.045115 | −0.004591 | −0.034645 | 0.035491 | 0.026003 | −0.003897 | 0.003254 | −0.002931 | −0.014642 | 0.012403 |
| 264 | 0.054664 | −0.023775 | −0.011841 | −0.000465 | 0.022548 | 0.055198 | 0.102329 | 0.021026 | −0.031015 | 0.025445 | −0.065274 | −0.027351 | 0.078188 | 0.046895 |
| 265 | 0.010589 | 0.013832 | 0.025744 | 0.001362 | 0.00045 | 0.034952 | 0.094177 | 0.033286 | 0.009798 | 0.020033 | −0.008206 | 0.007551 | −0.014489 | 0.007972 |
| 266 | −0.02351 | 0.041176 | 0.00295 | 0.023229 | 0.033237 | −0.040987 | 0.094156 | 0.019885 | 0.06438 | 0.041636 | 0.063302 | 0.019204 | −0.057518 | −0.105559 |
| 267 | −0.07787 | −0.12529 | −0.009326 | 0.038807 | 0.023055 | 0.037094 | −0.009741 | −0.098079 | −0.03661 | 0.011906 | −0.066396 | 0.073671 | −0.041993 | 0.04442 |
| 268 | −0.014155 | 0.012953 | −0.009296 | −0.004507 | −0.026123 | −0.032195 | 0.032156 | 0.015894 | −0.040921 | −0.030141 | 0.018617 | −0.007347 | −0.009541 | 0.050654 |
| 269 | 0.026934 | 0.026297 | −0.044889 | −0.00023 | 0.025844 | −0.044201 | 0.05767 | 0.027433 | −0.036075 | −0.044177 | −0.042831 | −0.019936 | −0.038624 | −0.000916 |
| 270 | 0.027602 | −0.005093 | −0.007764 | −0.085012 | 0.012489 | −0.013577 | 0.017522 | 0.030315 | −0.026716 | 0.037239 | 0.03052 | 0.020628 | −0.009852 | 0.033994 |
| 271 | 0.076508 | −0.021829 | −0.030535 | −0.01595 | 0.000735 | −0.030081 | 0.002464 | 0.090925 | 0.028548 | −0.04452 | −0.041183 | −0.044635 | 0.07379 | −0.025751 |
| 272 | 0.044264 | −0.027066 | 0.01435 | 0.033089 | −0.009902 | −0.023551 | 0.005399 | −0.085666 | 0.033946 | 0.005228 | −0.026842 | 0.03801 | 0.046714 | −0.061813 |
| 273 | 0.000178 | 0.014679 | −0.008415 | 0.0083 | −0.029408 | −0.034775 | −0.024771 | 0.009889 | −0.031335 | −0.013909 | 0.023418 | 0.052048 | −0.016933 | 0.007767 |
| 274 | 0.017131 | 0.027328 | −0.024884 | 0.004337 | 0.001548 | −0.042086 | −0.007519 | −0.005922 | −0.021252 | −0.0234 | 0.006338 | 0.037483 | −0.018918 | 0.002701 |
| 275 | 0.079743 | −0.047496 | −0.000725 | −0.057942 | 0.013542 | 0.009994 | 0.046671 | 0.052452 | −0.053877 | 0.068743 | 0.05442 | 0.109165 | 0.0117 | −0.003711 |
| 276 | 0.013775 | 0.037194 | −0.003996 | 0.000136 | −0.057626 | 0.010732 | −0.00471 | 0.029223 | 0.016203 | 0.100533 | −0.008635 | 0.07096 | −0.051872 | −0.009505 |
| 277 | 0.032587 | −0.015183 | 0.000316 | 0.075855 | −0.022612 | 0.046102 | 0.050388 | 0.072677 | −0.034244 | 0.00834 | −0.017128 | −0.00032 | −0.083682 | 0.056565 |
| 278 | 0.033885 | −0.001818 | −0.032166 | 0.017274 | 0.012827 | −0.016315 | 0.056219 | 0.019865 | 0.013741 | 0.00051 | −0.005497 | 0.061062 | 0.007721 | 0.022172 |
| 279 | 0.03374 | 0.020311 | −0.02724 | −0.014118 | −0.0652 | −0.030678 | 0.008502 | −0.00684 | −0.087947 | 0.028999 | −0.010472 | −0.033775 | 0.00047 | 0.001911 |
| 280 | 0.00004 | −0.011276 | −0.025868 | 0.047554 | −0.090565 | −0.006579 | −0.002748 | −0.035032 | −0.036315 | 0.040902 | 0.086429 | 0.024485 | 0.00954 | −0.001885 |
| 281 | −0.105456 | −0.033749 | −0.055212 | −0.017628 | −0.045866 | 0.017714 | −0.011527 | −0.081833 | −0.041358 | 0.026278 | −0.008167 | −0.072217 | −0.028723 | −0.022001 |
| 282 | −0.033718 | 0.002788 | −0.088705 | −0.025465 | 0.014592 | −0.022201 | −0.000433 | −0.015203 | −0.018129 | 0.016514 | −0.03878 | −0.043307 | 0.019848 | −0.015189 |
| 283 | 0.052185 | 0.046635 | −0.026608 | 0.032482 | 0.047372 | −0.063577 | −0.044964 | −0.088967 | −0.031446 | −0.023134 | 0.053662 | 0.031902 | 0.052603 | 0.021966 |
| 284 | −0.063496 | 0.0091 | 0.007768 | −0.020498 | −0.008565 | 0.088152 | −0.030851 | −0.017224 | 0.013912 | −0.003951 | 0.018128 | 0.043485 | 0.046227 | 0.028745 |
| 285 | −0.040989 | 0.039265 | −0.00323 | −0:067512 | 0.005976 | 0.086832 | −0.040077 | −0.001389 | 0.040321 | −0.04776 | −0.039239 | 0.05606 | 0.078305 | 0.006526 |
| 286 | −0.039033 | −0.062023 | −0.003261 | −0.001208 | −0.021535 | 0.011678 | −0.042648 | −0.026263 | 0.028146 | 0.05793 | −0.043945 | −0.057401 | 0.009123 | −0.027837 |
| 287 | −0.037376 | −0.022891 | −0.018257 | −0.023484 | −0.005307 | −0.006093 | −0.046312 | −0.035057 | 0.039258 | 0.041047 | 0.018641 | 0.003781 | 0.046982 | 0.016943 |
| 288 | 0.041796 | 0.054202 | 0.117021 | −0.082404 | −0.016013 | 0.005932 | −0.010085 | −0.033632 | −0.063953 | −0.002421 | −0.013335 | −0.041504 | −0.047918 | −0.01224 |
| 289 | 0.007148 | 0.063811 | 0.008227 | −0.049411 | 0.015526 | −0.01671 | 0.005405 | −0.035776 | −0.029248 | 0.070575 | 0.000089 | 0.0125 | −0.029338 | 0.007958 |
| 290 | −0.013222 | 0.028337 | −0.007887 | 0.015981 | 0.011347 | −0.022643 | −0.038563 | 0.021656 | 0.04189 | 0.043094 | 0.026336 | −0.026729 | 0.047078 | 0.062316 |
| 291 | −0.01681 | 0.016538 | −0.020939 | 0.014912 | 0.018757 | −0.023227 | −0.041739 | 0.030498 | 0.037252 | 0.049387 | 0.029682 | −0.027676 | 0.044257 | 0.064875 |
| 292 | −0.008272 | 0.042892 | −0.024998 | 0.003379 | −0.005689 | −0.009374 | −0.005049 | 0.013645 | 0.027013 | 0.03171 | 0.004783 | −0.024587 | 0.005889 | 0.031626 |
| 293 | −0.022977 | 0.0214 | −0.02917 | −0.037553 | −0.049964 | 0.005505 | 0.024244 | −0.088161 | −0.088011 | 0.013596 | −0.003233 | 0.06412 | −0.0181 | 0.013377 |
| 294 | 0.057733 | 0.024229 | −0.029359 | −0.017483 | 0.031868 | −0.042258 | 0.058918 | 0.01307 | −0.036419 | 0.096486 | 0.00992 | 0.053544 | 0.001592 | 0.068353 |
| 295 | 0.015544 | −0.028207 | 0.064789 | 0.002055 | 0.04432 | 0.00996 | 0.000314 | −0.053224 | 0.017535 | −0.010161 | 0.049198 | −0.012882 | 0.022511 | 0.022722 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 296 | 0.049099 | −0.014763 | 0.127828 | 0.075534 | 0.119544 | 0.00591 | 0.02216 | 0.05073 | 0.012983 | 0.028075 | −0.028644 | 0.072417 | 0.007305 | −0.036771 |
| 297 | −0.038241 | −0.051996 | 0.009045 | −0.030065 | 0.001363 | 0.052534 | −0.042451 | −0.028466 | 0.012361 | −0.025822 | −0.017567 | −0.002293 | −0.086942 | −0.042347 |
| 298 | −0.016185 | 0.003901 | 0.01792 | 0.054245 | 0.097941 | −0.094231 | −0.123055 | 0.059642 | −0.069729 | −0.021608 | −0.103076 | 0.012223 | 0.12386 | −0.021681 |
| 299 | −0.037999 | −0.015743 | 0.004627 | −0.055471 | 0.04554 | 0.029134 | −0.052088 | 0.034799 | −0.016963 | −0.003175 | −0.046678 | −0.090088 | −0.025993 | −0.041221 |
| 300 | −0.031437 | −0.033454 | −0.007775 | −0.161772 | −0.006598 | 0.04085 | 0.058112 | 0.080658 | 0.068468 | 0.041755 | −0.030725 | −0.114832 | 0.001721 | −0.019307 |
| 301 | −0.037331 | 0.003258 | 0.088808 | −0.032311 | 0.003289 | 0.030926 | −0.028464 | 0.038733 | 0.011546 | −0.019955 | 0.027186 | −0.006619 | 0.048513 | 0.00242 |
| 302 | −0.008163 | −0.009997 | 0.09317 | −0.046029 | 0.049721 | 0.066591 | −0.02499 | 0.044684 | 0.03954 | 0.064109 | 0.1035 | −0.017105 | 0.011343 | 0.000143 |
| 303 | −0.007299 | −0.011114 | 0.013359 | 0.014377 | 0.101809 | −0.016759 | 0.007799 | 0.026545 | −0.014151 | −0.036503 | −0.090913 | −0.035219 | 0.041796 | 0.0076 |
| 304 | 0.084405 | −0.039865 | 0.060119 | −0.041241 | 0.074899 | 0.050108 | −0.05786 | 0.012316 | −0.0356 | 0.034845 | 0.013549 | −0.016009 | −0.078823 | 0.017948 |
| 305 | −0.012787 | 0.030826 | −0.02788 | −0.055186 | 0.040594 | 0.009102 | 0.042662 | −0.126042 | 0.069933 | 0.065954 | −0.02148 | −0.078656 | −0.001675 | 0.0483 |
| 306 | −0.021698 | 0.002815 | −0.033869 | −0.035506 | −0.063436 | 0.086225 | 0.087328 | −0.055706 | −0.065375 | 0.067369 | 0.031775 | 0.017438 | 0.079113 | 0.008208 |
| 307 | 0.031913 | 0.045738 | −0.013527 | −0.009665 | 0.020474 | 0.112819 | 0.14346 | 0.006086 | 0.00222 | −0.025745 | 0.008915 | 0.100759 | −0.029669 | −0.028631 |
| 308 | −0.025852 | 0.052714 | −0.046411 | −0.035219 | −0.035139 | 0.051407 | −0.097163 | −0.03076 | −0.049793 | 0.007937 | −0.030961 | −0.032252 | −0.014027 | −0.025994 |
| 309 | 0.037884 | 0.003628 | −0.056886 | 0.023973 | 0.003198 | 0.01034 | −0.060045 | −0.004162 | −0.065021 | 0.054418 | −0.003872 | 0.036098 | 0.012894 | −0.020305 |
| 310 | 0.004756 | −0.006406 | 0.006044 | −0.019233 | 0.033865 | −0.044214 | 0.033049 | 0.046356 | −0.010874 | −0.102795 | 0.035931 | 0.091881 | 0.106598 | 0.010886 |
| 311 | −0.012178 | 0.026253 | −0.039133 | 0.035826 | −0.019808 | −0.033982 | 0.012385 | 0.082348 | −0.157377 | −0.082671 | 0.026984 | −0.052064 | 0.006563 | 0.009255 |
| 312 | −0.05978 | −0.022837 | −0.010175 | −0.128608 | 0.017007 | 0.040681 | 0.051871 | −0.124677 | 0.083721 | 0.015261 | −0.041472 | −0.041368 | −0.092443 | −0.027642 |
| 313 | −0.102193 | −0.053473 | 0.105032 | −0.065276 | 0.001907 | −0.010621 | 0.01394 | 0.131749 | −0.050728 | 0.034218 | 0.00531 | −0.017618 | −0.04242 | −0.006495 |
| 314 | 0.000235 | −0.100565 | −0.028361 | −0.056491 | 0.02829 | 0.018842 | −0.065115 | −0.045034 | 0.013887 | −0.03396 | −0.082696 | 0.061473 | 0.109746 | −0.138036 |
| 315 | −0.047243 | 0.028016 | −0.069084 | 0.03877 | 0.034604 | 0.042014 | 0.008291 | −0.046627 | −0.005565 | 0.012854 | 0.00342 | −0.114675 | −0.056946 | −0.047894 |
| 316 | 0.075489 | −0.034011 | 0.040076 | 0.076655 | 0.015321 | 0.080808 | 0.003362 | −0.04709 | −0.100703 | 0.02796 | 0.089711 | −0.009193 | 0.037827 | −0.067893 |
| 317 | 0.026816 | 0.000838 | −0.012832 | 0.036531 | 0.050539 | −0.014227 | −0.047792 | −0.029186 | −0.008504 | −0.000579 | 0.006425 | 0.06575 | 0.034039 | −0.018717 |
| 318 | 0.113683 | 0.118401 | 0.048711 | −0.001789 | −0.045691 | 0.011902 | 0.023837 | −0.006456 | 0.040855 | −0.070077 | −0.013822 | 0.016883 | 0.04395 | 0.00082 |
| 319 | −0.042832 | 0.033162 | −0.048402 | 0.086047 | 0.026412 | 0.03929 | −0.040915 | −0.049734 | 0.055373 | −0.005166 | 0.01485 | −0.027622 | 0.039364 | −0.011934 |
| 320 | 0.000003 | 0.067063 | 0.049107 | 0.080359 | −0.024155 | 0.042219 | 0.070337 | 0.04248 | 0.036388 | −0.046455 | −0.079341 | 0.028963 | 0.019487 | −0.083111 |
| 321 | 0.01145 | −0.00246 | 0.033355 | −0.056719 | −0.025895 | −0.013815 | 0.026622 | 0.023161 | −0.001506 | 0.09362 | 0.104781 | −0.086196 | −0.079587 | −0.123229 |
| 322 | 0.025244 | 0.042443 | −0.000072 | 0.121633 | 0.10629 | −0.203884 | −0.046202 | −0.074747 | −0.095909 | 0.009934 | 0.026609 | 0.058386 | 0.088832 | −0.019271 |
| 323 | −0.135792 | −0.020584 | −0.083886 | 0.102447 | 0.064885 | −0.006933 | 0.082727 | 0.042252 | 0.006359 | 0.014475 | 0.062455 | 0.052474 | −0.000344 | 0.021922 |
| 324 | −0.049797 | −0.002444 | 0.004361 | −0.078132 | −0.149945 | 0.000803 | 0.09227 | −0.055148 | 0.058485 | −0.106813 | 0.077597 | −0.002386 | −0.109863 | 0.012717 |
| 325 | 0.07188 | −0.027982 | −0.011702 | 0.099325 | −0.01605 | −0.143239 | −0.029213 | 0.044645 | 0.077641 | −0.011537 | −0.062477 | −0.01616 | −0.117202 | −0.054455 |
| 326 | 0.0463 | −0.085333 | −0.019059 | −0:015657 | −0.020833 | −0.20595 | 0.048472 | −0.140403 | 0.057758 | 0.002925 | −0.039386 | 0.057737 | 0.075517 | 0.156292 |
| 327 | 0.009698 | 0.051449 | 0.003663 | 0.050236 | 0.002583 | 0.010218 | −0.040721 | −0.009662 | −0.038709 | 0.064403 | −0.087614 | −0.074451 | 0.009641 | 0.000647 |
| 328 | 0.030782 | −0.049303 | −0.085215 | 0.132012 | −0.025665 | 0.08182 | 0.035696 | −0.101692 | 0.011775 | 0.08432 | 0.076605 | 0.035643 | −0.071935 | 0.120379 |
| 329 | 0.007652 | 0.038292 | 0.074981 | 0.058926 | −0.01209 | −0.027955 | −0.046026 | 0.086449 | 0.074973 | 0.091923 | −0.020314 | −0.029909 | 0.034389 | 0.040031 |
| 330 | −0.044478 | 0.012312 | 0.024747 | −0.026023 | 0.00235 | −0.059997 | 0.072861 | −0.059735 | −0.026741 | −0.01567 | 0.001452 | 0.043667 | −0.042916 | −0.074283 |
| 331 | 0.027182 | 0.031678 | −0.066275 | 0.00158 | −0.02886 | −0.063613 | 0.079857 | 0.00063 | 0.00937 | 0.082697 | −0.048286 | −0.05274 | 0.036656 | 0.066937 |
| 332 | 0.082126 | 0.055046 | 0.088014 | −0.063229 | −0.080963 | −0.021315 | −0.038466 | 0.041945 | 0.0759 | −0.099187 | 0.011194 | −0.002137 | −0.098302 | −0.012482 |
| 333 | 0.122352 | 0.044854 | −0.073501 | 0.079776 | −0.185555 | −0.044137 | −0.040252 | −0.008325 | 0.078499 | −0.014805 | −0.013988 | 0.005454 | 0.023907 | 0.037884 |
| 334 | −0.007012 | −0.102894 | 0.108646 | 0.074574 | 0.011957 | 0.018514 | −0.075576 | 0.039261 | 0.053254 | 0.066542 | 0.117206 | −0.029344 | 0.091851 | −0.09813 |
| 335 | 0.039216 | 0.002291 | −0.037622 | 0.035118 | −0.083733 | −0.029792 | 0.030634 | −0.071501 | 0.056514 | 0.061694 | −0.085154 | −0.027075 | 0.013473 | −0.012659 |
| 336 | 0.075311 | −0.044468 | −0.104872 | −0.051651 | −0.059267 | 0.022038 | −0.090606 | 0.05307 | −0.017377 | 0.035622 | 0.075203 | −0.065278 | −0.01117 | 0.027886 |
| 337 | 0.03176 | −0.015582 | 0.102152 | 0.126502 | −0.076616 | 0.087306 | 0.001221 | −0.059519 | 0.080542 | −0.138454 | −0.008389 | −0.022451 | −0.030491 | 0.065018 |
| 338 | −0.084558 | 0.028197 | −0.024067 | 0.074118 | 0.050849 | 0.086412 | −0.065903 | 0.056349 | 0.080218 | 0.033563 | −0.130372 | −0.031034 | −0.025639 | 0.048574 |
| 339 | 0.005908 | 0.127941 | −0.003964 | −0.013392 | −0.024807 | −0.043959 | −0.042599 | −0.037171 | −0.062645 | −0.012766 | 0.173628 | −0.043389 | 0.061277 | −0.024392 |
| 340 | −0.01055 | 0.083035 | −0.079871 | −0.140744 | 0.061764 | −0.011895 | 0.042465 | −0.042766 | −0.077076 | 0.038848 | −0.11878 | 0.077233 | −0.018016 | 0.026073 |

| | DF | DG | DH | DI | DJ | DK | DL | DM | DN | DO | DP | DQ | DR | DS |
|---|---|---|---|---|---|---|---|---|---|---|---|---|---|---|
| 1 | −0.077593 | −0.013928 | 0.028114 | −0.000104 | −0.038608 | −0.007501 | −0.0751 | −0.036849 | 0.130151 | 0.003251 | −0.074671 | −0.059299 | −0.014776 | −0.006873 |
| 2 | 0.021828 | −0.048991 | 0.007773 | 0.019561 | 0.017527 | 0.040158 | 0.026734 | 0.064326 | 0.0186 | −0.073486 | 0.000379 | 0.030272 | −0.015066 | 0.000581 |
| 3 | −0.048277 | 0.012063 | −0.055438 | −0.018476 | −0.009706 | −0.041407 | −0.050357 | −0.06435 | 0.040173 | −0.070119 | −0.123502 | −0.070382 | −0.024284 | −0.067737 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 4 | −0.079679 | −0.025265 | 0.009819 | 0.019531 | −0.012227 | 0.030516 | 0.023243 | −0.091506 | 0.010765 | 0.038076 | −0.021664 | −0.01947 | 0.077278 | 0.042216 |
| 5 | 0.105287 | −0.077338 | −0.089652 | −0.109616 | −0.019069 | −0.005471 | 0.044522 | −0.010012 | 0.073198 | −0.051743 | 0.010051 | 0.053497 | 0.107631 | 0.009183 |
| 6 | 0.030122 | −0.010584 | 0.032608 | 0.051996 | 0.119023 | 0.11815 | 0.092509 | −0.163362 | −0.050394 | 0.095343 | −0.143215 | −0.056485 | −0.008489 | −0.048641 |
| 7 | 0.018277 | 0.000381 | −0.008239 | 0.043717 | 0.036831 | 0.094716 | −0.064643 | 0.090635 | 0.155866 | 0.106657 | 0.022159 | −0.105199 | 0.021258 | 0.103338 |
| 8 | 0.012717 | −0.020473 | 0.056502 | −0.008667 | −0.014702 | −0.037866 | −0.024147 | 0.023799 | −0.095585 | 0.001225 | −0.105874 | 0.001949 | −0.073213 | 0.10393 |
| 9 | 0.038996 | 0.056087 | 0.0206 | 0.03024 | −0.047489 | 0.019808 | −0.031558 | 0.087849 | −0.096926 | 0.029781 | 0.08264 | −0.090827 | −0.088135 | −0.035416 |
| 10 | 0.034534 | 0.058214 | −0.110747 | 0.10226 | 0.002065 | 0.023949 | 0.016567 | −0.036319 | −0.00927 | −0.083504 | 0.012304 | 0.127595 | 0.113043 | 0.005063 |
| 11 | 0.110286 | 0.018533 | 0.013731 | 0.027058 | −0.017618 | 0.04598 | 0.023679 | −0.021726 | 0.092985 | −0.021838 | 0.0496 | 0.060408 | −0.016238 | 0.041743 |
| 12 | 0.107485 | 0.008667 | 0.022217 | −0.096739 | 0.028944 | 0.003448 | −0.009698 | −0.012022 | 0.012655 | −0.053796 | 0.036691 | −0.002132 | 0.066653 | −0.023817 |
| 13 | −0.030608 | 0.003836 | −0.103638 | 0.034586 | −0.014241 | 0.029456 | 0.005634 | 0.001778 | 0.055757 | −0.07284 | 0.090836 | 0.076628 | −0.017088 | 0.023161 |
| 14 | −0.044324 | 0.081916 | 0.006217 | 0.101075 | 0.0015 | −0.029171 | 0.112227 | 0.01771 | 0.054349 | −0.05717 | 0.041831 | 0.013219 | 0.017371 | 0.00612 |
| 15 | −0.087213 | −0.023128 | 0.000471 | −0.038329 | −0.069367 | 0.004627 | −0.011894 | 0.069222 | 0.070726 | 0.021184 | −0.060817 | −0.030784 | 0.068976 | 0.013189 |
| 16 | 0.036633 | 0.052397 | −0.08695 | −0.085775 | 0.06361 | 0.040776 | −0.021848 | 0.000867 | −0.001283 | 0.137422 | 0.0757 | 0.013463 | −0.015816 | 0.0407 |
| 17 | 0.056296 | 0.016069 | −0.125946 | 0.073523 | 0.051314 | −0.077162 | −0.006652 | −0.081592 | −0.024307 | 0.062571 | −0.051163 | −0.03932 | 0.03077 | −0.092853 |
| 18 | 0.015857 | 0.135856 | −0.051517 | 0.153278 | 0.03122 | 0.044304 | 0.0207 | −0.126072 | −0.01451 | −0.149093 | −0.094711 | −0.161405 | −0.001237 | −0.033584 |
| 19 | 0.078248 | −0.027851 | 0.1863 | −0.029826 | −0.027193 | −0.05681 | −0.02595 | −0.043097 | −0.061212 | 0.068228 | −0.028045 | −0.138895 | 0.027462 | −0.02874 |
| 20 | 0.009074 | 0.03402 | −0.024811 | −0.01425 | −0.022419 | 0.02908 | 0.016366 | 0.034192 | −0.021535 | −0.002833 | −0.050057 | 0.000559 | 0.022019 | 0.032466 |
| 21 | −0.07387 | −0.093044 | −0.033368 | −0.055055 | −0.041437 | −0.082432 | 0.131222 | 0.05219 | −0.06512 | 0.060466 | 0.056962 | −0.057304 | 0.108634 | 0.066055 |
| 22 | −0.064284 | 0.1576 | −0.040227 | −0.037412 | 0.024862 | −0.082268 | −0.000719 | 0.140087 | −0.021816 | 0.022021 | 0.035609 | −0.004509 | −0.089974 | 0.010288 |
| 23 | −0.00989 | 0.004354 | −0.074729 | 0.05603 | 0.048253 | 0.081843 | 0.004758 | −0.140835 | 0.010437 | −0.062168 | 0.111668 | 0.021191 | 0.000093 | −0.085524 |
| 24 | 0.000184 | 0.218259 | −0.000411 | 0.016779 | 0.059075 | −0.037652 | −0.101592 | 0.065311 | 0.000835 | −0.114416 | −0.038721 | −0.046825 | −0.068932 | −0.008015 |
| 25 | 0.033141 | 0.007307 | 0.076742 | −0.057998 | −0.018613 | −0.002732 | 0.044763 | 0.043683 | −0.103216 | 0.023103 | −0.003271 | 0.031442 | −0.042174 | −0.128584 |
| 26 | 0.018307 | 0.016745 | −0.042321 | −0.01181 | −0.02047 | 0.030212 | 0.010691 | 0.024652 | −0.032585 | 0.002514 | −0.043818 | 0.019896 | 0.01896 | 0.059473 |
| 27 | 0.013267 | −0.004898 | −0.00066 | −0.010696 | 0.009379 | 0.036942 | 0.001746 | 0.008173 | 0.0047 | −0.005272 | −0.012376 | −0.012757 | 0.009475 | −0.002975 |
| 28 | −0.03254 | −0.022462 | −0.024402 | 0.027797 | −0.04435 | 0.07017 | −0.024745 | 0.006898 | 0.045922 | 0.040733 | 0.00477 | −0.027525 | 0.002307 | 0.046479 |
| 29 | 0.052028 | −0.211518 | −0.060698 | 0.100955 | 0.019201 | −0.017577 | 0.045463 | −0.065158 | −0.001213 | 0.117151 | 0.160737 | 0.070115 | −0.080089 | −0.104722 |
| 30 | −0.00527 | −0.017092 | −0.045546 | 0.009472 | −0.020649 | 0.055156 | 0.054045 | 0.071005 | −0.051965 | −0.017814 | 0.063071 | −0.011414 | 0.023131 | −0.017574 |
| 31 | −0.037098 | −0.000991 | 0.052914 | −0.003895 | −0.020117 | 0.009645 | 0.037542 | 0.013565 | −0.066432 | −0.007854 | −0.003537 | −0.030368 | −0.102737 | 0.046862 |
| 32 | −0.009899 | 0.002546 | 0.034048 | −0.097611 | −0.148678 | 0.020455 | −0.043174 | 0.013025 | −0.029774 | −0.038973 | −0.021688 | −0.052108 | −0.048814 | 0.031048 |
| 33 | −0.031433 | 0.00401 | −0.038203 | −0.042117 | 0.069974 | −0.022586 | −0.085467 | −0.017406 | 0.008896 | −0.059319 | 0.032344 | 0.020229 | 0.001135 | −0.098087 |
| 34 | 0.060135 | −0.019351 | 0.044748 | 0.017453 | −0.013902 | −0.022118 | 0.065229 | 0.044829 | −0.000156 | −0.070736 | 0.035314 | 0.116308 | 0.057195 | 0.085986 |
| 35 | −0.035583 | 0.044866 | 0.119715 | −0.066321 | −0.029326 | 0.017649 | −0.089449 | −0.040061 | −0.076224 | 0.098319 | −0.078665 | −0.013129 | −0.005767 | −0.058251 |
| 36 | −0.043068 | 0.046063 | 0.016876 | 0.048813 | 0.061475 | 0.007378 | −0.09435 | −0.062403 | −0.022899 | 0.03722 | −0.110423 | 0.090431 | −0.030308 | 0.021472 |
| 37 | 0.014182 | −0.022079 | −0.089573 | 0.012236 | −0.009056 | 0.00062 | 0.090071 | −0.033105 | −0.07527 | 0.066328 | −0.024754 | −0.013213 | −0.007109 | 0.041941 |
| 38 | −0.019434 | 0.034987 | −0.016234 | −0.060439 | −0.070021 | −0.017367 | 0.018313 | −0.051694 | 0.055838 | 0.041665 | −0.082768 | 0.07904 | −0.040589 | 0.030931 |
| 39 | −0.106036 | 0.0750981 | −0.138167 | 0.003063 | −0.108025 | −0.081889 | −0.027625 | 0.006601 | −0.062382 | −0.017211 | −0.089735 | 0.058223 | 0.090741 | −0.005935 |
| 40 | −0.086668 | 0.076809 | −0.016109 | −0.012801 | −0.063949 | 0.034043 | 0.073017 | −0.00913 | −0.032352 | 0.009254 | 0.006647 | −0.011577 | 0.001972 | 0.031297 |
| 41 | −0.006775 | −0.048643 | 0.038912 | −0.010955 | 0.053014 | 0.012905 | −0.111214 | 0.051512 | −0.011038 | −0.010837 | −0.016281 | −0.047988 | −0.010663 | −0.07243 |
| 42 | 0.011864 | 0.054624 | −0.018742 | −0.043768 | −0.024111 | 0.004776 | −0.001202 | −0.041889 | −0.057963 | −0.029647 | 0.030526 | −0.014214 | −0.023111 | 0.044622 |
| 43 | −0.021379 | −0.051728 | −0.041504 | 0.018709 | 0.010356 | −0.033009 | −0.02093 | −0.042412 | −0.009179 | −0.062041 | 0.025394 | 0.053285 | −0.011583 | −0.103389 |
| 44 | 0.071324 | 0.009616 | 0.0267 | −0.062344 | 0.044231 | −0.008539 | −0.077971 | 0.050151 | 0.002299 | −0.001419 | −0.030721 | −0.000146 | 0.035682 | 0.029956 |
| 45 | −0.047928 | −0.041544 | −0.007675 | −0.081689 | −0.01276 | −0.04254 | 0.01396 | 0.029459 | −0.008748 | −0.038702 | 0.02852 | 0.01595 | −0.070949 | −0.046249 |
| 46 | −0.150306 | 0.015671 | 0.046401 | 0.118469 | 0.024595 | 0.152199 | −0.040353 | −0.019238 | −0.010942 | 0.122202 | 0.069418 | 0.001425 | 0.014393 | 0.129276 |
| 47 | 0.05179 | 0.030486 | 0.034486 | 0.06103 | 0.050753 | −0.008533 | 0.022853 | 0.071918 | −0.017362 | −0.020327 | −0.052112 | 0.059159 | 0.048264 | 0.074655 |
| 48 | −0.037117 | −0.077126 | 0.013542 | 0.058798 | 0.108306 | −0.015153 | 0.050971 | 0.07488 | 0.019911 | 0.071673 | 0.011049 | 0.008799 | −0.0752 | −0.068596 |
| 49 | −0.014748 | −0.013782 | −0.037068 | −0.037862 | 0.00635 | 0.02928 | 0.07896 | 0.051368 | −0.044153 | 0.018148 | 0.091602 | −0.007206 | −0.003003 | −0.02689 |
| 50 | −0.008233 | 0.026365 | −0.046937 | 0.011462 | 0.047833 | −0.133248 | −0.061684 | −0.021708 | 0.067703 | 0.039542 | 0.05409 | −0.069895 | −0.012079 | 0.05077 |
| 51 | 0.075728 | −0.06443 | 0.02797 | −0.035656 | 0.036556 | −0.017449 | 0.000799 | −0.013688 | 0.080938 | 0.004666 | 0.030557 | −0.043256 | −0.055723 | −0.036936 |
| 52 | 0.047605 | −0.064524 | −0.012947 | 0.003833 | 0.045226 | 0.073453 | −0.051702 | 0.143258 | −0.096533 | 0.00746 | 0.030344 | 0.124385 | 0.104788 | −0.065738 |
| 53 | 0.029004 | 0.023088 | 0.007333 | −0.008776 | −0.000819 | −0.025855 | 0.007923 | 0.063038 | 0.040272 | −0.029684 | −0.012426 | −0.051295 | −0.02447 | −0.014403 |
| 54 | −0.027834 | 0.025518 | −0.038748 | −0.015609 | 0.044617 | −0.020439 | 0.087161 | −0.096555 | 0.014425 | 0.00695 | 0.002491 | 0.02963 | −0.009135 | −0.047143 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 55 | −0.0281 | −0.00128 | 0.061243 | −0.083915 | −0.038767 | −0.062051 | 0.111288 | 0.008007 | −0.015212 | 0.000245 | −0.065753 | −0.02924 | 0.042541 | −0.039754 |
| 56 | −0.00271 | −0.039279 | 0.010785 | −0.043614 | 0.02533 | 0.017287 | 0.001143 | 0.004925 | 0.011379 | −0.042988 | 0.032816 | −0.057628 | 0.050932 | 0.025731 |
| 57 | −0.128327 | 0.005607 | −0.045863 | 0.066374 | 0.004866 | −0.01182 | −0.037852 | 0.007815 | −0.044956 | −0.031655 | 0.070569 | −0.045925 | 0.023323 | −0.031315 |
| 58 | 0.050402 | −0.056322 | −0.041813 | 0.074311 | −0.014398 | −0.142171 | 0.007407 | −0.052497 | −0.001085 | 0.007438 | −0.032571 | −0.018265 | 0.000066 | 0.008007 |
| 59 | 0.122072 | 0.010002 | 0.034149 | 0.047823 | −0.14703 | 0.026419 | −0.037926 | 0.033329 | 0.015339 | 0.026905 | −0.099018 | −0.102314 | 0.025837 | 0.085078 |
| 60 | 0.03231 | 0.033433 | 0.062366 | −0.007424 | −0.026226 | 0.060442 | 0.035152 | 0.00369 | −0.103454 | −0.032326 | 0.00203 | 0.115022 | −0.033664 | 0.052079 |
| 61 | −0.016205 | 0.034224 | 0.078371 | −0.012917 | 0.008605 | −0.009961 | −0.100702 | 0.034912 | 0.0993 | −0.022668 | 0.058691 | 0.045011 | −0.103447 | −0.049068 |
| 62 | 0.000841 | −0.016093 | −0.023093 | −0.045315 | 0.019367 | −0.032444 | 0.006497 | −0.042875 | −0.132851 | −0.019791 | −0.025355 | 0.050631 | 0.006643 | 0.108613 |
| 63 | 0.023766 | −0.013443 | −0.028774 | −0.00458 | 0.048433 | 0.029513 | −0.010605 | −0.145031 | −0.014068 | 0.057365 | 0.056535 | 0.015963 | −0.042208 | 0.084526 |
| 64 | 0.061109 | −0.009227 | 0.02185 | 0.012789 | −0.014947 | −0.032469 | 0.03379 | −0.022954 | −0.050494 | −0.092599 | −0.029002 | −0.027122 | 0.044174 | −0.147568 |
| 65 | −0.083211 | 0.057806 | 0.028814 | 0.002501 | 0.05183 | 0.042476 | 0.061803 | −0.015373 | −0.080274 | −0.040082 | 0.020856 | 0.017941 | −0.014157 | 0.027824 |
| 66 | 0.091384 | −0.081639 | 0.099518 | −0.019047 | 0.087952 | −0.036788 | 0.024085 | −0.045841 | 0.009915 | −0.033112 | −0.058 | 0.098316 | 0.004668 | 0.043971 |
| 67 | 0.08839 | 0.058484 | 0.014458 | −0.00603 | 0.007272 | −0.007825 | −0.053439 | 0.030134 | 0.121747 | 0.12063 | −0.052229 | 0.011867 | −0.045857 | 0.013637 |
| 68 | 0.002825 | −0.036137 | 0.017655 | −0.058766 | −0.025538 | −0.009379 | 0.081833 | 0.04968 | −0.081989 | −0.037503 | −0.046544 | −0.044975 | −0.059498 | −0.031309 |
| 69 | −0.071931 | −0.074057 | 0.041348 | −0.046101 | −0.034776 | −0.069153 | 0.007628 | 0.06606 | 0.101645 | −0.022649 | −0.025985 | 0.02929 | 0.004753 | −0.049096 |
| 70 | −0.003694 | −0.041846 | −0.006453 | −0.035453 | 0.026696 | 0.013624 | −0.026196 | 0.01719 | 0.032241 | 0.067183 | −0.013084 | 0.039992 | −0.0029 | 0.044793 |
| 71 | −0.032807 | 0.008093 | 0.04331 | −0.048788 | 0.158602 | 0.048824 | −0.015217 | −0.024175 | 0.018303 | 0.016267 | −0.150262 | 0.002429 | 0.054101 | 0.019742 |
| 72 | −0.003803 | 0.006221 | −0.067828 | 0.010575 | −0.021734 | −0.071484 | 0.009855 | −0.011293 | −0.012898 | −0.033149 | 0.034645 | 0.06741 | −0.006151 | −0.053938 |
| 73 | −0.005029 | 0.065258 | 0.03931 | 0.008886 | −0.041057 | −0.009175 | −0.056218 | 0.092578 | 0.051404 | 0.068125 | −0.070778 | 0.008082 | −0.042937 | 0.045165 |
| 74 | 0.086308 | 0.02639 | −0.055933 | −0.00174 | −0.051544 | 0.029722 | −0.007484 | 0.020726 | 0.093239 | −0.081654 | 0.034289 | −0.05949 | 0.081042 | 0.010166 |
| 75 | −0.005318 | −0.022904 | 0.021091 | −0.017285 | 0.004871 | 0.017965 | −0.015323 | 0.005036 | −0.004349 | −0.005617 | 0.031836 | 0.01396 | −0.011175 | −0.000887 |
| 76 | 0.032726 | −0.027877 | −0.003268 | −0.042701 | −0.008457 | 0.008215 | 0.031585 | −0.007068 | 0.016137 | 0.007727 | 0.033255 | −0.012823 | −0.037594 | 0.032481 |
| 77 | −0.005157 | −0.025872 | 0.01622 | −0.040161 | 0.003443 | 0.019666 | −0.03379 | 0.004005 | −0.02799 | 0.007686 | 0.007121 | −0.012156 | −0.004275 | 0.00193 |
| 78 | 0.015733 | −0.021484 | 0.02508 | −0.040611 | −0.006209 | 0.022931 | −0.04123 | −0.011762 | −0.034534 | 0.014058 | 0.009044 | −0.014641 | −0.005767 | −0.001647 |
| 79 | 0.010812 | 0.019586 | 0.023527 | −0.02753 | 0.021494 | 0.021878 | −0.044017 | 0.017103 | −0.065538 | −0.013801 | −0.012955 | −0.046734 | 0.081972 | −0.032971 |
| 80 | 0.086781 | 0.015381 | 0.072095 | −0.050888 | 0.027912 | −0.080776 | −0.101993 | 0.004971 | −0.053657 | 0.025698 | −0.027926 | 0.000272 | −0.011036 | 0.04617 |
| 81 | 0.032906 | −0.071291 | −0.028506 | −0.066495 | 0.026313 | 0.019262 | 0.087128 | −0.119283 | −0.117356 | 0.05129 | −0.034881 | −0.020443 | −0.067801 | 0.005107 |
| 82 | −0.009263 | −0.003928 | −0.004031 | −0.060279 | 0.035173 | 0.010238 | 0.025989 | −0.005568 | 0.010768 | −0.001793 | 0.003308 | −0.034646 | 0.026882 | 0.012841 |
| 83 | 0.015178 | −0.005612 | 0.001117 | −0.020168 | 0.012487 | 0.03231 | −0.005279 | −0.01421 | 0.006328 | 0.008338 | 0.007868 | −0.009782 | 0.024994 | −0.019969 |
| 84 | 0.015777 | −0.003925 | 0.015144 | −0.014782 | 0.018866 | 0.030523 | −0.027428 | 0.001067 | 0.019785 | −0.007252 | 0.004099 | −0.015511 | 0.009949 | −0.022883 |
| 85 | 0.086988 | 0.042833 | 0.055246 | 0.014278 | 0.013654 | −0.025459 | 0.039752 | 0.023047 | −0.005214 | −0.059292 | 0.051245 | −0.073478 | −0.052103 | 0.017993 |
| 86 | 0.025514 | −0.018144 | −0.024093 | −0.000058 | −0.037396 | −0.033165 | −0.021024 | −0.013037 | 0.060835 | −0.017823 | 0.051748 | 0.034401 | −0.026156 | 0.007912 |
| 87 | −0.009726 | 0.001929 | 0.01289 | 0.039156 | −0.110876 | −0.059654 | −0.067399 | −0.080332 | 0.051613 | −0.03436 | −0.037889 | 0.111782 | −0.023357 | 0.040395 |
| 88 | 0.017257 | −0.012439 | 0.02709 | −0.030831 | 0.03251 | 0.023668 | 0.009447 | 0.000925 | 0.03502 | 0.003702 | −0.011086 | −0.031077 | 0.029931 | −0.028161 |
| 89 | 0.005183 | 0.012677 | 0.011831 | −0.026352 | 0.013841 | 0.033011 | −0.006445 | 0.005678 | −0.013619 | −0.005287 | −0.003356 | −0.012615 | 0.022157 | −0.012689 |
| 90 | 0.002532 | 0.025618 | 0.018042 | −0.018283 | −0.003668 | 0.027954 | 0.001407 | −0.010014 | −0.001715 | −0.022201 | −0.037709 | 0.02608 | 0.053286 | −0.030327 |
| 91 | −0.002156 | 0.000442 | 0.021811 | 0.005151 | 0.014017 | −0.009423 | 0.007416 | 0.039017 | −0.030478 | −0.041644 | −0.000832 | −0.017669 | 0.013019 | −0.031941 |
| 92 | 0.0558 | −0.01322 | 0.054792 | 0.120109 | −0.019109 | 0.027513 | −0.024973 | 0.071962 | 0.024731 | 0.018197 | 0.065281 | −0.024797 | −0.027817 | −0.113593 |
| 93 | −0.012209 | −0.06792 | −0.009602 | −0.009679 | −0.018264 | 0.019125 | −0.008742 | −0.030598 | −0.016499 | 0.039473 | −0.01269 | 0.055947 | 0.032795 | 0.081903 |
| 94 | −0.019281 | −0.018832 | −0.024233 | −0.052147 | 0.080196 | −0.001819 | −0.022982 | 0.044844 | 0.062064 | 0.00565 | 0.043124 | −0.115321 | 0.064995 | 0.057423 |
| 95 | −0.098929 | 0.041241 | −0.015621 | 0.008424 | 0.022293 | −0.024857 | 0.096575 | 0.087493 | −0.009262 | 0.058635 | 0.087879 | −0.044708 | −0.003482 | −0.037379 |
| 96 | 0.010193 | 0.050441 | 0.121844 | 0.032674 | −0.020351 | 0.016907 | −0.019916 | −0.028291 | 0.025238 | 0.03461 | 0.15762 | −0.057745 | 0.027904 | 0.005402 |
| 97 | 0.121796 | −0.078888 | −0.058604 | −0.143477 | −0.046845 | 0.018127 | −0.090952 | 0.03832 | −0.055097 | 0.113935 | −0.043082 | 0.145639 | −0.046417 | −0.042641 |
| 98 | −0.036331 | −0.00188 | 0.0377 | −0.029276 | 0.038384 | −0.028437 | 0.014591 | 0.045943 | −0.038773 | 0.002614 | −0.063098 | −0.029668 | −0.021868 | −0.024622 |
| 99 | 0.056139 | −0.11844 | −0.081977 | −0.004792 | −0.045074 | 0.090421 | 0.013512 | −0.000734 | 0.106937 | −0.012117 | −0.065405 | 0.050065 | −0.005831 | −0.022307 |
| 100 | 0.023289 | 0.061998 | 0.041646 | 0.013387 | 0.101347 | −0.004397 | −0.00682 | 0.087797 | −0.035189 | 0.046116 | 0.026404 | 0.099195 | −0.037258 | −0.035803 |
| 101 | −0.036817 | −0.025448 | 0.06698 | −0.011975 | −0.006878 | −0.013375 | −0.054255 | 0.00804 | −0.053361 | −0.044708 | −0.000412 | 0.00119 | −0.045729 | −0.020749 |
| 102 | 0.055773 | −0.091121 | 0.083346 | −0.058793 | −0.040019 | 0.079203 | −0.036731 | −0.01856 | 0.060204 | −0.045087 | −0.008383 | −0.015131 | −0.070106 | 0.047191 |
| 103 | 0.078213 | −0.004147 | −0.057622 | 0.005772 | −0.109526 | −0.080838 | −0.100873 | −0.099127 | −0.020507 | −0.100954 | 0.066749 | −0.010352 | 0.005636 | 0.066829 |
| 104 | −0.036363 | 0.056374 | 0.128135 | 0.09886 | −0.007366 | −0.039702 | −0.043012 | 0.027451 | 0.05553 | −0.114274 | −0.046216 | −0.066395 | 0.117657 | −0.02259 |
| 105 | 0.014788 | −0.086034 | −0.038559 | −0.02191 | 0.010383 | −0.067749 | 0.004065 | 0.005528 | 0.104566 | 0.044161 | −0.01513 | 0.015774 | −0.05231 | 0.038138 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 106 | −0.021742 | −0.224054 | 0.033488 | 0.025281 | 0.131419 | −0.003633 | −0.176368 | 0.023444 | 0.01739 | −0.035394 | −0.089575 | −0.04476 | −0.108097 | 0.00367 |
| 107 | −0.021319 | −0.015241 | −0.022801 | 0.02166 | −0.004857 | −0.049582 | −0.058087 | 0.085241 | −0.075436 | 0.029982 | 0.097013 | −0.059479 | −0.014378 | −0.051459 |
| 108 | −0.038492 | −0.070576 | 0.043129 | −0.096799 | −0.056192 | −0.032012 | 0.102334 | 0.05568 | −0.043812 | −0.076243 | −0.02861 | 0.052986 | −0.060593 | 0.04118 |
| 109 | 0.014465 | 0.015701 | −0.04826 | −0.059567 | 0.019535 | 0.103897 | 0.096491 | −0.002615 | 0.010862 | 0.00902 | −0.009674 | 0.050926 | −0.015986 | −0.008936 |
| 110 | −0.063854 | −0.045143 | 0.031078 | 0.036711 | 0.064557 | 0.140999 | 0.072802 | 0.050472 | −0.092187 | 0.003873 | −0.032843 | 0.016448 | −0.051669 | 0.019825 |
| 111 | 0.022685 | −0.048859 | −0.057561 | 0.036312 | −0.114262 | −0.00518 | −0.109578 | −0.003932 | 0.015099 | 0.039286 | 0.001685 | −0.105658 | −0.084015 | −0.045437 |
| 112 | 0.016975 | −0.013281 | 0.007267 | 0.018638 | −0.043312 | 0.116344 | 0.092337 | 0.137398 | −0.003173 | 0.061323 | −0.102612 | −0.013964 | 0.027361 | −0.081385 |
| 113 | 0.09712 | 0.203162 | −0.01236 | −0.05371 | −0.000336 | −0.048766 | −0.013943 | −0.032479 | −0.000055 | 0.044742 | 0.164983 | 0.116268 | −0.010566 | −0.007785 |
| 114 | 0.002051 | 0.119503 | −0.010745 | 0.061601 | −0.010431 | 0.065183 | −0.072876 | −0.008722 | −0.117249 | 0.071003 | −0.077639 | 0.080634 | 0.044625 | 0.075405 |
| 115 | −0.018886 | −0.135163 | 0.03125 | −0.079261 | 0.025064 | −0.084985 | 0.065777 | 0.099904 | 0.013671 | 0.059045 | −0.063759 | −0.062915 | −0.039789 | 0.072791 |
| 116 | 0.011147 | −0.013601 | 0.040892 | 0.011555 | −0.010547 | −0.096737 | −0.168634 | 0.028238 | 0.018084 | 0.069525 | 0.084396 | 0.042201 | 0.191457 | −0.085032 |
| 117 | 0.039427 | −0.038812 | −0.00822 | −0.035586 | −0.012699 | −0.017096 | −0.038255 | 0.016424 | −0.054902 | 0.075211 | −0.028159 | −0.000336 | −0.053798 | −0.058704 |
| 118 | 0.008743 | 0.072943 | 0.112329 | −0.068481 | 0.09365 | −0.089682 | 0.058604 | −0.096047 | −0.116513 | 0.073603 | −0.04536 | 0.044275 | 0.136321 | −0.036213 |
| 119 | 0.007887 | 0.062869 | 0.077906 | −0.037198 | 0.045841 | −0.053098 | −0.037416 | 0.032227 | −0.051517 | −0.03718 | −0.003455 | −0.011041 | 0.06278 | 0.098248 |
| 120 | 0.015363 | −0.006255 | 0.044307 | −0.002326 | −0.04597 | −0.014402 | 0.04484 | 0.050905 | −0.115839 | 0.036269 | −0.043228 | 0.061844 | 0.111443 | 0.049758 |
| 121 | −0.002295 | −0.054477 | 0.00742 | −0.090507 | −0.035587 | 0.004163 | −0.04475 | −0.046149 | 0.059594 | −0.057944 | −0.036255 | −0.007752 | 0.078677 | −0.005382 |
| 122 | 0.132345 | 0.031192 | 0.009753 | −0.039977 | −0.014937 | 0.12436 | −0.014304 | −0.014822 | −0.073391 | 0.017445 | −0.034522 | −0.040302 | −0.010122 | −0.004707 |
| 123 | 0.078903 | −0.014855 | −0.012495 | 0.078573 | 0.006127 | 0.056963 | −0.022693 | −0.02434 | −0.00352 | −0.00055 | −0.044254 | 0.003707 | −0.08806 | 0.013561 |
| 124 | −0.040938 | 0.020047 | −0.009107 | −0.047454 | −0.039676 | 0.037782 | −0.035034 | 0.100897 | −0.014091 | 0.063391 | −0.037608 | −0.012776 | −0.033276 | −0.017082 |
| 125 | 0.026028 | −0.106808 | 0.078248 | −0.017208 | −0.061408 | 0.063139 | 0.084886 | 0.046706 | 0.010444 | −0.070339 | 0.043468 | 0.003078 | −0.04452 | −0.043195 |
| 126 | −0.01293 | −0.042839 | 0.045657 | −0.012707 | −0.01562 | 0.093488 | 0.026303 | −0.020217 | 0.101911 | 0.02756 | −0.009304 | −0.031599 | −0.003578 | −0.030387 |
| 127 | 0.080867 | 0.027331 | 0.042926 | 0.026923 | 0.012193 | 0.09964 | 0.036763 | −0.051241 | 0.04871 | 0.038477 | −0.038653 | −0.00628 | −0.007605 | −0.057267 |
| 128 | 0.025618 | 0.010801 | −0.015595 | 0.094143 | 0.021161 | −0.004569 | 0.060772 | −0.014005 | −0.021725 | −0.031573 | −0.05301 | 0.088771 | −0.134071 | −0.009209 |
| 129 | 0.036484 | 0.041413 | −0.047505 | −0.001935 | 0.008919 | −0.032758 | −0.01707 | 0.022299 | −0.025437 | 0.012684 | −0.03451 | 0.025261 | −0.003824 | −0.05432 |
| 130 | −0.02201 | −0.00082 | −0.041649 | −0.033548 | 0.034676 | −0.036588 | −0.158104 | 0.021882 | −0.077097 | 0.035611 | 0.053462 | −0.026299 | −0.082258 | −0.003507 |
| 131 | −0.015199 | 0.023106 | −0.017803 | 0.027762 | 0.033241 | 0.070047 | 0.063961 | 0.018501 | 0.028653 | −0.026876 | −0.019329 | −0.096631 | 0.006428 | 0.004245 |
| 132 | 0.045724 | −0.021651 | 0.057953 | −0.110645 | 0.169364 | −0.042036 | 0.113385 | −0.063532 | 0.113559 | −0.017407 | −0.016823 | −0.002933 | 0.078233 | 0.16009 |
| 133 | 0.103661 | 0.030907 | −0.037151 | −0.010364 | −0.139648 | −0.033949 | 0.007995 | 0.01781 | −0.000821 | 0.025277 | −0.011843 | −0.054398 | 0.031279 | −0.024831 |
| 134 | −0.023618 | −0.002102 | −0.041059 | −0.055365 | 0.043605 | 0.031677 | −0.067112 | −0.096602 | −0.065791 | −0.019419 | −0.002852 | 0.017568 | 0.02496 | −0.057382 |
| 135 | −0.02917 | 0.001267 | −0.060754 | 0.073769 | 0.061599 | −0.109557 | 0.008328 | 0.023215 | 0.022661 | 0.027891 | −0.03745 | −0.060046 | −0.05098 | −0.037806 |
| 136 | −0.054703 | −0.017039 | −0.054068 | 0.030982 | 0.002525 | −0.016174 | −0.002868 | −0.014517 | −0.004076 | 0.012648 | 0.026481 | 0.054624 | −0.079861 | −0.033702 |
| 137 | −0.033834 | −0.012069 | −0.040922 | −0.042262 | −0.037812 | 0.1011 | −0.052929 | −0.066978 | −0.024989 | −0.07507 | −0.053305 | 0.05876 | −0.093192 | 0.039743 |
| 138 | −0.046795 | −0.061323 | −0.12738 | −0.022889 | 0.045577 | −0.010088 | −0.093677 | −0.000258 | 0.06693 | −0.031427 | −0.020853 | −0.037101 | 0.021979 | 0.010871 |
| 139 | 0.002825 | 0.036965 | −0.069195 | −0.046729 | −0.130482 | 0.067588 | 0.002008 | −0.0052 | −0.055787 | 0.084168 | 0.026439 | 0.042656 | 0.063818 | −0.010545 |
| 140 | 0.02056 | 0.029612 | 0.05712 | −0.098659 | 0.037553 | 0.012026 | 0.020642 | 0.025986 | 0.033065 | 0.005151 | 0.035701 | 0.10293 | 0.065857 | 0.009134 |
| 141 | −0.059599 | 0.011839 | −0.058438 | −0.078008 | −0.020993 | −0.040046 | −0.168499 | 0.141741 | 0.056158 | 0.114451 | 0.085135 | 0.033406 | 0.031051 | 0.055637 |
| 142 | 0.068981 | −0.058101 | 0.070428 | −0.003148 | −0.036882 | −0.048633 | 0.057095 | 0.003975 | −0.04622 | −0.004129 | 0.057463 | −0.07127 | 0.06664 | −0.152727 |
| 143 | 0.015435 | −0.048764 | 0.094724 | −0.019642 | −0.048278 | 0.047119 | 0.049857 | −0.163432 | −0.003015 | −0.05646 | 0.149716 | −0.101018 | 0.011915 | 0.093935 |
| 144 | 0.043971 | 0.010236 | −0.051722 | 0.099685 | −0.019165 | 0.022302 | 0.025362 | −0.091799 | −0.001395 | 0.13096 | −0.041778 | 0.01696 | −0.027035 | 0.044841 |
| 145 | −0.154593 | −0.00652 | 0.016778 | −0.064937 | −0.150848 | −0.093169 | 0.02773 | 0.019032 | 0.143517 | −0.038668 | 0.055977 | 0.054672 | −0.079886 | −0.011036 |
| 146 | 0.021799 | −0.003299 | 0.052904 | 0.049252 | 0.033234 | −0.024301 | 0.065338 | 0.033173 | 0.083692 | −0.024385 | −0.025449 | 0.050818 | −0.011143 | −0.077564 |
| 147 | −0.025128 | 0.001603 | 0.025937 | 0.143132 | 0.042643 | −0.086211 | −0.017914 | 0.02298 | 0.010554 | 0.116544 | −0.028453 | 0.032469 | −0.031535 | 0.10769 |
| 148 | 0.073327 | 0.039522 | 0.003687 | −0.053089 | 0.13827 | −0.023331 | −0.023818 | −0.014787 | −0.021253 | −0.075769 | 0.028331 | −0.008568 | 0.067483 | −0.083664 |
| 149 | −0.067956 | −0.134977 | −0.009121 | 0.04316 | 0.033411 | −0.046763 | 0.070875 | −0.121824 | −0.052266 | −0.045107 | 0.06177 | 0.001433 | 0.033583 | −0.022129 |
| 150 | 0.004973 | −0.007162 | 0.114491 | 0.113489 | 0.002605 | −0.012376 | −0.109874 | 0.05769 | 0.094346 | 0.182217 | 0.07731 | 0.057354 | 0.03855 | 0.076528 |
| 151 | −0.112377 | −0.046555 | 0.030725 | 0.077119 | −0.095163 | 0.073115 | −0.037969 | −0.018068 | 0.037419 | 0.038749 | 0.043195 | −0.051332 | 0.004355 | 0.096174 |
| 152 | 0.033759 | 0.088593 | 0.084626 | −0.004875 | 0.009021 | 0.126448 | −0.072845 | 0.009172 | −0.066703 | −0.132425 | −0.101612 | −0.111426 | −0.026177 | −0.025352 |
| 153 | 0.030596 | 0.045344 | −0.193138 | −0.124825 | 0.099093 | 0.037923 | 0.010923 | −0.017701 | 0.048022 | −0.004201 | −0.055111 | −0.034913 | 0.064488 | 0.011325 |
| 154 | −0.054084 | −0.046766 | 0.151139 | 0.044318 | 0.057476 | −0.095651 | −0.01046 | −0.025302 | 0.02664 | 0.05868 | −0.009237 | 0.029011 | −0.017556 | 0.038885 |
| 155 | 0.066872 | 0.042887 | −0.121496 | 0.039929 | −0.134226 | −0.111919 | 0.031544 | 0.142206 | −0.063684 | −0.035704 | 0.042812 | −0.074813 | 0.18013 | 0.089526 |
| 156 | −0.117986 | 0.02258 | −0.065429 | −0.029121 | 0.059088 | −0.044023 | 0.028613 | 0.084853 | −0.078635 | −0.052786 | −0.089229 | 0.089794 | −0.062779 | 0.011037 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 157 | −0.006882 | 0.002285 | −0.122563 | −0.066732 | 0.107195 | 0.00539 | −0.00349 | 0.085719 | −0.045438 | −0.164979 | 0.038381 | −0.053592 | −0.063328 | −0.083286 |
| 158 | 0.03347 | 0.013414 | −0.015864 | 0.030473 | 0.020085 | 0.063216 | −0.049849 | −0.056296 | 0.057752 | 0.026855 | 0.090953 | −0.017273 | 0.029699 | −0.055552 |
| 159 | 0.004722 | −0.141327 | −0.026349 | −0.100108 | −0.032307 | 0.048747 | 0.048634 | −0.031426 | 0.00798 | 0.019563 | −0.026915 | −0.115453 | 0.116665 | 0.032929 |
| 160 | −0.04321 | 0.044964 | −0.035095 | −0.071799 | 0.076223 | −0.045961 | 0.035749 | 0.030629 | 0.053013 | 0.052391 | 0.002458 | −0.013772 | −0.076082 | 0.027844 |
| 161 | −0.033432 | −0.022974 | 0.058388 | 0.041609 | −0.061504 | 0.047973 | 0.009312 | −0.018809 | 0.069569 | −0.043772 | −0.03986 | −0.017294 | −0.056951 | −0.042602 |
| 162 | 0.091121 | −0.031705 | −0.024633 | 0.042827 | 0.020683 | 0.001433 | 0.018152 | 0.049792 | 0.071073 | −0.04765 | −0.048464 | 0.072065 | −0.037986 | 0.103613 |
| 163 | −0.066 | −0.066678 | −0.023067 | 0.034793 | −0.080351 | −0.023833 | −0.151506 | 0.011448 | −0.166075 | 0.004443 | 0.004456 | −0.088255 | 0.029973 | −0.051798 |
| 164 | −0.001901 | 0.023613 | 0.160058 | −0.039658 | 0.042706 | 0.059393 | −0.062467 | −0.052446 | 0.036726 | −0.077192 | 0.018599 | 0.039867 | −0.097595 | 0.039886 |
| 165 | −0.012836 | −0.0001 | −0.040853 | −0.055565 | 0.092845 | 0.046963 | −0.010754 | −0.029246 | 0.066777 | 0.093062 | 0.048896 | 0.063357 | 0.072089 | −0.116137 |
| 166 | −0.060852 | −0.137718 | 0.064947 | 0.005402 | −0.04621 | −0.021194 | 0.066695 | −0.014493 | −0.054178 | −0.028919 | −0.053089 | 0.036029 | 0.089295 | 0.01737 |
| 167 | −0.174903 | −0.112268 | 0.05083 | 0.007225 | −0.010945 | 0.063735 | −0.003466 | 0.03192 | −0.122659 | −0.042718 | −0.071145 | 0.083779 | −0.003403 | −0.030588 |
| 168 | −0.028361 | −0.059978 | 0.037099 | −0.082711 | −0.147634 | 0.001246 | −0.073321 | −0.100964 | −0.054907 | −0.118464 | −0.017654 | 0.027969 | −0.017479 | −0.026036 |
| 169 | 0.0608 | 0.002702 | −0.037548 | 0.03879 | −0.035315 | 0.011326 | 0.036286 | 0.006935 | −0.005423 | −0.009843 | −0.027495 | −0.033135 | −0.004265 | −0.002366 |
| 170 | 0.079155 | −0.052146 | −0.097695 | −0.00321 | −0.05409 | 0.021232 | −0.002153 | −0.013665 | 0.043958 | −0.011419 | −0.012882 | −0.02597 | −0.047613 | 0.039344 |
| 171 | 0.032747 | −0.022098 | −0.037025 | 0.078406 | 0.015061 | 0.05865 | 0.03446 | 0.03024 | 0.02489 | −0.01386 | −0.002719 | 0.044508 | 0.001471 | −0.001149 |
| 172 | 0.010926 | −0.056589 | 0.001229 | 0.007884 | −0.024533 | −0.034206 | 0.012179 | 0.091834 | 0.005019 | 0.006495 | −0.014251 | 0.1337 | 0.075831 | −0.0247 |
| 173 | 0.047365 | −0.095029 | −0.022182 | 0.010837 | 0.080321 | 0.004782 | 0.036428 | 0.050186 | −0.051824 | −0.035087 | 0.052504 | 0.137752 | −0.05474 | −0.005258 |
| 174 | −0.031471 | 0.018972 | 0.021811 | −0.072823 | −0.010568 | −0.056907 | −0.016745 | −0.046251 | −0.019059 | 0.010474 | 0.059007 | 0.006664 | −0.041932 | −0.011725 |
| 175 | −0.029579 | 0.037925 | 0.035494 | −0.107039 | 0.011272 | −0.099449 | 0.021526 | 0.098203 | −0.042263 | −0.06934 | −0.068527 | −0.058758 | 0.027328 | 0.047711 |
| 176 | −0.046195 | −0.042383 | −0.037564 | −0.035705 | −0.013723 | 0.156965 | 0.070467 | 0.024722 | 0.109168 | 0.038603 | 0.008065 | −0.000595 | −0.009754 | −0.078981 |
| 177 | 0.00257 | 0.044041 | 0.033805 | −0.005808 | −0.025539 | −0.021144 | −0.024365 | 0.003523 | −0.041163 | −0.001604 | −0.031536 | 0.029879 | −0.125153 | 0.002467 |
| 178 | −0.088584 | 0.002519 | 0.007151 | −0.055111 | −0.002449 | 0.023087 | 0.006554 | 0.015364 | 0.036048 | 0.071216 | 0.05393 | 0.027816 | 0.007656 | 0.018659 |
| 179 | −0.006066 | 0.044157 | 0.049192 | 0.007584 | −0.04976 | −0.010022 | 0.04281 | −0.01577 | −0.010919 | 0.006482 | −0.09335 | −0.047198 | 0.025481 | −0.027865 |
| 180 | −0.057066 | −0.031557 | 0.037712 | −0.0479 | −0.005844 | −0.001129 | 0.027429 | −0.018123 | −0.013327 | 0.002504 | 0.019967 | −0.017516 | 0.001823 | −0.028732 |
| 181 | −0.01232 | −0.012762 | 0.027336 | −0.043447 | 0.013766 | 0.00285 | 0.02195 | −0.026691 | 0.018736 | −0.004408 | −0.016349 | −0.075439 | 0.006764 | 0.0276 |
| 182 | 0.044261 | −0.025136 | −0.005737 | −0.037328 | 0.011632 | 0.0247 | −0.013092 | −0.038335 | −0.012143 | 0.037725 | 0.039156 | −0.015485 | 0.038599 | −0.019011 |
| 183 | 0.020102 | 0.078275 | −0.053672 | 0.079566 | 0.015746 | −0.027688 | 0.021849 | 0.04852 | −0.01729 | 0.010741 | −0.027419 | 0.004748 | −0.024885 | −0.002056 |
| 184 | 0.036033 | −0.051172 | 0.011289 | 0.058977 | 0.010703 | −0.11157 | 0.02883 | 0.022441 | −0.106475 | 0.072104 | 0.047076 | 0.030228 | −0.025333 | −0.004662 |
| 185 | −0.070161 | −0.012746 | −0.042388 | −0.158162 | −0.030942 | −0.064071 | 0.059715 | −0.023306 | 0.108168 | 0.014368 | −0.04736 | 0.001535 | −0.053716 | −0.114584 |
| 186 | −0.057349 | 0.006683 | 0.099359 | 0.021422 | 0.004073 | 0.079765 | −0.030373 | 0.0254 | 0.012113 | −0.067903 | 0.026052 | 0.041915 | 0.018347 | 0.0541 |
| 187 | 0.026273 | −0.050275 | −0.035247 | −0.046707 | 0.043756 | 0.084313 | −0.014198 | −0.022873 | −0.083764 | 0.096267 | 0.000513 | 0.012939 | 0.022874 | −0.112272 |
| 188 | −0.006239 | −0.046082 | −0.03642 | −0.053606 | 0.027581 | 0.064452 | −0.000964 | 0.038894 | −0.028175 | 0.084708 | −0.035746 | 0.06386 | 0.076606 | 0.002028 |
| 189 | −0.034498 | 0.029259 | 0.016341 | 0.102708 | 0.011218 | 0.054415 | 0.042063 | −0.019906 | −0.04541 | −0.031271 | −0.035113 | −0.003452 | 0.006783 | 0.015853 |
| 190 | −0.006426 | 0.034842 | −0.016563 | −0.090933 | −0.010985 | 0.083763 | −0.031118 | 0.032841 | 0.019259 | 0.014611 | 0.026876 | −0.00236 | −0.058976 | 0.089112 |
| 191 | 0.085167 | 0.040559 | 0.066186 | −0.151066 | −0.041725 | −0.032067 | 0.002704 | 0.055207 | −0.023384 | 0.016073 | −0.033675 | −0.069223 | −0.012968 | −0.030132 |
| 192 | −0.07772 | 0.016814 | 0.118467 | −0.017633 | −0.055696 | 0.000592 | 0.007375 | −0.028632 | 0.136666 | 0.014323 | −0.135982 | 0.003493 | 0.0424 | −0.101055 |
| 193 | 0.08992 | 0.010837 | −0.052674 | −0.043072 | −0.03389 | −0.058248 | −0.01577 | −0.088431 | −0.079477 | 0.060692 | −0.075897 | 0.114701 | −0.014964 | −0.068849 |
| 194 | 0.023363 | −0.004804 | −0.01665 | 0.150904 | 0.051688 | −0.017155 | 0.050902 | 0.083618 | 0.043656 | −0.036827 | 0.051065 | −0.127375 | −0.016957 | 0.103164 |
| 195 | −0.067513 | −0.07021 | 0.011041 | 0.034218 | 0.005973 | −0.095245 | −0.053678 | −0.07343 | −0.009099 | −0.047251 | 0.040347 | −0.051093 | −0.080491 | −0.062921 |
| 196 | −0.103427 | −0.069283 | 0.027853 | −0.052881 | 0.044451 | −0.05128 | −0.102774 | −0.030981 | 0.016836 | −0.028228 | 0.035799 | 0.101972 | 0.045049 | −0.067088 |
| 197 | 0.00923 | 0.15502 | −0.017207 | −0.02033 | −0.102549 | 0.016511 | −0.006036 | −0.033749 | 0.045294 | 0.031458 | −0.057296 | −0.013145 | 0.043172 | 0.002442 |
| 198 | 0.04265 | −0.031285 | −0.048094 | 0.089014 | −0.088937 | 0.007706 | −0.065793 | −0.024485 | −0.056871 | −0.016676 | −0.026016 | 0.074997 | −0.103515 | 0.136854 |
| 199 | −0.05397 | 0.023828 | 0.070053 | 0.048307 | −0.053231 | 0.078042 | 0.052931 | 0.040322 | −0.082771 | 0.154423 | 0.025046 | −0.0144 | 0.022459 | −0.097012 |
| 200 | −0.035592 | 0.101541 | −0.052466 | 0.073302 | 0.184202 | −0.12953 | 0.07989 | −0.054276 | 0.009709 | 0.026635 | −0.073214 | −0.120799 | −0.023464 | −0.161363 |
| 201 | −0.069791 | −0.002875 | 0.078386 | 0.022287 | −0.012602 | 0.063383 | −0.035741 | −0.037291 | −0.043546 | −0.077348 | 0.058999 | 0.028399 | −0.077605 | 0.038117 |
| 202 | −0.055063 | −0.060665 | −0.016303 | 0.028154 | −0.052006 | −0.052817 | 0.019097 | 0.085559 | −0.021133 | −0.156538 | 0.109226 | −0.036856 | 0.093307 | 0.039938 |
| 203 | −0.115085 | 0.019426 | −0.034709 | 0.001855 | 0.095468 | 0.007772 | −0.059657 | −0.048288 | 0.052339 | 0.002473 | −0.089292 | 0.087137 | −0.095615 | 0.058765 |
| 204 | 0.021015 | 0.018525 | 0.048807 | −0.097036 | 0.053528 | 0.083345 | 0.006646 | −0.025984 | 0.014833 | −0.014113 | −0.07498 | 0.053141 | −0.029608 | −0.049986 |
| 205 | 0.058691 | −0.074555 | −0.077116 | −0.025204 | 0.028244 | −0.033009 | −0.021416 | −0.05535 | −0.026202 | 0.018591 | −0.064255 | 0.013594 | −0.027611 | 0.00367 |
| 206 | −0.117858 | −0.054633 | −0.00369 | −0.003297 | 0.035253 | −0.018047 | 0.012886 | 0.027027 | 0.000305 | 0.045689 | −0.028414 | 0.013191 | −0.024715 | 0.058361 |
| 207 | 0.124643 | −0.011535 | 0.022204 | 0.024374 | −0.031515 | 0.015906 | −0.010303 | 0.060925 | 0.039245 | −0.07087 | 0.071478 | 0.019608 | −0.05804 | −0.003365 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 208 | 0.028648 | 0.097417 | 0.047657 | 0.048916 | −0.00859 | −0.124215 | 0.023081 | −0.020352 | −0.024091 | 0.083388 | 0.07964 | 0.060306 | 0.019096 | −0.096994 |
| 209 | 0.031478 | 0.091139 | −0.031884 | 0.011197 | 0.02977 | −0.118562 | 0.027148 | 0.056972 | −0.021783 | −0.029069 | −0.019356 | 0.023411 | −0.070431 | −0.022638 |
| 210 | 0.124228 | 0.013435 | −0.070044 | −0.033375 | 0.006518 | −0.000342 | 0.062641 | −0.034959 | −0.12278 | 0.005106 | 0.001791 | −0.017667 | 0.009197 | 0.094227 |
| 211 | −0.028546 | −0.009307 | 0.074436 | 0.04487 | −0.046694 | −0.122038 | 0.019471 | −0.015545 | −0.01215 | 0.013293 | −0.035418 | −0.013575 | 0.001233 | 0.036717 |
| 212 | −0.021304 | −0.0309 | −0.04317 | −0.055187 | 0.070391 | 0.047981 | −0.088721 | 0.028764 | −0.06277 | −0.063287 | 0.005914 | −0.000905 | −0.081168 | 0.035831 |
| 213 | −0.005394 | −0.079148 | 0.053256 | 0.12876 | −0.033484 | −0.054525 | 0.022146 | 0.03458 | −0.011306 | −0.0025 | 0.022617 | 0.074649 | 0.00949 | −0.05387 |
| 214 | −0.012385 | 0.02348 | 0.030704 | 0.041371 | 0.041393 | 0.008206 | 0.016966 | 0.042313 | 0.037045 | 0.001316 | −0.009266 | 0.016418 | −0.001897 | −0.035565 |
| 215 | 0.041982 | −0.033591 | 0.041365 | 0.09144 | 0.041526 | 0.078941 | −0.118321 | 0.0381 | −0.090325 | 0.021863 | 0.042523 | 0.004956 | 0.081205 | 0.023239 |
| 216 | −0.028792 | 0.022013 | 0.012341 | 0.013414 | −0.005046 | 0.051406 | 0.009856 | 0.005761 | −0.064708 | 0.070281 | 0.063727 | −0.078186 | −0.038743 | −0.029267 |
| 217 | −0.086828 | −0.003841 | 0.030257 | 0.006845 | 0.058481 | −0.058662 | −0.06569 | 0.024259 | 0.089165 | 0.167415 | 0.004313 | 0.013774 | −0.014574 | 0.041067 |
| 218 | 0.020334 | −0.014963 | 0.069418 | −0.004255 | 0.002762 | −0.04045 | −0.03558 | 0.000801 | −0.05607 | −0.037723 | 0.058755 | 0.015847 | 0.020999 | −0.044571 |
| 219 | −0.021789 | −0.042945 | −0.0201 | −0.019684 | 0.013002 | −0.01066 | −0.027441 | −0.034835 | −0.058907 | −0.040421 | 0.01609 | 0.04217 | −0.039919 | −0.035678 |
| 220 | 0.026034 | 0.000626 | 0.091583 | −0.004207 | 0.020896 | −0.005774 | 0.034511 | −0.062472 | 0.019947 | 0.035922 | 0.054892 | 0.04279 | 0.063575 | −0.010766 |
| 221 | −0.090455 | 0.059675 | −0.021052 | 0.025249 | 0.064155 | 0.001692 | 0.011205 | 0.020775 | −0.01095 | −0.033863 | 0.042847 | 0.059832 | 0.02702 | −0.066625 |
| 222 | −0.041408 | 0.029348 | −0.014137 | 0.032347 | 0.055921 | −0.039855 | −0.031512 | 0.027657 | 0.032895 | −0.020803 | 0.031639 | 0.097489 | 0.058564 | 0.037188 |
| 223 | 0.027521 | −0.029492 | −0.057482 | 0.011965 | 0.077061 | 0.045984 | −0.040949 | −0.029045 | −0.053723 | −0.002827 | 0.081699 | 0.025745 | −0.005825 | −0.008401 |
| 224 | −0.055475 | 0.039613 | 0.049301 | −0.065829 | 0.006951 | 0.031535 | 0.069431 | −0.013433 | 0.049815 | 0.026262 | −0.00271 | −0.028485 | 0.000626 | −0.014218 |
| 225 | −0.009582 | 0.023373 | 0.018638 | −0.047475 | −0.003025 | −0.041845 | −0.002644 | −0.035736 | 0.016121 | −0.031829 | −0.029604 | −0.026547 | −0.024056 | 0.008995 |
| 226 | 0.007086 | −0.000347 | 0.019607 | 0.006348 | −0.007869 | 0.015676 | −0.033967 | −0.000994 | −0.003026 | −0.042963 | 0.016302 | 0.014739 | 0.064257 | −0.02693 |
| 227 | 0.006915 | 0.014088 | 0.006894 | −0.035824 | 0.02113 | −0.083407 | −0.050123 | 0.007733 | 0.070219 | −0.067423 | −0.0156 | 0.033574 | −0.082737 | 0.049926 |
| 228 | 0.030505 | −0.096556 | 0.039744 | 0.066011 | −0.092024 | 0.074908 | −0.065822 | −0.007244 | 0.039453 | −0.015609 | −0.007861 | −0.059874 | 0.06824 | −0.005962 |
| 229 | 0.102076 | −0.05839 | −0.05224 | 0.03273 | 0.033384 | −0.075594 | −0.014833 | 0.018209 | −0.018249 | 0.053505 | −0.006531 | −0.101637 | −0.067984 | 0.050599 |
| 230 | 0.069952 | 0.005075 | −0.007204 | 0.060255 | 0.003236 | 0.022765 | −0.002735 | 0.008059 | 0.028696 | −0.007506 | 0.001089 | 0.013321 | −0.012738 | −0.018551 |
| 231 | 0.054203 | 0.018604 | 0.026325 | −0.04174 | 0.019982 | −0.093254 | −0.085654 | −0.017043 | −0.16214 | 0.098793 | −0.089625 | −0.011628 | −0.023954 | −0.058302 |
| 232 | 0.018996 | 0.008321 | −0.067355 | 0.062836 | −0.043746 | −0.018281 | 0.013561 | −0.017811 | −0.084029 | −0.083433 | −0.006185 | 0.122177 | 0.051389 | 0.14181 |
| 233 | −0.106196 | 0.035328 | −0.035067 | −0.059948 | −0.071503 | −0.096472 | −0.010141 | −0.065987 | 0.049885 | 0.08648 | 0.071482 | −0.000029 | −0.003442 | 0.022803 |
| 234 | −0.047534 | 0.021358 | −0.01033 | 0.035316 | −0.019996 | 0.056412 | −0.054612 | −0.160089 | 0.003222 | 0.028315 | 0.009973 | 0.068775 | 0.098236 | −0.045105 |
| 235 | −0.020189 | −0.02013 | −0.035846 | 0.033969 | −0.031069 | −0.027378 | −0.050065 | 0.099935 | 0.050439 | −0.003696 | −0.073444 | −0.034781 | 0.038253 | −0.007433 |
| 236 | 0.06422 | 0.022825 | −0.034769 | −0.031717 | 0.006147 | 0.055114 | 0.036841 | −0.045368 | 0.011415 | 0.026044 | 0.04076 | −0.044428 | 0.001665 | −0.05088 |
| 237 | −0.117204 | 0.008772 | −0.050103 | 0.130834 | 0.015359 | −0.005875 | 0.001157 | 0.028368 | −0.031553 | −0.078488 | −0.082133 | 0.000621 | 0.045072 | −0.042834 |
| 238 | 0.000931 | 0.018976 | −0.012633 | −0.033121 | 0.025005 | 0.02909 | 0.064264 | 0.00051 | 0.054499 | −0.059465 | −0.005196 | 0.014129 | −0.00505 | 0.040488 |
| 239 | 0.047247 | −0.028431 | 0.019785 | −0.046015 | −0.022836 | 0.028284 | −0.013605 | 0.024991 | 0.072378 | −0.015979 | 0.041113 | −0.010413 | −0.047721 | −0.034248 |
| 240 | −0.035103 | −0.078991 | 0.018888 | 0.018901 | 0.030494 | 0.030836 | 0.037057 | 0.078599 | 0.031051 | 0.027149 | −0.067806 | −0.066853 | −0.024508 | 0.003732 |
| 241 | −0.063364 | 0.006069 | −0.096623 | 0.012371 | −0.067108 | 0.002435 | −0.049773 | −0.093744 | 0.011465 | 0.045109 | 0.053524 | −0.074162 | −0.051357 | −0.017103 |
| 242 | 0.081228 | 0.027606 | 0.045229 | −0.052988 | 0.00806 | −0.015557 | −0.011781 | −0.025644 | 0.010326 | −0.025382 | 0.057722 | −0.009512 | −0.043937 | 0.055902 |
| 243 | −0.06151 | 0.025912 | −0.032971 | −0.07272 | −0.017957 | 0.012932 | 0.021505 | 0.083628 | −0.051806 | −0.01814 | 0.051574 | 0.002644 | −0.037349 | 0.009311 |
| 244 | 0.005971 | 0.0616 | −0.054793 | −0.046157 | −0.024469 | −0.014348 | −0.037774 | 0.011017 | 0.004038 | −0.010257 | 0.018453 | −0.011848 | 0.005473 | −0.031941 |
| 245 | 0.044058 | −0.065235 | −0.010919 | 0.036017 | −0.028501 | −0.059022 | −0.065745 | −0.02712 | 0.028789 | 0.051031 | −0.039334 | 0.010482 | 0.005522 | 0.052956 |
| 246 | 0.061618 | −0.034541 | 0.048104 | 0.019996 | −0.045758 | −0.051672 | −0.066525 | −0.011395 | 0.039315 | −0.056349 | −0.021529 | −0.038254 | −0.028024 | −0.044231 |
| 247 | −0.017771 | 0.011071 | −0.051174 | −0.026265 | −0.024332 | 0.083551 | −0.047786 | 0.080913 | 0.061016 | −0.025897 | −0.01252 | 0.009272 | 0.048425 | −0.035119 |
| 248 | −0.044187 | 0.035994 | −0.050427 | 0.023085 | −0.001696 | 0.018913 | −0.034566 | 0.057932 | −0.046386 | −0.02722 | −0.050834 | −0.045188 | 0.133759 | 0.00277 |
| 249 | −0.056113 | −0.048332 | −0.053679 | −0.008942 | −0.018821 | −0.087724 | 0.117025 | −0.022636 | 0.001372 | 0.022118 | −0.012619 | −0.061571 | −0.074029 | 0.055797 |
| 250 | −0.049099 | 0.01331 | −0.035152 | −0.040294 | 0.063476 | −0.02436 | 0.030261 | 0.077014 | −0.10303 | 0.028314 | 0.070631 | −0.018903 | −0.062163 | 0.00193 |
| 251 | 0.05503 | 0.03241 | −0.038964 | 0.052248 | 0.051888 | 0.033871 | −0.020322 | 0.072285 | 0.015043 | −0.02955 | 0.023481 | 0.066295 | −0.037471 | −0.017511 |
| 252 | 0.086727 | 0.031383 | 0.008427 | −0.050043 | −0.098929 | −0.025962 | −0.000545 | 0.053744 | 0.011534 | −0.053673 | −0.035074 | 0.001177 | −0.043413 | 0.046675 |
| 253 | 0.025088 | −0.007292 | 0.012673 | 0.060545 | 0.047263 | −0.015918 | 0.014693 | −0.075815 | −0.021681 | −0.002477 | −0.046225 | −0.140661 | −0.016932 | 0.025106 |
| 254 | 0.039553 | 0.080856 | −0.062536 | −0.108251 | −0.07083 | −0.058168 | −0.027638 | −0.09903 | 0.016708 | 0.023642 | 0.044412 | −0.043634 | −0.107926 | 0.066588 |
| 255 | 0.024783 | 0.037549 | −0.033778 | −0.067849 | −0.015899 | 0.015994 | −0.019467 | 0.003071 | −0.01986 | −0.001327 | 0.018338 | 0.016665 | −0.020522 | −0.012542 |
| 256 | 0.016486 | −0.04044 | −0.024111 | 0.024805 | −0.036924 | −0.030626 | 0.035228 | 0.038701 | −0.034075 | 0.039729 | −0.004428 | 0.02272 | −0.0142 | 0.073939 |
| 257 | −0.031753 | 0.027535 | 0.000539 | −0.048573 | −0.058381 | −0.033021 | 0.00532 | −0.000623 | −0.038396 | 0.030527 | 0.003564 | 0.010089 | 0.015987 | 0.017982 |
| 258 | −0.007742 | −0.017801 | 0.008246 | 0.011154 | −0.108307 | 0.018338 | −0.058832 | 0.013517 | 0.024655 | 0.030102 | −0.050446 | −0.021861 | 0.067616 | −0.052658 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 259 | 0.054034 | −0.05668 | −0.023019 | −0.020509 | 0.113672 | −0.025961 | 0.008397 | 0.009032 | 0.020457 | −0.029948 | 0.056024 | −0.027586 | 0.040327 | −0.060548 |
| 260 | 0.114788 | −0.084826 | −0.031132 | −0.015944 | −0.005617 | −0.048918 | −0.064133 | 0.013897 | −0.096095 | −0.068104 | 0.007153 | 0.048472 | 0.014377 | 0.002952 |
| 261 | 0.019099 | −0.021824 | −0.028043 | 0.123427 | −0.012097 | 0.005859 | −0.000069 | −0.066838 | −0.007411 | 0.003187 | −0.004521 | 0.026555 | 0.028055 | 0.010694 |
| 262 | −0.064 | 0.046518 | 0.033453 | 0.037346 | 0.045629 | 0.024689 | −0.001362 | −0.031825 | −0.006281 | 0.026909 | 0.079139 | −0.005743 | −0.025997 | −0.038232 |
| 263 | −0.049283 | 0.018581 | 0.013691 | 0.05937 | 0.081884 | 0.045954 | 0.042637 | −0.04834 | −0.015458 | −0.031508 | 0.018622 | 0.007041 | −0.023248 | 0.025783 |
| 264 | −0.021141 | −0.001346 | 0.018784 | 0.027043 | −0.009834 | −0.008212 | 0.070614 | 0.041836 | 0.014998 | 0.040106 | 0.041607 | −0.042975 | 0.049662 | 0.024273 |
| 265 | 0.044727 | 0.003551 | 0.051189 | 0.010236 | −0.050627 | 0.038237 | −0.056511 | −0.005153 | 0.013234 | 0.015634 | 0.000373 | −0.07366 | 0.022339 | −0.070987 |
| 266 | 0.05159 | 0.019309 | 0.016473 | 0.046697 | 0.023613 | 0.040839 | 0.00739 | −0.03142 | 0.018918 | 0.069994 | −0.090898 | 0.013652 | 0.013845 | −0.006934 |
| 267 | −0.038228 | 0.051299 | 0.076175 | −0.054571 | 0.0249 | 0.0338 | −0.126161 | −0.013171 | −0.0135 | −0.091045 | −0.013546 | 0.004486 | −0.010976 | 0.020741 |
| 268 | −0.020458 | −0.040543 | 0.051282 | −0.009529 | −0.005658 | 0.088746 | 0.007396 | 0.002724 | −0.025321 | −0.044902 | 0.006173 | 0.046518 | 0.028173 | −0.009605 |
| 269 | 0.011572 | −0.001179 | −0.035716 | 0.021782 | 0.01781 | 0.03861 | 0.040744 | 0.015972 | −0.052312 | −0.007743 | 0.003514 | −0.012598 | −0.037227 | 0.045254 |
| 270 | −0.005473 | 0.036802 | −0.019235 | 0.007768 | −0.004827 | −0.01778 | 0.005204 | −0.016839 | −0.035752 | 0.014588 | 0.002196 | −0.009227 | −0.019691 | 0.04434 |
| 271 | −0.027633 | 0.107258 | −0.046174 | −0.10753 | 0.069688 | 0.09303 | 0.013242 | −0.016293 | 0.059036 | 0.034182 | −0.018691 | −0.003791 | 0.063689 | 0.061682 |
| 272 | 0.012888 | 0.014418 | 0.061414 | 0.067872 | 0.01836 | −0.030278 | −0.066843 | 0.016133 | −0.026966 | 0.004146 | −0.058658 | −0.006531 | −0.020648 | −0.068446 |
| 273 | −0.017758 | −0.026221 | 0.016459 | 0.034794 | −0.016304 | 0.003877 | −0.00695 | 0.014841 | −0.033139 | 0.017987 | 0.024654 | −0.010261 | 0.013224 | −0.039279 |
| 274 | −0.015722 | −0.034439 | 0.002994 | 0.022734 | −0.026783 | 0.012232 | −0.021709 | 0.009046 | −0.033191 | 0.035234 | 0.000579 | −0.008113 | −0.01784 | −0.064368 |
| 275 | 0.053278 | 0.072926 | −0.106642 | 0.026441 | 0.035276 | −0.000462 | −0.023397 | −0.011637 | −0.021546 | −0.023884 | 0.103463 | −0.046664 | 0.028444 | 0.001584 |
| 276 | 0.021251 | 0.019749 | 0.044908 | −0.039389 | 0.002431 | 0.042265 | 0.086673 | −0.080873 | 0.050928 | 0.046771 | −0.029545 | −0.019991 | −0.011732 | −0.066103 |
| 277 | −0.040999 | −0.005762 | 0.038403 | −0.019772 | −0.004541 | 0.009001 | −0.003867 | −0.035931 | −0.057901 | 0.034781 | −0.038395 | 0.011771 | 0.025114 | 0.054757 |
| 278 | 0.010409 | −0.013083 | −0.033023 | −0.048067 | 0.056526 | 0.001873 | 0.02017 | −0.054811 | −0.040507 | 0.091719 | −0.091721 | −0.009717 | −0.021086 | 0.103988 |
| 279 | 0.056558 | −0.001788 | 0.012662 | 0.001428 | 0.027817 | 0.004717 | 0.090731 | −0.012418 | 0.044402 | 0.047493 | 0.008404 | −0.006267 | 0.013977 | 0.027553 |
| 280 | −0.075058 | 0.028591 | 0.003411 | 0.041096 | 0.022527 | 0.0401 | 0.075461 | 0.016897 | 0.026953 | 0.012727 | −0.020492 | 0.143811 | −0.008688 | −0.052838 |
| 781 | 0.040666 | −0.025839 | 0.063722 | 0.095799 | −0.028165 | −0.059225 | 0.042006 | 0.075954 | 0.030433 | −0.063092 | −0.006415 | 0.007302 | −0.015944 | −0.04921 |
| 282 | 0.064897 | −0.003325 | −0.057804 | −0.066809 | 0.045483 | 0.01387 | 0.050593 | 0.079725 | 0.030129 | −0.001763 | 0.01917 | −0.064991 | −0.081722 | 0.015596 |
| 283 | −0.027401 | 0.01183 | −0.022947 | 0.022276 | 0.071613 | 0.025859 | −0.05678 | 0.107117 | 0.007899 | 0.040263 | 0.012228 | −0.003796 | 0.006643 | −0.035956 |
| 284 | −0.004124 | 0.035849 | 0.044206 | −0.015181 | −0.025175 | −0.086554 | 0.07375 | −0.023572 | −0.004695 | 0.014495 | 0.058621 | 0.011493 | 0.006149 | 0.02301 |
| 285 | 0.006083 | −0.006662 | 0.035935 | −0.089318 | 0.023029 | −0.005977 | 0.008854 | −0.021243 | −0.019327 | 0.054564 | 0.061994 | −0.016745 | −0.022325 | 0.036711 |
| 286 | 0.003941 | −0.02038 | −0.032658 | 0.032425 | −0.009492 | −0.04301 | 0.042366 | −0.042934 | 0.019536 | 0.022952 | 0.000253 | 0.002384 | 0.034326 | 0.000321 |
| 287 | 0.039068 | −0.068248 | −0.074173 | −0.005974 | 0.010121 | −0.034748 | −0.003279 | −0.040773 | 0.004701 | 0.014712 | −0.01375 | −0.001012 | −0.018851 | 0.081215 |
| 288 | 0.021255 | −0.038324 | 0.021061 | 0.019743 | 0.058197 | 0.00851 | −0.063252 | 0.008815 | −0.044832 | 0.037193 | −0.023408 | −0.033969 | 0.015349 | 0.064946 |
| 289 | 0.010633 | 0.034571 | −0.055913 | −0.029836 | 0.050169 | 0.024705 | −0.063996 | −0.039985 | 0.021758 | 0.054764 | 0.079125 | −0.007411 | −0.019469 | −0.036472 |
| 290 | 0.069922 | 0.015402 | 0.014161 | −0.016089 | 0.033016 | 0.024554 | −0.023213 | 0.040509 | −0.012769 | 0.008014 | 0.028163 | 0.063975 | 0.02309 | 0.008785 |
| 291 | 0.071833 | 0.033079 | −0.000935 | −0.007905 | 0.03209 | 0.033153 | −0.005558 | 0.047447 | −0.001261 | −0.004773 | 0.019541 | 0.042271 | 0.013585 | 0.025527 |
| 292 | 0.034377 | 0.023312 | −0.029818 | 0.005402 | 0.042081 | 0.000262 | 0.001138 | 0.053108 | 0.03852 | −0.046486 | 0.048972 | 0.002645 | 0.032133 | 0.000474 |
| 293 | 0.068775 | −0.039971 | 0.086861 | 0.082818 | 0.072387 | −0.018564 | 0.05801 | 0.054733 | −0.043963 | 0.003688 | −0.045097 | −0.006898 | 0.146818 | 0.077329 |
| 294 | −0.077387 | 0.093841 | −0.040365 | −0.012387 | −0.099286 | −0.04582 | −0.018119 | −0.023938 | −0.035264 | 0.071556 | 0.015221 | −0.036233 | −0.019436 | 0.03989 |
| 295 | −0.021459 | 0.011916 | 0.035244 | −0.010054 | −0.00912 | −0.015115 | 0.00648 | 0.017405 | 0.051861 | 0.017474 | −0.062191 | 0.011098 | −0.039537 | −0.006742 |
| 296 | −0.127896 | 0.062032 | −0.007183 | −0.024554 | −0.00252 | −0.002614 | −0.012247 | −0.124927 | 0.048046 | −0.066938 | 0.004088 | 0.056953 | −0.081555 | 0.065082 |
| 297 | −0.006905 | −0.082214 | 0.030193 | −0.037073 | 0.005145 | −0.098721 | 0.078687 | −0.001329 | −0.004016 | 0.097563 | −0.044995 | −0.008751 | −0.041524 | 0.033134 |
| 298 | 0.031606 | −0.027575 | 0.031938 | 0.060227 | 0.085212 | −0.058756 | −0.003177 | −0.056139 | 0.031961 | −0.070805 | −0.038523 | −0.013338 | −0.081411 | 0.108381 |
| 299 | 0.096117 | −0.000518 | 0.001135 | 0.000928 | −0.008452 | 0.0982 | 0.00019 | −0.003861 | −0.045577 | 0.03976 | −0.017543 | 0.022846 | 0.027903 | 0.022151 |
| 300 | −0.03176 | −0.027846 | −0.070999 | 0.058697 | 0.019769 | −0.086538 | 0.024284 | 0.002976 | −0.004279 | 0.076522 | −0.076666 | 0.052163 | 0.029565 | −0.062163 |
| 301 | 0.012546 | 0.055918 | 0.029711 | 0.012368 | 0.017536 | −0.002578 | 0.076965 | −0.015331 | 0.014054 | −0.006109 | 0.046822 | 0.053158 | −0.00417 | 0.031477 |
| 302 | −0.029088 | 0.011021 | −0.026078 | 0.045305 | −0.012083 | 0.02393 | −0.002577 | −0.063651 | −0.021964 | 0.06389 | 0.066553 | −0.025013 | −0.008543 | 0.028291 |
| 303 | 0.049166 | 0.017424 | −0.048299 | −0.012997 | −0.048997 | 0.023129 | 0.009666 | −0.000489 | −0.002199 | 0.008626 | 0.003342 | −0.004396 | 0.046467 | −0.039131 |
| 304 | −0.015524 | 0.041827 | 0.066846 | −0.032893 | 0.07408 | −0.068348 | −0.024571 | −0.001523 | 0.011045 | 0.002788 | −0.048568 | 0.028548 | 0.110861 | −0.047751 |
| 305 | 0.070179 | −0.093643 | −0.083438 | −0.006624 | 0.012973 | −0.073184 | −0.004103 | 0.003355 | 0.145118 | −0.076452 | −0.126806 | 0.033825 | 0.045041 | −0.098329 |
| 306 | −0.005756 | 0.011493 | −0.000206 | 0.114713 | −0.038663 | 0.019938 | 0.072667 | 0.05844 | −0.03149 | −0.071902 | 0.008333 | −0.01688 | −0.027879 | −0.02691 |
| 307 | 0.057946 | 0.02935 | 0.09627 | −0.105736 | 0.035727 | 0.043411 | 0.096464 | 0.070494 | 0.013567 | 0.019588 | 0.027345 | −0.004372 | 0.028183 | −0.069125 |
| 308 | 0.020066 | −0.061961 | 0.072381 | −0.000026 | 0.048448 | 0.04002 | −0.014434 | −0.00007 | −0.051129 | 0.014695 | −0.039663 | 0.028353 | −0.044569 | 0.03803 |
| 309 | −0.008535 | −0.075023 | −0.022765 | −0.006446 | 0.005392 | 0.065767 | −0.016253 | 0.078701 | −0.069578 | −0.041633 | −0.011456 | −0.01904 | −0.037065 | 0.072603 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 310 | −0.009089 | −0.015634 | −0.023742 | 0.008875 | −0.053542 | 0.039602 | 0.006074 | 0.049391 | −0.055061 | 0.034003 | 0.018157 | −0.108108 | −0.074882 | −0.066276 |
| 311 | 0.02259 | 0.003496 | −0.036613 | 0.060343 | 0.108219 | −0.018379 | 0.001607 | −0.033214 | 0.017287 | 0.014228 | −0.011996 | 0.016083 | 0.090204 | 0.029244 |
| 312 | 0.009744 | −0.000891 | 0.006016 | 0.022958 | −0.01217 | −0.060557 | −0.015472 | −0.044314 | −0.026994 | 0.093887 | 0.001614 | −0.03124 | 0.010252 | 0.051815 |
| 313 | −0.054901 | 0.087043 | 0.019035 | −0.022327 | 0.015472 | −0.037652 | 0.098825 | −0.025212 | 0.069152 | −0.13498 | −0.050351 | −0.005687 | 0.088218 | 0.038737 |
| 314 | −0.044501 | −0.025818 | 0.009482 | 0.018021 | −0.04587 | −0.024623 | −0.035943 | 0.03748 | −0.099955 | −0.005271 | 0.000839 | −0.068029 | −0.062553 | −0.065713 |
| 315 | −0.034664 | −0.018456 | −0.013163 | 0.027365 | 0.017546 | 0.070659 | −0.046645 | −0.043926 | 0.017413 | −0.02293 | −0.0307 | 0.007108 | −0.027494 | −0.04354 |
| 316 | 0.023993 | 0.024696 | −0.061148 | −0.007966 | −0.13422 | 0.069537 | 0.084657 | −0.057406 | 0.033185 | 0.138302 | −0.004648 | −0.026989 | −0.078588 | −0.089116 |
| 317 | 0.022637 | −0.012815 | −0.02057 | −0.070881 | 0.079799 | 0.039307 | −0.019677 | 0.08276 | −0.115736 | −0.057608 | 0.024814 | −0.088781 | −0.072723 | 0.016201 |
| 318 | −0.124735 | −0.009746 | −0.16094 | −0.009366 | 0.034386 | 0.086247 | −0.045404 | 0.009521 | −0.039191 | 0.01035 | −0.067478 | −0.033787 | 0.114382 | 0.073162 |
| 319 | −0.029584 | −0.033162 | −0.021182 | 0.017969 | 0.026875 | 0.017563 | −0.000089 | −0.032207 | −0.074927 | −0.004999 | −0.036751 | −0.096255 | −0.005897 | −0.069067 |
| 320 | 0.06348 | 0.1038 | 0.161002 | −0.054884 | 0.021342 | −0.107853 | −0.072681 | −0.145077 | 0.000092 | 0.020561 | 0.068947 | −0.05199 | 0.073599 | 0.010059 |
| 321 | 0.011877 | −0.015876 | −0.05438 | 0.00677 | −0.108687 | 0.071496 | 0.061025 | 0.003766 | 0.021958 | −0.00665 | 0.12133 | 0.020382 | −0.050471 | −0.065889 |
| 322 | 0.08982 | −0.009408 | 0.057217 | −0.00068 | −0.067212 | 0.02775 | −0.039269 | 0.003856 | −0.007207 | −0.020676 | −0.003677 | 0.137622 | 0.034824 | −0.038892 |
| 323 | 0.040933 | 0.051027 | 0.009589 | 0.057611 | 0.024556 | −0.030767 | −0.015102 | 0.10878 | 0.078522 | 0.078592 | 0.020006 | 0.015162 | 0.014975 | 0.026754 |
| 324 | 0.040709 | −0.016881 | −0.04768 | 0.064639 | −0.066136 | 0.055868 | −0.001579 | −0.094288 | −0.036415 | 0.015965 | 0.005719 | −0.068044 | 0.072601 | 0.064613 |
| 325 | 0.03397 | 0.008851 | 0.098294 | 0.035578 | −0.055769 | −0.002394 | 0.153734 | 0.013356 | 0.008325 | −0.009216 | 0.125599 | 0.029527 | −0.046199 | 0.053569 |
| 326 | −0.02565 | 0.113678 | 0.023048 | −0.052979 | −0.029906 | −0.007313 | 0.092089 | −0.118306 | −0.065579 | −0.06257 | 0.075752 | 0.055137 | −0.096622 | −0.016723 |
| 327 | 0.048308 | 0.022275 | 0.043689 | 0.010146 | −0.031473 | 0.093036 | −0.103426 | 0.049503 | 0.101213 | 0.011936 | −0.021639 | 0.037964 | −0.069107 | 0.015337 |
| 328 | −0.029848 | −0.116458 | −0.048207 | −0.062407 | 0.072653 | −0.039638 | 0.02828 | 0.035748 | −0.022143 | 0.012402 | −0.007868 | −0.087257 | 0.067262 | 0.085173 |
| 329 | 0.021437 | 0.010913 | −0.043088 | 0.058128 | 0.003547 | 0.018446 | −0.049333 | 0.028754 | 0.047245 | 0.021055 | −0.018448 | 0.066438 | −0.039023 | −0.147042 |
| 330 | 0.051198 | 0.034563 | 0.029515 | 0.05213 | 0.103774 | 0.012213 | 0.064343 | 0.05973 | 0.010187 | −0.007622 | 0.030321 | −0.084187 | −0.069925 | −0.010214 |
| 331 | 0.043732 | −0.037625 | 0.028888 | 0.036809 | −0.012082 | 0.003273 | 0.0243 | 0.033639 | 0.02979 | −0.008803 | −0.00796 | 0.101711 | −0.064703 | 0.003425 |
| 332 | 0.011097 | 0.098324 | −0.067101 | 0.007503 | −0.06618 | 0.002325 | −0.04222 | 0.040882 | 0.035729 | −0.015586 | −0.12172 | 0.044683 | 0.104668 | −0.024723 |
| 333 | −0.024692 | 0.013359 | 0.027038 | −0.038096 | −0.05189 | −0.061097 | 0.085572 | 0.078831 | −0.027068 | 0.061869 | 0.015199 | 0.059781 | −0.022095 | 0.00915 |
| 334 | −0.075238 | 0.127657 | 0.125816 | −0.028496 | −0.036225 | 0.089228 | 0.010044 | 0.027148 | −0.055905 | 0.022161 | 0.025567 | 0.023343 | 0.031516 | −0.029619 |
| 335 | 0.094974 | 0.030724 | −0.000288 | 0.0436 | 0.050167 | −0.073625 | 0.074074 | 0.022067 | 0.05553 | 0.081244 | −0.038349 | −0.074675 | −0.058395 | −0.02042 |
| 336 | 0.024443 | 0.024356 | −0.083163 | −0.088621 | 0.183745 | 0.068139 | −0.097139 | 0.055601 | −0.008808 | −0.036981 | 0.06525 | −0.047027 | −0.006991 | 0.039435 |
| 337 | 0.084461 | −0.036777 | −0.0695 | 0.011 | −0.0555 | −0.131442 | 0.010166 | −0.045632 | 0.006048 | −0.037384 | −0.108068 | 0.089152 | −0.011665 | −0.077274 |
| 338 | 0.06157 | 0.033462 | 0.015876 | 0.108411 | 0.0183 | −0.019272 | −0.060736 | −0.055119 | −0.037087 | −0.026064 | −0.018741 | −0.026093 | −0.070145 | 0.01713 |
| 339 | −0.045907 | −0.147798 | 0.073559 | −0.027991 | 0.111751 | −0.085574 | −0.100886 | −0.114004 | 0.003623 | −0.071656 | 0.19966 | −0.01567 | 0.125255 | 0.033398 |
| 340 | −0.08248 | −0.081871 | −0.054774 | −0.062599 | −0.021786 | 0.041566 | −0.00471 | −0.03688 | 0.002606 | −0.000173 | 0.051367 | −0.084404 | 0.087821 | −0.039827 |

| | DT | DU | DV | DW | DX | DY | DZ | EA | EB | EC | ED | EE | EF | EG |
|---|---|---|---|---|---|---|---|---|---|---|---|---|---|---|
| 1 | −0.009425 | 0.028083 | 0.035391 | 0.085842 | 0.003171 | 0.000735 | −0.007812 | 0.001067 | −0.0685791 | 0.040132 | 0.0856591 | −0.062461 | −0.0128571 | −0.211336 |
| 2 | −0.075664 | 0.066999 | −0.055935 | 0.015441 | 0.005064 | 0.018786 | −0.005038 | −0.078168 | −0.070045 | 0.086522 | −0.036719 | −0.050303 | −0.039186 | 0.061047 |
| 3 | 0.001687 | 0.02845 | 0.023885 | 0.124731 | −0.059837 | −0.058697 | −0.076137 | −0.063971 | −0.005227 | 0.024037 | 0.100075 | −0.025325 | −0.020604 | −0.1272 |
| 4 | −0.053569 | −0.030699 | 0.015018 | 0.008266 | 0.078961 | 0.002823 | −0.097877 | 0.043124 | 0.062771 | 0.074369 | 0.065867 | 0.085288 | −0.029124 | 0.230781 |
| 5 | 0.08124 | −0.074437 | 0.001398 | −0.003438 | −0.167308 | 0.074319 | −0.044628 | −0.048629 | −0.043951 | −0.012116 | 0.003976 | 0.00684 | 0.056841 | 0.002509 |
| 6 | −0.092324 | −0.087802 | −0.061168 | −0.109371 | 0.075323 | 0.005464 | −0.017462 | 0.056761 | 0.018672 | 0.082822 | 0.111249 | −0.09544 | 0.102391 | −0.017094 |
| 7 | −0.031625 | 0.09392 | −0.081898 | 0.088008 | −0.029065 | −0.003466 | −0.019813 | −0.07274 | −0.027281 | −0.094037 | −0.051947 | 0.02954 | −0.06813 | −0.010056 |
| 8 | 0.079687 | −0.020473 | −0.019281 | −0.059904 | 0.076956 | −0.028667 | 0.038182 | 0.021598 | 0.002203 | 0.014488 | −0.013334 | −0.010969 | 0.01295 | 0.017244 |
| 9 | 0.019902 | −0.039849 | −0.037569 | 0.024382 | 0.024059 | 0.013863 | −0.020493 | −0.04156 | 0.095586 | −0.009687 | −0.079038 | −0.030678 | −0.016398 | −0.052319 |
| 10 | −0.048056 | 0.071391 | 0.040319 | −0.069779 | −0.014087 | −0.003013 | −0.021605 | −0.018463 | 0.027975 | −0.074712 | −0.147725 | −0.042884 | 0.074391 | 0.134774 |
| 11 | −0.076052 | 0.028264 | −0.094616 | −0.019783 | 0.021452 | 0.053589 | −0.032423 | −0.024724 | 0.007227 | −0.011933 | 0.023575 | 0.053705 | 0.053562 | −0.012484 |
| 12 | −0.079981 | 0.004751 | 0.05667 | −0.017459 | −0.017239 | 0.061787 | −0.036942 | 0.060836 | 0.05423 | −0.013362 | 0.017199 | 0.040807 | −0.032386 | −0.050198 |
| 13 | −0.009657 | −0.018679 | 0.079643 | −0.089387 | 0.058719 | 0.070203 | −0.0001 | −0.015349 | 0.054115 | 0.012902 | −0.002448 | −0.075382 | −0.048488 | −0.028918 |
| 14 | 0.061596 | −0.024428 | 0.095705 | −0.028716 | −0.009278 | 0.029332 | −0.016492 | 0.037619 | 0.046974 | −0.036557 | 0.071237 | −0.035729 | 0.048774 | 0.019542 |
| 15 | 0.004265 | 0.007113 | 0.012348 | −0.012953 | −0.001838 | 0.019833 | −0.021926 | −0.081536 | 0.068391 | 0.004984 | −0.011182 | −0.002036 | 0.037569 | −0.086917 |
| 16 | −0.037367 | 0.042715 | 0.0168261 | 0.050616 | −0.029767 | −0.029318 | 0.008225 | 0.046389 | 0.033537 | 0.090899 | −0.000436 | −0.01175 | 0.068687 | 0.04811 |
| 17 | 0.012967 | 0.008331 | −0.000296 | 0.019712 | 0.021487 | −0.103747 | 0.027125 | 0.029872 | −0.053271 | −0.099313 | 0.079977 | 0.034225 | −0.094673 | 0.032681 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 18 | 0.018683 | 0.025737 | −0.164685 | −0.031429 | 0.123664 | −0.011517 | 0.037448 | 0.00343 | 0.096027 | 0.017594 | 0.006304 | 0.04253 | −0.031731 | 0.076954 |
| 19 | −0.009401 | −0.044494 | 0.205747 | −0.004871 | −0.029095 | 0.087554 | −0.039643 | 0.033355 | −0.02357 | −0.037824 | 0.010549 | 0.068609 | −0.033007 | 0.037244 |
| 20 | −0.013512 | −0.01891 | 0.023917 | −0.006088 | 0.013727 | 0.018043 | −0.013952 | 0.002296 | −0.056778 | −0.00417 | 0.049417 | −0.019415 | −0.027686 | −0.124834 |
| 21 | −0.046546 | −0.03738 | −0.059886 | 0.012439 | 0.027757 | −0.012891 | 0.078738 | −0.046921 | −0.021384 | 0.058231 | −0.02607 | −0.008814 | −0.081083 | −0.114116 |
| 22 | −0.026872 | −0.078948 | −0.117626 | −0.03746 | 0.028426 | −0.084566 | −0.065631 | −0.018655 | 0.03928 | −0.070011 | −0.045873 | 0.095733 | 0.010385 | −0.002 |
| 23 | 0.059694 | 0.05964 | −0.064833 | −0.011417 | 0.11496 | −0.005772 | −0.03277 | 0.040757 | 0.12035 | 0.002487 | −0.080057 | −0.001876 | −0.064449 | 0.097618 |
| 24 | −0.00136 | −0.177279 | 0.041811 | −0.03102 | 0.035735 | 0.008885 | 0.040453 | −0.004598 | −0.023761 | 0.032294 | 0.134125 | −0.003314 | 0.031045 | −0.037899 |
| 25 | −0.088483 | 0.00792 | −0.054684 | −0.102253 | 0.042615 | 0.067051 | 0.054004 | 0.087618 | −0.009231 | −0.230191 | 0.018932 | 0.10406 | −0.056927 | 0.111045 |
| 26 | −0.00919 | −0.006407 | 0.05195 | −0.017063 | −0.003061 | 0.020794 | 0.008517 | 0.015268 | −0.019674 | −0.014868 | 0.014386 | 0.029463 | 0.012816 | 0.044211 |
| 27 | 0.001272 | −0.003059 | −0.01603 | 0.032075 | −0.017983 | 0.006869 | −0.015647 | −0.013053 | 0.001554 | 0.023847 | 0.036438 | −0.01048 | −0.034734 | −0.097856 |
| 28 | 0.037723 | 0.004187 | −0.016365 | 0.071885 | −0.003707 | −0.052782 | −0.095658 | 0.023742 | −0.020291 | −0.058468 | −0.116737 | −0.055432 | 0.037586 | 0.049074 |
| 29 | 0.109403 | 0.136416 | 0.013423 | −0.028471 | −0.052785 | −0.016971 | −0.068229 | 0.023034 | −0.005308 | −0.005456 | −0.023587 | 0.001757 | −0.01634 | −0.017706 |
| 30 | 0.051922 | 0.045573 | 0.051004 | −0.050799 | −0.002849 | −0.049227 | −0.000377 | −0.009941 | −0.02387 | 0.034451 | −0.013183 | −0.003205 | 0.042881 | −0.049655 |
| 31 | 0.04874 | −0.00827 | 0.043417 | 0.045692 | 0.013095 | 0.053079 | −0.020419 | −0.010279 | 0.064291 | −0.030699 | −0.046567 | −0.036657 | 0.015024 | 0.036037 |
| 32 | 0.062095 | 0.161498 | 0.011427 | −0.075199 | −0.118232 | 0.085325 | 0.097463 | −0.044778 | −0.008481 | −0.147122 | −0.069289 | −0.006191 | −0.009445 | −0.029114 |
| 33 | −0.050784 | −0.069884 | 0.027999 | 0.076137 | −0.018089 | −0.02865 | −0.03023 | −0.127217 | 0.065233 | −0.06662 | 0.026373 | −0.039087 | 0.034636 | 0.060809 |
| 34 | −0.020029 | −0.006753 | 0.006201 | −0.100509 | −0.004662 | −0.026534 | −0.077545 | 0.092204 | −0.040278 | 0.16239 | −0.019489 | 0.072309 | −0.078821 | −0.029972 |
| 35 | 0.091479 | 0.022836 | 0.01805 | −0.005925 | −0.009699 | 0.0448 | 0.018811 | −0.071572 | −0.102104 | 0.07349 | −0.04877 | 0.007292 | −0.033793 | 0.014879 |
| 36 | −0.050795 | 0.019904 | 0.110404 | −0.074379 | 0.045835 | −0.048895 | 0.001032 | 0.060506 | −0.021402 | 0.090068 | −0.082015 | −0.006563 | −0.013154 | 0.060104 |
| 37 | 0.007388 | −0.012558 | −0.035395 | 0.042349 | −0.050741 | 0.056014 | 0.090511 | 0.012546 | −0.05732 | 0.028449 | −0.028457 | −0.041475 | 0.069984 | −0.070956 |
| 38 | −0.004986 | −0.086553 | −0.094297 | −0.029255 | −0.117708 | 0.108633 | 0.058893 | 0.118253 | −0.091209 | −0.03937 | 0.087771 | 0.044469 | 0.030456 | −0.065372 |
| 39 | 0.075461 | 0.074209 | −0.101967 | −0:101045 | 0.055717 | −0.069475 | −0.025471 | 0.010843 | −0.05467 | 0.11137 | −0.068125 | 0.039222 | 0.042015 | 0.105201 |
| 40 | −0.031556 | −0.008553 | 0.004115 | 0.032831 | −0.042637 | 0.037435 | 0.011253 | −0.115373 | −0.00802 | −0.034014 | −0.037746 | 0.044623 | −0.072218 | −0.01035 |
| 41 | 0.011556 | 0.037169 | −0.042613 | −0.045754 | −0.009637 | 0.017522 | 0.065585 | 0.012226 | 0.080381 | 0.030785 | 0.059749 | 0.019102 | 0.040743 | −0.066001 |
| 42 | 0.013892 | −0.000033 | −0.009196 | −0.088793 | 0.029416 | −0.01105 | −0.000448 | −0.100648 | 0.031695 | −0.036361 | −0.001548 | −0.017285 | 0.061354 | −0.106521 |
| 43 | −0.029774 | −0.04117 | −0.015209 | 0.028985 | −0.04543 | 0.101619 | 0.071926 | 0.01005 | 0.103568 | 0.02496 | 0.023983 | −0.022873 | −0.035413 | 0.173729 |
| 44 | 0.07089 | 0.004075 | −0.019463 | −0.029709 | −0.044526 | 0.006536 | 0.004967 | −0.09476 | −0.023146 | 0.04552 | −0.028005 | 0.034405 | 0.073328 | −0.066839 |
| 45 | 0.092288 | −0.037482 | 0.007229 | 0.07985 | 0.090971 | 0.02427 | 0.058017 | −0.023694 | −0.06791 | 0.086613 | 0.06927 | −0.037473 | −0.016522 | 0.051081 |
| 46 | −0.109686 | 0.029876 | −0.02964 | 0.077584 | −0.007841 | −0.048428 | −0.028372 | 0.011899 | −0.085738 | −0.083999 | 0.00851 | 0.053887 | −0.026633 | −0.055246 |
| 47 | 0.068581 | 0.037082 | 0.074051 | 0.096547 | −0.062884 | 0.046853 | −0.027691 | −0.019533 | −0.078279 | −0.105783 | 0.058331 | −0.001819 | 0.045256 | 0.050821 |
| 48 | 0.073141 | 0.022445 | −0.016968 | 0.006659 | 0.044039 | 0.046011 | −0.071708 | 0.094761 | 0.052751 | −0.076019 | −0.064243 | 0.128416 | 0.052951 | −0.009052 |
| 49 | −0.047005 | −0.001893 | 0.139889 | −0.000981 | 0.02599 | −0.030485 | −0.004963 | 0.056348 | 0.010118 | 0.02286 | −0.051119 | −0.000802 | 0.115455 | −0.115065 |
| 50 | 0.006142 | 0.001205 | 0.086245 | −0.020406 | −0.022429 | 0.046419 | −0.061561 | 0.011502 | 0.078629 | −0.000241 | −0.039848 | 0.050514 | 0.060195 | 0.011955 |
| 51 | 0.082399 | 0.010729 | −0.158151 | −0.043987 | 0.037383 | 0.01754 | −0.018402 | −0.016351 | 0.012758 | 0.067315 | 0.008305 | −0.013092 | 0.112256 | −0.008229 |
| 52 | −0.061911 | 0.018638 | 0.001911 | −0.095874 | 0.023716 | −0.062291 | 0.027794 | −0.058834 | 0.049748 | 0.079168 | 0.154052 | −0.059087 | −0.052113 | −0.020883 |
| 53 | −0.04584 | 0.03914 | 0.013974 | −0.012906 | 0.064046 | −0.083778 | −0.001277 | 0.048577 | −0.022376 | 0.027426 | −0.023071 | −0.016686 | −0.053823 | 0.084836 |
| 54 | 0.041015 | 0.055491 | 0.155785 | −0.010783 | 0.002242 | 0.007796 | −0.010352 | −0.132299 | −0.138023 | −0.057555 | 0.05385 | 0.012755 | 0.010191 | 0.000895 |
| 55 | 0.017056 | 0.010932 | −0.001033 | −0.068081 | 0.040279 | −0.034666 | 0.006197 | −0.025566 | −0.016891 | −0.012773 | 0.069823 | 0.04074 | 0.005497 | 0.138041 |
| 56 | 0.075242 | −0.022203 | −0.021235 | 0.021881 | −0.012338 | 0.021403 | −0.071755 | −0.008215 | 0.006555 | −0.039076 | −0.025874 | 0.117787 | 0.010894 | 0.184019 |
| 57 | −0.00128 | 0.020746 | −0.0317 | 0.022037 | −0.126096 | 0.043878 | 0.056723 | 0.003446 | 0.014208 | −0.027116 | 0.022631 | −0.004466 | 0.024736 | −0.024653 |
| 58 | 0.033437 | −0.053051 | −0.005461 | 0.053435 | −0.076917 | 0.078369 | 0.135297 | 0.038769 | −0.051171 | 0.012107 | −0.076708 | 0.041154 | −0.057581 | 0.041276 |
| 59 | 0.019053 | −0.02036 | 0.004592 | −0.029415 | −0.01599 | −0.025091 | 0.034428 | 0.055586 | 0.057276 | 0.046329 | 0.05372 | −0.049778 | −0.033373 | 0.075694 |
| 60 | −0.000991 | 0.008673 | −0.027883 | −0.006015 | 0.053791 | −0.069634 | −0.044457 | −0.019398 | −0.037459 | −0.081875 | −0.051511 | 0.014216 | 0.013975 | −0.058549 |
| 61 | −0.011984 | 0.077177 | −0.020544 | 0.088923 | −0.117804 | −0.027024 | −0.085037 | 0.133286 | 0.042738 | −0.106482 | 0.164455 | −0.114576 | −0.02139 | −0.017743 |
| 62 | 0.003279 | −0.025214 | −0.068226 | 0.081892 | −0.038647 | 0.028507 | −0.006389 | −0.018525 | 0.059383 | −0.03341 | 0.025296 | 0.135271 | 0.007078 | −0.038521 |
| 63 | −0.013656 | −0.125965 | −0.017286 | −0.00084 | −0.017822 | 0.038202 | −0.019847 | −0.086477 | −0.006406 | −0.092069 | −0.086518 | −0.010025 | −0.026794 | −0.01405 |
| 64 | 0.046847 | −0.016157 | −0.023197 | −0.016861 | −0.061633 | −0.04911 | 0.004691 | 0.030104 | 0.019721 | 0.03467 | −0.012838 | 0.040006 | −0.011323 | −0.086933 |
| 65 | 0.075522 | −0.025776 | −0.0228 | −0.027224 | −0.095117 | 0.013867 | −0.047695 | −0.045 | 0.062877 | 0.047821 | −0.026833 | 0.074672 | −0.104597 | 0.066923 |
| 66 | −0.052018 | 0.035095 | 0.029358 | −0.03403 | −0.063769 | 0.031636 | −0.08067 | 0.107137 | −0.054656 | 0.064704 | −0.000996 | 0.009252 | 0.025964 | −0.008888 |
| 67 | −0.001219 | 0.012757 | −0.03128 | 0.040451 | 0.151465 | −0.032488 | 0.136161 | −0.085712 | 0.034835 | 0.023358 | −0.121529 | 0.092915 | 0.066226 | −0.058294 |
| 68 | 0.01842 | 0.090227 | 0.072231 | 0.015638 | 0.005978 | −0.025305 | −0.067381 | 0.057384 | 0.029763 | −0.066094 | −0.038407 | −0.030409 | −0.147209 | 0.033172 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 69 | 0.047334 | 0.049362 | −0.00844 | 0.027524 | 0.033548 | 0.035039 | −0.127332 | −0.108261 | 0.065042 | 0.024352 | 0.067851 | 0.035083 | −0.055522 | 0.099229 |
| 70 | −0.019871 | 0.019399 | −0.0054 | 0.022455 | 0.006008 | −0.029685 | 0.049701 | −0.010532 | −0.025894 | 0.003738 | 0.010748 | 0.027696 | 0.035726 | −0.136606 |
| 71 | 0.049204 | 0.050154 | −0.022722 | 0.034268 | −0.012955 | −0.024765 | 0.06148 | 0.007622 | −0.013311 | −0.001555 | −0.046394 | 0.042175 | 0.037842 | −0.00977 |
| 72 | −0.012064 | −0.063433 | −0.010951 | 0.004903 | −0.037508 | 0.026138 | −0.03188 | −0.044887 | −0.005724 | −0.001732 | 0.039109 | 0.038299 | −0.004093 | 0.021515 |
| 73 | 0.084927 | −0.027838 | 0.039841 | 0.044061 | −0.02028 | 0.051316 | −0.034411 | 0.00783 | 0.021908 | 0.095026 | 0.028604 | 0.115531 | −0.023636 | 0.049337 |
| 74 | 0.060146 | −0.086283 | −0.031941 | −0.08129 | 0.059202 | −0.034758 | −0.001102 | 0.042762 | −0.043602 | −0.033255 | −0.006356 | 0.081702 | −0.079992 | −0.038648 |
| 75 | 0.002818 | −0.009669 | −0.004576 | 0.02896 | −0.002741 | −0.009838 | 0.031856 | 0.028333 | −0.031035 | 0.012317 | −0.031777 | −0.011542 | 0.006419 | 0.033543 |
| 76 | −0.042501 | −0.009377 | −0.040556 | −0.027798 | 0.001762 | −0.076986 | −0.08006 | −0.007822 | −0.021873 | 0.003732 | −0.045877 | −0.016578 | 0.015124 | −0.128148 |
| 77 | −0.021925 | −0.000399 | −0.023177 | 0.04523 | 0.008581 | −0.011151 | 0.008126 | 0.033885 | −0.034869 | 0.020261 | −0.02139 | −0.006889 | −0.001144 | 0.133418 |
| 78 | −0.015988 | −0.013033 | −0.022023 | 0.053058 | 0.000957 | −0.011811 | 0.024679 | 0.035254 | −0.058307 | 0.015651 | −0.032933 | −0.000688 | −0.004703 | 0.067181 |
| 79 | −0.023247 | −0.011751 | −0.014749 | 0.030944 | −0.008737 | −0.020554 | 0.034344 | 0.017837 | −0.057076 | 0.016486 | −0.021371 | −0.017302 | −0.014922 | −0.056504 |
| 80 | −0.12819 | −0.173231 | 0.067523 | −0.017204 | −0.041287 | −0.0744 | −0.030036 | 0.054221 | 0.063433 | −0.058791 | −0.01605 | 0.036768 | 0.010143 | −0.044403 |
| 81 | 0.058538 | −0.015388 | −0.057967 | −0.063257 | −0.106168 | −0.012346 | 0.008488 | 0.06256 | 0.102365 | −0.029184 | −0.067308 | −0.057403 | −0.01096 | 0.010167 |
| 82 | −0.026441 | 0.011785 | −0.03556 | −0.007636 | −0.009739 | −0.010368 | 0.001551 | 0.032923 | −0.006101 | 0.00117 | 0.037024 | 0.055529 | 0.004883 | 0.013605 |
| 83 | 0.006843 | −0.008224 | −0.012963 | 0.02375 | −0.02822 | −0.008941 | −0.004561 | 0.013034 | 0.006034 | 0.013614 | 0.042121 | 0.011006 | −0.061738 | −0.016433 |
| 84 | 0.018706 | −0.005697 | −0.074555 | 0.008482 | −0.023577 | −0.029069 | −0.01982 | 0.003296 | 0.023732. | 0.041616 | 0.015986 | −0.014688 | −0.069958 | −0.028922 |
| 85 | 0.029491 | −0.037735 | −0.023034 | 0.067653 | 0.062943 | −0.020058 | −0.063588 | −0.006763 | 0.162766 | −0.004546 | −0.013909 | −0.05553 | −0.048434 | 0.00275 |
| 86 | −0.034931 | 0.007324 | 0.015007 | −0.048979 | −0.015524 | 0.031766 | −0.078489 | −0.052792 | −0.008019 | −0.016748 | 0.105052 | −0.076055 | −0.086517 | −0.062129 |
| 87 | −0.019798 | 0.059646 | −0.01736 | 0.039019 | 0.071767 | 0.004967 | 0.09123 | −0.045363 | −0.068314 | −0.011268 | −0.054108 | −0.00435 | 0.032365 | 0.060348 |
| 88 | 0.011283 | 0.017432 | 0.004248 | 0.02594 | 0.004127 | −0.001068 | −0.027646 | −0.026351 | −0.007007 | 0.02029 | 0.026619 | −0.000126 | −0.000808 | 0.038276 |
| 89 | 0.00891 | −0.02174 | −0.006782 | 0.034059 | −0.00047 | −0.028701 | −0.000635 | 0.020619 | −0.001353 | 0.038154 | 0.038691 | 0.011345 | −0.018105 | 0.031421 |
| 90 | 0.006561 | −0.035822 | −0.045429 | 0.022885 | −0.00681 | −0.038778 | −0.018077 | 0.008305 | 0.012107 | 0.006 | 0.029441 | 0.006222 | −0.026429 | −0.04442 |
| 91 | 0.000597 | −0.026366 | −0.048218 | 0.029669 | 0.00726 | −0.025246 | 0.050933 | 0.018497 | −0.01642 | 0.095267 | 0.022496 | 0.000422 | −0.022156 | 0.068828 |
| 92 | −0.022191 | 0.054205 | −0.038238 | 0.071686 | −0.027377 | 0.046323 | 0.001134 | −0.07308 | −0.13505 | −0.034925 | 0.018871 | −0.009452 | 0.040165 | −0.019369 |
| 93 | −0.056498 | −0.070439 | −0.017031 | −0.042422 | 0.033857 | −0.012125 | 0.044078 | 0.03734 | −0.002838 | 0.015584 | 0.045165 | −0.056244 | 0.040617 | −0.020967 |
| 94 | −0.015051 | 0.058605 | 0.096728 | −0.054056 | 0.123151 | 0.107584 | 0.041847 | 0.08414 | −0.027451 | −0.066567 | −0.002776 | −0.040337 | 0.049466 | 0.037098 |
| 95 | −0.0403 | −0.062179 | −0.035385 | −0.042626 | 0.032962 | −0.02271 | −0.028975 | 0.079628 | −0.007724 | 0.000737 | −0.013146 | 0.047056 | −0.035786 | −0.055067 |
| 96 | 0.041767 | −0.018769 | 0.031049 | −0.05499 | 0.00601 | −0.083803 | 0.109399 | 0.067961 | 0.079865 | 0.071067 | −0.068441 | 0.01576 | 0.080893 | 0.057879 |
| 97 | −0.027604 | 0.00071 | −0.040737 | 0.033555 | 0.068898 | 0.045883 | −0.00541 | 0.015662 | −0.001524 | 0.009389 | 0.117574 | 0.010121 | −0.149566 | −0.026828 |
| 98 | −0.014646 | 0.007253 | 0.017329 | 0.016512 | 0.001483 | −0.045203 | −0.001884 | 0.005563 | −0.001702 | 0.053118 | −0.049071 | 0.02263 | −0.086204 | 0.003721 |
| 99 | −0.068723 | −0.056871 | 0.080181 | 0.059841 | 0.020392 | −0.057781 | −0.02358 | 0.092089 | −0.035756 | −0.107833 | −0.068995 | 0.018654 | −0.019682 | 0.004215 |
| 100 | 0.022286 | 0.058783 | 0.089021 | −0.064096 | −0.095092 | −0.052507 | 0.026248 | −0.016763 | 0.004299 | 0.055732 | 0.105267 | −0.118932 | −0.019207 | 0.047699 |
| 101 | 0.00723 | 0.021867 | 0.013932 | 0.01101 | 0.037924 | −0.037375 | −0.017441 | 0.058025 | −0.017738 | 0.045818 | −0.055168 | 0.05226 | 0.011763 | −0.094444 |
| 102 | 0.016815 | −0.098491 | 0.048633 | 0.090727 | 0.012434 | −0.06131 | 0.032133 | 0.015645 | −0.020709 | −0.032045 | 0.119789 | 0.019603 | 0.123869 | 0.098617 |
| 103 | 0.033824 | 0.053746 | −0.152454 | 0.05808 | 0.028552 | 0.028597 | 0.168098 | 0.031602 | −0.000618 | 0.030938 | −0.073659 | −0.000443 | 0.053638 | −0.027062 |
| 104 | 0.056441 | 0.112162 | 0.007072 | −0.024116 | −0.022844 | 0.046887 | −0.095419 | 0.129469 | −0.031945 | −0.053696 | −0.082634 | −0.067733 | −0.005421 | −0.006133 |
| 105 | −0.072235 | 0.002293 | −0.014282 | 0.029711 | −0.001531 | −0.077444 | −0.07981 | −0.034075 | 0.056956 | 0.015846 | −0.064952 | −0.009234 | −0.059983 | −0.014228 |
| 106 | 0.008289 | 0.08718 | 0.090946 | 0.02139 | 0.039405 | −0.005825 | −0.035701 | −0.039332 | 0.07466 | −0.009364 | −0.038392 | 0.088814 | 0.014598 | −0.039837 |
| 107 | −0.00309 | 0.016307 | 0.034462 | −0.032406 | 0.101589 | 0.104133 | 0.102329 | 0.00659 | −0.046795 | 0.120678 | −0.004238 | 0.052488 | −0.043183 | −0.015108 |
| 108 | −0.129529 | −0.085298 | −0.031395 | −0.050362 | 0.03021 | 0.142647 | −0.17747 | 0.082217 | −0.069014 | 0.012039 | 0.055888 | −0.062623 | 0.063412 | 0.049851 |
| 109 | −0.027742 | 0.077111 | 0.023908 | −0.007545 | −0.068407 | −0.040633 | 0.033079 | 0.017628 | −0.017591 | 0.054489 | −0.032922 | −0.010116 | −0.006569 | 0.011243 |
| 110 | 0.098003 | 0.064006 | −0.091498 | −0.121498 | 0.006632 | 0.071001 | 0.040405 | 0.032349 | 0.056807 | −0.080199 | 0.015661 | −0.007306 | 0.027298 | 0.002312 |
| 111 | 0.036779 | 0.045056 | 0.049666 | 0.034561 | −0.015102 | 0.004988 | 0.0494 | −0.03346 | −0.057772 | −0.068045 | 0.078202 | 0.045993 | −0.096 | 0.111106 |
| 112 | 0.017706 | 0.036116 | 0.101652 | −0.032308 | 0.044702 | −0.161798 | −0.000966 | −0.0087 | 0.073147 | −0.037134 | 0.023651 | 0.062884 | −0.058973 | −0.019391 |
| 113 | 0.08868 | 0.013446 | −0.029951 | 0.110012 | 0.078318 | 0.009732 | 0.063565 | −0.000371 | −0.017793 | −0.016598 | 0.037982 | −0.045918 | −0.057953 | 0.015427 |
| 114 | −0.047503 | 0.112769 | 0.076298 | 0.020677 | 0.023755 | 0.103759 | −0.071143 | 0.016012 | 0.014084 | −0.011564 | 0.007722 | −0.022803 | −0.018551 | 0.057809 |
| 115 | −0.094162 | −0.006985 | −0.001719 | 0.043197 | 0.009836 | 0.048962 | 0.136805 | 0.023028 | 0.065528 | −0.07986 | −0.016181 | −0.008019 | −0.028987 | −0.03139 |
| 116 | 0.001935 | −0.029847 | −0.105489 | 0.053775 | 0.020453 | 0.014017 | −0.048927 | −0.068675 | −0.097368 | 0.002336 | 0.010591 | −0.015147 | 0.105728 | −0.065918 |
| 117 | 0.010284 | −0.000588 | −0.027654 | 0.015407 | −0.001473 | −0.046321 | −0.106346 | 0.053925 | 0.045457 | 0.003388 | −0.070839 | −0.060847 | −0.055277 | −0.012991 |
| 118 | −0.068106 | 0.131003 | −0.006027 | 0.085331 | 0.089353 | −0.010549 | −0.011284 | 0.011704 | 0.162896 | −0.02356 | −0.05731 | 0.058597 | 0.02991 | −0.047191 |
| 119 | −0.034555 | −0.032883 | −0.033779 | −0.078813 | −0.038708 | 0.035726 | 0.057004 | −0.072388 | 0.053141 | 0.028332 | 0.03599 | −0.176107 | −0.05867 | −0.005568 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 120 | 0.03604 | −0.046559 | −0.084907 | 0.00118 | 0.082995 | 0.09036 | 0.008206 | −0.043845 | 0.021163 | 0.052835 | 0.073902 | 0.019915 | 0.084354 | −0.004809 |
| 121 | −0.060786 | 0.103249 | 0.092713 | −0.078443 | −0.013938 | −0.00637 | 0.032562 | −0.087757 | 0.142596 | 0.027172 | −0.035318 | −0.086129 | −0.00907 | −0.037743 |
| 122 | −0.045555 | 0.005214 | 0.067308 | −0.04732 | 0.061869 | −0.011368 | −0.019419 | −0.085022 | −0.054043 | 0.04434 | 0.018071 | −0.037247 | −0.037433 | 0.078034 |
| 123 | 0.094276 | 0.070744 | −0.062201 | −0.075668 | 0.024437 | 0.000029 | −0.024842 | 0.057909 | −0.012155 | −0.012714 | −0.037357 | −0.01034 | 0.076784 | −0.061081 |
| 124 | 0.007852 | 0.03919 | 0.051714 | −0.030327 | −0.034037 | 0.021183 | −0.021715 | 0.022733 | 0.051984 | −0.089355 | 0.026782 | −0.08241 | 0.075025 | 0.063629 |
| 125 | −0.021854 | 0.018792 | −0.039589 | 0.05018 | 0.161796 | 0.002145 | −0.11242 | 0.031711 | −0.107465 | −0.002229 | 0.011533 | −0.041781 | 0.077124 | 0.018509 |
| 126 | −0.001528 | −0.030623 | 0.029453 | −0.05109 | −0.007915 | 0.000525 | 0.061323 | 0.020102 | −0.071164 | −0.023981 | 0.006044 | 0.0005r | 0.000728 | 0.037482 |
| 127 | −0.007358 | −0.015855 | 0.041393 | 0.019621 | −0.020916 | −0.005834 | 0.094832 | 0.055828 | −0.025697 | 0.008764 | 0.067187 | 0.023819 | 0.005467 | −0.03026 |
| 128 | 0.03797 | 0.078761 | 0.078018 | 0.16324 | 0.002202 | 0.108289 | 0.080739 | −0.08424 | −0.083963 | 0.028572 | 0.042994 | −0.032656 | −0.025623 | 0.024674 |
| 129 | 0.068099 | −0.024871 | −0.015307 | 0.038651 | −0.034942 | 0.078825 | 0.000974 | −0.001639 | −0.017118 | 0.057912 | 0.012539 | −0.033279 | −0.046064 | 0.019103 |
| 130 | −0.041117 | 0.005732 | 0.035934 | −0.127593 | 0.04423 | 0.011986 | −0.003785 | −0.00413 | 0.066196 | 0.035017 | 0.129396 | 0.054885 | −0.057608 | −0.03376 |
| 131 | 0.015714 | −0.069632 | 0.113481 | 0.027253 | −0.092155 | 0.011221 | 0.037241 | 0.001705 | −0.142041 | 0.009675 | −0.10999 | −0.034424 | −0.070296 | 0.026132 |
| 132 | 0.219928 | 0.016069 | −0.013964 | 0.011072 | 0.020203 | −0.018666 | 0.02698 | −0.062851 | −0.05759 | −0.04985 | 0.025482 | 0.075446 | −0.041205 | −0.031447 |
| 133 | 0.058136 | 0.038206 | 0.068573 | −0.067744 | −0.047 | 0.026309 | 0.012517 | −0.007818 | 0.05015 | −0.003187 | 0.028053 | 0.119551 | 0.047789 | 0.018011 |
| 134 | 0.028683 | −0.060371 | 0.078634 | −0.054709 | −0.002523 | 0.070813 | −0.045081 | −0.119414 | −0.023418 | −0.041494 | −0.016066 | 0.065058 | −0.011304 | −0.003748 |
| 135 | 0.017814 | −0.007817 | 0.064468 | −0.10778 | 0.011758 | −0.000933 | −0.011557 | −0.092356 | 0.043865 | 0.038562 | −0.11837 | −0.141474 | 0.067602 | −0.006819 |
| 136 | 0.098723 | −0.001313 | 0.084095 | −0.052032 | −0.08319 | −0.049125 | 0.03577 | 0.000807 | −0.048431 | 0.084211 | −0.078265 | 0.140706 | 0.140065 | −0.037603 |
| 137 | 0.063596 | −0.049947 | −0.02573 | −0.041135 | 0.006324 | −0.017611 | 0.054404 | 0.024382 | −0.105294 | −0.078645 | −0.021271 | −0.029878 | −0.027899 | 0.055159 |
| 138 | 0.016923 | 0.009369 | −0.025825 | −0.058013 | 0.007442 | 0.020553 | −0.013841 | 0.043881 | 0.067595 | −0.048097 | −0.031463 | −0.001394 | 0.10315 | −0.02316 |
| 139 | −0.125594 | 0.103266 | −0.050147 | −0.091276 | −0.008026 | 0.061029 | 0.07645 | 0.028146 | 0.021048 | 0.00856 | −0.057985 | −0.080895 | 0.013429 | −0.036984 |
| 140 | −0.018728 | 0.092411 | 0.005199 | 0.070375 | 0.034526 | 0.044747 | 0.061217 | 0.07753 | 0.005107 | 0.011856 | −0.013678 | −0.04821 | 0.02138 | −0.04743 |
| 141 | 0.032183 | −0.103802 | −0.010059 | 0.041437 | −0.047816 | 0.105993 | 0.032076 | 0.107176 | −0.012035 | −0.025178 | 0.042607 | 0.076336 | −0.061269 | 0.020817 |
| 142 | −0.126916 | 0.096965 | −0.034919 | 0.054709 | −0.101024 | −0.190862 | 0.038037 | 0.037072 | 0.031048 | 0.01801 | 0.146018 | 0.084305 | 0.030982 | 0.046571 |
| 143 | −0.017873 | −0.036788 | 0.094652 | 0.034281 | −0.001745 | −0.086812 | 0.066126 | −0.126854 | −0.023021 | 0.018755 | −0.006424 | 0.077283 | −0.005114 | −0.05158 |
| 144 | 0.014038 | 0.000083 | −0.104164 | 0.056155 | 0.045388 | −0.064351 | −0.098968 | −0.079511 | −0.012763 | −0.023215 | −0.018967 | −0.016832 | −0.015342 | 0.028183 |
| 145 | −0.002075 | −0.051253 | −0.02259 | −0.098951 | 0.031384 | 0.082087 | −0.050283 | 0.014763 | 0.021199 | −0.061844 | −0.023576 | −0.017443 | −0.0352 | 0.014645 |
| 146 | 0.001182 | 0.0014 | −0.094592 | 0.000942 | −0.110106 | 0.021213 | −0.025282 | −0.017758 | 0.030546 | 0.050623 | 0.036312 | 0.000442 | −0.119285 | 0.033638 |
| 147 | −0.005843 | 0.067691 | −0.064545 | −0.052604 | 0.058482 | −0.023954 | 0.067044 | −0.016695 | −0.105579 | −0.024384 | 0.006388 | 0.014239 | 0.021305 | 0.028981 |
| 148 | −0.015936 | −0.095987 | −0.017313 | −0.082758 | −0.007939 | −0.048509 | −0.017533 | −0.040419 | −0.014045 | −0.071935 | −0.051349 | 0.069726 | 0.012773 | 0.016318 |
| 149 | −0.003492 | 0.032319 | 0.066278 | 0.042964 | 0.041245 | −0.00507 | −0.037381 | 0.140071 | 0.005295 | −0.029904 | 0.056431 | −0.043938 | −0.003034 | −0.010416 |
| 150 | 0.001386 | −0.070108 | 0.145624 | −0.044593 | −0.01843 | −0.004253 | 0.087601 | 0.107856 | −0.003802 | 0.012623 | −0.074711 | −0.117931 | −0.047434 | 0.059789 |
| 151 | 0.048285 | 0.008226 | 0.012628 | 0.021473 | −0.05994 | −0.06468 | −0.055337 | 0.063494 | 0.028785 | 0.063257 | 0.087394 | −0.035193 | −0.069392 | −0.011086 |
| 152 | −0.104523 | 0.09917 | 0.05186 | 0.025433 | 0.004655 | 0.06833 | 0.080929 | 0.128094 | −0.029302 | 0.025841 | −0.00775 | −0.035439 | 0.111504 | −0.069076 |
| 153 | 0.061652 | −0.060072 | 0.003376 | 0.091572 | 0.026555 | 0.069029 | −0.113243 | 0.08816 | −0.04111 | −0.01846 | −0.072398 | 0.000288 | −0.032753 | 0.052551 |
| 154 | 0.044175 | 0.027165 | −0.056062 | −0.09356 | 0.135747 | −0.034248 | 0.05488 | 0.081945 | −0.043971 | −0.152036 | 0.03456 | −0.005885 | −0.058147 | −0.041984 |
| 155 | 0.024766 | 0.037106 | 0.072467 | −0.04209 | 0.064735 | −0.170875 | −0.048087 | 0.003282 | 0.009504 | 0.00371 | 0.005408 | 0.089726 | −0.037197 | −0.052056 |
| 156 | −0.04258 | 0.046874 | −0.031779 | 0.068631 | 0.032485 | −0.034391 | −0.089941 | 0.010201 | 0.044553 | 0.016204 | −0.045085 | 0.009848 | 0.065302 | −0.014118 |
| 157 | −0.094849 | 0.150502 | −0.071257 | −0.00947 | −0.085422 | −0.010397 | −0.100683 | −0.052272 | −0.12093 | −0.049015 | −0.017241 | −0.043342 | −0.07941 | 0.005586 |
| 158 | −0.048739 | −0.033293 | 0.013854 | 0.04114 | −0.045767 | 0.01413 | 0.038077 | −0.027204 | 0.03096 | 0.104333 | −0.038519 | 0.019511 | −0.009713 | −0.002755 |
| 159 | 0.038806 | −0.010202 | −0.012543 | 0.003886 | 0.000551 | 0.003229 | 0.030241 | 0.009116 | −0.033938 | 0.033749 | 0.072515 | 0.086114 | 0.003787 | 0.047809 |
| 160 | −0.032737 | −0.040256 | −0.07818 | 0.005834 | 0.0382 | 0.019845 | −0.042494 | 0.004278 | −0.052627 | 0.05034 | 0.086723 | −0.0213 | −0.07191 | −0.011932 |
| 161 | 0.01173 | −0.0603 | −0.014303 | 0.061337 | −0.007742 | −0.035972 | 0.080841 | −0.075992 | 0.119041 | 0.009527 | −0.027647 | −0.07024 | 0.022695 | 0.018507 |
| 162 | −0.067434 | 0.154859 | −0.045512 | 0.031793 | 0.016437 | −0.013213 | −0.009475 | −0.049563 | 0.073196 | 0.073803 | 0.002945 | 0.075132 | −0.011949 | 0.014447 |
| 163 | −0.113552 | 0.043588 | −0.032688 | −0.056486 | −0.024601 | 0.098835 | −0.063475 | −0.010272 | −0.054105 | 0.025592 | −0.062994 | 0.117501 | 0.008544 | 0.01377 |
| 164 | −0.008754 | −0.082492 | −0.013173 | 0.026504 | −0.004686 | −0.000896 | 0.013468 | −0.108458 | 0.085902 | 0.065334 | 0.012108 | 0.036853 | −0.030598 | 0.002961 |
| 165 | 0.003146 | −0.043498 | −0.070807 | −0.032584 | 0.079344 | 0.123623 | −0.025679 | 0.057363 | 0.063877 | −0.055985 | 0.010049 | 0.002774 | 0.030043 | 0.033891 |
| 166 | 0.086105 | 0.059637 | 0.106869 | 0.041687 | −0.007374 | −0.048405 | 0.056017 | 0.023365 | −0.073056 | −0.032793 | −0.009138 | −0.055886 | −0.021092 | −0.036104 |
| 167 | 0.073137 | −0.110083 | −0.062247 | 0.033729 | −0.002746 | −0.059924 | 0.112036 | −0.024339 | 0.042874 | −0.005316 | 0.052134 | −0.079784 | −0.002906 | −0.006718 |
| 168 | 0.000242 | −0.005281 | 0.031134 | −0.101881 | −0.018679 | 0.030861 | 0.012674 | −0.0359 | −0.029257 | −0.088524 | −0.019379 | −0.007156 | −0.011202 | 0.029048 |
| 169 | −0.013057 | 0.001912 | −0.029684 | −0.000823 | −0.019552 | 0.041339 | −0.000615 | −0.032284 | 0.018685 | −0.009337 | 0.011786 | −0.048543 | 0.068316 | 0.042853 |
| 170 | 0.021361 | −0.013791 | 0.006796 | 0.036615 | 0.126338 | 0.086732 | 0.001147 | −0.010236 | 0.030115 | −0.059781 | 0.087223 | −0.091661 | 0.065073 | −0.007443 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 171 | −0.006593 | 0.041678 | −0.012657 | −0.027124 | −0.05654 | 0.056267 | −0.034944 | 0.022235 | −0.018877 | 0.033833 | 0.049499 | −0.027454 | 0.019585 | 0.011851 |
| 172 | −0.003926 | −0.066281 | −0.046676 | −0.003142 | −0.068217 | −0.146819 | −0.026018 | −0.015077 | 0.009091 | −0.021733 | −0.042417 | −0.070094 | 0.04738 | 0.02672 |
| 173 | 0.009859 | −0.098804 | 0.020661 | −0.001703 | 0.008202 | −0.050814 | −0.039461 | −0.029251 | −0.067443 | −0.059204 | −0.094031 | −0.038386 | −0.028555 | 0.016614 |
| 174 | 0.101819 | −0.074268 | 0.033466 | 0.029442 | −0.031322 | −0.114395 | −0.039686 | 0.07795 | −0.068456 | 0.130102 | −0.00943 | 0.013025 | 0.027717 | 0.077976 |
| 175 | −0.021944 | 0.109041 | 0.001641 | 0.009165 | −0.035797 | 0.012423 | 0.01929 | 0.061878 | 0.005186 | −0.007405 | 0.051427 | 0.044978 | 0.031419 | 0.010453 |
| 176 | −0.009453 | −0.013723 | 0.026344 | −0.000019 | −0.043598 | 0.0445 | 0.050457 | 0.029737 | 0.016364 | 0.075957 | 0.068193 | 0.092135 | −0.033566 | −0.00434 |
| 177 | 0.089861 | −0.009212 | 0.057561 | −0.049058 | 0.160868 | −0.007063 | 0.042743 | −0.00698 | −0.021482 | −0.067964 | 0.044074 | −0.060347 | −0.049687 | 0.012052 |
| 178 | −0.010095 | 0.123023 | −0.006688 | 0.027693 | 0.041965 | 0.03489 | −0.008288 | −0.066397 | 0.022421 | 0.056685 | 0.046047 | −0.067748 | 0.057119 | −0.000411 |
| 179 | 0.045252 | 0.028298 | −0.051764 | 0.001842 | −0.040703 | −0.001996 | 0.08058 | 0.048815 | −0.00555 | 0.002453 | 0.117405 | 0.036938 | 0.035174 | −0.013169 |
| 180 | −0.062764 | 0.061267 | −0.03094 | 0.046008 | 0.064981 | 0.031009 | 0.033908 | 0.010534 | −0.01084 | 0.01254 | −0.005474 | 0.001525 | 0.01854 | 0.07725 |
| 181 | −0.00297 | 0.012478 | −0.007118 | 0.037696 | 0.02384 | 0.044629 | −0.015927 | 0.008816 | −0.04999 | 0.045672 | −0.007631 | −0.040457 | −0.079516 | 0.023295 |
| 182 | 0.092102 | 0.074755 | −0.07836 | −0.011671 | 0.111133 | −0.034094 | −0.007084 | −0.062017 | −0.021069 | 0.003515 | 0.04327 | −0.102087 | −0.088346 | 0.065984 |
| 183 | 0.095306 | 0.0361 | 0.004493 | −0.043758 | 0.05086 | 0.062898 | 0.024608 | −0.032476 | −0.004947 | −0.043934 | 0.024887 | 0.033906 | −0.038275 | 0.016033 |
| 184 | 0.024268 | 0.04601 | 0.102261 | 0.158361 | 0.01826 | 0.051585 | −0.106183 | −0.062718 | 0.048368 | 0.020218 | 0.017436 | −0.012365 | 0.027108 | −0.024722 |
| 185 | 0.038384 | 0.021833 | 0.036896 | −0.043176 | −0.027687 | −0.02655 | 0.055599 | −0.032299 | −0.072617 | 0.058492 | −0.035143 | −0.086761 | −0.033535 | −0.002295 |
| 186 | −0.08368 | −0.03406 | −0.048628 | −0.082063 | −0.058843 | 0.09704 | −0.00343 | −0.038921 | −0.052422 | 0.079415 | −0.114605 | 0.105343 | 0.06582 | −0.008581 |
| 187 | −0.016435 | −0.040756 | −0.023343 | −0.050489 | 0.11244 | −0.004061 | −0.042532 | −0.066692 | −0.088332 | 0.048374 | −0.044119 | −0.031941 | 0.025274 | −0.062337 |
| 188 | −0.009149 | −0.024344 | 0.022814 | −0.02974 | 0.010661 | 0.020174 | 0.002846 | 0.00468 | 0.040056 | 0.041955 | 0.008407 | −0.050508 | −0.041444 | −0.033566 |
| 189 | −0.041697 | −0.018353 | −0.022358 | −0.055698 | −0.118355 | 0.05887 | −0.00389 | −0.013706 | 0.045709 | −0.035283 | 0.006686 | 0.141147 | −0.087991 | −0.002701 |
| 190 | −0.027841 | 0.104036 | 0.056351 | −0.021094 | 0.090797 | 0.044463 | −0.031961 | −0.008867 | −0.03058 | −0.101832 | −0.010041 | 0.174314 | −0.086501 | −0.02365 |
| 191 | −0.022614 | 0.022723 | 0.030272 | 0.037261 | 0.005928 | −0.1466 | −0.033741 | 0.015398 | −0.012494 | −0.047241 | −0.039497 | −0.11107 | 0.007334 | 0.005425 |
| 192 | 0.104845 | −0.0255 | −0.128021 | 0.051689 | 0.013468 | −0.064358 | −0.118653 | −0.050161 | 0.1077 | −0.081712 | −0.133657 | 0.026166 | −0.036287 | −0.043826 |
| 193 | 0.11223 | 0.100951 | −0.057494 | 0.009791 | 0.021918 | −0.053009 | −0.028988 | 0.128063 | −0.068087 | −0.02165 | 0.152568 | −0.053249 | 0.072917 | −0.032632 |
| 194 | −0.023486 | 0.029763 | 0.147163 | −0.002012 | −0.028509 | 0.095921 | 0.009471 | 0.05799 | 0.066508 | −0.032922 | 0.051962 | −0.037286 | 0.038817 | 0.029386 |
| 195 | 0.0692751 | −0.045428 | 0.034812 | −0.044264 | 0.089155 | 0.008164 | −0.003703 | −0.001326 | 0.015271 | −0.100226 | −0.034252 | −0.016062 | 0.002269 | 0.013412 |
| 196 | −0.060336 | 0.008119 | 0.078984 | 0.079955 | −0.033112 | −0.057849 | 0.022496 | −0.124898 | −0.009278 | −0.047714 | 0.063037 | −0.004201 | 0.051639 | 0.045952 |
| 197 | 0.006319 | −0.112928 | −0.043696 | 0.085383 | −0.02037 | 0.033593 | −0.064237 | 0.087867 | 0.00844 | 0.033354 | 0.017507 | −0.014852 | −0.036261 | 0.006916 |
| 198 | 0.001963 | −0.063577 | −0.052179 | 0.056569 | −0.016858 | −0.045654 | −0.060016 | 0.026008 | 0.06075 | 0.025986 | 0.014013 | 0.045977 | −0.01543 | −0.046029 |
| 199 | −0.012656 | −0.028674 | −0.057926 | 0.086556 | 0.032789 | −0.019137 | −0.018173 | −0.112626 | −0.004769 | −0.079426 | −0.000793 | −0.022113 | −0.040053 | −0.062733 |
| 200 | −0.009817 | −0.027239 | 0.058185 | −0.056185 | 0.067617 | 0.025007 | 0.009227 | 0.050645 | −0.1098 | −0.008285 | 0.048352 | 0.059231 | 0.096007 | −0.08694 |
| 201 | 0.033359 | 0.007205 | 0.070935 | −0.006169 | −0.015286 | −0.013299 | 0.020798 | −0.013011 | 0.061686 | 0.038814 | 0.079058 | 0.014447 | −0.024193 | −0.018602 |
| 202 | 0.076306 | 0.04223 | −0.041544 | 0.045858 | −0.038936 | −0.032117 | 0.013432 | −0.060735 | −0.102916 | 0.037836 | 0.003643 | 0.073907 | 0.030669 | 0.054191 |
| 203 | −0.110299 | −0.012934 | 0.049833 | 0.010794 | 0.020453 | −0.069916 | 0.024437 | 0.062554 | 0.044461 | −0.019708 | 0.033792 | 0.014808 | 0.018076 | 0.010932 |
| 204 | −0.001475 | −0.044981 | 0.052313 | −0.02736 | 0.016852 | 0.060209 | −0.0549 | −0.02843 | −0.051254 | 0.048976 | −0.008575 | 0.095092 | 0.016758 | −0.066619 |
| 205 | −0.034221 | −0.044892 | 0.019367 | −0.027405 | 0.019835 | 0.020455 | −0.076356 | −0.029289 | −0.027906 | 0.046759 | 0.039422 | −0.028053 | 0.004999 | −0.006388 |
| 206 | 0.045434 | 0.045513 | −0.002487 | 0.114402 | 0.061294 | −0.067312 | −0.003828 | 0.037186 | −0.032766 | 0.029585 | 0.03606 | −0.013076 | 0.050331 | −0.007678 |
| 207 | −0.073458 | 0.00388 | −0.033027 | −0.024339 | −0.011722 | −0.034107 | −0.044584 | −0.000057 | −0.01744 | 0.012474 | 0.014528 | 0.044031 | −0.044491 | 0.003913 |
| 208 | −0.021349 | 0.043268 | −0.045024 | −0.017552 | −0.035366 | 0.097937 | −0.030836 | −0.027961 | 0.004248 | 0.007432 | −0.013473 | 0.069268 | −0.119291 | −0.006207 |
| 209 | −0.027696 | 0.025739 | −0.040949 | 0.028915 | −0.098541 | −0.019923 | −0.017259 | 0.026956 | −0.030494 | 0.013226 | −0.020316 | −0.062568 | −0.059147 | 0.020583 |
| 210 | −0.061713 | 0.086459 | 0.061769 | 0.070189 | −0.016166 | 0.014016 | 0.062709 | −0.047922 | 0.161801 | −0.00159 | 0.027642 | 0.015822 | −0.06836 | 0.039785 |
| 211 | −0.024989 | −0.008978 | −0.020697 | −0.06937 | 0.013613 | 0.012041 | −0.060565 | −0.011528 | −0.037735 | 0.038616 | 0.06355 | 0.03062 | 0.090682 | −0.013822 |
| 212 | 0.092133 | −0.005885 | 0.004254 | −0.035431 | −0.097483 | 0.007889 | 0.032333 | −0.101086 | −0.019838 | −0.020836 | 0.072445 | −0.025263 | −0.011601 | −0.021534 |
| 213 | −0.020207 | 0.004938 | −0.028894 | −0.036881 | 0.011007 | −0.033918 | −0.078376 | −0.025723 | −0.028629 | 0.045189 | −0.024951 | 0.015251 | 0.072357 | −0.019087 |
| 214 | −0.012388 | −0.0117 | −0.097595 | 0.005093 | −0.091439 | −0.030266 | 0.113752 | 0.040362 | 0.093286 | −0.001212 | 0.036027 | 0.052039 | 0.082077 | −0.030225 |
| 215 | 0.052681 | −0.188281 | 0.027534 | −0.023862 | 0.026744 | −0.044016 | −0.082226 | −0.021791 | −0.095306 | −0.132292 | 0.076407 | 0.049226 | −0.103118 | 0.023356 |
| 216 | −0.003981 | 0.04882 | 0.063105 | 0.003091 | −0.051271 | 0.041066 | 0.003293 | 0.027288 | −0.024515 | 0.025735 | −0.096003 | −0.027624 | −0.082322 | −0.049273 |
| 217 | −0.044796 | 0.041779 | −0.004548 | −0.026277 | 0.006876 | −0.015317 | 0.022961 | 0.002289 | 0.017352 | −0.050557 | 0.056052 | 0.06406 | −0.001026 | 0.09749 |
| 218 | 0.035036 | −0.021116 | −0.018709 | 0.064954 | 0.029271 | 0.037567 | 0.014939 | 0.066275 | 0.104348 | 0.021614 | −0.121627 | −0.033895 | −0.047027 | 0.045271 |
| 219 | 0.03909 | −0.040665 | 0.032161 | 0.078444 | −0.001399 | −0.02319 | 0.022346 | 0.021128 | 0.089585 | 0.05394 | −0.048346 | −0.024897 | −0.035337 | −0.043213 |
| 220 | −0.056912 | 0.015158 | −0.090653 | 0.007169 | 0.006496 | −0.052055 | 0.006192 | 0.019499 | −0.093761 | 0.006169 | 0.036635 | 0.029545 | 0.070177 | 0.025752 |
| 221 | 0.016785 | −0.070025 | 0.002113 | −0.011893 | −0.011522 | −0.063386 | 0.098008 | 0.03051 | 0.054473 | −0.072834 | −0.076212 | −0.022633 | −0.020166 | −0.043261 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 222 | −0.002417 | 0.040888 | 0.095439 | −0.05563 | 0.001761 | 0.018393 | 0.05883 | −0.011971 | −0.017953 | −0.011286 | −0.033077 | 0.006009 | −0.04244 | −0.079115 |
| 223 | 0.041609 | 0.021163 | 0.019399 | 0.041103 | 0.050988 | 0.01585 | 0.025377 | 0.064514 | 0.029995 | 0.052077 | 0.07526 | 0.062514 | −0.045145 | −0.020697 |
| 224 | −0.065499 | −0.016697 | 0.017188 | 0.058953 | −0.015307 | −0.026461 | −0.043182 | 0.009306 | 0.032275 | 0.002638 | −0.046 | −0.036798 | 0.016107 | 0.023923 |
| 225 | −0.050524 | −0.006569 | 0.029751 | 0.046122 | −0.027483 | −0.042335 | −0.050082 | −0.03275 | 0.017181 | 0.012692 | −0.068385 | −0.027285 | −0.032697 | −0.024387 |
| 226 | 0.040151 | −0.011362 | 0.006831 | −0.014486 | 0.033061 | 0.085988 | −0.026811 | −0.034435 | −0.008023 | −0.001458 | −0.005319 | −0.006954 | −0.137849 | −0.067021 |
| 227 | −0.063754 | 0.000635 | −0.05769 | −0.14303 | −0.008917 | −0.05692 | 0.075663 | −0.006836 | 0.088018 | −0.021715 | 0.099183 | 0.098818 | 0.054896 | −0.03017 |
| 228 | 0.121179 | 0.030194 | −0.03957 | −0.048746 | 0.022973 | 0.089533 | 0.025259 | −0.015149 | 0.079443 | 0.044094 | −0.017056 | −0.086545 | 0.063492 | 0.020329 |
| 229 | −0.061516 | 0.009337 | 0.000041 | −0.036573 | −0.05913 | −0.06503 | −0.013788 | −0.031207 | −0.013261 | 0.07664 | 0.045651 | −0.135598 | −0.016304 | 0.022606 |
| 230 | 0.030195 | −0.011536 | 0.012513 | 0.010012 | −0.008107 | 0.097452 | 0.002186 | −0.022256 | −0.074293 | −0.044993 | −0.03124 | −0.016597 | −0.027428 | −0.004531 |
| 231 | 0.003608 | 0.071645 | −0.066905 | −0.022591 | −0.155256 | 0.060184 | 0.061998 | −0.032557 | −0.095264 | −0.039206 | −0.051963 | −0.040074 | −0.047314 | 0.002356 |
| 232 | 0.003688 | 0.035858 | −0.010974 | 0.085662 | −0.052034 | −0.166326 | 0.14387 | 0.075452 | −0.049933 | −0.078113 | −0.036523 | −0.050678 | 0.071508 | −0.005537 |
| 233 | 0.061011 | 0.018319 | −0.029994 | −0.027577 | −0.12906 | 0.006544 | −0.073065 | 0.050181 | 0.059523 | −0.09537 | 0.041381 | −0.063163 | 0.074926 | −0.051003 |
| 234 | −0.051841 | −0.000325 | 0.053853 | −0.034249 | −0.079213 | 0.017774 | −0.0728 | −0.024526 | 0.081383 | 0.031907 | 0.062391 | 0.051354 | −0.066188 | −0.001353 |
| 235 | −0.122103 | −0.055245 | 0.007065 | −0.030361 | −0.001213 | −0.101742 | 0.041195 | −0.073946 | −0.159846 | −0.079139 | −0.008194 | 0.001785 | 0.079904 | 0.0464 |
| 236 | 0.024437 | 0.021313 | −0.07064 | −0.036225 | 0.0087 | 0.090851 | 0.009305 | −0.060942 | −0.000233 | −0.075095 | 0.01851 | 0.048052 | 0.053969 | 0.043515 |
| 237 | 0.019546 | 0.020346 | −0.003427 | 0.069762 | −0.03937 | 0.062214 | −0.090128 | 0.088065 | −0.051548 | 0.062397 | 0.056158 | 0.072882 | 0.02682 | −0.024876 |
| 238 | 0.01837 | −0.026366 | −0.015272 | −0.043181 | 0.052418 | −0.08639 | −0.033009 | 0.039978 | 0.014898 | 0.000017 | 0.032219 | 0.027071 | −0.029209 | −0.075565 |
| 239 | −0.030384 | −0.006209 | −0.010119 | −0.122351 | −0.016198 | −0.070046 | −0.008424 | 0.004716 | −0.018846 | −0.022064 | 0.011761 | −0.078613 | −0.074178 | −0.000123 |
| 240 | 0.041543 | 0.046072 | −0.053495 | −0.076619 | −0.029974 | −0.032658 | −0.007314 | 0.018601 | −0.008559 | 0.009326 | 0.021808 | 0.007189 | −0.032482 | −0.020482 |
| 241 | −0.074098 | 0.005551 | 0.03941 | −0.122728 | −0.036673 | −0.007135 | −0.039407 | 0.016102 | 0.011766 | 0.058503 | 0.031543 | −0.004107 | 0.061339 | 0.001506 |
| 242 | 0.018473 | 0.075892 | −0.009392 | −0.053952 | 0.066294 | −0.046547 | −0.01776 | −0.053616 | −0.026013 | −0.066036 | −0.055844 | 0.051744 | 0.01723 | 0.026328 |
| 243 | −0.010459 | −0.05399 | 0.053883 | 0.065457 | 0.062056 | 0.058095 | −0.054783 | 0.028069 | −0.008421 | 0.078709 | 0.022353 | 0.0716 | 0.045183 | 0.006605 |
| 244 | −0.01437 | 0.037043 | −0.023511 | 0:048825 | −0.004719 | 0.033169 | 0.050082 | −0.069739 | 0.000856 | −0.051164 | 0.017254 | −0.064405 | 0.041923 | 0.028978 |
| 245 | −0.104542 | −0.042697 | −0.068591 | 0.039409 | −0.058255 | 0.032338 | 0.127587 | −0.002912 | 0.006158 | −0.075619 | −0.034354 | −0.04003 | −0.086326 | −0.010875 |
| 246 | −0.006099 | 0.05684 | −0.021568 | −0.001511 | 0.010644 | −0.031898 | −0.00618 | −0.015363 | −0.017081 | 0.063932 | 0.034625 | −0.019082 | 0.032065 | 0.048785 |
| 247 | 0.024597 | 0.025202 | 0.026241 | −0.055997 | 0.038685 | 0.040569 | −0.009824 | −0.015072 | 0.071398 | 0.009978 | 0.039513 | −0.013934 | 0.046981 | 0.011966 |
| 248 | 0.035663 | −0.062246 | −0.001483 | −0.005699 | 0.045375 | 0.016992 | 0.034684 | 0.05723 | −0.029942 | 0.014349 | −0.029825 | −0.052741 | −0.149295 | −0.00798 |
| 249 | 0.027825 | −0.000993 | 0.032029 | −0.002288 | −0.001113 | 0.013979 | 0.107114 | −0.020199 | −0.044644 | 0.122322 | 0.076559 | 0.057956 | −0.069852 | 0.001409 |
| 250 | 0.009381 | 0.052544 | 0.017678 | −0.023943 | −0.004055 | −0.040776 | −0.054342 | −0.098112 | 0.012275 | −0.029991 | 0.025065 | −0.038758 | 0.170426 | 0.097713 |
| 251 | 0.002585 | 0.052898 | 0.032777 | 0.049311 | 0.015073 | −0.013861 | 0.052312 | 0.000023 | −0.033264 | −0.037095 | 0.045918 | 0.023348 | −0.003442 | 0.053807 |
| 252 | 0.00377 | −0.050899 | −0.049854 | 0.025681 | 0.075848 | 0.093606 | −0.017497 | 0.081986 | 0.016348 | 0.07864 | −0.035077 | 0.001173 | −0.05733 | −0.003488 |
| 253 | 0.011078 | −0.011549 | −0.04432 | 0.069364 | −0.044675 | 0.060502 | −0.088773 | 0.005219 | 0.00302 | −0.046252 | 0.034585 | −0.062662 | 0.053244 | 0.009504 |
| 254 | 0.088418 | 0.088974 | 0.055385 | 0.006385 | −0.015337 | −0.091495 | −0.125967 | 0.10274 | −0.029288 | −0.003458 | 0.019095 | 0.023069 | −0.023098 | −0.110203 |
| 255 | 0.088952 | 0.026827 | −0.010157 | −0.077148 | 0.035867 | 0.007917 | −0.041016 | −0.002846 | 0.00362 | 0.021062 | −0.012144 | −0.105089 | 0.035052 | −0.007604 |
| 276 | −0.014332 | −0.038449 | 0.037299 | 0.01392 | 0.067882 | 0.012178 | 0.016638 | −0.057155 | 0.070696 | 0.135436 | 0.035723 | −0.030847 | 0.011069 | −0.025701 |
| 257 | 0.004311 | −0.00971 | −0.001536 | 0.023094 | −0.041763 | −0.012291 | −0.032835 | −0.01838 | 0.036728 | −0.031151 | 0.011556 | −0.016071 | 0.067484 | −0.104133 |
| 258 | 0.012256 | 0.04673 | −0.006536 | −0.124877 | 0.01359 | −0.017879 | −0.075706 | 0.051926 | −0.035728 | −0.006136 | −0.033128 | −0.014553 | −0.053479 | −0.011549 |
| 259 | 0.041434 | −0.038199 | −0.006065 | −0.013118 | 0.012406 | 0.065271 | 0.029605 | −0.007403 | 0.070195 | −0.009161 | −0.008292 | −0.007524 | −0.069574 | −0.024677 |
| 260 | −0.014268 | −0.112141 | 0.019611 | 0.041617 | −0.10988 | 0.045188 | −0.085731 | 0.050493 | 0.044635 | −0.075938 | −0.078843 | −0.036111 | 0.071909 | −0.001806 |
| 261 | 0.013662 | −0.036055 | −0.017529 | 0.134192 | 0.039189 | −0.081465 | 0.007681 | 0.042936 | 0.036503 | 0.025417 | 0.002339 | 0.053257 | −0.070985 | −0.008919 |
| 262 | 0.01946 | 0.065013 | −0.060228 | −0.024402 | −0.009927 | −0.032999 | 0.02267 | 0.034221 | −0.012399 | 0.004712 | 0.027561 | −0.04561 | 0.008456 | −0.122939 |
| 263 | 0.053854 | 0.018894 | −0.014145 | −0.003619 | −0.084814 | −0.050873 | 0.002719 | 0.032914 | −0.01437 | 0.049655 | −0.010739 | −0.078574 | −0.087991 | −0.06195 |
| 264 | −0.132218 | −0.033749 | 0.013886 | −0.033851 | −0.078365 | 0.002221 | −0.016151 | −0.095195 | −0.004473 | −0.019924 | 0.06502 | −0.034451 | −0.10466 | 0.026475 |
| 265 | −0.068468 | −0.00337 | −0.014562 | −0.074575 | −0.00843 | −0.01333 | −0.057116 | 0.056224 | −0.062508 | −0.068548 | 0.04608 | −0.008785 | 0.062853 | 0.056368 |
| 266 | −0.054179 | −0.030968 | 0.027302 | 0.028615 | −0.026505 | 0.020564 | 0.013759 | −0.085893 | 0.024864 | 0.062231 | −0.051227 | −0.011642 | 0.048756 | 0.031965 |
| 267 | −0.074213 | 0.098244 | −0.073449 | 0.069399 | −0.034299 | −0.009787 | −0.069717 | 0.03313 | −0.030923 | 0.034811 | −0.023519 | 0.00838 | −0.000207 | 0.045252 |
| 268 | 0.010287 | 0.019522 | 0.084398 | −0.028727 | −0.006493 | 0.046657 | −0.030028 | −0.012527 | −0.025931 | −0.032047 | −0.02284 | −0.006616 | −0.038835 | −0.040295 |
| 269 | −0.039433 | −0.021824 | 0.048323 | −0.006961 | 0.051928 | 0.061346 | 0.033595 | −0.007072 | −0.050976 | 0.003084 | −0.053231 | 0.006774 | −0.013456 | −0.061529 |
| 270 | 0.005731 | 0.007801 | 0.020488 | −0.038794 | 0.062783 | 0.017788 | 0.017751 | 0.060366 | 0.024676 | 0.009763 | −0.059758 | −0.030659 | −0.046622 | 0.091859 |
| 271 | −0.014548 | 0.070199 | 0.031838 | −0.046693 | 0.048653 | −0.080731 | −0.000661 | 0.000762 | −0.004571 | −0.067015 | 0.026943 | −0.037478 | −0.022639 | 0.087457 |
| 272 | 0.050152 | −0.00022 | −0.02878 | −0.033929 | 0.034863 | −0.087351 | −0.059976 | 0.028918 | 0.016798 | 0.010028 | 0.04969 | 0.038603 | −0.01976 | 0.019211 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 273 | 0.094777 | 0.002718 | 0.054693 | 0.020747 | −0.018145 | 0.015275 | −0.02533 | −0.026931 | 0.03715 | −0.037276 | −0.002763 | 0.106184 | −0.017679 | −0.03975 |
| 274 | 0.073541 | −0.015022 | 0.050177 | 0.027173 | −0.001539 | −0.01068 | −0.00324 | −0.044975 | 0.045402 | 0.008477 | −0.007067 | 0.090628 | −0.01995 | −0.00024 |
| 275 | −0.030779 | −0.031831 | −0.019914 | 0.069111 | 0.061096 | −0.034686 | 0.014854 | −0.001543 | 0.054332 | 0.025549 | 0.100194 | 0.01755 | 0.008651 | −0.032268 |
| 276 | −0.044699 | 0.042013 | −0.016545 | 0.008289 | −0.015555 | 0.036091 | 0.075042 | −0.040746 | 0.024442 | 0.004355 | −0.052544 | 0.047556 | 0.013998 | −0.076277 |
| 277 | −0.012749 | −0.044178 | −0.000594 | 0.012903 | 0.040227 | −0.023872 | 0.027081 | −0.028502 | −0.010345 | 0.007857 | −0.060665 | 0.008994 | 0.053445 | 0.081209 |
| 278 | 0.052917 | −0.025529 | −0.071985 | −0.075835 | −0.044093 | −0.025577 | −0.050787 | 0.006244 | 0.003699 | 0.012281 | −0.005017 | 0.009237 | −0.026708 | 0.034442 |
| 279 | −0.052961 | −0.045807 | −0.028625 | −0.04582 | 0.016591 | −0.053837 | 0.010989 | 0.09742 | 0.014971 | −0.003738 | −0.050278 | −0.074463 | −0.091827 | 0.009376 |
| 280 | 0.046335 | −0.039685 | 0.06184 | −0.051956 | −0.027878 | 0.020873 | 0.015577 | −0.079969 | 0.044332 | −0.02139 | 0.037006 | 0.042708 | −0.032647 | −0.043601 |
| 281 | −0.045335 | −0.047352 | 0.021146 | 0.004368 | −0.003521 | −0.020992 | 0.043827 | −0.029443 | −0.044671 | 0.036837 | −0.013001 | −0.047733 | −0.029335 | 0.04651 |
| 282 | 0.018134 | 0.025187 | 0.000497 | 0.011401 | 0.018686 | 0.00349 | 0.016927 | −0.053549 | −0.04368 | −0.01531 | −0.032463 | 0.052603 | 0.009263 | −0.037263 |
| 283 | 0.011581 | 0.031287 | −0.031707 | 0.006517 | −0.041625 | 0.001923 | 0.04564 | 0.065232 | 0.055638 | 0.080401 | 0.019073 | 0.014814 | 0.030879 | 0.080121 |
| 284 | −0.057045 | −0.045133 | −0.001988 | 0.013611 | −0.050376 | −0.074177 | 0.007354 | −0.051445 | 0.050661 | −0.016903 | 0.027957 | 0.008666 | 0.101455 | 0.036032 |
| 285 | −0.013953 | −0.05103 | 0.017082 | 0.071584 | −0.02287 | −0.026082 | −0.007384 | −0.082056 | 0.032817 | −0.000085 | −0.006349 | 0.054631 | 0.086251 | 0.171089 |
| 286 | −0.022615 | 0.02292 | −0.036138 | −0.00506 | −0.027048 | −0.052834 | −0.026587 | 0.011936 | −0.020093 | −0.042791 | −0.047633 | −0.012686 | −0.01529 | 0.025603 |
| 287 | −0.040383 | 0.044741 | −0.032467 | 0.004221 | −0.016365 | −0.014064 | 0.030728 | 0.004512 | 0.028247 | 0.046853 | 0.026787 | 0.044474 | −0.011054 | 0.029375 |
| 288 | 0.056567 | −0.017189 | −0.013689 | −0.11828 | −0.040024 | −0.043244 | −0.070391 | −0.065147 | −0.03658 | 0.097273 | −0.071021 | 0.025044 | −0.000735 | −0.032383 |
| 289 | 0.025903 | 0.078308 | 0.022194 | −0.021772 | 0.048372 | −0.015083 | 0.018282 | −0.032747 | −0.001865 | −0.00211 | −0.024916 | −0.035602 | 0.040513 | 0.014634 |
| 290 | −0.016213 | 0.025886 | −0.015373 | 0.056756 | −0.031071 | 0.043612 | 0.025259 | 0.038619 | −0.017598 | −0.007184 | −0.043852 | 0.042073 | −0.026047 | −0.045886 |
| 291 | −0.023772 | 0.042491 | −0.01694 | 0.032183 | −0.047497 | 0.019867 | 0.035214 | 0.009144 | −0.015864 | 0.007546 | −0.046347 | 0.009743 | −0.032233 | −0.025576 |
| 292 | −0.086592 | 0.052723 | −0.007153 | 0.048216 | 0.055793 | 0.01981 | 0.053454 | −0.004371 | −0.026603 | −0.032941 | −0.026095 | −0.039259 | 0.041581 | 0.099513 |
| 293 | 0.031641 | 0.026733 | −0.006975 | −0.030039 | 0.050842 | 0.056184 | −0.108099 | −0.01875 | −0.003044 | −0.030868 | 0.02094 | −0.05354 | 0.074043 | −0.021907 |
| 294 | −0.04952 | −0.002012 | 0.083772 | 0.012926 | 0.02613 | 0.014582 | −0.036894 | −0.042011 | −0.065431 | 0.083887 | −0.051024 | −0.041363 | 0.026252 | 0.007253 |
| 295 | 0.029693 | 0.002633 | −0.047591 | 0.002965 | −0.04481 | 0.04397 | −0.000749 | 0.054001 | 0.0477 | 0.068444 | −0.059155 | −0.017387 | −0.022427 | −0.019153 |
| 296 | −0.081499 | 0.056051 | −0.048096 | 0.001531 | 0.028982 | 0.015935 | −0.050568 | 0.005363 | −0.096009 | 0.074626 | −0.033319 | −0.005191 | −0.066262 | 0.00841 |
| 297 | −0.058858 | 0.066603 | −0.040315 | −0.023891 | −0.104829 | 0.046885 | 0.049947 | 0.039716 | 0.016857 | 0.046517 | −0.04128 | 0.075585 | −0.033651 | 0.121236 |
| 298 | −0.031339 | 0.047815 | −0.065037 | −0.159635 | −0.169837 | −0.004381 | −0.023865 | −0.076477 | 0.021755 | −0.119091 | 0.045569 | −0.027537 | −0.068565 | 0.021778 |
| 299 | 0.056707 | 0.03833 | 0.053187 | 0.025296 | −0.092685 | 0.026142 | −0.074736 | 0.023548 | −0.011955 | −0.09911 | 0.042518 | −0.006314 | 0.081756 | −0.019789 |
| 300 | −0.118267 | 0.011191 | 0.0675 | −0.054354 | 0.027961 | 0.0253 | −0.03939 | 0.048345 | 0.001209 | 0.042052 | −0.083137 | −0.026539 | −0.027357 | 0.003043 |
| 301 | −0.034841 | −0.063739 | −0.022722 | −0.003513 | −0.073711 | 0.004107 | −0.014377 | −0.038213 | −0.136455 | 0.053025 | 0.017465 | 0.006655 | 0.050465 | 0.04342 |
| 302 | −0.00353 | −0.095363 | 0.019653 | −0.102969 | 0.038454 | −0.0443 | 0.068042 | −0.056136 | −0.052978 | −0.045655 | 0.034238 | −0.04898 | 0.005039 | −0.036869 |
| 303 | 0.022714 | −0.045463 | −0.050684 | −0.011369 | 0.022497 | 0.034266 | 0.06271 | −0.059527 | −0.030591 | −0.022462 | 0.051182 | 0.008791 | 0.060171 | −0.053886 |
| 304 | 0.09396 | −0.000912 | −0.008346 | 0.022412 | 0.035431 | 0.025428 | 0.076407 | −0.095325 | −0.04146 | −0.000767 | 0.137711 | −0.079814 | −0.01727 | 0.095917 |
| 305 | −0.072696 | 0.034631 | 0.042517 | 0.095984 | 0.059282 | 0.016667 | 0.082232 | −0.019969 | 0.074741 | −0.000988 | −0.017036 | −0.00643 | −0.024798 | −0.084103 |
| 306 | −0.02435 | 0.010885 | 0.071589 | −0.056543 | 0.024047 | −0.11683 | 0.057014 | −0.002559 | 0.033058 | −0.033153 | 0.099098 | −0.056063 | −0.020636 | 0.032825 |
| 307 | 0.019858 | 0.026311 | −0.000447 | −0.018043 | −0.063528 | −0.026308 | 0.050316 | −0.00534 | 0.047501 | −0.000021 | −0.051102 | 0.016066 | −0.029061 | −0.005349 |
| 308 | 0.00371 | −0.052885 | 0.017566 | 0.005961 | −0.015838 | −0.03799 | −0.039084 | −0.046714 | 0.007336 | −0.007142 | −0.012438 | 0.0215 | −0.012223 | −0.001481 |
| 309 | 0.041957 | 0.021472 | −0.061524 | −0.026793 | 0.054275 | 0.068839 | 0.000069 | 0.055503 | 0.045618 | 0.057577 | 0.000085 | 0.039792 | 0.003844 | −0.036874 |
| 310 | 0.146453 | −0.050434 | 0.014761 | 0.103444 | 0.069622 | −0.068479 | 0.013096 | 0.058635 | 0.024082 | −0.050229 | −0.062081 | −0.030228 | 0.018937 | −0.039031 |
| 311 | −0.013512 | 0.043673 | 0.036421 | 0.029447 | −0.018484 | 0.090931 | 0.030164 | 0.071225 | 0.055457 | −0.049312 | 0.026226 | −0.02856 | −0.043225 | −0.065014 |
| 312 | −0.028168 | 0.027786 | −0.00752 | 0.007234 | 0.037198 | −0.01186 | −0.073116 | 0.019048 | −0.000758 | −0.11553 | 0.084977 | −0.006411 | 0.022635 | 0.015215 |
| 313 | −0.04834 | −0.085553 | 0.028316 | 0.004841 | 0.101039 | 0.064664 | −0.056766 | −0.030113 | 0.00034 | −0.012448 | −0.01985 | −0.126584 | −0.030415 | −0.025389 |
| 314 | −0.130356 | −0.071171 | −0.14166 | 0.026381 | 0.041528 | 0.01365 | 0.060428 | −0.068897 | 0.08919 | −0.076727 | −0.037042 | −0.087428 | −0.060669 | −0.056464 |
| 315 | −0.110454 | −0.000866 | −0.04571 | 0.018122 | 0.046199 | 0.035093 | 0.003771 | 0.006957 | −0.020218 | 0.055431 | 0.029228 | −0.002835 | 0.000571 | 0.024834 |
| 316 | 0.004897 | 0.021952 | −0.020308 | −0.079861 | −0.063831 | −0.06035 | −0.000735 | 0.008729 | −0.053516 | 0.080228 | 0.028196 | −0.003618 | −0.076001 | 0.034867 |
| 317 | −0.03627 | −0.055087 | −0.070265 | 0.057059 | −0.058982 | −0.04013 | −0.007304 | 0.103024 | −0.063178 | 0.032392 | 0.000328 | −0.06195 | −0.012231 | 0.000581 |
| 318 | 0.041738 | 0.022996 | −0.04596 | 0.072353 | −0.045481 | −0.076002 | −0.059205 | −0.076056 | 0.067466 | −0.065072 | 0.070963 | −0.06553 | −0.047706 | 0.061115 |
| 319 | −0.061013 | 0.027326 | 0.008689 | 0.111529 | −0.016904 | 0.008392 | 0.005994 | 0.009511 | −0.081073 | 0.044964 | −0.066278 | 0.056069 | −0.027239 | 0.047569 |
| 320 | 0.041887 | 0.111169 | 0.093156 | 0.007039 | −0.005882 | −0.02037 | −0.108121 | −0.032885 | 0.030399 | 0.11442 | −0.025751 | −0.058395 | −0.003964 | −0.035994 |
| 321 | −0.074666 | 0.015198 | 0.032856 | 0.035295 | −0.000794 | 0.012369 | −0.066608 | 0.084993 | 0.038228 | −0.031602 | 0.063694 | 0.078903 | 0.11046 | −0.039109 |
| 322 | 0.037074 | −0.0711 | 0.093943 | −0.03061 | 0.004288 | 0.027741 | −0.039936 | 0.059098 | 0.017835 | 0.079958 | −0.004955 | −0.059911 | 0.034601 | 0.026425 |
| 323 | 0.159732 | −0.007897 | −0.045549 | −0.025526 | −0.125623 | 0.064773 | −0.067339 | 0.024346 | 0.005426 | 0.074941 | −0.021265 | −0.072738 | −0.059262 | −0.009484 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 324 | −0.002437 | −0.019335 | −0.049364 | −0.017726 | −0.063057 | −0.026273 | −0.081352 | −0.051719 | 0.042111 | 0.009987 | 0.042712 | −0.029708 | 0.04533 | −0.00282 |
| 325 | 0.000019 | 0.020703 | −0.121019 | 0.024206 | 0.028991 | 0.09338 | −0.007313 | 0.003574 | −0.008048 | −0.048538 | 0.065865 | 0.038957 | 0.018898 | −0.055653 |
| 326 | 0.020249 | 0.038066 | 0.074253 | −0.013768 | −0.061407 | 0.002097 | 0.099652 | 0.101592 | −0.007534 | −0.040593 | 0.015407 | −0.011271 | −0.007505 | 0.053926 |
| 327 | 0.009761 | 0.012412 | 0.005833 | 0.034018 | 0.020926 | −0.082504 | −0.010422 | 0.003929 | −0.059207 | 0.033605 | −0.071951 | −0.001637 | 0.005495 | 0.072271 |
| 328 | 0.057197 | −0.047961 | 0.029166 | −0.019179 | 0.019329 | 0.09549 | 0.04366 | 0.028801 | 0.039449 | −0.023683 | 0.006513 | −0.078488 | 0.081218 | 0.004235 |
| 329 | 0.005372 | −0.051885 | −0.033907 | 0.037217 | −0.042514 | 0.027261 | 0.03168 | 0.077713 | −0.03645 | −0.000992 | −0.121838 | −0.01548 | 0.105358 | 0.019388 |
| 330 | −0.117173 | 0.0044 | −0.039911 | −0.002433 | 0.023341 | −0.018037 | −0.062389 | −0.120185 | −0.127898 | 0.039491 | −0.05672 | −0.017926 | 0.003103 | −0.020041 |
| 331 | 0.024985 | 0.110313 | 0.011325 | −0.127749 | 0.000709 | −0.022348 | 0.012438 | −0.108574 | 0.069146 | 0.07389 | −0.005739 | 0.039146 | 0.015506 | 0.019354 |
| 332 | 0.03093 | 0.053972 | 0.042789 | −0.000835 | −0.033053 | −0.076677 | 0.031876 | −0.022559 | −0.004825 | −0.048564 | 0.002891 | 0.097504 | −0.000619 | −0.04901 |
| 333 | 0.028928 | 0.008519 | −0.051942 | −0.017156 | 0.060967 | 0.022025 | −0.031896 | −0.044106 | −0.012687 | −0.017575 | −0.001868 | −0.046317 | 0.016124 | 0.058796 |
| 334 | 0.071185 | −0.013188 | 0.015174 | 0.021327 | −0.048805 | −0.033378 | 0.0289 | 0.041979 | 0.039711 | −0.04761 | 0.017501 | 0.00086 | 0.067566 | −0.004364 |
| 335 | 0.069453 | −0.168524 | 0.037908 | 0.001737 | −0.091159 | 0.016596 | 0.016896 | 0.004882 | 0.013595 | −0.006107 | −0.033853 | −0.032352 | 0.077986 | 0.052731 |
| 336 | 0.083057 | −0.02513 | −0.039723 | −0.093355 | −0.0867 | −0.150314 | 0.043277 | 0.06914 | 0.006416 | 0.065469 | −0.009651 | 0.036025 | 0.046587 | 0.048804 |
| 337 | −0.007015 | −0.066049 | 0.109634 | −0.063614 | 0.075623 | −0.08645 | 0.063633 | 0.01354 | 0.019551 | −0.055951 | −0.023442 | 0.133188 | −0.047068 | −0.018217 |
| 338 | 0.01948 | −0.000142 | −0.014301 | −0.00261 | 0.043392 | 0.070836 | −0.065136 | −0.065658 | −0.035999 | 0.039067. | 0.095145 | 0.018497 | 0.028368 | −0.043661 |
| 339 | −0.002355 | 0.03525 | −0.083144 | −0.050514 | 0.084569 | −0.042487 | 0.055845 | 0.125939 | −0.140685 | 0.001242 | 0.010956 | −0.02328 | −0.115252 | −0.024365 |
| 340 | −0.010098 | −0.008403 | −0.049184 | −0.050448 | −0.086923 | −0.0059 | 0.032547 | 0.011132 | −0.001435 | 0.052836 | −0.012433 | −0.01819 | 0.050454 | 0.028244 |

| | EH | EI | EJ | EK | EL | EM | EN | EO | EP | EQ | ER | ES | ET | EU |
|---|---|---|---|---|---|---|---|---|---|---|---|---|---|---|
| 1 | −0.018676 | −0.000067 | 0.167624 | −0.027212 | 0.035091 | −0.014237 | −0.001131 | −0.058135 | −0.075447 | 0.07422 | 0.029017 | 0.083842 | −0.050222 | 0.002676 |
| 2 | 0.00993 | −0.031265 | −0.028798 | −0.059608 | −0.036928 | 0.051041 | 0.046815 | −0.020897 | −0.018571 | 0.047339 | 0.076841 | 0.098184 | −0.001397 | 0.078712 |
| 3 | 0.067404 | −0.033899 | 0.023665 | 0.023532 | 0.05354 | 0.060095 | 0.112847 | 0.073754 | 0.034585 | 0.004284 | −0.014133 | −0.124409 | 0.006802 | 0.020426 |
| 4 | −0.045057 | 0.117048 | −0.031941 | 0.01522 | −0.02533 | 0.097185 | −0.038227 | 0.033379 | 0.157747 | −0.012244 | −0.081755 | −0.00486 | 0.049302 | 0.015863 |
| 5 | −0.012344 | −0.031157 | −0.017135 | 0.037383 | −0.002423 | 0.029285 | 0.034643 | 0.030475 | 0.049531 | −0.039786 | 0.047038 | −0.001339 | −0.034548 | −0.022925 |
| 6 | 0.025694 | −0.045905 | −0.061583 | −0.00339 | 0.05199 | 0.044319 | −0.005289 | −0.000524 | 0.029546 | −0.018167 | −0.007782 | 0.06624 | 0.005686 | −0.018681 |
| 7 | −0.049965 | 0.066146 | −0.061529 | −0.029251 | 0.0512 | −0.037817 | −0.019147 | −0.025043 | −0.011738 | −0.031933 | −0.051023 | −0.015003 | 0.065037 | 0.028934 |
| 8 | 0.026336 | 0.007845 | 0.066558 | −0.007092 | 0.038475 | −0.004041 | −0.071104 | −0.015743 | 0.030956 | −0.009524 | −0.047785 | −0.014831 | −0.033864 | −0.071865 |
| 9 | 0.035614 | −0.032985 | −0.000145 | 0.072749 | 0.039865 | 0.102766 | 0.047727 | 0.005449 | −0.040402 | 0.045205 | 0.102199 | 0.090319 | 0.056755 | −0.024854 |
| 10 | 0.018772 | 0.045785 | −0.073548 | 0.069486 | 0.03922 | −0.076567 | −0.004483 | −0.038048 | 0.018812 | −0.050332 | 0.065217 | 0.00675 | 0.05709 | −0.011752 |
| 11 | 0.042906 | 0.01935 | −0.018155 | 0.022174 | 0.031846 | 0.022837 | 0.012553 | 0.05216 | 0.044566 | −0.018254 | −0.085662 | −0.04932 | −0.104786 | 0.07601 |
| 12 | 0.011255 | −0.052133 | 0.069111 | 0.059734 | −0.00935 | −0.005294 | 0.033123 | −0.003873 | 0.018823 | −0.014284 | −0.028586 | 0.000213 | 0.042835 | −0.041153 |
| 13 | −0.003078 | 0.044407 | −0.010177 | −0.031926 | 0.024722 | −0.044343 | 0.007496 | 0.056413 | −0.03971 | −0.033585 | 0.032658 | 0.192897 | −0.069092 | −0.128842 |
| 14 | −0.034996 | −0.025683 | −0.00865 | 0.039545 | −0.074809 | −0.063479 | −0.010667 | −0.045779 | −0.028338 | −0.040769 | −0.022864 | −0.05399 | −0.005804 | 0.032014 |
| 15 | −0.026529 | −0.047602 | −0.077201 | 0.078794 | −0.057682 | 0.022709 | 0.005877 | 0.01397 | 0.010834 | 0.028992 | 0.013789 | −0.172597 | −0.055405 | 0.021341 |
| 16 | 0.003067 | 0.052187 | −0.008663 | 0.013034 | 0.029618 | −0.092651 | −0.003164 | −0.071394 | 0.00863 | −0.023877 | −0.022095 | 0.051695 | −0.03443 | −0.067865 |
| 17 | 0.060762 | 0.036071 | 0.039219 | 0.011518 | 0.02481 | 0.002609 | 0.014235 | 0.013839 | −0.036479 | −0.014947 | −0.061316 | 0.089056 | 0.028418 | 0.100601 |
| 18 | 0.035565 | −0.027847 | 0.062664 | −0.042406 | 0.04944 | 0.041952 | 0.027851 | −0.034611 | 0.051791 | 0.029519 | 0.070238 | −0.003125 | −0.024642 | −0.032261 |
| 19 | −0.041073 | 0.052761 | −0.03207 | 0.098379 | 0.07677 | −0.087243 | −0.03961 | 0.028914 | 0.012743 | −0.062783 | −0.024849 | 0.094042 | 0.02241 | −0.051663 |
| 20 | 0.000255 | 0.082063 | 0.082537 | 0.136935 | −0.005777 | 0.081628 | 0.003385 | 0.0187 | 0.170513 | −0.017731 | 0.082805 | −0.085996 | 0.051261 | −0.086356 |
| 21 | 0.020636 | −0.029683 | −0.065758 | −0.019574 | 0.025287 | −0.019019 | −0.041085 | −0.00858 | −0.035503 | 0.065663 | 0.040829 | 0.03902 | 0.052749 | 0.013428 |
| 22 | −0.000321 | −0.048114 | 0.085531 | −0.004446 | −0.071869 | 0.04885 | 0.06387 | −0.08153 | −0.146631 | 0.029121 | 0.009759 | −0.00963 | 0.067528 | −0.069793 |
| 23 | −0.046452 | 0.010983 | −0.086925 | 0.004471 | −0.042002 | −0.062056 | −0.083262 | −0.052808 | 0.023879 | −0.006293 | −0.023855 | 0.015578 | −0.055483 | 0.094809 |
| 24 | −0.010097 | 0.107505 | 0.085442 | 0.036915 | −0.066976 | −0.05323 | −0.06336 | −0.01329 | −0.007798 | 0.037815 | 0.058246 | 0.029166 | −0.041358 | 0.080524 |
| 25 | 0.059371 | −0.109403 | −0.034038 | 0.094425 | 0.062604 | −0.015289 | −0.028853 | 0.035392 | −0.040903 | −0.029416 | −0.049764 | −0.089141 | −0.026087 | −0.015062 |
| 26 | −0.0001 | 0.1364871 | 0.003721 | 0.010373 | 0.034501 | 0.073 | −0.021536 | 0.021995 | 0.073893 | −0.042689 | −0.061082 | 0.105097 | 0.062268 | −0.16883 |
| 27 | 0.048757 | −0.124135 | −0.093426 | 0.067316 | −0.068288 | −0.054409 | −0.085073 | −0.095594 | 0.00831 | −0.067406 | 0.057414 | 0.093632 | 0.055481 | 0.082476 |
| 28 | −0.004741 | −0.051106 | −0.043922 | −0.233599 | −0.133969 | −0.031984 | −0.035651 | −0.061222 | 0.055782 | 0.014535 | −0.0195 | −0.123927 | −0.016655 | −0.048033 |
| 29 | −0.038756 | −0.003741 | −0.060691 | −0.013451 | 0.044345 | −0.039897 | 0.007289 | −0.037119 | −0.012596 | 0.029925 | 0.11354 | 0.045122 | −0.054127 | −0.003587 |
| 30 | 0.183237 | −0.026083 | 0.065525 | 0.12325 | 0.040657 | −0.06305 | −0.140745 | 0.03063 | −0.082957 | 0.009023 | 0.009908 | 0.077112 | −0.028499 | 0.000104 |
| 31 | −0.059331 | −0.01748 | −0.052683 | −0.105428 | 0.114957 | −0.007756 | 0.037527 | 0.050842 | 0.054264 | 0.078719 | −0.03853 | −0.175072 | −0.120803 | −0.052604 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 32 | −0.021411 | 0.098909 | −0.041467 | 0.032488 | 0.001735 | −0.02215 | 0.006549 | −0.0555 | −0.034523 | 0.010444 | −0.006431 | 0.025651 | 0.052704 | 0.004085 |
| 33 | 0.048133 | −0.019685 | −0.013401 | −0.016106 | 0.073651 | −0.005729 | −0.039119 | 0.010765 | 0.08301 | 0.047787 | 0.059057 | −0.032975 | −0.039936 | 0.012515 |
| 34 | −0.044012 | −0.026511 | −0.000903 | 0.09771 | 0.111212 | −0.054119 | −0.075657 | −0.017991 | −0.062798 | 0.013461 | 0.000414 | −0.089683 | −0.035761 | 0.070371 |
| 35 | 0.054379 | −0.016888 | −0.057903 | −0.059138 | −0.138033 | 0.010017 | 0.001637 | 0.008031 | 0.044817 | 0.038385 | −0.0243711 | 0.15926 | 0.051478 | 0.107033 |
| 36 | 0.071975 | 0.147821 | 0.003126 | 0.091853 | 0.205315 | 0.049091 | 0.08983 | 0.004842 | −0.06912 | −0.070569 | 0.023017 | −0.018297 | 0.03961 | −0.12021 |
| 37 | −0.004961 | −0.013559 | 0.009165 | −0.160459 | 0.023644 | 0.004734 | 0.069855 | 0.10975 | 0.04153 | 0.017815 | −0.054147 | 0.107757 | 0.038749 | −0.016679 |
| 38 | −0.025651 | −0.058245 | −0.052487 | −0.083993 | −0.070664 | −0.037007 | −0.009903 | −0.018342 | 0.089428 | −0.006782 | 0.003198 | −0.047634 | 0.021525 | −0.063233 |
| 39 | 0.035543 | −0.165296 | 0.0496 | 0.08174 | 0.002235 | 0.086232 | 0.074233 | −0.012476 | −0.040423 | 0.032612 | −0.060728 | 0.021799 | −0.000798 | 0.02755 |
| 40 | −0.001919 | −0.048408 | 0.125941 | 0.069305 | −0.003545 | 0.067173 | −0.042567 | −0.053692 | −0.035256 | −0.016489 | −0.133228 | 0.018216 | 0.109683 | 0.06542 |
| 41 | 0.0363771 | 0.03754 | 0.118397 | −0.099504 | 0.004459 | −0.134446 | 0.003859 | −0.050092 | −0.037319 | −0.007597 | 0.03935 | −0.116651 | −0.090998 | −0.009454 |
| 42 | 0.05784 | 0.008066 | −0.204418 | −0.100698 | 0.059301 | 0.023809 | −0.004775 | 0.047646 | 0.057729 | 0.016188 | −0.013915 | 0.001344 | 0.017709 | 0.042451 |
| 43 | 0.049195 | 0.022171 | 0.039818 | −0.109088 | −0.11057 | −0.040193 | −0.050795 | −0.013758 | 0.059322 | −0.063552 | 0.118688 | −0.004493 | 0.074758 | 0.015389 |
| 44 | −0.004329 | 0.022063 | 0.031554 | 0.037319 | −0.030894 | 0.00742 | −0.030915 | 0.065152 | −0.003892 | −0.04975 | −0.019922 | 0.025127 | −0.067756 | 0.062244 |
| 45 | −0.023125 | 0.022069 | −0.180272 | 0.050043 | −0.002666 | 0.02879 | 0.105472 | 0.078264 | −0.084184 | −0.027083 | −0.030797 | −0.014499 | −0.01787 | −0.099771 |
| 46 | −0.012661 | −0.051066 | −0.024279 | 0.034849 | 0.032543 | −0.030366 | −0.043745 | 0.024165 | 0.092979 | −0.05213 | −0.017367 | −0.022762 | −0.041735 | −0.104033 |
| 47 | −0.012242 | −0.030088 | 0.008082 | −0.049319 | 0.009219 | 0.092946 | 0.045134 | 0.007695 | 0.05447 | 0.051364 | 0.002863 | 0.005251 | 0.066549 | 0.139219 |
| 48 | 0.00294 | 0.035215 | −0.003709 | 0.021087 | −0.02079 | −0.05702 | 0.042053 | −0.059674 | −0.045652 | 0.023757 | −0.041195 | 0.133817 | −0.058036 | −0.032691 |
| 49 | 0.201176 | 0.088744 | −0.010157 | −0.044823 | −0.066494 | −0.033866 | 0.025151 | 0.009681 | 0.054076 | 0.079663 | 0.040516 | 0.044404 | −0.081577 | 0.077878 |
| 50 | −0.042201 | −0.039395 | 0.126743 | −0.038901 | 0.067394 | 0.002635 | −0.004818 | 0.074347 | −0.019354 | 0.00337 | 0.029327 | −0.039259 | 0.059674 | −0.039225 |
| 51 | 0.007483 | −0.058507 | 0.18106 | 0.088792 | 0.056547 | 0.013199 | −0.08779 | −0.03532 | 0.057156 | −0.073841 | −0.031034 | 0.073072 | 0.032807 | 0.013701 |
| 52 | 0.053219 | 0.033951 | −0.08975 | −0.022263 | −0.067152 | −0.025889 | 0.004179 | −0.058667 | 0.123787 | −0.005413 | 0.013334 | −0.08312 | 0.02557 | 0.093067 |
| 53 | −0.055291 | −0.012679 | −0.046796 | −0.00772 | −0.001688 | 0.023968 | −0.002108 | 0.084953 | 0.097918 | 0.043463 | 0.050954 | 0.018399 | −0.022373 | −0.006687 |
| 54 | −0.089125 | 0.123321 | −0.072533 | 0.010197 | −0.029824 | 0.033796 | −0.068467 | −0.00102 | 0.013184 | 0.045467 | −0.052813 | −0.100966 | −0.059598 | 0.020607 |
| 55 | 0.012661 | −0.001864 | 0.054346 | 0.061321 | 0.058595 | −0.080852 | 0.089161 | −0.08749 | −0.016274 | 0.025704 | −0.047279 | 0.068743 | −0.0543 | 0.192944 |
| 56 | 0.205784 | 0.074888 | −0.011925 | −0.022685 | 0.002206 | −0.049652 | −0.01651 | 0.025321 | −0.020765 | 0.044343 | 0.102587 | 0.048528 | 0.044325 | −0.094423 |
| 57 | 0.020913 | 0.036459 | −0.041675 | 0.13094 | −0.009463 | −0.036942 | −0.025533 | 0.090399 | −0.009651 | −0.093366 | −0.008301 | −0.105561 | −0.01727 | −0.049384 |
| 58 | 0.071028 | 0.016993 | −0.022324 | −0.093057 | 0.03344 | −0.032481 | −0.20843 | −0.127103 | 0.021311 | −0.053673 | 0.02019 | −0.033925 | −0.186435 | 0.048264 |
| 59 | 0.022939 | −0.057056 | 0.071154 | −0.002807 | 0.00725 | 0.075966 | −0.014818 | −0.017929 | 0.080202 | −0.00214 | 0.079337 | 0.041114 | 0.021881 | 0.015088 |
| 60 | −0.080678 | −0.015361 | −0.007106 | 0.099916 | 0.091236 | 0.05992 | −0.094859 | −0.087975 | −0.012281 | 0.033841 | 0.088602 | 0.088968 | −0.004035 | −0.004841 |
| 61 | 0.013971 | −0.003568 | 0.026749 | 0.06588 | −0.009353 | −0.021618 | 0.024467 | 0.04205 | −0.119968 | −0.035186 | 0.044646 | −0.044834 | −0.056113 | 0.067839 |
| 62 | 0.032406 | −0.077347 | −0.026416 | 0.178272 | 0.036094 | 0.058732 | −0.046531 | 0.001291 | 0.106897 | −0.016439 | 0.089216 | −0.02245 | −0.11057 | −0.020954 |
| 63 | 0.045117 | 0.024511 | 0.163096 | 0.154983 | 0.092455 | 0.118491 | −0.029483 | −0.078222 | −0.081835 | 0.049478 | 0.046498 | 0.011126 | 0.077255 | 0.024337 |
| 64 | −0.800151 | −0.038338 | 0.011508 | 0.010414 | 0.005574 | 0.003017 | −0.010351 | 0.006237 | 0.03165 | −0.024063 | 0.049772 | 0.053735 | 0.001562 | 0.030224 |
| 65 | 0.025638 | −0.007075 | 0.102379 | −0.011687 | 0.076519 | −0.027612 | −0.053854 | 0.054208 | 0.039371 | −0.006609 | 0.075314 | −0.014932 | −0.076308 | 0.002163 |
| 66 | 0.022632 | 0.015279 | −0.10668 | −0.036129 | 0.042414 | −0.039877 | 0.076209 | −0.061916 | −0.00236 | −0.021727 | −0.046898 | −0.055988 | 0.040886 | −0.048489 |
| 67 | −0.026436 | 0.038123 | −0.15181 | −0.03533 | 0.038948 | 0.066415 | 0.04231 | 0.016621 | 0.071995 | 0.009104 | −0.043114 | −0.041271 | 0.131245 | 0.045318 |
| 68 | 0.005133 | −0.104845 | −0.006438 | −0.074733 | −0.008116 | −0.010639 | −0.003632 | −0.039695 | 0.076056 | 0.011894 | 0.042241 | 0.190909 | −0.025977 | −0.036789 |
| 69 | 0.015753 | −0.027226 | −0.079076 | −0.060883 | 0.013885 | 0.032832 | −0.009078 | 0.089533 | −0.06412 | −0.090005 | −0.053901 | −0.029899 | 0.021622 | −0.004011 |
| 70 | 0.019129 | −0.024655 | 0.084792 | 0.086589 | −0.103764 | 0.085062 | −0.120928 | −0.138292 | 0.017393 | 0.039897 | 0.056337 | 0.026505 | 0.004485 | −0.046999 |
| 71 | 0.021885 | −0.012336 | −0.021968 | 0.030929 | 0.003331 | 0.028067 | −0.063131 | −0.011783 | 0.051633 | −0.000304 | 0.071111 | −0.031089 | 0.060435 | −0.030002 |
| 72 | 0.031427 | −0.007427 | 0.029387 | −0.009687 | −0.084095 | −0.010896 | 0.068013 | −0.026122 | 0.004064 | −0.007228 | 0.039767 | 0.0066 | −0.02893 | −0.074901 |
| 73 | −0.019246 | −0.009413 | 0.027781 | −0.081647 | 0.113281 | −0.030683 | 0.015928 | 0.080107 | −0.052043 | −0.027853 | 0.070613 | −0.035055 | 0.01471 | 0.036265 |
| 74 | −0.015648 | −0.026384 | −0.036881 | −0.005152 | −0.016802 | −0.004418 | 0.025973 | −0.004724 | −0.062746 | −0.027072 | −0.023907 | 0.014936 | 0.030369 | −0.043775 |
| 75 | 0.002091 | 0.001922 | 0.151686 | −0.113782 | 0.050155 | −0.019224 | 0.039786 | −0.037485 | −0.062893 | −0.040726 | 0.041243 | 0.160206 | 0.117762 | −0.003602 |
| 76 | 0.012051 | −0.014466 | −0.110787 | 0.041918 | 0.176621 | −0.097926 | −0.086431 | 0.022387 | 0.095783 | −0.060328 | 0.044383 | −0.105606 | 0.102558 | 0.165568 |
| 77 | −0.020618 | 0.012811 | −0.038926 | 0.043099 | −0.020026 | 0.035832 | 0.06597 | −0.023739 | −0.02543 | 0.065903 | 0.018872 | −0.158758 | −0.068105 | −0.092594 |
| 78 | −0.010807 | 0.006667 | 0.106662 | −0.070644 | 0.106722 | −0.021066 | 0.05251 | −0.048469 | 0.070196 | 0.124855 | −0.095849 | −0.062026 | 0.056771 | 0.30092 |
| 79 | 0.011491 | 0.006795 | −0.161209 | 0.009201 | −0.06219 | 0.05894 | 0.050222 | 0.065138 | −0.013643 | −0.042425 | −0.044938 | 0.116147 | −0.164258 | −0.178777 |
| 80 | 0.00482 | −0.027504 | −0.017755 | −0.041448 | −0.0966 | 0.080034 | 0.03578 | 0.076371 | −0.023464 | 0.007268 | 0.026472 | 0.060193 | −0.013471 | −0.034295 |
| 81 | −0.013743 | −0.034031 | 0.012861 | 0.103511 | −0.099211 | −0.016721 | −0.023161 | 0.051258 | −0.030495 | −0.010319 | 0.031356 | −0.057246 | −0.121231 | 0.009074 |
| 82 | 0.003475 | −0.014045 | 0.061453 | −0.120558 | −0.034263 | −0.067704 | 0.001485 | 0.075626 | −0.002807 | −0.044039 | −0.110847 | −0.035296 | 0.027978 | 0.020258 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 83 | 0.004671 | −0.008135 | 0.06956 | −0.026235 | −0.061017 | 0.060135 | −0.128536 | 0.037052 | −0.010423 | −0.021379 | 0.027126 | 0.03941 | −0.128422 | −0.048996 |
| 84 | 0.002674 | −0.00816 | 0.048624 | 0.005327 | 0.140153 | −0.096633 | −0.013626 | −0.072704 | −0.029654 | −0.022029 | −0.101885 | 0.014944 | 0.083467 | −0.079512 |
| 85 | 0.000466 | −0.024517 | −0.044148 | −0.018099 | 0.031493 | 0.057733 | 0.024779 | −0.039571 | 0.002964 | −0.036696 | 0.031551 | −0.015952 | 0.047425 | 0.045312 |
| 86 | 0.002683 | −0.015002 | 0.006528 | −0.036907 | 0.086292 | 0.04672 | −0.129354 | 0.003911 | 0.012081 | −0.051835 | 0.02447 | 0.099971 | −0.087746 | 0.085377 |
| 87 | −0.012704 | −0.030189 | −0.063857 | 0.217733 | −0.076256 | −0.021736 | 0.045057 | 0.064326 | −0.045333 | 0.02204 | −0.003656 | 0.096063 | −0.020488 | 0.037971 |
| 88 | −0.003422 | −0.023645 | 0.060644 | −0.081463 | −0.061567 | 0.088066 | 0.030091 | −0.074607 | −0.066927 | −0.11542 | 0.155524 | −0.048062 | 0.031036 | 0.108338 |
| 89 | 0.000998 | 0.0015 | 0.240404 | 0.058978 | −0.016843 | −0.099094 | 0.168225 | −0.009636 | −0.015505 | −0.078451 | −0.012762 | 0.042735 | −0.08522 | 0.108082 |
| 90 | 0.014924 | −0.018957 | −0.024975 | −0.007825 | −0.127564 | −0.107798 | −0.025103 | 0.036078 | −0.044268 | −0.13032 | −0.040867 | −0.026936 | 0.110078 | −0.039289 |
| 91 | 0.015403 | 0.007473 | −0.040857 | 0.043923 | 0.050387 | 0.051642 | −0.047544 | −0.053438 | 0.017216 | 0.013141 | 0.033024 | −0.005515 | 0.04533 | 0.050284 |
| 92 | −0.012532 | 0.031947 | 0.069819 | −0.024643 | −0.088318 | −0.020233 | −0.072443 | 0.049411 | 0.013482 | −0.020597 | −0.0968 | 0.079146 | 0.073343 | −0.103826 |
| 93 | −0.014301 | −0.013177 | −0.028553 | −0.102631 | 0.215058 | 0.064584 | 0.028767 | 0.061454 | −0.033018 | 0.047585 | −0.024882 | 0.025311 | −0.041515 | 0.078489 |
| 94 | −0.044122 | −0.013393 | 0.008373 | 0.120405 | −0.098956 | 0.139037 | 0.038601 | 0.030457 | 0.032997 | 0.055692 | 0.0710411 | 0.007798 | 0.004111 | −0.032115 |
| 95 | −0.038974 | 0.067963 | 0.025154 | 0.060325 | −0.045092 | −0.004832 | 0.035382 | −0.017886 | −0.025293 | 0.032342 | 0.022258 | −0.158155 | −0.064467 | 0.107147 |
| 96 | −0.015043 | 0.005682 | −0.02068 | −0.014607 | −0.02824 | −0.03612 | −0.022217 | 0.070583 | 0.04851 | −0.020293 | 0.041344 | 0.041265 | −0.057246 | 0.052104 |
| 97 | 0.031925 | 0.030947 | 0.018737 | −0.091726 | 0.007024 | 0.008584 | 0.011883 | 0.088429 | −0.075951 | 0.03221 | 0.0684411 | 0.080141 | 0.061583 | −0.094932 |
| 98 | 0.023158 | −0.001188 | 0.080338 | −0.007652 | 0.032437 | −0.099394 | −0.134827 | −0.022029 | 0.021627 | −0.030098 | −0.187798 | −0.050819 | 0.016135 | −0.054142 |
| 99 | −0.017409 | −0.033826 | 0.082457 | 0.089205 | 0.076263 | 0.039613 | 0.055087 | 0.024152 | 0.113095 | 0.025458 | −0.043571 | 0.04958 | −0.074626 | 0.000618 |
| 100 | −0.012658 | −0.009064 | 0.139705 | 0.054527 | −0.032594 | 0.107043 | 0.170707 | 0.148589 | 0.192761 | −0.076364 | 0.082037 | −0.099393 | 0.004241 | −0.007757 |
| 101 | 0.052594 | −0.167701 | −0.035879 | 0.08709 | 0.172405 | −0.046341 | 0.001681 | 0.069943 | 0.004416 | 0.04381 | 0.022872 | −0.06464 | −0.018573 | 0.037738 |
| 102 | −0.009445 | −0.014683 | −0.051863 | −0.091698 | −0.003538 | −0.083936 | −0.111693 | −0.042076 | −0.01105 | 0.09256 | 0.061589 | −0.041091 | −0.018839 | −0.02791 |
| 103 | −0.020699 | 0.026481 | −0.045951 | 0.053002 | 0.008841 | 0.000319 | 0.010457 | −0.041464 | −0.016913 | −0.010063 | −0.056672 | −0.008126 | 0.027405 | 0.038593 |
| 104 | 0.076392 | 0.045123 | 0.072521 | −0.001485 | −0.033543 | 0.069916 | 0.010191 | 0.168685 | 0.051226 | 0.003198 | −0.007559 | −0.020269 | 0.005932 | −0.110824 |
| 105 | 0.021379 | −0.013238 | −0.01969 | −0.016769 | −0.101458 | −0.02489 | 0.023381 | 0.028254 | −0.036701 | 0.003995 | 0.047309 | −0.049223 | −0.00495 | 0.039779 |
| 106 | 0.01549 | 0.000756 | 0.070776 | 0.008624 | −0.091134 | 0.02901 | 0.013039 | 0.005568 | −0.011374 | −0.014079 | −0.036422 | 0.007613 | −0.063244 | 0.087554 |
| 107 | −0.020934 | 0.04753 | 0.036614 | 0.014248 | −0.000186 | −0.010271 | −0.044827 | 0.027109 | 0.07713 | −0.024695 | 0.00334 | −0.1137451 | 0.043443 | −0.016021 |
| 108 | −0.034729 | 0.026024 | −0.076777 | 0.061227 | −0.012222 | −0.02384 | −0.081688 | −0.032171 | −0.115264 | −0.006421 | 0.043582 | −0.090776 | 0.053332 | 0.004948 |
| 109 | −0.034599 | 0.04494 | −0.008058 | 0.010223 | 0.052304 | −0.078429 | −0.05649 | 0.030827 | −0.017862 | 0.021013 | −0.024375 | 0.003632 | 0.044469 | 0.02919 |
| 110 | 0.010279 | −0.070296 | −0.03932 | −0.0323 | 0.013709 | 0.009428 | 0.000117 | 0.014098 | 0.046757 | −0.021228 | 0.060841 | −0.022561 | −0.04928 | 0.000874 |
| 111 | 0.028223 | −0.005728 | −0.040805 | 0.010411 | 0.014342 | −0.039608 | 0.063517 | −0.066792 | 0.049058 | 0.000496 | 0.052466 | 0.004752 | 0.03663 | −0.037001 |
| 112 | 0.000706 | 0.032236 | 0.020845 | −0.048322 | 0.002954 | −0.046299 | −0.067327 | −0.037168 | 0.048101 | 0.007986 | 0.057499 | −0.008694 | −0.015176 | −0.056261 |
| 113 | −0.00176 | −0.025073 | −0.041348 | −0.054721 | 0.052915 | 0.030692 | 0.001949 | 0.005613 | 0.005973 | −0.026345 | −0.110119 | −0.053618 | 0.006657 | 0.020583 |
| 114 | −0.045731 | 0.022255 | 0.006379 | −0.010469 | −0.011404 | −0.023373 | 0.003529 | 0.006561 | 0.035227 | 0.071156 | −0.062198 | −0.033077 | −0.037243 | −0.005971 |
| 115 | −0.010061 | −0.004326 | −0.007726 | −0.055675 | −0.037205 | −0.006446 | −0.014247 | 0.043224 | 0.048835 | 0.003094 | −0.046914 | −0.020954 | −0.086638 | 0.007202 |
| 116 | 0.029128 | 0.023517 | 0.053616 | 0.002049 | 0.038824 | −0.003598 | 0.089333 | −0.081291 | 0.060869 | −0.019457 | 0.020075 | −0.030535 | −0.026774 | −0.086615 |
| 117 | 0.003435 | −0.010142 | −0.066165 | 0.009342 | 0.029818 | 0.025431 | 0.019612 | −0.015329 | 0.080115 | −0.033995 | −0.052897 | 0.003366 | 0.005289 | 0.038353 |
| 118 | 0.029246 | −0.02283 | 0.053496 | −0.093623 | −0.040332 | −0.125678 | −0.034748 | −0.057116 | −0.067674 | −0.054983 | 0.001546 | −0.031458 | −0.097781 | −0.050654 |
| 119 | 0.011155 | −0.032124 | −0.081531 | 0.011504 | −0.007632 | −0.106578 | 0.109123 | −0.085787 | 0.001068 | 0.049738 | 0.034546 | −0.062455 | 0.071174 | 0.066187 |
| 120 | −0.037322 | 0.057946 | −0.011944 | −0.015269 | −0.053074 | −0.020768 | −0.051191 | 0.092669 | −0.047707 | 0.049608 | −0.012041 | 0.119154 | 0.003301 | −0.023696 |
| 121 | −0.004211 | −0.084264 | −0.011563 | −0.040388 | 0.108475 | 0.004747 | 0.019976 | −0.043827 | −0.082509 | −0.037337 | 0.014426 | −0.05989 | −0.015422 | −0.013613 |
| 122 | −0.038152 | −0.015076 | 0.029369 | 0.01088 | −0.048566 | 0.010558 | −0.104656 | −0.017815 | −0.112342 | −0.020414 | −0.018209 | −0.084339 | 0.025959 | −0.053364 |
| 123 | 0.017763 | −0.045687 | 0.01719 | 0.028154 | −0.037681 | 0.067472 | 0.071595 | −0.086849 | −0.068183 | 0.011636 | −0.048693 | 0.022744 | 0.054375 | −0.107594 |
| 124 | −0.017853 | −0.044143 | 0.088993 | −0.067601 | 0.022302 | 0.095664 | 0.002108 | −0.101194 | −0.061723 | 0.050833 | −0.043075 | −0.00334 | 0.045528 | 0.007571 |
| 125 | −0.014945 | 0.073716 | 0.034411 | −0.066598 | −0.021406 | 0.054717 | 0.058387 | 0.00898 | 0.027992 | −0.133863 | −0.118779 | −0.045294 | 0.027138 | −0.031613 |
| 126 | 0.010192 | 0.007026 | −0.114961 | 0.155829 | −0.041274 | −0.061849 | 0.00552 | −0.074708 | −0.065198 | −0.052845 | 0.022727 | 0.039019 | −0.116075 | −0.009506 |
| 127 | 0.017812 | −0.016576 | 0.094488 | 0.132428 | 0.059201 | −0.16011 | 0.015182 | 0.09824 | 0.056039 | 0.035568 | 0.076666 | −0.010849 | 0.114887 | 0.008811 |
| 128 | −0.055917 | −0.066283 | −0.03964 | −0.025106 | 0.031737 | −0.010428 | −0.004175 | −0.069613 | −0.04074 | −0.064743 | 0.012053 | −0.06403 | −0.06672 | −0.083901 |
| 129 | 0.008709 | 0.009893 | 0.003478 | 0.059631 | 0.155221 | −0.057453 | −0.068203 | −0.048736 | 0.05294 | −0.012955 | −0.063433 | −0.004204 | 0.036317 | −0.080617 |
| 130 | 0.008205 | −0.084242 | 0.023315 | 0.080033 | −0.066322 | −0.069878 | 0.033915 | −0.037667 | −0.008744 | −0.022242 | −0.036128 | −0.006758 | 0.015738 | −0.048457 |
| 131 | −0.004834 | 0.011172 | 0.061282 | 0.009693 | 0.01599 | −0.022091 | −0.020868 | 0.026308 | 0.038034 | −0.01189 | −0.019694 | −0.116935 | −0.024205 | −0.053883 |
| 132 | −0.008 | −0.042097 | 0.094786 | −0.076369 | −0.011734 | −0.008081 | 0.059399 | 0.03353 | −0.055093 | −0.02574 | −0.016681 | −0.053534 | −0.034119 | −0.039287 |
| 133 | 0.044701 | −0.07737 | −0.005644 | −0.087772 | 0.007589 | 0.081356 | −0.014764 | −0.013238 | −0.105473 | −0..030482 | 0.078352 | −0.047284 | 0.05753 | 0.124058 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 134 | −0.021253 | −0.006046 | 0.038475 | −0.032314 | −0.003813 | 0.049995 | 0.039423 | 0.072592 | −0.048823 | −0.003068 | −0.03451 | 0.042462 | 0.011266 | 0.047179 |
| 135 | −0.038376 | 0.032111 | 0.099181 | −0.056008 | 0.102206 | 0.099729 | −0.173025 | −0.081076 | −0.015885 | 0.097514 | 0.005113 | −0.069025 | −0.112647 | −0.161388 |
| 136 | 0.043075 | 0.020202 | −0.055597 | 0.044339 | −0.041476 | 0.038399 | −0.114682 | −0.012389 | −0.10796 | −0.009346 | −0.075574 | −0.065348 | 0.042538 | −0.015652 |
| 137 | 0.005507 | 0.095817 | 0.003032 | −0.077182 | −0.040083 | 0.108568 | 0.049103 | −0.041192 | −0.156575 | −0.07921 | 0.067078 | −0.062981 | 0.003685 | 0.093399 |
| 138 | 0.017145 | 0.054176 | −0.006328 | −0.05129 | 0.037837 | 0.030001 | 0.002698 | 0.035788 | 0.001605 | 0.014875 | 0.011821 | −0.041053 | −0.024576 | 0.050505 |
| 139 | −0.033482 | 0.075223 | 0.299753 | 0.014384 | −0.048264 | −0.005283 | 0.034068 | 0.04217 | −0.002992 | −0.028464 | −0.040533 | −0.031925 | −0.018271 | 0.008087 |
| 140 | 0.019634 | 0.156718 | 0.021175 | 0.224831 | −0.054593 | −0.006805 | −0.016883 | 0.009211 | 0.025971 | 0.043971 | −0.004084 | −0.02487 | 0.022696 | 0.053715 |
| 141 | −0.044935 | 0.029361 | −0.02229 | −0.043946 | 0.383767 | 0.019039 | −0.014362 | −0.008078 | −0.015905 | −0.039208 | 0.00171 | 0.034839 | −0.032219 | −0.022473 |
| 142 | 0.033064 | 0.062119 | −0.03748 | −0.008437 | 0.047184 | 0.551264 | −0.073742 | −0.057357 | −0.000871 | −0.036596 | −0.048415 | −0.00255 | −0.019203 | 0.01578 |
| 143 | −0.009568 | 0.017536 | −0.021824 | 0.014461 | 0.052053 | −0.080142 | 0.520938 | −0.095904 | −0.000776 | −0.011268 | 0.021045 | 0.028109 | −0.038649 | −0.075399 |
| 144 | −0.017661 | −0.045919 | 0.020108 | −0.015666 | −0.021905 | −0.052534 | −0.065489 | 0.61854 | −0.095745 | −0.013285 | 0.041367 | −0.033992 | −0.044369 | 0.078758 |
| 145 | 0.025088 | −0.018839 | 0.021032 | −0.0331 | −0.024235 | −0.021958 | 0.009472 | −0.065743 | 0.532986 | −0.060774 | −0.018885 | 0.079703 | −0.009106 | 0.013751 |
| 146 | 0.010578 | 0.00613 | −0.032755 | 0.09781 | −0.025881 | −0.027551 | 0.038215 | 0.022733 | −0.02751 | 0.757451 | −0.037413 | 0.026885 | 0.015362 | −0.050127 |
| 147 | −0.024903 | 0.013295 | −0.03643 | −0.028651 | 0.013064 | −0.036474 | 0.023924 | 0.003505 | 0.012723 | −0.01297 | 0.563481 | −0.031192 | 0.042083 | −0.013071 |
| 148 | −0.011351 | −0.106011 | −0.061183 | −0.012298 | 0.008789 | −0.010686 | −0.001956 | −0.001761 | 0.057405 | −0.032672 | −0.043733 | 0.253327 | −0.083899 | −0.007394 |
| 149 | −0.026175 | 0.019548 | −0.01863 | −0.01172 | −0.029608 | −0.048774 | −0.070915 | 0.007096 | 0.005018 | 0.025772 | 0.054083 | −0.042758 | 0.543789 | −0.023439 |
| 150 | 0.03503 | −0.075328 | −0.029653 | 0.054877 | −0.043977 | 0.03902 | −0.026675 | 0.026828 | −0.004392 | −0.029011 | −0.028086 | 0.069645 | −0.038831 | 0.331068 |
| 151 | −0.030205 | −0.02646 | −0.058977 | −0.067936 | −0.004645 | −0.022001 | −0.036606 | −0.059899 | −0.052097 | 0.03323 | −0.066284 | −0.012665 | −0.03788 | −0.015454 |
| 152 | 0.020424 | −0.074118 | −0.012462 | −0.064892 | 0.060541 | −0.04418 | −0.006723 | 0.021788 | 0.016194 | 0.046487 | 0.035185 | 0.038883 | −0.013357 | 0.023915 |
| 153 | 0.004936 | 0.009602 | −0.059238 | 0.052274 | 0.028535 | −0.059003 | 0.008285 | −0.046263 | −0.024331 | −0.019955 | −0.034497 | 0.010241 | 0.02776 | 0.061746 |
| 154 | −0.03088 | −0.006404 | 0.037777 | −0.065963 | 0.032005 | −0.107214 | −0.00448 | −0.031113 | −0.017165 | 0.03489 | −0.046287 | 0.007257 | −0.008031 | −0.017594 |
| 155 | 0.015389 | 0.090939 | −0.007661 | 0.009241 | 0.026444 | −0.095718 | −0.017848 | −0.025158 | 0.045244 | −0.023277 | 0.06308 | 0.025266 | −0.018342 | −0.015443 |
| 156 | −0.036784 | 0.014354 | 0.034209 | 0.027454 | −0.012145 | −0.034079 | 0.037594 | −0.002785 | 0.0621 | −0.024047 | 0.004675 | 0.030797 | 0.003161 | 0.01214 |
| 157 | −0.001613 | −0.02392 | −0.059065 | −0.040484 | 0.021378 | −0.035842 | 0.02766 | −0.019127 | −0.028912 | −0.043657 | 0.062512 | 0.049275 | 0.024653 | 0.066213 |
| 158 | 0.010507 | −0.036997 | 0.013631 | −0.011632 | −0.035381 | 0.004026 | −0.027431 | −0.041082 | 0.015074 | 0.031199 | −0.068665 | 0.021026 | −0.004949 | 0.013604 |
| 159 | −0.005423 | 0.049326 | 0.001535 | 0.000488 | 0.023963 | −0.05646 | 0.001144 | 0.014096 | −0.0475 | 0.043678 | 0.05679 | −0.053943 | −0.029785 | −0.038935 |
| 160 | −0.011843 | 0.045978 | −0.037961 | 0.014519 | 0.013558 | −0.027855 | −0.022973 | −0.016192 | 0.032484 | 0.004216 | −0.023255 | 0.018816 | −0.040371 | −0.023028 |
| 161 | 0.023734 | 0.055079 | −0.039283 | 0.050486 | −0.03506 | 0.00841 | −0.049388 | 0.04071 | −0.037159 | −0.033154 | −0.014297 | 0.037153 | 0.027872 | 0.034833 |
| 162 | 0.005578 | −0.061342 | 0.0094341 | 0.014349 | −0.069516 | 0.012742 | −0.042249 | −0.044303 | 0.021981 | −0.040321 | −0.007778 | 0.050428 | −0.007629 | −0.00509 |
| 163 | −0.029505 | 0.012986 | −0.002176 | 0.006421 | −0.059281 | −0.10777 | 0.002265 | 0.011116 | 0.015944 | 0.043999 | 0.055043 | −0.00521 | −0.076473 | 0.054618 |
| 164 | −0.046012 | 0.051545 | 0.015295 | 0.063827 | −0.025069 | −0.054051 | −0.036125 | 0.031076 | 0.016193 | −0.059446 | 0.024681 | 0.052128 | −0.009482 | −0.024553 |
| 165 | −0.027933 | 0.038335 | −0.004657 | 0.035875 | −0.012451 | 0.024006 | 0.035 | −0.040147 | −0.049939 | −0.012402 | 0.023537 | −0.002687 | −0.020232 | 0.036905 |
| 166 | 0.038306 | −0.00141 | 0.048652 | −0.020535 | −0.041811 | −0.009281 | 0.064847 | 0.01154 | 0.010873 | −0.010841 | 0.020477 | 0.022133 | 0.055626 | 0.0167 |
| 167 | 0.028641 | 0.00009 | 0.041892 | −0.008513 | 0.027281 | 0.016461 | 0.002674 | −0.02733 | −0.050272 | −0.026902 | 0.006247 | 0.011104 | −0.054595 | −0.019959 |
| 168 | 0.008609 | −0.070482 | 0.044073 | 0.02382 | −0.013417 | −0.009484 | −0.03412 | 0.015452 | −0.028856 | −0.007983 | 0.021292 | −0.094389 | 0.005775 | −0.017127 |
| 169 | 0.00287 | −0.00062 | −0.022369 | 0.009629 | −0.002221 | −0.013919 | −0.011235 | −0.033727 | 0.027957 | −0.026617 | 0.015965 | 0.003667 | −0.02716 | 0.006639 |
| 170 | 0.010772 | −0.012286 | 0.023233 | 0.006421 | −0.013055 | −0.005732 | −0.013634 | −0.031025 | 0.03845 | 0.014436 | 0.016253 | 0.022247 | −0.060456 | 0.001803 |
| 171 | −0.010947 | 0.013356 | 0.01563 | −0.0086 | −0.029027 | −0.003234 | −0.006127 | −0.018777 | 0.046516 | −0.006428 | 0.026154 | 0.041426 | −0.017957 | 0.062692 |
| 172 | 0.033781 | 0.017538 | −0.027613 | 0.029941 | 0.034737 | −0.015068 | −0.014646 | 0.001204 | 0.025859 | −0.042023 | −0.000391 | 0.01643 | 0.011313 | −0.065706 |
| 173 | −0.007741 | 0.015839 | 0.059561 | −0.0003 | −0.001906 | 0.012805 | 0.009251 | 0.030097 | 0.047396 | −0.004872 | −0.011522 | −0.034443 | −0.022083 | 0.015229 |
| 174 | 0.012012 | 0.005196 | 0.081983 | −0.016771 | −0.070831 | −0.040193 | 0.008012 | 0.0069 | 0.071688 | 0.040431 | −0.031838 | −0.059345 | −0.024794 | −0.028271 |
| 175 | −0.040275 | 0.085444 | −0.031085 | 0.042223 | 0.094559 | 0.025682 | −0.013896 | 0.073539 | 0.056719 | 0.003406 | 0.024244 | 0.000601 | −0.046609 | −0.02285 |
| 176 | −0.002837 | −0.045261 | −0.012059 | 0.055372 | 0.053825 | 0.077889 | −0.003727 | 0.069931 | −0.006643 | −0.014299 | 0.012629 | 0.047646 | 0.001117 | −0.023985 |
| 177 | 0.007926 | 0.040566 | −0.02037 | 0.031987 | 0.053421 | 0.063833 | 0.026849 | −0.039611 | 0.008569 | −0.021051 | 0.034776 | −0.028973 | 0.017363 | 0.005837 |
| 178 | −0.042579 | 0.017283 | 0.001843 | 0.008361 | 0.026041 | −0.000768 | −0.06336 | −0.006728 | −0.027485 | 0.024012 | −0.016504 | 0.059627 | 0.009598 | −0.010879 |
| 179 | 0.042821 | 0.014541 | 0.014167 | 0.000448 | 0.020295 | −0.03276 | −0.028747 | 0.009436 | −0.003469 | −0.007693 | −0.010642 | 0.015798 | 0.015598 | 0.017288 |
| 180 | −0.008856 | 0.017614 | 0.042305 | −0.013554 | 0.024354 | −0.038736 | −0.014744 | 0.025448 | −0.002899 | 0.021765 | −0.015622 | 0.027438 | −0.010493 | 0.016596 |
| 181 | 0.003731 | 0.022021 | 0.028809 | 0.003629 | 0.030525 | 0.009882 | −0.013592 | −0.001038 | 0.010457 | 0.021111 | 0.000453 | 0.040444 | −0.017172 | 0.029279 |
| 182 | 0.004731 | 0.033562 | 0.017996 | −0.003334 | 0.058897 | −0.00269 | −0.023874 | −0.031709 | 0.04467 | 0.021781 | −0.007227 | −0.008372 | −0.053522 | −0.063397 |
| 183 | −0.021587 | 0.033484 | 0.003715 | −0.003847 | 0.00412 | 0.0517 | 0.008089 | −0.001892 | −0.004541 | 0.001394 | 0.000221 | 0.033505 | 0.015911 | 0.014625 |
| 184 | 0.019406 | −0.037144 | 0.008444 | 0.001716 | 0.018529 | −0.008098 | −0.02727 | −0.029113 | −0.016705 | 0.018856 | −0.006176 | 0.035192 | 0.039622 | 0.041216 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 185 | 0.011713 | 0.033301 | −0.042541 | 0.08616 | −0.022802 | −0.015722 | 0.002125 | 0.040634 | −0.065891 | −0.006482 | 0.062689 | −0.019154 | 0.004764 | −0.015999 |
| 186 | −0.035314 | 0.01246 | −0.002681 | −0.104136 | 0.017474 | 0.032447 | −0.018769 | 0.004104 | 0.002064 | −0.00492 | 0.06177 | 0.039334 | 0.043091 | 0.003297 |
| 187 | 0.021207 | −0.033164 | −0.015957 | 0.022783 | 0.047427 | 0.026642 | 0.040518 | 0.017131 | 0.021152 | −0.032984 | 0.02578 | 0.009196 | 0.024643 | 0.032603 |
| 188 | 0.008165 | −0.085708 | 0.014421 | −0.018944 | −0.039215 | 0.02914 | 0.060737 | −0.014377 | −0.007204 | −0.02417 | 0.023142 | −0.022311 | 0.019627 | −0.00233 |
| 189 | 0.027447 | −0.004238 | −0.067986 | 0.028448 | 0.024957 | 0.0254 | 0.050489 | 0.018554 | 0.007032 | −0.039047 | −0.02482 | −0.033204 | 0.048379 | 0.045374 |
| 190 | −0.014257 | −0.028883 | −0.007853 | 0.000547 | −0.05191 | 0.044203 | −0.069609 | 0.013119 | 0.001069 | 0.047726 | 0.023506 | 0.014789 | −0.043631 | 0.06681 |
| 191 | 0.021698 | −0.009525 | −0.003016 | −0.0105 | −0.023726 | −0.063723 | −0.022375 | 0.001435 | 0.039424 | −0.017732 | 0.055265 | −0.017163 | −0.021285 | 0.013066 |
| 192 | 0.002204 | 0.024869 | 0.026725 | 0.045833 | 0.033335 | −0.004512 | 0.000099 | −0.053959 | 0.038846 | −0.036179 | 0.047602 | 0.053221 | 0.014131 | −0.019506 |
| 193 | 0.018046 | −0.01263 | −0.020904 | −0.000796 | 0.002236 | −0.037095 | 0.003566 | −0.04643 | −0.008777 | −0.032656 | 0.023615 | 0.003272 | −0.03769 | 0.012694 |
| 194 | −0.007487 | −0.026955 | −0.036781 | 0.051131 | 0.02064 | 0.05149 | −0.008829 | 0.040126 | −0.082139 | −0.012114 | −0.028762 | 0.055387 | 0.00927 | −0.059286 |
| 195 | 0.004043 | 0.052388 | 0.068263 | 0.012134 | −0.009311 | 0.017864 | 0.006261 | 0.071905 | 0.01211 | 0.032731 | 0.020132 | 0.032513 | 0.004881 | 0.07016 |
| 196 | −0.025114 | 0.008485 | −0.006746 | 0.014408 | 0.064342 | −0.021206 | −0.029707 | 0.008165 | 0.021424 | −0.000124 | 0.018073 | −0.016792 | −0.024548 | 0.007696 |
| 197 | 0.00978 | −0.035717 | −0.018509 | 0.022016 | −0.082016 | −0.000472 | −0.031867 | −0.061562 | −0.037361 | −0.026767 | 0.025694 | −0.012809 | −0.122692 | 0.037995 |
| 198 | −0.014592 | 0.112597 | 0.073211 | 0.004881 | 0.043263 | 0.011886 | 0.010023 | −0.026199 | −0.022762 | −0.002431 | −0.050065 | 0.034984 | 0.023799 | 0.014491 |
| 199 | 0.003402 | 0.007216 | 0.007188 | −0.025696 | 0.018801 | −0.020344 | 0.002086 | −0.001015 | −0.004936 | 0.001661 | 0.054321 | 0.00766C | −0.032729 | −0.007433 |
| 200 | 0.02822 | −0.064975 | −0.098565 | −0.017777 | −0.002532 | 0.00208 | 0.07725 | 0.015216 | 0.056197 | −0.006598 | −0.014978 | 0.036101 | −0.011892 | 0.055166 |
| 201 | −0.028776 | −0.042981 | −0.064792 | 0.015497 | −0.033997 | 0.01253 | −0.008882 | −0.010547 | 0.031768 | 0.01746 | 0.016677 | 0.003307 | −0.061036 | −0.012955 |
| 202 | −0.003559 | −0.050058 | 0.065395 | 0.02725 | 0.024386 | −0.021307 | −0.016174 | −0.000323 | −0.011159 | −0.046499 | 0.021911 | 0.011317 | −0.014302 | 0.0067 |
| 203 | −0.007563 | −0.033381 | −0.018956 | −0.040742 | −0.000298 | 0.043441 | 0.02778 | −0.012915 | −0.019459 | 0.022538 | −0.048773 | −0.004609 | 0.051028 | −0.009868 |
| 204 | 0.026242 | 0.018688 | 0.005348 | −0.012994 | −0.0714 | 0.079013 | −0.061496 | −0.05392 | 0.022935 | −0.012436 | 0.06104 | −0.044138 | −0.022191 | 0.009817 |
| 205 | 0.001249 | 0.005055 | 0.036035 | −0.02102 | 0.000372 | −0.03774 | −0.006666 | 0.020159 | 0.012565 | 0.021367 | −0.018076 | 0.015377 | 0.000324 | −0.070393 |
| 206 | −0.051481 | −0.005622 | 0.031794 | 0.039368 | −0.047662 | 0.031758 | −0.022292 | −0.009653 | 0.00585 | 0.003702 | 0.070171 | 0.052821 | 0.012264 | −0.005288 |
| 207 | 0.038375 | −0.093572 | −0.018577 | −0.019299 | 0.042234 | −0.004463 | 0.024567 | 0.089495 | −0.010407 | 0.011947 | −0.063533 | 0.018003 | −0.025587 | −0.010084 |
| 208 | 0.054567 | −0.043999 | −0.017426 | −0.005152 | −0.034544 | 0.073624 | 0.065671 | 0.024399 | −0.048297 | −0.039953 | 0.00774 | −0.03589 | 0.030733 | −0.011043 |
| 209 | 0.032103 | −0.036378 | 0.021503 | 0.040532 | −0.054944 | −0.029668 | −0.031832 | −0.004654 | 0.035875 | −0.014524 | 0.006358 | −0.001696 | 0.003576 | 0.022879 |
| 210 | −0.009011 | 0.033739 | 0.002676 | 0.071538 | 0.007898 | 0.033865 | 0.079264 | 0.027183 | 0.017587 | 0.004147 | −0.017269 | −0.04847 | −0.038411 | −0.008415 |
| 211 | −0.017979 | 0.060097 | 0.019407 | −0.037753 | 0.039549 | −0.001859 | −0.065354 | −0.003717 | −0.058596 | −0.035971 | 0.03692 | 0.041134 | −0.049129 | 0.026182 |
| 212 | −0.013558 | −0.025067 | −0.051012 | 0.008411 | −0.037389 | −0.038274 | −0.001972 | −0.013528 | 0.024506 | 0.025679 | −0.097858 | −0.011217 | 0.072621 | −0.007377 |
| 213 | −0.020083 | −0.016725 | 0.003114 | −0.06932 | −0.024931 | −0.021778 | 0.013073 | 0.004992 | −0.021061 | 0.008579 | −0.047276 | 0.036721 | −0.033318 | −0.032269 |
| 214 | 0.009189 | 0.026985 | 0.007817 | 0.002968 | 0.011235 | −0.035329 | 0.001572 | 0.031904 | 0.017959 | −0.016255 | −0.000591 | 0.015054 | 0.050569 | 0.000189 |
| 215 | −0.030356 | 0.050473 | 0.000472 | −0.01421 | −0.002299 | 0.004392 | −0.024765 | −0.060854 | 0.013622 | 0.069136 | 0.015974 | −0.029921 | 0.030012 | 0.007923 |
| 216 | −0.00383 | 0.077012 | −0.033124 | −0.003569 | −0.024192 | 0.030132 | 0.011523 | −0.016021 | −0.033984 | −0.003841 | −0.005194 | 0.014296 | −0.0157 | 0.026007 |
| 217 | −0.057761 | 0.030051 | −0.050694 | 0.053142 | −0.047322 | 0.018903 | 0.008591 | −0.049851 | −0.030769 | −0.015565 | −0.032399 | 0.036809 | 0.027999 | −0.064527 |
| 218 | 0.000057 | 0.009314 | −0.003843 | 0.004039 | 0.008629 | 0.006846 | −0.014659 | −0.001377 | −0.035845 | −0.039632 | 0.054169 | −0.03713 | 0.031309 | −0.019711 |
| 219 | −0.001066 | 0.003577 | −0.041029 | 0.0414 | −0.011592 | −0.003511 | −0.00225 | 0.002259 | −0.036844 | −0.037693 | 0.051982 | 0.01327 | 0.027262 | 0.038625 |
| 220 | 0.064556 | 0.004475 | 0.01049 | −0.090967 | 0.043206 | −0.002485 | 0.005626 | 0.005547 | 0.028278 | −0.000062 | −0.025886 | 0.008375 | 0.021636 | −0.020454 |
| 221 | −0.021791 | −0.009012 | −0.022099 | −0.032106 | 0.050151 | 0.019536 | −0.00263 | 0.064245 | −0.028834 | 0.006799 | −0.008118 | −0.025441 | −0.027486 | −0.02285 |
| 222 | −0.024408 | −0.018292 | 0.002425 | −0.059389 | −0.047219 | 0.043727 | 0.007642 | 0.02464 | 0.002994 | 0.002018 | 0.001335 | −0.053244 | −0.017429 | −0.023966 |
| 223 | −0.012808 | 0.001416 | 0.047985 | −0.061295 | −0.023451 | 0.046966 | 0.022576 | 0.027075 | 0.027572 | 0.024563 | −0.001604 | −0.014067 | −0.014467 | −0.025284 |
| 224 | −0.003691 | 0.007165 | 0.031521 | 0.005843 | 0.013812 | −0.005703 | 0.005192 | 0.021406 | 0.003894 | 0.005918 | 0.060097 | 0.025076 | −0.001652 | 0.01702 |
| 225 | 0.032214 | −0.004254 | 0.031954 | −0.033494 | 0.03391 | −0.008441 | −0.024768 | 0.013566 | 0.007959 | 0.015685 | 0.03677 | 0.013265 | 0.003908 | −0.008796 |
| 226 | 0.007161 | −0.034444 | −0.001034 | −0.014192 | −0.03298 | 0.01424 | −0.035429 | 0.011166 | −0.008369 | −0.018367 | −0.016437 | −0.023465 | 0.012414 | 0.011849 |
| 227 | −0.014122 | 0.044486 | −0.013385 | −0.016375 | −0.03843 | −0.041908 | −0.00516 | 0.059443 | 0.007072 | −0.012984 | −0.041646 | 0.027432 | 0.07482 | −0.021001 |
| 228 | 0.019818 | 0.048665 | −0.01669 | 0.063385 | −0.025469 | 0.008508 | 0.009922 | 0.041866 | 0.045549 | 0.013841 | −0.000182 | −0.005285 | −0.024639 | −0.008605 |
| 229 | −0.006513 | −0.076781 | −0.045741 | 0.021786 | 0.02356 | −0.015146 | −0.015344 | −0.006646 | 0.053549 | −0.010841 | −0.019223 | 0.009359 | −0.008553 | −0.069581 |
| 230 | 0.027779 | −0.010287 | −0.000105 | 0.023003 | −0.008934 | −0.003828 | 0.011419 | −0.006123 | 0.025246 | −0.02147 | 0.00177 | −0.063498 | −0.008198 | −0.053794 |
| 231 | −0.010869 | 0.207398 | −0.050486 | −0.062649 | −0.013354 | −0.031871 | 0.053205 | −0.000382 | −0.005824 | −0.011586 | −0.039953 | 0.058314 | −0.071624 | 0.041032 |
| 232 | −0.024927 | −0.000571 | 0.045496 | −0.035334 | −0.025025 | 0.004275 | 0.009876 | 0.023871 | 0.027958 | 0.020066 | −0.046394 | −0.017675 | −0.048213 | 0.008072 |
| 233 | −0.024914 | 0.026965 | −0.040171 | 0.043623 | −0.055989 | 0.041793 | 0.019836 | 0.027538 | −0.009454 | −0.044823 | −0.02388 | 0.011728 | 0.016808 | −0.042217 |
| 234 | 0.009843 | −0.065278 | 0.030058 | −0.018181 | −0.008101 | −0.057287 | −0.019352 | −0.000569 | 0.030434 | 0.004924 | 0.040713 | 0.044431 | −0.022507 | −0.048474 |
| 235 | 0.014461 | −0.205638 | −0.004651 | 0.051324 | 0.018027 | −0.065633 | −0.000939 | 0.007814 | −0.026431 | −0.01924 | −0.029264 | −0.015523 | 0.006797 | −0.005914 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 236 | −0.00937 | 0.009955 | 0.022891 | −0.017127 | 0.029183 | −0.017237 | −0.029148 | −0.00042 | 0.035341 | 0.014077 | −0.009766 | −0.073786 | 0.005682 | 0.003783 |
| 237 | 0.029354 | −0.026661 | −0.033587 | 0.015957 | 0.031922 | 0.011627 | 0.050066 | 0.002705 | 0.022704 | −0.015094 | −0.021516 | 0.046869 | −0.010002 | 0.034737 |
| 238 | 0.010197 | 0.089178 | −0.014719 | −0.041471 | 0.019967 | 0.023664 | 0.024615 | 0.015613 | −0.011968 | 0.003748 | 0.036923 | 0.019709 | −0.014872 | 0.004065 |
| 239 | 0.000239 | 0.026101 | −0.000631 | −0.009509 | 0.014818 | −0.006613 | 0.000142 | 0.021537 | −0.041404 | −0.021783 | −0.001038 | −0.016863 | −0.011881 | −0.048389 |
| 240 | −0.018933 | −0.026642 | 0.037908 | −0.000753 | 0.021206 | 0.018071 | 0.0468 | −0.026654 | −0.028986 | −0.020354 | −0.039594 | −0.074097 | 0.002996 | 0.054609 |
| 241 | −0.021716 | 0.059204 | 0.023025 | −0.012976, | 0.023419 | 0.008667 | −0.003586 | 0.006694 | 0.0178561 | 0.018491 | 0.021991 | −0.010699 | 0.024254 | 0.008089 |
| 242 | −0.005586 | −0.098286 | −0.013403 | 0.011772 | 0.037984 | 0.021066 | −0.0225 | 0.014215 | 0.061813 | 0.033796 | −0.017917 | −0.060094 | 0.035017 | −0.023768 |
| 243 | 0.007733 | −0.056818 | −0.022845 | −0.016052 | −0.008642 | 0.012639 | 0.026357 | 0.002734 | −0.022685 | −0.005981 | 0.032779 | 0.015929 | 0.02024 | −0.00708 |
| 244 | −0.001732 | 0.012317 | 0.008882 | 0.02646 | 0.044725 | −0.04988 | −0.068176 | 0.029732 | −0.009509 | −0.002107 | −0.007529 | 0.019581 | 0.009557 | −0.013578 |
| 245 | −0.015601 | 0.04505 | −0.017821 | 0.035131 | −0.065851 | −0.017461 | −0.056407 | −0.059472 | 0.0312941 | −0.012845 | −0.011425 | 0.015536 | 0.011356 | −0.007785 |
| 246 | 0.020944 | 0.024265 | −0.02259 | 0.023118 | −0.003543 | −0.041808 | 0.008227 | 0.006253 | 0.0552381 | 0.010819 | −0.027986 | 0.005513 | −0.004208 | −0.005072 |
| 247 | −0.009775 | 0.029661 | −0.045271 | −0.026618 | 0.011603 | −0.006916 | 0.022821 | 0.01605 | :0.035407 | 0.027557 | 0.012556 | 0.02674 | −0.023784 | −0.016163 |
| 248 | 0.002299 | 0.019474 | −0.051208 | −0.064128 | 0.021619 | 0.010882 | −0.004496 | 0.023113 | −0.023787 | −0.010285 | 0.011737 | 0.002329 | −0.000504 | −0.009561 |
| 249 | 0.025014 | −0.014875 | 0.044972 | −0.039148 | −0.015017 | 0.036585 | −0.023974 | −0.001361 | 0.006521 | −0.017177 | −0.028322 | 0.004213 | 0.007807 | 0.005967 |
| 250 | −0.026612 | 0.045194 | 0.026986 | −0.000808 | 0.069342 | −0.020858 | −0.001219 | −0.004256 | 0.011725 | 0.044858 | 0.025298 | 0.00542 | 0.020808 | 0.026811 |
| 251 | −0.016737 | 0.014786 | 0.018807 | −0.026511 | 0.018478 | −0.038731 | 0.004767 | −0.004789 | 0.010863 | −0.010313 | −0.018612 | −0.022033 | −0.026794 | 0.028186 |
| 252 | −0.00349 | −0.004941 | −0.031192 | −0.000163 | −0.065858 | 0.047301 | −0.016556 | 0.011171 | −0.031516 | −0.011081 | −0.015424 | −0.017913 | 0.030024 | 0.008158 |
| 253 | −0.002112 | 0.054639 | 0.024524 | 0.033806 | 0.017408 | 0.018097 | −0.012442 | −0.010443 | −0.002924 | −0.031929 | 0.008169 | −0.00096 | −0.026934 | 0.035004 |
| 254 | 0.002838 | 0.004995 | 0.027721 | 0.022326 | 0.005103 | 0.002068 | −0.034261 | 0.007688 | 0.002173 | 0.038495 | 0.003321 | 0.018305 | −0.006527 | −0.005522 |
| 255 | 0.018746 | 0.089377 | −0.014509 | 0.017922 | 0.029112 | −0.012443 | 0.006861 | 0.038952 | 0.002924 | 0.015364 | −0.048025 | 0.00633 | −0.003211 | 0.021026 |
| 256 | 0.012006 | −0.053007 | 0.005309 | −0.0105 | −0.05663 | 0.018489 | 0.0047 | −0.018267 | 0.02467e | 0.008213 | −0.02495 | 0.013815 | 0.012244 | 0.019586 |
| 257 | 0.00177 | −0.02166 | −0.070026 | −0.020362 | 0.002827 | 0.033968 | −0.022897 | −0.007476 | −0.013818 | 0.013918 | 0.028351 | 0.030311 | −0.00286 | 0.001842 |
| 258 | 0.018119 | 0.019077 | −0.065489 | −0.014926 | 0.018903 | 0.009959 | 0.033964 | −0.009125 | −0.040882 | −0.000119 | 0.008562 | −0.028292 | −0.043654 | −0.022878 |
| 259 | 0.017037 | −0.019513 | 0.009314 | −0.033466 | 0.001638 | 0.028874 | −0.012894 | −0.013231 | 0.006629 | 0.00442 | 0.024711 | −0.054833 | 0.007241 | 0.011481 |
| 260 | −0.026412 | 0.061268 | −0.013043 | −0.004535 | −0.00592 | 0.012654 | −0.020441 | 0.030212 | −0.009491 | 0.052621 | 0.039803 | 0.001266 | 0.045858 | −0.018845 |
| 261 | −0.012883 | 0.024336 | −0.027976 | 0.025595 | −0.010022 | −0.014679 | 0.013356 | −0.077031 | −0.010318 | 0.001867 | 0.03161 | −0.025638 | −0.069149 | 0.010861 |
| 262 | 0.019787 | −0.002389 | −0.034279 | 0.000714 | 0.007088 | −0.009373 | −0.01984 | −0.024492 | 0.020224 | 0.015792 | −0.006636 | −0.008322 | −0.007833 | 0.00505 |
| 263 | 0.072545 | 0.063451 | −0.030383 | 0.009752 | 0.016307 | 0.038591 | −0.038505 | −0.009625 | 0.007813 | −0.052021 | −0.02855 | 0.022201 | 0.016033 | −0.000948 |
| 264 | −0.035359 | 0.097842 | 0.020652 | −0.024689 | −0.030753 | 0.006519 | −0.017667 | −0.023685 | −0.083861 | −0.017988 | 0.000932 | −0.008213 | −0.025649 | 0.024773 |
| 265 | −0.0115 | −0.019885 | 0.013026 | −0.012761 | −0.041288 | −0.023101 | 0.01577 | −0.036342 | −0.050987 | 0.021627 | 0.004908 | −0.089621 | −0.006191 | 0.006606 |
| 266 | −0.025562 | −0.066734 | 0.000324 | 0.000104 | 0.010696 | −0.047369 | 0.024419 | −0.062525 | 0.0128 | −0.013180 | −0.010532 | −0.027832 | 0.035247 | −0.004212 |
| 267 | −0.00928 | −0.0089 | −0.0253 | −0.011779 | −0.000502 | 0.035254 | 0.009371 | 0.019245 | −0.043793 | 0.031799 | 0.024276 | 0.023072 | −0.023585 | 0.062554 |
| 268 | 0.003868 | −0.026156 | 0.057534 | −0.019217 | −0.000816 | 0.017229 | −0.024871 | 0.032506 | −0.004629 | 0.007631 | −0.018928 | 0.00672 | 0.019356 | 0.037238 |
| 269 | −0.016401 | 0.007405 | 0.037352 | −0.04514 | −0.017193 | −0.009762 | −0.011137 | 0.025495 | 0.011317 | 0.021122 | −0.008622 | 0.023021 | 0.007191 | 0.040813 |
| 270 | −0.041664 | −0.026386 | 0.034649 | 0.006905 | −0.032153 | −0.029772 | −0.00343 | 0.003102 | −0.006162 | −0.013358 | −0.004214 | −0.01197 | 0.018799 | −0.000694 |
| 271 | −0.042648 | −0.052496 | −0.019379 | −0.012926 | −0.077995 | −0.014475 | −0.033385 | 0.005492 | −0.014636 | −0.000597 | −0.006275 | 0.078325 | −0.027971 | −0.065722 |
| 272 | −0.009487 | 0.28753 | −0.028037 | 0.026509 | 0.0001 | −0.025793 | 0.025618 | −0.008533 | −0.032051 | −0.019089 | 0.000315 | 0.017218 | −0.021949 | 0.070822 |
| 273 | 0.00272 | −0.001287 | 0.021269 | 0.02144 | 0.002354 | −0.000757 | 0.000288 | −0.025006 | 0.033893 | −0.00986 | 0.007039 | −0.047062 | −0.003825 | −0.011338 |
| 274 | 0.017165 | −0.035455 | 0.018557 | 0.049202 | 0.014341 | −0.015097 | 0.003829 | −0.015909 | 0.04304 | −0.018119 | 0.013161 | −0.044246 | 0.000343 | −0.041307 |
| 275 | 0.02261 | 0.055495 | −0.010075 | 0.021931 | −0.019737 | −0.09934 | 0.004476 | −0.034372 | 0.013141 | −0.022244 | 0.032231 | −0.077265 | −0.014694 | −0.025731 |
| 276 | −0.004664 | 0.070774 | 0.018573 | −0.031163 | 0.049874 | −0.002136 | 0.002084 | −0.017899 | −0.002754 | 0.01084 | −0.003395 | −0.048399 | −0.022711 | 0.032825 |
| 277 | −0.003715 | 0.042222 | −0.001925 | −0.007108 | −0.007786 | 0.023916 | −0.004752 | −0.0265 | 0.018529 | 0.044688 | 0.0196 | −0.004748 | −0.025682 | −0.025323 |
| 278 | −0.029542 | 0.029713 | −0.019753 | 0.04173 | −0.018221 | 0.0165 | 0.06303 | −0.033267 | 0.051131 | −0.007149 | 0.005577 | −0.028594 | −0.046332 | 0.007287 |
| 279 | −0.029125 | −0.019468 | 0.002559 | −0.049562 | −0.009171 | −0.00816 | 0.034085 | 0.013594 | −0.0576 | −0.028394 | 0.030289 | −0.025556 | −0.013611 | −0.025067 |
| 280 | 0.028225 | 0.063728 | 0.016109 | −0.027081 | −0.001159 | 0.033666 | 0.070644 | −0.024517 | −0.009848 | −0.045892 | −0.033495 | −0.010523 | −0.006268 | 0.018066 |
| 281 | 0.026462 | 0.013125 | 0.017403 | −0.01419 | −0.015359 | −0.004045 | 0.036968 | −0.023169 | −0.023358 | −0.005784 | −0.029585 | −0.015369 | −0.031194 | −0.022365 |
| 282 | −0.011541 | 0.114572 | −0.00251 | −0.021608 | −0.074971 | 0.013023 | 0.0305 | −0.013545 | 0.032164 | 0.012907 | −0.003156 | −0.014096 | −0.043097 | 0.060171 |
| 283 | −0.025548 | 0.012565 | −0.026346 | −0.031054 | −0.00318 | −0.057701 | 0.04109 | 0.051249 | −0.035872 | −0.035034 | 0.002161 | 0.052509 | 0.035742 | −0.020035 |
| 284 | 0.00486 | −0.019899 | −0.014426 | −0.029446 | 0.002375 | −0.019384 | −0.028944 | −0.00694 | −0.047564 | 0.007791 | 0.025474 | 0.014472 | −0.010618 | −0.014451 |
| 285 | −0.057432 | 0.018127 | 0.029614 | −0:00055 | −0.035434 | 0.008933 | −0.040015 | 0.008632 | 0.005182 | 0.022975 | 0.029751 | 0.012959 | 0.012111 | −0.018896 |
| 286 | 0.0237 | 0.0216 | −0.015558 | −0.008163 | 0.033394 | 0.028806 | 0.046741 | −0.054114 | −0.069945 | −0.011807 | 0.001827 | −0.00929 | −0.05369 | 0.003923 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 287 | −0.030569 | 0.008358 | −0.012179 | 0.040373 | −0.012716 | 0.015151 | 0.013772 | −0.031864 | −0.018323 | −0.034243 | −0.019246 | −0.012744 | −0.024545 | 0.025549 |
| 288 | −0.001749 | 0.007599 | −0.024343 | 0.014761 | 0.020485 | −0.009232 | 0.014188 | 0.038204 | 0.0202891 | −0.016743 | −0.020358 | −0.036218 | 0.053204 | 0.006607 |
| 289 | −0.033452 | −0.045773 | 0.010382 | 0.009172 | −0.001289 | −0.030846 | −0.008705 | −0.00241 | 0.037507 | 0.016432 | −0.006422 | −0.002311 | 0.016895 | −0.014902 |
| 290 | −0.006315 | 0.000177 | 0.028248 | −0.006952 | −0.047982 | 0.015435 | 0.019193 | −0.00902 | 0.020981 | −0.015254 | 0.009269 | −0.013399 | 0.009005 | −0.01192 |
| 291 | 0.005 | −0.000248 | 0.016234 | −0.00297 | −0.033469 | 0.018554 | 0.005417 | −0.019441 | 0.017294 | −0.019079 | 0.01607 | −0.00606 | 0.00354 | −0.014416 |
| 292 | −0.032716 | 0.008652 | 0.050366 | −0.001455 | 0.007093 | −0.022719 | 0.007455 | 0.013343 | −0.040202 | −0.008698 | 0.014053 | −0.009419 | −0.004215 | −0.019705 |
| 293 | −0.019517 | −0.040982 | 0.035759 | 0.062081 | 0.024843 | −0.007315 | 0.048544 | −0.061925 | −0.02556 | −0.005501 | −0.064036 | −0.032 | 0.020011 | −0.007229 |
| 294 | −0.043936 | −0.0248 | −0.013733 | −0.003505 | −0.047615 | −0.018877 | −0.012856 | −0.024138 | −0.023291 | −0.022206 | 0.008773 | 0.069273 | 0.011414 | −0.009673 |
| 295 | 0.009158 | −0.08732 | −0.032774 | 0.052335 | 0.000714 | 0.058827 | 0.04377 | −0.004026 | 0.01361 | −0.049784 | 0.047879 | 0.000733 | 0.025185 | −0.044743 |
| 296 | 0.010969 | 0.027797 | 0.013099 | −0.042682 | 0.018008 | 0.018987 | 0.014652 | −0.008125 | 0.001802 | −0.030036 | 0.00593 | −0.000023 | −0.033163 | 0.033153 |
| 297 | 0.016291 | −0.031887 | −0.005284 | 0.002824 | −0.00619 | −0.006825 | 0.046525 | 0.000938 | −0.023769 | −0.033105 | −0.017386 | 0.005675 | 0.032978 | −0.000668 |
| 298 | 0.035901 | 0.117838 | 0.004652 | −0.043348 | 0.022425 | −0.023147 | −0.005787 | 0.011703 | 0.013073 | −0.035404 | −0.013503 | 0.084662 | −0.000148 | −0.00074 |
| 299 | 0.024293 | −0.048847 | 0.036628 | −0.028984 | 0.005115 | −0.013254 | −0.029728 | −0.031646 | 0.012727 | 0.008408 | 0.023202 | −0.012076 | −0.00927 | 0.019791 |
| 300 | −0.02504 | −0.016097 | −0.017719 | −0.007959 | −0.014875 | 0.007255 | 0.037071 | −0.087205 | −0.027757 | −0.002223 | −0.058039 | −0.0555 | −0.05732 | 0.024651 |
| 301 | 0.004476 | 0.011004 | 0.002919 | −0.038033 | −0.011852 | 0.022501 | −0.030715 | 0.015116 | 0.023499 | −0.003611 | 0.020695 | 0.037155 | 0.004389 | −0.004245 |
| 302 | −0.018422 | −0.020544 | −0.060279 | 0.012861 | −0.016554 | 0.056154 | −0.041515 | −0.000539 | −0.000631 | 0.014112 | −0.017094 | −0.006248 | 0.006498 | 0.027229 |
| 303 | −0.002285 | 0.013111 | 0.004402 | −0.033745 | 0.048407 | 0.031873 | −0.032399 | 0.032375 | −0.012657 | 0.030377 | 0.06601 | 0.006402 | −0.036118 | 0.025391 |
| 304 | 0.006908 | −0.165134 | −0.005885 | 0.06846 | 0.027276 | 0.006996 | −0.057142 | 0.020319 | −0.024988 | −0.030795 | 0.002943 | −0.042171 | −0.009842 | 0.006798 |
| 305 | −0.012167 | 0.154743 | −0.005782 | 0.017084 | 0.053406 | −0.031841 | −0.003908 | 0.032261 | −0.022314 | 0.004364 | 0.047196 | 0.029303 | 0.026051 | 0.052791 |
| 306 | −0.014208 | 0.00179 | −0.008311 | 0.039765 | 0.04454 | −0.068089 | −0.03181 | 0.019271 | −0.069365 | −0.049065 | −0.105968 | 0.033081 | −0.026905 | 0.017675 |
| 307 | 0.014418 | 0.0483 | −0.043117 | −0.003984 | 0.056522 | 0.015927 | −0.015792 | 0.033034 | 0.046097 | −0.003147 | 0.033889 | 0.001332 | 0.02632 | −0.020038 |
| 308 | −0.010052 | 0.057594 | −0.007615 | 0.02828 | −0.025452 | −0.040157 | −0.022522 | −0.001006 | −0.014875 | −0.080877 | −0.077374 | 0.006105 | 0.035033 | 0.044305 |
| 309 | 0.003761 | 0.096309 | −0.029118 | 0.004152 | −0.071106 | 0.011847 | 0.02714 | 0.00931 | −0.018035 | −0.027544 | −0.014656 | 0.001668 | 0.003992 | 0.037141 |
| 310 | 0.03041 | 0.006825 | −0.036702 | 0.033971 | −0.035716 | −0.001755 | −0.038517 | 0.046325 | 0.008228 | −0.049057 | −0.07595 | −0.065818 | 0.030683 | −0.014836 |
| 311 | 0.016766 | −0.06708 | −0.012313 | −0.041743 | 0.004176 | 0.011596 | −0.023223 | −0.018874 | 0.004523 | 0.032375 | 0.015552 | −0.018564 | 0.01906 | −0.036443 |
| 312 | −0.039801 | 0.000647 | −0.025094 | 0.063288 | −0.028123 | −0.042532 | −0.021186 | −0.020092 | 0.011338 | −0.03339 | −0.033201 | −0.021042 | −0.007758 | 0.035063 |
| 313 | 0.028872 | 0.14349 | 0.013153 | −0.065992 | 0.018128 | 0.025678 | −0.023013 | −0.024236 | −0.048556 | −0.010733 | 0.03684 | −0.024205 | −0.006238 | 0.026286 |
| 314 | −0.01313 | −0.082195 | 0.042763 | −0.028532 | −0.016815 | 0.023663 | 0.061593 | 0.036199 | −0.010851 | −0.005214 | −0.052878 | −0.047318 | 0.091155 | −0.06211 |
| 315 | −0.015997 | 0.006588 | −0.014803 | 0.051011 | 0.019453 | −0.009933 | −0.00873 | −0.011592 | −0.000465 | −0.010724 | 0.019771 | −0.014545 | −0.023974 | −0.016226 |
| 316 | −0.018419 | 0.012791 | 0.056855 | −0.035378 | 0.015543 | −0.03682 | 0.004282 | 0.004507 | 0.043561 | 0.001905 | 0.100047 | −0.032725 | 0.052906 | −0.051534 |
| 317 | 0.015796 | 0.027748 | −0.043885 | 0.009775 | −0.054668 | −0.014898 | 0.02742 | 0.014314 | 0.014521 | −0.019071 | 0.03991 | 0.021866 | −0.021175 | −0.0131 |
| 318 | −0.046429 | −0.016101 | −0.006376 | 0.04581 | −0.00939 | 0.01044 | 0.041996 | −0.021253 | 0.034061 | 0.008564 | −0.015229 | 0.053588 | 0.025859 | 0.050882 |
| 319 | −0.000493 | 0.029327 | −0.024837 | 0.060793 | 0.027665 | 0.023368 | −0.014574 | 0.003808 | 0.024989 | −0.030481 | 0.027553 | −0.000247 | −0.030565 | 0.008153 |
| 320 | 0.016025 | 0.014643 | −0.040113 | −0.066407 | −0.027626 | 0.019584 | −0.037819 | −0.018872 | −0.009841 | 0.019754 | −0.001155 | −0.019602 | 0.014167 | −0.011497 |
| 321 | 0.003495 | −0.016842 | 0.005517 | −0.028956 | 0.014296 | −0.031435 | 0.088442 | −0.007608 | −0.062646 | −0.001314 | 0.040488 | 0.001066 | −0.037949 | 0.016711 |
| 322 | −0.024375 | 0.01607 | 0.035733 | −0.018731 | −0.007842 | 0.026766 | 0.036227 | −0.004104 | −0.015463 | 0.011388 | −0.003437 | 0.012201 | −0.077445 | −0.033369 |
| 323 | −0.019288 | −0.015297 | −0.009153 | 0.005252 | −0.015188 | 0.014375 | 0.064828 | 0.004151 | 0.01761 | −0.007493 | −0.015732 | 0.020749 | 0.008534 | 0.014689 |
| 324 | 0.043294 | 0.043722 | −0.041787 | 0.013997 | −0.050145 | −0.00239 | −0.002677 | 0.007911 | 0.058633 | 0.034993 | −0.041385 | −0.049198 | 0.017268 | 0.008205 |
| 325 | 0.032451 | 0.060691 | 0.048296 | 0.012807 | −0.018587 | −0.008962 | 0.030514 | −0.01221 | 0.006893 | 0.015402 | −0.003962 | −0.044874 | −0.051002 | −0.017888 |
| 326 | 0.022677 | −0.106352 | 0.016026 | −0.064066 | 0.063913 | 0.009598 | −0.016439 | −0.031237 | −0.005082 | 0.008121 | 0.033539 | 0.063314 | 0.009957 | −0.009456 |
| 327 | −0.010483 | −0.038048 | −0.011374 | 0.03323 | −0.010719 | −0.003112 | 0.007341 | −0.012565 | −0.008951 | −0.015754 | −0.003841 | −0.0053 | −0.010845 | −0.069585 |
| 328 | −0.009091 | −0.082539 | −0.015989 | 0.021572 | 0.049109 | −0.012866 | 0.032825 | 0.036761 | −0.034914 | −0.019963 | −0.064031 | 0.084516 | −0.019408 | 0.055712 |
| 329 | −0.012836 | −0.023507 | −0.003367 | −0.052395 | 0.042673 | 0.016767 | 0.022099 | −0.018484 | −0.000802 | 0.034134 | −0.006481 | −0.062706 | −0.014047 | 0.008993 |
| 330 | 0.014138 | 0.006318 | 0.033446 | 0.064569 | −0.031567 | −0.012647 | −0.023042 | −0.011968 | −0.024646 | −0.041465 | 0.025761 | 0.020986 | 0.0164 | 0.009144 |
| 331 | 0.005357 | 0.00072 | 0.01129 | 0.025319 | 0.023465 | −0.028541 | −0.021019 | −0.017466 | −0.01584 | −0.025746 | −0.037132 | −0.007612 | 0.007213 | −0.003607 |
| 332 | 0.002115 | 0.046124 | −0.024403 | −0.05371 | −0.056987 | −0.045484 | −0.038538 | −0.019293 | −0.037561 | 0.009578 | 0.002504 | −0.03287 | 0.060795 | −0.045153 |
| 333 | −0.024172 | 0.013515 | 0.02598 | 0.033271 | −0.017511 | −0.033359 | 0.049169 | −0.007704 | 0.007593 | 0.024869 | −0.028813 | −0.015703 | −0.016263 | −0.008492 |
| 334 | −0.024637 | 0.07834 | −0.063234 | 0.011834 | 0.010309 | −0.009061 | −0.01831 | −0.001061 | 0.008494 | 0.030634 | −0.05951 | 0.039359 | 0.070039 | 0.030164 |
| 335 | 0.004995 | 0.010041 | 0.012123 | 0.092804 | −0.042778 | −0.025857 | 0.037118 | −0.029187 | −0.03432 | −0.054484 | −0.006472 | 0.002525 | 0.036398 | −0.02554 |
| 336 | −0.025221 | −0.009373 | 0.019297 | −0.055785 | −0.045466 | 0.02331 | −0.03875 | −0.035365 | 0.003379 | 0.037418 | −0.016755 | −0.053525 | 0.01182 | 0.006538 |
| 337 | 0.026828 | 0.006478 | 0.019906 | −0.02427 | −0.081658 | −0.036211 | −0.017802 | 0.064448 | 0.065232 | 0.078282 | −0.035131 | −0.024022 | 0.028299 | 0.01255 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 338 | −0.008144 | −0.034272 | −0.026748 | −0.006729 | 0.001113 | −0.007817 | 0.002851 | −0.050965 | 0.030706 | 0.012494 | −0.040359 | −0.064651 | −0.02427 | 0.005677 |
| 339 | −0.005664 | −0.023009 | 0.051697 | 0.041074 | −0.055335 | 0.081125 | −0.099219 | 0.043554 | −0.011153 | 0.024534 | −0.006521 | −0.017415 | −0.005217 | −0.037926 |
| 340 | −0.009946 | 0.024019 | 0.029022 | −0.006916 | −0.011917 | −0.004936 | −0.006074 | 0.0144 | 0.000442 | 0.01515 | −0.038307 | 0.004723 | 0.028489 | 0.016786 |

| | EV | EW | EX | EY | EZ | FA | FB | FC | FD | FE | FF | FG | FH | FI |
|---|---|---|---|---|---|---|---|---|---|---|---|---|---|---|
| 1 | −0.014525 | −0.168975 | −0.038303 | −0.185663 | −0.069341 | −0.046869 | 0.015273 | 0.003979 | 0.078718 | 0.085511 | 0.071294 | 0.013956 | −0.066994 | −0.010726 |
| 2 | 0.025705 | 0.034309 | 0.070151 | 0.047973 | 0.082674 | 0.106411 | −0.060356 | −0.010845 | 0.090166 | 0.024991 | 0.067372 | 0.069336 | 0.032351 | 0.060609 |
| 3 | −0.090862 | 0.056651 | 0.087171 | 0.121042 | 0.089224 | 0.095317 | 0.01591 | 0.104554 | −0.004529 | −0.072416 | −0.070226 | 0.080109 | 0.149147 | 0.108975 |
| 4 | 0.039392 | 0.140663 | −0.034279 | 0.0566 | 0.08213 | −0.06958 | 0.069952 | 0.073971 | 0.012328 | −0.085022 | 0.008717 | 0.018204 | 0.107433 | 0.060031 |
| 5 | −0.0745 | 0.01806 | −0.061089 | 0.088823 | 0.018006 | 0.000162 | −0.060524 | −0.036651 | −0.005777 | −0.004001 | −0.047759 | 0.002999 | −0.036129 | −0.016098 |
| 6 | −0.103469 | −0.061647 | 0.040112 | 0.027368 | 0.092738 | −0.002673 | 0.031112 | −0.04923 | −0.06233 | −0.010958 | 0.056048 | −0.021821 | −0.018818 | −0.020696 |
| 7 | 0.037347 | 0.016802 | −0.099247 | −0.023271 | −0.062544 | 0.018056 | −0.011392 | −0.076823 | −0.055836 | −0.070526 | 0.000282 | −0.043165 | −0.011793 | 0.056061 |
| 8 | 0.09732 | 0.070082 | 0.047653 | −0.045092 | −0.000669 | −0.126444 | −0.022364 | −0.145006 | −0.011256 | 0.051168 | −0.03518 | 0.00258 | 0.084002 | −0.025625 |
| 9 | 0.02307 | 0.019112 | 0.084355 | −0.001044 | −0.089451 | 0.033151 | 0.028892 | −0.017601 | −0.001684 | 0.002285 | −0.043859 | 0.05 | −0.02879 | −0.10585 |
| 10 | 0.067778 | 0.008101 | −0.035592 | 0.098985 | −0.113816 | −0.042201 | −0.081443 | 0.0704 | 0.005759 | 0.007879 | 0.033901 | 0.021411 | 0.071623 | −0.08987 |
| 11 | 0.023367 | 0.037376 | 0.04735 | 0.035116 | 0.039362 | 0.060572 | 0.063776 | −0.004981 | 0.048799 | −0.031544 | −0.055313 | 0.042756 | 0.015364 | 0.014996 |
| 12 | 0.004075 | 0.017476 | −0.056769 | 0.030635 | 0.016279 | 0.044391 | 0.037927 | 0.068591 | 0.029659 | −0.058371 | −0.024589 | −0.004936 | −0.026895 | 0.031109 |
| 13 | 0.086301 | −0.025625 | −0.033828 | −0.041434 | −0.089228 | 0.012284 | 0.09139 | 0.079503 | −0.024054 | 0.077003 | 0.084429 | 0.054266 | −0.003337 | 0.104273 |
| 14 | −0.031322 | 0.061571 | −0.055613 | −0.021057 | −0.057702 | −0.02085 | −0.014178 | 0.011263 | 0.064585 | 0.115245 | −0.010455 | 0.017677 | 0.031147 | 0.058951 |
| 15 | 0.008623 | −0.009563 | 0.014545 | 0.035859 | 0.013695 | −0.045239 | 0.01654 | −0.069911 | −0.067681 | −0.080024 | −0.112661 | −0.212699 | −0.057353 | −0.013063 |
| 16 | −0.088137 | −0.033539 | −0.002589 | 0.054731 | −0.00281 | −0.0488 | 0.014546 | 0.052685 | −0.033502 | 0.044417 | 0.016763 | 0.024352 | 0.014934 | 0.029462 |
| 17 | 0.141965 | 0.07055 | −0.061301 | 0.047082 | −0.155597 | 0.005991 | −0.120779 | 0.072668 | −0.082869 | 0.004993 | 0.064434 | −0.071176 | −0.023774 | 0.043474 |
| 18 | −0.005359 | −0.074613 | 0.086367 | −0.062316 | −0.001918 | −0.010578 | −0.046254 | 0.015055 | −0.041674 | −0.048719 | −0.082977 | −0.031887 | −0.072968 | −0.032003 |
| 19 | 0.089199 | −0.070247 | −0.001668 | 0.015311 | −0.014983 | 0.08699 | −0.031146 | −0.051938 | 0.087802 | −0.035907 | −0.071262 | −0.031347 | −0.025526 | −0.038725 |
| 20 | 0.036 | −0.014623 | 0.015626 | 0.071898 | −0.042961 | −0.173556 | 0.016197 | 0.011635 | −0.088638 | 0.003801 | 0.072483 | 0.007848 | 0.014012 | −0.049651 |
| 21 | −0.15755 | 0.030047 | 0.073222 | −0.031201 | −0.046334 | −0.012716 | 0.082083 | −0.057813 | −0.212188 | 0.038869 | −0.076848 | 0.021954 | 0.033507 | 0.042173 |
| 22 | 0.092936 | 0.066142 | 0.067105 | −0.044856 | −0.022555 | −0.026323 | −0.042577 | 0.008283 | −0.18186 | −0.077972 | 0.038353 | −0.072385 | 0.011367 | 0.046291 |
| 23 | 0.01366 | −0.017823 | −0.041373 | −0.006098 | 0.000267 | 0.012573 | 0.003576 | −0.002016 | 0.04085 | 0.009616 | −0.075982 | −0.013236 | −0.040613 | −0.033657 |
| 24 | −0.10728 | −0.016046 | −0.015507 | 0.092036 | 0.008431 | 0.003755 | −0.018753 | −0.030347 | 0.122937 | 0.012268 | 0.114627 | 0.077448 | 0.066903 | −0.037059 |
| 25 | −0.002031 | 0.014637 | −0.016434 | −0.036963 | 0.080933 | −0.162979 | −0.037174 | 0.001965 | 0.152441 | 0.02648 | 0.02934 | 0.07019 | 0.011242 | 0.017874 |
| 26 | −0.042928 | −0.009043 | 0.032256 | −0.024029 | −0.034196 | 0.050855 | −0.04143 | 0.132715 | −0.039912 | −0.007893 | 0.117138 | −0.121927 | 0.011382 | −0.08782 |
| 27 | 0.06075 | 0.012488 | −0.066915 | 0.00508 | 0.079938 | −0.016789 | 0.034354 | 0.030429 | 0.039434 | 0.00496 | 0.084044 | −0.077498 | 0.091671 | 0.054805 |
| 28 | −0.175012 | 0.043099 | 0.032128 | −0.021414 | −0.002462 | −0.108634 | −0.115429 | −0.053965 | 0.063247 | 0.057729 | −0.009096 | −0.039081 | −0.011299 | 0.01102 |
| 29 | −0.03461 | 0.056173 | 0.071644 | −0.001923 | −0.066115 | 0.029003 | −0.045241 | 0.072916 | 0.046331 | 0.019945 | 0.091635 | 0.041069 | −0.072773 | 0.024553 |
| 30 | 0.029805 | 0.000007 | 0.014704 | 0.067139 | 0.008679 | −0.000257 | −0.039263 | 0.004752 | −0.110988 | −0.034932 | 0.06531 | −0.062848 | −0.026807 | 0.029197 |
| 31 | 0.103465 | −0.030906 | 0.000572 | −0.017024 | −0.111426 | −0.072272 | 0.045879 | 0.009137 | 0.025557 | 0.012941 | 0.060215 | 0.005194 | −0.06714 | 0.108079 |
| 32 | −0.05409 | 0.002431 | 0.016927 | −0.000156 | 0.020841 | −0.05116 | −0.056318 | −0.016089 | −0.075248 | 0.103054 | −0.021504 | −0.015849 | −0.064666 | 0.043658 |
| 33 | 0.016431 | −0.073117 | −0.032936 | 0.006843 | −0.006425 | 0.041679 | −0.011655 | −0.13333 | 0.033501 | −0.039203 | 0.072994 | 0.122463 | −0.043279 | −0.053097 |
| 34 | 0.03365 | −0.029639 | −0.045645 | −0.053878 | −0.116319 | −0.123756 | −0.030492 | −0.020474 | −0.051412 | −0.094655 | 0.103581 | 0.053479 | −0.012614 | 0.016356 |
| 35 | 0.037216 | −0.052671 | −0.055321 | −0.016568 | −0.000703 | −0.105098 | −0.011086 | 0.04151 | −0.023723 | −0.052956 | 0.063909 | −0.083117 | −0.080965 | −0.064176 |
| 36 | −0.015022 | −0.008107 | 0.01898 | −0.113113 | −0.040159 | −0.007893 | 0.101153 | −0.036 | 0.008147 | 0.080149 | −0.09667 | −0.032262 | 0.072286 | −0.035185 |
| 37 | 0.101209 | −0.036859 | 0.059484 | −0.056183 | 0.03406 | 0.050362 | −0.029652 | 0.085813 | −0.024677 | 0.017032 | −0.135647 | 0.117224 | −0.078426 | −0.048641 |
| 38 | 0.037222 | −0.014971 | 0.03217 | −0.071398 | 0.015496 | 0.056027 | −0.006652 | 0.005429 | −0.026023 | −0.06398 | 0.094736 | −0.039986 | −0.027164 | 0.02102 |
| 39 | 0.002317 | −0.018378 | −0.075874 | 0.050315 | −0.032793 | −0.00072 | 0.012278 | 0.009524 | 0.066665 | −0.104779 | 0.016309 | 0.004831 | −0.015741 | 0.153074 |
| 40 | 0.048651 | 0.088569 | 0.067857 | 0.097484 | −0.008639 | −0.063805 | 0.033619 | −0.050225 | −0.081418 | −0.019093 | −0.119635 | 0.170884 | 0.082664 | 0.071017 |
| 41 | −0.004611 | −0.064852 | −0.007463 | 0.006012 | 0.020712 | 0.023306 | −0.04037 | −0.015204 | −0.01974 | −0.061348 | −0.020555 | 0.040384 | −0.059347 | −0.023387 |
| 42 | −0.025304 | −0.049154 | −0.048638 | 0.041805 | −0.085383 | −0.094738 | −0.016151 | −0.025202 | −0.060839 | 0.172803 | 0.063091 | −0.071512 | 0.044733 | 0.02473 |
| 43 | 0.033032 | 0.085673 | 0.032283 | −0.010559 | 0.008563 | −0.006594 | −0.070274 | −0.201432 | −0.00613 | 0.088643 | 0.025189 | −0.023023 | 0.098637 | −0.020505 |
| 44 | −0.024512 | 0.072762 | 0.059209 | 0.021817 | 0.07806 | 0.047872 | −0.028735 | 0.052334 | −0.01749 | −0.035508 | −0.056022 | −0.151049 | −0.027303 | −0.099411 |
| 45 | 0.010787 | −0.006475 | −0.048376 | −0.021389 | −0.016009 | 0.067671 | 0.053814 | 0.171782 | −0.0332 | −0.080632 | 0.012302 | 0.12671 | 0.031551 | −0.00699 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 46 | −0.002178 | −0.002391 | −0.058597 | −0.033822 | −0.012914 | 0.044952 | 0.071434 | −0.042186 | 0.046346 | −0.042093 | 0.060834 | 0.063691 | −0.078198 | −0.076059 |
| 47 | 0.035785 | 0.043792 | 0.069637 | −0.028016 | 0.01609 | 0.072137 | 0.051972 | −0.099032 | −0.06493 | 0.064801 | −0.128942 | 0.014999 | 0.053426 | 0.007237 |
| 48 | −0.007956 | 0.010476 | −0.060146 | 0.005613 | −0.034016 | 0.05701 | −0.116635 | −0.039636 | 0.071731 | 0.026942 | 0.077713 | −0.055781 | 0.02945 | 0.042639 |
| 49 | −0.044217 | 0.066308 | 0.083256 | 0.025935 | 0.046289 | −0.066045 | 0.042433 | 0.119077 | 0.072246 | 0.092221 | 0.014934 | −0.00098 | 0.029666 | 0.052787 |
| 50 | 0.030416 | 0.031483 | 0.024877 | −0.048153 | 0.050982 | −0.042446 | 0.04361 | 0.015997 | −0.116528 | −0.039533 | 0.081362 | −0.070763 | 0.027865 | 0.092743 |
| 51 | 0.045689 | 0.012512 | 0.035446 | 0.034015 | −0.04509 | 0.00386 | 0.055075 | −0.064719 | −0.005909 | 0.183615 | 0.031873 | −0.061014 | −0.057449 | 0.026564 |
| 52 | 0.073127 | −0.060325 | 0.032292 | −0.025418 | −0.112548 | −0.002377 | 0.024255 | 0.059642 | −0.042979 | 0.102786 | −0.088342 | −0.00344 | −0.052038 | 0.030961 |
| 53 | −0.082629 | −0.021448 | −0.051687 | 0.018861 | −0.04485 | −0.002475 | −0.03618 | 0.023111 | −0.029439 | −0.069218 | −0.058344 | −0.030728 | 0.031378 | −0.057153 |
| 54 | −0.000922 | −0.033301 | −0.051328 | −0.026223 | 0.094662 | 0.011859 | −0.023176 | 0.088522 | −0.133572 | 0.036015 | −0.061981 | −0.095898 | 0.005519 | −0.076672 |
| 55 | 0.029514 | −0.035717 | 0.03489 | −0.029478 | 0.019185 | 0.013573 | 0.030136 | −0.025038 | 0.004333 | 0.023179 | 0.055582 | −0.008103 | −0.063322 | −0.014018 |
| 56 | −0.084336 | −0.066898 | −0.070909 | −0.04272 | −0.049762 | 0.144367 | −0.033939 | 0.103396 | −0.030601 | −0.070087 | −0.031575 | 0.134252 | −0.080385 | 0.043989 |
| 57 | −0.079224 | 0.012093 | −0.080359 | −0.039655 | 0.016599 | −0.044718 | −0.069251 | −0.036539 | −0.083876 | 0.000675 | −0.025681 | 0.064049 | 0.010312 | 0.004312 |
| 58 | −0.063998 | 0.021585 | −0.045799 | −0.036654 | 0.000499 | 0.069162 | 0.078859 | −0.00927 | −0.098716 | −0.143028 | 0.005426 | 0.073313 | −0.009001 | 0.036291 |
| 59 | −0.018893 | −0.063704 | −0.016694 | 0.033446 | −0.078596 | −0.061941 | 0.086934 | −0.043319 | −0.039992 | −0.004978 | 0.039113 | −0.041354 | 0.021369 | −0.029566 |
| 60 | −0.106221 | 0.063659 | 0.010072 | −0.0312 | −0.067742 | 0.047472 | 0.016312 | 0.126021 | −0.089468 | −0.14352 | −0.070827 | 0.0388 | 0.067634 | −0.162894 |
| 61 | −0.016261 | −0.011539 | 0.033807 | 0.008556 | 0.071536 | 0.063562 | −0.002082 | 0.099929 | −0.055415 | 0.071681 | −0.081563 | 0.019904 | −0.02864 | −0.048972 |
| 62 | 0.107704 | 0.021151 | 0.1294 | 0.030418 | −0.087105 | 0.02084 | 0.065997 | 0.26292 | 0.053553 | 0.011918 | 0.005953 | 0.021028 | −0.018567 | 0.120786 |
| 63 | −0.025922 | −0.068808 | −0.095654 | −0.070243 | 0.030843 | −0.039574 | −0.02195 | −0.095903 | 0.123693 | 0.015146 | −0.052512 | −0.154886 | −0.066575 | −0.009064 |
| 64 | −0.021034 | −0.02423 | 0.034808 | −0.024037 | −0.012145 | −0.009025 | 0.006204 | −0.011242 | 0.016203 | 0.022825 | 0.01061 | 0.029856 | 0.000474 | 0.019358 |
| 65 | 0.038016 | 0.017241 | 0.013848 | 0.000378 | 0.088303 | −0.00123 | −0.018349 | 0.052162 | −0.122125 | 0.07123 | −0.038304 | −0.05031 | 0.029398 | −0.075496 |
| 66 | 0.085415 | 0.035911 | 0.050196 | −0.020037 | 0.030626 | 0.070166 | −0.067096 | −0.040324 | −0.09169 | −0.083239 | 0.013654 | 0.063074 | 0.027595 | 0.102678 |
| 67 | −0.060186 | 0.045549 | 0.050675 | 0.040962 | −0.000047 | 0.007785 | 0.113625 | 0.011029 | 0.142057 | 0.012475 | 0.037805 | −0.014057 | 0.051327 | 0.028526 |
| 68 | 0.066282 | −0.070572 | 0.012397 | −0.027147 | −0.045984 | −0.027518 | −0.000562 | 0.002738 | −0.060376 | 0.01398 | −0.017256 | −0.060561 | 0.019762 | 0.002294 |
| 69 | −0.065823 | −0.046576 | 0.043614 | −0.000729 | −0.126571 | 0.011211 | 0.088225 | −0.051701 | 0.040598 | 0.09647 | −0.103967 | 0.006331 | −0.034051 | −0.228361 |
| 70 | 0.084483 | 0.078535 | −0.024048 | 0.027266 | −0.142699 | 0.079272 | −0.035351 | −0.111209 | 0.139601 | 0.039967 | 0.035509 | 0.109701 | 0.049869 | −0.111881 |
| 71 | 0.02414 | −0.031867 | −0.016307 | 0.074189 | 0.054907 | 0.041132 | 0.042501 | 0.035089 | 0.103367 | 0.070647 | 0.057021 | 0.002439 | −0.030003 | −0.024529 |
| 72 | 0.086308 | 0.028217 | −0.013779 | −0.061529 | −0.022397 | −0.032594 | 0.097241 | −0.137297 | −0.023067 | −0.216655 | −0.047668 | −0.006062 | −0.147977 | −0.021291 |
| 73 | 0.015655 | −0.026303 | −0.017564 | −0.008919 | 0.039715 | −0.082934 | −0.097244 | 0.077586 | −0.134787 | 0.113918 | 0.158351 | 0.081597 | −0.064769 | −0.115238 |
| 74 | 0.005789 | 0.003035 | −0.043329 | 0.002197 | 0.025327 | −0.001475 | 0.005958 | −0.032641 | 0.007313 | 0.028468 | −0.032047 | −0.036029 | 0.047571 | 0.08715 |
| 75 | 0.080361 | 0.028507 | 0.051419 | −0.013199 | 0.091562 | −0.098158 | −0.050017 | 0.116315 | 0.061572 | 0.014547 | −0.168591 | −0.181881 | −0.005785 | 0.139181 |
| 76 | 0.021166 | −0.058021 | 0.007244 | −0.073782 | 0.034656 | 0.06147 | −0.127407 | 0.117726 | −0.016913 | −0.152015 | 0.055095 | 0.101836 | −0.048213 | −0.031171 |
| 77 | −0.141742 | −0.043614 | 0.050179 | 0.080489 | 0.130514 | −0.026763 | 0.02228 | −0.013436 | −0.1259 | 0.061144 | 0.019218 | 0.01042 | 0.00866 | 0.01325 |
| 78 | −0.131989 | −0.045863 | −0.053865 | −0.068078 | −0.001023 | 0.097675 | 0.072781 | −0.056557 | −0.122328 | −0.044338 | 0.091958 | 0.028816 | 0.081023 | 0.052938 |
| 79 | 0.081805 | 0.093189 | 0.023285 | 0.073618 | 0.095294 | −0.001107 | −0.046785 | −0.10643 | −0.063457 | −0.10013 | −0.017036 | −0.015949 | 0.077549 | 0.093024 |
| 80 | 0.024937 | −0.054236 | 0.057927 | −0.0195 | −0.077053 | 0.007907 | 0.00668 | −0.094922 | 0.014993 | 0.007217 | 0.046541 | 0.033855 | −0.012405 | −0.03642 |
| 81 | −0.002926 | 0.034115 | 0.022578 | 0.010481 | 0.05371 | −0.077473 | 0.021238 | 0.010569 | −0.001845 | −0.070812 | −0.017755 | −0.025822 | −0.102087 | −0.131555 |
| 82 | −0.062493 | −0.141264 | −0.124484 | −0.041006 | 0.064492 | −0.12045 | 0.19 | 0.169549 | 0.018371 | −0.009861 | −0.050807 | −0.034659 | 0.048028 | 0.090234 |
| 83 | 0.0122 | 0.022363 | 0.088708 | 0.035029 | 0.012267 | 0.186365 | 0.077468 | −0.034177 | −0.008869 | 0.086838 | 0.059437 | 0.105219 | 0.058441 | −0.055699 |
| 84 | −0.063907 | −0.049004 | 0.009422 | −0.000723 | −0.006072 | 0.087432 | 0.007873 | −0.097678 | 0.016225 | 0.033357 | 0.063291 | −0.020207 | 0.019065 | −0.068432 |
| 85 | −0.030225 | 0.035115 | −0.085718 | −0.032526 | 0.02774 | 0.10738 | 0.000182 | 0.088235 | 0.062051 | 0.107305 | 0.0181 | 0.023328 | 0.079762 | 0.055078 |
| 86 | −0.081674 | 0.065831 | 0.091508 | 0.018937 | 0.037526 | −0.136271 | −0.045965 | −0.003113 | 0.189321 | −0.190466 | −0.075457 | −0.104553 | 0.106756 | 0.026927 |
| 87 | −0.02686 | −0.004861 | −0.079822 | −0.010335 | 0.035711 | 0.132408 | 0.08122 | −0.0702 | −0.177943 | 0.138657 | 0.03883 | −0.171914 | −0.01314 | −0.042954 |
| 88 | 0.165634 | 0.043533 | −0.136604 | 0.157887 | −0.066137 | −0.00528 | −0.04103 | 0.093517 | −0.11133 | 0.05283 | −0.14122 | 0.029325 | −0.026568 | 0.046464 |
| 89 | −0.149692 | 0.059351 | 0.007176 | −0.039368 | 0.015296 | 0.057411 | −0.068175 | 0.015748 | 0.023586 | −0.064211 | 0.068817 | −0.131404 | −0.028682 | −0.094658 |
| 90 | −0.091071 | 0.059367 | 0.001555 | −0.02893 | −0.108102 | 0.058055 | −0.007757 | −0.05323 | 0.016253 | −0.016848 | −0.130703 | 0.037959 | 0.030174 | −0.100271 |
| 91 | −0.106067 | 0.020995 | 0.083767 | 0.061968 | −0.058852 | 0.108339 | −0.029765 | −0.080349 | 0.153504 | −0.030853 | −0.078379 | −0.093243 | 0.003993 | 0.223065 |
| 92 | 0.124415 | −0.07002 | 0.031762 | −0.060683 | 0.031967 | −0.010919 | −0.002705 | 0.016104 | −0.043652 | −0.162517 | −0.173496 | 0.055414 | −0.00596 | 0.024988 |
| 93 | 0.068218 | 0.013915 | −0.018024 | 0.029038 | 0.013034 | 0.040445 | −0.045579 | −0.098272 | −0.111067 | −0.022642 | −0.036674 | 0.101092 | 0.085168 | 0.025804 |
| 94 | 0.072018 | 0.065409 | 0.018338 | −0.009238 | 0.059158 | −0.019025 | −0.069459 | 0.074076 | −0.045109 | −0.000947 | 0.037343 | 0.108506 | 0.068688 | 0.072067 |
| 95 | 0.03007 | −0.004181 | 0.036122 | −0.03094 | −0.058287 | 0.054127 | 0.009501 | −0.062639 | 0.055661 | 0.191473 | 0.030447 | 0.006765 | −0.014835 | 0.027299 |
| 96 | −0.032696 | 0.020628 | 0.041594 | 0.042944 | −0.010573 | −0.061369 | 0.155147 | 0.042154 | −0.055959 | −0.044888 | −0.076912 | 0.054582 | −0.06984 | −0.068534 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 97 | −0.034097 | 0.060468 | −0.013215 | 0.011452 | 0.101088 | 0.03151 | 0.009301 | 0.055199 | 0.05765 | −0.081618 | 0.038195 | −0.00752 | 0.035348 | 0.002732 |
| 98 | −0.043791 | 0.102213 | 0.033782 | −0.024709 | −0.056302 | 0.184101 | −0.080187 | 0.061286 | 0.062082 | 0.039492 | 0.069859 | 0.042585 | −0.042119 | −0.102402 |
| 99 | −0.032692 | 0.004856 | −0.045195 | 0.110389 | 0.00525 | −0.005155 | 0.018173 | −0.003411 | −0.156603 | 0.003476 | 0.037372 | 0.024873 | −0.024959 | −0.04539 |
| 100 | 0.085941 | −0.077329 | 0.045146 | 0.010208 | 0.054797 | 0.103338 | −0.067128 | 0.002609 | −0.04456 | −0.103739 | 0.133292 | −0.046062 | 0.05219 | −0.011145 |
| 101 | 0.045924 | −0.11987 | −0.109095 | 0.010461 | −0.028191 | −0.115088 | 0.029695 | −0.115026 | −0.073238 | 0.109669 | −0.134439 | 0.079366 | −0.086429 | 0.054167 |
| 102 | −0.084581 | 0.00233 | 0.05645 | −0.016833 | −0.098765 | 0.02183 | 0.04402 | 0.152067 | −0.059618 | −0.018629 | −0.006182 | −0.069636 | 0.085417 | 0.043675 |
| 103 | 0.057928 | 0.046169 | 0.034715 | −0.042657 | 0.119451 | −0.016358 | −0.081191 | 0.050351 | −0.049907 | −0.039927 | 0.027968 | −0.006378 | −0.035296 | −0.119811 |
| 104 | −0.079826 | 0.010387 | 0.040539 | −0.000613 | −0.056836 | −0.018007 | 0.045933 | −0.066914 | 0.053174 | 0.034264 | −0.067026 | 0.058308 | 0.01436 | 0.048405 |
| 105 | −0.015812 | −0.003849 | −0.008722 | −0.056872 | 0.043422 | 0.0785 | 0.006067 | −0.008537 | 0.017976 | 0.001864 | 0.009511 | 0.010043 | 0.037293 | −0.017713 |
| 106 | 0.0091 | −0.006237 | −0.046434 | 0.009905 | −0.023441 | −0.164185 | −0.04866 | −0.0158 | −0.070062 | −0.151705 | 0.059854 | 0.026802 | −0.046462 | −0.024323 |
| 107 | 0.012055 | 0.097768 | 0.024229 | 0.092992 | −0.056476 | 0.077802 | −0.07698 | 0.05877 | 0.013221 | 0.045308 | −0.005809 | −0.042869 | −0.061058 | 0.040534 |
| 108 | 0.023228 | 0.077123 | −0.021312 | 0.032196 | 0.013889 | 0.015289 | 0.01634 | −0.043149 | −0.008042 | −0.057748 | 0.064433 | −0.106488 | −0.03755 | −0.075829 |
| 109 | 0.064355 | 0.029884 | −0.083966 | 0.040851 | −0.027828 | 0.026173 | 0.068535 | −0.060615 | −0.009131 | −0.037505 | −0.035693 | 0.026571 | 0.065438 | 0.070248 |
| 110 | −0.088757 | −0.046386 | −0.082481 | −0.033714 | 0.011928 | 0.041351 | 0.001505 | −0.006527 | −0.050857 | −0.050987 | −0.055707 | −0.016652 | 0.033934 | 0.053746 |
| 111 | 0.046867 | −0.012445 | 0.090398 | −0.075593 | −0.056418 | −0.012498 | 0.008376 | −0.044664 | 0.012017 | 0.004626 | 0.038339 | 0.009529 | −0.035148 | 0.044687 |
| 112 | 0.066811 | −0.0088 | 0.032874 | 0.01092 | −0.027264 | 0.043474 | 0.011657 | −0.032089 | −0.052069 | −0.018074 | −0.059711 | −0.033795 | −0.019888 | 0.022992 |
| 113 | 0.047033 | 0.005539 | −0.079118 | 0.043148 | 0.042366 | 0.016853 | −0.021899 | −0.082288 | 0.039321 | −0.065072 | 0.036725 | 0.00958 | 0.087195 | −0.062769 |
| 114 | −0.02772 | −0.070642 | 0.054764 | −0.037495 | 0.02276 | 0.04262 | 0.07575 | −0.011986 | 0.069621 | 0.004536 | 0.007549 | −0.035073 | −0.061578 | −0.044128 |
| 115 | 0.045887 | −0.001897 | 0.015868 | −0.071821 | −0.031369 | 0.02055 | 0.08045 | 0.019306 | 0.025594 | 0.090048 | 0.021145 | 0.01171 | −0.039011 | −0.062866 |
| 116 | −0.093552 | 0.018318 | 0.008369 | −0.003315 | −0.016254 | −0.038808 | 0.0388 | 0.040184 | 0.035364 | 0.002944 | −0.036413 | −0.023283 | 0.041057 | 0.004187 |
| 117 | −0.103601 | 0.01959 | −0.068126 | 0.031911 | 0.043844 | 0.023061 | −0.017061 | −0.063163 | 0.020358 | 0.150692 | −0.188988 | −0.020233 | 0.015139 | 0.007036 |
| 118 | 0.016904 | −0.02569 | 0.022546 | −0.028794 | −0.052922 | −0.014651 | 0.016474 | −0.037032 | −0.093635 | −0.033556 | 0.093881 | −0.095518 | 0.08115 | 0.011095 |
| 119 | 0.015289 | −0.021917 | −0.041444 | −0.066303 | −0.137161 | −0.089653 | −0.120132 | 0.069099 | 0.059243 | −0.123902 | −0.012994 | 0.066932 | −0.073564 | −0.035374 |
| 120 | −0.025581 | −0.097673 | 0.068495 | 0.057182 | −0.065652 | −0.020867 | −0.031751 | −0.044822 | 0.073348 | −0.03476 | −0.108175 | 0.053986 | −0.145039 | 0.012368 |
| 121 | 0.017481 | 0.127414 | 0.105259 | 4:02392 | 0.076944 | −0.081203 | 0.083988 | −0.017582 | −0.083995 | −0.102378 | 0.043371 | 0.109153 | 0.028917 | −0.091512 |
| 122 | 0.037208 | −0.007355 | −0.075796 | 0.033961 | 0.067234 | −0.039089 | −0.015776 | 0.089021 | −0.037391 | 0.085264 | 0.028563 | 0.017795 | −0.03406 | 0.09301 |
| 123 | −0.147694 | −0.060042 | 0.023684 | −0.001623 | −0.035037 | −0.040837 | 0.080606 | −0.054113 | −0.059881 | 0.009346 | 0.030926 | 0.171614 | 0.069754 | 0.006646 |
| 124 | 0.001794 | −0.036973 | −0.092085 | −0.049431 | 0.113936 | 0.110747 | 0.122116 | 0.13508 | 0.057108 | 0.043643 | −0.067997 | 0.05219 | 0.049038 | −0.07002 |
| 125 | −0.019374 | 0.050647 | 0.067839 | −0.036838 | −0.066677 | −0.168579 | −0.120466 | 0.055672 | 0.046522 | 0.022154 | 0.151954 | 0.007681 | 0.0461 | −0.034917 |
| 126 | −0.06842 | −0.103667 | 0.018091 | −0.076479 | −0.031151 | 0.175405 | −0.100452 | −0.096583 | −0.052996 | −0.067172 | −0.113732 | −0.080129 | 0.091233 | 0.039201 |
| 127 | 0.114847 | 0.006207 | 0.143709 | −0.022428 | −0.033419 | −0.009625 | 0.044193 | −0.003743 | −0.020344 | 0.059076 | −0.035745 | 0.029651 | 0.007724 | 0.004736 |
| 128 | −0.072196 | 0.041069 | 0.065319 | 0.090347 | 0.042379 | −0.050539 | −0.132387 | 0.003887 | −0.038419 | 0.129442 | −0.014363 | −0.02738 | 0.014459 | 0.015775 |
| 129 | 0.013762 | −0.02054 | −0.034257 | 0.029425 | −0.024382 | −0.016747 | −0.024301 | −0.036938 | 0.009757 | −0.021475 | −0.038938 | −0.045905 | 0.072286 | −0.002141 |
| 130 | −0.108674 | 0.073681 | −0.015231 | −0.065194 | −0.027399 | −0.060235 | 0.006543 | −0.023227 | −0.05583 | −0.019077 | −0.039982 | 0.039083 | 0.079023 | 0.028497 |
| 131 | 0.065041 | 0.015087 | 0.017963 | 0.037029 | −0.07355 | −0.073539 | 0.181145 | 0.012321 | 0.103721 | −0.030894 | −0.013234 | −0.018806 | −0.002381 | −0.005327 |
| 132 | 0.038864 | 0.016187 | −0.111707 | −0.07907 | −0.068893 | 0.011617 | −0.025125 | 0.046955 | 0.027573 | 0.059238 | −0.046192 | 0.028064 | 0.046856 | −0.023648 |
| 133 | −0.029818 | −0.113671 | 0.110663 | 0.113217 | −0.012216 | 0.017744 | 0.001887 | −0.031218 | 0.088786 | −0.051796 | 0.0828 | −0.009876 | 0.008801 | −0.059229 |
| 134 | −0.110602 | 0.016251 | 0.011182 | 0.056893 | 0.048861 | −0.027068 | −0.026249 | 0.012126 | 0.013613 | 0.062382 | 0.115152 | 0.046866 | −0.091473 | 0.011871 |
| 135 | −0.059744 | 0.011941 | −0.021953 | 0.009464 | 0.004727 | 0.042033 | −0.076239 | 0.011663 | −0.051686 | −0.084828 | 0.007874 | −0.070185 | −0.018952 | 0.072152 |
| 136 | 0.06646 | −0.009907 | −0.007276 | −0.067821 | −0.014829 | 0.020552 | 0.03043 | −0.012135 | 0.005085 | −0.043371 | 0.008909 | −0.064364 | 0.037945 | 0.000199 |
| 137 | 0.097653 | 0.024667 | 0.073744 | 0.025115 | −0.044561 | 0.029496 | 0.06363 | −0.012024 | 0.024181 | 0.035364 | −0.060171 | 0.005652 | −0.006051 | 0.03571 |
| 138 | 0.066966 | −0.049002 | 0.027712 | −0.010705 | −0.030169 | 0.097592 | −0.064205 | −0.03813 | 0.003851 | 0.059097 | −0.005354 | −0.037578 | 0.061599 | −0.032527 |
| 139 | −0.085048 | 0.015098 | −0.023185 | 0.05079 | −0.052436 | 0.015164 | −0.014061 | 0.014888 | −0.036899 | 0.001043 | −0.048918 | 0.005943 | 0.05421 | 0.02985 |
| 140 | −0.007483 | −0.057764 | 0.03283 | −0.037047 | 0.012785 | 0.028615 | −0.049489 | −0.028892 | −0.000442 | 0.009785 | −0.012611 | 0.041146 | −0.01165 | −0.009003 |
| 141 | −0.039051 | 0.090672 | 0.000085 | 0.049126 | 0.016756 | −0.05635 | 0.021237 | −0.007345 | 0.023944 | 0.002874 | −0.032419 | −0.039086 | −0.044417 | −0.003704 |
| 142 | −0.016468 | −0.030064 | −0.084222 | −0.107038 | −0.120649 | −0.01402 | −0.051313 | 0.009276 | −0.009699 | 0.01411 | 0.040464 | −0.046094 | −0.121055 | −0.044583 |
| 143 | 0.009917 | 0.050342 | −0.006306 | 0.042592 | −0.09048 | 0.028691 | 0.010039 | −0.02501 | 0.0475771 | −0.002376 | −0.002479 | −0.031862 | 0.024028 | −0.022859 |
| 144 | −0.024774 | 0.062923 | −0.005638 | −0.064888 | −0.098242 | −0.010843 | −0.058876 | −0.044558 | 0.032164 | 0.010588 | 0.033277 | −0.078055 | 0.037203 | 0.044423 |
| 145 | 0.004793 | 0.004409 | −0.057801 | −0.049297 | −0.001557 | 0.000709 | −0.060975 | −0.030919 | −0.016537 | 0.034386 | −0.051997 | −0.014651 | −0.016041 | −0.014151 |
| 146 | 0.03769 | 0.088812 | −0.019998 | 0.003393 | 0.027776 | −0.080278 | −0.020925 | 0.036227 | 0.010089 | 0.016928 | −0.010459 | −0.005293 | 0.064287 | −0.050723 |
| 147 | −0.058006 | 0.000611 | −0.059516 | −0.035114 | 0.049991 | −0.008826 | 0.048547 | 0.022963 | 0.04656 | −0.009534 | −0.041397 | 0.006255 | 0.00056 | 0.005423 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 148 | −0.038865 | 0.005166 | −0.030493 | −0.042862 | 0.007616 | −0.033149 | 0.05061 | 0.068228 | −0.042702 | 0.007019 | −0.011803 | 0.023322 | −0.034736 | −0.022301 |
| 149 | −0.090662 | −0.040269 | −0.006983 | −0.01818 | −0.007226 | 0.011826 | 0.026254 | −0.019861 | −0.062475 | −0.078897 | 0.036152 | −0.014933 | −0.039525 | −0.032469 |
| 150 | −0.001789 | 0.012026 | 0.052214 | −0.05173 | −0.031086 | −0.030433 | 0.025443 | 0.068873 | −0.071521 | −0.036825 | 0.013105 | 0.052597 | −0.036775 | 0.01826 |
| 151 | 0.352802 | −0.001441 | −0.00858 | 0.017937 | 0.074687 | 0.071363 | 0.008965 | −0.008392 | 0.023029 | −0.038364 | 0.02536 | −0.061683 | 0.077806 | −0.058319 |
| 152 | −0.021556 | 0.595961 | −0.082256 | −0.065664 | −0.064805 | 0.021599 | −0.010421 | −0.035313 | 0.010639 | 0.036609 | −0.000721 | −0.056869 | −0.136624 | −0.025344 |
| 153 | 0.007956 | −0.086761 | 0.580213 | −0.031662 | −0.058929 | −0.047154 | −0.054534 | 0.009404 | −0.059812 | 0.000362 | 0.001696 | −0.018669 | −0.01885 | 0.006157 |
| 154 | 0.009208 | −0.102634 | 0.000421 | 0.690172 | −0.048298 | 0.024229 | 0.020859 | −0.000529 | −0.018649 | −0.026615 | 0.008159 | −0.029789 | −0.086572 | −0.07486 |
| 155 | 0.048117 | −0.028534 | −0.029913 | −0.051161 | 0.528445 | 0.004594 | −0.016812 | −0.06677 | 0.053608 | 0.089172 | 0.014916 | 0.072775 | −0.065495 | −0.019234 |
| 156 | 0.06989 | 0.001196 | −0.03003 | −0.035852 | −0.028483 | 0.289798 | 0.013323 | 0.00569 | −0.028885 | −0.031819 | 0.034709 | −0.073706 | −0.084315 | 0.026704 |
| 157 | 0.024066 | 0.055137 | 0.015659 | 0.039903 | 0.004583 | 0.016164 | 0.530292 | −0.065492 | 0.023226 | −0.037655 | 0.08343 | −0.079246 | −0.037845 | −0.056865 |
| 158 | −0.054888 | −0.04167 | −0.032872 | −0.009715 | −0.049807 | −0.020682 | −0.039866 | 0.254564 | −0.036379 | 0.046668 | −0.06266 | −0.047377 | 0.026662 | −0.067788 |
| 159 | 0.073723 | 0.042978 | −0.01728 | −0.031995 | −0.024765 | −0.012532 | −0.008928 | −0.013686 | 0.177956 | −0.025471 | −0.007754 | 0.021528 | −0.005915 | −0.026768 |
| 160 | 0.055089 | 0.001671 | 0.007262 | −0.039793 | 0.049715 | 0.014294 | −0.021363 | 0.025514 | −0.075294 | 0.200563 | −0.006526 | −0.006405 | −0.08819 | 0.015771 |
| 161 | 0.012252 | −0.002471 | −0.006865 | 0.031647 | 0.053504 | 0.011527 | 0.054153 | −0.031049 | −0.002583 | −0.027178 | 0.313999 | 0.028055 | −0.020876 | 0.048178 |
| 162 | −0.031232 | −0.021782 | −0.000824 | −0.000102 | 0.088807 | −0.061143 | −0.078686 | −0.023481 | −0.003385 | −0.006033 | −0.032148 | 0.312814 | −0.050817 | 0.013152 |
| 163 | 0.054612 | −0.154897 | −0.013399 | −0.036012 | −0.075369 | −0.027681 | −0.011246 | 0.033596 | 0.035825 | 0.013524 | 0.011024 | −0.000772 | 0.562071 | −0.070658 |
| 164 | −0.102752 | −0.036948 | 0.01064 | −0.033888 | −0.011477 | 0.007425 | 0.034561 | −0.043272 | −0.061867 | −0.016219 | 0.075069 | 0.037345 | −0.107476 | 0.451984 |
| 165 | 0.023623 | −0.031792 | −0.071404 | −0.03629 | −0.027452 | 0.001897 | 0.001711 | −0.016161 | 0.01615 | −0.034181 | −0.009938 | −0.039829 | −0.040006 | 0.00383 |
| 166 | −0.057728 | 0.041024 | −0.023519 | −0.002794 | 0.002974 | −0.019009 | −0.024952 | −0.043849 | −0.000911 | −0.014214 | 0.080572 | −0.004051 | 0.079278 | −0.00442 |
| 167 | −0.002611 | −0.028099 | −0.000774 | 0.013823 | 0.058782 | −0.016869 | 0.032676 | 0.029023 | 0.018346 | −0.00725 | −0.01564 | 0.018395 | −0.023191 | −0.023896 |
| 168 | −0.032773 | −0.001341 | 0.00622 | −0.033223 | 0.065612 | 0.028902 | −0.011346 | 0.080277 | 0.02267 | 0.0792 | 0.007092 | 0.051868 | −0.091672 | −0.029231 |
| 169 | 0.035072 | 0.011349 | −0.005288 | 0.023393 | −0.034735 | 0.00072 | 0.006477 | 0.051217 | −0.01799 | 0.034117 | 0.03396 | −0.044774 | −0.007786 | −0.020748 |
| 170 | 0.018218 | −0.047932 | −0.027633 | −0.029265 | −0.033893 | −0.006608 | 0.063257 | 0.030632 | −0.055174 | −0.003576 | 0.009642 | −0.050272 | 0.007733 | −0.033352 |
| 171 | −0.007618 | −0.007917 | −0.01918 | 0.040729 | 0.005967 | −0.039122 | −0.001942 | 0.042914 | −0.032388 | −0.003285 | 0.018299 | −0.043654 | −0.010261 | 0.030003 |
| 172 | −0.011909 | 0.046259 | −0.004342 | 0.015518 | −0.061177 | −0.011695 | 0.018507 | 0.024027 | 0.011682 | 0.039595 | 0.008995 | −0.008228 | 0.0260541 | 0.017981 |
| 173 | 0.032344 | 0.02506 | −0.030261 | −0.013258 | 0.004371 | −0.00684 | 0.028974 | 0.008494 | 0.006972 | −0.020524 | −0.029316 | −0.032945 | 0.003034 | −0.017939 |
| 174 | −0.026085 | 0.027494 | −0.034232 | −0.010141 | −0.020089 | 0.041572 | 0.077825 | −0.009799 | −0.029398 | −0.024471 | −0.054132 | 0.051088 | −0.021958 | −0.021188 |
| 175 | 0.019341 | −0.059407 | 0.014062 | 0.005626 | −0.104832 | 0.006772 | −0.016594 | 0.029199 | 0.054185 | −0.042602 | −0.014561 | −0.01446 | 0.017877 | 0.02351 |
| 176 | −0.020367 | −0.006432 | −0.029958 | 0.043876 | 0.049653 | −0.004271 | −0.037902 | −0.06039 | −0.005955 | 0.022981 | −0.029796 | 0.022929 | 0.041655 | 0.043895 |
| 177 | 0.022184 | 0.000684 | 0.013633 | −0.037951 | 0.03537 | 0.015432 | −0.015232 | −0.045722 | −0.044643 | −0.038594 | −0.004984 | −0.081425 | 0.01698 | 0.031828 |
| 178 | 0.020677 | −0.001011 | 0.001755 | 0.001645 | −0.003856 | 0.021153 | 0.021047 | −0.040974 | −0.009756 | 0.018747 | −0.02453 | −0.032959 | −0.003729 | 0.034878 |
| 179 | 0.000664 | −0.012842 | −0.005082 | −0.012417 | 0.017375 | −0.001987 | 0.035147 | 0.040363 | −0.023891 | 0.026226 | 0.003823 | −0.031017 | 0.018382 | 0.033811 |
| 180 | 0.025478 | −0.030593 | −0.017232 | −0.008184 | 0.022956 | −0.014351 | 0.009628 | −0.003369 | −0.006625 | −0.002551 | 0.00824 | −0.031672 | −0.014619 | 0.003713 |
| 181 | −0.013227 | −0.032907 | −0.038273 | −0.004243 | 0.011956 | −0.01402 | −0.00325 | −0.01695 | −0.01878 | −0.000831 | 0.020137 | −0.02655 | 0.014138 | 0.004343 |
| 182 | 0.007309 | 0.00826 | 0.016084 | −0.066206 | −0.009514 | −0.010101 | 0.035814 | −0.040965 | −0.047799 | 0.0075 | 0.050277 | 0.014105 | 0.019427 | −0.01296 |
| 183 | −0.03837 | 0.015713 | −0.004475 | −0.014586 | 0.009437 | −0.013594 | 0.016434 | −0.002048 | −0.0349 | −0.011934 | 0.038501 | 0.002998 | 0.037113 | 0.01532 |
| 184 | −0.049893 | −0.005897 | −0.040993 | 0.064954 | −0.002168 | −0.017715 | −0.014553 | −0.060531 | 0.023715 | −0.060645 | −0.017847 | 0.010762 | −0.004207 | 0.07336 |
| 185 | −0.000162 | 0.010039 | −0.079492 | 0.033875 | −0.029472 | −0.025655 | −0.000786 | 0.010829 | 0.020316 | −0.000391 | 0.023674 | 0.039959 | −0.012133 | 0.003584 |
| 186 | −0.022823 | −0.045588 | −0.007745 | 0.023247 | 0.009038 | 0.067047 | −0.04155 | 0.021097 | −0.018816 | 0.015553 | −0.025983 | −0.011167 | 0.014924 | −0.054383 |
| 187 | 0.055577 | 0.039976 | −0.018917 | 0.01355 | 0.010415 | −0.005875 | −0.019635 | −0.070514 | −0.010112 | 0.053054 | 0.001948 | −0.000888 | −0.0013181 | −0.011639 |
| 188 | 0.014561 | 0.033868 | 0.003006 | −0.013443 | −0.021523 | −0.017348 | 0.01611 | −0.065804 | −0.016605 | 0.027314 | 0.012392 | 0.008396 | 0.004823 | 0.016906 |
| 189 | 0.005326 | 0.057127 | 0.024585 | −0.013315 | 0.010873 | 0.014184 | −0.043782 | −0.009844 | 0.002683 | 0.037116 | 0.012171 | 0.04677 | 0.009483 | −0.039092 |
| 190 | −0.062897 | 0.019865 | −0.00039 | 0.017977 | −0.004472 | 0.056381 | −0.049666 | −0.021652 | −0.029311 | −0.049167 | −0.024744 | −0.054412 | 0.011717 | 0.036237 |
| 191 | 0.041422 | 0.008676 | −0.017762 | 0.019841 | −0.022858 | −0.036304 | −0.05573 | 0.038893 | 0.016413 | −0.015408 | −0.038327 | −0.033806 | 0.02254 | 0.103874 |
| 192 | 0.070254 | 0.018218 | 0.004698 | −0.013738 | 0.030416 | −0.036077 | 0.010859 | 0.046853 | −0.016868 | −0.065492 | 0.015077 | 0.033338 | 0.003279 | 0.003335 |
| 193 | 0.037835 | 0.007004 | −0.055569 | −0.041743 | 0.010667 | −0.054176 | 0.013367 | −0.042267 | 0.02194 | −0.028948 | −0.020767 | 0.014599 | 0.020069 | 0.029888 |
| 194 | −0.020162 | −0.096413 | −0.009965 | 0.044003 | 0.00418 | 0.002659 | 0.027483 | −0.04942 | 0.049645 | −0.011667 | 0.031825 | −0.037603 | −0.00858 | 0.001931 |
| 195 | 0.034803 | 0.031663 | 0.056929 | −0.023032 | 0.051683 | 0.031349 | −0.024265 | 0.014721 | −0.003285 | −0.076912 | −0.055489 | 0.009066 | 0.007667 | −0.000762 |
| 196 | 0.023038 | 0.010278 | 0.038582 | 0.020477 | 0.013871 | −0.065574 | −0.018588 | −0.004977 | −0.012192 | 0.023092 | −0.043534 | −0.023962 | 0.057994 | 0.025909 |
| 197 | 0.014619 | 0.018843 | −0.059598 | 0.02852 | −0.033344 | −0.033926 | −0.0127 | −0.029149 | −0.040483 | 0.015325 | −0.024177 | 0.00058 | 0.019028 | −0.015242 |
| 198 | 0.049555 | 0.010091 | −0.01657 | 0.015277 | −0.005162 | 0.000712 | 0.047811 | 0.014265 | −0.029415 | 0.047717 | −0.081311 | 0.017116 | −0.034862 | 0.038024 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 199 | −0.018873 | 0.028677 | 0.018804 | −0.004263 | −0.002864 | −0.039463 | −0.046534 | 0.06179 | −0.09637 | 0.038278 | 0.033028 | −0.010901 | −0.010799 | −0.026569 |
| 200 | −0.0077 | 0.014792 | −0.049401 | 0.004068 | 0.012458 | 0.014197 | 0.02496 | 0.024362 | −0.052872 | −0.019993 | 0.013992 | 0.075875 | 0.006753 | −0.030613 |
| 201 | −0.016134 | −0.013408 | 0.007405 | 0.001396 | 0.025095 | −0.01549 | −0.020694 | 0.028529 | 0.07529 | −0.069973 | −0.057782 | 0.003776 | −0.0053 | −0.03238 |
| 202 | −0.041005 | 0.008582 | 0.020345 | −0.006484 | −0.063931 | −0.01247 | 0.007167 | −0.008442 | −0.073765 | 0.053262 | 0.129728 | −0.044887 | −0.000501 | −0.024027 |
| 203 | 0.024459 | 0.01906 | −0.040958 | 0.031502 | −0.008195 | 0.0293 | −0.055811 | 0.027587 | −0.033304 | −0.016001 | −0.046643 | 0.037089 | 0.030727 | −0.029354 |
| 204 | −0.020823 | −0.061177 | 0.026758 | −0.025286 | −0.001621 | 0.039423 | 0.001507 | −0.013584 | −0.047837 | 0.037025 | −0.023156 | 0.028929 | 0.058129 | 0.020111 |
| 205 | −0.048351 | −0.027711 | −0.055521 | −0.038903 | 0.038819 | −0.023172 | −0.009227 | 0.026212 | 0.008741 | 0.056404 | −0.068023 | −0.007424 | −0.061147 | −0.042196 |
| 206 | 0.015942 | 0.012616 | 0.044879 | −0.040669 | 0.0509 | −0.065944 | −0.001809 | −0.068603 | 0.088604 | −0.001431 | −0.021593 | 0.070204 | −0.026925 | −0.023388 |
| 207 | −0.007703 | −0.002325 | −0.00301 | 0.072781 | 0.051462 | 0.017606 | −0.072636 | 0.014855 | 0.032972 | 0.01451 | 0.011425 | −0.014048 | −0.01306 | −0.055963 |
| 208 | −0.006008 | −0.010078 | −0.023065 | 0.030445 | 0.002105 | 0.030334 | 0.017905 | 0.033342 | 0.009924 | 0.009029 | 0.072479 | 0.02553 | 0.006865 | −0.015853 |
| 209 | −0.03435 | 0.002181 | 0.091398 | 0.033805 | −0.044462 | −0.047594 | 0.009454 | −0.015354 | −0.016644 | 0.01698 | −0.092005 | 0.03231 | −0.059806 | 0.029701 |
| 210 | −0.080262 | −0.053642 | −0.033448 | 0.009149 | −0.063916 | −0.015727 | −0.008693 | 0.005305 | 0.038573 | −0.026567 | −0.095201 | −0.068823 | −0.036789 | −0.018612 |
| 211 | 0.046141 | 0.075317 | −0.034292 | −0.020731 | −0.016881 | −0.010897 | 0.040661 | 0.045285 | −0.036852 | 0.03919 | −0.014008 | −0.013728 | 0.092032 | −0.01211 |
| 212 | 0.02987 | −0.014927 | −0.016871 | 0.004399 | −0.02933 | −0.020755 | −0.043259 | −0.013527 | −0.002798 | 0.038756 | 0.037949 | 0.005738 | −0.047468 | 0.01645 |
| 213 | −0.028378 | 0.064105 | 0.056935 | 0.02324 | 0.00262 | −0.003254 | 0.045486 | 0.033023 | −0.046128 | 0.032979 | −0.039478 | 0.056499 | −0.010185 | 0.031517 |
| 214 | 0.042929 | −0.001219 | 0.02367 | −0.010731 | 0.035934 | −0.042604 | −0.002743 | 0.030046 | −0.000502 | 0.011446 | −0.01002 | −0.061841 | 0.010318 | 0.00602 |
| 215 | −0.050174 | 0.072045 | −0.022262 | −0.033855 | 0.023241 | 0.013457 | −0.019963 | −0.039929 | −0.030011 | −0.026951 | 0.003566 | 0.011421 | 0.011421 | −0.011536 |
| 216 | −0.045126 | −0.021726 | 0.006767 | 0.02373 | 0.040832 | 0.019745 | −0.013746 | 0.016816 | 0.006122 | 0.004555 | −0.009943 | 0.006843 | −0.030343 | −0.015483 |
| 217 | −0.062793 | 0.092514 | 0.092365 | 0.006375 | 0.026618 | −0.026121 | 0.015907 | 0.049759 | −0.04019 | 0.020587 | 0.0314 | 0.007752 | −0.023511 | −0.012972 |
| 218 | 0.071289 | 0.002113 | −0.025745 | −0.014644 | 0.040518 | 0.025484 | −0.002935 | 0.041252 | 0.017474 | 0.044659 | −0.036867 | −0.013851 | 0.013072 | −0.005319 |
| 219 | 0.006858 | 0.030293 | −0.043312 | 0.028327 | 0.047239 | −0.013183 | −0.046297 | 0.005008 | −0.029383 | 0.059756 | −0.074542 | −0.035027 | 0.052169 | −0.028528 |
| 220 | 0.019143 | 0.006625 | 0.026972 | −0.014454 | 0.032627 | −0.013464 | 0.005536 | −0.059462 | −0.064573 | 0.060737 | 0.038592 | −0.021089 | −0.015045 | 0.001781 |
| 221 | 0.005305 | −0.033902 | −0.017695 | −0.056046 | 0.005068 | 0.002542 | 0.025803 | 0.055294 | 0.067576 | −0.000601 | 0.027711 | −0.026168 | 0.017461 | 0.035884 |
| 222 | 0.006753 | −0.061896 | 0.041501 | −0.031559 | −0.00022 | −0.004239 | 0.011575 | −0.021944 | −0.002653 | −0.015019 | 0.020766 | −0.031064 | −0.04429 | −0.004391 |
| 223 | −0.005485 | −0.044781 | −0.02567 | −0.018875 | 0.046373 | 0.021356 | 0.031965 | −0.070425 | 0.008054 | −0.021901 | −0.003172 | −0.0379 | −0.043667 | −0.019655 |
| 224 | −0.009145 | −0.013801 | 0.000552 | 0.04028 | 0.044669 | −0.032984 | 0.011781 | −0.011508 | −0.001981 | −0.005095 | 0.011913 | 0.032452 | 0.042793 | −0.03633 |
| 225 | 0.022275 | −0.03428 | 0.007703 | 0.033876 | −0.005536 | 0.004407 | −0.00028 | −0.007241 | 0.037373 | 0.003002 | 0.036054 | 0.023342 | 0.010762 | −0.01101 |
| 226 | 0.010131 | 0.021483 | −0.024976 | −0.024719 | −0.002467 | 0.017604 | 0.009553 | 0.004374 | 0.013828 | −0.014029 | 0.003385 | −0.046003 | −0.005761 | 0.051709 |
| 227 | 0.021783 | −0.011386 | 0.013271 | 0.025097 | 0.025073 | 0.013231 | 0.009552 | 0.014932 | −0.024254 | −0.008266 | −0.048736 | −0.079774 | 0.01577 | −0.004346 |
| 228 | 0.018825 | −0.025302 | 0.003557 | 0.063983 | −0.003051 | 0.104002 | 0.040478 | 0.028507 | 0.016551 | −0.0167 | 0.000781 | −0.017923 | −0.028024 | −0.002282 |
| 229 | −0.052127 | −0.030315 | 0.017139 | 0.005223 | 0.008257 | 0.033383 | −0.002243 | −0.005243 | −0.002928 | 0.004946 | 0.064153 | −0.075879 | 0.003888 | 0.025111 |
| 230 | 0.033017 | −0.022874 | −0.005928 | −0.02532 | 0.027957 | −0.029484 | 0.054569 | 0.012192 | −0.025556 | −0.034216 | 0.005653 | −0.00445 | −0.023781 | −0.030787 |
| 231 | −0.010858 | −0.039058 | −0.015346 | −0.0118 | 0.005466 | 0.006227 | 0.013553 | −0.032101 | −0.022237 | 0.002511 | 0.044046 | 0.098476 | −0.021425 | 0.014672 |
| 232 | −0.014435 | −0.043855 | −0.006814 | 0.011737 | −0.007538 | 0.044834 | −0.080234 | −0.042146 | 0.006889 | −0.025072 | 0.021225 | 0.000264 | 0.019747 | 0.037806 |
| 233 | 0.007499 | 0.043495 | −0.042035 | 0.029175 | 0.010667 | −0.043389 | 0.017839 | −0.030889 | −0.020231 | −0.007104 | 0.028442 | −0.01562 | 0.028762 | 0.068778 |
| 234 | −0.017798 | 0.039875 | −0.023508 | 0.032643 | 0.002605 | −0.031174 | 0.029887 | −0.035987 | −0.033775 | 0.020056 | 0.044686 | 0.015671 | −0.026686 | 0.001916 |
| 235 | −0.019534 | −0.049358 | −0.008763 | −0.000126 | 0.024587 | 0.04574 | −0.062157 | 0.039713 | 0.060798 | 0.017424 | −0.029988 | −0.06875 | −0.036436 | 0.014575 |
| 236 | 0.05854 | 0.023696 | −0.02001 | −0.010668 | 0.001303 | 0.007328 | 0.03288 | −0.001817 | −0.008037 | −0.045756 | −0.002545 | 0.044938 | 0.002997 | 0.002121 |
| 237 | −0.01954 | −0.031721 | −0.00275 | 0.026099 | 0.012429 | −0.032312 | −0.013189 | 0.020033 | 0.01415 | 0.0031 | −0.018304 | −0.036784 | −0.050833 | −0.037991 |
| 238 | −0.035171 | −0.010015 | 0.012506 | 0.000005 | 0.000945 | −0.058378 | −0.013457 | 0.00917 | −0.016209 | −0.051669 | 0.006406 | −0.017001 | 0.032941 | −0.053331 |
| 239 | −0.006746 | −0.02009 | 0.017672 | −0.012029 | −0.001582 | −0.019897 | −0.033737 | 0.035914 | 0.01607 | −0.012787 | −0.015324 | 0.046489 | 0.009675 | 0.020053 |
| 240 | −0.05243 | 0.043468 | 0.023644 | −0.013864 | 0.044071 | 0.003688 | −0.009528 | 0.050267 | 0.003839 | −0.025905 | 0.011256 | −0.034626 | 0.02218 | 0.043859 |
| 241 | 0.041242 | 0.011372 | 0.024127 | 0.02928 | −0.022138 | 0.022386 | −0.002031 | −0.007809 | 0.008766 | 0.013299 | −0.025566 | 0.079342 | −0.029573 | −0.006133 |
| 242 | 0.023378 | −0.025732 | 0.02278 | −0.033632 | 0.017713 | 0.013689 | 0.007564 | −0.056431 | 0.00149 | 0.004696 | 0.037162 | −0.031757 | 0.012709 | −0.007806 |
| 243 | −0.034302 | −0.040151 | −0.059145 | −0.003432 | −0.031866 | −0.034494 | −0.023139 | −0.045528 | −0.048658 | −0.020565 | −0.027807 | −0.003387 | −0.014838 | 0.003935 |
| 244 | 0.0081 | −0.008213 | −0.038833 | −0.006058 | −0.046743 | 0.032624 | 0.011702 | 0.021794 | 0.039997 | −0.007739 | 0.021323 | 0.053935 | −0.005242 | 0.054108 |
| 245 | 0.048673 | 0.007203 | −0.014952 | 0.005894 | −0.031736 | −0.048548 | 0.035092 | 0.047548 | 0.024666 | 0.028866 | 0.026346 | 0.018561 | 0.022641 | 0.042897 |
| 246 | 0.025253 | −0.019436 | 0.01724 | −0.008692 | −0.02317 | −0.047251 | 0.014127 | −0.033664 | −0.054964 | 0.03298 | −0.013954 | −0.033514 | −0.011777 | −0.025836 |
| 247 | 0.000161 | 0.020744 | −0.004185 | 0.012498 | −0.043635 | 0.013947 | −0.023059 | −0.050846 | −0.048811 | −0.032686 | 0.012558 | 0.042199 | −0.002175 | −0.01464 |
| 248 | −0.002949 | 0.010872 | −0.062692 | −0.00389 | −0.048459 | 0.051156 | −0.056414 | −0.01535 | −0.018182 | −0.029281 | 0.033152 | 0.061274 | −0.02443 | −0.009334 |
| 249 | −0.026058 | −0.003842 | −0.018039 | 0.013801 | −0.017685 | 0.011958 | 0.007684 | −0.030257 | −0.039548 | −0.044955 | −0.045589 | −0.011287 | 0.01051 | −0.022375 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 250 | 0.0356 | 0.042941 | 0.034941 | 0.014801 | −0.011706 | −0.052443 | −0.008805 | −0.016934 | 0.020973 | −0.00686 | −0.004146 | 0.028167 | 0.012083 | −0.022145 |
| 251 | 0.00091 | −0.006206 | 0.029229 | −0.033475 | 0.004776 | −0.036469 | 0.005392 | 0.021711 | 0.062401 | −0.007966 | −0.021773 | −0.021468 | 0.003738 | −0.01175 |
| 252 | 0.010396 | −0.01895 | −0.009103 | 0.016042 | 0.002342 | −0.003189 | 0.045317 | 0.046973 | −0.021508 | 0.027615 | 0.009145 | −0.023098 | −0.011306 | 0.008849 |
| 253 | 0.009392 | −0.009809 | −0.002368 | 0.015282 | −0.009366 | −0.036149 | −0.006389 | 0.012606 | −0.020118 | −0.023071 | −0.061994 | 0.023302 | −0.019775 | −0.011068 |
| 254 | −0.056314 | −0.01022 | −0.080664 | 0.024742 | −0.075637 | 0.041499 | −0.008563 | 0.035901 | 0.049918 | −0.013716 | −0.017021 | 0.008333 | −0.010953 | −0.014256 |
| 255 | −0.022034 | 0.009172 | −0.025477 | −0.022818 | −0.027176 | 0.028505 | 0.034836 | 0.027795 | 0.00555 | −0.001049 | −0.014731 | 0.042516 | −0.000112 | −0.025691 |
| 256 | 0.000985 | 0.005549 | 0.021511 | 0.016401 | −0.022432 | −0.015561 | 0.043732 | 0.014989 | 0.040622 | 0.001788 | 0.009391 | −0.039008 | 0.011996 | −0.028141 |
| 257 | −0.015119 | −0.018487 | 0.035094 | 0.02151 | −0.017903 | −0.000973 | −0.034651 | −0.000207 | 0.02252 | −0.024014 | 0.010306 | 0.00989 | 0.033541 | 0.02598 |
| 258 | 0.002061 | 0.002556 | 0.024146 | −0.030014 | −0.061734 | 0.064384 | −0.03816 | 0.040722 | 0.008746 | 0.000246 | 0.022608 | 0.063053 | −0.038787 | 0.050846 |
| 259 | 0.034697 | 0.001451 | −0.00664 | 0.001524 | 0.012692 | 0.045868 | 0.002666 | −0.041252 | −0.028073 | 0.007773 | 0.005081 | −0.013945 | 0.02286 | −0.005354 |
| 260 | 0.027437 | 0.00909 | −0.046774 | 0.076534 | −0.004861 | 0.004149 | 0.040349 | 0.014173 | −0.028336 | 0.099881 | 0.046404 | −0.019847 | −0.014262 | 0.031844 |
| 261 | −0.070989 | 0.059871 | 0.025848 | 0.00696 | 0.000009 | −0.006574 | 0.047711 | 0.046577 | 0.007406 | 0.012265 | 0.0243 | −0.074274 | 0.036773 | −0.016471 |
| 262 | −0.030986 | −0.014669 | 0.073235 | −0.019562 | 0.034517 | −0.031205 | 0.018354 | −0.00007 | 0.041166 | −0.036083 | 0.010674 | −0.054955 | 0.01151 | 0.013029 |
| 263 | −0.02384 | −0.016162 | 0.023471 | 0.029836 | 0.035367 | −0.080147 | 0.00582 | −0.004381 | 0.059038 | −0.008193 | −0.026801 | −0.029173 | 0.031942 | −0.012826 |
| 264 | −0.022328 | 0.007578 | 0.024915 | 0.042956 | −0.012623 | 0.034284 | −0.031253 | −0.045971 | −0.06718 | 0.01248 | −0.026756 | 0.013111 | −0.047126 | 0.033737 |
| 265 | 0.00071 | 0.019579 | 0.037421 | 0.007359 | 0.027825 | 0.048498 | −0.038947 | −0.014509 | −0.032976 | 0.005798 | −0.00184 | 0.035443 | −0.061462 | 0.039698 |
| 266 | 0.032966 | 0.041958 | 0.001385 | 0.00843 | 0.031465 | −0.012832 | 0.000807 | 0.025144 | 0.015241 | −0.016506 | 0.026308 | −0.003531 | 0.009434 | −0.06903 |
| 267 | −0.007767 | −0.048454 | −0.020522 | 0.015708 | 0.024189 | −0.014028 | −0.032831 | −0.02482 | −0.028015 | 0.02205 | −0.00374 | −0.035541 | −0.00428 | 0.031084 |
| 268 | 0.006985 | −0.002258 | −0.001325 | 0.010039 | 0.028054 | 0.037677 | −0.018949 | 0.015859 | −0.008578 | 0.003782 | −0.014691 | 0.015903 | −0.006175 | 0.037681 |
| 269 | 0.012746 | −0.01298 | −0.00306 | 0.004235 | 0.011185 | 0.039653 | −0.001394 | −0.015887 | 0.016241 | −0.029383 | −0.009318 | 0.000831 | −0.023154 | 0.014102 |
| 270 | 0.009646 | 0.019357 | −0.01231 | −0.011651 | −0.014311 | 0.012896 | 0.019176 | 0.003537 | 0.008631 | −0.003314 | −0.017643 | 0.005718 | −0.028356 | 0.018486 |
| 271 | 0.038466 | −0.003302 | 0.005988 | −0.024267 | −0.023424 | −0.047607 | −0.025521 | −0.028697 | −0.014978 | 0.03492 | −0.029728 | 0.048364 | 0.013585 | −0.041276 |
| 272 | 0.005023 | 0.043066 | 0.004334 | −0.014921 | −0.024065 | −0.030749 | 0.018317 | −0.005607 | −0.019921 | −0.002024 | −0.055641 | 0.054293 | 0.003931 | 0.014958 |
| 273 | −0.022413 | 0.05014 | 0.017879 | −0.003147 | −0.020755 | 0.037328 | 0.019403 | −0.00418 | −0.039819 | 0.017843 | 0.027616 | 0.029015 | 0.007074 | 0.03375 |
| 274 | −0.019512 | 0.047483 | 0.024918 | 0.000063 | −0.011966 | 0.033414 | 0.024164 | −0.012312 | −0.015288 | 0.019218 | 0.010795 | 0.020054 | 0.002284 | 0.014339 |
| 275 | 0.026587 | 0.037627 | −0.042417 | 0.001479 | −0.043432 | −0.027952 | 0.017833 | −0.014423 | −0.063848 | −0.015946 | −0.019981 | 0.002511 | −0.049921 | −0.031687 |
| 276 | 0.033012 | −0.00659 | −0.001936 | 0.005458 | 0.025484 | −0.011928 | 0.002644 | 0.009979 | 0.061374 | −0.013493 | −0.036601 | 0.02857 | 0.026412 | 0.03035 |
| 277 | 0.001203 | 0.009239 | 0.036314 | 0.014103 | 0.033595 | 0.049798 | 0.015075 | 0.019992 | 0.027938 | −0.009731 | −0.017696 | 0.011292 | −0.02789 | 0.010237 |
| 278 | −0.03611 | 0.054305 | −0.017066 | 0.006335 | 0.014513 | 0.039242 | 0.011029 | −0.002157 | 0.00296 | 0.001863 | 0.010633 | 0.034678 | 0.021476 | −0.015698 |
| 279 | −0.000475 | 0.012296 | −0.010012 | −0.022507 | 0.028499 | −0.002413 | −0.024867 | 0.007777 | −0.008591 | −0.003963 | 0.000019 | 0.021321 | 0.039526 | 0.00232 |
| 280 | −0.01356 | −0.012621 | 0.032898 | −0.024792 | 0.01366 | −0.099851 | 0.033386 | 0.004453 | 0.049378 | −0.004897 | −0.005035 | −0.009451 | −0.008624 | 0.00397 |
| 281 | −0.003589 | −0.027624 | 0.011865 | −0.033829 | −0.000333 | −0.038325 | 0.00131 | −0.0436 | 0.028472 | 0.01484 | 0.005526 | −0.04785 | 0.005989 | 0.008677 |
| 282 | 0.009416 | 0.012441 | −0.044056 | 0.001009 | −0.027218 | −0.035419 | −0.000214 | −0.107784 | −0.042038 | −0.01173 | −0.01168 | −0.002618 | 0.0151 | −0.00983 |
| 283 | 0.015214 | 0.019795 | −0.065123 | 0.003526 | −0.024518 | −0.04193 | −0.033599 | −0.070073 | −0.008847 | −0.009078 | −0.016658 | 0.015547 | 0.007521 | −0.009557 |
| 284 | −0.013523 | 0.002342 | 0.031362 | 0.018495 | −0.004032 | −0.002404 | −0.0193 | −0.015102 | 0.021046 | −0.010524 | 0.015688 | −0.007732 | 0.028408 | −0.001612 |
| 285 | −0.029305 | 0.014491 | 0.009513 | 0.032682 | 0.012302 | 0.009692 | 0.005412 | −0.068909 | −0.034659 | −0.032347 | −0.041096 | 0.062465 | 0.015838 | −0.038448 |
| 286 | 0.027269 | −0.000926 | 0.011505 | −0.016258 | −0.001472 | −0.033947 | −0.038021 | 0.001655 | 0.043167 | 0.023665 | 0.024619 | 0.016457 | −0.016547 | 0.027521 |
| 287 | 0.000045 | 0.001966 | −0.019039 | 0.004143 | −0.022651 | −0.042114 | −0.014376 | −0.007194 | 0.048057 | 0.042364 | 0.006762 | 0.008801 | −0.006679 | −0.028183 |
| 288 | 0.031094 | 0.008013 | −0.040092 | 0.001155 | −0.001522 | 0.071911 | −0.032937 | 0.030295 | 0.045384 | 0.052603 | −0.022296 | −0.02644 | −0.035873 | −0.033644 |
| 289 | 0.030947 | 0.017816 | 0.029296 | −0.021424 | 0.018208 | 0.009314 | −0.012936 | −0.021394 | 0.008295 | −0.013267 | 0.01593 | −0.025664 | 0.007649 | 0.009819 |
| 290 | −0.002037 | −0.015813 | −0.048605 | 0.013633 | −0.020247 | 0.029935 | 0.021903 | 0.006956 | −0.011081 | −0.009303 | 0.040376 | 0.024948 | 0.026795 | −0.007747 |
| 291 | −0.010121 | −0.019863 | −0.037883 | 0.02266 | −0.02582 | 0.028081 | 0.010218 | 0.011332 | 0.005704 | −0.010599 | 0.045511 | 0.009052 | 0.034761 | −0.007108 |
| 292 | 0.018151 | −0.029021 | −0.024537 | −0.001028 | −0.007457 | −0.01603 | 0.001005 | 0.013194 | −0.001528 | −0.049545 | −0.000583 | 0.060271 | −0.013414 | −0.015266 |
| 293 | 0.004557 | −0.00315 | −0.064255 | −0.048915 | 0.024316 | 0.034418 | 0.020111 | 0.042637 | −0.004057 | 0.015548 | 0.003416 | −0.025838 | 0.035825 | 0.080338 |
| 294 | 0.011917 | 0.022717 | −0.033506 | 0.022438 | −0.040555 | 0.018948 | −0.00271 | 0.059817 | 0.052698 | 0.029069 | −0.017616 | 0.056926 | −0.048893 | 0.017603 |
| 295 | 0.002638 | −0.012512 | 0.006938 | 0.006393 | 0.024615 | −0.016131 | −0.007381 | 0.023327 | 0.015096 | 0.033536 | −0.001734 | −0.037315 | 0.032481 | −0.005973 |
| 296 | 0.020781 | 0.003735 | 0.019898 | 0.006926 | −0.020159 | 0.00582 | −0.041858 | −0.014979 | 0.050019 | −0.041979 | 0.008996 | −0.006019 | −0.043965 | 0.002569 |
| 297 | 0.010197 | −0.015998 | 0.005375 | −0.011681 | 0.043162 | −0.01401 | 0.003743 | 0.007059 | 0.028185 | 0.030629 | 0.017207 | −0.040383 | −0.007505 | 0.035159 |
| 298 | −0.053398 | 0.056619 | 0.024242 | −0.012666 | −0.034695 | 0.018289 | −0.008229 | −0.004624 | 0.004774 | 0.038353 | 0.006819 | 0.001564 | 0.052422 | 0.03456 |
| 299 | 0.006656 | −0.029362 | −0.028596 | −0.023082 | −0.024373 | −0.0204 | 0.009283 | −0.011696 | 0.010817 | 0.021139 | 0.020837 | −0.004387 | 0.009632 | 0.025065 |
| 300 | −0.018789 | −0.00236 | 0.022179 | −0.014705 | −0.012585 | 0.019504 | 0.044108 | 0.041406 | 0.04387 | −0.000585 | −0.016077 | 0.000265 | −0.072 | 0.055861 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 301 | −0.023466 | −0.018658 | −0.011657 | 0.00691 | 0.011342 | 0.002988 | −0.007817 | −0.029068 | −0.003287 | −0.000823 | −0.000084 | 0.033003 | 0.022679 | −0.032217 |
| 302 | −0.009603 | −0.02419 | 0.056421 | −0.027119 | 0.001673 | 0.030945 | 0.038967 | −0.01422 | 0.002607 | 0.029816 | −0.021591 | 0.022126 | 0.018432 | −0.014974 |
| 303 | −0.003205 | 0.0354 | 0.007955 | −0.021118 | −0.05048 | 0.059578 | 0.020909 | −0.051565 | −0.032809 | 0.008837 | 0.007492 | 0.047202 | 0.019763 | −0.015577 |
| 304 | 0.025716 | 0.035145 | 0.008296 | −0.037062 | −0.00649 | 0.002708 | 0.027388 | 0.023825 | 0.036826 | 0.022954 | −0.013562 | −0.012177 | 0.017113 | −0.0119 |
| 305 | −0.003709 | 0.00099 | −0.07277 | 0.005871 | 0.015978 | −0.06973 | −0.046254 | −0.029366 | −0.014437 | −0.01786 | −0.037931 | 0.004118 | 0.00475 | −0.025438 |
| 306 | −0.033732 | −0.033335 | 0.015957 | −0.023033 | −0.027969 | 0.074435 | 0.023063 | 0.0154 | −0.010707 | 0.027314 | −0.026121 | 0.049885 | 0.059443 | −0.017631 |
| 307 | −0.035192 | −0.001048 | −0.018309 | −0.005277 | 0.036746 | 0.018335 | 0.011266 | −0.021645 | −0.036802 | 0.001384 | −0.009479 | −0.084077 | 0.047194 | 0.010195 |
| 308 | 0.053951 | −0.01195 | −0.026596 | −0.013637 | 0.0123 | −0.053382 | 0.045984 | 0.019255 | −0.007458 | −0.004249 | −0.004231 | 0.037278 | 0.037593 | −0.00575 |
| 309 | −0.009219 | −0.02398 | −0.012461 | 0.009431 | 0.01243 | −0.051932 | 0.044175 | 0.007019 | −0.038181 | −0.026959 | −0.006572 | −0.013891 | 0.001248 | −0.026577 |
| 310 | −0.007663 | 0.02746 | −0.015338 | 0.02283 | 0.029073 | −0.005317 | 0.06178 | −0.012793 | −0.018381 | −0.075323 | 0.021758 | 0.037256 | 0.057615 | −0.038994 |
| 311 | −0.03321 | −0.020952 | 0.004313 | −0.010876 | 0.002185 | 0.065739 | 0.011079 | 0.011609 | −0.041862 | 0.033792 | 0.005337 | −0.045739 | 0.019991 | 0.061254 |
| 312 | −0.052033 | 0.074115 | 0.00838 | −0.020796 | 0.049243 | 0.01573 | 0.041364 | 0.009636 | 0.030451 | 0.028387 | −0.015365 | 0.009446 | −0.030548 | 0.005472 |
| 313 | −0.033484 | −0.00772 | −0.055049 | 0.020564 | 0.005492 | −0.006612 | −0.003088 | 0.024258 | −0.035477 | −0.006394 | 0.027124 | 0.001649 | 0.015447 | −0.041619 |
| 314 | 0.048262 | −0.062847 | 0.039135 | −0.005625 | 0.034068 | 0.10762 | −0.056677 | 0.058858 | −0.051933 | −0.002175 | 0.011828 | −0.027158 | 0.038579 | −0.016161 |
| 315 | −0.014411 | −0.040606 | −0.008597 | −0.002916 | 0.044254 | −0.022041 | −0.005608 | −0.004947 | 0.048914 | 0.010349 | 0.032037 | −0.04018 | −0.009606 | −0.043795 |
| 316 | −0.024429 | 0.029424 | −0.019741 | 0.023561 | −0.042457 | 0.037875 | −0.00706 | 0.023472 | −0.022308 | −0.029172 | 0.035285 | −0.01534 | −0.016461 | 0.044086 |
| 317 | −0.02139 | −0.052437 | −0.04002 | 0.041306 | 0.023532 | −0.033492 | −0.061017 | −0.021977 | −0.006332 | 0.008371 | 0.003673 | −0.014682 | 0.029138 | 0.001866 |
| 318 | 0.00498 | −0.002154 | −0.03572 | 0.026866 | −0.03414 | −0.005005 | −0.030066 | 0.025124 | 0.007548 | 0.033673 | 0.038024 | 0.060506 | −0.006265 | 0.062729 |
| 319 | 0.012866 | −0.03542 | −0.043134 | 0.044875 | 0.013682 | −0.063141 | −0.016199 | −0.013029 | 0.024114 | 0.032219 | 0.051756 | 0.017258 | 0.016612 | 0.021051 |
| 320 | 0.0799 | −0.017516 | 0.066792 | −0.00198 | 0.003977 | 0.095274 | −0.024498 | −0.068543 | −0.05115 | 0.039762 | −0.038199 | −0.016987 | −0.017794 | 0.02259 |
| 321 | 0.04723 | −0.052134 | 0.005004 | 0.00777 | −0.012413 | 0.021153 | −0.011745 | −0.030401 | −0.050098 | 0.022824 | −0.026416 | −0.025682 | −0.03841 | 0.002405 |
| 322 | 0.046023 | −0.003077 | 0.041106 | −0.027928 | 0.02885 | 0.048911 | 0.05002 | −0.045664 | 0.014115 | −0.02003 | 0.049485 | −0.026558 | −0.014311 | 0.035234 |
| 323 | −0.043996 | 0.06115 | 0.005 | −0.017297 | −0.02407 | −0.024306 | −0.007324 | 0.025649 | −0.038673 | −0.03343 | 0.019874 | −0.028712 | 0.005203 | −0.104471 |
| 324 | 0.061865 | −0.015171 | −0.012715 | 0.02149 | 0.028625 | −0.020658 | 0.004401 | −0.071827 | −0.017574 | 0.054224 | 0.04002 | −0.050163 | −0.051948 | 0.040083 |
| 325 | 0.003156 | 0.01898 | 0.02597 | −0.019219 | 0.010869 | 0.025662 | 0.060176 | 0.003045 | 0.022258 | −0.044103 | 0.031728 | −0.020818 | −0.014048 | 0.006751 |
| 326 | −0.039808 | −0.034482 | 0.006075 | −0.016156 | −0.003688 | −0.016009 | −0.079509 | −0.037722 | −0.014485 | 0.038304 | 0.016058 | 0.04785 | 0.087411 | −0.048846 |
| 327 | −0.004607 | −0.063374 | −0.014944 | −0.01421 | −0.008922 | −0.016508 | 0.015113 | −0.011982 | −0.02251 | −0.002877 | −0.036998 | −0.01404 | 0.002266 | −0.014141 |
| 328 | −0.050987 | 0.03268 | −0.013629 | −0.044991 | 0.013968 | 0.003612 | −0.017043 | −0.012078 | −0.018814 | −0.007041 | −0.018036 | 0.007349 | 0.014339 | −0.019339 |
| 329 | 0.046596 | −0.064464 | −0.028313 | −0.009191 | 0.002516 | −0.042094 | 0.004556 | 0.002205 | −0.005192 | 0.012636 | −0.044488 | 0.001831 | −0.043409 | 0.037664 |
| 330 | 0.041364 | −0.014465 | 0.009468 | 0.003479 | 0.061957 | −0.036528 | −0.054078 | −0.003456 | 0.006885 | −0.003642 | −0.009472 | 0.018128 | −0.046108 | −0.03754 |
| 331 | −0.016489 | 0.05592 | 0.027627 | −0.002959 | 0.005072 | 0.0174 | −0.000685 | −0.000574 | 0.023117 | 0.032987 | −0.021664 | −0.04202 | 0.027771 | −0.055976 |
| 332 | −0.059165 | −0.003479 | 0.004741 | 0.002264 | −0.031675 | −0.038977 | 0.052782 | 0.071483 | −0.06564 | 0.025893 | 0.017438 | −0.04576 | −0.029915 | −0.010484 |
| 333 | −0.019693 | 0.010811 | −0.034391 | −0.001383 | −0.014636 | −0.024297 | 0.016649 | −0.013341 | 0.017126 | −0.033253 | 0.024629 | 0.045061 | −0.011362 | 0.038453 |
| 334 | −0.023581 | −0.011164 | 0.00426 | −0.034619 | 0.048278 | −0.032615 | −0.00553 | −0.007403 | 0.026982 | −0.009994 | 0.07914 | −0.008114 | −0.051289 | 0.029796 |
| 335 | 0.030852 | 0.02368 | −0.069615 | 0.001177 | 0.020923 | −0.025382 | 0.042316 | −0.002476 | −0.027363 | 0.012053 | −0.047142 | 0.044331 | 0.058116 | −0.036761 |
| 336 | 0.023192 | −0.008952 | 0.009225 | 0.053647 | −0.001326 | −0.046429 | −0.007437 | −0.021787 | 0.040009 | 0.000554 | 0.028944 | −0.053419 | −0.017843 | 0.005147 |
| 337 | −0.015888 | 0.031538 | 0.010438 | −0.019578 | −0.025368 | 0.016089 | 0.015 | −0.034733 | 0.049262 | 0.030767 | −0.053201 | 0.013628 | −0.050564 | 0.047408 |
| 338 | 0.058053 | 0.007512 | −0.054361 | 0.035789 | −0.010325 | 0.018343 | −0.012884 | 0.039974 | −0.027704 | 0.030898 | −0.012801 | 0.008968 | 0.017122 | 0.039832 |
| 339 | 0.02937 | 0.007282 | 0.074625 | −0.01755 | 0.005292 | −0.04868 | 0.041111 | 0.060424 | −0.045752 | 0.106902 | 0.004904 | −0.012885 | −0.013821 | −0.002067 |
| 340 | −0.031093 | 0.02982 | −0.010314 | 0.050878 | 0.013835 | 0.05131 | −0.029808 | 0.014947 | 0.065561 | −0.051759 | −0.006319 | −0.022447 | 0.000691 | 0.007657 |

| | FJ | FK | FL | FM | FN | FO | FP | FQ | FR | FS | FT | FU | FV | FW |
|---|---|---|---|---|---|---|---|---|---|---|---|---|---|---|
| 1 | 0.023462 | 0.096439 | −0.002798 | −0.15481 | 0.096468 | 0.004466 | 0.06897 | 0.09146 | 0.043585 | 0.007402 | −0.034853 | 0.054584 | −0.008101 | −0.049715 |
| 2 | −0.003032 | 0.030986 | 0.037479 | −0.029114 | 0.029629 | 0.010724 | −0.01362 | 0.02909 | −0.049231 | −0.02455 | −0.03213 | 0.039738 | 0.20402 | 0.018423 |
| 3 | 0.062022 | 0.004045 | 0.048445 | 0.053427 | −0.059692 | −0.075952 | −0.031829 | 0.008567 | 0.022096 | −0.049252 | −0.039585 | 0.032325 | −0.059801 | 0.013418 |
| 4 | −0.013093 | 0.024845 | 0.125791 | −0.06478 | 0.014366 | 0.06664 | 0.0171 | −0.024656 | −0.013158 | −0.045716 | −0.010864 | −0.058458 | 0.001072 | −0.050573 |
| 5 | 0.029227 | −0.059184 | −0.028608 | 0.011002 | −0.001424 | 0.015207 | −0.015648 | 0.016363 | 0.0081911 | 0.014991 | −0.002273 | 0.01802 | −0.025458 | −0.076217 |
| 6 | 0.035292 | −0.083076 | 0.031254 | 0.095365 | −0.015064 | −0.019899 | −0.01494 | −0.000995 | −0.000489 | −0.076098 | −0.017229 | −0.013395 | −0.018707 | 0.012527 |
| 7 | −0.053355 | 0.019796 | 0.114879 | −0.033323 | −0.042693 | −0.057967 | −0.040144 | −0.020104 | 0.04404 | 0.035024 | −0.019528 | −0.007513 | 0.017244 | −0.031463 |
| 8 | −0.004603 | −0.003176 | −0.077436 | −0.014416 | −0.022503 | −0.033674 | 0.010394 | −0.019943 | 0.029755 | 0.039353 | −0.00153 | −0.084365 | 0.049153 | −0.005765 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 9 | −0.062629 | −0.030968 | −0.12182 | 0.054876 | −0.005988 | 0.016772 | 0.047452 | −0.011096 | −0.009591 | 0.006199 | 0.046516 | 0.06107 | −0.08086 | −0.020948 |
| 10 | 0.042418 | −0.070184 | 0.030793 | 0.098321 | −0.045046 | −0.005392 | −0.000174 | 0.00147 | −0.006592 | 0.064128 | 0.033831 | 0.116626 | 0.019935 | −0.005754 |
| 11 | −0.041274 | 0.052242 | 0.035529 | 0.079327 | 0.004782 | −0.014433 | 0.006627 | 0.00922 | −0.042928 | −0.030532 | 0.007857 | 0.026455 | 0.004929 | −0.013741 |
| 12 | −0.044087 | −0.047341 | 0.011137 | −0.009799 | 0.027763 | 0.033953 | 0.050509 | 0.0029 | −0.01158 | 0.051312 | 0.011482 | 0.029415 | 0.001544 | 0.008163 |
| 13 | 0.071604 | 0.013067 | −0.006688 | −0.076751 | −0.061288 | −0.130427 | −0.13287 | −0.059029 | −0.075526 | −0.069189 | 0.01073 | 0.009175 | −0.088755 | −0.031847 |
| 14 | −0.063449 | −0.035613 | 0.153472 | 0.065557 | −0.007048 | 0.024403 | −0.035841 | 0.024119 | −0.019188 | 0.016374 | 0.062916 | 0.015426 | 0.066675 | 0.031758 |
| 15 | 0.010785 | −0.048684 | −0.119625 | −0.03889 | 0.027964 | 0.05131 | −0.012077 | −0.027606 | −0.016372 | −0.006236 | −0.032522 | −0.144915 | 0.019688 | −0.004408 |
| 16 | −0.007894 | −0.013218 | −0.028781 | 0.027814 | 0.014466 | 0.046233 | −0.002424 | −0.045477 | 0.020853 | 0.014405 | 0.031022 | −0.028905 | 0.105972 | −0.026166 |
| 17 | −0.079209 | 0.050981 | −0.029853 | 0.090029 | 0.011014 | 0.010532 | 0.038444 | −0.005945 | 0.017445 | 0.079701 | 0.002088 | −0.022436 | 0.035577 | 0.067598 |
| 18 | −0.017716 | −0.0945 | 0.033882 | −0.003674 | −0.037023 | −0.029823 | 0.015752 | −0.00525 | 0.070566 | 0.038586 | −0.048897 | −0.039993 | 0.019295 | 0.021327 |
| 19 | −0.038088 | −0.068942 | 0.026295 | −0.040645 | −0.021538 | −0.007357 | −0.031481 | −0.009253 | −0.016754 | −0.009992 | −0.014312 | −0.020981 | −0.029111 | 0.005277 |
| 20 | 0.080145 | 0.038341 | −0.114427 | 0.073075 | 0.049544 | 0.030482 | 0.033952 | 0.039332 | 0.021332 | −0.047703 | −0.096449 | 0.027464 | −0.094842 | 0.02209 |
| 21 | 0.044074 | 0.051266 | 0.016081 | −0.068531 | 0.020786 | 0.00626 | 0.053514 | −0.027755 | 0.046807 | 0.038127 | 0.032973 | −0.047013 | −0.041589 | −0.053947 |
| 22 | 0.016007 | 0.01569 | −0.066887 | −0.031234 | −0.037507 | −0.039031 | −0.055972 | −0.01552 | −0.100823 | −0.091783 | −0.037201 | 0.053772 | 0.002859 | −0.023915 |
| 23 | 0.028761 | 0.006826 | −0.096663 | 0.049415 | 0.044984 | 0.021889 | −0.020611 | 0.061691 | 0.002462 | −0.057273 | 0.024463 | −0.005946 | −0.095576 | −0.055357 |
| 24 | −0.040105 | 0.024401 | −0.026503 | 0.068834 | 0.024526 | 0.04467 | 0.02102 | −0.020376 | 0.014524 | −0.019581 | 0.094704 | −0.044525 | 0.003887 | −0.004726 |
| 25 | −0.035768 | −0.0621 | −0.019566 | −0.086414 | 0.024165 | 0.060711 | 0.042766 | −0.015091 | 0.033016 | 0.05171 | −0.037081 | −0.072025 | 0.008948 | 0.031591 |
| 26 | 0.054871 | 0.070638 | 0.148259 | −0.026386 | −0.091731 | −0.062254 | −0.043037 | −0.021288 | 0.075357 | 0.036887 | −0.1787 | −0.070737 | −0.084059 | −0.042455 |
| 27 | −0.035511 | 0.032995 | −0.044834 | 0.004487 | −0.042325 | −0.02681 | −0.090087 | 0.101979 | 0.070369 | 0.130544 | 0.291536 | 0.07212 | −0.036974 | −0.022515 |
| 28 | 0.258806 | 0.024121 | 0.062596 | 0.081853 | 0.049496 | 0.060931 | 0.021775 | −0.043276 | −0.00184 | 0.005997 | 0.114621 | −0.005079 | −0.038582 | −0.010653 |
| 29 | −0.055781 | −0.053772 | −0.032206 | 0.006481 | −0.033626 | −0.033401 | −0.088531 | −0.064014 | −0.026539 | 0.018583 | −0.028385 | −0.080042 | −0.009193 | −0.054139 |
| 30 | 0.008519 | −0.077443 | 0.038891 | −0.032623 | −0.014967 | −0.007055 | 0.016067 | −0.050653 | 0.015858 | 0.096791 | 0.011742 | −0.03143 | 0.09207 | 0.03564 |
| 31 | −0.02762 | 0.061644 | −0.040555 | 0.131383 | −0.032741 | −0.007782 | 0.04734 | −0.009928 | −0.052311 | −0.068526 | −0.064882 | 0.075012 | 0.141136 | −0.013335 |
| 32 | −0.071009 | 0.002123 | 0.040327 | −0.093029 | −0.014314 | 0.006027 | 0.008137 | 0.028239 | 0.077969 | −0.036037 | −0.090292 | 0.014563 | 0.004694 | −0.004258 |
| 33 | 0.001905 | 0.072685 | 0.006165 | −0.169074 | −0.000127 | −0.044186 | −0.010083 | −0.032997 | −0.053306 | 0.031195 | 0.056148 | −0.033316 | −0.044617 | −0.01248 |
| 34 | 0.063505 | −0.016158 | 0.178412 | 0.072669 | 0.053423 | 0.028644 | 0.00711 | 0.016165 | 0.036075 | 0.066544 | −0.002806 | −0.060707 | −0.026218 | −0.003561 |
| 35 | −0.028087 | 0.023332 | −0.022585 | 0.01959 | 0.01134 | 0.029411 | −0.034676 | 0.019081 | 0.030423 | 0.049668 | 0.0322881 | 0.087884 | 0.012244 | 0.002109 |
| 36 | 0.004281 | −0.072401 | −0.077626 | −0.043242 | 0.047157 | 0.035419 | 0.048442 | −0.007736 | −0.058873 | 0.00722 | −0.056844 | 0.09083 | −0.104856 | 0.027334 |
| 37 | −0.022226 | −0.074173 | 0.065057 | −0.126818 | 0.043248 | 0.067607 | 0.067178 | 0.087483 | 0.049736 | 0.007162 | 0.152366 | 0.010966 | 0.078044 | −0.011008 |
| 38 | −0.011508 | −0.060035 | 0.150208 | 0.020514 | −0.050233 | −0.058214 | 0.006043 | 0.011109 | 0.063463 | 0.035759 | −0.02666 | −0.012364 | −0.056193 | −0.000915 |
| 39 | −0.079796 | 0.141834 | −0.006699 | −0:04397 | 0.038599 | 0.080483 | 0.024359 | −0.052716 | −0.028367 | −0.057307 | −0.079677 | 0.036452 | 0.008309 | 0.035634 |
| 40 | 0.065059 | −0.017856 | −0.023515 | 0.047473 | −0.058195 | −0.088778 | −0.076446 | 0.05965 | 0.058726 | 0.019588 | 0.0501 | −0.040725 | −0.102576 | −0.09784 |
| 41 | 0.194904 | 0.026552 | −0.010822 | −0.048752 | 0.066951 | 0.102464 | 0.045684 | 0.058975 | 0.029331 | −0.027752 | −0.065906 | 0.182999 | −0.076158 | 0.039606 |
| 42 | 0.040827 | 0.003793 | 0.067238 | −0.061021 | 0.00458 | −0.005311 | 0.007357 | −0.019821 | −0.088027 | −0.02014 | −0.041888 | −0.015305 | −0.134712 | 0.064546 |
| 43 | −0.128674 | −0.178105 | 0.026621 | −0.00614 | 0.023571 | −0.029888 | 0.021435 | −0.017717 | −0.012361 | −0.016611 | 0.05579 | 0.073148 | −0.046598 | 0.088939 |
| 44 | −0.035048 | 0.082574 | 0.112126 | 0.048229 | −0.044222 | −0.023133 | −0.022808 | −0.001332 | −0.023218 | −0.020466 | 0.000257 | −0.037677 | 0.13044 | −0.022379 |
| 45 | −0.04471 | 0.019987 | −0.05774 | 0.054633 | −0.004172 | −0.064782 | 0.042002 | 0.059379 | 0.125237 | 0.048426 | 0.0112 | −0.009011 | −0.069917 | −0.039883 |
| 46 | 0.034327 | 0.024483 | −0.066004 | −0.02456 | 0.036738 | 0.040404 | −0.003884 | 0.00296 | −0.043247 | −0.008849 | 0.015632 | 0.005736 | −0.021696 | 0.007597 |
| 47 | 0.072155 | −0.16913 | 0.032233 | −0.054652 | 0.059663 | 0.049519 | 0.06111 | 0.030786 | −0.021541 | 0.007329 | 0.002663 | 0.05198 | −0.045088 | 0.001352 |
| 48 | 0.089156 | −0.047873 | 0.015436 | 0.033941 | −0.062692 | −0.049326 | −0.009415 | −0.024279 | −0.008575 | −0.025463 | −0.056007 | 0.022812 | −0.02825 | −0.064655 |
| 49 | 0.226974 | −0.089258 | 0.012436 | −0.027766 | −0.034643 | −0.048207 | −0.000351 | −0.037532 | 0.000563 | −0.088132 | −0.019285 | 0.09203 | 0.028987 | −0.023316 |
| 50 | 0.143695 | 0.04568 | 0.125246 | −0.00203 | 0.134406 | 0.146123 | 0.121406 | 0.107894 | 0.134208 | 0.050034 | 0.053385 | 0.041399 | −0.094988 | −0.005921 |
| 51 | −0.047344 | 0.118809 | 0.0484 | 0.021161 | 0.083712 | 0.064868 | 0.056069 | 0.04373 | 0.051373 | 0.04573 | −0.033228 | −0.003206 | 0.033157 | 0.021698 |
| 52 | 0.005877 | 0.102072 | −0.010611 | −0.033053 | −0.043709 | −0.069343 | −0.052635 | −0.031559 | 0.020565 | −0.017832 | 0.035526 | 0.001965 | 0.038737 | 0.052056 |
| 53 | 0.018719 | 0.002826 | 0.157305 | −0.001204 | 0.021831 | −0.013814 | −0.001681 | 0.086452 | 0.043285 | 0.022666 | 0.003115 | 0.049431 | 0.125365 | 0.014933 |
| 54 | −0.157795 | 0.036853 | −0.064184 | 0.031265 | 0.023125 | 0.038826 | 0.001078 | 0.039732 | −0.011738 | −0.023422 | −0.01388 | 0.033911 | 0.048926 | −0.05018 |
| 55 | 0.050029 | 0.041177 | −0.190887 | −0.006338 | −0.010439 | 0.037125 | −0.001271 | 0.004471 | 0.075774 | 0.013769 | 0.031907 | −0.053355 | −0.015969 | −0.004501 |
| 56 | −0.130611 | 0.075069 | −0.008623 | 0.072997 | 0.031276 | 0.033018 | 0.018374 | 0.034249 | 0.00547 | −0.036744 | −0.026808 | −0.052981 | 0.007195 | 0.112914 |
| 57 | −0.025501 | −0.109418 | −0.02622 | −0.082932 | −0.003786 | 0.027986 | 0.058224 | −0.036252 | 0.010456 | 0.060884 | 0.036975 | −0.052022 | −0.076957 | 0.020143 |
| 58 | 0.103359 | 0.092621 | −0.175077 | 0.031955 | −0.059535 | −0.045882 | −0.034402 | −0.02862 | −0.051508 | −0.066891 | −0.056657 | 0.004185 | −0.053143 | 0.01993 |
| 59 | −0.057573 | −0.043603 | −0.089909 | −0.03167 | 0.02167 | 0.00367 | −0.04048 | −0.01961 | 0.007889 | 0.057826 | −0.014943 | 0.015881 | −0.023593 | 0.020797 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 60 | −0.031876 | −0.092852 | 0.14981 | 0.004058 | 0.092751 | 0.023701 | 0.056477 | 0.012412 | −0.001132 | 0.009717 | −0.025676 | 0.076438 | −0.045681 | 0.031213 |
| 61 | 0.033769 | 0.083304 | −0.007176 | −0.009007 | 0.023039 | −0.002901 | −0.0053 | 0.034043 | 0.041444 | 0.051605 | −0.020148 | −0.039026 | 0.035717 | −0.020272 |
| 62 | 0.028703 | −0.030825 | −0.133358 | −0.067466 | 0.057036 | 0.064404 | 0.056699 | 0.048062 | 0.027122 | 0.088607 | 0.107257 | 0.09495 | −0.016909 | 0.072879 |
| 63 | 0.027896 | −0.007629 | 0.027614 | 0.040886 | 0.001874 | −0.028319 | 0.021788 | −0.015682 | −0.072559 | 0.01562 | 0.1445 | 0.020195 | 0.115801 | −0.026646 |
| 64 | 0.017428 | 0.023778 | −0.066193 | −0.001166 | −0.024602 | −0.001563 | −0.011204 | −0.003428 | −0.02698 | −0.022632 | −0.030591 | 0.007425 | −0.005447 | 0.026037 |
| 65 | −0.046245 | 0.172172 | 0.049589 | −0.02355 | −0.006697 | 0.04223 | −0.01284 | 0.032412 | −0.010265 | −0.022956 | −0.036074 | 0.015875 | −0.003919 | −0.011385 |
| 66 | −0.043801 | 0.02292 | −0.097414 | 0.008655 | 0.023197 | 0.087957 | −0.030736 | −0.00771 | 0.035870 | −0.003721 | 0.06125 | −0.034933 | −0.014859 | −0.042957 |
| 67 | −0.058803 | 0.054466 | 0.050672 | 0.009533 | −0.008312 | −0.035085 | 0.053595 | −0.001317 | 0.000753 | 0.063178 | −0.006038 | 0.010788 | −0.008103 | 0.015113 |
| 68 | 0.018901 | −0.087952 | 0.024307 | 0.018493 | 0.001602 | −0.000202 | 0.000348 | −0.001626 | −0.035298 | −0.049565 | −0.093965 | −0.020551 | −0.025373 | −0.016954 |
| 69 | 0.040115 | −0.023596 | 0.014584 | −0.115148 | −0.014943 | 0.014975 | 0.019953 | −0.108582 | 0.036156 | 0.002691 | −0.006919 | −0.001086 | 0.000995 | −0.012158 |
| 70 | −0.07074 | −0.022953 | 0.027325 | 0.007366 | −0.008732 | −0.008364 | 0.016423 | 0.085893 | 0.044063 | −0.062163 | −0.083898 | −0.02798 | 0.11252 | −0.019746 |
| 71 | 0.05611 | 0.032387 | −0.009062 | 0.006976 | −0.00625 | 0.01578 | −0.041069 | −0.007284 | 0.029539 | 0.01697 | 0.011674 | −0.080029 | −0.074811 | 0.024356 |
| 72 | −0.101488 | −0.040713 | 0.133864 | −0.090625 | 0.005624 | −0.0236 | −0.00572 | 0.013427 | −0.016604 | −0.001713 | 0.043206 | 0.024221 | 0.056285 | −0.025066 |
| 73 | 0.108583 | −0.020799 | −0.045685 | 0.01384 | −0.011699 | 0.031152 | −0.030513 | 0.056308 | 0.001532 | 0.019773 | 0.001479 | −0.0407 | 0.040939 | 0.005483 |
| 74 | 0.029266 | −0.087716 | 0.033712 | −0.023582 | 0.007246 | −0.006793 | −0.021836 | −0.01424 | 0.029544 | 0.023395 | 0.027053 | −0.066769 | 0.021944 | 0.000141 |
| 75 | −0.032257 | 0.189933 | −0.007168 | 0.11999 | −0.012762 | 0.016597 | 0.02615 | −0.005682 | 0.010852 | 0.067329 | 0.102496 | −0.058402 | −0.200709 | −0.034752 |
| 76 | 0.042188 | −0.036674 | −0.017062 | −0.057616 | −0.002734 | 0.048371 | −0.014561 | −0.078002 | −0.045422 | 0.080771 | −0.090141 | −0.003462 | 0.132105 | 0.01357 |
| 77 | −0.094738 | 0.127058 | 0.009149 | −0.057868 | 0.054085 | 0.005685 | 0.010242 | −0.011372 | −0.004871 | −0.00003 | 0.051538 | 0.006518 | 0.032466 | −0.043719 |
| 78 | 0.083297 | −0.15301 | 0.036331 | −0.008014 | 0.024147 | 0.015147 | 0.008303 | 0.090545 | −0.015514 | −0.065372 | 0.046831 | 0.040372 | −0.053933 | 0.021198 |
| 79 | 0.029868 | −0.125756 | −0.139487 | −0.018966 | 0.04751 | 0.068603 | 0.095783 | 0.025436 | 0.028655 | −0.033582 | −0.036617 | −0.029315 | 0.035056 | 0.013649 |
| 80 | 0.127558 | 0.044384 | 0.030581 | 0.015766 | 0.001727 | −0.028508 | 0.043724 | 0.01453 | 0.008353 | 0.04724 | −0.053282 | 0.088142 | 0.046443 | 0.07316 |
| 81 | −0.010196 | 0.133608 | −0.026907 | 0.024472 | −0.02066 | −0.042001 | 0.034527 | 0.051347 | −0.030794 | −0.019253 | 0.028853 | 0.099725 | −0.08985 | 0.014608 |
| 82 | −0.067306 | −0.197039 | −0.004664 | 0.137107 | 0.044982 | −0.095221 | −0.007853 | 0.080708 | −0.019695 | 0.025821 | −0.069924 | 0.114027 | 0.180492 | 0.00376 |
| 83 | −0.0944 | −0.013582 | 0.094951 | 0.079178 | −0.041774 | −0.006092 | 0.008792 | −0.112834 | −0.002837 | −0.05042 | −0.0466 | 0.006757 | 0.127528 | −0.089709 |
| 84 | −0.102886 | 0.055593 | 0.043377 | 0.061998 | −0.014004 | −0.084633 | 0.059202 | 0.072306 | 0.083854 | 0.101284 | −0.002474 | 0.076824 | −0.015738 | 0.024701 |
| 85 | −0.049771 | 0.068923 | 0.008428 | −0.065938 | −0.058421 | −0.022078 | 0.008619 | −0.054471 | −0.017285 | −0.017322 | 0.03421 | 0.110533 | −0.114046 | 0.121667 |
| 86 | 0.033869 | −0.000829 | −0.044864 | −0.020085 | 0.015075 | −0.012127 | −0.045846 | −0.009937 | −0.047308 | 0.015526 | −0.164363 | −0.075872 | 0.002679 | −0.013806 |
| 87 | 0.111013 | −0.056978 | −0.006678 | 0.070867 | 0.003511 | −0.012517 | 0.066346 | 0.030744 | 0.021681 | −0.005771 | 0.039488 | −0.001992 | 0.050941 | −0.12625 |
| 88 | 0.066231 | −0.000447 | 0.000787 | −0.059309 | −0.018788 | 0.002681 | −0.011165 | −0.034714 | −0.044961 | −0.025072 | −0.025427 | −0.052468 | 0.085965 | −0.033168 |
| 89 | −0.150457 | −0.063266 | −0.05218 | −0.118505 | 0.012365 | 0.010455 | −0.024886 | 0.04326 | −0.019786 | −0.117225 | 0.017787 | 0.009459 | −0.030419 | 0.119145 |
| 90 | 0.086322 | 0.017678 | −0.010334 | −0.018538 | 0.015108 | 0.075364 | 0.062219 | −0.128377 | −0.021801 | −0.055522 | 0.078769 | −0.053561 | 0.082492 | 0.070406 |
| 91 | 0.030605 | 0.053853 | 0.012353 | −0.072178 | −0.002443 | 0.040203 | −0.051115 | −0.020583 | 0.022363 | −0.020834 | −0.07546 | −0.012763 | −0.082534 | −0.050791 |
| 92 | 0.08038 | 0.099919 | −0.017772 | 0.040633 | 0.033578 | −0.014605 | −0.028618 | 0.009928 | −0.069509 | −0.04959 | 0.006539 | 0.031589 | −0.001276 | 0.09038 |
| 93 | −0.021885 | 0.010906 | −0.059461 | 0.070126 | 0.020064 | 0.026167 | −0.018319 | 0.023324 | −0.006898 | 0.058905 | 0.03357 | 0.028716 | −0.0008 | 0.03325 |
| 94 | −0.033033 | −0.011978 | 0.112621 | 0.058306 | 0.04796 | −0.010134 | 0.056112 | 0.055986 | −0.00089 | 0.080027 | −0.039047 | 0.014266 | −0.059677 | 0.038068 |
| 95 | −0.090041 | −0.138167 | −0.000211 | 0.089318 | −0.011747 | 0.029024 | −0.005759 | −0.026615 | 0.028305 | 0.07108 | 0.054244 | −0.083763 | −0.165229 | −0.048729 |
| 96 | −0.080817 | −0.005681 | 0.037009 | −0.116422 | −0.016409 | −0.006665 | −0.019346 | 0.042068 | 0.039537 | −0.023037 | 0.017739 | 0.022118 | −0.030479 | 0.02539 |
| 97 | −0.093283 | −0.092317 | −0.015636 | 0.053612 | 0.104356 | 0.078947 | 0.063201 | 0.026244 | −0.042511 | −0.029733 | 0.014505 | −0.000219 | −0.046994 | −0.070712 |
| 98 | 0.008582 | −0.020809 | −0.155199 | 0.019531 | 0.032403 | 0.058915 | 0.064883 | 0.002875 | −0.031109 | −0.026066 | 0.054484 | 0.064689 | 0.049366 | −0.153604 |
| 99 | 0.019255 | 0.02784 | −0.012979 | −0.056394 | −0.082736 | −0.101404 | −0.101517 | −0.11167 | −0.074298 | −0.015248 | 0.067421 | −0.06018 | −0.086588 | 0.170928 |
| 100 | 0.105395 | 0.043428 | 0.115314 | −0.008162 | 0.020652 | 0.014365 | −0.041379 | −0.0375 | −0.069998 | −0.006896 | 0.0439 | −0.123338 | −0.014023 | −0.030926 |
| 101 | −0.193716 | 0.112399 | 0.151248 | −0.017288 | −0.026702 | −0.062886 | −0.001092 | −0.008838 | 0.006402 | −0.121108 | −0.007787 | −0.061191 | −0.032185 | −0.065461 |
| 102 | −0.142021 | 0.024809 | −0.065189 | 0.024785 | 0.005774 | −0.013324 | 0.05657 | −0.023274 | 0.001771 | −0.075396 | −0.005288 | −0.040366 | −0.080159 | −0.00067 |
| 103 | 0.082279 | 0.048806 | 0.071448 | −0.055813 | −0.025309 | −0.01632 | −0.017737 | −0.049281 | −0.01954 | 0.003927 | 0.037475 | 0.036903 | 0.032486 | 0.008941 |
| 104 | −0.035499 | 0.011424 | −0.108726 | 0.018629 | 0.004947 | 0.016343 | −0.025849 | 0.03585 | −0.010316 | −0.031924 | −0.000532 | 0.010372 | 0.016324 | 0.00777 |
| 105 | −0.069797 | −0.037811 | −0.009831 | −0.022993 | 0.003944 | 0.024941 | −0.032572 | −0.006019 | 0.012031 | 0.013444 | −0.052094 | −0.015802 | −0.031689 | 0.001681 |
| 106 | −0.158901 | −0.104045 | −0.024912 | 0.064404 | 0.016928 | −0.009216 | 0.015764 | −0.02235 | −0.024238 | −0.038805 | 0.012136 | 0.036773 | −0.112591 | −0.051995 |
| 107 | −0.009474 | 0.012239 | 0.055456 | −0.034305 | 0.022504 | 0.030021 | −0.039318 | 0.072018 | 0.017759 | −0.067586 | −0.044051 | −0.045505 | 0.015486 | 0.007615 |
| 108 | −0.003073 | 0.029731 | 0.00144 | −0.013859 | −0.021056 | −0.026429 | 0.002427 | −0.01794 | −0.014436 | −0.011267 | 0.015027 | 0.061959 | −0.010133 | 0.032282 |
| 109 | 0.010922 | −0.018384 | 0.015435 | −0.00183 | 0.044662 | 0.0636 | 0.019014 | −0.006873 | −0.035625 | −0.022544 | −0.024882 | 0.057151 | 0.057439 | −0.007 |
| 110 | 0.034278 | 0.006537 | −0.031478 | −0.019695 | −0.043328 | −0.040763 | −0.028399 | 0.03339 | 0.070181 | 0.041311 | 0.032204 | −0.026157 | 0.106401 | −0.062317 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 111 | 0.057846 | 0.06994 | 0.075917 | 0.047967 | −0.034306 | 0.012601 | 0.013643 | 0.007589 | −0.030791 | −0.04838 | 0.077181 | 0.060809 | 0.110335 | 0.006835 |
| 112 | 0.042828 | 0.001076 | 0.037206 | 0.082771 | 0.012401 | 0.01084 | 0.036047 | 0.009434 | −0.004492 | 0.095671 | 0.077244 | −0.009377 | −0.028534 | 0.00627 |
| 113 | 0.067036 | 0.030898 | −0.038039 | 0.040707 | 0.007263 | −0.0128 | 0.06978 | −0.001684 | 0.031974 | −0.042228 | −0.028097 | −0.018623 | −0.057925 | 0.009158 |
| 114 | 0.04313 | 0.050225 | 0.003237 | −0.014646 | −0.033506 | −0.057931 | −0.052794 | −0.020977 | −0.024221 | −0.00207 | 0.041738 | 0.088762 | −0.007407 | −0.012049 |
| 115 | 0.011751 | 0.011056 | 0.042864 | 0.014214 | 0.028155 | −0.012318 | 0.044154 | 0.019481 | −0.032354 | 0.064115 | −0.045678 | −0.010177 | −0.104041 | 0.035917 |
| 116 | −0.012471 | −0.053338 | −0.060702 | 0.041508 | −0.031686 | −0.076123 | −0.022515 | −0.056803 | 0.012817 | 0.022827 | −0.009788 | −0.001575 | −0.016776 | −0.020974 |
| 117 | −0.036578 | −0.005562 | 0.084042 | −0.012601 | 0.055846 | 0.073921 | 0.009394 | 0.025209 | 0.000262 | −0.067244 | −0.078608 | 0.009688 | −0.030463 | 0.021161 |
| 118 | −0.04953 | 0.016858 | 0.069842 | 0.023412 | 0.019353 | 0.046788 | −0.013262 | −0.021336 | 0.003592 | −0.019011 | −0.110741 | −0.017691 | 0.088124 | −0.002837 |
| 119 | −0.072512 | −0.019541 | 0.026086 | 0.030907 | 0.022134 | 0.015845 | 0.017098 | −0.012499 | −0.002113 | −0.043329 | −0.110994 | 0.126835 | −0.086276 | 0.008461 |
| 120 | 0.051748 | 0.062067 | −0.040952 | 0.050555 | −0.006214 | 0.00222 | −0.018698 | −0.020633 | 0.038425 | 0.103592 | −0.036994 | −0.004506 | −0.021459 | −0.055329 |
| 121 | −0.025566 | −0.015412 | −0.000121 | 0:043994 | −0.036312 | −0.061506 | −0.027316 | 0.015385 | 0.003999 | 0.054267 | 0.193818 | 0.012081 | 0.050059 | 0.031925 |
| 122 | 0.005824 | −0.096618 | −0.032827 | −0.317846 | −0.076813 | −0.068052 | −0.060657 | 0.041486 | −0.034714 | −0.022282 | −0.0266 | 0.012519 | −0.031948 | 0.041386 |
| 123 | 0.085977 | 0.024479 | −0.044679 | 0.121861 | 0.055468 | 0.082444 | −0.018126 | 0.01081 | 0.032502 | −0.015053 | 0.121333 | −0.104708 | 0.029274 | 0.033424 |
| 124 | −0.028155 | 0.009252 | −0.051708 | −0.094729 | −0.016184 | −0.066036 | −0.01408 | −0.072034 | −0.023486 | −0.014441 | 0.018648 | −0.078388 | 0.000307 | −0.015336 |
| 125 | −0.100454 | 0.058534 | 0.040799 | −0.154293 | 0.002521 | 0.03422 | 0.042477 | 0.022918 | −0.049968 | 0.016357 | 0.060217 | 0.04649 | 0.020568 | 0.020037 |
| 126 | −0.018696 | 0.052981 | 0.127766 | −0.009622 | 0.096149 | 0.013196 | 0.045525 | 0.102799 | −0.044212 | 0.030339 | 0.026027 | 0.050887 | −0.108298 | 0.057271 |
| 127 | −0.00018 | −0.007699 | 0.007205 | −0.011365 | −0.00948 | 0.015975 | 0.004962 | −0.070357 | 0.003257 | −0.080186 | −0.063843 | −0.013713 | −0.007876 | −0.087182 |
| 128 | −0.003638 | 0.033572 | 0.015088 | −0.0048 | 0.049431 | 0.045802 | 0.023544 | 0.036938 | 0.012886 | 0.089782 | 0.011509 | 0.074786 | −0.032768 | 0.032258 |
| 129 | 0.048813 | −0.04261 | −0.012611 | −0.014311 | −0.039802 | 0.0015 | 0.008019 | −0.051918 | −0.012469 | −0.027757 | 0.008407 | −0.004352 | −0.01896 | −0.032681 |
| 130 | 0.012428 | 0.000407 | −0.045535 | −0.042071 | −0.021339 | −0.070653 | 0.01524 | 0.013742 | 0.062704 | 0.004255 | −0.014923 | −0.032324 | 0.081952 | −0.002707 |
| 131 | −0.008271 | 0.013224 | 0.025005 | 0.008981 | −0.010508 | −0.01101 | −0.020934 | 0.022332 | 0.00726 | 0.01423 | 0.021923 | −0.031342 | 0.054793 | 0.038844 |
| 132 | 0.019657 | −0.054489 | −0.076012 | −0.027235 | −0.012072 | −0.049717 | 0.017255 | −0.017773 | 0.009307 | −0.049927 | 0.004735 | −0.030544 | 0.008892 | 0.041405 |
| 133 | −0.002726 | −0.084315 | −0.055368 | −0.032256 | −0.036034 | −0.049842 | 0.016436 | 0.087632 | 0.086899 | 0.040799 | −0.04254 | −0.054165 | 0.020412 | −0.014628 |
| 134 | 0.039502 | 0.008486 | 0.033631 | −0.00966 | 0.041489 | 0.068302 | −0.000421 | 0.032185 | 0.036305 | 0.003809 | 0.003014 | −0.001117 | −0.004344 | 0.02575 |
| 135 | −0.072725 | −0.021029 | 0.049899 | −0.026983 | −0.059763 | −0.048913 | 0.020936 | −0.004732 | 0.06947 | 0.023101 | 0.049469 | 0.034497 | −0.035245 | −0.027798 |
| 136 | 0.086452 | 0.065564 | −0.013303 | −0.040104 | 0.03344 | 0.076215 | −0.004861 | −0.026121 | −0.054017 | −0.092827 | 0.020037 | 0.004061 | −0.056518 | 0.041158 |
| 137 | −0.061931 | 0.025875 | −0.013889 | 0.01206 | 0.006765 | 0.001262 | 0.008236 | 0.012284 | −0.028159 | 0.091939 | −0.029936 | 0.015872 | −0.031673 | −0.047941 |
| 138 | −0.002397 | −0.002622 | −0.057088 | −0.036269 | −0.02577 | −0.056071 | −0.015646 | 0.016545 | 0.015904 | 0.085826 | 0.04208 | −0.010807 | −0.006163 | −0.012828 |
| 139 | −0.060259 | 0.019911 | −0.023445 | 0.020606 | −0.010078 | 0.015659 | −0.015103 | −0.050264 | −0.043899 | 0.036657 | 0.014681 | 0.023017 | −0.011377 | −0.024347 |
| 140 | −0.000416 | −0.000059 | 0.040127 | 0.03076 | −0.030851 | −0.02795 | −0.041763 | −0.013104 | −0.007416 | −0.027398 | 0.021623 | 0.03932 | −0.009193 | −0.016305 |
| 141 | −0.008259 | 0.003841 | 0.000162 | 0.027499 | 0.013192 | 0.009828 | −0.037629 | −0.02895 | −0.051235 | −0.077316 | 0.043936 | −0.011091 | 0.116906 | 0.035307 |
| 142 | 0.035689 | −0.005131 | 0.016489 | 0.083259 | 0.005462 | 0.03274 | −0.005893 | −0.00743 | 0.031829 | −0.020112 | 0.035252 | 0.041977 | 0.050803 | −0.012445 |
| 143 | 0.041259 | −0.009396 | 0.029554 | 0.026256 | −0.002565 | 0.043536 | −0.006542 | −0.040332 | 0.010638 | 0.030661 | −0.038859 | −0.031086 | 0.077193 | −0.020958 |
| 144 | −0.042786 | 0.006489 | −0.050588 | 0.020383 | −0.026307 | −0.047655 | −0.029545 | 0.006691 | 0.015736 | 0.043573 | 0.070471 | 0.027188 | −0.040646 | 0.000698 |
| 145 | −0.078088 | −0.004984 | −0.091285 | 0.00636 | 0.004745 | −0.021586 | 0.010732 | 0.023333 | 0.009109 | 0.039571 | 0.028147 | −0.001746 | 0.016619 | −0.062999 |
| 146 | 0.032081 | −0.016219 | −0.008729 | −0.059253 | −0.009424 | 0.021945 | −0.023187 | −0.033433 | −0.042177 | −0.002934 | −0.005599 | −0.039738 | 0.023151 | 0.038043 |
| 147 | 0.014836 | −0.004879 | −0.012267 | −0.016838 | −0.026904 | −0.016358 | −0.006706 | −0.010537 | 0.015167 | −0.035502 | 0.006497 | 0.017466 | 0.027428 | −0.012454 |
| 148 | 0.021213 | 0.030517 | −0.006481 | −0.000981 | 0.00683 | 0.022996 | 0.03454 | −0.018393 | −0.040862 | −0.011297 | 0.041916 | 0.027163 | −0.031792 | −0.003674 |
| 149 | 0.002984 | 0.009496 | −0.108437 | 0.018985 | 0.000517 | −0.016879 | −0.012328 | 0.003384 | −0.018003 | −0.047303 | −0.038417 | 0.006887 | 0.030943 | −0.014872 |
| 150 | −0.027205 | 0.025802 | −0.011799 | 0.040098 | 0.009766 | 0.019431 | 0.014389 | −0.01365 | 0.030556 | −0.00825 | −0.04397 | 0.003718 | 0.034292 | −0.007487 |
| 151 | 0.002483 | −0.060335 | 0.020713 | 0.046642 | 0.062538 | 0.021772 | 0.052412 | 0.010895 | 0.041548 | −0.018371 | 0.016749 | 0.012858 | −0.053937 | −0.006722 |
| 152 | −0.00088 | 0.012091 | −0.033036 | −0.002573 | 0.010077 | −0.008466 | −0.027196 | 0.034177 | 0.039954 | 0.055675 | −0.039676 | −0.012587 | −0.003468 | −0.013023 |
| 153 | −0.069919 | −0.017691 | 0.046133 | −0.023691 | −0.013732 | −0.052271 | −0.031588 | 0.007501 | −0.017085 | −0.029026 | −0.020862 | −0.007022 | 0.029585 | −0.004744 |
| 154 | 0.014296 | −0.028192 | 0.023182 | −0.04894 | 0.02914 | 0.001192 | 0.030607 | 0.019664 | −0.018572 | 0.007022 | 0.035432 | 0.085583 | −0.019407 | 0.023406 |
| 155 | −0.04391 | 0.000543 | −0.021038 | 0.082713 | 0.034433 | 0.024325 | 0.036152 | −0.009103 | 0.013938 | −0.015891 | −0.036925 | 0.045824 | −0.010722 | 0.03098 |
| 156 | −0.015631 | 0.012043 | −0.028223 | 0.011239 | −0.009947 | −0.024673 | −0.00271 | 0.005863 | 0.023969 | 0.0209 | −0.011863 | 0.003393 | 0.025913 | 0.053023 |
| 157 | 0.019052 | 0.031459 | 0.042174 | −0.002039 | −0.004598 | 0.066318 | 0.02703 | 0.003886 | −0.002825 | 0.040697 | −0.035699 | −0.023441 | −0.034399 | −0.002841 |
| 158 | 0.007461 | −0.028241 | −0.002372 | 0.021013 | 0.000984 | 0.01042 | 0.010273 | −0.035856 | −0.009613 | −0.026132 | 0.021228 | −0.066111 | −0.003843 | −0.028868 |
| 159 | 0.057911 | 0.019666 | 0.045448 | −0.020797 | −0.007794 | −0.025509 | 0.013416 | 0.021452 | 0.023582 | −0.011672 | 0.049603 | −0.020958 | −0.031457 | 0.014218 |
| 160 | −0.006738 | −0.037472 | 0.011598 | 0.068235 | 0.020411 | 0.00957 | −0.016905 | 0.009986 | −0.016041 | −0.015084 | −0.039246 | −0.000436 | 0.030203 | 0.039202 |
| 161 | −0.02482 | 0.009374 | −0.001773 | −0.051376 | 0.014421 | −0.000844 | −0.000057 | 0.007335 | −0.011418 | −0.05526 | −0.033432 | −0.028698 | 0.004087 | −0.017845 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 162 | 0.015572 | −0.030314 | 0.042764 | −0:038837 | −0.019148 | −0.008533 | −0.013167 | 0.000592 | −0.03323 | 0.043819 | −0.0068 | −0.014266 | −0.048113 | −0.027723 |
| 163 | −0.018448 | 0.111564 | 0.000688 | −0.0138 | −0.031312 | 0.002318 | −0.029897 | 0.014218 | 0.03716 | 0.01399 | 0.001731 | 0.005786 | 0.042103 | 0.00792 |
| 164 | −0.015974 | −0.09876 | −0.016868 | −0.004232 | 0.000755 | 0.007054 | 0.024726 | −0.02946 | 0.015313 | 0.0017811 | 0.001266 | −0.048594 | 0.0611 | 0.018146 |
| 165 | 0.206755 | 0.017915 | 0.013257 | 0.023376 | −0.005748 | −0.042158 | −0.014491 | 0.01597 | −0.016279 | 0.029115 | −0.002844 | −0.054336 | −0.03701 | −0.028682 |
| 166 | −0.022176 | 0.336626 | −0.023328 | −0.031697 | −0.016461 | −0.026671 | 0.011528 | −0.027106 | −0.007597 | 0.017702 | −0.015085 | −0.015132 | 0.038961 | 0.018866 |
| 167 | 0.006867 | −0.10604 | 0.356093 | 0.010138 | −0.020142 | 0.011628 | −0.042735 | −0.009729 | −0.020703 | −0.005148 | 0.02548 | −0.060762 | −0.048656 | −0.031924 |
| 168 | 0.022276 | 0.011788 | 0.01525 | 0.414779 | −0.048065 | −0.040892 | −0.061705 | −0.012912 | −0.017643 | −0.07032 | −0.016558 | −0.010908 | −0.024231 | 0.046995 |
| 169 | −0.002997 | 0.015005 | −0.016202 | −0.032641 | 0.811409 | −0.159901 | −0.13693 | −0.098373 | −0.018508 | −0.01737 | −0.005338 | −0.071658 | −0.026898 | −0.023752 |
| 170 | −0.036784 | −0.015024 | 0.007259 | −0.015135 | −0.170644 | 0.736302 | −0.129941 | −0.050263 | −0.023973 | 0.011523 | 0.005062 | −0.042582 | −0.039539 | −0.01839 |
| 171 | −0.007067 | 0.033606 | −0.017444 | −0.046764 | −0.113517 | −0.101873 | 0.798056 | −0.057946 | −0.047123 | −0.018955 | 0.010349 | −0.072979 | −0.003997 | −0.008231 |
| 172 | 0.034582 | 0.007849 | −0.024998 | −0.031597 | −0.06693 | −0.003876 | −0.060117 | 0.751236 | −0.095536 | −0.080933 | −0.060154 | −0.087312 | 0.010069 | −0.0068 |
| 173 | 0.02422 | 0.001479 | −0.011087 | −0.037128 | 0.009396 | 0.008772 | −0.03779 | −0.096035 | 0.786079 | −0.113117 | −0.026617 | 0.04213 | 0.019498 | 0.039054 |
| 174 | 0.026798 | 0.011357 | −0.011206 | −0.04732 | −0.012548 | −0.001051 | −0.047387 | −0.054954 | −0.107912 | 0.674963 | −0.122379 | 0.022792j | −0.006784 | 0.016956 |
| 175 | −0.006171 | −0.056851 | 0.012943 | −0.040917 | −0.006494 | −0.020523 | −0.017693 | −0.038844 | −0.030881 | −0.099604 | 0.521924 | −0.021526 | 0.028011 | −0.010324 |
| 176 | 0.009321 | 0.032965 | −0.030722 | −0.037433 | −0.033078 | 0.014081 | −0.062342 | −0.086229 | 0.027447 | 0.011292 | −0.061722 | 0.626954 | 0.024985 | −0.0411 |
| 177 | 0.014836 | 0.051091 | −0.05608 | −0.023865 | −0.009518 | −0.032081 | −0.019429 | −0.017588 | −0.000543 | 0.018009 | 0.062124 | −0.005264 | 0.33292 | 0.008638 |
| 178 | 0.023699 | −0.023833 | −0.010818 | 0.066546 | −0.023737 | −0.00822 | −0.008758 | −0.007101 | 0.047858 | 0.006292 | −0.024591 | −0.039976 | 0.006277 | 0.760413 |
| 179 | 0.023876 | −0.030581 | −0.018318 | −0.072851 | −0.034256 | −0.033091 | −0.060412 | 0.026147 | 0.032898 | 0.001967 | −0.021389 | 0.012421 | −0.020083 | −0.051629 |
| 180 | 0.073324 | −0.03107 | −0.030815 | 0.019159 | −0.025257 | −0.046413 | −0.011129 | 0.043357 | 0.019852 | 0.000988 | 0.00046 | 0.016934 | 0.006392 | −0.094869 |
| 181 | 0.056381 | −0.039284 | −0.025027 | 0.027777 | −0.020929 | −0.049739 | −0.023671 | 0.057275 | 0.029556 | 0.008052 | −0.003027 | 0.005838 | −0.036649 | −0.066804 |
| 182 | 0.012002 | −0.019355 | 0.017006 | −0.027168 | −0.013566 | −0.070338 | 0.001336 | 0.026207 | 0.01697 | 0.023145 | 0.016485 | 0.032143 | −0.075618 | −0.051944 |
| 183 | −0.030253 | 0.040392 | 0.016752 | −0.095817 | 0.012495 | −0.005139 | −0.064145 | 0.054505 | 0.023578 | 0.057257 | 0.013166 | 0.007844 | −0.044054 | −0.000119 |
| 184 | −0.084916 | −0.01682 | 0.032759 | −0.050779 | 0.014899 | 0.022662 | −0.069309 | 0.026327 | 0.007879 | 0.016908 | 0.016627 | −0.025691 | 0.024299 | −0.011088 |
| 185 | 0.02208 | −0.037802 | 0.009462 | 0.064631 | 0.039969 | 0.043067 | 0.045491 | −0.002096 | −0.008911 | −0.015284 | −0.004888 | 0.020567 | −0.005958 | −0.044405 |
| 186 | −0.015978 | −0.002659 | 0.000832 | 0.042595 | 0.02745 | 0.038798 | −0.018334 | 0.016497 | −0.00475 | 0.020897 | 0.033742 | 0.015446 | 0.017327 | 0.016911 |
| 187 | 0.018053 | 0.022813 | −0.002459 | 0.035503 | 0.016561 | 0.015821 | 0.036637 | −0.016277 | −0.082432 | −0.004296 | 0.044576 | 0.015095 | 0.00863 | 0.014649 |
| 188 | −0.020599 | 0.043642 | −0.030015 | 0.050247 | 0.019717 | 0.023737 | 0.019349 | −0.022934 | −0.047148 | −0.091372 | −0.021087 | −0.004821 | −0.010343 | 0.003735 |
| 189 | 0.029635 | 0.075785 | 0.034454 | −0.017478 | 0.02221 | 0.057545 | 0.047779 | −0.007299 | −0.008113 | −0.043547 | −0.129237 | −0.050849 | 0.038058 | 0.068329 |
| 190 | 0.078368 | 0.013396 | 0.002879 | −0.011674 | 0.005946 | −0.015495 | −0.001856 | 0.007414 | −0.0039 | 0.027508 | 0.01371 | −0.041409 | −0.004306 | −0.008509 |
| 191 | 0.061867 | 0.000603 | −0.006306 | 0.018106 | −0.036212 | −0.024236 | −0.015583 | −0.053509 | 0.015425 | −0.008935 | 0.015301 | 0.042225 | −0.054224 | −0.025748 |
| 192 | 0.049604 | −0.01008 | 0.027675 | −0.089482 | 0.01471 | 0.028404 | 0.01114 | −0.038144 | 0.01805 | −0.019646 | −0.032489 | 0.034074 | 0.014177 | 0.005501 |
| 193 | 0.026969 | −0.025092 | 0.050076 | −0.041798 | −0.008445 | −0.045485 | −0.002523 | −0.049661 | −0.021624 | 0.006614 | −0.014523 | −0.001591 | −0.001508 | −0.013767 |
| 194 | −0.013943 | −0.05135 | −0.013635 | 0.06098 | 0.01237 | 0.021865 | 0.007521 | 0.00879 | 0.021125 | 0.046475 | −0.079001 | −0.030741 | 0.060191 | −0.02736 |
| 195 | 0.089214 | −0.063752 | −0.010548 | −0.012626 | 0.057527 | 0.016443 | 0.045199 | 0.016856 | −0.051315 | −0.017851 | −0.013479 | 0.033694 | −0.00881 | 0.065236 |
| 196 | −0.015942 | −0.078975 | −0.032917 | 0.012698 | 0.008999 | 0.003467 | 0.020176 | −0.017625 | 0.001759 | 0.006963 | −0.084895 | 0.00214 | −0.018117 | −0.002372 |
| 197 | 0.014886 | 0.059353 | 0.027952 | −0.007604 | −0.021517 | −0.026406 | 0.02303 | −0.010941 | 0.013368 | −0.01869 | 0.017007 | 0.018177 | 0.053682 | 0.03877 |
| 198 | −0.019155 | 0.026773 | −0.004478 | −0.044893 | −0.001014 | −0.017127 | 0.00745 | −0.069174 | −0.011316 | −0.024125 | −0.036553 | −0.050239 | −0.020435 | −0.052303 |
| 199 | −0.019355 | 0.001358 | 0.041592 | 0.045847 | 0.011944 | 0.023226 | 0.001198 | 0.00619 | −0.009762 | 0.034581 | −0.004723 | 0.004023 | 0.028432 | −0.014247 |
| 200 | −0.027146 | 0.082575 | −0.002527 | 0.006144 | −0.015621 | −0.006418 | −0.048595 | −0.035944 | −0.012888 | −0.070202 | 0.002915 | 0.011535 | −0.043905 | −0.02758 |
| 201 | −0.009629 | 0.036095 | 0.019007 | 0.050855 | −0.012897 | −0.012574 | −0.007482 | 0.043034 | 0.023598 | 0.043739 | 0.068958 | −0.058311 | −0.029351 | −0.004254 |
| 202 | 0.030533 | −0.065687 | −0.017806 | −0.003584 | −0.015792 | −0.015541 | −0.005256 | −0.092674 | −0.056444 | −0.050437 | −0.01389 | 0.042381 | −0.02227 | −0.027741 |
| 203 | −0.025628 | 0.02726 | −0.007307 | −0:05142 | −0.029241 | −0.023232 | −0.013983 | −0.001836 | 0.015637 | −0.002104 | −0.006416 | −0.019133 | −0.000337 | −0.030163 |
| 204 | −0.044178 | 0.010955 | −0.051558 | −0.031736 | 0.016976 | −0.013994 | 0.005875 | 0.013164 | 0.003588 | 0.027698 | −0.044993 | −0.005446 | 0.00401 | 0.010094 |
| 205 | 0.047895 | −0.004278 | 0.000899 | −0.021091 | 0.006522 | 0.006092 | −0.000281 | 0.016443 | −0.020661 | −0.005972 | 0.008956 | −0.041737 | 0.030978 | 0.007952 |
| 206 | −0.0197 | −0.031728 | 0.016184 | 0.006658 | 0.003777 | 0.029352 | −0.021392 | −0.013121 | −0.010705 | −0.022528 | 0.024198 | 0.055024 | −0.019793 | −0.018004 |
| 207 | −0.033058 | 0.08796 | 0.022805 | 0.026603 | −0.009916 | 0.013875 | −0.0196 | 0.005866 | 0.012738 | −0.026179 | −0.037724 | −0.025875 | −0.075509 | −0.014163 |
| 208 | −0.033671 | 0.02282 | −0.011726 | −0.040613 | 0.025821 | 0.027149 | 0.006564 | 0.041915 | −0.001357 | 0.00442 | 0.056417 | 0.005856 | −0.090755 | 0.013575 |
| 209 | 0.005739 | 0.020384 | 0.060077 | 0.063209 | 0.031145 | 0.051159 | 0.0061 | −0.014252 | −0.042779 | −0.036513 | −0.009632 | 0.049501 | −0.0111971 | 0.027723 |
| 210 | 0.036119 | −0.005012 | −0.012821 | 0.062691 | −0.006182 | −0.014515 | −0.004338 | 0.026359 | −0.006359 | 0.032602 | −0.060938 | 0.000786 | −0.027084 | −0.030907 |
| 211 | 0.04 | −0.100595 | 0.041275 | 0.018833 | −0.006557 | −0.000414 | −0.02836 | −0.069833 | −0.065442 | −0.025329 | −0.032726 | 0.038451 | −0.001461 | −0.033987 |
| 212 | 0.068404 | −0.002856 | −0.028682 | −0.018442 | −0.002821 | −0.021425 | −0.020308 | −0.000696 | −0.009657 | 0.036149 | 0.01373 | 0.035246 | −0.004358 | 0.039458 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 213 | −0.04111 | −0.029101 | 0.014463 | 0.016809 | 0.011839 | 0.000567 | −0.013368 | −0.028609 | −0.015737 | 0.020239 | 0.02204 | 0.024134 | 0.075113 | −0.034966 |
| 214 | 0.007744 | 0.024926 | 0.016216 | −0.049848 | −0.023129 | 0.006594 | −0.052392 | −0.00668 | 0.018125 | 0.007934 | −0.005105 | −0.00495 | 0.025825 | −0.038238 |
| 215 | −0.030775 | 0.02983 | 0.023672 | −0.001564 | 0.00782 | 0.004852 | 0.003278 | 0.016003 | −0.009341 | 0.020895 | 0.028156 | 0.06529 | −0.038419 | −0.03586 |
| 216 | 0.020481 | −0.007344 | −0.037128 | −0.130365 | −0.008839 | 0.007258 | −0.01545 | 0.039305 | 0.008696 | 0.010605 | 0.008579 | −0.005818 | 0.047637 | 0.019658 |
| 217 | −0.001677 | 0.067773 | −0.004822 | 0.044963 | −0.025392 | −0.014169 | −0.026538 | −0.034142 | 0.02604 | 0.036209 | 0.025404 | 0.026869 | −0.024496 | 0.012559 |
| 218 | 0.034162 | 0.031104 | 0.033378 | −0.019069 | −0.007309 | −0.021575 | 0.004352 | −0.013316 | −0.036596 | −0.000818 | −0.037487 | −0.009721 | 0.000669 | 0.01187 |
| 219 | 0.005008 | −0.022042 | −0.034367 | −0.02824 | −0.034352 | −0.035435 | −0.044752 | −0.013211 | −0.036954 | −0.001928 | 0.000773 | −0.050129 | 0.000534 | 0.009792 |
| 220 | −0.002578 | 0.004828 | 0.014473 | 0.007702 | −0.060029 | −0.044531 | −0.047716 | −0.039937 | 0.007984 | −0.006371 | 0.027349 | −0.002706 | −0.062883 | 0.007971 |
| 221 | 0.011055 | 0.04003 | 0.03463 | −0.055972 | 0.050437 | 0.06798 | 0.027515 | −0.023001 | −0.059009 | −0.011068 | −0.014298 | −0.013519 | 0.042262 | 0.012184 |
| 222 | −0.040533 | 0.019531 | −0.051958 | −0.056647 | 0.036396 | 0.046003 | −0.002262 | 0.002745 | −0.057401 | −0.018419 | 0.005138 | 0.003058 | −0.024337 | 0.009338 |
| 223 | −0.030891 | 0.012792 | −0.043025 | −0.049493 | 0.004378 | −0.014885 | −0.024147 | 0.027524 | −0.040105 | −0.023322 | −0.015967 | −0.062872 | −0.014961 | 0.000815 |
| 224 | 0.008421 | 0.046001 | −0.033388 | 0.022093 | 0.014116 | 0.008175 | 0.009361 | −0.0154 | 0.000595 | −0.019756 | −0.029115 | −0.060936 | 0.036797 | −0.000063 |
| 225 | −0.005156 | 0.054708 | −0.008429 | 0.032098 | 0.021907 | 0.017554 | 0.01431 | −0.017504 | −0.007588 | −0.003237 | −0.011827 | −0.02386 | 0.037258 | 0.009349 |
| 226 | 0.01719 | 0.007613 | 0.050669 | −0.002521 | 0.010871 | 0.010957 | 0.008958 | −0.001459 | −0.001991 | 0.038542 | 0.013321 | −0.000078 | −0.007048 | 0.004482 |
| 227 | 0.013993 | 0.026884 | −0.036539 | −0.006572 | −0.012525 | 0.01123 | −0.037229 | 0.020951 | 0.000118 | 0.0079 | −0.008967 | 0.047247 | 0.008157 | 0.019466 |
| 228 | 0.054041 | −0.017177 | 0.00708 | −0.010816 | −0.034986 | −0.04109 | −0.012169 | −0.021872 | 0.030908 | 0.003548 | −0.020536 | −0.014146 | −0.00401 | −0.017643 |
| 229 | 0.039476 | 0.008487 | −0.013409 | 0.008278 | −0.011879 | −0.035962 | 0.004697 | −0.01575 | −0.016644 | 0.01605 | 0.037289 | 0.036854 | 0.019117 | 0.014062 |
| 230 | −0.008495 | 0.010664 | −0.011086 | −0.090011 | −0.02244 | −0.025054 | −0.007935 | −0.013802 | −0.022033 | −0.019484 | 0.019808 | 0.021826 | −0.00031 | 0.013533 |
| 231 | −0.076687 | −0.032561 | 0.044284 | 0.024089 | −0.03674 | −0.006676 | −0.017298 | −0.025392 | 0.023827 | 0.040438 | 0.023892 | −0.03582 | −0.072171 | 0.063486 |
| 232 | −0.065429 | −0.064074 | −0.025123 | −0.03573 | −0.014389 | 0.008808 | −0.017994 | −0.055294 | −0.018855 | −0.074697 | −0.03945 | 0.010255 | −0.043127 | 0.01866 |
| 233 | −0.053519 | 0.002614 | 0.022612 | −0.027418 | −0.010377 | −0.003653 | −0.017374 | −0.038834 | 0.015622 | −0.019362 | −0.035788 | 0.032719 | −0.014468 | −0.030594 |
| 234 | 0.044477 | 0.058321 | 0.055947 | −0.035603 | 0.006719 | 0.006182 | −0.002882 | 0.012297 | 0.021159 | −0.014811 | 0.057665 | −0.025489 | 0.045961 | −0.021156 |
| 235 | −0.034828 | −0.016013 | −0.026972 | −0.015247 | −0.022857 | −0.002876 | −0.007194 | −0.039853 | 0.002828 | 0.008402 | −0.027028 | −0.03034 | −0.048579 | −0.015774 |
| 236 | −0.027919 | 0.026124 | 0.008794 | 0.019717 | −0.005672 | −0.005355 | 0.009684 | 0.011395 | 0.017321 | −0.004114 | −0.031664 | −0.059802 | 0.008049 | −0.005401 |
| 237 | −0.044734 | −0.046883 | −0.044861 | 0.018725 | −0.013275 | −0.020918 | −0.009304 | 0.044778 | 0.054607 | 0.030422 | −0.014251 | 0.005998 | −0.017814 | 0.044075 |
| 238 | −0.042112 | 0.006193 | −0.025749 | 0.010699 | −0.017305 | −0.018907 | −0.016655 | −0.003033 | 0.019848 | −0.009792 | 0.015229 | 0.000145 | −0.051932 | 0.013427 |
| 239 | 0.002613 | 0.024485 | 0.003413 | −0.027218 | −0.004852 | 0.023781 | −0.000626 | −0.027994 | 0.005613 | −0.010558 | 0.019463 | −0.008729 | −0.013486 | −0.010691 |
| 240 | 0.048751 | −0.024831 | 0.001488 | −0.014848 | −0.01918 | −0.010236 | −0.017341 | −0.011449 | −0.039043 | −0.01424 | −0.007647 | 0.00875 | 0.015929 | 0.000057 |
| 241 | 0.003471 | 0.033575 | 0.007906 | −0.028695 | −0.003921 | −0.012499 | 0.008835 | 0.029717 | 0.047618 | −0.056281 | −0.065966 | −0.013744 | −0.02123 | 0.004898 |
| 242 | 0.022753 | −0.010996 | 0.000885 | 0.010385 | 0.011349 | 0.006625 | 0.01511 | −0.006442 | −0.015397 | 0.013666 | −0.009643 | 0.013809 | −0.011953 | −0.014861 |
| 243 | 0.02026 | −0.017322 | 0.003692 | 0.074046 | 0.015606 | −0.010476 | 0.01393 | 0.048781 | 0.024943 | 0.01771 | −0.00247 | 0.019739 | −0.011847 | −0.031085 |
| 244 | 0.031251 | 0.025668 | 0.055257 | 0:016816 | 0.031873 | 0.038957 | 0.040144 | 0.00225 | 0.017501 | 0.022151 | 0.019016 | −0.005659 | 0.031199 | −0.033169 |
| 245 | −0.019715 | −0.000441 | −0.051612 | 0.005537 | −0.000717 | 0.039915 | −0.026357 | −0.021884 | 0.001433 | −0.03937 | −0.005667 | 0.01244 | 0.034575 | 0.006503 |
| 246 | 0.037769 | −0.018684 | 0.007105 | 0.013485 | −0.008704 | −0.008797 | −0.005288 | 0.005893 | −0.00274 | −0.02952 | −0.001426 | 0.038804 | 0.012776 | −0.003843 |
| 247 | −0.019072 | 0.047133 | −0.035437 | 0.035222 | −0.013631 | −0.006744 | −0.023767 | −0.02429 | 0.020378 | −0.005654 | −0.014883 | −0.050004 | −0.013362 | −0.03959 |
| 248 | −0.030407 | 0.003518 | 0.000791 | 0.009398 | 0.007793 | 0.026199 | 0.007302 | −0.015752 | 0.013452 | 0.012718 | −0.020967 | −0.014893 | −0.049148 | 0.013641 |
| 249 | 0.008079 | 0.01161 | 0.023497 | 0.037567 | −0.00665 | −0.043633 | −0.008405 | −0.023401 | −0.01718 | −0.045617 | −0.001938 | −0.063873 | −0.056698 | 0.030296 |
| 250 | −0.005151 | −0.023397 | −0.01947 | 0.047846 | −0.011632 | −0.025792 | 0.023073 | 0.020444 | −0.004173 | 0.022732 | −0.054954 | 0.021635 | −0.000312 | −0.0344 |
| 251 | 0.018124 | −0.031089 | −0.015566 | 0.00937 | 0.013049 | 0.005175 | 0.01737 | 0.043694 | −0.026926 | −0.008534 | −0.028144 | 0.049917 | 0.019883 | −0.007241 |
| 252 | 0.048355 | 0.030812 | 0.017797 | −0.025429 | 0.017766 | 0.024332 | 0.020155 | 0.011369 | 0.028975 | −0.021379 | −0.000151 | 0.013608 | 0.030771 | 0.007932 |
| 253 | 0.071524 | 0.02927 | 0.022364 | −0.008632 | −0.046782 | −0.026587 | −0.031066 | 0.04154 | 0.039389 | 0.015579 | 0.013389 | 0.009153 | 0.050806 | −0.006127 |
| 254 | 0.009236 | −0.046658 | 0.080548 | −0.014574 | 0.019311 | −0.014859 | 0.023538 | 0.026691 | 0.021171 | −0.034351 | 0.003688 | −0.016438 | 0.010368 | 0.009753 |
| 255 | 0.033915 | −0.029086 | 0.027486 | −0.037364 | 0.008772 | −0.004407 | 0.034843 | 0.00289 | −0.001528 | −0.03364 | 0.006522 | 0.006657 | 0.022543 | −0.020047 |
| 256 | −0.013891 | 0.018588 | 0.009391 | −0.019169 | −0.002902 | −0.021476 | 0.020052 | −0.007933 | 0.027587 | −0.065464 | 0.053362 | −0.017137 | −0.070393 | −0.014284 |
| 257 | −0.032179 | 0.006375 | −0.039718 | −0.019461 | 0.014911 | 0.022423 | 0.019966 | −0.016263 | 0.024566 | 0.051073 | −0.029018 | −0.014045 | 0.031294 | −0.022469 |
| 258 | 0.028178 | 0.010118 | −0.008864 | −0.01609 | 0.014312 | 0.03405 | 0.020889 | −0.017426 | 0.020979 | 0.009013 | 0.005974 | −0.021394 | −0.005631 | −0.0036 |
| 259 | −0.00124 | 0.019162 | −0.0476 | 0.058023 | 0.008087 | −0.010663 | 0.009227 | 0.009321 | −0.038225 | 0.023898 | 0.000856 | 0.010773 | 0.005798 | 0.00564 |
| 260 | −0.02268 | 0.011788 | −0.014735 | 0.006703 | 0.002261 | 0.00168 | 0.000098 | −0.023974 | −0.010544 | 0.046702 | 0.016806 | 0.006494 | 0.066094 | −0.000069 |
| 261 | 0.016142 | −0.013241 | −0.020623 | 0.003675 | 0.004422 | −0.013582 | 0.003583 | 0.027365 | 0.003715 | 0.01998 | 0.044753 | 0.015764 | 0.040499 | 0.057178 |
| 262 | −0.034298 | 0.01198 | −0.020179 | 0.017016 | 0.015084 | 0.019188 | −0.002626 | −0.008376 | 0.021255 | 0.023359 | 0.015943 | 0.00766 | 0.010563 | −0.009825 |
| 263 | −0.007742 | −0.01007 | −0.050017 | 0.019128 | 0.018852 | 0.048335 | 0.004747 | −0.014665 | 0.0126 | 0.023135 | 0.015508 | −0.005496 | 0.023215 | 0.00111 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 264 | 0.039837 | 0.043687 | −0.032553 | −0.008097 | 0.008412 | 0.035436 | 0.00679 | 0.027501 | 0.017593 | 0.019705 | 0.051352 | −0.000903 | −0.005633 | −0.007596 |
| 265 | 0.047449 | −0.014224 | 0.010148 | −0.066004 | −0.008368 | 0.002611 | 0.008264 | 0.013425 | 0.023073 | 0.003866 | 0.037229 | 0.018862 | 0.001551 | 0.01219 |
| 266 | −0.025442 | −0.052141 | 0.02609 | −0.020216 | −0.015269 | −0.006486 | −0.00764 | 0.002992 | 0.014245 | 0.021006 | 0.036613 | −0.013795 | 0.00887 | 0.02818 |
| 267 | −0.007176 | 0.021888 | 0.021835 | 0.032554 | −0.018254 | −0.019665 | −0.040684 | −0.020554 | 0.005552 | −0.006589 | −0.018625 | −0.024129 | 0.036669 | −0.023263 |
| 268 | 0.011077 | −0.007206 | 0.016813 | 0.012395 | 0.01375 | 0.020478 | −0.005538 | −0.017199 | −0.018606 | 0.013772 | 0.000523 | −0.023491 | 0.016649 | −0.009084 |
| 269 | −0.05006 | 0.017408 | 0.018066 | 0.055865 | 0.004655 | −0.008082 | −0.019113 | 0.012283 | −0.021159 | 0.012243 | 0.003251 | 0.002507 | −0.05718 | 0.002202 |
| 270 | 0.032102 | −0.002853 | 0.026817 | −0.017456 | 0.000212 | 0.005692 | 0.008351 | 0.015627 | −0.003526 | −0.003575 | −0.014018 | 0.029288 | −0.000772 | 0.002753 |
| 271 | −0.063673 | −0.024885 | −0.060077 | −0.036469 | 0.015479 | 0.010791 | −0.024979 | 0.02566 | 0.043309 | −0.006455 | −0.005179 | −0.024514 | 0.078614 | 0.010394 |
| 272 | 0.033594 | −0.021899 | −0.009544 | 0.041514 | 0.019601 | 0.013666 | 0.019475 | −0.011102 | 0.00595 | 0.015255 | 0.018229 | −0.017837 | 0.016108 | 0.01448 |
| 273 | 0.025314 | −0.039711 | 0.010621 | 0.010882 | 0.014056 | 0.009678 | 0.030011 | −0.002698 | −0.008046 | −0.003305 | −0.011399 | 0.015384 | 0.017181 | 0.010967 |
| 274 | 0.043224 | −0.034813 | −0.005164 | 0.012388 | 0.012555 | 0.003441 | 0.034636 | −0.002474 | −0.000544 | −0.003603 | −0.018091 | 0.001335 | 0.001754 | 0.008042 |
| 275 | −0.007025 | 0.029904 | −0.020315 | −0.042341 | −0.024928 | −0.03056 | 0.000847 | 0.038715 | 0.004819 | −0.037858 | 0.004683 | 0.058042 | 0.0162 | −0.004278 |
| 276 | −0.020526 | −0.025481 | −0.029828 | 0.016701 | 0.009794 | 0.025183 | −0.001011 | 0.029762 | 0.022219 | 0.008689 | −0.032756 | −0.096227 | 0.024111 | −0.002118 |
| 277 | −0.015768 | −0.017016 | −0.02683 | −0.012713 | 0.019213 | 0.012607 | 0.024081 | 0.012919 | 0.001003 | −0.012268 | −0.01861 | 0.012599 | 0.002112 | −0.012845 |
| 278 | −0.024554 | −0.003631 | −0.034798 | −0.037493 | 0.017737 | 0.000179 | 0.004156 | 0.027904 | −0.019319 | −0.02487 | −0.016163 | 0.016097 | 0.029601 | 0.003346 |
| 279 | −0.005309 | 0.016715 | 0.025463 | −0.03833 | −0.004348 | 0.014992 | 0.00256 | 0.002848 | 0.000742 | −0.018337 | 0.026569 | −0.004625 | 0.008102 | −0.016481 |
| 280 | −0.00508 | −0.023358 | 0.028824 | 0.024063 | −0.001081 | −0.006622 | −0.004217 | −0.005246 | 0.007171 | 0.042452 | 0.025954 | 0.01096 | 0.029423 | 0.02663 |
| 281 | −0.001427 | −0.021698 | 0.025611 | 0.01616 | 0.002244 | −0.004265 | 0.006486 | 0.007812 | 0.001959 | 0.028709 | −0.000915 | 0.026495 | 0.031874 | 0.022325 |
| 282 | −0.032429 | −0.003067 | 0.024303 | 0.036955 | −0.014928 | −0.041165 | −0.036421 | 0.019647 | −0.040118 | −0.029939 | −0.042837 | 0.037839 | 0.007203 | −0.007943 |
| 283 | 0.032698 | 0.017894 | 0.021969 | 0.028635 | −0.010105 | 0.00948 | −0.022787 | −0.008906 | 0.03554 | 0.006476 | −0.010379 | −0.046444 | 0.003012 | −0.047448 |
| 284 | −0.019213 | 0.005057 | −0.018344 | −0.015981 | 0.003244 | 0.02067 | 0.024233 | −0.013724 | 0.023639 | 0.02244 | 0.012766 | 0.000819 | 0.036228 | −0.022853 |
| 285 | 0.034729 | 0.037477 | −0.025842 | −0.011307 | 0.005565 | 0.012335 | 0.025834 | 0.006855 | 0.01444 | −0.02549 | −0.017503 | −0.02375 | 0.047592 | −0.036345 |
| 286 | −0.023754 | 0.002402 | −0.01536 | −0.019109 | −0.010759 | −0.009876 | −0.000753 | 0.009366 | 0.015893 | 0.033309 | 0.019482 | 0.04455 | −0.053947 | 0.004741 |
| 287 | 0.008236 | 0.012461 | −0.001517 | −0.022359 | −0.018196 | −0.026713 | −0.008426 | −0.004661 | −0.01007 | 0.015302 | 0.003144 | 0.012904 | 0.004165 | 0.007148 |
| 288 | 0.031883 | −0.033489 | −0.006174 | −0.046491 | −0.006704 | 0.031767 | 0.026894 | −0.001206 | −0.006434 | −0.00615 | 0.016726 | 0.002945 | −0.016738 | −0.010376 |
| 289 | −0.034782 | −0.016822 | 0.029414 | −0.010951 | 0.013589 | 0.003344 | 0.036529 | −0.012167 | 0.015488 | 0.006982 | −0.008407 | −0.037186 | −0.003494 | −0.045704 |
| 290 | 0.005874 | −0.026639 | −0.026892 | −0.008574 | −0.01444 | −0.006508 | −0.013832 | −0.00946 | 0.011082 | 0.016061 | −0.005796 | −0.015073 | −0.009798 | −0.020575 |
| 291 | 0.014651 | −0.031741 | −0.02457 | −0.001891 | −0.017465 | −0.002269 | −0.012128 | −0.02093 | 0.010988 | 0.020755 | −0.011221 | −0.009764 | −0.016099 | −0.0222 |
| 292 | 0.036419 | 0.011464 | −0.029037 | −0.002482 | −0.02039 | −0.004838 | 0.016882 | 0.00156 | 0.030593 | 0.000988 | −0.016048 | −0.001931 | −0.036036 | −0.041001 |
| 293 | −0.021104 | 0.016959 | −0.005185 | 0.006831 | −0.006482 | −0.017064 | −0.005072 | −0.036266 | −0.049969 | 0.014759 | −0.001957 | 0.05841 | −0.032322 | −0.021371 |
| 294 | 0.004401 | 0.005462 | 0.057678 | 0.007813 | −0.026732 | −0.009463 | 0.008641 | −0.027225 | −0.000442 | −0.031533 | −0.010375 | −0.022647 | −0.019726 | 0.001694 |
| 295 | −0.016859 | −0.066497 | −0.033037 | 0.00556 | −0.026592 | −0.016394 | −0.00718 | −0.044511 | −0.011736 | 0.026889 | −0.018581 | −0.020581 | −0.010789 | 0.009856 |
| 296 | 0.043531 | −0.02909 | −0.048915 | −0.026843 | −0.022841 | −0.008142 | −0.010336 | 0.034956 | −0.00531 | −0.028844 | −0.008634 | 0.012872 | −0.035755 | −0.007608 |
| 297 | 0.024187 | −0.015883 | 0.006249 | −0.00291 | −0.021786 | 0.011936 | −0.002871 | −0.04649 | −0.019244 | −0.017045 | −0.028937 | −0.032888 | −0.012242 | 0.018351 |
| 298 | 0.000146 | 0.028601 | 0.052362 | −0.030983 | 0.025324 | 0.043696 | 0.000671 | −0.011096 | −0.007663 | 0.016634 | 0.009604 | 0.034568 | −0.027701 | −0.02043 |
| 299 | −0.038162 | −0.009383 | 0.041845 | 0.023843 | −0.036797 | −0.039395 | −0.009448 | −0.030905 | −0.009274 | −0.014606 | −0.035956 | 0.018685 | −0.044151 | 0.020497 |
| 300 | −0.015968 | 0.041043 | 0.046652 | −0.010674 | −0.019548 | −0.01541 | 0.008368 | 0.006055 | 0.059193 | 0.041902 | 0.016301 | 0.020476 | 0.092024 | −0.03147 |
| 301 | −0.015587 | −0.020911 | −0.00769 | −0.03108 | −0.0138 | 0.01323 | −0.013225 | −0.036507 | −0.025489 | −0.02576 | −0.025642 | −0.027089 | 0.044213 | 0.000647 |
| 302 | −0.018937 | −0.064622 | −0.026267 | −0.048252 | 0.001457 | −0.001637 | 0.032581 | 0.003166 | −0.011909 | 0.029062 | −0.026429 | 0.017098 | −0.004562 | −0.009026 |
| 303 | 0.002379 | 0.047989 | 0.015133 | 0.011641 | −0.013362 | −0.01272 | −0.005577 | −0.007366 | −0.016245 | −0.021783 | −0.051431 | −0.001298 | −0.017442 | −0.007767 |
| 304 | 0.047567 | −0.028901 | 0.043447 | 0.033006 | −0.019862 | 0.013676 | 0.004022 | −0.019262 | −0.008985 | −0.036601 | −0.075842 | 0.051826 | −0.029575 | −0.024685 |
| 305 | 0.003699 | 0.051069 | 0.000721 | 0.012437 | 0.037259 | 0.007859 | 0.034337 | 0.017086 | 0.051993 | 0.1242 | −0.018076 | −0.048903 | 0.039318 | −0.021704 |
| 306 | 0.032489 | 0.042489 | −0.049177 | 0.034949 | 0.025113 | 0.027573 | 0.014434 | −0.005651 | −0.002084 | 0.015953 | −0.012602 | −0.023334 | 0.043234 | −0.027793 |
| 307 | −0.030752 | 0.059526 | −0.052806 | −0.00499 | −0.002165 | 0.023664 | 0.004736 | −0.023001 | −0.0060521 | 0.030296 | 0.045008 | −0.016529 | −0.055035 | −0.023714 |
| 308 | 0.06657 | 0.022732 | 0.016026 | 0.008041 | 0.012657 | 0.022025 | 0.001363 | −0.022899 | −0.03996 | −0.048692 | 0.01021 | 0.013408 | 0.011693 | −0.005797 |
| 309 | −0.007844 | −0.004354 | 0.007015 | 0.015891 | 0.010466 | −0.011705 | −0.013449 | 0.004739 | −0.027353 | −0.0184 | −0.010313 | 0.007291 | 0.022697 | 0.004115 |
| 310 | −0.024217 | −0.019487 | 0.036089 | 0.019759 | −0.002602 | −0.028265 | −0.008449 | 0.000097 | −0.02611 | −0.012842 | −0.003112 | −0.005332 | −0.031509 | 0.000161 |
| 311 | −0.03957 | 0.062947 | 0.026174 | 0.01243 | 0.028183 | 0.020344 | −0.009291 | 0.00341 | −0.011146 | 0.036415 | −0.018722 | 0.01008 | 0.07457 | −0.018104 |
| 312 | 0.059253 | 0.036508 | 0.036716 | −0.054513 | −0.034923 | −0.033678 | −0.015433 | 0.00396 | 0.033111 | −0.019698 | −0.020049 | −0.03337 | −0.063467 | −0.019632 |
| 313 | −0.013109 | −0.004849 | −0.012117 | −0.002978 | −0.005642 | −0.004468 | −0.004112 | −0.011527 | −0.002132 | −0.003804 | 0.007221 | 0.017849 | 0.024641 | −0.015444 |
| 314 | 0.022883 | −0.110266 | 0.001032 | 0.021908 | −0.012882 | −0.004874 | 0.010404 | −0.006932 | 0.009493 | 0.038675 | −0.018716 | −0.014529 | 0.064269 | −0.017703 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 315 | −0.016797 | 0.000685 | 0.021782 | 0.000431 | 0.009611 | 0.001167 | 0.008897 | 0.025103 | 0.026096 | 0.029846 | −0.007937 | −0.019911 | 0.016072 | 0.001947 |
| 316 | −0.02112 | −0.036796 | −0.041577 | 0.076074 | 0.010249 | 0.009017 | −0.012926 | −0.009548 | 0.006263 | −0.038767 | 0.051125 | 0.004466 | 0.009535 | 0.019898 |
| 317 | 0.060308 | 0.010046 | −0.007938 | −0.007751 | 0.006692 | 0.012347 | −0.012576 | −0.021311 | −0.019065 | −0.000753 | −0.012984 | −0.027816 | 0.060461 | −0.001779 |
| 318 | 0.055345 | −0.004723 | −0.027966 | 0.040742 | 0.031933 | 0.038636 | 0.020246 | −0.002137 | 0.043718 | 0.002435 | 0.001666 | −0.011534 | −0.003224 | −0.028772 |
| 319 | 0.036429 | −0.025446 | 0.048506 | −0.024574 | 0.004964 | 0.017282 | 0.01065 | 0.009792 | 0.014343 | 0.011786 | −0.016348 | −0.038375 | 0.03534 | 0.012674 |
| 320 | −0.025937 | 0.000346 | 0.050152 | 0.006151 | −0.020096 | 0.029474 | 0.011442 | 0.037783 | 0.039395 | −0.064561 | 0.051782 | 0.044977 | −0.068664 | −0.062297 |
| 321 | −0.067359 | 0.011096 | −0.033662 | −0.036572 | 0.020292 | −0.002486 | 0.016532 | 0.073072 | 0.019226 | −0.009474 | 0.033557 | 0.027976 | −0.026739 | 0.015522 |
| 322 | 0.068558 | −0.036555 | −0.049325 | −0.020758 | −0.024785 | −0.033333 | −0.019442 | −0.020809 | 0.044658 | 0.007187 | −0.045408 | −0.0654 | −0.03355 | 0.000355 |
| 323 | −0.056095 | −0.106152 | −0.03662 | 0.042938 | −0.026384 | −0.010599 | −0.028462 | 0.017046 | 0.012214 | −0.010831 | 0.001148 | −0.00647 | 0.022083 | 0.037643 |
| 324 | −0.069804 | 0.039857 | −0.070508 | 0.018544 | 0.025353 | 0.001347 | 0.008768 | 0.061401 | 0.047791 | 0.023248 | −0.044518 | 0.025157 | 0.049672 | −0.010943 |
| 325 | 0.030042 | 0.067386 | 0.022865 | 0.001315 | 0.002146 | −0.021534 | −0.027047 | 0.031982 | −0.008787 | −0.021759 | 0.014631 | 0.033609 | −0.006598 | 0.021867 |
| 326 | 0.070074 | −0.01429 | −0.035324 | −0.067858 | 0.010098 | −0.005146 | −0.009201 | 0.025585 | 0.048271 | 0.027008 | −0.001035 | −0.048169 | 0.002787 | 0.016439 |
| 327 | 0.026303 | −0.013466 | −0.039484 | 0.027172 | 0.023476 | 0.021808 | 0.020391 | 0.012092 | 0.00633 | −0.037196 | 0.005619 | 0.023289 | −0.030836 | −0.014509 |
| 328 | 0.01264 | 0.074381 | −0.001219 | −0.048651 | 0.020876 | −0.01979 | 0.008424 | 0.024331 | −0.030135 | −0.017656 | −0.022364 | 0.01652 | 0.081832 | −0.019065 |
| 329 | −0.042409 | −0.028267 | −0.040026 | 0.00304 | 0.00944 | 0.031327 | 0.023468 | 0.016957 | 0.024817 | 0.016931 | −0.007236 | −0.007882 | 0.033484 | 0.00585 |
| 330 | 0.024239 | −0.021209 | −0.03061 | 0.003351 | −0.047075 | −0.018414 | −0.032279 | −0.028659 | −0.002935 | 0.025778 | −0.008815 | −0.102326 | −0.04819 | 0.001848 |
| 331 | 0.00442 | −0.027204 | −0.041865 | −0.008597 | 0.005115 | 0.015982 | 0.006669 | 0.010286 | 0.000697 | 0.009945 | 0.0112 | 0.01266 | −0.005756 | −0.00445 |
| 332 | −0.070183 | −0.052462 | 0.044836 | −0.013621 | 0.017545 | 0.02095 | 0.000477 | −0.021731 | 0.015816 | −0.017523 | −0.012123 | 0.02643 | −0.025452 | −0.01317 |
| 333 | 0.01729 | 0.009797 | −0.018677 | 0.00491 | 0.041955 | 0.023328 | 0.015901 | 0.007269 | −0.007097 | −0.015111 | 0.015495 | 0.028313 | 0.015806 | −0.007457 |
| 334 | −0.062769 | 0.023719 | −0.027155 | −0.001005 | −0.007341 | 0.012104 | 0.020005 | −0.044024 | 0.006688 | 0.030413 | 0.037099 | −0.014875 | −0.019557 | −0.025873 |
| 335 | −0.017221 | 0.028758 | 0.019056 | 0.016813 | −0.009812 | −0.007092 | −0.014098 | 0.006916 | −0.014053 | −0.049123 | 0.008461 | 0.00227 | 0.014667 | 0.040458 |
| 336 | −0.040975 | 0.034021 | 0.032352 | 0.035266 | −0.002462 | 0.020397 | −0.02505 | −0.017253 | 0.001693 | −0.005442 | 0.0181 | 0.030596 | −0.033173 | −0.017491 |
| 337 | 0.042381 | 0.028623 | 0.070672 | −0.049154 | 0.009091 | −0.021511 | −0.010629 | 0.007746 | −0.019373 | −0.009521 | 0.089447 | 0.030231 | 0.067202 | 0.061977 |
| 338 | −0.030385 | −0.018282 | 0.009787 | 0.020054 | −0.018171 | −0.009386 | −0.032567 | 0.031683 | −0.002776 | 0.041523 | 0.036338 | −0.00908 | −0.004862 | −0.002539 |
| 339 | −0.008643 | −0.065674 | −0.018161 | −0.044604 | 0.003126 | 0.005577 | −0.008652 | 0.004902 | −0.006997 | 0.005053 | 0.000618 | −0.018611 | 0.078462 | 0.034233 |
| 340 | −0.022465 | −0.042065 | 0.037309 | −0.058503 | 0.035785 | 0.07061 | 0.004484 | −0.004279 | 0.00002 | −0.039252 | 0.023786 | 0.034075 | 0.013181 | 0.022595 |

| | FX | FY | FZ | GA | GB | GC | GD | GE | GF | GG | GH | GI | GJ | GK |
|---|---|---|---|---|---|---|---|---|---|---|---|---|---|---|
| 1 | −0.070147 | −0.065169 | −0.072032 | −0.079937 | −0.067952 | 0.059341 | −0.04182 | −0.083738 | −0.027568 | −0.037226 | 0.03544 | 0.025903 | 0.018329 | −0.108682 |
| 2 | 0.032747 | 0.00022 | 0.000342 | 0.004684 | 0.025018 | 0.070324 | −0.025421 | 0.021144 | 0.029604 | 0.038716 | 0.042823 | −0.00443 | 0.02157 | 0.000621 |
| 3 | 0.018537 | 0.055984 | 0.032665 | 0.068128 | 0.073442 | −0.032148 | −0.006385 | 0.047449 | 0.044304 | 0.016757 | 0.008864 | 0.107769 | −0.019705 | 0.062207 |
| 4 | −0.005425 | −0.031354 | −0.0331 | −0.061706 | −0.03297 | −0.10909 | −0.067681 | 0.025543 | 0.021166 | −0.005861 | −0.071302 | −0.006039 | 0.00226 | −0.060995 |
| 5 | −0.019591 | 0.001092 | −0.026362 | 0.047104 | 0.034316 | −0.005583 | 0.033864 | −0.024238 | 0.031066 | −0.000871 | 0.077688 | 0.045213 | 0.000444 | 0.068243 |
| 6 | −0.00216 | 0.038263 | 0.02582 | 0.030582 | 0.029769 | 0.000941 | 0.010497 | 0.04723 | −0.021795 | −0.059301 | −0.005332 | −0.008144 | −0.036014 | −0.012051 |
| 7 | −0.011157 | −0.019936 | −0.009653 | −0.01939 | −0.031509 | 0.074759 | −0.060876 | −0.135343 | 0.011643 | −0.007202 | −0.044426 | −0.123188 | −0.052375 | −0.080409 |
| 8 | −0.007302 | 0.00542 | 0.01919 | −0.042933 | −0.020055 | −0.00311 | −0.010076 | 0.025727 | 0.024906 | 0.046576 | 0.037134 | 0.002549 | −0.019971 | 0.056996 |
| 9 | 0.028775 | −0.003679 | −0.022235 | 0.011177 | 0.039008 | −0.028803 | 0.002212 | −0.030538 | −0.033939 | −0.051903 | −0.019888 | −0.023755 | −0.091984 | 0.072143 |
| 10 | 0.005419 | −0.064366 | −0.053484 | −0.023389 | 0.037006 | 0.075412 | −0.052052 | −0.0418 | 0.013471 | 0.062113 | 0.057259 | 0.069238 | 0.003399 | −0.04642 |
| 11 | 0.039509 | −0.002289 | 0.005195 | 0.002045 | 0.033961 | 0.017712 | 0.010368 | 0.012083 | −0.010958 | 0.008187 | 0.015061 | −0.008981 | 0.056848 | 0.004277 |
| 12 | 0.03057 | −0.004148 | −0.007193 | −0.00309 | 0.019358 | −0.037092 | −0.010703 | −0.027505 | 0.000122 | 0.005009 | 0.012936 | 0.006577 | 0.057157 | 0.043468 |
| 13 | −0.02993 | −0.02628 | −0.037229 | −0.036581 | −0.03334 | −0.026163 | 0.006441 | 0.003798 | 0.058957 | 0.014111 | 0.101701 | −0.072647 | −0.072698 | 0.050804 |
| 14 | −0.001538 | 0.048964 | 0.057099 | 0.059412 | −0.037288 | −0.056923 | −0.075706 | 0.019785 | 0.036952 | −0.015493 | −0.018003 | 0.05655 | 0.027846 | 0.044952 |
| 15 | 0.029157 | 0.047574 | 0.041001 | 0.065221 | 0.029169 | −0.081216 | −0.007498 | −0.030039 | 0.021495 | −0.039091 | −0.014192 | 0.065479 | 0.062359 | 0.02482 |
| 16 | −0.010818 | 0.007064 | 0.000693 | 0.015671 | −0.009545 | −0.038004 | 0.043123 | 0.047358 | 0.016244 | 0.008585 | 0.017493 | −0.00326 | −0.026861 | −0.024455 |
| 17 | 0.026401 | 0.004641 | 0.005821 | 0.032862 | 0.067228 | 0.084004 | 0.056781 | 0.031174 | −0.031276 | 0.052593 | −0.01471 | 0.007039 | 0.021906 | 0.10394 |
| 18 | 0.000583 | 0.035348 | 0.038476 | 0.012735 | −0.034628 | −0.026268 | −0.033234 | 0.044154 | 0.018403 | 0.054778 | −0.014153 | 0.000019 | 0.026946 | −0.03401 |
| 19 | −0.03463 | −0.022466 | −0.025527 | 0.018718 | −0.005789 | −0.144558 | 0.065819 | −0.054277 | −0.032565 | 0.00716 | −0.038948 | −0.035793 | −0.055409 | −0.026438 |
| 20 | −0.005699 | 0.018379 | −0.028244 | −0.030449 | −0.047294 | −0.007898 | 0.045483 | −0.073069 | −0.031208 | −0.126511 | −0.119732 | −0.05127 | −0.074348 | −0.064911 |
| 21 | −0.005096 | 0.002091 | −0.013616 | −0.043684 | −0.001757 | −0.059864 | 0.045315 | 0.070944 | −0.050135 | −0.038258 | 0.03995 | −0.042315 | 0.020442 | 0.03176 |
| 22 | −0.00608 | 0.001936 | 0.016527 | 0.004303 | −0.064185 | −0.100879 | −0.022574 | 0.106445 | −0.002374 | 0.000448 | 0.031188 | −0.042542 | 0.001517 | −0.000381 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 23 | −0.000662 | −0.075141 | −0.035318 | −0.056972 | −0.006745 | 0.032368 | −0.019301 | −0.079385 | −0.041966 | −0.019902 | −0.041277 | −0.002606 | 0.051091 | −0.048222 |
| 24 | 0.012057 | 0.028964 | 0.005356 | 0.083171 | 0.0345 | 0.041278 | 0.026414 | 0.029673 | 0.008882 | 0.029717 | −0.006441 | −0.006184 | −0.014734 | 0.017985 |
| 25 | −0.005327 | 0.007405 | 0.021847 | 0.042383 | 0.031639 | 0.044495 | −0.055699 | 0.074297 | 0.07549 | 0.033958 | 0.0129 | −0.055028 | −0.065928 | 0.038144 |
| 26 | −0.04782 | 0.017948 | −0.007174 | 0.012203 | 0.023768 | 0.15354 | −0.006904 | 0.017944 | 0.112988 | 0.101469 | −0.015039 | 0.10742 | 0.083933 | −0.013395 |
| 27 | −:0.104505 | 0.006206 | −0.036882 | 0.007861 | −0.113201 | −0.160178 | −0.025843 | 0.055188 | 0.028076 | 0.059237 | 0.141222 | −0.005296 | −0.019574 | −0.002517 |
| 28 | 0.062238 | 0.041159 | 0.018669 | −0.004461 | 0.006611 | −0.034847 | 0.118681 | 0.061531 | 0.022875 | 0.05943 | 0.07685 | 0.072764 | 0.006031 | −0.090007 |
| 29 | 0.033594 | 0.027735 | 0.019924 | −0.024995 | −0.006124 | −0.062868 | 0.011093 | 0.030372 | 0.012276 | 0.015518 | 0.00811 | 0.009099 | −0.001071 | 0.040129 |
| 30 | −0.000233 | −0.001991 | 0.005014 | −0.022163 | −0.038262 | −0.112333 | −0.087605 | 0.046527 | −0.023252 | −0.019568 | −0.069519 | −0.063664 | −0.025793 | −0.140541 |
| 31 | 0.032784 | −0.031437 | 0.004265 | 0.065887 | 0.119302 | 0.062076 | 0.022352 | 0.012834 | −0.023246 | −0.032261 | 0.026987 | 0.018789 | −0.032169 | 0.022814 |
| 32 | 0.004482 | 0.019198 | 0.001272 | −0.005005 | −0.006753 | −0.001933 | −0.064263 | 0.050271 | 0.053867 | −0.051498 | −0.111199 | −0.003387 | 0.100258 | −0.062304 |
| 33 | 0.048195 | 0.000374 | 0.003913 | −0.085904 | 0.002813 | −0.018651 | −0.040035 | −0.005352 | 0.001867 | 0.102194 | 0.158798 | 0.012631 | −0.017969 | −0.055732 |
| 34 | 0.009563 | −0.006455 | −0.027291 | −0.027446 | 0.033035 | 0.022074 | −0.06041 | −0.020072 | 0.001371 | 0.027801 | −0.027179 | −0.025396 | −0.011612 | 0.039117 |
| 35 | −0.012878 | 0.033295 | 0.025126 | 0.051212 | −0.056601 | −0.036157 | 0.095179 | 0.029215 | −0.001054 | 0.048188 | 0.051991 | −0.008722 | −0.039492 | −0.015289 |
| 36 | 0.014211 | 0.021233 | 0.024977 | 0.012076 | −0.024464 | 0.062302 | 0.075304 | 0.048653 | −0.04504 | −0.011962 | −0.003779 | 0.017 | 0.057431 | −0.092188 |
| 37 | −0.023558 | −0.006946 | 0.020593 | 0.043013 | 0.008775 | −0.028319 | −0.022671 | −0.099484 | 0.008464 | 0.047043 | 0.031831 | 0.05364 | 0.042464 | −0.077928 |
| 38 | −0.016042 | 0.003373 | −0.005457 | 0.024231 | 0.084996 | 0.088363 | −0.04698 | 0.040021 | 0.009604 | −0.015002 | −0.045984 | 0.005153 | −0.017122 | −0.026124 |
| 39 | 0.020314 | 0.051661 | 0.054635 | 0:026947 | −0.017855 | 0.03275 | −0.074042 | −0.101576 | −0.032219 | −0.034812 | −0.022012 | 0.079827 | 0.085071 | −0.03824 |
| 40 | −0.086875 | −0.10925 | −0.093158 | −0.013754 | −0.030275 | 0.053132 | 0.237137 | −0.015975 | 0.065773 | 0.055016 | 0.012638 | −0.074869 | −0.038131 | −0.047999 |
| 41 | 0.009258 | 0.009381 | 0.039642 | 0.006265 | 0.03917 | 0.021891 | −0.037745 | −0.04648 | 0.01733 | 0.03122 | −0.010807 | 0.037857 | −0.054318 | −0.03804 |
| 42 | 0.037285 | 0.082103 | 0.059468 | 0.008018 | −0.006503 | −0.029331 | 0.065164 | 0.065025 | 0.00776 | 0.026213 | −0.045737 | 0.046979 | 0.056391 | 0.021218 |
| 43 | 0.041122 | 0.039957 | 0.035354 | 0.001927 | 0.001002 | −0.025139 | 0.033618 | −0.064588 | −0.014721 | −0.096364 | −0.115394 | 0.094844 | 0.010019 | 0.003326 |
| 44 | 0.014545 | 0.017592 | −0.004485 | 0.024575 | 0.03599 | 0.052578 | 0.050596 | −0.044227 | −0.064555 | −0.031642 | −0.00851 | −0.02178 | −0.028716 | −0.042958 |
| 45 | −0.05628 | −0.030613 | −0.045405 | −0.080977 | −0.083402 | 0.034915 | −0.034179 | 0.179033 | 0.043657 | 0.015733 | 0.027913 | 0.081229 | −0.015602 | −0.034973 |
| 46 | 0.054647 | 0.020705 | 0.002784 | 0.00473 | 0.07453 | 0.004393 | 0.022418 | 0.02108 | −0.010224 | 0.02545 | −0.001677 | 0.031253 | 0.09308 | 0.033169 |
| 47 | −0.001887 | 0.028673 | 0.004768 | 0.017998 | 0.041538 | 0.031329 | 0.06883 | 0.128002 | 0.032471 | 0.001213 | −0.063295 | −0.005619 | 0.027064 | 0.02768 |
| 48 | 0.016811 | −0.040752 | 0.003787 | 0.009883 | −0.05777 | −0.121924 | 0.087412 | 0.076194 | 0.029186 | 0.025403 | 0.03026 | 0.000176 | 0.029086 | −0.030456 |
| 49 | −0.037468 | −0.057637 | −0.040053 | −0.008969 | 0.085244 | 0.12888 | −0.070023 | 0.023029 | 0.024786 | 0.001627 | 0.042374 | −0.048821 | −0.098424 | 0.07894 |
| 50 | 0.029402 | 0.042741 | 0.04478 | 0.052678 | −0.056458 | −0.052292 | 0.076344 | 0.048074 | 0.123015 | 0.031286 | 0.001805 | −0.01311 | 0.002751 | −0.015868 |
| 51 | −0.029551 | 0.033999 | 0.030448 | −0.04465 | −0.023251 | 0.022869 | 0.048442 | 0.073288 | −0.069486 | 0.027088 | 0.112746 | 0.063671 | −0.014799 | −0.107608 |
| 52 | 0.051505 | 0.070098 | 0.084604 | 0.032899 | 0.066476 | 0.081822 | 0.109847 | 0.076082 | −0.008232 | −0.058515 | −0.004465 | 0.001059 | 0.011973 | 0.03804 |
| 53 | 0.082329 | 0.029578 | 0.027721 | 0.076892 | 0.009547 | −0.075393 | 0.103496 | −0.073375 | 0.083007 | 0.0724 | 0.038268 | −0.106786 | −0.086496 | 0.023739 |
| 54 | −0.01121 | −0.032648 | −0.005598 | 0.015324 | 0.051219 | 0.09062 | −0.029899 | −0.029014 | 0.053995 | 0.147323 | 0.098589 | −0.09870 | −0.020847 | −0.01081 |
| 55 | 0.016474 | 0.01167 | 0.001266 | 0.01787 | 0.029736 | 0.033038 | 0.006763 | 0.051813 | 0.035163 | −0.025377 | −0.041286 | 0.091816 | 0.047461 | 0.053597 |
| 56 | 0.035099 | 0.046909 | 0.040342 | 0.045354 | −0.013668 | −0.057576 | 0.001674 | −0.064952 | −0.009115 | 0.010913 | −0.047799 | −0.02077 | 0.116664 | 0.055842 |
| 57 | 0.026375 | 0.036513 | 0.055901 | 0.02556 | 0.074254 | 0.052434 | 0.067857 | 0.132477 | 0.045777 | 0.082101 | 0.036024 | −0.039734 | −0.012851 | 0.11768 |
| 58 | 0.010491 | 0.023693 | −0.016675 | 0.014127 | −0.003252 | −0.069671 | −0.055784 | −0.00002 | 0.045644 | 0.012812 | −0.021766 | −0.031466 | −0.02959 | 0.024085 |
| 59 | −0.042522 | 0.019087 | −0.011118 | −0.000545 | −0.045715 | 0.023202 | −0.033849 | 0.006057 | −0.00033/ | 0.038172 | 0.088127 | 0.066287 | −0.036432 | 0.041766 |
| 60 | 0.026824 | 0.098529 | 0.065491 | 0.010986 | −0.040969 | 0.011429 | 0.049354 | −0.138986 | 0.030804 | 0.053039 | 0.081386 | −0.01137 | 0.037949 | −0.07982 |
| 61 | −0.023905 | −0.009255 | −0.003142 | 0.019416 | −0.004785 | −0.006793 | −0.044169 | 0.111792 | 0.049239 | 0.011899 | 0.004443 | −0.012753 | −0.007773 | 0.026281 |
| 62 | 0.022931 | 0.000826 | 0.022775 | −0.011791 | 0.010742 | −0.022025 | 0.020847 | −0.017326 | −0.003293 | 0.034025 | −0.000651 | −0.044544 | −0.054556 | −0.039047 |
| 63 | 0.053584 | 0.005481 | −0.003233 | 0.02043 | 0.062502 | −0.015783 | −0.025345 | 0.019391 | −0.066675 | −0.05311 | 0.015827 | 0.006094 | 0.078689 | 0.021097 |
| 64 | 0.022541 | 0.00378 | −0.000034 | 0.0107 | 0.00643 | 0.02244 | 0.036851 | 0.029688 | −0.006187 | −0.005361 | 0.016965 | 0.023466 | 0.020872 | −0.011531 |
| 65 | −0.016171 | −0.003435 | −0.020748 | −0.031051 | −0.071621 | 0.040706 | −0.004883 | −0.067702 | 0.039027 | 0.028471 | 0.019306 | −0.000926 | 0.011819 | −0.061492 |
| 66 | 0.000384 | 0.020249 | 0.020568 | 0.046665 | −0.00929 | 0.011247 | 0.096959 | −0.10252 | 0.038189 | 0.01167 | 0.074296 | 0.009249 | −0.002721 | 0.030347 |
| 67 | 0.008303 | 0.02105 | 0.052198 | 0.040077 | −0.042847 | −0.095696 | 0.039961 | 0.065486 | −0.023238 | 0.007264 | 0.014387 | −0.102964 | −0.028687 | −0.071693 |
| 68 | 0.040826 | −0.01951 | −0.009192 | 0.019032 | 0.080448 | 0.026205 | −0.036288 | 0.03303 | 0.002904 | −0.027893 | 0.010629 | 0.009458 | 0.004151 | 0.011711 |
| 69 | −0.02679 | 0.015601 | −0.007124 | −0.037928 | −0.030489 | −0.089684 | 0.007523 | −0.058306 | 0.045112 | 0.043777 | 0.041552 | 0.071278 | 0.087577 | −0.062465 |
| 70 | 0.060325 | 0.032438 | 0.001383 | 0.015081 | 0.008323 | 0.001094 | −0.045931 | 0.092109 | −0.013517 | −0.026312 | −0.02337 | −0.017512 | 0.069591 | 0.107377 |
| 71 | −0.009411 | −0.00327 | −0.004618 | 0.029133 | −0.000693 | −0.043055 | −0.039504 | −0.066472 | 0.002567 | −0.012 | 0.02184 | 0.002545 | 0.001979 | −0.065589 |
| 72 | 0.004046 | 0.020434 | 0.042786 | −0.043514 | −0.002917 | 0.044119 | 0.173819 | 0.0723 | 0.026914 | 0.006571 | 0.045579 | 0.028785 | 0.046711 | −0.064696 |
| 73 | −0.022071 | −0.026003 | −0.025443 | 0.018 | −0.004328 | 0.093205 | −0.023168 | −0.013714 | 0.001674 | 0.009156 | −0.005123 | 0.022654 | 0.071222 | 0.134579 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 74 | 0.013109 | 0.003239 | −0.025985 | −0.041993 | −0.030441 | 0.034247 | −0.009413 | 0.022519 | 0.012919 | −0.005202 | −0.024339 | −0.031393 | 0.014016 | −0.041385 |
| 75 | 0.082777 | 0.0335214 | 0.030725 | 0.028218 | 0.103744 | 0.102225 | 0.09953 | −0.034401 | −0.03919 | −0.019353 | 0.00808 | 0.020186 | −0.076542 | 0.011306 |
| 76 | −0.025405 | 0.005895 | 0.020498 | 0.053672 | −0.014484 | −0.046278 | 0.025464 | −0.017265 | −0.058296 | 0.021345 | −0.143231 | 0.033945 | 0.000053 | −0.104402 |
| 77 | 0.000529 | −0.028974 | 0.000743 | 0.010555 | 0.034127 | −0.009366 | 0.007065 | 0.022542 | 0.084843 | 0.034067 | 0.067607 | −0.029059 | −0.031257 | 0.010776 |
| 78 | −0.021208 | −0.075234 | −0.070509 | −0.063135 | 0.007419 | 0.019761 | −0.06842 | −0.017314 | 0.001487 | −0.024011 | 0.017824 | −0.057328 | 0.041934 | 0.00013 |
| 79 | −0.026287 | −0.001981 | 0.01581 | −0.075331 | −0.024485 | 0.087904 | 0.045096 | −0.022615 | −0.128208 | −0.049564 | −0.002438 | 0.01424 | −0.057125 | −0.116753 |
| 80 | −0.013646 | −0.031253 | −0.035014 | 0.110365 | 0.012538 | −0.004819 | 0.035302 | −0.005895 | 0.022411 | 0.035676 | −0.026806 | −0.037185 | −0.012043 | 0.026042 |
| 81 | 0.006164 | −0.008627 | −0.007464 | 0.007646 | −0.005335 | 0.066131 | −0.000244 | 0.069106 | 0.00688 | −0.012313 | −0.021968 | −0.016112 | 0.002369 | 0.007088 |
| 82 | −0.059479 | −0.066531 | −0.063871 | −0.058248 | −0.011395 | −0.004511 | 0.060352 | −0.044567 | −0.060094 | 0.016628 | 0.092152 | 0.031086 | −0.053238 | 0.112936 |
| 83 | 0.052667 | 0.049211 | 0.04718 | −0.029871 | 0.033794 | −0.060941 | 0.092498 | −0.008801 | 0.047388 | −0.0238 | −0.04796 | 0.002896 | 0.003192 | −0.013905 |
| 84 | 0.023003 | −0.034808 | −0.016202 | −0.102911 | 0.038186 | 0.008587 | 0.123601 | 0.049561 | 0.018137 | 0.009828 | −0.057085 | 0.054389 | 0.004506 | 0.030338 |
| 85 | 0.019347 | 0.073001 | 0.060052 | 0.001642 | 0.016146 | 0.128329 | 0.05242 | −0.088779 | 0.017284 | 0.0244 | −0.011417 | 0.030874 | −0.072604 | −0.103764 |
| 86 | −0.019585 | 0.003306 | −0.006424 | −0.00816 | −0.018973 | −0.071133 | 0.058134 | 0.115115 | 0.021896 | 0.015589 | −0.078704 | −0.074133 | 0.00385 | −0.023891 |
| 77 | 0.032252 | −0.056435 | −0.028922 | 0.006298 | 0.010111 | 0.037458 | −0.09425 | −0.006114 | −0.076751 | −0.050088 | −0.038227 | −0.105123 | −0.058144 | 0.078085 |
| 88 | −0.02635 | −0.017217 | −0.016294 | −0.004967 | 0.011095 | −0.073031 | −0.063603 | 0.051497 | −0.136215 | −0.068553 | −0.031196 | −0.057921 | −0.069308 | −0.173698 |
| 89 | −0.082762 | −0.021426 | −0.023397 | 0.030805 | −0.06692 | −0.055726 | 0.079868 | 0.041173 | 0.033458 | −0.015072 | −0.042194 | −0.065626 | 0.017843 | 0.03503 |
| 90 | 0.063081 | 0.051453 | 0.123215 | 0.129072 | 0.105322 | 0.177577 | −0.079983 | −0.085723 | −0.080497 | −0.099282 | −0.037606 | −0.015673 | −0.069983 | 0.072664 |
| 91 | −0.075362 | −0.064902 | −0.066495 | −0.036033 | −0.046092 | −0.01217 | −0.006201 | −0.010469 | 0.051989 | 0.033338 | 0.092902 | −0.086339 | −0.060628 | 0.087148 |
| 92 | 0.033656 | 0.019151 | 0.018554 | 0.030369 | 0.001723 | 0.018818 | −0.094475 | −0.01004 | 0.111322 | 0.071341 | 0.02425 | 0.006606 | 0.026422 | −0.001028 |
| 93 | 0.016062 | 0.007558 | 0.000806 | 0.066652 | −0.038657 | −0.180628 | −0.036239 | −0.09594 | −0.070758 | −0.040379 | −0.016268 | 0.051555 | 0.013947 | 0.079793 |
| 94 | 0.086325 | 0.021518 | −0.008446 | −0.024436 | 0.030192 | 0.131119 | 0.022814 | 0.047027 | 0.00403 | 0.019896 | 0.0043 | −0.007448 | 0.067877 | 0.103661 |
| 95 | 0.01944 | 0.038316 | 0.020086 | 0.018288 | −0.038798 | −0.009735 | −0.087724 | −0.157441 | −0.015114 | 0.06671 | 0.129337 | −0.001956 | −0.007752 | −0.028649 |
| 96 | −0.020729 | −0.01023 | 0.021395 | 0.011515 | −0.031884 | −0.029698 | −0.127002 | 0.016166 | 0.039352 | 0.030218 | −0.016249 | 0.089276 | −0.006772 | −0.009497 |
| 97 | 0.002022 | −0.030072 | −0.022799 | −0.036642 | 0.047927 | −0.036091 | −0.107752 | 0.030108 | −0.058185 | −0.039993 | 0.095479 | 0.008293 | 0.005861 | 0.007558 |
| 98 | −0.037205 | −0.026458 | −0.036581 | −0.082369 | 0.02288 | 0.033847 | 0.025635 | 0.089524 | 0.035995 | 0.04057 | −0.004914 | 0.047735 | 0.045541 | −0.06498 |
| 99 | 0.030774 | 0.072591 | 0.048459 | −0.004922 | −0.053113 | −0.008208 | 0.095892 | 0.10476 | −0.016846 | 0.013611 | 0.039358 | −0.088406 | −0.044288 | −0.089341 |
| 100 | −0.015436 | −0.01815 | −0.029853 | −0.075384 | −0.090258 | −0.063743 | −0.036568 | −0.086214 | −0.056047 | −0.046752 | −0.054818 | −0.012639 | 0.010311 | −0.005957 |
| 101 | −0.032641 | −0.049972 | −0.059508 | −0.026096 | 0.053813 | −0.047957 | 0.028283 | 0.081756 | −0.0057 | −0.01968 | −0.060742 | 0.036792 | −0.032244 | 0.106355 |
| 102 | −0.003017 | 0.007178 | 0.010989 | −0.024828 | 0.019126 | 0.040438 | 0.036892 | −0.060216 | −0.050423 | −0.149174 | −0.084994 | −0.012635 | 0.00678 | 0.052449 |
| 103 | −0.021291 | −0.016248 | 0.013583 | 0.009229 | 0.001969 | −0.012195 | 0.097621 | −0.059116 | −0.018739 | 0.038284 | −0.044101 | −0.019269 | −0.025224 | 0.043706 |
| 104 | −0.018366 | 0.002496 | −0.011912 | 0.003894 | −0.033869 | −0.01634 | 0.086207 | 0.015788 | −0.060915 | −0.037767 | −0.000658 | −0.021195 | −0.048704 | −0.036832 |
| 105 | −0.01688 | −0.025427 | −0.030146 | 0.041263 | 0.00023 | 0.051334 | 0.001843 | 0.039547 | 0.020931 | −0.014235 | −0.057471 | −0.053521 | −0.099682 | −0.029467 |
| 106 | 0.068123 | 0.021394 | 0.036205 | 0.115088 | 0.083199 | −0.034909 | −0.109492 | 0.03293 | 0.075579 | 0.003961 | 0.099614 | −0.012563 | −0.015002 | −0.06125 |
| 107 | −0.019042 | 0.026278 | 0.022639 | −0.004225 | −0.121277 | −0.153698 | 0.065451 | 0.016209 | 0.004809 | −0.01368 | −0.018795 | −0.021485 | 0.008986 | 0.077937 |
| 108 | 0.035664 | −0.013196 | 0.009173 | 0.01982 | 0.054783 | 0.042684 | −0.008022 | −0.016032 | 0.00431 | 0.032009 | −0.021453 | 0.014548 | 0.069157 | −0.018477 |
| 109 | −0.00624 | 0.011689 | 0.012425 | 0.04076 | −0.018753 | 0.011158 | 0.031162 | −0.01798 | 0.036685 | −0.002874 | 0.027073 | 0.018469 | −0.048865 | 0.060703 |
| 110 | −0.032183 | −0.007031 | −0.011633 | −0.016112 | −0.02267 | 0.065338 | 0.028271 | −0.013845 | 0.014654 | −0.046437 | −0.039372 | 0.003565 | 0.033196 | −0.03529 |
| 111 | −0.039236 | −0.010928 | −0.001122 | −0.018454 | −0.019344 | −0.045505 | 0.016057 | 0.037107 | −0.028746 | −0.022161 | −0.014559 | 0.04875 | −0.028082 | −0.017088 |
| 112 | −0.005604 | −0.027366 | −0.019605 | −0.062816 | −0.006519 | 0.057345 | −0.053704 | 0.029523 | −0.06087 | −0.030591 | 0.036138 | −0.013394 | −0.033232 | 0.00283 |
| 113 | 0.032877 | 0.013068 | 0.009105 | −0.001213 | 0.0216 | −0.006497 | 0.022323 | 0.101151 | −0.003308 | −0.016966 | −0.021123 | −0.023485 | 0.055559 | −0.011945 |
| 114 | −0.007701 | −0.006037 | 0.009265 | −0.054241 | −0.066829 | −0.066709 | 0.008875 | −0.000014 | −0.033705 | −0.027084 | 0.021928 | −0.051903 | 0.015273 | 0.091204 |
| 115 | −0.025903 | −0.020411 | −0.012139 | −0.049129 | −0.027198 | 0.09876 | −0.044514 | −0.07741 | −0.017781 | −0.005416 | 0.011267 | −0.030908 | 0.048673 | 0.008839 |
| 116 | 0.023065 | −0.038449 | −0.035824 | −0.063872 | −0.000535 | −0.021584 | −0.069254 | −0.034629 | 0.024553 | 0.027302 | 0.058129 | 0.080378 | 0.0281 | −0.050603 |
| 117 | −0.052306 | 0.012456 | −0.072452 | −0.043141 | −0.026681 | 0.047143 | −0.056992 | 0.005112 | 0.025851 | 0.02833 | −0.026801 | −0.035273 | −0.063026 | −0.055008 |
| 118 | −0.049108 | −0.027855 | 0.016151 | 0.000558 | 0.010248 | −0.012705 | 0.075262 | 0.060415 | 0.034875 | −0.00961 | −0.020778 | 0.017085 | −0.000635 | −0.09905 |
| 119 | 0.046184 | 0.054597 | −0.00406 | −0.085059 | −0.048407 | −0.051318 | 0.036115 | 0.105475 | 0.02255 | −0.053484 | −0.021699 | −0.041489 | −0.172581 | −0.045797 |
| 120 | −0.028384 | −0.031819 | 0.024195 | 0.081913 | −0.01291 | −0.053134 | 0.005173 | −0.044324 | 0.01711 | 0.021386 | 0.034571 | −0.071972 | −0.054654 | 0.030033 |
| 121 | 0.039929 | 0.003631 | 0.021785 | −0.053172 | −0.015831 | 0.005453 | −0.078991 | −0.036313 | −0.078167 | −0.067631 | 0.050572 | 0.052124 | 0.039927 | 0.028999 |
| 122 | −0.033502 | 0.002529 | −0.001532 | 0.033312 | −0.013273 | −0.035367 | 0.01367 | −0.032658 | 0.002431 | 0.035956 | 0.041014 | 0.104937 | 0.051603 | 0.024732 |
| 123 | −0.003938 | 0.029395 | −0.017636 | 0.017452 | 0.001528 | 0.003212 | −0.038438 | −0.043635 | 0.065321 | 0.021684 | −0.105426 | −0.039661 | 0.100371 | 0.000837 |
| 124 | 0.049982 | 0.030382 | 0.085631 | 0.056215 | −0.016114 | −0.070454 | 0.12029 | −0.037472 | −0.018691 | −0.00089 | −0.015993 | −0.018269 | −0.038923 | 0.017473 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 125 | 0.064498 | −0.028275 | 0.003735 | −0.010858 | −0.013725 | −0.046685 | 0.014676 | 0.023817 | −0.143026 | −0.07183 | −0.063851 | −0.056044 | −0.060783 | 0.051459 |
| 126 | 0.053066 | 0.040165 | 0.012524 | 0.016099 | 0.029689 | −0.044382 | −0.03525 | 0.046747 | 0.005222 | 0.090283 | 0.07203 | −0.002843 | −0.007828 | 0.017892 |
| 127 | −0.069335 | −0.029692 | 0.047522 | 0.02713 | 0.078269 | 0.058316 | −0.177508 | 0.151286 | 0.005598 | 0.018743 | 0.073997 | 0.08473 | −0.036547 | −0.057449 |
| 128 | 0.010759 | 0.029808 | 0.057852 | −0.020771 | −0.089667 | −0.103964 | −0.111837 | −0.016671 | −0.089168 | −0.049552 | −0.072907 | −0.008337 | 0.006077 | 0.045803 |
| 129 | 0.005842 | 0.002499 | −0.003337 | 0.001032 | 0.013415 | 0.006485 | −0.064708 | 0.025353 | −0.014984 | 0.027817 | 0.027266 | 0.035071 | −0.053414 | 0.049281 |
| 130 | 0.007408 | −0.001906 | −0.016837 | −0.030705 | 0.031146 | 0.017678 | −0.00173 | −0.105747 | 0.031187 | 0.02095 | 0.006653 | 0.004716 | 0.041872 | −0.065246 |
| 131 | 0.008608 | 0.028501 | 0.017445 | 0.022375 | −0.036044 | 0.01755 | 0.013056 | 0.01545 | 0.04968 | 0.032108 | −0.010751 | 0.008495 | 0.019993 | 0.007823 |
| 132 | 0.011522 | 0.036774 | −0.013115 | 0.009321 | 0.017046 | −0.069069 | −0.068425 | 0.078489 | 0.131392 | 0.017176 | −0.027737 | −0.011392 | −0.080976 | −0.036386 |
| 133 | −0.020681 | 0.007272 | −0.005701 | −0.008685 | 0.015829 | 0.095989 | 0.108595 | −0.000762 | 0.075357 | 0.084558 | 0.083179 | −0.089062 | −0.018326 | −0.007949 |
| 134 | 0.058323 | 0.028466 | 0.018165 | 0.05957 | 0.006611 | 0.004455 | −0.107595 | 0.062687 | −0.04038 | −0.02847 | −0.055253 | −0.007682 | −0.037012 | 0.006992 |
| 135 | 0.009831 | −0.01746 | −0.035548 | −0.075604 | 0.028052 | 0.051376 | −0.080902 | 0.035493 | −0.021025 | −0.023512 | 0.049211 | 0.021059 | −0.063136 | −0.001948 |
| 136 | −0.032339 | −0.003585 | −0.000582 | 0.023517 | −0.053008 | 0.001493 | 0.030879 | −0.06943 | −0.076855 | −0.045658 | −0.008316 | −0.033373 | 0.005095 | 0.051845 |
| 137 | −0.059179 | −0.019126 | −0.015739 | −0.038851 | −0.05934 | 0.015594 | −0.062735 | 0.029833 | 0.06828 | 0.009439 | −0.008191 | 0.032595 | 0.055813 | 0.011077 |
| 138 | −0.029268 | −0.011138 | 0.005058 | 0.011355 | −0.012884 | 0.03301 | 0.02819 | −0.049276 | −0.018177 | −0.006203 | −0.058558 | −0.068666 | 0.001694 | 0.012669 |
| 139 | 0.010819 | 0.014148 | 0.0191 | 0.026728 | −0.002292 | 0.006796 | −0.030845 | −0.007658 | −0.018801 | 0.011644 | 0.000728 | −0.002422 | 0.021021 | 0.045388 |
| 140 | −0.013302 | −0.010156 | −0.00303 | −0.001165 | 0.011313 | −0.025063 | 0.066496 | −0.048176 | −0.007953 | −0.036378 | 0.034522 | 0.077305 | −0.058136 | 0.016248 |
| 141 | 0.030502 | 0.028807 | 0.038708 | 0.062218 | 0.020278 | 0.081093 | 0.000061 | 0.01781 | 0.022271 | −0.003537 | 0.030788 | −0.021677 | 0.002421 | −0.006161 |
| 142 | −0.039552 | −0.011574 | 0.013065 | −0.000003 | −0.000229 | −0.02802 | −0.054625 | 0.042673 | 0.043588 | 0.003827 | −0.011639 | 0.056304 | −0.009731 | 0.026125 |
| 143 | 0.004386 | 0.029863 | 0.014416 | 0.005169 | 0.017838 | 0.001254 | −0.043702 | −0.037906 | 0.00835 | 0.039059 | 0.027664 | −0.005254 | −0.014268 | −0.013704 |
| 144 | 0.01988 | 0.004447 | −0.007903 | −0.0691 | −0.011875 | 0.0171 | 0.001468 | 0.017157 | 0.006492 | −0.004179 | 0.026503 | −0.002595 | 0.014039 | −0.026701 |
| 145 | −0.014745 | −0.050449 | −0.01163 | 0.037533 | 0.005348 | 0.010104 | −0.062878 | −0.02457 | −0.01013 | 0.004834 | 0.042454 | −0.004399 | 0.029051 | −0.000851 |
| 146 | −0.013291 | 0.023416 | 0.027572 | 0.014771 | −0.022323 | −0.009021 | 0.027371 | 0.008142 | −0.011222 | 0.004594 | −0.052459 | 0.047673 | 0.046519 | −0.083971 |
| 147 | −0.0329 | −0.042573 | −0.014688 | −0.018144 | −0.012661 | 0.022536 | 0.099467 | 0.003526 | 0.015522 | 0.016608 | −0.025058 | 0.004993 | 0.027678 | 0.030592 |
| 148 | 0.005391 | −0.013715 | −0.000722 | −0.026582 | 0.008766 | 0.017209 | −0.042586 | 0.028173 | −0.012422 | −0.057157 | −0.079706 | 0.003519 | −0.001107 | 0.023206 |
| 149 | 0.014765 | −0.009565 | −0.013862 | −0.025501 | 0.004226 | −0.050689 | −0.055662 | 0.024579 | 0.03898 | 0.029762 | 0.048685 | −0.02199 | −0.040795 | −0.016474 |
| 150 | 0.036066 | 0.035244 | 0.020807 | −0.035419 | 0.008061 | 0.035077 | 0.042549 | 0.00051 | 0.022367 | 0.010288 | 0.050433 | 0.076686 | 0.044736 | −0.06821 |
| 151 | 0.017499 | 0.017732 | −0.015998 | 0.011574 | 0.054515 | −0.007878 | 0.02839 | 0.034257 | 0.038134 | 0.005135 | −0.008012 | −0.065444 | 0.010951 | 0.031335 |
| 152 | −0.038281 | −0.030543 | −0.036147 | 0.03036 | 0.008463 | −0.043327 | 0.023465 | −0.064764 | 0.044458 | 0.067472 | 0.057435 | −0.000377 | 0.017777 | −0.004037 |
| 153 | 0.017382 | 0.006074 | −0.023029 | −0.000246 | −0.032161 | −0.029199 | −0.019017 | −0.032093 | −0.001641 | −0.003541 | 0.008903 | 0.004584 | 0.024292 | 0.009682 |
| 154 | 0.003438 | −0.00101 | 0.007831 | −0.007518 | 0.011299 | 0.037673 | 0.007565 | −0.03802 | 0.009526 | 0.009886 | 0.023495 | 0.01737 | 0.042304 | 0.007957 |
| 155 | 0.026123 | 0.041097 | 0.021962 | −0.009103 | −0.015071 | −0.026546 | 0.004661 | 0.050323 | 0.006527 | −0.019317 | 0.007305 | 0.034596 | 0.006678 | −0.025178 |
| 156 | −0.002943 | −0.000611 | 0.0097 | 0.028183 | 0.021595 | 0.011979 | −0.003598 | 0.075072 | 0.031206 | −0.006013 | 0.029034 | 0.021804 | −0.066835 | −0.018209 |
| 157 | 0.049111 | 0.012156 | 0.018394 | 0.031783 | −0.00092 | 0.000663 | −0.033925 | 0.007429 | −0.033671 | 0.012866 | −0.083604 | −0.016814 | −0.014777 | 0.033761 |
| 158 | 0.023307 | −0.009647 | −0.013424 | −0.015771 | 0.008347 | −0.027283 | 0.07288 | 0.027019 | −0.020284 | −0.029681 | −0.03223 | −0.019667 | 0.037392 | 0.026744 |
| 159 | −0.016058 | 0.000139 | −0.003081 | −0.040017 | −0.013827 | 0.023337 | 0.02823 | 0.003958 | −0.006371 | −0.010161 | −0.045205 | −0.010953 | 0.021414 | 0.01832 |
| 160 | 0.026684 | 0.016972 | 0.009843 | 0.028946 | 0.032965 | −0.054901 | 0.034187 | −0.029198 | 0.020365 | 0.008433 | −0.037476 | −0.027259 | 0.004446 | −0.034636 |
| 161 | −0.00442 | 0.008581 | 0.011109 | 0.031155 | 0.0538 | 0.012737 | 0.065138 | −0.059455 | 0.032538 | 0.051186 | 0.037129 | 0.009766 | −0.015674 | −0.056842 |
| 162 | −0.012622 | −0.021724 | −0.000756 | 0:010221 | 0.01598 | 0.058546 | 0.051518 | −0.012036 | −0.034713 | −0.033492 | −0.006153 | −0.079487 | 0.01114 | 0.012233 |
| 163 | −0.009673 | 0.010395 | 0.024173 | 0.050598 | 0.010873 | −0.011949 | −0.045113 | −0.008154 | −0.009251 | −0.013586 | −0.020067 | 0.018 | 0.033756 | −0.021806 |
| 164 | 0.034673 | 0.040456 | 0.03209 | 0.02978 | 0.039356 | 0.032233 | 0.026582 | −0.032277 | −0.00141 | 0.016106 | −0.047147 | 0.036501 | 0.086768 | −0.035764 |
| 165 | −0.000971 | −0.008406 | 0.005756 | −0.025651 | −0.014781 | 0.000991 | −0.009842 | −0.008567 | −0.068033 | −0.070136 | 0.015892 | 0.031 | 0.051952 | −0.011991 |
| 166 | 0.005535 | −0.015175 | −0.009188 | 0.000732 | 0.059357 | −0.020993 | −0.021064 | 0.028266 | −0.012457 | −0.006523 | 0.030258 | 0.011022 | −0.009504 | 0.014737 |
| 167 | −0.053213 | −0.055385 | −0.044261 | 0.005748 | 0.004069 | 0.013538 | 0.036503 | 0.001558 | −0.03096 | 0.010499 | 0.02485 | −0.008147 | −0.013539 | 0.009427 |
| 168 | −0.06985 | 0.001296 | 0.02646 | −0.017583 | −0.086742 | −0.067947 | 0.021774 | −0.016283 | 0.041097 | 0.021775 | 0.005709 | −0.04208 | −0.015665 | −0.098353 |
| 169 | −0.022193 | −0.008338 | −0.001955 | −0.002491 | 0.004046 | 0.021183 | 0.038125 | 0.024117 | 0.023211 | 0.001413 | 0.005353 | 0.006999 | −0.006094 | 0.033459 |
| 170 | −0.011972 | −0.025241 | −0.024428 | −0.055262 | −0.000277 | 0.015479 | 0.099533 | 0.047954 | 0.03045 | 0.022667 | 0.061121 | −0.015384 | −0.013763 | 0.041062 |
| 171 | −0.055204 | −0.008614 | −0.019431 | 0.008266 | −0.079227 | −0.068763 | 0.041442 | −0.02854 | 0.052463 | 0.042384 | 0.027363 | −0.025591 | 0.008547 | 0.039449 |
| 172 | 0.027032 | 0.051829 | 0.065281 | 0.038082 | 0.041434 | −0.011525 | −0.013604 | −0.016371 | −0.000361 | −0.036052 | −0.023236 | 0.040817 | −0.004062 | −0.024287 |
| 173 | 0.040589 | 0.009944 | 0.021513 | 0.016012 | −0.000056 | −0.054746 | 0.016711 | −0.021169 | −0.061151 | −0.025308 | −0.002016 | −0.000848 | 0.005485 | 0.017478 |
| 174 | 0.000401 | 0.021237 | 0.005212 | 0.014967 | 0.02453 | −0.00931 | 0.009094 | 0.031411 | 0.018168 | −0.073363 | −0.055911 | −0.014908 | −0.026621 | 0.012547 |
| 175 | −0.019124 | 0.007983 | −0.009952 | −0.026154 | 0.002166 | 0.051644 | 0.02069 | 0.075157 | 0.053709 | 0.013959 | −0.083558 | −0.029472 | −0.009943 | −0.039441 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 176 | −0.001753 | 0.024108 | 0.01066 | 0.027104 | 0.006409 | 0.009836 | −0.00556 | 0.00375 | 0.009584 | −0.014183 | −0.081052 | −0.040975 | 0.073882 | 0.008344 |
| 177 | 0.009268 | 0.026044 | −0.00168 | −0.041987 | −0.035343 | 0.050198 | −0.01341 | −0.019373 | 0.036488 | 0.022925 | 0.069034 | −0.015158 | −0.018156 | −0.009492 |
| 178 | −0.059379 | −0.090469 | −0.079011 | −0.052689 | 0.022942 | 0.006439 | −0.038132 | 0.040277 | 0.025057 | 0.021057 | 0.070091 | −0.007528 | −0.014792 | 0.012953 |
| 179 | 0.838351 | −0.083437 | −0.084692 | −0.060474 | −0.098984 | −0.01879 | −0.007069 | −0.011375 | 0.027071 | 0.037938 | 0.019861 | −0.028953 | −0.032035 | −0.042103 |
| 180 | −0.081663 | 0.854137 | −0.111673 | −0.069413 | −0.005101 | 0.015583 | −0.030117 | −0.002368 | −0.011856 | 0.018226 | 0.023213 | −0.051636 | −0.056329 | 0.00484 |
| 181 | −0.072366 | −0.110551 | 0.863023 | −0.091619 | −0.025227 | 0.008074 | −0.029482 | 0.001219 | 0.007559 | 0.028662 | 0.021931 | −0.0492 | −0.044788 | 0.014777 |
| 182 | −0.052298 | −0.075119 | −0.093488 | 0.78018 | −0.080095 | 0.003212 | −0.006492 | 0.038181 | −0.041213 | −0.008838 | 0.03926 | −0.013446 | −0.02677 | −0.044511 |
| 183 | −0.090399 | −0.008806 | −0.030191 | −0.077376 | 0.741733 | −0.177281 | 0.038365 | −0.050363 | −0.012642 | −0.000872 | −0.009091 | −0.065502 | 0.005743 | −0.054054 |
| 184 | −0.018652 | 0.044768 | 0.025413 | 0.046802 | −0.194397 | 0.493022 | 0.031064 | −0.001762 | 0.001954 | −0.016302 | −0.034593 | −0.030186 | 0.014569 | −0.031213 |
| 185 | 0.002797 | −0.056558 | −0.041607 | −0.0088 | 0.003413 | −0.013634 | 0.415969 | −0.044791 | −0.043636 | −0.034055 | 0.009033 | 0.037627 | 0.020621 | −0.0342 |
| 186 | 0.009317 | −0.03594 | −0.020766 | 0.01109 | −0.020694 | 0.032088 | −0.022067 | 0.522945 | −0.069519 | −0.023919 | −0.003685 | 0.017538 | 0.043193 | −0.039416 |
| 187 | 0.027272 | −0.025905 | 0.010141 | −0.038702 | −0.01516 | −0.012467 | −0.012941 | −0.071536 | 0.709552 | −0.156232 | −0.080486 | 0.011427 | −0.010939 | −0.022485 |
| 188 | 0.015174 | −0.002319 | 0.004688 | −0.006634 | −0.013329 | −0.028071 | −0.035329 | −0.012095 | −0.16391 | 0.755738 | −0.179924 | 0.000337 | −0.018733 | 0.00571 |
| 189 | 0.024904 | 0.030353 | 0.026723 | 0.013408 | −0.032709 | −0.032287 | 0.034347 | 0.006815 | −0.086404 | −0.170586 | 0.603216 | −0.038613 | 0.023882 | −0.027441 |
| 190 | −0.003999 | −0.026411 | −0.019145 | 0.001364 | −0.030375 | −0.022343 | 0.069328 | −0.036703 | −0.007799 | 0.005216 | −0.019321 | 0.692125 | −0.171855 | 0.043115 |
| 191 | −0.021377 | −0.007729 | 0.002179 | 0.001369 | 0.004003 | −0.028633 | 0.000939 | 0.010309 | −0.009467 | 0.002732 | 0.066989 | −0.101028 | 0.695128 | 0.014211 |
| 192 | −0.033504 | 0.030088 | 0.008666 | −0.061507 | −0.051859 | −0.018522 | 0.032057 | −0.029679 | 0.013873 | 0.010532 | −0.000202 | 0.007186 | −0.036832 | 0.570831 |
| 193 | −0.036351 | −0.00195 | 0.022837 | −0.076172 | −0.023788 | 0.005203 | −0.019378 | −0.025022 | −0.088483 | −0.035023 | 0.061855 | 0.055068 | −0.0147 | −0.122047 |
| 194 | −0.022389 | −0.015384 | −0.010305 | 0.047178 | −0.034003 | −0.064915 | −0.006609 | −0.058417 | −0.039731 | −0.075807 | −0.0652 | 0.018067 | 0.020034 | 0.023787 |
| 195 | −0.009226 | −0.035601 | −0.021873 | −0.014183 | −0.010149 | 0.019634 | −0.030764 | −0.052127 | −0.023209 | 0.035937 | −0.012641 | −0.069566 | −0.020388 | 0.001419 |
| 196 | −0.021594 | −0.027313 | −0.013624 | −0.027568 | −0.013617 | −0.052953 | −0.028081 | −0.033886 | 0.024977 | 0.011408 | −0.036197 | −0.05869 | −0.048373 | 0.006338 |
| 197 | 0.005352 | 0.009059 | −0.000396 | −0.015402 | 0.026423 | 0.040198 | 0.009102 | −0.027897 | 0.028708 | 0.011493 | 0.024163 | −0.094799 | −0.127417 | −0.048984 |
| 198 | 0.016586 | 0.028177 | 0.019328 | −0.015106 | 0.013003 | −0.023351 | −0.008578 | 0.017368 | 0.018115 | 0.009892 | −0.005567 | 0.052 | 0.031146 | −0.038852 |
| 199 | 0.018876 | −0.007581 | 0.00289 | 0.023364 | 0.014425 | −0.015635 | 0.026557 | −0.049653 | −0.019048 | 0.000464 | −0.016982 | 0.016029 | 0.003399 | 0.041978 |
| 200 | −0.05123 | 0.002195 | −0.014133 | 0.00432 | −0.045426 | 0.046053 | 0.022858 | −0.031276 | −0.054819 | −0.013243 | −0.009904 | 0.058507 | 0.059345 | 0.006057 |
| 201 | 0.00541 | −0.025754 | −0.018563 | −0.00219 | −0.007523 | 0.024969 | −0.037612 | 0.009891 | 0.014924 | 0.018545 | −0.001195 | −0.045368 | −0.000115 | 0.031401 |
| 202 | 0.005144 | 0.000983 | 0.008546 | −0.011803 | 0.030655 | 0.050212 | 0.054768 | −0.04824 | 0.002022 | 0.010586 | 0.043166 | 0.005068 | −0.002599 | −0.044739 |
| 203 | −0.011822 | 0.001288 | 0.014551 | −0.002926 | −0.040871 | 0.014423 | 0.04078 | 0.080494 | −0.009572 | −0.025612 | −0.040653 | −0.021587 | −0.022812 | 0.01255 |
| 204 | 0.002605 | 0.007772 | −0.020503 | −0.024258 | −0.016936 | −0.005901 | −0.009256 | −0.03848 | −0.003857 | 0.035355 | 0.045639 | −0.05456 | 0.010239 | 0.04617 |
| 205 | 0.000327 | −0.016998 | −0.020691 | −0.030449 | −0.033057 | −0.021939 | 0.035059 | 0.00712 | 0.029861 | 0.037361 | 0.036988 | −0.084214 | −0.02211 | 0.057577 |
| 206 | 0.035087 | 0.032215 | 0.035435 | 0.04713 | 0.031769 | −0.084838 | −0.01802 | −0.035046 | 0.022831 | −0.012074 | 0.004632 | −0.007905 | 0.027309 | −0.045733 |
| 207 | 0.001182 | −0.018635 | −0.029833 | −0.020899 | −0.022003 | 0.021991 | −0.039118 | −0.085591 | −0.010873 | −0.025471 | −0.056083 | 0.001692 | 0.018329 | 0.01936 |
| 208 | 0.002482 | −0.013975 | −0.002966 | 0.035338 | 0.005702 | −0.019936 | −0.01127 | 0.00583 | 0.004444 | 0.010558 | −0.00014 | −0.031315 | −0.006974 | 0.045883 |
| 209 | 0.000693 | 0.010659 | 0.001579 | 0.008936 | 0.009404 | −0.04234 | −0.03209 | 0.012109 | 0.006979 | 0.00748 | 0.01864 | 0.064863 | 0.029433 | −0.003057 |
| 210 | 0.010406 | −0.032414 | −0.026806 | −0.019375 | 0.000957 | −0.025869 | −0.008707 | −0.004213 | 0.001283 | 0.036235 | 0.035618 | −0.002773 | 0.037694 | 0.000834 |
| 211 | −0.01088 | 0.003448 | 0.024047 | 0.069513 | 0.001482 | −0.008462 | −0.043639 | −0.001778 | 0.011026 | 0.015193 | 0.05362 | −0.002423 | −0.026846 | 0.017367 |
| 212 | 0.011166 | 0.045133 | 0.016558 | −0.004311 | −0.020043 | −0.006831 | −0.038355 | −0.012761 | 0.018647 | 0.034079 | 0.052323 | −0.019692 | 0.019199 | 0.040349 |
| 213 | −0.00455 | −0.014438 | 0.004597 | −0.057484 | −0.015367 | −0.038548 | −0.039287 | −0.003111 | 0.018236 | 0.029359 | −0.015635 | −0.001027 | −0.006868 | 0.024343 |
| 214 | −0.111647 | −0.053584 | −0.036052 | 0.000946 | −0.067732 | −0.047409 | 0.015973 | −0.047469 | 0.055716 | 0.025242 | −0.048 | −0.014067 | −0.010085 | −0.045161 |
| 215 | −0.055459 | −0.041558 | −0.057112 | −0.050721 | −0.028236 | 0.05262 | −0.026668 | −0.076269 | −0.00537 | 0.020392 | 0.017565 | 0.01142 | −0.018278 | −0.004181 |
| 216 | 0.024201 | 0.004458 | −0.001633 | −0.000107 | −0.010109 | −0.001293 | −0.040579 | −0.046026 | −0.022677 | 0.000153 | 0.000419 | −0.005959 | −0.017774 | 0.04009 |
| 217 | 0.003173 | 0.020855 | 0.032341 | −0.00057 | −0.027513 | 0.04395 | −0.025352 | −0.040548 | −0.013952 | −0.010211 | 0.012318 | −0.014423 | −0.017899 | 0.025714 |
| 218 | 0.035878 | −0.003471 | −0.00033 | −0.000868 | 0.03821 | 0.035351 | 0.022559 | −0.010596 | 0.026141 | 0.022903 | −0.002625 | 0.021473 | −0.003372 | −0.001688 |
| 219 | 0.030278 | 0.023008 | 0.017645 | 0.041084 | 0.008413 | −0.01044 | −0.005079 | −0.014114 | 0.007157 | 0.01967 | −0.011189 | 0.019251 | 0.013819 | 0.045448 |
| 220 | −0.007237 | −0.000873 | 0.006235 | −0.025128 | 0.012077 | 0.02845 | 0.039433 | −0.041345 | −0.031308 | 0.02449 | 0.038874 | 0.02726 | 0.005134 | 0.036835 |
| 221 | 0.002345 | 0.012219 | 0.022444 | 0.034086 | −0.033625 | −0.027674 | −0.010579 | −0.013319 | 0.014995 | 0.010084 | −0.000906 | −0.008378 | 0.013261 | 0.009578 |
| 222 | 0.011412 | 0.023706 | 0.013788 | 0.029979 | −0.015514 | −0.012391 | 0.035287 | 0.019991 | 0.02517 | −0.025025 | −0.0196 | −0.008328 | 0.004784 | −0.019949 |
| 223 | 0.015872 | 0.016149 | 0.00415 | −0.0106 | −0.007203 | 0.027477 | 0.049382 | 0.039178 | 0.000714 | −0.003086 | 0.009689 | −0.001856 | 0.058228 | 0.049642 |
| 224 | 0.020542 | −0.015027 | −0.019872 | 0.024062 | 0.045271 | −0.004661 | −0.002795 | 0.001019 | 0.025746 | 0.021167 | 0.006419 | −0.019564 | −0.014983 | −0.049139 |
| 225 | 0.036726 | 0.017999 | 0.006219 | 0.033059 | 0.02315 | −0.044272 | 0.015621 | −0.02493 | 0.020866 | 0.020638 | 0.021387 | 0.003028 | −0.009021 | −0.059064 |
| 226 | 0.016706 | 0.027348 | 0.013697 | −0.002157 | −0.021007 | −0.017218 | −0.006468 | 0.00877 | −0.005852 | −0.013709 | −0.029344 | −0.007808 | 0.032894 | −0.010219 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 227 | −0.028603 | 0.000429 | 0.029664 | 0.031849 | −0.033398 | −0.00313 | 0.027883 | −0.022378 | 0.025124 | 0.0513 | 0.003428 | 0.002262 | 0.047474 | −0.012187 |
| 228 | 0.008724 | −0.000987 | 0.000549 | −0.0064 | 0.043053 | 0.008994 | 0.03886 | 0.058702 | 0.023893 | 0.032614 | 0.00095 | 0.010342 | 0.010658 | −0.062846 |
| 229 | 0.008361 | 0.005278 | −0.014788 | −0.006446 | 0.015718 | −0.038966 | 0.029375 | −0.034492 | −0.031329 | −0.009554 | 0.056903 | 0.060536 | 0.008415 | 0.037305 |
| 230 | −0.020423 | −0.015008 | −0.017549 | 0.00061 | 0.014564 | 0.041489 | 0.00579 | −0.043515 | 0.006946 | −0.006766 | 0.030759 | 0.013666 | 0.000087 | −0.009598 |
| 231 | 0.013451 | 0.030546 | 0.006078 | −0.051571 | −0.049502 | −0.073601 | 0.024424 | −0.009201 | −0.055456 | −0.018051 | −0.009006 | 0.011164 | −0.006793 | 0.011065 |
| 232 | −0.016519 | 0.001692 | 0.024125 | 0.026163 | −0.012092 | −0.036455 | 0.003052 | −0.017729 | 0.081197 | 0.008269 | 0.023765 | 0.013965 | −0.031914 | 0.068807 |
| 233 | −0.015782 | 0.018456 | 0.032328 | 0.006346 | −0.030535 | −0.01505 | −0.057781 | 0.004651 | 0.002457 | 0.000016 | 0.021669 | 0.054346 | 0.006892 | −0.026896 |
| 234 | 0.009487 | 0.005573 | 0.001266 | 0.001285 | 0.026136 | 0.026365 | 0.008718 | 0.01987 | 0.002749 | −0.023963 | −0.004206 | −0.011581 | 0.046492 | 0.009535 |
| 235 | −0.029292 | −0.012366 | −0.000751 | 0.033782 | 0.020553 | 0.023262 | 0.013375 | −0.005433 | −0.007294 | −0.012077 | −0.012343 | 0.007904 | −0.00461 | −0.007836 |
| 236 | 0.006829 | 0.009349 | 0.016431 | −0.015716 | −0.007138 | 0.01453 | 0.009586 | −0.009702 | 0.001822 | −0.004459 | −0.004083 | −0.027094 | 0.000136 | 0.040898 |
| 237 | −0.014515 | 0.001902 | −0.008404 | 0.00592 | 0.019443 | 0.000401 | 0.017886 | −0.049719 | −0.013406 | −0.000566 | −0.039695 | 0.015616 | 0.040263 | −0.044224 |
| 238 | −0.009825 | 0.016467 | −0.001138 | 0.006687 | 0.007061 | 0.003701 | −0.000957 | 0.001644 | 0.010012 | 0.006395 | 0.022046 | 0.005558 | −0.019049 | −0.011801 |
| 239 | −0.01107 | 0.013065 | 0.004726 | −0.011004 | −0.002483 | 0.005125 | −0.031666 | 0.020873 | 0.022164 | 0.019949 | 0.043246 | 0.016396 | −0.037978 | −0.028899 |
| 240 | −0.016456 | −0.021549 | −0.004608 | 0.000674 | 0.015679 | 0.034915 | 0.003699 | 0.021055 | −0.039998 | −0.022275 | −0.024855 | −0.033924 | 0.0008 | −0.006946 |
| 241 | 0.010828 | 0.013525 | 0.014075 | 0.000317 | 0.000769 | 0.036685 | −0.005949 | −0.013336 | 0.006222 | −0.020042 | −0.032817 | 0.002622 | 0.009203 | 0.011492 |
| 242 | 0.01858 | −0.004447 | 0.004164 | −0.049513 | −0.035125 | −0.003317 | −0.035686 | 0.018488 | −0.035359 | −0.01347 | −0.004719 | −0.047791 | −0.052482 | 0.025367 |
| 243 | 0.013827 | −0.011632 | −0.010454 | 0.008633 | −0.012447 | −0.026698 | −0.031695 | −0.048251 | −0.028319 | −0.002622 | 0.008396 | −0.016302 | 0.000801 | 0.022493 |
| 244 | −0.005104 | −0.006216 | 0.013373 | 0:001868 | −0.021443 | −0.034579 | −0.011533 | −0.023165 | −0.030412 | −0.011799 | 0.019126 | −0.01166 | −0.026728 | −0.014153 |
| 245 | −0.013723 | 0.012619 | −0.011467 | 0.031583 | −0.00552 | −0.003553 | −0.017081 | −0.007446 | 0.083343 | −0.030928 | −0.03864 | 0.043579 | −0.011671 | −0.017558 |
| 246 | −0.000885 | −0.016784 | −0.014749 | −0.033033 | 0.01246 | 0.000523 | 0.002239 | 0.036723 | 0.020518 | 0.039258 | 0.027975 | 0.023164 | −0.012351 | −0.00312 |
| 247 | −0.0172 | −0.010747 | −0.008284 | −0.012864 | −0.039923 | −0.00211 | −0.006767 | 0.000527 | 0.028292 | −0.003848 | 0.004672 | −0.071988 | −0.010655 | 0.024647 |
| 248 | −0.008921 | 0.00842 | −0.013709 | −0.001794 | −0.034551 | −0.005616 | −0.031131 | −0.004151 | 0.011364 | −0.014725 | −0.003667 | −0.023358 | 0.01025 | 0.010929 |
| 249 | 0.026125 | 0.019828 | 0.010038 | 0.02016 | 0.029705 | 0.031311 | 0.001134 | −0.030695 | 0.026293 | −0.009269 | 0.010865 | 0.007298 | 0.042431 | −0.027178 |
| 250 | 0.028277 | −0.020412 | 0.00863 | −0.028065 | 0.017921 | 0.012607 | 0.029662 | −0.007917 | −0.043456 | 0.016013 | 0.045275 | 0.002316 | −0.0133 | 0.050398 |
| 251 | −0.003322 | −0.015752 | 0.001204 | 0.002314 | 0.007702 | 0.009397 | 0.030064 | −0.004888 | −0.019988 | 0.001577 | −0.004971 | 0.002133 | 0.0093 | −0.001327 |
| 252 | −0.020152 | 0.010665 | −0.012283 | 0.010517 | −0.02368 | −0.000376 | −0.11488 | −0.006015 | 0.040593 | −0.006111 | 0.004139 | −0.014071 | 0.005849 | −0.031811 |
| 253 | −0.024024 | −0.017322 | −0.0312 | −0.00143 | −0.003703 | −0.040302 | −0.010042 | 0.047852 | 0.014165 | 0.040235 | 0.023175 | 0.031073 | 0.018531 | 0.018261 |
| 254 | 0.036146 | 0.03907 | 0.021358 | 0.02323 | 0.03016 | −0.013997 | −0.029846 | −0.002581 | 0.014555 | 0.014216 | 0.044943 | −0.038035 | −0.02574 | 0.008555 |
| 255 | 0.020903 | −0.006185 | 0.006769 | −0.013667 | 0.025066 | −0.000081 | −0.008981 | 0.028875 | −0.04582 | −0.0154 | 0.009965 | −0.006817 | −0.0123 | 0.032776 |
| 256 | 0.010265 | −0.012017 | −0.016196 | 0.000219 | 0.050253 | 0.008428 | −0.037697 | 0.008917 | 0.043289 | −0.065816 | −0.009389 | 0.025784 | 0.011779 | 0.029802 |
| 257 | −0.015789 | −0.00338 | 0.005667 | 0.018145 | 0.004988 | 0.007638 | −0.037015 | 0.013491 | 0.02941 | 0.021774 | 0.013367 | −0.004361 | −0.012331 | −0.007287 |
| 258 | −0.001016 | 0.015368 | 0.009939 | 0.016735 | 0.014128 | 0.027081 | 0.010615 | 0.009076 | 0.014605 | −0.006535 | −0.019152 | −0.049957 | −0.047404 | −0.010305 |
| 259 | 0.024357 | −0.003061 | −0.010366 | −0.019696 | 0.010157 | 0.035421 | 0.029605 | 0.007754 | −0.038194 | −0.027256 | −0.035057 | 0.000384 | 0.011964 | −0.033124 |
| 260 | −0.003713 | 0.005795 | −0.003307 | 0.008718 | −0.015402 | −0.040118 | −0.007366 | 0.000137 | −0.014353 | 0.017028 | 0.016588 | 0.017194 | 0.003975 | −0.00266 |
| 261 | 0.0002 | 0.018283 | 0.002193 | −0.007684 | −0.024075 | −0.023805 | 0.007146 | 0.022489 | 0.006917 | 0.001136 | −0.023925 | −0.018816 | 0.042117 | −0.004346 |
| 262 | −0.008037 | 0.013782 | 0.001782 | 0.001359 | 0.007932 | 0.018441 | −0.011708 | 0.026019 | 0.036374 | 0.032086 | 0.035262 | −0.016 | 0.00677 | 0.032051 |
| 263 | 0.004901 | 0.021068 | −0.012953 | 0.012888 | 0.025616 | 0.010154 | −0.022463 | 0.022283 | 0.019937 | 0.014852 | 0.016124 | 0.051402 | 0.026504 | 0.019437 |
| 264 | 0.001921 | −0.016009 | −0.017951 | 0.003865 | 0.010411 | −0.014048 | 0.00392 | 0.007906 | −0.028582 | −0.035296 | −0.042184 | −0.011162 | −0.017051 | −0.058825 |
| 265 | −0.019312 | −0.014198 | 0.000861 | −0.007304 | 0.024079 | 0.029356 | 0.008073 | 0.021398 | −0.01745 | −0.013636 | −0.03234 | −0.043696 | −0.057399 | −0.014881 |
| 266 | 0.00295 | 0.016704 | 0.006263 | −0.006554 | −0.010108 | −0.038693 | −0.019151 | −0.020937 | 0.010652 | −0.024588 | −0.042164 | 0.022853 | 0.030266 | 0.037093 |
| 267 | 0.007256 | −0.015256 | −0.020475 | 0.009369 | 0.017173 | −0.01242 | 0.057044 | −0.023759 | 0.032471 | 0.004276 | 0.023579 | −0.032937 | −0.025507 | 0.084525 |
| 268 | 0.010984 | 0.011723 | 0.012514 | 0.016908 | −0.013675 | −0.031633 | −0.000758 | 0.011879 | −0.016051 | −0.016243 | −0.04001 | −0.018638 | 0.002067 | 0.003882 |
| 269 | 0.010644 | 0.009578 | 0.002989 | 0.002805 | −0.036315 | −0.028813 | −0.020503 | 0.001553 | −0.017787 | −0.018371 | −0.00659 | 0.006648 | 0.011535 | 0.052263 |
| 270 | 0.021935 | 0.002783 | 0.014306 | −0.002058 | −0.00222 | −0.004132 | −0.020142 | 0.070466 | −0.003402 | −0.012188 | −0.0058 | 0.005039 | 0.001547 | 0.020534 |
| 271 | 0.00424 | 0.004762 | −0.007149 | −0.034889 | −0.025675 | −0.008179 | 0.006624 | −0.059496 | 0.034895 | −0.010798 | 0.010757 | −0.022016 | 0.002131 | −0.017611 |
| 272 | 0.007349 | 0.010303 | −0.000609 | 0.014968 | 0.02351 | −0.003903 | 0.045715 | 0.014812 | −0.008344 | 0.033764 | −0.015026 | 0.015985 | 0.018177 | −0.024782 |
| 273 | −0.007713 | 0.005396 | 0.006199 | 0.015192 | 0.001237 | 0.008836 | 0.026597 | −0.009697 | −0.010246 | 0.000349 | −0.029311 | −0.04137 | 0.007593 | −0.051078 |
| 274 | −0.009809 | −0.004158 | 0.000839 | 0.002362 | 0.00845 | 0.022749 | 0.020465 | −0.002508 | −0.016836 | 0.00088 | −0.020166 | −0.0353 | 0.003599 | −0.051276 |
| 275 | −0.017162 | −0.004161 | 0.007353 | −0.006108 | −0.001935 | 0.003593 | 0.028497 | 0.050996 | −0.007216 | −0.023371 | −0.000085 | 0.01796 | 0.025553 | 0.068222 |
| 276 | 0.005156 | 0.00269 | −0.00118 | 0.027415 | 0.009797 | −0.001698 | −0.009372 | −0.026232 | 0.024934 | 0.020147 | 0.002035 | −0.01299 | 0.010205 | 0.025934 |
| 277 | −0.003934 | −0.018071 | −0.014044 | −0.035609 | −0.014109 | 0.005338 | 0.009421 | 0.008405 | −0.018712 | 0.000592 | 0.011351 | 0.004726 | 0.008403 | −0.026323 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 278 | −0.019793 | −0.012829 | −0.030322 | −0.083594 | −0.044827 | 0.016248 | 0.004951 | 0.049763 | −0.029493 | −0.012802 | −0.012948 | −0.001536 | 0.022801 | −0.000109 |
| 279 | −0.014969 | −0.004586 | −0.012475 | −0.003872 | 0.006748 | 0.004636 | 0.000847 | 0.043135 | 0.013054 | −0.00836 | 0.028159 | 0.029196 | −0.017159 | 0.008655 |
| 280 | 0.016959 | 0.019466 | 0.033305 | 0.020035 | −0.009177 | 0.010814 | 0.046683 | −0.058563 | 0.003622 | 0.001746 | −0.033906 | 0.030967 | 0.035231 | −0.022078 |
| 281 | 0.023781 | 0.009678 | 0.003125 | −0.000271 | −0.019381 | −0.03171 | 0.051378 | 0.028802 | 0.018232 | 0.008912 | −0.01036 | 0.041351 | 0.003336 | 0.016249 |
| 282 | 0.000329 | 0.004244 | −0.019085 | −0.052442 | −0.052631 | 0.004481 | 0.03403 | 0.049056 | −0.003028 | 0.005024 | 0.019627 | −0.012621 | −0.014312 | 0.046527 |
| 283 | −0.031948 | −0.032673 | −0.014261 | −0.00062 | −0.028832 | −0.008456 | 0.008566 | −0.019027 | 0.030618 | 0.020846 | 0.008569 | −0.038859 | 0.008265 | 0.034122 |
| 284 | −0.009285 | −0.020248 | 0.007997 | 0.026973 | 0.015872 | −0.008396 | −0.039197 | −0.00008 | 0.026575 | 0.017168 | 0.018055 | 0.016525 | −0.012113 | 0.002925 |
| 285 | 0.000979 | −0.041532 | −0.018564 | 0.004289 | 0.027666 | 0.014001 | −0.023204 | 0.024198 | 0.007509 | 0.017045 | 0.017009 | −0.019471 | −0.017892 | 0.002369 |
| 286 | −0.007918 | −0.006186 | −0.009624 | 0.012956 | 0.004663 | 0.03014 | −0.001011 | 0.009061 | −0.000815 | −0.004799 | 0.007216 | 0.043052 | −0.019098 | −0.023717 |
| 287 | 0.007014 | −0.004276 | 0.001974 | 0.00864 | 0.034141 | 0.039467 | 0.006349 | 0.026905 | 0.014189 | 0.005979 | −0.011818 | 0.03448 | 0.023914 | 0.019033 |
| 288 | 0.01351 | 0.018106 | 0.018194 | 0.029322 | 0.04106 | −0.021933 | 0.018229 | −0.004229 | −0.040143 | −0.006427 | −0.026155 | −0.006721 | 0.000694 | 0.039877 |
| 289 | 0.029568 | 0.009061 | 0.021075 | −0.020912 | 0.041477 | 0.040662 | 0.027328 | 0.054179 | 0.015583 | 0.011686 | 0.033976 | −0.022371 | −0.012022 | 0.055554 |
| 290 | 0.004415 | 0.011694 | 0.018838 | 0.016593 | −0.001836 | −0.01781 | 0.002177 | 0.017541 | 0.018303 | −0.003943 | 0.018991 | 0.004904 | 0.020907 | −0.006629 |
| 291 | 0.00834 | 0.01485 | 0.017254 | 0.012302 | 0.002861 | −0.008238 | −0.014746 | 0.011864 | 0.023388 | −0.003638 | 0.028375 | 0.012047 | 0.015404 | −0.002732 |
| 292 | 0.01791 | −0.013627 | 0.017072 | 0.025942 | 0.036707 | −0.00833 | −0.027285 | 0.029462 | 0.018355 | −0.010796 | 0.038212 | 0.027539 | −0.005654 | 0.001321 |
| 293 | −0.007374 | −0.00719 | −0.005935 | −0.008588 | 0.007775 | 0.007991 | 0.039605 | −0.002511 | 0.017724 | 0.02791 | 0.036556 | 0.009165 | −0.001647 | 0.03666 |
| 294 | 0.045017 | 0.027085 | 0.029277 | 0.022626 | 0.044455 | 0.005307 | −0.044828 | −0.017311 | −0.02199 | −0.015685 | −0.004613 | 0.02883 | 0.000129 | −0.005024 |
| 295 | −0.000185 | −0.004394 | −0.010895 | 0.009979 | 0.035766 | 0.054437 | −0.031209 | −0.027781 | 0.021848 | 0.03009 | 0.026573 | −0.008274 | −0.006111 | −0.038007 |
| 296 | 0.005725 | −0.035793 | −0.04355 | −0.024206 | 0.024026 | 0.044352 | −0.019528 | −0.011496 | −0.013244 | 0.005601 | 0.012578 | −0.033491 | 0.01151 | 0.017613 |
| 297 | −0.006456 | −0.022263 | −0.014812 | 0.028203 | 0.031631 | 0.034698 | −0.046465 | −0.017163 | 0.038115 | 0.008107 | 0.005829 | −0.016757 | −0.010929 | 0.001413 |
| 298 | −0.017529 | 0.016183 | −0.001329 | −0.022262 | −0.057698 | −0.020943 | −0.029013 | −0.028516 | 0.030144 | −0.004153 | −0.040008 | −0.003259 | −0.029865 | 0.020239 |
| 299 | 0.000486 | 0.043868 | 0.024265 | −0.001681 | −0.005234 | −0.016228 | 0.053108 | −0.005084 | 0.008151 | −0.01889 | −0.004717 | −0.034459 | −0.05327 | −0.004489 |
| 300 | 0.023423 | −0.004032 | 0.014873 | 0.048574 | 0.03261 | −0.031955 | 0.016225 | 0.027064 | 0.039739 | −0.024323 | −0.051994 | −0.036173 | −0.042791 | 0.011799 |
| 301 | 0.002232 | 0.013964 | 0.003411 | 0.013281 | −0.006791 | −0.013849 | −0.032906 | −0.020868 | 0.02037 | 0.042521 | 0.017144 | 0.010763 | 0.020123 | 0.013732 |
| 302 | 0.019425 | 0.021874 | 0.017363 | −0.009782 | 0.012236 | 0.020929 | 0.012682 | 0.034077 | −0.0034 | 0.034628 | 0.007882 | 0.028984 | 0.044956 | 0.022024 |
| 303 | −0.014725 | 0.024801 | 0.013438 | −0.019865 | −0.03608 | 0.037684 | −0.000122 | −0.017923 | −0.03905 | −0.019434 | −0.023048 | −0.011608 | 0.008434 | 0.01793 |
| 304 | −0.018996 | 0.021815 | 0.010196 | 0.003695 | −0.000484 | 0.013619 | −0.020246 | 0.016584 | −0.012656 | −0.016569 | 0.009777 | 0.009199 | 0.000179 | 0.007563 |
| 305 | 0.02746 | 0.014699 | −0.007668 | −0.018314 | 0.003796 | 0.013874 | −0.088187 | 0.00827 | 0.012205 | 0.043214 | 0.009582 | 0.054632 | 0.031396 | 0.030928 |
| 306 | −0.011311 | 0.006993 | 0.019177 | 0.01206 | −0.037834 | −0.019811 | 0.029103 | 0.017726 | 0.049904 | 0.019764 | 0.020386 | 0.00132 | 0.01148 | 0.035624 |
| 307 | −0.012007 | −0.013135 | −0.009009 | −0.006777 | 0.020025 | 0.041404 | −0.055309 | −0.013188 | −0.030613 | −0.021691 | −0.012101 | −0.049499 | −0.032799 | −0.045592 |
| 308 | 0.003655 | 0.010743 | 0.007215 | 0.013327 | 0.002496 | −0.038514 | 0.065495 | −0.001386 | −0.005661 | −0.00365 | 0.004441 | 0.02262 | −0.004218 | −0.020964 |
| 309 | 0.008201 | 0.006455 | 0.008685 | 0.013561 | 0.015763 | 0.008247 | 0.034979 | 0.001567 | 0.017798 | −0.00759 | 0.00343 | 0.01715 | 0.032353 | 0.03029 |
| 310 | −0.033372 | −0.015894 | −0.005229 | −0.037657 | −0.038948 | −0.030808 | −0.008976 | 0.070236 | −0.055059 | −0.038743 | 0.005063 | 0.057131 | 0.032444 | −0.008286 |
| 311 | −0.024094 | 0.005051 | 0.003948 | 0.023224 | −0.037269 | −0.027653 | −0.000525 | −0.004046 | 0.022817 | −0.016444 | −0.008932 | −0.038071 | 0.028139 | 0.042292 |
| 312 | −0.019659 | −0.001671 | −0.007353 | 0.002045 | −0.021062 | −0.024134 | −0.014861 | 0.023034 | −0.039925 | −0.046349 | −0.055835 | −0.037313 | −0.039112 | 0.021399 |
| 313 | −0.000126 | 0.010079 | −0.018903 | 0.024826 | −0.009245 | −0.009534 | −0.011442 | −0.003552 | 0.027289 | −0.002743 | 0.039682 | 0.021909 | 0.012403 | −0.017503 |
| 314 | 0.007833 | −0.013709 | −0.010321 | 0.006133 | 0.021879 | 0.025733 | 0.025509 | −0.040556 | 0.020024 | −0.000297 | 0.024598 | 0.028002 | 0.023638 | −0.001409 |
| 315 | 0.004986 | 0.003631 | 0.002157 | −0.008219 | 0.006136 | 0.031502 | 0.016269 | −0.026821 | 0.025273 | 0.016387 | 0.008282 | −0.004995 | 0.02073 | −0.007508 |
| 316 | −0.010523 | 0.019171 | −0.003236 | 0.013965 | 0.011188 | 0.001961 | 0.004071 | −0.008178 | −0.021485 | −0.003456 | 0.015488 | −0.028955 | −0.067735 | 0.056166 |
| 317 | 0.001534 | −0.020358 | −0.019674 | −0.008194 | 0.011005 | 0.021121 | −0.02755 | 0.003417 | 0.020018 | 0.014645 | 0.012939 | −0.000647 | −0.025334 | 0.046045 |
| 318 | −0.001825 | −0.001737 | −0.003937 | −0.014115 | −0.024782 | −0.035757 | −0.045141 | 0.045029 | 0.015413 | −0.0405 | −0.045348 | −0.008655 | −0.010879 | −0.025793 |
| 319 | −0.001642 | −0.022202 | −0.022713 | −0.013902 | 0.006455 | 0.006622 | −0.031326 | 0.002145 | −0.008447 | 0.011355 | −0.022422 | 0.003799 | 0.001409 | −0.030522 |
| 320 | −0.013372 | −0.023761 | −0.037873 | −0.02287 | 0.035559 | 0.013751 | −0.062804 | −0.013038 | 0.007106 | −0.017433 | 0.011295 | 0.010674 | 0.009767 | 0.049552 |
| 321 | 0.004496 | 0.03221 | 0.051195 | 0.038594 | −0.027142 | −0.093841 | 0.041908 | −0.010924 | 0.013748 | 0.015475 | 0.037363 | 0.015687 | 0.014323 | −0.087668 |
| 322 | 0.012074 | 0.022406 | 0.016475 | 0.013816 | 0.012532 | −0.011088 | −0.00615 | 0.017649 | 0.043678 | 0.003021 | −0.007162 | 0.02063 | 0.006888 | 0.037992 |
| 323 | −0.001254 | 0.027604 | −0.010976 | −0.017789 | −0.016892 | 0.024313 | −0.041506 | −0.011096 | 0.03236 | −0.009994 | 0.025219 | 0.012864 | 0.022874 | 0.009623 |
| 324 | −0.020235 | −0.00703 | 0.00158 | 0.002528 | −0.009059 | 0.036746 | 0.075716 | 0.039515 | 0.006335 | 0.01584 | −0.047556 | −0.00701 | −0.034549 | 0.025395 |
| 325 | −0.021345 | −0.013112 | −0.010793 | −0.022914 | −0.02233 | −0.022552 | −0.002253 | −0.037679 | 0.021685 | 0.014356 | −0.040497 | −0.000537 | 0.019485 | −0.016352 |
| 326 | −0.021015 | −0.018894 | −0.014512 | −0.010639 | −0.025929 | −0.005924 | 0.088927 | −0.037688 | 0.006549 | 0.001167 | −0.071401 | −0.044645 | −0.040463 | 0.004007 |
| 327 | 0.016675 | 0.001394 | −0.00888 | −0.008298 | 0.023545 | −0.000821 | 0.042247 | −0.030975 | 0.020176 | 0.008388 | 0.032499 | −0.030533 | −0.060704 | −0.033876 |
| 328 | 0.009116 | −0.002538 | −0.010595 | −0.004699 | 0.015721 | −0.011398 | 0.009585 | −0.006208 | −0.008299 | −0.003777 | 0.024987 | −0.014935 | −0.010354 | 0.00552 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 329 | 0.005154 | 0.009873 | 0.008438 | 0.005526 | 0.019955 | −0.004888 | 0.00462 | 0.011755 | 0.010693 | 0.014595 | −0.002941 | 0.032197 | −0.008587 | −0.063532 |
| 330 | 0.011564 | 0.022296 | 0.005912 | −0.011522 | −0.010032 | 0.037294 | −0.037639 | 0.02266 | −0.024779 | 0.009947 | −0.032857 | 0.003443 | −0.018764 | 0.012781 |
| 331 | −0.000291 | 0.004463 | 0.014101 | −0.026768 | −0.001931 | 0.010577 | 0.014504 | −0.012914 | 0.003778 | 0.00186 | −0.016285 | −0.015675 | −0.014764 | 0.012499 |
| 332 | −0.064839 | −0.014401 | −0.00863 | −0.027879 | −0.024078 | −0.006141 | −0.045135 | 0.029204 | 0.043572 | 0.002052 | −0.005774 | −0.036969 | −0.012599 | −0.005798 |
| 333 | 0.003479 | −0.024118 | −0.00141 | −0.034096 | −0.011032 | −0.06469 | −0.067038 | 0.028632 | 0.022297 | 0.022601 | 0.015219 | −0.007855 | −0.051925 | −0.025222 |
| 334 | −0.01058 | 0.014544 | 0.029176 | −0.00275 | 0.019287 | 0.019175 | −0.041206 | 0.000338 | 0.000486 | −0.014614 | −0.058459 | 0.01215 | 0.003971 | −0.032217 |
| 335 | −0.000396 | 0.020207 | 0.001493 | 0.00595 | −0.009115 | −0.030718 | −0.008661 | −0.013531 | −0.006143 | −0.009456 | −0.032793 | 0.074572 | 0.015056 | 0.008066 |
| 336 | 0.004295 | −0.000589 | 0.012614 | −0.000857 | 0.003844 | −0.030101 | −0.082123 | −0.082614 | −0.021572 | −0.005789 | 0.065437 | −0.029251 | −0.068944 | 0.021191 |
| 337 | −0.001087 | 0.009362 | 0.024858 | 0.032692 | −0.02626 | −0.009101 | −0.005563 | 0.021434 | −0.021 | 0.012907 | 0.021115 | −0.05083 | −0.031711 | 0.013544 |
| 338 | −0.002903 | 0.001205 | −0.016379 | −0.020522 | −0.025017 | 0.003009 | 0.009901 | −0.01963 | −0.004973 | 0.037519 | 0.042814 | −0.019507 | 0.000815 | −0.001925 |
| 339 | −0.014473 | −0.00139 | 0.008973 | −0.010702 | 0.004716 | 0.034896 | 0.088509 | −0.031747 | −0.024185 | 0.018447 | 0.044969 | −0.013761 | 0.026926 | 0.011445 |
| 340 | −0.02553 | −0.003587 | 0.000297 | 0.01478 | 0.013222 | 0.055089 | −0.025552 | 0.013969 | 0.00718 | −0.001804 | 0.049075 | 0.036884 | −0.020937 | 0.009593 |

| | GL | GM | GN | GO | GP | GQ | GR | GS | GT | GU | GV | GW | GX | GY |
|---|---|---|---|---|---|---|---|---|---|---|---|---|---|---|
| 1 | −0.048719 | −0.038534 | −0.012 | 0.048233 | −0.023775 | 0.049269 | 0.132338 | −0.0291 | 0.0081 | −0.019013 | 0.051005 | −0.174309 | −0.030461 | 0.028787 |
| 2 | 0.036173 | 0.053924 | −0.018474 | 0.089826 | 0.05065 | 0.05407 | 0.019313 | 0.025177 | −0.107738 | −0.025641 | 0.055027 | 0.024849 | −0.136226 | 0.042591 |
| 3 | 0.078722 | 0.039827 | 0.04393 | 0.026012 | 0.020118 | −0.064566 | 0.009392 | −0.050719 | −0.015752 | 0.006476 | −0.00707 | 0.056333 | 0.164376 | −0.020317 |
| 4 | 0.038428 | −0.030966 | −0.025662 | −0.03292 | −0.048206 | −0.012198 | 0.035786 | 0.044372 | −0.060388 | 0.060092 | −0.039532 | −0.036804 | 0.030292 | 0.091125 |
| 5 | 0.044938 | 0.059594 | 0.045074 | −0.010978 | 0.033746 | 0.013978 | −0.009161 | −0.033499 | 0.024372 | −0.079835 | 0.013985 | −0.053156 | 0.012911 | −0.009164 |
| 6 | −0.097339 | −0.00841 | 0.01735 | 0.005432 | −0.05716 | 0.024196 | 0.047533 | −0.062155 | 0.078274 | 0.054799 | −0.006996 | −0.050331 | −0.123676 | −0.018324 |
| 7 | 0.054962 | −0.083372 | −0.075402 | −0.059322 | −0.018382 | −0.057141 | 0.00241 | −0.000167 | −0.036655 | −0.051966 | −0.103892 | −0.025121 | 0.028919 | −0.050325 |
| 8 | −0.049289 | 0.019866 | 0.02944 | −0.018243 | −0.050287 | −0.025309 | 0.007849 | 0.000844 | 0.034483 | 0.023419 | 0.028491 | −0.000143 | 0.025238 | −0.008749 |
| 9 | 0.125479 | −0.022451 | −0.048166 | −0.009735 | −0.045912 | 0.097297 | −0.092414 | 0.010085 | −0.040888 | 0.004582 | 0.033212 | 0.036937 | 0.032198 | 0.02847 |
| 10 | −0.036087 | −0.062608 | −0.011251 | −0.091225 | −0.015608 | 0.059961 | 0.132596 | 0.054099 | 0.042155 | −0.037334 | 0.020202 | 0.001351 | −0.022179 | 0.139631 |
| 11 | −0.034064 | −0.009758 | −0.041521 | 0.040675 | −0.016836 | −0.032718 | −0.006619 | −0.021965 | 0.008911 | 0.004526 | −0.03522 | 0.015537 | 0.00764 | −0.015405 |
| 12 | 0.040185 | −0.033698 | 0.003061 | 0.000108 | −0.012758 | −0.031514 | 0.053489 | 0.016542 | −0.044924 | 0.002938 | 0.059556 | −0.000227 | −0.078134 | 0.047081 |
| 13 | 0.021558 | 0.018023 | −0.020197 | 0.022448 | −0.062693 | 0.034586 | −0.025665 | 0.118323 | 0.040304 | −0.06273 | 0.035158 | −0.034592 | 0.065739 | −0.009023 |
| 14 | −0.00941 | −0.085727 | −0.00824 | 0.009881 | −0.012373 | 0.035682 | −0.049529 | 0.022256 | −0.134877 | 0.039578 | 0.041217 | 0.001108 | 0.012833 | −0.025449 |
| 15 | 0.039185 | 0.066964 | 0.049427 | 0.005333 | 0.086521 | 0.019071 | −0.034943 | 0.095607 | 0.044443 | 0.129044 | 0.100834 | −0.001594 | −0.019346 | 0.069281 |
| 16 | 0.021709 | −0.017727 | 0.007173 | −0.025407 | 0.038791 | −0.017883 | 0.02159 | −0.031644 | 0.040363 | 0.010222 | 0.047436 | −0.01621 | −0.018953 | −0.03165 |
| 17 | 0.035467 | 0.096461 | −0.104223 | −0.021634 | −0.034408 | 0.029594 | 0.047297 | −0.03376 | 0.077511 | 0.038292 | 0.047659 | −0.053212 | −0.004355 | −0.023312 |
| 18 | 0.017444 | −0.039621 | 0.004837 | 0.031762 | 0.031095 | −0.01537 | 0.070524 | 0.042873 | 0.015286 | 0.072694 | 0.001906 | −0.084399 | 0.001097 | −0.075079 |
| 19 | 0.027908 | −0.034334 | −0.005358 | −0.008323 | −0.018866 | −0.02891 | −0.044154 | −0.010714 | 0.056139 | −0.046408 | −0.113208 | 0.162769 | −0.07014 | −0.1337 |
| 20 | −0.073568 | −0.140474 | −0.016072 | −0.016904 | −0.038434 | −0.032317 | −0.085082 | 0.021456 | 0.012457 | 0.023687 | −0.015366 | 0.034658 | −0.236873 | −0.039217 |
| 21 | −0.036003 | −0.017187 | 0.021312 | 0.018239 | 0.026288 | −0.02826 | −0.05252 | 0.009083 | −0.018278 | −0.002806 | 0.026808 | −0.12926 | 0.081102 | 0.03236 |
| 22 | 0.013171 | 0.00081 | −0.079427 | 0.017586 | 0.028878 | −0.114586 | 0.071157 | 0.013422 | 0.064972 | −0.084452 | −0.021411 | −0.107389 | −0.043366 | −0.012754 |
| 23 | −0.010077 | 0.02671 | −0.010279 | 0.037257 | 0.031317 | 0.057428 | −0.136302 | −0.062644 | −0.055177 | 0.03908 | 0.085226 | 0.011123 | 0.134877 | 0.012722 |
| 24 | 0.052574 | −0.015731 | 0.052637 | 0.014037 | −0.05882 | 0.014312 | −0.04711 | −0.105124 | 0.057711 | −0.005574 | 0.027915 | 0.022578 | 0.034269 | 0.082188 |
| 25 | −0.007996 | 0.02792 | 0.020865 | 0.021661 | −0.009007 | 0.032812 | −0.029666 | −0.017355 | −0.055913 | 0.098737 | 0.044442 | 0.084724 | 0.004787 | 0.037711 |
| 26 | −0.038762 | −0.00889 | 0.167466 | 0.108678 | 0.099706 | 0.034605 | −0.116683 | 0.031821 | −0.000119 | 0.107252 | 0.040008 | −0.113755 | 0.096744 | 0.154665 |
| 27 | −0.043767 | 0.074512 | 0.096341 | 0.058546 | 0.045268 | 0.183493 | 0.091786 | −0.055228 | −0.132502 | 0.123104 | 0.03448 | −0.018229 | 0.044498 | −0.137191 |
| 28 | −0.004783 | 0.035967 | 0.004284 | 0.078068 | 0.035557 | 0.050221 | 0.12125 | −0.044191 | −0.066237 | 0.010145 | −0.114405 | 0.020758 | −0.118355 | −0.117113 |
| 29 | 0.01603 | −0.063286 | 0.030882 | −0.013151 | 0.078227 | −0.066756 | −0.071877 | −0.126658 | 0.107307 | −0.079266 | 0.042037 | 0.024998 | −0.013238 | −0.016319 |
| 30 | 0.020725 | −0.098013 | 0.061117 | −0.045057 | −0.089204 | 0.075051 | −0.160318 | 0.159455 | 0.087896 | 0.013691 | −0.134795 | 0.03923 | −0.010433 | 0.020566 |
| 31 | 0.019618 | −0.044133 | 0.003305 | −0.044474 | −0.013782 | 0.001929 | −0.045143 | 0.098807 | −0.056582 | −0.008043 | 0.061358 | 0.007486 | 0.101445 | 0.011141 |
| 32 | −0.010802 | 0.06308 | 0.035837 | −0.026118 | 0.022295 | −0.039284 | 0.093225 | −0.077762 | −0.055153 | −0.050957 | 0.031467 | −0.026914 | 0.01998 | −0.101013 |
| 33 | −0.110522 | 0.048339 | −0.036577 | −0.065412 | −0.030766 | −0.016916 | −0.07266 | 0.073587 | −0.093323 | −0.031544 | 0.000071 | −0.043787 | −0.057233 | 0.016272 |
| 34 | −0.074762 | 0.042727 | 0.012728 | 0.045467 | −0.056081 | −0.100595 | 0.26947 | 0.048115 | −0.107559 | −0.115529 | 0.084947 | −0.021485 | 0.071278 | 0.06395 |
| 35 | −0.028064 | −0.018558 | 0.025962 | −0.001442 | −0.05646 | −0.001323 | 0.021496 | −0.041481 | 0.044238 | 0.056923 | −0.001684 | 0.001613 | 0.068615 | 0.02453 |
| 36 | 0.024672 | 0.028447 | −0.034645 | −0.048461 | 0.067165 | 0.025866 | 0.10484 | 0.023965 | −0.084035 | 0.006062 | −0.070602 | 0.041852 | −0.036501 | −0.096662 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 37 | 0.008503 | 0.069297 | −0.000924 | 0.035563 | −0.031939 | −0.058925 | 0.046321 | −0.039559 | −0.109088 | −0.01799 | 0.040944 | 0.169696 | −0.162125 | −0.052782 |
| 38 | 0.000048 | 0.028574 | 0.018409 | 0.000598 | −0.076007 | −0.010902 | −0.024748 | 0.074626 | −0.017532 | 0.005442 | 0.032658 | 0.033745 | 0.032486 | −0.009465 |
| 39 | −0.063354 | 0.002989 | −0.015749 | −0.033916 | −0.032878 | 0.037982 | 0.035329 | −0.094553 | −0.034662 | −0.094779 | −0.059151 | 0.032576 | 0.008509 | −0.126155 |
| 40 | 0.071148 | 0.047783 | 0.10246 | 0.039512 | 0.019081 | 0.074823 | −0.091943 | 0.006813 | −0.027404 | −0.042944 | −0.042434 | 0.026807 | 0.051459 | −0.045796 |
| 41 | −0.024678 | 0.013808 | 0.008151 | −0.065517 | −0.004346 | 0.087082 | −0.071125 | 0.049311 | 0.038857 | 0.053364 | −0.02458 | 0.001979 | 0.077711 | −0.057126 |
| 42 | 0.031501 | 0.063204 | −0.019078 | −0.009744 | 0.025303 | 0.060974 | −0.085095 | 0.020991 | 0.097087 | 0.075852 | −0.038087 | 0.106729 | −0.041788 | 0.152814 |
| 43 | 0.053709 | −0.018427 | −0.142081 | −0.104262 | 0.041727 | −0.088079 | 0.031289 | 0.028081 | −0.007964 | −0.081664 | 0.054342 | −0.010798 | 0.037524 | 0.033304 |
| 44 | 0.013975 | −0.039336 | −0.018923 | 0.016189 | −0.014127 | 0.074698 | −0.072286 | 0.046166 | −0.151137 | −0.039486 | 0.161211 | −0.037692 | −0.080023 | 0.043308 |
| 45 | −0.036991 | 0.000698 | 0.023576 | 0.064659 | 0.021852 | −0.049424 | 0.023233 | −0.078222 | −0.000228 | 0.018678 | −0.241163 | 0.003246 | −0.131519 | 0.039941 |
| 46 | 0.011911 | 0.031983 | 0.079413 | 0.02654 | 0.049623 | −0.036572 | 0.037233 | −0.063957 | 0.047366 | −0.04002 | 0.03223 | 0.075736 | 0.066603 | 0.014189 |
| 47 | 0.037194 | −0.095188 | 0.00305 | 0.015587 | 0.025079 | −0.068803 | 0.052897 | 0.09576 | 0.020768 | −0.015452 | 0.017036 | −0.061034 | −0.012004 | 0.019696 |
| 48 | 0.040166 | −0.001027 | 0.044113 | 0.060614 | 0.047164 | 0.022807 | −0.011669 | 0.004006 | −0.027695 | 0.00067 | 0.020621 | 0.058814 | −0.063069 | −0.110283 |
| 49 | 0.040866 | 0.038778 | −0.083125 | −0.056181 | −0.012472 | −0.03585 | 0.039024 | −0.122363 | 0.105008 | −0.013876 | −0.03522 | −0.000437 | −0.013735 | −0.042479 |
| 50 | 0.108675 | 0.005545 | −0.048844 | −0.057769 | 0.06466 | −0.002434 | −0.104522 | −0.019977 | 0.065535 | −0.047103 | 0.047642 | −0.035262 | −0.08631 | 0.023675 |
| 51 | −0.146058 | −0.013479 | −0.095222 | 0.036706 | −0.034338 | −0.077366 | −0.024599 | 0.010012 | 0.121686 | −0.027691 | 0.09801 | 0.0131 | −0.041546 | 0.072425 |
| 52 | 0.038318 | 0.125393 | 0.071014 | 0.050889 | −0.003381 | −0.009441 | 0.013308 | 0.039789 | −0.093878 | −0.03428 | −0.098896 | −0.044233 | 0.162224 | 0.014561 |
| 53 | 0.080894 | 0.060023 | −0.00311 | 0.043401 | −0.003415 | 0.162077 | 0.002787 | 0.025165 | 0.027831 | 0.052027 | −0.020626 | 0.08643 | 0.043303 | 0.076843 |
| 54 | 0.04126 | 0.091063 | −0.071896 | −0.122665 | −0.069837 | 0.037496 | −0.031475 | −0.048153 | −0.055348 | −0.050798 | 0.030598 | −0.059131 | −0.115924 | −0.02246 |
| 55 | 0.073506 | −0.069046 | −0.032691 | −0.010542 | 0.085591 | 0.020518 | −0.074242 | −0.170167 | 0.035204 | −0.0745 | −0.057722 | −0.031553 | 0.071361 | 0.071612 |
| 56 | −0.000547 | −0.017128 | −0.014273 | 0.083934 | 0.137874 | 0.040415 | 0.02502 | 0.010847 | −0.038362 | 0.041477 | 0.104564 | −0.133546 | −0.07034 | −0.016472 |
| 57 | −0.017728 | 0.037244 | −0.040052 | −0.04543 | −0.012612 | 0.057633 | 0.043757 | 0.079895 | −0.074109 | −0.036218 | −0.022804 | −0.115098 | −0.100066 | −0.049415 |
| 58 | 0.014999 | 0.034806 | 0.012443 | 0.007491 | −0.064473 | −0.039241 | 0.021871 | −0.068342 | −0.011478 | −0.072323 | 0.145515 | −0.008047 | −0.027058 | 0.077946 |
| 59 | 0.000256 | 0.057839 | 0.015537 | 0.04983 | 0.026893 | −0.066854 | −0.083502 | −0.02992 | 0.041669 | −0.049039 | 0.022058 | −0.011002 | 0.040685 | −0.104695 |
| 60 | −0.087955 | 0.085736 | −0.026435 | 0.015201 | 0.014188 | −0.085596 | −0.226212 | −0.051844 | 0.014496 | −0.107326 | −0.036999 | −0.019581 | 0.056338 | −0.070636 |
| 61 | −0.063327 | −0.086233 | −0.026228 | −0.051523 | −0.072607 | 0.043418 | 0.036216 | 0.026919 | 0.048015 | 0.063054 | 0.040033 | 0.162421 | 0.018758 | 0.084551 |
| 62 | 0.029303 | 0.068507 | 0.015708 | 0.001003 | −0.016243 | −0.014533 | 0.033063 | 0.085162 | −0.094815 | 0.037653 | 0.024844 | −0.120081 | −0.029245 | −0.026061 |
| 63 | 0.005863 | −0.031789 | 0.034902 | 0.080492 | 0.054778 | −0.102784 | −0.008964 | 0.053701 | 0.068557 | −0.059593 | 0.003519 | 0.047089 | 0.100509 | 0.060929 |
| 64 | 0.033261 | −0.004925 | 0.002971 | 0.021664 | 0.034069 | 0.019319 | 0.010558 | −0.002253 | −0.019712 | 0.033212 | −0.029015 | 0.005626 | 0.010626 | −0.01019 |
| 65 | 0.247851 | 0.040644 | 0.042411 | 0.006454 | −0.01269 | −0.065595 | 0.030659 | −0.095671 | 0.014352 | 0.010078 | −0.164021 | 0.152951 | 0.071673 | 0.123143 |
| 66 | −0.049053 | 0.005809 | −0.054676 | −0.051801 | 0.019473 | −0.032925 | 0.063659 | −0.036914 | 0.108665 | 0.105998 | −0.039154 | −0.0633 | −0.049385 | −0.00184 |
| 67 | 0.040223 | −0.00285 | 0.048991 | −0.094146 | −0.086445 | 0.046007 | 0.04078 | −0.059576 | 0.092574 | −0.017346 | −0.00117 | −0.085396 | 0.027288 | 0.034791 |
| 68 | −0.038238 | −0.038474 | −0.031837 | −0.008195 | 0.018899 | 0.056817 | −0.013389 | −0.019352 | −0.053307 | −0.010104 | 0.073531 | 0.000604 | −0.006717 | −0.039791 |
| 69 | 0.018442 | −0.087814 | −0.026662 | −0.054458 | 0.04456 | −0.086703 | 0.06684 | −0.10559 | 0.051016 | −0.1247 | 0.079707 | 0.032614 | 0.027489 | 0.018742 |
| 70 | 0.092582 | 0.038226 | 0.045314 | −0.013793 | −0.017241 | 0.033055 | −0.027482 | 0.001549 | −0.071385 | 0.148632 | −0.251412 | −0.12524 | −0.185589 | 0.020267 |
| 71 | 0.033984 | 0.033116 | −0.005066 | 0.0159 | 0.01909 | −0.030671 | 0.026703 | −0.037069 | −0.03436 | 0.015614 | 0.027404 | −0.081781 | 0.095681 | −0.010455 |
| 72 | −0.102979 | 0.058422 | 0.066763 | 0.074183 | 0.034274 | 0.035698 | −0.088049 | −0.182736 | 0.096783 | 0.042377 | −0.007465 | 0.135929 | −0.097913 | 0.06513 |
| 73 | 0.054155 | 0.033859 | 0.07576 | 0.012547 | −0.083504 | 0.034715 | −0.188111 | 0.103388 | −0.031555 | −0.050335 | −0.072968 | −0.002908 | −0.032901 | −0.062002 |
| 74 | 0.04245 | 0.018176 | 0.029188 | 0.013637 | −0.02245 | −0.069827 | −0.003359 | 0.06531 | 0.01725 | 0.0256 | −0.001279 | −0.01723 | 0.011447 | 0.00277 |
| 75 | −0.068846 | 0.098322 | 0.043679 | 0.038021 | −0.005943 | −0.156439 | −0.046401 | 0.044107 | −0.052087 | 0.016555 | 0.009124 | 0.07032 | −0.1192 | −0.027395 |
| 76 | 0.021769 | −0.02453 | −0.084003 | −0.006703 | 0.146255 | 0.048171 | −0.029724 | −0.054853 | 0.081837 | −0.016449 | 0.03642 | 0.02721 | 0.013961 | 0.031193 |
| 77 | 0.037715 | −0.079473 | 0.056976 | 0.025767 | −0.015165 | −0.090873 | −0.096319 | 0.024396 | −0.050038 | −0.07423 | −0.02708 | −0.039384 | 0.025461 | −0.098725 |
| 78 | −0.040178 | 0.120891 | −0.011173 | −0.022993 | −0.005879 | 0.155822 | 0.04319 | 0.057717 | 0.088494 | 0.052214 | −0.001839 | 0.112325 | −0.03234 | −0.111491 |
| 79 | −0.065229 | −0.002292 | 0.056224 | −0.021578 | −0.063367 | 0.043253 | 0.13379 | −0.064092 | −0.018817 | −0.090251 | 0.04257 | 0.071748 | 0.177587 | 0.222929 |
| 80 | 0.062486 | 0.021146 | −0.109873 | −0.00258 | −0.023925 | 0.00317 | 0.022982 | −0.063943 | −0.043616 | 0.023069 | 0.025364 | 0.038882 | 0.025512 | 0.01116 |
| 81 | −0.011557 | −0.02092 | −0.075041 | 0.062393 | −0.042432 | 0.008083 | 0.090124 | 0.022282 | 0.065044 | −0.032336 | 0.035326 | −0.070262 | 0.029921 | −0.042435 |
| 82 | −0.036372 | −0.099846 | −0.035177 | −0.041371 | 0.018469 | −0.059717 | −0.180361 | −0.119484 | −0.045449 | −0.111594 | −0.031122 | −0.08599 | −0.095728 | 0.215163 |
| 83 | 0.028868 | 0.042067 | 0.093982 | −0.09567 | −0.08034 | 0.027702 | 0.030497 | 0.100662 | 0.116638 | −0.068076 | 0.081337 | −0.155287 | 0.023349 | −0.28944 |
| 84 | 0.081717 | −0.066756 | 0.11244 | −0.030719 | 0.017095 | 0.038495 | 0.081346 | 0.239617 | 0.052199 | 0.006135 | −0.003965 | 0.020626 | 0.040367 | 0.073022 |
| 85 | −0.002298 | 0.033114 | 0.059979 | 0.029741 | −0.083491 | 0.040473 | 0.102191 | −0.080407 | 0.131174 | −0.048388 | 0.031167 | 0.020222 | −0.031557 | −0.031808 |
| 86 | −0.097194 | −0.078973 | −0.135588 | −0.156809 | 0.030007 | −0.071947 | 0.062985 | 0.093005 | −0.138599 | 0.044972 | −0.032154 | −0.028119 | 0.027443 | −0.107598 |
| 87 | 0.035211 | −0.037015 | −0.005202 | 0.043252 | 0.031103 | −0.083992 | 0.077882 | 0.040638 | 0.005047 | −0.011743 | 0.030264 | 0.113961 | 0.004093 | −0.002248 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 88 | −0.090888 | 0.115627 | −0.005262 | −0.038045 | −0.126597 | −0.047872 | −0.071614 | −0.02362 | 0.080902 | 0.004171 | −0.052843 | −0.065049 | 0.075556 | 0.021542 |
| 89 | 0.031423 | 0.010255 | −0.112773 | −0.044727 | −0.081519 | 0.075844 | 0.020308 | −0.035155 | −0.019815 | 0.005391 | −0.050122 | −0.073981 | 0.03015 | 0.12462 |
| 90 | −0.077689 | −0.063844 | 0.027854 | 0.111376 | −0.099869 | −0.001402 | −0.048731 | −0.044715 | −0.01933 | −0.045983 | −0.12768 | 0.116174 | −0.062556 | −0.022582 |
| 91 | 0.060645 | 0.092415 | −0.040263 | −0.03404 | 0.00848 | −0.024134 | −0.024568 | 0.044844 | 0.0315 | −0.077253 | 0.072825 | 0.06271 | −0.235231 | 0.17357 |
| 92 | 0.11961 | 0.062898 | −0.106559 | −0.018104 | 0.066221 | 0.048598 | 0.018224 | 0.074675 | 0.049976 | 0.063998 | 0.038471 | −0.135053 | 0.076793 | 0.073473 |
| 93 | 0.077548 | −0.098589 | −0.010644 | 0.027632 | 0.064 | −0.046069 | −0.104726 | −0.029681 | −0.006511 | 0.132805 | −0.09831 | 0.003912 | 0.1035 | −0.023315 |
| 94 | 0.018841 | 0.017749 | −0.125756 | −0.054243 | 0.046228 | 0.097183 | −0.002333 | −0.104993 | 0.018006 | 0.035688 | −0.036817 | 0.079009 | 0.182579 | −0.091154 |
| 95 | −0.027113 | 0.002088 | −0.02615 | 0.030836 | 0.041541 | −0.020405 | −0.052883 | 0.01597 | 0.02511 | 0.004992 | 0.02936 | −0.032375 | 0.023074 | 0.090673 |
| 96 | 0.023775 | 0.022458 | −0.005125 | 0.046932 | 0.005304 | −0.088849 | 0.109219 | 0.05911 | −0.04711 | −0.01513 | 0.02483 | 0.038126 | −0.005976 | −0.017659 |
| 97 | 0.017436 | −0.027972 | −0.038168 | 0.007853 | 0.081701 | 0.006689 | 0.031001 | 0.078663 | 0.030637 | 0.092608 | −0.003887 | 0.011592 | 0.056717 | −0.044022 |
| 98 | 0.034486 | 0.153059 | −0.011755 | 0.028932 | 0.037583 | −0.162719 | −0.014664 | 0.035227 | −0.024661 | 0.017003 | −0.098125 | 0.060302 | 0.038456 | 0.049284 |
| 99 | 0.060942 | −0.003602 | −0.056006 | −0.027845 | −0.043632 | −0.057585 | 0.08874 | −0.017705 | −0.138459 | −0.007512 | −0.017755 | 0.106734 | −0.115782 | 0.123395 |
| 100 | −0.063492 | 0.01602 | 0.029406 | 0.008648 | 0.012356 | 0.008719 | 0.066826 | −0.080414 | −0.04259 | −0.026493 | 0.000677 | −0.149116 | 0.04465 | −0.004077 |
| 101 | 0.040857 | 0.039614 | 0.032284 | −0.112672 | 0.008944 | −0.000943 | 0.014479 | −0.13649 | −0.096334 | 0.049216 | 0.027306 | −0.062723 | −0.037739 | 0.012874 |
| 102 | −0.027364 | −0.027424 | 0.074169 | −0.029692 | 0.051694 | 0.051545 | 0.047049 | 0.023822 | −0.085258 | 0.009345 | −0.057487 | 0.037413 | −0.043675 | 0.060958 |
| 103 | −0.052883 | 0.027585 | −0.055382 | −0.021724 | −0.04318 | −0.078243 | −0.087836 | 0.036417 | 0.072238 | 0.013904 | −0.057485 | −0.005245 | 0.011739 | −0.055275 |
| 104 | 0.062934 | −0.020892 | −0.015691 | 0.07691 | −0.026018 | 0.079948 | −0.063743 | −0.011872 | 0.070119 | −0.035776 | 0.010228 | −0.007508 | −0.006978 | −0.090057 |
| 105 | −0.022853 | −0.006699 | 0.010124 | 0.008501 | 0.056835 | 0.033413 | −0.053296 | −0.04157 | −0.048183 | −0.067966 | −0.058003 | −0.015018 | 0.059127 | 0.001732 |
| 106 | 0.0128 | 0.020353 | 0.077041 | 0.012343 | 0.010545 | −0.067428 | 0.077256 | 0.03454 | 0.107252 | −0.071692 | −0.097761 | 0.00848 | 0.030942 | 0.061323 |
| 107 | −0.044724 | −0.096022 | 0.01431 | 0.016708 | 0.060146 | 0.055153 | 0.058659 | 0.027333 | −0.062625 | −0.049889 | 0.066924 | 0.187001 | 0.02606 | −0.024887 |
| 108 | 0.081841 | 0.072253 | 0.026051 | −0.005811 | −0.053319 | 0.074019 | 0.07844 | −0.042793 | 0.027915 | −0.020019 | −0.009316 | −0.059786 | −0.00647 | −0.066454 |
| 109 | −0.009723 | −0.014346 | 0.052222 | 0.004305 | 0.003201 | −0.017114 | 0.067614 | 0.008652 | 0.020874 | 0.039091 | −0.016546 | −0.021229 | 0.027196 | 0.083367 |
| 110 | −0.005067 | 0.009909 | −0.001334 | 0.05532 | 0.050209 | 0.009984 | 0.012355 | −0.005205 | 0.074943 | 0.031062 | −0.004863 | −0.040074 | −0.045056 | −0.055389 |
| 111 | −0.109241 | 0.011005 | −0.047173 | 0.010617 | −0.039962 | −0.04701 | −0.049968 | −0.004046 | −0.115968 | −0.011849 | −0.070043 | −0.001674 | 0.137011 | 0.028974 |
| 112 | −0.016261 | −0.041956 | −0.036493 | −0.053823 | −0.001058 | 0.032474 | −0.041622 | −0.012124 | −0.108927 | −0.008198 | 0.061605 | −0.06042 | −0.031868 | 0.034919 |
| 113 | −0.056758 | −0.021038 | 0.060884 | 0.036091 | −0.03054 | −0.029313 | −0.05009 | −0.032926 | 0.011204 | −0.0562 | 0.068688 | −0.006102 | 0.00012 | 0.026436 |
| 114 | −0.041216 | 0.053141 | −0.021174 | −0.033623 | 0.015422 | −0.042795 | −0.04295 | −0.035014 | −0.012337 | 0.00282 | −0.010923 | −0.038153 | 0.015409 | −0.039553 |
| 115 | 0.01275 | −0.054395 | −0.087848 | −0.051132 | −0.018631 | −0.02654 | 0.004685 | −0.025083 | −0.018536 | −0.00968 | 0.013529 | 0.036329 | 0.007335 | 0.017147 |
| 116 | 0.020908 | 0.154518 | −0.028105 | −0.111037 | 0.051471 | −0.021175 | −0.023172 | 0.057698 | −0.063959 | −0.009539 | 0.041417 | 0.069803 | 0.020269 | −0.029893 |
| 117 | −0.05 | 0.098467 | 0.041904 | 0.034452 | −0.086943 | 0.015687 | −0.023917 | 0.049768 | 0.108026 | 0.119247 | −0.044759 | −0.149448 | 0.072298 | 0.066384 |
| 118 | −0.08057 | 0.055662 | 0.04899 | 0.049273 | −0.010926 | −0.006777 | −0.02188 | −0.015641 | −0.046635 | 0.033632 | −0.081798 | 0.086401 | −0.011325 | −0.018891 |
| 119 | 0.084626 | 0.060563 | 0.053174 | 0.031666 | −0.026417 | −0.030802 | −0.031837 | 0.021837 | −0.052835 | −0.020089 | 0.06651 | −0.010804 | −0.093869 | −0.028919 |
| 120 | −0.00215 | −0.129479 | −0.060333 | −0.090894 | −0.012698 | −0.058255 | 0.08602 | 0.014359 | −0.009515 | −0.012654 | −0.075862 | 0.029788 | 0.116996 | 0.049426 |
| 121 | −0.026556 | 0.021208 | 0.002296 | −0.011959 | 0.032893 | 0.14386 | −0.022898 | 0.043787 | 0.015393 | 0.018449 | 0.062299 | 0.027327 | −0.107521 | 0.036182 |
| 122 | 0.002885 | −0.073388 | 0.007864 | 0.043055 | 0.071559 | −0.064563 | −0.021751 | 0.042407 | 0.075056 | −0.061601 | −0.000978 | −0.00706 | −0.052419 | −0.009657 |
| 123 | 0.095734 | 0.002191 | −0.033698 | 0.008734 | −0.032064 | −0.045451 | 0.000934 | 0.017663 | −0.12127 | −0.025633 | 0.046863 | 0.016787 | 0.042103 | 0.113267 |
| 124 | −0.103907 | −0.000554 | −0.001897 | −0.017813 | −0.004287 | −0.052311 | 0.10249 | 0.010783 | −0.00703 | 0.091421 | −0.074237 | −0.066952 | 0.085042 | 0.114525 |
| 125 | 0.102869 | 0.11341 | 0.040982 | 0.046771 | 0.072913 | −0.023256 | −0.070655 | 0.015757 | 0.062219 | −0.008597 | 0.059767 | −0.01799 | 0.068806 | −0.013755 |
| 126 | 0.069842 | 0.001051 | −0.040614 | −0.033441 | −0.096779 | −0.051883 | −0.038578 | 0.019559 | 0.011584 | −0.004374 | 0.019085 | −0.073133 | 0.042029 | −0.031013 |
| 127 | −0.019171 | 0.084031 | 0.02495 | 0.02649 | 0.182974 | 0.028111 | 0.016163 | −0.064472 | 0.048113 | −0.006079 | 0.028487 | 0.066957 | 0.05773 | −0.044975 |
| 128 | −0.123265 | 0.038553 | 0.071006 | −0.030864 | 0.01548 | 0.001835 | −0.012541 | −0.051663 | 0.019733 | −0.045924 | −0.0041 | −0.092499 | −0.009023 | 0.101245 |
| 129 | 0.019749 | 0.02412 | 0.035997 | −0.004571 | 0.027143 | 0.069903 | −0.008217 | −0.077687 | −0.005619 | −0.047387 | −0.050527 | −0.059731 | 0.040397 | −0.024759 |
| 130 | −0.017072 | 0.073647 | 0.005274 | −0.019584 | −0.060834 | −0.036176 | −0.00077 | 0.045291 | 0.069111 | 0.022692 | 0.054523 | 0.047769 | −0.006918 | 0.014964 |
| 131 | 0.036551 | −0.017441 | −0.0133 | 0.019634 | −0.043179 | −0.048388 | 0.050129 | 0.014176 | 0.056432 | 0.03287 | 0.026487 | 0.016477 | −0.01502 | −0.055095 |
| 132 | 0.012503 | −0.020428 | 0.005311 | −0.06982 | 0.01485 | 0.006975 | 0.038851 | −0.007725 | −0.038142 | −0.011977 | −0.020019 | 0.019072 | 0.025286 | −0.023982 |
| 133 | 0.004468 | −0.001341 | −0.035574 | 0.052358 | −0.036968 | −0.013196 | 0.079929 | −0.03677 | −0.048813 | −0.055912 | 0.022448 | 0.027842 | 0.056125 | 0.01984 |
| 134 | 0.055796 | −0.001766 | −0.000315 | −0.057936 | 0.07362 | 0.021148 | 0.029247 | 0.000977 | −0.028697 | −0.026867 | −0.061842 | −0.027523 | 0.015992 | −0.027401 |
| 135 | 0.007769 | −0.094103 | −0.06958 | 0.051585 | −0.04658 | 0.049804 | 0.009823 | −0.060788 | −0.044547 | 0.053364 | −0.094553 | 0.123048 | 0.150971 | 0.053815 |
| 136 | −0.002234 | −0.070019 | −0.055418 | 0.002699 | 0.05003 | 0.12901 | 0.048044 | −0.039838 | 0.046569 | 0.057479 | 0.026978 | −0.01231 | 0.006745 | −0.052607 |
| 137 | −0.02177 | −0.034834 | −0.028795 | −0.023052 | −0.014626 | 0.08596 | −0.045468 | 0.080897 | −0.024291 | 0.070093 | 0.006553 | 0.093818 | −0.027542 | 0.038547 |
| 138 | −0.026285 | −0.010378 | 0.043039 | 0.063371 | 0.03018 | −0.057731 | −0.032561 | −0.099234 | −0.05722 | −0.081751 | −0.040819 | −0.041481 | −0.004342 | 0.005504 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 139 | 0.015869 | 0.039245 | 0.015496 | −0.007328 | 0.03124 | 0.018778 | 0.065175 | −0.041738 | −0.019057 | 0.001954 | 0.014645 | 0.000894 | −0.044352 | 0.036219 |
| 140 | −0.012252 | −0.021207 | 0.00335 | 0.031885 | −0.001924 | −0.001621 | −0.034429 | −0.010644 | −0.018637 | 0.024148 | 0.022938 | 0.02245 | −0.005002 | 0.034766 |
| 141 | 0.018362 | 0.045252 | −0.010815 | 0.037082 | −0.071622 | 0.032777 | 0.042964 | −0.043157 | 0.02041 | 0.031422 | −0.030585 | −0.059753 | −0.013929 | 0.00897 |
| 142 | 0.01247 | −0.011175 | 0.077236 | −0.006699 | 0.052521 | 0.011597 | 0.008916 | −0.007577 | 0.029538 | −0.036824 | 0.009341 | 0.088092 | −0.058745 | −0.007482 |
| 143 | −0.027027 | −0.065275 | 0.011374 | −0.023599 | 0.000344 | 0.047503 | −0.01549 | 0.050627 | 0.018615 | 0.016464 | 0.03354 | −0.021516 | 0.022951 | −0.004963 |
| 144 | −0.062807 | 0.099186 | 0.01493 | −0.017057 | −0.04069 | 0.018032 | −0.061592 | 0.033229 | 0.02746 | 0.037241 | −0.002188 | −0.037377 | −0.039841 | −0.006821 |
| 145 | −0.008239 | −0.043554 | 0.016023 | −0.014061 | −0.008301 | 0.025187 | 0.018694 | 0.049014 | 0.070111 | −0.019975 | −0.044992 | 0.00833 | −0.020652 | −0.052745 |
| 146 | −0.05768 | 0.031936 | 0.001957 | −0.005557 | −0.018952 | −0.020484 | −0.030547 | −0.000917 | 0.011993 | −0.024494 | 0.01188 | 0.029363 | −0.025909 | −0.007383 |
| 147 | 0.019332 | −0.013629 | 0.055821 | 0.013969 | −0.000852 | 0.012098 | −0.007586 | 0.02509 | 0.029016 | 0.041404 | −0.058199 | 0.062143 | 0.032655 | 0.067965 |
| 148 | 0.029366 | −0.008773 | 0.009547 | −0.034822 | 0.031516 | 0.051845 | −0.017933 | −0.02691 | −0.031282 | 0.022104 | −0.034695 | −0.02282 | 0.000976 | 0.001497 |
| 149 | 0.014841 | −0.001105 | −0.008495 | −0.045565 | −0.08611 | 0.017979 | −0.016011 | −0.010586 | −0.074919 | −0.023968 | 0.025226 | −0.000847 | 0.083024 | 0.025133 |
| 150 | 0.00666 | −0.056087 | 0.036677 | 0.061874 | 0.044576 | −0.088733 | 0.011747 | 0.027486 | −0.05094 | 0.03026 | −0.018838 | −0.031896 | −0.000796 | 0.026025 |
| 151 | 0.007722 | −0.014828 | −0.00634 | 0.001499 | −0.0099 | −0.009426 | −0.007546 | −0.003797 | 0.020001 | −0.059105 | −0.021258 | 0.003889 | −0.045501 | 0.037181 |
| 152 | 0.002874 | −0.069519 | 0.017934 | 0.041842 | 0.039844 | −0.03877 | −0.013424 | −0.049715 | −0.03766 | −0.07697 | 0.0366 | −0.117252 | 0.055982 | 0.04141 |
| 153 | −0.032703 | −0.011168 | 0.063129 | 0.024737 | −0.03267 | 0.025587 | 0.050636 | −0.053655 | 0.075181 | −0.005539 | −0.051303 | −0.002632 | −0.001267 | 0.05276 |
| 154 | −0.018014 | 0.019343 | −0.035427 | 0.038674 | 0.07408 | 0.017319 | 0.01056 | −0.011721 | −0.01588 | −0.0049 | 0.035248 | −0.062911 | −0.044833 | −0.019589 |
| 155 | −0.002249 | 0.021555 | 0.004638 | 0.036467 | 0.013583 | −0.031376 | 0.022283 | 0.028063 | 0.033988 | −0.036465 | 0.049058 | 0.017334 | −0.052976 | 0.015117 |
| 156 | −0.028597 | 0.042176 | −0.015704 | −0.037732 | −0.02701 | −0.034892 | −0.059477 | 0.024433 | −0.04367 | −0.001878 | 0.001147 | 0.076462 | 0.024596 | −0.003805 |
| 157 | 0.022883 | 0.031651 | −0.008844 | −0.009861 | 0.025921 | −0.016738 | −0.019285 | 0.011466 | 0.01233 | −0.005866 | −0.081839 | 0.000287 | −0.021794 | −0.068975 |
| 158 | 0.055212 | −0.0321 | −0.028801 | −0.046101 | −0.041196 | 0.020072 | 0.03015 | −0.000916 | 0.056186 | −0.023573 | 0.050931 | 0.043303 | −0.018798 | −0.041963 |
| 159 | 0.024035 | 0.049498 | −0.013646 | 0.013271 | −0.035268 | −0.014928 | −0.02129 | 0.050287 | 0.062142 | −0.028222 | 0.005816 | −0.009251 | −0.004593 | 0.025465 |
| 160 | −0.031556 | 0.003064 | −0.055038 | −0.018511 | 0.000604 | 0.005698 | 0.023475 | −0.047686 | −0.018231 | 0.018054 | −0.019121 | 0.049334 | 0.014183 | −0.01563 |
| 161 | −0.00917 | 0.004951 | −0.03941 | −0.014202 | −0.00065 | −0.059132 | −0.009743 | 0.008514 | −0.087884 | 0.043356 | 0.001488 | −0.009842 | 0.004312 | −0.009458 |
| 162 | 0.003027 | −0.009165 | −0.011179 | −0.017231 | 0.008566 | 0.002324 | −0.008657 | 0.024726 | 0.016814 | −0.005117 | −0.049997 | 0.05775 | 0.029323 | 0.019266 |
| 163 | −0.005831 | −0.021453 | 0.013774 | 0.014349 | 0.004712 | −0.042056 | −0.032897 | −0.043145 | 0.005047 | −0.025665 | 0.04248 | 0.01098 | −0.028373 | 0.03388 |
| 164 | 0.010247 | −0.00735 | −0.017618 | −0.000175 | −0.001516 | −0.008017 | −0.028943 | −0.044994 | −0.014211 | −0.012972 | −0.027196 | 0.003831 | 0.003656 | −0.024809 |
| 165 | 0.026864 | 0.021774 | 0.013704 | −0.018793 | −0.013303 | −0.009039 | −0.073207 | −0.009134 | −0.029464 | −0.01165 | −0.034257 | −0.050055 | −0.068467 | 0.042634 |
| 166 | −0.008098 | −0.009266 | −0.044346 | −0.036238 | 0.074601 | 0.045725 | −0.002992 | 0.051221 | 0.030394 | −0.061262 | −0.007786 | 0.063704 | −0.019239 | 0.013289 |
| 167 | 0.046287 | 0.010278 | −0.051832 | −0.031974 | 0.049448 | −0.020017 | −0.010886 | −0.023146 | 0.007428 | −0.009662 | −0.001286 | 0.026004 | −0.022222 | −0.038017 |
| 168 | −0.019292 | 0.039105 | −0.015586 | −0.00418 | 0.013278 | −0.000649 | −0.004603 | 0.002431 | 0.010735 | −0.034826 | −0.04041 | −0.029238 | −0.00762 | 0.030503 |
| 169 | 0.036584 | 0.008071 | 0.055603 | 0.015359 | −0.010101 | 0.038751 | −0.036725 | 0.00833 | −0.023743 | −0.019206 | −0.012516 | 0.04824 | 0.027457 | −0.018845 |
| 170 | 0.029052 | 0.003137 | 0.029744 | 0.018829 | −0.029212 | 0.005816 | −0.025452 | 0.030504 | −0.051163 | −0.068592 | −0.010702 | 0.002478 | 0.029811 | 0.018249 |
| 171 | 0.024649 | 0.012847 | 0.00593 | 0.016127 | 0.016655 | 0.019432 | −0.071044 | −0.012409 | −0.016446 | −0.010026 | −0.014657 | 0.015376 | 0.027957 | −0.018276 |
| 172 | −0.024452 | −0.012917 | 0.019162 | −0.061287 | 0.000115 | −0.054238 | −0.025869 | −0.028284 | 0.065392 | −0.074905 | 0.008819 | 0.031475 | 0.020653 | −0.041676 |
| 173 | −0.00122 | 0.005305 | −0.063538 | −0.044505 | 0.008011 | 0.013979 | −0.007837 | 0.024732 | 0.000602 | −0.022667 | 0.012629 | 0.00311 | 0.010117 | −0.007593 |
| 174 | 0.019736 | 0.036449 | 0.003804 | −0.009162 | −0.015496 | 0.019727 | 0.01251 | −0.02982 | 0.016842 | 0.005089 | −0.00121 | 0.001733 | 0.014455 | −0.014482 |
| 175 | −0.041491 | −0.071491 | −0.019375 | −0.056825 | 0.037971 | −0.042403 | −0.040273 | 0.017521 | 0.058372 | −0.05328 | 0.023954 | −0.017201 | 0.019092 | −0.001693 |
| 176 | −0.043559 | −0.038077 | 0.041889 | 0.029594 | 0.005607 | −0.028918 | −0.061544 | −0.01764 | −0.055288 | 0.042744 | 0.042472 | 0.005388 | −0.031626 | 0.006451 |
| 177 | 0.01289 | 0.054253 | −0.035935 | −0.017481 | 0.009592 | −0.038484 | 0.030821 | −0.031091 | 0.021338 | 0.004436 | 0.022433 | 0.009602 | 0.013383 | −0.058199 |
| 178 | −0.002397 | 0.018919 | 0.071491 | 0.00048 | 0.038051 | −0.04396 | −0.033334 | −0.00154 | 0.031845 | −0.016477 | 0.003332 | 0.016464 | 0.006372 | −0.049225 |
| 179 | −0.040686 | −0.027854 | −0.012746 | 0.005363 | −0.009479 | 0.01759 | −0.032483 | −0.036819 | 0.003997 | −0.02299 | −0.011546 | 0.006739 | 0.01282 | 0.037533 |
| 180 | 0.021849 | −0.011444 | −0.017775 | −0.028972 | −0.006581 | 0.052701 | −0.00663 | 0.023191 | −0.021958 | −0.016661 | −0.011493 | 0.01382 | 0.015672 | 0.015627 |
| 181 | 0.039434 | −0.001232 | −0.032009 | −0.019711 | −0.015701 | 0.035624 | −0.017983 | 0.013429 | −0.024069 | 0.000449 | 0.00725 | −0.010598 | 0.005878 | 0.033543 |
| 182 | −0.033975 | 0.032534 | −0.023911 | −0.023399 | −0.025699 | 0.0113 | −0.002886 | 0.03836 | −0.044745 | −0.014822 | 0.041658 | 0.010063 | −0.05313 | 0.03743 |
| 183 | −0.012693 | −0.069867 | −0.038463 | 0.025621 | 0.008484 | 0.002493 | 0.017466 | −0.033004 | 0.024418 | 0.015332 | −0.016567 | −0.013275 | −0.061689 | 0.015652 |
| 184 | 0.025795 | −0.121612 | 0.002384 | −0.030896 | 0.039572 | −0.032737 | 0.01552 | 0.063903 | 0.039497 | 0.053611 | 0.052677 | −0.020907 | 0.032691 | −0.05962 |
| 185 | 0.001085 | 0.002825 | −0.025947 | −0.051491 | 0.026795 | 0.001684 | 0.050345 | 0.024068 | −0.019074 | 0.017376 | 0.01305 | −0.026006 | 0.072121 | 0.010029 |
| 186 | −0.040851 | −0.029987 | −0.080335 | −0.0066 | −0.015257 | −0.02742 | −0.032202 | −0.072171 | 0.041142 | −0.078026 | 0.039999 | 0.001827 | 0.047656 | 0.033684 |
| 187 | −0.104861 | −0.044284 | −0.03853 | 0.016541 | −0.0217 | 0.003995 | −0.020073 | −0.042924 | −0.025413 | −0.033366 | 0.019228 | 0.015039 | 0.001721 | 0.009527 |
| 188 | −0.039868 | −0.082124 | 0.017119 | 0.007304 | −0.007997 | 0.021721 | −0.051867 | −0.018471 | 0.003774 | 0.006196 | −0.000946 | 0.041246 | −0.020566 | −0.003473 |
| 189 | −0.009752 | −0.095288 | 0.012309 | −0.025899 | −0.018689 | 0.00738 | −0.029809 | 0.015853 | −0.009372 | 0.035337 | −0.017725 | −0.009837 | 0.016547 | −0.030922 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 190 | 0.024408 | −0.029293 | −0.048987 | −0.04136 | −0.133246 | 0.029545 | 0.034614 | 0.060792 | 0.006633 | −0.016721 | −0.007613 | −0.038825 | −0.059988 | 0.010854 |
| 191 | 0.006575 | −0.014342 | 0.022415 | −0.023442 | −0.106419 | −0.012888 | −0.024467 | 0.037391 | 0.015566 | −0.031291 | −0.016426 | 0.025113 | −0.006758 | 0.027438 |
| 192 | −0.085162 | 0.055715 | 0.005611 | 0.001542 | −0.079954 | −0.03969 | 0.030722 | 0.011539 | 0.0356 | −0.014672 | 0.010473 | 0.035604 | 0.02801 | −0.00015 |
| 193 | 0.588121 | −0.016993 | 0.006149 | 0.014844 | −0.05174 | −0.02741 | −0.021199 | −0.009906 | −0.025499 | −0.03127 | 0.036989 | 0.004108 | −0.045809 | −0.012762 |
| 194 | −0.027755 | 0.573925 | −0.03366 | −0.006682 | 0.012403 | −0.005351 | −0.000496 | −0.034374 | −0.008424 | −0.045851 | −0.024443 | 0.028675 | 0.008691 | 0.068334 |
| 195 | −0.001069 | −0.062423 | 0.632988 | −0.141704 | −0.012273 | −0.060276 | 0.090266 | −0.03841 | −0.066541 | −0.025347 | −0.004082 | −0.022146 | −0.04003 | 0.018725 |
| 196 | 0.017385 | −0.03527 | −0.129772 | 0.716547 | −0.05979 | 0.011343 | 0.017955 | 0.046753 | 0.007372 | −0.047766 | −0.007191 | −0.046393 | 0.005987 | −0.036334 |
| 197 | −0.034344 | 0.023053 | 0.013202 | −0.056913 | 0.660447 | 0.009089 | 0.008948 | 0.074488 | 0.035681 | −0.017444 | −0.030104 | 0.006414 | −0.007532 | 0.048005 |
| 198 | −0.02157 | −0.030237 | −0.058621 | 0.009918 | −0.008439 | 0.508006 | 0.042597 | −0.052839 | −0.013372 | −0.17187 | −0.032992 | 0.00656 | −0.021824 | 0.029402 |
| 199 | 0.045653 | 0.022299 | −0.006098 | 0.021571 | 0.029649 | −0.008303 | 0.314524 | −0.027994 | 0.034155 | −0.002257 | −0.03945 | 0.008957 | −0.03148 | 0.029243 |
| 200 | −0.043811 | 0.015937 | −0.052978 | 0.028478 | 0.048037 | −0.086645 | −0.015258 | 0.450533 | 0.051642 | −0.138933 | −0.088938 | 0.031058 | 0.018093 | 0.02849 |
| 201 | 0.025031 | −0.027284 | −0.02751 | 0.013385 | 0.001842 | 0.001011 | 0.048572 | 0.018047 | 0.397672 | −0.020597 | −0.000568 | −0.057375 | −0.042232 | 0.021066 |
| 202 | 0.008417 | −0.02815 | −0.044964 | −0.027972 | −0.048316 | −0.150191 | 0.034809 | −0.101912 | 0.02886 | 0.571614 | 0.068576 | 0.024364 | −0.00309 | −0.001143 |
| 203 | 0.033792 | −0.015249 | 0.037611 | .02182 | −0.036092 | −0.048303 | −0.087474 | −0.060393 | 0.007559 | 0.062418 | 0.479068 | 0.045209 | −0.010875 | −0.014126 |
| 204 | −0.03703 | 0.023816 | −0.009117 | −0.036472 | −0.007271 | −0.008044 | 0.031741 | 0.055738 | −0.042293 | −0.023267 | 0.060109 | 0.296089 | 0.023205 | −0.021297 |
| 205 | 0.001198 | 0.001147 | −0.050476 | −0.051417 | 0.005502 | −0.003464 | −0.010082 | 0.002171 | −0.028603 | 0.074557 | 0.053346 | 0.022354 | 0.170707 | −0.067475 |
| 206 | −0.03986 | 0.026084 | 0.001857 | −0.02608 | −0.018647 | 0.05489 | −0.003323 | 0.034619 | 0.045547 | 0.013349 | 0.01969 | −0.009097 | −0.021801 | 0.308561 |
| 207 | −0.003821 | 0.002332 | −0.009004 | −0.038933 | −0.017047 | 0.012496 | −0.012233 | 0.015267 | −0.033135 | 0.042257 | −0.000026 | 0.039541 | 0.023472 | −0.044903 |
| 208 | 0.013643 | −0.039204 | −0.011959 | 0.053354 | −0.036121 | 0.011861 | 0.027119 | −0.017148 | −0.038838 | 0.00026 | −0.046651 | −0.021083 | 0.020916 | 0.003072 |
| 209 | −0.001724 | −0.066891 | 0.011078 | −0.039942 | −0.020243 | −0.002486 | −0.053678 | −0.04356 | 0.030705 | −0.004413 | −0.028783 | −0.043937 | −0.008967 | 0.016385 |
| 210 | −0.032122 | 0.02407 | −0.029121 | −0.004424 | −0.005432 | −0.010793 | −0.01204 | −0.021643 | 0.053122 | 0.037459 | −0.046524 | 0.015831 | −0.00065 | −0.035568 |
| 211 | −0.027529 | −0.001434 | 0.0454 | 0.011693 | −0.004892 | 0.03139 | 0.007564 | −0.040122 | −0.074964 | −0.039513 | 0.026716 | −0.068168 | −0.044567 | −0.016577 |
| 212 | 0.042061 | 0.046969 | −0.027161 | −0.038206 | −0.017872 | −0.053724 | 0.026511 | −0.022238 | 0.053126 | −0.01345 | −0.010422 | 0.041495 | −0.015832 | 0.049065 |
| 213 | −0.009499 | 0.046742 | 0.036547 | −0.023462 | −0.006531 | 0.013075 | −0.018961 | 0.031619 | 0.034865 | 0.041443 | 0.000908 | −0.008371 | 0.008274 | −0.00887 |
| 214 | 0.011754 | −0.025003 | −0.000012 | −0.045365 | −0.007466 | 0.026096 | −0.002391 | −0.004684 | 0.004554 | −0.015286 | −0.02027 | 0.014359 | 0.047061 | −0.023892 |
| 215 | −0.095879 | 0.017323 | −0.032167 | −0.059475 | −0.005947 | −0.020145 | −0.031373 | −0.063881 | 0.011458 | −0.014705 | 0.015901 | −0.015056 | −0.018769 | 0.004344 |
| 216 | 0.045017 | −0.012815 | 0.005022 | 0.029562 | −0.006946 | −0.009059 | −0.011555 | 0.044795 | −0.020662 | 0.039888 | −0.005333 | 0.015966 | −0.015751 | 0.053946 |
| 217 | 0.026166 | −0.001766 | −0.019308 | −0.040137 | 0.010812 | 0.013677 | −0.010995 | −0.020748 | 0.022979 | −0.029507 | −0.034964 | 0.003766 | −0.059859 | −0.000502 |
| 218 | −0.014385 | 0.008272 | −0.042831 | −0.017271 | −0.001568 | 0.01635 | 0.002007 | 0.068969 | −0.022606 | 0.013793 | −0.014302 | −0.003697 | −0.056868 | 0.031263 |
| 219 | 0.029549 | 0.055805 | −0.022956 | −0.025314 | 0.034317 | −0.017206 | −0.017002 | 0.036111 | −0.022841 | 0.025792 | −0.009619 | −0.014152 | −0.004607 | −0.034928 |
| 220 | −0.031516 | 0.044831 | 0.034594 | 0.007668 | −0.00777 | 0.013303 | 0.003619 | −0.018476 | −0.003535 | −0.034895 | 0.002109 | −0.030179 | 0.027429 | −0.000717 |
| 221 | 0.049051 | −0.009581 | −0.020023 | −0.008314 | 0.010409 | 0.013327 | 0.035064 | −0.008374 | 0.034965 | 0.004205 | −0.007992 | 0.011245 | 0.00786 | 0.025396 |
| 222 | 0.015711 | 0.001886 | 0.023747 | −0.004763 | 0.037411 | 0.039042 | −0.017561 | 0.028097 | 0.048044 | 0.050174 | −0.007468 | 0.00927 | −0.019671 | −0.018055 |
| 223 | −0.064431 | −0.045933 | −0.002325 | 0.027692 | 0.055479 | −0.005243 | −0.019211 | 0.036205 | −0.030624 | 0.059201 | 0.000765 | 0.000919 | −0.044201 | −0.003387 |
| 224 | 0.027427 | 0.017432 | −0.017595 | −0.022958 | −0.014538 | −0.004463 | 0.001966 | 0.019295 | 0.004101 | −0.015767 | 0.065596 | −0.000183 | 0.006297 | 0.009768 |
| 225 | 0.029065 | 0.000256 | −0.00313 | 0.00731 | 0.023388 | −0.045058 | −0.006731 | 0.018943 | −0.006837 | −0.019411 | 0.056762 | 0.005695 | −0.01507 | 0.010053 |
| 226 | 0.007179 | 0.020766 | 0.003623 | −0.000385 | 0.000308 | −0.026519 | −0.006854 | −0.039073 | 0.038313 | −0.033977 | 0.013478 | 0.010554 | −0.042689 | 0.043515 |
| 227 | −0.018007 | 0.005309 | 0.009615 | 0.018602 | 0.075046 | 0.032998 | 0.054469 | 0.016407 | −0.033332 | 0.021361 | −0.041614 | 0.008202 | −0.000073 | −0.018808 |
| 228 | −0.001884 | 0.008687 | −0.006921 | 0.004921 | −0.043696 | −0.000779 | −0.00796 | 0.003079 | −0.025242 | −0.002308 | −0.039038 | −0.007288 | −0.015795 | 0.029426 |
| 229 | 0.003274 | −0.050569 | −0.007708 | 0.015104 | 0.044865 | 0.016818 | 0.01723 | −0.020731 | −0.008875 | −0.019575 | −0.000621 | 0.023191 | 0.002054 | 0.021262 |
| 230 | −0.011523 | −0.035533 | 0.011151 | 0.005207 | −0.000817 | 0.031486 | −0.044147 | −0.038903 | 0.013935 | 0.007526 | 0.014781 | −0.034195 | −0.018052 | 0.049621 |
| 231 | −0.050316 | 0.011327 | 0.036645 | 0.029563 | −0.000756 | 0.038246 | −0.020604 | 0.022408 | 0.004073 | 0.032942 | 0.075687 | −0.022078 | 0.008433 | −0.002612 |
| 232 | −0.030997 | 0.013524 | −0.012204 | −0.055028 | −0.018688 | −0.043049 | −0.030857 | 0.022346 | 0.038653 | −0.057035 | −0.035437 | 0.003964 | 0.015499 | −0.019365 |
| 233 | −0.026528 | −0.010714 | −0.017174 | −0.014982 | 0.029877 | −0.0612 | 0.002296 | −0.034401 | 0.004431 | −0.032518 | −0.046095 | 0.014835 | 0.029368 | −0.008197 |
| 234 | 0.031918 | 0.04156 | 0.054966 | 0.000601 | −0.068895 | 0.025398 | −0.022145 | −0.032879 | −0.010443 | 0.015493 | −0.011935 | 0.018197 | −0.000799 | 0.063256 |
| 235 | 0.017002 | −0.050436 | 0.071348 | −0.003008 | 0.003525 | 0.086142 | −0.058739 | −0.075813 | 0.071134 | −0.022974 | −0.020425 | −0.014158 | 0.045119 | −0.04261 |
| 236 | −0.008767 | 0.002052 | 0.024866 | 0.019636 | −0.020751 | 0.028344 | 0.035772 | −0.014396 | 0.076921 | 0.054327 | 0.007371 | 0.011032 | −0.012073 | 0.01174 |
| 237 | −0.046507 | −0.029053 | −0.021913 | 0.009517 | −0.030058 | −0.007726 | 0.039735 | −0.017459 | −0.022091 | 0.022313 | 0.015268 | 0.034909 | 0.014586 | −0.024788 |
| 238 | 0.022805 | −0.000356 | −0.006818 | 0.01018 | 0.010948 | −0.027599 | −0.008607 | −0.009786 | −0.033416 | 0.001333 | 0.018131 | −0.027555 | 0.037979 | −0.048594 |
| 239 | 0.005453 | 0.005987 | −0.020606 | −0.012959 | 0.008769 | −0.035261 | −0.013181 | 0.014696 | −0.047187 | −0.002017 | −0.002593 | −0.000672 | −0.023707 | 0.01214 |
| 240 | 0.000213 | −0.000156 | −0.022229 | 0.023991 | 0.035645 | 0.004157 | −0.01294 | 0.015954 | −0.012242 | −0.023884 | −0.009966 | 0.027653 | −0.034869 | −0.01216 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 241 | 0.024969 | −0.008959 | −0.013845 | −0.016453 | 0.016685 | −0.053492 | 0.041741 | −0.033185 | −0.026345 | 0.015396 | −0.034471 | −0.051401 | −0.06283 | 0.015448 |
| 242 | 0.020097 | −0.015894 | 0.027711 | 0.039132 | 0.04066 | 0.012748 | 0.043332 | 0.007787 | −0.025801 | −0.00359 | −0.01991 | −0.004727 | −0.02569 | 0.001177 |
| 243 | −0.010607 | 0.00986 | 0.002305 | 0.017084 | 0.024203 | −0.004824 | 0.028138 | 0.003912 | −0.030246 | 0.000435 | 0.037687 | −0.068975 | −0.007391 | −0.037878 |
| 244 | −0.029856 | −0.02586 | 0.013255 | 0:03588 | 0.001443 | −0.014043 | 0.042389 | −0.005634 | 0.031393 | −0.019742 | 0.030079 | 0.054098 | −0.008387 | −0.016531 |
| 245 | 0.029984 | −0.001102 | 0.027134 | −0.035068 | 0.01494 | 0.035918 | −0.056952 | 0.013192 | 0.053292 | 0.041991 | −0.035113 | 0.008826 | −0.006975 | −0.000955 |
| 246 | −0.000599 | 0.027703 | 0.000143 | −0.005495 | 0.001554 | 0.031441 | 0.025717 | 0.014594 | −0.036924 | 0.018558 | −0.009344 | −0.000356 | −0.048501 | 0.03369 |
| 247 | 0.051154 | −0.022116 | −0.015014 | −0.023963 | −0.001822 | 0.001122 | 0.019614 | −0.034692 | 0.033437 | 0.018687 | −0.026168 | 0.004291 | −0.057293 | 0.008584 |
| 248 | 0.000985 | −0.02948 | −0.023082 | −0.009584 | −0.033924 | −0.002941 | −0.003996 | −0.026683 | 0.05142 | 0.008546 | 0.009806 | −0.001558 | −0.039703 | −0.006353 |
| 249 | −0.049419 | 0.024937 | 0.034051 | 0.054639 | 0.011761 | 0.014151 | −0.041611 | −0.006266 | −0.003899 | −0.042711 | 0.02131 | 0.007166 | 0.006043 | −0.028996 |
| 250 | −0.027114 | −0.028344 | −0.000211 | −0.027873 | 0.025506 | 0.051593 | 0.029205 | 0.06357 | −0.011615 | 0.019187 | 0.038136 | 0.001018 | −0.031418 | −0.040188 |
| 251 | −0.004396 | −0.025279 | 0.018165 | −0.008417 | 0.015337 | 0.008401 | 0.023722 | 0.027648 | −0.014056 | −0.016834 | 0.029047 | −0.033158 | 0.031808 | −0.03943 |
| 252 | 0.03312 | −0.009428 | −0.016262 | 0.013172 | −0.021859 | −0.04401 | 0.021147 | 0.023849 | 0.067164 | 0.028122 | 0.012703 | −0.052377 | −0.002607 | −0.005803 |
| 253 | −0.034291 | −0.005598 | −0.018693 | 0.011294 | 0.001227 | 0.03389 | 0.007472 | 0.029444 | −0.029041 | 0.056744 | 0.011097 | 0.031012 | −0.051153 | 0.026818 |
| 254 | −0.110412 | −0.028015 | 0.032534 | 0.068253 | 0.002626 | −0.033876 | −0.00175 | 0.041646 | −0.085384 | 0.021519 | −0.015731 | 0.009228 | 0.046056 | 0.032498 |
| 255 | −0.029863 | 0.006464 | 0.022425 | 0.05888 | 0.018365 | −0.012744 | 0.046127 | 0.017118 | −0.002045 | 0.018136 | 0.032161 | 0.003904 | 0.015568 | 0.020937 |
| 256 | 0.007559 | −0.012029 | −0.01472 | −0.037628 | −0.02729 | −0.002466 | −0.011963 | 0.003998 | 0.007672 | 0.024732 | −0.021629 | −0.01455 | −0.006235 | −0.003792 |
| 257 | −0.022718 | −0.0204 | −0.002993 | −0.038359 | −0.032422 | 0.001203 | −0.044111 | 0.018095 | 0.008989 | 0.020489 | 0.005059 | −0.029824 | −0.014613 | −0.008752 |
| 258 | −0.012883 | 0.001254 | −0.010643 | 0.00956 | −0.01795 | −0.005809 | −0.063134 | −0.008324 | 0.01399 | 0.015794 | 0.028291 | −0.017457 | −0.050087 | 0.060578 |
| 259 | −0.003749 | 0.001306 | 0.03474 | 0.021781 | 0.030228 | 0.079203 | 0.020262 | 0.02343 | 0.009989 | 0.023007 | 0.016579 | 0.006053 | −0.012566 | 0.004865 |
| 260 | −0.014974 | −0.028073 | 0.008227 | −0.000059 | 0.039496 | −0.041637 | 0.005463 | 0.041788 | 0.042244 | 0.012327 | −0.033836 | −0.004915 | −0.028872 | 0.023659 |
| 261 | 0.028549 | −0.005963 | −0.060014 | −0.04006 | −0.038423 | 0.006043 | −0.018316 | 0.02096 | −0.03382 | −0.013359 | −0.023597 | 0.027152 | 0.00405 | −0.018122 |
| 262 | 0.03388 | −0.006747 | −0.02947 | −0.014522 | 0.002949 | −0.038664 | −0.021384 | −0.052132 | −0.014218 | −0.06309 | −0.029648 | 0.003495 | 0.017212 | 0.000482 |
| 263 | 0.007425 | −0.022495 | −0.001679 | 0.010645 | 0.000979 | −0.033338 | −0.0262 | −0.016137 | −0.007576 | −0.014622 | −0.011979 | 0.000836 | 0.057811 | −0.013364 |
| 264 | −0.003212 | 0.004894 | 0.052898 | 0.01013 | −0.026458 | 0.039878 | −0.008917 | 0.044908 | 0.030024 | 0.051416 | 0.020084 | 0.046428 | 0.034029 | −0.034337 |
| 265 | −0.091593 | −0.015291 | −0.067524 | −0.029443 | −0.027704 | 0.019543 | −0.040601 | 0.016879 | −0.024585 | 0.015881 | −0.010302 | −0.01174 | 0.005217 | 0.012646 |
| 266 | 0.009407 | −0.041796 | −0.086389 | −0.068434 | −0.002529 | −0.018082 | −0.062165 | −0.004375 | −0.044773 | −0.000114 | −0.011582 | −0.009393 | 0.010188 | −0.000697 |
| 267 | 0.006059 | 0.007595 | 0.035471 | −0.029415 | 0.000727 | −0.004366 | −0.010105 | 0.032838 | 0.040811 | −0.039519 | −0.059878 | −0.007321 | −0.016582 | 0.020339 |
| 268 | 0.014104 | 0.005386 | −0.011154 | −0.002412 | 0.009309 | −0.040753 | −0.024953 | −0.004757 | 0.025439 | −0.017224 | −0.034975 | 0.010015 | 0.002807 | 0.018195 |
| 269 | 0.041306 | −0.004538 | 0.007618 | 0.018261 | 0.024065 | −0.046039 | 0.01013 | −0.033409 | 0.031371 | −0.014489 | 0.011854 | 0.003748 | −0.01941 | −0.012289 |
| 270 | −0.00236 | 0.005522 | 0.006654 | 0.019637 | −0.006172 | −0.013601 | 0.021392 | 0.047307 | 0.010449 | 0.004125 | −0.012009 | 0.029418 | −0.01081 | 0.006022 |
| 271 | 0.033307 | 0.019716 | 0.00934 | 0.02621 | 0.019356 | 0.040472 | −0.020193 | −0.031542 | 0.014655 | 0.032254 | 0.032399 | 0.027962 | −0.022264 | −0.037473 |
| 272 | −0.048406 | 0.041084 | −0.031886 | −0.00885 | 0.017464 | −0.045422 | −0.011479 | −0.021013 | −0.012102 | 0.025634 | 0.026567 | −0.053405 | 0.008702 | −0.050917 |
| 273 | −0.003682 | 0.0152 | −0.041847 | −0.016165 | −0.006484 | −0.007963 | −0.045276 | −0.029927 | −0.00085 | −0.031272 | 0.02528 | −0.033664 | 0.032757 | 0.022917 |
| 274 | −0.004456 | 0.022841 | −0.041127 | −0.025684 | 0.002082 | −0.006002 | −0.042127 | −0.033761 | −0.005849 | −0.028335 | 0.037766 | −0.043121 | 0.008202 | 0.009099 |
| 275 | −0.006523 | −0.023218 | 0.03586 | −0.00963 | −0.014604 | −0.019994 | 0.019678 | −0.049875 | −0.035002 | −0.007881 | −0.020085 | 0.013272 | 0.012915 | −0.016818 |
| 276 | 0.048544 | 0.031084 | 0.0374 | 0.011707 | −0.022164 | 0.034997 | 0.00085 | 0.024054 | 0.042806 | 0.07843 | −0.010496 | 0.014327 | 0.028933 | 0.004753 |
| 277 | 0.028193 | 0.015653 | −0.035792 | −0.005588 | −0.000092 | −0.018944 | 0.024087 | 0.026715 | 0.002314 | 0.008795 | −0.022268 | 0.000789 | 0.014948 | −0.005758 |
| 278 | −0.035305 | 0.068074 | −0.02018 | 0.007944 | −0.003564 | −0.00104 | 0.049457 | 0.023851 | −0.029243 | 0.024702 | −0.00453 | −0.020821 | −0.052708 | 0.02109 |
| 279 | 0.006874 | 0.006976 | 0.01354 | 0.011941 | −0.014791 | −0.016171 | −0.016575 | −0.00235 | −0.000301 | −0.004832 | 0.003468 | 0.008238 | 0.009894 | −0.015528 |
| 280 | −0.009664 | 0.018938 | −0.013568 | −0.037358 | 0.008352 | 0.008022 | −0.032684 | 0.015204 | −0.03085 | −0.008845 | 0.028612 | −0.002978 | 0.01934 | −0.027117 |
| 281 | 0.046952 | −0.033352 | 0.056863 | 0.012992 | −0.006642 | 0.030861 | −0.025566 | −0.00622 | 0.001741 | −0.022557 | −0.052526 | −0.026394 | 0.011303 | −0.013139 |
| 282 | 0.031165 | 0.027242 | 0.042733 | 0.026232 | 0.009292 | 0.043423 | 0.031269 | −0.045095 | −0.001988 | −0.026166 | 0.00611 | −0.034759 | 0.01912 | −0.004491 |
| 283 | −0.002644 | −0.022597 | 0.005324 | −0.027864 | 0.007782 | 0.004334 | 0.053385 | −0.064418 | 0.004113 | −0.047848 | −0.029935 | 0.016337 | −0.018225 | −0.035338 |
| 284 | 0.012452 | −0.025291 | 0.03463 | −0.03122 | −0.037201 | 0.025049 | −0.012487 | 0.012338 | −0.003923 | 0.005881 | −0.016865 | 0.003211 | 0.031671 | −0.012097 |
| 285 | 0.009981 | 0.016216 | 0.016806 | −0.025267 | −0.031587 | 0.046363 | 0.016507 | 0.035842 | 0.001643 | 0.020953 | 0.037497 | −0.031815 | 0.006213 | −0.025814 |
| 286 | −0.011171 | −0.012816 | 0.03848 | 0.001908 | −0.00657 | 0.002231 | −0.067433 | −0.005044 | −0.032713 | −0.014088 | 0.022387 | 0.00763 | 0.077931 | 0.001549 |
| 287 | −0.014104 | 0.003055 | 0.043024 | −0.004405 | 0.006453 | −0.013206 | −0.012554 | 0.013404 | −0.058064 | −0.028268 | 0.032619 | −0.009495 | 0.0613 | −0.015471 |
| 288 | −0.002101 | −0.017757 | 0.021259 | 0.006102 | 0.019432 | −0.000574 | 0.017867 | −0.003821 | −0.017232 | −0.01074 | 0.042789 | −0.031119 | 0.024868 | 0.01034 |
| 289 | 0.003916 | 0.01067 | −0.028432 | −0.030282 | 0.003505 | −0.057079 | −0.009073 | −0.030731 | 0.002822 | −0.064961 | −0.007413 | −0.017818 | −0.014208 | −0.007752 |
| 290 | −0.017693 | −0.016964 | 0.035996 | 0.017862 | 0.019772 | 0.007236 | 0.006821 | −0.010278 | 0.00366 | 0.013752 | −0.013185 | −0.016957 | 0.009293 | 0.033731 |
| 291 | −0.009471 | −0.027759 | 0.036103 | 0.012726 | 0.018921 | 0.008197 | 0.004574 | −0.010012 | −0.001563 | 0.007934 | −0.007195 | −0.010076 | 0.013785 | 0.035166 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 292 | 0.001313 | −0.06297 | 0.052595 | 0.000845 | 0.0167 | 0.035748 | 0.028724 | 0.004095 | 0.024949 | 0.010735 | 0.022329 | 0.007328 | 0.004754 | −0.016955 |
| 293 | −0.044014 | −0.040808 | 0.021698 | 0.008452 | −0.00472 | 0.017408 | 0.039338 | −0.016386 | 0.065984 | −0.00999 | −0.020399 | −0.000138 | 0.008044 | 0.001735 |
| 294 | −0.040552 | 0.037078 | −0.005376 | −0.012139 | −0.021994 | −0.031552 | 0.002363 | −0.023482 | −0.015494 | 0.015225 | 0.021557 | 0.035114 | −0.010902 | −0.032487 |
| 295 | −0.013976 | 0.003979 | −0.021851 | −0.002622 | −0.009052 | 0.020484 | −0.043924 | 0.030545 | −0.007647 | −0.005318 | −0.018542 | −0.009945 | −0.013739 | 0.007391 |
| 296 | 0.010277 | 0.049234 | −0.048382 | −0.026746 | 0.016845 | 0.025768 | −0.063362 | 0.040964 | −0.034183 | 0.035501 | −0.054991 | −0.013921 | −0.004501 | 0.006047 |
| 297 | 0.020874 | −0.028723 | 0.019762 | 0.003217 | −0.006407 | 0.065657 | 0.01432 | 0.079214 | 0.003994 | 0.004038 | −0.011795 | 0.016328 | −0.020437 | 0.008377 |
| 298 | −0.008328 | 0.008476 | 0.029319 | 0.014413 | 0.063461 | −0.040097 | −0.017629 | −0.030283 | −0.022667 | 0.038423 | −0.006623 | 0.068865 | −0.008429 | 0.070274 |
| 299 | −0.045055 | −0.026975 | 0.022187 | 0.006118 | −0.036741 | −0.00886 | 0.026559 | 0.044813 | −0.012374 | −0.024054 | −0.019706 | 0.025789 | 0.02377 | 0.024331 |
| 300 | −0.007143 | −0.009808 | 0.117328 | 0.010447 | −0.061521 | −0.007343 | −0.057176 | 0.036481 | 0.054013 | 0.026989 | 0.033286 | −0.002124 | −0.073625 | −0.00509 |
| 301 | −0.011062 | 0.01804 | 0.019409 | 0.006447 | −0.034563 | 0.007879 | 0.028992 | 0.014525 | 0.014285 | −0.008191 | −0.013941 | −0.008769 | 0.003188 | −0.026477 |
| 302 | 0.01353 | 0.019003 | −0.020935 | −0.029636 | 0.006812 | −0.005051 | 0.016541 | 0.030187 | −0.035252 | −0.024151 | 0.005198 | −0.022168 | 0.002527 | −0.007015 |
| 303 | −0.008744 | 0.05256 | −0.011813 | 0.014839 | 0.017527 | −0.028298 | 0.032153 | −0.043775 | 0.00909 | −0.037219 | 0.025817 | 0.060002 | −0.0507 | 0.024539 |
| 304 | −0.016947 | −0.006933 | −0.005932 | −0.049992 | 0.000187 | 0.072948 | 0.036441 | 0.011652 | 0.006867 | −0.032915 | 0.029361 | 0.071496 | 0.030717 | −0.012114 |
| 305 | −0.060066 | 0.026362 | −0.00819 | −0.011359 | −0.00195 | −0.090298 | 0.018535 | −0.07856 | 0.039449 | 0.013052 | −0.0587 | 0.027046 | −0.051207 | −0.124163 |
| 306 | −0.018646 | −0.053291 | 0.019092 | −0.007028 | 0.007952 | −0.017557 | 0.01033 | 0.037616 | 0.00254 | 0.036204 | −0.028851 | −0.038297 | −0.108313 | −0.00649 |
| 307 | −0.031812 | −0.001063 | 0.017314 | −0.020989 | −0.02589 | 0.004131 | 0.015119 | −0.022966 | −0.043868 | −0.035958 | −0.011042 | −0.0454 | −0.047305 | −0.044969 |
| 308 | −0.006171 | 0.017202 | 0.015044 | −0.011849 | −0.000001 | −0.024255 | −0.009035 | 0.015922 | 0.023393 | −0.011809 | 0.022083 | −0.019977 | 0.027288 | −0.017591 |
| 309 | 0.003223 | −0.020698 | 0.015391 | 0.048742 | 0.030838 | −0.038145 | 0.005447 | 0.017378 | −0.004249 | −0.02384 | 0.034749 | 0.009589 | 0.0197651 | −0.02877 |
| 310 | −0.057409 | −0.039632 | −0.04858 | 0.034236 | 0.05995 | 0.023255 | −0.052834 | −0.050111 | −0.057193 | 0.05313 | −0.003372 | 0.053232 | 0.008675 | −0.042377 |
| 311 | 0.026293 | −0.073946 | −0.015313 | 0.010872 | 0.01704 | −0.030364 | −0.010993 | −0.059298 | 0.013999 | −0.010448 | −0.045691 | −0.003936 | −0.021187 | 0.002562 |
| 312 | 0.002371 | −0.016044 | 0.004838 | 0.02288 | −0.000809 | −0.017859 | 0.002337 | −0.051846 | 0.027045 | 0.061544 | 0.057361 | 0.012415 | −0.02264 | −0.007452 |
| 313 | 0.045182 | −0.032974 | 0.01484 | 0.034322 | −0.052098 | −0.01042 | 0.053748 | −0.034353 | 0.011494 | 0.010643 | −0.019188 | −0.00504 | 0.041571 | −0.0073 |
| 314 | 0.074058 | −0.024167 | −0.025383 | −0.015861 | 0.042348 | −0.044819 | 0.059466 | −0.029561 | −0.054731 | −0.055947 | 0.050195 | −0.101816 | −0.0449 | 0.045368 |
| 315 | 0.016325 | −0.032526 | 0.019094 | −0.014929 | −0.020121 | −0.009877 | −0.027199 | −0.012639 | 0.00492 | −0.02683 | −0.026376 | −0.050033 | −0.055096 | −0.018916 |
| 316 | −0.003904 | −0.002609 | 0.00919 | 0.007118 | −0.032846 | −0.016613 | 0.044056 | 0.002803 | 0.12471 | −0.0383 | 0.04006 | 0.027856 | 0.00578 | −0.011218 |
| 317 | −0.018239 | −0.050005 | −0.001062 | 0.002164 | −0.004482 | −0.004077 | −0.007338 | −0.00633 | −0.029857 | −0.022772 | 0.0054861 | 0.010029 | −0.036409 | −0.016391 |
| 318 | 0.033372 | −0.044687 | 0.021112 | −0.012019 | 0.009714 | −0.037943 | 0.016878 | 0.021736 | 0.033899 | 0.017657 | 0.060664 | 0.022838 | −0.025059 | −0.048141 |
| 319 | −0.001409 | −0.03094 | −0.003805 | −0.00179 | −0.00252 | 0.017405 | −0.047313 | −0.014972 | −0.001106 | −0.028042 | 0.018807 | −0.024935 | 0.017404 | 0.023462 |
| 320 | 0.054025 | −0.014107 | −0.052856 | −0.021244 | 0.050188 | 0.003199 | −0.049669 | −0.046965 | −0.052671 | 0.094122 | −0.001889 | −0.083922 | −0.02986 | 0.044295 |
| 321 | −0.013695 | 0.013613 | 0.063204 | 0.000869 | −0.06717 | −0.028553 | 0.050891 | 0.046499 | −0.024286 | −0.019288 | −0.02924 | 0.001649 | 0.071078 | −0.007016 |
| 322 | −0.013226 | 0.000739 | 0.066913 | 0.001239 | 0.029328 | −0.03162 | −0.09496 | −0.020621 | 0.021532 | 0.00552 | 0.051758 | −0.025468 | 0.001558 | −0.045879 |
| 323 | 0.015407 | 0.008217 | 0.014777 | 0.032402 | −0.030327 | 0.047 | −0.032596 | 0.032591 | −0.050229 | 0.048561 | −0.011711 | 0.030013 | −0.027677 | 0.042154 |
| 324 | 0.041553 | −0.02206 | 0.007759 | 0.036766 | −0.049516 | −0.057286 | 0.029225 | 0.018097 | −0.045429 | −0.033065 | −0.024446 | −0.016842 | 0.004244 | 0.014001 |
| 325 | 0.02324 | 0.010086 | −0.021834 | 0.029985 | −0.018034 | −0.008228 | −0.016269 | −0.028239 | −0.044935 | −0.003428 | −0.005377 | 0.045428 | 0.041981 | 0.007958 |
| 326 | −0.054419 | 0.039641 | −0.056549 | −0.032133 | 0.004341 | −0.010898 | 0.01839 | −0.03378 | 0.010599 | 0.001414 | −0.107914 | −0.094782 | 0.009376 | 0.03308 |
| 327 | 0.02901 | 0.006297 | 0.008059 | −0.003283 | −0.015824 | −0.028509 | −0.038975 | 0.015492 | 0.016497 | 0.005346 | 0.003632 | −0.012916 | −0.001355 | −0.041076 |
| 328 | −0.011342 | 0.025591 | 0.006746 | 0.016292 | −0.035308 | 0.047791 | −0.031133 | 0.063473 | −0.007089 | −0.053505 | 0.037958 | −0.005865 | 0.048642 | 0.008253 |
| 329 | −0.013717 | 0.02572 | 0.011354 | −0.001574 | −0.026106 | 0.00897 | 0.009065 | 0.038457 | 0.002464 | 0.082978 | −0.025301 | −0.04939 | 0.053887 | −0.010542 |
| 330 | 0.038503 | 0.000789 | 0.036388 | 0.01293 | 0.002697 | −0.040571 | −0.027041 | −0.033227 | −0.134132 | −0.013907 | 0.029839 | −0.033669 | −0.044361 | −0.004927 |
| 331 | −0.006713 | 0.027821 | −0.015297 | −0.003183 | 0.041643 | −0.029462 | 0.013334 | 0.004842 | −0.000095 | 0.025463 | 0.002804 | −0.008071 | −0.061823 | 0.004845 |
| 332 | −0.020378 | 0.052733 | 0.010126 | −0.025115 | −0.014832 | 0.012167 | 0.021895 | 0.062443 | 0.094404 | −0.015126 | 0.105627 | 0.05556 | 0.05567 | 0.023612 |
| 333 | 0.000416 | 0.042185 | −0.010349 | 0.002946 | −0.028959 | −0.004645 | −0.029166 | 0.060923 | 0.014196 | 0.024352 | 0.035715 | 0.01414 | −0.011709 | −0.006725 |
| 334 | −0.031641 | 0.01335 | 0.015062 | −0.022133 | −0.024937 | 0.043257 | −0.05694 | 0.042225 | −0.059621 | −0.04311 | −0.002038 | 0.002586 | −0.005025 | −0.013051 |
| 335 | −0.014839 | −0.009587 | −0.012299 | 0.019925 | −0.001068 | −0.011655 | −0.007064 | −0.064896 | 0.023699 | 0.047795 | 0.004908 | −0.026396 | 0.017137 | −0.011947 |
| 336 | −0.013131 | 0.009682 | 0.045875 | −0.003265 | −0.012165 | −0.056392 | −0.003664 | 0.010026 | −0.002655 | −0.002915 | −0.03692 | 0.082652 | 0.037293 | −0.061286 |
| 337 | 0.014755 | 0.000536 | −0.017704 | 0.087007 | 0.029899 | 0.008185 | 0.002745 | 0.007486 | −0.027891 | 0.047978 | −0.094436 | −0.127151 | 0.002968 | 0.071991 |
| 338 | 0.00702 | −0.070779 | −0.033706 | 0.003715 | −0.018518 | −0.044597 | 0.037581 | −0.043235 | −0.012294 | 0.015153 | −0.034548 | 0.075582 | −0.026185 | −0.051081 |
| 339 | −0.052266 | −0.014742 | −0.001693 | −0.043291 | −0.004188 | 0.111009 | 0.017009 | −0.006808 | 0.024149 | −0.058937 | −0.010943 | −0.031671 | 0.022157 | −0.029673 |
| 340 | 0.022243 | 0.017752 | 0.02066 | 0.000331 | 0.026492 | 0.007636 | −0.06274 | 0.013463 | −0.010411 | 0.012302 | −0.038336 | −0.039326 | 0.050437 | −0.001878 |

APPENDIX B1-continued

PCA Transformation Matrix(340 × 340; Normal/Diseased)

| | GZ | HA | HB | HC | HD | HE | HF | HG | HH | HI | HJ | HK | HL | HM |
|---|---|---|---|---|---|---|---|---|---|---|---|---|---|---|
| 1 | 0.061809 | 0.028024 | 0.03968 | 0.098533 | −0.14903 | −0.041224 | 0.111792 | 0.012378 | −0.000626 | −0.020942 | −0.094898 | 0.002616 | 0.059509 | −0.018446 |
| 2 | 0.073633 | 0.010217 | 0.10007 | 0.153534 | 0.017532 | 0.025752 | −0.325065 | 0.054255 | 0.000046 | 0.010527 | 0.062239 | −0.079642 | −0.009402 | 0.093979 |
| 3 | 0.061709 | −0.108425 | −0.058973 | −0.060632 | −0.018222 | −0.052088 | 0.12002 | 0.023511 | 0.029216 | 0.006395 | −0.022789 | 0.038274 | −0.112839 | −0.010155 |
| 4 | −0.0031 | 0.01397 | 0.060429 | 0.063868 | −0.062419 | −0.009459 | 0.09014 | −0.005238 | −0.032308 | −0.04509 | 0.009296 | −0.046023 | 0.041658 | 0.04058 |
| 5 | −0.073093 | 0.027851 | −0.083584 | 0.040124 | 0.040994 | −0.057992 | 0.064997 | −0.036446 | −0.030364 | 0.013841 | 0.024033 | −0.008974 | −0.035763 | −0.006 |
| 6 | −0.018785 | −0.015644 | −0.050236 | 0.030347 | 0.023253 | 0.009155 | −0.048435 | 0.018247 | 0.000243 | 0.009632 | 0.024261 | 0.01451 | 0.021681 | −0.119171 |
| 7 | 0.055689 | 0.014266 | 0.016621 | −0.046285 | 0.045818 | −0.108586 | −0.072371 | −0.053614 | 0.058145 | −0.082691 | −0.094895 | 0.01208 | −0.027565 | −0.092141 |
| 8 | −0.04278 | 0.040549 | −0.08929 | −0.04195 | −0.065253 | 0.035056 | −0.021226 | −0.00012 | −0.044396 | 0.064417 | 0.031058 | 0.002558 | −0.0002 | −0.001914 |
| 9 | 0.032651 | −0.042184 | −0.019455 | −0.053441 | 0.018179 | 0.01061 | −0.189462 | 0.013003 | 0.004019 | −0.042226 | −0.038402 | −0.02622 | −0.017454 | 0.012366 |
| 10 | −0.027877 | −0.08832 | −0.020698 | −0.055 | −0.035791 | 0.054225 | −0.02188 | 0.000235 | −0.088561 | 0.037897 | 0.005711 | −0.059606 | −0.002526 | −0.027254 |
| 11 | 0.107281 | −0.028427 | 0.063339 | −0.04439 | −0.005218 | 0.02347 | 0.088633 | 0.042952 | 0.02517 | 0.015034 | −0.021046 | −0.014652 | 0.021151 | −0.052582 |
| 12 | 0.012341 | −0.011716 | 0.076463 | −0.059548 | −0.038152 | 0.018672 | −0.043685 | 0.038478 | 0.079921 | −0.018976 | −0.036713 | 0.012065 | 0.025711 | 0.002826 |
| 13 | 0.033377 | −0.035808 | 0.042702 | 0.013114 | −0.045538 | −0.148637 | −0.063898 | −0.009526 | 0.071085 | −0.060643 | 0.081842 | −0.007124 | 0.031561 | 0.037706 |
| 14 | 0.225923 | 0.074886 | −0.244276 | −0.108497 | −0.054508 | 0.107561 | −0.038011 | −0.017611 | −0.036996 | −0.00288 | −0.063078 | 0.01721 | −0.056355 | 0.055294 |
| 15 | 0.025817 | 0.215561 | 0.048288 | −0.08909 | 0.027849 | −0.001439 | −0.116778 | 0.004331 | 0.01501 | −0.137579 | 0.031273 | 0.002965 | −0.089508 | 0.096979 |
| 16 | 0.018245 | 0.054845 | −0.050142 | −0.001729 | −0.015846 | 0.008215 | 0.063323 | −0.052828 | −0.031711 | −0.001652 | −0.036057 | 0.005682 | −0.005343 | 0.018678 |
| 17 | −0.039955 | 0.059221 | 0.09273 | −0.050576 | 0.004454 | 0.062809 | 0.053351 | 0.003151 | −0.030563 | 0.016029 | −0.023654 | −0.037003 | 0.006515 | −0.095434 |
| 18 | 0.076762 | −0.00176 | −0.009508 | 0.050221 | −0.047708 | −0.10042 | −0.057572 | 0.001106 | −0.00624 | 0.015331 | −0.011202 | −0.000119 | −0.007636 | −0.00476 |
| 19 | 0.012838 | −0.066263 | 0.0196 | −0.034616 | −0.024257 | 0.04367 | −0.119212 | −0.003905 | 0.07549 | −0.006018 | −0.084281 | −0.06805 | −0.004197 | −0.041114 |
| 20 | 0.106797 | −0.071945 | −0.008618 | −0.041587 | 0.124826 | 0.011228 | 0.09186 | −0.002569 | −0.121183 | 0.001417 | −0.039015 | 0.00365 | 0.021261 | 0.102672 |
| 21 | 0.001165 | 0.130008 | −0.085392 | −0.040456 | 0.07323 | 0.032348 | 0.08445 | 0.025096 | 0.063758 | 0.000823 | 0.005471 | −0.03041 | −0.000206 | −0.025874 |
| 22 | 0.0259 | −0.108995 | −0.019522 | −0.015487 | −0.076593 | −0.03572 | −0.017606 | −0.030211 | 0.009745 | 0.006211 | −0.047913 | −0.013343 | −0.025629 | −0.04341 |
| 23 | −0.0894 | −0.010489 | −0.118538 | 0.029033 | −0.004764 | 0.081255 | −0.007603 | −0.007358 | 0.037599 | 0.031715 | 0.05774 | −0.000852 | 0.009571 | 0.061826 |
| 24 | −0.08535 | 0.079299 | −0.05552 | 0.082046 | 0.047985 | −0.053977 | 0.012226 | −0.020681 | 0.040535 | −0.037515 | 0.006059 | 0.056205 | −0.033204 | −0.010434 |
| 25 | −0.108522 | −0.077092 | 0.097237 | −0.077053 | −0.041818 | −0.106135 | 0.060888 | −0.005963 | 0.006253 | 0.023368 | 0.031236 | −0.051352 | 0.036052 | 0.054376 |
| 26 | −0.062535 | 0.055664 | 0.102828 | −0.091656 | −0.023579 | 0.130714 | −0.107568 | −0.010321 | −0.089758 | −0.009587 | −0.059663 | 0.021773 | 0.00512 | −0.093514 |
| 27 | 0.046755 | −0.050041 | 0.238838 | 0.159209 | −0.096301 | −0.054121 | −0.025591 | −0.088147 | −0.118567 | 0.071011 | 0.039593 | 0.082656 | 0.021982 | −0.026304 |
| 28 | 0.095117 | 0.042402 | −0.163254 | −0.028671 | 0.053467 | 0.105035 | −0.012742 | 0.042257 | 0.143305 | 0.031976 | −0.024044 | −0.016121 | 0.044305 | −0.094898 |
| 29 | 0.039828 | −0.065484 | 0.026117 | 0.01959 | 0.025027 | 0.019972 | 0.008542 | −0.003733 | 0.014773 | −0.059144 | −0.008454 | 0.048343 | −0.022219 | 0.027596 |
| 30 | 0.048351 | 0.065987 | −0.087858 | 0.013747 | 0.086983 | −0.086358 | 0.141602 | −0.013427 | 0.057938 | −0.020778 | −0.013843 | −0.005469 | 0.014358 | −0.045279 |
| 31 | −0.014194 | 0.06532 | −0.063082 | −0.02337 | −0.05245 | −0.097851 | 0.106259 | −0.007233 | 0.00872 | 0.141598 | 0.0767 | 0.034698 | 0.122705 | 0.052664 |
| 32 | −0.079813 | 0.100635 | −0.05272 | 0.021369 | 0.020352 | 0.029775 | 0.010492 | −0.011712 | −0.010876 | −0.039767 | −0.0103 | 0.027245 | −0.019111 | 0.004142 |
| 33 | −0.071493 | −0.026689 | −0.003069 | −0.044712 | 0.140117 | 0.013651 | −0.032033 | 0.058726 | −0.101397 | −0.083574 | −0.036072 | −0.103102 | −0.080201 | −0.056394 |
| 34 | −0.086265 | −0.086311 | −0.017954 | −0.055461 | −0.088708 | 0.01007 | 0.004537 | −0.002761 | −0.037699 | 0.091077 | 0.097851 | 0.004059 | 0.003473 | −0.012745 |
| 35 | 0.028019 | −0.059738 | −0.069271 | 0.035618 | 0.002027 | 0.042318 | 0.02575 | −0.01732 | 0.045897 | −0.079735 | 0.015505 | 0.020322 | −0.030096 | 0.023471 |
| 36 | 0.107614 | 0.028631 | −0.009871 | −0.096952 | −0.110683 | −0.019071 | 0.003558 | −0.00891 | 0.054052 | −0.004484 | 0.001562 | −0.065502 | −0.085735 | 0.020191 |
| 37 | −0.008497 | 0.032758 | 0.001636 | −0.026819 | −0.061718 | −0.070341 | 0.045335 | −0.075243 | 0.010711 | −0.072298 | 0.023611 | 0.036525 | −0.00885 | −0.003006 |
| 38 | 0.012824 | −0.042725 | 0.012052 | 0.013695 | 0.044885 | −0.02778 | −0.026341 | −0.014195 | −0.01174 | −0.045873 | −0.054145 | 0.004574 | −0.001249 | −0.022287 |
| 39 | −0.081931 | −0.035774 | −0.030119 | 0:014344 | 0.067502 | 0.03736 | −0.129423 | 0.007322 | 0.003931 | −0.058153 | −0.039566 | 0.02548 | 0.034799 | −0.000562 |
| 40 | 0.024653 | −0.085108 | −0.085895 | −0.014991 | −0.052312 | 0.150335 | −0.05917 | −0.036025 | −0.037518 | 0.041261 | −0.056807 | 0.044099 | 0.017477 | 0.002072 |
| 41 | −0.008055 | 0.111697 | 0.133474 | −0.135763 | −0.056708 | 0.092366 | −0.068668 | −0.018418 | −0.001806 | −0.060584 | 0.072479 | 0.004005 | 0.07821 | −0.037455 |
| 42 | −0.054367 | −0.14872 | 0.043006 | 0.007231 | −0.018934 | −0.063679 | −0.015705 | 0.034514 | 0.08529 | 0.040914 | 0.081268 | −0.024668 | −0.089678 | 0.00179 |
| 43 | 0.048226 | 0.109096 | 0.015188 | 0.17232 | −0.05793 | −0.064557 | 0.06944 | −0.036029 | 0.043394 | 0.06144 | 0.000128 | −0.042009 | −0.074465 | −0.02975 |
| 44 | −0.007805 | 0.02525 | −0.05592 | 0.041009 | −0.055145 | 0.001857 | 0.070401 | −0.017308 | 0.022504 | 0.023874 | −0.025775 | 0.001903 | −0.004647 | 0.061129 |
| 45 | 0.012401 | 0.04762 | 0.015607 | −0.012121 | 0.035074 | 0.067204 | 0.049106 | 0.01883 | 0.112718 | −0.021781 | 0.024828 | −0.009998 | 0.025407 | 0.116502 |
| 46 | −0.071485 | 0.029697 | −0.047811 | 0.039762 | −0.041966 | 0.026293 | 0.085669 | 0.037672 | −0.01702 | −0.024327 | −0.004877 | 0.005672 | 0.052672 | −0.0246 |
| 47 | −0.059364 | −0.012101 | −0.009073 | 0.119821 | −0.117616 | 0.003348 | −0.001085 | 0.062501 | −0.108288 | −0.203273 | 0.112467 | 0.017219 | 0.039168 | 0.017484 |
| 48 | 0.032503 | 0.070572 | 0.041099 | 0.038311 | −0.038899 | −0.074086 | 0.128308 | 0.020524 | 0.069804 | 0.006459 | 0.051548 | 0.004529 | −0.016475 | 0.072908 |
| 49 | −0.056856 | 0.011871 | −0.016232 | 0.027697 | −0.005995 | 0.055482 | −0.170955 | −0.025249 | −0.10765 | −0.033862 | −0.141093 | 0.009465 | −0.019039 | −0.065496 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 50 | 0.041146 | −0.1478 | 0.098535 | 0.155815 | 0.015937 | 0.034161 | −0.058049 | −0.023214 | 0.006684 | 0.140197 | 0.00646 | −0.034567 | 0.072062 | 0.090914 |
| 51 | 0.007545 | 0.108743 | −0.054935 | −0.036204 | −0.024003 | 0.080288 | −0.045587 | 0.048074 | 0.092466 | 0.021918 | −0.013647 | 0.069564 | 0.045783 | −0.005103 |
| 52 | 0.04032 | −0.143533 | 0.071548 | 0.038029 | 0.045109 | −0.000389 | 0.105062 | 0.042145 | 0.094073 | 0.044787 | −0.041603 | −0.023171 | 0.055975 | −0.031515 |
| 53 | −0.018391 | 0.10682 | 0.069668 | −0.122315 | −0.039129 | −0.039109 | −0.006772 | −0.006251 | 0.035802 | −0.006316 | −0.021341 | −0.051738 | −0.104961 | 0.015461 |
| 54 | 0.105344 | −0.036396 | 0.046891 | 0.075308 | 0.025809 | 0.031282 | −0.015582 | −0.00972 | 0.00939 | 0.022011 | −0.067509 | 0.061062 | 0.035266 | −0.032308 |
| 55 | 0.127329 | −0.079303 | 0.025955 | −0.059202 | −0.10611 | −0.170292 | −0.010942 | 0.055583 | 0.043267 | −0.031621 | −0.022244 | 0.051523 | 0.021523 | −0.021632 |
| 56 | −0.050817 | −0.175538 | −0.006003 | 0.064073 | 0.00392 | −0.09963 | 0.030521 | 0.080313 | −0.027815 | −0.10244 | −0.050455 | 0.016736 | 0.014165 | −0.087075 |
| 57 | 0.117585 | −0.031374 | −0.002762 | −0.048001 | −0.112326 | −0.059688 | −0.037301 | 0.023605 | 0.056604 | 0.004093 | −0.032935 | −0.018994 | −0.019871 | 0.014904 |
| 58 | 0.161753 | 0.00228 | −0.100225 | 0.00137 | −0.042976 | 0.000317 | −0.031335 | 0.063245 | 0.000401 | −0.040635 | 0.001352 | −0.072587 | −0.042704 | −0.060089 |
| 59 | −0.043531 | −0.014759 | −0.008887 | −0.02221 | −0.021142 | −0.121947 | 0.018545 | 0.006061 | −0.085339 | 0.055679 | 0.077933 | 0.028861 | −0.010709 | 0.014841 |
| 60 | 0.014756 | 0.070083 | 0.004467 | 0.103918 | −0.095656 | −0.0206 | 0.092055 | 0.077059 | −0.070104 | 0.058013 | −0.009312 | 0.008517 | 0.061789 | −0.017435 |
| 61 | −0.118957 | −0.05153 | −0.07183 | 0.019498 | −0.009045 | −0.0811 | −0.038774 | −0.018342 | 0.028392 | −0.005942 | 0.013305 | −0.080063 | −0.052116 | 0.003626 |
| 62 | 0.077467 | −0.01967 | −0.16295 | 0.004042 | 0.081184 | 0.028404 | −0.134354 | 0.004372 | 0.161642 | −0.06089 | 0.046713 | 0.016606 | −0.069575 | −0.090886 |
| 63 | 0.175847 | 0.075563 | 0.141582 | −0.068941 | 0.035308 | 0.101367 | 0.011629 | 0.019896 | −0.005033 | 0.000993 | 0.043997 | 0.049926 | −0.009337 | 0.012672 |
| 64 | 0.037873 | −0.079268 | 0.008126 | −0.022644 | −0.001571 | −0.031142 | −0.002393 | 0.014609 | −0.023975 | −0.024371 | −0.030409 | −0.046752 | −0.064671 | −0.04332 |
| 65 | −0.030894 | 0.07487 | −0.060226 | −0.038959 | 0.065522 | −0.041346 | −0.004199 | 0.000566 | 0.023639 | −0.089397 | −0.000126 | 0.043857 | 0.037212 | −0.012521 |
| 66 | −0.01666 | 0.08843 | −0.034363 | −0.007098 | 0.118139 | 0.014067 | −0.01238 | 0.035075 | 0.008826 | 0.012625 | 0.013241 | 0.036722 | 0.007388 | 0.017391 |
| 67 | −0.043767 | −0.010668 | −0.03545 | −0.018254 | −0.056906 | −0.057608 | −0.077957 | −0.031385 | 0.046937 | 0.059353 | −0.008619 | 0.062397 | 0.073283 | 0.03904 |
| 68 | 0.035095 | 0.018142 | −0.001866 | −0.051843 | 0.073529 | 0.062147 | 0.031844 | 0.043308 | −0.029265 | −0.006543 | −0.00089 | 0.008086 | −0.023359 | 0.019394 |
| 69 | −0.013274 | −0.103112 | −0.021569 | 0.021189 | 0.114724 | −0.006646 | −0.053289 | −0.019914 | 0.072057 | 0.055085 | −0.078419 | 0.056338 | 0.044046 | −0.074435 |
| 70 | −0.020547 | −0.0413 | 0.017716 | −0.054989 | −0.055279 | −0.024034 | 0.133667 | 0.046438 | 0.067804 | −0.002592 | 0.024981 | −0.016172 | −0.02601 | 0.038808 |
| 71 | −0.005923 | −0.064406 | −0.010284 | −0.082833 | 0.041955 | −0.098463 | 0.052468 | −0.001655 | −0.010571 | 0.034212 | −0.022062 | −0.038266 | −0.032839 | −0.037954 |
| 72 | 0.15739 | −0.033045 | −0.080025 | −0.136284 | 0.027385 | −0.067934 | −0.143015 | 0.003221 | −0.16075 | 0.097425 | 0.034969 | 0.023423 | 0.072474 | 0.004235 |
| 73 | 0.039222 | 0.01818 | 0.01712 | 0.082028 | −0.103757 | 0.109378 | −0.020952 | −0.009256 | 0.005131 | −0.0335 | −0.05254 | 0.007819 | −0.053161 | −0.038191 |
| 74 | 0.0413 | 0.017716 | 0.070864 | −0.070864 | −0.061186 | −0.089782 | 0.017214 | −0.067871 | −0.01393 | 0.020728 | −0.013964 | −0.089562 | 0.009892 | 0.004558 |
| 75 | −0.192404 | 0.034783 | −0.073343 | 0.037151 | −0.025638 | −0.025629 | −0.007649 | 0.022603 | −0.016542 | 0.024256 | 0.027251 | −0.106371 | −0.056762 | −0.054357 |
| 76 | 0.019442 | 0.028165 | −0.032654 | 0.078677 | −0.005542 | 0.224582 | 0.009959 | −0.061377 | −0.065729 | 0.012672 | 0.066955 | −0.046227 | −0.004175 | 0.071595 |
| 77 | −0.006858 | −0.127539 | −0.005505 | 0.015619 | −0.075181 | 0.020115 | 0.01837 | −0.038295 | −0.126872 | 0.030044 | −0.03911 | −0.004324 | 0.030518 | −0.018052 |
| 78 | −0.038358 | −0.003967 | 0.001773 | −0.099481 | 0.104049 | −0.126238 | −0.085259 | 0.022619 | −0.022914 | 0.018713 | 0.064265 | 0.101532 | 0.076578 | −0.004892 |
| 79 | 0.061726 | 0.080888 | 0.141898 | 0.182739 | 0.003528 | 0.02211 | 0.019453 | 0.000688 | −0.019497 | −0.018187 | −0.007521 | 0.068706 | 0.004045 | −0.103257 |
| 80 | −0.001606 | −0.045227 | −0.087229 | 0.018322 | −0.076752 | −0.049303 | 0.04523 | −0.015786 | −0.044151 | −0.080996 | −0.047092 | 0.019504 | 0.020748 | 0.020573 |
| 81 | −0.016422 | 0.040216 | 0.130401 | −0.084344 | −0.0305 | 0.061772 | −0.05724 | 0.0148 | 0.061542 | 0.045946 | −0.037399 | −0.005939 | −0.000567 | 0.022494 |
| 82 | −0.035753 | 0.067836 | −0.021683 | −0.111886 | −0.098568 | −0.126911 | −0.108086 | 0.033709 | 0.097449 | −0.039774 | 0.022009 | −0.038826 | −0.003953 | −0.079605 |
| 83 | −0.206807 | 0.028512 | 0.019651 | −0.081424 | −0.163874 | 0.130147 | −0.179295 | 0.006889 | 0.08089 | 0.040738 | 0.01969 | 0.001084 | 0.022721 | −0.001261 |
| 84 | 0.129712 | −0.014929 | −0.106332 | 0.201062 | 0.28927 | −0.077371 | −0.064459 | −0.028502 | 0.029469 | −0.008371 | −0.075487 | −0.063186 | 0.020315 | −0.013159 |
| 85 | 0.005492 | 0.069781 | 0.028306 | −0.066117 | −0.033978 | 0.034174 | 0.191016 | 0.006672 | −0.051646 | −0.039389 | −0.009314 | −0.107884 | −0.050804 | 0.027264 |
| 86 | −0.03927 | −0.00248 | 0.024207 | 0.061271 | 0.028896 | −0.085607 | −0.068447 | −0.016786 | −0.009437 | −0.009523 | −0.006493 | 0.069498 | 0.003747 | 0.034827 |
| 87 | −0.090624 | −0.079548 | 0.082932 | −0.001482 | 0.072378 | 0.077897 | 0.067921 | 0.085082 | 0.11309 | −0.053553 | −0.026099 | −0.00924 | −0.042696 | −0.009768 |
| 88 | 0.135415 | −0.034122 | 0.034791 | 0.015637 | −0.024435 | −0.089575 | −0.047814 | 0.022622 | −0.002376 | 0.018176 | 0.080729 | −0.041791 | −0.054952 | 0.066057 |
| 89 | −0.117627 | −0.09314 | −0.122111 | −0.000388 | 0.09588 | 0.220826 | 0.062021 | −0.069142 | 0.034559 | 0.043296 | 0.09196 | 0.028051 | 0.027817 | 0.027423 |
| 90 | 0.067958 | −0.098439 | −0.011306 | 0.154856 | −0.040807 | −0.01484 | −0.065311 | 0.075549 | 0.028172 | 0.006757 | 0.021735 | 0.015861 | 0.040033 | 0.037442 |
| 91 | 0.089421 | 0.048736 | 0.058924 | −0.00396 | −0.083362 | 0.129147 | 0.207545 | −0.038318 | −0.106021 | −0.00554 | −0.120155 | −0.030764 | 0.012129 | −0.071769 |
| 92 | −0.088968 | 0.047804 | −0.074349 | 0.139947 | −0.005349 | −0.080211 | 0.047279 | −0.000493 | 0.074556 | 0.01747 | −0.010123 | −0.012671 | −0.009206 | 0.037281 |
| 93 | −0.083202 | 0.013293 | 0.109574 | 0.050107 | −0.095002 | 0.069801 | −0.077228 | 0.005614 | 0.048671 | 0.004235 | −0.018444 | 0.038952 | −0.031612 | −0.040743 |
| 94 | 0.07953 | 0.117217 | −0.026181 | 0.051507 | 0.196614 | −0.051548 | −0.000674 | 0.079391 | −0.042811 | −0.009261 | −0.087995 | −0.02009 | −0.008821 | 0.005555 |
| 95 | −0.017322 | −0.008211 | −0.037114 | 0.11194 | 0.011836 | −0.000816 | −0.03712 | 0.041217 | −0.025982 | −0.037346 | −0.017959 | 0.017497 | −0.013954 | −0.027103 |
| 96 | 0.079474 | −0.070038 | 0.029534 | 0.010111 | 0.049279 | 0.059636 | −0.011136 | −0.051585 | −0.020008 | −0.032206 | −0.021307 | −0.014869 | 0.029381 | 0.037689 |
| 97 | 0.116033 | −0.147995 | −0.138292 | −0.074362 | 0.004181 | 0.11575 | −0.008718 | 0.037851 | −0.084094 | 0.060089 | −0.030495 | −0.023636 | 0.023 | −0.022835 |
| 98 | −0.027756 | 0.076668 | 0.089555 | −0.036984 | 0.057264 | −0.235458 | −0.094023 | −0.025873 | −0.209538 | −0.018 | 0.007744 | 0.015309 | −0.037899 | 0.028984 |
| 99 | −0.130223 | 0.124596 | −0.00663 | 0.091838 | −0.08315 | −0.02131 | −0.115769 | 0.049103 | 0.067682 | 0.058749 | −0.071927 | 0.11315 | 0.075201 | 0.006028 |
| 100 | 0.042957 | 0.002772 | −0.114478 | −0.05183 | 0.004532 | −0.029359 | 0.000886 | −0.085329 | 0.077996 | 0.058441 | 0.077981 | 0.010117 | 0.053643 | −0.010049 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 101 | 0.037191 | 0.042848 | 0.01751 | 0.159184 | 0.050737 | 0.082877 | −0.079232 | −0.035342 | −0.055019 | 0.03864 | 0.127737 | −0.013276 | −0.042671 | −0.043288 |
| 102 | 0.04266 | 0.080224 | 0.018573 | −0.048764 | −0.056805 | −0.032093 | −0.051505 | 0.010134 | −0.031447 | 0.101483 | 0.077247 | 0.064024 | 0.024248 | 0.065829 |
| 103 | 0.014467 | −0.029089 | 0.044537 | 0.033978 | 0.027468 | −0.129243 | 0.03678 | −0.076309 | 0.016225 | −0.007689 | 0.009095 | −0.043512 | −0.049399 | −0.002996 |
| 104 | −0.032774 | −0.052869 | 0.13419 | −0.0637 | 0.066744 | 0.023347 | 0.064634 | −0.005047 | −0.022723 | 0.000359 | 0.005731 | 0.0145911 | 0.040869 | −0.047795 |
| 105 | −0.016336 | 0.043916 | 0.034385 | −0.052065 | −0.057741 | 0.004931 | 0.006888 | −0.007654 | −0.022742 | 0.04114 | −0.044209 | −0.004244 | 0.012471 | −0.02385 |
| 106 | −0.004285 | −0.027049 | −0.043138 | 0.028545 | −0.07254 | 0.075592 | −0.074135 | 0.03415 | 0.016301 | −0.009966 | −0.075688 | −0.022328 | −0.068484 | 0.042969 |
| 107 | −0.04823 | 0.010473 | 0.027726 | −0.034473 | −0.056892 | −0.023131 | −0.075433 | −0.004632 | 0.007154 | −0.086389 | −0.044615 | −0.067438 | −0.064245 | −0.027964 |
| 108 | 0.007327 | 0.101862 | −0.000231 | 0.047266 | −0.077599 | −0.091201 | −0.025843 | 0.021896 | 0.032178 | 0.066093 | −0.05456 | −0.025128 | −0.011868 | −0.052143 |
| 109 | 0.066484 | −0.079032 | −0.006156 | −0.018617 | 0.018939 | −0.01219 | 0.033551 | −0.005325 | 0.03545 | −0.030214 | −0.040078 | −0.043335 | −0.013074 | 0.013918 |
| 110 | −0.074538 | 0.025216 | −0.023143 | 0.013446 | −0.001734 | 0.046669 | 0.040516 | −0.016476 | 0.016765 | 0.005039 | 0.002969 | 0.016616 | −0.015404 | −0.004742 |
| 111 | −0.065174 | 0.043843 | −0.013414 | −0.025963 | 0.040473 | 0.074622 | 0.025941 | 0.004845 | −0.079127 | −0.05476 | −0.038955 | −0.022014 | −0.017913 | −0.009255 |
| 112 | −0.018614 | −0.057989 | 0.03119 | −0.018592 | 0.077979 | 0.019743 | −0.029767 | 0.008956 | −0.001878 | −0.066029 | −0.015669 | −0.015339 | −0.03118 | 0.058589 |
| 113 | 0.036996 | 0.02852 | 0.051236 | −0.025314 | 0.005673 | 0.025801 | −0.012892 | 0.03151 | 0.066235 | 0.017437 | 0.048648 | −0.008646 | −0.000063 | 0.013209 |
| 114 | 0.040095 | 0.06534 | −0.077707 | 0.110848 | −0.001702 | 0.013764 | 0.059287 | 0.048592 | 0.002807 | 0.006463 | 0.006382 | −0.020074 | −0.069877 | 0.082575 |
| 115 | 0.038447 | −0.110698 | 0.054153 | 0.05357 | −0.004166 | 0.051684 | 0.033362 | −0.047023 | −0.00784 | 0.010446 | 0.094132 | −0.021537 | 0.029034 | 0.058636 |
| 116 | 0.008166 | −0.025133 | 0.071587 | −0.057884 | −0.001873 | 0.004599 | 0.038466 | 0.009374 | 0.03078 | 0.033008 | 0.098236 | −0.02914 | −0.021525 | 0.002954 |
| 117 | 0.020246 | 0.007397 | −0.073784 | 0.014313 | 0.005054 | −0.0718 | −0.06608 | −0.023478 | −0.076038 | −0.00958 | −0.003537 | −0.04923 | −0.041166 | −0.017605 |
| 118 | −0.016184 | −0.094824 | 0.032546 | 0.099703 | −0.073702 | 0.020662 | 0.040298 | −0.038707 | 0.021885 | −0.05369 | −0.04102 | −0.034529 | −0.031302 | −0.038846 |
| 119 | −0.123362 | 0.051558 | 0.017677 | 0.04804 | 0.031752 | −0.04188 | −0.035102 | 0.071733 | 0.052059 | −0.008287 | −0.086104 | 0.065121 | 0.052276 | −0.021453 |
| 120 | 0.005493 | 0.051693 | −0.013026 | −0.077641 | 0.00646 | 0.020477 | −0.021134 | −0.060633 | −0.084287 | 0.09097 | 0.011593 | 0.043472 | 0.073046 | 0.038905 |
| 121 | −0.122582 | 0.030381 | 0.006301 | 0:013445 | −0.046576 | 0.042317 | 0.122592 | 0.016897 | 0.001239 | −0.014424 | −0.128102 | −0.022913 | −0.0484 | −0.104264 |
| 122 | −0.076413 | 0.016064 | −0.089181 | 0.014956 | 0.044789 | −0.045631 | 0.049744 | 0.020443 | −0.001406 | −0.022229 | 0.107172 | −0.027577 | 0.011805 | 0.023705 |
| 123 | 0.063426 | −0.017916 | 0.095522 | −0.018837 | 0.09106 | −0.016482 | −0.112395 | −0.050082 | −0.002676 | 0.021394 | 0.012802 | −0.031849 | 0.020673 | 0.002409 |
| 124 | 0.091523 | 0.005689 | 0.121638 | 0.031877 | −0.008989 | 0.21397 | −0.026012 | −0.015529 | −0.053064 | −0.042373 | −0.107998 | −0.033645 | −0.03788 | −0.073376 |
| 125 | 0.029927 | −0.054365 | 0.040652 | 0.001183 | 0.076611 | 0.059639 | −0.031011 | 0.047886 | 0.042746 | −0.112841 | 0.015862 | 0.055952 | 0.031003 | −0.077699 |
| 126 | 0.005935 | −0.045077 | −0.031887 | −0.134408 | 0.019635 | −0.008773 | 0.001176 | 0.046323 | −0.090518 | −0.042331 | 0.103459 | 0.038945 | 0.001157 | 0.115707 |
| 127 | 0.089627 | 0.124135 | −0.024381 | 0.068859 | −0.037178 | −0.038723 | −0.021378 | −0.093239 | 0.17133 | 0.099152 | −0.027921 | 0.043784 | 0.028416 | −0.054665 |
| 128 | −0.044262 | −0.009234 | 0.052986 | −0.106721 | −0.054047 | −0.104698 | −0.121566 | 0.04345 | −0.045113 | −0.012442 | −0.180459 | 0.047287 | 0.008424 | 0.000809 |
| 129 | −0.038779 | −0.076028 | −0.011532 | −0.009411 | −0.03547 | 0.075498 | −0.010835 | −0.006018 | 0.007862 | −0.031971 | 0.030165 | 0.051696 | 0.009941 | 0.002445 |
| 130 | −0.026763 | 0.030133 | −0.000721 | 0.016339 | −0.031798 | 0.023461 | −0.015508 | 0.016055 | −0.000611 | −0.018902 | 0.029193 | 0.030921 | −0.019612 | 0.055087 |
| 131 | −0.054727 | −0.035849 | 0.112132 | 0.017309 | 0.01517 | 0.024564 | −0.038542 | 0.031618 | 0.00723 | −0.007328 | 0.050206 | 0.021457 | 0.025251 | 0.039182 |
| 132 | −0.003892 | 0.068505 | 0.077415 | 0.045918 | 0.102083 | 0.051788 | 0.038308 | −0.007235 | −0.041581 | 0.087809 | 0.026481 | −0.040641 | −0.040582 | 0.005849 |
| 133 | 0.040069 | 0.038835 | 0.019056 | −0.00218 | 0.07639 | 0.007044 | 0.089648 | 0.059234 | 0.085053 | −0.061154 | 0.10954 | −0.006851 | 0.01254 | 0.073548 |
| 134 | 0.019992 | 0.029469 | −0.026455 | −0.021021 | −0.081422 | −0.059427 | 0.034554 | 0.083481 | −0.076987 | 0.014996 | 0.008517 | 0.04524 | 0.027594 | 0.060635 |
| 135 | −0.043437 | −0.100998 | −0.050793 | 0.085897 | −0.073692 | 0.054204 | −0.007401 | 0.05718 | 0.071007 | −0.028665 | 0.087773 | −0.004618 | 0.083358 | 0.080937 |
| 136 | −0.064693 | −0.035763 | −0.0504 | −0.020853 | −0.025659 | −0.096464 | 0.019042 | −0.071922 | −0.034061 | −0.030258 | −0.049206 | −0.012 | −0.038852 | −0.003119 |
| 137 | −0.004455 | 0.00863 | −0.085115 | 0.025464 | −0.079253 | 0.033475 | 0.075962 | −0.064297 | 0.041472 | 0.07291 | 0.027669 | −0.032024 | 0.066872 | 0.011177 |
| 138 | −0.038988 | −0.081694 | −0.079076 | −0.060755 | −0.013807 | −0.010039 | 0.009473 | −0.064086 | −0.034325 | 0.034558 | 0.043102 | 0.001369 | −0.000036 | −0.002839 |
| 139 | 0.000406 | −0.016382 | 0.037173 | 0.004738 | −0.034229 | −0.015006 | −0.006473 | 0.009896 | 0.027984 | −0.031308 | 0.002558 | −0.004555 | −0.039967 | 0.04382 |
| 140 | 0.037082 | −0.041088 | −0.046913 | 0.069994 | −0.043668 | −0.053939 | −0.050112 | −0.020626 | −0.036254 | −0.018557 | 0.017504 | −0.031719 | 0.021561 | −0.064294 |
| 141 | −0.001939 | −0.001934 | −0.061012 | 0.062244 | 0.010959 | −0.036858 | 0.009906 | 0.02283 | −0.018818 | −0.017716 | −0.060248 | 0.002928 | −0.003497 | 0.02116 |
| 142 | −0.040676 | 0.066776 | −0.060526 | 0.061111 | 0.015528 | −0.058151 | −0.02722 | −0.05258 | 0.029406 | 0.050402 | 0.00025 | 0.033601 | 0.023482 | −0.010639 |
| 143 | −0.032553 | 0.005586 | −0.05643 | 0.035572 | −0.069065 | −0.018712 | 0.017263 | 0.007005 | −0.070942 | −0.00335 | 0.009593 | −0.03013 | −0.002125 | −0.008918 |
| 144 | 0.043191 | 0.020809 | 0.022583 | 0.002024 | 0.009082 | 0.013283 | 0.006865 | 0.031509 | −0.08019 | −0.035824 | −0.011874 | −0.015926 | −0.027687 | −0.010715 |
| 145 | 0.021635 | −0.021967 | −0.014153 | 0.008594 | −0.096039 | 0.030971 | 0.025512 | −0.016143 | −0.015403 | 0.019439 | −0.008922 | −0.023897 | −0.021539 | −0.020588 |
| 146 | −0.000777 | −0.026326 | −0.03599 | −0.009648 | −0.04695 | 0.01737 | 0.02766 | −0.038168 | 0.017094 | −0.008839 | 0.003616 | −0.032603 | −0.035908 | −0.018398 |
| 147 | −0.033127 | 0.048837 | 0.020651 | 0.017146 | 0.014701 | −0.023271 | −0.063861 | −0.033963 | 0.028676 | −0.002519 | −0.074638 | 0.054305 | 0.04013 | −0.01362 |
| 148 | 0.049514 | 0.075092 | −0.035912 | −0.10494 | 0.013427 | 0.030696 | 0.003998 | −0.03113 | 0.045524 | 0.031949 | −0.023794 | −0.029446 | −0.003283 | 0.027197 |
| 149 | −0.01327 | 0.021621 | −0.001366 | −0.029536 | −0.068068 | 0.073733 | −0.018948 | 0.016011 | 0.050109 | −0.028105 | 0.068406 | 0.020648 | −0.018628 | 0.036205 |
| 150 | 0.029087 | 0.001251 | −0.013166 | −0.079574 | 0.010748 | −0.035342 | 0.041698 | 0.024247 | −0.054202 | −0.008717 | −0.083783 | −0.029212 | 0.002354 | −0.041897 |
| 151 | −0.02855 | −0.004871 | −0.037674 | −0.052261 | 0.038792 | 0.057394 | 0.009144 | 0.053042 | −0.024609 | 0.017998 | 0.007671 | 0.034901 | 0.035271 | −0.011857 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 152 | 0.056246 | −0.070117 | −0.043879 | −0.052406 | 0.086468 | 0.011313 | −0.034673 | −0.003696 | 0.053979 | 0.006886 | 0.093946 | 0.003409 | 0.029908 | 0.022568 |
| 153 | 0.021107 | −0.003049 | 0.07844 | −0.04261 | −0.016643 | −0.025926 | 0.026644 | 0.017084 | 0.034418 | −0.000817 | 0.056114 | −0.046439 | −0.027065 | 0.037935 |
| 154 | 0.04083 | 0.001529 | −0.030884 | 0.050246 | 0.001978 | −0.005764 | 0.047433 | −0.000513 | −0.02391 | −0.016856 | −0.0094 | −0.009671 | 0.001416 | −0.016746 |
| 155 | 0.020624 | −0.030656 | −0.002768 | −0.047079 | −0.019052 | −0.019229 | 0.017105 | 0.052402 | 0.053091 | 0.058502 | 0.085813 | 0.019013 | 0.038739 | 0.04027 |
| 156 | −0.030881 | −0.002184 | 0.018212 | 0.013097 | 0.000825 | −0.012106 | −0.006799 | −0.025347 | 0.021699 | 0.026835 | −0.034327 | −0.003266 | −0.030767 | 0.023977 |
| 157 | −0.023466 | 0.046406 | −0.039499 | −0.011344 | −0.012257 | 0.004914 | 0.049262 | 0.009152 | −0.034804 | −0.017927 | 0.032415 | 0.032228 | −0.021545 | 0.033053 |
| 158 | 0.056302 | −0.009912 | 0.044425 | 0.001799 | 0.019653 | 0.029915 | −0.009028 | −0.00384 | −0.038855 | 0.037017 | 0.053368 | 0.037519 | 0.010603 | 0.028541 |
| 159 | 0.018352 | −0.011126 | 0.004338 | 0.038242 | 0.00717 | 0.038025 | −0.04508 | −0.016496 | 0.013211 | −0.009913 | −0.003707 | −0.014824 | −0.02158 | −0.032011 |
| 160 | 0.005283 | 0.011432 | 0.00763 | −0.015866 | 0.05324 | 0.002037 | 0.004277 | −0.016118 | −0.045235 | 0.039529 | 0.029833 | 0.033995 | 0.048969 | −0.001334 |
| 161 | 0.071744 | 0.088319 | −0.093207 | 0.021808 | −0.010575 | 0.007582 | −0.029468 | 0.004258 | −0.00445 | −0.023426 | 0.016849 | −0.036528 | −0.054769 | 0.01903 |
| 162 | −0.023133 | 0.003833 | −0.023535 | −0:080779 | −0.02143 | −0.018231 | 0.053091 | −0.032733 | 0.058655 | −0.000172 | −0.004337 | −0.002645 | −0.020366 | 0.000781 |
| 163 | −0.003149 | 0.050674 | −0.059687 | 0.02043 | 0.058605 | −0.037514 | −0.038192 | 0.005 | −0.013071 | 0.012944 | −0.008775 | 0.009395 | 0.031013 | 0.022824 |
| 164 | −0.099818 | −0.032997 | 0.073612 | −0.009758 | 0.065541 | 0.031861 | 0.037022 | 0.00062 | −0.002277 | −0.001085 | −0.056248 | 0.00385 | −0.004663 | −0.011311 |
| 165 | −0.121334 | −0.006728 | −0.014562 | 0.019733 | 0.026368 | −0.027446 | −0.075737 | −0.011793 | −0.01491 | 0.055638 | −0.011983 | 0.011568 | 0.006417 | −0.025554 |
| 166 | 0.05961 | 0.005037 | 0.023446 | −0.071753 | −0.054092 | −0.033489 | −0.03916 | 0.04326 | −0.001617 | −0.011793 | 0.062433 | 0.012957 | −0.00789 | −0.039171 |
| 167 | 0.070159 | 0.006008 | 0.122578 | −0.009221 | 0.033778 | −0.007757 | 0.000058 | −0.010107 | 0.022351 | −0.010559 | 0.040515 | 0.007598 | −0.043035 | −0.00714 |
| 168 | 0.008511 | 0.008623 | 0.040932 | 0.081185 | 0.053759 | −0.054881 | 0.02833 | −0.039242 | −0.036199 | −0.094581 | 0.000431 | −0.01842 | −0.018962 | 0.010268 |
| 169 | −0.034955 | −0.010181 | 0.006948 | 0.003461 | −0.027916 | 0.0088 | 0.03058 | −0.027449 | 0.058102 | −0.007833 | −0.026145 | −0.006943 | −0.027992 | −0.00747 |
| 170 | −0.019741 | −0.008642 | 0.006291 | 0.01622 | −0.004375 | −0.033375 | 0.045413 | −0.003833 | 0.062231 | 0.004654 | −0.010724 | −0.02359 | −0.035375 | −0.010978 |
| 171 | −0.036169 | −0.032936 | −0.019047 | −0.001178 | −0.03463 | −0.000592 | −0.009625 | −0.055294 | −0.004278 | 0.001338 | −0.020786 | −0.000378 | −0.028955 | −0.01528 |
| 172 | −0.007357 | 0.009562 | −0.038112 | 0.061007 | −0.036337 | 0.009967 | −0.020921 | −0.02013 | 0.05798 | 0.016018 | −0.026969 | −0.017852 | −0.022495 | −0.014343 |
| 173 | 0.001355 | −0.019753 | −0.027811 | −0.006204 | −0.028849 | −0.030979 | −0.01567 | 0.002948 | −0.024207 | −0.027514 | 0.014118 | −0.037734 | −0.046111 | −0.011209 |
| 174 | 0.007667 | 0.034495 | 0.025226 | 0.062324 | −0.002619 | −0.004879 | −0.018079 | 0.011142 | 0.016869 | 0.007414 | −0.022687 | 0.001029 | −0.018451 | −0.016243 |
| 175 | −0.009049 | 0.065107 | 0.003588 | −0.057014 | −0.005478 | 0.015446 | 0.04573 | 0.036518 | 0.014003 | −0.012883 | −0.003167 | −0.005514 | 0.02871 | 0.045576 |
| 176 | −0.021249 | −0.053468 | −0.013832 | 0.012667 | 0.048363 | 0.017141 | 0.037692 | −0.015443 | 0.0415 | 0.002969 | 0.05534 | 0.016906 | −0.020855 | 0.010681 |
| 177 | −0.004043 | −0.086427 | −0.041567 | −0.051599 | 0.009021 | −0.044714 | 0.022103 | 0.018273 | −0.006689 | 0.038282 | −0.005649 | −0.019436 | −0.018027 | −0.018486 |
| 178 | 0.061712 | 0.010989 | 0.010499 | −0.067655 | −0.053472 | 0.03895 | −0.031132 | −0.039344 | −0.039307 | 0.020662 | 0.005327 | 0.001296 | −0.003809 | 0.000072 |
| 179 | 0.020793 | −0.017359 | −0.011718 | 0.021945 | −0.043548 | 0.025354 | −0.012244 | −0.100861 | −0.051275 | 0.029582 | 0.002084 | 0.012636 | 0.028727 | −0.002699 |
| 180 | 0.047818 | −0.02948 | −0.008908 | −0.034511 | −0.010632 | 0.040301 | 0.007053 | −0.054218 | −0.009352 | 0.01454 | −0.009278 | −0.00455 | 0.016539 | −0.020975 |
| 181 | 0.012936 | −0.032703 | −0.00851 | −0.046074 | 0.009048 | 0.020586 | 0.012159 | −0.026485 | −0.029191 | −0.000485 | 0.016797 | −0.008531 | 0.007275 | −0.0089 |
| 182 | 0.016384 | 0.02239 | −0.018654 | −0.015482 | 0.028257 | −0.034179 | −0.004918 | 0.006938 | −0.023216 | −0.020069 | −0.013125 | −0.005609 | 0.012511 | −0.027327 |
| 183 | −0.016368 | −0.00308 | 0.029548 | 0.022345 | −0.019294 | −0.001151 | 0.005828 | −0.051458 | −0.000392 | 0.001408 | −0.013965 | 0.028792 | 0.025832 | 0.010052 |
| 184 | −0.020548 | −0.002431 | 0.033698 | −0.027711 | 0.006575 | −0.031789 | −0.066898 | −0.048201 | 0.053851 | 0.001971 | 0.043769 | 0.026715 | −0.034238 | 0.009566 |
| 185 | −0.077093 | −0.002898 | −0.019364 | −0.030418 | −0.059187 | −0.054713 | 0.006565 | 0.019753 | −0.005935 | 0.007992 | 0.021707 | 0.003627 | 0.006668 | 0.023817 |
| 186 | −0.022651 | −0.034582 | −0.011668 | −0.054821 | −0.004924 | 0.053958 | 0.024685 | −0.020073 | −0.059961 | −0.014933 | −0.017491 | −0.032756 | −0.008392 | −0.057988 |
| 187 | −0.010548 | −0.01849 | −0.001664 | −0.019524 | −0.037432 | −0.002 | 0.014342 | 0.027899 | 0.024342 | −0.045267 | −0.008042 | 0.013314 | −0.014375 | −0.052489 |
| 188 | −0.009632 | 0.005643 | 0.000653 | 0.009102 | 0.000427 | −0.020256 | 0.01133 | 0.004707 | 0.039893 | 0.007617 | −0.026858 | 0.019142 | 0.009125 | −0.007322 |
| 189 | −0.045125 | 0.020765 | 0.048702 | 0.029687 | 0.055318 | 0.011797 | −0.021366 | −0.02784 | 0.028452 | −0.022179 | −0.008057 | 0.011999 | 0.015568 | 0.021777 |
| 190 | 0.037218 | −0.039308 | 0.049281 | −0.001846 | 0.001345 | −0.012713 | −0.014843 | 0.002102 | 0.027342 | 0.012936 | −0.018343 | 0.035967 | 0.052159 | 0.01161 |
| 191 | 0.049787 | −0.00269 | 0.019185 | 0.018448 | −0.018467 | −0.000046 | −0.038818 | −0.009084 | 0.041684 | −0.00364 | −0.026122 | −0.002119 | 0.005757 | −0.017749 |
| 192 | 0.035276 | 0.079781 | −0.021005 | 0.042555 | 0.0054 | −0.007008 | 0.008118 | −0.038156 | −0.005542 | 0.030265 | 0.01392 | 0.000202 | 0.031685 | 0.030736 |
| 193 | 0.001001 | 0.027056 | −0.045979 | −0.039434 | −0.042613 | 0.031767 | 0.010985 | 0.008123 | −0.102314 | −0.01378 | −0.002173 | −0.032182 | −0.038366 | 0.005342 |
| 194 | 0.027634 | −0.098743 | −0.08903 | −0.005818 | 0.017471 | 0.078652 | 0.010897 | −0.009647 | 0.054354 | −0.022723 | −0.034266 | 0.029789 | 0.07427 | 0.02367 |
| 195 | 0.015516 | −0.02646 | −0.019652 | 0.043997 | 0.033986 | −0.029799 | 0.026978 | −0.001864 | −0.008646 | 0.014743 | 0.005137 | −0.007828 | 0.01434 | 0.014716 |
| 196 | −0.011049 | 0.065966 | 0.005724 | −0.01551 | 0.044181 | −0.015352 | −0.055378 | −0.051515 | 0.001208 | 0.045637 | 0.021348 | 0.01015 | −0.003294 | 0.024197 |
| 197 | −0.033752 | −0.046125 | 0.000371 | −0.01624 | −0.01882 | 0.019409 | −0.017202 | 0.008339 | 0.051446 | −0.031503 | 0.032531 | −0.027582 | 0.000161 | 0.051072 |
| 198 | 0.008382 | 0.001443 | −0.00532 | 0.010076 | 0.059505 | −0.069424 | 0.014754 | 0.027081 | −0.028353 | −0.051775 | 0.014782 | −0.020247 | −0.038852 | −0.003975 |
| 199 | −0.021015 | −0.008585 | −0.028017 | −0.057981 | 0.014497 | −0.044864 | 0.015263 | 0.019681 | −0.057691 | −0.036953 | −0.005995 | −0.021092 | −0.008792 | 0.030809 |
| 200 | −0.002813 | −0.016022 | −0.037274 | 0.020099 | −0.043905 | 0.036023 | −0.00965 | −0.027728 | −0.026721 | 0.058583 | 0.011046 | 0.053597 | 0.030783 | −0.021401 |
| 201 | 0.033054 | −0.063229 | −0.018546 | 0.025789 | −0.04465 | −0.069156 | 0.000357 | −0.002683 | 0.006474 | −0.009502 | −0.00853 | −0.001253 | −0.014586 | 0.020109 |
| 202 | 0.072712 | −0.071876 | −0.037573 | 0.026253 | −0.092871 | 0.008026 | 0.008713 | 0.00889 | 0.040838 | 0.035667 | −0.019739 | −0.023008 | 0.033541 | −0.04015 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 203 | 0.044856 | −0.039458 | 0.002186 | −0.049047 | 0.044982 | −0.034889 | −0.002529 | 0.016981 | 0.053998 | −0.018431 | −0.032484 | 0.020581 | 0.029291 | 0.029133 |
| 204 | −0.012287 | 0.00659 | −0.073589 | 0.027635 | −0.016015 | 0.049362 | 0.007324 | 0.033642 | −0.007026 | −0.0148 | 0.010025 | −0.00472 | −0.001973 | −0.02602 |
| 205 | 0.051679 | 0.026619 | −0.012494 | −0.015637 | −0.031073 | −0.021561 | 0.062871 | 0.020576 | −0.022918 | 0.003031 | −0.030988 | −0.004315 | −0.011251 | 0.006897 |
| 206 | −0.088396 | −0.042246 | −0.035289 | −0.048498 | −0.010685 | −0.00944 | −0.057801 | −0.008818 | 0.003116 | 0.010076 | 0.01328 | 0.036778 | 0.018655 | 0.036865 |
| 207 | 0.252282 | 0.005651 | 0.018269 | −0.06477 | −0.081509 | −0.01804 | −0.034322 | 0.000514 | 0.02668 | −0.010029 | 0.035726 | 0.002841 | 0.031595 | −0.031683 |
| 208 | 0.008127 | 0.367231 | −0.039993 | −0.01269 | −0.035774 | 0.03245 | −0.006211 | 0.012457 | −0.044164 | 0.033031 | −0.009461 | −0.053721 | 0.025859 | −0.020449 |
| 209 | −0.045575 | −0.001141 | 0.260151 | −0.022844 | 0.049114 | 0.03073 | 0.0395 | 0.003842 | 0.047182 | 0.023855 | 0.029204 | −0.008474 | 0.002523 | 0.020298 |
| 210 | 0.017859 | 0.035359 | −0.04653 | 0.28655 | −0.059123 | −0.003306 | −0.054857 | 0.013534 | −0.016562 | 0.013785 | 0.032309 | −0.00148 | −0.019679 | 0.035679 |
| 211 | −0.040489 | 0.017164 | 0.038028 | −0.038457 | 0.359913 | 0.015465 | 0.0415 | −0.0299 | −0.015767 | 0.047617 | −0.001467 | −0.0303 | −0.007962 | −0.008744 |
| 212 | −0.041677 | 0.024512 | 0.004476 | 0.023582 | −0.018419 | 0.174899 | −0.002061 | 0.01572 | −0.010152 | 0.025918 | 0.039803 | 0.027174 | 0.008438 | 0.046751 |
| 213 | −0.011665 | 0.024895 | −0.020174 | 0.016279 | −0.019363 | −0.007806 | 0.178298 | 0.007611 | −0.033948 | 0.00162 | −0.02962 | 0.031084 | 0.007604 | 0.010173 |
| 214 | 0.007672 | −0.004387 | −0.009699 | 0.012901 | −0.007726 | 0.029492 | −0.010409 | 0.823788 | −0.03373 | 0.062362 | −0.009326 | −0.005267 | 0.00656 | −0.006592 |
| 215 | 0.01461 | −0.013315 | 0.074663 | −0.063427 | −0.009359 | −0.000402 | 0.024393 | −0.048307 | 0.473764 | 0.006859 | −0.028065 | −0.037139 | −0.036794 | 0.029758 |
| 216 | −0.034368 | −0.013214 | 0.021054 | −0.036507 | 0.096152 | −0.022394 | −0.008735 | 0.053045 | 0.005002 | 0.678311 | −0.061801 | −0.022236 | −0.09447 | −0.034565 |
| 217 | 0.038044 | 0.039063 | −0.011483 | 0.026301 | −0.014727 | −0.009241 | −0.023083 | 0.005169 | −0.038366 | −0.045966 | 0.594036 | 0.01329 | −0.033974 | −0.148635 |
| 218 | 0.026656 | −0.041989 | −0.017466 | −0.037301 | 0.017062 | 0.001248 | 0.081424 | 0.007102 | −0.011439 | −0.043573 | −0.011758 | 0.811471 | −0.105015 | −0.012795 |
| 219 | −0.014528 | 0.013826 | 0.008534 | −0.039684 | 0.041333 | −0.040573 | 0.022657 | −0.008349 | −0.004979 | −0.099394 | −0.024549 | −0.097687 | 0.778828 | −0.016986 |
| 220 | −0.013182 | −0.003271 | 0.00909 | 0.00397 | −0.013541 | 0.001656 | −0.028021 | −0.002972 | 0.004399 | −0.014295 | −0.177738 | −0.00341 | −0.028019 | 0.706315 |
| 221 | 0.013061 | −0.006859 | 0.036582 | 0.02967 | −0.022045 | 0.039767 | 0.006353 | −0.017748 | 0.034548 | −0.02756 | 0.027409 | −0.036135 | −0.035669 | 0.010528 |
| 222 | −0.003315 | −0.025903 | −0.018852 | 0.001672 | 0.018212 | −0.001623 | −0.018898 | 0.002268 | −0.004952 | −0.013688 | 0.011286 | −0.020917 | −0.036727 | 0.000583 |
| 223 | −0.026101 | −0.01431 | 0.031916 | 0.001667 | 0.057696 | −0.020578 | −0.003796 | 0.023942 | −0.029338 | −0.051583 | −0.00271 | −0.037078 | −0.051385 | −0.047013 |
| 224 | 0.014925 | −0.024813 | 0.036156 | −0.015126 | 0.050043 | −0.013924 | 0.027069 | −0.012379 | 0.017799 | −0.005088 | 0.03996 | −0.037334 | −0.020284 | 0.006256 |
| 225 | 0.011686 | −0.006836 | 0.022622 | −0.019519 | 0.021583 | −0.042775 | 0.039881 | 0.011306 | 0.00986 | 0.003123 | 0.057486 | −0.018455 | 0.001366 | 0.016749 |
| 226 | 0.016301 | 0.016263 | 0.000504 | −0.022869 | −0.024457 | −0.028985 | 0.031485 | 0.002839 | −0.037519 | 0.035742 | 0.04717 | −0.007571 | 0.008737 | 0.033037 |
| 227 | 0.040545 | 0.034717 | 0.024652 | −0.053316 | 0.008787 | 0.05052 | −0.010422 | −0.048581 | 0.005013 | 0.027553 | −0.015825 | 0.047697 | 0.038202 | 0.009375 |
| 228 | −0.058533 | −0.013136 | 0.024497 | −0.044684 | −0.057097 | −0.039453 | −0.020032 | −0.013696 | 0.045055 | 0.038089 | 0.049307 | −0.034464 | −0.006385 | 0.022145 |
| 229 | −0.023673 | 0.006293 | −0.01423 | 0.007941 | 0.016322 | −0.048297 | 0.00047 | 0.013931 | 0.010328 | −0.018428 | −0.008151 | 0.01943 | 0.019515 | 0.015768 |
| 230 | −0.032773 | 0.010992 | 0.014125 | 0.001813 | 0.018634 | 0.040777 | 0.020757 | −0.014544 | −0.050351 | −0.073574 | 0.022476 | 0.004024 | 0.016925 | 0.015856 |
| 231 | 0.057374 | −0.030225 | −0.01892 | −0.006988 | 0.015253 | 0.045157 | −0.005982 | 0.038844 | 0.093815 | −0.031022 | 0.017272 | 0.066286 | 0.040785 | −0.010209 |
| 232 | 0.032477 | 0.056675 | 0.038461 | −0.024226 | 0.044575 | −0.002676 | −0.025606 | −0.038896 | 0.019012 | 0.062359 | −0.011219 | 0.017429 | −0.009878 | −0.06224 |
| 233 | 0.031689 | 0.004436 | 0.018022 | 0.014496 | −0.002852 | −0.024944 | −0.042789 | −0.001831 | 0.033934 | 0.0034 | −0.022675 | 0.011845 | 0.020454 | −0.000401 |
| 234 | 0.018833 | −0.045566 | 0.008638 | −0.015453 | 0.016544 | −0.067553 | −0.034951 | −0.000543 | −0.059411 | −0.007206 | 0.063508 | 0.002649 | −0.02507 | 0.020887 |
| 235 | −0.000209 | −0.023709 | −0.046754 | 0.08284 | −0.040995 | 0.056477 | −0.007652 | −0.027002 | −0.035477 | 0.082496 | 0.046568 | 0.050342 | 0.024131 | 0.011042 |
| 236 | −0.009133 | −0.010852 | −0.041682 | −0.018286 | 0.006895 | −0.008791 | 0.026186 | 0.020968 | 0.000406 | −0.021557 | −0.013058 | 0.017813 | 0.035975 | −0.012143 |
| 237 | −0.050723 | 0.007494 | −0.028467 | −0.032289 | 0.018946 | 0.001654 | −0.016053 | 0.013472 | 0.025594 | −0.006678 | −0.003298 | 0.005254 | 0.026797 | 0.041498 |
| 238 | 0.008971 | −0.003193 | 0.008479 | 0.026214 | 0.032829 | 0.001434 | 0.004035 | −0.017272 | 0.011834 | −0.020956 | −0.014713 | 0.049827 | −0.044139 | 0.017622 |
| 239 | 0.007642 | −0.025067 | −0.032632 | 0.017801 | 0.010689 | 0.008895 | −0.028338 | −0.010433 | −0.007086 | −0.037373 | −0.004504 | 0.041295 | −0.03358 | 0.039842 |
| 240 | 0.008324 | −0.031821 | 0.051014 | 0.047969 | −0.00952 | 0.016123 | 0.014288 | −0.007643 | −0.003355 | −0.000468 | −0.012176 | 0.00319 | 0.01991 | 0.019583 |
| 241 | 0.016565 | 0.059123 | 0.052755 | 0.04013 | 0.045973 | −0.016231 | −0.001344 | 0.026588 | −0.000126 | −0.004432 | −0.004411 | 0.015484 | 0.017192 | 0.023643 |
| 242 | −0.011467 | 0.006238 | 0.004485 | 0.039738 | −0.000246 | 0.014305 | −0.027221 | 0.054803 | −0.013781 | −0.032994 | −0.015106 | 0.017461 | 0.025168 | −0.041481 |
| 243 | −0.015849 | 0.016785 | 0.059517 | −0.022555 | −0.014194 | 0.011613 | 0.026437 | 0.03884 | −0.039814 | −0.039093 | 0.001446 | 0.000405 | −0.052829 | −0.009154 |
| 244 | 0.042847 | −0.015184 | −0.010796 | 0.007419 | −0.049356 | 0.027573 | −0.022463 | 0.01078 | 0.03026 | 0.046808 | 0.0171 | 0.032201 | 0.066357 | 0.012543 |
| 245 | 0.055685 | −0.044956 | −0.010484 | −0.008778 | 0.018144 | 0.068685 | −0.057819 | −0.035529 | −0.083057 | 0.031873 | −0.005341 | −0.016514 | 0.009557 | 0.062326 |
| 246 | 0.005996 | 0.0274 | 0.00477 | −0.037669 | −0.021558 | 0.028437 | −0.002568 | 0.010118 | 0.001387 | 0.003991 | 0.037772 | −0.016488 | 0.008071 | −0.041252 |
| 247 | 0.039708 | 0.0534691 | 0.032234 | 0.003421 | −0.013493 | −0.005962 | −0.002609 | −0.019066 | −0.006066 | 0.034134 | 0.005358 | 0.036534 | 0.016002 | −0.003103 |
| 248 | 0.002675 | 0.01214 | −0.00061 | 0.009646 | −0.022757 | −0.01626 | 0.031886 | 0.006253 | −0.040962 | −0.000788 | −0.002415 | −0.00908 | −0.024309 | −0.011672 |
| 249 | −0.016348 | −0.009926 | 0.028359 | 0.049962 | −0.025578 | −0.021017 | 0.048502 | 0.033109 | 0.051037 | 0.020569 | −0.018279 | −0.012902 | −0.011797 | −0.016271 |
| 250 | 0.008861 | 0.03269 | 0.042351 | −0.013166 | 0.000994 | −0.020251 | 0.033251 | 0.025859 | 0.007919 | −0.006572 | −0.007906 | −0.001831 | 0.008133 | −0.019211 |
| 251 | −0.0051 | −0.046136 | −0.000204 | 0.020809 | 0.034865 | 0.053558 | 0.008867 | −0.01122 | −0.068817 | 0.023202 | 0.015827 | 0.013457 | 0.011732 | 0.024643 |
| 252 | −0.046307 | 0.008592 | −0.003548 | 0.062365 | 0.03712 | 0.057176 | −0.005449 | 0.003955 | −0.004324 | −0.016495 | −0.0052 | 0.005738 | 0.01663 | 0.0713 |
| 253 | −0.008917 | 0.004536 | −0.036641 | −0.026132 | −0.001115 | 0.023546 | 0.049261 | 0.003823 | −0.00528 | −0.05165 | −0.001602 | 0.00321 | 0.012152 | −0.009354 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 254 | −0.019021 | −0.017413 | −0.020531 | 0.036371 | −0.050711 | −0.027935 | −0.011385 | 0.06303 | 0.045571 | −0.021308 | 0.030681 | 0.019694 | 0.023272 | −0.007128 |
| 255 | 0.052554 | 0.000774 | 0.045514 | 0.037729 | −0.041391 | 0.00912 | −0.012346 | 0.043839 | 0.050111 | −0.015454 | 0.030871 | 0.026238 | 0.022415 | −0.020188 |
| 256 | 0.001112 | −0.036635 | 0.031987 | −0.009106 | 0.037424 | −0.067732 | 0.004026 | −0.00338 | −0.001793 | 0.024354 | 0.024165 | −0.004349 | 0.008782 | 0.007044 |
| 257 | −0.001212 | −0.020331 | 0.019002 | −0.017269 | 0.015912 | −0.005467 | 0.005994 | −0.009296 | 0.004947 | −0.004322 | 0.034077 | 0.022242 | 0.009794 | 0.022118 |
| 258 | 0.049808 | 0.006137 | −0.002052 | 0.016558 | −0.050256 | 0.018072 | 0.005857 | 0.031713 | −0.0056 | −0.007494 | 0.012934 | 0.008048 | 0.030702 | 0.034118 |
| 259 | −0.011267 | −0.021604 | 0.000881 | 0.016823 | −0.00737 | 0.021154 | 0.014992 | 0.008755 | −0.033938 | −0.007781 | −0.01236 | −0.033759 | −0.020477 | 0.001192 |
| 260 | −0.055045 | −0.003987 | −0.024307 | −0.012114 | 0.00857 | 0.034887 | −0.023142 | −0.015421 | −0.032468 | 0.003766 | −0.01615 | −0.007429 | 0.008265 | 0.004651 |
| 261 | −0.057013 | −0.001486 | 0.029804 | 0.011525 | 0.015773 | 0.038775 | −0.015846 | −0.003216 | −0.004203 | −0.012045 | −0.022114 | 0.00596 | −0.003559 | 0.027603 |
| 262 | −0.021808 | 0.001611 | −0.035234 | 0.039464 | −0.018347 | −0.026079 | −0.001409 | −0.011297 | 0.020989 | −0.022826 | −0.049619 | 0.018422 | 0.030896 | −0.041721 |
| 263 | −0.014557 | −0.01612 | −0.04153 | −0.005236 | −0.019661 | −0.017713 | 0.010438 | 0.008569 | 0.017329 | −0.056283 | −0.013255 | −0.009428 | −0.014025 | −0.025535 |
| 264 | −0.008327 | −0.03878 | −0.027317 | −0.030269 | −0.02018 | −0.011492 | −0.029734 | 0.003665 | −0.028626 | −0.000888 | 0.019257 | 0.037291 | 0.024535 | 0.001468 |
| 265 | 0.036189 | 0.031671 | 0.004563 | 0.056789 | −0.024127 | −0.010379 | −0.01461 | −0.005995 | −0.06146 | 0.009752 | −0.044776 | 0.027147 | 0.045098 | −0.030981 |
| 266 | −0.012325 | 0.013672 | 0.019554 | 0.025686 | −0.00612 | −0.067464 | 0.004387 | −0.021215 | 0.011347 | 0.004988 | −0.042832 | 0.024587 | 0.027005 | −0.036955 |
| 267 | 0.058027 | −0.014316 | −0.006661 | 0.008957 | −0.006751 | 0.040292 | 0.010427 | −0.00728 | −0.010094 | −0.008336 | 0.004199 | −0.030903 | −0.006493 | −0.004954 |
| 268 | −0.000996 | 0.036411 | 0.003174 | −0.011246 | 0.001641 | −0.03092 | 0.004431 | 0.001365 | −0.004161 | 0.012868 | 0.053592 | 0.001928 | 0.005831 | 0.017909 |
| 269 | −0.040463 | 0.048291 | −0.013265 | 0.014569 | 0.019693 | −0.039422 | 0.020737 | −0.002282 | −0.013848 | 0.028481 | 0.026762 | 0.023302 | 0.004755 | −0.005372 |
| 270 | −0.001827 | 0.019667 | −0.026276 | 0.00554 | 0.040669 | 0.018098 | 0.03793 | 0.024761 | 0.0372 | −0.012416 | 0.001586 | −0.015606 | −0.003534 | 0.016223 |
| 271 | −0.026124 | 0.034463 | −0.013487 | 0.029545 | 0.004609 | 0.013629 | 0.009945 | 0.002415 | 0.002094 | 0.004977 | −0.012368 | 0.054753 | 0.028378 | 0.010558 |
| 272 | 0.016447 | −0.005979 | 0.050238 | 0.065863 | −0.039073 | 0.040046 | −0.011099 | −0.00506 | −0.050114 | 0.032712 | 0.026285 | 0.00665 | −0.02187 | 0.055685 |
| 273 | 0.00199 | 0.025215 | 0.072912 | 0.010514 | −0.024511 | 0.006917 | 0.013938 | −0.009286 | −0.0181341 | 0.066053 | 0.021075 | 0.000123 | 0.027805 | 0.023944 |
| 274 | 0.002626 | 0.042418 | 0.067285 | 0.016667 | −0.007316 | −0.001416 | 0.030669 | −0.010747 | −0.018289 | 0.079808 | 0.013571 | 0.002497 | 0.0211 | 0.022226 |
| 275 | −0.065965 | 0.024672 | 0.028508 | −0.003495 | 0.027771 | 0.048668 | −0.017431 | −0.018718 | −0.036148 | −0.043442 | −0.004275 | 0.014024 | −0.013914 | 0.008907 |
| 276 | −0.022956 | −0.038108 | −0.028259 | −0.044317 | 0.011856 | 0.020994 | 0.016822 | 0.00319 | 0.060723 | −0.057309 | 0.031153 | 0.010214 | 0.002436 | 0.000315 |
| 277 | 0.01013 | 0.015396 | −0.020423 | 0.011574 | 0.005356 | −0.016651 | −0.038755 | 0.012375 | 0.016167 | −0.000183 | 0.007161 | −0.024496 | 0.017235 | 0.053947 |
| 278 | −0.006625 | −0.008936 | −0.018859 | −0.020736 | −0.004668 | −0.01472 | −0.037927 | 0.000824 | −0.015516 | 0.003451 | 0.010127 | −0.00818 | 0.012755 | 0.069326 |
| 279 | −0.031482 | −0.0549 | −0.064911 | 0.024839 | 0.022597 | 0.02076 | −0.005558 | −0.031798 | −0.013292 | −0.037321 | 0.010769 | 0.010095 | −0.068432 | 0.027002 |
| 280 | −0.000884 | −0.002335 | 0.043933 | 0.009792 | 0.070638 | 0.032086 | −0.012407 | −0.000424 | −0.011095 | −0.043447 | 0.002135 | 0.000686 | 0.001463 | −0.010176 |
| 281 | −0.016528 | −0.004951 | −0.000874 | 0.018187 | −0.00031 | 0.042903 | −0.023183 | 0.011031 | 0.04086 | −0.006259 | 0.070989 | −0.017077 | 0.011599 | −0.029445 |
| 282 | 0.01207 | 0.029382 | −0.017161 | 0.00376 | −0.009427 | −0.002804 | −0.000995 | 0.006598 | 0.007097 | 0.002891 | 0.042245 | 0.017341 | 0.022782 | −0.033462 |
| 283 | 0.01282 | −0.002409 | −0.021244 | −0.000887 | −0.059524 | 0.013867 | 0.007537 | −0.066202 | −0.016596 | 0.046374 | −0.011911 | 0.011062 | −0.007655 | −0.020366 |
| 284 | −0.046457 | −0.032911 | 0.009894 | 0.016755 | 0.001502 | 0.019064 | −0.004412 | −0.024052 | 0.038766 | 0.012888 | 0.027394 | 0.02559 | 0.013944 | −0.000762 |
| 285 | 0.007827 | −0.012974 | 0.027997 | −0.015286 | 0.036791 | −0.003292 | 0.041803 | −0.001762 | −0.009288 | 0.0085 | −0.006296 | 0.019574 | 0.006432 | −0.002391 |
| 286 | −0.010132 | −0.01285 | −0.027328 | 0.014124 | −0.007282 | −0.013637 | −0.024168 | 0.013399 | 0.005214 | −0.035493 | −0.015662 | 0.010526 | 0.007733 | 0.00444 |
| 287 | −0.009275 | 0.007091 | −0.030056 | −0.038212 | −0.017656 | −0.011961 | −0.008468 | −0.000683 | 0.015302 | −0.024067 | −0.018761 | 0.002221 | −0.014648 | 0.024551 |
| 288 | −0.031056 | 0.00431 | −0.045817 | −0.011536 | −0.055511 | −0.076624 | −0.011432 | −0.003569 | −0.005519 | −0.005516 | 0.018797 | 0.001476 | −0.005646 | −0.003695 |
| 289 | 0.037503 | −0.000872 | −0.032397 | 0.031581 | 0.027621 | −0.056741 | 0.02928 | 0.017781 | −0.004224 | 0.000088 | −0.032199 | 0.01439 | 0.028797 | −0.045276 |
| 290 | 0.002765 | 0.021995 | 0.017551 | 0.009026 | −0.002841 | −0.017681 | 0.023989 | −0.001995 | −0.007268 | −0.014634 | 0.009349 | 0.004103 | 0.01022 | 0.015166 |
| 291 | 0.001986 | 0.022608 | 0.006754 | 0.005573 | −0.016113 | −0.01842 | 0.028174 | 0.004442 | 0.00416 | −0.01742 | 0.015019 | 0.006891 | 0.014511 | 0.028086 |
| 292 | 0.001964 | 0.048043 | −0.000413 | 0.029201 | −0.00071 | 0.018344 | 0.06049 | 0.002097 | 0.014286 | 0.006916 | 0.004199 | 0.019004 | 0.018942 | 0.011765 |
| 293 | 0.012087 | −0.019569 | −0.02485 | −0.024037 | −0.003213 | −0.049271 | −0.049487 | 0.012857 | −0.064189 | −0.006463 | 0.032821 | −0.033788 | −0.001786 | 0.041151 |
| 294 | −0.019653 | 0.005327 | −0.027468 | −0.008796 | 0.016976 | 0.006879 | 0.027669 | 0.045091 | 0.01349 | 0.013576 | 0.052236 | −0.026816 | −0.027894 | 0.039355 |
| 295 | −0.003398 | −0.008564 | 0.013791 | 0.0201 | 0.003465 | 0.018291 | 0.039945 | 0.003764 | 0.056028 | 0.039944 | 0.010594 | −0.030264 | −0.000273 | 0.009921 |
| 296 | 0.001969 | 0.020402 | −0.006908 | 0.004205 | 0.018952 | 0.00566 | −0.010115 | 0.031431 | 0.057065 | 0.050216 | −0.006801 | 0.016227 | 0.013419 | −0.038243 |
| 297 | −0.010018 | −0.061088 | −0.006123 | 0.018069 | 0.020336 | 0.009225 | 0.010232 | −0.004811 | 0.091085 | 0.014468 | −0.040306 | −0.018411 | 0.020723 | −0.030801 |
| 298 | 0.003926 | −0.020402 | −0.002795 | 0.025185 | −0.043199 | −0.027385 | −0.010406 | −0.034901 | −0.045673 | 0.02927 | 0.003115 | 0.033671 | 0.030166 | 0.006834 |
| 299 | 0.026651 | −0.032337 | 0.019461 | −0.005901 | 0.0378 | −0.037295 | 0.01655 | 0.008858 | −0.024029 | 0.035601 | −0.002774 | 0.002623 | 0.021979 | −0.017699 |
| 300 | 0.05224 | 0.053552 | 0.03264 | 0.038229 | 0.034357 | 0.018695 | 0.033669 | −0.025134 | 0.074415 | −0.041776 | −0.016955 | 0.013799 | 0.024663 | 0.002116 |
| 301 | −0.028619 | −0.044847 | 0.037591 | 0.02946 | 0.017635 | 0.00979 | −0.01192 | 0.018502 | −0.000741 | −0.010591 | 0.02734 | 0.017522 | −0.004505 | −0.030428 |
| 302 | 0.012928 | −0.036708 | 0.038354 | −0.003645 | 0.026792 | 0.000161 | −0.010278 | 0.029148 | −0.036514 | −0.034912 | −0.012204 | −0.002681 | −0.035949 | −0.041164 |
| 303 | 0.009084 | −0.031432 | 0.029604 | −0.000224 | −0.032332 | 0.029537 | 0.008453 | −0.006646 | −0.08888 | 0.048378 | 0.010183 | 0.000458 | −0.002297 | −0.001275 |
| 304 | −0.033963 | −0.02906 | −0.063372 | 0.010063 | −0.034068 | 0.020262 | −0.012068 | −0.001538 | −0.021172 | 0.049278 | −0.059029 | −0.024423 | −0.012162 | −0.017767 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 305 | −0.090289 | 0.002378 | −0.029684 | −0.058019 | 0.108733 | 0.005948 | −0.010696 | 0.016011 | −0.012726 | −0.026811 | 0.04945 | −0.008273 | −0.037444 | 0.031667 |
| 306 | 0.00092 | 0.062591 | 0.00193 | 0.028329 | 0.034034 | 0.038813 | −0.024017 | 0.008398 | −0.034245 | −0.000401 | 0.029595 | 0.0089 | −0.011899 | 0.039957 |
| 307 | 0.030009 | 0.007256 | −0.057273 | 0.021195 | −0.007658 | −0.006674 | −0.05753 | −0.036253 | 0.035985 | −0.028347 | 0.030285 | −0.010405 | 0.01992 | −0.000032 |
| 308 | 0.02312 | 0.039568 | 0.003808 | −0.006375 | 0.018252 | −0.040643 | −0.033813 | −0.014634 | −0.020191 | −0.010521 | −0.022887 | −0.012373 | −0.038818 | −0.024455 |
| 309 | 0.047574 | −0.024491 | 0.009434 | 0.056428 | −0.007607 | 0.002009 | 0.002194 | −0.002063 | −0.011133 | −0.007811 | −0.005063 | −0.030383 | −0.03824 | 0.010603 |
| 310 | −0.061783 | −0.03121 | −0.043433 | 0.024019 | −0.026795 | −0.057988 | 0.028616 | −0.014633 | −0.06616 | 0.02898 | −0.015147 | −0.026367 | −0.021756 | −0.015266 |
| 311 | 0.002982 | 0.01105 | −0.02935 | 0.012732 | 0.007562 | −0.002154 | −0.039904 | −0.012989 | −0.009739 | 0.010965 | 0.009818 | 0.015161 | 0.039045 | 0.044269 |
| 312 | −0.083588 | 0.006922 | 0.057238 | 0.019839 | 0.014089 | −0.029388 | −0.007974 | 0.012436 | 0.031721 | −0.019285 | −0.042032 | 0.013131 | −0.016198 | −0.048104 |
| 313 | 0.060293 | 0.012822 | 0.015198 | 0.010228 | −0.024019 | 0.004097 | −0.064686 | 0.014457 | 0.045608 | 0.016895 | 0.032074 | 0.005794 | 0.013837 | −0.002899 |
| 314 | −0.005251 | −0.030085 | −0.043372 | −0.063632 | 0.009469 | −0.00497 | 0.008936 | −0.010383 | −0.006739 | 0.032021 | 0.018162 | −0.018966 | 0.000306 | 0.019288 |
| 315 | 0.058428 | 0.052216 | 0.018446 | 0.007189 | −0.012306 | 0.018348 | 0.021902 | −0.001534 | −0.007844 | 0.014429 | −0.026945 | 0.012848 | 0.016223 | 0.006951 |
| 316 | 0.010971 | −0.016666 | 0.013143 | 0.017251 | −0.006708 | −0.007907 | 0.002425 | 0.018174 | 0.006693 | −0.06098 | −0.007842 | 0.015183 | 0.01059 | 0.007589 |
| 317 | 0.024801 | −0.004886 | −0.013865 | 0.039064 | 0.006836 | 0.002188 | −0.007557 | −0.00773 | −0.006284 | −0.021831 | 0.033565 | −0.018659 | −0.023234 | 0.037496 |
| 318 | 0.011575 | 0.058856 | −0.009178 | −0.002147 | 0.011575 | −0.021728 | −0.021332 | 0.00767 | 0.025018 | 0.054488 | −0.00663 | 0.060598 | 0.039974 | 0.04577 |
| 319 | 0.054641 | −0.009955 | 0.033122 | 0.002858 | −0.043648 | 0.053722 | 0.022363 | 0.011906 | 0.022685 | −0.024129 | 0.015421 | −0.018644 | 0.005166 | 0.021753 |
| 320 | −0.052716 | 0.016831 | −0.011301 | −0.065314 | −0.047583 | 0.026249 | −0.03374 | 0.021811 | 0.018815 | 0.003087 | 0.001818 | −0.002598 | 0.006918 | −0.029796 |
| 321 | 0.00678 | 0.021918 | 0.054656 | −0.076478 | −0.000933 | −0.020833 | 0.037612 | −0.017623 | −0.013516 | 0.028806 | 0.045777 | 0.010791 | 0.003995 | −0.02053 |
| 322 | 0.061578 | 0.069232 | −0.011985 | 0.049365 | 0.046789 | 0.015451 | −0.000625 | 0.027167 | 0.014171 | 0.002398 | −0.010378 | 0.001199 | −0.009756 | −0.034335 |
| 323 | −0.027273 | −0.014019 | 0.065 | −0.009779 | −0.030598 | −0.030653 | 0.058709 | 0.017156 | −0.044218 | −0.008878 | 0.00429 | 0.020355 | 0.045427 | 0.024706 |
| 324 | 0.010483 | −0.061504 | 0.04234 | −0.007657 | −0.05649 | 0.038838 | 0.023845 | −0.01603 | −0.026599 | 0.026531 | −0.012878 | 0.002359 | −0.011943 | −0.050591 |
| 325 | −0.056024 | −0.012447 | −0.03748 | −0.005301 | 0.010265 | 0.015632 | −0.01612 | −0.035395 | −0.004844 | 0.014521 | −0.018577 | −0.016882 | 0.002421 | −0.059935 |
| 326 | 0.00931 | −0.027541 | 0.044337 | −0.052164 | 0.042487 | −0.015283 | 0.001247 | −0.015442 | 0.039669 | −0.022196 | 0.056383 | −0.026347 | −0.057914 | 0.024689 |
| 327 | −0.000059 | 0.004066 | 0.032155 | 0.036717 | 0.036622 | −0.003136 | 0.003848 | 0.017489 | 0.014531 | 0.032791 | −0.003116 | 0.001886 | 0.002599 | −0.012754 |
| 328 | 0.066366 | −0.018513 | −0.036803 | −0.00002 | −0.013326 | −0.067262 | 0.037105 | −0.005981 | 0.010933 | −0.013324 | −0.015921 | −0.028016 | −0.028045 | 0.032682 |
| 329 | 0.020322 | −0.018028 | −0.002052 | 0.041066 | 0.03192 | −0.033258 | −0.004244 | −0.002548 | 0.021641 | 0.005275 | 0.035126 | 0.000885 | −0.005404 | −0.00237 |
| 330 | −0.001573 | −0.035384 | −0.009135 | −0.03092 | −0.031242 | −0.002977 | −0.004316 | 0.009453 | −0.007881 | −0.03716 | 0.048609 | −0.002423 | −0.011636 | −0.002389 |
| 331 | 0.019606 | 0.037183 | 0.00717 | 0.020947 | −0.009873 | −0.045381 | 0.004338 | 0.002434 | −0.023185 | −0.015461 | −0.025979 | 0.006625 | −0.02677 | −0.002776 |
| 332 | 0.012635 | 0.029255 | −0.031485 | −0.01803 | 0.043192 | −0.021905 | −0.015896 | −0.033185 | −0.00138 | 0.037827 | −0.013322 | 0.013762 | 0.021085 | −0.036866 |
| 333 | −0.002952 | −0.026282 | −0.009335 | 0.043948 | 0.042623 | 0.001026 | −0.021209 | 0.017368 | −0.00099 | −0.015882 | −0.014723 | 0.011125 | −0.006265 | −0.000269 |
| 334 | −0.055404 | 0.022902 | −0.031203 | 0.002455 | −0.023828 | −0.033293 | −0.051096 | −0.027897 | −0.017511 | −0.006528 | −0.012662 | −0.032876 | −0.004831 | 0.029466 |
| 335 | −0.034113 | −0.001118 | −0.009696 | 0.040115 | 0.055612 | −0.000076 | 0.020533 | −0.003297 | −0.015938 | −0.022796 | −0.020914 | −0.014697 | −0.042805 | −0.021284 |
| 336 | 0.033305 | 0.041936 | 0.079524 | −0.060942 | 0.043006 | −0.009572 | 0.029948 | −0.009422 | −0.061424 | −0.060279 | −0.060559 | 0.012933 | −0.007797 | −0.002016 |
| 337 | −0.015556 | 0.020473 | −0.063746 | 0.064414 | 0.058975 | 0.015393 | 0.018936 | 0.026378 | 0.012998 | 0.035558 | −0.0024 | 0.047377 | 0.032291 | −0.016986 |
| 338 | −0.02031 | −0.031194 | 0.014598 | −0.034826 | 0.038421 | 0.048012 | −0.029058 | 0.004033 | 0.033854 | 0.017379 | −0.020389 | 0.012479 | −0.012823 | −0.015108 |
| 339 | 0.000685 | −0.027098 | −0.062775 | 0.012787 | −0.005583 | −0.029761 | −0.039347 | 0.010414 | −0.065474 | −0.011654 | −0.015252 | 0.009096 | 0.002375 | 0.009183 |
| 340 | −0.049525 | −0.000163 | 0.020241 | 0.034815 | 0.019303 | 0.022917 | 0.003623 | −0.004022 | 0.032641 | −0.002927 | 0.012527 | 0.02984 | −0.004627 | 0.031802 |

| | HN | HO | HP | HQ | HR | HS | HT | HU | HV | H | HX | HY | HZ | IA |
|---|---|---|---|---|---|---|---|---|---|---|---|---|---|---|
| 1 | −0.086363 | −0.09882 | −0.026921 | 0.09895 | 0.053775 | −0.019997 | 0.133592 | 0.050583 | −0.048268 | −0.026262 | 0.087618 | 0.025366 | 0.062051 | 0.084986 |
| 2 | −0.04869 | −0.009969 | 0.00264 | −0.134401 | −0.117549 | −0.020247 | −0.135826 | −0.101719 | −0.054746 | −0.026968 | −0.027844 | 0.004006 | −0.01273 | −0.056996 |
| 3 | 0.075318 | 0.055752 | 0.02031 | 0.0843 | 0.042847 | −0.048555 | −0.020985 | −0.040686 | −0.00756 | 0.031963 | −0.06048 | −0.087153 | −0.026776 | −0.063471 |
| 4 | −0.012415 | 0.04115 | 0.001081 | −0.039384 | −0.009663 | −0.010096 | −0.013883 | −0.107571 | 0.054274 | 0.002018 | −0.063545 | −0.073534 | −0.070531 | −0.079812 |
| 5 | 0.058657 | 0.008841 | 0.014255 | 0.052803 | 0.070817 | −0.03437 | −0.007195 | 0.043315 | 0.008238 | −0.009904 | −0.00636 | 0.035831 | −0.047667 | −0.048966 |
| 6 | −0.06442 | −0.058978 | −0.093018 | 0.012045 | 0.037376 | 0.022026 | 0.009921 | −0.019236 | −0.007275 | 0.0439 | 0.07155 | 0.017209 | 0.04702 | 0.049285 |
| 7 | 0.029646 | 0.027108 | −0.012163 | 0.031886 | −0.002163 | −0.017654 | −0.006246 | −0.019497 | 0.044023 | −0.069992 | −0.037488 | 0.024618 | −0.037 | −0.058036 |
| 8 | 0.045911 | 0.021227 | 0.018628 | −0.006856 | −0.03424 | −0.038287 | −0.069891 | 0.003811 | −0.039716 | −0.007287 | −0.031599 | 0.010615 | 0.048473 | −0.022517 |
| 9 | 0.054286 | 0.038334 | 0.036641 | 0.02352 | 0.021634 | 0.009106 | −0.028408 | −0.00717 | 0.042952 | −0.053523 | −0.034263 | 0.043683 | −0.01455 | 0.028504 |
| 10 | 0.056809 | −0.070819 | −0.022832 | −0.028319 | 0.026802 | 0.051784 | 0.005491 | −0.000996 | −0.059114 | −0.0581 | 0.040729 | −0.013224 | 0.019547 | −0.023445 |
| 11 | −0.038488 | −0.044748 | −0.039236 | 0.00077 | −0.012488 | −0.009969 | −0.071413 | −0.038754 | −0.026459 | −0.015242 | −0.040902 | 0.012509 | 0.044302 | 0.067113 |
| 12 | −0.040415 | −0.035551 | −0.004715 | −0.008894 | −0.011848 | 0.034198 | 0.045186 | 0.040439 | 0.013176 | 0.031097 | −0.005697 | −0.007482 | 0.053315 | −0.000304 |

APPENDIX B1-continued

| PCA Transformation Matrix(340 × 340; Normal/Diseased) | | | | | | | | | | | | | | |
|---|---|---|---|---|---|---|---|---|---|---|---|---|---|---|
| 13 | −0.016103 | 0.009714 | 0.01642 | −0.06559 | −0.092577 | 0.024036 | −0.042987 | −0.008443 | −0.066087 | −0.053334 | −0.004723 | −0.03657 | −0.005822 | −0.145147 |
| 14 | −0.016127 | −0.065219 | −0.029039 | 0.093153 | 0.092671 | −0.046026 | −0.02557 | 0.254444 | 0.198255 | 0.083848 | 0.048702 | 0.060658 | −0.061689 | 0.071611 |
| 15 | −0.067356 | −0.081804 | −0.05709 | −0.046856 | −0.033865 | −0.004978 | 0.027571 | −0.03943 | −0.055845, | −0.023378 | 0.067722 | −0.059667 | −0.047681 | 0.047701 |
| 16 | −0.010039 | −0.053619 | 0.003308 | −0.039463 | −0.025347 | 0.03717 | −0.016381 | −0.040918 | 0.029134 | −0.024604 | −0.059066 | −0.007328 | 0.020433 | 0.002847 |
| 17 | −0.024616 | 0.051026 | −0.004759 | −0.011758 | −0.026107 | 0.04193 | 0.043865 | −0.000609 | −0.059686 | 0.027762 | 0.023566 | 0.014307 | −0.052807 | −0.105692 |
| 18 | −0.007008 | 0.036104 | −0.008358 | 0.025869 | 0.023313 | −0.011175 | −0.004455 | 0.019113 | 0.043653 | 0.045989 | 0.007644 | 0.004811 | 0.023833 | −0.011118 |
| 19 | −0.01784 | −0.017445 | 0.030176 | 0.03653 | 0.024324 | −0.0225 | 0.125663 | −0.027059 | 0.02314 | 0.052306 | −0.019203 | 0.021561 | −0.002961 | 0.06223 |
| 20 | 0.10308 | −0.033028 | 0.002999 | −0.081156 | −0.094695 | 0.014609 | −0.062843 | 0.02284 | −0.129502 | −0.100435 | −0.000642 | −0.079214 | −0.061983 | 0.017669 |
| 21 | 0.049461 | 0.035281 | 0.00263 | −0.010859 | 0.027781 | 0.020433 | 0.05384 | 0.060099 | −0.006257 | −0.006345 | 0.003712 | 0.06623 | −0.03497 | 0.040311 |
| 22 | −0.055691 | −0.026172 | −0.041326 | −0.036084 | −0.032583 | 0.009894 | −0.158375 | 0.051197 | −0.00294 | 0.056582 | 0.054486 | −0.042597 | 0.007922 | 0.124896 |
| 23 | 0.030181 | 0.086334 | 0.049126 | −0.057547 | −0.024561 | −0.015965 | 0.001508 | −0.033962 | 0.013198 | −0.00244 | 0.048537 | −0.023804 | 0.004895 | −0.071222 |
| 24 | 0.001967 | 0.027433 | 0.047081 | −0.062588 | −0.069279 | 0.028793 | −0.039279 | 0.02228 | 0.027159 | 0.018245 | −0.056668 | −0.04926 | 0.035048 | −0.059364 |
| 25 | −0.033579 | 0.044473 | 0.043181 | 0.036065 | 0.046085 | 0.043211 | 0.042512 | 0.094593 | −0.006848 | −0.054301 | 0.028453 | −0.002148 | 0.00071 | 0.069263 |
| 26 | 0.034745 | 0.000535 | −0.041735 | −0.018735 | −0.014635 | −0.015823 | −0.121239 | 0.00962 | −0.015844 | −0.055992 | 0.029115 | 0.109344 | 0.042439 | 0.054775 |
| 27 | 0.047624 | 0.028225 | −0.003184 | 0.065147 | 0.041025 | −0.052262 | −0.066983 | 0.049852 | −0.105991 | −0.072241 | −0.04153 | 0.042668 | −0.052402 | −0.012319 |
| 28 | −0.013549 | 0.016812 | 0.04646 | −0.060345 | −0.097571 | 0.037644 | −0.022038 | 0.0582 | −0.10036 | 0.064791 | −0.044199 | 0.042169 | −0.03628 | −0.004136 |
| 29 | −0.010985 | −0.046413 | −0.021634 | 0.100044 | 0.094888 | −0.033101 | 0.042351 | −0.019355 | 0.032331 | 0.008924 | −0.043192 | −0.060126 | −0.017698 | −0.001908 |
| 30 | −0.008182 | −0.028904 | 0.071167 | −0.004211 | −0.016697 | −0.124252 | −0.045278 | −0.082835 | −0.049501 | −0.010845 | −0.094262 | −0.011811 | 0.026414 | −0.058896 |
| 31 | −0.044261 | −0.011545 | −0.013795 | −0.017941 | −0.044571 | 0.035127 | 0.080841 | −0.023724 | −0.087178 | −0.023391 | 0.06698 | −0.83458 | 0.011534 | 0.140685 |
| 32 | 0.050709 | 0.049699 | 0.101728 | 0.022997 | 0.057341 | −0.007892 | 0.015727 | −0.101584 | 0.071498 | 0.040582 | −0.063809 | −0.028255 | −0.013704 | −0.113359 |
| 33 | −0.064512 | −0.063638 | −0.140793 | 0.03956 | 0.060089 | 0.063528 | 0.103818 | −0.099236 | 0.078244 | 0.004482 | 0.048316 | −0.036539 | −0.057053 | −0.09017 |
| 34 | −0.020123 | 0.052985 | 0.04484 | 0.067918 | 0.04777 | −0.073092 | 0.058782 | −0.054398 | 0.15313 | 0.06921 | 0.038436 | 0.030439 | 0.03208 | −0.025076 |
| 35 | 0.040627 | 0.002786 | −0.026943 | −0.08018 | −0.098014 | 0.007654 | 0.017448 | −0.015981 | 0.023255 | −0.108623 | 0.095342 | −0.103941 | −0.068845 | 0.009161 |
| 36 | 0.003972 | −0.076733 | −0.052855 | 0.076216 | 0.080652 | −0.002699 | 0.014017 | 0.020535 | 0.055185 | 0.04 | 0.004069 | 0.095673 | −0.047345 | −0.168567 |
| 37 | 0.008818 | 0.000779 | 0.031429 | −0.14452 | −0.137377 | 0.030269 | −0.03218 | 0.001458 | −0.022344 | −0.042094 | 0.021616 | −0.046575 | 0.151787 | 0.023968 |
| 38 | −0.003178 | −0.016734 | 0.061112 | −0.034211 | −0.012075 | 0.000417 | 0.010563 | −0.0374 | −0.049793 | −0.019892 | 0.03249 | 0.042483 | −0.139065 | −0.060794 |
| 39 | −0.011099 | 0.004562 | 0.0064391 | 0.028911 | 0.000379 | −0.021213 | 0.008321 | 0.091797 | −0.10054 | −0.029393 | 0.088858 | −0.010795 | −0.02772 | 0.024928 |
| 40 | 0.047436 | −0.025807 | 0.052978 | −0.09275 | −0.050355 | 0.077882 | 0.03967 | 0.032947 | 0.033911 | 0.023838 | 0.079142 | −0.013703 | 0.020993 | 0.017521 |
| 41 | 0.081964 | 0.013879 | −0.023735 | 0.01595 | 0.000707 | −0.002097 | −0.252445 | −0.076512 | 0.100614 | −0.055602 | −0.016082 | −0.076341 | −0.085952 | −0.025795 |
| 42 | −0.144054 | −0.138093 | −0.062287 | 0.033822 | −0.020042 | 0.006592 | 0.078518 | −0.029216 | 0.028893 | 0.045892 | −0.067582 | 0.017995 | 0.098153 | −0.060105 |
| 43 | 0.028469 | 0.022753 | −0.006191 | 0.023492 | −0.000209 | −0.044417 | 0.043635 | −0.033212 | −0.071849 | 0.020141 | 0.119494 | −0.07988 | −0.00414 | 0.0829 |
| 44 | 0.013776 | 0.036108 | 0.007319 | 0.073882 | 0.054306 | 0.030297 | 0.109536 | −0.029585 | −0.025921 | 0.044365 | −0.037779 | 0.069632 | −0.049685 | −0.082579 |
| 45 | 0.008364 | 0.018584 | 0.031948 | 0.069317 | 0.077129 | −0.040815 | 0.024423 | −0.094938 | −0.046895 | −0.024103 | 0.013387 | 0.04938 | −0.042688 | 0.146846 |
| 46 | −0.024665 | −0.006484 | −0.080537 | −0.030817 | 0.003905 | −0.065309 | −0.017644 | 0.052443 | −0.024517 | −0.034874 | −0.035105 | 0.169093 | 0.008865 | −0.071389 |
| 47 | 0.002755 | −0.034693 | −0.001621 | 0.01577 | 0.00916 | 0.000326 | 0.062437 | −0.002091 | 0.031227 | −0.242898 | −0.013032 | 0.030478 | 0.073183 | 0.015626 |
| 48 | 0.005596 | 0.041472 | 0.011494 | −0.01864 | −0.015991 | 0.070239 | 0.015385 | −0.00658 | 0.034913 | −0.027843 | 0.017863 | 0.039845 | −0.034545 | 0.044829 |
| 49 | −0.017289 | 0.068745 | 0.031257 | 0.068422 | 0.123238 | 0.061737 | 0.172748 | −0.023563 | 0.010871 | 0.003396 | 0.145957 | 0.005738 | 0.048282 | 0.058407 |
| 50 | −0.025051 | −0.011913 | 0.066646 | 0.033678 | 0.027295 | −0.098568 | 0.004973 | 0.012625 | −0.005812 | 0.085622 | 0.143403 | 0.012264 | −0.13439 | −0.072183 |
| 51 | 0.074879 | 0.05152 | −0.009846 | 0.003286 | 0.004981 | 0.009113 | 0.003297 | −0.031821 | 0.014847 | −0.070456 | −0.069255 | 0.018399 | −0.025896 | 0.011096 |
| 52 | 0.111508 | −0.006787 | 0.020744 | 0.055048 | 0.043176 | −0.046608 | −0.086579 | −0.034271 | −0.000517 | 0.030078 | −0.003068 | −0.040068 | 0.010968 | −0.025862 |
| 53 | 0.031548 | −0.027352 | 0.015642 | −0.037323 | −0.011136 | −0.014827 | 0.063219 | −0.043044 | −0.123722 | 0.023222 | 0.167388 | −0.058403 | 0.021926 | 0.005382 |
| 54 | 0.041678 | −0.011791 | 0.030864 | −0.031943 | 0.004863 | 0.03025 | −0.093245 | 0.076786 | 0.146721 | −0.0202 | 0.007568 | 0.046584 | 0.065516 | 0.152466 |
| 55 | 0.077591 | −0.021691 | −0.022896 | −0.076423 | −0.026578 | 0.038852 | 0.008116 | 0.011055 | 0.007336 | 0.046839 | −0.083241 | 0.061959 | 0.014067 | 0.032368 |
| 56 | 0.082456 | 0.019213 | −0.069727 | −0.064322 | −0.089364 | 0.05494 | −0.043215 | 0.019785 | 0.038929 | 0.053787 | −0.04989 | 0.020795 | −0.009224 | 0.037669 |
| 57 | −0.129203 | 0.042378 | 0.013093 | −0.04193 | 0.00481 | −0.028109 | −0.095803 | −0.101816 | −0.104342 | −0.024097 | −0.133997 | −0.140976 | −0.057683 | 0.017945 |
| 58 | 0.032307 | −0.032781 | −0.007606 | −0.006211 | −0.012758 | −0.024696 | 0.103934 | 0.037898 | −0.138386 | −0.033044 | 0.01111 | −0.07009 | 0.019562 | 0.010962 |
| 59 | −0.038119 | −0.011325 | −0.040592 | 0.010951 | 0.014882 | 0.020706 | −0.00679 | 0.027438 | 0.016659 | 0.053275 | −0.014739 | 0.037244 | 0.002693 | 0.017572 |
| 60 | 0.003053 | 0.06533 | 0.065582 | −0.022577 | −0.038808 | 0.041899 | 0.027021 | 0.025052 | 0.041267 | 0.037176 | 0.000506 | −0.154107 | −0.043585 | 0.053513 |
| 61 | 0.012019 | −0.020834 | −0.03668 | −0.204837 | −0.113224 | −0.015612 | 0.038001 | 0.004688 | 0.039439 | 0.050998 | 0.093834 | −0.018613 | −0.03369 | −0.014376 |
| 62 | −0.017185 | −0.013786 | 0.001248 | 0.044222 | −0.006167 | 0.011241 | −0.013015 | −0.05242 | −0.012745 | 0.019996 | 0.02509 | −0.026821 | −0.029805 | −0.046626 |
| 63 | 0.02447 | 0.021351 | 0.024984 | 0.019763 | −0.000675 | −0.012331 | 0.03466 | 0.012581 | −0.075609 | −0.041389 | 0.037793 | −0.140931 | −0.028418 | −0.012902 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 64 | −0.010694 | −0.023726 | −0.04285 | 0.00006 | 0.017977 | 0.015192 | −0.041287 | −0.047998 | −0.04226 | 0.008967 | −0.0101 | −0.001182 | −0.007928 | −0.046826 |
| 65 | −0.158388 | −0.005599 | 0.015295 | 0.019086 | 0.002172 | −0.017196 | −0.005668 | 0.105293 | −0.002899 | −0.050019 | 0.073127 | 0.176269 | 0.008989 | −0.049021 |
| 66 | 0.032093 | 0.012381 | 0.034156 | 0.091419 | 0.057001 | 0.052564 | −0.017835 | 0.14939 | 0.049016 | −0.021119 | −0.063345 | −0.048549 | −0.027119 | −0.027671 |
| 67 | −0.033692 | −0.072965 | 0.023762 | −0.025876 | −0.022451 | −0.02707 | −0.075822 | −0.099354 | 0.010626 | −0.023131 | 0.056605 | −0.038052 | 0.083665 | 0.033121 |
| 68 | 0.025186 | 0.036583 | 0.017401 | −0.002991 | 0.001725 | −0.005862 | 0.01542 | −0.027808 | −0.021936 | 0.017778 | 0.049141 | −0.037005 | 0.054932 | −0.05624 |
| 69 | 0.000769 | 0.024827 | 0.063346 | −0.028262 | −0.054279 | 0.014388 | −0.083422 | −0.063033 | −0.108168 | −0.03568 | −0.05295/ | −0.058991 | −0.089102 | 0.04937 |
| 70 | 0.056555 | 0.047588 | −0.033075 | 0.004125 | 0.012852 | 0.015838 | 0.067874 | −0.083997 | 0.040872 | 0.048782 | 0.080132 | −0.006531 | 0.011509 | −0.032228 |
| 71 | −0.031553 | 0.006531 | 0.107445 | −0.037768 | −0.025369 | 0.030947 | 0.021231 | −0.008152 | 0.081328 | −0.025428 | 0.029002 | −0.035744 | 0.015203 | −0.0123 |
| 72 | 0.047955 | −0.033607 | −0.072905 | 0.082344 | 0.031575 | −0.07693 | 0.043787 | −0.045952 | 0.061029 | −0.090252 | −0.079889 | 0.018866 | 0.008924 | −0.13283 |
| 73 | −0.046932 | 0.028111 | 0.026923 | 0.047477 | 0.061732 | 0.066453 | 0.034625 | 0.031115 | 0.045083 | 0.039463 | −0.039625 | −0.126551 | 0.089592 | −0.016221 |
| 74 | 0.017117 | −0.02971 | −0.044902 | −0.0635 | −0.011547 | 0.011341 | −0.046743 | 0.008493 | −0.01015 | −0.000831 | 0.057622 | −0.040253 | −0.003992 | −0.012725 |
| 75 | 0.015286 | −0.006831 | −0.058231 | 0.023727 | 0.015177 | −0.063308 | −0.050899 | −0.104339 | 0.01931 | −0.015445 | −0.049119 | 0.034093 | 0.108463 | 0.079398 |
| 76 | −0.028575 | 0.024439 | 0.074314 | −0.043438 | −0.050618 | −0.022894 | −0.077521 | 0.010258 | −0.051279 | −0.036452 | 0.073717 | 0.128893 | 0.059673 | 0.104064 |
| 77 | 0.036698 | −0.050348 | −0.090001 | −0.019763 | −0.009906 | 0.059063 | 0.171158 | −0.056778 | −0.105563 | −0.059541 | 0.189435 | 0.02355 | 0.000857 | −0.088155 |
| 78 | 0.072174 | 0.010184 | 0.008392 | 0.053925 | 0.084346 | −0.023729 | −0.042171 | 0.01795 | 0.017413 | 0.044025 | −0.112609 | −0.084366 | 0.037148 | −0.001765 |
| 79 | −0.053174 | 0.004809 | 0.027929 | 0.004225 | 0.041043 | 0.02533 | 0.020562 | 0.057916 | 0.032262 | 0.049598 | −0.066331 | −0.092865 | −0.090318 | 0.003244 |
| 80 | −0.020679 | 0.021699 | 0.070456 | 0.029655 | −0.002908 | −0.048015 | −0.114765 | 0.065266 | −0.066965 | 0.00035 | −0.110025 | 0.0971 | −0.020953 | −0.030958 |
| 81 | −0.02058 | −0.004553 | −0.01897 | 0.005228 | 0.009212 | −0.028372 | 0.042223 | −0.000763 | 0.086117 | 0.024376 | −0.103045 | 0.013052 | 0.060248 | −0.028085 |
| 82 | 0.026384 | 0.117129 | 0.063946 | 0.022098 | 0.01476 | −0.030543 | −0.039489 | −0.041882 | −0.069865 | −0.013376 | −0.015975 | −0.012073 | −0.08779 | −0.0463 |
| 83 | 0.016377 | 0.035475 | −0.007227 | −0.042742 | 0.004542 | −0.027139 | 0.061729 | −0.014229 | −0.007528 | 0.017103 | −0.124076 | −0.051141 | −0.025966 | 0.027715 |
| 84 | 0.036094 | 0.09943 | 0.044758 | −0.003968 | −0.004613 | 0.095755 | 0.020426 | 0.035092 | −0.014184 | 0.083381 | −0.000217 | 0.065416 | 0.108415 | 0.080504 |
| 85 | −0.033441 | 0.022896 | 0.066251 | −0.042672 | −0.032805 | −0.002765 | −0.002377 | 0.01145 | −0.058384 | 0.017484 | 0.027819 | −0.072598 | −0.086166 | 0.058709 |
| 86 | 0.050413 | −0.030294 | −0.06048 | −0.059588 | −0.03285 | 0.013386 | −0.069791 | 0.047006 | −0.018968 | 0.044767 | 0.135556 | 0.0725 | −0.052606 | 0.005885 |
| 87 | 0.064762 | −0.010261 | −0.042343 | 0.015047 | 0.015822 | 0.007139 | −0.087653 | 0.022865 | −0.005254 | 0.032701 | 0.015368 | 0.025238 | −0.065371 | 0.039351 |
| 88 | −0.003647 | 0.091774 | 0.078754 | −0.037662 | 0.002559 | −0.020158 | 0.086569 | −0.024636 | 0.10136 | 0.080019 | 0.039092 | 0.320146 | 0.051565 | −0.077643 |
| 89 | −0.036825 | −0.021359 | −0.043399 | 0.002492 | 0.059336 | 0.022744 | −0.011977 | −0.05101 | −0.067486 | −0.090631 | −0.001507 | −0.104765 | 0.04591 | −0.044411 |
| 90 | 0.00134 | −0.032424 | 0.00235 | 0.06787 | 0.066663 | −0.008048 | 0.039058 | 0.017296 | 0.033457 | −0.053597 | 0.153318 | −0.033175 | −0.010856 | −0.075068 |
| 91 | −0.042281 | 0.028568 | 0.014897 | −0.047079 | −0.065018 | −0.091631 | −0.045967 | 0.04133 | 0.112223 | 0.051813 | 0.008882 | −0.0729 | 0.066995 | −0.017699 |
| 92 | −0.04269 | −0.096156 | −0.067515 | 0.101054 | 0.072655 | −0.020849 | 0.063225 | 0.043758 | 0.049548 | −0.035022 | −0.043033 | 0.005985 | −0.000581 | 0.047693 |
| 93 | −0.009705 | 0.011796 | −0.004518 | −0.033956 | −0.05299 | 0.0393 | −0.001341 | 0.044388 | −0.002005 | 0.054374 | −0.004136 | −0.022958 | −0.001876 | 0.051196 |
| 94 | −0.024428 | −0.063291 | −0.056626 | −0.041298 | −0.017653 | −0.018205 | 0.015791 | −0.022602 | 0.004558 | −0.019958 | −0.017745 | −0.087688 | 0.048158 | 0.054495 |
| 95 | −0.01807 | −0.004561 | −0.011056 | −0.015378 | −0.022082 | −0.073815 | −0.028875 | −0.043401 | −0.091582 | 0.016926 | −0.030928 | 0.062979 | −0.022976 | −0.004269 |
| 96 | −0.001249 | 0.001125 | 0.016509 | −0.011003 | 0.0104 | 0.011472 | 0.011276 | −0.01025 | 0.049247 | 0.025189 | −0.076763 | −0.00327 | −0.040581 | 0.007666 |
| 97 | 0.023534 | 0.005618 | −0.000492 | −0.017639 | −0.014334 | −0.016382 | 0.024551 | 0.039073 | −0.093303 | 0.021298 | −0.007731 | 0.045022 | 0.03326 | −0.024389 |
| 98 | −0.004099 | −0.063037 | −0.041412 | 0.038272 | −0.039052 | −0.063775 | 0.047205 | −0.036034 | −0.027102 | 0.078036 | 0.142618 | −0.082088 | 0.006599 | −0.051659 |
| 99 | 0.073365 | 0.065248 | 0.051149 | 0.06447 | 0.03539 | 0.017217 | −0.010552 | −0.053769 | 0.024052 | 0.027752 | 0.027999 | −0.068412 | 0.009851 | 0.073062 |
| 10 | −0.005339 | −0.048084 | −0.003433 | −0.069386 | −0.052432 | 0.012081 | 0.036964 | −0.008922 | −0.014517 | −0.010796 | −0.025914 | −0.062022 | 0.072107 | 0.054653 |
| 101 | −0.006223 | −0.034381 | −0.035031 | −0.06564 | −0.057782 | 0.029673 | 0.00299 | 0.089087 | −0.011873 | −0.041 | 0.004619 | −0.048343 | −0.029187 | −0.081181 |
| 102 | −0.014174 | −0.008874 | −0.009017 | 0.015888 | 0.01571 | −0.024305 | −0.095583 | 0.017806 | 0.000729 | −0.018786 | 0.023934 | 0.069148 | 0.052926 | −0.054336 |
| 103 | 0.017071 | 0.016158 | −0.016438 | 0.042944 | 0.023811 | 0.050247 | 0.004182 | 0.074409 | −0.021102 | −0.029348 | −0.00777 | −0.02905 | −0.046733 | 0.04039 |
| 104 | −0.001361 | 0.007287 | 0.016817 | −0.017802 | 0.005593 | −0.002791 | −0.045869 | −0.090068 | 0.124866 | 0.008402 | 0.068459 | 0.090048 | −0.00625 | 0.008457 |
| 105 | −0.027126 | −0.051516 | −0.039809 | −0.028143 | −0.045004 | 0.013519 | −0.026669 | 0.034907 | 0.014208 | 0.031133 | −0.02286 | −0.016863 | 0.013979 | 0.06803 |
| 106 | 0.007061 | −0.056527 | 0.0327 | −0.100201 | −0.108054 | 0.040621 | −0.036816 | 0.029882 | 0.092845 | −0.018755 | 0.044203 | 0.022435 | 0.000214 | 0.047318 |
| 107 | −0.01344 | −0.015457 | −0.082889 | 0.161669 | 0.114356 | 0.054763 | −0.009762 | 0.003537 | −0.046612 | 0.013966 | 0.020942 | 0.062749 | 0.063218 | 0.074976 |
| 108 | 0.04705 | 0.040184 | 0.079944 | −0.034107 | −0.007371 | −0.000785 | −0.022789 | −0.069612 | 0.037605 | −0.024238 | 0.052333 | 0.018544 | 0.05558 | −0.025816 |
| 109 | −0.058165 | −0.043327 | −0.033332 | 0.003507 | −0.008277 | 0.000915 | −0.000731 | −0.027719 | −0.012628 | −0.004599 | −0.013416 | −0.058153 | −0.003354 | 0.007342 |
| 110 | −0.009865 | −0.032669 | −0.045801 | 0.045883 | 0.033854 | −0.008303 | 0.000729 | −0.073256 | −0.025848 | 0.017767 | 0.05256 | −0.023441 | −0.018152 | −0.031514 |
| 111 | −0.025737 | 0.037044 | 0.046954 | −0.034598 | −0.048197 | 0.035682 | −0.01884 | 0.035459 | −0.015891 | −0.03343 | −0.015065 | −0.01144 | 0.00854 | 0.044138 |
| 112 | −0.023137 | −0.015204 | −0.029472 | −0.007735 | 0.021367 | −0.003507 | 0.024079 | 0.08693 | −0.011117 | −0.01612 | −0.056625 | −0.109099 | 0.036065 | −0.00157 |
| 113 | −0.039776 | 0.034894 | −0.057754 | 0.005186 | −0.010851 | −0.055672 | 0.004239 | 0.007918 | 0.049311 | −0.013536 | −0.055112 | 0.050999 | −0.048826 | −0.047892 |
| 114 | −0.024193 | −0.009386 | 0.038422 | −0.025123 | −0.029162 | −0.00002 | −0.019197 | −0.00314 | −0.010299 | 0.016724 | −0.037136 | 0.036875 | 0.010391 | −0.048556 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 115 | 0.015658 | 0.030845 | −0.037654 | −0.033691 | −0.018362 | −0.026616 | −0.007385 | −0.016631 | 0.047603 | 0.003362 | −0.071673 | 0.054082 | −0.008488 | −0.035354 |
| 116 | 0.000236 | −0.008781 | 0.047058 | −0.040803 | −0.038344 | −0.024588 | 0.058987 | 0.028735 | 0.040329 | 0.004112 | −0.023037 | 0.003934 | 0.001896 | 0.048975 |
| 117 | 0.062767 | 0.029191 | −0.015812 | 0.002572 | 0.024956 | 0.011635 | 0.0035 | 0.016736 | −0.011032 | 0.003727 | 0.001213 | −0.054325 | −0.004198 | 0.095289 |
| 118 | 0.008458 | −0.033893 | −0.016541 | −0.049619 | −0.057835 | 0.029018 | −0.070982 | 0.008112 | 0.052222 | −0.006166 | −0.061749 | −0.094035 | 0.016771 | −0.006474 |
| 119 | 0.033619 | −0.017721 | 0.086858 | −0.000582 | −0.017236 | −0.019405 | 0.109 | 0.033433 | −0.038121 | 0.023062 | −0.057932 | 0.048097 | 0.004042 | 0.063683 |
| 120 | 0.02374 | 0.05095 | 0.026764 | 0.024804 | 0.042353 | 0.012058 | −0.02679 | −0.053929 | 0.000091 | 0.072401 | 0.009688 | −0.116767 | −0.015379 | −0.004838 |
| 121 | −0.014901 | 0.017824 | 0.028432 | −0.026776 | −0.033996 | −0.016575 | −0.027096 | −0.025488 | −0.008247 | −0.023398 | 0.076799 | 0.096374 | 0.048432 | −0.064579 |
| 122 | 0.084638 | −0.035447 | −0.074804 | 0.016401 | −0.030978 | −0.051592 | −0.020391 | 0.0345 | −0.024517 | −0.083723 | 0.062163 | −0.032062 | −0.014345 | 0.070177 |
| 123 | −0.00741 | 0.018987 | −0.024684 | −0.022866 | 0.017892 | −0.056225 | 0.053781 | −0.110731 | 0.065811 | 0.017923 | 0.025192 | 0.021697 | 0.084133 | −0.003388 |
| 124 | −0.063172 | 0.068951 | 0.010718 | 0.050586 | 0.076839 | 0.006242 | −0.020203 | −0.009505 | 0.003934 | −0.007701 | −0.016653 | −0.011054 | −0.072115 | −0.005854 |
| 125 | −0.002598 | −0.03502 | −0.023176 | −0.014165 | 0.027 | −0.048151 | 0.086654 | 0.120773 | −0.004396 | −0.030292 | −0.034756 | −0.050554 | −0.037584 | −0.009181 |
| 126 | −0.069456 | 0.059623 | 0.132628 | −0.049794 | −0.060116 | 0.011144 | −0.02486 | −0.040842 | −0.111584 | −0.015543 | 0.06306 | 0.085394 | 0.074311 | 0.018546 |
| 127 | 0.008187 | 0.01019 | −0.004304 | −0.063638 | −0.032194 | 0.094926 | −0.047738 | −0.008167 | −0.064778 | 0.048443 | 0.127383 | −0.042658 | −0.128091 | −0.005552 |
| 128 | 0.063996 | 0.031449 | 0.063289 | −0.021372 | −0.040486 | 0.003102 | 0.0307 | 0.047625 | −0.048092 | −0.006347 | −0.050804 | 0.003276 | 0.007168 | −0.059438 |
| 129 | 0.013659 | 0.062022 | 0.014943 | 0.011348 | −0.022364 | −0.035583 | 0.009379 | −0.085119 | 0.008256 | −0.027021 | 0.020989 | 0.067722 | 0.012391 | 0.01555 |
| 130 | 0.038763 | 0.015422 | −0.024477 | −0.036613 | −0.025193 | 0.023132 | −0.026683 | 0.035045 | −0.010704 | 0.011924 | −0.005047 | 0.059475 | 0.039214 | −0.016504 |
| 131 | −0.016108 | 0.030902 | 0.044457 | −0.060853 | −0.037311 | −0.009896 | −0.016672 | 0.040324 | 0.014068 | −0.000805 | 0.033758 | 0.003809 | −0.006326 | −0.024269 |
| 132 | −0.009226 | −0.020867 | −0.037126 | −0.012968 | −0.022235 | −0.021731 | −0.051042 | 0.000088 | 0.031748 | 0.040271 | −0.01628 | −0.067414 | 0.038286 | −0.013761 |
| 133 | 0.039333 | −0.038524 | −0.074858 | −0.012507 | −0.056837 | 0.006631 | 0.04389 | 0.013588 | −0.000508 | −0.026092 | 0.008654 | 0.091212 | 0.043205 | −0.00294 |
| 134 | −0.006035 | −0.00918 | 0.024566 | 0.02157 | −0.035732 | −0.01131 | −0.034098 | 0.002479 | −0.003316 | −0.01198 | −0.085825 | 0.074914 | −0.05452 | 0.006927 |
| 135 | −0.000861 | 0.006226 | 0.056893 | 0.030275 | 0.015876 | 0.043372 | 0.034894 | −0.076292 | −0.109625 | −0.017767 | −0.084725 | 0.025321 | −0.030568 | −0.01108 |
| 136 | −0.028002 | −0.030878 | −0.003238 | −0.032797 | −0.001645 | 0.042618 | −0.022871 | −0.034326 | −0.031537 | −0.008439 | 0.010524 | −0.013284 | 0.030546 | 0.028274 |
| 137 | −0.038587 | −0.015472 | 0.074221 | 0.098259 | 0.063517 | 0.025537 | 0.027261 | −0.10899 | 0.08955 | −0.02896 | 0.013931 | −0.12479 | −0.09681 | 0.07394 |
| 138 | −0.023692 | −0.044973 | 0.023035 | −0.006638 | −0.00616 | −0.005173 | −0.036201 | −0.015442 | 0.035053 | 0.031569 | 0.060036 | −0.019387 | −0.036811 | 0.05674 |
| 139 | −0.067158 | −0.044848 | 0.041704 | −0.035892 | −0.033284 | 0.029922 | −0.027483 | 0.048632 | −0.010586 | −0.002108 | −0.01213 | 0.042608 | −0.043185 | 0.06349 |
| 140 | −0.010214 | 0.001358 | 0.017631 | −0.018166 | −0.015574 | 0.030026 | −0.006219 | 0.009745 | −0.007591 | 0.014447 | −0.051459 | 0.02415 | −0.027203 | −0.028315 |
| 141 | −0.010473 | −0.036114 | −0.020159 | −0.009531 | 0.025669 | −0.009503 | −0.04311 | 0.036319 | 0.042793 | −0.000962 | −0.006981 | −0.005446 | −0.044309 | 0.012669 |
| 142 | −0.001971 | 0.046735 | 0.017603 | 0.023401 | 0.029568 | 0.021355 | −0.042066 | 0.022351 | −0.019367 | 0.019249 | 0.029565 | 0.0113 | 0.004966 | −0.052393 |
| 143 | −0.00732 | 0.018278 | 0.002103 | 0.009957 | −0.026743 | −0.016322 | −0.005526 | −0.021739 | −0.031188 | 0.01935 | 0.055029 | −0.022763 | −0.015056 | −0.018399 |
| 144 | 0.059269 | 0.036224 | 0.027799 | 0.022594 | 0.03583 | 0.01606 | 0.042899 | 0.040774 | 0.049002 | −0.004053 | 0.033906 | 0.0194 | 0.017632 | 0.003015 |
| 145 | 0.008036 | 0.001825 | 0.01935 | 0.017306 | 0.013865 | −0.007005 | −0.019743 | −0.008189 | 0.06239 | 0.007976 | 0.018658 | −0.000284 | −0.011681 | −0.012102 |
| 146 | −0.029822 | 0.012806 | 0.016651 | −0.0008 | 0.001857 | −0.021094 | −0.034619 | 0.001575 | 0.016475 | −0.032729 | −0.015663 | 0.029193 | −0.006858 | −0.032757 |
| 147 | −0.002066 | −0.015995 | −0.019929 | 0.036602 | 0.050471 | 0.026501 | 0.005553 | −0.010832 | 0.013189 | 0.003125 | −0.056867 | −0.073092 | 0.020389 | 0.044532 |
| 148 | −0.059204 | −0.055194 | 0.009397 | −0.006547 | −0.002682 | −0.03976 | 0.004435 | 0.011049 | −0.031795 | −0.013728 | 0.051019 | −0.029473 | 0.009171 | 0.040083 |
| 149 | −0.056818 | −0.014024 | −0.010568 | −0.011652 | −0.017026 | 0.024563 | 0.042406 | −0.049047 | −0.008423 | 0.013108 | −0.035838 | −0.012269 | −0.003208 | −0.016674 |
| 150 | −0.006525 | −0.007193 | 0.006409 | 0.003641 | −0.018557 | 0.037876 | −0.010047 | −0.057481 | −0.058578 | −0.020282 | −0.007262 | −0.003953 | −0.012008 | −0.074976 |
| 151 | 0.073685 | 0.008505 | −0.027768 | −0.001685 | 0.016018 | 0.029999 | 0.008855 | −0.009102 | −0.062023 | 0.036716 | 0.032014 | −0.008299 | −0.009669 | −0.014349 |
| 152 | 0.011848 | −0.014187 | −0.013404 | −0.024578 | −0.040835 | −0.004969 | −0.005138 | −0.04372 | −0.010525 | 0.010548 | −0.026909 | −0.010419 | 0.033846 | 0.012301 |
| 153 | −0.022421 | 0.010923 | −0.051972 | 0.024399 | 0.037864 | −0.031639 | 0.02963 | 0.000764 | 0.021825 | −0.001899 | −0.019845 | −0.018956 | −0.024743 | −0.010217 |
| 154 | −0.021655 | −0.019678 | −0.004789 | 0.040551 | 0.034938 | −0.029195 | −0.024602 | 0.016955 | −0.030111 | −0.029049 | 0.016357 | 0.003672 | 0.011452 | 0.015158 |
| 155 | −0.00228 | −0.018459 | −0.007955 | 0.022031 | −0.009335 | −0.0051 | 0.034392 | −0.029054 | 0.04826 | 0.043558 | 0.033411 | 0.001041 | 0.007488 | −0.007269 |
| 156 | −0.054226 | −0.008904 | 0.003742 | −0.014925 | −0.017199 | 0.001567 | 0.027279 | 0.085805 | 0.010453 | 0.011806 | 0.009 | −0.007364 | −0.014578 | −0.00428 |
| 157 | −0.024599 | −0.014552 | 0.004547 | −0.006517 | −0.032385 | 0.029055 | 0.008333 | 0.1037 | −0.037768 | 0.02056 | −0.018152 | −0.008692 | 0.040477 | 0.065906 |
| 158 | −0.003275 | −0.045512 | −0.054341 | −0.006589 | −0.012726 | −0.000432 | 0.029017 | 0.040896 | 0.038856 | 0.024272 | −0.036334 | −0.050854 | 0.006865 | −0.034591 |
| 159 | 0.026479 | −0.003871 | −0.007117 | −0.017047 | 0.012051 | 0.026486 | −0.032376 | 0.011809 | −0.03557 | 0.002393 | −0.00413 | −0.02213 | 0.007187 | −0.003626 |
| 160 | 0.0247 | −0.024012 | 0.004885 | 0.019024 | 0.007641 | −0.017613 | 0.004048 | −0.024615 | 0.025985 | 0.00373 | −0.004042 | −0.027382 | −0.009681 | −0.024771 |
| 161 | 0.054381 | 0.047714 | 0.001631 | 0.023336 | 0.044356 | −0.019272 | 0.004907 | 0.02398 | 0.050157 | 0.001745 | 0.009084 | 0.043139 | 0.015324 | −0.012524 |
| 162 | −0.014241 | −0.049999 | −0.008978 | 0.053979 | 0.049934 | −0.002235 | −0.039694 | 0.015596 | −0.077053 | 0.020473 | 0.065882 | 0.010257 | 0.012778 | −0.006532 |
| 163 | 0.018023 | −0.018656 | 0.003424 | 0.034936 | 0.014646 | −0.01203 | 0.039614 | −0.026966 | 0.044011 | 0.013259 | −0.044218 | 0.022215 | 0.009183 | −0.04533 |
| 164 | 0.013415 | 0.030866 | −0.014028 | −0.01244 | 0.00764 | 0.04339 | 0.037405 | −0.000742 | 0.00387 | −0.005597 | 0.024742 | 0.077771 | 0.017986 | −0.010614 |
| 165 | −0.024021 | −0.006325 | −0.02714 | −0.034058 | −0.017583 | −0.003329 | 0.023127 | 0.024203 | 0.017197 | 0.012814 | 0.029885 | −0.05085 | −0.031305 | 0.02436 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 166 | 0.010887 | 0.023405 | 0.022313 | −0.016733 | −0.0129 | −0.009406 | 0.001076 | −0.015549 | −0.012979 | 0.013448 | −0.015882 | −0.061843 | 0.008037 | 0.022332 |
| 167 | −0.000808 | −0.023724 | −0.074012 | −0.005714 | 0.00252 | 0.033357 | −0.032486 | 0.025856 | −0.000286 | 0.030666 | 0.014585 | 0.019073 | 0.014745 | 0.030018 |
| 168 | −0.023128 | −0.035827 | −0.037104 | −0.00104 | −0.007766 | −0.020508 | −0.011776 | −0.021906 | 0.003784 | −0.096275 | 0.027013 | −0.020542 | 0.002113 | −0.066501 |
| 169 | 0.00999 | 0.021736 | 0.006875 | 0.011333 | 0.013168 | 0.015728 | −0.022382 | −0.001377 | −0.007144 | 0.009275 | −0.015572 | 0.020038 | −0.013258 | −0.012209 |
| 170 | 0.022502 | 0.035659 | 0.002635 | 0.011224 | 0.016438 | 0.007934 | 0.009309 | −0.040906 | −0.024376 | 0.014457 | 0.019056 | 0.031972 | −0.001885 | −0.031093 |
| 171 | 0.009411 | 0.003372 | −0.021167 | 0.006526 | 0.009535 | 0.012277 | −0.028115 | 0.025551 | 0.037455 | 0.029381 | 0.015559 | 0.011184 | −0.016322 | −0.022344 |
| 172 | −0.067687 | −0.020354 | −0.002812 | −0.001426 | −0.009917 | 0.017154 | −0.000574 | 0.001373 | −0.007744 | 0.009252 | −0.004592 | −0.051198 | −0.057455 | −0.015793 |
| 173 | −0.087643 | −0.054833 | −0.053112 | 0.003252 | 0.000841 | 0.004222 | 0.021583 | 0.040787 | 0.014339 | −0.008122 | 0.009379 | −0.012517 | 0.025792 | 0.006196 |
| 174 | 0.003326 | −0.019619 | −0.058933 | 0.016412 | 0.023854 | 0.052902 | 0.022862 | 0.017402 | 0.000084 | −0.01489 | 0.030184 | −0.018882 | 0.016161 | 0.00074 |
| 175 | 0.006729 | −0.024 | −0.049284 | −0.012459 | −0.031143 | 0.014087 | −0.019121 | −0.006682 | 0.023045 | 0.023916 | 0.00939 | 0.057948 | 0.020719 | 0.064359 |
| 176 | −0.021689 | 0.004115 | −0.058223 | −0.048554 | −0.025483 | −0.013282 | 0.013547 | −0.009193 | 0.061284 | 0.033113 | −0.019172 | −0.001677 | 0.025241 | −0.034553 |
| 177 | −0.001816 | −0.011635 | 0.019647 | 0.008411 | 0.01081 | −0.033446 | −0.041902 | 0.022136 | 0.02996 | −0.009503 | −0.02606 | −0.050509 | −0.036353 | 0.002016 |
| 178 | 0.024794 | −0.000934 | −0.008796 | −0.022142 | −0.001673 | 0.011495 | 0.041651 | −0.006308 | 0.003813 | 0.013626 | 0.052812 | 0.032571 | −0.019107 | −0.017171 |
| 179 | 0.016995 | 0.021878 | 0.01 | 0.003058 | 0.01064 | 0.013414 | −0.016821 | 0.007106 | 0.013018 | −0.016749 | 0.024112 | 0.01653 | −0.002486 | 0.015583 |
| 180 | 0.017233 | 0.025786 | 0.004888 | −0.02181 | 0.005953 | 0.022187 | 0.017726 | 0.014605 | 0.010138 | −0.004097 | 0.010619 | 0.032317 | 0.038676 | −0.007481 |
| 181 | 0.030209 | 0.024166 | −0.004802 | −0.015236 | 0.001227 | 0.002633 | 0.033904 | 0.007373 | −0.012365 | −0.006427 | −0.020749 | 0.047349 | 0.039525 | 0.013218 |
| 182 | 0.008864 | 0.031578 | 0.019936 | 0.020032 | 0.027594 | −0.007578 | 0.053665 | −0.035304 | −0.01325 | 0.001094 | −0.049225 | 0.036748 | 0.012761 | −0.018203 |
| 183 | −0.008766 | −0.009359 | 0.016317 | 0.034233 | 0.024908 | −0.022116 | −0.006536 | 0.013013 | 0.029829 | 0.016068 | 0.006998 | 0.009399 | −0.036978 | 0.025807 |
| 184 | 0.009826 | 0.010062 | 0.024006 | −0.035589 | −0.060377 | −0.011902 | −0.026715 | −0.005087 | −0.029302 | 0.054047 | −0.010051 | −0.00014 | −0.041762 | 0.007979 |
| 185 | −0.025428 | 0.007879 | 0.024813 | 0.004132 | 0.001924 | −0.045808 | −0.019582 | 0.028748 | 0.045786 | 0.012523 | 0.020374 | 0.057973 | −0.02419 | −0.001535 |
| 186 | 0.036128 | 0.019336 | 0.021604 | −0.019014 | −0.030875 | 0.011664 | 0.003005 | 0.059345 | −0.020172 | −0.002372 | 0.035858 | −0.058452 | 0.018383 | −0.001387 |
| 187 | 0.002425 | 0.049252 | 0.024129 | 0.004285 | 0.015983 | −0.004817 | 0.019629 | 0.029364 | −0.015717 | 0.030725 | −0.007739 | 0.068915 | −0.016882 | −0.026523 |
| 188 | 0.01789 | −0.008115 | 0.007674 | 0.05227 | 0.062318 | −0.012412 | 0.045894 | 0.012411 | 0.00271 | 0.021129 | 0.015479 | −0.020932 | −0.038734 | −0.008685 |
| 189 | 0.015634 | −0.017774 | 0.00161 | 0.020706 | 0.022097 | −0.036471 | 0.004377 | −0.002977 | 0.020501 | 0.011159 | −0.031551 | 0.002402 | 0.022206 | 0.034759 |
| 190 | 0.032086 | −0.003732 | −0.002316 | 0.027014 | 0.041121 | −0.025009 | 0.032541 | −0.021132 | 0.023009 | −0.001619 | 0.010735 | −0.009911 | 0.032046 | 0.001523 |
| 191 | −0.011405 | 0.037855 | 0.044405 | 0.043622 | 0.033501 | 0.0053 | 0.027006 | −0.007237 | −0.043625 | 0.002009 | 0.026429 | −0.028505 | −0.067813 | 0.048715 |
| 192 | 0.002073 | −0.046849 | 0.063841 | −0.055162 | −0.064501 | −0.014977 | 0.005786 | −0.043445 | 0.056171 | −0.019093 | 0.005724 | 0.083191 | 0.015508 | −0.028883 |
| 193 | 0.012125 | 0.001881 | −0.052118 | −0.022674 | −0.026738 | 0.012778 | −0.047862 | −0.011865 | −0.007975 | −0.020935 | −0.045532 | −0.03491 | −0.037234 | −0.012863 |
| 194 | 0.040261 | −0.019071 | −0.012772 | 0.032988 | 0.018817 | 0.03608 | −0.009558 | −0.052521 | −0.074382 | −0.031298 | 0.040646 | −0.050592 | −0.044447 | 0.042584 |
| 195 | −0.009315 | 0.009779 | −0.014524 | 0.021407 | 0.00933 | −0.005003 | −0.005196 | 0.020658 | −0.004787 | −0.002081 | −0.004462 | 0.007743 | 0.02014 | 0.021281 |
| 196 | −0.032549 | 0.005801 | 0.019081 | 0.006984 | 0.021885 | 0.008759 | −0.013766 | 0.022936 | 0.028405 | 0.026729 | −0.003997 | −0.058075 | 0.029537 | 0.021544 |
| 197 | −0.032111 | 0.020768 | 0.077394 | 0.024598 | 0.04205 | −0.005302 | 0.075001 | −0.076965 | 0.064508 | −0.034866 | −0.010896 | −0.076923 | 0.054461 | −0.003852 |
| 198 | 0.012999 | 0.037528 | −0.007049 | −0.008861 | −0.029626 | −0.020615 | 0.058408 | −0.019924 | 0.019221 | 0.002799 | 0.064559 | −0.033972 | −0.020602 | 0.027833 |
| 199 | 0.031157 | 0.055112 | 0.045903 | −0.054213 | −0.05725 | −0.027616 | −0.013842 | −0.006283 | 0.011305 | −0.025659 | −0.014301 | −0.008471 | −0.056972 | −0.056529 |
| 200 | 0.040539 | 0.032354 | 0.022019 | −0.016585 | 0.00179 | −0.000383 | −0.01228 | 0.017633 | −0.021561 | −0.028203 | 0.014644 | 0.052865 | −0.048782 | −0.05138 |
| 201 | 0.023842 | 0.059029 | 0.012819 | 0.030678 | 0.030975 | 0.005401 | −0.029876 | −0.006174 | 0.020563 | 0.003872 | 0.021312 | 0.014391 | −0.038057 | −0.023739 |
| 202 | 0.002554 | 0.015669 | 0.057627 | −0.023836 | −0.028264 | −0.008488 | 0.043401 | −0.05776 | 0.015008 | 0.006221 | 0.054642 | −0.037346 | −0.007215 | 0.000994 |
| 203 | 0.002232 | −0.006041 | 0.020399 | 0:077482 | 0.065984 | −0.002017 | −0.019928 | −0.036793 | −0.023108 | 0.006591 | 0.024514 | −0.016581 | −0.007235 | 0.002523 |
| 204 | 0.032043 | 0.044566 | −0.021701 | −0.028612 | −0.007657 | −0.003173 | −0.032917 | 0.015775 | −0.039646 | −0.013593 | −0.043071 | 0.033262 | 0.005753 | 0.037448 |
| 205 | −0.012545 | −0.00518 | −0.014271 | −0.002319 | −0.023368 | −0.009165 | −0.010747 | 0.009752 | 0.034777 | −0.040494 | −0.019763 | 0.01911 | 0.049068 | −0.003764 |
| 206 | 0.04227 | −0.039007 | −0.006065 | 0.012141 | −0.014321 | 0.051025 | −0.003908 | 0.106337 | 0.020178 | 0.038228 | −0.019858 | 0.040822 | −0.017199 | −0.019714 |
| 207 | −0.016335 | 0.024008 | 0.007326 | 0.027858 | 0.031189 | 0.035602 | −0.011756 | −0.084965 | −0.005184 | −0.020292 | 0.037849 | −0.031967 | 0.018148 | 0.014437 |
| 208 | 0.009053 | −0.051249 | −0.034627 | −0.020534 | −0.017312 | 0.012392 | −0.0021 | −0.059929 | −0.025294 | 0.004539 | 0.004334 | 0.016712 | 0.002288 | −0.065993 |
| 209 | 0.009045 | −0.029937 | 0.023012 | 0.028845 | 0.026598 | 0.026989 | 0.012567 | 0.036186 | −0.033751 | 0.023272 | −0.015554 | 0.021085 | 0.042799 | 0.030117 |
| 210 | 0.02215 | −0.01077 | −0.031141 | 0.006436 | 0.008626 | −0.042894 | −0.032968 | 0.001069 | 0.013315 | 0.005123 | −0.025653 | 0.018996 | 0.05082 | −0.013029 |
| 211 | −0.029956 | −0.009879 | 0.010086 | 0.018376 | 0.010475 | 0.007501 | 0.014774 | −0.035613 | 0.044497 | −0.032593 | 0.038616 | −0.008073 | 0.012066 | 0.023482 |
| 212 | 0.048091 | −0.030618 | −0.011519 | 0.034933 | 0.012508 | −0.013635 | 0.029683 | −0.008814 | −0.024329 | 0.042076 | −0.001099 | 0.016279 | −0.004202 | −0.031463 |
| 213 | 0.000676 | −0.002969 | −0.005815 | −0.009143 | 0.014642 | 0.00883 | −0.039303 | −0.050509 | −0.043641 | 0.024179 | 0.013827 | 0.018046 | −0.015132 | −0.038257 |
| 214 | −0.021019 | 0.000497 | 0.006591 | −0.002773 | 0.017095 | 0.013524 | −0.027678 | −0.002747 | 0.011579 | 0.008645 | 0.058518 | −0.041873 | −0.000229 | 0.013105 |
| 215 | −0.011786 | −0.000698 | −0.041234 | −0.046024 | −0.021173 | −0.022303 | −0.008919 | 0.03605 | 0.004316 | −0.047585 | 0.0866 | 0.051906 | 0.080357 | −0.032169 |
| 216 | −0.022451 | −0.009144 | −0.024119 | −0.023784 | −0.0244 | 0.008812 | −0.01322 | 0.0365 | −0.016479 | −0.055347 | −0.021869 | 0.028656 | −0.041967 | −0.019602 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 217 | 0.012272 | 0.007133 | 0.042064 | 0.018479 | 0.029073 | 0.04842 | 0.018712 | 0.069878 | 0.003603 | 0.07297 | 0.029933 | −0.012565 | −0.032589 | 0.047438 |
| 218 | −0.053901 | −0.010708 | −0.029842 | −0.026446 | −0.0168 | −0.011663 | 0.020736 | −0.033374 | −0.006589 | −0.001437 | 0.024928 | 0.022375 | 0.008277 | −0.002149 |
| 219 | −0.053687 | −0.0069 | −0.048756 | −0.026175 | −0.017568 | 0.001969 | −0.000385 | 0.057557 | 0.031371 | 0.051468 | 0.030881 | 0.020146 | −0.006089 | −0.029879 |
| 220 | 0.024362 | 0.030361 | −0.01021 | 0.001297 | 0.011574 | 0.018937 | −0.052694 | −0.002823 | −0.00707 | 0.045887 | 0.00667 | −0.045316 | −0.023343 | −0.010781 |
| 221 | 0.754754 | −0.066969 | −0.002428 | −0.000454 | −0.0099 | −0.001633 | 0.068693 | −0.002157 | 0.037689 | 0.013878 | 0.010036 | −0.009799 | 0.040628 | 0.033377 |
| 222 | −0.08938 | 0.755495 | −0.148771 | 0.007043 | 0.000569 | −0.010312 | 0.051225 | 0.036722 | 0.034559 | −0.009361 | 0.022749 | −0.071059 | 0.029676 | 0.032535 |
| 223 | −0.037865 | −0.145152 | 0.72267 | 0.0373 | 0.046076 | −0.009185 | 0.028908 | 0.023927 | 0.01128 | 0.011517 | 0.023559 | −0.008993 | 0.00545 | −0.016945 |
| 224 | 0.005558 | 0.023872 | 0.014262 | 0.610962 | −0.321353 | 0.030698 | −0.134181 | 0.0084 | −0.052435 | −0.014947 | 0.026676 | 0.022817 | 0.030637 | −0.011634 |
| 225 | −0.002201 | −0.002693 | 0.010851 | −0.323187 | 0.66277 | 0.014037 | −0.137894 | 0.012722 | −0.070415 | −0.02478 | −0.003159 | 0.016195 | 0.032172 | −0.005564 |
| 226 | −0.016158 | −0.024299 | 0.000757 | 0.055761 | 0.035543 | 0.805978 | −0.053769 | −0.053843 | 0.024753 | −0.006313 | −0.037975 | 0.012444 | 0.008598 | −0.035377 |
| 227 | 0.022992 | 0.021334 | 0.0267 | −0.113435 | −0.124994 | −0.034909 | 0.501226 | −0.009814 | −0.024113 | −0.022716 | −0.130607 | −0.002442 | −0.019061 | −0.002006 |
| 228 | 0.018 | 0.02508 | 0.0311 | 0.001713 | 0.010222 | −0.026579 | −0.013272 | 0.557824 | −0.039323 | −0.030978 | 0.014211 | −0.097999 | 0.02242 | −0.073439 |
| 229 | 0.00137 | 0.007982 | 0.032886 | −0.07298 | −0.09672 | 0.041817 | −0.00068 | −0.046853 | 0.507734 | −0.087885 | 0.045194 | −0.0534 | −0.031884 | 0.003662 |
| 230 | 0.008861 | −0.019119 | −0.00931 | −0.012156 | −0.014981 | −0.013171 | −0.044286 | −0.036224 | −0.089001 | 0.765528 | −0.030483 | −0.002718 | 0.024107 | −0.013457 |
| 231 | 0.013691 | 0.045849 | 0.022352 | 0.013569 | −0.019281 | −0.044599 | −0.102534 | 0.004789 | 0.039198 | −0.006201 | 0.484414 | −0.0241 | −0.016857 | −0.043839 |
| 232 | −0.02169 | −0.050367 | −0.013537 | 0.013924 | 0.008913 | 0.047764 | −0.001129 | −0.126144 | −0.031935 | 0.003824 | −0.026249 | 0.343734 | −0.098616 | 0.094183 |
| 233 | 0.017493 | 0.018448 | 0.029745 | 0.055479 | 0.048682 | 0.006846 | −0.054421 | −0.008755 | −0.067989 | 0.028559 | 0.026045 | −0.111693 | 0.650642 | −0.083222 |
| 234 | 0.017794 | 0.049097 | 0.026556 | −0.008449 | 0.018324 | −0.059722 | 0.017642 | −0.103836 | 0.012832 | −0.01043 | −0.032754 | 0.040087 | −0.069644 | 0.570752 |
| 235 | 0.001486 | 0.012721 | 0.061585 | −0.008944 | −0.00061 | 0.005881 | −0.047288 | −0.104209 | 0.029998 | 0.005837 | −0.069491 | −0.045431 | 0.034782 | −0.152448 |
| 236 | 0.007205 | 0.025084 | 0.008918 | 0.015637 | 0.01942 | 0.01841 | 0.011427 | −0.002883 | −0.008751 | −0.041793 | −0.02879 | −0.004876 | 0.016782 | −0.025229 |
| 237 | 0.075023 | 0.040502 | 0.019864 | 0.012613 | −0.017034 | 0.052531 | −0.004365 | 0.000919 | −0.019623 | −0.003662 | −0.024326 | 0.023716 | 0.036499 | 0.0269 |
| 238 | 0.033103 | 0.013078 | −0.003483 | −0.002324 | 0.000225 | 0.055102 | 0.007162 | 0.040968 | −0.00568 | −0.019233 | −0.033127 | 0.008418 | −0.031068 | −0.031125 |
| 239 | 0.005083 | 0.004615 | 0.012764 | 0.025742 | 0.010799 | 0.00869 | −0.007899 | −0.01252 | −0.002339 | −0.032888 | −0.073009 | −0.010003 | −0.042225 | −0.040476 |
| 240 | −0.006589 | 0.039247 | 0.042267 | 0.007297 | 0.020725 | 0.010412 | 0.025697 | 0.001301 | −0.002833 | 0.021107 | −0.001568 | 0.044843 | −0.039471 | −0.011416 |
| 241 | 0.044636 | 0.051119 | 0.043489 | 0.010749 | 0.017765 | 0.018666 | 0.004002 | −0.014209 | −0.059129 | 0.004867 | 0.034824 | −0.041349 | −0.146475 | −0.096188 |
| 242 | 0.009023 | −0.030533 | −0.014963 | 0.055449 | 0.035278 | 0.017505 | 0.021335 | −0.026538 | −0.007025 | 0.006158 | 0.034417 | −0.023144 | −0.074133 | −0.050036 |
| 243 | 0.026069 | −0.007337 | −0.033545 | −0.018953 | −0.016587 | 0.030024 | 0.002843 | −0.023986 | 0.005468 | 0.027215 | 0.049903 | 0.031811 | −0.037688 | −0.046859 |
| 244 | −0.072666 | 0.020478 | 0.045617 | 0:011969 | −0.021672 | 0.019265 | 0.030971 | −0.025965 | 0.013853 | 0.006737 | −0.032741 | −0.038514 | 0.028183 | 0.051149 |
| 245 | −0.037524 | −0.013518 | 0.036631 | 0.021686 | 0.005968 | 0.028272 | −0.046502 | 0.023165 | 0.029029 | −0.006646 | −0.035047 | −0.029695 | 0.007459 | 0.05698 |
| 246 | 0.036788 | 0.028889 | 0.017536 | 0.020928 | −0.003326 | 0.022906 | −0.048364 | −0.012234 | −0.028022 | 0.000804 | 0.003742 | 0.061385 | −0.000877 | −0.010149 |
| 247 | 0.015892 | −0.005142 | −0.013344 | 0.000225 | 0.007324 | 0.008847 | 0.026391 | 0.01366 | 0.025055 | −0.022497 | 0.009667 | 0.036996 | −0.014973 | −0.019264 |
| 248 | −0.025673 | −0.030381 | −0.013119 | −0.017801 | −0.019668 | −0.028702 | 0.026606 | −0.034823 | 0.017538 | −0.039975 | −0.040753 | −0.089393 | 0.019915 | 0.000788 |
| 249 | 0.014213 | −0.088246 | −0.062348 | −0.017144 | −0.019108 | −0.0065 | 0.014396 | 0.005539 | 0.010228 | −0.014984 | −0.044352 | −0.099279 | −0.036384 | −0.027593 |
| 250 | 0.020706 | 0.05731 | 0.013586 | −0.018138 | 0.003284 | 0.046904 | 0.017322 | 0.034336 | −0.028483 | 0.036149 | −0.021982 | 0.024987 | −0.023568 | −0.043605 |
| 251 | −0.031242 | 0.008454 | 0.016108 | 0.003029 | 0.001158 | 0.023693 | 0.02768 | 0.003459 | 0.003545 | 0.001022 | 0.028042 | 0.031802 | 0.072195 | −0.014319 |
| 252 | −0.000329 | −0.012935 | 0.011051 | 0.032217 | 0.020038 | −0.015261 | 0.009261 | −0.005376 | 0.012622 | −0.027986 | 0.004697 | 0.021498 | −0.01676 | 0.026152 |
| 753 | 0.046597 | 0.046491 | 0.000456 | −0.00091 | 0.007453 | 0.001665 | −0.017648 | −0.078227 | −0.074836 | 0.008599 | −0.014911 | 0.010997 | −0.012791 | −0.009912 |
| 254 | 0.016596 | −0.031107 | −0.122927 | −0.007319 | −0.038835 | 0.029558 | −0.015539 | −0.007932 | −0.017448 | 0.034502 | −0.002758 | −0.042557 | −0.050335 | 0.008848 |
| 255 | −0.044688 | 0.03229 | 0.008922 | −0.014766 | −0.017565 | 0.033467 | 0.008564 | −0.035273 | −0.019114 | 0.007977 | −0.02962 | 0.052471 | 0.033292 | 0.045936 |
| 256 | −0.010192 | 0.021645 | 0.025671 | −0.043323 | −0.009548 | 0.030067 | 0.017776 | −0.031278 | −0.075025 | −0.020392 | 0.073188 | −0.018208 | 0.018222 | 0.000189 |
| 257 | −0.003102 | −0.02173 | 0.012995 | 0.011453 | 0.003403 | −0.011697 | −0.018804 | 0.053078 | 0.047486 | 0.001519 | 0.02261 | −0.035005 | −0.032431 | −0.00381 |
| 258 | −0.006795 | −0.027731 | 0.026351 | −0.009771 | −0.046877 | −0.021406 | 0.003735 | −0.003317 | 0.047855 | −0.020734 | −0.054861 | 0.002224 | 0.028776 | 0.028161 |
| 259 | −0.021931 | −0.107968 | −0.087449 | 0.002318 | −0.006276 | −0.013506 | 0.018911 | −0.006875 | 0.00469 | 0.00242 | 0.010771 | 0.062708 | 0.027546 | −0.004488 |
| 260 | 0.00709 | −0.001827 | −0.03427 | −0.007663 | −0.043629 | −0.000168 | −0.023928 | −0.013409 | −0.021741 | 0.021853 | −0.061365 | 0.001926 | −0.042421 | −0.007124 |
| 261 | −0.028665 | 0.014551 | 0.003077 | 0.026151 | 0.018206 | 0.005304 | 0.040443 | −0.032067 | 0.038387 | 0.008764 | −0.006269 | 0.033688 | 0.042191 | −0.049077 |
| 262 | −0.005628 | −0.000493 | 0.000856 | 0.002262 | 0.002876 | 0.0058 | −0.002226 | −0.022223 | −0.003374 | −0.014799 | −0.001873 | −0.010447 | −0.032706 | −0.019654 |
| 263 | −0.006727 | −0.016799 | −0.014243 | −0.002712 | −0.007763 | 0.000696 | −0.003705 | −0.032944 | 0.009402 | −0.0183 | −0.037357 | −0.010836 | −0.007457 | −0.012815 |
| 264 | 0.023849 | −0.1031 | −0.034314 | −0.011926 | −0.00497 | 0.009782 | −0.004486 | −0.004298 | 0.006181 | 0.038483 | −0.035631 | −0.020317 | 0.007663 | 0.013872 |
| 265 | 0.063846 | −0.030528 | −0.064106 | 0.006319 | 0.013102 | 0.012536 | −0.00856 | −0.029368 | 0.004404 | 0.032855 | −0.023301 | −0.007444 | 0.018371 | 0.025887 |
| 266 | 0.029812 | 0.033746 | −0.025517 | −0.009408 | 0.010287 | 0.006668 | 0.033788 | 0.000276 | 0.007848 | 0.007278 | −0.013422 | 0.00299 | 0.026533 | 0.004986 |
| 267 | 0.008638 | −0.001836 | −0.025346 | −0.006021 | −0.004548 | −0.058068 | 0.05843 | 0.038088 | −0.093024 | 0.041555 | −0.043574 | −0.053131 | 0.008333 | 0.013214 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 268 | 0.002593 | −0.017808 | −0.010377 | 0.01719 | 0.022479 | −0.127411 | −0.015613 | −0.024696 | 0.039409 | 0.019398 | −0.019061 | −0.013503 | −0.009783 | −0.031764 |
| 269 | 0.00661 | −0.013489 | −0.015477 | 0.01775 | 0.02857 | −0.105498 | −0.021288 | −0.002228 | 0.033187 | 0.029152 | 0.001403 | −0.052591 | −0.003166 | −0.000471 |
| 270 | 0.00768 | 0.001651 | 0.008466 | 0.007956 | 0.021508 | −0.100327 | −0.125216 | −0.037609 | 0.056081 | 0.005508 | −0.029264 | 0.005817 | 0.02025 | −0.008705 |
| 271 | 0.025476 | 0.007836 | 0.024493 | 0.049261 | 0.059988 | −0.004036 | −0.016875 | −0.003441 | −0.081286 | 0.016088 | 0.008949 | 0.037505 | 0.021361 | 0.03008 |
| 272 | −0.011054 | 0.010683 | −0.001815 | 0.00341 | −0.001044 | −0.002778 | 0.07677 | −0.035103 | −0.193056 | −0.025948 | −0.068457 | 0.058779 | 0.075432 | 0.022873 |
| 273 | 0.012234 | −0.016302 | −0.003211 | 0.01325 | 0.015646 | −0.037693 | 0.016837 | −0.036807 | −0.046212 | −0.072684 | 0.006613 | 0.027242 | 0.03496 | 0.006675 |
| 274 | 0.013132 | 0.002048 | 0.001253 | 0.002796 | 0.007614 | −0.034443 | 0.013005 | −0.03235 | −0.049678 | −0.067277 | 0.016263 | 0.042647 | 0.052559 | 0.002893 |
| 275 | 0.007468 | 0.0137 | −0.006939 | 0.024361 | 0.040496 | 0.015158 | −0.11194 | −0.014836 | −0.022046 | −0.127835 | 0.034875 | 0.005392 | 0.040722 | 0.008095 |
| 276 | −0.024273 | 0.001159 | 0.006898 | −0.028218 | −0.012031 | 0.02721 | 0.062273 | 0.010031 | −0.031565 | −0.01052 | −0.013255 | −0.019508 | 0.047491 | −0.023834 |
| 277 | 0.018864 | 0.003909 | 0.008682 | −0.023804 | −0.004931 | 0.066034 | 0.087453 | −0.000443 | 0.024616 | 0.034466 | 0.018986 | 0.005444 | 0.003672 | 0.004045 |
| 278 | 0.040169 | 0.033224 | −0.006209 | −0.026337 | 0.0064 | 0.0614 | 0.025333 | −0.005665 | −0.007066 | 0.027069 | −0.006792 | 0.014888 | −0.033038 | 0.002427 |
| 279 | 0.007544 | 0.012334 | 0.013907 | −0.032933 | 0.005401 | 0.01831 | 0.04345 | −0.008002 | −0.003662 | −0.027547 | 0.00665 | −0.034163 | −0.030679 | −0.056603 |
| 280 | −0.049242 | −0.042285 | −0.007667 | −0.042031 | −0.032453 | 0.019932 | −0.021066 | −0.069513 | 0.027711 | 0.012137 | 0.015951 | −0.021434 | −0.051808 | −0.035618 |
| 281 | −0.021789 | −0.021714 | 0.00738 | −0.002757 | −0.01053 | −0.0071 | 0.029602 | −0.018285 | −0.014665 | 0.006239 | −0.001638 | 0.008684 | −0.007523 | 0.031337 |
| 282 | 0.021366 | −0.003388 | −0.028449 | 0.0009 | 0.030616 | 0.004309 | −0.012604 | 0.034842 | 0.00204 | 0.02892 | −0.002604 | 0.029879 | −0.069776 | 0.057297 |
| 283 | 0.005494 | 0.041953 | −0.005169 | 0.004635 | 0.034701 | −0.021661 | −0.022439 | −0.018512 | −0.011977 | −0.022484 | −0.003647 | 0.027489 | −0.014258 | −0.034439 |
| 284 | −0.013241 | −0.003835 | 0.036736 | 0.006141 | 0.014946 | 0.012073 | −0.016331 | 0.025419 | 0.005886 | 0.004821 | 0.060588 | −0.044481 | −0.021398 | −0.028055 |
| 285 | 0.036343 | 0.022875 | 0.003488 | −0.013518 | 0.027507 | 0.004535 | −0.014932 | 0.036297 | 0.019049 | 0.002955 | 0.037785 | 0.017396 | 0.024782 | −0.032454 |
| 286 | −0.005436 | −0.026672 | 0.014029 | 0.004316 | −0.01123 | 0.011054 | 0.010441 | 0.039002 | 0.032478 | 0.004987 | 0.002609 | −0.017694 | −0.027251 | 0.049877 |
| 287 | 0.004039 | −0.017594 | −0.022092 | −0.014671 | −0.017339 | −0.002546 | −0.040736 | 0.031739 | 0.022703 | 0.004447 | 0.035682 | −0.011982 | −0.000244 | 0.051295 |
| 288 | 0.033935 | 0.043801 | 0.043756 | −0.025837 | −0.028786 | −0.012883 | −0.056558 | −0.054224 | −0.02984 | 0.007577 | 0.012479 | 0.001156 | 0.02679 | 0.024745 |
| 289 | 0.015561 | 0.022249 | 0.008937 | −0.025617 | −0.01215 | −0.009767 | −0.003075 | −0.003154 | 0.001066 | −0.002017 | 0.024814 | 0.005884 | 0.013088 | −0.024936 |
| 290 | 0.014636 | 0.017488 | −0.004562 | −0.023913 | −0.011781 | 0.004612 | 0.025011 | 0.020483 | 0.031653 | 0.004061 | 0.037819 | 0.01761 | 0.013914 | −0.0167 |
| 291 | 0.009705 | 0.014957 | 0.008886 | −0.025126 | −0.01952 | 0.012563 | 0.035752 | 0.018541 | 0.016247 | 0.002137 | 0.037216 | 0.008604 | 0.014238 | −0.005479 |
| 292 | 0.018656 | 0.016116 | 0.013413 | −0.038485 | −0.016274 | 0.023989 | 0.050591 | 0.00819 | 0.005135 | −0.011207 | 0.049045 | 0.001128 | 0.051111 | −0.027114 |
| 293 | −0.002171 | 0.003839 | −0.012261 | −0.002786 | 0.016006 | 0.003028 | 0.027886 | −0.015176 | −0.062666 | −0.025783 | 0.036515 | −0.003672 | −0.032754 | −0.016171 |
| 294 | 0.012333 | 0.006178 | 0.001698 | −0.052873 | −0.04459 | −0.011343 | −0.005437 | 0.015504 | 0.029477 | 0.016256 | −0.052082 | 0.001114 | −0.028474 | −0.01384 |
| 295 | 0.011234 | 0.005014 | 0.000077 | 0.00099 | 0.001416 | 0.005711 | 0.011533 | 0.015878 | −0.042673 | −0.054624 | −0.012994 | 0.044133 | −0.019734 | 0.033116 |
| 296 | 0.04058 | −0.028425 | −0.037242 | 0.016757 | 0.015118 | −0.011937 | −0.023728 | 0.012427 | 0.029097 | −0.020905 | −0.064068 | 0.005211 | 0.042576 | 0.023695 |
| 297 | 0.009354 | −0.006613 | −0.00877 | −0.023802 | −0.008566 | 0.024568 | 0.001562 | 0.032745 | −0.05251 | −0.042245 | −0.043366 | 0.023876 | −0.009369 | 0.004098 |
| 298 | −0.015398 | 0.005721 | −0.022454 | 0.044893 | 0.014996 | 0.009888 | −0.000511 | 0.032077 | −0.064177 | −0.00185 | −0.033214 | −0.006977 | −0.049781 | −0.022405 |
| 299 | 0.025073 | 0.012749 | −0.018764 | −0.006418 | −0.013106 | −0.020363 | 0.01363 | 0.002698 | −0.070373 | −0.008229 | −0.033813 | −0.050563 | −0.047775 | 0.018392 |
| 300 | 0.007577 | 0.010254 | −0.000921 | −0.015889 | −0.011264 | −0.000679 | −0.005465 | −0.010022 | 0.010134 | −0.024698 | −0.056048 | −0.000078 | 0.01249 | −0.029826 |
| 301 | −0.005612 | 0.005933 | 0.010354 | −0.031945 | −0.019578 | 0.019542 | 0.003909 | 0.031862 | −0.033512 | −0.015172 | 0.002226 | −0.02015 | 0.003656 | −0.019465 |
| 302 | −0.023672 | −0.021474 | 0.016318 | −0.043382 | −0.03145 | −0.013713 | −0.058203 | 0.002922 | 0.017733 | 0.013808 | 0.014138 | 0.011562 | 0.034589 | 0.029483 |
| 303 | −0.021213 | 0.000988 | −0.034842 | −0.03523 | −0.039619 | −0.026295 | 0.024122 | 0.018013 | −0.008274 | 0.042995 | 0.032411 | 0.029071 | −0.000116 | 0.020262 |
| 304 | −0.038364 | −0.005883 | −0.000008 | 0.015775 | 0.005606 | −0.035031 | −0.012108 | −0.026834 | −0.008162 | 0.018172 | 0.036973 | 0.049182 | 0.049672 | 0.044984 |
| 305 | −0.02692 | 0.025908 | −0.022777 | −0.001988 | −0.010386 | −0.050022 | −0.028386 | −0.035022 | −0.029236 | 0.011974 | −0.013004 | −0.019639 | −0.016408 | −0.005554 |
| 306 | −0.053105 | −0.026654 | −0.003743 | 0.024693 | −0.006636 | 0.027105 | 0.013831 | 0.020436 | 0.027455 | 0.002569 | 0.022171 | −0.078999 | 0.041681 | 0.040594 |
| 307 | 0.027488 | −0.013625 | −0.041973 | 0.000829 | 0.025031 | −0.012573 | −0.002029 | −0.042017 | −0.000321 | 0.005478 | −0.016184 | −0.040857 | 0.00239 | 0.015325 |
| 308 | −0.020287 | 0.005025 | 0.01517 | −0.014698 | −0.007428 | −0.002159 | −0.012984 | −0.010382 | −0.011908 | −0.010182 | −0.013131 | −0.031936 | 0.017898 | −0.010869 |
| 309 | 0.008479 | −0.022626 | −0.047227 | 0.002119 | 0.013156 | −0.000084 | −0.01787 | −0.005677 | 0.047168 | 0.009616 | −0.002532 | 0.045528 | 0.022561 | 0.009582 |
| 310 | 0.004645 | 0.022271 | −0.01528 | −0.021865 | −0.021889 | 0.010299 | 0.006312 | −0.002218 | 0.044941 | 0.033214 | 0.024519 | 0.025523 | −0.015128 | 0.033085 |
| 311 | −0.001294 | −0.041601 | −0.024223 | 0.014684 | 0.006318 | −0.045078 | −0.001822 | 0.004459 | −0.03142 | −0.031804 | 0.097518 | 0.014643 | −0.040856 | −0.038767 |
| 312 | 0.027406 | 0.011585 | −0.026499 | −0.041554 | −0.023481 | −0.013899 | 0.054067 | −0.002979 | −0.018742 | −0.006461 | 0.004963 | 0.004262 | −0.036808 | −0.044279 |
| 313 | −0.001912 | −0.028084 | 0.008111 | −0.014131 | −0.011339 | −0.009608 | 0.016221 | −0.00377 | −0.017618 | −0.011167 | 0.04548 | −0.002798 | −0.014815 | −0.04152 |
| 314 | −0.017418 | 0.027828 | −0.010318 | 0.037755 | 0.040658 | −0.008109 | 0.02658 | −0.009715 | 0.038141 | 0.023249 | −0.03458 | 0.026525 | 0.027644 | −0.025341 |
| 315 | −0.0066 | 0.010598 | −0.005281 | −0.009266 | −0.013106 | −0.028396 | −0.011326 | −0.017484 | 0.011602 | 0.004899 | −0.00516 | −0.009958 | 0.034735 | −0.01591 |
| 316 | −0.018333 | 0.022841 | 0.022216 | −0.001396 | −0.014859 | 0.025331 | 0.044349 | 0.012589 | −0.0105 | 0.000224 | 0.039157 | 0.056132 | −0.043597 | −0.038233 |
| 317 | −0.018689 | 0.022719 | −0.030113 | 0.005799 | 0.020861 | 0.024967 | −0.018748 | 0.014675 | 0.014037 | 0.011329 | −0.02571 | 0.033481 | 0.00934 | −0.003934 |
| 318 | −0.029084 | −0.014803 | −0.022919 | 0.052331 | 0.043222 | 0.004462 | 0.076314 | −0.019675 | 0.017078 | 0.015075 | 0.009602 | −0.021406 | −0.005223 | −0.005468 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 319 | −0.027281 | 0.022886 | −0.004207 | −0.053801 | −0.057217 | −0.014178 | 0.00929 | 0.000234 | 0.021634 | −0.003839 | −0.071458 | 0.02449 | 0.042315 | −0.002876 |
| 320 | 0.065035 | 0.002179 | 0.011766 | 0.038329 | 0.002975 | 0.002874 | −0.028266 | −0.005127 | −0.031972 | −0.035756 | −0.021191 | −0.027055 | −0.029681 | −0.006456 |
| 321 | 0.025031 | −0.003129 | 0.017699 | −0.022891 | −0.011875 | 0.027648 | −0.009806 | −0.0182 | 0.02415 | 0.007669 | 0.079556 | −0.007693 | 0.008658 | −0.028049 |
| 322 | 0.040819 | 0.022214 | 0.003313 | −0.065403 | −0.061863 | 0.002963 | 0.022837 | −0.045012 | 0.023618 | −0.016564 | 0.017692 | 0.036471 | 0.043281 | −0.008728 |
| 323 | 0.044005 | −0.017622 | −0.009331 | 0.01902 | 0.017418 | −0.039489 | 0.014428 | 0.02653 | −0.005842 | −0.032197 | −0.009992 | 0.001619 | 0.005604 | 0.01544 |
| 324 | 0.009315 | 0.005686 | 0.022584 | −0.03879 | −0.042 | −0.010531 | −0.02119 | −0.055023 | 0.035447 | 0.030793 | 0.048584 | −0.032381 | 0.029462 | 0.037409 |
| 325 | 0.00532 | 0.011319 | 0.012561 | 0.042235 | 0.050605 | −0.011848 | −0.012385 | −0.115276 | 0.037205 | −0.005925 | 0.041454 | 0.025402 | −0.001374 | −0.021641 |
| 326 | −0.003654 | 0.004659 | 0.012068 | −0:057659 | −0.044088 | 0.027585 | −0.025271 | 0.045817 | 0.033056 | 0.007683 | −0.038066 | −0.001195 | −0.016541 | 0.010989 |
| 327 | 0.013432 | −0.022895 | −0.000808 | 0.017555 | 0.007914 | 0.007456 | 0.027549 | −0.030066 | −0.021038 | −0.011885 | 0.00156 | −0.03806 | 0.04479 | 0.026757 |
| 328 | 0.002656 | 0.000932 | 0.013987 | 0.029757 | 0.044667 | 0.03452 | 0.024565 | −0.046167 | −0.018427 | −0.012294 | 0.015509 | 0.011059 | 0.000349 | 0.002258 |
| 329 | −0.013536 | −0.047835 | −0.014705 | 0.017937 | 0.001441 | 0.003021 | 0.014163 | 0.000095 | 0.015045 | 0.00605 | −0.042394 | 0.013776 | 0.046517 | 0.041234 |
| 330 | 0.053033 | 0.033861 | 0.0498 | 0.042286 | 0.025046 | 0.006699 | 0.051334 | −0.012297 | −0.01505 | −0.017224 | 0.042809 | −0.059933 | −0.014481 | 0.038939 |
| 331 | 0.008842 | −0.01415 | −0.019641 | −0.001562 | −0.002539 | −0.007903 | −0.02675 | −0.004207 | −0.019581 | 0.023174 | 0.005299 | −0.005515 | 0.007234 | 0.017395 |
| 332 | −0.004967 | −0.004118 | 0.034331 | −0.016316 | 0.008082 | 0.006134 | 0.030661 | 0.039108 | 0.06147 | 0.011201 | −0.019247 | −0.027133 | −0.016854 | −0.013517 |
| 333 | −0.02488 | 0.001633 | 0.035115 | −0.00627 | 0.005976 | 0.007565 | −0.0157 | −0.038897 | 0.040912 | 0.009556 | −0.015211 | 0.009286 | −0.007518 | −0.020841 |
| 334 | −0.023692 | −0.022003 | 0.010728 | 0.00861 | 0.025467 | −0.029197 | 0.020731 | 0.035367 | −0.064693 | −0.009407 | −0.012908 | 0.006658 | −0.089951 | −0.029297 |
| 335 | −0.000553 | 0.034188 | 0.023557 | −0.020265 | −0.004003 | 0.027484 | −0.040758 | −0.004391 | −0.022706 | −0.007387 | −0.026927 | −0.00901 | −0.018757 | 0.026905 |
| 336 | −0.01504 | 0.021329 | 0.01922 | 0.005485 | −0.034061 | 0.030451 | −0.006112 | 0.012016 | −0.032847 | 0.002048 | 0.014822 | −0.000526 | −0.004745 | 0.056361 |
| 337 | −0.007196 | 0.035796 | 0.022272 | 0.012725 | −0.040941 | 0.009566 | −0.041453 | 0.043512 | −0.033681 | −0.000644 | −0.018312 | 0.057284 | 0.041504 | −0.050796 |
| 338 | −0.022131 | −0.000403 | −0.021903 | −0.025901 | −0.005892 | 0.020397 | 0.060134 | 0.054957 | 0.001433 | 0.019717 | −0.024726 | −0.026478 | 0.007301 | 0.009713 |
| 339 | −0.015077 | −0.01492 | 0.013462 | −0.034277 | −0.056935 | −0.035458 | −0.032988 | −0.006779 | −0.016616 | −0.00539 | 0.028617 | −0.003146 | 0.030357 | −0.009547 |
| 340 | −0.025645 | −0.008286 | −0.022429 | −0.002765 | −0.00343 | 0.027714 | 0.034918 | 0.026152 | 0.029851 | 0.025843 | 0.013212 | 0.017101 | −0.043881 | 0.007044 |

| | IB | IC | ID | IE | IF | IG | IH | II | IJ | IK | IL | IM | IN | IO |
|---|---|---|---|---|---|---|---|---|---|---|---|---|---|---|
| 1 | 0.041839 | −0.010107 | −0.033995 | 0.06608 | 0.071382 | 0.015315 | 0.011749 | 0.039603 | 0.007715 | −0.083085 | 0.047138 | 0.008356 | 0.011439 | −0.035298 |
| 2 | −0.049603 | 0.064782 | 0.049542 | 0.044785 | 0.003063 | −0.139564 | −0.106411 | −0.009925 | 0.043573 | 0.008768 | −0.007302 | 0.014347 | 0.019351 | 0.040095 |
| 3 | −0.102596 | −0.02749 | −0.025197 | −0.109035 | −0.084244 | 0.012805 | 0.049963 | 0.009731 | −0.026971 | 0.036795 | 0.077249 | 0.051479 | 0.077249 | 0.03838 |
| 4 | −0.026653 | −0.073529 | −0.02792 | 0.010015 | −0.001974 | −0.05023 | −0.127548 | −0.113934 | −0.083547 | 0.001976 | −0.00332 | −0.039859 | −0.027851 | −0.058875 |
| 5 | 0.002627 | −0.014327 | 0.019939 | 0.006502 | −0.000939 | −0.004012 | −0.019572 | 0.036294 | −0.014929 | 0.033598 | 0.004636 | 0.005201 | −0.025298 | 0.027726 |
| 6 | 0.060548 | −0.039789 | 0.085693 | 0.055883 | 0.045808 | −0.015505 | −0.003896 | −0.00376 | −0.040732 | 0.026363 | −0.033418 | 0.021886 | 0.007072 | −0.012261 |
| 7 | −0.030629 | −0.035578 | 0.023996 | −0.040944 | −0.057388 | −0.036687 | −0.040106 | 0.000657 | −0.051396 | −0.027664 | −0.02649 | 0.027381 | −0.084168 | −0.062195 |
| 8 | −0.044972 | −0.066503 | 0.01559 | 0.018172 | 0.01796 | 0.036505 | 0.048972 | −0.056029 | −0.037016 | 0.050866 | 0.037843 | −0.035823 | 0.00573 | −0.012168 |
| 9 | 0.039536 | 0.034234 | −0.006092 | −0.052158 | −0.0465 | 0.049135 | −0.010139 | 0.025542 | 0.00631 | 0.034966 | −0.024763 | 0.007532 | 0.032223 | 0.02254 |
| 10 | 0.045178 | −0.022911 | −0.009124 | 0.004013 | 0.007638 | 0.088972 | 0.027111 | 0.007626 | 0.03298 | 0.0 7312 | −0.041409 | −0.058815 | −0.025989 | −0.005481 |
| 11 | 0.023102 | −0.009882 | 0.00182 | 0.027031 | 0.013412 | 0.048424 | 0.005138 | −0.011562 | 0.057159 | −0.011843 | 0.012945 | −0.016872 | −0.026799 | −0.029936 |
| 12 | 0.009689 | −0.003896 | 0.06355 | 0.004235 | −0.029469 | −0.046539 | 0.027267 | 0.055016 | −0.012208 | −0.009559 | −0.004986 | 0.027939 | 0.01078 | −0.036191 |
| 13 | 0.038459 | −0.030002 | −0.021558 | −0.034663 | −0.037463 | 0.127664 | 0.036221 | −0.029965 | −0.049849 | −0.02642 | −0.01412 | −0.006509 | −0.048688 | −0.008187 |
| 14 | 0.100728 | −0.012236 | 0.01076 | 0.01176 | 0.009173 | 0.007928 | 0.027062 | 0.039183 | 0.007151 | 0.006357 | −0.008664 | 0.042692 | −0.042912 | −0.027375 |
| 15 | −0.020919 | −0.041008 | −0.037992 | 0.001328 | 0.017963 | −0.032378 | −0.00944 | −0.048228 | −0.055491 | 0.002057 | −0.038314 | 0.014303 | −0.013385 | 0.008162 |
| 16 | −0.01949 | 0.049003 | −0.011585 | 0.000469 | −0.003142 | 0.012538 | 0.007346 | 0.047894 | −0.060777 | −0.02341 | 0.001553 | −0.019514 | −0.011663 | 0.05206 |
| 17 | −0.104997 | −0.060311 | −0.036421 | 0.020821 | 0.069752 | 0.038841 | −0.081411 | −0.015926 | 0.022637 | 0.020303 | 0.033871 | −0.046949 | −0.013862 | −0.067326 |
| 18 | 0.030285 | −0.006021 | −0.03754 | −0.040097 | 0.022645 | −0.062454 | −0.079046 | 0.016575 | 0.030772 | 0.038009 | 0.039042 | −0.057948 | −0.036197 | −0.041665 |
| 19 | 0.031877 | 0.044042 | −0.055043 | 0.059962 | 0.05686 | 0.016335 | 0.022313 | −0.019123 | 0.062749 | −0.06242 | 0.027072 | 0.042862 | 0.059904 | 0.051624 |
| 20 | 0.082797 | −0.030633 | −0.070394 | −0.090621 | −0.062427 | −0.023699 | −0.140599 | 0.032533 | 0.022831 | 0.009676 | −0.133064 | −0.01265 | −0.014294 | −0.016868 |
| 21 | 0.077372 | 0.086713 | −0.043763 | −0.050838 | −0.005181 | −0.007032 | −0.047546 | 0.055148 | −0.032318 | 0.016488 | 0.054353 | 0.026547 | −0.016725 | −0.035994 |
| 22 | 0.023957 | 0.034287 | 0.002611 | −0.022782 | 0.018572 | −0.050764 | 0.040198 | −0.009762 | −0.009064 | 0.02581 | 0.067907 | 0.003468 | 0.007611 | 0.019079 |
| 23 | 0.002794 | −0.045239 | −0.000079 | 0.004578 | 0.017997 | 0.033745 | −0.038532 | −0.013978 | 0.007059 | −0.02162 | 0.015467 | 0.037829 | 0.02879 | 0.017705 |
| 24 | −0.046304 | 0.035122 | 0.048292 | −0.018438 | −0.017516 | 0.011889 | −0.049765 | 0.066637 | 0.010563 | −0.038699 | −0.087278 | 0.021369 | 0.015637 | −0.000955 |
| 25 | 0.04166 | −0.089871 | −0.063546 | −0.001859 | −0.057583 | 0.007771 | 0.028392 | 0.030221 | 0.064507 | −0.027508 | −0.088559 | −0.013483 | 0.000971 | −0.00221 |
| 26 | 0.042535 | 0.118084 | 0.01364 | −0.033718 | 0.032338 | 0.025963 | 0.007847 | 0.116401 | 0.022148 | 0.049367 | −0.009264 | −0.019745 | 0.049045 | 0.048149 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 27 | −0.048572 | 0.025078 | 0.019809 | 0.000836 | 0.02566 | −0.026338 | 0.077551 | −0.03189 | 0.00104 | −0.034806 | −0.066614 | −0.009114 | −0.001326 | −0.001514 |
| 28 | 0.005649 | 0.00831 | 0.012841 | −0.007288 | −0.028271 | 0.05516 | 0.042511 | −0.027166 | 0.043105 | −0.020176 | −0.00062 | −0.11834 | 0.01265 | 0.060401 |
| 29 | −0.041578 | −0.024814 | 0.006694 | −0.008663 | −0.004909 | −0.025799 | −0.073024 | −0.005706 | 0.054655 | 0.030629 | −0.005383 | 0.032304 | 0.009383 | 0.025813 |
| 30 | −0.08011 | 0.005377 | 0.060564 | 0.094226 | 0.06126 | −0.002576 | 0.023515 | 0.042032 | 0.110031 | 0.029957 | 0.039062 | 0.011166 | −0.00461 | −0.022249 |
| 31 | 0.070674 | 0.016012 | 0.076781 | 0.085084 | 0.089165 | −0.087503 | 0.002 | 0.015551 | −0.022671 | −0.08461 | −0.021741 | 0.049167 | 0.021266 | 0.039835 |
| 32 | −0.044319 | −0.021857 | 0.056124 | 0.028527 | −0.014718 | −0.028192 | −0.044113 | −0.03851 | 0.012578 | 0.048474 | −0.092704 | −0.042149 | −0.037163 | −0.023359 |
| 33 | 0.028502 | −0.017648 | 0.103371 | 0.026499 | −0.019303 | 0.066724 | 0.005009 | −0.073967 | −0.063476 | 0.00139 | 0.0588 | 0.019225 | 0.011202 | −0.000008 |
| 34 | 0.023751 | 0.003317 | −0.030711 | −0.045354 | −0.059847 | 0.003545 | 0.011991 | −0.041131 | −0.030403 | −0.019307 | 0.056342 | −0.011951 | 0.046004 | 0.021232 |
| 35 | 0.062269 | 0.052633 | −0.057833 | 0.008003 | 0.054307 | −0.031939 | −0.033273 | 0.051657 | −0.018098 | 0.021544 | 0.029203 | 0.012179 | 0.027358 | −0.049511 |
| 36 | −0.094901 | 0.120393 | 0.029893 | −0.016838 | −0.044064 | −0.046273 | −0.106203 | −0.072237 | −0.036898 | 0.107866 | 0.028555 | −0.018444 | 0.025508 | 0.019964 |
| 37 | 0.017948 | −0.029113 | −0.092351 | −0.011918 | −0.01237 | 0.116709 | 0.011301 | 0.090191 | −0.018463 | −0.009264 | 0.008986 | 0.08242 | 0.070394 | −0.026638 |
| 38 | 0.019866 | −0.004213 | −0.00014 | 0.011538 | 0.009955 | −0.023832 | −0.030667 | 0.010068 | −0.030395 | 0.046292 | 0.004435 | 0.011382 | 0.023158 | 0.009483 |
| 39 | 0.048972 | 0.037615 | −0.038673 | 0.034405 | 0.042222 | −0.007883 | −0.025851 | 0.070954 | 0.062286 | −0.006521 | −0.021774 | 0.02767 | 0.013268 | 0.016061 |
| 40 | −0.057962 | −0.068055 | 0.058507 | 0.059651 | 0.059336 | −0.050653 | −0.039852 | −0.010885 | −0.039576 | −0.039134 | −0.063407 | 0.06362 | 0.003123 | 0.010537 |
| 41 | 0.006565 | −0.055209 | −0.028402 | 0.026856 | 0.019927 | 0.065555 | −0.049741 | −0.067326 | −0.070786 | 0.034751 | 0.0202061 | −0.087693 | −0.051988 | 0.015144 |
| 42 | −0.023371 | −0.024008 | 0.011283 | −0.021205 | −0.004229 | −0.000064 | 0.081985 | −0.006542 | 0.035847 | −0.024301 | 0.014697 | −0.033821 | −0.00928 | −0.023361 |
| 43 | 0.142656 | 0.114518 | −0.026888 | 0.031166 | 0.061248 | 0.126346 | 0.023208 | 0.081201 | 0.005039 | −0.005465 | −0.0443 | −0.016995 | 0.063642 | 0.024487 |
| 44 | −0.038844 | 0.032655 | −0.071682 | −0.05634 | −0.024389 | −0.042324 | 0.001761 | 0.001139 | −0.001052 | −0.031044 | 0.03563 | −0.006039 | 0.012103 | 0.099078 |
| 45 | 0.073106 | −0.021948 | −0.01627 | −0.038532 | −0.065255 | −0.006581 | 0.015011 | 0.008092 | −0.048231 | 0.017053 | 0.027971 | −0.014924 | −0.044408 | −0.059171 |
| 46 | 0.037285 | 0.055052 | −0.019184 | 0.016406 | 0.021561 | −0.031325 | −0.020155 | 0.080921 | 0.072792 | 0.040993 | −0.000513 | 0.048018 | 0.076432 | 0.023749 |
| 47 | 0.013684 | −0.083505 | −0.022868 | 0.000961 | 0.042062 | −0.012517 | 0.056482 | −0.038231 | 0.059123 | 0.041328 | 0.039588 | −0.023075 | −0.023682 | −0.03277 |
| 48 | 0.020324 | 0.045888 | 0.004132 | −0.04228 | −0.011597 | −0.047592 | −0.017855 | 0.011419 | −0.086136 | −0.010351 | 0.043389 | −0.002852 | −0.087768 | −0.001276 |
| 49 | −0.015524 | 0.013968 | −0.025069 | −0.067249 | −0.027051 | −0.08116 | −0.060336 | −0.006044 | −0.065197 | −0.019011 | −0.015168 | 0.059593 | −0.013337 | 0.028719 |
| 50 | −0.00101 | −0.020002 | 0.066522 | 0.064268 | 0.018831 | 0.016974 | −0.101499 | −0.05608 | −0.008309 | −0.018497 | −0.078687 | 0.022388 | 0.032424 | 0.056447 |
| 51 | −0.001873 | −0.042207 | 0.038576 | −0.091372 | −0.160556 | 0.019251 | 0.004525 | −0.065674 | −0.015708 | −0.108312 | 0.027338 | 0.034897 | 0.019753 | 0.028704 |
| 52 | 0.063881 | −0.005534 | −0.0708 | 0.022942 | 0.010921 | −0.049647 | −0.051835 | 0.038436 | 0.055572 | 0.021484 | −0.034779 | −0.004419 | 0.044614 | 0.051654 |
| 53 | 0.084614 | 0.016024 | 0.082281 | −0.073657 | −0.056465 | −0.012047 | −0.055778 | 0.029488 | −0.028416 | 0.062218 | 0.111391 | 0.003319 | −0.072436 | −0.046224 |
| 54 | 0.063198 | 0.010025 | −0.062454 | −0.061012 | −0.028024 | 0.048457 | 0.098832 | 0.019703 | 0.036256 | 0.033341 | 0.011404 | −0.047475 | 0.010623 | 0.053974 |
| 55 | −0.098383 | 0.037093 | 0.044249 | −0.024822 | −0.047653 | 0.056575 | 0.04928 | −0.019449 | −0.021764 | 0.045582 | −0.082198, | −0.030473 | −0.028086 | 0.090427 |
| 56 | −0.027843 | −0.103831 | −0.002715 | −0.018503 | −0.036715 | 0.013513 | −0.014999 | −0.09067 | −0.129557 | −0.053239 | 0.083047 | 0.064482 | 0.001171 | −0.040348 |
| 57 | 0.010326 | 0.003071 | 0.061952 | 0.035046 | −0.019808 | −0.036718 | 0.011457 | 0.095784 | −0.024788 | −0.188074 | 0.016553 | 0.122213 | 0.046189 | −0.03686 |
| 58 | 0.065457 | −0.081279 | −0.00227 | 0.068645 | 0.09663 | 0.033351 | −0.023683 | −0.031368 | 0.024539 | 0.004751 | −0.110807 | −0.060497 | 0.002227 | −0.077885 |
| 59 | −0.04656 | 0.037826 | 0.069102 | −0.017786 | 0.000068 | 0.006441 | 0.047709 | −0.089829 | −0.081875 | −0.044711 | 0.0156 | 0.03653 | 0.013645 | −0.016961 |
| 60 | −0.005036 | −0.034079 | 0.009027 | 0.012887 | 0.080983 | 0.004048 | 0.034506 | 0.003833 | 0.01249 | −0.014887 | 0.009747 | −0.024048 | −0.001698 | −0.018494 |
| 61 | 0.021116 | 0.041325 | 0.008808 | 0.084279 | 0.03288 | 0.001454 | 0.010363 | 0.03093 | 0.059636 | 0.026912 | 0.038385 | −0.061967 | −0.059892 | −0.060369 |
| 62 | 0.011424 | 0.083605 | −0.028658 | 0.010269 | 0.011809 | 0.04222 | 0.013016 | −0.040601 | −0.022568 | −0.002291 | 0.001004 | −0.094081 | −0.027743 | −0.024711 |
| 63 | 0.028134 | 0.002013 | 0.069927 | −0.079554 | −0.072248 | −0.03369 | −0.007974 | −0.031695 | −0.033986 | 0.021988 | −0.037844 | 0.030196 | 0.016584 | −0.028529 |
| 64 | −0.015674 | 0.002685 | 0.012539 | 0.008103 | 0.005492 | −0.013506 | −0.019806 | −0.015774 | −0.006617 | 0.02322 | −0.010424 | −0.015291 | −0.002787 | −0.031127 |
| 65 | 0.08778 | −0.03857 | 0.073787 | 0.00434 | 0.005298 | 0.00952 | 0.004866 | −0.063263 | 0.013023 | −0.085501 | 0.051474 | 0.03873 | −0.019369 | 0.059072 |
| 66 | 0.087758 | −0.03162 | 0.007262 | 0.00602 | −0.01549 | −0.083349 | −0.100059 | 0.072908 | 0.095052 | −0.01598 | −0.069829 | −0.00274 | −0.044232 | 0.000676 |
| 67 | −0.05915 | −0.038496 | 0.061921 | 0.0152 | 0.017137 | 0.096429 | 0.074412 | −0.013597 | 0.042969 | −0.054508 | −0.005163 | 0.009972 | −0.014057 | −0.007041 |
| 68 | −0.072236 | −0.007315 | −0.006985 | 0.028054 | 0.010869 | 0.009136 | 0.071777 | −0.038473 | −0.040025 | 0.001282 | −0.022006 | −0.030469 | 0.021148 | −0.028518 |
| 69 | 0.010663 | 0.000375 | −0.054738 | −0.017337 | −0.026377 | −0.044135 | −0.058159 | 0.069336 | 0.029049 | −0.00714 | 0.010305 | −0.01852 | −0.048837 | −0.081333 |
| 70 | 0.07563 | −0.034741 | 0.03058 | 0.045939 | 0.063129 | 0.039979 | −0.103944 | −0.039823 | −0.026307 | 0.046122 | −0.023703 | −0.01333 | −0.002386 | 0.065833 |
| 71 | −0.05333 | 0.030197 | 0.014701 | −0.01786 | 0.047636 | −0.005957 | 0.012885 | −0.019349 | 0.06889 | −0.040947 | −0.074284 | 0.021374 | −0.003931 | −0.041312 |
| 72 | −0.025706 | −0.055917 | −0.041347 | 0.029498 | 0.001931 | 0.062267 | 0.049378 | −0.001112 | 0.037891 | −0.028306 | −0.019233 | −0.040085 | −0.070296 | −0.012801 |
| 73 | −0.044243 | 0.006524 | −0.037157 | −0.025531 | −0.037585 | −0.01332 | −0.008921 | 0.02831 | −0.000461 | −0.033291 | −0.006885 | −0.004579 | −0.036617 | −0.114937 |
| 74 | 0.005091 | −0.048907 | 0.030056 | 0.018109 | 0.035017 | −0.024874 | 0.01233 | −0.056909 | 0.021419 | 0.028037 | −0.019256 | 0.042045 | −0.005886 | −0.011675 |
| 75 | 0.025716 | −0.001925 | −0.023384 | 0.014411 | −0.012033 | −0.029113 | 0.043702 | 0.069912 | 0.026521 | −0.018702 | 0.03811 | −0.006349 | 0.025617 | −0.001394 |
| 76 | −0.091904 | 0.014693 | −0.008562 | 0.036473 | 0.001184 | −0.013837 | 0.077968 | −0.09585 | −0.073202 | −0.033642 | −0.034619 | 0.021767 | 0.032634 | 0.004209 |
| 77 | −0.027784 | 0.029015 | 0.030722 | −0.025844 | −0.010977 | 0.01293 | 0.033839 | −0.019666 | 0.015562 | 0.084782 | 0.059789 | 0.002464 | −0.010785 | 0.015824 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 78 | −0.001571 | 0.050501 | −0.047208 | 0.008143 | 0.023501 | −0.074667 | 0.005475 | 0.004947 | 0.001032 | −0.032519 | −0.008227 | −0.016005 | 0.104218 | 0.064411 |
| 79 | −0.027919 | 0.036224 | 0.057976 | −0.036797 | −0.045608 | −0.01366 | −0.029261 | −0.029155 | 0.006882 | −0.024254 | 0.047292 | −0.018261 | −0.042729 | −0.024387 |
| 80 | −0.016799 | 0.004852 | 0.013834 | −0:008514 | −0.026295 | −0.013488 | −0.009483 | 0.03071 | 0.031692 | 0.041049 | −0.006357 | −0.012394 | 0.01022 | −0.013269 |
| 81 | −0.083399 | −0.060472 | 0.027964 | 0.02336 | 0.05144 | −0.024185 | 0.036617 | 0.044243 | 0.033346 | 0.02876 | 0.038105 | 0.067241 | 0.022072 | −0.010074 |
| 82 | 0.036522 | −0.000599 | −0.018653 | 0.058504 | 0.054036 | −0.054338 | −0.022146 | −0.013153 | 0.019966 | 0.026994 | 0.064394 | −0.076956 | 0.091618 | 0.071901 |
| 83 | 0.044249 | −0.001611 | 0.029296 | −0.018405 | −0.074974 | 0.032707 | 0.02766 | 0.025624 | 0.054863 | −0.028477 | 0.049294 | −0.012176 | −0.027821 | −0.023789 |
| 84 | −0.02869 | −0.097466 | −0.133506 | −0.011509 | 0.050752 | −0.015983 | 0.046711 | −0.035946 | 0.051548 | −0.015814 | −0.000093 | −0.005249 | 0.020691 | 0.042555 |
| 85 | 0.015691 | 0.013234 | −0.057722 | −0.004907 | 0.025161 | −0.0227 | −0.020733 | −0.031911 | −0.044868 | 0.055524 | 0.042652 | 0.002848 | 0.033371 | 0.028626 |
| 86 | 0.082396 | 0.031815 | −0.03276 | −0.094998 | −0.075878 | −0.038906 | −0.020188 | 0.050106 | 0.046017 | 0.063771 | 0.064492 | 0.060672 | 0.051173 | 0.078388 |
| 87 | 0.065601 | −0.041266 | 0.025879 | 0.103677 | 0.083623 | 0.051029 | 0.061176 | −0.107719 | −0.097078 | −0.071582 | 0.011664 | −0.041011 | 0.02186 | 0.083682 |
| 88 | 0.06701 | −0.028185 | 0.035257 | 0.020422 | −0.005066 | −0.054885 | 0.037858 | 0.173307 | 0.010643 | −0.00435 | −0.010592 | 0.000633 | −0.023449 | −0.006463 |
| 89 | −0.04122 | −0.060524 | −0.072394 | −0.045024 | 0.006221 | −0.043071 | 0.014887 | 0.084798 | 0.031494 | 0.069979 | 0.089749 | 0.02485 | −0.066883 | −0.093705 |
| 90 | −0.165951 | 0.022924 | 0.018993 | 0.028582 | 0.006397 | −0.025385 | −0.009506 | −0.112613 | −0.059184 | −0.052848 | 0.079841 | 0.027186 | 0.006157 | −0.037882 |
| 91 | −0.030403 | 0.053512 | 0.087459 | 0.069791 | 0.001243 | −0.040202 | 0.042389 | 0.018107 | 0.023192 | −0.034227 | 0.005813 | −0.013845 | −0.050459 | −0.089184 |
| 92 | −0.003311 | −0.034386 | 0.051943 | −0.014582 | −0.078164 | 0.036308 | −0.038508 | −0.063801 | −0.057026 | 0.034186 | −0.070993 | −0.024215 | −0.032725 | 0.018498 |
| 93 | 0.045772 | 0.017282 | −0.055493 | −0.04341 | 0.028801 | 0.008666 | −0.002868 | 0.035497 | −0.040913 | 0.013634 | 0.071591 | 0.03989 | −0.051375 | −0.064124 |
| 94 | 0.020296 | −0.032969 | −0.020986 | 0.031251 | 0.054067 | 0.076734 | 0.039115 | −0.00172 | −0.001961 | −0.022047 | 0.029664 | 0.082622 | −0.004745 | −0.080232 |
| 95 | −0.034309 | −0.033374 | 0.016431 | −0.023067 | −0.050228 | −0.012944 | −0.002904 | 0.02156 | −0.018716 | 0.0782 | 0.073499 | 0.037545 | 0.003524 | −0.012933 |
| 96 | 0.153198 | −0.009714 | 0.030497 | −0.005244 | 0.034244 | −0.039739 | −0.061637 | 0.028379 | 0.063103 | −0.009015 | −0.009796 | −0.025487 | 0.03042 | 0.074194 |
| 97 | 0.000771 | 0.030264 | 0.069308 | 0.024237 | 0.037113 | 0.01203 | 0.036966 | 0.002139 | −0.035495 | −0.009423 | −0.011104 | 0.002685 | −0.041485 | −0.032837 |
| 98 | 0.062351 | 0.030075 | 0.043373 | 0.037837 | −0.043253 | −0.008406 | −0.008672 | 0.001322 | 0.015557 | −0.009624 | −0.006651 | −0.005696 | −0.014925 | −0.069615 |
| 99 | −0.006871 | 0.049054 | −0.056375 | 0.026962 | 0.014715 | 0.010396 | −0.001092 | −0.023529 | 0.063405 | 0.036691 | 0.003094 | −0.016916 | −0.034595 | 0.011909 |
| 100 | −0.016012 | −0.001256 | 0.042983 | 0.056784 | 0.00937 | 0.019864 | 0.065759 | −0.055792 | −0.004314 | −0.056667 | 0.055798 | −0.00789 | 0.01568 | 0.023687 |
| 101 | −0.113451 | 0.076703 | −0.029125 | −0.052102 | −0.007954 | 0.078165 | −0.080439 | −0.026726 | −0.126973 | 0.040542 | 0.04318 | −0.069957 | −0.02152 | 0.02454 |
| 102 | −0.104168 | −0.074216 | 0.055081 | −0.04261 | −0.038479 | 0.071142 | 0.000046 | −0.006087 | 0.000181 | −0.0076 | −0.098501 | 0.005802 | −0.079767 | −0.001493 |
| 103 | 0.009236 | 0.008873 | 0.103999 | −0.029979 | −0.03869 | −0.033086 | 0.005425 | −0.047859 | 0.023873 | 0.026775 | −0.006302 | −0.000553 | 0.006416 | 0.029771 |
| 104 | −0.01921 | 0.029557 | −0.044137 | 0.02221 | 0.047664 | −0.052646 | 0.049264 | 0.014162 | −0.003171 | 0.003488 | −0.032586 | −0.05719 | 0.01112 | 0.0033 |
| 105 | 0.006384 | −0.017743 | 0.009365 | −0.0195 | 0.004608 | −0.03178 | 0.03171 | −0.058686 | 0.036669 | −0.018818 | −0.048799 | −0.018866 | 0.000001 | 0.045889 |
| 106 | −0.017741 | 0.046285 | −0.015584 | 0.005902 | −0.015814 | −0.015003 | 0.04216 | 0.008837 | −0.020886 | −0.014974 | −0.106729 | 0.004335 | −0.006424 | 0.022459 |
| 107 | 0.028988 | −0.047898 | 0.015816 | 0.054934 | 0.019725 | 0.041725 | 0.023139 | −0.035341 | −0.036763 | −0.027962 | −0.098132 | −0.072759 | 0.017363 | −0.002773 |
| 108 | 0.00333 | −0.080018 | −0.07071 | −0.035373 | 0.055141 | 0.003678 | −0.022109 | 0.006221 | −0.015277 | 0.010249 | 0.07956 | 0.021802 | −0.020691 | −0.025932 |
| 109 | −0.020078 | 0.025067 | 0.043318 | −0.007777 | −0.039066 | 0.025373 | 0.006064 | 0.055174 | 0.026291 | 0.003698 | −0.021538 | 0.048253 | 0.032329 | −0.007941 |
| 110 | 0.012729 | −0.011829 | 0.025687 | −0.008504 | −0.036396 | −0.005623 | 0.012353 | 0.016899 | 0.05024 | −0.015743 | −0.029243 | 0.010118 | −0.010121 | −0.010613 |
| 111 | 0.01482 | −0.003976 | 0.044881 | 0.01928 | −0.085263 | −0.032027 | 0.010967 | −0.019929 | 0.038834 | 0.000448 | −0.076256 | −0.057917 | 0.051421 | −0.003552 |
| 112 | 0.072401 | 0.004277 | 0.032889 | −0.04874 | −0.053685 | 0.022356 | 0.043251 | −0.010338 | 0.019305 | 0.017062 | 0.04624 | 0.061655 | 0.00025 | −0.014393 |
| 113 | 0.037325 | −0.014417 | −0.024065 | −0.001116 | 0.031987 | 0.036791 | −0.027658 | 0.002039 | 0.066578 | −0.041922 | 0.004973 | 0.02646 | −0.010204 | −0.000162 |
| 114 | 0.018862 | −0.009131 | 0.041173 | 0.014006 | 0.026156 | 0.025839 | 0.02281 | −0.006564 | 0.0128 | −0.029496 | −0.006122 | 0.029368 | −0.002147 | 0.009409 |
| 115 | 0.002914 | −0.001743 | 0.093217 | 0.004978 | −0.032945 | −0.082944 | −0.030216 | 0.008713 | 0.072698 | 0.030984 | −0.024841 | −0.011113 | −0.039886 | −0.040874 |
| 116 | −0.036267 | −0.019094 | −0.000967 | 0.031072 | 0.038306 | −0.006027 | −0.025293 | 0.041673 | −0.007012 | −0.00711 | 0.022737 | 0.027088 | −0.01717 | −0.012183 |
| 117 | 0.004637 | −0.001709 | −0.036308 | 0.045542 | 0.030548 | 0.054934 | −0.014544 | −0.033603 | 0.025899 | 0.051655 | −0.046764 | 0.003273 | 0.03708 | −0.052213 |
| 118 | 0.04779 | 0.009008 | 0.016827 | −0.049304 | −0.010393 | 0.024722 | 0.087229 | −0.014648 | −0.061347 | 0.001439 | −0.024655 | 0.058409 | 0.038341 | −0.018906 |
| 119 | 0.013687 | 0.031844 | 0.119311 | −0.008578 | −0.035641 | 0.00451 | −0.016955 | −0.081852 | −0.028222 | 0.002927 | 0.046801 | 0.003654 | −0.038614 | −0.064631 |
| 120 | −0.106068 | 0.012779 | −0.018339 | 0.03347 | 0.010544 | 0.065246 | 0.009772 | −0.015961 | −0.038757 | −0.088273 | −0.013398 | 0.019508 | −0.033836 | 0.014403 |
| 121 | 0.03174 | −0.019271 | 0.089448 | 0:007145 | −0.026745 | −0.06226 | −0.021467 | −0.015762 | 0.020597 | −0.006419 | −0.002047 | −0.070197 | −0.055237 | 0.008574 |
| 122 | −0.0623011 | 0.020571 | 0.029967 | 0.045712 | −0.03674 | −0.002453 | −0.025659 | 0.017585 | 0.0514221 | −0.006712 | 0.023417 | 0.008097 | 0.044804 | 0.028653 |
| 123 | 0.1691261 | 0.050094 | −0.017969 | 0.029965 | 0.033599 | −0.013596 | 0.109678 | 0.065868 | 0.0028991 | 0.038473 | 0.085991 | −0.003504 | −0.081654 | −0.002179 |
| 124 | 0.013784 | −0.057456 | 0.088177 | 0.072529 | 0.009694 | −0.003876 | −0.08452 | −0.006067 | 0.034731 | −0.067749 | −0.033665 | 0.027023 | 0.020391 | 0.097589 |
| 125 | 0.062852 | −0.041594 | 0.117534 | −0.003819 | −0.012539 | −0.018484 | 0.02773 | −0.055534 | 0.036311 | −0.006616 | 0.027313 | −0.004084 | 0.015509 | 0.027188 |
| 126 | −0.092773 | 0.062175 | 0.051495 | 0.029837 | −0.039147 | −0.070319 | −0.056711 | 0.055819 | 0.006932 | −0.081827 | −0.088301 | −0.062308 | 0.050855 | 0.061391 |
| 127 | 0.027606 | −0.065499 | 0.050448 | 0.007242 | 0.02318 | −0.079543 | −0.094027 | −0.024106 | 0.113147 | −0.008217 | 0.105284 | −0.057377 | −0.042331 | 0.074839 |
| 128 | −0.038064 | 0.037342 | −0.081968 | 0.023505 | 0.028298 | −0.048885 | −0.012847 | −0.046976 | −0.146284 | 0.004375 | 0.112042 | 0.044272 | 0.009163 | 0.016112 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 129 | 0.038087 | −0.010226 | 0.001923 | 0.022243 | −0.029963 | 0.014202 | 0.045215 | 0.007682 | −0.009917 | −0.0179 | −0.016064 | −0.052023 | −0.021887 | −0.009473 |
| 130 | 0.008173 | −0.005964 | −0.036801 | −0.001643 | 0.003949 | 0.04462 | 0.024432 | −0.016906 | 0.00211 | −0.017804 | −0.00807 | −0.024456 | 0.018054 | 0.0449 |
| 131 | −0.02354 | −0.023046 | −0.050725 | 0.025301 | 0.027388 | −0.004446 | −0.00996 | 0.022699 | 0.000256 | −0.032584 | 0.007631 | 0.026296 | 0.004797 | −0.029284 |
| 132 | −0.06278 | 0.063363 | 0.065806 | −0.045084 | −0.005965 | −0.004357 | 0.057319 | 0.000819 | 0.053808 | 0.027392 | −0.052289 | 0.035117 | 0.062901 | 0.017166 |
| 133 | 0.053771 | −0.01671 | −0.043941 | −0.030985 | −0.006088 | 0.006374 | −0.047703 | −0.061917 | −0.054563 | 0.00755 | 0.130523 | −0.005288 | −0.043241 | 0.035564 |
| 134 | 0.042602 | −0.007634 | −0.041979 | −0.044766 | −0.028001 | −0.010339 | −0.056642 | −0.053509 | 0.008298 | −0.020968 | 0.020996 | 0.006709 | −0.016278 | −0.023868 |
| 135 | −0.070606 | 0.002305 | −0.044591 | 0.003319 | −0.042079 | −0.047395 | −0.043311 | −0.008707 | 0.090223 | −0.068541 | 0.010611 | 0.019608 | 0.018038 | −0.023347 |
| 136 | −0.003028 | −0.011195 | −0.01578 | −0.017182 | 0.020605 | 0.011764 | 0.006777 | 0.049343 | 0.041159 | 0.059222 | 0.081318 | 0.032062 | 0.002389 | 0.005636 |
| 137 | −0.009704 | 0.032549 | 0.008513 | −0.010879 | −0.038573 | 0.009319 | 0.016015 | −0.004823 | −0.000381 | −0.056845 | −0.070762 | 0.00101 | 0.031234 | 0.030255 |
| 138 | 0.001597 | 0.029284 | 0.002808 | −0.019335 | 0.039346 | −0.044751 | −0.05429 | −0.011042 | 0.028794 | 0.001113 | −0.01982 | −0.001197 | −0.031387 | 0.000334 |
| 139 | 0.00673 | 0.01747 | 0.024558 | 0.00072 | −0.007775 | −0.001673 | −0.001949 | −0.010031 | 0.000349 | −0.003221 | −0.039933 | −0.028173 | −0.058002 | −0.022192 |
| 140 | 0.021594 | −0.011493 | 0.027432 | −0.036124 | −0.020141 | −0.019502 | −0.042357 | 0.016879 | 0.01675 | −0.004339 | −0.035898 | −0.007783 | 0.003151 | −0.028239 |
| 141 | 0.001002 | −0.025977 | 0.038194 | 0.047999 | 0.03537 | 0.000322 | 0.047727 | 0.027985 | −0.007392 | −0.007321 | −0.078231 | −0.006786 | 0.009981 | 0.032473 |
| 142 | −0.068742 | −0.013218 | 0.007291 | 0.016816 | 0.015658 | 0.012879 | 0.01694 | −0.019716 | −0.020053 | −0.036253 | −0.039279 | −0.017911 | 0.001697 | 0.017998 |
| 143 | 0.026105 | −0.02828 | 0.002821 | 0.023257 | 0.018049 | 0.047749 | −0.017897 | −0.016598 | 0.052389 | −0.049038 | −0.083357 | −0.014776 | 0.020967 | −0.003968 |
| 144 | 0.033982 | −0.01704 | 0.023289 | 0.002161 | 0.009298 | −0.016279 | −0.015124 | −0.015158 | 0.002801 | 0.028691 | −0.081592 | −0.03005 | −0.007526 | 0.031315 |
| 145 | −0.079961 | −0.003385 | −0.012961 | −0.015528 | −0.002416 | −0.005004 | 0.016479 | 0.034481 | −0.025454 | 0.019837 | 0.068717 | 0.012221 | −0.039831 | −0.012074 |
| 146 | 0.021546 | 0.006647 | 0.005505 | 0.016537 | −0.012272 | 0.009906 | 0.047264 | 0.022553 | 0.017648 | −0.022036 | −0.040367 | −0.025252 | 0.019497 | 0.014494 |
| 147 | −0.048782 | −0.022003 | −0.000424 | 0.017137 | 0.001028 | −0.020966 | 0.017796 | −0.000786 | 0.055929 | 0.002828 | −0.015433 | 0.031967 | 0.024791 | 0.006297 |
| 148 | 0.014259 | −0.02896 | 0.045385 | 0.012372 | −0.028461 | −0.035542 | 0.016329 | −0.007766 | 0.011544 | −0.001063 | −0.001135 | 0.024754 | 0.040567 | −0.009828 |
| 149 | 0.024831 | 0.022496 | −0.012696 | −0.038929 | −0.034688 | 0.004867 | −0.008467 | 0.032662 | 0.01844 | −0.020009 | −0.018562 | −0.017488 | −0.023653 | 0.000384 |
| 150 | −0.001701 | 0.028809 | 0.013792 | −0.014445 | −0.043629 | 0.041243 | 0.005687 | −0.003283 | −0.023577 | 0.024084 | −0.001105 | −0.011377 | −0.03273 | −0.058098 |
| 151 | −0.02563 | 0.042986 | −0.029752 | −0.03693 | −0.006167 | −0.009179 | 0.022888 | −0.010595 | −0.051607 | 0.020589 | 0.043025 | −0.003441 | 0.006687 | −0.012832 |
| 152 | −0.026263 | 0.018886 | −0.056648 | 0.005075 | 0.003836 | 0.017806 | 0.02488 | −0.004932 | −0.04502 | −0.013279 | 0.018118 | 0.005628 | 0.027273 | 0.012957 |
| 153 | 0.018763 | −0.014351 | 0.020916 | 0.046113 | 0.04959 | 0.035084 | 0.014755 | 0.024521 | −0.025546 | −0.036875 | −0.030323 | 0.033813 | 0.014276 | −0.015453 |
| 154 | 0.006329 | 0.020539 | 0.033609 | −0.014891 | −0.024984 | −0.026775 | 0.01124 | −0.028121 | −0.007355 | 0.021887 | −0.017784 | −0.003335 | 0.050572 | 0.006028 |
| 155 | 0.01848 | 0.016367 | 0.000518 | −0.01289 | 0.004205 | 0.016814 | −0.024454 | 0.024302 | −0.019277 | −0.007212 | −0.021601 | −0.015864 | −0.022523 | −0.063615 |
| 156 | 0.044044 | 0.013458 | −0.032561 | −0.039746 | −0.013272 | −0.004323 | 0.014941 | 0.02513 | −0.0461 | −0.001683 | −0.043636 | −0.013967 | 0.038789 | 0.040412 |
| 157 | −0.014723 | −0.0146 | 0.004084 | −0.02595 | −0.013217 | 0.014262 | −0.030418 | −0.012949 | −0.028058 | −0.034027 | 0.031296 | 0.017943 | −0.048107 | −0.043523 |
| 158 | 0.006419 | 0.020817 | 0.027577 | 0.008121 | 0.018927 | 0.001393 | 0.004747 | −0.022906 | −0.017138 | 0.002288 | −0.013016 | −0.005414 | −0.0258 | 0.007249 |
| 159 | 0.027518 | 0.018806 | −0.003472 | 0.010008 | 0.038182 | 0.00157 | 0.014827 | 0.006787 | −0.039687 | 0.028036 | 0.050334 | −0.029645 | 0.011616 | 0.00804 |
| 160 | −0.01952 | 0.003541 | 0.002589 | 0.00286 | 0.030103 | −0.031792 | −0.012529 | −0.003913 | 0.010904 | −0.002575 | −0.012051 | −0.010055 | 0.00309 | −0.00543 |
| 161 | −0.028234 | −0.022074 | −0.02071 | −0.001356 | −0.029055 | 0.001222 | −0.022511 | 0.053249 | 0.002899 | 0.039096 | 0.035121 | −0.00946 | −0.010459 | −0.005264 |
| 162 | −0.040389 | 0.022386 | −0.022341 | 0.009145 | 0.048607 | −0.045218 | 0.0356 | 0.002241 | 0.013632 | −0.009597 | −0.03995 | −0.032033 | 0.03998 | 0.068002 |
| 163 | −0.049118 | −0.022824 | −0.044168 | 0.032626 | 0.014231 | 0.004856 | −0.027203 | 0.029911 | −0.000307 | 0.013291 | −0.018121 | 0.001289 | −0.015553 | −0.036245 |
| 164 | 0.067959 | −0.019935 | −0.048512 | −0.015934 | 0.027242 | 0.008778 | 0.000896 | 0.045849 | 0.022376 | 0.036084 | 0.00254 | −0.027821 | −0.001894 | 0.017973 |
| 165 | −0.034891 | −0.027043 | −0.006891 | −0.004738 | −0.013254 | −0.015313 | −0.018362 | 0.009866 | 0.000342 | −0.01552 | 0.023436 | 0.046751 | −0.023343 | −0.021658 |
| 166 | 0.013087 | 0.000485 | −0.019875 | 0.027144 | 0.031139 | −0.029697 | 0.036421 | 0.01807 | −0.00655 | 0.027014 | 0.012998 | −0.017593 | 0.010221 | −0.026657 |
| 167 | −0.016156 | −0.001802 | −0.065149 | 0.004668 | 0.026814 | −0.030939 | −0.008076 | 0.008827 | 0.001706 | 0.020783 | −0.021764 | −0.012721 | −0.02155 | −0.024328 |
| 168 | −0.060808 | 0.018313 | 0.074858 | 0.021803 | −0.049643 | −0.00015 | −0.066282 | 0.02305 | 0.049144 | −0.006705 | −0.019646 | 0.037258 | −0.004561 | −0.01228 |
| 169 | −0.01607 | −0.004663 | −0.00436 | 0.000243 | 0.001052 | −0.029059 | −0.007153 | 0.029002 | 0.024702 | 0.0005 | −0.024816 | 0.005399 | 0.001052 | 0.033148 |
| 170 | −0.013719 | −0.010004 | 0.009796 | −0.001551 | 0.010839 | −0.033138 | −0.012972 | 0.018244 | 0.023672 | 0.011075 | −0.003781 | −0.00577 | 0.020277 | 0.052329 |
| 171 | −0.006007 | 0.010212 | −0.006639 | 0.008091 | 0.012803 | −0.016989 | −0.000969 | 0.002852 | 0.00596 | 0.010002 | −0.032065 | −0.00116 | −0.001459 | 0.035576 |
| 172 | −0.029173 | 0.037256 | 0.027987 | −0.00174 | −0.023963 | 0.006145 | 0.015721 | 0.019007 | 0.013327 | −0.006639 | −0.030921 | 0.021292 | −0.003702 | −0.004942 |
| 173 | −0.013246 | 0.041305 | 0.066295 | 0.023501 | −0.004245 | 0.009137 | 0.038159 | −0.008113 | −0.007991 | 0.002964 | −0.010949 | 0.010226 | 0.036187 | 0.011356 |
| 171 | 0.011132 | 0.016464 | 0.028024 | 0.001193 | −0.000243 | 0.008441 | −0.031191 | −0.003273 | −0.014258 | 0.033416 | −0.053969 | −0.011837 | 0.01137 | 0.017401 |
| 175 | 0.041206 | 0.006015 | −0.031145 | −0.024929 | −0.000917 | −0.015964 | −0.024355 | −0.032357 | −0.00277 | 0.033451 | 0.035867 | −0.015125 | −0.003546 | 0.025659 |
| 176 | −0.001631 | −0.030793 | −0.000483 | −0.012563 | −0.03132 | −0.009126 | 0.028291 | 0.030472 | 0.024003 | −0.021253 | 0.003806 | 0.016718 | −0.043172 | −0.022557 |
| 177 | −0.014966 | −0.016903 | −0.041253 | −0.03269 | 0.011859 | 0.025631 | −0.041238 | 0.015382 | 0.013136 | −0.000005 | −0.007897 | 0.032302 | −0.012435 | −0.029147 |
| 178 | 0.037717 | −0.012064 | 0.035867 | 0.005938 | −0.00671 | 0.006834 | 0.000102 | 0.010429 | 0.001151 | −0.035401 | −0.009553 | −0.001805 | −0.028717 | 0.006383 |
| 179 | −0.00301 | −0.001854 | −0.024149 | −0.007121 | 0.006205 | −0.015803 | 0.013764 | 0.007907 | 0.010981 | −0.007536 | −0.007047 | 0.000962 | 0.006062 | −0.002824 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 180 | −0.007175 | −0.027508 | −0.006608 | 0.006522 | 0.021079 | −0.003664 | 0.009139 | −0.00692 | −0.00942 | −0.023164 | 0.02318 | 0.006782 | 0.006237 | 0.007293 |
| 181 | 0.031413 | −0.013616 | −0.016028 | −0.003432 | 0.014937 | 0.005078 | 0.012383 | 0.002892 | 0.005491 | 0.00493 | 0.002156 | −0.008108 | 0.0048 | −0.00915 |
| 182 | 0.061991 | −0.026264 | 0.015545 | −0.011368 | −0.023864 | 0.001454 | −0.004663 | −0.033327 | 0.022844 | −0.008745 | 0.023065 | −0.032728 | −0.014643 | −0.022632 |
| 183 | 0.025445 | −0.01645 | 0.020576 | 0.015992 | 0.012991 | −0.002067 | −0.010714 | −0.037396 | −0.006863 | −0.014224 | 0.008425 | −0.017104 | −0.051089 | −0.03393 |
| 184 | 0.005095 | 0.006749 | 0.033754 | 0.027082 | 0.02265 | 0.032654 | 0.012889 | 0.023765 | −0.023538 | −0.015178 | −0.029135 | −0.017772 | −0.039193 | −0.038142 |
| 185 | 0.01366 | −0.007913 | 0.006428 | 0.036061 | 0.035702 | 0.024428 | 0.013688 | −0.041087 | −0.078972 | −0.028609 | 0.030164 | −0.009464 | −0.015257 | −0.017856 |
| 186 | −0.021311 | −0.034335 | −0.045747 | 0.010951 | 0.029516 | 0.041383 | −0.027279 | −0.015743 | −0.047927 | 0.000302 | 0.01413 | 0.008244 | −0.002216 | −0.022845 |
| 187 | 0.016717 | 0.00671 | 0.00437 | 0.035798 | 0.020733 | −0.023798 | −0.020677 | −0.016644 | −0.021839 | −0.027846 | 0.063944 | −0.027881 | 0.008096 | 0.002556 |
| 188 | 0.011084 | 0.016524 | 0.010569 | 0.013636 | 0.001898 | −0.028283 | −0.020112 | −0.00319 | −0.009084 | −0.003404 | −0.046986 | −0.006408 | −0.00627 | −0.002629 |
| 189 | 0.041278 | −0.008727 | −0.053274 | 0.008803 | 0.036603 | 0.001434 | −0.009045 | −0.011746 | 0.007563 | 0.031179 | −0.015371 | 0.004694 | 0.017394 | 0.008248 |
| 190 | 0.010582 | −0.044164 | 0.031388 | 0.000133 | 0.006714 | −0.014114 | 0.007478 | −0.023171 | 0.002886 | −0.006544 | 0.034389 | 0.037879 | −0.033395 | −0.02811 |
| 191 | 0.010431 | −0.0046 | 0.032298 | −0.016848 | −0.031002 | −0.010554 | −0.016137 | −0.028226 | −0.016007 | −0.043786 | 0.017822 | 0.007607 | 0.008553 | 0.007408 |
| 192 | 0.056139 | 0.019153 | −0.004509 | −0.012979 | −0.004237 | 0.00445 | 0.009945 | 0.021974 | 0.080943 | 0.014435 | −0.045504 | −0.007263 | 0.004117 | 0.017128 |
| 193 | 0.046707 | 0.009467 | 0.010994 | −0.017886 | −0.044513 | −0.006393 | 0.025798 | 0.019702 | 0.002786 | −0.030072 | −0.016867 | −0.003175 | 0.049318 | 0.007611 |
| 194 | −0.038936 | 0.01224 | −0.07561 | −0.003783 | −0.004534 | 0.009827 | 0.006516 | 0.017953 | 0.005423 | 0.007511 | −0.000604 | −0.005699 | 0.006243 | 0.011454 |
| 195 | 0.020916 | −0.013118 | −0.00023 | −0.014734 | −0.020922 | 0.026214 | −0.013229 | −0.006289 | 0.000895 | 0.002892 | 0.048397 | 0.006979 | 0.004272 | −0.000877 |
| 196 | −0.001475 | −0.00249 | −0.013165 | −0.00207 | 0.005278 | 0.046407 | 0.010803 | 0.0196 | 0.007294 | −0.010878 | −0.023834 | 0.000826 | −0.004311 | 0.031044 |
| 197 | 0.017959 | −0.014258 | −0.025368 | −0.000153 | −0.017387 | 0.026345 | 0.032338 | 0.070578 | 0.061315 | −0.018589 | −0.034532 | 0.005323 | 0.01787 | −0.037269 |
| 198 | 0.091776 | 0.014337 | 0.030183 | −0.012084 | −0.030806 | −0.00584 | −0.023726 | 0.018643 | 0.018535 | 0.013535 | 0.007407 | 0.023044 | 0.012791 | −0.021143 |
| 199 | 0.020249 | 0.001285 | 0.040237 | 0.008506 | 0.012595 | 0.009238 | −0.016235 | 0.029947 | −0.009633 | 0.005571 | −0.008475 | 0.024821 | 0.006053 | 0.007975 |
| 200 | −0.048171 | 0.027148 | −0.020759 | −0.003958 | 0.022468 | 0.012323 | −0.04042 | −0.005739 | 0.002459 | 0.023871 | −0.013644 | −0.033881 | −0.015703 | 0.014005 |
| 201 | 0.074134 | 0.042154 | −0.027302 | −0.037599 | −0.025502 | −0.005422 | −0.026929 | 0.012218 | −0.055534 | 0.005224 | 0.041295 | 0.014959 | −0.002538 | 0.012648 |
| 202 | −0.036193 | 0.021902 | 0.001029 | 0.00706 | −0.009839 | −0.005517 | 0.035687 | −0.023707 | −0.009246 | −0.005804 | −0.000731 | −0.007076 | 0.034956 | 0.01523 |
| 203 | 0.001751 | −0.014234 | 0.007004 | 0.002329 | −0.011315 | 0.000508 | −0.035781 | −0.010407 | 0.031004 | −0.002441 | 0.014177 | 0.032808 | −0.017227 | 0.012415 |
| 204 | 0.044232 | −0.024828 | 0.037589 | −0.002756 | 0.007952 | −0.034069 | −0.028021 | −0.007523 | −0.060104 | 0.047704 | 0.043514 | −0.007741 | −0.024596 | −0.008227 |
| 205 | 0.003188 | −0.022041 | 0.02026 | −0.013402 | −0.027201 | −0.009816 | 0.002254 | −0.01553 | −0.025587 | −0.010915 | 0.010911 | −0.042325 | −0.053027 | −0.02301 |
| 206 | −0.018159 | 0.004139 | −0.041704 | −0.000237 | 0.036212 | 0.002369 | 0.026702 | −0.015758 | −0.016064 | −0.00957 | −0.046674 | 0.005854 | 0.053386 | 0.04375 |
| 207 | −0.001573 | −0.00953 | −0.038939 | 0.027896 | −0.00728 | 0.00662 | −0.013147 | 0.005745 | 0.014616 | −0.014479 | −0.004626 | −0.022652 | 0.025218 | 0.015328 |
| 208 | −0.044809 | −0.025796 | −0.028014 | 0.015135 | 0.013624 | 0.006488 | 0.031377 | 0.005993 | 0.00608 | −0.002244 | −0.027816 | 0.023901 | 0.075405 | 0.009522 |
| 209 | −0.028847 | 0.002121 | −0.05695 | 0.023555 | 0.009264 | 0.055048 | 0.029169 | 0.022184 | 0.011458 | −0.001895 | −0.021579 | −0.02232 | 0.047897 | 0.018906 |
| 210 | 0.031411 | −0.028902 | −0.003086 | −0.00743 | −0.013467 | 0.056298 | 0.033406 | 0.02185 | −0.008816 | −0.009419 | 0.011344 | −0.015103 | −0.029591 | −0.002724 |
| 211 | −0.01933 | 0.023634 | 0.038157 | −0.001074 | −0.002796 | 0.035487 | 0.010993 | −0.008394 | −0.005153 | −0.020184 | −0.012887 | −0.023322 | −0.018262 | −0.015194 |
| 212 | −0.013978 | 0.003865 | 0.010692 | 0.002176 | −0.017187 | 0.007795 | −0.031455 | 0.008875 | 0.036981 | 0.043364 | 0.017775 | −0.00625 | −0.008829 | 0.007919 |
| 211 | −0.04156 | 0.007648 | −0.012396 | 0.028086 | 0.00441 | 0.003694 | −0.006947 | −0.025342 | −0.002247 | −0.007449 | −0.000786 | 0.021359 | 0.007269 | 0.016002 |
| 214 | −0.009687 | 0.013553 | −0.018059 | −0.007089 | 0.012302 | −0.000801 | 0.005719 | 0.028281 | 0.023056 | 0.000069 | −0.035197 | 0.01104 | 0.008499 | 0.015703 |
| 215 | −0.057152 | 0.023122 | 0.027746 | −0.023311 | 0.011521 | −0.000015 | 0.026672 | −0.014714 | −0.077045 | 0.025223 | −0.041512 | 0.032441 | −0.001386 | −0.040974 |
| 216 | 0.068831 | −0.01786 | 0.005863 | −0.000562 | −0.031 | 0.012506 | −0.034404 | −0.021052 | −0.04716 | 0.031607 | 0.00394 | −0.012927 | −0.008473 | −0.016309 |
| 217 | 0.02357 | −0.000497 | −0.016846 | 0.00776 | 0.017422 | −0.032964 | 0.0085 | 0.009513 | −0.025294 | 0.014792 | 0.012996 | 0.031192 | 0.002497 | 0.020965 |
| 218 | 0.049016 | −0.00536 | 0.01629 | 0.035851 | 0.020063 | 0.023756 | 0.004256 | −0.000305 | 0.006806 | 0.02831 | 0.002365 | −0.014414 | 0.008627 | −0.006414 |
| 219 | 0.035892 | 0.025764 | 0.036487 | −0.014668 | −0.010212 | 0.003674 | −0.005803 | 0.028522 | −0.034932 | 0.03267 | −0.001785 | 0.002748 | −0.016234 | −0.017199 |
| 220 | 0.000013 | −0.003792 | 0.014503 | 0.028574 | 0.042597 | 0.018896 | 0.019712 | −0.009535 | 0.001084 | 0.038363 | 0.047202 | −0.060125 | −0.005928 | −0.029892 |
| 221 | −0.002282 | 0.012093 | 0.081794 | 0.022286 | 0.001433 | −0.029761 | 0.035296 | 0.026207 | 0.020039 | −0.087377 | −0.011474 | 0.037606 | −0.02356 | −0.046652 |
| 222 | −0.004092 | 0.031515 | 0.057667 | 0.00286 | 0.000276 | 0.021035 | 0.036623 | −0.022503 | 0.003775 | 0.027391 | −0.00164 | 0.034779 | −0.002622 | −0.026725 |
| 223 | 0.055333 | 0.004096 | 0.037405 | −0.000068 | 0.002371 | 0.026426 | 0.01987 | −0.038191 | −0.042548 | 0.039729 | 0.059652 | 0.03463 | 0.00013 | −0.010309 |
| 224 | 0.0019 | 0.01555 | 0.030648 | 0.007656 | 0.027328 | 0.006469 | 0.008025 | 0.037251 | −0.017791 | 0.014075 | 0.02121 | 0.012561 | −0.029958 | −0.025451 |
| 225 | 0.000871 | 0.019743 | 0.021156 | −0.001563 | 0.010862 | 0.024623 | 0.002179 | 0.017773 | −0.013838 | −0.006892 | 0.009075 | 0.002676 | −0.029895 | −0.034491 |
| 226 | 0.014952 | 0.015885 | 0.044008 | 0.037435 | 0.010065 | −0.001642 | 0.030096 | 0.034687 | 0.043614 | 0.006006 | 0.019347 | 0.02636 | 0.009096 | −0.021588 |
| 227 | −0.065574 | 0.022173 | −0.009054 | 0.008599 | 0.012871 | 0.011245 | 0.002271 | 0.013577 | −0.007559 | −0.022839 | −0.024284 | −0.007936 | 0.039225 | 0.062736 |
| 228 | −0.051475 | −0.021002 | −0.040526 | 0.024573 | 0.017706 | −0.002474 | 0.002764 | 0.045519 | 0.024509 | 0.015815 | 0.037537 | −0.022243 | −0.004583 | −0.036471 |
| 229 | −0.007929 | 0.020301 | 0.023944 | 0.022292 | 0.003873 | −0.009616 | −0.034663 | 0.021326 | 0.02428 | −0.018851 | −0.019015 | −0.007339 | 0.034776 | −0.002413 |
| 230 | −0.025409 | −0.022207 | −0.00298 | −0.033411 | −0.039458 | 0.021921 | 0.014994 | 0.023736 | 0.015003 | 0.010951 | −0.039362 | 0.012673 | −0.003234 | −0.017391 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 231 | −0.039674 | −0.045098 | 0.005763 | −0.041279 | −0.06331 | −0.019088 | 0.006231 | 0.020877 | 0.053632 | −0.04825 | −0.01098 | 0.016867 | 0.001348 | −0.011105 |
| 232 | −0.078034 | −0.040479 | 0.003581 | −0.016454 | −0.000165 | 0.007714 | −0.039775 | −0.050378 | −0.004592 | −0.051538 | −0.007952 | 0.049293 | −0.011995 | −0.112153 |
| 233 | 0.014138 | 0.014853 | 0.04031 | 0.015668 | −0.019265 | −0.040292 | −0.163593 | −0.091063 | −0.039215 | −0.012907 | −0.011851 | −0.03856 | −0.007773 | 0.052224 |
| 234 | −0.139246 | −0.002852 | 0.072223 | 0.004535 | −0.026933 | −0.01367 | −0.094761 | −0.010469 | 0.007287 | 0.046144 | −0.016489 | −0.025762 | −0.03342 | −0.017397 |
| 235 | 0.56956 | −0.006369 | 0.004368 | 0.004382 | −0.028268 | −0.038417 | 0.002257 | −0.081322 | −0.065439 | −0.004317 | −0.021802 | 0.013151 | 0.018102 | −0.030091 |
| 236 | −0.002535 | 0.774662 | −0.009995 | 0.009258 | 0.001735 | 0.006888 | −0.00152 | −0.056403 | 0.018026 | −0.015208 | 0.001374 | −0.008778 | −0.060269 | −0.04714 |
| 237 | 0.023066 | −0.010636 | 0.67614 | −0.047859 | 0.054028 | 0.02306 | −0.003927 | 0.043385 | −0.011952 | 0.023483 | 0.046124 | −0.022029 | 0.033451 | 0.011058 |
| 238 | 0.007599 | 0.025306 | −0.054454 | 0.816602 | −0.114706 | −0.010343 | −0.027388 | 0.021888 | −0.036744 | 0.033755 | 0.019794 | 0.033687 | −0.008248 | −0.003062 |
| 239 | −0.033637 | 0.021086 | 0.042516 | −0.138945 | 0.792647 | 0.001991 | −0.022891 | −0.000408 | −0.023815 | −0.010674 | −0.033584 | 0.031192 | −0.009346 | −0.018403 |
| 240 | 0.00181 | 0.023551 | 0.045536 | 0.003744 | −0.014039 | 0.755981 | −0.101317 | 0.026903 | 0.031507 | 0.005279 | 0.013794 | 0.009173 | 0.006638 | 0.010523 |
| 241 | −0.01832 | −0.018179 | 0.023011 | −0.008462 | −0.023605 | −0.114479 | 0.708164 | −0.026927 | −0.00156 | 0.025087 | −0.020262 | −0.01729 | −0.039528 | −0.005783 |
| 242 | −0.116863 | −0.066758 | 0.043605 | 0.015881 | −0.011178 | 0.023574 | −0.012826 | 0.704636 | −0.158128 | −0.003925 | 0.046165 | −0.043935 | −0.016524 | 0.00983 |
| 243 | −0.07652 | 0.011096 | −0.018069 | −0.016372 | 0.003543 | 0.039673 | 0.004207 | −0.134564 | 0.673889 | −0.003165 | 0.07279 | 0.017084 | −0.014644 | −0.017838 |
| 244 | −0.02671 | −0.023202 | 0.021742 | 0:042854 | 0.008803 | 0.005575 | 0.02016 | −0.010766 | 0.006216 | 0.797796 | −0.049547 | 0.031059 | 0.011563 | −0.003245 |
| 245 | −0.030185 | 0.009403 | 0.058099 | 0.034862 | −0.018103 | 0.0215 | −0.000796 | 0.014738 | 0.065004 | −0.058732 | 0.663085 | −0.030543 | 0.03623 | 0.043621 |
| 246 | 0.019274 | 0.018535 | −0.015276 | 0.02412 | 0.002394 | 0.031012 | −0.001713 | −0.03763 | 0.021565 | 0.040659 | −0.04169 | 0.820912 | −0.041837 | 0.020521 |
| 247 | 0.003996 | −0.055803 | 0.025447 | −0.03089 | −0.028298 | −0.002458 | −0.029847 | −0.017075 | −0.015036 | 0.027732 | 0.036689 | −0.040015 | 0.806347 | −0.106932 |
| 248 | −0.019255 | −0.054309 | 0.010235 | −0.019134 | −0.01514 | −0.004345 | 0.004694 | 0.036212 | 0.007246 | 0.019714 | 0.015253 | 0.028215 | −0.12013 | 0.775801 |
| 249 | −0.00065 | −0.023699 | 0.046447 | −0.016499 | 0.011731 | −0.118778 | −0.087203 | 0.039574 | 0.015649 | 0.052839 | 0.008472 | 0.033306 | 0.009029 | −0.063431 |
| 250 | −0.005841 | −0.027256 | 0.012702 | 0.028389 | 0.043299 | −0.119396 | −0.118482 | 0.005597 | 0.017943 | −0.007222 | 0.075684 | −0.034557 | −0.015909 | 0.028683 |
| 251 | −0.085119 | 0.024768 | −0.007809 | 0.006396 | 0.013485 | −0.130341 | −0.05631 | −0.010407 | −0.030884 | −0.044618 | −0.019001 | 0.009035 | 0.046476 | 0.036592 |
| 252 | −0.025923 | −0.01745 | 0.022657 | −0.005323 | −0.030602 | −0.01868 | −0.041629 | −0.069853 | −0.110951 | −0.018806 | −0.090411 | 0.039576 | 0.00928 | −0.013655 |
| 253 | 0.024696 | −0.009268 | −0.024166 | 0.02918 | 0.021744 | 0.026827 | 0.01131 | −0.020797 | −0.105795 | 0.001675 | 0.008937 | −0.018624 | 0.042215 | 0.045716 |
| 254 | 0.040022 | 0.010353 | 0.027547 | 0.003388 | −0.002585 | 0.020727 | −0.033736 | −0.023839 | −0.016543 | −0.045967 | 0.012244 | 0.012827 | 0.033303 | 0.009636 |
| 255 | 0.017975 | 0.011549 | 0.051149 | 0.024039 | 0.006574 | −0.033 | −0.011301 | 0.011032 | 0.00566 | −0.096003 | −0.005954 | −0.031757 | −0.018433 | −0.007583 |
| 256 | −0.000081 | 0.022327 | 0.077764 | 0.014235 | 0.009726 | 0.002034 | −0.026503 | 0.085508 | 0.045966 | 0.003895 | −0.159946 | −0.013468 | −0.011656 | 0.003506 |
| 257 | 0.00703 | 0.005669 | 0.033832 | 0.016627 | 0.016267 | 0.031409 | 0.01642 | 0.006529 | 0.033123 | 0.01244 | 0.003838 | 0.011098 | 0.006415 | 0.018641 |
| 258 | 0.012788 | −0.042996 | 0.024059 | 0.010673 | −0.022332 | −0.020221 | −0.019586 | 0.017644 | 0.015402 | 0.010989 | 0.007367 | 0.019867 | −0.070248 | −0.081221 |
| 259 | 0.003154 | −0.010515 | 0.013439 | 0.018092 | 0.024747 | −0.055016 | −0.003818 | −0.055244 | −0.047474 | 0.019412 | 0.018034 | 0.012096 | 0.006767 | −0.009678 |
| 260 | 0.016585 | −0.022552 | −0.015092 | 0.037036 | 0.025306 | −0.00198 | −0.028911 | −0.02058 | −0.024702 | −0.01591 | −0.017869 | 0.012745 | 0.007226 | −0.004882 |
| 261 | −0.02805 | 0.011704 | −0.020899 | −0.008753 | 0.01407 | −0.069207 | −0.014551 | −0.005801 | −0.024501 | 0.009785 | −0.030688 | 0.00892 | 0.016347 | 0.00855 |
| 262 | −0.007488 | −0.060074 | −0.008031 | −0.007053 | −0.012504 | 0.004624 | −0.000573 | −0.066522 | 0.002749 | 0.027167 | −0.009843 | −0.010596 | −0.019728 | −0.004262 |
| 263 | 0.002035 | −0.033208 | −0.020812 | −0.005863 | −0.012066 | 0.036476 | 0.041487 | −0.025957 | −0.00715 | 0.035953 | −0.033742 | −0.009165 | 0.016339 | −0.023101 |
| 264 | −0.001925 | 0.047244 | 0.021063 | 0.004134 | −0.008047 | −0.016383 | −0.002022 | 0.04646 | −0.000183 | −0.005958 | −0.007166 | 0.00717 | 0.014647 | −0.004837 |
| 265 | −0.018235 | 0.037141 | 0.020083 | 0.000418 | −0.045357 | −0.000421 | 0.016359 | 0.018602 | −0.035771 | 0.010731 | 0.019642 | −0.00338 | 0.002746 | 0.006153 |
| 266 | −0.024399 | 0.002814 | 0.029935 | 0.008247 | −0.010468 | 0.012434 | 0.017948 | 0.026579 | 0.002827 | 0.008501 | −0.036684 | 0.002176 | −0.0201 | −0.006419 |
| 267 | 0.033479 | 0.034151 | 0.049244 | 0.027145 | 0.015154 | 0.013461 | 0.024938 | −0.019955 | 0.003646 | 0.018258 | 0.005985 | 0.001324 | −0.015033 | 0.018517 |
| 268 | 0.001481 | 0.024747 | 0.048412 | 0.027656 | 0.001849 | 0.00178 | 0.012938 | 0.000168 | 0.010083 | 0.023646 | 0.058915 | 0.039728 | 0.007233 | −0.000973 |
| 269 | −0.030499 | 0.017968 | 0.035264 | 0.020586 | 0.034203 | −0.003414 | −0.009904 | −0.003411 | −0.004719 | 0.022824 | 0.061558 | 0.051855 | 0.016156 | −0.015638 |
| 270 | −0.016169 | 0.029037 | 0.049425 | 0.056561 | 0.018837 | −0.0011 | 0.01855 | 0.013466 | 0.004976 | 0.007258 | 0.034858 | 0.034113 | 0.044356 | −0.004706 |
| 271 | −0.085001 | −0.015547 | −0.038764 | −0.005146 | −0.004047 | 0.036426 | −0.032526 | −0.055371 | −0.051056 | −0.00088 | −0.031731 | 0.005403 | −0.020639 | 0.002362 |
| 272 | 0.089107 | 0.028609 | 0.014549 | −0.02267 | 0.012681 | −0.019812 | 0.027089 | 0.089937 | 0.039682 | 0.006689 | 0.022821 | 0.017888 | 0.014249 | 0.012099 |
| 273 | 0.030911 | 0.005007 | 0.029588 | 0.027215 | 0.037519 | −0.004858 | 0.041867 | 0.022452 | 0.007345 | 0.018385 | 0.050879 | 0.040645 | 0.009426 | 0.001946 |
| 274 | 0.008044 | 0.005321 | 0.026321 | 0.027803 | 0.039003 | −0.011205 | 0.032016 | 0.025494 | 0.003878 | 0.014012 | 0.05787 | 0.037202 | 0.004752 | −0.001987 |
| 275 | −0.0009 | −0.021438 | 0.016427 | 0.004392 | 0.012942 | 0.019285 | 0.011329 | 0.035228 | −0.022567 | −0.011047 | −0.024379 | 0.008749 | −0.009218 | −0.030616 |
| 276 | 0.01996 | −0.177541 | 0.022645 | 0.008557 | 0.006354 | 0.00206 | 0.021297 | −0.028423 | 0.03821 | 0.011277 | 0.000142 | 0.010826 | −0.03968 | −0.025974 |
| 277 | 0.002533 | −0.039141 | −0.051276 | −0.003658 | 0.005287 | 0.032395 | 0.006969 | −0.039551 | 0.006937 | 0.024549 | 0.045647 | 0.006657 | −0.011553 | 0.002589 |
| 278 | 0.05943 | −0.026182 | −0.024326 | −0.004945 | −0.015295 | 0.012003 | 0.00088 | −0.028309 | 0.025143 | 0.020394 | 0.005195 | −0.005891 | 0.006569 | 0.022883 |
| 279 | −0.033082 | 0.024798 | 0.078471 | −0.121896 | −0.166479 | −0.022778 | −0.020637 | 0.032716 | −0.008349 | 0.013416 | −0.028458 | 0.062037 | 0.010297 | −0.044242 |
| 280 | −0.044548 | 0.02889 | −0.005484 | 0.003453 | 0.018432 | 0.033786 | 0.035596 | −0.093837 | −0.225114 | 0.010245 | 0.036936 | 0.02294 | 0.018561 | 0.049304 |
| 281 | −0.020592 | 0.024462 | 0.050539 | 0.039377 | 0.013982 | −0.007815 | 0.011235 | −0.037361 | 0.0035861 | 0.052118 | −0.005527 | −0.096739 | −0.055169 | −0.036069 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 282 | 0.039183 | 0.002692 | 0.108664 | 0.037443 | 0.028378 | −0.008116 | −0.01305 | −0.059599 | −0.026287 | 0.045159 | −0.011415 | −0.070322 | −0.0482 | 0.008647 |
| 283 | −0.006002 | −0.061455 | 0.045691 | 0.007821 | −0.010934 | −0.018292 | −0.013353 | 0.030693 | −0.013716 | 0.011117 | 0.027733 | 0.000836 | −0.129471 | −0.112122 |
| 284 | −0.031604 | 0.004709 | 0.051256 | 0.021547 | 0.020923 | 0.022765 | 0.011653 | 0.009716 | 0.02169 | 0.011336 | 0.028707 | 0.024692 | 0.02831 | 0.033633 |
| 285 | −0.001275 | −0.016511 | 0.067778 | 0.034021 | 0.032968 | 0.034058 | 0.026043 | 0.011791 | 0.003031 | 0.008934 | 0.04587 | 0.028827 | 0.037869 | 0.047445 |
| 286 | 0.009125 | 0.030981 | 0.003393 | 0.003569 | 0.011569 | −0.013741 | −0.025686 | 0.009986 | −0.012799 | 0.025182 | 0.019753 | 0.064024 | 0.03819 | 0.016787 |
| 287 | 0.03135 | 0.036633 | 0.031176 | 0.026692 | 0.028161 | −0.004935 | −0.010062 | 0.025678 | −0.018862 | 0.015751 | −0.010403 | 0.065068 | 0.059327 | 0.035964 |
| 288 | −0.009893 | −0.065354 | −0.002009 | 0.049784 | 0.036183 | −0.019593 | −0.017407 | 0.029104 | 0.029293 | 0.042204 | 0.027084 | 0.00175 | −0.020417 | −0.076405 |
| 289 | −0.040133 | −0.073722 | 0.070038 | 0.036062 | −0.004492 | 0.020189 | 0.009468 | −0.04583 | 0.016553 | −0.004268 | −0.002185 | −0.013787 | −0.030115 | −0.010433 |
| 290 | 0.028026 | 0.010001 | −0.033047 | −0.019161 | 0.02086 | 0.004842 | 0.024963 | 0.004433 | −0.031476 | 0.006796 | 0.00301 | 0.027955 | 0.010451 | 0.008919 |
| 291 | 0.023668 | 0.016579 | −0.034372 | −0.024216 | 0.011127 | 0.001949 | 0.019927 | 0.002905 | −0.02733 | 0.003523 | −0.002414 | 0.024298 | 0.004341 | 0.003317 |
| 292 | −0.052654 | 0.017372 | −0.036723 | −0.050803 | −0.015908 | −0.005893 | −0.004373 | 0.021413 | −0.038515 | −0.013996 | 0.035314 | 0.025904 | 0.001213 | −0.003274 |
| 293 | −0.030019 | −0.042696 | 0.014561 | 0.023025 | 0.004586 | −0.010031 | 0.041651 | −0.05528 | −0.039019 | 0.052022 | 0.029676 | −0.0079 | −0.012707 | 0.008652 |
| 294 | −0.045702 | 0.012269 | 0.01041 | 0.025955 | −0.004651 | 0.022498 | −0.022655 | −0.002135 | −0.04527 | −0.006458 | 0.01293 | 0.006608 | −0.012263 | −0.019786 |
| 295 | 0.004172 | 0.014611 | 0.001073 | 0.003614 | −0.019171 | −0.001813 | 0.034741 | −0.032529 | −0.021218 | 0.036572 | 0.006299 | −0.014746 | −0.002079 | 0.011829 |
| 296 | 0.004944 | 0.025647 | 0.017831 | 0.007128 | 0.000579 | 0.022377 | 0.000671 | 0.011723 | −0.004993 | 0.012881 | 0.007401 | −0.001056 | −0.018226 | −0.014314 |
| 297 | −0.03614 | 0.002162 | 0.031111 | 0.016353 | −0.018517 | −0.0029 | 0.031093 | −0.035678 | −0.002552 | 0.043842 | −0.02013 | 0.005328 | 0.022071 | 0.025395 |
| 298 | 0.057444 | −0.015513 | 0.018269 | −0.017978 | −0.026075 | 0.011714 | −0.005844 | 0.013481 | 0.022911 | −0.052427 | −0.03604 | 0.023085 | 0.003056 | 0.005643 |
| 299 | 0.020515 | −0.031735 | −0.011635 | −0.014256 | −0.027685 | −0.001586 | −0.019247 | −0.018606 | −0.025629 | −0.001434 | 0.000796 | 0.02496 | −0.008239 | 0.007294 |
| 300 | −0.030382 | 0.007176 | −0.033678 | −0.006601 | −0.007548 | −0.033012 | −0.015462 | 0.048519 | 0.022302 | −0.016948 | −0.011885 | 0.041946 | 0.049967 | 0.016781 |
| 301 | −0.014394 | −0.026745 | 0.019274 | 0.002229 | −0.017613 | 0.04085 | 0.031483 | −0.020494 | −0.019932 | 0.011618 | −0.001067 | −0.018404 | 0.010768 | −0.003467 |
| 302 | −0.025525 | 0.013082 | 0.050331 | 0.016392 | −0.021061 | 0.030182 | 0.028312 | 0.00338 | 0.002279 | 0.027402 | −0.013524 | −0.023461 | 0.022451 | 0.000968 |
| 303 | 0.056484 | −0.009015 | 0.015688 | −0.005173 | −0.000415 | −0.028515 | −0.040625 | 0.001218 | −0.045251 | −0.038279 | 0.015292 | 0.028597 | −0.037114 | −0.008963 |
| 304 | 0.007157 | 0.002223 | −0.02961 | 0.024797 | 0.004537 | −0.010003 | 0.06013 | 0.029655 | −0.020414 | −0.022924 | −0.008304 | 0.006532 | 0.003605 | −0.011471 |
| 305 | 0.073917 | −0.00317 | −0.009288 | 0.01018 | 0.026787 | 0.032868 | 0.01907 | 0.045599 | 0.039761 | −0.035472 | 0.011757 | −0.025083 | 0.011839 | 0.012724 |
| 306 | −0.020162 | 0.006863 | 0.008655 | −0.014665 | −0.023449 | 0.002118 | 0.03052 | −0.020617 | −0.007126 | −0.030411 | −0.004315 | −0.023644 | −0.048721 | −0.021225 |
| 307 | 0.014614 | 0.00521 | 0.037173 | 0.001061 | 0.017121 | 0.018504 | 0.043732 | −0.052759 | −0.003593 | 0.018458 | 0.003812 | 0.034425 | 0.064299 | 0.032417 |
| 308 | 0.032759 | −0.002508 | 0.043276 | −0.003177 | −0.003975 | 0.029074 | 0.029478 | 0.039108 | 0.027307 | 0.005861 | −0.037 | −0.007563 | 0.02185 | 0.022736 |
| 309 | 0.017697 | 0.007828 | 0.012955 | −0.023283 | 0.001763 | −0.006322 | 0.029992 | 0.018392 | −0.014288 | 0.045193 | −0.007595 | −0.002616 | 0.004699 | 0.009832 |
| 310 | −0.001766 | 0.013989 | −0.001619 | 0.023646 | 0.035839 | −0.027156 | 0.032598 | 0.008793 | −0.010666 | −0.020791 | 0.017667 | −0.01704 | 0.007865 | −0.005306 |
| 311 | −0.013027 | 0.009853 | 0.023137 | 0.020223 | 0.006723 | 0.002367 | −0.000527 | −0.039358 | −0.006373 | 0.01492 | 0.010305 | 0.03629 | −0.003807 | −0.012923 |
| 312 | −0.011566 | 0.035372 | −0.032254 | 0.026014 | 0.043628 | 0.002546 | −0.029742 | −0.023055 | 0.005028 | −0.004802 | 0.052417 | 0.002156 | −0.018673 | 0.001912 |
| 313 | 0.006882 | 0.030144 | 0.016639 | −0.012406 | 0.003415 | 0.049324 | 0.01708 | 0.036485 | 0.045812 | −0.001651 | −0.017269 | −0.006197 | −0.010669 | −0.033773 |
| 314 | −0.066001 | −0.011379 | 0.000248 | 0.03987 | 0.00916 | −0.042363 | −0.036148 | −0.010845 | −0.007298 | −0.007148 | −0.065429 | 0.019922 | 0.012366 | −0.007097 |
| 315 | −0.037709 | 0.003707 | −0.026489 | −0.009718 | −0.002002 | 0.021547 | −0.023623 | 0.010785 | 0.01506 | −0.004752 | −0.014176 | 0.004013 | −0.007067 | 0.004934 |
| 316 | 0.026875 | −0.003675 | −0.013371 | −0.011072 | −0.010113 | 0.036705 | −0.023488 | −0.005267 | −0.051967 | −0.018556 | −0.002797 | 0.00488 | 0.022046 | 0.025129 |
| 317 | −0.018272 | 0.01669 | 0.011981 | 0.004443 | −0.006047 | 0.018014 | 0.036466 | 0.002999 | −0.014161 | 0.010138 | −0.029096 | −0.012033 | 0.012111 | 0.012375 |
| 318 | 0.003988 | −0.038127 | −0.071558 | −0.00013 | 0.029824 | −0.006313 | −0.008965 | 0.016039 | 0.023096 | −0.026909 | 0.023173 | 0.013979 | −0.035374 | −0.038009 |
| 319 | 0.010431 | 0.016482 | −0.023988 | 0.012324 | 0.022254 | 0.014359 | 0.017164 | 0.033823 | 0.012377 | −0.019094 | −0.004402 | 0.011502 | 0.028252 | 0.016846 |
| 320 | 0.058432 | 0.024148 | −0.009659 | 0.003305 | 0.000278 | 0.029636 | −0.044549 | 0.012804 | 0.035128 | 0.039547 | 0.023339 | −0.054565 | −0.017067 | 0.02303 |
| 321 | −0.034404 | 0.012124 | −0.008442 | −0.010144 | −0.006676 | 0.033367 | −0.04334 | −0.001179 | −0.03622 | 0.028915 | −0.0007 | −0.020093 | 0.000476 | 0.044878 |
| 322 | −0.035861 | −0.011654 | −0.01585 | −0.013512 | 0.006921 | 0.014306 | 0.0087 | 0.006991 | −0.033504 | 0.037607 | 0.017399 | −0.01243 | −0.032999 | −0.017429 |
| 323 | 0.002797 | 0.024195 | −0.027149 | −0.006552 | −0.004983 | −0.025874 | −0.000059 | −0.007912 | 0.005808 | 0.037071 | 0.018279 | −0.017033 | −0.010326 | −0.009038 |
| 324 | 0.017498 | −0.01111 | 0.000932 | 0.014867 | 0.025716 | 0.004088 | −0.027589 | 0.002297 | 0.034832 | −0.015403 | 0.020579 | −0.010207 | −0.009342 | −0.013719 |
| 325 | 0.031275 | −0.01168 | −0.014973 | −0.005733 | 0.035204 | 0.004626 | 0.011474 | −0.00188 | −0.000685 | 0.021156 | 0.011237 | −0.005149 | 0.0340231 | 0.04039 |
| 326 | 0.040042 | −0.019954 | −0.001119 | −0.00755 | 0.00361 | −0.046428 | −0.08713 | −0.022761 | −0.023752 | 0.006964 | −0.022182 | 0.02516 | −0.016474 | 0.003856 |
| 327 | −0.036029 | 0.008994 | −0.00205 | −0.014347 | −0.016094 | 0.003166 | 0.006308 | −0.00092 | −0.001654 | 0.010533 | 0.00791 | −0.010464 | 0.007988 | 0.004863 |
| 328 | −0.02384 | 0.013038 | −0.005843 | −0.009581 | 0.000976 | 0.003005 | 0.028068 | 0.033368 | −0.005392 | 0.036695 | 0.021298 | −0.002148 | −0.004826 | 0.015502 |
| 329 | −0.035169 | −0.00546 | −0.043984 | −0.010752 | −0.027691 | 0.007538 | −0.003552 | 0.015593 | −0.001828 | −0.001857 | 0.001394 | 0.009066 | 0.014051 | −0.007207 |
| 330 | −0.019672 | −0.006165 | −0.018866 | 0.021335 | 0.002795 | 0.004671 | −0.029678 | −0.060123 | 0.007117 | 0.006892 | 0.006719 | −0.040212 | 0.016587 | 0.024105 |
| 331 | 0.005417 | −0.011836 | 0.010843 | −0.018933 | −0.013393 | −0.03565 | −0.036001 | −0.022866 | −0.001713 | 0.011403 | 0.030782 | 0.004451 | −0.023295 | 0.001209 |
| 332 | −0.03145 | 0.007981 | 0.0132 | −0.015291 | 0.001375 | −0.025329 | −0.000375 | 0.014545 | 0.010501 | 0.019315 | 0.015466 | 0.011455 | 0.004739 | −0.02481 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 333 | −0.014338 | −0.021309 | 0.036141 | −0.010997 | −0.010081 | −0.011113 | 0.014644 | −0.012784 | −0.019438 | −0.011521 | 0.022647 | 0.014042 | 0.013362 | −0.007535 |
| 334 | 0.018148 | 0.008426 | 0.001978 | −0.007392 | −0.016807 | 0.004285 | −0.015135 | −0.028378 | −0.000728 | −0.00396 | 0.004287 | 0.031067 | −0.020199 | −0.010507 |
| 355 | −0.000161 | 0.0005 | 0.005599 | 0.004208 | 0.022029 | −0.01943 | −0.010805 | 0.025229 | −0.013561 | 0.010164 | −0.009803 | −0.008631 | 0.033814 | 0.030811 |
| 336 | 0.065411 | −0.0462 | −0.074779 | −0.021623 | 0.003757 | −0.002977 | 0.021399 | −0.026205 | −0.046751 | 0.023208 | 0.050059 | −0.008111 | −0.074559 | −0.05206 |
| 337 | −0.01333 | 0.013017 | 0.024087 | −0.021815 | 0.002751 | −0.027014 | −0.020987 | −0.002349 | −0.007682 | 0.002557 | 0.033584 | −0.007976 | −0.009359 | 0.011709 |
| 338 | −0.009032 | −0.04251 | 0.055437 | 0.010368 | 0.010459 | −0.034896 | −0.019335 | 0.009518 | 0.036632 | −0.015976 | 0.001886 | 0.028663 | −0.029958 | −0.021888 |
| 339 | −0.029576 | −0.007019 | −0.007837 | −0.01857 | −0.049853 | 0.001564 | 0.011165 | −0.016492 | 0.01765 | 0.009138 | −0.028319 | −0.000594 | 0.051836 | 0.009838 |
| 340 | 0.025908 | 0.052135 | −0.01038 | 0.002037 | 0.001828 | −0.005375 | −0.013538 | 0.018895 | −0.012889 | 0.0076 | −0.054538 | −0.010917 | 0.003998 | −0.001505 |

| | IP | IQ | IR | IS | IT | IU | IV | IW | IX | IY | IZ | JA | JB | JC |
|---|---|---|---|---|---|---|---|---|---|---|---|---|---|---|
| 1 | −0.0295 | 0.02971 | −0.015373 | 0.063959 | 0.014096 | −0.02634 | −0.006469 | 0.051215 | −0.029678 | −0.08132 | −0.015859 | 0.134025 | 0.075053 | 0.012287 |
| 2 | −0.095516 | −0.085126 | −0.06698 | −0.0275 | 0.086201 | 0.037225 | −0.007339 | 0.040799 | 0.034017 | 0.004732 | −0.061275 | −0.033098 | −0.036482 | 0.010398 |
| 3 | 0.041857 | 0.028168 | −0.004541 | 0.089579 | −0.07946 | 0.010146 | 0.065206 | 0.075403 | −0.04635 | 0.068896 | 0.056046 | 0.129731 | 0.036803 | −0.005147 |
| 4 | −0.038123 | −0.047078 | −0.038133 | −0.115029 | −0.135477 | −0.00357 | −0.040171 | 0.007261 | 0.076462 | −0.054022 | 0.025961 | 0.031547 | −0.039408 | −0.00486 |
| 5 | 0.002965 | −0.019555 | 0.000196 | −0.021398 | −0.048513 | 0.00682 | 0.022365 | 0.045428 | 0.003908 | −0.007835 | −0.044715 | −0.084157 | 0.021799 | 0.015844 |
| 6 | −0.070355 | 0.085426 | 0.0829 | −0.065321 | −0.084013 | 0.017583 | −0.001416 | −0.161749 | −0.004794 | −0.017222 | −0.025273 | 0.03596 | 0.050058 | −0.020787 |
| 7 | −0.01714 | −0.030144 | −0.039402 | −0.03114 | 0.044354 | −0.007343 | 0.027272 | 0.017895 | 0.013444 | −0.011104 | −0.015692 | −0.001572 | −0.032529 | −0.005134 |
| 8 | −0.013857 | −0.016389 | −0.029557 | −0.036919 | −0.064269 | 0.083359 | 0.020027 | 0.03809 | −0.018197 | −0.008639 | −0.010473 | −0.016722 | −0.031169 | −0.012933 |
| 9 | 0.015678 | 0.013297 | 0.069788 | −0.034204 | 0.030376 | 0.02914 | 0.0463 | −0.048366 | −0.045822 | −0.00541 | 0.006285 | −0.011982 | −0.061461 | −0.029659 |
| 10 | 0.059166 | −0.077951 | −0.006587 | 0.074733 | −0.071555 | 0.007096 | 0.007127 | −0.065238 | 0.006431 | 0.Q81219 | −0.028248 | 0.009425 | 0.050011 | 0.014755 |
| 11 | −0.006353 | 0.073534 | 0.000769 | −0.028538 | 0.036486 | 0.03161 | −0.019105 | −0.041685 | 0.018868 | −0.016087 | −0.012624 | 0.037109 | −0.011299 | 0.000866 |
| 12 | −0.034702 | −0.033353 | 0.015339 | 0.001432 | 0.007719 | −0.01179 | −0.01676 | −0.018181 | −0.038299 | −0.001234 | −0.031678 | −0.048636 | −0.011433 | −0.013591 |
| 13 | 0.058116 | 0.063904 | 0.071471 | −0.01085 | −0.056201 | −0.051839 | −0.032331 | −0.036696 | 0.022936 | −0.039962 | 0.057452 | −0.000557 | 0.022265 | −0.042997 |
| 14 | −0.029909 | 0.022161 | 0.008121 | −0.025156 | 0.086125 | −0.043524 | 0.051846 | 0.062438 | −0.002879 | −0.033777 | −0.011319 | −0.001408 | −0.007414 | 0.036543 |
| 15 | 0.007198 | 0.006647 | 0.055317 | −0.033918 | 0.004309 | −0.024763 | −0.004248 | −0.049791 | 0.038934 | 0.03786 | −0.025806 | −0.007278 | 0.023187 | 0.029755 |
| 16 | −0.056673 | −0.01389 | 0.000392 | 0.041033 | −0.023789 | 0.031282 | 0.020537 | 0.060286 | −0.014212 | −0.019486 | 0.000223 | 0.04155 | −0.011794 | −0.007002 |
| 17 | −0.026559 | 0.003898 | −0.002529 | −0.011969 | 0.011469 | −0.010024 | 0.020054 | −0.055296 | −0.013526 | 0.002491 | 0.013925 | 0.00078 | −0.054561 | −0.007257 |
| 18 | −0.055711 | −0.022089 | −0.029669 | −0.096919 | −0.017909 | 0.026532 | −0.033075 | −0.043044 | 0.03099 | 0.021879 | 0.027993 | 0.021289 | −0.058623 | −0.003141 |
| 19 | −0.01392 | 0.067722 | −0.010141 | −0.018771 | −0.041658 | −0.027047 | −0.007182 | 0.052752 | 0.04488 | −0.007689 | −0.008693 | −0.074567 | −0.071514 | −0.007528 |
| 20 | −0.065301 | −0.03043 | −0.023962 | −0.004715 | 0.032724 | 0.006545 | 0.071099 | −0.009609 | 0.04362 | 0.010981 | −0.028605 | −0.002451 | 0.028851 | 0.045156 |
| 21 | −0.02249 | −0.013723 | 0.053499 | −0.042753 | 0.023877 | 0.013369 | −0.006159 | −0.015355 | 0.014834 | 0.011308 | 0.017362 | −0.020727 | −0.032972 | −0.036637 |
| 22 | 0.062185 | −0.073859 | −0.024349 | 0.013213 | −0.003369 | −0.000692 | −0.030953 | 0.040374 | −0.010734 | 0.015511 | 0.025531 | 0.011399 | 0.024614 | −0.01449 |
| 23 | 0.054259 | −0.020891 | −0.015375 | −0.0149 | 0.08747 | 0.037982 | 0.019299 | 0.009885 | 0.024761 | −0.001408 | 0.017436 | 0.013703 | 0.022145 | −0.001808 |
| 24 | 0.018321 | −0.036856 | −0.064799 | −0.066027 | −0.018614 | −0.002043 | −0.000038 | −0.006379 | −0.054937 | −0.055654 | −0.005208 | −0.123526 | −0.038431 | −0.016629 |
| 25 | −0.024715 | 0.025096 | 0.033562 | 0.020726 | 0.068798 | 0.03936 | 0.027385 | 0.070551 | 0.013938 | −0.024168 | 0.03923 | 0.061434 | 0.127541 | 0.022246 |
| 26 | −0.029041 | 0.024358 | −0.015805 | −0.007206 | −0.030115 | −0.039645 | −0.061675 | −0.047832 | −0.060686 | −0.019751 | 0.045078 | 0.047001 | 0.085662 | 0.139337 |
| 27 | 0.029712 | 0.024713 | −0.026862 | −0.075006 | −0.050789 | −0.041952 | 0.002827 | −0.020832 | −0.015643 | 0.07379 | −0.038822 | −0.095847 | −0.090319 | −0.077458 |
| 28 | 0.058454 | 0.027368 | 0.051062 | 0.067901 | −0.031141 | −0.019713 | −0.006379 | 0.043956 | 0.000671 | 0.016878 | 0.059288 | 0.007227 | 0.023431 | −0.020886 |
| 29 | −0.03899 | −0.042016 | −0.055077 | 0.031403 | 0.036287 | 0.003343 | 0.018025 | 0.058289 | −0.01698 | −0.029834 | −0.020051 | −0.028362 | 0.010246 | −0.021997 |
| 30 | −0.0307 | −0.045375 | 0.069116 | 0.075748 | 0.069786 | 0.075961 | 0.041479 | −0.034106 | −0.119163 | −0.035249 | 0.021731 | 0.032534 | 0.079098 | −0.011433 |
| 31 | −0.015383 | −0.118403 | −0.170894 | −0.093703 | −0.122832 | −0.101732 | −0.086037 | −0.041902 | −0.021624 | −0.052644 | −0.087373 | −0.156002 | −0.13386 | −0.014789 |
| 32 | −0.034427 | 0.023926 | 0.015323 | −0.044902 | −0.036891 | 0.022822 | 0.010874 | −0.077131 | −0.022564 | 0.017544 | 0.015846 | −0.013592 | −0.03096 | −0.078622 |
| 33 | −0.018114 | −0.057021 | 0.053517 | 0.068712 | −0.048278 | 0.015959 | 0.055236 | 0.038312 | −0.05173 | 0.039782 | −0.021327 | 0.004143 | 0.060907 | 0.016311 |
| 34 | 0.002547 | 0.037461 | −0.014994 | −0.034121 | 0.074565 | −0.060797 | −0.029421 | −0.024514 | 0.000475 | 0.012674 | 0.017659 | 0.00491 | −0.011689 | 0.006181 |
| 35 | −0.03627 | −0.05957 | −0.044005 | 0.007308 | −0.038087 | −0.077866 | −0.021922 | 0.01777 | −0.057532 | 0.013007 | −0.032616 | 0.026584 | −0.017533 | −0.013286 |
| 36 | 0.017669 | −0.044374 | −0.054504 | 0.004952 | 0.01355 | 0.043443 | 0.059403 | 0.145323 | 0.022254 | −0.021783 | −0.059202 | −0.026123 | −0.093506 | −0.026897 |
| 37 | 0.016757 | 0.074388 | 0.031726 | −0.058798 | −0.035252 | 0.012115 | 0.016811 | −0.091294 | −0.010941 | 0.012245 | 0.097474 | 0.028953 | 0.049226 | −0.040415 |
| 38 | −0.015037 | 0.058012 | 0.048214 | −0.037906 | 0.029491 | 0.017015 | 0.037313 | 0.019042 | −0.007924 | −0.04219 | 0.0043 | −0.019684 | −0.002344 | −0.034242 |
| 39 | −0.000906 | −0.023719 | 0.032359 | −0:030288 | 0.012873 | 0.001049 | 0.030437 | −0.049715 | −0.038675 | −0.007688 | 0.048892 | 0.029932 | 0.000237 | −0.005435 |
| 40 | −0.168223 | −0.050762 | −0.014936 | 0.042381 | −0.001277 | −0.023635 | 0.020038 | −0.01323 | 0.012931 | −0.022302 | −0.062178 | 0.038595 | 0.041053 | 0.016681 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 41 | 0.095375 | 0.000178 | 0.012768 | −0.029225 | −0.053754 | −0.025764 | 0.007692 | 0.037059 | −0.020018 | −0.054127 | 0.002248 | −0.024798 | −0.018026 | −0.06304 |
| 42 | −0.03669 | −0.076705 | −0.056087 | 0.019397 | 0.113477 | −0.043428 | −0.048661 | 0.026227 | :0.018683 | −0.011112 | −0.085279 | −0.124992 | −0.095555 | −0.002844 |
| 43 | 0.053874 | 0.072489 | 0.05637 | 0.043367 | 0.020923 | 0.060359 | 0.018179 | −0.054087 | 0.023404 | 0.118896 | −0.001827 | −0.015596 | 0.027535 | 0.046764 |
| 44 | 0.058142 | −0.039747 | −0.037951 | −0.001327 | −0.042074 | −0.008761 | −0.018911 | 0.013472 | −0.00451 | 0.009911 | 0.012009 | −0.012107 | −0.006735 | 0.004702 |
| 45 | −0.074154 | 0.069257 | 0.059006 | −0.140578 | −0.075237 | 0.066243 | 0.003918 | −0.019657 | −0.012338 | −0.021694 | −0.026287 | −0.070669 | −0.016063 | −0.007781 |
| 46 | 0.00288 | −0.035864 | 0.021755 | 0.077316 | 0.004481 | −0.033475 | 0.025548 | −0.015921 | 0.065278 | 0.081545 | 0.032391 | 0.007452 | −0.001277 | −0.022906 |
| 47 | 0.019426 | −0.022802 | −0.000721 | 0.040795 | −0.020916 | 0.062767 | −0.001145 | −0.016816 | −0.029036 | −0.062676 | −0.011084 | −0.017682 | 0.036237 | −0.024042 |
| 48 | 0.013169 | −0.083456 | −0.033126 | 0.048377 | 0.008898 | 0.00356 | −0.041484 | −0.041707 | 0.022292 | 0.034813 | 0.00447 | 0.11498 | 0.036643 | 0.064317 |
| 49 | 0.079657 | 0.015145 | −0.085959 | −0.115128 | 0.040905 | 0.011263 | −0.0729 | −0.08956 | 0.08582 | 0.026148 | 0.04994 | 0.037926 | −0.083958 | −0.071405 |
| 50 | 0.04649 | 0.028808 | −0.010594 | −0.064592 | 0.002944 | 0.070615 | 0.076299 | −0.053038 | −0.030056 | −0.01499 | 0.034056 | 0.033499 | 0.052007 | 0.03085 |
| 51 | 0.01895 | 0.008912 | 0.024067 | −0.13755 | −0.046733 | −0.060276 | −0.059873 | 0.069161 | 0.00031 | 0.041126 | −0.024969 | −0.053908 | −0.01117 | −0.036981 |
| 52 | −0.087856 | 0.039359 | −0.008013 | −0.021635 | 0.009473 | 0.07136 | 0.032713 | −0.020628 | 0.045073 | −0.018045 | −0.035126 | 0.037462 | 0.019025 | −0.033748 |
| 53 | −0.085334 | −0.029665 | 0.042548 | 0.062769 | 0.002121 | −0.026837 | 0.04923 | −0.00348 | 0.037604 | −0.011235 | −0.000108 | 0.044765 | 0.042923 | 0.054446 |
| 54 | 0.020576 | 0.010671 | 0.006784 | 0.064994 | 0.046274 | 0.002257 | 0.006359 | 0.094456 | −0.00725 | 0.043674 | 0.01308 | 0.068953 | 0.030452 | −0.050966 |
| 55 | 0.042821 | 0.00861 | 0.074219 | 0.028026 | −0.030006 | 0.021083 | −0.020206 | −0.14262 | 0.007519 | −0.000825 | 0.025153 | 0.079928 | 0.004577 | −0.040831 |
| 56 | −0.012116 | 0.014525 | 0.006042 | 0.045874 | −0.018934 | −0.126113 | −0.013565 | 0.184876 | 0.049787 | −0.051185 | −0.082774 | −0.046523 | 0.051904 | 0.041613 |
| 57 | 0.02911 | −0.007612 | 0.029936 | 0.03513 | −0.026938 | −0.058445 | −0.154564 | −0.061768 | 0.025763 | −0.013225 | 0.09083 | 0.065634 | 0.051029 | 0.013821 |
| 58 | −0.08746 | 0.013514 | −0.026359 | −0.013259 | −0.052737 | 0.057146 | 0.011693 | −0.005566 | 0.027346 | 0.019996 | −0.053744 | 0.045027 | −0.00557 | 0.030629 |
| 59 | 0.040923 | 0.017954 | −0.003864 | −0.024524 | 0.049564 | 0.018779 | 0.003624 | 0.022165 | −0.002666 | 0.010385 | 0.041172 | −0.001182 | −0.006088 | −0.018577 |
| 60 | −0.086297 | −0.042027 | 0.054708 | 0.029676 | 0.029429 | −0.168863 | −0.056867 | −0.056124 | 0.008945 | −0.004611 | 0.113618 | 0.00839 | −0.043486 | −0.069167 |
| 61 | 0.031026 | 0.015209 | 0.016831 | 0.001678 | −0.086013 | −0.071266 | −0.01453 | 0.061547 | 0.003832 | −0.026793 | 0.014337 | 0.022186 | −0.00556 | −0.039363 |
| 62 | 0.060385 | 0.006693 | −0.022302 | 0.055114 | −0.029553 | −0.073908 | −0.055451 | −0.039703 | −0.023739 | 0.011118 | −0.012841 | −0.02089 | −0.003738 | 0.062009 |
| 63 | −0.110918 | 0.077037 | 0.024768 | −0.031846 | −0.081865 | 0.001198 | −0.004127 | −0.002521 | 0.06276 | 0.045347 | 0.003237 | 0.000313 | 0.020554 | −0.001607 |
| 64 | 0.047533 | 0.024791 | 0.009541 | 0.028633 | −0.015928 | 0.029614 | 0.005732 | 0.006536 | 0.007774 | 0.026026 | −0.008788 | −0.00977 | 0.013152 | 0.000374 |
| 65 | 0.084484 | 0.015549 | −0.040055 | −0.033064 | −0.031877 | 0.037809 | −0.056113 | 0.022511 | 0.028493 | 0.121965 | −0.019408 | 0.05611 | −0.018 | −0.023224 |
| 66 | 0.018493 | −0.097932 | −0.014018 | −0.013653 | 0.058981 | 0.048174 | −0.016705 | −0.063002 | −0.0817 | −0.09439 | 0.084579 | −0.006366 | 0.008781 | 0.006329 |
| 67 | 0.032361 | 0.054476 | 0.005989 | 0.059113 | 0.101608 | −0.021561 | −0.010371 | 0.000517 | 0.005719 | −0.000337 | 0.003524 | 0.093781 | 0.009934 | 0.023079 |
| 68 | 0.033048 | −0.013647 | −0.057122 | −0.007408 | 0.025434 | 0.022165 | −0.006965 | −0.018691 | −0.055249 | −0.023649 | −0.029141 | 0.002957 | −0.023974 | 0.016872 |
| 69 | −0.096695 | 0.017312 | −0.005348 | −0.070561 | −0.02994 | 0.017799 | −0.025582 | −0.106044 | −0.01497 | −0.08074 | 0.021871 | −0.044331 | −0.013541 | −0.030311 |
| 70 | 0.106532 | −0.058802 | 0.01012 | 0.025503 | −0.106761 | −0.04221 | 0.013223 | −0.051728 | −0.038726 | 0.04018 | 0.029535 | 0.023192 | −0.021538 | −0.021782 |
| 71 | −0.074613 | 0.046905 | 0.005184 | 0.01885 | 0.098676 | 0.069605 | 0.01947 | −0.041181 | 0.011447 | 0.040435 | 0.006129 | 0.03832 | −0.060362 | −0.005003 |
| 72 | 0.08296 | 0.039206 | −0.004049 | 0.058662 | −0.005426 | 0.029606 | 0.007363 | 0.045154 | 0.014296 | −0.062989 | −0.011975 | −0.037948 | 0.003859 | −0.00355 |
| 73 | 0.04912 | −0.019905 | −0.020034 | −0.036758 | −0.013551 | 0.042335 | −0.011094 | 0.034663 | 0.040851 | 0.006249 | 0.07428 | −0.033297 | −0.018088 | 0.029502 |
| 74 | 0.01408 | 0.037075 | −0.039928 | −0.024957 | 0.022993 | −0.009625 | 0.029789 | 0.01149 | −0.006743 | 0.017021 | −0.034818 | 0.059826 | −0.007413 | −0.047691 |
| 75 | −0.046949 | −0.050272 | −0.027218 | 0.08209 | 0.009046 | 0.006857 | −0.01162 | 0.009132 | 0.115265 | 0.02214 | −0.037989 | 0.012952 | 0.047364 | 0.00818 |
| 76 | 0.161213 | 0.064949 | −0.01008 | −0.039388 | −0.108256 | 0.106 | 0.004958 | 0.109422 | −0.041239 | −0.046357 | −0.045615 | −0.020741 | −0.005126 | −0.038143 |
| 77 | −0.012325 | 0.030752 | 0.022027 | −0.047517 | 0.08645 | 0.003817 | 0.066606 | −0.078425 | −0.058917 | 0.034299 | −0.025159 | −0.114289 | −0.073646 | −0.079575 |
| 78 | −0.080475 | −0.039696 | −0.049144 | 0.004306 | −0.073529 | −0.035414 | −0.025891 | −0.00738 | 0.014096 | 0.103706 | −0.024919 | 0.045182 | 0.015569 | 0.115855 |
| 79 | 0.037307 | −0.014807 | −0.032404 | 0.087508 | 0.107531 | 0.046092 | −0.060355 | 0.109829 | 0.020929 | −0.009376 | −0.00171 | 0.093618 | 0.048597 | 0.037702 |
| 80 | −0.057289 | 0.006092 | 0.050977 | −0.023128 | 0.01391 | −0.016733 | 0.018103 | 0.012278 | 0.00711 | 0.001521 | −0.011575 | −0.034595 | 0.006693 | −0.012696 |
| 81 | −0.069209 | −0.059764 | 0.007457 | 0.063791 | −0.01053 | 0.015855 | 0.018546 | 0.028554 | −0.03104 | −0.030484 | −0.007723 | 0.049141 | 0.022679 | −0.006364 |
| 82 | −0.006198 | −0.078839 | 0.009158 | 0.11602 | 0.007659 | 0.019432 | 0.016019 | 0.051545 | 0.006074 | 0.064532 | 0.050974 | 0.021464 | 0.040516 | −0.046502 |
| 83 | 0.024808 | 0.016289 | 0.010363 | 0.027671 | 0.061973 | 0.05868 | 0.029952 | 0.051602 | 0.027378 | 0.014988 | −0.007494 | 0.035783 | 0.025363 | 0.034479 |
| 84 | 0.120752 | −0.060149 | −0.062482 | 0.048688 | 0.003945 | 0.049541 | −0.024309 | −0.017249 | 0.059579 | 0.02305 | −0.002491 | 0.014141 | −0.014387 | −0.016792 |
| 85 | 0.035098 | −0.001123 | 0.048862 | −0.034417 | 0.021031 | 0.080519 | 0.03464 | −0.056593 | −0.029092 | 0.016128 | −0.012341 | 0.049898 | 0.069842 | 0.058006 |
| 86 | −0.000234 | −0.028279 | −0.046802 | 0.044663 | −0.030972 | −0.063403 | 0.037445 | −0.069519 | −0.097708 | 0.061163 | 0.040543 | 0.072248 | −0.022837 | −0.055938 |
| 87 | 0.03764 | 0.03719 | 0.058225 | −0.092902 | 0.027934 | −0.050225 | −0.054474 | 0.024344 | 0.037678 | 0.027885 | 0.012333 | −0.072274 | 0.029539 | 0.049254 |
| 88 | 0.064151 | 0.04286 | 0.061363 | 0.013046 | −0.054709 | 0.028856 | −0.043993 | −0.044491 | 0.011904 | −0.068574 | 0.017831 | 0.008545 | 0.038731 | 0.140436 |
| 89 | −0.029984 | 0.063077 | −0.032602 | 0.034404 | 0.043877 | 0.043636 | 0.032733 | 0.003332 | 0.099376 | 0.031489 | 0.021965 | 0.060833 | −0.099132 | −0.005744 |
| 90 | −0.105749 | 0.01106 | −0.068287 | −0.001211 | 0.017759 | −0.099361 | −0.071988 | −0.007898 | −0.048901 | −0.024431 | −0.022882 | 0.145926 | 0.011002 | 0.030863 |
| 91 | −0.010395 | 0.023277 | 0.057587 | 0.001165 | −0.035231 | 0.018676 | 0.020391 | 0.000351 | −0.042468 | −0.10435 | 0.009601 | −0.022465 | −0.048867 | −0.070855 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 92 | −0.12127 | 0.080745 | 0.024954 | −0.146857 | −0.009087 | 0.029623 | 0.056735 | −0.03593 | 0.014813 | −0.003103 | −0.045892 | −0.00746 | −0.002412 | −0.0789 |
| 93 | −0.049023 | −0.011548 | 0.051749 | 0.042817 | 0.057045 | −0.002915 | −0.013329 | 0.064092 | −0.021233 | −0.019218 | −0.012885 | 0.00835 | 0.050156 | 0.030621 |
| 94 | −0.012059 | −0.023947 | 0.006483 | 0.039541 | −0.023214 | 0.02496 | 0.019782 | 0.054172 | 0.018074 | −0.000818 | −0.092999 | −0.04867 | −0.044464 | −0.057239 |
| 95 | −0.028113 | 0.006228 | 0.021389 | 0.004201 | −0.051825 | −0.024073 | 0.048804 | 0.019155 | 0.021637 | −0.030534 | −0.002002 | −0.003227 | −0.027286 | −0.039203 |
| 96 | −0.034978 | −0.070389 | −0.048569 | 0.015891 | −0.043127 | −0.001829 | −0.045783 | −0.010818 | 0.01267 | 0.02512 | −0.001333 | 0.017767 | −0.067742 | −0.018878 |
| 97 | 0.053854 | −0.015889 | −0.045614 | −0.024677 | 0.028928 | 0.020097 | −0.033134 | −0.09499 | 0.000674 | −0.033105 | 0.008642 | 0.016773 | 0.037598 | 0.054726 |
| 98 | −0.003788 | 0.054409 | −0.000698 | −0.000603 | 0.065793 | −0.02299 | −0.018613 | −0.029126 | 0.014236 | −0.034529 | −0.051047 | −0.017937 | 0.003169 | −0.000371 |
| 99 | 0.066078 | 0.093198 | 0.071549 | −0.005838 | −0.061519 | −0.021395 | 0.063123 | 0.053078 | −0.023506 | −0.110607 | 0.048999 | −0.092798 | −0.098966 | 0.0415 |
| 100 | −0.04396 | 0.013376 | −0.018767 | −0.034857 | 0.082554 | −0.043976 | −0.06124 | −0.017441 | 0.046696 | 0.038159 | −0.050056 | −0.025048 | 0.051736 | −0.026862 |
| 101 | −0.008696 | 0.025978 | 0.020178 | 0.052781 | −0.019655 | −0.04097 | −0.020492 | −0.105891 | 0.013381 | 0.029433 | 0.067232 | 0.130036 | 0.107891 | 0.038183 |
| 102 | −0.000391 | 0.04233 | 0.0453 | 0.005976 | 0.079016 | −0.005637 | −0.008121 | −0.121893 | −0.021258, | 0.002799 | 0.00188 | 0.033902 | 0.020781 | −0.0068 |
| 103 | 0.031135 | 0.037759 | −0.016795 | 0.018942 | 0.00688 | −0.017099 | 0.020214 | 0.090946 | −0.025925 | −0.024294 | −0.002219 | 0.05177 | −0.006681 | 0.026383 |
| 104 | 0.06691 | 0.006886 | −0.03321 | −0.01015 | −0.048379 | 0.036259 | −0.054962 | −0.045278 | 0.022551 | 0.04156 | 0.001364 | −0.021303 | 0.013951 | −0.003885 |
| 105 | 0.025189 | 0.032391 | −0.005179 | 0.045758 | 0.009136 | −0.018592 | −0.000012 | 0.002877 | 0.04965 | −0.032063 | −0.011985 | 0.040139 | 0.016924 | −0.04314 |
| 106 | −0.012685 | 0.070825 | −0.017743 | −0.047395 | 0.058951 | −0.02367 | 0.01336 | −0.007592 | 0.020076 | 0.010538 | −0.016494 | −0.042989 | 0.066929 | 0.004435 |
| 107 | −0.042526 | −0.005972 | 0.05535 | 0.049004 | −0.018784 | −0.053616 | −0.030046 | −0.076235 | 0.001926 | −0.016153 | 0.013056 | 0.135831 | 0.043921 | −0.01962 |
| 108 | −0.063341 | −0.073726 | 0.026304 | −0.014121 | −0.01435 | 0.057833 | 0.028829 | 0.047276 | 0.022794 | −0.000556 | −0.010947 | −0.028844 | −0.007123 | −0.00518 |
| 109 | 0.064691 | 0.058978 | −0.033041 | −0.017659 | 0.056229 | 0.003956 | 0.006352 | 0.02177 | 0.032993 | −0.00234 | 0.044358 | −0.016401 | −0.019605 | −0.003637 |
| 110 | 0.035095 | 0.045883 | 0.000158 | 0.040109 | −0.022841 | −0.003263 | −0.007297 | −0.003098 | −0.037273 | −0.070135 | −0.006879 | 0.02421 | −0.021327 | −0.046626 |
| 111 | 0.041578 | 0.036651 | −0.007871 | 0.038977 | −0.018916 | 0.02169 | 0.068282 | 0.013345 | 0.033776 | −0.005036 | 0.069705 | 0.068235 | −0.003476 | 0.009798 |
| 112 | −0.006527 | 0.017279 | −0.009533 | −0.022508 | −0.034939 | 0.002819 | 0.039412 | 0.021781 | −0.050652 | −0.010263 | 0.004631 | −0.008334 | −0.043992 | 0.000039 |
| 113 | −0.019286 | 0.065248 | −0.01074 | −0.008874 | 0.031112 | −0.096272 | −0.046058 | −0.046329 | 0.014989 | 0.035324 | 0.003906 | 0.008605 | −0.057907 | −0.085746 |
| 114 | 0.079395 | 0.022063 | −0.007341 | 0.006769 | 0.044112 | −0.005354 | −0.050837 | −0.008654 | 0.001146 | −0.021076 | 0.053273 | 0.064308 | 0.051316 | 0.027574 |
| 115 | −0.032745 | −0.039506 | −0.02777 | −0.003402 | 0.042097 | 0.011079 | 0.005874 | −0.076914 | −0.027757 | 0.028776 | 0.015053 | 0.085244 | 0.063537 | 0.059896 |
| 117 | −0.041782 | −0.023395 | −0.028148 | −0.007586 | 0.022167 | 0.060522 | −0.004895 | −0.014061 | −0.04954 | −0.013356 | 0.004658 | −0.016873 | −0.055931 | 0.003369 |
| 113 | 0.017179 | 0.052211 | 0.017552 | −0.105659 | 0.007532 | −0.111597 | −0.015843 | 0.051614 | −0.012086 | −0.027137 | −0.008572 | −0.05298 | 0.022625 | −0.034938 |
| 118 | −0.068501 | 0.088075 | 0.055581 | −0.027676 | −0.051792 | 0.006317 | 0.086969 | 0.029707 | 0.009023 | 0.038287 | −0.061261 | −0.040102 | −0.04157 | −0.023643 |
| 119 | 0.022707 | −0.026645 | 0.035085 | −0.030111 | 0.018621 | 0.057303 | −0.034568 | 0.003249 | −0.013742 | 0.005191 | 0.009083 | 0.054433 | 0.095921 | −0.00771 |
| 120 | 0.116473 | −0.031665 | −0.010379 | 0.003041 | −0.027493 | 0.051309 | 0.05422 | 0.057259 | −0.00291 | 0.088568 | 0.067551 | −0.057522 | 0.079135 | 0.029217 |
| 121 | −0.020697 | −0.037593 | −0.037495 | 0.025909 | 0.011903 | 0.062267 | −0.018915 | 0.002959 | 0.06563 | −0.011577 | −0.069233 | 0.04351 | −0.063039 | −0.002388 |
| 122 | 0.004733 | 0.036335 | −0.051115 | −0.039226 | 0.045338 | −0.026212 | 0.038236 | 0.057975 | 0.080622 | 0.057896 | 0.031318 | −0.009967 | 0.034461 | 0.094793 |
| 123 | 0.078479 | 0.081915 | 0.075365 | 0.05839 | −0.043791 | 0.016615 | 0.002543 | 0.048878 | 0.013086 | −0.057421 | 0.037994 | 0.12226 | 0.021814 | −0.017339 |
| 124 | 0.041488 | −0.121695 | −0.051536 | 0.006266 | 0.011231 | −0.058416 | −0.088637 | −0.030883 | −0.02891 | 0.063299 | −0.010327 | −0.13567 | −0.007258 | 0.015008 |
| 125 | 0.06961 | −0.033916 | 0.017736 | −0.010423 | −0.040342 | −0.005278 | −0.060695 | −0.044174 | −0.034679 | −0.021061 | 0.07512 | 0.036552 | 0.043259 | −0.031851 |
| 126 | 0.035257 | 0.007392 | −0.160275 | −0.039379 | −0.012072 | 0.026708 | −0.076608 | −0.035927 | 0.041914 | −0.018564 | 0.025196 | 0.088408 | −0.079095 | 0.011318 |
| 127 | −0.090896 | −0.125752 | 0.039842 | 0.112675 | 0.044194 | −0.05019 | −0.007512 | 0.06778 | 0.008846 | 0.038015 | −0.015954 | −0.022038 | 0.099973 | −0.048155 |
| 128 | −0.064941 | −0.058216 | −0.099176 | 0.00256 | −0.028302 | 0.098039 | 0.064451 | 0.040217 | 0.024718 | 0.040451 | −0.036856 | 0.002601 | −0.067881 | 0.010796 |
| 129 | −0.004134 | 0.017417 | 0.044519 | 0.021674 | 0.024784 | −0.028351 | 0.007264 | 0.054629 | 0.038721 | 0.00542 | 0.016047 | −0.015273 | 0.032439 | −0.003685 |
| 130 | −0.032384 | −0.012198 | 0.018829 | 0.008893 | −0.000838 | −0.099618 | −0.053835 | −0.015521 | −0.024635 | 0.003836 | −0.041312 | −0.043187 | −0.043212 | −0.012055 |
| 131 | 0.002264 | −0.000641 | 0.009378 | 0.022094 | 0.00278 | 0.066252 | 0.007887 | −0.001027 | 0.002217 | 0.005149 | 0.029339 | 0.010196 | 0.026925 | 0.053209 |
| 132 | −0.059236 | 0.017106 | 0.016437 | −0.004124 | 0.025492 | −0.106231 | 0.024959 | −0.016785 | 0.025311 | −0.020321 | −0.013068 | 0.010687 | −0.050231 | 0.040015 |
| 133 | −0.03304 | −0.003011 | −0.002966 | −0.073746 | 0.019951 | −0.072261 | −0.00036 | 0.045435 | −0.01272 | −0.037244 | 0.000947 | 0.027563 | 0.001146 | −0.004805 |
| 134 | 0.018536 | 0.042538 | 0.035831 | 0.013125 | 0.056705 | −0.01775 | −0.038494 | 0.011238 | 0.032025 | −0.032153 | 0.011499 | −0.01061 | 0.018223 | −0.035511 |
| 135 | −0.01741 | −0.021054 | 0.093253 | 0.062146 | −0.017161 | −0.109744 | −0.067225 | −0.067358 | 0.02697 | −0.042083 | 0.004976 | 0.044095 | 0.036002 | −0.03316 |
| 136 | −0.007081 | −0.019014 | 0.021113 | −0.002183 | −0.042401 | 0.050703 | 0.022432 | −0.025461 | −0.006506 | 0.050345 | 0.022666 | −0.059846 | −0.001842 | −0.002836 |
| 137 | 0.033464 | 0.032309 | 0.014326 | −0.001582 | −0.03802 | 0.039918 | −0.008426 | −0.02465 | −0.035099 | 0.014155 | 0.039805 | 0.036846 | 0.042239 | 0.030995 |
| 138 | −0.056213 | −0.007999 | −0.007732 | 0.078395 | −0.028686 | −0.024039 | −0.042391 | −0.012531 | −0.001919 | 0.025108 | −0.070515 | −0.004146 | 0.051487 | −0.01051 |
| 139 | 0.030624 | 0.018739 | −0.014473 | −0.0456 | 0.054931 | 0.029127 | −0.033462 | 0.008773 | −0.065539 | −0.090624 | −0.010245 | −0.070432 | −0.030471 | −0.025621 |
| 140 | 0.024979 | −0.020234 | −0.051701 | −0.005133 | −0.016831 | 0.057947 | −0.018863 | −0.044007 | −0.014858 | 0.004668 | −0.004059 | 0.030118 | 0.043449 | −0.007614 |
| 141 | 0.010403 | 0.042787 | 0.020302 | −0.034025 | 0.048697 | 0.023831 | 0.007432 | −0.023836 | 0.011718 | 0.067119 | −0.003969 | −0.00463 | 0.039427 | 0.003192 |
| 142 | 0.024795 | −0.003126 | −0.033064 | 0.032064 | 0.017373 | 0.002865 | 0.013591 | 0.024155 | 0.044667 | 0.044044 | 0.011324 | 0.038768 | −0.02873 | −0.024587 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 143 | 0.016694 | −0.008178 | 0.019207 | 0.01115 | −0.043281 | −0.065151 | 0.009843 | −0.02352 | −0.032879 | 0.023679 | 0.019464 | −0.03051 | 0.005941 | −0.010015 |
| 144 | 0.005794 | −0.017674 | −0.000695 | 0.008913 | −0.032472 | 0.030475 | 0.017932 | −0.041928 | −0.022324 | −0.019869 | −0.020408 | 0.034143 | −0.07254 | −0.017205 |
| 145 | −0.030565 | −0.013778 | −0.002059 | 0.024773 | 0.037919 | 0.032572 | 0.019354 | 0.045401 | 0.002693 | −0.012962 | −0.000944 | 0.026417 | 0.018605 | 0.011782 |
| 146 | 0.025169 | 0.048629 | −0.017512 | −0.001252 | −0.012735 | 0.014341 | −0.026643 | 0.010362 | 0.02843 | 0.003943 | 0.011538 | 0.017708 | −0.020891 | 0.008928 |
| 147 | −0.027981 | 0.015056 | −0.009098 | −0.005478 | 0.00291 | −0.003371 | −0.008768 | −0.014727 | −0.014282 | −0.01478 | 0.03422 | 0.06111 | −0.000134 | −0.014663 |
| 148 | −0.015247 | 0.044513 | 0.030225 | −0.003967 | −0.024034 | 0.022607 | 0.019458 | −0.005753 | 0.016867 | −0.022863 | −0.02647 | 0.008697 | −0.010986 | −0.01002 |
| 149 | 0.033254 | 0.003993 | −0.044145 | 0.008847 | 0.036361 | −0.025872 | −0.034336 | 0.035849 | 0.016982 | −0.0193 | −0.018908 | −0.002587 | −0.064697 | −0.004834 |
| 150 | 0.075922 | 0.019996 | 0.012939 | 0.040518 | 0.004539 | 0.011657 | −0.001937 | 0.041175 | 0.009877 | −0.054277 | 0.033921 | −0.027448 | 0.016018 | 0.005499 |
| 151 | −0.043699 | 0.062829 | 0.046046 | 0.032295 | −0.001257 | −0.080334 | 0.007374 | 0.007804 | −0.00594 | −0.010252 | −0.008456 | 0.038522 | −0.03248 | −0.031205 |
| 152 | −0.003563 | 0.052768 | −0.008522 | −0.037705 | −0.044196 | −0.011143 | 0.03885 | 0.049144 | −0.009275 | −0.010076 | 0.001811 | −0.017126 | 0.049066 | −0.012305 |
| 153 | 0.005143 | 0.011815 | 0.014042 | −0.009714 | −0.010363 | −0.101402 | −0.049219 | −0.00103 | 0.021557 | 0.007641 | −0.001213 | −0.008712 | 0.01344 | 0.034363 |
| 154 | 0.004827 | 0.02315 | −0.027386 | −0.015275 | −0.019255 | 0.005832 | −0.014521 | 0.01981 | 0.030663 | 0.00927 | −0.008231 | 0.05085 | 0.027865 | −0.010942 |
| 155 | −0.037449 | −0.007107 | 0.01482 | −0.001876 | −0.03165 | −0.063921 | −0.024606 | −0.087444 | −0.032554 | −0.069023 | −0.002884 | 0.015083 | −0.00127 | 0.019622 |
| 156 | −0.023751 | −0.019754 | 0.008661 | −0.022552 | 0.030294 | 0.017551 | 0.048209 | −0.016332 | −0.009177 | 0.006011 | 0.058224 | 0.004705 | −0.026974 | −0.011686 |
| 157 | 0.009462 | −0.021114 | −0.020197 | −0.012621 | 0.021113 | −0.002929 | −0.038406 | 0.010408 | −0.010666 | −0.027287 | 0.003631 | 0.007647 | 0.030852 | 0.000908 |
| 158 | −0.027983 | −0.003161 | −0.002074 | −0.009851 | 0.029927 | 0.056789 | 0.006291 | −0.005143 | −0.019747 | −0.018921 | −0.041443 | 0.006417 | −0.017877 | −0.015807 |
| 159 | −0.040452 | 0.004157 | 0.065458 | −0.037664 | 0.005852 | 0.006678 | −0.016316 | −0.03911 | −0.006719 | 0.020054 | 0.007548 | −0.011773 | −0.025524 | 0.019063 |
| 160 | −0.047075 | 0.005114 | 0.001298 | 0.044211 | −0.002532 | 0.006469 | 0.012831 | −0.0091 | −0.034983 | 0.001754 | 0.001689 | 0.055749 | 0.003969 | −0.017789 |
| 161 | −0.068722 | −0.015367 | 0.024842 | 0.022398 | −0.029339 | −0.0252 | 0.000513 | −0.004622 | 0.031699 | 0.020119 | −0.008139 | 0.030314 | 0.037705 | −0.025943 |
| 162 | −0.03926 | 0.024891 | −0.029251 | −0.03478 | 0.028473 | 0.00753 | −0.010196 | −0.076493 | 0.036243 | 0.036451 | 0.009699 | −0.012868 | −0.023849 | 0.035541 |
| 163 | −0.012172 | 0.044912 | 0.046673 | −0.007084 | 0.001687 | 0.030353 | 0.05365 | 0.009497 | 0.007784 | −0.056596 | 0.022942 | −0.01059 | 0.016378 | −0.002471 |
| 164 | −0.015576 | 0.01069 | −0.000542 | 0.011553 | 0.008652 | −0.013415 | 0.000147 | −0.036087 | −0.002669 | 0.024789 | 0.019097 | 0.021692 | −0.036322 | −0.000927 |
| 165 | 0.036035 | 0.009918 | −0.02492 | 0.010387 | 0.026853 | 0.045949 | −0.004899 | −0.032586 | −0.027707 | −0.007743 | −0.016288 | 0.013146 | 0.018239 | −0.030975 |
| 166 | 0.009723 | 0.032455 | 0.031427 | 0.043904 | 0.027953 | 0.01068 | −0.018338 | −0.034306 | 0.037795 | −0.006558 | 0.033086 | 0.011237 | 0.013612 | 0.022629 |
| 167 | 0.022592 | −0.031094 | −0.043719 | 0.044095 | 0.025932 | 0.07312 | 0.010444 | 0.062352 | 0.00261 | 0.004928 | −0.058223 | −0.032914 | −0.048878 | −0.008945 |
| 168 | 0.03522 | 0.038045 | 0.019312 | −0.030239 | 0.031266 | −0.021279 | −0.008797 | −0.033208 | 0.013282 | −0.047047 | 0.077833 | 0.022801 | 0.026949 | 0.020974 |
| 169 | −0.005125 | −0.004896 | −0.00806 | 0.01824 | −0.042675 | 0.008161 | 0.004572 | −0.013428 | 0.003109 | −0.016164 | 0.012591 | 0.018211 | −0.015671 | 0.025282 |
| 170 | −0.044212 | −0.019204 | −0.021195 | 0.03959 | −0.027904 | −0.00009 | 0.003205 | −0.016379 | 0.021177 | 0.017566 | −0.007213 | 0.028872 | −0.017812 | 0.011153 |
| 171 | 0.005885 | 0.003861 | −0.008274 | 0.005622 | −0.040241 | −0.00379 | 0.032989 | 0.024514 | 0.002174 | 0.006321 | 0.011782 | −0.01984 | −0.02096 | −0.001376 |
| 172 | 0.014368 | 0.035663 | 0.027443 | −0.00922 | 0.007742 | −0.010142 | −0.000884 | −0.013778 | −0.031838 | −0.043284 | 0.025607 | −0.042231 | −0.019906 | −0.001773 |
| 173 | 0.033838 | −0.014626 | −0.028486 | 0.012232 | 0.021142 | −0.005752 | −0.012669 | 0.016017 | 0.024475 | 0.037666 | −0.014538 | −0.046086 | −0.013536 | 0.02824 |
| 174 | 0.003017 | 0.025762 | 0.008488 | −0.010919 | 0.05208 | −0.044388 | −0.008839 | −0.054528 | 0.05645 | 0.030777 | 0.024219 | 0.060026 | 0.018161 | 0.003408 |
| 175 | 0.041179 | −0.037608 | −0.042967 | −0.010318 | 0.011697 | −0.029456 | −0.012172 | 0.037097 | −0.020396 | −0.031393 | 0.010799 | 0.030952 | 0.029099 | −0.002488 |
| 176 | −0.036817 | 0.034115 | 0.016742 | −0.009008 | 0.014034 | −0.057518 | −0.032692 | −0.005523 | −0.027668 | −0.042822 | 0.003112 | −0.004461 | 0.0206 | 0.018751 |
| 177 | −0.020744 | 0.007362 | 0.00365 | −0.030284 | 0.054704 | 0.035565 | 0.005873 | −0.068703 | 0.006027 | −0.02179 | 0.036201 | 0.053169 | 0.035063 | −0.001503 |
| 178 | 0.018706 | −0.029285 | −0.004652 | −0.011967 | −0.004618 | −0.004868 | −0.02297 | −0.003315 | −0.012517 | −0.002149 | 0.012619 | −0.013481 | 0.048714 | −0.021193 |
| 179 | 0.001839 | 0.02099 | −0.005872 | −0.021511 | −0.018163 | −0.00509 | 0.016493 | 0.030415 | −0.000348 | −0.0041 | 0.018055 | 0.005177 | −0.000976 | −0.013624 |
| 180 | −0.00761 | −0.041681 | −0.029258 | 0.001109 | −0.001708 | 0.008239 | 0.003226 | 0.017444 | 0.009185 | 0.011234 | −0.00449 | 0.007444 | 0.002274 | −0.002993 |
| 181 | −0.003248 | −0.004847 | 0.002527 | −0.015644 | −0.02767 | −0.009758 | −0.000322 | −0.000564 | 0.005521 | −0.002268 | −0.000373 | 0.006246 | −0.003414 | −0.015863 |
| 182 | 0.036864 | −0.033966 | 0.004802 | 0.013618 | −0.019512 | 0.030054 | −0.044609 | −0.00406 | 0;006605 | −0.022227 | 0.005363 | 0.046458 | 0.00867 | −0.008026 |
| 183 | 0.03239 | −0.01549 | 0.004914 | −0.014012 | −0.020771 | 0.037922 | 0.00081 | 0.048947 | −0.018589 | −0.001755 | 0.016898 | 0.010218 | 0.012103 | 0.002559 |
| 184 | 0.018399 | −0.002361 | 0.048238 | 0.027773 | −0.027631 | 0.004609 | 0.025583 | −0.006421 | −0.011451 | 0.040703 | 0.034375 | −0.014381 | −0.001439 | 0.006118 |
| 185 | −0.038893 | 0.003679 | 0.020062 | −0.106545 | 0.037603 | −0.036849 | −0.028519 | −0.019866 | −0.016683 | 0.018261 | −0.002645 | −0.023822 | 0.016956 | −0.009563 |
| 186 | −0.048781 | −0.034806 | −0.021658 | 0.004805 | 0.027151 | −0.013521 | 0.031507 | 0.00389 | −0.00012 | 0.030831 | −0.023928 | −0.003985 | 0.018012 | 0.031265 |
| 187 | 0.03521 | −0.072124 | −0.014041 | 0.062852 | 0.002499 | 0.008719 | −0.057913 | 0.025496 | 0.01 6053 | 0.011664 | −0.031367 | −0/014878 | 0.011682 | 0.033542 |
| 188 | 0.003613 | 0.011511 | 0.014994 | 0.015675 | 0.019096 | 0.038908 | −0.0111 | −0.055895 | 0.019115 | 0.0089 | −0.02179 | 0.033571 | 0.026112 | 0.016574 |
| 189 | 0.010595 | 0.014569 | 0.015616 | 0.030757 | 0.013396 | 0.035669 | 0.002809 | −0.028593 | −0.002094 | −0.016671 | −0.015346 | 0.050996 | 0.009827 | 0.015551 |
| 190 | −0.039934 | 0.010483 | 0.02195 | −0.007352 | 0.020602 | −0.037593 | 0.013612 | 0.03723 | −0.001126 | −0.033244 | 0.002618 | 0.012451 | 0.001873 | −0.007515 |
| 191 | 0.019711 | −0.004761 | 0.020944 | −0.006977 | 0.01202 | −0.011891 | −0.003616 | 0.041411 | 0.015193 | −0.010957 | 0.034391 | 0.015947 | 0.030306 | −0.004359 |
| 192 | −0.005721 | 0.035827 | 0.035436 | −0.012514 | 0.034219 | 0.02216 | 0.024858 | 0.03735 | −0.036934 | −0.053371 | −0.039411 | −0.005434 | 0.006572 | −0.004004 |
| 193 | −0.066221 | −0.029759 | −0.021132 | 0.031419 | −0.004193 | −0.123268 | −0.041222 | 0.004227 | 0.002781 | 0.010807 | −0.058102 | −0.036143 | −0.008336 | 0.018419 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 194 | 0.021637 | −0.004419 | −0.01189 | 0.028923 | −0.044178 | 0.007099 | 0.036557 | 0.00679 | −0.036823 | −0.013342 | 0.015849 | 0.004282 | 0.034974 | 0.011067 |
| 195 | 0.009429 | −0.009877 | 0.015847 | −0.019104 | −0.002587 | −0.009387 | 0.012746 | −0.000685 | −0.010755 | 0.00277 | 0.009353 | −0.01987 | −0.055695 | −0.029311 |
| 196 | 0.074763 | −0.02595 | −0.027113 | 0.015559 | 0.003807 | 0.049204 | 0.029922 | −0.032099 | −0.036029 | 0.001015 | 0.05466 | 0.030437 | −0.060826 | −0.025013 |
| 197 | 0.002125 | 0.047214 | 0.007808 | −0.023057 | 0.018735 | 0.002994 | −0.010326 | −0.017418 | −0.023729 | −0.026589 | 0.035183 | 0.064057 | −0.038176 | 0.00843 |
| 198 | −0.011332 | 0.041192 | 0.012431 | −0.047449 | 0.01485 | 0.004579 | −0.016054 | −0.03106 | 0.011548 | 0.020421 | 0.025884 | −0.04098 | −0.004841 | −0.021531 |
| 199 | −0.001108 | −0.034323 | 0.026914 | 0.00463 | −0.015813 | −0.002724 | 0.029007 | 0.00444 | −0.041838 | −0.058991 | 0.029132 | −0.069953 | −0.027437 | −0.017474 |
| 200 | −0.013226 | 0.018865 | 0.011487 | 0.023834 | −0.003679 | 0.009217 | 0.010125 | −0.016706 | 0.010564 | 0.036656 | 0.000772 | 0.014989 | 0.014883 | −0.051009 |
| 201 | −0.03392 | −0.029511 | 0.024848 | 0.036569 | 0.007067 | −0.013073 | 0.04047 | 0.019599 | −0.007359 | 0.029817 | 0.004484 | 0.028726 | 0.006269 | 0.009943 |
| 202 | −0.018225 | 0.032894 | 0.016291 | 0.005831 | 0.005623 | 0.05593 | 0.035767 | 0.000613 | 0.036299 | −0.01057 | 0.026971 | 0.023003 | 0.007538 | −0.04402 |
| 203 | 0.009964 | 0.016034 | 0.035627 | 0.00491 | −0.010996 | 0.020505 | 0.006159 | −0.029177 | −0.008256 | 0.012776 | 0.03641 | 0.00466 | −0.004988 | −0.015518 |
| 204 | 0.025762 | −0.0326 | −0.050451 | −0.032939 | −0.005279 | 0.007614 | −0.018232 | −0.01499 | −0.018139 | −0.007945 | −0.008078 | 0.009194 | 0.034403 | 0.004398 |
| 205 | −0.007135 | −0.03372 | 0.003415 | 0.019753 | −0.05933 | 0.021417 | −0.007144 | 0.039052 | −0.015398 | −0.001704 | −0.00736 | −0.021342 | 0.006844 | 0.045712 |
| 206 | −0.055889 | −0.021041 | −0.021498 | −0.028036 | 0.007917 | −0.036681 | 0.026604 | −0.024114 | −0.021665 | 0.051652 | −0.010672 | 0.004431 | −0.043506 | −0.027522 |
| 207 | −0.002342 | −0.022813 | 0.006988 | −0.005251 | 0.006594 | −0.017909 | 0.012113 | −0.01319 | 0.020764 | 0.020045 | 0.010646 | −0.032108 | −0.008582 | 0.001684 |
| 208 | −0.022795 | 0.019691 | −0.040781 | 0.018111 | 0.002988 | −0.019941 | 0.013406 | −0.033013 | −0.0022 | 0.007888 | −0.029897 | 0.020469 | 0.021333 | 0.032549 |
| 209 | 0.020069 | −0.014654 | −0.026573 | −0.003436 | −0.026128 | −0.020008 | 0.015236 | −0.002327 | 0.034129 | 0.038676 | 0.001422 | −0.026745 | −0.006795 | −0.018039 |
| 210 | 0.010518 | −0.003829 | −0.003295 | −0.006867 | 0.003221 | 0.006823 | −0.001973 | 0.000057 | −0.018928 | 0.002559 | −0.005687 | 0.010135 | −0.034292 | 0.021421 |
| 211 | −0.011341 | −0.001202 | 0.037496 | 0.025574 | 0.024092 | −0.071636 | −0.014398 | 0.026015 | 0.006638 | −0.014446 | 0.013526 | −0.015969 | 0.024279 | −0.015316 |
| 212 | −0.013455 | −0.007283 | 0.025812 | 0.041204 | −0.006118 | −0.011108 | 0.00974 | −0.02385 | 0.005221 | 0.009867 | 0.016538 | 0.050586 | 0.03375 | −0.024931 |
| 213 | 0.023498 | 0.004442 | −0.005378 | −0.006756 | 0.010773 | −0.015427 | −0.024431 | 0.010586 | 0.020085 | 0.006951 | −0.007435 | −0.021447 | −0.03285 | 0.025272 |
| 214 | 0.015287 | 0.009 | −0.025407 | −0.014483 | −0.007747 | 0.024744 | 0.042579 | 0.012566 | −0.007769 | 0.024173 | 0.013874 | −0.017422 | −0.021465 | −0.027743 |
| 215 | 0.052467 | −0.023523 | −0.070994 | −0.02774 | −0.022188 | 0.039037 | 0.009156 | −0.074538 | −0.000721 | 0.008773 | −0.048076 | −0.028889 | −0.05823 | 0.00706 |
| 216 | 0.045329 | 0.010052 | 0.049862 | −0.002416 | −0.05568 | −0.004741 | −0.013951 | −0.000683 | −0.007712 | −0.010565 | 0.023754 | 0.019318 | 0.028776 | −0.005079 |
| 217 | −0.012278 | −0.02475 | 0.015322 | 0.014133 | −0.024386 | 0.070841 | 0.070541 | 0.039696 | −0.014829 | −0.026836 | 0.015183 | −0.00368 | −0.050831 | −0.038532 |
| 218 | 0.023063 | −0.0013 | 0.0252 | 0.020953 | −0.005363 | 0.028315 | 0.01883 | 0.003704 | 0.028626 | −0.005018 | −0.010502 | 0.000849 | 0.012297 | 0.014434 |
| 219 | 0.008621 | −0.016881 | −0.001908 | 0.035 | 0.029449 | 0.004888 | 0.014071 | 0.023165 | 0.007731 | 0.030877 | −0.015874 | −0.011892 | −0.012703 | 0.033423 |
| 220 | 0.00224 | −0.014586 | 0.022714 | 0.053271 | −0.028644 | 0.025103 | −0.00057 | 0.002173 | 0.000408 | 0.014219 | 0.012099 | 0.003639 | 0.015339 | −0.016042 |
| 221 | 0.036622 | 0.007382 | −0.024383 | −0.006279 | 0.053422 | 0.006584 | −0.078235 | −0.012338 | 0.004748 | −0.030631 | 0.019538 | −0.013083 | −0.012495 | −0.000791 |
| 222 | −0.071456 | 0.047599 | −0.003985 | −0.001786 | 0.044311 | −0.014552 | 0.02793 | 0.010191 | −0.018874 | −0.01663 | −0.075959 | −0.002401 | 0.011483 | −0.011717 |
| 223 | −0.02005 | 0.00607 | −0.00577 | 0.004583 | −0.024487 | −0.110411 | −0.003781 | 0.013648 | 0.009987 | 0.024287 | −0.075744 | −0.018576 | −0.018582 | −0.017078 |
| 224 | −0.017807 | −0.013471 | 0.012652 | 0.00664 | 0.018634 | −0.02685 | −0.005605 | −0.011594 | 0.011943 | −0.001032 | −0.004815 | 0.004645 | 0.004424 | −0.012221 |
| 225 | −0.027437 | 0.004195 | 0.012715 | 0.003879 | 0.031149 | −0.044664 | −0.000256 | 0.005126 | 0.010564 | −0.028927 | −0.019603 | −0.031699 | −0.001908 | −0.006598 |
| 226 | 0.000114 | 0.043138 | 0.018985 | −0.024091 | −0.007785 | 0.036883 | 0.007604 | 0.000628 | −0.023134 | −0.018475 | −0.008496 | 0.000225 | 0.011227 | −0.000303 |
| 227 | −0.003262 | −0.014735 | −0.011073 | 0.018178 | 0.005589 | −0.003988 | −0.002257 | 0.034596 | 0.013774 | 0.035331 | 0.004799 | −0.009874 | 0.020227 | 0.021975 |
| 228 | −0.009029 | 0.014042 | 0.028142 | 0.04608 | −0.080601 | 0.022651 | −0.010228 | −0.01939 | 0.018803 | −0.021268 | −0.013616 | −0.029607 | −0.030157 | −0.022387 |
| 229 | −0.020165 | 0.001306 | 0.002701 | 0.034792 | −0.044329 | 0.008574 | 0.001312 | −0.07246 | 0.031091 | 0.048964 | 0.015121 | 0.015942 | 0.01435 | 0.017077 |
| 230 | −0.005987 | 0.038119 | −0.011094 | −0.029598 | 0.008485 | 0.020135 | 0.015688 | −0.014058 | 0.015198 | 0.014712 | −0.00027 | −0.002815 | −0.011297 | −0.027958 |
| 231 | −0.021413 | −0.049504 | 0.015369 | 0.026715 | −0.013586 | −0.013325 | −0.044313 | 0.059364 | 0.013646 | −0.0261 | 0.020029 | −0.027188 | −0.014181 | −0.019598 |
| 232 | −0.091981 | −0.001223 | −0.037554 | −0.032618 | −0.042302 | −0.024773 | 0.00953 | 0.012233 | −0.003957 | 0.010781 | 0.034782 | −0.022613 | −0.013992 | −0.031122 |
| 233 | 0.002423 | −0.024754 | 0.019471 | −0.030054 | −0.028497 | −0.02444 | −0.000034 | 0.022105 | −0.026846 | 0.02603 | 0.032202 | −0.031376 | 0.046798 | 0.016755 |
| 234 | 0.025671 | −0.042138 | −0.018027 | 0.039094 | 0.001974 | 0.038519 | 0.033415 | −0.041211 | −0.032394 | 0.011902 | 0.022272 | 0.00726 | −0.036581 | −0.004767 |
| 235 | −0.008632 | −0.004474 | −0.098246 | −0.014505 | 0.011631 | 0.04174 | 0.025503 | 0.016503 | −0.003328 | −0.008226 | −0.006076 | 0.020502 | −0.026529 | −0.012434 |
| 236 | −0.002767 | −0.035027 | 0.003499 | 0.004444 | −0.010076 | 0.021227 | −0.005178 | 0.014789 | 0.018726 | −0.019251 | −0.005233 | 0.00526 | 0.030378 | −0.041386 |
| 237 | −0.006247 | 0.013573 | −0.001181 | 0.027822 | −0.014374 | −0.013368 | 0.023807 | 0.020585 | 0.046948 | 0.001588 | 0.01481 | 0.015415 | −0.038003 | −0.004616 |
| 238 | −0.01241 | 0.010042 | −0.010554 | −0.004699 | 0.021462 | −0.010864 | 0.023331 | 0.020128 | 0.016489 | 0.03989 | 0.017844 | 0.03714 | −0.01772 | −0.009273 |
| 239 | 0.033274 | 0.052661 | 0.009002 | −0.034159 | 0.016224 | −0.002215 | 0.025589 | 0.053853 | 0.021711 | 0.006368 | 0.023848 | 0.012646 | 0.014879 | −0.002349 |
| 240 | −0.112472 | −0.113416 | −0.09041 | −0.016922 | 0.000216 | 0.020231 | −0.027116 | 0.002434 | 0.037793 | −0.023526 | −0.043473 | −0.010408 | −0.038291 | 0.02146 |
| 241 | −0.092437 | −0.106568 | −0.074614 | −0.050341 | 0.008908 | 0.020327 | 0.00173 | −0.049258 | 0.021275 | −0.007112 | 0.008166 | 0.018209 | 0.002197 | 0.025603 |
| 242 | 0.042332 | 0.000936 | −0.018824 | −0.069404 | −0.060895 | −0.004671 | −0.009081 | 0.077297 | 0.013432 | 0.013036 | −0.054364 | −0.018142 | 0.014082 | −0.032669 |
| 243 | −0.00543 | 0.011481 | −0.012209 | −0.075954 | −0.094498 | −0.01222 | −0.005009 | 0.031759 | 0.025511 | 0.022334 | −0.053522 | 0.016134 | 0.009105 | 0.025004 |
| 244 | 0.02315 | −0.022937 | −0.047086 | −0 015066 | 0.020255 | −0.079568 | −0.117696 | 0.021789 | 0.045071 | 0.002688 | −0.001937 | −0.03343 | 0.006383 | 0.021782 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 245 | 0.053859 | 0.077119 | −0.012674 | −0.076045 | −0.005357 | 0.024649 | 0.007869 | −0.118079 | 0.012983 | 0.000013 | 0.007373 | −0.036751 | −0.027825 | 0.005432 |
| 246 | 0.039458 | −0.005855 | 0.024505 | 0.039586 | −0.002839 | 0.016308 | −0.013636 | −0.029622 | 0.021505 | 0.003528 | 0.018008 | 0.02178 | 0.032871 | 0.029506 |
| 247 | 0.010333 | −0.002493 | 0.013827 | −0.003131 | 0.037738 | 0.035744 | −0.003105 | 0.017892 | 0.00319 | −0.071244 | −0.002067 | 0.00724 | 0.011844 | −0.011132 |
| 248 | −0.050932 | 0.04415 | 0.018694 | −0.025091 | 0.015808 | 0.025227 | 0.008745 | 0.013764 | −0.000114 | −0.082996 | −0.015661 | −0.003047 | −0.015674 | −0.024167 |
| 249 | 0.6027 | −0.049958 | −0.004912 | −0.033705 | 0.04629 | −0.061652 | 0.045728 | −0.05475 | 0.012211 | 0.013698 | −0.113022 | 0.002618 | −0.027277 | −0.019496 |
| 250 | −0.058774 | 0.710962 | −0.10952 | 0.074004 | 0.011967 | −0.004837 | −0.050606 | 0.000015 | −0.016083 | 0.035098 | −0.028728 | −0.028299 | 0.007382 | 0.033956 |
| 251 | −0.016594 | −0.131967 | 0.748612 | −0.052493 | 0.011144 | 0.015791 | −0.053596 | 0.02424 | 0.047782 | 0.026848 | −0.072223 | −0.02358 | −0.09964 | 0.0246 |
| 252 | −0.031605 | 0.088969 | −0.035218 | 0.67265 | −0.050489 | −0.005434 | −0.011312 | −0.065271 | 0.00122 | −0.020236 | −0.032451 | −0.143522 | −0.110615 | −0.046208 |
| 253 | 0.037377 | −0.001743 | 0.014584 | −0.039648 | 0.669236 | −0.032915 | −0.022362 | −0.021513 | −0.013488 | −0.001 | −0.003034 | −0.034296 | −0.027939 | −0.003136 |
| 254 | −0.101417 | −0.010739 | 0.025814 | −0.00348 | −0.015499 | 0.667475 | −0.098247 | −0.033188 | 0.025107 | −0.002099 | −0.03711 | −0.05749 | −0.017021 | −0.013636 |
| 255 | 0.009478 | −0.04329 | −0.037724 | −0.008337 | 0.013071 | −0.113759 | 0.807722 | −0.072911 | 0.045119 | −0.00875 | 0.002769 | 0.003019 | 0.021169 | 0.026026 |
| 256 | −0.024056 | 0.051714 | 0.039704 | −0.074854 | 0.006459 | 0.008927 | −0.054205 | 0.611853 | −0.049286 | 0.016137 | 0.078737 | 0.0766 | 0.009573 | −0.00898 |
| 257 | 0.020758 | −0.0121 | 0.015474 | −0.016513 | −0.008691 | 0.011369 | 0.016968 | −0.025445 | 0.810319 | −0.061011 | 0.016601 | −0.032664 | 0.022341 | −0.017058 |
| 258 | −0.024522 | 0.041186 | 0.031685 | −0.029861 | 0.002728 | −0.011982 | −0.004226 | 0.038693 | −0.048846 | 0.760323 | −0.006607 | −0.038052 | −0.009776 | −0.022848 |
| 259 | −0.120276 | −0.055687 | −0.06415 | −0.01946 | −0.010079 | −0.015576 | 0.007476 | 0.067869 | 0.025332 | 0.005733 | 0.796805 | −0.100885 | −0.06141 | −0.010326 |
| 260 | −0.035035 | −0.055538 | −0.016245 | −0.153654 | −0.049284 | −0.06135 | 0.010604 | 0.04983 | −0.001822 | −0.004907 | −0.115038 | 0.593374 | −0.163113 | −0.042842 |
| 261 | −0.043901 | −0.028634 | −0.093379 | −0.117942 | −0.047023 | −0.024915 | 0.00186 | −0.009922 | 0.011677 | −0.03081 | −0.076442 | −0.161499 | 0.704005 | −0.095076 |
| 262 | 0.008103 | 0.026996 | 0.034601 | −0.058746 | −0.049741 | −0.004309 | 0.02426 | −0.002678 | −0.019948 | −0.020304 | 0.001887 | −0.072449 | −0.083403 | 0.813653 |
| 263 | −0.007611 | 0.056424 | 0.050163 | −0.059254 | −0.083887 | −0.017165 | 0.005042 | −0.026036 | −0.030648 | −0.010998 | −0.005072 | −0.05529 | −0.052261 | −0.136717 |
| 264 | −0.107045 | 0.000934 | 0.015175 | 0.034633 | −0.017863 | −0.028877 | −0.000316 | −0.009911 | 0.015448 | 0.002377 | −0.084948 | −0.005686 | 0.016318 | 0.057016 |
| 265 | −0.013727 | 0.006241 | 0.045195 | 0.005324 | −0.050538 | −0.088974 | −0.007782 | −0.010545 | 0.027932 | −0.042912 | −0.044214 | −0.060777 | −0.028375 | 0.009767 |
| 266 | 0.034422 | −0.000757 | 0.011313 | −0.02002 | −0.034759 | −0.04002 | −0.019986 | −0.117559 | 0.013654 | 0.008047 | 0.037595 | −0.011092 | −0.098389 | −0.0439 |
| 267 | 0.027646 | 0.003604 | 0.044362 | 0.008838 | −0.11492 | −0.018659 | 0.02662 | −0.009426 | −0.00841 | −0.017723 | 0.013501 | −0.024578 | 0.015196 | −0.016324 |
| 268 | 0.004597 | 0.024279 | 0.039137 | −0.014797 | −0.014255 | 0.027145 | 0.021397 | 0.01789 | −0.026463 | 0.012822 | 0.010673 | −0.002396 | 0.036683 | −0.00577 |
| 269 | −0.016149 | −0.002388 | −0.013584 | −0.019282 | −0.012113 | 0.046653 | 0.02439 | 0.003331 | −0.017974 | 0.052353 | 0.00752 | 0.019882 | 0.023151 | −0.00251 |
| 270 | 0.006506 | −0.004678 | −0.013552 | −0.019377 | −0.028045 | 0.018154 | −0.002691 | 0.030827 | −0.009779 | 0.000724 | 0.001331 | 0.005954 | −0.003003 | 0.011946 |
| 271 | 0.051706 | 0.014608 | −0.031883 | −0.040102 | −0.097649 | −0.000568 | −0.028692 | 0.017884 | 0.035575 | 0.021974 | 0.030065 | 0.063969 | 0.042899 | 0.014648 |
| 272 | −0.004091 | −0.029068 | −0.015825 | 0.064018 | −0.042747 | −0.002805 | −0.021977 | 0.008098 | 0.015778 | −0.007365 | −0.01205 | 0.003833 | −0.020192 | 0.023526 |
| 273 | −0.02376 | 0.014361 | 0.011643 | 0.011187 | 0.041644 | 0.022949 | 0.031271 | 0.046421 | −0.020787 | −0.00408 | −0.026881 | 0.000803 | −0.01455 | −0.010884 |
| 274 | −0.029912 | 0.00222 | −0.010407 | 0.011077 | 0.05236 | 0.028762 | 0.026071 | 0.036704 | −0.013266 | −0.003634 | −0.024106 | 0.01199 | −0.024022 | −0.004002 |
| 275 | 0.009499 | 0.001675 | −0.040748 | 0.03127 | 0.006408 | 0.017132 | −0.003353 | 0.034018 | 0.045677 | 0.03595 | −0.018052 | 0.037039 | −0.049074 | −0.01325 |
| 276 | 0.011872 | −0.004306 | 0.010689 | 0.026838 | −0.024963 | 0.015039 | 0.014289 | 0.02892 | −0.005847 | −0.02794 | 0.007145. | 0.038617 | 0.012009 | −0.059063 |
| 277 | 0.052517 | 0.004224 | 0.048096 | 0.03771 | 0.041863 | 0.044842 | 0.051052 | 0.07104 | 0.031947 | 0.00475 | 0.026476 | 0.004785 | 0.001857 | −0.015893 |
| 278 | 0.073232 | 0.009699 | 0.041245 | 0.042459 | 0.006937 | 0.002119 | 0.008005 | 0.043507 | 0.036541 | 0.026018 | 0.026848 | 0.00486 | 0.00356 | 0.004715 |
| 279 | 0.017995 | 0.034011 | −0.020271 | −0.032952 | 0.01612 | 0.015134 | 0.027534 | 0.021822 | 0.037794 | 0.051451 | 0.012516 | 0.008886 | −0.003754 | 0.014178 |
| 280 | 0.025916 | 0.061383 | 0.008821 | −0.012773 | −0.118664 | 0.028399 | −0.007915 | −0.00376 | 0.021467 | −0.009362 | −0.0082 | 0.082712 | −0.013065 | −0.006861 |
| 281 | −0.009219 | 0.02015 | 0.020416 | 0.027287 | 0.019138 | 0.060048 | 0.013225 | 0.021433 | 0.036357 | −0.032913 | −0.015231 | 0.008884 | 0.006366 | 0.001585 |
| 282 | 0.014617 | −0.000876 | 0.017443 | 0.006888 | −0.020881 | 0.024586 | −0.018848 | 0.015272 | 0.024976 | 0.014032 | −0.00889 | 0.030463 | 0.048511 | 0.012196 |
| 283 | −0.023059 | −0.023114 | −0.016607 | 0.005823 | 0.020115 | 0.025081 | 0.015443 | −0.002041 | 0.034576 | −0.022841 | 0.00192 | −0.016639 | −0.009609 | −0.018088 |
| 284 | −0.000287 | −0.028522 | 0.000518 | 0.021099 | 0.004915 | 0.036173 | 0.038073 | −0.024763 | −0.138707 | −0.013933 | 0.016798 | 0.000354 | 0.025797 | 0.009793 |
| 285 | 0.00602 | −0.057963 | −0.01315 | 0:004406 | −0.028356 | 0.037506 | 0.019492 | −0.01758 | −0.126444 | 0.016698 | 0.00604 | 0.003439 | 0.037817 | 0.035544 |
| 286 | −0.012622 | 0.015102 | −0.017351 | −0.000796 | −0.031638 | 0.006801 | 0.026218 | 0.039923 | −0.063936 | −0.145765 | −0.020587 | 0.006403 | −0.019347 | 0.000118 |
| 287 | −0.039328 | 0.02997 | −0.026828 | −0.025685 | −0.031394 | −0.021311 | 0.022028 | −0.003392 | −0.056392 | −0.092965 | −0.022151 | 0.002601 | −0.034256 | 0.011485 |
| 288 | −0.00331 | −0.006053 | 0.016311 | 0.022584 | −0.011523 | −0.002903 | −0.016491 | −0.038313 | 0.002315 | −0.12071 | 0.020228 | −0.02946 | 0.008484 | −0.015621 |
| 289 | 0.031351 | −0.009643 | −0.001996 | −0.013907 | 0.008219 | 0.003108 | −0.026751 | −0.054669 | −0.015403 | −0.022094 | 0.019268 | −0.010013 | −0.007388 | −0.084104 |
| 290 | 0.03225 | 0.018033 | −0.013624 | −0.011956 | −0.038281 | −0.004118 | 0.004758 | −0.007721 | −0.000512 | 0.013638 | 0.000683 | 0.005906 | −0.02605 | −0.00454 |
| 291 | 0.028682 | 0.017672 | −0.014231 | −0.010861 | −0.03474 | −0.002869 | 0.003678 | −0.012385 | −0.002003 | 0.002521 | 0.006183 | 0.017255 | −0.024204 | −0.005322 |
| 292 | 0.013086 | −0.041807 | −0.070443 | 0.013945 | −0.02893 | 0.024375 | 0.000986 | 0.004654 | 0.028253 | 0.03214 | 0.005519 | 0.069856 | −0.000137 | 0.031158 |
| 293 | 0.056341 | −0.015373 | 0.038794 | 0.04187 | −0.030784 | 0.021436 | 0.010956 | −0.023539 | −0.008721 | −0.007706 | 0.003538 | 0.026204 | 0.034745 | 0.001521 |
| 294 | −0.01574 | −0.002728 | 0.02016 | 0.018308 | 0.033772 | −0.051087 | −0.002 | −0.007134 | 0.016617 | −0.002856 | 0.023797 | 0.045496 | 0.011776 | 0.025707 |
| 295 | −0.009935 | 0.028649 | 0.031552 | −0.018313 | 0.004159 | −0.010737 | 0.025284 | 0.007551 | −0.028724 | −0.004675 | −0.012141 | −0.007042 | −0.004349 | −0.028154 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 296 | −0.031379 | 0.009996 | −0.005743 | −0.005566 | −0.022901 | −0.038033 | −0.002195 | 0.037528 | 0.032227 | −0.020074 | −0.000562 | 0.012869 | −0.043996 | −0.024178 |
| 297 | −0.030068 | 0.031422 | 0.029817 | −0.029888 | 0.009889 | 0.01878 | 0.052787 | −0.007361 | −0.012358 | 0.01602 | 0.00236 | 0.003787 | 0.000976 | −0.019755 |
| 298 | 0.014417 | 0.0011 | 0.017125 | 0.024818 | −0.029472 | −0.038729 | −0.020524 | 0.043904 | 0.02971 | 0.017815 | 0.002013 | −0.055661 | 0.035635 | 0.003152 |
| 299 | 0.019674 | −0.005123 | −0.009255 | −0.002097 | −0.032509 | −0.020062 | 0.014302 | 0.01974 | 0.030092 | 0.013663 | −0.001461 | −0.02234 | 0.009095 | −0.004098 |
| 300 | −0.018259 | 0.004747 | −0.008521 | −0.011414 | −0.030162 | −0.032429 | −0.014053 | 0.031711 | 0.00818 | −0.004915 | −0.01116 | −0.032552 | −0.04946 | −0.045684 |
| 301 | 0.017815 | −0.005303 | 0.014529 | 0.007097 | −0.007021 | 0.019602 | 0.0003 | −0.016515 | −0.057789 | 0.033295 | 0.031518 | 0.012955 | 0.039427 | −0.004085 |
| 302 | 0.033884 | −0.006928 | −0.000858 | 0.033937 | −0.000487 | 0.059996 | 0.000105 | −0.003244 | −0.051285 | 0.003031 | 0.011221 | 0.02942 | 0.025148 | −0.008985 |
| 303 | 0.027013 | −0.030013 | −0.039317 | 0.001316 | −0.035383 | 0.00621 | −0.01776 | 0.044276 | 0.042022 | −0.022762 | −0.037257 | −0.030515 | −0.004383 | 0.029399 |
| 304 | 0.04205 | 0.001591 | −0.044099 | 0.011921 | −0.061934 | 0.028808 | 0.012291 | 0.049145 | 0.066175 | −0.017252 | −0.017885 | 0.023104 | −0.02547 | −0.001477 |
| 305 | 0.00411 | −0.019825 | 0.017874 | 0.031475 | −0.030546 | −0.037298 | −0.033748 | −0.003482 | −0.026013 | 0.053023 | −0.010258 | −0.053599 | −0.0276 | 0.000887 |
| 306 | −0.000244 | −0.007127 | −0.043403 | 0.016617 | 0.006028 | 0.026405 | −0.009782 | 0.040174 | −0.003096 | −0.000596 | −0.015369 | 0.012848 | −0.001684 | 0.029699 |
| 307 | 0.007487 | 0.030211 | 0.04001 | 0.007628 | −0.087643 | −0.007626 | 0.028839 | 0.030333 | −0.017329 | 0.012379 | −0.01015 | 0.005327 | 0.06227 | −0.005511 |
| 308 | 0.010745 | 0.013738 | 0.00146 | −0.008019 | −0.022867 | 0.047897 | 0.007159 | −0.027083 | 0.013948 | 0.047331 | 0.039036 | 0.002793 | 0.005995 | 0.004903 |
| 309 | −0.031712 | 0.020949 | 0.009328 | −0.017658 | 0.014157 | 0.006234 | 0.001585 | −0.019891 | 0.015913 | 0.02523 | −0.007048 | 0.014531 | 0.007486 | −0.002548 |
| 310 | −0.00471 | −0.025331 | −0.007809 | 0.006805 | −0.040151 | −0.037204 | −0.039441 | −0.020561 | −0.005099 | 0.03043 | −0.008215 | −0.01054 | 0.000833 | 0.016587 |
| 311 | 0.008279 | 0.055522 | 0.012609 | −0.047918 | 0.009046 | 0.001027 | 0.041952 | 0.02886 | −0.018191 | 0.019715 | −0.038681 | −0.055518 | −0.030632 | −0.030364 |
| 312 | 0.059015 | −0.002445 | 0.00627 | 0.008381 | −0.011959 | −0.025147 | −0.013384 | 0.029991 | 0.017806 | −0.003324 | 0.025825 | 0.013603 | −0.006096 | −0.004869 |
| 313 | 0.02197 | 0.057755 | 0.04615 | −0.003753 | 0.014093 | −0.011726 | −0.01516 | 0.008052 | −0.014623 | 0.022796 | −0.000033 | 0.001508 | 0.00306 | 0.004874 |
| 314 | 0.001549 | −0.011361 | −0.006076 | −0.021407 | −0.062796 | 0.043765 | 0.029315 | 0.000406 | 0.015962 | 0.000343 | −0.024391 | 0.014064 | 0.02119 | −0.006085 |
| 315 | 0.025715 | 0.019956 | −0.015134 | −0.01208 | 0.021549 | 0.007406 | 0.012648 | 0.007038 | 0.028089 | −0.01797 | 0.023715 | 0.007821 | −0.029395 | −0.00864 |
| 316 | −0.00372 | 0.046859 | 0.043751 | 0.049584 | −0.059399 | −0.074395 | −0.011587 | 0.030739 | 0.016357 | −0.035645 | 0.003434 | 0.016822 | −0.00256 | −0.019707 |
| 317 | 0.024784 | −0.010349 | 0.018155 | −0.013224 | −0.016175 | −0.022713 | −0.004622 | −0.017902 | −0.032741 | 0.018894 | 0.010652 | −0.041424 | −0.002071 | −0.013505 |
| 318 | −0.00357 | −0.040774 | −0.014862 | 0.012102 | 0.022703 | 0.014284 | 0.001731 | 0.030108 | −0.014722 | −0.008836 | 0.001436 | 0.008228 | −0.013353 | 0.000695 |
| 319 | 0.012522 | 0.004938 | 0.010677 | 0.000041 | −0.01746 | −0.019514 | 0.001731 | −0.006462 | −0.004657 | −0.041129 | 0.030043 | −0.009997 | −0.020057 | 0.010644 |
| 320 | 0.039736 | 0.001628 | 0.039686 | 0.008233 | −0.009177 | −0.000374 | 0.004384 | −0.038511 | −0.038553 | −0.044144 | 0.042634 | 0.02371 | 0.054079 | 0.021982 |
| 321 | 0.026323 | −0.01203 | −0.041685 | −0.014207 | 0.042157 | 0.041867 | 0.029492 | −0.018556 | 0.000403 | 0.028738 | 0.009414 | 0.017568 | −0.009601 | −0.005464 |
| 322 | −0.022343 | 0.006246 | −0.026337 | −0.034349 | 0.030425 | 0.022783 | −0.032355 | −0.032194 | −0.0037 | −0.021403 | 0.008072 | 0.045893 | 0.017103 | 0.011816 |
| 323 | −0.036258 | −0.006341 | −0.025437 | −0.024775 | −0.009053 | −0.034393 | −0.031301 | −0.039004 | −0.026494 | 0.003243 | −0.028238 | 0.063974 | 0.023556 | 0.019887 |
| 324 | 0.009029 | −0.019658 | −0.00485 | 0.020455 | 0.052894 | 0.03213 | −0.025005 | 0.039678 | −0.017566 | −0.020064 | −0.002599 | −0.03909 | −0.005693 | −0.010831 |
| 325 | −0.017236 | 0.008304 | 0.01121 | 0.00975 | 0.000468 | 0.009227 | 0.017448 | 0.009481 | 0.031464 | 0.02703 | −0.007993 | −0.011937 | −0.056626 | −0.031535 |
| 326 | −0.064073 | −0.04994 | −0.035452 | 0.009268 | 0.022997 | −0.036487 | 0.010693 | −0.002287 | −0.000484 | −0.038815 | −0.034079 | −0.020477 | −0.02166 | −0.008486 |
| 327 | −0.008186 | 0.003001 | −0.039458 | 0.000537 | 0.035422 | 0.00374 | 0.014705 | 0.023975 | 0.02718 | −0.014763 | 0.013351 | 0.037271 | 0.004687 | 0.01022 |
| 328 | −0.061458 | −0.016953 | −0.006922 | 0.001202 | −0.053806 | 0.032696 | 0.011523 | 0.006944 | 0.013707 | 0.04278 | −0.021405 | −0.021885 | −0.002568 | −0.003741 |
| 329 | 0.023145 | −0.009879 | −0.057288 | −0.004176 | 0.024226 | 0.00065 | −0.000115 | 0.042036 | −0.016912 | −0.036636 | −0.039906 | −0.004625 | 0.016107 | 0.025662 |
| 330 | 0.039761 | −0.032988 | −0.030851 | −0.014571 | −0.002834 | 0.024953 | 0.017874 | 0.057546 | 0.006603 | 0.010985 | −0.013751 | −0.062162 | −0.021571 | 0.001114 |
| 331 | −0.018074 | −0.025466 | −0.015192 | 0.038467 | 0.036302 | −0.01409 | −0.026212 | −0.023934 | 0.047561 | −0.010501 | −0.007407 | 0.056338 | 0.027238 | 0.027143 |
| 332 | 0.014144 | 0.011491 | −0.004125 | −0.03563 | −0.040351 | 0.018346 | 0.019715 | −0.034707 | −0.014801 | −0.003785 | 0.051706 | −0.027803 | −0.033235 | 0.001435 |
| 333 | −0.024657 | −0.030567 | 0.004068 | 0.002162 | 0.050462 | 0.018948 | −0.012404 | −0.011151 | −0.007436 | 0.005946 | 0.015932 | 0.018726 | 0.015281 | 0.021173 |
| 334 | 0.017907 | 0.016501 | 0.014181 | −0.023796 | 0.043165 | 0.034026 | 0.023101 | 0.021344 | −0.036521 | −0.036583 | 0.031628 | 0.028466 | 0.003986 | −0.028312 |
| 335 | −0.021689 | −0.033699 | −0.028806 | 0.028987 | −0.032551 | 0.003693 | −0.020297 | −0.031773 | 0.037556 | 0.048689 | −0.002561 | 0.006798 | 0.002749 | 0.046907 |
| 336 | 0.009208 | −0.004247 | 0.050944 | 0.019279 | 0.027643 | 0.01716 | 0.025756 | 0.001204 | 0.007597 | −0.045349 | 0.001471 | −0.025468 | 0.026978 | −0.038545 |
| 337 | −0.034864 | −0.012901 | −0.013367 | −0.000336 | 0.002987 | −0.0199 | −0.014479 | −0.003369 | 0.019673 | −0.012522 | −0.003532 | −0.072609 | −0.011219 | 0.030746 |
| 338 | −0.007397 | 0.0033 | −0.001995 | −0.037524 | −0.013073 | 0.018242 | −0.005172 | −0.000443 | −0.016469 | −0.023449 | 0.035998 | 0.013414 | 0.00777 | −0.011679 |
| 339 | 0.001276 | 0.016995 | −0.014072 | −0.011813 | −0.008215 | −0.019445 | 0.023189 | 0.029396 | −0.002276 | −0.024553 | −0.038178 | −0.007167 | −0.01973 | 0.001042 |
| 340 | 0.006357 | 0.037145 | 0.011797 | −0.011147 | 0.021013 | −0.003391 | −0.004184 | −0.006406 | 0.005154 | 0.014033 | −0.001766 | −0.010771 | 0.014156 | 0.042706 |

| | JD | JE | JF | JG | JH | JI | JJ | JK | JL | JM | JN | JO | JP | JQ |
|---|---|---|---|---|---|---|---|---|---|---|---|---|---|---|
| 1 | 0.025765 | −0.031694 | 0.009224 | 0.09264 | 0.010846 | 0.031861 | 0.021791 | 0.051123 | −0.063054 | −0.035289 | −0.045668 | −0.046722 | 0.008047 | −0.048934 |
| 2 | 0.037871 | 0.034928 | 0.064343 | 0.06491 | 0.035598 | −0.0372 | −0.031115 | −0.046164 | 0.012 | 0.034677 | −0.035139 | −0.043151 | 0.037756 | 0.070143 |
| 3 | −0.040629 | 0.055433 | 0.076843 | 0.014883 | −0.020355 | −0.03256 | −0.060739 | −0.017108 | 0.064394 | −0.010351 | −0.019046 | −0.023887 | −0.037299 | −0.07299 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 4 | −0.060857 | 0.020772 | 0.016012 | −0.047123 | 0.053079 | −0.005659 | 0.034347 | −0.058534 | −0.189014 | −0.008601 | 0.019112 | 0.024054 | −0.00212 | −0.030715 |
| 5 | −0.017824 | −0.015868 | −0.045592 | 0.011001 | −0.096767 | −0.055679 | −0.006765 | −0.012442 | −0.040655 | 0.059623 | −0.015237 | −0.007759 | −0.034958 | 0.006017 |
| 6 | −0.030785 | −0.07452 | −0.057568 | 0.000527 | 0.011752 | −0.010853 | −0.028018 | 0.008691 | 0.041472 | 0.044392 | 0.013395 | 0.013002 | 0.010285 | −0.041221 |
| 7 | 0.02361 | −0.00282 | −0.04559 | −0.056112 | −0.008595 | −0.000296 | 0.030051 | 0.04122 | 0.018299 | 0.043385 | −0.032635 | −0.011322 | −0.026947 | 0.023842 |
| 8 | −0.045916 | 0.022812 | 0.020664 | −0.00899 | 0.036326 | −0.002062 | −0.033733 | −0.038781 | −0.030044 | −0.05817 | −0.004765 | −0.022429 | 0.015259 | −0.04908 |
| 9 | −0.004623 | −0.013525 | 0.000573 | −0.007631 | 0.108821 | 0.030613 | 0.015651 | 0.007336 | 0.157722 | 0.105008 | −0.022045 | −0.026931 | −0.033566 | 0.060356 |
| 10 | −0.031812 | −0.041815 | 0.009438 | −0.047654 | −0.036107 | 0.045733 | 0.033019 | 0.002661 | 0.00814 | −0.036579 | 0.020026 | 0.020044 | −0.019143 | −0.022041 |
| 11 | 0.017996 | 0.024872 | 0.031833 | −0.00689 | 0.012343 | 0.010558 | −0.009153 | −0.001282 | −0.002216 | −0.048403 | −0.006162 | −0.005854 | −0.019157 | 0.0438 |
| 12 | −0.044924 | −0.043563 | −0.023568 | −0.024568 | −0.048201 | 0.004734 | 0.027588 | 0.01282 | −0.058272 | −0.022054 | 0.010563 | 0.025443 | −0.021574 | −0.063682 |
| 13 | −0.029981 | 0.060049 | 0.036836 | 0.002897 | −0.088124 | −0.01558 | 0.003952 | −0.014953 | −0.073618 | 0.054597 | 0.049251 | 0.063065 | −0.003622 | −0.041895 |
| 14 | 0.038629 | −0.023976 | −0.005644 | −0.032385 | 0.063203 | −0.038773 | −0.056059 | −0.072438 | 0.032844 | 0.158945 | 0.031091 | 0.056096 | −0.032808 | 0.030323 |
| 15 | 0.0178 | −0.039094 | −0.022496 | −0.057576 | −0.062019 | −0.007231 | 0.012073 | 0.078297 | −0.098442 | 0.01122 | 0.036587 | 0.023232 | 0.053614 | −0.10583 |
| 16 | −0.014293 | −0.074316 | −0.015863 | 0.007497 | 0.056669 | 0.012844 | 0.002108 | 0.012878 | −0.060471 | 0.027628 | 0.005763 | −0.003916 | −0.041828 | 0.095345 |
| 17 | −0.031725 | 0.041194 | 0.032184 | 0.011819 | 0.019622 | 0.032324 | 0.01972 | 0.059035 | 0.076233 | −0.015313 | 0.009978 | −0.001015 | 0.021828 | −0.052409 |
| 18 | 0.03079 | 0.01079 | −0.000593 | 0.038643 | −0.058347 | 0.01649 | −0.017651 | −0.033364 | 0.058784 | −0.029141 | 0.026054 | 0.008858 | −0.04381 | 0.02779 |
| 19 | −0.004856 | 0.015518 | 0.033477 | −0.032595 | −0.0223 | −0.044096 | −0.010824 | 0.015376 | 0.016986 | −0.021338 | −0.015783 | −0.006746 | 0.084682 | −0.024167 |
| 20 | 0.035363 | −0.050285 | 0.014248 | 0.050559 | 0.035422 | 0.039846 | 0.017316 | 0.061376 | 0.046641 | −0.042484 | 0.003476 | −0.003576 | −0.061831 | 0.023761 |
| 21 | −0.00594 | −0.034316 | 0.013414 | −0.004957 | 0.068723 | 0.034635 | 0.012342 | −0.019229 | −0.021155 | 0.021017 | −0.012565 | −0.017138 | −0.07722 | 0.093696 |
| 22 | 0.057056 | 0.007508 | −0.042485 | 0.010002 | −0.033288 | 0.003499 | −0.016622 | −0.064005 | −0.113986 | −0.017324 | 0.017901 | 0.036443 | −0.047213 | 0.081267 |
| 23 | 0.014113 | 0.08785 | 0.07953 | 0.054942 | −0.048923 | −0.043374 | −0.030535 | −0.018 | 0.050584 | −0.005856 | −0.004228 | −0.014889 | 0.007015 | −0.020562 |
| 24 | −0.027532 | −0.029817 | 0.001352 | 0.028314 | 0.038057 | 0.03037 | 0.00041 | 0.001386 | −0.021893 | −0.064625 | 0.025466 | 0.027805 | −0.004499 | −0.006465 |
| 25 | 0.025075 | 0.02502 | −0.027416 | 0.065671 | 0.024734 | 0.038842 | 0.090343 | 0.044802 | −0.086943 | 0.004615 | −0.031729 | −0.026093 | 0.022223 | −0.061989 |
| 26 | 0.0612 | −0.006826 | 0.031872 | 0.056348 | 0.039275 | 0.006467 | −0.011248 | −0.026795 | 0.01805 | −0.082156 | −0.040534 | −0.045891 | −0.014403 | 0.098875 |
| 27 | −0.05548 | 0.002233 | −0.013163 | −0.072908 | 0.004912 | 0.02837 | 0.000562 | 0.057655 | −0.058762 | −0.043145 | −0.05062 | −0.039883 | −0.091029 | 0.049203 |
| 28 | −0.023605 | 0.024832 | 0.009601 | 0.057473 | −0.064616 | 0.019753 | 0.063533 | 0.033844 | 0.033028 | −0.032764 | 0.045251 | 0.055299 | 0.081911 | −0.049004 |
| 29 | −0.005155 | −0.032011 | 0.050269 | 0.064124 | 0.016388 | −0.025114 | −0.080902 | −0.025857 | −0.15859 | −0.025304 | −0.011187 | −0.01849 | −0.014333 | −0.021019 |
| 30 | −0.04099 | −0.027614 | 0.045601 | 0.047381 | −0.057606 | −0.145062 | −0.070554 | −0.065416 | −0.009126 | 0.000816 | −0.072041 | −0.062153 | 0.0729 | −0.009218 |
| 31 | 0.008092 | −0.019801 | −0.056845 | −0.036895 | −0.092552 | 0.032445 | 0.025042 | −0.024258 | 0.054834 | −0.080136 | −0.126065 | −0.123724 | −0.076718 | −0.02122 |
| 32 | −0.058647 | −0.030583 | −0.000694 | 0.05176 | −0.051051 | −0.013282 | −0.001113 | −0.027757 | 0.046548 | 0.009403 | −0.00803 | 0.007511 | −0.018891 | −0.04725 |
| 33 | 0.004938 | −0.022528 | −0.002421 | 0.053179 | 0.030524 | 0.033379 | 0.040919 | 0.011677 | 0.004708 | 0.03991 | −0.006509 | −0.009055 | −0.082302 | 0.006466 |
| 34 | 0.004545 | 0.015626 | 0.004683 | −0.00837 | 0.108824 | −0.012973 | −0.01033 | 0.01463 | 0.088922 | 0.046667 | 0.050373 | 0.045606 | 0.067906 | 0.048648 |
| 35 | −0.043241 | 0.02839 | 0.032951 | −0.027469 | −0.024782 | −0.017689 | −0.017993 | −0.010819 | 0.008994 | 0.054606 | 0.092269 | 0.103394 | 0.033898 | 0.034677 |
| 36 | −0.058007 | 0.02917 | 0.009275 | 0.002298 | −0.033718 | −0.038927 | 0.008589 | −0.047586 | −0.026312 | −0.058244 | −0.018064 | −0.029066 | 0.071701 | 0.014084 |
| 37 | −0.041554 | 0.067736 | 0.075791 | −0.050695 | 0.127755 | −0.001083 | −0.071152 | −0.009193 | −0.054033 | 0.108521 | 0.034472 | 0.029425 | 0.028322 | −0.090156 |
| 38 | 0.006803 | −0.052683 | −0.055521 | 0.012205 | 0.046015 | −0.004238 | 0.026729 | 0.003985 | 0.056208 | 0.047137 | −0.021194 | −0.002232 | 0.04126 | −0.004672 |
| 39 | 0.004896 | 0.08361 | 0.049396 | −0.033327 | −0.106342 | 0.004741 | −0.010283 | −0.004574 | −0.107663 | −0.019136 | 0.046805 | 0.039683 | 0.004392 | 0.022984 |
| 40 | −0.000828 | −0.124038 | 0.002691 | 0.049916 | 0.006252 | 0.022949 | 0.020236 | 0.041306 | −0.092475 | −0.007893 | −0.052907 | −0.053758 | 0.01797 | −0.098947 |
| 41 | −0.037933 | 0.013475 | −0.096959 | −0.060919 | 0.067824 | 0.009543 | 0.007525 | −0.05656 | −0.005959 | 0.113 | 0.013314 | 0.020556 | −0.134871 | −0.01469 |
| 42 | −0.009185 | 0.019423 | 0.019121 | −0.026556 | 0.073793 | 0.024997 | 0.033145 | 0.064792 | 0.11075 | 0.000205 | −0.013684 | 0.009898 | 0.042999 | −0.034415 |
| 43 | −0.001154 | 0.016135 | −0.067798 | −0.111293 | 0.007347 | −0.024448 | −0.046422 | −0.022564 | −0.13562 | −0.080531 | −0.071202 | −0.082972 | 0.001536 | 0.130801 |
| 44 | 0.049 | 0.043956 | 0.0048 | −0.025089 | −0.008664 | 0.041856 | 0.051694 | 0.116396 | 0.073889 | −0.038749 | 0.030585 | 0.034422 | 0.165505 | 0.039859 |
| 45 | −0.018967 | 0.041411 | 0.030832 | 0.078755 | −0.060304 | −0.01816 | −0.012455 | −0.035686 | −0.002239 | −0.032759 | 0.04004 | 0.025051 | 0.020618 | 0.003893 |
| 46 | −0.019887 | −0.033664 | −0.038112 | −0.038356 | −0.083522 | −0.060069 | −0.062011 | −0.076959 | −0.029065 | −0.011781 | −0.01661 | −0.011686 | −0.046626 | 0.079263 |
| 47 | −0.037794 | −0.003252 | 0.029237 | 0.043247 | −0.073781 | −0.021222 | 0.035153 | 0.045299 | 0.099239 | −0.020722 | −0.003023 | 0.032824 | −0.10774 | −0.039757 |
| 48 | 0.038719 | −0.016734 | 0.046289 | 0.018048 | 0.145736 | 0.033802 | 0.020885 | 0.012381 | 0.102853 | −0.013144 | −0.060245 | −0.061528 | −0.025292 | 0.041493 |
| 49 | −0.02136 | 0.080983 | −0.017995 | −0.033066 | 0.008204 | 0.037428 | 0.013586 | 0.086056 | −0.056191 | −0.035088 | 0.011362 | −0.002 | −0.049639 | 0.003141 |
| 50 | 0.081135 | 0.032685 | 0.052522 | 0.049664 | −0.044209 | −0.024178 | −0.019256 | −0.051352 | 0.023715 | −0.01649 | −0.047202 | −0.047531 | 0.02461 | 0.01474 |
| 51 | −0.050947 | 0.039329 | −0.082807 | −0.014471 | 0.049966 | −0.030255 | 0.014351 | −0.021385 | −0.019265 | 0.009762 | −0.074101 | −0.06447 | −0.026395 | −0.003503 |
| 52 | −0.027671 | −0.054094 | 0.017748 | 0.089652 | −0.026157 | −0.060294 | 0.003846 | −0.018785 | −0.026681 | −0.011461 | −0.029539 | 0.000685 | −0.027665 | −0.014032 |
| 53 | 0.079873 | −0.039191 | −0.044267 | −0.000161 | −0.10816 | −0.027667 | −0.012881 | −0.005875 | −0.193085 | −0.039856 | −0.006406 | −0.005065 | 0.044103 | 0.013828 |
| 54 | −0.020529 | −0.021789 | −0.044084 | −0.008324 | 0.027313 | 0.010359 | 0.051224 | 0.004837 | 0.092596 | −0.005055 | −0.056812 | −0.047628 | −0.060752 | 0.025902 |

APPENDIX B1-continued

| PCA Transformation Matrix(340 × 340; Normal/Diseased) | | | | | | | | | | | | | | |
|---|---|---|---|---|---|---|---|---|---|---|---|---|---|---|
| 55 | −0.036643 | −0.113026 | −0.17761 | −0.209457 | −0.033322 | 0.007239 | 0.041593 | 0.046764 | −0.064529 | −0.006264 | 0.077565 | 0.075814 | 0.098577 | 0.01876 |
| 56 | 0.021316 | −0.080669 | −0.07564 | 0.06012 | 0.043631 | 0.038321 | 0.016979 | 0.049035 | 0.036379 | −0.011351 | −0.000518 | 0.016719 | −0.000782 | −0.057012 |
| 57 | −0.004072 | 0.053407 | −0.003209 | −0.052056 | 0.012779 | −0.008061 | 0.007318 | −0.010456 | 0.107536 | −0.061918 | −0.026422 | −0.035083 | −0.029889 | 0.020429 |
| 58 | −0.00227 | 0.024201 | 0.083049 | 0.004924 | 0.056385 | 0.025021 | −0.023799 | 0.001076 | 0.058211 | −0.001594 | −0.023784 | −0.016271 | 0.010676 | −0.061433 |
| 59 | −0.025376 | 0.042221 | 0.089649 | 0.049913 | −0.049692 | −0.011468 | −0.020504 | −0.052686 | −0.041253 | −0.000378 | 0.004053 | −0.009711 | 0.007283 | 0.047642 |
| 60 | −0.030831 | 0.071137 | −0.038047 | −0.129203 | 0.008009 | 0.00194 | 0.011172 | 0.070193 | 0.015349 | 0.013046 | −0.033703 | −0.019187 | 0.078464 | −0.014795 |
| 61 | −0.026041 | −0.054506 | −0.033136 | 0.047925 | −0.115771 | −0.05224 | 0.005088 | −0.028596 | 0.002183 | 0.009983 | 0.039898 | 0.041344 | −0.017082 | 0.017753 |
| 62 | 0.036293 | −0.08011 | −0.039774 | 0.028278 | 0.042974 | 0.035091 | 0.039561 | −0.009475 | −0.065027 | 0.004079 | 0.015268 | 0.000788 | 0.032818 | 0.079538 |
| 63 | −0.064987 | −0.038191 | 0.074319 | 0.057043 | −0.041023 | −0.022953 | −0.021724 | 0.014727 | 0.024068 | −0.010831 | 0.041973 | 0.052838 | −0.018476 | −0.004637 |
| 64 | 0.004745 | −0.023078 | 0.016723 | 0.019215 | 0.011836 | 0.013099 | −0.001443 | −0.013208 | −0.010761 | −0.01869 | −0.006795 | 0.009608 | −0.002703 | −0.003748 |
| 65 | −0.022292 | −0.027798 | 0.143891 | 0.0328 | 0.032036 | −0.023869 | −0.032335 | 0.003082 | −0.068152 | 0.084853 | −0.016643 | −0.008517 | −0.056123 | −0.05434 |
| 66 | 0.008576 | 0.030789 | 0.000064 | −0.02089 | −0.000013 | −0.008372 | 0.019162 | 0.011021 | 0.01847 | −0.020368 | −0.002365 | 0.010953 | −0.002022 | −0.044874 |
| 67 | 0.089666 | −0.047186 | −0.026427 | −0.061787 | 0.085531 | 0.032824 | −0.037933 | −0.034661 | 0.102297 | 0.044554 | −0.018881 | −0.035063 | −0.073435 | −0.075879 |
| 68 | 0.034944 | 0.039895 | −0.012567 | −0.018149 | 0.052581 | 0.015585 | 0.010893 | −0.039033 | 0.006361 | 0.036952 | 0.000367 | −0.008798 | 0.018171 | −0.009676 |
| 69 | −0.058025 | −0.024247 | 0.048948 | −0.000722 | 0.053923 | 0.092775 | 0.114115 | 0.060753 | 0.060465 | −0.037068 | −0.001064 | −0.016387 | 0.00174 | 0.055499 |
| 70 | 0.018024 | 0.113336 | 0.081356 | −0.038053 | −0.038973 | 0.002183 | −0.007417 | 0.006206 | −0.033646 | 0.008149 | −0.005097 | −0.012589 | −0.018137 | −0.100323 |
| 71 | −0.03501 | 0.060819 | 0.111369 | −0.014706 | −0.054591 | 0.018413 | 0.017727 | −0.000038 | 0.00573 | 0.060657 | 0.007366 | −0.01729 | −0.031737 | 0.011037 |
| 72 | 0.047145 | 0.007606 | −0.03304 | 0.021479 | 0.004922 | 0.021998 | 0.042347 | 0.032187 | −0.049228 | −0.014424 | −0.02523 | −0.03063 | −0.039078 | 0.056837 |
| 73 | −0.000516 | −0.010747 | −0.022314 | −0.052917 | −0.044081 | 0.039326 | 0.029362 | 0.008548 | −0.042181 | −0.022906 | 0.067895 | 0.058541 | −0.008255 | −0.011354 |
| 74 | −0.055238 | −0.016777 | −0.001115 | −0.020928 | 0.08919 | 0.024367 | 0.01169 | −0.006854 | −0.016842 | 0.005836 | −0.041234 | −0.032495 | −0.042933 | −0.097431 |
| 75 | −0.023941 | −0.076804 | −0.034983 | 0.002834 | −0.025444 | −0.030943 | −0.04726 | −0.067938 | −0.002254 | −0.106866 | 0.017238 | −0.000629 | −0.063981 | 0.004539 |
| 76 | −0.037246 | 0.04292 | −0.015006 | 0.00342 | −0.002727 | −0.053113 | 0.007016 | −0.02384 | −0.094935 | −0.074254 | −0.069185 | −0.052952 | −0.035557 | −0.006904 |
| 77 | −0.038446 | −0.002012 | −0.073949 | −0.058863 | 0.023607 | 0.017429 | 0.021012 | 0.094967 | 0.080173 | −0.007494 | −0.037422 | −0.03193 | 0.069164 | 0.012888 |
| 78 | 0.116941 | −0.10312 | −0.063191 | 0.042024 | −0.042767 | −0.047019 | −0.05386 | −0.050488 | 0.000613 | 0.011219 | 0.011407 | 0.023222 | 0.102452 | 0.049439 |
| 79 | 0.055035 | −0.045611 | −0.022133 | 0.078573 | 0.007562 | 0.03804 | 0.027634 | 0.046446 | −0.014645 | 0.009059 | 0.005553 | 0.001754 | −0.019187 | 0.006205 |
| 80 | 0.005628 | 0.023203 | 0.022975 | −0.007332 | 0.008331 | −0.02424 | −0.008515 | −0.023357 | −0.049432 | −0.050158 | −0.011824 | −0.012275 | −0.006941 | −0.002153 |
| 81 | −0.056029 | 0.040106 | 0.015537 | −0.018423 | 0.07607 | −0.025764 | −0.066792 | −0.053275 | 0.003578 | 0.048862 | −0.013413 | −0.025376 | 0.038145 | −0.016853 |
| 82 | −0.046585 | 0.106938 | 0.111081 | 0.064376 | −0.040057 | −0.036587 | −0.02727 | −0.005489 | 0.072701 | 0.011929 | −0.011531 | 0.009057 | −0.026308 | −0.00655 |
| 83 | 0.022909 | −0.055194 | 0.021148 | 0.01727 | −0.09874 | −0.037893 | 0.010879 | 0.031983 | −0.117131 | −0.04312 | 0.007648 | 0.032985 | 0.023119 | 0.001008 |
| 84 | 0.003759 | 0.097493 | 0.046126 | −0.067503 | −0.013164 | 0.098151 | 0.046863 | 0.014708 | −0.060377 | 0.109982 | 0.131546 | 0.090582 | 0.038772 | −0.036816 |
| 85 | 0.047114 | 0.008398 | 0.04838 | 0.103498 | 0.024652 | 0.007253 | 0.016746 | 0.063979 | 0.036282 | 0.045103 | −0.005873 | 0.008142 | 0.095492 | 0.039589 |
| 86 | −0.076824 | −0.016123 | −0.008416 | −0.005659 | 0.053636 | −0.019394 | 0.000026 | −0.007317 | 0.077715 | 0.025951 | 0.024834 | 0.02692 | 0.030754 | −0.000087 |
| 87 | 0.055999 | −0.011043 | 0.023686 | 0.048736 | 0.015005 | −0.008258 | −0.010555 | −0.079495 | 0.019303 | 0.074298 | −0.016501 | −0.015602 | −0.037058 | −0.005308 |
| 88 | 0.070721 | −0.078496 | −0.100196 | −0.042269 | 0.029224 | −0.020152 | 0.075671 | 0.019764 | 0.080414 | −0.110907 | −0.022296 | −0.015974 | 0.035372 | −0.038986 |
| 89 | 0.060893 | 0.025394 | −0.005736 | −0.03959 | 0.078935 | 0.016471 | 0.013108 | −0.005012 | 0.045719 | −0.077135 | −0.118099 | −0.108676 | −0.155816 | −0.093184 |
| 90 | −0.021242 | −0.021712 | −0.021894 | 0.028963 | 0.049498 | −0.014582 | 0.006171 | −0.093708 | −0.096285 | 0.035335 | −0.028081 | −0.044402 | −0.092102 | 0.07532 |
| 91 | −0.017999 | 0.017963 | −0.085281 | −0.014672 | −0.157352 | −0.027268 | −0.029809 | −0.062505 | 0.16815 | 0.131547 | 0.053666 | 0.031383 | 0.0787 | 0.05649 |
| 92 | −0.032897 | 0.013164 | −0.016763 | −0.057079 | 0.001999 | −0.047217 | −0.060243 | 0.061443 | 0.018918 | 0.00822 | 0.046105 | 0.046713 | 0.152251 | −0.02529 |
| 93 | −0.00402 | −0.032694 | 0.022284 | 0.000885 | 0.042166 | −0.005473 | −0.014274 | 0.034628 | 0.059797 | 0.012339 | 0.010842 | 0.021667 | 0.007102 | 0.005233 |
| 94 | −0.038275 | 0.014315 | −0.042959 | −0.008393 | 0.0369 | −0.017952 | −0.045722 | −0.056553 | 0.016636 | 0.000844 | −0.000767 | 0.015807 | −0.01854 | 0.013722 |
| 95 | 0.005174 | 0.026127 | −0.000616 | 0.039217 | −0.061488 | −0.048878 | −0.075322 | −0.049119 | −0.035349 | −0.125005 | −0.02907 | −0.020347 | 0.068872 | −0.118281 |
| 96 | −0.01802 | −0.082885 | −0.037156 | 0.01978 | −0.067681 | −0.000964 | −0.006862 | −0.044244 | 0.019043 | −0.138152 | 0.008686 | 0.024353 | −0.026276 | −0.053081 |
| 97 | 0.039158 | 0.001986 | −0.000089 | −0.03288 | −0.097846 | −0.030468 | −0.044306 | −0.003955 | −0.021348 | −0.049528 | 0.003297 | −0.013688 | 0.05756 | −0.019658 |
| 98 | −0.028501 | −0.080206 | −0.037575 | 0.001467 | 0.061816 | −0.076223 | −0.034977 | 0.007231 | 0.117595 | −0.030641 | −0.031619 | −0.024001 | 0.011685 | 0.034931 |
| 99 | 0.060711 | 0.01839 | −0.045764 | −0.028113 | −0.033145 | −0.033637 | −0.042056 | −0.023042 | −0.034467 | 0.0595 | 0.020561 | 0.01274 | 0.004904 | 0.095139 |
| 100 | −0.056032 | −0.026989 | −0.001135 | −0.004151 | −0.009019 | −0.020673 | 0.015416 | 0.020441 | 0.060054 | 0.081922 | −0.003782 | −0.013011 | 0.047101 | 0.034503 |
| 101 | 0.052481 | 0.064968 | 0.003851 | 0.006488 | −0.124409 | −0.021217 | −0.044027 | 0.033284 | 0.037873 | 0.007365 | 0.027086 | 0.010143 | −0.017573 | 0.062212 |
| 102 | −0.012169 | 0.040166 | 0.073284 | 0.027748 | 0.034227 | −0.011176 | −0.000372 | 0.03138 | −0.10058 | 0.03811 | 0.029104 | 0.02276 | −0.0438 | −0.022509 |
| 103 | 0.05808 | 0.049471 | −0.0209 | −0.005642 | −0.086701 | 0.032538 | 0.048787 | 0.015785 | 0.095656 | −0.060213 | −0.011292 | −0.003595 | −0.056721 | −0.048724 |
| 104 | −0.039391 | 0.016489 | −0.03009 | −0.017197 | 0.081365 | −0.0293 | −0.013703 | −0.031279 | −0.062769 | 0.110052 | 0.03779 | 0.039581 | 0.052703 | 0.086578 |
| 105 | −0.016273 | −0.029287 | −0.036401 | 0.017675 | −0.060302 | −0.007373 | 0.004999 | 0.036667 | 0.034811 | −0.01041 | 0.035916 | 0.039593 | 0.10554 | −0.061437 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 106 | 0.000438 | 0.068061 | 0.113581 | 0.120656 | 0.013076 | 0.009734 | 0.018275 | −0.006186 | 0.081912 | 0.043279 | −0.026076 | −0.000685 | 0.003252 | 0.0386 |
| 107 | −0.019724 | 0.028862 | 0.021341 | 0.036566 | 0.04705 | 0.055882 | 0.061768 | 0.02574 | 0.038541 | −0.02687 | −0.01818 | −0.004412 | −0.084131 | −0.043184 |
| 108 | 0.031888 | −0.020926 | 0.001805 | 0.034479 | −0.0345 | 0.014773 | −0.024404 | −0.017981 | 0.044714 | 0.01453 | 0.026098 | 0.013789 | −0.036145 | −0.02041 |
| 109 | −0.036641 | −0.011524 | 0.004208 | −0.021752 | 0.051485 | −0.016805 | −0.017794 | −0.020351 | 0.037786 | −0.027314 | −0.00766 | −0.002631 | −0.022048 | −0.02102 |
| 110 | −0.003449 | 0.030102 | −0.020112 | −0.01994 | 0.000476 | 0.008586 | 0.026861 | −0.034521 | 0.008472 | 0.005028 | 0.017394 | 0.021117 | 0.021235 | 0.009251 |
| 111 | 0.003526 | 0.040703 | −0.03228 | −0.027507 | −0.001821 | 0.019028 | 0.037942 | −0.020437 | 0.048766 | 0.045132 | −0.009915 | −0.013039 | −0.027743 | 0.037467 |
| 112 | −0.008506 | 0.025583 | 0.043771 | −0.012729 | 0.042817 | −0.01307 | −0.001168 | 0.004188 | 0.030649 | −0.001401 | −0.02111 | −0.030529 | 0.019383 | −0.012029 |
| 113 | −0.038881 | 0.005903 | 0.045201 | 0.003385 | −0.030131 | 0.017623 | 0.006944 | 0.013735 | −0.109655 | −0.002078 | 0.017717 | 0.010392 | −0.018339 | −0.002099 |
| 114 | 0.019595 | −0.001965 | −0.037045 | 0.010418 | 0.0705 | −0.009201 | −0.01237 | −0.041279 | −0.017806 | −0.053969 | −0.015791 | −0.020006 | 0.009607 | 0.023329 |
| 115 | 0.082935 | 0.016736 | 0.019797 | −0.048131 | −0.008013 | −0.025076 | −0.065257 | −0.025265 | −0.097179 | 0.033231 | 0.005509 | 0.004494 | 0.026177 | −0.024129 |
| 116 | 0.045919 | −0.006148 | 0.064575 | −0.01751 | 0.068132 | −0.013722 | −0.008003 | 0.00137 | −0.101327 | 0.008883 | −0.009522 | −0.023936 | −0.004296 | −0.022277 |
| 117 | −0.097891 | 0.029446 | 0.027721 | 0.048905 | 0.038674 | 0.025938 | 0.003679 | −0.041009 | −0.131526 | −0.031978 | −0.019358 | −0.035035 | 0.012103 | −0.005085 |
| 118 | −0.010686 | −0.047938 | −0.000556 | 0.022513 | −0.089482 | 0.013549 | 0.007958 | −0.016966 | 0.023136 | 0.003978 | 0.052277 | 0.054584 | −0.032607 | −0.017512 |
| 119 | 0.001895 | −0.013657 | 0.036081 | −0.014122 | −0.006779 | −0.015101 | −0.082252 | −0.044571 | −0.062261 | −0.028152 | −0.00328 | −0.011348 | −0.033933 | 0.045584 |
| 120 | 0.064152 | −0.053414 | −0.037058 | 0.059903 | −0.065309 | −0.064963 | −0.051942 | 0.030759 | 0.024792 | −0.039815 | −0.013999 | 0.001381 | 0.027475 | 0.013867 |
| 121 | 0.014469 | 0.028333 | 0.03582 | −0.047137 | 0.059071 | 0.005004 | 0.011565 | −0.00459 | 0.029046 | 0.064402 | 0.027233 | 0.011667 | −0.029648 | −0.027919 |
| 122 | 0.09376 | −0.012846 | −0.062384 | −0.078205 | 0.082671 | −0.025987 | −0.039209 | −0.052268 | −0.001281 | 0.134976 | 0.019383 | 0.001614 | −0.030112 | 0.04683 |
| 123 | −0.023971 | 0.066304 | −0.007036 | −0.015467 | −0.067584 | −0.059067 | 0.017338 | 0.017821 | 0.015303 | −0.141365 | −0.126781 | −0.095571 | 0.050527 | −0.048055 |
| 124 | 0.071517 | 0.070806 | −0.052368 | −0.034369 | −0.039998 | −0.026215 | 0.016617 | −0.036177 | 0.082591 | 0.003868 | 0.019563 | 0.015069 | 0.052799 | 0.009967 |
| 125 | −0.023686 | 0.009501 | −0.005095 | −0.007755 | −0.064809 | −0.052448 | −0.035149 | −0.017281 | 0.056946 | 0.021559 | 0.021854 | 0.033143 | 0.022154 | −0.038452 |
| 126 | 0.017665 | −0.068819 | 0.01041 | 0.047595 | 0.010474 | 0.044841 | 0.022444 | 0.007928 | −0.075498 | −0.087491 | 0.050395 | 0.030602 | −0.049171 | 0.013434 |
| 127 | 0.062741 | 0.036347 | −0.020175 | 0.004938 | 0.113424 | 0.044122 | 0.040929 | 0.064347 | 0.04267 | 0.012045 | 0.00946 | −0.019329 | 0.044861 | −0.051928 |
| 128 | 0.030356 | 0.01175 | 0.017994 | −0.032308 | −0.005325 | −0.035854 | −0.02842 | 0.007301 | −0.016015 | 0.012345 | −0.02748 | −0.032444 | 0.015718 | 0.054358 |
| 129 | −0.025186 | 0.061864 | −0.004801 | −0.009278 | −0.004076 | −0.019725 | 0.004824 | −0.016508 | 0.019565 | 0.032233 | 0.011748 | 0.007412 | −0.002592 | −0.004686 |
| 130 | −0.007574 | −0.030539 | −0.003777 | 0.009966 | −0.017939 | 0.049343 | 0.081644 | 0.031777 | 0.03174 | 0.005845 | 0.024667 | 0.017749 | 0.000738 | −0.000208 |
| 131 | 0.016551 | −0.011206 | −0.005977 | −0.03082 | 0.046714 | −0.01221 | −0.037274 | −0.031181 | 0.032493 | 0.025416 | 0.013706 | 0.004701 | 0.001875 | −0.024805 |
| 132 | 0.006036 | 0.048435 | 0.007327 | −0.035471 | −0.039783 | −0.028106 | −0.005914 | −0.014774 | −0.053996 | 0.005454 | 0.008654 | 0.026507 | 0.048899 | −0.006952 |
| 133 | −0.011463 | 0.025036 | −0.048525 | −0.004995 | 0.004371 | −0.021584 | −0.0157 | 0.01079 | −0.064572 | −0.009668 | −0.021432 | −0.025001 | 0.022298 | 0.001798 |
| 134 | −0.033624 | −0.016712 | 0.035687 | 0.047738 | −0.005349 | −0.033933 | 0.002535 | 0.014192 | 0.060074 | −0.005685 | −0.033254 | −0.036197 | 0.059679 | 0.018141 |
| 135 | −0.028758 | −0.091985 | −0.080799 | −0.047975 | 0.026882 | 0.01898 | 0.043274 | −0.004708 | −0.055043 | 0.022409 | 0.037873 | 0.056231 | 0.010696 | 0.000348 |
| 136 | −0.036524 | −0.016222 | 0.015921 | 0.049506 | −0.021089 | 0.014757 | −0.02158 | 0.013313 | −0.051519 | −0.018414 | 0.005299 | −0.00743 | 0.028007 | −0.004603 |
| 137 | −0.017968 | −0.037194 | 0.011117 | 0.029731 | 0.09683 | 0.028142 | 0.026141 | 0.036535 | −0.027099 | 0.00467 | 0.025139 | 0.043146 | 0.061424 | 0.050549 |
| 138 | −0.089402 | 0.052279 | 0.025513 | 0.004232 | −0.010004 | 0.002561 | −0.023453 | −0.015446 | −0.033719 | 0.037562 | 0.027203 | 0.035195 | 0.011636 | 0.052494 |
| 139 | −0.022073 | 0.000348 | 0.026097 | 0.034322 | 0.012708 | 0.040563 | 0.039084 | 0.03956 | 0.005715 | 0.013685 | 0.010879 | 0.016159 | −0.005826 | 0.012117 |
| 140 | −0.029003 | 0.000348 | 0.010362 | 0.010336 | −0.009082 | 0.004462 | −0.004441 | −0.002759 | 0.007178 | −0.01279 | 0.024325 | 0.052376 | −0.016981 | −0.034557 |
| 141 | 0.003524 | −0.027014 | 0.008281 | 0.044288 | 0.024979 | 0.00166 | −0.002797 | 0.011499 | −0.033942 | 0.007396 | −0.007088 | 0.003403 | −0.013811 | 0.003258 |
| 142 | −0.013546 | 0.008858 | 0.006603 | −0.024195 | 0.045935 | 0.014671 | −0.011163 | −0.012799 | −0.00234 | 0.005347 | −0.016374 | −0.018222 | −0.094524 | −0.020947 |
| 143 | −0.033059 | −0.014882 | −0.006357 | −0.012828 | 0.004646 | −0.007549 | −0.000731 | 0.016889 | −0.077931 | 0.011268 | 0.022084 | 0.028839 | 0.039743 | −0.006341 |
| 144 | 0.000683 | −0.014344 | −0.016389 | −0.021014 | 0.017887 | 0.038594 | 0.034493 | 0.014075 | −0.016824 | −0.006967 | 0.031742 | 0.032475 | −0.019624 | −0.014019 |
| 145 | 0.013437 | −0.000247 | 0.041401 | 0.036588 | −0.00115 | −0.008798 | −0.008467 | 0.030313 | 0.095418 | −0.002324 | 0.03629 | 0.034041 | 0.043959 | −0.034994 |
| 146 | −0.034324 | 0.0133 | 0.026999 | −0.005715 | 0.004176 | 0.002071 | 0.049494 | −0.003053 | 0.011889 | −0.038888 | −0.017413 | −0.015247 | −0.028945 | 0.005244 |
| 147 | −0.019331 | 0.015149 | 0.002588 | −0.001276 | −0.013215 | 0.010039 | −0.000199 | −0.008217 | 0.050956 | −0.000225 | 0.006925 | 0.010322 | 0.00419 | −0.034602 |
| 148 | −0.005477 | −0.004621 | −0.057781 | −0.016872 | −0.024884 | −0.01495 | 0.007549 | −0.023448 | 0.07627 | 0.022331 | −0.014422 | −0.019772 | −0.014534 | −0.01575 |
| 149 | 0.017789 | −0.000714 | 0.011368 | 0.023359 | 0.033712 | 0.028868 | 0.036365 | 0.019455 | −0.04041 | −0.009529 | 0.004336 | 0.01466 | −0.003075 | 0.008226 |
| 150 | −0.008888 | 0.03946 | 0.010183 | −0.009983 | 0.053271 | 0.031797 | 0.034246 | −0.02393 | −0.033559 | 0.01149 | −0.013315 | −0.023028 | −0.010711 | 0.031599 |
| 151 | −0.02438 | −0.03883 | −0.055254 | 0.009688 | 0.019824 | 0.019094 | 0.021672 | 0.007467 | 0.065376 | 0.027882 | −0.011975 | −0.00743 | 0.019572 | 0.023903 |
| 152 | −0.026559 | −0.005561 | −0.00599 | 0.057584 | −0.061247 | −0.024531 | −0.013573 | 0.008197 | −0.027437 | 0.002333 | 0.001728 | 0.012551 | 0.041306 | −0.008186 |
| 153 | 0.001348 | 0.057055 | 0.043996 | −0.012167 | −0.068293 | −0.015827 | −0.006484 | −0.034873 | 0.005396 | 0.013197 | −0.000287 | 0.020491 | −0.03986 | −0.013972 |
| 154 | 0.00158 | 0.029556 | 0.01106 | 0.03777 | 0.002883 | −0.008093 | −0.011177 | −0.028521 | −0.02672 | −0.031214 | −0.005717 | 0.002317 | −0.00034 | 0.007004 |
| 155 | −0.006031 | 0.014594 | 0.03784 | 0.03803 | 0.016623 | −0.001089 | 0.001483 | −0.012935 | 0.017033 | −0.025476 | −0.02395 | −0.014998 | −0.001233 | 0.025073 |
| 156 | 0.000518 | 0.058054 | 0.043139 | 0.003938 | −0.020116 | 0.046044 | 0.036545 | 0.028709 | 0.032302 | −0.009752 | 0.014824 | 0.012628 | −0.019313 | 0.009171 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 157 | −0.01321 | −0.019545 | 0.007922 | 0.002507 | 0.019579 | 0.004532 | −0.010869 | 0.035257 | 0.016396 | −0.040353 | 0.004702 | 0.004362 | −0.014016 | −0.023416 |
| 158 | −0.007165 | −0.017498 | −0.014244 | −0.032312 | −0.004795 | 0.012018 | 0.011479 | 0.014965 | 0.013653 | 0.004118 | −0.015052 | −0.024945 | 0.023264 | 0.007973 |
| 159 | 0.03814 | −0.028627 | −0.004428 | −0.003332 | −0.031196 | −0.010859 | 0.002848 | −0.015732 | −0.006196 | 0.005936 | −0.017978 | −0.005896 | −0.037291 | 0.050862 |
| 160 | −0.011276 | −0.036307 | −0.025016 | −0.033767 | −0.00197 | 0.008762 | −0.016105 | 0.013796 | 0.018482 | 0.013344 | 0.023247 | 0.022636 | −0.002356 | 0.031013 |
| 161 | −0.046762 | −0.017461 | −0.016652 | −0.011533 | −0.057473 | −0.027673 | −0.0064 | 0.006918 | 0.026048 | −0.035886 | 0.026724 | 0.0193 | 0.009651 | −0.048473 |
| 162 | 0.017088 | −0.080274 | −0.03781 | −0.018136 | −0.021895 | 0.027026 | 0.032166 | 0.017967 | −0.014126 | 0.024866 | 0.047207 | 0.036461 | 0.007153 | 0.022806 |
| 163 | 0.032999 | −0.033251 | −0.043341 | 0.012627 | −0.018812 | −0.015063 | −0.026412 | 0.002246 | 0.080545 | 0.029078 | −0.01693 | −0.013135 | −0.013869 | −0.004707 |
| 164 | 0.002923 | 0.028032 | 0.003799 | −0.078136 | 0.045678 | 0.027446 | 0.050495 | 0.04327 | −0.019921 | −0.019662 | −0.023016 | −0.03646 | −0.002774 | −0.018529 |
| 165 | 0.022835 | 0.028198 | 0.019952 | 0.009166 | 0.048623 | −0.010382 | −0.023782 | 0.013832 | −0.048231 | 0.0285351 | −0.003129 | −0.003128 | 0.054115 | −0.006757 |
| 166 | 0.008177 | −0.020075 | −0.029495 | −0.001123 | 0.053296 | −0.02125 | 0.024746 | 0.006233 | −0.039228 | −0.014628 | −0.044461 | −0.035397 | 0.006506 | −0.029502 |
| 167 | −0.027582 | −0.05463 | −0.016855 | 0.014079 | 0.063347 | 0.010558 | 0.025062 | 0.025163 | −0.002069 | −0.040511 | −0.019812 | −0.035007 | −0.016194 | −0.030526 |
| 168 | 0.065338 | 0.01116 | −0.094556 | −0.061073 | 0.028061 | −0.018405 | 0.022079 | −0.024328 | −0.052186 | 0.082323 | −0.00013 | −0.015125 | −0.033992 | 0.046104 |
| 169 | 0.033293 | −0.003814 | 0.014946 | −0.015848 | 0.001966 | 0.017603 | 0.015841 | −0.004535 | −0.011768 | 0.02781 | 0.026618 | 0.024789 | −0.011485 | 0.003906 |
| 170 | 0.036546 | 0.028648 | 0.040844 | 0.001842 | 0.006589 | 0.007197 | −0.00457 | −0.005774 | −0.028362 | 0.039414 | 0.037307 | 0.034625 | 0.00411 | 0.006054 |
| 171 | 0.001481 | −0.002525 | 0.007629 | −0.002508 | −0.035681 | −0.013005 | −0.000928 | 0.002463 | −0.036915 | 0.03082 | 0.021316 | 0.033102 | 0.015381 | 0.02302 |
| 172 | −0.011351 | −0.009604 | 0.001287 | −0.000966 | −0.016151 | 0.002599 | 0.042631 | 0.013378 | 0.013671 | −0.021485 | −0.005749 | 0.000533 | 0.005583 | 0.024176 |
| 173 | 0.00495 | −0.005462 | 0.004026 | −0.015836 | 0.003049 | −0.027503 | −0.017371 | −0.015107 | 0.027679 | 0.008362 | −0.006979 | −0.000861 | −0.007958 | 0.044111 |
| 174 | 0.024728 | 0.053263 | 0.002953 | −0.007203 | 0.001052 | 0.022924 | 0.003381 | −0.002559 | 0.059259 | −0.001233 | −0.03979 | −0.041719 | −0.039609 | 0.011527 |
| 175 | 0.015608 | 0.029864 | 0.010549 | 0.056429 | −0.015208 | −0.003892 | 0.0044 | −0.012444 | 0.009105 | −0.048955 | −0.01309 | −0.009193 | 0.023208 | −0.010059 |
| 176 | 0.007795 | −0.039559 | −0.029528 | 0.008638 | −0.03419 | −0.013344 | 0.031862 | 0.030117 | −0.005516 | −0.023188 | 0.016914 | 0.012924 | 0.063111 | −0.068136 |
| 177 | 0.000491 | 0.03588 | 0.07508 | 0.058434 | 0.033515 | −0.001039 | −0.054092 | −0.017293 | 0.008845 | −0.001217 | 0.016111 | 0.002886 | 0.017085 | −0.002351 |
| 178 | −0.014527 | −0.011772 | 0.03335 | 0.045354 | −0.011167 | 0.006547 | 0.02343 | 0.00956 | −0.009963 | −0.024216 | −0.009132 | −0.007229 | −0.000835 | −0.020653 |
| 179 | −0.007407 | 0.022685 | −0.000785 | 0.018765 | 0.024175 | 0.020427 | 0.022685 | 0.017042 | −0.005903 | 0.005 | −0.019878, | −0.018022 | −0.006308 | 0.001748 |
| 180 | 0.009985 | 0.011684 | 0.019523 | 0.017478 | 0.004017 | 0.016556 | 0.01394 | −0.003055 | −0.001256 | 0.01464 | −0.009573 | −0.021635 | −0.00642 | −0.027279 |
| 181 | −0.023494 | 0.011613 | 0.030288 | 0.016506 | −0.011189 | 0.015166 | 0.008465 | 0.00531 | −0.024585 | −0.013686 | −0.007001 | −0.012926 | 0.011299 | −0.026697 |
| 182 | −0.011022 | 0.022177 | 0.024813 | 0.018702 | 0.034983 | 0.019768 | 0.018504 | −0.0105 | −0.079475 | −0.0058 | 0.025956 | 0.014124 | 0.008771 | 0.010556 |
| 183 | −0.000532 | 0.017495 | 0.033536 | 0.023726 | 0.028199 | −0.01153 | −0.024572 | −0.025599 | −0.063017 | 0.019138 | −0.001443 | 0.008775 | 0.014634 | 0.01676 |
| 184 | 0.005169 | −0.023261 | 0.020678 | −0.047704 | 0.000057 | −0.009338 | −0.023716 | −0.013489 | 0.035629 | 0.019962 | −0.002053 | 0.01423 | −0.014316 | −0.021347 |
| 185 | 0.008707 | 0.049023 | 0.066766 | 0.019334 | 0.049421 | −0.028828 | −0.035661 | −0.030386 | 0.044378 | 0.036988 | −0.016822 | −0.020338 | 0.038685 | −0.019489 |
| 186 | 0.002917 | 0.020628 | 0.00777 | −0.044608 | −0.03745 | −0.005031 | −0.009997 | 0.025025 | −0.091809 | 0.029594 | −0.011298 | −0.008211 | 0.037641 | −0.032063 |
| 187 | 0.033363 | −0.011637 | −0.023018 | −0.011106 | −0.004241 | −0.008277 | −0.000525 | −0.023676 | 0.017503 | 0.013454 | 0.015773 | 0.004066 | −0.026121 | 0.029049 |
| 188 | 0.021416 | −0.026302 | −0.010926 | −0.012504 | 0.003588 | −0.014522 | −0.009484 | −0.001561 | 0.015141 | 0.035967 | 0.008994 | 0.007379 | 0.013304 | 0.023027 |
| 189 | 0.003228 | −0.028948 | −0.022341 | −0.035018 | −0.025225 | −0.031201 | −0.025517 | −0.010628 | 0.016921 | −0.022095 | 0.00303 | 0.005319 | 0.034342 | −0.017705 |
| 190 | 0.020702 | −0.023074 | −0.025993 | 0.019278 | −0.006976 | −0.033922 | −0.039489 | −0.014105 | −0.021457 | 0.016043 | −0.041279 | −0.033288 | −0.004557 | −0.025789 |
| 191 | 0.012435 | 0.017589 | 0.008084 | 0.035561 | 0.007799 | 0.002736 | −0.003517 | −0.011418 | −0.025921 | 0.016741 | −0.009308 | −0.011163 | −0.036444 | 0.01019 |
| 192 | −0.012561 | −0.027059 | 0.007856 | 0.035817 | 0.027199 | −0.006927 | 0.038607 | 0.011019 | −0.043884 | −0.012849 | −0.046786 | −0.035057 | 0.029355 | 0.002933 |
| 193 | 0.006814 | −0.016566 | −0.072465 | 0.019789 | 0.025436 | 0.042276 | 0.066888 | −0.001277 | 0.034317 | −0.037552 | 0.022653 | 0.025355 | −0.052899 | 0.039452 |
| 194 | −0.021908 | −0.05194 | −0.030581 | −0.007834 | 0.036415 | 0.029666 | 0.020249 | 0.017269 | 0.005831 | 0.020724 | 0.009043 | 0.024362 | −0.010554 | 0.00304 |
| 195 | 0.001687 | 0.041501 | −0.091532 | −0.095976 | 0.015619 | −0.031294 | −0.020336 | −0.005149 | 0.015026 | −0.042622 | −0.028596 | −0.025788 | 0.014983 | 0.000043 |
| 196 | 0.005625 | 0.040935 | −0.007768 | −0.067678 | −0.015607 | −0.007233 | 0.008511 | 0.020599 | 0.027954 | −0.007999 | −0.010044 | −0.011815 | 0.007798 | −0.046793 |
| 197 | −0.008854 | 0.011633 | 0.027274 | 0.002358 | 0.009943 | 0.022908 | 0.026462 | −0.023555 | 0.007326 | 0.023075 | 0.001482 | 0.006027 | −0.06017 | −0.032572 |
| 198 | −0.061236 | −0.00181 | 0.008836 | −0.008163 | −0.021911 | −0.035895 | −0.030072 | −0.043188 | 0.06451 | −0.052166 | −0.012228 | −0.000963 | −0.056983 | 0.010862 |
| 199 | 0.010442 | 0.004065 | −0.003366 | −0.027146 | −0.019502 | −0.028206 | −0.003247 | −0.010674 | −0.000454 | −0.022008 | −0.05956 | −0.04757 | −0.015643 | 0.012602 |
| 200 | −0.017976 | 0.049683 | −0.001737 | −0.01778 | −0.004936 | 0.005151 | −0.024496 | 0.01125 | −0.052211 | −0.009012 | −0.02017 | −0.013936 | −0.027655 | 0.057119 |
| 201 | 0.014922 | 0.024555 | 0.015443 | −0.013111 | 0.01299 | 0.008567 | 0.01467 | 0.013632 | 0.002438 | 0.02175 | −0.013961 | −0.013599 | −0.008414 | 0.044185 |
| 202 | −0.046768 | 0.025057 | 0.017541 | 0.01223 | −0.027305 | −0.015076 | 0.015141 | −0.004918 | −0.021704 | 0.04427 | −0.021075 | −0.003208 | 0.020956 | 0.053369 |
| 203 | −0.022324 | 0.021399 | 0.022114 | −0.016311 | −0.048723 | −0.051587 | −0.02055 | −0.034381 | −0.042238 | −0.005964 | 0.016059 | 0.021801 | −0.008253 | −0.037496 |
| 204 | 0.005619 | 0.033906 | −0.015244 | 0.006037 | −0.045018 | 0.003964 | 0.000596 | 0.007825 | 0.02028 | −0.086363 | −0.035963 | −0.038475 | −0.005175 | −0.037477 |
| 205 | 0.04582 | 0.036084 | 0.047024 | 0.026872 | 0.033301 | 0.016246 | −0.002239 | 0.009613 | 0.006138 | 0.016502 | 0.015605 | −0.007329 | −0.026142 | −0.004513 |
| 206 | −0.05878 | −0.048785 | −0.005664 | −0.024318 | 0.001018 | 0.024208 | 0.016367 | 0.019663 | :0.050125 | 0.024461 | 0.03596 | 0.034836 | 0.007139 | −0.015215 |
| 207 | −0.009287 | 0.001896 | −0.007257 | 0.003677 | −0.005388 | −0.001637 | 0.004558 | 0.010644 | −0.014296 | 0.015871 | −0.003788 | 0.00135 | −0.0427 | −0.020393 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 208 | 0.018062 | −0.043207 | 0.007043 | 0.017203 | −0.011686 | 0.04066 | 0.048104 | 0.013388 | 0.018384 | −0.019867 | 0.002644 | 0.008953 | −0.013873 | −0.014296 |
| 209 | −0.027463 | −0.03982 | 0.008907 | 0.006863 | 0.045154 | 0.02848 | −0.00445 | −0.025077 | 0.022759 | 0.00714 | 0.018245 | 0.01099 | 0.010527 | −0.00891 |
| 210 | 0.001861 | 0.01006 | 0.058821 | 0.013523 | −0.014232 | −0.024997 | −0.000894 | −0.00811 | 0.008667 | 0.014315 | −0.000332 | 0.001565 | −0.009402 | −0.048028 |
| 211 | −0.002394 | 0.013546 | 0.012624 | −0.012886 | −0.036424 | 0.004737 | 0.01357 | 0.033234 | −0.040649 | −0.041351 | −0.010645 | 0.008948 | −0.014164 | 0.013438 |
| 212 | −0.02573 | −0.051098 | −0.023011 | −0.03777 | 0.011494 | −0.024995 | −0.026725 | 0.024551 | 0.013601 | −0.003406 | 0.009938 | 0.009441 | 0.033609 | 0.003162 |
| 213 | 0.034629 | −0.031202 | −0.003858 | 0.029334 | 0.010518 | 0.006729 | −0.009523 | −0.01814 | −0.032806 | −0.029788 | 0.010271 | 0.002323 | −0.019193 | 0.017671 |
| 214 | −0.006551 | 0.027184 | 0.0027 | −0.024963 | −0.00753 | 0.023254 | 0.01743 | 0.023812 | −0.025262 | 0.011297 | −0.00246 | −0.004811 | 0.008133 | 0.000102 |
| 215 | 0.005863 | 0.001175 | −0.035326 | −0.012828 | −0.037299 | 0.005648 | −0.011981 | 0.017535 | 0.040609 | −0.035302 | −0.003356 | −0.008488 | −0.04333 | 0.071665 |
| 216 | −0.028877 | −0.036283 | −0.003856 | 0.006689 | −0.023179 | −0.003335 | 0.013149 | −0.005522 | −0.024886 | 0.05699 | 0.074558 | 0.080731 | −0.035431 | −0.035163 |
| 217 | −0.007104 | 0.006465 | −0.021166 | −0.019474 | 0.008569 | 0.037634 | 0.017059 | 0.035077 | 0.066941 | 0.042102 | 0.020985 | 0.016102 | 0.065853 | 0.018365 |
| 218 | 0.0088 | 0.047462 | 0.034341 | 0.000187 | −0.04034 | −0.007946 | 0.022547 | −0.010583 | −0.011335 | −0.024149 | 0.01054 | 0.008745 | 0.019919 | −0.01901 |
| 219 | 0.015458 | 0.023372 | 0.046251 | −0.007604 | −0.005555 | −0.002094 | 0.004281 | 0.006456 | 0.032114 | 0.001575 | 0.03823 | 0.030076 | 0.012197 | −0.006538 |
| 220 | −0.019243 | −0.003219 | −0.044257 | −0.005294 | −0.007494 | 0.032101 | 0.01783 | 0.000387 | 0.051287 | 0.022308 | 0.0139 | 0.015151 | −0.01185 | 0.01498 |
| 221 | 0.00072 | 0.019465 | 0.037131 | 0.015479 | −0.008912 | −0.000571 | 0.01944 | 0.024077 | 0.01738 | −0.021037 | 0.0026 | 0.01099 | 0.030855 | −0.014492 |
| 222 | −0.024456 | −0.107154 | −0.027927 | 0.021541 | 0.035039 | −0.029096 | −0.02926 | 0.013034 | −0.015535 | 0.022371 | −0.014191 | −0.001081 | 0.029474 | −0.001973 |
| 223 | −0.011217 | −0.056833 | −0.092023 | −0.048269 | 0.023066 | −0.005261 | −0.015741 | −0.001763 | 0.002002 | −0.002401 | 0.000877 | 0.007828 | −0.01448 | −0.009423 |
| 224 | −0.012539 | −0.006368 | 0.011659 | −0.027983 | −0.004665 | −0.000874 | 0.006566 | −0.013226 | 0.013051 | 0.055018 | 0.007245 | −0.007566 | −0.002035 | −0.00694 |
| 225 | −0.014177 | −0.012321 | 0.014259 | −0.021956 | 0.005721 | −0.004501 | −0.000198 | 0.002807 | 0.018922 | 0.048708 | 0.007414 | 0.001473 | 0.009768 | 0.009824 |
| 226 | 0.005458 | 0.007807 | 0.025808 | 0.027387 | −0.078584 | −0.11967 | −0.106859 | −0.089772 | −0.02062 | −0.026575 | −0.033409 | −0.02258 | −0.001327 | 0.027276 |
| 227 | 0.018674 | −0.011777 | 0.003707 | 0.014121 | 0.027456 | −0.022637 | −0.045541 | −0.115704 | 0.001523 | 0.058455 | 0.012783 | 0.006826 | −0.108115 | 0.074392 |
| 228 | −0.034507 | 0.001195 | −0.02014 | −0.005313 | 0.028206 | −0.005158 | 0.005189 | −0.019313 | 0.006295 | −0.082512 | −0.032292 | −0.041178 | −0.019441 | −0.022573 |
| 229 | 0.015894 | −0.000377 | 0.034195 | −0.016006 | −0.049227 | 0.047862 | 0.015083 | 0.053456 | −0.06582 | −0.167473 | −0.047996 | −0.06371 | −0.00286 | −0.052212 |
| 230 | −0.028402 | 0.02607 | 0.020673 | −0.002446 | 0.032032 | 0.016028 | 0.011636 | 0.005278 | −0.010095 | −0.007205 | −0.069107 | −0.070185 | −0.140297 | −0.000809 |
| 231 | −0.017468 | −0.041009 | 0.005971 | −0.004161 | −0.062523 | −0.018785 | −0.03913 | −0.020468 | −0.003208 | −0.063586 | 0.031959 | 0.043861 | 0.016169 | −0.040574 |
| 232 | −0.034084 | 0.026882 | 0.008907 | 0.014559 | 0.019729 | 0.020778 | −0.021014 | 0.026577 | 0.017527 | 0.030265 | 0.003393 | 0.005064 | 0.019172 | −0.027834 |
| 233 | 0.042799 | 0.012431 | 0.008317 | 0.051628 | −0.003328 | 0.00347 | 0.035464 | 0.019018 | 0.032141 | 0.014057 | 0.001874 | 0.018665 | 0.04531 | 0.053068 |
| 234 | 0.008567 | 0.042411 | 0.042268 | −0.008451 | −0.045524 | −0.050646 | −0.021903 | −0.026193 | 0.097571 | 0.045364 | 0.003129 | 0.006616 | 0.00606 | −0.023292 |
| 235 | −0.025828 | 0.000441 | −0.005206 | −0.004188 | 0.051778 | −0.001471 | −0.021784 | −0.000886 | 0.004268 | 0.074614 | 0.022074 | −0.000318 | 0.026327 | −0.005219 |
| 236 | −0.015174 | 0.035285 | 0.020759 | −0.001658 | 0.058353 | 0.031022 | 0.016053 | 0.020847 | 0.009475 | 0.031682 | 0.01383 | 0.015968 | −0.034305 | −0.16702 |
| 237 | −0.009542 | 0.02843 | 0.005043 | −0.021671 | 0.065308 | 0.059066 | 0.046668 | 0.057712 | −0.037744 | 0.014609 | 0.029579 | 0.02536 | 0.026153 | 0.008781 |
| 238 | −0.012605 | 0.014955 | 0.023309 | −0.000525 | 0.030655 | 0.047576 | 0.022708 | 0.060663 | 0.028342 | −0.018093 | 0.037441 | 0.037839 | −0.004274 | 0.007517 |
| 239 | −0.006117 | −0.012625 | −0.017771 | 0.015764 | 0.020176 | 0.009083 | 0.025395 | 0.031095 | 0.039825 | −0.022547 | 0.029918 | 0.034372 | 0.001497 | 0.010817 |
| 240 | 0.0315 | −0.036759 | −0.018418 | 0.030181 | −0.02696 | −0.0098 | 0.024531 | 0.008857 | 0.021882 | −0.038813 | −0.014216 | −0.010182 | 0.017206 | 0.023587 |
| 241 | 0.053503 | 0.016181 | 0.025386 | 0.025372 | 0.002338 | −0.001197 | −0.018232 | 0.004752 | −0.031593 | −0.027654 | 0.007999 | −0.005907 | 0.008147 | −0.000092 |
| 242 | −0.035165 | 0.017419 | 0.005788 | 0.040736 | 0.023784 | −0.003208 | −0.002023 | −0.009898 | −0.063063 | 0.077509 | 0.020865 | 0.02004 | 0.02533 | −0.018745 |
| 243 | −0.014998 | 0.001611 | 0.007787 | 0.014543 | 0.027309 | 0.007252 | −0.004859 | 0.006244 | 0.004569 | 0.023415 | −0.003068 | −0.002323 | −0.00333 | 0.015019 |
| 244 | 0.015398 | −0.023448 | −0.018089 | 0.001086 | 0.020217 | 0.02501 | 0.025547 | 0.014088 | −0.01289 | −0.002771 | 0.000106 | 0.001735 | −0.01482 | 0.008858 |
| 245 | −0.015989 | −0.026625 | −0.0062 | −0.028258 | −0.025092 | 0.046153 | 0.04995 | 0.033654 | −0.03425 | −0.000884 | 0.041411 | 0.046059 | 0.016564 | −0.001389 |
| 246 | 0.035151 | 0.00042 | −0.029008 | 0.006479 | −0.026975 | 0.034251 | 0.055406 | 0.014023 | −0.006605 | −0.024309 | 0.028832 | 0.024093 | −0.000054 | 0.03679 |
| 247 | 0.03361 | 0.01061 | −0.007813 | −0.015562 | 0.007987 | 0.00678 | 0.010656 | 0.033666 | −0.021841 | −0.02243 | −0.017137 | −0.014735 | −0.021479 | −0.021214 |
| 248 | −0.036401 | −0.002479 | 0.015871 | −0.004851 | 0.033799 | 0.004226 | −0.015162 | −0.014447 | 0.01118 | −0.020108 | −0.027452 | −0.022887 | −0.057396 | −0.032146 |
| 249 | −0.036364 | −0.087328 | 0.029847 | 0.045071 | 0.017743 | −0.011591 | −0.029546 | 0.009635 | 0.027647 | 0.031695 | −0.016013 | −0.013356 | 0.021993 | −0.021344 |
| 250 | 0.047375 | 0.000081 | 0.003357 | −0.003545 | −0.011775 | 0.016638 | 0.006451 | −0.008767 | −0.018016 | −0.015253 | 0.012588 | 0.000425 | −0.007434 | −0.00112 |
| 251 | 0.005264 | −0.006343 | 0.015965 | 0.026596 | 0.04394 | 0.028626 | 0.018449 | −0.005772 | −0.009394 | −0.047565 | −0.029305 | −0.036435 | −0.045395 | 0.019948 |
| 252 | −0.054311 | 0.023832 | 0.005391 | −0.003786 | 0.013619 | 0.004517 | −0.006279 | −0.004574 | −0.013203 | 0.014814 | −0.004244 | −0.00207 | 0.000085 | −0.004303 |
| 253 | −0.051369 | −0.028405 | −0.05084 | −0.015118 | −0.110147 | 0.007462 | 0.017222 | −0.023795 | −0.075503 | −0.080365 | 0.034513 | 0.036541 | 0.000458 | −0.033724 |
| 254 | −0.008194 | −0.056622 | −0.130368 | −0.070016 | 0.013158 | 0.029912 | 0.028327 | 0.007356 | 0.000824 | 0.021892 | 0.014153 | 0.02524 | −0.001656 | 0.008273 |
| 255 | 0.015023 | −0.028034 | −0.056286 | −0.026845 | 0.016724 | 0.033515 | 0.04293 | −0.003523 | −0.016019 | −0.06302 | 0.007405 | 0.001116 | −0.033656 | 0.028458 |
| 256 | 0.000286 | 0.024443 | −0.007471 | −0.111448 | −0.021054 | 0.032515 | 0.016849 | 0.041029 | 0.035689 | 0.012647 | 0.040801 | 0.023736 | 0.03469 | −0.00435 |
| 257 | −0.016446 | 0.020594 | 0.021965 | 0.048914 | 0.012818 | −0.012809 | 0.007566 | −0.002898 | 0.050192 | 0.042075 | −0.014073 | −0.005799 | 0.019216 | 0.000174 |
| 258 | −0.004398 | −0.007344 | −0.038028 | 0.028098 | 0.003019 | −0.011993 | 0.028997 | 0.002028 | 0.026966 | −0.030099 | −0.021421 | −0.008697 | 0.009983 | −0.031529 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 259 | −0.024049 | −0.102041 | −0.035356 | 0.026498 | 0.030089 | −0.000983 | 0.008031 | 0.009088 | −0.008402 | 0.003828 | −0.015151 | −0.00836 | 0.003874 | −0.003775 |
| 260 | −0.028118 | −0.043276 | −0.082658 | −0.044006 | −0.032122 | 0.010492 | 0.016845 | 0.012597 | 0.028308 | 0.01823 | 0.017412 | 0.025114 | 0.023228 | 0.021954 |
| 261 | −0.063192 | 0.008886 | −0.052659 | −0.104184 | 0.010388 | 0.036039 | 0.040797 | 0.010197 | 0.04044 | 0.014139 | 0.008704 | 0.011218 | −0.022608 | −0.006959 |
| 262 | −0.133703 | 0.03933 | −0.017755 | −0.03949 | −0.005364 | 0.015987 | 0.018847 | 0.024815 | −0.012699 | 0.037862 | 0.015433 | 0.026876 | 0.001481 | −0.054456 |
| 263 | 0.801765 | −0.011276 | 0.001185 | −0.016436 | −0.000995 | 0.008711 | 0.030829 | 0.009419 | −0.026313 | 0.007835 | 0.015741 | 0.026 | −0.007284 | −0.049954 |
| 264 | 0.017456 | 0.712691 | −0.132132 | 0.028396 | 0.001317 | 0.00173 | 0.005487 | 0.0175 | −0.026253 | −0.041178 | 0.012274 | 0.019313 | −0.000005 | 0.021334 |
| 265 | 0.041806 | −0.1576 | 0.688564 | −0.13802 | −0.019291 | 0.000782 | 0.024748 | 0.010086 | 0.005778 | −0.029051 | 0.014838 | 0.019138 | 0.027784 | 0.052728 |
| 266 | −0.013322 | 0.014564 | −0.159762 | 0.699019 | 0.027083 | 0.008061 | −0.001333 | 0.013934 | −0.032372 | 0.044535 | 0.041274 | 0.032301 | 0.02937 | −0.004354 |
| 267 | 0.002847 | 0.016537 | 0.000994 | 0.036362 | 0.579947 | −0.074683 | −0.042692 | −0.011223 | −0.10012 | −0.102898 | 0.05355 | 0.062114 | 0.059825 | −0.03838 |
| 268 | −0.01299 | 0.003202 | 0.013949 | 0.030024 | −0.098981 | 0.850225 | −0.115659 | −0.077637 | −0.029662 | −0.006212 | −0.030997 | −0.014234 | 0.034636 | 0.011697 |
| 269 | −0.007421 | 0.019615 | 0.056322 | 0.017677 | −0.033524 | −0.107932 | 0.830811 | −0.09607 | −0.041739 | 0.033461 | −0.00086 | −0.004449 | 0.006297 | 0.016981 |
| 270 | −0.008399 | 0.001985 | 0.012943 | 0.025827 | −0.023328 | −0.080718 | −0.092768 | 0.815761 | −0.044946 | 0.033256 | −0.022932 | −0.030369 | −0.09094 | 0.049298 |
| 271 | −0.017575 | −0.033368 | −0.021955 | −0.029493 | −0.049501 | −0.007103 | −0.019723 | −0.029547 | 0.331594 | −0.118031 | 0.007624 | −0.006916 | −0.017464 | −0.005956 |
| 272 | 0.003257 | −0.04321 | −0.001438 | 0.042921 | −0.148164 | 0.008961 | 0.014875 | 0.03982 | −0.054089 | 0.607606 | −0.105856 | −0.10036 | −0.037258 | −0.082433 |
| 273 | 0.000245 | 0.01244 | 0.009566 | 0.036917 | 0.034417 | −0.036752 | −0.018334 | −0.02084 | 0.028038 | −0.100784 | 0.801288 | −0.182851 | −0.083506 | −0.014547 |
| 274 | 0.009881 | 0.026516 | 0.014213 | 0.019885 | 0.050518 | −0.023494 | −0.018529 | −0.025315 | 0.020633 | −0.088797 | −0.186599 | 0.808734 | −0.084024 | −0.007316 |
| 275 | −0.016792 | −0.015784 | 0.0159 | 0.01079 | 0.060224 | 0.052025 | 0.011473 | −0.06917 | −0.009877 | −0.013072 | −0.079368 | −0.083334 | 0.668067 | 0.012859 |
| 276 | −0.044819 | 0.031952 | 0.056771 | 0.006656 | −0.010752 | 0.012369 | 0.010543 | 0.041177 | 0.017132 | −0.039245 | −0.002842 | 0.006705 | 0.010057 | 0.727436 |
| 277 | 0.003225 | 0.017861 | 0.011425 | 0.001008 | 0.023958 | 0.022014 | 0.017686 | 0.022026 | 0.018092 | 0.032171 | 0.016432 | 0.01218 | 0.034949 | −0.050698 |
| 278 | 0.015425 | 0.041021 | 0.021906 | −0.01467 | 0.042724 | 0.046164 | 0.03275 | 0.008214 | 0.003579 | 0.023234 | 0.033777 | 0.021682 | 0.013045 | −0.006731 |
| 279 | −0.004295 | −0.017184 | 0.002521 | −0.013719 | 0.031265 | 0.023481 | 0.007102 | −0.001021 | 0.031123 | 0.016121 | 0.047446 | 0.040578 | −0.030992 | 0.004895 |
| 280 | −0.055672 | −0.024746 | −0.009537 | −0.012478 | −0.008759 | −0.018572 | 0.018357 | 0.017944 | −0.039775 | −0.015836 | −0.016015 | −0.001203 | 0.025473 | −0.023487 |
| 281 | −0.003645 | −0.048477 | −0.005212 | 0.012757 | −0.045295 | 0.006188 | 0.023031 | 0.003346 | −0.005938 | −0.033902 | 0.021489 | 0.023675 | 0.005157 | −0.002399 |
| 282 | 0.008852 | −0.012506 | 0.012529 | 0.0099 | −0.0079 | 0.00393 | −0.025659 | −0.008637 | −0.036165 | −0.010594 | 0.014611 | 0.019242 | −0.013025 | 0.0152 |
| 283 | 0.01127 | 0.029332 | 0.012214 | −0.047126 | −0.00634 | 0.023303 | 0.005903 | −0.013993 | −0.006786 | −0.040868 | −0.01904 | −0.031434 | −0.065071 | −0.022127 |
| 284 | 0.004105 | −0.013568 | 0.03474 | 0.055439 | 0.016218 | 0.004936 | 0.00615 | −0.018616 | 0.039007 | 0.03023 | −0.019661 | −0.019577 | −0.020656 | −0.020337 |
| 285 | 0.01666 | 0.001636 | 0.030017 | −0.04942 | 0.013675 | −0.004587 | −0.009963 | −0.051126 | 0.031735 | 0.016294 | −0.035469 | −0.050631 | −0.019596 | −0.009524 |
| 286 | −0.021275 | −0.032637 | 0.002673 | 0.043152 | 0.019169 | 0.013244 | 0.017589 | −0.004375 | 0.010065 | 0.002219 | 0.009265 | 0.016123 | 0.004836 | −0.000554 |
| 287 | −0.017262 | −0.001341 | 0.028841 | 0.015472 | 0.022573 | 0.007444 | 0.002024 | −0.030745 | 0.031839 | 0.022795 | 0.008393 | 0.004772 | −0.021539 | 0.014437 |
| 288 | −0.020436 | 0.024058 | −0.00265 | −0.064451 | 0.052726 | 0.020625 | 0.005964 | −0.031116 | 0.018928 | 0.0214 | 0.017606 | 0.002506 | −0.045827 | −0.028712 |
| 289 | −0.047401 | 0.043255 | −0.045237 | −0.079093 | 0.012475 | −0.001903 | −0.00213 | −0.029847 | −0.035975 | 0.050317 | 0.009421 | 0.000692 | −0.029373 | −0.032355 |
| 290 | −0.001638 | 0.03693 | 0.021929 | −0.012929 | 0.003268 | −0.000729 | −0.003871 | −0.000557 | 0.0107 | 0.034771 | 0.010233 | 0.015533 | −0.009055 | 0.012058 |
| 291 | −0.010243 | 0.026541 | 0.027062 | −0.011825 | 0.000875 | 0.006558 | 0.00314 | 0.005299 | −0.006337 | 0.030566 | 0.016744 | 0.020901 | −0.008349 | 0.013873 |
| 292 | 0.026409 | −0.000895 | 0.011838 | −0.002069 | 0.008656 | 0.016496 | −0.012783 | −0.011161 | 0.002857 | 0.014156 | 0.027492 | 0.016739 | −0.033053 | 0.010692 |
| 293 | 0.013295 | 0.01496 | −0.009451 | −0.018109 | −0.004855 | −0.013593 | 0.01688 | 0.018518 | 0.024532 | −0.018615 | −0.000256 | 0.016398 | −0.002911 | −0.026983 |
| 294 | 0.034197 | −0.012109 | −0.015301 | −0.041781 | 0.000449 | −0.016387 | −0.0223 | −0.040285 | −0.021378 | 0.03133 | −0.007768 | −0.01605 | −0.036113 | 0.019337 |
| 295 | −0.024147 | 0.03592 | 0.003792 | −0.014804 | 0.007159 | 0.011038 | 0.047622 | 0.010577 | −0.008813 | −0.016315 | −0.078865 | −0.084665 | −0.004113 | 0.008709 |
| 296 | −0.041654 | −0.019714 | −0.026919 | −0.014228 | −0.040009 | −0.005209 | −0.012213 | −0.055324 | −0.020533 | −0.034979 | −0.060185 | −0.072533 | −0.097772 | 0.019793 |
| 297 | −0.029834 | 0.005623 | 0.019973 | −0.004316 | 0.002855 | 0.01426 | 0.023859 | −0.002266 | 0.026187 | 0.007711 | −0.047587 | −0.052194 | 0.028234 | −0.040365 |
| 298 | −0.019452 | −0.026807 | 0.001767 | 0.013572 | 0.002262 | 0.015432 | −0.000027 | 0.024574 | −0.030312 | −0.048957 | 0.003842 | 0.016654 | 0.024719 | 0.008757 |
| 299 | 0.010962 | 0.025337 | −0.018951 | −0.029397 | −0.00346 | −0.016633 | −0.006672 | 0.020911 | −0.024101 | −0.006497 | −0.008756 | 0.003796 | 0.030461 | 0.003656 |
| 300 | −0.022343 | −0.016442 | −0.025278 | −0.032349 | 0.027125 | 0.013335 | 0.016495 | −0.020985 | 0.01589 | 0.021978 | −0.00282 | 0.000719 | −0.004915 | −0.024393 |
| 301 | −0.025801 | 0.02508 | 0.032424 | 0.012556 | 0.020118 | 0.007171 | 0.016151 | 0.003073 | 0.045958 | 0.014664 | 0.004812 | 0.008916 | 0.011478 | −0.023363 |
| 302 | −0.028403 | −0.00637 | 0.002114 | 0.022164 | 0.020221 | −0.007702 | 0.006188 | −0.038288 | 0.003573 | 0.031498 | 0.016724 | 0.014443 | −0.024113 | 0.02874 |
| 303 | 0.071366 | 0.027885 | 0.005728 | −0.008725 | −0.026639 | −0.008456 | −0.025847 | 0.022666 | 0.031941 | −0.01422 | 0.038506 | 0.036069 | 0.051619 | 0.014333 |
| 304 | 0.008967 | 0.03673 | 0.014405 | 0.000311 | −0.037116 | 0.0049 | 0.027006 | −0.02382 | 0.012822 | −0.005812 | 0.003829 | 0.002485 | −0.013194 | 0.013141 |
| 305 | −0.016588 | −0.025957 | −0.010355 | −0.044246 | −0.003054 | −0.012986 | −0.015738 | 0.002345 | −0.004929 | −0.085654 | 0.046577 | 0.040341 | −0.020175 | −0.029341 |
| 306 | −0.002973 | −0.04710 | 0.020579 | 0.080996 | −0.019227 | −0.003481 | 0.02082 | 0.016221 | 0.002003 | −0.055908 | 0.002777 | 0.00732 | −0.036161 | 0.01267 |
| 307 | −0.036191 | −0.02541 | 0.019102 | 0.017969 | −0.023366 | −0.015635 | −0.012968 | −0.013336 | −0.032861 | −0.024299 | −0.01195 | −0.020714 | −0.027553 | −0.038301 |
| 308 | −0.045333 | 0.005084 | 0.04607 | 0.028971 | −0.03194 | −0.013335 | −0.011492 | −0.006104 | 0.003702 | −0.052654 | −0.008945 | −0.006242 | −0.018036 | −0.006557 |
| 109 | −0.037841 | −0.001377 | 0.014708 | 0.011787 | −0.010977 | −0.008924 | −0.025535 | −0.019439 | −0.008216 | −0.005721 | 0.016661 | 0.019794 | −0.023765 | 0.022069 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 310 | −0.02082 | −0.010047 | −0.046574 | −0.024612 | 0.027845 | 0.002527 | 0.000572 | −0.001201 | −0.03356 | 0.024048 | 0.017881 | 0.004384 | −0.006119 | 0.078564 |
| 311 | −0.019578 | −0.007687 | −0.018852 | −0.022786 | 0.043555 | −0.052371 | −0.051135 | −0.024936 | 0.010514 | 0.061027 | −0.039208 | −0.021698 | −0.007001 | 0.011196 |
| 312 | 0.036605 | 0.001094 | −0.014113 | 0.006306 | 0.018273 | 0.000158 | −0.024838 | −0.005721 | 0.003702 | −0.042045 | −0.033992 | −0.038026 | −0.001173 | 0.019787 |
| 313 | −0.03929 | −0.051106 | −0.007603 | 0.001887 | 0.015621 | −0.009344 | −0.012075 | −0.008369 | 0.07985 | −0.014478 | −0.006839 | 0.013647 | −0.027411 | −0.017855 |
| 314 | −0.016994 | −0.024304 | −0.006936 | −0.048873 | −0.004204 | −0.004146 | −0.011997 | 0.015091 | −0.051406 | 0.036883 | 0.023497 | 0.011948 | 0.02724 | −0.016884 |
| 315 | 0.00066 | 0.027767 | −0.020878 | −0.062559 | −0.011458 | −0.007551 | −0.031108 | 0.001617 | −0.020397 | 0.016946 | 0.04589 | 0.029465 | 0.038612 | 0.00192 |
| 316 | −0.02795 | −0.026776 | −0.000726 | 0.042618 | −0.05268 | 0.014692 | 0.015122 | 0.003539 | 0.056071 | −0.012048 | 0.027148 | 0.026672 | −0.031219 | −0.013445 |
| 317 | −0.04577 | 0.00567 | −0.018816 | −0.007841 | −0.008449 | 0.018702 | 0.011499 | −0.014066 | −0.028968 | 0.024384 | 0.039646 | 0.032693 | −0.009159 | 0.036485 |
| 318 | −0.015561 | −0.012361 | 0.027996 | 0.021815 | 0.068346 | 0.00488 | 0.008851 | 0.02031 | −0.035733 | −0.00999 | −0.034709 | −0.032971 | −0.00167 | 0.005441 |
| 319 | −0.009349 | 0.018443 | −0.009235 | −0.026261 | −0.031475 | −0.006526 | −0.000815 | 0.000845 | 0.011705 | −0.0015 | 0.019024 | 0.014638 | 0.054355 | 0.004911 |
| 320 | 0.017376 | −0.006639 | −0.034093 | −0.009218 | 0.023804 | 0.00408 | 0.015364 | 0.026362 | 0.004214 | −0.026733 | −0.04122 | −0.030151 | −0.015036 | 0.033991 |
| 321 | 0.008358 | 0.020949 | 0.025836 | 0.021756 | 0.030341 | −0.002188 | −0.007413 | 0.005862 | 0.087301 | 0.042922 | −0.020329 | −0.015242 | −0.033633 | −0.019588 |
| 322 | −0.002916 | 0.051807 | 0.021451 | 0.004403 | 0.046864 | 0.001671 | 0.017607 | 0.003983 | 0.027794 | 0.012932 | −0.01758 | −0.030829 | −0.003426 | −0.004804 |
| 323 | 0.002605 | −0.007351 | −0.005519 | −0.008932 | −0.028935 | −0.022378 | −0.019014 | −0.013661 | 0.02919 | 0.033672 | −0.017834 | −0.015814 | 0.01596 | 0.033832 |
| 324 | −0.00326 | −0.028816 | −0.030309 | 0.010201 | 0.015208 | −0.004495 | −0.010505 | −0.025922 | −0.08307 | −0.003509 | −0.009557 | −0.010131 | −0.049123 | 0.013967 |
| 325 | −0.007095 | 0.019135 | 0.0073 | −0.005215 | 0.043159 | 0.000501 | −0.033266 | −0.015301 | 0.049927 | 0.024966 | 0.000493 | 0.008536 | −0.022442 | −0.01034 |
| 326 | −0.00086 | 0.02685 | 0.016096 | −0:006417 | −0.029488 | −0.011792 | 0.027007 | −0.001178 | −0.077378 | 0.03235 | 0.015636 | 0.012772 | 0.017637 | −0.025941 |
| 327 | −0.01255 | 0.009369 | 0.006397 | 0.01689 | −0.010649 | −0.00093 | −0.008339 | −0.008448 | −0.025766 | −0.030131 | −0.027575 | −0.040747 | −0.002881 | 0.007586 |
| 328 | −0.011375 | 0.002438 | 0.017333 | 0.027096 | −0.014906 | 0.020151 | 0.01893 | −0.011788 | −0.030203 | 0.006425 | −0.018755 | −0.018721 | −0.009581 | 0.03235 |
| 329 | 0.009364 | −0.018034 | −0.040709 | 0.007596 | 0.021645 | 0.006329 | 0.012828 | −0.010539 | 0.030043 | −0.02904 | −0.005042 | −0.006857 | 0.022499 | −0.020232 |
| 330 | −0.006125 | −0.030264 | 0.01635 | 0.028355 | −0.031779 | 0.002155 | −0.022185 | 0.008203 | −0.033544 | −0.004569 | 0.025829 | 0.026677 | −0.020115 | −0.033241 |
| 331 | 0.0273 | −0.001981 | −0.018332 | −0.065736 | 0.029145 | −0.016706 | −0.030407 | −0.000462 | −0.021953 | −0.007932 | 0.029876 | 0.011408 | 0.03307 | −0.002167 |
| 332 | −0.009218 | 0.002026 | −0.026173 | −0.032308 | 0.002954 | −0.020518 | −0.022882 | −0.004206 | −0.03691 | 0.011242 | −0.021455 | −0.01392 | 0.032137 | 0.00011 |
| 333 | 0.026527 | 0.011562 | 0.022161 | 0.008889 | 0.06422 | −0.007106 | −0.026489 | −0.048358 | 0.0366 | 0.027313 | 0.006393 | 0.000089 | −0.006953 | −0.001493 |
| 334 | 0.028373 | 0.068064 | 0.044557 | 0.000429 | −0.026094 | −0.035771 | −0.004546 | 0.026398 | −0.047345 | −0.052847 | −0.000571 | 0.021231 | 0.028849 | −0.02008 |
| 335 | 0.010419 | 0.002078 | 0.008618 | −0.045855 | 0.041421 | 0.025522 | −0.009924 | −0.020418 | 0.020768 | −0.017212 | 0.026646 | 0.013908 | −0.016814 | 0.006609 |
| 336 | −0.015891 | 0.027013 | 0.006662 | 0.020811 | −0.04861 | 0.029882 | 0.034375 | 0.023393 | −0.037795 | 0.006419 | 0.016665 | 0.020806 | −0.018238 | −0.01762 |
| 337 | 0.048579 | 0.005864 | −0.024888 | 0.009184 | 0.009267 | −0.007059 | −0.010527 | −0.004626 | −0.000562 | −0.040879 | −0.013599 | −0.015523 | 0.011791 | 0.020234 |
| 338 | −0.003168 | 0.029202 | 0.037618 | −0.005488 | −0.013394 | −0.004325 | −0.025202 | 0.020516 | −0.019359 | −0.016286 | −0.008607 | −0.005229 | −0.015639 | −0.046666 |
| 339 | −0.005726 | −0.014605 | −0.016807 | 0.088464 | −0.02958 | −0.004776 | 0.044432 | 0.028124 | 0.066881 | 0.010202 | 0.023075 | 0.02782 | 0.022958 | 0.013695 |
| 340 | 0.016656 | 0.017202 | 0.015487 | 0.003922 | 0.008653 | 0.001602 | 0.011407 | 0.013596 | 0.1154911 | 0.004127 | −0.008795 | −0.009654 | −0.003265 | 0.031098 |

| | JR | JS | JT | JU | JV | JW | JX | JY | JZ | KA | KB | KC | KD | KE |
|---|---|---|---|---|---|---|---|---|---|---|---|---|---|---|
| 1 | 0.008217 | 0.046737 | 0.104594 | 0.051278 | 0.007929 | 0.033325 | 0.030384 | 0.003276 | 0.010876 | −0.073134 | −0.025948 | 0.025393 | 0.025035 | 0.012964 |
| 2 | −0.047244 | −0.081567 | 0.001546 | −0.000428 | −0.046525 | −0.052984 | 0.028589 | 0.027806 | 0.011475 | 0.034572 | 0.017357 | 0.048581 | 0.042 | 0.056819 |
| 3 | 0.040783 | 0.016698 | −0.091795 | 0.012069 | 0.092894 | 0.047614 | 0.066444 | −0.032025 | −0.027734 | 0.015118 | 0.01895 | 0.021431 | 0.005535 | 0.0341 |
| 4 | 0.000543 | 0.028802 | 0.028222 | −0.069501 | 0.008938 | 0.026714 | −0.008374 | 0.061095 | −0.001347 | 0.005699 | −0.000585 | −0.053601 | −0.006851 | −0.014288 |
| 5 | 0.043312 | 0.032485 | 0.007881 | 0.021799 | 0.010867 | −0.004539 | 0.00816 | 0.015554 | −0.004578 | −0.014083 | 0.005759 | −0.009769 | −0.005251 | −0.045171 |
| 6 | 0.040117 | 0.019767 | −0.001704 | −0.10356 | −0.046573 | −0.068433 | −0.029113 | −0.045762 | −0.01229 | −0.04399 | −0.040177 | −0.038533 | −0.003314 | −0.008824 |
| 7 | 0.062701 | 0.061347 | −0.018438 | −0.014129 | 0.063063 | 0.010969 | −0.110033 | 0.049559 | 0.055711 | 0.048964 | 0.043808 | 0.042018 | −0.032145 | 0.005301 |
| 8 | −0.004332 | −0.060212 | −0.015711 | 0.005634 | −0.0085 | −0.028341 | −0.039451 | −0.017036 | −0.043998 | 0.033381 | −0.013139 | −0.058611 | −0.031987 | 0.019228 |
| 9 | 0.031108 | 0.044948 | −0.036684 | 0.123833 | 0.037727 | 0.014894 | 0.042183 | −0.023081 | −0.033624 | −0.023155 | −0.000663 | 0.010409 | 0.037096 | −0.015006 |
| 10 | 0.024217 | −0.00926 | 0.002102 | 0.043706 | 0.059467 | 0.07406 | −0.051509 | −0.023392 | −0.0322 | 0.029381 | 0.039993 | 0.032978 | −0.009088 | 0.020735 |
| 11 | −0.016608 | −0.03119 | 0.047301 | 0.060395 | −0.030223 | −0.027388 | −0.002839 | 0.027515 | 0.009633 | 0.018908 | 0.018257 | −0.012167 | −0.002441 | −0.05487 |
| 12 | −0.014628 | −0.045713 | −0.043896 | 0.030438 | −0.014404 | 0.002257 | 0.051157 | −0.044916 | −0.023718 | 0.011259 | −0.005921 | 0.054789 | −0.005678 | 0.002029 |
| 13 | −0.014975 | −0.025169 | −0.013715 | −0.096724 | 0.046973 | 0.03697 | 0.044608 | 0.046016 | 0.079777 | 0.033124 | 0.057367 | 0.035459 | −0.042054 | −0.025095 |
| 14 | 0.022431 | −0.004092 | −0.008406 | 0.021837 | −0.016361 | −0.068355 | −0.047717 | −0.002895 | 0.047102 | −0.056564 | −0.082313 | 0.012068 | 0.018755 | 0.031005 |
| 15 | −0.046837 | −0.033088 | 0.007588 | −0.085097 | 0.023792 | 0.045273 | 0.072424 | 0.078211 | 0.10861 | 0.090925 | 0.081596 | 0.007563 | 0.024928 | 0.031405 |
| 16 | −0.00717 | −0.040348 | 0.006933 | −0.018362 | 0.035983 | 0.029011 | 0.012769 | −0.011053 | −0.027677 | 0.00939 | −0.001698 | 0.007372 | −0.018353 | 0.006444 |
| 17 | 0.00161 | 0.007902 | 0.061542 | −0.012196 | −0.013444 | −0.013188 | −0.016306 | −0.005639 | 0.007948 | 0.013861 | −0.003572 | 0.022442 | −0.04944 | 0.012675 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 18 | −0.021121 | 0.028213 | 0.016022 | 0.068296 | −0.016383 | 0.057234 | 0.004791 | 0.025534 | 0.038288 | 0.076619 | 0.071082 | 0.009194 | −0.005878 | 0.019383 |
| 19 | −0.014529 | 0.037534 | 0.037867 | 0.031312 | −0.010442 | 0.062146 | 0.045222 | 0.03197 | 0.039741 | −0.008547 | 0.011013 | −0.015979 | 0.015367 | 0.00905 |
| 20 | 0.01633 | −0.050743 | −0.018265 | 0.07143 | 0.051195 | 0.014765 | 0.032152 | 0.102364 | 0.063414 | 0.073655 | 0.067388 | 0.093826 | 0.090867 | 0.01623 |
| 21 | −0.033247 | −0.020127 | −0.056992 | 0.026072 | −0.025969 | −0.02568 | −0.025886 | 0.028413 | 0.031459 | −0.00411 | 0.014951 | −0.047871 | −0.001571 | −0.075432 |
| 22 | 0.018147 | 0.004695 | 0.021422 | 0.072453 | 0.036084 | −0.021357 | 0.063996 | −0.013298 | −0.020035 | 0.004818 | 0.032708 | −0.02139 | −0.014245 | −0.022052 |
| 23 | −0.055398 | −0.034747 | −0.061981 | 0.054129 | 0.031443 | 0.011956 | −0.03033 | −0.017077 | −0.03472 | −0.03002 | −0.023294 | −0.026778 | −0.024635 | −0.016955 |
| 24 | 0.046111 | 0.052417 | −0.010509 | −0.03262 | −0.051374 | −0.02948 | 0.015803 | −0.072203 | −0.041576 | −0.060497 | −0.057271 | −0.08272 | −0.004881 | 0.032601 |
| 25 | −0.032473 | −0.001946 | −0.002048 | 0.005913 | −0.024641 | 0.041678 | 0.028972 | −0.00117 | 0.022545 | −0.008637 | 0.031011 | 0.0967 | 0.04016 | 0.004011 |
| 26 | 0.107013 | 0.083495 | 0.035226 | −0.00868 | 0.007887 | −0.012774 | 0.080604 | −0.038972 | −0.070352 | −0.073625 | −0.110448 | 0.026945 | 0.077954 | −0.066732 |
| 27 | 0.096853 | 0.031221 | 0.017513 | 0.071353 | −0.007167 | −0.038157 | −0.063665 | −0.003784 | 0.051065 | 0.046616 | 0.055959 | −0.012966 | 0.007491 | −0.03878 |
| 28 | −0.049274 | −0.016188 | 0.013888 | −0.00015 | −0.106028 | −0.072087 | 0.061396 | 0.007522 | 0.016108 | 0.032611 | 0.067823 | 0.118953 | 0.005397 | 0.048923 |
| 29 | 0.057921 | 0.052985 | 0.005906 | −0.001846 | 0.016728 | −0.023144 | −0.01138 | −0.010874 | 0.001772 | −0.052714 | −0.024788 | −0.036802 | −0.046841 | −0.025846 |
| 30 | 0.081764 | 0.160588 | 0.115757 | 0.047424 | −0.043278 | 0.048762 | 0.03975 | −0.112355 | −0.045227 | −0.019302 | 0.037333 | 0.003854 | −0.010217 | 0.114845 |
| 31 | 0.029505 | 0.05479 | 0.057367 | −0.036218 | −0.000255 | −0.029765 | 0.003999 | −0.032845 | −0.045708 | −0.076201 | −0.074558 | −0.029231 | −0.016926 | 0.0316 |
| 32 | 0.021425 | −0.007255 | 0.001735 | 0.020354 | −0.008277 | −0.055204 | −0.066579 | −0.030737 | −0.031441 | 0.017502 | −0.011705 | 0.011293 | −0.0375 | −0.075234 |
| 33 | −0.086608 | −0.054433 | 0.003423 | −0.058238 | 0.03744 | 0.006712 | 0.027311 | −0.088252 | −0.118332 | −0.026692 | 0.004562 | 0.049851 | −0.020603 | 0.067403 |
| 34 | 0.070002 | 0.004537 | −0.081794 | 0.078 | 0.018822 | 0.025663 | −0.046244 | −0.002592 | 0.014239 | 0.017413 | −0.026069 | −0.05604 | 0.007503 | 0.056962 |
| 35 | 0.00966 | 0.022923 | 0.027588 | −0.069405 | 0.034412 | 0.004618 | 0.013362 | 0.000349 | 0.022704 | −0.021455 | −0.039543 | −0.022067 | 0.035702 | −0.022335 |
| 36 | −0.051472 | −0.009862 | −0.0285 | −0.100794 | −0.091617 | −0.017874 | 0.019566 | 0.028045 | 0.041801 | −0.057133 | −0.032048 | −0.017937 | 0.014783 | 0.01781 |
| 37 | −0.041366 | −0.033407 | −0.079033 | 0.008475 | 0.131677 | 0.11621 | 0.003086 | −0.007915 | −0.017821 | 0.018391 | −0.018752 | −0.105918 | −0.039604 | −0.008913 |
| 38 | −0.047146 | −0.010957 | −0.026838 | −0.075305 | −0.063973 | 0.034552 | 0.029358 | −0.000613 | 0.060727 | −0.03468 | 0.001187 | −0.000968 | 0.019656 | 0.028865 |
| 39 | 0.026994 | −0.017412 | 0.027912 | 0:041694 | −0.010207 | −0.009126 | −0.019184 | −0.010305 | 0.01019 | −0.046641 | −0.039194 | −0.023446 | −0.009792 | −0.027242 |
| 40 | −0.004291 | 0.018631 | 0.032867 | −0.109575 | −0.01515 | −0.051077 | −0.015129 | −0.015503 | −0.048153 | −0.076635 | −0.069425 | 0.018277 | −0.004973 | 0.023719 |
| 41 | 0.040397 | 0.028887 | 0.101046 | −0.096689 | −0.0233 | −0.091372 | −0.063285 | −0.008135 | −0.017321 | −0.064338 | −0.076435 | −0.092878 | −0.0359 | −0.027295 |
| 42 | −0.009898 | 0.02313 | 0.019592 | 0.075618 | 0.013566 | 0.060862 | 0.052723 | 0.025076 | 0.09837 | 0.075106 | 0.096043 | −0.034926 | −0.004782 | −0.087715 |
| 43 | 0.028354 | 0.05204 | 0.042196 | −0.02273 | −0.018823 | 0.005093 | 0.047705 | 0.000518 | −0.020615 | 0.0427 | 0.013791 | 0.129732 | −0.007249 | −0.00303 |
| 44 | −0.024188 | −0.068906 | 0.018261 | 0.016721 | 0.059327 | 0.011367 | 0.046023 | 0.007282 | −0.021914 | 0.005049 | −0.008449 | −0.025645 | 0.013204 | 0.009613 |
| 45 | −0.039314 | −0.052617 | −0.041745 | 0.057849 | −0.013632 | 0.003383 | −0.044807 | 0.017768 | −0.012488 | 0.040203 | 0.036447 | 0.079304 | 0.024244 | 0.021032 |
| 46 | −0.025239 | −0.04562 | −0.035485 | 0.097581 | 0.07543 | 0.026098 | −0.037762 | 0.031823 | 0.020992 | 0.047731 | −0.008528 | 0.024423 | 0.027451 | 0.008489 |
| 47 | 0.001945 | 0.044507 | 0.026428 | 0.021494 | −0.062564 | −0.025677 | 0.012717 | −0.01843 | −0.015125 | −0.04442 | −0.003113 | −0.069343 | −0.009866 | −0.011521 |
| 48 | −0.02279 | −0.001268 | −0.045551 | −0.039675 | −0.031078 | −0.065517 | −0.101357 | 0.000093 | −0.020066 | −0.011923 | 0.000138 | 0.040706 | 0.041218 | 0.047182 |
| 49 | −0.027697 | 0.009203 | −0.053026 | −0.047299 | 0.045861 | −0.003765 | −0.012278 | 0.070888 | 0.10689 | 0.018928 | 0.037708 | 0.020412 | −0.023484 | −0.007287 |
| 50 | −0.052986 | −0.05565 | −0.035892 | 0.013141 | 0.004361 | 0.054766 | −0.043231 | −0.079274 | −0.053949 | 0.006059 | 0.034141 | −0.065738 | −0.073872 | 0.002865 |
| 51 | 0.043171 | 0.057066 | −0.090421 | −0.001745 | 0.109018 | 0.104008 | 0.110323 | 0.049921 | 0.036033 | 0.050513 | 0.049518 | 0.141836 | −0.035048 | −0.01124 |
| 52 | −0.04081 | −0.043803 | 0.064626 | −0.044841 | 0.042997 | 0.040071 | 0.100237 | 0.054293 | 0.053188 | 0.012534 | −0.0366 | 0.03599 | 0.015747 | 0.034181 |
| 53 | 0.042468 | 0.043117 | −0.127593 | 0.070852 | −0.018295 | −0.049925 | −0.144882 | −0.019507 | −0.056514 | 0.049939 | 0.001265 | −0.070641 | −0.015266 | −0.03872 |
| 54 | −0.012304 | 0.024238 | 0.045471 | −0.032526 | 0.03041 | 0.000476 | 0.061409 | −0.004768 | −0.025361 | 0.042662 | 0.031276 | −0.012513 | −0.074702 | −0.023553 |
| 55 | −0.034137 | −0.041736 | −0.021319 | −0.038078 | −0.031403 | −0.019499 | 0.013725 | −0.003506 | −0.006374 | −0.021732 | 0.015333 | 0.050742 | −0.052194 | 0.075316 |
| 56 | −0.06623 | −0.068219 | −0.014226 | −0.017298 | 0.044311 | −0.027009 | 0.02217 | 0.022002 | −0.028087 | −0.042053 | 0.003148 | −0.039491 | 0.03226 | 0.012001 |
| 57 | 0.085615 | −0.006901 | −0.015583 | −0.035901 | 0.110119 | 0.003988 | −0.080873 | 0.057019 | 0.002423 | 0.01945 | −0.072017 | −0.106257 | −0.047941 | −0.042632 |
| 58 | 0.048749 | 0.048539 | 0.062825 | 0.077694 | −0.015094 | −0.046755 | 0.026799 | 0.039737 | −0.00721 | 0.043552 | −0.005957 | −0.016778 | −0.000085 | −0.048033 |
| 59 | −0.041406 | −0.041752 | −0.024995 | −0.049199 | −0.019898 | 0.017193 | −0.023333 | −0.03157 | −0.014674 | −0.030625 | −0.04631 | 0.017723 | 0.001054 | 0.013709 |
| 60 | −0.087956 | −0.059457 | 0.091647 | −0.057894 | −0.050028 | −0.081314 | 0.061814 | 0.062545 | 0.078734 | 0.07096 | 0.12031 | 0.024506 | −0.06583 | 0.003075 |
| 61 | 0.03221 | 0.014873 | −0.017358 | 0.057365 | −0.099124 | −0.040645 | −0.047145 | 0.035704 | 0.047376 | 0.027299 | 0.044213 | 0.021849 | 0.013585 | −0.059556 |
| 62 | 0.061804 | 0.052686 | 0.04011 | −0.005189 | −0.044483 | 0.042505 | −0.03941 | −0.034385 | 0.013512 | −0.01971 | −0.010676 | −0.010291 | 0.063913 | 0.013805 |
| 63 | 0.001156 | −0.009761 | −0.104202 | −0.006561 | −0.005906 | −0.020215 | −0.022322 | 0.028071 | 0.005518 | −0.01543 | −0.042493 | −0.083969 | 0.033603 | −0.023954 |
| 64 | 0.026162 | 0.001084 | −0.011612 | 0.012374 | 0.016406 | −0.007594 | −0.005288 | 0.01929 | −0.014137 | 0.029352 | 0.002202 | −0.017226 | −0.008523 | −0.00087 |
| 65 | 0.004199 | 0.028083 | 0.009247 | −0.016332 | 0.037861 | −0.032646 | 0.009996 | −0.032096 | −0.06008 | 0.019571 | 0.054578 | 0.127031 | 0.031128 | 0.011915 |
| 66 | −0.025617 | −0.035927 | −0.033719 | 0.077135 | 0.090267 | 0.09281 | −0.009867 | −0.04564 | −0.022427 | −0.001651 | 0.035821 | −0.000271 | −0.015267 | −0.004404 |
| 67 | −0.031387 | 0.00172 | −0.021841 | −0.028614 | −0.027675 | −0.023498 | −0.011294 | −0.028377 | −0.003361 | 0.005881 | −0.01165 | −0.026305 | −0.027188 | 0.028951 |
| 68 | 0.022505 | 0.013813 | 0.005796 | 0.049546 | 0.003956 | 0.039417 | −0.000043 | −0.019033 | −0.039856 | 0.019541 | 0.023041 | −0.012003 | −0.037704 | 0.021427 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 69 | 0.072739 | 0.063377 | 0.025731 | −0.032928 | −0.037204 | 0.023281 | −0.113211 | −0.044428 | −0.003308 | −0.073976 | −0.088877 | −0.120682 | 0.021613 | 0.08238 |
| 70 | −0.037911 | −0.08788 | 0.037503 | 0.018312 | −0.004598 | −0.058774 | 0.025302 | −0.024915 | −0.053293 | 0.04617 | −0.011819 | −0.042246 | −0.032886 | −0.115108 |
| 71 | −0.001641 | 0.030069 | 0.042594 | 0.052237 | 0.014803 | −0.013473 | 0.024011 | 0.036328 | −0.004521 | 0.016746 | −0.012547 | 0.010879 | −0.015479 | −0.02368 |
| 72 | 0.043573 | 0.000287 | 0.022012 | −0.005419 | −0.032485 | −0.038914 | −0.038418 | 0.051772 | 0.012506 | −0.009059 | 0.023257 | 0.037652 | −0.034746 | −0.008721 |
| 73 | 0.007646 | −0.01185 | −0.07684 | 0.064574 | −0.025121 | 0.046772 | −0.078196 | 0.017374 | 0.024925 | 0.04229 | 0.049966 | 0.00221 | 0.043818 | 0.052047 |
| 74 | −0.012062 | −0.033866 | 0.019045 | −0.005938 | 0.009492 | −0.026172 | −0.005688 | −0.005746 | −0.003937 | −0.012161 | −0.024756 | 0.036238 | −0.023414 | −0.013727 |
| 75 | 0.029178 | 0.081909 | −0.006179 | 0.007594 | −0.031226 | 0.052414 | −0.077297 | 0.073959 | 0.080338 | 0.008705 | 0.040713 | −0.063786 | −0.027944 | 0.074339 |
| 76 | −0.001169 | 0.000422 | 0.039934 | −0.115256 | 0.042239 | 0.037941 | 0.046779 | 0.00853 | 0.025279 | 0.009305 | 0.006943 | −0.02913 | 0.008996 | −0.002295 |
| 77 | −0.03159 | 0.010001 | −0.054058 | 0.081076 | −0.008107 | 0.028412 | −0.010305 | −0.063224 | −0.097086 | −0.009955 | −0.017985 | 0.03938 | −0.046604 | −0.035031 |
| 78 | 0.038936 | 0.002363 | 0.025696 | 0.053043 | 0.086198 | 0.011929 | 0.115866 | 0.014001 | −0.087251 | 0.037353 | 0.025855 | 0.13014 | 0.100435 | −0.052277 |
| 79 | −0.054736 | −0.051021 | −0.071538 | 0.035929 | −0.067195 | −0.120845 | −0.036386 | −0.000998 | 0.011421 | −0.050501 | 0.049742 | 0.007009 | 0.006667 | 0.002489 |
| 80 | 0.006248 | 0.011802 | −0.002036 | 0.026905 | −0.00162 | 0.026028 | −0.059788 | 0.010988 | 0.009484 | 0.056355 | 0.020582 | −0.031643 | −0.012349 | −0.007133 |
| 81 | −0.046772 | −0.042639 | 0.008523 | 0.016521 | 0.036322 | 0.025407 | 0.012755 | −0.025695 | −0.041255 | −0.006934 | −0.007252 | −0.024147 | −0.027426 | −0.001509 |
| 82 | −0.000424 | −0.008903 | 0.056785 | 0.013654 | −0.065198 | −0.046519 | 0.015148 | −0.011974 | 0.036767 | 0.010701 | 0.002323 | −0.028619 | −0.006768 | −0.00479 |
| 83 | −0.048816 | −0.018304 | −0.056073 | 0.025021 | −0.017193 | 0.010058 | −0.015044 | 0.016311 | 0.015857 | 0.046413 | 0.04315 | 0.046944 | 0.030522 | 0.038347 |
| 84 | −0.071125 | −0.080792 | 0.017801 | −0.006172 | −0.022711 | 0.012062 | 0.000125 | 0.044949 | 0.023414 | −0.020366 | −0.016321 | −0.124396 | −0.092191 | −0.124595 |
| 85 | 0.026422 | 0.001455 | 0.031451 | −0.07379 | 0.020565 | 0.003437 | 0.081552 | −0.03109 | 0.010871 | −0.02425 | −0.010489 | 0.013858 | 0.096235 | −0.040764 |
| 86 | 0.017374 | −0.045385 | −0.041241 | −0.046765 | 0.111713 | 0.062135 | 0.061351 | −0.067162 | −0.056435 | −0.023007 | −0.063526 | 0.042742 | −0.029896 | 0.008179 |
| 87 | −0.027008 | −0.04438 | 0.072647 | −0.025046 | 0.035077 | −0.049077 | 0.03467 | 0.023714 | −0.038212 | 0.071233 | 0.003749 | −0.007862 | −0.046184 | 0.053977 |
| 88 | −0.034662 | −0.062457 | −0.036869 | 0.029438 | 0.027507 | −0.052298 | −0.054313 | 0.023088 | −0.060638 | −0.010088 | −0.015072 | −0.092751 | 0.029348 | −0.064383 |
| 89 | −0.038301 | −0.083709 | −0.058577 | −0.024375 | −0.04035 | 0.003016 | −0.099537 | 0.023198 | 0.065243 | 0.087646 | 0.094514 | 0.002555 | 0.025086 | 0.046432 |
| 90 | 0.078314 | 0.1202 | −0.001183 | −0.03483 | 0.046246 | 0.151813 | −0.014762 | −0.091532 | −0.075793 | 0.025104 | 0.006558 | 0.000307 | −0.032421 | −0.079525 |
| 91 | −0.002877 | 0.028721 | 0.028285 | 0.085812 | 0.036317 | 0.069875 | −0.05706 | 0.00534 | −0.021807 | 0.023287 | 0.025682 | 0.023897 | −0.048536 | 0.030767 |
| 92 | 0.062722 | 0.127863 | 0.015867 | −0.031015 | −0.070248 | −0.059107 | −0.013079 | 0.043354 | 0.022657 | 0.029525 | 0.036804 | 0.07888 | 0.027475 | −0.004443 |
| 93 | 0.003609 | 0.040296 | 0.012302 | 0.03164 | −0.026565 | 0.041646 | −0.009687 | −0.031732 | 0.022902 | −0.045822 | −0.01141 | −0.023409 | 0.073515 | −0.000436 |
| 94 | −0.028863 | 0.029618 | 0.021339 | −0.024475 | 0.037618 | 0.019815 | 0.007452 | 0.039079 | 0.007065 | −0.056251 | −0.053031 | 0.038263 | −0.09012 | 0.057786 |
| 95 | 0.024523 | 0.01076 | −0.0226 | −0.018843 | 0.030091 | −0.01882 | −0.035214 | −0.006802 | 0.020114 | −0.008549 | 0.023963 | −0.020678 | −0.024322 | −0.112983 |
| 96 | −0.0511 | 0.012883 | 0.041072 | −0.057912 | −0.053411 | 0.015683 | 0.040366 | −0.044063 | −0.019181 | −0.003124 | 0.033298 | 0.038568 | 0.016104 | −0.005481 |
| 97 | −0.006414 | 0.041666 | 0.040675 | −0.028622 | 0.027643 | −0.024863 | −0.023014 | 0.021565 | 0.000159 | −0.034545 | −0.036333 | −0.043477 | −0.027121 | −0.026544 |
| 98 | −0.020837 | −0.030743 | −0.003066 | 0.007031 | 0.014154 | 0.03981 | 0.04507 | 0.035535 | 0.056933 | 0.021572 | 0.004181 | −0.078876 | −0.027863 | −0.007935 |
| 99 | 0.000067 | −0.020679 | 0.083802 | 0.043024 | 0.025848 | −0.032631 | 0.028419 | −0.017032 | −0.019222 | −0.14386 | −0.144513 | −0.081485 | 0.036402 | −0.070926 |
| 100 | 0.008697 | −0.027905 | 0.002679 | −0.01934 | −0.070694 | −0.033048 | −0.035787 | 0.028947 | 0.020599 | 0.080232 | 0.032331 | −0.040638 | −0.070185 | −0.083315 |
| 101 | 0.063564 | 0.091819 | 0.029727 | −0.105421 | −0.012766 | −0.020458 | 0.043581 | 0.027911 | 0.04527 | 0.002102 | 0.00737 | 0.09055 | 0.014917 | 0.055769 |
| 102 | −0.003299 | 0.001944 | −0.003841 | 0.068632 | 0.028225 | 0.016567 | −0.039159 | −0.032675 | −0.023102 | 0.056374 | 0.019073 | −0.009334 | −0.018751 | 0.055044 |
| 103 | −0.026206 | −0.012271 | −0.033919 | 0.010587 | −0.046518 | −0.031116 | 0.002697 | −0.052198 | −0.016126 | −0.110276 | −0.110722 | 0.056876 | 0.010372 | 0.032851 |
| 104 | 0.043301 | 0.01713 | 0.03278 | 0.014283 | −0.004545 | −0.02248 | −0.004861 | 0.056908 | 0.003542 | 0.067019 | 0.078883 | −0.036739 | −0.01272 | −0.011092 |
| 105 | 0.011835 | 0.053174 | 0.027344 | 0.024793 | 0.001449 | 0.054643 | 0.030654 | 0.021487 | 0.053379 | −0.03253 | 0.013384 | −0.02002 | −0.0008 | −0.039776 |
| 106 | −0.003041 | −0.017085 | 0.030598 | 0.040877 | 0.03401 | −0.010557 | 0.010189 | 0.041652 | 0.025833 | 0.032984 | −0.013206 | 0.049003 | −0.001514 | −0.06965 |
| 107 | 0.017604 | 0.030737 | 0.079958 | 0.00601 | −0.02243 | −0.016635 | 0.001355 | 0.018978 | 0.021317 | 0.021641 | −0.003464 | −0.018878 | −0.008444 | 0.010169 |
| 108 | −0.030065 | 0.00779 | 0.036845 | 0.049576 | 0.041733 | 0.082097 | 0.031548 | −0.013756 | −0.002053 | 0.029917 | 0.043479 | 0.019052 | 0.063559 | 0.037477 |
| 109 | −0.01844 | −0.026894 | −0.033499 | −0.051264 | −0.036147 | −0.042659 | 0.012196 | 0.002967 | 0.013605 | −0.05241 | −0.041595 | 0.039554 | 0.036577 | 0.017475 |
| 110 | 0.015188 | −0.032744 | −0.020779 | 0.061029 | −0.005696 | 0.00174 | 0.015421 | 0.001579 | 0.004593 | −0.035827 | −0.032228 | −0.035601 | −0.034529 | −0.008927 |
| 111 | −0.019021 | −0.032532 | −0.083132 | 0.023072 | −0.003692 | 0.039253 | 0.029535 | 0.008597 | 0.018158 | 0.017634 | 0.036785 | −0.047725 | −0.035162 | −0.045874 |
| 112 | −0.014146 | −0.020377 | −0.049195 | −0.055365 | 0.032277 | −0.001574 | 0.006355 | −0.004982 | −0.04894 | −0.001287 | 0.019522 | 0.056725 | −0.019928 | −0.02332 |
| 113 | 0.026895 | 0.023827 | 0.039538 | 0.046331 | 0.061709 | 0.049369 | −0.02805 | 0.00242 | 0.020099 | −0.007246 | −0.007771 | −0.002966 | −0.05566 | −0.007861 |
| 114 | −0.015519 | −0.008829 | 0.010457 | 0.024412 | 0.043694 | 0.011958 | −0.013549 | −0.000079 | −0.03861 | −0.009894 | −0.009397 | −0.014838 | 0.001297 | 0.018596 |
| 115 | 0.020387 | −0.022139 | −0.048725 | 0.008873 | 0.001578 | −0.055496 | 0.004422 | −0.012293 | −0.004155 | 0.005249 | −0.014398 | 0.035174 | 0.020012 | 0.036984 |
| 116 | −0.00652 | 0.03108 | 0.032535 | 0.006369 | −0.021015 | 0.046384 | −0.047067 | −0.056307 | −0.062978 | −0.040168 | −0.016993 | 0.02451 | −0.012497 | −0.020679 |
| 117 | −0.005233 | −0.148999 | −0.017615 | 0.140286 | 0.070135 | −0.038839 | −0.020549 | 0.051306 | −0.01765 | −0.01358 | −0.017125 | −0.094333 | −0.00574 | 0.131668 |
| 118 | 0.029816 | 0.010656 | −0.098169 | −0.030701 | 0.059867 | 0.040596 | −0.051006 | −0.017882 | 0.010528 | −0.011746 | −0.028434 | 0.101644 | 0.017705 | −0.064352 |
| 119 | 0.004783 | −0.039163 | −0.046715 | −0.013836 | −0.040518 | −0.100487 | 0.001684 | −0.007516 | −0.007261 | −0.011021 | 0.017445 | −0.02188 | −0.052741 | 0.010109 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 120 | −0.090661 | 0.028296 | 0.054651 | −0.006919 | −0.003674 | 0.029956 | −0.010735 | −0.030746 | −0.020279 | 0.104528 | 0.080677 | 0.084369 | 0.051691 | −0.096937 |
| 121 | 0.069653 | 0.060454 | −0.025595 | −0.060962 | −0.0311 | 0.005478 | 0.00294 | 0.026906 | 0.030876 | 0.006713 | −0.01276 | 0.018803 | 0.003121 | 0.023581 |
| 122 | −0.070676 | −0.023878 | −0.058638 | 0.037944 | −0.037498 | 0.000259 | 0.015301 | 0.049626 | 0.038994 | 0.01454 | −0.011185 | −0.027414 | −0.004225 | −0.012802 |
| 123 | 0.00153 | −0.005595 | 0.093858 | −0.130962 | 0.01952 | 0.05821 | −0.042237 | 0.046109 | 0.032524 | 0.025673 | 0.021265 | 0.049745 | 0.05251 | 0.026481 |
| 124 | 0.071204 | 0.052399 | 0.026439 | 0.048828 | 0.062949 | 0.095072 | −0.028356 | −0.019908 | −0.059244 | 0.096883 | 0.072102 | 0.082331 | −0.052607 | 0.021126 |
| 125 | 0.067941 | 0.037617 | −0.0219 | 0.045033 | −0.03009 | −0.045998 | 0.031576 | −0.010288 | −0.052163 | 0.014966 | −0.010759 | −0.023481 | −0.06186 | 0.023643 |
| 126 | 0.072747 | 0.066065 | −0.024382 | 0.033126 | −0.067074 | 0.00777 | 0.063536 | 0.01465 | 0.034612 | −0.018559 | −0.028803 | 0.046149 | −0.008921 | 0.060688 |
| 127 | −0.012204 | −0.025775 | 0.024054 | 0.154395 | 0.062512 | −0.009121 | −0.076267 | −0.03272 | −0.044727 | 0.054709 | 0.022044 | −0.035941 | −0.05163 | 0.026695 |
| 128 | −0.011826 | −0.017709 | 0.040409 | −0.099567 | 0.019518 | 0.055341 | 0.011143 | 0.015493 | 0.012392 | −0.029117 | −0.028946 | 0.059468 | 0.033311 | −0.014322 |
| 129 | −0.038027 | −0.033327 | 0.003286 | −0.031468 | −0.100154 | −0.023801 | −0.03482 | 0.030001 | 0.044564 | 0.036579 | 0.036536 | 0.041065 | 0.011089 | −0.006974 |
| 130 | −0.000274 | −0.021028 | 0.030751 | 0.033551 | −0.00992 | 0.027395 | −0.001643 | −0.029031 | −0.043542 | 0.029165 | −0.018746 | −0.005258 | 0.02176 | 0.042012 |
| 131 | −0.033332 | −0.008253 | 0.023232 | 0.003666 | −0.01528 | −0.000541 | 0.019561 | −0.009936 | −0.008586 | −0.023604 | 0.021465 | 0.023051 | −0.005009 | 0.014763 |
| 132 | 0.017084 | 0.0035 | −0.033015 | −0.007001 | −0.017326 | −0.000112 | 0.061453 | 0.000371 | 0.01072 | −0.064168 | −0.041716 | −0.02836 | 0.026669 | −0.005803 |
| 133 | 0.024503 | 0.042398 | 0.021135 | 0.000246 | 0.032721 | −0.034409 | 0.017206 | 0.019825 | −0.000311 | 0.00074 | −0.020549 | 0.058472 | −0.018595 | 0.003071 |
| 134 | 0.022524 | 0.006771 | 0.038782 | −0.036329 | 0.004371 | 0.028243 | 0.003082 | 0.066907 | 0.05812 | 0.008245 | 0.030112 | −0.043811 | −0.015959 | −0.014603 |
| 135 | −0.059135 | −0.022437 | −0.013066 | 0.067937 | −0.001315 | 0.062319 | 0.070542 | −0.015052 | 0.064579 | −0.042336 | 0.041935 | −0.006993 | −0.007554 | 0.063488 |
| 136 | −0.055339 | −0.045705 | −0.020486 | 0.057628 | 0.052225 | 0.009157 | −0.046845 | −0.031594 | −0.090424 | 0.026839 | 0.029158 | −0.074727 | 0.036838 | 0.0173 |
| 137 | −0.010431 | −0.079185 | −0.033656 | −0.136415 | 0.023794 | −0.020348 | 0.043325 | −0.0273 | 0.025077 | −0.016335 | −0.004717 | 0.021905 | 0.047587 | −0.025484 |
| 138 | 0.055571 | 0.00932 | 0.000879 | −0.005095 | 0.019427 | −0.054165 | −0.020979 | 0.042152 | 0.07283 | 0.020731 | 0.001631 | −0.029221 | −0.024622 | 0.010237 |
| 139 | −0.003607 | −0.001198 | 0.003018 | 0.030024 | 0.005529 | −0.023586 | 0.005434 | −0.021429 | 0.019696 | −0.035347 | −0.039756 | −0.006937 | −0.002307 | 0.013349 |
| 140 | −0.011766 | 0.062495 | −0.02214 | −0.040435 | −0.010684 | −0.025191 | 0.021341 | −0.018567 | −0.005225 | −0.024097 | 0.021674 | 0.015552 | −0.001923 | 0.00022 |
| 141 | −0.014818 | −0.026169 | 0.026738 | −0.031533 | 0.004804 | −0.071114 | −0.01377 | 0.016093 | −0.023935 | 0.100858 | 0.043963 | 0.054435 | −0.021381 | −0.037674 |
| 142 | −0.010147 | −0.004054 | 0.007706 | −0.020897 | −0.020128 | −0.027993 | −0.040898 | −0.015742 | 0.026312 | −0.001825 | 0.003011 | 0.028148 | 0.001142 | 0.021365 |
| 143 | 0.016204 | 0.038865 | 0.054908 | 0.04451 | 0.032875 | 0.027249 | 0.059171 | −0.021438 | −0.003645 | 0.026081 | 0.023816 | 0.031295 | 0.014528 | 0.026767 |
| 144 | 0.003856 | −0.028161 | 0.000872 | −0.020504 | −0.021275 | −0.031431 | 0.034575 | −0.013626 | −0.008243 | −0.055312 | −0.029266 | 0.048553 | −0.01397 | 0.001658 |
| 145 | −0.010837 | 0.026774 | −0.010008 | −0.028711 | −0.037859 | −0.016302 | −0.058572 | −0.009256 | 0.010618 | −0.017927 | 0.002461 | −0.03178 | 0.012276 | −0.007853 |
| 146 | 0.056318 | 0.006986 | −0.011565 | −0.061964 | −0.011253 | 0.033637 | −0.026552 | 0.019624 | 0.035305 | 0.014263 | −0.022587 | −0.012593 | −0.003725 | −0.034625 |
| 147 | −0.020664 | −0.028098 | −0.003711 | 0.028195 | 0.005743 | 0.01759 | 0.007784 | −0.023206 | −0.026742 | −0.03882 | −0.056336 | −0.007101 | 0.014334 | 0.01405 |
| 148 | 0.010806 | −0.019794 | −0.025756 | 0.001325 | 0.030266 | 0.031697 | 0.048438 | 0.014178 | 0.008335 | 0.007227 | −0.026217 | −0.004212 | 0.011319 | −0.004697 |
| 149 | −0.005492 | −0.003246 | −0.031684 | 0.052992 | −0.030215 | −0.009055 | 0.012495 | −0.000937 | 0.023047 | −0.019175 | 0.00148 | 0.028654 | 0.018306 | 0.027806 |
| 150 | −0.031325 | −0.01764 | −0.053082 | 0.016991 | 0.000531 | 0.060627 | −0.035299 | 0.026584 | −0.00165 | −0.00745 | 0.012936 | −0.020493 | −0.022916 | −0.019307 |
| 151 | −0.002956 | −0.002368 | −0.000564 | −0.008094 | −0.018238 | −0.001032 | 0.022895 | −0.006491 | −0.007953 | −0.017948 | −0.025088 | 0.018396 | 0.002912 | −0.015665 |
| 152 | −0.010973 | 0.047618 | 0.023108 | 0.015783 | 0.021086 | 0.049433 | 0.013187 | 0.001923 | 0.007716 | −0.013538 | −0.008312 | 0.00884 | 0.026646 | −0.028332 |
| 153 | 0.018894 | −0.028492 | 0.027177 | −0.001931 | −0.000831 | −0.066187 | −0.028393 | 0.038158 | 0.022852 | −0.000809 | 0.006617 | −0.013888 | −0.020241 | −0.044259 |
| 154 | 0.018468 | 0.009022 | −0.044901 | −0.011108 | 0.003501 | 0.010668 | 0.018189 | 0.017597 | 0.018211 | 0.007961 | 0.006143 | −0.008784 | 0.01217 | 0.027438 |
| 155 | 0.024544 | 0.014443 | 0.029538 | −0.007741 | 0.008507 | 0.008778 | 0.006384 | −0.010863 | 0.018575 | −0.023817 | −0.02628 | −0.013433 | 0.011517 | −0.033007 |
| 156 | 0.003273 | 0.020278 | −0.005937 | −0.052118 | −0.015493 | 0.018051 | −0.003177 | −0.008004 | 0.032936 | −0.032492 | −0.048034 | 0.027064 | 0.011198 | 0.033417 |
| 157 | 0.025134 | 0.027131 | −0.004946 | 0.020493 | −0.022236 | −0.042415 | −0.035031 | −0.004111 | −0.004234 | −0.022517 | −0.032296 | −0.029426 | −0.041739 | 0.003022 |
| 158 | 0.009631 | 0.015645 | 0.011672 | −0.032291 | −0.042464 | −0.049095 | −0.012715 | −0.012163 | −0.045752 | −0.018579 | −0.033776 | 0.009603 | −0.023107 | −0.018355 |
| 159 | 0.00534 | −0.021258 | 0.016957 | 0.011129 | 0.025432 | −0.023545 | 0.039358 | −0.003621 | −0.027689 | 0.037111 | 0.021743 | 0.018583 | −0.001863 | 0.006049 |
| 160 | 0.001252 | −0.00905 | 0.011675 | −0.004822 | −0.018595 | −0.009069 | 0.003372 | −0.030939 | −0.030881 | 0.024692 | 0.023818 | −0.012754 | −0.024614 | 0.003032 |
| 161 | −0.019236 | 0.023971 | −0.020696 | 0.010633 | −0.007112 | −0.001604 | −0.054474 | 0.032084 | 0.001416 | 0.024625 | 0.021564 | −0.034307 | −0.017935 | 0.011487 |
| 162 | 0.00257 | 0.00981 | 0.004943 | 0.047183 | −0.003029 | −0.007336 | 0.0217 | 0.011049 | 0.028395 | 0.018229 | −0.008203 | −0.019653 | −0.022791 | 0.059465 |
| 163 | −0.048949 | −0.00701 | 0.035432 | 0.001318 | 0.008635 | 0.010395 | 0.014726 | 0.023365 | 0.037877 | −0.007426 | 0.003608 | −0.053532 | 0.008865 | −0.024079 |
| 164 | 0.023394 | 0.009135 | 0.047143 | −0.038015 | 0.01183 | 0.018045 | 0.000527 | −0.009928 | −0.032291 | 0.035413 | −0.006616 | −0.010863 | −0.013634 | −0.050224 |
| 165 | 0.027265 | 0.026288 | −0.008109 | 0.003522 | 0.043346 | 0.036236 | 0.020663 | −0.014146 | −0.005563 | −0.008679 | 0.017979 | 0.048565 | −0.038861 | 0.021905 |
| 166 | −0.006583 | −0.015205 | 0.008346 | −0.055469 | −0.063003 | −0.029311 | −0.031438 | 0.005064 | 0.03628 | 0.01366 | 0.015252 | −0.033326 | −0.009483 | −0.032397 |
| 167 | −0.0253 | −0.001799 | 0.042412 | 0.023742 | 0.028994 | 0.053437 | −0.022374 | 0.005976 | −0.000012 | 0.01862 | 0.029565 | −0.046449 | 0.017896 | −0.036048 |
| 168 | 0.005881 | 0.015775 | −0.046521 | 0.04123 | 0.025108 | 0.040673 | −0.00421 | 0.010634 | −0.002238 | −0.009728 | −0.014485 | −0.046795 | −0.021896 | 0.005462 |
| 169 | 0.020092 | 0.009618 | 0.005718 | −0.008599 | 0.019769 | 0.001384 | 0.010044 | −0.010859 | 0.001645 | −0.031043 | −0.044719 | −0.018721 | 0.008557 | −0.01437 |
| 170 | 0.012957 | 0.013011 | 0.003016 | −0.008173 | −0.011838 | −0.033162 | 0.03162 | 0.008176 | 0.006868 | −0.017385 | −0.039523 | 0.019239 | −0.013279 | −0.009373 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 171 | 0.016563 | 0.004049 | 0.016354 | −0.02605 | 0.021016 | −0.003066 | 0.004113 | −0.000717 | 0.010381 | −0.004913 | −0.014824 | 0.010083 | 0.011586 | −0.011569 |
| 172 | 0.020241 | 0.03439 | −0.002948 | −0.049478 | 0.001498 | 0.038706 | −0.005055 | −0.040527 | 0.001622 | −0.042237 | −0.033455 | −0.002519 | 0.016727 | −0.000489 |
| 173 | 0.003817 | 0.011124 | −0.015841 | −0.046378 | −0.03397 | −0.035865 | 0.016533 | 0.005977 | −0.005264 | 0.008009 | 0.003928 | −0.010368 | 0.01657 | −0.010024 |
| 174 | −0.026836 | −0.046385 | 0.001075 | 0.013244 | 0.019595 | −0.038527 | 0.009438 | 0.043442 | 0.006269 | 0.045273 | 0.026489 | 0.006256 | 0.014445 | −0.004992 |
| 175 | −0.017161 | −0.031959 | 0.023481 | 0.000198 | 0.021786 | −0.013824 | 0.037111 | 0.017841 | 0.00851 | −0.011863 | −0.027299 | 0.016062 | −0.000448 | −0.009586 |
| 176 | 0.04861 | 0.022313 | −0.018274 | 0.018203 | 0.030297 | 0.040126 | −0.017897 | 0.00999 | 0.00233 | 0.026589 | 0.011416 | 0.008943 | −0.012891 | 0.001386 |
| 177 | 0.022887 | 0.047252 | 0.034921 | −0.001166 | 0.052406 | 0.03031 | 0.032871 | 0.036352 | 0.048876 | −0.032882 | 0.004209 | 0.016022 | 0.001161 | −0.037327 |
| 178 | −0.019297 | −0.013091 | −0.018089 | 0.05595 | 0.029556 | −0.009451 | −0.034295 | 0.001287 | −0.037272 | 0.017599 | 0.001524 | −0.009381 | −0.037118 | 0.00534 |
| 179 | −0.017866 | −0.025677 | −0.008074 | 0.020603 | 0.031293 | 0.018454 | −0.004319 | 0.000958 | 0.014494 | −0.001307 | 0.009949 | −0.002646 | 0.021356 | 0.011575 |
| 180 | −0.0171341 | 0.010007 | 0.002698 | 0.042563 | 0.022145 | 0.017977 | −0.023668 | −0.008422 | −0.044816 | 0.002927 | 0.003351 | 0.004754 | −0.007167 | 0.009409 |
| 181 | −0.007499 | −0.015728 | 0.008767 | 0.043533 | 0.010667 | −0.004609 | −0.005228 | 0.013863 | −0.017216 | −0.004001 | 0.002969 | −0.000617 | 0.003091 | 0.026987 |
| 182 | −0.001986 | −0.028386 | −0.011308 | 0.031483 | 0.011752 | −0.014147 | 0.008677 | 0.019384 | −0.017573 | −0.028109 | −0.000802 | 0.008141 | −0.00944 | 0.041907 |
| 183 | −0.006824 | −0.029336 | 0.003453 | 0.010846 | −0.014047 | −0.037085 | −0.027427 | −0.000979 | −0.002677 | 0.02665 | 0.044283 | 0.009514 | 0.005585 | 0.019892 |
| 184 | −0.009925 | 0.011701 | 0.000481 | 0.024632 | −0.05933 | −0.039477 | −0.05802 | −0.01588 | 0.006246 | 0.047591 | 0.037013 | −0.046745 | 0.002241 | −0.022538 |
| 185 | 0.024631 | 0.045444 | 0.089376 | 0.011979 | 0.026252 | 0.031151 | −0.003582 | −0.0161 | −0.015749 | 0.047294 | 0.035797 | 0.046996 | 0.028129 | −0.024222 |
| 186 | 0.012315 | 0.054367 | 0.019634 | 0.005284 | 0.031955 | 0.04005 | −0.033032 | −0.013195 | −0.02754 | 0.034011 | 0.045839 | 0.037513 | 0.008654 | 0.003043 |
| 187 | 0.016954 | 0.00728 | 0.008195 | 0.002105 | −0.011488 | −0.008227 | −0.004343 | 0.015526 | 0.005952 | 0.005055 | 0.006624 | −0.052092 | −0.015819 | −0.000365 |
| 188 | 0.016781 | −0.00373 | −0.004637 | −0.00356 | −0.000505 | 0.00429 | 0.013574 | 0.033267 | 0.03121 | 0.020878 | 0.024935 | 0.007574 | 0.020498 | −0.000635 |
| 189 | 0.031469 | −0.009074 | 0.030615 | −0.051838 | −0.013948 | 0.01781 | 0.038 | 0.019727 | 0.034573 | −0.004089 | −0.00963 | −0.031534 | 0.023266 | 0.021301 |
| 190 | 0.009917 | −0.005258 | 0.002801 | 0.041827 | 0.027778 | −0.05033 | −0.023014 | 0.011598 | −0.023861 | 0.033699 | 0.002102 | −0.041551 | −0.032037 | −0.003751 |
| 191 | 0.008863 | 0.030743 | −0.02016 | 0.006763 | −0.008961 | −0.010056 | −0.004971 | −0.005746 | 0.016233 | −0.010263 | 0.009034 | −0.009934 | −0.009723 | −0.001225 |
| 192 | −0.017734 | −0.009669 | 0.01813 | 0.00834 | 0.016117 | 0.014965 | 0.06594 | −0.014875 | −0.001312 | −0.053144 | 0.000112 | −0.002103 | 0.015392 | −0.021372 |
| 193 | 0.027994 | −0.013668 | −0.048296 | −0.012237 | 0.043 | 0.047135 | 0.006713 | 0.006502 | 0.029068 | −0.022538 | −0.018188 | 0.029001 | −0.002082 | −0.035869 |
| 194 | −0.003416 | 0.022907 | 0.005793 | −0.012787 | −0.016635 | 0.034871 | 0.02681 | −0.039092 | 0.007762 | −0.033764 | −0.005586 | −0.013922 | 0.021459 | −0.029776 |
| 195 | −0.025259 | 0.018951 | 0.009885 | −0.015069 | 0.032981 | 0.03786 | 0.021198 | −0.000924 | −0.002507 | 0.040602 | 0.048677 | 0.030115 | −0.05813 | 0.020497 |
| 196 | −0.012746 | 0.037641 | 0.041203 | −0.03987 | −0.004599 | 0.019127 | −0.001133 | −0.038709 | −0.021802 | −0.024074 | −0.014021 | 0.020443 | −0.01729 | 0.014281 |
| 197 | 0.010016 | 0.005619 | −0.031271 | 0.037721 | −0.005212 | 0.027496 | 0.027934 | −0.024098 | 0.0045 | −0.012699 | −0.005561 | 0.016706 | 0.016547 | 0.012284 |
| 198 | −0.020519 | 0.009192 | −0.039471 | 0.003564 | −0.000629 | 0.019632 | 0.015747 | 0.012132 | 0.01275 | −0.017864 | −0.030441 | −0.000804 | −0.062802 | 0.027079 |
| 199 | 0.007966 | 0.037855 | 0.000056 | −0.028541 | −0.000803 | 0.030775 | 0.031693 | −0.038723 | −0.026647 | −0.045216 | 0.00173 | −0.029802 | −0.048048 | 0.026974 |
| 200 | 0.03231 | −0.014303 | −0.007722 | 0.017515 | 0.01669 | −0.048928 | −0.03069 | 0.011383 | 0.024656 | 0.014172 | 0.012889 | 0.039831 | −0.041291 | 0.021721 |
| 201 | −0.009924 | −0.015583 | 0.005713 | −0.051366 | −0.006993 | −0.004595 | −0.005934 | −0.014218 | −0.021346 | −0.013926 | −0.033422 | 0.024821 | 0.021016 | 0.018006 |
| 202 | −0.012511 | 0.012088 | −0.014386 | −0.030337 | −0.023729 | −0.00259 | 0.01361 | −0.002922 | 0.011676 | −0.034555 | −0.033364 | −0.02672 | −0.053955 | 0.019234 |
| 203 | −0.023493 | −0.017128 | −0.00077 | 0.029713 | 0.016196 | 0.012943 | 0.004424 | −0.003871 | −0.007428 | 0.021632 | 0.025409 | 0.025684 | −0.0282 | −0.024725 |
| 204 | 0.010457 | −0.045716 | 0.025779 | 0.012708 | −0.007038 | −0.076109 | −0.030534 | 0.004275 | −0.047901 | 0.00911 | −0.018035 | −0.03348 | −0.018765 | −0.027442 |
| 205 | 0.031017 | −0.01223 | 0.01134 | 0.009915 | 0.018207 | −0.002185 | −0.026953 | 0.018753 | −0.041401 | 0.077096 | 0.037888 | 0.018417 | 0.01658 | 0.012371 |
| 206 | −0.019632 | −0.000884 | 0.007142 | −0.025675 | 0.017481 | 0.005269 | 0.014558 | −0.01736 | −0.027375 | 0.002065 | −0.021349 | 0.009665 | −0.013601 | 0.032013 |
| 207 | −0.016611 | 0.00883 | 0.013076 | −0.00003 | −0.002217 | 0.025409 | 0.011104 | −0.012663 | 0.010013 | −0.002367 | 0.018478 | −0.0025 | 0.029443 | −0.010154 |
| 208 | −0.013009 | −0.04109 | −0.016204 | −0.002257 | 0.030593 | 0.0697 | 0.049985 | −0.019379 | −0.015966 | 0.001147 | 0.011591 | −0.015057 | 0.008042 | −0.032647 |
| 209 | −0.013022 | −0.007159 | −0.005733 | 0.006463 | −0.019841 | −0.040505 | −0.006368 | 0.009329 | 0.012267 | −0.007183 | −0.015139 | −0.018931 | 0.01386 | −0.011757 |
| 210 | 0.011599 | 0.023638 | 0.01819 | 0.03662 | 0.022283 | 0.0163 | −0.001144 | 0.021151 | −0.02002 | 0.016636 | −0.043773 | 0.034933 | 0.017089 | 0.01212 |
| 211 | 0.027922 | 0.019042 | −0.00243 | 0.056883 | −0.012394 | −0.008384 | −0.032528 | −0.01205 | 0.023251 | 0.020811 | −0.012942 | −0.020271 | 0.017029 | −0.007839 |
| 212 | −0.029355 | −0.029578 | 0.010433 | 0.027588 | −0.01004 | −0.055393 | 0.001818 | 0.007088 | −0.000913 | −0.027126 | −0.033161 | −0.050474 | −0.019361 | −0.006695 |
| 213 | −0.021349 | −0.051845 | −0.010265 | 0.012912 | −0.012071 | −0.004769 | −0.022895 | −0.005254 | 0.007123 | −0.027098 | −0.021787 | 0.021529 | 0.037862 | 0.013015 |
| 214 | 0.006097 | 0.002436 | −0.017937 | 0.007305 | 0.011014 | 0.018455 | −0.043096 | −0.019336 | −0.000549 | 0.006741 | −0.000461 | −0.014385 | 0.009206 | 0.009102 |
| 215 | 0.022833 | 0.024871 | −0.012183 | −0.045981 | 0.031454 | 0.026438 | 0.000831 | 0.008425 | −0.030604 | −0.017014 | 0.008383 | 0.015152 | 0.003129 | 0.015622 |
| 216 | 0.027351 | 0.018392 | −0.016422 | −0.066868 | −0.00112 | −0.016362 | 0.001583 | 0.017203 | 0.011369 | −0.006525 | 0.000124 | −0.01308 | −0.001681 | 0.013067 |
| 217 | −0.014159 | −0.021052 | 0.038847 | −0.033856 | 0.060495 | 0.027813 | 0.024374 | 0.003596 | −0.014769 | −0.022478 | −0.021283 | 0.019987 | −0.015523 | 0.001125 |
| 218 | −0.014771 | 0.003336 | 0.003927 | −0.030504 | −0.02723 | 0.005282 | −0.013429 | 0.032412 | 0.017917 | 0.011361 | 0.013882 | −0.011352 | −0.006575 | −0.00636 |
| 219 | 0.034564 | 0.023354 | −0.040033 | −0.006362 | −0.006177 | −0.019029 | −0.059047 | 0.021069 | 0.012258 | 0.019446 | −0.008078 | −0.019686 | −0.000215 | 0.005715 |
| 220 | 0.043793 | 0.043809 | 0.044287 | 0.001241 | −0.017031 | −0.03102 | −0.036271 | −0.016074 | −0.01632 | −0.009874 | −0.00387 | −0.033325 | −0.024672 | 0.007207 |
| 221 | 0.01316 | 0.052335 | −0.024641 | −0.005272 | −0.047177 | 0.016336 | −0.03406 | −0.004579 | 0.038292 | 0.015016 | 0.045827 | −0.00157 | 0.012948 | 0.03538 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 222 | 0.014993 | 0.047165 | −0.006499 | −0.0277 | −0.011749 | 0.012204 | 0.042107 | −0.00626 | 0.010464 | −0.010041 | 0.009198 | 0.019593 | 0.019928 | 0.015531 |
| 223 | 0.019725 | 0.013923 | −0.013784 | −0.043615 | 0.023153 | −0.009293 | −0.002236 | 0.023825 | 0.003898 | 0.001081 | 0.001381 | 0.016745 | −0.012586 | 0.005674 |
| 224 | −0.009064 | −0.028808 | −0.016923 | −0.02095 | −0.023396 | −0.038379 | −0.026188 | 0.018474 | −0.018188 | 0.016539 | −0.008785 | −0.009834 | −0.021758 | −0.016069 |
| 225 | −0.010169 | −0.006372 | −0.001752 | −0.02499 | −0.036374 | −0.023394 | 0.00557 | 0.024477 | 0.017257 | 0.000897 | −0.008312 | −0.012641 | −0.010533 | −0.011793 |
| 226 | 0.07437 | 0.057549 | 0.017983 | 0.027021 | 0.015295 | 0.019441 | 0.00542 | 0.005031 | 0.011906 | 0.02209 | 0.006289 | −0.008568 | −0.001393 | 0.030937 |
| 227 | 0.036143 | −0.017592 | 0.069646 | −0.023029 | 0.074873 | −0.004208 | 0.002572 | 0.000606 | −0.015236 | 0.020916 | −0.042612 | −0.02213 | 0.01845 | 0.029153 |
| 228 | −0.018482 | −0.023663 | 0.027042 | 0.002551 | 0.026998 | 0.065031 | −0.022206 | 0.016288 | 0.004652 | 0.03648 | 0.013133 | −0.092897 | −0.010118 | −0.018357 |
| 229 | 0.010371 | −0.027255 | −0.013887 | 0.027372 | −0.016324 | 0.000273 | −0.003924 | 0.00913 | 0.00933 | 0.027233 | 0.001278 | 0.019304 | 0.023198 | 0.012103 |
| 230 | 0.051306 | 0.048421 | −0.023017 | −0.00594 | 0.027807 | 0.036181 | −0.001996 | 0.027634 | 0.021367 | 0.027371 | 0.027848 | 0.03757 | 0.008077 | 0.006072 |
| 231 | 0.025637 | −0.001773 | −0.008204 | 0.015136 | 0.015543 | 0.014178 | 0.005568 | 0.021588 | 0.051195 | −0.004907 | 0.038793 | 0.014278 | 0.023912 | 0.042765 |
| 232 | 0.002463 | 0.021145 | −0.019672 | −0.000362 | 0.024682 | 0.036737 | −0.017911 | 0.00007 | 0.00606 | 0.023134 | 0.032124 | 0.01482 | −0.004867 | 0.018479 |
| 233 | −0.001793 | −0.038352 | 0.017728 | −0.058171 | −0.001738 | −0.048051 | −0.012455 | −0.022446 | −0.007465 | −0.00836 | −0.010745 | 0.045408 | 0.013067 | 0.044869 |
| 234 | 0.013338 | −0.00722 | −0.045922 | 0.012018 | 0.01342 | 0.026418 | −0.029122 | −0.032535 | −0.032808 | 0.03402 | 0.021966 | 0.013856 | −0.015596 | 0.012728 |
| 235 | 0.001617 | 0.02367 | −0.036021 | 0.004222 | −0.009375 | 0.03479 | −0.004119 | −0.024198 | 0.003558 | 0.006582 | 0.025477 | −0.035143 | −0.022811 | −0.014913 |
| 236 | −0.015542 | −0.036481 | 0.000037 | 0.038464 | 0.035544 | −0.008675 | −0.055447 | 0.022965 | 0.0009 | 0.067187 | 0.0599 | −0.045285 | −0.062565 | 0.000145 |
| 237 | −0.053898 | −0.045049 | 0.077198 | −0.017155 | 0.079624 | 0.11544 | 0.072078 | 0.078325 | 0.101315 | 0.009692 | 0.021634 | −0.019173 | 0.041731 | −0.049938 |
| 238 | −0.004999 | −0.011623 | −0.111638 | −0.004134 | 0.063365 | 0.031489 | 0.009719 | 0.019575 | 0.031997 | 0.003015 | 0.013455 | 0.033629 | 0.034883 | −0.006081 |
| 239 | 0.000058 | −0.009062 | −0.158267 | 0.001913 | 0.038754 | 0.044898 | −0.010026 | 0.018635 | 0.033302 | 0.010211 | 0.025449 | 0.047362 | 0.032339 | 0.012448 |
| 240 | 0.020072 | −0.012567 | −0.02848 | 0.003512 | −0.020441 | −0.01815 | −0.014363 | 0.017796 | 0.023125 | −0.009504 | −0.014993 | −0.030427 | 0.028703 | 0.005741 |
| 241 | 0.026204 | 0.006278 | −0.005061 | 0.019933 | −0.000851 | −0.038559 | −0.031991 | 0.012115 | −0.007434 | −0.000627 | −0.016239 | 0.002734 | 0.005241 | 0.028324 |
| 242 | −0.005868 | 0.001295 | 0.014799 | −0.091777 | −0.013143 | −0.031676 | 0.022689 | 0.003209 | −0.011678 | 0.022991 | 0.032412 | 0.000448 | −0.037495 | −0.003251 |
| 243 | −0.0041 | −0.001621 | −0.003836 | −0.216071 | 0.015738 | −0.031566 | −0.028855 | 0.033308 | 0.001708 | 0.014741 | −0.011319 | 0.00901 | 0.012167 | −0.032638 |
| 244 | −0.002467 | 0.031367 | 0.023123 | 0:020883 | 0.018368 | 0.040695 | 0.020622 | 0.033756 | 0.041298 | 0.030732 | 0.042149 | 0.039539 | −0.007684 | 0.016808 |
| 245 | 0.00458 | −0.005884 | 0.014992 | 0.006555 | −0.0271 | −0.002933 | 0.044022 | 0.018915 | 0.042744 | −0.005582 | −0.001511 | 0.063281 | 0.028811 | 0.015774 |
| 246 | 0.0075571 | 0.017879 | 0.065142 | 0.029612 | −0.08658 | −0.041431 | −0.016176 | 0.00896 | 0.011651 | 0.033996 | 0.026496 | 0.01091 | 0.012495 | 0.002574 |
| 247 | 0.021663 | 0.027364 | 0.003756 | 0.031449 | −0.03299 | −0.06332 | −0.147895 | 0.026532 | 0.014972 | 0.025377 | 0.028896 | −0.014382 | −0.020167 | 0.009615 |
| 248 | 0.030504 | 0.025714 | −0.035696 | 0.04641 | −0.002942 | −0.001745 | −0.128441 | 0.040423 | 0.043201 | 0.012038 | 0.021476 | −0.060568 | −0.013419 | 0.004644 |
| 249 | 0.053594 | 0.056842 | −0.002158 | 0.01922 | −0.006622 | −0.005434 | −0.006882 | 0.000798 | 0.001098 | 0.01465 | −0.012065 | 0.051055 | 0.019767 | 0.021066 |
| 250 | 0.006084 | 0.015304 | 0.038974 | 0.043723 | −0.01 | −0.019224 | −0.022642 | −0.039396 | −0.057236 | 0.019244 | 0.020206 | −0.013076 | −0.022589 | 0.021347 |
| 251 | 0.026197 | 0.046364 | −0.001511 | −0.019317 | −0.01745 | 0.009119 | 0.020801 | 0.016198 | 0.005908 | −0.008021 | −0.006744 | −0.001314 | 0.011375 | −0.021601 |
| 252 | 0.025582 | 0.0179 | −0.021975 | −0.026858 | 0.035158 | 0.00376 | 0.022042 | 0.035344 | 0.024005 | 0.028657 | 0.000334 | 0.019579 | 0.007453 | −0.01067 |
| 253 | 0.031047 | −0.008251 | 0.032895 | −0.121786 | 0.057083 | 0.021474 | 0.023132 | −0.016614 | −0.055095 | −0.021153 | −0.038715 | −0.028194 | 0.012179 | −0.025793 |
| 254 | 0.037312 | 0.005628 | 0.015349 | 0.007474 | 0.023675 | −0.019899 | 0.025654 | 0.031654 | 0.049161 | −0.001144 | −0.008449 | 0.000923 | −0.030294 | −0.008359 |
| 255 | 0.04397 | 0.033233 | 0.022269 | 0.023674 | −0.015895 | −0.015481 | −0.019853 | 0.037604 | 0.026342 | 0.030399 | 0.016414 | −0.025976 | −0.022684 | 0.01574 |
| 256 | 0.064343 | 0.05276 | 0.009009 | 0.030825 | 0.015899 | 0.00709 | −0.012218 | −0.037352 | −0.029578 | 0.006183 | −0.029313 | 0.015839 | −0.035289 | 0.003512 |
| 257 | 0.040566 | 0.047238 | 0.038169 | 0.042736 | 0.027567 | 0.034621 | 0.056419 | −0.139464 | −0.117108 | −0.064284 | −0.052584 | 0.014145 | −0.014767 | 0.014636 |
| 258 | 0.023045 | 0.028141 | 0.010462 | −0.00145 | −0.036444 | −0.000722 | −0.015518 | −0.009577 | 0.021917 | −0.119551 | −0.081504 | −0.123878 | −0.016587 | 0.006737 |
| 259 | 0.028519 | 0.034524 | 0.023802 | −0.047257 | −0.021296 | −0.010167 | 0.017961 | 0.022378 | 0.01687 | −0.008147 | 0.000788 | 0.018202 | 0.021847 | 0.002283 |
| 260 | −0.007209 | −0.002445 | 0.023212 | 0.039115 | −0.012563 | −0.007401 | −0.014728 | 0.011626 | 0.009747 | 0.016679 | 0.014692 | −0.033667 | −0.015835 | −0.003287 |
| 261 | 0.008537 | 0.021513 | −0.007294 | −0.017166 | −0.028499 | 0.01922 | 0.020089 | 0.018964 | 0.051702 | −0.016393 | −0.002916 | −0.005819 | −0.025982 | −0.005204 |
| 262 | 0.006767 | 0.005795 | 0.001575 | −0.00328 | 0.00654 | 0.01208 | −0.014648 | 0.00348 | 0.044083 | 0.020522 | 0.03023 | −0.025314 | −0.092262 | 0.024455 |
| 263 | 0.015427 | 0.008229 | 0.001868 | −0.040692 | 0.009127 | 0.038197 | 0.002761 | −0.00458 | 0.023145 | 0.00165 | 0.003509 | −0.038436 | −0.05143 | 0.022373 |
| 264 | 0.001315 | 0.018272 | −0.005322 | −0.018855 | −0.026832 | −0.0002 | 0.02569 | −0.034286 | −0.021545 | −0.045682 | −0.011179 | 0.01862/ | 0.075369 | 0.043822 |
| 265 | −0.006225 | 0.010837 | −0.017465 | −0.029088 | 0.002161 | 0.018524 | 0.021439 | 0.011292 | 0.019998 | −0.024056 | 0.010701 | 0.016027 | −0.009247 | 0.013849 |
| 266 | 0.012881 | 0.006029 | −0.022583 | −0.031766 | −0.006835 | −0.013126 | −0.033706 | 0.02703 | 0.03265 | 0.010151 | 0.010315 | −0.021492 | −0.083289 | 0.000613 |
| 267 | 0.028658 | 0.045998 | 0.022527 | −0.006264 | −0.023368 | −0.008431 | 0.007057 | −0.009743 | 0.007362 | −0.022075 | −0.010157 | 0.060073 | 0.004045 | 0.000322 |
| 268 | 0.030068 | 0.045702 | 0.007297 | −0.0151 | 0.00955 | 0.01257 | 0.024805 | −0.011521 | −0.010224 | 0.025318 | 0.020176 | 0.023007 | 0.000575 | 0.004457 |
| 269 | 0.035571 | 0.03124 | −0.000834 | 0.010304 | 0.026983 | −0.029146 | 0.007299 | −0.010081 | −0.026062 | 0.017679 | 0.004246 | 0.011749 | −0.009516 | 0.001519 |
| 270 | 0.037839 | 0.019416 | 0.00466 | 0.007311 | 0.031761 | 0.014928 | 0.005332 | −0.018757 | −0.044767 | −0.01094 | −0.038386 | −0.021869 | −0.028133 | 0.006446 |
| 271 | 0.058941 | 0.016121 | 0.013123 | −0.032443 | 0.084017 | 0.001478 | −0.015581 | 0.016772 | −0.037811 | 0.019155 | 0.025257 | 0.011503 | −0.028281 | 0.016207 |
| 272 | 0.006103 | −0.005612 | 0.004596 | −0.018565 | −0.021565 | 0.015426 | −0.019491 | −0.015195 | −0.005185 | −0.009087 | 0.004788 | 0.00861 | 0.041064 | 0.019686 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 273 | −0.005176 | 0.000013 | 0.035213 | −0.020495 | 0.001867 | 0.004331 | 0.022292 | −0.018462 | −0.020746 | 0.018122 | 0.017463 | 0.021427 | −0.004122 | −0.006682 |
| 274 | 0.003404 | 0.004996 | 0.031864 | −0.004632 | 0.006376 | 0.009087 | −0.000039 | −0.012417 | −0.030069 | 0.019489 | 0.010931 | 0.008998 | −0.017003 | −0.009558 |
| 275 | 0.018354 | −0.003343 | −0.009961 | −0.009966 | −0.000072 | −0.040121 | −0.056307 | 0.011793 | 0.012235 | 0.002476 | −0.02511 | −0.020763 | −0.024518 | 0.007571 |
| 276 | −0.042833 | −0.039285 | −0.016782 | −0.008006 | −0.015696 | −0.023216 | −0.029654 | −0.003548 | 0.008866 | 0.025975 | 0.039703 | −0.027476 | −0.03567 | −0.000821 |
| 277 | 0.800456 | −0.153224 | −0.030434 | 0.007276 | −0.026425 | −0.0047 | 0.012678 | 0.013431 | 0.002555 | 0.013542 | 0.046456 | −0.012589 | −0.01071 | −0.001988 |
| 278 | −0.142178 | 0.747215 | −0.061353 | 0.027306 | 0.020828 | −0.054484 | −0.020767 | 0.039622 | −0.012091 | 0.02832 | 0.001201 | −0.041184 | −0.010467 | 0.004106 |
| 279 | −0.007465 | −0.0575 | 0.750638 | 0.047064 | 0.03074 | 0.003536 | −0.073226 | 0.009528 | −0.001534 | 0.016213 | 0.010767 | −0.00635 | 0.003641 | 0.008093 |
| 280 | −0.036587 | 0.002538 | 0.031977 | 0.576609 | −0.069523 | −0.025027 | 0.044753 | 0.002985 | 0.042936 | −0.060712 | −0.038761 | 0.020872 | 0.019934 | −0.01204 |
| 281 | −0.011795 | 0.027509 | −0.004882 | −0.046116 | 0.742601 | −0.13217 | −0.078672 | −0.010739 | 0.037696 | −0.042386 | −0.003564 | −0.022522 | 0.020238 | 0.020537 |
| 282 | 0.005713 | −0.063717 | 0.006402 | −0.045769 | −0.153116 | 0.714014 | −0.087942 | 0.017418 | −0.031685 | −0.03333 | −0.058069 | −0.033551 | −0.005152 | 0.006185 |
| 283 | 0.056402 | 0.009434 | −0.050835 | 0.063769 | −0.013864 | −0.071685 | 0.706576 | 0.017004 | −0.021122 | 0.026406 | −0.022988 | −0.106545 | −0.057092 | 0.001693 |
| 284 | 0.013402 | 0.03985 | 0.004943 | 0.032312 | −0.007019 | 0.025545 | 0.015694 | 0.822626 | −0.145759 | −0.079025 | −0.063034 | −0.000133 | 0.001121 | 0.016635 |
| 285 | 0.018067 | 0.013453 | 0.019576 | 0.073088 | 0.05651 | 0.000761 | 0.003542 | −0.142777 | 0.767355 | −0.035652 | −0.065917 | −0.001511 | −0.017057 | −0.004154 |
| 286 | 0.011164 | 0.031757 | 0.008456 | −0.077838 | −0.051339 | −0.037194 | 0.045753 | −0.077002 | −0.038025 | 0.750604 | −0.185041 | −0.079952 | 0.028468 | 0.016136 |
| 287 | 0.045568 | 0.020501 | 0.01752 | −0.065037 | −0.015661 | −0.055602 | 0.015656 | −0.061249 | −0.068867 | −0.197744 | 0.764191 | −0.086077 | 0.01176 | −0.009172 |
| 288 | 0.008365 | −0.045631 | −0.005528 | 0.051717 | −0.020157 | −0.05855 | −0.130767 | 0.001376 | −0.010374 | −0.066442 | −0.112199 | 0.645057 | −0.092953 | −0.063899 |
| 289 | 0.019921 | 0.010778 | −0.009088 | 0.027042 | 0.004539 | −0.031009 | −0.045113 | −0.003063 | −0.023572 | 0.020335 | −0.001403 | −0.067408 | 0.833153 | −0.007018 |
| 290 | −0.003576 | −0.006626 | −0.003994 | −0.025296 | 0.021631 | −0.004661 | −0.002953 | 0.010978 | 0.000743 | 0.003074 | −0.014173 | −0.039498 | −0.017648 | 0.743956 |
| 291 | −0.00667 | −0.004052 | −0.005324 | −0.028904 | 0.01041 | −0.002251 | 0.000658 | 0.004527 | 0.008578 | −0.011358 | −0.021325 | −0.038468 | −0.011262 | −0.245955 |
| 292 | −0.001233 | 0.049963 | −0.040895 | 0.003127 | 0.016094 | 0.035349 | −0.010336 | −0.00516 | −0.020525 | −0.004646 | −0.003 | −0.016253 | 0.00033 | −0.223271 |
| 293 | −0.025081 | −0.030537 | −0.029273 | −0.068929 | −0.040306 | −0.004376 | −0.023691 | −0.021975 | 0.017189 | −0.014183 | 0.00361 | −0.079569 | −0.006081 | −0.019264 |
| 294 | −0.009248 | 0.009286 | 0.00086 | −0.046645 | −0.023165 | −0.011867 | −0.01289 | 0.016801 | 0.038061 | 0.01092 | 0.012881 | −0.006472 | −0.021036 | −0.006435 |
| 295 | 0.026417 | 0.022285 | −0.001528 | −0.02781 | −0.00383 | 0.038767 | −0.011887 | −0.014769 | 0.011605 | 0.021009 | 0.024948 | 0.007862 | −0.021122 | −0.023788 |
| 296 | −0.003166 | −0.002569 | 0.018597 | 0.013788 | 0.006144 | −0.006403 | −0.024593 | 0.031527 | 0.016749 | 0.0103 | 0.008108 | −0.016372 | −0.029892 | −0.013565 |
| 297 | −0.006839 | −0.001547 | −0.018391 | −0.033971 | −0.024608 | 0.01127 | −0.009036 | −0.035553 | −0.023243 | −0.004845 | −0.004174 | 0.012037 | 0.007676 | 0.000723 |
| 298 | 0.004538 | −0.050501 | −0.019756 | −0.015549 | 0.004264 | −0.029159 | −0.034862 | 0.001945 | 0.005484 | −0.001783 | 0.010807 | 0.028514 | 0.030683 | −0.01244 |
| 299 | 0.019838 | 0.002121 | −0.015723 | −0.040874 | 0.000051 | −0.029948 | −0.015647 | 0.039515 | 0.041828 | 0.015037 | 0.024971 | 0.001352 | 0.009027 | 0.014053 |
| 300 | 0.017298 | 0.012699 | −0.039869 | −0.029837 | −0.018456 | 0.0313 | 0.043633 | 0.0094 | 0.014854 | 0.00304 | 0.009968 | 0.047 | −0.000525 | −0.031389 |
| 301 | 0.005813 | −0.000151 | −0.020473 | 0.008904 | −0.003623 | 0.014865 | −0.00506 | −0.065631 | −0.066935 | 0.043061 | 0.035257 | −0.000677 | −0.010457 | 0.001571 |
| 302 | 0.003647 | 0.009648 | −0.014556 | −0.008447 | −0.025185 | −0.003926 | 0.027489 | −0.043397 | −0.043252 | 0.011106 | −0.000758 | −0.015974 | −0.036067 | 0.023376 |
| 303 | 0.008719 | −0.030504 | −0.022577 | −0.016164 | 0.000366 | −0.059735 | −0.036091 | 0.050625 | 0.031171 | 0.001107 | −0.007217 | −0.003033 | 0.029303 | 0.038456 |
| 304 | −0.012024 | −0.002629 | 0.009867 | −0.048739 | −0.002747 | 0.023981 | −0.026145 | 0.048196 | 0.058853 | −0.002546 | −0.011979 | −0.036845 | 0.024429 | 0.020723 |
| 305 | 0.058226 | 0.043603 | 0.00463 | 0.014746 | −0.043591 | −0.032297 | −0.02583 | −0.014809 | −0.008977 | 0.006024 | 0.000767 | 0.037464 | −0.010706 | 0.033345 |
| 306 | 0.009022 | 0.030653 | −0.003568 | −0.01316 | −0.05962 | 0.027571 | 0.004554 | −0.025151 | 0.015083 | 0.031074 | 0.045293 | 0.082724 | 0.043168 | −0.012109 |
| 307 | −0.011871 | −0.04699 | −0.017761 | −0.019685 | −0.011844 | −0.043397 | 0.023473 | −0.042683 | −0.043713 | −0.025803 | −0.026742 | −0.048161 | −0.012931 | −0.006482 |
| 308 | −0.003343 | −0.005977 | −0.016512 | −0.005808 | 0.005517 | −0.006878 | −0.017257 | 0.000038 | −0.034445 | 0.030808 | −0.00141 | −0.011472 | 0.008767 | −0.008251 |
| 309 | 0.00196 | −0.009134 | −0.019647 | −0.006398 | 0.012432 | −0.026769 | −0.012215 | 0.020191 | −0.001637 | 0.015793 | −0.021576 | −0.001807 | 0.002873 | −0.008912 |
| 310 | 0.025018 | 0.006095 | 0.012495 | 0.01347 | 0.024649 | −0.004313 | 0.009302 | 0.020575 | −0.002076 | 0.039584 | 0.038386 | 0.037297 | −0.005452 | −0.014546 |
| 311 | −0.007091 | 0.000294 | −0.031409 | −0.003688 | 0.017483 | 0.008109 | 0.006061 | −0.0058 | 0.010557 | 0.016463 | 0.008658 | 0.02636 | −0.018288 | −0.001148 |
| 312 | 0.013727 | −0.015482 | 0.037152 | 0.022179 | −0.000552 | 0.016375 | 0.032569 | 0.026999 | 0.036815 | −0.003122 | −0.001322 | 0.016281 | 0.010535 | 0.003919 |
| 313 | −0.030651 | −0.004408 | −0.00919 | 0.018821 | −0.034386 | −0.015591 | 0.049478 | −0.020843 | 0.009767 | 0.006618 | 0.021255 | 0.061187 | 0.036278 | 0.035196 |
| 314 | 0.011873 | 0.013826 | −0.002086 | −0.002796 | −0.015344 | 0.000164 | −0.01648 | 0.01218 | 0.014435 | −0.01026 | −0.003138 | 0.007066 | −0.001637 | 0.027537 |
| 315 | 0.008207 | 0.017623 | −0.000876 | 0.01977 | −0.006207 | 0.004993 | −0.005226 | 0.031968 | 0.026255 | −0.014575 | −0.02116 | −0.000029 | −0.011662 | 0.004649 |
| 316 | −0.001349 | −0.021573 | −0.005328 | −0.09705 | 0.010206 | 0.015096 | 0.030111 | 0.004853 | 0.029135 | −0.019206 | −0.003383 | 0.016234 | 0.014086 | 0.019509 |
| 317 | 0.002995 | −0.017882 | −0.015115 | 0.037121 | 0.011713 | −0.003417 | −0.044594 | −0.031511 | −0.048544 | 0.005295 | −0.012573 | 0.012593 | −0.011637 | −0.009716 |
| 318 | −0.0362 | −0.015518 | 0.044855 | 0.042167 | 0.042635 | 0.069951 | −0.0004 | 0.003641 | −0.011265 | 0.018728 | 0.032392 | 0.016943 | 0.024587 | 0.024189 |
| 319 | −0.000383 | 0.007574 | 0.020515 | 0.023598 | 0.014534 | 0.023006 | 0.008566 | 0.001461 | −0.014928 | −0.043473 | −0.04189 | 0.00587 | 0.015309 | −0.006375 |
| 320 | −0.02901 | −0.005172 | 0.040067 | 0.071701 | 0.053583 | 0.032033 | 0.035093 | −0.033457 | −0.038839 | −0.005475 | 0.015055 | −0.037733 | 0.010272 | 0.007276 |
| 321 | −0.01228 | 0.018494 | −0.013628 | −0.008476 | −0.043743 | −0.0322 | 0.026597 | −0.0184 | 0.004085 | −0.003663 | 0.008111 | 0.016688 | −0.003913 | −0.00708 |
| 322 | 0.01465 | 0.028658 | −0.013019 | −0.024324 | −0.02242 | 0.01785 | 0.009416 | 0.005618 | 0.001017 | 0.010398 | 0.011686 | −0.00704 | −0.043693 | −0.01999 |
| 323 | 0.064907 | 0.022647 | 0.031534 | −0.005305 | 0.023208 | 0.021608 | 0.045074 | −0.008161 | 0.003798 | 0.007757 | 0.023745 | 0.065466 | 0.018945 | 0.010552 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 324 | 0.021213 | 0.008287 | −0.002193 | 0.052425 | −0.017067 | −0.01239 | 0.011033 | −0.004909 | −0.006387 | 0.014677 | 0.007599 | −0.009348 | −0.027372 | 0.042307 |
| 325 | −0.000436 | −0.007828 | 0.014154 | −0.006989 | 0.002794 | −0.017856 | 0.022733 | 0.009152 | 0.019295 | 0.000218 | −0.004138 | −0.006246 | 0.024013 | −0.008662 |
| 326 | 0.045101 | 0.027004 | −0.0028 | −0.002371 | −0.001533 | 0.024289 | −0.036897 | 0.001638 | 0.029536 | −0.03387 | −0.034382 | 0.008722 | −0.018944 | −0.022069 |
| 327 | 0.001249 | 0.032709 | −0.006024 | 0.036555 | 0.000264 | 0.016599 | −0.006076 | 0.013441 | −0.011448 | −0.001077 | 0.010954 | −0.014086 | −0.00627 | −0.031352 |
| 328 | −0.018366 | −0.044602 | −0.007934 | 0.032624 | 0.02035 | −0.029334 | −0.030988 | −0.000425 | −0.041048 | 0.009001 | −0.021505 | 0.029584 | −0.008403 | 0.011597 |
| 329 | 0.015192 | 0.043691 | −0.003783 | 0.034416 | 0.008505 | 0.040172 | 0.021082 | −0.009926 | −0.003561 | −0.047544 | −0.004158 | 0.011259 | 0.013651 | −0.00808 |
| 330 | −0.01357 | 0.000075 | 0.013624 | 0.003041 | −0.044439 | −0.036784 | 0.028638 | −0.00814 | 0.009455 | −0.029527 | −0.010477 | −0.013984 | 0.006858 | 0.023173 |
| 331 | 0.037079 | 0.005546 | −0.004654 | −0.019806 | 0.007708 | −0.023853 | −0.028978 | 0.031405 | 0.028215 | −0.013623 | −0.034395 | −0.062406 | −0.018441 | −0.02361 |
| 332 | −0.01598 | 0.011515 | −0.034083 | −0.034612 | 0.039974 | −0.009501 | 0.013325 | −0.01538 | −0.015007 | 0.001237 | 0.017682 | 0.017153 | 0.006164 | 0.006721 |
| 333 | −0.001553 | −0.005652 | −0.016027 | 0.001273 | 0.021595 | 0.012937 | −0.000685 | −0.02763 | −0.043394 | 0.000714 | −0.001573 | −0.002056 | −0.001254 | −0.017958 |
| 334 | 0.0171 | 0.014753 | 0.017901 | 0.014848 | 0.034291 | −0.01125 | −0.010405 | 0.004155 | 0.004289 | −0.02551 | −0.013156 | 0.000917 | 0.021201 | −0.011459 |
| 335 | 0.031983 | −0.010845 | −0.010368 | −0.025155 | −0.006536 | −0.026042 | −0.028354 | −0.002523 | −0.018289 | −0.010819 | −0.022583 | −0.017803 | 0.014287 | 0.003969 |
| 336 | 0.000901 | 0.050107 | 0.069563 | −0.049601 | −0.002358 | 0.039367 | −0.049677 | 0.000134 | 0.038112 | −0.041964 | −0.024435 | −0.031683 | −0.009967 | 0.024585 |
| 337 | 0.004958 | 0.014937 | −0.005916 | 0.003084 | −0.033571 | −0.022562 | 0.01684 | −0.016655 | −0.010278 | 0.014114 | 0.021658 | 0.009948 | 0.016918 | −0.011836 |
| 338 | 0.031176 | 0.006727 | −0.025881 | 0.030347 | −0.046464 | −0.079918 | −0.021376 | −0.013557 | 0.004592 | −0.018666 | −0.02171 | −0.019532 | −0.026817 | −0.01914 |
| 339 | 0.019533 | 0.026567 | −0.048736 | 0.028283 | 0.006353 | 0.056849 | 0.033795 | −0.005718 | 0.005579 | −0.015352 | −0.01368 | −0.012702 | 0.022422 | −0.016647 |
| 340 | −0.0235 | −0.012897 | 0.000327 | −0.00108 | −0.024281 | 0.012497 | 0.020488 | 0.008988 | 0.025283 | −0.014776 | −0.009115 | 0.009734 | 0.049855 | −0.002871 |

| | KF | KG | KH | KI | KJ | KK | KL | KM | KN | KO | KP | KQ | KR | KS |
|---|---|---|---|---|---|---|---|---|---|---|---|---|---|---|
| 1 | 0.014763 | −0.004219 | −0.019053 | 0.030815 | 0.019146 | −0.08122 | 0.061559 | −0.02703 | 0.042228 | −0.020373 | 0.059734 | 0.037442 | 0.027359 | 0.017498 |
| 2 | 0.048955 | 0.068052 | −0.041869 | −0.047608 | −0.045113 | −0.045602 | −0.065461 | 0.002831 | −0.012348 | −0.040572 | −0.053465 | −0.007266 | −0.086123 | −0.019083 |
| 3 | 0.031275 | 0.002805 | −0.054891 | −0.049135 | −0.045712 | −0.003345 | 0.033197 | −0.074256 | −0.071089 | −0.063539 | −0.053536 | −0.082184 | −0.053113 | −0.091742 |
| 4 | −0.020457 | −0.067472 | −0.042206 | −0.065297 | 0.035631 | −0.022976 | −0.028905 | −0.000868 | −0.017501 | −0.073884 | 0.041225 | 0.020884 | 0.088704 | −0.031146 |
| 5 | −0.036409 | −0.021223 | −0.044958 | 0.015311 | −0.019013 | −0.0096 | 0.014074 | 0.020674 | −0.038534 | −0.007504 | −0.002635 | −0.001913 | −0.015354 | −0.068842 |
| 6 | −0.009396 | 0.015885 | −0.050037 | 0.022596 | 0.007975 | 0.077518 | −0.022336 | −0.031554 | −0.053624 | −0.033349 | −0.011436 | −0.017939 | −0.063207 | −0.072273 |
| 7 | 0.001331 | 0.010863 | 0.043857 | 0.067956 | 0.021718 | −0.031924 | 0.02571 | −0.007857 | −0.033707 | −0.012096 | 0.05065 | 0.021239 | −0.019221 | 0.013158 |
| 8 | 0.021489 | −0.001677 | 0.063098 | 0.039861 | 0.032537 | 0.039542 | 0.052577 | −0.058974 | 0.08477 | 0.009371 | 0.021895 | 0.044713 | −0.005927 | 0.030665 |
| 9 | −0.006221 | 0.004145 | 0.007654 | 0.002959 | −0.067842 | 0.03219 | 0.013973 | 0.087037 | 0.026914 | −0.044307 | 0.041813 | −0.011098 | 0.007973 | 0.030129 |
| 10 | 0.007146 | −0.050825 | −0.010502 | 0.035431 | −0.021569 | −0.005816 | −0.030468 | 0.040753 | 0.009317 | 0.148373 | −0.015712 | 0.051486 | 0.081614 | 0.03169 |
| 11 | −0.0592 | −0.043776 | 0.010658 | 0.009499 | 0.016285 | −0.02093 | 0.033273 | 0.040302 | 0.01312 | 0.01115 | 0.007632 | −0.004789 | 0.047288 | 0.055049 |
| 12 | −0.000946 | −0.000389 | 0.002666 | −0.005899 | 0.011316 | −0.006963 | −0.024672 | 0.005731 | 0.000292 | −0.037173 | −0.0189 | −0.03848 | −0.00632 | 0.018938 |
| 13 | −0.031911 | −0.01346 | −0.127292 | −0.020555 | −0.025406 | −0.02057 | −0.049832 | −0.056582 | −0.072635 | −0.044476 | −0.049068 | 0.029531 | 0.014249 | 0.01274 |
| 14 | 0.025689 | 0.057604 | 0.026402 | −0.06844 | 0.096706 | 0.04295 | 0.096432 | −0.047743 | −0.006763 | 0.044914 | 0.085597 | 0.031518 | −0.03277 | −0.045043 |
| 15 | 0.027564 | 0.050068 | −0.042169 | 0.015195 | −0.002253 | 0.145124 | 0.056625 | 0.182336 | 0.102536 | 0.035164 | 0.110038 | 0.102378 | 0.059656 | 0.097026 |
| 16 | 0.004571 | −0.013145 | −0.004984 | −0.020718 | −0.009458 | −0.001728 | 0.011828 | −0.024897 | 0.028307 | −0.000393 | −0.047393 | 0.00557 | 0.007884 | 0.033228 |
| 17 | 0.022384 | 0.001542 | 0.082137 | −0.037033 | 0.03067 | 0.006295 | 0.022792 | 0.028703 | 0.074479 | −0.004305 | 0.02477 | −0.011894 | 0.029347 | 0.058632 |
| 18 | 0.006053 | −0.03264 | −0.06892 | −0.027345 | −0.05315 | −0.084922 | 0.006561 | 0.044616 | 0.035281 | 0.091351 | −0.030177 | −0.043505 | 0.02547 | −0.00069 |
| 19 | 0.02476 | 0.049721 | 0.029594 | 0.024858 | 0.024069 | 0.008609 | −0.005613 | 0.039204 | 0.008764 | 0.022084 | 0.042435 | 0.067932 | 0.06913 | 0.017964 |
| 20 | 0.012613 | 0.009093 | 0.043929 | 0.003657 | 0.001579 | −0.003475 | 0.055359 | −0.071108 | −0.130491 | 0.028896 | 0.007529 | 0.002205 | −0.128502 | −0.017069 |
| 21 | −0.07756 | −0.086359 | 0.015099 | −0.098523 | −0.039336 | −0.081321 | −0.064304 | −0.024325 | −0.036107 | −0.023463 | 0.013612 | −0.036733 | −0.026687 | 0.0084 |
| 22 | −0.015185 | −0.028477 | −0.011869 | 0.020685 | 0.031146 | −0.008454 | 0.06931 | 0.037497 | 0.069334 | −0.044637 | −0.009106 | −0.052929 | 0.045921 | 0.029166 |
| 23 | −0.015502 | −0.045233 | 0.033518 | −0.012267 | −0.019147 | −0.034549 | 0.041415 | −0.078714 | 0.039402 | −0.058248 | 0.001773 | 0.010209 | −0.017463 | 0.031383 |
| 24 | 0.026781 | 0.020922 | 0.037824 | 0.030123 | 0.070456 | 0.077677 | 0.035979 | 0.038507 | 0.044936 | 0.032919 | −0.008875 | 0.032288 | 0.052551 | 0.054128 |
| 25 | −0.005181 | −0.032227 | −0.006054 | 0.028915 | −0.037365 | 0.0608 | −0.067672 | −0.187023 | −0.036987 | −0.136234 | −0.012698 | 0.010099 | 0.014065 | −0.067241 |
| 26 | −0.067607 | −0.062264 | 0.052025 | 0.042587 | 0.006561 | −0.021648 | 0.005071 | −0.053301 | 0.058794 | −0.060707 | −0.003017 | −0.029734 | −0.016093 | 0.032692 |
| 27 | −0.029008 | 0.046552 | −0.030218 | 0.033785 | −0.062469 | −0.005869 | 0.018792 | −0.068485 | −0.053154 | 0.030637 | −0.006105 | 0.014964 | 0.02795 | −0.003663 |
| 28 | 0.042679 | 0.034482 | 0.026066 | −0.001215 | 0.018109 | 0.011013 | −0.019582 | 0.022575 | −0.034994 | −0.015885 | −0.045591 | −0.030362 | 0.03821 | 0.027776 |
| 29 | −0.029159 | −0.035583 | 0.067804 | 0.010137 | 0.063349 | 0.051665 | 0.047121 | −0.033567 | 0.027935 | −0.042112 | 0.078293 | 0.030913 | 0.056392 | 0.114997 |
| 30 | 0.102363 | 0.098991 | −0.038014 | −0.000353 | −0.050382 | 0.025331 | −0.08145 | 0.044401 | −0.094235 | −0.041304 | −0.059823 | −0.052934 | −0.067557 | 0.024427 |
| 31 | 0.02614 | 0.005495 | 0.027936 | −0.020706 | −0.073512 | −0.146293 | −0.039491 | 0.058049 | −0.083042 | −0.064874 | 0.05676 | 0.025117 | −0.064276 | −0.10206 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 32 | −0.083157 | −0.047637 | 0.039018 | −0.020203 | 0.02705 | 0.013308 | −0.01553 | −0.043267 | 0.041615 | 0.060707 | 0.01105 | 0.004387 | 0.045422 | 0.055443 |
| 33 | 0.070856 | 0.066898 | 0.047883 | −0.020188 | 0.04119 | −0.074382 | 0.076951 | 0.014623 | 0.075174 | 0.178491 | −0.015147 | −0.07549 | 0.001059 | 0.007855 |
| 34 | 0.067292 | 0.061368 | −0.12386 | −0.014998 | −0.021294 | 0.093008 | −0.01286 | 0.159984 | −0.075607 | 0.079823 | −0.077797 | −0.010924 | −0.072638 | −0.036094 |
| 35 | −0.026545 | 0.022338 | −0.037158 | −0.035643 | 0.025772 | 0.040319 | 0.063391 | −0.020219 | −0.028989 | −0.066263 | −0.039562 | −0.031402 | −0.006873 | −0.077316 |
| 36 | 0.020773 | 0.018587 | −0.039533 | 0.000793 | −0.066272 | −0.04726 | −0.089461 | −0.017759 | −0.003094 | −0.095765 | 0.028047 | −0.029637 | 0.018939 | −0.035397 |
| 37 | 0.00182 | −0.026147 | 0.127525 | −0.038035 | 0.062832 | 0.036147 | −0.017883 | 0.031568 | 0.016194 | −0.054072 | −0.053117 | −0.066877 | −0.049159 | 0.014223 |
| 38 | 0.03314 | 0.07515 | 0.030486 | −0.038013 | −0.023741 | −0.031032 | −0.039491 | 0.050482 | −0.009628 | 0.004514 | 0.029407 | 0.000183 | 0.033308 | −0.009465 |
| 39 | −0.037917 | −0.022202 | −0.017643 | 0.028046 | 0.052702 | 0.001884 | 0.006381 | 0.002588 | 0.026987 | 0.01145 | 0.010008 | 0.024445 | −0.045623 | −0.049625 |
| 40 | 0.024623 | 0.018081 | −0.10127 | −0.0525 | −0.016324 | −0.00624 | −0.049921 | −0.014427 | 0.014247 | 0.01632 | 0.00373 | 0.016905 | 0.043198 | 0.044411 |
| 41 | −0.021061 | −0.021668 | −0.029813 | 0.013279 | 0.043781 | −0.020595 | 0.043404 | −0.048332 | −0.048176 | −0.010585 | 0.015965 | 0.021832 | 0.030331 | 0.019261 |
| 42 | −0.096361 | −0.043402 | −0.017957 | −0.039904 | −0.006228 | −0.030926 | 0.001814 | −0.122279 | −0.035813 | 0.124168 | −0.04112 | −0.080392 | −0.036275 | −0.009358 |
| 43 | 0.001345 | 0.015301 | 0.137766 | 0.04809 | −0.022498 | 0.012573 | 0.023699 | −0.098821 | 0.007905 | −0.064763 | 0.023761 | 0.001682 | 0.01848 | 0.031842 |
| 44 | 0.009275 | 0.016972 | 0.001537 | 0.026031 | 0.008688 | 0.078438 | −0.000043 | −0.124748 | −0.036792 | −0.019773 | 0.003254 | 0.082802 | −0.060384 | −0.059125 |
| 45 | 0.031964 | 0.023315 | 0.076715 | 0.047183 | −0.015415 | 0.041178 | 0.040238 | 0.079096 | 0.077677 | −0.001582 | 0.008224 | 0.011095 | −0.0001 | −0.028083 |
| 46 | 0.012325 | 0.016374 | −0.061068 | −0.063523 | −0.005125 | −0.05987 | −0.010079 | −0.037206 | 0.025645 | 0.013532 | 0.00085 | 0.011284 | 0.041624 | 0.022548 |
| 47 | −0.007788 | 0.005172 | −0.084287 | 0.128023 | 0.056246 | 0.093384 | 0.061047 | −0.009927 | −0.01116 | −0.001363 | −0.020321 | −0.041092 | 0.008069 | −0.044792 |
| 48 | 0.043553 | 0.000417 | −0.008803 | −0.011384 | −0.038609 | 0.026282 | −0.057393 | 0.137957 | 0.000269 | 0.035124 | 0.035601 | 0.05638 | 0.039431 | 0.05701 |
| 49 | −0.012102 | −0.008495 | 0.051154 | 0.001354 | 0.054075 | −0.031719 | 0.07043 | −0.03576 | −0.001825 | −0.033319 | 0.059246 | 0.024868 | −0.057495 | −0.00567 |
| 50 | 0.003602 | −0.022119 | 0.00682 | 0.021391 | 0.052576 | 0.033783 | 0.020606 | 0.00324 | 0.02949 | 0.122176 | 0.047262 | 0.005527 | −0.035043 | −0.060114 |
| 51 | −0.008222 | −0.035877 | 0.003873 | 0.033974 | −0.016999 | 0.013335 | 0.029882 | 0.043952 | 0.027818 | 0.026058 | 0.043402 | 0.038323 | 0.056153 | 0.025613 |
| 52 | 0.043069 | 0.08432 | 0.127165 | 0.128662 | 0.126022 | 0.076766 | 0.076284 | 0.098614 | 0.021599 | 0.010004 | 0.105352 | 0.03319 | 0.006292 | −0.010127 |
| 53 | −0.040416 | −0.072569 | 0.04553 | −0.016539 | −0.003757 | 0.016826 | 0.034311 | −0.049344 | −0.02896 | 0.001825 | −0.00943 | 0.002957 | −0.022908 | 0.007927 |
| 54 | −0.026711 | −0.026066 | −0.043813 | −0.059429 | −0.109861 | −0.075376 | −0.068725 | 0.125696 | −0.014534 | −0.006252 | −0.078957 | −0.096929 | 0.033563 | −0.079757 |
| 55 | 0.058606 | 0.026187 | −0.064906 | −0.049155 | −0.002733 | −0.067857 | −0.07762 | 0.006841 | −0.027922 | 0.036081 | −0.038938 | −0.092252 | −0.043928 | −0.026284 |
| 56 | 0.021936 | 0.010445 | 0.031015 | 0.028708 | 0.100377 | 0.066131 | 0.013681 | −0.10096 | −0.028867 | 0.003944 | 0.000744 | 0.059664 | −0.053382 | 0.066804 |
| 57 | −0.035319 | −0.029423 | −0.027396 | 0.017524 | 0.015143 | 0.011407 | 0.025523 | −0.030574 | −0.021533 | 0.03146 | 0.023434 | 0.029365 | −0.008452 | 0.023087 |
| 58 | −0.050367 | −0.057528 | −0.032413 | 0.007048 | 0.024233 | 0.022422 | −0.039189 | 0.038246 | −0.034363 | 0.001799 | −0.06541 | −0.031318 | −0.066278 | −0.07376 |
| 59 | −0.003721 | 0.038542 | 0.024529 | −0.00938 | −0.06095 | 0.010102 | 0.008033 | 0.020809 | 0.012646 | 0.024838 | −0.036231 | −0.068259 | −0.067657 | −0.043229 |
| 60 | 0.003692 | 0.080734 | 0.00887 | −0.017339 | 0.005901 | −0.004468 | 0.119218 | −0.021714 | −0.020268 | −0.000739 | 0.007515 | −0.005121 | −0.016721 | 0.033299 |
| 61 | −0.05228 | −0.07433 | 0.037031 | −0.005197 | 0.007813 | −0.044632 | 0.043903 | 0.044476 | 0.010809 | 0.006268 | 0.058854 | 0.010505 | −0.013698 | −0.073833 |
| 67 | 0.015215 | 0.015216 | 0.078208 | 0.030328 | −0.006135 | −0.036725 | 0.001204 | −0.048395 | 0.051033 | −0.064003 | 0.065327 | 0.021706 | 0.084474 | 0.029329 |
| 63 | −0.033307 | −0.031808 | 0.009841 | 0.065975 | 0.022588 | −0.035527 | 0.015163 | −0.043748 | −0.024897 | 0.072004 | −0.041316 | −0.020688 | −0.026553 | 0.004376 |
| 64 | 0.012815 | 0.00434 | 0.002262 | 0.010587 | 0.01548 | −0.015808 | 0.006585 | −0.030621 | 0.013452 | 0.0118 | 0.004332 | −0.024011 | 0.007963 | 0.029606 |
| 65 | 0.007948 | 0.017548 | 0.098679 | 0.096831 | 0.037392 | 0.018896 | 0.017467 | −0.077011 | −0.000248 | 0.116269 | −0.027106 | 0.037586 | −0.059184 | −0.055734 |
| 66 | 0.003931 | 0.034855 | −0.107422 | 0.030799 | −0.036478 | −0.075152 | −0.024737 | −0.036065 | 0.055081 | −0.055376 | −0.03078 | 0.048305 | 0.109144 | 0.113691 |
| 67 | 0.029909 | −0.001617 | 0.031408 | −0.008035 | 0.057423 | 0.04447 | 0.056355 | 0.066661 | 0.071419 | −0.022672 | 0.033076 | −0.034269 | −0.009097 | −0.013126 |
| 68 | 0.015473 | 0.029372 | −0.050989 | −0.010181 | 0.0188 | 0.090436 | −0.005379 | −0.019362 | −0.011027 | −0.034096 | −0.02027 | 0.00265 | 0.032936 | −0.021513 |
| 69 | 0.066955 | 0.076245 | 0.033771 | −0.015147 | −0.071594 | −0.040314 | −0.051747 | −0.084974 | −0.014582 | 0.029496 | −0.055814 | −0.03662 | −0.044552 | −0.134923 |
| 70 | −0.106217 | −0.050018 | −0.017116 | −0.050092 | −0.065384 | −0.09635 | −0.002626 | 0.043137 | −0.037512 | −0.011398 | −0.082634 | −0.053837 | −0.094445 | −0.015881 |
| 71 | −0.034214 | 0.001838 | 0.10595 | −0.004278 | −0.012132 | −0.058815 | −0.001231 | 0.137728 | 0.057556 | 0.090459 | 0.062284 | 0.035331 | 0.084599 | −0.03859 |
| 72 | 0.015036 | 0.012457 | −0.013175 | 0.001744 | 0.021112 | 0.008469 | 0.045858 | −0.039592 | −0.051002 | −0.095205 | 0.033738 | 0.038606 | −0.088935 | −0.02197 |
| 73 | 0.04548 | 0.007049 | 0.101763 | 0.047628 | 0.032147 | −0.008944 | 0.001888 | 0.050311 | 0.04212 | −0.00125 | −0.023268 | 0.048901 | −0.016717 | 0.000669 |
| 74 | −0.015593 | 0.013938 | 0.067502 | 0.035086 | −0.020571 | −0.013333 | −0.037793 | −0.023963 | 0.001873 | −0.056372 | 0.016174 | −0.029141 | −0.024217 | 0.011942 |
| 75 | 0.066547 | −0.001425 | −0.035738 | −0.1014 | −0.025207 | −0.083698 | −0.014099 | −0.019946 | −0.03975 | −0.000259 | 0.065522 | 0.051679 | 0.005 | −0.042878 |
| 76 | −0.002621 | 0.023484 | −0.048397 | −0.001232 | −0.064617 | −0.009073 | −0.015269 | −0.003965 | 0.001921 | −0.011001 | −0.025438 | −0.073995 | −0.02902 | −0.033515 |
| 77 | −0.021977 | −0.054625 | −0.0913 | 0.15327 | −0.016107 | 0.166313 | −0.073498 | 0.025994 | 0.029781 | −0.121628 | −0.016249 | 0.086812 | 0.134516 | 0.190717 |
| 78 | −0.033613 | −0.074701 | 0.097187 | 0.062899 | 0.072621 | −0.040997 | −0.00331 | 0.009635 | 0.028967 | −0.046895 | 0.016516 | 0.046445 | 0.019976 | 0.030402 |
| 79 | 0.001004 | −0.020205 | 0.083753 | 0.036539 | 0.049206 | −0.005093 | 0.079612 | 0.024673 | 0.010868 | 0.108943 | −0.010332 | −0.057176 | −0.072863 | −0.001613 |
| 80 | 0.004131 | 0.037932 | 0.006014 | 0.01337 | 0.000078 | 0.048008 | −0.001659 | −0.008887 | 0.020327 | −0.080719 | 0.037429 | −0.010641 | 0.025388 | 0.024705 |
| 81 | 0.002433 | −0.003441 | 0.03377 | 0.062406 | 0.030181 | 0.013078 | −0.016547 | 0.028497 | −0.030053 | −0.025868 | 0.015887 | −0.049516 | 0.012813 | −0.007928 |
| 82 | −0.003618 | 0.046372 | −0.072988 | 0.061643 | 0.029843 | 0.046982 | 0.008316 | 0.047995 | 0.04993 | 0.092921 | 0.035745 | 0.010326 | 0.137906 | 0.075666 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 83 | 0.024282 | 0.013817 | 0.029955 | −0.051742 | 0.017134 | 0.016997 | 0.016279 | 0.014658 | −0.063488 | 0.000762 | −0.045253 | −0.074057 | −0.056382 | −0.136178 |
| 84 | −0.121694 | −0.117833 | −0.051611 | 0.079884 | 0.037826 | 0.075077 | 0.030958 | −0.011262 | −0.021435 | −0.113636 | 0.062006 | −0.000927 | 0.036089 | −0.027445 |
| 85 | −0.055546 | −0.021727 | −0.216701 | −0.060046 | −0.069456 | 0.152367 | −0.019076 | 0.036183 | −0.043216 | 0.012349 | −0.012975 | 0.066557 | 0.003634 | 0.092988 |
| 86 | 0.000831 | 0.008067 | 0.080577 | 0.06689 | 0.049533 | −0.033529 | 0.027972 | −0.041342 | 0.021606 | 0.026427 | −0.031871 | −0.047422 | 0.04926 | 0.006194 |
| 87 | 0.067049 | 0.083984 | −0.039051 | −0.079048 | 0.003489 | −0.039025 | −0.040017 | −0.094141 | 0.009156 | −0.065899 | −0.009763 | −0.028817 | −0.022461 | −0.031625 |
| 88 | −0.048694 | −0.030556 | −0.051127 | −0.019232 | 0.02643 | 0.036263 | 0.050626 | −0.022466 | 0.018653 | −0.051225 | 0.002756 | 0.059427 | −0.03829 | −0.025887 |
| 89 | 0.059197 | 0.048283 | −0.071412 | 0.017028 | −0.024652 | −0.069837 | −0.059296 | 0.021081 | −0.044794 | 0.014 | −0.015028 | 0.083376 | 0.000129 | −0.046026 |
| 90 | −0.085473 | −0.141664 | 0.00064 | −0.080442 | −0.078801 | −0.033335 | −0.032331 | 0.083214 | 0.085284 | 0.016745 | −0.053307 | 0.000781 | 0.125385 | 0.02244 |
| 91 | 0.021739 | 0.028766 | 0.118361 | 0.026507 | 0.008956 | −0.060289 | −0.006512 | −0.05591 | 0.06419 | −0.092311 | 0.026216 | −0.019117 | −0.080476 | −0.062478 |
| 92 | 0.002973 | −0.007996 | −0.022807 | 0.023093 | −0.047235 | 0.000916 | −0.070035 | −0.002739 | −0.035899 | 0.085202 | −0.071869 | 0.045285 | −0.0248 | 0.053468 |
| 93 | 0.000887 | −0.014295 | −0.004965 | 0.037456 | 0.019024 | −0.011783 | 0.020178 | −0.001406 | 0.019685 | 0.074074 | −0.007546 | 0.014223 | −0.001383 | 0.053488 |
| 94 | 0.062402 | 0.002783 | −0.085619 | −0.014439 | 0.014533 | −0.005056 | 0.008704 | 0.038478 | −0.016638 | 0.026493 | 0.014826 | −0.055833 | −0.011178 | −0.108092 |
| 95 | −0.108423 | −0.064005 | 0.025222 | 0.035311 | 0.008726 | −0.009804 | −0.001634 | −0.016322 | −0.008779 | 0.003071 | −0.023743 | −0.048888 | −0.053301 | −0.062178 |
| 96 | −0.008343 | −0.052677 | −0.022319 | −0.058056 | 0.001659 | 0.028284 | −0.014661 | −0.019353 | 0.016144 | −0.008161 | −0.027609 | −0.028979 | 0.0068 | 0.06546 |
| 97 | −0.02606 | −0.022845 | −0.000491 | −0.011451 | 0.003338 | −0.007053 | −0.049391 | 0.141803 | −0.004509 | 0.268736 | 0.041115 | 0.035975 | −0.030905 | −0.075962 |
| 98 | −0.010787 | 0.047073 | −0.098689 | −0.025181 | 0.084599 | 0.028508 | 0.088266 | −0.096826 | −0.020908 | −0.002292 | 0.008103 | −0.041628 | −0.039276 | −0.014833 |
| 99 | −0.07988 | −0.024053 | −0.022687 | 0.000917 | −0.007849 | −0.003611 | 0.022885 | −0.004923 | −0.046048 | 0.095479 | 0.023615 | 0.043971 | −0.032063 | 0.024374 |
| 100 | −0.09244 | −0.030395 | 0.026843 | −0.012905 | −0.035115 | −0.020328 | −0.009768 | −0.116755 | 0.047081 | −0.07051 | −0.021997 | 0.039688 | 0.09308 | 0.07846 |
| 101 | 0.067222 | 0.007357 | 0.029103 | −0.051758 | 0.037349 | 0.003896 | 0.040465 | 0.060191 | −0.031259 | −0.072308 | 0.01739 | 0.004792 | −0.005701 | −0.013629 |
| 102 | 0.053255 | 0.055552 | −0.038133 | −0.008119 | 0.018723 | −0.036259 | 0.039904 | −0.102701 | −0.028518 | 0.054546 | −0.001902 | −0.008111 | −0.012483 | 0.019261 |
| 103 | 0.036153 | 0.017121 | 0.033792 | 0.005352 | −0.009938 | 0.02158 | −0.041583 | −0.010002 | 0.023987 | −0.056428 | 0.029393 | 0.036753 | −0.029852 | −0.0033 |
| 104 | 0.008802 | −0.006442 | −0.043298 | 0.048004 | −0.011787 | 0.017234 | 0.021969 | 0.026991 | −0.032385 | 0.077309 | −0.000424 | 0.005126 | −0.017017 | −0.037463 |
| 105 | −0.038177 | −0.055731 | −0.047364 | 0.025555 | −0.007191 | −0.041679 | −0.040512 | −0.031168 | 0.001928 | 0.08534 | 0.016616 | 0.074406 | −0.005474 | −0.044265 |
| 106 | −0.053602 | −0.050698 | 0.071232 | −0.02875 | −0.025506 | −0.046197 | −0.067408 | −0.105995 | −0.022124 | −0.085294 | 0.039038 | 0.018202 | 0.003261 | 0.002597 |
| 107 | 0.015434 | 0.044842 | −0.034671 | 0.04436 | −0.034398 | 0.017333 | −0.055965 | 0.02804 | 0.052964 | −0.035278 | −0.046169 | −0.038358 | 0.028816 | −0.053924 |
| 108 | 0.03632 | −0.002561 | 0.000503 | −0.007278 | 0.026986 | −0.052637 | 0.016898 | −0.034624 | 0.033391 | 0.012324 | −0.024035 | 0.033035 | −0.001411 | −0.013649 |
| 109 | 0.006922 | 0.024462 | 0.023609 | 0.012108 | 0.042709 | −0.021484 | −0.01393 | −0.060048 | 0.002461 | −0.077257 | 0.02448 | 0.012917 | 0.024756 | 0.000886 |
| 110 | −0.015794 | −0.012254 | 0.007302 | 0.032339 | 0.015562 | 0.029567 | 0.011244 | 0.003817 | −0.010082 | 0.039278 | 0.011937 | −0.026198 | −0.040445 | −0.068443 |
| 111 | −0.049452 | −0.03871 | −0.056577 | −0.059695 | −0.036412 | 0.036899 | −0.082479 | 0.016617 | −0.035982 | 0.089389 | −0.020053 | −0.004011 | 0.053473 | 0.002129 |
| 112 | −0.029556 | −0.008732 | 0.004494 | 0.025082 | 0.009065 | 0.040004 | −0.023579 | 0.022309 | −0.049903 | −0.010832 | 0.007572 | −0.018216 | 0.029524 | 0.015579 |
| 113 | −0.004692 | −0.007731 | −0.00559 | −0.014203 | −0.012757 | 0.0056 | −0.024516 | 0.043042 | −0.040271 | −0.090187 | 0.020635 | 0.067371 | −0.025761 | −0.024011 |
| 114 | 0.022168 | 0.023952 | −0.040399 | −0.045394 | 0.046835 | 0.06059 | 0.085092 | −0.003053 | −0.024049 | 0.073285 | −0.003174 | 0.008578 | −0.015207 | −0.014529 |
| 115 | 0.03223 | 0.038421 | −0.042546 | −0.013068 | −0.031727 | 0.100944 | −0.065763 | −0.030926 | −0.001794 | 0.02933 | 0.027824 | −0.014552 | −0.007504 | 0.027371 |
| 116 | −0.01356 | −0.01633 | −0.037245 | −0.030647 | 0.033876 | 0.041572 | 0.049526 | 0.027451 | −0.013022 | 0.015784 | −0.023699 | 0.027046 | −0.012988 | 0.015812 |
| 117 | 0.137123 | 0.215717 | −0.013558 | 0.043594 | −0.078855 | −0.043668 | −0.054885 | 0.022932 | −0.03236 | 0.060391 | −0.010717 | 0.027248 | 0.065854 | 0.049894 |
| 118 | −0.046503 | −0.003845 | −0.00439 | 0.054429 | 0.01921 | −0.005276 | −0.02435 | −0.0131 | −0.010287 | −0.002303 | 0.030347 | 0.05717 | −0.030809 | −0.028334 |
| 119 | −0.007887 | −0.040431 | −0.025384 | −0.001279 | −0.007036 | −0.022833 | −0.033011 | −0.044065 | 0.01168 | 0.026493 | 0.022283 | 0.005616 | 0.070028 | −0.007247 |
| 120 | −0.0874 | −0.14837 | −0.079264 | −0.034995 | 0.044932 | 0.041271 | 0.020141 | −0.032009 | −0.037834 | −0.053426 | 0.004928 | 0.062366 | −0.050286 | −0.026134 |
| 121 | 0.018498 | −0.050834 | 0.02425 | 0.047405 | 0.026946 | −0.00844 | 0.015962 | 0.033274 | 0.075111 | −0.112717 | 0.067352 | 0.011576 | −0.01082 | −0.077639 |
| 122 | −0.006198 | −0.068226 | 0.019675 | −0.08499 | 0.015995 | −0.045752 | 0.022485 | 0.101345 | −0.032062 | 0.024272 | 0.022065 | −0.030943 | 0.016506 | −0.038604 |
| 123 | 0.034769 | 0.092522 | 0.011825 | 0.017226 | −0.042398 | −0.034451 | 0.025032 | −0.056631 | 0.029162 | −0.000581 | 0.044077 | 0.040236 | 0.018053 | 0.049862 |
| 124 | 0.044053 | 0.01924 | 0.023731 | −0.003387 | 0.000877 | 0.111977 | −0.005756 | 0.00588 | −0.117149 | −0.069718 | −0.029783 | −0.067677 | −0.048503 | −0.011298 |
| 125 | 0.046141 | 0.013807 | −0.024519 | −0.018262 | 0.023172 | −0.071082 | 0.015007 | 0.005814 | −0.017131 | −0.018784 | −0.066981 | −0.014356 | −0.030564 | 0.053545 |
| 126 | 0.038245 | −0.004429 | 0.038832 | 0.021769 | 0.080318 | 0.031906 | 0.073273 | −0.030832 | 0.06597 | −0.011181 | 0.032875 | −0.090868 | 0.005069 | 0.013115 |
| 127 | 0.032319 | 0.001492 | −0.019418 | 0.062649 | −0.023162 | 0.093052 | −0.045751 | −0.042096 | −0.031862 | 0.034228 | −0.0197 | 0.03658 | −0.069507 | −0.029702 |
| 128 | −0.019803 | −0.026501 | −0.056371 | −0.001547 | −0.00962 | 0.053233 | −0.001866 | 0.009553 | −0.061896 | −0.00768 | −0.014612 | 0.021742 | −0.057296 | −0.084673 |
| 129 | −0.017948 | −0.000258 | 0.040605 | 0.012738 | 0.035064 | −0.021434 | 0.047731 | −0.038335 | 0.049911 | 0.006278 | 0.031682 | 0.030144 | 0.008432 | −0.039278 |
| 130 | 0.040694 | 0.061172 | 0.042652 | 0.015694 | −0.012488 | −0.010149 | −0.01971 | 0.01809 | −0.014471 | 0.040462 | −0.015601 | −0.047271 | 0.012156 | −0.021134 |
| 131 | 0.017183 | 0.017157 | 0.035882 | −0.041239 | 0.0219 | −0.001635 | 0.035211 | −0.022999 | 0.016325 | −0.057482 | −0.03018 | −0.001161 | −0.0009 | 0.064134 |
| 132 | 0.008147 | −0.004534 | 0.003934 | 0.046185 | 0.040728 | 0.057699 | 0.012024 | −0.067401 | 0.018352 | −0.044241 | 0.039582 | 0.053475 | 0.05417 | −0.002787 |
| 133 | −0.008026 | 0.007504 | 0.031975 | −0.030645 | −0.015286 | −0.033086 | −0.010284 | 0.060654 | −0.081342 | 0.054143 | 0.03211 | 0.032827 | −0.019944 | 0.050339 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 134 | −0.0139 | 0.009123 | 0.064766 | −0.028122 | 0.000299 | 0.003089 | 0.003295 | −0.002237 | 0.034039 | −0.043553 | 0.060741 | 0.014413 | 0.057137 | 0.051877 |
| 135 | 0.023481 | 0.014839 | 0.007868 | −0.078166 | 0.007464 | 0.010253 | 0.039235 | −0.02502 | 0.034984 | −0.087981 | 0.044688 | 0.047176 | 0.00223 | 0.010256 |
| 136 | 0.019735 | 0.006587 | 0.000237 | 0.033472 | 0.077999 | 0.038895 | −0.017759 | 0.021805 | 0.00295 | 0.049637 | 0.01591 | 0.013507 | −0.012402 | −0.03152 |
| 137 | −0.034735 | −0.007439 | 0.010551 | 0.054909 | −0.017551 | −0.030098 | −0.013294 | −0.079533 | 0.031728 | 0.099511 | −0.004955 | −0.027611 | 0.047762 | 0.051392 |
| 138 | 0.017804 | 0.025721 | −0.018093 | 0.046327 | −0.022669 | −0.000766 | 0.022586 | −0.062099 | −0.050865 | −0.004347 | 0.016003 | −0.042447 | −0.05416 | 0.039045 |
| 139 | 0.007695 | 0.039559 | 0.015903 | −0.026271 | −0.027572 | 0.0169 | 0.002446 | −0:003276 | 0.04571 | −0.029682 | 0.007636 | −0.081234 | −0.004616 | 0.040045 |
| 140 | −0.008817 | −0.023419 | 0.009922 | −0.050879 | 0.003584 | −0.02897 | −0.014997 | −0.005816 | −0.031096 | −0.015215 | −0.034782 | −0.00288 | 0.001104 | 0.01634 |
| 141 | −0.019856 | 0.024884 | −0.024188 | −0.079353 | −0.033485 | −0.009013 | −0.026838 | 0.042754 | −0.011764 | −0.006741 | −0.063248 | −0.038534 | 0.009227 | 0.037102 |
| 142 | 0.02053 | 0.004698 | −0.018173 | 0.018793 | 0.029451 | 0.005326 | −0.043295 | −0.018766 | −0.000187 | 0.01094 | 0.005469 | 0.047675 | 0.050795 | −0.000142 |
| 143 | 0.010438 | 0.027622 | 0.013244 | −0.012732 | 0.048864 | 0.041797 | 0.048726 | −0.021854 | −0.02985 | 0.054206 | −0.016422 | −0.005497 | −0.040384 | −0.045588 |
| 144 | −0.001855 | 0.0164721 | −0.034751 | 0.017855 | 0.000792 | −0.026689 | 0.004611 | −0.019171 | −0.007406 | −0.066544 | −0.007802 | −0.019372 | −0.007046 | 0.04662 |
| 145 | 0.00571 | −0.045164 | −0.01717 | 0.020118 | 0.015171 | −0.011859 | −0.001474 | 0.046192 | 0.040113 | −0.050177 | 0.005432 | 0.014699 | 0.006634 | 0.002811 |
| 146 | −0.02769 | −0.008413 | −0.007532 | 0.026363 | −0.022758 | −0.010867 | −0.016363 | −0.013158 | 0.029757 | 0.025188 | 0.001629 | 0.008044 | 0.049885 | −0.019073 |
| 147 | 0.015299 | −0.005877 | −0.062045 | −0.023084 | 0.000602 | −0.03151 | −0.044791 | 0.010958 | 0.000579 | −0.05375 | −0.023921 | −0.039388 | 0.018057 | −0.010357 |
| 148 | −0.001751 | −0.006412 | −0.032282 | 0.040588 | −0.019012 | −0.004522 | −0.003764 | 0.041576 | −0.004154 | −0.069831 | 0.005230. | −0.028515 | 0.016065 | −0.056144 |
| 149 | 0.022387 | 0.004575 | 0.046806 | 0.027798 | 0.046316 | 0.029854 | 0.040709 | −0.024744 | −0.024088 | −0.047534 | 0.007203 | −0.015933 | −0.037393 | −0.038654 |
| 150 | −0.015791 | −0.011243 | 0.003535 | −0.00826 | −0.030712 | 0.006216 | 0.026392 | 0.030646 | 0.009774 | −0.006203 | 0.002417 | −0.028131 | 0.023191 | 0.004574 |
| 151 | −0.018336 | −0.009876 | 0.013729 | −0.004893 | 0.006968 | 0.01984 | −0.01113 | −0.032543 | −0.017046 | −0.044819 | 0.010492 | −0.015565 | 0.010821 | 0.022593 |
| 152 | −0.028572 | −0.014983 | −0.016861 | 0.01234 | −0.002698 | −0.000733 | 0.001134 | 0.029594 | −0.021958 | 0.059618 | 0.00409 | 0.029147 | 0.022002 | 0.029189 |
| 153 | −0.010562 | 0.008965 | −0.038247 | −0.011799 | 0.01447 | 0.006599 | 0.008025 | 0.033475 | −0.027496 | 0.020928 | 0.024407 | 0.040119 | 0.016273 | 0.008315 |
| 154 | 0.036686 | 0.01917 | −0.015818 | 0.03517 | 0.008457 | −0.017374 | −0.013667 | −0.014841 | 0.012053 | −0.007794 | 0.010834 | −0.026235 | 0.007042 | −0.022099 |
| 155 | −0.030402 | −0.006637 | 0.000384 | −0.012413 | −0.013098 | −0.024056 | 0.03581 | −0.053417 | 0.035808 | −0.015722 | 0.017814 | 0.010215 | 0.006293 | 0.037385 |
| 156 | 0.036982 | 0.006084 | 0.001498 | −0.011492 | −0.007595 | 0.02256 | −0.005302 | 0.059849 | −0.00361 | 0.088543 | 0.020093 | 0.057332 | 0.014007 | 0.008501 |
| 157 | −0.006919 | −0.037086 | 0.059901 | 0.020323 | 0.031507 | −0.016593 | 0.008518 | −0.029263 | 0.032866 | −0.021324 | −0.017743 | 0.048859 | −0.012368 | 0.074957 |
| 158 | −0.019978 | 0.000695 | 0.009496 | 0.037673 | 0.006654 | 0.017897 | 0.013898 | 0.012321 | 0.023443 | 0.030096 | −0.010268 | −0.008338 | −0.037344 | 0.028974 |
| 159 | 0.01492 | 0.021916 | −0.00812 | −0.013537 | −0.007115 | 0.031673 | −0.027866 | 0.011134 | 0.008739 | 0.003363 | −0.020735 | −0.022037 | −0.004413 | 0.055856 |
| 160 | 0.006878 | −0.005226 | 0.039653 | −0.003389 | 0.026207 | −0.057711 | 0.000162 | 0.013421 | 0.050746 | −0.049062 | −0.020643 | −0.005354 | 0.0255 | 0.048944 |
| 161 | 0.010263 | −0.01987 | −0.026333 | 0.003216 | −0.017726 | 0.013893 | 0.015399 | 0.003718 | 0.019586 | 0.021166 | 0.008257 | −0.004126 | 0.032544 | −0.000148 |
| 162 | 0.042218 | 0.069898 | 0.036037 | 0:024232 | 0.022141 | −0.02231 | −0.007597 | −0.041461 | 0.001819 | 0.064124 | 0.021699 | 0.012108 | −0.013496 | −0.00382 |
| 163 | −0.016253 | −0.00655 | −0.002472 | −0.072029 | 0.00485 | −0.008664 | −0.005175 | 0.043964 | −0.002154 | −0.045412 | 0.001906 | 0.002022 | −0.020254 | −0.0006 |
| 164 | −0.038067 | −0.006435 | 0.034031 | −0.019813 | −0.050453 | 0.052326 | 0.001606 | 0.007407 | −0.019135 | 0.036193 | −0.05622 | −0.029621 | −0.016682 | −0.046015 |
| 165 | 0.039872 | 0.032956 | −0.031029 | 0.040239 | −0.04032 | 0.016241 | −0.023724 | 0.030283 | −0.057074 | −0.088881 | −0.023011 | −0.036867 | −0.025647 | −0.021357 |
| 166 | −0.027558 | 0.014291 | 0.014506 | 0.02613 | 0.007861 | 0.01523 | −0.000373 | 0.041693 | −0.007757 | 0.063851 | 0.022068 | −0.014994 | 0.036986 | −0.008531 |
| 167 | −0.030379 | −0.034285 | −0.045319 | 0.00962 | −0.062593 | −0.04496 | 0.003865 | 0.042155 | 0.037955 | 0.047 | −0.026706 | −0.029009 | 0.019631 | 0.035688 |
| 168 | 0.016761 | −0.012316 | 0.046599 | −0.008506 | 0.0148 | −0.04247 | 0.017952 | 0.050597 | −0.011448 | 0.015353 | 0.016799 | −0.022677 | −0.00653 | −0.006215 |
| 169 | −0.022199 | −0.015575 | −0.004859 | −0.034473 | −0.014706 | 0.006199 | −0.005196 | 0.001649 | −0.030653 | 0.001238 | −0.003655 | 0.002045 | −0.031624 | −0.033459 |
| 170 | −0.009367 | −0.009227 | −0.005572 | 0.014019 | 0.014857 | 0.051588 | 0.023174 | 0.019823 | −0.034018 | −0.01593 | 0.020613 | −0.013405 | −0.012642 | −0.005657 |
| 171 | −0.014795 | 0.012911 | −0.021795 | −0.002952 | −0.015847 | −0.001755 | −0.003258 | −0.022344 | −0.01568 | 0.03419 | −0.020001 | 0.016317 | 0.004756 | 0.017658 |
| 172 | −0.009824 | 0.004321 | −0.03128 | −0.041724 | −0.03208 | 0.022825 | −0.018323 | −0.024894 | 0.000222 | −0.021802 | −0.018355 | 0.017428 | −0.004543 | −0.016478 |
| 173 | −0.008228 | 0.000512 | −0.055147 | −0.00876 | 0.006211 | −0.006847 | −0.016737 | −0.009688 | −0.017717 | 0.013627 | −0.028733 | −0.021277 | 0.02168 | 0.000979 |
| 174 | −0.002029 | 0.020605 | 0.004167 | −0.038543 | −0.0314 | −0.061457 | −0.052395 | −0.008626 | −0.033783 | 0.005721 | −0.027737 | 0.014656 | −0.009366 | −0.031774 |
| 175 | −0.018809 | −0.016319 | −0.019351 | 0.045078 | −0.003434 | −0.011455 | −0.000198 | 0.029737 | −0.003614 | 0.057015 | 0.011342 | 0.00473 | −0.042624 | −0.049374 |
| 176 | 0.000925 | 0.004758 | 0.049288 | −0.002345 | −0.001891 | 0.0258 | 0.021668 | 0.035132 | 0.065778 | 0.03649 | 0.012521 | 0.050491 | −0.009537 | 0.037145 |
| 177 | −0.044199 | −0.046198 | −0.010376 | 0.016187 | 0.017787 | −0.009418 | 0.023603 | −0.028501 | −0.006142 | 0.00507 | 0.069805 | 0.024391 | 0.010083 | 0.021571 |
| 178 | 0.004546 | −0.010299 | −0.009303 | −0.024943 | 0.009785 | −0.005484 | −0.006942 | −0.016542 | −0.002924 | −0.027667 | −0.00631 | −0.015659 | −0.035352 | −0.050695 |
| 179 | 0.013911 | 0.027246 | −0.009728 | 0.041979 | −0.021457 | −0.003181 | −0.014323 | 0.002721 | −0.002603 | 0.04347 | −0.000433 | 0.017183 | −0.003463 | −0.022525 |
| 18 0 | 0.01511 | −0.01919 | 0.016922 | 0.015781 | 0.003117 | −0.019729 | −0.027805 | 0.039441 | 0.019368 | −0.007628 | 0.010086 | 0.031076 | 0.023166 | −0.003358 |
| 181 | 0.02747 | 0.028157 | 0.015525 | 0.021804 | −0.006245 | −0.032867 | −0.020754 | 0.005392 | 0.01167 | 0.021009 | 0.012798 | 0.024112 | 0.019634 | 0.003743 |
| 182 | 0.03485 | 0.028133 | 0.003047 | 0.051038 | 0.038513 | 0.022227 | 0.036725 | 0.004817 | −0.000569 | 0.038132 | 0.021501 | −0.015345 | −0.008413 | −0.025646 |
| 183 | 0.020226 | 0.021898 | −0.001214 | 0.047596 | 0.007809 | 0.00503 | 0.02594 | −0.018095 | 0.001822 | 0.055488 | −0.014661 | −0.022154 | −0.00857 | 0.006735 |
| 184 | −0.0146 | −0.017094 | 0.000147 | −0.012554 | 0.027906 | 0.016944 | −0.008453 | 0.008725 | −0.021212 | 0.009144 | −0.015524 | −0.02444 | 0.033179 | −0.01417 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 185 | −0.022878 | −0.026867 | 0.078738 | −0.000306 | 0.000381 | −0.000879 | 0.008457 | −0.002479 | 0.07464 | −0.026023 | −0.0176 | 0.020515 | −0.006088 | −0.004267 |
| 186 | −0.001648 | −0.00079 | 0.05397 | −0.020308 | −0.02487 | −0.027922 | 0.019931 | −0.021671 | 0.005328 | 0.027443 | −0.015964 | 0.023142 | 0.018282 | 0.066894 |
| 187 | 0.002097 | −0.012673 | −0.021585 | −0.018278 | 0.016831 | 0.014913 | 0.032927 | 0.073732 | 0.015317 | 0.013978 | 0.013611 | −0.020695 | −0.01063 | −0.015594 |
| 188 | 0.004308 | 0.001502 | −0.008207 | 0.00075 | −0.0045 | −0.000931 | −0.003913 | −0.001488 | −0.009787 | −0.0498 | 0.028253 | 0.020357 | −0.013768 | −0.028345 |
| 189 | 0.025516 | 0.024974 | 0.005508 | 0.003696 | 0.00535 | 0.001513 | −0.013394 | −0.0463 | −0.003657 | −0.067661 | 0.002765 | 0.003697 | −0.00935 | 0.010264 |
| 190 | 0.000364 | 0.001783 | 0.005384 | −0.002989 | −0.005961 | −0.049395 | −0.035174 | −0.049102 | −0.034278 | −0.032862 | 0.007946 | 0.036635 | −0.0165 | 0.021419 |
| 191 | −0.007531 | −0.025717 | −0.03169 | −0.016347 | −0.022698 | 0.005995 | −0.023214 | −0.01969 | −0.041168 | −0.035715 | 0.02137 | 0.044565 | 0.012201 | −0.034414 |
| 192 | −0.025845 | 0.009609 | 0.026555 | 0.039184 | −0.01746 | 0.001535 | −0.003927 | −0.008551 | −0.025266 | 0.051393 | 0.015448 | 0.00846 | 0.008143 | −0.012152 |
| 193 | −0.034931 | −0.034712 | −0.050203 | 0.004002 | 0.01112 | 0.05248 | 0.035897 | 0.034058 | −0.011874 | 0.0014 | 0.024293 | 0.009581 | 0.00125 | −0.024223 |
| 194 | −0.04213 | −0.072898 | −0.032344 | 0.026905 | 0.002157 | 0.005863 | −0.006991 | 0.008185 | 0.009108 | −0.007159 | 0.01057 | −0.017808 | 0.059233 | 0.001109 |
| 195 | 0.024902 | 0.00435 | 0.035881 | 0.016811 | 0.023775 | −0.022828 | 0.004789 | 0.025703 | 0.015453 | 0.050421 | 0.00984 | −0.022452 | 0.005824 | 0.005928 |
| 196 | 0.011379 | −0.007346 | 0.03253 | 0.033047 | 0.03221 | 0.001303 | 0.012465 | 0.016333 | −0.0172 | 0.014118 | 0.004041 | −0.004102 | −0.013316 | −0.070589 |
| 197 | 0.002213 | 0.004487 | 0.028825 | −0.023497 | −0.012938 | −0.014253 | −0.003175 | 0.034362 | −0.012144 | −0.035914 | 0.005144 | 0.011772 | 0.029691 | −0.023431 |
| 198 | 0.025033 | 0.022434 | 0.024687 | −0.018413 | 0.042633 | 0.01956 | 0.026868 | 0.015597 | 0.022517 | −0.021992 | 0.011001 | −0.043351 | 0.006819 | 0.034946 |
| 199 | 0.031492 | 0.039405 | 0.026239 | −0.000974 | 0.019228 | 0.008676 | 0.033335 | −0.028724 | 0.032608 | −0.018381 | 0.039341 | 0.038849 | 0.012224 | 0.064945 |
| 200 | 0.026196 | 0.026949 | 0.002181 | −0.044699 | −0.002308 | 0.030627 | 0.030005 | −0.024634 | 0.045053 | 0.003148 | −0.010752 | 0.00051 | −0.03207 | 0.008904 |
| 201 | 0.015135 | 0.028087 | 0.028341 | 0.005835 | 0.001159 | 0.009076 | −0.007195 | −0.006217 | −0.004833 | −0.023812 | 0.013517 | 0.014943 | 0.006991 | −0.020156 |
| 202 | 0.009911 | 0.00781 | −0.004766 | 0.016465 | 0.020631 | 0.036285 | −0.002749 | 0.043232 | 0.015169 | 0.039016 | 0.007267 | −0.000754 | 0.00383 | −0.046675 |
| 203 | −0.019075 | −0.003255 | 0.01595 | 0:012691 | 0.00384 | −0.046418 | 0.004938 | 0.019565 | −0.015345 | 0.012931 | −0.034444 | −0.012346 | 0.008069 | 0.04474 |
| 204 | −0.02568 | −0.000322 | −0.045063 | 0.046545 | −0.016501 | 0.00108 | 0.001561 | 0.029053 | −0.017177 | 0.00592 | −0.007928 | 0.003501 | 0.018848 | 0.058875 |
| 205 | 0.015736 | −0.015681 | 0.033723 | −0.019354 | 0.001121 | −0.022857 | 0.016112 | 0.003407 | 0.037851 | −0.055557 | −0.004246 | −0.00141 | 0.002125 | 0.008659 |
| 206 | 0.03077 | 0.01973 | −0.014732 | −0.022377 | −0.000306 | 0.013663 | −0.01191 | 0.0342 | 0.000561 | −0.054116 | −0.023361 | −0.001104 | 0.061034 | −0.01735 |
| 207 | −0.016646 | −0.031403 | 0.019624 | 0.021711 | 0.013208 | −0.037572 | −0.012158 | −0.029744 | 0.046245 | 0.032817 | −0.004033 | 0.019028 | 0.051249 | −0.024352 |
| 208 | −0.024101 | −0.015894 | −0.018012 | 0.00293 | −0.006677 | −0.027799 | −0.030407 | −0.009915 | 0.007583 | 0.027104 | −0.023634 | −0.049773 | −0.001426 | −0.058417 |
| 209 | −0.019366 | −0.020575 | 0.008464 | −0.039435 | 0.012724 | 0.010362 | −0.007256 | −0.005628 | 0.023425 | −0.028874 | 0.007813 | 0.024042 | 0.033481 | −0.028273 |
| 210 | 0.007858 | −0.003292 | −0.008503 | −0.012476 | 0.03289 | 0.010423 | 0.017548 | 0.022391 | 0.015109 | 0.024393 | 0.031075 | −0.002711 | −0.004758 | 0.014893 |
| 211 | −0.016518 | −0.026551 | −0.017176 | −0.013012 | −0.011529 | 0.03511 | 0.003371 | −0.061516 | 0.02992 | −0.037861 | 0.007256 | 0.023449 | 0.011157 | 0.018874 |
| 212 | −0.016993 | 0.000188 | −0.060669 | 0.011893 | 0.008873 | −0.005103 | 0.002801 | 0.001903 | −0.023721 | −0.012284 | −0.006988 | −0.028068 | 0.001288 | 0.003715 |
| 213 | 0.020217 | 0.02688 | −0.000019 | 0.010866 | 0.047889 | 0.002954 | 0.042144 | −0.026606 | 0.047341 | −0.015068 | 0.018436 | 0.008068 | −0.039211 | 0.010165 |
| 214 | 0.013139 | 0.012875 | 0.024038 | 0.045576 | −0.026776 | 0.014767 | −0.032099 | −0.03707 | −0.017781 | −0.012397 | −0.015808 | 0.014925 | −0.01121 | −0.018895 |
| 215 | 0.019968 | 0.000365 | −0.060362 | 0.017766 | 0.057242 | 0.087361 | 0.080787 | −0.018711 | −0.012718 | −0.007448 | 0.005871 | −0.03844 | −0.087426 | −0.050713 |
| 216 | 0.010104 | 0.024168 | 0.000398 | 0.003426 | 0.050092 | 0.020169 | 0.032358 | 0.043886 | 0.033595 | −0.002045 | 0.014518 | −0.035797 | 0.034003 | 0.048063 |
| 217 | 0.002439 | 0.003197 | 0.040155 | 0.016952 | 0.018752 | 0.005939 | −0.003377 | −0.031861 | 0.013224 | −0.006319 | 0.011455 | −0.036462 | −0.052928 | −0.049252 |
| 218 | −0.001561 | 0.005526 | −0.038874 | −0.013879 | −0.019715 | 0.006262 | −0.022566 | 0.037505 | −0.000636 | 0.014694 | 0.0257 | 0.007034 | 0.027338 | −0.008441 |
| 219 | 0.010806 | 0.02401 | 0.002572 | −0.006563 | 0.010586 | 0.042388 | 0.018557 | 0.017477 | 0.006957 | 0.044729 | 0.007552 | −0.020901 | −0.020633 | −0.003791 |
| 220 | 0.011568 | 0.014474 | 0.039981 | 0.047468 | 0.031206 | −0.033509 | 0.003538 | 0.025 | 0.016642 | 0.054069 | −0.012673 | −0.026897 | 0.020609 | −0.014998 |
| 221 | 0.031344 | 0.02414 | −0.014219 | 0.004351 | 0.016165 | −0.002184 | 0.016951 | −0.001135 | 0.018847 | 0.032827 | −0.000243 | −0.012363 | −0.018613 | −0.024644 |
| 222 | 0.021604 | 0.020961 | −0.018209 | −0.016181 | −0.005721 | −0.044878 | −0.01772 | −0.007689 | −0.011434 | 0.013255 | −0.024823 | −0.033497 | 0.005661 | 0.004451 |
| 223 | 0.01891 | 0.018521 | −0.050648 | 0.001209 | −0.012974 | −0.034428 | −0.011974 | 0.013855 | −0.036748 | −0.011126 | −0.026699 | −0.028717 | −0.027445 | 0.007489 |
| 224 | −0.018229 | −0.020324 | 0.03783 | −0.033509 | −0.002317 | −0.007094 | −0.017332 | 0.042199 | −0.003436 | −0.002871 | 0.006474 | 0.015204 | −0.015706 | 0.013282 |
| 225 | −0.017587 | −0.010301 | 0.0325 | −0.029308 | 0.016336 | 0.002985 | 0.003693 | 0.008672 | −0.013265 | −0.028132 | 0.013442 | 0.009743 | −0.016453 | 0.016537 |
| 226 | 0.036965 | 0.04483 | −0.011037 | −0.006213 | 0.03379 | 0.007903 | 0.060403 | 0.003038 | 0.011813 | −0.006109 | 0.026634 | 0.001342 | −0.022784 | −0.020828 |
| 227 | 0.026655 | 0.040005 | 0.016509 | −0.022584 | 0.001738 | −0.043563 | 0.01701 | −0.0396 | 0.01097 | 0.008098 | −0.01096 | −0.036291 | −0.003665 | 0.017635 |
| 228 | −0.01845 | −0.011066 | −0.001049 | −0.000939 | −0.003293 | −0.020127 | 0.030446 | 0.009265 | 0.033762 | 0.016416 | 0.030076 | 0.008859 | 0.0242 | −0.018782 |
| 229 | −0.004035 | −0.00229 | 0.003102 | 0.029475 | −0.020262 | 0.035204 | −0.062622 | −0.018713 | −0.02316 | −0.010579 | −0.014956 | 0.000127 | −0.00716 | 0.009043 |
| 230 | 0.010733 | −0.000148 | 0.007473 | 0.013828 | −0.056771 | −0.057414 | −0.023993 | 0.031048 | −0.000511 | −0.018972 | 0.004296 | 0.008787 | 0.050387 | 0.018555 |
| 231 | 0.037946 | 0.044832 | −0.036003 | −0.054788 | −0.008252 | −0.01853 | −0.046349 | −0.022458 | −0.068745 | 0.004674 | −0.012136 | 0.01357 | −0.025455 | 0.01609 |
| 232 | 0.020304 | −0.007846 | 0.048499 | 0.04743 | 0.040723 | −0.00953 | 0.03048 | 0.020136 | −0.053081 | 0.011838 | −0.019476 | 0.044479 | −0.006228 | 0.010757 |
| 233 | 0.048475 | 0.062949 | −0.027704 | −0.005674 | −0.012233 | 0.045229 | −0.005223 | −0.008999 | −0.038114 | 0.065089 | −0.012157 | 0.010043 | −0.011822 | 0.025371 |
| 234 | 0.016874 | 0.019559 | −0.021526 | −0.001996 | 0.036303 | 0.041846 | −0.005337 | −0.007739 | 0.004655 | 0.011597 | −0.012889 | 0.024947 | 0.012453 | 0.027603 |
| 235 | −0.02011 | −0.057106 | 0.000649 | −0.014695 | 0.00044 | 0.014714 | 0.006211 | 0.027944 | 0.027165 | −0.038117 | −0.008803 | −0.007871 | 0.032105 | −0.01649 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 236 | 0.003067 | −0.006395 | −0.064703 | 0.020331 | 0.020898 | 0.043687 | 0.006906 | −0.018699 | −0.033188 | 0.025085 | −0.027682 | 0.012747 | −0.026599 | −0.020769 |
| 237 | −0.049423 | −0.034698 | −0.003952 | −0.014534 | −0.022379 | −0.006121 | 0.013069 | 0.016907 | −0.006641 | −0.061431 | 0.020772 | 0.041214 | 0.037295 | 0.005009 |
| 238 | −0.010366 | −0.027913 | 0.042797 | 0.024605 | −0.008278 | 0.003285 | 0.01055 | −0.01237 | −0.019029 | 0.011083 | −0.024094 | −0.000189 | −0.0342 | 0.003319 |
| 239 | 0.004011 | −0.019771 | 0.034218 | 0.00625 | 0.008585 | 0.012213 | 0.000131 | −0.029552 | −0.020342 | 0.017493 | −0.020642 | −0.015775 | −0.041866 | −0.02873 |
| 240 | 0.000374 | 0.001564 | −0.030947 | 0.025185 | −0.004625 | 0.004867 | −0.024275 | 0.001394 | 0.003404 | 0.002165 | 0.034532 | 0.021143 | −0.004412 | −0.007431 |
| 241 | 0.022719 | −0.007015 | 0.030897 | −0.012482 | 0.026133 | 0.026004 | −0.000468 | 0.025129 | −0.021424 | 0.020187 | 0.011601 | 0.024331 | −0.019565 | 0.045414 |
| 242 | −0.006218 | −0.01159 | −0.042993 | 0.012676 | −0.013104 | 0.01806 | −0.010665 | 0.021139 | −0.011757 | 0.058812 | −0.030229 | −0.018415 | 0.010155 | −0.005464 |
| 243 | −0.025658 | −0.03012 | −0.008455 | −0.038392 | −0.010007 | −0.020951 | 0.014914 | 0.023963 | −0.001833 | −0.005605 | −0.017635 | −0.010085 | −0.036137 | −0.014175 |
| 244 | 0.010891 | −0.02437 | 0.036838 | −0.015678 | 0.05562 | 0.004153 | 0.050814 | −0.023624 | 0.008845 | −0.008106 | 0.043569 | 0.035355 | −0.019859 | −0.031073 |
| 245 | 0.007626 | 0.036172 | −0.003656 | −0.006348 | −0.012511 | −0.005105 | −0.034827 | −0.078902 | −0.018428 | 0.021643 | 0.015503 | −0.007247 | −0.0288 | −0.031738 |
| 246 | −0.004533 | −0.007202 | −0.028563 | −0.004005 | −0.018099 | 0.005164 | −0.025252 | 0.001817 | 0.015214 | 0.043809 | −0.00947 | −0.011304 | 0.047899 | 0.003782 |
| 247 | 0.008326 | −0.00807 | −0.008956 | −0.001532 | −0.014438 | −0.014177 | 0.003812 | −0.019591 | −0.021487 | 0.017232 | 0.008846 | 0.036362 | −0.041124 | 0.0049 |
| 248 | 0.002954 | 0.00051 | 0.017737 | −0.003264 | 0.004423 | −0.027701 | 0.026134 | 0.02052 | 0.025144 | 0.005889 | 0.035031 | 0.026142 | 0.00576 | −0.01482 |
| 249 | 0.021166 | 0.029826 | 0.035724 | 0.002519 | −0.006499 | −0.001717 | −0.033417 | 0.020882 | 0.043366 | 0.01587 | 0.007194 | 0.043561 | 0.045817 | 0.052086 |
| 250 | 0.009996 | −0.04114 | −0.05051 | −0.006289 | 0.011244 | 0.033247 | −0.011831 | 0.044812 | −0.020592 | 0.028849 | −0.015378 | −0.012364 | 0.015266 | −0.002299 |
| 251 | −0.02706 | −0.073416 | 0.030915 | 0.022472 | 0.035221 | −0.00089 | 0.02067 | 0.030866 | −0.018365 | 0.007588 | 0.019739 | −0.025001 | −0.009252 | −0.070199 |
| 252 | −0.005869 | 0.021059 | 0.038115 | −0.009795 | −0.01747 | −0.020498 | −0.00194 | 0.003484 | 0.008944 | −0.000518 | 0.010731 | 0.029257 | −0.021331 | 0.011406 |
| 253 | −0.02402 | −0.042119 | −0.000655 | 0.013439 | 0.008296 | −0.039352 | 0.001194 | −0.010824 | −0.012479 | 0.008086 | −0.021414 | −0.007519 | −0.034537 | −0.07538 |
| 254 | −0.005656 | 0.01881 | 0.030615 | −0.037138 | 0.010507 | −0.012021 | 0.022464 | −0.03572 | −0.029694 | −0.04885 | 0.03259 | 0.029819 | 0.023287 | 0.055662 |
| 255 | 0.010594 | −0.011863 | 0.009339 | −0.024707 | 0.021998 | −0.01677 | 0.034035 | 0.001601 | 0.019752 | −0.015968 | 0.033388 | −0.009291 | 0.02085 | 0.011216 |
| 256 | −0.001964 | 0.015184 | −0.016986 | −0.01109 | −0.022958 | 0.01784 | −0.038904 | 0.024786 | 0.007987 | −0.Q00453 | 0.000323 | 0.004798 | 0.028835 | 0.038206 |
| 257 | 0.017195 | 0.03117 | −0.009047 | 0.029428 | −0.026399 | 0.032797 | −0.006068 | −0.000215 | 0.018758 | −0.020121 | −0.054048 | −0.041377 | 0.029123 | 0.05387 |
| 258 | 0.006242 | 0.029044 | −0.013725 | −0.012169 | 0.010893 | −0.008166 | 0.021987 | −0.049193 | 0.006857 | −0.078316 | 0.040796 | 0.009811 | −0.017801 | 0.001732 |
| 259 | 0.003625 | 0.007952 | −0.028693 | 0.02461 | −0.009467 | 0.021045 | −0.011082 | −0.012094 | −0.0078 | −0.014433 | 0.013275 | −0.007652 | −0.014319 | −0.02541 |
| 260 | 0.008909 | 0.044267 | −0.018667 | 0.001196 | 0.00927 | 0.040357 | −0.004909 | −0.049242 | −0.04976 | −0.021532 | 0.00119 | 0.030043 | −0.032986 | 0.029879 |
| 261 | −0.003225 | 0.023164 | 0.029901 | 0.018807 | −0.003579 | −0.030494 | 0.009252 | 0.026768 | −0.008226 | −0.02557 | 0.012162 | −0.02338 | −0.019464 | −0.029244 |
| 262 | 0.023559 | 0.055951 | −0.022545 | 0.025552 | −0.040628 | −0.035029 | −0.03657 | −0.022711 | −0.019965 | −0.011792 | −0.029709 | −0.028577 | 0.008123 | 0.006715 |
| 263 | 0.015428 | 0.054544 | −0.013686 | 0.011764 | −0.039183 | −0.050428 | −0.020886 | −0.011527 | 0.022337 | 0.015435 | −0.020036 | −0.028479 | 0.070845 | 0.019034 |
| 264 | 0.036777 | 0.005147 | 0.005588 | −0.039542 | 0.051123 | −0.009283 | 0.010929 | −0.013623 | 0.03254 | 0.009224 | 0.012344 | 0.012018 | 0.000546 | 0.024458 |
| 265 | 0.016434 | −0.011105 | −0.021106 | −0.028926 | 0.019928 | −0.004294 | 0.006656 | −0.006403 | −0.029528 | −0.074474 | 0.013882 | 0.002815 | −0.025211 | −0.000842 |
| 266 | −0.000516 | 0.005124 | −0.011344 | −0.015543 | −0.013776 | −0.00366 | −0.019465 | 0.021172 | −0.056862 | −0.040234 | −0.012981 | −0.018613 | −0.006846 | −0.022678 |
| 267 | −0.009715 | −0.002684 | 0.004761 | 0.007103 | 0.005426 | −0.026839 | −0.001348 | −0.006817 | −0.018275 | −0.001386 | 0.018157 | 0.048796 | −0.047291 | −0.034401 |
| 268 | 0.011157 | 0.016035 | −0.027121 | −0.011396 | 0.020693 | 0.002723 | 0.023373 | 0.015522 | −0.007532 | −0.017177 | −0.001877 | 0.010326 | 0.005832 | 0.017013 |
| 269 | 0.007019 | −0.006791 | 0.005478 | −0.006855 | 0.040719 | 0.004463 | 0.035197 | 0.017327 | 0.004268 | −0.009065 | −0.002431 | 0.001902 | −0.007879 | 0.027813 |
| 270 | 0.007304 | −0.008259 | 0.027924 | −0.053006 | 0.011009 | −0.064382 | 0.011206 | 0.047469 | 0.032911 | −0.013954 | 0.025831 | −0.036813 | 0.038998 | −0.031758 |
| 271 | 0.01085 | −0.023985 | 0.050879 | −0.015756 | 0.011887 | −0.007335 | 0.047026 | −0.021944 | 0.011225 | −0.004928 | 0.018151 | 0.019407 | 0.041796 | 0.014724 |
| 272 | 0.017698 | 0.001184 | −0.017056 | 0.005078 | −0.022685 | −0.016027 | −0.029579 | −0.041797 | 0.020476 | −0.006635 | 0.008292 | 0.02316 | −0.016375 | 0.02448 |
| 273 | 0.003636 | 0.025762 | 0.001611 | −0.012301 | −0.076252 | −0.065104 | −0.049297 | 0.000458 | 0.001044 | −0.023111 | 0.011998 | −0.000076 | 0.02713 | 0.031578 |
| 274 | −0.000283 | 0.011764 | 0.019871 | −0.012542 | −0.078835 | −0.058622 | −0.041987 | 0.026319 | 0.011264 | −0.019488 | 0.020308 | 0.003426 | 0.023576 | 0.018403 |
| 275 | 0.007896 | −0.00954 | 0.024496 | −0.041428 | −0.011238 | −0.112541 | 0.031704 | 0.030801 | 0.028718 | 0.01724 | 0.025307 | −0.05454 | 0.017488 | −0.041778 |
| 276 | −0.000086 | 0.009247 | −0.025108 | 0.042353 | 0.00684 | 0.013669 | −0.026859 | 0.00316 | −0.001826 | 0.007759 | −0.021638 | 0.020363 | −0.00964 | 0.012591 |
| 277 | −0.005421 | 0.002717 | 0.000329 | −0.025746 | −0.000333 | −0.018043 | −0.011578 | 0.018275 | 0.005163 | 0.007572 | −0.014483 | −0.015494 | −0.020247 | −0.001914 |
| 278 | 0.005758 | 0.048737 | −0.005312 | 0.013659 | −0.005813 | −0.00061 | −0.012094 | −0.041636 | −0.008775 | 0.042058 | −0.018804 | −0.015504 | −0.04556 | 0.008243 |
| 279 | 0.007252 | −0.027752 | 0.042369 | 0.019116 | 0.019622 | 0.018221 | −0.002894 | 0.01396 | −0.003275 | 0.037253 | −0.019016 | −0.014616 | −0.038892 | −0.032574 |
| 280 | −0.013756 | 0.005292 | −0.0391 | −0.028417 | −0.014895 | −0.04071 | −0.000705 | 0.008882 | 0.002206 | −0.057682 | −0.00097 | −0.030622 | 0.014713 | −0.021984 |
| 281 | 0.012871 | 0.008581 | −0.022229 | 0.009706 | 0.000221 | −0.001157 | −0.01856 | 0.014804 | 0.014274 | −0.018067 | 0.008645 | −0.006126 | 0.029047 | −0.006053 |
| 282 | 0.005881 | 0.036371 | −0.020539 | 0.025482 | 0.016045 | 0.012541 | 0.000843 | −0.04149 | −0.036697 | 0.033907 | −0.014258 | −0.015045 | −0.051537 | 0.009546 |
| 283 | 0.006084 | −0.00843 | 0.001619 | −0.000795 | −0.018284 | −0.000659 | −0.021908 | −0.0045 | −0.018086 | 0.07788 | 0.00878 | 0.051515 | −0.035705 | −0.034008 |
| 284 | 0.014411 | −0.001204 | 0.008338 | 0.01422 | −0.010869 | 0.02704 | −0.027631 | −0.001843 | 0.034867 | −0.000722 | −0.064724 | −0.027772 | 0.033983 | 0.024869 |
| 285 | 0.004131 | −0.027245 | 0.030558 | 0.017734 | −0.001524 | 0.031958 | −0.023482 | 0.023392 | 0.031561 | 0.00691 | −0.072987 | −0.023607 | 0.016413 | 0.013956 |
| 286 | 0.010041 | 0.014863 | 0.003025 | 0.026909 | 0.031993 | 0.020842 | 0.018932 | −0.011738 | 0.008445 | −0.057837 | 0.03292 | −0.003506 | −0.005979 | −0.016829 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 287 | −0.00937 | 0.00847 | 0.009943 | 0.011507 | 0.02339 | 0.029167 | 0.005463 | −0.010466 | 0.016787 | −0.050092 | 0.026803 | −0.006455 | −0.009392 | −0.015272 |
| 288 | −0.06596 | −0.02431 | −0.082113 | −0.035499 | 0.001043 | 0.016393 | 0.001558 | −0.003701 | −0.00959 | 0.04977 | 0.005039 | −0.021909 | 0.016704 | −0.037153 |
| 289 | −0.006971 | −0.012077 | −0.014122 | −0.006887 | 0.010907 | 0.007734 | −0.003701 | 0.015377 | −0.008719 | −0.0067 | −0.003238 | −0.043116 | 0.015776 | −0.008803 |
| 290 | −0.248488 | −0.213583 | −0.014255 | 0.011589 | 0.003584 | 0.006161 | 0.016338 | −0.032654 | −0.002692 | −0.044131 | 0.002887 | 0.009857 | 0.005592 | 0.009072 |
| 291 | 0.750916 | −0.213428 | −0.012094 | 0.001477 | 0.001441 | 0.001095 | 0.015038 | −0.040656 | −0.001734 | −0.033649 | 0.005142 | 0.007805 | 0.005466 | 0.001549 |
| 292 | −0.227487 | 0.699285 | 0.013176 | −0.01177 | 0.033293 | −0.000932 | 0.014118 | 0.017437 | 0.019506 | −0.061571 | 0.01039 | 0.020404 | 0.012958 | −0.034887 |
| 293 | −0.023936 | −0.01516 | 0.585624 | −0.067737 | −0.121902 | 0.031107 | −0.120165 | −0.00093 | −0.117136 | −0.005989 | −0.108942 | −0.028013 | 0.0176 | −0.018686 |
| 294 | −0.013521 | −0.016826 | −0.055816 | 0.768115 | −0.073158 | −0.086679 | −0.044699 | −0.001081 | −0.065893 | −0.025882 | −0.039416 | −0.049934 | −0.045351 | −0.048539 |
| 797 | −0.027602 | 0.007741 | −0.090646 | −0.072862 | 0.766164 | −0.112042 | −0.156017 | 0.006348 | −0.067491 | 0.003273 | −0.086807 | −0.045919 | 0.023035 | −0.004442 |
| 296 | −0.016176 | −0.013277 | 0.094068 | −0.100114 | −0.088679 | 0.666318 | −0.047456 | −0.038757 | −0.007951 | 0.035683 | −0.018178 | −0.057808 | −0.018917 | −0.04019 |
| 297 | −0.005093 | 0.004501 | −0.085235 | −0.044317 | −0.167447 | −0.096115 | 0.753871 | 0.01035 | −0.067486 | −0.008281 | −0.085434 | −0.013739 | 0.036498 | −0.014963 |
| 298 | −0.018832 | −0.002216 | 0.025054 | 0.00669 | 0.027768 | −0.039951 | −0.014076 | 0.548448 | −0.060144 | −0.158469 | −0.033752 | −0.000808 | −0.083519 | −0.010407 |
| 299 | 0.0124 | 0.024781 | −0.12037 | −0.033059 | −0.053872 | 0.001969 | −0.091736 | −0.058261 | 0.739468 | 0.002459 | −0.088089 | −0.045148 | −0.148309 | −0.134016 |
| 300 | −0.021643 | −0.049657 | 0.033767 | −0.01733 | −0.032457 | −0.023187 | −0.046199 | −0.161203 | −0.012752 | 0.449811 | −0.002064 | −0.020078 | 0.023129 | 0.026146 |
| 301 | −0.002874 | 0.006842 | −0.081885 | −0.044053 | −0.086928 | −0.036538 | −0.093497 | −0.031392 | −0.076627 | 0.041978 | 0.805522 | −0.10142 | −0.043935 | −0.041994 |
| 302 | 0.016739 | 0.018528 | 0.001941 | −0.044781 | −0.015602 | −0.052198 | −0.008233 | −0.005269 | −0.048847 | 0.026104 | −0.103143 | 0.772285 | −0.075717 | −0.11351 |
| 303 | 0.040459 | 0.033844 | 0.009297 | −0.010165 | 0.037275 | 0.029356 | 0.03201 | −0.089489 | −0.145511 | 0.012058 | −0.057513 | −0.055082 | 0.67995 | −0.193739 |
| 304 | 0.011064 | −0.000516 | −0.024771 | −0.025757 | −0.010124 | −0.057714 | −0.021039 | −0.005142 | −0.116268 | 0.042839 | −0.024058 | −0.08485 | −0.194591 | 0.631787 |
| 305 | 0.038379 | 0.010968 | −0.088654 | −0.000571 | 0.001097 | 0.064687 | 0.036014 | −0.016388 | 0.011 | −0.050374 | −0.030965 | 0.016544 | −0.036963 | 0.04055 |
| 306 | −0.022003 | −0.05168 | −0.05609 | 0.006884 | 0.035872 | 0.007299 | 0.022626 | −0.011229 | −0.008469 | −0.006025 | 0.002043 | −0.031752 | −0.014784 | −0.049499 |
| 307 | −0.004601 | 0.009223 | 0.025298 | 0.025587 | −0.020498 | 0.00188 | −0.005782 | 0.026894 | 0.002329 | 0.005791 | 0.011605 | 0.015643 | −0.067511 | −0.032889 |
| 308 | −0.002393 | −0.008589 | −0.03105 | 0.020742 | 0.049058 | −0.006447 | −0.021435 | 0.00527 | −0.027289 | 0.059273 | −0.003055 | −0.017116 | 0.027255 | −0.040234 |
| 309 | −0.004072 | 0.002438 | −0.03519 | −0.005647 | −0.000983 | −0.015862 | −0.009956 | −0.010094 | 0.00231 | 0.009984 | 0.001932 | −0.028109 | 0.015727 | 0.015962 |
| 310 | −0.004859 | −0.000916 | 0.033233 | 0.005273 | 0.046838 | 0.025765 | 0.080022 | 0.035326 | 0.00688 | 0.050863 | 0.049308 | −0.034191 | −0.020285 | −0.038252 |
| 311 | 0.004559 | 0.014754 | −0.074894 | 0.007235 | −0.028669 | 0.016198 | −0.032381 | −0.020388 | −0.004115 | −0.036187 | −0.013876 | 0.016743 | 0.01412 | 0.034337 |
| 312 | 0.01507 | −0.014252 | 0.023365 | −0.026173 | 0.025523 | 0.006196 | −0.037278 | 0.071934 | 0.012785 | 0.045667 | 0.071865 | 0.066223 | −0.006096 | −0.000373 |
| 313 | 0.027771 | 0.017446 | −0.013106 | −0.004377 | 0.005014 | −0.046553 | −0.004666 | −0.026193 | 0.028686 | −0.040799 | −0.021891 | 0.011464 | 0.034104 | 0.025173 |
| 314 | 0.024441 | 0.026466 | −0.005618 | −0.009395 | −0.012448 | 0.014046 | −0.034221 | −0.033531 | 0.006693 | 0.003239 | 0.032915 | 0.000216 | −0.044064 | −0.05173 |
| 315 | 0.002291 | −0.016946 | 0.015522 | 0.014357 | 0.028268 | 0.001889 | 0.012745 | 0.0037 | −0.023212 | −0.03467 | 0.012736 | 0.016216 | −0.028899 | −0.004464 |
| 316 | 0.010361 | 0.05267 | 0.013614 | −0.021619 | −0.003587 | −0.026114 | 0.002832 | −0.042508 | 0.000493 | 0.024689 | −0.017124 | 0.008597 | −0.01239 | 0.009628 |
| 317 | −0.012689 | −0.003726 | −0.022073 | −0.010638 | −0.035383 | −0.019165 | −0.030326 | −0.045872 | 0.025382 | 0.0031 | −0.041477 | −0.007794 | 0.036483 | 0.046587 |
| 318 | 0.018619 | −0.021926 | −0.040749 | −0.030289 | −0.019507 | −0.020461 | −0.024072 | −0.034377 | −0.023486 | −0.047782 | −0.018626 | −0.00545 | −0.002249 | −0.052365 |
| 319 | −0.006914 | −0.010457 | 0.041077 | 0.001981 | 0.02378 | −0.004014 | −0.001068 | 0.006498 | 0.005073 | −0.007832 | 0.012496 | 0.024624 | −0.021801 | 0.002574 |
| 320 | 0.003856 | 0.016459 | 0.009102 | −0.049487 | −0.012376 | −0.098523 | −0.014602 | −0.071438 | −0.001555 | 0.022001 | −0.018825 | −0.022336 | 0.016219 | −0.00093 |
| 321 | −0.000294 | −0.022192 | 0.025804 | −0.005205 | −0.013268 | −0.022592 | −0.045387 | 0.043421 | −0.088133 | 0.01255 | −0.048887 | −0.07367 | −0.045693 | −0.014385 |
| 322 | −0.013381 | −0.018799 | 0.011518 | −0.00311 | −0.005768 | −0.005556 | 0.051521 | 0.031889 | 0.065134 | −0.040547 | −0.015166 | −0.02845 | 0.030601 | 0.005469 |
| 323 | 0.002068 | 0.014893 | 0.06479 | 0.006654 | −0.036649 | 0.012359 | −0.004839 | −0.043493 | −0.02153 | 0.045703 | −0.013124 | −0.004562 | 0.002035 | −0.010488 |
| 324 | 0.042003 | 0.046391 | −0.011898 | 0.022527 | 0.049609 | 0.035817 | 0.035129 | 0.034937 | −0.024767 | −0.006012 | −0.012247 | −0.07386 | −0.02079 | 0.02781 |
| 325 | 0.003407 | 0.021232 | 0.006889 | 0.018193 | 0.024542 | −0.054439 | 0.012553 | −0.039924 | 0.017732 | 0.019915 | −0.013781 | 0.000395 | −0.026419 | −0.001155 |
| 326 | −0.020794 | 0.008224 | 0.043657 | −0.0304 | −0.020155 | −0.028425 | 0.014009 | 0.022063 | 0.002307 | 0.053679 | 0.025668 | 0.032966 | −0.029262 | 0.027333 |
| 327 | −0.03342 | −0.051653 | 0.036816 | −0.015551 | −0.018249 | −0.063701 | −0.005945 | −0.0177 | −0.035001 | 0.002257 | −0.005454 | −0.018921 | 0.005672 | −0.037954 |
| 328 | 0.013276 | −0.009929 | 0.022763 | −0.008952 | −0.004449 | −0.075913 | −0.017641 | −0.098362 | 0.02291 | −0.013529 | 0.040843 | −0.012352 | 0.006494 | −0.047262 |
| 329 | −0.008187 | −0.03272 | 0.063365 | −0.009047 | −0.010085 | −0.013766 | −0.000087 | 0.015253 | −0.048514 | −0.032984 | −0.021042 | −0.046113 | −0.036347 | −0.04348 |
| 330 | 0.006414 | 0.009733 | 0.045089 | −0.017309 | 0.047415 | 0.021788 | 0.043409 | −0.022695 | 0.025359 | 0.031995 | −0.002811 | −0.019569 | −0.006379 | −0.003002 |
| 331 | −0.029207 | −0.029398 | −0.041516 | −0.020742 | 0.018492 | 0.034315 | 0.009251 | −0.059209 | −0.035194 | −0.017266 | 0.011476 | 0.014479 | −0.05277 | −0.019942 |
| 332 | 0.009376 | 0.008322 | 0.005105 | −0.014887 | −0.023214 | 0.010316 | −0.031418 | −0.001057 | −0.033017 | −0.063579 | −0.020467 | −0.006983 | −0.015127 | −0.028775 |
| 333 | −0.012834 | −0.033463 | −0.02416 | −0.016476 | 0.022102 | 0.008113 | −0.006307 | −0.005895 | 0.040942 | −0.002476 | −0.019036 | −0.001084 | 0.029961 | 0.012169 |
| 334 | −0.006595 | 0.024254 | −0.001576 | −0.029469 | 0.007595 | 0.01449 | 0.023177 | −0.030194 | −0.061575 | −0.000475 | −0.033228 | −0.045376 | −0.071168 | −0.008278 |
| 335 | 0.007157 | −0.005149 | −0.01482 | −0.014311 | 0.015645 | 0.033336 | −0.011446 | −0.001405 | −0.024249 | 0.051939 | −0.014288 | −0.010245 | −0.019766 | −0.047812 |
| 336 | 0.006713 | 0.033881 | −0.059508 | −0.075109 | −0.049386 | 0.008957 | −0.035775 | −0.037202 | −0.058979 | 0.002992 | −0.025479 | −0.013494 | −0.024534 | −0.056801 |
| 337 | −0.002017 | −0.008784 | 0.006735 | 0.024641 | 0.004139 | −0.003515 | −0.025181 | −0.026929 | −0.019689 | −0.037905 | −0.034797 | −0.007448 | −0.044069 | 0.019124 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 338 | −0.018332 | −0.001156 | −0.023086 | 0.01085 | 0.011566 | −0.052006 | 0.026331 | −0.114141 | −0.011274 | −0.019229 | −0.005272 | −0.000569 | −0.00525 | 0.029785 |
| 339 | −0.012413 | −0.02139 | −0.032038 | 0.01915 | 0.007673 | 0.044893 | 0.044978 | 0.047074 | 0.027549 | 0.07921 | −0.020962 | −0.036779 | −0.011402 | −0.061503 |
| 340 | −0.01784 | −0.00656 | −0.077038 | 0.003687 | −0.039607 | −0.044137 | −0.060245 | 0.020739 | −0.014482 | −0.009066 | 0.003882 | 0.02433 | −0.012054 | −0.036503 |

| | KT | KU | KV | KW | KX | KY | KZ | LA | LB | LC | LD | LE | LF | LG |
|---|---|---|---|---|---|---|---|---|---|---|---|---|---|---|
| 1 | −0.059364 | −0.009606 | 0.095188 | 0.024247 | 0.030688 | 0.03691 | −0.011822 | 0.043251 | −0.052643 | 0.038038 | −0.036106 | 0.131241 | 0.033628 | −0.079507 |
| 2 | −0.007079 | −0.01676 | −0.065677 | 0.009064 | −0.086766 | 0.027549 | −0.0986 | 0.118895 | −0.049151 | −0.002204 | −0.069088 | 0.056898 | −0.132252 | −0.049463 |
| 3 | −0.046149 | 0.014307 | −0.022754 | −0.017339 | −0.032928 | −0.113182 | 0.016133 | 0.128778 | −0.019715 | −0.126079 | 0.046715 | 0.021515 | 0.002672 | −0.080946 |
| 4 | 0.068768 | −0.011171 | −0.06992 | −0.08434 | −0.025434 | −0.041304 | 0.070459 | −0.074668 | 0.047848 | −0.024864 | −0.026589 | 0.121327 | 0.056927 | −0.109047 |
| 5 | −0.012891 | 0.022558 | 0.063359 | 0.012303 | −0.037419 | 0.023541 | −0.019436 | −0.02935 | −0.023736 | −0.001171 | 0.0034 | −0.047685 | −0.011685 | 0.027376 |
| 6 | 0.037234 | −0.068151 | −0.070576 | −0.047536 | 0.006416 | 0.037111 | −0.029118 | −0.051686 | 0.015971 | −0.0475 | 0.015332 | 0.016667 | 0.025728 | 0.054162 |
| 7 | 0.02841 | −0.002928 | −0.090285 | −0.000303 | 0.009361 | 0.014873 | −0.026799 | −0.013913 | 0.025604 | 0.012758 | −0.000226 | 0.064644 | 0.025216 | −0.041357 |
| 8 | −0.011426 | −0.028195 | 0.042963 | 0.010976 | −0.022604 | −0.056074 | −0.001349 | −0.000794 | −0.020724 | −0.006636 | −0.009924 | −0.027121 | −0.038066 | 0.016344 |
| 9 | −0.047273 | 0.033325 | −0.032134 | 0.032322 | 0.049664 | 0.041655 | 0.063776 | 0.096706 | 0.041225 | −0.034566 | 0.097103 | 0.006098 | 0.070498 | 0.103192 |
| 10 | 0.067 | 0.045274 | 0.091968 | −0.006591 | 0.024565 | 0.069131 | 0.064517 | 0.010072 | −0.024055 | −0.Q20978 | 0.027127 | 0.032147 | 0.001283 | 0.018771 |
| 11 | 0.010164 | −0.050693 | 0.000469 | −0.018104 | 0.002916 | 0.030724 | 0.02815 | −0.084282 | 0.023081 | 0.043521 | −0.022147 | −0.033181 | 0.05056 | −0.012237 |
| 12 | −0.017285 | −0.05593 | −0.042624 | −0.01867 | −0.033731 | 0.002543 | 0.027239 | −0.095734 | −0.01536 | 0.068064 | 0.007751 | −0.063542 | −0.023205 | 0.008 |
| 13 | 0.041707 | −0.081348 | 0.002866 | −0.039291 | 0.009468 | 0.100166 | −0.023332 | 0.021835 | −0.075959 | 0.066069 | 0.035864 | −0.249092 | 0.048665 | 0.01514 |
| 14 | 0.139975 | −0.081096 | 0.018542 | 0.025679 | −0.042452 | −0.073674 | −0.073623 | 0.081274 | −0.039995 | −0.016655 | −0.012167 | 0.09316 | 0.007789 | −0.03371 |
| 15 | −0.028236 | 0.004732 | −0.131015 | 0.077452 | 0.029234 | −0.013157 | −0.044967 | 0.0045 | 0.029221 | −0.047286 | 0.035409 | 0.101012 | 0.058592 | −0.004439 |
| 16 | −0.019751 | −0.032585 | −0.021536 | −0.000505 | 0.019333 | 0.019982 | 0.011954 | −0.000781 | 0.035776 | 0.011149 | 0.049607 | −0.039674 | −0.032148 | −0.060313 |
| 17 | 0.007822 | −0.009318 | −0.011238 | 0.012066 | 0.019052 | −0.016058 | −0.033605 | 0.091233 | −0.033176 | −0.035326 | −0.01737 | −0.022267 | −0.027687 | −0.098929 |
| 18 | 0.000858 | −0.022011 | 0.055957 | 0.038144 | −0.053048 | 0.025333 | −0.011838 | −0.028756 | −0.013333 | 0.007443 | −0.051636 | −0.073794 | −0.003477 | 0.006312 |
| 19 | −0.019578 | 0.044363 | −0.061114 | −0.043307 | 0.015089 | −0.014684 | −0.033754 | −0.045151 | −0.002793 | 0.137535 | −0.014298 | −0.140037 | 0.054111 | 0.104185 |
| 20 | −0.064872 | −0.05266 | 0.00126 | −0.045905 | −0.05562 | −0.048012 | −0.008356 | −0.035801 | −0.043046 | −0.024842 | −0.101225 | −0.194522 | −0.054089 | −0.11722 |
| 21 | −0.033992 | −0.006745 | −0.085526 | 0.025438 | 0.007411 | −0.041699 | −0.058687 | −0.065288 | −0.019263 | −0.069091 | 0.005317 | −0.086675 | 0.005317 | 0.026267 |
| 22 | 0.047004 | 0.006005 | 0.077406 | 0.040678 | −0.012391 | 0.019751 | 0.022174 | −0.017049 | −0.023091 | −0.041587 | 0.060583 | 0.068176 | −0.023883 | −0.006259 |
| 23 | −0.06857 | 0.041886 | 0.003021 | 0.030905 | 0.030891 | −0.067335 | −0.014557 | 0.011778 | 0.027158 | 0.09043 | −0.025371 | 0.057193 | 0.041806 | −0.057966 |
| 24 | 0.017667 | 0.018164 | −0.063948 | −0.03927 | 0.052562 | 0.100499 | 0.062238 | −0.047207 | −0.047854 | 0.013124 | −0.029373 | −0.042711 | −0.038937 | 0.020369 |
| 25 | −0.002489 | −0.010383 | 0.080002 | −0.002988 | 0.027399 | 0.023707 | 0.026886 | 0.094427 | 0.022057 | −0.071126 | −0.014485 | 0.002444 | −0.017936 | −0.008536 |
| 26 | −0.058803 | −0.008704 | −0.03781 | −0.001525 | −0.040334 | −0.022177 | 0.018826 | −0.043366 | −0.04599 | 0.047737 | −0.01697 | 0.068119 | 0.030038 | 0.079329 |
| 27 | 0.000871 | 0.003809 | −0.133975 | −0.007669 | 0.019687 | −0.097639 | −0.066284 | −0.048648 | −0.020866 | 0.033266 | 0.02232 | 0.109159 | −0.008618 | 0.037472 |
| 28 | −0.095355 | −0.012852 | 0.023125 | −0.021242 | 0.042981 | 0.021596 | 0.067377 | 0.046259 | −0.082372 | 0.16866 | 0.032172 | −0.031274 | 0.041619 | 0.036909 |
| 29 | −0.057026 | 0.057027 | 0.022034 | 0.02002 | −0.005428 | 0.108789 | −0.00413 | −0.014695 | 0.149182 | 0.038325 | −0.033819 | −0.115124 | 0.038742 | −0.001729 |
| 30 | −0.015404 | −0.057368 | −0.028803 | −0.007482 | 0.018016 | −0.014705 | −0.011179 | 0.097135 | −0.001538 | 0.066779 | −0.021791 | 0.141272 | 0.004402 | −0.003211 |
| 31 | 0.154486 | 0.017884 | −0.104216 | 0.023401 | 0.033692 | −0.023726 | 0.01403 | 0.149052 | 0.054421 | 0.01591 | 0.073234 | −0.033489 | 0.034961 | 0.013263 |
| 32 | −0.033531 | −0.007174 | −0.086585 | −0.000569 | −0.01755 | −0.00179 | 0.02875 | 0.022754 | −0.000368 | −0.033741 | 0.076982 | −0.059154 | −0.020171 | 0.053448 |
| 33 | −0.0783 | −0.030222 | −0.188 | −0.021011 | 0.03976 | −0.07475 | 0.073763 | 0.006227 | 0.042719 | −0.134393 | 0.038734 | −0.034092 | −0.051916 | −0.017896 |
| 34 | −0.161584 | 0.029431 | −0.065249 | 0.01706 | −0.002415 | 0.055584 | 0.007628 | −0.023555 | 0.041711 | −0.014848 | −0.000987 | 0.023098 | 0.01248 | −0.034337 |
| 35 | −0.026895 | 0.070254 | 0.05747 | 0.015115 | −0.029879 | 0.007037 | −0.018251 | 0.140969 | −0.025845 | −0.002938 | −0.010276 | −0.125452 | −0.037367 | −0.134413 |
| 36 | 0.029246 | 0.006813 | −0.08766 | −0.000587 | 0.006329 | 0.089049 | −0.059809 | −0.017339 | −0.107551 | −0.108864 | −0.068279 | 0.058566 | 0.038044 | 0.064707 |
| 37 | 0.120069 | 0.113086 | 0.042887 | −0.003586 | −0.01216 | 0.073224 | −0.01671 | −0.053333 | 0.004611 | −0.10743 | −0.033203 | 0.102079 | −0.022686 | 0.00191 |
| 38 | 0.061338 | 0.0722 | 0.073199 | −0.006165 | 0.053855 | 0.002978 | −0.002244 | −0.00668 | 0.062773 | 0.071763 | 0.023175 | −0.035479 | 0.047808 | −0.002675 |
| 39 | −0.090268 | −0.005473 | −0.040688 | 0:018673 | 0.036487 | −0.018777 | 0.010695 | 0.055631 | 0.034006 | −0.076597 | 0.018009 | −0.0672 | 0.065688 | 0.066814 |
| 40 | 0.108705 | −0.003995 | 0.090083 | −0.015908 | 0.023827 | 0.015069 | 0.028675 | −0.047674 | 0.044118 | −0.047468 | 0.055711 | −0.005987 | 0.064379 | −0.03606 |
| 41 | −0.02474 | 0.0803 | 0.094373 | −0.02861 | −0.03956 | 0.09055 | −0.002715 | 0.049291 | −0.012089 | 0.124451 | −0.079674 | −0.017072 | −0.045802 | 0.042913 |
| 42 | 0.086627 | −0.033895 | 0.102698 | −0.012675 | −0.032731 | −0.051155 | 0.002262 | −0.016761 | −0.008641 | 0.025754 | 0.042019 | 0.173765 | −0.037092 | −0.054311 |
| 43 | −0.075976 | 0.013897 | −0.076996 | −0.014272 | −0.002778 | −0.061532 | −0.022259 | −0.030969 | −0.056624 | −0.079241 | −0.038971 | −0.049547 | −0.011963 | −0.048711 |
| 44 | 0.009271 | 0.017424 | 0.051569 | −0.018775 | 0.025345 | 0.09196 | 0.056011 | −0.213824 | −0.002997 | −0.042881 | −0.038448 | −0.021462 | 0.017282 | 0.030959 |
| 45 | 0.062334 | −0.051257 | −0.085072 | 0.004741 | −0.003619 | −0.044302 | 0.040106 | 0.140052 | 0.021708 | 0.129919 | 0.02473 | 0.044278 | −0.026511 | −0.02014 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 46 | 0.089189 | 0.032198 | −0.031862 | −0.013495 | −0.022671 | 0.01692 | −0.0124 | −0.025091 | 0.029836 | −0.013854 | −0.042694 | −0.079438 | −0.06785 | −0.035978 |
| 47 | 0.019713 | −0.03624 | −0.092516 | 0.015672 | 0.014612 | 0.045768 | −0.00661 | 0.017434 | 0.012802 | 0.072068 | 0.057845 | −0.081307 | 0.041549 | −0.010137 |
| 48 | 0.031788 | 0.006237 | 0.135584 | −0.006568 | −0.041137 | −0.105555 | 0.015291 | −0.162494 | −0.009985 | −0.138926 | 0.027895 | −0.0119 | −0.019403 | −0.069434 |
| 49 | 0.04643 | 0.025475 | 0.018645 | 0.029191 | −0.035809 | −0.080881 | 0.028892 | 0.019001 | 0.011281 | −0.030721 | −0.006485 | 0.038551 | −0.03238 | 0.037263 |
| 50 | 0.053193 | −0.055627 | −0.050102 | −0.035415 | 0.034393 | 0.027901 | −0.017837 | 0.015246 | 0.053841 | −0.038786 | 0.025546 | −0.029371 | 0.066536 | −0.009601 |
| 51 | 0.043797 | −0.021134 | 0.05481 | −0.017843 | 0.010319 | −0.0514 | −0.032044 | −0.003499 | −0.003727 | 0.049373 | 0.030831 | 0.050165 | 0.058792 | 0.0284 |
| 52 | 0.079086 | 0.042351 | 0.069284 | −0.03458 | −0.050643 | 0.066868 | −0.025857 | −0.068213 | 0.000393 | −0.022507 | 0.011196 | 0.072455 | 0.073488 | 0.037997 |
| 53 | −0.014427 | 0.008344 | 0.082201 | 0.003609 | 0.033102 | 0.052914 | 0.017547 | 0.088521 | 0.039872 | 0.134474 | 0.046441 | 0.049645 | 0.031092 | 0.120911 |
| 54 | −0.023097 | −0.047095 | −0.167157 | 0.031311 | 0.019653 | 0.058201 | 0.006187 | 0.058276 | −0.020986 | −0.011666 | −0.014769 | −0.054642 | 0.050039 | 0.023179 |
| 55 | 0.016685 | −0.016192 | −0.031671 | 0.015283 | −0.009646 | 0.024043 | 0.049854 | −0.014326 | −0.016571 | 0.054617 | −0.068458 | 0.020785 | −0.042833 | −0.020728 |
| 56 | 0.070865 | 0.014335 | −0.07534 | 0.083824 | 0.01453 | −0.039408 | −0.037902 | 0.039479 | −0.04308 | 0.078448 | 0.059015 | −0.045953 | 0.053784 | 0.085001 |
| 57 | −0.062683 | 0.073828 | 0.005868 | −0.023093 | −0.010622 | −0.018172 | 0.022674 | 0.061996 | 0.02672 | 0.049462 | −0.059279 | 0.02017 | −0.005455 | 0.039701 |
| 58 | −0.025649 | −0.026604 | −0.045579 | −0.063976 | 0.00786 | 0.033831 | −0.050604 | −0.062924 | −0.072922 | 0.104342 | 0.045406 | 0.188876 | 0.04543 | 0.046149 |
| 59 | −0.017434 | 0.032286 | 0.052786 | 0.055252 | −0.018195 | 0.007587 | 0.047437 | −0.028758 | 0.057567 | 0.073493 | 0.04895 | −0.057512 | −0.008712 | 0.028719 |
| 60 | −0.004126 | −0.003583 | −0.023206 | −0.03835 | −0.037893 | −0.099591 | 0.054778 | 0.107438 | 0.000489 | 0.05629 | −0.030138 | 0.037124 | 0.012975 | 0.028295 |
| 61 | −0.048847 | −0.078621 | −0.054555 | 0.032034 | 0.00997 | −0.118808 | −0.033616 | −0.195748 | −0.002834 | −0.074838 | 0.011054 | 0.006524 | −0.025101 | 0.001129 |
| 62 | 0.040582 | 0.012685 | 0.0863 | 0.00644 | 0.027382 | 0.052504 | 0.034245 | −0.102764 | 0.045017 | −0.001887 | 0.006064 | 0.01491 | −0.005118 | −0.090348 |
| 63 | 0.074845 | 0.08888 | −0.010965 | −0.070885 | −0.047954 | 0.074832 | −0.011701 | 0.135313 | −0.034113 | −0.005539 | −0.013971 | 0.013088 | −0.015453 | −0.002679 |
| 64 | 0.043864 | 0.002068 | 0.041233 | −0.024144 | −0.014869 | −0.032576 | 0.009118 | 0.013779 | −0.021684 | −0.041481 | 0.012926 | 0.018446 | −0.009248 | 0.006321 |
| 65 | 0.05059 | 0.034123 | −0.049688 | −0.024289 | 0.032179 | 0.057102 | −0.113784 | −0.028266 | −0.073192 | 0.059082 | 0.00032 | −0.031582 | 0.013068 | −0.044826 |
| 66 | −0.034244 | −0.087311 | 0.071569 | −0.056434 | 0.012906 | 0.073987 | −0.055531 | 0.098278 | −0.012444 | 0.00866 | 0.034043 | 0.045846 | −0.047039 | 0.013479 |
| 67 | −0.084318 | 0.028649 | −0.067545 | −0.0059 | 0.015529 | 0.010347 | −0.082868 | −0.060017 | −0.072621 | −0.044622 | −0.088136 | −0.115889 | 0.086013 | 0.063505 |
| 68 | 0.0465 | −0.059313 | −0.026817 | 0.021207 | 0.039875 | 0.014185 | −0.016805 | −0.005685 | 0.026094 | −0.014188 | 0.043137 | −0.000133 | −0.021716 | −0.027042 |
| 69 | −0.049494 | 0.019094 | 0.069004 | −0.005685 | 0.026516 | 0.0137 | 0.03355 | −0.011362 | −0.035627 | −0.086317 | 0.019211 | 0.09353 | 0.04025 | −0.01422 |
| 70 | −0.079324 | 0.053586 | −0.009883 | 0.081226 | 0.085701 | 0.041363 | −0.006818 | −0.06274 | 0.079604 | 0.006831 | −0.020183 | 0.065368 | 0.039671 | 0.060851 |
| 71 | 0.063649 | −0.038803 | 0.019153 | −0.019832 | 0.000818 | −0.043647 | 0.05548 | 0.035556 | −0.049039 | 0.035307 | 0.022459 | −0.018325 | 0.044118 | −0.022534 |
| 72 | 0.007755 | 0.031818 | 0.007321 | 0.03796 | 0.013462 | −0.060611 | 0.005363 | −0.052442 | 0.043549 | −0.061113 | −0.008437 | 0.090232 | 0.029514 | −0.022087 |
| 73 | −0.105958 | −0.088136 | −0.056851 | 0.003116 | 0.027429 | 0.005463 | 0.025974 | −0.050201 | −0.043458 | −0.000515 | −0.073877 | 0.006041 | −0.009053 | 0.036693 |
| 74 | −0.075828 | 0.013213 | −0.044705 | −0.024352 | 0.001563 | −0.006969 | 0.033112 | −0.023163 | −0.012839 | −0.025507 | 0.002549 | −0.038924 | −0.005207 | −0.06268 |
| 75 | −0.132913 | −0.004925 | −0.127985 | −0.041233 | −0.013326 | 0.026 | 0.079409 | 0.025305 | 0.090572 | 0.043504 | 0.018846 | 0.098123 | 0.014101 | 0.020512 |
| 76 | −0.047467 | −0.000894 | 0.072613 | −0.009343 | 0.014653 | −0.043805 | −0.016806 | −0.031912 | 0.018795 | −0.072141 | 0.045538 | −0.024286 | −0.015858 | 0.016247 |
| 77 | −0.011421 | 0.110414 | 0.076143 | 0.00879 | −0.084007 | 0.030983 | −0.170369 | 0.008506 | −0.085969 | 0.050179 | −0.088524 | 0.114088 | −0.119768 | −0.069596 |
| 78 | 0.006871 | 0.046384 | −0.045785 | 0.013857 | 0.042518 | −0.015687 | 0.040199 | −0.029257 | 0.005173 | −0.016532 | 0.022772 | −0.028462 | 0.013279 | −0.040965 |
| 79 | 0.122796 | 0.03114 | −0.013522 | 0.011532 | 0.015545 | 0.02367 | 0.110235 | 0.026673 | 0.033923 | 0.065525 | 0.014393 | 0.009995 | 0.008759 | 0.085464 |
| 80 | −0.000554 | 0.075412 | −0.100558 | −0.012598 | −0.004432 | 0.02384 | −0.03251 | 0.032446 | 0.09019 | 0.01878 | 0.021118 | 0.039794 | −0.013418 | 0.015439 |
| 81 | 0.056915 | −0.059868 | −0.076411 | −0.057772 | −0.050852 | −0.109907 | 0.032941 | −0.026739 | 0.021465 | 0.013145 | −0.023869 | −0.086648 | −0.040335 | 0.021198 |
| 82 | 0.001772 | −0.029402 | 0.051694 | −0.083533 | −0.033203 | −0.06711 | −0.038618 | −0.059581 | −0.027908 | −0.141461 | 0.003353 | −0.002616 | −0.046544 | 0.06474 |
| 83 | 0.137421 | −0.045322 | 0.076507 | −0.060122 | −0.010558 | 0.017325 | 0.005029 | 0.068476 | −0.004478 | −0.031039 | −0.010505 | 0.085753 | 0.00384 | −0.122934 |
| 84 | 0.077344 | −0.031889 | −0.029718 | −0.017304 | −0.049132 | −0.054267 | 0.063585 | 0.124318 | 0.127307 | −0.015762 | −0.050634 | 0.056257 | −0.038283 | −0.022342 |
| 85 | 0.03084 | −0.035074 | −0.116334 | 0.046574 | 0.032816 | 0.052909 | −0.018201 | −0.034282 | 0.002808 | 0.034515 | −0.013812 | −0.026201 | −0.019615 | 0.036857 |
| 86 | 0.060814 | 0.025614 | −0.009524 | −0.00772 | −0.006812 | 0.014458 | −0.033692 | 0.001722 | −0.014228 | 0.228204 | 0.019605 | 0.060667 | −0.024455 | 0.031872 |
| 87 | −0.055828 | 0.030409 | 0.12667 | −0.010941 | −0.046026 | 0.044918 | −0.014556 | −0.036372 | 0.000155 | 0.008492 | 0.039723 | 0.035293 | −0.001552 | −0.028934 |
| 88 | −0.057264 | 0.108333 | 0.030178 | −0.072954 | −0.032903 | 0.018006 | 0.031748 | 0.118756 | −0.088127 | 0.052588 | 0.03211 | −0.075776 | −0.043745 | −0.016674 |
| 89 | 0.04947 | −0.01871 | 0.043898 | 0.048349 | 0.051446 | 0.102827 | −0.016685 | −0.012441 | −0.009814 | 0.11402 | 0.051954 | 0.024392 | 0.092435 | 0.013855 |
| 90 | 0.0659 | −0.111365 | 0.003103 | 0.00755 | −0.027167 | −0.052494 | −0.055067 | −0.038451 | −0.020848 | 0.093061 | 0.035556 | −0.054359 | −0.082477 | −0.035041 |
| 91 | 0.128399 | 0.03975 | 0.111726 | 0.084009 | 0.043561 | 0.022536 | −0.009539 | −0.007913 | 0.044679 | −0.023862 | −0.039645 | −0.073726 | −0.029616 | 0.025551 |
| 92 | −0.037964 | 0.000413 | 0.140814 | −0.003409 | −0.026929 | 0.013701 | −0.007524 | 0.016555 | 0.054662 | −0.165842 | −0.040553 | −0.115822 | −0.017824 | 0.06299 |
| 93 | −0.014732 | −0.039818 | 0.080418 | 0.011324 | −0.007826 | −0.045283 | −0.007132 | −0.030738 | −0.059148 | −0.011921 | 0.025115 | −0.006015 | 0.044216 | −0.034938 |
| 94 | −0.20228 | 0.043402 | 0.170616 | 0.008428 | −0.011346 | 0.03969 | −0.109732 | −0.13402 | −0.091209 | 0.080302 | −0.03294 | 0.114586 | −0.024798 | −0.033222 |
| 95 | 0.040953 | −0.023526 | 0.002399 | −0.014596 | −0.022977 | 0.03472 | 0.034016 | −0.009125 | 0.003283 | 0.057456 | −0.017404 | −0.032867 | −0.020239 | 0.04726 |
| 96 | −0.075559 | −0.045317 | 0.113883 | 0.009855 | −0.040075 | −0.042915 | 0.084295 | −0.029608 | −0.008557 | 0.04208 | 0.038056 | −0.006713 | 0.017469 | 0.036755 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 97 | 0.028573 | 0.092673 | 0.026822 | −0.001183 | −0.036376 | −0.046024 | −0.002816 | −0.041775 | −0.005536 | −0.018828 | −0.03864 | −0.046322 | 0.017026 | 0.047434 |
| 98 | −0.06625 | −0.198756 | 0.12185 | −0.093032 | 0.035311 | −0.066403 | −0.002363 | −0.002871 | −0.059655 | 0.007551 | 0.03994 | −0.035162 | 0.12489 | 0.006338 |
| 99 | 0.002091 | −0.039955 | 0.036365 | 0.023898 | 0.014702 | −0.074654 | −0.012681 | 0.081319 | −0.007946 | 0.000771 | −0.026901 | 0.002502 | −0.061734 | −0.085268 |
| 100 | 0.033706 | −0.012302 | −0.017097 | 0.005655 | 0.014502 | −0.027711 | 0.002794 | 0.110931 | 0.005649 | −0.087341 | 0.015753 | 0.022001 | −0.061555 | 0.08277 |
| 101 | 0.063808 | −0.029506 | 0.081752 | −0.059175 | −0.030994 | −0.020646 | 0.046977 | −0.045505 | 0.011894 | 0.159456 | −0.04948 | −0.006809 | 0.000273 | 0.069034 |
| 102 | −0.018093 | 0.05616 | 0.071367 | 0.024196 | −0.025287 | 0.033029 | −0.026777 | 0.044684 | −0.017454 | −0.071553 | −0.014657 | −0.067912 | −0.045749 | −0.018316 |
| 103 | 0.094478 | 0.012343 | −0.068135 | 0.047384 | 0.006848 | 0.032417 | 0.009065 | −0.047023 | 0.043811 | −0.036413 | 0.025021 | 0.074854 | 0.009099 | 0.048436 |
| 104 | −0.005802 | 0.082217 | 0.018005 | 0.014649 | 0.010238 | −0.099229 | −0.002792 | 0.0162 | 0.045396 | 0.011733 | 0.029566 | 0.114206 | 0.016583 | 0.044316 |
| 105 | 0.056749 | 0.020271 | −0.04852 | −0.04358 | 0.010791 | 0.035752 | 0.003553 | −0.025387 | 0.027918 | 0.026579 | −0.013594 | 0.005107 | 0.001719 | −0.053784 |
| 106 | 0.039414 | 0.002476 | −0.021157 | −0.023931 | −0.044395 | −0.014754 | 0.023533 | −0.102581 | 0.029986 | −0.003228 | 0.028506 | 0.079983 | 0.020977 | 0.028882 |
| 107 | 0.041246 | −0.049675 | −0.073817 | 0.019864 | −0.065094 | −0.036312 | 0.031151 | 0.112457 | 0.003216 | −0.003888 | 0.007919 | −0.117662 | −0.095346 | 0.00361 |
| 108 | 0.080554 | 0.061177 | 0.036012 | −0.005539 | −0.012654 | 0.01293 | 0.06901 | −0.031503 | −0.092366 | −0.05963 | −0.033294 | −0.053504 | 0.026971 | 0.073735 |
| 109 | −0.049555 | −0.013158 | −0.048383 | −0.014495 | 0.009176 | 0.015504 | −0.002601 | −0.094696 | −0.042632 | 0.083176 | −0.002117 | 0.000901 | 0.019276 | −0.015662 |
| 110 | −0.011206 | −0.07043 | −0.102266 | −0.004974 | −0.038243 | 0.026523 | −0.011501 | −0.127677 | 0.014629 | −0.016092 | −0.035957 | −0.071479 | −0.013126 | −0.091472 |
| 111 | 0.029521 | −0.010637 | 0.02558 | −0.017327 | 0.041692 | −0.023233 | −0.074451 | −0.093983 | 0.042579 | 0.012073 | 0.003403 | −0.000624 | 0.007569 | 0.054697 |
| 112 | −0.005357 | −0.013058 | 0.00277 | −0.050489 | 0.022403 | −0.003274 | 0.028536 | 0.010524 | 0.056798 | −0.017586 | 0.046442 | 0.032069 | −0.019942 | −0.034 |
| 113 | −0.036521 | −0.009891 | 0.053474 | 0.022207 | 0.033278 | 0.037677 | −0.026497 | −0.016456 | −0.073942 | −0.005412 | −0.031566 | −0.010157 | 0.012066 | 0.008424 |
| 114 | 0.014749 | −0.018047 | −0.009996 | −0.015208 | −0.022036 | −0.007304 | −0.061037 | 0.020984 | 0.052582 | 0.053888 | 0.027186 | 0.009032 | −0.012403 | 0.050718 |
| 115 | −0.047547 | 0.013866 | −0.069627 | 0.024324 | −0.073388 | −0.063637 | 0.014478 | 0.089091 | 0.028162 | 0.009746 | 0.036001 | 0.092792 | 0.000085 | 0.046041 |
| 116 | −0.019226 | 0.025526 | 0.030805 | 0.021048 | 0.02915 | 0.000018 | −0.007894 | −0.034979 | 0.012933 | 0.041088 | −0.001305 | −0.014472 | 0.011487 | −0.037281 |
| 117 | 0.012795 | 0.058916 | −0.004898 | −0.00597 | −0.010664 | 0.001709 | 0.015729 | −0.068081 | 0.010976 | 0.020891 | −0.023846 | −0.061931 | −0.062488 | −0.003653 |
| 118 | −0.068427 | −0.040798 | 0.015787 | −0.032686 | −0.046288 | −0.07603 | −0.049342 | 0.082629 | 0.008514 | −0.068583 | −0.01976 | −0.04226 | −0.02877 | 0.129427 |
| 119 | 0.050163 | 0.034487 | 0.012585 | −0.046085 | −0.026791 | 0.045203 | −0.046225 | −0.078682 | −0.087932 | −0.043504 | 0.012303 | 0.053134 | −0.019547 | −0.140275 |
| 120 | −0.040559 | −0.123841 | −0.154297 | −0.003485 | 0.018007 | 0.073702 | −0.055539 | −0.024096 | −0.082545 | −0.025069 | −0.054868 | 0.131483 | −0.023596 | −0.069972 |
| 121 | −0.042437 | −0.018318 | 0.098363 | −0.008356 | −0.019024 | −0.001416 | 0.012836 | 0.123585 | −0.041558 | 0.070052 | −0.054776 | −0.123147 | 0.087575 | 0.007141 |
| 122 | 0.091037 | 0.067743 | 0.047944 | −0.005361 | 0.039389 | 0.016026 | 0.021484 | 0.019425 | 0.03686 | 0.079933 | −0.023883 | 0.077985 | 0.072231 | 0.056186 |
| 123 | 0.108289 | 0.060914 | −0.070386 | 0.045811 | −0.018269 | 0.055939 | −0.020289 | 0.004132 | 0.012273 | −0.0154 | 0.032093 | −0.04954 | 0.011121 | −0.020933 |
| 124 | −0.005141 | −0.04803 | 0.10125 | −0.02822 | 0.042559 | 0.007087 | 0.002443 | −0.042826 | 0.017362 | −0.046162 | 0.001842 | −0.049802 | 0.036791 | −0.009744 |
| 125 | 0.028997 | 0.008593 | −0.131381 | −0.056634 | −0.01242 | −0.041944 | 0.061236 | −0.139492 | −0.056837 | −0.033856 | 0.00364 | 0.009596 | −0.008701 | 0.029743 |
| 126 | −0.004004 | −0.162194 | 0.072006 | −0.033531 | 0.016571 | −0.029142 | 0.034443 | 0.051815 | 0.009539 | −0.151075 | −0.056857 | −0.046829 | −0.024303 | 0.037475 |
| 127 | −0.016032 | 0.036715 | −0.111954 | 0.050285 | 0.082752 | 0.013432 | −0.017184 | −0.011934 | 0.067898 | 0.022567 | 0.038508 | −0.053265 | 0.053277 | −0.045173 |
| 128 | −0.012974 | −0.005895 | 0.069659 | 0.029885 | 0.074774 | 0.030593 | 0.004238 | −0.055887 | 0.13982 | 0.052563 | 0.027709 | −0.047557 | 0.07934 | −0.008786 |
| 129 | −0.035151 | −0.009292 | −0.039844 | 0.027978 | 0.004566 | 0.006171 | −0.048553 | 0.013567 | −0.020539 | 0.026651 | −0.050765 | −0.000046 | −0.08966 | −0.015049 |
| 130 | 0.011382 | −0.014321 | −0.02946 | −0.018568 | −0.022642 | 0.056328 | 0.040305 | 0.003446 | 0.012488 | −0.03725 | −0.01539 | 0.055767 | −0.045068 | −0.021338 |
| 131 | −0.044978 | −0.010558 | −0.017719 | 0.070362 | 0.059642 | −0.026239 | 0.003345 | −0.044168 | −0.054869 | −0.001926 | 0.003445 | 0.071086 | 0.02427 | 0.057202 |
| 132 | −0.04567 | 0.059339 | 0.021818 | −0.008433 | 0.02369 | 0.070757 | 0.03301 | 0.008002 | −0.010345 | −0.062041 | 0.025515 | −0.039676 | 0.015561 | 0.011735 |
| 133 | −0.000017 | −0.098518 | 0.045207 | −0.085409 | −0.092686 | −0.131036 | 0.032245 | 0.045931 | −0.030871 | −0.036796 | −0.047705 | −0.015791 | 0.002005 | 0.012144 |
| 134 | 0.02544 | −0.03319 | 0.02297 | −0.017854 | 0.013762 | 0.00145 | 0.01734 | 0.00554 | 0.060683 | 0.02412 | 0.025549 | 0.036692 | 0.042415 | −0.048763 |
| 135 | 0.011323 | 0.092345 | −0.019049 | 0.178325 | 0.079172 | −0.048113 | −0.02854 | −0.106367 | −0.110787 | −0.115185 | 0.024053 | −0.082276 | 0.012188 | 0.023009 |
| 136 | 0.066124 | 0.019041 | 0.037279 | −0.185999 | −0.076567 | −0.163283 | 0.047469 | −0.009343 | 0.08396 | 0.099573 | 0.033394 | −0.010966 | −0.031613 | −0.023128 |
| 137 | 0.017496 | −0.068612 | 0.02974 | −0.004126 | −0.010353 | −0.041762 | −0.015871 | −0.01918 | −0.021784 | 0.103633 | 0.036337 | 0.022213 | −0.006665 | 0.057772 |
| 138 | 0.025511 | 0.049206 | −0.014822 | 0.021931 | −0.039284 | −0.001101 | −0.045113 | 0.072992 | 0.042445 | −0.000964 | −0.019531 | −0.000727 | −0.033986 | −0.033935 |
| 139 | 0.012375 | −0.075813 | −0.101051 | −0.02291 | −0.043211 | −0.049453 | −0.025437 | 0.027153 | 0.012685 | 0.030996 | 0.012398 | 0.035976 | −0.013827 | −0.003218 |
| 140 | 0.002848 | 0.055084 | 0.003925 | 0.017408 | −0.002508 | 0.002593 | 0.00758 | 0.060994 | −0.102721 | 0.013692 | 0.076549 | −0.014536 | 0.005657 | 0.037771 |
| 141 | 0.009437 | 0.028268 | 0.053329 | −0.017491 | −0.042415 | −0.054403 | −0.001151 | 0.034409 | 0.032901 | −0.011151 | 0.022297 | 0.054167 | −0.058417 | 0.004387 |
| 142 | −0.033203 | −0.05569 | 0.006391 | −0.007949 | 0.008301 | 0.044587 | −0.022329 | −0.008815 | 0.012534 | 0.064787 | −0.00811 | −0.035538 | −0.028448 | −0.035267 |
| 143 | −0.035619 | −0.052898 | −0.007414 | −0.02638 | 0.038749 | −0.059767 | 0.00584 | −0.055856 | −0.003112 | 0.056132 | −0.004894 | 0.044556 | 0.014234 | 0.005485 |
| 144 | −0.04758 | 0.004833 | 0.038934 | 0.025835 | 0.012181 | 0.032592 | 0.00075 | 0.006067 | −0.02121 | 0.009273 | −0.019191 | 0.015506 | −0.003954 | 0.013625 |
| 145 | −0.024638 | −0.027747 | −0.008693 | −0.027973 | −0.023304 | 0.034059 | 0.026081 | 0.078535 | −0.046915 | 0.000755 | −0.028199 | 0.035859 | 0.03147 | 0.029651 |
| 146 | 0.002611 | −0.080253 | 0.00512 | −0.091776 | −0.021834 | −0.014123 | 0.035023 | −0.015311 | 0.00254 | 0.053353 | −0.013326 | 0.011012 | 0.012085 | 0.045121 |
| 147 | 0.056142 | −0.091349 | 0.021209 | −0.049964 | −0.024504 | −0.054174 | 0.040194 | −0.052963 | 0.017915 | −0.045263 | 0.011976 | 0.029384 | 0.017188 | −0.049483 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 148 | 0.046036 | −0.003453 | −0.063331 | −0.033374 | −0.003306 | −0.044971 | −0.037246 | −0.007659 | −0.06178 | −0.015946 | −0.038878 | −0.006264 | −0.011459 | 0.000945 |
| 149 | 0.021712 | −0.030741 | 0.018831 | 0.020499 | 0.004686 | 0.040442 | 0.011563 | −0.001347 | −0.000093 | 0.050133 | −0.016652 | 0.043944 | 0.005798 | 0.001814 |
| 150 | 0.085539 | 0.011114 | −0.026326 | 0.009106 | 0.019026 | 0.000747 | −0.014754 | 0.059897 | 0.03684 | 0.003907 | 0.010897 | −0.044171 | 0.015782 | 0.020624 |
| 151 | −0.009333 | 0.006718 | −0.020362 | 0.035323 | −0.001534 | 0.006944 | −0.028169 | −0.052944 | −0.035125 | −0.044162 | −0.025468 | −0.035548 | 0.009422 | 0.031921 |
| 152 | 0.002842 | 0.002427 | −0.016593 | −0.019476 | −0.038347 | 0.017431 | −0.052091 | 0.04265 | −0.020473 | −0.091039 | −0.028365 | −0.013625 | −0.056696 | −0.011963 |
| 153 | −0.059376 | 0.032668 | −0.015555 | −0.026868 | −0.04357 | 0.0052 | −0.007646 | 0.001854 | −0.043256 | 0.025514 | −0.024724 | −0.028628 | −0.031396 | −0.026044 |
| 154 | 0.018302 | 0.015624 | −0.041448 | 0.004412 | −0.003511 | 0.050875 | −0.033764 | 0.007194 | 0.006792 | −0.037017 | 0.018359 | 0.051735 | 0.027866 | 0.053935 |
| 155 | 0.01652 | −0.004785 | 0.029504 | 0.056833 | 0.010722 | 0.026327 | 0.012934 | 0.021515 | 0.000191 | 0.006884 | 0.045908 | −0.034491 | 0.006517 | −0.037533 |
| 156 | −0.035365 | 0.056334 | −0.024467 | −0.000142 | −0.035121 | 0.0222 | 0.013088 | −0.027929 | 0.021342 | 0.079675 | −0.035594 | 0.015438 | −0.019519 | −0.024044 |
| 157 | −0.077586 | −0.01494 | 0.0051 | 0.025102 | 0.014171 | 0.061712 | 0.012017 | −0.007023 | −0.019709 | 0.025991 | −0.03482 | 0.000144 | −0.029412 | −0.002307 |
| 158 | 0.015614 | 0.007988 | −0.068443 | 0.027665 | 0.00649 | −0.004403 | 0.00463 | 0.002727 | 0.051139 | −0.015794 | −0.008404 | 0.003825 | −0.007661 | 0.017227 |
| 159 | −0.010969 | −0.000277 | 0.024696 | 0.031342 | −0.035122 | −0.011567 | −0.017671 | 0.036292 | 0.005335 | −0.000831 | 0.063432 | 0.002787 | −0.030389 | 0.001797 |
| 160 | −0.026732 | 0.043464 | 0.031231 | −0.015897 | 0.001915 | −0.026824 | 0.026595 | 0.023747 | 0.034764 | 0.005503 | 0.030385 | 0.00807 | 0.011108 | 0.074485 |
| 161 | −0.016816 | −0.005349 | 0.052427 | −0.009837 | −0.036072 | 0.007931 | 0.008372 | 0.003501 | 0.002306 | 0.004872 | −0.018227 | −0.03989 | −0.004009 | 0.062748 |
| 162 | 0.002508 | 0.035294 | −0.105148 | 0:010683 | −0.019989 | −0.012101 | 0.003814 | 0.040648 | 0.014483 | 0.009979 | −0.011734 | 0.006261 | 0.016431 | 0.076038 |
| 163 | 0.023721 | −0.001719 | 0.019396 | 0.028926 | −0.001093 | 0.053062 | 0.008365 | 0.022775 | 0.043858 | 0.054712 | 0.008406 | −0.026299 | 0.02578 | 0.018663 |
| 164 | −0.047791 | −0.00718 | 0.053963 | −0.016442 | 0.002232 | 0.001323 | 0.037227 | 0.025016 | 0.01779 | 0.00013 | −0.017808 | 0.040213 | 0.01512 | 0.014228 |
| 165 | 0.052738 | −0.010402 | −0.049858 | 0.01509 | 0.026462 | −0.03114 | −0.030249 | 0.021933 | 0.003753 | 0.008658 | −0.030587 | 0.038187 | 0.061335 | 0.026378 |
| 166 | 0.071333 | 0.025263 | 0.039994 | −0.015777 | 0.008994 | −0.007665 | 0.047222 | −0.063836 | 0.018202 | −0.071903 | 0.011762 | −0.009672 | 0.007716 | −0.023147 |
| 167 | −0.029965 | −0.018765 | 0.009641 | 0.022491 | 0.025369 | 0.054546 | −0.003582 | 0.025759 | −0.03073 | 0.01407 | 0.003244 | −0.112888 | 0.000564 | −0.04298 |
| 168 | 0.036292 | 0.044638 | −0.029652 | 0.013322 | 0.028493 | 0.01045 | 0.01206 | −0.068467 | 0.016265 | −0.037516 | −0.048446 | 0.063672 | 0.021834 | 0.049458 |
| 169 | 0.046691 | 0.000385 | −0.022712 | 0.015641 | 0.012349 | −0.001701 | 0.012729 | −0.000461 | 0.021157 | 0.002085 | 0.012304 | 0.012887 | 0.016768 | 0.002295 |
| 170 | 0.015421 | 0.017523 | 0.032518 | 0.005282 | −0.020021 | −0.023337 | 0.002416 | 0.022783 | 0.00908 | −0.05805 | −0.007296 | 0.01907 | 0.005792 | 0.016812 |
| 171 | 0.022609 | 0.002382 | 0.010534 | 0.024472 | 0.004744 | 0.00499 | −0.021123 | 0.039079 | 0.020208 | 0.03597 | 0.022408 | −0.042878 | 0.00818 | 0.004297 |
| 172 | −0.014978 | −0.013048 | −0.041937 | −0.006186 | 0.01876 | 0.029269 | −0.016589 | 0.010243 | 0.001545 | 0.018147 | 0.024176 | −0.022328 | −0.007284 | −0.031869 |
| 173 | 0.001446 | −0.005425 | 0.016393 | −0.044159 | −0.004121 | −0.014722 | −0.016438 | 0.014122 | −0.018932 | 0.003007 | 0.011769 | −0.019502 | −0.014996 | 0.041037 |
| 174 | 0.117819 | 0.031424 | 0.053039 | −0.012565 | −0.004797 | 0.00932 | 0.011251 | −0.028106 | 0.009979 | 0.013477 | 0.012892 | −0.098091 | −0.007195 | 0.02892 |
| 175 | −0.012116 | −0.020185 | 0.00194 | −0.004538 | −0.030364 | 0.005692 | −0.01346 | −0.030541 | 0.02956 | 0.043034 | −0.012027 | −0.008282 | −0.003277 | 0.000399 |
| 176 | −0.065281 | −0.026068 | −0.078307 | 0.056446 | 0.020278 | 0.010221 | 0.01559 | 0.003982 | 0.030308 | 0.011632 | 0.017781 | 0.022983 | 0.000203 | −0.002572 |
| 177 | −0.026339 | −0.010272 | −0.010221 | −0.030075 | −0.001992 | −0.04007 | 0.079727 | −0.048208 | −0.002896 | 0.078998 | 0.001863 | −0.040243 | 0.06929 | 0.010262 |
| 178 | 0.002903 | 0.004287 | −0.025859 | −0.027346 | 0.000599 | 0.022923 | 0.011232 | −0.0529 | 0.006292 | 0.013832 | 0.021041 | 0.003531 | 0.031622 | −0.045118 |
| 179 | 0.05976 | 0.02308 | −0.034409 | 0.018215 | 0.009698 | −0.007113 | −0.01667 | −0.004567 | 0.00664 | 0.042761 | 0.015956 | −0.007708 | 0.013031 | 0.016516 |
| 180 | 0.037664 | 0.046588 | −0.008184 | 0.009183 | 0.015171 | 0.012077 | 0.018965 | −0.042989 | 0.014002 | −0.015637 | −0.004432 | −0.006867 | 0.002351 | −0.023986 |
| 181 | 0.018851 | 0.056369 | 0.000767 | 0.000114 | 0.003642 | 0.008979 | 0.023786 | −0.046003 | 0.002889 | −0.015424 | −0.000973 | −0.01373 | −0.013672 | −0.02256 |
| 182 | 0.005773 | 0.02029 | 0.013518 | −0.00976 | −0.008445 | −0.048916 | 0.033389 | −0.019071 | 0.007667 | −0.011493 | −0.005193 | 0.00882 | −0.006916 | −0.034507 |
| 183 | −0.000041 | −0.034147 | 0.021873 | 0.008705 | −0.015362 | −0.042643 | −0.037002 | −0.007616 | −0.030497 | 0.063004 | 0.015211 | −0.009464 | 0.016186 | −0.00847 |
| 184 | 0.02994 | −0.016204 | 0.068831 | −0.031205 | −0.007347 | −0.020835 | −0.040215 | −0.023729 | −0.049463 | 0.001347 | 0.019813 | −0.034452 | 0.030307 | −0.0165 |
| 185 | −0.049426 | 0.030605 | −0.05165 | 0.055446 | 0.016043 | 0.010451 | 0.006152 | −0.048515 | −0.004477 | 0.041577 | −0.005587 | −0.017425 | −0.003799 | 0.001383 |
| 186 | −0.020324 | 0.023789 | 0.000495 | −0.005736 | −0.011716 | 0.002569 | 0.01679 | 0.090859 | 0.001599 | −0.016086 | −0.008611 | −0.002035 | 0.000657 | 0.014709 |
| 187 | −0.005019 | 0.022834 | −0.000175 | −0.007884 | 0.020797 | −0.021899 | 0.020217 | −0.039494 | 0.005137 | 0.024869 | 0.003828 | −0.015259 | 0.00924 | 0.01828 |
| 188 | 0.035831 | 0.022394 | −0.005471 | −0.009389 | 0.003009 | 0.005755 | −0.010506 | −0.049625 | 0.00459 | 0.017329 | 0.009026 | −0.039622 | 0.01093 | −0.031876 |
| 189 | −0.001031 | 0.003032 | −0.009976 | 0.00525 | 0.000716 | 0.03986 | −0.00613 | −0.057688 | 0.018765 | 0.0337 | −0.012818 | 0.016874 | 0.014521 | −0.026773 |
| 190 | 0.011393 | 0.032391 | −0.076488 | 0.0129 | −0.020912 | 0.060177 | −0.049124 | −0.041022 | −0.005966 | −0.020822 | −0.024516 | −0.052873 | −0.024373 | −0.036696 |
| 191 | 0.022311 | 0.008917 | −0.024309 | −0.031109 | −0.000604 | 0.045513 | −0.015648 | −0.056701 | 0.000298 | 0.006412 | −0.021269 | −0.068409 | −0.045032 | −0.085698 |
| 192 | 0.017427 | 0.0226 | −0.02081 | −0.065726 | 0.000316 | 0.027442 | 0.017811 | −0.00479 | −0.047956 | −0.01437 | −0.001938 | 0.040004 | 0.038965 | −0.029156 |
| 193 | −0.098468 | −0.03465 | −0.040068 | −0.010663 | 0.006711 | −0.03817 | 0.014155 | 0.024607 | 0.037259 | 0.063201 | 0.026235 | 0.03348 | −0.013929 | 0.054558 |
| 194 | 0.02082 | −0.067659 | −0.037199 | −0.019031 | −0.02535 | −0.015253 | −0.035741 | −0.010723 | −0.036862 | 0.026711 | −0.030627 | −0.010953 | −0.020071 | −0.05635 |
| 195 | −0.030627 | −0.024858 | 0.051001 | −0.000537 | 0.012963 | −0.026844 | −0.012141 | 0.023094 | −0.025627 | −0.018851 | 0.003004 | 0.021922 | −0.000164 | 0.013585 |
| 196 | −0.017155 | −0.027437 | −0.028791 | −0.02121 | 0.030631 | 0.062942 | 0.005189 | 0.010762 | 0.005228 | −0.003875 | −0.043805 | 0.020639 | 0.006762 | −0.005502 |
| 197 | −0.028288 | −0.03172 | −0.020575 | −0.016629 | −0.009868 | 0.030834 | 0.012952 | −0.002563 | −0.034188 | −0.016945 | −0.039106 | −0.023729 | −0.023744 | 0.000819 |
| 198 | −0.032406 | −0.051551 | 0.007685 | −0.056195 | −0.05698 | −0.019391 | −0.006472 | 0.011275 | −0.037606 | −0.048639 | 0.024086 | 0.021576 | −0.0009 | −0.061791 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 199 | 0.020665 | 0.011191 | 0.013413 | −0.016299 | 0.017933 | −0.040011 | −0.01964 | −0.018663 | 0.02104 | −0.01746 | −0.016847 | −0.009532 | 0.016349 | 0.026485 |
| 200 | −0.018156 | 0.049624 | −0.006031 | 0.024262 | 0.021292 | −0.000545 | −0.046272 | 0.001181 | −0.016992 | 0.031389 | 0.034539 | 0.020331 | −0.005489 | 0.051522 |
| 201 | 0.000025 | −0.000214 | −0.039602 | 0.029579 | 0.005001 | 0.020087 | −0.015249 | 0.002017 | −0.035484 | −0.034954 | −0.016553 | 0.055091 | −0.0035 | −0.021601 |
| 202 | 0.057424 | 0.023838 | −0.067318 | −0.030934 | −0.018286 | 0.048359 | 0.024009 | 0.040974 | −0.007083 | −0.043709 | 0.001405 | −0.046222 | 0.019657 | 0.022739 |
| 203 | −0.057745 | −0.013817 | 0.020675 | 0.009900 | 0.021787 | 0.014364 | −0.055357 | 0.008419 | −0.019062. | 0.101472 | −0.035142 | −0.014629 | 0.025084 | 0.043737 |
| 204 | −0.032993 | 0.019912 | 0.000389 | −0.010677 | −0.01632 | 0.045321 | 0.008556 | −0.01622 | −0.000118 | −0.04392 | −0.017208 | 0.062126 | −0.000907 | 0.06405 |
| 205 | 0.011686 | −0.095665 | −0.053591 | 0.015594 | 0.002074 | 0.030398 | 0.012418 | 0.060777 | 0.04213 | 0.015757 | −0.017711 | −0.020213 | −0.06522 | −0.0746 |
| 206 | −0.040996 | 0.011594 | −0.012028 | −0.043741 | −0.033955 | −0.035073 | −0.01476 | 0.101422 | −0.00358 | 0.074816 | −0.000203 | −0.053527 | 0.003163 | −0.034032 |
| 207 | −0.043732 | −0.017113 | 0.049253 | −0.009525 | 0.045704 | 0.000031 | 0.037885 | −0.018823 | 0.043964 | 0.001919 | 0.036276 | −0.000842 | 0.001591 | −0.01174 |
| 208 | 0.001173 | 0.059121 | 0.019288 | 0.012001 | −0.014765 | −0.021426 | 0.037973 | −0.018772 | 0.020665 | −0.047067 | 0.030955 | −0.045576 | 0.028869 | −0.033097 |
| 209 | 0.013041 | 0.00362 | 0.026997 | 0.013091 | 0.029442 | 0.018608 | 0.01818 | −0.002987 | 0.056748 | 0.022897 | 0.032899 | 0.000421 | 0.010967 | 0.031431 |
| 210 | −0.020112 | 0.023386 | 0.09133 | 0.010659 | 0.015062 | 0.02029 | −0.005247 | 0.040471 | −0.032318 | −0.080285 | −0.011695 | 0.019256 | 0.039212 | −0.031963 |
| 211 | 0.063995 | −0.000189 | −0.031514 | 0.01563 | −0.013246 | 0.025031 | 0.001767 | 0.007756 | −0.069299 | −0.000904 | −0.021067 | 0.00153 | −0.003706 | 0.006241 |
| 212 | −0.013198 | 0.006195 | −0.010979 | −0.033365 | −0.029197 | −0.003908 | 0.000379 | 0.012557 | −0.008878 | −0.030223 | 0.003259 | 0.013799 | −0.025384 | 0.000269 |
| 213 | −0.050097 | −0.053361 | −0.084408 | −0.002508 | −0.020558 | −0.041193 | −0.022916 | 0.006184 | 0.013572 | 0.039224 | 0.013952 | 0.001214 | −0.012568 | 0.014667 |
| 214 | 0.032203 | 0.04094 | −0.048482 | 0.018167 | 0.018171 | 0.037347 | −0.013914 | 0.036728 | 0.029706 | 0.001402 | −0.001433 | 0.011591 | 0.013226 | 0.007957 |
| 215 | −0.020658 | 0.000895 | 0.010068 | 0.005806 | −0.003859 | −0.057661 | 0.010563 | 0.040119 | 0.027842 | −0.014741 | 0.012467 | 0.044495 | −0.012085 | 0.03567 |
| 216 | −0.037061 | −0.035158 | −0.014834 | −0.014922 | −0.007045 | −0.006529 | 0.001534 | −0.010359 | −0.006767 | −0.002228 | −0.004824 | −0.014244 | −0.023796 | 0.008211 |
| 217 | 0.012439 | −0.015 | 0.026983 | −0.006088 | 0.015779 | −0.031974 | 0.011774 | −0.024328 | 0.046223 | 0.060851 | −0.009937 | −0.015287 | 0.037678 | −0.014538 |
| 218 | −0.051949 | −0.006879 | 0.00385 | −0.033942 | −0.012251 | −0.019585 | 0.012684 | 0.016709 | 0.011644 | −0.034191 | −0.011417 | 0.022398 | −0.013552 | 0.037761 |
| 219 | −0.079983 | −0.029509 | 0.032521 | −0.02352 | −0.015917 | −0.026379 | 0.006534 | 0.002438 | 0.012248 | −0.053931 | 0.002559 | 0.026431 | −0.023555 | 0.018872 |
| 220 | 0.037382 | 0.038002 | 0.007474 | −0.004347 | 0.026627 | 0.003872 | 0.039415 | −0.036809 | −0.022604 | 0.069656 | 0.013808 | 0.013184 | 0.029148 | 0.059221 |
| 221 | −0.019879 | −0.066398 | −0.036712 | −0.016241 | 0.000114 | −0.006134 | −0.026856 | −0.010054 | −0.012743 | 0.019932 | −0.002143 | −0.005902 | −0.003094 | −0.004626 |
| 222 | 0.026769 | −0.015866 | 0.017878 | −0.030086 | −0.018534 | 0.017719 | −0.034633 | −0.051842 | −0.020931 | 0.035493 | 0.010797 | 0.020284 | 0.007366 | −0.011228 |
| 223 | −0.033905 | 0.029343 | −0.000803 | 0.02328 | −0.018971 | 0.000485 | −0.034953 | −0.026239 | −0.00881 | 0.004631 | −0.010118 | 0.026734 | −0.017734 | 0.000567 |
| 224 | −0.002778 | 0.041225 | −0.00624 | 0.003378 | 0.009616 | −0.010399 | −0.006121 | −0.070128 | −0.022545 | −0.006037 | −0.009437 | 0.010598 | −0.024791 | −0.000283 |
| 225 | 0.003613 | −0.004196 | 0.035473 | −0.019666 | 0.004955 | −0.010711 | −0.02612 | −0.036749 | −0.04208 | −0.011053 | −0.013462 | 0.009989 | −0.011191 | −0.030446 |
| 226 | −0.030028 | 0.017015 | −0.005346 | −0.002365 | −0.025984 | −0.001338 | −0.03411 | 0.003606 | −0.018068 | 0.006121 | −0.012352 | 0.028358 | 0.018874 | 0.012263 |
| 227 | −0.041638 | 0.018485 | 0.02681 | 0.015422 | −0.020398 | 0.032301 | −0.00026 | 0.086842 | 0.018205 | 0.044563 | −0.021369 | −0.032707 | 0.00458 | 0.023508 |
| 228 | −0.064896 | 0.033676 | −0.025852 | −0.020688 | −0.022001 | −0.03636 | 0.025274 | −0.025796 | 0.009426 | −0.032345 | −0.017735 | 0.003914 | −0.01844 | −0.07044 |
| 229 | −0.006243 | −0.002249 | 0.031737 | −0.041417 | 0.023367 | 0.017929 | −0.044372 | −0.024153 | −0.020998 | 0.03375 | −0.014897 | 0.021022 | −0.013779 | −0.01679 |
| 230 | 0.014903 | 0.033009 | −0.000013 | −0.015155 | −0.012422 | 0.000024 | −0.035826 | 0.001052 | −0.013745 | −0.003405 | −0.015843 | 0.035793 | −0.020587 | 0.01333 |
| 231 | −0.037114 | −0.00949 | −0.017466 | −0.023183 | −0.033111 | −0.015523 | 0.058575 | −0.036842 | 0.022676 | −0.040973 | −0.010592 | 0.02981 | −0.019312 | −0.023547 |
| 232 | −0.021921 | −0.06567 | −0.00408 | −0.03999 | 0.035432 | −0.036582 | 0.015722 | −0.076965 | 0.009065 | 0.023617 | −0.006266 | 0.037999 | 0.021832 | −0.038343 |
| 233 | 0.024196 | 0.014194 | −0.013584 | −0.007177 | 0.036902 | 0.013638 | −0.025469 | −0.009457 | 0.006852 | 0.091158 | 0.016423 | −0.007454 | 0.049345 | −0.012366 |
| 234 | −0.02195 | 0.05382 | 0.03884 | 0.002025 | 0.015292 | 0.080337 | −0.028461 | −0.049301 | −0.041379 | 0.00399 | −0.020895 | −0.078886 | 0.001499 | 0.010397 |
| 235 | 0.039696 | −0.022037 | −0.062465 | 0.009633 | 0.011382 | −0.02513 | 0.01875 | −0.041644 | 0.014944 | −0.026477 | −0.041278 | −0.013519 | −0.029809 | −0.011949 |
| 236 | −0.016273 | −0.001442 | 0.015683 | −0.005602 | −0.000288 | −0.003837 | −0.00683 | 0.048644 | 0.023212 | 0.044141 | 0.025676 | 0.015235 | 0.014095 | −0.01154 |
| 237 | −0.007964 | 0.009287 | 0.060351 | 0.0267 | 0.003279 | 0.005897 | 0.002178 | −0.007042 | 0.005105 | −0.001431 | −0.02906 | 0.018219 | 0.017676 | −0.066431 |
| 238 | 0.018209 | 0.038899 | −0.001382 | −0.000427 | −0.024422 | 0.011402 | 0.022508 | 0.030888 | −0.033209 | −0.006398 | −0.003861 | −0.025335 | −0.003475 | −0.006099 |
| 239 | 0.019214 | −0.024256 | −0.025247 | −0.019285 | 0.001948 | 0.024053 | 0.014467 | 0.021382 | −0.023838 | −0.043814 | −0.010328 | −0.022766 | −0.007965 | −0.002536 |
| 240 | 0.081291 | −0.013454 | −0.064818 | −0.002407 | −0.017726 | −0.022551 | 0.01128 | 0.023039 | 0.055997 | −0.009657 | 0.028603 | 0.034385 | 0.000418 | 0.015945 |
| 241 | 0.015501 | −0.028943 | 0.046707 | −0.003559 | 0.014044 | 0.044845 | 0.001239 | −0.031788 | 0.009566 | −0.000516 | −0.039131 | −0.0223 | 0.028776 | −0.005427 |
| 242 | 0.05564 | −0.0202 | −0.043627 | 0.013388 | 0.01438 | −0.020863 | −0.035569 | −0.040013 | 0.008762 | 0.000911 | 0.023365 | −0.021666 | 0.005491 | −0.020679 |
| 243 | 0.038591 | 0.013059 | 0.036299 | 0.009371 | −0.022867 | −0.011871 | 0.001661 | −0.0121 | −0.002899 | −0.015044 | 0.013161 | −0.046039 | −0.004469 | −0.00158 |
| 244 | −0.017122 | −0.053318 | −0.008101 | −0.006318 | 0.023073 | −0.031076 | 0.001132 | −0.035068 | −0.02344 | −0.002341 | 0.002947 | 0.004406 | 0.03367 | −0.037447 |
| 245 | −0.031134 | −0.056847 | −0.020943 | −0.036914 | −0.000552 | 0.013685 | 0.022381 | 0.050236 | 0.023178 | −0.094735 | −0.02129 | −0.029116 | −0.018704 | −0.008771 |
| 246 | 0.007264 | −0.049464 | 0.032361 | −0.004785 | 0.002617 | 0.020681 | 0.037039 | 0.027784 | 0.003129 | −0.001469 | −0.010887 | −0.00591 | −0.017567 | 0.00314 |
| 247 | 0.020998 | −0.01812 | 0.033614 | 0.036456 | −0.010325 | 0.023908 | −0.017408 | 0.00777 | −0.008069 | 0.030113 | 0.003096 | −0.006513 | 0.010676 | −0.038768 |
| 248 | −0.010534 | −0.020838 | 0.0242 | 0.004309 | −0.01432 | −0.03309 | −0.019688 | −0.032378 | −0.03545 | 0.011578 | 0.015355 | 0.023963 | −0.004263 | −0.045165 |
| 249 | 0.020001 | −0.001931 | 0.032668 | −0.022193 | −0.049158 | −0.019907 | 0.017408 | 0.046946 | 0.016168 | −0.0042 | 0.023756 | −0.020118 | −0.011998 | 0.032221 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 250 | 0.002892 | −0.025358 | −0.007886 | 0.010204 | 0.006626 | −0.010988 | 0.033514 | −0.010031 | 0.026527 | 0.010844 | 0.005426 | 0.045136 | −0.016222 | −0.020496 |
| 251 | −0.057539 | −0.051195 | −0.001138 | −0.033352 | −0.017643 | −0.019168 | 0.028123 | −0.023325 | 0.040793 | −0.000725 | 0.000839 | 0.06298 | 0.016585 | −0.011885 |
| 252 | 0.036934 | 0.000832 | −0.004107 | −0.019929 | −0.044312 | −0.026704 | −0.017048 | 0.022303 | 0.007688 | −0.055457 | −0.000882 | 0.022274 | −0.008365 | 0.032566 |
| 253 | 0.027193 | 0.010777 | −0.021541 | −0.016614 | 0.019101 | −0.00562 | 0.039157 | −0.027664 | 0.010978 | 0.024774 | 0.027633 | −0.051916 | −0.007572 | 0.014574 |
| 254 | 0.006086 | 0.033772 | −0.015005 | 0.037313 | 0.003462 | −0.007154 | 0.000178 | −0.012382 | −0.01272 | −0.00621 | −0.001169 | −0.024066 | −0.011493 | 0.002995 |
| 255 | 0.019803 | −0.024039 | 0.008974 | −0.007868 | −0.025949 | −0.036074 | 0.050459 | −0.037501 | −0.000068 | 0.009068 | 0.015945 | 0.011498 | 0.00325 | −0.001441 |
| 256 | 0.000307 | 0.01611 | 0.041451 | −0.019935 | −0.022665 | −0.014481 | 0.055178 | 0.012879 | 0.015943 | −0.015316 | −0.014109 | 0.000783 | −0.027583 | 0.050441 |
| 257 | −0.035379 | −0.021729 | −0.031331 | 0.022125 | 0.016966 | 0.014359 | −0.02722 | 0.007366 | −0.021784 | 0.014659 | 0.022503 | 0.012306 | −0.037037 | −0.009773 |
| 258 | 0.034133 | −0.042744 | −0.004872 | 0.01264 | 0.004489 | 0.042881 | 0.008475 | −0.002424 | 0.006217 | −0.013292 | 0.005736 | −0.033788 | 0.017244 | −0.010292 |
| 259 | 0.003215 | 0.012336 | 0.014864 | 0.011792 | −0.00037 | 0.010611 | −0.030214 | 0.012453 | 0.003084 | −0.033248 | 0.029374 | 0.009103 | 0.003518 | −0.012216 |
| 260 | −0.056364 | 0.042021 | 0.001267 | 0.016823 | 0.034064 | 0.017687 | −0.04933 | 0.039907 | 0.011554 | −0.008837 | 0.013434 | 0.056821 | −0.012042 | 0.000711 |
| 261 | −0.004508 | −0.003201 | 0.045251 | 0.025152 | 0.001865 | −0.013866 | −0.013422 | 0.05324 | 0.000972 | −0.010033 | −0.018126 | −0.01176 | −0.001222 | 0.025955 |
| 262 | −0.000047 | 0.025245 | −0.001594 | 0.015879 | −0.003145 | 0.016506 | −0.045084 | 0.013642 | −0.007379 | −0.021145 | −0.018 | −0.029179 | −0.020836 | 0.031895 |
| 263 | −0.018394 | −0.002695 | 0.009849 | −0.047911 | −0.039661 | −0.041634 | −0.007257 | 0.018126 | −0.033433 | −0.008605 | 0.001047 | −0.020506 | −0.052555 | 0.001987 |
| 264 | 0.003141 | −0.032195 | 0.001545 | −0.014326 | 0.024444 | 0.023405 | 0.042411 | −0.066789 | −0.032135 | −0.008819 | 0.030889 | −0.017624 | 0.01888 | −0.017638 |
| 265 | 0.024288 | 0.003612 | −0.015797 | 0.034071 | 0.044649 | 0.017599 | 0.029465 | −0.019854 | −0.008046 | 0.008561 | −0.011298 | 0.00492 | 0.005034 | 0.035652 |
| 266 | −0.013962 | 0.052366 | 0.026813 | 0.009618 | 0.020351 | −0.01421 | 0.009474 | 0.039327 | −0.007703 | 0.003465 | −0.043652 | 0.034997 | 0.009271 | 0.009529 |
| 267 | 0.03132 | −0.031973 | −0.033749 | 0.029607 | −0.011105 | 0.016882 | 0.023417 | 0.070565 | 0.009489 | −0.025484 | −0.007222 | −0.094944 | −0.008056 | 0.060942 |
| 268 | −0.011756 | −0.000212 | 0.018699 | −0.010075 | −0.019609 | −0.001626 | −0.042149 | −0.007307 | −0.028058 | 0.031793 | −0.000119 | 0.00149 | 0.004875 | 0.007246 |
| 269 | −0.019927 | 0.012302 | 0.044542 | −0.01075 | −0.042046 | −0.043571 | −0.034424 | −0.015878 | −0.017349 | 0.039531 | −0.013826 | −0.006915 | −0.012091 | 0.000683 |
| 270 | −0.007263 | −0.005954 | 0.022996 | −0.001515 | −0.028228 | −0.02994 | −0.000946 | −0.028431 | 0.01803 | 0.027318 | 0.007256 | −0.034453 | −0.001838 | 0.000873 |
| 271 | 0.048971 | 0.006575 | −0.014968 | 0.010735 | −0.004062 | −0.016454 | 0.029731 | 0.02832 | 0.064829 | −0.053515 | 0.014816 | 0.025659 | −0.012247 | −0.116223 |
| 272 | −0.08698 | −0.049612 | −0.019171 | −0.039907 | −0.024615 | 0.008777 | 0.041329 | −0.057457 | −0.008757 | −0.008299 | 0.022831 | 0.012745 | 0.000119 | −0.013156 |
| 273 | 0.037696 | 0.016661 | −0.03415 | −0.003546 | −0.004111 | 0.001373 | −0.04623 | −0.055403 | 0.000948 | 0.008611 | 0.035429 | 0.059541 | 0.022334 | −0.003973 |
| 274 | 0.03082 | 0.013648 | −0.036527 | −0.001109 | 0.001144 | −0.011555 | −0.032307 | −0.050289 | 0.026734 | −0.000999 | 0.019808 | 0.052851 | 0.018417 | −0.010147 |
| 275 | −0.0219 | −0.027762 | −0.017462 | 0.005272 | −0.024441 | −0.040686 | −0.013411 | 0.020616 | 0.006774 | −0.004202 | 0.021712 | −0.033636 | −0.008532 | −0.003675 |
| 276 | −0.028309 | 0.015867 | −0.008843 | −0.001565 | 0.008065 | 0.050951 | 0.001675 | 0.030627 | −0.010654 | 0.035679 | 0.017375 | −0.015517 | 0.022915 | 0.01954 |
| 277 | 0.028551 | 0.024509 | 0.004357 | 0.011414 | 0.019786 | −0.006526 | 0.004788 | −0.00216 | 0.006645 | 0.017971 | 0.002813 | −0.008781 | 0.00484 | −0.01489 |
| 278 | 0.007955 | 0.05067 | −0.020045 | 0.014761 | 0.009347 | −0.002256 | 0.009588 | −0.000778 | 0.053333 | 0.026544 | 0.011658 | −0.023295 | −0.025488 | −0.013497 |
| 279 | 0.00857 | 0.036773 | −0.041451 | −0.020648 | 0.004789 | −0.005582 | −0.001783 | 0.018718 | −0.004884 | −0.030331 | 0.016648 | −0.01366 | −0.009971 | 0.037928 |
| 280 | 0.021293 | −0.009875 | 0.047295 | −0.026874 | −0.015368 | 0.029237 | 0.013262 | 0.029111 | −0.001183 | 0.049633 | 0.005844 | −0.043537 | 0.042538 | 0.014538 |
| 281 | −0.038308 | −0.061725 | −0.025806 | 0.000648 | 0.004765 | 0.018977 | 0.013652 | −0.010322 | −0.01221 | −0.031722 | −0.024746 | 0.006697 | 0.006277 | 0.052766 |
| 282 | −0.024006 | 0.036647 | −0.032612 | −0.00778 | −0.040183 | −0.013138 | 0.025834 | 0.049783 | 0.009388 | 0.030484 | 0.00584 | −0.0022 | −0.024097 | 0.052394 |
| 283 | −0.015754 | 0.053476 | 0.001856 | 0.016379 | −0.009336 | 0.024928 | −0.007354 | 0.050346 | 0.073303 | 0.021205 | −0.001008 | 0.009961 | −0.018973 | −0.010073 |
| 284 | −0.019498 | −0.014556 | −0.047526 | 0.023324 | 0.042439 | 0.037286 | −0.011804 | −0.016431 | −0.019049 | 0.022236 | 0.027458 | −0.007093 | −0.020002 | 0.012641 |
| 285 | −0.012656 | 0.047345 | −0.027012 | 0:003605 | 0.021055 | 0.015917 | 0.019717 | −0.016575 | 0.011377 | 0.028048 | 0.03213 | −0.004499 | −0.041317 | −0.008353 |
| 286 | 0.005559 | 0.016893 | −0.004948 | 0.010782 | 0.018616 | 0.033695 | 0.026255 | −0.022018 | −0.008246 | 0.001984 | −0.00012 | −0.022135 | 0.028771 | 0.003451 |
| 287 | −0.019605 | 0.035011 | 0.006814 | 0.001374 | −0.014887 | 0.031222 | 0.013393 | 0.012739 | 0.015949 | −0.01151 | −0.019196 | −0.003426 | −0.000829 | 0.001842 |
| 288 | 0.021266 | 0.052704 | −0.02327 | −0.025326 | 0.0051 | 0.025758 | 0.028537 | 0.028998 | 0.071789 | −0.001939 | 0.018527 | 0.032421 | 0.004032 | 0.021705 |
| 289 | −0.009 | 0.004625 | −0.002839 | −0.002629 | 0.004196 | −0.008796 | −0.00408 | 0.026978 | 0.031873 | 0.002505 | 0.002951 | 0.03274 | 0.002636 | 0.024607 |
| 290 | 0.016233 | −0.028544 | −0.037051 | −0.016459 | −0.007223 | −0.01709 | −0.018523 | 0.010702 | 0.013383 | 0.008769 | 0.007835 | 0.001016 | −0.016224 | 0.014658 |
| 291 | 0.018002 | −0.049634 | −0.039096 | −0.018215 | −0.008248 | −0.023156 | −0.01219 | 0.011677 | 0.008212 | 0.003718 | 0.005808 | −0.010312 | −0.020179 | 0.003245 |
| 292 | 0.022125 | −0.05792 | −0.013269 | −0.023923 | −0.002548 | −0.004397 | 0.015313 | −0.044962 | −0.015907 | 0.016835 | −0.018747 | 0.003711 | 0.000484 | −0.022253 |
| 293 | −0.110618 | −0.037412 | 0.009422 | −0.011665 | −0.002412 | 0.047218 | −0.070897 | 0.056872 | −0.012041 | 0.04776 | 0.02359 | −0.00967 | −0.012185 | −0.005662 |
| 294 | −0.011316 | −0.045134 | 0.030157 | 0.019539 | 0.014777 | −0.045914 | 0.024171 | −0.015091 | 0.016225 | −0.049044 | 0.007149 | 0.014449 | 0.000658 | −0.034694 |
| 295 | −0.012206 | 0.014055 | −0.04973 | 0.04264 | 0.019992 | 0.012123 | −0.033946 | 0.045835 | 0.02682 | −0.035896 | 0.005328 | −0.004742 | −0.023259 | 0.001014 |
| 296 | 0.041543 | −0.001503 | 0.015234 | −0.00937 | −0.015701 | −0.043125 | 0.050627 | −0.02053 | 0.00412 | −0.02016 | −0.031805 | −0.043898 | −0.014864 | −0.000356 |
| 297 | 0.00355 | 0.01757 | −0.01749 | 0.001313 | 0.000923 | 0.055032 | −0.032213 | −0.03221 | −0.004399 | −0.007943 | −0.01329 | −0.013795 | −0.024517 | 0.004791 |
| 298 | −0.031443 | 0.002784 | 0.071093 | −0.020499 | −0.003851 | 0.025066 | −0.025024 | 0.043442 | −0.032857 | −0.022575 | 0.005521 | −0.029005 | −0.039251 | −0.055379 |
| 299 | −0.005391 | 0.002274 | 0.023875 | −0.039347 | −0.005167 | 0.00883 | −0.03381 | 0.007056 | −0.008106 | 0.035179 | −0.0271 | 0.009006 | 0.018483 | −0.023328 |
| 300 | −0.048882 | 0.013419 | −0.001166 | 0.030289 | 0.021696 | 0.106747 | −0.021424 | 0.053951 | −0.04068 | −0.026996 | −0.025578 | 0.01746 | 0.017368 | −0.04859 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 301 | −0.041985 | −0.011461 | 0.015261 | 0.005465 | 0.016734 | 0.033163 | −0.019222 | 0.032173 | −0.048755 | 0.054866 | 0.010135 | −0.037079 | −0.046977 | 0.029181 |
| 302 | −0.005424 | −0.073593 | 0.020662 | −0.040141 | −0.015791 | −0.055659 | 0.03419 | 0.037885 | −0.004035 | −0.026535 | 0.005048 | 0.013076 | −0.015138 | 0.009823 |
| 303 | −0.02475 | 0.011068 | −0.030948 | 0.042903 | 0.013616 | −0.013008 | −0.010482 | 0.010973 | 0.005561 | −0.018567 | −0.014774 | −0.024358 | 0.042671 | 0.019917 |
| 304 | 0.056021 | −0.037659 | −0.019685 | −0.040689 | 0.003309 | −0.005583 | 0.014452 | −0.00694 | 0.02525 | 0.026605 | −0.010028 | −0.01641 | 0.051356 | −0.035663 |
| 305 | 0.460094 | −0.002561 | 0.028994 | 0.027122 | 0.024726 | 0.002837 | −0.033427 | −0.011005 | −0.036922 | 0.029303 | −0.015957 | −0.051013 | 0.010052 | 0.018817 |
| 306 | −0.066948 | 0.626505 | −0.058062 | −0.096223 | −0.025669 | −0.097339 | 0.001305 | −0.01518 | −0.031436 | −0.012728 | 0.00864 | −0.020529 | −0.001736 | −0.044031 |
| 307 | −0.021887 | −0.048567 | 0.251242 | 0.032022 | 0.048745 | −0.016188 | −0.044263 | 0.003176 | 0.028072 | −0.042581 | 0.014797 | 0.062603 | 0.01696 | 0.023523 |
| 308 | 0.004226 | −0.086025 | 0.067726 | 0.775875 | −0.092613 | −0.063554 | 0.044101 | −0.004949 | −0.007998 | 0.046426 | −0.023687 | 0.012557 | −0.037978 | −0.043097 |
| 300 | 0.008337 | −0.010768 | 0.050766 | −0.08412 | 0.834702 | −0.097895 | −0.001267 | 0.078435 | −0.019866 | −0.01535 | −0.044189 | −0.016432 | −0.097889 | −0.040526 |
| 310 | 0.029136 | −0.107492 | −0.009142 | −0.088254 | −0.064743 | 0.641038 | 0.033535 | 0.01599 | 0.021793 | −0.070813 | 0.030493 | 0.059486 | −0.045813 | −0.030841 |
| 311 | −0.03465 | 0.030554 | −0.01797 | 0.051622 | −0.009469 | 0.038103 | 0.76978 | −0.007887 | −0.093585 | 0.027991 | −0.0302 | 0.032941 | −0.028426 | −0.022293 |
| 312 | −0.026083 | −0.005304 | 0.019174 | 0.031722 | 0.035633 | 0.012839 | −0.059083 | 0.323462 | −0.034557 | −0.075079 | −0.052994 | 0.022838 | 0.047595 | −0.026371 |
| 313 | −0.080765 | −0.014431 | 0.062669 | −0.019756 | −0.041238 | 0.021161 | −0.083825 | −0.049023 | 0.721287 | 0.008919 | −0.052262 | −0.038087 | −0.032057 | −0.016061 |
| 314 | −0.010543 | −0.032185 | −0.021052 | 0.006267 | −0.005698 | −0.063196 | −0.031471 | −0.071047 | −0.052826 | 0.370805 | −0.039881 | −0.023996 | −0.05376 | −0.103498 |
| 315 | −0.052863 | −0.010691 | 0.017848 | −0.019565 | −0.054958 | 0.010884 | −0.047122 | −0.023105 | −0.067005 | −0.035073 | 0.81994 | −0.034615 | −0.045627 | −0.032652 |
| 316 | −0.030375 | −0.000366 | 0.012807 | 0.030672 | 0.011792 | 0.02506 | 0.010204 | 0.005076 | −0.025784 | −0.009499 | −0.029017 | 0.2887 | −0.005411 | 0.03154 |
| 317 | −0.018992 | −0.002313 | −0.021385 | −0.014723 | −0.0928 | −0.046107 | −0.044231 | 0.06757 | −0.024941 | −0.069211 | −0.073877 | −0.005876 | 0.77867 | −0.086696 |
| 318 | 0.036755 | −0.040493 | 0.04803 | −0.040075 | −0.048671 | −0.014555 | −0.051165 | −0.058968 | −0.041317 | −0.04487 | −0.048245 | 0.016684 | −0.079237 | 0.631818 |
| 319 | 0.007983 | 0.018622 | −0.009232 | −0.034396 | −0.055393 | −0.046246 | −0.006086 | −0.030076 | −0.030844 | −0.01464 | −0.12212 | −0.007176 | −0.100365 | −0.069261 |
| 320 | 0.131266 | −0.015013 | −0.027066 | −0.041643 | 0.017086 | −0.034985 | −0.019349 | −0.01421 | −0.028908 | 0.006564 | 0.002181 | 0.089398 | −0.027457 | −0.073055 |
| 321 | 0.061214 | −0.049505 | −0.037791 | −0.022448 | −0.028888 | 0.016392 | −0.001713 | 0.026062 | −0.061912 | −0.036473 | −0.057631 | −0.027125 | 0.020978 | 0.039969 |
| 322 | 0.032355 | 0.028928 | −0.070434 | 0.020987 | −0.014273 | −0.021975 | 0.012624 | −0.018368 | 0.050282 | −0.034512 | 0.04319 | 0.029766 | 0.004222 | −0.000798 |
| 323 | 0.093643 | −0.015709 | −0.008837 | 0.05711 | −0.002563 | −0.033544 | −0.020236 | −0.010878 | −0.021583 | 0.010584 | 0.006068 | −0.05892 | 0.027281 | 0.034803 |
| 324 | −0.035812 | −0.049214 | 0.046119 | −0.00033 | −0.026275 | −0.052157 | 0.010476 | −0.00598 | −0.001483 | −0.01032 | 0.010291 | −0.102421 | 0.034435 | −0.008609 |
| 325 | 0.029694 | 0.070841 | 0.012866 | 0.014117 | −0.062957 | −0.011943 | −0.027097 | 0.045846 | −0.051271 | 0.016865 | −0.042857 | −0.011537 | −0.045484 | 0.017499 |
| 326 | −0.000676 | −0.006098 | −0.060261 | −0:09963 | 0.044344 | 0.043079 | −0.052935 | −0.04662 | 0.044989 | −0.107824 | 0.00292 | 0.076005 | −0.037652 | 0.033962 |
| 327 | 0.042091 | −0.028806 | 0.014289 | −0.088256 | −0.067416 | −0.040395 | 0.012673 | 0.011267 | 0.004815 | 0.007782 | −0.065349 | −0.030343 | −0.050978 | −0.069394 |
| 328 | −0.072927 | −0.026926 | 0.022522 | −0.050028 | −0.03787 | 0.017312 | 0.03065 | −0.040486 | 0.050832 | −0.000811 | 0.015221 | −0.024566 | −0.013658 | 0.027766 |
| 329 | 0.000312 | 0.008238 | 0.011618 | 0.019342 | −0.012023 | 0.003067 | −0.012244 | −0.035853 | −0.030138 | −0.000927 | −0.045424 | −0.004315 | −0.011531 | −0.025085 |
| 330 | 0.002973 | −0.045159 | 0.031137 | −0.014804 | 0.012697 | −0.020362 | 0.012777 | 0.029357 | −0.017224 | −0.003342 | 0.000964 | 0.051126 | −0.030829 | 0.025183 |
| 331 | −0.026058 | −0.035691 | −0.039754 | 0.001628 | −0.03408 | −0.010273 | −0.017839 | −0.020646 | 0.006752 | 0.007767 | −0.061577 | −0.010024 | 0.014961 | −0.007874 |
| 332 | 0.024553 | 0.068277 | −0.069187 | 0.00782 | −0.002791 | −0.026409 | −0.060338 | −0.017063 | −0.016346 | 0.066485 | 0.035705 | −0.014021 | 0.001486 | −0.018322 |
| 333 | 0.008976 | 0.016429 | 0.021147 | −0.0067 | −0.058961 | −0.009449 | −0.019932 | 0.002536 | −0.018996 | 0.030849 | −0.037325 | −0.038054 | −0.063883 | −0.084333 |
| 334 | −0.000962 | 0.068509 | 0.04196 | 0.028915 | 0.002605 | 0.013793 | 0.011193 | −0.015941 | 0.009472 | −0.002308 | −0.013309 | −0.007234 | 0.010803 | 0.000155 |
| 335 | −0.017034 | −0.029522 | −0.007681 | −0.073971 | −0.045141 | −0.069427 | −0.000998 | −0.016552 | 0.003356 | 0.057937 | −0.029691 | 0.02538 | −0.048102 | −0.008178 |
| 336 | 0.022281 | −0.026942 | 0.00155 | 0.031089 | −0.010962 | −0.019722 | −0.026197 | −0.039182 | 0.03783 | −0.016068 | −0.005043 | −0.030609 | −0.027739 | −0.070636 |
| 337 | −0.050218 | −0.041436 | −0.013317 | 0.030725 | 0.034319 | 0.003586 | −0.020639 | −0.048801 | 0.003758 | −0.004395 | 0.014196 | −0.085017 | 0.029841 | 0.029736 |
| 338 | −0.079202 | −0.016022 | −0.044491 | −0.004721 | −0.004214 | −0.00655 | −0.018797 | −0.050709 | 0.011084 | −0.018389 | −0.013093 | −0.038238 | 0.007299 | 0.052318 |
| 339 | 0.035089 | −0.030586 | −0.056966 | 0.040613 | 0.025336 | 0.005642 | −0.06996 | −0.0233 | −0.008135 | −0.037486 | −0.024373 | −0.047747 | −0.008191 | 0.037941 |
| 340 | −0.015286 | −0.033588 | −0.010677 | 0.00484 | −0.018967 | 0.009735 | −0.004677 | 0.035274 | 0.013047 | 0.008335 | −0.001342 | −0.033674 | 0.009914 | −0.054663 |

| | LH | LI | LJ | LK | LL | LM | LN | LO | LP | LQ | LR | LS | LT | LU |
|---|---|---|---|---|---|---|---|---|---|---|---|---|---|---|
| 1 | −0.038658 | −0.039816 | 0.019608 | 0.089589 | 0.055043 | −0.040706 | 0.000848 | −0.017709 | −0.042947 | −0.076659 | −0.050715 | 0.060205 | 0.029523 | 0.05696 |
| 2 | −0.078001 | 0.005354 | 0.028623 | −0.02011 | −0.002058 | −0.070962 | −0.109451 | −0.082869 | −0.035479 | −0.050498 | 0.005133 | 0.058634 | −0.103579 | 0.064008 |
| 3 | 0.028452 | −0.037042 | −0.079843 | −0.060807 | −0.038182 | −0.107479 | 0.006081 | 0.157621 | −0.025714 | −0.016126 | −0.030949 | −0.016938 | 0.027415 | −0.086018 |
| 4 | −0.074637 | −0.069684 | 0.038482 | 0.073913 | 0.021807 | −0.069682 | 0.010717 | 0.054897 | −0.01081 | −0.036737 | 0.005517 | 0.064255 | −0.029389 | −0.010462 |
| 5 | 0.043338 | 0.021967 | 0.029489 | −0.058609 | −0.019651 | −0.039414 | −0.033429 | −0.131346 | −0.020524 | −0.018465 | −0.025969 | 0.078479 | −0.026794 | 0.026742 |
| 6 | 0.050626 | 0.063671 | −0.04443 | 0.063165 | 0.028873 | −0.05764 | 0.027126 | 0.039313 | 0.032016 | −0.050675 | 0.022127 | 0.012862 | 0.001015 | −0.00053 |
| 7 | 0.000009 | −0.042832 | 0.037888 | −0.035793 | 0.01848 | −0.05243 | −0.015578 | −0.036418 | −0.035921 | 0.029155 | −0.012823 | −0.035433 | 0.054555 | 0.053588 |
| 8 | −0.030226 | 0.000393 | 0.053712 | 0.063808 | −0.016746 | 0.050725 | 0.01493 | −0.027048 | 0.00689 | −0.083242 | 0.031622 | 0.034558 | −0.018704 | 0.00696 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 9 | 0.063601 | −0.052272 | −0.012591 | 0.032388 | −0.010684 | −0.006987 | −0.024245 | 0.072931 | 0.019723 | −0.071404 | 0.043363 | −0.073599 | 0.075717 | −0.005668 |
| 10 | 0.005249 | 0.051902 | −0.033114 | 0.11677 | −0.103674 | 0.068741 | 0.084845 | −0.004807 | 0.001796 | 0.096578 | −0.023642 | 0.007109 | −0.008327 | 0.089003 |
| 11 | 0.025132 | −0.032417 | 0.012536 | 0.026917 | 0.053778 | −0.006275 | 0.005433 | 0.017368 | −0.007632 | −0.013727 | 0.002208 | 0.007845 | −0.027647 | −0.063474 |
| 12 | −0.008575 | 0.008888 | −0.052625 | −0.060426 | 0.033705 | 0.024907 | 0.034658 | 0.025352 | −0.002685 | 0.023018 | −0.032964 | 0.045937 | −0.009967 | −0.035109 |
| 13 | 0.082924 | 0.070603 | −0.062487 | −0.104077 | −0.052391 | −0.014551 | 0.039417 | 0.063847 | 0.040885 | −0.144069 | 0.100717 | 0.113338 | 0.039827 | −0.016234 |
| 14 | 0.008585 | −0.004796 | −0.038745 | 0.070221 | −0.086643 | −0.00908 | −0.071015 | −0.049642 | 0.069702 | −0.037547 | 0.000632 | −0.015817 | −0.069018 | −0.002071 |
| 15 | 0.081619 | 0.041987 | 0.020655 | −0.069519 | −0.048522 | 0.059777 | 0.081713 | −0.006081 | 0.056153 | 0.121504 | 0.015283 | 0.000775 | −0.060853 | −0.122193 |
| 16 | −0.000568 | −0.042348 | 0.007712 | −0.041402 | −0.012611 | 0.038703 | −0.02073 | −0.047513 | −0.020118 | −0.025731 | −0.005354 | −0.009193 | 0.011989 | −0.015002 |
| 17 | −0.054198 | −0.005221 | −0.066166 | −0.0605 | −0.068058 | 0.032544 | −0.00761 | −0.001858 | 0.008052 | 0.01858 | −0.066984 | 0.036961 | 0.020567 | −0.028043 |
| 18 | −0.004113 | 0.022199 | −0.014566 | −0.044386 | 0.038514 | 0.005317 | 0.045608 | 0.033024 | 0.01355 | 0.01132 | 0.02539 | −0.050688 | 0.040652 | 0.045835 |
| 19 | −0.055924 | −0.034046 | −0.032426 | −0.119856 | −0.00203 | −0.068094 | −0.06426 | −0.025931 | −0.021613 | −0.040254 | 0.011719 | −0.013899 | 0.000689 | −0.045828 |
| 20 | −0.075609 | 0.012262 | −0.045823 | 0.091669 | −0.07692 | −0.115496 | −0.046256 | −0.009562 | −0.115605 | 0.082391 | −0.037229 | −0.039314 | −0.051717 | 0.011937 |
| 21 | 0.030406 | −0.028214 | −0.069449 | 0.104867 | −0.003666 | 0.023259 | 0.02112 | −0.023197 | 0.046165 | −0.052173 | 0.025566 | −0.026729 | 0.010201 | −0.017456 |
| 22 | 0.078032 | −0.043958 | 0.007879 | 0.005737 | 0.01887 | 0.061536 | −0.012531 | −0.034865 | −0.002599 | −0.041983 | −0.046986 | −0.000152 | −0.010105 | −0.012678 |
| 23 | −0.032033 | −0.0378 | −0.028064 | −0.0438 | −0.053256 | −0.024634 | 0.034135 | 0.002992 | −0.0548 | 0.079481 | −0.043311 | −0.028747 | −0.035442 | 0.024654 |
| 24 | −0.012743 | 0.034587 | 0.037661 | 0.046226 | 0.141831 | 0.050769 | 0.060458 | −0.02856 | 0.035435 | 0.186444 | 0.017514 | 0.053041 | 0.070991 | 0.014233 |
| 25 | −0.012549 | 0.041374 | 0.060074 | −0.063735 | −0.026817 | 0.12488 | 0.054994 | −0.012114 | −0.02329 | −0.04472 | −0.061006 | −0.081777 | 0.006454 | 0.035081 |
| 26 | −0.042627 | −0.07965 | 0.04823 | −0.195916 | −0.054985 | −0.038308 | −0.024984 | 0.022672 | 0.013239 | 0.036794 | 0.017106 | −0.00583 | −0.010254 | −0.123992 |
| 27 | 0.038881 | −0.063615 | −0.036323 | 0.083813 | −0.099471 | 0.033914 | 0.039044 | 0.047673 | 0.019472 | 0.006548 | 0.035488 | −0.094172 | 0.030072 | −0.06843 |
| 28 | 0.038924 | 0.026077 | −0.010177 | 0.00486 | 0.003636 | −0.066062 | 0.043471 | 0.084013 | −0.006398 | 0.038545 | −0.05029 | −0.008653 | 0.095263 | 0.042849 |
| 29 | 0.005258 | 0.046032 | 0.016092 | 0.158021 | −0.034419 | −0.006725 | 0.009959 | 0.006686 | −0.025963 | −0.012495 | −0.019486 | −0.03932 | −0.072512 | 0.019714 |
| 30 | −0.019181 | 0.033866 | −0.098453 | −0.027506 | −0.070181 | −0.008124 | 0.022422 | 0.014844 | −0.038201 | −0.012034 | −0.057969 | 0.02628 | −0.031462 | −0.020525 |
| 31 | 0.027364 | −0.005402 | −0.125224 | −0.00951 | −0.057951 | −0.051006 | −0.002836 | 0.012199 | −0.035786 | −0.082381 | −0.109531 | −0.000872 | 0.076524 | −0.005131 |
| 32 | 0.028512 | 0.008273 | −0.026871 | 0.042765 | −0.023687 | −0.085473 | −0.053787 | −0.016189 | 0.049332 | −0.085918 | 0.04797 | 0.073505 | −0.001399 | 0.06539 |
| 33 | −0.002082 | −0.035202 | −0.043612 | −0.059545 | 0.1036 | 0.04139 | −0.013841 | −0.014294 | 0.021749 | −0.179995 | 0.034954 | −0.019061 | 0.080687 | 0.024163 |
| 34 | 0.008303 | 0.02061 | −0.052778 | −0.081589 | 0.019044 | −0.121487 | −0.063575 | −0.050061 | 0.047128 | 0.077627 | 0.001336 | 0.029434 | −0.030922 | −0.050976 |
| 35 | −0.017226 | −0.068909 | 0.060829 | −0.048772 | −0.030892 | −0.057113 | 0.079924 | 0.003447 | 0.00059 | 0.059766 | −0.007225 | 0.023919 | 0.007832 | −0.034991 |
| 36 | 0.033954 | 0.046783 | −0.050432 | 0.062629 | 0.028647 | 0.099218 | 0.082389 | −0.030368 | −0.040354 | 0.051841 | −0.015273 | 0.056644 | −0.052474 | −0.029481 |
| 37 | −0.019821 | 0.035574 | −0.181716 | 0.018947 | 0.013198 | −0.003929 | −0.039794 | −0.075634 | 0.025201 | −0.031775 | −0.071061 | −0.072086 | 0.029089 | −0.063061 |
| 38 | 0.023289 | −0.056799 | 0.021778 | 0.126122 | 0.00903 | 0.03686 | −0.021457 | −0.015152 | 0.034013 | −0.036249 | 0.023557 | −0.016176 | 0.071885 | 0.094623 |
| 39 | 0.030037 | 0.096094 | 0.030547 | 0.047464 | 0.003472 | −0.057566 | 0.059266 | 0.113618 | 0.046321 | −0.014609 | 0.025984 | −0.049186 | 0.031234 | −0.017581 |
| 40 | 0.033605 | 0.093606 | 0.055944 | −0.043301 | 0.063924 | −0.062973 | 0.006712 | −0.114525 | 0.037389 | −0.013712 | 0.111865 | −0.058566 | 0.003669 | 0.024171 |
| 41 | −0.022169 | −0.056157 | −0.120079 | −0.006465 | −0.015498 | 0.019665 | −0.090365 | 0.050398 | −0.043658 | 0.026907 | −0.047926 | −0.051429 | −0.063516 | −0.025376 |
| 42 | −0.035921 | −0.090678 | −0.012906 | 0.108544 | 0.047154 | −0.033173 | −0.043629 | −0.087794 | −0.002141 | −0.013134 | −0.044445 | −0.063463 | −0.00418 | −0.063697 |
| 43 | −0.022609 | −0.046811 | 0.025857 | −0.031406 | 0.031959 | −0.128633 | 0.035885 | −0.030075 | 0.025055 | −0.007872 | 0.018664 | 0.027724 | −0.017166 | −0.04303 |
| 44 | 0.010923 | −0.001029 | 0.042571 | 0.015062 | −0.181069 | 0.153453 | 0.051564 | 0.209097 | 0.007985 | −0.261258 | −0.024452 | 0.050485 | −0.048166 | 0.173914 |
| 45 | −0.009145 | 0.044973 | 0.028223 | −0.003816 | −0.032611 | 0.153046 | 0.00838 | −0.065734 | 0.004122 | 0.006745 | −0.010588 | 0.028148 | 0.052925 | 0.092172 |
| 46 | −0.082943 | 0.017273 | −0.032727 | 0.015495 | 0.017982 | −0.016791 | −0.063949 | −0.008344 | 0.007999 | −0.068026 | 0.093161 | 0.072681 | 0.004886 | −0.017224 |
| 47 | −0.008861 | −0.096883 | 0.085087 | −0.011631 | −0.062803 | −0.01931 | 0.012872 | −0.009833 | 0.017871 | 0.011584 | −0.010684 | −0.047759 | −0.00616 | −0.036534 |
| 48 | −0.036794 | 0.056658 | −0.092666 | −0.102388 | 0.009933 | 0.049638 | 0.043797 | 0.042627 | −0.004102 | 0.04009 | −0.057513 | 0.005864 | 0.009423 | −0.070805 |
| 49 | 0.012146 | −0.015059 | 0.048469 | −0.098634 | 0.056449 | 0.055229 | −0.080681 | −0.021958 | −0.026676 | 0.085121 | 0.04676 | 0.076465 | −0.052003 | 0.053061 |
| 50 | 0.029745 | −0.094807 | −0.067117 | −0.069125 | 0.009269 | 0.033416 | 0.043421 | −0.034751 | −0.043724 | −0.023649 | −0.00361 | −0.008786 | −0.001374 | 0.062808 |
| 51 | 0.049059 | 0.038702 | 0.015304 | −0.086069 | −0.019212 | −0.123629 | 0.001428 | 0.04037 | 0.010431 | −0.013338 | −0.004363 | 0.019852 | −0.013174 | −0.002122 |
| 52 | 0.02327 | 0.019734 | −0.031898 | 0.040191 | 0.020677 | −0.060313 | −0.006309 | 0.021215 | 0.033788 | −0.014337 | 0.006412 | 0.002484 | 0.021671 | 0.015061 |
| 53 | 0.046561 | 0.009785 | 0.021776 | 0.132856 | 0.025504 | −0.09078 | 0.019556 | −0.113634 | −0.053273 | −0.118826 | 0.026789 | 0.068368 | −0.041136 | −0.034511 |
| 54 | 0.01793 | −0.026768 | −0.020167 | 0.070417 | −0.004051 | −0.081958 | 0.044215 | 0.046521 | −0.03624 | 0.083369 | −0.036064 | 0.16493 | −0.049977 | −0.002736 |
| 55 | −0.084472 | −0.105457 | −0.044078 | −0.059845 | −0.072702 | −0.073367 | −0.018002 | −0.082962 | 0.015177 | −0.097271 | −0.043414 | −0.118724 | −0.072286 | 0.115903 |
| 56 | 0.043019 | −0.007257 | −0.003673 | 0.143153 | 0.008309 | −0.017905 | 0.003254 | 0.011882 | 0.029252 | 0.076696 | −0.006706 | −0.101237 | 0.005817 | −0.027312 |
| 57 | −0.068186 | 0.074338 | 0.10948 | 0.046851 | 0.033467 | 0.012351 | 0.025468 | 0.049314 | 0.029803 | 0.089545 | 0.032739 | 0.110251 | −0.079118 | 0.124695 |
| 58 | 0.009773 | 0.035797 | 0.062945 | −0.143224 | 0.033542 | 0.084325 | −0.029309 | 0.011302 | −0.002763 | −0.04777 | 0.002515 | −0.048657 | −0.015336 | 0.010778 |
| 59 | 0.021381 | 0.154862 | 0.019521 | −0.040986 | 0.035041 | −0.066829 | −0.028112 | −0.129634 | −0.06401 | 0.093192 | −0.073558 | 0.01607 | −0.032619 | −0.04041 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 60 | −0.010614 | 0.031036 | −0.018991 | −0.024363 | 0.001746 | 0.116818 | −0.023067 | 0.01263 | −0.048439 | −0.034463 | 0.092819 | 0.054365 | −0.024193 | −0.081304 |
| 61 | 0.035024 | 0.036388 | −0.058926 | −0.043777 | −0.021234 | −0.066072 | −0.010003 | −0.064406 | 0.008533 | 0.073869 | 0.020377 | 0.065057 | 0.034616 | −0.043602 |
| 62 | −0.035899 | −0.016582 | 0.054068 | 0.015104 | 0.06737 | −0.07187 | −0.04112 | −0.049638 | −0.018001 | 0.001215 | −0.069883 | 0.058278 | −0.045629 | 0.038076 |
| 63 | −0.040624 | 0.010356 | 0.03878 | −0.00094 | 0.033756 | 0.078846 | −0.01026 | 0.000891 | −0.009361 | −0.036798 | 0.010348 | −0.083843 | 0.033901 | 0.03495 |
| 64 | 0.007107 | −0.05063 | −0.000234 | −0.019465 | 0.007693 | 0.046152 | 0.010421 | 0.02968 | −0.010942 | 0.001377 | −0.01692 | −0.020095 | 0.021179 | −0.007706 |
| 65 | −0.00465 | −0.074325 | −0.032727 | 0.034344 | −0.086954 | 0.084961 | −0.067448 | 0.043325 | 0.006477 | 0.047782 | 0.00671 | −0.03036 | 0.007231 | −0.003317 |
| 66 | 0.038934 | −0.226141 | 0.009975 | −0.066156 | 0.060165 | 0.001894 | 0.060319 | −0.095356 | −0.000112 | −0.03556 | 0.023716 | −0.072355 | 0.012056 | −0.078706 |
| 67 | −0.005212 | 0.058 | −0.024428 | −0.044249 | −0.055795 | 0.010577 | −0.017925 | 0.056394 | −0.062561 | −0.012571 | −0.07846 | −0.043974 | −0.083871 | −0.009016 |
| 68 | 0.009366 | 0.002495 | 0.023781 | 0.065943 | 0.00679 | −0.006611 | 0.031425 | −0.009553 | 0.02367 | 0.118692 | 0.03565 | 0.009517 | 0.028546 | 0.064028 |
| 69 | 0.009649 | −0.101234 | 0.04478 | 0.008201 | −0.020313 | 0.152784 | 0.030619 | −0.070155 | −0.043594 | −0.021997 | −0.00397 | 0.075371 | −0.058818 | −0.079736 |
| 70 | 0.012793 | −0.118896 | −0.020911 | −0.059107 | −0.04379 | −0.021328 | −0.002156 | −0.098726 | 0.011029 | 0.08045 | 0.010093 | −0.110398 | −0.032175 | 0.106576 |
| 71 | 0.014963 | 0.076821 | 0.059895 | 0.095419 | 0.067484 | −0.015262 | −0.01849 | −0.045659 | −0.00748 | 0.015937 | 0.048753 | 0.037959 | 0.022104 | 0.036766 |
| 72 | 0.02727 | 0.00058 | −0.04643 | −0.104606 | 0.009793 | −0.034397 | −0.028314 | 0.056321 | 0.034517 | 0.124653 | −0.020357 | 0.109296 | 0.017568 | 0.087922 |
| 73 | −0.026073 | 0.073841 | 0.029618 | 0.013284 | −0.065678 | −0.088268 | 0.12889 | 0.017752 | 0.009513 | −0.108424 | 0.004372 | −0.167129 | −0.002247 | −0.127335 |
| 74 | −0.025449 | 0.016344 | −0.045302 | 0.121263 | −0.020979 | 0.039033 | 0.020464 | −0.017464 | −0.028798 | −0.003198 | −0.055062 | 0.074493 | −0.002206 | −0.018283 |
| 75 | 0.062287 | −0.036228 | 0.00876 | 0.006305 | 0.07692 | 0.037037 | −0.028119 | 0.027088 | −0.077123 | 0.005506 | −0.022128 | −0.091082 | −0.05082 | 0.129336 |
| 76 | −0.016469 | 0.072874 | 0.099493 | 0.060087 | 0.137276 | −0.066982 | 0.027771 | 0.025047 | 0.090081 | −0.001916 | 0.038762 | −0.061719 | 0.087839 | 0.032867 |
| 77 | −0.058876 | 0.018603 | −0.070445 | −0.007684 | 0.087348 | −0.098687 | −0.077733 | 0.155684 | −0.054955 | 0.055918 | −0.003174 | 0.010207 | 0.053391 | −0.016585 |
| 78 | −0.023685 | 0.001858 | 0.022003 | 0.076991 | −0.100252 | 0.197986 | 0.006259 | −0.026797 | −0.020283 | −0.035732 | −0.082618 | 0.138657 | 0.021495 | −0.065796 |
| 79 | −0.006349 | 0.053269 | −0.113627 | −0.062344 | −0.023254 | −0.136265 | 0.023121 | 0.016527 | −0.038656 | −0.031678 | −0.045114 | −0.101333 | 0.016237 | −0.013601 |
| 80 | 0.00668 | 0.071966 | 0.001652 | 0.020372 | 0.017366 | −0.007195 | 0.043427 | 0.010674 | 0.003466 | −0.027241 | −0.001443 | 0.070915 | −0.027 | 0.000706 |
| 81 | −0.042694 | −0.039723 | 0.068447 | 0.057707 | −0.006176 | −0.092037 | 0.063052 | −0.039837 | −0.007521 | −0.013056 | 0.000901 | 0.076166 | 0.01848 | −0.039554 |
| 82 | −0.032406 | −0.059303 | 0.044754 | 0.093216 | 0.046444 | −0.058933 | −0.03749 | −0.041469 | 0.03263 | −0.025402 | 0.092242 | −0.14038 | 0.047662 | −0.017097 |
| 83 | −0.030511 | −0.15714 | 0.021664 | 0.042692 | 0.055744 | 0.078238 | 0.030444 | 0.042673 | −0.044837 | 0.134182 | 0.004454 | −0.075699 | 0.055372 | −0.042022 |
| 84 | −0.002109 | 0.102271 | 0.016888 | −0.091657 | 0.075839 | −0.016103 | −0.001653 | −0.003706 | −0.050321 | −0.017838 | −0.024081 | 0.087461 | −0.078433 | −0.038062 |
| 85 | −0.011704 | −0.084115 | −0.033599 | 0.05008 | −0.007634 | 0.023182 | −0.021079 | −0.13457 | 0.030242 | −0.00389 | 0.055056 | 0.009745 | −0.08131 | 0.041209 |
| 86 | 0.020225 | 0.03824 | −0.00532 | −0.002422 | 0.000839 | 0.055574 | −0.040166 | −0.093901 | 0.045875 | −0.012961 | 0.010116 | −0.07706 | −0.039636 | 0.00128 |
| 87 | 0.030857 | −0.029622 | 0.039018 | 0.001584 | 0.136403 | −0.062573 | −0.025279 | 0.055147 | −0.049331 | 0.006253 | 0.073445 | −0.066291 | −0.021072 | −0.004763 |
| 88 | −0.087494 | 0.024732 | 0.007542 | 0.074265 | 0.129079 | 0.086638 | 0.040627 | 0.031471 | 0.015929 | −0.014243 | −0.022647 | 0.047764 | 0.019411 | −0.104416 |
| 89 | 0.097504 | 0.049935 | −0.061089 | 0.036164 | 0.000979 | −0.016491 | −0.095529 | −0.041456 | 0.052753 | −0.056825 | 0.070127 | 0.049374 | 0.017868 | −0.042459 |
| 90 | 0.038613 | 0.004067 | 0.055559 | −0.054794 | −0.130641 | 0.093993 | 0.061137 | 0.014767 | −0.06847 | −0.036309 | −0.014953 | −0.047888 | 0.001057 | 0.014938 |
| 91 | −0.074396 | −0.06609 | 0.108866 | 0.000083 | −0.046043 | −0.012887 | 0.058403 | 0.078403 | 0.035484 | 0.072315 | 0.082262 | 0.030385 | 0.032483 | −0.046939 |
| 92 | −0.015136 | 0.062711 | −0.001599 | 0.05823 | −0.016545 | 0.032811 | −0.07154 | −0.006674 | −0.060494 | 0.088833 | −0.096992 | 0.001762 | −0.045657 | −0.057002 |
| 93 | 0.032772 | −0.03346 | −0.015494 | −0.083313 | −0.074392 | −0.041349 | 0.030153 | 0.081979 | 0.018322 | 0.106965 | 0.000072 | 0.374243 | 0.011946 | 0.48011 |
| 94 | −0.032281 | 0.049894 | 0.107917 | −0.006407 | 0.054831 | 0.134219 | 0.03166 | 0.003021 | 0.042993 | −0.186615 | −0.005916 | −0.032614 | 0.079954 | −0.026303 |
| 95 | −0.045082 | 0.007583 | −0.024928 | −0.037583 | −0.001921 | 0.018666 | −0.070547 | 0.060765 | −0.025698 | 0.043651 | −0.063038 | −0.041662 | −0.02701 | 0.007143 |
| 96 | 0.023278 | 0.021418 | −0.019412 | −0.063029 | −0.048271 | −0.030254 | −0.007529 | 0.020924 | 0.024076 | 0.025145 | −0.002066 | −0.065442 | 0.025041 | 0.004261 |
| 97 | −0.02195 | −0.065011 | −0.006246 | 0.020363 | −0.04946 | −0.016548 | −0.031771 | 0.071383 | −0.026844 | −0.037973 | −0.00362 | −0.005459 | −0.043236 | −0.09951 |
| 98 | 0.126603 | 0.010494 | 0.027757 | 0.144988 | −0.063948 | −0.100396 | 0.048072 | 0.081795 | 0.018036 | 0.001801 | 0.007501 | −0.015166 | −0.113933 | 0.044075 |
| 99 | −0.043922 | 0.036865 | −0.029583 | 0.086265 | 0.014885 | 0.061753 | −0.013414 | 0.013292 | −0.055037 | 0.043144 | −0.006452 | −0.165148 | 0.014296 | 0.024935 |
| 100 | 0.007339 | −0.011122 | 0.047239 | −0.144668 | −0.071334 | 0.066507 | 0.002317 | −0.089355 | −0.010254 | −0.010326 | 0.015707 | −0.153818 | −0.000859 | 0.140321 |
| 101 | −0.083188 | −0.10463 | −0.024031 | 0.03558 | 0.051349 | 0.067316 | 0.041049 | −0.03086 | −0.080657 | −0.00278 | −0.07554 | −0.03053 | −0.006601 | −0.058936 |
| 102 | 0.058559 | 0.026729 | 0.043399 | −0.108834 | 0.097225 | 0.033896 | 0.045916 | −0.091152 | −0.010862 | −0.090475 | 0.007384 | 0.125385 | −0.007298 | −0.039934 |
| 103 | −0.006966 | −0.038336 | 0.01414 | 0.058016 | −0.010473 | −0.032768 | −0.010857 | −0.134583 | 0.014406 | 0.049378 | −0.017444 | 0.026248 | −0.007965 | 0.005939 |
| 104 | 0.008196 | −0.05163 | 0.054298 | 0.047343 | −0.036929 | −0.018907 | 0.003893 | −0.016241 | −0.004489 | −0.065683 | 0.037856 | 0.031306 | 0.042069 | 0.053649 |
| 105 | −0.025957 | 0.0233 | −0.046551 | −0.008661 | 0.01288 | −0.001166 | −0.017131 | −0.0098 | −0.084521 | 0.024848 | −0.027673 | −0.031314 | −0.048492 | −0.001036 |
| 106 | −0.012609 | 0.008077 | −0.061091 | 0.0367 | −0.023286 | −0.000182 | 0.07423 | 0.013185 | 0.014811 | −0.13724 | −0.003839 | −0.001477 | 0.020974 | 0.02073 |
| 107 | −0.037592 | −0.009701 | −0.078156 | 0.045915 | 0.030154 | 0.019882 | −0.057095 | 0.021896 | 0.040031 | −0.014546 | 0.028009 | 0.010782 | 0.008738 | 0.074003 |
| 108 | 0.024203 | 0.028421 | −0.043996 | −0.057571 | −0.040735 | −0.053246 | −0.150023 | −0.01413 | 0.00924 | −0.013429 | 0.011653 | −0.093656 | 0.005058 | 0.035779 |
| 109 | −0.022388 | −0.013397 | −0.011304 | −0.010188 | 0.059003 | 0.117488 | 0.01066 | 0.053677 | −0.029375 | 0.047504 | −0.016408 | −0.045789 | 0.008597 | −0.002969 |
| 110 | −0.007512 | −0.000654 | −0.018457 | −0.031255 | 0.03309 | −0.007701 | −0.01893 | −0.026151 | −0.029728 | −0.085435 | −0.051497 | −0.006499 | −0.067443 | 0.022947 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 111 | −0.010262 | −0.076124 | 0.006675 | 0.040446 | −0.025346 | 0.113134 | 0.037051 | −0.05537 | −0.057122 | 0.10615 | −0.030148 | 0.139997 | −0.03879 | −0.034821 |
| 112 | −0.025594 | −0.046418 | 0.061333 | 0.019323 | 0.034634 | 0.005855 | 0.090617 | 0.007297 | 0.005474 | −0.052847 | 0.073064 | 0.007383 | 0.03149 | −0.004841 |
| 113 | −0.016708 | −0.012186 | 0.002551 | 0.107986 | 0.029038 | −0.005015 | −0.025068 | −0.026851 | 0.015938 | −0.012467 | 0.067212 | 0.012185 | 0.026584 | −0.001654 |
| 114 | 0.015705 | −0.035995 | 0.061268 | −0.039731 | 0.001619 | 0.013704 | −0.004624 | −0.021034 | −0.018203 | 0.032856 | −0.008249 | 0.001209 | −0.030802 | −0.001854 |
| 115 | 0.037722 | 0.101729 | 0.038884 | 0.026284 | −0.030607 | 0.025048 | 0.005688 | 0.117307 | 0.08299 | 0.087565 | 0.06856 | 0.016703 | 0.032175 | 0.041131 |
| 116 | −0.008394 | 0.006891 | 0.033819 | −0.030252 | −0.041328 | −0.060734 | −0.006721 | −0.037918 | −0.013289 | −0.023922 | −0.055015 | −0.031811 | 0.027849 | 0.038034 |
| 117 | −0.023861 | −0.046533 | 0.009017 | −0.082046 | −0.076635 | −0.005545 | 0.050929 | 0.01839 | −0.01704 | −0.045422 | −0.091778 | −0.021078 | 0.007146 | 0.090169 |
| 118 | −0.043521 | 0.02648 | 0.057551 | 0.00919 | 0.055771 | 0.033299 | −0.06137 | −0.109221 | 0.01274 | −0.045621 | −0.008036 | 0.058658 | −0.025006 | 0.050287 |
| 119 | 0.085669 | −0.049715 | 0.072888 | −0.052393 | −0.126176 | −0.022401 | 0.04627 | 0.131843 | −0.04908 | −0.010744 | 0.06989 | −0.017435 | −0.006127 | −0.059796 |
| 120 | −0.023909 | −0.025521 | −0.033363 | 0.111114 | 0.098998 | 0.09313 | −0.037745 | −0.006253 | 0.013962 | 0.007154 | 0.038644 | −0.033783 | −0.022929 | −0.005678 |
| 121 | −0.013263 | −0.083201 | 0.011922 | 0.00592 | 0.021441 | 0.04597 | −0.084098 | 0.042564 | 0.003139 | 0.033385 | 0.014805 | −0.064584 | −0.093026 | −0.033645 |
| 122 | −0.005565 | −0.035084 | 0.010383 | −0.041649 | −0.035496 | 0.027243 | 0.08903 | 0.119649 | −0.0375 | 0.044307 | −0.017383 | −0.012091 | 0.005828 | 0.096549 |
| 123 | −0.001087 | −0.042735 | 0.054934 | −0.014953 | −0.104345 | 0.058439 | −0.068817 | −0.045869 | −0.019642 | 0.009218 | −0.015089 | −0.012242 | −0.005111 | −0.054009 |
| 124 | 0.058605 | 0.157863 | −0.132064 | 0.039244 | −0.039973 | −0.03855 | 0.020683 | −0.102657 | 0.009049 | −0.032963 | −0.09808 | 0.014951 | 0.011718 | 0.042116 |
| 125 | −0.028887 | 0.047322 | −0.045605 | 0.059048 | 0.065279 | 0.083764 | −0.051057 | −0.010398 | −0.003641 | 0.082977 | 0.067104 | −0.005362 | −0.031931 | 0.051381 |
| 126 | −0.016324 | 0.011792 | −0.151983 | 0.052559 | 0.044183 | −0.040083 | 0.001717 | −0.019998 | −0.05879 | −0.062475 | 0.03642 | −0.105289 | 0.043543 | 0.128039 |
| 127 | 0.031308 | −0.051498 | 0.02668 | 0.032856 | 0.096744 | 0.040805 | 0.004967 | 0.041438 | 0.061725 | 0.054872 | 0.070542 | 0.02564 | −0.015258 | −0.039138 |
| 128 | −0.009984 | 0.077616 | −0.063592 | −0.062449 | 0.038247 | 0.067261 | 0.078707 | −0.087059 | 0.04589 | 0.008722 | 0.01616 | −0.007419 | −0.017402 | −0.045455 |
| 129 | −0.05543 | 0.009242 | 0.032233 | 0.06842 | 0.013155 | −0.015313 | −0.029893 | −0.094626 | −0.020223 | −0.088752 | −0.072307 | 0.041877 | −0.0011 | 0.053835 |
| 130 | −0.025367 | 0.006029 | 0.015235 | 0.055452 | −0.00858 | −0.032594 | 0.003515 | 0.007655 | −0.02651 | 0.005519 | 0.063881 | −0.010096 | 0.019738 | 0.02516 |
| 131 | −0.037518 | 0.050575 | 0.01963 | −0.006567 | −0.036632 | −0.064728 | 0.036831 | 0.02152 | 0.032424 | −0.071281 | −0.045652 | 0.021735 | 0.010115 | −0.006819 |
| 132 | 0.017414 | −0.007355 | −0.009833 | −0.064664 | −0.032141 | −0.040965 | −0.044162 | 0.081414 | −0.013128 | 0.060849 | 0.072569 | −0.081437 | 0.014382 | 0.063103 |
| 133 | −0.056855 | −0.087934 | −0.064158 | 0.020493 | 0.013476 | 0.03458 | 0.011762 | 0.054701 | −0.052455 | 0.085069 | 0.042982 | 0.023115 | −0.035631 | 0.070681 |
| 134 | −0.007939 | 0.022658 | 0.00645 | −0.076494 | 0.071148 | −0.060745 | 0.077029 | −0.081112 | 0.037931 | −0.018491 | 0.064931 | −0.031388 | 0.034831 | −0.033843 |
| 135 | −0.040641 | −0.139986 | 0.146929 | 0.080372 | 0.014521 | −0.023056 | −0.018288 | −0.125834 | 0.038806 | 0.11812 | −0.041282 | −0.075422 | −0.060424 | −0.068939 |
| 136 | −0.019993 | −0.054157 | 0.041626 | −0.030746 | 0.064661 | −0.039419 | −0.013663 | 0.038151 | −0.054617 | −0.038447 | 0.046972 | 0.037197 | −0.008125 | −0.043824 |
| 137 | 0.047362 | −0.008715 | −0.034713 | −0.006919 | 0.042044 | −0.090185 | −0.099376 | 0.042828 | 0.014498 | −0.043771 | 0.010258 | 0.024599 | 0.037816 | −0.057001 |
| 138 | 0.006699 | 0.01837 | −0.051263 | −0.028355 | −0.028722 | 0.013021 | −0.020148 | 0.022032 | 0.024094 | −0.047088 | 0.009718 | 0.011173 | −0.050174 | −0.109833 |
| 139 | −0.010197 | −0.030054 | −0.026688 | 0.017896 | −0.008129 | −0.016612 | 0.07895 | −0.01367 | −0.023791 | −0.069958 | −0.03738 | 0.066317 | −0.018318 | −0.089538 |
| 140 | 0.08378 | −0.037062 | −0.037955 | 0.054732 | 0.011063 | 0.018259 | 0.003429 | −0.017885 | 0.036578 | −0.022853 | −0.055763 | 0.01142 | 0.042698 | −0.037784 |
| 141 | 0.009116 | 0.029287 | 0.047633 | 0.066948 | −0.033181 | −0.029287 | 0.034614 | 0.058694 | 0.005099 | 0.062596 | 0.027253 | −0.029001 | 0.022647 | −0.019988 |
| 142 | 0.01898 | 0.03363 | −0.042531 | 0.02563 | 0.010361 | 0.00468 | −0.033274 | 0.054655 | 0.014677 | −0.046395 | 0.031845 | 0.007716 | 0.011561 | 0.008099 |
| 143 | −0.031671 | −0.045083 | 0.062773 | 0.032956 | 0.027737 | −0.016045 | 0.009607 | 0.000183 | 0.021916 | 0.001718 | 0.031498 | 0.01135 | −0.025103 | −0.00831 |
| 144 | 0.005037 | 0.004124 | −0.017582 | −0.007469 | 0.00291 | 0.002718 | −0.045848 | −0.060407 | 0.015856 | 0.033336 | −0.004592 | −0.012866 | −0.033405 | 0.030814 |
| 145 | 0.029145 | 0.023218 | −0.093896 | −0.050549 | 0.024303 | 0.05733 | −0.004985 | 0.045206 | −0.017712 | −0.040666 | 0.011065 | −0.01458 | −0.016759 | −0.013875 |
| 146 | −0.010395 | 0.04259 | −0.015659 | −0.011259 | −0.025504 | 0.026538 | −0.015491 | 0.010916 | −0.003093 | −0.0247 | 0.034386 | −0.014121 | −0.021894 | 0.055686 |
| 147 | 0.010791 | 0.045524 | 0.005538 | −0.003381 | −0.034366 | −0.016972 | −0.006281 | 0.014918 | −0.014832 | −0.012869 | −0.024543 | 0.028537 | −0.003249 | −0.010608 |
| 148 | −0.02542 | −0.008504 | 0.038344 | −0.00658 | 0.047942 | −0.006774 | −0.044964 | 0.006933 | −0.014864 | 0.098919 | −0.016424 | 0.067121 | −0.009389 | 0.001949 |
| 149 | −0.00805 | 0.013059 | −0.065487 | −0.093647 | −0.003222 | −0.013408 | −0.011048 | 0.011794 | −0.017417 | −0.028951 | −0.051906 | −0.026161 | 0.006078 | 0.054745 |
| 150 | 0.016746 | −0.065564 | −0.006613 | −0.035551 | −0.030087 | −0.017387 | 0.00552 | −0.026098 | −0.065056 | 0.032046 | −0.046475 | −0.021926 | 0.000736 | −0.026035 |
| 151 | 0.018227 | 0.049958 | 0.045692 | 0.054058 | 0.009231 | 0.028675 | 0.00304 | −0.033346 | −0.008673 | −0.044532 | 0.009647 | 0.009643 | −0.013991 | −0.064466 |
| 152 | −0.064475 | −0.041118 | −0.037422 | 0.021726 | 0.050478 | 0.026232 | 0.004315 | −0.042737 | −0.046156 | 0.001348 | −0.065558 | −0.015029 | 0.036793 | −0.003379 |
| 153 | −0.047723 | 0.057624 | −0.03092 | 0.061827 | −0.047634 | −0.010252 | 0.045473 | −0.014906 | −0.013647 | −0.040825 | −0.021185 | 0.004015 | 0.037722 | 0.030145 |
| 154 | 0.057889 | −0.022637 | 0.017934 | −0.004527 | −0.000093 | 0.057216 | −0.023184 | −0.017748 | 0.010898 | −0.016903 | 0.007291 | 0.023015 | −0.002195 | 0.031564 |
| 155 | 0.007167 | −0.019466 | −0.016444 | −0.02047 | −0.035474 | 0.055321 | 0.030855 | −0.042948 | 0.007663 | −0.047771 | 0.008376 | 0.056995 | −0.0021 | −0.023566 |
| 156 | −0.066136 | 0.015055 | 0.040259 | 0.039677 | −0.022844 | −0.010537 | 0.010251 | −0.008527 | −0.006837 | 0.049361 | −0.016656 | −0.010672 | −0.005302 | 0.006027 |
| 157 | −0.019236 | 0.04347 | −0.038218 | 0.005498 | 0.001797 | −0.037151 | 0.062515 | −0.024719 | 0.034418 | 0.000635 | −0.001537 | −0.048041 | −0.035665 | 0.044018 |
| 158 | −0.032044 | −0.0572 | 0.012731 | −0.072638 | −0.001225 | −0.064287 | 0.058104 | −0.020651 | −0.017375 | 0.006932 | −0.005276 | −0.016564 | −0.021848 | 0.066679 |
| 159 | 0.029256 | −0.013987 | −0.060315 | 0.033046 | −0.011519 | −0.011816 | 0.011901 | −0.019112 | −0.005459 | −0.007135 | 0.014855 | 0.012445 | 0.007684 | −0.007469 |
| 160 | 0.041374 | −0.004691 | 0.047228 | −0.048938 | −0.011782 | −0.005473 | −0.039457 | 0.019369 | 0.020135 | 0.032659 | 0.030906 | −0.040705 | 0.039466 | 0.010206 |
| 161 | 0.007951 | −0.008935 | 0.010114 | 0.043495 | −0.026535 | 0.056524 | 0.057453 | 0.049643 | −0.017158 | 0.000515 | −0.030902 | −0.0161 | −0.040166 | 0.05401 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 162 | −0.002339 | −0.014689 | −0.033821 | −0.033911 | 0.003151 | −0.069073 | −0.013993 | 0.017432 | −0.015306 | 0.032649 | −0.011556 | 0.037144 | −0.059261 | −0.006364 |
| 163 | 0.007621 | 0.005729 | −0.019719 | −0.027179 | 0.035275 | −0.014104 | −0.004294 | 0.054652 | 0.039531 | 0.026341 | −0.002788 | −0.04334 | 0.035506 | −0.001718 |
| 164 | 0.016051 | 0.044662 | −0.013788 | 0.004698 | −0.104419 | 0.052191 | 0.003845 | −0.025724 | −0.026501 | 0.03529 | −0.008904 | 0.015425 | −0.023029 | 0.003795 |
| 165 | 0.011618 | −0.041999 | −0.037546 | 0.070171 | 0.009421 | −0.090527 | 0.039123 | 0.028021 | 0.000905 | −0.010848 | −0.065828 | 0.035345 | 0.008879 | −0.049409 |
| 166 | −0.03832 | 0.029896 | 0.015896 | −0.00291 | −0.006778 | 0.002311 | 0.047716 | −0.006874 | 0.048642 | 0.065481 | 0.030943 | 0.002695 | 0.010954 | −0.011562 |
| 167 | 0.010941 | 0.040156 | 0.019845 | −0.034989 | −0.011987 | −0.0617 | 0.04388 | −0.030785 | −0.04039 | 0.032227 | −0.063661 | −0.07542 | −0.028834 | −0.004456 |
| 168 | −0.01268 | 0.02095 | −0.045174 | −0.0445 | 0.066208 | 0.061163 | 0.009146 | −0.050523 | −0.003787 | 0.011782 | 0.016526 | 0.058592 | −0.010485 | 0.009368 |
| 169 | 0.003566 | −0.002383 | 0.020253 | −0.009009 | −0.02391 | 0.056007 | 0.013155 | 0.014107 | 0.017987 | 0.026889 | 0.021579 | −0.001788 | 0.006647 | 0.010825 |
| 170 | 0.008878 | 0.047902 | 0.013174 | −0.004346 | 0.007303 | 0.009255 | −0.012931 | −0.000701 | 0.013376 | −0.014186 | 0.032657 | 0.007402 | 0.022155 | 0.017979 |
| 171 | 0.014153 | 0.012461 | 0.017732 | −0.000572 | −0.038658 | 0.006889 | 0.009874 | 0.009443 | 0.029738 | 0.030218 | 0.025362 | −0.004804 | 0.021243 | −0.018317 |
| 172 | −0.003896 | 0.005947 | 0.044 | −0.011396 | 0.028363 | 0.089296 | 0.01719 | 0.022688 | 0.00212 | 0.034599 | 0.00143 | 0.017825 | 0.020778 | −0.037663 |
| 173 | 0.01049 | 0.052939 | 0.011141 | 0.051295 | 0.011962 | 0.020315 | 0.004406 | 0.042231 | −0.004248 | 0.003592 | −0.018832 | 0.009823 | 0.00924 | −0.02072 |
| 174 | 0.019861 | −0.038245 | −0.010271 | 0.040432 | −0.026676 | 0.040843 | −0.008794 | 0.025703 | −0.044409 | 0.018682 | −0.002416 | −0.020459 | 0.011341 | −0.024911 |
| 175 | −0.034428 | 0.002298 | −0.004497 | −0.068629 | −0.004653 | −0.011387 | −0.004448 | 0.048866 | −0.018039 | 0.028132 | 0.017118 | 0.000842 | −0.015956 | −0.028544 |
| 176 | −0.007833 | 0.052236 | 0.050881 | −0.072886 | 0.000429 | 0.058847 | 0.018681 | −0.041841 | 0.038 | −0.026496 | −0.00221 | −0.081968 | 0.018886 | 0.019861 |
| 177 | 0.049277 | −0.018982 | −0.027209 | −0.027564 | 0.062286 | −0.023138 | −0.001883 | 0.006655 | −0.01919 | 0.078441 | 0.041081 | −0.028283 | −0.005432 | −0.004584 |
| 178 | 0.01166 | −0.065719 | 0.013918 | −0.041942 | 0.032341 | −0.019208 | 0.01739 | 0.055985 | 0.009105 | 0.004129 | 0.023446 | −0.013616 | 0.003838 | −0.008167 |
| 179 | 0.004926 | −0.002602 | 0.009126 | −0.015113 | −0.007983 | −0.000224 | −0.01017 | −0.00557 | 0.017026 | 0.034086 | 0.020089 | 0.041383 | 0.021309 | −0.045831 |
| 180 | −0.018913 | 0.017123 | 0.008422 | −0.015464 | 0.03166 | −0.017108 | −0.011423 | −0.02997 | 0.001043 | 0.017031 | 0.002714 | 0.029329 | 0.017185 | 0.003287 |
| 181 | −0.0251 | −0.019261 | 0.036287 | −0.016127 | −0.00877 | −0.019849 | −0.004834 | −0.019694 | −0.005621 | 0.00558 | 0.013854 | 0.011041 | 0.021766 | 0.007595 |
| 182 | −0.004758 | −0.031052 | 0.052589 | −0.020397 | 0.014038 | −0.025979 | −0.028497 | −0.028105 | −0.008535 | 0.020121 | 0.017776 | −0.00677 | −0.013933 | −0.017074 |
| 183 | 0.030522 | 0.022591 | −0.012049 | 0.012752 | −0.023587 | −0.019506 | 0.011218 | −0.015364 | −0.001642 | 0.000274 | −0.002651 | −0.003086 | 0.006099 | −0.028297 |
| 184 | 0.009733 | −0.003953 | −0.077315 | 0.079443 | 0.008802 | −0.035141 | 0.009449 | 0.063821 | 0.0246661 | −0.024516 | −0.000234 | 0.021595 | 0.029566 | 0.016543 |
| 185 | −0.035784 | 0.01594 | −0.007932 | −0.001444 | −0.036313 | 0.039242 | −0.030862 | 0.024799 | 0.002983 | 0.002838 | −0.034677 | −0.016159 | 0.001886 | −0.038548 |
| 186 | −0.002362 | −0.005087 | −0.037183 | 0.0023 | −0.060889 | −0.00536 | 0.033086 | −0.02078 | −0.047 | −0.012002 | −0.047145 | 0.023433 | −0.009492 | 0.001968 |
| 187 | 0.0103 | 0.045533 | −0.000426 | 0.036731 | 0.037847 | −0.02611 | 0.03933 | −0.025423 | 0.02674 | −0.034946 | −0.001696 | −0.030406 | −0.006525 | 0.019028 |
| 188 | 0.027989 | 0.007801 | 0.010487 | 0.023122 | 0.026741 | −0.00055 | −0.008199 | −0.008815 | −0.003527 | −0.040179 | 0.016398 | −0.013155 | −0.00966 | −0.006636 |
| 189 | −0.000771 | 0.071876 | 0.004923 | 0.016505 | 0.014475 | −0.040465 | −0.051555 | −0.075842 | 0.0106061 | 0.005087 | −0.001974 | −0.030379 | −0.044986 | −0.003094 |
| 190 | −0.003919 | 0.055962 | −0.003174 | 0.035823 | 0.061612 | 0.032347 | −0.042703 | −0.016622 | −0.022832 | −0.009554 | 0.061498 | 0.027415 | −0.025028 | 0.009974 |
| 191 | −0.013101 | −0.027745 | −0.008572 | −0.017187 | 0.067025 | −0.019264 | −0.022003 | 0.029313 | −0.047868 | 0.004913 | 0.042157 | −0.004731 | −0.001594 | 0.040277 |
| 192 | 0.009499 | 0.007165 | −0.052959 | 0.036052 | −0.033896 | −0.009476 | −0.015635 | 0.014839 | −0.035768 | 0.025978 | −0.030421 | 0.042168 | 0.0085 | 0.01082 |
| 193 | 0.019814 | 0.0424 | −0.003128 | −0.017302 | 0.025677 | 0.031237 | 0.038671 | −0.054711 | 0.051395 | −0.038566 | 0.023147 | 0.008295 | 0.007149 | −0.013367 |
| 194 | −0.041122 | −0.064 | −0.032831 | 0.020223 | 0.006071 | −0.051823 | −0.011152 | 0.077883 | −0.02591 | −0.027262 | −0.004541 | −0.006511 | 0.022037 | 0.059615 |
| 195 | 0.004789 | −0.018682 | 0.045155 | 0.107675 | 0.042737 | −0.020997 | −0.015329 | −0.028544 | 0.025287 | 0.053399 | 0.001967 | 0.022655 | 0.009778 | 0.021232 |
| 196 | −0.04707 | −0.010456 | −0.037407 | 0.079326 | 0.043757 | 0.017805 | −0.009693 | −0.028552 | −0.022572 | 0.03188 | −0.012558 | −0.021746 | −0.013572 | −0.021493 |
| 197 | −0.021582 | 0.013635 | −0.048686 | 0.036175 | −0.057933 | −0.007378 | −0.001712 | 0.001144 | −0.051659 | −0.083462 | −0.023779 | 0.011636 | 0.008481 | 0.013458 |
| 198 | 0.012209 | −0.005763 | −0.0107 | −0.054204 | 0.032488 | −0.006027 | −0.005213 | 0.043326 | 0.000226 | 0.067305 | −0.01 | −0.069168 | −0.005065 | 0.049581 |
| 199 | −0.029523 | −0.049652 | 0.000948 | −0.089442 | −0.060806 | 0.034821 | −0.028997 | 0.029511 | −0.006631 | −0.006021 | 0.019502 | −0.013723 | −0.020483 | 0.018556 |
| 200 | 0.005128 | −0.0193 | 0.02147 | 0.041981 | −0.021434 | 0.055962 | 0.001529 | −0.058488 | 0.041151 | 0.035784 | 0.00735 | −0.023872 | 0.026576 | 0.038602 |
| 201 | 0.035823 | 0.058581 | 0.012387 | 0.046851 | −0.034852 | −0.000021 | −0.00936 | 0.01323 | 0.031121 | −0.008374 | −0.005494 | −0.068017 | −0.009108 | 0.068086 |
| 202 | −0.018 | 0.048759 | −0.006295 | −0.000186 | 0.021243 | −0.003639 | −0.009073 | 0.028034 | −0.00751 | −0.058522 | 0.03213 | −0.01933 | 0.007049 | −0.013155 |
| 203 | 0.010342 | 0.031033 | −0.023301 | 0.028332 | −0.026675 | −0.010492 | 0.008631 | −0.084899 | −0.0143 | −0.001583 | −0.052185 | −0.016839 | −0.034465 | 0.046928 |
| 204 | −0.014876 | −0.039896 | 0.021098 | −0.004051 | −0.019001 | 0.012582 | 0.053886 | −0.029507 | −0.012486 | −0.004668 | −0.044621 | −0.007285 | −0.041116 | 0.081755 |
| 205 | −0.005032 | −0.014104 | 0.06382 | −0.008246 | 0.027237 | 0.008969 | 0.001361 | 0.016412 | −0.012782 | 0.036382 | 0.015474 | −0.060324 | −0.0113 | 0.076489 |
| 206 | 0.001719 | −0.03488 | 0.02979 | 0.033041 | 0.014154 | 0.023835 | 0.039986 | 0.100177 | −0.030315 | 0.031236 | 0.047984 | 0.016496 | 0.036448 | 0.023728 |
| 207 | 0.032857 | −0.066212 | −0.001768 | 0.08768 | 0.035355 | −0.033295 | −0.036313 | −0.004173 | −0.040856 | 0.033507 | 0.028472 | −0.01997 | 0.027954 | −0.030144 |
| 208 | 0.001251 | −0.022975 | −0.014119 | 0.02187 | 0.028149 | −0.052013 | −0.016439 | 0.021481 | −0.014448 | −0.015028 | −0.019171 | −0.004855 | 0.031641 | 0.035922 |
| 209 | 0.021648 | 0.037776 | 0.005385 | 0.01085 | 0.030604 | −0.00992 | −0.048424 | 0.062317 | 0.01864 | −0.029452 | −0.023542 | 0.052635 | −0.021817 | 0.026899 |
| 210 | 0.012771 | −0.013788 | −0.051218 | 0.006134 | −0.053651 | 0.017819 | 0.007606 | −0.048172 | 0.040471 | 0.027533 | −0.000799 | −0.037684 | 0.00028 | 0.009419 |
| 211 | −0.006173 | 0.000309 | −0.065349 | −0.005896 | −0.045018 | −0.03718 | 0.014701 | 0.047231 | 0.024039 | 0.013318 | 0.010836 | −0.041211 | −0.003852 | 0.021212 |
| 212 | 0.021913 | 0.037131 | −0.015459 | 0.021737 | −0.013735 | 0.023718 | 0.029653 | −0.032246 | −0.034282 | −0.005354 | −0.053521 | 0.020603 | −0.046257 | −0.02837 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 213 | 0.005426 | 0.053096 | 0.048923 | −0.017542 | 0.00481 | 0.011933 | −0.036577 | 0.003921 | 0.001212 | −0.019333 | −0.013278 | −0.015979 | −0.04734 | 0.014509 |
| 214 | 0.020442 | 0.038028 | −0.029334 | 0.016521 | −0.0183 | −0.019505 | −0.025549 | 0.001242 | 0.010974 | 0.041845 | −0.008801 | 0.058808 | 0.014577 | −0.025112 |
| 215 | 0.01669 | 0.046379 | −0.000633 | −0.022863 | −0.054656 | −0.041928 | 0.014841 | 0.002376 | 0.023187 | 0.019164 | 0.028466 | −0.030188 | −0.00019 | −0.026804 |
| 216 | −0.018003 | −0.024119 | 0.024147 | 0.03024 | 0.012902 | 0.022475 | 0.029777 | −0.022721 | 0.028268 | −0.018152 | 0.029906 | −0.009766 | −0.005283 | 0.022472 |
| 217 | 0.000378 | 0.007938 | 0.00313 | 0.011053 | 0.000228 | −0.001759 | −0.010403 | 0.035038 | −0.000982 | −0.020931 | 0.033859 | 0.022384 | −0.015318 | −0.010608 |
| 218 | −0.011974 | −0.028095 | 0.019528 | −0.016833 | 0.048775 | −0.009959 | −0.02237 | −0.02535 | 0.006938 | −0.020209 | 0.014355 | 0.01916 | −0.004433 | 0.04062 |
| 219 | −0.003314 | 0.013153 | 0.026535 | 0.004676 | 0.031144 | −0.038466 | 0.038405 | −0.054378 | 0.020378 | −0.008541 | 0.005796 | −0.006884 | −0.023161 | 0.013654 |
| 220 | 0.023755 | −0.047656 | −0.006428 | 0.003413 | 0.025834 | −0.058857 | −0.023478 | 0.03655 | 0.017336 | −0.00532 | 0.00337 | −0.013121 | 0.028695 | −0.030341 |
| 221 | −0.012937 | 0.014324 | 0.009581 | −0.01741 | 0.065711 | 0.010437 | −0.010763 | −0.044643 | −0.011511 | −0.055278 | −0.031673 | 0.040655 | 0.005177 | −0.05492 |
| 222 | 0.00821 | −0.040125 | −0.010641 | −0.005986 | 0.026777 | −0.004248 | −0.017503 | −0.019238 | −0.042466 | 0.011786 | −0.037958 | −0.003307 | −0.02006 | −0.044599 |
| 223 | 0.00704 | −0.027606 | −0.006201 | −0.033412 | 0.017602 | −0.006194 | −0.01441 | 0.03573 | 0.006564 | 0.073129 | −0.012259 | −0.007724 | −0.001706 | −0.001579 |
| 224 | −0.02996 | 0.036548 | 0.012179 | −0.04025 | −0.003258 | −0.024835 | 0.015146 | −0.080239 | 0.001534 | 0.016856 | 0.022052 | 0.037957 | 0.021431 | 0.020283 |
| 225 | −0.027221 | −0.009762 | 0.00014 | −0.056748 | 0.004415 | −0.037772 | 0.033213 | −0.029839 | −0.006784 | 0.016268 | 0.010248 | 0.019058 | 0.027111 | 0.011294 |
| 226 | 0.010344 | 0.002064 | 0.024152 | 0.00321 | −0.030314 | −0.011861 | −0.039313 | 0.020601 | 0.022194 | 0.035267 | 0.016727 | 0.024807 | −0.02304 | 0.00906 |
| 227 | 0.004356 | 0.015908 | −0.00928 | 0.086213 | −0.000927 | −0.016921 | −0.007395 | −0.021825 | 0.004287 | 0.029581 | 0.014637 | 0.03149 | −0.058989 | −0.03972 |
| 228 | −0.015357 | −0.028453 | 0.011648 | −0.015904 | 0.035482 | −0.038537 | −0.095281 | 0.014692 | −0.025533 | −0.064828 | −0.014782 | 0.004092 | −0.013052 | 0.048507 |
| 229 | −0.020631 | 0.033525 | 0.012214 | 0.07775 | 0.015912 | 0.020159 | 0.015599 | 0.018578 | −0.035244 | −0.015233 | −0.001493 | −0.008155 | −0.005117 | 0.030287 |
| 230 | −0.014969 | −0.027194 | 0.004182 | −0.018939 | −0.028618 | 0.069224 | −0.043855 | 0.00447 | −0.036439 | 0.012865 | −0.016135 | −0.009509 | 0.033828 | 0.023022 |
| 231 | −0.035263 | −0.009968 | 0.033029 | −0.015685 | −0.014621 | 0.057074 | 0.015018 | −0.005867 | 0.016839 | 0.045543 | 0.009557 | −0.027028 | 0.011257 | −0.019619 |
| 232 | 0.008713 | −0.008219 | −0.003686 | −0.009251 | −0.011476 | −0.020163 | 0.037137 | −0.014443 | −0.054176 | −0.047143 | −0.039447 | −0.052872 | −0.017425 | −0.062554 |
| 233 | 0.017817 | −0.052461 | −0.019974 | 0.082131 | −0.022943 | 0.001279 | 0.026851 | 0.034571 | 0.018457 | 0.043013 | 0.019958 | 0.025999 | −0.001786 | −0.004306 |
| 234 | −0.003198 | 0.015557 | −0.013967 | 0.042652 | −0.027127 | 0.016622 | −0.007575 | 0.02898 | 0.043009 | −0.010271 | 0.039189 | 0.049359 | 0.024501 | 0.014632 |
| 235 | −0.037924 | 0.039299 | −0.009069 | −0.013475 | 0.004358 | −0.001091 | 0.023854 | 0.03536 | −0.056349 | −0.008782 | −0.042467 | 0.011443 | 0.001508 | −0.013344 |
| 236 | 0.032972 | 0.034757 | 0.005591 | 0.004153 | 0.018351 | 0.015652 | −0.027766 | 0.006634 | 0.010405 | −0.03408 | −0.004504 | 0.00008 | −0.000771 | 0.008258 |
| 237 | −0.028876 | −0.026342 | −0.021784 | −0.009272 | −0.033949 | 0.016952 | 0.017865 | 0.004871 | 0.010685 | −0.041274 | −0.01756 | 0.023901 | −0.004483 | −0.008201 |
| 238 | 0.00533 | −0.004587 | −0.011866 | −0.033586 | −0.021881 | 0.03138 | −0.005134 | 0.012247 | −0.021405 | 0.047806 | −0.014425 | −0.000313 | −0.002111 | −0.014864 |
| 239 | 0.002927 | −0.010097 | 0.00325 | 0.011488 | 0.007149 | 0.047361 | 0.005131 | 0.02144 | −0.024311 | 0.070567 | −0.023865 | −0.031843 | −0.007553 | 0.015524 |
| 240 | 0.007192 | 0.027681 | 0.04017 | 0.023111 | 0.029909 | 0.029805 | −0.011183 | −0.038551 | 0.026474 | 0.03936 | 0.050636 | 0.012221 | −0.017027 | −0.000013 |
| 241 | 0.003697 | −0.009389 | −0.041577 | 0.02114 | −0.002465 | 0.002708 | 0.022549 | −0.05325 | −0.010463 | 0.040334 | 0.007107 | −0.03953 | −0.043285 | 0.011676 |
| 242 | 0.030295 | −0.012117 | 0.00882 | −0.004574 | −0.003584 | −0.032858 | −0.01658 | 0.008668 | −0.03015 | 0.03942 | −0.004486 | −0.028069 | −0.026792 | 0.005584 |
| 243 | 0.001165 | 0.009689 | −0.022987 | −0.005866 | 0.005085 | 0.008557 | 0.012193 | −0.034394 | −0.006817 | −0.003398 | −0.016256 | 0.019247 | −0.009123 | 0.041349 |
| 244 | 0.003775 | 0.024005 | 0.021218 | −0.033903 | 0.034626 | −0.008206 | 0.015314 | 0.024629 | −0.005353 | −0.045906 | 0.002825 | −0.043721 | 0.01661 | 0.007372 |
| 245 | −0.033771 | 0.014464 | 0.012587 | 0.045583 | 0.002317 | 0.00679 | 0.021169 | 0.006229 | −0.020583 | −0.011372 | −0.012962 | −0.029509 | 0.008507 | 0.002378 |
| 246 | −0.015437 | −0.070075 | −0.002532 | 0.049037 | −0.01454 | −0.023224 | 0.017366 | 0.034509 | −0.016263 | 0.014871 | −0.00915 | −0.033233 | −0.008467 | 0.000452 |
| 247 | 0.033945 | −0.000678 | 0.010347 | −0.0237 | −0.015154 | 0.016144 | 0.003685 | −0.001271 | −0.012202 | 0.001905 | −0.009231 | 0.008793 | −0.013782 | −0.013413 |
| 248 | 0.011544 | 0.011254 | 0.065795 | −0.006776 | 0.009435 | 0.014705 | 0.040057 | −0.016509 | 0.007808 | −0.039023 | 0.005115 | 0.037733 | 0.032268 | −0.036685 |
| 249 | −0.011112 | 0.060489 | 0.042267 | 0.007875 | 0.001016 | 0.046137 | −0.023312 | −0.087638 | 0.014411 | −0.067317 | 0.03943 | 0.043763 | 0.012431 | 0.016757 |
| 250 | 0.011936 | −0.006257 | −0.014378 | −0.011767 | −0.01805 | −0.037167 | 0.037687 | −0.026044 | 0.022549 | −0.00918 | 0.020879 | −0.043477 | −0.024568 | 0.005801 |
| 251 | −0.00014 | 0.024665 | −0.061513 | −0.036243 | −0.028328 | −0.002772 | 0.004843 | 0.00167 | −0.047059 | −0.008052 | −0.049695 | −0.045139 | −0.010322 | 0.017321 |
| 252 | 0.006809 | 0.002188 | −0.015569 | −0.047325 | −0.018416 | 0.056178 | −0.020858 | 0.023114 | −0.021368 | 0.015335 | −0.000298 | 0.018147 | 0.010953 | 0.016624 |
| 253 | −0.015309 | −0.027341 | 0.009321 | 0.021067 | −0.018228 | 0.039352 | 0.006752 | 0.015471 | 0.042396 | −0.050218 | 0.026363 | 0.0189 | 0.031075 | −0.004219 |
| 254 | 0.003971 | −0.010925 | −0.030297 | −0.036376 | −0.044644 | 0.004857 | 0.015268 | 0.020468 | 0.013105 | 0.014475 | 0.029122 | 0.017865 | −0.001093 | 0.005 |
| 255 | 0.016103 | 0.005713 | 0.025639 | −0.088527 | 0.013102 | −0.014763 | 0.028521 | 0.007525 | −0.001298 | −0.041559 | 0.010686 | −0.011203 | −0.012522 | 0.007069 |
| 256 | −0.009323 | −0.006985 | −0.008989 | −0.004971 | 0.028294 | 0.024571 | −0.011224 | −0.038552 | 0.005238 | −0.045927 | 0.025656 | 0.025815 | −0.015784 | −0.018705 |
| 257 | −0.000923 | −0.051905 | −0.019006 | −0.016813 | −0.020618 | −0.012694 | 0.039991 | −0.022059 | 0.022928 | −0.025852 | −0.023977 | 0.047445 | 0.031969 | −0.032992 |
| 258 | 0.001486 | −0.049245 | 0.010308 | −0.06898 | 0.032375 | 0.016402 | 0.010105 | −0.048679 | −0.001506 | −0.016025 | −0.005112 | 0.024944 | −0.012496 | −0.002103 |
| 259 | 0.01954 | 0.029923 | 0.019776 | 0.005469 | −0.003336 | −0.037329 | −0.006927 | −0.035543 | 0.0228 | −0.022866 | −0.007104 | 0.004347 | 0.004699 | 0.022043 |
| 260 | 0.012172 | 0.027376 | 0.000888 | −0.014493 | 0.025726 | −0.054806 | 0.020855 | 0.007722 | 0.057109 | −0.044064 | 0.017758 | −0.009775 | 0.050078 | −0.033513 |
| 261 | −0.007842 | 0.033297 | −0.042303 | −0.009053 | −0.015004 | −0.000599 | −0.059365 | −0.01712 | 0.011676 | −0.021754 | 0.00791 | −0.021166 | 0.030555 | −0.011571 |
| 262 | 0.014221 | −0.016356 | −0.010412 | 0.011214 | 0.004457 | −0.001514 | −0.047236 | 0.014761 | 0.021003 | −0.02007 | 0.014672 | 0.017628 | 0.012581 | −0.006205 |
| 263 | −0.020729 | −0.042531 | 0.03338 | −0.007913 | −0.00374 | −0.011671 | 0.003258 | 0.00905 | 0.005972 | −0.043529 | 0.006334 | 0.021068 | 0.021503 | 0.002804 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 264 | 0.005356 | −0.018017 | −0.008416 | 0.043308 | 0.038217 | −0.034255 | −0.005106 | −0.018022 | 0.009124 | −0.011028 | 0.029153 | −0.060248 | −0.00166 | 0.011624 |
| 265 | 0.001219 | −0.022154 | 0.001581 | 0.020756 | 0.038717 | −0.020653 | −0.005037 | 0.017571 | 0.027271 | 0.053728 | 0.02773 | −0.010961 | −0.008244 | 0.002417 |
| 266 | −0.009662 | 0.003691 | 0.002567 | 0.009139 | −0.040957 | −0.006918 | −0.005602 | 0.06874 | 0.012681 | 0.065894 | 0.007799 | 0.013643 | −0.015434 | −0.030876 |
| 267 | 0.003959 | 0.025211 | 0.023611 | −0.018298 | −0.034233 | 0.009168 | 0.035415 | −0.046834 | −0.002261 | 0.045778 | 0.037931 | −0.026612 | −0.002581 | −0.002608 |
| 268 | 0.011419 | 0.020562 | 0.015046 | 0.017103 | −0.000648 | −0.011032 | −0.028393 | −0.01549 | 0.019207 | 0.043178 | 0.009908 | 0.01169 | −0.015737 | −0.008558 |
| 269 | 0.013248 | 0.04031 | −0.000201 | 0.016395 | −0.016354 | −0.029746 | −0.039259 | 0.032437 | −0.000318 | 0.028982 | 0.001832 | −0.017831 | −0.014847 | −0.028475 |
| 270 | 0.015342 | 0.019247 | 0.013144 | 0.003147 | 0.000411 | −0.020814 | −0.018769 | −0.018571 | 0.000206 | −0.022202 | 0.007901 | 0.018452 | −0.014581 | 0.014674 |
| 271 | 0.052763 | −0.005934 | 0.04219 | −0.018035 | 0.027525 | −0.063802 | 0.023778 | −0.033549 | −0.052709 | 0.003844 | 0.025889 | 0.047494 | −0.038445 | −0.058318 |
| 272 | −0.004234 | 0.035782 | 0.012356 | −0.005417 | 0.02268 | 0.016171 | 0.011984 | −0.002182 | −0.010757 | 0.024171 | −0.00273 | −0.058723 | −0.005588 | 0.012148 |
| 273 | 0.014068 | −0.001185 | −0.033838 | 0.007401 | −0.004976 | 0.01454 | −0.044544 | −0.006422 | −0.004847 | 0.001994 | −0.001798 | 0.019352 | 0.01542 | 0.010765 |
| 274 | 0.006235 | 0.013427 | −0.025805 | −0.020326 | −0.001766 | 0.008601 | −0.034167 | −0.013162 | −0.021613 | 0.013022 | −0.005156 | 0.025606 | 0.002841 | 0.018232 |
| 275 | 0.035623 | −0.015833 | −0.042627 | 0.016253 | 0.010857 | −0.015765 | −0.038635 | 0.00603 | −0.007818 | −0.02961 | 0.030336 | −0.054094 | 0.025501 | 0.033086 |
| 276 | 0.013735 | 0.05618 | −0.030847 | 0.013378 | 0.009056 | 0.01839 | −0.024572 | 0.013142 | 0.011408 | −0.012705 | −0.033653 | −0.029754 | 0.011419 | −0.00754 |
| 277 | −0.005243 | −0.009875 | 0.006843 | 0.018275 | 0.032854 | 0.009386 | 0.020418 | 0.006058 | −0.005209 | −0.005481 | −0.011557 | −0.042817 | 0.016253 | −0.006105 |
| 278 | 0.007703 | 0.042957 | 0.019576 | 0.018431 | −0.008587 | −0.00476 | 0.017317 | −0.002466 | 0.023544 | −0.018434 | 0.028138 | −0.012537 | −0.006456 | 0.009126 |
| 279 | 0.02446 | 0.020874 | 0.001169 | −0.039564 | 0.000123 | 0.006243 | 0.011665 | 0.009993 | −0.007555 | 0.033891 | −0.002998 | −0.012117 | 0.013928 | 0.007846 |
| 280 | 0.01305 | 0.03004 | 0.014525 | −0.004294 | 0.039431 | 0.044216 | −0.028157 | −0.022038 | 0.004974 | 0.022367 | 0.008602 | 0.040552 | −0.014819 | −0.011294 |
| 281 | −0.00495 | 0.020866 | 0.0105 | 0.006676 | 0.003006 | −0.048724 | 0.009323 | −0.004022 | −0.021542 | 0.005341 | −0.026964 | −0.030639 | −0.008449 | 0.035972 |
| 282 | 0.003833 | 0.051955 | 0.015141 | 0.059657 | −0.00657 | −0.044566 | −0.008151 | 0.068878 | −0.000557 | 0.030634 | 0.019997 | −0.003112 | −0.01888 | −0.005764 |
| 283 | 0.002462 | 0.060721 | 0.019181 | 0.035259 | −0.004688 | 0.002437 | 0.006207 | −0.024286 | −0.000406 | −0.015476 | 0.006796 | 0.024042 | −0.010078 | 0.027455 |
| 284 | 0.005322 | −0.035718 | −0.042898 | 0.003362 | −0.006118 | −0.01357 | 0.012352 | −0.038586 | 0.004691 | −0.038477 | −0.028329 | 0.015699 | 0.021233 | −0.010511 |
| 285 | −0.015379 | −0.006072 | −0.003497 | −0.00002 | −0.008385 | 0.003593 | 0.023304 | −0.020133 | −0.009953 | −0.027624 | −0.024094 | 0.020479 | 0.024916 | 0.013489 |
| 286 | −0.018172 | −0.028205 | −0.026539 | −0.040883 | 0.009463 | −0.004905 | 0.003135 | −0.028092 | −0.003378 | 0.00022 | −0.032916 | 0.004381 | −0.003623 | 0.010453 |
| 287 | −0.039145 | 0.030018 | −0.002473 | −0.009211 | 0.013468 | 0.018195 | −0.005149 | −0.028176 | 0.010099 | 0.005684 | −0.007782 | 0.037936 | −0.023554 | 0.033577 |
| 288 | 0.028172 | −0.007305 | 0.021123 | 0.013547 | 0.041981 | −0.021676 | 0.039138 | 0.019623 | 0.011548 | −0.022455 | 0.037511 | 0.038526 | −0.043124 | 0.016251 |
| 289 | 0.032384 | 0.005263 | 0.004127 | −0.0294 | 0.021514 | −0.026638 | 0.01822 | 0.033167 | 0.009339 | −0.029221 | 0.020828 | 0.016788 | −0.007609 | 0.017528 |
| 290 | −0.01119 | 0.011591 | −0.004961 | 0.040804 | −0.018333 | 0.028583 | −0.002874 | −0.000558 | 0.005967 | 0.014062 | 0.016407 | 0.040929 | −0.00152 | 0.015847 |
| 291 | −0.016275 | −0.00033 | 0.001815 | 0.04225 | −0.018172 | 0.029325 | 0.003349 | −0.005234 | −0.002868 | 0.017262 | 0.01836 | 0.02603 | −0.007886 | 0.015639 |
| 292 | −0.019949 | 0.001618 | −0.027711 | 0.016571 | −0.006019 | 0.041062 | 0.004682 | 0.032517 | −0.038277 | 0.013059 | −0.007186 | −0.012971 | −0.006237 | 0.033945 |
| 293 | 0.048514 | −0.019314 | 0.017132 | −0.000779 | 0.060262 | −0.021485 | −0.001041 | 0.038048 | 0.026525 | 0.018104 | 0.070544 | 0.05143 | −0.017595 | 0.006358 |
| 294 | 0.008512 | −0.029624 | −0.020453 | 0.017951 | −0.010006 | 0.029894 | 0.013977 | −0.045308 | −0.003462 | 0.019599 | 0.019043 | −0.025134 | −0.02198 | 0.019225 |
| 295 | 0.001424 | −0.029758 | −0.015763 | −0.035706 | −0.048305 | 0.035075 | 0.023322 | −0.027253 | −0.028071 | 0.051793 | −0.020561 | 0.063442 | 0.002995 | 0.006149 |
| 296 | −0.024345 | −0.077638 | −0.023747 | −0.053532 | −0.013249 | 0.021384 | −0.038447 | −0.049642 | −0.069299 | −0.033788 | −0.027984 | −0.035618 | −0.016549 | 0.039539 |
| 297 | −0.017098 | 0.014987 | −0.024692 | 0.033494 | 0.00783 | 0.0381 | −0.008452 | 0.023219 | −0.010496 | 0.026573 | 0.006779 | 0.053003 | 0.02213 | 0.016287 |
| 298 | −0.006959 | 0.00985 | 0.050518 | 0.038572 | −0.003608 | 0.018394 | −0.019184 | 0.039831 | −0.000423 | −0.069736 | 0.027773 | −0.040412 | −0.022532 | 0.001223 |
| 299 | 0.011956 | 0.016095 | −0.063132 | 0.043873 | −0.024112 | −0.033147 | −0.010125 | 0.045949 | −0.027127 | 0.05504 | −0.009255 | 0.036061 | −0.020133 | 0.001023 |
| 300 | −0.013967 | 0.032806 | 0.008864 | −0.064798 | 0.068338 | 0.023636 | 0.003894 | 0.03456 | 0.017859 | 0.008243 | −0.00807 | 0.035235 | 0.013348 | −0.049982 |
| 301 | −0.006294 | −0.001049 | −0.019955 | −0.010393 | −0.044148 | 0.006007 | 0.021878 | −0.015052 | −0.014169 | 0.009915 | −0.046197 | −0.016725 | 0.013115 | −0.012904 |
| 302 | −0.003441 | −0.023539 | −0.025066 | −0.026786 | 0.009951 | −0.067889 | 0.031138 | −0.014873 | −0.019014 | −0.023055 | −0.040947 | −0.031299 | 0.004627 | −0.023749 |
| 303 | 0.007714 | 0.051462 | −0.039782 | −0.029202 | −0.037249 | −0.023912 | −0.032609 | −0.021029 | 0.008306 | 0.051235 | −0.027958 | −0.033213 | −0.053886 | −0.035525 |
| 304 | −0.006831 | −0.028719 | −0.000233 | 0.012317 | −0.001662 | 0.028423 | −0.020962 | 0.039317 | −0.029456 | −0.018238 | −0.001607 | 0.012155 | −0.01924 | −0.017502 |
| 305 | 0.005022 | 0.051402 | 0.082602 | −0.035276 | 0.019369 | −0.079573 | 0.036293 | 0.059947 | 0.031833 | −0.085633 | −0.001337 | −0.024484 | −0.022013 | −0.032088 |
| 306 | 0.026749 | −0.01056 | −0.033889 | 0.004764 | 0.016209 | −0.034415 | 0.036056 | −0.019902 | −0.033677 | −0.115796 | 0.024511 | −0.038601 | −0.022215 | 0.032404 |
| 307 | 0.008981 | −0.012697 | −0.081991 | −0.003737 | −0.02966 | −0.018211 | 0.01276 | −0.04814 | 0.008669 | 0.032136 | 0.017545 | 0.076344 | −0.056018 | −0.043266 |
| 308 | −0.041903 | −0.011643 | −0.014936 | 0.03439 | 0.057843 | 0.009387 | −0.016661 | 0.089924 | −0.060204 | −0.066645 | 0.034792 | −0.007284 | 0.005909 | 0.029166 |
| 309 | −0.054437 | 0.003554 | −0.000161 | −0.038233 | 0.032238 | −0.009203 | −0.065856 | 0.046447 | −0.045366 | −0.003255 | 0.002635 | 0.021454 | −0.027725 | 0.001926 |
| 310 | −0.017937 | −0.046744 | 0.034491 | −0.043959 | −0.001193 | −0.083005 | 0.00156 | 0.01881 | −0.006106 | 0.025978 | 0.033414 | 0.040385 | 0.026422 | −0.012331 |
| 311 | 0.001467 | −0.031354 | 0.006001 | 0.033068 | −0.017849 | 0.015845 | −0.042106 | −0.001289 | 0.015086 | −0.001341 | −0.004404 | 0.034226 | −0.012949 | −0.064759 |
| 312 | 0.009835 | −0.002574 | −0.004725 | −0.042638 | −0.021105 | −0.021623 | −0.028116 | −0.015455 | 0.033957 | −0.046138 | 0.032088 | −0.010519 | −0.032704 | 0.00801 |
| 313 | −0.016133 | −0.038145 | 0.011904 | 0.043294 | −0.033997 | 0.034224 | −0.015255 | 0.068397 | −0.006031 | −0.023574 | −0.018215 | −0.019404 | 0.025779 | −0.01824 |
| 314 | −0.021605 | 0.001803 | 0.002354 | −0.009283 | −0.0215 | 0.001181 | 0.025602 | 0.00155 | 0.038349 | 0.046561 | 0.022305 | 0.024413 | 0.012223 | −0.005858 |

APPENDIX B1-continued

PCA Transformation Matrix(340 × 340; Normal/Diseased)

| | | | | | | | | | | | | | | |
|---|---|---|---|---|---|---|---|---|---|---|---|---|---|---|
| 315 | −0.109552 | −0.004626 | −0.026404 | −0.006465 | −0.028237 | −0.000341 | −0.042031 | 0.015458 | −0.068443 | 0.03145 | −0.053185 | −0.008468 | −0.083532 | 0.016735 |
| 316 | −0.033859 | 0.020823 | −0.010162 | −0.004232 | −0.057127 | −0.048882 | 0.000758 | −0.026453 | −0.002745 | −0.028759 | −0.012643 | 0.055065 | −0.006597 | −0.012558 |
| 317 | −0.117405 | −0.025443 | 0.016661 | −0.00176 | 0.03358 | 0.031516 | −0.038124 | −0.065389 | −0.035106 | −0.03515 | −0.015856 | −0.010373 | −0.000979 | 0.008966 |
| 318 | −0.074578 | −0.063928 | −0.024318 | −0.006276 | 0.04775 | 0.006491 | −0.022293 | 0.031997 | −0.048439 | 0.041244 | −0.002219 | 0.033535 | 0.01383 | −0.021939 |
| 319 | 0.800251 | −0.061386 | 0.00387 | 0.014726 | 0.019849 | 0.028342 | −0.039771 | −0.054836 | −0.040819 | 0.024574 | −0.045323 | −0.019422 | −0.024627 | 0.003837 |
| 320 | −0.057116 | 0.557413 | 0.00959 | 0.006623 | −0.010057 | 0.034698 | −0.00832 | −0.000089 | −0.035992 | 0.062885 | 0.027745 | −0.084371 | −0.019972 | −0.011573 |
| 321 | 0.02039 | 0.051317 | 0.644775 | −0.007523 | −0.082109 | −0.062685 | −0.044765 | 0.033521 | −0.050004 | −0.044599 | −0.100305 | −0.040459 | −0.017431 | 0.016374 |
| 322 | 0.03714 | −0.021351 | −0.026939 | 0.349341 | −0.055698 | 0.010366 | −0.005436 | 0.020086 | −0.020733 | −0.046265 | −0.027835 | 0.004102 | 0.004217 | 0.026421 |
| 323 | 0.0386 | −0.012237 | −0.03981 | −0.065727 | 0.585776 | 0.041526 | 0.067352 | 0.083316 | −0.028343 | −0.025657 | −0.0774 | 0.013286 | −0.048876 | 0.069563 |
| 324 | 0.040047 | 0.03278 | −0.036982 | −0.082419 | 0.03707 | 0.44184 | −0.041679 | 0.03403 | 0.016361 | −0.020284 | 0.014929 | −0.040804 | 0.010976 | −0.039519 |
| 325 | −0.021692 | −0.008854 | −0.056671 | −0.000174 | 0.038957 | −0.045703 | 0.709432 | −0.048035 | −0.013184 | 0.024612 | −0.011916 | −0.025607 | −0.039247 | 0.016805 |
| 326 | −0.012957 | −0.004374 | 0.006678 | 0i005992 | 0.060725 | 0.012629 | −0.050407 | 0.450398 | 0.018604 | −0.046811 | −0.053434 | −0.029376 | −0.087409 | −0.072442 |
| 327 | −0.066266 | −0.074378 | −0.048364 | −0.022623 | −0.02575 | 0.015771 | −0.036103 | 0.004793 | 0.814426 | 0.032844 | −0.097774 | −0.021978 | −0.069519 | 0.013132 |
| 328 | 0.011727 | 0.055274 | −0.009384 | −0.009815 | −0.057458 | −0.005075 | 0.013562 | −0.002977 | −0.00813 | 0.339774 | −0.008401 | −0.064123 | −0.000419 | −0.0541 |
| 329 | −0.047021 | −0.014788 | −0.080013 | −0.033727 | −0.111811 | 0.002642 | 0.008087 | −0.056374 | −0.096994 | −0.000803 | 0.740577 | −0.00685 | −0.06299 | −0.014367 |
| 330 | −0.01299 | −0.057282 | −0.014081 | −0.012379 | −0.029935 | −0.011276 | −0.031606 | −0.007071 | −0.005368 | −0.070937 | −0.011222 | 0.319366 | 0.023628 | −0.137986 |
| 331 | −0.013651 | 0.006378 | 0.01132 | −0.008886 | −0.044803 | −0.014652 | −0.051876 | −0.060429 | −0.049717 | 0.063911 | −0.032941 | 0.037241 | 0.797891 | −0.010511 |
| 332 | −0.013523 | −0.043076 | −0.016017 | 0.002502 | 0.071325 | −0.014753 | −0.014476 | −0.060241 | −0.016078 | −0.018781 | −0.009321 | −0.155498 | 0.003437 | 0.366234 |
| 333 | −0.050464 | 0.023215 | −0.006435 | 0.005726 | 0.030307 | −0.038456 | −0.139313 | −0.052441 | −0.044624 | −0.015512 | −0.047141 | 0.030319 | −0.071341 | −0.039118 |
| 334 | −0.005627 | 0.038443 | 0.017129 | −0.017133 | 0.015999 | −0.032768 | −0.086923 | −0.042875 | 0.018316 | 0.031603 | −0.06407 | 0.014289 | 0.004351 | 0.007229 |
| 335 | −0.061139 | −0.033823 | −0.014929 | 0.046234 | −0.047908 | −0.008337 | −0.064321 | −0.0592 | −0.062824 | −0.033329 | −0.050799 | −0.014936 | −0.07249 | −0.005053 |
| 336 | 0.014785 | −0.006467 | −0.035482 | −0.035378 | −0.023559 | 0.018874 | 0.018441 | −0.03934 | −0.002828 | −0.039329 | 0.000171 | −0.000366 | −0.030336 | 0.009244 |
| 337 | 0.010212 | 0.005411 | 0.010769 | −0.064 | 0.022431 | −0.094867 | 0.023142 | −0.024877 | 0.042211 | −0.059982 | −0.009689 | 0.054376 | 0.003858 | −0.057365 |
| 338 | 0.003849 | 0.022804 | 0.04007 | −0.041641 | −0.033276 | −0.054665 | 0.017994 | 0.010319 | −0.055139 | −0.004336 | −0.034041 | 0.043176 | −0.041962 | −0.051529 |
| 339 | −0.023415 | −0.015939 | −0.006393 | −0.041406 | −0.104417 | 0.047464 | 0.056763 | −0.068532 | 0.022815 | −0.021279 | −0.035865 | −0.00927 | −0.002294 | 0.007715 |
| 340 | −0.009603 | 0.018756 | −0.008497 | 0.006597 | 0.051622 | 0.026822 | 0.027954 | −0.05462 | 0.00003 | 0.038344 | −0.003569 | −0.020945 | 0.018697 | −0.062842 |

| | LV | LW | LX | LY | LZ | MA | MB | MC |
|---|---|---|---|---|---|---|---|---|
| 1 | 0.009734 | 0.038324 | 0.047365 | 0.090755 | 0.020958 | 0.13411 | 0.005696 | 0.097078 |
| 2 | −0.135157 | 0.06846 | −0.059857 | 0.065006 | −0.04544 | 0.014237 | 0.051749 | −0.024435 |
| 3 | 0.005275 | 0.12216 | −0.046505 | 0.040142 | −0.003257 | −0.017434 | 0.100565 | 0.007499 |
| 4 | −0.058446 | −0.082506 | −0.05713 | −0.026288 | −0.011381 | −0.000218 | 0.043848 | −0.047754 |
| 5 | 0.014245 | −0.074264 | −0.031987 | −0.061961 | 0.034086 | 0.01749 | 0.005082 | −0.026606 |
| 6 | 0.02695 | 0.071871 | −0.040446 | −0.0339 | 0.02794 | 0.02625 | −0.0307 | −0.002025 |
| 7 | 0.090098 | −0.044847 | 0.08932 | 0.028008 | 0.023668 | 0.016615 | 0.069406 | −0.120716 |
| 8 | −0.030185 | −0.009104 | −0.008262 | 0.076142 | −0.068972 | 0.016353 | −0.052061 | 0.002784 |
| 9 | 0.049416 | 0.035702 | 0.026529 | 0.186661 | 0.055127 | 0.103044 | −0.000442 | 0.063653 |
| 10 | 0.044727 | 0.032551 | −0.015766 | −0.002091 | 0.154297 | 0.077543 | 0.072798 | −0.071845 |
| 11 | 0.006309 | 0.0387651 | 0.036544 | 0.014866 | 0.022289 | −0.022552 | 0.029957 | 0.021991 |
| 12 | 0.003345 | −0.001683 | −0.011803 | 0.010531 | −0.021978 | −0.040399 | 0.073828 | 0.031705 |
| 13 | −0.002769 | 0.051874 | 0.078316 | 0.015333 | −0.12416 | 0.148893 | −0.020222 | 0.032155 |
| 14 | −0.081636 | −0.116003 | −0.099423 | 0.014247 | 0.007012 | −0.062972 | 0.132072 | −0.022705 |
| 15 | 0.018248 | 0.17848 | 0.023593 | −0.045436 | 0.094598 | 0.139773 | 0.024621 | −0.048356 |
| 16 | −0.009679 | 0.07557 | −0.037392 | 0.058669 | 0.00663 | −0.083043 | 0.031839 | 0.034469 |
| 17 | −0.026352 | −0.071681 | −0.005149 | 0.03248 | −0.032104 | −0.044595 | −0.081683 | 0.105992 |
| 18 | 0.05148 | −0.023121 | 0.073205 | −0.053937 | −0.031223 | −0.076171 | −0.043465 | −0.000749 |
| 19 | −0.007522 | −0.10784 | −0.073665 | 0.039038 | −0.010914 | −0.143134 | −0.06592 | −0.012961 |
| 20 | −0.057067 | −0.071417 | −0.090084 | −0.029883 | 0.014513 | −0.025102 | −0.049715 | 0.194677 |
| 21 | 0.048748 | −0.092931 | 0.03546 | −0.030415 | −0.048278 | 0.091261 | −0.061862 | −0.057963 |
| 22 | −0.047011 | −0.095987 | −0.017141 | −0.093895 | −0.037605 | −0.106283 | −0.020137 | 0.042901 |

APPENDIX B1-continued

PCA Transformation Matrix(340 × 340; Normal/Diseased)

| | | | | | | | | |
|---|---|---|---|---|---|---|---|---|
| 23 | −0.01583 | −0.067781 | 0.034812 | 0.000548 | −0.021443 | −0.018581 | −0.131616 | 0.046395 |
| 24 | 0.014171 | 0.067013 | −0.044309 | 0.010515 | −0.041589 | 0.029139 | 0.047001 | 0.064305 |
| 25 | 0.004732 | 0.062283 | 0.047617 | −0.073819 | 0.000347 | −0.0316 | 0.077985 | −0.04287 |
| 26 | 0.02795 | −0.059171 | −0.023606 | 0.137221 | −0.089545 | −0.02498 | 0.054346 | −0.153281 |
| 27 | 0.089688 | 0.005749 | −0.011561 | −0.037474 | 0.010808 | −0.142294 | −0.015513 | 0.112758 |
| 28 | 0.055736 | 0.001376 | 0.077658 | 0.05538 | −0.147698 | −0.080509 | 0.014185 | −0.072667 |
| 29 | −0.023126 | 0.101255 | 0.018144 | 0.034728 | 0.089746 | −0.083266 | 0.046075 | −0.047051 |
| 30 | −0.027978 | −0.023417 | 0.015725 | −0.063785 | −0.004566 | −0.050176 | −0.007292 | −0.013211 |
| 31 | 0.055727 | 0.010264 | 0.041765 | 0.027137 | −0.00329 | −0.031422 | 0.02733 | −0.042301 |
| 32 | −0.001414 | 0.009319 | 0.003078 | −0.014677 | −0.010489 | 0.103022 | 0.012823 | 0.115512 |
| 33 | −0.064811 | −0.143674 | 0.035806 | −0.0471 | −0.021625 | −0.118266 | 0.118939 | 0.076541 |
| 34 | −0.044026 | 0.071046 | 0.031679 | 0.005548 | −0.07293 | 0.054428 | −0.134491 | 0.071454 |
| 35 | 0.04003 | −0.03545 | 0.052098 | 0.019823 | 0.066773 | 0.045992 | −0.006315 | −0.061731 |
| 36 | 0.098738 | 0.052108 | 0.083691 | 0.126294 | 0.073524 | −0.06901 | 0.006694 | 0.06318 |
| 37 | −0.011422 | −0.043665 | 0.017255 | 0.00487 | 0.060996 | −0.033911 | 0.012853 | −0.113231 |
| 38 | 0.016398 | 0.043548 | 0.00133 | −0.036038 | 0.004851 | −0.044666 | 0.076453 | 0.033322 |
| 39 | 0.020204 | −0.073229 | 0.055691 | 0.019809 | −0.013218 | −0.085924 | 0.004456 | −0.00912 |
| 40 | −0.002573 | 0.091044 | 0.05354 | 0.024051 | 0.033887 | −0.066844 | −0.086041 | −0.001026 |
| 41 | −0.051048 | 0.010906 | −0.016313 | −0.172243 | 0.084289 | 0.017799 | 0.054054 | 0.015333 |
| 42 | −0.043315 | −0.02383 | 0.012777 | 0.057174 | −0.048926 | 0.071642 | −0.006369 | −0.023286 |
| 43 | 0.064135 | 0.09149 | −0.022358 | 0.079839 | −0.102044 | 0.091199 | 0.044228 | −0.022467 |
| 44 | 0.067771 | −0.088375 | −0.001206 | −0.016854 | −0.009256 | −0.058674 | −0.056959 | 0.005159 |
| 45 | −0.042034 | −0.044079 | −0.022136 | 0.050403 | 0.004136 | 0.113072 | −0.000094 | −0.005104 |
| 46 | −0.045771 | 0.10273 | −0.016948 | 0.011248 | 0.090494 | −0.047258 | −0.003036 | 0.011131 |
| 47 | −0.001227 | −0.034469 | 0.003855 | 0.022493 | −0.056951 | −0.068436 | −0.003099 | 0.090582 |
| 48 | −0.01379 | 0.014898 | −0.016692 | 0.035829 | 0.014171 | 0.153063 | 0.086591 | 0.105422 |
| 49 | 0.011822 | 0.001723 | 0.009295 | 0.014327 | −0.007236 | −0.11627 | 0.054266 | 0.078753 |
| 50 | 0.011054 | 0.038828 | −0.022425 | 0.066496 | 0.058692 | 0.066467 | −0.010744 | −0.149614 |
| 51 | −0.032158 | 0.138483 | 0.00552 | 0.0189 | 0.066334 | −0.157076 | −0.054173 | −0.076054 |
| 52 | 0.0465 | −0.018095 | 0.0786 | 0.018861 | −0.034229 | 0.01018 | 0.006055 | 0.041481 |
| 53 | −0.007734 | −0.021483 | −0.001505 | 0.002713 | −0.059726 | −0.042738 | 0.059673 | 0.313786 |
| 54 | −0.021293 | 0.084197 | 0.025358 | −0.088678 | −0.015203 | 0.016799 | −0.070222 | −0.046195 |
| 55 | −0.039714 | −0.15719 | −0.05638 | 0.102002 | 0.048366 | 0.115993 | 0.041487 | 0.009169 |
| 56 | 0.041993 | 0.113018 | −0.030236 | 0.078685 | 0.003238 | 0.06526 | −0.059836 | 0.02105 |
| 57 | −0.01685 | −0.153735 | −0.003786 | 0.192299 | 0.117666 | −0.070064 | −0.007503 | 0.006098 |
| 58 | −0.002898 | 0.014598 | −0.084198 | 0.063471 | 0.091598 | 0.002349 | 0.109276 | 0.072281 |
| 59 | −0.051539 | −0.025622 | −0.047479 | −0.065139 | −0.009316 | 0.03619 | 0.085579 | −0.060542 |
| 60 | −0.007411 | 0.029814 | 0.002388 | 0.050008 | 0.029859 | 0.014006 | 0.115633 | 0.016224 |
| 61 | 0.056292 | −0.107479 | 0.050245 | 0.149941 | 0.105998 | −0.098421 | −0.117268 | −0.032511 |
| 62 | −0.060946 | −0.00249 | 0.019845 | −0.03995 | −0.12509 | 0.03436 | −0.029631 | −0.083679 |
| 63 | 0.008017 | −0.082596 | −0.030463 | −0.002722 | −0.057101 | 0.029125 | −0.053031 | −0.097424 |
| 64 | 0.018741 | 0.026521 | 0.000418 | 0.042511 | 0.004007 | −0.019716 | 0.036154 | −0.00005 |
| 65 | 0.038155 | 0.073934 | −0.011502 | −0.03744 | 0.037086 | 0.05062 | −0.018913 | 0.149047 |
| 66 | 0.014425 | 0.013452 | 0.002066 | 0.075548 | −0.064519 | 0.001132 | 0.019663 | 0.068871 |
| 67 | −0.047047 | −0.034328 | −0.034724 | 0.007521 | −0.019775 | 0.000913 | 0.003036 | 0.105501 |
| 68 | −0.02561 | 0.009341 | 0.014218 | −0.047139 | 0.053649 | −0.116193 | 0.011555 | −0.042782 |
| 69 | 0.019916 | 0.184989 | −0.060313 | −0.082103 | 0.005287 | −0.132614 | −0.060805 | 0.072789 |
| 70 | 0.078517 | 0.13151 | −0.002398 | −0.011914 | −0.042223 | −0.097908 | −0.035233 | −0.077956 |
| 71 | −0.009695 | −0.027583 | −0.018832 | 0.031129 | −0.007791 | 0.041192 | 0.040602 | −0.080905 |
| 72 | 0.038996 | 0.00522 | 0.034764 | −0.003856 | −0.107653 | 0.117497 | −0.052356 | 0.064919 |
| 73 | 0.046874 | 0.082521 | 0.016175 | −0.054005 | −0.007772 | −0.058516 | 0.041351 | −0.013164 |

APPENDIX B1-continued

PCA Transformation Matrix(340 × 340; Normal/Diseased)

| | | | | | | | | |
|---|---|---|---|---|---|---|---|---|
| 74 | 0.019 | 0.008464 | −0.025878 | 0.082233 | −0.007415 | −0.005168 | 0.053908 | 0.041472 |
| 75 | 0.035834 | −0.018898 | −0.043376 | −0.093585 | 0.104805 | 0.093915 | 0.139052 | 0.061499 |
| 76 | 0.057261 | −0.179111 | 0.085457 | 0.090514 | −0.01283 | 0.094961 | 0.063648 | 0.100437 |
| 77 | −0.080162 | −0.066305 | 0.053514 | −0.021898 | 0.057154 | 0.021967 | 0.008146 | −0.053995 |
| 78 | −0.056197 | 0.002918 | 0.026178 | 0.074796 | 0.013687 | 0.016967 | −0.068193 | −0.059494 |
| 79 | 0.026607 | −0.031514 | 0.01763 | 0.02413 | 0.086573 | −0.068316 | −0.079565 | −0.09569 |
| 80 | −0.044442 | −0.0582 | −0.037465 | −0.022225 | −0.001508 | 0.093714 | −0.041796 | −0.054846 |
| 81 | 0.070456 | 0.120852 | −0.03818 | 0.03773 | −0.066539 | −0.051205 | 0.04617 | 0.07346 |
| 82 | 0.014384 | 0.033923 | −0.02036 | −0.004199 | −0.003779 | 0.041494 | −0.092953 | 0.034064 |
| 83 | 0.042971 | −0.183084 | 0.047589 | −0.02195 | 0.157221 | 0.196643 | −0.104618 | 0.014738 |
| 84 | −0.051879 | −0.013804 | −0.030646 | −0.056837 | 0.030321 | −0.002037 | 0.060796 | 0.106765 |
| 85 | 0.011616 | −0.085097 | −0.061129 | −0.090441 | 0.054043 | −0.104533 | −0.031426 | −0.113517 |
| 86 | −0.037494 | 0.02254 | 0.045828 | 0.04742 | 0.069139 | 0.084592 | −0.06298 | 0.006355 |
| 87 | −0.061791 | 0.024891 | 0.018649 | 0.091841 | 0.032922 | −0.070244 | 0.158936 | 0.039014 |
| 88 | −0.044373 | 0.13644 | −0.045482 | 0.047156 | 0.004311 | −0.067432 | 0.058252 | −0.06873 |
| 89 | −0.028232 | −0.023191 | −0.016141 | 0.068912 | −0.098408 | 0.013548 | 0.12227 | −0.203076 |
| 90 | −0.039695 | −0.003056 | −0.02708 | −0.015517 | −0.063131 | 0.165412 | −0.064421 | 0.059639 |
| 91 | 0.036672 | 0.090964 | 0.140164 | −0.093115 | 0.002826 | 0.096033 | −0.005329 | 0.037604 |
| 92 | −0.066564 | −0.085353 | −0.037472 | 0.087093 | −0.115516 | −0.126347 | 0.01806 | −0.06353 |
| 93 | 0.029378 | 0.072509 | 0.013515 | −0.070898 | −0.018486 | −0.078325 | 0.101223 | 0.01385 |
| 94 | 0.047893 | 0.083564 | −0.042517 | −0.077504 | 0.036714 | 0.043914 | −0.201593 | −0.032895 |
| 95 | −0.062819 | −0.050627 | −0.016381 | −0.043205 | −0.039634 | −0.007613 | −0.030797 | −0.007244 |
| 96 | 0.014949 | −0.039984 | 0.0058 | −0.080702 | −0.015489 | 0.022785 | −0.002149 | 0.051768 |
| 97 | −0.053668 | 0.038397 | 0.010463 | −0.027973 | −0.044244 | 0.031294 | 0.061452 | 0.068947 |
| 98 | 0.014563 | −0.04803 | 0.053293 | −0.035471 | 0.009774 | −0.023253 | −0.016777 | −0.108352 |
| 99 | 0.024166 | 0.063708 | 0.002427 | −0.027525 | −0.029162 | 0.060558 | 0.02925 | −0.047601 |
| 100 | 0.041971 | 0.099617 | 0.031862 | 0.001161 | 0.068291 | −0.011448 | 0.018286 | 0.090548 |
| 101 | 0.009343 | 0.015679 | −0.085596 | 0.057675 | −0.00682 | −0.034759 | 0.069092 | −0.027492 |
| 102 | 0.075045 | −0.098329 | 0.091636 | 0.000192 | 0.080981 | −0.160402 | −0.056732 | −0.046015 |
| 103 | 0.001586 | 0.051789 | −0.045297 | −0.041042 | −0.029159 | 0.054904 | −0.084976 | 0.007763 |
| 104 | −0.005391 | −0.008792 | −0.017219 | 0.048378 | −0.063926 | 0.060429 | 0.066397 | −0.085572 |
| 105 | −0.020719 | 0.067477 | −0.038737 | −0.044478 | −0.115312 | −0.015914 | 0.012908 | −0.013784 |
| 106 | −0.00091 | −0.04476 | 0.056177 | −0.103926 | −0.011424 | 0.010487 | −0.028091 | 0.035656 |
| 107 | −0.016214 | 0.02312 | 0.021484 | −0.041184 | −0.028108 | −0.002135 | −0.102675 | −0.092096 |
| 108 | −0.04704 | −0.010879 | −0.020347 | 0.049347 | 0.020524 | 0.00155 | 0.015144 | 0.033769 |
| 109 | 0.020525 | −0.067467 | −0.002225 | −0.058557 | −0.032369 | 0.009419 | 0.002629 | −0.001338 |
| 110 | −0.019855 | 0.060797 | −0.038183 | 0.003113 | −0.007915 | −0.004733 | 0.049406 | −0.051696 |
| 111 | −0.008023 | 0.052142 | −0.051032 | 0.031241 | 0.041847 | 0.03309 | −0.016016 | 0.030415 |
| 112 | 0.029213 | 0.019071 | 0.008938 | 0.06622 | −0.031717 | 0.027005 | 0.047061 | −0.02568 |
| 113 | 0.055334 | −0.03134 | 0.048052 | −0.002044 | 0.011322 | −0.0315 | 0.109423 | −0.005013 |
| 114 | −0.032457 | 0.003673 | 0.009213 | −0.059494 | −0.033884 | −0.022357 | −0.046517 | 0.010757 |
| 115 | 0.009072 | −0.022038 | 0.052901 | −0.031618 | −0.021696 | 0.005297 | −0.00282 | 0.015151 |
| 116 | −0.059776 | −0.00326 | −0.014269 | 0.059293 | 0.034718 | 0.0228 | −0.006914 | 0.054925 |
| 117 | 0.008665 | −0.034587 | −0.013854 | 0.074398 | −0.010875 | 0.09156 | −0.006527 | 0.035532 |
| 118 | −0.02939 | 0.059572 | −0.008895 | 0.028014 | 0.033814 | 0.003857 | 0.004626 | −0.001838 |
| 119 | −0.111857 | 0.043926 | −0.006525 | 0.024298 | 0.073314 | −0.098618 | 0.057179 | −0.128753 |
| 120 | −0.024385 | 0.067277 | 0.033737 | 0.12347 | −0.046105 | −0.087813 | 0.048379 | −0.011954 |
| 121 | −0.062763 | −0.003351 | −0.028548 | 0.121406 | −0.044299 | 0.029448 | −0.086912 | −0.0619 |
| 122 | 0.075637 | 0.039711 | 0.015832 | 0.134665 | 0.020602 | −0.108239 | −0.086039 | 0.149678 |
| 123 | 0.002396 | −0.117072 | 0.030342 | −0.097082 | 0.095206 | −0.071397 | −0.004752 | 0.100061 |
| 124 | −0.031593 | 0.003463 | −0.071368 | −0.023806 | −0.00659 | 0.143121 | −0.004292 | 0.039033 |

APPENDIX B1-continued

PCA Transformation Matrix(340 × 340; Normal/Diseased)

| | | | | | | | | |
|---|---|---|---|---|---|---|---|---|
| 125 | −0.02845 | 0.029183 | 0.036414 | 0.002417 | 0.063489 | 0.039416 | −0.034443 | 0.021533 |
| 126 | 0.017749 | 0.124538 | −0.037616 | −0.008914 | −0.041524 | 0.002461 | −0.043151 | −0.049209 |
| 127 | 0.000649 | −0.116038 | −0.007058 | 0.032974 | −0.092915 | 0.078011 | 0.053518 | −0.02601 |
| 128 | 0.017208 | −0.08915 | 0.035603 | −0.04267 | −0.052375 | 0.056546 | 0.058845 | 0.000271 |
| 129 | −0.045481 | 0.010921 | −0.019407 | −0.07412 | 0.021966 | 0.044561 | −0.094055 | −0.085134 |
| 130 | 0.019443 | 0.021536 | −0.029797 | 0.032819 | 0.015156 | −0.040604 | 0.113706 | −0.010587 |
| 131 | 0.015167 | −0.028849 | −0.026017 | −0.017245 | −0.000554 | 0.007606 | 0.087114 | 0.031203 |
| 132 | 0.009536 | −0.014222 | −0.01596 | 0.035688 | −0.017143 | 0.055031 | −0.005435 | 0.113727 |
| 133 | 0.067069 | −0.036482 | 0.019703 | 0.006227 | 0.044615 | 0.030795 | 0.079603 | −0.04244 |
| 134 | 0.04191 | −0.017494 | 0.063902 | −0.100846 | −0.059745 | −0.016422 | 0.016788 | 0.033845 |
| 135 | −0.043457 | −0.051722 | −0.029509 | −0.031538 | −0.021571 | −0.020246 | 0.08166 | 0.026796 |
| 136 | 0.046751 | 0.066653 | −0.077234 | −0.046318 | 0.004439 | 0.038959 | 0.023377 | −0.102357 |
| 137 | −0.053054 | 0.007402 | −0.018119 | 0.023613 | 0.062652 | 0.019444 | 0.013904 | 0.125449 |
| 138 | 0.015596 | 0.017411 | 0.001065 | 0.005374 | 0.003753 | −0.023732 | −0.050834 | −0.047994 |
| 139 | 0.019354 | −0.013908 | 0.012213 | 0.02403 | −0.006123 | −0.035591 | −0.01823 | 0.033384 |
| 140 | 0.017697 | −0.013528 | 0.041071 | −0.047571 | 0.053692 | 0.019442 | 0.08049 | −0.052272 |
| 141 | −0.005111 | 0.041154 | −0.032822 | −0.021419 | −0.084045 | −0.024263 | −0.061316 | −0.02032 |
| 142 | 0.013868 | −0.011148 | 0.0126 | 0.009305 | 0.013211 | 0.041132 | 0.051881 | 0.00249 |
| 143 | 0.034935 | 0.013338 | −0.009788 | −0.049892 | −0.031962 | −0.017182 | −0.061441 | −0.016032 |
| 144 | −0.034522 | −0.006156 | −0.013452 | 0.008812 | 0.027363 | 0.032846 | 0.002334 | 0.006152 |
| 145 | 0.005765 | 0.003197 | 0.016577 | 0.059304 | 0.060332 | 0.001861 | −0.047947 | 0.00817 |
| 146 | 0.017601 | 0.032074 | −0.043086 | 0.048482 | 0.027136 | −0.000807 | −0.033052 | 0.003803 |
| 147 | −0.013793 | −0.047085 | 0.014921 | −0.007038 | 0.000177 | −0.050596 | −0.078844 | −0.059241 |
| 148 | −0.001222 | 0.070076 | 0.001284 | −0.039166 | 0.008177 | −0.034089 | −0.023039 | 0.01835 |
| 149 | −0.004656 | 0.056339 | 0.033631 | −0.049645 | 0.043485 | −0.008454 | −0.020296 | −0.037674 |
| 150 | −0.001841 | 0.011856 | −0.058992 | −0.028479 | −0.054703 | −0.00365 | −0.042358 | 0.009057 |
| 151 | 0.006508 | −0.039581 | 0.03127 | 0.011416 | 0.022567 | 0.052623 | 0.064455 | 0.003237 |
| 152 | 0.015835 | 0.006243 | 0.0309 | −0.000696 | 0.02032 | 0.013163 | −0.021901 | 0.068543 |
| 153 | 0.027309 | 0.020665 | −0.035522 | 0.014837 | 0.06349 | −0.039375 | 0.040045 | 0.024146 |
| 154 | 0.009578 | −0.037425 | 0.033465 | 0.05895 | −0.036599 | 0.039279 | −0.078341 | 0.001036 |
| 155 | −0.010381 | 0.055679 | 0.054701 | 0.02144 | −0.011887 | −0.016053 | −0.001958 | 0.001711 |
| 156 | −0.031409 | 0.022173 | 0.01561 | −0.033328 | −0.033691 | −0.0113 | −0.088505 | 0.055686 |
| 157 | 0.025297 | −0.003421 | 0.027837 | −0.008489 | −0.017647 | −0.041088 | 0.038102 | −0.128042 |
| 158 | −0.004196 | 0.021309 | 0.000893 | 0.004959 | −0.05792 | −0.023275 | 0.034006 | 0.017959 |
| 159 | 0.003532 | −0.012922 | 0.004288 | 0.013193 | 0.058044 | −0.077305 | −0.014917 | 0.070465 |
| 160 | 0.005584 | −0.001116 | 0.001844 | 0.012096 | 0.014235 | −0.018487 | 0.038547 | 0.01463 |
| 161 | 0.045255 | 0.029678 | −0.027665 | −0.003885 | −0.021259 | −0.013621 | −0.060029 | −0.032632 |
| 162 | 0.04102 | −0.034815 | 0.014093 | −0.00609 | −0.071497 | 0.041699 | 0.013693 | −0.036479 |
| 163 | 0.028692 | −0.018195 | 0.057722 | −0.008668 | −0.036257 | −0.017705 | 0.013937 | 0.019717 |
| 164 | 0.009538 | −0.013218 | −0.033755 | −0.007544 | 0.035958 | −0.01254 | −0.022288 | 0.036575 |
| 165 | 0.002864 | −0.063226 | −0.000943 | 0.040442 | −0.025189 | −0.0722 | −0.025653 | 0.037264 |
| 166 | −0.000463 | −0.019843 | 0.030025 | 0.030347 | −0.054984 | −0.054103 | −0.093361 | 0.010344 |
| 167 | −0.001278 | −0.052167 | 0.024382 | 0.027816 | 0.049947 | −0.045921 | −0.041409 | 0.002558 |
| 168 | 0.024077 | −0.026854 | 0.054914 | 0.056422 | −0.086398 | −0.016756 | −0.03294 | −0.016788 |
| 169 | 0.037419 | −0.027463 | −0.008238 | 0.029081 | 0.029073 | −0.016881 | 0.022689 | 0.026674 |
| 170 | 0.013548 | −0.0125 | 0.0015 | 0.082827 | −0.004902 | −0.009929 | −0.002149 | 0.07809 |
| 171 | 0.028362 | 0.026659 | 0.023785 | 0.027939 | −0.018381 | −0.008934 | −0.003074 | 0.018292 |
| 172 | 0.002232 | −0.053022 | −0.005642 | −0.007126 | 0.011402 | 0.050987 | −0.006486 | −0.003078 |
| 173 | −0.015968 | 0.035301 | −0.010395 | 0.017392 | −0.011269 | −0.005945 | −0.042515 | 0.002547 |
| 174 | 0.005167 | 0.066859 | −0.018718 | −0.029222 | 0.007914 | 0.005837 | 0.013774 | −0.052584 |
| 175 | −0.020635 | 0.040662 | 0.026238 | 0.002637 | −0.010631 | 0.011872 | −0.005853 | 0.000558 |

APPENDIX B1-continued

PCA Transformation Matrix(340 × 340; Normal/Diseased)

| | | | | | | | | |
|---|---|---|---|---|---|---|---|---|
| 176 | 0.00862 | −0.015225 | 0.033164 | 0.060354 | −0.002623 | 0.00362 | 0.003054 | −0.038994 |
| 177 | 0.022244 | −0.005988 | 0.021975 | 0.014604 | 0.023751 | −0.012338 | 0.073908 | −0.01938 |
| 178 | 0.003581 | −0.02993 | 0.048571 | −0.000248 | 0.06083 | 0.024205 | 0.010421 | 0.035062 |
| 179 | 0.022853 | 0.010919 | 0.023554 | 0.032509 | −0.020268 | −0.023345 | −0.027448 | −0.018877 |
| 180 | −0.02213 | 0.001882 | 0.037915 | 0.028356 | 0.004157 | 0.010806 | −0.026028 | 0.028909 |
| 181 | −0.004626 | 0.031468 | 0.021319 | 0.02764 | 0.018269 | −0.024167 | −0.012705 | 0.026529 |
| 182 | −0.043871 | −0.013038 | 0.016109 | −0.004578 | 0.022428 | 0.011407 | −0.041117 | −0.022233 |
| 183 | 0.005476 | 0.038243 | 0.014616 | 0.026471 | −0.021476 | −0.006892 | −0.0032 | −0.027216 |
| 184 | −0.013515 | 0.054904 | −0.011565 | 0.01896 | 0.002685 | −0.012634 | 0.039623 | 0.049509 |
| 185 | −0.087386 | −0.08675 | −0.010398 | −0.077507 | −0.045714 | −0.040315 | 0.08926 | −0.01523 |
| 186 | 0.033911 | −0.011719 | −0.011171 | −0.035573 | 0.055723 | 0.014803 | −0.0183 | 0.036736 |
| 187 | 0.001826 | 0.035405 | −0.006515 | −0.00641 | 0.00636 | −0.001916 | −0.026599 | −0.037352 |
| 188 | −0.01081 | 0.018444 | −0.016689 | 0.01488 | 0.034651 | 0.043987 | 0.037808 | 0.018886 |
| 189 | −0.022664 | −0.043109 | −0.028272 | 0.046491 | 0.014875 | 0.030877 | 0.048797 | 0.042716 |
| 190 | −0.037087 | 0.004207 | 0.063606 | 0.004673 | −0.017372 | −0.009085 | −0.011164 | −0.013921 |
| 191 | −0.053178 | 0.013109 | −0.015572 | −0.066648 | −0.000291 | 0.041007 | 0.037179 | −0.021998 |
| 192 | −0.001209 | −0.029472 | 0.004582 | −0.00651 | 0.007712 | −0.044066 | 0.027877 | −0.036249 |
| 193 | −0.005428 | −0.034305 | −0.008437 | −0.036952 | −0.026038 | 0.036476 | −0.086013 | −0.058029 |
| 194 | 0.005452 | −0.009207 | −0.036624 | 0.025985 | 0.018735 | −0.026387 | −0.001101 | 0.060997 |
| 195 | −0.011981 | 0.016164 | −0.009407 | 0.087907 | −0.092635 | 0.009606 | −0.013194 | −0.022358 |
| 196 | 0.005736 | −0.018844 | −0.005311 | 0.010673 | 0.026547 | −0.002544 | −0.035365 | −0.009073 |
| 197 | −0.031959 | 0.024424 | −0.027663 | −0.043667 | 0.057494 | −0.019026 | −0.006161 | −0.032163 |
| 198 | 0.001357 | 0.04524 | −0.019064 | −0.076634 | 0.035251 | −0.004945 | 0.048441 | −0.025804 |
| 199 | −0.061458 | −0.009989 | −0.044322 | 0.023329 | −0.005425 | 0.062713 | 0.025499 | −0.035579 |
| 200 | 0.055618 | 0.068717 | −0.057839 | 0.023697 | 0.004289 | 0.005674 | 0.011002 | 0.002428 |
| 201 | 0.008824 | −0.001573 | 0.054114 | −0.0044 | 0.011161 | −0.033658 | 0.049201 | −0.05568 |
| 202 | 0.013597 | −0.01501 | 0.030994 | −0.001599 | 0.080038 | −0.014832 | −0.058801 | 0.026252 |
| 203 | −0.00483 | −0.047276 | 0.009376 | −0.027032 | −0.069572 | −0.024046 | −0.012333 | 0.005396 |
| 204 | 0.025227 | −0.096972 | −0.009767 | 0.013888 | −0.080652 | 0.068039 | −0.019588 | −0.096965 |
| 205 | −0.0459 | 0.015654 | −0.021164 | −0.006829 | −0.019109 | −0.015693 | −0.047038 | −0.043892 |
| 206 | 0.015861 | −0.045797 | 0.006496 | 0.008208 | 0.015067 | −0.04389 | −0.024641 | −0.007571 |
| 207 | 0.011129 | 0.019907 | 0.028761 | 0.007657 | 0.068816 | 0.006305 | −0.00397 | −0.092999 |
| 208 | −0.044222 | 0.004691 | 0.017738 | 0.076111 | −0.013607 | −0.025856 | −0.01006 | 0.028751 |
| 209 | −0.030567 | −0.027757 | −0.040678 | 0.031591 | −0.043869 | 0.040724 | −0.043175 | 0.00538 |
| 210 | 0.033934 | −0.053895 | 0.060509 | 0.016656 | 0.034968 | −0.022717 | −0.038218 | −0.010159 |
| 211 | 0.02956 | −0.026203 | 0.045054 | 0.033255 | 0.059124 | 0.032992 | 0.013691 | 0.015379 |
| 212 | 0.02507 | −0.021644 | −0.025289 | 0.022936 | 0.03483 | 0.029628 | −0.023203 | 0.015085 |
| 213 | −0.045101 | −0.009916 | −0.008241 | 0.06073 | 0.000429 | 0.043168 | −0.026241 | 0.021875 |
| 214 | 0.035027 | −0.025454 | 0.014047 | 0.011974 | −0.001284 | −0.010803 | −0.0158 | 0.008579 |
| 215 | 0.017845 | −0.044719 | −0.030236 | −0.084284 | −0.003426 | −0.011205 | −0.012603 | −0.000761 |
| 216 | −0.01169 | −0.011428 | −0.003491 | −0.055235 | 0.040243 | 0.058657 | −0.019709 | −0.055403 |
| 217 | −0.009108 | −0.031787 | −0.019766 | −0.004579 | −0.006085 | 0.013857 | −0.003376 | 0.029872 |
| 218 | −0.004477 | −0.075276 | −0.023538 | 0.016774 | 0.000332 | 0.019487 | 0.003467 | 0.088865 |
| 219 | 0.02607 | −0.016765 | −0.037785 | 0.025141 | −0.009845 | −0.001502 | 0.006703 | −0.026099 |
| 220 | 0.020428 | 0.004855 | 0.01867 | 0.000575 | 0.011907 | −0.009737 | −0.025795 | −0.005142 |
| 221 | −0.005169 | 0.017465 | −0.003109 | −0.028586 | −0.036114 | −0.022126 | −0.02326 | −0.062682 |
| 222 | −0.016193 | −0.034591 | 0.002167 | 0.024327 | 0.000729 | −0.041139 | −0.005179 | 0.015808 |
| 223 | 0.022664 | −0.052782 | 0.023934 | 0.028883 | 0.007842 | −0.040449 | 0.015836 | −0.015105 |
| 224 | 0.008031 | −0.015791 | 0.000697 | 0.039484 | 0.059718 | −0.016148 | −0.034111 | −0.018397 |
| 225 | 0.026302 | 0.015402 | 0.015187 | −0.004553 | −0.003026 | −0.007595 | −0.05173 | −0.010938 |
| 226 | −0.00736 | −0.041956 | 0.015585 | 0.007817 | 0.019734 | −0.025312 | −0.04678 | 0.002318 |

APPENDIX B1-continued

PCA Transformation Matrix(340 × 340; Normal/Diseased)

| | | | | | | | | |
|---|---|---|---|---|---|---|---|---|
| 227 | −0.009601 | −0.015718 | −0.018318 | −0.045214 | −0.029618 | 0.012319 | −0.007208 | −0.039932 |
| 228 | −0.03975 | 0.01152 | −0.017007 | −0.023211 | 0.007698 | 0.048376 | 0.01969 | 0.017752 |
| 229 | −0.002772 | −0.037219 | −0.043121 | 0.033649 | −0.005265 | −0.001506 | −0.00066 | 0.005421 |
| 230 | 0.003886 | −0.001967 | −0.011818 | 0.002058 | 0.016095 | 0.023668 | −0.028528 | 0.044753 |
| 231 | 0.004248 | 0.020095 | −0.021977 | −0.040129 | 0.010828 | −0.04184 | 0.003059 | −0.042634 |
| 232 | 0.008132 | 0.072273 | −0.037979 | −0.034181 | 0.011116 | −0.00999 | −0.019312 | 0.050505 |
| 233 | −0.013372 | −0.051618 | −0.04033 | 0.001204 | 0.02723 | 0.001304 | 0.006162 | 0.00754 |
| 234 | 0.014611 | −0.027054 | 0.032909 | 0.035704 | 0.012191 | 0.032228 | 0.01349 | −0.005703 |
| 235 | 0.003519 | 0.033254 | −0.021478 | 0.078752 | −0.016869 | 0.001362 | −0.002289 | 0.018776 |
| 236 | −0.037601 | 0.021778 | −0.025956 | −0.042403 | 0.017383 | −0.00327 | 0.037425 | 0.026533 |
| 237 | 0.024218 | −0.029051 | 0.008337 | −0.056228 | −0.042655 | 0.014903 | 0.024609 | 0.018831 |
| 238 | 0.009669 | −0.01604 | −0.01337 | −0.017779 | 0.00671 | 0.010001 | 0.014552 | −0.060757 |
| 239 | −0.005711 | 0.015645 | −0.00227 | −0.00656 | 0.033657 | 0.027711 | −0.046552 | −0.075858 |
| 240 | −0.010169 | 0.000221 | 0.003281 | −0.009509 | −0.009093 | −0.029109 | −0.014244 | 0.020029 |
| 241 | 0.004997 | −0.000135 | −0.03993 | −0.001306 | 0.004903 | −0.028783 | −0.000235 | −0.009192 |
| 242 | −0.053591 | 0.000022 | 0.001448 | −0.037814 | −0.030088 | 0.04937 | −0.014874 | 0.029167 |
| 243 | −0.014537 | −0.001605 | −0.007586 | 0.018816 | 0.017126 | 0.038796 | 0.04107 | −0.049289 |
| 244 | 0.016509 | 0.085313 | 0.014615 | 0.611405 | 0.002737 | 0.006231 | 0.00929 | 0.011393 |
| 245 | 0.024071 | 0.086149 | −0.037542 | 0.014411 | 0.000708 | 0.018851 | −0.016585 | −0.013587 |
| 246 | −0.013534 | 0.000881 | 0.011888 | −0.059125 | −0.061259 | 0.038712 | −0.019762 | −0.013039 |
| 247 | −0.001039 | −0.068374 | 0.032329 | −0.047514 | 0.009804 | −0.010153 | 0.051925 | −0.030249 |
| 248 | 0.016978 | −0.019746 | 0.017409 | −0.028142 | 0.037252 | −0.029755 | 0.020746 | −0.034926 |
| 249 | −0.034558 | −0.024479 | −0.022287 | 0.03897 | −0.004058 | −0.05755 | −0.002248 | 0.031488 |
| 250 | −0.022325 | −0.009681 | −0.012429 | −0.047862 | 0.017594 | 0.031028 | 0.015204 | 0.037283 |
| 251 | 0.018016 | 0.039854 | −0.011681 | −0.002459 | −0.027563 | 0.019172 | −0.055962 | 0.009659 |
| 252 | −0.004115 | −0.003958 | −0.003582 | 0.031462 | 0.003906 | −0.06725 | −0.006232 | −0.058933 |
| 253 | 0.03 | 0.061522 | −0.03009 | 0.010995 | 0.007066 | 0.046173 | −0.014709 | −0.022714 |
| 254 | 0.018952 | 0.041863 | 0.02418 | −0.010584 | −0.010983 | 0.013193 | −0.001589 | −0.010226 |
| 255 | −0.001991 | 0.018443 | 0.0143 | −0.022995 | −0.010519 | −0.000515 | 0.009015 | −0.063222 |
| 256 | −0.01941 | −0.047322 | −0.017863 | 0.020765 | 0.025678 | 0.015789 | 0.056838 | −0.030811 |
| 257 | −0.01895 | −0.018994 | 0.017037 | 0.01356 | −0.022822 | −0.011293 | −0.021018 | 0.008768 |
| 258 | −0.007769 | −0.020752 | 0.018712 | −0.026415 | −0.050879 | −0.020625 | −0.029446 | 0.020102 |
| 259 | 0.005061 | 0.001567 | −0.003091 | −0.021366 | 0.005215 | 0.010923 | −0.034155 | 0.024861 |
| 260 | 0.033584 | 0.033705 | 0.005438 | −0.0374 | −0.057175 | −0.016075 | −0.016847 | −0.005425 |
| 261 | 0.036951 | 0.019364 | 0.007596 | 0.038606 | −0.034112 | 0.026422 | −0.038354 | 0.003282 |
| 262 | 0.016121 | −0.015883 | 0.035899 | −0.032219 | 0.007925 | −0.006464 | −0.030278 | 0.017721 |
| 263 | 0.031348 | 0.024078 | 0.004252 | −0.035123 | 0.041042 | 0.005813 | −0.026568 | 0.011831 |
| 264 | 0.001068 | 0.049662 | −0.006259 | −0.011178 | 0.026166 | 0.004061 | 0.039449 | 0.031685 |
| 265 | 0.009554 | 0.021852 | 0.0095061 | −0.007038 | −0.031622 | 0.051976 | 0.043542 | 0.002215 |
| 266 | 0.013712 | −0.034819 | −0.030958 | 0.079768 | 0.044431 | 0.038567 | 0.099326 | 0.015366 |
| 267 | 0.063642 | −0.012441 | 0.0699421 | −0.070546 | 0.042695 | 0.008035 | −0.052099 | −0.021219 |
| 268 | −0.017583 | −0.056888 | 0.024652 | 0.024842 | 0.025667 | −0.023322 | −0.017527 | −0.016986 |
| 269 | −0.027512 | −0.018849 | −0.016089 | 0.033642 | 0.041692 | −0.027935 | 0.025869 | −0.017666 |
| 270 | −0.042744 | −0.0024 | −0.0086511 | −0.01542 | 0.018196 | 0.04533 | 0.005093 | −0.007941 |
| 271 | −0.039928 | −0.037208 | 0.003569 | −0.013296 | −0.019984 | 0.022994 | 0.058208 | 0.011016 |
| 272 | 0.017216 | −0.017746 | −0.010346 | −0.011564 | −0.062828 | −0.031353 | −0.00183 | −0.068846 |
| 273 | 0.000329 | 0.011323 | 0.019727 | 0.031323 | −0.013651 | −0.054157 | 0.02399 | 0.0191 |
| 274 | −0.003509 | 0.020675 | 0.008659 | 0.039503 | −0.025847 | −0.041496 | 0.029201 | 0.019235 |
| 275 | 0.03177 | 0.050578 | −0.015473 | −0.048823 | 0.040932 | 0.001057 | 0.01635 | −0.001831 |
| 276 | −0.016542 | 0.022001 | 0.008225 | 0.002826 | 0.022518 | −0.023726 | 0.019991 | −0.010749 |
| 277 | 0.009035 | 0.008794 | 0.020703 | −0.002201 | 0.005285 | 0.01929 | 0.042384 | 0.029598 |

APPENDIX B1-continued

PCA Transformation Matrix(340 × 340; Normal/Diseased)

| | | | | | | | | |
|---|---|---|---|---|---|---|---|---|
| 278 | −0.014297 | 0.000314 | −0.00122 | 0.030828 | 0.032898 | 0.027305 | 0.042401 | 0.007231 |
| 279 | 0.007337 | 0.034587 | −0.028786 | 0.067533 | 0.074555 | 0.03136 | −0.03993 | −0.048568 |
| 280 | −0.001652 | 0.011143 | 0.003944 | 0.002557 | 0.020926 | 0.016591 | 0.004869 | −0.037451 |
| 281 | 0.011392 | 0.025056 | −0.011009 | −0.022296 | −0.041868 | −0.063094 | −0.035091 | −0.006844 |
| 282 | −0.008497 | 0.004189 | −0.020647 | 0.048797 | 0.031684 | −0.077623 | 0.026387 | −0.023468 |
| 283 | 0.005405 | −0.061553 | 0.003102 | −0.028259 | 0.06063 | 0.029932 | 0.024352 | 0.002659 |
| 284 | −0.027089 | 0.00705 | −0.01442 | −0.020961 | −0.017748 | −0.000662 | −0.011336 | 0.025808 |
| 285 | −0.04863 | −0.009466 | −0.023499 | 0.023318 | 0.005201 | 0.029367 | 0.006572 | 0.028354 |
| 286 | 0.01028 | 0.002696 | −0.021742 | −0.026477 | 0.002881 | −0.007296 | −0.056744 | 0.021613 |
| 287 | 0.000188 | −0.009391 | −0.02145 | 0.018023 | 0.019097 | −0.012663 | −0.072642 | 0.018514 |
| 288 | 0.015504 | −0.023722 | −0.024314 | −0.045339 | 0.035942 | −0.03139 | −0.007337 | 0.014394 |
| 289 | −0.005801 | −0.00762 | 0.020508 | −0.001459 | 0.021308 | 0.031773 | 0.001582 | 0.015475 |
| 290 | 0.011362 | 0.004389 | 0.003319 | 0.023697 | 0.004371 | 0.01899 | −0.027824 | 0.000418 |
| 291 | 0.014941 | 0.006294 | −0.00004 | −0.00003 | 0.01288 | 0.027333 | −0.019243 | −0.013242 |
| 292 | 0.002272 | 0.015653 | −0.012428 | 0.005027 | 0.032632 | 0.059327 | −0.029532 | −0.025189 |
| 293 | −0.021732 | −0.022056 | −0.019832 | −0.023877 | 0.016879 | −0.017772 | −0.024493 | −0.030884 |
| 294 | −0.006826 | −0.01352 | −0.023774 | −0.027204 | 0.027019 | −0.016 | 0.035939 | 0.018075 |
| 295 | 0.004653 | −0.009449 | 0.014776 | −0.000717 | −0.028851 | −0.005198 | −0.027089 | 0.040135 |
| 296 | 0.018586 | −0.003404 | 0.04794 | 0.042534 | −0.005123 | −0.060821 | 0.007381 | −0.016842 |
| 297 | −0.007098 | 0.004773 | 0.018596 | 0.017838 | −0.011374 | 0.031432 | −0.013057 | −0.014464 |
| 298 | 0.000678 | −0.013845 | 0.0074771 | −0.023832 | −0.002157 | −0.070503 | 0.082975 | 0.01351 |
| 299 | 0.027874 | −0.025482 | −0.02604 | −0.025189 | 0.014014 | −0.009617 | 0.020967 | −0.004239 |
| 300 | 0.000638 | −0.018343 | 0.035784 | 0.056947 | −0.012389 | −0.010776 | 0.040698 | −0.002929 |
| 301 | −0.027196 | −0.003978 | −0.020444 | −0.013564 | −0.019594 | −0.027518 | −0.033186 | −0.018028 |
| 302 | 0.003705 | −0.023354 | −0.004421 | −0.001035 | −0.014174 | −0.017784 | −0.068652 | 0.010715 |
| 303 | 0.022666 | −0.01688 | −0.031826 | 0.006076 | −0.024681 | −0.022692 | 0.012172 | −0.05308 |
| 304 | 0.036199 | 0.038305 | −0.027279 | −0.049836 | −0.004493 | 0.029121 | −0.048355 | −0.04949 |
| 305 | 0.018187 | −0.006922 | −0.023664 | 0.020625 | −0.078376 | −0.041194 | 0.010318 | 0.004004 |
| 306 | 0.022445 | 0.070973 | −0.038241 | −0.064255 | −0.084584 | 0.028301 | −0.019674 | −0.050085 |
| 307 | −0.00012 | 0.010894 | −0.055706 | −0.008242 | −0.062566 | −0.037071 | 0.002574 | 0.023385 |
| 308 | 0.002595 | 0.059431 | −0.063111 | 0.014795 | 0.041797 | 0.025082 | 0.01242 | −0.009122 |
| 309 | −0.049049 | −0.030348 | −0.037111 | −0.004858 | 0.039754 | 0.00621 | 0.013454 | −0.018857 |
| 310 | 0.010062 | 0.0222 | −0.058928 | 0.033463 | −0.050326 | 0.022893 | 0.037778 | 0.058525 |
| 311 | −0.023652 | 0.002037 | 0.001812 | 0.011172 | 0.010229 | 0.006676 | −0.064634 | 0.020222 |
| 312 | 0.027568 | 0.007594 | −0.012417 | −0.048862 | −0.028373 | 0.013523 | −0.068772 | 0.020175 |
| 313 | 0.013376 | 0.034552 | −0.007491 | 0.050496 | 0.052261 | −0.029961 | 0.011376 | −0.009827 |
| 314 | 0.058257 | 0.061845 | 0.009078 | 0.026604 | 0.018803 | −0.056568 | 0.004964 | 0.041484 |
| 315 | −0.025053 | −0.032749 | −0.042593 | −0.001534 | 0.013583 | −0.011601 | −0.040842 | −0.025061 |
| 316 | 0.005522 | 0.003851 | −0.019239 | −0.041666 | −0.061094 | −0.01322 | −0.072514 | −0.032047 |
| 317 | −0.07222 | 0.000297 | −0.051892 | −0.045534 | 0.024208 | 0.055388 | −0.003056 | 0.005426 |
| 318 | −0.071006 | −0.012553 | −0.012367 | −0.051406 | 0.010539 | 0.090409 | 0.045956 | −0.02669 |
| 319 | −0.047493 | −0.028492 | −0.056995 | 0.01193 | −0.025143 | 0.039399 | −0.024551 | 0.021876 |
| 320 | 0.023086 | 0.009077 | −0.035273 | −0.023668 | −0.048945 | 0.017347 | 0.011796 | 0.065887 |
| 321 | −0.001469 | −0.005181 | −0.011736 | −0.03217 | 0.02255 | 0.008031 | −0.02198 | −0.02994 |
| 322 | −0.012373 | −0.043949 | 0.022208 | −0.006686 | −0.015258 | −0.063225 | −0.040849 | −0.001137 |
| 323 | 0.013189 | −0.003054 | −0.009658 | −0.08813 | 0.048346 | −0.04627 | −0.087012 | 0.01593 |
| 324 | −0.027378 | −0.013337 | 0.019533 | 0.020579 | −0.113879 | −0.058439 | 0.038696 | 0.009217 |
| 325 | −0.141208 | −0.064982 | −0.070416 | 0.044066 | −0.009133 | 0.024306 | 0.031769 | 0.009579 |
| 326 | −0.047387 | −0.034716 | −0.05948 | −0.019359 | −0.057021 | 0.034992 | −0.061583 | −0.026864 |
| 327 | −0.052845 | 0.034218 | −0.073452 | −0.029933 | 0.027503 | −0.011954 | 0.008731 | 0.022717 |
| 328 | −0.024821 | −0.009964 | −0.009087 | −0.013675 | −0.020094 | −0.008543 | 0.029669 | 0.000387 |

APPENDIX B1-continued

PCA Transformation Matrix(340 × 340; Normal/Diseased)

| | | | | | | | | |
|---|---|---|---|---|---|---|---|---|
| 329 | −0.051547 | −0.051622 | −0.063994 | −0.053553 | −0.018792 | 0.016215 | −0.061079 | −0.012043 |
| 330 | 0.032687 | 0.009133 | −0.0186 | −0.048188 | 0.036759 | 0.072774 | 0.000806 | −0.0259 |
| 331 | −0.088132 | −0.041634 | −0.091489 | −0.041713 | −0.002395 | −0.023952 | 0.006818 | −0.045327 |
| 332 | −0.037037 | 0.02514 | −0.020963 | 0.029319 | −0.034253 | −0.016014 | −0.01621 | −0.005704 |
| 333 | 0.7572 | −0.074089 | −0.091575 | −0.00759 | −0.035023 | 0.045334 | 0.040593 | −0.021802 |
| 334 | −0.073618 | 0.28951 | 0.039668 | 0.075422 | 0.02251 | 0.003495 | −0.006571 | 0.014347 |
| 335 | −0.090428 | 0.042105 | 0.762663 | −0.026893 | −0.027118 | 0.045112 | 0.042238 | 0.005653 |
| 336 | −0.014111 | 0.003393 | 0.002224 | 0.460842 | −0.021349 | 0.025044 | −0.061793 | −0.055631 |
| 337 | −0.013641 | −0.007294 | −0.000241 | −0.00741 | 0.564386 | 0.014779 | −0.023226 | −0.032466 |
| 338 | 0.011316 | 0.029534 | −0.012014 | 0.053542 | 0.011431 | 0.261348 | 0.026567 | −0.075435 |
| 339 | 0.049912 | 0.028583 | 0.042981 | −0.078666 | −0.041396 | 0.006734 | 0.421246 | −0.037304 |
| 340 | 0.03931 | −0.010611 | 0.0073251 | −0.043475 | −0.001611 | −0.02642 | −0.026543 | 0.188782 |

APPENDIX B2

PCA Transformation Matrix (340 × 340; Benign/Malignant)

| | A | B | C | D | E | F | G | H | I | J | K |
|---|---|---|---|---|---|---|---|---|---|---|---|
| 1 | 409.4/255.3>GPA:Lyso 16:0 | −0.072906 | −0.00279 | 0.065196 | 0.126547 | 0.040083 | 0.011985 | −0.040261 | −0.024067 | 0.058069 | 0.000796 |
| 2 | 433.4/279.3>GPA:Lyso 18:2 | −0.029572 | 0.063815 | 0.047916 | 0.158016 | 0.030831 | −0.035309 | 0.011406 | 0.036279 | 0.051752 | −0.013216 |
| 3 | 435.4/281.3>GPA:Lyso 18:1 | −0.047698 | 0.048574 | 0.070717 | 0.138994 | 0.020402 | −0.029311 | −0.008363 | 0.020279 | 0.073379 | −0.016482 |
| 4 | 437.4/283.3>GPA:Lyso 18:0 | −0.032751 | −0.09578 | 0.001071 | 0.089485 | 0.002671 | 0.061765 | −0.063224 | −0.023486 | 0.029791 | 0.018863 |
| 5 | 451.4/283.3>GPA:Lyso 18:0 | −0.016026 | 0.026825 | −0.016302 | 0.029254 | −0.007184 | 0.099403 | −0.117715 | −0.062037 | −0.011923 | −0.076524 |
| 6 | 459.6/305.5>GPA:Lyso 20:3 | −0.037424 | 0.038996 | 0.047521 | 0.104831 | 0.029923 | −0.062384 | 0.040324 | −0.067334 | 0.063622 | 0.095707 |
| 7 | 461.6/307.5>GPA:Lyso 20:2 | −0.016355 | 0.077341 | 0.045118 | 0.115207 | −0.019826 | −0.01239 | −0.063803 | 0.030503 | 0.041534 | −0.01581 |
| 8 | 463.7/309.5>GPA:Lyso 20:1 | −0.029677 | −0.029731 | 0.017736 | 0.087472 | −0.027058 | −0.030302 | −0.051602 | 0.019768 | 0.047734 | −0.119239 |
| 9 | 465.7/311.5>GPA:Lyso 20:0 | −0.038753 | −0.088505 | −0.053178 | 0.040222 | 0.009393 | 0.057639 | −0.048983 | −0.071118 | 0.027943 | −0.020895 |
| 10 | 481.4/327.3>GPA:Lyso 22:6 | −0.019348 | 0.047196 | 0.070919 | 0.116125 | 0.066385 | 0.002284 | 0.066784 | −0.00433 | 0.020503 | 0.010864 |
| 11 | 483.4/329.3>GPA:Lyso 22:5 | −0.023949 | 0.014569 | −0.004665 | 0.079987 | −0.002676 | −0.001841 | −0.019279 | −0.116601 | −0.001063 | −0.001209 |
| 12 | 641.8/251.3>GPA:16.1/16:2 | −0.018005 | 0.015919 | −0.024331 | −0.001554 | −0.022618 | 0.044011 | −0.085001 | 0.110684 | −0.037949 | 0.009867 |
| 13 | 643.8/253.3>GPA:16.1/16:1 | −0.005615 | −0.034928 | 0.006974 | −0.050132 | −0.03024 | 0.092119 | 0.06356 | 0.149541 | 0.101984 | 0.092088 |
| 14 | 645.8/255.3>GPA:16.1/16:0 | −0.023948 | −0.038283 | −0.008299 | −0.031097 | −0.039958 | 0.076685 | 0.045204 | 0.119717 | 0.113584 | 0.059233 |
| 15 | 647.8/255.3>GPA:16.0/16:0 | −0.079394 | 0.020039 | 0.066461 | 0.098874 | −0.01426 | 0.047204 | 0.002358 | −0.007458 | 0.075476 | 0.015136 |
| 16 | 667.8/279.3>GPA:34:4 | 0.022392 | 0.02734 | −0.041662 | 0.057892 | 0.025566 | 0.005918 | −0.03678 | 0.003649 | 0.057555 | −0.148574 |
| 17 | 669.8/279.3>GPA:34:3 | −0.049446 | 0.040381 | −0.045312 | 0.090603 | −0.009072 | 0.018517 | −0.056775 | 0.090127 | −0.000103 | 0.125815 |
| 18 | 669.8/281.3>GPA:34:4 | −0.043446 | −0.004437 | −0.048136 | 0.079993 | 0.052357 | 0.028106 | 0.006096 | −0.052865 | 0.091132 | −0.109116 |
| 19 | 671.8/279.3>GPA:18:2/16:0 | −0.012948 | 0.045193 | −0.015042 | 0.153229 | 0.010966 | 0.049227 | −0.000976 | 0.035719 | 0.04988 | −0.0365 |
| 20 | 673.8/281.3>GPA:18:1/16:0 | −0.055302 | −0.009334 | 0.044559 | 0.041599 | −0.171616 | 0.038643 | 0.05704 | −0.006391 | 0.034396 | 0.040834 |
| 21 | 695.8/279.3>GPA:36:4 | −0.018276 | 0.060179 | 0.03645 | 0.140041 | 0.020986 | −0.031774 | −0.000097 | 0.07334 | 0.011046 | 0.002886 |
| 22 | 695.8/303.3>GPA:36:4 | −0.028035 | 0.019999 | 0.048404 | 0.131097 | 0.029854 | 0.08565 | 0.030493 | −0.044899 | 0.063682 | −0.030125 |
| 23 | 697.8/281.3>GPA:20:3/16:0 | −0.034111 | 0.038237 | 0.041832 | 0.095187 | −0.0229 | 0.039721 | −0.01805 | −0.001887 | 0.058739 | −0.014468 |
| 24 | 697.8/305.3>GPA:18:1/18:2 | −0.041347 | 0.040649 | 0.051789 | 0.12811 | −0.028146 | −0.005728 | −0.011247 | 0.027599 | 0.026704 | −0.015302 |
| 25 | 699.8/279.3>GPA:36:2 | −0.041217 | 0.036538 | 0.042618 | 0.128951 | −0.039388 | −0.04286 | 0.015066 | 0.056591 | −0.019035 | 0.0304 |
| 26 | 699.8/281.3>GPA:36:2 | −0.052185 | −0.010561 | 0.061257 | 0.022549 | −0.182442 | 0.02368 | 0.042162 | −0.020886 | 0.015211 | 0.030985 |
| 27 | 701.8/283.3>GPA:36:1 | −0.046291 | −0.006736 | 0.042175 | 0.044049 | −0.181579 | 0.021953 | 0.058833 | −0.032566 | 0.002649 | 0.025328 |
| 28 | 703.8/283.3>GPA:36:0 | −0.079738 | −0.060299 | 0.023124 | 0.063483 | −0.075068 | 0.050334 | −0.009086 | −0.048035 | 0.010517 | 0.029764 |
| 29 | 721.8/255.3>GPA:18:1/20:4 | −0.01424 | −0.005479 | 0.053419 | 0.092455 | −0.077675 | 0.066322 | 0.062593 | 0.009618 | −0.01327 | −0.035228 |
| 30 | 721.8/281.3>GPA:16:0/22:5 | −0.084716 | −0.080469 | 0.022543 | 0.033101 | −0.002304 | 0.027823 | −0.069143 | 0.003707 | 0.007283 | 0.020949 |
| 31 | 723.8/283.3>GPA:18:0/20:4 | −0.040122 | −0.003305 | 0.061996 | 0.042198 | −0.158814 | 0.039098 | 0.070559 | −0.072529 | −0.008807 | −0.003327 |
| 32 | 725.8/305.3>GPA:20:3/18:0 | −0.011875 | −0.004898 | 0.07168 | 0.045935 | −0.068782 | −0.037203 | 0.049227 | −0.081143 | 0.029614 | 0.035545 |
| 33 | 729.8/281.3>GPA:38:1 | −0.053509 | 0.040185 | −0.013236 | 0.081675 | −0.11092 | 0.030894 | 0.001458 | 0.004201 | −0.059819 | 0.022522 |
| 34 | 731.8/283.3>GPA:38:0 | −0.080236 | −0.058188 | 0.018634 | 0.068217 | −0.062033 | 0.045104 | −0.044294 | −0.009986 | 0.034849 | 0.022238 |
| 35 | 751.8/303.3>GPA:40:4 | 0.035078 | 0.093794 | 0.059084 | 0.05515 | 0.01272 | −0.008037 | 0.029992 | −0.018064 | −0.091602 | −0.018237 |
| 36 | 757.8/281.3>GPA:40:1 | −0.075795 | −0.002905 | 0.061827 | −0.015566 | −0.079214 | −0.029368 | −0.012374 | 0.014414 | −0.108888 | −0.044691 |
| 37 | 759.8/283.3>GPA:40:0 | −0.070858 | −0.00481 | −0.032553 | 0.060562 | −0.132694 | 0.021167 | 0.04651 | −0.061431 | 0.011088 | 0.008228 |
| 38 | 777.8/329.3>GPA:42:5 | −0.012977 | 0.043147 | −0.046673 | 0.036401 | 0.005109 | 0.076895 | −0.130603 | 0.082809 | 0.032544 | −0.026191 |
| 39 | 481.4/253.3>GPGro:Lyso 16:1 | 0.005131 | −0.035472 | 0.001762 | 0.067 | −0.076077 | 0.115119 | −0.108642 | −0.006033 | −0.017963 | 0.02472 |
| 40 | 483.4/255.3>GPGro:Lyso 16:0 | −0.065954 | −0.061735 | 0.008791 | 0.072747 | 0.028646 | 0.096638 | −0.049179 | 0.010615 | 0.026736 | 0.052043 |
| 41 | 507.4/279.3>GPGro:Lyso 18:2 | −0.048874 | −0.045014 | −0.000334 | 0.097071 | 0.020193 | 0.094266 | −0.049062 | 0.035877 | 0.023521 | 0.066759 |
| 42 | 509.4/281.3>GPGro:Lyso 18:1 | −0.009961 | −0.045458 | 0.003227 | 0.073793 | −0.02699 | 0.127747 | −0.090852 | −0.029569 | 0.012441 | −0.007033 |
| 43 | 511.4/283.3>GPGro:Lyso 18:0 | −0.052597 | −0.0829331 | 0.004427 | 0.063209 | 0.017353 | 0.091822 | −0.046193 | 0.031684 | 0.0206681 | 0.057554 |
| 44 | 531.4/303.3>GPGro:Lyso 20:4 | −0.054517 | −0.030067 | 0.041537 | 0.082642 | 0.039479 | 0.119268 | −0.026043 | −0.004226 | 0.045951 | 0.089766 |
| 45 | 555.4/327.3>GPGro:Lyso 22:6 | −0.039758 | −0.047232 | 0.034572 | 0.085003 | 0.048066 | 0.110903 | −0.024568 | 0.015705 | 0.008566 | 0.076274 |
| 46 | 557.4/329.3>GPGro:Lyso 22:5 | −0.027698 | 0.003738 | −0.012708 | 0.090443 | 0.033185 | 0.129573 | −0.036836 | 0.001142 | 0.005686 | 0.106963 |
| 47 | 717.8/253.3>GPGro:16:1/16:1 | −0.005401 | 0.0019691 | 0.017922 | −0.066789 | −0.118231 | −0.015302 | −0.077523 | −0.034419 | 0.059115 | 0.022424 |

APPENDIX B2-continued

| PCA Transformation Matrix (340 × 340; Benign/Malignant) | | | | | | | | | | | |
|---|---|---|---|---|---|---|---|---|---|---|---|
| 48 | 719.8/253.3>GPGro:16:1/16:0 | 0.010246 | −0.006183 | −0.040735 | 0.017951 | −0.087709 | 0.079878 | −0.043937 | −0.007133 | −0.0249991 | −0.006816 |
| 49 | 721.8/255.3>GPGro:16:0/16:0 | −0.081083 | −0.086789 | 0.016615 | 0.028665 | −0.004156 | 0.028886 | −0.060648 | 0.014521 | 0.00857 | 0.012753 |
| 50 | 743.8/279.3>GPGro:18:2/16:1 | 0.022684 | 0.087982 | −0.022165 | −0.094655 | −0.029264 | −0.028047 | 0.063997 | 0.097453 | −0.073931 | −0.049243 |
| 51 | 743.8/281.3>GPGro:18:1/16:2 | −0.015723 | 0.024573 | 0.04087 | −0.143106 | −0.068335 | −0.017364 | −0.043515 | −0.007912 | −0.011913 | −0.000923 |
| 52 | 745.8/279.3>GPGro:18:2/16:0 | 0.016682 | 0.0851171 | −0.062057 | −0.06854 | −0.028644 | 0.006708 | 0.02891 | 0.107199 | −0.042208 | −0.060283 |
| 53 | 745.8/281.3>GPGro:18:1/16:1 | −0.0429031 | 0.022799 | 0.017171 | −0.151931 | −0.071616 | −0.011315 | −0.023571 | −0.041729 | 0.0169031 | −0.02268 |
| 54 | 747.8/255.2>GPGro:16:0/18:1 | 0.031428 | −0.014287 | −0.072488 | 0.003016 | −0.064691 | 0.137095 | −0.060115 | −0.002505 | 0.022901 | −0.026559 |
| 55 | 747.8/281.1>GPGro:16:0/18:1 | −0.068755 | −0.002116 | 0.109206 | −0.081304 | −0.065079 | −0.035255 | −0.019591 | −0.046946 | −0.008987 | −0.014219 |
| 56 | 749.8/283.3>GPGro:18:0/16:0 | −0.078982 | −0.084161 | 0.026657 | 0.028299 | −0.001837 | 0.024681 | −0.057859 | 0.027822 | −0.007796 | 0.031933 |
| 57 | 767.8/303.3>GPGro:20:4/16:1 | 0.04149 | 0.0792191 | 0.065277 | −0.082892 | 0.01521 | 0.074149 | 0.022654 | −0.093807 | −0.005918 | 0.009831 |
| 58 | 769.8/279.3>GPGro:18:2/18:2 | 0.037191 | 0.078961 | −0.1225031 | 0.0349131 | −0.019191 | −0.025908 | 0.003265 | 0.054102 | −0.0311981 | −0.018533 |
| 59 | 769.8/303.3>GPGro:20:4/16:0 | −0.003808 | −0.003942 | 0.024017 | −0.027454 | 0.002786 | 0.147378 | 0.002896 | −0.047428 | 0.047732 | 0.090066 |
| 60 | 771.8/279.3>GPGro:18:2/18:1 | 0.004129 | 0.025454 | 0.066307 | −0.039228 | −0.034749 | −0.154116 | 0.008129 | 0.067538 | −0.119856 | 0.034165 |
| 61 | 773.8/279.3>GPGro:18:2/18:0 | −0.006231 | −0.077227 | 0.014137 | 0.01674 | −0.036394 | 0.002178 | −0.021062 | 0.12065 | −0.027496 | 0.115571 |
| 62 | 773.8/281.3>GPGro:18:1/18:1 | −0.004185 | −0.010853 | 0.046984 | −0.05047 | −0.083026 | −0.142422 | −0.056561 | −0.009425 | −0.036585 | 0.100105 |
| 63 | 775.8/281.3>GPGro:18:1/18:0 | −0.007038 | −0.096265 | 0.020121 | 0.020999 | −0.045413 | 0.081202 | −0.084503 | 0.03551 | 0.045634 | 0.081416 |
| 64 | 777.8/283.3>GPGro:18:0/18:0 | −0.077705 | −0.087246 | 0.004205 | 0.039829 | 0.009745 | 0.010106 | −0.064888 | 0.01681 | −0.008358 | 0.046171 |
| 65 | 795.8/303.3>GPGro:20:4/18:1 | 0.02931 | 0.051746 | 0.110836 | −0.062185 | 0.021584 | −0.009179 | 0.019708 | −0.095509 | −0.028905 | 0.071946 |
| 66 | 797.8/303.3>GPGro:20:4/18:0 | −0.018421 | −0.075912 | 0.049837 | −0.010175 | 0.039709 | 0.102743 | 0.008627 | −0.005113 | 0.013751 | 0.124013 |
| 67 | 821.8/327.3>GPGro:22:6/18:0 | −0.029127 | −0.054747 | 0.06511 | 0.021038 | 0.050633 | 0.099359 | −0.007161 | 0.03465 | −0.010858 | 0.099849 |
| 68 | 823.8/329.3>GPGro:22:5/18:0 | 0.01287 | 0.007761 | 0.057241 | 0.009907 | 0.019047 | 0.064869 | −0.118053 | 0.01013 | −0.016833 | 0.098039 |
| 69 | 494.4/407.4>Lyso GPSer:16:1 | 0.011796 | −0.045719 | 0.010685 | −0.049731 | −0.023048 | 0.079847 | 0.058184 | 0.118538 | 0.06862 | 0.072088 |
| 70 | 496.4/409.4>Lyso GPSer:16:0 | −0.003528 | −0.022591 | 0.001044 | −0.032985 | −0.00472 | 0.096726 | 0.043313 | 0.128206 | 0.106134 | 0.035433 |
| 71 | 522.4/435.4>Lyso GPSer:18:1 | −0.045761 | 0.005627 | −0.008728 | 0.049898 | −0.137847 | 0.063557 | 0.104241 | 0.02484 | 0.063096 | −0.004589 |
| 72 | 524.4/437.4>Lyso GPSer:18:0 | −0.044601 | −0.002443 | −0.01208 | 0.073569 | −0.094147 | 0.037454 | 0.048974 | −0.013533 | 0.012935 | −0.108309 |
| 73 | 544.4/457.4>Lyso GPSer:20:4 | −0.003452 | 0.0344571 | 0.041751 | 0.078289 | −0.047209 | 0.052753 | 0.014751 | 0.003881 | −0.0165471 | −0.087225 |
| 74 | 570.4/483.4>Lyso GPSer:22:5 | −0.004316 | 0.011212 | −0.105457 | 0.032964 | 0.009438 | −0.032707 | 0.047033 | −0.036198 | 0.003293 | 0.062343 |
| 75 | 732.6/645.6>GPSer:32:1 | 0.005558 | −0.032852 | 0.002337 | −0.069059 | −0.010399 | 0.073707 | 0.066387 | 0.130911 | 0.112486 | 0.080504 |
| 76 | 734.6/647.6>GPSer:32:0 | −0.013677 | −0.031477 | −0.044161 | −0.060299 | 0.009959 | 0.045976 | 0.114082 | 0.071237 | 0.087508 | 0.092259 |
| 77 | 758.6/671.6>GPSer:34:2 | 0.00734 | −0.036502 | −0.006805 | −0.061664 | −0.007733 | 0.077294 | 0.070304 | 0.124738 | 0.109876 | 0.090407 |
| 78 | 760.8/673.8>GPSer:34:1 | 0.0025251 | −0.033161 | 0.005564 | −0.0602 | −0.030853 | 0.080877 | 0.070657 | 0.127677 | 0.1172721 | 0.07421 |
| 79 | 762.8/675.7>GPSer:34:0 | −0.0123 | −0.031389 | 0.012325 | −0.06362 | −0.027866 | 0.076376 | 0.07195 | 0.12937 | 0.102893 | 0.061001 |
| 80 | 782.6/695.7>GPSer:36:4 | −0.011661 | −0.073752 | −0.044275 | 0.046729 | 0.023889 | 0.080339 | 0.036033 | 0.052212 | −0.021215 | −0.023715 |
| 81 | 784.8/697.8>GPSer:36:3 | −0.025298 | −0.033275 | −0.085462 | −0.018794 | 0.003812 | 0.051238 | 0.123562 | 0.010816 | 0.053126 | 0.029762 |
| 82 | 786.8/699.8>GPSer:36:2 | −0.038485 | −0.009332 | −0.013759 | 0.031962 | −0.180279 | 0.051644 | 0.115769 | −0.004856 | −0.002901 | 0.033961 |
| 83 | 788.8/701.8>GPSer:36:1 | −0.04011 | −0.002518 | 0.029083 | 0.043159 | −0.18944 | 0.033402 | 0.076514 | −0.036836 | −0.00751 | 0.01634 |
| 84 | 790.8/703.8>GPSer:36:0 | −0.039723 | −0.00183 | 0.022833 | 0.043161 | −0.193975 | 0.029932 | 0.059279 | −0.03578 | −0.0036261 | 0.014487 |
| 85 | 808.6/721.6>GPSer:38:6 | −0.00345 | −0.028096 | −0.009406 | 0.025579 | −0.07778 | 0.072463 | 0.076233 | 0.041965 | −0.039018 | −0.142724 |
| 86 | 810.8/723.8>GPSer:38:5 | 0.004134 | 0.030992 | −0.014991 | 0.024516 | −0.128117 | 0.078472 | 0.085155 | −0.010566 | −0.057646 | −0.055244 |
| 87 | 812.8/725.8>GPSer:38:4 | −0.009345 | 0.01159 | 0.023134 | 0.060708 | −0.153004 | 0.047916 | 0.090822 | −0.031396 | 0.052078 | −0.062164 |
| 88 | 814.6/727.6>GPSer:38:3 | −0.03768 | −0.008842 | 0.028992 | 0.044622 | −0.18569 | 0.049666 | 0.068137 | −0.015153 | −0.011375 | 0.008645 |
| 89 | 816.8/729.8>GPSer:38:2 | −0.040624 | −0.0012951 | 0.0342681 | 0.046509 | −0.18351 | 0.02538 | 0.062123 | −0.032608 | 0.0111951 | 0.017632 |
| 90 | 818.8/731.8>GPSer:38:1 | −0.0397191 | −0.0041421 | 0.0349431 | 0.038921 | −0.185644 | 0.028423 | 0.054726 | −0.03129 | 0.002638 | 0.003305 |
| 91 | 834.8/747.8>GPSer:40:6 | −0.033574 | −0.001756 | 0.036376 | 0.041471 | −0.18821 | 0.056321 | 0.071914 | −0.033881 | −0.039512 | 0.017987 |
| 92 | 836.8/749.8>GPSer:40:5 | −0.007244 | 0.004666 | 0.008451 | 0.021012 | −0.136259 | 0.035526 | 0.116218 | −0.023085 | −0.045257 | −0.018881 |
| 93 | 838.8/751.8>GPSer:40:4 | −0.018992 | −0.017534 | 0.034309 | 0.035154 | −0.189558 | 0.052686 | 0.067247 | −0.012018 | −0.006058 | −0.043073 |
| 94 | 840.6/753.7>GPSer:40:3 | −0.0271051 | −0.0523541 | −0.030102 | 0.038043 | −0.099102 | 0.062261 | 0.15178 | 0.001546 | −0.01071 | −0.0575 |
| 95 | 778.9/97>Sulfatide:16:0 | 0.045674 | 0.007117 | −0.036683 | 0.110753 | 0.018181 | 0.043504 | 0.047246 | 0.008336 | −0.038476 | −0.105828 |
| 96 | 806.9/97>Sulfatide:18:0 | 0.008653 | −0.060138 | 0.025617 | 0.059528 | 0.021283 | 0.094126 | −0.089013 | −0.011621 | −0.044667 | −0.041094 |
| 97 | 822.9/97>Sulfatide:18:0 (OH) | −0.080177 | 0.033602 | −0.028756 | 0.023822 | 0.074658 | −0.008279 | 0.076047 | −0.013758 | −0.04378 | −0.032455 |
| 98 | 834.9/97>Sulfatide:20:0 | 0.026578 | −0.0994981 | −0.056681 | 0.05001 | 0.068661 | 0.079955 | 0.061035 | 0.012147 | −0.009998 | −0.000264 |

APPENDIX B2-continued

| PCA Transformation Matrix (340 × 340; Benign/Malignant) | | | | | | | | | | | |
|---|---|---|---|---|---|---|---|---|---|---|---|
| 99 | 850.9/97>Sulfatide:20:0 (OH) | −0.0906721 | 0.045077 | 0.0278941 | 0.0068061 | 0.069424 | 0.03415 | 0.046637 | −0.017156 | −0.0293641 | −0.075368 |
| 100 | 862.9/97>Sulfatide:22:1 | 0.0480731 | −0.076934 | −0.079818 | 0.0625661 | 0.04794 | 0.08714 | 0.027714 | −0.012783 | −0.034974 | −0.002282 |
| 101 | 878.9/97>Sulfatide:22:1 (OH) | 0.00495 | −0.097621 | −0.055742 | 0.027042 | 0.081479 | 0.069818 | 0.081227 | 0.029209 | −0.01566 | 0.03026 |
| 102 | 888.9/97>Sulfatide:24:1 | 0.0609 | 0.017362 | −0.009428 | 0.062025 | −0.00374 | 0.074771 | −0.021281 | −0.051274 | −0.062013 | −0.02817 |
| 103 | 890.9/97>Sulfatide:24:0 | 0.001421 | −0.0460441 | −0.074314 | 0.07251 | 0.057748 | 0.058687 | 0.026752 | −0.035141 | −0.051278 | 0.005735 |
| 104 | 906.7/97>Sulfatide:24:0 (OH) | −0.0138121 | 0.0257991 | −0.0583081 | 0.056666 | 0.052272 | 0.005253 | 0.067656 | −0.114635 | −0.064113 | 0.108502 |
| 105 | 1147/281.3>CardioliGPlnsn:52:3 | −0.026976 | −0.061299 | 0.030583 | 0.017241 | −0.010143 | 0.016381 | −0.114602 | 0.00017 | −0.007208 | −0.043818 |
| 106 | 1376/281.3>CardioliGPlnsn:66:2 | −0.083078 | −0.004467 | 0.073416 | −0.035515 | −0.002018 | −0.092733 | −0.050099 | −0.017245 | 0.002775 | 0.017578 |
| 107 | 1400/281.3>CardioliGPlnsn:68:4 | −0.079651 | −0.013241 | 0.079167 | −0.030472 | −0.024831 | −0.087839 | −0.029823 | 0.007094 | −0.008875 | 0.00908 |
| 108 | 1402/281.3>CardioliGPlnsn:68:3 | −0.064922 | −0.013236 | 0.090093 | −0.004344 | −0.006519 | −0.078451 | −0.06802 | 0.009713 | 0.018373 | 0.003482 |
| 109 | 1404/281.3>CardioliGPlnsn:68:2 | −0.064494 | −0.021809 | 0.078175 | −0.013724 | −0.014469 | −0.024557 | −0.024735 | −0.007303 | 0.009593 | 0.006456 |
| 110 | 1406/281.3>CardioliGPlnsn:68:1 | −0.038016 | −0.067954 | 0.064092 | −0.050329 | 0.024282 | 0.005732 | −0.002594 | 0.0376 | −0.01703 | −0.029614 |
| 111 | 1426/281.3>CardioliGPlnsn:70:5 | −0.08534 | −0.021429 | 0.069062 | 0.002551 | −0.008485 | −0.027816 | −0.072165 | −0.026929 | 0.016402 | 0.000426 |
| 112 | 1428/281.3>CardioliGPlnsn:70:4 | −0.077685 | −0.02416 | 0.068978 | 0.000754 | 0.005201 | −0.000149 | −0.071418 | −0.032041 | 0.000683 | −0.021926 |
| 113 | 1430/281.3>CardioliGPlnsn:70:3 | −0.081106 | −0.008975 | 0.07878 | −0.005339 | 0.003699 | −0.03613 | −0.057642 | 0.004141 | −0.010801 | −0.007045 |
| 114 | 1432/281.3>CardioliGPlnsn:70:2 | −0.063567 | −0.057026 | 0.058901 | 0.0059551 | −0.036431 | −0.022611 | −0.074933 | −0.00207 | 0.0316771 | −0.022051 |
| 115 | 1434/281.3>CardioliGPlnsn:70:1 | −0.086215 | −0.032163 | 0.043753 | 0.001678 | −0.009699 | −0.015966 | −0.04956 | −0.044907 | −0.01127 | 0.031523 |
| 116 | 1436/281.3>CardioliGPlnsn:70:0 | −0.067223 | −0.048606 | 0.062015 | −0.023881 | −0.041409 | −0.023594 | −0.050079 | 0.021462 | 0.007595 | 0.050364 |
| 117 | 436.6/196.1>Lyso GPEtn:Lyso16:1e/16:0p | 0.043885 | 0.071478 | −0.066839 | 0.034421 | −0.040777 | 0.042979 | −0.067024 | 0.021023 | −0.067332 | −0.088975 |
| 118 | 450.4/196.1>Lyso GPEtn:Lyso 16:1 | 0.016683 | 0.036111 | −0.101938 | 0.038854 | −0.069401 | −0.033515 | −0.093591 | −0.033405 | 0.060841 | −0.045438 |
| 119 | 452.4/196.1>Lyso GPEtn:Lyso 16:0 | −0.059769 | 0.018356 | −0.079268 | 0.016832 | −0.041971 | −0.018727 | −0.066455 | −0.064329 | 0.068395 | −0.055831 |
| 120 | 462.4/196.1>Lyso GPEtn:Lyso18:2e/18:1p | 0.015348 | 0.064403 | −0.097771 | 0.008847 | −0.057356 | 0.072281 | −0.074253 | 0.004502 | −0.098351 | −0.038455 |
| 121 | 464.5/196.1>Lyso GPEtn:Lyso18:1e/18:0p | −0.027338 | 0.07044 | −0.06157 | 0.033246 | −0.0419 | 0.082775 | −0.072327 | 0.048312 | −0.093585 | −0.074779 |
| 122 | 476.6/196.1>Lyso GPEtn:Lyso18:2a | 0.028457 | 0.052934 | −0.016709 | 0.094476 | −0.03922 | −0.108414 | −0.044661 | 0.048659 | −0.005223 | −0.008814 |
| 123 | 478.4/196.1>Lyso GPEtn:Lyso 18:1 | 0.013986 | 0.051077 | −0.076324 | 0.072902 | −0.06273 | −0.063223 | −0.058516 | −0.014545 | 0.034427 | −0.075284 |
| 124 | 480.4/196.1>Lyso GPEtn:Lyso 18:0 | −0.058519 | 0.037477 | −0.086294 | 0.02505 | −0.041092 | −0.03372 | −0.04173 | −0.046807 | 0.120152 | −0.048174 |
| 125 | 492.5/196.1>Lyso GPEtn:Lyso20:1e/20:0p | −0.00742 | 0.068257 | −0.110217 | −0.005658 | −0.02853 | 0.064838 | −0.062552 | −0.043453 | −0.021434 | −0.041597 |
| 126 | 500.4/196.1>Lyso GPEtn:Lyso 20:4 | 0.04682 | 0.084445 | −0.040185 | 0.027135 | −0.019567 | 0.014338 | −0.045128 | −0.042739 | −0.003418 | −0.082465 |
| 127 | 524.4/196.1>Lyso GPEtn:Lyso 22:6 | 0.051516 | 0.099857 | −0.022403 | 0.036521 | −0.008648 | 0.020756 | −0.038594 | −0.061888 | −0.023695 | −0.06118 |
| 128 | 688.6/196.1>GPEtn:16:0/16:1 | −0.012175 | −0.01929 | −0.132624 | −0.005622 | −0.00614 | 0.022355 | 0.018394 | −0.081776 | −0.016546 | 0.090389 |
| 129 | 690.7/196.1>GPEtn 16:0/16:0 | −0.029677 | 0.025573 | −0.074556 | −0.004071 | −0.012344 | 0.020304 | −0.000006 | −0.050578 | 0.002647 | −0.086188 |
| 130 | 698.6/196.1>GPEtn:34:2p, 34:3e | −0.005076 | 0.02706 | −0.114915 | 0.004218 | −0.009697 | 0.065498 | 0.009489 | −0.027928 | −0.029958 | −0.02908 |
| 131 | 700.6/196.1>GPEtn:34:1p, 34:2e | −0.002012 | 0.023802 | −0.040793 | 0.019836 | 0.030939 | 0.025512 | −0.064194 | 0.017732 | −0.008069 | −0.175125 |
| 132 | 702.6/196.1>GPEtn:34:0p, 34:1e | −0.016195 | 0.012816 | −0.132621 | 0.000852 | −0.024758 | 0.003157 | 0.02935 | −0.070703 | −0.065128 | 0.086649 |
| 133 | 710.8/196.1>GPEtn:18:1/16:1 | −0.026057 | 0.025012 | −0.118244 | 0.000375 | 0.019641 | 0.053919 | −0.03469 | 0.060614 | 0.02938f | 0.012175 |
| 134 | 712.8/196.1>GPEtn:18:2/16:1 | −0.001288 | 0.040537 | −0.098996 | −0.011303 | −0.035684 | 0.02249 | −0.071727 | 0.008407 | 0.034557 | −0.069531 |
| 135 | 714.7/196.1>GPEtn:18:1/16:1 | −0.018838 | 0.061533 | −0.152859 | −0.005728 | −0.025768 | −0.00978 | 0.025639 | −0.036405 | 0.019551 | 0.09074 |
| 136 | 716.7/196.1>GPEtn:18:1/16:0 | −0.021798 | 0.055897 | −0.111635 | −0.050075 | −0.052508 | 0.017384 | −0.060832 | −0.030104 | 0.050164 | 0.028678 |
| 137 | 718.6/196.1>GPEtn:18:0/16:0 | 0.01802 | 0.00649 | −0.128636 | 0.032303 | −0.0056 | 0.048243 | 0.03729 | −0.09998 | −0.014574 | −0.017906 |
| 138 | 722.6/196.1>GPEtn:36:4p | −0.027832 | 0.018137 | −0.0242 | −0.003291 | 0.027505 | 0.033365 | −0.139121 | 0.011796 | −0.014852 | −0.032333 |
| 139 | 724.6/196.1>GPEtn:36:3p, 36:4e | −0.014742 | 0.022503 | −0.058987 | 0.020957 | 0.020259 | 0.041668 | −0.081291 | 0.075648 | −0.075213 | 0.10739 |
| 140 | 726.6/196.1>GPEtn:36:2p, 36:3e | −0.008988 | 0.018926 | −0.083266 | 0.022315 | −0.030975 | −0.007667 | 0.053721 | −0.037211 | 0.012809 | −0.06308 |
| 141 | 728.6/196.1>GPEtn:36:1p, 36:2e | −0.030646 | 0.030014 | −0.144423 | 0.014506 | −0.014034 | −0.019378 | 0.053285 | −0.067773 | −0.000192 | 0.067666 |
| 142 | 738.8/196.1>GPEtn:20:4/16:0 | 0.023548 | 0.110648 | −0.036581 | −0.055656 | −0.019769 | 0.060777 | −0.0414 | −0.015764 | 0.046239 | 0.001782 |
| 143 | 740.8/196.1>GPEtn:18:2/18:1 | −0.009056 | 0.053579 | −0.130281 | 0.033283 | −0.005761 | −0.030487 | 0.029974 | 0.000218 | 0.04379 | 0.0787 |
| 144 | 742.8/196.1>GPEtn:18:1/18:1 | −0.006148 | 0.068758 | −0.098411 | 0.004172 | −0.055751 | −0.042216 | −0.051946 | 0.026179 | 0.074409 | 0.009707 |
| 145 | 744.6/196.1>GPEtn:18:0/18:1 | −0.020328 | 0.067964 | −0.126269 | 0.005047 | −0.019861 | 0.009648 | −0.048232 | 0.009403 | 0.021994 | 0.081102 |
| 146 | 746.8/196.1>GPEtn:18:0/18:0 | −0.010901 | 0.072861 | −0.134156 | −0.011803 | −0.010594 | 0.054536 | −0.058206 | 0.029621 | −0.021755 | 0.063727 |
| 147 | 748.6/196.1>GPEtn:38:5p, 38:6e | 0.004564 | 0.07701 | −0.063297 | −0.008831 | −0.015094 | 0.090567 | −0.117283 | 0.062151 | −0.032998 | −0.008248 |
| 148 | 750.6/196.1>GPEtn:38:4p, 38:5e | −0.005834 | 0.042416 . | −0.079837 | 0.075507 | −0.009586 | 0.025994 | 0.001858 | 0.010805 | −0.034729 | 0.032755 |
| 149 | 752.6/196.1>GPEtn:38:3p, 38:4e | −0.01744 | 0.020978 | −0.134493 | 0.025863 | −0.001418 | −0.040848 | 0.085956 | −0.083817 | 0.003319 | 0.076734 |

APPENDIX B2-continued

PCA Transformation Matrix (340 × 340; Benign/Malignant)

| | | | | | | | | | | | |
|---|---|---|---|---|---|---|---|---|---|---|---|
| 150 | 754.6/196.1>GPEtn:38:2p, 38:3e | −0.019753 | 0.013293 | −0.118531 | 0.012017 | −0.004529 | 0.001418 | 0.045335 | −0.116926 | −0.000939 | 0.03627 |
| 151 | 756.6/196.1>GPEtn:38:1p, 38:2e | 0.000402 | 0.011037 | −0.012471 | −0.028528 | −0.033896 | 0.071581 | −0.043519 | −0.053825 | −0.024704 | −0.149045 |
| 152 | 762.8/196.1>GPEtn:20:4/18:2 | 0.034602 | 0.113264 | −0.018441 | −0.025762 | −0.031007 | 0.064146 | −0.064717 | −0.041483 | −0.013458 | 0.024039 |
| 153 | 764.8/196.1>GPEtn:20:4/18:1 | 0.026498 | 0.101221 | −0.050319 | −0.029069 | −0.027447 | 0.034052 | −0.071046 | −0.00543 | 0.004217 | 0.080043 |
| 154 | 766.8/196.1>G PEtn:20:4/18:0 | 0.03289 | 0.097617 | −0.034881 | −0.059054 | −0.029543 | 0.03073 | −0.017039 | −0.050139 | 0.060444 | 0.026563 |
| 155 | 768.8/196.1>GPEtn:20:3/18:0 | 0.018748 | 0.090745 | −0.0739 | −0.022169 | −0.042063 | 0.018571 | −0.071224 | −0.070666 | 0.024625 | 0.058421 |
| 156 | 770.6/196.1>GPEtn:20:2/18:0 | −0.000549 | 0.030693 | −0.122343 | −0.001015 | −0.026781 | −0.00684 | −0.006522 | −0.08292 | −0.061273 | 0.027544 |
| 157 | 772.6/196.1>GPEtn:20:1/18:0 | −0.037848 | −0.015661 | −0.139596 | −0.006715 | −0.010895 | −0.042577 | 0.066801 | −0.07117 | 0.015315 | 0.041909 |
| 158 | 776.6/196.1>GPEtn:40:5p, 40:6e | −0.005066 | 0.01002 | −0.033543 | 0.014156 | 0.01766 | −0.049868 | −0.029952 | −0.105951 | −0.037695 | −0.033941 |
| 159 | 778.6/196.1>GPEtn:40:4p, 40:5e | −0.038168 | −0.020331 | 0.011993 | −0.007505 | 0.023916 | 0.017548 | −0.019732 | −0.10279 | −0.036647 | 0.023617 |
| 160 | 780.6/196.1>GPEtn:40:3p, 40:4e | −0.015306 | −0.021714 | −0.021912 | 0.004198 | −0.006231 | 0.011908 | 0.006681 | −0.042525 | −0.055116 | 0.031938 |
| 161 | 784.6/196.1>GPEtn:40:1p, 40:2e | −0.015923 | 0.000972 | −0.08726 | 0.022998 | −0.029255 | −0.039902 | −0.010016 | −0.076692 | −0.041761 | 0.102347 |
| 162 | 788.8/196.1>GPEtn:22:4/18:3 | −0.003818 | 0.05636 | −0.077226 | 0.02654 | −0.03089 | 0.00761 | 0.048328 | −0.064546 | 0.021104 | 0.074598 |
| 163 | 790.8/196.1>GPEtn:22:4/18:2 | 0.022073 | 0.078682 | −0.045835 | −0.021537 | −0.019512 | 0.006342 | 0.052556 | −0.143985 | 0.019799 | 0.09909 |
| 164 | 792.6/196.1>GPEtn:40:5a | 0.025644 | 0.074015 | −0.025952 | −0.063763 | −0.038837 | 0.0356 | −0.078514 | −0.078321 | 0.043042 | −0.054562 |
| 165 | 794.6/196.1>GPEtn:40:4a | 0.030367 | 0.048035 | −0.07949 | −0.056761 | 0.017478 | 0.007544 | −0.036841 | −0.114635 | 0.021641 | 0.007741 |
| 166 | 796.8/196.1>GPEtn:40:3a | −0.027897 | −0.040908 | −0.014734 | −0.040989 | −0.027475 | −0.029825 | −0.022589 | 0.003211 | 0.066722 | −0.138484 |
| 167 | 798.6/196.1>GPEtn:40:2a | −0.041401 | −0.016512 | −0.121112 | −0.004345 | −0.023351 | −0.043524 | 0.033284 | −0.065723 | −0.03063 | 0.083236 |
| 168 | 569.4/241.1>GPIns:Lyso 16:1 | 0.023775 | −0.002423 | 0.005583 | 0.097485 | 0.000391 | −0.047001 | −0.08565 | −0.045639 | 0.143145 | 0.023867 |
| 169 | 571.3/241.1>GPIns:Lyso 16:0 | −0.029828 | −0.052726 | −0.077626 | 0.108811 | 0.048908 | −0.0333 | 0.035638 | 0.034239 | 0.099895 | −0.034527 |
| 170 | 595.4/241.1>GPIns:Lyso 18:2 | −0.023809 | −0.056246 | −0.049537 | 0.10776 | 0.060693 | −0.026385 | 0.054228 | 0.064928 | 0.076799 | −0.023364 |
| 171 | 597.4/241.1>GPIns:Lyso 18:1 | −0.007871 | −0.031717 | −0.071707 | 0.14425 | 0.035978 | −0.062698 | 0.021002 | 0.044427 | 0.101814 | −0.025296 |
| 172 | 599.4/241.1>GPIns:Lyso 18:0 | −0.051682 | −0.028463 | −0.074846 | 0.097855 | 0.044753 | −0.056329 | −0.021013 | −0.025345 | 0.124121 | −0.079202 |
| 173 | 619.5/241.1>GPIns:Lyso 20:4 | 0.01745 | 0.071415 | 0.014736 | 0.137194 | 0.061641 | −0.024327 | −0.020286 | −0.035842 | 0.126452 | 0.024991 |
| 174 | 621.5/241.1>GPIns:Lyso 20:3 | 0.037471 | 0.04834 | 0.007476 | 0.122303 | 0.001751 | −0.075253 | −0.03205 | −0.032016 | 0.133141 | 0.057119 |
| 175 | 623.5/241.1>GPIns:Lyso 20:2 | 0.018314 | 0.024821 | −0.05421 | 0.119644 | 0.014096 | −0.098066 | −0.013956 | −0.016047 | 0.092482 | 0.021671 |
| 176 | 625.5/241.1>GPIns:Lyso 20:1 | −0.02822 | −0.045251 | −0.114251 | 0.06724 | 0.007799 | −0.0614 | 0.009312 | −0.011969 | 0.082461 | −0.072865 |
| 177 | 627.5/241.1>GPIns:Lyso 20:0 | 0.006963 | −0.057154 | 0.024857 | 0.043269 | 0.027628 | 0.01492 | −0.09319 | 0.013739 | −0.036611 | −0.045946 |
| 178 | 679.5/241.1>GPIns:Lyso 24:2 | 0.026215 | −0.092682 | −0.060814 | 0.061083 | 0.067266 | 0.074794 | 0.027532 | −0.032655 | 0.01094 | 0.001251 |
| 179 | 835.7/241.1>GPIns:34:1 | 0.044855 | −0.11323 | −0.024904 | 0.036836 | 0.060695 | 0.048921 | 0.012964 | 0.003216 | −0.002429 | 0.02172 |
| 180 | 857.7/241.1>GPIns:36:4 | 0.04577 | −0.110753 | −0.015424 | 0.033064 | 0.062555 | 0.063359 | 0.017265 | 0.00104 | −0.004589 | 0.035858 |
| 181 | 859.8/241.1>GPIns:36:3 | 0.034686 | −0.118011 | −0.020804 | 0.033371 | 0.057749 | 0.051681 | 0.022498 | 0.02151 | −0.014339 | 0.030846 |
| 182 | 861.8/241.1>GPIns:36:2 | 0.050335 | −0.110481 | −0.011567 | 0.023475 | 0.070376 | 0.02961 | 0.024265 | 0.012248 | −0.01447 | 0.023844 |
| 183 | 863.7/241.1>GPIns:36:1 | 0.062499 | −0.099054 | −0.01549 | 0.04194 | 0.044311 | −0.007493 | −0.005259 | −0.011441 | −0.023104 | 0.017464 |
| 184 | 865.8/241.1>GPIns:36:0 | 0.055777 | −0.081765 | −0.060211 | 0.049443 | 0.027516 | 0.018036 | −0.016165 | −0.056181 | 0.005635 | 0.01101 |
| 185 | 873.8/241.1>GPIns:37:3 | 0.060563 | −0.060947 | −0.010556 | 0.033151 | 0.013533 | 0.02403 | −0.079508 | −0.078554 | −0.016687 | −0.001265 |
| 186 | 883.8/241.1>GPIns:38:5 | 0.05039 | −0.070109 | 0.022692 | 0.042448 | 0.009385 | −0.036307 | −0.074096 | −0.030613 | −0.020439 | 0.018546 |
| 187 | 885.8/241.1>GPIns:38:4 | 0.091134 | 0.012892 | 0.044545 | 0.000197 | 0.040366 | 0.018017 | −0.019762 | −0.099786 | 0.005905 | 0.039424 |
| 188 | 887.8/241.1>GPIns:38:3 | 0.089218 | 0.001424 | 0.041702 | 0.010875 | 0.011446 | −0.00966 | −0.033708 | −0.084645 | 0.024006 | 0.067868 |
| 189 | 889.8/241.1>GPIns:38:2 | 0.078163 | −0.038858 | −0.029923 | 0.053236 | 0.028366 | 0.000549 | −0.017984 | −0.034937 | 0.020771 | 0.048434 |
| 190 | 891.8/241.1>GPIns:38:1 | −0.037391 | −0.092666 | −0.110161 | −0.011445 | 0.038806 | −0.027904 | 0.055548 | −0.024509 | 0.001029 | 0.004486 |
| 191 | 893.8/241.1>GPIns:38:0 | −0.037422 | −0.067936 | −0.11838 | −0.006791 | 0.039252 | −0.023218 | 0.085681 | −0.067579 | 0.003997 | 0.037729 |
| 192 | 909.8/241.1>GPIns:40:6 | 0.084815 | 0.030298 | 0.048455 | 0.040873 | 0.029336 | 0.011349 | −0.022421 | −0.106234 | −0.033711 | 0.017964 |
| 193 | 911.8/241.1>GPIns:40:5 | 0.084715 | −0.001342 | 0.070557 | 0.033414 | 0.040335 | −0.010971 | −0.028983 | −0.095906 | −0.009022 | 0.058071 |
| 194 | 913.8/241.1>GPIns:40:4 | 0.054895 | −0.070173 | 0.030849 | 0.012373 | 0.014758 | −0.03805 | −0.069095 | −0.086327 | −0.007112 | 0.076281 |
| 195 | 915.8/241.1>GPIns:40:3 | −0.025864 | −0.107292 | −0.024498 | −0.076653 | 0.004314 | −0.016086 | −0.037076 | 0.00549 | −0.000767 | 0.006344 |
| 196 | 917.8/241.1>GPIns:40:2 | −0.016173 | −0.134804 | −0.041884 | −0.006358 | 0.038058 | 0.011309 | −0.01509 | 0.02688 | −0.015215 | 0.020268 |
| 197 | 919.8/241.1>GPIns:40:1 | −0.048378 | −0.089344 | −0.09804 | −0.014296 | 0.041671 | −0.037698 | 0.046681 | −0.03631 | −0.006099 | 0.032374 |
| 198 | 963.9/241.1>GPInsP:38:5 | −0.063111 | −0.061261 | −0.046366 | −0.050192 | 0.001892 | −0.053534 | −0.064698 | −0.039092 | −0.004438 | −0.063875 |
| 199 | 963.9/321.1>GPInsP:38:5 | −0.030356 | −0.028252 | −0.070671 | 0.023612 | 0.027113 | −0.016253 | 0.016417 | −0.069847 | −0.007218 | 0.030715 |
| 200 | 965.9/241.1>GPInsP:38:4 | −0.065508 | −0.081627 | 0.000484 | −0.024357 | −0.019816 | −0.040385 | −0.062368 | −0.028504 | −0.021181 | −0.068228 |

APPENDIX B2-continued

PCA Transformation Matrix (340 × 340; Benign/Malignant)

| | | | | | | | | | | | |
|---|---|---|---|---|---|---|---|---|---|---|---|
| 201 | 965.9/321.1>GPInsP:38:4 | −0.041148 | 0.008884 | −0.050156 | 0.01687T | −0.050423 | −0.05332 | 0.016211 | −0.056036 | −0.019377 | 0.096118 |
| 202 | 967.9/241.1>GPInsP:38:3 | −0.060621 | −0.076559 | 0.002821 | −0.045025 | 0.002192 | −0.047561 | −0.071535 | −0.012569 | 0.007126 | −0.071771 |
| 203 | 967.9/321.1>GPInsP:38:3 | 4.069346 | −0.051435 | −0.018768 | 0.008802 | 0.007093 | −0.043651 | −0.072583 | −0.083783 | −0.003599 | −0.000678 |
| 204 | 1045.9/241.1>GPInsP2: 38:4 | −0.04929 | −0.059736 | −0.046782 | 0.006129 | 0.033627 | −0.011446 | 0.027263 | −0.049906 | −0.019637 | 0.047421 |
| 205 | 1045.9/321.1>GPInsP2: 38:4 | −0.00415 | −0.000462 | 0.028555 | −0.002658 | −0.00122 | 0.029377 | −0.03957 | −0.02448 | 0.004334 | −0.032657 |
| 206 | 1045.9/401.1>GPInsP2: 38:4 | −0.020605 | −0.010422 | 0.012088 | 0.010791 | 0.034931 | 0.006001 | 0.00221 | −0.019561 | 0.016272 | −0.086093 |
| 207 | 1047.9/321.1>GPInsP2: 38:3 | −0.015791 | −0.022604 | −0.000951 | 0.028631 | 0.045388 | 0.013455 | −0.03283 | −0.017293 | 0.0418 | −0.0841 |
| 208 | 1047.9/401.1>GPInsP2: 38:3 | −0.055863 | −0.023641 | −0.004295 | −0.018381 | 0.000213 | −0.030885 | −0.060003 | −0.06087 | −0.010742 | −0.099614 |
| 209 | 1047.9/241.1>GPInsP2: 38:3 | −0.010692 | −0.070646 | 0.001472 | 0.037953 | 0.002682 | −0.047222 | −0.08253 | −0.002409 | 0.033501 | −0.051604 |
| 210 | 1125.9/241.1>GPInsP3: 38:4 | −0.030242 | −0.03125 | −0.042851 | −0.030425 | 0.00976 | −0.015107 | −0.042259 | −0.097283 | 0.031554 | −0.018597 |
| 211 | 1125.9/321.1>GPInsP3: 38:4 | −0.016599 | −0.009729 | −0.101672 | 0.060954 | 0.026662 | −0.031309 | 0.063737 | −0.022814 | 0.080266 | −0.073373 |
| 212 | 1125.9/401.1>GPInsP3: 38:4 | −0.005029 | −0.005891 | −0.028816 | 0.020174 | −0.012667 | 0.003098 | −0.035818 | 0.075497 | 0.012557 | −0.050406 |
| 213 | 1125.9/481.1>GPInsP3: 38:4 | 0.008512 | −0.034043 | 0.025386 | 0.000747 | 0.028806 | 0.037127 | 0.002546 | −0.009896 | 0.072441 | −0.002171 |
| 214 | 835.7/281.1>GPIns:34:1 | 0.053021 | −0.09791 | −0.051244 | 0.051195 | 0.05575 | 0.064423 | 0.02007 | −0.002622 | 0.010134 | 0.00358 |
| 215 | 821.8/241.1>GPIns: 34:1 | 0.040711 | −0.093957 | −0.026511 | 0.052598 | 0.041218 | 0.028745 | −0.008477 | −0.030932 | −0.036581 | −0.021981 |
| 216 | 494.4/184.1>GPCho:Lyso 16:1 | −0.007197 | −0.015633 | 0.027765 | 0.070577 | −0.088468 | −0.097919 | −0.114163 | −0.002684 | 0.097486 | 0.065256 |
| 217 | 490.4/184.1>GPCho:Lyso 16:0 | −0.05783 | 0.003396 | 0.006907 | 0.052563 | −0.032052 | −0.072792 | −0.098447 | 0.020264 | 0.059159 | 0.000126 |
| 218 | 520.4/184.1>GPCho:Lyso 18:2 | −0.030144 | 0.074393 | −0.022304 | 0.122329 | 0.012572 | −0.102165 | −0.008262 | 0.103359 | 0.034247 | 0.037417 |
| 219 | 522.4/184.1>GPCho:Lyso 18:1 | −0.062803 | 0.030173 | 0.021117 | 0.074919 | −0.041057 | −0.088042 | −0.073513 | 0.050913 | 0.082384 | 0.042922 |
| 220 | 524.4/184.1>GPCho:Lyso 18:0 | −0.050247 | 0.001854 | −0.014935 | 0.073046 | −0.03881 | −0.142516 | −0.06783 | 0.021315 | 0.018164 | 0.06451 |
| 221 | 544.4/184.1>GPCho:Lyso 20:4 | 0.005811 | 0.106194 | 0.06389 | 0.064921 | 0.054423 | 0.023036 | −0.006017 | −0.062734 | 0.050154 | 0.07204 |
| 222 | 568.4/184.1>GPCho:Lyso 22:6 | 0.012696 | 0.095594 | 0.067971 | 0.09505 | 0.047159 | 0.002385 | −0.000853 | −0.026309 | −0.007573 | 0.06539 |
| 223 | 570.4/184.1>GPCho:Lyso 22:5 | 0.021668 | 0.088732 | 0.074235 | 0.09995 | 0.029593 | −0.026078 | −0.014144 | −0.023998 | 0.011436 | 0.090507 |
| 224 | 678.5/184.1>GPCho:28:0 | −0.050297 | −0.06399 | −0.038798 | 0.003113 | −0.058753 | −0.067997 | −0.09642 | −0.001433 | −0.07166 | 0.011495 |
| 225 | 678.5/184.1>GPCho:28:0a | −0.052884 | −0.055378 | −0.043095 | 0.010275 | −0.058183 | −0.071163 | −0.094991 | −0.013136 | −0.071232 | 0.010535 |
| 226 | 704.6/184.1>GPCho:30:1a | −0.098161 | 0.034928 | 0.025845 | −0.016733 | 0.065402 | 0.025315 | 0.061764 | 0.017562 | −0.007589 | −0.075475 |
| 227 | 700.6/184.1>GPCho:30:0a | −0.073662 | 0.019098 | 0.03745 | −0.014939 | 0.033794 | −0.007062 | 0.023411 | −0.033233 | −0.035601 | −0.02025 |
| 228 | 718.6/184.1>GPCho:32:0p, 32.1e | −0.071956 | −0.040124 | −0.001555 | 0.043081 | 0.004493 | −0.037141 | 0.033367 | −0.025692 | −0.136361 | −0.036946 |
| 229 | 730.8/184.1>GPCho:32:2 | −0.064141 | 0.012355 | 0.01945 | 0.019987 | 0.038821 | −0.026908 | 0.048558 | −0.02101 | 0.027242 | −0.0232 |
| 230 | 732.6/184.1>GPCho:32:1a | −0.05463 | −0.046615 | 0.015611 | −0.064967 | −0.034381 | 0.006155 | −0.046436 | −0.075384 | 0.113451 | 0.015974 |
| 231 | 734.6/184.1>GPCho:32:0a | −0.040376 | −0.055883 | 0.02506 | −0.113048 | −0.009901 | 0.054704 | −0.008414 | −0.062158 | 0.021046 | −0.064823 |
| 232 | 742.6/184.1>GPCho:34:2p, 34.3e | −0.030669 | −0.068179 | 0.016245 | 0.070036 | −0.040885 | −0.087776 | −0.007114 | 0.062602 | −0.098268 | −0.013058 |
| 233 | 744.6/184.1>GPCho:34:1p, 34.2e | 0.055527 | 0.007884 | 0.006485 | 0.095315 | −0.021901 | −0.076416 | 0.005613 | 0.092777 | −0.120475 | −0.003526 |
| 234 | 740.6/184.1>GPCho:34:0p, 34.1e | −0.005905 | −0.071779 | 0.016101 | 0.031273 | −0.041762 | 0.01183 | −0.016034 | 0.026839 | −0.113658 | −0.062552 |
| 235 | 748.6/184.1>GPCho:34:0e | −0.025896 | −0.084904 | −0.003618 | 0.008419 | −0.023021 | −0.000754 | 0.013578 | −0.009898 | −0.148857 | −0.023706 |
| 236 | 750.6/184.1>GPCho:34:3a | −0.038074 | −0.109372 | −0.057378 | −0.005479 | −0.048274 | −0.050646 | −0.046878 | 0.064727 | 0.013296 | −0.03096 |
| 237 | 758.7/184.1>GPCho:34:2a | 0.075569 | −0.028951 | −0.071458 | −0.02836 | −0.034602 | 0.040906 | 0.004554 | 0.080722 | −0.017794 | −0.069348 |
| 238 | 760.6/184.1>GPCho:34:1a | 0.026355 | −0.084339 | 0.004248 | −0.090204 | −0.082982 | 0.055059 | −0.075737 | −0.022352 | 0.048312 | −0.018352 |
| 239 | 762.6/184.1>GPCho:34:0a | 0.008555 | −0.081809 | 0.022504 | −0.096224 | −0.08003 | 0.020691 | −0.083969 | −0.039421 | 0.066988 | −0.001067 |
| 240 | 768.6/184.1>GPCho:36:3p, 30.4e | 0.072766 | 0.044583 | 0.072378 | 0.06934 | 0.005623 | 0.041908 | 0.022526 | −0.037355 | −0.053947 | −0.000231 |
| 241 | 770.6/184.1>GPCho:36:2p, 30.3e | 0.066236 | −0.002706 | 0.041564 | 0.114543 | −0.031341 | −0.039619 | 0.012724 | 0.052369 | −0.094926 | 0.0058 |
| 242 | 772.6/184.1>GPCho:36:1p, 30.2e | 0.01739 | −0.084196 | −0.043945 | 0.060234 | −0.029579 | −0.067031 | −0.010498 | 0.046592 | −0.138063 | −0.029389 |
| 243 | 774.6/184.1>GPCho:36:0p, 30.1e | 0.009224 | −0.091585 | −0.012893 | 0.047348 | −0.02338 | −0.025297 | −0.016033 | −0.027742 | −0.167107 | 0.042971 |
| 244 | 782.6/184.1>GPCho:36:4a | −0.08391 | 0.037087 | 0.042778 | −0.047275 | 0.012652 | 0.088205 | 0.003954 | −0.099569 | 0.021389 | 0.027686 |
| 245 | 784.6/184.1>GPCho:36:3a | 0.09813 | 0.002063 | 0.006218 | 0.015703 | −0.054305 | −0.014677 | −0.0467 | −0.034242 | 0.016437 | 0.075317 |
| 246 | 780.6/184.1>GPCho:36:2a | 0.0762 | −0.009856 | −0.070893 | 0.039562 | −0.045103 | −0.080225 | −0.039095 | 0.063666 | −0.042581 | 0.0342 |
| 247 | 788.6/184.1>GPCho:36:1a | −0.010787 | −0.095629 | −0.0704611 | −0.016442 | −0.055894 | −0.110174 | −0.057515 | 0.034781 | 0.0072871 | 0.053323 |
| 248 | 790.8/184.1>GPCho:36:0 | −0.023928 | −0.109802 | −0.025847 | −0.011982 | −0.049354 | −0.10491 | −0.047259 | 0.016121 | −0.009013 | 0.06784 |
| 249 | 792.6/184.1>GPCho:38:5p, 38.6e | 0.053533 | 0.028543 | 0.075561 | 0.083865 | −0.002581 | 0.005931 | −0.000661 | −0.022882 | −0.103585 | 0.00126 |
| 250 | 194.6/184.1>GPCho:38:4p, 38.5e | 0.071368 | 0.040939 | 0.076383 | 0.072008 | 0.017777 | 0.059705 | 0.022868 | −0.031797 | −0.063604 | −0.000004 |
| 251 | 790.6/184.1>GPCho:38:3p, 38.4e | 0.071743 | 0.019785 | 0.07237 | 0.064986 | 0.016523 | 0.069748 | 0.01925 | −0.036678 | −0.087863 | 0.016563 |

APPENDIX B2-continued

PCA Transformation Matrix (340 × 340; Benign/Malignant)

| | | | | | | | | | | | |
|---|---|---|---|---|---|---|---|---|---|---|---|
| 252 | 798.6/184.1>GPCho:38:2p 38.3e | 0.039227 | −0.095544 | 0.011752 | 0.040671 | −0.012354 | 0.055588 | −0.027571 | −0.0354 | −0.10794 | −0.000127 |
| 253 | 800.6/184.1>GPCho:38:1p, 38.2e | −0.045709 | −0.0762261 | −0.000774 | 0.066898 | 0.004778 | −0.032031 | 0.021276 | 0.023981 | −0.1598671 | −0.028425 |
| 254 | 808.6/184.1>GPCho:38:5a | 0.092807 | 0.040764 | 0.0597791 | 0.023702 | 0.002377 | 0.030533 | −0.015685 | −0.072884 | −0.038339 | 0.077767 |
| 255 | 810.6/184.1>GPCho:38:4a | 0.089966 | 0.027429 | 0.046071 | −0.020931 | 0.012288 | 0.04398 | −0.002545 | −0.103361 | 0.00022 | 0.07807 |
| 256 | 812.6/184.1>GPCho:38:3a | 0.044293 | −0.025244 | 0.050093 | −0.013563 | −0.008801 | −0.019034 | −0.019898 | −0.112159 | 0.017277 | 0.120069 |
| 257 | 814.6/184.1>GPCho:38:2a | −0.105396 | −0.0216081 | 0.027721 | −0.023283 | 0.065997 | 0.004261 | 0.048282 | −0.03577 | −0.012326 | −0.036407 |
| 258 | 810.6/184.1>GPCho:38:1a | −0.082438 | −0.053516 | −0.039274 | 0.002349 | 0.041196 | −0.068668 | 0.048149 | 0.034096 | −0.043071 | 0.00977 |
| 259 | 820.6/184.1>GPCho:40:5p, 40:6e | 0.074398 | 0.032526 | 0.066651 | 0.079365 | 0.022856 | 0.028619 | 0.014791 | −0.040825 | −0.117416 | 0.014994 |
| 260 | 822.6/184.1>GPCho:40:4p, 40:5e | 0.049023 | −0.062032 | 0.034176 | 0.037748 | 0.024426 | 0.076041 | −0.004824 | −0.047816 | −0.11186 | −0.024185 |
| 261 | 824.6/184.1>GPCho:40:3p, 40:4e | 0.033716 | −0.092179 | 0.020613 | 0.009409 | 0.003679 | 0.081721 | −0.024939 | −0.020573 | −0.115283 | −0.015245 |
| 262 | 820.6/184.1>GPCho:40:2p, 40:3e | −0.045233 | −0.118315 | −0.057077 | −0.021514 | −0.020921 | 0.010859 | −0.048378 | 0.015224 | −0.042028 | −0.040148 |
| 263 | 828.6/184.1>GPCho:40:1p, 40:2e | −0.060723 | −0.087637 | −0.068761 | −0.017467 | −0.031426 | 0.033227 | −0.060322 | 0.023668 | −0.100091 | −0.009896 |
| 264 | 834.6/184.1>GPCho:40:6a | 0.077876 | 0.043459 | 0.0667651 | 0.035034 | −0.00172 | 0.005796 | −0.007026 | −0.070938 | −0.046758 | 0.068188 |
| 265 | 830.6/184.1>GPCho:40:5a | 0.064731 | −0.029729 | 0.040998 | −0.021407 | −0.003205 | −0.013989 | −0.041162 | −0.075754 | −0.052456 | 0.09237 |
| 266 | 838.6/184.1>GPCho:40:4a | 0.033892 | −0.089979 | 0.003811 | −0.052758 | −0.025292 | −0.014126 | −0.061929 | −0.04418 | −0.021127 | 0.090342 |
| 267 | 701.5/184.1>SM:18/16:1 | −0.087714 | 0.037564 | 0.01664 | 0.013516 | 0.053162 | 0.008721 | 0.038882 | 0.034889 | 0.002696 | −0.056178 |
| 268 | 703.5/184.1>SM:18/16:0 | −0.10233 | 0.04679 | 0.003785 | −0.011494 | 0.058824 | 0.038973 | 0.042827 | 0.016083 | −0.0115261 | −0.063321 |
| 269 | 703.8/184.4>SM:d18:1/16:0 | −0.097386 | 0.036473 | 0.032376 | −0.005535 | 0.069929 | 0.035052 | 0.071308 | 0.027352 | −0.013777 | −0.063656 |
| 270 | 705.8/184.4>SM: d18:0/16:0 | −0.096599 | 0.038011 | 0.034631 | −0.021579 | 0.07137 | 0.019621 | 0.069324 | −0.00657 | −0.00118 | −0.040246 |
| 271 | 727.6/184.1>SM:18/18:2 | −0.059605 | −0.02319 | −0.043122 | 0.023235 | 0.041557 | −0.044637 | 0.084455 | −0.009104 | −0.030171 | −0.023593 |
| 272 | 729.6/184.1>SM:18/18:1 | −0.086006 | 0.015385 | 0.001476 | −0.012172 | 0.053917 | 0.016219 | 0.058136 | −0.029595 | 0.03207 | −0.046213 |
| 273 | 731.6/184.1>SM:18/18:0 | −0.096787 | 0.011405 | 0.000826 | −0.054267 | 0.063376 | 0.023033 | 0.06037 | −0.060887 | 0.042063 | −0.037006 |
| 274 | 731.8/184.4>SM: d18:1/18:0 | −0.095385 | 0.009158 | 0.010818 | −0.054171 | 0.065372 | 0.02341 | 0.065567 | −0.057801 | 0.042064 | −0.04004 |
| 275 | 733.8/184.4>SM: d18:0/18:0 | −0.070415 | −0.02856 | 0.012369 | −0.081549 | 0.009041 | 0.013904 | −0.000201 | −0.089677 | 0.097251 | 0.039161 |
| 276 | 757.6/184.1>SM:18/20:1 | −0.059285 | −0.091074 | −0.048111 | 0.013933 | −0.034289 | −0.052056 | −0.01256 | 0.067193 | 0.001643 | −0.036607 |
| 277 | 759.6/184.1>SM:18/20:0 | 0.078391 | −0.010629 | −0.05075 | −0.028992 | −0.028663 | 0.012277 | 0.014544 | 0.114733 | −0.012809 | −0.020873 |
| 278 | 759.8/184.4>SM: d18:1/20:0 | 0.075649 | −0.005513 | −0.047461 | −0.020632 | −0.032881 | 0.001086 | 0.028929 | 0.115206 | 0.0065071 | −0.029864 |
| 279 | 761.8/184.4>SM: d18:0/20:0 | 0.01245 | −0.079977 | 0.0311241 | −0.08238 | −0.089715 | 0.031005 | −0.077739 | −0.010807 | 0.078319 | 0.019202 |
| 280 | 773.6/184.1>SM:18/21:0 | −0.004892 | −0.016545 | −0.007809 | 0.065998 | 0.005054 | −0.083984 | 0.050273 | 0.038298 | −0.183974 | 0.030953 |
| 281 | 787.6/184.1>SM:18/22:0 | 0.028739 | 0.002919 | −0.049299 | 0.053471 | −0.027365 | −0.147549 | 0.016891 | 0.075347 | −0.082965 | 0.087543 |
| 282 | 787.9/184.4>SM: d18:1/22:0 | 0.004685 | −0.000071 | −0.030025 | 0.069616 | −0.003707 | −0.163506 | 0.077881 | 0.079918 | −0.054715 | 0.094857 |
| 283 | 789.9/184.4>SM: d18:0/22:0 | −0.0160931 | −0.092546 | −0.0466041 | −0.010951 | −0.066241 | −0.107589 | −0.051865 | 0.031801 | 0.0289751 | 0.08213 |
| 284 | 813.6/184.1>SM:18/24:1 | −0.104831 | 0.004875 | 0.0408191 | −0.017665 | 0.067953 | 0.01734 | 0.065979 | −0.046799 | −0.013327 | −0.029844 |
| 285 | 813.9/184.4>SM: d18:1/24:1 | −.103018 | 0.003346 | 0.045369 | −0.014905 | 0.059346 | 0.015853 | 0.075921 | −0.044597 | −0.011606 | −0.034153 |
| 286 | 815.6/184.1>SM:18/24:0 | −0.078437 | 0.013561 | 0.047804 | 0.017455 | 0.078663 | −0.041681 | 0.093336 | 0.01526 | −0.060292 | 0.023681 |
| 287 | 815.9/184.4>SM: d18:0/24:1 | −0.0757661 | 0.040863 | −0.003314 | 0.020897 | 0.069992 | −0.024008 | 0.101334 | 0.024874 | −0.049474 | 0.011265 |
| 288 | 817.9/184.4>SM: d18:0/24:0 | −0.026056 | −0.071671 | −0.073139 | 0.029063 | 0.014539 | −0.060145 | 0.049845 | 0.038783 | −0.031478 | −0.005398 |
| 289 | 841.9/184.4>SM: d18:1/26:1 | −0.057013 | −0.096867 | −0.071902 | −0.045004 | −0.007675 | −0.031755 | −0.00936 | −0.011209 | −0.000881 | −0.036257 |
| 290 | 843.9/184.4>SM: d18:0/26:1 | 0.067 | −0.038473 | −0.038665 | 0.010803 | −0.016538 | 0.057546 | −0.043259 | −0.045753 | −0.030444 | −0.054166 |
| 291 | 843.9/184.4>SM: d18:1/26:0 | 0.066855 | −0.041004 | −0.036048 | 0.0125 | −0.016 | 0.053414 | −0.037957 | −0.045317 | −0.027671 | −0.054549 |
| 292 | 845.9/184.4>SM: d18:0/26:0 | 0.066946 | −0.042691 | −0.016296 | 0.00965 | −0.0242 | 0.069094 | −0.057862 | −0.05861 | −0.030732 | −0.041333 |
| 293 | 538.7/264.4>Cer:d18:1/16:0 | −0.079533 | 0.025348 | 0.004107 | 0.065166 | 0.076365 | 0.065863 | −0.062139 | −0.015495 | 0.010052 | −0.006462 |
| 294 | 540.7/260.4>Cer:d18:0/16:0 | −0.107352 | 0.04385 | −0.014221 | 0.006162 | 0.057301 | 0.033264 | −0.010763 | −0.023773 | 0.014175 | 0.006372 |
| 295 | 560.7/264.4>Cer:d18:1/18:0 | −0.098567 | 0.006839 | −0.014539 | −0.019642 | 0.060461 | 0.027429 | 0.002529 | −0.075405 | 0.053489 | −0.020914 |
| 296 | 568.7/260.4>Cer:d18:0/18:0 | −0.09257 | 0.046565 | −0.018122 | −0.046417 | 0.045523 | 0.049197 | −0.035247 | −0.008251 | −0.004646 | 0.038005 |
| 297 | 594.7/264.4>Cer:d18:1/20:0 | −0.105037 | 0.025385 | −0.020729 | −0.01604 | 0.035735 | 0.025951 | .031531 | −0.027818 | 0.022814 | 0.006197 |
| 298 | 590.7/260.4>Cer:d18:0/20:0 | −0.0678141 | −0.041446 | 0.032606 | 0.037849 | 0.071876 | 0.062801 | −0.026536 | −0.038284 | −0.044081 | 0.060952 |
| 299 | 622.8/264.4>Cer:d18:1/22:0 | −0.104571 | 0.039364 | −0.012178 | −0.006463 | 0.028839 | 0.009659 | −0.042138 | −0.00207 | −0.000378 | 0.061085 |
| 300 | 624.8/260.4>Cer:d18:0/22:0 | −0.003066 | −0.080586 | −0.018198 | 0.027863 | 0.058259 | 0.105066 | 0.030493 | −0.028166 | −0.052294 | 0.051145 |
| 301 | 648.9/264.4>Cer:d18:1/24:1 | −0.1117 | 0.011661 | 0.008665 | −0.007081 | 0.040356 | 0.031572 | −0.022828 | −0.042294 | 0.019088 | −0.004543 |
| 302 | 650.9/260.4>Cer:d18:0/24:1 | −0.105688 | 0.042368 | −0.005419 | −0.034196 | 0.030394 | 0.021841 | −0.044273 | −0.023771 | 0.003449 | 0.040693 |

APPENDIX B2-continued

PCA Transformation Matrix (340 × 340; Benign/Malignant)

| | | | | | | | | | | | |
|---|---|---|---|---|---|---|---|---|---|---|---|
| 303 | 650.9/264.4>Cer:d18:1/24:0 | −0.094808 | 0.054452 | 0.012735 | −0.014986 | 0.011717 | −0.022019 | −0.007138 | 0.012197 | −0.03347 | 0.049613 |
| 304 | 652.9/260.4>Cer:d18:0/24:0 | −0.084569 | 0.068192 | −0.004998 | −0.018891 | 0.009862 | 0.003119 | −0.041571 | 0.037869 | −0.03732 | 0.075964 |
| 305 | 670.9/264.4>Cer:d18:1/26:1 | −0.099091 | −0.005464 | 0.033081 | −0.026115 | 0.03094 | 0.003895 | −0.006505 | −0.070633 | 0.003816 | −0.057829 |
| 306 | 678.9/260.4>Cer:d18:0/26:1 | −0.029244 | 0.060517 | −0.070253 | −0.005143 | −0.007193 | 0.078334 | −0.137664 | 0.054547 | −0.02994 | 0.042906 |
| 307 | 678.9/264.4>Cer:d18:1/26:0 | −0.049536 | −0.033992 | 0.011337 | 0.05476 | −0.025494 | −0.01013 | −0.037457 | −0.032513 | −0.045536 | 0.005522 |
| 308 | 680.9/260.4>Cer:d18:0/26:0 | −0.009249 | 0.060144 | −0.060622 | −0.001932 | −0.001228 | 0.065265 | −0.110698 | 0.105775 | −0.029842 | 0.078026 |
| 309 | 700.7/264.4>MonoHexCer:d18.1/10.0 | −0.081818 | 0.076034 | −0.032147 | −0.020114 | 0.007524 | 0.059978 | −0.050754 | 0.073853 | −0.059767 | 0.036222 |
| 310 | 702.7/260.4>MonoHexCer:d18.0/10.0 | −0.055154 | 0.061293 | −0.043269 | −0.01625 | 0.000432 | 0.048934 | −0.112984 | 0.087344 | −0.053294 | 0.045833 |
| 311 | 728.7/264.4>MonoHexCer:d18.1/18.0 | −0.108949 | 0.041279 | 0.013633 | −0.005533 | 0.026457 | 0.027594 | 0.010594 | −0.00115 | −0.021886 | −0.016392 |
| 312 | 730.7/260.4>MonoHexCer:d18.0/18.0 | −0.065543 | 0.011342 | −0.071314 | −0.008928 | −0.027027 | −0.027866 | 0.024501 | −0.070189 | −0.033357 | −0.022316 |
| 313 | 750.7/264.4>MonoHexCer:d18.1/20.0 | −0.095854 | 0.0675 | −0.006678 | −0.012292 | −0.009559 | 0.042957 | −0.025632 | 0.040095 | −0.056043 | 0.002218 |
| 314 | 758.7/260.4>MonoHexCe r.d18.0/20.0 | −0.059666 | 0.01 7761 | −0.033717 | −0.021174 | −0.06976 | 0.016533 | −0.024598 | −0.032985 | −0.05858 | −0.05708 |
| 315 | 784.8/264.4>MonoHexCer:d18.1/22.0 | −0.082036 | 0.082759 | −0.027146 | −0.008499 | 0.011133 | 0.036582 | −0.030669 | 0.07177 | −0.088197 | 0.029817 |
| 316 | 780.8/260.4>MonoHexCer:d18.0/22.0 | −0.069379 | −0.003498 | −0.020866 | −0.016314 | −0.024684 | −0.00986 | 0.046229 | −0.007671 | −0.090473 | −0.001528 |
| 317 | 810.9/264.4>MonoHexCer:d18.1/24.1 | −0.095439 | 0.064787 | −0.0048 | −0.013397 | 0.021349 | 0.056199 | −0.01916 | 0.035028 | −0.065076 | 0.020827 |
| 318 | 812.9/260.4>MonoHexCer:d18.0/24.1 | −0.073959 | 0.0786751 | −0.009801 | −0.012705 | 0.020699 | 0.068362 | −0.060549 | 0.07078 | −0.074312 | 0.002653 |
| 319 | 812.9/264.4>MonoHexCer:d18.1/24.0 | −0.071755 | 0.084802 | −0.032919 | −0.006241 | 0.010731 | 0.0526 | −0.043835 | 0.075866 | −0.096365 | 0.03944 |
| 320 | 814.9/260.4>MonoHexCer:d18.0/24.0 | −0.077936 | 0.076081 | −0.037414 | −0.015573 | 0.023202 | 0.039981 | −0.048126 | 0.051546 | −0.071529 | 0.068162 |
| 321 | 838.9/264.4>MonoHexCer:d18.1/26.1 | −0.08882 | 0.063369 | −0.027837 | 0.00916 | 0.00086 | 0.035614 | −0.035799 | −0.00579 | −0.047376 | 0.062716 |
| 322 | 840.9/260.4>MonoHexCer:d18.0/26.1 | −0.065416 | −0.020002 | −0.019982 | −0.025428 | −0.03149 | −0.008631 | 0.01883 | −0.020455 | −0.020781 | 0.055325 |
| 323 | 840.9/264.4>MonoHexCer:d18.1/26.0 | −0.097367 | −0.000805 | 0.052257 | −0.004 | −0.010513 | −0.024525 | 0.006062 | −0.029172 | 0.002014 | 0.005262 |
| 324 | 842.9/260.4>MonoHexCer:d18.0/26.0 | −0.062378 | −0.01952 | −0.054352 | −0.032513 | −0.016231 | −0.058133 | 0.064285 | −0.112522 | −0.04509 | 0.082191 |
| 325 | 862.7/264.4>DiHexCer:d18:1/16:0 | −0.093744 | 0.06651 | −0.014178 | −0.023513 | 0.029557 | 0.046263 | −0.005932 | 0.044434 | −0.060887 | 0.012995 |
| 326 | 864.7/260.4>DiHexCer:d18:0/16:0 | −0.082293 | 0.028071 | 0.014314 | −0.035333 | 0.010702 | 0.043277 | 0.025685 | −0.047138 | −0.066783 | −0.011519 |
| 327 | 890.7/264.4>DiHexCer:d18:1/18:0 | −0.093603 | 0.068909 | −0.023574 | −0.017546 | 0.019234 | 0.042681 | −0.044454 | 0.040637 | −0.054889 | 0.060697 |
| 328 | 892.7/260.4>DiHexCer:d18:0/18:0 | −0.064418 | −0.033211 | 0.012602 | −0.01527 | 0.037684 | 0.015322 | −0.011855 | −0.053713 | −0.045605 | 0.013982 |
| 329 | 918.7/264.4>DiHexCer:dl 8:1/20:0 | −0.105069 | 0.052818 | 0.026335 | −0.00963 | −0.002171 | 0.012723 | 0.007061 | −0.009349 | −0.039577 | 0.042666 |
| 330 | 920.7/260.4>DiHexCer:d18:0/20:0 | −0.011219 | −0.0126 | −0.083924 | −0.017346 | −0.005253 | 0.033536 | 0.060485 | −0.062116 | −0.030738 | 0.048387 |
| 331 | 940.8/264.4>DiHexCer:d18:1/22:0 | −0.094925 | 0.072279 | −0.014203 | −0.004203 | 0.020608 | 0.025745 | −0.010825 | 0.036425 | −0.078696 | 0.047674 |
| 332 | 948.8/260.4>DiHexCer:d18:0/22:0 | −0.03663 | −0.036261 | −0.006624 | −0.020603 | 0.010845 | 0.062945 | 0.056993 | 0.006979 | −0.067896 | 0.045558 |
| 333 | 972.9/264.4>DiHexCer:d18:1/24:1 | −0.101749 | 0.052846 | 0.009418 | −0.013148 | 0.031185 | 0.030356 | 0.006719 | 0.012825 | −0.053202 | 0.016136 |
| 334 | 974.9/260.4>DiHexCer:d18:0/24:1 | −0.0863 | 0.018773 | 0.01969 | −0.005727 | 0.066953 | −0.01181 | 0.041227 | −0.0164 | 0.008123 | −0.011405 |
| 335 | 974.9/264.4>DiHexCer:d18:1/24:0 | −0.087683 | 0.074271 | −0.008607 | −0.003858 | 0.020992 | 0.032119 | −0.031498 | 0.07224 | −0.074687 | 0.069099 |
| 336 | 970.9/260.4>DiHexCer:d18:0/24:0 | −0.088147 | 0.019535 | −0.028565 | −0.020736 | 0.037354 | −0.0452 | 0.013089 | −0.077788 | −0.008575 | 0.014512 |
| 337 | 1000.9/264.4>DiHexCer:d18:1/26:1 | −0.095828 | −0.027501 | −0.012076 | 0.009757 | −0.003942 | −0.00446 | 0.005324 | −0.08819 | −0.032199 | 0.042799 |
| 338 | 1002.9/260.4>DiHexCer:d18:0/26:1 | −0.053135 | −0.009878 | 0.054421 | −0.032177 | 0.005249 | −0.046359 | −0.057205 | −0.040167 | −0.006481 | −0.016486 |
| 339 | 1002.9/264.4>DiHexCer:d18:1/26:0 | −0.097022 | −0.041291 | 0.0377 | 0.022591 | 0.00538 | 0.015732 | −0.055319 | −0.039289 | −0.01519 | −0.03126 |
| 340 | 1004.9/260.4>DiHexCer:d18:0/26:0 | −0.024918 | −0.059481 | 0.0267591 | −0.022514 | 0.007059 | 0.021753 | −0.020292 | −0.039727 | −0.024426 | 0.012623 |

| | L | M | N | O | P | Q | R | S | T | U | V | W | X | Y |
|---|---|---|---|---|---|---|---|---|---|---|---|---|---|---|
| 1 | 0.029381 | −0.049893 | 0.019059 | −0.031939 | 0.027215 | −0.050836 | 0.012222 | −0.056757 | −0.0416541 | 0.0194441 | −0.0111391 | −0.0381171 | −0.0129191 | 0.012025 |
| 2 | 0.026389 | −0.039384 | 0.015541 | 0.001025 | 0.003014 | −0.09207 | 0.055926 | −0.038452 | −0.010441 | 0.029151 | 0.0377011 | −0.008815 | −0.021671 | −0.026067 |
| 3 | 0.032733 | −0.078848 | 0.048897 | 0.020935 | −0.001291 | −0.039634 | 0.042868 | −0.02268 | 0.006212 | −0.002625 | −0.020747 | 0.002398 | 0.006085 | −0.011426 |
| 4 | −0.007164 | 0.053251 | −0.011323 | −0.004619 | −0.037088 | −0.035161 | 0.007963 | −0.061197 | −0.047887 | −0.031603 | 0.039094 | −0.057287 | −0.073526 | 0.127669 |
| 5 | 0.102166 | −0.006508 | 0.057522 | −0.001044 | −0.021628 | 0.054116 | 0.036342 | 0.026861 | −0.039651 | 0.040063 | 0.020718 | −0.007436 | 0.015567 | −0.133309 |
| 6 | 0.017699 | −0.031272 | −0.001536 | 0.012487 | −0.00871 | −0.005206 | 0.070975 | −0.08501 | 0.025206 | 0.015723 | −0.09518 | 0.009251 | 0.090999 | 0.026711 |
| 7 | −0.027727 | −0.012255 | 0.012402 | 0.032385 | −0.015197 | 0.089558 | 0.083284 | −0.015021 | 0.004757 | −0.00802 | −0.01067 | 0.010829 | 0.117999 | −0.006035 |
| 8 | 0.0160791 | 0.007093 | −0.023292 | −0.003264 | 0.049884 | 0.055808 | 0.108877 | 0.056456 | −0.061013 | 0.013819 | 0.053509 | −0.072863 | −0.01973 | −0.105183 |
| 9 | 0.003044 | 0.064038 | −0.009619 | −0.003477 | −0.056838 | −0.027785 | 0.019358 | −0.027193 | 0.013602 | −0.004553 | 0.059963 | −0.043318 | −0.052544 | 0.111713 |
| 10 | −0.00438 | −0.032874 | 0.003261 | 0.084848 | −0.045491 | 0.016018 | 0.144787 | −0.037716 | −0.012633 | 0.061067 | −0.090726 | −0.048396 | 0.019614 | −0.034706 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 11 | 0.073345 | −0.046549 | 0.041411 | −0.032802 | −0.054609 | −0.067481 | 0.115824 | 0.092687 | −0.061014 | 0.12041 | −0.018708 | −0.07873 | −0.048687 | −0.004763 |
| 12 | −0.055346 | −0.008553 | −0.042709 | −0.03162 | 0.02157 | 0.031257 | 0.013525 | −0.102801 | −0.076075 | 0.003211 | −0.059531 | 0.172023 | 0.077223 | −0.139436 |
| 13 | 0.062275 | 0.010575 | 0.107332 | −0.070012 | −0.03168 | 0.038579 | 0.039386 | −0.018392 | 0.05069 | 0.007243 | 0.031124 | −0.046017 | 0.062359 | 0.024909 |
| 14 | 0.123642 | −0.013175 | 0.102938 | −0.088932 | −0.023101 | 0.011818 | 0.068068 | −0.00322 | 0.025954 | 0.015975 | −0.021858 | −0.048556 | 0.077847 | 0.010869 |
| 15 | 0.029666 | −0.015902 | 0.080018 | −0.048044 | 0.054488 | −0.034661 | −0.03151 | 0.035589 | −0.010177 | 0.006387 | −0.035163 | 0.011619 | 0.006136 | −0.023221 |
| 16 | −0.017724 | 0.026426 | −0.002409 | −0.038539 | 0.117282 | −0.011743 | 0.043603 | 0.033213 | 0.047515 | 0.09972 | −0.021804 | −0.129142 | 0.024507 | 0.048327 |
| 17 | 0.02179 | −0.028625 | 0.026312 | −0.012592 | −0.01379 | −0.00526 | −0.064558 | −0.064751 | 0.1185051 | −0.0012671 | 0.001321 | 0.0494911 | −0.0273681 | −0.011342 |
| 18 | 0.050554 | −0.018904 | 0.0036221 | −0.059437 | 0.118305 | 0.063918 | −0.004021 | 0.089758 | 0.060945 | −0.0053 | 0.0676 | −0.00281 | −0.088613 | −0.00448 |
| 19 | −0.014368 | −0.098013 | −0.031061 | −0.091451 | 0.050375 | −0.067452 | 0.063305 | −0.008085 | 0.078197 | 0.023242 | −0.018027 | −0.005148 | 0.009747 | −0.014725 |
| 20 | −0.022253 | 0.061074 | 0.053834 | −0.053453 | 0.008313 | 0.037384 | −0.056045 | 0.047317 | 0.019889 | 0.019311 | −0.006551 | −0.015675 | 0.036042 | −0.050233 |
| 21 | −0.023757 | −0.033904 | 0.024102 | −0.022344 | −0.001022 | −0.113452 | 0.075231 | −0.074307 | 0.045179 | −0.002702 | 0.029854 | 0.019885 | −0.069565 | −0.02301 |
| 22 | −0.020088 | −0.008128 | 0.0366921 | 0.004958 | −0.028405 | 0.027897 | 0.018478 | −0.014907 | 0.0488381 | −0.0289281 | −0.0750961 | 0.118811 | 0.1142031 | −0.072222 |
| 23 | −0.048344 | −0.068506 | 0.0572241 | −0.078322 | 0.143041 | −0.069078 | 0.102963 | 0.037119 | −0.061786 | −0.006299 | 0.040892 | −0.002518 | 0.036109 | −0.004292 |
| 24 | 0.032807 | −0.064282 | 0.049472 | −0.038939 | 0.047629 | −0.0938 | 0.049765 | −0.016877 | 0.073022 | −0.0438 | 0.038364 | 0.095513 | 0.005764 | −0.063265 |
| 25 | 0.062339 | −0.023559 | −0.015786 | −0.04461 | 0.075304 | −0.068651 | 0.070677 | 0.029999 | 0.023756 | 0.010355 | 0.05651 | −0.032608 | 0.015662 | −0.020223 |
| 26 | −0.038028 | 0.049022 | 0.041482 | −0.034255 | 0.004781 | 0.025772 | −0.054223 | 0.072514 | 0.009117 | 0.019318 | −0.016755 | −0.008107 | 0.038376 | −0.039154 |
| 27 | −0.068794 | 0.081467 | 0.018866 | −0.032968 | −0.005316 | 0.037714 | −0.07797 | 0.065481 | −0.00614 | 0.022945 | −0.009172 | −0.007366 | 0.018175 | −0.035925 |
| 28 | −0.013057 | 0.087227 | −0.008999 | −0.036197 | −0.036017 | −0.032946 | −0.005294 | −0.022898 | −0.003319 | −0.017017 | 0.022602 | −0.034956 | −0.009014 | 0.036919 |
| 29 | −0.075735 | 0.016677 | 0.017702 | 0.035238 | 0.021017 | −0.045803 | −0.014336 | −0.034846 | 0.012596 | −0.070092 | −0.061987 | 0.061023 | 0.167167 | −0.086516 |
| 30 | 0.022278 | 0.06552 | −0.04121 | 0.01205 | −0.022858 | 0.013392 | −0.018421 | −0.036012 | −0.038833 | −0.03493 | −0.022335 | −0.032736 | −0.06035 | 0.018692 |
| 31 | −0.071611 | 0.055534 | −0.019488 | −0.000705 | −0.001628 | −0.01046 | 0.0642 | −0.057536 | −0.052513 | 0.043422 | −0.001532 | 0.043632 | −0.011599 | 0.043367 |
| 32 | −0.068488 | 0.017762 | −0.027209 | −0.037558 | 0.063615 | 0.036209 | −0.00726 | −0.032699 | 0.164401 | 0.147308 | 0.031541 | 0.051873 | 0.044115 | 0.003505 |
| 33 | 0.045728 | −0.007986 | 0.024091 | −0.045328 | 0.041604 | 0.053861 | −0.099581 | 0.061746 | 0.012236 | 0.045749 | 0.03624 | −0.005048 | −0.098991 | −0.066941 |
| 34 | 0.005146 | 0.096274 | −0.069898 | −0.027691 | −0.017883 | 0.001002 | −0.032877 | 0.065104 | 0.002635 | −0.019401 | 0.007418 | 0.023922 | 0.01295 | 0.028572 |
| 35 | 0.096217 | 0.012305 | 0.055179 | −0.01044 | −0.056575 | 0.046467 | 0.047186 | 0.026548 | −0.031029 | 0.007514 | −0.026784 | 0.034217 | −0.029603 | −0.001361 |
| 36 | 0.002898 | −0.031325 | 0.090459 | −0.014424 | −0.040494 | −0.028409 | −0.000327 | 0.089333 | 0.03472 | −0.061702 | 0.021221 | 0.009341 | −0.033236 | −0.017883 |
| 37 | −0.035407 | 0.056332 | 0.029961 | −0.034151 | 0.008466 | 0.072002 | −0.069385 | 0.059264 | 0.037126 | −0.047209 | −0.04191 | 0.034959 | 0.021724 | −0.011299 |
| 38 | −0.072297 | −0.054097 | 0.028957 | −0.069088 | 0.018999 | 0.025543 | −0.020222 | −0.033457 | −0.06077 | −0.073689 | −0.000209 | −0.031742 | −0.038837 | 0.024625 |
| 39 | 0.134324 | −0.102384 | −0.073716 | 0.010814 | 0.043195 | −0.015436 | −0.057725 | −0.018307 | −0.013766 | −0.01279 | 0.022397 | −0.02572 | 0.045788 | 0.045853 |
| 40 | 0.087998 | 0.035139 | −0.104188 | −0.031868 | −0.004688 | −0.007505 | −0.066693 | 0.015936 | −0.001574 | −0.017497 | −0.065611 | 0.015055 | −0.03467 | −0.023051 |
| 41 | 0.11352 | 0.048939 | −0.138844 | −0.04865 | −0.011236 | −0.031968 | −0.037679 | 0.020972 | 0.033809 | −0.02491 | −0.000416 | 0.023381 | 0.003213 | −0.0481 |
| 42 | 0.118714 | −0.085903 | −0.13705 | −0.067172 | −0.006263 | −0.019169 | −0.035298 | 0.027661 | 0.099598 | 0.016111 | −0.032374 | 0.014842 | 0.039501 | 0.002021 |
| 43 | 0.075188 | 0.059319 | −0.126819 | −0.024218 | −0.030475 | 0.016059 | −0.034889 | 0.021795 | −0.007483 | −0.044624 | −0.047826 | −0.022664 | −0.032955 | 0.001201 |
| 44 | 0.092982 | 0.05586 | −0.088168 | −0.030222 | −0.006742 | 0.027349 | −0.038563 | 0.048942 | −0.023611 | −0.030521 | −0.019177 | 0.057349 | −0.050983 | −0.040835 |
| 45 | 0.074612 | 0.042452 | −0.140101 | 0.038894 | −0.035329 | 0.04782 | −0.025438 | 0.026715 | 0.011304 | −0.011734 | −0.027049 | −0.054765 | 0.020803 | −0.101732 |
| 46 | 0.106655 | −0.006814 | −0.08406 | 0.048371 | −0.037349 | 0.044645 | −0.001976 | 0.061235 | −0.016561 | 0.02188 | −0.002943 | 0.101372 | −0.00694 | −0.032688 |
| 47 | 0.09277 | −0.128934 | 0.025554 | 0.155302 | 0.065273 | −0.038181 | −0.082371 | −0.033359 | 0.003534 | −0.065306 | 0.030744 | −0.072676 | 0.028146 | 0.042404 |
| 48 | 0.145284 | −0.120473 | −0.064211 | 0.113486 | 0.115122 | 0.014361 | −0.026974 | −0.105136 | −0.0234841 | 0.003061 | 0.1590911 | 0.0042311 | 0.0726551 | 0.046034 |
| 49 | 0.026337 | 0.071182 | −0.036674 | 0.012765 | −0.019378 | 0.026003 | −0.017466 | −0.046108 | −0.026695 | −0.054783 | 0.002468 | −0.055453 | −0.055703 | 0.026678 |
| 50 | 0.023596 | −0.020158 | −0.056416 | −0.092879 | 0.012444 | −0.060183 | −0.035099 | −0.003878 | 0.027788 | 0.043476 | 0.026683 | −0.021519 | 0.041477 | −0.054156 |
| 51 | 0.023447 | −0.179791 | 0.027425 | 0.081444 | 0.002493 | 0.000696 | −0.036282 | 0.04185 | 0.005519 | −0.014428 | −0.058698 | 0.019625 | −0.087848 | −0.039694 |
| 52 | 0.038668 | 0.02043 | −0.095764 | −0.041596 | 0.07704 | −0.006217 | −0.045607 | −0.054338 | 0.000002 | 0.017078 | 0.052043 | 0.023369 | −0.026308 | −0.055892 |
| 53 | 0.001264 | −0.135389 | 0.038881 | 0.048139 | 0.003766 | 0.046304 | −0.064548 | 0.033588 | 0.013675 | 0.009217 | −0.046748 | 0.009348 | −0.076274 | −0.060077 |
| 54 | 0.089185 | −0.094938 | −0.082081 | −0.010342 | 0.101105 | 0.030432 | 0.006823 | 0.012562 | −0.026908 | −0.041324 | 0.071406 | −0.01998 | 0.037262 | −0.029416 |
| 55 | −0.024213 | −0.056654 | 0.027711 | 0.0182 | 0.003332 | 0.009932 | −0.022492 | 0.0036 | −0.007184 | 0.014063 | −0.009315 | −0.021776 | −0.033804 | −0.02725 |
| 56 | 0.028992 | 0.092258 | −0.049081 | 0.003552 | −0.022334 | 0.020214 | 0.016408 | −0.016262 | −0.067326 | −0.049813 | −0.015099 | −0.050481 | −0.049008 | 0.048129 |
| 57 | −0.010397 | −0.025577 | −0.026988 | −0.090127 | 0.021927 | 0.029974 | 0.007036 | −0.068634 | −0.026995 | −0.071062 | 0.025116 | 0.025752 | −0.004765 | 0.052152 |
| 58 | 0.044027 | 0.014845 | 0.015501 | −0.018931 | 0.049266 | 0.011675 | −0.046061 | 0.085913 | 0.022762 | −0.054036 | −0.021953 | 0.056989 | −0.030873 | 0.045606 |
| 59 | 0.066599 | 0.038243 | −0.095284 | −0.059672 | 0.011762 | 0.047031 | 0.058805 | −0.029299 | −0.091503 | −0.145853 | 0.077217 | −0.004177 | −0.124493 | 0.005015 |
| 60 | 0.018076 | 0.062298 | −0.030712 | −0.00236 | 0.034309 | −0.066742 | 0.09605 | −0.025654 | 0.045513 | 0.039389 | 0.056596 | 0.031659 | 0.024062 | 0.057388 |
| 61 | 0.078744 | 0.113958 | −0.127806 | −0.035261 | 0.025049 | −0.022432 | 0.066522 | −0.026287 | −0.014248 | −0.037187 | 0.058747 | −0.020253 | −0.03311 | 0.055067 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 62 | 0.028642 | −0.083575 | 0.05895 | 0.081314 | 0.03937 | 0.026617 | 0.038526 | 0.066962 | 0.06296 | −0.035125 | −0.026861 | 0.072691 | −0.000385 | 0.121575 |
| 63 | 0.08172 | 0.007542 | −0.113989 | −0.002376 | 0.036504 | 0.024309 | 0.035673 | −0.042803 | −0.026633 | −0.029802 | 0.042061 | −0.038983 | 0.018819 | 0.035323 |
| 64 | 0.035286 | 0.083502 | −0.055606 | 0.020416 | −0.017447 | 0.017868 | 0.034844 | −0.018096 | −0.015492 | −0.047097 | −0.02599 | −0.043788 | −0.063175 | 0.066955 |
| 65 | −0.031929 | 0.014809 | −0.024558 | −0.071096 | 0.031599 | 0.05808 | 0.090805 | −0.045933 | −0.034525 | −0.067349 | 0.035429 | 0.051591 | 0.004345 | 0.114139 |
| 66 | 0.017703 | 0.107304 | −0.054199 | −0.03064 | 0.006016 | 0.06555 | 0.058801 | −0.010515 | −0.061239 | −0.080447 | 0.053672 | 0.019531 | −0.135039 | 0.092721 |
| 67 | 0.059237 | 0.064708 | −0.10502 | 0.075203 | −0.000476 | 0.087702 | 0.042403 | 0.01942 | −0.091511 | −0.009901 | 0.008011 | −0.067844 | −0.031912 | −0.043504 |
| 68 | 0.055103 | −0.000559 | −0.03088 | −0.044727 | 0.004282 | 0.096088 | −0.001767 | 0.106061 | −0.130174 | 0.052751 | 0.054715 | 0.025814 | −0.027037 | 0.011813 |
| 69 | 0.087599 | −0.027305 | 0.152397 | −0.074981 | −0.009841 | 0.07468 | 0.043168 | 0.000951 | 0.021931 | 0.05554 | 0.013758 | 0.667743 | 0.050672 | −0.01972 |
| 70 | 0.077907 | 0.010046 | 0.174719 | −0.069889 | −0.055085 | 0.009721 | 0.083385 | −0.038437 | −0.040327 | 0.020322 | −0.023891 | −0.003736 | 0.035027 | 0.07149 |
| 71 | −0.032077 | −0.033841 | 0.053554 | −0.003435 | −0.059209 | −0.008227 | 0.049577 | −0.116238 | 0.000631 | 0.074124 | −0.019082 | −0.005382 | −0.04162 | 0.642524 |
| 72 | −0.072461 | −0.070098 | −0.028332 | 0.038663 | −0.024274 | −0.030955 | 0.128835 | −0.172592 | −0.013215 | 0.038575 | −0.077164 | −0.01873 | −0.107937 | 0.102357 |
| 73 | −0.016511 | −0.092677 | 0.011348 | 0.081077 | 0.01399 | −0.08103 | 0.143914 | −0.166687 | −0.044944 | 0.078356 | −0.096877 | −0.010706 | −0.117595 | 0.070581 |
| 74 | −0.059861 | −0.072553 | −0.055558 | −0.097145 | −0.000338 | −0.087387 | 0.062229 | 0.026234 | −0.035285 | −0.027072 | 0.040719 | 0.014757 | −0.085446 | −0.002479 |
| 75 | 0.103436 | −0.021248 | 0.143724 | −0.074164 | −0.041322 | 0.009291 | 0.052342 | −0.023421 | 0.032031 | 0.03834 | 0.026945 | −0.030015 | 0.030205 | 0.045043 |
| 76 | 0.091337 | −0.060142 | 0.131628 | −0.054621 | −0.08246 | 0.014542 | 0.042708 | −5.041805 | 0.068567 | 0.0383 361 | −0.665654 | 0.012889 | 0.015676 | −0.016949 |
| 77 | 0.101575 | −0.027749 | 0.140694 | −0.076092 | −0.043501 | 0.01962 | 0.039072 | −0.038907 | 0.038735 | 0.051671 | 0.023887 | −0.034167 | 0.619997 | 0.034811 |
| 78 | 0.096724 | −0.013653 | 0.141329 | −0.079368 | −0.034929 | 0.03408 | 0.030662 | −0.032793 | 0.028514 | 0.0406051 | 0.029803 | −0.039818 | 0.025847 | 0.027436 |
| 79 | 0.072562 | −0.007227 | 0.14833 | −0.09185 | −0.035102 | −0.014094 | 0.04079 | −0.003831 | 0.036091 | 0.065493 | 0.0235211 | −0.044974 | 0.009321 | 0.050632 |
| 80 | −0.066198 | 0.015796 | 0.042776 | 0.7068 | 0.031185 | 0.005457 | 0.090587 | 0.070813 | −0.03094 | 0.018891 | −0.029249 | −0.0477961 | 0.012831 | 0.0049 |
| 81 | −0.005886 | −0.06685 | 0.035775 | 0.011349 | 0.033471 | 0.053921 | −0.080729 | −0.0666 | 0.143163 | −0.050263 | −0.01503 | −0.6117774 | −0.049682 | −0.007527 |
| 82 | −0.041278 | 0.014008 | −0.001656 | −0.035345 | 0.012366 | 0.007683 | −0.061838 | 0.054264 | −0.014288 | 0.023784 | −0.039055 | 0.007507 | −0.007358 | −0.000247 |
| 83 | −0.068318 | 0.059103 | 0.005801 | −0.017412 | −0.002251 | 0.038644 | −0.08158 | 0.034606 | −0.018471 | 0.035949 | −0.006807 | 0.010287 | 0.002117 | −0.031653 |
| 84 | −0.079942 | 0.050761 | 0.001237 | −0.026554 | −0.025193 | 0.027052 | −0.066424 | 0.027911 | −0.030513 | 0.030624 | 0.001762 | 0.009495 | 0.002865 | −0.030204 |
| 85 | −0.048286 | −0.036438 | −0.020278 | 0.103525 | 0.097307 | −0.009967 | 0.072341 | −0.136161 | 0.002893 | −0.092117 | −0.04852 | 0.051343 | −0.023956 | 0.080926 |
| 86 | −0.010151 | −0.088159 | −0.063267 | 0.080254 | 0.065898 | −0.042454 | 0.095175 | −0.154114 | −0.028312 | 0.052767 | −0.028359 | 0.017481 | −0.074359 | 0.09254 |
| 87 | −0.085109 | 0.012656 | −0.010177 | 0.075214 | 0.052322 | −0.001384 | −0.011914 | −0.10197 | 0.006423 | −0.030829 | 0.031716 | −0.020216 | −0.076333 | −0.020418 |
| 88 | −0.082018 | 0.067804 | 0.013662 | −0.007295 | 0.020298 | 0.027526 | −0.059111 | 0.067251 | −0.027499 | 0.045183 | −0.014417 | −0.018241 | 0.000712 | −0.027337 |
| 89 | −0.065364 | 0.087004 | 0.011803 | −0.024625 | 0.003994 | 0.041426 | −0.092709 | 0.075628 | −0.014734 | 0.025044 | 0.001592 | −0.002229 | 0.009665 | −0.046931 |
| 90 | −0.060159 | 0.094332 | 0.018575 | −0.024 | −0.004275 | 0.026482 | −0.068839 | 0.071895 | −0.018498 | 0.014108 | 0.002567 | −0.003155 | 0.004119 | −0.029636 |
| 91 | −0.05582 | −0.010797 | −0.004019 | 0.00077 | −0.010097 | 0.010484 | −0.006409 | −0.015326 | 0.022125 | −0.037012 | −0.004758 | −0.059331 | 0.008142 | 0.029843 |
| 92 | −0.043462 | −0.074046 | −0.006495 | 0.027489 | −0.025314 | −0.045934 | 0.094269 | −0.119398 | 0.002555 | 0.074726 | 0.080568 | 0.02047 | −0.026909 | 0.043123 |
| 93 | −0.049258 | 0.068869 | −0.007152 | 0.029475 | 0.052491 | 0.011752 | −0.02233 | −0.019298 | 0.002611 | 0.064406 | −0.003438 | 0.001108 | 0.014256 | 0.063576 |
| 94 | −0.072708 | 0.018782 | 0.005819 | 0.032783 | 0.062361 | 0.064337 | 0.066684 | 0.022892 | 0.025628 | −0.054732 | 0.029243 | 0.038799 | 0.052486 | −0.039862 |
| 95 | 0.050035 | −0.032959 | 0.035877 | −0.034124 | 0.023492 | 0.015628 | −0.107887 | 0.017207 | −0.11928 | 0.061998 | 0.020325 | 0.040853 | −0.087409 | 0.090437 |
| 96 | 0.030546 | −0.075025 | 0.027909 | −0.001338 | 0.01227 | −0.087917 | −0.029666 | −0.097748 | −0.033461 | 0.033137 | −0.062942 | 0.001237 | 0.096804 | 0.079641 |
| 97 | 0.009352 | −0.055624 | 0.016132 | −0.061924 | 0.144967 | 0.079473 | −0.055003 | 0.009313 | −0.000503 | −0.022109 | −0.017185 | −0.001979 | −0.019512 | 0.064689 |
| 98 | 4.090818 | −0.004023 | 0.044945 | 0.091968 | 0.03006 | −0.007819 | 0.005936 | 0.023186 | 0.000682 | −0.054966 | −0.006138 | −0.005986 | 0.057028 | −0.045736 |
| 99 | 0.028996 | −0.015422 | 0.051041 | −0.069365 | 0.088946 | 0.014129 | −0.015136 | 0.039921 | −0.023356 | 0.031428 | −0.038028 | −0.035935 | −0.033288 | 0.021838 |
| 100 | −0.039813 | −0.041575 | 0.039438 | 0.044938 | 0.078703 | −0.054007 | 0.006741 | −0.00946 | 0.008526 | −0.00648 | 0.020998 | 0.00076 | 0.070038 | −0.016349 |
| 101 | −0.094329 | 0.015435 | 0.029311 | 0.10668 | 0.020503 | 0.005511 | 0.039116 | 0.041264 | −0.002426 | −0.049742 | −0.042324 | −0.015122 | 0.017934 | −0.059283 |
| 102 | 0.06824 | −0.050334 | 0.08013 | −0.01781 | 0.133395 | −0.119433 | −0.0958 | −0.05787 | −0.100121 | 0.060502 | 0.055032 | 0.074131 | 0.004472 | 0.03807 |
| 103 | 0.021098 | −0.021023 | 0.100252 | 0.001893 | 0.069753 | −0.037764 | −0.120651 | −0.056786 | −0.020478 | 0.012723 | 0.085223 | 0.139605 | −0.020237 | −0.011524 |
| 104 | 0.047003 | −0.010814 | 0.027866 | −0.050351 | 0.069091 | 0.009174 | −0.033846 | −0.059798 | −0.019457 | 0.068501 | −0.101246 | 0.155515 | −0.090252 | 0.049676 |
| 105 | −0.037542 | −0.017852 | −0.029433 | −0.059372 | −0.08424 | 0.045428 | 0.0512 | 0.0149 | 0.125039 | 0.006349 | 0.075582 | 0.067317 | 0.015819 | 0.015127 |
| 106 | 0.006503 | 0.016115 | 0.045645 | 0.047327 | −0.00487 | −0.049838 | 0.036192 | −0.013244 | −0.031657 | −0.01215 | 0.02532 | 0.02358 | −0.055733 | −0.049048 |
| 107 | 0.014394 | −0.021404 | 0.060633 | 0.036086 | 0.028576 | −0.067059 | 0.030157 | −0.007258 | −0.055358 | −0.016883 | −0.065398 | 0.046729 | −0.102735 | −0.014829 |
| 108 | 0.020669 | −0.040681 | 0.063943 | −0.018265 | −0.013513 | −0.068004 | 0.005532 | −0.038511 | 0.023748 | −0.05931 | −0.081227 | 0.031766 | 0.009782 | −0.072488 |
| 109 | 0.001773 | −0.007855 | 0.077724 | 0.008086 | −0.003366 | 0.03162 | 0.010625 | 0.070968 | 0.061039 | 0.023169 | 0.086185 | 0.040897 | −0.060592 | −0.068003 |
| 110 | −0.007623 | 0.00554 | 0.027877 | 0.073048 | −0.002144 | 0.068001 | 0.064621 | −0.049224 | 0.023311 | 0.064359 | 0.065449 | −0.032669 | −0.12758 | 0.064527 |
| 111 | 0.033361 | −0.0014 | 0.02492 | −0.001124 | 0.037812 | −0.005303 | −0.033591 | −0.044968 | 0.076398 | −0.046287 | −0.069138 | 0.050294 | −0.018258 | −0.024429 |
| 112 | 0.032061 | −0.015346 | 0.051492 | −0.011102 | −0.037987 | −0.085975 | 0.019253 | −0.082712 | −0.023219 | −0.00921 | 0.062446 | 0.060428 | 0.05232 | −0.063302 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 113 | 0.031918 | 0.010812 | 0.075281 | −0.030911 | 0.004953 | −0.021783 | 0.011836 | −0.080239 | −0.014571 | −0.034231 | −0.018051 | 0.0308 | −0.049652 | −0.067218 |
| 114 | −0.002978 | 0.030578 | −0.038347 | −0.023255 | −0.079621 | −0.024424 | 0.016141 | −0.053245 | 0.015341 | 0.063828 | 0.019798 | 0.051794 | −0.028114 | −0.086608 |
| 115 | 0.046266 | 0.047791 | 0.045777 | −0.049468 | −0.042342 | −0.039082 | 0.035875 | −0.036988 | 0.039035 | −0.01055 | −0.032322 | −0.002863 | −0.070026 | −0.031772 |
| 116 | −0.02619 | 0.01607 | 0.042622 | 0.060916 | −0.07384 | −0.019017 | 0.078539 | 0.028927 | 0.029669 | 0.020588 | −0.000771 | −0.007559 | −0.040877 | 0.026943 |
| 117 | 0.059718 | −0.018502 | 0.039255 | 0.014452 | −0.033884 | 0.025985 | −0.026601 | 0.001989 | −0.044056 | 0.050601 | −0.067476 | 0.083291 | 0.183125 | 0.058526 |
| 118 | 0.058888 | 0.013765 | 0.081008 | 0.04297 | −0.006403 | 0.039594 | −0.039777 | 0.062068 | −0.064624 | −0.021071 | 0.045661 | −0.043747 | −0.048078 | 0.076678 |
| 119 | −0.066722 | −0.062421 | 0.021409 | −0.094436 | −0.050824 | 0.012162 | 0.095962 | 0.014526 | 0.017399 | −0.025122 | 0.086334 | −0.096132 | −0.005367 | −0.025167 |
| 120 | 0.074365 | −0.051036 | 0.013021 | 0.029375 | −0.010016 | −0.005805 | −0.013346 | −0.051103 | −0.036138 | 0.064237 | −0.004554 | 0.042732 | 0.120266 | 0.016481 |
| 121 | 0.049134 | −0.029718 | 0.030795 | 0.049535 | 0.046432 | 0.049631 | −0.001623 | −0.003535 | −0.028804 | 0.048911 | 0.011417 | 0.063207 | 0.11883 | 0.079454 |
| 122 | 0.087458 | 0.099133 | 0.095274 | −0.018649 | −0.059911 | −0.044965 | −0.007003 | −0.010243 | −0.015915 | 0.005531 | 0.099604 | −0.022138 | −0.107554 | 0.000721 |
| 123 | 0.083852 | 0.066386 | 0.110816 | −0.015849 | −0.056843 | 0.018167 | 0.055195 | 0.074299 | 0.028426 | −0.050492 | 0.001837 | −0.015564 | −0.103347 | −0.010533 |
| 124 | −0.046491 | 0.004682 | 0.010115 | −0.07294 | 0.042891 | −0.012615 | 0.10852 | 0.090539 | −0.0132791 | −0.0855081 | 0.0924481 | −0.0586851 | 0.0140921 | 0.008794 |
| 125 | 0.083205 | 0.077632 | 0.072418 | 0.009061 | −0.012589 | 0.046554 | −0.015388 | −0.021628 | −0.009728 | 0.033743 | −0.105572 | −0.06061 | −0.013928 | 0.005938 |
| 126 | 0.080194 | 0.136331 | 0.090622 | −0.012055 | −0.079166 | 0.073114 | −0.002689 | 0.012013 | −0.002548 | −0.012147 | −0.132435 | 0.022263 | −0.02471 | 0.018021 |
| 127 | 0.06618 | 0.0778 | 0.05883 | 0.007714 | −0.088599 | 0.075549 | −0.00655 | 0.005183 | −0.002647 | 0.011597 | −0.125998 | −0.034418 | 0.018386 | −0.023705 |
| 128 | 0.006531 | −0.040947 | −0.017973 | −0.021778 | −0.164792 | 0.017553 | 0.012422 | −0.078789 | −0.046755 | 0.070923 | −0.014615 | 0.041982 | −0.054009 | 0.021992 |
| 129 | 0.055275 | 0.098272 | 0.036962 | 0.021965 | −0.038247 | 0.073718 | 0.050634 | −0.083931 | 0.043354 | −0.008063 | 0.130715 | −0.018624 | 0.016897 | 0.021725 |
| 130 | 0.094808 | 0.031786 | 0.011892 | 0.0686 | −0.058946 | 0.052062 | 0.077354 | −0.079769 | −0.0484891 | 0.029731 | −0.0239641 | 0.008148 | 0.008381 | 0.01608 |
| 131 | 0.077335 | 0.070593 | −0.005303 | 0.092094 | −0.009238 | 0.173777 | 0.034768 | −0.068843 | 0.086055 | −0.000693 | 0.083682 | 0.04343 | 0.04455 | 0.049305 |
| 132 | 0.018748 | −0.063004 | 0.013534 | 0.028921 | −0.066246 | −0.017594 | 0.009591 | −0.080294 | −0.040793 | 0.037571 | −0.046334 | −0.007602 | −0.078493 | 0.007868 |
| 133 | −0.138798 | 0.007385 | 0.008301 | −0.011851 | −0.041803 | 0.099782 | 0.020703 | 0.056467 | −0.052059 | 0,030616 | 0.022147 | 0.109723 | −0.014295 | 0.02959 |
| 134 | 0.022801 | 0.106422 | 0.066732 | 0.057035 | −0.009258 | 0.021949 | −0.057915 | 0.072211 | 0.000116 | 0.007427 | −0.029734 | 0.095969 | 0.023897 | 0.092855 |
| 135 | −0.016742 | −0.023488 | −0.000895 | −0.029 | −0.017444 | −0.014405 | −0.012249 | 0.013487 | 0.002931 | −0.0074981 | 0.02533 | −0.0280571 | −0.005711 | −0.041005 |
| 136 | −0.03262 | 0.01346 | 0.027926 | 0.010185 | −0.0139 | −0.060409 | 0.13944 | 0.023066 | −0.03578 | −0.000589 | 0.058592 | −0.07561 | −0.058069 | −0.073628 |
| 137 | 0.033283 | 0.025305 | 0.098726 | 0.042372 | −0.062763 | −0.004366 | 0.030704 | 0.01053 | −0.022813 | −0.032732 | −0.046292 | 0.070164 | 0.060329 | −0.084994 |
| 138 | −0.05366 | 0.030522 | 0.056539 | 0.046223 | 0.018252 | 0.043298 | −0.007839 | −0.113397 | 0.124312 | 0.018046 | 0.041199 | 0.04441 | −0.118205 | −0.044771 |
| 139 | −0.14312 | −0.043947 | −0.00959 | −0.031456 | −0.077438 | −0.001016 | −0.007435 | 0.001864 | −0.051319 | 0.057371 | 0.031565 | −0.049645 | −0.040508 | 0.043927 |
| 140 | 0.113018 | −0.005367 | −0.010774 | 0.037202 | 0.017183 | 0.052732 | 0.058102 | 0.149198 | −0.068908 | −0.011267 | 0.040135 | 0.052115 | −0.041022 | 0.083186 |
| 141 | 0.037961 | −0.018359 | −0.031252 | 0.035938 | −0.05076 | 0.003797 | −0.068564 | −0.008864 | 0.011807 | 0.046623 | 0.018042 | −0.006258 | −0.039522 | −0.017406 |
| 142 | −0.045436 | 0.013792 | 0.032123 | −0.050624 | −0.05006 | −0.06793 | 0.063713 | 0.003418 | −0.009654 | −0.126829 | −0.005794 | −0.053459 | 0.042472 | 0.04085 |
| 143 | −0.01914 | −0.040774 | 0.002181 | −0.023421 | 0.047279 | −0.060667 | 0.009591 | 0.056306 | 0.013471 | −0.112734 | 0.121314 | 0.009399 | −0.056047 | −0.003262 |
| 144 | −0.021791 | 0.053669 | 0.006055 | −0.042733 | 0.056644 | −0.08741 | 0.107594 | 0.099206 | −0.018857 | −0.099589 | 0.052216 | −0.050741 | 0.015592 | −0.032083 |
| 145 | −0.070241 | 0.023601 | 0.053735 | 0.007715 | −0.016017 | −0.021237 | 0.01989 | 0.022477 | 0.0377461 | −0.080635 | 0.019596 | 0.0143541 | −0.0215011 | −0.03807 |
| 146 | −0.061465 | 0.016002 | 0.042521 | −0.006193 | −0.060259 | 0.044683 | −0.039086 | 0.005946 | −0.02377 | −0.00859 | −0.082448 | 0.000119 | −0.001554 | 0.017675 |
| 147 | −0.03224 | 0.082325 | 0.068108 | 0.001191 | −0.032017 | 0.03539 | −0.019033 | 0.023258 | −0.061285 | 0.036484 | −0.040169 | −0.025367 | −0.000683 | 0.016802 |
| 148 | −0.01277 | −0.014019 | −0.00734 | 0.021919 | −0.110172 | 0.088031 | −0.009999 | −0.073981 | −0.082073 | 0.095499 | 0.066462 | 0.131408 | −0.022667 | −0.051248 |
| 149 | 0.053366 | −0.060842 | −0.031269 | 0.014036 | −0.032822 | 0.029607 | −0.029917 | −0.017685 | 0.01896 | 0.016018 | 0.037982 | 0.024145 | −0.061373 | −0.043082 |
| 150 | 0.110082 | −0.044744 | −0.020964 | −0.005634 | −0.035426 | −0.006998 | 0.012527 | −0.061693 | 0.009805 | 0.00623 | 0.000319 | −0.001922 | 0.0084 | −0.052685 |
| 151 | 0.107417 | 0.059488 | 0.065718 | 0.019746 | 0.059829 | −0.068456 | 0.024609 | −0.01597 | −0.001274 | 0.049642 | −0.133029 | −0.093241 | −0.118625 | −0.0029 |
| 152 | −0.067993 | −0.01111 | −0.02051 | −0.025289 | −0.038353 | −0.019208 | 0.049947 | −0.044148 | 0.013859 | −0.054341 | 0.022141 | −0.145073 | 0.051188 | −0.049071 |
| 153 | −0.097348 | −0.015372 | −0.021451 | −0.031572 | −0.008077 | −0.060613 | 0.029282 | 0.000648 | −0.001049 | −0.13654 | 0.059592 | −0.10424 | 0.020829 | 0.033508 |
| 154 | −0.047754 | 0.091051 | 0.002028 | −0.059899 | 0.009318 | −0.042242 | 0.083155 | −0.039563 | 0.041149 | −0.158568 | 0.005895 | −0.084145 | 0.020318 | 0.018088 |
| 155 | −0.005387 | 0.096254 | 0.062039 | −0.012437 | −0.031556 | 0.035635 | 0.092791 | −0.080347 | 0.014865 | −0.058793 | −0.071641 | −0.042099 | 0.007769 | −0.018919 |
| 156 | 0.097684 | 0.0509311 | 0.020245 | −0.028883 | −0.066081 | −0.010275 | 0.073006 | −0.036613 | −0.033296 | −0.019881 | −0.123624 | −0.04521 | −0.006666 | 0.02218 |
| 157 | 0.045033 | −0.034182 | −0.000971 | −0.041381 | 0.026583 | −0.028015 | 0.008219 | −0.018796 | −0.003482 | −0.006565 | −0.049846 | −0.052592 | −0.038716 | −0.036663 |
| 158 | 0.062111 | 0.113645 | 0.112458 | −0.02537 | −0.020939 | 0.056432 | 0.097773 | 0.025524 | 0.095234 | 0.011823 | −0.062808 | −0.094253 | −0.019636 | −0.143262 |
| 159 | 0.028711 | −0.043703 | −0.016271 | −0.037121 | −0.121435 | −0.071724 | 0.099769 | 0.049147 | 0.0365 | 0.059289 | 0.143868 | 0.104245 | 0.152455 | −0.027564 |
| 160 | −0.001886 | −0.067989 | 0.003289 | −0.081874 | −0.055021 | 0.012504 | 0.110133 | 0.087385 | −0.009907 | 0.142971 | 0.174974 | 0.038552 | −0.013166 | 0.123111 |
| 161 | 0.029088 | −0.040584 | −0.024756 | −0.037543 | −0.174872 | −0.029642 | −0.012904 | −0.053543 | 0.018592 | 0.126243 | 0.05058 | 0.035632 | −0.051864 | 0.002816 |
| 162 | 0.00762 | −0.105756 | −0.012443 | 0.004662 | −0.001509 | −0.098635 | 0.058582 | 0.022143 | −0.03751 | −0.127792 | 0.072385 | −0.039646 | 0.092779 | −0.135227 |
| 163 | −0.003958 | −0.038377 | −0.0421 | −0.026401 | −0.04121 | −0.026042 | 0.012342 | −0.080484 | −0.002418 | −0.063443 | −0.030077 | −0.091835 | 0.10898 | −0.050648 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 164 | −0.023735 | 0.0562961 | 0.047596 | −0.022528 | 0.060278 | 0.059484 | 0.100967 | −0.050469 | 0.093946 | −0.060411 | −0.043067 | −0.096778 | 0.033035 | −0.095385 |
| 165 | −0.022436 | 0.035044 | 0.012027 | −0.061539 | −0.010299 | 0.066892 | 0.012369 | −0.064696 | 0.0399891 | −0.0429471 | 0.0118271 | 0.0438081 | −0.0570691 | 0.044699 |
| 166 | −0.012587 | 0.009867 | −0.023756 | −0.077576 | 0.120346 | 0.019062 | 0.211596 | 0.103388 | −0.0106781 | −0.0571571 | 0.0778971 | 0.06781 | 0.0354331 | −0.006022 |
| 167 | 0.025047 | −0.048377 | −0.05029 | −0.048655 | 0.00709 | −0.019677 | 0.084228 | 0.014123 | 0.017952 | −0.00594 | −0.026862 | 0.050596 | 0.01854 | −0.001108 |
| 168 | 0.001779 | −0.057024 | 0.016804 | 0.07334 | 0.000013 | −0.039698 | −0.070823 | −0.037069 | 0.02431 | 0.024695 | −0.047777 | −0.158793 | 0.058412 | 0.048672 |
| 169 | −0.063985 | −0.014813 | −0.049099 | 0.109731 | −0.050921 | 0.083625 | 0.004336 | 0.022795 | 0.000787 | −0.020067 | 0.006463 | −0.018245 | 0.04467 | 0.029178 |
| 170 | −0.071158 | 0.016237 | −0.06601 | 0.123636 | −0.085657 | 0.066409 | 0.047275 | 0.014614 | −0.004815 | −0.007554 | −0.000476 | −0.024976 | 0.059703 | −0.003599 |
| 171 | −0.042589 | −0.022134 | −0.017181 | 0.087735 | −0.063672 | 0.044994 | 0.004513 | 0.063657 | 0.0020141 | 0.0085231 | 0.0139781 | −0.005549 | 0.0506521 | 0.047418 |
| 172 | −0.042646 | −0.032415 | −0.016251 | −0.032939 | 0.036304 | 0.063351 | −0.016736 | −0.006637 | −0.039676 | 0.003628 | 0.063487 | 0.005084 | −0.003768 | −0.00027 |
| 173 | −0.026495 | −0.019702 | 0.01972 | −0.010074 | −0.007889 | 0.032842 | −0.037648 | −0.034321 | −0.025408 | 0.046274 | 0.031468 | 0.058503 | 0.009869 | 0.021063 |
| 174 | −0.003436 | 0.008468 | 0.039699 | 0.01097 | 0.061509 | 0.018561 | −0.05548 | −0.061999 | −0.019164 | 0.064414 | 0.031809 | 0.000128 | 0.016622 | 0.039381 |
| 175 | 0.014255 | −0.035071 | 0.048783 | −0.014765 | 0.012051 | 0.019595 | −0.036045 | −0.032814 | −0.060467 | 0.068211 | 0.088221 | −0.017026 | 0.009352 | −0.040196 |
| 176 | −0.019859 | −0.05228 | −0.017043 | −0.052261 | 0.057221 | 0.025978 | 0.016053 | 0.093541 | −0.064512 | −0.023374 | 0.020951 | 0.035554 | −0.012784 | −0.002585 |
| 177 | −0.034815 | −0.051784 | −0.068286 | −0.110336 | −0.074972 | −0.03392 | −0.044565 | 0.09167 | 0.097685 | 0.093865 | −0.112026 | −0.058644 | −0.003264 | 0.08001 |
| 178 | −0.093864 | 0.006697 | 0.068383 | 0.059942 | 0.041523 | −0.009316 | −0.015753 | 0.006847 | 0.014669 | −0.046444 | 0.072413 | 0.01233 | 0.005466 | −0.065012 |
| 179 | −0.073721 | 0.023769 | 0.067542 | 0.099065 | −0.00964 | −0.037527 | 0.009818 | 0.023001 | −0.006381 | 0.018892 | −0.021171 | −0.033165 | 0.055728 | −0.025333 |
| 180 | −0.076922 | 0.04225 | 0.067916 | 0.093207 | 0.000277 | −0.027599 | 0.028713 | 0.006965 | −0.020027 | −0.005346 | 0.005872 | 0.000708 | 0.035907 | −0.035775 |
| 181 | −0.081532 | 0.045771 | 0.060361 | 0.09395 | −0.005273 | −0.038221 | 0.043346 | 0.011654 | −0.0160521 | −0.0001721 | −0.0086661 | −0.0019971 | 0.0427411 | −0.038426 |
| 182 | −0.090459 | 0.045859 | 0.036892 | 0.064732 | −0.009609 | −0.060996 | 0.050933 | −0.012041 | −0.005065 | 0.041794 | 0.010675 | −0.015578 | 0.050084 | −0.056515 |
| 183 | −0.04984 | 0.041518 | 0.09528 | 0.053982 | −0.027703 | −0.071609 | −0.008514 | 0.012043 | 0.01504 | 0.068961 | −0.013126 | −0.047731 | 0.038671 | 0.004646 |
| 184 | 0.000108 | 0.019832 | 0.126269 | 0.001176 | 0.026072 | −0.048605 | −0.07124 | 0.025995 | 0.026621 | 0.040912 | −0.04441 | −0.049714 | 0.022276 | 0.006017 |
| 185 | −0.010904 | 0.058715 | 0.153864 | −0.002183 | 0.072625 | −0.051987 | −0.00464 | −0.014965 | −0.001568 | −0.050812 | −0.010708 | 0.016489 | −0.006394 | 0.06607 |
| 186 | −0.030866 | 0.048323 | 0.146761 | −0.067389 | 0.069079 | −0.050739 | −0.050493 | −0.015403 | −0.0587471 | 0.002946 | 0.0858641 | 0.0883061 | 0.0324961 | 0.044143 |
| 187 | −0.018521 | 0.064379 | 0.056237 | −0.071045 | 0.035008 | −0.03534 | −0.057486 | −0.033715 | −0.066414 | 0.056441 | 0.065635 | 0.024585 | −0.024782 | −0.003521 |
| 188 | −0.014791 | 0.061628 | 0.073818 | −0.056324 | 0.096931 | −0.039584 | −0.066634 | −0.062009 | −0.040582 | 0.058292 | 0.068861 | −0.008863 | −0.015017 | 0.006761 |
| 189 | −0.009329 | 0.045812 | 0.105759 | −0.014466 | 0.11102 | −0.021578 | −0.081755 | −0.052924 | 0.001531 | 0.06086 | 0.060379 | −0.029424 | 0.011751 | −0.037637 |
| 190 | −0.051671 | −0.016021 | −0.010217 | 0.0293 | 0.042178 | 0.034584 | 0.045339 | 0.031388 | 0.071682 | 0.035457 | −0.035617 | 0.032264 | 0.008418 | −0.007182 |
| 191 | −0.015076 | 0.012376 | −0.028705 | 0.064236 | 0.007003 | 0.024276 | 0.008923 | 0.048246 | 0.032947 | 0.041334 | −0.054876 | 0.021636 | −0.009945 | 0.019438 |
| 192 | −0.001719 | 0.014898 | 0.025629 | −0.004742 | −0.026008 | −0.028695 | −0.047933 | 0.020478 | 0.012373 | 0.090098 | −0.012654 | −0.130451 | 0.058283 | −0.014407 |
| 193 | −0.039541 | 0.018146 | 0.03602 | −0.024598 | 0.025007 | −0.031207 | −0.059884 | −0.00072 | −0.024112 | 0.073086 | 0.081594 | −0.066519 | 0.015995 | −0.041929 |
| 194 | −0.029392 | −0.015664 | 0.105199 | −0.065488 | 0.097653 | −0.023942 | −0.044113 | −0.001195 | −0.06524 | 0.096307 | 0.075711 | −0.006555 | 0.01091 | −0.04633 |
| 195 | −0.024882 | −0.019084 | 0.045122 | −0.093537 | 0.042195 | 0.083228 | 0.071351 | −0.019006 | −0.052563 | 0.11958 | −0.016706 | 0.060894 | 0.007545 | −0.061112 |
| 196 | −0.029701 | −0.00201 | 0.036588 | −0.022111 | 0.045326 | 0.062327 | 0.052704 | −0.006898 | −0.026213 | 0.052253 | −0.028317 | 0.015017 | 0.012674 | −0.053663 |
| 197 | −0.020081 | 0.031253 | −0.034493 | 0.035552 | 0.004042 | 0.035595 | 0.017156 | −0.029985 | 0.043326 | 0.034616 | −0.029491 | 0.03929 | 0.021744 | −0.009474 |
| 198 | −0.03445 | 0.033804 | 0.044226 | −0.076299 | 0.027267 | 0.029985 | 0.017247 | −0.080296 | −0.114671 | 0.081314 | 0.017732 | 0.031035 | 0.019372 | −0.094539 |
| 199 | 0.047343 | −0.108342 | 0.001205 | −0.086925 | 0.016136 | −0.061532 | −0.012697 | 0.008184 | −0.093635 | −0.0171 | 0.035975 | 0.004906 | −0.13909 | −0.132415 |
| 200 | −0.053746 | 0.024639 | 0.015233 | −0.09727 | 0.016334 | 0.02292 | 0.050611 | −0.051142 | −0.092255 | 0.04935 | 0.067208 | −0.000067 | 0.005023 | −0.054577 |
| 201 | −0.069195 | 0.001528 | −0.029021 | −0.004306 | 0.003435 | −0.004365 | −0.056145 | 0.161179 | −0.0049891 | 0.1013751 | 0.1015671 | −0.059204 | −0.094042 | 0.014525 |
| 202 | −0.038978 | 0.031373 | −0.002593 | −0.067653 | 0.000081 | 0.064633 | 0.008341 | −0.113345 | −0.073224 | 0.065706 | 0.056115 | 0.020729 | 0.056337 | −0.102773 |
| 203 | −0.030801 | 0.052197 | −0.068507 | 0.000585 | −0.099982 | −0.014258 | 0.044598 | −0.086473 | 0.024953 | 0.089051 | 0.048504 | 0.056359 | 0.03844 | 0.063948 |
| 204 | −0.034617 | −0.042434 | 0.024069 | −0.00061 | −0.037318 | 0.063978 | −0.03933 | −0.136306 | 0.180919 | 0.022192 | 0.086129 | −0.093795 | 0.022836 | −0.02486 |
| 205 | 0.020042 | −0.079592 | −0.050319 | −0.068166 | −0.007712 | −0.052336 | −0.000622 | 0.003694 | 0.022826 | −0.097611 | −0.182798 | −0.053598 | −0.091931 | −0.073528 |
| 206 | −0.010418 | 0.025599 | −0.036145 | 0.01114 | 0.069199 | 0.139423 | −0.12297 | −0.098859 | 0.334233 | −0.109265 | 0.110234 | 0.007227 | −0.00655 | 0.015498 |
| 207 | 0.011533 | 0.008943 | −0.02061 | 0.0484 | −0.014288 | 0.114913 | −0.096361 | −0.132624 | 0.130783 | −0.004055 | 0.181966 | −0.098461 | −0.11296 | −0.002791 |
| 208 | −0.03454 | 0.141279 | −0.031616 | 0.006944 | −0.009848 | 0.073526 | 0.060542 | −0.020311 | 0.037647 | 0.018712 | 0.074289 | 0.00781 | 0.037618 | 0.024868 |
| 209 | −0.015577 | 0.020648 | 0.026708 | −0.063266 | 0.01022 | −0.037542 | 0.076814 | 0.005791 | −0.08325 | 0.122698 | 0.083571 | −0.03894 | −0.083909 | −0.099443 |
| 210 | 0.028594 | 0.085919 | 0.084185 | 0.046035 | −0.022781 | 0.048225 | 0.029072 | −0.139157 | 0.087263 | 0.017793 | −0.082999 | 0.086732 | −0.103499 | −0.084714 |
| 211 | 0.008102 | −0.051138 | −0.07558 | 0.006327 | 0.060622 | 0.10071 | −0.036095 | 0.014787 | 0.067421 | −0.097326 | 0.048082 | 0.0127891 | −0.100679 | −0.008441 |
| 212 | −0.096929 | −0.026721 | −0.050137 | −0.034012 | 0.096491 | 0.00695 | 0.067556 | −0.01202 | −0.165581 | −0.015916 | −0.067148 | −0.015822 | −0.036776 | 0.182066 |
| 213 | 0.007754 | −0.043092 | 0.08365 | 0.002075 | 0.052008 | 0.09589 | −0.011454 | −0.083031 | 0.212069 | −0.04573 | 0.067724 | 0.051064 | −0.022648 | −0.05653 |
| 214 | −0.059652 | 0.013283 | 0.090165 | 0.071141 | 0.004591 | −0.013304 | −0.018377 | 0.042461 | 0.010854 | −0.002513 | −0.018942 | −0.025331 | 0.069001 | −0.03657 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 215 | −0.040817 | 0.049429 | 0.151898 | 0.066815 | 0.06465 | −0.043574 | −0.010278 | 0.037169 | −0.004275 | −0.042204 | 0.015708 | −0.082628 | −0.022212 | 0.045835 |
| 216 | 0.052091 | −0.089176 | 0.043721 | 0.110649 | 0.002529 | −0.030449 | −0.061936 | −0.008672 | −0.044644 | −0.076858 | −0.012689 | −0.052155 | −0.010495 | 0.011549 |
| 217 | −0.074297 | −0.118412 | −0.018945 | −0.061483 | 0.017105 | 0.090396 | 0.013409 | −0.000715 | −0.048294 | 0.035347 | −0.097337 | 0.001252 | 0.008789 | −0.04351 |
| 218 | −0.042469 | −0.001921 | −0.017931 | 0.031553 | −0.034562 | −0.060885 | −0.00849 | 0.003808 | 0.016675 | −0.014619 | 0.024188 | 0.017558 | −0.0192911 | −0.03757 |
| 219 | −0.030185 | −0.099624 | 0.04582 | 0.108629 | −0.051008 | −0.006987 | −0.020735 | 0.051777 | −0.005758 | −0.046014 | −0.04192 | 0.029098 | −0.051015 | −0.025142 |
| 220 | −0.046843 | −0.040302 | −0.001927 | 0.003237 | 0.038395 | 0.10705 | 0.092124 | 0.033902 | 0.013713 | −0.051473 | −0.079527 | 0.033447 | 0.043966 | 0.100593 |
| 221 | −0.040054 | −0.022617 | 0.022073 | −0.010326 | −0.007424 | 0.04938 | 0.013639 | −0.054234 | 0.000275 | −0.082259 | −0.037292 | 0.0658781 | 0.005634 | 0.030602 |
| 222 | −0.025906 | −0.060487 | −0.008616 | 0.055303 | −0.023095 | 0.060163 | 0.026277 | −0.018451 | −0.005202 | 0.032218 | −0.058137 | −0.079286 | 0.045704 | −0.072704 |
| 223 | −0.000962 | −0.046425 | 0.006296 | 0.074267 | 0.003088 | 0.064986 | 0.031207 | −0.003881 | −0.009846 | 0.01098 | −0.029178 | −0.03482 | 0.004815 | −0.059777 |
| 224 | 0.037755 | −0.013917 | 0.021547 | −0.002743 | 0.025451 | 0.091409 | −0.084713 | −0.047383 | −0.058886 | 0.012498 | 0.018404 | −0.086122 | 0.141096 | 0.050826 |
| 225 | 0.03787 | −0.001134 | 0.021783 | −0.003109 | 0.011969 | 0.104154 | −0.096235 | −0.03068 | −0.058869 | 0.007632 | 0.019348 | −0.08448 | 0.135824 | 0.060913 |
| 226 | −0.008378 | −0.017037 | 0.043537 | −0.016783 | −0.050877 | 0.025669 | −0.02877 | 0.041322 | −0.042474 | 0.001674 | 0.043883 | −0.063656 | −0.001068 | 0.045713 |
| 227 | 0.075646 | −0.028447 | 0.071715 | 0.072267 | −0.03932 | 0.039015 | −0.079092 | 0.034438 | −0.086914 | 0.010783 | 0.136937 | −0.166638 | 0.085436 | 0.117826 |
| 228 | 0.008437 | −0.037268 | 0.007314 | −0.003929 | −0.102192 | 0.063214 | −0.044147 | −0.02816 | −0.036556 | −0.089233 | 0.085543 | −0.100425 | 0.008502 | −0.028823 |
| 229 | 0.031583 | 0.014046 | 0.024036 | −0.061133 | −0.055058 | −0.02187 | −0.137158 | −0.042961 | −0.160356 | −0.102527 | −0.009891 | 0.090448 | 0.077494 | 0.018433 |
| 230 | 0.046553 | −0.081362 | 0.045626 | 0.118324 | −0.007442 | −0.076481 | −0.097912 | −0.000723 | −0.06425 | −0.067616 | 0.006466 | −0.059148 | 0.063331 | 0.06737 |
| 231 | −0.041921 | −0.087925 | 0.00821 | 0.067207 | −0.124145 | 0.001282 | 0.016125 | 0.036366 | −0.003954 | −0.018299 | 0.055392 | −0.042024 | −0.012784 | 0.025605 |
| 232 | 0.026661 | −0.022139 | 0.013903 | −0.065889 | −0.057806 | 0.074057 | −0.006075 | −0.059364 | −0.054803 | −0.059635 | −0.03684 | −0.048516 | 0.053542 | 0.006396 |
| 233 | 0.072446 | 0.040028 | 0.071335 | 0.007262 | −0.071893 | −0.026011 | −0.044392 | 0.021446 | 0.002032 | −0.01449 | 0.08562 | 0.030655 | −0.113946 | 0.011415 |
| 234 | 0.020249 | −0.110435 | 0.094241 | 0.046186 | −0.138418 | −0.046521 | −0.006052 | 0.078433 | 0.068647 | −0.114508 | 0.098603 | 0.034612 | −0.107354 | 0.039979 |
| 235 | −0.033532 | −0.098183 | 0.096588 | 0.014375 | −0.110675 | −0.035686 | −0.028032 | 0.021819 | 0.031645 | −0.141632 | 0.078394 | 0.005845 | −0.017452 | 0.042 |
| 236 | 0.025797 | −0.001 | −0.02067 | −0.049742 | 0.023303 | −0.027585 | 0.007941 | −0.027641 | 0.000867 | −0.072392 | −0.060987 | 0.04798 | 0.040269 | −0.015293 |
| 237 | 0.040023 | 0.071622 | −0.089625 | −0.012951 | −0.001181 | −0.103367 | −0.000005 | 0.042804 | 0.0674211 | 0.0715661 | −0.0143941 | −0.046532 | 0.017236 | −0.096129 |
| 238 | 0.013642 | −0.089364 | 0.006264 | 0.111803 | −0.032763 | −0.033411 | −0.035211 | 0.037173 | 0.031262 | 0.029598 | −0.041657 | 0.016491 | −0.062857 | −0.079923 |
| 239 | −0.001946 | −0.080283 | 0.025835 | 0.128145 | −0.05017 | 0.00097 | −0.038014 | −0.005871 | −0.030897 | 0.020684 | 0.005185 | 0.038789 | −0.07792 | −0.072012 |
| 240 | 0.027417 | −0.029961 | 0.025595 | −0.016105 | −0.075441 | 0.104279 | 0.040032 | 0.061023 | 0.053026 | −0.032719 | 0.021618 | 0.082786 | −0.059016 | 0.059698 |
| 241 | 0.068441 | 0.00289 | 0.075607 | −0.014521 | −0.051503 | 0.01781 | 0.031424 | 0.058671 | 0.055516 | −0.026964 | 0.040836 | 0.044138 | −0.084015 | 0.046689 |
| 242 | 0.007879 | 0.018968 | 0.053586 | −0.044086 | −0.053321 | −0.097688 | 0.020949 | −0.03278 | 0.016451 | −0.108153 | 0.032778 | 0.024488 | −0.002816 | 0.001696 |
| 243 | −0.020706 | −0.030229 | 0.081742 | −0.022024 | −0.035981 | −0.01924 | −0.018624 | −0.046973 | −0.013387 | −0.134644 | −0.000164 | −0.078377 | 0.00372 | −0.042961 |
| 244 | −0.01803 | 0.046341 | −0.003543 | −0.046327 | 0.011543 | 0.027898 | −0.000169 | −0.058759 | −0.03186 | −0.092785 | 0.032241 | 0.043161 | −0.016209 | 0.029415 |
| 245 | 0.008622 | 0.060535 | 0.027895 | −0.001108 | 0.130006 | −0.028796 | 0.001981 | −0.04874 | 0.008082 | −0.050712 | 0.018235 | 0.053402 | 0.014775 | 0.030424 |
| 246 | 0.043366 | 0.090188 | −0.016983 | 0.046701 | 0.033695 | −0.044734 | 0.06328 | 0.03586_ | 0.064014 | 0.024902 | −0.002749 | 0.043768 | 0.0156011 | 0.05722 |
| 247 | 0.04295 | −0.049562 | 0.032255 | 0.042216 | 0.049278 | 0.032862 | 0.038988 | 0.020188 | 0.0408641 | 0.0080381 | −0.0750361 | 0.047101 | 0.000361 | 0.048858 |
| 248 | 0.036187 | −0.071211 | 0.032189 | 0.028869 | 0.020563 | 0.069915 | 0.020598 | 0.026703 | 0.012701 | −0.038258 | −0.083186 | 0.001286 | 0.011894 | 0.041606 |
| 249 | 0.01551 | −0.074291 | −0.015863 | 0.02188 | −0.075976 | 0.125223 | 0.058741 | 0.072831 | 0.044479 | 0.021972 | −0.025121 | −0.076085 | 0.059653 | −0.011618 |
| 250 | 0.030817 | −0.053638 | 0.022946 | −0.006177 | −0.072073 | 0.042838 | 0.05917 | 0.087365 | 0.058806 | −0.032213 | 0.030473 | 0.07304 | −0.043845 | 0.042762 |
| 251 | −0.021611 | −0.029389 | 0.069378 | −0.051068 | −0.061358 | 0.042933 | 0.0485 | 0.067486 | 0.056234 | −0.07808 | 0.044496 | 0.056287 | −0.026642 | 0.057619 |
| 252 | −0.042568 | −0.05723 | 0.080067 | −0.098393 | 0.004411 | 0.029658 | 0.070323 | 0.022905 | 0.00794 | −0.08768 | 0.005872 | 0.006477 | 0.026715 | −0.032973 |
| 253 | −0.003539 | −0.006246 | 0.037731 | −0.075718 | −0.045353 | 0.018401 | −0.006327 | −0.09632 | −0.039717 | −0.105256 | −0.056368 | −0.091788 | 0.015052 | −0.0006 |
| 254 | 0.009236 | 0.0020251 | −0.008082 | 0.024423 | 0.052395 | 0.072088 | 0.0188 | −0.029548 | −0.025085 | −0.033655 | 0.02376 | −0.005313 | 0.015275 | −0.017286 |
| 255 | −0.020461 | 0.047695 | 0.00714 | −0.030521 | 0.047962 | 0.061599 | 0.054686 | −0.04248 | −0.003809 | −0.098296 | 0.022863 | 0.068747 | 0.003758 | 0.081246 |
| 256 | −0.033975 | 0.022626 | 0.046399 | −0.058831 | 0.160725 | 0.087156 | 0.064261 | −0.083941 | 0.013707 | −0.022716 | −0.036552 | 0.076873 | 0.00717 | 0.10515 |
| 257 | −0.010075 | −0.034507 | 0.03178 | −0.041805 | 0.003895 | 0.011882 | 0.013567 | 0.022745 | −0.009183 | 0.041151 | −0.042058 | −0.018447 | −0.030998 | 0.023485 |
| 258 | 0.02565 | −0.035253 | −0.002095 | −0.068231 | 0.074705 | 0.107128 | 0.004008 | −0.017324 | −0.018479 | 0.029929 | −0.093634 | −0.102378 | −0.011574 | −0.00739 |
| 259 | 0.00038 | −0.062654 | 0.004684 | 0.017736 | −0.043271 | 0.058542 | 0.044931 | 0.056152 | 0.009042 | −0.00285 | 0.017819 | −0.050718 | 0.046957 | −0.051954 |
| 260 | −0.020011 | −0.108333 | −0.014223 | −0.050132 | −0.024409 | 0.072855 | 0.100052 | 0.096058 | −0.007209 | −0.015356 | 0.029014 | 0.000499 | 0.019287 | −0.117226 |
| 261 | −0.02459 | −0.111663 | 0.02413 | −0.07867 | −0.016794 | 0.089632 | 0.103328 | 0.066177 | 0.016913 | −0.006146 | 0.0002 | 0.018707 | −0.025739 | −0.015922 |
| 262 | −0.024409 | −0.04723 | −0.007332 | −0.075262 | 0.002986 | 0.016149 | 0.057673 | −0.037358 | −0.025954 | −0.011133 | −0.023573 | 0.016963 | 0.025491 | −0.026814 |
| 263 | −0.04804 | −0.049852 | 0.000412 | −0.050011 | −0.001239 | −0.007792 | 0.024323 | −0.062595 | −0.026707 | −0.042264 | −0.011159 | −0.004746 | 0.054566 | −0.008197 |
| 264 | 0.0009661 | −0.045661 | −0.061164 | 0.067149 | 0.014998 | 0.090298 | 0.041952 | −0.001703 | −0.017372 | 0.023348 | 0.031386 | −0.078579 | 0.087699 | −0.032725 |
| 265 | −0.012239 | −0.071635 | −0.049533 | 0.002045 | 0.098463 | 0.182008 | 0.068738 | 0.006178 | −0.02951 | 0.069668 | 0.025293 | −0.035224 | 0.037754 | −0.099925 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 266 | −0.011088 | −0.063392 | 0.014834 | −0.058418 | 0.139157 | 0.145291 | 0.077519 | 0.001632 | −0.020056 | 0.03305f | −0.013764 | 0.045718 | −0.012845 | −0.039669 |
| 267 | −0.01344 | −0.002544 | 0.023158 | −0.036667 | −0.080948 | 0.057879 | −0.07075 | −0.082956 | −0.070458 | −0.041412 | 0.052648 | 0.032243 | 0.015747 | 0.022897 |
| 268 | −0.012825 | −0.020622 | 0.033768 | −0.010537 | −0.043166 | 0.026715 | −0.026371 | 0.003368 | −0.02733 | 0.018422 | 0.063155 | −0.011288 | −0.007756 | 0.036245 |
| 269 | −0.014168 | −0.021178 | 0.039093 | −0.023451 | −0.044755 | 0.025697 | −0.033124 | 0.035833 | −0.009689 | 0.0108 | 0.030641 | −0.033552 | −0.000266 | 0.049905 |
| 270 | 0.003416 | −0.01222 | 0.032033 | −0.01319 | −0.042588 | 0.015465 | −0.021429 | 0.029896 | −0.039226 | 0.019945 | 0.081838 | −0.080488 | 0.016093 | 0.063596 |
| 271 | 0.027524 | 0.027762 | 0.009791 | −0.109615 | −0.046302 | −0.059248 | −0.07798 | −0.061217 | −0.046496 | −0.153344 | −0.028026 | 0.089866 | 0.03632 | −0.05191 |
| 272 | −0.027603 | −0.004101 | −0.009053 | −0.06973 | −0.076048 | 0.007224 | −0.067552 | −0.017552 | −0.105264 | −0.083501 | −0.009783 | 0.099922 | 0.028449 | −0.008964 |
| 273 | −0.030636 | −0.017849 | −0.002574 | −0.035207 | −0.028263 | −0.038107 | −0.027562 | 0.026532 | −0.054662 | −0.016252 | −0.000817 | 0.014494 | 0.053795 | 0.03299 |
| 274 | −0.032111 | −0.012765 | 0.003809 | −0.039078 | −0.029093 | −0.040882 | −0.026308 | 0.034778 | −0.048504 | −0.017562 | −0.010177 | 0.004014 | 0.059484 | 0.03835 |
| 275 | 0.019755 | −0.063624 | −0.005222 | 0.05704 | −0.000931 | −0.054073 | −0.077224 | −0.000298 | −0.045324 | −0.031658 | 0.047918 | −0.099987 | 0.108496 | 0.09711 |
| 276 | 0.033222 | −0.001552 | −0.012594 | −0.068703 | −0.003277 | −0.023435 | −0.02784 | −0.065321 | −0.042459 | −0.112393 | −0.077704 | 0.091353 | 0.019062 | −0.024387 |
| 277 | 0.004621 | 0.051157 | −0.108993 | −0.021679 | −0.002839 | −0.131038 | −0.028062 | −0.064794 | 0.002215 | 0.087577 | 0.087927 | −0.020996 | −0.021578 | −0.13535 |
| 278 | 0.014078 | 0.092697 | −0.088058 | −0.011821 | −0.01697 | −0.112578 | −0.035864 | −0.07047 | −0.013219 | 0.086798 | 0.070972 | −0.006175 | 0.014304 | −0.145116 |
| 279 | −0.021465 | −0.091625 | 0.011563 | 0.115937 | −0.040849 | −0.008737 | −0.048273 | −0.004186 | −0.022937 | 0.004776 | 0.031379 | 0.045355 | −0.058534 | −0.080035 |
| 280 | −0.013712 | 0.028506 | 0.06612 | −0.042825 | −0.007661 | −0.015613 | −0.048157 | −0.118103 | −0.055057 | −0.141893 | 0.012167 | −0.11208 | 0.030488 | −0.044013 |
| 281 | 0.060095 | 0.088464 | −0.026509 | 0.017656 | 0.056333 | −0.033369 | 0.051383 | −0.024031 | 0.05476 | 0.045435 | 0.023961 | −0.002621 | 0.029416 | 0.090502 |
| 282 | 0.032114 | 0.069893 | −0.022506 | 0.00559 | 0.07752 | 0.009694 | 0.00954 | −0.036261 | 0.031633 | 0.032174 | 0.013127 | 0.00572 | 0.041504 | 0.083024 |
| 283 | 0.03562 | −0.056013 | 0.045943 | 0.03755 | 0.052457 | 0.059742 | 0.013644 | 0.02998 | 0.020351 | −0.034653 | −0.05018 | 0.030478 | 0.01405 | 0.080542 |
| 284 | −0.004292 | −0.021428 | 0.015432 | −0.034176 | 0.001944 | 0.002173 | 0.007833 | 0.014052 | −0.009793 | 0.019319 | −0.004397 | −0.01398 | −0.013297 | 0.034403 |
| 285 | −0.009526 | −0.005994 | 0.015862 | −8.032241 | −0.007036 | 0.000289 | 0.001042 | 0.004822 | −0.018765 | 0.026824 | −0.007421 | −0.034396 | −0.026922 | 0.030518 |
| 286 | 0.023847 | 0.00144 | 0.005363 | −0.042629 | 0.061084 | 0.076707 | −0.022229 | −0.035625 | −0.037359 | 0.046665 | −0.042369 | −0.140556 | −0.036711 | 0.001864 |
| 287 | 0.023488 | 0.006905 | 0.019534 | −0.041552 | 0.072752 | 0.12339 | −0.055193 | −0.030571 | −0.044446 | 0.02784 | −0.059627 | −0.135754 | −0.033352 | −0.002639 |
| 288 | 0.026758 | −0.087439 | −0.030416 | −0.125552 | 0.107989 | 0.061748 | −0.059004 | 0.003049 | 0.03519 | 0.021537 | −0.112465 | −0.118026 | 0.041374 | 0.019994 |
| 289 | −0.029145 | −0.053816 | −0.020877 | −0.121173 | 0.064529 | 0.045316 | 0.030409 | −0.00732 | −0.015003 | −0.010335 | −0.014371 | 0.027667 | 0.038912 | −0.010902 |
| 290 | −0.017516 | −0.083521 | −0.041502 | −0.156494 | 0.032376 | −0.080471 | −0.059291 | 0.053098 | 0.143632 | 0.061677 | −0.068854 | −0.046877 | −0.005441 | 0.07208 |
| 291 | −0.015104 | −0.090631 | −0.046431 | −0.157757 | 0.03749 | −0.081946 | −0.059535 | 0.054155 | 0.139033 | 0.065236 | −0.059454 | −0.041767 | −0.006016 | 0.073418 |
| 292 | −0.019216 | −0.103489 | −0.017433 | −0.128626 | 0.015735 | −0.08144 | −0.069395 | 0.045246 | 0.145385 | 0.049878 | −0.061194 | −0.043085 | −0.033536 | 0.079154 |
| 293 | −0.016959 | −0.011179 | 0.007623 | 0.017109 | −0.02508 | −0.059361 | −0.052681 | −0.014656 | 0.031565 | 0.057314 | −0.051293 | 0.070547 | 0.001361 | 0.050018 |
| 294 | −0.014869 | 0.010966 | 0.004345 | 0.018095 | 0.031339 | −0.045389 | −0.040438 | 0.03228 | 0.008765 | 0.0223961 | 0.0317541 | 0.0058561 | 0.009659 | 0.009221 |
| 295 | −0.018818 | −0.003287 | −0.008481 | 0.013257 | −0.010411 | −0.091937 | 0.000855 | 0.017975 | 0.003882 | 0.028164 | −0.045477 | 0.080281 | 0.042143 | 0.051101 |
| 296 | −0.07221 | −0.013119 | 0.01545 | 0.004641 | 0.026151 | −0.023491 | −0.004698 | 0.007304 | 0.005411 | 0.033484 | 0.012969 | 0.004314 | 0.082677 | 0.10207 |
| 297 | −0.058008 | −0.003587 | 0.011009 | 0.026553 | −0.000061 | −0.070892 | −0.002989 | 0.003891 | 0.009816 | 0.026592 | −0.044375 | 0.100755 | 0.018578 | 0.045233 |
| 298 | 0.01442 | 0.075787 | 0.05211 | 0.010069 | 0.105166 | −0.101984 | −0.015936 | 0.046264 | 0.073172 | −0.01807 | −0.045679 | 0.036089 | −0.048879 | −0.052981 |
| 299 | −0.07271 | 0.043518 | 0.007166 | 0.029805 | 0.002924 | −0.020507 | −0.004906 | −0.023871 | 0.0343831 | 0.043183 | −0.039334 | 0.043725 | −0.0075841 | 0.02036 |
| 300 | −0.050088 | 0.060523 | 0.066175 | 0.063624 | 0.07765 | −0.064051 | −0.038052 | 0.030936 | −0.038272 | −0.065184 | 0.006532 | −0.029532 | −0.103579 | −0.032021 |
| 301 | −0.011937 | 0.016112 | −0.003793 | 0.029951 | −0.00156 | −0.052601 | 0.003049 | −0.001831 | 0.036419 | 0.032948 | −0.025472 | 0.061308 | 0.005831 | 0.009828 |
| 302 | −0.074726 | 0.022958 | 0.010756 | 0.023892 | 0.021527 | −0.012144 | −0.014394 | −0.003286 | 0.022199 | 0.035773 | 0.016924 | −0.011946 | 0.003216 | 0.005549 |
| 303 | −0.02407 | 0.075413 | 0.022455 | 0.017504 | 0.078559 | 0.044759 | −0.00735 | −0.043351 | −0.00185 | 0.03474 | −0.002032 | −0.027332 | −0.052872 | −0.064171 |
| 304 | −0.070524 | 0.044621 | 0.017822 | 0.013803 | 0.065636 | 0.066225 | −0.038669 | −0.026547 | 0.013604 | 0.028867 | 0.030877 | −0.060183 | −0.040447 | −0.017824 |
| 305 | 0.005505 | 0.033415 | 0.005995 | −0.009021 | 0.041945 | −0.08436 | −0.005206 | −0.012588 | −0.029172 | 0.025624 | 0.071744 | −0.006425 | 0.035364 | 0.080716 |
| 306 | −0.117371 | 0.012422 | 0.014136 | −0.022807 | −0.066647 | 0.000265 | −0.038946 | 0.014447 | 0.073382 | 0.038489 | −0.046105 | −0.004242 | 0.015092 | 0.075275 |
| 307 | 0.00576 | 0.058978 | −0.068144 | −0.057967 | −0.042424 | −0.082414 | −0.022375 | −0.022323 | 0.133158 | −0.041612 | −0.019554 | −0.128513 | 0.013658 | 0.008385 |
| 308 | −0.182681 | −0.026421 | 0.011638 | −0.031628 | −0.027433 | 0.019169 | −0.043794 | −0.003104 | 0.009393 | 0.003655 | 0.008288 | −0.003746 | −0.008326 | 0.033295 |
| 309 | −0.077254 | −0.02602 | 0.0291 | 0.035998 | 0.021149 | 0.0058 | −0.012657 | 0.008912 | 0.014397 | 0.012951 | 0.032138 | 0.001594 | 0.011456 | −0.005889 |
| 310 | −0.137878 | −0.019056 | 0.025841 | 0.002932 | 0.007882 | 0.015371 | −0.022173 | 0.021054 | 0.017166 | 0.044507 | 0.071778 | −0.024131 | −0.01253 | 0.074243 |
| 311 | 0.045709 | 0.003821 | 0.026048 | 0.026845 | 0.041291 | −0.041287 | 0.008479 | 0.032197 | 0.019369 | 0.002834 | 0.042856 | 0.023812 | 0.021626 | −0.036031 |
| 312 | 0.088749 | 0.048434 | 0.016814 | 0.057464 | 0.008945 | 0.025953 | 0.033386 | 0.069916 | −0.021669 | −0.005311 | 0.027634 | 0.015356 | 0.102885 | −0.001363 |
| 313 | 0.018985 | −0.000199 | 0.023048 | 0.063029 | 0.076663 | 0.015937 | 0.011256 | 0.019033 | −0.000262 | −0.002575 | 0.028936 | 0.018792 | 0.022047 | −0.018162 |
| 314 | 0.152431 | 0.05751 | 0.015736 | 0.092024 | 0.08072 | −0.006333 | 0.042646 | −0.022855 | −0.002197 | 0.022945 | 0.074758 | −0.0075411 | 0.061426 | −0.060042 |
| 315 | −0.005166 | −0.002209 | 0.029911 | 0.034921 | 0.073988 | 0.017928 | 0.001366 | −0.009464 | 0.024819 | 0.006698 | 0.000025 | −0.006036 | −0.006917 | −0.037588 |
| 316 | 0.085435 | −0.032058 | −0.045055 | 0.039854 | 0.030596 | −0.076218 | 0.028274 | −0.106076 | 0.032743 | 0.074626 | 0.098585 | 0.001481 | 0.117875 | −0.015222 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 317 | −0.003783 | −0.036653 | 0.016803 | 0.047153 | 0.060707 | −0.031917 | 0.013705 | 0.016426 | 0.015991 | 0.017349 | 0.016755 | 0.037488 | −0.008946 | −0.036976 |
| 318 | −0.040634 | 0.008579 | 0.03084 | 0.027443 | 0.047285 | −0.026446 | 0.002321 | 0.053705 | 0.025527 | 0.012774 | 0.003634 | −0.014363 | −0.014322 | −0.053445 |
| 319 | −0.011073 | −0.032616 | 0.010775 | 0.048834 | 0.082954 | 0.02881 | −0.00371 | −0.022797 | 0.009055 | 0.018272 | 0.022423 | −0.006012 | −0.022156 | −0.027706 |
| 320 | −0.052441 | −0.045936 | 0.016469 | 0.031122 | 0.045496 | 0.02062 | −0.013661 | −0.010489 | 0.065574 | 0.031459 | 0.02225 | −0.000853 | −0.035735 | 0.012486 |
| 321 | −0.060143 | 0.059191 | −0.011144 | −0.031493 | −0.020919 | −0.063813 | 0.049639 | 0.000013 | 0.068945 | 0.035665 | −0.033196 | 0.00033 | 0.038482 | 0.011823 |
| 322 | 0.088867 | −0.018799 | −0.059946 | 0.057336 | 0.029829 | −0.058512 | 0.057484 | 0.097204 | −0.003332 | −0.051885 | 0.066438 | 0.064333 | 0.118385 | −0.042835 |
| 323 | 0.029373 | 0.052293 | 0.000136 | −0.010576 | −0.03333 | −0.070156 | 0.098909 | 0.02434 | 0.097037 | −0.02627 | 0.041005 | −0.03694 | 0.092594 | 0.024851 |
| 324 | −0.00059 | −0.045126 | −0.007294 | 0.042134 | −0.038593 | −0.005742 | 0.019925 | −0.021212 | 0.048761 | 0.047827 | 0.052671 | 0.005753 | 0.039767 | 0.065367 |
| 325 | 0.003102 | −0.021388 | 0.048469 | 0.038516 | 0.066471 | 0.02852 | −0.008249 | 0.032031 | −0.008356 | 0.006177 | −0.01295 | −0.009384 | 0.001859 | −0.040741 |
| 326 | 0.124182 | 0.035213 | 0.052912 | 0.055353 | 0.073612 | −0.005358 | 0.078983 | 0.023762 | −0.024711 | 0.007805 | −0.064147 | −0.047693 | 0.024935 | −0.029718 |
| 327 | −0.073761 | −0.005984 | 0.019609 | 0.000186 | 0.017251 | −0.017075 | −0.000385 | −0.010502 | 0.035965 | −0.005261 | 0.021609 | −0.003724 | 0.017856 | 0.004613 |
| 328 | 0.019819 | 0.127321 | 0.003046 | −0.00388 | 0.064742 | −0.106261 | 0.023448 | 0.044694 | 0.074332 | −0.037705 | −0.033298 | −0.030344 | 0.069388 | 0.101539 |
| 329 | 0.010514 | 0.002952 | −0.000243 | 0.022482 | 0.05617 | −0.038189 | 0.069485 | −0.001274 | 0.005126 | −0.018227 | 0.0508631 | 0.003566 | 0.045775 | −0.010175 |
| 330 | 0.055209 | 0.044333 | −0.052058 | 0.080839 | 0.076128 | −0.047153 | 0.070541 | 0.09904 | −0.031328 | 0.004935 | −0.021877 | −0.012485 | −0.090001 | 0.078272 |
| 331 | 0.020869 | −0.012114 | 0.034647 | 0.016025 | 0.072146 | −0.003274 | 0.008924 | 0.0004 | 0.019068 | 0.001598 | −0.011523 | −0.014664 | −0.000597 | −0.039909 |
| 332 | 0.050071 | 0.021349 | 0.008978 | 0.144234 | 0.149618 | −0.077474 | 0.067564 | 0.069998 | 0.010363 | −0.01989 | 0.010522 | 0.02545 | −0.060995 | 0.063502 |
| 333 | 0.046458 | −0.03105 | 0.041915 | 0.030987 | 0.065442 | −0.017121 | 0.005839 | 0.054341 | 0.018974 | 0.000295 | −0.012119 | 0.004333 | −0.008659 | −0.063139 |
| 334 | 0.053487 | −0.021254 | 0.043214 | 0.01648 | 0.080017 | 0.034799 | −0.023672 | 0.018806 | 0.067675 | −0.019548 | 0.029691 | 0.033696 | −0.042626 | −0.063086 |
| 335 | −0.040802 | −0.024497 | 0.035247 | 0.006714 | 0.048137 | 0.008513 | 0.011497 | 0.003991 | 0.00645 | 0.000337 | 0.004382 | −0.028444 | −0.011499 | −0.025147 |
| 336 | 0.096649 | 0.072011 | 0.032818 | 0.045005 | 0.012971 | −0.046567 | −0.01672 | 0.088514 | 0.034177 | 0.033123 | −0.053815 | 0.013035 | 0.01523 | −0.059094 |
| 337 | 0.0377864 | 0.015788 | −0.059211 | −0.021011 | −0.045612 | −0.055011 | 0.03385 | −0.023309 | 0.114057 | 0.075132 | −0.018118 | −0.003748 | 0.018427 | 0.055249 |
| 338 | 0.01169 | 0.064932 | 0.012503 | −0.028703 | −0.042812 | 0.009462 | −0.054615 | 0.116068 | 0.056607 | 0.017289 | −0.007369 | 0.188591 | 0.134441 | 0.059202 |
| 339 | 0.038366 | 0.051998 | −0.023297 | −0.011595 | −0.02229 | −0.041304 | 0.03359 | −0.005545 | 0.062025 | 0.019793 | 0.05968 | −0.031654 | 0.083735 | 0.008747 |
| 340 | −0.07094 | 0.033965 | −0.009831 | 0.070704 | −0.006766 | −0.023978 | 0.093913 | 0.050573 | −0.006227 | 0.15477 | −0.071676 | −0.043815 | −0.094374 | 0.024154 |

| | Z | AA | AB | AC | AD | AE | AF | AG | AH | AI | AJ | AK | AL | AM |
|---|---|---|---|---|---|---|---|---|---|---|---|---|---|---|
| 1 | −0.0729631 | 0.009427 | −0.002843 | −0.001952 | −0.018722 | 0.038465 | 0.025806 | −0.027368 | −0.056191 | 0.0114711 | −0.037041 | −0.034119 | −0.011322 | 0.032879 |
| 2 | 0.007843 | 0.004203 | 0.005459 | 0.023855 | 0.013064 | −0.013457 | 0.013177 | −0.06387 | 0.01105 | −0.065348 | −0.031394 | −0.034293 | 0.037969 | 0.021828 |
| 3 | 0.037949 | 0.037198 | 0.048035 | 0.011304 | −0.051909 | −0.008632 | 0.03706 | −0.017395 | −0.020441 | −0.009068 | 0.000179 | −0.058803 | −0.027917 | 0.028628 |
| 4 | −0.068871 | 0.036043 | −0.049544 | −0.095754 | 0.056213 | −0.027428 | −0.050827 | −0.060291 | −0.018623 | 0.079478 | −0.069757 | 0.009416 | 0.032442 | 0.004338 |
| 5 | −0.001798 | −0.057229 | 0.112796 | −0.046955 | 0.035214 | −0.08452 | −0.054203 | 0.010461 | −0.004225 | 0.024779 | −0.130544 | −0.046473 | 0.015461 | −0.073564 |
| 6 | 0.049548 | 0.019096 | 0.067812 | 0.01891 | −0.053905 | −0.008583 | −0.028747 | −0.092402 | −0.099712 | 0.031847 | 0.025362 | 0.082518 | 0.040654 | −0.04865 |
| 7 | 0.112424 | −0.01425 | 0.00073 | 0.029542 | −0.014401 | −0.011248 | −0.055163 | −0.143054 | −0.034281 | 0.050381 | 0.01573 | 0.053557 | 0.022241 | −0.036464 |
| 8 | −0.0128261 | −0.0800141 | −0.043719 | −0.050185 | 0.024027 | −0.047247 | 0.066582 | −0.147292 | 0.013854 | 0.092076 | 0.176532 | 0.033757 | 0.107113 | 0.2034 |
| 9 | −0.058345 | −0.014285 | −0.021761 | −0.111755 | 0.000894 | −0.027828 | −0.04926 | −0.004609 | 0.011508 | 0.077078 | −0.134276 | 0.030131 | 0.03758 | 0.078794 |
| 10 | 0.026565 | −0.009426 | −0.034026 | 0.043829 | −0.120408 | −0.024978 | 0.016741 | −0.08196 | 0.037731 | −0.041577 | −0.019126 | −0.026364 | 0.011599 | 0.049596 |
| 11 | 0.034635 | 0.016977 | −0.01687 | −0.108073 | −0.025523 | 0.070689 | −0.036855 | −0.03331 | −0.109252 | −0.172372 | −0.088122 | 0.082254 | 0.04155 | 0.032732 |
| 12 | 0.128114 | −0.03095 | 0.041116 | 0.048834 | 0.172096 | 0.049372 | −0.090147 | 0.086677 | 0.107614 | 0.0506191 | 0.038229 | −0.1318491 | 0.0647931 | 0.010632 |
| 13 | 0.021516 | −0.049407 | −0.037359 | 0.005339 | −0.026263 | 0.01865 | −0.007556 | 0.002316 | 0.005196 | −0.068359 | 0.067168 | 0.000518 | 0.004979 | −0.011979 |
| 14 | −0.005665 | −0.038248 | −0.066283 | 0.058739 | 0.004066 | 0.001002 | −0.028518 | −0.02014 | 0.03955 | −0.080797 | 0.077675 | −0.006742 | 0.008872 | −0.046252 |
| 15 | −0.070054 | −0.039155 | 0.020356 | 0.027959 | −0.02727 | 0.017439 | 0.055371 | −0.02115 | −0.02942 | 0.00038 | −0.059825 | −0.031155 | −0.023822 | −0.032645 |
| 16 | −0.0343421 | 0.0414991 | −0.11914 | −0.057882 | 0.045398 | 0.128902 | −0.098334 | 0.064693 | 0.086828 | −0.070841 | 0.094809 | −0.036231 | −0.114231 | −0.16629 |
| 17 | 0.007908 | 0.013635 | 0.107649 | −0.030952 | 0.059899 | 0.008589 | 0.070496 | −0.014582 | 0.022698 | −0.014626 | −0.044197 | 0.009366 | 0.083066 | 0.00023 |
| 18 | 0.0000291 | 0.0530051 | −0.082178 | 0.02118 | 0.069531 | −0.021066 | −0.023528 | 0.190063 | 0.031549 | −0.00439 | 0.050892 | −0.020281 | 0.005912 | −0.062362 |
| 19 | 0.016526 | 0.041213 | 0.001937 | 0.003428 | −0.078225 | −0.014022 | 0.060489 | −0.061533 | −0.05429 | −0.055782 | −0.035171 | −0.04536 | −0.112872 | 0.068912 |
| 20 | −0.036506 | 0.01586 | 0.027726 | −0.003625 | −0.035382 | −0.012187 | −0.012106 | −0.028624 | −0.035545 | −0.013797 | 0.006427 | −0.000103 | 0.007429 | 0.015949 |
| 21 | 0.087053 | 0.000067 | 0.008488 | 0.02041 | −0.02999 | −0.072474 | 0.048525 | −0.147016 | −0.021629 | −0.07945 | 0.006441 | −0.10435 | −0.001437 | 0.018846 |
| 22 | 0.010628 | −0.01233 | 0.00791 | −0.056992 | 0.02724 | 0.005914 | 0.118334 | 0.00343 | −0.056245 | 0.005059 | −0.055577 | 0.04247 | −0.049701 | −0.042391 |
| 23 | 0.046011 | 0.03328 | −0.013927 | 0.124618 | 0.006353 | −0.030917 | −0.006512 | −0.016582 | −0.106143 | −0.024088 | 0.015719 | 0.023442 | −0.149333 | −0.105733 |
| 24 | −0.022423 | −0.01551 | −0.038235 | −0.094632 | 0.021663 | −0.080294 | 0.00815 | −0.077756 | 0.005877 | −0.028068 | −0.094741 | −0.028944 | −0.033555 | −0.008152 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 25 | −0.014995 | 0.016448 | −0.034971 | −0.016079 | −0.136546 | −0.114899 | −0.090649 | 0.034786 | −0.029761 | −0.0487 | −0.048405 | −0.064222 | 0.010281 | −0.083528 |
| 26 | −0.020714 | 0.016715 | 0.025372 | −0.007609 | −0.025571 | 0.004166 | −0.010866 | −0.011728 | −0.019482 | −0.00576 | −0.014176 | 0.004588 | −0.008431 | 0.008758 |
| 27 | −0.029886 | 0.016185 | 0.033899 | −0.004645 | −0.026123 | 0.000868 | −0.018163 | −0.000809 | 0.012978 | −0.001462 | −0.003608 | 0.011725 | 0.018409 | 0.002437 |
| 28 | −0.047623 | 0.015146 | −0.037259 | −0.075912 | 0.028348 | 0.004649 | 0.000781 | −0.044004 | −0.034003 | 0.082032 | −0.046039 | 0.003709 | 0.062698 | −0.046653 |
| 29 | −0.010768 | 0.026905 | 0.035038 | −0.063126 | 0.05958 | −0.00742 | −0.029116 | 0.0154 | −0.029487 | −0.017007 | −0.073649 | −0.057171 | 0.079325 | −0.117899 |
| 30 | 0.012125 | 0.046093 | −0.056744 | −0.036936 | −0.055195 | −0.018074 | 0.021651 | −0.019255 | 0.020151 | 0.052052 | 0.045753 | 0.038609 | −0.009954 | −0.055132 |
| 31 | −0.005386 | −0.043288 | 0.009135 | −0.009205 | 0.044654 | −0.001158 | 0.025739 | 0.068959 | −0.018612 | −0.034604 | 0.016108 | −0.0375 | 0.014087 | −0.022669 |
| 32 | −0.022862 | 0.039005 | 0.001686 | 0.143383 | 0.027216 | −0.129495 | −0.034666 | 0.036425 | 0.022715 | −0.054111 | 0.045234 | −0.034343 | −0.124828 | −0.048848 |
| 33 | 0.022601 | −0.016382 | −0.015273 | −0.043072 | −0.087948 | 0.034892 | −0.07256 | 0.009625 | −0.125569 | −0.16933 | −0.049013 | 0.023681 | 0.038121 | 0.043958 |
| 34 | −0.006933 | 0.027414 | −0.093531 | 0.036321 | −0.004089 | −0.042595 | −0.000288 | 0.005633 | 0.034804 | −0.037575 | −0.036782 | −0.003133 | 0.008046 | −0.052967 |
| 35 | 0.067941 | −0.014603 | −0.060908 | −0.041335 | −0.044185 | 0.002031 | −0.045506 | 0.059126 | 0.058426 | 0.016403 | −0.014523 | −0.073882 | −0.003979 | 0.051559 |
| 36 | −0.069507 | 0.031765 | 0.0377071 | 0.082109 | −0.007983 | −0.05639 | 0.019025 | −0.021537 | 0.029872 | −0.032498 | 0.012399 | 0.02944 | 0.058425 | −0.090525 |
| 37 | −0.035407 | −0.013519 | 0.019409 | −0.068059 | 0.024194 | −0.007906 | 0.032123 | −0.060613 | −0.016805 | −0.025921 | 0.0414951 | −0.004839 | 0.0311571 | −0.067781 |
| 38 | −0.079658 | 0.045914 | 0.039912 | 0.030261 | −0.113894 | −0.09492 | −0.054237 | −0.050562 | 0.105199 | −0.136156 | 0.047534 | −0.020178 | 0.008829 | 0.127633 |
| 39 | 0.018071 | −0.027472 | 0.042684 | 0.007162 | −0.0255 | −0.017149 | −0.082371 | −0.055067 | 0.090897 | −0.027183 | 0.016659 | 0.046329 | −0.018521 | 0.014573 |
| 40 | −0.025235 | 0.025937 | −0.009847 | 0.073334 | 0.026501 | 0.013772 | 0.009679 | 0.051455 | 0.011456 | −0.055442 | −0.020917 | −0.032913 | 0.020901 | 0.015565 |
| 41 | 0.042113 | 0.041417 | 0.010603 | 0.040806 | 0.009618 | −0.020411 | −0.006553 | 0.029955 | 0.041395 | −0.054422 | 0.022263 | −0.013362 | 0.003823 | 0.027225 |
| 42 | 0.012159 | 0.020518 | 0.035392 | −0.005773 | 0.002686 | −0.044889 | −0.061744 | −0.000909 | 0.018532 | −0.01255 | 0.001688 | 0.055302 | −0.050748 | 0.005338 |
| 43 | 0.020104 | 0.023499 | −0.005676 | 0.070511 | 0.02362 | −0.008398 | 0.00477 | 0.070317 | 0.023048 | −0.032804 | −0.005803 | −0.021631 | 0.023734 | −0.001159 |
| 44 | −0.012714 | −0.004593 | 0.017806 | 0.004656 | 0.052016 | −0.015515 | −0.011488 | 0.006869 | −0.025584 | −0.033272 | −0.024052 | −0.089035 | −0.029499 | −0.024081 |
| 45 | 0.029333 | 0.002654 | −0.03333 | 0.062788 | 0.010262 | −0.026068 | −0.029299 | 0.106884 | 0.020474 | −0.049431 | 0.004148 | −0.037232 | 0.015848 | −0.046808 |
| 46 | −0.001124 | −0.026861 | −0.037159 | −0.092618 | 0.050257 | 0.029354 | 0.102361 | −0.007321 | 0.078703 | 0.042362 | −0.037829 | 0.037335 | −0.008487 | −0.087585 |
| 47 | 0.060075 | −0.055047 | 0.056481 | 0.03006 | −0.004523 | 0.006227 | −0.048248 | −0.027941 | −0.013015 | 0.042233 | 0.024567 | −0.017021 | −0.012991 | −0.067758 |
| 48 | 0.002169 | 0.002019 | 0.049005 | −0.034544 | −0.047612 | −0.040849 | −0.10984 | −0.057326 | 0.0594631 | −0.0349511 | 0.0082211 | 0.0342641 | −0.0085551 | 0.046588 |
| 49 | 0.02475 | 0.0605041 | −0.0471761 | −0.032671 | −0.055325 | −0.019182 | 0.04169 | −0.015265 | 0.030198 | 0.07861 | 0.049634 | 0.047531 | −0.024016 | −0.032582 |
| 50 | −0.002147 | −0.004855 | −0.033518 | −0.01615 | −0.061369 | 0.003227 | 0.0432 | −0.041786 | −0.071055 | 0.066554 | −0.003505 | 0.000595 | 0.010837 | −0.052351 |
| 51 | 0.05159 | −0.005232 | −0.008163 | 0.026312 | −0.077909 | −0.039999 | −0.026239 | 0.031782 | 0.001498 | 0.021801 | 0.009671 | 0.02209 | 0.037573 | −0.044952 |
| 52 | −0.005221 | −0.014843 | −0.070696 | −0.082514 | −0.011727 | 0.019144 | 0.116029 | −0.055133 | −0.014629 | −0.020595 | 0.045023 | 0.057954 | 0.009873 | −0.053124 |
| 53 | 0.066912 | 0.014076 | −0.053994 | 0.022754 | −0.021286 | −0.025033 | 0.031633 | −0.026145 | 0.003731 | 0.037458 | −0.020793 | −0.022421 | −0.037416 | −0.004322 |
| 54 | −0.035528 | 0.054021 | −0.009584 | −0.064695 | −0.074049 | −0.101952 | −0.024931 | −0.028915 | 0.006133 | 0.043749 | 0.087691 | 0.038252 | −0.084596 | 0.042701 |
| 55 | −0.00645 | −0.022131 | −0.100003 | −0.012988 | −0.002819 | 0.021469 | 0.034346 | −0.059606 | 0.000314 | −0.000784 | −0.008622 | 0.016736 | 0.012105 | −0.024495 |
| 56 | 0.02275 | 0.05019 | −0.027354 | 0.005631 | −0.064093 | −0.002482 | 0.052761 | 0.010938 | 0.023853 | 0.096941 | 0.068887 | 0.023556 | −0.032636 | −0.012027 |
| 57 | 0.023049 | −0.001931 | 0.008237 | −0.033151 | 0.02779 | 0.04534 | −0.054175 | −0.039774 | −0.066697 | −0.073468 | −0.023746 | −0.014747 | 0.026045 | 0.022406 |
| 58 | −0.008504 | −0.034805 | 0.003863 | −0.024134 | −0.005564 | −0.033506 | 0.013543 | 0.04941 | 0.024267 | −0.0118281 | 0.0100231 | 0.0073011 | 0.0244491 | −0.067481 |
| 59 | −0.0531391 | 0.07029 | 0.025781 | −0.066261 | 0.005832 | −0.027971 | −0.08386 | −0.104135 | −0.093008 | −0.034447 | −0.020312 | −0.091027 | −0.076226 | 0.032225 |
| 60 | −0.095007 | −0.070639 | 0.016612 | −0.000426 | −0.000201 | −0.00637 | −0.005342 | −0.0201 | 0.047336 | −0.056225 | 0.02081 | 0.029524 | 0.007044 | −0.045136 |
| 61 | −0.096421 | −0.02459 | 0.065544 | −0.061287 | −0.005521 | −0.010614 | 0.051549 | 0.039219 | 0.052168 | 0.027712 | 0.055095 | 0.025729 | 0.007424 | 0.046223 |
| 62 | −0.02401 | −0.038727 | 0.06328 | 0.015156 | −0.035002 | −0.072542 | −0.0321 | −0.000038 | 0.040463 | 0.0027 | 0.039553 | −0.033404 | −0.080987 | −0.048174 |
| 63 | −0.035552 | 0.040278 | 0.03251 | −0.099719 | −0.025845 | −0.026872 | 0.031384 | 0.04907 | 0.047359 | 0.059975 | 0.047851 | 0.04022 | −0.0673 | 0.050935 |
| 64 | 0.023552 | 0.02943 | −0.021564 | −0.02548 | −0.03071 | −0.032979 | 0.012947 | 0.016749 | 0.033167 | 0.071078 | 0.057364 | 0.044933 | −0.004928 | −0.030955 |
| 65 | −0.019467 | −0.035855 | −0.000977 | −0.012706 | 0.055555 | 0.02082 | −0.088914 | −0.009624 | −0.040928 | −0.074869 | −0.002068 | 0.037747 | 0.044362 | 0.023559 |
| 66 | −0.019944 | −0.004001 | 0.040295 | −0.040621 | 0.041877 | 0.025181 | −0.013934 | −0.068385 | −0.072911 | −0.068166 | 0.023046 | −0.043227 | −0.051503 | −0.001947 |
| 67 | −0.068283 | −0.101118 | −0.006137 | 0.082195 | 0.029108 | 0.032625 | 0.093487 | 0.04292 | 0.011705 | −0.004979 | −0.028698 | −0.041122 | 0.035142 | −0.069029 |
| 68 | −0.012368 | −0.17421 | 0.026543 | 0.007166 | 0.023034 | 0.111919 | 0.187727 | −0.058224 | −0.204537 | 0.018356 | 0.058733 | 0.0493 | −0.007586 | 0.04048 |
| 69 | −0.021249 | −0.04438 | −0.0303 | 0.015386 | −0.01709 | 0.048152 | 0.084033 | −0.026944 | 0.122264 | 0.090663 | 0.00929 | 0.048914 | 0.001094 | 0.023131 |
| 70 | 0.039382 | −0.00221 | −0.085916 | 0.052774 | −0.061314 | 0.061484 | −0.022731 | −0.015868 | 0.00014 | 0.060169 | −0.042868 | 0.050599 | −0.041488 | 0.02678 |
| 71 | 0.073267 | −0.05099 | −0.027184 | −0.035772 | 0.031644 | −0.024638 | 0.037524 | 0.017788 | 0.066336 | −0.055474 | 0.104866 | −0.030441 | 0.088054 | −0.022843 |
| 72 | 0.054732 | −0.06124 | −0.02095 | −0.042786 | 0.067904 | −0.032881 | 0.12543 | 0.050247 | 0.041438 | 0.001686 | 0.048894 | −0.012568 | −0.001675 | 0.032968 |
| 73 | 0.111741 | −0.06106 | −0.01332 | −0.047503 | 0.06447 | 0.029391 | 0.082944 | −0.066316 | 0.0068711 | −0.0433211 | 0.1057791 | 0.004003 | 0.0196561 | 0.00082 |
| 74 | −0.0512081 | 0.014344 | −0.040617 | −0.144935 | −0.042672 | 0.067218 | −0.056843 | 0.144685 | −0.150668 | −0.014754 | 0.074701 | −0.089992 | −0.027789 | −0.045694 |
| 75 | 0.000257 | −0.037596 | −0.075418 | 0.022912 | 0.004425 | 0.026632 | −0.038998 | −0.006216 | 0.014341 | −0.022069 | 0.030647 | 0.013159 | 0.01535 | −0.03367 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 76 | 0.029838 | −0.024834 | −0.048039 | 0.026954 | 0.046558 | 0.050865 | −0.085515 | 0.093481 | −0.005957 | 0.03513 | −0.010333 | −0.0466 | 0.074164 | −0.011149 |
| 77 | 0.003597 | −0.016898 | −0.074097 | 0.015524 | −0.009938 | 0.025688 | −0.042473 | −0.01583 | 0.030503 | −0.003742 | 0.00753 | 0.018677 | 0.024961 | −0.023136 |
| 78 | 0.005588 | −0.021759 | −0.078027 | 0.012358 | −0.007319 | 0.013965 | −0.032741 | −0.013653 | 0.016574 | −0.012006 | 0.002703 | 0.024159 | 0.026877 | −0.040669 |
| 79 | −0.038697 | −0.039344 | −0.08387 | 0.019955 | 0.005366 | 0.025441 | −0.03457 | −0.028875 | −0.00475 | −0.013235 | 0.015197 | 0.001155 | −0.009199 | −0.022825 |
| 80 | 0.050534 | 0.042094 | 0.080749 | 0.040024 | −0.15546 | −0.004116 | −0.080715 | 0.084658 | −0.047869 | −0.058479 | −0.023478 | 0.088602 | −0.096391 | 0.007972 |
| 81 | 0.016094 | −0.03804 | −0.080249 | −0.059829 | 0.013579 | 0.039635 | −0.009392 | 0.02715 | −0.046872 | 0.014341 | −0.078039 | 0.063731 | 0.006167 | −0.024259 |
| 82 | −0.031301 | 0.026925 | 0.010524 | 0.046778 | 0.003341 | 0.035007 | −0.073616 | −0.01875 | 0.006099 | 0.023097 | −0.058096 | 0.072164 | −0.017183 | 0.006578 |
| 83 | −0.0241591 | 0.0221091 | 0.0335041 | 0.007704 | −0.015359 | 0.011886 | −0.029508 | 0.016857 | 0.019869 | 0.005774 | −0.006589 | 0.0213881 | 0.0250181 | 0.006628 |
| 84 | −0.032607 | 0.009673 | 0.043616 | 0.001361 | −0.021286 | −0.002317 | −0.056736 | 0.021976 | 0.049282 | 0.020211 | 0.001569 | −0.002102 | 0.007983 | 0.059402 |
| 85 | −0.051686 | −0.087132 | 0.029781 | 0.000834 | 0.045266 | 0.065798 | 0.038753 | 0.114529 | 0.059719 | 0.04909 | 0.012937 | −0.003535 | −0.001023 | 0.074676 |
| 86 | 0.043269 | −0.040428 | −0.001323 | 0.036688 | 0.020095 | 0.036806 | 0.078475 | 0.029475 | 0.083294 | −0.070728 | 0.031247 | −0.040489 | −0.002467 | 0.029127 |
| 87 | −0.005728 | −0.012531 | −0.039698 | 0.021611 | 0.008185 | 0.026835 | 0.016435 | 0.056222 | 0.036789 | 0.004073 | 0.132951 | −0.067617 | 0.127894 | 0.010791 |
| 88 | −0.004173 | 0.016345 | 0.031926 | 0.008865 | 0.00147 | 0.002769 | −0.061648 | −0.000063 | 0.001102 | 0.010038 | −0.011425 | 0.030418 | 0.023657 | 0.007214 |
| 89 | −0.026793 | 0.012671 | 0.03966 | 0.005294 | −0.025522 | 0.010043 | −0.036527 | 0.004873 | 0.004129 | 0.016919 | −0.009619 | 0.010267 | 0.041251 | 0.020681 |
| 90 | −0.0548481 | 0.014918 | 0.051141 | 0.002576 | −0.033035 | −0.013091 | −0.007234 | −0.000648 | 0.004189 | 0.049 | 0.032002 | −0.025452 | 0.065535 | 0.013892 |
| 91 | 4.044995 | 0.039648 | 0.0112961 | 0.037757 | −0.030444 | 0.03039 | −0.017626 | 0.011296 | 0.022369 | 0.002091 | −0.054883 | 0.052009 | −0.065641 | 0.053701 |
| 92 | −0.004311 | −0.04034 | −0.094008 | 0.051567 | 0.050595 | −0.021868 | 0.097788 | 0.039993 | −0.114236 t | 0.051534 | −0.098972 | −0.057957 | −0.087299 | 0.03218 |
| 93 | −0.037337 | −0.051664 | 0.035695 | 0.005776 | −0.019554 | 0.042111 | 0.062854 | 0.093005 | −0.016845 | 0.007322 | 0.003408 | 0.029353 | −0.007104 | −0.014744 |
| 94 | 0.018501 | −0.035098 | 0.000852 | −0.029841 | 0.006359 | 0.044374 | −0.024569 | −0.023785 | −0.024921 | 0.049681 | −0.020594 | 0.0638 | −0.088164 | −0.029259 |
| 95 | −0.014898 | −0.058514 | −0.012388 | −0.032124 | −0.082176 | 0.091297 | −0.005039 | −0.053552 | 0.092774 | −0.034227 | −0.004946 | −0.055666 | −0.037019 | −0.052023 |
| 96 | −0.090372 | −0.032459 | 0.161691 | 0.053125 | −0.143642 | 0.064524 | 0.040784 | −0.099271 | −0.044866 | 0.047051 | 0.042079 | 0.00939 | 0.102707 | −0.010029 |
| 97 | −0.02166 | −0.031025 | 0.049291 | 0.041509 | −0.057624 | −0.05433 | −0.045827 | −0.030429 | −0.013644 | 0.070282 | 0.0319711 | 0.002481 | 0.0407071 | −0.049219 |
| 98 | 0.007236 | −0.000108 | 0.004707 | 0.005152 | 0.029478 | −0.027737 | −0.045071 | −0.021447 | 0.004328 | −0.006138 | 0.008067 | −0.040504 | −0.026288 | −0.025789 |
| 99 | −0.061252 | 0.010127 | 0.028634 | −0.000869 | 0.008721 | 0.017152 | 0.031404 | −0.041942 | −0.017724 | 0.042296 | 0.027534 | −0.049398 | 0.009383 | 0.001067 |
| 100 | −0.0351371 | 0.0417561 | 0.0112611 | −0.072413 | −0.041946 | −0.005791 | 0.002484 | −0.021627 | 0.03425 | −0.007966 | 0.041146 | −0.00158 | −0.043136 | −0.028139 |
| 101 | 0.03525 | −0.020561 | 0.0228811 | −0.017784 | −0.015416 | −0.036571 | −0.048444 | 0.011161 | −0.023021 | 0.002838 | 0.029305 | −0.039617 | −0.034852 | −0.004338 |
| 102 | 0.000318 | 0.084539 | −0.050628 | −0.001089 | −0.060258 | 0.038254 | 0.035012 | −0.008436 | 0.076317 | 0.048742 | 0.003231 | 0.078226 | 0.043411 | 0.081562 |
| 103 | 0.013603 | 0.019897 | −0.072733 | −0.006046 | −0.05785 | 0.116873 | −0.035936 | −0.120082 | 0.146598 | 0.103184 | 0.0636 | 0.017516 | 0.054606 | −0.062975 |
| 104 | −0.038524 | 0.052662 | 0.003876 | 0.002382 | −0.032845 | 0.122205 | −0.018817 | −0.040964 | 0.100096 | −0.028939 | 0.062898 | −0.052867 | −0.031274 | −0.12872 |
| 105 | 0.146577 | 0.042559 | 0.107535 | −0.005903 | 0.078305 | −0.017483 | −0.076587 | 0.027917 | 0.054413 | −0.095296 | 0.116958 | 0.01661 | 0.286353 | −0.046683 |
| 106 | 0.004963 | 0.026756 | −0.086186 | 0.032001 | 0.030622 | 0.033007 | −0.031978 | −0.058065 | 0.033885 | 0.023085 | −0.088238 | 0.041651 | −0.051165 | −0.041184 |
| 107 | −0.03436 | 0.022908 | −0.029889 | −0.078493 | 0.026506 | 0.002034 | −0.033908 | −0.020203 | −0.016784 | 0.016882 | 0.03227f | 0.020807 | −0.034104 | −0.044772 |
| 108 | −0.021808 | 0.030772 | 0.051105 | 0.002266 | −0.01574 | 0.092603 | −0.069272 | 0.089637 | −0.152103 | 0.036047 | 0.030692 | −0.0191 | −0.06922 | −0.04765 |
| 109 | −0.115257 | 0.05313 | 0.092823 | −0.037386 | −0.121592 | 0.103824 | 0.080546 | 0.040963 | 0.018116 | 0.077758 | 0.057026 | 0.017297 | −0.183133 | 0.041988 |
| 110 | 0.00383 | 0.077302 | 0.057951 | −0.047464 | −0.077231 | −0.071696 | 0.068122 | 0.040797 | 0.117362 | 0.019307 | −0.151141 | 0.022287 | −0.051899 | 0.01962 |
| 111 | 0.027818 | 0.012344 | −0.00906 | −0.109136 | 0.032125 | 0.031399 | 0.001678 | 0.047181 | −0.106923 | −0.06688 | −0.017657 | −0.051285 | −0.003269 | 0.040791 |
| 112 | −0.046926 | 0.128161 | 0.040369 | 0.047496 | 0.043281 | 0.048079 | −0.01004 | 0.071069 | 0.082234 | 0.081358 | 0.032871 | −0.033661 | 0.059098 | −0.049148 |
| 113 | −0.034148 | 0.060076 | 0.041022 | 0.051586 | −0.110855 | 0.043761 | 0.053864 | 0.029274 | −0.126587 | 0.103497 | 0.036863 | −0.051689 | −0.020981 | 0.012882 |
| 114 | 0.140749 | 0.065297 | 0.071152 | 0.038154 | −0.030796 | −0.023693 | −0.031034 | 0.042479 | 0.0406061 | 0.0622511 | −0.0178941 | −0.1227651 | 0.020834 | −0.010179 |
| 115 | 0.0163431 | 0.0208491 | 0.004183 | −0.052813 | 0.118289 | 0.05356 | 0.007033 | 0.086549 | 0.080016 | 0.024812 | −0.008144 | −0.04037 | −0.193924 | −0.039163 |
| 116 | 0.057127 | −0.001862 | 0.002113 | −0.025401 | 0.119634 | −0.08459 | −0.024367 | 0.108163 | −0.065599 | 0.060546 | 0.196523 | 0.032068 | −0.034836 | 0.024245 |
| 117 | 0.005631 | 0.045669 | −0.02849 | −0.029521 | 0.009851 | 0.051334 | −0.023296 | 0.026834 | 0.005469 | −0.024765 | 0.032885 | −0.007251 | −0.008302 | 0.072522 |
| 118 | −0.004699 | −0.058137 | −0.01667 | 0.088052 | 0.04909 | −0.021765 | 0.057282 | −0.027651 | −0.037716 | −0.00485 | −0.091018 | −0.142591 | −0.026849 | 0.007613 |
| 119 | −0.044455 | −0.032118 | 0.046392 | −0.088053 | −0.070753 | 0.076586 | 0.080592 | 0.029117 | 0.079847 | 0.084773 | −0.042622 | −0.003548 | −0.054071 | 0.050179 |
| 120 | 0.017507 | 0.077659 | −0.028329 | −0.064517 | −0.027914 | −0.031676 | −0.066698 | 0.031058 | −0.005556 | −0.021773 | 0.053908 | 0.016795 | −0.043603 | 0.059778 |
| 121 | −0.001581 | 0.06404 | −0.002761 | −0.073485 | −0.035886 | 0.001262 | −0.065039 | 0.076902 | 0.028719 | −0.029389 | 0.008982 | −0.018508 | −0.066392 | 0.076082 |
| 122 | 0.033976 | −0.022645 | 0.017633 | −0.004492 | 0.001 | −0.02633 | 0.008058 | −0.009562 | 0.066236 | −0.046326 | −0.052375 | −0.098887 | 0.00979 | 0.035084 |
| 123 | 0.043535 | 0.022035 | 0.023994 | −0.110516 | 0.032737 | −0.047149 | 0.047876 | −0.005584 | 0.077879 | −0.019635 | −0.079602 | −0.063469 | −0.018559 | 0.031463 |
| 124 | −0.010685 | 0.00684 | −0.031969 | −0.0517 | −0.035385 | −0.007869 | −0.007525 | 0.019617 | 0.05744 | 0.017896 | −0.009336 | −0.013293 | −0.007384 | −0.001553 |
| 125 | −0.01846 | 0.05062 | −0.005459 | 0.083654 | −0.001823 | −0.109876 | 0.04842 | 0.041972 | −0.051926 | −0.089594 | 0.033014 | −0.032223 | −0.016053 | 0.012691 |
| 126 | 0.051783 | 0.003748 | −0.028021 | −0.020322 | 0.015995 | −0.022914 | 0.021301 | 0.016824 | 0.025781 | 0.005083 | −0.015053 | −0.054143 | −0.014713 | 0.00915 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 127 | 0.001562 | −0.018455 | −0.069516 | −0.024055 | 0.004025 | −0.00636 | 0.019278 | −0.011644 | 0.064853 | 0.041549 | −0.012401 | −0.025724 | −0.006464 | −0.002968 |
| 128 | −0.046849 | 0.056844 | 0.036001 | −0.038897 | −0.03744 | 0.025906 | 0.058654 | −0.012971 | −0.022041 | −0.006954 | −0.041157 | 0.057509 | −0.059272 | −0.083568 |
| 129 | 0.018138 | −0.137175 | 0.162481 | 0.000664 | −0.073077 | 0.101092 | 0.100963 | 0.046673 | −0.033244 | 0.126664 | −0.004283 | 0.03539 | −0.010048 | −0.220759 |
| 130 | −0.015427 | 0.068841 | 0.053128 | 0.037994 | −0.009014 | 0.037144 | −0.066258 | 0.006263 | −0.0586821 | 0.1308531 | 0.0127461 | 0.0228051 | −0.0913151 | −0.113034 |
| 131 | 0.0512131 | 0.021931 | 0.029657 | 0.037422 | −0.051261 | −0.009585 | −0.071098 | −0.072541 | −0.056652 | 0.061301 | 0.025748 | 0.00221 | 0.068845 | 0.05432 |
| 132 | 0.026915 | 0.089639 | 0.049398 | 0.068142 | −0.090289 | 0.01667 | 0.020482 | −0.044014 | −0.060029 | −0.134953 | 0.044294 | 0.095984 | −0.071749 | 0.032326 |
| 133 | −0.081059 | 0.037052 | 0.019547 | −0.011319 | 0.044574 | 0.042207 | 0.03915 | −0.091352 | 0.028151 | 0.029265 | −0.036133 | 0.09301 | −0.068876 | −0.062489 |
| 134 | 0.019502 | −0.163282 | −0.07247 | −0.008741 | 0.08357 | 0.060559 | 0.021561 | 0.069786 | −0.039941 | 0.021965 | 0.013272 | −0.053277 | 0.011549 | 0.112054 |
| 135 | 0.032933 | 0.032223 | 0.01974 | 0.017687 | 0.01678 | −0.015344 | 0.004748 | 0.007862 | 0.030752 | −0.029271 | 0.02056 | 0.015029 | 0.024011 | −0.02406 |
| 136 | −0.016661 | 0.039906 | 0.011575 | 0.049242 | 0.008431 | −0.065763 | 0.076697 | 0.04567 | −0.018888 | −0.04324 | 0.037466 | −0.042201 | 0.05464 | 0.03359 |
| 137 | 0.020754 | −0.049388 | 0.009379 | −0.043822 | 0.078257 | −0.021815 | 0.054558 | −0.105476 | −0.020584 | 0.150272 | −0.010505 | −0.026831 | −0.047486 | −0.069853 |
| 138 | −0.158667 | −0.091339 | 0.009943 | 0.046488 | −0.13377 | −0.001634 | −0.129491 | 0.074176 | −0.232469 | 0.115497 | 0.099074 | −0.100285 | 0.019284 | 0.026949 |
| 139 | 0.0715431 | −0.113075 | 0.059064 | 0.052618 | −0.086807 | −0.053301 | 0.07856 | 0.032976 | −0.041823 | −0.10082 | −0.066778 | 0.040287 | 0.057615 | 0.044471 |
| 140 | −0.094811 | −0.053539 | −0.007453 | 0.176578 | 0.204801 | 0.041478 | 0.022702 | −0.087547 | −0.098603 | 0.0124491 | −0.082442 | −0.001608 | 0.029182 | 0.041767 |
| 141 | 0.016086 | −0.0093891 | −0.010828 | 0.041966 | 0.006053 | −0.003387 | 0.025896 | −0.033607 | 0.043651 | −0.038076 | −0.013646 | 0.05444 | −0.018878 | 0.002033 |
| 142 | 0.01869 | 0.005643 | 0.06809 | 0.046958 | 0.008141 | 0.049207 | 0.031024 | 0.001287 | 0.025315 | −0.021318 | 0.013398 | −0.099073 | 0.018627 | −0.017691 |
| 143 | −0.003235 | 0.009701 | 0.007483 | 0.009576 | 0.014719 | −0.026718 | −0.001745 | −0.017903 | 0.043451 | −0.018929 | 0.01903 | 0.028339 | 0.001207 | −0.112046 |
| 144 | 0.019905 | −0.006685 | 0.005286 | −0.070613 | 0.031328 | 0.016868 | 0.07115 | 0.019096 | 0.114457 | 0.079328 | 0.046656 | −0.030332 | −0.044337 | −0.078967 |
| 145 | 0.05527 | 0.0524081 | 0.001142 | −0.046714 | −0.054101 | −0.009138 | 0.071605 | 0.004614 | 0.090946 | 0.0382281 | −0.032511 | 0.0317641 | 0.0374921 | −0.099204 |
| 146 | 0.020582 | 0.024447 | −0.010518 | 0.007053 | 0.000688 | −0.000509 | 0.025188 | 0.019754 | −0.041448 | 0.010747 | 0.010061 | −0.003244 | −0.018988 | −0.010278 |
| 147 | −0.012674 | −0.062 | 0.017939 | 0.131418 | 0.020488 | 0.029891 | −0.104235 | 0.031747 | −0.139767 | −0.033825 | 0.021937 | −0.017454 | −0.050257 | −0.008903 |
| 148 | −0.051709 | −0.00142 | 0.019656 | 0.014478 | 0.04594 | −0.026953 | −0.061855 | −0.136125 | 0.000023 | 0.166243 | 0.050658 | −0.199901 | 0.016493 | −0.035157 |
| 149 | 0.048623 | −0.03357 | −0.004317 | −0.034155 | −0.002449 | 0.025547 | −0.020171 | −0.035858 | 0.036783 | −0.01238 | −0.005953 | 0.005724 | 0.022269 | 0.034385 |
| 150 | −0.066482 | 0.043509 | 0.0338 | 0.074298 | −0.011422 | −0.09777 | 0.032728 | 0.133438 | −0.029661 | −0.07542 | 0.032372 | −0.042478 | 0.054539 | 0.002335 |
| 151 | 0.009583 | −0.139506 | 0.041976 | −0.015157 | 0.047371 | 0.019515 | −0.186805 | 0.046468 | 0.097667 | −0.072653 | −0.023253 | 0.102156 | −0.027648 | −0.095638 |
| 152 | −0.042637 | 0.023965 | −0.005772 | 0.046875 | −0.028217 | 0.021757 | −0.016555 | 0.015184 | 0.045658 | −0.012478 | 0.012682 | 0.017107 | −0.000243 | 0.032086 |
| 153 | −0.010601 | 0.017777 | 0.041967 | 0.015133 | 0.001067 | 0.003312 | −0.066704 | 0.012396 | 0.110221 | 0.027582 | 0.018172 | 0.037558 | −0.021642 | 0.031309 |
| 154 | 0.025482 | 0.025363 | 0.0164051 | 0.026072 | 0.031458 | 0.019221 | −0.020004 | 0.068904 | 0.037685 | 0.003103 | 0.037441 | −0.038072 | 0.063302 | 0.055874 |
| 155 | 0.02053 | 0.0497511 | 0.024583 | 0.031754 | −0.023327 | −0.046918 | 0.078537 | −0.025829 | 0.0213691 | 0.0113971 | −0.0087561 | 0.0216271 | −0.0188111 | 0.065038 |
| 156 | −0.0530851 | 0.080013 | −0.0214191 | −0.009024 | −0.028022 | −0.00358 | 0.056652 | 0.000661 | −0.088495 | 0.028792 | −0.026386 | −0.048231 | −0.005106 | 0.033961 |
| 157 | −0.052806 | 0.085711 | −0.043809 | 0.01568 | −0.03768 | −0.079985 | −0.000247 | 0.00346 | 0.077429 | −0.045756 | −0.020045 | −0.037852 | −0.010061 | 0.035927 |
| 158 | −0.106586 | 0.019671 | 0.013998 | 0.007982 | 0.020675 | −0.059606 | −0.114649 | 0.051091 | −0.03283 | −0.061791 | 0.04459 | 0.081851 | −0.190847 | 0.097814 |
| 159 | −0.035465 | −0.131663 | 0.158982 | −0.02271 | −0.049625 | −0.031625 | 0.107317 | 0.02558 | −0.010144 | −0.01833 | −0.07159 | 0.043295 | 0.156604 | −0.11434 |
| 160 | 0.026324 | 0.109744 | 0.015475 | 0.032508 | −0.101831 | −0.115883 | −0.113317 | 0.074054 | 0.001284 | 0.197011 | −0.272185 | −0.16686 | 0.170179 | 0.011221 |
| 161 | −0.101335 | −0.052355 | 0.101804 | −0.011403 | −0.004841 | 0.011165 | −0.056968 | 0.005626 | −0.090401 | 0.103622 | 0.184257 | 0.112936 | −0.018891 | 0.047109 |
| 162 | 0.007215 | −0.120066 | 0.079941 | −0.066109 | −0.006659 | 0.080271 | −0.112842 | 0.051259 | 0.033806 | 0.110444 | 0.02822 | 0.014043 | −0.057763 | 0.103601 |
| 163 | −0.037702 | 0.006441 | 0.027305 | 0.018466 | 0.018502 | 0.098563 | 0.009748 | 0.023256 | 0.092064 | 0.062822 | −0.01837 | −0.036809 | 0.089171 | 0.020357 |
| 164 | −0.008825 | −0.034825 | 0.008644 | 0.065172 | −0.024325 | 0.07143 | 0.052068 | −0.014963 | 0.039404 | 0.065724 | −0.059915 | 0.020615 | 0.087125 | 0.040349 |
| 165 | −0.0463311 | −0.067489 | 0.0793891 | 0.107703 | −0.002032 | 0.135997 | −0.044348 | −0.019982 | 0.1104481 | −0.085822 | 0.0093621 | −0.036324 | −0.055407 | 0.055645 |
| 166 | −0.029195 | −0.020839 | −0.009906 | 0.022806 | −0.100538 | −0.021028 | −0.173631 | −0.01154 | −0.0311281 | 0.0692321 | −0.0245811 | −0.0779461 | 0.0130481 | −0.046619 |
| 167 | −0.023261 | 0.037044 | 0.000571 | 0.039224 | 0.010137 | 0.06121 | 0.140505 | 0.011779 | 0.031293 | 0.04503 | −0.028201 | −0.040819 | −0.062452 | −0.042422 |
| 168 | −0.038794 | −0.01014 | 0.080301 | 0.051615 | −0.028491 | 0.02427 | 0.081314 | −0.037179 | −0.030653 | 0.027151 | 0.044349 | −0.004873 | 0.010026 | −0.093456 |
| 169 | 0.057818 | 0.024257 | 0.017903 | 0.021027 | −0.003594 | 0.035003 | −0.026276 | 0.005734 | −0.015966 | 0.010615 | 0.011042 | 0.027149 | 0.032577 | 0.044106 |
| 170 | 0.054538 | 0.018372 | 0.04535 | 0.061521 | −0.03078 | 0.030532 | −0.036377 | 0.040309 | −0.016335 | 0.007309 | 0.018822 | 0.047446 | −0.003835 | 0.046767 |
| 171 | 0.025709 | 0.005393 | 0.022422 | 0.004205 | 0.013652 | 0.062539 | −0.001712 | 0.010981 | −0.02825 | −0.032377 | −0.002727 | −0.005628 | 0.014415 | −0.006502 |
| 172 | 0.030521 | −0.001064 | −0.051182 | −0.030228 | 0.038926 | 0.048903 | −0.053315 | 0.069801 | 0.020936 | 0.005777 | −0.02152 | 0.107857 | 0.031044 | 0.009463 |
| 173 | −0.027392 | −0.048948 | −0.005194 | −0.047926 | 0.080039 | 0.076337 | −0.020825 | 0.061507 | 0.022657 | −0.001001 | −0.034694 | 0.077114 | −0.009588 | 0.060415 |
| 174 | 0.041777 | −0.026691 | 0.001411 | 0.083224 | 0.066685 | 0.026041 | 0.022656 | 0.049391 | −0.084158 | 0.03061 | −0.032848 | 0.157476 | 4.046697 | 0.057619 |
| 175 | 0.048483 | 0.023168 | −0.061214 | 0.166528 | 0.051581 | 0.008003 | −0.009261 | 0.087592 | −0.07066 | 0.042364 | −0.050305 | 0.141762 | 0.049868 | 0.09448 |
| 176 | −0.04215 | 0.050437 | −0.083835 | 0.029752 | 0.023209 | 0.023802 | 0.018696 | −0.034308 | −0.049648 | −0.030291 | 0.055842 | 0.094272 | 0.066005 | −0.0143 |
| 177 | 0.061676 | −0.111457 | 0.077604 | 0.100146 | −0.00961 | 0.108044 | −0.130552 | 0.004769 | 0.075042 | 0.025487 | −0.040109 | 0.086112 | −0.026963 | −0.00383 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 178 | 0.017872 | −0.031866 | −0.002787 | −0.028561 | 0.049721 | −0.035269 | −0.061813 | −0.095348 | 0.022684 | −0.019336 | −0.022298 | −0.031316 | −0.02346 | −0.040844 |
| 179 | −0.020333 | −0.007203 | 0.064557 | 0.01666 | 0.023432 | −0.011286 | −0.00766 | −0.037391 | 0.007595 | −0.019804 | −0.004272 | −0.075317 | 4.006349 | 0.005492 |
| 180 | −0.007728 | −0.015009 | 0.058564 | 0.021635 | 0.028412 | −0.039634 | −0.031107 | −0.026473 | 0.005306 | −0.01356 | 0.018044 | −0.062245 | −0.021926 | 0.045631 |
| 181 | −0.014788 | −0.01414 | 0.048827 | 0.024157 | 0.026089 | −0.037615 | −0.028061 | −0.015001 | 0.006213 | −0.043529 | −0.005194 | −0.045224 | −0.0346 | 0.031793 |
| 182 | −0.058286 | 0.007176 | 0.062452 | 0.0056 | 0.04114 | 0.008405 | −0.002431 | 0.022471 | 0.027507 | −0.039131 | 0.006544 | −0.005976 | −0.015107 | 0.025902 |
| 183 | −0.06957 | 0.023923 | 0.04817 | −0.030322 | 0.00904 | 0.022866 | 0.043302 | 0.038176 | 0.016919 | −0.060678 | 0.014122 | −0.067911 | 0.011141 | −0.031404 |
| 184 | −0.040119 | 0.060391 | 0.037737 | −0.060428 | −0.052945 | −0.080263 | 0.060478 | 0.054872 | −0.045623 | −0.014302 | −0.012094 | −0.078278 | 0.013426 | −0.101585 |
| 185 | 0.110021 | 0.007078 | −0.041718 | −0.048984 | 0.007698 | −0.045565 | 0.101228 | −0.057277 | 0.032569 | 0.018707 | 0.03829 | 0.026813 | 0.05869 | −0.001437 |
| 186 | −0.033258 | −0.031416 | 0.047892 | 0.032622 | −0.036102 | 0.044493 | −0.027922 | 0.015607 | 0.068518 | −0.011061 | 0.032023 | −0.007985 | −0.052526 | 0.066196 |
| 187 | −0.002073 | 0.039135 | −0.004946 | −0.046124 | 0.029792 | 0.007918 | 0.030138 | 0.101482 | 0.050997 | −0.009993 | 0.041985 | 0.021529 | 0.009856 | 0.088523 |
| 188 | 0.050655 | 0.040628 | 0.00682 | 0.036018 | 0.04854 | −0.016649 | 0.064923 | 0.098089 | −0.002976 | 0.070813 | 0.025672 | 0.092147 | 0.001868 | 0.078614 |
| 189 | 0.066128 | 0.080553 | 0.013711 | 0.093428 | 0.03548 | −0.03954 | 0.057442 | 0.155 | −0.039335 | 0.0909 | −0.003642 | 0.09833 | 0.043257 | 0.096854 |
| 190 | −0.027777 | −0.004135 | −0.010181 | −0.000872 | −0.019981 | 0.00543 | −0.020059 | −0.030346 | 0.019079 | −0.009196 | 0.011362 | 0.036213 | 0.009419 | 0.059977 |
| 191 | −0.004304 | 0.011806 | −0.002877 | 0.0058 | −0.039564 | 0.011355 | −0.035997 | −0.053965 | 0.016272 | −0.012388 | −0.011998 | −0.01911 | 0.019868 | 0.079561 |
| 192 | −0.064237 | 0.049215 | −0.074975 | 0.024167 | −0.024618 | −0.033905 | 0.020127 | 0.030726 | 0.037101 | 0.003544 | 0.054382 | −0.023638 | 0.036334 | −0.073089 |
| 193 | −0.021497 | 0.036139 | −0.094371 | −0.040915 | −0.011311 | 0.001998 | 0.035404 | 0.040481 | 0.036722 | 0.021192 | 0.034189 | 0.04456 | 0.079024 | −0.000189 |
| 194 | 0.01268 | 0.022205 | −0.033575 | 0.026134 | 0.064409 | −0.002744 | 0.020953 | 0.014766 | 0.065226 | 0.025509 | 0.065614 | 0.032462 | 0.042396 | 0.085837 |
| 195 | 0.03677 | −0.034623 | 0.065066 | −0.019864 | 0.023718 | −0.039895 | 0.008603 | 0.025269 | 0.05528 | −0.070671 | −0.111427 | 0.004032 | 0.002679 | 0.05965 |
| 196 | 0.038247 | −0.030643 | 0.056184 | 0.001922 | 0.033464 | −0.026675 | −0.006681 | 0.015841 | 0.048855 | 0.006234 | −0.057175 | 0.001459 | −0.013938 | 0.06939 |
| 197 | −0.040785 | 0.034962 | 0.0133421 | −0.003905 | 0.001077 | 0.042414 | 0.002454 | −0.087118 | 0.049505 | −0.005081 | 0.00151 | 0.060716 | 0.007737 | 0.084589 |
| 198 | 0.093907 | 0.032649 | 0.027456 | 0.02249 | −0.035208 | 0.024361 | −0.035697 | 0.009369 | 0.032128 | −0.104185 | −0.02753 | −0.028288 | −0.03272 | −0.05569 |
| 199 | 0.09833 | −0.089541 | −0.031495 | 0.090926 | −0.045313 | 0.12386 | −0.148462 | 0.011726 | −0.031132 | 0.136533 | 0.152779 | −0.031027 | 0.015418 | −0.050358 |
| 200 | 0.025439 | −0.041146 | 0.098229 | 0.036175 | 0.070312 | 0.009706 | −0.026322 | 0.001597 | 0.03547 | −0.024151 | −0.058222 | 0.064732 | −0.063059 | −0.039953 |
| 201 | 0.101333 | −0.10768 | 0.020542 | 0.034991 | 0.028487 | −0.040676 | 0.028287 | −0.131869 | −0.034333 | −0.106075 | 0.172251 | −0.16872 | 0.062986 | 0.114436 |
| 202 | 0.093589 | −0.007488 | 0.069664 | −0.038002 | 0.0132 | 0.095909 | −0.03818 | 0.019644 | 0.087478 | −0.125344 | −0.065745 | 0.013611 | −0.04622 | −0.019614 |
| 203 | 0.048161 | −0.015276 | −0.122043 | −0.005702 | −0.010023 | −0.038693 | −0.091679 | −0.086366 | 0.081638 | 0.015034 | 0.015523 | 0.05544 | 0.062889 | −0.04455 |
| 204 | 0.077713 | −0.094702 | 0.000891 | −0.051279 | −0.037819 | 0.001254 | 0.106936 | 0.03884 | −0.026411 | −0.115354 | 0.107756 | −0.063453 | −0.041334 | −0.072108 |
| 205 | −0.230994 | −0.161189 | 0.159319 | 0.189012 | 0.02258 | 0.158182 | −0.036938 | −0.135681 | 0.187 | −0.063837 | −0.13526 | 0.029343 | 0.095799 | −0.007515 |
| 206 | 0.017678 | 0.057514 | −0.020083 | 0.057926 | −0.066025 | 0.055856 | 0.02536 | −0.010832 | 0.012557 | −0.072362 | 0.058808 | −0.047066 | −0.006816 | −0.04363 |
| 207 | −0.02237 | −0.185121 | −0.038155 | 0.147229 | −0.005754 | −0.012644 | 0.099892 | 0.128413 | −0.021315 | −0.004124 | −0.114795 | −0.115758 | −0.090611 | 0.052761 |
| 208 | −0.014054 | 0.080121 | −0.100454 | 0.152148 | −0.174242 | 0.063697 | 0.087557 | −0.158918 | 0.119668 | −0.009185 | 0.049813 | 0.072723 | −0.061479 | −0.039636 |
| 209 | −0.118339 | −0.141879 | 0.039104 | 0.047982 | 0.072679 | 0.01667 | −0.133386 | −0.045247 | −0.006536 | −0.066975 | 0.152479 | 0.038218 | −0.009754 | −0.064677 |
| 210 | −0.077574 | 0.073767 | −0.036466 | −0.111967 | −0.117163 | 0.007568 | −0.128969 | 0.02179 | −0.056862 | −0.080194 | 0.055961 | −0.007965 | 0.290679 | 0.054477 |
| 211 | 0.003405 | −0.079173 | −0.113831 | −0.042945 | 0.082458 | −0.000689 | −0.004249 | 0.056827 | −0.045084 | 0.017979 | 0.015578 | −0.073242 | 0.064594 | −0.047641 |
| 212 | −0.060963 | 0.068267 | −0.035149 | 0.260854 | 0.080203 | −0.02531 | 0.001042 | −0.027882 | −0.049067 | 0.03655 | −0.005354 | −0.074246 | 0.091603 | −0.096102 |
| 213 | −0.204516 | −0.027043 | 0.027759 | −0.005434 | −0.072692 | −0.013932 | 0.002288 | −0.135159 | −0.060821 | 0.004429 | −0.161463 | 0.058806 | 0.057062 | 0.139231 |
| 214 | −0.003205 | 0.017653 | 0.050246 | −0.004845 | 0.002211 | −0.038817 | 0.010817 | −0.008747 | 0.018468 | 0.011625 | 0.001453 | −0.10348 | −0.026056 | −0.015739 |
| 215 | −0.040452 | 0.0211691 | −0.008781 | 0.04272 | −0.029726 | −0.027927 | −0.021926 | −0.054883 | 0.021431 | −0.098551 | 0.002701 | −0.065697 | 0.04262 | −0.045349 |
| 216 | 0.03928 | 0.003222 | 0.057807 | −0.013816 | 0.002133 | 0.061076 | −0.003642 | 0.029067 | −0.014333 | −0.013747 | −0.04373 | 0.012244 | 0.005694 | −0.044037 |
| 217 | 0.013427 | 0.005894 | −0.036222 | −0.0932 | −0.113984 | 0.166771 | 0.092028 | 0.056684 | −0.032253 | −0.029219 | −0.049555 | 0.010601 | −0.006944 | 0.044539 |
| 218 | 0.012312 | 0.01087 | −0.015202 | −0.010489 | −0.009501 | 0.026263 | −0.007514 | −0.008083 | 0.027178 | −0.013434 | −0.031897 | 0.017583 | 0.023648 | −0.01833 |
| 219 | 0.035749 | 0.045467 | 0.003007 | −0.013364 | −0.038348 | 0.017453 | −0.021195 | 0.031291 | 0.010727 | −0.013235 | −0.03778 | −0.010557 | −0.031379 | −0.007006 |
| 220 | 0.001532 | −0.021619 | −0.003213 | −0.095372 | −0.057233 | 0.048974 | −0.008283 | 0.062448 | −0.001064 | −0.020511 | −0.008127 | 0.037698 | −0.035732 | −0.018444 |
| 221 | −0.027557 | −0.007318 | 0.007659 | −0.057832 | 0.032046 | 0.04187 | −0.070264 | −0.001398 | −0.037136 | −0.073249 | −0.09166 | −0.015358 | 0.007207 | 0.044834 |
| 222 | −0.112268 | −0.039726 | −0.101813 | 0.028588 | −0.021125 | −0.001332 | −0.034906 | 0.014419 | 0.057373 | 0.022035 | −0.015039 | 0.009815 | 0.058449 | −0.018489 |
| 223 | −0.067644 | −0.032386 | −0.120304 | −0.000765 | 0.010049 | 0.008273 | −0.01304 | −0.001947 | 0.039237 | 0.002428 | −0.007342 | 0.07909 | 0.014319 | −0.02863 |
| 224 | 0.002748 | −0.023941 | −0.035104 | −0.057463 | 0.021495 | 0.10147 | 0.017335 | −0.020804 | −0.046445 | −0.107583 | −0.015652 | −0.136316 | −0.019073 | −0.090703 |
| 225 | 0.024015 | −0.0280591 | −0.040016 | −0.048955 | 0.021022 | 0.111119 | 0.012807 | −0.031527 | −0.044525 | −0.097463 | −0.033281 | −0.123611 | −0.006038 | −0.094796 |
| 226 | −0.001903 | 0.06413 | 0.053143 | −0.050138 | 0.001544 | −0.044267 | 0.00051 | 0.018039 | 0.018259 | 0.012565 | 0.03026 | 0.065399 | 0.017884 | −0.034044 |
| 227 | −0.021788 | 0.060599 | 0.046716 | −0.138813 | 0.059542 | 0.102544 | 0.012344 | 0.0094 | −0.042982 | −0.09942 | 0.053513 | −0.034389 | 0.091369 | −0.052287 |
| 228 | 0.007927 | −0.025311 | −0.133276 | 0.073685 | −0.01584 | −0.030781 | 0.061377 | 0.024985 | 0.043105 | 0.041369 | −0.078837 | 0.028941 | −0.034816 | −0.033483 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 229 | 0.024237 | −0.219186 | −0.01325 | 0.03852 | −0.176958 | −0.189273 | 0.047011 | 0.09471 | 0.087747 | −0.080579 | 0.014906 | 0.009873 | −0.020618 | 0.050718 |
| 230 | 0.004995 | −0.113274 | 0.008962 | 0.021887 | −0.012784 | −0.037655 | −0.006592 | −0.010011 | 0.042308 | 0.011687 | 0.022743 | −0.046081 | 0.026403 | 0.037848 |
| 231 | −0.05903 | 0.079693 | −0.010805 | −0.073317 | 0.076519 | 0.052832 | −0.022582 | 0.020228 | −0.076331 | −0.07315 | 0.041355 | 0.146085 | 0.03768 | 0.010985 |
| 232 | −0.005887 | 0.000828 | −0.073235 | 0.061118 | −0.031678 | 0.021355 | −0.01623 | 0.116284 | 0.034448 | 0.075354 | 0.007908 | −0.051207 | −0.058669 | 0.055479 |
| 233 | 0.01084 | −0.027202 | 0.003357 | 0.02003 | −0.01532 | 0.011521 | −0.018686 | 0.057538 | 0.079919 | 0.010991 | −0.026838 | −0.026614 | 0.018296 | 0.030935 |
| 234 | −0.044172 | 0.098825 | 0.022439 | 0.089503 | 0.077238 | −0.014757 | 0.033182 | −0.047626 | 0.01004 | −0.015474 | 0.033266 | 0.104045 | 4.011313 | −0.04422 |
| 235 | −0.049848 | 0.058598 | −0.048577 | 0.046927 | 0.078486 | 0.076818 | 0.000391 | −0.039989 | −0.028652 | −0.007176 | 0.04561 | 0.096874 | −0.010696 | −0.006853 |
| 236 | −0.067757 | 0.041683 | −0.044347 | 0.063995 | 0.001563 | 0.052818 | 0.030701 | 0.017321 | −0.052748 | 0.01622 | 0.053476 | 0.016476 | 0.083842 | 0.054946 |
| 237 | 0.026072 | −0.039728 | −0.002316 | 0.040404 | −0.036933 | 0.029318 | 0.060511 | −0.010196 | −0.084501 | 0.024934 | −0.006729 | 0.019317 | 0.016601 | 0.016684 |
| 238 | 0.065011 | 0.020492 | −0.034942 | 0.053992 | −0.002788 | −0.013677 | −0.01265 | −0.01676 | 0.011544 | 0.035696 | −0.020002 | −0.021134 | −0.010559 | 0.022373 |
| 239 | 0.021882 | 0.050951 | −0.081428 | 0.012441 | 0.036741 | −0.012275 | 0.001365 | −0.042422 | 0.047064 | −0.009391 | −0.032789 | −0.010436 | −0.007849 | −0.000942 |
| 240 | 0.060159 | 0.022595 | 0.0225721 | 0.010907 | 0.014232 | 0.049939 | −0.019145 | 0.020542 | 0.042235 | 0.024041 | 0.044823 | −0.04568 | −0.038408 | 0.048579 |
| 241 | 0.050215 | 0.030692 | 0.023682 | 0.082571 | 0.019173 | −0.004096 | 0.026894 | 0.026473 | 0.02074 | 0.022354 | 0.022522 | −0.017607 | −0.015193 | 0.056072 |
| 242 | −0.083679 | −0.017638 | −0.10227 | 0.000026 | 0.060334 | 0.025926 | −0.021181 | 0.011129 | −0.059778 | −0.021798 | −0.005371 | 0.068842 | 0.061592 | 0.01858 |
| 747 | 0.024432 | −0.08225 | −0.124199 | −0.036302 | 0.043228 | −0.007423 | −0.064501 | −0.040914 | −0.038022 | 0.005537 | −0.046253 | −0.006301 | 0.027414 | −0.001273 |
| 244 | 0.038819 | 0.012414 | −0.006272 | −0.048834 | 0.015392 | 0.020779 | −0.057668 | −0.070064 | −0.057438 | −0.066104 | −0.01493 | −0.040831 | −0.020785 | 0.004575 |
| 245 | 0.046124 | 0.025831 | −0.013493 | 0.025071 | 0.003142 | −0.004463 | 0.025247 | −0.03306 | −0.039283 | −0.018462 | −0.017694 | 0.006494 | −0.01353 | −0.06366 |
| 246 | −0.085022 | −0.053993 | 0.026702 | −0.014662 | 0.014167 | −0.034816 | 0.019139 | 0.075562 | 0.030242 | −0.023581 | −0.0124061 | 0.032671 | 0.03894 | −0.065942 |
| 247 | −0.059291 | −0.0350721 | 0.0038321 | −0.007515 | 0.015593 | −0.059303 | −0.016858 | 0.022256 | 0.036661 | −0.018851 | 0.0081231 | −0.0018491 | 0.0565671 | −0.001319 |
| 248 | −0.053607 | −0.023667 | −0.0030451 | 0.0042 | 0.011915 | −0.026612 | 0.012107 | 0.038739 | 0.027481 | −0.0048731 | 0.0170641 | −0.0344791 | 0.0222011 | 0.045794 |
| 249 | −0.051649 | −0.015084 | −0.0875361 | 0.078418 | −0.053461 | 0.04941 | −0.039192 | 0.091156 | 0.049727 | 0.065937 | 0.10161 | 0.000479 | −0.009187 | 0.010027 |
| 250 | −0.00134 | 0.019143 | 0.009456 | 0.034888 | 0.024691 | 0.020061 | −0.002353 | 0.022051 | 0.026287 | −0.040922 | 0.058386 | −0.017215 | −0.025957 | 0.030608 |
| 251 | 0.052757 | 0.036636 | −0.012279 | 0.017111 | 0.003425 | 0.057017 | 0.013933 | −0.032701 | −0.00491 | −0.024584 | 0.060194 | −0.051713 | −0.04843 | 0.082187 |
| 252 | 0.072104 | 0.002287 | −0.052504 | −0.013477 | 0.028764 | 0.008923 | 0.070547 | −0.025304 | −0.029633 | −0.077289 | 0.007571 | 0.032381 | 0.02727 | 0.025994 |
| 253 | 0.026815 | −0.048415 | −0.040042 | −0.008649 | 0.019377 | −0.060274 | −0.006721 | 0.005474 | −0.042267 | 0.036059 | −0.058908 | 0.023516 | 0.04504 | −0.026724 |
| 254 | −0.027873 | −0.024539 | −0.0918331 | 0.019304 | −0.008684 | −0.017149 | −0.036795 | 0.006862 | −0.00201 | 0.010077 | 0.035385 | 0.042056 | −0.011467 | −0.048324 |
| 255 | 0.015098 | −0.013685 | 0.014109 | −0.020671 | 0.029297 | −0.010784 | −0.058233 | 0.009154 | −0.042347 | −0.024714 | 0.022284 | 0.025648 | −0.01024 | −0.005365 |
| 256 | 0.092449 | −0.024685 | 0.089171 | 0.104693 | 0.030698 | −0.097794 | 0.025276 | 0.007206 | −0.038424 | 0.024022 | −0.011447 | 0.088537 | −0.004572 | −0.088045 |
| 257 | −0.018024 | 0.062182 | 0.05903 | 0.041385 | 0.052812 | −0.002258 | 0.025151 | −0.00592 | 0.03173 | 0.037384 | −0.005779 | −0.01962 | 0.035791 | 0.001362 |
| 258 | −0.000201 | 0.051419 | 0.054794 | −0.009838 | 0.05126 | 0.016966 | 0.002691 | −0.049092 | −0.017151 | 0.043526 | −0.009849 | −0.013655 | 0.065889 | 0.063791 |
| 259 | −0.051241 | −0.032161 | −0.124805 | 0.034459 | −0.031441 | 0.008022 | −0.006711 | 0.028635 | 0.04725 | 0.013546 | 0.038897 | 0.002093 | 0.021747 | 0.015541 |
| 260 | −0.007637 | −0.038003 | −0.093944 | 0.01348 | −0.013448 | −0.005208 | 0.100842 | 0.048917 | 0.04867 | −0.104273 | −0.012319 | −0.014344 | 0.015724 | −0.008613 |
| 261 | 0.010416 | −0.010745 | −0.024642 | −0.028841 | −0.008395 | 0.026203 | 0.103945 | 0.018139 | 0.001635 | −0.05644 | −0.020905 | −0.009875 | 0.030749 | 0.060811 |
| 262 | −0.01316 | 0.006302 | −0.044371 | −0.007194 | 0.020533 | 0.007952 | 0.046136 | 0.031682 | −0.027822 | −0.043186 | 0.001816 | −0.000937 | 0.007652 | 0.00293 |
| 263 | −0.014854 | 0.036002 | −0.06239 | −0.013582 | 0.019488 | 0.014209 | 0.010403 | 0.019743 | −0.019751 | −0.0288361 | 0.0036571 | −0.0003181 | 0.0044251 | 0.003494 |
| 264 | −0.1071991 | −0.0236231 | −0.0926881 | 0.032227 | −0.024586 | −0.04576 | −0.018082 | 0.020839 | 0.04834 | 0.055059 | 0.067377 | −0.013927 | 0.029253 | −0.076505 |
| 265 | −0.03923 | −0.063805 | −0.083153 | 0.011865 | 0.004902 | −0.072412 | 0.053054 | 0.032703 | 0.026744 | 0.034498 | −0.005205 | 0.002517 | 0.035118 | −0.127621 |
| 266 | 0.026359 | −0.05651 | −0.007387 | −0.025675 | 0.024565 | −0.053256 | 0.091777 | 0.003326 | −0.015521 | −0.023371 | −0.032459 | 0.007872 | 0.004651 | −0.056192 |
| 267 | 0.105295 | −0.022081 | 0.069529 | 0.028425 | −0.085959 | −0.123418 | −0.029129 | 0.05627 | −0.035594 | −0.01771 | −0.01506 | 0.104673 | 0.005414 | −0.122131 |
| 268 | 0.010762 | 0.047132 | 0.042249 | −0.035205 | 0.015041 | −0.024084 | −0.035463 | 0.024722 | 0.014647 | −0.00612 | 0.029279 | 0.069244 | 0.013865 | −0.062601 |
| 269 | 0.000863 | 0.022594 | 0.072657 | −0.011306 | 0.022865 | 0.004641 | −0.003139 | 0.039863 | 0.002446 | −0.017881 | 0.030213 | 0.047488 | −0.01068 | −0.018928 |
| 270 | −0.003936 | 0.050879 | 0.067464 | −0.064144 | 0.04991 | 0.021452 | 0.00644 | 0.01319 | 0.004847 | −0.026707 | 0.028365 | 0.000933 | 0.009668 | −0.009577 |
| 271 | −0.018993 | −0.080247 | 0.023965 | 0.034917 | −0.081483 | −0.094988 | 0.049398 | 0.086452 | −0.024475 | −0.108781 | 0.052887 | 0.043008 | −0.070715 | −0.061765 |
| 272 | 0.052435 | −0.123305 | −0.048963 | 0.033027 | −0.152773 | −0.197522 | 0.010628 | 0.029698 | 0.053069 | 0.003822 | 0.014487 | 0.052145 | −0.069736 | 0.041099 |
| 273 | −0.017941 | −0.101427 | −0.038772 | −0.013826 | −0.064207 | −0.07093 | −0.024787 | 0.0166 | 0.032673 | −0.006396 | 0.036972 | −0.035522 | −0.019307 | 0.086942 |
| 274 | −0.025906 | −0.100644 | −0.027621 | −0.002052 | −0.060183 | −0.06967 | −0.013073 | 0.019833 | 0.027381 | −0.007797 | 0.036918 | −0.050725 | −0.030808 | 0.104482 |
| 275 | −0.018366 | −0.052136 | 0.022721 | −0.051646 | −0.008191 | 0.007272 | 0.001773 | 0.002935 | 0.014077 | 0.009989 | 0.024848 | −0.11428 | −0.011307 | 0.083344 |
| 276 | −0.036587 | −0.002409 | −0.034137 | 0.094475 | −0.052382 | −0.011348 | 0.015845 | 0.00038 | −0.034677 | 0.024804 | 0.069367 | 0.034768 | 0.070101 | 0.060319 |
| 277 | −0.044803 | −0.004778 | −0.038155 | 0.014341 | −0.029975 | 0.048087 | 0.013616 | −0.045799 | −0.047654 | −0.01241 | −0.031784 | −0.016784 | 0.015712 | −0.006979 |
| 278 | −0.044523 | −0.017951 | −0.053121 | −0.012626 | 0.019697 | 0.086795 | 0.0792 | −0.059554 | −0.021867 | −0.02458 | −0.029059 | −0.040703 | −0.039878 | 0.025465 |
| 279 | 0.0309541 | 0.0434351 | −0.0672961 | 0.034398 | 0.03036 | −0.014821 | 0.007682 | −0.050596 | 0.044345 | 0.006607 | −0.02888 | −0.071778 | −0.075642 | 0.039464 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 280 | 0.015813 | −0.102543 | −0.069346 | −0.021124 | −0.002713 | 0.032096 | −0.118101 | −0.039152 | −0.06347 | 0.077838 | −0.089527 | 0.000977 | 0.028146 | −0.012951 |
| 281 | −0.082543 | −0.059379 | 0.039272 | −0.041464 | −0.039952 | −0.07018 | −0.077996 | −0.0062 | 0.078801 | 0.024495 | 0.006677 | −0.013247 | −0.021998 | −0.00365 |
| 282 | −0.064569 | −0.07454 | 0.05996 | −0.050498 | 0.046093 | 0.015973 | −0.048553 | −0.026094 | 0.087869 | 0.001003 | −0.001887 | −0.012867 | −0.033791 | 0.023911 |
| 283 | −0.067261 | −0.006149 | −0.0042 | −0.026159 | 0.003195 | −0.093681 | 0.007161 | −0.016288 | 0.041921 | −0.01826 | 0.020903 | −0.068782 | −0.029085 | 0.053232 |
| 284 | 0.000451 | 0.06211 | 0.055103 | 0.048912 | 0.028787 | −0.012582 | 0.006767 | −0.023781 | 0.038328 | 0.062815 | 0.012124 | −0.04365 | −0.006729 | 0.000568 |
| 285 | −0.022653 | 0.074348 | 0.057491 | 0.054105 | 0.049853 | 0.000602 | 0.02118 | −0.005549 | 0.043524 | 0.010005 | 0.02763 | −0.051008 | −0.01504 | 0.011941 |
| 286 | 0.053769 | 0.066454 | 0.109086 | 0.008044 | 0.021129 | 0.027592 | −0.028461 | −0.078576 | 0.007002 | 0.081716 | 0.01495 | −0.053027 | 0.000557 | 0.058442 |
| 287 | 0.062854 | 0.078127 | 0.089796 | −0.019329 | 0.045604 | 0.020367 | −0.014627 | −0.062616 | 0.012205 | 0.070761 | 0.016669 | −0.06666 | −0.01322 | 0.064723 |
| 288 | −0.024878 | 0.090659 | 0.041875 | −0.052852 | 0.049895 | −0.025349 | 0.055194 | −0.032735 | −0.038011 | 0.0730641 | 0.0286471 | −0.0662261 | −0.000371 | 0.105216 |
| 289 | 0.012955 | 0.021716 | −0.01418 | 0.002516 | 0.020498 | 0.007839 | 0.026186 | 0.001373 | −0.018183 | −0.042244 | 0.005814 | −0.011366 | 0.003821 | −0.008285 |
| 290 | 0.069256 | −0.044383 | 0.014555 | −0.031074 | 0.018044 | −0.066251 | 0.00108 | −0.018971 | −0.040713 | 0.103769 | −0.022795 | −0.009922 | −0.00935 | −0.025708 |
| 291 | 0.069026 | −0.049023 | 0.012194 | −0.036889 | 0.020304 | −0.063118 | −0.006707 | −0.020363 | −0.041346 | 0.106106 | −0.02253 | −0.00673 | −0.011026 | −0.028009 |
| 292 | 0.076557 | −0.027217 | 0.007436 | −0.013898 | 0.008674 | −0.087037 | −0.003356 | −0.016359 | −0.026473 | 0.113312 | −0.005044 | −0.01232 | 0.005679 | −0.028902 |
| 293 | −0.155212 | 0.017729 | −0.083755 | 0.012186 | 0.10436 | −0.025285 | −0.027098 | 0.069375 | −0.012916 | 0.013376 | 0.009564 | 0.047173 | 0.006375 | −0.048464 |
| 294 | −0.049494 | −0.009912 | −0.052828 | 0.008486 | 0.071802 | −0.016186 | −0.010275 | 0.002319 | −0.00874 | −0.025693 | −0.036338 | 0.034298 | 0.070618 | 0.006768 |
| 295 | −0.108283 | −0.0645461 | −0.119937 | 0.006236 | 0.02239 | −0.054464 | −0.014215 | 0.035638 | 0.011432 | 0.020024 | −0.021326 | −0.011056 | −0.008144 | 0.057597 |
| 296 | −0.048267 | −0.062302 | −0.110453 | −0.021861 | −0.000136 | −0.017499 | −0.026281 | 0.006534 | 0.005884 | 0.031633 | −0.024156 | −0.036579 | 0.01109 | 0.082923 |
| 297 | −0.087095 | −0.053965 | −0.121241 | 0.012193 | 0.0196 | −0.061995 | −0.016275 | 0.006656 | 0.018129 | .01939 | 0.003332 | 0.014434 | −0.010666 | 0.029983 |
| 298 | 0.087443 | −0.035073 | −0.050131 | 0.049951 | −0.040231 | 0.085943 | 0.013673 | −0.024209 | −0.027373 | 0.055762 | 0.052525 | −0.022936 | −0.081308 | 0.010465 |
| 299 | −0.006053 | 0.008627 | −0.132996 | 0.008474 | 0.011515 | −0.025402 | −0.058132 | −0.026778 | 0.015562 | 0.01502 | 0.003466 | 0.017709 | −0.001529 | −0.004318 |
| 300 | 0.103514 | −0.078452 | 0.017301 | 0.021297 | −0.065279 | 0.06401 | −0.006161 | −0.013429 | −0.024012 | 0.073163 | 0.022819 | −0.028837 | −0.048618 | −0.020668 |
| 301 | −0.06579 | 0.032247 | −0.119993 | 0.036641 | 0.066889 | −0.002611 | 0.00107 | 0.020121 | 0.026339 | −0.003545 | −0.024423 | −0.013246 | −0.000565 | −0.029827 |
| 302 | −0.02088 | 0.00848 | −0.060877 | −0.00408 | 0.004754 | 0.048537 | −0.023586 | 0.00821 | 0.023354 | −0.006378 | −0.083433 | −0.044955 | 0.005965 | −0.041985 |
| 303 | 0.091336 | −0.00282 | −0.11175 | 0.004555 | 0.014018 | −0.007147 | −0.057745 | −0.096355 | 0.025588 | −0.003999 | −0.062996 | 0.03987 | 0.024966 | 0.011205 |
| 304 | 0.081674 | 0.006321 | −0.0895181 | −0.026476 | −0.023194 | −0.002933 | −0.067058 | −0.073272 | 0.0134171 | 0.012357 | −0.0758971 | 0.0003251 | 0.0165851 | 0.016849 |
| 305 | −0.075803 | 0.043363 | −0.0677131 | 0.015885 | −0.006912 | 0.007369 | 0.06811 | −0.005332 | 0.031301 | −0.046837 | −0.081515 | 0.014575 | −0.080344 | −0.033428 |
| 306 | 0.01717 | −0.100007 | −0.027807 | 0.009819 | 0.042979 | 0.012813 | −0.017747 | −0.056818 | −0.03473 | 0.006098 | −0.034062 | 0.023287 | −0.005272 | −0.045099 |
| 307 | 0.177948 | −0.090698 | −0.013744 | −0.034062 | 0.14721 | 0.000354 | −0.071919 | −0.105099 | 0.101332 | 0.03271 | −0.080101 | 0.137435 | −0.102175 | 0.103897 |
| 308 | 0.001816 | 0.030716 | −0.020146 | 0.013965 | −0.028199 | −0.005508 | −0.033023 | 0.045419 | −0.017519 | −0.028778 | −0.026529 | −0.022933 | −0.01897 | −0.015861 |
| 309 | −0.017087 | 0.021638 | 0.021722 | 0.000931 | 0.011562 | 0.010817 | 0.003793 | 0.034078 | 0.011953 | 0.012381 | 0.018585 | 0.018828 | 0.001158 | −0.009493 |
| 310 | −0.004017 | −0.024656 | 0.004792 | 0.068358 | 0.000089 | 0.012936 | −0.018676 | −0.009213 | −0.03852 | −0.022091 | −0.011373 | 0.000426 | −0.029441 | −0.012281 |
| 311 | 0.000097 | −0.071087 | 0.008578 | −0.02352 | 0.048975 | −0.033124 | 0.075143 | 0.014972 | 0.019739 | −0.007043 | 0.028643 | 0.025126 | 0.045101 | 0.043837 |
| 312 | 0.080856 | −0.098825 | 0.009276 | 0.008267 | 0.11535 | −0.111309 | −0.00635 | −0.063307 | −0.112283 | 0.011268 | 0.060009 | 0.147681 | −0.073171 | 0.068647 |
| 313 | −0.02681 | −0.008752 | −0.000668 | −0.029067 | 0.050869 | −0.051061 | 0.050144 | −0.031783 | 0.016518 | 0.023169 | 0.058658 | 0.025081 | 0.022586 | −0.030544 |
| 314 | 0.005316 | 0.017729 | −0.021699 | 0.057342 | −0.040974 | −0.08586 | 0.000448 | −0.152816 | −0.063632 | −0.10437 | 0.003998 | 0.078061 | −0.022495 | 0.008894 |
| 315 | −0.005338 | 0.009803 | 0.010407 | −0.037594 | 0.037752 | −0.011103 | 0.028961 | −0.012774 | 0.005828 | −0.007969 | 0.043371 | 0.028363 | 0.00266 | 0.015743 |
| 316 | −0.054106 | 0.065624 | −0.002217 | 0.064407 | 0.109311 | 0.052193 | −0.071675 | 0.072166 | −0.093957 , | −0.06937 | −0.106664 | −0.112803 | −0.099552 | 0.10001 |
| 317 | −0.068143 | 0.013444 | 0.026622 | 0.010182 | 0.069328 | −0.001132 | 0.066976 | 0.033748 | 0.025492 | −0.007308 | 0.006784 | 0.01541 | 0.012358 | 0.003314 |
| 318 | −0.073002 | −0.008216 | −0.021489 | 0.000675 | −0.019325 | −0.002177 | 0.030131 | 0.038642 | 0.012848 | −0.069383 | 0.023824 | 0.027395 | 0.009889 | 0.051689 |
| 319 | −0.003085 | 0.037542 | 0.0173541 | −0.042734 | 0.021483 | 0.006878 | −0.003944 | 0.003617 | 0.002335 | 0.0044381 | 0.0190371 | 0.026321 | −0.0208391 | 0.018455 |
| 320 | −0.0106851 | 0.0101831 | 0.0098 | −0.032088 | 0.020578 | 0.02939 | 0.005544 | 0.020359 | 0.014419 | 0.044327 | −0.043087 | 0.024892 | −0.019802 | 0.034434 |
| 321 | 0.045548 | 0.00255 | −0.052612 | −0.00151 | −0.020385 | −0.028445 | 0.046173 | −0.046808 | −0.010255 | 0.004762 | 0.050923 | −0.001116 | 0.056565 | −0.001282 |
| 322 | 0.192801 | 0.087967 | −0.086244 | 0.096908 | −0.041999 | 0.195227 | −0.078772 | 0.028648 | −0.029899 | −0.003976 | −0.039382 | −0.052313 | −0.013349 | 0.024505 |
| 323 | 0.063663 | 0.015189 | −0.007464 | 0.058526 | −0.012365 | 0.028372 | 0.018994 | −0.076465 | −0.065997 | 0.01353 | 0.094204 | −0.058767 | 0.056302 | 0.009721 |
| 324 | 0.027085 | −0.03695 | −0.020117 | 0.134636 | 0.025232 | 0.019237 | −0.019513 | −0.05172 | 0.039984 | −0.042515 | −0.033588 | −0.083628 | −0.12162 | −0.029452 |
| 325 | −0.009667 | −0.02742 | 0.032821 | −0.000394 | 0.042804 | −0.024421 | 0.014948 | 0.03826 | 0.026133 | 0.042993 | 0.011339 | 0.006441 | 0.016246 | 0.009649 |
| 326 | 0.039885 | −0.032331 | 0.023548 | −0.028785 | 0.050065 | −0.05399 | 0.031014 | 0.081087 | 0.019935 | 0.026242 | −0.056567 | −0.011976 | 0.098 | 0.017729 |
| 327 | −0.004208 | −0.008547 | 0.004928 | 0.031117 | −0.048397 | 0.001382 | 0.01769 | 0.021024 | 0.013146 | 0.0225 | 0.01294 | −0.023751 | −0.015497 | 0.033248 |
| 328 | 0.087542 | 0.005145 | −0.087852 | 0.096564 | −0.059498 | 0.138187 | 0.094118 | 0.056119 | −0.052532 | −0.03014 | −0.012151 | −0.001681 | 0.083121 | 0.030591 |
| 329 | 0.024267 | −0.017477 | 0.00581 | 0.003544 | −0.004414 | −0.004689 | −0.0082 | −0.030875 | 0.009967 | 0.014727 | 0.032271 | −0.066963 | 0.047563 | 0.023888 |
| 330 | 0.092956 | 0.058402 | −0.031154 | 0.099038 | −0.22215 | 0.148062 | 0.005082 | 0.0827 | 0.047406 | −0.072423 | −0.025418 | 0.077741 | 0.127716 | 0.004513 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 331 | 0.031031 | −0.013996 | 0.031499 | 0.005311 | 0.032321 | −0.043531 | −0.006044 | 0.001608 | 0.000827 | 0.013949 | 0.026487 | 0.009548 | 0.003796 | 0.015304 |
| 332 | 0.080322 | −0.081282 | 0.054006 | −0.026609 | −0.080306 | 0.100024 | −0.008279 | 0.166036 | −0.051283 | 0.020528 | −0.187893 | 0.105337 | 0.113366 | 0.051925 |
| 333 | −0.035695 | −0.012356 | 0.049974 | 0.017083 | 0.052286 | 0.004092 | 0.026498 | 0.046449 | 0.052215 | 0.002506 | 0.02848 | 0.008617 | 0.004347 | 0.013005 |
| 334 | 0.008504 | −0.101212 | 0.107549 | −0.032364 | 0.031003 | 0.085237 | 0.001209 | 0.041577 | 0.066643 | −0.080229 | 0.086819 | 0.021845 | 0.033722 | −0.009127 |
| 335 | 0.024588 | 0.010352 | 0.04643 | 0.004604 | 0.03383 | −0.008577 | 0.005487 | 0.040277 | 0.025384 | 0.035489 | −0.002818 | 0.010743 | −0.020398 | 0.021123 |
| 336 | 0.0609051 | −0.0233531 | 0.0261741 | 0.062515 | −0.003902 | −0.050009 | 0.05707 | −0.060713 | −0.030041 | 0.018852 | −0.027612 | 0.005651 | 0.043761 | −0.057029 |
| 337 | 0.03658 | −0.032495 | −0.029444 | 0.029605 | 0.034307 | −0.033091 | −0.085549 | 0.017769 | 0.02596 | −0.040528 | 0.070172 | 0.008645 | −0.083357 | 0.024472 |
| 338 | 0.022133 | −0.023202 | −0.032538 | −0.0403 | −0.09304 | 0.190556 | 0.082636 | −0.058556 | 0.045813 | 0.029404 | 0.057637 | −0.124143 | −0.03528 | 0.134494 |
| 339 | −0.014526 | 0.019389, | 0.030001 | −0.020641 | 0.039139 | 0.03606 | 0.043284 | 0.016698 | −0.021049 | 0.02668 | −0.004641 | 0.004597 | −0.004349 | 0.076194 |
| 340 | 0.0173261 | −0.2160191 | −0.0774791 | −0.176656 | −0.19806 | 0.04298 | −0.063628 | −0.002065 | −0.0284931 | 0.0581391 | 0.0244121 | −0.0494821 | −0.036989 | −0.051544 |

| | AN | AO | AP | AQ | AR | AS | AT | AU | AV | AW | AX | AY | AZ | BA |
|---|---|---|---|---|---|---|---|---|---|---|---|---|---|---|
| 1 | −0.033248 | 0.041548 | 0.004407 | 0.04232 | −0.00978 | −0.046593 | −0.025963 | −0.004158 | −0.014118 | 0.043322 | −0.014375 | −0.004204 | 0.024545 | −0.027333 |
| 2 | −0.016607 | −0.019613 | −0.026613 | 0.026211 | 0.006355 | −0.046715 | −0.065869 | −0.011114 | −0.006262 | 0.001651 | 0.046025 | 0.033135 | 0.014284 | −0.015258 |
| 3 | −0.05265 | −0.013401 | −0.018818 | 0.077979 | 0.022912 | −0.032306 | −0.050926 | 0.030873 | 0.045651 | 0.040659 | 0.002472 | 0.013646 | 0.003027 | −0.01591 |
| 4 | −0.012606 | 0.060281 | 0.033821 | 0.031613 | −0.043503 | −0.073967 | −0.060501 | −0.054319 | 0.020464 | 0.05627 | −0.010574 | 0.002087 | 0.027923 | 0.004241 |
| 5 | −0.15201 | 0.046777 | 0.061807 | −0.137806 | −0.194528 | −0.027707 | 0.094907 | −0.028433 | −0.070493 | −0.096681 | −0.020509 | −0.075121 | −0.021568 | 0.063253 |
| 6 | 0.023685 | −0.074812 | 0.003761 | −0.040449 | −0.14402 | −0.061101 | −0.044236 | −0.048966 | 0.140316 | −0.109684 | −0.034067 | −0.026783 | −0.091175 | −0.061655 |
| 7 | −0.001563 | 0.002954 | −0.060204 | 0.055554 | 0.013825 | 0.079292 | 0.039423 | −0.024628 | 0.19843 | −0.026984 | 0.01995 | −0.012649 | −0.067224 | −0.076952 |
| 8 | −0.056451 | −0.150326 | −0.158833 | −0.081455 | −0.098171 | 0.15138 | 0.041052 | −0.071036 | 0.012042 | 0.112861 | 0.136027 | −0.068473 | −0.062882 | −0.060355 |
| 9 | 0.047876 | 0.088331 | 0.029459 | 0.097767 | −0.056627 | −0.001841 | −0.026809 | −0.090912 | 0.040739 | 0.117904 | −0.038304 | −0.10834 | −0.073996 | −0.042568 |
| 10 | 0.00019 | 0.002423 | 0.003001 | 0.021972 | 0.102896 | −0.081142 | −0.122618 | −0.052353 | 0.014024 | −0.010041 | −0.005395 | 0.034293 | 0.053066 | 0.006743 |
| 11 | 0.016791 | 0.006126 | 0.179326 | 0.064198 | 0.071943 | 0.123363 | 0.204447 | −0.165658 | −0.03074 | 0.124479 | 0.016116 | 0.012266 | 0.102513 | 0.0218 |
| 12 | 0.062304 | 0.090816 | −0.111351 | −0.073283 | −0.032103 | −0.139217 | 0.114992 | −0.042636 | 0.153074 | 0.168284 | −0.056001 | 0.025552 | 0.018972 | −0.239318 |
| 13 | 0.000888 | 0.014771 | −0.003823 | −0.02448 | −0.021511 | 0.037025 | −0.065015 | 0.030802 | 0.056416 | 0.038375 | −0.020982 | 0.019855 | 0.018981 | −0.000255 |
| 14 | 0.047248 | −0.010695 | 0.01228 | −0.015426 | −0.042696 | 0.030896 | −0.067585 | −0.014063 | 0.04066 | 0.058038 | −0.040202 | 0.019984 | 0.043749 | 0.00411 |
| 15 | 0.001685 | −0.007827 | 0.001451 | 0.024818 | −0.009502 | −0.022272 | −0.008226 | 0.003953 | −0.055861 | 0.022073 | −0.012972 | −0.004879 | 0.020361 | −0.033392 |
| 16 | 0.063683 | 0.130969 | −0.017917 | 0.105488 | −0.087477 | −0.057301 | 0.073156 | −0.022333 | 0.007525 | 0.089321 | 0.071178 | −0.085276 | −0.108799 | −0.105817 |
| 17 | −0.009746 | −0.001474 | 0.00047 | −0.037478 | −0.097758 | 0.072046 | 0.006467 | −0.020948 | −0.041931 | 0.048773 | 0.037643 | 0.064115 | −0.094815 | −0.06507 |
| 18 | −0.027927 | 0.043027 | 0.00501 | 0.059821 | −0.081144 | 0.080007 | −0.050265 | 0.050613 | −0.08276 | −0.053644 | −0.048717 | −0.141404 | 0.007569 | 0.050038 |
| 19 | −0.087855 | 0.029241 | −0.016549 | 0.078346 | 0.052613 | −0.002305 | −0.056119 | 0.028027 | −0.013135 | −0.010591 | −0.06284 | 0.025354 | −0.068882 | 0.06976 |
| 20 | 0.009458 | 0.002567 | −0.010992 | −0.019586 | −0.004321 | 0.014642 | 0.023047 | −0.00845 | 0.05319f | 0.023319 | −0.021063, | −0.020048 | 0.023572 | −0.00181 |
| 21 | −0.042766 | 0.04277 | −0.019222 | 0.016015 | 0.013073 | −0.001647 | −0.015524 | 0.040036 | 0.03026 | 0.0629 | −0.032276 | 0.109351 | 0.032396 | 0.004737 |
| 2 2 | 0.111472 | −0.075926 | 0.06224 | −0.081419 | 0.045029 | −0.090365 | −0.02697 | −0.043455 | 0.048642 | 0.092379 | −0.008529 | −0.028869 | −0.088543 | 0.070964 |
| 23 | 0.162589 | −0.012925 | 0.013996 | −0.06753 | −0.123196 | −0.078654 | 0.033405 | 0.02446 | 0.000223 | −0.057683 | −0.068049 | 0.088917 | −0.026053 | −0.062475 |
| 24 | −0.004921 | 0.177506 | −0.014458 | −0.045695 | 0.042382 | 0.061688 | −0.015162 | 0.075689 | 0.056242 | 0.046542 | −0.007948 | 0.050513 | 0.123237 | 0.103451 |
| 25 | 0.044471 | 0.067764 | −0.016141 | 0.124483 | −0.060531 | 0.058091 | −0.071884 | −0.006915 | 0.139175 | 0.004151 | 0.090942 | 0.000197 | −0.026465 | 0.053847 |
| 26 | −0.007138 | 0.010159 | −0.000694 | −0.018583 | 0.000976 | 0.016672 | 0.031339 | −0.012571 | 0.050234 | −0.030464 | 0.011993 | −0.018484 | 0.041871 | 0.013348 |
| 27 | −0.006255 | 0.027648 | −0.003926 | −0.020408 | 0.013527 | 0.008904 | 0.015912 | −0.016269 | 0.020001 | −0.000003 | −0.022493 | −0.008629 | 0.013235 | 0.016076 |
| 28 | −0.020208 | 0.020737 | −0.018827 | 0.028042 | −0.061104 | −0.03721 | −0.007205 | −0.032307 | 0.043842 | 0.023256 | −0.015267 | 0.03047 | 0.026065 | −0.027957 |
| 29 | −0.217987 | −0.066112 | 0.011162 | 0.103064 | −0.062796 | 0.007716 | −0.134052 | 0.006099 | −0.125231 | −0.042773 | 0.070471 | 0.035908 | 0.021583 | −0.112658 |
| 30 | −0.009782 | −0.04731 | 0.030713 | −0.145005 | 0.022579 | −0.009676 | −0.005099 | −0.052412 | −0.005304 | −0.030265 | −0.011164 | −0.019858 | 0.058839 | 0.003081 |
| 3 1 | 0.022526 | 0.009144 | 0.032992 | 0.03611 | −0.005026 | 0.020896 | 0.066498 | 0.071296 | −0.029006 | −0.034857 | −0.033089 | 0.087726 | −0.025644 | −0.006412 |
| 32 | 0.092225 | −0.154763 | 0.141944 | 0.052366 | −0.03884 | −0.133646 | 0.010664 | −0.242222 | −0.013145 | 0.049062 | 0.003695 | −0.016949 | 0.140465 | 0.019276 |
| 33 | 0.061938 | 0.02269 | 0.007168 | −0.095531 | −0.065216 | 0.062249 | −0.139797 | 0.054842 | −0.076361 | 0.02367 | −0.000543 | −0.039795 | −0.016014 | 0.005144 |
| 34 | 0.002405 | 0.02786 | −0.007339 | −0.005571 | 0.061784 | 0.01914 | −0.02392 | 0.06603 | −0.02695 | 0.016121 | −0.004706 | −0.04625 | −0.05798 | −0.035434 |
| 35 | 0.018135 | 0.060235 | 0.091494 | −0.0622 | 0.035138 | 0.02397 | −0.053112 | −0.09661 | −0.018301 | 0.009784 | 0.022985 | 0.020692 | 0.036936 | −0.009207 |
| 36 | 0.062674 | 0.047281 | −0.045314 | −0.126692 | 0.093786 | 0.000041 | 0.008439 | −0.035666 | 0.006677 | 0.021567 | 0.042531 | −0.035223 | 0.021678 | 0.019943 |
| 37 | 0.045863 | −0.025549 | −0.005249 | −0.025385 | −0.006622 | 0.003587 | 0.034004 | −0.052867 | −0.016813 | −0.010022 | −0.01616 | 0.030167 | 0.001445 | −0.050904 |
| 38 | −0.031387 | −0.092828 | −0.107197 | −0.025523 | 0.033714 | −0.187177 | 0.064562 | 0.084861 | −0.016384 | 0.017468 | 0.0068 | −0.076182 | −0.026917 | 0.117308 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 39 | −0.001184 | 0.037901 | −0.024755 | 4.002459 | 0.013931 | −0.012332 | 0.090986 | −0.029122 | −0.017214 | −0.031228 | 0.039048 | 0.0495 | −0.029568 | 0.015264 |
| 40 | 0.04325 | −0.021915 | 0.032091 | 0.0207 | 0.049609 | −0.021577 | −0.001595 | 0.042704 | −0.052284 | 0.013137 | −0.006089 | −0.032642 | 0.001597 | −0.016935 |
| 41 | 0.009151 | 0.015572 | −0.031693 | 0.099249 | 0.053247 | −0.002881 | 0.022938 | 0.028083 | −0.03781 | 0.006717 | 0.024869 | −0.016324 | −0.046715 | −0.065647 |
| 42 | −0.045117 | 0.02835 | 0.001727 | 0.018397 | 0.037463 | −0.0157 | 0.065528 | −0.009286 | −0.023168 | 0.001663 | 0.012394 | 0.000753 | −0.066643 | −0.021137 |
| 43 | 0.023434 | −0.04371 | 0.030395 | 0.045672 | 0.051096 | −0.002216 | 0.000024 | 0.038514 | 0.009949 | −0.006426 | 0.00225 | −0.028726 | −0.024304 | 0.000216 |
| 44 | 0.028851 | −0.042693 | 0.015323 | 0.018041 | 0.043975 | 0.028803 | −0.000293 | 0.027492 | −0.013294 | 0.022738 | 0.024804 | 0.039405 | −0.029431 | −0.053812 |
| 45 | 0.041093 | −0.030622 | −0.00529 | 0.067362 | 0.033801 | 0.056792 | −0.019643 | 0.061283 | 0.002986 | 0.010103 | −0.037983 | −0.026412 | 0.019571 | −0.093253 |
| 46 | 0.146923 | −0.008616 | −0.063157 | 0.022102 | −0.078346 | 0.067804 | −0.019563 | 0.015482 | 0.050164 | −0.037756 | −0.020818 | 0.013783 | −0.028259 | 0.031216 |
| 47 | 0.084038 | −0.024222 | −0.054831 | 0.001061 | −0.029999 | 0.033684 | −0.014541 | 0.035625 | −0.070483 | 0.036144 | 0.018234 | 0.075245 | 0.050234 | 0.009665 |
| 48 | 0.024219 | −0.033326 | −0.004097 | −0.052062 | −0.061408 | 0.050408 | 0.05895 | −0.051622 | 0.007623 | −0.052919 | −0.043802 | −0.02162 | 0.0307011 | 0.021041 |
| 49 | −0.048261 | −0.046478 | 0.037791 | −0.117223 | 0.010459 | 0.015745 | 0.0009 | −0.037907 | 0.016662 | −0.041664 | −0.015625 | −0.020458 | 0.056938 | 0.030827 |
| 50 | 0.024599 | 0.022882 | −0.002615 | −0.00629 | −0.047101 | 0.002635 | 0.033425 | −0.094921 | 0.02984 | −0.018032 | −0.008292 | 0.000877 | −0.028697 | −0.016395 |
| 51 | 0.039714 | 0.044096 | 0.040828 | 0.013422 | 0.0453 | −0.008394 | −0.051269 | 0.00921 | −0.034144 | −0.021102 | −0.016826 | 0.014186 | −0.01903 | 0.017765 |
| 52 | 0.038866 | 0.012241 | −0.067329 | −0.016172 | −0.040345 | 0.016652 | −0.019347 | −0.084819 | −0.048527 | −0.044921 | 0.009053 | 0.03773 | −0.045162 | −0.007094 |
| 53 | 0.015526 | 0.002757 | −0.021288 | 0.036492 | 0.006999 | 0.005824 | 0.023022 | 0.034129 | 0.055297 | 0.014826 | −0.008204 | 0.025411 | −0.077178 | −0.019396 |
| 54 | −0.041489 | 0.046656 | 0.0075 | −0.069253 | −0.032208 | −0.017253 | 0.023872 | 0.015206 | 0.007767 | 0.007095 | 0.021503 | −0.063861 | −0.031106 | 0.010207 |
| 55 | 0.001385 | −0.018027 | −0.027301 | −0.021133 | −0.033044 | 0.000567 | 0.077537 | 0.063201 | −0.018537 | −0.017714 | −0.011598 | 0.030787 | 0.025155 | −0.004344 |
| 56 | −0.027948 | −0.061021 | 0.037078 | −0.06279 | −0.00716 | −0.02179 | 0.001081 | −0.015544 | 0.012849 | −0.049244 | 0.010801 | 0.038897 | 0.036796 | 0.059599 |
| 57 | 0.046569 | −0.025667 | −0.033116 | −0.047731 | −0.007254 | 0.022453 | −0.030299 | −0.005362 | −0.047325 | −0.012304 | −0.031756 | −0.032068 | −0.01164 | 0.036642 |
| 58 | −0.002497 | 0.00175 | −0.006302 | −0.020009 | 0.025987 | −0.031545 | −0.00757 | −0.008558 | 0.034173 | −0.014561 | −0.04985 | −0.032888 | −0.021141 | −0.051559 |
| 59 | 0.019478 | −0.119606 | −0.000076 | 0.038635 | 0.063566 | −0.008252 | 0.039451 | −0.084867 | 0.120527 | 0.049102 | −0.021812 | 0.137952 | −0.048788 | −0.012048 |
| 60 | −0.027867 | 0.042475 | 0.040202 | 0.002428 | −0.039922 | 0.00184 | −0.029677 | 0.006261 | −0.026128 | 0.016761 | 0.053641 | 0.035026 | 0.04685 | 0.010476 |
| 61 | −0.010401 | 0.029005 | 0.05377 | 0.081074 | 0.003339 | −0.048424 | −0.045288 | −0.036654 | 0.010883 | 0.004652 | 0.094885 | −0.038658 | 0.022834 | −0.026038 |
| 62 | −0.037986 | −0.042774 | 0.004228 | 0.064681 | −0.040354 | 0.009229 | 0.018789 | 0.029184 | 0.045778 | 0.06003 | 0.066852 | −0.019624 | −0.03336 | 0.009016 |
| 63 | −0.016646 | 0.055785 | 0.004172 | −0.028618 | 0.01138 | −0.06942 | 0.00135 | 0.007721 | −0.015033 | 0.008913 | 0.041754 | −0.03436 | 0.057794 | −0.012068 |
| 64 | −0.02247 | −0.0403451 | 0.027992 | −0.090554 | 0.007844 | −0.004927 | −0.025251 | −0.045901 | 0.00416 | −0.016432 | 0.007422 | −0.009523 | 0.023531 | 0.03036 |
| 65 | −0.035208 | −0.022178 | −0.025163 | −0.028321 | 0.004813 | −0.004579 | −0.027097 | 0.011233 | −0.025528 | 0.016265 | 0.02067 | −0.035615 | 0.027844 | 0.053115 |
| 66 | −0.021263 | 0.016306 | −0.052121 | −0.016653 | 0.045557 | −0.056628 | −0.005709 | −0.017579 | −0.055538 | −0.025872 | 0.017401 | 0.082631 | 0.011928 | −0.0064 |
| 67 | −0.022823 | −0.052003 | −0.0508 | −0.017168 | 0.01234 | −0.085253 | −0.052692 | 0.045797 | 0.029856 | −0.034042 | 0.108144 | 0.026158 | 0.000983 | 0.015271 |
| 68 | −0.011292 | 0.034782 | 0.050841 | 0.161149 | 0.007035 | 0.050341 | −0.039472 | 0.053431 | 0.053992 | 0.105175 | −0.003149 | −0.137159 | 0.111098 | 0.015593 |
| 69 | 0.006956 | 0.00641 | 0.010789 | 0.005925 | −0.031618 | −0.018356 | 0.107472 | −0.022775 | −0.016086 | −0.054496 | −0.043543 | −0.05846 | 0.003833 | −0.07062 |
| 70 | −0.027227 | −0.003418 | −0.052101 | 0.009455 | 0.030938 | 0.023291 | 0.012578 | 0.04573 | −0.065385 | −0.025354 | 0.089846 | 0.066761 | −0.002332 | 0.009364 |
| 71 | 0.021711 | 0.003627 | 0.075069 | −0.033504 | 0.038584 | 0.014914 | 0.047436 | 0.011285 | −0.046305 | 0.006011 | −0.004871 | −0.035458 | −0.004655 | −0.034005 |
| 72 | 0.022262 | 0.02743 | 0.040499 | −0.037565 | 0.027443 | 0.011986 | −0.045995 | 0.0718 | 0.004141 | 0.01871 | −0.004321 | −0.005893 | −0.024788 | −0.046556 |
| 73 | 0.131251 | −0.033079 | 0.006574 | 0.079655 | −0.032109 | −0.124887 | −0.048421 | 0.011931 | −0.055245 | −0.043652 | −0.030372 | −0.11885 | −0.051318 | 0.050619 |
| 74 | −0.1121921 | 0.164921 | 0.055327 | −0.073231 | −0.006781 | 0.080409 | 0.026626 | 0.04478 | −0.023288 | −0.129045 | −0.01481 | 0.103789 | −0.097355 | −0.084203 |
| 75 | −0.004335 | −0.016523 | 0.03578 | −0.007853 | −0.004017 | 0.024289 | −0.000691 | 0.037583 | −0.036526 | 0.003075 | −0.001111 | 0.007408 | 0.018546 | 0.006662 |
| 76 | 0.001082 | −0.029243 | −0.004237 | −0.062678 | 0.043416 | 0.104992 | 0.039155 | −0.020562 | 0.001326 | −0.055587 | 0.029217 | −0.044653 | −0.046207 | −0.001016 |
| 77 | −0.013913 | −0.002817 | 0.034246 | 0.002427 | 0.023129 | 0.021509 | 0.03431 | 0.036069 | −0.042673 | −0.035728 | 0.027662 | 0.020536 | 0.004752 | 0.005845 |
| 78 | 0.000803 | −0.013168 | 0.022343 | 0.000829 | −0.01706 | 0.024591 | 0.001113 | 0.048995 | −0.043754 | −0.026064 | −0.006184 | 0.000668 | −0.000996 | 0.024639 |
| 79 | −0.033168 | −0.021381 | 0.011933 | −0.043665 | −0.000088 | 0.02901 | −0.032998 | −0.071234 | −0.068961 | −0.000669 | 0.022539 | −0.020505 | −0.060876 | 0.049605 |
| 80 | 0.123248 | 0.02173 | 0.147467 | 0.012027 | −0.057993 | −0.064044 | 0.009801 | 0.027107 | −0.178725 | −0.029985 | 0.099996 | 0.096644 | 0.130366 | −0.043023 |
| 81 | −0.080191 | −0.124281 | −0.043376 | 0.065895 | 0.154893 | −0.023805 | 0.120196 | 0.014767 | 0.088418 | −0.02638 | 0.114322 | −0.001164 | 0.175985 | −0.035587 |
| 82 | −0.043442 | 0.030728 | 0.01482 | −0.027942 | 0.011598 | 0.02289 | −0.012866 | 0.000588 | 0.032171 | −0.014923 | −0.008651 | 0.027084 | 0.014601 | 0.053954 |
| 83 | −0.0221621 | 0.0275951 | −0.0090421 | −0.011657 | −0.003247 | 0.006077 | −0.019077 | 0.000323 | 0.0177251 | 0.023277 | −0.031192 | −0.022215 | 0.0120671 | 0.030994 |
| 84 | 0.0212091 | 0.0125191 | −0.0311541 | −0.027824 | 0.002605 | −0.015849 | −0.00886 | 0.017588 | −0.003371 | 0.0032781 | 0.0182261 | −0.037248 | −0.054854 | 0.022868 |
| 85 | 0.000811 | −0.106493 | −0.05775 | −0.071656 | 0.055386 | 0.064203 | 0.029927 | 0.005178 | −0.018069 | 0.011857 | −0.000109 | 0.035247 | −0.148131 | 0.03924 |
| 86 | 0.029772 | −0.041954 | −0.026639 | 0.062116 | 0.079154 | −0.011929 | 0.019178 | 0.045894 | −0.029416 | 0.001653 | −0.050961. | −0.005 | −0.027794 | 0.01504 |
| 87 | 0.039111 | 0.054622 | 0.048902 | 0.041755 | 0.001184 | 0.032445 | 0.00437 | 0.04697 | −0.099886 | −0.007946 | 0.052663 | 0.051881 | 0.007237 | −0.02675 |
| 88 | −0.033879 | 0.040754 | 0.015747 | −0.012592 | −0.023485 | 0.000782 | −0.004666 | 0.00544 | 0.019117 | 0.003117 | −0.037258 | 0.009682 | 0.071724 | 0.027145 |
| 89 | −0.02294 | 0.023133 | −0.014499 | −0.000979 | −0.009259 | −0.02217 | −0.00682 | 0.001119 | 0.023491 | 0.010681 | −0.028404 | −0.026941 | −0.015515 | 0.044228 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 90 | −0.06819 | 0.002657 | 0.014495 | 0.028084 | −0.030635 | −0.030477 | 0.020341 | −0.02896 | 0.010265 | 0.025582 | 0.008412 | 0.008979 | −0.048331 | 0.067454 |
| 91 | −0.02782 | −0.002874 | −0.101405 | 0.01049 | −0.003323 | 0.010945 | −0.063627 | 0.003354 | 0.022223 | −0.031298 | 0.023629 | 0.028193 | −0.065207 | 0.007736 |
| 92 | 0.012499 | −0.090615 | −0.074939 | −0.015471 | 0.073548 | −0.101484 | −0.122333 | 0.090199 | 0.005572 | 0..020302 | −0.026636 | −0.131553 | 0.089601 | −0.031478 |
| 93 | −0.079833 | 0.01509 | 0.014922 | 0.037335 | 0.041089 | 0.017883 | 0.013341 | −0.034913 | −0.015112 | 0.001195 | 0.021086 | −0.033135 | 0.004877 | 0.045877 |
| 94 | 0.07245 | −0.046675 | −0.021265 | −0.024453 | −0.037362 | 0.031497 | 0.017018 | −0.02516 | 0.05021 | 0.093957 | −0.052327 | 0.060399 | 0.022386 | 0.039327 |
| 95 | 0.022754 | −0.08434 | 0.010426 | 0.077924 | 0.066986 | −0.06883 | −0.053648 | 0.01191 | 0.037624 | −0.106567 | 0.082091 | −0.154955 | 0.015441 | −0.124012 |
| 96 | 0.022806 | 0.025037 | −0.01375 | −0.10577 | 0.092071 | 0.119415 | 0.026978 | 0.032618 | −0.010718 | 0.021609 | 0.099678 | 0.078798 | 0.014643 | −0.130519 |
| 97 | 0.076049 | 0.063426 | 0.023221 | 0.025771 | 0.043643 | 0.027696 | −0.041252 | −0.028887 | −0.053756 | 0.017646 | 0.03826 | 0.02406 | 0.016681 | −0.000852 |
| 98 | 0.024003 | 0.02542 | 0.040758 | −0.019808 | −0.018131 | −0.022141 | 0.020112 | −0.023989 | −0.019975 | 0.010098 | 0.021588 | −0.003542 | 0.016077 | 0.016736 |
| 99 | 0.0569311 | 0.012762 | −0.037521 | −0.06982 | −0.013677 | −0.012783 | −0.002634 | 0.008823 | −0.038986 | −0.022184 | 0.03421 | −0.012964 | 0.0466521 | 0.032818 |
| 100 | −0.0094061 | 0.037088 | 0.009218 | −0.048179 | −0.010762 | 0.061893 | 0.049482 | −0.00829 | 0.016943 | 0.003252 | 0.018927 | −0.017368 | −0.019525 | 0.050678 |
| 101 | 0.021594 | 0.023672 | 0.049025 | −0.006576 | 0.005735 | −0.020684 | 0.005403 | −0.008427 | −0.006807 | −0.029307 | 0.027931 | −0.01897 | 0.004042 | 0.045049 |
| 102 | 0.027479 | −0.023186 | 0.096452 | 0.016426 | 0.062977 | −0.056046 | −0.054992 | 0.003113 | 0.02623f | −0.044873 | −0.007914 | −0.018017 | −0.01307 | −0.001509 |
| 103 | 0.013633 | 0.035937 | 0.138102 | 0.090776 | −0.00083 | 0.031638 | −0.133186 | 0.040765 | 0.119055 | −0.02776 | −0.039219 | −0.055191 | 0.048574 | 0.011008 |
| 104 | −0.0223591 | −0.014981 | 0.0358741 | −0.027168 | −0.095458 | −0.031972 | 0.035274 | 0.14662 | 0.0791061 | −0.024645 | 0.0243521 | −0.002017 | −0.030011 | −0.061533 |
| 105 | 0.0945051 | −0.062514 | 0.056626 | 0.034445 | 0.00891 | 0.068846 | −0.063305 | −0.023982 | −0.167677 | 0.106612 | −0.082432 | −0.044242 | −0.006969 | 0.147769 |
| 106 | −0.05214 | 0.003947 | −0.023864 | −0.087642 | 0.016482 | −0.077619 | 0.060265 | 0.080421 | −0.051756 | −0.031082 | −0.043269 | 0.049275 | 0.011396 | 0.068054 |
| 107 | 0.055122 | 0.022295 | −0.029034 | −0.026171 | 0.046412 | 0.035738 | 0.130713 | 0.009279 | −0.069859 | −0.04415 | 0.015911 | 0.027161 | 0.095519 | 0.065032 |
| 108 | 0.075624 | 0.034713 | 0.100699 | 0.086678 | 0.006672 | 0.048666 | 0.003829 | −0.087876 | 0.029259 | −0.119554 | 0.022968 | −0.037796 | −0.01747 | −0.068147 |
| 109 | 0.024483 | −0.122809 | 0.125682 | 0.086211 | −0.124911 | 0.091867 | 0.007984 | 0.191088 | −0.018089 | 0.012328 | −0.141907 | −0.030745 | −0.015488 | −0.072239 |
| 110 | 0.187612 | 0.215095 | 0.050954 | −0.15648 | 0.047854 | 0.059774 | −0.134412 | 0.025888 | −0.01659 | −0.029472 | −0.008506 | −0.067067 | −0.089014 | 0.010056 |
| 111 | 0.068181 | −0.015726 | 0.066744 | −0.090905 | 0.057488 | −0.088986 | 0.070289 | 0.011942 | −0.072285 | −0.144921 | 0.138305 | 0.035053 | −0.070297 | −0.105132 |
| 112 | 0.058855 | −0.027547 | 0.131653 | −0.024186 | 0.01708 | −0.074101 | 0.119194 | −0.042153 | 0.027983 | −0.135268 | 0.044923 | −0.098583 | −0.021315 | −0.041171 |
| 113 | 0.062122 | −0.085141 | −0.004268 | −0.050382 | −0.059399 | −0.105675 | −0.018183 | −0.070306 | −0.002554 | 0.017493 | −0.114752 | −0.025233 | 0.033287 | 0.08698 |
| 114 | −0.117005 | −0.001643 | −0.091291 | 0.078717 | −0.071444 | 0.047111 | −0.0663 | −0.061239 | −0.004597 | −0.009791 | 0.022927 | −0.077314 | 0.026139 | −0.082388 |
| 115 | −0.073674 | 0.080921 | −0.115285 | −0.038713 | −0.015749 | 0.05596 | 0.005248 | −0.015434 | −0.050979 | 0.000073 | −0.004954 | 0.00118 | −0.119398 | 0.159256 |
| 116 | 0.051776 | 0.006777 | 0.019266 | −0.044124 | 0.053391 | 0.043857 | 0.061354 | 0.014824 | 0.077331 | −0.216242 | −0.027457 | −0.019383 | 0.001591 | 0.136983 |
| 117 | 0.010485 | −0.016294 | −0.005221 | −0.043977 | 0.020803 | 0.0337 | 0.032428 | −0.003631 | 0.039781 | 0.066355 | 0.009052 | 0.014684 | 0.055757 | 0.060193 |
| 118 | −0.043512 | −0.007461 | 0.0213 | −0.045969 | −0.00612 | 0.059385 | 0.037779 | −0.037037 | −0.024201 | 0.018633 | 0.052084 | 0.024791 | 0.086694 | 0.01842 |
| 119 | 0.012931 | 0.018954 | −0.007336 | −0.022974 | 0.022044 | 0.068666 | 0.03272 | 0.016556 | −0.041627 | −0.067794 | 0.031207 | 0.016041 | 0.048904 | −0.057075 |
| 120 | −0.008486 | −0.093443 | −0.032968 | −0.001693 | −0.016372 | 0.025489 | 0.031472 | 0.038164 | 0.026697 | 0.032782 | −0.051268 | 0.050684 | 0.011818 | 0.064681 |
| 121 | 0.03019 | −0.05982 | 0.019301 | 0.067161 | −0.028255 | 0.050841 | 0.015189 | 0.035949 | 0.039284 | 0.067577 | −0.068905 | 0.057023 | 0.036677 | 0.077641 |
| 122 | 0.022015 | −0.079313 | −0.02312 | 0.012099 | 0.057484 | −0.041711 | 0.088546 | −0.077873 | 0.072982 | 0.006064 | −0.008101 | 0.00652 | 0.072064 | 0.006645 |
| 123 | 0.006656 | −0.086379 | −0.013599 | 0.027167 | 0.101336 | 0.032906 | 0.077586 | −0.081316 | 0.065938 | 0.026355 | 0.010895 | 0.01882 | 0.016273 | 0.054219 |
| 124 | 0.028247 | −0.014285 | −0.011514 | 0.003919 | −0.010052 | −0.01543 | 0.045274 | 0.007374 | 0.0190441 | −0.066226 | 0.053814 | −0.002549 | 0.008788 | 0.007476 |
| 125 | −0.008747 | 0.033652 | 0.024965 | 0.023786 | −0.030535 | −0.017736 | −0.040558 | 0.016511 | −0.002459 | 0.039291 | −0.028952 | −0.022024 | −0.004603 | −0.031686 |
| 126 | 0.002277 | −0.023823 | 0.027397 | 0.015792 | −0.009222 | 0.006156 | 0.014259 | −0.018874 | 0.006798 | 0.019305 | −0.024973 | 0.051058 | 0.035683 | 0.026822 |
| 127 | 0.046344 | −0.000115 | 0.036585 | 0.000731 | −0.016837 | 0.008067 | 0.031548 | −0.018963 | 0.027139 | 0.016385 | 0.018826 | 0.0511 | 0.023617 | 0.02787 |
| 128 | 0.044616 | 0.041169 | −0.020123 | −0.006607 | −0.063626 | 0.094387 | −0.054081 | −0.020153 | −0.038242 | 0.042794 | 0.054341 | 0.058995 | 0.065453 | −0.007331 |
| 129 | −0.081825 | 0.077399 | 0.1099 | 0.052643 | 0.223655 | −0.170637 | 0.086469 | 0.018953 | 0.00526 | 0.081983 | −0.076008 | 0.093433 | −0.147122 | 0.057783 |
| 130 | −0.117665 | −0.209752 | −0.075875 | 0.04531 | −0.06216 | 0.014533 | −0.120166 | −0.003783 | −0.128965 | −0.077552 | −0.077902 | 0.030602 | −0.034292 | 0.003623 |
| 131 | 0.024647 | 0.085778 | 0.209598 | 0.024147 | −0.000382 | 0.065473 | −0.027795 | −0.061061 | −0.105564 | −0.033659 | −0.094566 | −0.026265 | 0.021673 | 0.016828 |
| 132 | 0.002429 | 0.074579 | 0.056502 | 0.008736 | −0.03873 | 0.026449 | −0.011771 | −0.089435 | 0.012291 | 0.014368 | 0.024246 | −0.077814 | −0.043632 | −0.086927 |
| 133 | 0.120211 | 0.035786 | −0.004034 | −0.025598 | 0.013608 | −0.021113 | −0.055679 | −0.047299 | −0.010458 | 0.067393 | −0.030522 | 0.02876 | 0.020969 | −0.013276 |
| 134 | 0.092442 | 0.09829 | −0.005176 | −0.024859 | 0.115187 | −0.053732 | −0.114566 | 0.05828 | 0.172891 | −0.126745 | −0.006872 | 0.057622 | −0.047195 | −0.045328 |
| 135 | 0.027091 | −0.016186 | −0.010658 | −0.013096 | −0.029992 | 0.009019 | −0.026569 | −0.020359 | −0.006287 | −0.019947 | 0.0248 | −0.008676 | 0.026603 | −0.047108 |
| 136 | 0.041495 | 0.061785 | −0.06362 | −0.00462 | 0.014795 | 0.064454 | −0.075986 | 0.089202 | 0.028038 | 0.032661 | 0.012594 | −0.00904 | −0.027995 | 0.032647 |
| 137 | −0.002078 | 0.022366 | 0.025231 | −0.042996 | −0.108986 | −0.022414 | −0.025873 | 0.005426 | −0.054165 | 0.020407 | −0.001321 | 0.017275 | −0.030714 | 0.038977 |
| 138 | 0.052242 | 0.014756 | −0.096696 | 0.03428 | 0.102252 | 0.109755 | −0.031812 | −0.039971 | 0.034715 | 0.049573 | −0.013884 | −0.006283 | 0.140456 | −0.110262 |
| 139 | −0.049198 | −0.046946 | 0.0944421 | 0.008887 | −0.070321 | 0.050521 | −0.113526 | 0.015842 | 0.050602 | −0.159901 | −0.026045 | 0.030441 | −0.070146 | 0.014952 |
| 140 | −0.015579 | 0.1264461 | −0.073297 | 0.061443 | 0.014175 | 0.04567 | −0.026558 | −0.023619 | −0.052391 | −0.060145 | 0.043593 | −0.058515 | −0.177388 | −0.062749 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 141 | 0.04937 | −0.013763 | −0.05573 | 0.026655 | 0.068101 | 0.045654 | −0.019206 | −0.003581 | −0.01533 | 0.021685 | −0.010469 | −0.070215 | 0.116331 | −0.109569 |
| 142 | 0.010152 | −0.059341 | 0.022336 | 0.063513 | 0.031061 | 0.007212 | −0.036292 | −0.024362 | 0.008829 | 0.015753 | −0.06381 | −0.07029 | −0.020212 | −0.02412 |
| 143 | 0.057651 | −0.084155 | −0.080905 | −0.035293 | 0.092585 | −0.003243 | 0.01254 | −0.097093 | 0.058905 | −0.030411 | −0.058907 | −0.090715 | 0.034589 | −0.028594 |
| 144 | 0.034865 | −0.013554 | −0.039433 | 0.046555 | 0.102761 | −0.064044 | 0.008081 | −0.012806 | −0.038014 | −0.056933 | 0.002197 | −0.00033 | 0.083907 | −0.006596 |
| 145 | 0.058968 | 0.037438 | −0.024146 | 0.040396 | 0.030521 | −0.032989 | −0.05592 | −0.062952 | 0.016471 | 0.056214 | 0.059047 | 0.039465 | 0.093459 | −0.000989 |
| 146 | 0.021986 | 0.025609 | −0.019097 | 0.018048 | −0.01811 | 0.005224 | −0.037926 | −0.020884 | 0.0365 | −0.0135 | −0.004568 | 0.028957 | −0.033618 | 0.001496 |
| 147 | −0.044901 | 0.03484 | 0.027649 | −0.042233 | 0.03111 | −0.070939 | 0.055851 | −0.03623 | 0.037286 | 0.043754 | −0.079071 | −0.005937 | −0.014802 | 0.036152 |
| 148 | 0.046738 | 0.097436 | −0.099867 | 0.179459 | −0.036233 | 0.004665 | −0.026415 | −0.132382 | −0.147368 | −0.183688 | 0.16303 | 0.010507 | −0.048747 | 0.14408 |
| 149 | 0.026677 | −0.004747 | −0.022924 | −0.074454 | −0.054363 | 0.057956 | 0.039797 | 0.036269 | −0.053 | 0.023908 | 0.077913 | −0.007191 | 0.088085 | 0.033975 |
| 150 | −0.06136 | −0.071361 | 0.014745 | 0.027404 | −0.083556 | 0.002839 | −0.034029 | −0.013645 | 0.12613 | −0.118208 | −0.099991 | −0.138397 | 0.036343 | 0.131195 |
| 151 | −0.094002 | 0.06289 | −0.096984 | −0.039827 | −0.001931 | 0.010282 | −0.076639 | −0.062038 | 0.114295 | −0.121647 | 0.026992 | 0.06543 | 0.033748 | 0.008881 |
| 152 | 0.05102 | 0.038391 | 0.018251 | −0.035055 | 0.007841 | −0.04057 | 0.016846 | 0.041273 | −0.029187 | −0.047118 | 0.044718 | −0.048455 | −0.021809 | −0.005039 |
| 153 | 0.047904 | 0.000406 | −0.012541 | −0.017192 | −0.028646 | 0.020847 | 0.050113 | 0.011414 | −0.007802 | −0.05758 | −0.036754 | 0.018072 | −0.069136 | 0.025659 |
| 154 | 0.025364 | −0.041706 | 0.044366 | 0.027433 | −0.013549 | 0.012101 | −0.056987 | 0.034599 | −0.0312 | 0.014041 | 0.001614 | −0.069041 | −0.070884 | 0.000414 |
| 155 | 0.020965 | −0.036798 | 0.026059 | 0.066517 | −0.02724 | −0.0193 | 0.016017 | 0.077561 | −0.003172 | 0.0161721 | 0.060758 | −0.038343 | −0.024431 | 0.001584 |
| 156 | 0.02262 | 0.011422 | 0.029758 | −0.02702 | 0.002817 | 0.038281 | 0.047026 | 0.049423 | 0.106879 | −0.058545 | −0.179992 | −0.025674 | 0.041401 | −0.104343 |
| 157 | −0.074654 | −0.023875 | −0.054309 | −0.030871 | −0.009974 | −0.012318 | −0.038583 | −0.028359 | −0.020753 | 0.036032 | 0.040772 | −0.031579 | −0.046693 | 0.04299 |
| 158 | 0.201278 | −0.120355 | 0.000783 | 0.049337 | 0.020012 | −0.02415 | −0.086904 | 0.159396 | −0.055698 | 0.088064 | 0.104511 | 0.063575 | −0.114637 | 0.015346 |
| 159 | 0.074441 | −0.024436 | −0.021322 | −0.049018 | −0.078618 | −0.022337 | −0.053567 | 0.193519 | 0.128974 | 0.009653 | 0.086213 | −0.00388 | 0.041973 | 0.213481 |
| 160 | 0.075659 | −0.170628 | 0.020781 | −0.167803 | 0.132489 | −0.039079 | −0.050472 | 0.079567 | −0.021223 | 0.046127 | −0.066545 | 0.14318 | −0.084618 | −0.133484 |
| 161 | 0.053739 | −0.008718 | −0.026322 | 0.07787 | 0.002451 | −0.02014 | 0.136974 | −0.006198 | 0.008803 | −0.041028 | 0.060665 | 0.067077 | −0.120492 | 0.024239 |
| 162 | −0.043606 | 0.080289 | 0.100897 | −0.067098 | 0.050308 | −0.024875 | −0.017199 | −0.013932 | −0.009363 | −0.019176 | 0.080994 | −0.116117 | 0.072296 | −0.111896 |
| 163 | 0.106316 | 0.040669 | 0.051032 | −0.053065 | −0.04537 | −0.029136 | 0.09146 | 0.000788 | 0.011608 | 0.039699 | 0.009019 | −0.113344 | 0.003374 | −0.053618 |
| 164 | −0.01104 | 0.039311 | 0.032541 | 0.049563 | −0.064107 | 0.047846 | −0.093887 | −0.00615 | −0.030941 | 0.07581 | 0.07732 | −0.053317 | 0.108391 | −0.002365 |
| 165 | 0.0217231 | −0.0315251 | −0.0116081 | 0.054347 | 0.019181 | −0.009301 | 0.064143 | −0.022145 | −0.096874 | 0.1249471 | 0.152261 | 0.0634281 | 0.1330261 | 0.029762 |
| 166 | 0.019856 | −0.084709 | −0.029433 | 0.121794 | 0.002074 | −0.019745 | −0.07144 | 0.004797 | −0.015139 | −0.054272 | −0.079758 | 0.033548 | 0.034725 | −0.099392 |
| 167 | 0.056047 | −0.018699 | −0.043785 | 0.016768 | −0.072803 | −0.073398 | 0.049079 | 0.00194 | −0.060679 | −0.054787 | −0.073566 | 0.063407 | 0.122353 | −0.010431 |
| 168 | −0.009529 | 0.045967 | −0.192872 | 0.000839 | 0.037947 | 0.16125 | 0.027167 | −0.050601 | −0.069898 | 0.126829 | −0.13754 | 0.152222 | −0.095906 | 0.002532 |
| 169 | −0.025432 | −0.047501 | 0.009172 | −0.047624 | 0.022576 | −0.01145 | 0.029843 | 0.063362 | −0.008296 | −0.027803 | −0.024056 | −0.060615 | 0.008456 | −0.000064 |
| 170 | −0.049823 | −0.04775 | 0.002583 | −0.032304 | 0.04748 | 0.008039 | 0.043662 | 0.090807 | −0.010931 | −0.034445 | −0.006918 | −0.043937 | 0.041239 | 0.012777 |
| 171 | 0.013952 | −0.032362 | −0.047489 | −0.034991 | 0.053543 | 0.055561 | 0.045942 | 0.063709 | −0.005035 | −0.039866 | −0.066442 | −0.032763 | −0.01161 | 0.013402 |
| 172 | −0.02465 | −0.048346 | −0.017095 | 0.006348 | −0.023778 | 0.016395 | −0.016897 | 0.016493 | 0.022259 | −0.040918 | 0.023933 | 0.014284 | −0.015356 | 0.006361 |
| 173 | −0.012143 | −0.02453 | 0.023767 | 0.008955 | −0.01287 | −0.020459 | −0.017685 | 0.004351 | −0.011809 | 0.026659 | 0.035066 | 0.073526 | −0.01798 | 0.021004 |
| 174 | 0.00848 | 0.003081 | −0.027192 | 0.009541 | −0.03965 | −0.048944 | −0.011597 | −0.026791 | −0.021026 | 0.00837 | −0.0042 | 0.084078 | −0.038452 | 0.008255 |
| 175 | −0.099291 | −0.0855851 | −0.007079 | −0.01733 | −0.054277 | −0.109664 | 0.006224 | −0.091639 | −0.00088 | −0.009493 | −0.006148 | 0.117325 | −0.007755 | 0.058796 |
| 176 | 0.0141761 | −0.054421 | −0.057833 | −0.070265 | 0.005553 | −0.009335 | 0.039115 | −0.002362 | −0.047762 | −0.054164 | −0.004756 | 0.0315911 | −0.013227 | 0.05007 |
| 177 | 0.020932 | −0.013196 | −0.14624 | 0.030663 | −0.121643 | −0.1034 | 0.011451 | 0.220552 | 0.023739 | −0.076558 | 0.065968 | −0.0713 | 0.056766 | 0.048987 |
| 178 | −0.011026 | 0.052579 | 0.038671 | −0.010624 | −0.023002 | −0.081188 | 0.009645 | 0.009402 | −0.041354 | −0.01213 | 0.04145 | −0.006356 | 0.032252 | 0.051811 |
| 179 | 0.018622 | 0.019728 | −0.036045 | −0.011925 | 0.012965 | 0.023922 | 0.022197 | −0.016976 | −0.040444 | 0.006376 | −0.052162 | −0.012027 | 0.023349 | −0.002272 |
| 180 | −0.004798 | 0.028113 | 0.0200631 | −0.006347 | 0.013659 | −0.031258 | 0.001121 | 0.003396 | −0.054672 | −0.011976 | −0.01718 | −0.014551 | 0.043412 | 0.001986 |
| 181 | 0.006342 | 0.030239 | 0.0101461 | −0.021032 | −0.006483 | −0.030637 | 0.022667 | 0.001319 | −0.033499 | −0.018235 | −0.025665 | −0.023286 | 0.0364 | 0.004261 |
| 182 | −0.017368 | 0.011178 | −0.040331 | −0.016924 | −0.01202 | 0.006826 | 0.043672 | −0.006468 | −0.040501 | −0.032401 | −0.02125 | −0.016909 | 0.030456 | 0.002218 |
| 183 | 0.023174 | 0.010291 | −0.056346 | −0.031591 | 0.027865 | 0.11565 | 0.054813 | −0.013354 | 0.001188 | −0.029409 | −0.072921 | −0.013704 | −0.009136 | −0.005109 |
| 184 | 0.044133 | 0.02466 | −0.057758 | 0.008618 | 0.051218 | 0.054878 | 0.01185 | −0.01983 | 0.036825 | −0.009518 | −0.049772 | 0.012934 | −0.077404 | −0.02844 |
| 185 | 0.027309 | −0.0133 | −0.046993 | −0.00673 | −0.073895 | 0.013848 | 0.017455 | −0.081685 | 0.044315 | −0.044948 | 0.096137 | −0.1356 | 0.075768 | −0.023138 |
| 186 | −0.123537 | −0.030795 | −0.106298 | 0.065267 | 0.010883 | 0.126424 | 0.004826 | 0.078372 | 0.021611 | −0.070422 | −0.016633 | −0.028478 | −0.123514 | −0.071129 |
| 187 | −0.045346 | 0.033071 | 0.030893 | 0.044358 | 0.035297 | −0.003103 | −0.055673 | 0.039097 | 0.01249 | 0.018567 | 0.026432 | 0.027925 | 0.012017 | −0.031117 |
| 188 | −0.00407 | 0.035674 | 0.020002 | 0.028021 | 0.021034 | −0.007646 | −0.041093 | 0.00272 | −0.004747 | −0.001214 | 0.016813 | 0.030319 | 0.010593 | −0.028134 |
| 189 | −0.009894 | 0.005677 | 0.046075 | 0.042056 | 0.039922 | −0.005707 | −0.015427 | −0.057446 | 0.010372 | 0.012535 | −0.041868 | 0.027007 | −0.047319 | 0.012163 |
| 190 | −0.019051 | −0.001862 | −0.024142 | −0.021563 | 0.037906 | 0.051537 | −0.016801 | −0.037141 | 0.023526 | −0.006496 | −0.029832 | 0.061782 | −0.011851 | 0.019977 |
| 191 | −0.039596 | 0.01269 | −0.026601 | 0.024844 | 0.097822 | 0.070817 | −0.026445 | 0.055895 | −0.005616 | 0.001334 | −0.01548 | 0.002147 | −0.083746 | −0.040993 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 192 | 0.045963 | −0.036202 | −0.094154 | −0.03127 | 0.046978 | 0.026073 | 0.00668 | 0.009455 | −0.004284 | −0.088373 | −0.051952 | 0.086628 | 0.042455 | −0.071416 |
| 193 | 0.035068 | −0.052668 | −0.028468 | 0.012518 | 0.067405 | 0.061884 | −0.029346 | −0.022582 | −0.003968 | −0.024006 | 0.012245 | 0.080693 | 0.025036 | −0.043805 |
| 194 | 0.009614 | −0.042097 | 0.000731 | 0.004264 | 0.156044 | 0.025972 | −0.092725 | −0.055753 | 0.006143 | −0.001594 | −0.014005 | 0.00142 | 0.032573 | 0.007579 |
| 195 | 0.008308 | −0.030452 | 0.028681 | 0.071698 | 0.018553 | 0.049989 | 0.031831 | −0.038692 | −0.009369 | −0.052674 | 0.019586 | 0.011385 | −0.091222 | −0.076114 |
| 196 | 0.0039841 | −0.001365 | −0.0172661 | 0.017729 | −0.041393 | −0.010588 | 0.00265 | −0.060753 | 0.0518991 | −0.071751 | 0.0197081 | 0.0204031 | −0.082573 | −0.002293 |
| 197 | −0.043754 | −0.0086121 | −0.0564041 | −0.033889 | 0.009086 | 0.053435 | −0.002957 | −0.003418 | 0.044841 | 0.049168 | 0.067473 | 0.058909 | −0.01016 | −0.03484 |
| 198 | −0.054003 | −0.036482 | −0.006233 | 0.078135 | 0.018022 | 0.018019 | 0.059147 | 0.001614 | 0.008175 | −0.071832 | 0.06607 | 0.046661 | 0.007954 | 0.075993 |
| 199 | −0.111381 | 0.119215 | 0.008208 | −0.006018 | −0.024185 | −0.064257 | −0.009451 | 0.020522 | −0.058438 | 0.223873 | −0.178539 | −0.026193 | −0.013466 | 0.145393 |
| 200 | 0.007373 | 0.021155 | 0.077871 | 0.079093 | −0.065503 | 0.04582 | −0.028411 | 0.030245 | 0.003175 | 0.03997 | 0.026514 | 0.065245 | 0.04828 | −0.037808 |
| 201 | 0.115128 | −0.037873 | 0.150069 | −0.039756 | 0.008415 | −0.031675 | 0.17065 | −0.009615 | −0.128935 | −0.124357 | 0.030279 | 0.022541 | −0.071561 | −0.066006 |
| 202 | −0.013489 | −0.044456 | −0.013454 | 0.056742 | 0.033734 | −0.017542 | 0.016116 | 0.013999 | 0.048786 | 0.022143 | 0.030938 | 0.126635 | 0.005583 | −0.002651 |
| 203 | −0.14007 | 0.070666 | 0.003168 | −0.008408 | 0.10116 | 0.021346 | 0.033417 | −0.002998 | −0.0958 | 0.028879 | −0.085686 | −0.016361 | 0.030277 | 0.089038 |
| 204 | −0.101952 | 0.013508 | 0.003537 | −0.008758 | −0.022068 | −0.071548 | −0.034191 | −0.047859 | 0.139753 | −0.001873 | 0.027132 | 0.01681 | −0.022191 | −0.056252 |
| 205 | 0.017488 | −0.088611 | 0.175125 | −0.063245 | 0.043503 | 0.086559 | −0.077004 | −0.153274 | 0.025371 | −0.106716 | −0.114674 | 0.084008 | −0.09248 | −0.017213 |
| 206 | 0.06879 | 0.015625 | 0.045358 | 0.086451 | −0.032197 | 0.1002 | −0.015378 | −0.134131 | 0.066266 | −0.110037 | −0.10165 | 0.035693 | −0.10226 | 0.040782 |
| 207 | −0.039737 | −0.032705 | −0.017839 | −0.243799 | −0.223648 | 0.054937 | 0.054788 | −0.014393 | 0.078246 | −0.026239 | 0.023083 | −0.01307 | 0.122449 | −0.018458 |
| 208 | −0.119076 | 0.010683 | 0.02256 | −0.065381 | 0.044923 | 0.039647 | −0.012099 | 0.07745 | −0.047251 | −0.076664 | 0.008041 | −0.029353 | −0.050426 | −0.073174 |
| 209 | 0.143162 | 0.027256 | −0.121844 | −0.197796 | 0.072141 | −0.09384 | −0.206954 | −0.058865 | 0.150849 | −0.014273 | −0.050752 | −0.069501 | 0.014636 | −0.002045 |
| 210 | −0.013778 | 0.07848 | −0.071809 | −0.001687 | −0.037698 | −0.10674 | −0.008356 | 0.189018 | 0.118644 | 0.00525 | 0.070201 | 0.087013 | 0.031671 | 0.022077 |
| 211 | 0.061068 | −0.0363011 | 0.038239 | 0.011798 | −0.032998 | 0.01061 | −0.076064 | 0.108469 | 0.015979 | −0.031844 | 0.0945851 | 0.173415 | 0.0352071 | 0.041115 |
| 212 | 0.017 | 0.020951 | 0.161231 | 0.108521 | −0.041313 | 0.205817 | 0.244904 | 0.143994 | 0.235301 | 0.05847 | −0.008512 | −0.046768 | 0.096204 | 0.122455 |
| 213 | 0.078042 | 0.177937 | −0.133183 | 0.168773 | 0.105801 | −0.21411 | 0.231233 | 0.110813 | −0.03587 | −0.058299 | −0.097638 | −0.142155 | −0.01503 | 0.05527 |
| 214 | 0.01951 | 0.021304 | −0.012657 | −0.001538 | 0.006264 | 0.046963 | 0.015312 | 0.009665 | 0.022636 | 0.023515 | −0.012327 | −0.002298 | −0.057096 | 0.015497 |
| 215 | −0.01482 | −0.038482 | −0.017028 | 0.004009 | 0.023718 | −0.012125 | −0.015833 | 0.010504 | −0.078715 | 0.051173 | 0.03291 | −0.027155 | 0.003362 | −0.022902 |
| 216 | −0.018437 | 0.017794 | −0.01218 | −0.02092 | 0.039252 | 0.007083 | 0.020624 | 0.003381 | −0.100567 | 0.013362 | 0.000136 | 0.005677 | 0.035703 | 0.033444 |
| 217 | −0.101412 | 0.087648 | 0.068217 | −0.052081 | 0.081269 | 0.05251 | 0.000389 | −0.006921 | −0.035752 | −0.024206 | −0.004238 | −0.091377 | 0.047242 | 0.017839 |
| 218 | −0.021103 | −0.011199 | 0.003039 | −0.013012 | −0.026546 | 0.017248 | 0.003791 | −0.033718 | −0.002964 | −0.028149 | 0.031248 | −0.029753 | −0.064165 | 0.014444 |
| 219 | −0.044705 | −0.024531 | 0.019057 | 0.026637 | 0.028999 | −0.028779 | 0.007009 | 0.005897 | 0.021954 | −0.012564 | 0.031081 | −0.082831 | −0.040801 | 0.031197 |
| 220 | −0.084264 | 0.027425 | 0.06307 | −0.040531 | 0.01597 | 0.037732 | −0.028581 | 0.000376 | 0.056711 | −0.016753 | 0.046875 | −0.056836 | −0.023972 | 0.028411 |
| 221 | 0.008029 | −0.078721 | 0.013408 | −0.062755 | −0.032507 | 0.013231 | −0.029765 | −0.044198 | −0.037589 | −0.008585 | 0.011394 | −0.061793 | −0.032959 | −0.003932 |
| 222 | 0.061754 | 0.001994 | 0.010097 | −0.021848 | 0.047169 | −0.001065 | −0.013894 | −0.016132 | 0.006691 | −0.016326 | 0.015562 | 0.025485 | −0.021516 | −0.000235 |
| 223 | 0.054606 | −0.045245 | 0.04862 | 0.005832 | 0.050229 | 0.019775 | 0.008239 | −0.01312 | 0.018865 | 0.002502 | −0.003398 | 0.040272 | −0.067253 | 0.068857 |
| 224 | 0.033366 | −0.049476 | −0.036553 | 0.005227 | 0.002555 | −0.064798 | −0.037776 | 0.092488 | −0.074931 | −0.035736 | −0.006017 | 0.030388 | 0.052844 | −0.049251 |
| 225 | 0.035895 | −0.066009 | −0.028717 | 0.004358 | 0.029655 | −0.042674 | −0.015316 | 0.085649 | −0.081625 | −0.010938 | −0.027435 | 0.008682 | 0.031672 | −0.035616 |
| 226 | 0.02088 | −0.025079 | −0.004455 | 0.066349 | 0.018952 | −0.030569 | 0.032107 | −0.026116 | 0.054343 | 0.02864 | 0.01069 | −0.009666 | −0.026629 | −0.053549 |
| 227 | 0.010372 | 0.007879 | −0.006761 | 0.058915 | −0.042641 | −0.095453 | −0.065653 | 0.0231 | 0.015126 | −0.035959 | −0.055583 | −0.050051 | 0.01186 | −0.012279 |
| 228 | −0.00282 | −0.018658 | 0.00436 | 0.033106 | 0.011541 | −0.047538 | −0.025934 | 0.021747 | −0.008568 | 0.135772 | 0.026285 | 0.021393 | −0.055967 | −0.025122 |
| 229 | 0.049745 | 0.056128 | −0.003786 | 0.011014 | −0.01609 | 0.049547 | 0.013229 | 0.03698 | −0.089332 | 0.030494 | −0.028558 | −0.057311 | 0.012786 | −0.055598 |
| 230 | 0.037429 | 0.038257 | −0.001331 | 0.027645 | −0.076648 | −0.010815 | −0.06628 | 0.004674 | −0.044708 | 0.044333 | −0.020332 | 0.107115 | 0.015426 | −0.012178 |
| 231 | 0.025923 | 0.003058 | −0.023773 | 0.023293 | −0.039007 | −0.034384 | −0.0263 | −0.014836 | 0.044413 | 0.0083 | −0.02168 | 0.02618 | 0.035307 | −0.087209 |
| 232 | 0.123426 | 0.068588 | −0.013864 | 0.050108 | −0.031553 | −0.045493 | −0.025791 | −0.01538 | −0.071406 | 0.067991 | 0.118863 | 0.052824 | −0.07636 | 0.002918 |
| 233 | 0.05013 | 0.056976 | 0.005739 | 0.030071 | −0.088568 | −0.000501 | 0.040275 | 0.067468 | −0.067735 | −0.001623 | −0.042626 | −0.008881 | −0.072054 | −0.012163 |
| 234 | −0.032913 | −0.005492 | 0.000538 | 0.036088 | −0.08064 | −0.003313 | −0.033529 | 0.012009 | 0.030255 | 0.101359 | 0.034479 | 0.001316 | −0.024036 | −0.096148 |
| 235 | −0.052774 | −0.063323 | −0.014758 | 0.044376 | −0.027811 | −0.027523 | −0.048758 | 0.021921 | 0.042253 | 0.083904 | 0.012511 | 0.006186 | 0.044141 | −0.052008 |
| 236 | −0.015473 | 0.00148 | −0.00213 | 0.007029 | −0.008766 | −0.051203 | −0.051123 | −0.066685 | −0.039637 | −0.057645 | −0.009963 | 0.024265 | 0.055647 | −0.022039 |
| 237 | −0.017845 | −0.020264 | 0.018001 | 0.011419 | 0.019031 | −0.026909 | −0.004436 | 0.041109 | −0.024995 | 0.000527 | 0.01546 | −0.061525 | 0.012139 | 0.012682 |
| 238 | 0.005157 | −0.005826 | 0.030495 | 0.039431 | 0.024625 | 0.002285 | −0.03827 | 0.04393 | 0.035776 | 0.018205 | 0.017163 | −0.008196 | −0.037098 | −0.024055 |
| 239 | 0.030991 | 0.006847 | 0.017698 | 0.021603 | −0.003084 | −0.030256 | 0.02161 | 0.026301 | 0.032484 | 0.019041 | −0.003966 | 0.027505 | −0.057162 | −0.016839 |
| 240 | −0.07038 | 0.074806 | −0.014864 | −0.041536 | 0.000682 | −0.038678 | 0.027984 | −0.049887 | −0.035053 | −0.033026 | −0.020921 | 0.071892 | 0.077391 | −0.077447 |
| 241 | −0.018911 | 0.100512 | −0.067754 | −0.011563 | −0.061482 | −0.029989 | 0.062378 | −0.007391 | −0.046913 | −0.029727 | −0.046648 | 0.071393 | 0.016014 | −0.034376 |
| 242 | −0.003669 | −0.08134 | 0.055871 | 0.021179 | −0.003248 | 0.009093 | −0.025834 | −0.015782 | −0.071995 | −0.028704 | −0.057637 | 0.029372 | −0.023199 | 0.018554 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 243 | −0.011757 | −0.091479 | 0.029199 | 0.062979 | −0.023819 | 0.009357 | 0.021808 | 0.051002 | 0.021357 | 0.001968 | −0.015282 | −0.086847 | −0.076824 | 0.010052 |
| 244 | 0.009147 | −0.02365 | −0.019065 | −0.046365 | 0.019038 | 0.024997 | −0.021278 | 0.003131 | −0.036187 | −0.027374 | −0.046928 | 0.005121 | −0.026193 | 0.03018 |
| 245 | 0.035485 | 0.059659 | −0.069534 | −0.071898 | −0.028853 | −0.007064 | 0.013839 | 0.010977 | −0.059679 | −0.06437 | −0.123683 | −0.017731 | 0.042172 | −0.070197 |
| 246 | −0.025646 | 0.012933 | 0.045114 | −0.011107 | −0.045204 | −0.015059 | −0.030128 | 0.011784 | −0.028711 | 0.057762 | 0.028328 | −0.02798 | 0.00258 | −0.030954 |
| 247 | −0.014841 | −0.013174 | 0.040081 | 0.005807 | −0.017312 | −0.057418 | −0.016725 | −0.034204 | −0.007994 | 0.04008 | 0.0037631 | 0.004721 | 0.002314 | 0.033208 |
| 248 | 0.005346 | 0.004559 | 0.0323721 | 0.040568 | −0.01723 | −0.063371 | −0.040231 | −0.077419 | 0.0419161 | 0.026941 | 0.0373661 | 0.0004171 | 0.0026971 | −0.006675 |
| 249 | −0.003767 | 0.115556 | −0.014927 | 0.019216 | 0.021589 | −0.031927 | 0.045127 | −0.06934 | 0.00631 | −0.053095 | 0.061586 | 0.069062 | 0.066633 | −0.065212 |
| 250 | −0.099748 | 0.052803 | −0.025286 | −0.026855 | 0.004033 | −0.016326 | 0.016968 | −0.030063 | 0.000322 | 0.001791 | 0.022588 | 0.086708 | 0.043916 | −0.062226 |
| 251 | −0.126775 | 0.022055 | −0.02337 | −0.024076 | −0.019348 | −0.007815 | −0.010429 | −0.011162 | 0.014115 | 0.012167 | −0.020285 | 0.040988 | 0.019012 | −0.047915 |
| 252 | 0.020982 | 0.057277 | −0.083482 | −0.017799 | −0.106585 | −0.003932 | 0.049245 | −0.03737 | −0.011762 | −0.054107 | −0.086372 | −0.025691 | −0.00714 | −0.001369 |
| 253 | 0.086629 | 0.018944 | −0.027645 | 0.008593 | 0.04089 | 0.076834 | 0.035018 | −0.038123 | −0.016362 | −0.00887 | 0.030247 | −0.094835 | −0.030333 | 0.009667 |
| 254 | 0.002081 | −0.021074 | −0.0029941 | −0.000059 | 0.057227 | 0.00768 | 0.015172 | 0.010712 | −0.003825 | −0.036333 | 0.004753 | 0.035285 | −0.025308 | 0.088866 |
| 255 | −0.050551 | −0.025313 | −0.021065 | −0.031803 | 0.011393 | 0.020298 | −0.047873 | 0.017712 | −0.044526 | 0.012887 | 0.009816 | −0.019025 | 0.016518 | 0.058697 |
| 256 | 0.04206 | 0.052223 | −0.109669 | −0.042157 | −0.037166 | 0.068809 | 0.002851 | 0.018853 | −0.114009 | −0.009917 | 0.03136 | −0.078075 | 0.041693 | −0.08718 |
| 257 | −0.003877 | 0.025515 | −0.028653 | −0.039198 | 0.016445 | 0.05018 | −0.009689 | −0.023606 | 0.014581 | −0.018142 | 0.04781 | 0.00524 | 0.030181 | −0.019145 |
| 258 | 0.004749 | 0.042733 | −0.001588 | −0.025262 | −0.002348 | −0.047077 | −0.021349 | −0.005726 | −0.026672 | 0.0041661 | −0.028366 | −0.002061 | 0.0434731 | 0.035676 |
| 259 | −0.04029 | 0.008059 | 0.024109 | 0.010551 | 0.019367 | −0.018105 | 0.021927 | −0.022408 | 0.00669 | −0.032739 | 0.014136 | 0.054513 | 0.033479 | −0.012073 |
| 260 | −0.020855 | 0.023183 | −0.039977 | −0.000196 | −0.067646 | −0.049292 | 0.040777 | −0.01984 | 0.01891 | −0.03647 | −0.107127 | 0.026938 | 0.016669 | 0.056544 |
| 261 | −0.032253 | 0.031546 | 0.00674 | 0.018464 | −0.040153 | −0.01405 | 0.027167 | −0.045051 | 0.020239 | 0.005186 | −0.062639 | 0.009036 | −0.005816 | −0.010844 |
| 262 | 0.04962 | 0.014614 | 0.034732 | −0.002586 | −0.007834 | −0.033047 | −0.022145 | −0.048064 | 0.009179 | 0.008097 | 0.003395 | 0.06817 | 0.020518 | 0.015877 |
| 263 | 0.0185281 | 0.020594 | 0.008769 | −0.003744 | 0.003137 | −0.011099 | −0.013103 | −0.056818 | 0.0225241 | −0.023785 | 0.0129861 | 0.0582871 | 0.0205351 | 0.004741 |
| 264 | 0.0185431 | 0.028406 | −0.052445 | −0.001676 | 0.033265 | 0.003178 | 0.0172 | 0.010057 | 0.027261 | −0.031933 | 0.016009 | 0.010301 | 0.031176 | 0.029499 |
| 265 | 0.003845 | 0.015905 | −0.009669 | 0.062469 | 0.069014 | 0.062729 | 0.028041 | 0.002082 | −0.00231 | 0.026741 | 0.005303 | −0.004045 | −0.076006 | 0.022422 |
| 266 | −0.010596 | −0.00019 | 0.038888 | 0.052845 | 0.062157 | 0.079958 | 0.022105 | 0.017357 | −0.014741 | 0.039382 | −0.028729 | 0.002712 | −0.077913 | −0.014226 |
| 267 | 0.10473 | 0.044105 | −0.054638 | −0.003618 | 0.017021 | 0.012062 | 0.080059 | −0.041993 | −0.030004 | 0.0173 | 0.052427 | 0.002935 | −0.074291 | −0.021233 |
| 268 | 0.033461 | −0.023597 | −0.0283091 | 0.038436 | 0.010357 | −0.018511 | 0.052948 | −0.024866 | 0.0262141 | 0.0127771 | 0.0285511 | 0.0162091 | −0.009741 | −0.007065 |
| 269 | 0.030006 | −0.036437 | −0.034248 | 0.064287 | 0.026114 | −0.013758 | 0.019572 | −0.020435 | 0.049347 | 0.022539 | 0.046287 | −0.016832 | −0.000747 | −0.01565 |
| 270 | −0.009546 | 0.017324 | −0.025682 | 0.060379 | 0.015018 | −0.045791 | −0.011875 | −0.038102 | 0.069336 | −0.003644 | 0.013362 | −0.005875 | −0.015656 | 0.018841 |
| 271 | −0.006478 | 0.031042 | −0.140675 | −0.011543 | 0.164865 | 0.031231 | 0.086717 | 0.018034 | 0.003565 | −0.010661 | −0.080203 | 0.014374 | 0.051555 | 0.047445 |
| 272 | 0.044546 | 0.014984 | −0.003309 | 0.028743 | 0.012299 | 0.03966 | 0.0432 | −0.035026 | −0.028669 | 0.047567 | −0.001399 | 0.001057 | 0.024012 | −0.032214 |
| 273 | −0.020849 | 0.019549 | 0.010739 | 0.051236 | −0.072675 | −0.004989 | −0.01142 | −0.029471 | 0.039335 | −0.016521 | −0.013283 | 0.070361 | −0.011078 | 0.015193 |
| 274 | −0.02639 | 0.021585 | 0.013281 | 0.066202 | −0.069035 | −0.004906 | −0.020789 | −0.026647 | 0.037062 | −0.019078 | −0.018486 | 0.057697 | −0.002677 | 0.01131 |
| 275 | −0.034847 | 0.079754 | 0.039799 | 0.062121 | −0.087721 | −0.049507 | −0.073553 | −0.052921 | 0.031484 | −0.01034 | −0.057419 | 0.088207 | 0.006018 | 0.061367 |
| 276 | −0.001012 | 0.008544 | −0.015977 | 0.007538 | −0.007877 | −0.032096 | −0.040558 | −0.076779 | −0.046141 | −0.059065 | −0.011552 | 0.042717 | 0.055616 | −0.033679 |
| 277 | 0.021474 | −0.027403 | 0.031173 | −0.002327 | −0.020279 | −0.011248 | 0.055838 | −0.000592 | −0.037003 | −0.012074 | −0.027681 | 0.033856 | −0.004003 | 0.017602 |
| 278 | 0.049487 | −0.004924 | 0.018538 | −0.009011 | −0.029427 | −0.014893 | 0.056003 | 0.000493 | −0.010827 | 0.006238 | −0.04228 | 0.063378 | −0.011393 | −0.006043 |
| 279 | 0.036066 | −0.007528 | −0.0166921 | 0.035924 | 0.001455 | −0.021087 | 0.002651 | 0.009232 | 0.071907 | 0.033358 | −0.011473 | 0.056619 | −0.054207 | −0.017941 |
| 280 | 0.037741 | −0.109893 | 0.023954 | 0.019129 | 0.008097 | 0.079985 | 0.036128 | 0.060775 | −0.055655 | −0.036045 | 0.006375 | −0.057639 | −0.089455 | 0.001997 |
| 281 | −0.013063 | 0.002636 | 0.084526 | −0.018327 | −0.025019 | −0.026906 | 0.027773 | 0.046599 | 0.02567 | 0.066247 | −0.061101 | 0.021506 | 0.002029 | −0.002914 |
| 282 | 0.034121 | 0.017543 | 0.023938 | −0.045204 | −0.055084 | −0.006092 | 0.004521 | 0.04416 | 0.060845 | 0.050014 | −0.062887 | 0.045979 | 0.009917 | 0.00333 |
| 283 | 0.00159 | −0.037585 | 0.025184 | 0.065723 | −0.041056 | −0.064235 | −0.016628 | −0.038476 | 0.071393 | 0.021112 | −0.036283 | 0.03137 | −0.02055 | −0.003464 |
| 284 | 0.001777 | −0.002963 | −0.040046 | −0.027154 | −0.004822 | 0.066941 | −0.015575 | −0.017035 | 0.023899 | −0.016392 | 0.031154 | 0.010967 | 0.034046 | −0.020965 |
| 285 | −0.007609 | 0.010961 | −0.04096 | −0.022471 | 0.000258 | 0.060592 | −0.016809 | −0.005409 | 0.036933 | −0.01025 | 0.037369 | 0.024258 | 0.020281 | 0.000103 |
| 286 | 0.026874 | 0.054367 | −0.018516 | −0.042184 | 0.000776 | 0.007904 | 0.012593 | 0.061033 | −0.00255 | −0.013724 | −0.050408 | −0.014417 | 0.050654 | 0.066343 |
| 287 | 0.040659 | 0.0473781 | −0.036474 | −0.028463 | −0.007785 | −0.003117 | −0.002967 | 0.051838 | 0.021853 | −0.013034 | −0.049807 | 0.018499 | 0.030873 | 0.063452 |
| 288 | 0.003939 | 0.033474 | 0.001172 | −0.038607 | −0.00578 | −0.081137 | −0.061347 | −0.001459 | −0.024737 | 0.060639 | −0.044944 | 0.018439 | 0.039576 | 0.034139 |
| 289 | −0.017699 | 0.027685 | 0.034499 | 0.007219 | 0.031682 | −0.018506 | −0.030987 | −0.025776 | −0.012813 | 0.010563 | 0.018367 | 0.070102 | 0.009774 | 0.01626 |
| 290 | −0.014315 | −0.068724 | 0.029737 | −0.031901 | 0.04751 | −0.049881 | 0.017062 | 0.037667 | −0.016972 | −0.004826 | 0.079157 | −0.001232 | 0.000882 | 0.01304 |
| 291 | −0.015519 | −0.070573 | 0.025265 | −0.040011 | 0.043165 | −0.048795 | 0.020466 | 0.033169 | −0.017402 | −0.009531 | 0.082028 | −0.000696 | 0.00162 | 0.007882 |
| 292 | −0.022054 | −0.068097 | 0.01942 | −0.029898 | 0.049915 | −0.035568 | −0.006414 | 0.031738 | 0.015804 | 0.022662r | 0.086185 | 0.024272 | −0.019614 | −0.001717 |
| 293 | 0.053237 | −0.011183 | 0.027014 | −0.011249 | −0.007222 | −0.008555 | 0.016133 | 0.006074 | −0.121073 | 0.045508 | −0.01862 | −0.047976 | 0.097277 | 0.022768 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 294 | −0.005444 | 0.012094 | 0.038294 | −0.000114 | −0.02988 | −0.043168 | −0.001579 | 0.024432 | 0.0045461 | 0.013031 | −0.041181 | −0.016121 | −0.051352 | −0.026048 |
| 295 | 0.00162 | 0.006601 | 0.034857 | 0.01891 | −0.073573 | 0.035901 | 0.01492 | 0.009488 | −0.039393 | −0.003772 | −0.034538 | 0.026039 | 0.007322 | −0.021231 |
| 296 | −0.035522 | 0.023759 | 0.045242 | 0.009563 | −0.03282 | −0.051944 | 0.021367 | −0.039159 | −0.02108 | 0.03058 | −0.08569 | 0.031795 | −0.095786 | 0.046422 |
| 297 | 0.007132 | 0.026521 | 0.023683 | −0.044342 | −0.046498 | 0.014041 | 0.0187 | 0.011582 | −0.041958 | −0.022788 | −0.025941 | 0.042706 | 0.021845 | −0.045423 |
| 298 | 0.001341 | −0.05143 | 0.050748 | −0.035827 | −0.037224 | 0.053037 | 0.019587 | 0.057772 | 0.054343 | 0.034344 | 0.106408 | −0.012093 | −0.058979 | 0.081733 |
| 299 | −0.015701 | −0.006704 | −0.002315 | −0.006387 | −0.021316 | 0.003038 | 0.056717 | 0.031557 | −0.010176 | 0.000258 | −0.036642 | −0.020032 | 0.021748 | −0.067106 |
| 300 | 0.030302 | −0.05718 | 0.131946 | 0.015973 | 0.027957 | 0.048324 | 0.03137 | 0.028564 | 0.147924 | 0.050262 | 0.110812 | 0.081821 | 0.007172 | 0.138759 |
| 301 | 0.005059 | −0.022201 | 0.018409 | −0.016913 | −0.024822 | 0.056194 | 0.027431 | −0.006381 | −0.027688 | 0.029611 | 0.007403 | −0.041154 | 0.023574 | −0.056367 |
| 302 | −0.061014 | 0.006407 | 0.038652 | −0.013595 | −0.008908 | 0.000081 | 0.024983 | 0.00217 | 0.028214 | −0.004502 | 0.027593 | −0.000054 | 0.010959 | −0.036987 |
| 303 | 0.007062 | −0.027317 | −0.021261 | −0.011516 | −0.05568 | −0.012439 | 0.065559 | 0.048716 | 0.021313 | 0.026801 | −0.050031 | −0.045693 | −0.028154 | −0.084165 |
| 304 | −0.005078 | 0.009972 | 0.0214991 | −0.002098 | −0.06468 | −0.026971 | 0.013174 | −0.032109 | 0.025697 | 0.0058661 | −0.018345 | −0.064296 | −0.027681 | −0.070375 |
| 305 | −0.015695 | 0.020103 | 0.003891 | −0.064033 | −0.03263 | −0.005525 | 0.066601 | −0.039753 | −0.024639 | 0.040744 | 0.028774 | −0.024107 | −0.070057 | −0.006716 |
| 306 | −0.008949 | 0.002836 | −0.00011 | −0.04196 | 0.004591 | −0.03847 | 0.026832 | −0.093403 | 0.004789 | −0.017634 | 0.015749 | −0.021426 | 0.026932 | 0.047551 |
| 307 | 0.133415 | 0.075792 | 0.003603 | 0.16912 | 0.022613 | 0.131495 | −0.07703 | 0.044678 | 0.010229 | −0.146173 | −0.203585 | 0.144978 | 0.131456 | 0.01907 |
| 308 | 0.000487 | 0.05334 | −0.046349 | 0.001201 | 0.015413 | −0.027071 | −0.040402 | −0.021144 | 0.000237 | −0.005841 | 0.027317 | 0.016288 | −0.011145 | −0.001317 |
| 309 | −0.04461 | 0.001263 | −0.041393 | 0.010352 | 0.050485 | 0.005029 | −0.028883 | −0.027413 | −0.007783 | −0.011209 | 0.026357 | 0.022456 | −0.002046 | 0.010551 |
| 310 | −0.046177 | 0.030779 | −0.041994 | −0.031211 | 0.048904 | −0.012908 | −0.000804 | −0.006981 | −0.013563 | −0.043621 | 0.026157 | −0.026996 | 0.044272 | 0.018498 |
| 311 | −0.013006 | −0.051795 | 0.007621 | 0.050005 | 0.009865 | 0.000519 | 0.015986 | −0.011454 | −0.051583 | −0.062818 | −0.015529 | 0.057829 | 0.014024 | 0.048086 |
| 312 | 0.01673 | 0.020125 | 0.06229 | −0.060588 | 0.064009 | −0.064251 | 0.009785 | 0.074915 | 0.009291 | −0.016589 | 0.003573 | −0.045378 | −0.079736 | −0.16179 |
| 313 | −0.017354 | −0.015209 | 0.023382 | 0.01769 | 0.002997 | 0.044209 | 0.024495 | −0.012193 | −0.013317 | −0.022529 | 0.05722 | 0.044954 | −0.011488 | 0.037513 |
| 314 | −0.085824 | 0.066131 | 0.061264 | −0.064063 | 0.0372 | −0.011435 | −0.058373 | −0.009593 | 0.067008 | −0.094084 | 0.111371 | 0.058345 | 0.013214 | −0.038913 |
| 315 | −0.039402 | −0.039526 | −0.021932 | 0.011939 | 0.049348 | 0.024521 | −0.008377 | 0.023119 | −0.05847 | 0.020323 | −0.010189 | 0.051499 | 0.001776 | 0.01306 |
| 316 | 0.05771 | 0.00809 | −0.084169 | 0.014356 | 0.010498 | 0.15204 | 0.046251 | −0.09318 | 0.017848 | 0.066002 | 0.179601 | −0.11503 | −0.025695 | 0.113791 |
| 317 | −0.039233 | −0.046676 | −0.025111 | 0.012264 | 0.06366 | 0.047369 | −0.009248 | −0.013058 | −0.023857 | −0.014637 | 0.022472 | 0.02968 | 0.009562 | 0.010928 |
| 318 | −0.013927 | −0.008981 | 0.043322 | 0.008022 | 0.054636 | 0.040053 | −0.036761 | 0.038616 | −0.031095 | −0.028821 | −0.032622 | 0.022617 | 0.018973 | 0.005277 |
| 319 | −0.019831 | −0.052567 | −0.03571 | 0.020284 | 0.02234 | 0.038778 | −0.013551 | 0.017729 | −0.033777 | −0.001824 | −0.020445 | 0.02539 | 0.020863 | −0.005659 |
| 320 | −0.018784 | −0.010189 | 0.01235 | −0.010456 | −0.042954 | −0.005455 | −0.001588 | 0.037344 | −0.023514 | 0.011175 | 0.047034 | −0.022664 | −0.007635 | 0.031623 |
| 321 | 0.018609 | 0.092144 | −0.051134 | 0.023843 | −0.087477 | 0.026706 | −0.050403 | 0.059883 | −0.011825 | 0.036468 | −0.019069 | 0.115304 | 0.016328 | −0.022282 |
| 322 | 0.097585 | 0.100752 | −0.012662 | −0.098405 | 0.133 | 0.065354 | −0.110192 | 0.009689 | 0.021961 | 0.08284 | −0.016566 | −0.0798 | −0.012252 | 0.026028 |
| 323 | −0.018925 | −0.013488 | −0.002902 | 0.021384 | −0.053405 | 0.026667 | 0.048667 | 0.064203 | −0.008173 | 0.016738 | 0.097745 | 0.045579 | −0.006412 | −0.087244 |
| 324 | −0.075189 | 0.035133 | 0.049763 | 0.033139 | 0.144903 | −0.10736 | −0.06325 | −0.080811 | 0.0312281 | −0.083355 | −0.011453 | −0.064153 | 0.0107411 | 0.056998 |
| 325 | −0.055376 | −0.03394 | −0.01527 | 0.032375 | 0.014199 | −0.021175 | −0.043241 | −0.047143 | −0.027673 | 0.050536 | −0.074542 | −0.030582 | −0.049605 | 0.010039 |
| 326 | −0.105391 | −0.011159 | −0.053457 | 0.064177 | 0.055436 | −0.050082 | 0.109039 | 0.030225 | 0.020191 | −0.111934 | −0.092525 | 0.030079 | 0.038267 | −0.019523 |
| 327 | −0.02607 | −0.021562 | −0.008041 | 0.016047 | −0.028628 | 0.003446 | −0.017094 | 0.003615 | −0.001781 | −0.010764 | 0.005395 | 0.022585 | −0.020243 | 0.011468 |
| 328 | −0.01228 | 0.101575 | −0.035475 | −0.094006 | 0.026387 | −0.120053 | 0.024364 | −0.12285 | 0.021167 | 0.097624 | 0.111694 | 0.038469 | −0.21133 | 0.115012 |
| 329 | −0.044115 | −0.011091 | 0.027753 | 0.006785 | −0.003051 | −0.009486 | 0.071561 | 0.025124 | 0.027755 | 0.002302 | 0.032686 | 0.029313 | −0.021671 | −0.033902 |
| 330 | 0.08516 | −0.051764 | −0.138181 | 0.072886 | −0.152329 | −0.11489 | 0.128471 | −0.049846 | −0.025631 | −0.011504 | −0.037938 | 0.0895761 | −0.042563 | 0.045411 |
| 331 | −0.002446 | −0.029553 | −0.001239 | 0.020675 | 0.053672 | −0.026527 | −0.000689 | 0.010322 | −0.055562 | 0.018912 | −0.003801 | 0.016193 | 0.024067 | −0.004516 |
| 337 | 0.071219 | 0.005125 | −0.163178 | 0.08708 | −0.060274 | 0.024925 | 0.041973 | −0.160442 | 0.047465 | −0.051537 | 0.003323 | 0.014217 | 0.117983 | −0.038524 |
| 333 | −0.045442 | −0.029147 | −0.014269 | 0.021094 | 0.051611 | −0.004921 | −0.04229 | −0.008949 | −0.084411 | 0.018681 | −0.035814 | 0.002633 | 0.020277 | −0.009069 |
| 334 | −0.059377 | −0.073284 | 0.08464 | −0.155578 | −0.000722 | −0.034407 | 0.031666 | 0.024015 | 0.003151 | 0.163927 | −0.088854 | 0.01084 | −0.054031 | −0.096282 |
| 335 | −0.032119 | −0.021415 | −0.018096 | 0.059081 | 0.014729 | −0.002544 | −0.040639 | 0.003531 | −0.007663 | −0.015736 | −0.040102 | −0.022538 | 0.0287641 | −0.018059 |
| 336 | −0.046491 | 0.0388471 | −0.025026 | 0.046529 | 0.015151 | −0.061199 | −0.05807 | 0.026334 | −0.114068 | 0.003414 | 0.042166 | −0.054663 | 0.015864 | 0.018387 |
| 337 | −0.063847 | −0.037266 | −0.053001 | −0.016778 | 0.088961 | 0.069352 | 0.012927 | −0.015204 | 0.008972 | 0.064453 | −0.110632 | −0.128574 | 0.023239 | −0.03099 |
| 338 | 0.174551 | −0.126417 | −0.109918 | −0.022812 | 0.005404 | 0.039786 | −0.063962 | −0.052411 | −0.011051 | −0..090892 | 0.012803 | −0.062862 | 0.01562 | 0.152052 |
| 339 | 0.0218831 | −0.009175 | 0.001034 | 0.001706 | 0.044073 | −0.000066 | 0.107048 | 0.041798 | 0.006906 | 0.021745 | −0.081414 | 0.036535 | 0.080339 | −0.071796 |
| 340 | −0.006317 | −0.1320891 | −0.117791 | 0.054825 | −0.046091 | 0.009063 | 0.015449 | −0.162181 | −0.095257 | 0.1060921 | −0.10826 | −0.103507 | −0.051619 | −0.057423 |

APPENDIX B2-continued

| PCA Transformation Matrix (340 × 340; Benign/Malignant) | | | | | | | | | | | | | | |
|---|---|---|---|---|---|---|---|---|---|---|---|---|---|---|
| | BB | BC | BD | BE | BF | BG | BH | BI | BJ | BK | BL | BM | BN | BO |
| 1 | 0.010321 | 0.015235 | −0.078844 | 0.018027 | −0.025941 | −0.036885 | −0.019735 | −0.060176 | 0.031432 | 0.008088 | −0.00732 | 0.023785 | −0.00702 | −0.002315 |
| 2 | 0.029521 | −0.04017 | −0.041832 | 0.023561 | 0.005695 | −0.019711 | 0.020769 | −0.026461 | 0.051366 | 0.039071 | 0.013947 | −0.050184 | −0.037735 | 0.014361 |
| 3 | 0.016464 | 0.021028 | 0.008561 | −0.023777 | 0.002365 | −0.047679 | −0.000782 | −0.041402 | −0.020315 | −0.031657 | 0.011578 | −0.002294 | −0.050247 | 0.006967 |
| 4 | −0.11628 | −0.013165 | −0.062836 | 0.095628 | −0.080736 | 0.039752 | −0.109802 | −0.02687 | 0.000784 | −0.061442 | 0.016161 | 0.049813 | 0.060702 | −0.007814 |
| 5 | 0.034501 | −0.182703 | −0.058022 | −0.119438 | −0.021252 | 0.075357 | −0.147187 | −0.27347 | 0.116987 | −0.040314 | 0.042021 | 0.003193 | −0.00224 | 0.035884 |
| 6 | 0.003777 | −0.07351 | 0.039153 | −0.036564 | −0.06995 | 0.003004 | 0.055735 | 0.055162 | 0.028091 | 0.014819 | 0.026321 | 0.044093 | −0.006174 | 0.011548 |
| 7 | 0.088066 | −0.040312 | 0.099547 | −0.043582 | 0.107546 | −0.011175 | 0.030709 | 0.035065 | 0.104539 | −0.020135 | 0.069712 | −0.01274 | −0.067295 | −0.035703 |
| 8 | −0.035113 | −0.00697 | 0.033772 | 0.083963 | 0.043144 | 0.041643 | −0.055928 | −0.144621 | −0.002308 | −0.065093 | −0.017193 | −0.021935 | 0.036824 | 0.027162 |
| 9 | −0.107322 | −0.095635 | −0.15671 | 0.075254 | −0.043499 | −0.008628 | −0.112291 | −0.02633 | −0.039049 | −0.04598 | −0.084324 | −0.11263 | 0.035163 | −0.033971 |
| 10 | −0.059446 | −0.088321 | 0.090835 | −0.030495 | −0.010876 | 0.040941 | −0.015586 | −0.003626 | 0.085343 | 0.043014 | 0.008826 | −0.072926 | −0.083123 | 0.082923 |
| 11 | −0.17007 | 0.134103 | −0.062541 | −0.117212 | 0.118167 | 0.128622 | 0.123582 | −0.107283 | −0.004863 | 0.089261 | −0.017562 | 0.107308 | −0.086688 | −0.068868 |
| 12 | −0.041122 | −0.044243 | −0.117531 | 0.072843 | 0.113801 | −0.054505 | 0.080688 | −0.00635 | −0.004063 | 0.048331 | −0.062299 | 0.030989 | 0.082708 | −0.018795 |
| 13 | −0.046646 | 0.009034 | −0.011192 | −0.051821 | 0.048884 | 0.035249 | 0.01602 | −0.070396 | −0.146583 | −0.019376 | 0.02877 | −0.023674 | −0.016323 | 0.050716 |
| 14 | −0.027463 | 0.06917 | −0.049176 | −0.046477 | −0.066852 | 0.005838 | 0.067471 | −0.096179 | −0.063382 | −0.058931 | 0.014344 | .065483 | 0.085284 | 0.071538 |
| 15 | 0.030355 | 0.063122 | −0.05494 | 0.036049 | −0.034121 | −0.009155 | 0.031428 | −0.008609 | 0.014888 | 0.021397 | 0.048764 | 0.037008 | 0.002693 | 0.035962 |
| 16 | −0.089933 | −0.024093 | 0.0267611 | 0.077836 | −0.015762 | −0.086006 | 0.043975 | −0.020964 | 0.01176 | 0.051852 | 0.135023 | 0.077954 | −0.25542 | 0.119644 |
| 17 | 0.025171 | −0.01284 | −0.077967 | −0.174873 | −0.05858 | −0.014025 | 0.113062 | −0.059195 | 0.0307 | 0.053781 | 0.033806 | 0.028483 | −0.043071 | −0.062346 |
| 18 | 0.041259 | 0.12806 | 0.003459 | 0.01855 | −0.00043 | 0.023144 | 0.035498 | −0.045195 | 0.128403 | 0.040202 | −0.004355 | −0.121559 | −0.024903 | 0.056953 |
| 19 | −0.048641 | 0.047597 | −0.001732 | −0.047747 | −0.022384 | 0.035733 | 0.018145 | 0.023148 | 0.022741 | −0.045204 | 0.047427 | 0.021991 | −0.071784 | 0.033494 |
| 20 | −0.01598 | −0.040575 | −0.002358 | −0.057842 | −0.004459 | −0.007022 | 0.001473 | −0.004295 | −0.047161 | −0.002605 | 0.003474 | −0.038161 | −0.025912 | 0.063387 |
| 21 | 0.001986 | −0.034473 | −0.020849 | 0.035914 | 0.043655 | −0.100579 | −0.03252 | −0.042545 | 0.123584 | 0.079588 | 0.071988 | −0.004162 | 0.09268 | −0.061682 |
| 22 | −0.04406 | −0.103901 | 0.019054 | 0.034765 | −0.004058 | 0.008155 | −0.049173 | 0.079792 | −0.01684 | −0.121006 | 0.030589 | 0.087737 | −0.058506 | 0.051585 |
| 23 | −0.046473 | −0.119281 | −0.030503 | 0.028918 | −0.019081 | 0.020788 | 0.0014 | 0.022201 | −0.062962 | −0.015351 | −0.167477 | 0.171779 | −0.017229 | 0.119274 |
| 24 | 0.036102 | 0.010166 | 0.067111 | −0.009768 | 0.073581 | −0.059287 | 0.003682 | 0.090121 | −0.073384 | −0.099711 | −0.005486 | −0.117064 | −0.062901 | 0.048854 |
| 25 | 0.010003 | −0.040982 | −0.040634 | 0.038357 | −0.04085 | 0.032753 | −0.02483 | 0.034943 | 0.111671 | −0.033615 | 0.01247 | −0.056046 | 0.028727 | −0.019003 |
| 26 | 0.003228 | 0.004602 | −0.007004 | −0.045647 | −0.001961 | −0.039499 | 0.016239 | −0.021347 | −0.017106 | 0.023567 | −0.004082 | −0.046191 | 0.00641 | 0.036875 |
| 27 | −0.004722 | 0.000645 | 0.004977 | −0.034838 | 0.007471 | −0.013401 | 0.00086 | −0.009074 | −0.02281 | 0.003683 | −0.009655 | −0.012342 | −0.018525 | 0.034681 |
| 28 | −0.008705 | −0.009598 | −0.006937 | 0.031851 | −0.047929 | 0.011841 | −0.058127 | 0.013624 | 0.045778 | −0.019548 | 0.00069 | 0.107247T | 0.04989 | −0.116152 |
| 29 | −0.091971 | 0.141753 | 0.093469 | 0.155941 | 0.014097 | −0.023685 | −0.01117 | −0.101365 | −0.036402 | −0.017432 | −0.067108 | 0.082347 | 0.06393 | −0.21796 |
| 30 | 0.039265 | 0.03956 | 0.036775 | 0.018931 | 0.046278 | −0.001525 | 0.013144 | 0.028603 | 0.006454 | 0.015376 | −0.038106 | −0.015316 | 0.020986 | 0.007462 |
| 31 | 0.013787 | 0.008132 | 0.024999 | −0.040034 | 0.065091 | −0.003741 | −0.003953 | −0.008252 | 0.05199 | −0.048288 | 0.025354 | −0.005857 | 0.055656 | −0.01852 |
| 32 | 0.098124 | 0.016104 | −0.090847 | 0.063567 | 0.013953 | 0.020689 | 0.007157 | 0.080208 | 0.049647 | −0.103381 | 0.01884 | 0.004288 | −0.005533 | −0.026655 |
| 33 | 0.008873 | 0.047869 | 0.0546661 | 0.084791 | −0.054788 | 0.04895 | 0.027604 | −0.101019 | 0.043057 | 0.017828 | 0.014876 | −0.010122 | 0.065499 | 0.065678 |
| 34 | −0.019367 | −0.01536 | −0.005207 | −0.00491 | −0.043618 | 0.031248 | 0.064879 | 0.017396 | 0.020376 | −0.114575 | 0.025273 | −0.047981 | −0.080229 | −0.072072 |
| 35 | −0.117855 | 0.05974 | −0.022742 | −0.022503 | −0.028966 | 0.104139 | −0.091215 | 0.015104 | −0.010321 | −0.09014 | −0.021977 | 0.080436 | 0.037935 | −0.001397 |
| 36 | 0.037299 | −0.036915 | 0.00671 | −0.090829 | 0.027898 | −0.041344 | −0.068854 | −0.028595 | −0.077629 | 0.028597 | −0.00737 | 0.097436 | −0.054867 | 0.045068 |
| 37 | 0.017448 | 0.038332 | 0.070643 | −0.068914 | 0.002806 | −0.00267 | −0.039387 | 0.005071 | −0.057993 | −0.02013 | −0.089524 | −0.072318 | −0.090197 | 0.015186 |
| 38 | −0.101064 | −0.012121 | −0.011397 | 0.109992 | 0.036184 | 0.062553 | −0.02764 | 0.017267 | −0.025355 | −0.014156 | 0.009636 | 0.053296 | −0.030983 | −0.026718 |
| 39 | −0.016886 | −0.089766 | 0.020861 | .050546 | 0.062175 | 0.006309 | −0.014985 | 0.037013 | −0.059414 | 0.101825 | −0.037611 | −0.038344 | −0.015568 | −0.016021 |
| 40 | 0.035799 | −0.021144 | −0.00672 | −0.017343 | −0.003849 | −0.027414 | 0.0707 | 0.019467 | 0.009384 | −0.005097 | −0.013967 | −0.008321 | −0.038767 | −0.032636 |
| 41 | 0.055531 | −0.033118 | −0.000042 | 0.0028661 | 0.034083 | −0.011773 | 0.032394 | 0.005521 | −0.022553 | 0.018008 | −0.019216 | 0.012319 | −0.03105 | −0.007217 |
| 42 | 0.068172 | −0.051517 | −0.008216 | 0.062095 | 0.04186 | −0.026969 | −0.015942 | 0.010322 | −0.06012 | −0.003453 | −0.033397 | 0.027494 | −0.010409 | −0.058156 |
| 43 | 0.044493 | −0.022209 | 0.004196 | −0.03293 | 0.004111 | 0.003378 | 0.051005 | 0.012507 | −0.02483 | −0.04445 | −0.013926 | −0.011633 | −0.029692 | −0.030314 |
| 44 | 0.05245 | 0.009925 | 0.053223 | 0.003294 | 0.007706 | −0.004225 | 0.032582 | 0.070448 | −0.004363 | 0.038724 | 0.030227 | 0.013165 | −0.026753 | 0.042106 |
| 45 | 0.081742 | −0.023762 | 0.062644 | −0.023115 | 0.003687 | 0.063286 | −0.009519 | 0.040618 | −0.030302 | −0.079141 | 0.052375 | 0.044316 | −0.02044 | −0.046796 |
| 46 | 0.102494 | 0.066933 | −0.029018 | 0.035651 | −0.099254 | 0.047409 | 0.039317 | 0.012628 | 0.019647 | −0.10771 | −0.003774 | −0.013479 | 0.075542 | 0.025174 |
| 47 | −0.043021 | −0.017363 | 0.062869 | −0.009413 | 0.083977 | 0.030081 | 0.007424 | 0.033638 | 0.03206 | −0.145591 | 0.029905 | 0.046297 | −0.070552 | 0.063937 |
| 48 | −0.042964 | 0.001334 | 0.046895 | 0.043832 | −0.023152 | 0.018976 | 0.007507 | 0.027643 | 0.008263 | 0.009623 | 0.042055 | −0.001865 | −0.019189 | −0.052338 |
| 49 | 0.03537 | 0.026757 | 0.005576 | 0.017068 | 0.028103 | 0.022063 | 0.034828 | 0.020274 | 0.02787 | 0.024498 | −0.016211 | 0.012601 | 0.011965 | 0.00558 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 50 | −0.034526 | 0.055316 | −0.00647 | 0.031155 | 0.030194 | 0.045884 | 0.033475 | −0.009952 | −0.00017 | 0.011156 | −0.025644 | −0.008155 | 0.010211 | −0.023863 |
| 51 | −0.018087 | −0.022104 | 0.058225 | 0.040536 | −0.037607 | −0.019993 | −0.033564 | −0.03008 | 0.03959 | −0,023074 | 0.03087f | −0.005381 | 0.008981 | −0.025539 |
| 52 | −0.078064 | −0.046545 | 0.023636 | 0.069747 | −0.053311 | −0.018505 | −0.008782 | 0.053539 | 0.042174 | 0.011816 | 0.076538 | −0.036673 | −0.023608 | 0.092533 |
| 53 | −0.007295 | 0.041215 | 0.003415 | 0.024345 | −0.036305 | 0.008507 | 0.010503 | −0.030441 | 0.004319 | 0.011532 | −0.001153 | −0.029971 | −0.020848 | −0.025265 |
| 54 | −0.000053 | 0.010903 | −0.00342 | 0.051814 | 0.00447 | −0.018031 | 0.0283 | 0.0514 | 0.045302 | 0.004856 | −0.048173 | −0.038219 | 0.003253 | −0.034407 |
| 55 | −0.024101 | −0.045758 | −0.025794 | 0.034298 | −0.063851 | −0.006827 | −0.007686 | −0.001495 | 0.030502 | −0.030237 | 0.038745 | 0.012823 | 0.037865 | −0.110308 |
| 56 | 0.031061 | 0.041497 | 0.025802 | −0.02064 | −0.010503 | 0.03254 | 0.04349 | 0.005729 | 0.003557 | 0.019968 | 0.040379 | −0.018586 | −0.024611 | 0.005004 |
| 57 | −0.029276 | 0.049332 | −0.032655 | −0.019077 | −0.015403 | −0.08838 | −0.004718 | 0.038152 | −0.008786 | 0.059533 | −0.006427 | 0.024671 | 0.019554 | 0.011538 |
| 58 | −0.04343 | −0.042956 | 0.104935 | 0.03066 | 0.016585 | −0.041581 | −0.001074 | −0.022829 | 0.00534 | 0.007468 | 0.007485 | −0.010435 | 0.002879 | 0.045536 |
| 59 | 0.017386 | 0.066541 | 0.1005111 | −0.042852 | −0.056826 | −0.052638 | 0.058819 | 0.043537 | 0.039672 | 0.120601 | 0.076167 | 0.06742 | 0.048617 | 0.0805 |
| 60 | 0.043613 | −0.118882 | −0.005251 | 0.021195 | −0.012697 | 0.026912 | −0.022312 | −0.014769 | 0.051466 | −0.071376 | 0.077766 | 0.010833 | −0.015219 | 0.017808 |
| 61 | 0.022463 | −0.064732 | 0.093914 | 0.048473 | 0.027568 | 0.002989 | 0.021177 | −0.03974 | 0.063611 | 0.060559 | −0.066691 | 0.009923 | 0.019 | −0.044594 |
| 62 | 0.082186 | 0.010366 | 0.034984 | −0.046775 | −0.075194 | −0.007793 | −0.005406 | −0.004237 | −0.012697 | 0.031387 | −0.01922 | 0.038023 | 0.070196 | 0.003962 |
| 63 | 0.002827 | 0.043713 | 0.064909 | 0.006818 | −0.037757 | −0.015095 | −0.053548 | −0.037313 | 0.057524 | 0.077179 | −0.078703 | 0.019213 | −0.058664 | −0.017309 |
| 64 | 0.03562 | 0.038851 | 0.043746 | −0.045756 | 0.051035 | 0.009469 | 0.046653 | 0.02395 | −0.002517 | 0.031477 | 0.017612 | −0.003987 | 0.008227 | −0.005185 |
| 65 | −0.022086 | −0.002501 | −0.056973 | −0.046103 | −0.014262 | −0.074666 | 0.013686 | 0.011233 | 0.020051 | −0.004455 | 0.033646 | 0.030691 | −0.018872 | −0.053161 |
| 66 | 0.001133 | 0.023445 | 0.011449 | −0.023522 | 0.020612 | 0.014805 | −0.044615 | 0.019151 | 0.012015 | 0.068631 | −0.009387 | −0.089325 | 0.076551 | 0.053704 |
| 67 | −0.05263 | 0.012668 | 0.007786 | −0.026807 | −0.031615 | −0.045731 | −0.054789 | −0.090599 | 0.016076 | 0.009743 | −0.028181 | 0.020929 | 0.07353 | 0.062777 |
| 68 | 0.031637 | −0.020437 | −0.029627 | 0.002337 | 0.0657 | −0.094507 | −0.014835 | −0.003169 | −0.059874 | 0.094536 | 0.156936 | 0.040271 | −0.018664 | −0.036172 |
| 69 | 0.114227 | 0.036959 | −0.042 | 0.024266 | −0.066645 | 0.067185 | −0.003155 | 0.065749 | 0.030386 | 0.058451 | 0.004233 | 0.126462 | 0.117387 | 0.001171 |
| 70 | 0.028442 | −0.053577 | 0.023897 | 0.061929 | −0.006834 | −0.168192 | −0.066229 | 0.063629 | 0.080593 | −0.054521 | −0.009114 | 0.015759 | −0.007258 | −0.015287 |
| 71 | 0.066809 | 0.032919 | 0.032281 | −0.042473 | 0.120961 | 0.050767 | −0.010644 | −0.060775 | −0.069171 | 0.037409 | 0.017464 | −0.00533 | 0.035179 | 0.037848 |
| 72 | 0.044934 | −0.002433 | 0.004608 | −0.019968 | 0.025721 | 0.049269 | 0.020334 | 0.061535 | −0.020552 | 0.000974 | −0.001957 | 0.059218 | −0.014777 | 0.029023 |
| 73 | 0.083039 | −0.039315 | 0.022613 | −0.055208 | −0.057761 | 0.041371 | −0.044761 | −0.042277 | −0.041099 | 0.018225 | −0.111763 | −0.042708 | 0.047644 | −0.046404 |
| 74 | 0.109878 | −0.107065 | 0.053885 | −0.053211 | 0.005838 | 0.061602 | −0.212384 | 0.071994 | 0.049892 | 0.00442 | −0.057674 | −0.023662 | −0.0129 | 0.085323 |
| 75 | −0.045148 | 0.008525 | 0.024192 | 0.032797 | 0.039202 | 0.007845 | 0.003078 | −0.026011 | 0.023514 | 0.021267 | −0.021557 | 0.006087 | 0.013368 | −0.033566 |
| 76 | 0.001477 | −0.020739 | 0.006648 | −0.035645 | −0.002661 | 0.033739 | −0.06104 | 0.063338 | 0.035695 | −0.044076 | 0.064561 | −0.026972 | −0.032947 | −0.08357 |
| 77 | −0.016494 | 0.025375 | 0.022555 | 0.041859 | 0.027407 | 0.01141 | −0.023508 | 0.000784 | 0.022639 | 0.025841 | −0.030726 | 0.031364 | −0.010624 | −0.046108 |
| 78 | −0.041489 | −0.006707 | 0.019285 | 0.037195 | 0.045413 | 0.009805 | −0.03573 | −0.00749 | 0.029398 | 0.037797 | −0.048508 | 0.018112 | −0.005944 | −0.061279 |
| 79 | 0.020409 | −0.026798 | −0.036887 | −0.038849 | 0.04164 | −0.042419 | −0.022596 | 0.026082 | −0.035797 | 0.036824 | 0.047826 | −0.058525 | −0.05919 | 0.044744 |
| 80 | 0.028726 | 0.038229 | 0.044084 | 0.143243 | 0.021864 | −0.138277 | 0.099059 | −0.042075 | 0.135572 | 0.093163 | 0.02085 | −0.029144 | 0.034383 | 0.07597 |
| 81 | 0.053428 | −0.122428 | 0.028343 | 0.107602 | −0.05041 | 0.16897 | −0.054337 | 0.062738 | 0.066198 | −0.02447 | −0.031226 | −0.005551 | −0.044903 | −0.018603 |
| 82 | 0.025768 | 0.014957 | −0.056873 | 0.006104 | −0.052261 | −0.037671 | −0.035968 | 0.046956 | 0.025473 | −0.001342 | 0.070017 | −0.006391 | 0.045485 | −0.074574 |
| 83 | −0.021581 | 0.002816 | −0.028387 | 0.01493 | 0.022214 | −0.001143 | 0.019478 | 0.001981 | 0.037004 | 0.005735 | 0.056537 | −0.005379 | 0.005825 | −0.020006 |
| 84 | −0.040715 | 0.003399 | 0.036202 | −0.003905 | −0.040461 | −0.017627 | 0.053262 | −0.027114 | 0.00825 | −0.004484 | −0.007358 | 0.014442 | 0.006704 | 0.029101 |
| 85 | 0.127643 | −0.00906 | −0.12606 | 0.083621 | 0.085972 | 0.106086 | 0.015164 | −0.044532 | 0.075606 | 0.075785 | −0.018852 | −0.062997 | −0.035033 | 0.003342 |
| 86 | 0.067085 | 0.017358 | 0.042035 | −0.044613 | 0.052304 | 0.105221 | −0.016951 | −0.057129 | 0.044108 | −0.040578 | 0.047182 | 0.02877 | 0.065825 | −0.014062 |
| 87 | 0.067038 | 0.056108 | 0.013688 | −0.032164 | 0.053505 | −0.05551 | −0.008691 | 0.077335 | 0.05214 | 0.013082 | 0.060308 | 0.007191 | 0.147136 | 0.079222 |
| 88 | −0.039737 | 0.022302 | 0.014057 | −0.007196 | −0.033217 | 0.019753 | −0.016908 | −0.082898 | 0.005371 | 0.007516 | −0.007219 | 0.034362 | −0.022674 | 0.021971 |
| 89 | −0.027898 | −0.044321 | −0.006829 | −0.016749 | 0.013414 | 0.007663 | 0.015602 | 0.023185 | 0.005954 | 0.016465 | 0.036479 | −0.008573 | 0.010451 | 0.019266 |
| 90 | −0.035112 | −0.068281 | −0.019856 | −0.053848 | 0.027916 | 0.027825 | 0.048425 | 0.008581 | −0.001663 | 0.011944 | 0.05505 | 0.007935 | 0.001937 | −0.028273 |
| 91 | −0.012858 | −0.070892 | 0.03246 | 0.02719 | −0.088508 | −0.04015 | 0.000188 | 0.025766 | −0.023561 | 0.011412 | 0.002661 | −0.015909 | 0.027789 | −0.011217 |
| 92 | −0.110995 | −0.122042 | −0.021602 | 0.047538 | −0.125751 | −0.106959 | 0.019248 | 0.040216 | −0.054917 | 0.103165 | −0.132804 | 0.016017 | −0.038905 | −0.011142 |
| 93 | −0.06597 | 0.025947 | 0.007599 | 0.117219 | −0.012825 | −0.004537 | −0.01999 | 0.011502 | 0.02832 | −0.001337 | 0.010655 | −0.031886 | 0.031387 | 0.049064 |
| 94 | 0.013995 | −0.04139 | 0.014287 | −0.026437 | 0.055104 | −0.019001 | −0.019812 | −0.031146 | −0.027609 | −0.020632 | 0.061528 | 0.053108 | −0.0793 | −0.028127 |
| 95 | 0.042324 | −0.049593 | −0.122409 | −0.092528 | 0.037053 | 0.010354 | −0.101149 | 0.087606 | −0.051857 | 0.030217 | 0.223133 | 0.036892 | −0.007953 | 0.006682 |
| 96 | 0.037046 | 0.026779 | 0.003755 | −0.058006 | 0.0172 | −0.13936 | −0.027679 | −0.117686 | 0.003692 | −0.066754 | −0.036267 | −0.211387 | −0.004918 | −0.014643 |
| 97 | 0.088259 | −0.023801 | −0.009177 | 0.02476 | 0.023652 | −0.031778 | −0.005447 | 0.043734 | 0.032314 | 0.008389 | −0.013058 | 0.012007 | −0.002107 | −0.117961 |
| 98 | −0.008712 | −0.013042 | 0.004301 | −0.004181 | −0.006274 | 0.014123 | −0.003445 | 0.016246 | 0.012551 | 0.014723 | 0.010857 | −0.022361 | −0.008314 | −0.032584 |
| 99 | 0.020981 | −0.002746 | −0.045852 | 0.006081 | 0.026861 | −0.032859 | 0.066232 | −0.013485 | 0.00775 | −0.011256 | −0.03861 | 0.050729 | −0.045375 | −0.065649 |
| 100 | 0.057152 | 0.0069 | −0.026352 | −0.012662 | −0.030616 | −0.037431 | −0.063458 | 0.024284 | 0.018211 | 0.005052 | −0.029586 | −0.002553 | −0.017217 | −0.079115 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 101 | −0.024502 | −0.037832 | 0.03714 | −0.001609 | 0.025333 | 0.006507 | −0.025836 | 0.011237 | 0.015852 | 0.000282 | −0.012291 | 0.002653 | −0.048272 | 0.017562 |
| 102 | 0.026593 | 0.034551 | 0.039756 | −0.015137 | −0.006896 | −0.006675 | −0.068394 | −0.026523 | 0.033622 | −0.13669 | 0.014668 | 0.040145 | −0.053124 | −0.070766 |
| 103 | −0.018362 | −0.027047 | −0.006509 | −0.054021 | −0.057429 | −0.056247 | 0.017562 | −0.102763 | −0.132998 | −0.003386 | 0.022904 | 0.048877 | 0.041379 | 0.032553 |
| 104 | −0.086719 | 0.014728 | 0.088899 | −0.000978 | 0.016595 | −0.033089 | 0.015353 | −0.06307 | 0.046634 | 0.002871 | −0.057763 | −0.106045 | −0.073062 | 0.039597 |
| 105 | −0.045493 | −0.018644 | 0.03632 | 0.039818 | −0.158575 | −0.062984 | −0.094697 | −0.056331 | −0.005587 | 0.044119 | −0.092188 | −0.045617 | −0.009624 | 0.04794 |
| 106 | 0.044748 | 0.124272 | 0.019531 | 0.040463 | 0.001426 | 0.060796 | 0.010275 | −0.037105 | −0.072642 | 0.00121 | 0.094462 | −0.122252 | 0.090563 | 0.070759 |
| 107 | 0.071093 | −0.088667 | 0.010209 | 0.023686 | −0.055483 | 0.071541 | 0.016404 | −0.069019 | −0.010165 | 0.139157 | −0.001039 | 0.086684 | −0.053941 | −0.004374 |
| 108 | −0.042096 | 0.106633 | 0.147368 | 0.010463 | 0.078713 | −0.077714 | −0.088917 | −0.081752 | −0.117854 | 0.059829 | −0.035334 | 0.037467 | 0.109061 | −0.008509 |
| 109 | −0.017096 | 0.009163 | −0.11327 | 0.077781 | 0.075183 | 0.127454 | −0.060015 | 0.027175 | 0.119076 | −0.034753 | −0.10048 | −0.168121 | −0.086865 | −0.200039 |
| 110 | −0.142527 | 0.020459 | −0.062238 | 0.075117 | 0.104229 | −0.016691 | 0.033725 | 0.064312 | −0.211297 | 0.007128 | 0.017421 | −0.064264 | 0.022562 | −0.019034 |
| 111 | −0.048859 | −0.004516 | 0.054696 | −0.013415 | −0.059527 | −0.034976 | 0.027364 | −0.005313 | −0.077545 | −0.052701 | 0.120048 | −0.006374 | 0.09968 | −0.146435 |
| 112 | 0.008791 | 0.144666 | 0.052671 | −0.075565 | 0.017904 | 0.056261 | 0.076959 | −0.074823 | −0.035052 | −0.025179 | −0.114815 | 0.072627 | 0.000031 | 0.115456 |
| 113 | 0.085188 | 0.01889 | 0.021442 | 0.026297 | −0.107838 | −0.053376 | 0.061612 | 0.02805 | −0.084355 | 0.077438 | 0.113451 | −0.18049 | −0.062284 | −0.081594 |
| 114 | 0.067841 | −0.06487 | 0.043892 | −0.041727 | 0.000666 | 0.070054 | −0.16727 | 0.001182 | −0.08798 | 0.152016 | −0.020418 | −0.129032 | −0.171107 | −0.052583 |
| 115 | −0.10085 | −0.124438 | 0.136051 | −0.074375 | −0.001172 | −0.11027 | −0.008762 | −0.073943 | −0.011618 | −0.019994 | −0.082595 | 0.127098 | 0.0180−67 | −0.012167 |
| 116 | 0.002372 | 0.057563 | −0.12453 | 0.126131 | 0.072299 | −0.026949 | 0.026789 | 0.110156 | −0.085444 | −0.02991 | 0.021229 | −0.017732 | −0.093063 | −0.032813 |
| 117 | 0.037293 | 0.017014 | 0.121235 | 0.024166 | −0.066348 | −0.05729 | 0.109148 | 0.025485 | −0.128676 | 0.003017 | −0.079321 | −0.020241 | 0.025361 | −0.092012 |
| 118 | −0.017461 | −0.002288 | −0.036529 | −0.093797 | 0.077099 | −0.097165 | −0.039229 | 0.112958 | 0.056448 | 0.045526 | −0.138012 | 0.005471 | 0.036974 | −0.111291 |
| 119 | 0.029528 | −0.037853 | 0.010652 | −0.139078 | −0.053314 | −0.02856 | 0.087197 | 0.003483 | −0.028815 | 0.006975 | 0.013604 | −0.007147 | 0.015687 | −0.0458 |
| 120 | 0.015665 | −0.011207 | 0.040981 | −0.002127 | −0.066482 | 0.004923 | 0.041219 | 0.017327 | −0.0686 | 0.033363 | 0.026008 | 0.024695 | 0.077128 | −0.006944 |
| 121 | 0.02136 | 0.042623 | 0.075034 | .010493 | −0.098097 | 0.004711 | −0.011108 | 0.061201 | −0.017088 | −0.02239 | 0.060268 | 0.05453 | 0.008754 | −0.013928 |
| 122 | −0.015851 | −0.068198 | 0.059818 | 0.065077 | 0.014206 | −0.014941 | 0.102783 | −0.020519 | 0.043631 | −0.026843 | −0.035846 | −0.06618 | 0.023778 | −0.053255 |
| 123 | −0.033423 | −0.053141 | −0.003432 | 0.028739 | 0.001074 | −0.035755 | −0.001732 | 0.002985 | −0.037128 | 0.017415 | 0.037002 | 0.010574 | 0.080047 | −0.020014 |
| 124 | 0.05153 | −0.039739 | 0.005348 | −0.070637 | −0.00756 | −0.017062 | 0.070017 | 0.001798 | −0.00564 | −0.015299 | −0.009905 | 0.058945 | 0.026308 | −0.034013 |
| 125 | 0.048924 | 0.006856 | −0.047 | 0.009019 | 0.060984 | 0.039879 | −0.015812 | 0.035716 | 0.019052 | 0.055442 | −0.000861 | 0.032238 | −0.025528 | 0.113853 |
| 126 | 0.005294 | −0.041386 | −0.027501 | −0.025964 | 0.026381 | 0.041473 | −0.018727 | 0.058876 | −0.013856 | −0.06245 | −0.041403 | −0.008976 | −0.013938 | 0.029987 |
| 127 | −0.013401 | −0.049569 | −0.664569 | −0.027543 | 0.061059 | 0.051996 | −0.009626 | 0.019648 | −0.062097 | −0.009227 | −0.076733 | −0.035697 | −0.001746 | −0.013973 |
| 128 | 0.003423 | 0.02326 | 0.007746 | 0.074008 | 0.611309 | −0.022357 | 0.042136 | 0.051821 | 0.018206 | −0.040207 | −0.08064 | −0.020803 | −0.01197 | −0.043178 |
| 129 | 0.007223 | 0.063061 | 0.0018231 | 0.057783 | 0.024614 | −0.001823 | 0.08137 | −0.078199 | −0.09189 | −0.011437 | −0.039118 | −0.008211 | 0.044896 | 0.08167 |
| 130 | −0.124207 | −0.005926 | −0.195241 | −0.142378 | 0.06122 | 0.043498 | 0.060612 | −0.10507 | 0.058868 | 0.019772 | −0.05056 | 0.098585 | −0.013331 | −0.100329 |
| 131 | 0.091919 | −0.102613 | −0.099471 | 0.0718151 | −0.149267 | −0.075631 | −0.004405 | 0.022507 | 0.010922 | 0.070653 | 0.128074 | 0.138797 | 0.03157 | −0.095978 |
| 132 | 0.059479 | −0.057919 | 0.048722 | 0.616547 | −0.034196 | 0.060607 | 0.08628 | −0.032371 | −0.021066 | −0.046317 | −0.021868 | 0.040042 | 0.101566 | 0.002856 |
| 133 | 0.083902 | 0.023902 | 0.092184 | −0.027832 | 0.032761 | 0.072626 | −0.054575 | −0.034153 | −0.09724 | 0.015556 | −0.07083 | 0.002242 | −0.668143 | 0.007494 |
| 134 | −0.088583 | −0.088713 | 0.031427 | −0.102986 | 0.028869 | −0.010295 | 0.055817 | −0.068784 | 0.145264 | 0.086562 | −0.055625 | 0.083602 | −0.11419 | −0.06856 |
| 135 | −0.006909 | 0.039734 | 0.002559 | −0.051038 | 0.064326 | −0.007095 | 0.013376 | −0.016058 | 0.038877 | 0.021702 | 0.005151 | −0.027157 | 0.01608 | 0.040401 |
| 136 | 0.072802 | −0.066957 | −0.096635 | −0.024029 | −0.021249 | −0.119571 | 0.088568 | −0.077875 | −0.026582 | −0.016705 | 0.117856 | −0.0041 | 0.042739 | −0.084178 |
| 137 | 0.0384931 | 0.05602 | −0.665786 | 0.001652 | 0.053704 | −0.020103 | −0.00062 | 0.071935 | 0.012672 | 0.16064 | 0.09307 | −0.060674 | −0.035203 | 0.022586 |
| 138 | −0.144453 | −0.042931 | 0.0014991 | 0.001516 | 0.063892 | 0.140518 | 0.058706 | 0.10011 | 0.0122 | −0.004 | 0.001483 | −0.011284 | 0.121416 | −0.043601 |
| 139 | −0.037756 | 0.669106 | 0.204124 | 0.082474 | −0.046521 | 0.021264 | −0.035872 | −0.074419 | −0.12082 | −0.03507 | 0.094823 | 0.03089 | −0.108398 | −0.02096 |
| 140 | 0.110792 | 0.132323 | 0.150417 | 0.183267 | −0.078076 | 0.145149 | 0.160903 | 0.022258 | −0.043799 | −0.063087 | −0.091936 | 0.110313 | 0.090538 | −0.152988 |
| 141 | −0.06916 | 0.021639 | −0.027623 | −0.015481 | 0.044197 | 0.039924 | −0.060504 | −0.009621 | −00267274 | 0.047941 | −0.073561 | −0.025004 | 0.031368 | 0.093259 |
| 142 | −0.619598 | −0.024628 | 0.039698 | 0.045079 | 0.025066 | 0.043898 | −0.01118 | 0.017202 | −0.032469 | −0.039212 | −0.026854 | −0.07361 | −0.065644 | −0.046645 |
| 143 | −0.087495 | 0.035509 | 0.0935791 | 0.126837 | −0.062344 | −0.004272 | −0.043845 | −0.011635 | 0.045883 | 0.027463 | + 0.019427 | −0.028064 | 0.01688 | −0.011667 |
| 144 | −0.657888 | −0.012745 | −0.009199 | 0.05352 | −0.01834 | −0.048833 | 0.0982 | −0.011914 | 0.001476 | −0.078489 | 0.150606 | −0.033806 | −0.015788 | −0.003754 |
| 145 | 0.05796 | −0.01972 | 0.002918 | −0.019581 | 0.048149 | −0.023198 | 0.002795 | 0.060966 | 0.027454 | 0.008897 | 0.013852 | −0.025453 | 0.04207 | −0.145715 |
| 146 | 0.0371451 | 0.0465391 | 0.004688 | −0.03723 | 0.018852 | 0.030834 | 0.00314 | −0.02285 | −0.027375 | 0.0254514 | −0.007791 | −0.014882 | −0.006228 | 0.046625 |
| 147 | −0.627673 | −0.023983 | −0.6114571 | −0.011503 | −0.074426 | 0.001651 | 0.046689 | −0.000593 | 0.071054 | 0.023194 | −0.017431 | −0.05363 | −0.056149 | −0.04297 |
| 148 | −0.040448 | 0.085373 | 0.024473 | −0.008536 | 0.007205 | −0.083747 | 0.011457 | 0.005325 | 0.612278 | −0.101613 | 0.014908 | −0.145965 | −0.069766 | −0.665535 |
| 149 | 0.051863 | −0.016086 | 0.010358 | 0.076371 | 0.01513 | −0.067754 | 0.008569 | −0.038736 | 0.0540311 | 0.022888 | 0.01916 | 0.049823 | −0.105275 | 0.034908 |
| 150 | 0.049399 | 0.041586 | −0.073116 | 0.057789 | 0.085376 | −0.064856 | 0.023125 | 0.035216 | 0.019737 | 0.145223 | −0.105475 | 0.035319 | 0.032204 | 0.07955 |
| 151 | 0.070969 | 0.046765 | 0.052063 | 0.056174 | −0.078162 | −126964 | −0.011198 | 0.007639 | −0.05493 | f 0.097499 | −0.053217 | −0.086252 | −0.148466 | −0.039542 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 152 | 0.03155 | 0.004784 | −0.001195 | −0.016629 | −0.095373 | −0.01103 | 0.031744 | 0.018914 | 0.008535 | 0.038521 | 0.024601 | −0.004349 | −0.040056 | −0.021253 |
| 153 | −0.059605 | −0.013002 | −0.066084 | 0.019311 | −0.011177 | −0.069496 | 0.040835 | −0.028997 | −0.035857 | −0.022341 | −0.031666 | −0.037716 | −0.011856 | 0.0318 |
| 154 | −0.035612 | 0.020334 | −0.0882711 | 0.031367 | −0.037928 | −0.035673 | −0.010469 | −0.001765 | 0.013284 | −0.069142 | 0.023314 | −0.00402 | 0.015224 | −0.099683 |
| 155 | 0.007514 | −0.013871 | 0.02303 | 0.020641 | −0.002987 | 0.003657 | 0.013031 | −0.07104 | 0.06027 | −0.060279 | 0.109055 | 0.027051 4 | 0.063887 | 0.054131 |
| 156 | −0.009389 | −0.044083 | 0.002086 | 0.086934 | 0.003862 | −0.052068 | −0.211121 | −0.094043 | 0.140582 | −0.129002 | 0.042301 | 0.101065 t | −0.046834 | 0.012974 |
| 157 | −0.031667 | 0.041347 | 0.045621 | −0.006381 | −0.02681 | 0.102089 | 0.104341 | 0.041353 | −0.068961 | −0.054368 | −0.020451 | −0.000514 | −0.042072 | 0.016805 |
| 158 | 0.042809 | 0.0051591 | 0.175358 | −0.034202 | 0.089859 | −0.019388 | −0.152518 | −0.022718 | 0.0220811 | 0.03921 | 0.094851 | −0.103062 | 0.119455 | −0.12704 |
| 153 | −0.106663 | 0.124761 | 0.621199 | 0.036894 | 0.085726 | −0.007854 | −0.048446 | 0.15738 | 0.11854 | −0.001358 | −0.072515 | 0.097133 | −0.044846 | −0.001221 |
| 160 | 0.085616 | 0.022506 | 0.005594 | 0.045386 | −0.027068 | 0.033979 | 0.076542 | −0.058715 | −0.016468 | 0.071124 | 0.045421 | −0.012999 | −0.128705 | 0.102162 |
| 161 | −0.106089 | −0.056559 | −0.076914 | 0.118547 | 0.021096 | 0.012114 | 0.047154 | 0.032863 | −0.063229 | −0.034931 | 0.067906 | −0.001097 | −0.089602 | 0.018083 |
| 162 | 0.0409791 | 0.104327 | −0.103696 | 0.071706 | 0.040108 | −0.067305 | −0.023621 | 0.093784 | −0.086014 | 0.043575 | 0.125888 | 0.076452 | −0.040314 | 0.007164 |
| 163 | 0.054919 | −0.015693 | 0.046156 | 0.013359 | −0.06102 | 0.032944 | 0.001957 | −0.021887 | 0.05748 | 0.083532 | −0.016186 | 0.0058641 | 0.06186 | 0.055423 |
| 164 | 0.109565 | −0.016899 | 0.1493 | 0.047365 | −0.07556 | 0.016677 | −0.072009 | −0.002072 | −0.150028 | 0.041092 | −0.122845 | 0.026186 | −0.038957 | 0.013398 |
| 165 | 0.1327841 | 0.153378 | −0.0856851 | −0.022003 | −0.128773 | 0.028145 | −0.077983 | −0.141394 | −0.011272 | −0.165033 | 0.0641641 | −0.035202 | −0.148821 | 0.054336 |
| 166 | 0.05044 | 0.051229 | −0.021472 | −0.106388 | 0.078592 | 0.079838 | −0.023047 | −0.034979 | −0.146971 | −0.152382 | −0.097923 | −0.057281 | 0.0082721 | 0.093877 |
| 167 | −0.135935 | −0.101885 | 0.061213 | −0.019438 | −0.002437 | 0.023535 | −0.02405 | −0.089566 | −0.074112 | 0.058686 | 0.127796 | −0.071999 | 0.206367 | −0.029965 |
| 168 | 0.035949 | 0.088617 | −0.112659 | 0.019754 | 0.020075 | −0.03232 | −0.057722 | −0.000397 | 0.032181 | 0.026712 | −0.003419 | 0.016536 | 0.041771 | 0.029937 |
| 169 | −0.024212 | 0.023197 | 0.010303 | −0.012806 | 0.018146 | 0.028254 | −0.007646 | −0.028753 | −0.027211 | −0.012894 | 0.022376 | −0.056413 | 0.055144 | 0.058531 |
| 170 | 0.009134 | 0.007092 | −0.008942 | −0.013396 | 0.011987 | 0.014004 | 0.021461 | −0.040361 | −0.014152 | −0.031311 | 0.019358 | −0.033807 | −0.000206 | 0.04384 |
| 171 | −0.002834 | 0.012819 | −0.002984 | 0.013663 | −0.062805 | 0.00776 | −0.047218 | −0.023521 | −0.051563 | 0.018831 | 0.016009 | 0.010948 | 0.040801 | 0.053339 |
| 172 | −0.0158911 | 0.03916 | 0.004174 | −0.029349 | −0.008183 | 0.003084 | −0.001645 | 0.025963 | −0.017885 | 0.043155 | 0.021795 | −0.029595 | 0.051938 | 0.000566 |
| 173 | −0.010035 | 0.034945 | 0.015227 | 0.026971 | 0.044622 | 0.006069 | −0.036285 | 0.003506 | −0.085759 | 0.031877 | −0.001773 | 0.011422 | −0.035072 | 0.00736 |
| 174 | 0.00655 | −0.006129 | 0.007754 | 0.024847 | 0.058121 | 0.033066 | −0.01815 | 0.034672 | −0.050235 | −0.014813 | −0.023629 | −0.028297 | −0.031785 | −0.001687 |
| 175 | 0.068092 | −0.057729 | −0.017293 | 0.03613 | 0.006058 | −0.101298 | 0.023058 | −0.000076 | 0.007397 | 0.020683 | −0.032907 | −0.046773 | 0.005242 | −0.030548 |
| 176 | −0.01052 | −0.014104 | −0.041571 | −0.067108 | −0.067979 | −0.030997 | −0.130767 | 0.015191 | −0.036761 | −0.025298 | 0.059712 | 0.040024 | 0.07076 | −0.020239 |
| 177 | 0.00756 | −0.02272 | −0.016744 | −0.088017 | 0.026253 | −0.077359 | 0.089143 | −0.005591 | −0.04068 | −0.1142 | 0.07767 | 0.071554 | 0.142116 | −0.056014 |
| 178 | −0.044669 | −0.004522 | −0.018182 | −0.018322 | 0.009189 | 0.097251 | −0.052959 | 0.036555 | −0.008448 | 0.035932 | 0.037226 | 0.000012 | 0.059894 | −0.044553 |
| 179 | −0.012721 | 0.002119 | 0.014015 | −0.007567 | −0.048213 | 0.001183 | −0.028789 | 0.017881 | −0.003846 | 0.022125 | 0.002313 | 0.002107 | 0.03805 | −0.028712 |
| 180 | −0.041141 | −0.02485 | −0.002425 | −0.020071 | 0.015469 | 0.031561 | 0.015412 | 0.01888 | 0.001245 | 0.020573 | −0.011584 | 0.002874 | 0.005409 | −0.008351 |
| 181 | −0.027686 | −0.029989 | 0.003482 | −0.004773 | −0.014796 | 0.017538 | 0.011943 | 0.001058 | −0.002665 | 0.002486 | 0.004659 | 0.002473 | −0.016155 | −0.021991 |
| 182 | 0.040071 | −0.006749 | −0.010098 | −0.02251 | −0.001234 | −0.032831 | −0.003281 | 0.041575 | 0.017818 | −0.002141 | −0.044347 | 0.043284 | −0.02104 | −0.031317 |
| 183 | 0.087185 | 0.012281 | −0.009248 | 0.013628 | −0.112439 | −0.071123 | −0.085215 | 0.049352 | −0.005965 | 0.001375 | −0.004922 | 0.064548 | 0.045675 | −0.006889 |
| 184 | 0.081142 | 0.091916 | −0.024337 | 0.041707 | −0.133574 | −0.010326 | −0.10378 | −0.017927 | 0.016924 | −0.05828 | 0.073274 | 0.076913 | 0.072433 | 0.0087 |
| 185 | −0.08715 | −0.028273 | 0.005507 | −0.011571 | 0.053681 | 0.031323 | 0.075174 | 0.082239 | 0.066689 | −0.000453 | −0.094529 | −0.127385 | 0.03584 | 0.014296 |
| 186 | −0.0322811 | −0.0232671 | −0.160841 | 0.041467 | −0.06467 | 0.016533 | 0.110742 | 0.015333 | −0.086236 | 0.0898911 | 0.0039411 | 0.0234021 | 0.0242281 | 0.106302 |
| 187 | 0.034856 | 0.033033 | 0.046535 | −0.07083 | 0.038542 | −0.030177 | −0.04352 | 0.020948 | −0.026997 | −0.016916 | −0.015622 | 0.036565 | −0.0191 | 0.041032 |
| 188 | 0.030555 | 0.01442 | 0.045507 | −0.03685 | 0.045062 | −0.001368 | −0.049055 | 0.008975 | 0.004766 | −0.086733 | −0.012882 | −0.000386 | −0.010736 | 0.004187 |
| 189 | 0.020335 | −0.032911 | 0.118816 | −0.007773 | 0.056155 | −0.084414 | −0.028654 | 0.042943 | −0.023819 | −0.108488 | −0.058276 | −0.043754 | −0.044264 | −0.042832 |
| 190 | −0.044842 | −0.04218 | 0.014017 | −0.009362 | −0.030263 | −0.084593 | −0.038566 | 0.04036 | −0.01731 | 0.010696 | 0.029791 | −0.011468 | −0.002358 | 0.083684 |
| 191 | −0.062618 | −0.046964 | 0.042004 | −0.026879 | −0.038657 | −0.023784 | 0.03709 | −0.00295 | 0.021302 | −0.058003 | −0.020907 | −0.009201 | 0.003473 | 0.056942 |
| 192 | 0.09065 | 0.038665 | −0.007967 | 0.047394 | 0.01535 | 0.023044 | 0.039797 | 0.056735 | 0.008899 | 0.107541 | −0.020481 | 0.056272 | −0.016671 | −0.019042 |
| 193 | 0.017676 | −0.04658 | 0.003241 | −0.002092 | −0.064006 | 0.046833 | 0.062124 | −0.008087 | −0.02395. | 0.084563 | 0.010976 | 0.015504 | 0.043453 | −0.020719 |
| 194 | 0.022839 | −0.037055 | 0.094831 | −0.008976 | −0.014803 | 0.01842 | −0.013268 | −0.030689 | 0.077892 | −0.024491 | 0.005806 | 0.042617 | 0.08809 | 0.006275 |
| 195 | −0.062844 | −0.059933 | 0.010783 | 0.072726 | 0.031483 | −0.02305 | 0.023964 | 0.019865 | −0.004471 | 0.072513 | 0.106109 | 0.039492 | −0.00009 | 0.039364 |
| 196 | −0.051202 | −0.028036 | 0.038435 | 0.024888 | 0.03541 | −0.010363 | 0.017534 | −0.005851 | 0.027729 | −0.02955 | 0.041998 | 0.011527 | −0.00676 | 0.019279 |
| 197 | −0.062232 | −0.0307011 | 0.048074 | −0.023958 | −0.003238 | −0.077349 | −0.001091 | −0.008739 | 0.036938 | 0.026944 | −0.000678 | 0.017074 | −0.023752 | 0.046037 |
| 198 | 0.007736 | 0.00597 | −0.037523 | −0.004265 | −0.059278 | 0.043314 | 0.014868 | 0.142666 | 0.115896 | −0.039532 | 0.011787 | 0.008109 | 0.103729 | 0.025788 |
| 199 | −0.02229 | −0.102455 | 0.130263 | 0.067516 | −0.070682 | 0.135881 | 0.001361 | 0.05423 | −0.048957 | 0.001345 | 0.013807 | 0.059343 | 0.010802 | 0.003314 |
| 200 | 0.00148 | −0.002922 | 0.033255 | 0.059999 | −0.010244 | 0.051202 | −0.007408 | 0.017715 | −0.008924 | 0.105233 | −0.043828 | 0.066901 | 0.019639 | 0.000499 |
| 201 | 0.034937 | −0.063657 | −0.038993 | 0.002145 | 0.021211 | −0.086253 | −0.037251 | −0.00902 | −0.018467 | −0.061454 | −0.142348 | 0.048145 | −0.132045 | −0.08203 |
| 202 | 0.021773 | 0.019138 | 0.011006 | 0.010984 | −0.056201 | 0.047371 | 0.022022 | −0.01775 | 0.064338 | 0.015384 | −0.047949 | −0.056018 | −0.023192 | 0.012591 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 203 | 0.006906 | 0.023117 | 0.131109 | 01.040199 | 0.076257 | −0.013622 | −0.038861 | 0.127811 | 0.04213 | −0.04631 | 0.033182 | 0.052171 | 0.024731 | −0.04255 |
| 204 | −0.125802 | 0.15696 | −0.060667 | −0.11754 | −0.266675 | 0.01517 | 0.078657 | 0.016243 | 0.017525 | −0.11451 | −0.003211 | −0.057117 | −0.046288 | −0.071874 |
| 205 | −0.044853 | −0.056053 | −0.031261 | 0.102696 | 0.011226 | −0.012533 | −0.023425 | 0.25464 | 0.013438 | −0.081441 | −0.041954 | −0.086567 | 0.055011 | 0.044389 |
| 206 | −0.031744 | −0.037843 | 0.058397 | −0.082181 | 0.163306 | −0.045085 | 0.035835 | −0.039144 | −0.014677 | 0.116737 | 0.082056 | 0.05822 | 0.005666 | −0.007276 |
| 207 | 0.040994 | −0.030034 | 0.131622 | 0.008102 | −0.053606 | −0.06379 | 0.034029 | −0.029168 | −0.060433 | −0.080514 | 0.04871 | 0.038382 | 0.004276 | 0.084587 |
| 208 | −0.134373 | 0.07404 | 0.054273 | 0.017419 | 0.13347 | −0.039143 | −0.037169 | 0.007529 | 0.034378 | −0.013761 | 0.015344 | 0.147179 | 0.013406 | −0.042225 |
| 209 | 0.045051 | 0.15005 | −0.027117 | −0.092903 | 0.023315 | 0.064972 | −0.11118 | −0.007876 | 0.121701 | −0.033639 | 0.025665 | 0.048473 | 0.020882 | −0.086769 |
| 210 | 0.015289 | −0.002344 | −0.100009 | 0.097947 | 0.094759 | −0.027572 | 0.079419 | 0.041524 | −0.081184 | 0.050464 | 0.070079 | 0.042752 | 0.020493 | 0.040017 |
| 211 | −0.059694 | 0.06404 | −0.074892 | 0.086106 | −0.004336 | −0.052076 | −0.018097 | −0.026591 | −0.019527 | −0.016098 | −0.120743 | 0.10932 | −0.064622 | −0.081235 |
| 212 | −0.147207 | 0.125399 | 0.099249 | −0.02242 | −0.064924 | −0.056284 | −0.062527 | 0.019101 | 0.040033 | 0.053091 | 0.063545 | −0.091233 | −0.001031 | 0.022732 |
| 213 | 0.082024 | −0.001865 | 0.103303 | −0.152658 | −0.050878 | 0.033195 | 0.018387 | −0.007346 | 0.072725 | 0.041359 | −0.137932 | 0.015151 | −0.054411 | 0.01878 |
| 214 | 0.002494 | 0.021717 | −0.004249 | 0.023725 | −0.024794 | −0.004055 | −0.034002 | −0.008705 | −0.029951 | 0.019024 | −0.01552 | 0.013641 | 0.022055 | −0.018634 |
| 215 | −0.072706 | −0.038267 | 0.0276 | 0.099712 | 0.002136 | 0.059923 | 0.133917 | −0.025644 | −0.041048 | 0.115747 | −0.010577 | −0.012004 | −0.00221 | 0.003975 |
| 216 | −0.037322 | −0.0107 | −0.018663 | −0.032768 | 0.077621 | −0.004606 | 0.031411 | 0.028521 | −0.000993 | −0.060142 | 0.026063 | 0.028875 | −0.044641 | 0.059177 |
| 217 | 0.043918 | 0.02319 | −0.066596 | 0.046883 | −0.050331 | −0.042599 | 0.047676 | 0.061486 | 0.097556 | 0.050567 | −0.111563 | −0.07108 | 0.052165 | 0.015857 |
| 218 | −0.044091 | 0.011346 | −0.010956 | 0.060643 | 0.030476 | 0.05206 | 0.028837 | −0.013639 | −0.007678 | 0.055101 | 0.021814 | −0.029788 | 0.011855 | −0.040292 |
| 219 | −0.013468 | 0.066978 | −0.007169 | 0.017573 | 0.026663 | 0.021268 | −0.03811 | −0.023697 | −0.067417 | 0.016053 | 0.037716 | 0.007353 | −0.026477 | −0.022186 |
| 220 | 0.096046 | 0.002101 | 4.041624 | −0.058895 | −0.049346 | −0.01252 | 0.037077 | 0.056229 | 0.032602 | 0.042558 | −0.065333 | 0.000315 | 0.051513 | 0.012817 |
| 221 | −0.015476 | 0.075384 | −0.058344 | 0.021298 | 0.01709 | −0.011804 | −0.023846 | 0.017808 | −0.003402 | −0.003472 | 0.033935 | 0.075713 | −0.041509 | 0.002203 |
| 222 | −0.078197 | 0.034204 | 0.032496 | 0.01584 | 0.032461 | 0.052596 | −0.047211 | −0.042396 | 0.007941 | 0.084787 | 0.018051 | 0.013237 | −0.019437 | −0.030181 |
| 223 | −0.04967 | −0.046664 | −0.003029 | −0.018827 | −0.047959 | 0.040294 | −0.007196 | −0.09417 | −0.044118 | 0.049739 | −0.036932 | 0.001524 | 0.037894 | 0.014011 |
| 224 | 0.025339 | −0.063525 | −0.008114 | 0.040267 | −0.000192 | 0.058882 | −0.074513 | 0.054897 | −0.068636 | 0.004949 | 0.017043 | −0.063357 | 0.0045191 | −0.02608 |
| 225 | 0.044656 | −0.060753 | −0.007287 | 0.05288 | 0.024858 | 0.057323 | −0.047851 | 0.095885 | −0.102293 | 0.001858 | 0.03388 | −0.054287 | 0.001621 | −0.032264 |
| 226 | 0.007625 | −0.020921 | −0.01837 | 0.049892 | −0.013226 | −0.032585 | −0.011665 | 0.013621 | 0.022087 | −0.074603 | −0.010517 | −0.034749 | 0.038189 | 0.008766 |
| 227 | 0.0279 | −0.114704 | 0.035184 | 0.024245 | 0.064731 | 0.007297 | 0.017025 | 0.025816 | −0.023138 | −0.044736 | 0.013083 | −0.061487 | 0.060476 | 0.039861 |
| 228 | 0.0209 | 0.072112 | 0.011203 | −0.054693 | 0.047453 | −0.070027 | −0.015903 | 0.07587 | 0.05575 | 0.030892 | −0.003448 | 0.060905 | −0.077516 | 0.022204 |
| 229 | −0.021198 | 0.029923 | −0.025226 | −0.076588 | −0.015265 | 0.021482 | −0.039328 | 0.020691 | −0.023821 | 0.079991 | 0.020516 | 0.07207 | −0.030405 | −0.039031 |
| 230 | −0.069401 | −0.048466 | 0.042137 | −0.0098 | 0.073089 | 0.057903 | 0.02057 | 0.022068 | 0.014361 | −0.028164 | 0.023849 | 0.000334 | −0.070718 | 0.048698 |
| 231 | 0.074063 | −0.035823 | −0.027285 | 0.012145 | 0.005768 | −0.090675 | 0.018003 | −0.084657 | 0.099748 | −0.075148 | −0.016548 | −0.021342 | −0.041963 | 0.053756 |
| 232 | −0.137478 | 0.071242 | −0.088038 | −0.078662 | −0.11108 | 0.012149 | −0.09857 | 0.10265 | 0.074043 | 0.077521 | −0.127951 | 0.000372 | 0.021514 | 0.115256 |
| 233 | −0.016549 | 0.044668 | 0.010653 | −0.067848 | −0.090084 | 0.029399 | 0.016799 | 0.049424 | 0.087061 | 0.039494 | 0.038416 | −0.037217 | 0.058407 | 0.036432 |
| 234 | 0.086099 | −0.012463 | 0.020723 | −0.028241 | 0.080221 | 0.007169 | −0.046811 | 0.008684 | 0.012401 | 0.082082 | 0.047648 | 0.045417 | −0.032238 | 0.100964 |
| 235 | 0.058349 | 0.020421 | −0.015645 | 0.004999 | 0.028077 | 0.022274 | 0.050437 | −0.022902 | 0.008512 | 0.045452 | 0.062834 | 0.034013 | −0.09073 | −0.020046 |
| 236 | −0.037879 | −0.040512 | −0.030317 | −0.029115 | −0.004466 | −0.021629 | −0.020559 | −0.024688 | 0.008452 | −0.066567 | 0.02541 | 0.050972 | −0.023333 | 0.082117 |
| 237 | −0.018876 | −0.001712 | −0.002591 | 0.008809 | 0.037997 | −0.024234 | 0.003003 | 0.017882 | −0.006943 | −0.026747 | −0.02513 | −0.008207 | −0.008578 | 0.039604 |
| 238 | −0.025414 | 0.030609 | 0.013662 | 0.0199 | −0.028665 | −0.021409 | −0.043558 | −0.025446 | 0.035807 | −0.023987 | 0.008206 | 0.02311 | −0.042687 | −0.014047 |
| 239 | −0.021758 | 0.039778 | −0.011632 | 0.020065 | −0.051442 | −0.02287 | −0.021094 | −0.015976 | 0.037742 | −0.041456 | 0.041293 | 0.02373 | −0.040988 | −0.035586 |
| 240 | −0.01051 | 0.052734 | 0.001154 | 0.066168 | −0.022185 | −0.03547 | −0.033422 | 0.029806 | 0.044465 | −0.063152 | 0.017133 | −0.061069 | 0.043496 | 0.065008 |
| 241 | −0.044991 | 0.062645 | 0.008978 | 0.02574 | −0.046358 | 0.005206 | 0.013808 | 0.030855 | 0.026946 | −0.047921 | −0.001032 | −0.029838 | 0.027564 | 0.038156 |
| 242 | −0.000177 | −0.006755 | 0.071588 | −0.106413 | −0.034435 | −0.030346 | 0.056513 | 0.006831 | −0.005518 | 0.031368 | −0.033256 | 0.011222 | −0.044089 | −0.016647 |
| 243 | 0.030071 | 0.027339 | −0.011932 | 0.008002 | 0.038934 | −0.048056 | 0.062774 | 0.02215 | 0.008646 | −0.020574 | −0.019358 | −0.007928 | −0.05923 | 0.002323 |
| 244 | −0.008874 | 0.032444 | −0.028085 | −0.031932 | −0.002637 | −0.048333 | −0.016019 | 0.04473 | −0.008382 | 0.04183 | −0.000543 | 0.023687 | 0.014026 | 0.047284 |
| 245 | −0.043677 | 0.020899 | 0.077258 | 0.088709 | 0.025222 | 0.057105 | 0.022603 | −0.028514 | 0.01165 | −0.024466 | 0.066858 | −0.015584 | −0.011607 | 0.011179 |
| 246 | 0.020383 | −0.05859 | 0.057809 | 0.007313 | 0.018023 | 0.012875 | −0.015799 | 0.003662 | −0.021846 | −0.004679 | 0.02936 | 0.032637 | −0.021684 | −0.00145 |
| 247 | 0.028381 | −0.012988 | 0.016724 | 0.010907 | −0.014132 | −0.001741 | −0.019828 | 0.009446 | −0.009269 | 0.004408 | 0.029459 | 0.038514 | 0.02211 | 0.02763 |
| 248 | −0.012781 | 0.046209 | −0.012192 | −0.011477 | −0.032529 | −0.01123 | 0.021065 | 0.001147 | 0.015703 | 0.032274 | −0.02974 | 0.068521 | 0.037899 | 0.019946 |
| 249 | −0.074547 | −0.020625 | −0.020971 | 0.083173 | −0.028695 | 0.022977 | 0.037375 | −0.01641 | 0.084271 | 0.012772 | 0.00705 | −0.020788 | 0.005275 | 0.016459 |
| 250 | 0.001369 | −0.080935 | −0.019279 | 0.048304 | 0.035989 | −0.029303 | −0.053945 | 0.003602 | −0.019905 | −0.052698 | 0.00235 | 0.022955 | 0.095472 | 0.060496 |
| 251 | −0.007508 | 0.058012 | 0.030885 | 0.026197 | 0.03178 | −0.004723 | −0.028536 | −0.004704 | −0.058729 | −0.042147 | −0.006392 | −0.024964 | −0.001501 | −0.014726 |
| 252 | −0.004598 | 0.056249 | 0.018019 | 0.016592 | 0.008834 | 0.033544 | 0.081994 | 0.037704 | 0.055531 | −0.041988 | −0.020062 | −0.067962 | −0.025761 | −0.053694 |
| 253 | −0.008954 | 0.008344 | −0.030232 | 0.003466 | 0.001698 | 0.004934 | −0.014037 | −0.066632 | 0.039319 | −0.065186 | 0.015315 | −0.008961 | 0.005593 | 0.053166 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 254 | −0.036316 | −0.065572 | −0.055507 | −0.062935 | −0.047815 | −0.000632 | 0.022695 | −0.062689 | −0.06873 | 0.029692 | −0.05214 | −0.007673 | 0.014877 | 0.03442 |
| 255 | −0.004258 | 0.000498 | −0.030581 | −0.058225 | 0.025247 | −0.026347 | −0.002391 | 0.013663 | −0.011931 | −0.004311 | −0.015737 | 0.003326 | −0.023132 | 0.019151 |
| 256 | −0.04699 | −0.001158 | 0.001791 | −0.017145 | 0.026902 | 0.10579 | 0.087324 | 0.038829 | 0.103967\ | −0.022637 | 0.09209 | 0.006658 | −0.074023 | −0.009141 |
| 257 | −0.009297 | −0.075648 | 0.035585 | −0.007383 | −0.000537 | 0.069228 | 0.048827 | 0.023514 | −0.025191 | 0.031984 | 0.055951 | 0.053209 | −0.0233 | −0.051411 |
| 258 | −0.018849 | 0.002555 | 0.000051 | 0.044119 | 0.030617 | 0.011871 | 0.008236 | −0.016428 | −0.042633 | −0.031257 | 0.035817 | 0.049833 | −0.028818 | 0.011367 |
| 259 | −0.027373 | −0.023807 | 0.01336 | 0.000667 | 0.042622 | −0.001482 | 0.032938 | −0.027014 | −0.06285 | −0.003087 | 0.002639 | −0.019465 | −0.000054 | −0.042763 |
| 260 | 0.073701 | 0.018049 | −0.064473 | −0.010488 | 0.096876 | 0.008658 | 0.043568 | 0.047111 | −0.09041 | −0.041328 | 0.014574 | −0.018684 | 0.058831 | −0.037876 |
| 261 | 0.019093 | 0.016192 | −0.026629 | 0.028011 | 0.132659 | −0.074627 | 0.014081 | −0.016456 | −0.033336 | −0.048114 | 0.055693 | −0.050171 | −0.036262 | −0.018032 |
| 262 | −0.001468 | −0.037441 | −0.000433 | 0.018434 | 0.019522 | 0.015943 | 0.01142 | 0.004299 | 0.048955 | −0.020155 | 0.02336 | −0.04957 | −0.059482 | −0.010711 |
| 263 | 0.024922 | −0.026764 | 0.025337 | −0.003117 | 0.011793 | 0.057907 | 0.017645 | −0.030023 | 0.055918 | −0.014045 | 0.009338 | −0.019575 | −0.070068 | −0.033759 |
| 264 | −0.022052 | −0.000567 | −0.015153 | −0.013755 | −0.000805 | −0.002548 | −0.055324 | −0.071417 | 0.007494 | 0.061241 | 0.037681 | −0.049619 | 0.001191 | −0.058548 |
| 265 | 0.010023 | −0.114437 | −0.049326 | 0.003479 | −0.028228 | −0.010042 | −0.020127 | −0.087195 | −0.060742 | 0.022663 | 0.01218 | −0.084233 | 0.001727 | −0.017353 |
| 266 | −0.03446 | −0.068011 | −0.053253 | 0.054608 | 0.032555 | −0.062348 | 0.008679 | −0.051417 | −0.04149 | −0.032929 | −0.021563 | −0.031363 | −0.026423 | 0.018594 |
| 267 | 0.023209 | −0.019699 | −0.031575 | 0.002809 | 0.007525 | −0.040857 | −0.007587 | −0.05351 | 0.03857 | −0.062248 | −0.007809 | 0.085236 | 0.102056 | 0.001784 |
| 268 | 0.005343 | −0.033746 | 0.025969 | 0.028639 | −0.029094 | −0.005328 | −0.00367 | 0.025495 | 0.032292 | −0.049897 | −0.023025 | −0.02696 | 0.039001 | 0.009618 |
| 269 | 0.010352 | −0.01133 | 0.029707 | 0.008887 | −0.046838 | −0.040853 | −0.008009 | 0.016903 | 0.0205 | −0.024684 | −0.057622 | −0.044954 | 0.045589 | 0.009175 |
| 270 | 0.046869 | −0.018627 | 0.02862 | 0.001545 | 0.034093 | −0.036744 | −0.004445 | −0.008322 | 0.01173 | −0.041534 | −0.023848 | −0.047331 | 0.094767 | 0.017566 |
| 271 | 0.018323 | −0.003586 | −0.03593 | 0.189318 | 0.05514 | −0.035291 | −0.027278 | −0.21456 | −0.074425 | −0.033825 | −0.074196 | 0.015531 | −0.020715 | −0.080215 |
| 272 | −0.004884 | 0.038029 | 0.007823 | −0.015217 | −0.008481 | −0.017142 | −0.049842 | −0.051317 | −0.03806 | 0.023796 | 0.021748 | 0.012942 | 0.012232 | −0.085239 |
| 273 | 0.037463 | −0.030338 | 0.043339 | 0.004568 | −0.026303 | 0.066005 | 0.030531 | −0.004655 | 0.001678 | 0.034607 | 0.011189 | −0.052775 | 0.030954 | −0.001177 |
| 274 | 0.045017 | −0.025672 | 0.03528 | −0.007365 | −0.021449 | 0.051551 | 0.032922 | −0.006085 | −0.009413 | 0.048322 | −0.002485 | −0.052049 | 0.028637 | −0.01072 |
| 275 | −0.012475 | −0.021202 | 0.068708 | −0.0039 | 0.143443 | 0.0216 | 0.019802 | −0.060322 | 0.025869 | −0.041296 | 0.010089 | −0.004844 | 0.067509 | 0.074625 |
| 276 | −0.029569 | −0.043603 | −0.043485 | −0.059122 | −0.022205 | −0.052722 | −0.06629 | −0.032907 | −0.018266 | −0.064599 | 0.051202 | 0.044605 | 0.000127 | 0.021219 |
| 277 | 0.018496 | 0.04059 | −0.014684 | −0.015676 | 0.002407 | 0.002347 | 0.00625 | −0.002424 | 0.000029 | 0.040674 | 0.049188 | 0.008897 | 0.022312 | −0.009832 |
| 278 | 0.0165 | 0.071727 | −0.023445 | −0.052494 | 0.010793 | −0.026994 | 0.00013 | 0.001673 | −0.022171 | 0.043703 | 0.012572 | −0.02728 | −0.008459 | 0.005028 |
| 279 | −0.022176 | 0.104067 | −0.029804 | −0.004909 | −0.038072 | −0.038031 | −0.053961 | −0.039125 | 0.01557 | −0.008367 | 0.006755 | 0.040892 | −0.021246 | −0.041741 |
| 280 | 0.067366 | −0.014164 | 0.043452 | −0.015947 | 0.088459 | −0.036174 | 0.060928 | −0.018101 | 0.050106 | −0.064378 | −0.007242 | −0.059629 | −0.033294 | 0.041553 |
| 281 | 0.084266 | −0.002067 | −0.012795 | 0.005358 | 0.041537 | −0.022835 | 0.008738 | −0.052934 | −0.016207 | −0.053204 | −0.022496 | 0.036621 | −0.04007 | −0.057865 |
| 282 | 0.072289 | 0.030093 | −0.014986 | −0.019555 | 0.020942 | −0.002329 | −0.018347 | −0.042044 | −0.037362 | −0.019975 | −0.054087 | −0.002086 | −0.029222 | −0.070337 |
| 283 | 0.051912 | 0.077374 | −0.073926 | −0.028131 | 0.001488 | −0.029161 | −0.001636 | −0.011358 | −0.004232 | 0.030328 | −0.032859 | 0.040454 | 0.018783 | −0.006331 |
| 284 | 0.021284 | −0.036905 | 0.009636 | −0.025362 | −0.021725 | 0.060385 | 0.024649 | −0.001978 | −0.026335 | 0.028423 | 0.045358 | 0.041688 | −0.019453 | −0.055284 |
| 285 | 0.006126 | −0.032782 | −0.016296 | −0.033107 | −0.024921 | 0.068566 | 0.033021 | 0.008546 | −0.044068 | 0.063773 | 0.002146 | 0.035846 | −0.033147 | −0.065223 |
| 286 | −0.002288 | 0.010172 | 0.011929 | 0.000692 | −0.013542 | 0.006952 | 0.038275 | −0.035947 | −0.035457 | −0.019222 | −0.010907 | 0.040292 | −0.054424 | −0.084294 |
| 287 | −0.010077 | 0.056224 | 0.005404 | −0.009199 | 0.008449 | −0.001157 | 0.028296 | −0.00816 | −0.029206 | −0.01388 | −0.032584 | 0.012353 | −0.051372 | −0.05096 |
| 288 | −0.0370291 | 0.1142981 | 0.001218 | −0.019451 | 0.061756 | −0.06307 | 0.00773 | −0.035201 | −0.037148 | −0.005061 | 0.0089231 | 0.0248811 | −0.015864 | −0.008741 |
| 289 | 0.019794 | −0.036646 | −0.015062 | −0.004549 | 0.033696 | 0.018283 | 0.036054 | 0.004193 | 0.008832 | 0.011773 | 0.053391 | −0.004364 | −0.02702 | 0.015547 |
| 290 | −0.019912 | 0.03219 | −0.004452 | −0.043551 | 0.041829 | 0.003788 | −0.015109 | −0.02969 | 0.017324 | 0.068616 | −0.008191 | −0.023825 | 0.099732 | 0.011788 |
| 291 | −0.023018 | 0.040847 | −0.003066 | −0.036872 | 0.048879 | −0.003152 | −0.012074 | −0.029089 | 0.016195 | 0.066059 | −0.006053 | −0.017008 | 0.099532 | 0.006083 |
| 292 | −0.052355 | 0.021232 | −0.005068 | −0.019011 | 0.006588 | −0.012501 | −0.029271 | −0.050421 | 0.02658 | 0.048155 | −0.016267 | −0.012245 | 0.104933 | 0.015685 |
| 293 | −0.085561 | −0.018847 | −0.014752 | −0.009494 | −0.013255 | −0.116433 | 0.087922 | −0.064487 | −0.004891 | −0.055671 | 0.070574 | −0.095908 | −0.034797 | 0.007311 |
| 294 | 0.003336 | 0.014053 | −0.04113 | 0.052663 | 0.047416 | −0.005577 | 0.023114 | −0.060939 | 0.0080711 | 0.00821 | 0.0057261 | −0.049557 | 0.0884061 | 0.013476 |
| 295 | 0.006826 | −0.0412621 | 0.0213471 | −0.009298 | −0.032478 | 0.004704 | 0.08116 | −0.046774 | 0.002967 | −0.007753 | 0.008296 | −0.063265 | 0.01995 | 0.003709 |
| 296 | 0.069741 | 0.029575 | 0.012456 | 0.02171 | 0.08105 | 0.050907 | 0.003384 | −0.042423 | 0.098045 | −0.005148 | 0.013982 | −0.05463 | 0.114322 | 0.045932 |
| 297 | 0.022622 | −0.003136 | 0.004137 | −0.028581 | −0.045935 | −0.020066 | 0.067154 | −0.007918 | −0.017385 | −0.009638 | 0.019917 | −0.075536 | 0.0152 | −0.045143 |
| 298 | 0.08397 | 0.002359 | −0.064017 | 0.064833 | 0.01639 | 0.01901 | −0.048161 | −0.021098 | −0.068997 | 0.006656 | −0.044731 | 0.060962 | 0.072983 | 0.060349 |
| 299 | 0.020661 | 0.0257521 | −0.046794 | 0.042195 | 0.009992 | −0.079659 | −0.005436 | −0.020683 | −0.041603 | −0.05626 | −0.051395 | −0.049528 | −0.004841 | 0.006593 |
| 300 | 0.043972 | −0.12571 | −0.0733 | 0.016751 | −0.042779 | 0.03298 | 0.078752 | −0.037312 | −0.005385 | −0.100879 | −0.02953 | −0.004907 | 0.036741 | 0.079644 |
| 301 | 0.003191 | −0.028766 | −0.009667 | −0.008683 | 0.000217 | −0.026324 | −0.005823 | 0.023614 | −0.018522 | 0.019113 | 0.004476 | −0.009881 | −0.036766 | 0.001856 |
| 302 | 0.015985 | −0.017923 | −0.00614 | 0.015429 | 0.093732 | 0.002295 | −0.014328 | −0.022964 | 0.036584 | −0.014066 | 0.017027 | 0.020767 | 0.009153 | −0.022285 |
| 303 | 0.043916 | 0.042462 | −0.06781 | 0.080673 | 0.035357 | −0.122446 | −0.103206 | 0.034577 | −0.031528 | 0.016391 | −0.059746 | −0.016641 | 0.048158 | 0.042344 |
| 304 | 0.036207 | 0.0477261 | −0.030979 | 0.046994 | 0.06955 | −0.086602 | −0.103168 | −0.021897 | −0.004568 | −0.065523 | −0.050183 | 0.01691 | 0.0439361 | 0.036826 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 305 | −0.0628521 | −0.0912721 | −0.0160811 | 0.014879 | −0.011262 | −0.113596 | −0.017925 | 0.018914 | 0.010374 | 0.046258 | −0.001821 | −0.024677 | −0.030734 | −0.032028 |
| 306 | 0.024009 | −0.025326 | −0.011397 | −0.003326 | 0.01092 | 0.083124 | −0.032026 | 0.028712 | −0.020582 | 0.03527 | 0.037439 | −0.022862 | 0.023579 | 0.012019 |
| 307 | −0.003309 | 0.038326 | −0.077019 | 0.03906 | −0.02997 | 0.066258 | 0.011581 | −0.070462 | 0.072508 | 0.092696 | 0.000856 | 0.022851 | 0.005283 | 0.039006 |
| 308 | 0.012406 | 0.031976 | 0.016589 | −0.038974 | 0.015793 | 0.056816 | −0.032377 | −0.01087 | 0.0104 | 0.018044 | −0.017725 | 0.009105 | −0.029795 | −0.005876 |
| 309 | 0.007445 | 0.011838 | 0.019858 | −0.019438 | 0.022856 | −0.010963 | −0.021353 | −0.026346 | 0.050105 | −0.006003 | −0.033744 | 0.024457 | −0.017384 | 0.017299 |
| 310 | 0.08133 | 0.003836 | 0.008564 | 0.007645 | 0.059588 | 0.038706 | −0.049119 | −0.052356 | 0.044245 | 0.069291 | −0.081123 | 0.037278 | 0.024898 | −0.002788 |
| 311 | −0.046318 | 0.010101 | 0.006553 | −0.040495 | −0.077052 | −0.036889 | −0.000526 | 0.061755 | −0.022081 | 0.044009 | 0.047094 | −0.034407 | −0.014868 | 0.017334 |
| 312 | −0.087878 | 0.11078 | 0.031866 | −0.077077 | −0.095598 | 0.025252 | −0.071821 | 0.080773 | −0.043269 | 0.085892 | 0.062927 | −0.214335 | 0.00698 | 0.053212 |
| 313 | 0.042244 | −0.015114 | −0.015887 | −0.095358 | −0.065473 | 0.003456 | −0.040105 | 0.053151 | −0.068732 | 0.016967 | 0.028893 | 0.017127 | 0.003009 | −0.001482 |
| 314 | 0.009251 | 0.093773 | −0.122394 | −0.006877 | −0.029451 | 0.061183 | 0.05257 | −0.072925 | −0.040853 | −0.04001 | −0.137621 | −0.063159 | 0.016579 | 0.060922 |
| 315 | −0.005274 | 0.018598 | −0.030732 | −0.014609 | −0.023838 | −0.044258 | −0.029216 | 0.048971 | −0.021599 | −0.024343 | −0.054872 | −0.007916 | −0.027587 | 0.036092 |
| 316 | −0.025091 | 0.017171 | 0.025879 | −0.018203 | 0.159954 | 0.002625 | −0.036775 | 0.038448 | −0.06463 | −0.059941 | 0.048185 | 0.005654 | 0.122152 | 0.061883 |
| 317 | 0.01197 | −0.034992 | −0.015537 | −0.051745 | 0.030936 | 0.047902 | 0.017064 | 0.014232 | 0.003915 | 0.007421 | −0.024493 | 0.022824 | −0.047444 | 0.023587 |
| 318 | −0.082831 | −0.026847 | −0.062357 | −0.062778 | −0.003612 | 0.035006 | 0.049544 | 0.012523 | −0.012766 | −0.129541 | −0.080483 | 0.109183 | 0.036627 | 0.071009 |
| 319 | −0.023147 | 0.00763 | −0.0342791 | −0.021964 | −0.010547 | 0.032126 | −0.045864 | 0.03281 | 0.0203241 | −0.020391 | −0.028969 | 0.0329031 | −0.037778 | 0.040451 |
| 320 | −0.0676791 | 0.0140651 | −0.030364 | 0.002048 | 0.027067 | 0.196456 | −0.027669 | 0.029793 | −0.02051 | −0.060784 | 0.07513 | 0.022434 | 0.032207 | −0.027877 |
| 321 | 0.0769 | 0.045051 | −0.030614 | 0.037569 | 0.001336 | 0.018805 | 0.061176 | 0.049995 | −0.036546 | 0.024653 | −0.012097 | 0.032964 | 0.034225 | −0.006812 |
| 322 | 0.030533 | −0.106641 | −0.048024 | −0.115946 | −0.006836 | −0.044211 | 0.120158 | −0.009825 | 0.131986 | −0.057354 | −0.04792 | −0.062066 | 0.061207 | −0.087479 |
| 323 | −0.028508 | −0.097448 | 0.0175 | 0.050199 | −0.129175 | 0.027997 | −0.042304 | 0.029428 | −0.098722 | 0.042915 | −0.07502 | 0.022709 | 0.028345 | 0.030255 |
| 324 | 0.049407 | 0.015726 | −0.063419 | 0.030312 | 0.014619 | −0.153298 | −0.036562 | −0.145248 | −0.027358 | 0.052276 | 0.01795 | −0.017217 | 0.047889 | −0.073512 |
| 325 | 0.045271 | 0.009454 | −0.003338 | −0.036941 | 0.054133 | −0.110584 | −0.026273 | 0.046128 | 0.073757 | 0.032619 | 0.033004 | −0.018645 | 0.017852 | 0.004107 |
| 326 | −0.01993 | 0.098659 | 0.064047 | 0.007709 | 0.023914 | −0.013389 | −0.025444 | −0.007501 | 0.061668 | −0.052847 | 0.109006 | 0.019204 | −0.044639 | 0.031222 |
| 327 | −0.022799 | 0.019027 | 0.028955 | 0.002063 | −0.006401 | −0.025271 | −0.044107 | 0.003597 | 0.025448 | 0.043369 | −0.030433 | 0.052215 | −0.017734 | 0.016825 |
| 328 | 0.054318 | 0.117602 | −0.067193 | 0.075195 | −0.026998 | 0.172844 | −0.089698 | −0.037037 | 0.026757 | 0.04989 | 0.134349 | −0.025761 | −0.107265 | −0.084157 |
| 329 | −0.039262 | 0.045668 | 0.042578 | 0.026635 | −0.077325 | −0.045224 | −0.065852 | 0.082984 | −0.005917 | 0.02743 | 0.0054021 | 0.0897221 | −0.048206 | −0.044306 |
| 330 | −0.06648 | 0.004006 | −0.016926 | −0.134497 | 0.089901 | −0.043281 | −0.17286 | 0.108087 | −0.111274 | 0.050441 | −0.094282 | −0.036245 | 0.014885 | −0.147524 |
| 331 | −0.052434 | 0.05117 | 0.003369 | 0.036327 | −0.049079 | −0.062894 | −0.05322 | 0.03818 | 0.002641 | 0.018986 | −0.000826 | 0.005675 | 0.034215 | 0.041627 |
| 332 | −0.031102 | 0.068873 | −0.056375 | −0.05934 | −0.03721 | −0.002401 | −0.063909 | −0.085257 | −0.081292 | 0.043452 | 0.043498 | −0.011334 | −0.031077 | −0.02412 |
| 333 | −0.046118 | −0.004991 | 0.020613 | −0.031892 | −0.020718 | −0.071045 | −0.001687 | 0.050625 | 0.047683 | 0.023098 | 0.029673 | 0.030922 | 0.021737 | 0.034287 |
| 334 | −0.150923 | −0.001459 | 0.082858 | −0.036063 | 0.018922 | −0.029768 | 0.02505 | −0.02598 | 0.154375 | 0.063116 | −0.018661 | −0.083575 | 0.0757 | −0.134217 |
| 335 | −0.064565 | 0.042817 | −0.012264 | −0.008901 | −0.021064 | −0.022995 | −0.035013 | 0.026008 | −0.008725 | 0.038473 | 0.014939 | 0.009112 | −0.014535 | 0.07693 |
| 336 | 0.031562 | −0.058951 | −0.0818491 | 0.02597 | 0.022529 | 0.007885 | 0.050383 | 0.099905 | 0.045025 | −0.017542 | −0.024403 | 0.012533 | −0.00867 | 0.154631 |
| 337 | 0.015408 | −0.013142 | −0.041454 | 0.015721 | −0.008292 | 0.037317 | −0.086594 | 0.012031 | −0.045246 | −0.004215 | 0.010317 | −0.050908 | −0.011668 | 0.030304 |
| 338 | 0.003841 | 0.024993 | 0.045267 | 0.195983 | 0.030429 | 0.025972 | −0.055594 | −0.138696 | 0.151391 | 0.096954 | −0.023609 | 0.030407 | −0.048728 | 0.145404 |
| 339 | −0.073559 | 0.039717 | 0.009634 | −0.049523 | −0.073229 | 0.029601 | −0.087231 | 0.089353 | −0.026069 | −0.060643 | 0.03473 | 0.049437 | −0.042031 | 0.056061 |
| 340 | 0.047951 | 0.121217 | 0.147531 | −0.022929 | −0.016296 | −0.176393 | 0.177725 | 0.074812 | 0.001585 | −0.102727 | −0.045333 | 0.129652 | −0.001646 | 0.04649 |

| | BP | BQ | BR | BS | BT | BU | BV | BW | BX | BY | BZ | CA | CB | CC |
|---|---|---|---|---|---|---|---|---|---|---|---|---|---|---|
| 1 | 0.026496 | −0.03312 | 0.030796 | 0.059297 | 0.041538 | 0.007998 | −0.043809 | 0.03144 | −0.012279 | −0.026041 | 0.013455 | −0.007481 | −0.054495 | −0.030831 |
| 2 | 0.018805 | −0.053456 | −0.009028 | 0.025909 | −0.022549 | −0.007583 | −0.010575 | 0.010482 | −0.021074 | 0.01118 | −0.037832 | 0.036187 | 0.001121 | −0.002659 |
| 3 | 0.06663 | −0.051164 | 0.0482 | 0.033556 | −0.004971 | −0.012492 | −0.007493 | 0.049267 | 0.003129 | −0.0335 | 0.011637 | −0.022816 | −0.015843 | −0.02476 |
| 4 | −0.038358 | −0.081837 | −0.016698 | −0.064831 | 0.061225 | 0.044902 | 0.049199 | 0.050932 | −0.010461 | 0.00502 | 0.093857 | −0.005694 | −0.003001 | 0.060503 |
| 5 | 0.024061 | −0.047637 | −0.038654 | 0.048438 | −0.054225 | 0.013928 | −0.039219 | −0.096405 | −0.0586 | 0.000728 | −0.033731 | −0.017865 | −0.034241 | −0.030001 |
| 6 | 0.056974 1 | −0.01503 | 0.05673 | −0.140225 | −0.111571 | −0.021526 | −0.021189 | 0.06288 | −0.155377 | −0.016501 | −0.007644 | 0.06318 | 0.069099 | 0.025903 |
| 7 | 0.018962 | 0.071934 | −0.0507411 | 0.084363 | −0.024507 | −0.004772 | 0.051286 | 0.100304 | 0.0253461 | 0.154875 | −0.109699 | 0.0660951 | 0.03397 | 0.037094 |
| 8 | −0.0422241 | 0.06848 | 0.0781081 | 0.176963 | −0.068492 | −0.05944 | −0.029176 | 0.07799 | −0.093822 | −0.10591 | −0.099747 | −0.012326 | −0.047094 | −0.065772 |
| 9 | −0.063813 | 0.043474 | −0.030283 | −0.04985 | 0.025482 | 0.044938 | −0.005308 | −0.02941 | −0.040054 | 0.093437 | 0.073304 | 0.113764 | −0.054365 | 0.04276 |
| 10 | −0.044682 | −0.057799 | 0.042013 | 0.024516 | −0.019037 | 0.0529 | −0.001662 | −0.026351 | −0.019954 | 0.038966 | 0.095352 | −0.039732 | −0.057872 | −0.037453 |
| 11 | 0.118642 | 0.074955 | −0.0159 | 0.087327 | 0.062699 | −0.07405 | −0.099734 | 0.022257 | −0.035322 | −0.020331 | 0.022993 | −0.038841 | 0.053671 | −0.050112 |
| 12 | −0.078009 | 0.029229 | 0.152571 | 0.226732 | 0.002656 | 0.014793 | −0.052913 | −0.016076 | −0.017856 | −0.005455 | 0.04115 | −0.030149 | −0.088574 | −0.049481 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 13 | −0.037453 | 0.002077 | −0.005815 | −0.032782 | 0.024694 | 0.101247 | −0.072378 | 0.119423 | 0.023798 | −0.055804 | −0.048127 | 0.031685 | 0.001658 | −0.014567 |
| 14 | −0.047578 | 0.01218 | −0.062857 | 0.019795 | 0.03767 | 0.129379 | 0.036905 | 0.117859 | −0.097945 | −0.090889 | 0.093102 | 0.12866 | −0.011545 | −0.036247 |
| 15 | 0.018452 | 0.054112 | −0.069271 | 0.018913 | 0.034413 | −0.052701 | −0.053113 | 0.033345 | 0.030117 | 0.035943 | −0.011865 | 0.039339 | −0.072329 | −0.084135 |
| 16 | −0.11141 | 0.1269031 | −0.106354 | −0.140367 | −0.211428 | 0.014934 | 0.093615 | −0.094814 | 0.024721 | 0.063184 | 0.023689 | −0.095963 | −0.093592 | −0.127303 |
| 17 | −0.072895 | 0.089948 | −0.0031111 | −0.232316 | 0.0756 | 0.018715 | 0.072973 | −0.08655 | 0.020068 | −0.0216 | 0.03802 | 0.019035 | −0.077996 | 0.010864 |
| 18 | −0.0343091 | −0.0283181 | 0.0421091 | 0.045655 | −0.059111 | −0.010149 | −0.036126 | 0.067381 | 0.067719 | −0.015472 | 0.058523 | 0.112193 | 0.042618 | −0.040112 |
| 19 | 0.08889 | −0.103437 | −0.001191 | 0.03627 | 0.048637 | −0.044359 | 0.082899 | 0.060247 | −0.001464 | −0.028422 | 0.070868 | −0.088883 | 0.074777 | −0.096326 |
| 20 | −0.006937 | 0.004769 | 0.030042 | 0.048555 | 0.019908 | −0.038269 | 0.0292 | 0.047954 | 0.035269 | −0.024503 | −0.027605 | −0.00729 | −0.014911 | −0.01772 |
| 21 | −0.114716 | −0.035601 | 0.058306 | −0.047643 | 0.04836 | −0.011099 | 0.003492 | −0.065635 | −0.015135 | −0.025622 | −0.000223 | −0.033829 | 0.014652 | 0.095878 |
| 22 | 0.0048231 | −0.0929211 | −0.1214061 | −0.097934 | 0.078672 | −0.023491 | −0.045598 | −0.047327 | 0.122511 | −0.041161 | −0.037437 | −0.079237 | 0.06029 | 0.053505 |
| 23 | −0.018856 | 0.096852 | 0.070026 | 0.031349 | 0.049781 | −0.03554 | −0.133501 | 0.043809 | −0.024551 | 0.00949 | 0.002163 | −0.048677 | 0.05875 | 0.004336 |
| 24 | 0.033264 | −0.001649 | 0.002024 | 0.022559 | 0.010598 | −0.00497 | 0.034003 | 0.037515 | 0.025941 | −0.017057 | −0.021675 | −0.023927 | 0.183112 | 0.037833 |
| 25 | 0.007543 | −0.066028 | −0.044005 | 0.112284 | 0.12317 | −0.000246 | 0.007092 | −0.094648 | 0.071731 | −0.047583 | −0.044593 | 0.134556 | 0.061171 | 0.069743 |
| 26 | −0.029786 | 0.003946 | 0.03833 | 0.031805 | 0.002463 | −0.01223 | 0.012522 | 0.038937 | 0.029014 | −0.020509 | −0.023863 | −0.041377 | −0.007603 | 0.0042 |
| 27 | 0.004738 | −0.002633 | 0.026639 | −0.01055 | 0.008197 | −0.007559 | −0.009378 | 0.00715 | 0.01341 | −0.007601 | −0.013721 | −0.003721 | −0.001119 | −0.033678 |
| 28 | −0.052484 | −0.081927 | −0.021029 | 0.021769 | 0.024578 | 0.08392 | 0.007178 | −0.003982 | −0.001786 | 0.086562 | 0.052002 | −0.051677 | 0.006451 | −0.007517 |
| 29 | −0.025021 | −0.062098 | 0.226699 | −0.075151 | −0.037296 | 0.138592 | −0.019164 | −0.055364 | 0.112657 | 0.024732 | −0.065312 | 0.13159 | −0.033534 | −0.012933 |
| 30 | −0.032566 | 0.097958 | 0.00374 | 0.040738 | 0.027075 | −0.027158 | −0.049428 | −0.028717 | −0.004415 | 0.046979 | 0.074015 | 0.056663 | −0.021335 | −0.066445 |
| 31 | −0.01833 | 0.114718 | −0.094645 | 0.002054 | 0.053536 | −0.039719 | −0.012055 | −0.07672 | −0.012233 | 0.000742 | 0.003845 | 0.026102 | 0.051242 | −0.007068 |
| 32 | 0.02067 | 0.0172421 | 0.02614 | 0.027689 | 0.07358 | −0.029002 | 0.052078 | −0.010988 | −0.046548 | −0.052589 | 0.1809041 | −0.028348 | −0.001805 | 0.003118 |
| 33 | −0.063358 | 0.027587 | −0.0598191 | −0.000505 | 0.008036 | 0.004031 | −0.074268 | −0.002024 | 0.013523 | 0.116521 | 0.000111 | −0.109868 | 0.066163 | 0.006841 |
| 34 | −0.012515 | 0.019662 | 0.015986 | 0.02645 | 0.004959 | −0.018088 | −0.038059 | −0.033805 | −0.048554 | 0.0015 | −0.044472 | −0.079265 | 0.000128 | 0.02037 |
| 35 | −0.124803 | 0.045854 | 0.062129 | 0.038655 | −0.029902 | −0.115005 | 0.030144 | −0.045535 | −0.117021 | 0.039856 | −0.17266 | 0.016822 | 0.069796 | −0.10458 |
| 36 | 0.035122 | 0.121529 | 0.065483 | −0.027075 | 0.063583 | 0.031572 | −0.012044 | −0.00926 | 0.005213 | −0.077087 | −0.075094 | −0.108842 | 0.061633 | 0.052138 |
| 37 | 0.036622 | 0.040383 | 0.025035 | 0.033941 | 0.015556 | 0.007995 | 0.016318 | −0.084363 | −0.041139 | 0.033862 | −0.043133 | −0.082818 | −0.019621 | −0.002094 |
| 38 | −0.042643 | 0.116986 | 0.070168 | −0.146194 | 0.088066 | −0.080328 | −0.061968 | 0.007003 | 0.107856 | 0.019314 | −0.10845 | −0.029676 | −0.033574 | −0.03759 |
| 39 | −0.02049 | 0.073485 | 0.032115 | 0.015239 | −0.013065 | −0.022906 | 0.168382 | 0.119777 | −0.023581 | 0.021523 | 0.028186 | 0.015647 | −0.055665 | −0.018867 |
| 40 | 0.049006 | 0.027055 | −0.006202 | 0.036576 | 0.004156 | 0.09382 | −0.014227 | −0.029646 | −0.032979 | −0.017517 | −0.048878 | 0.038545 | −0.044467 | 0.027804 |
| 41 | 0.0302221 | −0.057896 | −0.030628 | 0.037057 | −0.0143 | 0.076519 | 0.024222 | −0.008066 | −0.023401 | −0.021397 | −0.048262 | −0.022161 | −0.002289 | 0.013259 |
| 42 | 0.0133061 | 0.0166221 | −0.033821 | 0.019095 | −0.041815 | 0.081431 | 0.018435 | 0.01237 | 0.0218331 | −0.035551 | −0.016832 | −0.006585 | −0.003496 | −0.051689 |
| 43 | 0.0218361 | 0.0141771 | −0.003987 | 0.015914 | −0.014702 | 0.062462 | −0.01131 | −0.024363 | −0.03081 | −0.027189 | −0.068459 | −0.028597 | −0.023054 | 0.053941 |
| 44 | −0.03204 | 0.006662 | −0.050355 | −0.006874 | −0.085505 | 0.072156 | −0.018358 | 0.028706 | −0.015661 | 0.026002 | −0.019605 | 0.010856 | 0.083621 | −0.035658 |
| 45 | 0.014336 | 0.023835 | 0.022951 | −0.015057 | −0.059066 | −0.034041 | −0.022609 | −0.000064 | −0.051417 | −0.031518 | −0.004081 | −0.042481 | 0.011395 | 0.039536 |
| 46 | 0.026728 | −0.041401 | −0.002797 | −0.09415 | 0.025616 | −0.025406 | 0.025605 | 0.063249 | 0.004174 | 0.02826 | −0.014458. | 0.105972 | 0.016678 | −0.107808 |
| 47 | −0.080261 | −0.026314 | 0.039585 | 0.018279 | −0.002184 | 0.021828 | −0.011491 | 0.024592 | −0.014526 | 0.012833 | 0.007951 | −0.015327 | −0.007625 | −0.011291 |
| 48 | 0.064474 | 0.028329 | −0.008176 | 0.035906 | 0.020176 | −0.065181 | 0.070197 | 0.005791 | −0.020827 | 0.0634581 | −0.075736 | 0.001647 | −0.036523 | 0.037112 |
| 49 | −0.01939 | 0.068311 | 0.0062931 | 0.031009 | 0.010035 | −0.049499 | −0.057722 | −0.038665 | 0.02261 | 0.010492 | 0.090002 | 0.044821 | −0.018902 | −0.09702 |
| 50 | −0.038366 | −0.042156 | −0.006718 | −0.025982 | −0.039708 | −0.035247 | −0.061261 | −0.064918 | −0.063613 | 0.016807 | −0.004042 | 0.047939 | 0.020128 | −0.064918 |
| 51 | −0.012336 | 0.048529 | −0.010733 | −0.062999 | 0.096303 | −0.002487 | 0.121206 | −0.00754 | −0.022034 | 0.0065 | −0.005141 | −0.000609 | −0.004422 | −0.040116 |
| 52 | 0.007537 | −0.043633 | 0.031165 | 0.095372 | 0.024192 | 0.021603 | 0.016671 | 0.000732 | −0.019268 | 0.042378 | 0.055979 | −0.015784 | 0.001535 | 0.054937 |
| 53 | 0.0933751 | −0.0370961 | −0.004816 | −0.05031 | 0.013943 | 0.007987 | 0.059593 | 0.021013 | 0.0105851 | 0.0186271 | 0.0255431 | −0.022349 | 0.025631 | −0.001634 |
| 54 | 0.0215851 | −0.0333111 | 0.0749551 | −0.043501 | −0.0188 | 0.017958 | −0.019939 | 0.084748 | −0.011776 | −0.004338 | 0.022777 | 0.024613 | −0.011988 | 0.048087 |
| 55 | 0.05749 | 0.006762 | −0.010101 | −0.018943 | 0.037402 | −0.007821 | −0.036152 | 0.026466 | −0.047958 | −0.015213 | −0.014716 | 0.000638 | 0.00618 | −0.035884 |
| 56 | 0.015898 | 0.032445 | −0.010926 | 0.025678 | 0.011163 | −0.039279 | −0.038846 | −0.035498 | −0.041557 | 0.043465 | −0.013929 | 0.013914 | 0.000999 | −0.052018 |
| 57 | 0.002437 | −0.0035421 | 0.025587 | −0.009073 | 0.029459 | 0.024771 | 0.004983 | −0.065533 | −0.051267 | −0.041007 | −0.007485 | 0.031889 | −0.069699 | 0.017103 |
| 58 | −0.003722 | −0.0065061 | 0.0452821 | −0.025221 | 0.010182 | 0.03029 | 0.133133 | 0.022042 | 0.0208021 | −0.047906 | 0.0401591 | −0.016091 | 0.0058651 | 0.031601 |
| 59 | −0.0173531 | −0.0153091 | 0.015181 | 0.008137 | −0.018607 | 0.002552 | 0.004749 | −0.034864 | −0.004426 | −0.016057 | 0.136441 | 0.026102 | −0.00611 | −0.055493 |
| 60 | −0.001676 | 0.00297 | 0.039299 | 0.017033 | −0.071555 | 0.012467 | −0.02085 | 0.035086 | 0.025466 | 0.00011 | −0.050463 | 0.12715 | 0.073229 | −0.011821 |
| 61 | 0.045204 | −0.048647 | 0.009497 | −0.044561 | −0.004439 | −0.008728 | −0.00364 | −0.004337 | 0.021352 | 0.005442 | −0.0591 | −0.049426 | 0.033399 | −0.014499 |
| 62 | −0.00799 | −0.018281 | −0.001001 | 0.039835 | −0.071953 | −0.043361 | −0.095448 | 0.044752 | −0.036587 | 0.08698 | −0.009231 | −0.038706 | 0.089465 | 0.022409 |
| 63 | 0.0224621 | −0.0406911 | 0.013912 | −0.021824 | −0.047267 | 0.00404 | −0.060185 | −0.017759 | 0.0633211 | 0.0306991 | 0.0002771 | −0.125681 | 0.0663951 | 0.067808 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 64 | −0.0260651 | 0.1014381 | 0.0035641 | 0.054822 | −0.016755 | −0.036434 | 0.025508 | −0.028005 | −0.016459 | −0.003472 | 0.058814 | 0.023279 | 0.002058 | −0.03314 |
| 65 | −0.081717 | −0.01369 | 0.034277 | −0.01752 | 0.004115 | −0.058869 | 0.051219 | −0.085445 | −0.020432 | −0.024899 | −0.024207 | 0.004559 | −0.010421 | −0.00241 |
| 66 | 0.025085 | −0.023863 | −0.02636 | −0.049903 | −0.038828 | −0.019626 | 0.029662 | 0.017802 | 0.075708 | −0.092126 | −0.035647 | −0.036715 | 0.139407 | −0.043638 |
| 67 | −0.109964 | 0.015388 | 0.0151841 | −0.015127 | 0.061962 | −0.025137 | 0.054453 | 0.01764 | 0.167345 | −0.00348 | 0.040362 | −0.097153 | 0.032731 | −0.007035 |
| 68 | 0.033676 | −0.166802 | 0.097149 | −0.041444 | −0.032649 | −0.054229 | 0.039893 | −0.032877 | −0.109618 | −0.052036 | −0.048749 | 0.0269581 | −0.014492 | 0.014806 |
| 69 | −0.018104 | −0.093305 | 0.019338 | 0.062211 | 0.084669 | −0.076805 | −0.010811 | −0.055149 | 0.098547 | 0.054272 | 0.039539 | 0.056689 | −0.081448 | −0.006111 |
| 70 | 0.030923 | 0.029576 | 0.013279 | −0.02843 | −0.0843 | −0.084599 | 0.05628 | −0.014774 | 0.013437 | 0.106124 | −0.015108 | −0.07075 | −0.027825 | −0.038309 |
| 71 | 0.0093 | −0.068521 | −0.009694 | 0.006637 | −0.029081 | −0.047302 | −0.011472 | −0.076014 | 0.063675 | 0.021304 | 0.049587 | −0.00309 | 0.002996 | 0.051762 |
| 72 | −0.032025 | −0.102265 | 0.032337 | −0.050939 | 0.021718 | −0.021588 | −0.003664 | −0.040804 | −0.000423 | 0.051001 | 0.097292 | −0.002332 | 0.014495 | 0.052194 |
| 73 | −0.021328 | 0.046992 | 0.002499 | −0.037871 | −0.078762 | 0.035203 | −0.107126 | 0.071133 | 0.08185 | −0.08728 | −0.079454 | −0.079444 | 0.001932 | −0.026072 |
| 74 | 0.0363141 | −0.0235851 | −0.0839751 | −0.008944 | −0.023679 | −0.055428 | 0.033414 | 0.004516 | −0.085528 | −0.009904 | −0.097204 | 0.048887 | −0.11245 | −0.095706 |
| 75 | 0.021669 | 0.006422 | 0.005267 | −0.008419 | 0.010574 | −0.006548 | 0.002151 | 0.016203 | −0.007561 | 0.004867 | −0.005444 | −0.037988 | −0.011415 | 0.027365 |
| 76 | −0.013834 | 0.028846 | 0.037526 | 0.038376 | −0.065166 | 0.021392 | 0.001672 | −0.075774 | −0.01517 | 0.010181 | 0.005597 | −0.064144 | 0.017402 | 0.129621 |
| 77 | 0.040154 | −0.0223661 | 0.007299 | −0.002847 | −0.008792 | −0.060835 | 0.015429 | −0.01908 | 0.011926 | 0.019691 | −0.032519 | −0.047683 | −0.03107 | 0.050589 |
| 78 | 0.058222 | 0.022131 | 0.043539 | 0.00188 | −0.016669 | −0.068496 | 0.022649 | −0.040632 | 0.0109651 | 0.0093121 | −0.019899 | −0.084151 | 0.0007141 | 0.028036 |
| 79 | 0.0274631 | 0.0487741 | −0.0171511 | −0.008553 | 0.072476 | 0.140481 | −0.101985 | 0.025658 | −0.03992 | 0.007502 | 0.022321 | 0.078505 | −0.051154 | −0.030363 |
| 80 | −0.018148 | 0.055756 | −0.027522 | 4.010783 | −0.036274 | 0.013314 | 0.10552 | −0.015983 | −0.097194 | −0.13991 | −0.041814 | −0.058381 | 0.018742 | 0.014519 |
| 81 | −0.137039 | −0.043998 | −0.155053 | 0.070209 | 0.003801 | −0.001069 | −0.024708 | −0.018486 | −0.072746 | −0.00376 | −0.115298 | 0.000038 | 0.120735 | −0.090711 |
| 82 | −0.028605 | 0.030008 | −0.013306 | −0.052995 | −0.003433 | 0.00867 | −0.030499 | 0.055721 | −0.019513 | 0.061667 | −0.026281 | 0.077075 | −0.026454 | 0.038757 |
| 83 | 0.024974 | −0.015092 | 0.025769 | −0.054017 | −0.01338 | 0.016463 | 0.000574 | 0.016507 | −0.015893 | −0.01469 | 0.027172 | 0.026179 | 0.045289 | −0.051019 |
| 84 | 0.010875 | −0.003747 | 0.04637 | −0.015389 | −0.088376 | 0.002327 | 0.007378 | −0.037902 | −0.015073 | 0.028562 | −0.044434 | 0.050838 | −0.005996 | 0.018974 |
| 85 | −0.035134 | 0.055906 | −0.069299 | 0.010369 | 0.09161 | 0.037014 | −0.062829 | 0.024075 | −0.147281 | 0.010767 | −0.023852 | 0.107811 | 0.070293 | −0.102725 |
| 86 | 0.043624 | −0.01063 | 0.051444 | −0.077419 | 0.014137 | 0.009413 | −0.03254 | −0.10706 | −0.017386 | −0.007401 | −0.008718 | 0.049859 | −0.050964 | −0.023844 |
| 87 | −0.027357 | −0.043997 | −0.015009 | 0.057808 | 0.055705 | 0.059013 | 0.039592 | 0.003148 | 0.000607 | −0.010651 | 0.042998 | −0.013711 | 0.1270481 | −0.00281 |
| 88 | 0.015295 | 0.047174 | 0.061041 | −0.005343 | −0.007309 | 0.010533 | 0.048165 | 0.035751 | −0.007415 | −0.006488 | −0.028621 | 0.059096 | −0.011656 | −0.08799 |
| 89 | 0.014503 | −0.041397 | 0.014547 | −0.001305 | −0.001058 | −0.034241 | 0.015142 | 0.025478 | −0.006226 | −0.015783 | 0.01175 | −0.010931 | 0.025845 | −0.04769 |
| 90 | 0.026756 | −0.065988 | −0.063175 | 0.019974 | −0.000162 | 0.003353 | −0.000791 | 0.033562 | 0.000625 | −0.059303 | 0.018701 | −0.051347 | 0.051854 | 0.031303 |
| 91 | 0.0660751 | 0.025018 | −0.09447 | −0.008098 | −0.075026 | −0.007824 | −0.002065 | 0.035539 | −0.06406 | −0.049145 | 0.027377 | −0.015646 | −0.086858 | 0.018155 |
| 92 | 0.039777 | 0.112715 | −0.08151 | 0.092208 | −0.03397 | 0.008194 | 0.163257 | −0.005137 | 0.030306 | −0.019127 | −0.030344 | 0.014651 | −0.063011 | −0.032605 |
| 93 | −0.009562 | −0.031159 | 0.015609 | −0.011332 | −0.019577 | −0.095966 | −0.025117 | −0.036746 | −0.046517 | −0.099491 | −0.063051 | −0.07777 | −0.013692 | 0.134953 |
| 94 | 0.050629 | 0.016202 | 0.007076 | −0.031123 | −0.095921 | 0.025527 | −0.098556 | −0.046323 | 0.155197 | 0.102092 | −0.015658 | 0.07481 | −0.117573 | −0.01461 |
| 95 | −0.057712 | 0.051068 | 0.055709 | −0.054551 | 0.025039 | 0.032528 | −0.026551 | 0.046248 | −0.081903 | 0.074175 | −0.000688 | −0.012065 | 0.019052 | 0.005954 |
| 96 | 0.130222 | 0.012494 | −0.082323 | −0.056972 | −0.040216 | −0.032929 | −0.040065 | −0.091808 | −0.021263 | 0.045355 | −0.048319 | 0.071394 | −0.000673 | 0.037085 |
| 97 | −0.028546 | 0.037949 | −0.078649 | 0.062818 | −0.001511 | 0.065437 | 0.002339 | −0.011941 | 0.08194 | −0.102438 | −0.082532 | −0.024797 | 0.0712211 | −0.051473 |
| 98 | −0.008604 | 0.00895 | −0.046126 | 0.020339 | 0.005904 | −0.017338 | 0.019828 | 0.049749 | −0.035109 | −0.006416 | 0.004831 | 0.012047 | 0.009733 | 0.032736 |
| 99 | −0.027887 | −0.015974 | −0.03425 | 0.049519 | 0.041898 | −0.069121 | 0.015909 | 0.008833 | 0.014187 | −0.008519 | 0.01714 | 0.051379 | −0.019811 | 0.058877 |
| 100 | −0.040039 | −0.005514 | 0.086535 | 0.027996 | 0.085432 | 0.053601 | −0.003476 | 0.061438 | −0.069631 | 0.03755 | 0.037916 | −0.049348 | −0.018615 | −0.028359 |
| 101 | −0.0289841 | −0.0055611 | 4.006646 | 0.0306 | −0.029562 | −0.055437 | −0.019824 | −0.011135 | 0.026301 | −0.033207 | 0.010459 | 0.036488 | 0.048226 | 0.0324 |
| 102 | −0.076542 | 0.017577 | 0.005742 | 0.056706 | 0.013121 | 0.025654 | 0.022034 | −0.031497 | −0.034098 | 0.050412 | −0.028036 | −0.035322 | 0.0271641 | 0.054664 |
| 103 | −0.058445 | −0.027429 | 0.011858 | 0.027103 | −0.029037 | −0.003821 | 0.03613 | −0.000049 | −0.07477 | −0.145302 | −0.000589 | −0.089058 | −0.005814 | −0.11122 |
| 104 | −0.137148 | 0.107363 | 0.108597 | 0.049731 | 0.05186 | −0.025499 | −0.0334 | 0.01054 | 0.09188 | −0.079934 | −0.048455 | −0.012129 | 0.036742 | 0.048016 |
| 105 | −0.092829 | −0.004624 | 0.109666 | −0.018401 | −0.095783 | −0.188214 | 0.083103 | 0.003086 | −0.071631 | 0.159966 | −0.028301 | −0.047201 | 0.001638 | −0.027865 |
| 106 | −0.001 | 0.039628 | 0.025156 | −0.060912 | −0.01405 | 0.00171 | −0.044966 | −0.059302 | −0.05921 | −0.052241 | −0.018137 | −0.126771 | −0.097795 | 0.015674 |
| 107 | −0.025186 | −0.014508 | −0.005467 | −0.118494 | −0.088625 | 0.090045 | −0.0731 | −0.075102 | 0.067031 | −0.083761 | 0.000208 | −0.01242 | −0.065771 | 0.050733 |
| 108 | −0.096407 | −0.007025 | 0.055353 | 0.001542 | 0.059077 | −0.030584 | −0.025693 | −0.038786 | 0.006562 | 0.001823 | −0.033292 | 0.170706 | −0.024777 | 0.110836 |
| 109 | −0.169933 | −0.004267 | 0.059066 | −0.056582 | −0.097189 | 0.049592 | 0.075624 | −0.056244 | −0.073787 | 0.030124 | 0.096864 | 0.059673 | 0.03959 | −0.06038 |
| 110 | 0.139885 | −0.016918 | 0.042517 | 0.058308 | 0.066896 | 0.055453 | −0.0081 | −0.042754 | 0.057223 | 0.001821 | −0.035744 | 0.019123 | −0.023312 | −0.028671 |
| 111 | 0.011962 | 0.084852 | 0.07031 | 0.108949 | −0.069612 | 0.068273 | −0.107521 | 0.118569 | −0.02029 | 0.079768 | 0.040371 | 0.123151 | 0.007905 | −0.044161 |
| 112 | 0.028098 | −0.07282 | −0.006307 | −0.086225 | 0.062831 | −0.107896 | 0.154745 | 0.054834 | 0.015763 | −0.072835 | −0.129023 | −0.005781 | 0.044558 | −0.002957 |
| 113 | −0.090272 | 0.021261 | −0.096404 | 0.044937 | −0.127663 | −0.134819 | −0.057605 | 0.097774 | 0.046592 | 0.058937 | −0.083896 | −0.023514 | −0.116499 | 0.001296 |
| 114 | 0.067234 | 0.073324 | −0.121193 | −0.096832 | 0.274213 | −0.140098 | 0.025849 | −0.101197 | −0.044662 | −0.020095 | −0.007158 | −0.018927 | −0.110652 | 0.067809 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 115 | 0.074206 | −0.036582 | −0.065081 | −0.04578 | −0.096072 | −0.043976 | −0.060539 | −0.014428 | 0.048827 | 0.061494 | −0.023771 | 0.074905 | 0.065892 | 0.002532 |
| 116 | −0.152985 | −0.1775251 | 0.040274 | −0.112577 | −0.061808 | 0.032136 | −0.013114 | 0.055112 | −0.087667 | −0.013413 | 0.007507 | −0.001864 | 0.05552 | −0.042121 |
| 117 | 0.015807 | −0.075307 | −0.024341 | −0.107737 | 0.032777 | 0.023984 | −0.06061 | −0.1187 | 0.039328 | −0.079677 | 0.048711 | 0.040707 | 0.0200061 | −0.037344 |
| 118 | −0.080328 | 0.072503 | 0.026499 | −0.049483 | 0.036941 | 0.121966 | −0.072158 | −0.068804 | 0.127981 | 0.032994 | 0.026466 | 0.095451 | 0.078644 | −0.037994 |
| 119 | −0.035185 | 0.032795 | 0.063265 | −0.001719 | −0.009028 | 0.044621 | 0.003855 | −0.026448 | 0.071539 | −0.030661 | 0.025933 | −0.080807 | 0.016935 | −0.016272 |
| 120 | −0.009528 | −0.017387 | −0.00666 | −0.031655 | 0.022967 | 0.052608 | −0.075143 | −0.031018 | 0.017238 | −0.065367 | 0.009021 | 0.057356 | −0.017148 | 0.030738 |
| 121 | 0.079908 | −0.076559 | −0.029475 | −0.038955 | 0.051131 | −0.050991 | −0.024016 | 0.028349 | −0.031334 | 0.006586 | 0.037263 | 0.004656 | −0.009308 | 0.03291 |
| 122 | −0.011096 | 0.049772 | 0.034975 | −0.076293 | −0.093018 | −0.0128 | −0.014768 | 0.004265 | −0.063327 | −0.036201 | −0.013876 | 0.038811 | 0.078387 | −0.000887 |
| 123 | −0.009211 | 0.039974 | 0.03087 | −0.036923 | −0.042978 | −0.021506 | −0.021556 | −0.059575 | −0.045619 | −0.031433 | −0.004129 | −0.016342 | −0.003478 | −0.002144 |
| 124 | −0.0545491 | 0.0113141 | 0.0671071 | −0.023863 | 0.010516 | −0.010968 | 0.02621 | −0.012479 | 0.0769961 | −0.010446 | −0.020344 | −0.056565 | −0.019756 | −0.01818 |
| 125 | 0.030151 | −0.029188 | 0.008238 | 0.030525 | −0.049788 | −0.015573 | 0.041126 | −0.011655 | −0.043096 | 0.028334 | −0.059069 | 0.090125 | −0.014669 | 0.087092 |
| 126 | −0.046018 | 0.004997 | −0.000205 | −0.011369 | −0.028969 | −0.022488 | −0.002194 | 0.01158 | −0.006587 | 0.04458 | −0.010246 | −0.037406 | −0.119035 | −0.032456 |
| 127 | −0.013724 | −0.003691 | 0.006615 | −0.003528 | −0.033918 | 0.040293 | 0.06637 | 0.053703 | 0.025957 | −0.021414 | 0.04722 | −0.044739 | −0.036533 | −0.011086 |
| 128 | −0.001882 | −0.003528 | 0.022253 | 0.011288 | 0.000817 | −0.025614 | −0.008612 | 0.018071 | 0.011799 | 0.0156 | −0.063287 | −0.090386 | 0.0131331 | −0.020662 |
| 129 | 0.072582 | 0.061217 | −0.050326 | 0.056481 | 0.034998 | 0.036732 | 0.094175 | −0.039745 | −0.00392 | 0.081862 | −0.063191 | 0.103601 | −0.005514 | 0.024757 |
| 130 | 0.012892 | 0.06141 | 0.051634 | 0.045866 | −0.002208 | −0.071095 | 0.043796 | 0.013534 | 0.012378 | 0.005996 | −0.006179 | −0.111686 | 0.229719 | 0.106837 |
| 131 | −0.0069561 | 0.0518171 | 0.034016 | −0.063397 | 0.014129 | 0.056421 | −0.073903 | 0.038998 | 0.062033 | −0.10568 | −0.075203 | −0.082329 | 0.041837 | −0.040654 |
| 132 | 4.070456 | 0.0368371 | −0.0343014 | −0.035917 | −0.054446 | −0.011585 | 0.012132 | −0.055365 | −0.032063 | 0.08745 | 0.094068 | 0.04296 | 0.054768 | −0.052777 |
| 133 | −0.112815 | −0.046783 | −0.00189 | −0.013903 | 0.011612 | 0.148112 | 0.022241 | 0.048415 | −0.033018 | −0.03539 | 0.02491 | −0.012917 | −0.020875 | 0.05867 |
| 134 | −0.008086 | −0.062251 | 0.045847 | −0.033261 | −0.008298 | −0.120977 | 0.053959 | 0.052614 | 0.007483 | −0.088287 | 0.03039 | 0.092194 | 0.015667 | −0.056811 |
| 135 | 0.023186 | 0.001104 | −0.057343 | −0.028579 | −0.036278 | 0.039683 | −0.02848 | −0.020831 | −0.038143 | −0.053596 | 0.003902 | −0.035543 | −0.07729 | −0.01264 |
| 136 | −0.068432 | 0.009088 | −0.016834 | 0.047955 | −0.064809 | −0.036017 | −0.039614 | 0.013204 | −0.051012 | 0.070813 | 0.063399 | 0.009679 | −0.003632 | 0.137949 |
| 137 | 0.002261 | −0.049858 | 0.020619 | 0.019275 | −0.023809 | −0.09084 | 0.044649 | 0.062442 | 0.05024 | 0.108349 | −0.03593 | 0.002131 | 0.066808 | −0.014581 |
| 138 | 0.047933 | −0.019355 | 0.012615 | −0.126586 | −0.097907 | −0.03067 | 0.003871 | 0.095292 | 0.128596 | −0.031126 | −0.003419 | −0.083085 | −0.095881 | −0.026242 |
| 139 | −0.01496 | −0.066015 | 0.018185 | 0.139178 | −0.065757 | 0.00171 | −0.127092 | −0.040409 | 0.076291 | 0.116233 | 0.054461 | 0.012951 | 0.023692 | 0.00143 |
| 140 | −0.012401 | 0.044499 | −0.026687 | −0.044352 | 0.04885 | −0.156228 | 0.053484 | 0.017333 | −0.087811 | −0.066246 | 0.007441 | −0.041356 | −0.051253 | 0.000527 |
| 141 | 0.034317 | −0.077869 | 0.1262441 | −0.051195 | 0.082419 | −0.041415 | −0.06958 | 0.050376 | −0.058639 | 0.139404 | −0.023241 | −0.04823 | −0.046491 | −0.082146 |
| 142 | 0.015981 | 0.051826 | −0.03545 | 0.028363 | 0.03954 | 0.02005 | −0.093493 | −0.032242 | −0.025245 | −0.045856 | −0.061547 | −0.057888 | 0.114359 | −0.136159 |
| 143 | 0.023775 | 0.023076 | 0.054494 | 0.020981 | 0.070835 | −0.027097 | 0.0271 | −0.158699 | −0.06311 | −0.060721 | −0.082568 | 0.080753 | 0.0314281 | 0.155968 |
| 144 | 0.018429 | −0.016665 | 0.042775 | 0.018012 | 0.076298 | −0.036681 | 0.05875 | 0.01495 | −0.031577 | −0.011722 | 0.035273 | −0.049211 | −0.066425 | −0.012775 |
| 145 | −0.039592 | 0.038058 | −0.14544 | 0.032679 | −0.077935 | −0.05636 | −0.014044 | −0.059454 | −0.012966 | −0.103235 | −0.035888 | 0.059067 | 0.020617 | 0.121112 |
| 146 | −0.018984 | −0.002107 | −0.039749 | 0.002797 | −0.021561 | 0.050532 | 0.021753 | 0.054894 | −0.016105 | −0.008503 | −0.039243 | −0.011668 | −0.015775 | 0.033359 |
| 147 | −0.042545 | 0.040109 | −0.085369 | 0.030269 | 0.119198 | −0.02935 | 0.027563 | −0.002438 | −0.109238 | −0.008234 | −0.052684 | −0.052244 | −0.020242 | 0.015801 |
| 148 | −0.016095 | 0.029729 | −0.058757 | 0.002995 | 0.023104 | 0.101215 | −0.171007 | 0.018309 | 0.007482 | 0.006391 | 0.114161 | −0.13709 | −0.006974 | −0.064529 |
| 149 | 0.093136 | −0.013854 | 0.009139 | −0.047362 | 0.039889 | −0.116603 | −0.107575 | 0.036621 | −0.057604 | −0.021939 | 0.019518 | 0.143001 | 0.049375 | −0.11765 |
| 150 | 0.011633 | 0.045628 | −0.059498 | 0.087576 | −0.086828 | 0.094979 | 0.041027 | −0.008912 | 0.114709 | −0.027315 | −0.093902 | 0.050946 | −0.063016 | 0.040406 |
| 151 | −0.066615 | −0.129005 | 0.086349 | 0.087809 | 0.000757 | −0.115115 | −0.053167 | −0.076489 | −0.003531 | −0.127206 | 0.191552 | 0.043385 | 0.106521 | 0.016785 |
| 152 | 0.062884 | −0.080302 | −0.0418081 | 0.003177 | 0.005873 | −0.069362 | 0.068172 | 0.077828 | 0.012568 | −0.000925 | 0.018327 | 0.026063 | 0.040295 | −0.062989 |
| 153 | 0.00532 | −0.076574 | −0.09585 | 0.11295 | −0.017162 | −0.03904 | 0.004678 | −0.000225 | −0.05036 | 0.047888 | −0.013986 | 0.024995 | 0.054604 | −0.07656 |
| 154 | 0.017643 | 0.048218 | −0.028336 | 0.070468 | 0.030932 | −0.030195 | −0.064834 | 0.040993 | 0.000154 | −0.031801 | −0.036939 | −0.068917 | 0.052873 | −0.041194 |
| 155 | 0.0646 | 0.097524 | 0.028316 | 0.020436 | 0.012666 | 0.073828 | 0.079137 | 0.005091 | 0.086776 | 0.115526 | 0.035555 | 0.039345 | −0.044063 | 0.053517 |
| 156 | 0.0556351 | −0.040702 | −0.0119171 | 0.073849 | 0.033448 | 0.165881 | −0.048716 | 0.059415 | 0.0367 | −0.145688 | −0.019958 | −0.02769 | −0.049424 | 0.053163 |
| 157 | −0.0427161 | 0.011153 | −0.0360411 | −0.063035 | −0.072434 | 0.117003 | −0.024048 | −0.01204 | −0.029379 | −0.032234 | −0.074321 | −0.009177 | −0.092058 | 0.028696 |
| 158 | 0.047722 | −0.040105 | 0.112383 | 0.042488 | 0.27651 | −0.052588 | 0.034984 | 0.020557 | −0.020537 | −0.030056 | −0.101438 | 0.032372 | −0.075047 | −0.075582 |
| 159 | −0.049038 | 0.169141 | 0.009811 | −0.002418 | −0.077438 | 0.03899 | −0.067513 | 0.067879 | −0.08209 | −0.160428 | 0.080354 | 0.028575 | −0.078478 | −0.029924 |
| 160 | −0.103553 | −0.170318 | 0.083713 | 0.039482 | −0.040886 | 0.001164 | −0.095882 | 0.031777 | 0.014404 | −0.053431 | 0.002324 | 0.020923 | −0.085211 | −0.006668 |
| 161 | 0.053023 | −0.069525 | 0.086118 | 0.086292 | 0.091718 | −0.030658 | −0.0029 | −0.252075 | 0.124185 | −0.039913 | 0.013827 | −0.078247 | 0.036554 | −0.027203 |
| 162 | −0.069379 | 0.003813 | −0.000813 | −0.154904 | 0.027249 | −0.013851 | −0.032308 | −0.007258 | 0.033902 | 0.042892 | −0.104553 | 0.025111 | 0.021008 | 0.081422 |
| 163 | 0.05981 | −0.104908 | −0.058598 | −0.060004 | −0.002016 | 0.013547 | −0.116831 | −0.016299 | 0.040799 | −0.051996 | −0.045434 | −0.032757 | 0.028273 | −0.073902 |
| 164 | −0.094392 | −0.089543 | −0.082587 | −0.010971 | 0.067341 | 0.011025 | −0.061078 | 0.100186 | −0.05106 | −0.060245 | 0.014124 | −0.059195 | 0.098378 | −0.028179 |
| 165 | 0.115173 | −0.026129 | 0.137178 | 0.047608 | −0.124629 | 0.08891 | 0.075868 | −0.051277 | 0.062217 | −0.00173 | 0.078613 | 0.135258 | 0.018356 | 0.135691 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 166 | 0.038149 | −0.001488 | −0.042449 | −0.13787 | −0.0867 | 0.021651 | −0.064381 | −0.064798 | −0.02831 | 0.021755 | 0.07059 | 0.058071 | 0.076135 | 0.002439 |
| 167 | −0.138734 | 0.066499 | −0.095367 | 0.022664 | −0.009467 | −0.10103 | 0.048038 | 0.076687 | −0.085491 | 0.02999 | 0.090563 | 0.020703 | 0.038681 | 0.102123 |
| 168 | −0.095293 | −0.116096 | 0.010584 | 0.029423 | −0.031987 | 0.023661 | 0.046777 | −0.067604 | −0.061952 | −0.086106 | −0.117424 | −0.035181 | −0.009315 | −0.007708 |
| 169 | 0.004985 | 0.008586 | −0.030132 | 0.000468 | 0.040053 | −0.015875 | 0.030704 | 0.021687 | 0.034469 | −0.03706 | 0.021091 | 0.00366 | −0.024621 | 0.044175 |
| 170 | 0.007236 | −0.014417 | −0.014864 | 0.004156 | 0.040927 | −0.041395 | 0.000657 | 0.048232 | 0.068796 | −0.055504 | 0.005891 | −0.010055 | −0.017168 | 0.018798 |
| 171 | 0.046061 | −0.042808 | 0.000811 | 0.002313 | 0.035101 | −0.024513 | 0.025572 | 0.00939 | 0.020938 | −0.003553 | 0.043684 | −0.003763 | −0.029857 | −0.010797 |
| 172 | −0.032522 | −0.032661 | −0.024707 | 0.044864 | 0.072479 | −0.030466 | −0.004446 | 0.023567 | 0.041971 | 0.039586 | 0.032823 | −0.01978 | −0.034961 | 0.092363 |
| 173 | 0.026594 | 0.013569 | −0.05441 | 0.029711 | 0.023698 | −0.014936 | −0.000646 | 0.040857 | 0.034185 | 0.041072 | 0.032236 | 0.009459 | 0.014716 | 0.046456 |
| 174 | 0.052061 | −0.019503 | −0.004345 | 0.040767 | −0.008336 | −0.004042 | −0.029203 | −0.014607 | −0.034677 | −0.031344 | 0.053884 | −0.035621 | 0.035061 | −0.020454 |
| 175 | 0.020552 | −0.022781 | 0.082839 | −0.073627 | −0.085171 | 0.069297 | 0.121167 | −0.094691 | 0.102777 | −0.012788 | −0.084929 | 0.105926 | 0.033036 | −0.067305 |
| 176 | −0.074544 | −0.09876 | 0.01601 | −0.052925 | 0.00014 | 0.026167 | 0.0035 | 0.028551 | 0.084412 | 0.015728 | 0.023577 | 0.021209 | −0.020835 | 0.024667 |
| 177 | −0.026057 | −0.026403 | −0.09061 | 0.040111 | 0.004155 | 0.034554 | −0.131887 | −0.172971 | −0.065133 | −0.034038 | −0.05638 | −0.078262 | −0.081329 | −0.018239 |
| 178 | 0.027778 | −0.064009 | 0.018461 | 0.050263 | −0.022793 | 0.021956 | 0.005714 | −0.034516 | 0.018685 | 0.055185 | −0.0715 | −0.032326 | −0.00987 | 0.012526 |
| 179 | 0.00439 | 0.036395 | −0.033991 | 0.028047 | −0.034668 | 0.015769 | 0.018003 | −0.033527 | −0.019055 | −0.022087 | −0.013295 | 0.005616 | 0.029512 | −0.018749 |
| 180 | 0.025601 | 0.022647 | −0.029413 | 0.018475 | −0.012343 | −0.015443 | −0.019466 | 0.010504 | −0.016021 | 0.019729 | −0.024681 | 0.037018 | 0.004572 | 0.030482 |
| 181 | −0.000627 | 0.008328 | −0.013305 | 0.015026 | −0.020288 | −0.015788 | 0.017955 | −0.019461 | −0.008953 | 0.01798 | 0.0141961 | 0.038995 | 0.023606 | −0.023546 |
| 182 | −0.021621 | 0.032792 | 0.02607 | 0.019706 | 0.064361 | 0.047944 | −0.007876 | 0.036747 | 0.011824 | 0.059224 | 0.002276 | 0.006286 | 0.020574 | −0.060525 |
| 183 | −0.000246 | 0.068144 | −0.005766 | 0.041081 | −0.014931 | 0.01456 | 0.047992 | −0.015008 | −0.045222 | 0.028245 | 0.002415 | −0.037971 | −0.012583 | −0.081073 |
| 184 | 0.051251 | 0.018404 | 0.050327 | 0.000012 | −0.052923 | −0.106554 | 0.005447 | −0.068807 | 0.002598 | −0.04686 | 0.12568 | −0.066854 | 0.006727 | −0.097009 |
| 185 | 0.222223 | −0.123936 | −0.01292 | −0.04492 | −0.031832 | 0.017255 | −0.080392 | 0.026372 | 0.033027 | 0.085342 | −0.015673 | 0.029654 | −0.035691 | −0.019179 |
| 186 | 0.043173 | 0.053072 | −0.054177 | 0.045547 | 0.084844 | 0.006437 | −0.044446 | 0.060161 | −0.051126 | 0.053371 | 0.071638 | −0.027429 | 0.139549 | 0.114538 |
| 187 | −0.059825 | 0.128384 | −0.035087 | 0.020919 | 0.045958 | −0.013123 | −0.020467 | 0.052503 | 0.037781 | 0.042571 | 0.02636 | −0.024296 | 0.013793 | 0.058083 |
| 188 | −0.006726 | 0.085711 | −0.013825 | 0.021909 | 0.018333 | 0.011841 | −0.066964 | 0.010578 | −0.001322 | 0.027657 | 0.036342 | −0.06272 | −0.034855 | 0.049567 |
| 189 | −0.025726 | 0.082741 | 0.025493 | −0.042596 | −0.050482 | 0.024691 | −0.07027 | 0.021245 | −0.062881 | 0.011542 | 0.048005 | −0.046247 | −0.036625 | −0.019243 |
| 190 | −0.062948 | 0.049893 | 0.059689 | −0.039221 | 0.014115 | −0.114256 | −0.046472 | −0.021772 | 0.062859 | 0.003298 | −0.010941 | 0.010212 | 0.016603 | 0.03556 |
| 191 | −0.048737 | 0.072599 | 0.063791 | −0.03663 | 0.002376 | −0.028552 | −0.011142 | −0.03612 | −0.022782 | −0.042251 | 0.028308 | 0.030245 | 0.017045 | −0.006214 |
| 192 | 0.021183 | 0.053783 | 0.031617 | −0.042303 | 0.033453 | 0.028191 | −0.008464 | 0.059353 | 0.031426 | 0.10891 | −0.00973 | −0.078406 | 0.09424 | 0.056076 |
| 193 | −0.025613 | −0.037777 | 0.002138 | −0.015426 | 0.04644 | 0.028444 | −0.092448 | 0.032631 | 0.015219 | −0.006519 | −0.006902 | −0.044198 | 0.097581 | −0.033463 |
| 194 | −0.044969 | 0.04401 | −0.146702 | 0.016008 | −0.107398 | −0.009714 | 0.049393 | −0.063036 | 0.058103 | −0.04253 | −0.070538 | 0.10903 | 0.00124 | −0.017716 |
| 195 | 0.000789 | 0.048937 | −0.094621 | −0.122007 | 0.024462 | 0.045747 | 0.006425 | 0.012941 | 0.008015 | −0.061933 | −0.019054 | 0.054745 | 0.086418 | −0.016818 |
| 196 | −0.011157 | 0.011656 | 0.012935 | −0.131573 | 0.018038 | −0.034414 | 0.010192 | −0.043608 | 0.011988 | −0.018073 | 0.000736 | 0.062693 | 0.061143 | 0.007014 |
| 197 | −0.026143 | 0.079577 | 0.080137 | −0.085162 | 0.110018 | −0.067064 | −0.053571 | 0.125405 | −0.054033 | −0.07794 | −0.017548 | 0.017032 | 0.042943 | 0.015825 |
| 198 | −0.033114 | −0.125406 | −0.008782 | −0.0002 | −0.015396 | 0.053112 | 0.003253 | 0.021025 | 0.034759 | −0.053862 | −0.163124 | −0.109679 | −0.008318 | −0.081463 |
| 199 | 0.13676 | 0.140084 | 0.087881 | 0.02609 | 0.00168 | 0.073459 | −0.035533 | 0.118558 | 0.042144 | 0.005144 | 0.072631 | 0.098427 | 0.076887 | 0.024046 |
| 200 | −0.057526 | −0.147814 | −0.082814 | 0.094661 | 0.048402 | 0.033323 | 0.053073 | −0.009316 | −0.036055 | 0.125404 | 0.035231 | −0.008497 | −0.09612 | −0.085578 |
| 201 | 0.001523 | −0.089112 | −0.053766 | −0.014516 | 0.002822 | 0.05004 | 0.018583 | 0.138379 | 0.049449 | 0.049903 | 0.034309 | 0.060573 | −0.06487 | 0.122113 |
| 202 | 0.013864 | −0.089084 | −0.060892 | −0.033367 | −0.034601 | −0.013588 | −0.016541 | 0.148213 | 0.015753 | 0.019339 | −0.066865 | −0.026776 | −0.047355 | 0.108884 |
| 203 | −0.008537 | 0.024366 | −0.02725 | 0.047841 | 0.00428 | 0.052861 | −0.009877 | −0.003578 | −0.121009 | −0.039489 | 0.033815 | 0.031742 | −0.02801 | 0.008404 |
| 204 | −0.09057 | −0.014652 | 0.001029 | 0.022985 | 0.070721 | −0.083731 | 0.021427 | 0.051378 | 0.091378 | −0.021969 | −0.047661 | 0.103885 | −0.092981 | −0.088901 |
| 205 | −0.004683 | 0.018865 | 0.011411 | 0.039191 | −0.071078 | −0.060836 | −0.00917 | 0.018391 | 0.091689 | 0.037966 | 0.02986 | −0.047863 | −0.020009 | 0.006426 |
| 206 | 0.028384 | 0.011624 | 0.039195 | 0.05254 | 0.060498 | 0.022052 | −0.125314 | −0.058386 | 0.014765 | −0.029071 | −0.027134 | −0.025349 | −0.084315 | 0.015435 |
| 207 | 0.015419 | 0.007476 | 0.088224 | −0.106626 | 0.064434 | 0.120911 | 0.057404 | −0.074031 | −0.107919 | 0.036281 | −0.029241 | −0.095089 | 0.146808 | −0.042535 |
| 208 | 0.069333 | −0.118574 | −0.102222 | 0.077141 | −0.151675 | −0.027086 | −0.013473 | 0.07164 | 0.004281 | −0.105888 | 0.013455 | 0.111667 | −0.043244 | −0.047516 |
| 209 | 0.126383 | 0.031335 | −0.095873 | −0.078601 | 0.001144 | 0.028332 | 0.056135 | −0.033324 | 0.050847 | 0.014683 | 0.002468 | 0.026755 | −0.007685 | −0.052497 |
| 210 | 0.000587 | −0.008975 | −0.039369 | −0.021919 | −0.016527 | 0.094727 | 0.09731 | 0.014206 | −0.076247 | 0.146372 | −0.015396 | 0.005929 | 0.098846 | −0.040118 |
| 211 | 0.142497 | 0.078473 | −0.142249 | 0.066134 | 0.00496 | −0.060235 | −0.041827 | −0.057727 | −0.110169 | 0.038169 | −0.057132 | −0.061614 | −0.118226 | 0.087502 |
| 212 | −0.008867 | 0.012876 | 0.012155 | −0.07226 | 0.062445 | 0.015572 | −0.050094 | −0.001069 | 0.057658 | 0.165752 | −0.061189 | −0.000107 | 0.059135 | −0.025616 |
| 213 | −0.103066 | −0.026553 | 0.105502 | 0.07219 | −0.071873 | −0.066991 | −0.056597 | −0.027456 | −0.073432 | 0.037295 | 0.050786 | 0.060734 | 0.01123 | 0.045682 |
| 214 | 0.021764 | 0.04351 | −0.043948 | −0.01277 | −0.057406 | −0.00039 | −0.036293 | −0.025976 | −0.031938 | 0.015214 | −0.02129 | −0.03558 | −0.009525 | 0.024703 |
| 215 | 0.027853 | −0.061673 | −0.017365 | 0.010453 | −0.035769 | 0.01937 | −0.014697 | −0.152514 | 0.004212 | −0.055875 | 0.073361 | 0.114079 | −0.000572 | −0.094158 |
| 216 | −0.104365 | 0.033972 | 0.043107 | −0.02761 | 0.040585 | 0.04285 | 0.103646 | 0.074582 | −0.032349 | −0.056673 | 0.001356 | 0.030517 | −0.019628 | −0.058217 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 217 | 0.022892 | 0.113633 | 0.058795 | 0.076087 | 0.035943 | 0.025908 | 0.01775 | −0.040496 | 0.041251 | −0.048667 | 0.057951 | −0.062555 | −0.110864 | 0.011887 |
| 218 | 0.03095 | −0.016489 | −0.089829 | −0.047219 | −0.032314 | 0.029126 | −0.035358 | −0.018014 | −0.032848 | −0.025275 | 0.034683 | 0.02302 | 0.039886 | −0.003711 |
| 219 | 0.019292 | 0.002865 | −0.042624 | −0.005966 | 0.003877 | 0.038591 | −0.030589 | −0.008482 | −0.027071 | −0.02398 | 0.037452 | −0.04436 | 0.029829 | −0.010747 |
| 220 | 0.038098 | 0.059061 | 0.081866 | 0.044006 | −0.034426 | 0.0298 | 0.024122 | 0.015844 | −0.022062 | 0.008658 | 0.075899 | −0.048086 | −0.028828 | 0.011651 |
| 221 | −0.025291 | 0.007743 | −0.061968 | −0.027701 | −0.020424 | −0.013767 | −0.019872 | 0.01746 | −0.070376 | 0.020986 | −0.006442 | 0.0135711 | −0.064865 | 0.000415 |
| 222 | 0.008895 | 0.001102 | 0.000255 | −0.007187 | −0.048586 | 0.057978 | 0.026575 | −0.026715 | −0.073811 | 0.053075 | 0.034849 | −0.036017 | −0.041058 | −0.005504 |
| 223 | −0.044852 | −0.048336 | −0.030124 | 0.012527 | −0.055938 | 0.038574 | 0.059293 | −0.064403 | −0.049462 | 0.033211 | −0.023432 | 0.054034 | 0.039936 | −0.040767 |
| 224 | 0.058108 | 0.008629 | 0.023979 | −0.000769 | −0.035221 | −0.115883 | −0.053819 | 0.019076 | 0.03868 | 0.007176 | 0.014669 | 0.044146 | 0.043416 | −0.021229 |
| 225 | 0.045844 | 0.004172 | −0.010446 | 0.051312 | −0.047548 | −0.095092 | −0.004714 | 0.026096 | 0.050955 | −0.007188 | 0.020082 | 0.049407 | 0.069683 | 0.031575 |
| 226 | 0.043051 | −0.011829 | 0.01778 | −0.005513 | −0.001397 | 0.00326 | 0.000424 | 0.020513 | −0.042013 | 0.063173 | −0.031791 | −0.001966 | 0.035416 | −0.010096 |
| 227 | 0.016753 | 0.024522 | 0.057116 | −0.010417 | −0.005274 | −0.050366 | −0.062204 | −0.02471 | −0.000185 | −0.058508 | 0.002059 | 0.031759 | −0.005148 | 0.096846 |
| 228 | −0.010021 | 0.036805 | 0.030705 | −0.109497 | −0.032589 | −0.118298 | −0.095512 | −0.016657 | −0.057544 | 0.145084 | −0.032992 | 0.039753 | 0.006004 | 0.002076 |
| 229 | −0.085271 | 0.009892 | −0.05282 | 0.005551 | −0.047722 | −0.068861 | 0.061865 | −0.044544 | 0.025112 | −0.135155 | 0.073857 | 0.025525 | −0.001487 | −0.026429 |
| 230 | −0.062841 | −0.026042 | −0.00228 | 0.041205 | 0.001042 | −0.015655 | 0.070147 | −0.001872 | 0.005463 | −0.004427 | −0.057253 | 0.007032 | −0.030686 | 0.010978 |
| 231 | −0.024323 | 0.058585 | −0.058249 | 0.006851 | 0.06804 | −0.038785 | −0.086627 | 0.035515 | 0.049216 | −0.043642 | 0.064622 | 0.03729 | 0.054383 | −0.046547 |
| 232 | 0.089666 | −0.050195 | 0.072476 | −0.019453 | −0.029706 | 0.084899 | −0.139268 | 0.018959 | −0.192894 | −0.094347 | −0.049415 | 0.084615 | 0.089927 | 0.133043 |
| 233 | 0.005598 | −0.059526 | −0.03251 | 0.032594 | 0.012983 | 0.024182 | −0.002392 | 0.076339 | 0.025011 | −0.005108 | −0.073865 | 0.010915 | −0.071809 | 0.03395 |
| 234 | −0.027217 | −0.030082 | −0.073657 | 0.056666 | 0.011114 | 0.00367 | −0.000353 | 0.052786 | 0.068919 | 0.004251 | −0.059191 | −0.025423 | 0.003689 | 0.007441 |
| 235 | −0.019111 | 0.003131 | −0.066195 | 0.023143 | −0.03802 | 0.019323 | −0.081554 | −0.071874 | 0.035332 | −0.044096 | 0.04282 | −0.052726 | −0.060183 | −0.00518 |
| 236 | −0.005163 | −0.047656 | 0.021407 | 0.005369 | 0.062406 | 0.00504 | −0.012234 | −0.046153 | −0.070741 | 0.025894 | −0.027237 | 0.04401 | 0.003585 | −0.026555 |
| 237 | −0.066592 | −0.0263541 | −0.009478 | −0.056783 | −0.001051 | −0.025668 | −0.051436 | −0.000461 | 0.012074 | −0.017951 | 0.026477 | 0.06296 | 0.042619 | 0.083393 |
| 238 | −0.016519 | −0.007182 | −0.021064 | 0.009714 | −0.01306 | −0.011781 | 0.00338 | 0.027448 | 0.070935 | −0.028461 | 0.040122 | 0.031298 | 0.031743 | 0.043432 |
| 239 | 0.048132 | −0.001683 | −0.01803 | 0.03289 | 0.01472 | 0.025774 | 0.032673 | 0.022037 | 0.043237 | −0.029327 | 0.021201 | −0.013435 | 0.029299 | 0.011686 |
| 240 | −0.019001 | 0.010495 | −0.053099 | −0.00245 | −0.0085 | −0.080265 | −0.058512 | 0.037981 | 0.057584 | −0.014174 | −0.018324 | 0.035006 | −0.054138 | −0.051152 |
| 241 | −0.037086 | −0.033945 | −0.077783 | −0.040181 | 0.0009 | 0.012328 | 0.007664 | 0.001984 | 0.045536 | −0.018955 | −0.029639 | 0.006049 | −0.061008 | 0.001477 |
| 242 | 0.032759 | −0.040003 | 0.016078 | 0.029743 | 0.044154 | 0.061909 | 0.058948 | 0.019729 | −0.013037 | 0.004051 | 0.056639 | −0.063798 | −0.031576 | −0.03452 |
| 243 | 0.008615 | −0.004499 | −0.010188 | 0.024448 | 0.015877 | 0.064012 | 0.03821 | 0.000233 | 0.061073 | −0.05457 | 0.072419 | −0.054377 | −0.031856 | −0.011561 |
| 244 | −0.000962 | −0.017874 | 0.001781 | 0.007072 | 0.027378 | 0.003333 | −0.00776 | −0.030701 | −0.039348 | −0.013949 | −0.013051 | −0.016095 | −0.062077 | 0.037781 |
| 245 | 0.055136 | −0.028561 | 0.001504 | −0.00174 | 0.039992 | −0.008112 | −0.003583 | −0.037567 | −0.02969 | −0.002771 | 0.013837 | −0.023998 | −0.066598 | 0.045225 |
| 246 | 0.010003 | −0.015269 | 0.025107 | 0.018982 | −0.00353 | 0.007428 | 0.007609 | 0.072089 | 0.056303 | 0.0364821 | 0.020443 | −0.033304 | 0.001617 | −0.01209 |
| 247 | −0.002286 | −0.034008 | −0.064797 | 0.07256 | 0.011793 | −0.020293 | −0.013488 | −0.019303 | 0.052172 | 0.072241 | −0.019093 | −0.019988 | −0.003965 | −0.016663 |
| 248 | 0.020035 | −0.004769 | −0.035489 | 0.048742 | −0.01052 | −0.001481 | −0.090087 | −0.05501 | −0.011755 | −0.004787 | 0.007769 | 0.010378 | 0.023522 | 0.008833 |
| 249 | 0.003853 | −0.031345 | −0.015208 | −0.023273 | 0.012838 | 0.012718 | −0.099793 | 0.040563 | 0.021939 | 0.001101 | 0.050162 | −0.034022 | −0.037616 | 0.109387 |
| 250 | −0.024395 | 0.035604 | −0.0417 | 0.001737 | 0.001048 | 0.017288 | −0.000216 | −0.003164 | 0.080747 | 0.025755 | −0.072078 | 0.061135 | 0.003916 | −0.038614 |
| 251 | −0.009591 | −0.046155 | −0.047806 | 0.003074 | −0.020393 | −0.036685 | 0.040184 | −0.012565 | 0.032005 | −0.017759 | −0.044556 | 0.001527 | 0.001818 | −0.071835 |
| 252 | 0.050472 | −0.037702 | 0.039939 | −0.025565 | 0.069428 | 0.070471 | 0.091251 | −0.033988 | −0.054518 | −0.05751 | −0.014744 | −0.029457 | 0.036849 | 0.034307 |
| 253 | −0.029069 | 0.004162 | 0.043465 | −0.028886 | −0.060882 | −0.025211 | 0.151654 | 0.022873 | 0.055553 | −0.034251 | 0.038261 | −0.024553 | 0.022844 | 0.029787 |
| 254 | −0.018588 | −0.056738 | −0.038043 | 0.000669 | −0.000942 | −0.007555 | 0.007398 | −0.073446 | 0.003709 | −0.014071 | 0.016281 | 0.018208 | 0.036491 | −0.004615 |
| 255 | −0.054961 | −0.037981 | 0.00753 | 0.003701 | 0.024719 | −0.036248 | −0.003387 | −0.021483 | 0.001402 | −0.000723 | −0.019296 | −0.032715 | −0.036758 | −0.041651 |
| 256 | −0.001053 | −0.025537 | 0.017456 | −0.047222 | 0.001092 | −0.001529 | −0.044757 | 0.002637 | −0.010062 | 0.00718 | −0.00413 | 0.026847 | −0.056831 | −0.008738 |
| 257 | 0.00482 | −0.016624 | 0.053278 | 0.055886 | −0.015253 | 0.050726 | 0.084585 | 0.015653 | −0.017307 | 0.016914 | −0.05766 | 0.029548 | 0.008055 | 0.048385 |
| 258 | 0.007441 | −0.01186 | −0.084577 | 0.046799 | 0.018258 | −0.004317 | 0.017859 | −0.035858 | 0.012353 | 0.009272 | 0.01978 | 0.031606 | 0.041983 | 0.018265 |
| 259 | 0.000165 | 0.018029 | −0.005481 | 0.02131 | 0.033658 | −0.022183 | 0.022353 | −0.029737 | −0.011496 | 0.055576 | 0.053364 | −0.02148 | −0.020436 | 0.011117 |
| 260 | 0.024973 | 0.008315 | 0.060399 | 0.060331 | −0.008453 | 0.021548 | 0.043482 | −0.043375 | −0.002559 | 0.002323 | −0.022705 | 0.015325 | 0.104399 | 0.103382 |
| 261 | −0.017821 | 0.019716 | −0.006347 | −0.038632 | −0.003499 | −0.059758 | 0.041019 | 0.020022 | −0.038523 | −0.048397 | 0.053187 | 0.009383 | 0.061675 | 0.010016 |
| 262 | 0.027402 | −0.026551 | 0.062766 | −0.007635 | 0.003012 | −0.019908 | 0.014454 | −0.040767 | −0.050139 | 0.013312 | 0.007498 | −0.02713 | −0.045032 | 0.00313 |
| 263 | −0.007408 | 0.000202 | 0.062574 | 0.019315 | 0.026185 | 0.005443 | 0.053272 | −0.039906 | −0.085249 | 0.029636 | 0.009838 | −0.038903 | −0.042824 | 0.021616 |
| 264 | −0.058436 | 0.037274 | 0.018987 | −0.066722 | 0.009045 | −0.036029 | −0.050348 | −0.013874 | 0.008385 | 0.052039 | 0.04496 | 0.027803 | −0.071887 | 0.034171 |
| 265 | 4.010491 | 0.046609 | 4.010836 | −0.06651 | 0.049386 | 0.022022 | −0.033834 | −0.028936 | 0.028894 | −0.046628 | −0.022509 | 0.043096 | 0.003638 | −0.0338 |
| 266 | −0.004367 | 0.031516 | −0.053769 | −0.051603 | 0.026607 | 0.022465 | 0.013567 | 0.042429 | 0.010473 | −0.091385 | −0.076505 | −0.033688 | 0.018585 | −0.092512 |
| 267 | −0.006975 | 0.01743 | −0.020359 | 0.083158 | −0.027967 | −0.048923 | −0.031977 | 0.082283 | 0.078865 | −0.025893 | 0.128481 | 0.023196 | 0.072915 | −0.03769 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 268 | 0.042364 | 0.035594 | 0.013768 | −0.026925 | 0.007223 | 0.031607 | 0.015318 | 0.033037 | −0.041784 | 0.035514 | −0.016685 | −0.003857 | 0.047153 | −0.012788 |
| 269 | 0.035721 | 0.04206 | 0.032765 | −0.030847 | −0.036902 | 0.037523 | −0.011331 | −0.013972 | −0.020176 | 0.007423 | −0.02159 | −0.008743 | 0.002044 | −0.048453 |
| 270 | 0.043598 | 0.015033 | 0.069141 | −0.040342 | 0.007709 | 0.018299 | −0.002753 | 0.004338 | −0.015092 | −0.026297 | −0.025585 | −0.027789 | 0.015017 | −0.041446 |
| 271 | −0.045935 | −0.088483 | 0.008527 | −0.093693 | −0.001604 | 0.052879 | −0.055676 | 0.114878 | −0.006319 | 0.161018 | 0.046591 | −0.10307 | −0.03104 | −0.035189 |
| 272 | −0.046065 | −0.003351 | −0.094725 | −0.002277 | −0.007622 | −0.060269 | −0.011085 | −0.033314 | 0.042118 | −0.017393 | 0.040591 | −0.008285 | 0.03448 | −0.058734 |
| 273 | 0.061813 | 0.02887 | −0.001802 | −0.006084 | 0.01149 | 0.011312 | 0.029149 | −0.027981 | −0.020246 | 0.028304 | −0.026468 | −0.001861 | 0.005669 | −0.006715 |
| 274 | 0.03417 | 0.028619 | 0.009291 | −0.009641 | 0.008827 | 0.008752 | 0.011588 | −0.033099 | 0.005656 | 0.019616 | −0.030268 | −0.007438 | 0.002123 | −0.009836 |
| 275 | −0.082107 | −0.049796 | 0.017654 | −0.012636 | 0.006704 | 0.021329 | −0.017761 | −0.038511 | −0.011476 | −0.036757 | −0.022826 | −0.048469 | −0.05416 | −0.052024 |
| 276 | −0.000999 | −0.022565 | −0.017837 | −0.021032 | 0.026843 | −0.025064 | 0.040027 | −0.050418 | −0.084372 | −0.016729 | 0.009234 | 0.012153 | 0.02427 | −0.053477 |
| 277 | 0.007207 | 0.048012 | −0.014564 | −0.008274 | −0.027904 | −0.047811 | −0.059303 | −0.034947 | −0.002194 | −0.03948 | −0.057781 | 0.024534 | 0.069983 | −0.03653 |
| 278 | −0.025604 | 0.027454 | 0.025945 | 0.017374 | −0.069543 | −0.054352 | −0.065249 | −0.007038 | −0.000182 | −0.021259 | −0.041477 | 0.002036 | 0.040557 | −0.116746 |
| 279 | 0.039103 | 0.024296 | −0.010397 | 0.01767 | −0.031647 | −0.000204 | −0.011313 | 0.020373 | 0.032081 | −0.046356 | −0.02052 | −0.016017 | 0.043569 | −0.058398 |
| 280 | −0.00947 | 0.005932 | −0.031101 | −0.063272 | 0.059855 | 0.006066 | 0.107152 | 0.099079 | 0.058826 | −0.050881 | 0.057313 | −0.008466 | −0.022413 | −0.016574 |
| 281 | 0.03112 | 0.010682 | −0.028307 | 0.016076 | 0.045567 | −0.040657 | 0.00873 | 0.045092 | −0.004536 | −0.021434 | −0.004225 | 0.00608 | 4.002201 | −0.032329 |
| 282 | 0.031992 | −0.008945 | 0.00684 | 0.014867 | 0.050763 | 0.015898 | 0.051455 | 0.016816 | 0.039592 | 0.018602 | −0.022826 | −0.049478 | −0.037399 | −0.10105 |
| 283 | −0.001845 | −0.039375 | −0.05675 | 0.033963 | −0.009947 | −0.069813 | −0.05343 | −0.028606 | 0.015917 | 0.042047 | −0.054511 | −0.06118 | 0.021093 | −0.045707 |
| 284 | −0.004379 | −0.001279 | 0.033774 | 0.025753 | −0.016824 | 0.015543 | 0.037927 | 0.031365 | −0.037882 | 0.022432 | −0.018501 | 0.03283 | 0.013068 | 0.04376 |
| 285 | −0.004031 | −0.037722 | 0.094787 | 8.034615 | −0.0099 | 0.019708 | 0.081011 | 0.014222 | −0.021006 | 0.02667 | −0.038715 | −0.008584 | 0.014987 | 0.04843 |
| 286 | −0.041987 | −0.016157 | −0.082829 | 0.013061 | 0.032728 | 0.016943 | 0.056439 | −0.025421 | 0.007362 | −0.001737 | 0.017668 | 0.036132 | 0.010669 | 0.00779 |
| 287 | −0.039623 | −0.048948 | −0.048537 | 0.0241661 | 0.026071 | 0.025726 | 0.075458 | −0.008718 | 0.002188 | −0.005034 | −0.007298 | −0.017028 | −0.006883 | 0.023539 |
| 288 | −0.014962 | 0.011834 | −0.056079 | −0.010526 | −0.063493 | −0.092492 | −0.041948 | −0.036507 | 0.009901 | 0.036499 | −0.038021 | −0.039358 | 0.114663 | −0.023722 |
| 289 | 0.004149 | −0.031115 | 0.069523 | −0.020958 | −0.007958 | 0.061083 | 0.002727 | 0.005088 | 0.017363 | −0.002641 | −0.059194 | −0.048673 | −0.040599 | −0.081214 |
| 290 | 0.016064 | −0.012495 | −0.001866 | −0.022236 | −0.012987 | 0.006803 | 0.060031 | 0.047383 | −0.002403 | 0.01476 | 0.027924 | −0.016651 | 0.035036 | −0.024993 |
| 291 | 0.013539 | −0.014319 | −0.011712 | −0.02275 | 0.001551 | −0.000553 | 0.06427 | 0.05481 | 0.003307 | 0.021162 | 0.028932 | −0.007742 | 0.027149 | −0.028911 |
| 292 | 0.008938 | −0.011971 | −0.023847 | −0.018974 | −0.024315 | 0.008489 | 0.041156 | 0.024395 | 0.028375 | −0.008505 | 0.003338 | −0.012308 | −0.016057 | −0.008065 |
| 293 | −0.012069 | −0.04625 | −0.101111 | 0.053754 | 0.059811 | −0.025757 | −0.004969 | 0.034704 | −0.005694 | 0.029975 | −0.108384 | 0.150842 | 0.041061 | −0.047241 |
| 294 | 0.027861 | −0.020561 | −0.031011 | −0.054887 | 0.061519 | −0.032455 | −0.074301 | 0.015315 | 0.010477 | −0.021904 | 0.021615 | −0.024684 | −0.041081 | −0.01997 |
| 295 | 0.0627371 | 0.026649 | −0.002284 | 0.0105 | −0.004064 | −0.05452 | −0.018072 | 0.02663 | 0.089834 | −0.007294 | −0.017439 | −0.025725 | −0.019233 | 0.039174 |
| 296 | 0.00808 | 0.054275 | 0.062035 | −0.041762 | −0.034143 | −0.050174 | 0.012473 | −0.009656 | 0.055233 | 0.005818 | 0.016793 | −0.083877 | 0.013551 | 0.055959 |
| 297 | 0.050836 | 0.031913 | 0.015346 | 0.005173 | −0.053094 | −0.053988 | 0.005688 | 0.015477 | 0.044261 | −0.054016 | −0.048538 | −0.020226 | −0.004469 | 0.026527 |
| 298 | 0.016441 | −0.017089 | 0.079619 | 0.024262 | −0.003887 | −0.043017 | 0.016085 | −0.084689 | −0.071818 | 0.043785 | 0.051648 | −0.014905 | −0.049813 | 0.022685 |
| 299 | 0.040551 | −0.008036 | 0.0005281 | 0.001107 | 0.007122 | −0.059488 | 0.016278 | −0.007786 | −0.012907 | −0.074611 | −0.037749 | 0.0192441 | 0.085531 | 0.012224 |
| 300 | 0.03673 | −0.05398 | 0.062334 | −0.032289 | −0.017279 | −0.072599 | −0.080701 | −0.01417 | −0.057021 | −0.084434 | −0.008946 | −0.0008 | −0.182846 | 0.08651 |
| 301 | 0.062953 | −0.05265 | 0.053149 | 0.006138 | −0.033011 | −0.035005 | 0.04906 | 0.029566 | −0.015167 | −0.028322 | −0.014834 | −0.02232 | 0.011033 | 0.019743 |
| 302 | 0.056167 | −0.02437 | 0.057302 | −0.031385 | −0.028805 | −0.028994 | 0.045379 | −0.009065 | 0.015996 | −0.016366 | 0.023674 | −0.055835 | 0.005791 | −0.016222 |
| 303 | 0.007065 | 0.0014 | −0.019287 | 0.010713 | −0.052468 | −0.05308 | 0.014327 | −0.053247 | 0.005954 | −0.050374 | −0.002148 | 0.0015 | −0.008057 | 0.02779 |
| 304 | 0.024702 | −0.016216 | −0.001227 | −0.04842 | −0.042473 | −0.076358 | 0.032763 | −0.076564 | 0.039721 | −0.040811 | 0.001859 | −0.026754 | 0.10094 | 0.021886 |
| 305 | −0.13811 | −0.104831 | 0.0094041 | 0.033789 | 0.072217 | 0.058058 | −0.059869 | 0.05376 | −0.000958 | −0.008573 | −0.120488 | 0.051167 | −0.021533 | 0.043374 |
| 306 | −0.059933 | 0.01368 | −0.042969 | −0.006171 | 0.051904 | 0.025047 | −0.017208 | 0.067347 | −0.041481 | −0.043087 | 0.002536 | 0.102297 | 0.006501 | −0.004463 |
| 307 | −0.067682 | 0.129988 | 0.040543 | −0.061239 | −0.022414 | 0.017159 | −0.074562 | 0.040908 | 0.08112 | 0.022636 | −0.090409 | 0.050914 | −0.005805 | 0.065438 |
| 308 | −0.040827 | −0.011249 | 0.029511 | 0.006332 | 0.000475 | −0.006975 | 0.042366 | 0.031415 | −0.034752 | 0.007677 | −0.025009 | −0.006959 | 0.099449 | 0.049482 |
| 309 | 0.022183 | −0.046679 | −0.008727 | 0.042723 | −0.003754 | 0.006828 | −0.039882 | −0.008455 | 0.011855 | 0.009505 | 0.007985 | 0.004838 | −0.00333 | −0.012793 |
| 310 | −0.032799 | 0.043258 | 0.013223 | 0.041914 | 0.049953 | 0.052447 | −0.053541 | −0.011935 | −0.024679 | 0.021161 | 0.031974 | 0.03114 | −0.03621 | −0.043475 |
| 311 | 0.02949 | 0.0433 | 0.021307 | 0.047707 | 0.005377 | 0.020122 | 0.064857 | −0.023689 | 0.023659 | −0.003886 | −0.043369 | 0.009166 | −0.031886 | −0.024949 |
| 312 | −0.05656 | 0.045949 | 0.048436 | 0.118898 | −0.142862 | 0.18354 | −0.034694 | −0.175635 | −0.045979 | 0.024074 | −0.077356 | −0.12478 | 0.065796 | −0.066519 |
| 313 | −0.009306 | 0.014532 | −0.064968 | 0.055876 | −0.019084 | 0.021978 | 0.052359 | −0.003122 | −0.042111 | −0.046318 | 0.017703 | 0.004905 | −0.057544 | 0.093321 |
| 314 | −0.117158 | 0.039202 | −0.122824 | −0.105102 | 0.065468 | 0.026058 | 0.023531 | −0.018694 | 0.062004 | 0.09322 | 0.003031 | −0.051228 | −0.068582 | 0.100466 |
| 315 | −0.001486 | 0.001468 | −0.008156 | 0.008672 | −0.013406 | 0.030855 | −0.046976 | −0.000672 | 0.035763 | −0.053969 | −0.022664 | 0.03554 | 0.012358 | 0.042798 |
| 316 | −0.141436 | −0.031096 | −0.064938 | 0.061653 | −0.117924 | −0.093639 | 0.071628 | 0.057541 | 0.024192 | −0.018233 | 0.136567 | −0.051891 | −0.076131 | 0.024723 |
| 317 | −0.000378 | −0.021969 | 0.002473 | −0.001579 | −0.013377 | −0.018877 | −0.019506 | −0.02266 | 0.018542 | 0.026384 | −0.018392 | 0.017902 | −0.008825 | −0.045684 |
| 318 | −0.024521 | −0.023789 | 0.004484 | −0.03261 | −0.050936 | −0.061468 | −0.033048 | −0.017992 | −0.03575 | 0.120166 | −0.096776 | −0.03928 | −0.055641 | 0.014014 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 319 | 0.0088 | −0.016933 | −0.000569 | −0.002545 | −0.036326 | 0.004793 | 0.007799 | 0.011735 | 0.022618 | −0.035569 | −0.007451 | 0.061687 | −0.015906 | 0.012894 |
| 320 | 0.00578 | 0.0258181 | −0.002301 | 0.03259 | 0.016388 | 0.050142 | 0.045857 | −0.051248 | 0.024691 | −0.009785 | −0.053301 | 0.024887 | 0.057418 | −0.082025 |
| 321 | 0.079282 | 0.070334 | −0.002112 | −0.097757 | −0.066083 | −0.032926 | 0.049555 | −0.026276 | −0.041996 | −0.001194 | −0.012443 | −0.01499 | −0.01968 | −0.030166 |
| 322 | −0.038147 | −0.092635 | −0.006886 | 0.042236 | 0.078484 | 0.032567 | 0.002633 | −0.137981 | 0.091292 | 0.162376 | 0.030842 | −0.028193 | 0.089246 | −0.108636 |
| 323 | −0.020407 | 0.087949 | −0.018392 | −0.020523 | 0.055331 | 0.071953 | 0.063896 | −0.014212 | 0.043736 | −0.021253 | 0.105694 | −0.005931 | 0.025759 | −0.08177 |
| 324 | 0.102714 | −0.028864 | 0.035647 | −0.046807 | −0.042162 | 0.048999 | 0.010639 | 0.13986 | −0.219012 | 0.06013 | −0.076021 | −0.050872 | 0.008522 | −0.058756 |
| 325 | 0.078015 | −0.010499 | −0.014515 | −0.101895 | −0.025415 | 0.009432 | −0.013687 | −0.003645 | −0.050727 | 0.07237 | 0.076886 | 0.002383 | −0.051267 | −0.023571 |
| 326 | −0.049292 | 0.017699 | −0.076163 | 0.015606 | 0.097871 | 0.016111 | −0.086874 | 0.026101 | −0.070986 | 0.016585 | 0.05799 | −0.024556 | −0.034134 | −0.0733 |
| 327 | −0.003905 | 0.030715 | 0.032537 | 0.051649 | 0.004511 | −0.021175 | 0.01292 | −0.002074 | 0.014119 | 0.028604 | 0.049471 | −0.011476 | 0.053665 | −0.019047 |
| 328 | −0.101057 | 0.049383 | 0.072477 | −0.042057 | 0.009828 | 0.003356 | −0.04275 | 0.083626 | 0.106049 | −0.055611 | −0.05013 | −0.003569 | 0.073482 | 0.057598 |
| 329 | 0.061645 | 0.004671 | −0.042552 | 0.008533 | 0.030455 | 0.026421 | 0.035998 | −0.050047 | −0.002244 | 0.017363 | 0.091135 | −0.030151 | −0.003866 | −0.019479 |
| 330 | −0.017952 | −0.096564 | −0.028711 | −0.078472 | 0.026109 | 0.016579 | 0.064814 | 0.013928 | 0.021596 | −0.004229 | 0.015876 | 0.021052 | −0.048436 | −0.101464 |
| 331 | 0.007604 | 0.043166 | −0.009454 | 0.001241 | 0.058828 | 0.064267 | −0.051249 | −0.009037 | −0.005972 | −0.01781 | 0.044466 | 0.014752 | −0.023454 | −0.045617 |
| 332 | 0.157492 | 0.037513 | −0.004241 | 0.078559 | −0.084149 | 0.037403 | 0.035507 | 0.115558 | 0.084753 | 0.018835 | −0.050259 | −0.109987 | 0.005161 | −0.026916 |
| 333 | 0.115731 | −0.020357 | 0.065838 | −0.073368 | 0.015405 | 0.033333 | −0.036172 | 0.073417 | 0.007203 | 0.001566 | 0.071542 | 0.000155 | −0.053779 | −0.059942 |
| 334 | −0.010002 | −0.143448 | −0.176039 | −0.086943 | −0.045291 | 0.059415 | −0.058164 | 0.046772 | −0.066618 | 0.008679 | 0.13299 | −0.18763 | 0.085801 | 0.152595 |
| 335 | −0.007838 | 0.001194 | 0.003478 | −0.018828 | 0.013164 | 0.029884 | 0.017323 | 0.010634 | 0.019653 | −0.050437 | 0.063353 | 0.013117 | −0.005498 | −0.098779 |
| 336 | −0.015227 | −0.058351 | 0.037479 | −0.011449 | 0.127577 | −0.083268 | −0.091222 | −0.071533 | 0.028811 | 0.080641 | 0.041183 | 0.018378 | 0.020926 | −0.047239 |
| 337 | −0.027163 | −0.053386 | 0.0019 | 0.007532 | −0.024965 | −0.012525 | −0.038209 | 0.026262 | 0.122168 | −0.050079 | −0.030574 | −0.034772 | 0.006612 | 0.023953 |
| 338 | 0.019158 | 0.0518 | −0.099993 | 0.026395 | 0.043812 | 0.145827 | 0.100495 | −0.086106 | 0.02343 | 0.092093 | 0.02557 | −0.011434 | 0.066815 | 0.015924 |
| 339 | 0.059092 | 0.032397 | −0.091781 | −0.059116 | 0.003204 | 0.041927 | 0.051854 | −0.105767 | −0.032471 | 0.021125 | 0.077643 | 0.059554 | 0.077654 | 0.091076 |
| 340 | −0.124769 | −0.050133 | −0.020209 | 0.046547 | 0.122714 | 0.112405 | 0.02255 | 0.029765 | −0.021787 | 0.097315 | −0.19858 | 0.017679 | −0.006174 | 0.118657 |

| | CD | CE | CF | CG | CH | CI | CJ | CK | CL | CM | CN | CO | CP | CQ |
|---|---|---|---|---|---|---|---|---|---|---|---|---|---|---|
| 1 | 0.027663 | 0.006079 | −0.023488 | 0.020872 | 0.009951 | −0.03284 | −0.01799 | 0.106885 | −0.117681 | 0.01783 | −0.021327 | 0.027008 | 0.051079 | −0.000553 |
| 2 | 0.023967 | 0.012491 | 0.024669 | 0.083483 | −0.0383 | −0.052176 | 0.040618 | 0.032497 | 0.036019 | 0.000755 | 0.021864 | 0.021626 | 0.065336 | 0.064784 |
| 3 | 0.006165 | −0.031646 | −0.024125 | −0.00877 | −0.000532 | 0.055604 | 0.00209 | 0.054891 | −0.095484 | 0.017798 | −0.024856 | 0.060114 | 0.070711 | 0.052182 |
| 4 | −0.05162 | 0.014996 | −0.039091 | −0.026612 | −0.013994 | −0.044854 | 0.000868 | −0.01392 | −0.05867 | 0.022858 | −0.096598 | −0.01398 | −0.113873 | −0.052028 |
| 5 | 0.055088 | −0.059539 | −0.016502 | 0.072578 | −0.051106 | −0.014651 | −0.01046 | −0.023111 | −0.066631 | −0.073569 | 0.069974 | −0.018752 | 0.10508 | 0.024373 |
| 6 | 0.046643 | −0.081724 | 0.039695 | 0.089412 | 0.041612 | −0.033642 | 0.078606 | 0.057406 | 0.015547 | 0.084597 | −0.12617 | −0.082773 | −0.033452 | 0.008609 |
| 7 | 0.135544 | 0.017475 | 0.068266 | −0.131018 | −0.061836 | 0.044347 | −0.103827 | 0.084656 | −0.099735 | −0.042655 | −0.0438 | 0.037992 | 0.03694 | 0.012571 |
| 8 | −0.055777 | 0.000212 | −0.101789 | 0.021137 | 0.010263 | −0.045468 | −0.031517 | −0.057495 | 0.059325 | 0.06935 | −0.008492 | 0.038887 | 0.005017 | −0.000741 |
| 9 | 0.015154 | −0.004088 | −0.102278 | −0.014743 | 0.058588 | −0.021373 | 0.002438 | 0.012062 | 0.011213 | 0.01057 | 0.087196 | −0.053761 | 0.056192 | 0.027197 |
| 10 | −0.079906 | 0.02161 | 0.029368 | −0.053556 | 0.013608 | 0.031712 | 0.142645 | −0.035399 | 0.047494 | 0.093969 | −0.053194 | 0.010698 | 0.056882 | 0.0333 |
| 11 | 0.003169 | 0.06855 | 0.02014 | −0.012801 | −0.03932 | 0.02366 | 0.021679 | −0.094087 | 0.081562 | 0.025883 | 0.017662 | −0.140009 | 0.083947 | −0.063542 |
| 12 | 0.001727 | −0.069574 | 0.018415 | 0.010259 | −0.120007 | 0.01406 | 0.008492 | 0.077594 | 0.100467 | −0.04037 | −0.044483 | −0.045016 | −0.02285 | −0.006776 |
| 13 | −0.089887 | −0.018169 | 0.047784 | −0.010104 | −0.064983 | −0.034479 | 0.048918 | −0.022162 | −0.031903 | −0.022559 | 0.122722 | 0.002065 | −0.048526 | −0.035505 |
| 14 | 0.015032 | −0.091329 | −0.045853 | −0.056485 | 0.124631 | 0.032364 | 0.001066 | −0.05345 | −0.07757 | −0.066416 | −0.068635 | −0.002338 | 0.034066 | 0.006289 |
| 15 | −0.067888 | −0.04396 | 0.00085 | −0.019065 | −0.086621 | 0.000384 | 0.033967 | 0.026819 | −0.074384 | 0.017352 | 0.005799 | 0.079635 | −0.004546 | 0.005519 |
| 16 | −0.041372 | −0.004341 | 0.069873 | −0.027045 | 0.025827 | 0.043883 | −0.021134 | −0.001907 | 0.028674 | −0.062324 | 0.06669 | 0.062305 | −0.052068 | −0.016793 |
| 17 | −0.039847 | −0.048019 | 0.090973 | −0.01634 | 0.113492 | 0.164055 | 0.03408 | 0.048175 | −0.070139 | 0.041117 | 0.022986 | 0.066572 | 0.138443 | −0.042664 |
| 18 | 0.032693 | −0.086647 | 0.039746 | 0.052451 | 0.070314 | 0.024679 | −0.082023 | 0.038964 | −0.030092 | 0.106412 | −0.045647 | −0.107745 | −0.072798 | 0.060906 |
| 19 | −0.048252 | −0.001126 | 0.012965 | 0.086572 | 0.008673 | −0.093581 | 0.008814 | 0.017688 | 0.002002 | 0.042922 | 0.038259 | 0.081362 | −0.001154 | −0.104271 |
| 20 | 0.015772 | −0.079084 | 0.001106 | 0.03293 | −0.01625 | −0.0042 | −0.000333 | 0.018707 | 0.032551 | −0.010652 | −0.023974 | 0.021482 | 0.013524 | −0.038016 |
| 21 | −0.118476 | 0.032144 | 0.175164 | 0.039219 | 0.067316 | −0.017551 | −0.033295 | −0.101425 | 0.041522 | 0.01126 | −0.02108 | −0.000082 | −0.04521 | −0.011529 |
| 22 | −0.018068 | −0.091884 | −0.1762451 | −0.035923 | −0.005563 | 0.080667 | −0.130495 | −0.083742 | 0.082847 | −0.02035 | −0.019735 | 0.0182071 | 0.1019061 | −0.052835 |
| 23 | 0.132381 | −0.117963 | 0.061288 | −0.156282 | 0.02813 | −0.0289 | 0.050068 | −0.036622 | −0.061194 | 0.037091 | 0.053794 | −0.120914 | −0.101031 | 0.038838 |
| 24 | −0.102352 | −0.188418 | −0.089674 | −0.013498 | 0.115323 | 0.006035 | −0.092053 | 0.06017 | −0.118967 | −0.109098 | −0.096525 | −0.049925 | −0.001013 | −0.11732 |
| 25 | −0.014094 | −0.098744 | 0.063023 | 0.000387 | 0.000586 | 0.070684 | −0.039118 | −0.029014 | 0.129411 | 0.069156 | 0.123381 | 0.030961 | 0.028106 | −0.059876 |
| 26 | 0.018948 | −0.052905 | 0.023827 | 0.026879 | −0.006588 | 0.010829 | 0.071946 | −0.032913 | 0.016774 | −0.033042 | 0.056993 | 0.019555 | −0.031704 | −0.049827 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 27 | 0.001884 | 0.000094 | 0.057227 | 0.021149 | 0.00563 | 0.012781 | −0.000657 | 0.022495 | 0.012209 | −0.035703 | 0.001091 | −0.01081 | −0.007813 | −0.001126 |
| 28 | −0.075474 | 0.032496 | −0.018365 | −0.076955 | −0.005106 | 0.00352 | −0.052133 | 0.109688 | −0.119665 | 0.027734 | 0.016953 | 0.016569 | 0.117957 | 0.055075 |
| 29 | 0.085454 | 0.16679 | 0.060138 | −0.049476 | −0.017406 | 0.05764 | 0.00715 | −0.110208 | −0.049855 | −0.021924 | 0.07692 | 0.028722 | −0.038327 | 0.000158 |
| 30 | −0.018027 | −0.029395 | 0.000384 | 0.02437 | 0.028188 | −0.032214 | 0.012659 | −0.027086 | 0.028177 | −0.020655 | 0.084639 | −0.019475 | −0.026818 | −0.018778 |
| 31 | −0.070413 | −0.026332 | −0.058501 | 0.023372 | 0.076212 | −0.053991 | −0.036143 | 0.075147 | −0.012303 | −0.032458 | 0.074475 | −0.002014 | −0.003071 | 0.087422 |
| 32 | 0.013766 | 0.071058 | −0.149584 | 0.104125 | −0.089511 | −0.127407 | −0.054278 | 0.026916 | 0.00861 | 0.108693 | 0.154994 | 0.055705 | 0.027598 | 0.092621 |
| 33 | 0.075155 | −0.0457091 | −0.033049 | 0.086655 | −0.050542 | 0.104471 | 0.088716 | 0.063828 | −0.077777 | 0.038281 | −0.032468 | 0.007704 | −0.010667 | 0.029955 |
| 34 | −0.009636 | −0.054844 | −0.006558 | −0.056994 | −0.134184 | −0.068827 | 0.053642 | −0.121133 | 0.049468 | −0.078517 | −0.006424 | 0.044016 | −0.084778 | −0.033522 |
| 35 | 0.101817 | −0.047379 | −0.076583 | 0.048627 | −0.041972 | 0.002786 | −0.012945 | 0.046946 | 0.014831 | 0.110881 | −0.013625 | 0.071831 | 0.002738 | −0.018966 |
| 36 | 0.048334 | 0.01186 | −0.065213 | 0.000914 | 0.12003 | −0.019615 | 0.122887 | −0.016988 | −0.038552 | 0.06727 | 0.015722 | 0.057575 | −0.012112 | −0.04992 |
| 37 | 0.040587 | 0.0089 | 0.09184 | 0.069499 | 0.16269 | 0.019106 | −0.010969 | −0.013101 | 0.004581 | −0.011662 | −0.017743 | −0.043505 | 0.030898 | 0.140782 |
| 38 | −0.012456 | −0.044727 | 0.03384 | −0.056044 | −0.023054 | −0.017053 | −0.053653 | 0.029583 | −0.033314 | 0.052952 | 0.023049 | −0.049656 | 0.11063 | 0.005851 |
| 39 | −0.103943 | 0.060543 | −0.052723 | e.147245 | −0.013328 | 0.06211 | 0.013965 | −0.12725 | 0.009113 | 0.053349 | 0.026696 | 0.010901 | −0.037399 | 0.013937 |
| 40 | 0.019071 | 0.009167 | 0.003886 | 0.023195 | −0.004539 | 0.018278 | −0.003151 | −0.005098 | −0.018445 | 0.037561 | −0.018554 | −0.016205 | −0.055535 | 0.044172 |
| 41 | 0.00014 | 0.0799 | −0.041466 | 0.027706 | 0.026668 | 0.002556 | −0.056194 | 0.0408 | 0.015064 | 0.031588 | −0.013489 | −0.013866 | −0.081656 | −0.002035 |
| 42 | −0.02135 | −0.0151551 | −0.002491 | 0.011389 | −0.028675 | −0.029944 | −0.035043 | −0.036842 | 0.0299731 | 0.061239 | 0.004149 | −0.026394. | −0.059749 | 0.013253 |
| 43 | 0.028238 | 0.021227 | 0.0265441 | 0.010383 | 0.00327 | 0.039428 | 0.013344 | −0.007516 | −0.05863 | −0.001571 | 0.005686 | −0.026883 | −0.053556 | 0.033278 |
| 44 | −0.002342 | 0.046079 | −0.072909 | −0.007696 | −0.029187 | −0.004174 | 0.017952 | 0.006758 | 0.016613 | −0.026509 | 0.001868 | 0.02107 | 0.041011 | −0.00647 |
| 45 | −0.030198 | 0.024615 | −0.057959 | 0.020363 | 0.047436 | 0.026189 | 0.000543 | 0.007141 | −0.026968 | −0.091344 | 0.009823 | −0.071645 | −0.008419 | −0.013315 |
| 46 | −0.124648 | 0.062306 | 0.033202 | −0.162653 | 0.070712 | −0.200083 | 0.047839 | 0.058812 | 0.091848 | 0.01718 | −0.034929 | 0.052157 | −0.0386 | −0.097256 |
| 47 | −0.083988 | 0.021503 | 0.048344 | 0.020297 | 0.079138 | 0.022506 | 0.04776 | 0.025446 | 0.061377 | −0.07026 | −0.024934 | 0.066886 | 0.054724 | −0.012448 |
| 48 | 0.118564 | 0.08269 | −0.071426 | −0.008184 | 0.087761 | 0.033396 | 0.01546 | −0.000884 | 0.037421 | −0.069521 | −0.061419 | −0.036447 | −0.012952 | −0.031795 |
| 49 | −0.029541 | −0.024772 | 0.011177 | −0.045716 | 0.010346 | −0.02791 | 0.030788 | −0.006611 | 0.043491 | −0.053167 | 0.077113 | −0.019788 | −0.02822 | −0.018138 |
| 50 | −0.032195 | −0.01908 | 0.007449 | −0.061746 | 0.084045 | −0.050664 | 0.011144 | −0.07149 | −0.037259 | −0.074079 | 0.013196 | 0.00119 | 0.039606 | −0.055924 |
| 51 | 0.049248 | −0.024314 | 0.007873 | 0.040435 | −0.099276 | −0.058367 | −0.11281 | −0.019507 | 0.019124 | 0.007693 | −0.025556 | −0.069978 | 0.0613661 | 0.054516 |
| 52 | 0.061815 | 0.008119 | −0.005348 | 0.071474 | −0.074037 | 0.052258 | 0.033628 | 0.088866 | 0.114962 | −0.064307 | −0.094397 | 0.09583 | −0.078709 | −0.062177 |
| 53 | 0.044033 | −0.026898 | −0.041963 | −0.022248 | 0.018763 | −0.04782 | −0.00475 | −0.017257 | −0.013821 | −0.02173 | 0.027162 | −0.005732 | 0.026887 | −0.027775 |
| 54 | 0.045744 | −0.02489 | −0.022224 | −0.030189 | 0.044097 | 0.026628 | 0.099256 | −0.03435 | −0.017208 | 0.031818 | 0.025994 | 0.010071 | 0.006628 | −0.046691 |
| 55 | −0.082162 | −0.030701 | −0.007161 | 0.021009 | −0.081219 | −0.000925 | −0.07637 | −0.00227 | −0.048332 | 0.038808 | −0.042323 | 0.033706 | 0.009671 | −0.008163 |
| 56 | −0.0103 | −0.045584 | −0.010084 | 0.024368 | 0.001808 | −0.035024 | −0.031381 | −0.080146 | 0.002926 | −0.021733 | 0.068767 | −0.024545 | 0.0186271 | −0.031601 |
| 57 | 0.001513 | −0.041066 | −0.0041691 | 0.048479 | −0.008995 | 0.023839 | −0.028287 | 0.042641 | −0.067322 | −0.009254 | 0.057681 | 0.062286 | −0.091224 | 0.030769 |
| 58 | 0.011801 | 0.037657 | −0.001634 | −0.041936 | −0.000586 | −0.002724 | 0.049885 | −0.094294 | −0.024267 | −0.010451 | 0.008758 | −0.003611 | 0.076343 | 0.089306 |
| 59 | 0.0432991 | 0.109182 | 0.0185471 | −0.169097 | 0.043266 | 0.004659 | 0.001861 | 0.059311 | 0.031159 | 0.04144 | −0.025208 | 0.003085 | 0.109395 | −0.015371 |
| 60 | 0.0022181 | 0.006446 | −0.0411931 | 0.006496 | −0.021036 | 0.014834 | −0.010477 | 0.026701 | 0.136018 | 0.020077 | −0.02731 | −0.029523 | 0.054589 | −0.017842 |
| 61 | 0.123138 | −0.036144 | −0.026601 | −0.011124 | −0.077262 | 0.086559 | −0.080684 | 0.060317 | −0.012457 | 0.016223 | −0.022949 | 0.056321 | 0.069928 | −0.034716 |
| 62 | −0.055617 | 0.048825 | 0.002699 | −0.030817 | 0.067308 | 0.0381 | 0.104825 | −0.081324 | 0.058837 | −0.062843 | 0.00031 | 0.019905 | −0.02794 | 0.038446 |
| 63 | −0.03505 | −0.078663 | 0.076134 | −0.039477 | 0.013824 | 0.010635 | −0.008569 | 0.022187 | 0.011171 | 0.026327 | 0.061328 | −0.004662 | 0.038888 | −0.007322 |
| 64 | −0.050691 | −0.116871 | 0.072674 | 0.058713 | 0.008822 | 0.0423 | 0.002773 | −0.071735 | −0.003189 | 0.036307 | 0.073904 | −0.00216 | 0.012737 | 0.016002 |
| 65 | −0.02917 | −0.03546 | −0.109844 | 0.028113 | −0.018387 | 0.053763 | −0.008111 | 0.01238 | −0.023912 | −0.005775 | 0.020491 | 0.040075 | −0.123875 | 0.074375 |
| 66 | 0.15844 | −0.007135 | 0.028072 | 0.022125 | −0.06286 | −0.066624 | 0.04241 | −0.005111 | 0.070003 | −0.027698 | −0.070694 | 0.05062 | 0.017421 | 0.069506 |
| 67 | 0.047345 | −0.0128 | −0.000404 | 0.038042 | 0.011496 | −0.055764 | −0.020475 | −0.008544 | −0.019216 | −0.037587 | 0.002642 | −0.079112 | 0.04951 | −0.03071 |
| 68 | −0.013297 | −0.066695 | 0.008157 | 0.014981 | 0.029562 | 0.003441 | −0.123688 | −0.025827 | −0.035318 | −0.093444 | 0.082683 | −0.025413 | −0.087342 | 0.050859 |
| 69 | 0.019161 | −0.02573 | −0.049922 | 0.007854 | −0.068901 | −0.033622 | 0.017808 | −0.094752 | −0.10042 | −0.022114 | −0.076238 | 0.081334 | 0.058474 | 0.009954 |
| 70 | 0.019599 | 0.125282 | 0.014573 | 0.005626 | −0.073592 | −0.016156 | 0.069183 | 0.019242 | −0.009287 | −0.020345 | −0.082175 | 0.010826 | 0.025315 | −0.039142 |
| 71 | −0.065363 | −0.018959 | −0.04907 | −0.030083 | 0.042788 | 0.035566 | −0.11131 | 0.034551 | 0.06108 | −0.08162 | −0.05948 | −0.016033 | −0.052518 | 0.041806 |
| 72 | 0.029944 | 0.020839 | 0.058579 | 0.01408 | 0.031721 | 0.034408 | −0.012886 | −0.099648 | 0.012181 | −0.015912 | 0.010697 | 0.054777 | 0.008532 | −0.052271 |
| 73 | 0.05166 | 0.007929 | −0.130126 | 0.007042 | −0.0566 | 0.024491 | 0.069904 | −0.027425 | 0.012841 | −0.178202 | 0.012773 | −0.067024 | −0.043967 | −0.045643 |
| 74 | −0.145073 | 0.1088851 | −0.0321731 | −0.021154 | −0.125186 | −0.014874 | 0.003142 | −0.146481 | −0.065964 | −0.042037 | 0.049429 | −0.094003 | 0.032518 | −0.137743 |
| 75 | −0.011628 | 0.0313451 | −0.0116371 | 0.010786 | −0.014018 | −0.01055 | −0.011733 | 0.006168 | 0.01558 | −0.027999 | 0.044576 | −0.071432 | −0.015811 | 0.00932 |
| 76 | 0.09183 | −0.078637 | 0.053733 | −0.155109 | −0.050375 | −0.080733 | −0.040328 | 0.017586 | 0.078018 | 0.009937 | 0.053245 | 0.026765 | 0.1502031 | 0.056264 |
| 77 | −0.013892 | 0.023673 | −0.031695 | 0.021487 | 0.01051 | 0.0062 | −0.01474 | 0.038696 | 0.05893 | 0.013339 | 0.006239 | −0.043228 | −0.047919 | 0.023824 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 78 | 0.006136 | 0.038495 | −0.00921 | 0.013169 | 0.004024 | −0.025403 | −0.02077 | 0.021312 | 0.04839 | 0.039558 | 0.050867 | −0.107486 | −0.032759 | −0.013323 |
| 79 | −0.023174 | −0.006661 | −0.05019 | 0.105125 | 0.008772 | −0.01763 | 0.044861 | 0.000719 | −0.013985 | 0.061964 | −0.088516 | 0.097375 | −0.089542 | −0.046503 |
| 80 | −0.02453 | −0.0334 | −0.036576 | −0.098543 | −0.143265 | 0.094137 | −0.012231 | 0.03674 | −0.006791 | −0.091153 | −0.014228 | 0.028542 | 0.041644 | 0.027303 |
| 81 | 0.008265 | 0.038841 | 0.136311 | −0.005032 | 0.16637 | 0.10979 | 0.018983 | 0.005398 | −0.081206 | 0.042604 | 0.045802 | −0.048028 | −0.01482 | 0.14289 |
| 82 | 0.074938 | 0.000096 | 0.002779 | −0.057081 | 0.047355 | 0.048182 | −0.068327 | −0.08406 | 0.054151 | −0.023556 | 0.024401 | −0.022894 | −0.058117 | 0.018029 |
| 83 | −0.0187551 | 0.0299991 | 0.07061 | −0.065165 | −0.02132 | 0.061338 | −0.029142 | 0.009177 | A.0369551 | −0.023775 | 0.0097951 | −0.007336 | −0.065012 | −0.021905 |
| 84 | −0.0434091 | 0.0613521 | −0.031831 | −0.052961 | −0.002117 | 0.008612 | −0.078467 | −0.024972 | 0.0091 | 0.0387691 | 0.0175391 | −0.045286 | 0.0147691 | 0.034927 |
| 85 | −0.03828 | −0.048332 | −0.050406 | −0.114362 | −0.093258 | −0.035887 | −0.080448 | −0.049198 | −0.040129 | −0.024915 | −0.052956 | −0.063398 | −0.005917 | 0.034913 |
| 86 | 0.041026 | −0.027199 | −0.045884 | −0.040592 | 0.059577 | 0.004806 | −0.003038 | −0.065607 | 0.031551 | 0.066396 | 0.018597 | 0.049071 | −0.032193 | −0.015389 |
| 87 | 0.118997 | 0.001043 | −0.027521 | 0.047044 | 0.001796 | −0.003471 | 0.133738 | −0.002258 | −0.072981 | 0.050829 | 0.073401 | −0.0628 | 0.09285 | −0.01381 |
| 88 | 0.031882 | 0.029662 | 0.018535 | 0.034202 | 0.006125 | −0.057125 | −0.036034 | 0.045738 | −0.015132 | −0.016241 | −0.074309 | −0.047168 | 0.034234 | −0.02575 |
| 89 | −0.037941 | −0.025978 | 0.017851 | 0.013915 | −0.014659 | 0.019481 | −0.034123 | 0.03012 | 0.027459 | −0.035352 | −0.017422 | 0.004455 | −0.038549 | −0.043089 |
| 90 | −0.056389 | −0.0452731 | −0.0062951 | −0.047391 | −0.031859 | 0.059878 | 0.010877 | −0.065463 | −0.006365 | 0.044537 | −0.113481 | 0.014443 | 0.068261 | −0.018869 |
| 91 | −0.09919 | 0.009674 | −0.022358 | 0.114407 | 0.004447 | 0.029446 | 0.017654 | −0.016555 | 0.085312 | −0.069456 | 0.021018 | 0.037859 | −0.022989 | 0.118508 |
| 92 | 0.088947 | 0.068166 | 0.082506 | −0.021719 | 0.112554 | 0.005337 | −0.016246 | 0.06494 | 0.070386 | −0.003678 | 0.06076 | −0.02757 | 0.034514 | −0.094619 |
| 93 | −0.076571 | 0.091954 | 0.097055 | −0.095178 | −0.078297 | −0.151742 | 0.08473 | −0.000356 | 0.085704 | 0.088561 | −0.10153 | 0.078288 | 0.017874 | 0.009242 |
| 94 | −0.012491 | 0.0880431 | −0.0395731 | 0.016589 | −0.020554 | −0.146078 | 0.115918 | 0.097381 | −0.072906 | 0.024128 | 0.0118261 | −0.07169 | −0.030275 | −0.074594 |
| 95 | 0.062568 | 0.069404 | −0.061041 | 0.03684 | 0.071183 | 0.048897 | −0.08714 | 0.026093 | 0.061945 | −0.002722 | −0.066889 | −0.004692 | −0.004259 | 0.044772 |
| 96 | 0.046294 | −0.031576 | −0.006912 | −0.068492 | 0.001309 | −0.045318 | −0.056955 | 0.04866 | −0.056651 | −0.030694 | 0.120525 | 0.010282 | −0.033375 | −0.057397 |
| 97 | −0.037055 | 0.048453 | 0.085178 | −0.022141 | −0.119816 | 0.044887 | 0.024315 | 0.002232 | 0.011604 | −0.007126 | −0.034042 | 0.058797 | −0.040429 | −0.033607 |
| 98 | −0.0214351 | 0.00861 | −0.010095 | 0.009816 | 0.06768 | 0.039189 | −0.017773 | 0.016159 | −0.023675 | −0.05739 | 0.00458 | 0.05766 | −0.010741 | −0.010978 |
| 99 | 0.026821 | 0.037171 | 0.114719 | −0.073925 | −0.087204 | 0.055489 | 0.09108 | 0.065517 | −0.008423 | −0.060005 | 0.0455541 | −0.008428 | 0.1139231 | −0.016622 |
| 100 | 0.0312031 | 0.037751 | −0.0443951 | 0.011627 | 0.083909 | 0.038709 | −0.008334 | 0.027354 | 0.045955 | −0.028934 | −0.046278 | 0.071199 | −0.033293 | −0.015994 |
| 101 | −0.043685 | 0.025843 | −0.038536 | 0.023901 | 0.026182 | −0.002776 | −0.033755 | −0.022961 | −0.008567 | −0.00382 | 0.0232 | −0.005587 | −0.00963 | −0.011746 |
| 102 | −0.051311 | 0.009782 | 0.070561 | 0.03616 | −0.056271 | −0.016278 | 0.028983 | 0.0691 | −0.044609 | −0.059305 | 0.028292 | −0.10098 | 0.122605 | −0.062153 |
| 103 | −0.07056 | 0.035505 | 0.057912 | 0.071641 | −0.150107 | 0.057828 | 0.0097 | −0.011694 | 0.048845 | 0.046106 | 0.120078 | −0.079524 | −0.012375 | 0.080769 |
| 104 | −0.031186 | −0.124161 | −0.0721041 | −0.000938 | −0.036048 | 0.012338 | 0.003437 | −0.02074 | −0.050475 | 0.0438431 | −0.032016 | 0.0630911 | −0.041384 | 0.031581 |
| 105 | 0.012588 | −0.028858 | 0.0674641 | −0.031711 | 0.068704 | −0.099448 | 0.049292 | −0.118728 | −0.056134 | −0.080532 | 0.024637 | 0.054428 | 0.113671 | 0.021237 |
| 106 | −0.010914 | 0.102921 | 0.132996 | 0.095906 | 0.035048 | 0.027205 | −0.02665 | 0.051258 | −0.063724 | −0.069011 | 0.057102 | 0.083203 | −0.03392 | −0.049046 |
| 107 | 0.106531 | −0.026818 | 0.007586 | −0.03033 | 0.001132 | −0.032854 | −0.092331 | 0.081055 | 0.006522 | 0.013209 | −0.064282 | −0.08656 | −0.059688 | −0.06748 |
| 108 | −0.036359 | 0.007319 | 0.033105 | 0.005936 | 0.024352 | −0.002367 | −0.063953 | −0.072564 | 0.139965 | 0.068389 | −0.066279 | −0.000381 | −0.027719 | 0.012477 |
| 109 | 0.088954 | 0.026203 | −0.03248 | 0.026656 | 0.01429 | 0.043063 | 0.113093 | 0.050114 | 0.103412 | −0.037064 | −0.041291 | −0.039098 | −0.016002 | −0.02645 |
| 110 | −0.022354 | 0.106811 | −0.026154 | −0.112393 | 0.091138 | 0.135277 | −0.118729 | −0.043163 | −0.040802 | 0.070275 | 0.002835 | −0.026704 | −0.033031 | 0.126575 |
| 111 | 0.06938 | −0.043071 | 0.07003 | 0.077412 | 0.006663 | 0.048774 | 0.011063 | 0.024695 | −0.010615 | 0.07379 | 0.144035 | 0.096134 | −0.016143 | −0.093608 |
| 112 | −0.109797 | 0.118998 | −0.041166 | −0.02592 | 0.032741 | −0.0955 | −0.02138 | 0.072564 | −0.034906 | 0.000097 | −0.090953 | 0.070878 | −0.015555 | −0.053994 |
| 113 | 0.040841 | 0.037255 | −0.143441 | −0.035924 | 0.061639 | 0.071256 | −0.011843 | −0.038333 | 0.141248 | 0.041812 | 0.018685 | −0.080983 | 0.065661 | −0.001027 |
| 114 | −0.0592631 | −0.048952 | 0.0632251 | −0.04219 | −0.122565 | 0.104583 | 0.175133 | 0.011123 | 0.0577561 | −0.000492 | −0.072591 | 0.0347891 | −0.098922 | −0.002988 |
| 115 | −0.0041171 | 0.0876251 | −0.0263891 | 0.154859 | 0.044013 | 0.031197 | −0.05957 | 0.000937 | 0.058191 | −0.038853 | −0.036397 | 0.019213 | 0.078145 | 0.042359 |
| 116 | 0.033843 | −0.028682 | 0.029219 | 0.133905 | −0.125606 | 0.137154 | 0.043338 | 0.040114 | −0.039537 | −0.005695 | 0.006066 | 0.123886 | 0.161739 | −0.102088 |
| 117 | 0.00768 | 0.000595 | 0.018796 | 0.029355 | 0.009102 | −0.001033 | 0.013913 | 0.017157 | 0.018904 | −0.008176 | −0.001718 | 0.014754 | 0.094905 | 0.054594 |
| 118 | −0.129342 | −0.066305 | −0.087407 | −0.027609 | 0.014407 | 0.082686 | 0.188433 | −0.046639 | 0.045649 | 0.00159 | −0.14144 | −0.003736 | −0.014061 | 0.050043 |
| 119 | −0.015631 | −0.087316 | −0.023071 | 0.04565 | −0.030145 | −0.127396 | −0.021092 | 0.00215 | 0.02264 | 0.014954 | −0.036126 | 0.049924 | −0.07916 | 0.07891 |
| 120 | −0.00152 | 0.027988 | 0.021522 | 0.067619 | 0.014701 | −0.027802 | 0.032618 | 0.029092 | 0.043431 | 0.008797 | −0.121619 | 0.028473 | 0.022377 | 0.013144 |
| 121 | 0.007967 | −0.017849 | 0.071104 | 0.057231 | −0.080698 | −0.018043 | 0.032949 | 0.064765 | −0.062752 | 0.010006 | −0.006872 | 0.019355 | −0.073348 | −0.010135 |
| 122 | −0.096152 | 0.044709 | −0.000085 | −0.061048 | −0.005051 | −0.008892 | 0.057041 | 0.170354 | −0.023696 | −0.01052 | 0.034322 | −0.025502 | −0.033849 | 0.00853 |
| 123 | 0.063169 | 0.000741 | 0.0600681 | −0.063223 | −0.030909 | −0.01632 | −0.081398 | −0.022836 | 0.01336 | −0.031657 | −0.011086 | −0.041827 | −0.067099 | 0.042946 |
| 124 | −0.0103951 | 0.020940 | −0.023493 | −0.00665 | 0.025124 | −0.017191 | −0.028158 | 0.010878 | −0.018390 | 0.009089 | 0.004616 | −0.020789 | −0.064437 | −0.012655 |
| 125 | 0.027825 | 0.064821 | 0.033115 | −0.023279 | −0.019809 | −0.035418 | 0.019619 | 0.048417 | 0.069918 | −0.040022 | 0.030185 | −0.031437 | 0.145535 | −0.0465 |
| 126 | 0.03469 | 0.041823 | −0.00637 | −0.046084 | −0.097076 | −0.00091 | −0.026365 | 0.017878 | −0.021899 | 0.063866 | 0.043665 | −0.008511 | −0.056623 | −0.026055 |
| 127 | 0.007449 | 0.048438 | 0.046418 | −0.017568 | −0.040716 | 0.043909 | 0.012541 | 0.026664 | 0.013697 | 0.035387 | −0.022773 | −0.084343 | −0.067691 | −0.011211 |
| 128 | 0.028701 | −0.062699 | 0.010767 | 0.09659 | 0.061658 | −0.018899 | 0.019798 | 0.025265 | 0.028605 | −0.037164 | −0.011413 | −0.04905 | 0.026961 | 0.089857 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 129 | 0.005024 | −0.071276 | 0.014898 | 0.140931 | −0.016242 | 0.076264 | 0.105259 | 0.137823 | −0.0436 | 0.013512 | −0.010424 | −0.036959 | 0.007154 | 0.063475 |
| 130 | −0.040584 | 0.035744 | 0.034121 | −0.024608 | 0.075945 | 0.048378 | −0.060965 | −0.024384 | −0.017589 | 0.043283 | 0.075946 | 0.111841 | −0.127835 | −0.099967 |
| 131 | −0.074015 | −0.070594 | 0.054138 | 0.012336 | 0.09539 | −0.070229 | −0.005698 | 0.021189 | −0.016619 | −0.078325 | 0.013254 | −0.014065 | 0.006368 | 0.0357 |
| 132 | 0.037056 | −0.027461 | 0.095643 | 0.011743 | −0.111571 | −0.059946 | −0.024161 | −0.066069 | −0.100004 | 0.033477 | −0.135052 | −0.080433 | −0.029444 | 0.008219 |
| 133 | −0.018044 | −0.027878 | 0.066749 | 0.133981 | −0.072596 | −0.039623 | 0.048455 | −0.099622 | 0.011276 | 0.011621 | 0.120073 | −0.032642 | −0.026733 | −0.067292 |
| 134 | 0.039916 | −0.004294 | −0.072285 | 0.030195 | 0.078784 | 0.023107 | 0.116374 | −0.096768 | −0.009574 | 0.164051 | 0.043657 | 0.030144 | −0.060039 | −0.104371 |
| 135 | 0.076678 | 0.012442 | −0.045436 | 0.019102 | 0.064773 | −0.04999 | −0.000256 | −0.042081 | −0.013834 | −0.014002 | −0.013898 | 0.042105 | 0.049845 | 0.032066 |
| 136 | 0.076841 | 0.079414 | 0.029986 | 0.135351 | 0.027044 | 0.028804 | −0.027362 | 0.010071 | −0.08233 | −0.050776 | 0.098902 | 0.062183 | 0.003952 | −0.034643 |
| 137 | −0.052333 | −0.060463 | 0.081212 | −0.048121 | −0.006924 | −0.043042 | 0.002812 | 0.056558 | 0.014918 | 0.057787 | 0.146986 | −0.101296 | 0.053038 | 0.011896 |
| 138 | −0.044082 | −0.023856 | 0.007422 | 0.011073 | 0.022716 | −0.057521 | 0.07426 | 0.030624 | −0.134244 | −0.037349 | 0.003303 | 0.010028 | −0.030899 | 0.058296 |
| 139 | 0.020369 | 0.02933 | −0.064657 | −0.126276 | −0.049086 | −0.112187 | 0.071275 | 0.095637 | 0.083735 | 0.136555 | 0.000828 | 0.041684 | −0.140496 | 0.111992 |
| 140 | −0.029851 | −0.029955 | −0.037359 | 0.011184 | 0.002425 | 0.084371 | 0.036222 | 0.010772 | 0.0243 | −0.099137 | 0.031968 | −0.046749 | 0.024822 | −0.045966 |
| 141 | 0.060428 | 0.005871 | −0.029211 | −0.05044 | −0.024814 | 0.012572 | −0.114802 | 0.080949 | −0.0404 | −0.111144 | 0.028508 | 0.121014 | 0.035464 | −0.045462 |
| 142 | 0.025529 | −0.000592 | 0.124172 | 0.06867 | −0.054881 | 0.073245 | −0.037742 | −0.069575 | −0.019487 | 0.042786 | −0.0562 | 0.079389 | −0.073168 | −0.009198 |
| 143 | −0.01766 | −0.010288 | −0.018852 | 0.076301 | 0.036481 | −0.050746 | 0.050936 | 0.046818 | −0.039066 | −0.016795 | 0.053466 | −0.143044 | −0.034016 | −0.106436 |
| 144 | 0.06003 | 0.057503 | −0.006002 | 0.048162 | 0.010075 | −0.025409 | −0.041437 | −0.068943 | 0.006897 | 0.075198 | −0.101587 | −0.02542 | 0.069929 | −0.007249 |
| 145 | 0.021765 | 0.02814 | −0.077273 | −0.050553 | −0.12236 | −0.063481 | −0.009994 | −0.117877 | −0.019642 | −0.029202 | 0.096524 | 0.033496 | −0.01104 | −0.044411 |
| 146 | 0.071652 | 0.001188 | −0.001366 | −0.058432 | 0.02439 | −0.04516 | −0.029798 | −0.02831 | 0.008913 | −0.009401 | −0.039376 | 0.041791 | 0.075703 | 0.08116 |
| 147 | −0.002625 | 0.066631 | −0.031318 | −0.005889 | 0.04676 | −0.002869 | −0.066286 | 0.015252 | 0.082771 | 0.016441 | −0.097376 | 0.111132 | −0.025269 | −0.042094 |
| 148 | 0.049278 | 0.088925 | 0.007399 | 0.046204 | 0.022183 | 0.008552 | −0.050091 | 0.028171 | 0.004668 | 0.032622 | −0.073529 | −0.098913 | 0.023333 | −0.058294 |
| 149 | −0.033914 | 0.171056 | −0.058733 | 0.044765 | 0.023751 | 0.046029 | 0.060042 | −0.011663 | −0.100233 | −0.004512 | −0.010476 | 0.019609 | 0.021357 | 0.071369 |
| 150 | −0.086142 | 0.065488 | −0.040135 | 0.065553 | −0.05129 | −0.096591 | −0.010743 | 0.051297 | −0.094143 | −0.019678 | −0.11285 | 0.018458 | −0.011557 | −0.117152 |
| 151 | 0.017822 | −0.001599 | −0.044269 | −0.059128 | −0.022283 | −0.073785 | −0.077012 | 0.096394 | −0.144821 | 0.007426 | 0.015064 | 0.080294 | −0.055917 | 0.053394 |
| 152 | −0.052043 | −0.037439 | −0.043807 | 0.017523 | −0.00745 | 0.103611 | 0.031736 | 0.092681 | 0.058477 | 0.023577 | 0.092055 | −0.110763 | −0.137195 | 0.012559 |
| 153 | −0.032043 | −0.05413 | 0.043531 | −0.141841 | −0.002485 | 0.061101 | 0.002053 | −0.057628 | −0.025914 | −0.078353 | −0.075099 | −0.076919 | −0.021302 | 0.101547 |
| 154 | 0.032145 | 0.077875 | 0.002425 | 0.054575 | 0.03689 | −0.013999 | −0.073348 | −0.084629 | −0.064845 | 0.044087 | −0.047133 | 0.008292 | 0.020416 | −0.101763 |
| 155 | 0.014468 | −0.062 | 0.051718 | 0.082778 | −0.03854 | 0.098963 | 0.061033 | −0.085792 | −0.008675 | −0.027841 | −0.043573 | 0.005718 | −0.010009 | −0.024766 |
| 156 | −0.028507 | −0.001477 | 0.023065 | 0.072238 | 0.097228 | −0.070417 | −0.027655 | −0.073154 | 0.04906 | −0.104671 | 0.027859 | 0.0772 | 0.010173 | 0.150928 |
| 157 | 0.11542 | −0.10015 | −0.081768 | −0.008898 | −0.06067 | 0.04137 | −0.020856 | 0.081082 | 0.0694 | 0.040343 | 0.101289 | 0.11897 | 0.026345 | 0.094501 |
| 158 | −0.051561 | 0.02195 | 0.024048 | 0.002418 | 0.014497 | −0.018692 | −0.025454 | 0.113865 | 0.036477 | −0.020749 | −0.011388 | −0.052473 | −0.019395 | −0.028645 |
| 159 | 0.138943 | 0.09171 | 0.063277 | −0.026776 | −0.106439 | 0.097196 | −0.103467 | −0.021798 | −0.0292 | −0.024574 | −0.03398 | 0.00345 | −0.041531 | 0.000039 |
| 160 | −0.120891 | 0.019096 | −0.018774 | 0.083318 | −0.003179 | 0.074466 | −0.063948 | −0.050606 | 0.037661 | −0.066612 | −0.057445 | −0.039033 | −0.025242 | −0.047494 |
| 161 | 0.021962 | −0.075004 | 0.032441 | −0.073793 | −0.002233 | −0.014328 | 0.015866 | −0.032687 | −0.079403 | −0.051838 | −0.004969 | −0.014356 | −0.033048 | 0.035049 |
| 162 | 0.001968 | −0.086137 | −0.059879 | 4.007781 | 0.074184 | −0.069255 | 0.063022 | −0.024881 | 0.160943 | 0.07355 | 0.005426 | 0.051369 | 0.039805 | 0.065391 |
| 163 | 0.002256 | 0.049861 | 0.044034 | 0.042265 | 0.005944 | 0.06794 | 0.028832 | 0.011714 | 0.029012 | 0.073729 | 0.134976 | 0.133108 | −0.118371 | −0.081177 |
| 164 | 0.089947 | 0.045171 | −0.015007 | −0.025487 | 0.010063 | −0.032549 | 0.006324 | 0.123576 | 0.033875 | 0.043226 | −0.007312 | −0.04808 | 0.02589 | −0.031473 |
| 165 | −0.053746 | −0.014834 | 0.002324 | −0.131339 | −0.033884 | 0.145621 | 0.029928 | −0.104698 | 0.028474 | 0.015272 | −0.077303 | −0.073755 | 0.008489 | −0.140575 |
| 166 | 0.022623 | 0.012168 | −0.032649 | 0.031087 | −0.014849 | −0.053942 | −0.022714 | 0.058575 | −0.00842 | 0.016747 | −0.002514 | 0.00095 | 0.044857 | 0.114829 |
| 167 | −0.12112 | 0.028592 | −0.117526 | −0.084748 | −0.032432 | 0.032258 | 0.083893 | 0.074442 | −0.10047 | −0.040738 | −0.025502 | 0.069132 | 0.012691 | 0.075637 |
| 168 | 0.065157 | 0.053959 | −0.082635 | −0.029601 | −0.041745 | −0.030162 | 0.016026 | 0.083495 | 0.017564 | 0.190813 | 0.121403 | 0.013161 | 0.005647 | 0.018675 |
| 169 | 0.054238 | 0.015871 | 0.027289 | −0.009998 | −0.014043 | 0.055284 | −0.006712 | 0.044659 | 0.019226 | 0.074673 | −0.023418 | −0.006512 | 0.013032 | 0.030172 |
| 170 | 0.056359 | 0.042859 | 0.0779 | 0.001636 | −0.025891 | 0.023329 | −0.002303 | 0.017164 | −0.011699 | 0.055472 | −0.014034 | −0.116069 | 0.033253 | 0.011715 |
| 171 | 0.062831 | −0.0065911 | 0.022111 | −0.04713 | −0.055504 | 0.063163 | 0.019719 | 0.022814 | 0.05218 | 0.023539 | −0.047861 | 0.028904 | −0.039603 | 0.032541 |
| 172 | 0.0017751 | 0.02725 | 0.046133 | 0.026957 | −0.045834 | 0.05887 | −0.009795 | −0.003049 | 0.022782 | −0.008335 | −0.052064 | 0.095445 | 0.065155 | 0.022349 |
| 173 | −0.014401 | 0.016965 | 0.049756 | 0.0192 | 0.012765 | −0.009358 | 0.060242 | −0.009952 | 0.107065 | −0.093617 | 0.045207 | 0.061906 | 0.097176 | 0.047037 |
| 174 | −0.006824 | −0.050562 | −0.058255 | 0.072807 | −0.018581 | 0.057608 | −0.062872 | −0.070042 | −0.082484 | −0.042347 | 0.018007 | 0.003668 | −0.000647 | −0.019274 |
| 175 | 0.018852 | −0.069826 | −0.166058 | 0.061834 | −0.006301 | 0.048989 | −0.062075 | −0.095105 | 0.028718 | 0.001871 | −0.001136 | −0.016538 | −0.014695 | 0.070146 |
| 176 | −0.045965 | 0.029421 | 0.102701 | −0.096584 | −0.056054 | 0.074854 | −0.111548 | 0.085689 | −0.048982 | −0.029449 | −0.011765 | −0.033448 | −0.09649 | −0.07524 |
| 177 | −0.095561 | 0.037499 | −0.071774 | 0.016345 | 0.11117 | −0.101936 | 0.09121 | 0.059426 | 0.006171 | 0.089809 | −0.024258 | −0.169661 | 0.116522 | −0.070535 |
| 178 | 0.023827 | −0.009109 | −0.052706 | −0.001154 | 0.006667 | −0.01065 | 0.006966 | 0.022634 | −0.000097 | −0.005914 | −0.051743 | 0.017094 | −0.086455 | −0.013583 |
| 179 | 0.007503 | −0.074777 | −0.007885 | 0.034913 | 0.010378 | 0.052746 | −0.025779 | 0.021144 | −0.00300f | 0.048857 | −0.04589 | −0.008643 | −0.017739 | 0.015051 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 180 | −0.03391 | −0.003984 | 0.021204 | 0.003115 | 0.002272 | −0.016124 | 0.015966 | 0.02723 | 0.027381 | −0.019282 | 0.017743 | 0.004011 | −0.012538 | 0.008648 |
| 181 | −0.0738831 | −0.006408 | 0.015385 | 0.008887 | 0.002502 | −0.029125 | 0.001146 | 0.008237 | −0.028113 | −0.009353 | 0.001443 | −0.004851 | 0.010369 | 0.032011 |
| 182 | −0.0521651 | 0.069266 | 0.005475 | 0.060646 | −0.021787 | −0.019331 | −0.003005 | −0.033128 | 0.012014 | 0.074421 | −0.040626 | −0.070095 | 0.004544 | −0.007342 |
| 183 | 0.066898 | −0.036573 | −0.044607 | 0.020396 | 0.033845 | 0.066943 | 0.010287 | 0.026251 | 0.061698 | 0.039177 | −0.053678 | −0.037038 | −0.000769 | −0.002962 |
| 184 | 0.004378 | −0.01458 | −0.031799 | −0.00311 | −0.05572 | 0.086154 | 0.029479 | 0.017035 | 0.125226 | −0.040048 | −0.060326 | 0.005567 | −0.040631 | 0.034672 |
| 185 | −0.117652 | 0.065561 | 0.031069 | 0.034392 | −0.099625 | −0.005557 | 0.005554 | 0.020743 | −0.038587 | 0.028255 | 0.089085 | 0.022845 | 0.046727 | 0.146119 |
| 186 | 0.062586 | 0.113227 | −0.031783 | −0.022783 | −0.024105 | −0.055468 | 0.00689 | −0.000328 | 0.06475 | −0.077531 | 0.071046 | −0.026823 | −0.03852 | −0.014214 |
| 187 | −0.027192 | 0.042332 | 0.01898 | −0.023424 | 0.051118 | −0.037435 | 0.052583 | 0.063873 | 0.060403 | −0.022515 | 0.038 | 0.031741 | 0.06511 | −0.064398 |
| 188 | −0.055833 | 0.022481 | 0.036001 | −0.002548 | 0.016092 | 0.009401 | 0.001943 | 0.012602 | −0.017018 | −0.054554 | −0.031394 | 0.048025 | 0.013438 | −0.055345 |
| 189 | −0.048276 | −0.060173 | 0.049534 | −0.148558 | 0.078314 | 0.026352 | −0.069333 | −0.037291 | −0.062929 | 0.018034 | 0.010125 | 0.08176 | −0.063668 | −0.055973 |
| 190 | 0.02972 | −0.050137 | −0.027882 | 0.01794 | −0.02491 | −0.016104 | 0.024219 | 0.02179 | 0.053041 | −0.035854 | 0.104298 | −0.024694 | −0.041451 | −0.083102 |
| 191 | 0.023213 | −0.092574 | −0.053637 | 0.066526 | −0.024127 | −0.067032 | 0.025292 | 0.002633 | −0.036614 | −0.042763 | 0.06988 | 0.015463 | 0.095516 | 0.03 |
| 192 | 0.002245 | 0.008175 | −0.12981 | 0.012743 | 0.015717 | 0.022414 | −0.071724 | −0.143928 | −0.148038 | 0.092664 | −0.059122 | −0.04449 | 0.061373 | 0.020499 |
| 193 | 0.101341 | 0.001768 | 0.064753 | 0.081138 | 0.047705 | −0.00663 | 0.016747 | −0.088049 | 0.099109 | 0.024695 | −0.076638 | −0.106217 | 0.068911 | −0.013189 |
| 194 | 0.021766 | −0.035091 | 0.036072 | −0.055349 | 0.073602 | −0.026378 | −0.070892 | 0.081798 | −0.007773 | −0.053687 | −0.039422 | −0.025172 | −0.093411 | −0.001663 |
| 195 | 0.011012 | −0.022245 | 0.02327 | 0.013687 | 0.026368 | 0.017491 | 0.000583 | 0.026935 | −0.059052 | 0.032408 | 0.127044 | −0.011586 | 0.101952 | −0.006645 |
| 196 | 0.024523 | 0.065549 | −0.017327 | 0.090881 | −0.048903 | −0.009409 | 0.035074 | 0.000525 | −0.026044 | 0.016731 | −0.023789 | 0.064196 | 0.024541 | −0.064802 |
| 197 | 0.008211 | −0.032363 | −0.077231 | 0.021081 | −0.025974 | −0.011687 | −0.034846 | −0.060352 | −0.019316 | −0.015034 | −0.029053 | −0.053953 | 0.027526 | −0.00561 |
| 198 | −0.063998 | −0.011543 | −0.003759 | −0.129356 | 0.04774 | 0.05333 | 0.053415 | −0.13509 | 0.043156 | −0.026719 | 0.084539 | 0.068374 | −0.015968 | 0.003534 |
| 199 | 0.008777 | 0.097298 | 0.025826 | −0.062929 | 0.021407 | 0.06477 | −0.075732 | −0.013878 | 0.067374 | 0.033406 | 0.006587 | 0.05761 | 0.058066 | −0.013707 |
| 200 | 0.080457 | −0.107881 | −0.037491 | −0.00552 | 0.180006 | −0.02239 | 0.043753 | −0.052852 | −0.095838 | 0.040523 | −0.093482 | 0.047805 | 0.010441 | −0.030251 |
| 201 | −0.041072 | −0.030863 | 0.069706 | −0.022171 | −0.000185 | −0.068275 | 0.012053 | 0.12738 | 0.019075 | 0.0229491 | 0.01416 | 0.014541 | −0.055165 | −0.013453 |
| 202 | 0.088742 | −0.007398 | −0.049311 | 0.051072 | 0.053583 | −0.077251 | 0.002987 | −0.084912 | −0.022346 | −0.051735 | 0.061096 | 0.018321 | −0.02646 | 0.045646 |
| 203 | 0.063991 | −0.046471 | −0.019554 | −0.026428 | 0.06524 | 0.057959 | 0.135666 | 0.057054 | −0.019596 | 0.075568 | −0.055597 | 0.060658 | −0.087779 | −0.013156 |
| 204 | −0.058286 | 0.014111 | 0.023294 | 0.01149 | 0.016165 | 0.024056 | −0.079301 | 0.042913 | 0.007179 | −0.039862 | −0.012698 | −0.125355 | 0.002838 | −0.051095 |
| 205 | −0.037157 | −0.007267 | 0.118754 | 0.06671 | 0.028899 | 0.000613 | −0.015097 | −0.014175 | 0.01742 | 0.001615 | −0.009044 | −0.009988 | 0.07278 | −0.08001 |
| 206 | 0.073957 | 0.119603 | −0.138113 | −0.045486 | −0.010186 | 0.044149 | 0.010015 | −0.025501 | −0.041802 | −0.114474 | −0.001202 | −0.036057 | 0.05553 | −0.041058 |
| 207 | −0.011607 | 0.043936 | 0.108635 | −0.071682 | −0.097346 | −0.030129 | −0.029204 | −0.070629 | 0.100152 | −0.055264 | 0.032687 | 0.032701 | 0.002816 | −0.053323 |
| 208 | −0.014929 | −0.108949 | −0.026436 | −0.031327 | 0.014946 | 0.028216 | 0.036192 | 0.025543 | 0.119032 | −0.062102 | −0.01294 | 0.034564 | 0.080771 | −0.005156 |
| 209 | 0.044933 | 0.05188 | 0.048603 | −0.044347 | −0.053441 | 0.065372 | 0.113328 | −0.12052 | −0.01071 | −0.05852 | −0.001292 | 0.034656 | 0.011695 | 0.130818 |
| 210 | −0.049904 | −0.026794 | 0.00130 | −0.015099 | −0.000834 | −0.125903 | 0.02441 | −0.035415 | 0.098617 | 0.002083 | −0.031702 | −0.034123 | −0.077031 | −0.006806 |
| 211 | −0.056938 | −0.103361 | 0.008771 | 0.055762 | 0.002125 | −0.118235 | −0.038006 | −0.011262 | 0.093841 | 0.04911 | −0.085939 | 0.072231 | 0.07563 | 0.042038 |
| 212 | −0.033183 | 0.031805 | −0.108504 | 0.140985 | −0.032283 | 0.024311 | −0.047024 | −0.012364 | 0.056971 | 0.031191 | 0.087879 | 0.022859 | 0.008741 | 0.039315 |
| 213 | 0.012435 | 0.03422 | 0.026049 | 0.007491 | −0.075652 | −0.03275 | −0.07117 | −0.1486 | 0.062469 | 0.036348 | −0.013526 | 0.11834 | 0.011603 | 0.056651 |
| 214 | 0.02127 | −0.036584 | 0.021652 | 0.004526 | 0.026739 | 0.055477 | −0.067336 | 0.013147 | −0.015121 | −0.013807 | −0.055832 | 0.008265 | −0.029355 | −0.006543 |
| 215 | −0.000451 | −0.068806 | 0.028307 | 0.067122 | 0.063549 | −0.138335 | −0.03025 | −0.020622 | 0.040902 | −0.054758 | −0.028381 | 0.10353 | 0.054601 | −0.215722 |
| 216 | 0.01728 | 0.112618 | −0.104824 | −0.046699 | −0.001648 | −0.059081 | 0.000983 | 0.059641 | 0.019111 | 0.066545 | 0.106185 | 0.038919 | −0.075331 | 0.061967 |
| 217 | 0.032845 | 0.040093 | −0.027353 | −0.007558 | 0.040838 | −0.08829 | −0.037536 | 0.049841 | −0.056222 | −0.029628 | −0.052784 | 0.026517 | −0.015369 | −0.073002 |
| 218 | 0.006271 | 0.011224 | 0.051719 | 0.020561 | 0.014391 | −0.074129 | 0.007048 | −0.061987 | 0.022318 | −0.049727 | −0.000964 | −0.049442 | 0.001809 | 0.01421 |
| 219 | 0.041228 | 0.020089 | 0.002039 | −0.033904 | −0.018409 | −0.034787 | 0.024995 | −0.027898 | −0.048355 | −0.075526 | 0.00668 | −0.010354 | −0.010686 | 0.047452 |
| 220 | −0.045567 | 0.02625 | 0.024933 | −0.045028 | 0.017566 | −0.023879 | −0.006247 | 0.016825 | 0.026111 | 0.01693 | −0.035071 | −0.041068 | 0.069058 | −0.071552 |
| 221 | −0.031141 | 0.007267 | −0.027352 | 0.007438 | 0.014677 | 0.011643 | 0.028293 | 0.012501 | −0.02218 | −0.036096 | 0.009459 | 0.000969 | −0.029917 | 0.023424 |
| 222 | −0.042514 | 0.033489 | −0.076435 | 0.020114 | 0.00348 | 0.007617 | 0.085115 | −0.015848 | −0.027266 | −0.045891 | 0.005892 | 0.064192 | −0.008526 | −0.032636 |
| 223 | −0.046588 | 0.099827 | 0.014975 | −0.011619 | 0.020224 | 0.067893 | 0.040103 | 0.002054 | 0.01784 | −0.043154 | −0.02161 | −0.018702 | −0.033021 | −0.030068 |
| 224 | −0.054198 | −0.002965 | 0.011248 | 0.023231 | −0.046253 | −0.03094 | −0.109578 | −0.097181 | −0.058253 | 0.008946 | −0.043842 | 0.016704 | 0.066383 | −0.048963 |
| 225 | −0.050113 | −0.00608 | −0.013374 | 0.053565 | −0.030875 | 0.036128 | −0.031514 | −0.100018 | −0.059793 | 0.031982 | 0.053347 | 0.021698 | 0.079364 | −0.0101 |
| 226 | −0.046279 | 0.002258 | 0.000884 | 0.012138 | 0.025425 | −0.033832 | 0.036885 | −0.022763 | −0.013695 | 0.006508 | 0.020953 | 0.022411 | −0.027539 | −0.03558 |
| 227 | 0.028308 | −0.069601 | −0.053834 | −0.076371 | −0.053087 | 0.026211 | −0.003449 | −0.026672 | 0.051937 | 0.099332 | −0.055007 | −0.066215 | 0.034486 | −0.020267 |
| 228 | 0.033818 | −0.053634 | 0.052726 | 0.077294 | −0.077608 | −0.048575 | −0.022237 | 0.018323 | −0.07572 | 0.114888 | −0.05816 | −0.084084 | −0.099371 | 0.010067 |
| 229 | 0.01236 | 0.062357 | 0.025281 | 0.042901 | 0.028094 | −0.043654 | −0.02204 | 0.001366 | −0.030541 | 0.04556 | 0.00113 | 0.001943 | 0.029895 | 0.066194 |
| 230 | 0.005998 | 0.032565 | 0.06374 | 0.061394 | 0.0438 | −0.034725 | 0.000597 | 0.016887 | 0.021779 | 0.017726 | 0.028762 | −0.036221 | 0.021579 | −0.003985 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 231 | −0.103844 | 0.141847 | 0.004663 | −0.001081 | 0.027808 | 0.115981 | −0.022962 | 0.063806 | 0.071994 | 0.095012 | 0.03423 | 0.078936 | 0.072725 | 0.079457 |
| 232 | −0.015957 | −0.034311 | 0.049127 | −0.021304 | −0.0226 | 0.056962 | −0.000979 | 0.088099 | 0.017159 | −0.05084 | −0.019683 | −0.009237 | 0.075873 | −0.013631 |
| 233 | 0.037153 | −0.008618 | −0.060539 | −0.117814 | 0.027003 | 0.013104 | −0.008791 | −0.018495 | −0.059237 | 0.104093 | 0.081856 | 0.018106 | 0.039907 | 0.070409 |
| 234 | −0.010713 | 0.031587 | 0.050159 | 0.020051 | −0.017113 | −0.009563 | 0.006003 | −0.047967 | −0.064285 | 0.104857 | −0.053554 | 0.052946 | −0.089193 | −0.038969 |
| 235 | 0.002647 | −0.051023 | −0.002634 | −0.014991 | −0.052254 | 0.029133 | −0.031617 | 0.061914 | −0.013715 | 0.045212 | −0.019662 | 0.108642 | 0.124088 | −0.043278 |
| 236 | 0.021581 | 0.021013 | 0.040145 | −0.005618 | 0.009217 | 0.089256 | −0.01501 | 0.019652 | 0.03299 | 0.001874 | 0.023764 | −0.1174 | −0.014684 | −0.018184 |
| 237 | −0.026258 | 0.000165 | −0.072675 | −0.057897 | 0.078954 | 0.066354 | 0.054284 | −0.053156 | −0.018166 | −0.025774 | −0.027929 | 0.032606 | −0.022954 | 0.014033 |
| 238 | −0.019757 | −0.037615 | −0.057307 | −0.014208 | −0.021624 | −0.011553 | 0.000665 | −0.049099 | −0.027714 | 0.00142 | −0.000313 | −0.066657 | 0.008784 | −0.011004 |
| 239 | 0.046271 | −0.011492 | −0.026556 | 0.004209 | −0.065657 | −0.020665 | −0.027617 | 0.019274 | −0.010747 | 0.047274 | 0.058699 | −0.010904 | −0.000019 | −0.006607 |
| 240 | 0.090223 | −0.005437 | −0.004361 | 0.036276 | 0.01073 | 0.004137 | −0.081155 | −0.010863 | 0.001866 | −0.014294 | 0.022522 | 0.059623 | −0.04551 | −0.000554 |
| 241 | 0.06598 | −0.004558 | −0.027174 | −0.005335 | 0.05453 | −0.007883 | 0.0204 | −0.045841 | −0.057129 | 0.144283 | 0.110815 | −0.02532 | −0.055454 | −0.069812 |
| 242 | −0.0188 | −0.011974 | −0.047475 | −0.049484 | −0.030536 | −0.052237 | 0.014932 | −0.037714 | 0.075169 | 0.023218 | 0.096529 | −0.013353 | 0.036714 | −0.02331 |
| 243 | 0.027091 | −0.089457 | −0.038506 | −0.032942 | −0.036636 | −0.048124 | 0.015485 | 0.018301 | 0.046381 | −0.151141 | 0.033855 | −0.013978 | −0.042671 | 0.015512 |
| 244 | −0.01125 | −0.058006 | 0.015022 | −0.0001 | −0.024897 | 0.030717 | 0.008674 | 0.051853 | 0.004304 | 0.01505 | 0.030386 | −0.026622 | 0.017606 | 0.018219 |
| 245 | −0.007347 | −0.016724 | 0.085736 | 0.003692 | −0.005439 | 0.012731 | −0.0339 | 0.003903 | −0.023373 | 0.074147 | −0.081008 | −0.013271 | 0.08089 | 0.025966 |
| 246 | 0.037664 | 0.010636 | 0.003196 | 0.000547 | −0.015694 | −0.015824 | −0.053928 | 0.013673 | −0.006134 | 0.063737 | 0.003645 | 0.005261 | 0.026806 | 0.009383 |
| 247 | −0.007489 | 0.042111 | −0.012245 | 0.021667 | −0.041985 | 0.058929 | 0.0115 | 0.062757 | −0.012243 | −0.00989 | −0.005218 | −0.007346 | −0.076528 | −0.050848 |
| 248 | −0.041316 | −0.030536 | −0.001464 | 0.031907 | 0.010987 | 0.069923 | 0.036547 | 0.040911 | −0.01483 | −0.048095 | −0.036896 | 0.005878 | −0.034984 | −0.022062 |
| 249 | 0.048615 | −0.005951 | 0.0813 | 0.078932 | 0.069068 | 0.007025 | −0.029699 | −0.036091 | −0.032069 | −0.058393 | 0.035538 | −0.049258 | −0.059604 | 0.056042 |
| 250 | 0.061413 | 0.037437 | −0.014612 | 0.014362 | 0.040739 | −0.028921 | −0.048815 | 0.001188 | 0.065785 | −0.038797 | −0.020706 | 0.017123 | −0.009145 | −0.003702 |
| 251 | 0.044645 | 0.010006 | −0.066987 | −0.002023 | 0.016894 | 0.038028 | 0.007777 | −0.010693 | 0.012339 | −0.066335 | 0.001857 | 0.005244 | 0.023998 | −0.053265 |
| 252 | −0.021837 | −0.024947 | −0.039468 | 0.045562 | −0.034315 | 0.016309 | −0.005261 | 0.007255 | 0.06916 | −0.014386 | 0.052103 | −0.052846 | 0.007721 | 0.047455 |
| 253 | −0.002024 | −0.003213 | 0.01785 | 0.047063 | 0.040991 | 0.022787 | −0.008857 | 0.059823 | 0.027294 | 0.03268 | −0.085104 | 0.003485 | 0.024571 | 0.042468 |
| 254 | 0.0092161 | 0.0188381 | 0.0184671 | −0.039971 | −0.06751 | 0.042839 | 0.010681 | −0.056686 | −0.003837 | 0.053497 | 0.056676 | −0.053542 | 0.024572 | 0.052778 |
| 255 | −0.012691 | −0.021335 | −0.043505 | −0.026467 | −0.056909 | −0.008175 | −0.021855 | −0.000203 | 0.019717 | 0.046562 | 0.015868 | −0.019163 | −0.001799 | 0.032327 |
| 256 | −0.030042 | 0.006482 | 0.046824 | 0.045529 | 0.052184 | −0.063867 | −0.001643 | −0.01453 | 0.058721 | 0.01813 | −0.119224 | −0.056485 | −0.001302 | −0.018504 |
| 257 | −0.033307 | 0.013272 | −0.043276 | −0.009684 | −0.014754 | 0.027474 | −0.056963 | 0.044423 | 0.019381 | −0.000237 | −0.020602 | 0.009375 | 0.016393 | 0.004197 |
| 258 | 0.020282 | 0.052094 | −0.000346 | −0.015782 | −0.032399 | 0.013799 | −0.024735 | −0.003146 | −0.031942 | 0.06628 | 0.031559 | 0.036917 | −0.041432 | −0.055698 |
| 259 | 0.002905 | 0.012789 | 0.021736 | 0.000721 | 0.00725 | 0.004141 | 0.018966 | −0.06041 | −0.056647 | −0.097212 | −0.008391 | −0.016606 | −0.026147 | 0.010827 |
| 260 | −0.04829 | 0.034521 | 0.122452 | −0.019731 | 0.064269 | 0.029704 | 0.091197 | 0.031181 | 0.046397 | −0.044347 | 0.045039 | 0.065934 | 0.027065 | 0.067299 |
| 261 | 0.042015 | 0.109032 | 0.036045 | −0.004409 | 0.027168 | 0.021739 | 0.031449 | −0.022941 | −0.020609 | 0.02654 | −0.052336 | 0.016355 | 0.00881 | 0.005768 |
| 262 | 0.01133 | 0.067569 | −0.051409 | −0.004345 | 0.078121 | 0.03609 | −0.011303 | 0.000172 | 0.017059 | 0.062647 | −0.013307 | −0.000721 | −0.048849 | 0.008956 |
| 263 | −0.006961 | −0.001614 | −0.044005 | −0.015324 | 0.072863 | 0.007657 | 0.026473 | 0.009358 | 0.0051771 | −0.003857 | −0.020447 | 0.0204611 | −0.037099 | 0.065296 |
| 264 | −0.0054871 | −0.0402431 | −0.0327451 | −0.066889 | −0.017291 | −0.022051 | 0.01563 | 0.006259 | 0.018587 | −0.029821 | 0.013453 | 0.133595 | 0.008251 | −0.032272 |
| 265 | 0.021494 | −0.012642 | 0.014578 | −0.05518 | −0.045501 | −0.018448 | −0.007809 | 0.059588 | 0.007886 | 0.083717 | 0.026011 | 0.033839 | 0.019967 | −0.062118 |
| 266 | −0.040661 | 0.072994 | 0.058953 | −0.030171 | −0.025634 | 0.006589 | 0.058619 | 0.022101 | 0.022339 | 0.094708 | −0.09998 | −0.001203 | 0.010208 | 0.029918 |
| 267 | −0.028497 | 0.021571 | 0.020477 | 0.013303 | 0.054297 | −0.034732 | −0.057996 | 0.018935 | 0.123594 | −0.003233 | 0.046552 | 0.101237 | −0.03682 | −0.026426 |
| 268 | −0.000894 | −0.027929 | 0.007799 | 0.006532 | −0.012022 | −0.017932 | 0.054152 | 0.024221 | 0.009189 | −0.006894 | 0.053248 | 0.061591 | −0.038042 | −0.044339 |
| 269 | −0.07107 | −0.027721 | 0.025061 | 0.040296 | 0.046165 | −0.01063 | 0.064069 | −0.009994 | 0.02383 | −0.022441 | 0.048999 | 0.004445 | −0.008802 | −0.01643 |
| 270 | −0.011556 | −0.018183 | −0.013223 | −0.016828 | 0.03323 | −0.002151 | 0.039989 | −0.026081 | 0.024088 | 0.005958 | −0.005479 | −0.017809 | −0.008557 | 0.024367 |
| 271 | −0.040674 | −0.043537 | −0.12832 | 0.006777 | −0.052817 | 0.082436 | 0.089573 | 0.017856 | 0.056737 | 0.035939 | −0.008075 | −0.03616 | 0.064561 | −0.047365 |
| 272 | −0.007869 | 0.00759 | −0.001361 | 0.016884 | 0.00371 | 0.011858 | −0.059143 | −0.055302 | −0.014265 | −0.014053 | −0.033768 | 0.014155 | 0.010696 | −0.073482 |
| 273 | 0.041801 | −0.004248 | 0.012971 | 0.043658 | 0.010182 | 0.017731 | −0.032621 | 0.006324 | −0.061417 | −0.040037 | 0.016348 | 0.019496 | −0.02038 | −0.032677 |
| 274 | 0.023104 | 0.010757 | 0.01848 | 0.0506 | 0.015169 | 0.014351 | −0.020337 | 0.014655 | −0.071923 | −0.028325 | 0.020243 | 0.009156 | −0.007582 | −0.032236 |
| 275 | 0.066085 | −0.062188 | 0.033458 | 0.009542 | −0.015483 | 0.027241 | −0.021708 | 0.016326 | 0.077051 | −0.06313 | −0.046008 | −0.0447 | −0.020644 | −0.028541 |
| 276 | −0.00356 | 0.06486 | 0.012411 | 0.022492 | −0.046084 | 0.056888 | −0.033613 | 0.014372 | −0.018224 | −0.009104 | −0.02005 | −0.080776 | −0.03952 | 0.012912 |
| 277 | −0.014672 | −0.0106 | 0.004455 | 0.044253 | −0.007856 | 0.014597 | 0.009398 | 0.049239 | −0.00075 | 0.007644 | −0.008274 | 0.037479 | 0.006416 | 0.015101 |
| 278 | −0.027019 | −0.013581 | 0.042065 | 0.033069 | −0.000628 | 0.01989 | −0.042273 | −0.006239 | 0.012641 | 0.052755 | −0.070425 | 0.026822 | 0.022357 | 0.079754 |
| 279 | 0.0622721 | −0.060405 | 0.025818 | −0.005845 | −0.028702 | −0.058671 | 0.013553 | −0.045703 | −0.010491 | −0.009813 | −0.025182 | −0.007303 | 0.010572 | 0.029102 |
| 280 | 0.118701 | −0.036285 | 0.001584 | −0.03008 | 0.004875 | −0.05144 | 0.036945 | −0.013455 | −0.022124 | −0.064677 | −0.024213 | 0.047938 | −0.042599 | −0.028243 |
| 281 | 0.07935 | 0.061427 | 0.061908 | 0.010575 | 0.039149 | −0.050467 | −0.070266 | −0.020139 | −0.023976 | −0.033582 | 0.030102 | 0.076996 | 0.037079 | −0.003661 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 282 | 0.056672 | 0.033228 | 0.014476 | 0.053823 | 0.001571 | −0.016861 | −0.042108 | −0.011003 | 0.019775 | −0.037659 | 0.059134 | −0.035599 | 0.000865 | 0.045138 |
| 283 | 0.058966 | 0.040838 | 0.049457 | −0.01355 | 0.02908 | 0.042036 | 0.054807 | 0.031446 | 0.012313 | −0.109465 | −0.041123 | 0.013458 | −0.110404 | 0.039892 |
| 284 | 0.012146 | −0.010633 | −0.01105 | −0.014384 | −0.00985 | −0.006722 | −0.036378 | 0.00809 | 0.043277 | −0.025475 | −0.026705 | 0.018753 | 0.037043 | 0.008916 |
| 285 | −0.015433 | 0.010502 | −0.01769 | 0.035785 | −0.028795 | −0.004396 | −0.041307 | 0.063596 | 0.019994 | −0.076764 | −0.009566 | −0.016504 | 0.021973 | −0.023055 |
| 286 | 0.014725 | 0.067858 | −0.013929 | −0.022973 | 0.00217 | −0.040582 | 0.032605 | −0.100037 | −0.005284 | 0.021406 | 0.0061 | 0.014241 | 0.020094 | 0.032758 |
| 287 | 0.034297 | 0.068054 | 0.023309 | −0.020187 | −0.012513 | −0.057211 | 0.036361 | −0.059348 | 0.023376 | −0.01037 | −0.008127 | −0.009311 | −0.036827 | 0.062243 |
| 288 | 0.049533 | −0.008204 | 0.001851 | −0.067419 | 0.041552 | −0.022601 | 0.039998 | −0.049662 | 0.011302 | −0.012722 | 0.01291 | 0.079382 | −0.061068 | −0.012401 |
| 289 | 0.039106 | 0.023243 | −0.01856 | −0.039202 | 0.045654 | 0.030321 | 0.027426 | 0.020658 | 0.001843 | 0.029357 | 0.028748 | −0.021291 | −0.010916 | −0.015176 |
| 290 | 0.063837 | 0.01765 | 0.012441 | 0.006492 | −0.052628 | 0.041295 | 0.016585 | 0.012947 | 0.04696 | −0.024459 | −0.029794 | −0.011773 | 0.008314 | 0.019654 |
| 291 | 0.065546 | 0.01207 | 0.00025 | 0.007413 | −0.046043 | 0.030745 | 0.008275 | 0.010345 | 0.053539 | −0.010931 | −0.025187 | −0.011243 | 0.00546 | 0.036504 |
| 292 | 0.054291 | 0.004593 | −0.009742 | 0.015529 | −0.051647 | 0.000822 | 0.016356 | 0.010402 | 0.016053 | −0.028116 | −0.01958 | −0.018192 | 0.02562 | −0.001074 |
| 293 | 0.108797 | −0.030575 | 0.047594 | −0.027008 | −0.026766 | −0.09494 | 0.037919 | −0.077962 | 0.061523 | −0.058038 | −0.142152 | 0.054666 | −0.00843 | 0.008742 |
| 294 | 0.026327 | −0.008145 | −0.001747 | −0.066421 | 0.023878 | −0.014424 | 0.048483 | 0.000764 | 0.017918 | 0.01437 | 0.047813 | 0.077436 | 0.004649 | −0.026675 |
| 295 | 0.066591 | 0.015126 | 0.005011 | −0.085203 | 0.011512 | 0.021536 | 0.008017 | −0.004028 | −0.006775 | 0.01711 | −0.034066 | −0.01491 | 0.005629 | 0.081052 |
| 296 | −0.035416 | −0.006745 | 0.008936 | −0.025139 | 0.040379 | 0.028979 | 0.035882 | 0.03569 | 0.033265 | 0.079313 | 0.027947 | 0.000566 | 0.016415 | 0.032968 |
| 297 | 0.01862 | 0.083675 | 0.058176 | −0.005272 | 0.045172 | 0.020069 | −0.02694 | −0.071499 | 0.016792 | 0.020002 | −0.006324 | 0.040775 | −0.032913 | 0.074215 |
| 298 | 0.016942 | −0.050605 | 0.10741 | 0.047202 | 0.082792 | 0.005504 | −0.024706 | −0.052437 | −0.020587 | 0.109712 | 0.017194 | 0.077843 | −0.028263 | 0.103598 |
| 299 | 0.023694 | 0.053617 | −0.00105 | −0.005527 | 0.050524 | 0.090825 | 0.047961 | −0.005804 | 0.004696 | 0.035293 | 0.011883 | −0.036825 | 0.010684 | −0.037858 |
| 300 | 0.094506 | 0.108897 | −0.031023 | 0.012953 | 0.048385 | 0.05443 | 0.033913 | −0.077142 | −0.048749 | 0.016336 | −0.048671 | 0.06934 | 0.000993 | −0.046899 |
| 301 | 0.060638 | −0.030805 | −0.005724 | −0.060561 | 0.009984 | 0.044856 | −0.009108 | 0.023091 | 0.05309 | 0.004648 | −0.027917 | 0.00873 | 0.023396 | 0.007932 |
| 302 | 0.053303 | 0.020308 | −0.061455 | −0.096113 | 0.058226 | 0.00116 | −0.036066 | 0.07294 | −0.002708 | 0.069716 | −0.018284 | −0.015535 | 0.010069 | −0.050095 |
| 303 | 0.002162 | 0.030724 | 0.004827 | 0.044032 | 0.00499 | 0.084163 | 0.022225 | −0.005894 | −0.000897 | 0.03788 | 0.007467 | −0.038917 | 0.03503 | −0.055155 |
| 304 | 0.060204 | 0.0235651 | −0.088455 | 0.084686 | 0.033062 | 0.060741 | 0.024495 | 0.013105 | −0.023209 | −0.010896 | −0.127631 | −0.000934 | 0.035061 | −0.035981 |
| 305 | 0.1115541 | 0.0794461 | 0.080234 | −0.036899 | −0.068627 | −0.044793 | 0.151073 | −0.077559 | −0.102869 | −0.045842 | −0.031826 | −0.085002 | 0.054538 | 0.041715 |
| 306 | 0.071449 | 0.017618 | −0.015601 | −0.044154 | 0.023054 | 0.031164 | −0.074764 | 0.028487 | 0.067047 | −0.022508 | 0.023546 | 0.014288 | 0.007504 | −0.075537 |
| 307 | −0.09951 | −0.017565 | 0.012709 | −0.012472 | −0.142873 | 0.040688 | −0.073843 | 0.030127 | 0.075622 | −0.043321 | −0.029149 | 0.030422 | 0.005878 | −0.002557 |
| 308 | −0.001846 | 0.036147 | −0.032365 | 0.058393 | 0.045541 | −0.046428 | −0.026729 | 0.003705 | −0.00174 | −0.038206 | 0.006676 | 0.007485 | 0.01745 | −0.013241 |
| 309 | 0.002167 | 0.013151 | −0.016536 | 0.052966 | −0.002228 | −0.01014 | −0.058237 | −0.000689 | 0.062678 | −0.038739 | 0.025427 | −0.029526 | −0.059751 | 0.071187 |
| 310 | −0.009896 | −0.032257 | 0.016637 | 0.035502 | 0.024495 | 0.037336 | −0.089051 | 0.081864 | 0.081166 | −0.041968 | 0.074255 | −0.055619 | 0.085848 | −0.030592 |
| 311 | 0.069268 | −0.07235 | 0.038803 | 0.02195 | −0.029296 | 0.050742 | 0.095468 | −0.021959 | −0.029099 | −0.00579 | −0.02991 | 0.039086 | −0.085118 | 0.050677 |
| 312 | −0.091777 | 0.180425 | −0.065914 | −0.041318 | 0.026865 | −0.046462 | −0.044996 | −0.021174 | −0.045134 | 0.012268 | −0.03284 | 0.025887 | 0.08604 | −0.060431 |
| 313 | −0.022271 | −0.084595 | −0.079505 | 0.018968 | 0.002439 | −0.054583 | 0.000072 | −0.025672 | −0.014184 | 0.065985 | −0.04827 | −0.033475 | 0.042576 | 0.025284 |
| 314 | −0.010054 | 0.053174 | 0.0268 | 0.010506 | −0.013654 | 0.030113 | −0.147687 | −0.068247 | 0.125628 | 0.088081 | −0.011809 | 0.007883 | −0.013679 | 0.001147 |
| 315 | −0.02964 | 0.052545 | −0.006298 | 0.01152 | 0.015814 | −0.030729 | 0.010976 | 0.026144 | −0.030625 | 0.094211 | −0.006923 | −0.05859 | −0.040561 | 0.022854 |
| 316 | −0.037323 | −0.035871 | 0.079781 | −0.010246 | −0.050135 | −0.024388 | −0.02282 | −0.082143 | −0.056453 | 0.055216 | 0.046009 | −0.119321 | −0.066582 | 0.014558 |
| 317 | −0.001904 | −0.028509 | 0.048732 | 0.03644 | −0.004458 | 0.016749 | −0.08406 | 0.085065 | 0.075765 | −0.04507 | 0.010033 | 0.010063 | 0.00736 | 0.120542 |
| 318 | −0.05 | −0.007897 | −0.031568 | −0.044006 | −0.049348 | 0.108034 | −0.01622 | 0.052361 | −0.087144 | −0.022876 | −0.044904 | 0.070722 | −0.018776 | 0.046652 |
| 319 | −0.0497511 | 0.0356221 | 0.025098 | 0.039933 | 0.035839 | −0.004468 | −0.009738 | 0.055439 | −0.013241 | 0.023642 | 0.016954 | −0.00535 | −0.025114 | 0.082743 |
| 320 | −0.0301861 | −0.0753961 | −0.0459071 | 0.023856 | −0.078477 | −0.018512 | 0.008886 | 0.026335 | −0.011005 | 0.070379 | −0.007953 | 0.046979 | −0.032267 | −0.068388 |
| 321 | 0.038073 | 0.033612 | −0.057496 | −0.068518 | −0.034939 | 0.008472 | −0.02306 | −0.028902 | 0.072164 | 0.055048 | 0.007143 | −0.086689 | −0.027424 | −0.058685 |
| 322 | 0.040656 | 0.034302 | −0.009419 | 0.01529 | −0.105913 | −0.054615 | 0.032735 | 0.048581 | 0.020674 | 0.010651 | −0.034238 | 0.053315 | 0.05668 | 0.022588 |
| 323 | −0.053159 | 0.033938 | −0.050499 | −0.029324 | −0.047254 | −0.007201 | −0.094937 | −0.022167 | −0.022941 | −0.001306 | −0.041968 | 0.104676 | −0.015384 | 0.111736 |
| 324 | −0.029508 | −0.11726 | 0.059711 | −0.126734 | −0.017839 | −0.104931 | −0.044947 | −0.020169 | −0.048321 | 0.07491 | −0.006144 | 0.015843 | −0.000664 | −0.026762 |
| 325 | −0.030305 | 0.000852 | 0.077628 | 0.030328 | −0.020477 | −0.044566 | −0.07087 | −0.079464 | 0.066246 | 0.046253 | −0.017294 | −0.080625 | −0.015009 | 0.009566 |
| 326 | 0.037757 | −0.092428 | 0.029474 | −0.059224 | 0.060938 | 0.024161 | 0.027407 | −0.022401 | 0.040078 | 0.002485 | 0.065629 | −0.097092 | 0.00468 | −0.048386 |
| 327 | −0.002905 | 0.024678 | −0.074692 | −0.033933 | −0.035671 | 0.00692 | 0.007491 | 0.023428 | −0.046793 | −0.017234 | 0.065407 | −0.027011 | 0.063914 | −0.017794 |
| 328 | −0.042961 | 0.085943 | 0.019395 | 0.051843 | 0.028066 | −0.150116 | 0.052701 | 0.078603 | −0.072477 | −0.129372 | −0.079473 | −0.055473 | −0.014934 | 0.182967 |
| 329 | −0.049969 | 0.026277 | −0.063729 | −0.066958 | 0.00664 | 0.134596 | 0.0318 | 0.032397 | −0.063755 | −0.029778 | 0.024006 | −0.061929 | 0.068453 | 0.049446 |
| 330 | 0.05126 | −0.06138 | 0.104102 | −0.003041 | 0.095747 | −0.044267 | −0.13079 | 0.042706 | 0.058911 | −0.02481 | −0.022249 | 0.087184 | 0.044305 | −0.057801 |
| 331 | 0.016609 | 0.031586 | −0.047189 | −0.035231 | −0.036645 | −0.064354 | 0.072576 | −0.08784 | 0.017507 | 0.014688 | 0.032781 | 0.006045 | −0.023702 | 0.025062 |
| 332 | 0.006334 | −0.083278 | −0.019253 | 0.053657 | −0.00739 | 0.064049 | 0.102304 | −0.038377 | 0.025986 | 0.017271 | −0.004958 | 0.027704 | −0.00788 | −0.105232 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 333 | −0.073742 | −0.040698 | −0.007392 | 0.002655 | −0.065514 | −0.032904 | −0.018765 | −0.038661 | 0.051669 | −0.036682 | −0.009776 | −0.029513 | 0.015088 | 0.082964 |
| 334 | −0.043725 | 0.013304 | −0.057824 | 0.01248 | −0.020411 | 0.029117 | −0.128037 | 0.021921 | 0.044835 | 0.035432 | −0.045598 | −0.086478 | −0.124507 | −0.055718 |
| 335 | −0.040645 | −0.021584 | 0.014123 | −0.041155 | 0.023475 | −0.03468 | −0.039349 | −0.061579 | −0.063086 | −0.061704 | −0.019789 | −0.049219 | 0.098862 | 0.032631 |
| 336 | 0.030923 | 0.076213 | −0.102717 | −0.020514 | 0.064738 | 0.026588 | 0.018626 | −0.020607 | 0.101797 | −0.186569 | 0.078468 | −0.047087 | −0.118625 | −0.003031 |
| 337 | 0.005836 | −0.044087 | 0.100864 | −0.010422 | 0.024206 | 0.055785 | 0.064964 | −0.00194 | −0.031239 | 0.028783 | 0.027303 | −0.021193 | 0.060057 | −0.062142 |
| 338 | −0.042673 | −0.020682 | 0.002848 | −0.02793 | 0.112143 | 0.019306 | −0.074048 | −0.031867 | −0.036847 | 0.075286 | 0.073386 | 0.03032 | −0.044462 | −0.032728 |
| 339 | 0.181777 | 0.068252 | −0.005089 | 0.069623 | −0.126485 | −0.107954 | 0.010883 | −0.017598 | −0.014994 | −0.048053 | 0.011227 | −0.027446 | −0.091176 | −0.064819 |
| 340 | −0.080535 | 0.004796 | 0.003398 | 0.045453 | −0.083443 | 0.058619 | −0.116528 | −0.078074 | −0.059798 | −0.007371 | 0.008067 | 0.01706 | −0.001741 | −0.008555 |

| | CR | CS | CT | CU | CV | CW | CX | CY | CZ | DA | DB | DC | DD | DE |
|---|---|---|---|---|---|---|---|---|---|---|---|---|---|---|
| 1 | −0.0778721 | 0.0403381 | −0.0210661 | −0.061642 | 0.129158 | 0.066947 | 0.040786 | −0.083018 | −0.087215 | −0.007825 | −0.089877 | −0.024334 | 0.0003571 | 0.002546 |
| 2 | 0.022861 | 0.055309 | 0.0796391 | 0.06772 | −0.210856 | 0.146124 | 0.037481 | 0.118911 | 0.1323051 | 0.1155271 | 0.0287991 | 0.0267021 | −0.023478 | 0.031839 |
| 3 | −0.09574 | 0.002447 | −0.012745 | −0.106934 | 0.139756 | −0.00192 | −0.040958 | 0.01183 | 0.004236 | −0.050072 | −0.078264 | 0.026646 | −0.001674 | −0.045474 |
| 4 | −0.03091 | −0.023056 | −0.0001 | −0.039743 | −0.078157 | −0.014465 | −0.008224 | −0.040062 | 0.013191 | 0.051822 | 0.085537 | 0.125989 | 0.030354 | 0.142005 |
| 5 | 0.166962 | −0.085552 | −0.019581 | −0.077451 | 0.003647 | −0.041615 | −0.00649 | −0.046372 | −0.028748 | 0.077336 | −0.021252 | −0.015826 | −0.021739 | 0.121223 |
| 6 | 0.005186 | −0.111501 | 0.005929 | 0.030403 | 0.029655 | 0.030783 | 0.015326 | −0.035415 | −0.002217 | −0.056598 | −0.060444 | 0.003929 | 0.024988 | −0.04684 |
| 7 | −0.051917 | 0.101633 | −0.065097 | −0.089298 | 0.060748 | −0.027696 | −0.019552 | 0.01591 | 0.053286 | −0.046262 | 0.119621 | 0.046312 | −0.006153 | −0.035415 |
| 8 | 0.035407 | 0.0838241 | −0.0203021 | −0.01617 | −0.135692 | −0.015093 | 0.050874 | −0.026218 | 0.017192 | −0.011346 | −0.091224 | 0.055689 | 0.061092 | 0.152667 |
| 9 | 0.048816 | −0.033608 | −0.162734 | 0.011199 | 0.03785 | −0.049987 | −0.024358 | 0.012579 | −0.007818 | −0.004639 | −0.174656 | 0.004569 | 0.004496 | −0.024062 |
| 10 | −0.011157 | −0.025466 | −0.008429 | 0.158406 | 0.021717 | −0.013148 | −0.024534 | −0.069217 | −0.026572 | −0.029548 | −0.085534 | 0.075834 | 0.008551 | 0.08315 |
| 11 | −0.004495 | 0.011347 | −0.006683 | 0.041727 | 0.041634 | 0.005531 | −0.020138 | −0.0191 | 0.003498 | 0.080493 | −0.040091 | 0.053781 | −0.067538 | −0.05841 |
| 12 | 0.077667 | −0.034915 | −0.041696 | 0.028763 | 0.043445 | −0.013342 | −0.010767 | 0.037167 | −0.039461 | −0.094685 | 0.017791 | 0.039741 | −0.002291 | −0.050807 |
| 13 | 0.011522 | 0.1007 | −0.057905 | −0.185787 | −0.056191 | 0.032478 | 0.030447 | −0.002824 | −0.094726 | −0.064112 | 0.04808 | −0.092153 | −0.012532 | 0.079582 |
| 14 | 0.03562 | −0.078145 | 0.051328 | 0.024846 | −0.015054 | −0.005577 | 0.028802 | 0.04537 | 0.044395 | 0.022956 | 0.010014 | 0.030158 | 0.031933 | −0.056236 |
| 15 | −0.021349 | −0.073922 | −0.033288 | −0.102639 | −0.014578 | −0.029978 | 0.017273 | 0.036637 | 0.019239 | 0.023124 | −0.066845 | 0.002897 | 0.033565 | −0.068404 |
| 16 | −0.040447 | −0.044305 | −0.0217231 | 0.090675 | −0.11174 | 0.002372 | −0.012205 | 0.035973 | −0.063445 | −0.044863 | −0.016442 | −0.011039 | −0.091969 | 0.009858 |
| 17 | −0.052211 | 0.108437 | 0.0093051 | −0.131519 | −0.100644 | 0.011855 | 0.074634 | −0.034265 | −0.065353 | −0.029565 | −0.068262 | −0.034535 | 0.0326011 | 0.131784 |
| 18 | −0.075164 | 0.0640011 | −0.0215651 | 0.039093 | 0.01026 | 0.016316 | −0.034615 | 0.043118 | −0.048977 | −0.077002 | −0.145895 | 0.030433 | −0.04269 | −0.044095 |
| 19 | 0.111211 | −0.158911 | −0.056516 | 0.026102 | 0.015751 | −0.102675 | −0.021366 | −0.02821 | −0.007487 | −0.03381 | 0.045583 | −0.010168 | −0.003767 | −0.031924 |
| 20 | 0.001389 | 0.030834 | −0.052371 | 0.059306 | −0.063813 | −0.028887 | −0.02692 | 0.009183 | 0.010586 | −0.012799 | 0.093989 | 0.001321 | −0.062951 | 0.106563 |
| 21 | 0.04912 | 0.00196 | 0.0262151 | 0.075264 | 0.132899 | −0.001255 | 0.004466 | −0.026761 | −0.08728 | −0.051382 | −0.056389 | −0.134177 | −0.032463 | −0.113919 |
| 22 | −0.021638 | 0.039093 | −0.007917 | −0.004745 | −0.088888 | 0.033609 | −0.078128 | −0.043431 | 0.0030131 | 0.0284831 | −0.005881 | 0.0582481 | 0.0356331 | −0.065137 |
| 23 | −0.029248 | 0.058154 | −0.013307 | −0.111078 | −0.0206 | 0.005354 | −0.012056 | 0.015865 | −0.040067 | −0.126163 | 0.038338 | 0.07701 | −0.00356 | 0.000837 |
| 24 | 0.030665 | 0.07706 | −0.048944 | 0.032695 | −0.088011 | −0.050239 | 0.046904 | −0.059012 | 0.019657 | −0.024292 | 0.036203 | −0.030737 | −0.010275 | 0.040923 |
| 25 | 0.035988 | 0.03618 | 0.017911 | −0.068033 | −0.007191 | 0.000511 | −0.016509 | 0.021025 | 0.04537 | 0.070244 | 0.091021 | 0.047152 | 0.003388 | −0.016989 |
| 26 | 0.026959 | −0.028001 | −0.01699 | −0.13506 | 0.206652 | −0.051546 | −0.006124 | −0.006922 | −0.099657 | 0.002907 | −0.013657 | 0.020107 | 0.03408 | 0.036645 |
| 27 | 0.006537 | −0.008767 | 0.024268 | 0.042589 | 0.04366 | 0.093651 | 0.012394 | −0.049512 | −0.027831 | 0.095861 | 0.065727 | −0.164038 | −0.062135 | −0.019821 |
| 28 | 0.006733 | 0.024194 | 0.027493 | 0.071287 | 0.092326 | −0.027118 | 0.049546 | 0.013395 | −0.004722 | 0.101469 | 0.051723 | 0.027331 | 0.035804 | −0.049203 |
| 29 | −0.004891 | −0.075997 | −0.002813 | −0.03664 | −0.4824 | −0.031059 | −0.018604 | −0.029787 | 0.00044 | −0.022671 | 0.037944 | −0.020373 | −0.020385 | −0.079102 |
| 30 | 0.00247 | −0.036615 | 0.043912 | −0.019011 | −0.023386 | −0.006911 | −0.022759 | 0.116449 | 0.113908 | 0.037304 | 0.053967 | −0.137938 | −0.08264 | 0.005045 |
| 31 | 0.028527 | −0.109978 | 0.044207 | 0.101688 | −0.000022 | 0.008658 | −0.010875 | −0.067875 | 0.044265 | −0.126705 | 0.014659 | −0.009179 | 0.107257 | 0.068819 |
| 32 | −0.022607 | 0.0237831 | −0.013268 | 0.093929 | −0.049349 | −0.000145 | 0.002637 | −0.022966 | −0.002168 | −0.011521 | −0.017516 | 0.0677641 | −0.018932 | 0.040588 |
| 33 | −0.01323 | −0.07711 | −0.016622 | −0.039751 | −0.029353 | 0.048424 | 0.019677 | 0.012815 | 0.072327 | −0.051777 | 0.070977 | −0.06023 | 0.04399 | 0.057393 |
| 34 | 0.00662 | 0.013094 | 0.005993 | 0.117142 | 0.000673 | 0.011296 | 0.030813 | −0.050017 | −0.124108 | −0.08207 | −0.02206 | 0.014551 | 0.043343 | 0.020765 |
| 35 | 0.12511 | −0.00891 | 0.015249 | −0.047977 | −0.03441 | −0.006831 | −0.004805 | −0.06831 | −0.112081 | −0.061805 | 0.113715 | 0.0055 | 0.031643 | −0.124079 |
| 36 | −0.060234 | −0.0115851 | 0.012271 | 0.085953 | −0.063124 | −0.029097 | −0.001425 | −0.007409 | 0.052372 | −0.116825 | −0.041654 | −0.079498 | −0.137624 | −0.019666 |
| 37 | 0.045342 | −0.098848 | −0.012588 | 0.004982 | 0.023506 | −0.018974 | −0.000714 | 0.117084 | 0.0810111 | 0.0531411 | −0.197799 | 0.034531 | 0.0171581 | 0.004634 |
| 38 | 0.1600411 | 0.022484 | −0.02232 | 0.036501 | 0.001142 | −0.020881 | −0.013706 | −0.032938 | 0.037258 | −0.008111 | −0.020589 | −0.015137 | −0.025959 | −0.008893 |
| 39 | −0.075391 | 0.053034 | −0.07749 | G.002007 | −0.031203 | −0.070731 | −0.026478 | −0.016049 | −0.094525 | −0.004427 | −0.157909 | 0.013571 | 0.176829 | −0.041138 |
| 40 | 0.042854 | −0.012871 | −0.100693 | 0.205321 | −0.000012 | 0.060711 | 0.061927 | 0.04642 | −0.022203 | 0.079508 | 0.033307 | −0.0418 | −0.021364 | 0.012637 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 41 | 0.002451 | −0.026994 | −0.104655 | −0.033152 | 0.058061 | 0.038441 | 0.060596 | 0.008854 | −0.012485 | 0.111117 | 0.149039 | 0.009673 | 0.038006 | 0.055954 |
| 42 | 0.005186 | 0.0039241 | 0.8648251 | −0.127917 | 0.059426 | −0.019276 | −0.001798 | −0.010536 | −0.007004 | −0.031902 | −0.024744 | 0.0098871 | −0.012452 | 0.015572 |
| 43 | 0.062874 | 0.011148 | −0.060087 | 0.019081 | 0.026804 | 0.016904 | 0.033076 | −0.13487 | −0.001591 | −0.084092 | −0.026239 | 0.0347331 | −0.036344 | −0.008082 |
| 44 | 0.035602 | −0.032145 | −0.053832 | 0.000213 | 0.022554 | 0.00855 | −0.032897 | 0.066032 | 0.171728 | −0.093463 | 0.110574 | 0.040946 | −0.060233 | 0.03355 |
| 45 | 0.045367 | 0.04036 | −0.062126 | −0.084148 | −0.065696 | −0.023733 | −0.038222 | 0.010014 | −0.019363 | 0.134956 | −0.098065 | 0.034409 | 0.186184 | −0.005612 |
| 46 | −0.00872 | 0.076485 | −0.015064 | 0.042302 | −0.027672 | −0.052212 | −0.007317 | 0.021349 | −0.095783 | −0.045347 | −0.065953 | 0.06404 | −0.02212 | 0.080515 |
| 47 | 0.0402941 | −0.008327 | 0.002126 | −0.001616 | −0.014184 | 0.020416 | −0.007764 | −0.026042 | 0.087287 | 0.176775 | −0.057816 | 0.009041 | 0.000164 | −0.026427 |
| 48 | 0.02851 | −0.074308 | −0.041603 | −0.041421 | 0.003549 | −0.05809 | 0.032142 | −0.06143 | −0.018165 | −0.019768 | 0.003417 | 0.075133 | −0.108005 | −0.141449 |
| 49 | −0.006831 | −0.095399 | −0.014782 | −0.015726 | −0.030382 | −0.015849 | 0.005405 | −0.110222 | 0.012774 | −0.010503 | −0.021533 | −0.074124 | −0.030585 | −0.042014 |
| 50 | −0.018622 | 0.002328 | −0.002332 | −0.082721 | 0.004063 | −0.010948 | 0.066211 | −0.072421 | 0.069956 | 0.048305 | −0.014282 | 0.040971 | 0.018388 | 0.005611 |
| 51 | 0.031555 | −0.011659 | −0.027224 | −0.05221 | −0.0218 | 0.05041 | 0.017488 | −0.059699 | −0.243674 | −0.057415 | 0.000895 | −0.012453 | 0.003876 | 0.083988 |
| 52 | 0.0035791 | −0.029226 | 0.016371 | −0.061187 | −0.005733 | −0.014043 | 0.024272 | 0.075924 | 0.058897 | −0.05363 | −0.090733 | −0.018081 | −0.019904 | 0.005886 |
| 53 | −0.104275 | 0.028498 | −0.003644 | −0.048686 | −0.036927 | −0.018781 | −0.012531 | −0.009756 | 0.0996891 | 0.016989 | 0.063183 | −0.050149 | −0.125782 | 0.056885 |
| 54 | 0.057579 | −0.042647 | −0.050252 | 0.081095 | 0.082673 | −0.095299 | −0.070624 | −0.00864 | 0.044804 | 0.064694 | 0.073979 | 0.013639 | 0.014206 | 0.030977 |
| 55 | −0.017419 | −0.079351 | −0.010806 | −0.066327 | −0.017683 | −0.050036 | 0.016441 | 0.023265 | −0.050116 | −0.096158 | 0.026888 | −0.114289 | −0.036473 | 0.011391 |
| 56 | 0.046184 | −0.021455 | −0.024482 | −0.138373 | −0.018677 | 0.058613 | −0.083915 | 0.092838 | −0.051755 | 0.027206 | 0.069123 | 0.004134 | −0.056996 | −0.056765 |
| 57 | 0.057383 | 0.033225 | 0.001062 | −0.002038 | 0.018117 | −0.014752 | 0.0327 | −0.001089 | 0.008972 | −0.070482 | −0.057782 | 0.078678 | 0.032257 | −0.089345 |
| 58 | 0.074295 | 0.064717 | −0.014528 | −0.041768 | 0.07144 | 0.053482 | −0.025107 | 0.092316 | 0.0509571 | 0.0006871 | −0.029311 | 0.1103431 | −0.001067 | −0.009762 |
| 59 | −0.048071 | −0.005103 | 0.0020831 | 0.026523 | −0.032187 | 0.01096 | 0.017001 | 0.008601 | −0.050249 | 0.02058 | 0.066213 | −0.052379 | 0.040453 | 0.124154 |
| 60 | −0.010929 | 0.004036 | 0.003085 | −0.02188 | 0.01755 | 0.051702 | −0.024378 | 0.056251 | 0.027947 | 0.015015 | 0.027987 | 0.059498 | −0.031391 | −0.013994 |
| 61 | −0.081407 | 0.031235 | −0.017377 | −0.008264 | 0.015865 | −0.058306 | −0.056892 | 0.041448 | −0.016389 | −0.034287 | 0.007456 | −0.01842Y | −0.047535 | 0.046786 |
| 62 | 0.033802 | −0.012323 | 0.002641 | 0.056809 | 0.001885 | −0.023017 | 0.065011 | 0.05194 | 0.045723 | 0.022515 | −0.15276 | −0.058304 | 0.025065 | 0.060288 |
| 63 | 0.06307 | −0.006671 | −0.054951 | −0.074164 | −0.023244 | 0.025491 | 0.065059 | −0.036465 | 0.1726751 | −0.047438 | −0.001992 | 0.0206111 | −0.023874 | 0.0231 |
| 64 | −0.003706 | −0.046169 | −0.012633 | 0.031208 | −0.060285 | 0.03697 | −0.036272 | −0.093346 | −0.107706 | −0.096113 | −0.011012 | 0.004333 | 0.030704 | −0.083531 |
| 65 | 0.112583 | −0.00407 | 0.000016 | −0.103537 | 0.051823 | −0.01034 | 0.003157 | 0.10358 | 0.009365 | 0.088676 | −0.073099 | 0.000921 | −0.053386 | 0.067097 |
| 66 | 0.002784 | −0.051385 | 0.003968 | 0.038395 | −0.058546 | −0.019857 | 0.006969 | 0.014009 | −0.004219 | 0.028092 | −0.106589 | 0.027141 | −0.050562 | −0.075861 |
| 67 | −0.048781 | −0.000788 | 0.003723 | −0.043428 | 0.074966 | 0.041987 | −0.02436 | 0.019471 | −0.000687 | −0.076678 | −0.095713 | 0.028911 | −0.04064 | −0.014242 |
| 68 | −0.04787 | −0.005069 | 0.015202 | 0.066049 | −0.051754 | 0.005601 | 0.012058 | −0.0332 | −0.047491 | −0.002114 | 0.021011 | −0.022208 | −0.091423 | −0.062648 |
| 69 | −0.008883 | −0.048256 | 0.005347 | 0.019518 | −0.006249 | 0.054717 | 0.013787 | 0.044683 | 0.016081 | −0.027424 | 0.0439 | 0.020275 | 0.017024 | 0.073988 |
| 70 | −0.016681 | 0.02667 | −0.003198 | −0.009678 | −0.011041 | −0.039317 | 0.015935 | −0.102745 | −0.031237 | 0.087023 | −0.054493 | −0.042798 | −0.020446 | −0.000815 |
| 71 | 0.019584 | 0.037808 | 0.009584 | 0.015942 | 0.012206 | −0.047606 | −0.050241 | 0.034902 | −0.082019 | −0.08403 | −0.078306 | −0.098737 | −0.059947 | 0.060681 |
| 72 | 0.063615 | −0.017815 | 0.008505 | −0.085651 | 0.013594 | 0.044927 | 0.043531 | 0.024612 | 0.120852 | 0.041757 | 0.002514 | 0.029725 | −0.08037 | 0.047158 |
| 73 | 0.025787 | −0.056769 | −0.001933 | −0.037076 | 0.018909 | 0.021177 | −0.033821 | −0.012064 | −0.064315 | −0.023854 | 0.034893 | 0.021246 | −0.024778 | −0.019299 |
| 74 | −0.034677 | 0.0237651 | −0.034117 | 0.010028 | −0.021226 | 0.014042 | −0.035107 | −0.006998 | 0.018299 | −0.037437 | 0.00913 | 0.017457 | −0.00817 | −0.036319 |
| 75 | 0.032107 | 0.02486 | 0.014767 | 0.077062 | 0.011214 | −0.061396 | −0.004547 | 0.045089 | −0.009293 | 0.027936 | −0.029376 | 0.08202 | −0.012096 | 0.007152 |
| 76 | −0.049694 | −0.121901 | 0.027376 | 0.044121 | −0.046493 | 0.008607 | −0.002244 | −0.098298 | −0.000073 | −0.02956 | −0.134674 | 0.066872 | 0.034498 | 0.006646 |
| 77 | −0.023427 | 0.01651 | −0.003972 | 0.057114 | 0.023168 | 0.02433 | −0.040898 | 0.039792 | 0.048829 | −0.039475 | −0.036392 | 0.005107 | −0.107766 | −0.00084 |
| 78 | 0.023748 | 0.021801 | −0.010129 | −0.016728 | 0.035997 | 0.108074 | 0.070524 | −0.033335 | −0.011108 | 0.050111 | −0.074562 | −0.008835 | 0.017629 | −0.040243 |
| 79 | 0.010317 | 0.020219 | 0.005403 | 0.019559 | −0.005254 | −0.074629 | −0.036442 | 0.081292 | 0.01651 | 0.038656 | 0.244605 | 0.002274 | 0.068551 | −0.115155 |
| 80 | 0.042096 | −0.066433 | −0.022826 | k0.09969 | −0.003962 | −0.033969 | −0.035558 | 0.005728 | 0.047593 | −0.024731 | 0.045072 | −0.008639 | 0.01556 | 0.078539 |
| 81 | 0.009914 | −0.070535 | −0.022452 | −0.049568 | 0.015264 | −0.014817 | −0.050958 | 0.007297 | −0.046056 | −0.062307 | 0.05182 | 0.021729 | 0.023712 | 0.040177 |
| 82 | −0.047906 | −0.023464 | −0.015469 | 0.040704 | 0.078738 | 0.005634 | −0.029328 | 0.036674 | 0.101852 | 0.006598 | −0.039145 | 0.000546 | 0.047749 | 0.009941 |
| 83 | 0.0679791 | 0.0446851 | −0.010058 | −0.076009 | 0.064057 | 0.009921 | −0.000305 | 0.014116 | 0.0197881 | 0.0478281 | −0.017156 | 0.0574971 | −0.048819 | 0.003453 |
| 84 | −0.023861 | 0.0878151 | 0.004249 | 0.02995 | 0.067766 | 0.025047 | 0.014902 | 0.034249 | −0.001325 | 0.0067151 | 0.0126961 | 0.1079221 | −0.02995 | −0.157756 |
| 85 | −0.057973 | −0.030233 | −0.011571 | 0.041541 | −0.015682 | −0.021204 | 0.019435 | −0.037509 | 0.057422 | 0.153281 | 0.026828 | 0.019946 | −0.112231 | 0.036569 |
| 86 | −0.014064 | 0.04309 | −0.02143 | −0.051317 | 0.059416 | −0.04829 | 0.036511 | 0.002978 | 0.072653 | −0.083652 | −0.023508 | 0.000797 | 0.078406 | −0.016546 |
| 87 | −0.09732 | 0.107102 | 0.026349 | −0.015491 | 0.003432 | −0.051781 | −0.010414 | −0.08074 | −0.094197 | 0.060063 | 0.017414 | 0.026648 | 0.004475 | −0.068182 |
| 88 | −0.021291 | −0.086932 | 0.008493 | −0.034876 | 0.032349 | 0.019567 | 0.010826 | −0.041961 | 0.03827 | 0.029195 | −0.104043 | −0.005465 | 0.004004 | 0.032529 |
| 89 | 0.008614 | 0.004573 | 0.01424 | −0.006875 | −0.037126 | 0.004604 | 0.050564 | 0.004318 | −0.053491 | −0.062097 | 0.0104 | 0.09052 | 0.178139 | 0.048363 |
| 90 | 0.019141 | −0.002937 | 0.0271171 | 0.079587 | −0.051405 | −0.004952 | −0.011108 | 0.080094 | −0.052349 | −0.079074 | 0.013969 | 0.094886 | −0.1241 | −0.15274 |
| 91 | 0.024811 | 0.051731 | −0.023468 | 0.005892 | −0.000493 | 0.037513 | 0.000216 | −0.024783 | −0.125376 | −0.037438 | 0.127059 | −0.017567 | −0.097589 | 0.074723 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 92 | 0.061697 | −0.016024 | 0.030171 | −0.009109 | −0.016725 | −0.007897 | −0.000286 | −0.017507 | −0.021411 | 0.106505 | 0.029995 | 0.009691 | 0.003553 | 0.066066 |
| 93 | 0.029378 | 0.035291 | −0.001894 | −0.045751 | 0.009778 | 0.079137 | −0.010705 | 0.057654 | 0.041506 | 0.016676 | −0.087823 | −0.091835 | 0.11378 | −0.019852 |
| 94 | 0.008377 | 0.117254 | 0.028015 | 0.071767 | 0.080702 | −0.024927 | −0.018895 | −0.081596 | 0.017573 | 0.039849 | −0.041083 | −0.013695 | −0.037664 | 0.045307 |
| 95 | 0.000909 | −0.022835 | 0.014669 | −0.001902 | −0.016978 | −0.074493 | 0.049258 | −0.149681 | −0.060514 | −0.059179 | 0.139419 | 0.02357 | 0.021522 | 0.098276 |
| 96 | −0.019083 | −0.043432 | −0.005532 | 0.063756 | 0.011037 | 0.033604 | −0.02338 | 0.033365 | 0.004788 | −0.040695 | −0.008916 | 0.080267 | 0.046771 | −0.045304 |
| 97 | 0.118813 | 0.078567 | −0.035079 | 0.079847 | −0.00423 | −0.045155 | −0.047601 | −0.104882 | −0.070772 | −0.008338 | −0.05186 | 0.061978 | −0.024762 | 0.009063 |
| 98 | −0.032414 | −0.0081281 | 0.015112 | 0.008413 | 0.037937 | −0.036314 | −0.120661 | −0.020488 | 0.076903 | −0.02644 | −0.061345 | −0.003473 | 0.105502 | 0.140024 |
| 99 | −0.027335 | −0.0146431 | 0.028351 | 0.014066 | −0.042197 | 0.001631 | 0.023318 | −0.091927 | 0.0112251 | −0.050505 | 0.0128631 | 0.0324891 | −0.054395 | 0.064892 |
| 100 | 0.0375191 | −0.0161011 | −0.012121 | −0.002878 | 0.022026 | 0.841827 | −0.025365 | −0.032207 | −0.043565 | −0.031624 | 0.014969 | 0.014853 | −0.004302 | −0.004152 |
| 101 | −0.019325 | −0.010186 | 0.015585 | −0.00715 | 0.027461 | −0.034402 | 0.892511 | 0.039581 | −0.014117 | −0.021229 | 0.01724 | 0.023408 | −0.019476 | −0.034361 |
| 102 | −0.007118 | −0.04362 | 0.011729 | 0.050313 | −0.034586 | −0.041748 | 0.027455 | 0.715748 | −0.127097 | −0.046851 | −0.014765 | −0.019254 | 0.014873 | 0.042683 |
| 103 | 0.008363 | 0.092787 | −0.009496 | −0.007595 | 0.043586 | −0.022957 | −0.002018 | −0.119017 | 0.601186 | −0.084665 | −0.016958 | −0.027187 | 0.02712 | −0.025167 |
| 104 | −0.1032361 | 0.0356461 | 0.0295241 | 0.017232 | 0.02017 | −0.024733 | −0.008754 | −0.057137 | −0.096471 | 0.637188 | 0.0206691 | −0.012765 | −0.017098 | −0.012246 |
| 105 | −0.1247331 | 0.0245581 | 0.027371 | 0.079866 | 0.114358 | −0.005595 | −0.006668 | −0.009924 | 0.013429 | 0.012802 | 0.464621 | 0.018777 | 0.050808 | 0.012201 |
| 106 | −0.081489 | 0.008339 | 0.019626 | −0.019854 | −0.002388 | 0.009402 | 0.012561 | 0.000771 | −0.010395 | 0.006289 | 0.022919 | 0.732473 | −0.057176 | 0.022556 |
| 107 | 0.10594 | 0.107016 | 0.005924 | 0.10233 | −0.022728 | 0.004765 | −0.001397 | 0.039555 | 0.034535 | 0.002156 | 0.066019 | −0.034509 | 0.658993 | −0.064309 |
| 108 | 0.116898 | −0.011461 | −0.014489 | 0.055539 | 0.139233 | −0.009985 | −0.017847 | 0.010897 | −0.015929 | −0.010349 | 0.022348 | 0.050103 | −0.070503 | 0.572223 |
| 109 | −0.038763 | 0.005121 | 0.01767 | 0.027356 | 0.050567 | −0.045544 | 0.017932 | −0.040903 | −0.017302 | −0.089883 | 0.029303 | 0.01292 | 0.004294 | −0.052927 |
| 110 | 0.081361 | 0.00174 | 0.030945 | 0.039032 | −0.0173 | −0.007884 | −0.006363 | 0.035033 | −0.012296 | 0.032954 | 0.038775 | −0.000865 | 0.020751 | −0.009064 |
| 111 | 0.032815 | 0.100548 | −0.05262 | 0.040767 | 0.115317 | 0.00016 | 0.018283 | −0.002338 | 0.027613 | −0.002529 | −0.021705 | −0.037586 | −0.049841 | −0.101943 |
| 112 | −0.072356 | −0.075901 | −0.004482 | 0.015535 | 0.00092 | 0.003617 | −0.001874 | −0.048442 | −0.009995 | −0.024117 | −0.041704 | −0.066387 | 0.000677 | −0.093348 |
| 113 | 0.021315 | 0.041479 | 0.025652 | −0.083821 | −0.103823 | 0.002522 | 0.021915 | 0.008636 | 0.003723 | 0.012703 | −0.026339 | −0.032307 | −0.017777 | −0.036877 |
| 114 | 0.022879 | 0.054522 | −0.002896 | 0.047601 | 0.010182 | −0.000764 | 0.027005 | 0.02922 | 0.028444 | −0.006746 | −0.021644 | 0.018593 | −0.016396 | −0.066786 |
| 115 | 0.0040561 | −0.0545911 | −0.0241921 | 0.012908 | 0.051623 | −0.00796 | −0.023214 | 0.024806 | 0.050092 | −0.010018 | −0.001753 | 0.012455 | −0.049932 | −0.055562 |
| 116 | 0.100008 | 0.006232 | 0.014043 | 0.02743 | −0.052798 | −0.011702 | −0.015026 | 0.001434 | 0.010957 | 0.064974 | −0.072262 | −0.020155 | −0.02688 | 0.001564 |
| 117 | −0.027811 | −0.035165 | −0.028087 | 0.038359 | 0.038122 | −0.018813 | 0.021387 | −0.037315 | −0.043409 | 0.003414 | −0.006769 | 0.026085 | −0.01395 | −0.004589 |
| 118 | −0.106841 | −0.112952 | 0.010241 | −0.02001 | −0.003635 | 0.001643 | 0.010124 | 0.029246 | 0.065168 | −0.056736 | 0.075544 | 0.096391 | 0.043878 | 0.001555 |
| 119 | 0.005453 | 0.047455 | −0.013491 | −0.036985 | −0.019253 | −0.005774 | 0.01639 | 0.048034 | 0.012386 | 0.011584 | 0.039463 | 0.022832 | −0.013865 | −0.001833 |
| 120 | 0.086197 | −0.041526 | −0.034652 | 0.029691 | −0.008987 | −0.032456 | 0.019969 | −0.036952 | −0.011657 | 0.008505 | 0.020244 | 0.016021 | −0.060342 | −0.028287 |
| 121 | −0.119218 | −0.066662 | −0.011405 | 8.027977 | −0.036967 | −0.018697 | 0.018323 | −0.052776 | −0.016457 | 0.027114 | −0.041159 | −0.019105 | 0.029839 | 0.075935 |
| 122 | −0.014275 | −0.022887 | 0.033269 | −0.036802 | −0.023802 | 0.040901 | 0.007563 | −0.0252 | −0.009594 | 0.00018 | 0.015531 | −0.021565 | −0.026752 | 0.034905 |
| 123 | −0.080585 | 0.026896 | −0.005985 | −0.044961 | −0.012726 | 0.031111 | 0.015834 | 0.043645 | 0.018352 | 0.05455 | −0.024873 | −0.010058 | −0.035828 | −0.006414 |
| 124 | −0.003297 | −0.061454 | 0.010913 | 0.08281 | −0.06073 | −0.008591 | 0.005453 | 0.007086 | 0.0165761 | 0.016958 | 0.021524 | −0.006265 | −0.026371 | 0.020054 |
| 125 | −0.058561 | −0.04944 | 0.022342 | −0.022897 | 0.015849 | 0.019456 | 0.004028 | −0.027801 | 0.028722 | 0.016123 | −0.013165 | 0.022697 | 0.048379 | −0.007565 |
| 126 | −0.025321 | −0.076812 | 0.004464 | −0.022525 | 0.001675 | 0.028051 | 0.025627 | 0.016061 | 0.029808 | 0.011795 | −0.011012 | −0.010797 | −0.002036 | 0.03281 |
| 127 | −0.035589 | −0.06142 | −0.015947 | −0.034704 | 0.037828 | 0.015228 | 0.018357 | 0.022429 | −0.004426 | 0.004179 | 0.055034 | −0.006904 | −0.004187 | 0.011873 |
| 128 | 0.094247 | 0.08752 | −0.010478 | −0.01633 | −0.065439 | −0.039312 | 0.01708 | −0.006705 | −0.02087 | −0.056665 | 0.018047 | 0.015131 | −0.020421 | 0.015318 |
| 129 | 0.05479 | 0.020659 | −0.002061 | 0.007532 | −0.034264 | 0.02948 | 0.036719 | −0.030975 | −0.033031 | −0.010204 | 0.033603 | −0.015498 | 0.044695 | 0.006389 |
| 130 | 0.035205 | 0.127738 | −0.004367 | 0.059399 | 0.046131 | −0.007282 | −0.021252 | 0.04968 | −0.007132 | −0.055037 | 0.035179 | −0.003146 | 0.01258 | 0.025333 |
| 131 | 0.051721 | −0.048431 | −0.025503 | 0.060181 | 0.035924 | −0.014493 | 0.00526 | 0.008881 | −0.052504 | 0.085314 | −0.099624 | 0.034026 | −0.046792 | 0.018234 |
| 132 | 0.081976 | 0.135769 | −0.015652 | 0.012611 | −0.092384 | 0.011276 | 0.012496 | −0.025871 | −0.008227 | −0.009802 | −0.009722 | 0.042762 | −0.062982 | −0.048183 |
| 133 | 0.016872 | −0.06509 | −0.022956 | −0.068178 | 0.022328 | −0.01352 | −0.003433 | −0.020948 | −0.098272 | 0.009901 | 0.003279 | −0.029054 | −0.000668 | −0.04009 |
| 134 | 0.122161 | −0.025233 | 0.023449 | −0.057597 | −0.050692 | 0.023169 | −0.022526 | 0.020714 | −0.027052 | −0.004832 | 0.051583 | 0.109731 | 0.017155 | −0.003088 |
| 135 | 0.013965 | −0.0604721 | 0.007597 | −0.005576 | −0.031885 | −0.008623 | 0.0014 | 0.016373 | −0.000867 | −0.0055 | 0.001239 | −0.015248 | 0.007799 | 0.003987 |
| 136 | −0.029251 | −0.13039 | 0.051897 | 0.012836 | 0.015691 | −0.020812 | −0.019867 | −0.013832 | 0.02148 | 0.062553 | −0.066855 | −0.016109 | 0.047194 | 0.027718 |
| 137 | 0.068458 | 0.094951 | 0.021828 | 0.001775 | 0.000137 | 0.006736 | −0.028889 | 0.022736 | −0.057052 | −0.015653 | 0.014767 | −0.000886 | 0.023898 | −0.007326 |
| 138 | 0.047867 | 0.043959 | 0.04419 | 0.004552 | 0.022621 | 0.05836 | 0.005235 | 0.083298 | 0.002468 | 0.031226 | 0.036215 | 0.007367 | −0.042643 | −0.016796 |
| 139 | 0.003606 | −0.04686 | 0.002063 | 0.02094 | 0.04863 | 0.000909 | −0.025731 | −0.012949 | −0.017904 | 0.028724 | −0.022659 | 0.075934 | 0.033434 | −0.062133 |
| 140 | −0.041403 | 0.101771 | −0.018171 | 0.005165 | 0.13193 | 0.032635 | 0.024342 | −0.002461 | 0.011285 | 0.020657 | 0.033892 | −0.051323 | 0.012689 | −0.036225 |
| 141 | 0.111943 | 0.075441 | 0.069404 | 0.030248 | −0.002285 | −0.015155 | 0.020228 | 0.008455 | −0.022365 | 0.002195 | −0.049829 | −0.009601 | 0.000182 | 0.005974 |
| 142 | −0.125617 | −0.107446 | −0.018985 | −0.029619 | 0.05932 | 0.016412 | 0.007905 | 0.019 | 0.00846 | −0.00725 | −0.037413 | −0.000918 | 0.074781 | 0.052418 |

APPENDIX B2-continued

PCA Transformation Matrix (340 × 340; Benign/Malignant)

| | | | | | | | | | | | | | |
|---|---|---|---|---|---|---|---|---|---|---|---|---|---|
| 143 | −0.00686 | −0.071383 | 0.034527 | 0.044118 | 0.032066 | −0.003249 | −0.021292 | −0.057276 | −0.016232 | −0.019362 | 0.008007 | −0.016925 | −0.028961 | −0.044427 |
| 144 | 0.0349 | 0.017018 | 0.018639 | −0.025317 | −0.01583 | −0.008116 | 0.014732 | −0.017902 | 0.000193 | 0.034791 | 0.02993 | −0.035867 | 0.026895 | 0.029677 |
| 145 | 0.041481 | 0.013271 | −0.006789 | −0.025545 | 0.063186 | 0.018867 | −0.018922 | −0.005637 | −0.032351 | 0.00672 | 0.005613 | 0.03076 | −0.016437 | −0.021289 |
| 146 | 0.076142 | −0.004979 | 0.012356 | −0.027065 | −0.020469 | −0.00649 | 0.00081 | 0.017418 | 0.006203 | 0.005112 | −0.002244 | 0.019269 | 0.000815 | −0.043441 |
| 147 | −0.068141 | 0.103255 | 0.021462 | 0.01198 | −0.093907 | −0.014658 | 0.002949 | 0.029736 | 0.076783 | 0.000337 | −0.012591 | −0.02554 | 0.012656 | 0.013113 |
| 148 | −0.050471 | 0.029074 | 0.007962 | −0.025998 | 0.057872 | −0.016216 | −0.015567 | −0.014674 | −0.045182 | −0.051142 | 0.020221 | −0.061287 | −0.013158 | 0.031815 |
| 149 | 0.009228 | 0.009264 | 0.009142 | −0.029569 | 0.017665 | −0.004239 | −0.027661 | 0.040165 | −0.042011 | −0.049794 | −0.001864 | 0.008078 | 0.016949 | 0.033288 |
| 150 | 0.081416 | 0.045139 | −0.05354 | −0.00922 | −0.021237 | 0.012467 | −0.004335 | −0.001907 | 0.017596 | −0.054766 | 0.028398 | 0.033713 | −0.021359 | −0.014327 |
| 151 | −0.033258 | 0.07987 | −0.028212 | 0.00215 | 0.009939 | −0.018484 | −0.023522 | −0.006481 | −0.037201 | −0.099484 | 0.011688 | −0.025393 | −0.025961 | −0.02696 |
| 152 | −0.149214 | −0.045893 | −0.006094 | 0.072005 | −0.055262 | 0.004974 | 0.00677 | 0.003467 | 0.007286 | 0.030128 | 0.005951 | 0.011605 | 0.048267 | 0.076613 |
| 153 | 0.042423 | 0.077347 | −0.008221 | −0.032111 | −0.019653 | 0.010395 | 0.004717 | −0.002154 | 0.000512 | 0.001748 | −0.035361 | 0.019999 | 0.036144 | 0.010518 |
| 154 | −0.05665 | 0.122765 | 0.012529 | −0.005066 | 0.015623 | 0.008852 | −0.002894 | 0.013007 | 0.042124 | −0.006131 | −0.074216 | 0.005064 | 0.050258 | 0.062425 |
| 155 | −0.044961 | 0.015791 | 0.028638 | 0.04987 | −0.009734 | 0.021764 | 0.024787 | −0.020957 | 0.048382 | −0.023912 | −0.00665 | 0.002126 | 0.042019 | 0.010414 |
| 156 | −0.124281 | 0.088321 | −0.000337 | 0.03874 | −0.020858 | −0.034385 | 0.001219 | −0.017732 | −0.006515 | −0.061338 | 0.087842 | −0.008465 | −0.006473 | −0.050366 |
| 157 | −0.019138 | 0.095291 | −0.027575 | −0.038686 | 0.084278 | −0.009056 | 0.02457 | 0.011908 | −0.020088 | −0.056087 | 0.027189 | −0.031857 | −0.028192 | 0.05822 |
| 158 | −0.016657 | −0.016634 | −0.001518 | −0.066868 | −0.027944 | −0.015791 | −0.009312 | 0.01967 | 0.071387 | −0.017988 | 0.015349 | −0.032161 | 0.034829 | −0.109756 |
| 159 | −0.0266 | −0.030664 | −0.00314 | 0.041703 | 0.066858 | −0.026581 | 0.007657 | 0.02885 | −0.018715 | −0.031319 | −0.043484 | −0.036038 | 0.003549 | 0.046828 |
| 160 | −0.048328 | 0.03638 | −0.005314 | −0.049943 | −0.039627 | 0.008321 | −0.00189 | −0.023829 | −0.011605 | −0.034709 | −0.052054 | −0.064052 | −0.004035 | 0.009507 |
| 161 | −0.071146 | −0.145513 | −0.050142 | −0.034787 | −0.060353 | 0.028392 | 0.015891 | −0.008444 | 0.041208 | −0.024349 | 0.033839 | 0.012291 | 0.019964 | 0.026623 |
| 162 | −0.134685 | 0.03127 | −0.032919 | 4.058276 | 0.025156 | −0.02501 | −0.019244 | 0.022181 | −0.027023 | 0.012427 | 0.033635 | 0.031962 | 0.013297 | −0.094555 |
| 163 | 0.01722 | −0.066339 | −0.007576 | 0.053568 | 0.000548 | −0.016284 | 0.010838 | 0.018844 | −0.037434 | −0.002219 | 0.043153 | −0.02687 | −0.033655 | −0.008805 |
| 164 | 0.052431 | −0.033592 | 0.027363 | 0.014682 | −0.039156 | −0.013844 | 0.009961 | −0.009684 | −0.057682 | 0.051038 | −0.039065 | 0.024366 | −0.00766 | −0.03231 |
| 165 | 0.16214 | 0.002244 | 0.008623 | −0.010086 | 0.030393 | 0.017164 | 0.00715 | −0.037594 | −0.011916 | −0.068468 | 0.036384 | 0.017091 | −0.029866 | −0.010265 |
| 166 | 0.025861 | −0.034419 | 0.010397 | −0.041581 | 0.009042 | 0.059478 | −0.005981 | 0.028202 | −0.029691 | 0.039546 | −0.003991 | −0.04655 | −0.000448 | −0.055674 |
| 167 | 0.009525 | 0.041228 | 0.057418 | 0.06299 | −0.117447 | 0.02474 | −0.00788 | 0.002562 | −0.002417 | −0.055342 | 0.024809 | −0.039894 | −0.011896 | −0.066504 |
| 168 | 0.046678 | −0.01776 | −0.032274 | 0.016183 | 0.046668 | −0.034253 | 0.029683 | 0.042992 | 0.008313 | 0.021941 | 0.03527 | −0.00559 | −0.010653 | 0.015617 |
| 169 | 0.021981 | −0.040527 | 0.019919 | 0.007792 | 0.01304 | −0.008704 | −0.021237 | 0.041007 | −0.004271 | 0.010982 | 0.024606 | −0.018767 | 0.008169 | −0.006644 |
| 170 | 0.03415 | 0.046173 | 0.012355 1 | 0.01963 | −0.036805 | −0.004383 | −0.036752 | 0.049201 | −0.003864 | 0.016844 | 0.037012 | −0.013817 | −0.018815 | 0.024783 |
| 171 | 0.014251 | −0.005823 | 0.015171 | 0.027095 | −0.017519 | −0.027343 | −0.002994 | 0.056746 | −0.002298 | 0.031233 | −0.009262 | −0.005571 | −0.012862 | −0.008642 |
| 172 | 0.022473 | −0.040732 | 0.02492 | 0.01041 | −0.001954 | −0.022765 | 0.019879 | −0.034383 | −0.020632 | −0.004052 | −0.001015 | −0.030049 | 0.048618 | −0.031143 |
| 173 | 0.050422 | 0.006637 | 0.004055 | −0.028884 | 0.043559 | −0.005097 | 0.014985 | −0.030918 | −0.02523 | −0.008255 | 0.020106 | −0.012582 | 0.046605 | −0.032896 |
| 174 | −0.041996 | −0.059607 | 0.004552 | 0.043047 | −0.079152 | 0.020207 | 0.014188 | −0.023519 | 0.021415 | 0.009743 | 0.030916 | −0.04424 | 0.041789 | 0.069653 |
| 175 | −0.040107 | 0.028882 | −0.038537 | −0.000975 | 0.090293 | 0.026385 | 0.027935 | 0.003381 | 0.030836 | −0.009583 | −0.005421 | 0.00277 | 0.018121 | 0.018491 |
| 176 | 0.029762 | −0.029489 | 0.000984 | 0.030836 | 0.048748 | −0.016255 | 0.003673 | −0.02088 | −0.00645 | 0.038053 | −0.001713 | −0.032772 | −0.069481 | −0.021578 |
| 177 | −0.008898 | 0.054516 | −0.066346 | −0.036452 | −0.073255 | 0.031459 | −0.002983 | 0.000939 | −0.001037 | 0.000033 | 0.042227 | −0.033774 | −0.051115 | 0.015309 |
| 178 | −0.049063 | −0.022825 | 0.009183 | 0.008081 | 0.060886 | −0.041114 | −0.053082 | 0.015281 | −0.027733 | 0.002587 | −0.004909 | −0.033646 | −0.030396 | 0.028167 |
| 179 | −0.035541 | −0.021027 | 0.01612 | 0.04182 | −0.028975 | −0.039812 | −0.044776 | 0.02178 | 0.003032 | 0.006614 | −0.001436 | 0.00567 | −0.032813 | 0.01399 |
| 180 | −0.087331 | −0.012008 | 0.013076 | −0.064992 | −0.012759 | −0.026094 | −0.061116 | 0.016427 | −0.006683 | 0.008603 | 0.00522 | −0.006782 | 0.004383 | 0.010423 |
| 181 | −0.054115 | 0.036543 | 0.012873 | −0.004643 | 0.014978 | −0.024509 | −0.067522 | 0.019647 | −0.000117 | −0.000885 | −0.001864 | −0.003585 | −0.008381 | 0.003588 |
| 182 | −0.006136 | 0.094159 | −0.016484 | −0.010212 | 0.036778 | −0.061115 | −0.040308 | 0.012964 | 0.007136 | −0.006672 | 0.029825 | 0.024512 | −0.01851 | −0.000497 |
| 183 | 0.081658 | 0.100657 | 0.009585 | −0.005012 | −0.031187 | −0.086487 | −0.002578 | 0.006029 | −0.00276 | 0.021205 | −0.019018 | 0.030876 | −0.063414 | −0.017124 |
| 184 | 0.11691 | −0.000135 | −0.011314 | −0.073541 | −0.040728 | −0.076651 | 0.005246 | −0.027015 | −0.043068 | 0.043781 | 0.037953 | 0.010793 | −0.007914 | −0.048469 |
| 185 | −0.043259 | −0.012174 | 0.028275 | −0.036551 | 0.005981 | −0.000261 | 0.005624 | −0.045909 | −0.067214 | 0.007466 | 0.037004 | 0.003914 | 0.080297 | 0.056065 |
| 186 | 0.056155 | −0.067058 | 0.013853 | −0.01228 | −0.030307 | −0.024895 | 0.017701 | −0.040683 | −0.062314 | 0.004748 | 0.032323 | 0.007559 | 0.044371 | 0.019489 |
| 187 | 0.040446 | −0.066299 | 0.020632 | −0.073264 | 0.031284 | −0.016375 | 0.007209 | −0.092307 | −0.023576 | −0.022346 | 0.008639 | 0.022102 | 0.037416 | −0.016169 |
| 188 | 0.031665 | −0.012011 | 0.019928 | −0.025019 | −0.007897 | −0.018779 | 0.012845 | −0.102381 | −0.008132 | −0.00078 | 0.029324 | −0.019251 | 0.015128 | −0.0019 |
| 189 | 0.060909 | 0.022062 | 0.005586 | 0.070596 | −0.006252 | −0.039831 | −0.004645 | −0.065841 | −0.001719 | 0.00358 | −0.020245 | 0.009109 | −0.009205 | −0.015209 |
| 190 | −0.035323 | 0.029008 | 0.022536 | −0.021967 | −0.026714 | −0.010532 | −0.034211 | 0.034301 | −0.015829 | −0.025089 | −0.020788 | 0.015699 | 0.005445 | 0.007953 |
| 191 | −0.102436 | −0.069146 | 0.031873 | 0.041395 | −0.037547 | 0.002659 | −0.030368 | −0.001988 | −0.006668 | −0.07315 | −0.034705 | 0.012303 | 0.037979 | 0.054697 |
| 192 | 0.060829 | −0.062362 | −0.02078 | −0.013375 | 0.006551 | −0.020452 | 0.017265 | −0.007024 | 0.061464 | 0.000405 | −0.009269 | 0.023698 | −0.018372 | 0.0568 |
| 193 | −0.000386 | 0.036298 | 0.010333 | 0.030832 | 0.030555 | −0.021199 | 0.022034 | −0.031687 | −0.0379 | 0.037703 | −0.012867 | 0.024279 | −0.033809 | 0.015092 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 194 | −0.015861 | 0.010866 | −0.003152 | −0.058671 | −0.058242 | 0.025069 | 0.001502 | −0.078688 | −0.025621 | 0.027218 | −0.024573 | 0.0027 | −0.061992 | −0.013591 |
| 195 | 0.009429 | 0.03258 | 0.006099 | 0.069581 | −0.002063 | 0.055824 | −0.000325 | 0.019452 | 0.01723 | 0.016782 | −0.015069 | 0.013789 | −0.019556 | −0.017057 |
| 196 | 0.008541 | −0.010035 | 0.002411 | −0.027928 | 0.061482 | −0.000099 | −0.030632 | 0.013627 | 0.024219 | 0.001752 | 0.010779 | −0.006269 | 0.014107 | −0.032159 |
| 197 | 0.081511 | −0.031401 | 0.019317 | 0.005047 | −0.03202 | −0.026699 | −0.01516 | 0.027246 | −0.013353 | −0.060335 | 0.017029 | 0.041896 | 0.013844 | 0.014982 |
| 198 | 0.062946 | 0.0572 | −0.019925 | −0.050017 | 0.038059 | −0.003428 | 0.009162 | 0.018211 | −0.026546 | 0.001528 | −0.030964 | −0.031511 | −0.0119 | 0.017915 |
| 199 | −0.023009 | −0.026852 | −0.009324 | 0.000765 | −0.056461 | 0.008619 | 0.001619 | 0.020953 | −0.03892 | −0.020522 | −0.042375 | −0.026941 | −0.015925 | 0.027619 |
| 200 | −0.014635 | −0.009144 | 0.014878 | −0.013842 | 0.005467 | −0.007206 | 0.021523 | 0.019854 | 0.019777 | 0.024659 | −0.092749 | 0.006041 | 0.007226 | −0.04172 |
| 201 | 0.028857 | 0.029176 | −0.025494 | −0.039951 | −0.103495 | −0.00042 | −0.024465 | −0.019281 | 0.049603 | 0.028069 | −0.017874 | 0.067638 | −0.04763 | 0.002319 |
| 202 | 0.026932 | 0.044691 | 0.022305 | 0.128266 | −0.034001 | −0.000917 | 0.014497 | 0.004341 | 0.017174 | −0.015399 | −0.065837 | −0.0305 | −0.030211 | 0.032075 |
| 203 | −0.041545 | 0.049697 | −0.04481 | 4.134787 | −0.098938 | −0.014161 | 0.022027 | 0.012075 | −0.00059 | 0.008897 | −0.042884 | −0.044418 | −0.011807 | 0.104247 |
| 204 | 0.003913 | −0.02847 | 0.035214 | −0.008386 | 0.043581 | −0.027174 | −0.012412 | 0.011345 | 0.001618 | −0.030083 | 0.016041 | 0.046563 | 0.10015 | −0.020232 |
| 205 | 0.048895 | −0.031002 | −0.02653 | −0.042194 | −0.056423 | 0.00807 | 0.021555 | −0.030061 | 0.026253 | −0.005091 | 0.001987 | −0.035555 | 0.033611 | 0.012619 |
| 206 | −0.059304 | 0.001141 | −0.018068 | −0.033734 | −0.063346 | −0.006704 | −0.003734 | 0.040273 | −0.055142 | −0.005991 | −0.033377 | 0.037322 | 0.044505 | −0.016656 |
| 207 | −0.042521 | 0.069667 | 0.013887 | 0.061158 | 0.046727 | −0.001054 | 0.012097 | 0.043119 | −0.012464 | 0.025898 | 0.034126 | −0.043285 | 0.046933 | −0.002429 |
| 208 | 0.021226 | −0.038835 | −0.003108 | 0.057008 | 0.042973 | 0.026172 | 0.026855 | −0.018031 | −0.057281 | 0.010144 | 0.054668 | 0.028267 | 0.094579 | 0.036581 |
| 209 | −0.025727 | 0.008591 | 0.042513 | 0.071106 | −0.019761 | 0.010327 | 0.032312 | 0.000088 | −0.017826 | 0.051566 | −0.024879 | −0.033011 | 0.047525 | 0.027526 |
| 210 | −0.093868 | 0.003548 | 0.002239 | −0.002495 | −0.020738 | 0.022878 | 0.003813 | 0.001715 | −0.017785 | −0.049791 | −0.069895 | 0.018255 | −0.000344 | 0.026461 |
| 211 | 0.034015 | −0.062651 | −0.008325 | −0.022504 | −0.031079 | −0.006401 | −0.00303 | 0.001671 | 0.011406 | −0.002943 | 0.028109 | 0.027543 | 0.011644 | −0.014535 |
| 212 | 0.081676 | 0.051514 | 0.052551 | −0.073102 | −0.092873 | 0.001457 | 0.004265 | −0.003049 | −0.042217 | −0.076053 | −0.009103 | 0.017867 | 0.029032 | −0.011238 |
| 213 | 0.028728 | −0.02409 | −0.01253 | −0.032418 | −0.084699 | −0.017581 | −0.025981 | −0.014479 | 0.014975 | 0.003646 | 0.015781 | −0.000097 | −0.021065 | −0.049283 |
| 214 | −0.047324 | −0.037217 | −0.007042 | −0.054178 | 0.047268 | −0.058328 | −0.047719 | 0.022325 | −0.009693 | 0.008448 | −0.006497 | −0.005343 | −0.020564 | −0.015006 |
| 215 | 0.045148 | 0.056358 | 0.005782 | −0.070611 | 0.058409 | −0.009046 | −0.034929 | 0.011664 | −0.006535 | −0.018633 | −0.024288 | −0.007759 | −0.027745 | 0.010874 |
| 216 | 0.012492 | −0.045241 | −0.018126 | 0.01147 | 0.02763 | −0.007087 | 0.008516 | 0.014734 | 0.010232 | −0.013276 | 0.00021 | −0.043863 | −0.022387 | −0.014573 |
| 217 | −0.052532 | 0.021394 | 0.016961 | 0.014676 | −0.012995 | −0.02967 | 0.02842 | 0.009943 | 0.060568 | −0.016944 | 0.004142 | −0.021531 | −0.011271 | 0.00864 |
| 218 | 0.031887 | 0.028801 | −0.008596 | −0.036274 | 0.02965 | 0.004809 | −0.004569 | 0.010548 | −0.01249 | 0.024548 | 0.00541 | −0.019981 | −0.018095 | −0.014227 |
| 219 | 0.006908 | 0.00978 | −0.004212 | −0.014802 | 0.023146 | 0.012772 | −0.005618 | 0.019875 | −0.002968 | 0.021067 | −0.009138 | −0.039216 | −0.016626 | −0.028713 |
| 220 | −0.049078 | −0.028975 | 0.005624 | −0.026527 | −0.081845 | −0.033247 | 0.00701 | 0.016301 | 0.014205 | −0.00027 | 0.020184 | 0.008077 | 0.007942 | −0.010378 |
| 221 | 0.021562 | 0.069717 | 0.02043 | 0.01406 | 0.025707 | 0.005528 | −0.001072 | 0.024865 | 0.022796 | −0.013407 | −0.013718 | −0.024405 | −0.020611 | −0.021123 |
| 222 | 0.01163 | 0.060266 | 0.014312 | −0.009289 | 0.029633 | −0.012145 | −0.001875 | 0.009829 | 0.006253 | −0.003952 | −0.003334 | −0.041346 | −0.005641 | −0.004451 |
| 223 | −0.056614 | 0.065182 | 0.007694 | 0.0183 | 0.021512 | 0.003839 | −0.01104 | 0.003884 | −0.029459 | −0.002565 | −0.017782 | −0.038637 | −0.036808 | −0.037343 |
| 224 | −0.054668 | −0.047058 | 0.004926 | 0.058441 | 0.032371 | 0.027014 | 0.001868 | −0.000777 | 0.029591 | −0.025599 | −0.034781 | −0.014339 | 0.002474 | 0.018468 |
| 225 | −0.021447 | 0.061978 | −0.018926 | −0.041425 | 0.056633 | 0.042536 | 0.000206 | 0.012379 | −0.009597 | −0.022721 | −0.030592 | −0.013846 | 0.023136 | 0.031715 |
| 226 | 0.052554 | 0.053574 | 0.002523 | −0.026189 | −0.005872 | 0.003137 | 0.011855 | −0.007295 | 0.003625 | 0.029214 | −0.021266 | 0.008499 | 0.03479 | 0.001928 |
| 227 | −0.052857 | 0.037038 | 0.030165 | −0.005016 | −0.021586 | 0.023709 | 0.013125 | −0.013128 | −0.012732 | −0.02878 | −0.011886 | 0.023109 | −0.011049 | −0.003113 |
| 228 | 0.088842 | −0.021636 | 0.027275 | 0.034505 | −0.011369 | 0.024324 | 0.007327 | 0.012527 | 0.037753 | 0.04005 | 0.005648 | 0.025556 | 0.00154 | 0.04151 |
| 229 | −0.080661 | 0.047036 | −0.013417 | −0.069301 | −0.024707 | 0.022788 | −0.024312 | 0.007078 | −0.030216 | 0.013061 | 0.020503 | 0.027487 | −0.010582 | 0.01881 |
| 230 | 0.076006 | 0.025692 | 0.022821 | 0.065308 | −0.016279 | 0.013492 | −0.013743 | −0.031545 | −0.0082 | −0.007986 | 0.030549 | −0.011496 | −0.018792 | −0.000098 |
| 231 | 0.080996 | 0.025447 | 0.009505 | −0.019465 | −0.028744 | −0.006001 | 0.004235 | 0.000854 | −0.012197 | 0.002789 | 0.05984 | 0.014054 | 0.020021 | −0.067362 |
| 232 | −0.075396 | 0.085934 | 0.062147 | 0.011261 | −0.039485 | −0.006863 | −0.012541 | 0.001285 | 0.00434 | −0.003773 | −0.030726 | −0.006302 | −0.010814 | −0.023684 |
| 233 | 0.089109 | −0.081331 | 0.0462 | 0.027885 | −0.03467 | 0.005563 | 0.015081 | −0.03168 | −0.007544 | −0.021985 | −0.056101 | −0.00129 | −0.008348 | 0.005949 |
| 234 | 0.019369 | −0.059739 | −0.041602 | −0.036766 | −0.045391 | 0.010356 | 0.004261 | 0.009719 | −0.028871 | −0.001238 | −0.020278 | 0.00804 | 0.011579 | −0.010494 |
| 235 | −0.03086 | −0.017298 | 0.006305 | 0.013369 | 0.083158 | 0.010911 | 0.007163 | −0.00327 | −0.041899 | −0.010946 | 0.019457 | −0.007323 | −0.010795 | 0.005264 |
| 236 | 0.010111 | −0.038833 | 0.01783 | 0.039915 | 0.012771 | −0.006863 | 0.00598 | −0.050774 | −0.039719 | 0.038096 | −0.012824 | 0.010675 | −0.003068 | −0.039603 |
| 237 | 0.018796 | 0.007986 | −0.015755 | −0.048461 | 0.039997 | −0.008335 | −0.03127 | 0.008555 | 0.004226 | 0.008829 | −0.015404 | 0.046277 | 0.025219 | −0.025509 |
| 238 | −0.02668 | 0.034711 | −0.022609 | 0.006522 | −0.000354 | 0.029737 | −0.019741 | −0.009285 | 0.007573 | −0.016817 | −0.019365 | 0.029501 | −0.002445 | −0.030337 |
| 239 | −0.003151 | 0.002327 | −0.014498 | −0.025479 | −0.019653 | 0.026093 | 0.012593 | −0.017128 | 0.009663 | 0.00718 | 0.013563 | −0.02657 | −0.003766 | 0.020223 |
| 240 | −0.026189 | 0.000028 | −0.003108 | 0.070549 | −0.025761 | 0.021692 | 0.016311 | 0.018902 | 0.035309 | −0.026542 | −0.030828 | −0.032582 | 0.014197 | 0.014304 |
| 241 | 0.009769 | −0.08846 | 0.004691 | 0.095059 | 0.016873 | 0.023033 | 0.011726 | 0.006781 | 0.03695 | −0.002758 | −0.019421 | −0.024779 | −0.014997 | 0.022281 |
| 242 | −0.038178 | 0.020419 | 0.002152 | −0.029717 | 0.020125 | −0.017183 | 0.006384 | −0.018986 | −0.04463 | 0.010243 | −0.046481 | 0.008855 | 0.01311 | −0.002689 |
| 243 | 0.045641 | −0.024966 | 0.016558 | 0.050065 | −0.037932 | −0.007261 | −0.006644 | −0.003295 | −0.018303 | −0.019716 | 0.022248 | 0.00336 | −0.007191 | 0.012556 |
| 244 | 0.020785 | 0.030374 | 0.003941 | −0.062334 | −0.053431 | 0.006308 | 0.002124 | 0.008094 | −0.006908 | −0.005283 | −0.012102 | −0.01549 | −0.015487 | 0.014222 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 245 | −0.002461 | 0.084994 | 0.015138 | 0.035293 | −0.005412 | −0.000581 | 0.015687 | −0.049551 | −0.004809 | −0.025917 | 0.032202 | −0.060391 | −0.044896 | −0.01 |
| 246 | −0.06193 | 0.004488 | −0.023016 | −0.058567 | 0.07899 | −0.018077 | 0.006009 | −0.021227 | −0.017375 | −0.027442 | −0.017925 | 0.018737 | 0.014473 | 0.015876 |
| 247 | 0.032542 | −0.027824 | −0.005415 | −0.013395 | 0.024114 | −0.000441 | −0.00217 | −0.020424 | −0.004775 | 0.007441 | −0.001144 | 0.004163 | −0.012202 | −0.011773 |
| 248 | 0.06101 | 0.106588 | 0.027466 | 0.045029 | −0.019244 | 0.007074 | −0.013269 | 0.005997 | −0.012785 | 0.002977 | 0.027357 | 0.027913 | −0.021987 | −0.044228 |
| 249 | 0.032299 | 0.030334 | −0.022859 | −0.074172 | −0.00279 | −0.012456 | 0.002015 | 0.009577 | 0.01406 | 0.02028 | 0.046681 | −0.026285 | −0.009494 | −0.024685 |
| 250 | −0.020292 | −0.052362 | −0.047431 | −0.030685 | 0.040677 | 0.00926 | 0.008715 | 0.020582 | 0.043142 | −0.002779 | −0.00887 | 0.013865 | −0.002911 | −0.024951 |
| 251 | −0.024851 | 0.062708 | 0.001027 | 0.049377 | 0.014823 | 0.01605 | −0.001831 | 0.012017 | −0.007014 | −0.019274 | −0.041438 | 0.003534 | 0.043394 | 0.033973 |
| 252 | 0.000776 | 0.027631 | −0.008669 | −0.010974 | −0.011218 | −0.020462 | −0.004077 | −0.008429 | 0.004193 | 0.012622 | −0.000477 | −0.005997 | 0.028029 | 0.029063 |
| 253 | −0.057191 | −0.06211 | 0.026423 | −0.009647 | −0.012696 | −0.00867 | −0.011759 | 0.001787 | 0.015234 | 0.014228 | −0.011764 | 0.000324 | −0.005705 | −0.027603 |
| 254 | −0.068109 | 0.018893 | −0.01514 | −0.017685 | −0.009625 | 0.021492 | −0.002063 | 0.004039 | −0.045966 | −0.012219 | 0.001666 | −0.010216 | −0.009535 | 0.016274 |
| 255 | 0.044706 | 0.005304 | 0.0083341 | 0.035001 | −0.0092 | 0.007024 | −0.002617 | 0.013241 | −0.002481 | −0.034991 | −0.011835 | 0.023249 | −0.006899 | 0.024217 |
| 256 | −0.023959 | −0.036503 | −0.007608 | −0.048533 | 0.013114 | 0.004472 | −0.002313 | 0.023616 | 0.07252 | −0.024553 | 0.057906 | 0.000265 | −0.03899 | −0.001742 |
| 257 | 0.002163 | −0.048944 | 0.009244 | 0.047203 | 0.021449 | −0.001807 | −0.004167 | 0.004849 | 0.014977 | 0.004473 | 0.019164 | 0.021248 | −0.023202 | −0.015033 |
| 258 | −0.001924 | 0.003437 | 0.025355 | 0.095612 | 0.016198 | 0.028372 | −0.008838 | 0.014741 | 0.002762 | 0.013438 | 0.01379 | −0.000059 | 0.006019 | 0.014093 |
| 259 | 0.066348 | 0.033238 | −0.005182 | −0.000907 | 0.00684 | −0.004287 | −0.001734 | −0.010072 | −0.001234 | 0.020679 | 0.00257 | −0.0121 | 0.023372 | 0.003322 |
| 260 | 0.057648 | −0.040911 | −0.024007 | −0.024054 | 0.004951 | −0.013254 | −0.021946 | 0.007392 | 0.004909 | 0.062436 | 0.022697 | −0.01492 | 0.061465 | 0.005308 |
| 261 | −0.008158 | 0.079121 | −0.009303 | 0.014431 | −0.020125 | 0.005309 | −0.012096 | 0.026389 | 0.008937 | 0.01388 | −0.006375 | 0.010824 | 0.054502 | 0.011693 |
| 262 | −0.0414531 | 0.017348 | −0.013622 | −0.10972 | 0.036944 | −0.030597 | −0.0123 | 0.020677 | 0.011941 | 0.010894 | −0.000385 | −0.010338 | −0.000136 | −0.007995 |
| 263 | −0.025812 | 0.043245 | −0.003958 | −0.020508 | 0.016581 | −0.048576 | −0.008087 | −0.014413 | 0.0016531 | −0.006426 | −0.008571 | −0.004076 | −0.015454 | −0.01534 |
| 264 | 0.023594 | −0.054586 | 0.015927 | 0.025188 | 0.045311 | −0.024973 | 0.012596 | 0.00927 | 0.039515 | −0.015777 | 0.008941 | −0.009053 | −0.00522 | −0.030722 |
| 265 | 4.033075 | 4.060729 | −0.021047 | −0.028268 | −0.027329 | 0.014173 | 0.020693 | 0.031212 | 0.023185 | −0.004613 | 0.017625 | −0.002178 | −0.016487 | 0.005751 |
| 266 | 0.008855 | −0.070893 | −0.02854 | 0.00689 | 0.013604 | 0.014684 | 0.01325 | 0.024997 | −0.006664 | −0.016238 | 0.037723 | 0.023235 | 0.0065021 | −0.007873 |
| 267 | −0.129961 | 0.025816 | −0.035001 | −0.015437 | −0.055938 | 0.003419 | −0.004618 | 0.047318 | 0.027368 | 0.038795 | −0.011638 | 0.012567 | 0.032165 | −0.033149 |
| 268 | 0.05153 | −0.030759 | −0.011563 | −0.04506 | 0.012403 | −0.003294 | 0.02068 | −0.002694 | 0.0074881 | 0.0164411 | −0.030234 | −0.010595 | 0.0092611 | 0.009875 |
| 269 | 0.0074811 | −0.005111 | −0.006744 | −0.018126 | 0.01631 | −0.001379 | 0.002858 | 0.009241 | −0.009489 | 0.005891 | −0.012774 | 0.008042 | 0.017712 | −0.015248 |
| 270 | −0.003682 | 0.028543 | 0.014364 | 0.049194 | −0.031688 | 0.000927 | 0.010628 | 0.015113 | −0.008701 | 0.005553 | 0.000635 | 0.005354 | 0.021144 | 0.005816 |
| 271 | −0.063521 | −0.017791 | −0.024394 | 0.019506 | 0.035273 | −0.035587 | 0.019842 | −0.015896 | −0.009855 | −0.012443 | −0.004134 | 0.032389 | −0.036716 | 0.011647 |
| 272 | −0.060478 | 0.033952 | 0.003601 | 0.078185 | −0.010074 | 0.032317 | −0.014079 | 0.019617 | 0.013025 | 0.033463 | −0.00093 | 0.026067 | −0.007109 | 0.005648 |
| 273 | 0.066406 | −0.013863 | 0.029578 | 0.053166 | −0.022032 | 0.011637 | −0.002128 | 0.003507 | 0.015047 | 0.022426 | 0.016586 | −0.016202 | −0.009815 | 0.027881 |
| 274 | 0.037471 | −0.029039 | 0.029057 | 0.063128 | −0.023347 | 0.012402 | −0.007956 | 0.004273 | 0.012549 | 0.018579 | 0.023111 | −0.009418 | −0.003996 | 0.024606 |
| 275 | −0.015 | 0.038507 | 0.020885 | 0.066245 | 0.032752 | 0.00695 | −0.000912 | −0.008739 | −0.024879 | −0.010142 | 0.043863 | −0.012178 | −0.004036 | −0.026423 |
| 276 | −0.058863 | −0.077265 | −0.015226 | −0.06201 | 0.028889 | 0.006015 | −0.000296 | −0.035209 | −0.047712 | 0.050775 | −0.012808 | −0.003364 | 0.011111 | −0.027114 |
| 277 | 0.018909 | −0.018847 | 0.004494 | 0.058086 | 0.017448 | 0.005935 | −0.003329 | −0.017034 | −0.016024 | 0.021282 | 0.001564 | −0.009081 | −0.008428 | 0.017058 |
| 278 | 0.01207 | 0.001768 | 0.000445 | −0.012856 | 0.001335 | −0.001865 | −0.003931 | 0.002264 | −0.031041 | 0.0095971 | 0.0227881 | −0.003317 | 0.0214421 | 0.010258 |
| 279 | −0.0365681 | 0.0066331 | −0.01924 | 0.000403 | −0.033991 | 0.029537 | 0.007628 | 0.01304 | 0.012464 | 0.015457 | −0.000314 | −0.01322 | 0.015445 | 0.010038 |
| 280 | 0.136004 | −0.025942 | 0.039372 | 0.052162 | 0.053827 | −0.004888 | −0.001091 | 0.024619 | 0.015228 | −0.025731 | 0.017354 | −0.013355 | −0.033536 | −0.030854 |
| 281 | 0.052746 | 0.056491 | −0.0049 | 0.02502 | −0.022144 | −0.030929 | 0.009111 | −0.027267 | −0.030524 | −0.026207 | 0.01532 | −0.012671 | 0.0031911 | 0.028378 |
| 282 | −0.012827 | 0.0032821, | −0.005737 | 0.00891 | −0.005427 | −0.032222 | 0.013149 | −0.014184 | −0.055256 | −0.038868 | 0.042259 | −0.012008 | 0.015621 | 0.038448 |
| 283 | −0.043655 | −0.012526 | 0.009523 | 0.009683 | −0.019573 | −0.011675 | −0.00105 | 0.00923 | −0.013755 | 0.015318 | 0.0260321 | 0.0005921 | 0.0230551 | −0.002827 |
| 284 | −0.03161 | −0.084451 | 0.001173 | −0.026673 | 0.016849 | −0.008177 | 0.000369 | 0.013821 | 0.009956 | 0.013005 | 0.008732 | 0.011372 | 0.004591 | −0.02024 |
| 285 | −0.048967 | −0.097514 | −0.002124 | −8.094822 | 0.009554 | −0.015873 | −0.005181 | 0.000115 | 0.005659 | 0.00856 | 0.007478 | 0.002475 | 0.014478 | 0.011748 |
| 286 | −0.012758 | 0.009535 | −0.016589 | −0.144049 | 0.010753 | 0.003952 | −0.013276 | 0.026071 | −0.012263 | −0.004056 | 0.013564 | −0.00016 | 0.0197 | −0.002909 |
| 287 | −0.035748 | 0.030527 | 0.015619 | 0.017584 | −0.030486 | −0.003521 | −0.011561 | 0.016393 | −0.021791 | −0.018333 | 0.030763 | −0.002809 | 0.020255 | 0.017835 |
| 288 | −0.015381 | −0.0371171 | −0.0028081 | −0.005777 | −0.003203 | 0.001609 | −0.006491 | 0.00808 | −0.010886 | 0.0088871 | −0.017967 | 0.0273461 | 0.071641 | 0.034944 |
| 289 | −0.0373581 | 0.0019671 | −0.03263 | −0.050455 | 0.049891 | −0.005811 | 0.009858 | 0.02845 | −0.020051 | 0.0040841 | −0.008593 | −0.008348 | −0.00351 | 0.033215 |
| 290 | 0.03334 | 0.046815 | −0.056399 | 0.050594 | −0.036692 | −0.007443 | 0.032586 | −0.014101 | −0.013495 | 0.011257 | −0.007675 | 0.018306 | 0.011662 | 0.002122 |
| 291 | 0.01736 | 0.049024 | −0.066691 | 0.018655 | −0.024768 | −0.006482 | 0.03443 | −0.008887 | −0.011831 | 0.009485 | −0.003115 | 0.019603 | 0.020933 | −0.005919 |
| 292 | −0.050076 | 0.062744 | −0.05658 | 0.050607 | 0.081264 | 0.007635 | 0.028366 | −0.006946 | −0.007426 | −0.011183 | −0.03168 | 0.01638 | 0.009488 | −0.012656 |
| 293 | 0.001934 | −0.016905 | −0.011251 | −0.050645 | 0.03333 | 0.005476 | 0.027409 | −0.022583 | 0.022154 | −0.058418 | −0.061147 | −0.002358 | 0.019778 | −0.017203 |
| 294 | 0.031143 | −0.0413341 | 0.001497 | −0.028758 | 0.023446 | 0.002611 | 0.023848 | −0.000276 | −0.006006 | 0.0025221 | 0.0064291 | −0.046147 | 0.0220761 | −0.004831 |
| 295 | 0.019499 | −0.010882 | −0.0009741 | −0.080106 | 0.02267 | 0.00702 | 0.010887 | 0.011879 | 0.010121 | −0.031398 | 0.054327 | −0.023903 | −0.023435 | −0.005398 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 296 | −0.059876 | 0.072886 | 0.006464 | −0.034442 | 0.006421 | 0.010891 | −0.000804 | −0.000673 | 0.017008 | −0.013062 | 0.039514 | −0.041563 | 0.018713 | 0.018546 |
| 297 | −0.021375 | −0.045806 | −0.019014 | −0.020891 | 0.039522 | −0.01032 | −0.001864 | 0.007785 | −0.012791 | −0.019439 | 0.050208 | −0.05247 | −0.017684 | −0.009317 |
| 298 | −0.035923 | 0.055369 | −0.020874 | 0.081651 | −0.013422 | −0.051328 | −0.031635 | 0.013524 | −0.065628 | −0.023727 | −0.009443 | −0.03837 | −0.016256 | −0.064968 |
| 299 | 0.039642 | −0.082545 | 0.013634 | 0.04327 | 0.002593 | 0.001164 | −0.002624 | −0.009127 | −0.023329 | −0.024472 | 0.032248 | −0.027676 | −0.000356 | −0.001425 |
| 300 | −0.018888 | −0.051598 | 0.043677 | −0.001754 | −0.023438 | −0.054057 | −0.058183 | 0.02743 | −0.070298 | −0.011834 | 0.032117 | −0.042122 | −0.050686 | −0.011933 |
| 301 | 0.034307 | −0.021365 | 0.000467 | −0.007346 | 0.009724 | −0.013584 | 0.012977 | 0.009627 | −0.003843 | −0.011955 | 0.011848 | −0.009884 | −0.020932 | −0.002769 |
| 302 | 0.046485 | 0.011288 | 0.006536 | −0.019731 | 0.081432 | 0.002167 | 0.001877 | 0.028158 | 0.016241 | −0.005065 | 0.05896 | −0.016733 | −0.032226 | −0.010074 |
| 303 | −0.0002151 | −0.0347711 | 0.0047071 | −0.050605 | 0.004696 | 0.021109 | 0.003929 | −0.005709 | −0.027396 | −0.003396 | 0.021378 | −0.052672 | 0.006702 | −0.018111 |
| 304 | 0.029397 | 0.0343571 | 0.033523 | 0.002238 | 0.001981 | 0.018546 | −0.007144 | −0.011383 | −0.005344 | 0.0022671 | −0.004985 | −0.016269 | 0.0111411 | −0.004149 |
| 305 | −0.0907871 | 0.0494561 | 0.0175521 | 0.108975 | 0.020288 | −0.026276 | 0.039587 | −0.058215 | −0.002367 | −0.069278 | −0.001002 | −0.024306 | 0.002269 | 0.02868 |
| 306 | −0.017977 | 0.019001 | 0.006642 | 0.087337 | −0.030652 | 0.005032 | 0.00659 | 0.04302 | 0.040469 | 0.041822 | −0.013474 | 0.000715 | −0.027437 | −0.018528 |
| 307 | −0.05981 | −0.065128 | −0.022446 | −0.007019 | 0.002211 | 0.037715 | 0.004808 | 0.008388 | −0.015546 | 0.012255 | −0.034399 | −0.014214 | −0.064944 | −0.044607 |
| 308 | 0.003516 | −0.028245 | 0.024481 | 0.065084 | −0.008911 | −0.016709 | −0.027773 | −0.017826 | 0.021833 | 0.012778 | −0.045075 | 0.017158 | 0.014102 | 0.003861 |
| 309 | 0.011674 | 0.030377 | −0.010964 | 0.017877 | 0.002877 | −0.018616 | −0.011947 | −0.016763 | −0.023036 | 0.012688 | 0.019138 | 0.020309 | −0.000498 | −0.012502 |
| 310 | −0.033624 | −0.005765 | −0.006711 | −0.031488 | −0.043288 | −0.020542 | 0.005357 | −0.024596 | −0.000116 | 0.030129 | 0.012334 | 0.000064 | −0.008063 | −0.021718 |
| 311 | 0.028678 | 0.071816 | −0.008156 | −0.050482 | −0.028317 | 0.005097 | 0.015105 | 0.00318 | −0.010558 | 0.006405 | −0.035281 | −0.016486 | 0.000236 | 0.043506 |
| 312 | 0.018822 | 0.002057 | 0.003248 | 0.024179 | −0.009375 | 0.007775 | −0.021676 | −0.025039 | −0.012918 | −0.004563 | 0.012236 | −0.082225 | −0.002091 | 0.003074 |
| 313 | 0.034221 | 0.044232 | 0.002858 | 0.061719 | −0.020949 | −0.000642 | −0.010698 | −0.001655 | −0.002521 | 0.014132 | 0.002641 | 0.028213 | −0.047469 | −0.007227 |
| 314 | −0.083119 | 0.017154 | −0.025462 | 0.022229 | −0.002856 | −0.023927 | 0.026529 | −0.04955 | −0.026838 | −0.009448 | 0.041931 | −0.051485 | 0.004911 | −0.034824 |
| 315 | −0.017327 | 0.011209 | −0.00916 | 0.034428 | −0.0309 | −0.003017 | −0.016351 | −0.008229 | −0.011575 | −0.019969 | 0.023258 | 0.011301 | −0.034509 | 0.029643 |
| 316 | −0.000199 | −0.138491 | −0.026127 | −0.043598 | −0.055068 | 0.025755 | −0.01277 | 0.009888 | 0.006512 | 0.034301 | 0.047757 | −0.013274 | 0.044356 | −0.062425 |
| 317 | −0.04009 | 0.050895 | −0.003285 | 0.039749 | −0.07152 | −0.012439 | −0.002352 | −0.022868 | −0.011821 | 0.000281 | 0.026505 | 0.006289 | −0.031139 | 0.023954 |
| 318 | −0.040722 | 0.082299 | 0.039708 | 0.027808 | 0.003711 | 0.008261 | −0.007356 | −0.030091 | −0.007872 | 0.019233 | −0.083125 | −0.002952 | −0.009332 | 0.043602 |
| 319 | −0.039734 | 0.001708 | −0.011864 | −0.020335 | 0.059498 | −0.004022 | −0.016949 | −0.008089 | −0.022975 | −0.011236 | 0.0262391 | −0.001145 | −0.014285 | −0.002832 |
| 320 | −0.069076 | −0.034761 | 0.00316 | 0.065246 | 0.014972 | 0.037447 | 0.00811 | −0.005638 | 0.023754 | −0.016514 | 0.013173 | −0.009033 | 0.016581 | 0.055834 |
| 321 | 0.019455 | −0.11794 | −0.009733 | 0.051654 | 0.003223 | 0.007186 | 0.017306 | 0.032363 | 0.013763 | 0.045943 | −0.009375 | 0.01107 | −0.026725 | 0.035777 |
| 322 | 0.084988 | 0.004799 | 0.015573 | 0.007857 | −0.054614 | −0.016041 | 0.003799 | −0.03028 | 0.002027 | 0.011947 | −0.06225 | 0.028657 | 0.030159 | 0.03807 |
| 323 | 0.11907 | 0.026568 | −0.031945 | 0.018796 | 0.072726 | −0.006911 | 0.00699 | 0.067773 | 0.018559 | −0.001385 | −0.026691 | 0.019068 | −0.030661 | −0.066379 |
| 324 | −0.004793 | −0.05432 | −0.043741 | −0.091273 | −0.06467 | 0.002256 | 0.017984 | 0.02007 | −0.028112 | 0.043184 | −0.017269 | −0.020714 | 0.051257 | 0.003687 |
| 325 | 0.04313 | 0.016471 | −0.022437 | −0.040811 | −0.002593 | −0.003425 | 0.001149 | 0.003728 | 0.006692 | 0.056985 | 0.025983 | 0.021539 | 0.015281 | −0.01832 |
| 326 | 0.02781 | 0.023501 | 0.026737 | 8.121725 | 0.004135 | 0.014003 | 0.004504 | −0.017222 | 0.04698 | 0.004347 | 0.049927 | −0.022245 | −0.026588 | −0.006336 |
| 327 | −0.055628 | 0.025552 | 0.022035 | 0.040758 | 0.000918 | 0.00207 | −0.011099 | −0.014754 | −0.007282 | −0.019252 | −0.033621 | 0.018743 | 0.042034 | 0.020461 |
| 328 | 0.105992 | −0.013634 | −0.004362 | −0.081922 | 0.009205 | −0.035024 | −0.011616 | −0.044895 | 0.064944 | −0.013525 | 0.037024 | −0.033801 | −0.002236 | 0.041357 |
| 329 | 0.044965 | −0.030798 | 0.005899 | −0.009087 | 0.039945 | −0.01147 | −0.003694 | −0.022452 | −0.010379 | 0.011834 | 0.023521 | 0.008374 | 0.003478 | 0.003759 |
| 330 | −0.024466 | −0.002356 | −0.018155 | −0.049485 | −0.032348 | −0.027583 | 0.008796 | 0.001198 | 0.071998 | −0.011838 | 0.008888 | −0.00774 | −0.012051 | 0.001918 |
| 331 | −0.009209 | −0.046008 | −0.026109 | −0.052684 | 0.075372 | −0.00113 | 0.004681 | 0.016041 | −0.002742 | 0.001387 | −0.012262 | −0.002725 | 0.02149 | −0.02791 |
| 332 | −0.087833 | −0.014457 | 0.034978 | 0.05994 | −0.036562 | 0.014111 | 0.009211 | −0.004233 | −0.011065 | 0.019013 | 0.03421 | −0.014022 | 0.016206 | 0.029545 |
| 333 | 0.03356 | 0.005222 | −0.016651 | −0.012628 | 0.022418 | 0.000373 | 0.006413 | 0.009588 | −0.00939 | 0.016675 | 0.009059 | 0.017916 | 0.015376 | 0.001875 |
| 334 | 0.023052 | −0.077045 | −0.013237 | −0.079203 | −0.027404 | −0.023762 | −0.020252 | −0.015568 | −0.008916 | −0.025696 | 0.045401 | 0.011081 | −0.026992 | 0.015553 |
| 335 | 0.07885 | −0.08003 | 0.016266 | −0.012674 | 0.038091 | 0.017045 | −0.0101 | 0.001529 | −0.007294 | 0.016272 | −0.01563 | 0.010811 | 0.027453 | −0.027862 |
| 336 | −0.00466 | 0.025491 | 0.026309 | 0.012981 | −0.020481 | −0.008207 | −0.020841 | 0.027835 | 0.011181 | 0.009757 | −0.009702 | −0.015203 | 0.013927 | 0.039049 |
| 337 | −0.056623 | 0.02759 | −0.038038 | −0.046592 | −0.031129 | 0.019046 | 0.00611 | 0.025499 | 0.000537 | −0.023042 | −0.024872 | −0.010168 | −0.008032 | 0.046042 |
| 338 | 0.029019 | 0.012065 | 0.009733 | −0.066314 | −0.01173 | 0.018086 | 0.002242 | −0.030243 | −0.021468 | −0.022459 | −0.059767 | −0.000677 | −0.005303 | −0.016573 |
| 339 | −0.003926 | 0.177326 | −0.027991 | −0.14706 | −0.014421 | 0.028419 | 0.018893 | 0.014914 | 0.036301 | 0.06295 | −0.006038 | −0.042827 | −0.043898 | 0.033194 |
| 340 | −0.041204 | −0.084619 | 0.015411 | 0.003572 | 0.064411 | 0.003462 | −0.013856 | −0.029173 | 0.013188 | −0.019565 | −0.0252 | 0.030957 | 0.051 | −0.070689 |

| | DF | DG | DH | DI | DJ | DK | DL | DM | DN | DO | DP | DQ | DR | DS |
|---|---|---|---|---|---|---|---|---|---|---|---|---|---|---|
| 1 | −0.0645441 | −0.0888571 | −0.0254331 | −0.022942 | −0.007185 | 0.066906 | 0.126224 | 0.056396 | 0.0820581 | 0.1733351 | 0.0618511 | 0.051621 | −0.028761 | −0.019779 |
| 2 | −0.013115 | 0.103368 | 0.012368 | −0.01299 | −0.158235 | −0.140226 | 0.015196 | −0.112743 | 0.113431 | 0.010051 | −0.043622 | 0.064816 | 0.095508 | −0.03772 |
| 3 | 0.092127 | 0.037115 | −0.015949 | −0.141453 | −0.019367 | 0.012982 | −0.101564 | −0.002555 | −0.09426 | −0.034334 | −0.086574 | −0.026933 | −0.029022 | −0.016234 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 4 | 0.041338 | −0.005658 | 0.05445 | 0.127266 | −0.001766 | 0.026672 | 0.040711 | 0.036685 | 0.023221 | −0.118783 | 0.015214 | −0.005987 | −0.082732 | −0.01113 |
| 5 | 0.099561 | 0.064475 | 0.023048 | 0.035779 | 0.064482 | 0.001342 | −0.115286 | 0.06611 | 0.01064 | 0.101171 | 0.000835 | −0.027273 | −0.007979 | 0.018656 |
| 6 | 0.000161 | 0.052132 | 0.046341 | −0.133087 | 0.038742 | 0.036386 | 0.01385 | −0.036469 | 0.036983 | 0.063855 | 0.046192 | 0.008348 | 0.018258 | −0.005204 |
| 7 | 0.018001 | 0.079453 | −0.09553 | 0.054273 | −0.046181 | −0.066227 | 0.030759 | 0.107594 | −0.040011 | 0.0154771 | −0.078781 | −0.032981 | −0.060003 | 0.032417 |
| 8 | 0.043197 | −0.0102471 | 0.039629 | 0.011513 | 0.00394 | −0.014946 | 0.048673 | 0.053132 | 0.062277 | −0.017755 | −0.065957 | 0.028467 | 0.038754 | −0.067184 |
| 9 | −0.14057 | 0.000381 | −0.035686 | 0.002698 | −0.012776 | −0.108515 | −0.010093 | 0.018473 | 0.008902 | 0.017218 | −0.013363 | −0.003908 | 0.081567 | 0.079988 |
| 10 | 0.017297 | 0.094608 | −0.000945 | 0.115335 | 0.066584 | −0.063824 | 0.150896 | 0.017172 | −0.026862 | 0.065866 | 0.103502 | −0.017659 | −0.022975 | −0.019799 |
| 11 | 0.098663 | 0.034121 | −0.022393 | 0.01585 | 0.053314 | 0.053853 | 0.019321 | 0.060507 | −0.024749 | −0.031951 | −0.026877 | −0.032043 | 0.008202 | −0.044937 |
| 12 | −0.024111 | 0.001982 | −0.03792 | 0.029035 | 0.053592 | −0.031112 | −0.025236 | 0.01025 | 0.020821 | 0.044925 | 0.036485 | −0.001895 | 0.03868 | 0.02009 |
| 13 | 0.101617 | −0.079476 | −0.094414 | −0.036932 | −0.015002 | 0.104086 | −0.0816 | −0.174303 | 0.022022 | 0.111488 | 0.063137 | 0.020904 | 0.046693 | −0.009817 |
| 14 | −0.04146 | 0.03389 | 0.075644 | 0.0868871 | −0.029864 | −0.012696 | 0.084232 | 0.157318 | −0.05153 | −0.077482 | 0.04532 | −0.044785 | −0.011446 | −0.016468 |
| 15 | −0.033307 | −0.000654 | −0.117592 | 0.033694 | −0.098052 | −0.043861 | −0.01645 | −0.139907 | 0.079685 | −0.003339 | 0.02216 | 0.034109 | −0.005474 | 0.033441 |
| 16 | 0.049544 | 0.041962 | 0.10026 | −0.05321 | 0.019814 | −0.029628 | 0.000462 | 0.033443 | 0.010185 | 0.070931 | −0.028144 | 0.035937 | 0.002617 | −0.006955 |
| 17 | −0.118141 | 0.007553 | 0.035675 | 0.032657 | −0.015255 | −0.108805 | 0.015592 | 0.034614 | 0.000931 | −0.087366 | −0.089481 | −0.002224 | −0.008881 | −0.064173 |
| 18 | −0.1568651 | 0.062241 | 0.021966 | 0.027965 | 0.014091 | 0.02193 | −0.095517 | −0.016269 | 0.004694 | −0.000304 | −0.011488 | 0.026054 | −0.015895 | 0.033697 |
| 19 | −0.002585 | 0.012752 | −0.040126 | −0.006565 | −0.005747 | −0.114171 | −0.06362 | 0.005574 | 0.008587 | 0.075814 | −0.002742 | 0.016708 | −0.002771 | 0.105541 |
| 20 | 0.118028 | 0.073784 | −0.007009 | 0.021461 | 0.086932 | 0.236335 | 0.038308 | −0.00007 | −0.010921 | 0.025308 | −0.045433 | −0.050395 | 0.01538 | −0.038169 |
| 21 | 0.114195 | 0.08736 | 0.015454 | −0.019988 | −0.08838 | −0.055476 | −0.071864 | 0.068378 | −0.033367 | −0.099859 | −0.000514 | −0.072379 | 0.017487 | −0.132298 |
| 22 | 0.043068 | 0.022857 | −0.018493 | −0.049345 | −0.079035 | 0.165092 | −0.157759 | −0.014481 | −0.032852 | 0.0751551 | 0.0056531 | −0.002421 | −0.005055 | 0.127766 |
| 23 | 0.056358 | 0.052828 | −0.017975 | 0.062271 | −0.058001 | 0.064391 | 0.095635 | 0.088478 | 0.039339 | −0.031673 | 0.032257 | 0.028974 | −0.031811 | −0.015894 |
| 24 | 0.037095 | −0.060671 | 0.041396 | −0.084403 | 0.058278 | −0.018263 | 0.047557 | −0.095567 | 0.003661 | −0.008528 | −0.055416 | 0.030676 | 0.003102 | −0.033954 |
| 25 | 0.015279 | −0.115997 | 0.049937 | 0.157399 | 0.015718 | 0.014227 | −0.03707 | 0.071819 | 0.054881 | −0.031443 | 0.064186 | 0.047417 | 0.026359 | −0.022469 |
| 26 | −0.133545 | 0.146933 | 0.06025 | 0.012453 | −0.062233 | −0.047012 | 0.079218 | −0.069404 | 0.02359 | −0.006279 | −0.033708 | 0.004658 | −0.014016 | −0.029355 |
| 27 | 0.02359 | 0.042313 | 0.00026 | −0.035571 | −0.11938 | −0.065661 | 0.06362 | −0.067274 | 0.0037 | 0.162169 | 0.026925 | −0.01554 | 0.01671 | 0.000304 |
| 28 | 0.054549 | 0.011204 | 0.094336 | −0.134049 | 0.159101 | 0.012937 | −0.081528 | 0.033569 | 0.056123 | 0.010183 | −0.029092 | 0.051074 | 0.053504 | −0.063884 |
| 29 | 0.01012 | 0.059341 | −0.037477 | −0.016465 | 0.01746 | 0.038631 | 0.031413 | 0.033603 | −0.033648 | −0.008368 | 0.065768 | −0.021429 | 0.023672 | 0.010209 |
| 30 | −0.055703 | 0.028477 | 0.021973 | 0.050781 | −0.067264 | −0.127938 | 0.029202 | −0.052999 | 0.082385 | −0.025029 | −0.036777 | 0.071964 | 0.074322 | 0.048501 |
| 31 | 0.004564 | −0.000826 | 0.010978 | 0.005467 | 0.053954 | 0.013303 | −0.111635 | 0.05865 | −0.065686 | −0.064517 | 0.058938 | −0.038457 | −0.048545 | −0.07966 |
| 32 | −0.043443 | 0.007424 | 0.000307 | −0.026753 | −0.055276 | 0.008858 | 0.084004 | −0.012914 | −0.004809 | 0.02627 | −0.007529 | 0.035006 | 0.009855 | −0.094098 |
| 33 | −0.0536911 | −0.0277151 | −0.044543 | 0.100969 | 0.047206 | −0.024845 | −0.067596 | −0.01517 | 0.062953 | 0.028062 | −0.020252 | 0.001043 | −0.02433 | −0.021678 |
| 34 | 0.029596 | −0.040929 | −0.035831 | 0.039013 | 0.103722 | 0.003839 | −0.011069 | 0.045885 | 0.044738 | −0.039887 | −0.071348 | 0.022895 | 0.009728 | 0.027147 |
| 35 | −0.156917 | −0.117449 | −0.067103 | −0.016014 | −0.122431 | −0.037914 | 0.006469 | −0.061635 | −0.050809 | −0.080305 | 0.014887 | −0.028699 | −0.04474 | −0.053146 |
| 36 | 0.018222 | −0.050725 | −0.036494 | −0.112032 | −0.050742 | 0.019174 | −0.047958 | 0.121019 | −0.019453 | −0.098277 | 0.02473 | 0.033394 | 0.012443 | −0.003765 |
| 37 | −0.047344 | 0.1075721 | −0.0147271 | 0.011651 | 0.0112 | −0.037635 | −0.022554 | 0.014783 | 0.0019691 | −0.013464 | −0.000646 | 0.0040321 | −0.022737 | 0.043042 |
| 38 | −0.040205 | −0.015572 | 0.022552 | −0.011684 | −0.020953 | −0.066456 | 0.063248 | −0.02177 | −0.068281 | 0.054295 | 0.011007 | −0.111146 | −0.051522 | −0.031238 |
| 39 | 0.124218 | 0.00198 | −0.062102 | 0.032564 | −0.080319 | −0.035808 | −0.094155 | −0.076703 | −0.010532 | 0.009 | 0.034629 | 0.002718 | −0.006535 | 0.064078 |
| 40 | 0.022516 | −0.201059 | −0.210878 | −0.023504 | −0.143109 | 0.087915 | −0.059245 | −0.004094 | 0.025162 | 0.084064 | −0.048587 | −0.005074 | −0.044189 | −0.005708 |
| 41 | 0.013156 | 0.078559 | 0.044052 | 0.00184 | 0.128246 | −0.073878 | 0.09392 | 0.03791 | −0.023215 | −0.157402 | 0.085551 | 0.044262 | 0.066443 | −0.041974 |
| 42 | −0.019356 | −0.011326 | −0.024106 | 0.000155 | 0.01846 | 0.016305 | 0.008796 | −0.008679 | −0.00732 | 0.029632 | −0.011238 | −0.01441 | −0.001168 | 0.013275 |
| 43 | 0.031591 | 0.027114 | −0.031037 | 0.034299 | 0.022855 | −0.128779 | −0.014471 | 0.011284 | −0.033418 | 0.023902 | 0.071265 | −0.030758 | 0.033465 | 0.01937 |
| 44 | 0.110444 | 0.153575 | −0.046268 | 0.006821 | 0.062161 | −0.141365 | −0.123258 | −0.014665 | −0.021984 | −0.061712 | 0.048398 | −0.086909 | −0.051406 | −0.022165 |
| 45 | 0.044803 | −0.129642 | 0.091186 | 0.011423 | −0.077966 | 0.024494 | 0.164053 | 0.112207 | −0.040022 | 0.089622 | 0.025365 | −0.019675 | −0.062301 | 0.049727 |
| 46 | −0.077571 | 0.027739 | 0.058855 | −0.100792 | 0.012858 | 0.010444 | 0.003793 | −0.010271 | −0.060601 | 0.06403 | −0.037656 | −0.081411 | −0.072401 | −0.043247 |
| 47 | −0.03744 | −0.050132 | −0.057473 | 0.011596 | 0.020325 | 0.021383 | −0.078293 | −0.085012 | 0.003457 | −0.076697 | 0.014245 | 0.001772 | −0.042307 | −0.044043 |
| 48 | −0.040778 | −0.025488 | −0.021802 | −0.105086 | −0.034398 | −0.062516 | −0.032883 | −0.014373 | −0.064974 | 0.062001 | 0.04993 | −0.177115 | −0.10128 | −0.020766 |
| 49 | −0.049622 | −0.026037 | 0.052851 | −0.139775 | −0.083053 | 0.055139 | −0.085621 | −0.030715 | −0.04399 | −0.04228 | −0.028125 | −0.056836 | 0.01123 | 0.023159 |
| 50 | 0.005042 | 0.166758 | −0.123112 | 0.045896 | −0.147117 | 0.01127 | 0.07196 | −0.071433 | −0.143137 | 0.046267 | 0.055927 | −0.061811 | −0.041595 | 0.02962 |
| 51 | 0.092039 | 0.039462 | 0.197346 | 0.028234 | −0.009467 | −0.062462 | 0.071142 | 0.031336 | 0.019637 | 0.122095 | 0.085126 | −0.009787 | −0.028542 | 0.146634 |
| 52 | −0.060396 | 0.008066 | −0.059234 | 0.119117 | −0.012033 | 0.158115 | −0.01821 | 0.031811 | 0.03714 | 0.064646 | −0.014543 | −0.078146 | 0.000727 | −0.035825 |
| 53 | −0.07703 | −0.109392 | 0.058951 | 0.031322 | −0.109815 | −0.010963 | −0.088297 | 0.078254 | 0.047497 | 0.02415 | −0.004712 | 0.037722 | 0.022204 | −0.041981 |
| 54 | −0.119871 | −0.104119 | −0.026458 | 0.048713 | 0.016872 | 0.085255 | 0.060343 | −0.085634 | 0.015019 | −0.106388 | −0.002954 | −0.023047 | −0.01429 | −0.019204 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 55 | −0.039535 | 0.019818 | −0.182279 | 0.020342 | 0.031557 | −0.048927 | 0.152102 | 0.095558 | 0.053012 | 0.007785 | −0.107024 | 0.043099 | 0.028201 | 0.066746 |
| 56 | 0.025181 | 0.102131 | −0.074731 | −0.014814 | −0.03874 | 0.052693 | −0.018113 | −0.036059 | 0.054426 | −0.076347 | −0.074144 | −0.003053 | 0.040022 | −0.04647 |
| 57 | 0.010816 | 0.081481 | −0.042137 | 0.048562 | 0.073856 | −0.051825 | −0.005666 | −0.032669 | −0.049475 | −0.136047 | 0.000606 | −0.031085 | 0.023586 | 0.042985 |
| 58 | 0.126056 | −0.174091 | 0.010534 | 0.02069 | 0.017852 | −0.034288 | −0.016705 | −0.003509 | 0.052807 | −0.087564 | −0.006668 | 0.093016 | 0.147833 | −0.001671 |
| 59 | −0.027369 | 0.032326 | −0.036153 | 0.046223 | 0.01799 | 0.201006 | −0.018591 | 0.059389 | −0.047817 | 0.0043 | 0.04657 | 0.005568 | −0.004417 | −0.029057 |
| 60 | −0.05295 | 0.137995 | 0.012833 | 0.039672 | −0.068678 | −0.001483 | −0.055217 | 0.003265 | 0.052509 | 0.03468 | 0.008421 | 0.015325 | 0.064541 | 0.009282 |
| 61 | −0.015478 | 0.014392 | 0.020487 | −0.059896 | −0.018252 | 0.020928 | 0.012047 | −0.102337 | 0.008422 | 0.143608 | 0.055579 | 0.063464 | −0.034427 | −0.06096 |
| 62 | 0.043388 | 0.034462 | 0.008946 | 0.095393 | −0.066347 | 0.029511 | 0.00388 | 0.068473 | 0.007758 | 0.001615 | 0.014475 | −0.039703 | −0.039352 | 0.030917 |
| 63 | 0.026043 | 0.017115 | 0.053514 | −0.060605 | −0.027027 | 0.033957 | 0.00083 | 0.076357 | −0.041293 | −0.034057 | −0.086244 | −0.040705 | −0.077173 | 0.029333 |
| 64 | −0.020178 | 0.023639 | −0.057565 | −0.003543 | −0.045134 | −0.069105 | −0.027237 | −0.032315 | 0.088251 | 0.10526 | 0.026981 | 0.093639 | 0.038349 | −0.101832 |
| 65 | 0.126509 | −0.058942 | 0.12353 | 0.068546 | −0.039621 | −0.006829 | −0.05051 | −0.032824 | −0.024511 | 0.067355 | −0.064565 | −0.017134 | −0.0257 | 0.001091 |
| 66 | 0.044985 | −0.065091 | 0.021885 | −0.034077 | −0.098303 | −0.035205 | −0.089959 | 0.089857 | 0.046057 | 0.003961 | −0.01471 | 0.015915 | 0.062438 | 0.034223 |
| 67 | 0.09239 | 0.028938 | −0.078509 | 0.063748 | −0.024773 | −0.00408 | 0.081678 | −0.086716 | 0.064738 | −0.005558 | −0.019609 | 0.086392 | 0.108613 | 0.065197 |
| 68 | −0.134808 | 0.061317 | 0.02209 | 0.134465 | −0.011656 | 0.047368 | 0.033745 | −0.056874 | −0.015974 | 0.025116 | 0.02419 | −0.001316 | −0.007472 | 0.00793 |
| 69 | 0.131276 | 0.028767 | 0.120763 | −0.063847 | −0.03517 | −0.026192 | 0.009719 | 0.103533 | −0.043295 | −0.048914 | −0.047584 | −0.03067 | −0.034333 | 0.056825 |
| 70 | −0.154349 | 0.118782 | −0.026255 | 0.031651 | −0.0074 | 0.062119 | −0.145702 | −0.111259 | 0.017062 | 0.058824 | 0.041711 | 0.030118 | −0.009034 | −0.034378 |
| 71 | 0.083372 | −0.122926 | −0.048778 | −0.026488 | 0.013033 | 0.065039 | −0.000248 | −0.083774 | −0.061702 | 0.029704 | 0.011953 | 0.020962 | 0.01052 | −0.012302 |
| 72 | 0.00059 | −0.037671 | 0.023355 | 0.1348 | 0.070182 | 0.045107 | −0.029358 | −0.161532 | −0.002593 | −0.038181 | −0.024566 | −0.042686 | 0.019073 | 0.030155 |
| 73 | −0.129661 | −0.029682 | 0.035441 | −0.043106 | 0.011771 | −0.006699 | −0.037756 | 0.064551 | −0.007015 | −0.095283 | −0.034987 | 0.0356741 | 0.0735731 | −0.069666 |
| 74 | −0.039341 | −0.006226 | 0.025721 | −0.0298 | 0.0280−42 | −0.066704 | −0.017484 | 0.053976 | 0.092434 | 0.026643 | −0.01712 | 0.07322 | 0.003652 | 0.05696 |
| 75 | −0.161867 | −0.004672 | −0.070478 | 0.047687 | −0.05083 | −0.024254 | −0.07684 | −0.080897 | −0.048923 | −0.083746 | −0.071172 | 0.000471 | 0.004449 | 0.053247 |
| 76 | −0.043949 | 0.007599 | 0.030345 | 0.049012 | −0.008535 | −0.022775 | 0.048441 | −0.117183 | −0.036663 | −0.073453 | −0.039377 | 0.019827 | −0.030881 | −0.067605 |
| 77 | 0.029028 | −0.06127 | 0.122152 | −0.038191 | 0.058899 | −0.111166 | −0.010755 | 0.04825 | 0.014708 | 0.012609 | 0.067104 | 0.007913 | −0.011827 | 0.053454 |
| 78 | 0.035928 | 0.088206 | −0.057187 | −0.120083 | 0.020355 | 0.041099 | 0.076749 | 0.134073 | 0.106068 | 0.058313 | −0.012638 | 0.052482 | 0.072444 | −0.092312 |
| 79 | 0.080575 | −0.093128 | 0.053783 | 0.027314 | 0.110363 | −0.023522 | 0.046458 | 0.029031 | 0.036072 | 0.030235 | −0.068623 | −0.062484 | −0.01131 | 0.103991 |
| 80 | −0.050811 | −0.05373 | 0.07788 | 0−.019071 | −0.0253 | 0.071625 | 0.070488 | −0.021601 | −0.019636 | −0.064518 | −0.030671 | 0.004105 | 0.028444 | −0.00289 |
| 81 | −0.115051 | −0.011744 | 0.004161 | 0.080273 | 0.022179 | 0.114483 | 0.023256 | 0.046397 | 0.073085 | −0.004628 | 0.002472 | 0.062291 | 0.130325 | −0.029593 |
| 82 | 0.05602 | −0.0337051 | −0.094111 | 0.045691 | −0.025433 | −0.004354 | 0.05533 | −0.024989 | 0.069907 | −0.003002 | 0.130234 | 0.084799 | −0.003562 | 0.016451 |
| 83 | 0.0308591 | −0.1032291 | −0.0759841 | −0.038771 | 0.089094 | −0.126839 | −0.012949 | 0.043097 | −0.046495 | 0.0286471 | −0.001601 | 0.033945 | −0.040608 | −0.036329 |
| 84 | −0.072491 | −0.0558481 | −0.041057 | 0.098091 | −0.01176 | 0.122504 | −0.073298 | 0.058973 | −0.012406 | 0.0869031 | −0.022295 | 0.0088861 | 0.1587151 | 0.071149 |
| 85 | 0.065108 | 0.023305 | 0.026961 | −0.015076 | −0.098511 | 0.019223 | 0.047024 | −0.092324 | −0.015494 | 0.053874 | 0.058556 | −0.026831 | −0.025586 | −0.018314 |
| 86 | −0.057655 | 0.037283 | −0.040922 | −0.046506 | 0.033833 | −0.011182 | 0.069059 | 0.100113 | 0.149886 | 0.073869 | −0.0267 | 0.0725 | 0.043704 | 0.113174 |
| 87 | −0.005731 | 0.076689 | −0.067339 | −0.05501 | 0.129961 | 0.005716 | 0.076655 | −0.057276 | −0.014095 | −0.001055 | −0.057129 | −0.083154 | −0.083613 | 0.078897 |
| 88 | 0.025674 | −0.024234 | 0.031344 | −0.012656 | 0.05989 | 0.13253 | −0.110642 | 0.013696 | 0.003569 | −0.12094 | −0.009284 | 0.006098 | −0.070069 | 0.047769 |
| 89 | −0.124173 | 0.098335 | 0.118061 | −0.045126 | −0.081799 | −0.008885 | 0.06858 | −0.001086 | −0.016791 | −0.058319 | −0.073749 | 0.025998 | 0.001307 | 0.020261 |
| 90 | −0.0991071 | −0.099805 | 0.1064231 | −0.032756 | −0.111976 | −0.128812 | −0.032965 | −0.080034 | 0.039079 | −0.062305 | 0.029049 | −0.043421 | 0.103587 | 0.00445 |
| 91 | −0.016992 | 0.057362 | −0.04594 | 0.11567 | −0.070514 | −0.114466 | −0.050596 | 0.129109 | −0.072321 | −0.01944 | −0.09057 | −0.03783 | −0.074786 | −0.080625 |
| 92 | 0.096059 | −0.162883 | 0.02817 | 0.069406 | −0.060609 | −0.052342 | −0.031142 | 0.01188 | −0.038345 | 0.077082 | −0.013226 | −0.061961 | −0.032313 | 0.015164 |
| 93 | 0.023233 | 0.007066 | 0.106575 | −0.071727 | 0.095448 | −0.093534 | 0.019744 | −0.015148 | −0.093859 | −0.002949 | 0.037579 | −0.030313 | −0.10412 | −0.035563 |
| 94 | 0.02215 | 0.00984 | 0.035525 | 0.125489 | −0.083342 | −0.047855 | −0.036089 | 0.055135 | 0.0405921 | −0.029327 | 0.0189751 | 0.0093761 | 0.0260571 | 0.032488 |
| 95 | −0.031843 | −0.011016 | 0.042256 | 0.006694 | −0.077611 | 0.008076 | 0.03703 | 0.03057 | 0.067184 | −0.094259 | 0.00782 | 0.001798 | 0.033872 | −0.04913 |
| 96 | 0.028982 | −0.110578 | 0.022205 | 0.031765 | −0.040583 | −0.031566 | 0.01482 | 0.14366 | −0.035906 | −0.021873 | −0.034423 | 0.092749 | 0.093353 | −0.02716 |
| 97 | 0.052409 | 0.064532 | −0.039885 | 0.028584 | 0.10927 | 0.079361 | 0.068004 | −0.027637 | 0.020702 | 0.004753 | −0.040222 | −0.00302 | 0.012839 | 0.032111 |
| 98 | −0.051316 | 0.117365 | 0.058188 | −0.067507 | −0.053873 | −0.022326 | 0.030754 | −0.051383 | 0.141367 | 0.045794 | 0.107712 | 0.040582 | 0.001683 | −0.013594 |
| 99 | −0.087148 | −0.061474 | 0.006766 | 0.011952 | 0.035192 | −0.042493 | 0.041508 | −0.039313 | −0.062978 | −0.025848 | 0.0078181 | −0.007609 | −0.084042 | 0.07002 |
| 100 | −0.0371071 | −0.017034 | −0.0269171 | 0.027846 | 0.022424 | 0.020745 | 0.000452 | −0.021385 | −0.035185 | −0.00053 | −0.022922 | −0.041746 | −0.03387 | 0.052181 |
| 101 | −0.006419 | −0.013412 | −0.009912 | 0.00972 | 0.002356 | −0.0013 | −0.024927 | −0.012067 | 0.009073 | 0.01571 | 0.00775 | 0.008349 | 0.000329 | 0.017912 |
| 102 | 0.00139 | 0.04821 | −0.020577 | −0.023832 | −0.005953 | 0.056233 | 0.039257 | 0.007255 | −0.046597 | 0.023531 | 0.048531 | −0.034037 | −0.064289 | −0.021875 |
| 103 | −0.010099 | −0.012963 | 0.010671 | −0.037048 | −0.013454 | 0.007721 | 0.040686 | 0.02807 | −0.040036 | 0.101842 | −0.018611 | −0.019144 | −0.02813 | 0.005619 |
| 104 | −0.054037 | 0.062869 | −0.026852 | −0.033075 | 0.00495 | −0.029545 | 0.02215 | 0.074678 | −0.023147 | −0.023223 | −0.001266 | −0.014479 | 0.0012521 | 0.007844 |
| 105 | 0.00956 | 0.032575 | −0.001972 | −0.033306 | −0.028449 | 0.017192 | −0.01547 | −0.022557 | 0.010637 | 0.07281 | 0.04252 | 0.041264 | 0.007023 | 0.029813 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 106 | 0.025557 | −0.032046 | −0.022079 | −0.042319 | −0.025428 | 0.021259 | −0.019889 | −0.040273 | −0.00011 | 0.067893 | 0.018205 | −0.009624 | −0.009691 | −0.015931 |
| 107 | −0.019465 | 0.006009 | −0.047061 | 0.021132 | −0.061798 | −0.038075 | −0.071422 | −0.086673 | −0.024755 | 0.034903 | −0.027596 | −0.047006 | 0.017499 | −0.023697 |
| 108 | −0.06261 | −0.054331 | −0.123069 | −0.126359 | −0.04608 | −0.078051 | −0.076772 | −0.045004 | 0.000838 | 0.025275 | −0.037979 | −0.036998 | 0.06683 | 0.049984 |
| 109 | 0.464164 | 0.008392 | −0.031505 | 0.031413 | −0.072498 | 0.009529 | 0.024156 | −0.095663 | 0.019105 | −0.067474 | −0.044596 | 0.017113 | 0.016703 | −0.02602 |
| 110 | 0.028195 | 0.476368 | 0.004694 | 0.014574 | −0.005404 | 0.035684 | −0.034555 | 0.034505 | 0.024357 | 0.01925 | −0.026845 | 0.047049 | 0.015851 | 0.007909 |
| 111 | 0.026425 | −0.0007 | 0.588814 | 0.034841 | −0.048109 | 0.091644 | −0.018136 | −0.081516 | −0.033876 | 0.032959 | −0.001381 | −0.0074 | −0.001235 | 0.002761 |
| 112 | 0.032571 | 0.016339 | 0.03102 | 0.621168 | 0.025087 | −0.046761 | −0.037517 | −0.032193 | 0.022617 | 0.055154 | −0.03113 | 0.005235 | 0.009506 | −0.049387 |
| 113 | −0.029646 | −0.023163 | −0.03442 | 0.006518 | 0.570826 | −0.054214 | 0.004633 | −0.031598 | 0.00624 | 0.015195 | 0.03173 | 0.004896 | 0.021661 | −0.01236 |
| 114 | −0.06052 | 0.038293 | 0.051937 | −0.006054 | −0.046963 | 0.464418 | 0.018321 | −0.000927 | 0.004017 | −0.055699 | 0.019839 | −0.003335 | 0.002905 | 0.018602 |
| 115 | 0.0075951 | −0.05637 | −0.043424 | −0.009415 | −0.019213 | 0.054385 | 0.622599 | −0.081527 | −0.041405 | −0.067547 | −0.010218 | −0.042396 | 0.012648 | −0.031712 |
| 116 | −0.048377 | −0.000362 | −0.096864 | 0.00512 | −0.045573 | 0.019471 | −0.023159 | 0.524432 | −0.012268 | 0.039024 | 0.06192 | −0.005372 | 0.007765 | 0.004747 |
| 117 | 0.049003 | 0.01815 | 0.026087 | −0.001236 | 0.012047 | 0.010127 | −0.02278 | −0.000241 | 0.736051 | −0.05371 | −0.008641 | −0.15316 | −0.150578 | −0.027627 |
| 118 | −0.05079 | −0.003218 | 0.051081 | 0.045184 | 0.050109 | −0.027068 | −0.001681 | 0.054041 | −0.087174 | 0.571757 | −0.0587 | −0.011395 | 0.014243 | −0.079874 |
| 119 | −0.041386 | −0.014188 | −0.031433 | −0.011192 | −0.001456 | 0.004571 | −0.026361 | 0.039557 | −0.005573 | −0.050577 | 0.767318 | −0.008708 | 0.007896 | 0.001455 |
| 120 | 0.023799 | 0.064195 | 0.015778 | −0.001487 | −0.00236 | 0.016704 | −0.014216 | −0.034202 | −0.139042 | −0.001007 | −0.023332 | 0.804006 | −0.131889 | 0.005011 |
| 121 | 0.037784 | 0.044008 | 0.015175 | −0.018868 | 0.039148 | −0.015081 | 0.02609 | 0.000068 | −0.12857 | 0.014246 | 0.00332 | −0.121158 | 0.749119 | −0.007867 |
| 122 | −0.001387 | 0.02832 | 0.001851 | −0.01382 | −0.01081 | 0.025151 | 0.001068 | 0.004416 | 0.001773 | −0.069862 | 0.005565 | 0.00698 | −0.006881 | 0.755545 |
| 123 | 0.021292 | −0.045714 | 0.001784 | 0.039875 | 0.026565 | −0.010151 | −0.028504 | 0.015146 | −0.008263 | −0.034517 | −0.054105 | 0.002921 | −0.029491 | −0.113853 |
| 124 | −0.000661 | −0.0170981 | −0.010622 | −0.037712 | 0.016717 | 0.025834 | −0.0081 | −0.004586 | 0.0052171 | −0.033076 | −0.119781 | 0.0041321 | 0.0015641 | −0.023188 |
| 125 | 0.0122 | 0.039302 | 0.034325 | −0.029704 | −0.033186 | 0.003548 | 0.004128 | 0.003606 | 0.01126 | −0.009006 | 0.06292 | −0.011009 | −0.00183 | −0.006842 |
| 126 | 0.001809 | 0.011987 | 0.005761 | 0.011915 | −0.032446 | −0.011791 | 0.001256 | −0.004796 | −0.018767 | −0.042491 | 0.001515 | −0.001884 | −0.042623 | −0.057566 |
| 127 | −0.027979 | −0.014288 | 0.031378 | −0.008221 | −0.00528 | −0.008027 | −0.021234 | 0.019038 | −0.034835 | −0.053472 | −0.017949 | −0.01421 | −0.020287 | −0.049236 |
| 128 | −0.004578 | −0.047982 | 0.03426 | 0.040872 | −0.030668 | 0.011624 | −0.013097 | 0.000018 | −0.019797 | 0.004049 | −0.035917 | −0.017686 | 0.022451 | 0.024433 |
| 129 | −0.001608 | −0.036511 | −0.006607 | −0.047167 | −0.006334 | 0.016536 | −0.001442 | 0.035584 | −0.007247 | −0.030935 | −0.025597 | −0.002734 | −0.008663 | −0.066281 |
| 130 | −0.083846 | 0.0322931 | 0.012141 | −0.022955 | 0.052654 | −0.010127 | −0.039811 | 0.017558 | 0.0714591 | 0.025391 | −0.031086 | −0.003262 | 0.0182091 | 0.056364 |
| 131 | 0.034268 | −0.0501391 | −0.056292 | 0.058239 | −0.018688 | 0.035632 | 0.059616 | −0.023347 | −0.040898 | −0.014664 | −0.033662 | −0.032755 | −0.042447 | 0.022114 |
| 132 | −0.010609 | −0.001339 | −0.033986 | 0.008432 | 0.01845 | 0.01285 | 0.000982 | −0.017629 | −0.016544 | 0.025799 | −0.020807 | −0.043387 | −0.004132 | 0.005905 |
| 133 | −0.044752 | −0.016621 | 0.022941 | 0.007511 | 0.034069 | 0.005749 | 0.030862 | −0.008807 | −0.056779 | 0,013049 | −0.046282 | −0.01874 | −0.043756 | 0.036523 |
| 134 | 0.032011 | 0.035136 | −0.048837 | −0.028893 | 0.03189 | 0.033398 | −0.020045 | −0.056517 | −0.033951 | −0.058281 | −0.009673 | 0.004682 | −0.006441 | −0.045908 |
| 135 | 0.029487 | 0.026744 | 0.023661 | −0.021163 | 0.012545 | 0.032628 | 0.004361 | −0.007073 | −0.003087 | 0.017766 | −0.030393 | −0.022477 | 0.024691 | 0.024503 |
| 136 | 0.023939 | 0.004387 | −0.052793 | 0.033809 | −0.047535 | 0.103207 | −0.045859 | −0.07107 | 0.008736 | 0.029604 | −0.023689 | −0.00455 | −0.009277 | 0.016126 |
| 137 | 0.023195 | −0.033844 | −0.01602 | 0.040474 | −0.080142 | −0.018021 | 0.040445 | 0.029006 | 0.012175 | −0.004895 | 0.01687 | 0.038281 | 0.014612 | 0.009021 |
| 138 | −0.011053 | 0.031841 | −0.006543 | 0.00403 | −0.06596 | 0.0145 | 0.050928 | −0.001788 | 0.01811 | −0.021747 | −0.033104 | −0.00756 | −0.007689 | −0.050091 |
| 139 | −0.004594 | −0.067414 | −0.01669 | 0.033095 | −0.049282 | −0.020347 | 0.024072 | 0.038196 | 0.022477 | 0.005882 | −0.067916 | −0.014639 | −0.033078 | −0.005787 |
| 140 | 0.031392 | 0.060889 | 0.009905 | −0.051144 | 0.010364 | 0.018556 | 0.00071 | 0.015971 | −0.038437 | −0.0038 | 0.050902 | 0.047454 | 0.050806 | −0.022896 |
| 141 | 0.06105 1 | −0.0166771 | 0.046985 | −0.006858 | 0.073666 | −0.010777 | 0.025554 | 0.007004 | 0.041491 | 0.051505 | 0.009438 | 0.032518 | 0.04001 | −0.008343 |
| 142 | −0.026819 | 0.016403 | 0.033889 | 0.00259 | 0.026947 | −0.066246 | −0.008785 | −0.010433 | −0.040398 | −0.056558 | −0.029938 | 0.00022 | −0.025907 | −0.017266 |
| 143 | 0.021992 | 0.050015 | 0.035525 | −0.026055 | 0.04911 | −0.014512 | 0.0127 | 0.013461 | 0.015872 | 0.033168 | 0.002507 | −0.004485 | −0.012003 | −0.074009 |
| 144 | 0.017785 | −0.026065 | 0.008343 | −0.0136 | −0.012188 | 0.031566 | −0.013101 | −0.014637 | 0.028768 | 0.056001 | −0.087358 | 0.021693 | 0.028232 | −0.019185 |
| 145 | −0.000392 | 0.024734 | −0.005735 | 0.047172 | −0.028834 | −0.041432 | 0.035448 | 0.019459 | −0.005733 | 0.019667 | −0.018431 | −0.000718 | 0.003454 | −0.024903 |
| 146 | 0.057911 | 0.010418 | 0.024738 | −0.007107 | −0.02186 | 0.01857 | 0.016196 | −0.021838 | −0.010358 | 0.029536 | −0.008124 | −0.030581 | 0.019571 | 0.025318 |
| 147 | 0.004734 | 0.080651 | 0.053449 | −0.052419 | −0.059336 | −0.061667 | 0.028022 | −0.011254 | 0.006724 | −0.021403 | 0.022445 | −0.005193 | −0.013041 | −0.013158 |
| 148 | 0.068089 | −0.033314 | −0.007376 | 0.029684 | −0.089265 | −0.009161 | −0.035775 | −0.018038 | −0.01624 | −0.049261 | −0.00151 | 0.010876 | 0.045128 | −0.003497 |
| 149 | 0.043428 | 0.004594 | 0.0125 | −0.009909 | 0.021126 | 0.012833 | −0.03983 | −0.002584 | −0.033786 | −0.038591 | 0.038443 | −0.015931 | −0.023324 | −0.044663 |
| 150 | −0.016427 | 0.080501 | 0.070422 | −0.075741 | −0.070779 | 0.026945 | 0.002569 | −0.023713 | 0.049393 | −0.0519 | 0.004545 | −0.051366 | 0.033072 | −0.02971 |
| 151 | 0.059797 | −0.004045 | −0.030607 | 0.019264 | 0.016678 | −0.023213 | −0.020027 | −0.029678 | −0.049867 | 0.021712 | −0.028378 | −0.024716 | −0.047978 | −0.035243 |
| 152 | 0.01659 | −0.002739 | −0.00626 | −0.061881 | −0.036147 | −0.01511 | −0.002947 | 0.020635 | −0.004566 | −0.009262 | −0.041075 | 0.011865 | −0.06651 | −0.007895 |
| 153 | −0.000052 | −0.049526 | 0.044419 | −0.0106 | −0.009679 | 0.015039 | −0.0076 | −0.020739 | 0.050214 | −0.002526 | −0.018725 | 0.020619 | 0.030262 | −0.012683 |
| 154 | 0.004694 | −0.000465 | −0.02826 | 0.020252 | −0.031378 | 0.049968 | −0.014343 | −0.000783 | 0.039305 | 0.032719 | −0.012778 | 0.034765 | 0.028278 | 0.022587 |
| 155 | −0.002871 | −0.000078 | −0.047053 | 0.021352 | 0.023095 | 0.000466 | 0.001568 | 0.029999 | 0.009744 | −0.042651 | −0.007137 | −0.008676 | −0.015983 | 0.024143 |
| 156 | −0.046544 | 0.0349741 | 0.013755 | 0.019464 | 0.020792 | 0.026306 | −0.020358 | −0.025243 | −0.010012 | −0.008314 | −0.029311 | −0.05228 | −0.027048 | 0.035842 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 157 | 0.039715 | 0.036882 | −0.040468 | 0.046209 | −0.044847 | 0.023099 | −0.035213 | −0.011771 | −0.038438 | 0.023858 | −0.022613 | −0.024004 | 0.018999 | −0.005 |
| 158 | −0.057952 | −0.027921 | −0.040717 | −0.005386 | −0.009042 | −0.060817 | −0.0229 | 0.035508 | 0.005035 | 0.035386 | 0.00112 | −0.041925 | −0.04444 | −0.004572 |
| 159 | −0.072504 | −0.020815 | 0.033254 | −0.003988 | 0.036999 | 0.025246 | 0.030041 | −0.042894 | 0.034569 | 0.012153 | 0.020131 | 0.01257 | 0.006529 | 0.017859 |
| 160 | −0.042372 | −0.068592 | 0.030472 | −0.085619 | −0.074422 | −0.04101 | 0.100506 | 0.005427 | 0.0124 | −0.016535 | −0.045874 | −0.043856 | −0.052698 | −0.039031 |
| 161 | −0.014044 | −0.031233 | 0.05395 | −0.019111 | 0.038379 | −0.058261 | 0.017845 | −0.077769 | −0.004114 | 0.014276 | −0.027409 | −0.010207 | −0.005572 | 0.022471 |
| 162 | 0.014803 | 0.016493 | −0.028181 | −0.034161 | 0.00307 | −0.026774 | 0.034179 | 0.016891 | −0.009988 | −0.029724 | −0.108584 | 0.014851 | 0.022048 | 0.037099 |
| 163 | 0.057155 | 0.026605 | −0.04247 | −0.078614 | −0.011535 | −0.021501 | −0.005675 | 0.002148 | −0.045008 | 0.024293 | −0.030554 | −0.022863 | −0.03131 | 0.010525 |
| 164 | 0.048965 | 0.028859 | 0.034442 | −0.015475 | −0.080103 | −0.082213 | −0.020416 | 0.01849 | −0.043631 | 0.004129 | −0.028002 | 0.007673 | 0.013844 | −0.003798 |
| 165 | −0.03113 | 0.056555 | −0.00247 | −0.002367 | −0.00715 | 0.011652 | 0.051374 | 0.058734 | 0.025287 | −0.012266 | −0.000381 | 0.007118 | 0.009147 | 0.004807 |
| 166 | −0.074066 | 0.011314 | 0.015715 | −0.039508 | 0.015547 | 0.005941 | 0.001198 | −0.045065 | −0.022706 | 0.000275 | −0.068433 | −0.029656 | −0.004965 | −0.026754 |
| 167 | −0.014485 | 0.019509 | −0.028684 | −0.029847 | −0.056563 | −0.007625 | −0.006843 | 0.02441 | 0.038977 | −0.012349 | −0.050637 | −0.012349 | 0.004742 | −0.043653 |
| 168 | −0.031337 | 0.024416 | 0.075358 | 0.05603 | −0.02651 | 0.070372 | 0.023087 | −0.036127 | 0.019825 | 0.010903 | −0.000915 | −0.003566 | 0.025329 | 0.036662 |
| 169 | 0.02309 | −0.000139 | 0.001875 | 0.008229 | −0.006083 | −0.013757 | 0.046672 | 0.013754 | −0.01848 | 0.022165 | −0.000147 | −0.014907 | −0.015768 | 0.019934 |
| 170 | −0.006382 | 0.00897 | 0.036839 | 0.020653 | −0.00943 | −0.029989 | 0.033186 | 0.004108 | −0.010299 | 0.048165 | −0.003862 | −0.012036 | −0.0135 | 0.015373 |
| 171 | 0.010294 | −0.007002 | 0.017711 | 0.012853 | 0.012891 | −0.042978 | 0.025104 | −0.010213 | −0.023644 | 0.002202 | −0.014597 | −0.017154 | −0.035309 | 0.009671 |
| 172 | 0.039651 | 0.0013621 | −0.0217731 | −0.003667 | −0.02098 | −0.038782 | 0.01958 | −0.003296 | −0.013762 | −0.006228 | −0.015556 | −0.011337 | −0.009087 | 0.044806 |
| 173 | −0.006142 | −0.006988 | −0.012672 | 0.017955 | −0.008984 | −0.006896 | −0.015378 | 0.033888 | −0.022235 | −0.008585 | 0.012625 | 0.005953 | 0.009844 | 0.017505 |
| 174 | 0.00297 | −0.019824 | 0.022994 | 0.042711 | 0.008618 | 0.004661 | −0.002682 | −0.044818 | −0.022961 | −0.023811 | 0.034678 | 0.006585 | −0.025753 | 0.029398 |
| 175 | −0.020853 | 0.048566 | 0.020082 | 0.021857 | −0.036137 | 0.062902 | −0.017392 | 0.007959 | −0.062252 | −0.119341 | −0.011228 | −0.029249 | 0.015752 | −0.031526 |
| 176 | 0.061913 | 0.020592 | −0.029837 | 0.00742 | 0.001516 | 0.023103 | 0.021683 | −0.016506 | 0.001952 | −0.000438 | −0.000008 | −0.014144 | −0.02573 | 0.007503 |
| 177 | 0.029695 | 0.050365 | 0.004091 | 0.032747 | −0.026116 | 0.075633 | −0.07309 | −0.01053 | −0.05121 | −0.000815 | −0.033488 | −0.055802 | 0.023164 | −0.010372 |
| 178 | 0.008582 | −0.025518 | −0.015793 | 0.020312 | 0.025472 | 0.009961 | 0.012806 | 0.032134 | 0.026117 | −0.016681 | −0.015263 | 0.022322 | −0.001548 | 0.013663 |
| 179 | −0.00207 | −0.009755 | −0.00896 | 0.03762 | 0.008055 | 0.002858 | −0.008224 | −0.004676 | −0.023353 | −0.034596 | −0.00756 | −0.009345 | −0.01612 | 0.009847 |
| 180 | −0.003134 | −0.006464 | −0.001511 | 0.001001 | 0.009319 | −0.011177 | −0.007678 | 0.029676 | 0.00959 | −0.024587 | 0.00101 | 0.016142 | −0.005992 | −0.014489 |
| 181 | −0.029061 | −0.022944 | −0.011844 | 0.007064 | 0.022968 | 0.010973 | −0.013074 | 0.009307 | −0.00424 | −0.023688 | −0.004809 | 0.010904 | −0.006655 | −0.016737 |
| 182 | −0.058202 | −0.0178121 | −0.0000321 | 0.020884 | 0.01125 | 0.005398 | −0.040595 | 0.01153 | −0.005489 | −0.04631 | −0.033413 | 0.000937 | 0.013935 | 0.006599 |
| 183 | −0.015294 | −0.000573 | −0.041502 | 0.047574 | −0.043275 | 0.005893 | −0.032701 | −0.047496 | −0.009867 | −0.01162 | −0.011652 | −0.014818 | 0.013416 | 0.007178 |
| 184 | 0.00449 | 0.000134 | −0.050081 | 0.021986 | −0.042989 | −0.030019 | 0.010699 | −0.050563 | 0.010427 | 0.020284 | −0.001671 | −0.027162 | −0.007253 | 0.008758 |
| 185 | 0.077896 | −0.082002 | −0.011894 | −0.003362 | 0.000007 | −0.000466 | −0.018172 | −0.012988 | −0.061752 | −0.064849 | 0.035765 | 0.003298 | −0.045652 | −0.05613 |
| 186 | −0.052128 | 0.010603 | 0.029218 | −0.023737 | 0.0384 | 0.008953 | −0.01 | 0.016234 | 0.034055 | 0.056754 | −0.024214 | −0.004221 | −0.01189 | −0.009116 |
| 187 | 0.026676 | 0.036921 | −0.011844 | −0.019563 | −0.024088 | −0.015505 | −0.014858 | 0.056948 | 0.032704 | 0.00494 | 0.002024 | 0.015382 | 0.041377 | −0.006044 |
| 188 | 0.019699 | 0.00891 | −0.004417 | 0.000492 | −0.01768 | −0.034465 | −0.008282 | 0.00756 | 0.033506 | 0.003189 | 0.015455 | 0.008434 | 0.030765 | 0.007257 |
| 189 | 0.006312 | −0.034912 | −0.02393 | 0.032666 | −0.022454 | −0.02206 | 0.003052 | −0.000169 | −0.000691 | 0.00581 | 0.010896 | −0.009529 | 0.01251 | −0.023531 |
| 190 | 0.037537 | 0.019284 | 0.001174 | 0.05571 | −0.004965 | −0.024128 | −0.010833 | 0.015299 | 0.003323 | 0.008358 | −0.013362 | 0.004826 | −0.020377 | 0.01621 |
| 191 | 0.008716 | 0.050338 | −0.006578 | 0.044211 | 0.075908 | 0.065788 | −0.020183 | 0.002806 | −0.039647 | −0.014306 | −0.01882 | −0.011969 | −0.015535 | 0.008195 |
| 192 | 0.022964 | −0.019549 | 0.045178 | 0.012923 | 0.013212 | 0.052988 | −0.01221 | −0.047379 | −0.011193 | −0.008532 | −0.014125 | −0.015713 | 0.014001 | 0.020081 |
| 193 | 0.000986 | 0.005101 | 0.009476 | 0.030533 | −0.012093 | −0.006096 | −0.024216 | −0.018728 | −0.033526 | 0.018151 | −0.031511 | −0.023748 | 0.02527 | 0.03515 |
| 194 | 0.05736 | 0.05046 | 0.012073 | −0.047386 | −0.010709 | 0.038126 | −0.024246 | 0.059212 | 0.010437 | 0.008152 | 0.00564 | −0.014756 | 0.011258 | −0.059657 |
| 195 | 0.006072 | −0.058894 | −0.075857 | 0.00007 | 0.057504 | −0.013057 | −0.014971 | −0.039755 | −0.009093 | 0.013871 | 0.001764 | 0.009269 | −0.000639 | −0.029663 |
| 196 | −0.007883 | −0.006565 | −0.041446 | −0.026128 | 0.054018 | −0.016954 | −0.05633 | −0.063461 | −0.009179 | −0.011581 | −0.001757 | −0.008184 | −0.008303 | −0.025837 |
| 197 | 0.048059 | 0.0182681 | 0.0317641 | 0.034077 | 0.057375 | −0.01248 | −0.023699 | 0.01298 | −0.00208 | 0.016797 | −0.001201 | −0.014685 | −0.003595 | 0.025274 |
| 198 | 0.036476 | 0.023976 | 0.002776 | −0.031746 | −0.033862 | −0.0363 | 0.025061 | −0.049001 | 0.021708 | 0.008209 | −0.006181 | −0.004955 | 0.026385 | 0.00359 |
| 199 | 0.021462 | 0.029688 | 0.038352 | 0.040217 | −0.077577 | −0.006169 | −0.096892 | 0.042527 | 0.00629 | 0.005722 | 0.020404 | −0.020361 | 0.023933 | −0.030359 |
| 200 | −0.046432 | −0.055913 | 0.010753 | −0.044414 | 0.004518 | −0.031872 | −0.000877 | 0.005335 | 0.007237 | −0.029298 | −0.032587 | 0.02852 | 0.02443 | 0.055803 |
| 201 | −0.022452 | 0.078482 | −0.061722 | −0.034994 | 0.007348 | 0.001782 | 0.03147 | −0.089067 | 0.059785 | −0.018576 | −0.00757 | 0.047704 | 0.037516 | −0.050107 |
| 202 | −0.024042 | 0.036804 | 0.012004 | −0.025538 | −0.012981 | −0.012607 | −0.017905 | 0.011824 | −0.010801 | 0.078657 | −0.036569 | −0.026596 | −0.05147 | 0.012605 |
| 203 | 0.06628 | 0.014119 | 0.010143 | 0.055843 | 0.011972 | −0.037012 | −0.015249 | −0.029032 | −0.004665 | −0.030027 | 0.009388 | −0.01962 | −0.010415 | −0.009922 |
| 204 | 0.024868 | 0.014748 | −0.063533 | −0.052088 | −0.052239 | 0.01126 | −0.020196 | −0.002115 | 0.01021 | −0.003214 | −0.005804 | 0.009596 | 0.01793 | −0.005361 |
| 205 | −0.02155 | −0.04239 | 0.026558 | 0.01421 | 0.005782 | 0.112464 | 0.015951 | 0.027213 | 0.03414 | −0.041211 | −0.023243 | 0.047716 | 0.040942 | −0.009558 |
| 206 | −0.005992 | −0.099298 | 0.024982 | 0.01878 | −0.037189 | −0.051117 | −0.01921 | 0.005473 | 0.030001 | 0.012544 | 0.013774 | 0.03 | 0.013037 | 0.017574 |
| 207 | 0.00111 | 0.000621 | −0.011762 | −0.015885 | 0.034344 | −0.050757 | −0.010843 | 0.027911 | 0.002479 | −0.076605 | −0.04312 | 0.045907 | −0.009747 | −0.047939 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 208 | −0.068177 | −0.054691 | 0.013892 | −0.005586 | 0.01621 | 0.046777 | −0.065514 | −0.00621 | 0.025431 | −0.007676 | 0.008637 | 0.014729 | 0.014097 | 0.041923 |
| 209 | 0.008927 | −0.042725 | 0.038216 | −0.00987 | 0.011111 | −0.029104 | 0.001391 | −0.055812 | 0.002217 | −0.042499 | 0.025716 | 0.02703 | −0.004578 | 0.02014 |
| 210 | 0.021384 | −0.014261 | −0.046977 | 0.008604 | −0.026676 | 0.046431 | 0.091187 | 0.024167 | 0.002334 | 0.021054 | 0.01868 | −0.01166 | −0.021328 | −0.021809 |
| 211 | 0.054087 | 0.046287 | 0.000535 | 0.025854 | 0.005409 | 0.006644 | −0.012687 | 0.025871 | 0.004982 | −0.025382 | 0.000701 | 0.005249 | 0.019361 | 0.042251 |
| 212 | 0.003704 | −0.007261 | 0.081462 | −0.034605 | −0.035118 | 0.055886 | 0.037209 | −0.0463 | −0.023241 | −0.056636 | 0.03242 | 0.008461 | −0.034111 | 0.010723 |
| 213 | −0.03254 | 0.015296 | −0.018916 | −0.018865 | −0.033747 | 0.05443 | −0.026477 | 0.010172 | 0.039873 | −0.003925 | −0.051416 | 0.031366 | 0.057561 | −0.01148 |
| 214 | 0.002351 | −0.020443 | −0.004027 | 0.025457 | 0.007453 | −0.007296 | −0.03368 | 0.000912 | −0.019843 | −0.010156 | 0.00907 | −0.012498 | −0.015515 | 0.001964 |
| 215 | −0.022426 | −0.002763 | −0.037263 | 0.004951 | 0.036418 | 0.059557 | −0.001433 | 0.03832 | −0.044967 | −0.009337 | 0.014901 | −0.014364 | 0.014568 | −0.029001 |
| 216 | −0.036552 | 0.013927 | −0.014782 | −0.061408 | 0.028909 | 0.073821 | 0.015885 | 0.006099 | 0.031833 | −0.01329 | −0.030132 | 0.024041 | 0.029191 | −0.04218 |
| 217 | −0.020767 | −0.002369 | −0.013524 | −0.015367 | −0.038306 | 0.007611 | 0.024789 | 0.092167 | −0.012173 | −0.039994 | −0.07239 | 0.014278 | 0.013588 | 0.016486 |
| 218 | −0.034326 | −0.025629 | −0.006133 | 0.027972 | 0.015843 | 0.005807 | −0.022174 | −0.008897 | −0.015644 | 0.015073 | 0.014597 | −0.003295 | 0.013015 | −0.026926 |
| 219 | −0.034197 | −0.014789 | −0.019955 | 0.000238 | 0.009602 | −0.031659 | −0.011065 | −0.05083 | −0.006698 | 0.005133 | 0.005055 | 0.009213 | 0.008415 | −0.011879 |
| 220 | −0.008439 | −0.01551 | −0.0426 | 0.010883 | −0.000159 | 0.018804 | 0.001316 | −0.019875 | −0.015394 | −0.039021 | −0.027814 | −0.005054 | −0.008229 | 0.017919 |
| 221 | 0.005205 | −0.00728 | −0.05025 | −0.005405 | −0.023425 | 0.023001 | 0.020884 | −0.001532 | 0.023667 | 0.003089 | 0.029812 | 0.028688 | −0.002251 | 0.012835 |
| 222 | −0.036017 | −0.012951 | −0.003979 | −0.015127 | 0.014225 | 0.035314 | −0.012627 | −0.012073 | 0.018361 | −0.003016 | 0.008943 | 0.016477 | 0.022701 | 0.006696 |
| 223 | −0.047498 | −0.026821 | 0.015122 | −0.048743 | 0.013871 | 0.044612 | −0.048889 | −0.020644 | −0.001327 | −0.012761 | 0.032427 | −0.002144 | 0.015105 | −0.02111 |
| 224 | 0.00083 | 0.02137 | −0.043076 | 0.017496 | 0.008804 | 0.003154 | −0.011688 | 0.017367 | −0.062731 | −0.048497 | 0.006204 | −0.045048 | −0.061646 | −0.000952 |
| 225 | 0.004455 | 0.025687 | −0.053634 | 0.041826 | −0.024998 | 0.003947 | 0.010424 | 0.008199 | −0.059913 | −0.031028 | 0.024505 | −0.025274 | −0.040178 | −0.006278 |
| 226 | −0.005261 | −0.01507 | −0.013299 | −0.009527 | 0.013573 | 0.019267 | 0.016945 | −0.027372 | 0.024 | 0.04044 | 0.00593 | 0.005416 | 0.001037 | −0.027504 |
| 227 | 0.027006 | −0.007638 | −0.007451 | 0.029392 | −0.049343 | −0.0284 | 0.02034 | 0.011094 | −0.012513 | −0.01856 | 0.009014 | −0.014134 | −0.003833 | −0.026081 |
| 228 | 0.007894 | −0.01213 | 0.048193 | 0.025706 | 0.032255 | 0.005276 | −0.040657 | 0.042836 | 0.024364 | −0.036625 | −0.025254 | 0.013862 | −0.016014 | −0.018148 |
| 229 | −0.010101 | 0.014637 | 0.034321 | −0.009041 | 0.016071 | 0.012206 | 0.026401 | 0.079328 | −0.005086 | 0.006191 | −0.038234 | 0.013044 | 0.004562 | 0.004229 |
| 230 | −0.017018 | 0.011296 | 0.021818 | 0.000804 | 0.010397 | 0.03989 | 0.009634 | 0.012472 | 0.021782 | 0.003707 | −0.002644 | 0.004852 | 0.032084 | 0.018859 |
| 231 | 0.009574 | −0.014691 | −0.033916 | −0.021331 | −0.049446 | 0.00798 | 0.008127 | −0.053965 | −0.005816 | 0.001315 | 0.028062 | −0.016122 | 0.037514 | 0.01143 |
| 232 | 0.055051 | −0.012312 | −0.01506 | −0.024133 | 0.04082 | −0.033471 | −0.057172 | −0.027558 | 0.011185 | −0.00545 | 0.016095 | −0.00457 | −0.004135 | −0.006695 |
| 233 | 0.035427 | −0.046384 | −0.025672 | −0.014195 | −0.043063 | 0.069297 | 0.022083 | 0.006795 | 0.025298 | 0.029554 | 0.017871 | 0.007251 | −0.002284 | −0.038503 |
| 234 | −0.004148 | 0.004618 | 0.054338 | −0.046316 | 0.031061 | −0.042167 | 0.029255 | −0.004333 | 0.035758 | 0.009307 | 0.016745 | −0.003556 | −0.003109 | 0.03054 |
| 235 | 4.015454 | 0.065743 | 0.010422 | 0.023569 | −0.026906 | −0.015157 | 0.024263 | −0.033185 | −0.045666 | 0.000032 | 0.024921 | −0.017766 | 0.003522 | 0.027054 |
| 236 | 0.039729 | 0.018036 | −0.01953 | −0.023088 | −0.00824 | −0.024745 | −0.0016 | −0.004709 | −0.014223 | 0.006681 | 0.018322 | 0.001449 | 0.002708 | 0.01973 |
| 237 | 0.002752 | 0.019508 | 0.046024 | 0.000875 | −0.005446 | −0.025301 | 0.001643 | 0.026639 | −0.004789 | −0.022495 | 0.013409 | −0.007453 | 0.023734 | −0.00416 |
| 238 | −0.030626 | 0.02449 | 0.003771 | −0.011195 | 0.001591 | −0.020579 | −0.007858 | −0.008166 | 0.007553 | −0.027105 | 0.011767 | 0.000257 | 0.008443 | 0.007344 |
| 239 | −0.000268 | 0.00378 | −0.032659 | −0.018034 | 0.001219 | 0.009939 | 0.00106 | −0.03247 | 0.016069 | 0.006253 | 0.014891 | 0.0173 | 0.001314 | −0.006387 |
| 240 | 0.021865 | 0.00539 | −0.038162 | 0.006397 | −0.000331 | 0.028392 | 0.016313 | −0.003868 | −0.004032 | 0.028478 | −0.001688 | 0.006265 | −0.035579 | 0.001508 |
| 241 | −0.001505 | −0.022399 | −0.018419 | −0.003957 | −0.002807 | 0.05726 | −0.000663 | −0.033422 | −0.014167 | 0.015094 | 0.011584 | −0.000822 | −0.025349 | −0.02353 |
| 242 | −0.004637 | 0.036525 | −0.003128 | −0.022155 | −0.037582 | 0.02478 | 0.000035 | 0.025369 | −0.032487 | 0.002772 | −0.021732 | −0.005105 | −0.009229 | 0.004593 |
| 243 | −0.022956 | 0.058716 | 0.019195 | 0.005012 | −0.000641 | 0.016555 | 0.035619 | −0.004097 | −0.00131 | −0.004128 | −0.006342 | −0.001568 | 0.01073 | −0.006148 |
| 244 | 0.074957 | −0.001951 | 0.000055 | 0.020545 | −0.02862 | −0.015158 | 0.038448 | 0.00221 | 0.031387 | 0.01513 | 0.014934 | 0.015185 | −0.000848 | 0.017974 |
| 245 | 0.026569 | −0.04118 | −0.008126 | 0.01795 | −0.013623 | −0.031233 | 0.028221 | −0.001551 | 0.005304 | 0.048056 | 0.037656 | 0.000608 | 0.001712 | 0.005241 |
| 246 | −0.001956 | −0.00369 | −0.035501 | 0.03072 | 0.019945 | 0.027754 | −0.015498 | 0.041097 | −0.015274 | −0.004419 | 0.00905 | 0.008587 | −0.015188 | −0.006831 |
| 247 | 0.029035 | 0.017165 | −0.032774 | 0.003967 | −0.020106 | −0.009951 | −0.004983 | −0.007941 | −0.007443 | −0.033255 | 0.033282 | −0.010338 | −0.024155 | −0.006351 |
| 248 | 0.028606 | 0.004906 | −0.035782 | 0.008134 | 0.009753 | −0.027527 | −0.009678 | −0.026621 | −0.008119 | −0.04016 | 0.010938 | −0.003291 | 0.014671 | 0.008926 |
| 249 | 0.007388 | 0.009797 | −0.019502 | 0.005245 | 0.033445 | 0.034721 | −0.033838 | −0.023331 | −0.005324 | 0.061303 | −0.028683 | −0.00633 | 0.000703 | 0.019069 |
| 250 | −0.005109 | 0.022962 | −0.007481 | 0.00423 | 0.052239 | 0.056589 | −0.03625 | 0.018825 | −0.006237 | −0.017145 | −0.00071 | −0.016154 | 0.005824 | −0.014185 |
| 251 | −0.033659 | 0.01917 | 0.023908 | 0.010784 | −0.012229 | −0.001119 | 0.00142 | −0.021546 | −0.016359 | 0.015243 | 0.026805 | 0.011776 | −0.01193 | 0.00199 |
| 252 | −0.022448 | 0.000066 | 0.019131 | −0.000948 | −0.005329 | −0.002045 | 0.025151 | −0.052994 | −0.020391 | 0.038511 | −0.006843 | 0.00651 | −0.005928 | 0.005101 |
| 253 | 0.059583 | −0.006432 | 0.006168 | −0.059677 | 0.001964 | 0.052965 | −0.015029 | −0.008449 | 0.018929 | 0.01182 | 0.000531 | 0.011268 | 0.023714 | −0.011768 |
| 254 | 0.01522 | −0.00063 | 0.029171 | −0.012323 | 0.009397 | 0.005242 | −0.025136 | −0.023531 | −0.019835 | −0.010716 | 0.013473 | −0.00508 | −0.006837 | 0.015183 |
| 255 | 0.015548 | 0.007607 | 0.019075 | 0.025497 | −0.017023 | 0.002798 | 0.024379 | −0.008514 | 0.020652 | 0.001169 | 0.000978 | 0.013528 | 0.001307 | 0.04162 |
| 256 | −0.01205 | −0.024068 | −0.002587 | −0.011554 | 0.00148 | −0.012624 | −0.000354 | −0.001934 | 0.041431 | −0.002178 | 0.002802 | 0.018791 | 0.038122 | 0.041944 |
| 257 | 0.005217 | −0.04001 | −0.016253 | −0.031416 | −0.005015 | −0.005397 | −0.030176 | −0.019514 | 0.015133 | 0.013381 | −0.019014 | 0.013866 | 0.022005 | 0.004786 |
| 258 | 0.03242 | −0.042626 | −0.008642 | 0.005918 | −0.016933 | −0.006161 | 0.000443 | 0.008959 | 0.004025 | 0.023723 | 0.020818 | 0.020722 | −0.005787 | 0.023811 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 259 | −0.024677 | 0.003992 | 0.020998 | −0.001639 | 0.041213 | 0.012212 | −0.007085 | 0.003355 | −0.008142 | 0.020038 | −0.012535 | −0.000018 | 0.006432 | 0.008174 |
| 260 | −0.017551 | −0.020768 | 0.034541 | 0.00184 | 0.037027 | 0.022043 | 0.009543 | −0.026439 | 0.004427 | 0.019441 | −0.02491 | −0.002799 | 0.022391 | 0.004036 |
| 261 | −0.052214 | −0.04357 | 0.026342 | −0.000898 | 0.000381 | 0.002994 | 0.016845 | −0.017254 | 0.011884 | 0.029308 | −0.011731 | 0.018488 | −0.001618 | 0.004843 |
| 262 | −0.004768 | −0.037991 | −0.000089 | −0.018204 | −0.044545 | −0.012067 | −0.004049 | 0.017264 | −0.008188 | 0.011043 | −0.021877 | −0.002428 | −0.008241 | 0.005072 |
| 263 | −0.005012 | 0.005807 | −0.003509 | −0.021772 | −0.001403 | −0.026213 | 0.012439 | 0.006851 | −0.020563 | 0.01428 | −0.031941 | −0.022803 | −0.016017 | 0.018054 |
| 264 | −0.012663 | 0.032929 | −0.010286 | 0.004832 | 0.018067 | −0.005514 | 0.002202 | −0.028364 | 0.0065 | −0.022046 | −0.002409 | −0.00981 | 0.013508 | 0.026888 |
| 265 | −0.003162 | 0.012273 | −0.005751 | −0.002182 | 0.020707 | −0.047214 | −0.012039 | −0.027827 | 0.000153 | −0.035307 | 0.004342 | 0.000373 | 0.026658 | −0.00612 |
| 266 | −0.04338 | −0.026578 | 0.036014 | −0.029371 | 0.01464 | −0.024078 | −0.008886 | −0.023095 | 0.020508 | −0.042782 | −0.000415 | 0.000494 | 0.033522 | −0.01025 |
| 267 | 0.060045 | −0.028304 | −0.044371 | −0.040189 | 0.026438 | 0.021183 | 0.00317 | 0.038699 | 0.026044 | 0.013945 | −0.006357 | 0.009 | −0.000723 | 0.000608 |
| 268 | 0.019076 | 0.030062 | −0.040437 | −0.018197 | 0.023897 | 0.006109 | 0.00886 | −0.037932 | 0.002766 | 0.030134 | 0.008445 | −0.01329 | −0.017503 | −0.03774 |
| 269 | −0.006639 | 0.011843 | −0.015971 | −0.005951 | 0.012588 | 0.020801 | −0.013361 | −0.000915 | −0.021906 | −0.003143 | −0.008954 | −0.016219 | −0.004597 | −0.029725 |
| 270 | 0.017667 | −0.033847 | 0.018293 | 0.004573 | 0.019064 | 0.0099 | −0.00406 | −0.000808 | −0.003356 | −0.00147 | −0.022034 | −0.005828 | 0.004681 | −0.018247 |
| 271 | −0.046767 | 0.057229 | 0.037187 | 0.058537 | −0.044884 | 0.00569 | −0.041797 | −0.058362 | −0.043751 | −0.047985 | 0.024382 | −0.010215 | −0.005495 | −0.061786 |
| 272 | −0.012142 | −0.006422 | 0.033905 | 0.017415 | 0.001726 | −0.043427 | 0.015319 | 0.02036 | −0.014927 | −0.002976 | −0.009404 | 0.003441 | −0.015679 | 0.024103 |
| 273 | 0.009579 | 0.023315 | −0.006136 | 0.021796 | 0.010077 | 0.001066 | 0.007968 | −0.016549 | −0.009472 | 0.03805 | −0.008023 | −0.017146 | −0.018412 | 0.013221 |
| 274 | −0.002063 | 0.018123 | 0.002645 | 0.021742 | 0.004711 | 0.003346 | 0.002397 | −0.009561 | −0.017428 | 0.015875 | −0.017797 | −0.015442 | −0.015634 | 0.010525 |
| 275 | −0.019372 | 0.014003 | 0.030927 | 0.023681 | 0.004402 | 0.000252 | −0.003868 | 0.008136 | 0.015098 | −0.025325 | −0.027006 | 0.001596 | 0.024718 | 0.031948 |
| 276 | 0.049751 | 0.045127 | −0.002905 | −0.033338 | −0.004767 | −0.022381 | 0.001118 | 0.003618 | −0.01117 | 0.008484 | 0.010493 | −0.002789 | −0.015055 | 0.003344 |
| 277 | 0.010139 | 0.030555 | 0.011123 | −0.00641 | −0.009571 | −0.003182 | 0.011188 | 0.024036 | 0.007199 | 0.002947 | −0.000186 | −0.017057 | −0.002908 | −0.01439 |
| 278 | −0.002554 | −0.019939 | 0.033372 | 0.001377 | −0.029208 | 0.018842 | −0.005927 | 0.047922 | −0.000675 | −0.024788 | −0.024834 | −0.004154 | 0.014769 | −0.011443 |
| 279 | −0.018091 | 0.010823 | 0.013689 | −0.012791 | 0.028383 | −0.00371 | −0.009535 | −0.019018 | 0.014639 | −0.030495 | −0.008734 | 0.009694 | 0.007369 | 0.003771 |
| 280 | −0.000274 | 0.08082 | −0.005243 | −0.034629 | 0.009474 | 0.030992 | 0.03491 | 0.010751 | 0.010428 | 0.035702 | 0.006344 | −0.009648 | 0.018851 | −0.017745 |
| 281 | −0.04748 | −0.01277 | −0.003881 | 0.026079 | 0.053042 | 0.04765 | −0.001974 | −0.015909 | −0.013234 | 0.061554 | 0.02747 | −0.017781 | −0.027887 | −0.007042 |
| 282 | −0.060973 | −0.039459 | 0.025717 | 0.043056 | 0.035664 | 0.051862 | −0.005024 | 0.025452 | −0.040182 | 0.00903 | 0.006232 | 0.000497 | −0.034113 | −0.003155 |
| 283 | −0.019907 | 0.001883 | 0.028969 | −0.005705 | 0.009658 | −0.024539 | 0.012692 | −0.009262 | 0.000492 | −0.043749 | 0.005261 | 0.000662 | −0.019988 | 0.003963 |
| 284 | −0.007344 | −0.008662 | −0.004198 | −0.027261 | −0.008235 | −0.01862 | −0.030277 | −0.023086 | 0.011206 | 0.009683 | −0.01975 | 0.007451 | 0.013082 | 0.015356 |
| 285 | −0.012014 | −0.005491 | 0.021119 | .−04306 | −0.004086 | −0.006752 | −0.041912 | −0.021547 | 0.021282 | 0.01255 | −0.019085 | 0.022019 | 0.014036 | −0.003557 |
| 286 | −0.017415 | −0.042342 | 0.030717 | −0.0102 | −0.056419 | 0.000247 | −0.034365 | −0.002422 | 0.000663 | 0.005163 | 0.006954 | 0.02193 | 0.028825 | 0.001538 |
| 287 | −0.019855 | −0.045636 | 0.066424 | −0.005616 | −0.034425 | −0.004903 | 0.000389 | 0.02546 | 0.00172 | 0.020563 | −0.015029 | 0.013275 | −0.003515 | 0.012972 |
| 288 | 0.044623 | −0.015513 | 0.018934 | 0.020256 | −0.03782 | 0.020886 | −0.006447 | 0.047924 | −0.008181 | 0.006606 | 0.001746 | 0.016789 | −0.005453 | 0.038842 |
| 289 | 0.015359 | −0.014868 | −0.011417 | 0.00629 | −0.021083 | 0.003556 | 0.015166 | 0.018586 | −0.007777 | −0.001004 | −0.028566 | 0.00862 | 0.01311 | 0.011739 |
| 290 | 0.007234 | 0.045241 | −0.038098 | 0.004234 | 0.020847 | 0.007507 | 0.015188 | −0.006258 | −0.003439 | 0.010762 | −0.016045 | −0.022254 | −0.006709 | 0.026362 |
| 291 | 0.012165 | 0.042965 | −0.040197 | −0.001517 | 0.020328 | 0.011572 | 0.013832 | 0.004165 | −0.004126 | 0.007333 | −0.018639 | −0.018566 | −0.005897 | 0.026719 |
| 292 | 0.009427 | 0.063537 | −0.036306 | 0.000809 | 0.022574 | 0.013632 | −0.004411 | 0.010653 | −0.009352 | 0.000389 | −0.005271 | −0.025855 | −0.006229 | 0.022693 |
| 293 | 0.002754 | 0.03664 | −0.026607 | −0.064489 | −0.049358 | 0.034058 | −0.017175 | 0.024506 | −0.031793 | −0.020788 | 0.02277 | −0.014521 | −0.00489 | 0.013928 |
| 294 | 0.022027 | −0.00763 | −0.019231 | −0.014259 | −0.002944 | 0.015792 | 0.037691 | 0.010643 | −0.005529 | 0.002273 | 0.035398 | 0.005593 | 0.013682 | 0.00227 |
| 295 | 0.015426 | 0.001349 | −0.003266 | −0.007719 | −0.062567 | 0.010666 | −0.018829 | 0.051603 | −0.018419 | −0.008344 | −0.009657 | −0.009947 | 0.014474 | 0.005777 |
| 290 | 0.008966 | 0.002953 | 0.014775 | 0.025055 | −0.014799 | 0.051449 | 0.018734 | 0.056068 | 0.005273 | −0.027877 | 0.000567 | −0.003627 | −0.007186 | −0.000324 |
| 297 | 0.006384 | −0.020484 | −0.025714 | −0.021554 | −0.036246 | 0.04817 | −0.01748 | 0.018749 | −0.039938 | 0.018566 | −0.019485 | −0.032448 | −0.014547 | 0.026929 |
| 298 | −0.033982 | −0.037472 | −0.033697 | 0.001747 | 0.059327 | −0.008537 | −0.025758 | −0.018805 | −0.021769 | 0.041003 | −0.000384 | −0.013441 | −0.015629 | 0.080715 |
| 299 | −0.004962 | −0.003421 | −0.001655 | −0.022082 | −0.01107 | 0.000495 | −0.011262 | −0.057332 | −0.021828 | 0.013171 | 0.0542361 | −0.014752 | 0.0041951 | −0.004845 |
| 300 | 0.020672 | 0.012086 | 0.037793 | −0.033334 | −0.008247 | −0.000005 | −0.004432 | −0.052436 | −0.006253 | 0.053858 | 0.016237 | −0.029719 | −0.032165 | 0.009653 |
| 301 | −0.006993 | −0.004039 | −0.008571 | −0.031255 | −0.026338 | −0.027727 | −0.022862 | −0.015715 | 0.00272 | 0.014135 | 0.014167 | 0.012195 | 0.019709 | 0.017614 |
| 302 | −0.016317 | −0.021109 | −0.019386 | −0.0182 | 0.006381 | 0.012623 | −0.011735 | 0.020497 | 0.035517 | 0.002534 | −0.000864 | 0.033 | 0.043218 | −0.023285 |
| 303 | 0.009304 | −0.01352 | 0.005311 | 0.012858 | −0.041193 | −0.009813 | 0.000354 | −0.021067 | 0.021663 | −0.008831 | 0.078514 | 0.014195 | 0.02786 | −0.014774 |
| 304 | 0.021464 | −0.0122041 | 0.0176841 | −0.003386 | 0.004018 | −0.007046 | −0.019264 | −0.041779 | 0.0265971 | −0.018618 | 0.0520211 | 0.0210841 | 0.0344761 | −0.008214 |
| 305 | −0.058601 | −0.043363 | −0.005594 | 0.004479 | −0.016061 | −0.008914 | −0.04283 | 0.006246 | −0.020821 | −0.079435 | −0.003884 | 0.011543 | −0.009101 | −0.001302 |
| 306 | 0.049594 | 0.012645 | −0.028012 | 0.014108 | 0.017392 | −0.013962 | 0.022052 | −0.043243 | −0.023318 | −0.014071 | 0.019887 | −0.013387 | −0.016715 | 0.00187 |
| 307 | −0.030914 | −0.036141 | 0.060003 | 0.042087 | 0.044762 | 0.001905 | −0.010386 | −0.045759 | 0.063796 | 0.003188 | −0.03408 | −0.005429 | 0.026178 | −0.025695 |
| 308 | 0.01631 | 0.016883 | 0.013061 | −0.015857 | 0.045041 | 0.024864 | −0.005014 | −0.01893 | 0.008121 | 0.02807 | −0.01427 | −0.006131 | −0.011402 | 0.01368 |
| 309 | −0.001607 | 0.00419 | 0.021524 | 0.001038 | 0.018448 | 0.009426 | −0.029664 | 0.020303 | −0.012174 | 0.0088 | −0.020055 | −0.024771 | −0.027627 | 0.021686 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 310 | 0.014673 | 0.016463 | −0.01067 | 0.027999 | 0.022037 | 0.004771 | −0.00868 | −0.006216 | −0.021917 | −0.064901 | 0.014852 | −0.002628 | 0.00896 | −0.006005 |
| 311 | 0.020576 | 0.027074 | −0.025833 | 0.007691 | −0.016114 | −0.036761 | 0.029824 | −0.004343 | 0.011621 | −0.005421 | −0.021724 | 0.002245 | −0.001173 | 0.014424 |
| 312 | −0.039328 | −0.03649 | −0.034088 | 0.003348 | −0.056865 | 0.092736 | 0.074594 | −0.060314 | 0.010663 | 0.018561 | 0.003269 | −0.018924 | 0.046951 | 0.029479 |
| 313 | 0.022854 | 0.036741 | −0.004674 | 0.001841 | −0.009583 | −0.011651 | 0.009083 | −0.036813 | −0.013695 | 0.007973 | −0.018043 | −0.039734 | −0.018524 | 0.062236 |
| 314 | 0.005104 | −0.04549 | 0.031632 | −0.066902 | 0.024826 | −0.010654 | 0.051467 | 0.012323 | −0.027341 | −0.019483 | 0.022885 | −0.024506 | 0.000671 | 0.056714 |
| 315 | 0.005805 | 0.00091 | 0.034678 | 0.014572 | 0.004295 | 0.02765 | −0.008948 | 0.021961 | −0.027758 | −0.014448 | −0.005368 | −0.048456 | −0.04265 | −0.003196 |
| 316 | 0.032189 | −0.009669 | 0.016633 | −0.061953 | −0.007179 | 0.051649 | −0.039919 | 0.03802 | 0.015867 | −0.010051 | −0.000187 | −0.015964 | −0.042131 | 0.016871 |
| 317 | −0.006989 | 0.00082 | 0.026208 | −0.008637 | 0.026733 | −0.009448 | −0.027834 | 0.008185 | −0.026957 | −0.014357 | −0.015722 | −0.015944 | −0.019919 | 0.010852 |
| 318 | 0.026068 | −0.003832 | 0.024824 | −0.040193 | 0.034495 | 0.037167 | −0.032058 | −0.030195 | 0.025372 | −0.002603 | 0.013766 | 0.016713 | −0.011414 | −0.015054 |
| 319 | −0.0148111 | 0.01359 | 0.015487 | −0.014832 | 0.025006 | 0.031256 | −0.020038 | 0.017599 | −0.011904 | 0.0001891 | 0.0002081 | −0.042657 | −0.042644 | 0.00035 |
| 320 | −0.039699 | 0.000765 | −0.040211 | −0.004062 | 0.06317 | 0.008748 | 0.01912 | −0.022237 | −0.004194 | −0.040193 | −0.005862 | −0.006988 | −0.042993 | 0.011292 |
| 321 | −0.006048 | −0.037578 | 0.045437 | 0.02245 | −0.023453 | 0.006994 | 0.012772 | −0.00416 | −0.009752 | 0.046119 | 0.008283 | −0.023818 | −0.013193 | 0.019559 |
| 322 | −0.021534 | −0.001947 | 0.017294 | −0.009587 | 0.008099 | 0.005162 | 0.001351 | −0.001357 | −0.060924 | −0.07478 | −0.022721 | −0.009126 | 0.007392 | −0.013171 |
| 323 | −0.041703 | −0.005482 | −0.037448 | −0.017039 | 0.038289 | −0.038618 | −0.006595 | −0.021017 | −0.012488 | 0.000006 | −0.037312 | −0.026374 | 0.048262 | 0.019683 |
| 324 | 0.067877 | 0.000736 | −0.015719 | −0.019346 | 0.048715 | 0.06496 | −0.033713 | −0.044617 | 0.053426 | 0.01451 | −0.014825 | 0.026864 | 0.021786 | −0.040041 |
| 325 | −0.023536 | −0.013623 | 0.024155 | 0.04401 | −0.012109 | 0.018543 | −0.030859 | 0.035501 | −0.004096 | −0.014166 | −0.005006 | −0.019366 | −0.027101 | 0.015103 |
| 326 | 0.009682 | 0.040255 | −0.04095 | 0.024123 | −0.010606 | −0.033464 | 0.019248 | −0.036769 | 0.003777 | 0.000733 | 0.018343 | −0.002496 | −0.002929 | 0.006731 |
| 327 | −0.019226 | 0.008501 | 0.005844 | 0.002495 | −0.001514 | −0.000555 | −0.01218 | 0.012397 | 0.013342 | −0.023055 | 0.006817 | 0.019652 | −0.007325 | 0.001089 |
| 328 | 0.030499 | −0.011363 | 0.000807 | 0.018116 | −0.023878 | 0.05427 | 0.004202 | 0.019931 | 0.016005 | 0.016657 | 0.009487 | 0.000523 | 0.022464 | −0.007293 |
| 329 | 0.002914 | −0.022358 | −0.015339 | −0.000298 | −0.012617 | −0.038754 | −0.002126 | −0.029402 | −0.010124 | −0.02995 | 0.03926 | 0.009561 | −0.000347 | −0.005282 |
| 330 | −0.006597 | −0.024782 | 0.008458 | 0.016391 | 0.005122 | 0.003289 | −0.020286 | 0.006738 | −0.023192 | −0.006171 | −0.012658 | −0.024694 | −0.005642 | 0.021433 |
| 331 | −0.001388 | 0.010917 | −0.00521 | 0.002569 | 0.008869 | 0.012054 | 0.008648 | 0.033501 | −0.011235 | −0.02669 | −0.010369 | −0.023175 | −0.012234 | 0.008948 |
| 332 | 0.061333 | 0.00369 | −0.036131 | −0.004029 | −0.049404 | −0.046256 | 0.040499 | 0.012328 | 0.035496 | −0.014151 | 0.003237 | 0.029826 | −0.018901 | 0.026715 |
| 333 | −0.007457 | −0.002057 | 0.012255 | 0.009875 | 0.02217 | 0.023056 | −0.043117 | 0.038367 | −0.001567 | −0.021446 | −0.035657 | −0.015595 | −0.016756 | 0.006032 |
| 334 | −0.100769 | 0.040785 | 0.004383 | 0.024369 | −0.053706 | 0.034928 | −0.024458 | 0.044398 | 0.004643 | 0.024612 | 0.006958 | 0.002662 | −0.057354 | −0.023363 |
| 335 | −0.000292 | −0.031286 | 0.031263 | −0.015788 | 0.0228 | 0.03061 | −0.0137 | −0.011802 | 0.012747 | −0.000473 | −0.005107 | −0.005258 | 0.022074 | 0.009108 |
| 336 | 0.007287 | −0.026616 | 0.068295 | −0.000036 | 0.003993 | −0.068825 | −0.004268 | 0.048162 | 0.026277 | −0.035185 | 0.030333 | 0.051528 | 0.057446 | 0.01467 |
| 337 | −0.007689 | 0.039701 | 0.028837 | 0.043932 | −0.02187 | −0.061346 | −0.030918 | −0.068278 | −0.008527 | 0.008787 | 0.032793 | −0.024262 | −0.006574 | 0.011358 |
| 338 | −0.008782 | −0.027704 | 0.023439 | −0.028615 | 0.007166 | 0.013533 | 0.016236 | 0.045426 | −0.017285 | 0.015922 | 0.042822 | 0.022663 | −0.016967 | −0.014034 |
| 339 | −0.073582 | 0.061279 | −0.012682 | −0.023344 | 0.017601 | −0.0525 | −0.005146 | −0.018221 | 0.016858 | 0.063406 | −0.037595 | 0.004276 | −0.040222 | −0.008791 |
| 340 | 0.068227 | 0.004407 | 0.017418 | −0.033203 | −0.048284 | 0.027071 | −0.03869 | 0.008564 | 0.003723 | 0.014254 | −0.002807 | 0.011167 | −0.025405 | 0.016374 |

| | DT | DU | DV | DW | DX | DY | DZ | EA | EB | EC | ED | EE | EF | EG |
|---|---|---|---|---|---|---|---|---|---|---|---|---|---|---|
| 1 | 0.040192 | 0.091089 | 0.011247 | 0.022545 | 0.057896 | −0.005584 | 0.055363 | 0.061463 | −0.035906 | −0.159549 | 0.02845 | 0.010929 | 0.068786 | 0.056986 |
| 2 | −0.025234 | −0.068913 | −0.060095 | −0.008899 | −0.001046 | −0.035285 | 0.138294 | 0.032893 | 0.09041 | −0.02741 | 0.044899 | −0.026505 | −0.08286 | −0.096215 |
| 3 | 0.015568 | −0.020536 | 0.004571 | 0.083858 | 0.058834 | 0.058171 | −0.134892 | 0.06117 | 0.015639 | 0.008217 | 0.089713 | 0.048068 | 0.001534 | −0.055341 |
| 4 | −0.034632 | 0.027602 | 0.049297 | −0.040267 | −0.020406 | −0.029394 | 0.063607 | −0.071649 | −0.067747 | −0.005372 | −0.047816 | −0.082496 | 0.060175 | −0.051911 |
| 5 | 0.000244 | 0.021042 | −0.045059 | −0.023705 | −0.021747 | 0.018681 | −0.115373 | −0.028099 | −0.089697 | −0.005994 | −0.037481 | −0.005795 | −0.02671 | −0.046361 |
| 6 | 0.094341 | 0.018045 | 0.0211471 | 0.064264 | 0.042728 | −0.018555 | −0.011165 | −0.046611 | 0.008973 | −0.061255 | 0.034524 | −0.002387 | −0.029029 | 0.017982 |
| 7 | −0.052959 | −0.0583561 | 0.0119191 | −0.022181 | −0.025276 | 0.056638 | −0.080825 | −0.029156 | −0.023752 | −0.059133 | −0.062741 | −0.020991 | 0.0202451 | −0.057916 |
| 8 | −0.073884 | −0.0377961 | 0.0474221 | 0.024176 | 0.025713 | 0.026426 | 0.100649 | 0.03295 | 0.057433 | 0.062948 | 0.081482 | 0.037128 | 0.014381 | 0.025391 |
| 9 | 0.05576 | −0.021427 | 0.033578 | 0.000078 | −0.014691 | −0.004131 | −0.00352 | 0.008835 | −0.087932 | 0.104202 | −0.05768 | 0.066828 | −0.021801 | 0.015479 |
| 10 | 0.012484 | 0.074121 | 0.010245 | −0.035906 | −0.021443 | 0.099811 | 0.048434 | 0.040153 | −0.023814 | 0.024605 | 0.025793 | −0.040486 | 0.011404 | 0.113558 |
| 11 | −0.089469 | −0.009371 | −0.023899 | −0.00074 | −0.018498 | −0.091454 | 0.014814 | −0.021293 | 0.005023 | −0.090244 | 0.012138 | 0.009862 | −0.036887 | −0.007445 |
| 12 | 0.018448 | 0.0487561 | 0.01855 | 0.033085 | 0.018554 | −0.001467 | 0.007224 | 0.011527 | 0.072975 | −0.035925 | −0.046754 | 0.022217 | 0.015056 | −0.007138 |
| 13 | 0.094818 | 0.0613761 | 0.016343 | 0.022577 | 0.003019 | −0.045158 | 0.002716 | −0.024174 | −0.06072 | 0.015317 | −0.108834 | 0.001687 | −0.010336 | 0.005461 |
| 14 | −0.001086 | 0.040086 | 0.008477 | 0.007504 | 0.003121 | 0.0947 | 0.001996 | 0.137943 | 0.070013 | 0.009448 | −0.030601 | 0.077446 | −0.012932 | −0.019232 |
| 15 | −0.009387 | 0.024561 | −0.043693 | −0.007763 | 0.037139 | −0.010098 | −0.095357 | 0.077377 | 0.049328 | 0.031328 | 0.070827 | −0.044493 | 0.027134 | 0.016834 |
| 16 | −0.021009 | −0.078317 | 0.001984 | −0.034445 | −0.018645 | 0.064835 | 0.042482 | 0.078542 | −0.03837 | −0.039077 | 0.001819 | −0.005946 | −0.009871 | 0.016397 |
| 17 | −0.059406 | −0.00188 | 0.017272 | 0.031422 | 0.042707 | 0.003179 | 0.027967 | −0.104423 | −0.065751 | −0.048087 | 0.002959 | −0.002456 | −0.063508 | −0.056111 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 18 | −0.0231371 | 0.0130211 | −0.0343361 | 0.011721 | 0.006274 | −0.01401 | 0.162415 | −0.087716 | 0.027869 | −0.011083 | 0.001966 | 0.039815 | −0.027801 | −0.013497 |
| 19 | 0.0978 | −0.009746 | 0.014413 | 0.050127 | 0.033214 | −0.029627 | 0.117955 | 0.000295 | 0.001877 | 0.038418 | −0.037405 | 0.053294 | 0.013628 | −0.042734 |
| 20 | −0.042317 | −0.067718 | −0.043027 | −0.057747 | −0.085096 | 0.035414 | 0.019358 | 0.016649 | 0.024567 | −0.042281 | 0.058242 | −0.045044 | −0.013906 | −0.008042 |
| 21 | −0.064148 | −0.033938 | 0.002358 | −0.019574 | −0.003854 | 0.002877 | −0.000698 | −0.119824 | −0.135656 | 0.051969 | 0.047351 | −0.026223 | 0.000784 | −0.087321 |
| 22 | 0.004344 | 0.01635 | 0.021212 | 0.009032 | 0.024853 | 0.036925 | 0.040255 | −0.050608 | −0.008836 | 0.00351 | −0.03608 | −0.004503 | −0.005643 | 0.022972 |
| 23 | 0.010605 | −0.026216 | −0.032806 | −0.053332 | −0.05837 | −0.014161 | 0.028207 | −0.050229 | 0.010468 | 0.011004 | −0.013773 | −0.051464 | 0.038355 | 0.093656 |
| 24 | −0.035602 | −0.04552 | 0.068605 | 0.059819 | 0.03851 | −0.07016 | −0.074324 | 0.044174 | 0.028798 | 0.01502 | 0.055495 | 0.054716 | 0.00268 | 0.045948 |
| 25 | −0.045886 | 0.021229 | −0.052057 | 0.027999 | 0.002674 | −0.000398 | 0.022312 | 0.072832 | −0.030846 | 0.033136 | 0.017407 | 0.012679 | 0.079204 | 0.002539 |
| 26 | −0.052524 | −0.047071 | 0.024236 | −0.070728 | −0.050951 | 0.025522 | 0.182591 | −0.033101 | 0.074817 | 0.217531 | −0.132334 | −0.026887 | −0.040932 | −0.046505 |
| 27 | 0.050305 | 0.002249 | −0.035005 | −0.028118 | −0.00029 | −0.001398 | 0.092505 | 0.103405 | −0.005138 | 0.001355 | −0.022138 | 0.059176 | 0.004231 | 0.090401 |
| 28 | −0.048469 | −0.043254 | −0.004065 | −0.022819 | −0.029095 | −0.03311 | −0.001732 | −0.115204 | 0.069967 | 0.006653 | −0.011031 | 0.144042 | 0.015834 | 0.137528 |
| 29 | 0.020593 | −0.022914 | 0.045209 | 0.018764 | 0.041197 | −0.016191 | −0.009532 | −0.051793 | 0.046386 | 0.013242 | 0.003065 | 0.030512 | 0.001405 | 0.046066 |
| 30 | 0.047879 | 0.036352 | 0.068622 | −0.00746 | −0.039857 | −0.040889 | 0.003477 | −0.038438 | 0.083712 | −0.003565 | −0.030284 | 0.123369 | −0.004599 | 0.031123 |
| 31 | 0.053376 | 0.015114 | 0.005052 | 0.007564 | 0.001694 | −0.001796 | −0.070039 | 0.079947 | 0.138281 | 0.12485 | 0.088066 | −0.054797 | −0.003876 | −0.028276 |
| 32 | −0.029432 | −0.035259 | −0.009431 | −0.034165 | 0.049705 | −0.012169 | −0.057479 | 0.021696 | −0.050329 | −0.054026 | −0.015087 | 0.0926331 | −0.017966 | −0.004573 |
| 33 | 0.017045 | −0.001975 | 0.013821 | 0.000415 | 0.037817 | −0.07213 | −0.109986 | −0.051803 | 0.100526 | −0.114958 | −0.061415 | 0.024559 | −0.019573 | −0.130663 |
| 34 | −0.027618 | −0.090938 | 0.008068 | −0.030267 | 0.037405 | −0.021831 | 0.061117 | −0.145052 | −0.075896 | −0.030856 | 0.050063 | −0.10928 | −0.012785 | −0.034121 |
| 35 | −0.054618 | 0.012386 | −0.030916 | −0.141061 | −0.071405 | −0.00041 | −0.030518 | −0.080089 | −0.035843 | −0.017029 | 0.019188 | −0.084573 | 0.003264 | 0.079671 |
| 36 | −0.014099 | 0.012156 | −0.016094 | 0.042005 | 0.04294 | −0.009268 | 0.052841 | 0.042654 | 0.035146 | 0.021808 | −0.111201 | −0.002682 | −0.004299 | −0.004751 |
| 37 | −0.052591 | −0.031688 | −0.006348 | −0.016581 | −0.021322 | −0.034456 | −0.171947 | −0.08832 | −0.154621 | 0.0652761 | −0.018722 | −0.113101 | −0.027163 | 0.029691 |
| 38 | −0.035239 | −0.037448 | −0.02179 | −0.000412 | 0.05413 | 0.031261 | −0.031842 | −0.01259 | −0.027164 | 0.01459 | 0.003881 | 0.124059 | 0.021929 | 0.041199 |
| 39 | 0.023659 | 0.001421 | 0.003394 | 4.023408 | −0.049952 | −0.03498 | 0.049594 | −0.040213 | 0.081503 | −0.047625 | −0.084009. | −0.051734 | 0.021259 | −0.041088 |
| 40 | −0.04254 | 0.008654 | −0.000441 | −0.05513 | −0.072092 | 0.067482 | −0.1574 | −0.015484 | −0.061017 | 0.052043 | 0.018028 | 0.104743 | 0.045333 | −0.060322 |
| 41 | 0.02901 | 0.049532 | −0.092905 | 0.014884 | 0.008511 | 0.079442 | 0.003785 | −0.024275 | −0.071584 | 0.024831 | 0.006087 | −0.072863 | −0.033199 | 0.000669 |
| 42 | 0.001678 | −0.004675 | −0.000264 | −0.003444 | −0.007385 | 0.022835 | −0.02626 | 0.010428 | −0.031194 | 0.014089 | −0.002015 | 0.019671 | 0.006543 | 0.004277 |
| 43 | 0.011514 | 0.029026 | 0.004353 | −0.00199 | 0.011508 | −0.002122 | −0.04229 | 0.046855 | 0.141362 | −0.025089 | 0.072191 | 0.118865 | 0.061905 | 0.022411 |
| 44 | 0.00634 | 0.050676 | −0.00124 | −0.041354 | 0.001152 | 0.002797 | 0.189521 | −0.011075 | 0.11042 | −0.005909 | 0.094611 | −0.071359 | −0.040465 | 0.10599 |
| 45 | 0.024483 | −0.015526 | −0.038997 | 0.011926 | −0.005 | −0.04225 | 0.070587 | 0.065519 | −0.050265 | 0.016167 | −0.012973 | 0.058997 | −0.032126 | −0.060008 |
| 46 | −0.002439 | −0.007903 | 0.019087 | −0.021597 | −0.032835 | −0.075992 | −0.028936 | −0.050999 | −0.035752 | 0.00586 | −0.056855 | −0.029785 | 0.031095 | 0.047604 |
| 47 | 0.021783 | −0.011754 | 0.050949 | 0.003479 | 0.032474 | 0.132512 | −0.025008 | 0.022637 | −0.077783 | 0.183553 | 0.095244 | −0.100474 | 0.110844 | 0.011536 |
| 48 | 0.0156191 | 0.095841 | −0.0329631 | 0.051743 | 0.023511 | −0.067873 | 0.083675 | −0.028634 | −0.160362 | −0.104082 | 0.1475391 | 0.0662741 | −0.026121 | 0.077126 |
| 49 | 0.05113 | −0.0594541 | −0.021868 | 0.043466 | 0.024408 | −0.035887 | 0.007865 | −0.078642 | 0.021962 | −0.094829 | −0.039731 | 0.041442 | −0.047278 | −0.112476 |
| 50 | 0.010344 | 0.082742 | −0.01133f | 0.041374 | 0.04369 | 0.047472 | 0.112512 | 0.020339 | 0.036008 | −0.066113 | 0.063454 | −0.014324 | −0.005682 | −0.006834 |
| 51 | 0.075131 | 0.086896 | −0.035145 | 0.043089 | 0.005749 | −0.032183 | −0.024675 | −0.038054 | 0.078332k | −0.035465 | −0.039165 | 0.032918 | −0.029437 | 0.056413 |
| 52 | −0.015923 | −0.003008 | −0.027834 | 0.002717 | 0.029973 | −0.058911 | 0.001975 | −0.058357 | 0.007673 | −0.035944 | −0.018994 | 0.000038 | −0.076446 | −0.048787 |
| 53 | −0.074159 | −0.00919 | 0.033798 | −0.020635 | −0.022952 | 0.012536 | 0.072702 | −0.020589 | 0.043875 | 0.122194 | 0.110111 | 0.02912 | 0.05702 | 0.069812 |
| 54 | 0.002618 | −0.090462 | 0.005392 | 0.06766 | 0.03925 | 0.011683 | 0.085756 | 0.09736 | −0.043328 | −0.072568 | −0.025213 | −0.005897 | −0.022668 | −0.063623 |
| 55 | 0.023391 | −0.027599 | 0.112688 | 0.049633 | 0.0289 | 0.040196 | 0.081897 | −0.098038 | −0.062938 | 0.006257 | 0.113289 | 0.107406 | 0.026045 | −0.043674 |
| 56 | −0.06036 | 0.00522 | −0.00806 | −0.008712 | 0.046967 | 0.035468 | −0.051367 | 0.007688 | 0.01816 | −0.067651 | −0.090315 | −0.036873 | 0.021658 | 0.101684 |
| 57 | 0.030021 | 0.018761 | −0.026621 | −0.042224 | −0.012627 | −0.025901 | 0.054665 | 0.125012 | −0.06047 | −0.027263 | −0.024393 | 0.003869 | 0.013921 | −0.017327 |
| 58 | 0.006063 | 0.020549 | −0.023803 | 0.013521 | −0.000399 | −0.058281 | −0.152542 | −0.043665 | 0.0332881 | −0.018201 | 0.0550691 | −0.052311 | −0.038206 | 0.048317 |
| 59 | −0.0288251 | −0.0264231 | −0.015249 | 0.014413 | −0.008589 | 0.048103 | −0.012804 | −0.075813 | 0.076793 | 0.014274 | 0.034736 | 0.003153 | −0.012047 | −0.015816 |
| 60 | 0.097239 | 0.058451 | −0.003766 | 0.028311 | −0.010883 | −0.003386 | 0.035758 | −0.140375 | −0.025604 | 0.078523 | 0.04997 | 0.096609 | 0.084964 | −0.017873 |
| 61 | −0.011339 | −0.007014 | 0.069834 | 0.01107 | 0.035273 | −0.006297 | −0.001643 | 0.107196 | 0.081345 | 0.074996 | 0.04758 | −0.017589 | −0.013928 | −0.019599 |
| 62 | −0.035614 | −0.002394 | −0.010691 | 0.001296 | 0.03103 | −0.009843 | 0.023609 | 0.035033 | −0.023585 | −0.070085 | −0.040098 | 0.306142 | −0.028553 | −0.020333 |
| 63 | 0.082246 | −0.035645 | −0.031138 | 0.038925 | 0.009964 | −0.065404 | −0.02773 | −0.075932 | 0.0515941 | 0.0633591 | −0.047799 | −0.058521 | 0.034351 | 0.05141 |
| 64 | −0.0685581 | −0.006181 | 0.0376391 | 0.003443 | 0.018001 | 0.047311 | −0.073476 | −0.058135 | −0.03645 | 0.064169 | −0.006399 | −0.072511 | 0.0336 | 0.004415 |
| 65 | −0.083064 | −0.007056 | 0.11924 | 0.016682 | 0.076924 | −0.014414 | 0.088399 | −0.151724 | −0.066672 | −0.037235 | 0.111164 | 0.005136 | 0.063555 | −0.069643 |
| 66 | −0.015107 | −0.025388 | −0.015539 | 0.058565 | 0.06005 | −0.024356 | 0.054801 | 0.080499 | −0.111844 | −0.005156 | 0.028167 | 0.052746 | −0.03922 | 0.023283 |
| 67 | −0.012856 | 0.011478 | 0.003484 | 0.015847 | 0.03265 | −0.003213 | 0.034434 | 0.094826 | −0.135588 | −0.024252 | 0.01074 | 0.005699 | 0.025449 | −0.040625 |
| 68 | 0.001134 | 0.028801 | −0.056501 | 0.029183 | 0.038531 | −0.012565 | −0.105526 | 0.013152 | −0.054725 | 0.007287 | −0.089277 | −0.020502 | 0.031378 | −0.078143 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 69 | 0.028726 | −0.035951 | −0.01758 | −0.041662 | 0.020315 | −0.026917 | 0.009682 | 0.069663 | −0.069029 | 0.051903 | 0.016815 | −0.06157 | −0.039754 | 0.064763 |
| 70 | −0.054196 | 0.022199 | −0.065202 | −0.074834 | −0.040688 | −0.04882 | −0.032271 | 0.053432 | 0.078994 | −0.042711 | −0.011641 | 0.013811 | 0.021986 | −0.10436 |
| 71 | −0.011142 | −0.009679 | 0.033617 | 0.013768 | 0.00655 | −0.030801 | 0.02979 | 0.045016 | −0.031803 | 0.062283 | 0.016738 | 0.060106 | −0.030805 | −0.0576 |
| 72 | −0.053683 | −0.023562 | −0.033031 | −0.046443 | −0.01568 | −0.029452 | −0.005822 | 0.035811 | −0.006088 | −0.119035 | 0.002151 | 0.029184 | −0.006823 | −0.067431 |
| 73 | −0.05397 | −0.010838 | 0.019816 | −0.003277 | −0.092744 | 0.043221 | 0.021642 | −0.083129 | −0.008476 | −0.028181 | −0.019301 | −0.016693 | 0.05366 | 0.04527 |
| 74 | 0.0097711 | −0.0302321 | 0.003211 | 0.018119 | 0.095535 | 0.089946 | 0.01945 | 0.103873 | 0.049193 | −0.021988 | 0.033646 | 0.059193 | 0.0127 | 0.033648 |
| 75 | 0.113437 | −0.009178 | 0.056828 | 0.018324 | 0.012584 | −0.041117 | −0.015194 | −0.062232 | −0.039403 | −0.036225 | 0.018461 | −0.109709 | 0.052241 | 0.110452 |
| 76 | −0.054444 | 0.01071 | −0.078662 | −0.032147 | −0.005068 | −0.016542 | 0.10999 | 0.037521 | 0.005917k | −0.008422 | 0.006846 | 0.044534 | −0.019481 | −0.055646 |
| 77 | −0.041674 | −0.037373 | 0.02509 | 0.005297 | −0.026383 | −0.030948 | −0.080751 | −0.133934 | 0.02199 | −0.019141 | −0.034027 | 0.013869 | 0.019209 | 0.071088 |
| 78 | −0.028975 | −0.062468 | −0.000912 | 0.008966 | 0.017948 | 0.087762 | −0.024805 | −0.032371 | 0.004783 | 0.02795 | 0.104603 | 0.0176 | −0.010672 | −0.041468 |
| 79 | 0.022989 | 0.00549 | 0.016027 | 0.065988 | 0.023886 | 0.03349 | −0.001178 | −0.095673 | 0.033357 | 0.067618 | −0.007431 | 0.046094 | −0.056155 | −0.024128 |
| 80 | 0.024209 | 0.006726 | −0.003061 | a 004263 | −0.00311 | −0.075047 | −0.008921 | −0.012847 | −0.143273 | 0.018706 | −0.005654 | 0.130222 | −0.032235 | 0.06719 |
| 81 | −0.02153 | 0.015765 | 0.071943 | 0.030676 | −0.008594 | −0.087671 | 0.028565 | 0.003832 | 0.030302 | −0.084325 | 0.019641 | 0.002864 | −0.021543 | 0.041216 |
| 82 | 0.017654 | 0.089558 | 0.054364 | 0.08881 | 0.122418 | 0.081631 | 0.045046 | −0.055256 | −0.030182 | 0.07252 | 0.111233 | 0.089401 | 0.047453 | 0.00661 |
| 83 | −0.070512 | −0.0381871 | −0.0206321 | −0.087444 | −0.109145 | 0.038663 | 0.121704 | −0.053382 | −0.045894 | −0.054162 | −0.059611 | −0.085359 | 0.0424141 | 0.050509 |
| 84 | −0.010885 | 0.016913 | −0.059144 | 0.092829 | 0.071292 | −0.048497 | 0.060988 | −0.078914 | 0.021642 | 0.035934 | 0.082971 | −0.017671 | −0.037305 | −0.042628 |
| 85 | −0.015686 | −0.018263 | −0.032222 | −0.036047 | 0.01949 | 0.059845 | −0.05249 | 0.027549 | −0.083609 | 0.010112 | 0.027363 | −0.065613 | −0.002085 | −0.02983 |
| 86 | 0.080794 | 0.018699 | −0.019965 | −0.012372 | 0.058841 | 0.009305 | −0.02696 | −0.089318 | 0.135775 | −0.047127 | −0.035589 | −0.08676 | −0.03964 | 0.039031 |
| 87 | 0.029505 | 0.006088 | −0.02917 | 0.031026 | −0.01718 | 0.011396 | −0.103729 | −0.064835 | −0.100247 | −0.035759 | −0.089903 | 0.031089 | 0.006978 | −0.059138 |
| 88 | −0.024533 | −0.069282 | −0.034949 | −0.080566 | −0.041216 | 0.076847 | 0.064757 | 0.114515 | −0.019484 | 0.00025 | −0.01289 | 0.020655 | −0.065501 | −0.113853 |
| 89 | 0.080977 | −0.001714 | 0.062697 | 0.020412 | 0.00786 | −0.024556 | −0.105903 | 0.077041 | −0.04183 | −0.010647 | 0.025259 | −0.019825 | 0.014478 | 0.044011 |
| 90 | 0.0451821 | −0.002219 | 0.0171421 | 0.029516 | −0.027533 | 0.064058 | −0.041146 | −0.01658 | 0.104238 | −0.103962 | 0.018599 | −0.133435 | 0.02302 | 0.014509 |
| 91 | −0.008669 | −0.007724 | 0.040366 | 0.05119 | 0.016696 | −0.104545 | −0.107739 | 0.08343 | 0.001041 | −0.085119 | −0.008381 | 0.043196 | 0.001474 | 0.032965 |
| 92 | 0.015226 | 0.004278 | −0.011164 | 0.048846 | 0.059855 | −0.007786 | 0.000757 | −0.03162 | 0.027352 | 0.032895 | −0.050074 | −0.157471 | −0.014099 | −0.112619 |
| 93 | −0.084634 | 0.119984 | −0.062409 | 0.018293 | −0.018806 | 0.038841 | −0.031798 | 0.047782 | 0.05836 | −0.039035 | −0.02895 | 0.100654 | 0.048313 | 0.100788 |
| 94 | 0.04918 | 0.040852 | 0.018529 | 0.012303 | 0.044549 | −0.060184 | −0.049151 | 0.014214 | −0.047702 | −0.032142 | 0.013556 | 0.109333 | 0.003466 | 0.002878 |
| 95 | −0.040184 | −0.017643 | −0.045591 | −0.003921 | −0.039503 | −0.034649 | −0.045497 | 0.055792 | −0.007011 | 0.036939 | 0.025614 | 0.050048 | 0.022953 | 0.071356 |
| 96 | 0.008978 | 0.063048 | −0.042052 | −0.052946 | −0.037324 | −0.098028 | −0.009576 | −0.009679 | 0.067989 | −0.043648 | −0.025977 | 0.026333 | −0.023283 | −0.038852 |
| 97 | 0.139927 | −0.030591 | 0.126541 | 0.179712 | 0.135258 | −0.013394 | 0.047766 | 0.027651 | −0.033776 | −0.011483 | −0.11471 | −0.046252 | −0.024785 | 0.017548 |
| 98 | 0.1013871 | 0.0401961 | −0.2468021 | 0.005648 | 0.041497 | 0.063242 | 0.001308 | −0.208085 | 0.019792 | 0.037481 | 0.127929 | −0.001318 | 0.01334 | −0.172329 |
| 99 | 0.048375 | −0.073416 | −0.023889 | −0.012483 | 0.005005 | 0.004863 | 0.016604 | −0.136008 | −0.106892 | 0.016843 | 0.055434 | 0.061151 | 0.043574 | −0.02422 |
| 100 | 0.012647 | −0.021999 | 0.0508181 | 0.019333 | 0.002252 | −0.010122 | 0.016982 | 0.009738 | −0.007207 | 0.036596 | −0.023157 | −0.000276 | 0.002644 | −0.00886 |
| 101 | 0.006012 | −0.003394 | 0.016214 | 0.007734 | 0.001752 | 0.005361 | 0.020127 | −0.016959 | 0.017307 | 0.004006 | −0.028661 | −0.029794 | 0.00781 | 0.004504 |
| 102 | 0.024629 | 0.008154 | −0.017253 | 0.011312 | 0.020021 | 0.030274 | 0.022951 | 0.049769 | −0.033877 | −0.001448 | −0.004108 | 0.007738 | 0.019476 | −0.030682 |
| 103 | −0.018142 | 0.007959 | 0.041959 | −0.01759 | −0.027069 | 0.002342 | −0.017312 | −0.012066 | −0.065245 | −0.027674 | −0.048996 | −0.034712 | 0.001644 | 0.008997 |
| 104 | 0.0508221 | 0.017262 | 0.029697 | 0.008988 | 0.002209 | −0.060246 | −0.004979 | −0.020206 | 0.0791021 | −0.035487 | −0.017764 | −0.009871 | −0.015816 | 0.051496 |
| 105 | 0.014068 | 0.013613 | 0.007086 | 0.046221 | 0.066425 | −0.010817 | 0.029258 | 0.044364 | −0.08542 | 0.005357 | 0.02635 | 0.051072 | 0.003323 | −0.037745 |
| 106 | −0.008159 | −0.002288 | 0.018916 | 0.013844 | 0.008938 | 0.016598 | −0.024342 | 0.016264 | 0.032893 | 0.036212 | −0.034025 | 0.110027 | −0.021061 | −0.049335 |
| 107 | −0.052753 | −0.039137 | 0.025349 | 0.002244 | 0.003563 | −0.009665 | 0.034413 | 0.040465 | −0.046222 | −0.048973 | 0.001232 | 0.006911 | 0.014052 | 0.009829 |
| 108 | 0.004045 | −0.018008 | 0.008062 | 0.040965 | 0.022974 | 0.011241 | −0.002002 | 0.002055 | 0.003309 | −0.076994 | −0.00851 | −0.043328 | 0.011701 | 0.013328 |
| 109 | 0.003941 | 0.012755 | −0.004887 | 0.000523 | −0.019086 | −0.028552 | −0.017781 | −0.043093 | 0.034272 | −0.020831 | −0.037233 | −0.021279 | 0.027112 | −0.011891 |
| 110 | −0.036822 | −0.006054 | 0.029991 | 0.017027 | −0.004658 | −0.022772 | −0.037171 | 0.048038 | −0.026048 | −0.031716 | 0.032624 | 0.018405 | 0.027088 | −0.029385 |
| 111 | −0.009297 | 0.015958 | 0.037062 | 0.008172 | 0.017666 | 0.051071 | −0.016545 | 0.042823 | −0.045532 | −0.000834 | 0.026529 | −0.068053 | 0.040314 | −0.03446 |
| 112 | 0.040102 | −0.063212 | 0.011432 | 0.037689 | 0.009299 | 0.040562 | −0.058158 | −0.054492 | −0.001203 | 0.027795 | 0.021624 | 0.021496 | −0.009908 | 0.05863 |
| 113 | 0.013838 | 0.013769 | −0.017543 | −0.035402 | 0.010988 | −0.029924 | −0.002448 | 0.046536 | −0.034282 | 0.054175 | 0.034935 | 0.009701 | 0.011641 | −0.034924 |
| 114 | 0.032266 | 0.0541 | 0.017639 | −0.020058 | −0.004058 | −0.005249 | 0.025983 | −0.026981 | 0.0191221 | 0.0213771 | 0.0446661 | 0.0388291 | 0.0317181 | 0.062925 |
| 115 | −0.0296631 | −0.008669 | −0.009721 | −0.011028 | −0.011027 | −0.061378 | −0.050793 | −0.047893 | 0.039616 | 0.007113 | −0.009257 | −0.045374 | 0.007845 | −0.046761 |
| 116 | 0.034619 | 0.043268 | −0.031218 | −0.012164 | 0.011762 | −0.035375 | −0.011292 | 0.039729 | −0.007427 | 0.007913 | −0.006745 | −0.083798 | 0.011798 | −0.07167 |
| 117 | −0.036729 | 0.001447 | −0.004286 | −0.018611 | −0.040967 | −0.00171 | 0.033768 | 0.06792 | −0.069637 | 0.004516 | −0.018545 | −0.012652 | 0.017094 | 0.022593 |
| 118 | −0.044082 | −0.048136 | −0.034624 | −0.030306 | −0.050026 | −0.01459 | −0.003541 | 0.037708 | −0.041182 | −0.001985 | −0.008352 | −0.063839 | −0.005059 | 0.021838 |
| 119 | −0.041488 | −0.102449 | 0.072825 | 0.015525 | 0.001667 | −0.03633 | −0.026364 | −0.049355 | −0.045817 | −0.042948 | −0.014812 | 0.006356 | −0.015196 | −0.043322 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 120 | −0.022614 | −0.015709 | −0.023417 | −0.012827 | −0.016083 | −0.007328 | 0.012143 | −0.012325 | −0.066363 | −0.026658 | −0.014144 | −0.017046 | −0.00881 | −0.010036 |
| 121 | −0.038224 | −0.003203 | −0.00472 | −0,035677 | −0.024755 | 0.055513 | 0.022165 | 0.017769 | −0.055592 | 0.039734 | −0.024444 | −0.025402 | 0.03384 | 0.001567 |
| 122 | −0.118012 | −0.017367 | −0.018183 | −0.038851 | −0.022598 | 0.025135 | −0.016354 | 0.040047 | −0.015227 | 0.01578 | 0.044775 | −0.028022 | 0.019357 | −0.007385 |
| 123 | 0.782466 | −0.041644 | −0.007091 | −0.077106 | −0.048185 | 0.027091 | 0.023557 | 0.022773 | −0.017683 | −0.011814 | 0.019709 | 0.016125 | 0.012451 | −0.032239 |
| 124 | −0.051382 | 0.840566 | 0.027462 | −0.025566 | −0.021802 | 0.007822 | −0.003372 | −0.013648 | 10.024174 | 0.0119361 | −0.021554 | −0.046801 | −0.027462 | −0.065322 |
| 125 | −0.006032 | 0.0390431 | 0.7917641 | −0.052413 | −0.027583 | −0.005415 | −0.011867 | −0.025567 | 0.0112941 | −0.013009 | 0.018094 | −0.012513 | −0.023307 | −0.064917 |
| 126 | −0.081707 | −0.011385 | −0.070231 | 0.833838 | −0.116741 | 0.001114 | 0.012867 | 0.000781 | −0.011184 | 0.014002 | −0.017267 | −0.038241 | 0.005997 | −0.014562 |
| 127 | −0.066396 | −0.005651 | −0.056982 | −0.118304 | 0.841592 | −0.017953 | −0.01752 | −0.010191 | 0.01303 | 0.012225 | −0.034793 | −0.010284 | 0.010995 | 0.014141 |
| 128 | 0.026678 | 0.020165 | −0.009103 | 0.012845 | 0.00186 | 0.776869 | −0.009704 | −0.021795 | −0.002751 | −0.091663 | −0.046979 | 0.048402 | −0.03823 | 0.00155 |
| 129 | −0.026414 | 0.0018 | −0.015108 | 0.005447 | −0.001926 | −0.012731 | 0.486811 | −0.033632 | −0.042645 | −0.000217 | 0.012566 | 0.030457 | 0.055349 | 0.007105 |
| 130 | 0.018226 | −0.012026 | 0.0142061 | 0.000944 | −0.005915 | −0.036269 | −0.010006 | 0.455433 | −0.037914 | 0.0166051 | 0.045516 | −0.024353 | 0.0035861 | −0.021514 |
| 131 | −0.037322 | −0.031253 | 0.0001841 | −0.011996 | 0.014283 | 0.01434 | −0.004639 | −0.030743 | 0.568276 | 0.022988 | 0.03137 | −0.017895 | 0.032501 | −0.022679 |
| 132 | −0.013065 | 0.020962 | −0.034519 | 0.02444 | 0.023136 | −0.086344 | 0.013684 | 0.022153 | −0.005428 | 0.649323 | −0.011241 | 0.020581 | −0.010052 | −0.019186 |
| 133 | −0.002509 | −0.003547 | −0.012672 | −0.019535 | −0.055509 | −0.0597 | −0.041532 | 0.042996 | 0.025647 | −0.060035 | 0.694373 | −0.013011 | −0.022284 | −0.030222 |
| 134 | 0.012805 | −0.032611 | −0.010325 | −0.039496 | −0.037748 | 0.028297 | −0.033325 | −0.047425 | 0.000013 | 0.049549 | −0.01719 | 0.525459 | −0.001789 | −0.005814 |
| 135 | 0.001564 | −0.03174 | −0.022026 | 0.005247 | 0.013609 | −0.05329 | 0.036035 | 0.004492 | 0.026055 | −0.037974 | −0.03418 | −0.000995 | 0.881072 | −0.050765 |
| 136 | −0.007139 | −0.050164 | −0.041256 | 0.022851 | 0.037643 | 0.009132 | 0.022641 | −0.044561 | −0.003475 | −0.012404 | −0.00214 | −0.028081 | −0.053973 | 0.689341 |
| 137 | −0.013081 | 0.030987 | −0.042587 | −0.029106 | −0.032437 | −0.061846 | −0.052802 | −0.045028 | −0.012095 | 0.000136 | −0.015789 | 0.001268 | 0.024979 | 0.02207 |
| 138 | 0.005545 | 0.006252 | −0.006919 | −0.029721 | −0.03125 | −0.024991 | −0.013096 | −0.060747 | −0.083492 | 0.015976 | 0.032391 | −0.062661 | −0.009217 | 0.007079 |
| 139 | 0.025789 | −0.017614 | 0.023603 | 0.008633 | 0.033959 | 0.026498 | 0.064126 | 0.035721 | −0.003119 | −0.045701 | 0.008684 | −0.048774 | 0.002619 | −0.030462 |
| 140 | 0.006195 | 0.003517 | −0.009745 | 0.015134 | −0.00458 | −0.012042 | −0.03908 | −0.001024 | −0.035431 | −0.035391 | −0.061498 | −0.028988 | 0.023598 | −0.012822 |
| 141 | −0.003666 | 0.025113 | −0.013944 | 0.00725 | 0.028687 | −0.039759 | 0.052355 | −0.053923 | 0.055895 | −0.047179 | 0.01586 | 0.037258 | −0.04562 | −0.004455 |
| 142 | −0.047082 | −0.006155 | 0.011447 | −0.03665 | −0.028001 | 0.002169 | −0.01313 | −0.042029 | −0.012557 | 0.011445 | −0.019838 | 0.048483 | −0.013509 | −0.02824 |
| 143 | −0.049535 | −0.064611 | 0.00999 | 0.046187 | 0.04043 | 0.022562 | −0.05003 | 0.035741 | 0.0509 | 0.024116 | −0.063548 | −0.000108 | −0.031486 | −0.033495 |
| 144 | −0.061075 | −0.085278 | 0.033928 | −0.01226 | −0.007679 | 0.006853 | −0.035189 | 0.010212 | 0.065777 | 0.037543 | −0.002553 | −0.024244 | −0.040765 | −0.071898 |
| 145 | −0.063197 | −0.019215 | −0.01403 | −0.041927 | −0.021659 | −0.010511 | 0.034657 | 0.027067 | 0.028324 | −0.022382 | −0.069828 | −0.014833 | −0.045416 | −0.082266 |
| 146 | −0.001995 | 0.013335 | −0.053557 | −0.024832 | −0.014407 | −0.064537 | 0.019697 | −0.005772 | 0.013605 | −0.056356 | −0.04926 | −0.017926 | −0.058445 | −0.02842 |
| 147 | 0.01264 | 0.016751 | −0.031009 | −0.031928 | −0.004146 | −0.005059 | −0.037033 | −0.083792 | −0.013783 | 0.005249 | 0.019144 | −0.039979 | 0.003911 | 0.02338 |
| 148 | 0.013822 | 0.014829 | 0.064968 | −0.028082 | −0.034573 | −0.075476 | 0.02684 | −0.041101 | −0.015871 | 0.015038 | −0.029533 | 0.077659 | −0.026546 | −0.004458 |
| 149 | 0.005392 | 0.006928 | −0.001383 | 0.014369 | 0.012729 | −0.027882 | 0.035776 | 0.038856 | −0.003938 | −0.001838 | 0.020158 | −0.070265 | −0.031088 | −0.003126 |
| 150 | 0.008602 | −0.022937 | −0.090639 | −0.033663 | −0.024121 | −0.016666 | −0.053617 | −0.110638 | −0.025258 | −0.036001 | 0.066898 | 0.014834 | −0.029004 | −0.011003 |
| 151 | −0.027126 | 0.003973 | 0.007769 | −0.007174 | 0.001579 | 0.051295 | −0.001321 | −0.046583 | 0.028385 | 0.022097 | 0.072474 | −0.084288 | 0.03574 | −0.016455 |
| 152 | 0.021919 | −0.046837 | −0.005695 | 0.006194 | −0.030072 | 0.021393 | −0.047793 | −0.002979 | −0.005307 | 0.037061 | 0.024054 | −0.003464 | 0.00824 | −0.023353 |
| 153 | −0.0299 | −0.013688 | 0.021207 | 0.030689 | 0.00778 | −0.021741 | −0.048169 | 0.010928 | 0.067042 | −0.04299 | 0.026687 | 0.046835 | −0.017107 | −0.006006 |
| 154 | −0.013935 | −0.033782 | 0.011667 | −0.012938 | 0.001016 | 0.006974 | 0.025263 | −0.080627 | −0.031735 | −0.003968 | 0.062379 | −0.001931 | −0.021203 | −0.065442 |
| 155 | −0.017572 | −0.012185 | −0.061795 | −0.014865 | −0.025355 | −0.008034 | −0.029233 | −0.002642 | 0.010422 | −0.081194 | 0.012441 | 0.025571 | −0.010557 | −0.071959 |
| 156 | −0.041314 | 0.009581 | −0.056309 | −0.015618 | −0.004074 | −0.067471 | 0.085332 | −0.050907 | −0.090597 | −0.004153 | −0.017298 | 0.019869 | −0.059908 | −0.04085 |
| 157 | −0.019585 | 0.004679 | −0.039168 | −0.037565 | −0.009436 | −0.053833 | 0.0011 | 0.014723 | 0.063917 | −0.018952 | −0.008768 | 0.074348 | −0.049206 | −0.031432 |
| 158 | −0.040871 | −0.013523 | −0.048643 | −0.029402 | −0.044562 | −0.010228 | 0.058108 | 0.015851 | 0.034633 | −0.000641 | −0.010907 | −0.028381 | 0.002871 | −0.005527 |
| 159 | −0.020521 | −0.01063 | 0.028278 | −0.007647 | −0.023426 | −0.031868 | −0.010736 | 0.01736 | 0.076113 | 0.068599 | 0.014219 | 0.000599 | −0.042937 | −0.019548 |
| 160 | −0.023209 | −0.031299 | 0.003506 | 0.012828 | 0.000796 | −0.012665 | −0.057029 | 0.00833 | −0.018698 | 0.0568 | −0.079034 | −0.001933 | 0.011363 | −0.016319 |
| 161 | −0.007196 | −0.000086 | 0.021259 | 0.016385 | 0.002603 | −0.049939 | −0.061864 | −0.036559 | −0.000247 | −0.018346 | 0.034914 | 0.054855 | −0.011451 | −0.000695 |
| 162 | −0.005572 | −0.059479 | 0.038833 | 0.053847 | 0.044168 | 0.023933 | −0.010547 | 0.04695 | −0.027855 | 0.032602 | 0.034212 | −0.00372 | −0.038805 | −0.007194 |
| 163 | 0.023881 | −0.03769 | 0.019333 | 0.002251 | −0.015643 | 0.011449 | −0.018074 | 0.011424 | −0.024656 | 0.014028 | 0.001385 | −0.003144 | −0.044153 | −0.028371 |
| 164 | 0.000142 | −0.023325 | −0.048703 | −0.033691 | −0.041881 | −0.019206 | −0.000357 | 0.056376 | −0.06848 | 0.002997 | −0.017679 | 0.016746 | −0.004451 | −0.033725 |
| 165 | 0.033217 | −0.003255 | −0.026462 | 0.004288 | −0.019531 | 0.012742 | −0.045428 | −0.025578 | 0.058736 | −0.038592 | −0.034886 | −0.025879 | 0.005021 | 0.014777 |
| 166 | −0.023664 | −0.072193 | 0.014406 | 0.00113 | 0.028739 | 0.04139 | −0.041534 | −0.069654 | 0.003627 | −0.009483 | −0.051195 | 0.009232 | −0.024471 | −0.033903 |
| 167 | −0.021724 | −0.035523 | 0.024479 | 0.024465 | 0.014638 | −0.012933 | 0.005588 | −0.042261 | 0.050523 | −0.074801 | −0.022929 | 0.027065 | −0.029336 | −0.070941 |
| 168 | 0.021093 | 0.010614 | −0.02851 | −0.009501 | 0.008098 | −0.025724 | −0.055113 | −0.061901 | 0.035088 | 0.059623 | 0.006248 | 0.023796 | −0.020472 | −0.03246 |
| 169 | 0.005409 | −0.009189 | 0.022519 | 0.004133 | 0.001626 | 0.028584 | −0.006504 | −0.01499 | 0.004316 | 0.016015 | 0.003137 | 0.009139 | −0.00161 | 0.019376 |
| 170 | 0.006988 | −0.007571 | 0.026294 | 0.008364 | −0.000573 | −0.000379 | −0.004391 | −0.048398 | −0.005614 | −0.007022 | 0.020702 | 0.006153 | 0.014186 | 0.028431 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 171 | −0.025783 | −0.011932 | 0.0378041 | 0.003896 | 0.00788 | 0.023968 | −0.010713 | −0.00701 | 0.0049621 | 0.014181 | −0.000776 | −0.005503 | 0.013863 | 0.024627 |
| 172 | 0.017356 | −0.024659 | 0.0095121 | −0.000367 | 0.006331 | 0.024688 | −0.004179 | 0.000208 | 0.026362 | 0.058227 | −0.017433 | 0.00844 | −0.003029 | −0.016139 |
| 173 | 0.016821 | 0.034498 | −0.009625 | 0.014379 | −0.005771 | −0.017961 | −0.02297 | −0.000661 | 0.037204 | 0.071117 | −0.050641 | 0.010402 | 0.005646 | 0.025306 |
| 174 | 0.021943 | 0.020704 | 0.0022 | 0.00077 | 0.003677 | −0.018103 | 0.00746 | −0.028471 | 0.003522 | −0.000524 | −0.046945 | 0.010187 | −0.019428 | 0.013264 |
| 175 | −0.009816 | −0.029536 | 0.00634 | 0.005519 | −0.007123 | −0.000514 | −0.005398 | −0.01306 | −0.014633 | 0.006969 | 0.012656 | −0.006007 | −0.004178 | 0.033621 |
| 176 | −0.038104 | −0.064918 | 0.023865 | −0.027171 | −0.025212 | 0.052855 | 0.049975 | −0.004095 | −0.003384 | −0.001152 | −0.046787 | 0.033046 | 0.01506 | −0.028174 |
| 177 | 0.032705 | −0.056343 | 0.028331 | 0.012947 | 0.028762 | −0.015858 | 0.083843 | 0.000625 | 0.001489 | 0.000163 | 0.041018 | −0.042882 | −0.056919 | −0.021227 |
| 178 | −0.013962 | −0.02361 | 0.038198 | −0.002589 | −0.006542 | 0.033114 | −0.003667 | 0.026015 | 0.016091 | 0.040859 | −0.037894 | 0.026834 | −0.001423 | 0.021728 |
| 179 | −0.008774 | 0.01069 | 0.034431 | 0.022311 | 0.016785 | −0.005279 | 0.00804 | 0.003173 | −0.01674f | −0.017335 | −0.004621 | 0.031882 | 0.01099 | 0.008713 |
| 180 | −0.008506 | 0.019145 | 0.001382 | 0.015107 | 0.01163 | 0.019309 | 0.005277 | −0.000684 | 0.014061 | 0.010952 | −0.009876 | 0.015838 | 0.008963 | 0.003654 |
| 181 | −0.003462 | 0.012871 | 0.0174621 | 0.026053 | 0.015123 | 0.008698 | 0.020841 | 0.000624 | 0.0092761 | −0.02671 | −0.012846 | 0.014047 | 0.021048 | 0.009059 |
| 182 | 0.0159981 | −0.002848 | 0.0372851 | 0.019019 | −0.002278 | −0.012282 | 0.016153 | −0.017212 | 0.025433 | −0.028213 | −0.019488 | 0.015524 | 0.035653 | 0.024003 |
| 183 | −0.011615 | 0.00717 | 0.030181 | 0.017853 | 0.025547 | −0.045056 | −0.003141 | 0.027065 | −0.014246 | −0.038721 | 0.036076 | −0.000144 | 0.02031 | −0.000608 |
| 184 | −0.035817 | 0.014584 | −0.009827 | −0.00522 | 0.013432 | −0.020696 | −0.018088 | 0.039231 | −0.001579 | −0.039986 | 0.037102 | −0.03114 | 0.0049 | −0.019233 |
| 185 | −0.01804 | 0.024118 | −0.030146 | −0.042528 | −0.016515 | 0.029698 | 0.06577 | 0.078007 | 0.043569 | 0.032457 | 0.04763 | 0.004819 | −0.010451 | 0.018009 |
| 186 | −0.010769 | −0.000987 | 0.013334 | 0.026181 | 0.051891 | 0.07765 | −0.025981 | −0.134249 | 0.012933 | 0.022988 | 0.04265 | −0.020614 | 0.02472 | −0.061737 |
| 187 | 0.040398 | 0.012474 | −0.031566 | −0.0013 | 0.005721 | 0.005483 | −0.006894 | −0.008342 | 0.031415 | 0.032757 | 0.009123 | −0.009105 | −0.004645 | −0.035161 |
| 188 | 0.034848 | 0.018116 | −0.006789 | −0.001004 | 0.010261 | −0.001462 | 0.013545 | −0.002163 | 0.010708 | −0.008945 | 0.013808 | 0.03028 | −0.0179 | −0.028012 |
| 189 | −0.020117 | 0.001933 | 0.02972 | −0.025134 | −0.000621 | −0.008624 | 0.02935 | −0.020614 | −0.058323 | −0.04435 | 0.028973 | 0.017818 | −0.011708 | 0.000026 |
| 190 | −0.018662 | −0.013639 | 0.00551 | 0.004861 | 0.018203 | −0.00403 | −0.012065 | −0.003987 | 0.006289 | −0.000221 | −0.014367 | −0.04532 | 0.023077 | −0.004544 |
| 191 | 0.001271 | 0.000845 | −0.004401 | 0.019485 | 0.037702 | −0.024388 | 0.002703 | 0.004179 | −0.02259 | −0.04814 | −0.021256 | −0.031229 | −0.014803 | −0.03095 |
| 192 | 0.036117 | −0.007858 | 0.001158 | 0.009141 | −0.01607 | −0.014623 | 0.062245 | −0.028171 | −0.011467 | −0.002344 | 0.008068 | −0.003293 | −0.015921 | −0.039563 |
| 193 | 0.004823 | 0.002655 | 0.0179 | 0.047166 | 0.007532 | −0.028757 | 0.037347 | 0.011238 | −0.010757 | −0.015232 | 0.004267 | 0.021341 | 0.002246 | −0.007615 |
| 194 | −0.04083 | −0.011195 | 0.014136 | 0.022 | 0.026477 | 0.032173 | 0.003414 | 0.054047 | −0.005629 | −0.035399 | 0.040681 | 0.016376 | −0.009052 | 0.008617 |
| 195 | −0.038028 | 0.00431 | −0.007683 | 0.025944 | 0.039438 | 0.007742 | −0.007775 | −0.003261 | −0.058943 | −0.01979 | 0.002442 | −0.018403 | 0.007185 | −0.016279 |
| 196 | −0.010112 | −0.002007 | 0.008451 | 0.010927 | 0.00867 | 0.030726 | 0.003173 | −0.001146 | 0.036118 | −0.008168 | −0.017383 | −0.07002 | 0.012198 | −0.010294 |
| 197 | 0.007862 | 0.008337 | 0.023592 | 0.023764 | 0.018138 | −0.045311 | 0.046247 | −0.004372 | −0.01348 | −0.030744 | −0.037464 | −0.069813 | −0.005353 | 0.024064 |
| 198 | −0.00287 | −0.019068 | −0.001557 | −0.029802 | 0.01333 | −0.048682 | 0.031006 | −0.030478 | −0.024995 | 0.025419 | 0.010767 | −0.007074 | −0.028234 | 0.020824 |
| 199 | −0.005591 | 0.015522 | −0.020659 | −0.013816 | −0.015559 | −0.007209 | −0.105467 | −0.009989 | −0.048719 | −0.022507 | 0.013266 | 0.036243 | 0.004548 | 0.002645 |
| 200 | 0.02797 | −0.013582 | 0.00791 | 0.034863 | 0.025871 | −0.038149 | −0.052423 | 0.037438 | 0.004798 | −0.021196 | −0.039616 | 0.005585 | −0.025986 | −0.000032 |
| 201 | 0.017882 | −0.006532 | −0.001394 | 0.007675 | 0.002463 | 0.011721 | 0.017345 | 0.080325 | −0.001527 | −0.057481 | −0.011157 | −0.036811 | −0.02188 | −0.014123 |
| 202 | 0.007934 | −0.01681 | 0.035015 | 0.010559 | 0.031008 | −0.032856 | −0.032012 | −0.033316 | 0.000902 | 0.039014 | −0.043133 | −0.012513 | −0.022377 | −0.009134 |
| 203 | 0.014872 | 0.019001 | 0.013771 | −0009216 | −0.00323 | −0.030077 | −0.060651 | 0.072202 | −0.039743 | 0.0129 | −0.00064 | −0.012429 | −0.004087 | 0.05427 |
| 204 | 0.03354 | −0.009518 | −0.008047 | 0.002008 | −0.001888 | −0.037644 | −0.108376 | 0.049921 | 0.047007 | −0.018746 | 0.044008 | −0.021199 | 0.003272 | 0.021752 |
| 205 | −0.011333 | 0.014703 | 0.002448 | −0.020985 | −0.037595 | −0.03973 | 0.013575 | 0.039538 | −0.011995 | −0.030802 | −0.030299 | 0.041795 | 0.012892 | 0.034484 |
| 206 | −0.041376 | −0.014987 | −0.015817 | −0.014432 | 0.003398 | 0.059814 | −0.021724 | 0.047974 | −0.085231 | 0.056534 | 0.024313 | −0.024089 | −0.016636 | 0.021956 |
| 207 | −0.01821 | −0.007614 | −0.008995 | 0.025766 | 0.007385 | 0.011103 | 0.054017 | 0.020097 | −0.002958 | −0.016361 | 0.0167 | 0.053104 | 0.028052 | 0.030815 |
| 208 | 0.039852 | 0.019864 | −0.05271 | 0.01066 | 0.000598 | 0.000255 | −0.076399 | −0.067722 | −0.072882 | 0.040758 | 0.008964 | −0.029611 | −0.007618 | 0.021425 |
| 209 | 0.034694 | 0.002608 | 0.009896 | 0.050915 | 0.034334 | 0.016758 | 0.018128 | 0.006671 | 0.051236 | −0.005321 | −0.027663 | −0.076223 | −0.043665 | −0.030483 |
| 210 | −0.020742 | 0.012885 | −0.077592 | −0.022248 | −0.019436 | −0.010737 | −0.026495 | 0.070859 | −0.027085 | −0.04057 | 0.033627 | −0.009317 | 0.022599 | −0.026994 |
| 211 | 0.007808 | −0.008023 | −0.004644 | −0.021458 | −0.001382 | −0.045252 | −0.030645 | 0.020274 | −0.02258 | 0.103469 | −0.008095 | −0.026977 | −0.039602 | 0.001856 |
| 212 | 0.047715 | −0.002029 | 0.013154 | 0.032278 | 0.05721 | 0.008953 | 0.00405 | 0.058405 | 0.003799 | 0.030722 | 0.016786 | −0.029754 | 0.013654 | −0.015215 |
| 213 | −0.002442 | −0.004883 | 0.011326 | 0.005949 | 0.028488 | 0.074424 | −0.020896 | 0.071118 | 0.029987 | −0.005519 | −0.059585 | −0.052704 | 0.042238 | −0.002509 |
| 214 | −0.045279 | 0.012955 | 0.019883 | −0.002589 | −0.007266 | 0.003603 | −0.003846 | 0.010338 | −0.003259 | 0.008729 | −0.007745 | 0.040787 | 0.001389 | −0.025 |
| 215 | −0.018865 | 0.025525 | −0.041898 | 0.046726 | 0.035017 | 0.029412 | −0.050956 | −0.00357 | 0.025092 | −0.0414 | 0.005346 | −0.012333 | 0.00284 | 0.014852 |
| 216 | −0.017211 | −0.03881 | 0.005925 | −0.008258 | 0.002205 | 0.001374 | 0.008335 | −0.017328 | 0.032871 | 0.027008 | 0.002983 | −0.005171 | −0.038574 | −0.005854 |
| 217 | 0.015691 | −0.025655 | 0.017432 | 0.002231 | −0.00173 | −0.000598 | −0.011951 | 0.00845 | −0.042845 | 0.010206 | 0.061221 | 0.026792 | 0.011414 | 0.017876 |
| 218 | −0.032093 | 0.019189 | 0.016084 | 0.030237 | 0.012917 | −0.010394 | 0.018031 | 0.033614 | 0.003795 | −0.033112 | −0.029757 | 0.010511 | −0.016806 | 0.011892 |
| 219 | −0.039613 | 0.010498 | 0.019576 | 0.015477 | 0.017524 | 0.006889 | 0.055523 | 0.001473 | 0.004773 | −0.021672 | −0.004564 | 0.013386 | −0.022897 | −0.017823 |
| 220 | −0.00388 | −0.038662 | −0.026351 | −0.012908 | −0.017939 | −0.006644 | 0.016844 | 0.011835 | −0.023097 | −0.022106 | 0.008977 | −0.055063 | 0.006751 | 0.019202 |
| 221 | 0.007763 | 0.010083 | 0.01156 | −0.005707 | 0.003542 | −0.003247 | 0.059052 | −0.002061 | 0.007584 | 0.022584 | −0.025777 | 0.006692 | −0.011038 | 0.031582 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 222 | 0.037189 | 0.017426 | 0.001945 | 0.019324 | −0.037113 | 0.007807 | 0.004073 | −0.00561 | 0.036322 | 0.041974 | −0.021242 | −0.018378 | −0.014222 | 0.00163 |
| 223 | −0.012249 | −0.000403 | −0.007171 | 0.01375 | −0.044184 | 0.014869 | −0.0274 | −0.008784 | 0.047171 | −0.00705 | −0.025327 | 0.010426 | 0.023579 | 0.018116 |
| 224 | 0.003491 | 0.005763 | −0.015902 | −0.01247 | −0.005344 | 0.014635 | 0.048767 | −0.027927 | −0.006502 | 0.005441 | −0.002542 | −0.004338 | −0.002682 | 0.007882 |
| 225 | 0.008534 | 0.035899 | −0.022 | −0.012324 | −0.012706 | 0.006307 | 0.009039 | −0.036641 | 0.010821 | 0.021349 | −0.010476 | −0.005866 | 0.006799 | 0.009371 |
| 226 | −0.014303 | −0.000549 | −0.002079 | −0.003396 | 0.011753 | −0.008068 | −0.04713 | −0.012582 | −0.005852 | −0.017649 | −0.004274 | 0.001037 | 0.008588 | −0.002218 |
| 227 | −0.016603 | −0.010368 | −0.024392 | 0.003979 | 0.024606 | 0.01573 | −0.004151 | 0.02656 | 0.021875 | −0.029859 | 0.044426 | −0.019631 | −0.014735 | 0.003773 |
| 228 | 0.000236 | −0.007376 | 0.009074 | −0.017571 | −0.011325 | −0.018681 | −0.043108 | −0.006468 | 0.009991 | −0.045047 | 0.017374 | −0.01444 | 0.015904 | −0.00055 |
| 229 | 0.006729 | −0.009019 | −0.008528 | −0.003118 | −0.012295 | 0.027173 | 0.063048 | 0.016525 | 0.012155 | −0.025341 | 0.037789 | −0.040513 | −0.011163 | 0.004505 |
| 230 | 0.037057 | −0.019774 | −0.03498 | 0.006401 | −0.001621 | −0.052586 | 0.0019 | 0.00048 | 0.051739 | −0.010388 | −0.001789 | −0.050381 | −0.032306 | −0.013759 |
| 231 | 0.053942 | 0.009161 | −0.015104 | 0.028056 | 0.038677 | −0.03628 | 0.010826 | −0.005847 | 0.008542 | −0.021768 | 0.014372 | −0.043638 | −0.001745 | −0.021774 |
| 232 | 0.007192 | 0.048364 | −0.045835 | 0.028281 | 0.015704 | −0.02498 | −0.010072 | −0.032242 | 0.019175 | 0.016194 | 0.044718 | 0.013067 | 0.001445 | 0.032366 |
| 233 | 0.00819 | −0.004959 | 0.01305 | −0.021568 | 0.029575 | 0.019224 | 0.031662 | 0.055788 | −0.031857 | 0.004554 | 0.039911 | −0.062623 | −0.023168 | −0.023153 |
| 234 | 0.009299 | 0.009659 | −0.015281 | −0.010327 | 0.005035 | −0.003996 | 0.014596 | −0.012566 | 0.001166 | −0.051994 | −0.042617 | −0.008413 | −0.012102 | 0.003166 |
| 235 | 0.026159 | 0.037621 | −0.005817 | 0.008031 | 0.019479 | 0.009449 | 0.04151 | −0.012615 | −0.001861 | 0.016041 | 0.001601 | 0.048266 | −0.012955 | −0.001246 |
| 236 | 0.008433 | −0.019373 | −0.022012 | −0.001628 | 0.009693 | 0.006967 | 0.025704 | 0.006357 | −0.013329 | −0.001018 | 0.008241 | −0.023518 | 0.003542 | −0.00591 |
| 237 | 0.015922 | 0.010159 | 0.000912 | 0.020993 | 0.020772 | 0.020512 | −0.014341 | −0.026071 | −0.001877 | 0.007365 | 0.026016 | −0.023652 | −0.002116 | −0.016695 |
| 238 | 0.001511 | 0.017598 | 0.000656 | 0.019336 | 0.013983 | −0.000906 | 0.033864 | 0.007806 | −0.00924 | −0.038076 | 0.010953 | −0.038377 | 0.003601 | −0.018495 |
| 239 | −0.004858 | 0.01862 | 0.007171 | 0.008048 | 0.01024 | −0.00144 | 0.019834 | 0.028632 | 0.010105 | −0.007567 | −0.004977 | −0.011668 | 0.001556 | −0.03089 |
| 240 | −0.017783 | 0.008209 | 0.033335 | −0.038218 | −0.000856 | 0.006169 | −0.003896 | 0.019001 | −0.022116 | 0.014006 | 0.025453 | 0.00153 | 0.007476 | 0.029757 |
| 241 | −0.000127 | −0.018865 | 0.015549 | −0.039131 | −0.008572 | 0.014165 | −0.004678 | 0.01728 | −0.010788 | −0.004271 | −0.002663 | −0.05404L | −0.010298 | −0.011472 |
| 242 | 0.0098 | −0.004568 | 0.006417 | −0.000566 | −0.004416 | 0.006919 | 0.036652 | −0.011408 | −0.006039 | 0.014221 | −0.023913 | −0.015904 | 0.006113 | 0.043573 |
| 243 | −0.006528 | 0.001439 | 0.012908 | 0.000518 | −0.008956 | −0.00036 | 0.014908 | 0.01515 | 0.001876 | 0.011578 | 0.025341 | 0.050224 | −0.015589 | 0.034021 |
| 244 | 0.005212 | 0.015012 | −0.002501 | −0.008737 | 0.011319 | −0.006482 | −0.010389 | 0.017279 | 0.017087 | 0.022468 | −0.012967 | 0.025526 | −0.004441 | 0.022122 |
| 245 | 0.012936 | 0.024763 | −0.006195 | 0.020067 | 0.025393 | −0.001889 | 0.017512 | 0.061471 | 0.035866 | −0.032924 | 0.006215 | 0.042415 | −0.01063 | 0.026344 |
| 246 | −0.013714 | −0.002782 | −0.016303 | −0.0191 | −0.019087 | 0.011864 | 0.013437 | 0.014069 | 0.00824 | 0.007496 | 0.001641 | −0.023533 | 0.00744 | −0.011903 |
| 247 | −0.008946 | −0.011427 | −0.023094 | −0.026963 | −0.014127 | 0.020541 | −0.007241 | 0.024886 | 0.002137 | 0.0022961 | 0.006724 | −0.025743 | 0.015058 | −0.019809 |
| 248 | −0.000574 | 0.006883 | −0.01011 | 0.022503 | 0.018024 | −0.01526 | 0.009394 | −0.020109 | −0.010568 | −0.043458 | 0.036764 | −0.033638 | 0.002251 | 0.00533 |
| 249 | 0.007864 | 0.005639 | 0.018644 | 0.010922 | −0.033341 | −0.015478 | −0.014604 | −0.002461 | −0.012038 | 0.011241 | 0.030306 | −0.026612 | −0.013121 | −0.030908 |
| 250 | −0.034129 | −0.006869 | −0.002017 | −0.022993 | −0.014929 | 0.009459 | −0.001567 | 0.027295 | 0.002369 | 0.000404 | 0.009094 | 0.009595 | 0.009312 | 0.010923 |
| 251 | 0.003836 | 0.02485 | 0.008828 | −0.013797 | −0.008314 | 0.000921 | 0.008289 | −0.00738 | 0.022598 | 0.015454 | 0.009069 | 0.001633 | 0.017096 | 0.0509 |
| 252 | 0.017859 | 0.012712 | 0.004256 | 0.019003 | 0.005366 | −0.018788 | 0.035737 | 0.060826 | 0.039504 | −0.006402 | −0.022162 | 0.029402 | −0.000116 | 0.032391 |
| 253 | 0.008585 | 0.000399 | −0.011912 | 0.007199 | −0.021734 | −0.000484 | −0.008111 | 0.021793 | 0.012909 | −0.004224 | 0.048389 | 0.031494 | 0.006975 | 0.023746 |
| 254 | −0.002883 | 0.000593 | 0.00454 | −0.003733 | −0.027978 | 0.030166 | −0.023666 | −0.030388 | 0.048954 | 0.002629 | 0.006092 | 0.008463 | 0.012773 | 0.006336 |
| 255 | 0.027525 | −0.013013 | 0.01452 | −0.028909 | −0.002294 | −0.005593 | 0.022821 | −0.036857 | 0.018635 | 0.01433 | 0.00032 | −0.009436 | −0.000864 | 0.030566 |
| 256 | 0.050294 | −0.001582 | −0.022282 | 0.01528 | 0.020243 | −0.024177 | 0.039125 | 0.026587 | 0.02291 | −0.033181 | −0.010493 | 0.0096 | 4.034662 | 0.022541 |
| 257 | 0.003947 | −0.009084 | −0.018925 | −0.008215 | −0.015385 | −0.000816 | 0.024055 | −0.006711 | −0.01684 | 0.018265 | −0.010579 | 0.020529 | 0.015563 | −0.014585 |
| 258 | 0.006544 | 0.0150021 | −0.022297 | −0.018168 | −0.014952 | 0.035415 | −0.006122 | −0.040205 | −0.005187 | 0.004453 | 0.010361 | 0.0312391 | 0.013319 | −0.001009 |
| 259 | 0.006703 | 0.002587 | 0.02837 | 0.00965 | −0.038526 | 0.010012 | 0.003759 | −0.019089 | 0.021833 | −0.005054 | 0.018877 | 0.010258 | 0.008437 | −0.005784 |
| 260 | 0.007882 | 0.000118 | −0.01081 | 0.029878 | −0.009914 | 0.001603 | 0.002329 | −0.030182 | 0.032161 | 0.024129 | −0.003884 | 0.060365 | 0.010476 | −0.04539 |
| 261 | −0.011388 | 0.013557 | 0.011304 | 0.014283 | −0.005899 | 0.011228 | 0.020843 | −0.022261 | 0.032035 | −0.0151 | 0.02309 | −0.011273 | 0.018689 | −0.003821 |
| 262 | 0.001499 | −0.016646 | 0.002423 | −0.003982 | −0.013029 | −0.014459 | 0.019817 | 0.028855 | 0.035083 | 0.033762 | −0.011834 | −0.039537 | −0.006565 | −0.005677 |
| 263 | 0.019479 | −0.014601 | 0.0106121 | 0.018645 | 0.001355 | −0.028865 | 0.026056 | 0.02118 | 0.019021 | 0.0048471 | −0.017051 | −0.017545 | −0.012091 | 0.004788 |
| 264 | 0.039287 | −0.0106491 | 0.022851 | 0.021216 | −0.007202 | 0.041161 | 0.011672 | −0.016508 | 0.021845 | 0.053273 | 0.025778 | −0.004621 | −0.014013 | −0.045839 |
| 265 | −0.00493 | −0.007567 | 0.007212 | −0.002427 | −0.021153 | 0.031415 | −0.065633 | 0.009792 | −0.004225 | 0.022117 | 0.018924 | 0.026819 | 0.007632 | −0.019593 |
| 266 | −0.011465 | −0.002795 | −0.005237 | −0.02121 | −0.029819 | −0.010252 | −0.060027 | 0.004799 | −0.019622 | 0.008922 | 0.000995 | 0.004614 | 0.005516 | 0.021087 |
| 267 | −0.017322 | −0.007711 | 0.003017 | 0.010759 | 0.010908 | 0.00479 | −0.053749 | −0.034993 | −0.026945 | −0.026546 | 0.016587 | 0.039499 | 0.00863 | 0.008627 |
| 268 | −0.008639 | −0.001057 | 0.001969 | −0.0065 | 0.005958 | −0.007667 | −0.066162 | 0.005843 | −0.006954 | 0.00602 | −0.027782 | −0.001046 | 0.001922 | 0.001587 |
| 269 | −0.007874 | −0.005728 | 0.005873 | 0.003758 | 0.005319 | −0.01795 | −0.043845 | 0.000169 | −0.014005 | 0.001236 | −0.021556 | −0.001913 | −0.000754 | 0.013675 |
| 270 | 4.019154 | −0.025081 | 0.014611 | 0.011965 | 0.015144 | −0.017839 | −0.028067 | −0.001771 | −0.007781 | −0.019127 | 0.006277 | −0.001285 | −0.010581 | 0.014658 |
| 271 | −0.015632 | 0.010861 | 0.001866 | −0.025253 | −0.029691 | −0.006822 | −0.072613 | 0.059819 | 0.033699 | 0.016859 | −0.024678 | −0.00135 | 0.025242 | −0.008079 |
| 272 | −0.009237 | −0.010371 | 0.017467 | −0.009819 | −0.015671 | 0.010089 | 0.045604 | −0.007584 | −0.02284 | −0.039907 | −0.002713 | 0.019684 | 0.017675 | 0.013307 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 273 | 0.015751 | −0.021651 | 0.002236 | −0.000735 | 0.001996 | −0.003422 | 0.002817 | 0.005428 | −0.005301 | −0.020778 | 0.000566 | −0.029761 | 0.00035 | −0.01625 |
| 274 | 0.016801 | −0.028347 | −0.002142 | −0.00444 | −0.002838 | 0.002543 | 0.01124 | −0.002124 | −0.014159 | −0.015129 | 0.003601 | −0.031758 | 0.003351 | −0.023085 |
| 275 | −0.000554 | −0.025106 | −0.014309 | 0.016229 | 0.00383 | −0.034498 | −0.013158 | 0.021564 | 0.048497 | −0.032093 | 0.007148 | 0.001363 | −0.032382 | 0.006026 |
| 276 | −0.006995 | −0.008007 | −0.004308 | −0.018265 | −0.011451 | 0.032838 | 0.063789 | 0.013295 | −0.019094 | −0.011147 | 0.004632 | −0.010404 | 0.001758 | −0.010234 |
| 277 | 0.023756 | 0.009152 | 0.028493 | 0.043486 | 0.045846 | 0.006341 | −0.037418 | −0.030992 | −0.050056 | 0.016298 | 0.019014 | 0.049009 | 0.009631 | −0.005172 |
| 278 | 0.006386 | 0.021658 | 0.035062 | 0.021378 | 0.014062 | −0.021305 | −0.030389 | −0.002904 | −0.012441 | 0.002031 | −0.004866 | 0.039581 | 0.0126811 | 0.020766 |
| 279 | −0.021845 | 0.019574 | 0.026408 | 0.032719 | 0.024457 | −0.018532 | 0.029497 | 0.010645 | 0.00372 | −0.019835 | −0.009477 | −0.004131 | −0.010503 | −0.008374 |
| 280 | 0.023875 | 4.00057 | 0.042831 | 0.004464 | −0.012661 | 0.011568 | −0.008527 | −0.023655 | 0.016738 | −0.000106 | 0.032866 | 0.00829 | −0.014577 | 0.053081 |
| 281 | −0.013669 | 0.005628 | 0.000066 | 0.005284 | 0.007485 | −0.000075 | −0.000654 | −0.03131 | −0.016796 | −0.007626 | 0.021169 | −0.025571 | −0.002229 | −0.003651 |
| 282 | −0.009732 | −0.000659 | 0.027169 | −0.003187 | −0.023178 | −0.00844 | 0.000287 | 0.032876 | 0.025116 | 0.020428 | −0.032997 | −0.006797 | 0.001533 | 0.033436 |
| 283 | −0.040319 | −0.018386 | −0.014211 | −0.005592 | 0.000405 | 0.007749 | 0.035213 | −0.024387 | 0.0121951 | 0.012827 | 0.0193141 | −0.011397 | −0.008201 | −0.022397 |
| 284 | −0.000954 | −0.000405 | −0.013983 | 0.003343 | −0.00282 | 0.005736 | 0.034408 | −0.00515 | −0.009605 | 0.018711 | −0.019096 | 0.027625 | 0.001054 | −0.02692 |
| 285 | 0.003321 | 0.003975 | −0.03225 | 0.00056 | −0.019551 | 0.000615 | 0.012559 | −0.009522 | 0.021222 | 0.036136 | −0.025926 | 0.02901 | 0.010749 | −0.034236 |
| 286 | 0.008364 | 0.038306 | −0.007686 | 0.003824 | −0.014423 | 0.018277 | 0.000596 | 0.019864 | 0.026451 | 0.002956 | −0.005597 | 0.01708 | −0.003175 | −0.001801 |
| 287 | −0.008201 | 0.018402 | −0.015763 | −0.023381 | −0.038804 | −0.000314 | −0.000376 | −0.012364 | 0.032596 | 0.011868 | −0.017183 | 0.039961 | −0.007442 | 0.014149 |
| 288 | 0.001394 | 0.025451 | −0.017769 | 0.008408 | 0.010011 | 0.01338 | 0.011211 | −0.050863 | 0.006043 | 0.035669 | 0.029383 | 0.00933 | −0.01161 | 0.006289 |
| 289 | −0.007282 | −0.031217 | −0.008822 | −0.016301 | −0.015907 | −0.010059 | −0.023826 | 0.024945 | −0.013048 | 0.040802 | −0.015048 | −0.016942 | −0.012445 | 0.008514 |
| 290 | −0.012828 | 0.007107 | −0.001639 | 0.002507 | −0.011748 | 0.021363 | −0.03581 | −0.013898 | 0.032522 | 0.019568 | 0.044263 | −0.006495 | 0.004846 | 0.045675 |
| 291 | −0.013079 | 0.006497 | 0.005851 | 0.005873 | −0.009632 | 0.025598 | −0.036115 | −0.004684 | 0.041174 | 0.026621 | 0.043604 | −0.006139 | 0.004446 | 0.051335 |
| 292 | −0.017642 | 0.013149 | −0.005302 | 0.002715 | −0.013501 | 0.027857 | −0.025181 | −0.008213 | 0.03561 | 0.028845 | 0.048006 | 0.012064 | 0.00224 | 0.028146 |
| 293 | 0.020623 | 0.0371061 | −0.01219 | 0.024138 | 0.02467 | −0.013778 | −0.016347 | 0.042705 | 0.027717 | 0.007482 | −0.000955 | 0.017436 | 0.006897 | 0.030504 |
| 294 | 0.014416 | 0.0047571 | −0.008132 | 0.016286 | 0.021837 | 0.035463 | −0.005444 | 0.043902 | −0.000714 | 0.021966 | 0.000809 | −0.028268 | −0.026747 | −0.017366 |
| 295 | 0.012691 | −0.014102 | −0.000324 | −0.00087 | −0.010309 | −0.006569 | 0.039142 | 0.03332 | 0.011647 | 0.013531 | 0.026039 | −0.029285 | 0.002335 | −0.00502 |
| 296 | 0.023613 | −0.010769 | −0.010683 | 0.015535 | −0.00267 | 0.020449 | −0.012704 | 0.013176 | 0.010069 | 0.007126 | 0.013902 | −0.03035 | 0.01297 | 0.017519 |
| 297 | 0.019834 | −0.020431 | 0.008544 | −0.002081 | −0.018623 | −0.005356 | 0.065976 | 0.014292 | −0.009448 | 0.020127 | −0.019838 | −0.038554 | −0.006832 | −0.024026 |
| 298 | 0.004714 | −0.000105 | 0.036211 J | 0.01562 | 0.012255 | 0.011707 | 0.030671 | −0.017713 | 0.007431 | −0.033297 | 0.026792 | 0.019982 | 0.00488 | −0.007472 |
| 299 | 0.037155 | 0.00472 | −0.023496 | 0.003022 | −0.011453 | −0.010271 | 0.01229 | 0.002135 | 0.005314 | 0.027515 | −0.007289 | −0.035972 | −0.002213 | −0.003933 |
| 300 | −0.025163 | −0.034512 | 0.027431 | −0.02977 | −0.007741 | 0.018308 | 0.008113 | 0.023317 | 0.035702 | 0.013836 | 0.003251 | −0.071659 | −0.035595 | −0.054465 |
| 301 | 0.018332 | 0.008182 | −0.017849 | 0.001248 | −0.009962 | −0.017337 | 0.046293 | 0.005224 | 0.007274 | 0.043951 | 0.006384 | −0.002015 | 0.000259 | 0.01447 |
| 302 | 0.005981 | −0.019967 | 0.000757 | 0.000783 | −0.014857 | 0.009378 | 0.022097 | −0.015197 | 0.026455 | 0.035262 | 0.031121 | −0.038365 | −0.011006 | 0.01505 |
| 303 | 0.006946 | 0.027774 | −0.04502 | −0.013455 | −0.021115 | 0.031119 | −0.003449 | 0.062348 | 0.030526 | 0.03385 | −0.00035 | 0.017862 | −0.004966 | −0.008859 |
| 304 | 0.027252 | 0.013762 | −0.017501 | 0.024594 | 0.010755 | 0.007644 | 0.0147 | 0.028148 | 0.020411 | −0.014801 | 0.02282 | −0.010445 | −0.014661 | 0.014439 |
| 305 | −0.015121 | −0.026034 | −0.01932 | 0.007811 | 0.000033 | −0.000774 | −0.03626 | 0.064586 | 0.030133 | 0.015161 | −0.020532 | 0.01396 | 0.02005 | −0.028158 |
| 306 | −0.02037 | 0.001187 | −0.025154 | −0.021095 | −0.015649 | 0.00485 | 0.007466 | 0.026822 | −0.007731 | −0.00973 | −0.052068 | −0.019837 | −0.003967 | 0.028429 |
| 307 | −0.04695 | 0.007351 | −0.023658 | −0.017178 | −0.008186 | 0.029356 | 0.014436 | 0.048813 | −0.055808 | 0.001982 | −0.012727 | 0.012615 | 0.019138 | 0.024286 |
| 308 | 0.041654 | −0.007906 | −0.014489 | 0.026776 | 0.016487 | −0.02851 | 0.034484 | −0.029142 | 0.028075 | −0.009472 | −0.069734 | −0.037951 | −0.021031 | −0.027133 |
| 309 | 0.004379 | −0.001123 | 0.010419 | 0.011536 | 0.009789 | −0.004805 | −0.004689 | −0.019284 | 0.017918 | 0.009033 | −0.021664 | −0.006308 | −0.009201 | −0.002273 |
| 310 | 0.013225 | 0.006426 | −0.035494 | 0.0289 | 0.02357 | 0.002447 | −0.016644 | 0.042284 | 0.004883 | 0.003239 | −0.034712 | −0.006384 | −0.009984 | −0.007918 |
| 311 | −0.007781 | 0.002498 | 0.029715 | 0.006402 | 0.007789 | 0.018578 | −0.055985 | 0.018282 | 0.007254 | 0.029663 | 0.038151 | −0.006581 | 0.010816 | 0.023253 |
| 312 | 0.026747 | −0.00245 | −0.033954 | −0.012619 | 0.005198 | 0.030734 | −0.019712 | −0.02521 | −0.036277 | −0.007936 | −0.013744 | 0.009221 | −0.024926 | 0.011005 |
| 313 | 0.018982 | −0.013632 | 0.006104 | 0.000844 | 0.004087 | 0.001956 | 0.009515 | 0.000245 | −0.037431 | −0.017574 | −0.029885 | 0.008427 | −0.012081 | −0.005637 |
| 314 | 0.018051 | −0.012908 | −0.049046 | −0.012953 | −0.015145 | 0.019102 | −0.031145 | −0.012396 | 0.023801 | −0.074399 | 0.004599 | 0.033361 | −0.003385 | −0.006734 |
| 315 | −0.002157 | −0.004697 | −0.007825 | −0.018086 | −0.014969 | 0.011421 | −0.013421 | −0.013338 | −0.009808 | 0.014571 | −0.010363 | 0.006382 | 0.002752 | 0.013785 |
| 316 | −0.013592 | −0.016837 | 0.007159 | −0.014885 | −0.035891 | −0.000321 | 0.024789 | −0.00648 | 0.06829 | −0.046039 | −0.024369 | 0.025077 | −0.020087 | −0.023151 |
| 317 | −0.01168 | 0.008542 | 0.000339 | 0.012266 | 0.015876 | −0.012702 | 0.009211 | −0.008997 | 0.017108 | 0.011932 | 0.010187 | 0.053198 | 0.007596 | 0.016291 |
| 318 | 0.006553 | −0.003472 | −0.014218 | −0.017291 | 0.009084 | 0.013094 | 0.01746 | −0.019478 | 0.023177 | −0.020784 | 0.036598 | −0.000299 | 0.0064 | −0.028831 |
| 319 | 0.004358 | 0.010791 | −0.01503 | −0.001654 | −0.008676 | 0.015363 | 0.005498 | −0.036171 | 0.013333 | 0.038514 | −0.01923 | 0.015348 | −0.006459 | 0.00833 |
| 320 | 0.014998 | 0.002831 | −0.000303 | −0.010176 | −0.008854 | 0.020957 | −0.016515 | −0.010775 | −0.000521 | −0.014781 | −0.027105 | 0.011256 | 0.008496 | 0.040333 |
| 321 | 0.012654 | −0.018481 | −0.049861 | −0.028877 | −0.033129 | −0.026197 | 0.019796 | 0.055606 | −0.011699 | −0.028644 | −0.016999 | −0.022261 | −0.020889 | −0.027783 |
| 322 | 0.035951 | −0.024353 | 0.051534 | 0.024013 | 0.033337 | −0.00512 | −0.013769 | 0.025395 | −0.005512 | −0.063171 | 0.056546 | −0.03774 | 0.009661 | −0.023184 |
| 323 | 0.010545 | −0.016657 | 0.033245 | 0.004399 | −0.009337 | 0.002858 | 0.002479 | 0.009504 | −0.039942 | −0.049911 | 0.032591 | 0.050173 | 0.00982 | 0.011868 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 324 | −0.035959 | 0.005818 | 0.021174 | 0.025115 | 0.033051 | 0.003055 | −0.020862 | −0.052143 | −0.062937 | −0.061498 | 0.017879 | −0.053713 | −0.034433 | −0.017122 |
| 325 | −0.029211 | 0.014988 | −0.008598 | −0.013261 | −0.009118 | 0.025054 | 0.019634 | 0.000425 | −0.001102 | −0.02742 | −0.00901 | −0.009401 | −0.006075 | −0.001798 |
| 326 | −0.024379 | −0.005042 | −0.005797 | −0.009071 | 0.017786 | 0.029599 | −0.026398 | −0.008235 | −0.019989 | 0.032906 | 0.057089 | −0.003506 | −0.003294 | −0.005279 |
| 327 | 0.021677 | 0.00154 | −0.01718 | 0.016166 | 0.008803 | 0.017984 | 0.009287 | −0.021096 | 0.020649 | 0.018877 | 0.016639 | −0.01191 | 0.005949 | −0.00962 |
| 328 | 0.028751 | −0.002704 | −0.000085 | 0.024055 | 0.005994 | 0.005344 | −0.085925 | 0.078482 | −0.053501 | 0.001582 | 0.012604 | −0.027265 | 0.016005 | −0.015653 |
| 329 | 0.0166011 | 0.001225 | 0.0087181 | 0.017083 | −0.002626 | 0.033427 | −0.005843 | 0.067295 | −0.002541 | 0.064407 | 0.0367991 | 0.010685 | 0.0054151 | −0.001565 |
| 330 | −0.019356 | −0.03803 | 0.01392 | −0.001652 | −0.014105 | −0.022744 | 0.036572 | −0.048179 | 0.082089 | −0.03069 | −0.001219 | 0.04195 | −0.045438 | −0.002469 |
| 331 | −0.0144 | 0.008516 | −0.003655 | −0.003115 | −0.0016 | 0.046506 | −0.006856 | 0.036688 | 0.003569 | 0.022499 | −0.010544 | 0.004152 | −0.021698 | −0.002239 |
| 332 | 0.016971 | −0.01718 | 0.040197 | 0.026452 | 0.021583 | 0.040678 | −0.040253 | −0.092594 | 0.006499 | 0.067722 | 0.039956 | −0.03719 | 0.001386 | 0.020153 |
| 333 | −0.016408 | 0.010825 | 0.005931 | 0.004997 | 0.003636 | 0.016278 | 0.024721 | 0.003274 | −0.020651 | 0.002059 | 0.006945 | 0.002481 | −0.010823 | 0.018072 |
| 334 | −0.018888 | 0.024836 | 0.05039 | 0.006984 | −0.009908 | 0.052279 | 0.004503 | 0.0226 | 0.019552 | 0.018348 | −0.032091 | −0.012761 | −0.01048 | 0.006794 |
| 335 | 0.000147 | 0.012374 | −0.013955 | 0.019475 | 0.010899 | 0.002981 | 0.019517 | 0.002403 | −0.000511 | −0.008659 | −0.013717 | 0.010946 | −0.033573 | 0.000715 |
| 336 | −0.001539 | −0.005654 | −0.043412 | −0.01056 | 0.02019 | −0.012265 | 0.001007 | −0.026335 | 0.02076 | 0.00104 | 0.046521 | 0.022168 | −0.013346 | −0.016116 |
| 337 | 0.009499 | 0.034721 | −0.03455 | −0.006817 | −0.006255 | −0.017265 | −0.008427 | −0.025781 | −0.008432 | −0.005336 | 0.021038 | 0.020786 | 0.005578 | 0.024251 |
| 338 | 0.000287 | 0.012796 | 0.045078 | 0.019451 | 0.013285 | 0.033649 | 0.035397 | −0.00555 | 0.005032 | 0.036732 | −0.009145 | −0.048728 | 0.02225 | 0.059187 |
| 339 | −0.040317 | 0.028364 | 0.008716 | 0.017586 | 0.016679 | 0.054705 | −0.056804 | 0.003039 | 0.069874 | −0.012734 | 0.002354 | 0.036166 | 0.027372 | 0.026158 |
| 340 | 0.0243891 | −0.016025 | 0.0035551 | −0.008109 | 0.016463 | −0.007198 | −0.0127 | −0.007715 | 0.032816 | −0.007527 | −0.055424 | 0.0833251 | 0.0351691 | −0.030413 |

| | EH | EI | EJ | EK | EL | EM | EN | EO | EP | EQ | ER | ES | ET | EU |
|---|---|---|---|---|---|---|---|---|---|---|---|---|---|---|
| 1 | 0.030347 | 0.011698 | −0.119222 | −0.064858 | 0.002395 | 0.149015 | 0.06372 | 0.073169 | 0.037467 | 0.005958 | 0.012563 | 0.030799 | −0.027071 | 0.012415 |
| 2 | −0.04358 | −0.001419 | 0.054439 | 0.168452 | −0.010763 | −0.059081 | 0.051161 | −0.045237 | −0.10014 | −0.034572 | −0.061444 | 0.082545 | −0.040771 | −0.073161 |
| 3 | 0.003573 | 0.018308 | −0.043102 | −0.027047 | −0.020555 | −0.078736 | −0.007811 | −0.056487 | 0.059494 | 0.029181 | 0.065322 | −0.119391 | −0.056395 | 0.00546 |
| 4 | −0.042143 | −0.152268 | −0.0359 | 0.012071 | 0.096826 | −0.019829 | 0.052938 | 0.030297 | −0.021462 | 0.006548 | −0.023353 | −0.10117 | 0.026575 | 0.009705 |
| 5 | −0.057521 | 0.110307 | 0.014143 | 0.035882 | 0.029306 | 0.043901 | 0.015192 | −0.00165 | −0.000484 | −0.00683 | −0.021993 | −0.004596 | 0.007607 | 0.00175 |
| 6 | 0.007948 | 0.059805 | −0.084963 | −0.04375 | 0.00028 | −0.016745 | −0.080037 | 0.043631 | 0.091965 | 0.005284 | 0.009664 | −0.013354 | −0.022319 | −0.017673 |
| 7 | −0.051108 | −0.025479 | −0.033932 | −0.109882 | 0.106668 | −0.06284 | 0.01166 | −0.038962 | −0.100351 | −0.041408 | −0.06393 | −0.014906 | 0.036333 | 0.005199 |
| 8 | 0.025044 | −0.023669 | 0.012743 | −0.021394 | −0.073817 | 0.004444 | −0.005316 | −0.053305 | 0.085141 | 0.063549 | 0.040735 | −0.032919 | −0.042825 | 0.021527 |
| 9 | 0.038826 | −0.038179 | 0.123381 | 0.006798 | 0.017573 | 0.003519 | 0.009375 | 0.030922 | −0.073621 | 0.014047 | 0.020687 | −0.050042 | 0.050008 | 0.020218 |
| 10 | 0.025566 | 0.006386 | −0.068169 | 0.094028 | 0.005312 | −0.029653 | 0.040089 | 0.009099 | 0.051566 | 0.031501 | 0.039006 | −0.05403 | 0.068578 | 0.061408 |
| 11 | −0.008661 | 0.059305 | −0.057233 | −0.045564 | −0.037493 | −0.00942 | −0.038622 | −0.039987 | −0.038946 | −0.004395 | −0.061315 | −0.011652 | −0.103182 | 0.093725 |
| 12 | −0.015914 | 0.022172 | 0.070978 | 0.069609 | −0.004995 | 0.040685 | 0.031705 | 0.003271 | 0.005154 | 0.016746 | 0.021731 | 0.028008 | 0.043564 | 0.069266 |
| 13 | 0.041787 | −0.033242 | 0.104064 | 0.054428 | 0.006304 | 0.031622 | 0.056995 | 0.061032 | 0.036276 | −0.01414 | 0.042235 | −0.046434 | −0.042646 | 0.068138 |
| 14 | 0.147782 | 0.070282 | −0.069268 | 0.050363 | 0.006037 | −0.012574 | 0.003966 | 0.030717 | 0.007597 | −0.04409 | −0.073075 | 0.148412 | 0.076376 | −0.007674 |
| 15 | −0.057487 | −0.095325 | −0.096914 | 0.057286 | 0.028442 | 0.030981 | 0.075745 | 0.043446 | 0.032067 | 0.00477 | −0.03137 | 0.122214 | −0.000237 | −0.078883 |
| 16 | −0.02972 | 0.009749 | 0.009662 | 0.03334 | 0.014883 | −0.020742 | 0.03976 | −0.020856 | 0.028282 | −0.010687 | −0.051179 | 0.025456 | 0.044792 | 0.079165 |
| 17 | −0.00854 | 0.000726 | 0.055743 | −0.029231 | −0.042851 | −0.038785 | −0.000276 | −0.07219 | −0.032001 | −0.018121 | −0.013487 | −0.054821 | −0.053514 | 0.070304 |
| 18 | −0.010937 | −0.0017 | 0.088046 | −0.041366 | 0.002984 | 0.000032 | 0.003795 | 0.008557 | 0.071502 | 0.009153 | 0.036466 | −0.064481 | −0.046784 | −0.038902 |
| 19 | 0.015234 | −0.006872 | 0.034198 | 0.022213 | −0.024508 | −0.00539 | 0.001186 | −0.057651 | 0.039961 | 0.013421 | 0.046484 | −0.024925 | −0.035736 | 0.126041 |
| 20 | −0.020492 | −0.068327 | 0.13278 | −0.003538 | −0.077589 | 0.061537 | −0.006444 | −0.052919 | −0.0195 | −0.067331 | −0.081731 | 0.122986 | 0.033993 | −0.155617 |
| 21 | −0.057934 | −0.113839 | 0.040213 | 0.058076 | 0.041916 | 0.027191 | −0.045792 | −0.001538 | −0.027346 | 0.016132 | −0.095823 | −0.146548 | −0.045114 | −0.101554 |
| 22 | −0.0031971 | 0.109257 | −0.0613811 | 0.07185 | 0.058746 | 0.051608 | 0.0668 | 0.025002 | 0.0099811 | −0.02923 | −0.051289 | −0.005079 | 0.077024 | 0.027222 |
| 23 | −0.083249 | −0.073811 | −0.0342 | −0.027332 | 0.00983 | −0.049218 | −0.014173 | 0.027028 | 0.038687 | −0.019535 | −0.012118 | 0.016516 | 0.019653 | 0.012132 |
| 24 | −0.054909 | 0.033858 | 0.116829 | −0.005271 | −0.001835 | −0.017818 | −0.039491 | −0.092344 | −0.022228 | 0.018923 | 0.025026 | −0.038757 | 0.103911 | −0.020371 |
| 25 | −0.032768 | 0.124745 | 0.052581 | 0.035991 | 0.110297 | 0.050826 | −0.050448 | 0.049336 | −0.037214 | 0.055106 | 0.065334 | 0.074161 | 0.045548 | 0.029247 |
| 26 | −0.023748 | 0.073265 | −0.052883 | 0.101229 | 0.034034 | −0.038083 | −0.040237 | −0.039585 | −0.113528 | −0.022458 | 0.028275 | −0.058737 | 0.031204 | −0.050461 |
| 27 | −0.059168 | −0.003519 | −0.051254 | −0.042529 | 0.054275 | 0.044196 | 0.024249 | 0.007399 | 0.092726 | −0.035224 | −0.043529 | −0.138035 | 0.064925 | 0.017425 |
| 28 | −0.007204 | −0.040891 | 0.017309 | −0.031029 | −0.202232 | −0.03301 | −0.073995 | 0.018024 | 0.095255 | −0.002677 | −0.006131 | 0.100151 | 0.047924 | 0.009217 |
| 29 | −0.006725 | 0.066974 | −0.065378 | −0.020177 | 0.029662 | 0.013065 | −0.029237 | −0.005685 | 0.013454 | 0.003507 | 0.051391 | −0.045123 | 0.010761 | −0.024457 |
| 30 | −0.00031 | −0.177956 | −0.001142 | 0.037373 | −0.062088 | 0.093054 | −0.004246 | 0.005561 | 0.028706 | 0.01089 | −0.072063 | −0.176048 | 0.076926 | 0.041227 |
| 31 | −0.036706 | 0.110013 | 0.045129 | −0.023066 | 0.033468 | 0.012202 | −0.00298 | 0.018714 | 0.018574 | 0.032699 | 0.010899 | −0.05479 | −0.118541 | 0.02822 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 32 | 0.019164 | 0.00559 | 0.046767 | 0.028435 | −0.024207 | 0.022752 | −0.078482 | −0.083746 | −0.091587 | 0.054199 | 0.004118 | −0.108919 | −0.011819 | −0.061171 |
| 33 | 0.014683 | −0.057149 | −0.062908 | −0.131025 | −0.050937 | −0.03846 | −0.004662 | 0.036883 | 0.053031 | −0.02252 | 0.025052 | −0.086133 | −0.037144 | 0.012495 |
| 34 | 0.070713 | 0.003004 | −0.029236 | −0.042385 | −0.06902 | −0.054568 | 0.032238 | −0.076913 | −0.025002 | 0.00702 | 0.00938 | −0.112268 | 0.071047 | 0.003632 |
| 35 | −0.024455 | −0.051504 | −0.101261 | −0.000089 | −0.094474 | −0.035647 | 0.009926 | 0.016997 | −0.0649f | −0.012301 | −0.062043 | 0.000506 | −0.001762 | 0.024255 |
| 36 | 0.05681 | −0.045695 | 0.161719 | −0.097095 | 0.026078 | 0.013912 | −0.093331 | 0.072299 | 0.001502 | 0.056778 | −0.040328 | 0.081264 | −0.026877 | 0.01866 |
| 37 | −0.030564 | 0.004839 | 0.046922 | 0.017379 | 0.034373 | −0.049843 | −0.051921 | 0.015808 | 0.103571 | −0.04687 | −0.03664 | 0.036553 | −0.061606 | 0.062619 |
| 38 | 0.02381 | −0.066338 | 0.051681 | 0.038266 | −0.003389 | −0.072452 | −0.085898 | 0.017981 | 0.003404 | −0.02174 | −0.033263 | 0.069108 | 0.074893 | −0.068711 |
| 39 | −0.054597 | 0.111157 | 0.042564 | −01 40941 | −0.019634 | 0.052621 | 0.052743 | 0.034307 | 0.02028 | −0.022988 | −0.034436 | −0.059615 | −0.010119 | −0.004154 |
| 40 | 0.062941 | −0.076807 | −0.00038 | 0.029996 | 0.078085 | −0.108796 | 0.071182 | −0.034997 | 0.02618 | 0.015557 | −0.031462 | −0.040034 | 0.072786 | −0.11971 |
| 41 | 0.082204 | 0.033059 | −0.033956 | −0.264703 | −0.009135 | −0.069917 | 0.044669 | 0.136027 | 0.03953 | 0.007611 | −0.084397 | 0.009413 | −0.00162 | −0.11265 |
| 42 | 0.010845 | −0.027603 | 0.0341 | −0.006108 | −0.00379 | −0.01218 | 0.007547 | −0.006477 | −0.005765 | 0.002973 | 0.005919 | 0.001398 | 0.017886 | 0.017733 |
| 43 | 0.07967 | 0.163925 | −0.084539 | 0.166825 | −0.029861 | −0.028794 | −0.035525 | 0.010345 | −0.009679 | 0.019432 | 0.025505 | 0.056878 | −0.015885 | 0.002113 |
| 44 | 0.059543 | 0.003257 | 0.008973 | 0.040131 | 0.01505 | 0.003605 | −0.020772 | 0.03045 | −0.041368 | −0.028792 | 0.002692 | 0.048471 | −0.024889 | −0.046113 |
| 45 | −0.029531 | −0.142709 | −0.033519 | −0.107997 | −0.033437 | 0.022403 | −0.080598 | −0.070377 | −0.045595 | 0.011097 | 0.016749 | 0.039958 | −0.026531 | 0.068907 |
| 46 | −0.096848 | 0.032715 | −0.05254 | −0.002068 | −0.016003 | 0.081605 | 0.007098 | 0.014551 | −0.054471 | −0.020332 | 0.026312 | −0.038625 | −0.094266 | −0.070584 |
| 47 | 0.091423 | −0.101144 | 0.025852 | 0.072792 | 0.095917 | −0.008158 | 0.093723 | −0.054393 | 0.073623 | 0.081443 | −0.038985 | 0.05736 | 0.040056 | 0.20126 |
| 48 | 0.048403 | −0.106015 | −0.020132 | 0.121924 | −0.049374 | 0.062105 | −0.00738 | 0.125516 | 0.083865 | 0.005076 | 0.027771 | −0.02536 | −0.082309 | −0.178192 |
| 49 | −0.0266551 | 0.1410521 | −0.01961 | −0.059204 | 0.128048 | −0.048088 | −0.012218 | −0.074156 | 0.014191 | −0.033145 | −0.066047 | 0.016795 | 0.073412 | −0.05797 |
| 50 | 0.084602 | −0.054911 | 0.186258 | −0.06122 | −0.040851 | −0.053118 | 0.027371 | 0.029833 | −0.00876 | −0.007874 | −0.020642 | −0.044798 | 0.012424 | 0.005999 |
| 51 | −0.094286 | −0.002419 | 0.097175 | 0.086917 | −0.052877 | −0.062777 | 0.034925 | −0.035032 | −0.034619 | −0.036775 | 0.010888 | 0.015905 | −0.041398 | −0.055082 |
| 52 | 0.010856 | 0.026863 | −0.101782 | 0.095822 | −0.079474 | −0.061722 | −0.111495 | −0.054602 | 0.003226 | −0.035738 | −0.110018 | −0.020848 | 0.017498 | −0.037307 |
| 53 | −0.037858 | 0.025386 | −0.180926 | −0.033537 | −0.015291 | 0.034255 | −0.042609 | 0.009775 | 0.026685 | 0.023095 | −0.039997 | −0.104078 | 0.007813 | 0.022673 |
| 54 | −0.035519 | 0.075949 | −0.073985 | −0.020308 | 0.019529 | 0.01535 | −0.103205 | −0.054939 | −0.038801 | 0.010117 | 0.094086 | 0.035614 | −0.109964 | 0.015385 |
| 55 | 0.036863 | 0.061206 | 0.089066 | 0.101429 | 0.065246 | −0.004549 | 0.076224 | −0.019337 | 0.010797 | 0.100276 | 0.052823 | 0.056622 | 0.026186 | 0.099921 |
| 56 | −0.080039 | 0.04528 | −0.039468 | 0.115206 | 0.02872 | 0.013929 | 0.077241 | 0.066715 | −0.014526 | −0.004784 | 0.089017k | 0.062376 | −0.044892 | 0.014847 |
| 57 | 0.011838 | 0.043861 | −0.006366 | −0.093095 | 0.046568 | −0.053962 | −0.026937 | 0.050296 | −0.00005 | −0.01348 | −0.045534 | −0.061652 | −0.043312 | −0.033566 |
| 58 | −0.101986 | −0.0696521 | 0.042909 | 0.040957 | 0.017523 | 0.131106 | −0.037193 | −0.080646 | −0.017531 | −0.051567 | 0.002534 | −0.119435 | −0.02658 | −0.085928 |
| 59 | −0.0270741 | −0.0233771 | 0.0937171 | 0.047395 | 0.038894 | 0.020482 | 0.007373 | −0.030641 | 0.01659 | 0.028785 | 0.025031 | −0.101141 | −0.031949 | 0.076004 |
| 60 | 4.001106 | −0.131281 | −0.07784 | −0.183729 | 0.058049 | −0.043023 | 0.018563 | −0.015851 | −0.018064 | 0.023598 | 0.031763 | −0.122266 | 0.015353 | −0.004866 |
| 61 | 0.100226 | 0.012639 | 0.020455 | 0.018588 | −0.001281 | −0.024929 | 0.005977 | −0.068944 | 0.0282 r | 0.022081 | −0.098848 | −0.044376 | −0.028958 | 0.071629 |
| 62 | 0.000455 | 0.142239 | −0.13658 | 0.02453 | 0.002817 | −0.025331 | 0.039857 | 0.026978 | −0.049826 | −0.036437 | 0.031756 | −0.00934 | 0.027247 | 0.022939 |
| 63 | 0.006343 | 0.049758 | 0.00187 | 0.078363 | −0.024563 | 0.102248 | 0.036122 | 0.010281 | 0.043819 | 0.013456 | 0.023867 | 0.024457 | 0.024084 | −0.059515 |
| 64 | −0.007159 | 0.056272 | −0.034651 | 0.015251 | 0.066866 | −0.103789 | −0.252382 | −0.109445 | −0.166961 | 0.05189 | 0.043958 | 0.163462 | −0.008752 | 0.010381 |
| 65 | 0.121263 | 0.042134 | −0.03402 | 0.047565 | −0.0078 | −0.024549 | 0.05931 | 0.020978 | 0.030196 | 0.013064 | −0.114338 | 0.123656 | −0.004906 | 0.015294 |
| 66 | 0.004181 | −0.091444 | 0.043784 | −0.066569 | −0.028646 | 0.044179 | 0.062208 | 0.0102 | −0.02353 | −0.0568 | 0.058385 | 0.000535 | 0.038209 | 0.066714 |
| 67 | −0.040574 | 0.067063 | −0.095725 | −0.070811 | −0.001919 | −0.058595 | 0.027706 | −0.004723 | 0.019347 | −0.016638 | −0.021389 | −0.154603 | 0.057268 | 0.005074 |
| 68 | −0.08654 | −0.125629 | 0.075519 | −0.036848 | −0.110455 | 0.079787 | −0.090982 | 0.005148 | −0.004262 | 0.009381 | 0.011882 | 0.084614 | 0.035161 | 0.001957 |
| 69 | −0.019891 | −0.050233 | 0.049624 | −0.074729 | −0.031889 | 0.008185 | −0.012259 | −0.067199 | −0.069115 | −0.047637 | −0.02768 | 0.044832 | −0.077109 | 0.020537 |
| 70 | 0.011341 | 0.073065 | 0.103671 | −0.110489 | 0.013382 | 0.008465 | 0.025258 | −0.083734 | −0.070229 | 0.013039 | 0.013295 | −0.077036 | −0.036619 | 0.0512 |
| 71 | −0.032661 | −0.010192 | −0.073053 | −0.006395 | −0.100391 | −0.032872 | 0.073381 | 0.067572 | 0.015176 | −0.003153 | 0.124469 | −0.041409 | −0.117219 | −0.014661 |
| 72 | 0.051791 | −0.013633 | −0.014595 | −0.018341 | −0.034674 | −0.005291 | 0.009896 | 0.003016 | −0.021023 | 0.030223 | 0.130102 | 0.098087 | −0.015035 | −0.04815 |
| 73 | 0.014262 | 0.024069 | 0.090187 | −0.045708 | 0.048598 | −0.053572 | −0.008855 | 0.06537 | −0.016544 | 0.06568 | 0.070377 | −0.066961 | 0.02531 | −0.073791 |
| 74 | 0.050484 | 0.004434 | −0.008506 | 0.041803 | 0.0259 | −0.021491 | −0.056212 | 0.022248 | −0.00491 | 0.057961 | 0.004638 | 0.034029 | −0.058485 | −0.113487 |
| 75 | −0.143212 | 0.040207 | −0.084522 | 0.040772 | 0.046296 | −0.078171 | 0.061191 | −0.004045 | 0.122191 | 0.068186 | −0.053762 | 0.039658 | −0.021704 | −0.012415 |
| 76 | −0.029285 | −0.048942 | −0.120596 | 0.062161 | 0.022043 | 0.045359 | −0.018453 | 0.090656 | −0.023019 | −0.065857 | 0.013785 | −0.001884 | 0.099978 | 0.0348 |
| 77 | 0.052355 | 0.059912 | 0.119205 | −0.101885 | 0.063773 | −0.061061 | −0.113712 | 0.037761 | −0.076449 | 0.03371 | −0.074493 | −0.031156 | 0.10222 | 0.019924 |
| 78 | 0.025843 | −0.065287 | −0.036165 | −0.01065 | −0.028813 | 0.132718 | −0.071131 | −0.017345 | 0.005856 | 0.057566 | 0.094181 | 0.116278 | 0.019108 | −0.073661 |
| 79 | 0.008858 | 0.052226 | −0.078005 | 0.119267 | −0.011861 | −0.022566 | 0.000667 | −0.071418 | 0.031936 | −0.023331 | 0.00182 | −0.168802 | −0.067631 | −0.048225 |
| 80 | 0.050881 | 0.029151 | 0.095523 | 0027996 | 0.008126 | 0.028012 | 0.081801 | 0.004785 | −0.024804 | −0.013368 | −0.028214 | 0.046357 | −0.015013 | −0.022507 |
| 81 | 0.013589 | −0.105787 | 0.052082 | 0.032058 | −0.016351 | −0.060344 | 0.030416 | 0.005522 | −0.019262 | −0.014875 | 0.033925 | −0.00151 | −0.099675 | 0.02362 |
| 82 | −0.143235 | 0.113335 | 0.119616 | −0.040121 | −0.084144 | 0.031449 | −0.03204 | 0.079122 | 0.003685 | 0.069674 | −0.015276 | 0.015775 | −0.043184 | 0.128638 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 83 | −0.0404421 | 0.0052221 | 0.023557 | −0.004594 | −0.111267 | −0.029326 | 0.108846 | −0.010181 | −0.063052 | −0.004227 | −0.017827 | −0.022312 | −0.046642 | 0.066735 |
| 84 | −0.01121 | 0.045756 | −0.051537 | −0.062677 | 0.050037 | 0.066383 | 0.008025 | −0.049514 | −0.061678 | −0.042303 | 0.052357 | 0.054338 | 0.045195 | 0.014407 |
| 85 | −0.03567 | 0.034188 | 0.077127 | −0.135406 | 0.034157 | 0.031662 | −0.037428 | −0.026792 | −0.037872 | −0.033946 | −0.034153 | −0.045072 | −0.051778 | 0.014914 |
| 86 | 0.078397 | 0.028764 | −0.045059 | −0.039455 | −0.05579 | 0.017108 | 0.052484 | −0.018522 | 0.026813 | −0.042852 | −0.114989 | 0.087756 | 0.081661 | 0.074441 |
| 87 | −0.0385 | −0.04182 | 0.071464 | 0.071653 | 0.031715 | 0.004613 | −0.009146 | 0.022591 | −0.035991 | −0.023595 | 0.038774 | 0.02411 | 0.123905 | 0.005291 |
| 88 | 0.160078 | −0.024941 | −0.043795 | 0.210652 | 0.054644 | −0.069077 | −0.039976 | −0.016767 | 0.004622 | 0.022612 | 0.06908 | −0.050781 | −0.012288 | −0.012671 |
| 89 | 0.053193 | −0.034431 | 0.028386 | −0.036544 | 0.067511 | −0.061197 | 0.058179 | 0.051724 | 0.054986 | 0.070597 | −0.037394 | 0.034667 | −0.003741 | −0.036361 |
| 90 | 0.044405 | −0.060141 | −0.04128 | 0.034539 | 0.010565 | 0.082046 | 0.064883 | −0.002932 | −0.010145 | −0.038417 | −0.037847 | −0.008885 | 0.005488 | −0.070698 |
| 91 | 0.02306 | −0.094348 | −0.070816 | −0.056176 | 0.106811 | 0.101461 | −0.042297 | 0.086879 | −0.048052 | 0.05138 | 0.002746 | 0.02938 | −0.008767 | 0.077153 |
| 92 | 0.026498 | 0.015094 | −0.087196 | 0.011191 | −0.07565 | −0.013199 | −0.112944 | −0.076415 | 0.011278 | −0.002238 | 0.019865 | 0.069264 | 0.021305 | 0.0096 |
| 93 | −0.008052 | −0.001623 | −0.023687 | −0.074086 | 0.05083 | −0.118304 | −0.035449 | −0.057941 | −0.005913 | −0.01645 | −0.13071 | 0.017195 | 0.011709 | 0.028214 |
| 94 | −0.079196 | −0.005488 | 0.020493 | 0.065918 | −0.094878 | 0.037727 | 0.019598 | 0.027324 | 0.002865 | 0.023492 | 0.037421 | −0.032303 | −0.045274 | −0.136404 |
| 95 | 0.022902 | 0.147131 | 0.059004 | 0.083068 | −0.011291 | 0.007687 | 0.009714 | −0.119243 | 0.108452 | −0.017806 | −0.061059 | −0.125232 | 0.011536 | 0.057603 |
| 96 | −0.068137 | −0.081138 | −0.075733 | 0.160641 | −0.056529 | −0.089723 | 0.053099 | 0.091981 | −0.10641 | −0.080347 | 0.006299 | −0.072128 | 0.039099 | 0.100773 |
| 97 | 0.106836 | −0.081802 | −0.13848 | −0.005143 | −0.019349 | 0.010605 | −0.137507 | 0.033723 | −0.128326 | −0.014628 | −0.017455 | −0.051558 | −0.029786 | 0.03109 |
| 98 | −0.024323 | −0.040315 | −0.022529 | 0.069201 | −0.02378 | 0.003699 | 0.000182 | 0.063453 | −0.005623 | 0.009154 | −0.138309 | 0.071574 | −0.021862 | −0.165251 |
| 99 | −0.036234 | 0.030003 | 0.009188 | −0.032717 | 0.03864 | 0.085226 | 0.074342 | 0.077248 | 0.0698431 | 0.0604721 | −0.008848 | 0.0363371 | −0.024069 | 0.044364 |
| 100 | −0.003222 | 0.0269231 | 0.0312181 | 0.001361 | −0.032262 | 0.004692 | 0.002666 | −0.027991 | 0.008194 | 0.003843 | −0.002075 | −0.013564 | −0.006692 | 0.035714 |
| 101 | −0.040564 | −0.006518 | −0.029142 | 0.020262 | 0.020277 | −0.006634 | −0.027635 | −0.000167 | −0.040362 | −0.006937 | −0.012056 | −0.026679 | −0.024082 | 0.028246 |
| 102 | 0.014627 | 0.071904 | 0.000045 | −0.035681 | 0.003358 | 0.039618 | −0.059559 | −0.001399 | −0.009818 | 0.032669 | 0.04502 | −0.011675 | 0.003863 | 0.01395 |
| 103 | −0.046218 | 0.001745 | −0.010258 | −0.020642 | 0.009246 | −0.025699 | 0.017312 | −0.012076 | −0.051813 | 0.00287 | 0.056216 | −0.042796 | −0.014804 | 0.010503 |
| 104 | −0.000708 | 0.01464 | 0.013615 | 0.037158 | −0.03265 | −0.010987 | −0.043368 | 0.031831 | −0.011742 | 0.0187471 | 0.0202441 | −0.002824 | −0.041987 | −0.012931 |
| 105 | 0.0060841 | 0.030982 | −0.034876 | 0.015717 | −0.00862 | 0.018492 | −0.020911 | 0.004148 | 0.018944 | 0.020918 | 0.009289 | 0.020625 | −0.026734 | 0.063438 |
| 106 | 0.018518 | 0.018181 | 0.058699 | −0.030511 | −0.022199 | 0.010607 | −0.029734 | −0.021076 | 0.023134 | 0.010829 | −0.018044 | −0.029568 | 0.003932 | 0.020419 |
| 107 | 0.010544 | −0.02756 | 0.019937 | 0.042809 | 0.009877 | 0.092731 | −0.023027 | −0.015089 | −0.015425 | 0.004473 | 0.020026 | −0.02059 | 0.010442 | 0.004603 |
| 108 | 0.033736 | −0.043141 | −0.061561 | −0.021835 | 0.01094 | −0.003213 | −0.040277 | −0.016993 | −0.007752 | −0.024165 | 0.013494 | 0.020775 | 0.082357 | −0.028312 |
| 109 | 0.016191 | −0.049033 | −0.009733 | 0.014025 | 0.050685 | −0.032599 | 0.01497 | 0.040007 | 0.019407 | 0.032168 | 0.002843 | 0.05033 | 0.03772 | 0.026949 |
| 110 | 0.018081 | −0.027254 | −0.074011 | 0.029366 | −0.039196 | 0.023619 | 0.024468 | −0.031601 | 0.013925 | 0.006181 | 0.045886 | −0.004996 | −0.020737 | 0.037163 |
| 111 | 0.00182 | −0.053269 | 0.016926 | −0.029401 | 0.016113 | 0.007184 | 0.050818 | 0.008347 | 0.015408 | 0.039449 | 0.046909 | −0.009066 | 0.005839 | 0.059079 |
| 112 | 0.020674 | −0.009548 | 0.089763 | −0.015404 | −0.011655 | −0.003568 | −0.038607 | −0.026523 | 0.040974 | 0.01514 | −0.008493 | −0.005058 | 0.019501 | −0.069346 |
| 113 | −0.064769 | −0.054048 | −0.005349 | 0.009032 | 0.056291 | 0.017091 | 0.046407 | −0.033138 | −0.036001 | −0.032176 | −0.09616 | −0.053009 | 0.000546 | −0.011861 |
| 114 | −0.005245 | −0.021508 | 0.012542 | −0.005619 | −0.020681 | −0.039281 | 0.011539 | 0.04758 | −0.017692 | 0.018593 | −0.039337 | −0.031018 | 0.012747 | 0.017959 |
| 115 | −0.002891 | 0.0066151 | 0.0533821 | 0.042079 | 0.024379 | 0.001517 | 0.01929 | −0.0124 | −0.004789 | −0.025592 | −0.001356 | −0.057781 | −0.047933 | −0.012355 |
| 116 | −0.052176 | −0.022219 | 0.027954 | 0.01393 | −0.026333 | −0.00984 | 0.060963 | −0.014957 | 0.043534 | −0.031501 | −0.013293 | −0.078209 | −0.008307 | −0.052505 |
| 117 | 0.016374 | −0.013619 | 0.026888 | −0.066144 | 0.028747 | −0.032751 | 0.011826 | 0.009357 | 0.002851 | 0.002786 | −0.023405 | −0.018621 | −0.018119 | 0.012641 |
| 118 | 0.012946 | −0.033441 | 0.011666 | −0.016372 | 0.029928 | −0.05028 | 0.001039 | 0.060099 | −0.002838 | 0.020286 | −0.01129 | −0.007297 | −0.036971 | −0.043908 |
| 119 | 0.000575 | −0.053079 | −0.047784 | 0.043397 | 0.021356 | −0.029269 | 0.038997 | −0.051526 | −0.026594 | −0.001719 | 0.0177561 | −0.008954 | 0.0299431 | 0.001693 |
| 120 | 0.0131621 | −0.022536 | −0.009067 | 0.017742 | 0.002063 | 0.00883 | −0.008675 | −0.017743 | 0.012222 | −0.03385 | −0.029517 | 0.011765 | 0.009108 | −0.059571 |
| 121 | 0.029347 | −0.01809 | −0.021067 | −0.004002 | 0.033685 | −0.032623 | −0.011653 | 0.002908 | 0.035055 | 0.020868 | −0.036893 | 0.048782 | −0.000462 | 0.035397 |
| 122 | 0.004992 | −0.020573 | −0.042393 | −0.003223 | −0.019969 | 0.005847 | −0.094894 | 0.001768 | −0.025319 | 0.02884 | −0.003618 | 0.017627 | −0.048682 | −0.016326 |
| 123 | 0.02819 | 0.025655 | −0.015874 | 0.013667 | −0.010323 | −0.061134 | −0.043629 | −0.048102 | −0.052651 | 0.002681 | 0.010374 | 0.033665 | 0.014255 | 0.013884 |
| 124 | 0.006403 | −0.000443 | −0.008871 | 0.006546 | 0.009247 | −0.012217 | −0.021341 | −0.083306 | −0.046261 | 0.000512 | 0.018666 | 0.014158 | 0.016127 | 0.016917 |
| 125 | −0.055466 | 0.007153 | 0.016235 | −0.019862 | −0.041069 | 0.007336 | 0.00681 | 0.023277 | −0.010143 | −0.060919 | −0.051242 | 0.022678 | 0.008495 | −0.103418 |
| 126 | −0.021715 | −0.024609 | −0.003614 | 0.029506 | −0.018471 | −0.036393 | 0.055808 | 0.007162 | −0.019529 | −0.033418 | −0.030701 | −0.009499 | 0.026486 | −0.008619 |
| 127 | −0.03276 | −0.033531 | 0.044492 | 0.022588 | 0.007867 | −0.037208 | 0.057095 | 0.001585 | −0.013542 | −0.033917 | −0.012368 | −0.03804 | 0.029894 | −0.012684 |
| 128 | −0.068205 | −0.019559 | 0.000405 | −0.030361 | −0.057126 | 0.046839 | 0.007522 | 0.012228 | −0.017904 | −0.050406 | 0.000916 | −0.07738 | −0.049188 | −0.016118 |
| 129 | −0.054164 | −0.023984 | 0.028762 | −0.038983 | 0.03612 | 0.002876 | −0.054548 | −0.041734 | 0.029429 | 0.031577 | −0.017046 | 0.00799 | 0.03806 | −0.043405 |
| 130 | −0.08389 | −0.059543 | 0.080169 | 0.031406 | −0.012964 | −0.02635 | 0.041667 | 0.031726 | −0.00955 | −0.005154 | −0.052925 | −0.036236 | 0.056823 | −0.074021 |
| 131 | −0.033193 | −0.067571 | 0.021168 | −0.039938 | 0.062001 | 0.003388 | 0.056696 | 0.031971 | 0.018264 | 0.020599 | 0.012909 | −0.023708 | 0.008907 | 0.023026 |
| 132 | 0.017027 | 0.005049 | −0.042618 | −0.036643 | −0.029373 | 0.028046 | 0.023445 | 0.045296 | 0.019813 | −0.029439 | −0.016112 | 0.040253 | −0.004408 | −0.051209 |
| 133 | −0.026889 | 0.012873 | −0.011167 | −0.056698 | 0.004609 | −0.042336 | −0.030631 | −0.00066 | −0.089551 | −0.Q65856 | 0.007666 | −0.018118 | 0.061375 | 0.071023 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 134 | −0.033191 | −0.074085 | −0.00274 | −0.05424 | 0.020813 | −0.003584 | 0.014953 | −0.023133 | −0.01789 | −0.038673 | −0.073285 | 0.047274 | −0.019489 | 0.012309 |
| 135 | 0.000829 | 0.001491 | 0.009624 | 0.011409 | −0.047742 | −0.007928 | −0.0305 | −0.044554 | −0.061763 | −0.061209 | 0.005411 | −0.040152 | −0.026995 | −0.048092 |
| 136 | 0.0277371 | −0.013705 | −0.009986 | −0.019409 | 0.029375 | −0.021873 | −0.017077 | −0.069905 | −0.076531 | −0.021657 | −0.007031 | −0.045647 | −0.02442 | −0.043497 |
| 137 | 0.715439 | 0.014009 | 0.006101 | −0.038135 | −0.014545 | 0.023353 | 0.020703 | 0.008527 | −0.010911 | −0.025116 | 0.00687 | −0.076798 | −0.026946 | 0.011352 |
| 138 | 0.012029 | 0.526188 | 0.028279 | −0.021706 | −0.038921 | 0.027663 | 0.016516 | 0.025278 | −0.004207 | −0.017356 | −0.039248 | −0.037882 | 0.017379 | −0.035275 |
| 139 | 0.029075 | 0.068649 | 0.468927 | 0.072235 | 0.040764 | 0.000382 | 0.001072 | 0.034401 | −0.000993 | −0.042433 | −0.016219 | 0.028724 | 0.009526 | 0.01433 |
| 140 | −0.006495 | −0.006019 | 0.057783 | 0.443319 | 0.027692 | −0.025315 | −0.029442 | −0.001897 | 0.010799 | −0.000822 | −0.039192 | −0.090364 | 0.025906 | 0.020806 |
| 141 | −0.019737 | −0.034248 | 0.002736 | −0.018415 | 0.713378 | 0.031916 | −0.034322 | 0.007156 | 0.008502 | −0.020135 | 0.021157 | 0.004536 | −0.075563 | −0.033059 |
| 142 | 0.026569 | 0.033765 | −0.020485 | 0.015594 | 0.005571 | 0.70923 | −0.026336 | −0.045577 | −0.034098 | 0.005527 | −0.03399 | −0.037551 | 0.026024 | −0.01155 |
| 143 | 0.024408 | 0.036211 | −0.038211 | −0.088858 | −0.022978 | −0.015864 | 0.669961 | −0.106026 | −0.103981 | 0.029146 | 0.025163 | 0.048075 | −0.014861 | −0.009282 |
| 144 | −0.008161 | 0.052443 | 0.019429 | −0.005744 | −0.014196 | −0.057079 | −0.077063 | 0.741861 | −0.072786 | −0.011391 | 0.003131 | −0.057583 | −0.004928 | 0.057363 |
| 145 | −0.018159 | −0.003292 | −0.001683 | −0.008717 | 0.020225 | −0.031536 | −0.077538 | −0.059266 | 0.7394811 | −0.044412 | 0.0317451 | 0.0044831 | −0.011744 | 0.012125 |
| 146 | −0.03065 | −0.010294 | −0.0362861 | −0.001312 | −0.046032 | −0.008855 | 0.031736 | −0.016632 | −0.044222 | 0.87503 | −0.056199 | −0.048004 | 0.028533 | −0.027008 |
| 147 | 0.028017 | −0.000381 | 0.000248 | −0.050601 | 0.003902 | −0.055728 | 0.018786 | −0.009605 | 0.02884 | −0.050192 | 0.723202 | −0.012272 | 0.054125 | −0.014512 |
| 148 | −0.061081 | −0.042259 | −0.018884 | −0.067863 | 0.004089 | −0.016818 | 0.028033 | −0.061332 | 0.008496 | −0.013337 | −0.009856 | 0.473291 | −0.054014 | 0.010184 |
| 149 | −0.036497 | 0.029515 | −0.008936 | −0.02029 | −0.045801 | 0.008951 | −0.030941 | 0.008268 | 0.000898 | 0.013334 | 0.041463 | −0.017209 | 0.746247 | −0.024205 |
| 150 | −0.04951 | −0.063377 | 0.007778 | 0.048557 | −0.013078 | 0.005164 | −0.016528 | 0.039067 | −0.010655 | −0.027428 | −0.024006 | −0.010857 | 0.011715 | 0.608433 |
| 151 | −0.004064 | 0.0273 | −0.113174 | 0.004374 | −0.002725 | 0.01322 | −0.024537 | 0.002078 | −0.002973 | 0.029908 | −0.041737 | 0.01699 | −0.049159 | −0.030695 |
| 152 | −0.020766 | −0.005249 | −0.029002 | 0.008015 | 0.04326 | −0.046216 | −0.005607 | −0.021143 | 0.013885 | 0.026499 | −0.032835 | −0.003205 | −0.020787 | 0.039415 |
| 153 | −0.01603 | 0.041138 | −0.023797 | −0.005327 | −0.036865 | −0.076605 | −0.050153 | −0.089739 | −0.016565 | −0.035668 | −0.032046 | −0.040143 | −0.008262 | 0.00196 |
| 154 | 0.010186 | 0.015521 | 0.021274 | 0.014488 | 0.02882 | −0.13415 | 0.002371 | −0.085402 | −0.032197 | −0.00292 | −0.057233 | −0.033748 | −0.000278 | −0.039154 |
| 155 | −0.001359 | −0.005279 | 0.02448 | 0.028606 | −0.001747 | −0.022421 | 0.014254 | −0.036891 | 0.007495 | −0.011849 | 0.020461 | 0.01448 | −0.001189 | −0.017907 |
| 156 | 0.0602721 | 0.0002781 | −0.0130391 | 0.035985 | −0.004642 | −0.067309 | 0.002483 | −0.006365 | −0.002566 | −0.067476 | −0.052386 | 0.046884 | −0.016063 | −0.059472 |
| 157 | −0.018325 | −0.010009 | 0.014999 | −0.064093 | −0.049158 | 0.004313 | 0.01924 | 0.001804 | −0.042827 | −0.039248 | 0.024883 | −0.029214 | 0.004174 | −0.052737 |
| 158 | −0.048894 | −0.018858 | 0.001294 | −0.012825 | −0.056628 | −0.011028 | −0.023106 | −0.019922 | 0.039401 | −0.006195 | −0.046738 | 0.034748 | −0.012953 | 0.051573 |
| 159 | 0.00845 | 0.017301 | 0.007159 | 0.009258 | −0.003255 | −0.046391 | 0.024011 | 0.004361 | −0.066585 | 0.01365 | 0.039785 | −0.069791 | −0.058816 | −0.104422 |
| 160 | −0.009343 | 0.001174 | −0.025383 | −0.019729 | −0.006406 | −0.012535 | −0.028121 | 0.0058 | 0.0406811 | 0.0081311 | −0.028205 | 0.0223161 | −0.018255 | −0.017108 |
| 161 | 0.013942 | −0.035853 | −0.0798161 | 0.027911 | 0.011087 | −0.036471 | −0.04855 | −0.017037 | 0.037791 | 0.024493 | 0.006595 | −0.109648 | −0.0106 | −0.005666 |
| 162 | −0.05 | 0.005223 | −0.025735 | 0.016415 | 0.006755 | −0.029942 | −0.04347 | −0.085248 | −0.029219 | 0.024579 | 0.028192 | 0.040291 | −0.042911 | 0.027404 |
| 163 | −0.043589 | 0.011909 | 0.046509 | 0.019107 | −0.036907 | −0.097326 | −0.025944 | 0.002464 | −0.022534 | 0.025848 | 0.039218 | 0.003298 | −0.051272 | −0.048214 |
| 164 | −0.054044 | 0.0488361 | −0.051418 | −0.014513 | −0.024981 | −0.041835 | 0.028009 | −0.004071 | −0.042137 | −0.033024 | −0.024352 | −0.037336 | −0.044855 | 0.010313 |
| 165 | −0.005357 | 0.028031 | 0.0456251 | 0.009645 | 0.009394 | 0.02748 | −0.048277 | −0.025876 | 0.0021091 | 0.0133031 | 0.045262 | −0.037846 | −0.060366 | −0.004011 |
| 166 | 0.038438 | −0.095724 | −0.006659 | 0.001438 | 0.000649 | −0.033331 | −0.00769 | −0.031345 | 0.009576 | −0.000571 | 0.0315 | −0.036744 | 0.027096 | 0.028989 |
| 167 | −0.031129 | 0.000868 | −0.031813 | −0.017009 | −0.023998 | 0.060537 | −0.052596 | −0.056332 | −0.068473 | −0.02021 | 0.015713 | 0.031527 | −0.033737 | 0.000072 |
| 168 | −0.024655 | 0.012657 | 0.019788 | 0.008536 | 0.008253 | 0.004702 | −0.036396 | −0.011662 | −0.008514 | −0.009421 | 0.011622 | 0.019755 | 0.02216 | −0.023544 |
| 169 | −0.000902 | −0.000281 | −0.011537 | −0.005883 | −0.023851 | 0.013666 | −0.019137 | −0.014318 | 0.015009 | −0.003405 | 0.000477 | −0.010713 | −0.002194 | 0.004873 |
| 170 | −0.013402 | −0.010687 | −0.007864 | 0.026348 | −0.014661 | 0.027799 | 0.004714 | −0.015247 | 0.032135 | 0.002196 | −0.019342 | −0.02424 | −0.016878 | 0.001455 |
| 171 | 0.0200471 | 0.0214941 | −0.032147 | −0.022811 | −0.04145 | 0.000939 | −0.015404 | −0.017775 | 0.0325481 | 0.0022821 | −0.008462 | 0.0174381 | −0.002571 | 0.022584 |
| 172 | 0.0031721 | 0.017025 | −0.0006251 | −0.016138 | −0.032609 | 0.017789 | 0.002226 | −0.022598 | −0.013427 | −0.005277 | 0.00735 | −0.007217 | 0.01635 | −0.013729 |
| 173 | −0.029367 | 0.013934 | −0.006687 | −0.030319 | −0.020815 | 0.014745 | 0.02478 | 0.021184 | −0.008909 | −0.018006 | 0.013539 | −0.000224 | −0.010722 | 0.011517 |
| 174 | 0.024841 | 0.020003 | 0.025604 | −0.006531 | −0.005619 | −0.025916 | 0.024393 | 0.042836 | 0.002723 | −0.000781 | −0.026357 | 0.001525 | −0.018627 | 0.031534 |
| 175 | 0.02031 | 0.013513 | −0.022241 | 0.012304 | 0.047006 | 0.024976 | 0.003306 | 0.026733 | −0.001863 | 0.007843 | −0.015633 | 0.047138 | −0.030289 | −0.040813 |
| 176 | −0.001543 | 0.018027 | −0.013244 | −0.029756 | −0.021772 | 0.039437 | −0.043644 | −0.02399 | −0.021335 | 0.01468 | 0.04079 | −0.007334 | 0.023354 | 0.01663 |
| 177 | 0.0474 | −0.010033 | −0.03324 | 0.006808 | 0.04875 | 0.077736 | −0.014311 | −0.033925 | −0.008747 | −0.002645 | −0.037064 | −0.077545 | −0.028137 | −0.031543 |
| 178 | −0.045603 | −0.002384 | −0.04764 | 0.017091 | −0.004707 | −0.001995 | −0.052792 | −0.027218 | −0.046353 | 0.016533 | 0.01017 | −0.032353 | 0.0104 | 0.057654 |
| 179 | −0.014688 | 0.011117 | 0.021256 | 0.002676 | 0.024408 | −0.026074 | −0.015567 | 0.006604 | 0.012427 | 0.017497 | −0.018139 | −0.033435 | 0.015303 | 0.021209 |
| 180 | −0.028422 | −0.01469 | −0.001329 | 0.006316 | 0.004209 | −0.017004 | −0.016951 | 0.003522 | −0.001447 | 0.012856 | −0.028242 | −0.027871 | 0.004133 | 0.019834 |
| 181 | −0.029351 | −0.010807 | −0.017994 | −0.000208 | 0.018176 | −0.00531 | −0.00983 | 0.006999 | 0.009153 | 0.014715 | −0.026215 | −0.008322 | −0.006204 | 0.021413 |
| 182 | −0.021445 | 0.004457 | −0.012225 | 0.034209 | 0.020201 | −0.008235 | 0.02988 | −0.006782 | 0.033212 | 0.023118 | −0.020035 | −0.029527 | −0.002931 | −0.014027 |
| 183 | 0.002048 | 0.026504 | 0.017102 | −0.00977 | 0.000739 | 0.028236 | 0.019372 | −0.002157 | 0.039251 | 0.001483 | −0.019937 | −0.011927 | 0.012061 | −0.017263 |
| 184 | 0.006594 | 0.014917 | −0.000165 | −0.050714 | −0.010009 | 0.007294 | 0.000315 | −0.018733 | 0.001344 | −0.01632 | 0.018194 | 0.010293 | 0.015696 | 0.011322 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 185 | −0.050852 | −0.085703 | −0.002279 | 0.04632 | −0.049654 | −0.035843 | −0.00399 | −0.000286 | −0.021147 | 0.011546 | 0.048562 | −0.011584 | −0.05022 | −0.004279 |
| 186 | 0.034683 | −0.009913 | −0.03832 | 0.00076 | −0.02374 | −0.014971 | −0.013056 | −0.011824 | 0.039784 | 0.014952 | −0.024962 | 0.008378 | 0.03663 | −0.021539 |
| 187 | −0.005591 | 0.010785 | −0.016038 | 0.020748 | −0.0104 | 0.025381 | 0.031085 | 0.022841 | −0.013655 | −0.010301 | 0.017604 | −0.017801 | 0.024752 | −0.036057 |
| 188 | 0.026609 | 0.002327 | 0.002906 | 0.005441 | −0.021307 | 0.011591 | 0.025937 | 0.013711 | −0.013639 | −0.00827 | −0.001145 | −0.027244 | 0.019619 | −0.015003 |
| 189 | 0.021172 | −0.017551 | −0.023702 | −0.006437 | −0.024769 | 0.000464 | 0.045701 | 0.042286 | −0.016581 | −0.013466 | −0.030048 | −0.014874 | 0.030299 | 0.002756 |
| 190 | −0.016594 | −0.006525 | −0.027188 | 0.001787 | −0.027557 | 0.051746 | −0.039098 | 0.020461 | 0.002593 | 0.02512 | 0.0091 | 0.036848 | −0.023193 | 0.026129 |
| 191 | 0.030187 | −0.01139 | 0.024166 | −0.048869 | −0.024068 | 0.02117 | −0.019205 | 0.041352 | 0.035377 | 0.009688 | 0.019812 | 0.012476 | −0.04232 | 0.026547 |
| 192 | 0.013863 | −0.027228 | 0.042853 | 0.050987 | −0.02502 | 0.004014 | 0.020503 | −0.025288 | −0.01246 | −0.013263 | 0.035153 | 0.005671 | −0.012282 | −0.025165 |
| 193 | 0.019987 | 0.021001 | 0.006599 | 0.039395 | 0.012891 | −0.014281 | 0.017231 | −0.020196 | 0.009045 | 0.00922 | 0.027908 | −0.010458 | 0.016914 | 0.034129 |
| 194 | 0.040038 | 0.01158 | −0.00938 | 0.004887 | 0.02902 | 0.033881 | −0.058484 | 0.01341 | −0.026224 | 0.017335 | 0.008197 | 0.01038 | 0.015636 | −0.041043 |
| 195 | −0.017877 | −0.008377 | −0.027757 | −0.00717 | 0.027554 | 0.006037 | 0.007333 | 0.0299 | 0.020381 | 0.01876 | 0.035834 | 0.003012 | −0.007338 | −0.004783 |
| 196 | 0.008964 | 0.000545 | −0.025576 | −0.017386 | 0.015324 | 0.0016 | −0.022242 | −0.009557 | 0.008676 | 0.013169 | 0.019378 | −0.00903 | −0.020531 | −0.000654 |
| 197 | −0.001495 | 0.009841 | 0.05784 | −0.006091 | −0.06056 | 0.04264 | −0.006634 | 0.012379 | 0.011762 | −0.00636 | 0.022318 | 0.032895 | −0.076699 | 0.043651 |
| 198 | −0.026222 | −0.03642 | 0.012926 | 0.007468 | −0.029393 | −0.007702 | 0.039731 | −0.005748 | −0.035951 | −0.026764 | −0.010572 | −0.039 | 0.025597 | −0.014294 |
| 199 | −0.024525 | −0.01913 | 0.013507 | −0.022418 | −0.008507 | −0.060109 | 0.021038 | −0.014668 | 0.015256 | −0.03225 | −0.107735 | −0.017671 | −0.059853 | 0.001658 |
| 200 | −0.00435 | 0.02154 | −0.03719 | −0.015627 | −0.00357 | 0.010408 | 0.029956 | −0.019291 | 0.028206 | −0.001292 | −0.014306 | −0.004602 | 0.027927 | 0.001844 |
| 201 | −0.00226 | 0.054928 | −0.084098 | −0.008525 | −0.005335 | 0.055547 | 0.024826 | 0.004329 | 0.03134 | −0.010772 | −0.031166 | −0.052655 | −0.014458 | 0.017661 |
| 202 | 0.032998 | −0.022736 | −0.006081 | 0.065057 | −0.014093 | 0.04795 | 0.015967 | −0.007084 | −0.020525 | −0.01268 | −0.01775 | 0.033589 | 0.007322 | 0.046855 |
| 203 | 0.002632 | 0.03416 | −0.00153 | 0.047363 | 0.023442 | 0.043957 | 0.023849 | 0.029076 | 0.007197 | 0.014959 | −0.01677 | −0.039486 | −0.030161 | 0.016967 |
| 204 | 0.008837 | −0.053006 | 0.031441 | −0.02441 | −0.002358 | 0.032529 | −0.039011 | −0.004875 | 0.000715 | −0.005255 | −0.038806 | −0.011783 | 0.021068 | −0.035917 |
| 205 | 0.002913 | −0.002304 | 0.0022 | −0.055676 | −0.03475 | −0.05488 | −0.018538 | 0.000169 | 0.060709 | 0.041279 | 0.025183 | 0.033749 | 0.033685 | −0.054423 |
| 206 | 0.057801 | −0.043644 | −0.007807 | 0.069198 | −0.021306 | −0.008542 | −0.01371 | 0.017535 | −0.044253 | 0.011545 | 0.053448 | −0.007951 | −0.005953 | −0.038866 |
| 207 | 0.019353 | 0.010509 | −0.054874 | −0.029372 | −0.035656 | 0.002729 | −0.001147 | 0.070946 | 0.055645 | 0.026096 | −0.041616 | 0.049091 | −0.061115 | 0.003441 |
| 208 | −0.020684 | −0.007131 | −0.011643 | −0.028426 | 0.00054 | 0.026618 | 0.049093 | 0.022208 | −0.020359 | 0.004895 | 0.056126 | 0.031251 | −0.00792 | −0.009181 |
| 209 | 0.044721 | −0.100164 | 0.03224 | −0.036563 | 0.011478 | 0.006812 | −0.002267 | 0.001246 | −0.00317 | −0.001701 | −0.02975 | 0.031145 | −0.021733 | 0.0139 |
| 210 | −0.017616 | −0.065943 | −0.029833 | 0.098775 | 0.031711 | 0.059782 | 0.041535 | 0.034312 | 0.010336 | 0.003213 | −0.009682 | 0.028423 | −0.036233 | −0.055502 |
| 211 | 0.006932 | 0.026626 | 0.022432 | −0.088815 | 0.02021 | 0.023763 | −0.022726 | −0.037305 | −0.048745 | −0.034338 | −0.016655 | −0.055717 | −0.017377 | −0.040682 |
| 212 | 0.031576 | −0.028013 | −0.0886 | −0.021304 | −0.016719 | −0.009836 | −0.016535 | 0.009483 | 0.076258 | 0.004081 | −0.0786 | −0.011247 | 0.004137 | −0.03721 |
| 213 | 0.024101 | 0.000051 | −0.003638 | −0.009726 | −0.040973 | −0.01298 | 0.029184 | 0.036291 | −0.010169 | 0.011905 | −0.020064 | −0.031581 | 0.000675 | 0.00656 |
| 214 | −0.004787 | −0.00394 | 0.042858 | −0.027963 | 0.002401 | −0.048523 | −0.021985 | −0.009652 | −0.020975 | −0.006469 | −0.008927 | −0.0576 | 0.0253 | 0.008809 |
| 215 | 4.021438 | 0.001494 | 0.031649 | −0.073406 | −0.019322 | −0.019988 | −0.072774 | −0.018616 | −0.012509 | 0.038291 | −0.01354 | 0.0301 | 0.006689 | −0.049455 |
| 216 | 0.032025 | −0.007954 | 0.016698 | −0.000013 | −0.049685 | 0.03223 | −0.02224 | −0.029739 | −0.027345 | −0.010011 | 0.013287 | 0.038093 | −0.049996 | 0.02029 |
| 217 | 0.072105 | −0.042675 | 0.021531 | 0.012672 | 0.010317 | 0.024605 | 0.031476 | 0.011876 | 0.016329 | 0.007898 | −0.056206 | 0.001919 | 0.020417 | −0.078948 |
| 218 | 0.004612 | 0.011127 | −0.014943 | −0.009202 | 0.012209 | −0.003508 | −0.038864 | −0.011098 | −0.040834 | −0.013551 | 0.014304 | −0.013389 | −0.005558 | 0.018227 |
| 219 | 0.038983 | −0.012735 | −0.01571 | −0.002675 | −0.024976 | −0.025674 | −0.014355 | 0.002334 | −0.040201 | −0.032203 | 0.002541 | −0.016066 | −0.014227 | 0.007005 |
| 220 | 0.010029 | 0.001974 | 0.053594 | 0.034092 | 0.016948 | 0.034822 | 0.058565 | 0.024624 | 0.029117 | −0.021255 | −0.026262 | 0.039655 | 0.032243 | −0.0324 |
| 221 | −0.006175 | −0.021211 | 0.012374 | −0.020261 | 0.003508 | −0.000782 | −0.009421 | 0.039126 | 0.00124 | −0.00326 | 0.009669 | 0.0211311 | −0.026865 | −0.018928 |
| 222 | 0.010219 | −0.045574 | 0.019913 | −0.00424 | −0.019492 | 0.039733 | −0.00397 | 0.016551 | −0.00289 | −0.006386 | 0.002554 | −0.000639 | −0.018465 | −0.020026 |
| 223 | 0.020476 | 0.027571 | 0.02931 | 0.007904 | 0.016435 | 0.029367 | −0.021353 | 0.030845 | 0.016753 | 0.004653 | −0.012729 | 0.034406 | −0.007744 | −0.004037 |
| 224 | 0.011555 | −0.002213 | 0.000338 | 0.019356 | −0.027127 | −0.053741 | 0.010811 | −0.013852 | −0.027832 | 0.009981 | 0.005886 | −0.001483 | −0.040725 | 0.028537 |
| 225 | −0.023477 | −0.011066 | 0.016521 | −0.01292 | −0.00624 | −0.05133 | 0.020646 | −0.005447 | −0.053505 | 0.003621 | 0.011691 | 0.002097 | −0.043526 | 0.01675 |
| 226 | 0.010416 | 0.012158 | 0.007719 | −0.006129 | −0.024872 | −0.003116 | −0.024081 | −0.013907 | 0.000343 | 0.00107 | −0.000181 | 0.02812e | 0.008657 | 0.007855 |
| 227 | 0.030452 | 0.06619 | −0.033788 | 0.005053 | 0.00634 | −0.019435 | −0.030557 | −0.034707 | −0.030069 | 0.014603 | 0.014823 | 0.00656 | 0.006498 | 0.00412 |
| 228 | −0.041209 | 0.027786 | −0.039534 | 0.050054 | −0.021262 | 0.031081 | 0.009522 | 0.043705 | 0.002841 | 0.016361 | 0.04507 | 0.021532 | −0.037082 | 0.00543 |
| 229 | −0.001279 | 0.007689 | −0.02952 | 0.048165 | 0.032986 | −0.011991 | 0.031703 | 0.016036 | −0.017306 | 0.014484 | 0.016882 | 0.018187 | −0.020429 | −0.027729 |
| 230 | −0.055902 | 0.010641 | 0.01859 | −0.029719 | −0.031497 | 0.015938 | −0.02967 | −0.039358 | −0.001663 | −0.018735 | −0.002725 | −0.010582 | −0.017187 | 0.001362 |
| 231 | 0.004381 | 0.042914 | −0.002333 | −0.000851 | −0.012338 | 0.000639 | 0.03189 | 0.0197 | 0.017303 | −0.016793 | −0.029401 | 0.009767 | −0.061562 | −0.028002 |
| 232 | −0.014745 | 0.016035 | 0.11436 | 0.042039 | −0.053691 | 0.028984 | 0.001008 | 0.04388 | 0.035686 | −0.02094 | −0.025942 | −0.092241 | −0.015786 | 0.008903 |
| 233 | −0.028254 | −0.005121 | −0.045949 | 0.004659 | −0.013884 | 0.063551 | 0.007571 | −0.005761 | 0.005465 | −0.022729 | 0.011536 | −0.03496 | 0.001344 | 0.029559 |
| 234 | −0.03204 | 0.04739 | −0.015399 | 0.045543 | 0.000982 | −0.030397 | 0.015902 | 0.034165 | −0.0173 | −0.010609 | 0.017689 | 0.055533 | 0.008778 | −0.030297 |
| 235 | −0.02067 | 0.010353 | −0.006453 | −0.028958 | 0.003986 | −0.039595 | 0.01758 | 0.031979 | −0.038562 | −0.003521 | 0.015397 | −0.008853 | 0.004333 | −0.044887 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 236 | 0.008958 | 0.028093 | 0.009344 | −0.002173 | −0.00691 | 0.011484 | −0.030287 | −0.03009 | 0.017695 | 0.011398 | 0.017653 | −0.028233 | −0.007891 | 0.022648 |
| 237 | 0.007619 | −0.014681 | −0.025494 | 0.000761 | 0.009847 | 0.02292 | −0.000332 | 0.000241 | −0.030029 | 0.007022 | 0.003547 | 0.028486 | −0.024831 | 0.012052 |
| 238 | 0.017881 | −0.028552 | −0.005154 | −0.029894 | 0.014833 | 0.014824 | −0.014246 | 0.014311 | −0.016086 | −0.010336 | −0.015987 | −0.002073 | −0.021266 | 0.006434 |
| 239 | 0.013821 | 0.018009 | 0.003261 | −0.02514 | 0.003416 | 0.006176 | −0.014203 | −0.003658 | −0.011516 | −0.009694 | −0.013594 | −0.031418 | −0.012141 | 0.016195 |
| 240 | 0.020185 | −0.00631 | −0.000911 | −0.003739 | −0.01693 | −0.013153 | 0.009124 | −0.005703 | 0.023257 | 0.020119 | −0.011087 | −0.031831 | −0.020742 | 0.036385 |
| 241 | 0.007267 | −0.013668 | −0.018741 | −0.033335 | 0.041997 | 0.033425 | −0.023947 | −0.017455 | 0.0084 | 0.011477 | 0.000796 | −0.032556 | 0.019904 | 0.035832 |
| 242 | −0.030716 | 0.009844 | −0.039902 | −0.014642 | 0.033477 | 0.019894 | 0.038025 | 0.012816 | 0.01563 | −0.00455 | −0.023205 | 0.012222 | 0.043569 | 0.016398 |
| 243 | −0.018159 | −0.006617 | −0.018561 | −0.007011 | −0.004444 | 0.008838 | 0.011357 | 0.031954 | −0.002039 | −0.017091 | −0.000289 | −0.009078 | 0.014834 | −0.022616 |
| 244 | −0.037673 | 0.006459 | 0.011104 | 0.007767 | −0.006137 | −0.009875 | −0.025767 | 0.004647 | 0.013136 | −0.001617 | −0.001549 | −0.013598 | 0.019262 | −0.013006 |
| 245 | −0.012128 | 0.020089 | −0.004321 | −0.040891 | −0.025852 | −0.003581 | −0.068644 | −0.077494 | −0.000243 | 0.002591 | −0.010091 | 0.000241 | 0.005433 | 0.036855 |
| 246 | −0.017339 | 0.002276 | −0.03691 | 0.026513 | 0.002072 | −0.002033 | 0.030148 | −0.026108 | −0.017499 | 0.011386 | 0.024701 | 0.022997 | 0.000752 | 0.024367 |
| 247 | −0.01782 | 0.003048 | −0.018519 | −0.010444 | −0.005127 | 0.019199 | −0.0135 | 0.001055 | −0.011283 | 0.011641 | 0.012722 | −0.000959 | −0.008509 | −0.03672 |
| 248 | −0.00689 | −0.010595 | 0.037673 | −0.036347 | −0.012008 | 0.022145 | 0.007299 | 0.035213 | 0.002647 | −0.000934 | 0.006499 | −0.013074 | −0.006423 | −0.061202 |
| 249 | 0.040733 | −0.075216 | 0.053191 | −0.003666 | −0.011435 | 0.029684 | −0.004755 | −0.044752 | 0.002657 | −0.006273 | −0.005546 | −0.080005 | 0.007354 | 0.016485 |
| 250 | 0.043921 | 0.008742 | −0.006917 | 0.019258 | −0.006294 | −0.00721 | −0.011121 | −0.005223 | 0.008982 | 0.010432 | 0.011879 | 0.024906 | −0.001133 | 0.001364 |
| 251 | −0.009106 | 0.003816 | −0.010906 | −0.032011 | 0.016661 | −0.027655 | 0.017204 | 0.020572 | 0.009797 | 0.002537 | −0.024509 | 0.010844 | −0.001093 | 0.023487 |
| 252 | −0.021061 | 0.041829 | −0.002782 | −0.051817 | 0.04063 | −0.020515 | −0.028099 | −0.01541 | −0.004951 | −0.012317 | −0.02371 | −0.00322 | 0.032205 | 0.030877 |
| 253 | 0.003666 | 0.007599 | 0.015402 | 0.034852 | 0.023487 | 0.034496 | 0.001314 | −0.004712 | 0.047858 | −0.003368 | 0.022563 | −0.016112 | 0.001812 | −0.005175 |
| 254 | 0.012153 | 0.003342 | 0.014828 | 0.041795 | 0.034046 | −0.007068 | 0.004079 | 0.0059 | 0.006848 | 0.01174 | −0.003608 | −0.010192 | 0.004376 | 0.006729 |
| 255 | −0.037119 | −0.013573 | −0.026784 | 0.038695 | 0.006793 | −0.009867 | 0.017349 | 0.01174 | 0.007249 | 0.00402 | 0.000884 | 0.007541 | 0.006326 | −0.005417 |
| 256 | −0.008573 | −0.038539 | 0.026773 | −0.019023 | 0.002023 | 0.003375 | −0.036667 | −0.030317 | 0.010763 | 0.009525 | 0.013011 | −0.013266 | −0.006314 | 0.015388 |
| 257 | −0.010617 | 0.011728 | 0.010692 | −0.025168 | 0.0073 | 0.008511 | 0.010345 | 0.006723 | 0.000759 | −0.002648 | 0.017069 | 0.010317 | 0.012528 | −0.018398 |
| 258 | −0.01092 | 0.053493 | −0.019531 | −0.010918 | 0.031769 | 0.000972 | 0.024813 | 0.006356 | −0.002261 | 0.011958 | 0.003283 | −0.017264 | −0.020204 | −0.026786 |
| 259 | 0.019526 | −0.021651 | 0.012934 | −0.016838 | −0.002573 | 0.022767 | 0.020347 | −0.006262 | 0.002063 | 0.005044 | 0.003494 | −0.010346 | 0.003974 | 0.003671 |
| 260 | −0.025676 | 0.048735 | −0.026042 | 0.008847 | 0.036203 | −0.013943 | 0.021194 | 0.019407 | −0.012878 | −0.011378 | 0.032694 | 0.027149 | 0.037371 | −0.0438 |
| 261 | 0.00629 | 0.031932 | −0.045368 | 0.014794 | 0.068573 | −0.02229 | 0.055171 | 0.001169 | 0.012409 | 0.005312 | −0.007061 | 0.016704 | −0.012469 | −0.007474 |
| 262 | 0.010214 | −0.001571 | −0.0369171 | 0.013374 | 0.029481 | −0.001288 | −0.005595 | −0.041306 | −0.011929 | −0.005222 | −0.020178 | −0.010575 | −0.004944 | 0.025515 |
| 263 | 0.015104 | −0.000297 | −0.039483 | −0.00704 | 0.012487 | 0.017072 | −0.007846 | −0.021914 | −0.008672 | −0.026125 | −0.026362 | −0.000367 | 0.0108 | 0.034153 |
| 264 | 0.028441 | −0.044689 | 0.013963 | −0.001084 | −0.038931 | 0.039893 | −0.010084 | −0.007239 | −0.010991 | 0.013363 | 0.026045 | −0.021027 | −0.004123 | −0.011106 |
| 265 | 0.02896 | 0.007888 | 0.021654 | 0.028333 | 0.016409 | −0.009791 | 0.000143 | 0.010032 | 0.012749 | 0.023128 | 0.004087 | −0.030801 | 0.003809 | −0.012817 |
| 266 | 0.009228 | 0.005449 | −0.005493 | 0.012737 | 0.047655 | −0.050415 | 0.025815 | −0.011082 | 0.023994 | −0.004198 | −0.00398 | 0.00765 | 0.006024 | −0.026911 |
| 267 | 0.041704 | 0.026411 | −0.02547 | 0.040541 | −0.007581 | −0.005848 | 0.027712 | 0.028842 | 0.005059 | 0.011694 | −0.023881 | −0.005226 | −0.006122 | 0.021436 |
| 268 | 0.011542 | −0.003952 | 0.016536 | −0.017972 | −0.035275 | −0.001924 | −0.038918 | −0.003675 | −0.010083 | −0.00075 | 0.004013 | 0.00268 | 0.005836 | 0.014969 |
| 269 | 0.018768 | −0.023966 | 0.023118 | −0.022176 | −0.007222 | −0.011578 | −0.021748 | 0.018333 | 0.007398 | 0.004573 | 0.007364 | 0.006798 | 0.013363 | −0.008875 |
| 270 | 0.02181 | 0.018957 | −0.005454 | 0.003323 | −0.001746 | −0.013277 | 0.003667 | −0.004272 | 0.018141 | 0.000792 | 0.012484 | 0.004452 | 0.011844 | 0.005154 |
| 271 | 0.034409 | −0.023709 | −0.043948 | 0.016063 | −0.061272 | −0.015201 | −0.048145 | −0.042771 | 0.014485 | 0.020349 | 0.013304 | 0.026683 | −0.033727 | 0.002944 |
| 272 | 0.006026 | 0.001681 | −0.015677 | 0.01404 | 0.007563 | −0.031475 | 0.016238 | 0.023742 | −0.018668 | 0.01731 | −0.009773 | −0.005365 | −0.009983 | 0.016767 |
| 273 | −0.015448 | −0.012706 | 0.001698 | −0.024077 | −0.008069 | −0.011553 | 0.006718 | 0.009711 | 0.024047 | −0.008437 | −0.008997 | −0.008465 | 0.011073 | −0.014019 |
| 274 | −0.016072 | −0.018582 | −0.004562 | −0.013211 | 0.003772 | −0.02047 | 0.017719 | 0.017609 | 0.028699 | −0.00316 | −0.006423 | −0.009924 | 0.016817 | −0.025506 |
| 275 | −0.007773 | 0.023199 | −0.00728 | −0.029669 | −0.020758 | −0.039136 | 0.001404 | −0.026319 | 0.014212 | −0.010968 | 0.017618 | −0.049239 | 0.033507 | −0.021479 |
| 276 | 0.034739 | 0.012382 | 0.006524 | 0.014306 | 0.017624 | −0.012828 | −0.020953 | −0.029095 | −0.002759 | 0.013356 | 0.021326 | −0.036507 | −0.021828 | 0.023814 |
| 277 | −0.014538 | 0.009365 | −0.051313 | 0.019087 | 0.031761 | 0.000883 | −0.002258 | 0.023141 | 0.005039 | 0.029009 | 0.012562 | −0.010227 | −0.011981 | −0.005494 |
| 278 | −0.041246 | 0.038245 | −0.035837 | 0.046864 | 0.020684 | −0.032545 | 0.055804 | 0.012028 | 0.023838 | 0.007889 | 0.00705 | −0.031372 | −0.00415 | 0.004185 |
| 279 | 0.025957 | 0.003348 | 0.013631 | −0.017245 | −0.000245 | −0.033228 | 0.000861 | 0.008144 | 0.002768 | −0.023874 | −0.015857 | −0.030217 | −0.003119 | 0.012628 |
| 280 | −0.020138 | −0.040247 | 0.008937 | −0.01848 | −0.024898 | 0.029062 | 0.012379 | −0.002197 | 0.026924 | −0.013185 | 0.015565 | −0.021171 | −0.016882 | 0.010651 |
| 281 | 0.005871 | 0.032533 | 0.036426 | 0.021931 | −0.023998 | 0.020594 | 0.048331 | −0.012313 | 0.014655 | 0.004209 | −0.011431 | 0.043486 | −0.023697 | 0.009246 |
| 282 | 0.002606 | 0.035794 | 0.022797 | 0.012428 | −0.010496 | 0.007352 | 0.034541 | −0.003635 | 0.03028 | 0.011947 | 0.017437 | 0.026254 | −0.009454 | 0.031857 |
| 283 | 0.009784 | 0.007153 | 0.007835 | −0.009966 | −0.016242 | −0.025526 | 0.013087 | 0.013643 | −0.000212 | −0.008106 | 0.007384 | 0.000775 | 0.016176 | −0.027343 |
| 284 | 0.003975 | 0.018348 | 0.029552 | −0.027274 | 0.000435 | −0.016298 | 0.009088 | 0.001585 | 0.002078 | −0.007753 | 0.021976 | −0.003305 | 0.011179 | −0.003331 |
| 285 | −0.000525 | 0.015718 | 0.041956 | −0.019832 | −0.010033 | −0.012279 | −0.002214 | 0.005543 | 0.009298 | −0.003187 | 0.017233 | −0.003306 | 0.027055 | −0.03109 |
| 286 | 0.015567 | 0.044183 | 0.024969 | −0.024606 | 0.0441 | −0.007507 | 0.028368 | −0.021152 | −0.00932 | −0.012458 | −0.013059 | −0.032367 | −0.024039 | −0.014032 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 287 | −0.006209 | 0.048907 | 0.000735 | −0.00899 | 0.026902 | 0.000018 | 0.032932 | −0.017038 | −0.002679 | −0.028791 | −0.025755 | −0.038331 | 0.002137 | −0.007817 |
| 288 | −0.03292 | 0.051866 | 0.015821 | 0.009507 | 0.019086 | −0.015573 | 0.043222 | 0.011462 | −0.016024 | −0.002177 | 0.022387 | 0.002279 | −0.009914 | −0.001907 |
| 289 | −0.019888 | −0.008125 | −0.009284 | 0.012636 | 0.013227 | −0.012826 | 0.023628 | −0.028576 | −0.000512 | −0.00163 | 0.019692 | −0.010676 | 0.007664 | 0.008875 |
| 290 | −0.030565 | −0.015032 | 0.02231 | 0.033856 | −0.007574 | 0.022297 | 0.045182 | −0.000332 | 0.026032 | 0.000199 | 0.00728 | 0.038857 | 0.021062 | 0.005611 |
| 291 | −0.026039 | −0.015387 | 0.016351 | 0.026669 | −0.003091 | 0.021655 | 0.041987 | −0.006888 | 0.026527 | 0.003332 | 0.009483 | 0.038765 | 0.018409 | 0.009025 |
| 292 | 0.002314 | −0.05621 | 0.017204 | 0.002987 | 0.00687 | 0.01651 | 0.010902 | −0.001582 | 0.004356 | 0.002604 | 0.010122 | 0.033767 | 0.022924 | −0.006648 |
| 293 | 0.010554 | 0.015553 | 0.053255 | 0.005826 | −0.004347 | −0.013009 | −0.028556 | −0.042667 | 0.003052 | 0.006895 | −0.045981 | −0.029257 | −0.029228 | 0.005036 |
| 294 | 0.014208 | −0.001653 | −0.005111 | −0.054042 | −0.030452 | −0.005414 | −0.011988 | −0.004101 | −0.001288 | −0.000912 | −0.001337 | 0.0258421 | 0.0055341 | 0.004602 |
| 295 | −0.011536 | −0.043586 | 0.0096541 | −0.034946 | 0.005857 | 0.008802 | 0.020758 | −0.01844 | 0.015571 | −0.012954 | −0.006839 | −0.02289 | 0.000025 | 0.005797 |
| 296 | −0.023678 | −0.027042 | −0.047421 | −0.00802 | 0.043336 | 0.005355 | 0.024504 | 0.019277 | 0.041292 | −0.011974 | −0.026238 | 0.01192 | 0.043687 | 0.016472 |
| 297 | 0.002425 | −0.039436 | 0.016065 | −0.017389 | 0.033373 | −0.007925 | 0.028565 | −0.019027 | −0.011173 | −0.020289 | −0.024147 | −0.006378 | 0.003166 | 0.03637 |
| 298 | 0.006976 | 0.010362 | −0.004902 | 0.043405 | 0.031375 | −0.002895 | 0.060571 | 0.033258 | 0.050683 | 0.007521 | 0.016572 _ | 0.072647 | 0.002163 | 0.039345 |
| 299 | 0.004898 | 0.0064581 | 0.0393121 | 0.011092 | −0.003619 | 0.007086 | −0.028004 | 0.000622 | −0.008358 | −0.013619 | −0.021213 | −0.004978 | −0.038085 | 0.029647 |
| 300 | 0.075986 | −0.038217 | 0.012422 | 0.011777 | 0.008863 | 0.007054 | −0.010056 | −0.046238 | −0.023543 | −0.019859 | −0.027111 | 0.035724 | −0.042605 | 0.04039 |
| 301 | −0.02204 | −0.003884 | 0.057671 | −0.002144 | −0.028267 | 0.011476 | 0.015136 | 0.003175 | 0.001113 | −0.007455 | 0.005908 | 0.006771 | −0.003421 | 0.015488 |
| 302 | −0.001749 | −0.031798 | −0.029942 | 0.014376 | −0.018855 | 0.021066 | −0.003904 | −0.01364 | −0.021581 | −0.01065 | 0.004859 | −0.001131 | −0.004035 | 0.004103 |
| 303 | 0.000565 | 0.043447 | 0.0329241 | 0.020067 | −0.008995 | 0.018427 | −0.029737 | 0.009558 | −0.026163 | −0.003035 | 0.004351 | 0.015587 | −0.032595 | −0.013837 |
| 304 | 0.031572 | 0.033949 | −0.005707 | 0.03935 | −0.015298 | 0.027165 | −0.025308 | 0.004738 | −0.022511 | −0.015441 | −0.002172 | −0.001085 | −0.04992 | 0.015931 |
| 305 | 0.0120341 | 0.0561641 | 0.018432 | 0.025709 | 0.019657 | 0.000827 | −0.030369 | −0.025736 | −0.00766 | 0.030333 | 0.011788 | 0.050926 | −0.014696 | 0.02729 |
| 306 | 0.001997 | 0.006374 | −0.051738 | −0.000047 | −0.027414 | −0.016998 | 0.001149 | 0.018518 | −0.023968 | −0.048885 | −0.087896 | −0.000056 | 0.012246 | 0.041436 |
| 307 | 0.006091 | 0.058653 | −0.042954 | 0.047723 | −0.066392 | −0.003456 | −0.016876 | −0.010988 | −0.005656 | −0.014199 | 0.041432 | 0.06002 | 0.028012 | −0.006939 |
| 308 | 0.017012 | −0.016131 | −0.076042 | 0.040082 | −0.016163 | −0.002802 | −0.022071 | 0.004088 | −0.043578 | −0.066602 | −0.061183 | −0.016387 | 0.018336 | 0.042662 |
| 309 | 0.0189471 | −0.010956 | −0.066335 | 0.031589 | −0.013039 | −0.008868 | −0.008042 | −0.008255 | −0.025001 | −0.024494 | −0.021329 | −0.03111 | 0.0035981 | 0.012907 |
| 310 | 0.027561 | 0.0006991 | −0.054761 | −0.017534 | −0.053035 | −0.008564 | −0.015654 | 0.027269 | 0.004505 | −0.030983 | −0.064083 | −0.04554 | 0.012238 | −0.008057 |
| 311 | −0.024817 | 0.022155 | 0.003778 | 0.012635 | 0.016591 | 0.000301 | 0.010503 | −0.02898 | 0.013905 | 0.021735 | 0.021341 | −0.007548 | 0.015273 | −0.012001 |
| 312 | −0.094421 | 0.045949 | −0.004998 | −0.001181 | −0.025993 | 0.008456 | −0.016634 | 0.009777 | 0.015437 | −0.019922 | −0.07366 | −0.021349 | 0.035586 | −0.034409 |
| 313 | −0.012038 | 0.00972 | 0.01463 | −0.01108 | 0.063556 | 0.053775 | 0.027255 | −0.010781 | −0.027804 | −0.025192 | −0.002204 | −0.023066 | 0.036834 | 0.006288 |
| 314 | 0.041697 | 0.044319 | 0.054183 | −0.04431 | −0.022729 | 0.065132 | 0.035755 | −0.000994 | 0.031141 | 0.0121261 | −0.052094 | 0.0160451 | 0.0615381 | −0.008724 |
| 315 | 0.002792 | 0.004536 | −0.035126 | 0.073677 | 0.032913 | 0.016337 | −0.010494 | −0.004121 | −0.009057 | −0.003071 | −0.009159 | −0.007873 | −0.011009 | −0.00002 |
| 316 | −0.003753 | −0.078404 | 0.027798 | −0.02498 | 0.04835 | 0.003471 | 0.026943 | 0.032396 | 0.021151 | 0.011347 | 0.048589 | −0.071932 | 0.028633 | −0.083068 |
| 317 | −0.001235 | 0.009957 | −0.009642 | 0.030678 | −0.030278 | −0.004931 | 0.031526 | 0.025584 | 0.02522 | 0.007085 | 0.007053 | −0.007113 | 0.001979 | 0.001249 |
| 318 | 0.055776 | −0.051179 | −0.015386 | 0.013593 | −0.061803 | 0.023196 | 0.030938 | 0.008743 | 0.009209 | −0.004989 | −0.020446 | 0.036317 | 0.004381 | 0.00927 |
| 319 | 0.0122861 | −0.045085 | −0.0242111 | 0.03279 | 0.003583 | 0.001885 | −0.016055 | 0.001599 | −0.010605 | −0.015021 | 0.0123581 | −0.003714 | −0.010234 | −0.009106 |
| 320 | 0.0081451 | −0.0183661 | −0.0535271 | 0.015406 | 0.023919 | −0.04586 | −0.003363 | 0.033929 | 0.002044 | 0.005475 | −0.001354 | 0.021434 | 0.015078 | 0.012442 |
| 321 | −0.016788 | 0.001883 | −0.014366 | −0.008631 | 0.03171 | 0.02835 | 0.034254 | −0.018272 | −0.042164 | −0.038399 | 0.005589 | 0.009827 | 0.008924 | 0.038699 |
| 322 | −0.008413 | 0.016343 | 0.069366 | 0.007741 | −0.05062 | −0.013672 | −0.012034 | −0.016928 | 0.007929 | 0.029409 | −0.02961 | 0.005948 | −0.026858 | −0.004396 |
| 323 | 0.014285 | −0.014459 | 0.010226 | −0.008688 | −0.016213 | −0.0132 | 0.061842 | −0.009307 | 0.009093 | −0.007139 | 0.007877 | 0.030567 | −0.001143 | 0.00756 |
| 324 | −0.013898 | 0.040317 | −0.002409 | 0.008706 | −0.059606 | −0.030665 | 0.000205 | −0.014788 | 0.034175 | −0.024415 | −0.02804 | −0.013476 | −0.001918 | −0.059252 |
| 325 | −0.02252 | −0.0128831 | 0.0070141 | 0.022264 | 0.016201 | −0.015874 | 0.026927 | −0.017951 | 0.00334 | −0.010374 | −0.007927 | −0.015572 | 0.025979 | −0.012305 |
| 326 | −0.012079 | 0.035277 | −0.01218 | −0.066971 | −0.001925 | −0.007668 | −0.011665 | −0.025765 | 0.031781 | 0.01502 | −0.000321 | −0.043884 | 0.019873 | −0.011367 |
| 327 | −0.008288 | −0.010174 | −0.062206 | 0.026567 | −0.013052 | −0.001129 | 0.000232 | 0.014003 | −0.010955 | −0.010914 | −0.015392 | −0.013181 | −0.024338 | −0.002252 |
| 328 | −0.022069 | 0.022942 | −0.057846 | 0.002128 | 0.076043 | 0.016947 | −0.008352 | 0.004475 | −0.00897 | −0.037984 | 0.020018 | 0.077342 | 0.011288 | 0.015847 |
| 329 | −0.01184 | −0.005225 | 0.018621 | −0.051183 | 0.013658 | 0.011245 | −0.017388 | −0.022798 | −0.013678 | 0.01421 | 0.032082 | −0.038314 | −0.031952 | 0.015079 |
| 330 | 0.029109 | 0.016506 | 0.016855 | 0.029226 | −0.062181 | −0.017006 | 0.018644 | −0.018451 | −0.03413 | −0.019412 | 0.011046 | 0.001661 | 0.046008 | −0.035437 |
| 331 | 0.027335 | −0.010714 | −0.037993 | 0.003495 | −0.005837 | −0.022903 | −0.02984 | −0.040523 | −0.025802 | −0.005633 | 0.006859 | −0.000756 | −0.012503 | 0.003646 |
| 332 | 0.020568 | −0.057832 | 0.017306 | 0.005962 | 0.012555 | −0.016836 | −0.00021 | −0.00561 | 0.004092, | 0.020132 | 0.017821 | 0.026675 | 0.026628 | −0.04672 |
| 333 | −0.006671 | −0.045051 | 0.017801 | 0.003298 | −0.033332 | −0.006453 | 0.025833 | −0.029711 | 0.017822 | 0.0035 | 0.030789 | 0.010215 | −0.012292 | 0.002362 |
| 334 | 0.013727 | −0.014646 | 0.048444 | 0.051826 | 0.047597 | −0.014925 | −0.070881 | −0.004096 | −0.053016 | 0.048586 | −0.028306 | 0.064453 | 0.050784 | 0.046154 |
| 335 | −0.003802 | −0.034747 | −0.004829 | 0.012079 | −0.04058 | −0.022706 | −0.009885 | −0.032201 | −0.012474 | −0.044932 | 0.016684 | −0.032778 | 0.00374 | −0.027865 |
| 336 | −0.027229 | 0.04593 | 0.028739 | −0.025803 | −0.096369 | 0.035717 | −0.00642 | 0.006841 | −0.011217 | 0.029491 | 0.01034 | −0.01592 | −0.082975 | 0.038017 |
| 337 | −0.016269 | −0.054435 | 0.056075 | 0.061288 | −0.032674 | −0.027255 | −0.00207 | 0.039018 | 0.035197 | 0.012163 | −0.007016 | 0.042073 | 0.00823 | −0.054903 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 338 | −0.023241 | 0.052739 | 0.002917 | 0.037587 | 0.003319 | −0.022755 | −0.063451 | 0.001767 | 0.025984 | 0.017317 | 0.040989 | −0.054756 | −0.037422 | −0.040302 |
| 339 | 0.053579 | 0.007234 | 0.039656 | 0.033059 | 0.014799 | 0.014805 | −0.035728 | −0.027521 | −0.016754 | 0.040237 | −0.013769 | 0.039301 | 0.018658 | 0.008926 |
| 340 | 0.008903 | −0.030596 | 0.016355 | −0.016391 | 0.022206 | −0.008284 | −0.017766 | 0.003264 | −0.024461 | −0.003298 | −0.00456 | −0.010269 | 0.027472 | −0.002131 |

| | EV | EW | EX | EY | EZ | FA | FB | FC | FD | FE | FF | FG | FH | FI |
|---|---|---|---|---|---|---|---|---|---|---|---|---|---|---|
| 1 | −0.101768 | 0.051889 | 0.020976 | −0.011426 | 0.049431 | −0.014482 | 0.076736 | −0.076278 | −0.069408 | −0.008679 | 0.063507 | 0.176336 | 0.180036 | 0.018831 |
| 2 | 0.133735 | −0.072742 | −0.040788 | −0.064434 | −0.042547 | −0.053949 | 0.04552 | −0.093008 | −0.05508 | 0.005024 | −0.002028 | −0.035381 | −0.070092 | −0.055017 |
| 3 | −0.039689 | −0.032532 | −0.038645 | 0.014426 | 0.020663 | 0.044871 | −0.050227 | 0.074055 | 0.050162 | −0.086654 | −0.034961 | −0.117652 | −0.002888 | 0.037899 |
| 4 | 0.064087 | 0.005954 | 0.018144 | −0.050198 | −0.022603 | −0.078703 | 0.046672 | 0.080414 | 0.082557 | −0.07786 | −0.104993 | 0.030629 | 0.040069 | 0.084962 |
| 5 | −0.059175 | 0.018013 | 0.000328 | 0.059525 | −0.003762 | −0.004957 | 0.01386 | 0.039571 | −0.018769 | 0.097018 | 0.03338 | 0.136449 | −0.012584 | −0.014132 |
| 6 | −0.076681 | −0.054715 | −0.054169 | 0.002595 | 0.00523 | 0.084251 | 0.053537 | 0.182899 | −0.055204 | −0.075727 | 0.008389 | −0.038684 | −0.069 | −0.036373 |
| 7 | −0.054439 | 0.01885 | 0.018112 | −0.013357 | −0.063766 | −0.053517 | −0.040765 | −0.108167 | −0.028431 | −0.028668 | 0.041043 | 0.018026 | 0.047967 | −0.015378 |
| 8 | 0.015744 | −0.001932 | −0.063192 | −0.065889 | −0.046161 | 0.00469 | −0.087307 | −0.020489 | 0.030344 | −0.071467 | −0.013227 | 0.016356 | 0.043719 | −0.042509 |
| 9 | 0.064494 | 0.05148 | 0.048837 | −0.040777 | 0.03482 | −0.031439 | −0.059471 | 0.069568 | −0.080031 | −0.088621 | 0.059063 | −0.107899 | −0.041438 | −0.056067 |
| 10 | 0.020207 | 0.02627 | 0.083 | 0.09584 | 0.019727 | 0.017383 | −0.000042 | 0.009056 | 0.052075 | −0.005539 | −0.036639 | 0.020326 | −0.010797 | 0.085334 |
| 11 | 0.0457 | −0.004293 | −0.013249 | 0.004527 | 0.035598 | −0.025176 | 0.036202 | 0.013515 | −0.046036 | 0.011263 | −0.077734 | −0.049835 | −0.005781 | 0.002427 |
| 12 | 0.025968 | 0.052754 | −0.03035 | 0.038165 | −0.003577 | 0.013104 | 0.08629 | 0.049117 | 0.003414 | −0.105625 | −0.060864 | −0.0009 | 0.019779 | 0.094215 |
| 13 | 0.078323 | 0.046638 | 0.048391 | 0.007889 | 0.068641 | −0.069509 | −0.052921 | 0.013358 | 0.162115 | 0.041887 | −0.030518 | 0.074548 | −0.02209 | 0.045839 |
| 14 | −0.067153 | 0.075614 | −0.041523 | 0.055566 | 0.032741 | −0.00449 | 0.006085 | 0.097346 | 0.086325 | 0.082697 | 0.154818 | 0.024568 | 0.096135 | −0.029127 |
| 15 | −0.116037 | 0.016634 | 0.018022 | 0.049467 | −0.001029 | 0.059761 | 0.016951 | −0.048287 | −0.187427 | 0.074342 | −0.065489 | −0.009959 | 0.038666 | −0.004003 |
| 16 | −0.078418 | −0.071528 | −0.019837 | 0.053403 | 0.032496 | 0.059802 | −0.015038 | 0.073937 | 0.126811 | 0.059434 | −0.043119 | −0.070857 | −0.087308 | 0.000827 |
| 17 | 0.121318 | 0.003891 | −0.087195 | −0.064884 | −0.082615 | 0.058439 | −0.038549 | 0.039303 | 0.038997 | −0.019907 | −0.088532 | −0.055991 | −0.003337 | 0.039193 |
| 18 | −0.101204 | −0.002778 | 0.022927 | −0.014513 | 0.021202 | −0.0533 | −0.022026 | −0.059334 | 0.069284 | −0.007032 | 0.12931 | 0.071318 | 0.027251 | −0.03695 |
| 19 | 0.042157 | −0.004813 | 0.042943 | 0.011426 | 0.008604 | −0.030363 | −0.030109 | −0.014337 | 0.145329 | 0.050942 | 0.033143 | 0.027664 | 0.005173 | −0.169818 |
| 20 | −0.085457 | −0.019061 | −0.025267 | −0.079265 | −0.048594 | −0.065398 | −0.083332 | −0.041858 | 0.031842 | 0.082484 | 0.108208 | −0.073268 | −0.031567 | −0.081713 |
| 21 | −0.085766 | 0.067609 | 0.089735 | 0.002469 | 0.012757 | −0.035515 | 0.045624 | −0.066935 | −0.016812 | −0.0264 | 0.032758 | −0.045273 | −0.009218 | 0.009743 |
| 22 | 0.10407 | −0.003067 | 0.017706 | −0.0407 | −0.034677 | −0.127489 | 0.033872 | −0.050395 | 0.054752 | 0.01676 | −0.038434 | −0.046219 | 0.006688 | −0.024272 |
| 23 | 0.050764 | −0.037131 | −0.095624 | −0.00798 | 0.007875 | −0.031027 | −0.009778 | 0.012983 | −0.064098 | 0.023626 | −0.021077 | −0.027187 | −0.016814 | −0.022331 |
| 24 | −0.066756 | −0.001742 | −0.067365 | −0.018687 | 0.022297 | 0.060084 | 0.017576 | 0.051611 | −0.067917 | 0.026259 | −0.045724 | −0.101184 | 0.096273 | 0.026664 |
| 25 | 0.057275 | −0.007825 | 0.004316 | 0.02961 | −0.038515 | −0.012142 | 0.011647 | −0.033791 | 0.048936 | −0.103528 | 0.074093 | 0.082716 | 0.00436 | 0.063466 |
| 26 | −0.062718 | −0.019121 | −0.079565 | −0.033496 | 0.090154 | −0.057848 | 0.001696 | −0.012704 | −0.062851 | −0.192752 | 0.071098 | −0.00153 | −0.009891 | −0.029963 |
| 27 | 0.058031 | 0.064791 | 0.076985 | 0.076246 | 0.03572 | 0.05844 | −0.057921 | 0.027939 | 0.096984 | −0.039321 | −0.032897 | 0.099234 | 0.024502 | 0.015309 |
| 28 | −0.023256 | −0.006379 | −0.056146 | 0.052725 | 0.092848 | −0.088714 | −0.051081 | −0.069358 | 0.051375 | −0.00471 | −0.059703 | 0.045444 | −0.089801 | −0.067466 |
| 29 | −0.064318 | 0.047249 | 0.059401 | −0.001439 | 0.020561 | −0.00642 | 0.029583 | 0.036562 | −0.045842 | −0.017682 | 0.060889 | −0.021422 | 0.01704 | −0.063646 |
| 30 | 0.032197 | 0.006275 | −0.000417 | 0.098918 | 0.020752 | 0.042443 | 0.027251 | −0.019215 | 0.004262 | 0.071599 | −0.09954 | 0.020256 | 0.090146 | 0.052273 |
| 31 | −0.037412 | −0.009079 | 0.009354 | 0.017554 | 0.033132 | −0.023353 | 0.03745 | −0.144947 | −0.054552 | −0.132915 | 0.017038 | 0.116149 | −0.022273 | 0.00906 |
| 32 | −0.088403 | 0.018125 | 0.092242 | −0.016792 | 0.042827 | 0.068806 | −0.048644 | 0.041705 | 0.007095 | 0.070749 | −0.036557 | 0.030145 | 0.027326 | 0.00959 |
| 33 | 0.003484 | 0.013502 | 0.027391 | −0.001727 | −0.050834 | 0.093373 | −0.075765 | −0.101534 | 0.058059 | −0.102986 | −0.047425 | −0.010195 | 0.015402 | 0.023897 |
| 34 | −0.023387 | 0.040482 | −0.091624 | −0.058497 | −0.052053 | −0.035695 | −0.002245 | 0.039331 | −0.018246 | 0.06526 | 0.015095 | 0.152043 | 0.053662 | 0.075909 |
| 35 | −0.050442 | 0.063185 | 0.035346 | 0.01946 | 0.113794 | 0.056883 | −0.084913 | −0.003641 | 0.050913 | −0.031284 | 0.026491 | −0.080399 | −0.030144 | −0.053402 |
| 36 | −0.031558 | 0.058933 | 0.142313 | 0.079365 | 0.060401 | −0.002884 | −0.037993 | −0.027585 | −0.046489 | −0.076337 | 0.06631 | −0.002864 | −0.018634 | 0.004003 |
| 37 | 0.090765 | 0.010452 | −0.012518 | −0.014375 | −0.022801 | −0.10054 | 0.091158 | −0.042023 | 0.0672 | −0.025224 | −0.124725 | 0.053768 | 0.037056 | 0.069774 |
| 38 | 0.112228 | 0.034353 | −0.016421 | −0.021547 | −0.020779 | 0.037467 | −0.060797 | −0.083371 | −0.042449 | 0.023719 | −0.009606 | 0.058713 | 0.053685 | 0.084048 |
| 39 | −0.094143 | −0.012607 | −0.015898 | 0.036079 | 0.022364 | 0.123818 | 0.0227 | 0.013294 | 0.030147 | 0.02773 | 0.045797 | 0.083662 | 0.104178 | 0.067056 |
| 40 | 0.057687 | −0.14697 | −0.099334 | −0.101822 | −0.047195 | −0.024596 | −0.087956 | 0.155541 | −0.033089 | −0.186302 | 0.056925 | 0.081809 | −0.098091 | 0.062599 |
| 41 | 0.023555 | 0.053428 | 0.122299 | 0.045131 | 0.075083 | −0.10966 | −0.010365 | 0.107647 | −0.046979 | 0.00924 | 0.027428 | 0.025338 | −0.03537 | −0.019757 |
| 42 | 0.0094111 | 0.005558 | 0.0089021 | −0.023362 | 0.000419 | −0.014208 | −0.025356 | 0.009391 | −0.002706 | −0.030025 | 0.0151311 | −0.033538 | −0.005102 | −0.006501 |
| 43 | −0.093021 | 0.0154461 | −0.0859571 | −0.004442 | −0.06538 | 0.051376 | −0.04935 | −0.125208 | 0.1339121 | 0.0796711 | −0.201387 | 0.0394071 | 0.026871 | −0.026778 |
| 44 | 0.051998 | 0.081802 | 0.103761 | 0.042166 | 0.025577 | 0.061485 | −0.058207 | 0.105066 | −0.04239 | 0.134082 | 0.125215 | 0.090635 | 0.014463 | 0.14146 |
| 45 | 0.034246 | −0.081361 | 0.001049 | −0.058201 | −0.010903 | 0.070377 | 0.080117 | −0.258459 | 0.054533 | −0.058837 | −0.008422 | −0.093103 | −0.008928 | −0.038914 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 46 | 0.020143 | −0.000248 | 0.062059 | 0.101866 | 0.077661 | 0.019541 | 0.001587 | −0.004253 | −0.143568 | −0.055808 | 0.005421 | 0.0238 | 0.010411 | 0.018814 |
| 47 | −0.031846 | 0.016712 | −0.020688 | 0.000652 | 0.045583 | 0.062291 | 0.157777 | −0.012892 | −0.065414 | −0.006258 | 0.048444 | −0.004498 | 0.110399 | −0.02671 |
| 48 | −0.008144 | 0.0216411 | −0.001162 | 0.058801 | −0.015791 | −0.130564 | 0.031823 | −0.040769 | 0.0860161 | 0.034651 | −0.136085 | −0.078339 | −0.079747 | 0.00918 |
| 49 | 0.059011 | −0.037835 | −0.103078 | −0.039804 | −0.038989 | −0.057719 | 0.034654 | 0.065556 | 0.04968 | −0.094379 | −0.048417 | 0.018702 | 0.011881 | 0.11474 |
| 50 | −0.03289 | 0.01106 | 0.002452 | −0.069291 | 0.040026 | −0.058574 | −0.047923 | 0.045834 | −0.032324 | −0.128039 | 0.019473 | 0.070191 | −0.054267 | 0.007367 |
| 51 | 0.010757 | −0.000877 | −0.045515 | 0.006781 | 0.023217 | 0.01387 | −0.056278 | 0.057733 | −0.188586 | −0.00061 | 0.05793 | −0.022531 | −0.002106 | −0.038809 |
| 52 | −0.065951 | 0.043949 | −0.033205 | −0.036292 | 0.041498 | −0.040378 | −0.014083 | −0.056357 | −0.069285 | 0.036301 | −0.028132 | 0.109147 | 0.021173 | 0.032093 |
| 53 | −0.125467 | −0.025825 | −0.004991 | 0.02215 | 0.090436 | −0.015481 | 0.05021 | −0.051439 | 0.1216 | −0.03043 | −0.12739 | 0.088557 | 0.058978 | 0.038939 |
| 54 | 0.073317 | −0.038756 | −0.054224 | 0.020071 | −0.02071 | −0.038058 | −0.012593 | 0.076676 | −0.054661 | 0.029967 | 0.050054 | −0.118863 | −0.064382 | −0.001673 |
| 55 | −0.063485 | 0.013009 | 0.098619 | −0.022938 | 0.019614 | 0.071676 | 0.051882 | 0.006238 | 0.058233 | −0.02037 | −0.02723 | −0.03508 | −0.071754 | 0.119946 |
| 56 | 0.028583 | 0.072493 | 0.060565 | 0.122451 | 0.03743 | 0.128324 | −0.016511 | 0.063237 | 0.101214 | −0.186267 | 0.091183 | −0.056794 | 0.051191 | 0.025323 |
| 57 | 0.024371 | −0.027877 | −0.038339 | −0.028835 | −0.060218 | −0.036782 | −0.008747 | −0.076782 | −0.062981 | 0.05328 | −0.047724 | −0.000978 | −0.022611 | −0.035579 |
| 58 | −0.046513 | 0.090391 | −0.028988 | 0.041692 | 0.000453 | 0.074757 | −0.043226 | 0.163606 | 0.076955 | 0.067366 | −0.00207 | 0.002458 | 0.126561 | 0.049315 |
| 59 | −0.101322 | −0.028801 | −0.018846 | −0.050237 | −0.043239 | 0.089 | 0.015 | 0.024267 | 0.011026 | 0.098451 | −0.02014 | 0.050138 | −0.002654 | 0.005164 |
| 60 | 0.040813 | −0.037096 | 0.001998 | −0.022382 | −0.022928 | −0.028044 | −0.007404 | 0.088773 | 0.006824 | 0.135963 | −0.037214 | 0.002031 | 0.075883 | −0.006966 |
| 61 | 0.051555 | 0.011094 | 0.028086 | −0.036578 | 0.049711 | 0.059775 | −0.031485 | −0.072267 | −0.159219 | 0.042627 | −0.047692 | −0.033249 | −0.075985 | 0.000392 |
| 62 | 0.148342 | 0.025924 | −0.009031 | −0.009237 | −0.063273 | 0.076833 | −0.071251 | 0.033598 | −0.056933 | 0.047324 | 0.033124 | 0.053336 | −0.035891 | −0.124103 |
| 63 | −0.108182 | −0.044434 | 0.019279 | 0.084161 | 0.044075 | 0.050503 | 0.03247 | −0.066827 | −0.025403 | −0.010829 | −0.024784 | −0.065001 | −0.052716 | −0.030513 |
| 64 | −0.128821 | 0.005358 | 0.042584 | −0.087111 | −0.042877 | −0.155475 | 0.057609 | −0.000619 | −0.002753 | 0.134968 | 0.01718 | −0.057301 | −0.048607 | −0.044408 |
| 65 | −0.072586 | 0.048267 | −0.011662 | −0.068761 | 0.087055 | −0.034957 | 0.024686 | 0.163009 | 0.040573 | 0.025 | 0.07625 | 0.004387 | 0.058661 | 0.011164 |
| 66 | −0.005399 | 0.009651 | −0.018955 | −0.000909 | 0.052437 | −0.025917 | −0.001012 | −0.137329 | 0.099971 | −0.014127 | 0.097099 | −0.020597 | 0.049109 | −0.061607 |
| 67 | −0.09835 | 0.010329 | 0.011173 | −0.095146 | −0.029702 | −0.069111 | 0.004994 | 0.042688 | −0.085049 | −0.082471 | −0.039452 | −0.067184 | −0.060095 | −0.18496 |
| 68 | 0.019851 | 0.020701 | 0.052248 | 0.109415 | −0.014159 | 0.002717 | 0.093214 | −0.001685 | 0.018873 | 0.071722 | −0.05495 | −0.007947 | 0.062048 | 0.049169 |
| 69 | 0.000411 | −0.004132 | −0.01129 | 0.005392 | −0.045943 | −0.062311 | 0.044446 | 0.047943 | 0.149919 | −0.034613 | −0.082606 | −0.053947 | −0.075068 | −0.000916 |
| 70 | 0.068171 | 0.043559 | 0.006768 | 0.023508 | −0.100098 | −0.016062 | −0.025046 | 0.055005 | −0.047103 | 0.047483 | 0.044332 | 0.016922 | 0.006511 | 0.029298 |
| 71 | −0.056543 | −0.022052 | 0.011599 | 0.022453 | 0.008585 | −0.058287 | −0.061001 | 0.16475 | −0.150801 | −0.070998 | 0.018653 | −0.002616 | −0.121766 | 0.053546 |
| 72 | −0.000507 | −0.143494 | 0.056369 | 0.000004 | −0.003537 | −0.034077 | 0.012667 | −0.056389 | 0.016288 | 0.040254 | −0.08887 | −0.105544 | 0.023309 | 0.01865 |
| 73 | 0.004106 | −0.000927 | 0.0278181 | −0.021449 | −0.007463 | 0.110365 | 0.059598 | −0.087858 | −0.062424 | 0.2144091 | −0.033466 | 0.1048871 | 0.0134941 | −0.018862 |
| 74 | 0.016616 | 0.002812 | −0.04383 | −0.050507 | 0.052164 | −0.103556 | 0.083914 | 0.030268 | −0.003912 | −0.08003 | −0.075846 | −0.093482 | −0.006313 | 0.111127 |
| 75 | −0.02895 | −0.112678 | 0.007258 | −0.13113 | 0.013005 | 0.115284 | 0.003431 | −0.126237 | 0.107936 | 0.051305 | 0.112351 | −0.082783 | −0.077135 | −0.096611 |
| 76 | −0.069971 | 0.055069 | 0.051977 | 0.075991 | 0.027745 | −0.014773 | −0.090125 | 0.060039 | −0.040718 | 0.027975 | −0.102327 | −0.055491 | 0.140823 | 0.019037 |
| 77 | −0.019976 | −0.035783 | −0.035219 | −0.064853 | 0.03109 | 0.09818 | 0.033358 | 0.023033 | −0.118837 | −0.076435 | −0.081466 | 0.11554 | 0.047963 | −0.033232 |
| 78 | 0.174393 | 0.014398 | 0.063502 | 0.015481 | −0.024173 | 0.108173 | 0.062455 | −0.005427 | 0.041775 | −0.130108 | 0.081651 | 0.026562 | 0.028966 | 0.038505 |
| 79 | −0.114021 | −0.000254 | 0.035116 | −0.011576 | −0.03283 | −0.087848 | 0.020342 | −0.157536 | −0.14119 | −0.034226 | −0.106717 | −0.086256 | −0.023577 | −0.003385 |
| 80 | 0.029035 | 0.020166 | −0.015939 | −0.04618 | −0.040487 | −0.07105 | −0.040668 | −0.084354 | −0.039484 | −0.123095 | −0.033688 | 0.038534 | 0.066784 | 0.01835 |
| 81 | 0.011226 | 0.058116 | −0.070526 | −0.006285 | 0.041235 | −0.049406 | 0.017585 | 0.090477 | −0.077435 | 0.055872 | −0.011555 | 0.08025 | 0.036534 | −0.022068 |
| 82 | 0.048999 | −0.06022 | −0.072989 | 0.05075 | 0.004454 | 0.083966 | 0.00637 | −0.067962 | −0.004305 | 0.088696 | −0.012453 | −0.11289 | −0.026638 | 0.169953 |
| 83 | −0.078062 | −0.042268 | 0.014983 | −0.052468 | −0.062242 | 0.114052 | 0.041515 | −0.04167 | −0.011457 | 0.035311 | 0.0864061 | −0.034123 | −0.021375 | −0.128294 |
| 84 | 0.002833 | 0.114902 | 0.008647 | −0.045244 | 0.080348 | 0.006284 | −0.116502 | 0.023471 | −0.065287 | 0.146507 | −0.104176 | −0.217573 | 0.077541 | 0.076994 |
| 85 | −0.076696 | −0.025457 | −0.089816 | −0.026846 | 0.132923 | 0.198672 | 0.030188 | 0.019484 | 0.08686 | 0.041094 | 0.011344 | −0.034931 | −0.014195 | −0.145252 |
| 86 | 0.105585 | −0.016126 | 0.057886 | −0.049088 | −0.119086 | −0.12396 | −0.092005 | 0.007175 | 0.069742 | 0.01108 | 0.123595 | −0.031725 | −0.016884 | 0.116024 |
| 87 | 0.092946 | −0.001239 | 0.023453 | 0.010102 | −0.045646 | −0.031741 | 0.078159 | 0.050338 | 0.133888 | 0.145113 | 0.015038 | 0.002422 | −0.071818 | −0.044266 |
| 88 | 0.089516 | −0.060441 | 0.094423 | −0.03912 | −0.080462 | 0.014321 | 0.028503 | 0.029785 | −0.113865 | 0.124093 | −0.020719 | 0.022875 | 0.023578 | 0.018454 |
| 89 | 0.056521 | −0.049054 | 0.050748 | 0.048209 | 0.062032 | 0.095565 | 0.048367 | 0.09029 | −0.030222 | 0.083832 | −0.140236 | −0.016442 | −0.070739 | −0.057135 |
| 90 | 0.0364641 | 0.0297471 | −0.064683 | 0.028252 | −0.060107 | 0.024719 | 0.06426 | 0.00468 | −0.03877 | −0.135789 | 0.007943 | 0.145135 | −0.018085 | 0.021086 |
| 91 | −0.100744 | 4.190576 | −0.038724 | 0.068037 | −0.015104 | −0.101499 | −0.145545 | 0.00961 | 0.052245 | −0.018395 | 0.050531 | −0.078188 | −0.043945 | −0.063696 |
| 92 | 0.051992 | −0.008726 | 0.068788 | 0.056103 | 0.016897 | 0.037942 | −0.00019 | 0.037853 | −0.024825 | −0.098622 | −0.012907 | 0.052653 | −0.02449 | −0.033801 |
| 93 | −0.068595 | 0.053299 | −0.065528 | −0.049169 | 0.015378 | −0.048302 | 0.118853 | −0.024604 | 0.088201 | −0.023967 | −0.035842 | −0.030151 | 0.063658 | 0.007117 |
| 94 | 0.081201 | 0.168268 | 0.019433 | −0.064017 | −0.018332 | −0.018449 | 0.060315 | 0.05821 | 0.008919 | 0.007376 | 0.135648 | 0.039059 | 0.010768 | −0.022784 |
| 95 | 0.090302 | −0.008216 | 0.024754 | 0.00656 | −0.012042 | −0.057537 | 0.061722 | 0.032991 | 0.040283 | −0.100214 | 0.098149 | −0.095574 | 0.132791 | 0.010336 |
| 96 | −0.007142 | −0.008728 | −0.014655 | 0.01699 | 0.012525 | −0.007799 | 0.055085 | 0.065677 | 0.063179 | 0.072538 | −0.007702 | 0.059036 | −0.07412 | −0.071628 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 97 | −0.016188 | −0.006887 | −0.046003 | 0.001568 | 0.104095 | 0.11909 | 0.048463 | 0.089601 | 0.036105 | −0.078831 | −0.00647 | −0.021578 | −0.011919 | 0.025935 |
| 98 | −0.100057 | −0.092679 | 0.013726 | −0.08341 | −0.011091 | 0.023739 | −0.055271 | −0.016067 | 0.06845 | −0.056706 | 0.032469 | 0.009205 | 0.026638 | −0.019098 |
| 99 | −0.070258 | −0.037033 | 0.096948 | 0.035414 | −0.017716 | −0.082116 | 0.047002 | 0.027143 | −0.062265 | −0.030139 | −0.000822 | 0.039853 | 0.034993 | −0.008193 |
| 100 | −0.0199691 | 0.0097191 | 0.013471 | −0.002182 | 0.02311 | −0.000258 | −0.017146 | −0.04135 | −0.023662 | 0.032729 | 0.032423 | −0.021081 | −0.016503 | −0.008767 |
| 101 | −0.027479 | 4.006748 | 0.001566 | 0.012314 | 0.018687 | 0.007293 | 0.010346 | −0.011994 | −0.012206 | 0.011289 | 0.008586 | −0.025121 | −0.00078 | 0.009641 |
| 102 | −0.025472 | 0.009673 | 0.021324 | −0.01123 | −0.009101 | −0.020509 | −0.002253 | −0.004549 | 0.033902 | −0.008964 | 0.018957 | 0.000893 | 0.034071 | −0.017431 |
| 103 | −0.039525 | −0.00667 | −0.012517 | −0.007357 | 0.026744 | −0.027306 | −0.031328 | 0.019223 | −0.064387 | −0.012993 | 0.031213 | 0.003169 | −0.055347 | −0.049236 |
| 104 | −0.0646481 | 0.0222361 | 0.054815 | 0.037166 | −0.027192 | −0.065401 | −0.068662 | 0.003689 | −0.056961 | −0.020832 | −0.057737 | 0.0012581 | −0.042766 | 0.039907 |
| 105 | −0.0034471 | −0.004278 | −0.047759 | −0.063508 | 0.004111 | 0.051073 | 0.097641 | 0.044621 | −0.043249 | −0.051999 | 0.01199 | 0.048484 | 0.048474 | −0.011414 |
| 106 | 0.026918 | 0.026829 | 0.032546 | 0.014219 | 0.000005 | 0.012099 | −0.023859 | 0.01794 | 0.000435 | −0.051983 | 0.039777 | 0.028125 | −0.035902 | 0.034409 |
| 107 | −0.085737 | 0.035448 | 0.039279 | 0.070552 | 0.03734 | −0.017162 | −0.038918 | 0.060566 | 0.065524 | −0.011071 | −0.001187 | 0.023925 | 0.0134371 | −0.040105 |
| 108 | 0.001437 | 0.0506141 | 0.01338 | 0.023576 | 0.000279 | −0.006998 | 0.056528 | −0.125103 | 0.049142 | 0.10802 | −0.02611 | −0.068025 | −0.002038 | −0.018501 |
| 109 | 0.033825 | 0.003158 | 0.014136 | −0.002209 | −0.022541 | −0.044907 | 0.004818 | −0.094071 | −0.056686 | 0.019059 | −0.050853 | −0.011269 | 0.047309 | 0.01136 |
| 110 | −0.056984 | −0.013528 | −0.092202 | −0.031623 | 0.003172 | 0.048193 | 0.02355 | −0.037065 | −0.036482 | −0.036492 | −0.0127 | 0.080745 | 0.048865 | −0.000026 |
| 111 | 0.029197 | −0.002595 | 0.064146 | −0.047217 | −0.050255 | 0.012917 | −0.039692 | −0.043735 | 0.029891 | 0.01595 | 0.059368 | −0.015794 | −0.039701 | 0.040082 |
| 112 | 0.060256 | −0.052366 | −0.007379 | −0.010548 | 0.016653 | 0.031053 | 0.030545 | −0.016761 | 0.037015 | −0.040645 | 0.015973 | −0.064238 | −0.076076 | −0.009695 |
| 113 | 0.037237 | −0.027499 | −0.007125 | −0.027736 | 0.03917 | 0.020749 | −0.029482 | 0.005847 | 0.049635 | −0.092773 | 0.05449 | −0.030545 | 0.011872 | −0.050224 |
| 114 | −0.009233 | 0.015835 | 0.053269 | 0.038868 | 0.005713 | 0.053498 | −0.008818 | −0.025839 | 0.066771 | 0.034526 | 0.037943 | −0.006576 | 0.016993 | −0.068209 |
| 115 | −0.011444 | 0.0255451 | −0.032752 | −0.00136 | −0.023563 | −0.029584 | 0.003048 | −0.012227 | 0.074616 | 0.039287 | 0.023002 | 0.085641 | 0.03714 | 0.029152 |
| 116 | 4.005632 | 0.0157851 | −0.004726 | −0.022883 | 0.006467 | 0.031415 | −0.0136 | 0.050894 | −0.065151 | −0.019879 | −0.056262 | −0.024071 | 0.005636 | 0.002669 |
| 117 | −0.076416 | 0.000071 | 0.026572 | 0.026417 | 0.046601 | 0.005459 | −0.016385 | −0.026485 | −0.011262 | −0.006898 | −0.024155 | −0.017293 | −0.024279 | −0.053717 |
| 118 | 0.019434 | −0.003269 | 0.016591 | 0.03888 | −0.024914 | 0.002551 | 0.007205 | 0.024989 | 0.039397 | 0.002568 | 0.018336 | −0.048575 | 0.031583 | −0.005695 |
| 119 | 0.002565 | −0.039466 | −0.0235651 | −0.026385 | −0.028973 | 0.006813 | −0.023813 | −0.000951 | 0.020617 | −0.018243 | −0.030595 | −0.063265 | −0.019703 | −0.024461 |
| 120 | −0.007138 | 0.027353 | 0.016694 | 0.024924 | 0.006939 | −0.016557 | −0.013118 | −0.047071 | −0.000145 | −0.043516 | −0.031511 | 0.00814 | −0.004281 | −0.006684 |
| 121 | 4.0275 | −0.056893 | 0.015858 | 0.011263 | 0.002547 | −0.005616 | 0.015099 | −0.046904 | −0.050145 | −0.066765 | 0.008316 | 0.015059 | −0.009046 | −0.000553 |
| 122 | −0.063943 | −0.01525 | −0.013463 | 0.036087 | 0.023332 | −0.00686 | 0.001865 | −0.007066 | 0.045 | −0.017626 | 0.021209 | 0.025087 | −0.002519 | −0.005351 |
| 123 | −0.05617 | 0.019492 | −0.02223 | −0.024882 | −0.020445 | −0.039361 | −0.000042 | −0.04113 | −0.012616 | −0.014033 | −0.013217 | 0.020299 | 0.026399 | −0.008177 |
| 124 | −0.016797 | −0.058657 | −0.022742 | −0.03638 | −0.020086 | 0.034489 | −0.005086 | −0.039011 | −0.01533 | −0.032199 | −0.00727 | −0.022962 | −0.017415 | −0.036871 |
| 125 | −0.004839 | −0.006622 | 0.017481 | −0.007054 | −0.040061 | −0.042747 | −0.041726 | −0.038376 | 0.022903 | 0.016623 | 0.02696 | −0.012811 | 0.012248 | −0.037879 |
| 126 | −0.017716 | −0.013277 | 0.026875 | −0.00914 | −0.041978 | −0.01629 | −0.017382 | −0.031284 | −0.000449 | 0.024515 | 0.032551 | 0.061651 | −0.015005 | −0.057445 |
| 127 | −0.003528 | −0.041815 | −0.003004 | 0.002502 | −0.046781 | −0.023907 | −0.003157 | −0.054116 | −0.012548 | 0.046854 | 0.023557 | 0.056404 | −0.021454 | −0.078358 |
| 128 | −0.011714 | 0.024143 | 0.000375 | 0.025389 | 0.004261 | −0.036859 | −0.036583 | 0.002745 | 0.002741 | 0.034714 | −0.047425 | 0.005252 | 0.004881 | −0.031695 |
| 129 | 0.025218 | −0.031306 | −0.005354 | 0.041233 | −0.07783 | 0.060861 | −0.004298 | 0.012535 | −0.016204 | −0.013205 | −0.070241 | −0.02385 | 0.036571 | 0.037579 |
| 130 | −0.045194 | 0.027024 | −0.004606 | −0.079832 | −0.006021 | −0.027858 | 0.00736 | 0.039596 | 0.001194 | 0.042073 | −0.063268 | 0.03686 | 0.029155 | 0.126669 |
| 131 | 0.022523 | 0.009758 | 0.0471131 | −0.045823 | 0.00239 | −0.095469 | 0.056264 | 0.027675 | 0.041766 | 0.004965 | −0.018468 | −0.056008 | −0.013424 | −0.050567 |
| 132 | −0.008151 | 0.022176 | −0.018213 | 0.012996 | −0.057911 | 0.011938 | −0.003901 | 0.027647 | 0.058998 | 0.041564 | −0.009746 | 0.077949 | 0.033122 | −0.009932 |
| 133 | 0.062773 | −0.000586 | 0.027634 | 0.06102 | −0.017701 | 0.006735 | −0.012362 | −0.008693 | −0.016425 | −0.062108 | 0.051129 | 0.032705 | −0.029235 | −0.085032 |
| 134 | −0.079589 | −0.032938 | 0.025418 | −0.014407 | 0.024648 | 0.003783 | 0.075149 | −0.023807 | −0.043791 | 0.004536 | 0.020744 | 0.042134 | −0.027879 | 0.00989 |
| 135 | 0.0441841 | 0.022911 | 0.000404 | −0.013225 | −0.000857 | −0.020662 | −0.052083 | 0.011871 | −0.033074 | −0.00661 | −0.007813 | −0.03251 | −0.051517 | −0.001358 |
| 136 | 0.0190521 | −0.0355531 | −0.014225 | −0.091658 | −0.056695 | −0.009693 | 0.00314 | 0.033926 | −0.044588 | −0.024742 | −0.007785 | −0.006941 | −0.002118 | 0.012685 |
| 137 | −0.024762 | −0.035987 | −0.028916 | 0.016546 | −0.013543 | 0.034517 | 0.006267 | −0.071297 | 0.023963 | 0.020878 | −0.002875 | −0.07761 | −0.011183 | −0.009099 |
| 138 | 0.018006 | −0.003383 | 0.044175 | 0.022395 | 0.013262 | −0.030428 | −0.006765 | −0.018201 | 0.014839 | 0.018231 | −0.060027 | −0.006678 | 0.017558 | −0.012091 |
| 139 | −0.106989 | −0.058755 | −0.049336 | 0.040949 | 0.021926 | 0.000946 | 0.013781 | 0.05591 | 0.013036 | −0.02482 | −0.07495 | −0.027524 | 0.015816 | −0.056271 |
| 140 | −0.009466 | 0.008571 | 0.0460931 | −0.021732 | 0.024149 | −0.000878 | −0.041752 | 0.005893 | 0.003582 | −0.003745 | 0.036946 | −0.000605 | 0.017809 | −0.043544 |
| 141 | −0.041609 | 0.0304741 | −0.014093 | 0.012991 | 0.021041 | 0.004988 | −0.030112 | −0.010688 | 0.050575 | 0.019108 | 0.015031 | 0.003788 | −0.064325 | −0.040554 |
| 142 | 0.042172 | −0.039421 | −0.04184 | −0.127845 | −0.044391 | −0.04827 | −0.015901 | 0.041772 | −0.067696 | 0.001932 | −0.035518 | −0.02436 | −0.111731 | −0.052766 |
| 143 | −0.039867 | −0.035814 | −0.005666 | 0.002251 | 0.012781 | 0.010745 | −0.004326 | −0.044321 | 0.025279 | 0.045825 | −0.066677 | −0.040302 | −0.02246 | 0.007809 |
| 144 | 0.009272 | −0.018504 | −0.058083 | −0.100812 | −0.047407 | 0.029999 | 0.004988 | −0.030512 | −0.007337 | 0.0121 | −0.003905 | −0.059322 | 0.005669 | −0.019338 |
| 145 | −0.026991 | 0.00391 | −0.0150061 | −0.04487 | −0.014339 | 0.020878 | −0.027731 | 0.010812 | −0.051306 | 0.051963 | 0.0344551 | −0.038915 | −0.026839 | −0.059005 |
| 146 | 0.021566 | 0.0361531 | −0.0277981 | −0.006497 | −0.012538 | −0.045565 | −0.021292 | 0.020997 | 0.015734 | 0.019591 | 0.017702 | 0.000887 | 0.001115 | −0.035926 |
| 147 | −0.030624 | −0.011002 | −0.014044 | −0.056234 | 0.020769 | −0.05138 | 0.03063 | −0.008259 | 0.018442 | 0.02178 | 0.025038 | 0.004884 | 0.007319 | −0.013414 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 148 | −0.006091 | 0.020064 | −0.006599 | −0.032012 | 0.00661 | 0.045296 | −0.020432 | 0.068593 | −0.010613 | −0.024864 | −0.088769 | 0.01834 | 0.032414 | −0.001401 |
| 149 | −0.045543 | −0.01622 | −0.003231 | 0.006286 | 0.020063 | −0.020112 | 0.004855 | −0.038638 | −0.019385 | −0.058983 | −0.012245 | −0.02786 | −0.080251 | −0.020338 |
| 150 | −0.005171 | 0.029162 | −0.00371 | −0.042854 | −0.026386 | −0.060849 | −0.035778 | 0.034776 | −0.077872 | −0.008317 | 0.008082 | 0.010718 | −0.013615 | 0.024641 |
| 151 | 0.489004 | −0.024417 | −0.022467 | 0.00329 | 0.084693 | 0.007336 | −0.003234 | −0.035841 | 0.000836 | −0.005014 | −0.048173 | 0.003477 | 0.030948 | −0.072934 |
| 152 | −0.020446 | 0.768052 | −0.084341 | −0.050175 | −0.054937 | 0.006679 | −0.004381 | −0.053872 | 0.005549 | −0.054117 | −0.005823 | −0.053559 | −0.085962 | −0.055338 |
| 153 | −0.020325 | −0.077026 | 0.747065 | −0.087747 | −0.036115 | 0.001793 | 0.020264 | 0.003405 | 0.030005 | −0.039152 | −0.055583 | 0.000349 | 0.004397 | 0.000396 |
| 154 | −0.00647 | −0.046722 | −0.080836 | 0.754261 | −0.070103 | −0.056609 | 0.02385 | −0.028694 | −0.034913 | 0.000117 | 0.022813 | −0.016559 | −0.034933 | −0.042158 |
| 155 | 0.1183441 | −0.046327 | −0.0181871 | −0.060088 | 0.776386 | −0.066715 | 0.011849 | −0.059256 | −0.005006 | 0.0162371 | −0.008527 | 0.0106121 | −0.005462 | 0.019412 |
| 156 | 0.033106 | 0.0375371 | 0.0193621 | −0.057373 | −0.083842 | 0.525784 | −0.021985 | −0.028108 | 0.000039 | −0.059895 | −0.019605 | −0.034459 | −0.058617 | 0.00324 |
| 157 | 0.002746 | 0.014396 | 0.036715 | 0.007017 | −0.022907 | −0.007613 | 0.734857 | 0.033774 | −0.025154 | −0.021761 | 0.03881 | −0.044898 | −0.041795 | −0.0362 |
| 158 | −0.043369 | −0.058462 | −0.00882 | −0.037634 | −0.061977 | −0.033214 | 0.051837 | 0.421994 | 0.033128 | 0.024866 | −0.089272 | 0.019872 | 0.002504 | −0.046823 |
| 159 | 0.014673 | 0.027852 | 0.021725 | −0.019952 | 0.019407 | −0.016636 | −0.005945 | 0.045861 | 0.394842 | −0.029573 | −0.019358 | 0.028739 | −0.02828 | −0.001772 |
| 160 | 0.043078 | −0.012272 | −0.026092 | 0.021129 | 0.034261 | −0.066399 | 0.005098 | −0.027204 | −0.031494 | 0.306775 | 0.034331 | 0.03114 | −0.023111 | 0.026145 |
| 161 | −0.037894 | −0.026678 | −0.049658 | 0.031949 | −0.008859 | 0.016099 | 0.018373 | −0.073963 | 0.00604 | 0.048017 | 0.533139 | −0.054749 | −0.005405 | 0.090897 |
| 162 | −0.019159 | −0.071231 | −0.016324 | −0.051186 | 0.009174 | 0.011586 | −0.064092 | −0.013854 | 0.042095 | 0.030656 | −0.037328 | 0.561713 | −0.10416 | −0.047692 |
| 163 | 0.047257 | −0.10627 | −0.006181 | −0.057561 | −0.035247 | −0.047733 | −0.049547 | 0.003333 | −0.011353 | −0.03379 | 0.006032 | −0.097034 | 0.689461 | −0.094862 |
| 164 | −0.113141 | −0.077229 | −0.012754 | −0.06895 | −0.000566 | 0.005173 | −0.009599 | −0.057979 | 0.008535 | 0.050473 | 0.116764 | −0.057967 | −0.095346 | 0.627028 |
| 165 | −0.042938 | −0.028016 | −0.044781 | −0.013295 | −0.096983 | 0.050019 | 0.010195 | −0.044156 | −0.005851 | −0.095325 | −0.064605 | 0.0064821 | −0.040324 | −0.016862 |
| 166 | −0.044091 | 0.042109 | −0.008592 | 0.023549 | 0.033924 | 0.018146 | −0.036858 | 0.005364 | 0.007962 | −0.12863 | −0.000365 | −0.023319 | 0.058247 | −0.022127 |
| 167 | 0.058849 | −0.002286 | −0.036915 | 0.038183 | −0.041555 | −0.028619 | 0.025421 | −0.017266 | 0.032982 | 0.005902 | 0.047961 | 0.023939 | −0.002213 | −0.0097 |
| 168 | −0.012721 | −0.000072 | 0.011634 | 0.008327 | 0.059844 | −0.006922 | −0.066103 | 0.006141 | −0.004684 | 0.020389 | −0.051671 | −0.010743 | −0.04788 | 0.013495 |
| 169 | 0.049064 | 0.006544 | 0.023304 | 0.015262 | 0.010812 | 0.038558 | −0.006703 | 0.012972 | −0.030977 | 0.030631 | 0.01797 | −0.010273 | −0.014934 | 0.012665 |
| 170 | 0.009403 | −0.006112 | 0.001708 | −0.001478 | 0.024731 | 0.018952 | 0.0255 | −0.000072 | −0.041234 | 0.000481 | 0.005022 | −0.004323 | 0.018651 | 0.010446 |
| 171 | 0.019443 | 0.000955 | −0.000466 | 0.031742 | 0.026615 | 0.009467 | 0.01695 | 0.024358 | −0.031971 | −0.010924 | −0.000826 | 0.012102 | −0.017604 | 0.024663 |
| 172 | −0.005258 | 0.0352811 | 0.025465 | 0.001974 | 0.004271 | 0.081067 | −0.014264 | −0.003269 | −0.015776 | 0.022062 | 0.023841 | −0.01656 | −0.003136 | −0.009399 |
| 173 | 0.012344 | 0.039658 | −0.005804 | 0.023713 | 0.004713 | 0.03239 | −0.006248 | −0.004184 | 0.004182 | 0.014526 | 0.000404 | −0.055546 | −0.00515 | −0.001716 |
| 174 | 0.010442 | 0.013467 | 0.024698 | 0.006714 | −0.009481 | −0.001879 | 0.013738 | 0.005342 | −0.028107 | −0.030187 | −0.065762 | 0.059647 | 0.007319 | 0.012462 |
| 175 | −0.014744 | −0.010499 | 0.013708 | 0.027799 | −0.020679 | −0.005912 | −0.02768 | −0.018089 | 0.047023 | −0.063841 | −0.075405 | −0.01541 | 0.034157 | 0.062405 |
| 176 | −0.010144 | −0.014599 | −0.004325 | 0.026005 | 0.026923 | 0.034607 | −0.002076 | −0.034268 | −0.007485 | −0.005804 | −0.005074 | 0.059161 | 0.0074721 | −0.002287 |
| 177 | −0.079846 | 0.009603 | −0.031968 | −0.036124 | 0.061634 | 0.004611 | 0.025712 | −0.071951 | −0.00037 | 0.043929 | −0.054837 | −0.033259 | 0.009183 | −0.008181 |
| 178 | −0.009403 | −0.021786 | −0.004562 | 0.019735 | 0.006222 | 0.068942 | −0.02003 | −0.008219 | 0.01909 | 0.049353 | −0.005351 | −0.056134 | −0.014953 | 0.001986 |
| 179 | 0.013934 | −0.001933 | 0.003799 | 0.010536 | 0.007617 | −0.005013 | 0.004177 | 0.019403 | −0.016525 | 0.016251 | 0.019352 | 0.004023 | −0.004078 | 0.01905 |
| 180 | 0.019005 | −0.010735 | −0.017213 | 0.012717 | 0.011176 | 0.017731 | −0.003657 | 0.002784 | 0.0127 | 0.012917 | 0.022435 | −0.047238 | 0.005379 | 0.026067 |
| 181 | −0.011759 | −0.009018 | −0.026563 | 0.012281 | 0.002086 | −0.005689 | 0.016417 | −0.007344 | 0.0120931 | 0.005607 | 0.022887 | −0.011659 | 0.026281 | 0.038461 |
| 182 | −0.0151151 | −0.010792 | −0.0129031 | −0.018567 | 0.000897 | 0.002107 | 0.026141 | −0.024405 | 0.000416 | 0.014083 | 0.046768 | −0.00351 | 0.028556 | 0.007732 |
| 183 | −0.01137 | 0.011528 | −0.007494 | −0.01004 | 0.014464 | −0.028477 | 0.012732 | 0.006435 | −0.007798 | 0.031502 | 0.050732 | 0.044903 | 0.011453 | 0.00259 |
| 184 | −0.011683 | 0.017976 | 0.008173 | 0.016653 | −0.005603 | −0.034055 | 0.001748 | −0.028461 | −0.021049 | −0.033668 | −0.002187 | 0.062222 | −0.027625 | 0.025487 |
| 185 | −0.009506 | −0.013098 | −0.008581 | 0.003418 | −0.032183 | 0.003291 | −0.031132 | 0.026544 | 0.038842 | 0.086166 | 0.030529 | 0.014092 | −0.045649 | 0.01429 |
| 186 | −0.040442 | 0.015393 | −0.041263 | −0.03371 | 0.01917 | 0.050476 | 0.03553 | 0.072208 | 0.005718 | 0.01793 | −0.076456 | −0.011957 | 0.026095 | 0.047176 |
| 187 | 0.012105 | 0.015066 | 0.012051 | −0.018967 | −0.005415 | 0.058669 | −0.000869 | −0.002569 | 0.01243 | 0.045917 | 0.040329 | −0.027827 | 0.005638 | −0.042671 |
| 188 | 0.034536 | 0.0385 | 0.011844 | −0.030554 | −0.028615 | −0.001713 | 0.010396 | −0.002194 | 0.011399 | 0.020897 | 0.01988 | 0.024325 | 0.006626 | −0.027361 |
| 189 | −0.004557 | 0.050187 | 0.008995 | −0.031913 | 0.005501 | −0.033214 | −0.007052 | −0.027474 | −0.02846 | −0.008605 | 0.02144 | 0.066308 | 0.01126 | −0.04047 |
| 190 | −0.04769 | −0.015918 | 0.025709 | 0.043138 | 0.017404 | 0.041571 | −0.011288 | −0.023985 | 0.009746 | −0.007433 | −0.034478 | −0.004994 | 0.020323 | 0.008614 |
| 191 | 0.005893 | 0.02519 | 0.061923 | 0.030076 | −0.01395 | −0.043184 | −0.039632 | −0.009381 | 0.005648 | −0.054693 | −0.044165 | 0.017883 | 0.0255 | 0.045416 |
| 192 | −0.004159 | 0.004208 | 0.012289 | −0.022688 | −0.00115 | 0.004579 | 0.022919 | 0.034899 | −0.005992 | −0.027195 | 0.007498 | 0.032764 | 0.010837 | −0.008581 |
| 193 | 0.025436 | 0.003899 | 0.007404 | −0.029337 | 0.01725 | 0.027918 | 0.009794 | 0.023549 | 0.024143 | −0.041126 | −0.003666 | 0.001297 | −0.007215 | −0.054582 |
| 194 | 0.007928 | 0.000212 | −0.026204 | 0.011682 | 0.011768 | 0.002068 | −0.001984 | −0.026782 | 0.024906 | −0.022152 | 0.003992 | 0.006513 | −0.005441 | −0.009682 |
| 195 | −0.007893 | 0.019269 | 0.0335841 | 0.014332 | −0.017621 | −0.006151 | −0.012417 | −0.00699 | −0.019503 | −0.024739 | −0.011086 | −0.025588 | 0.001729 | 0.008807 |
| 196 | −0.014279 | 0.0302571 | 0.039651 | 0.023124 | −0.018008 | 0.039538 | −0.000549 | −0.015897 | −0.002429 | 0.0126311 | −0.004009 | −0.008009 | 0.0011781 | 0.030515 |
| 197 | 0.0081621 | 0.0352781 | 0.0427661 | 0.03047 | 0.006232 | −0.007075 | 0.013095 | −0.063023 | −0.045049 | −0.000545 | 0.003219 | 0.045348 | 0.023085 | −0.017625 |
| 198 | 0.011033 | 0.011493 | −0.006647 | −0.007295 | 0.011294 | 0.000769 | −0.050109 | 0.00067 | −0.033565 | 0.016579 | −0.017256 | −0.010175 | −0.065719 | −0.006033 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 199 | 0.010559 | 0.016233 | 0.010929 | −0.029693 | 0.003647 | −0.049535 | −0.041022 | 0.0247 | −0.024923 | −0.000586 | −0.014393 | −0.006271 | −0.042785 | −0.084898 |
| 200 | −0.027876 | 0.001517 | −0.036347 | −0.00094 | −0.013099 | 0.058952 | 0.022006 | −0.028403 | 0.004157 | 0.01074 | −0.006243 | −0.023973 | 0.026216 | −0.077712 |
| 201 | 0.0491331 | −0.025499 | −0.0358551 | 0.028654 | 0.046455 | −0.018758 | 0.004316 | 0.028247 | 0.0927251 | −0.028104 | −0.014071 | −0.037188 | 0.0107411 | 0.00222 |
| 202 | −0.04771 | 0.0067541 | 0.038708 | 0.024737 | 0.009539 | −0.030005 | −0.00938 | 0.042513 | −0.027738 | −0.054636 | 0.045903 | −0.00302 | −0.001401 | −0.006491 |
| 203 | 0.006654 | 0.003078 | 0.015856 | 0.023411 | 0.01863 | 0.038248 | −0.05141 | 0.01921 | −0.06361 | −0.006796 | 0.016503 | 0.021297 | 0.011896 | −0.041896 |
| 204 | 0.031039 | −0.054046 | −0.003808 | −0.009099 | −0.004461 | 0.076335 | −0.022569 | −0.027049 | −0.055773 | 0.051665 | 0.011035 | 0.043408 | 0.0338 | 0.037652 |
| 205 | −0.060523 | 0.020179 | −0.016223 | −0.022766 | 0.019611 | −0.011526 | 0.010486 | 0.014193 | 0.007951 | −0.010771 | 0.00935 | −0.002381 | −0.052551 | −0.025408 |
| 206 | 0.016827 | 0.026928 | 0.01013 | −0.001549 | 0.038292 | 0.035898 | 0.000568 | −0.017527 | −0.039813 | −0.029129 | −0.016191 | 0.069191 | 0.0336321 | 0.007931 |
| 207 | 0.0219861 | 0.0014141 | 0.021011 | 0.018839 | −0.003666 | −0.026805 | −0.000485 | 0.025181 | −0.032791 | −0.009802 | 0.074355 | −0.011026 | −0.040228 | −0.077221 |
| 208 | 0.062924 | −0.029126 | −0.03206 | 0.001891 | −0.021176 | −0.02954 | −0.026122 | 0.006103 | −0.081523 | 0.023857 | 0.010631 | 0.031625 | 0.041698 | −0.004654 |
| 209 | −0.051248 | −0.008783 | 0.001721 | 0.023806 | 0.012245 | −0.04792 | 0.007759 | −0.036023 | −0.128142 | 0.031502 | −0.009892 | −0.014591 | 0.019699 | 0.077165 |
| 210 | −0.031377 | −0.038596 | 0.005962 | −0.006773 | −0.076238 | −0.035914 | −0.008331 | −0.064217 | −0.016776 | −0.025198 | −0.047014 | −0.034887 | 0.031957 | −0.04532 |
| 211 | 0.048219 | 0.077989 | 0.032872 | −0.021209 | 0.031614 | −0.008806 | −0.035663 | 0.005849 | −0.012914 | 0.0917871 | 0.0272611 | −0.044836 | 0.0478811 | −0.015465 |
| 212 | 0.026838 | −0.005151 | −0.013295 | −0.016601 | −0.017745 | −0.041452 | 0.020881 | 0.06346 | −0.044908 | 0.004002 | 0.006189 | 0.050772 | −0.019398 | 0.022261 |
| 213 | −0.00862 | 0.011157 | 0.005271 | 0.041916 | −0.003621 | 0.001267 | 0.016823 | −0.007829 | −0.010508 | −0.017795 | −0.021196 | 0.015699 | −0.061925 | −0.051662 |
| 214 | 0.029134 | 0.025761 | −0.007522 | −0.009235 | 0.008874 | −0.005222 | −0.013855 | 0.016172 | −0.035849 | 0.014876 | 0.027074 | −0.001728 | −0.001088 | 0.019813 |
| 215 | −0.051633 | 0.041233 | −0.013562 | −0.014534 | 0.007792 | 0.098993 | −0.041113 | −0.005705 | 0.027699 | −0.044725 | −0.000113 | 0.037739 | −0.001119 | 0.022966 |
| 216 | 0.005677 | −0.010327 | 0.006309 | 0.02554 | 0.016234 | −0.022147 | −0.043582 | 0.007248 | −0.030228 | −0.008819 | 0.021672 | −0.035123 | −0.033385 | 0.01115 |
| 217 | 0.001501 | 0.00356 | 0.05891 | −0.026261 | 0.008568 | 0.013753 | 0.018118 | 0.085628 | 0.003401 | 0.099818 | 0.061675 | 0.00591 | 0.002572 | −0.022282 |
| 218 | 0.027044 | 0.03199 | −0.022818 | 0.001098 | 0.015092 | 0.011604 | −0.001928 | 0.04634 | 0.000514 | 0.014735 | 0.003528 | 0.002901 | 0.013162 | 0.030297 |
| 219 | 0.001854 | 0.031001 | −0.012829 | −0.012901 | 0.008056 | −0.030317 | −0.012426 | 0.03462 | −0.003387 | 0.018677 | −0.000395 | −0.016489 | 0.010903 | 0.009897 |
| 220 | 0.013701 | 0.008733 | 0.02466 | −0.010073 | −0.005802 | 0.015579 | 0.035524 | −0.021253 | −0.010949 | 0.004164 | 0.06153 | 0.026153 | 0.026927 | 0.000666 |
| 221 | 0.027754 | −0.004609 | −0.016642 | −0.018992 | −0.004646 | −0.015223 | −0.024441 | 0.018726 | −0.028767 | −0.060864 | 0.0696591 | −0.03671 | −0.03553 | 0.022937 |
| 222 | 0.026962 | −0.021481 | −0.011591 | 0.009908 | −0.022986 | −0.019153 | −0.011556 | −0.026174 | −0.011295 | −0.024673 | 0.04425 | 0.003442 | −0.039481 | 0.001396 |
| 223 | 0.020444 | −0.034273 | −0.050036 | 0.017924 | −0.019109 | −0.000872 | 0.023738 | −0.046712 | 0.034791 | −0.04448 | 0.02122 | 0.04658 | −0.014353 | 0.001225 |
| 224 | −0.004269 | 0.011247 | 0.033039 | −0.011081 | 0.012318 | −0.018065 | 0.03017 | −0.000348 | −0.001766 | −0.023232 | 0.008868 | 0.03045 | −0.015163 | 0.010076 |
| 225 | −0.002319 | 0.006827 | 0.021079 | −0.020679 | 0.012698 | −0.011427 | −0.006681 | 0.021437 | −0.008823 | −0.02272 | 0.020935 | 0.008462 | −0.026334 | 0.006789 |
| 226 | 0.001121 | 0.009839 | −0.019918 | −0.020016 | −0.009602 | −0.006175 | 0.023151 | −0.028923 | 0.042103 | 0.024767 | −0.013376 | 0.015856 | −0.001502 | 0.026246 |
| 227 | −0.026414 | 0.008025 | 0.004254 | 0.005217 | 0.029748 | 0.028136 | −0.017025 | 0.040808 | −0.030697 | 0.025871 | −0.017725 | −0.005405 | −0.000559 | 0.008269 |
| 228 | 0.016595 | −0.022962 | 0.020506 | 0.020705 | 0.00628 | 0.077313 | 0.002154 | −0.004197 | −0.036834 | 0.007656 | 0.037598 | 0.009537 | 0.01617 | 0.002155 |
| 229 | −0.03627 | −0.006676 | 0.00516 | −0.027403 | 0.037262 | 0.007396 | −0.007112 | 0.017074 | −0.086189 | 0.038424 | 0.00905 | −0.060119 | −0.018111 | 0.016625 |
| 230 | 0.014769 | 0.019018 | −0.01549 | 0.001241 | −0.000784 | −0.00509 | −0.02913 | −0.010579 | −0.006926 | 0.008773 | −0.001743 | −0.014312 | −0.010798 | −0.003451 |
| 231 | −0.038514 | −0.000215 | −0.013645 | −0.004064 | 0.014872 | −0.036582 | 0.031982 | −0.015442 | 0.004881 | 0.009499 | 0.023003 | 0.013791 | −0.037528 | −0.009569 |
| 232 | 0.00024 | −0.008526 | −0.019907 | −0.023064 | 0.013578 | −0.032713 | −0.027865 | −0.029628 | −0.044634 | −0.006175 | 0.032374 | 0.003108 | −0.018308 | −0.019957 |
| 233 | 0.003056 | −0.000772 | −0.018908 | 0.000159 | 0.015409 | 0.019762 | 0.014053 | −0.009549 | 0.005549 | −0.005011 | −0.009957 | 0.026416 | −0.022985 | 0.026529 |
| 234 | 0.028033 | 0.01115 | 0.011113 | 0.012641 | 0.006702 | 0.0166 | 0.043296 | −0.014281 | −0.014864 | −0.030612 | −0.020159 | 0.003984 | −0.014815 | −0.00451 |
| 235 | −0.001303 | 0.030774 | 0.027835 | 0.000075 | 0.023116 | 0.012073 | −0.045289 | 0.035443 | −0.033135 | 0.011124 | −0.029555 | −0.044222 | −0.005046 | 0.009155 |
| 236 | 0.027926 | −0.017425 | 0.006186 | 0.006643 | −0.002202 | −0.010747 | −0.007373 | −0.011488 | 0.026682 | 0.0307 | −0.014345 | 0.01428 | 0.005971 | −0.032831 |
| 237 | −0.0243121 | 0.0036551 | 0.012425 | 0.015084 | 0.020866 | 0.017557 | 0.006497 | 0.042848 | −0.030663 | 0.013198 | −0.004759 | −0.044723 | 0.012653 | −0.032689 |
| 238 | −0.031955 | −0.010177 | −0.000303 | −0.01656 | −0.022538 | −0.058282 | 0.020478 | −0.000867 | 0.02125 | −0.039223 | 0.005305 | −0.008985 | 0.043917 | −0.01441 |
| 239 | −0.009191 | −0.016951 | 0.000448 | −0.01667 | −0.021658 | −0.036773 | −0.011453 | 0.009479 | 0.027816 | 0.011413 | −0.004665 | 0.010516 | 0.008499 | −0.000183 |
| 240 | −0.016763 | −0.007447 | 0.007001 | −0.011227 | 0.000254 | −0.013044 | 0.033985 | 0.043064 | −0.004917 | −0.044841 | −0.010226 | −0.017113 | −0.029931 | 0.02036 |
| 241 | 0.01207 | −0.022948 | 0.018872 | 0.004202 | −0.001544 | 0.025075 | 0.018109 | 0.032569 | −0.006186 | 0.020253 | −0.036885 | 0.030014 | −0.002068 | 0.021716 |
| 242 | −0.000092 | −0.020219 | −0.002672 | 0.00516 | 0.019463 | −0.001584 | −0.010555 | −0.046809 | 0.019809 | −0.030904 | 0.00522 | 0.029144 | 0.039277 | 0.009185 |
| 243 | −0.006931 | −0.011374 | −0.021989 | 0.013981 | −0.013356 | −0.062343 | −0.026952 | −0.0016 | −0.018297 | −0.01511 | −0.037376 | −0.022469 | −0.006765 | 0.013793 |
| 244 | −0.000781 | −0.017337 | −0.036394 | −0.002449 | 0.013777 | 0.039827 | −0.023566 | 0.01507 | −0.001589 | −0.040434 | 0.020416 | −0.008547 | −0.007575 | 0.009626 |
| 245 | 0.009568 | 0.026611 | −0.0126 | −0.008256 | −0.016092 | −0.035897 | −0.007878 | 0.02248 | 0.018664 | 0.004744 | 0.03821 | 0.018965 | 0.012003 | −0.007058 |
| 246 | −0.041954 | −0.003713 | 0.01886 | −0.017877 | −0.018324 | −0.013471 | −0.007473 | −0.03527 | −0.027782 | −0.006056 | 0.010184 | −0.012445 | 0.009042 | −0.031861 |
| 247 | −0.004142 | −0.00664 | 0.008437 | 0.015618 | −0.023936 | 0.016952 | −0.010544 | −0.036437 | 0.040268 | 0.000799 | −0.006575 | 0.0172651 | −0.017989 | −0.020275 |
| 248 | −0.002269 | 0.024149 | 0.001573 | −0.001098 | −0.013904 | −0.026852 | −0.019445 | 0.005966 | 0.016575 | 0.004082 | 0.019377 | 0.009987 | −0.014137 | −0.002072 |
| 249 | −0.008239 | −0.01656 | −0.017488 | −0.003783 | −0.003661 | −0.039487 | 0.014699 | 0.021901 | −0.016595 | 0.050868 | −0.048514 | −0.026253 | −0.037374 | −0.002283 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 250 | 0.014248 | 0.013952 | −0.008385 | 0.011953 | 0.000664 | −0.008574 | 0.038811 | −0.005216 | 0.033327 | 0.00762 | −0.037791 | −0.035181 | 0.00736 | 0.017969 |
| 251 | −0.001675 | −0.016014 | −0.029918 | −0.020141 | 0.013324 | 0.007123 | 0.025553 | 0.013468 | 0.004619 | −0.046041 | −0.001553 | 0.000888 | 0.028377 | 0.004236 |
| 252 | 0.029733 | −0.025122 | −0.003827 | 0.011711 | −0.001463 | −0.021744 | −0.01937 | 0.007445 | −0.039927 | 0.056203 | 0.003042 | 0.016142 | 0.00242 | 0.006784 |
| 253 | 0.025733 | −0.023215 | 0.013262 | 0.011576 | −0.037344 | −0.033133 | 0.020945 | −0.001004 | 0.014466 | 0.041748 | 0.000519 | −0.006112 | −0.009596 | 0.019458 |
| 254 | −0.025885 | −0.04527 | −0.056132 | 0.001643 | −0.001668 | 0.037207 | −0.005752 | −0.000111 | 0.007884 | −0.020702 | −0.051427 | 0.013797 | −0.000635 | 0.006812 |
| 255 | −0.023298 | −0.021768 | −0.026492 | −0.01822 | 0.000797 | 0.040837 | −0.006197 | −0.026175 | −0.024307 | −0.039502 | −0.02225 | −0.004693 | −0.004448 | −0.00179 |
| 256 | 0.070382 | 0.016061 | 0.028779 | 0.001084 | −0.029062 | 0.004827 | −0.010266 | −0.02046 | −0.018095 | −0.034265 | −0.014423 | −0.01349 | −0.018307 | 0.016084 |
| 257 | 0.020203 | 0.009031 | 0.034153 | 0.021502 | 0.000165 | −0.011106 | −0.022614 | −0.025043 | 0.013535 | −0.022211 | 0.002403 | 0.01461 | −0.003243 | −0.014087 |
| 258 | −0.001249 | −0.003453 | 0.019719 | −0.008907 | −0.01533 | −0.0103 | −0.027943 | 0.017662 | 0.009007 | 0.031753 | −0.000466 | 0.010924 | −0.028816 | −0.038592 |
| 259 | 0.007522 | −0.002674 | −0.039502 | 0.00685 | −0.001184 | 0.023467 | 0.036586 | −0.012024 | −0.003912 | 0.022236 | −0.023079 | 0.022901 | 0.023905 | 0.011923 |
| 260 | 0.036419 | 0.016904 | −0.013398 | 0.034093 | 0.03561 | 0.019311 | 0.006245 | 0.036801 | −0.04298 | 0.076557 | −0.013837 | −0.03476 | −0.012498 | 0.015726 |
| 261 | −0.007547 | 0.014559 | −0.000931 | −0.013455 | 0.022689 | −0.005011 | 0.043736 | 0.033327 | −0.072981 | −0.011667 | 0.013888 | 0.002773 | 0.033047 | 0.006685 |
| 262 | −0.008357 | −0.014515 | 0.019138 | 0.008668 | 0.016937 | 0.006382 | −0.022479 | −0.030208 | −0.012257 | −0.00116 | −0.00087 | 0.000819 | 0.002421 | −0.00615 |
| 263 | −0.005925 | −0.011859 | 0.006535 | 0.023618 | −0.000284 | −0.031273 | −0.028972 | −0.015302 | 0.019548 | 0.007168 | 0.008759 | −0.002304 | 0.018102 | −0.000431 |
| 264 | 0.010551 | −0.01115 | −0.003979 | 0.020132 | −0.011241 | 0.017696 | −0.008177 | −0.021939 | −0.014942 | 0.022567 | −0.024149 | −0.034505 | −0.035821 | 0.021525 |
| 265 | 0.025447 | −0.013634 | 0.021487 | 0.012803 | −0.00291 | 0.024942 | −0.01667 | −0.043033 | 0.018004 | −0.003509 | −0.042406 | −0.00842 | −0.040549 | −0.036611 |
| 266 | 0.071923 | 0.020353 | 0.011779 | 0.001817 | −0.001807 | −0.026326 | 0.011023 | −0.02283 | −0.005919 | 0.006092 | −0.008724 | 0.002185 | −0.010741 | −0.037137 |
| 267 | −0.002164 | −0.027962 | −0.0097 | −0.01409 | −0.011195 | −0.023161 | 0.051506 | 0.005669 | −0.016197 | −0.004289 | −0.02885 | −0.017716 | −0.024699 | 0.048028 |
| 268 | 0.0087611 | 0.0020961 | 0.003702 | 0.017084 | −0.005525 | 0.035385 | −0.003318 | −0.014627 | 0.007086 | 0.052394 | −0.021121 | 0.017862 | −0.024523 | 0.013777 |
| 269 | 0.004799 | 0.006708 | 0.009158 | 0.011617 | 0.005219 | 0.002334 | 0.013372 | −0.029982 | 0.003753 | 0.03038 | −0.01128 | 0.015176 | −0.015722 | 0.032094 |
| 270 | −0.007449 | 0.00837 | −0.002576 | 0.004431 | 0.008112 | −0.00791 | 0.016474 | −0.018678 | −0.003878 | 0.009191 | −0.020616 | 0.014452 | −0.000774 | 0.030786 |
| 271 | −0.012636 | −0.029942 | −0.003055 | 0.022777 | −0.022532 | −0.054232 | −0.024235 | 0.012337 | 0.066546 | 0.019567 | 0.004023 | −0.050116 | 0.018184 | −0.017713 |
| 272 | 0.002174 | −0.006223 | −0.006469 | −0.033334 | −0.010515 | 0.00792 | 0.034795 | −0.012028 | −0.004974 | 0.006165 | −0.013549 | −0.012556 | 0.015379 | 0.003838 |
| 273 | 0.010757 | 0.017855 | 0.006764 | 0.002467 | −0.015311 | 0.027562 | −0.006022 | −0.009778 | −0.001663 | 0.019631 | −0.024224 | 0.040277 | −0.006185 | 0.021677 |
| 274 | 0.002258 | 0.012333 | 0.012182 | −0.002103 | −0.009128 | 0.026517 | 0.000123 | −0.011137 | 0.003728 | 0.017391 | −0.021955 | 0.029481 | −0.004849 | 0.017102 |
| 275 | 0.050595 | 0.020382 | −0.033423 | 0.010391 | −0.017003 | −0.009451 | −0.052635 | 0.027943 | −0.031085 | −0.021745 | −0.013921 | −0.011723 | −0.013953 | 0.008964 |
| 276 | 0.024505 | −0.01549 | 0.00601 | −0.001239 | 0.003783 | −0.017235 | 0.013065 | −0.023375 | 0.030606 | 0.051742 | −0.024264 | 0.013999 | 0.015171 | −0.00765 |
| 277 | 0.017335 | −0.011071 | −0.020834 | 0.024418 | 0.035836 | 0.041703 | 0.000614 | 0.058774 | 0.007874 | 0.01295 | −0.025807 | −0.020122 | −0.007685 | 0.020898 |
| 278 | 0.027078 | 0.001761 | −0.006373 | 0.019064 | 0.041146 | 0.033135 | 0.015169 | 0.051044 | −0.001157 | 0.007675 | 0.004228 | −0.004004 | −0.000416 | 0.017336 |
| 279 | 0.019647 | 0.007251 | −0.026718 | −0.021761 | −0.003484 | −0.055052 | 0.012377 | 0.026499 | 0.017644 | −0.007693 | −0.0081 | −0.010204 | 0.033714 | 0.023347 |
| 280 | 0.024316 | 0.00879 | −0.006792 | 0.011756 | −0.01767 | −0.009225 | 0.00622 | −0.039737 | 0.005198 | 0.012601 | −0.011473 | −0.00426 | −0.026564 | 0.022033 |
| 281 | −0.039703 | 0.050668 | −0.01693 | −0.02916 | 0.0082 | −0.070756 | 0.010982 | −0.064305 | −0.022219 | −0.033533 | −0.016623 | 0.01471 | 0.012184 | 0.024663 |
| 282 | −0.021442 | 0.010578 | −0.013935 | 0.01052 | 0.012441 | −0.053868 | 0.007316 | −0.070566 | −0.003673 | −0.010988 | −0.013382 | 0.016255 | 0.002456 | 0.030006 |
| 283 | 0.0058631 | 0.010523 | −0.02693 | 0.003555 | 0.008721 | −0.033704 | −0.0101 | −0.00147 | 0.036624 | −0.005915 | −0.0233 | −0.01815 | −0.003487 | 0.026928 |
| 284 | 0.03823 | 0.020412 | 0.017659 | 0.011408 | 0.00738 | −0.003623 | −0.01877 | −0.011199 | 0.009161 | −0.027965 | −0.000003 | −0.011541 | 0.000192 | −0.00294 |
| 285 | 0.013755 | −0.003394 | 0.009516 | 0015393 | 0.018132 | 0.025765 | −0.020397 | −0.02194 | 0.023412 | −0.019479 | −0.007789 | 0.013873 | 0.009327 | 0.001445 |
| 286 | 0.014041 | 0.017922 | −0.037039 | −0.01593 | 0.012173 | −0.010157 | −0.021696 | 0.007341 | 0.024035 | 0.024485 | 0.00915 | −0.009649 | −0.004302 | −0.018717 |
| 287 | −0.007983 | 0.001174 | −0.023948 | −0.004395 | 0.009928 | −0.044026 | −0.025371 | −0.001099 | 0.016404 | 0.013812 | 0.015256 | −0.003327 | −0.001878 | −0.022664 |
| 288 | 0.030135 | 0.012166 | −0.002363 | −0.008614 | 0.029717 | 0.018377 | −0.044067 | 0.038039 | 0.012444 | 0.034746 | −0.003622 | −0.035217 | −0.029482 | −0.006445 |
| 289 | 0.017349 | −0.012852 | 0.025255 | 0.010777 | 0.01512 | 0.023671 | −0.058571 | −0.017133 | −0.008889 | −0.031873 | −0.006485 | −0.021319 | −0.012779 | −0.018479 |
| 290 | −0.004549 | −0.000151 | 0.006437 | 0.010065 | −0.0089 | 0.027588 | 0.003866 | −0.028508 | −0.029582 | −0.05914 | 0.008759 | 0.00411 | 0.000235 | 0.009727 |
| 291 | −0.005597 | −0.002101 | 0.003155 | 0.01131 | −0.003962 | 0.033174 | −0.000554 | −0.032588 | −0.025488 | −0.053599 | 0.005112 | −0.012032 | 0.003908 | 0.015419 |
| 292 | −0.006473 | −0.001084 | 0.006651 | −0.007084 | −0.022894 | −0.004461 | −0.009104 | −0.023441 | −0.015707 | −0.058382 | −0.001866 | 0.00039 | 0.024401 | 0.027108 |
| 293 | 0.038899 | 0.024147 | −0.047568 | −0.011974 | −0.005182 | 0.029059 | −0.001727 | −0.016561 | 0.0299 | 0.011195 | −0.040536 | −0.026002 | 0.000168 | 0.024499 |
| 294 | 0.016144 | 0.017192 | −0.002762 | −0.003535 | 0.013362 | 0.025477 | −0.014556 | 0.007271 | 0.008497 | 0.013867 | 0.004036 | −0.024033 | −0.047655 | 0.003072 |
| 295 | 0.0027911 | 0.01974 | −0.0178 | 0.005108 | 0.005416 | 0.012154 | −0.019834 | 0.002423 | 0.029668 | 0.017414 | −0.020602 | 0.000797 | 0.004248 | 0.008337 |
| 296 | 0.039828 | −0.012972 | −0.008905 | 0.002829 | −0.026767 | 0.007091 | 0.004117 | 0.011144 | 0.043899 | −0.011602 | 0.011075 | −0.014765 | 0.001112 | 0.049943 |
| 297 | 0.011347 | 0.01212 | 0.006927 | −0.004823 | 0.016991 | −0.013636 | 0.004774 | 0.001344 | 0.009831 | 0.002377 | −0.007687 | 0.003613 | −0.015226 | 0.029828 |
| 298 | −0.00622 | 0.038377 | 0.036948 | −0.006354 | −0.017459 | −0.019189 | 0.009005 | −0.036098 | −0.022108 | 0.059673 | −0.028956 | −0.04619 | −0.010286 | 0.010412 |
| 299 | −0.009766 | −0.01866 | −0.013597 | −0.008042 | 0.011668 | 0.001923 | 0.029693 | −0.003053 | 0.043118 | 0.03705 | −0.013368 | 0.016725 | −0.018517 | −0.031205 |
| 300 | −0.004976 | 0.048618 | 0.043436 | 0.004882 | 0.022591 | 0.01653 | −0.000086 | 0.015792 | −0.051137 | −0.031731 | −0.014856 | 0.000811 | −0.026229 | 0.004075 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 301 | 0.004656 | 0.004318 | 0.008061 | 0.008735 | 0.025288 | 0.002978 | −0.02133 | −0.003638 | 0.013191 | 0.003124 | 0.016828 | −0.005024 | −0.019649 | −0.030461 |
| 302 | −0.033288 | −0.007338 | −0.007494 | −0.006179 | 0.019998 | 0.026614 | −0.002263 | −0.003767 | 0.019348 | 0.034068 | 0.020987 | −0.00626 | −0.007351 | −0.024468 |
| 303 | −0.0228071 | −0.011121 | −0.017309 | −0.008871 | −0.000282 | 0.007413 | 0.027237 | 0.003474 | 0.045793 | 0.045614 | 0.046906 | −0.003726 | −0.016422 | −0.049277 |
| 304 | −0.030027 | −0.000634 | −0.021981 | −0.018208 | −0.009408 | 0.012279 | 0.044087 | 0.050114 | 0.080628 | 0.04395 | 0.040053 | −0.003357 | 0.007111 | −0.046359 |
| 305 | −0.042948 | −0.004949 | −0.02472 | −0.010566 | 0.007636 | −0.015187 | −0.019461 | 0.004997 | −0.009791 | −0.027534 | 0.011114 | −0.006602 | 0.036123 | −0.019243 |
| 306 | −0.015835 | −0.021648 | −0.002369 | 0.007842 | −0.002505 | 0.004088 | 0.014457 | 0.017769 | −0.020553 | −0.00651 | 0.023291 | 0.004194 | −0.018284 | −0.054207 |
| 307 | −0.025244 | 0.006826 | −0.047264 | 0.018352 | −0.051362 | −0.041454 | 0.037426 | 0.031538 | 0.009386 | 0.001526 | 0.044858 | −0.019998 | 0.014017 | −0.002865 |
| 308 | −0.007856 | −0.031021 | −0.01844 | −0.008846 | 0.005413 | 0.008492 | 0.0354 | 0.031016 | 0.028104 | −0.020176 | 0.025575 | 0.018829 | 0.015379 | −0.020464 |
| 309 | −0.027078 | −0.023703 | −0.029175 | 0.00864 | 0.006292 | −0.025877 | 0.008052 | 0.008366 | 0.009035 | −0.028592 | −0.007623 | −0.000021 | 0.005596 | 0.005541 |
| 310 | −0.012728 | −0.022342 | −0.027376 | 0.018126 | 0.011787 | 0.01266 | 0.01522 | 0.013636 | 0.022413 | −0.010281 | 0.033313 | 0.004208 | 0.021159 | −0.028811 |
| 311 | 0.010939 | 0.000591 | −0.009188 | 0.008867 | −0.01289 | 0.057235 | −0.018007 | 0.021121 | −0.049386 | 0.035356 | −0.027148 | −0.014725 | 0.012253 | 0.031618 |
| 312 | −0.019886 | 0.03556 | 0.019968 | −0.03165 | 0.019309 | −0.019014 | 0.028461 | −0.069621 | −0.004338 | −0.044164 | −0.040533 | −0.02517 | −0.0168 | 0.015525 |
| 313 | 0.025057 | 0.018145 | 0.025197 | 0.012999 | −0.003344 | 0.010415 | −0.005446 | 0.00199 | 0.00599 | 0.021746 | 0.011973 | −0.001935 | 0.067868 | −0.006429 |
| 314 | −0.011941 | 0.010842 | 0.042422 | 0.02658 | −0.029948 | 0.053289 | −0.036758 | 0.039833 | −0.010627 | 0.040794 | 0.053424 | −0.041216 | 0.070625 | −0.006475 |
| 315 | −0.045062 | −0.020812 | 0.004316 | 0.003663 | 0.020987 | −0.00426 | 0.002312 | −0.002858 | 0.013246 | −0.007143 | 0.002473 | −0.008385 | 0.024494 | −0.026252 |
| 316 | 0.070888 | −0.021594 | −0.010586 | 0.027395 | −0.000896 | 0.079208 | 0.010887 | −0.048899 | −0.104432 | −0.006219 | −0.055014 | 0.012653 | −0.013039 | 0.03131 |
| 317 | −0.014851 | 0.000611 | 0.005292 | 0.040615 | 0.024076 | −0.019063 | −0.035117 | 0.015604 | 0.008029 | −0.054534 | −0.001594 | −0.026115 | 0.008084 | 0.012361 |
| 318 | 0.017696 | −0.018629 | −0.044978 | −0.001167 | −0.004576 | 0.029454 | −0.017631 | 0.066417 | 0.007196 | 0.017301 | 0.055454 | 0.022632 | 0.037653 | 0.001992 |
| 319 | −0.013749 | −0.0188721 | −0.006062 | 0.020686 | 0.009186 | −0.029952 | −0.02237 | 0.004702 | 0.0158271 | −0.009192 | 0.0085581 | −0.01824 | 0.0073641 | 0.010957 |
| 320 | 0.065935 | −0.040061 | 0.017274 | −0.011457 | −0.065737 | 0.030729 | −0.026528 | −0.018239 | 0.004947 | 0.025774 | −0.052522 | −0.014516 | −0.027736 | −0.001237 |
| 321 | 0.041129 | −0.035838 | 0.000748 | 0.008249 | −0.009416 | 0.052585 | 0.016484 | 0.010155 | −0.067259 | 0.014133 | 0.008565 | 0.036272 | 0.023485 | −0.042218 |
| 322 | 0.025138 | −0.005168 | −0.028261 | −0.031769 | 0.020501 | 0.060818 | 0.032521 | 0.003108 | 0.075487 | −0.012878 | 0.020495 | −0.036528 | −0.040297 | 0.010571 |
| 323 | 0.02939 | 0.024008 | −0.016274 | −0.016865 | −0.034996 | −0.024802 | 0.025034 | −0.02277 | −0.046621 | 0.031623 | −0.015624 | 0.030666 | 0.002094 | −0.05118 |
| 324 | 0.019186 | 0.01201 | −0.056313 | −0.034128 | 0.016374 | −0.0439 | 0.022703 | −0.044464 | 0.043758 | 0.008038 | 0.0067 | −0.029748 | −0.007638 | 0.042717 |
| 325 | 0.023291 | 0.023388 | −0.006956 | −0.007199 | −0.002248 | −0.009417 | 0.024677 | −0.034713 | 0.008849 | −0.022668 | 0.047662 | 0.002473 | 0.023417 | 0.040814 |
| 326 | −0.01701 | 0.006652 | 0.013174 | −4012387 | −0.032392 | −0.08565 | −0.021495 | 0.008937 | −0.04238 | −0.020312 | 0.018139 | −0.018975 | 0.002068 | −0.013905 |
| 327 | −0.031442 | −0.047459 | −0.041213 | −0.023834 | −0.017185 | 0.006122 | 0.024963 | 0.003125 | −0.01628 | −0.005322 | 0.001531 | 0.002069 | 0.030574 | −0.018342 |
| 328 | −0.018549 | 0.020225 | 0.033564 | −0.0129 | −0.007643 | −0.03316 | −0.006582 | 0.014616 | −0.020585 | −0.009507 | −0.010994 | −0.011215 | 0.010688 | 0.002518 |
| 329 | −0.003414 | −0.029014 | −0.039827 | −0.003227 | 0.000638 | 0.008371 | 0.002634 | −0.003434 | −0.04753 | 0.000387 | 0.00211 | −0.018003 | 0.015573 | −0.026159 |
| 330 | −0.060719 | 0.025473 | −0.036196 | −0.026165 | 0.045336 | 0.018365 | −0.039237 | −0.04467 | −0.017629 | 0.04328 | −0.017126 | 0.049297 | 0.011201 | −0.007612 |
| 331 | 0.00152 | −0.006437 | −0.012671 | −0.011179 | −0.016527 | −0.005794 | −0.005225 | −0.028344 | −0.015377 | 0.023231 | −0.013342 | −0.053278 | −0.013447 | −0.015878 |
| 332 | −0.029539 | −0.013329 | 0.01936 | −0.022945 | −0.019598 | −0.006706 | 0.026785 | 0.111451 | 0.013545 | −0.001878 | 0.034368 | −0.026882 | −0.013266 | 0.018761 |
| 333 | 0.017787 | 0.007112 | −0.004982 | 0.012737 | −0.006555 | −0.035828 | −0.002959 | −0.043117 | −0.006929 | −0.039487 | 0.027262 | −0.012189 | 0.006091 | 0.028872 |
| 334 | 0.022099 | 0.006056 | 0.030052 | 0.011876 | 0.058579 | 0.012881 | 0.011321 | −0.002595 | −0.045679 | −0.009158 | 0.067114 | 0.008658 | −0.046928 | −0.006764 |
| 335 | 0.012525 | 0.016373 | −0.059894 | −0.010893 | −0.008234 | −0.004081 | 0.031329 | 0.003458 | −0.01854 | −0.00972 | −0.003676 | 0.013871 | 0.022988 | −0.004753 |
| 336 | −0.037262 | −0.012942 | 0.017826 | 0.031029 | 0.000427 | 0.013098 | −0.012223 | 0.013177 | 0.009865 | −0.037997 | −0.043787 | −0.036934 | −0.036428 | −0.025211 |
| 337 | −0.02291 | −0.000399 | 0.002688 | −0.01942 | 0.009453 | −0.040126 | −0.02777 | −0.008652 | 0.021181 | −0.034567 | −0.046241 | −0.029003 | −0.025419 | −0.006587 |
| 338 | 0.07548 | 0.016475 | −0.019781 | −0.009388 | −0.054089 | −0.02883 | 0.063969 | 0.013675 | −0.063985 | 0.030206 | −0.027901 | 0.025477 | −0.051543 | 0.024033 |
| 339 | −0.003717 | 0.004564 | −0.004844 | −0.015485 | −0.00692 | −0.003508 | −0.016367 | 0.05419 | −0.07642 | −0.00018 | −0.000175 | −0.016909 | 0.023091 | −0.00628 |
| 340 | 0.03381 | 0.026057 | 0.026227 | 0.02286 | −0.004718 | 0.026842 | −0.022313 | 0.01512 | 0.015724 | −0.050164 | 0.032225 | −0.009848 | 0.023158 | −0.009197 |

| | FJ | FK | FL | FM | FN | FO | FP | FQ | FR | FS | FT | FU | FV | FW |
|---|---|---|---|---|---|---|---|---|---|---|---|---|---|---|
| 1 | 0.001162 | 0.01776 | 0.01156 | −0.031749 | −0.021433 | −0.067909 | −0.021191 | 0.069916 | 0.076592 | 0.000504 | 0.0140541 | −0.031871 | −0.052233 | 0.052033 |
| 2 | 0.112354 | −0.005464 | −0.107432 | −0.003331 | 0.043281 | −0.008789 | 0.03788 | 0.032563 | −0.001439 | −0.061729 | −0.04314 | 0.073669 | −0.04319 | 0.087867 |
| 3 | −0.029184 | −0.087535 | 0.03475 | 0.024066 | −0.041169 | −0.04058 | −0.02678 | −0.001401 | 0.019277 | 0.078701 | −0.003468 | 0.027039 | 0.087035 | 0.011911 |
| 4 | −0.00785 | 0.128845 | −0.02837 | −0.00968 | 0.022365 | 0.044342 | 0.022897 | 0.036475 | −0.011934 | −0.036477 | −0.025848 | −0.043124 | 0.071303 | −0.051291 |
| 5 | −0.006814 | 0.023991 | 0.00562 | 0.031838 | 0.014764 | −0.000997 | 0.021203 | 0.016968 | 0.009497 | 0.020747 | −0.01059 | −0.012587 | −0.037653 | −0.066987 |
| 6 | 0.062778 | −0.051447 | 0.08618 | −0.016627 | −0.026928 | −0.004921 | −0.022326 | −0.029444 | −0.068837 | −0.118654 | −0.074595 | 0.081361 | −0.02748 | 0.001747 |
| 7 | 0.078912 | −0.0974671 | −0.0604 | −0.02852 | −0.068394 | −0.064701 | −0.045817 | −0.053297 | 0.006802 | −0.001692 | −0.026543 | −0.073776 | 0.016914 | −0.01869 |
| 8 | −0.043825 | −0.0167521 | 0.052581 | −0.033955 | 0.015094 | 0.035787 | 0.018664 | −0.028457 | −0.005602 | −0.034514 | −0.06003 | 0.013309 | 0.128689 | 0.007813 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 9 | 0.039742 | −0.169571 | −0.025646 | −0.042155 | −0.031877 | 0.026114 | 0.029224 | −0.056762 | −0.045417 | −0.015234 | −0.018702 | 0.056182 | −0.063121 | −0.075475 |
| 10 | 0.053795 | 0.02237 | 0.050425 | −0.011394 | −0.013471 | −0.007926 | −0.031234 | 0.048054 | 0.003375 | 0.021921 | 0.056195 | 0.026238 | 0.034239 | −0.043154 |
| 11 | −0.030437 | 0.068323 | 0.02071 | −0.008425 | 0.003424 | −0.02471 | −0.024659 | −0.008732 | −0.051382 | −0.006907 | 0.077339 | 0.008827 | −0.025362 | −0.020477 |
| 12 | 0.01075 | 0.036426 | −0.003855 | 0.02096 | 0.016324 | −0.013925 | 0.01287 | 0.016707 | −0.021506 | −0.037965 | 0.018209 | 0.059729 | −0.038073 | 0.008582 |
| 13 | 0.074043 | −0.006187 | 0.057166 | −0.067224 | 0.026864 | 0.017417 | 0.046199 | 0.046178 | −0.030053 | −0.068844 | 0.036791 | 0.01067 | −0.055112 | 0.046656 |
| 14 | 0.074003 | −0.050172 | −0.088021 | 0.037258 | −0.000069 | 0.042036 | −0.016209 | −0.034973 | −0.034128 | 0.020159 | −0.004906 | 0.012357 | 0.037976 | 0.039508 |
| 15 | 0.094377 | 0.03065 | 0.049135 | −0.028686 | 0.031344 | 0.0835 | −0.021809 | −0.083383 | −0.104576 | −0.045414 | 0.001387 | 0.01501 | −0.02876 | −0.034538 |
| 16 | 0.04681 | 0.003376 | 0.04234 | −0.007344 | 0.053506 | 0.057967 | 0.011277 | 0.037299 | 0.046651 | 0.057461 | 0.062029 | 0.001561 | 0.026157 | 0.001555 |
| 17 | −0.039722 | 0.088586 | −0.114903 | −0.052866 | −0.016281 | 0.003234 | −0.024934 | −0.023921 | −0.048467 | −0.053002 | −0.037652 | −0.010548 | −0.042038 | 0.035328 |
| 18 | −0.109986 | −0.1047651 | 0.0128241 | −0.00506 | −0.066124 | −0.063185 | −0.062272 | −0.056848 | −0.002158 | −0.032738 | −0.043072 | −0.067273 | −0.093742 | 0.002889 |
| 19 | −0.024049 | −0.040795 | −0.077355 | −0.033981 | 0.000898 | 0.00746 | −0.001205 | 0.00992 | −0.000075 | 0.014567 | 0.136044 | −0.030852 | −0.024646 | −0.00026 |
| 20 | −0.02159 | 0.098697 | 0.021265 | −0.074887 | −0.060027 | −0.077687 | −0.033911 | 0.064862 | 0.067085 | 0.043685 | −0.024678 | −0.030099 | −0.105563 | −0.016991 |
| 21 | −0.027922 | 0.045581 | 0.037823 | −0.066323 | −0.011334 | −0.030682 | 0.01226 | −0.072618 | −0.024275 | 0.007296 | −0.167713 | −0.068006 | −0.083695 | −0.032703 |
| 22 | 0.046955 | −0.000653 | −0.014234 | 0.099248 | −0.009929 | −0.00461 | 0.004966 | −0.016054 | −0.053036 | −0.118986 | −0.088918 | −0.037636 | −0.098653 | −0.020087 |
| 23 | −0.010891 | −0.054785 | −0.079101 | −0.015583 | 0.028156 | 0.021092 | −0.003194 | 0.039588 | 0.009482 | −0.026341 | −0.017841 | −0.075921 | 0.034177 | −0.034036 |
| 24 | 0.016967 | −0.010255 | 0.006918 | 0.06947 | 0.089033 | 0.066956 | 0.058294 | 0.031742 | 0.011087 | −0.053672 | 0.020836 | 0.061357 | 0.040267 | −0.060584 |
| 25 | −0.002903 | 0.11382 | 0.151266 | −0.085115 | 0.027191 | 0.020384 | 0.00959 | −0.010506 | −0.028496 | 0.025537 | 0.03266 | 0.055466 | 0.134824 | 0.032083 |
| 26 | −0.090246 | −0.03129 | 0.08082 | −0.069514 | 0.046659 | 0.02315 | 0.026122 | 0.026971 | 0.000645 | 0.107768 | 0.040566 | −0.043187 | −0.036305 | −0.020457 |
| 27 | −0.07717 | −0.082413 | 0.009554 | 0.041182 | −0.007522 | −0.003257 | 0.057003 | −0.032614 | −0.018017 | −0.050807 | −0.011776 | −0.041636 | −0.013583 | 0.012279 |
| 28 | 0.07434 | −0.009191 | −0.045115 | −0.177208 | 0.044565 | 0.071987 | −0.01462 | −0.006358 | 0.012852 | 0.009935 | 0.034033 | −0.118679 | 0.02981 | −0.014591 |
| 29 | −0.046138 | −0.062933 | −0.003583 | 0.010586 | 0.00339 | −0.031883 | −0.008778 | 0.005687 | 0.0287 | 0.034094 | 0.019715 | −0.012099 | 0.004716 | −0.035608 |
| 30 | 0.061827 | 0.026683 | −0.034592 | −0.011076 | −0.07333 | −0.103418 | −0.052009 | 0.005874 | 0.012184 | 0.010266 | 0.043957 | 0.000183 | −0.074354 | −0.077136 |
| 31 | 0.111147 | −0.047985 | −0.138249 | 0.021061 | 0.067736 | 0.109547 | 0.098785 | 0.060251 | −0.002887 | −0.032094 | −0.035384 | 0.109819 | −0.102026 | 0.02967 |
| 32 | −0.057625 | −0.080077 | −0.022391 | −0.063145 | 0.027727 | 0.013572 | 0.033872 | 0.039796 | 0.028739 | −0.053404 | −0.064656 | 0.049207 | 0.0647 | 0.002498 |
| 33 | −0.017399 | −0.1099 | −0.013331 | 0.012443 | 0.031392 | 0.017147 | 0.01536 | 0.007928 | 0.025028 | −0.015602 | 0.109424 | 0.073061 | −0.026834 | 0.016741 |
| 34 | 0.087655 | −0.073421 | −0.01476 | 0.028669 | 0.008802 | −0.004788 | −0.029886 | −0.028688 | 0.047003 | −0.005428 | 0.106833 | 0.025512 | −0.149073 | 0.01772 |
| 35 | 0.092508 | −0.070503 | −0.028573 | −0.047373 | −0.030156 | 0.011666 | −0.015741 | −0.028709 | −0.043468 | −0.011137 | −0.020844 | 0.00314 | 0.075378 | −0.001916 |
| 36 | 0.004718 | −0.008674 | 0.006594 | 0.001578 | 0.07954 | 0.10522 | 0.054944 | 0.065709 | 0.008191 | 0.028809 | 0.040137 | 0.030585 | 0.020996 | −0.004999 |
| 37 | −0.034238 | −0.049117 | 0.156651 | −0.037086 | −0.050259 | −0.056807 | −0.095058 | 0.038672 | −0.034982 | −0.035738 | −0.042939 | 0.030793 | 0.145986 | 0.049557 |
| 38 | 0.104679 | −0.063861 | 0.104959 | 0.013534 | −0.076356 | −0.071837 | −0.036417 | −0.036684 | −0.003693 | 0.044565 | 0.029267 | −0.047528 | −0.066619 | 0.004634 |
| 39 | 0.110426 | 0.102593 | −0.056079 | 0−.021439 | −0.000542 | 0.017098 | −0.00529 | −0.087082 | −0.049175 | −0.076102 | −0.0661 | −0.002919 | 0.011305 | 0.034315 |
| 40 | −0.082983 | 0.033447 | 0.034631 | 0.014501 | 0.037082 | 0.040356 | 0.020818 | 0.039732 | 0.021675 | 0.029609 | 0.00763 | 0.025115 | 0.114787 | 0.016671 |
| 41 | 0.074201 | −0.052225 | 0.144658 | −0.050251 | 0.011302 | 0.050662 | −0.001564 | 0.036127 | 0.027675 | −0.070747 | −0.05922 | 0.029128 | −0.0896 | −0.005003 |
| 42 | 0.001079 | −0.037753 | 0.019943 | −0.012841 | −0.006974 | 0.005504 | 0.004062 | 0.003652 | −0.005704 | −0.003688 | 0.006443 | 0.011724 | 0.001675 | −0.025116 |
| 43 | −0.166464 | 0.046263 | 0.070483 | 0.005981 | −0.023001 | −0.045441 | −0.012625 | −0.070833 | −0.063554 | −0.055183 | −0.203573 | −0.073652 | −0.001211 | −0.019142 |
| 44 | 0.02946 | 0.162928 | −0.025485 | −0.034119 | −0.054891 | −0.046337 | −0.044391 | −0.02463 | −0.020711 | −0.008079 | 0.03325 | 0.0069 | 0.069891 | 0.021181 |
| 45 | −0.006412 | 0.005386 | −0.001102 | −0.033088 | −0.033352 | −0.04266 | −0.011905 | −0.016757 | −0.009955 | 0.007542 | 0.048985 | 0.014118 | −0.084384 | −0.028168 |
| 46 | 0.041851 | −0.006143 | −0.044797 | −0.021671 | 0.04928 | 0.002436 | −0.026527 | 0.061727 | 0.031149 | 0.106151 | 0.038095 | −0.038223 | −0.005323 | 0.036371 |
| 47 | −0.093911 | −0.098073 | 0.072801 | −0.03467 | 0.033836 | −0.005128 | 0.009097 | 0.049808 | 0.005118 | 0.003396 | 0.117832 | 0.028492 | −0.129228 | 0.031593 |
| 48 | −0.03207 | 0.087642 | −0.001017 | 0.030198 | 0.071725 | 0.077637 | 0.074377 | 0.09532 | 0.053606 | 0.069857 | 0.039701 | 0.128834 | −0.001451 | 0.018779 |
| 49 | 0.099937 | −0.0009011 | −0.037079 | 0.09523 | 0.060797 | 0.045177 | 0.080078 | 0.050158 | 0.038729 | 0.027484 | 0.023169 | −0.00516 | −0.016234 | 0.080905 |
| 50 | 0.082687 | −0.013693 | 0.076513 | 0.01659 | 0.067159 | 0.039507 | 0.041751 | 0.050829 | 0.097463 | −0.03904 | −0.073919 | 0.018943 | −0.040599 | 0.156265 |
| 51 | 0.023014 | −0.014561 | 0.078165 | −0.060285 | 0.004939 | −0.021733 | 0.040269 | 0.028692 | 0.021618 | 0.021061 | 0.063972 | 0.050036 | 0.079917 | 0.037532 |
| 52 | 0.054629 | −0.002955 | −0.094403 | 0.016076 | 0.015139 | 0.08601 | 0.000116 | −0.022622 | 0.041977 | 0.039641 | 0.051793 | −0.066741 | 0.027985 | −0.050271 |
| 53 | 0.242051 | 0.125238 | 0.103286 | −0.065203 | 0.031116 | 0.029047 | −0.003593 | −0.001772 | 0.001574 | −0.06739 | −0.09174 | 0.019678 | 0.004783 | −0.05843 |
| 54 | 0.017081 | −0.028979 | 0.012257 | 0.018631 | −0.045274 | −0.034009 | −0.020865 | 0.03615 | 0.081258 | 0.022148 | −0.071299 | −0.074128 | 0.098891 | −0.066194 |
| 55 | −0.058174 | 0.077052 | −0.019918 | −0.016006 | 0.021891 | 0.060296 | 0.017635 | −0.026506 | 0.079702 | 0.029351 | 0.033032 | −0.068362 | 0.009237 | −0.042626 |
| 56 | 0.021541 | −0.109322 | 0.020739 | 0.036011 | 0.000194 | 0.000321 | 0.020481 | 0.057147 | 0.04351 | 0.013869 | −0.058855 | 0.075214 | 0.040053 | −0.050857 |
| 57 | 0.025913 | 0.143414 | 0.042039 | 0.021723 | 0.064595 | 0.107781 | 0.053077 | 0.028891 | 0.032926 | 0.080288 | 0.107637 | 0.009932 | 0.008978 | 0.05026 |
| 58 | 0.048714 | −0.008061 | −0.04847 | 0.012395 | 0.00825 | 0.032908 | 0.048319 | 0.020314 | 0.046853 | 0.078656 | −0.02342 | 0.035769 | −0.014709 | 0.009897 |
| 59 | −0.168488 | −0.143071 | 0.022062 | 0.001969 | 0.015621 | 0.019183 | 0.048561 | 0.002771 | −0.027777 | 0.015669 | 0.034836 | 0.028378 | −0.021667 | 0.011811 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 60 | 0.004726 | −0.078693 | 0.025149 | 0.030831 | 0.008922 | −0.00331 | 0.019965 | 0.044567 | −0.012193 | 0.027708 | −0.061006 | 0.006812 | 0.026141 | 0.029815 |
| 61 | 0.090292 | 0.061673 | 0.08765 | 0.08529 | −0.033584 | −0.071576 | −0.013732 | 0.011344 | 0.051901 | 0.044594 | 0.110682 | 0.083797 | −0.108823 | −0.023358 |
| 62 | −0.050313 | 0.066332 | −0.098202 | −0.045121 | 0.004167 | 0.039169 | −0.018069 | 0.004823 | −0.004008 | −0.031056 | 0.048258 | −0.002758 | −0.067898 | −0.026857 |
| 63 | −0.063475 | 0.020908 | −0.0266831 | −0.051508 | −0.032839 | −0.033746 | −0.024155 | −0.094782 | −0.105957 | −0.017222 | 0.031905 | −0.035033 | 0.0016721 | 0.093435 |
| 64 | 0.0081931 | 0.089685 | −0.091857 | 0.036047 | 0.018599 | 0.041047 | 0.060375 | 0.008188 | 0.050992 | 0.003881 | 0.080915 | 0.056976 | 0.028104 | 0.038044 |
| 65 | 0.071467 | −0.10514 | −0.039233 | −0.008655 | 0.016528 | −0.004381 | −0.031335 | 0.034833 | 0.049987 | 0.015818 | −0.039142 | 0.011263 | −0.009512 | 0.033993 |
| 66 | 0.111784 | −0.061321 | 0.012445 | 0.059976 | 0.036674 | 0.052276 | 0.018618 | −0.018246 | −0.013601 | 0.028968 | 0.002116 | −0.04557 | 0.192173 | −0.046176 |
| 67 | 0.038543 | 0.089474 | 0.018067 | 0.025072 | 0.018695 | −0.021352 | 0.025528 | 0.031472 | 0.042602 | 0.053656 | 0.042901 | 0.007876 | 0.008739 | 0.035095 |
| 68 | −0.028535 | 0.033125 | −0.063124 | −0.045537 | 0.058851 | 0.040353 | 0.030793 | 0.047682 | −0.020329 | −0.079973 | −0.042087 | −0.030335 | 0.061535 | 0.010334 |
| 69 | −0.117609 | 0.016322 | 0.002915 | 0.061573 | 0.015826 | 0.017409 | −0.012293 | −0.026869 | 0.001664 | 0.001568 | 0.004422 | 0.091919 | −0.133371 | −0.077441 |
| 70 | −0.048764 | 0.061867 | 0.006952 | −0.07298 | 0.065126 | 0.08866 | 0.006086 | −0.012562 | −0.067104 | −0.010392 | −0.044519 | −0.011237 | 0.128757 | −0.018882 |
| 71 | 0.098386 | 0.052092 | −0.055674 | −0.015587 | −0.097391 | −0.06555 | −0.116468 | −0.044891 | −0.074973 | −0.02417 | 0.02296 | −0.066024 | 0.11863 | −0.040542 |
| 72 | −0.081025 | −0.10537 | 0.089444 | −0.016409 | 0.049536 | 0.036467 | 0.037979 | −0.003873 | 0.041873 | −0.0135 | −0.044156 | −0.084504 | −0.084896 | 0.055013 |
| 73 | −0.085038 | 0.012516 | −0.018178 | 0.091557 | 0.008484 | −0.009507 | 0.02429 | 0.060076 | −0.006642 | 0.007642 | 0.024305 | 0.027484 | −0.072064 | −0.041075 |
| 74 | −0.004395 | −0.064422 | 0.0315631 | 0.021008 | 0.017065 | −0.019232 | −0.040996 | 0.007127 | −0.017072 | −0.021617 | −0.003287 | −0.049683 | 0.02522 | 0.010824 |
| 75 | 0.042015 | 0.059405 | 0.095605 | −0.076671 | 0.011925 | −0.048954 | 0.001626 | 0.037674 | 0.02321 | 0.000282 | −0.093229 | 0.077921 | −0.062539 | −0.050423 |
| 76 | −0.097421 | −0.071417 | 0.023708 | 0.085284 | 0.017062 | 0.04229 | 0.011337 | −0.022946 | −0.012371 | 0.01965 | 0.016836 | 0.010931 | 0.061901 | 0.02182 |
| 77 | −0.086331 | 0.011802 | 0.125452 | −0.019044 | 0.024653 | −0.011685 | 0.009642 | 0.071731 | 0.102243 | −0.042279 | 0.004537 | −0.069318 | 0.057384 | −0.016892 |
| 78 | 0.1051331 | −0.051825 | −0.154693 | 0.083954 | −0.03531 | −0.03573 | 0.021273 | −0.004826 | 0.0290911 | 0.1162981 | −0.009296 | −0.053368 | −0.113694 | 0.061855 |
| 79 | −0.040583 | −0.065058 | 0.008893 | −0.012546 | −0.027435 | −0.028399 | −0.009864 | −0.038987 | −0.025721 | −0.063253 | 0.002487 | −0.005864 | 0.020967 | 0.032298 |
| 80 | −0.075007 | 0.001462 | −0.035945 | −0.007089 | −0.035647 | −0.049072 | −0.011919 | −0.004096 | −0.025111 | −0.117571 | −0.187261 | 0.042111 | 0.018551 | 0.041719 |
| 81 | 0.08139 | 0.040038 | −0.04955 | 0.096085 | 0.005234 | −0.040721 | 0.062345 | 0.012725 | 0.005487 | −0.009431 | 0.037216 | 0.051606 | 0.025395 | 0.003478 |
| 82 | 0.0289171 | 0.04326 | −0.073414 | 0.043853 | −0.045183 | −0.002812 | −0.044853 | 0.008834 | 0.034702 | 0.017849 | −0.018291 | −0.118683 | 0.063825 | −0.080748 |
| 83 | −0.057462 | 0.014478 | 0.128732 | 0.379066 | 0.071132 | 0.056215 | 0.082961 | 0.001411 | −0.060865 | 0.005632 | 0.035102 | 0.010191 | 0.170552 | 0.000725 |
| 84 | −0.007277 | 0.073716 | 0.095077 | −0.144184 | 0.046409 | 0.017706 | 0.059307 | 0.037535 | −0.077471 | 0.089121 | −0.054797 | 0.103972 | −0.151884 | 0.019189 |
| 85 | −0.032733 | 0.013867 | −0.004511 | −0.158388 | −0.02818 | −0.023517 | −0.018763 | −0.027484 | 0.010564 | −0.01263 | 0.061012 | −0.068565 | −0.022602 | 0.03198 |
| 86 | −0.120749 | 0.074133 | 0.030681 | −0.057588 | 0.030344 | 0.055422 | 0.038589 | 0.037517 | 0.025455 | 0.003309 | −0.047127 | 0.097457 | 0.148618 | 0.014418 |
| 87 | 0.185392 | −0.023282 | −0.009041 | −0.061918 | −0.054217 | −0.029479 | −0.042622 | −0.071738 | −0.024594 | 0.005105 | 0.064188 | 0.000673 | 0.116386 | −0.034541 |
| 88 | 0.126419 | 0.003041 | 0.066947 | −0.045436 | 0.00453 | 0.030002 | 0.044275 | 0.003062 | 0.132807 | −0.073404 | −0.109395 | −0.059634 | −0.069835 | −0.064885 |
| 89 | 0.031194 | 0.064827 | 0.068392 | −0.020333 | −0.030861 | −0.001948 | −0.00884 | −0.05428 | 0.00128 | −0.050462 | −0.063861 | 0.008513 | 0.0943 | 0.060438 |
| 90 | −0.170928 | −0.010131 | −0.187601 | −0.028294 | −0.021431 | −0.019747 | −0.073217 | 0.000853 | 0.069988 | 0.041816 | 0.019952 | −0.048272 | 0.023654 | 0.023841 |
| 91 | 0.055137 | −0.036451 | −0.080326 | 0.066805 | 0.026105 | −0.020555 | 0.013479 | 0.04776 | 0.009345 | 0.008307 | −0.016692 | 0.020933 | −0.182468 | 0.018717 |
| 92 | 0.043617 | 0.049407 | −0.010007 | 0.023695 | −0.083093 | −0.060798 | −0.115508 | −0.041007 | −0.026799 | −0.044156 | −0.005182 | −0.004166 | 0.051092 | −0.00244 |
| 93 | 0.095439 | 0.041596 | −0.088051 | −0.003424 | −0.026007 | −0.055047 | −0.038779 | 0.008329 | −0.029767 | 0.009448 | 0.072898 | 0.093358 | −0.000501 | 0.003116 |
| 94 | −0.055306 | 0.018616 | 0.021872 | 0.081257 | 0.006452 | −0.038625 | 0.014252 | −0.040154 | −0.054664 | 0.016712 | 0.098985 | −0.009032 | −0.007512 | 0.014719 |
| 95 | −0.050813 | 0.008561 | 0.002684 | 0.093794 | −0.021536 | −0.026837 | −0.037109 | −0.041724 | −0.022066 | 0.054887 | 0.053577 | −0.024395 | −0.12027 | −0.012368 |
| 96 | −0.075936 | −0.050752 | 0.053493 | −0.134649 | −0.007313 | −0.012326 | 0.015083 | 0.095901 | 0.052064 | 0.031872 | 0.076524 | 0.043015 | −0.055879 | 0.03736 |
| 97 | −0.085046 | 0.00835 | −0.001245 | 0.010631 | 0.041186 | 0.055907 | 0.039306 | −0.029309 | −0.035595 | −0.015465 | −0.053386 | −0.051596 | −0.062889 | −0.09434 |
| 98 | 0.021513 | 0.038932 | −0.0066761 | −0.000911 | 0.027988 | −0.008117 | 0.075158 | 0.012369 | 0.044634 | 0.037547 | 0.085055 | 0.054853 | 0.07771 | −0.084667 |
| 99 | 0.061403 | 0.053584 | −0.036035 | 0.007154 | −0.017307 | −0.055977 | −0.00101 | −0.050913 | −0.005338 | −0.034364 | 0.047484 | −0.025473 | 0.001644 | 0.048523 |
| 100 | 0.035725 | 0.047571 | 0.021763 | −0.027048 | −0.000994 | 0.022743 | −0.02221 | −0.031471 | −0.015268 | 0.007783 | 0.022328 | −0.026122 | 0.068191 | −0.054297 |
| 101 | 0.030348 | −0.013946 | −0.001001 | 0.028402 | −0.032193 | −0.036382 | −0.015913 | 0.012282 | 0.022406 | 0.02276 | 0.025266 | 0.004188 | 0.018368 | −0.062033 |
| 102 | −0.019227 | 0.028736 | 0.017247 | 0.049084 | 0.034319 | 0.038176 | 0.052667 | −0.035185 | −0.047381 | −0.04428 | −0.023372 | −0.05343 | −0.002636 | 0.010244 |
| 103 | 0.006005 | −0.036623 | −0.023012 | −0.004467 | 0.002332 | 0.012529 | −0.001402 | −0.003856 | 0.002344 | 0.029357 | 0.025177 | −0.011989 | −0.030077 | −0.0205 |
| 104 | −0.022851 | 0.042379 | −0.088304 | 0.052741 | 0.01083 | 0.030793 | 0.027077 | 0.001975 | 0.018194 | 0.005827 | 0.004764 | 0.014548 | 0.017821 | −0.003903 |
| 105 | −0.027751 | 0.035614 | −0.004221 | 0.035143 | 0.004414 | 0.012922 | −0.013629 | −0.026786 | −0.022833 | 0.025398 | −0.002354 | −0.017062 | 0.034988 | −0.005205 |
| 106 | 0.021677 | −0.015703 | −0.042253 | −0.004678 | −0.042277 | −0.029076 | −0.018318 | −0.042999 | −0.021598 | −0.036117 | 0.02357 | −0.0332 | −0.04465 | −0.027567 |
| 107 | 0.000208 | −0.017317 | 0.01264 | −0.020352 | 0.025249 | −0.003593 | −0.007213 | 0.039833 | 0.059548 | 0.038227 | 0.016681 | −0.048987 | 0.005369 | 0.001029 |
| 108 | 0.039942 | −0.035773 | −0.038442 | 0.015566 | 0.009812 | 0.036147 | 0.005773 | −0.02757 | −0.001749 | 0.041341 | 0.032614 | −0.009494 | 0.031338 | 0.025079 |
| 109 | 0.003306 | −0.043506 | −0.012337 | −0.010082 | 0.030097 | 0.039819 | 0.028097 | 0.024941 | −0.009747 | 0.009492 | 0.000711 | 0.04353 | 0.048388 | 0.016405 |
| 110 | 0.001432 | 0.010969 | 0.009761 | 0.025998 | −0.017849 | −0.016188 | −0.019287 | 0.008388 | 0.023768 | −0.012283 | 0.045452 | 0.020078 | 0.058738 | −0.008319 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 111 | 0.027189 | 0.045912 | −0.013392 | 0.060821 | 0.022005 | 0.040124 | 0.023862 | 0.012849 | −0.007175 | 0.006618 | −0.010236 | −0.016911 | 0.01577 | 0.000565 |
| 112 | 0.030234 | −0.066562 | −0.021456 | 0.063302 | −0.020561 | −0.012921 | 0.018129 | −0.022732 | 0.00813 | 0.033065 | 0.021982 | −0.000889 | 0.037205 | −0.0093 |
| 113 | 0.030484 | 0.023844 | −0.054493 | −0.01879 | 0.025275 | 0.013154 | 0.030911 | −0.004276 | 0.004603 | 0.004052 | −0.062578 | 0.009056 | 0.006962 | 0.046122 |
| 114 | 0.030274 | −0.01812 | −0.024713 | 0.034831 | −0.001104 | 0.001213 | −0.008894 | −0.027417 | 0.000732 | 0.03367 | 0.041394 | 0.045414 | 0.063836 | 0.022134 |
| 115 | 0.033238 | 0.008366 | −0.0105991 | −0.011973 | 0.046484 | 0.04649 | 0.030557 | −0.010344 | −0.046079 | −0.033858 | −0.038313 | 0.036904 | 0.000495 | 0.012005 |
| 116 | 0.042125 | 0.049412 | 0.04828 | −0.030055 | −0.010347 | −0.030549 | −0.017545 | −0.012476 | −0.003447 | −0.017128 | 0.016879 | 0.002267 | 0.022806 | 0.037266 |
| 117 | 0.0264 | −0.026961 | 0.02684 | 0.018904 | −0.009983 | −0.007538 | −0.025518 | −0.015369 | −0.033904 | −0.001731 | −0.040036 | −0.011465 | −0.030396 | 0.037796 |
| 118 | −0.008711 | −0.011725 | 0.014147 | 0.008882 | 0.00525 | 0.034784 | 0.002296 | 0.005575 | 0.013118 | −0.005815 | −0.103609 | 0.003317 | 0.003915 | −0.008783 |
| 119 | 0.0136 | −0.038293 | −0.027952 | −0.001733 | −0.006121 | −0.012675 | −0.008836 | −0.029059 | 0.00562 | 0.007833 | −0.025344 | 0.002778 | −0.014019 | 0.009132 |
| 120 | 0.031677 | −0.008702 | −0.022943 | −0.008262 | −0.017188 | −0.011569 | −0.029651 | −0.03954 | −0.014221 | 0.01226 | −0.006102 | −0.034938 | −0.009443 | 0.014238 |
| 121 | 0.045814 | −0.002101 | 0.017602 | 0028869 | −0.027634 | −0.024896 | −0.057375 | −0.037312 | −0.017258 | −0.021218 | 0.021583, | −0.036992 | 0.041787 | 0.000983 |
| 122 | −0.029714 | −0.009081 | −0.063265 | 0.013953 | 0.019129 | 0.025383 | 0.007889 | 0.041364 | 0.021564 | 0.030629 | −0.002584 | 0.002429 | −0.010723 | 0.003592 |
| 123 | 0.015007 | 0.000766 | 0.00406 | −0.000891 | 0.013478 | 0.015203 | −0.029748 | 0.020332 | 0.021839 | 0.019243 | 0.008948 | −0.013259 | 0.036063 | 0.011826 |
| 124 | 0.015494 | −0.0467471 | −0.0089941 | 0.008852 | −0.011517 | −0.015126 | −0.006051 | −0.04528 | 0.0147871 | −0.011124 | −0.012561 | −0.058608 | −0.014055 | −0.011141 |
| 125 | −0.026204 | 0.0149971 | 0.0156591 | −0.024264 | 0.025208 | 0.030489 | 0.03696 | 0.012507 | −0.007316 | 0.027251 | 0.0274851 | 0.0319771 | 0.0268271 | 0.015108 |
| 126 | −0.007091 | 0.01804 | 0.019026 | −0.03634 | 0.009687 | 0.014894 | 0.005503 | 0.017395 | 0.015888 | −0.002465 | 0.010382 | 0.007547 | 0.02094 | 0.017918 |
| 127 | −0.020288 | 0.007089 | 0.000896 | −0.010506 | 0.002593 | 0.0048 | 0.008165 | 0.020997 | −0.002826 | 0.0069 | 0.017537 | 0.016628 | 0.01585 | 0.015451 |
| 128 | −0.023897 | 0.060231 | −0.010695 | −0.030857 | 0.019401 | 0.006953 | 0.020577 | −0.009522 | −0.02201 | 0.010468 | 0.02408 | 0.036996 | −0.02846 | 0.006056 |
| 129 | −0.064845 | −0.066098 | −0.008627 | −0.046854 | −0.025264 | −0.027539 | −0.023498 | 0.002777 | −0.017812 | 0.002457 | −0.04487 | 0.045662 | 0.039112 | −0.007924 |
| 130 | 0.031751 | −0.044198 | −0.006396 | −0.049786 | −0.001086 | −0.022799 | 0.016477 | −0.010436 | 0.008852 | −0.024312 | −0.009344 | −0.000467 | 0.022642 | −0.011604 |
| 131 | 0.069515 | 0.018131 | 0.090833 | 0.008366 | −0.015581 | −0.023331 | −0.017066 | 0.003925 | 0.015948 | 0.022947 | 0.008239 | −0.03017 | 0.041236 | −0.000535 |
| 132 | −0.009681 | 0.038284 | −0.044058 | 0.06546 | 0.011266 | −0.021323 | 0.006904 | 0.036969 | 0.082019 | 0.013306 | 0.019583 | −0.006976 | 0.028071 | 0.049377 |
| 133 | −0.038391 | −0.037401 | 0.001013 | −0.022985 | −0.01691 | −0.001093 | −0.016193 | −0.011528 | −0.034058 | −0.013739 | 0.037047 | −0.015867 | 0.057154 | −0.004153 |
| 134 | −0.003941 | 0.049336 | 0.043691 | 0.00473 | 0.003161 | 0.000179 | −0.012855 | 0.019543 | 0.008621 | −0.009486 | −0.001647 | 0.046546 | 0.009702 | 0.026126 |
| 135 | 0.022365 | −0.006491 | −0.0345221 | −0.018307 | −0.019151 | 0.001622 | 0.004762 | −0.029622 | 0.0003291 | −0.008346 | 0.0023021 | 0.0020471 | −0.031535 | −0.011296 |
| 136 | 0.037247 | 0.003523 | −0.050925 | −0.001346 | 0.004226 | 0.00547 | 0.015383 | −0.024112 | 0.01415 | −0.006055 | 0.020231 | −0.032282 | 0.009838 | 0.020503 |
| 137 | 0.021422 | 0.037782 | −0.023829 | −0.021047 | 0.008024 | −0.000797 | 0.019277 | 0.030181 | −0.014787 | 0.037598 | 0.016613 | 0.013159 | 0.037139 | −0.041393 |
| 138 | 0.035654 | −0.075906 | −0.047877 | −0.029006 | 0.004868 | −0.000652 | 0.012018 | 0.022296 | 0.027257 | 0.015034 | 0.019482 | 0.011732 | 0.00389 | −0.018918 |
| 139 | 0.041271 | 0.05164 | −0.014291 | −0.008499 | −0.023652 | −0.010327 | −0.053422 | −0.034381 | −0.025347 | −0.016165 | −0.034501 | −0.003751 | −0.036705 | −0.037345 |
| 140 | 0.04645 | −0.024771 | 0.005275 | 0.015593 | 0.003118 | 0.016089 | −0.01664 | 0.004487 | −0.027608 | −0.032702 | −0.008952 | −0.014896 | 0.0212421 | 0.026262 |
| 141 | −0.01549 | 0.0095891 | −0.0711081 | −0.017492 | −0.004797 | 0.013775 | −0.034889 | −0.028805 | −0.01959 | −0.01895 | 0.007343 | −0.037184 | 0.077877 | −0.012099 |
| 142 | 0.050272 | −0.01787 | 0.052756 | −0.007231 | 0.014397 | 0.022703 | 0.002716 | 0.036779 | 0.031549 | −0.011451 | 0.023186 | 0.051519 | 0.067244 | −0.00099 |
| 143 | −0.021187 | 0.013305 | −0.059804 | −0.041821 | −0.016393 | 0.009388 | −0.025221 | −0.021787 | 0.018503 | −0.001936 | −0.004753 | −0.074666 | −0.002577 | −0.04125 |
| 144 | −0.054522 | −0.002001 | −0.065342 | −0.00081 | −0.006133 | −0.019438 | −0.003451 | −0.027487 | −0.009701 | 0.000643 | 0.040415 | 0.007548 | −0.023789 | 0.003453 |
| 145 | −0.0364861 | 0.00146 | −0.0566191 | −0.040207 | 0.022066 | 0.031418 | 0.033596 | 0.013062 | 0.012921 | 0.0214471 | 0.0152891 | 0.0019341 | 0.0216631 | −0.007657 |
| 146 | −0.0090981 | 0.0108831 | −0.0191941 | −0.025929 | −0.010343 | −0.001752 | −0.007684 | −0.004387 | −0.006863 | 0.01941 | 0.033565 | 0.019446 | 0.007656 | 0.016346 |
| 147 | 0.025529 | 0.05836 | 0.010933 | 0.006869 | 0.006307 | 0.000819 | 0.002175 | 0.001048 | 0.013058 | 0.012115 | 0.022956 | 0.042323 | −0.036202 | −0.001038 |
| 148 | −0.023554 | −0.035805 | 0.006646 | 0.026284 | 0.012586 | 0.003807 | 0.037043 | 0.006137 | −0.001989 | −0.027114 | 0.000993 | 0.003796 | −0.063237 | −0.035473 |
| 149 | −0.038881 | 0.022351 | −0.032787 | 0.016228 | −0.019955 | −0.019271 | −0.019525 | −0.006868 | −0.017641 | −0.000601 | −0.033671 | −0.003926 | −0.007579 | 0.006776 |
| 150 | 0.044724 | 0.003222 | −0.029666 | −0.008853 | 0.020248 | 0.007543 | 0.03662 | 0.011318 | 0.038101 | 0.027975 | −0.070442 | −0.009113 | 0.0086271 | 0.006218 |
| 151 | −0.036903 | −0.025142 | 0.031217 | −0.017442 | 0.042008 | 0.039135 | 0.01422 | −0.035664 | −0.00206 | −0.038758 | −0.029738 | −0.004176 | −0.030965 | 0.005964 |
| 152 | −0.023088 | 0.025861 | 0.004519 | 0.015395 | 0.004155 | −0.011024 | −0.001999 | 0.013199 | 0.018722 | −0.018038 | −0.027083 | −0.005078 | 0.01192 | −0.014457 |
| 153 | −0.061478 | −0.000715 | −0.038625 | 0.011612 | 0.010127 | −0.008003 | −0.015272 | 0.010137 | −0.002324 | 0.001343 | 0.018103 | −0.002521 | 0.010999 | 0.001941 |
| 154 | −0.029857 | 0.027621 | 0.032509 | 0.027395 | 0.033441 | −0.006057 | 0.048878 | 0.039675 | 0.033679 | −0.011986 | 0.012786 | 0.042831 | −0.025291 | 0.015408 |
| 155 | −0.1058731 | 0.047477 | −0.03337 | 0.091648 | −0.005269 | −0.016782 | 0.005045 | 0.003464 | 0.0023911 | −0.019312 | −0.016357 | 0.018931 | 0.0458451 | 0.027365 |
| 156 | 0.0730171 | 0.010942 | −0.029943 | 0.000743 | 0.008987 | 0.010804 | −0.010335 | 0.021165 | 0.01529 | 0.00825 | 0.033766 | 0.028426 | 0.03067 | 0.061197 |
| 157 | −0.012984 | −0.012586 | −0.019087 | −0.060682 | 0.017527 | 0.043119 | 0.024431 | 0.003868 | 0.00329 | 0.018689 | −0.074029 | −0.003222 | 0.035989 | −0.012681 |
| 158 | 0.007902 | 0.032703 | −0.04375 | 0.03796 | 0.000597 | −0.017093 | −0.003764 | −0.00979 | 0.001817k | −0.001154 | 0.035071 | −0.036516 | −0.1064 | −0.026573 |
| 159 | 0.050906 | 0.0241191 | 0.022721 | 0.004089 | −0.005678 | −0.013879 | −0.014462 | 0.004366 | 0.013788 | 0.011937 | 0.05634 | −0.011023 | −0.026981 | −0.000847 |
| 160 | 0.0234811 | −0.0919811 | −0.006597 | 0.052109 | 0.01132 | 0.002607 | −0.001836 | 0.003975 | 0.0368471 | 0.0420451 | −0.025583 | −0.001548 | 0.0693841 | 0.019875 |
| 161 | −0.0042571 | 0.079983 | 0.0376961 | −0.032382 | 0.003551 | −0.00459 | −0.014422 | −0.025715 | −0.037285 | −0.085929 | −0.047879 | −0.019401 | −0.046782 | −0.009813 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 162 | −0.009358 | −0.020797 | 0.020086 | 0.011813 | 0.005167 | 0.018344 | 0.019265 | −0.005619 | −0.036528 | 0.055098 | −0.03742 | 0.033892 | −0.0201 | −0.056028 |
| 163 | 0.030648 | 0.039841 | −0.014275 | −0.070722 | −0.014122 | 0.014679 | −0.01274 | 0.00012 | 0.01965 | 0.005394 | 0.010978 | −0.012442 | 0.042376 | −0.014272 |
| 164 | −0.048853 | −0.031154 | −0.005963 | −0.02925 | 0.004588 | −0.003853 | 0.01632 | −0.002402 | −0.00929 | 0.012377 | 0.036179 | 0.014138 | −0.050209 | 0.026489 |
| 165 | 0.41578 | −0.043302 | 0.025813 | 0.014252 | 0.003025 | −0.022188 | 0.001332 | 0.01287 | −0.011519 | −0.006849 | −0.023039 | −0.046139 | −0.024864 | −0.004426 |
| 166 | −0.020712 | 0.600804 | −0.026963 | 0.053944 | −0.018289 | −0.012088 | −0.002449 | −0.018735 | 0.030765 | 0.009851 | −0.013482 | −0.032235 | −0.049845 | 0.01174 |
| 167 | 0.011994 | −0.031004 | 0.598387 | 0.035232 | −0.041733 | −0.012047 | −0.027792 | −0.035145 | 0.008153 | 0.011978 | 0.06369 | −0.069148 | −0.035962 | 0.007815 |
| 168 | 0.016435 | 0.051263 | 0.018805 | 0.583155 | −0.031854 | −0.018453 | −0.059352 | 0.005493 | 0.016318 | −0.0417 | −0.05364 | −0.015895 | −0.052082 | 0.003789 |
| 169 | 0.027014 | −0.006008 | −0.009411 | −0.042448 | 0.861269 | −0.130416 | −0.116166 | −0.071862 | −0.020597 | −0.011136 | −0.023 | −0.061893 | −0.026271 | −0.016271 |
| 170 | 0.009657 | −0.005765 | 0.020784 | −0.022514 | −0.121313 | 0.822687 | −0.102145 | −0.030484 | 0.003458 | 0.008314 | 0.000543 | −0.031251 | −0.077226 | 0.004315 |
| 171 | 0.022205 | 0.005948 | −0.005225 | −0.076761 | −0.11241 | −0.107104 | 0.842289 | −0.064658 | −0.027394 | −0.01934 | −0.013185 | −0.069324 | 0.009114 | −0.009336 |
| 172 | 0.026115 | 0.013338 | 0.0020061 | −0.010015 | −0.071681 | −0.037682 | −0.056232 | 0.833346 | −0.107788 | −0.060371 | −0.054508 | −0.075917 | 0.024688 | −0.014334 |
| 173 | −0.046742 | 0.01541 | 0.027936 | −0.005637 | −0.024776 | −0.003293 | −0.028059 | −0.095752 | 0.808616 | −0.072286 | −0.056529 | 0.015034 | 0.043987 | −0.004679 |
| 174 | 0.030391 | 0.01774 | 0.04338 | −0.03176 | −0.023472 | −0.021744 | −0.020766 | −0.061948 | −0.077653 | 0.79495 | −0.136653 | −0.000126 | 0.020189 | 0.014979 |
| 175 | −0.018513 | 0.006303 | 0.041014 | −0.048388 | −0.001967 | −0.000632 | −0.003731 | −0.031431 | −0.04508 | −0.134272 | 0.630686 | −0.049817 | 0.004639 | 0.000818 |
| 176 | −0.013877 | −0.01594 | −0.050004 | −0.050939 | −0.055873 | −0.04326 | −0.076746 | −0.068819 | 0.006783 | −0.024536 | −0.042408 | 0.75806 | 0.027248 | −0.02353 |
| 177 | 0.019328 | −0.068533 | −0.057061 | −0.011692 | −0.020049 | −0.054716 | 0.015515 | 0.003713 | 0.041649 | 0.017527 | 0.041572 | −0.001518 | 0.413956 | −0.007371 |
| 178 | 0.005989 | 0.004192 | −0.003292 | −0.015678 | −0.024244 | 0.010937 | −0.023783 | −0.020112 | −0.002739 | −0.010356 | −0.024632 | −0.029262 | −0.008875 | 0.830762 |
| 179 | 0.027539 | 0.004073 | −0.009071 | −0.042651 | −0.031006 | −0.029605 | −0.042805 | 0.02565 | 0.044754 | 0.009886 | 0.006695 | −0.003094 | −0.02422 | −0.053668 |
| 180 | 0.030404 | −0.014219 | −0.008853 | 0.026132 | −0.017591 | −0.018228 | −0.012485 | 0.021476 | 0.004432 | 0.026652 | 0.029325 | 0.021737 | −0.000155 | −0.07464 |
| 181 | 0.016865 | −0.015925 | −0.027576 | 0.037514 | −0.014423 | −0.026586 | −0.01343 | 0.033103 | 0.0179171 | 0.02293 | 0.014273 | 0.015266 | −0.007627 | −0.059804 |
| 182 | 0.024808 | 0.014584 | 0.0222711 | −0.002078 | 0.009238 | −0.032336 | 0.002961 | 0.036825 | 0.018075 | 0.022836 | −0.019265 | 0.026839 | −0.028872 | −0.028277 |
| 183 | 0.004899 | 0.054852 | 0.017729 | −0.087522 | 0.003421 | −0.013073 | −0.053406 | 0.0297 | 0.033843 | 0.030534 | 0.006233 | −0.005185 | −0.032566 | 0.005475 |
| 184 | −0.035056 | 0.029969 | 0.016386 | −0.10491 | −0.001951 | 0.018215 | −0.069658 | −0.008542 | 0.013365 | 0.002984 | 0.045035 | −0.029771 | 0.052081 | 0.009526 |
| 185 | 0.066303 | −0.020992 | 0.027124 | 0.048956 | 0.013185 | 0.048252 | 0.031439 | −0.030758 | −0.010918 | −0.031467 | −0.023647 | 0.013594 | 0.038074 | −0.032036 |
| 186 | 0.00844 | −0.031268 | 0.028464 | −0.026737 | 0.009719 | −0.003201 | −0.026643 | −0.038054 | −0.060361 | −0.039215 | 0.027954 | 0.015652 | 0.034795 | 0.0201 |
| 187 | −0.032992 | 0.029754 | 0.020286 | 0.024965 | 0.02717 | 0.033119 | 0.052562 | −0.03009 | −0.085867 | −0.012491 | 0.017744 | 0.026392 | 0.016979 | 0.014403 |
| 188 | −0.002171 | 0.033464 | 0.012739 | 0.025824 | 0.021122 | 0.022613 | 0.043448 | −0.034082 | −0.051771 | −0.079639 | −0.01486 | 0.00472 | 0.017513 | 0.01978 |
| 189 | 0.05253 | 0.037578 | 0.019075 | 0.013232 | 0.016023 | 0.010258 | 0.026731 | 0.000906 | 0.000932 | −0.086281 | −0.058928 | −0.021144 | 0.052764 | 0.03587 |
| 190 | −0.00194 | 0.015187 | −0.025318 | −0.018454 | −0.023096 | −0.036185 | −0.038193 | −0.013731 | 0.000697 | 0.008799 | −0.027028 | −0.048751 | 0.020105 | 0.006476 |
| 191 | 0.034397 | −0.012544 | −0.019725 | 0.008761 | −0.034856 | −0.038247 | −0.02635 | 0.000354 | 0.017541 | −0.010653 | −0.016974 | 0.006632 | −0.009734 | 0.029098 |
| 192 | 0.04856 | 0.0144 | 0.005701 | −0.048187 | 0.030133 | 0.010909 | 0.024286 | 0.011634 | 0.021526 | −0.044739 | −0.036572 | 0.03085 | 0.008438 | 0.029783 |
| 193 | 0.067309 | 0.036464 | 0.064597 | −0.025072 | 0.025125 | −0.002445 | 0.012681 | −0.014452 | −0.026346 | −0.020351 | −0.034862 | 0.029549 , | −0.00891 | 0.013549 |
| 194 | −0.00403 | −0.004705 | −0.006134 | −0.007511 | 0.012628 | 0.020057 | 0.008815 | 0.00725 | 0.01117 | −0.001599 | −0.062839 | −0.071697 | −0.02291 | −0.01587 |
| 195 | 0.032265 | −0.044173 | −0.034882 | 0.036755 | 0.017452 | 0.008222 | 0.02749 | 0.016895 | 0.002634 | 0.025439 | 0.002339 | 0.007041 | −0.002585 | 0.031153 |
| 196 | 0.021423 | −0.024731 | −0.02662 | 0.014495 | −0.009295 | 0.001699 | −0.000068 | −0.014136 | −0.002294 | −0.001103 | −0.038561 | −0.00549 | 0.014065 | −0.011595 |
| 197 | −0.02681 | 0.053614 | −0.02861 | 0.007723 | −0.026239 | −0.048918 | −0.019386 | −0.007737 | 0.007074 | −0.005662 | 0.0068 | −0.009183 | 0.035518 | 0.041504 |
| 198 | −0.034191 | 0.029064 | 0.030187 | −0.061043 | 0.011908 | 0.005348 | 0.00208 | −0.031357 | 0.01409 | 0.017249 | −0.006147 | −0.026659 | −0.046065 | −0.038961 |
| 199 | −0.040428 | −0.004848 | −0.027204 | 0.019764 | 0.007385 | 0.011126 | 0.00354 | 0.000429 | −0.020264 | −0.014518 | −0.035192 | 0.013127 | 0.034223 | 0.013664 |
| 200 | 0.028351 | −0.006956 | 0.002462 | 0.036018 | 0.023671 | 0.036533 | 0.022119 | −0.047404 | −0.024316 | −0.024309 | −0.016531 | 0.03584 | −0.0356 | −0.044469 |
| 201 | −0.01428 | 0.000606 | 0.003275 | 0.055672 | 0.001732 | −0.005001 | −0.000617 | 0.03716 | 0.017089 | 0.054038 | 0.069174 | −0.041667 | 0.007022 | 0.000166 |
| 202 | −0.040747 | −0.032261 | 0.007188 | −0.001595 | 0.001254 | −0.01457 | 0.000331 | −0.063982 | −0.044062 | −0.031775 | −0.026887 | 0.029099 | 0.035735 | −0.015088 |
| 203 | −0.009578 | 0.040289 | 0.027336 | −0033921 | −0.025547 | −0.026028 | −0.012844 | −0.012212 | 0.012294 | 0.007316 | 0.016214 | 0.012746 | −0.094453 | −0.021323 |
| 204 | −0.089844 | 0.077026 | 0.0096 | 0.018649 | −0.000718 | −0.002587 | 0.018469 | −0.018774 | 0.009039 | 0.029574 | 0.000385 | −0.020909 | 0.035803 | −0.017398 |
| 205 | −0.025952 | 0.010242 | 0.014352 | −0.041241, | 0.019054 | 0.012917 | 0.015216 | −0.007192 | −0.019499 | −0.001761 | 0.010807 | −0.021258 | −0.005714 | 0.035531 |
| 206 | 0.086143 | 0.007455 | 0.001557 | −0.031127 | 0.005948 | 0.010926 | −0.002324 | −0.020093 | 0.016208 | −0.020024 | 0.002625 | 0.026088 | 0.021813 | −0.01643 |
| 207 | −0.068496 | 0.045626 | 0.010949 | 0.017199 | −0.032364 | −0.027168 | −0.038811 | −0.017353 | −0.026155 | −0.017909 | −0.058369 | 0.002929 | −0.033873 | −0.00087 |
| 208 | −0.04084 | 0.010566 | 0.012666 | −0.031891 | −0.025874 | −0.033685 | −0.013862 | −0.029958 | −0.04257 | −0.017677 | 0.007466 | −0.013376 | 0.003245 | 0.011148 |
| 209 | −0.015806 | −0.063306 | 0.050771 | −0.003158 | −0.009251 | −0.003802 | −0.037678 | −0.044757 | −0.01674 | −0.02773 | −0.042612 | −0.044622 | −0.012256 | −0.014063 |
| 210 | −0.066123 | −0.002553 | 0.007121 | 0.064217 | 0.009741 | 0.011314 | 0.017962 | 0.02082 | −0.003483 | 0.046066 | −0.015334 | 0.010555 | −0.06642 | −0.034725 |
| 211 | −0.006052 | −0.026782 | 0.043289 | 0.025009 | −0.020174 | 0.020581 | −0.006052 | −0.087055 | −0.094061 | −0.005626 | 0.013237 | 0.011018 | −0.057423 | −0.038112 |
| 212 | −0.024001 | −0.043949 | −0.00241 | 0.037424 | −0.01945 | −0.029716 | −0.032403 | −0.025513 | 0.007324 | 0.009397 | −0.009635 | −0.011838 | −0.021089 | 0.028838 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 213 | −0.015933 | −0.031188 | −0.006184 | −0.002141 | 0.013616 | 0.029903 | −0.003946 | −0.007961 | −0.011006 | −0.03359 | 0.014676 | 0.013097 | 0.03842 | −0.02706 |
| 214 | 0.049339 | −0.014259 | 0.009099 | −0.026985 | −0.014108 | 0.002441 | −0.033032 | 0.021733 | 0.028172 | 0.021274 | 0.037813 | −0.006688 | 0.025657 | −0.055204 |
| 215 | −0.058754 | −0.000855 | 0.04111 | 0.015677 | 0.017524 | 0.032342 | 0.005926 | 0.024005 | −0.012875 | 0.016387 | −0.007881 | 0.022493 | 0.017281 | −0.062975 |
| 216 | −0.001143 | 0.011133 | −0.026801 | −0.114802 | −0.042115 | −0.017873 | −0.042041 | −0.019782 | −0.035018 | −0.038508 | −0.050142 | −0.021953 | 0.027459 | 0.003586 |
| 217 | 0.045894 | 0.07674 | 0.030203 | −0.001055 | −0.019065 | −0.0116 | −0.006813 | −0.041826 | −0.012233 | −0.007521 | −0.02096 | 0.007976 | 0.01305 | 0.041975 |
| 218 | 0.026561 | 0.012134 | 0.024678 | 0.011963 | −0.012178 | −0.016471 | −0.019577 | −0.007973 | −0.043883 | −0.015318 | −0.007258 | 0.012023 | 0.017457 | −0.001985 |
| 219 | 0.031998 | −0.015035 | 0.016061 | 0.005648 | −0.03269 | −0.031911 | −0.042786 | −0.011393 | −0.028541 | −0.025958 | −0.003185 | 0.008893 | 0.000196 | 0.014417 |
| 220 | 0.010862 | 0.018244 | 0.055978 | 0.044507 | −0.014706 | −0.024334 | −0.009393 | −0.03449 | 0.00145 | −0.002081 | 0.034594 | 0.006469 | −0.016552 | 0.047534 |
| 221 | −0.022375 | 0.011462 | 0.024996 | −0.004741 | −0.002353 | 0.013365 | −0.003934 | −0.009469 | −0.044704 | −0.013975 | −0.009279 | 0.001757 | 0.024288 | −0.018119 |
| 222 | −0.016498 | 0.024505 | −0.050175 | −0.016023 | 0.008567 | 0.024902 | 0.003117 | −0.009552 | −0.048212 | −0.017124 | −0.021786 | 0.020071 | 0.014439 | −0.018337 |
| 223 | −0.013812 | −0.000165 | −0.027641 | −0.011529 | −0.001733 | 0.001747 | −0.017527 | −0.005047 | −0.027905 | −0.012595 | −0.042702 | −0.025759 | 0.013656 | −0.009403 |
| 224 | −0.015805 | −0.038221 | −0.044246 | 0.011476 | −0.001381 | 0.018062 | −0.012778 | −0.021346 | −0.007853 | −0.056843 | −0.014842 | −0.023019 | 0.031538 | −0.016987 |
| 225 | −0.031237 | −0.041842 | −0.039138 | −0.020585 | −0.005929 | 0.009345 | −0.013771 | −0.0089 | −0.019025 | −0.040874 | −0.025902 | −0.000787 | 0.008985 | −0.005174 |
| 226 | −0.010739 | −0.000165 | 0.014795 | 0.007601 | 0.007004 | 0.005074 | 0.005085 | 0.000955 | 0.006346 | 0.016424 | 0.015766 | 0.004968 | −0.006715 | 0.021058 |
| 227 | 0.018178 | 0.01051 | −0.008974 | −0.010186 | −0.024522 | −0.00227 | −0.025476 | −0.016693 | 0.024307 | −0.012493 | −0.014795 | −0.000607 | −0.025522 | −0.006113 |
| 228 | 0.031406 | 0.012667 | 0.053827 | −0.009575 | 0.018904 | −0.005245 | 0.029257 | 0.02084 | 0.050996 | 0.005525 | −0.036592 | 0.008014 | 0.022026 | 0.005652 |
| 229 | 0.008313 | −0.010689 | −0.005116 | −0.017077 | 0.010353 | −0.011449 | 0.019066 | 0.02191 | 0.017196 | 0.016824 | 0.037703 | 0.005834 | −0.010653 | 0.009224 |
| 230 | −0.029972 | 0.009016 | −0.02889 | −0.066016 | −0.012169 | −0.003095 | 0.015505 | −0.013159 | −0.027617 | −0.012847 | 0.011612 | 0.010651 | −0.015092 | −0.019761 |
| 231 | −0.017125 | −0.000182 | 0.003338 | −0.001021 | −0.03498 | −0.025353 | −0.006192 | −0.048074 | −0.018098 | 0.033396 | 0.006828 | −0.01554. | −0.008642 | 0.063037 |
| 232 | −0.043549 | −0.014905 | −0.015591 | 0.017386 | 0.033885 | 0.021666 | 0.027762 | 0.018179 | 0.042972 | 0.018162 | 0.052176 | 0.007868 | −0.017642 | 0.009615 |
| 233 | 0.001354 | 0.056276 | −0.017666 | −0.025402 | −0.009721 | −0.004462 | −0.010779 | −0.005526 | 0.026783 | 0.005411 | 0.0171 | −0.0159 | −0.032129 | −0.007957 |
| 234 | 0.033023 | 0.036846 | 0.033414 | −0.016645 | −0.009499 | −0.01304 | 0.00089 | 0.007331 | 0.044411 | 0.023354 | 0.025635 | −0.006253 | −0.000919 | −0.009459 |
| 235 | 0.019466 | 0.020502 | 0.025042 | −0.001103 | −0.00223 | 0.010249 | 0.014449 | −0.013427 | −0.002498 | 0.012505 | −0.033602 | 0.002056 | −0.023257 | −0.011019 |
| 236 | −0.018699 | −0.017737 | −0.017796 | −0.003421 | −0.00686 | −0.009768 | −0.002261 | −0.008361 | 0.028177 | 0.00349 | −0.024256 | −0.077054 | −0.021711 | 0.010594 |
| 237 | −0.004548 | −0.030967 | −0.032624 | 0.022998 | −0.002298 | −0.002327 | 0.004889 | 0.017523 | 0.023193 | 0.019663 | 0.010215 | −0.007594 | −0.023462 | 0.003627 |
| 238 | −0.026562 | −0.019696 | −0.008309 | 0.039352 | 0.003686 | −0.008249 | 0.01091 | 0.030006 | 0.029474 | 0.009768 | −0.013699 | 0.016501 | −0.010735 | 0.027078 |
| 239 | −0.02911 | 0.012927 | 0.014657 | −0.006107 | −0.004343 | −0.001228 | −0.00175 | 0.006901 | 0.001084 | −0.007708 | −0.025943 | 0.003736 | 0.014593 | 0.011904 |
| 240 | −0.025683 | 0.021702 | −0.001826 | −0.003821 | −0.017331 | −0.016133 | −0.017904 | −0.000701 | −0.010097 | −0.016246 | −0.016629 | 0.000316 | 0.013372 | 0.004516 |
| 241 | −0.004258 | 0.034 | −0.012691 | −0.057682 | −0.01963 | −0.027575 | −0.009172 | 0.026047 | 0.037128 | −0.026611 | −0.019687 | −0.012828 | −0.058255 | 0.004532 |
| 242 | 0.036055 | 0.013668 | 0.033005 | 0.042708 | 0.019345 | 0.009573 | 0.012056 | −0.009762 | −0.012008 | −0.001455 | −0.0482 | 0.001744 | 0.015623 | 0.002701 |
| 243 | 0.019649 | 0.002359 | 0.060559 | 0.048029 | 0.002792 | 0.009805 | −0.002247 | −0.00534 | −0.006841 | 0.002869 | −0.021906 | 0.016248 | 0.027608 | −0.009372 |
| 244 | −0.017751 | 0.00587 | 0.022258 | −0.032038 | 0.003645 | 0.01393 | −0.001341 | 0.000344 | 0.005733 | 0.009227 | 0.033786 | −0.003953 | 0.003513 | −0.035721 |
| 245 | 0.011153 | 0.010062 | −0.0549 | −0.015601 | −0.010347 | −0.004819 | −0.011439 | −0.006488 | 0.008812 | −0.029799 | 0.042131 | −0.004772 | 0.00571 | −0.015896 |
| 246 | 0.009184 | 0.003939 | 0.011103 | 0.022088 | 0.025154 | 0.019738 | 0.016984 | 0.014029 | −0.010663 | −0.008109 | −0.010304 | 0.004377 | 0.023296 | −0.004362 |
| 247 | −0.002509 | −0.002233 | −0.028105 | −0.003831 | −0.002883 | 0.015011 | −0.009548 | −0.017901 | −0.000395 | 0.001148 | −0.018359 | −0.0573 | 0.011508 | −0.014114 |
| 248 | −0.002544 | −0.016803 | −0.027045 | 0.031766 | 0.015847 | 0.019071 | 0.013282 | 0.007824 | 0.025627 | 0.015676 | 0.010416 | −0.005679 | −0.008097 | 0.013559 |
| 249 | −0.004785 | 0.016579 | −0.01569 | 0.026044 | 0.004587 | −0.01242 | 0.012797 | −0.00883 | −0.015867 | 0.012421 | 0.037892 | 0.008285 | −0.028854 | 0.018716 |
| 250 | −0.025288 | −0.001491 | −0.006486 | −0.010409 | 0.003115 | 0.006146 | −0.006998 | 0.022037 | −0.017578 | 0.01974 | −0.037882 | −0.012251 | −0.030129 | −0.012867 |
| 251 | −0.055296 | 0.009182 | 0.001834 | 0.00215 | 0.007415 | −0.002227 | 0.002261 | 0.03226 | −0.010416 | −0.005158 | −0.026278 | 0.027131 | −0.018725 | −0.016884 |
| 252 | 0.005172 | 0.00737 | 0.00748 | 0.002143 | −0.000171 | 0.009464 | 0.005021 | 0.005527 | 0.026162 | 0.006413 | −0.007366 | 0.008615 | −0.016403 | −0.018318 |
| 253 | −0.02667 | 0.021527 | 0.008851 | −0.001548 | −0.028342 | −0.01836 | −0.014549 | −0.010702 | 0.037468 | 0.02939 | 0.003706 | −0.016273 | 0.005422 | 0.003856 |
| 254 | −0.008129 | −0.033969 | 0.010074 | −0.020717 | 0.005017 | −0.009178 | −0.002001 | 0.003047 | 0.001642 | −0.025336 | −0.043864 | −0.009105 | −0.008754 | −0.004394 |
| 255 | −0.034688 | 0.002325 | 0.037549 | −0.035573 | 0.003044 | −0.003672 | 0.008814 | −0.002712 | 0.000029 | −0.025731 | −0.021099 | −0.002648 | −0.003913 | −0.026244 |
| 256 | 0.001723 | −0.00379 | 0.021504 | −0.005657 | 0.001771 | −0.004324 | 0.024387 | −0.000102 | 0.025038 | −0.024242 | 0.033874 | 0.004354 | −0.036773 | −0.015626 |
| 257 | 0.006957 | 0.030855 | −0.02567 | −0.009143 | 0.004302 | 0.011214 | 0.010371 | −0.002408 | 0.014704 | 0.023448 | −0.003591 | −0.012062 | −0.009753 | −0.006748 |
| 258 | 0.001209 | 0.014919 | −0.027573 | −0.027378 | −0.027171 | −0.018289 | −0.009067 | −0.006312 | 0.007171 | −0.008665 | −0.01295 | −0.020294 | −0.016344 | 0.005402 |
| 259 | −0.012192 | −0.001496 | −0.031659 | 0.059087 | 0.010066 | −0.00392 | 0.011881 | −0.003308 | −0.031881 | −0.00254 | −0.005494 | 0.007642 | −0.005548 | 0.002936 |
| 260 | 0.003325 | −0.051926 | −0.033367 | −0.003408 | −0.011086 | −0.003955 | −0.000295 | −0.009984 | −0.020065 | 0.048264 | 0.032704 | −0.00824 | −0.054522 | −0.022501 |
| 261 | −0.005109 | −0.026938 | −0.035782 | 0.027977 | 0.000002 | −0.010914 | 0.016236 | 0.022394 | 0.016903 | 0.037915 | 0.031622 | 0.025658 | −0.021556 | 0.025316 |
| 262 | −0.003444 | −0.00992 | −0.01828 | 0.011873 | 0.013792 | 0.03126 | 0.021537 | −0.009788 | 0.020555 | 0.017305 | −0.016202 | −0.006706 | 0.006598 | −0.028422 |
| 263 | 0.003039 | 0.009669 | −0.029758 | 0.030263 | 0.016424 | 0.034334 | 0.020988 | −0.013535 | 0.014909 | 0.022874 | −0.004701 | 0.006867 | 0.023061 | −0.029222 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 264 | −0.010993 | 0.001914 | −0.063298 | −0.019534 | 0.001875 | 0.025722 | −0.005451 | −0.029777 | −0.033862 | −0.009474 | −0.016115 | −0.033274 | 0.054326 | −0.004903 |
| 265 | 0.006308 | −0.045412 | −0.014341 | −0.037928 | 0.013359 | 0.01742 | 0.010875 | 0.015669 | 0.026568 | 0.012948 | −0.023952 | −0.021031 | 0.011533 | 0.022717 |
| 266 | 0.024132 | −0.032565 | −0.009231 | −0.046675 | 0.001032 | 0.005437 | 0.008263 | 0.017879 | 0.024276 | 0.034255 | 0.03305 | 0.006129 | 0.015332 | 0.024788 |
| 267 | 0.035987 | 0.00987 | 0.031509 | 0.009619 | −0.017132 | −0.024242 | −0.027152 | −0.019842 | −0.005819 | −0.003477 | 0.011749 | −0.004516 | 0.017044 | 0.024597 |
| 268 | −0.014094 | 0.00658 | 0.011973 | −0.0022 | −0.008496 | 0.006214 | −0.014972 | −0.019735 | −0.014241 | 0.011417 | 0.00391 | −0.01514 | 0.011548 | 0.005254 |
| 269 | −0.006274 | −0.007956 | 0.021915 | 0.014155 | 0.003643 | 0.005398 | 0.000106 | 0.00257 | −0.000871 | 0.016724 | 0.002443 | 0.005748 | −0.040685 | 0.015488 |
| 270 | 0.010217 | −0.000279 | 0.013259 | −0.001098 | −0.006216 | −0.007481 | −0.008995 | 0.001319 | 0.013784 | −0.001706 | −0.008595 | 0.019667 | −0.033316 | 0.005629 |
| 271 | −0.059112 | 0.008485 | −0.064445 | −0.043709 | 0.024567 | 0.006592 | −0.02336 | 0.026414 | 0.002776 | 0.002874 | −0.03011 | −0.001915 | 0.049027 | 0.011348 |
| 272 | −0.006228 | −0.017479 | −0.009064 | 0.042688 | 0.009627 | −0.015566 | 0.016136 | 0.0083 | 0.016694 | −0.005151 | 0.009044 | −0.009095 | 0.028683 | 0.019817 |
| 273 | −0.005032 | −0.021148 | −0.012613 | 0.036119 | 0.005078 | 0.006768 | 0.012942 | −0.011878 | −0.000524 | −0.012544 | −0.003754 | −0.001002 | 0.02149 | −0.004926 |
| 274 | 0.010786 | −0.024818 | −0.012117 | 0.0329 | 0.0097 | 0.005696 | 0.021863 | −0.003226 | 0.006837 | −0.008574 | −0.000702 | 0.006619 | 0.006509 | −0.002631 |
| 275 | 0.023157 | −0.002053 | −0.028096 | −0.038911 | −0.007474 | 0.017374 | 0.002888 | −0.005831 | −0.008998 | −0.019672 | −0.011395 | 0.022495 | 0.018736 | −0.033023 |
| 276 | −0.003112 | −0.035266 | −0.045351 | −0.004997 | −0.009127 | −0.009672 | −0.004974 | −0.000173 | 0.043521 | −0.003814 | −0.030355 | −0.090578 | −0.021169 | 0.011364 |
| 277 | 0.036101 | −0.007034 | −0.01668 | −0.01919 | 0.01167 | 0.00984 | 0.010449 | 0.010337 | 0.00563 | 0.006174 | −0.020599 | −0.006939 | 0.003135 | −0.030852 |
| 278 | 0.025491 | 0.003606 | −0.007561 | −0.023003 | 0.019997 | 0.01281 | 0.011265 | 0.023465 | 0.000551 | 0.002928 | −0.013377 | 0.019956 | 0.032252 | −0.023208 |
| 279 | −0.007713 | −0.014032 | 0.018879 | −0.00246 | 0.007432 | −0.001543 | −0.005907 | 0.030558 | 0.005279 | −0.004611 | −0.016384 | 0.036465 | 0.014886 | 0.008598 |
| 280 | 0.016869 | 0.001903 | 0.037836 | 0.016371 | −0.037845 | −0.040782 | −0.032066 | −0.012603 | 0.000244 | 0.006947 | −0.024027 | −0.004217 | 0.04978 | 0.013021 |
| 281 | −0.00048 | −0.021609 | 0.029796 | 0.032191 | 0.026335 | −0.000766 | 0.015945 | 0.020755 | −0.023309 | −0.001799 | 0.041525 | 0.036751 | 0.024539 | 0.031625 |
| 282 | 0.004805 | −0.011513 | 0.034542 | −0.00307 | 0.011217 | −0.002809 | −0.012299 | 0.011759 | −0.03681 | −0.030735 | −0.021454 | 0.022166 | 0.011807 | 0.001013 |
| 283 | 0.066802 | −0.04481 | 0.000214 | −0.005719 | 0.011186 | 0.026512 | −0.011317 | −0.007265 | −0.000671 | 0.00401 | 0.021067 | −0.014659 | 0.041004 | −0.013899 |
| 284 | 0.014363 | −0.0001 | −0.010488 | 0.003534 | 0.002895 | 0.010061 | 0.003146 | −0.005874 | 0.002313 | 0.02354 | 0.014177 | 0.003316 | 0.00519 | 0.003776 |
| 285 | −0.002365 | 0.020941 | 0.001149 | −0.007238 | 0.017416 | 0.020237 | 0.012532 | −0.001586 | −0.004146 | 0.016759 | 0.008434 | 0.001955 | 0.014977 | −0.015942 |
| 286 | 0.002686 | 0.01827 | −0.006067 | −0.017181 | −0.012802 | −0.016619 | −0.004314 | 0.016461 | −0.005351 | 0.022724 | 0.014944 | 0.039436 | −0.051093 | 0.014939 |
| 287 | 0.020551 | 0.030534 | −0.00455 | −0.039301 | −0.022128 | −0.026096 | −0.016959 | 0.00005 | −0.007491 | 0.011538 | 0.024852 | 0.030777 | −0.028496 | −0.001279 |
| 288 | 0.0292471 | 0.016431 | −0.0195191 | −0.047074 | −0.003514 | 0.020777 | 0.005305 | 0.000865 | −0.013641 | −0.006629 | 0.0061671 | 0.003789 | 0.0043541 | −0.003279 |
| 289 | −0.001837 | −0.015245 | 0.000393 | −0.024855 | 0.015562 | 0.020188 | 0.020277 | 0.005468 | 0.024178 | 0.024079 | −0.029709 | −0.01784 | −0.010823 | −0.029646 |
| 290 | 0.016413 | −0.005559 | −0.018244 | 0.000212 | 0.009705 | 0.02183 | 0.007329 | −0.009093 | −0.004384 | 0.014138 | 0.012118 | 0.0053 | −0.060098 | −0.002081 |
| 291 | 0.024873 | −0.009957 | −0.016524 | 0.001981 | 0.009365 | 0.025217 | 0.007229 | −0.012221 | −0.011442 | 0.014546 | 0.001523 | 0.005306 | −0.061687 | −0.004121 |
| 292 | 0.037411 | −0.004 | −0.023263 | −0.006388 | 0.019615 | 0.035987 | 0.020158 | 0.005509 | 0.002672 | 0.015787 | −0.019761, | 0.008276 | −0.058015 | −0.001843 |
| 293 | −0.052236 | 0.032216 | 0.006457 | 0.026812 | −0.009189 | −0.004902 | −0.010581 | −0.022798 | −0.057836 | 0.022554 | −0.026266 | −0.001983 | −0.012091 | −0.001495 |
| 294 | 0.034525 | 0.003969 | 0.001838 | −0.005551 | −0.021646 | 0.008105 | −0.013455 | −0.027738 | −0.035381 | −0.005375 | 0.000489 | −0.005256 | 0.014195 | −0.004322 |
| 295 | −0.002074 | −0.0242031 | −0.022037 | 0.0314 | −0.008863 | −0.009046 | −0.000014 | −0.019079 | −0.023304 | 0.015011 | −0.003063 | −0.000618 | 0.008762 | 0.011797 |
| 296 | 0.004433 | −0.003975 | −0.015751 | 0.001995 | −0.00657 | 0.007278 | 0.01654 | 0.006165 | −0.010027 | 0.004746 | −0.015768 | 0.02863 | 0.006954 | −0.008775 |
| 297 | 0.011188 | −0.005544 | 0.001108 | 0.016891 | −0.008051 | −0.004732 | 0.007838 | −0.020612 | −0.017834 | 0.003499 | 0.008962 | −0.009904 | 0.012347 | 0.003479 |
| 298 | 0.050696 | −0.009131 | 0.04562 | 0.015009 | 0.000342 | 0.004939 | 0.000526 | 0.010111 | 0.018109 | −0.002292 | 0.028231 | 0.032939 | −0.063194 | −0.02291 |
| 299 | −0.049772 | −0.006019 | 0.016877 | −0.015252 | −0.022101 | −0.025086 | −0.002294 | −0.003361 | −0.003046 | −0.000517 | 0.015929 | 0.002348 | −0.037616 | 0.023587 |
| 300 | 0.013445 | −0.008046 | 0.03397 | 0.009608 | −0.032213 | −0.032293 | −0.024845 | −0.017281 | 0.043957 | 0.005902 | 0.040419 | 0.019014 | −0.041136 | −0.035265 |
| 301 | −0.027275 | 0.00777 | 0.015919 | −0.00709 | 0.002316 | 0.008183 | −0.000121 | −0.010315 | −0.015519 | 0.016415 | 0.008323 | 0.001079 | 0.02379 | 0.003021 |
| 302 | −0.034733 | −0.001605 | 0.004186 | −0.02245 | 0.00131 | 0.011223 | 0.014316 | 0.013011 | 0.002437k | 0.015703 | −0.009926 | 0.015603 | −0.03321 | −0.025431 |
| 303 | −0.016124 | 0.000936 | 0.017135 | −0.027258 | −0.007396 | 0.00763 | 0.007387 | −0.007439 | −0.000078 | −0.004108 | −0.012315 | −0.00853 | −0.031764 | 0.012402 |
| 304 | −0.044683 | −0.018791 | 0.019005 | 0.00093 | −0.008195 | 0.00913 | 0.009116 | −0.006833 | 0.006594 | −0.021702 | −0.038547 | 0.015663 | −0.028284 | −0.003443 |
| 305 | 0.056482 | 0.081195 | −0.01808 | −0.035131 | 0.039122 | 0.015511 | 0.03209 | −0.008881 | −0.00664 | 0.007038 | −0.011428 | −0.003043 | 0.027071 | 0.00892 |
| 306 | −0.02314 | 0.031747 | 0.002476 | 0.000077 | −0.006176 | 0.00565 | −0.013911 | 0.005952 | −0.008213 | 0.000565 | 0.01003 | −0.00513 | −0.012919 | −0.004071 |
| 307 | −0.014257 | −0.009392 | −0.027237 | −0.007628 | 0.000172 | 0.004451 | −0.02201 | −0.017754 | −0.001163 | 0.007963 | 0.031567 | 0.027508 | 0.043961 | −0.003481 |
| 308 | −0.031436 | 0.016315 | 0.000001 | −0.003242 | 0.009641 | 0.010588 | 0.015172 | −0.002412 | −0.013629 | −0.013433 | 0.017921 | 0.023866 | −0.003882 | −0.024646 |
| 309 | 0.004563 | 0.001515 | 0.037733 | −0.009715 | 0.011937 | 0.005804 | 0.000232 | −0.001333 | −0.011533 | −0.003459 | −0.022275 | 0.007851 | 0.020678 | −0.010028 |
| 310 | 0.000906 | 0.009672 | 0.043071 | 0.021918 | 0.014679 | 0.018393 | 0.006112 | 0.003129 | −0.019478 | 0.001263 | −0.010251 | 0.008389 | −0.035636 | −0.005977 |
| 311 | −0.009044 | 0.029433 | −0.002146 | 0.001203 | −0.000995 | −0.007148 | −0.017776 | −0.00523 | −0.002574 | 0.009588 | −0.031786 | −0.01222 | 0.020948 | −0.014514 |
| 312 | 0.020568 | 0.006092 | −0.016095 | −0.022513 | −0.018377 | −0.000834 | 0.021166 | −0.020029 | 0.034545 | −0.035996 | −0.002064 | −0.030458 | −0.051202 | −0.042948 |
| 313 | 0.002102 | −0.020245 | −0.009576 | 0.009317 | −0.000437 | −0.009006 | 0.013363 | 0.000204 | 0.021629 | 0.00278 | 0.004543 | −0.00705 | −0.018009 | 0.006561 |
| 314 | −0.028569 | −0.045454 | 0.04944 | 0.059996 | −0.007398 | 0.001127 | 0.027549 | −0.040806 | 0.010596 | 0.009233 | −0.008264 | −0.027026 | 0.08767 | −0.004724 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 315 | −0.013655 | −0.007201 | 0.022229 | −0.036957 | 0.00377 | −0.017734 | 0.012656 | 0.026613 | 0.030187 | 0.013553 | 0.002159 | −0.004335 | −0.022086 | 0.003537 |
| 316 | −0.027568 | 0.011562 | −0.033557 | −0.003636 | −0.0226 | −0.024661 | −0.002643 | −0.013865 | −0.003589 | −0.024926 | 0.019109 | −0.020361 | −0.006638 | −0.007281 |
| 317 | 0.040488 | −0.024888 | 0.032644 | 0.009737 | 0.021556 | 0.009799 | 0.007532 | 0.005469 | −0.012415 | 0.013061 | −0.020017 | 0.000883 | 0.04107 | −0.003724 |
| 318 | 0.007855 | −0.018704 | −0.026653 | 0.025975 | 0.019991 | 0.0127 | 0.007844 | 0.014314 | 0.035596 | 0.025463 | 0.023783 | −0.021728 | 0.005146 | −0.014756 |
| 319 | 0.010511 | −0.030676 | 0.010051 | −0.023096 | 0.00187 | 0.009446 | 0.005759 | 0.003084 | −0.006226 | 0.010188 | −0.011801 | −0.011345 | 0.028706 | −0.013587 |
| 320 | −0.036501 | 0.030927 | 0.0053311 | 0.00546 | −0.009751 | 0.00795 | 0.003371 | 0.014413 | 0.000474 | −0.03211 | −0.049548 | 0.01306 | −0.022565 | −0.043655 |
| 321 | −0.029758 | 0.000719 | 0.008631 | −0.034982 | 0.01384 | 0.004473 | 0.012091 | 0.039695 | 0.03552 | 0.012828 | 0.036767 | 0.024628 | −0.022106 | 0.013597 |
| 322 | 0.054549 | −0.022328 | −0.008533 | 0.005329 | −0.024099 | −0.032068 | −0.026804 | −0.000977 | 0.057128 | 0.0560884 | −0.040236 | −0.00455 | −0.044586 | −0.001611 |
| 323 | −0.007875 | −0.037414 | −0.07291 | 0.024892 | −0.007166 | −0.001008 | −0.017649 | 0.015256 | 0.014132 | 0.024207 | 0.010823 | −0.009971 | 0.043147 | 0.028606 |
| 324 | −0.035498 | 0.001396 | −0.040721 | 0.027532 | 0.019092 | 0.00873 | 0.003199 | 0.056215 | 0.048307 | 0.015603 | 0.018179 | 0.02534 | −0.055863 | −0.005724 |
| 325 | 0.036929 | −0.019621 | 0.049909 | 0.014439 | 0.024924 | 0.016462 | 0.024127 | 0.023782 | 0.013318 | 0.012501 | −0.008903 | 0.010576 | 0.029414 | 0.027717 |
| 326 | 0.049184 | −0.011381 | −0.003733 | .0.02469 | −0.008622 | −0.026841 | −0.002182 | 0.014012 | 0.014099 | 0.011679 | 0.028535 | 0.014149 | −0.027499 | 0.037718 |
| 327 | −0.003072 | 0.022934 | −0.02957 | 0.016751 | 0.024215 | 0.010913 | 0.021593 | 0.018254 | −0.004695 | −0.007634 | −0.016155 | 0.028977 | 0.008413 | 0.01217 |
| 328 | −0.076121 | 0.059809 | 0.013205 | −0.042929 | 0.009872 | −0.001125 | 0.021879 | 0.020095 | −0.021479 | 0.000373 | −0.015266 | −0.010473 | 0.055989 | −0.015848 |
| 329 | −0.018925 | −0.009026 | −0.024295 | 0.030414 | 0.011683 | 0.01741 | 0.009085 | 0.002661 | −0.009974 | 0.011706 | 0.016802 | −0.011381 | 0.021904 | 0.001061 |
| 330 | 0.037156 | −0.08141 | −0.056929 | −0.011577 | −0.001704 | 0.006247 | −0.006705 | −0.027785 | −0.010973 | −0.032329 | −0.053966 | −0.103679 | −0.055092 | −0.003684 |
| 331 | 0.007795 | 0.00944 | −0.009513 | −0.0111 | 0.005046 | 0.014161 | −0.002652 | 0.01331 | −0.006527 | 0.012197 | −0.009349 | 0.016882 | 0.012975 | 0.005856 |
| 332 | −0.041978 | −0.050602 | −0.002586 | 0.018265 | −0.011237 | −0.014914 | −0.022928 | −0.026611 | −0.003778 | −0.043231 | −0.06979 | 0.007634 | −0.018129 | −0.005609 |
| 333 | 0.007495 | −0.01157 | −0.006787 | 0.025797 | 0.019121 | 0.008309 | 0.002438 | 0.015959 | −0.005325 | 0.008533 | −0.011291 | 0.008015 | 0.045221 | 0.021812 |
| 334 | 0.040841 | 0.023984 | −0.028961 | −0.00676 | −0.026597 | 0.009426 | −0.000471 | −0.029736 | 0.010719 | 0.003527 | 0.063765 | −0.040005 | 0.039063 | −0.037382 |
| 335 | −0.011795 | −0.010838 | −0.014144 | 0.025644 | 0.002636 | −0.001387 | 0.007175 | 0.007626 | −0.014022 | −0.004789 | 0.011316 | 0.014031 | 0.025722 | 0.024521 |
| 336 | 0.033504 | −0.012073 | 0.028715 | 0.007611 | 0.013327 | 0.008456 | −0.000698 | 0.009959 | 0.005459 | −0.015623 | −0.013847 | 0.008283 | 0.006373 | −0.005838 |
| 337 | −0.031561 | 0.002611 | 0.023238 | −0.034693 | −0.005869 | −0.035202 | −0.006673 | 0.019206 | 0.01993 | 0.018782 | 0.029853 | 0.011831 | −0.029198 | 0.02575 |
| 338 | −0.095999 | 0.012515 | −0.022233 | 0.022217 | −0.016555 | 0.008561 | −0.032139 | 0.02431 | −0.008795 | 0.014739 | 0.007191 | −0.01996 | −0.011836 | 0.023698 |
| 339 | −0.051085 | −0.07361 | −0.000434 | −0.011791 | −0.004648 | −0.029061 | −0.027784 | 0.023529 | −0.000355 | 0.006591 | 0.001249 | 0.012157 | −0.000337 | 0.014214 |
| 340 | 0.0574591 | −0.0245961 | 0.053776 | −0.019452 | 0.022309 | 0.036725 | 0.037814 | −0.019092 | 0.0285181 | 0.038881 | 0.025661 | −0.006672 | −0.001629 | 0.037999 |

| | FX | FY | FZ | GA | GB | GC | GD | GE | GF | GG | GH | GI | GJ | GK |
|---|---|---|---|---|---|---|---|---|---|---|---|---|---|---|
| 1 | 0.028444 | 0.052914 | −0.012638 | −0.005961 | −0.035372 | −0.026993 | 0.12858 | 0.015343 | 0.05406 | 0.033355 | 0.001676 | 0.029723 | −0.006255 | 0.014867 |
| 2 | 0.0376121 | 0.036637 | 0.0325591 | 0.049961 | 0.038452 | 0.08238 | 0.039009 | 0.1443 | 0.052384 | 0.040424 | 0.068147 | 0.0515 | 0.072154 | 0.024033 |
| 3 | −0.017273 | −0.037203 | −0.028848 | −0.002538 | 0.039738 | 0.045131 | −0.048329 | 0.066467 | 0.031051 | 0.064645 | 0.056725 | 0.013326 | −0.050091 | −0.010405 |
| 4 | −0.035905 | −0.03394 | −0.029957 | −0.019616 | 0.007819 | −0.020165 | −0.010393 | 0.041477 | −0.014975 | −0.020509 | −0.040307 | 0.034099 | 0.030462 | 0.026073 |
| 5 | −0.023935 | −0.013221 | −0.02415 | −0.002423 | −0.036817 | −0.0644 | 0.026765 | 0.041279 | 0.012489 | 0.009222 | 0.022341 | 0.04012 | 0.046147 | 0.018684 |
| 6 | −0.00316 | 0.008131 | 0.007694 | 0.022241 | 0.028463 | 0.03699 | −0.042843 | −0.069176 | 0.003073 | −0.022205 | −0.01099 | 0.073349 | −0.009024 | −0.073557 |
| 7 | −0.024004 | −0.022639 | −0.0237 | −0.030714 | 0.012066 | 0.044988 | 0.043975 | 0.030206 | 0.042901 | 0.025755 | −0.008982 | −0.021268 | −0.018479 | −0.010491 |
| 8 | −0.008367 | 0.002798 | 0.014484 | −0.006754 | −0.012284 | 0.031418 | −0.112181 | −0.083147 | 0.001564 | −0.023308 | −0.023338 | −0.031672 | −0.041721 | −0.042169 |
| 9 | −0.004929 | −0.004249 | 0.00776 | 0.028731 | 0.062035 | 0.096905 | 0.001373 | 0.008277 | 0.00499 | 0.009682 | −0.009532 | 0.019907 | −0.053565 | 0.008896 |
| 10 | −0.042362 | −0.04268 | −0.026358 | −0.003146 | 0.017743 | −0.004545 | −0.02431 | 0.068172 | −0.00556 | 0.007461 | −0.035087 | −0.000649 | −0.04917 | −0.04103 |
| 11 | −0.001012 | −0.026345 | −0.012567 | −0.014443 | 0.010504 | −0.01849 | −0.014245 | 0.005878 | −0.009964 | 0.012372 | 0.052761 | 0.032906 | 0.018554 | 0.032001 |
| 12 | −0.011635 | −0.0274521 | −0.0332971 | −0.058534 | 0.009562 | −0.021404 | 0.03019 | −0.072013 | 0.0037491 | −0.02249 | −0.005179 | −0.006602 | 0.0003191 | 0.094159 |
| 13 | 0.06231 | 0.013223 | 0.031573 | 0.037156 | 0.058553 | 0.053738 | −0.061525 | 0.021717 | −0.017738 | −0.038756 | −0.011943 | 0.0108 | −0.014372 | −0.051225 |
| 14 | −0.002349 | 0.011062 | −0.007581 | 0.036694 | 0.018478 | 0.076272 | 0.137926 | −0.056782 | 0.004318 | 0.040707 | 0.010642 | 0.043326 | 0.026609 | 0.058319 |
| 15 | −0.010985 | −0.016788 | −0.002122 | −0.008108 | −0.102279 | −0.191761 | −0.115922 | −0.010588 | −0.057698 | −0.042345 | −0.012557 | −0.037736 | 0.074139 | 0.017623 |
| 16 | −0.00026 | 0.028112 | −0.005176 | 0.024154 | −0.012071 | −0.029303 | 0.056089 | 0.028516 | 0.016893 | 0.041499 | −0.022215 | −0.017625 | 0.018692 | −0.009105 |
| 17 | −0.013623 | −0.025163 | −0.01076 | −0.000005 | −0.003602 | −0.00052 | 0.015998 | −0.058922 | −0.028157 | −0.060899 | −0.057426 | −0.019409 | −0.036568 | 0.039766 |
| 18 | −0.04456 | −0.004647 | −0.015091 | 0.002832 | −0.024572 | −0.036493 | −0.034514 | 0.049762 | 0.031189 | 0.009492 | −0.029078 | 0.032234 | −0.007995 | 0.040245 |
| 19 | 0.003733 | 0.011153 | 0.009294 | 0.006926 | 0.015436 | −0.001672 | 0.049849 | 0.024264 | 0.006146 | 0.023808 | 0.056261 | −0.035504 | −0.045479 | 0.028296 |
| 20 | −0.048837 | −0.002884 | −0.021412 | −0.018964 | −0.06219 | 0.017396 | 0.069874 | 0.071791 | 0.029621 | 0.025028 | −0.03743 | −0.007252 | −0.0753 | −0.008898 |
| 21 | 0.021596 | 0.015865 | 0.017181 | −0.011489 | 0.036639 | 0.060711 | 0.032604 | −0.008109 | −0.0166 | −0.020063 | −0.075413 | −0.009563 | 0.051298 | 0.020018 |
| 22 | −0.009697 | 0.000955 | −0.019609 | 0.009461 | 0.022531 | 0.00718 | 0.031331 | 0.016307 | 0.023679 | −0.019764 | −0.052642 | −0.015961 | −0.01055 | 0.027672 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 23 | 0.006296 | −0.031524 | 0.001796 | 0.02216 | 0.014208 | 0.026365 | −0.0249 | −0.036467 | 0.008033 | −0.000509 | −0.032308 | −0.025544 | 0.08106 | −0.040263 |
| 24 | 0.011742 | 0.023059 | 0.01375 | 0.036863 | 0.015581 | 0.002365 | 0.014296 | 0.004527 | −0.014852 | −0.049386 | −0.050638 | 0.056462 | 0.081777 | −0.032292 |
| 25 | 0.003981 | 0.003357 | 0.011468 | 0.019654 | −0.012174 | −0.058815 | −0.053031 | 0.010687 | 0.032983 | 0.058672 | 0.123687 | −0.021761 | 0.013071 | 0.038639 |
| 26 | 0.034458 | 0.01363 | 0.014471 | −0.030711 | −0.019663 | 0.004782 | 0.017596 | −0.014396 | −0.035739 | 0.029754 | 0.05709 | 0.010929 | 0.093871 | 0.02828 |
| 27 | 0.018536 | 0.012189 | 0.004283 | 0.055976 | 0.065464 | −0.010094 | −0.012825 | 0.024867 | −0.0015 | −0.045551 | −0.023206 | 0.002999 | 0.028936 | 0.101263 |
| 28 | 0.004041 | 0.024579 | 0.003521 | −0.021298 | −0.025735 | −0.070775 | −0.054098 | −0.018023 | 0.021938 | −0.001452 | −0.018134 | 0.029812 | 0.028727 | −0.000209 |
| 29 | −0.022066 | −0.027145 | −0.009157 | −0.021988 | 0.006399 | −0.023315 | 0.015354 | 0.001218 | 0.045635 | 0.043268 | 0.019932 | 0.0273 | 0.013997 | 0.014135 |
| 30 | −0.051868 | −0.072315 | −0.056843 | −0.066602 | −0.03873 | 0.04499 | 0.067504 | 0.040495 | 0.030511 | 0.012813 | 0.060349 | −0.012877 | 0.031275 | −0.07264 |
| 31 | −0.020404 | 0.00094 | −0.022124 | −0.008328 | 0.0017 | 0.03256 | 0.008938 | 0.091772 | −0.060614 | −0.03372 | −0.035278 | 0.022184 | −0.069866 | −0.067322 |
| 32 | −0.003409 | −0.005103 | −0.024378 | −0.05344 | −0.020896 | −0.033644 | −0.049118 | −0.042358 | 0.00421 | −0.01577 | −0.027488 | −0.00796 | 0.001921 | −0.056606 |
| 33 | 0.011281 | 0.026265 | 0.025346 | 0.028554 | 0.023826 | −0.021393 | 0.093455 | −0.121566 | −0.02833 | −0.007118 | 0.069111 | 0.015819 | −0.08736 | −0.038754 |
| 34 | 0.002204 | 0.008792 | 0.004632 | 0.01962 | −0.019871 | −0.062454 | −0.009167 | −0.103173 | 0.021842 | −0.008216 | −0.057933 | −0.041127 | −0.11372 | 0.020498 |
| 35 | 0.042545 | 0.029963 | 0.049366 | 0.085089 | 0.026096 | −0.040503 | 0.010433 | 0.044194 | −0.009641 | −0.002463 | −0.045965 | −0.019106 | 0.037406 | 0.072141 |
| 36 | −0.038757 | −0.028744 | −0.024552 | −0.036807 | −0.042736 | 0.015581 | 0.050946 | 0.011243 | 0.008783 | 0.045714 | 0.046389 | −0.05204 | −0.052157 | −0.039713 |
| 37 | 0.024401 | 0.051711 | 0.042637 | 0.07428 | −0.025212 | −0.090619 | 0.122438 | −0.000905 | 0.105071 | 0.100702 | 0.061018 | −0.039375 | −0.062214 | 0.040378 |
| 38 | −0.008518 | −0.003069 | −0.021724 | −0.019734 | 0.004229 | −0.006307 | −0.061325 | −0.047951 | −0.002454 | 0.029376 | −0.007686 | 0.040612 | 0.012217 | 0.002472 |
| 39 | 0.012805 | 0.01665 | 0.002847 | −0.028388 | −0.014522 | 0.028473 | −0.038948 | −0.002479 | 0.020848 | 0.026382 | 0.003869 | −0.055779 | −0.032213 | −0.051236 |
| 40 | −0.001517 | 0.016665 | 0.01982 | 0.006605 | 0.024743 | 0.041482 | 0.022009 | 0.002484 | 0.07555 | 0.05565 | 0.003803 | 0.111159 | 0.096241 | −0.019616 |
| 41 | −0.004099 | −0.001026 | 0.015369 | 0.029571 | 0.031645 | 0.026803 | −0.075565 | −0.004847 | 0.026598 | −0.025738 | −0.020341 | 0.170636 | 0.065811 | −0.00067 |
| 42 | −0.0040451 | −0.0002491 | 0.0045011 | 0.013891 | 0.010983 | 0.011842 | 0.009505 | 0.002675 | 0.000405 | 0.000654 | −0.01087 | 0.012571 | −0.015893 | −0.002704 |
| 43 | 0.045443 | 0.040061 | 0.034674 | 0.001991 | 0.029444 | 0.079986 | −0.021641 | 0.01324 | −0.040409 | −0.063546 | −0.042802 | 0.01336 | 0.045573 | 0.045365 |
| 44 | −0.019322 | 0.003534 | 0.011353 | 0.006021 | −0.016022 | −0.048871 | −0.03888 | −0.059527 | −0.040456 | −0.017929 | −0.003086 | −0.02133 | −0.036373 | −0.092544 |
| 45 | 0.005569 | −0.005718 | −0.006406 | 0.00735 | 0.001418 | −0.09067 | 0.041826 | 0.09637 | −0.0124 | −0.017816 | −0.031525 | −0.009317 | 0.026438 | −0.062752 |
| 46 | 0.018518 | 0.017265 | −0.007909 | −0.033624 | −0.029265 | −0.020695 | 0.031171 | 0.004904 | 0.044102 | 0.084088 | 0.020247 | −0.016538 | −0.004613 | 0.001303 |
| 47 | −0.00043 | −0.032439 | −0.020069 | 0.008534 | 0.020218 | 0.020552 | 0.003559 | −0.041555 | −0.02961 | −0.055598 | −0.031095 | 0.061081 | 0.059843 | 0.0724 |
| 48 | −0.015005 | 0.006862 | 0.012325 | 0.021569 | −0.058714 | −0.006551 | 0.01722 | −0.03235 | 0.0151731 | 0.015231 | 0.0076851 | 0.0245231 | 0.0372261 | −0.010666 |
| 49 | 0.0131861 | −0.0217061 | −0.032593 | −0.012373 | 0.009814 | 0.011575 | −0.055244 | −0.075049 | −0.052674 | −0.065768 | −0.030927 | 0.074928 | 0.023694 | −0.013887 |
| 50 | 0.028834 | 0.083292 | 0.071411 | 0.024242 | −0.054069 | −0.099981 | 0.014769 | 0.070237 | 0.051131 | −0.019165 | −0.085401 | 0.018936 | −0.018692 | −0.096097 |
| 51 | 0.045259 | 0.026885 | 0.051233 | 0.049537 | 0.099911 | 0.0199 | −0.027971 | 0.018271 | 0.041662 | 0.p42915 | 0.114736 | 0.024128 | 0.02248 | −0.00134 |
| 52 | 0.0298921 | 0.03372 | 0.044775 | 0.069494 | 0.04348 | 0.06682 | 0.005184 | 0.023978 | 0.072873 | 0.069485 | 0.082464 | −0.002336 | 0.03179 | 0.085538 |
| 53 | 0.049013 | 0.024097 | 0.042742 | 0.022418 | 0.035952 | −0.016434 | −0.046598 | −0.060007 | 0.017081 | −0.031898 | −0.072043 | −0.000943 | 0.037513 | −0.047475 |
| 54 | −0.001385 | −0.007702 | −0.029683 | −0.032291 | 0.013896 | −0.078096 | −0.043615 | 0.083608 | 0.091894 | 0.034162 | −0.050507 | −0.043021 | 0.012502 | 0.019082 |
| 55 | −0.030844 | 0.020872 | −0.000392 | 0.034053 | −0.017146 | −0.095387 | 0.022844 | 0.05421 | 0.051744 | 0.011164 | 0.040548 | 0.07351 | 0.04124 | −0.022266 |
| 56 | −0.026229 | −0.055258 | −0.041778 | −0.016886 | 0.031407 | 0.022172 | 0.077189 | 0.081591 | 0.005508 | 0.044767 | 0.0208 | −0.061709 | −0.064734 | 0.053895 |
| 57 | 0.033831 | 0.033836 | 0.040599 | 0.031932 | 0.001155 | −0.026068 | 0.077069 | 0.087189 | −0.043531 | −0.020856 | 0.012523 | 0.038153 | −0.018197 | 0.014745 |
| 58 | 0.023852 | 0.032082 | −0.001849 | 0.016909 | 0.000022 | 0.067996 | −0.079997 | 0.106613 | 0.037673 | 0.052658 | 0.035111 | 0.035761 | 0.026071 | 0.048825 |
| 59 | 0.036036 | 0.03178 | 0.018637 | 0.046739 | 0.048443 | −0.009081 | −0.026052 | −0.070637 | −0.025878 | 0.055061 | 0.10255 | −0.008315 | −0.024087 | 0.04922 |
| 60 | 0.032903 | 0.028397 | 0.003067 | −0.043532 | 0.006039 | 0.029219 | 0.042307 | −0.014391 | −0.00177 | 0.011784 | 0.079566 | −0.010997 | 0.028669 | −0.001861 |
| 61 | −0.009429 | −0.045079 | −0.007794 | 0.001105 | 0.000218 | 0.089181 | −0.009971 | 0.030259 | 0.044576 | 0.026799 | 0.000681 | 0.026802 | 0.012446 | 0.086262 |
| 62 | 0.013387 | 0.044659 | 0.059425 | 0.048452 | −0.01983 | −0.010101 | 0.02845 | −0.065117 | −0.002927 | −0.017346 | −0.044664 | 0.039419 | 0.053617 | −0.014511 |
| 63 | 0.074891 | 0.048201 | 0.065607 | 0.015862 | 0.06009 | 0.041799 | 0.107041 | 0.052601 | −0.088977 | −0.019107 | 0.058776 | −0.018525 | 0.061884 | −0.066943 |
| 64 | 0.012489 | 0.040275 | 0.030914 | 0.064451 | 0.038859 | −0.021685 | −0.040019 | 0.047342 | −0.008553 | −0.035469 | −0.047828 | 0.018223 | 0.021711 | −0.008385 |
| 65 | −0.032202 | −0.008011 | −0.017959 | −0.038219 | −0.082357 | −0.030784 | 0.011942 | −0.101131 | 0.03066 | 0.018571 | 0.025183 | −0.054807 | 0.009716 | −0.052915 |
| 66 | 0.002447 | −0.020994 | 0.010035 | 0.034761 | 0.005436 | −0.058058 | −0.041194 | 0.0466 | −0.053909 | −0.046656 | −0.03358 | 0.036377 | 0.012161 | 0.037976 |
| 67 | −0.010809 | 0.011937 | 0.001787 | −0.0107 | −0.019931 | −0.026406 | 0.123323 | 0.009869 | −0.02225 | 0.001433 | 0.012083 | −0.064055 | −0.052988 | 0.001385 |
| 68 | 0.013936 | 0.001908 | −0.000897 | 0.044831 | 0.039434 | 0.069995 | −0.028847 | −0.048372 | 0.026123 | −0.000948 | −0.003361 | −0.027098 | −0.012932 | 0.034263 |
| 69 | 0.017397 | 0.004213 | 0.012226 | 0.049369 | 0.056957 | 0.00745 | −0.123412 | −0.014223 | 0.07705 | 0.058836 | 0.189486 | 0.058367 | 0.023441 | −0.070584 |
| 70 | 0.009325 | 0.00103 | 0.001207 | 0.012759 | −0.054304 | −0.146005 | −0.020042 | −0.026193 | −0.019811 | −0.050321 | 0.011556 | 0.052018 | 0.042187 | 0.056433 |
| 71 | −0.028956 | −0.012125 | −0.027938 | 0.025063 | −0.04314 | −0.044572 | −0.036644 | 0.056536 | 0.006216 | 0.025031 | 0.039521 | −0.001109 | −0.000581 | 0.042249 |
| 72 | 0.072232 | 0.083685 | 0.06426 | 0.050224 | 0.051834 | −0.010982 | −0.000903 | 0.045739 | 0.086831 | 0.039955 | 0.022271 | −0.033168 | −0.018701 | −0.081979 |
| 73 | −0.0097871 | −0.044254 | −0.033769 | −0.025482 | 0.046209 | 0.040582 | −0.038177 | −0.003131 | 0.0144711 | 0.033747 | 0.106442 | 0.001655 | 0.015004 | 0.096121 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 74 | 0.027086 | −0.016393 | −0.024873 | −0.065808 | −0.02832 | 0.020823 | 0.031936 | −0.136211 | −0.03068 | −0.007496 | 0.021381 | −0.038975 | −0.042963 | 0.013207 |
| 75 | −0.071618 | −0.024955 | −0.072797 | −0.199315 | −0.118056 | 0.054546 | −0.045866 | −0.009645 | 0.060318 | 0.078415 | 0.043635 | 0.016488 | 0.034727 | −0.072288 |
| 76 | 0.003296 | −0.012018 | −0.006526 | 0.06624 | 0.010787 | −0.008074 | −0.05251 | 0.004648 | −0.030929 | −0.012579 | −0.073844 | −0.023307 | −0.09812 | 0.030223 |
| 77 | −0.064652 | 0.014095 | 0.025108 | 0.013349 | −0.060387 | −0.018882 | 0.218678 | 0.098131 | 0.032543 | −0.004346 | −0.100335 | −0.08074 | 0.021012 | 0.000534 |
| 78 | 0.115984 | 0.037788 | 0.067915 | 0.06583 | 0.097077 | 0.057261 | −0.011964 | −0.057219 | −0.04618 | −0.006834 | 0.034217 | −0.03821 | 0.014374 | 0.007237 |
| 79 | 0.019869 | 0.004876 | 0.01977 | −0.030008 | 0.054503 | −0.008701 | −0.013069 | −0.10682 | −0.004507 | −0.052254 | −0.066149 | −0.01826 | 0.01794 | 0.027493 |
| 80 | −0.042203 | −0.025215 | −0.036213 | −a015224 | −0.02128 | −0.03029 | 0.042071 | 0.068239 | 0.030029 | −0.030446 | −0.104067 | 0.002479 | −0.061762 | −0.083133 |
| 81 | 0.003284 | −0.002756 | −0.032313 | −0.051793 | 0.02492 | 0.084171 | −0.042615 | 0.040816 | 0.028963 | −0.001671 | −0.065438 | 0.044531 | −0.013707 | −0.05949 |
| 82 | −0.067922 | −0.063315 | −0.053063 | 0.041131 | 0.03347 | 0.065982 | 0.003665 | 0.04156 | 0.110956 | 0.091679 | 0.043853 | −0.048546 | −0.011932 | 0.061233 |
| 83 | 0.1105 | 0.006922 | 0.011541 | −0.007501 | 0.116327 | 0.125156 | −0.092773 | −0.05609 | −0.078255 | −0.045464 | −0.07527 | 0.052429 | 0.117605 | −0.053929 |
| 84 | 0.018018 | 0.005119 | 0.017237 | −0.022509 | −0.033903 | 0.028275 | 0.171439 | −0.083288 | −0.078035 | 0.02744 | 0.03291 | 0.012393 | 0.007756 | −0.080847 |
| 85 | 0.021166 | 0.027595 | 0.048309 | 0.036173 | −0.007587 | 0.0137 | 0.057773 | −0.07982 | 0.017608 | 0.021891 | −0.002436 | 0.017443 | 0.044964 | 0.01008 |
| 86 | 0.05793 | 0.036086 | 0.032021 | −0.00132 | 0.01457 | 0.018952 | 0.061243 | 0.112636 | −0.029902 | −0.060136 | −0.08142 | 0.029895 | −0.002058 | 0.073352 |
| 87 | −0.048469 | −0.027382 | 0.003851 | −0.042597 | −0.086118 | −0.033108 | −0.00969 | −0.117295 | −0.059224 | −0.036575 | 0.015067 | 0.007208 | 0.017732 | −0.105224 |
| 88 | −0.025184 | 0.00339 | 0.010195 | −0.01708 | 0.05231 | 0.10048 | −0.101769 | 0.105332 | 0.036844 | −0.011838 | 0.038207 | 0.020365 | −0.041656 | −0.105849 |
| 89 | 0.0327441 | 0.045739 | 0.08061 | 0.065186 | 0.049027 | −0.001517 | 0.019794 | −0.063604 | −0.053137 | −0.025077 | −0.040668 | −0.055641 | −0.058978 | 0.115544 |
| 90 | −0.006238 | 0.0476971 | 0.010572 | −0.009539 | −0.060336 | −0.143535 | 0.052742 | −0.010208 | 0.04502 | −0.006961 | −0.034018 | 0.057022 | 0.076713 | −0.119784 |
| 91 | 0.000567 | −0.027459 | −0.025145 | 0.021039 | −0.017735 | −0.043353 | −0.079682 | 0.01343 | 0.043079 | 0.008042 | 0.011094 | −0.063902 | −0.042131 | 0.175951 |
| 92 | −0.044072 | −0.022762 | −0.007314 | 0.024496 | −0.058098 | −0.043658 | 0.024647 | −0.120752 | −0.041834 | −0.015803 | −0.022524 | −0.02642 | −0.025024 | −0.01228 |
| 93 | −0.012052 | −0.060041 | −0.074116 | −0.021901 | 0.07641 | 0.051178 | −0.038231 | 0.025941 | 0.082783 | 0.0412 | 0.067646 | 0.020519 | 0.008377 | 0.078459 |
| 94 | 0.012618 | −0.004852 | −0.010074 | −0.048223 | −0.033659 | 0.015764 | −0.030102 | 0.129743 | −0.07761 | −0.132718 | −0.127026 | −0.02984 | 0.039775 | 0.062028 |
| 95 | −0.016964 | 0.004685 | 0.033299 | −0.042349 | −0.112175 | −0.082285 | 0.072937 | −0.083134 | −0.077493 | −0.01552 | 0.097706 | 0.028407 | 0.024582 | −0.082354 |
| 96 | −0.05553 | −0.032138 | −0.013077 | 0.015447 | −0.021657 | −0.026105 | −0.179194 | −0.044336 | −0.005169 | −0.007575 | −0.049196 | −0.006175 | −0.00866 | −0.013562 |
| 97 | −0.008623 | 0.012043 | −0.004918 | 0.016806 | 0.02843 | 0.008231 | 0.097223 | 0.033116 | 0.007204 | −0.009308 | 0.015732 | −0.013525 | 0.011434 | 0.005565 |
| 98 | −0.006887 | −0.130462 | −0.087785 | −0.017141 | 0.060048 | 0.008518 | 0.009663 | −0.147562 | −0.079916 | −0.024107 | 0.03869 | −0.058042 | −0.038712 | −0.00113 |
| 99 | 0.0282081 | 0.061469 | 0.031762 | 0.026318 | 0.087069 | 0.158351 | 0.003828 | 0.011915 | 0.0442671 | 0.0173951 | −0.000149 | 0.005641 | −0.053715 | 0.024864 |
| 100 | −0.02961 | −0.006661 | −0.00924 | −0.047132 | −0.074687 | −0.064144 | −0.003979 | −0.020216 | −0.031339 | −0.025345 | −0.044674 | −0.008932 | 0.000188 | −0.03264 |
| 101 | −0.049139 | −0.055473 | −0.059539 | −0.034932 | −0.005406 | −0.008482 | −0.013851 | 0.025389 | 0.036072 | 0.039437 | 0.017423 | −0.037594 | −0.026098 | 0.031217 |
| 102 | 0.03188 | 0.008904 | 0.016017 | 0.013018 | 0.012625 | −0.004735 | −0.04013 | −0.040556 | −0.117659 | −0.126242 | −0.106056 | −0.005262 | −0.025377 | −0.009508 |
| 103 | −0.002996 | 0.004731 | −0.002293 | 0.013397 | −0.0133 | −0.077308 | −0.053748 | −0.037574 | −0.009291 | −0.007605 | −0.021725 | 0.003195 | −0.013185 | 0.072667 |
| 104 | 0.006746 | 0.0150761 | 0.0124971 | 0.021731 | 0.032064 | 0.028399 | −0.000894 | 0.025812 | −0.016078 | −0.002543 | 0.0063041 | −0.050031 | −0.089552 | −0.024207 |
| 105 | 0.004971 | 0.003403 | −0.019382 | 0.003472 | −0.014445 | 0.01376 | −0.008121 | 0.076816 | 0.003932 | 0.006177 | −0.026529 | −0.028261 | −0.026724 | 0.019855 |
| 106 | 0.007421 | −0.005277 | −0.000809 | 0.029026 | 0.038104 | 0.032122 | −0.006052 | −0.001995 | 0.019405 | −0.018106 | 0.022123 | 0.007214 | 0.008581 | 0.037689 |
| 107 | −0.009961 | 0.023112 | 0.012534 | 0.004321 | −0.042609 | −0.00365 | 0.02658 | 0.006107 | 0.067347 | 0.048414 | 0.040341 | −0.014223 | 0.024571 | −0.021256 |
| 108 | 0.008606 | 0.025796 | 0.020418 | −0.003831 | −0.019251 | −0.0442 | 0.052946 | 0.003484 | −0.027389 | −0.024336 | −0.054187 | 0.01648 | 0.055663 | 0.005117 |
| 109 | 0.012295 | 0.010911 | −0.000059 | −0.005571 | −0.015658 | −0.019538 | 0.053498 | −0.034902 | −0.005896 | 0.006294 | 0.01557 | 0.019911 | −0.008068 | 0.069764 |
| 110 | −0.016606 | −0.000786 | −0.022617 | −0.025698 | −0.031844 | −0.011249 | −0.081432 | −0.037865 | 0.024634 | −0.010631 | −0.050711 | 0.022012 | 0.028909 | −0.035642 |
| 111 | 0.011968 | 0.014501 | 0.006775 | 0.005126 | −0.006448 | 0.025552 | −0.004391 | 0.056886 | 0.014963 | 0.012896 | −0.022378 | −0.003988 | −0.004071 | 0.027231 |
| 112 | 0.025453 | −0.011505 | −0.003794 | −0.006132 | 0.051961 | 0.049731 | −0.02714 | −0.009339 | −0.038674 | −0.029096 | −0.013709 | 0.042679 | 0.028368 | −0.012829 |
| 113 | 0.027803 | 0.016777 | 0.035024 | 0.019168 | −0.022573 | −0.016948 | 0.010807 | 0.03335 | 0.012399 | 0.007243 | −0.02695 | −0.008308 | 0.087125 | −0.00936 |
| 114 | −0.006072 | 0.003027 | 0.009256 | −0.00456 | −0.020894 | −0.011454 | −0.008948 | −0.015469 | −0.032055 | −0.034023 | −0.023248 | 0.014718 | 0.052112 | 0.012355 |
| 115 | −0.0150141 | −0.0094791 | −0.015485 | −0.035324 | −0.024771 | 0.000077 | −0.07355 | −0.04054 | −0.018313 | −0.011406 | 0.015421 | 0.008748 | −0.023927 | −0.026444 |
| 116 | −0.013817 | −0.001372 | −0.008458 | −0.017369 | −0.055225 | −0.024966 | −0.016975 | 0.027337 | 0.005556 | −0.007411 | −0.021252 | −0.011353 | 0.004777 | −0.008033 |
| 117 | −0.010866 | 0.009267 | 0.001177 | 0.002984 | −0.005184 | 0.006756 | −0.026366 | 0.002715 | −0.00389 | 0.021208 | −0.003874 | 0.003381 | −0.015643 | −0.015997 |
| 118 | −0.023966 | −0.019377 | −0.011651, | −0.020268 | 0.004696 | 0.038772 | −0.050704 | 0.068023 | −0.000581 | 0.014108 | 0.009217 | −0.000383 | −0.033581 | −0.023567 |
| 119 | −0.003224 | 0.011073 | 0.001207 | −0.0243 | −0.010256 | 0.008587 | 0.002275 | −0.024088 | 0.003995 | 0.00503 | 0.003816 | −0.010167 | −0.020771 | −0.009491 |
| 120 | −0.005081 | 0.017643 | 0.019643 | 0.003446 | −0.020425 | −0.028534 | 0.04316 | −0.046938 | −0.016263 | 0.002636 | 0.001051 | −0.008973 | −0.004397 | −0.046789 |
| 121 | −0.010754 | −0.008667 | −0.001912 | 0.011641 | 0.004364 | −0.012093 | 0.008427 | −0.032134 | 0.003779 | 0.010446 | 0.00654 | −0.022787 | −0.009805 | 0.003694 |
| 122 | 0.003515 | −0.019941 | −0.012837 | 0.029947 | 0.00931 | −0.00706 | −0.061788 | −0.02495 | −0.000461 | 0.009401 | −0.002964 | −0.006341 | 0.000781 | 0.036874 |
| 123 | −0.007455 | 0.004233 | 0.008033 | 0.018071 | −0.028688 | −0.054127 | −0.01313 | −0.020334 | 0.023466 | 0.020527 | −0.006314 | −0.021506 | 0.001232 | 0.011622 |
| 124 | 0.02885 | 0.028546 | 0.026262 | 0.0155 | 0.034514 | 0.019226 | −0.002787 | −0.002783 | −0.000416 | 0.000252 | −0.006003 | −0.010674 | −0.008299 | −0.013707 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 125 | 0.020437 | −0.02579 | 0.001363 | 0.021361 | 0.011417 | −0.019443 | −0.025027 | −0.035724 | −0.053956 | −0.017468 | 0.017121 | 0.004959 | 0.005066 | −0.003176 |
| 126 | 0.017605 | 0.011443 | 0.024274 | 0.020738 | 0.003855 | 0.008989 | −0.035743 | 0.015107 | −0.016468 | −0.005355 | −0.015302 | 0.010925 | 0.018781 | −0.024546 |
| 127 | 0.006947 | 0.008595 | 0.019459 | 0.008793 | 0.000546 | 0.006214 | −0.032245 | 0.028159 | −0.008198 | 0.006641 | 0.013599 | 0.032506 | 0.036893 | −0.035648 |
| 128 | −0.0039 | 0.014135 | 0.012746 | −0.018465 | −0.054439 | −0.033715 | −0.035931 | 0.025554 | −0.006743 | −0.000403 | 0.032242 | −0.011309 | −0.000953 | −0.011592 |
| 129 | −0.005867 | −0.002095 | 0.007757 | 0.013682 | −0.008012 | −0.01291 | 0.018763 | −0.035167 | 0.011 | 0.021652 | 0.036062 | 0.020525 | −0.006195 | 0.024635 |
| 130 | 0.006175 | −0.003428 | −0.001843 | −0.010847 | 0.04336 | 0.040427 | 0.032664 | −0.104527 | 0.038672 | 0.022685 | 0.009505 | 0.010197 | 0.023063 | −0.037452 |
| 131 | 0.000011 | 0.004983 | 0.01037 | 0.029313 | −0.002767 | −0.000598 | 0.030212 | −0.003662 | 0.032603 | 0.027615 | −0.012335 | −0.022889 | −0.016806 | 0.02967 |
| 132 | −0.014501 | 0.017866 | −0.020676 | −0.033273 | −0.054696 | −0.051751 | 0.012935 | 0.026116 | 0.046653 | 0.008426 | −0.028153 | −0.018053 | −0.03627 | 0.002356 |
| 133 | −0.014304 | −0.004156 | −0.001989 | −0.013889 | 0.000201 | 0.003752 | 0.028903 | 0.035374 | −0.005092 | 0.007082 | 0.018461 | 0.000103 | 0.006678 | 0.014066 |
| 134 | −0.001973 | −0.000201 | −0.00233 | 0.010106 | −0.013666 | −0.032422 | 0.008132 | 0.007403 | −0.023477 | 0.00862 | −0.017366 | −0.006953 | −0.018073 | −0.021254 |
| 135 | 0.005846 | 0.011889 | 0.01942 | 0.027621 | 0.017901 | 0.009384 | −0.020355 | 0.029102 | −0.000457 | −0.007196 | −0.004434 | 0.012782 | −0.017892 | −0.009408 |
| 136 | 0.000656 | −0.014935 | −0.007755 | 0.01329 | 0.011777 | 0.003862 | 0.009066 | −0.045778 | −0.028912 | −0.026795 | −0.007409 | 0.001236 | −0.026061 | −0.00776 |
| 137 | −0.016656 | −0.034939 | −0.037053 | −0.023384 | 0.000574 | 0.009823 | −0.069523 | 0.02451 | 0.02762 | 0.056083 | 0.044627 | −0.021693 | 0.028202 | 0.033539 |
| 138 | −0.000824 | −0.015133 | 0.001205 | 0.038281 | 0.030913 | 0.006108 | −0.03401 | 0.028911 | 0.044403 | 0.024498 | 0.01592 | −0.006365 | −0.000348 | −0.009734 |
| 139 | 0.011983 | 0.000581 | −0.011678 | 0.004797 | 0.006549 | −0.037281 | 0.014144 | −0.081653 | −0.017036 | −0.018042 | −0.058425 | −0.009266 | 0.038176 | 0.020885 |
| 140 | 0.002781 | 0.0082441 | 0.005567 | 0.002057 | −0.005129 | −0.04268 | 0.073798 | 0.012213 | 0.004108 | −0.015098 | −0.013949 | 0.03981 | −0.020104 | −0.009749 |
| 141 | 0.016574 | 0.015853 | 0.013242 | 0.010695 | −0.006022 | −0.0009 | −0.044374 | −0.013489 | −0.008243 | −0.026818 | −0.037112 | −0.026858 | −0.017571 | −0.04195 |
| 142 | −0.043969 | −0.017002 | −0.006823 | −0.011638 | 0.004663 | 0.017901 | −0.024943 | 0.009965 | 0.016386 | 0.001146 | −0.010785 | 0.037838 | 0.007637 | −0.02127 |
| 143 | −0.002498 | 0.01316 | 0.014765 | 0.031011 | 0.010574 | −0.025312 | 0.009665 | −0.020563 | 0.018976 | 0.012004 | 0.028901 | −0.056858 | −0.026957 | −0.001015 |
| 144 | 0.017139 | 0.014697 | 0.013053 | −0.013342 | 0.00276 | −0.018401 | −0.002746 | −0.027579 | −0.02828 | −0.036581 | −0.004183 | 0.024911 | 0.017307 | −0.05046 |
| 145 | 0.0100611 | 0.011064 | 0.020921 | 0.037089 | 0.021345 | −0.014615 | −0.006639 | 0.029228 | −0.010581 | −0.005582 | −0.011547 | −0.006364 | 0.02118 | −0.003666 |
| 146 | −0.00486 | 0.008183 | 0.011945 | 0.012929 | −0.025775 | −0.024082 | 0.009963 | 0.002718 | −0.015645 | −0.008581 | −0.015981 | 0.027409 | 0.0153 | −0.029292 |
| 147 | −0.012156 | −0.015333 | −0.009745 | −0.013255 | −0.019953 | 0.035318 | 0.063432 | 0.011608 | 0.00955 | −0.002207 | −0.005917 | 0.04737 | 0.057991 | 0.017998 |
| 148 | −0.001401 | −0.008471 | −0.001226 | −0.037171 | 0.023822 | 0.047314 | −0.043996 | 0.013506 | 0.008756 | −0.02021 | −0.015904 | 0.01068 | 0.002816 | −0.014836 |
| 149 | 0.030219 | 0.008516 | −0.002188 | −0.001158 | 0.040037 | 0.013056 | −0.047122 | 0.047308 | 0.036352 | 0.046188 | 0.056038 | −0.023937 | −0.032668 | 0.026324 |
| 150 | 0.018065 | 0.008343 | 0.009068 | −0.024224 | −0.005919 | 0.021105 | 0.001729 | −0.016387 | −0.005507 | 0.001409 | −0.020239 | 0.004418 | 0.034782 | −0.057128 |
| 151 | 0.013603 | 0.025331 | −0.007864 | 0.01024 | 0.010384 | −0.026998 | −0.003393 | −0.048798 | 0.011182 | 0.008948 | −0.022608 | −0.032704 | −0.011701 | −0.011011 |
| 152 | −0.004375 | −0.009492 | −0.006823 | 0.00041 | 0.022168 | 0.011944 | −0.028826 | 0.011347 | 0.035663 | 0.031916 | 0.037274 | 0.013186 | 0.017957 | 0.005376 |
| 153 | −0.00711 | −0.003046 | −0.014743 | −0.011456 | −0.020395 | −0.014768 | −0.000525 | −0.019832 | 0.041115 | 0.008565 | 0.000954 | 0.020568 | 0.026713 | 0.005067 |
| 154 | 0.005361 | 0.010619 | −0.000451 | −0.033321 | −0.00268 | 0.035452 | 0.01672 | 0.012939 | −0.000891 | −0.025195 | −0.029304 | 0.025578 | 0.016383 | −0.031193 |
| 155 | 0.006811 | 0.003122 | 0.0001711 | 0.000307 | 0.006402 | −0.004245 | −0.031828 | 0.00742 | −0.011106 | −0.038169 | −0.009811 | 0.007023 | −0.021165 | −0.014577 |
| 156 | 0.001117 | 0.014862 | 0.011382 | 0.012091 | −0.029063 | −0.061744 | −0.010937 | 0.04054 | 0.014412 | −0.02733 | −0.007227 | 0.023991 | −0.031427 | 0.003291 |
| 157 | −0.003025 | 0.006354 | 0.014062 | 0.017299 | −0.013557 | −0.004039 | −0.018112 | 0.011787 | 0.001971 | 0.014794 | −0.007674 | −0.02254 | −0.053605 | −0.003128 |
| 158 | 0.003615 | −0.016312 | −0.010955 | −0.021013 | 0.002108 | −0.018057 | 0.050706 | 0.065608 | −0.016242 | −0.013345 | −0.002892 | −0.022644 | 0.003102 | 0.019057 |
| 159 | 0.00662 | 0.018748 | 0.031609 | −0.008304 | −0.015515 | −0.017969 | 0.018873 | 0.042257 | 0.004264 | −0.002006 | −0.004635 | 0.022686 | 0.036211 | 0.014249 |
| 160 | 0.01018 | −0.001916 | −0.004115 | 0.00532 | 0.024762 | −0.027171 | 0.078023 | 0.048767 | 0.047596 | 0.024221 | 0.012888 | −0.006901 | −0.011946 | −0.03196 |
| 161 | 0.015981 | 0.003549 | 0.015859 | 0.029551 | 0.04152 | −0.011752 | 0.040678 | −0.051178 | −0.000219 | −0.022951 | −0.004157 | −0.028202 | −0.016751 | −0.000056 |
| 162 | 0.007628 | −0.02783 | −0.008429 | −0.01007 | 0.032762 | 0.053206 | 0.047114 | −0.00479 | −0.042034 | 0.014161 | 0.033449 | −0.018242 | 0.001099 | 0.02886 |
| 163 | −0.015354 | 0.010285 | 0.023406 | 0.016643 | 0.002397 | −0.008603 | −0.05628 | 0.036507 | 0.015825 | 0.005441 | −0.004361 | 0.015781 | 0.029453 | −0.009656 |
| 164 | 0.00449 | 0.016291 | 0.029759 | −0.003685 | −0.031321 | 0.005038 | 0.002943 | −0.000003 | −0.059409 | −0.030251 | −0.035669 | −0.013317 | 0.030496 | 0.028533 |
| 165 | 0.006546 | 0.016346 | 0.012572 | 0.010591 | 0.005732 | −0.038768 | 0.052783 | −0.012941 | −0.007636 | −0.017703 | 0.020451 | 0.007544 | 0.025895 | 0.013318 |
| 166 | 0.014624 | −0.002601 | −0.006467 | 0.025932 | 0.067072 | 0.024228 | −0.019261 | −0.057049 | 0.04926 | 0.04736 | 0.041586 | −0.025776 | −0.059348 | 0.035252 |
| 167 | −0.012042 | −0.009936 | −0.020006 | 0.030436 | 0.023201 | 0.007692 | 0.024327 | 0.02028 | 0.019632 | 0.005167 | 0.025387 | −0.026174 | −0.017228 | 0.016892 |
| 168 | −0.044444 | 0.024316 | 0.029071 | −0.008057 | −0.080162 | −0.079415 | 0.066961 | −0.020048 | 0.035804 | 0.032966 | 0.026329 | −0.010277 | −0.011657 | −0.064162 |
| 169 | −0.020048 | −0.006576 | 0.000163 | −0.008029 | −0.009425 | 0.00072 | 0.008611 | −0.010043 | 0.029736 | 0.030709 | 0.016198 | −0.0311 | −0.016147 | 0.020175 |
| 170 | −0.015484 | −0.013965 | −0.01779 | −0.041716 | −0.015889 | 0.014589 | 0.037248 | −0.02155 | 0.04943 | 0.049122 | 0.035128 | −0.037533 | −0.015655 | 0.026098 |
| 171 | −0.036257 | −0.001207 | −0.003774 | −0.020449 | −0.067487 | −0.074447 | 0.030453 | −0.036346 | 0.041046 | 0.033876 | 0.012472 | −0.024168 | −0.005966 | −0.003612 |
| 172 | 0.031827 | 0.020046 | 0.037264 | 0.008832 | 0.026221 | 0.010383 | −0.032284 | −0.051942 | −0.065373 | −0.060952 | −0.040662 | −0.01174 | 0.023597 | −0.009945 |
| 173 | 0.029835 | −0.009782 | 0.011764 | 0.000962 | 0.019148 | 0.009193 | −0.013553 | −0.07403 | −0.097313 | −0.062949 | −0.018741 | 0.008927 | 0.033334 | 0.011213 |
| 174 | 0.000029 | 0.012598 | 0.013132 | 0.013657 | 0.034809 | 0.022872 | −0.027845 | −0.008959 | 0.004561 | −0.070124 | −0.094273 | 0.002047 | −0.017704 | −0.020397 |
| 175 | 0.022435 | 0.040949 | 0.015756 | −0.006666 | 0.028035 | 0.038369 | 0.009501 | 0.054529 | 0.043138 | −0.00316 | −0.079611 | −0.010017 | −0.000552 | −0.042161 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 176 | 0.011286 | 0.02658 | 0.022101 | 0.00798 | 0.002099 | −0.035584 | 0.019559 | 0.032737 | 0.020433 | −0.007641 | −0.042458 | −0.044964 | 0.030448 | 0.013305 |
| 177 | 0.01027 | 0.005321 | −0.004057 | −0.008816 | 0.011853 | 0.061038 | 0.007745 | 0.000378 | 0.038423 | 0.035262 | 0.07194 | 0.006701 | −0.015819 | 0.02545 |
| 178 | −0.054744 | −0.058425 | −0.049638 | −0.022658 | 0.004642 | 0.016653 | −0.053503 | 0.005141 | 0.035067 | 0.024518 | 0.035366 | −0.003463 | 0.017093 | 0.003552 |
| 179 | 0.890472 | −0.058942 | −0.066912 | −0.063933 | −0.091976 | −0.034373 | −0.005439 | 0.017218 | 0.049274 | 0.036014 | 0.010849 | −0.01608 | −0.032021 | −0.014831 |
| 180 | −0.065025 | 0.904993 | −0.078953 | −0.053546 | −0.02061 | 0.009697 | −0.043692 | −0.028979 | 0.006563 | 0.0141 | 0.02028 | −0.018947 | −0.017012 | 0.029961 |
| 181 | −0.070002 | −0.077678 | 0.905673 | −0.069315 | −0.032252 | 0.005056 | −0.032579 | 0.003822 | 0.039057 | 0.03416 | 0.02331 | −0.009946 | −0.022691 | 0.02634 |
| 182 | −0.053875 | −0.046377 | −0.071194 | 0.86141 | −0.078713 | 0.006129 | −0.00822 | −0.010372 | 0.003703 | 0.010447 | −0.002712 | −0.005808 | 0.005051 | −0.051888 |
| 183 | −0.086155 | −0.00961 | −0.032604 | −0.093659 | 0.791981 | −0.144707 | 0.03557 | −0.008782 | −0.002224 | 0.00063 | −0.030853 | −0.013335 | 0.003184 | −0.065605 |
| 184 | −0.058382 | 0.005411 | 0.000712 | −0.015169 | −0.169094 | 0.685244 | 0.015491 | −0.039706 | −0.028009 | −0.050168 | −0.059998 | −0.014051 | 0.005408 | −0.048331 |
| 185 | 0.014607 | −0.036 | −0.020383 | 0.000746 | 0.058198 | 0.020184 | 0.617058 | −0.060464 | −0.000521 | −0.043966 | −0.02656 | 0.025376 | 0.01828 | 0.003451 |
| 186 | 0.013827 | −0.02359 | −0.004071 | −0.026088 | −0.019935 | −0.031581 | −0.003725 | 0.616017 | −0.089061 | −0.056196 | −0.018538 | −0.021961 | −0.024514 | −0.046054 |
| 187 | 0.024093 | −0.020809 | 0.011221 | −0.015944 | −0.013095 | −0.008403 | 0.004357 | −0.092926 | 0.803429 | −0.140196 | −0.099485 | −0.000234 | 0.016389 | −0.027247 |
| 188 | 0.017483 | −0.003357 | 0.015059 | −0.007601 | −0.00708 | −0.023814 | −0.033646 | −0.038196 | −0.133836 | 0.827729 | −0.165348 | 0.017319 | 0.020946 | −0.025987 |
| 189 | −0.007433 | 0.015257 | 0.008276 | −0.010485 | −0.037863 | −0.031255 | 0.009228 | 0.03219 | −0.073212 | −0.145665 | 0.71292 | −0.00629 | −0.005986 | −0.01174 |
| 190 | −0.007855 | −0.00966 | −0.00752 | −0.013897 | −0.030389 | −0.039331 | 0.059489 | −0.020562 | 0.003266 | 0.030434 | 0.008014 | 0.845907 | −0.080515 | 0.038862 |
| 191 | −0.027452 | −0.017182 | −0.025728 | −0.003593 | −0.002195 | 0.006397 | 0.034 | −0.006242 | 0.016761 | 0.03204 | 0.020118 | −0.09908 | 0.815081 | 0.02761 |
| 192 | −0.017523 | 0.016069 | 0.006284 | −0.048724 | −0.045907 | 0.007724 | −0.010581 | −0.037951 | −0.023065 | −0.031368 | −0.039381 | 0.026664 | −0.005301 | 0.714894 |
| 193 | −0.014762 | 0.00437 | 0.008326 | −0.05329 | −0.059798 | −0.032788 | −0.00868 | −0.06052 | −0.052644 | −0.047844 | −0.028612 | −0.006218 | 0.006816 | −0.110493 |
| 194 | −0.030203 | −0.026316 | −0.008645 | 0.007425 | −0.042628 | −0.043077 | 0.003072 | −0.004969 | −0.058173 | −0.075025 | −0.093419 | −0.022065 | 0.000513 | 0.025716 |
| 195 | −0.014485 | −0.012909 | −0.025579 | −0.004484 | 0.004103 | 0.043488 | 0.005784 | −0.058459 | 0.000246 | 0.031601 | 0.007173 | −0.041276 | −0.045273 | 0.043628 |
| 196 | −0.014872 | −0.019039 | −0.029748 | −0.028963 | 0.000687 | −0.008337 | −0.005158 | −0.032265 | −0.003381 | 0.002212 | −0.007127 | −0.051222 | −0.034244 | 0.009654 |
| 197 | −0.004632 | 0.011661 | 0.00716 | −0.028241 | −0.018501 | 0.002739 | 0.046244 | −0.018734 | 0.00145 | 0.016607 | 0.00485 | −0.101658 | −0.098255 | −0.024478 |
| 198 | 0.003736 | 0.006492 | 0.01667 | 0.008075 | −0.022632 | −0.038176 | −0.024454 | −0.021458 | −0.011509 | −0.013627 | −0.028153 | 0.007332 | 0.036588 | 0.00873 |
| 199 | 0.001504 | −0.004079 | 0.018474 | 0.015686 | 0.010519 | 0.008856 | 0.057952 | −0.013526 | −0.027231 | −0.023546 | −0.063676 | 0.006489 | −0.01623 | 0.007048 |
| 200 | −0.009004 | −0.003544 | −0.012557 | −0.015123 | −0.0114 | 0.06408 | 0.019526 | 0.012924 | −0.018001 | −0.015362 | −0.011773 | 0.045736 | 0.043431 | 0.009929 |
| 201 | 0.002002 | −0.043567 | −0.023405 | −0.011753 | −0.002521 | 0.039007 | −0.021288 | 0.0282 | −0.01038 | −0.004822 | −0.011655 | 0.009949 | 0.005463 | 0.027584 |
| 202 | 0.021603 | 0.01839 | 0.019385 | 0.014542 | 0.036062 | 0.072191 | −0.006911 | −0.083765 | 0.002926 | 0.005571 | 0.018837 | −0.000961 | −0.0034 | −0.027385 |
| 203 | −0.015358 | −0.010462 | 0.011766 | −4.002236 | −0.042163 | 0.017747 | 0.025456 | 0.046784 | −0.021632 | −0.00671 | −0.015718 | −0.035192 | −0.033441 | 0.028917 |
| 204 | −0.00938 | −0.004293 | −0.012551 | −0.020071 | −0.0307 | −0.066083 | −0.028389 | 0.046936 | −0.017889 | −0.00152 | 0.015964 | −0.024189 | 0.005011 | 0.039913 |
| 205 | −0.013956 | 0.004155 | 0.002986 | −0.033119 | −0.039383 | 0.022308 | 0.054064 | 0.008328 | 0.01534 | 0.016437 | −0.004116 | −0.068591 | −0.03598 | −0.041034 |
| 206 | 0.037693 | 0.022729 | 0.040297 | 0.039672 | 0.036676 | 0.007912 | 0.008356 | −0.004114 | 0.033667 | 0.025184 | −0.006954 | −0.050316 | −0.01295 | −0.035457 |
| 207 | 0.008622 | 0.011483 | −0.007319 | −0.022395 | −0.01621 | −0.00388 | 0.014445 | 0.033755 | 0.028913 | 0.001914 | −0.019654 | 0.002168 | 0.038643 | 0.046009 |
| 208 | 0.031086 | 0.010421 | 0.027315 | 0.045125 | 0.043076 | 0.022325 | −0.015518 | −0.058355 | −0.009106 | 0.00461 | 0.024403 | −0.001692 | −0.029229 | 0.041836 |
| 209 | −0.007617 | 0.001832 | −0.007976 | −0.010934 | −0.017706 | −0.041599 | −0.0442 | 0.051085 | 0.029999 | −0.004552 | 0.023125 | 0.042564 | 0.041159 | −0.044554 |
| 210 | 0.010463 | −0.022221 | −0.02312 | −0.018201 | 0.002179 | 0.009852 | 0.002456 | −0.011118 | −0.004054 | 0.047956 | 0.057883 | −0.04241 | −0.02914 | 0.006079 |
| 211 | 0.018946 | −0.000989 | 0.031038 | 0.027301 | 0.02471 | 0.01939 | −0.010227 | 0.029169 | −0.03469 | −0.018603 | 0.025047 | 0.0224 | 0.011931 | −0.007993 |
| 212 | 0.014416 | 0.014025 | 0.006445 | 0.008963 | −0.003405 | 0.000458 | −0.054235 | −0.049675 | 0.025043 | 0.017455 | 0.021025 | −0.014786 | −0.001531 | 0.006205 |
| 213 | −0.026526 | −0.041411 | −0.036605 | −0.051553 | 0.001199 | −0.014332 | 0.004541 | −0.033179 | −0.021777 | −0.033541 | −0.063303 | −0.017942 | −0.038685 | −0.003602 |
| 214 | −0.085233 | −0.053729 | −0.048051 | −0.036441 | −0.080109 | −0.068914 | −0.010141 | −0.008966 | 0.019782 | 0.008557 | −0.01743 | −0.004991 | −0.012772 | −0.025292 |
| 215 | −0.045554 | −0.059607 | −0.064937 | −0.019875 | −0.024364 | −0.034408 | −0.034914 | −0.059225 | 0.013505 | 0.027142 | 0.019123 | −0.016896 | −0.026201 | 0.023787 |
| 216 | 0.031257 | 0.019259 | 0.020836 | 0.032649 | 0.028561 | 0.007302 | 0.023618 | −0.016161 | 0.006998 | 0.008048 | 0.003182 | 0.013916 | −0.022919 | 0.031958 |
| 217 | 0.032532 | 0.037272 | 0.039882 | 0.005067 | −0.012328 | 0.03435 | 0.009817 | −0.015213 | −0.035099 | −0.028378 | −0.030866 | −0.006653 | 0.000554 | 0.010193 |
| 218 | 0.005749 | 0.00063 | −0.006941 | 0.002042 | 0.004246 | −0.011811 | −0.022466 | −0.039308 | 0.029738 | 0.022517 | 0.021024 | 0.007025 | 0.006039 | 0.024555 |
| 219 | 0.007332 | 0.011404 | 0.002977 | 0.025853 | 0.007896 | −0.009285 | 0.007355 | −0.027396 | 0.031771 | 0.019283 | 0.005088 | 0.01516 | −0.013386 | 0.02321 |
| 220 | 0.0243 | 0.019645 | 0.021291 | 0.000217 | −0.02007 | −0.0211 | −0.023503 | −0.009676 | −0.015513 | −0.008427 | −0.006971 | −0.013822 | −0.013397 | 0.034596 |
| 221 | 0.010065 | 0.001957 | −0.000235 | 0.004292 | 0.013752 | 0.034808 | −0.016206 | 0.027081 | 0.026985 | 0.027248 | 0.038457 | 0.0197741 | 0.026659 | 0.018752 |
| 222 | 0.006099 | 0.004181 | −0.003707 | 0.010621 | 0.007333 | 0.021834 | 0.011492 | 0.04812 | 0.013739 | 0.006041 | 0.017494 | 0.033554 | 0.01556 | −0.053873 |
| 223 | 0.001697 | 0.003284 | −0.009948 | 0.001304 | −0.000587 | 0.004666 | 0.012573 | 0.044574 | 0.035215 | 0.023253 | 0.029892 | 0.017032 | 0.020511 | 0.016332 |
| 224 | −0.011999 | −0.001303 | −0.00814 | 0.01404 | 0.031417 | 0.012893 | −0.032233 | 0.005508 | 0.029959 | 0.008984 | 0.011783 | 0.018364 | −0.005995 | −0.074157 |
| 225 | −0.01084 | −0.003571 | −0.00735 | 0.01446 | 0.01275 | 0.003755 | −0.031417 | 0.002712 | 0.030705 | 0.02623 | 0.029629 | 0.023658 | 0.007423 | −0.063155 |
| 226 | 0.02333 | 0.019727 | 0.016455 | 0.008055 | −0.006972 | −0.024236 | −0.011572 | −0.006195 | −0.008882 | −0.010001 | −0.022467 | 0.002489 | 0.010891 | 0.005189 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 227 | −0.004006 | 0.00189 | 0.020115 | 0.018801 | −0.014106 | −0.03013 | −0.032287 | 0.012639 | −0.005758 | −0.009033 | −0.022753 | −0.005093 | 0.004225 | −0.032972 |
| 228 | 0.014186 | 0.025597 | 0.012077 | −0.01387 | 0.020041 | 0.048733 | −0.001762 | 0.016408 | 0.025128 | 0.024208 | −0.01333 | −0.010699 | −0.006468 | −0.064036 |
| 229 | −0.012125 | −0.024485 | −0.033615 | −0.002907 | 0.017424 | −0.006452 | 0.020244 | −0.025686 | −0.01698 | 0.008391 | 0.024108 | 0.034425 | 0.002522 | 0.038133 |
| 230 | −0.010291 | −0.015435 | −0.012664 | 0.010236 | 0.0186 | 0.030025 | −0.001395 | 0.017168 | −0.003628 | −0.00202 , | 0.026762 | 0.002111 | −0.021361 | 0.024701 |
| 231 | 0.02624 | 0.022735 | 0.019892 | −0.016478 | −0.012316 | −0.028452 | −0.031436 | 0.037907 | −0.035778 | −0.011364 | 0.011395 | −0.000029 | 0.035053 | 0.021867 |
| 232 | −0.01969 | −0.021972 | −0.010376 | −0.000841 | −0.016062 | 0.006654 | −0.046826 | −0.016138 | 0.015043 | −0.006977 | −0.000259 | −0.007935 | −0.015054 | 0.038879 |
| 233 | −0.005111 | 0.003374 | 0.002646 | 0.01306 | −0.017162 | 0.009805 | −0.035902 | −0.046817 | −0.020026 | −0.014974 | −0.040607 | 0.032657 | 0.005369 | −0.025043 |
| 234 | 0.002224 | 0.005979 | 0.010708 | −0.001245 | 0.013015 | 0.025137 | 0.009378 | 0.002925 | −0.003411 | 0.008587 | 0.00677 | 0.016688 | 0.039691 | −0.009061 |
| 235 | −0.000109 | 0.003073 | 0.004054 | 0.012466 | 0.025722 | 0.050362 | −0.008266 | 0.022541 | −0.00095 | 0.012173 | 0.01768 | 0.022776 | 0.02537 | 0.000455 |
| 236 | 0.007436 | 0.007151 | 0.005964 | −0.006646 | −0.004697 | −0.010579 | −0.005422 | 0.010011 | 0.011452 | −0.000443 | −0.01283 | −0.040245 | −0.004138 | 0.035572 |
| 237 | 0.00285 | −0.006413 | −0.004298 | 0.005987 | 0.009273 | −0.01685 | 0.020343 | 0.006269 | −0.01189 | −0.009321 | −0.032682 | −0.013864 | −0.00219 | 0.003835 |
| 238 | −0.00705 | 0.003682 | −0.010163 | 0.006072 | 0.005522 | −0.00042 | 0.042776 | 0.030455 | 0.021065 | 0.014729 | −0.000409 | −0.017899 | −0.048742 | −0.000944 |
| 239 | −0.005125 | 0.006311 | 0.000271 | 0.00464 | −0.006461 | 0.004562 | 0.021087 | 0.005934 | 0.008932 | 0.011408 | 0.014484 | −0.001475 | −0.022444 | −0.006141 |
| 240 | 0.006985 | 0.010986 | 0.019078 | 0.0195 | 0.015704 | 0.029536 | 0.011525 | 0.000196 | −0.006586 | −0.006408 | −0.000946 | −0.017587 | −0.000687 | −0.001306 |
| 241 | −0.009408 | 0.00981 | 0.003206 | 0.002862 | −0.001847 | 0.034213 | 0.007825 | −0.025041 | 0.001533 | −0.001312 | −0.026466 | −0.007268 | −0.007497 | −0.021268 |
| 242 | 0.013691 | −0.003738 | −0.013324 | −0.032659 | −0.005754 | 0.019105 | −0.02518 | −0.010248 | −0.005299 | 0.006228 | −0.02511 | 0.003113 | 0.010668 | 0.000491 |
| 243 | 0.009784 | 0.008765 | 0.00781 | 0.024791 | 0.008134 | −0.006667 | −0.027116 | −0.039845 | 0.020493 | 0.017055 | −0.004303 | 0.00997 | −0.010846 | 0.014212 |
| 244 | −0.015635 | −0.020736 | −0.003727 | 1100075 | −0.009146 | 0.009639 | −0.02268 | 0.00051 | 0.001844 | 0.010359 | 0.033271 | 0.001734 | 0.017945 | 0.001521 |
| 245 | −0.021211 | −0.009431 | −0.016843 | −0.013374 | −0.017779 | −0.02437 | −0.058226 | 0.004716 | 0.008178 | −0.044465 | −0.028398 | 0.024619 | 0.019368 | −0.034276 |
| 246 | 0.007915 | −0.004538 | −0.008769 | −0.020514 | −0.008325 | −0.017997 | −0.029415 | −0.000234 | −0.028291 | −0.020331 | −0.020074 | 0.0059451 | 0.01037 | −0.012505 |
| 247 | −0.002571 | −0.003984 | −0.0009 | 0.003316 | −0.012469 | −0.033383 | −0.013486 | 0.002462 | 0.000359 | 0.001146 | 0.004502 | −0.037367 | 0.00712 | 0.020534 |
| 248 | −0.020541 | −0.006144 | −0.012505 | −0.001425 | −0.027294 | −0.034469 | −0.02181 | 0.019102 | 0.024562 | 0.005324 | −0.002947 | −0.025689 | −0.010252 | 0.028341 |
| 249 | 0.022469 | 0.001938 | 0.017436 | 0.019657 | 0.013986 | 0.00523 | −0.020851 | −0.048281 | −0.010537 | −0.019821 | 0.010207 | 0.007015 | 0.021339 | −0.052484 |
| 250 | 0.006966 | −0.003462 | 0.008782 | −0.000151 | −0.001115 | 0.020453 | 0.042058 | −0.021956 | −0.032662 | 0.004258 | 0.031809 | −0.012708 | 0.007175 | −0.016248 |
| 251 | −0.006505 | −0.00466 | −0.006894 | 0.005901 | 0.003853 | 0.027204 | 0.014404 | 0.002165 | −0.002902 | 0.012209 | 0.021629 | 0.006441 | 0.014918 | 0.010177 |
| 252 | −0.027883 | −0.014492 | −0.021531 | −0.027298 | −0.025497 | −0.01924 | −0.092602 | −0.019149 | 0.026364 | 0.013726 | 0.016111 | 0.01086 | 0.015823 | −0.010254 |
| 253 | −0.010382 | 0.008337 | 0.001566 | 0.006741 | −0.021481 | −0.051225 | −0.03787 | 0.024794 | 0.014785 | 0.006527 | 0.018016 | 0.013766 | 0.009294 | 0.00853 |
| 254 | 0.004987 | −0.005126 | −0.005436 | 0.000517 | 0.024257 | 0.017286 | −0.021236 | −0.017762 | 0.024133 | 0.01413 | 0.020582 | 0.008227 | 0.003937 | −0.013453 |
| 255 | 0.008091 | 0.002196 | 0.004248 | −0.005115 | 0.025337 | 0.031547 | −0.026458 | −0.004383 | 0.00109 | −0.002133 | 0.006707 | 0.004185 | 0.011713 | 0.000347 |
| 256 | 0.003183 | −0.018463 | −0.009566 | −0.016271 | 0.030092 | −0.003257 | −0.080035 | −0.019272 | 0.00551 | −0.039012 | 0.001555 | 0.009895 | 0.000081 | 0.006295 |
| 257 | −0.010598 | −0.004969 | −0.00207 | −0.008 | −0.003253 | 0.026157 | 0.000844 | 0.008651 | 0.002143 | 0.007812 | 0.012846 | 0.012663 | 0.000431 | −0.021375 |
| 258 | −0.001623 | 0.00201 | 0.002288 | 0.000754 | 0.017652 | 0.026211 | 0.021226 | 0.013497 | 0.015617 | 0.007989 | −0.009402 | −0.019549 | 0.004353 | 0.018973 |
| 259 | 0.016247 | 0.001932 | −0.004254 | 0.002045 | 0.015213 | 0.029861 | 0.013632 | −0.016363 | −0.012739 | −0.012748 | −0.010641 | 0.023589 | 0.020204 | −0.051697 |
| 260 | −0.021587 | −0.033246 | −0.024296 | −0.018104 | −0.011306 | −0.005823 | −0.003035 | −0.046459 | −0.033619 | 0.005656 | 0.013282 | 0.012962 | 0.039136 | −0.016563 |
| 261 | 0.001908 | −0.001363 | −0.010771 | −0.016755 | 0.003398 | 0.010391 | 0.016041 | −0.004243 | −0.004174 | 0.014534 | −0.00138 | −0.002671 | 0.025927 | 0.014686 |
| 262 | 0.006392 | −0.002955 | −0.002814 | −0.004699 | 0.003642 | −0.009952 | −0.024472 | 0.038454 | 0.009983 | 0.007172 | 0.00022 | −0.004476 | 0.036668 | −0.001353 |
| 263 | 0.001273 | 0.003264 | −0.006589 | −0.000548 | −0.003789 | −0.002885 | −0.012475 | 0.038324 | 0.011995 | 0.002545 | −0.001083 | 0.012154 | 0.017773 | −0.009446 |
| 264 | 0.021779 | 0.014209 | 0.02001 | 0.033768 | 0.02822 | 0.007424 | 0.031132 | 0.010177 | −0.025728 | −0.027395 | −0.02007 | 0.008094 | 0.006045 | −0.063949 |
| 265 | 0.006671 | 0.013959 | 0.022881 | 0.022421 | 0.009182 | 0.000907 | 0.035655 | 0.006986 | −0.005369 | 0.000037 | −0.016434 | −0.014312 | −0.015737 | 0.000484 |
| 266 | −0.002364 | 0.007018 | 0.013652 | −0.00163 | −0.002127 | −0.014548 | 0.007753 | −0.012532 | −0.01589 | −0.005803 | −0.007286 | 0.006591 | 0.000043 | 0.026988 |
| 267 | 0.026292 | 0.011223 | 0.016343 | 0.01524 | 0.019055 | −0.047766 | 0.031707 | −0.003678 | 0.003014 | 0.001108 | −0.00775 | 0.001354 | 0.021464 | 0.062368 |
| 268 | 0.019553 | 0.01795 | 0.026818 | 0.020823 | −0.007528 | −0.020152 | −0.000275 | −0.011921 | −0.017571 | −0.003348 | −0.010622 | −0.009978 | 0.005199 | 0.010256 |
| 269 | 0.005916 | 0.010002 | 0.008379 | 0.004833 | −0.010044 | −0.020086 | −0.016418 | 0.01288 | −0.004008 | 0.002993 | −0.009533 | 0.001701 | −0.002371 | 0.02489 |
| 270 | 0.001968 | 0.015516 | 0.013793 | 0.002145 | −0.010654 | −0.021519 | −0.009445 | 0.018381 | 0.002079 | −0.002996 | −0.02109 | 0.003162 | −0.005489 | −0.001244 |
| 271 | 0.009077 | 0.013115 | 0.004838 | −0.013236 | −0.015259 | −0.033831 | 0.021673 | −0.033013 | 0.008582 | 0.017026 | 0.017113 | −0.007301 | −0.005484 | −0.075596 |
| 272 | 0.001571 | 0.009039 | −0.006466 | 0.010539 | 0.039516 | 0.030731 | 0.045267 | 0.022863 | 0.017609 | 0.013837 | 0.006636 | −0.000817 | 0.001551 | 0.02384 |
| 273 | −0.007218 | −0.000092 | −0.00334 | 0.015528 | 0.012728 | 0.023225 | 0.001394 | −0.019838 | 0.008809 | 0.007552 | 0.009306 | −0.009642 | −0.01862 | −0.002484 |
| 274 | −0.01039 | −0.007323 | −0.010615 | 0.007503 | 0.018501 | 0.034752 | −0.000592 | −0.020468 | 0.003336 | 0.007286 | 0.009422 | −0.009388 | −0.021761 | −0.003539 |
| 275 | −0.021409 | −0.012364 | −0.000118 | 0.017566 | 0.005047 | −0.016269 | 0.020471 | 0.044132 | 0.006497 | −0.010133 | 0.000666 | −0.01562 | −0.020723 | 0.034238 |
| 276 | 0.004012 | 0.001834 | −0.002888 | 0.001093 | 0.013104 | −0.018536 | 0.008486 | 0.019954 | 0.02544 | 0.006316 | −0.000652 | −0.024532 | −0.001977 | 0.037211 |
| 277 | −0.020491 | −0.008078 | −0.01306 | −0.010585 | 0.001307 | 0.011447 | 0.045988 | 0.008547 | 0.011817 | 0.02009 | 0.017008 | −0.002668 | 0.010345 | 0.001086 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 278 | −0.039264 | −0.016553 | −0.029991 | −0.045691 | −0.025754 | 0.000232 | 0.029677 | 0.038803 | 0.007553 | 0.01523 | 0.004631 | 0.019225 | 0.026316 | −0.013975 |
| 279 | −0.027636 | −0.003862 | −0.014223 | −0.004638 | −0.015182 | 0.000047 | 0.064026 | 0.017841 | 0.025533 | 0.022977 | 0.018946 | 0.000804 | −0.034089 | −0.005015 |
| 280 | 0.027277 | 0.035382 | 0.026364 | 0.019951 | 0.008635 | 0.01476 | 0.031835 | −0.021812 | 0.022975 | 0.018653 | −0.02032 | 0.013573 | −0.002447 | −0.001943 |
| 281 | 0.019174 | 0.003392 | −0.004405 | −0.005846 | −0.009949 | −0.015461 | 0.034366 | −0.033722 | −0.018239 | −0.018238 | −0.018758 | 0.004605 | −0.008444 | 0.015743 |
| 282 | −0.002259 | 0.001005 | −0.012839 | −0.029423 | −0.02295 | −0.013697 | 0.004118 | −0.007222 | 0.009084 | 0.007231 | 0.01912 | 0.006535 | −0.001481 | 0.002044 |
| 283 | −0.009526 | −0.01788 | −0.006796 | 0.012434 | −0.006036 | −0.05045 | −0.008685 | −0.035655 | 0.008386 | 0.00436 | 0.014861 | −0.024803 | 0.002406 | 0.025125 |
| 284 | −0.005621 | −0.010924 | 0.001383 | −0.001202 | 0.000191 | 0.009748 | 0.01672 | −0.014265 | −0.008376 | 0.003396 | 0.019826 | 0.007232 | −0.007757 | −0.017389 |
| 285 | −0.009182 | −0.026619 | −0.010663 | −0011404 | −0.004214 | 0.003144 | 0.004138 | −0.031376 | −0.02082 | −0.00008 | 0.0375 | 0.009526 | 0.002551 | −0.027714 |
| 286 | −0.002039 | −0.022732 | −0.014774 | −0.019659 | −0.009342 | −0.001954 | 0.025959 | 0.002114 | −0.007476 | −0.000702 | 0.010606 | 0.023587 | 0.014912 | −0.000985 |
| 287 | −0.001304 | −0.009464 | −0.00352 | −0.01261 | 0.002181 | 0.004487 | 0.023698 | 0.001854 | 0.002878 | 0.000675 | 0.00551 | 0.022351 | 0.01474 | 0.000293 |
| 288 | −0.006494 | −0.011688 | 0.0087611 | 0.02489 | 0.01091 | −0.039346 | 0.026097 | 0.006226 | −0.024361 | −0.017927 | −0.039022 | −0.041595 | −0.005081 | 0.007349 |
| 289 | 0.015115 | 0.006676 | 0.012926 | 0.011377 | 0.019255 | 0.011253 | 0.007681 | 0.031075 | 0.009834 | 0.022756 | 0.010549 | −0.018318 | 0.008018 | 0.016565 |
| 290 | 0.017188 | 0.021621 | 0.031577 | 0.025937 | 0.004648 | −0.044414 | −0.029067 | −0.00876 | −0.001735 | −0.009079 | 0.005835 | 0.008366 | 0.018695 | −0.014552 |
| 291 | 0.02136 | 0.020637 | 0.031647 | 0.023702 | 0.009077 | −0.039957 | −0.029268 | −0.008244 | −0.003985 | −0.006514 | 0.010456 | 0.008936 | 0.021794 | −0.014619 |
| 292 | 0.02164 | 0.024405 | 0.029092 | 0.03254 | 0.018993 | −0.024896 | −0.021616 | 0.014918 | 0.005239 | −0.005115 | 0.013725 | 0.004164 | 0.002909 | −0.017594 |
| 293 | 0.014591 | −0.013 | 0.000297 | −0.011596 | 0.004508 | 0.030318 | 0.007245 | −0.002702 | −0.01395 | 0.006765 | 0.028117 | −0.01446 | 0.004443 | 0.027061 |
| 294 | 0.021935 | 0.004273 | 0.019468 | 0.029878 | 0.021211 | −0.009876 | −0.006472 | −0.018451 | −0.023288 | −0.015353 | −0.020839 | −0.011979 | −0.00044 | 0.008173 |
| 295 | 0.009865 | −0.008398 | 0.003688 | 0.002559 | 0.003574 | 0.000844 | −0.018257 | −0.031674 | −0.015256 | −0.000857 | 0.014101 | −0.021712 | −0.008812 | −0.016977 |
| 296 | −0.002368 | −0.012703 | −0.007283 | 0.005004 | 0.011928 | −0.007175 | −0.003851 | 0.014001 | −0.009285 | −0.004272 | 0.000395 | −0.02432 | −0.008259 | −0.001244 |
| 297 | 0.003765 | −0.004875 | −0.00064 | 0.000644 | 0.01625 | 0.007301 | −0.017505 | −0.007539 | −0.003543 | −0.002968 | 0.007962 | 0.001374 | 0.003083 | −0.013306 |
| 298 | −0.019837 | −0.00275 | −0.016934 | −0.010875 | −0.014822 | −0.00761 | −0.030333 | −0.001051 | 0.026543 | −0.001114 | −0.025853 | 0.013178 | −0.016809 | 0.028315 |
| 299 | 0.004721 | 0.014382 | 0.017798 | 0.01286 | −0.006082 | 0.000101 | 0.003137 | −0.013025 | −0.006434 | 0.00868 | 0.016768 | −0.023591 | −0.013124 | −0.000594 |
| 300 | 0.002296 | −0.007367 | 0.010462 | 0.031684 | 0.010423 | −0.023516 | −0.015755 | −0.002016 | 0.024589 | −0.00791 | −0.018207 | −0.008256 | −0.015863 | 0.032866 |
| 301 | 0.001996 | 0.007491 | 0.015771 | 0.006835 | −0.019385 | −0.003788 | −0.009356 | 0.002924 | −0.006854 | 0.008894 | 0.009115 | −0.002311 | 0.007366 | −0.011765 |
| 302 | 0.013358 | 0.016631 | 0.01512 | 0.014229 | 0.000328 | 0.007543 | 0.013519 | 0.017119 | −0.001121 | 0.0139 | 0.007124 | 0.008641 | 0.024081 | −0.015692 |
| 303 | 0.011257 | 0.018872 | 0.024326 | 0.017747 | −0.009404 | −0.006029 | −0.003911 | 0.0183 | −0.009012 | −0.00113 | 0.007659 | −0.013382 | 0.019837 | 0.005741 |
| 304 | 0.004858 | 0.028691 | 0.020896 | 0.022496 | −0.012763 | −0.024423 | −0.004017 | 0.037431 | 0.003342 | −0.008027 | 0.00519 | −0.014159 | 0.005732 | −0.008997 |
| 305 | 0.04601 | 0.024525 | 0.017769 | −0.014954 | 0.02773 | 0.085678 | −0.014261 | −0.022178 | −0.005493 | 0.004961 | 0.030559 | −0.008595 | −0.0066 | 0.000399 |
| 306 | −0.00345 | 0.010202 | 0.012433 | 0.015706 | −0.006497 | 0.021554 | 0.021883 | 0.029625 | 0.028746 | 0.030641 | 0.020658 | −0.009516 | 0.028185 | 0.027702 |
| 307 | −0.016259 | −0.019252 | −0.006577 | −0.006573 | −0.002997 | −0.009241 | −0.002023 | −0.064425 | −0.008304 | −0.020859 | 0.025878 | −0.051239 | −0.022232 | −0.060606 |
| 308 | −0.011477 | −0.00582 | −0.013011 | −0.002422 | 0.004709 | 0.008523 | 0.021504 | −0.015155 | −0.015458 | −0.00851 | 0.005655 | 0.012694 | 0.00388 | −0.024765 |
| 309 | 0.002938 | 0.002595 | 0.002407 | −0.009904 | 0.001734 | −0.016482 | −0.010634 | −0.017768 | 0.007609 | −0.001963 | −0.003621 | 0.004958 | 0.011698 | −0.000207 |
| 310 | −0.0016411 | −0.01473 | −0.003537 | −0.007607 | −0.014949 | 0.003488 | −0.008678 | −0.000871 | −0.014607 | −0.009476 | 0.005337 | 0.006962 | 0.01914 | 0.019686 |
| 311 | −0.015512 | −0.006816 | −0.003214 | −0.012783 | −0.034058 | −0.012082 | 0.011203 | 0.005449 | 0.001509 | 0.001972 | −0.009352 | −0.01726 | 0.006967 | 0.01176 |
| 312 | −0.000297 | 0.011117 | −0.004986 | 0.012481 | 0.03662 | 0.051884 | −0.025445 | 0.028869 | 0.018912 | −0.021607 | −0.01417 | 0.032075 | 0.00682 | 0.016801 |
| 313 | −0.012234 | 0.012439 | 0.002582 | −0.004649 | −0.012046 | 0.027456 | 0.034177 | 0.037394 | 0.01718 | 0.012475 | 0.003263 | 0.008377 | −0.013602 | −0.006724 |
| 314 | 0.039439 | 0.008317 | 0.016635 | 0.000265 | 0.044202 | 0.034521 | −0.033337 | −0.042611 | −0.025777 | −0.031271 | 0.009276 | −0.003181 | 0.012726 | −0.01234 |
| 315 | −0.003666 | 0.000127 | 0.001406 | −0.01993 | 0.004215 | 0.027005 | 0.012949 | −0.002454 | 0.004002 | 0.011767 | −0.000802 | −0.023436 | −0.013435 | −0.004604 |
| 316 | −0.005707 | −0.002098 | 0.002302 | 0.003758 | 0.021679 | 0.004366 | 0.043802 | 0.004041 | 0.002134 | 0.007435 | −0.003118 | 0.001695 | 0.008683 | 0.050586 |
| 317 | −0.01174 | −0.018218 | −0.014125 | −0.021889 | −0.003042 | 0.005736 | −0.026012 | 0.001618 | 0.006706 | 0.006346 | 0.006708 | −0.006507 | −0.011292 | 0.018128 |
| 318 | −0.009125 | −0.020834 | −0.020945 | −0.008279 | −0.012147 | 0.016763 | −0.022113 | 0.028003 | 0.003141 | −0.012339 | −0.01888 | −0.006359 | −0.012371 | −0.010308 |
| 319 | 0.000314 | −0.009011 | −0.005231 | −0.003697 | 0.018691 | 0.006949 | −0.014807 | 0.001524 | 0.001869 | 0.007378 | 0.01526 | 0.002708 | 0.001216 | 0.013201 |
| 320 | −0.017736 | −0.000951 | −0.006939 | 0.006793 | 0.02568 | 0.037189 | 0.017467 | 0.038525 | 0.025738 | 0.018795 | 0.027085 | −0.004568 | −0.021201 | 0.035515 |
| 321 | −0.003819 | 0.013448 | 0.01794 | 0.00607 | −0.022824 | −0.037308 | 0.022731 | −0.005534 | 0.001154 | 0.014456 | 0.015358 | −0.006591 | 0.004057 | −0.058623 |
| 322 | −0.00191 | 0.010987 | −0.010311 | −0.025002 | −0.007028 | 0.051783 | −0.020352 | 0.028932 | 0.037638 | 0.043416 | 0.039886 | −0.010237 | −0.045989 | 0.012371 |
| 323 | −0.002879 | 0.023421 | −0.003264 | −0.013108 | −0.024839 | −0.008842 | 0.011216 | −0.004371 | 0.016071 | 0.010205 | 0.005911 | 0.034528 | 0.004087 | −0.029446 |
| 324 | −0.015206 | −0.01889 | −0.020643 | 0.002056 | −0.006697 | 0.022706 | 0.015756 | −0.012411 | 0.04012 | 0.020347 | −0.030928 | 0.013237 | −0.025695 | −0.000871 |
| 325 | −0.001489 | −0.000786 | −0.0053831 | −0.03115 | −0.008468 | −0.021289 | −0.017783 | 0.00701 | 0.01099 | −0.002676 | −0.050409 | 0.008757 | 0.011557 | −0.014738 |
| 326 | −0.00741 | 0.007821 | 0.003441 | 41010405 | −0.022245 | −0.006468 | 0.040082 | −0.002537 | −0.007973 | −0.008293 | −0.040945 | −0.026139 | −0.034611 | −0.002549 |
| 327 | 0.011178 | 0.001144 | −0.006926 | −0.005557 | 0.011227 | 0.022276 | 0.018322 | −0.00611 | −0.006316 | 0.003542 | −0.000381 | −0.017102 | −0.014042 | −0.005924 |
| 328 | 0.021516 | 0.013949 | 0.001288 | 0.00807 | 0.013215 | −0.051342 | −0.014425 | −0.049846 | −0.016752 | −0.018032 | 0.027941 | 0.000277 | 0.003238 | −0.039436 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 329 | −0.00236 | 0.000869 | −0.002179 | 0.004192 | −0.010245 | −0.004965 | −0.011185 | 0.018444 | −0.009571 | −0.00104 | 0.006684 | 0.024802 | 0.014265 | −0.017667 |
| 330 | −0.006938 | 0.011745 | 0.00053 | −0.01864 | −0.011519 | 0.022588 | −0.012531 | 0.049425 | 0.002736 | −0.000206 | −0.054614 | −0.014903 | 0.010044 | −0.007341 |
| 331 | 0.014242 | 0.003883 | 0.009105 | −0.003682 | 0.008353 | −0.007668 | 0.030915 | −0.019256 | −0.015533 | −0.004694 | −0.012911 | −0.010718 | −0.009833 | −0.015333 |
| 332 | −0.019928 | 0.008822 | 0.006494 | −0.008413 | −0.019767 | −0.007769 | −0.046707 | −0.015612 | 0.022933 | 0.000649 | −0.003132 | −0.017647 | 0.02066 | 0.006989 |
| 333 | −0.001117 | −0.00891 | −0.011116 | −0.026145 | 0.00103 | −0.020426 | −0.022798 | −0.010955 | 0.006063 | −0.002296 | −0.026402 | −0.003134 | −0.029676 | −0.025878 |
| 334 | −0.030845 | −0.023529 | 0.003655 | 0.015721 | 0.020351 | 0.010284 | −0.046612 | −0.017132 | 0.022026 | 0.011942 | 0.010139 | −0.000991 | 0.023175 | 0.00369 |
| 335 | −0.005643 | −0.000387 | −0.011138 | −0.003989 | −0.000471 | −0.012098 | 0.010718 | −0.01233 | −0.015039 | −0.015683 | −0.03102 | 0.011442 | −0.010474 | −0.009646 |
| 336 | 0.034187 | −0.00882 | 0.005614 | 0.006535 | 0.023688 | −0.041775 | −0.049061 | −0.060731 | 0.002161 | −0.007748 | 0.006031 | −0.056274 | −0.040066 | 0.019377 |
| 337 | −0.01406 | −0.0054 | 0.002314 | −0.000821 | −0.025724 | −0.007451 | 0.01625 | −0.003128 | −0.000856 | 0.012957 | 0.023782 | −0.049867 | −0.029633 | 0.002489 |
| 338 | −0.007358 | 0.007198 | 0.000216 | 0.003884 | −0.020178 | 0.017474 | −0.04777 | −0.041049 | 0.01126 | 0.018264 | 0.032597 | −0.003359 | 0.019575 | −0.017782 |
| 339 | −0.00361 | −0.012173 | −0.010159 | −0.034585 | −0.048321 | −0.024243 | 0.047461 | −0.073644 | 0.004107 | 0.004718 | 0.037667 | −0.036417 | 0.005557 | 0.000707 |
| 340 | −0.01141 | −0.002616 | 0.004323 | −0.036106 | −0.005776 | 0.054949 | −0.042687 | 0.027208 | −0.010988 | 0.010187 | 0.006128 | −0.000368 | −0.011788 | −0.056916 |

| | GL | GM | GN | GO | GP | GQ | GR | GS | GT | GU | GV | GW | GX | GY |
|---|---|---|---|---|---|---|---|---|---|---|---|---|---|---|
| 1 | 0.0880561 | 0.0014341 | 0.024706 | 0.019529 | −0.055872 | 0.070416 | 0.052527 | −0.02662 | −0.025299 | 0.0105981 | −0.085773 | 0.0392511 | −0.057181 | −0.004309 |
| 2 | 0.007435 | 0.008898 | −0.071177 | 0.038005 | 0.042353 | −0.060861 | 0.018287 | −0.040898 | −0.089569 | −0.030351 | −0.002347 | 0.1111321 | −0.008276 | 0.033354 |
| 3 | 0.031426 | 0.016063 | 0.052899 | 0.030304 | 0.020922 | 0.073166 | −0.042706 | 0.010596 | −0.117425 | 0.044779 | −0.04594 | −0.153041 | 0.14811 | −0.010831 |
| 4 | 0.027126 | 0.008655 | 0.056382 | 0.04493 | 0.016407 | 0.096039 | −0.040338 | 0.033654 | −0.001942 | 0.119635 | −0.032639 | 0.063696 | 0.096322 | 0.126989 |
| 5 | 0.027934 | 0.00492 | −0.028329 | −0.032895 | 0.026744 | −0.033406 | −0.032439 | −0.044303 | 0.038988 | −0.022284 | −0.037868 | 0.050768 | −0.011287 | 0.014479 |
| 6 | −0.085431 | 0.033237 | 0.041182 | −0.010605 | 0.005962 | 0.106058 | 0.054499 | −0.01924 | 0.043876 | −0.006844 | 0.042102 | 0.001785 | −0.059267 | 0.0744 |
| 7 | 0.0461211 | −0.059158 | −0.065224 | −0.06982 | −0.02384 | 0.047501 | −0.049048 | 0.003641 | 0.0373451 | −0.025634 | −0.064995 | 0.0219551 | 0.0211341 | −0.106019 |
| 8 | −0.0518391 | −0.1036491 | −0.026364 | −0.015036 | −0.12237 | −0.008658 | −0.014158 | −0.028984 | −0.079107 | −0.054114 | −0.03832 | 0.036212 | −0.030858 | 0.043162 |
| 9 | 0.013006 | 0.051098 | −0.039684 | −0.027132 | 0.003353 | 0.017914 | −0.0672 | −0.075458 | 0.052902 | −0.102001 | −0.110528 | 0.091969 | 0.017818 | −0.008335 |
| 10 | −0.04977 | −0.048356 | −0.005743 | 0.001371 | 0.031323 | −0.018956 | 0.014013 | 0.044554 | −0.041661 | 0.00367 | −0.035665 | 0.121 | −0.087132 | 0.011419 |
| 11 | −0.095754 | 0.038807 | −0.01184 | 0.043518 | −0.004418 | −0.018885 | −0.0845 | −0.00166 | −0.081166 | −0.015123 | 0.003308 | −0.03454 | 0.088543 | 0.0764 |
| 12 | 0.012742 | 0.056213 | 0.000867 | −0.014599 | −0.04996 | 0.04509 | −0.026623 | −0.017921 | 0.037534 | −0.003008 | 0.047356 | −0.007612 | 0.068408 | 0.049963 |
| 13 | −0.025913 | 0.020976 | −0.027421 | −0.003879 | −0.048155 | −0.032022 | −0.062974 | 0.105141 | −0.067072 | −0.014432 | −0.070092 | −0.059277 | 0.12348 | −0.057442 |
| 14 | 0.042445 | −0.015995 | −0.033957 | 0.01284 | 0.045425 | 0.041069 | −0.043164 | −0.167274 | 0.062731 | −0.098508 | 0.109481 | −0.055117 | −0.069083 | 0.038313 |
| 15 | 0.005841 | −0.049659 | −0.045704 | −0.035448 | 0.063492 | −0.068045 | −0.020692 | −0.116779 | 0.015242 | 0.03586 | −0.040238 | −0.14494 | −0.007426 | 0.045632 |
| 16 | 0.04178 | −0.000688 | −0.031376 | 0.00784 | 0.045977 | 0.013004 | 0.018703 | −0.003079 | −0.000887 | 0.007587 | 0.056263 | 0.010897 | 0.080564 | −0.046576 |
| 17 | −0.019351 | −0.021836 | −0.040524 | −0.041727 | −0.035641 | 0.073788 | 0.009767 | 0.018654 | −0.054373 | 0.1071841 | 0.0226471 | −0.059449 | −0.049674 | −0.114318 |
| 18 | −0.017501 | −0.088541 | 0.00975 | 0.022152 | 0.066784 | 0.019454 | −0.091962 | −0.043249 | 0.041446 | 0.001614 | 0.068373 | 0.014569 | 0.05232 | 0.064634 |
| 19 | 0.026708 | 0.143033 | 0.036948 | 0.010385 | −0.079966 | 0.035777 | −0.071094 | −0.017487 | −0.017748 | 0.073427 | −0.010168 | 0.026148 | 0.02769 | −0.016105 |
| 20 | 0.065986 | −0.066124 | 0.14081 | 0.08362 | −0.010231 | 0.094188 | −0.085222 | 0.154947 | −0.075117 | 0.123653 | −0.004237 | 0.002015 | −0.034467 | 0.21365 |
| 21 | −0.00185 | −0.056409 | 0.008173 | −0.024001 | −0.014718 | −0.202057 | −0.142895 | −0.003926 | 0.075305 | −0.129143 | −0.026341 | −0.009904 | 0.002739 | 0.049675 |
| 22 | −0.00148 | −0.059935 | −0.06762 | −0.044731 | 0.004012 | −0.023878 | 0.072528 | −0.018068 | −0.049558 | −0.073388 | 0.1114431 | −0.037397 | −0.038079 | −0.035573 |
| 23 | 0.009363 | −0.005675 | 0.024436 | 0.043567 | 0.031702 | −0.071697 | −0.104155 | −0.043806 | −0.102236 | 0.030896 | 0.016289 | 0.091808 | −0.027565 | −0.007488 |
| 24 | 0.006183 | 0.015661 | 0.053736 | 0.056484 | 0.03715 | 0.009757 | 0.070123 | −0.075641 | 0.131631 | −0.01497 | −0.020065 | −0.023649 | 0.027057 | 0.002889 |
| 25 | −0.067134 | −0.000807 | 0.026585 | 0.039992 | 0.029433 | 0.02768 | 0.077313 | 0.059749 | 0.073399 | 0.084009 | −0.00835 | −0.090388 | −0.024322 | −0.093975 |
| 26 | 0.011559 | 0.056839 | 0.049208 | 0.033748 | 0.039259 | −0.114464 | 0.339117 | −0.000123 | −0.103285 | −0.059013 | 0.080445 | −0.016948 | 0.020506 | −0.014577 |
| 27 | 0.014591 | −0.032312 | −0.072421 | −0.046564 | 0.049893 | −0.07298 | −0.050747 | 0.050026 | 0.004523 | 0.003736 | −0.003596 | −0.076853 | −0.104864 | 0.061316 |
| 28 | 0.001253 | −0.019744 | −0.015499 | −0.009446 | −0.00852 | −0.101721 | −0.047466 | −0.058211 | 0.061535 | 0.02101 | 0.072159 | −0.076901 | −0.135013 | 0.005653 |
| 29 | 0.046995 | 0.009488 | 0.032574 | 0.014729 | 0.016661 | −0.000565 | −0.017094 | 0.00902 | 0.00031 | −0.031734 | −0.040585 | −0.018238 | −0.001742 | −0.034214 |
| 30 | −0.039679 | 0.024351 | 0.162431 | 0.06202 | 0.036492 | 0.098225 | 0.010622 | −0.015591 | −0.070107 | 0.0587 | −0.136083 | −0.080987 | 0.021932 | −0.066558 |
| 31 | 0.019422 | −0.014588 | −0.028436 | −0.042138 | −0.030242 | 0.125732 | −0.038113 | 0.026268 | −0.007745 | 0.040073 | −0.005989 | −0.013571 | 0.087621 | 0.021906 |
| 32 | 0.027253 | −0.00332 | −0.037467 | −0.007501 | 0.024805 | 0.013064 | 0.068883 | 0.024966 | −0.108817 | −0.070559 | 0.066971 | −0.0716 | 0.037248 | −0.088733 |
| 33 | 0.010224 | 0.0384181 | −0.088795 | −0.041617 | 0.025425 | −0.014778 | −0.0116 | −0.034308 | −0.014176 | −0.070419 | 0.053029 | 0.066592 | 0.066248 | 0.067406 |
| 34 | 0.002553 | 0.04757 | −0.010494 | 0.010563 | −0.039158 | −0.125756 | 0.153589 | −0.013019 | 0.108715 | −0.008049 | −0.084563 | 0.067862 | −0.046626 | −0.101545 |
| 35 | 0.067464 | 0.012263 | 0.061139 | −0.002275 | 0.05453 | 0.027733 | −0.03186 | 0.042697 | 0.069578 | 0.114202 | 0.010135 | −0.032264 | −0.073012 | −0.00721 |
| 36 | −0.005323 | −0.004937 | −0.052122 | −0.015581 | −0.063391 | 0.062572 | −0.009911 | 0.000406 | 0.091089 | 0.017452 | 0.002478 | 0.189519 | −0.210822 | −0.036383 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 37 | 0.030128 | 0.109485 | 0.063625 | 0.043474 | −0.051649 | 0.084872 | 0.005876 | 0.030891 | −0.045223 | −0.029908 | 0.058814 | −0.026812 | 0.033024 | −0.057805 |
| 38 | 0.04094 | 0.075814 | −0.026996 | 0.007895 | 0.017931 | −0.028857 | 0.024524 | 0.097797 | 0.092435 | 0.03103 | 0.118421 | −0.037433 | 0.108008 | 0.034776 |
| 39 | 0.035397 | 0.15324 | 0.05908 | −0.02043 | −0.065116 | 0.041154 | −0.044872 | 0.01746 | −0.011985 | −0.002451 | 0.064874 | −0.041661 | −0.170032 | −0.065649 |
| 40 | 0.015638 | 0.053755 | 0.001767 | 0.061183 | 0.12953 | 0.050521 | −0.126766 | 0.073705 | −0.01225 | −0.046526 | 0.073505 | −0.029041 | −0.151265 | −0.08831 |
| 41 | 0.035142 | −0.002645 | 0.031613 | 0.049728 | 0.141339 | 0.033241 | 0.040793 | −0.033839 | −0.14471 | 0.115523 | −0.030947 | 0.134659 | 0.132741 | −0.009158 |
| 42 | 0.007479 | 0.001821 | −0.011857 | −0.00135 | 0.010559 | 0.017286 | −0.027981 | −0.001274 | 0.017573 | −0.012266 | −0.01597 | 0.028736 | 0.009288 | 0.027197 |
| 43 | −0.061536 | −0.091704 | 0.072553 | 0.028616 | 0.053602 | 0.010352 | −0.009088 | 0.018713 | 0.03412 | 0.023403 | −0.007514 | 0.07328 | 0.076403 | 0.043322 |
| 44 | −0.009215 | 0.010671 | −0.046968 | −0.088277 | −0.142586 | −0.064412 | 0.059031 | 0.145013 | 0.005535 | −0.094205 | −0.006246 | −0.0495 | −0.014881 | −0.008509 |
| 45 | −0.024038 | −0.014448 | 0.084768 | 0.041385 | 0.01234 | −0.009282 | 0.068199 | −0.023666 | 0.159257 | 0.041821 | 0.021154 | −0.029017 | −0.027308 | −0.065118 |
| 46 | −0.005807 | −0.014951 | −0.023225 | −0.0117 | −0.000754 | −0.048735 | −0.057624 | 0.051324 | −0.026262 | −0.015541 | −0.027509 | −0.068111 | 0.052761 | 0.080492 |
| 47 | 0.053115 | −0.024091 | 0.02394 | 0.028202 | 0.07558 | −0.035042 | −0.103061 | 0.023483 | −0.076053 | 0.002979 | −0.043683 | 0.041784 | 0.001216 | −0.000699 |
| 48 | −0.003195 | −0.086584 | −0.094383 | −0.038826 | −0.017221 | −0.026436 | 0.06268 | −0.077817 | −0.007971 | −0.030353 | −0.021914 | 0.013878 | −0.011445 | −0.11798 |
| 49 | −0.004473 | −0.128516 | 0.017446 | 0.03807 | 0.075473 | −0.01468 | −0.05023 | −0.061037 | −0.095875 | 0.05284 | 0.003883 | 0.076007 | −0.043756 | 0.22677 |
| 50 | −0.120611 | 0.002993 | 0.061779 | 0.033121 | 0.01808 | −0.0105 | −0.007711 | 0.07389 | 0.127619 | 0.068296 | 0.009307 | −0.018776 | 0.082171 | −0.074383 |
| 51 | −0.018821 | 0.013271 | 0.056216 | 0.064271 | −0.040394 | 0.016496 | −0.160949 | 0.086517 | 0.07955 | −0.000786 | 0.026683 | 0.040651 | −0.009655 | 0.001975 |
| 52 | 0.0338 | 0.038132 | 0.092693 | 0.059586 | 0.019467 | 0.031076 | −0.080158 | −0.000479 | −0.030237 | −0.014806 | −0.008945 | −0.021661 | −0.00938 | −0.098313 |
| 53 | −0.019836 | −0.006664 | 0.046124 | 0.012275 | 0.083584 | −0.011465 | −0.09941 | 0.0037 | −0.023965 | −0.018057 | 0.022067 | 0.166241 | 0.029889 | −0.083567 |
| 54 | 0.004338 | 0.063473 | 0.001626 | −0.098102 | −0.033584 | −0.013292 | −0.066552 | 0.110885 | −0.066802 | 0.044687 | 0.080714 | −0.034273 | 0.01385 | 0.028034 |
| 55 | −0.023671 | 0.040428 | 0.027537 | 0.031326 | 0.082255 | −0.042988 | 0.112227 | 0.000375 | −0.018419 | 0.047141 | 0.08769 | −0.07497 | 0.005365 | 0.106023 |
| 56 | −0.017991 | −0.034104 | 0.008299 | −0.048161 | −0.048786 | −0.008415 | −0.00569 | −0.045708 | 0.082701 | 0.027205 | −0.048225 | 0.101954 | 0.079517 | −0.047064 |
| 57 | 0.067693 | −0.009876 | 0.048672 | 0.058635 | 0.013644 | 0.020834 | 0.005896 | 0.001806 | −0.080011 | 0.156416 | −0.090506 | −0.032635 | −0.059043 | −0.015761 |
| 58 | 0.088731 | 0.036297 | −0.09729 | −0.046292 | 0.065439 | −0.026161 | 0.089192 | −0.087039 | −0.020205 | 0.0914161 | −0.040332 | −0.003244 | 0.083391 | 0.006927 |
| 59 | 0.00353 | 0.041383 | −0.065518 | −0.016526 | 0.024061 | 0.007141 | −0.033217 | −0.014571 | 0.175841 | 0.027627 | −0.008049 | −0.003972 | −0.05643 | −0.053791 |
| 60 | −0.006349 | 0.087522 | 0.059621 | −0.006364 | 0.015328 | 0.037022 | −0.046136 | 0.086577 | 0.129068 | 0.077088 | 0.144407 | 0.026612 | −0.061014 | 0.172112 |
| 61 | 0.032856 | 0.027439 | 0.00746 | −0.041498 | −0.015771 | −0.023286 | −0.052242 | −0.063385 | −0.094976 | −0.057618 | −0.017608 | 0.076405 | −0.053522 | 0.001211 |
| 62 | −0.008272 | 0.034635 | 0.055816 | 0.099093 | 0.023476 | −0.054963 | −0.112348 | −0.045489 | 0.043766 | 0.003122 | −0.138201 | 0.074115 | 0.095518 | −0.026378 |
| 63 | 0.040386 | 0.036012 | 0.065577 | 0.039601 | −0.006044 | 0.043124 | 0.092089 | −0.003879 | 0.025722 | −0.066623 | −0.03498 | 0.057087 | −0.006284 | 0.128443 |
| 64 | 0.050187 | −0.003564 | −0.005629 | −0.004994 | −0.002201 | 0.069751 | −0.087862 | 0.082092 | 0.106845 | 0.056119 | −0.064419 | 0.030987 | 0.016555 | −0.033265 |
| 65 | −0.03338 | −0.04837 | 0.022274 | −0.009922 | −0.035126 | 0.011734 | 0.004481 | 0.088349 | 0.060213 | −0.015925 | −0.053319 | 0.059343 | 0.083983 | 0.020889 |
| 66 | −0.083367 | −0.088998 | 0.048677 | 0.042914 | −0.008891 | 0.010204 | −0.000873 | 0.009406 | −0.066901 | −0.026333 | 0.046666 | −0.031195 | 0.071539 | −0.061398 |
| 67 | −0.088205 | 0.017877 | −0.104648 | −0.043359 | −0.045887 | −0.027877 | −0.003359 | −0.030836 | 0.019449 | 0.027352 | 0.120163 | −0.073696 | −0.057653 | 0.035568 |
| 68 | 0.029394 | 0.008929 | −0.047582 | 0.03014 | −0.016465 | 0.06238 | 0.025819 | −0.01683 | 0.011317 | −0.017425 | 0.095448 | 0.044297 | 0.079566 | −0.012498 |
| 69 | 0.03135 | 0.060915 | 0.077627 | 0.028705 | 0.012104 | −0.091286 | −0.039151 | −0.058324 | 0.097684 | −0.085278 | 0.056871 | −0.012786 | 0.011171 | −0.037836 |
| 70 | 0.020802 | −0.056568 | 0.043402 | −0.083194 | 0.083602 | −0.006346 | 0.090529 | −0.003695 | 0.046739 | −0.005231 | 0.049263 | 0.073525 | 0.073539 | 0.138017 |
| 71 | 0.036766 | −0.004714 | −0.01663 | 0.041233 | 0.066682 | −0.016188 | 0.053431 | 0.030563 | 0.051098 | 0.032245 | −0.05762 | 0.102954 | 0.050896 | −0.084329 |
| 72 | 0.015699 | 0.065614 | −0.040035 | −0.056325 | 0.005788 | −0.003111 | 0.023356 | −0.03101 | −0.08827 | 0.007459 | −0.024247 | 0.023024 | −0.32068 | 0.011584 |
| 73 | 0.041541 | 0.000017 | 0.054863 | −0.015561 | 0.000837 | 0.031467 | −0.006423 | 0.10288 | 0.0317731 | 0.073762 | 0.073131 | −0.095931 | 0.0456891 | −0.069573 |
| 74 | 0.0611921 | −0.0010651 | −0.022096 | 0.017418 | 0.024392 | −0.02498 | −0.10544 | 0.040273 | −0.044369 | 0.002979 | 0.067983 | −0.012535 | −0.017337 | −0.032513 |
| 75 | −0.093255 | 0.108743 | −0.0481 | −0.023255 | −0.005544 | 0.010327 | 0.016822 | −0.069667 | 0.039181 | 0.000562 | −0.059943 | −0.005569 | −0.091516 | 0.035208 |
| 76 | 0.059866 | 0.036549 | 0.006026 | 0.030311 | 0.021069 | 0.00964 | −0.08982 | 0.102824 | −0.06787 | 0.04383 | −0.034978 | 0.006118 | 0.006619 | 0.006154 |
| 77 | −0.015026 | −0.107602 | −0.031928 | 0.019694 | −0.03252 | −0.06242 | −0.052569 | −0.038402 | −0.019476 | −0.021193 | −0.120511 | −0.099823 | 0.007684 | −0.009615 |
| 78 | −0.0054 | −0.067266 | −0.060694 | −0.007378 | 0.014896 | 0.109119 | 0.073776 | 0.111803 | −0.079042 | 0.064883 | 0.08516 | 0.003406 | 0.005053 | −0.10939 |
| 79 | 0.022709 | 0.060389 | −0.024896 | −0.059272 | −0.078627 | 0.108948 | 0.016026 | 0.067408 | 0.073543 | 0.074593 | −0.01326 | 0.099011 | 0.020247 | −0.044328 |
| 80 | 0.053733 | 0.035803 | −0.041537 | 0.612272 | −0.078237 | −0.067244 | −0.020881 | 0.00792 | 0.06835 | 0.030592 | −0.019484 | 0.133575 | −0.034492 | −0.005916 |
| 81 | −0.061203 | −0.019579 | −0.006404 | 0.063279 | −0.051377 | −0.062402 | 0.034654 | −0.035636 | 0.054488 | −0.02119 | 0.004053 | −0.095934 | −0.047533 | 0.006155 |
| 82 | 0.137489 | −0.016049 | −0.056228 | 0.006053 | −0.035025 | −0.026947 | 0.017451 | 0.018794 | −0.047027 | 0.048033 | −0.009668 | 0.055819 | −0.003783 | 0.126274 |
| 83 | −0.018774 | 0.027575 | −0.045814 | −0.015482 | −0.019604 | 0.002329 | −0.104448 | −0.054211 | −0.05033 | −0.045728 | 0.025901 | 0.078786 | 0.067341 | 0.032937 |
| 84 | −0.11313 | −0.011548 | −0.045064 | 0.018274 | 0.000018 | −0.020536 | −0.08427 | −0.012893 | 0.017768 | −0.006166 | 0.069566 | 0.048722 | 0.002124 | −0.060439 |
| 85 | 0.011827 | −0.022232 | 0.004857 | 0.041642 | −0.024161 | 0.012859 | 0.083573 | 0.003683 | 0.040077 | 0.035585 | 0.016865 | 0.046937 | 0.043196 | −0.059065 |
| 86 | 0.077865 | 0.031824 | 0.048402 | 0.009246 | 0.023869 | −0.091806 | 0.00002 | −0.054414 | 0.0527 | −0.09248 | −0.037555 | −0.097424 | 0.134749 | 0.054994 |
| 87 | −0.136695 | −0.000621 | −0.011205 | 0.024026 | 0.050362 | −0.034105 | 0.018059 | −0.033859 | −0.045812 | −0.016325 | −0.045045 | 0.139749 | 0.011051 | −0.021368 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 88 | −0.044627 | −0.037802 | 0.033396 | −0.033028 | 0.002097 | 0.073986 | 0.063636 | −0.06616 | 0.134212 | 0.034527 | −0.029881 | −0.064381 | 0.087635 | −0.137682 |
| 89 | −0.006878 | −0.048732 | 0.03313 | −0.00217 | −0.055732 | −0.051175 | −0.133673 | −0.011958 | −0.024648 | 0.013708 | −0.098149 | −0.075472 | −0.136724 | −0.053791 |
| 90 | −0.038356 | 0.041795 | 0.088923 | 0.011644 | −0.024214 | 0.004996 | −0.066607 | 0.009267 | −0.011413 | 0.042785 | 0.055674 | 0.027019 | 0.142707 | −0.079086 |
| 91 | 0.019749 | −0.061579 | −0.014957 | 0.050032 | 0.016568 | −0.025202 | 0.030243 | 0.032228 | −0.0076 | −0.091776 | −0.060599 | −0.054193 | 0.046055 | 0.057226 |
| 92 | −0.052804 | −0.063904 | −0.020603 | 0.006104 | −0.004129 | 0.03294 | −0.059789 | −0.050603 | 0.078166 | 0.002907 | 0.013301 | −0.063758 | 0.092812 | 0.116659 |
| 93 | −0.000647 | 0.065406 | −0.021501 | −0.066484 | 0.04021 | 0.061317 | 0.068479 | 0.014635 | 0.055818 | 0.048438 | 0.02743 | 0.078851 | −0.07857 | 0.022026 |
| 94 | 0.023755 | 0.0159 | 0.092186 | 0.044834 | 0.017854 | 0.094247 | −0.074926 | −0.017694 | −0.03351 | 0.033551 | 0.026872 | 0.013508 | −0.093311 | −0.091036 |
| 95 | −0.100612 | −0.010084 | 0.005286 | 0.030041 | −0.016036 | 0.0061 | −0.04816 | 0.032935 | −0.054672 | 0.022933 | −0.061641 | −0.009897 | −0.077468 | 0.010877 |
| 96 | 0.028332 | −0.01908 | 0.003381 | 0.033434 | 0.001082 | 0.029388 | 0.093562 | 0.084696 | −0.02593 | −0.010833 | 0.137521 | −0.019516 | −0.089171 | 0.076628 |
| 97 | −0.034244 | −0.104321 | −0.020199 | −0.048538 | 0.021244 | −0.014143 | −0.010716 | −0.017671 | −0.10667 | −0.010201 | −0.009295 | 0.005413 | −0.024001 | −0.004781 |
| 98 | 0.033604 | 0.024152 | 0.027104 | −0.037246 | 0.032593 | −0.011099 | −0.055935 | 0.020471 | −0.028827 | −0.016187 | −0.003756 | −0.099131 | 0.040762 | −0.07883 |
| 99 | −0.011068 | 0.099582 | −0.03379 | 0.043469 | −0.025807 | 0.091373 | 0.090769 | 0.002067 | −0.010045 | −0.087472 | 0.121209 | 0.028012 | 0.108506 | −0.014925 |
| 100 | −0.040066 | 0.020509 | 0.040127 | 0.003873 | −0.027367 | −0.010559 | −0.012041 | −0.023397 | 0.01884 | 0.008491 | −0.017914 | −0.006686 | 0.058513 | −0.006246 |
| 101 | 0.030732 | 0.01709 | −0.003861 | −0.041817 | −0.018254 | 0.009966 | −0.020725 | 0.0207 | −0.011726 | 0.007033 | 0.026882 | −0.004578 | 0.032003 | 0.025098 |
| 102 | −0.051839 | −0.099029 | 0.005901 | 0.006941 | 0.004099 | 0.028845 | −0.007698 | 0.031908 | −0.016582 | 0.02173 | −0.015875 | 0.010217 | −0.007712 | 0.014777 |
| 103 | −0.024903 | −0.032527 | 0.016237 | 0.01099 | 0.005132 | −0.030034 | −0.027867 | 0.045792 | 0.08654 | 0.030828 | 0.026223 | −0.018343 | 0.002549 | −0.036978 |
| 104 | 0.012399 | 0.01549 | 0.009487 | −0.000131 | −0.088411 | −0.012886 | −0.037439 | 0.011907 | 0.013931 | −0.033781 | −0.025816 | −0.019522 | 0.003656 | 0.014624 |
| 105 | −0.031143 | −0.011202 | 0.029555 | 0.02806 | 0.003565 | 0.008956 | 0.004034 | −0.07266 | −0.049444 | −0.060909 | −0.014813 | −0.069137 | −0.000899 | −0.008788 |
| 106 | 0.012681 | 0.012337 | 0.016463 | −0.002905 | 0.034051 | −0.008545 | −0.015491 | 0.026129 | 0.05267 | −0.026753 | −0.033905 | 0.015905 | −0.017553 | 0.006827 |
| 107 | −0.049969 | −0.034831 | −0.031436 | 0.0126 | −0.004809 | 0.00905 | −0.010743 | −0.019035 | −0.079427 | −0.050472 | −0.010093 | 0.063653 | 0.109027 | 0.009302 |
| 108 | −0.023112 | −0.011787 | −0.006492 | −0.033185 | 0.001567 | 0.008102 | 0.031174 | −0.047473 | 0.006044 | 0.017172 | 0.097265 | −0.004979 | 0.004139 | −0.05534 |
| 109 | −0.000773 | 0.027102 | 0.004306 | −0.015815 | 0.050803 | 0.039654 | 0.056898 | −0.04684 | 0.005289 | 0.024977 | 0.055548 | −0.034011 | −0.02942 | −0.009659 |
| 110 | 0.015551 | 0.021905 | −0.030657 | 0.008142 | −0.012155 | 0.026931 | 0.009463 | −0.00633 | 0.043056 | 0.033533 | 0.042421 | −0.019118 | 0.003022 | −0.060085 |
| 111 | −0.025517 | 0.019766 | −0.076863 | −0.020506 | 0.025278 | −0.012044 | 0.025006 | 0.004486 | −0.029296 | −0.01478 | 0.003741 | −0.008891 | 0.013877 | −0.025172 |
| 112 | 0.02325 | −0.044975 | −0.005163 | −0.039183 | −0.011012 | −0.038789 | 0.031093 | −0.000476 | −0.029063 | −0.053154 | −0.011656 | −0.018838 | 0.014386 | 0.009078 |
| 113 | 0.00021 | 0.022552 | 0.046438 | 0.048881 | 0.02648 | −0.046633 | −0.097186 | 0.009142 | 0.036886 | −0.025269 | 0.012626 | −0.050443 | −0.062183 | −0.066848 |
| 114 | 0.011483 | 0.047593 | −0.04093 | −0.031815 | −0.004626 | −0.023258 | −0.003429 | −0.047271 | 0.004839 | −0.039653 | −0.025902 | −0.019189 | 0.087603 | 0.024036 |
| 115 | −0.016889 | −0.025006 | −0.037269 | −0.055659 | −0.031788 | −0.007899 | −0.074241 | −0.005176 | 0.018749 | −0.051752 | −0.003639 | −0.010735 | 0.015265 | −0.031372 |
| 116 | −0.016078 | 0.040439 | −0.058959 | −0.057341 | 0.021351 | −0.033072 | 0.042541 | −0.005715 | −0.084996 | 0.036847 | −0.04458 | −0.020059 | 0.01877 | 0.043411 |
| 117 | −0.040897 | −0.018816 | −0.008991 | 0.001209 | −0.007637 | 0.013255 | −0.023499 | 0.018197 | 0.059791 | 0.016192 | −0.01797 | 0.05573 | 0.032568 | 0.027195 |
| 118 | 0.008333 | 0.014424 | 0.030481 | 0.020537 | −0.001566 | −0.000486 | 0.045054 | −0.018801 | −0.063721 | 0.094769 | −0.035496 | 0.012349 | −0.012892 | −0.033673 |
| 119 | −0.025957 | −0.006465 | −0.015266 | −0.003179 | −0.008869 | −0.017667 | 0.041233 | −0.018954 | −0.006017 | −0.02753 | 0.009011 | −0.04763 | 0.00745 | 0.000224 |
| 120 | −0.061151 | −0.025671 | −0.005555 | −0.010279 | −0.030699 | −0.008214 | −0.029529 | 0.002537 | 0.020946 | −0.026503 | −0.018478 | 0.032013 | 0.036707 | 0.007774 |
| 121 | −0.010471 | −0.009716 | 0.000222 | −0,016078 | −0.007896 | 0.018904 | −0.009365 | 0.005222 | 0.046082 | −0.036017 | −0.04223 | 0.02635 | 0.030964 | 0.015684 |
| 122 | 0.039826 | −0.052367 | −0.009159 | −0.006942 | 0.009331 | −0.006754 | −0.003644 | 0.0714 | −0.091094 | 0.002204 | −0.003533 | 0.022611 | −0.025165 | 0.000249 |
| 123 | −0.009801 | −0.034176 | −0.015409 | −0.005564 | 0.005187 | −0.003719 | 0.039527 | 0.041817 | 0.004996 | 0.009414 | 0.032429 | 0.032711 | −0.021452 | −0.032195 |
| 124 | −0.006441 | 0.002814 | 0.002501 | 0.007097 | −0.011326 | −0.036272 | 0.037628 | −0.011369 | −0.041257 | −0.042431 | 0.00865 | −0.026001 | 0.03496 | −0.016382 |
| 125 | 0.018912 | 0.000031 | 0.008535 | 0.007967 | 0.028476 | 0.000963 | 0.002063 | 0.009728 | 0.002596 | 0.023543 | 0.036157 | −0.0052 | 0.000772 | −0.015411 |
| 126 | 0.029035 | 0.027011 | 0.021972 | 0.015075 | 0.023806 | −0.033864 | 0.022879 | −0.001898 | 0.019355 | −0.02204 | 0.004881 | 0.016237 | −0.043018 | −0.002651 |
| 127 | −0.004184 | 0.021377 | 0.033125 | 0.025166 | 0.023046 | −0.001311 | −0.005083 | 0.019169 | 0.015322 | 0.010987 | −0.0038 | 0.02184 | −0.046474 | 0.013939 |
| 128 | −0.025382 | 0.022851 | −0.000204 | 0.019197 | −0.0454 | −0.04709 | 0.034582 | −0.051144 | 0.007075 | −0.041179 | −0.033632 | −0.013436 | −0.02639 | 0.045636 |
| 129 | 0.044791 | −0.004038 | −0.016462 | 0.01617 | 0.051979 | 0.016003 | −0.047762 | −0.02186 | 0.011349 | −0.038222 | −0.057731 | −0.062046 | 0.003005 | −0.00645 |
| 130 | 0.032169 | 0.070323 | 0.01574 | 0.008278 | 0.01638 | −0.051842 | 0.00647 | 0.036038 | 0.095419 | −0.030327 | 0.043484 | 0.021119 | 0.043338 | 0.009499 |
| 131 | −0.017968 | 0.027267 | −0.048399 | 0.027964 | −0.005806 | −0.038472 | 0.006195 | 0.002601 | −0.033055 | 0.011364 | −0.013961 | 0.0052 | 0.010509 | −0.107565 |
| 132 | −0.02653 | −0.035428 | −0.023392 | −0.025608 | −0.054959 | 0.035154 | 0.035984 | −0.029988 | −0.033205 | 0.020444 | −0.008347 | −0.067581 | −0.009671 | 0.016299 |
| 133 | −0.016295 | 0.010412 | −0.010466 | −0.007258 | −0.004313 | 0.016278 | 0.019744 | −0.045784 | 0.015754 | −0.021601 | −0.003873 | 0.063745 | −0.007559 | 0.047223 |
| 134 | −0.000756 | −0.032833 | −0.006993 | −0.031511 | −0.041512 | −0.01417 | 0.048395 | −0.012198 | −0.043 | −0.029913 | −0.018054 | −0.040595 | 0.066557 | −0.005708 |
| 135 | −0.011697 | −0.012716 | −0.005109 | −0.003568 | −0.017777 | −0.021041 | 0.046491 | −0.031734 | −0.00363 | −0.025414 | 0.000001 | −0.010654 | 0.01296 | −0.027324 |
| 136 | −0.009857 | −0.01514 | 0.016374 | 0.003485 | 0.033633 | 0.070915 | 0.028714 | 0.014704 | −0.037744 | 0.025776 | 0.055614 | −0.024708 | 0.068363 | 0.002163 |
| 137 | 0.039798 | 0.05378 | −0.019891 | 0.024185 | 0.011335 | −0.004388 | 0.000036 | 0.001985 | 0.007015 | 0.03478 | 0.040347 | 0.010444 | −0.010778 | 0.068749 |
| 138 | 0.01421 | −0.017196 | 0.023182 | 0.026977 | 0.017048 | −0.020006 | −0.044614 | 0.01116 | 0.036726 | 0.005383 | −0.001435 | −0.00413 | −0.031902 | −0.063255 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 139 | −0.000018 | −0.00878 | 0.013791 | −0.027123 | 0.054867 | 0.027333 | 0.012496 | −0.060605 | −0.081534 | −0.019142 | 0.024452 | −0.044509 | −0.013707 | −0.02745 |
| 140 | 0.023413 | 0.005858 | 0.036096 | 0.003638 | 0.016902 | 0.057819 | −0.031297 | 0.027695 | −0.019243 | 0.074629 | 0.019272 | 0.066301 | −0.067733 | 0.065655 |
| 141 | −0.012728 | 0.006703 | 0.028772 | 0.017035 | −0.043979 | 0.027696 | 0.003132 | −0.012905 | −0.00537 | −0.001214 | 0.050909 | 0.023508 | 0.013507 | −0.017957 |
| 142 | −0.024344 | 0.011439 | −0.002002 | −0.000633 | 0.050746 | −0.003598 | −0.0494 | 0.009635 | 0.068474 | 0.036252 | 0.009815 | 0.036909 | −0.098804 | 0.01749 |
| 143 | 0.001629 | −0.037891 | 0.007788 | −0.026687 | −0.024879 | 0.050595 | −0.012255 | 0.051328 | −0.019126 | 0.021673 | 0.014723 | −0.032218 | −0.011255 | −0.021312 |
| 144 | −0.042891 | −0.002804 | 0.02363 | −0.000069 | −0.005665 | 0.015762 | −0.005755 | 0.012817 | 0.023768 | 0.005847 | −0.001337 | −0.020212 | −0.014896 | 0.029176 |
| 145 | 0.01189 | −0.027812 | 0.005855 | −0.001437 | 0.002328 | −0.000358 | 0.011319 | 0.04098 | 0.026953 | −0.003233 | 0.005213 | 0.031994 | 0.027607 | 0.012177 |
| 146 | −0.004972 | 0.001588 | 0.014798 | 0.015534 | −0.00214 | −0.016459 | 0.015889 | −0.005526 | −0.017097 | −0.015978 | 0.031376 | 0.010768 | 0.004751 | 0.022783 |
| 147 | 0.036142 | 0.009515 | 0.045925 | 0.020138 | 0.042065 | −0.047458 | −0.059698 | −0.036927 | −0.043046 | −0.036979 | −0.034274 | −0.008489 | −0.035493 | 0.047236 |
| 148 | −0.010897 | 0.051449 | 0.017518 | −0.012897 | 0.008619 | −0.016509 | 0.014058 | 0.013586 | −0.017565 | 0.030441 | −0.050191 | −0.004267 | −0.006761 | −0.024202 |
| 149 | 0.022751 | 0.040575 | −0.010008 | −0.04137 | −0.072314 | 0.030444 | −0.035532 | 0.031412 | −0.010553 | 0.034184 | −0.012387 | 0.008071 | 0.060708 | −0.033134 |
| 150 | 0.052896 | −0.017266 | 0.023469 | 0.004284 | 0.033398 | −0.027522 | −0.00442 | 0.031261 | −0.028022 | 0.008922 | 0.026433 | 0.008298 | −0.076734 | −0.057363 |
| 151 | 0.031614 | 0.016597 | 0.017027 | −0.024308 | 0.000466 | 0.015281 | 0.006466 | −0.025403 | 0.058378 | −0.034448 | −0.002785 | −0.029738 | −0.049446 | 0.020222 |
| 152 | −0.00427 | 0.00163 | 0.010433 | 0.027373 | 0.022436 | 0.001137 | 0.013569 | 0.006227 | −0.007935 | −0.027612 | −0.017318 | −0.062222 | 0.003264 | 0.025153 |
| 153 | −0.004745 | −0.006669 | 0.044801 | 0.042346 | 0.012832 | −0.001112 | 0.03347 | −0.002394 | −0.062805 | 0.017666 | 0.040559 | −0.025419 | −0.101239 | 0.010787 |
| 154 | −0.021667 | 0.031092 | 0.020931 | 0.023858 | 0.009855 | 0.014691 | −0.014066 | 0.024474 | 0.017102 | 0.005193 | 0.022514 | −0.034462 | −0.051169 | −0.031531 |
| 155 | −0.00664 | 0.005339 | −0.012015 | −0.002953 | −0.012252 | 0.028796 | 0.028583 | 0.001178 | 0.026952 | 0.017855 | 0.012345 | −0.004464 | 0.02081 | 0.007908 |
| 156 | −0.002485 | 0.028217 | 0.007443 | 0.02055 | 0.000939 | −0.003582 | 0.00689 | 0.037194 | −0.015957 | 0.00637 | 0.027693 | 0.061131 | 0.048016 | −0.004671 |
| 157 | 0.005898 | −0.015327 | −0.026928 | −0.012437 | −0.013099 | −0.061093 | −0.059602 | 0.017792 | 0.052863 | −0.025041 | −0.032299 | −0.009028 | −0.000775 | 0.048512 |
| 158 | 0.002716 | −0.013001 | 0.00707 | −0.018492 | −0.049568 | −0.009258 | 0.018577 | −0.036531 | 0.001312 | 0.016185 | 0.004987 | 0.022455 | 0.009351 | −0.036333 |
| 159 | 0.031253 | 0.015454 | 0.028764 | 0.011724 | −0.018143 | −0.024548 | −0.043543 | 0.01355 | 0.048751 | −0.003396 | −0.091137 | 0.006541 | 0.001306 | 0.002027 |
| 160 | −0.053703 | 0.007292 | −0.00525 | −0.006831 | 0.007586 | 0.040989 | 0.054301 | −0.014667 | −0.065413 | −0.011881 | 0.050936 | 0.0105 | 0.018045 | 0.039305 |
| 161 | −0.001426 | −0.018381 | −0.022118 | −0.022163 | 0.019573 | −0.024422 | −0.031432 | −0.051006 | −0.034519 | 0.057408 | −0.022433 | −0.0283 | −0.039063 | −0.016793 |
| 162 | −0.016909 | −0.012879 | −0.012876 | −0.007253 | 0.017002 | 0.012562 | −0.049996 | −0.04166 | −0.00122 | 0.021127 | 0.010211 | 0.017568 | 0.020514 | 0.080011 |
| 163 | −0.034471 | −0.007741 | −0.016984 | −0.005316 | 0.023558 | −0.020187 | −0.020637 | −0.007817 | 0.037646 | −0.006089 | 0.022484 | 0.037116 | −0.001838 | 0.009974 |
| 164 | −0.039881 | −0.010934 | 0.001942 | 0.024233 | −0.023644 | 0.020289 | −0.058219 | −0.038912 | 0.0189 | 0.009494 | −0.035553 | 0.001069 | 0.005096 | −0.025746 |
| 165 | 0.032655 | −0.009475 | 0.054385 | 0.018147 | −0.022791 | −0.031237 | −0.057687 | 0.010038 | −0.056691 | −0.026285 | 0.014259 | −0.069008 | −0.044117 | 0.030509 |
| 166 | 0.038187 | 0.020417 | −0.052208 | −0.053145 | 0.009853 | −0.006171 | −0.005123 | 0.001583 | 0.013792 | −0.028471 | 0.014945 | 0.069737 | −0.017309 | 0.018626 |
| 167 | 0.047222 | −0.017857 | −0.020299 | −0.007277 | −0.039533 | 0.067104 | 0.033072 | 0.015342 | −0.023903 | 0.030187 | −0.008624 | 0.041601 | 0.034294 | −0.022223 |
| 168 | −0.025815 | 0.017947 | 0.040547 | 0.027238 | 0.016484 | −0.01771 | 0.041677 | 0.011004 | 0.094916 | 0.022844 | −0.018943 | −0.003931 | 0.013058 | −0.031346 |
| 169 | 0.014104 | 0.032931 | 0.037825 | −0.000256 | −0.026772 | 0.035601 | −0.010745 | 0.058305 | 0.029396 | 0.019992 | −0.008599 | −0.007336 | 0.031493 | −0.005682 |
| 170 | 0.008655 | 0.052771 | 0.032512 | 0.006789 | −0.040326 | 0.025429 | −0.008105 | 0.067878 | 0.014482 | −0.012494 | −0.008271 | −0.025932 | 0.030748 | −0.001631 |
| 171 | −0.009435 | 0.033476 | 0.050769 | 0.012242 | −0.009438 | 0.024242 | −0.00486 | 0.036362 | 0.01258 | 0.010762 | 0.001088 | 0.009856 | 0.033694 | −0.001183 |
| 172 | −0.03725 | 0.007992 | 0.019578 | −0.011906 | −0.002307 | −0.018769 | −0.010678 | −0.021278 | 0.065565 | −0.025694 | 0.011051 | −0.013323 | −0.008823 | −0.025109 |
| 173 | −0.036582 | −0.005014 | 0.006483 | 0.006263 | 0.014997 | 0.011789 | −0.034169 | −0.00646 | 0.04985 | −0.019576 | 0.040883 | 0.059473 | −0.046109 | 0.01858 |
| 174 | −0.031158 | −0.001951 | −0.020472 | −0.014634 | −0.019741 | 0.005202 | −0.034425 | −0.017594 | 0.083071 | −0.015875 | −0.020636 | 0.0424 | 0.006683 | −0.010001 |
| 175 | −0.036999 | −0.034931 | −0.00453 | −0.03448 | 0.001987 | −0.040847 | −0.046421 | 0.003237 | 0.064348 | −0.008508 | 0.004536 | 0.031808 | 0.016964 | 0.034087 |
| 176 | 0.004835 | −0.028291 | 0.035821 | 0.011685 | −0.003001 | −0.014663 | −0.004375 | 0.039504 | −0.067702 | 0.034846 | 0.002359 | −0.013213 | −0.004197 | 0.015984 |
| 177 | 0.045445 | 0.020633 | −0.000981 | −0.011609 | 0.016675 | −0.036867 | 0.02686 | −0.03195 | −0.019782 | 0.004866 | −0.05575 | 0.009316 | −0.04434 | −0.030361 |
| 178 | −0.007268 | −0.013219 | 0.032045 | −0.016633 | 0.035882 | −0.018076 | −0.016225 | −0.052193 | −0.000995 | −0.019817 | −0.021283 | 0.014976 | 0.035379 | 0.00547 |
| 179 | −0.015931 | −0.028135 | −0.015888 | −0.014162 | −0.005162 | 0.013515 | 0.010583 | −0.006326 | −0.006645 | 0.021686 | −0.028098 | 0.014623 | 0.00493 | 0.033943 |
| 180 | 0.010496 | −0.030128 | −0.000528 | −0.019677 | 0.009909 | 0.01412 | −0.016886 | 0.004345 | −0.033561 | 0.014059 | −0.008947 | 0.013319 | 0.000899 | 0.017092 |
| 181 | 0.022491 | −0.008117 | −0.015641 | −0.029153 | 0.003689 | 0.021934 | 0.01679 | 0.000205 | −0.025339 | 0.015387 | 0.013438 | 0.003861 | 0.00499 | 0.045766 |
| 182 | −0.033812 | 0.0204211 | −0.0052321 | −0.021901 | −0.01931 | 0.011126 | 0.014022 | −0.004763 | 0.003119 | 0.00455 | −0.000741 | 0.001301 | 0.001329 | 0.019548 |
| 183 | −0.055435 | −0.026141 | 0.001225 | 0.012954 | −0.007744 | −0.026049 | 0.037499 | −0.013969 | −0.019899 | 0.015333 | −0.034723 | −0.014012 | 0.007236 | 0.008908 |
| 184 | −0.046349 | −0.03033 | 0.021333 | −0.020384 | −0.00207 | −0.028474 | 0.032375 | 0.049526 | 0.037092 | 0.053004 | 0.019237 | −0.053057 | −0.013125 | −0.004139 |
| 185 | 0.004165 | 0.001239 | −0.00647 | −0.023793 | 0.023763 | −0.0293 | 0.019144 | 0.05282 | 0.039554 | 0.033999 | 0.051743 | −0.003813 | 0.015181 | −0.016809 |
| 186 | −0.052451 | −0.032264 | −0.048374 | −0.02535 | −0.018618 | −0.014981 | −0.051268 | 0.013764 | 0.023333 | −0.059012 | 0.089911 | 0.011641 | −0.052358 | −0.044326 |
| 187 | −0.049608 | −0.085969 | −0.000438 | 0.015738 | 0.002377 | −0.004506 | −0.032523 | −0.007775 | −0.008855 | −0.006246 | −0.001432 | 0.001836 | 0.017734 | −0.004448 |
| 188 | −0.048995 | −0.078882 | 0.012054 | 0.006488 | 0.003485 | 0.003002 | −0.031217 | −0.000837 | −0.002084 | 0.010925 | −0.006745 | 0.006578 | 0.03031 | −0.01069 |
| 189 | −0.026359 | −0.074607 | −0.015805 | 0.007228 | −0.031251 | −0.023979 | −0.054325 | 0.001323 | −0.008283 | −0.001202 | −0.021407 | 0.015301 | 0.025086 | 0.000971 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 190 | 0.010428 | −0.003463 | −0.041849 | −0.049439 | −0.094606 | −0.007477 | −0.012142 | 0.034163 | 0.01382 | −0.012934 | −0.018743 | −0.05561 | −0.04194 | −0.05256 |
| 191 | 0.007414 | 0.001056 | −0.055483 | −0.046729 | −0.106502 | 0.034739 | 0.007892 | 0.040174 | 0.008899 | 0.005821 | −0.019566 | −0.03014 | −0.004317 | −0.011953 |
| 192 | −0.119935 | 0.001055 | 0.000402 | 0.0188 | −0.045903 | 0.03222 | −0.009784 | −0.004016 | 0.015768 | −0.007451 | −0.030951 | 0.049685 | 0.014134 | −0.022584 |
| 193 | 0.792016 | −0.050965 | −0.018995 | −0.001164 | −0.020765 | 0.013715 | 0.007092 | −0.012479 | 0.047306 | −0.005446 | 0.005202 | −0.013629 | 0.035703 | −0.040237 |
| 194 | −0.049963 | 0.737866 | −0.024272 | −0.008888 | 0.025268 | −0.036153 | −0.023809 | −0.01062 | −0.071765 | 0.00124 | −0.067825 | 0.003089 | −0.001103 | 0.026043 |
| 195 | 0.00494 | −0.056629 | 0.743612 | −0.109795 | −0.028751 | −0.076969 | 0.057524 | −0.068695 | −0.008867 | −0.0725 | 0.009726 | 0.046915 | −0.044423 | 0.022005 |
| 196 | 0.008472 | −0.020336 | −0.115966 | 0.85381 | −0.044052 | −0.018501 | 0.021208 | −0.014556 | 0.024749 | −0.0248 | 0.012474 | 0.004583 | −0.037356 | 0.010516 |
| 197 | −0.016466 | 0.022327 | −0.0487931 | −0.047621 | 0.792896 | 0.00364 | −0.012139 | 0.034529 | 0.024135 | −0.03824 | −0.034163 | −0.034134 | −0.002045 | −0.051737 |
| 198 | −0.011294 | −0.033654 | −0.067722 | −0.017853 | 0.017816 | 0.6935 | −0.004013 | −0.102229 | 0.025835 | −0.146575 | −0.040869 | −0.015227 | −0.04052 | 0.044452 |
| 199 | −0.010371 | −0.032546 | 0.019571 | 0.028649 | −0.006783 | −0.005664 | 0.483884 | 0.023331 | −0.004891 | 0.009077 | −0.089661 | 0.01866 | −0.05183 | 0.031255 |
| 200 | −0.034921 | −0.045506 | −0.057859 | −0.007187 | 0.043527 | −0.075235 | 0.061643 | 0.706552 | 0.018611 | −0.086551 | −0.048021 | 0.004975 | 0.012799 | 0.013571 |
| 201 | 0.022623 | −0.04625 | −0.005976 | 0.016685 | 0.030846 | 0.023714 | 0.018488 | −0.013937 | 0.505953 | −0.008957 | −0.03367 | −0.030043 | −0.021356 | 0.044129 |
| 202 | −0.044012 | −0.01534 | −0.077242 | −0.033517 | −0.043276 | −0.125957 | 0.014106 | −0.119142 | 0.016343 | 0.699859 | 0.011544 | −0.019848 | 0.009314 | 0.01853 |
| 203 | 0.004458 | −0.053221 | −0.003435 | 0.025536 | −0.032908 | −0.077458 | −0.088823 | −0.056387 | −0.023682 | −0.002009 | 0.637131 | 0.008329 | 0.060435 | −0.034827 |
| 204 | 0.012174 | −0.008958 | 0.02126 | −0.017361 | −0.035047 | −0.046367 | 0.055757 | 0.031198 | −0.027679 | −0.038026 | 0.053831 | 0.550869 | 0.006235 | −0.050084 |
| 205 | 0.001938 | −0.007125 | −0.050778 | −0.038907 | −0.032355 | −0.015003 | −0.036124 | −0.040546 | −0.007092 | −0.002158 | −0.008399 | 0.074072 | 0.371969 | −0.01945 |
| 206 | −0.011476 | 0.057005 | −0.008294 | −0.014579 | −0.037593 | 0.006774 | 0.043884 | 0.023649 | 0.071359 | −0.005602 | −0.027702 | −0.060901 | 0.001124 | 0.546344 |
| 207 | 0.003904 | 0.084511 | 0.045863 | −0.016812 | −0.003652 | 0.031275 | −0.019642 | 0.065228 | 0.011184 | 0.055874 | 0.055304 | −0.09701 | 0.067927 | −0.078629 |
| 208 | 0.022911 | −0.013045 | −0.013582 | 0.026455 | −0.045321 | −0.060671 | 0.01034 | −0.020563 | −0.000972 | −0.024851 | −0.110596 | −0.037667 | −0.026411 | −0.11811 |
| 209 | −0.00527 | −0.058832 | 0.041017 | −0.00394 | 0.027317 | −0.038945 | −0.043966 | −0.0233 | 0.031291 | −0.034644 | −0.036451 | −0.027289 | −0.003427 | 0.027327 |
| 210 | −0.003797 | 0.018466 | −0.002416 | 0.003873 | −0.032719 | −0.008503 | 0.006259 | −0.013243 | 0.004486 | −0.018071 | −0.023767 | −0.005712 | 0.051271 | 0.011968 |
| 211 | 0.012204 | 0.043088 | 0.064719 | 0.024868 | −0.00007 | 0.036127 | 0.005891 | −0.017591 | −0.072578 | −0.013978 | 0.041488 | −0.014466 | −0.010543 | −0.017797 |
| 212 | 0.050247 | 0.043705 | −0.007981 | −0.004528 | −0.01577 | −0.05294 | −0.028932 | −0.033463 | −0.009787 | −0.014615 | 0.009474 | 0.02956 | −0.047444 | 0.004896 |
| 213 | 0.013341 | 0.000049 | 0.02813 | −0.022753 | −0.010006 | 0.055711 | −0.025211 | 0.036754 | −0.00795 | 0.034017 | −0.013385 | 0.05499 | −0.011057 | −0.047108 |
| 214 | −0.008236 | −0.023767 | 0.005199 | −0.014751 | 0.007866 | 0.016671 | −0.005409 | 0.009331 | −0.002915 | 0.025554 | 0.020968 | 0.009362 | 0.003727 | 0.015928 |
| 215 | −0.030371 | −0.056473 | −0.019267 | −0.035131 | 0.018442 | 0.017974 | 0.000071 | −0.043443 | −0.002343 | 0.038117 | 0.031711 | −0.0264 | −0.03988 | −0.00652 |
| 216 | 0.034258 | −0.008165 | 0.025 | 0.008855 | −0.00779 | −0.020005 | −0.012992 | 0.030829 | 0.018728 | −0.032669 | 0.00177 | 0.010454 | 0.016445 | 0.012525 |
| 217 | 0.010078 | −0.019699 | 0.013653 | 0.02365 | 0.011179 | −0.02324 | −0.031064 | −0.001593 | 0.053069 | −0.024257 | −0.023609 | −0.044967 | −0.048711 | −0.027677 |
| 218 | −0.020498 | 0.010339 | −0.012382 | −0.012586 | −0.004284 | 0.012786 | 0.013036 | 0.025141 | 0.007325 | −0.005222 | 0.024083 | −0.005829 | −0.030261 | 0.001298 |
| 219 | 0.016278 | 0.022375 | −0.002693 | −0.003889 | 0.006023 | 0.014993 | −0.005781 | 0.037064 | 0.030156 | 0.001223 | 0.02833 | 0.013317 | 0.008135 | 0.004218 |
| 220 | 0.013344 | 0.02558 | 0.010914 | 0.019867 | −0.019287 | −0.02531 | 0.010325 | 0.010085 | 0.02632 | 0.016075 | −0.017541 | −0.067591 | 0.003058 | −0.025373 |
| 221 | 0.023902 | 0.032397 | −0.000755 | 0.003026 | 0.010611 | −0.001833 | 0.082596 | −0.00523 | 0.027658 | −0.016066 | 0.02098 | 0.040916 | −0.040865 | −0.010894 |
| 222 | −0.015073 | 0.008741 | 0.024336 | 0.004342 | 0.019429 | 0.027892 | 0.017614 | −0.016027 | 0.040089 | 0.008588 | −0.017119 | 0.033635 | −0.002939 | −0.005867 |
| 223 | −0.032672 | −0.025024 | 0.02846 | 0.003829 | 0.035606 | 0.024265 | 0.028335 | 0.010799 | 0.023063 | 0.033494 | 0.01449 | −0.000575 | 0.019381 | 0.006126 |
| 224 | −0.02583 | −0.001586 | −0.017954 | −0.012857 | −0.00323 | −0.009957 | −0.028575 | −0.017568 | −0.019555 | −0.064976 | 0.023283 | −0.001934 | −0.014183 | 0.020425 |
| 225 | −0.007647 | 0.003711 | −0.029674 | −0.00162 | 0.029788 | −0.039213 | −0.058371 | −0.006141 | −0.013353 | −0.046652 | −0.013389 | 0.041974 | −0.032975 | 0.034975 |
| 226 | 0.017994 | 0.023183 | −0.003053 | −0.004556 | 0.000617 | −0.035398 | 0.014389 | −0.007727 | −0.001789 | −0.015051 | 0.02055 | −0.006428 | −0.000399 | 0.03429 |
| 227 | −0.031799 | −0.009012 | 0.046562 | 0.021701 | −0.004173 | 0.003477 | −0.023111 | 0.025108 | −0.017745 | 0.002713 | −0.027784 | −0.019019 | 0.05828 | −0.047658 |
| 228 | −0.003487 | 0.029349 | 0.004118 | −0.017478 | −0.05581 | 0.053542 | 0.024104 | −0.018768 | 0.005285 | −0.044917 | −0.023662 | −0.055992 | 0.028569 | 0.003086 |
| 229 | 0.015267 | −0.025783 | −0.024158 | 0.005937 | 0.045986 | 0.015227 | 0.006139 | −0.00911 | −0.012969 | 0.027587 | −0.028843 | −0.005051 | 0.034432 | 0.043961 |
| 230 | −0.00411 | −0.015979 | 0.010474 | 0.003068 | −0.006342 | 0.017075 | −0.004987 | −0.022246 | −0.039571 | −0.017109 | 0.020225 | −0.036439 | −0.032611 | 0.045684 |
| 231 | 0.009532 | 0.026368 | 0.008872 | 0.003291 | −0.021182 | 0.013442 | 0.032037 | 0.043806 | 0.025463 | 0.040497 | 0.029427 | −0.031849 | 0.024867 | −0.022325 |
| 232 | −0.001687 | 0.021194 | −0.024451 | −0.017092 | −0.040772 | −0.032052 | −0.035791 | 0.013631 | 0.008638 | −0.029367 | 0.002352 | −0.049721 | 0.068569 | 0.013663 |
| 233 | 0.002133 | −0.007991 | 0.006594 | 0.03151 | 0.010108 | −0.027038 | 0.006716 | −0.024227 | −0.06173 | −0.030143 | 0.018062 | −0.033282 | 0.020408 | 0.000759 |
| 234 | 0.009825 | 0.003875 | 0.030525 | 0.020642 | 0.00217 | 0.031895 | 0.017395 | −0.048559 | 0.011028 | 0.02592 | −0.007514 | 0.010815 | 0.024637 | −0.024597 |
| 235 | 0.004123 | 0.011329 | 0.02447 | 0.018938 | 0.033312 | 0.053585 | −0.009008 | −0.020339 | 0.078222 | 0.058927 | 0.02285 | 0.00883 | 0.028474 | −0.045928 |
| 236 | −0.004645 | −0.014209 | −0.011178 | −0.020237 | −0.031602 | −0.011548 | 0.016266 | 0.008604 | 0.026022 | 0.025999 | −0.008964 | −0.038111 | −0.010255 | −0.041902 |
| 237 | 0.024003 | −0.002248 | 0.017454 | 0.002015 | −0.011782 | 0.005723 | −0.028651 | 0.01737 | −0.021861 | 0.02536 | −0.023161 | 0.007633 | 0.025966 | 0.01297 |
| 238 | 0.011932 | −0.014145 | −0.021307 | −0.014073 | −0.033894 | 0.042796 | −0.026379 | 0.022096 | −0.02932 | −0.003499 | 0.016176 | −0.033545 | −0.010238 | 0.022828 |
| 239 | 0.005504 | −0.011497 | −0.034968 | −0.018028 | −0.012871 | 0.013554 | −0.023603 | 0.019246 | −0.025097 | −0.02212 | −0.009353 | −0.016147 | −0.017822 | 0.022987 |
| 240 | −0.008951 | −0.00984 | 0.014606 | 0.001652 | 0.0016 | 0.023011 | 0.010664 | 0.011471 | 0.006531 | −0.02401 , | 0.001706 | −0.016541 | −0.023512 | −0.011353 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 241 | 0.002861 | 0.001115 | −0.013309 | −0.007103 | 0.000745 | 0.006052 | 0.029516 | −0.020626 | −0.015787 | −0.020016 | −0.003683 | −0.05028 | 0.026055 | 0.006629 |
| 242 | −0.019576 | 0.019014 | 0.02012 | 0.026826 | 0.002407 | −0.00743 | −0.004643 | −0.01756 | 0.016406 | 0.000365 | −0.020025 | −0.019865 | 0.004568 | −0.043596 |
| 243 | 0.012411 | 0.004253 | 0.005498 | 0.010601 | 0.011247 | −0.009898 | −0.015957 | 0.007244 | −0.049795 | −0.030828 | 0.02285 | −0.014812 | −0.024011 | −0.002466 |
| 244 | 0.002806 | 0.006564 | 0.009119 | 0.026689 | 0.017004 | −0.027839 | 0.035367 | −0.013584 | −0.021615 | −0.008223 | −0.028139 | 0.031145 | −0.028505 | −0.042199 |
| 245 | −0.038451 | −0.009486 | 0.0054 | 0.006907 | 0.006803 | 0.04348 | −0.005952 | 0.008905 | 0.001828 | 0.027887 | −0.027831 | 0.027725 | 0.014442 | −0.014816 |
| 246 | −0.015046 | −0.00241 | 0.014588 | 0.016606 | 0.012559 | 0.041418 | −0.010339 | −0.000844 | 0.015552 | 0.03714 | −0.015961 | 0.0128661 | 0.025693 | 0.022133 |
| 247 | 0.0239331 | −0.0359951 | −0.0121661 | −0.023789 | 0.010381 | 0.00414 | 0.004459 | −0.008222 | −0.012218 | 0.0294171 | −0.004197 | −0.015664 | −0.036332 | 0.009955 |
| 248 | 0.012328 | −0.025067 | −0.032878 | −0.030308 | −0.015247 | 0.004275 | 0.038882 | 0.001513 | −0.003867 | 0.024698 | 0.02567 | −0.034365 | −0.013569 | −0.010501 |
| 249 | −0.0502 | −0.018369 | 0.021749 | 0.000207 | 0.004489 | 0.016926 | −0.012146 | 0.016225 | −0.014172 | −0.01575 | 0.003177 | −0.05737 | −0.017893 | −0.01719 |
| 250 | −0.02268 | −0.038796 | 0.022151 | 0.003246 | 0.014491 | 0.026611 | −0.016789 | 0.006857 | −0.015494 | 0.027276 | 0.008928 | 0.030604 | −0.020965 | −0.01048 |
| 251 | −0.000746 | −0.005528 | 0.023394 | 0.011731 | 0.020438 | 0.011067 | −0.004925 | −0.000112 | 0.004916 | 0.005142 | −0.002401 | −0.018962 | 0.020228 | −0.023876 |
| 252 | −0.006798 | 0.008676 | −0.036207 | −0.041222 | 0.003316 | −0.039453 | −0.018393 | 0.022257 | −0.008341 | −0.010855 | −0.022366 | −0.028862 | 0.003248 | 0.00999 |
| 253 | 0.013989 | −0.012994 | 0.007282 | −0.019644 | 0.014509 | 0.00271 | 0.016366 | 0.00972 | 0.003686 | 0.024522 | −0.014001 | −0.02728 | 0.020129 | 0.032998 |
| 254 | −0.040395 | −0.0110221 | 0.0156181 | 0.009877 | 0.030064 | 0.001939 | 0.007861 | 0.020441 | 0.028619 | 0.023909 | 0.000068 | −0.000667 | 0.031062 | −0.019212 |
| 255 | −0.000497 | 0.0135231 | 0.028763 | 0.023737 | 0.001194 | −0.018472 | 0.0398 | −0.011831 | 0.026543 | −0.005716 | −0.001295 | 0.011277 | 0.023104 | −0.014214 |
| 256 | −0.023 | −0.014957 | −0.032688 | −0.037917 | −0.017002 | −0.014785 | 0.027608 | −0.03736 | 0.021252 | 0.017056 | −0.02216 | −0.033775 | 0.031269 | −0.000691 |
| 257 | 0.005434 | −0.013898 | −0.022411 | −0.013223 | −0.001005 | −0.015247 | −0.033181 | −0.02083 | −0.000741 | 0.015516 | 0.007947 | 0.028609 | 0.008996 | 0.010035 |
| 258 | 0.034329 | −0.009599 | −0.036636 | −0.038941 | 0.004704 | 0.005595 | −0.03742 | −0.012178 | 0.019329 | 0.013989 | 0.00362 | 0.018543 | −0.005992 | 0.005249 |
| 259 | −0.032538 | −0.013382 | 0.029547 | 0.010449 | 0.015426 | 0.036897 | −0.003399 | 0.006916 | −0.020587 | 0.01498 | 0.000404 | −0.007513 | −0.014417 | −0.011372 |
| 260 | −0.004327 | −0.009199 | −0.022386 | −0.023143 | 0.06489 | −0.026941 | −0.052174 | 0.036438 | −0.033695 | 0.025746 | −0.009696 | 0.051551 | −0.061735 | 0.018459 |
| 261 | 0.009442 | 0.000075 | −0.050067 | −0.050157 | 0.003941 | 0.02674 | 0.012484 | 0.016722 | −0.001096 | 0.015992 | 4.023492 | 0.012721 | −0.013409 | −0.022833 |
| 262 | 0.006741 | 4.006747 | −0.01048 | −0.035133 | 0.002923 | −0.044097 | −0.01 | −0.050329 | 0.037353 | −0.028139 | −0.038589 | −0.019516 | 0.012288 | −0.010542 |
| 263 | −0.002758 | −0.007971 | 0.00335 | −0.015431 | −0.001917 | −0.031921 | 0.020382 | −0.054527 | 0.017027 | −0.04285 | −0.035266 | −0.016522 | 0.054396 | 0.000271 |
| 264 | −0.025611 | −0.008722 | 0.046134 | 0.013788 | 0.007142 | 0.047786 | 0.012759 | 0.008513 | −0.005955 | 0.02607 | 0.005896 | −0.006646 | 0.053545 | −0.014873 |
| 265 | −0.029443 | −0.047837 | −0.077064 | −0.034572 | 0.014383 | −0.014075 | −0.032315 | 0.000777 | −0.027436 | 0.019565 | −0.029498 | −0.014229 | 0.024277 | −0.002336 |
| 266 | −0.007734 | −0.038048 | −0.091358 | −0.044142 | −0.00428 | −0.049248 | 0.00267 | −0.013571 | −0.026625 | 0.002338 | −0.005045 | 0.003308 | −0.036023 | 0.017003 |
| 267 | 0.021921 | 0.031649 | −0.006206 | 0.004662 | 0.03157 | −0.02371 | −0.026441 | −0.002668 | 0.011166 | −0.009704 | −0.004595 | 0.005971 | 0.040777 | −0.014226 |
| 268 | 0.016896 | 0.0121121 | −0.0121171 | −0.010349 | −0.004993 | −0.055059 | −0.023158 | −0.009828 | 0.0012721 | −0.030061 | −0.021843 | 0.010911 | 0.002471 | 0.030532 |
| 269 | 0.0220561 | 0.0162231 | −0.0014741 | 0.000962 | 0.005899 | −0.043807 | 0.015807 | −0.002774 | 0.019894 | −0.01325 | 0.033135 | −0.011016 | −0.007606 | 0.020903 |
| 270 | −0.005608 | 0.012702 | 0.012121 | 0.006244 | −0.013174 | −0.034776 | 0.020197 | 0.003311 | 0.020456 | −0.02132 | 0.003322 | −0.001702 | 0.037554 | −0.017153 |
| 271 | −0.02278 | 0.055608 | 0.025255 | 0.024368 | −0.00694 | 0.035893 | −0.062966 | −0.00909 | 0.009112 | −0.023757 | −0.00609 | 0.044272 | 0.033123 | −0.029098 |
| 272 | 0.002723 | 0.014009 | −0.034879 | −0.004195 | 0.006502 | 0.02627 | −0.001575 | −0.021368 | 0.012227 | 0.013779 | −0.003681 | 0.004402 | 0.041778 | 0.021527 |
| 273 | −0.001515 | −0.001137 | −0.031963 | −0.022009 | −0.006319 | −0.01037 | −0.024411 | −0.019872 | −0.009676 | −0.023531 | 0.006065 | −0.00569 | −0.007053 | 0.019951 |
| 274 | 0.000374 | 0.001924 | −0.030805 | −0.019162 | 0.001059 | −0.000457 | −0.009647 | −0.017303 | −0.007583 | −0.013003 | 0.018386 | −0.008606 | −0.00793 | 0.006938 |
| 275 | −0.030883 | −0.026817 | 0.030295 | −0.00629 | −0.000503 | 0.015259 | 0.035621 | −0.014886 | 0.011118 | 0.008875 | 0.012273 | −0.036025 | 0.003545 | −0.049818 |
| 276 | 0.021842 | −0.01355 | −0.001408 | −0.033219 | −0.0192 | 0.004387 | 0.006188 | 0.024991 | 0.032013 | 0.057119 | −0.027115 | −0.012818 | −0.018842 | −0.028448 |
| 277 | −0.009965 | −0.006386 | −0.030661 | −0.009935 | 0.012152 | −0.006162 | −0.000598 | 0.004137 | −0.00864 | −0.017582 | −0.007925 | 0.031229 | −0.018018 | −0.010546 |
| 278 | −0.018468 | 0.003222 | −0.003826 | 0.008418 | 0.008403 | −0.008286 | 0.026931 | −0.005022 | 0.004569 | −0.013063 | 0.013629 | 0.012772 | −0.036037 | −0.001148 |
| 279 | −0.0105161 | −0.014576 | −0.025223 | −0.014028 | −0.022274 | 0.020106 | 0.00294 | 0.009557 | −0.015894 | −0.030639 | 0.019275 | −0.014793 | −0.020914 | 0.004978 |
| 280 | 0.006214 | 0.01911 | 0.010129 | −0.007584 | −0.017612 | −0.010458 | −0.009445 | −0.005984 | −0.038483 | −0.043452 | 0.008505 | 0.032595 | −0.019668 | 0.024281 |
| 281 | 0.00222 | −0.004193 | −0.000241 | 0.008748 | −0.011884 | 0.032054 | −0.006183 | 0.003771 | −0.05751 | −0.003078 | −0.009594 | 0.011363 | 0.01581 | 0.01657 |
| 282 | −0.003689 | 0.011365 | 0.019374 | 0.010469 | 0.000149 | 0.026654 | 0.020662 | −0.008503 | −0.015146 | −0.014437 | 0.034945 | −0.001602 | −0.003045 | 0.001697 |
| 283 | 0.007239 | −0.022611 | 0.008509 | −0.016357 | 0.01973 | 0.008852 | 0.087428 | 0.00044 | −0.009885 | 0.013094 | 0.051015 | −0.019376 | −0.013826 | −0.026773 |
| 284 | −0.007048 | −0.000895 | 0.000155 | −0.009019 | −0.005169 | 0.003771 | −0.029079 | −0.013788 | 0.004206 | 0.026447 | 0.013217 | 0.01702 | 0.01123 | −0.011114 |
| 285 | −0.001118 | −0.007587 | 0.017693 | .0.00658 | 0.009974 | −0.00435 | −0.023776 | −0.012041 | −0.010335 | 0.016577 | 0.022018 | −0.006761 | −0.00838 | −0.017111 |
| 286 | 0.020237 | −0.009247 | 0.022975 | −0.014514 | 0.021159 | −0.008386 | −0.055836 | −0.014693 | −0.025839 | 0.036253 | −0.005997 | −0.002883 | 0.003718 | −0.002744 |
| 287 | 0.01511 | 0.014576 | 0.042146 | −0.000153 | 0.019021 | −0.00623 | −0.010532 | −0.004639 | −0.015407 | −0.015355 | 0.035228 | −0.004098 | 0.020533 | 0.001951 |
| 288 | 0.015526 | −0.040499 | 0.004707 | −0.016929 | −0.011645 | 0.000245 | −0.021582 | 0.013679 | 0.046313 | 0.02505 | 0.003956 | −0.009798 | 0.007362 | −0.020799 |
| 289 | −0.002391 | −0.01497 | −0.047596 | −0.018982 | 0.005951 | −0.091648 | −0.020127 | −0.058938 | 0.0416 | −0.041763 | −0.037642 | −0.011982 | 0.006371 | −0.036042 |
| 290 | −0.029941 | −0.021056 | −0.000815 | 0.005515 | 0.01724 | 0.017483 | 0.01103 | 0.012557 | 0.004284 | 0.018326 | −0.006356 | 0.007205 | 0.015456 | −0.000178 |
| 291 | −0.027687 | −0.023212 | 0.000434 | 0.003728 | 0.019498 | 0.018596 | 0.010032 | 0.008257 | 0.004905 | 0.022727 | −0.009529 | 0.007841 | 0.013755 | 0.000594 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 292 | −0.029027 | −0.02151 | 0.010309 | 0.002987 | 0.021349 | 0.045339 | 0.016486 | 0.018611 | 0.02729 | 0.030357 | 0.024214 | −0.015713 | 0.025501 | −0.004664 |
| 293 | −0.030101 | −0.03224 | 0.050712 | 0.011144 | −0.014586 | 0.024791 | 0.003791 | 0.011663 | 0.019214 | 0.037197 | −0.057118 | −0.001027 | −0.026279 | 0.02184 |
| 294 | −0.005281 | 0.003509 | 0.007006 | 0.002516 | −0.004521 | 0.013003 | 0.009499 | 0.005328 | 0.001909 | 0.020472 | −0.006149 | 0.025501 | −0.037101 | −0.032033 |
| 295 | −0.012036 | −0.001835 | 0.025085 | 0.018679 | −0.020149 | 0.020253 | −0.033467 | 0.037538 | 0.004653 | 0.032548 | −0.026611 | 0.015392 | −0.031834 | −0.006333 |
| 296 | 0.008041 | −0.007201 | 0.009454 | 0.003635 | 0.01188 | 0.023482 | −0.010009 | 0.044615 | 0.004131 | 0.034831 | −0.041973 | 0.025434 | −0.023469 | −0.005744 |
| 297 | −0.016438 | 0.003376 | 0.028233 | 0.014769 | −0.007249 | 0.007886 | −0.016828 | 0.044877 | 0.004566 | 0.018398 | −0.020095 | 0.004419 | −0.014531 | 0.028274 |
| 298 | −0.005221 | 0.027757 | 0.019294 | −0.003404 | 0.017663 | 0.015979 | −0.007441 | −0.037162 | 0.014457 | 0.030135 | 0.032256 | 0.058305 | 0.031464 | 0.020413 |
| 299 | 0.000225 | 0.021257 | −0.005688 | 0.001251 | −0.037328 | −0.003981 | −0.010908 | 0.042099 | −0.022597 | 0.016777 | −0.053429 | −0.002715 | 0.01062 | 0.013714 |
| 300 | −0.011368 | 0.021284 | 0.055416 | −0.037172 | −0.021476 | −0.019093 | −0.051674 | −0.020412 | 0.002952 | −0.032826 | 0.038763 | 0.001253 | 0.018811 | −0.04376 |
| 301 | −0.010724 | 0.013612 | 0.011501 | 0.022995 | −0.020097 | −0.011424 | −0.016268 | 0.00778 | 0.005764 | 0.012827 | −0.045858 | 0.033929 | −0.000643 | 0.004273 |
| 302 | 0.014069 | 0.002326 | −0.000513 | −0.000297 | 0.000853 | −0.017236 | 0.008675 | −0.012157 | −0.002309 | −0.000434 | −0.034387 | 0.024871 | −0.001233 | −0.022869 |
| 303 | 0.020396 | 0.01484 | −0.009554 | −0.00394 | 0.006128 | −0.00859 | −0.001778 | 0.00648 | −0.03772 | 0.021254 | −0.023907 | 0.026751 | −0.033464 | −0.004589 |
| 304 | 0.001601 | 0.000395 | −0.008823 | −0.040063 | −0.013339 | 0.011136 | 0.021336 | 0.007318 | −0.03823 | 0.014468 | −0.042963 | 0.014856 | 0.006853 | −0.016711 |
| 305 | −0.046055 | 0.042262 | 0.00384 | 0.019638 | −0.023524 | −0.004091 | 0.072892 | −0.033292 | 0.011887 | −0.039999 | −0.021376 | −0.035503 | 0.052447 | −0.072635 |
| 306 | 0.000533 | −0.0038 | −0.025721 | −0.002388 | 0.003812 | 0.001646 | −0.010131 | −0.008226 | −0.031263 | −0.003562 | −0.040022 | −0.003268 | −0.018003 | −0.002887 |
| 307 | −0.041112 | −0.027601 | −0.018433 | −0.027013 | −0.032103 | 0.042353 | 0.006325 | 0.012157 | −0.01346f | −0.037724 | 0.033356 | 0.006563 | −0.072078 | −0.083018 |
| 308 | −0.017029 | −0.008458 | −0.003985 | −0.013668 | −0.000269 | 0.006233 | 0.016651 | −0.009833 | −0.020255 | −0.051392 | 0.01164 | −0.011164 | 0.035463 | 0.032621 |
| 309 | −0.012612 | −0.018137 | 0.025175 | 0.005017 | 0.009507 | 0.000694 | 0.018993 | 0.011252 | 0.002295 | −0.024399 | 0.021632 | −0.004916 | 0.016966 | −0.002542 |
| 310 | −0.005807 | −0.032704 | 0.009947 | 0.026453 | 0.038828 | 0.017538 | 0.003584 | −0.013103 | −0.062486 | 0.033559 | −0.008286 | −0.002492 | 0.012738 | −0.040461 |
| 311 | −0.008213 | −0.021912 | −0.004169 | 0.003804 | 0.017821 | −0.042677 | 0.013847 | −0.009019 | −0.019091 | 0.002192 | −0.062671 | −0.013484 | −0.016183 | 0.011616 |
| 312 | 0.032174 | 0.024156 | 0.024254 | 0.035186 | 0.045135 | −0.034984 | 0.021784 | −0.01544 | 0.017517 | 0.032173 | 0.031703 | −0.047287 | 0.086771 | 0.041743 |
| 313 | 0.002104 | 0.00846 | −0.011901 | 0.017062 | −0.016973 | −0.000522 | 0.044988 | −0.024255 | −0.04521 | −0.004773 | −0.031769 | 0.004101 | 0.048065 | 0.031156 |
| 314 | −0.011779 | 0.001145 | 0.042791 | 0.014968 | −0.015039 | −0.010972 | 0.082355 | −0.019964 | −0.022202 | −0.031967 | 0.024451 | −0.108545 | 0.023641 | 0.019475 |
| 315 | 0.000727 | −0.005905 | 0.002114 | 0.011457 | −0.019591 | 0.003612 | −0.000847 | 0.026735 | −0.029095 | −0.015185 | −0.028789 | −0.009798 | 0.010714 | 0.007754 |
| 316 | 0.057174 | −0.04344 | 0.008078 | 0.00394 | 0.00079 | −0.042839 | 0.069514 | −0.031007 | 0.037667 | −0.010395 | 0.00161 | 0.012423 | −0.039093 | −0.021517 |
| 317 | −0.019664 | −0.036175 | −0.00951 | 0.005881 | 0.015538 | 0.009371 | 0.028909 | 0.015237 | −0.006195 | 0.003158 | 0.01255 | 0.03522 | −0.012538 | 0.016547 |
| 318 | 0.016204 | −0.034193 | 0.027781 | 0.011562 | 0.012274 | −0.017336 | 0.032898 | 0.000689 | −0.044452 | −0.001916 | −0.019694 | −0.003232 | −0.026727 | 0.006876 |
| 319 | 0.008875 | −0.019424 | 0.003743 | −0.005565 | 0.018174 | −0.001395 | 0.011604 | 0.018829 | 0.00495 | −0.001367 | 0.017621 | 0.008317 | 0.010779 | 0.026753 |
| 320 | 0.017351 | −0.011569 | −0.044015 | −0.038947 | 0.019806 | −0.008484 | −0.011277 | −0.014288 | 0.043273 | 0.025999 | −0.018964 | −0.008799 | 0.000988 | 0.032675 |
| 321 | −0.018545 | 0.018417 | 0.010465 | 0.017873 | −0.040758 | 0.01314 | −0.01575 | 0.004441 | −0.006846 | −0.004833 | −0.040962 | −0.023482 | 0.0445 | −0.001236 |
| 322 | −0.002548 | −0.003392 | 0.050038 | 0.00354 | 0.015072 | 0.003376 | −0.033646 | 0.006491 | 0.010135 | 0.025536 | 0.004087 | 0.021433 | 0.012578 | 0.004851 |
| 323 | 0.01406 | 0.039291 | 0.009159 | 0.02482 | −0.022489 | 0.013928 | −0.030816 | −0.011858 | −0.052917 | 0.03676 | 0.03381 | −0.007569 | 0.050559 | 0.043919 |
| 324 | 0.036279 | −0.029284 | −0.00454 | 0.014952 | −0.027099 | −0.022844 | 0.011224 | −0.008861 | −0.091196 | −0.002327 | −0.052126 | −0.025344 | −0.008698 | −0.023709 |
| 325 | −0.002782 | −0.001727 | −0.003537 | −0.010864 | −0.003908 | 0.029255 | 0.006114 | 0.022044 | 0.006123 | 0.026013 | 0.02693 | 0.010022 | −0.060429 | 0.014531 |
| 326 | −0.01242 | 0.015469 | −0.064305 | −0.012274 | −0.020286 | −0.013233 | 0.055918 | −0.002277 | 0.015594 | −0.014191 | −0.013652 | −0.019748 | 0.017799 | 0.00833 |
| 327 | 0.017948 | 0.019629 | −0.003727 | 0.005 | −0.007222 | 0.02737 | −0.008906 | 0.007511 | 0.007041 | 0.017509 | 0.003836 | −0.014426 | 0.012713 | −0.045048 |
| 328 | 0.001943 | 0.004896 | 0.027377 | −0.017677 | −0.034507 | 0.013448 | −0.033433 | 0.08731 | −0.031312 | −0.042556 | 0.023514 | −0.080163 | −0.014678 | −0.017507 |
| 329 | 0.027271 | 0.015116 | −0.013274 | 0.019119 | 0.00406 | −0.002007 | −0.016647 | −0.015138 | −0.044841 | 0.044349 | −0.029769 | −0.008506 | 0.01964 | 0.002021 |
| 330 | −0.007257 | 0.023045 | −0.004121 | −0.013191 | 0.004932 | −0.018971 | 0.013178 | −0.029029 | −0.07828 | −0.002507 | 0.003917 | 0.02952 | −0.056371 | 0.011092 |
| 331 | −0.003404 | 0.005903 | 0.006981 | −0.003389 | −0.010587 | 0.003952 | −0.022812 | −0.000189 | 0.028569 | 0.02144 | 0.004803 | 0.005365 | −0.010603 | −0.008597 |
| 332 | −0.010251 | 0.047543 | −0.016772 | −0.01662 | 0.032388 | −0.014359 | 0.023343 | 0.010556 | 0.086127 | −0.022147 | 0.064721 | 0.02489 | 0.02853 | −0.026998 |
| 333 | −0.011362 | 0.001267 | −0.005412 | −0.002041 | −0.042451 | 0.012079 | −0.036094 | 0.035279 | 0.016993 | 0.011295 | 0.023454 | 0.015806 | −0.07236 | −0.000844 |
| 334 | −0.006352 | −0.038846 | 0.021312 | 0.006603 | −0.029229 | 0.044746 | −0.042925 | 0.007659 | −0.049074 | −0.030991 | −0.02187 | −0.055503 | −0.062649 | −0.029345 |
| 335 | 0.000926 | −0.017742 | −0.028078 | −0.007936 | −0.016884 | 0.001729 | 0.015149 | −0.005293 | 0.022614 | 0.02526 | 0.057083 | −0.029688 | −0.049767 | 0.009269 |
| 336 | 0.005007 | 0.029684 | 0.023666 | −0.005551 | −0.02265 | −0.025815 | −0.020696 | 0.015848 | 0.022456 | 0.015295 | 0.007546 | −0.003136 | 0.013926 | −0.010154 |
| 337 | −0.006531 | −0.016168 | −0.016745 | 0.022885 | −0.00475 | −0.02506 | −0.069236 | 0.014116 | −0.007763 | 0.010209 | −0.085791 | −0.043076 | −0.023349 | −0.008042 |
| 338 | 0.030723 | −0.063164 | −0.016036 | 0.000604 | 0.01704 | −0.007823 | 0.017791 | 0.011691 | −0.01759 | 0.036168 | 0.00772 | 0.09817 | 0.008542 | −0.027655 |
| 339 | −0.005692 | −0.026615 | −0.017197 | −0.041637 | −0.002097 | 0.030134 | −0.018578 | 0.016519 | 0.00045 | −0.02861 | −0.089196 | 0.000883 | 0.034029 | −0.002663 |
| 340 | 0.00226 | 0.001975 | 0.001079 | −0.006469 | 0.002484 | −0.010924 | −0.025686 | 0.015969 | −0.043964 | 0.028263 | −0.022974 | −0.066437 | 0.04196 | 0.043334 |

APPENDIX B2-continued

PCA Transformation Matrix (340 × 340; Benign/Malignant)

| | GZ | HA | HB | HC | HD | HE | HF | HG | HH | HI | HJ | HK | HL | HM |
|---|---|---|---|---|---|---|---|---|---|---|---|---|---|---|
| 1 | 0.074011 | −0.087042 | −0.03885 | −0.051106 | 0.122855 | 0.010848 | −0.007142 | 0.069161 | 0.020263 | −0.08015 | −0.085281 | −0.031135 | −0.085542 | −0.0032 |
| 2 | 0.059603 | 0.005961 | −0.063071 | 0.000425 | 0.02602 | 0.028835 | −0.002416 | 0.104262 | 0.120187 | −0.016222 | 0.007663 | −0.018908 | −0.068817 | −0.023205 |
| 3 | 0.017605 | −0.018806 | 0.094952 | 0.106177 | 0.001257 | −0.004769 | −0.027072 | −0.050001 | −0.036987 | 0.056527 | 0.02716 | 0.01573 | −0.027152 | 0.021345 |
| 4 | −0.00227 | 0.122918 | 0.021949 | −0.098178 | −0.012104 | −0.011148 | 0.091912 | −0.022783 | 0.018355 | 0.030886 | 0.089629 | 0.010795 | −0.003319 | 0.073537 |
| 5 | −0.057888 | −0.059149 | −0.036069 | 0.136465 | 0.027499 | 0.020091 | −0.069983 | −0.030404 | −0.035965 | 0.089218 | 0.069217 | −0.014329 | 0.058388 | 0.090654 |
| 6 | −0.066693 | 0.003188 | 0.006738 | −0.047033 | −0.018504 | −0.016684 | −0.008131 | 0.010383 | −0.027479 | −0.02528 | 0.06278 | −0.071884 | −0.031067 | 0.007209 |
| 7 | 0.082202 | 0.000067 | −0.068661 | 0.006572 | 0.080144 | −0.012573 | −0.064835 | −0.056481 | 0.049411 | −0.028413 | −0.023381 | 0.019531 | −0.025918 | −0.038175 |
| 8 | −0.061739 | −0.122743 | −0.077653 | −0.010488 | −0.064168 | −0.072217 | 0.025797 | 0.00827 | −0.062247 | 0.023415 | −0.002199 | −0.000427 | 0.047241 | 0.058949 |
| 9 | 0.153137 | 0.051654 | 0.091241 | 0.001933 | −0.028127 | 0.04495 | −0.068094 | −0.020807 | 0.01188 | −0.050592 | −0.038805 | −0.004335 | 0.004285 | 0.013511 |
| 10 | 0.297002 | 0.037539 | −0.068677 | −0.031566 | 0.089414 | 0.223097 | −0.053695 | −0.001437 | −0.015524 | 0.052806 | −0.021237 | 0.004619 | 0.0125 | −0.017276 |
| 11 | 0.079011 | 0.088862 | 0.034008 | −0.021207 | −0.072044 | −0.040478 | −0.035134 | 0.02609 | −0.037004 | −0.090908 | −0.009529 | −0.044681 | −0.044476 | 0.008177 |
| 12 | 0.02912 | 0.058675 | 0.04137 | −0.071602 | 0.052717 | 0.065373 | −0.030479 | −0.006524 | 0.047629 | 0.018327 | 0.020249 | −0.025732 | −0.000433 | −0.053783 |
| 13 | 0.016466 | −0.027224 | −0.074659 | −0.067214 | 0.002752 | −0.024844 | 0.071002 | 0.035136 | 0.006083 | −0.050487 | 0.104883 | −0.024248 | −0.023641 | 0.014189 |
| 14 | −0.016438 | 0.084118 | −0.032103 | −0.001413 | −0.034615 | −0.025726 | 0.081856 | −0.01795 | −0.043451 | −0.037902 | −0.071925 | −0.027339 | −0.031375 | 0.029544 |
| 15 | 0.021407 | 0.045011 | −0.195245 | −0.130913 | −0.103521 | −0.010716 | 0.02397 | −0.030765 | −0.049796 | 0.030808 | −0.076732 | 0.00214 | −0.012352 | −0.075771 |
| 16 | −0.039218 | 0.032174 | −0.040579 | 0.016555 | 0.045986 | −0.069406 | −0.012734 | −0.026113 | −0.017883 | −0.009466 | 0.045271 | −0.000695 | −0.001644 | 0.049286 |
| 17 | −0.074765 | 0.089667 | 0.051211 | 0.069826 | 0.03243 | 0.103528 | −0.025089 | −0.019873 | −0.048605 | −0.045846 | 0.011679 | −0.072281 | −0.013327 | 0.00252 |
| 18 | −0.005655 | 0.04895 | −0.016565 | 0.051426 | −0.042269 | −0.053202 | 0.009508 | −0.035307 | −0.062768 | −0.014154 | −0.032491 | 0.003991 | −0.040078 | −0.044381 |
| 19 | −0.04317 | −0.10697 | 0.157083 | −0.052626 | −0.091659 | −0.052843 | −0.02245 | −0.00132 | −0.016054 | 0.020097 | −0.026964 | −0.007122 | −0.014332 | 0.008662 |
| 20 | −0.000579 | 0.103532 | 0.114166 | −0.082177 | 0.050159 | 0.102203 | −0.09685 | −0.017403 | −0.03663 | −0.099427 | −0.079394 | 0.051236 | 0.011238 | −0.072494 |
| 21 | −0.129991 | 0.044281 | −0.116994 | −0.085118 | −0.026512 | −0.044439 | 0.033031 | 0.008876 | 0.020408 | −0.03398 | −0.064802 | −0.044621 | −0.002766 | 0.032493 |
| 22 | −0.055488 | −0.048639 | −0.00081 | 0.042642 | −0.05075 | 0.082344 | −0.048628 | −0.02194 | 0.04518 | 0.028334 | 0.018226 | −0.013962 | −0.043736 | −0.006613 |
| 23 | −0.015032 | 0.022168 | 0.051199 | 0.054162 | −0.034075 | −0.049134 | 0.031507 | −0.024319 | 0.047171 | 0.05045 | 0.063707 | 0.059136 | 0.100811 | 0.041848 |
| 24 | 0.032708 | 0.067268 | 0.000445 | −0.011307 | −0.031941 | 0.006703 | 0.048312 | −0.008654 | 0.009256 | 0.014455 | −0.010646 | −0.013251 | −0.023439 | −0.028662 |
| 25 | 0.00293 | −0.03556 | 0.072983 | 0.026671 | −0.015108 | −0.041891 | −0.016046 | 0.002969 | −0.110656 | 0.059353 | 0.004826 | −0.098237 | 0.03707 | −0.107356 |
| 26 | 0.043545 | 0.012453 | 0.046979 | 0.073754 | 0.038936 | −0.007242 | 0.041098 | −0.005756 | 0.051672 | −0.027464 | 0.095177 | 0.021332 | −0.016531 | 0.053915 |
| 27 | −0.080145 | 0.14069 | 0.051413 | 0.066572 | 0.065845 | −0.007408 | −0.030076 | 0.044623 | 0.069248 | 0.030418 | −0.007462 | −0.000588 | 0.004478 | −0.026104 |
| 28 | −0.100557 | −0.005957 | −0.053873 | 0.131777 | 0.118271 | 0.0915 | 0.061403 | 0.006537 | 0.031674 | −0.111567 | 0.032109 | 0.054891 | 0.005971 | 0.001274 |
| 29 | 0.082255 | 0.042252 | 0.074433 | −0.000185 | −0.012772 | −0.014225 | −0.013781 | −0.00363 | −0.021382 | −0.03474 | 0.007305 | −0.008954 | −0.012579 | −0.010072 |
| 30 | −0.193689 | −0.050063 | −0.142046 | −0.020541 | −0.029692 | 0.114045 | −0.018554 | −0.008006 | −0.02943 | −0.039958 | −0.056007 | −0.014569 | −0.04381 | 0.019782 |
| 31 | −0.034832 | 0.098062 | 0.051789 | −0.10044 | −0.107784 | −0.057503 | −0.00304 | 0.008929 | −0.009218 | −0.025912 | 0.096412 | 0.06936 | 0.081349 | 0.07678 |
| 32 | −0.021081 | 0.10263 | −0.031191 | 0.077222 | 0.029328 | −0.01022 | −0.041907 | 0.033984 | −0.029452 | −0.054948 | 0.023929 | 0.011439 | 0.03453 | 0.062121 |
| 33 | 0.061239 | 0.10133 | −0.045219 | 0.048541 | 0.058625 | 0.159772 | 0.00839 | −0.020549 | 0.072315 | 0.055059 | 0.016584 | 0.010756 | −0.03162 | 0.030866 |
| 34 | 0.008254 | −0.140129 | 0.048552 | −0.020584 | −0.047399 | −0.061008 | −0.107416 | 0.008113 | −0.049805 | −0.027917 | −0.034307 | 0.003196 | −0.041538 | −0.052881 |
| 35 | 0.015119 | −0.072981 | 0.033731 | 0.159973 | −0.029942 | −0.104415 | 0.095919 | 0.010325 | 0.00643 | −0.0637 | −0.020805 | −0.017616 | −0.078868 | −0.014763 |
| 36 | −0.025214 | 0.112368 | −0.1317 | −0.047982 | 0.045109 | −0.003098 | −0.124637 | −0.006648 | −0.099564 | −0.064942 | −0.011705 | 0.026032 | −0.01616 | 0.017423 |
| 37 | 0.021775 | 0.022725 | −0.044285 | −0.011331 | −0.1455 | −0.012151 | 0.117711 | −0.02229 | 0.027234 | −0.055096 | −0.016804 | −0.050437 | −0.096202 | −0.094532 |
| 38 | 0.050192 | 0.017838 | 0.045005 | −0.086727 | −0.027163 | −0.117689 | −0.137904 | −0.038011 | −0.106795 | 0.007168 | 0.021358 | −0.034575 | −0.06555 | 0.032204 |
| 39 | 0.04495 | 0.072921 | 0.039639 | 0.104698 | 0.002085 | 0.027457 | −0.059621 | −0.001567 | 0.087373 | −0.004038 | 0.008193 | 0.029109 | 0.00968 | −0.078242 |
| 40 | −0.030433 | −0.0466 | 0.020206 | −0.035707 | −0.027295 | 0.013281 | −0.055925 | −0.00381 | 0.017441 | −0.005773 | −0.070535 | 0.008876 | 0.006749 | 0.0688 |
| 41 | −0.126786 | −0.064799 | −0.085791 | 0.011307 | −0.123066 | 0.00519 | −0.082123 | −0.018296 | −0.046387 | 0.029188 | 0.052857 | −0.011682 | −0.013165 | 0.019861 |
| 42 | 0.074232 | 0.015518 | 0.01772 | −0.027325 | 0.006954 | 0.029115 | −0.01177 | −0.012324 | −0.001736 | −0.008284 | −0.023087 | 0.002823 | −0.009711 | −0.000048 |
| 43 | 0.003803 | 0.127607 | 0.040748 | −0.008254 | 0.057663 | 0.06202 | 0.043715 | 0.071271 | 0.046359 | −0.009233 | 0.05948 | 0.03963 | −0.007337 | 0.104498 |
| 44 | −0.017444 | −0.018102 | 0.06886 | 0.162663 | −0.015331 | −0.049771 | 0.227463 | −0.02506 | −0.011628 | −0.071261 | −0.027632 | −0.052796 | −0.03319 | 0.016772 |
| 45 | −0.038189 | 0.06936 | −0.089762 | −0.078324 | −0.00903 | −0.055839 | 0.145537 | −0.014765 | 0.012544 | 0.020492 | 0.087326 | 0.02295 | 0.063406 | 0.064631 |
| 46 | 0.000319 | 0.01436 | 0.014533 | −0.039092 | −0.011236 | 0.074432 | −0.00853 | 0.005672 | 0.067591 | 0.00312 | 0.015353 | −0.005483 | 0.032807 | −0.021588 |
| 47 | −0.047309 | −0.054589 | −0.020374 | 0.138813 | 0.076593 | 0.005576 | −0.040985 | 0.02263 | 0.013347 | −0.170241 | 0.089564 | 0.072148 | −0.005854 | 0.035807 |
| 48 | −0.010123 | 0.025137 | 0.095001 | −0.090234 | 0.068952 | 0.013979 | 0.01072 | −0.0036 | −0.009978 | 0.003108 | 0.036831 | 0.03554 | 0.024912 | 0.026743 |
| 49 | 0.2740371 | −0.094567 | −0.05195 | 0.128116 | 0.100696 | −0.140793 | 0.235447 | 0.007368 | −0.094483 | −0.013522 | −0.065193 | −0.0473 | 0.000559 | −0.068024 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 50 | −0.029921 | 0.082522 | −0.046169 | 0.102225 | 0.178993 | 0.058915 | −0.013127 | 0.008613 | −0.0193 | 0.090871 | −0.034718 | −0.03077 | −0.017053 | 0.006348 |
| 51 | −0.005605 | 0.01183 | −0.131544 | −0.032164 | −0.04073 | −0.041453 | 0.105055 | 0.037242 | 0.036133 | −0.084092 | 0.06885 | 0.005445 | −0.050299 | 0.058663 |
| 52 | −0.039117 | −0.012268 | 0.018223 | −0.108452 | −0.085618 | 0.050501 | 0.055741 | 0.045449 | −0.097166 | 0.006336 | 0.029557 | −0.023055 | 0.083639 | 0.068039 |
| 53 | 0.063544 | 0.080052 | 0.166724 | 0.04681 | −0.026547 | −0.082291 | −0.110648 | −0.003614 | 0.055123 | −0.029729 | −0.111205 | −0.010853 | −0.060104 | 0.02752 |
| 54 | −0.164854 | 0.058672 | −0.100359 | 0.054716 | 0.097398 | 0.118078 | −0.003698 | −0.018105 | 0.065231 | −0.066037 | −0.025146 | −0.01806 | −0.051413 | −0.011806 |
| 55 | −0.040871 | 0.10216 | 0.08813 | 0.016479 | −0.061865 | 0.146778 | 0.068102 | −0.036142 | −0.08424 | −0.002541 | −0.128868 | 0.044656 | 0.01307 | −0.080859 |
| 56 | −0.101782 | 0.004471 | 0.138879 | −0.090437 | 0.027545 | 0.063535 | −0.093173 | 0.002823 | −0.110407 | −0.013877 | 0.084222 | 0.021487 | 0.033191 | 0.00181 |
| 57 | 0.030982 | 0.03276 | 0.036484 | 0.073377 | −0.075305 | 0.009728 | −0.091039 | 0.012832 | 0.067666 | 0.015331 | −0.089248 | 0.073421 | 0.043939 | −0.018501 |
| 58 | 0.0358571 | 0.054252 | 0.0295911 | −0.013429 | 0.018383 | 0.009426 | 0.126367 | 0.05026 | −0.041313 | −0.053149 | −0.072572 | −0.008275 | 0.0028631 | −0.023235 |
| 59 | 0.0087491 | −0.063737 | −0.0631621 | −0.017283 | 0.06876 | −0.089243 | −0.009823 | 0.043874 | −0.085232 | 0.045843 | 0.015393 | 0.022782 | 0.005498 | −0.080715 |
| 60 | 0.040137 | 0.009708 | 0.007354 | 0.025525 | −0.025539 | 0.011486 | 0.048054 | 0.041182 | 0.089947 | 0.011622 | 0.014367 | −0.000141 | 0.03683 | 0.011576 |
| 61 | −0.010883 | 0.13458 | 0.001454 | 0.08168 | −0.069007 | −0.166521 | 0.057479 | −0.048247 | 0.023087 | 0.024022 | −0.020527 | −0.005916 | 0.0143 | −0.05117 |
| 62 | −0.0917 | −0.026233 | 0.1173681 | −0.001295 | 0.089736 | −0.042894 | −0.019574 | 0.005759 | 0.026547 | −0.043031 | 0.008166 | −0.023522 | −0.094509 | −0.110241 |
| 63 | 0.021043 | 0.0176971 | −0.030819 | −0.004192 | −0.052798 | −0.019688 | −0.202629 | 0.087781 | 0.1230551 | −0.024741 | −0.141301 | 0.0440081 | 0.0377831 | −0.092028 |
| 64 | −0.024124 | −0.065528 | −0.013625 | 0.061007 | −0.004163 | 0.108276 | −0.009067 | 0.029518 | 0.083751 | 0.041566 | 0.039137 | 0.011611 | −0.013345 | 0.002594 |
| 65 | −0.004741 | 0.174002 | −0.040325 | −0.019083 | 0.019628 | −0.127677 | −0.027739 | −0.000773 | 0.115601 | 0.034259 | −0.037351 | 0.054185 | 0.010897 | −0.020082 |
| 66 | 0.075466 | −0.050833 | −0.122073 | 0.071078 | 0.006963 | 0.208905 | −0.115785 | 0.000627 | 0.023213 | 0.017867 | 0.072629 | 0.015103 | 0.041558 | 0.017737 |
| 67 | −0.111567 | 0.095995 | 0.099197 | −0.073262 | 0.028627 | −0.156161 | 0.008348 | −0.005939 | −0.040158 | 0.017293 | 0.00504 | 0.026078 | −0.016096 | 0.026918 |
| 68 | 0.068493 | −0.029791 | 0.098767 | 0.069716 | 0.099557 | −0.113395 | −0.041992 | 0.016316 | −0.048825 | −0.030828 | −0.051905 | 0.008782 | −0.00158 | −0.001556 |
| 69 | 0.086153 | −0.033839 | −0.072327 | 0.056183 | −0.057415 | 0.004903 | −0.113751 | 0.033581 | 0.005937 | 0.049829 | −0.048347 | 0.040859 | −0.0129 | 0.015653 |
| 70 | −0.027221 | 0.00479 | 0.023324 | −0.096605 | −0.053691 | 0.046411 | −0.137675 | −0.049273 | −0.061455 | −0.089317 | 0.036784 | −0.007638 | 0.010266 | 0.069457 |
| 71 | 0.009665 | −0.080225 | 0.01313 | 0.005318 | 0.142574 | −0.003391 | 0.049354 | −0.041351 | −0.007563 | −0.098384 | −0.035446 | −0.029331 | −0.0548 | 0.039455 |
| 72 | 0.037731 | −0.008181 | −0.01785 | −0.037106 | −0.036815 | −0.094048 | 0.006025 | 0.045909 | −0.070807 | 0.053054 | 0.112004 | −0.010474 | 0.023758 | 0.024137 |
| 73 | 0.000074 | 0.037705 | −0.088752 | 0.060397 | 0.081603 | 0.01719 | −0.02989 | −0.003049 | −0.037061 | −0.006148 | −0.048567 | −0.039856 | −0.069132 | −0.024861 |
| 74 | −0.054963 | 0.081346 | −0.055734 | −0.073262 | 0.009983 | −0.01989 | −0.022066 | 0.016975 | 0.027532 | −0.039794 | −0.100832 | −0.037606 | −0.03315 | −0.084472 |
| 75 | −0.060955 | −0.005883 | 0.002636 | 0.013554 | 0.118433 | −0.055587 | 0.005148 | 0.039724 | −0.062678 | 0.054778 | 0.015941 | −0.006252 | 0.066689 | −0.027905 |
| 76 | −0.139856 | 0.040822 | −0.084348 | −0.099049 | −0.087943 | −0.053123 | −0.051147 | −0.00274 | 0.089125 | 0.050997 | 0.012117 | 0.013241 | −0.026866 | −0.091734 |
| 77 | 0.103422 | −0.064097 | 0.029433 | 0.056825 | 0.014843 | 0.109602 | 0.104471 | −0.08297 | −0.022664 | 0.120992 | −0.002222 | 0.034991 | 0.053234 | 0.027226 |
| 78 | −0.030064 | 0.011388 | 0.124807 | −0.001509 | −0.022516 | 0.013674 | 0.07636 | 0.079275 | 0.0494 | −0.024577 | −0.049251 | 0.008266 | 0.017637 | −0.016487 |
| 79 | 0.063762 | −0.008767 | 0.025682 | 0.093896 | 0.045392 | −0.015438 | −0.087159 | 0.015848 | 0.026969 | −0.013616 | 0.010266 | 0.006653 | 0.00366 | 0.013931 |
| 80 | −0.037124 | −0.092286 | 0.086767 | 0.036821 | −0.034424 | 0.031751 | 0.079664 | −0.025324 | −0.019145 | −0.074756 | −0.077818 | 0.023618 | −0.032329 | −0.059497 |
| 81 | −0.00289 | 0.03231 | 0.084433 | −0.025717 | −0.027613 | −0.005411 | −0.212907 | −0.000805 | 0.071548 | 0.030659 | 0.016371 | −0.046358 | −0.017016 | 0.041989 |
| 82 | 0.105522 | −0.0609131 | −0.115063 | 0.019685 | 0.042254 | −0.178889 | −0.034549 | −0.044991 | 0.062953 | 0.022225 | 0.160983 | −0.004073 | −0.002476 | 0.128819 |
| 83 | −0.0694921 | 0.0189921 | 0.0079221 | −0.143612 | 0.056645 | 0.119417 | 0.045354 | 0.045929 | −0.071601 | 0.0154951 | −0.041099 | −0.050023 | −0.046225 | −0.053599 |
| 84 | 0.02701 | −0.131627 | −0.049365 | −0.019276 | −0.079011 | 0.159762 | 0.076643 | −0.015011 | −0.055683 | 0.01543 | 0.023233 | −0.03716 | −0.016981 | 0.077434 |
| 85 | 0.039651 | 0.043631 | 0.079545 | −0.039402 | −0.122099 | 0.163751 | 0.018874 | 0.002764 | 0.008305 | −0.041484 | −0.028011 | −0.023096 | −0.002453 | −0.055555 |
| 86 | −0.06151 | 0.00746 | −0.042879 | 0.074592 | 0.047885 | −0.086935 | −0.049708 | 0.077725 | 0.054753 | −0.070477 | −0.052506 | 0.06712 | 0.047033 | −0.008281 |
| 87 | 0.003903 | 0.044704 | 0.016364 | −0.052481 | −0.007374 | −0.105109 | 0.028516 | −0.02815 | 0.057307 | 0.03854 | −0.015263 | −0.008554 | −0.010746 | 0.021872 |
| 88 | 0.072305 | −0.032191 | −0.084438 | −0.028424 | 0.024477 | −0.030505 | 0.031718 | −0.021439 | 0.110679 | −0.005867 | −0.082155 | 0.02763 | 0.008083 | −0.069646 |
| 89 | 0.029282 | −0.1604091 | 0.081012 | −0.036783 | 0.076271 | −0.041932 | −0.122829 | 0.084637 | −0.012455 | −0.039599 | −0.148105 | 0.0524091 | 0.0833471 | −0.007353 |
| 90 | 0.0236961 | −0.015966 | −0.09637 | −0.052686 | 0.075106 | −0.155291 | −0.122442 | −0.015944 | 0.003655 | 0.069402 | 0.122781 | 0.012741 | 0.020187 | 0.00889 |
| 91 | 0.011966 | −0.092427 | −0.033472 | −0.06325 | −0.026287 | −0.013447 | 0.099608 | 0.019181 | 0.013513 | −0.011272 | 0.002552 | −0.049549 | −0.02209 | −0.022707 |
| 92 | −0.06081 | 0.004178 | −0.061243 | 0.143244 | −0.01228 | 0.068101 | −0.022945 | −0.012374 | −0.102287 | −0.001358 | −0.03172 | 0.021457 | 0.000212 | −0.009558 |
| 93 | −0.122598 | 0.00972 | 0.067932 | 0.067612 | 0.009501 | 0.025869 | 0.018708 | −0.025507 | −0.088204 | 0.092503 | −0.037075 | −0.063183 | −0.025223 | 0.006145 |
| 94 | −0.015197 | 0.004569 | 0.024201 | 0.149587 | −0.164023 | −0.059728 | 0.067401 | −0.035123 | −0.020101 | 0.137027 | −0.061779 | 0.021299 | 0.02679 | −0.034086 |
| 95 | −0.021634 | −0.017812 | −0.028475 | −0.051258 | −0.001597 | −0.006551 | 0.086267 | −0.015161 | 0.087529 | 0.022797 | −0.02943 | 0.01978 | 0.018758 | −0.06606 |
| 96 | 0.013978 | 0.017383 | 0.013709 | −0.008408 | 0.064303 | −0.050422 | 0.019549 | −0.073234 | −0.01095 | 0.026273 | −0.038877 | 0.012572 | 0.023726 | 0.02202 |
| 97 | 0.010242 | 0.002322 | −0.081419 | 0.068518 | −0.058702 | −0.084287 | −0.040874 | 0.030593 | −0.098727 | .0.006716 | 0.00183 | −0.039611 | −0.005922 | 0.038136 |
| 98 | 0.065968 | −0.050506 | 0.075532 | −0.089686 | 0.05672 | 0.019476 | −0.049345 | −0.039162 | −0.159963 | −0.024998 | −0.002946 | 0.052426 | 0.013967 | 0.006256 |
| 99 | −0.129344 | −0.088613 | −0.096222 | 0.007913 | −0.011542 | 0.061609 | 0.128872 | 0.101185 | 0.113783 | 0.03555 | 0.001049 | 0.076418 | 0.074034 | 0.011431 |
| 100 | 0.0274691 | 0.023455 | 0.018941 | 0.027122 | 0.000364 | −0.038243 | −0.020386 | −0.048741 | −0.022806 | −0.00663 | −0.020789 | 0.023013 | 0.018175 | −0.012405 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 101 | 0.030412 | 0.033454 | 0.019968 | 0.024087 | 0.006581 | −0.000765 | −0.016058 | −0.050279 | −0.025524 | 0.000042 | 0.019703 | −0.003113 | −0.008602 | 0.009901 |
| 102 | 0.050311 | −0.015532 | −0.000813 | 0.022608 | 0.000151 | −0.013826 | −0.006174 | 0.017679 | 0.00586 | 0.012933 | 0.00502 | 0.01864 | 0.008583 | 0.013778 |
| 103 | −0.014888 | −0.025071 | −0.008559 | −0.047633 | −0.016676 | −0.007265 | −0.047035 | −0.016221 | −0.002957 | −0.005035 | 0.061925 | 0.008727 | −0.002893 | 0.032982 |
| 104 | 0.053193 | −0.044576 | 0.0442741 | −0.046448 | 0.013868 | −0.074872 | −0.015086 | 0.009307 | −0.013714 | 0.0220671 | −0.020104 | 0.034148 | 0.03153 | 0.026363 |
| 105 | 0.018572 | 0.015118 | −0.018212 | −0.068923 | −0.055962 | −0.001177 | −0.016624 | 0.013055 | −0.032668 | 0.023882 | −0.004189 | −0.00239 | 0.031007 | −0.02914 |
| 106 | −0.051172 | 0.010369 | 0.007015 | 0.016236 | 0.004918 | −0.031472 | −0.004704 | −0.010589 | −0.025354 | −0.037394 | −0.056706 | −0.040679 | −0.051172 | −0.029361 |
| 107 | 0.056012 | 0.018241 | 0.041571 | −0.036428 | 0.019767 | 0.010622 | 0.010489 | 0.002847 | −0.052559 | −0.007783 | −0.021979 | −0.030449 | −0.034453 | −0.009777 |
| 108 | 0.045254 | −0.007149 | 0.014301 | 0.010295 | −0.016814 | −0.011222 | −0.080089 | −0.003502 | 0.00579 | 0.009749 | 0.002747 | −0.004712 | −0.01677 | 0.017904 |
| 109 | −0.008704 | −0.05038 | −0.013036 | −0.044212 | 0.057949 | 0.002318 | −0.069013 | 0.007876 | −0.018686 | −0.012624 | −0.026222 | −0.015065 | −0.023299 | −0.011944 |
| 110 | −0.079756 | −0.043809 | −0.064586 | −0.016276 | 0.040565 | −0.044378 | 0.008475 | −0.018176 | 0.012154 | 0.009284 | −0.008278 | −0.006502 | −0.007881 | 0.015222 |
| 111 | 0.015884 | −0.008443 | 0.06314 | −0.075418 | 0.019528 | 0.05058 | −0.022897 | 0.016169 | −0.049121 | −0.003954 | −0.027198 | −0.001969 | −0.0124 | −0.000366 |
| 112 | 0.025976 | −0.037435 | −0.013691 | 0.006407 | 0.03733 | −0.001028 | −0.023448 | 0.016647 | 0.030968 | −0.040134 | −0.015775 | −0.001957 | −0.008318 | −0.012608 |
| 113 | 0.035804 | 0.042281 | 0.01228 | −0.015197 | 0.005956 | −0.079968 | −0.03017 | 0.017466 | 0.075843 | −0.003721 | −0.012478 | 0.010098 | 0.003698 | 0.001047 |
| 114 | −0.011028 | 0.046733 | −0.026425 | 0.067224 | −0.021539 | 0.004247 | 0.116727 | −0.009242 | 0.0569911 | 0.0328991 | −0.007832 | 0.0089111 | −0.039656 | 0.049401 |
| 115 | 0.0338451 | −0.051988 | 0.006493 | 0.037114 | −0.011109 | 0.014257 | −0.004192 | −0.023612 | −0.00242 | −0.013956 | 0.018088 | −0.014907 | −0.001504 | −0.023995 |
| 116 | 0.015416 | 0.007708 | −0.00861 | −0.0498 | 0.010862 | −0.048632 | 0.048635 | −0.005347 | −0.002026 | 0.021289 | 0.043224 | 0.01132 | −0.010122 | −0.010356 |
| 117 | −0.004087 | −0.001016 | 0.00738 | 0.013853 | 0.028314 | −0.041685 | 0.047584 | −0.01144 | −0.043264 | 0.04001 | −0.006558 | 0.003812 | 0.017572 | 0.001838 |
| 118 | −0.105619 | −0.048998 | −0.018798 | −0.010847 | −0.04037 | −0.11075 | 0.042859 | −0.006306 | −0.031457 | −0.013738 | −0.025646 | 0.017064 | 0.013425 | −0.030631 |
| 119 | −0.061332 | −0.003315 | 0.030849 | 0.025767 | 0.014757 | 0.026087 | −0.047097 | 0.011378 | 0.008466 | −0.01974 | −0.089001 | −0.004592 | −0.006766 | −0.050018 |
| 120 | 0.053438 | 0.026553 | 0.039663 | 0.004828 | 0.008117 | −0.02928 | 0.025247 | −0.003968 | −0.020886 | 0.017953 | 0.010874 | 0.009555 | 0.015534 | 0.01161 |
| 121 | −0.018402 | 0.02353 | −0.02815 | 0.014955 | 0.0199 | −0.049213 | 0.049634 | −0.01285 | 0.023012 | 0.00753 | 0.006038 | 0.011529 | −0.003103 | −0.009091 |
| 122 | −0.062219 | 0.021917 | 0.018568 | −0.023618 | 0.016262 | −0.017502 | −0.015196 | 0.009455 | −0.018056 | −0.036884 | 0.035082 | −0.023559 | −0.003492 | 0.018874 |
| 123 | −0.053139 | 0.059096 | 0.016349 | −0.01361 | 0.008139 | 0.041995 | −0.001102 | −0.032952 | 0.002395 | −0.005629 | −0.007171 | −0.022185 | −0.044749 | −0.010996 |
| 124 | 0.0115811 | −0.0211871 | −0.0004951 | 0.010335 | 0.001134 | 0.037047 | 0.002263 | 0.024168 | 0.0339641 | −0.032826 | −0.040508 | 0.0041111 | −0.00542 | −0.056404 |
| 125 | −0.0017471 | −0.021885 | 0.016932 | −0.064139 | −0.022281 | 0.008964 | −0.021738 | −0.013598 | −0.037286 | 0.0114461 | 0.0047151 | 0.0284341 | 0.0171361 | −0.012588 |
| 126 | −0.015614 | 0.044748 | 0.04701 | −0.022485 | 0.017196 | 0.006707 | 0.025013 | 0.000555 | 0.046518 | −0.036198 | −0.029803 | 0.033686 | 0.003009 | −0.018136 |
| 127 | −0.017208 | 0.005294 | 0.034824 | −0.025882 | 0.016957 | 0.019639 | 0.024929 | −0.011064 | 0.040475 | −0.008601 | −0.024765 | 0.010959 | 0.003782 | −0.020532 |
| 128 | 0.02263 | −0.006138 | 0.019039 | −0.033277 | −0.053396 | −0.033512 | 0.052168 | 0.007928 | 0.012364 | 0.030425 | −0.041123 | 0.00776 | 0.029381 | −0.008718 |
| 129 | 0.029932 | −0.066015 | −0.00706 | −0.057688 | −0.023356 | −0.035982 | −0.018614 | −0.005431 | −0.008588 | −0.002296 | 0.005067 | 0.01879 | 0.023571 | 0.015907 |
| 130 | 0.0537171 | −0.005475 | −0.02611 | 0.025265 | −0.0038 | 0.080762 | 0.106418 | −0.005481 | 0.0229811 | −0.014474 | 0.0142171 | −0.006182 | −0.022046 | −0.012835 |
| 131 | −0.0271721 | −0.0551 | 0.052894 | −0.045881 | −0.034066 | 0.031618 | 0.015778 | −0.002213 | 0.005679 | 0.012456 | −0.009041 | −0.002913 | 0.008319 | −0.032976 |
| 132 | −0.037244 | 0.010297 | 0.00907 | −0.041201 | 0.085827 | 0.008296 | −0.031706 | 0.009673 | −0.047919 | 0.068972 | −0.028888 | −0.023062 | −0.003318 | −0.05239 |
| 133 | −0.008836 | −0.000493 | −0.032039 | 0.02902 | 0.042599 | −0.009789 | −0.050354 | −0.018037 | −0.015142 | 0.007549 | 0.00594 | −0.02004 | −0.015041 | −0.017169 |
| 134 | 0.041105 | −0.029917 | −0.093342 | −0.006953 | −0.035662 | 0.022524 | −0.050445 | 0.014554 | −0.024404 | 0.002763 | 0.030825 | 0.027977 | 0.042501 | 0.00029 |
| 135 | 0.037886 | −0.025929 | −0.0131941 | 0.010556 | −0.053554 | 0.035082 | 0.030511 | −0.004798 | −0.021911 | −0.003771 | −0.015987 | −0.024662 | −0.009181 | −0.016969 |
| 136 | 0.060327 | 0.018618 | −0.0081 | −0.03118 | −0.040642 | 0.007682 | −0.012213 | −0.032856 | −0.013464 | 0.00372 | −0.010008 | −0.005209 | −0.00367 | −0.014345 |
| 137 | 0.007903 | 0.047873 | 0.027723 | −0.049459 | 0.014982 | −0.035173 | 0.038312 | −0.015451 | 0.012904 | 0.021498 | 0.067167 | −0.000515 | 0.015428 | 0.033272 |
| 138 | −0.029966 | −0.029099 | −0.089853 | −0.089429 | −0.033472 | 0.001922 | −0.014846 | 0.0156 | −0.00764f | −0.012625 | −0.000881 | 0.007929 | 0.019485 | 0.046781 |
| 139 | −0.103668 | 0.009103 | 0.0112531 | 0.028791 | 0.002126 | −0.023448 | 0.011625 | 0.020702 | 0.044858 | −0.036888 | 0.004504 | −0.02825 | −0.051484 | −0.000745 |
| 140 | 0.045015 | −0.014073 | −0.0294881 | 0.076841 | −0.049826 | 0.045797 | −0.090773 | −0.023193 | −0.014831 | 0.0308741 | 0.0325711 | −0.027559 | 0.0093691 | 0.026421 |
| 141 | −0.0657891 | 0.0201591 | −0.004531 | 0.036412 | −0.004615 | −0.020729 | −0.029282 | 0.013569 | −0.025514 | −0.008663 | 0.009704 | 0.012311 | −0.000042 | 0.054216 |
| 142 | −0.004518 | 0.026026 | 0.005142 | 0.059279 | 0.043939 | −0.007938 | 0.05033 | −0.050158 | −0.024486 | 0.033822 | 0.02106 | −0.00218 | −0.00801 | 0.054425 |
| 143 | 0.034094 | 0.002866 | −0.033315 | 0.08149 | −0.027988 | −0.014488 | 0.027274 | 0.002975 | −0.030989 | −0.00478 | 0.023062 | −0.034607 | −0.010913 | 0.030257 |
| 144 | 0.045028 | 0.008321 | 0.012372 | 0.087662 | −0.009012 | 0.043375 | 0.011379 | 0.014669 | 0.002833 | −0.02493 | −0.028147 | −0.017838 | −0.007423 | −0.010899 |
| 145 | 0.0954461 | 0.0022711 | 0.015178 | −0.000134 | −0.023122 | 0.064321 | −0.010229 | −0.010406 | 0.0022721 | −0.004502 | 0.0114461 | −0.028094 | −0.026291 | 0.02554 |
| 146 | 0.0252061 | 0.039786 | 0.011031 | 0.003591 | −0.023153 | 0.002769 | −0.001541 | −0.020374 | 0.023129 | 0.007291 | −0.013132 | −0.003509 | −0.012936 | −0.01181 |
| 147 | −0.039948 | 0.062761 | −0.053132 | 0.02682 | −0.023555 | −0.091979 | 0.0216 | 0.002386 | 0.010471 | −0.006058 | −0.053952 | 0.020602 | 0.009519 | −0.00294 |
| 148 | 0.033875 | 0.06169 | 0.04914 | 0.017663 | −0.021539 | −0.016781 | −0.025879 | −0.015598 | 0.027838 | 0.020857 | −0.016235 | −0.029569 | −0.00965 | 0.026125 |
| 149 | −0.039318 | 0.017718 | 0.009923 | −0.03966 | −0.032235 | −0.024142 | −0.016186 | 0.030126 | −0.000154 | −0.027161 | 0.04321 | −0.014137 | 0.00242 | 0.016979 |
| 150 | 0.032129 | 0.023279 | 0.045135 | −0.07329 | −0.016846 | −0.021463 | −0.00648 | −0.001145 | −0.009004 | −0.000573 | −0.050153 | 0.009896 | 0.012996 | −0.014259 |
| 151 | −0.036609 | 0.022779 | −0.037124 | −0.046439 | 0.018047 | 0.045188 | −0.042183 | 0.0234 | −0.076141 | −0.01547 | −0.000258 | 0.020422 | −0.002982 | 0.023502 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 152 | 0.002969 | −0.06736 | −0.038474 | −0.02098 | 0.057 | −0.009097 | 0.014031 | 0.021963 | 0.036811 | −0.016112 | 0.018344 | 0.003659 | 0.018759 | 0.002854 |
| 153 | 0.023485 | −0.014009 | 0.000928 | 0.027723 | −0.010557 | −0.027864 | 0.001976 | −0.011034 | 0.003244 | 0.004677 | 0.053951 | −0.039953. | −0.024136 | 0.045347 |
| 154 | 0.032401 | 0.018899 | 0.021324 | 0.013739 | 0.01614 | 0.023669 | 0.070759 | −0.00163 | −0.002841 | 0.04518 | −0.010906 | −0.007101 | 0.008475 | −0.006618 |
| 155 | −0.026556 | −0.035471 | 0.0031931 | −0.040636 | 0.049463 | −0.035106 | 0.008639 | 0.005358 | 0.0099961 | 0.0394161 | −0.011036 | 0.0118811 | 0.0068261 | −0.036324 |
| 156 | −0.0176361 | −0.043701 | −0.019807 | 0.002136 | −0.033289 | −0.023248 | 0.007092 | −0.008071 | 0.067491 | 0.012004 | −0.012414 | 0.020306 | −0.015192 | 0.002583 |
| 157 | 0.004144 | −0.015958 | 0.027801 | −0.033511 | 0.008442 | 0.024978 | 0.012054 | −0.01923 | −0.038967 | −0.029213 | 0.007617 | 0.005854 | −0.000616 | 0.023596 |
| 158 | 0.034957 | 0.037808 | −0.080142 | −0.00044 | 0.054221 | 0.061879 | −0.015642 | 0.00736 | 0.016565 | 0.027035 | 0.086276 | 0.039413 | 0.015252 | 0.038379 |
| 159 | 0.011698 | −0.05202 | −0.109456 | −0.022747 | −0.018717 | 0.028023 | −0.050936 | −0.022627 | 0.084345 | −0.033273 | −0.02263 | −0.003715 | −0.009241 | 0.002031 |
| 160 | −0.023264 | 0.055651 | 0.096428 | −0.013988 | 0.000467 | −0.020666 | −0.030893 | −0.02257 | −0.059943 | 0.0369741 | 0.0470671 | 0.0225121 | 0.0340061 | 0.033919 |
| 161 | 0.056281 | 0.027164 | −0.050673 | −0.026539 | −0.011613 | 0.078969 | 0.053942 | 0.011541 | 0.020062 | 0.012202 | 0.0034 | −0.006752 | −0.031284 | 0.034132 |
| 162 | −0.005357 | 0.02869 | −0.026372 | −0–.06359 | −0.02704 | 0.087244 | 0.061371 | 0.005012 | −0.005609 | −0.041076 | −0.000787 | −0.010437 | −0.005258 | 0.011425 |
| 163 | −0.006943 | 0.015038 | 0.01479 | 0.002102 | 0.048307 | −0.024651 | 0.003848 | −0.017204 | −0.024578 | −0.000476 | 0.013376 | 0.011668 | 0.026022 | 0.030429 |
| 164 | −0.103405 | −0.022615 | 0.085034 | −0.053471 | 0.010275 | 0.032464 | −0.0385 | 0.014723 | 0.009548 | −0.004401 | −0.01282 | 0.03305 | 0.012598 | −0.018344 |
| 165 | −0.074519 | −0.023871 | −0.044186 | 0.026635 | 0.032338 | 0.037009 | −0.04928 | 0.017981 | −0.037307 | 0.03892 | 0.053633 | 0.053831 | 0.032526 | −0.016979 |
| 166 | 0.033013 | −0.027881 | −0.08209 | −0.040683 | −0.001603 | −0.005448 | −0.065503 | 0.017334 | −0.009711 | 0.01032 | 0.067002 | −0.005329 | −0.023713 | −0.005135 |
| 167 | 0.000712 | −0.015208 | 0.062547 | 0.036944 | 0.001488 | −0.052086 | −0.033359 | 0.023982 | 0.066046 | −0.02354 | 0.023138 | −0.000994 | −0.000203 | 0.005113 |
| 168 | 0.036509 | 0.014912 | 0.018871 | 0.02756 | 0.019815 | −0.003411 | 0.018553 | −0.026617 | −0.003219 | −0.110401 | 0.008824 | 0.021338 | 0.014299 | 0.021119 |
| 169 | −0.024764 | 0.006252 | 0.010428 | 0.049999 | 0.002429 | −0.033764 | 0.002717 | −0.015517 | 0.027825 | −0.028126 | −0.04437Y | −0.023639 | −0.029799 | −0.030112 |
| 170 | −0.024587 | 0.006803 | 0.015511 | 0.074188 | 0.047431 | −0.013702 | 0.0282 | −0.006927 | 0.048713 | −0.015296 | −0.045363 | −0.030545 | −0.038794 | −0.036666 |
| 171 | −0.036927 | 0.01972 | −0.029307 | 0.060754 | 0.000927 | −0.028717 | −0.016259 | −0.030775 | 0.020107 | −0.033376 | −0.03197 | −0.024703 | −0.038537 | −0.027636 |
| 172 | −0.017277 | 0.017121 | −0.015171 | 0.026213 | −0.071298 | −0.033408 | −0.018402 | 0.008547 | 0.0231 | −0.000547 | −0.059842 | −0.01121 | −0.007744 | −0.030383 |
| 173 | −0.024522 | 0.018481 | −0.031544 | −0.005493 | −0.072976 | −0.001278 | −0.00019 | 0.005376 | −0.00871 | −0.026074 | −0.013845 | −0.040958 | −0.032731 | −0.007248 |
| 174 | −0.037245 | 0.002411 | −0.041341 | 0.029839 | −0.003181 | 0.011071 | 0.005889 | 0.013274 | 0.020506 | −0.017995 | −0.016445 | −0.02867 | −0.03188 | −0.0338 |
| 175 | −0.088651 | 0.021471 | −0.030061 | −0.040785 | 0.041988 | −0.002768 | 0.03172 | 0.048383 | 0.006876 | −0.045882 | −0.001483 | −0.023831 | 0.00389 | 0.006854 |
| 176 | 0.038029 | −0.001208 | −0.01622 | 0.048149 | 0.023707 | 0.008398 | 0.013826 | 0.000258 | 0.043443 | −0.02971 | 0.007774 | −0.003367 | −0.006215 | −0.005912 |
| 177 | 0.03991 | 0.001491 | −0.020328 | −0.019597 | −0.047911 | 0.010675 | 0.021867 | 0.026474 | −0.011193 | −0.01056 | −0.022931 | −0.020141 | −0.031574 | −0.068579 |
| 178 | −0.008624 | 0.022421 | −0.035287 | −0.02982 | −0.017362 | 0.027283 | −0.026112 | −0.044821 | −0.059562 | −0.020316 | 0.027977 | −0.010486 | −0.010339 | 0.04432 |
| 179 | −0.007112 | 0.011674 | −0.019948 | 0.024825 | 0.029261 | −0.011497 | −0.00349 | −0.072331 | −0.048449 | 0.020577 | 0.012434 | 0.009055 | 0.015079 | 0.019215 |
| 180 | −0.001769 | 0.017688 | −0.014429 | 0.004251 | 0.00877 | −0.002077 | −0.021221 | −0.060332 | −0.058283 | −0.006546 | 0.015789 | −0.009059 | −0.004229 | 0.021058 |
| 181 | −0.027001 | 0.01935 | −0.02447 | 0.007768 | 0.037124 | −0.013922 | −0.019588 | −0.047575 | −0.057653 | −0.000414 | 0.022481 | −0.013687 | −0.006612 | 0.015379 |
| 182 | −0.039306 | 0.0432091 | −0.0124831 | 0.011843 | 0.084904 | −0.020955 | −0.018201 | −0.027969 | −0.015599 | 0.006599 | −0.009084 | −0.002774 | 0.014246 | 0.001677 |
| 183 | −0.009235 | 0.023585 | −0.019206 | 0.013676 | 0.031882 | −0.032766 | 0.001625 | −0.062418 | −0.023202 | 0.019831 | −0.024071 | 0.021359 | 0.018824 | −0.020262 |
| 184 | 0.035884 | 0.03192 | −0.051181 | 0.039041 | −0.004221 | 0.010493 | −0.06556 | −0.0841 | −0.020518 | 0.009641 | 0.000489 | 0.032747 | −0.012035 | −0.02017 |
| 185 | −0.020639 | −0.011009 | −0.043314 | −0.018593 | 0.004842 | −0.120567 | 0.013316 | 0.001852 | −0.028876 | 0.023067 | 0.035369 | −0.008696 | 0.01213 | 0.000804 |
| 186 | −0.000365 | 0.019038 | −0.020544 | 0.007925 | 0.059869 | −0.015611 | −0.005324 | −0.016558 | −0.03701 | −0.058208 | −0.028631 | −0.034021 | −0.046449 | −0.015872 |
| 187 | 0.035914 | 0.001964 | 0.026608 | −0.00436 | −0.013898 | 0.035368 | 0.00804 | −0.003249 | −0.005776 | −0.007937 | −0.027654 | 0.028097 | 0.022815 | −0.001056 |
| 188 | 0.009848 | 0.016213 | 0.013343 | 0.049801 | −0.01692 | 0.021934 | 0.009143 | −0.008247 | 0.023114 | 0.006283 | −0.024043 | 0.018534 | 0.009697 | −0.005195 |
| 189 | −0.025516 | 0.027687 | 0.051189 | 0.051821 | 0.010777 | 0.031938 | 0.008517 | −0.028015 | 0.036705 | 0.007226 | −0.006775 | 0.019705 | 0.012341 | 0.003506 |
| 190 | −0.014463 | −0.006539 | 0.014403 | 0.006401 | 0.03432 | −0.035252 | 0.014256 | −0.002122 | 0.00517 | 0.001188 | −0.018142 | 0.022205 | 0.020485 | −0.015741 |
| 191 | 0.001758 | −0.033075 | 0.033178 | −0.003393 | 0.021399 | 0.001117 | −0.032423 | −0.00525 | −0.03448 | 0.006348 | −0.02262 | 0.016665 | 0.019611 | −0.033254 |
| 192 | 0.022375 | −0.006195 | −0.021874 | −0.003476 | 0.020182 | −0.001539 | 0.000684 | −0.017757 | 0.007368 | 0.046989 | 0.001912 | −0.000484 | 0.023152 | 0.002401 |
| 193 | −0.038128 | 0.004578 | −0.00224 | −0.017926 | 0.015813 | 0.052409 | 0.031584 | −0.010089 | −0.051829 | 0.066314 | 0.003415 | −0.017721 | 0.026594 | 0.01071 |
| 194 | 0.061444 | −0.013821 | −0.048716 | 0.002492 | 0.02493 | 0.071855 | 0.022432 | −0.022617 | −0.041903 | −0.008151 | 0.001727 | 0.005496 | 0.028445 | 0.030252 |
| 195 | 0.001273 | −0.032489 | −0.015423 | −0.027009 | 0.08131 | −0.002397 | 0.088159 | 0.004608 | −0.026051 | 0.015424 | 0.011615 | −0.004939 | −0.002461 | 0.013232 |
| 196 | −0.026236 | 0.031948 | −0.029471 | 0.016629 | 0.06081 | −0.008873 | 0.006747 | −0.015575 | −0.029292 | −0.009721 | 0.003212 | −0.001716 | 0.003681 | 0.004948 |
| 197 | −0.016297 | −0.047811 | 0.016341 | 0.030232 | 0.034773 | −0.02968 | −0.002629 | 0.014098 | 0.03607 | 0.011312 | 0.007313 | 0.014288 | 0.028344 | −0.012772 |
| 198 | 0.029267 | −0.017703 | −0.042587 | −0.001586 | 0.037658 | −0.007225 | 0.049591 | −0.001473 | 0.023584 | −0.022504 | −0.018679 | 0.021923 | −0.00364 | 0.016754 |
| 199 | −0.030277 | 0.04264 | −0.03133 | −0.010256 | 0.000394 | −0.010477 | −0.009 | 0.004173 | 0.019144 | −0.021279 | −0.033209 | 0.011401 | 0.000715 | −0.003148 |
| 200 | −0.006545 | −0.059849 | −0.03124 | −0.049198 | −0.049617 | −0.010299 | 0.04475 | 0.00317 | −0.081069 | 0.032426 | −0.031098 | −0.003005 | 0.014059 | −0.002858 |
| 201 | 0.065745 | −0.029785 | 0.026393 | 0.041302 | −0.07961 | 0.03977 | 0.007881 | 0.000785 | 0.000517 | 0.011084 | 0.023166 | −0.013445 | −0.000234 | 0.011652 |
| 202 | 0.014941 | −0.024385 | −0.077856 | 0.000462 | 0.003758 | 0.007016 | 0.038115 | 0.030158 | 0.0336 | −0.018635 | −0.03596 | −0.008105 | 0.000146 | 0.017075 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 203 | 0.035538 | –0.136515 | 0.029877 | –0.045706 | 0.020104 | –0.012299 | –0.020367 | 0.017906 | 0.000991 | 0.008121 | –0.036629 | 0.003213 | 0.014065 | –0.049645 |
| 204 | –0.063719 | –0.015296 | –0.037791 | 0.044148 | –0.037325 | 0.031815 | 0.011607 | –0.015826 | 0.010461 | 0.025899 | –0.028171 | 0.038801 | 0.053945 | –0.034186 |
| 205 | –0.005353 | –0.005212 | –0.011759 | 0.108179 | 0.034308 | –0.062322 | 0.016695 | 0.008551 | –0.025833 | 0.001692 | –0.081563 | –0.000789 | 0.040044 | –0.034418 |
| 206 | –0.069909 | –0.100717 | 0.045716 | 0.001951 | –0.01511 | 0.036166 | –0.079402 | –0.010737 | 0.012193 | 0.010765 | 0.018796 | –0.013197 | –0.02033 | 0.006183 |
| 207 | 0.407754 | 0.052778 | –0.024613 | –0.047923 | –0.061493 | –0.02527 | –0.021714 | 0.002985 | 0.015467 | –0.024461 | 0.019131 | –0.00351 | –0.013262 | –0.004343 |
| 208 | 0.024996 | 0.555707 | –0.014408 | 0.026328 | –0.033288 | 0.025718 | 0.007371 | 0.026545 | –0.026967 | 0.018758 | 0.032684 | –0.028571 | 0.001695 | 0.00875 |
| 209 | –0.054464 | –0.060359 | 0.494589 | –0.0151 | –0.018803 | 0.042022 | 0.655499 | 0.011783 | 0.053481 | 0.022125 | 0.049347 | –0.018722 | –0.013758 | 0.015191 |
| 210 | –0.069051 | 0.00416 | –0.00868 | 0.497564 | –0.082158 | –0.014862 | –0.078985 | 0.025533 | –0.082061 | 0.0087781 | 0.018008 | –0.001325 | 0.019603 | 0.005043 |
| 211 | 0.007497 | 0.004038 | 0.011039 | –0.078535 | 0.584952 | –0.026216 | 0.005746 | –0.029181 | –0.0036 | 0.0541681 | –0.015564 | –0.015298 | 0.008234 | –0.00413 |
| 212 | –0.026574 | –0.02393 | –0.026384 | 0.026466 | –0.019275 | 0.367531 | 0.014121 | 0.014532 | 0.014721 | 0.037044 | 0.042414 | –0.001509 | –0.002982 | 0.017326 |
| 213 | –0.016766 | 0.05067 | 0.05255 | –0.649882 | 0.039523 | 0.004532 | 0.384044 | –0.005818 | –0.011012 | –0.001823 | 0.020737 | 0.043077 | 0.019102 | 0.029972 |
| 214 | 0.036297 | 0.037198 | 0.007117 | 0.032304 | –0.025079 | –0.001475 | 0.000762 | 0.881723 | –0.042182 | 0.0291751 | 0.011387 | –0.003775 | –0.669081 | 0.019194 |
| 215 | –0.031382 | –0.072516 | 0.042304 | –0.055783 | –0.022517 | –0.015509 | –0.009431 | –0.053562 | 0.657356 | 0.017461 | 0.018911 | –0.046449 | 0.009055 | 0.025613 |
| 216 | –0.015711 | 0.022132 | 0.008018 | –0.019497 | 0.03716 | 0.3653 | –0.665783 | 0.043635 | –0.002529 | 0.7573991 | –0.060438 | –0.028327 | –0.076228 | –0.030686 |
| 217 | 0.010631 | 0.003016 | 0.062195 | 0.039195 | 0.000952 | –0.002361 | –0.001153 | 0.025968 | 0.014685 | –0.042979 | 0.682906 | –0.000796 | –0.021278 | –0.152393 |
| 218 | 0.000887 | –0.01158 | –0.012847 | 0.000214 | –0.014306 | –0.007503 | 0.018825 | –0.010383 | –0.049024 | 0.001407 | –0.009968 | 0.888542 | –0.065198 | –0.02579 |
| 219 | 0.0024211 | 0.019436 | –0.035567 | 0.010969 | 0.003103 | 0.014959 | 0.016679 | –0.012992 | 0.668617 | –0.060673 | –0.051537 | –0.07389 | 0.859943 | –0.05048 |
| 220 | 0.013209 | 0.661352 | 0.626836 | –0.005812 | –0.013747 | 0.005488 | 0.002876 | 0.009945 | 0.027515 | 0.0128771 | –0.157881 | 0.006051 | –0.016874 | 0.773264 |
| 221 | –0.005197 | 0.020451 | –0.022082 | –0.031659 | –0.013167 | 0.018512 | 0.617549 | 0.0101 | –0.007042 | –0.042252 | –0.006959 | –0.031468 | –0.031283 | –0.021206 |
| 222 | –0.020906 | –0.035411 | –0.04367 | –0.026822 | –0.040428 | –0.03708 | –0.017221 | –0.000635 | –0.03009 | –0.014242 | –0.009559 | –0.033543 | –0.023369 | –0.014689 |
| 223 | –0.630676 | 0.014879 | –0.017036 | –0.041927 | 0.002478 | –0.014155 | –0.019217 | 0.001265 | –0.014761 | –0.008951 | 0.020846 | –0.027892 | –0.012794 | –0.033096 |
| 224 | 0.002508 | –0.01223 | –0.01787 | 0.015049 | –0.043515 | 0.030922 | 0.004608 | –0.662771 | –0.056024 | –0.016041 | –0.013358 | 0.661923 | 0.004662 | –0.004013 |
| 225 | 0.035635 | –0.612485 | –0.667614 | 0.009781 | –0.017973 | 0.013546 | 0.66751 | –0.004056 | –0.053273 | –0.019455 | –0.001431 | –0.004265 | –0.008205 | 0.007889 |
| 226 | 0.02083 | 0.032975 | 0.009123 | –0.003201 | 0.010056 | –0.032036 | 0.016584 | 0.012601 | 0.668635 | 0.02523 | 0.030116 | 0.0082291 | 0.004314 | 0.009142 |
| 227 | 0.00976 | 0.013382 | 0.001942 | –0.020923 | –0.010314 | 0.076245 | –0.01535 | 0.005536 | –0.037328 | –0.003216 | 0.012772 | 0.01187 | 0.011097 | –0.004094 |
| 228 | –0.043717 | –0.018404 | 0.010245 | 0.026699 | –0.023661 | –0.03458 | –0.009105 | 0.009225 | 0.033113 | 0.019537 | 0.024121 | –0.0064 | 0.009428 | 0.013414 |
| 229 | 0.003571 | –0.009545 | 0.015297 | 0.052069 | 0.04003 | 0.074722 | –0.051164 | –0.667816 | –0.014605 | –0.015121 | 0.003807 | –0.663115 | –0.66699 | 0.006001 |
| 230 | –0.0213461 | 0.627013 | 0.620341 | –0.669415 | –0.056747 | 0.004352 | 0.029949 | 0.008734 | –0.046418 | –0.072525 | 0.038031 | 0.012535 | 0.00804 | 0.037907 |
| 231 | 0.00906 | 0.020322 | –0.019979 | –0.013493 | –0.006325 | –0.04364 | –0.6i 3486 | 0.039174 | 0.637586 | 0.003678 | 0.013751 | 0.0441111 | 0.022675 | 0.007085 |
| 232 | –0.008326 | –0.00038 | 0.00682 | 0.036107 | –0.034494 | –0.013608 | –0.018191 | –0.029509 | 0.010639 | 0.048169 | –0.015444 | 0.014398 | 0.01491 | –0.031551 |
| 233 | 0.621632 | 0.01965 | 0.005031 | 0.028242 | 0.021328 | –0.008828 | –0.071027 | 0.012413 | 0.019119 | –0.021266 | 0.036841 | –0.005362 | 0.011385 | 0.017219 |
| 234 | 0.019533 | –0.006602 | 0.029075 | –0.006982 | 0.01987 | 0.009308 | 0.668788 | 0.666461 | –0.014613 | 0.663291 | 0.068067 | 0.009554 | –0.007585 | 0.021782 |
| 235 | 0.012816 | –0.6355181 | 0.0205311 | 0.01629 | –0.04435 | 0.025645 | 0.04708 | –0.010079 | –0.068085 | 0.030051 | 0.030373 | 0.004402 | –0.007074 | 0.023445 |
| 236 | –0.0075621 | –0.020546 | –0.004112 | –0.016257 | 0.002889 | 0.012699 | 0.010161 | 0.018423 | 0.023481 | –0.018816 | –0.009804 | 0.016075 | 0.008929 | –0.009672 |
| 237 | 0.033421 | –0.029819 | 0.00857 | 0.025865 | 0.018907 | 0.02348 | –0.034404 | –0.007291 | 0.011547 | 0.005027 | 0.025477 | –0.002328 | 0.016117 | 0.038979 |
| 238 | 0.013781 | –0.009903 | –0.018131 | –0.005775 | –0.002915 | –0.006838 | 0.008648 | –0.002459 | 0.020213 | –0.003611 | 0.0036531 | 0.003811 | –0.041566 | 0.021639 |
| 239 | –0.008345 | –0.002185 | –0.037315 | –0.021433 | –0.008148 | –0.025322 | 0.00672 | 0.004252 | 0.021607 | –0.02956 | –0.012432 | –0.062463 | –0.056458 | 0.624982 |
| 240 | –0.032462 | –0.01 i 181 | 0.037828 | 0.01641 | 0.019362 | 0.029373 | 0.006686 | 0.022887 | 0.006732 | –0.009208 | –0.024787 | 0.024899 | 0.027263 | 0.032097 |
| 241 | –0.004856 | –0.022929 | 0.023088 | 0.013217 | 0.040062 | 0.003775 | 0.012761 | 0.018436 | –0.004992 | –0.025802 | 0.0094241 | 0.001393 | 0.023267 | 0.009885 |
| 242 | –0.029823 | –0.01628 | –0.003571 | –0.004554 | 0.001232 | –0.011873 | –0.022536 | 0.027518 | –0.027572 | –0.000722 | 0.009083 | –0.016722 | 0.010922 | –0.037112 |
| 243 | –0.012953 | –0.006862 | –0.013722 | –0.015011 | –0.022292 | 0.005428 | 0.006935 | 0.002371 | –0.034656 | –0.036788 | –0.014093 | –0.020633 | –0.03391 | –0.001717 |
| 244 | 0.0249971 | 0.003112 | 0.017233 | –0.014543 | –0.020623 | 0.004209 | –0.007155 | –0.607596 | –0.023656 | –0.001405 | 0.017354 | 0.02015 | 0.622965 | 0.028413 |
| 245 | –0.017395 | –0.034445 | 0.001478 | 0.025692 | –0.009247 | –0.007258 | –0.031987 | –0.003734 | –0.037409 | 0.014286 | 0.012181 | –0.013046 | 0.011443 | 0.0273 |
| 246 | 0.003272 | –0.013331 | 0.003355 | –0.026039 | 0.026553 | 0.04366 | –0.000239 | 0.001218 | –0.014906 | –0.004801 | 0.019375 | –0.007551 | 0.003325 | –0.038023 |
| 247 | 0.041841 | 0.030901 | –0.010244 | –0.040974 | –0.012057 | –0.017007 | 0.008934 | –0.006233 | –0.000654 | –0.020942 | –0.004769 | 0.016947 | –0.015751 | –0.037012 |
| 248 | 0.018022 | 0.009682 | –0.026169 | –0.013101 | –0.039777 | 0.003185 | 0.01223 | –0.020133 | –0.018502 | 0.031475 | –0.018187 | 0.015926 | –0.016087 | –0.047009 |
| 249 | 0.021823 | –0.037854 | 0.008794 | 0.037336 | –0.036164 | 0.011275 | –0.006378 | –0.010934 | –0.003254 | 0.016171 | –0.057797 | –0.024197 | –0.014851 | –0.012764 |
| 250 | –0.015968 | –0.004873 | 0.046379 | –0.027778 | 0.016728 | 0.053659 | 0.027878 | 0.009712 | –0.024099 | –0.02203 | 0.009804 | 0.016358 | 0.019456 | 0.029539 |
| 251 | –0.032344 | –0.051939 | 0.018113 | 0.003981 | 0.034838 | 0.045248 | 0.049005 | 0.008408 | –0.029363 | 0.017227 | 0.032083 | 0.020132 | 0.019844 | 0.034584 |
| 252 | –0.026283 | –0.000197 | –0.038012 | 0.002768 | 0.045709 | –0.030536 | –0.039882 | –0.001336 | –0.006997 | 0.012656 | –0.008932 | 0.002888 | 0.016771 | 0.008806 |
| 253 | –0.001337 | 0.0086 | 0.012574 | 0.010494 | 0.014839 | –0.028267 | –0.020454 | –0.000853 | 0.008385 | –0.00497 | –0.020693 | 0.018133 | 0.03983 | –0.034403 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 254 | −0.014131 | 0.001533 | −0.0236951 | −0.020787 | 0.005524 | 0.008515 | −0.012967 | 0.006978 | −0.001671 | −0.004411 | 0.036364 | 0.000969 | −0.00485 | −0.004679 |
| 255 | 0.007503 | 0.004695 | −0.000053 | −0.024712 | 0.011002 | 0.017478 | 0.012754 | 0.030416 | 0.002879 | −0.028809 | 0.033688 | 0.032493 | 0.024003 | 0.000064 |
| 256 | 0.026242 | −0.032652 | 0.003062 | 0.001958 | 0.024242 | −0.024962 | −0.019688 | 0.008566 | −0.050055 | −0.012866 | 0.013584 | −0.004253 | 0.02617 | −0.031316 |
| 257 | −0.010851 | 0.006682 | 0.033804 | −0.008026 | 0.016741 | −0.002532 | 0.01171 | −0.003448 | 0.010117 | 0.003929 | 0.010494 | 0.026985 | 0.02388 | 0.008315 |
| 258 | −0.016315 | 0.016076 | 0.00082 | −0.036416 | −0.002566 | 0.000468 | 0.010621 | 0.008253 | 0.002803 | −0.01282 | −0.023309 | 0.014134 | 0.009828 | −0.000908 |
| 259 | −0.027872 | −0.025081 | −0.003567 | 0.024129 | −0.023418 | 0.021255 | 0.002236 | 0.00299 | −0.013364 | 0.013489 | −0.010542 | −0.018425 | −0.016695 | 0.005324 |
| 260 | −0.02925 | 0.010473 | −0.026836 | 0.010751 | 0.003833 | 0.062964 | −0.041376 | −0.027056 | 0.020039 | 0.020683 | −0.009171 | 0.01382 | −0.00556 | 0.011264 |
| 261 | −0.035979 | −0.007044 | −0.001861 | −0.005042 | 0.04572 | 0.027798 | −0.011311 | 0.006822 | 0.017239 | 0.023574 | −0.016853 | 0.019027 | 0.01154 | −0.00258 |
| 262 | 0.020793 | 0.024416 | −0.015457 | −0.00806 | −0.019236 | −0.028615 | 0.005909 | −0.005173 | 0.006599 | 0.004705 | −0.036485 | 0.01726 | 0.020197 | −0.012898 |
| 263 | 0.009803 | 0.0124 | −0.010253 | −0.007332 | −0.031309 | −0.02522 | 0.008721 | 0.000412 | 0.004904 | 0.003763 | −0.031606 | 0.011689 | 0.011531 | −0.008597 |
| 264 | 0.0033231 | −0.044797 | −0.035084 | 0.017752 | −0.056429 | −0.029807 | −0.018018 | 0.002709 | −0.014909 | −0.01574 | 0.018849 | 0.003966 | 0.003031 | 0.015501 |
| 265 | 0.003205 | 0.006751 | 0.009566 | 0.004592 | 0.006534 | 0.00348 | 0.030662 | −0.000549 | −0.000132 | −0.004564 | −0.008643 | 0.030525 | 0.008647 | −0.014937 |
| 266 | 0.033195 | −0.009757 | 0.017238 | −0.000062 | −0.005903 | 0.00297 | 0.042604 | −0.002137 | 0.038382 | −0.018496 | −0.012923 | 0.039943 | 0.019315 | −0.015542 |
| 267 | −0.004888 | −0.013553 | 0.02167 | −0.008964 | 0.014887 | 0.011062 | −0.018804 | 0.011128 | 0.023029 | −0.00929 | −0.008122 | −0.002275 | −0.005738 | −0.009881 |
| 268 | 0.014659 | 0.020515 | 0.003353 | −0.014293 | 0.002524 | −0.040323 | 0.011018 | 0.011842 | 0.001526 | −0.001513 | 0.019804 | 0.002471 | 0.000588 | 0.014899 |
| 269 | 0.009398 | 0.022444 | 0.000003 | 0.013035 | −0.000609 | −0.029593 | 0.011261 | −0.002465 | −0.006364 | 0.025836 | 0.016688 | 0.008361 | 0.013208 | −0.003509 |
| 270 | −0.020394 | 0.021084 | −0.024055 | 0.001103 | 0.024108 | 0.024307 | 0.016318 | 0.009687 | 0.018489 | 0.023066 | 0.020574 | 0.015881 | 0.016006 | −0.003988 |
| 271 | −0.005804 | −0.035934 | 0.010095 | −0.016853 | 0.01282 | −0.020086 | 0.011923 | −0.00015 | 0.019116 | 0.005206 | 0.042339 | 0.014144 | 0.010929 | 0.04248 |
| 272 | −0.028791 | −0.019861 | 0.012469 | 0.049648 | 0.027768 | 0.012903 | 0.028966 | 0.005764 | 0.026132 | 0.068001 | 0.032732 | 0.008083 | 0.007112 | 0.031141 |
| 273 | −−0.026964 | 0.045268 | 0.001555 | 0.0,11956 | 0.005919 | −0.005238 | 0.019503 | −0.002063 | −0.003917 | 0.051912 | 0.017801 | 0.013064 | 0.020925 | 0.012896 |
| 274 | −0.025461 | 0.045739 | 0.01149 | 0.023139 | 0.019259 | 0.0034 | 0.017739 | −0.005248 | −0.00284 | 0.053263 | 0.012651 | 0.01998 | 0.025397 | 0.007394 |
| 275 | −0.067092 | 0.0065 | 0.023615 | −0.011632 | −0.028939 | 0.061713 | 0.015044 | −0.022047 | −0.043993 | −0.022837 | 0.01835 | 0.014346 | 0.00805 | 0.032293 |
| 276 | 0.005815 | −0.001586 | −0.000829 | −0.003428 | 0.009308 | 0.021621 | −0.010558 | 0.010915 | 0.045809 | −0.026983 | 0.006226 | 0.007204 | −0.002316 | −0.002388 |
| 277 | 0.005473 | −0.028337 | −0.011097 | 0.008716 | −0.006169 | −0.014101 | −0.011085 | 0.000721 | 0.003917 | 0.020371 | 0.035322 | −0.020164 | 0.022661 | 0.080161 |
| 278 | −0.017577 | −0.013349 | 0.000271 | 0.025213 | −0.001753 | −0.009386 | −0.054667 | −0.020553 | 0.019638 | 0.039079 | 0.032156 | −0.01205 | 0.036919 | 0.081372 |
| 279 | −0.031149 | −0.01176 | −0.067935 | 0.004791 | −0.031776 | 0.004185 | 0.012609 | −0.021646 | 0.024298 | −0.002008 | 0.005048 | −0.010828 | −0.062376 | 0.043643 |
| 280 | −0.00631 | 0.014335 | 0.018523 | 0.036424 | 0.028703 | −0.000579 | 0.005487 | 0.029484 | −0.027074 | −0.064764 | 0.003763 | −0.032481 | 0.001152 | 0.01864 |
| 281 | 0.011817 | −0.01339 | −0.035098 | 0.002995 | −0.009762 | 0.023165 | −0.010176 | 0.006835 | −0.015998 | 0.016429 | 0.036212 | −0.011314 | 0.002636 | −0.032121 |
| 282 | −0.024833 | 0.020898 | −0.076199 | −0.00364 | 0.000404 | −0.007532 | 0.002573 | −0.000612 | 0.009625 | −0.001243 | 0.026801 | −0.014837 | 0.006814 | −0.022999 |
| 283 | 0.036507 | 0.033834 | −0.057824 | −0.022523 | −0.04634 | 0.024663 | −0.006826 | −0.039482 | 0.020471 | 0.001577 | 0.007306 | 0.008469 | −0.037426 | −0.027985 |
| 284 | −0.015144 | 0.004318 | 0.02643 | 0.012552 | −0.00556 | 0.000714 | −0.001219 | −0.018849 | 0.003616 | 0.019127 | 0.025491 | 0.011242 | 0.010496 | 0.007216 |
| 285 | −0.001721 | 0.0138 | 0.030328 | 0.008957 | 0.002652 | −0.002398 | −0.005337 | −0.029748 | −0.017172 | 0.009113 | 0.006984 | 0.012285 | 0.010048 | 0.00381 |
| 286 | −0.003071 | 0.030334 | 0.000082 | −0.008632 | −0.013017 | −0.034215 | −0.053489 | −0.019452 | −0.021945 | −0.017194 | −0.00161 | −0.017339 | −0.008023 | 0.009481 |
| 287 | −0.031448 | 0.051757 | −0.005171 | −0.018052 | −0.024646 | −0.010211 | −0.033874 | −0.013328 | 0.023896 | −0.020968 | −0.010259 | −0.001403 | 0.002231 | 0.02016 |
| 288 | 0.020835 | 0.0026031 | −0.017922 | −0.014363 | −0.049484 | 0.016056 | −0.010283 | −0.031581 | −0.001049 | 0.0057061 | −0.008711 | 0.0171311 | 0.0146931 | 0.007219 |
| 289 | 0.023834 | −0.012674 | 0.007481 | −0.023833 | 0.019602 | 0.020977 | 0.052892 | 0.003909 | −0.002141 | −0.015208 | −0.029432 | 0.027093 | 0.019916 | −0.011201 |
| 290 | 0.002633 | 0.010029 | −0.007919 | 0.003385 | −0.00524 | −0.013376 | 0.005996 | 0.006885 | 0.00372 | 0.02635 | 0.010728 | 0.022247 | 0.024344 | −0.000405 |
| 291 | 0.005653 | 0.008785 | −0.011737 | −0.001268 | −0.011336 | −0.01655 | 0.005644 | 0.009123 | 0.0032 | 0.020457 | 0.011942 | 0.017092 | 0.022413 | 0.004394 |
| 292 | 0.012667 | 0.004351 | −0.000595 | −0.000109 | −0.025588 | −0.004324 | 0.04572 | 0.000663 | −0.009025 | 0.022936 | 0.012817 | 0.018423 | 0.018943 | 0.015205 |
| 293 | −0.030469 | −0.000529 | −0.013329 | −0.040818 | −0.002586 | −0.059299 | −0.036373 | 0.025112 | −0.064801 | −0.012095 | 0.01784 | −0.025234 | 0.005549 | 0.051756 |
| 294 | 0.003973 | −0.012618 | −0.021435 | −0.003681 | −0.017583 | −0.008716 | 0.000985 | 0.002917 | −0.036981 | 0.003224 | 0.001349 | −0.02338 | −0.013908 | 0.012958 |
| 295 | 0.008195 | 0.020282 | 0.017108 | 0.03551 | 0.006467 | −0.019537 | −0.024159 | −0.002679 | 0.030726 | 0.033729 | −0.007892 | −0.001956 | 0.004558 | −0.000218 |
| 296 | −0.003992 | 0.019281 | 0.01195 | 0.015892 | 0.032828 | −0.028424 | −0.011901 | −0.002604 | 0.02585 | 0.045714 | −0.017998 | 0.007168 | 0.021527 | −0.03537 |
| 297 | 0.00635 | 0.007424 | −0.002289 | 0.029961 | −0.001806 | −0.011829 | −0.032852 | −0.003042 | 0.034954 | 0.030805 | −0.00674 | −0.003211 | 0.014315 | −0.010161 |
| 298 | −0.030133 | 0.03039 | 0.009876 | −0.03996 | −0.048835 | 0.029058 | 0.029577 | −0.036816 | −0.010623 | 0.044485 | −0.005154 | 0.005251 | −0.007383 | −0.029971 |
| 299 | 0.017752 | −0.052476 | 0.010011 | −0.004398 | 0.008128 | −0.020071 | 0.016938 | 0.016314 | 0.029371 | 0.029652 | −0.001316 | 0.006909 | 0.004615 | −0.01146 |
| 300 | 0.00389 | 0.088247 | 0.019052 | 0.062661 | −0.063289 | −0.000995 | 0.052645 | −0.04311 | −0.009698 | −0.010142 | −0.013447 | 0.024489 | 0.000119 | −0.027819 |
| 301 | −0.007615 | −0.045938 | 0.020012 | 0.008474 | −0.005696 | −0.000163 | 0.003108 | 0.000676 | 0.011878 | 0.022316 | 0.003603 | 0.006923 | 0.001705 | 0.000494 |
| 302 | −0.012712 | −0.047516 | 0.019307 | −0.009565 | 0.002944 | 0.028646 | 0.036415 | 0.008898 | −0.00744 | −0.012076 | −0.033106 | −0.008011 | −0.019786 | −0.017298 |
| 303 | 0.021984 | −0.05005 | 0.029365 | −0.031479 | −0.026632 | −0.019411 | −0.020362 | 0.003288 | 0.009627 | 0.027839 | −0.014827 | −0.002527 | 0.001321 | 0.004368 |
| 304 | −0.016272 | −0.048598 | −0.008354 | −0.016182 | −0.006251 | 0.013413 | −0.002947 | 0.016644 | 0.003556 | 0.031095 | −0.020324 | −0.003842 | −0.00751 | −0.012211 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 305 | −0.070862 | −0.068557 | 0.01363 | 0.036741 | 0.081315 | −0.001873 | 0.039649 | 0.038496 | 0.013271 | −0.021241 | −0.001284 | −0.008444 | −0.002741 | 0.02498 |
| 306 | −0.061593 | 0.011602 | −0.017789 | 0.015593 | 0.047984 | −0.017555 | 0.038462 | 0.018574 | −0.003794 | −0.007316 | −0.011453 | −0.007102 | −0.002405 | −0.019044 |
| 307 | 0.001396 | 0.03538 | 0.027803 | 0.035565 | 0.001396 | −0.046618 | −0.086158 | −0.008113 | 0.025876 | 0.012962 | 0.025946 | −0.001786 | 0.048861 | 0.03853 |
| 308 | −0.001287 | 0.016105 | −0.014372 | 0.013904 | 0.012844 | −0.003418 | −0.011563 | 0.002465 | −0.003036 | −0.007032 | −0.023961 | −0.009763 | −0.011007 | −0.016307 |
| 309 | 0.0179951 | −0.0014681 | −0.008646 | 0.023329 | 0.004351 | 0.000911 | −0.013415 | 0.000021 | 0.014505 | −0.009209 | −0.001061 | −0.011803 | −0.018525 | 0.017197 |
| 310 | −0.035051 | −0.036182 | −0.002592 | 0.02481 | −0.021489 | −0.048034 | −0.016053 | −0.00811 | −0.048455 | 0.012646 | −0.043472 | −0.012421 | −0.016799 | −0.026486 |
| 311 | 0.006682 | 0.023809 | 0.009212 | 0.012233 | 0.015682 | 0.016839 | −0.013896 | 0.001725 | 0.012345 | 0.003102 | 0.010046 | 0.007244 | 0.007862 | 0.032474 |
| 312 | −0.011052 | 0.050218 | 0.008185 | 0.006545 | 0.028599 | −0.031501 | −0.025008 | 0.013829 | 0.016251 | 0.028436 | 0.01943 | 0.029415 | 0.023745 | −0.024062 |
| 313 | 0.064136 | −0.005818 | 0.03721 | 0.012593 | −0.041818 | 0.007217 | 0.013734 | 0.010982 | 0.037591 | 0.029246 | 0.023795 | 0.008474 | 0.005708 | −0.029121 |
| 314 | −0.033636 | −0.049116 | −0.038508 | −0.069081 | −0.049785 | −0.037926 | −0.001286 | 0.017898 | −0.005105 | 0.026848 | −0.0179 | 0.015606 | 0.041835 | −0.028848 |
| 315 | 0.04836 | 0.013873 | 0.047595 | 0.009866 | 0.026432 | 0.018598 | 0.014257 | 0.013456 | 0.032369 | −0.004708 | −0.003752 | 0.01306 | 0.018562 | −0.004651 |
| 316 | 0.005006 | −0.011812 | 0.017131 | 0.019841 | 0.025594 | 0.005242 | −0.01129 | −0.011794 | 0.030189 | −0.036424 | 0.013463 | −0.01565 | −0.009396 | 0.005527 |
| 317 | 0.003256 | 0.019408 | 0.011339 | 0.009184 | 0.009908 | 0.005215 | −0.007609 | −0.005007 | 0.005874 | 0.006921 | 0.020189 | 0.004829 | 0.003888 | 0.026762 |
| 318 | 0.015019 | −0.011186 | −0.012816 | 0.015162 | −0.0013 | 0.022873 | −0.017713 | −0.006546 | 0.038431 | 0.000917 | −0.00388 | 0.025697 | 0.011238 | 0.006173 |
| 319 | 0.054542 | 0.010241 | 0.020492 | 0.009738 | 0.000772 | 0.013821 | −0.010935 | 0.000708 | 0.011514 | −0.027303 | 0.011833 | −0.002973 | 0.002088 | 0.018241 |
| 320 | −0.057232 | 0.0072521 | −0.006441 | −0.047458 | 0.040835 | 0.001276 | 0.047962 | 0.021045 | −0.019715 | −0.010982 | 0.002439 | −0.003864 | −0.014086 | −0.00033 |
| 321 | 0.033404 | −0.042896 | 0.005373 | −0.075645 | −0.014836 | 0.022321 | 0.018384 | −0.001725 | 0.023595 | 0.040756 | 0.006104 | −0.001677 | 0.04137 | −0.027706 |
| 322 | 0.018876 | 0.051337 | −0.021211 | −0.007356 | 0.051782 | −0.040027 | 0.031311 | 0.028376 | −0.020993 | −0.017014 | −0.061873 | 0.010787 | 0.011114 | 0.003397 |
| 323 | −0.010527 | −0.017614 | 0.069667 | −0.01938 | −0.005367 | −0.030547 | 0.005188 | 0.007523 | −0.006769 | −0.003271 | 0.01736 | 0.001791 | 0.008549 | 0.009933 |
| 324 | −0.056594 | −0.0501 | −0.033939 | 0.011672 | −0.041268 | 0.045887 | −0.0017 | −0.017284 | 0.001617 | 0.029852 | 0.038247 | −0.009646 | −0.028115 | −0.046046 |
| 325 | 0.003177 | 0.04217 | −0.013047 | 0.017254 | 0.006651 | 0.001558 | −0.024977 | −0.016324 | 0.004585 | 0.031539 | 0.015728 | −0.01923 | −0.003755 | −0.018709 |
| 326 | −0.011717 | −0.021158 | 0.030476 | −0.022657 | 0.008316 | −0.015706 | 0.008932 | 0.003248 | 0.012681 | 0.009719 | 0.023213 | 0.009532 | −0.017305 | 0.029068 |
| 327 | −0.029315 | −0.027711 | 0.016951 | 0.01491 | 0.026577 | −0.008392 | 0.00882 | 0.013879 | 0.028151 | 0.003321 | −0.01611 | 0.001489 | −0.014203 | −0.013381 |
| 328 | 0.068095 | 0.001174 | −0.021278 | 0.01331 | 0.072985 | −0.004194 | 0.046034 | −0.004124 | 0.007932 | −0.036573 | −0.003854 | −0.046005 | −0.03137 | −0.005781 |
| 329 | 0.048966 | −0.057783 | 0.000287 | 0.016424 | −0.03519 | −0.031229 | 0.02657 | −0.0104 | 0.034724 | 0.022006 | 0.026674 | 0.000764 | −0.015267 | 0.005891 |
| 330 | 0.064597 | −0.069259 | 0.029159 | −0.055762 | −0.022998 | −0.00551 | 0.005193 | −0.00286 | −0.080367 | 0.017698 | 0.03679 | −0.026231 | −0.000143 | 0.033125 |
| 331 | 0.004383 | 0.013031 | 0.000176 | 0.008216 | 0.008578 | −0.006855 | −0.010972 | 0.006591 | −0.003614 | −0.033508 | −0.008463 | −0.012054 | −0.022683 | 0.014654 |
| 332 | −0.03755 | 0.013069 | −0.035915 | −0.052515 | −0.009345 | 0.001862 | 0.044445 | 0.01133 | 0.004669 | 0.016272 | 0.014296 | 0.012487 | −0.003286 | −0.00124 |
| 333 | −0.000862 | −0.011517 | −0.015557 | 0.047195 | 0.026744 | 0.028339 | −0.027753 | 0.003781 | 0.005596 | −0.014583 | 0.014444 | −0.007339 | −0.009741 | 0.001919 |
| 334 | 0.014196 | −0.031117 | −0.0268 | −0.000006 | −0.041754 | 0.005228 | −0.003401 | −0.042684 | −0.014381 | 0.040019 | 0.013789 | −0.036548 | −0.000159 | −0.010301 |
| 335 | 0.007875 | −0.007747 | 0.007558 | 0.05451 | 0.018743 | 0.013569 | −0.00643 | −0.005754 | −0.018694 | −0.010373 | −0.006634 | −0.021251 | −0.026635 | −0.005208 |
| 336 | −0.001666 | 0.034058 | 0.003384 | −0.031244 | 0.057667 | 0.047511 | −0.027892 | 0.018098 | −0.016303 | −0.06581 | −0.017059 | −0.000915 | −0.023946 | −0.001037 |
| 337 | 0.029166 | −0.037697 | −0.01294 | 0.046793 | 0.078667 | 0.042362 | 0.075613 | −0.005238 | 0.004144 | 0.058056 | 0.01188 | 0.026058 | 0.014638 | −0.014988 |
| 338 | −0.032513 | 0.008246 | −0.026666 | −0.045311 | 0.025748 | −0.017346 | 0.028197 | −0.007522 | −0.017478 | 0.012939 | −0.017564 | −0.023452 | −0.008136 | 0.005324 |
| 339 | −0.056786 | 0.013541 | −0.036193 | −0.015631 | 0.066866 | −0.033776 | −0.050538 | 0.002212 | −0.018173 | −0.020392 | −0.020961 | −0.032335 | −0.037936 | 0.016935 |
| 340 | −0.04896 | 0.033317 | −0.007119 | −0.017921 | 0.034473 | 0.063478 | −0.045332 | −0.009132 | 0.039284 | 0.019417 | 0.002757 | 0.036124 | 0.034076 | 0.000217 |

| | HN | HO | HP | HQ | HR | HS | HT | HU | HV | HW | HX | HY | HZ | IA |
|---|---|---|---|---|---|---|---|---|---|---|---|---|---|---|
| 1 | −0.0533 | −0.003431 | 0.023282 | −0.018323 | −0.04473 | −0.017498 | −0.032824 | −0.144912 | −0.060338 | 0.0266311 | −0.023694 | −0.067728 | −0.122882 | −0.108472 |
| 2 | −0.048638 | −0.048711 | −0.029826 | −0.005042 | −0.024797 | −0.044175 | −0.03457 | −0.022272 | −0.094175 | −0.070436 | −0.084141 | −0.022909 | 0.050894 | −0.057947 |
| 3 | 0.04133 | 0.012953 | 0.017823 | −0.016078 | −0.007287 | −0.07138 | −0.12793 | −0.076333 | −0.112796 | −0.031171 | −0.061624 | −0.016858 | 0.023583 | −0.018136 |
| 4 | −0.034235 | 0.031114 | 0.058145 | 0.068925 | 0.074901 | −0.028828 | −0.019702 | 0.020784 | −0.00955 | −0.048563 | −0.018472 | 0.09197 | −0.025779 | −0.086542 |
| 5 | 0.059399 | −0.009904 | 0.019328 | 0.040815 | 0.043457 | −0.022638 | 0.009571 | 0.022187 | −0.013701 | 0.046703 | 0.031567 | 0.095161 | −0.045747 | 0.01302 |
| 6 | −0.124456 | −0.068375 | −0.08349 | 0.082107 | 0.123947 | −0.005885 | −0.019181 | −0.022913 | 0.070428 | −0.040623 | 0.015283 | 0.002225 | 0.006537 | 0.03537 |
| 7 | 0.010957 | 0.020815 | 0.015971 | −0.02538 | −0.054231 | 0.060977 | 0.013237 | 0.067337 | 0.069627 | 0.016404 | 0.004636 | 0.170996 | 0.091061 | −0.008463 |
| 8 | 0.010106 | −0.0516611 | −0.005578 | 0.014523 | 0.019584 | 0.00156 | 0.06197 | −0.013806 | 0.01975 | −0.021097 | 0.057339 | −0.04216 | 0.005216 | 0.023038 |
| 9 | −0.061485 | −0.051578 | 4.011303 | −0.034865 | −0.067387 | −0.017365 | −0.031802 | 0.018366 | −0.008521 | −0.0415 | 0.004447 | −0.054723 | 0.030457 | 0.050413 |
| 10 | −0.005195 | −0.091909 | −0.036112 | −0.017002 | 0.003029 | −0.001401 | −0.097377 | 0.076314 | 0.08388 | 0.038801 | 0.059896 | 0.040232 | 0.000847 | 0.041012 |
| 11 | −0.023961 | 0.004219 | −0.038909 | 0.007459 | 0.004419 | 0.010829 | −0.033648 | −0.003556 | −0.025719 | −0.042675 | −0.072319 | −0.024364 | −0.006477 | 0.006931 |
| 12 | 0.0141581 | 0.050541 | 0.0328741 | 0.057981 | 0.079696 | 0.014319 | 0.080767 | 0.029663 | −0.001359 | 0.030687 | 0.033246 | −0.046094 | 0.035595 | −0.001642 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 13 | 0.000982 | −0.052652 | −0.053401 | −0.055984 | −0.088413 | −0.08265 | −0.093194 | 0.074946 | 0.134291 | 0.004719 | −0.088798 | −0.01155 | 0.025252 | −0.011512 |
| 14 | 0.009526 | −0.007931 | −0.030713 | −0.032976 | 0.001488 | 0.004033 | 0.01595 | 0.073798 | −0.099938 | −0.029495 | 0.046477 | 0.058037 | 0.009619 | 0.076351 |
| 15 | −0.045915 | 0.001023 | 0.011932 | 0.015751 | 0.011893 | −0.02037 | −0.018172 | 0.087549 | 0.117345 | 0.052151 | −0.091113 | 0.099401 | 0.049877 | 0.023458 |
| 16 | 0.014957 | −0.038865 | −0.025865 | 0.038345 | 0.073736 | 0.005837 | 0.040522 | −0.112411 | 0.021752 | 0.010835 | −0.02846 | 0.044075 | −0.032623 | −0.105011 |
| 17 | −0.028609 | 0.0235251 | −0.004192 | 0.016839 | 0.003555 | 0.058338 | −0.022661 | 0.062081 | −0.024666 | −0.015998 | 0.030785 | −0.002837 | −0.073103 | −0.008599 |
| 18 | −0.0094911 | 0.0477511 | −0.010677 | −0.045655 | −0.038252 | 0.005183 | −0.062229 | 0.051734 | 0.025525 | 0.010131 | −0.053274 | −0.064354 | −0.02953 | −0.055641 |
| 19 | 0.028267 | 0.012269 | 0.05251 | 0.066637 | 0.086827 | 0.079632 | 0.213052 | 0.138909 | 0.101121 | 0.01627 | 0.081132 | 0.047427 | 0.092381 | 0.064831 |
| 20 | 0.019339 | −0.005785 | −0.03047 | 0.036086 | 0.023115 | −0.004103 | 0.008274 | 0.061713 | −0.032589 | −0.075276 | 0.07981 | 0.060252 | 4.004803 | 0.050445 |
| 21 | 0.014813 | 0.011639 | −0.002545 | −0.019948 | 0.000792 | 0.023676 | 0.053209 | −0.048865 | 0.042525 | 0.004933 | 0.042726 | −0.007948 | −0.046777 | 0.010001 |
| 22 | −0.0729181 | −0.003896 | −0.070017 | −0.069082 | −0.063894 | 0.035366 | 0.011136 | 0.01209 | 0.003558 | 0.0460251 | 0.000631 | −0.010794 | 0.0201321 | 0.018405 |
| 23 | −0.023784 | 0.027405 | 0.019635 | −0.055748 | −0.093581 | 0.012091 | −0.05953 | −0.025956 | −0.083093 | −0.01449 | 0.105852 | −0.142827 | −0.013083 | 0.016957 |
| 24 | 0.033639 | 0.033271 | 0.061606 | 0.037195 | 0.066 | −0.013136 | 0.007778 | −0.011954 | 0.074229 | 0.02461 | 0.082949 | −0.043189 | 0.0063 | −0.094742 |
| 25 | −0.022516 | −0.024537 | −0.102374 | 0.07233 | 0.039427 | 0.007961 | −0.009852 | −0.022404 | −0.025151 | −0.022631 | −0.012589 | −0.088011 | −0.060441 | −0.004701 |
| 26 | −0.087333 | −0.001893 | 0.00768 | 0.063178 | 0.013678 | −0.009614 | 0.045157 | 0.068096 | 0.059521 | 0.041591 | −0.016816 | 0.115655 | −0.02249 | −0.061109 |
| 27 | 0.004593 | 0.045603 | 0.008832 | 0.045882 | 0.059392 | 0.021634 | 0.081993 | 0.074822 | −0.125403 | −0.160394 | −0.019039 | −0.037675 | −0.031695 | 0.063209 |
| 28 | −0.027957 | −0.024183 | −0.048794 | 0.003768 | 0.029591 | −0.056903 | 0.016489 | −0.004296 | 0.098247 | −0.030975 | −0.050276 | −0.099644 | 0.064303 | 0.011616 |
| 29 | −0.023024 | 0.012598 | 0.013868 | −0.01218 | 0.011713 | 0.019719 | −0.013605 | 0.026985 | 0.028034 | 0.005068 | −0.003861 | 0.029869 | 0.007044 | −0.008636 |
| 30 | −0.012667 | −0.106696 | −0.031289 | 0.019248 | 0.031314 | 0.084068 | 0.034945 | −0.063097 | 0.014101 | −0.006566 | 0.048115 | 0.072101 | 0.030232 | 0.012843 |
| 31 | 0.027955 | −0.039823 | −0.008781 | −0.127829 | −0.098337 | 0.028748 | −0.075266 | −0.088333 | 0.080086 | −0.094635 | −0.062996 | −0.042227 | −0.060125 | 0.061136 |
| 32 | 0.034816 | 0.099079 | 0.118976 | −0.037673 | −0.034706 | −0.016108 | −0.023981 | 0.040519 | −0.021947 | 0.022783 | 0.000471 | 0.099872 | 0.004845 | 0.064171 |
| 33 | −0.021456 | 0.029023 | 0.03783 | 0.00458 | −0.026091 | 0.017058 | 0.069875 | −0.055013 | −0.02951 | 0.061808 | 0.054895 | 0.014649 | −0.065339 | 0.002057 |
| 34 | 0.0200541 | 0.021373 | 0.045965 | −0.071653 | −0.033429 | −0.031974 | −0.089612 | −0.00962 | −0.019186 | −0.059574 | 0.043899 | 0.010767 | −0.008422 | 0.093456 |
| 35 | −0.031242 | −0.073427 | −0.053986 | 0.010788 | 0.004765 | −0.009961 | 0.007596 | −0.08113 | −0.014229 | −0.015156 | 0.025349 | −0.046286 | −0.07332 | −0.014767 |
| 36 | −0.072127 | −0.05749 | −0.034236 | 0.046947 | 0.038494 | 0.006395 | −0.003558 | 0.031833 | 0.013427 | −0.004828 | −0.0546 | 0.045435 | 0.041209 | −0.119918 |
| 37 | −0.02044 | −0.00154 | −0.0143611 | −0.041249 | −0.027433 | −0.037859 | 0.070307 | −0.042921 | 0.050862 | −0.020459 | 0.033079 | −0.005731 | 0.085094 | 0.008071 |
| 38 | −0.034366 | 0.053139 | 0.06678 | −0.016258 | −0.004912 | −0.0714 | −0.024396 | −0.040548 | −0.034249 | 0.015341 | −0.033605 | 0.014714 | −0.046862 | −0.036736 |
| 39 | 0.027243 | −0.022646 | −0.029863 | −0.040658 | −0.079253 | −0.024514 | −0.020743 | 0.018321 | 0.028074 | −0.045026 | −0.057363 | −0.005886 | −0.011347 | −0.078743 |
| 40 | −0.076766 | −0.060751 | −0.029882 | −0.019419 | −0.037525 | 0.040784 | 0.068732 | −0.025435 | 0.099796 | 0.066364 | 0.093186 | −0.044417 | −0.014449 | 0.084859 |
| 41 | 0.027065 | 0.011914 | 0.016763 | −0.009415 | −0.036668 | 0.035203 | 0.007152 | 0.012775 | −0.098708 | 0.021025 | 0.006689 | 0.022475 | 0.002475 | −0.112467 |
| 42 | −0.01933 | −0.009612 | 0.004974 | −0.001382 | −0.006567 | −0.004192 | 0.006908 | 0.017298 | 0.031209 | 0.008691 | 0.022678 | −0.001227 | 0.009226 | 0.015178 |
| 43 | 0.048919 | 0.057186 | −0.082267 | 0.043414 | 0.018656 | 0.004138 | −0.028059 | 0.022358 | 0.063755 | −0.011159 | −0.067968 | 0.02956 | 0.006178 | −0.058909 |
| 44 | −0.064263 | 0.00807 | 0.089176 | −0.095722 | −0.07569 | 0.034222 | −0.019355 | −0.082526 | −0.030022 | −0.021769 | 0.049829 | −0.020122 | 0.00264 | 0.00035 |
| 45 | −0.028555 | −0.072975 | −0.0184 | −0.001716 | −0.024644 | −0.075567 | −0.028972 | −0.003384 | −0.034367 | −0.016626 | 0.022909 | 0.135234 | 0.068563 | 0.055969 |
| 46 | 0.052769 | −0.016846 | −0.101461 | 0.056232 | 0.063692 | −0.020827 | 0.146468 | −0.036607 | −0.106695 | 0.060268 | 0.034272 | −0.036747 | −0.058055 | −0.019781 |
| 47 | 0.049366 | 0.066067 | 0.043474 | −0.02844 | −0.042099 | 0.0164 | 0.002533 | 0.085338 | −0.052313 | −0.15514 | −0.04249 | −0.028555 | −0.045111 | −0.000856 |
| 48 | −0.03097 | −0.011809 | −0.001722 | −0.035503 | −0.00676 | 0.012575 | −0.016159 | 0.082057 | −0.001775 | −0.041602 | 0.025178 | 0.04634 | −0.018204 | −0.010415 |
| 49 | 0.0480241 | 0.044285 | 0.0083311 | −0.005771 | 0.001124 | 0.006649 | 0.036169 | 0.068762 | 0.038391 | −0.002099 | 0.000445 | 0.100609 | 0.039395 | 0.005326 |
| 50 | 0.035634 | −0.000097 | 0.027743 | 0.00237 | −0.017751 | −0.01752 | 0.002943 | 0.027447 | −0.008541 | 0.13469 | 0.030333 | −0.143624 | 0.023795 | 0.104626 |
| 51 | 0.021281 | 0.023716 | 0.029312 | −0.03 | −0.049501 | 0.079839 | −0.009301 | −0.055549 | −0.083993 | −0.159662 | −0.014192 | 0.0372 | 0.086543 | −0.060287 |
| 52 | 0.033235 | 0.033051 | 0.016754 | −0.03974 | 0.005946 | −0.04465 | −0.134303 | 0.065833 | 0.099484 | −0.061774 | −0.103748 | −0.013456 | −0.016737 | −0.056846 |
| 53 | 0.063342 | −0.008595 | −0.017186 | 0.03079 | 0.034645 | −0.038334 | 0.02174 | −0.013806 | 0.023915 | 0.038506 | 0.063623 | 0.089248 | 0.007075 | 0.049005 |
| 54 | 0.031939 | 0.050902 | 0.024015 | −0.028353 | −0.000875 | −0.013707 | −0.116524 | −0.032531 | 0.123428 | −0.029096 | −0.087024 | 0.043013 | 0.044321 | 0.05228 |
| 55 | 0.002404 | −0.019838 | −0.011127 | −0.194845 | −0.164574 | 0.011408 | −0.072784 | −0.009465 | −0.12409 | 0.001096 | 0.012461 | −0.017742 | 0.01818 | 0.015313 |
| 56 | 0.021799 | 0.086301 | 0.022046 | −0.032238 | −0.038465 | −0.004684 | −0.051278 | −0.106041 | 0.061906 | 0.018302 | 0.0284 | −0.003802 | 0.094311 | −0.080327 |
| 57 | −0.073024 | −0.0043 | 0.005793 | 0.038447 | 0.030473 | 0.040504 | 0.044883 | 0.013381 | −0.023965 | 0.046976 | −0.049527 | 0.003749 | 0.044734 | 0.028124 |
| 58 | −0.03567 | −0.019003 | −0.005781 | 0.099943 | 0.005964 | −0.008753 | 0.015514 | 0.034563 | −0.052453 | −0.010148 | 0.074329 | −0.030171 | −0.049708 | 0.072833 |
| 59 | −0.0285091 | −0.024256 | −0.0697421 | 0.037293 | 0.01332 | −0.006909 | 0.052221 | 0.060214 | −0.02025 | 0.048447 | −0.100627 | 0.020258 | 0.04624 | 0.025215 |
| 60 | 0.039133 | 0.026327 | 0.005235 | −0.094266 | −0.105123 | 0.011584 | −0.040543 | 0.02627 | 0.130057 | 0.062143 | −0.071387 | 0.063648 | 0.060749 | 0.02172 |
| 61 | 0.041458 | 0.022185 | 0.024876 | 0.064293 | 0.069508 | −0.005928 | −0.016265 | 0.011826 | 0.024542 | 0.030485 | 0.083751 | −0.110795 | −0.076913 | 0.034001 |
| 62 | −0.009973 | 0.009733 | −0.003667 | −0.031994 | −0.046022 | −0.018639 | −0.039196 | −0.06014 | 0.059612 | 0.044229 | 0.105415 | −0.024324 | −0.078244 | −0.136288 |
| 63 | 0.022579 | −0.03386 | 0.028284 | −0.070685 | −0.054431 | 0.028265 | −0.028654 | −0.043594 | −0.055651 | −0.013819 | −0.050865 | −0.077762 | 0.02891 | 0.070521 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 64 | 0.020795 | 0.024432 | 0.051781 | 0.029792 | −0.012729 | −0.045966 | −0.001291 | −0.016982 | −0.120468 | 0.029845 | −0.002497 | 0.039161 | −0.011065 | −0.035117 |
| 65 | −0.067966 | 0.038205 | −0.015588 | 0.08599 | 0.062619 | −0.007319 | 0.009907 | −0.002738 | −0.000607 | 0.097442 | −0.081644 | 0.053912 | 0.096831 | 0.067773 |
| 66 | 0.009951 | 0.099643 | 0.038489 | −0.022247 | 0.037993 | 0.066769 | −0.025531 | 0.027497 | −0.055503 | 0.035316 | 0.044322 | −0.034908 | −0.113057 | −0.012316 |
| 67 | 0.056856 | 0.007894 | 0.031582 | 0.011669 | 0.036892 | 0.017282 | −0.011667 | 0.034578 | 0.007572 | −0.023627 | −0.016868 | −0.038806 | 0.001354 | −0.002405 |
| 68 | −0.011959 | −0.026474 | −0.025891 | −0.065934 | −0.063292 | 0.018531 | −0.035044 | −0.018403 | 0.022759 | −0.024868 | 0.102712 | −0.002748 | 0.04132 | 0.056488 |
| 69 | 0.004605 | 0.015228 | 0.079901 | −0.069949 | −0.064241 | 0.010396 | −0.014517 | 0.01955 | 0.069213 | 0.010718 | 0.007565 | −0.006339 | −0.136884 | −0.08427 |
| 70 | −0.050796 | −0.065727 | −0.066602 | −0.010304 | −0.008416 | −0.052884 | 0.033826 | −0.045835 | −0.066446 | −0.090335 | 0.047487 | −0.002252 | 0.061767 | 0.045381 |
| 71 | −0.089356 | −0.027294 | −0.022629 | −0.017017 | −0.067987 | 0.097528 | 0.006008 | 0.161089 | −0.129657 | 0.012366 | −0.02966 | 0.120652 | 0.014297 | 0.050077 |
| 72 | 0.030785 | 0.025386 | 0.03653 | −0.027678 | −0.030654 | −0.02793 | 0.062999 | −0.128385 | −0.037723 | −0.016134 | 0.059399 | 0.076029 | 0.016106 | −0.070036 |
| 73 | 0.0189711 | −0.031023 | −0.0780371 | 0.056053 | 0.070483 | 0.015566 | 0.003704 | 0.073413 | 0.002043 | 0.025244 | 0.061154 | −0.052333 | 0.075698 | 0.065583 |
| 74 | −0.035319 | 0.0321551 | 0.0027441 | −0.078211 | −0.038337 | −0.005388 | −0.033284 | 0.102131 | −0.031849 | 0.033115 | 0.032274 | 0.035871 | −0.03299 | −0.000483 |
| 75 | −0.031116 | −0.018114 | 0.000295 | −0.018826 | −0.029073 | 0.040712 | 0.042464 | −0.089724 | −0.088642 | −0.04355 | 0.028808 | 0.039252 | −0.029375 | 0.009624 |
| 76 | 0.026713 | 0.011892 | 0.06675 | 0.014516 | 0.01859 | 0.046009 | −0.046655 | 0.023722 | 0.023249 | 0.052315 | 0.095255 | −0.107708 | −0.04618 | 0.10627 |
| 77 | 0.065911 | 0.072 | −0.022882 | −0.014178 | −0.003883 | −0.00749 | −0.079512 | 0.007246 | 0.070434 | 0.005609 | 0.063228 | −0.034923 | 0.095793 | −0.001212 |
| 78 | 0.02716 | 0.001866 | −0.005695 | 0.0915 | 0.101732 | −0.006436 | 0.018893 | −0.006161 | 0.054358 | 0.026386 | −0.031971 | 0.112958 | −0.022423 | −0.044012 |
| 79 | 0.002226 | −0.021798 | 0.049097 | 0.069685 | 0.087229 | −0.00699 | 0.043815 | −0.071806 | −0.05016 | 0.027795 | −0.035905 | −0.145859 | 0.033131 | −0.064441 |
| 80 | 0.01241 | −0.053069 | 0.005051 | 0.081349 | 0.078222 | 0.003479 | 0.083792 | 0.088603 | 0.043105 | 0.036911 | −0.07448 | −0.046542 | 0.001956 | 0.013571 |
| 81 | 0.016401 | 0.019939 | −0.03141 | 0.026202 | 0.013162 | −0.019601 | 0.086197 | −0.020661 | −0.004504 | −0.017735 | −0.08696 | 0.083643 | 0.012003 | −0.038924 |
| 82 | −0.016948 | 0.026162 | 0.016576 | 0.0264961 | 0.016716 | −0.019254 | 0.088767 | −0.021622 | 0.055604 | 0.069276 | 0.025753 | −0.057143 | −0.076269 | −0.00043 |
| 83 | −0.036646 | −0.023693 | 0.01641 | −0.082009 | −0.064757 | −0.031348 | −0.014635 | −0.058751 | 0.029145 | 0.071343 | 0.011098 | −0.004242 | 0.052639 | 0.005884 |
| 84 | 0.027664 | −0.002314 | 0.056253 | 0.065629 | 0.028412 | 0.013804 | −0.056254 | 0.020957 | −0.087523 | −0.076351 | 0.002656 | −0.013836 | −0.018837 | 0.030235 |
| 85 | −0.06813 | 0.026071 | −0.015309 | 0.027193 | 0.055814 | 0.015172 | −0.03573 | −0.011389 | 0.043925 | 0.006604 | −0.055079 | −0.038656 | −0.045747 | 0.003666 |
| 86 | −0.031504 | −0.053594 | −0.003067 | 0.086566 | 0.096648 | −0.035801 | 0.030822 | 0.015563 | 0.032005 | −0.009555 | −0.019117 | 0.035305 | −0.035025 | −0.000022 |
| 87 | 0.091897 | −0.012179 | −0.016819 | 0.063367 | 0.002989 | −0.037387 | 0.013752 | 0.005651 | 0.024998 | 0.00022r | 0.004912 | −0.090894 | −0.04304 | −0.05734 |
| 88 | 0.033241 | −0.014445 | −0.029738 | −0.04337 | 0.059231 | 0.074732 | 0.031388 | −0.112854 | −0.052805 | 0.064764 | 0.09555 | −0.060158 | −0.00841 | −0.032781 |
| 89 | 0.063174 | 0.104495 | 0.091074 | 0.044421 | 0.02024 | −0.015963 | −0.065634 | −0.015941 | −0.015013 | 0.041737 | −0.044258 | 0.130504 | 0.009243 | −0.05393 |
| 90 | 0.0761181 | −0.082725 | −0.102766 | −0.011307 | 0.001775 | −0.002777 | −0.083533 | 0.020127 | 0.020282 | 0.02141 | −0.063626 | −0.031455 | −0.058636 | −0.050508 |
| 91 | −0.020643 | −0.012864 | −0.022707 | 0.061514 | 0.013918 | −0.003071 | −0.01155 | −0.014367 | −0.014491 | 0.017974 | −0.021368 | −0.154271 | 0.043068 | 0.051156 |
| 92 | 0.060709 | 0.035994 | 0.023876 | −0.070975 | −0.063232 | 0.027901 | −0.032483 | −0.012034 | 0.003594 | −0.009017 | −0.011523 | 0.014386 | −0.059858 | −0.052151 |
| 93 | 0.021092 | −0.000267 | −0.043439 | −0.083147 | −0.069994 | 0.001718 | −0.012739 | 0.068456 | −0.006802 | 0.061166 | 0.054215 | −0.04619 | 0.124573 | 0.005963 |
| 94 | −0.02679 | −0.010212 | 0.02518 | 0.038323 | 0.040533 | −0.029224 | 0.030546 | −0.110839 | 0.055929 | −0.014507 | −0.062309 | 0.008856 | 0.072539 | −0.022444 |
| 95 | 0.005102 | 0.036128 | 0.018438 | −0.064252 | −0.053854 | −0.027824 | −0.093128 | −0.006645 | −0.019276 | 0.045303 | −0.005878 | −0.040954 | 0.021888 | 0.023184 |
| 96 | 0.066399 | 0.080504 | 0.078582 | −0.051169 | −0.026001 | −0.039729 | −0.004121 | −0.010787 | 0.010946 | −0.007894 | −0.059529 | −0.035019 | −0.031111 | −0.053929 |
| 97 | −0.024808 | −0.093655 | −0.033628 | −0.041335 | −0.044101 | −0.024203 | 0.076514 | −0.00419 | −0.07109 | −0.032181 | 0.05441 | 0.011315 | 0.048634 | 0.022427 |
| 98 | 0.014895 | −0.036292 | −0.013046 | −0.020604 | −0.03237 | 0.028067 | 0.03833 | −0.017901 | −0.08496 | −0.042942 | 0.030156 | −0.136964 | 0.025794 | −0.03362 |
| 99 | −0.028814 | 0.041264 | 0.012251 | 0.006709 | 0.070491 | −0.018533 | −0.035039 | −0.016813 | 0.037704 | −0.026333 | −0.034183 | 0.039944 | 0.0369121 | 0.0073 |
| 100 | 0.005512 | −0.018586 | −0.001534 | 0.016168 | 0.017988 | −0.002615 | 0.018741 | 0.03242 | 0.019067 | 0.024298 | 0.00838 | 0.040629 | 0.0138 | 0.031258 |
| 101 | 0.005501 | 0.009509 | −0.00033 | −0.013385 | −0.014666 | −0.002016 | −0.0073 | 0.004625 | −0.006316 | −0.011154 | −0.011189 | −0.000552 | 0.021916 | 0.00896 |
| 102 | −0.002352 | −0.004464 | −0.014359 | 0.025484 | 0.025905 | 0.002838 | 0.007711 | 0.007279 | −0.019815 | −0.007676 | 0.023383 | 0.009937 | −0.012714 | 0.034688 |
| 103 | 0.002427 | 0.010316 | −0.028294 | 0.010254 | −0.009122 | 0.021599 | −0.018742 | 0.018583 | −0.053814 | −0.019116 | −0.002662 | 0.021082 | −0.030902 | −0.01449 |
| 104 | 0.022196 | −0.003949 | 0.021924 | −0.055654 | −0.04671 | 0.028315 | −0.03972 | 0.020518 | 0.006905 | 0.020803 | 0.027475 | 0.020531 | 0.013501 | 0.010072 |
| 105 | −0.019828 | −0.004521 | −0.036193 | −0.05336 | −0.025492 | −0.024872 | −0.024528 | 0.018294 | 0.038824 | 0.004993 | −0.025328 | 0.006743 | 0.00686 | 0.013007 |
| 106 | −0.023148 | −0.036341 | −0.050507 | −0.024283 | −0.021528 | 0.034861 | 0.036176 | 0.014762 | 0.026839 | −0.01035 | 0.019148 | −0.005804 | 0.013123 | 0.021647 |
| 107 | 0.024743 | 0.018377 | −0.011191 | 0.005866 | 0.027262 | 0.019961 | −0.023705 | 0.024372 | 0.030588 | −0.010173 | 0.016754 | 0.01069 | 0.015923 | 0.017839 |
| 108 | 0.02121 | 0.015028 | 0.005073 | −0.002889 | 0.03092 | −0.019795 | −0.040716 | −0.000575 | 0.025076 | −0.011974 | −0.037996 | −0.006404 | 0.016099 | −0.025671 |
| 109 | −0.007932 | −0.014905 | −0.044876 | 0.037162 | 0.033721 | −0.010798 | 0.015369 | 0.034539 | −0.030382 | 0.004557 | −0.016332 | 0.019467 | 0.010298 | 0.004145 |
| 110 | 0.02479 | 0.008526 | −0.003016 | 0.024127 | 0.02657 | −0.014503 | −0.010676 | 0.023295 | 0.01642 | 0.013398 | −0.000254 | 0.009284 | −0.081789 | 0.038477 |
| 111 | −0.034427 | −0.026529 | −0.009394 | −0.060108 | −0.082152 | 0.000827 | 0.014328 | 0.052611 | 0.029078 | 0.020659 | 0.019641 | −0.013182 | 0.018204 | 0.067257 |
| 112 | −0.008957 | −0.016047 | −0.018347 | 0.006494 | 0.037331 | −0.033706 | 0.001622 | −0.01348 | 0.041682 | 0.018596 | −0.011355 | −0.040487 | 0.009762 | −0.019706 |
| 113 | −0.012122 | 0.02073 | 0.022865 | 0.001563 | −0.025141 | 0.014225 | −0.003192 | 0.012938 | 0.007423 | 0.004057 | −0.024739 | 0.02536 | −0.0673 | 0.00672 |
| 114 | 0.0108741 | 0.00951 | 0.061268 | −0.010607 | −0.009443 | 0.023423 | 0.042418 | −0.046572 | −0.006728 | 0.0058041 | 0.0116941 | −0.035631 | 0.012995 | −0.029202 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 115 | −0.003283 | 0.026167 | −0.032867 | −0.02976 | −0.022688 | 0.013083 | 0.045471 | 0.016461 | 0.055176 | −0.000183 | −0.041146 | −0.015629 | 0.010872 | 0.033453 |
| 116 | −0.002056 | −0.002413 | 0.009903 | 0.026034 | −0.001985 | −0.010598 | 0.02764 | 0.020637 | 0.037211 | −0.005378 | −0.047636 | −0.053333 | 0.013302 | 0.006052 |
| 117 | 0.022229 | 0.016512 | 0.004495 | −0.038022 | −0.038609 | 0.020965 | −0.030358 | 0.050398 | −0.025701 | 0.03225 | 0.001427 | 0.00877 | 0.032011 | 0.054597 |
| 118 | 0.027167 | 0.02255 | 0.008676 | −0.020643 | −0.018732 | 0.045085 | −0.00972 | −0.016096 | −0.012629 | 0.010778 | 0.015704 | 0.010279 | 0.043161 | 0.003389 |
| 119 | 0.015617 | 0.013054 | 0.023975 | 0.002616 | 0.005237 | −0.001316 | 0.0073 | −0.021918 | −0.021971 | 0.014814 | −0.003848 | 0.037715 | 0.011251 | 0.005006 |
| 120 | 0.02053 | 0.015765 | 0.008384 | −0.037929 | −0.027032 | 0.007855 | −0.034815 | −0.008192 | 0.00797 | −0.005396 | −0.000764 | 0.002949 | −0.003108 | −0.000546 |
| 121 | −0.012004 | 0.001018 | 0.005409 | 0.04674 | −0.038416 | 0.013784 | −0.009891 | −0.027336 | −0.011284 | 0.026321 | 0.06161 | −0.035236 | −0.005883 | 0.009942 |
| 122 | 0.008642 | 0.0153 | −0.007646 | 0.008266 | 0.002006 | −0.016306 | −0.023242 | −0.000234 | 0.013958 | 0.014914 | 0.012104 | −0.030457 | −0.047692 | 0.028911 |
| 123 | 0.007152 | 0.037858 | −0.003362 | 0.012962 | 0.02084 | −0.016172 | −0.02012 | 0.001632 | 0.023299 | 0.048525 | 0.038981 | −0.000593 | 0.0044 | −0.001406 |
| 124 | 0.016151 | 0.0258181 | 0.0147811 | −0.002739 | 0.017087 | −0.009584 | −0.009411 | −0.010488 | 0.0032081 | −0.007375 | 0.0014521 | 0.0466191 | 0.0085761 | 0.014043 |
| 125 | 0.007299 | 0.004301 | 0.010075 | −0.020435 | −0.020465 | 0.006715 | −0.021365 | −0.01073 | −0.027917 | −0.025532 | 0.008391 | −0.089793 | 0.00029 | −0.014359 |
| 126 | −0.012041 | 0.002356 | 0.004314 | −0.008123 | −0.004186 | 0.007873 | 0.003303 | −0.025889 | 0.012252 | 0.002094 | 0.026389 | −0.010673 | −0.046772 | −0.006872 |
| 127 | 0.010286 | −0.031146 | −0.040148 | −0.010696 | −0.018991 | 0.011249 | −0.002947 | −0.008258 | 0.0111 | 0.005964 | 0.024158 | −0.030079 | 0.003465 | 0.018023 |
| 128 | −0.010309 | 0.02105 | 0.041123 | 0.023641 | 0.006502 | −0.020489 | −0.003154 | −0.00932 | 0.031506 | −0.012409 | −0.064953 | 0.001192 | 0.012785 | −0.006203 |
| 129 | 0.038075 | 0.014934 | −0.01569 | 0.017302 | −0.028124 | −0.034453 | −0.019852 | −0.063328 | 0.01543 | 0.015134 | 0.063561 | 0.013199 | 0.008627 | 0.049768 |
| 130 | −0.022391 | −0.006019 | −0.012869 | −0.011022 | −0.028584 | −0.012564 | 0.031714 | 0.001012 | 0.0250611 | −0.000612 | −0.008671 | −0.017321 | 0.0377451 | −0.018911 |
| 131 | −0.003435 | 0.0602431 | 0.0484891 | 0.008769 | 0.011218 | −0.003423 | −0.001978 | 0.039048 | −0.021034 | 0.014427 | 0.000678 | 0.02164 | −0.043562 | −0.006461 |
| 132 | 0.0187021 | 0.038111 | −0.007579 | −0.001121 | 0.024011 | −0.021721 | −0.037664 | −0.075496 | 0.019549 | 0.020558 | −0.040164 | 0.011395 | 0.049885 | −0.062135 |
| 133 | 0.014485 | −0.018091 | −0.020042 | 0.001389 | −0.025646 | −0.004489 | 0.005959 | 0.007222 | 0.036274 | 0.009159 | −0.009983 | 0.019518 | 0.0343861 | −0.064935 |
| 134 | 0.032352 | 0.002207 | 0.027705 | −0.025373 | −0.036406 | 0.015991 | −0.022504 | −0.011005 | −0.063873 | −0.062323 | −0.045792 | −0.00038 | −0.035205 | 0.012564 |
| 135 | −0.011689 | −0.00976 | 0.020675 | −0.000591 | 0.015934 | 0.004766 | −0.007556 | −0.002992 | 0.004935 | −0.012678 | −0.012511 | 0.007307 | −0.013827 | −0.034164 |
| 136 | 0.009082 | 0.008209 | −0.003354 | 0.008554 | 0.01095 | 0.025849 | 0.034948 | 0.030449 | −0.021963 | 0.011656 | −0.022449 | 0.051565 | 0.003066 | −0.006418 |
| 137 | −0.016224 | 0.024864 | 0.017923 | 0.004604 | −0.028202 | −0.002594 | 0.002031 | −0.042613 | −0.002905 | −0.048027 | −0.000491 | 0.011541 | −0.025242 | −0.016413 |
| 138 | −0.01277 | −0.049449 | 0.019039 | −0.005401 | −0.007761 | 0.029942 | 0.04273 | 0.031932 | −0.01042 | −0.01059 | 0.047929 | 0.019583 | −0.010877 | 0.021725 |
| 139 | 0.0032151 | −0.008996 | −0.006713 | 0.009026 | 0.026655 | 0.012943 | −0.014124 | −0.045709 | −0.041998 | −0.014398 | −0.009831 | 0.094112 | −0.067751 | −0.061704 |
| 140 | −0.016691 | 0.001909 | 0.012327 | 0.007157 | −0.020596 | 0.00782 | −0.033865 | 0.034083 | 0.026611 | 0.037857 | −0.000019 | 0.071676 | 0.016404 | 0.001089 |
| 141 | −0.011437 | −0.053543 | −0.020067 | −0.012761 | 0.0097 | −0.015995 | 0.007871 | −0.048091 | 0.038878 | 0.007331 | −0.008789 | −0.031781 | −0.010075 | 0.005634 |
| 142 | 0.02141 | 0.031493 | 0.032392 | −0.051673 | −0.040374 | −0.005464 | −0.013383 | 0.002849 | −0.001786 | −0.000468 | 0.007116 | 0.030555 | 0.060812 | −0.040583 |
| 143 | 0.018645 | −0.009509 | −0.010619 | 0.009228 | 0.00952 | −0.031953 | −0.027803 | −0.01201 | 0.022645 | 0.009842 | 0.055111 | 0.020134 | 0.020984 | 0.013952 |
| 144 | 0.020736 | 0.000647 | 0.024693 | −0.009392 | −0.005255 | −0.005089 | −0.00433 | 0.000216 | 0.000012 | −0.01004 | 0.026352 | 0.059173 | −0.000873 | 0.048304 |
| 145 | 0.012543 | 0.006769 | 0.022838 | −0.000004 | −0.020362 | −0.012064 | −0.010694 | −0.008118 | −0.027635 | 0.011769 | 0.0103 | 0.022653 | −0.023557 | −0.039051 |
| 146 | −0.000729 | 0.0114141 | 0.025032 | −0.003413 | −0.001544 | −0.000027 | −0.009842 | 0.007529 | 0.022623 | −0.00814 | −0.027802 | −0.022401 | −0.036597 | −0.031319 |
| 147 | −0.018369 | −0.01315 | −0.00615 | 0.016498 | 0.016817 | −0.012187 | 0.009011 | 0.023368 | 0.029965 | −0.001343 | −0.029636 | −0.020572 | 0.00488 | 0.003949 |
| 148 | −0.030179 | −0.027758 | −0.000405 | −0.016218 | −0.005715 | 0.026002 | 0.008074 | 0.008886 | 0.037421 | 0.023393 | 0.03114 | −0.011315 | −0.011777 | 0.066679 |
| 149 | −0.040213 | −0.001864 | −0.020023 | −0.016496 | −0.021589 | 0.019594 | 0.019118 | −0.020991 | −0.017514 | 0.006915 | −0.062234 | 0.013315 | 0.003725 | 0.00112 |
| 150 | −0.012428 | −0.010017 | 0.002504 | −0.003564 | −0.004421 | 0.005627 | −0.009545 | −0.023804 | −0.027406 | −0.015603 | 0.04372 | 0.032958 | 0.005973 | −0.027607 |
| 151 | 0.016356 | −0.001616 | 0.007216 | −0.03276 | −0.028691 | 0.025121 | −0.001409 | 0.037485 | −0.033496 | 0.00874 | −0.002198 | 0.031309 | 0.014182 | 0.046792 |
| 152 | −0.023251 | −0.030916 | −0.035302 | −0.01956 | −0.01673 | 0.015603 | 0.017389 | −0.025435 | −0.003286 | 0.026307 | 0.027123 | −0.036944 | 0.007832 | 0.036141 |
| 153 | −0.018961 | 0.00067 | −0.035598 | 0.008182 | 0.005649 | −0.011892 | 0.002085 | 0.014212 | 0.066319 | −0.017286 | 0.002268 | −0.004434 | 0.001281 | 0.030502 |
| 154 | −0.036402 | 0.010166 | 0.016313 | −0.011151 | −0.006378 | −0.001967 | 0.009256 | 0.023379 | −0.005309 | 0.010369 | 0.007482 | 0.01934 | 0.023061 | 0.0229511 |
| 155 | −0.007191 | −0.010926 | −0.015231 | −0.009996 | −0.004254 | 0.011169 | 0.027244 | −0.006411 | 0.007362 | 0.021566 | 0.034336 | −0.002012 | 0.030844 | 0.006843 |
| 156 | −0.0092091 | 0.017937 | 0.036459 | 0.015474 | 0.020553 | −0.000111 | 0.013455 | 0.109771 | 0.018094 | 0.029598 | −0.088523 | −0.006985 | 0.01705 | −0.025935 |
| 157 | −0.0101281 | −0.024277 | 0.0119881 | 0.030796 | 0.002373 | 0.037551 | 0.035704 | 0.010912 | −0.007286 | −0.009455 | 0.06673 | −0.038581 | −0.025273 | 0.034358 |
| 158 | 0.022526 | −0.009612 | −0.01802 | −0.014339 | 0.010588 | −0.008449 | −0.003177 | −0.022652 | 0.025023 | 0.013894 | −0.012859 | −0.051258 | −0.040019 | −0.043439 |
| 159 | −0.002007 | −0.000083 | 0.039527 | 0.010902 | 0.020127 | 0.027032 | −0.029314 | −0.03013 | −0.064002 | −0.008851 | −0.007782 | −0.033122 | 0.00962 | −0.017257 |
| 160 | −0.00742 | −0.029971 | −0.028853 | −0.020152 | −0.016029 | 0.0024 | 0.028033 | −0.050346 | 0.060401 | −0.012987 | 0.0137691 | −0.045034 | −0.000421 | −0.027428 |
| 161 | 0.051234 | −0.002658 | −0.003275 | 0.030242 | 0.039286 | −0.015342 | 0.007639 | 0.034091 | 0.015761 | 0.013039 | 0.008243 | 0.023107 | 0.018091 | −0.037378 |
| 162 | −0.040357 | −0.011627 | 0.032775 | 0.030905 | 0.027793 | 0.016539 | −0.008064 | −0.009182 | −0.086998 | −0.018916 | 0.044881 | 0.02139 | 0.028351 | 0.022501 |
| 163 | −0.016301 | −0.039775 | −0.018367 | −0.017611 | −0.012352 | −0.000105 | −0.021375 | −0.016565 | 0.001559 | −0.021881 | −0.020665 | −0.026558 | −0.004605 | −0.014403 |
| 164 | 0.002546 | 0.030179 | 0.008459 | 0.03486 | 0.031194 | 0.037374 | 0.005437 | 0.013584 | 0.018646 | −0.002801 | −0.049484 | −0.021746 | 0.01502 | −0.003696 |
| 165 | −0.030283 | 0.005134 | −0.004945 | −0.017105 | −0.029549 | 0.027183 | 0.009545 | 0.00672 | 0.015719 | −0.024682 | 0.024443 | −0.066836 | −0.008205 | 0.006936 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 166 | 0.019291 | 0.040161 | 0.024325 | −0.019027 | −0.008174 | −0.001471 | 0.009776 | 0.009446 | 0.039549 | 0.012932 | −0.030955 | −0.018241 | 0.026197 | 0.014028 |
| 167 | −0.010149 | −0.021256 | −0.031973 | −0.016908 | −0.014989 | 0.034962 | −0.001192 | 0.025351 | 0.005454 | 0.006409 | −0.02806 | 0.01808 | −0.007788 | 0.002967 |
| 168 | 0.002803 | −0.026116 | −0.024815 | 0.026375 | 0.001768 | 0.008981 | −0.025922 | −0.001972 | −0.035435 | −0.080132 | 0.003416 | 0.000894 | −0.030748 | −0.0174 |
| 169 | 0.001649 | 0.014214 | 0.008209 | −0.009261 | −0.01647 | 0.00438 | −0.047933 | −0.013847 | 0.005018 | 0.011845 | −0.02009 | 0.001567 | −0.014007 | −0.0019 |
| 170 | 0.01157 | 0.030731 | 0.013849 | 0.007276 | 0.000624 | 0.007253 | −0.020844 | −0.026888 | −0.012998 | 0.011006 | −0.019504 | −0.009816 | −0.00225 | 0.003335 |
| 171 | 0.0036991 | 0.0055231 | −0.0087771 | −0.023351 | −0.023874 | 0.000686 | −0.048213 | −0.001924 | 0.018133 | 0.031612 | −0.013305 | 0.00069 | −0.015514 | −0.003401 |
| 172 | −0.0118141 | −0.0102151 | −0.0043921 | −0.003345 | −0.010152 | −0.001081 | −0.008619 | −0.010619 | −0.008498 | 0.012002 | −0.019934 | −0.005242 | −0.013561 | 0.003861 |
| 173 | −0.064449 | −0.050426 | −0.040715 | 0.018758 | −0.01 | 0.000767 | 0.009784 | 0.047388 | 0.003455 | −0.016911 | −0.025358 | 0.008996 | 0.01702 | 0.026521 |
| 174 | −0.015868 | −0.017179 | −0.031355 | −0.018464 | −0.016429 | 0.008957 | 0.019508 | 0.001867 | 0.017187 | 0.00399 | −0.002521 | −0.030563 | 0.026718 | −0.009986 |
| 175 | 0.019724 | −0.016734 | −0.0639 | −0.010192 | −0.011063 | 0.005604 | 0.015655 | −0.011731 | 0.012723 | 0.015875 | 0.026309 | 0.034145 | 0.010884 | 0.013714 |
| 176 | 0.0142921 | 0.0246361 | −0.0274471 | −0.018111 | −0.006479 | 0.009281 | −0.008748 | −0.002935 | 0.023164 | 0.029542 | 0.004289 | 0.015533 | 0.000236 | −0.013814 |
| 177 | −0.005628 | 0.021088 | 0.030482 | −0.012022 | −0.006392 | 0.016904 | −0.028139 | 0.052233 | 0.000919 | −0.019633 | −0.025448 | 0.001181 | −0.050608 | 0.015694 |
| 178 | −0.008227 | −0.02425 | −0.02245 | −0.027123 | −0.023753 | 0.012598 | −0.014589 | −0.002459 | 0.019753 | −0.017752 | 0.077764 | 0.035323 | −0.007601 | −0.004923 |
| 179 | 0.00902 | 0.014157 | 0.005117 | −0.019457 | −0.015794 | 0.012625 | −0.020651 | 0.016181 | 0.001373 | −0.005715 | 0.01122 | 0.005768 | 0.013346 | 0.011118 |
| 180 | −0.003346 | −0.000651 | −0.001791 | 0.001094 | −0.000585 | 0.018545 | 0.003545 | 0.024111 | −0.004846 | −0.013329 | 0.024692 | −0.012252 | 0.017531 | 0.017147 |
| 181 | −0.009023 | −0.003033 | −0.014826 | −0.013714 | −0.011082 | 0.014523 | 0.013242 | 0.025974 | −0.007887 | −0.009886 | 0.005573 | 0.014393 | 0.023472 | 0.022326 |
| 182 | 0.004508 | −0.006436 | −0.008706 | 0.005335 | 0.006283 | 0.00904 | 0.015145 | −0.000126 | 0.011386 | 0.013421 | −0.013451 | 0.053306 | 0.034632 | 0.021164 |
| 183 | 0.002252 | 0.008106 | 0.005708 | 0.000541 | −0.01038 | −0.007326 | −0.030531 | 0.024089 | 0.020373 | 0.024022 | −0.030162 | 0.02728 | −0.007721 | 0.03203 |
| 184 | 0.008048 | 0.003093 | 0.026252 | −0.018753 | −0.019457 | −0.019014 | −0.032471 | −0.007596 | 0.003538 | 0.023043 | −0.051458 | −0.010239 | 0.00207 | 0.014842 |
| 185 | 0.001471 | 0.020477 | 0.027267 | −0.002659 | −0.004571 | −0.011267 | 0.01902 | 0.024498 | 0.016788 | 0.017893 | −0.011021 | −0.019334 | −0.042417 | −0.002032 |
| 186 | −0.002447 | 0.018094 | 0.008449 | 0.013031 | 0.006303 | 0.004226 | 0.045914 | 0.033184 | −0.036596 | 0.012186 | 0.035725 | −0.006178 | −0.04339 | −0.008185 |
| 187 | −0.015493 | −0.001322 | 0.020364 | 0.035905 | 0.023594 | 0.00728 | −0.008449 | 0.013816 | −0.018825 | −0.005101 | −0.027909 | 0.019728 | −0.004312 | 0.015959 |
| 188 | −0.002643 | −0.000812 | 0.010229 | 0.034952 | 0.03859 | 0.002164 | 0.013297 | 0.001642 | 0.014391 | 0.004319 | −0.022823 | 0.000015 | 0.00578 | 0.005785 |
| 189 | 0.019413 | 0.021226 | 0.016025 | 0.039785 | 0.058941 | −0.026409 | 0.000517 | −0.024999 | 0.049746 | 0.018344 | −0.016919 | 0.005602 | −0.014462 | 0.007351 |
| 190 | 0.02567 | 0.012544 | 0.00257 | 0.008168 | 0.001386 | 0.003492 | −0.000037 | −0.014939 | 0.02325 | 0.012015 | −0.008741 | 0.00697 | 0.052668 | 0.030451 |
| 191 | 0.015114 | 0.018575 | 0.011438 | −0.007013 | 0.00215 | 0.014707 | 0.007824 | 0.011423 | −0.000286 | 0.017602 | −0.004717 | −0.005363 | 0.031289 | 0.036783 |
| 192 | 0.040565 | −0.067198 | −0.006501 | −0.055262 | −0.04672 | 0.000326 | −0.005787 | −0.054529 | 0.013962 | 0.030361 | 0.010195 | 0.022336 | −0.017083 | −0.009654 |
| 193 | 0.033623 | −0.011507 | −0.031204 | 0.002115 | 0.008225 | 0.0022 | −0.031269 | −0.01435 | 0.014187 , | 0.010263 | −0.019564 | 0.004594 | 0.049133 | 0.010234 |
| 194 | 0.004576 | 0.021439 | −0.044197 | 0.029635 | 0.032449 | −0.002928 | −0.024886 | 0.022684 | −0.010659 | −0.007163 | 0.008351 | 0.018461 | 0.012023 | 0.013488 |
| 195 | −0.015639 | 0.02342 | 0.014304 | 0.00115 | −0.009224 | −0.005297 | 0.034385 | 0.041367 | −0.040761 | 0.000329 | −0.002241 | −0.008209 | 0.008986 | 0.022763 |
| 196 | 0.008887 | −0.010456 | −0.005605 | −0.024936 | −0.022417 | 0.000366 | 0.0169 | −0.011667 | 0.001153 | −0.001128 | 0.008634 | −0.004643 | 0.032933 | 0.023231 |
| 197 | 0.023755 | 0.024718 | 0.041946 | −0.00015 | 0.011076 | 0.003835 | 0.006635 | −0.042175 | 0.050346 | 0.014754 | −0.04016 | −0.018705 | 0.023817 | −0.015038 |
| 198 | 0.011057 | 0.038541 | 0.044686 | −0.01861 | −0.039857 | −0.021524 | 0.004994 | 0.036242 | −0.005584 | −0.017437 | 0.01051 | −0.038902 | −0.060761 | 0.01159 |
| 199 | 0.07358 | 0.028891 | 0.004687 | 0.005797 | −0.000549 | 0.016266 | −0.002862 | 0.018423 | 0.043066 | −0.020233 | −0.026535 | −0.047901 | −0.030556 | 0.013061 |
| 200 | 0.001563 | −0.008793 | −0.012124 | −0.001795 | 0.001758 | −0.005399 | 0.019626 | 0.007981 | −0.01322 | −0.008891 | 0.037073 | 0.023268 | 0.005731 | −0.020544 |
| 201 | 0.001805 | 0.023092 | 0.020864 | 0.028479 | 0.012826 | −0.012202 | −0.006476 | −0.001923 | 0.014394 | −0.01333 | −0.013923 | 0.00168 | −0.025492 | −0.007656 |
| 202 | −0.01325 | 0.005134 | 0.024049 | −0.054237 | −0.048416 | −0.017478 | 0.007177 | −0.015174 | 0.023911 | −0.010106 | 0.016303 | −0.024457 | −0.027822 | 0.016951 |
| 203 | 0.002653 | −0.013222 | 0.006726 | 0.663111 | 0.013711 | 0.014752 | 0.013411 | −0.04347 | −0.047586 | 0.011244 | 0.032405 | −0.046292 | −0.016505 | 0.016424 |
| 204 | −0.015703 | 0.027331 | −0.000886 | −0.025169 | −0.002974 | −0.003496 | 0.004615 | −0.025623 | 0.000894 | −0.00042 | −0.032546 | −0.031782 | 0.004545 | 0.061569 |
| 205 | −0.017975 | −0.050192 | −0.023183 | −0.010699 | −0.020579 | 0.007593 | 0.035472 | −0.021617 | 0.014537 | −0.051864 | 0.014572 | 0.023523 | 0.0175 | −0.012586 |
| 206 | 0.003325 | −0.032477 | −0.007976 | 0.011904 | 0.01452 | 0.027654 | −0.019966 | −0.024147 | −0.00814 | 0.023957 | 0.05443 | −0.013283 | −0.01247 | −0.033644 |
| 207 | −0.021652 | −0.003659 | −0.023914 | 0.003017 | 0.020335 | 0.025022 | 0.008298 | −0.032391 | 0.006198 | −0.030474 | −0.012324 | −0.02495 | 0.045231 | 0.015522 |
| 208 | −0.004448 | −0.005821 | 0.013363 | 0.009072 | −0.015165 | 0.016221 | 0.054469 | −0.035227 | −0.044721 | 0.018289 | 0.039529 | −0.027914 | −0.0149 | −0.024306 |
| 209 | 0.005393 | −0.048768 | −0.013879 | −0.011515 | −0.004209 | 0.016686 | 0.005049 | 0.024519 | 0.03157 | 0.029705 | −0.053746 | 0.014918 | 0.004262 | −0.025704 |
| 210 | −0.018285 | −0.017706 | −0.005247 | −0.021091 | −0.006246 | −0.010572 | −0.036691 | 0.037149 | 0.047179 | −0.002122 | 0.014403 | 0.033688 | 0.046306 | 0.036225 |
| 211 | −0.034731 | −0.012257 | 0.032997 | 0.001681 | 0.014619 | −0.006089 | 0.005925 | −0.023826 | 0.049029 | −0.007951 | −0.018239 | −0.008455 | 0.009017 | 0.019142 |
| 212 | 0.029178 | −0.023348 | 0.010895 | 0.054189 | 0.038621 | −0.028719 | 0.066201 | −0.007191 | 0.00925 | 0.026266 | 0.025892 | 0.001635 | −0.033397 | 0.018831 |
| 213 | 0.018466 | −0.013336 | −0.018826 | 0.00817 | 0.021244 | 0.012963 | 0.020341 | −0.040777 | −0.050314 | 0.01396 | −0.036487 | −0.00164 | −0.043296 | −0.024755 |
| 214 | 0.011178 | 0.005572 | 0.002323 | −0.024097 | −0.01708 | 0.003855 | −0.007766 | 0.017354 | 0.013302 | 0.01296 | 0.034629 | −0.008378 | 0.017667 | 0.01665 |
| 215 | 0.003129 | −0.030004 | −0.027877 | −0.071119 | −0.072723 | −0.005721 | −0.043664 | 0.027985 | −0.004009 | −0.048047 | 0.06911 | 0.024472 | 0.061086 | 0.023126 |
| 216 | −0.049367 | −0.032513 | −0.034488 | −0.015278 | −0.019988 | 0.023284 | −0.006166 | 0.020413 | −0.003661 | −0.072107 | −0.004607 | 0.002808 | −0.028421 | 0.014024 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 217 | −0.020048 | −0.026545 | −0.011828 | −0.018701 | −0.0109 | 0.016745 | 0.000535 | 0.028828 | −0.007605 | 0.06062 | 0.012985 | −0.008176 | 0.035972 | 0.087597 |
| 218 | −0.018359 | −0.020142 | −0.02865 | 0.005219 | 0.00431 | −0.006638 | 0.02115 | 0.010404 | 0.000192 | 0.011416 | 0.029227 | −0.009206 | −0.006088 | 0.00555 |
| 219 | −0.033503 | −0.028144 | −0.026198 | 0.001535 | 0.002047 | 0.004503 | 0.031261 | 0.013881 | 0.00946 | 0.010916 | 0.001229 | −0.032601 | −0.009074 | −0.021893 |
| 220 | −0.003026 | 0.013629 | −0.008043 | −0.018673 | −0.006156 | 0.006271 | 0.000089 | 0.016387 | −0.000352 | 0.040772 | −0.021893 | −0.084131 | 0.019469 | 0.026059 |
| 221 | 0.852368 | −0.060469 | −0.038523 | 0.010113 | −0.005853 | 0.010439 | 0.009123 | 0.008535 | 0.004107 | −0.005364 | 0.017529 | −0.001901 | 0.0088581 | 0.012204 |
| 222 | −0.055701 | 0.823785 | −0.128706 | 0.00406 | −0.00418 | 0.006446 | 0.042028 | −0.009941 | −0.004492 | −0.007507 | 0.04115 | −0.05198 | 0.007948 | 0.043437 |
| 223 | −0.035322 | −0.092016 | 0.8234 | 0.021807 | 0.018932 | −0.000596 | 0.017028 | 0.022417 | 0.020028 | 0.006557 | −0.004077 | −0.047208 | 0.037153 | 0.034377 |
| 224 | 0.011082 | 0.003228 | 0.013151 | 0.732237 | −0.236666 | 0.02086 | −0.10961 | −0.040177 | −0.003992 | −0.025316 | 0.010254 | −0.023159 | 0.030298 | 0.024615 |
| 225 | −0.000799 | −0.007415 | 0.008853 | −0.234423 | 0.733586 | 0.019392 | −0.101425 | −0.020078 | −0.039758 | −0.023448 | 0.014467 | −0.028802 | 0.010802 | 0.026192 |
| 226 | 0.014821 | 0.009483 | 0.013145 | 0.016644 | 0.006286 | 0.884533 | −0.060261 | −0.021431 | 0.032559 | 0.011075 | −0.05617 | −0.008832 | −0.012078 | −0.026233 |
| 227 | 0.0382961 | 0.049747 | 0.055361 | −0.132701 | −0.122677 | −0.047707 | 0.702577 | −0.029503 | 0.05485 | −0.036595 | −0.070002 | −0.000558 | −0.006563 | −0.022119 |
| 228 | 0.010268 | −0.017798 | 0.00437 | −0.035216 | −0.015652 | −0.031427 | −0.004205 | 0.693224 | −0.047658 | −0.006878 | 0.0284431 | −0.10113 | −0.05049 | −0.082374 |
| 229 | −0.01648 | 0.002516 | 0.00444 | 0.008932 | 0.003508 | 0.03479 | 0.056479 | −0.045654 | 0.605973 | −0.079073 | 0.059663 | −0.058243 | −0.033313 | 0.021283 |
| 230 | −0.00689 | −0.002219 | −0.002543 | −0.019078 | −0.014655 | 0.003952 | −0.036909 | −0.014187 | −0.067743 | 0.795007 | −0.032865 | −0.00423 | 0.006266 | 0.007076 |
| 231 | −0.009627 | 0.043587 | 0.02193 | 0.037462 | 0.028809 | −0.055334 | −0.092114 | 0.023187 | 0.077415 | −0.013097 | 0.695783 | 0.044323 | 0.0186971 | −0.083218 |
| 232 | 0.020705 | −0.011212 | −0.007188 | −0.027058 | −0.007865 | 0.006032 | 0.017411 | −0.08485 | −0.022001 | 0.009902 | 0.033033 | 0.590559 | −0.05989 | 0.031343 |
| 233 | 0.016547 | 0.035773 | 0.036994 | 0.016257 | 0.029035 | 0.016439 | −0.00319 | −0.032903 | −0.047054 | −0.016465 | 0.015078 | −0.051365 | 0.746484 | −0.075249 |
| 234 | 0.042403 | 0.050188 | 0.031943 | 0.019354 | 0.025328 | −0.032341 | −0.021299 | −0.105025 | 0.000344 | −0.023496 | −0.085368 | 0.011393 | −0.071846 | 0.724607 |
| 235 | 0.001571 | 0.003715 | 0.022138 | −0.016251 | −0.019596 | 0.00961 | −0.038766 | −0.046787 | 0.004167 | 0.008489 | −0.077264 | 0.010924 | −0.01779 | −0.15771 |
| 236 | 0.020618 | 0.025068 | 0.004602 | −0.005118 | 0.012731 | 0.026747 | 0.012881 | −0.010142 | 0.019127 | −0.022904 | −0.019589 | −0.061633 | 0.019642 | 00.004708 |
| 237 | 0.0370241 | 0.0316051 | 0.028959 | 0.013688 | 0.000933 | 0.026677 | 0.01162 | 0.01031 | −0.00472 | 0.034575 | 0.00362 | 0.01768 | −0.007424 | 0.005307 |
| 238 | 0.011585 | 0.007147 | −0.001026 | 0.011279 | 0.018657 | 0.017184 | 0.034818 | 0.00187 | 0.0341481 | −0.009321 | −0.041756 | −0.000146 | 0.010167 | −0.022257 |
| 239 | −0.003194 | −0.013525 | −0.010117 | 0.01932 | 0.013974 | 0.005694 | 0.029085 | −0.001495 | 0.047738 | −0.011513 | −0.052207 | −0.004781 | −0.013996 | −0.021427 |
| 240 | −0.032224 | 0.012137 | 0.018444 | 0.001517 | 0.017494 | −0.007506 | −0.009279 | −0.012523 | 0.022297 | 0.009527 | −0.018025 | 0.016933 | −0.035127 | −0.034285 |
| 241 | 0.019632 | 0.02779 | 0.023726 | 0.01828 | 0.030956 | 0.00838 | 0.008471 | −0.020414 | −0.000204 | −0.006169 | 0.018185 | 0.009663 | −0.118613 | −0.066128 |
| 242 | 0.009945 | −0.0065 | −0.009777 | 0.009108 | 0.005156 | 0.023692 | 0.016394 | −0.016745 | 0.002617 | 0.02524 | −0.012897 | −0.005893 | −0.055697 | −0.054078 |
| 243 | −0.025368 | −0.009913 | 0.006329 | −0.023341 | −0.030072 | 0.003315 | −0.01504 | −0.049248 | 0.021326 | 0.010028 | 0.008864 | −0.011932 | −0.039918 | −0.032312 |
| 244 | −0.062326 | 0.005413 | 0.022124 | 0.00581 | −0.016715 | 0.02838 | −0.025103 | −0.00018 | 0.011314 | −0.011088 | 0.033377 | −0.00552 | −0.000934 | 0.014284 |
| 245 | −0.006021 | 0.002704 | 0.019611 | −0.031626 | −0.025637 | 0.042966 | −0.017018 | 0.017287 | 0.002575 | −0.022975 | 0.022748 | 0.02878 | 0.006423 | 0.028835 |
| 246 | 0.027693 | 0.004704 | 0.002882 | −0.022019 | −0.016104 | 0.04068 | 0.021885 | 0.021464 | −0.037261 | 0.008894 | 0.025291 | 0.03154 | −0.024101 | −0.016661 |
| 247 | 0.0090651 | −0.008553 | −0.028722 | −0.015413 | −0.013428 | 0.021347 | 0.030984 | 0.000555 | 0.0076821 | −0.027725 | −0.001811 | 0.002513 | −0.005281 | −0.02032 |
| 248 | −0.006202 | −0.012941 | −0.015582 | −0.005343 | −0.001647 | 0.009239 | 0.011078 | −0.020141 | 0.0081251 | −0.025581 | −0.027431 | −0.104078 | 0.0232361 | −0.008803 |
| 249 | 0.0167451 | −0.077864 | −0.032577 | 0.018296 | 0.021799 | −0.003882 | 0.029125 | −0.028548 | −0.000653 | −0.002307 | −0.002638 | −0.106913 | −0.023894 | 0.010243 |
| 250 | 0.004302 | 0.013374 | −0.012897 | 0.016027 | 0.028391 | −0.013231 | −0.017797 | 0.025664 | 0.027507 | 0.002409 | −0.029149 | 0.052502 | −0.000718 | −0.060986 |
| 251 | −0.034065 | 0.006986 | −0.003402 | 0.003405 | −0.007872 | 0.00266 | −0.009419 | 0.020492 | 0.017441 | 0.006771 | −0.001601 | 0.032553 | −0.002499 | −0.049648 |
| 252 | 0.006551 | 0.015339 | 0.035377 | 0.009887 | −0.01069 | −0.007455 | −0.022794 | −0.001335 | 0.012798 | 0.012233 | −0.032405 | −0.029971 | −0.027221 | −0.019759 |
| 253 | 0.008085 | 0.007258 | −0.002964 | −0.028355 | −0.029765 | −0.014951 | −0.021562 | −0.050473 | −0.069526 | 0.025873 | −0.009038 | −0.06143 | −0.018469 | −0.000351 |
| 254 | −0.004889 | −0.031317 | −0.085993 | 0.002251 | −0.003925 | 0.040019 | 0.013421 | 0.007016 | −0.006928 | 0.016319 | 0.020293 | −0.022895 | 0.023022 | 0.024335 |
| 255 | −0.05706 | 0.009995 | 0.009355 | 0.009056 | 0.007894 | 0.029593 | −0.003495 | −0.012503 | −0.001366 | −0.020873 | 0.011795 | 0.044418 | −0.003547 | −0.016685 |
| 256 | −0.019674 | 0.015171 | 0.032305 | 0.006331 | 0.020548 | 0.014849 | 0.035524 | −0.01373 | −0.052242 | −0.023396 | 0.030398 | −0.002816 | 0.024447 | −0.007636 |
| 257 | 0.021247 | −0.000027 | 0.006275 | 0.021682 | 0.015387 | −0.026891 | −0.001702 | 0.024193 | 0.007849 | −0.006509 | 0.006952 | −0.004548 | −0.006881 | −0.020865 |
| 258 | 0.003236 | −0.004474 | −0.007464 | −0.027939 | −0.039208 | −0.008581 | −0.032715 | 0.002945 | 0.0269061 | 0.004244 | 0.0078351 | 0.000411 | 0.022471 | 0.010647 |
| 259 | −0.00668 | −0.083714 | −0.070032 | 0.005311 | 0.001823 | 0.002227 | 0.023764 | −0.037054 | 0.002915 | 0.003748 | 0.015909 | −0.001374 | 0.001526 | 0.00216 |
| 260 | 0.021669 | −0.003335 | −0.003178 | 0.019305 | −0.016654 | −0.003414 | −0.013666 | −0.018969 | −0.026131 | −0.000961 | −0.046483 | −0.018587 | −0.008054 | −0.035775 |
| 261 | −0.010368 | 0.010869 | 0.009145 | 0.009358 | −0.005948 | −0.005483 | −0.028235 | −0.029124 | −0.020522 | 0.016992 | −0.059087 | 0.026395 | 0.026437 | −0.050284 |
| 262 | 0.019835 | −0.016993 | 0.001332 | −0.019561 | −0.021007 | 0.003734 | −0.003366 | −0.012991 | 0.000423 | 0.001688 | −0.019872 | −0.023926 | 0.01629 | 0.00707 |
| 263 | 0.0077411 | −0.031474 | −0.002126 | −0.020436 | −0.018155 | 0.00296 | 0.001372 | −0.015603 | 0.0132141 | −0.003323 | −0.011371 | −0.022979 | 0.0189411 | 0.008408 |
| 264 | −0.007736 | −0.112516 | −0.068325 | −0.024848 | −0.003645 | 0.021992 | 0.009238 | −0.022579 | 0.00358 | 0.005186 | 0.024001 | 0.006718 | 0.007071 | 0.038643 |
| 265 | 0.031024 | −0.030816 | −0.065833 | −0.011773 | −0.005539 | 0.01431 | 0.005823 | −0.005913 | 0.008043 | 0.032449 | −0.000911 | −0.010285 | 0.031527 | 0.03157 |
| 266 | 0.013188 | 0.035778 | −0.010217 | 0.003001 | 0.002779 | 0.006703 | 0.013665 | 0.006989 | 0.008094 | 0.006642 | −0.042764 | 0.040388 | 0.031988 | −0.019096 |
| 267 | 0.010193 | 0.024861 | 0.006054 | 0.017224 | 0.018605 | −0.077354 | −0.016282 | −0.011959 | −0.097899 | 0.037857 | −0.065139 | −0.033377 | 0.030251 | −0.011564 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 268 | 0.0199771 | 0.002197 | 0.0158751 | 0.010621 | −0.003238 | −0.091519 | −0.04884 | −0.011453 | 0.0455191 | 0.0179751 | −0.038112 | −0.011715 | −0.014633 | −0.015449 |
| 269 | 0.0145211 | 0.013647 | 0.015021 | 0.002871 | −0.000816 | −0.083707 | −0.049407 | 0.002475 | 0.015333 | 0.017252 | −0.043081 | −0.012612 | 0.001653 | −0.011096 |
| 270 | 0.022944 | 0.033894 | 0.033703 | −0.013581 | −0.003907 | −0.07575 | −0.124815 | −0.006586 | 0.047205 | 0.002691 | −0.054041 | 0.016794 | 0.008374 | −0.015978 |
| 271 | 0.027848 | −0.031786 | −0.008432 | −0.003668 | −0.00152 | 0.004893 | 0.044434 | −0.002373 | −0.082125 | 0.043981 | 0.033211 | 0.062552 | 0.044092 | 0.047279 |
| 272 | −0.001666 | 0.007485 | −0.011357 | 0.032803 | 0.044326 | −0.0213 | 0.07131 | −0.042436 | −0.206622 | −0.01173 | 0.017257 | −0.001841 | 0.031604 | 0.000751 |
| 273 | 0.013265 | 0.005281 | 0.007196 | 0.006912 | 0.016134 | −0.025748 | 0.005591 | −0.004568 | −0.060959 | −0.065541 | 0.007441 | −0.001642 | −0.000166 | 0.018942 |
| 274 | 0.016415 | 0.011355 | 0.010272 | 0.005551 | 0.018195 | −0.016523 | 0.007108 | −0.002187 | −0.079087 | −0.064941 | 0.008594 | 0.003796 | 0.004033 | 0.016154 |
| 275 | −0.000057 | 0.009179 | 0.010163 | −0.035296 | −0.008278 | 0.010954 | −0.121214 | −0.001371 | 0.012905 | −0.148381 | −0.004788 | 0.021356 | 0.077697 | 0.035061 |
| 276 | 0.019141 | 0.015958 | −0.004432 | −0.008856 | 0.008862 | 0.031855 | 0.055133 | −0.021388 | −0.082386 | −0.0028 | 0.009631 | −0.058966 | 0.010599 | −0.010639 |
| 277 | 0.01545 | 0.010819 | 0.009977 | −0.010144 | −0.008114 | 0.031587 | 0.025466 | −0.023964 | 0.006552 | 0.01883 | 0.026314 | 0.040001 | −0.005578 | 0.006861 |
| 278 | 0.017123 | 0.019858 | 0.009637 | −0.027264 | −0.021458 | 0.035712 | 0.015468 | −0.040362 | −0.005539 | 0.013523 | 0.006131 | 0.037321 | −0.001749 | 0.007971 |
| 279 | −0.001165 | −0.001463 | −0.002097 | 0.005301 | 0.019006 | 0.014055 | 0.042558 | −0.017653 | 0.045448 | −0.012029 | −0.02894 | −0.014034 | 0.024014 | −0.027673 |
| 280 | −0.0148 | −0.003859 | 0.008433 | −0.056978 | −0.065759 | −0.005443 | −0.033684 | −0.078732 | −0.00427 | 0.004986 | 0.035975 | 0.021326 | −0.070528 | −0.016099 |
| 281 | 0.014977 | 0.008527 | −0.001905 | −0.000511 | 0.004438 | 0.011471 | 0.04505 | 0.029871 | −0.033845 | −0.008149 | 0.014231 | 0.019805 | −0.021961 | 0.017432 |
| 282 | 0.009685 | −0.00755 | −0.018859 | −0.024254 | −0.01976 | 0.022177 | 0.021726 | 0.039564 | −0.019102 | −0.000525 | 0.036562 | 0.044033 | −0.01174 | 0.039391 |
| 283 | −0.001655 | 0.005145 | −0.017205 | −0.007376 | 0.00965 | 0.015442 | 0.03156 | −0.00527 | −0.010007 | −0.019541 | 0.0018361 | −0.030631 | 0.0278621 | −0.02518 |
| 284 | 0.019398 | 0.0067641 | 0.0160081 | 0.0208 | 0.01918 | −0.022218 | 0.003071 | 0.016725 | 0.000212 | 0.008051 | 0.011533 | −0.011454 | 0.006809 | −0.021117 |
| 285 | 0.023179 | −0.012551 | 0.001146 | 0.011214 | 0.002857 | −0.01402 | 0.010585 | 0.01883 | −0.007121 | 0.005724 | 0.042003 | −0.033044 | 0.014487 | −0.002616 |
| 286 | 0.011421 | −0.009141 | −0.00619 | 0.0045 | −0.028684 | −0.005173 | −0.020655 | 0.049506 | −0.005819 | 0.018052 | 0.02912 | 0.019254 | −0.003084 | 0.042197 |
| 287 | 0.000818 | −0.005726 | 0.000139 | −0.001656 | −0.018062 | −0.015936 | −0.03901 | 0.014023 | 0.005811 | 0.005433 | 0.045369 | 0.000772 | −0.001353 | 0.040253 |
| 288 | 0.016284 | 0.004325 | 0.024686 | −0.032535 | −0.039638 | −0.00428 | −0.023367 | −0.015747 | 0.017475 | 0.005042 | 0.023141 | −0.020149 | 0.045332 | 0.016598 |
| 289 | 0.028724 | 0.008177 | 0.015996 | −0.019675 | −0.026818 | 0.013689 | 0.002961 | 0.008929 | −0.002506 | −0.009415 | 0.025681 | −0.002701 | 0.025012 | 0.009898 |
| 290 | 0.017563 | 0.00194 | 0.008523 | 0.015026 | 0.013223 | 0.005533 | 0.04143 | 0.002714 | 0.023646 | 0.017205 | 0.030721 | −0.002332 | 0.026897 | 0.005215 |
| 291 | 0.014628 | −0.000323 | 0.009026 | 0.017983 | 0.013638 | 0.006105 | 0.042417 | 0.006663 | 0.020115 | 0.021368 | 0.032971 | 0.011369 | 0.027638 | 0.008258 |
| 292 | 0.015498 | −0.011615 | −0.009561 | 0.008527 | 0.014316 | 0.010216 | 0.043519 | 0.020326 | 0.033207 | 0.022062 | 0.037703 | 0.012608 | 0.039004 | 0.001723 |
| 293 | −0.019141 | −0.00482 | −0.027604 | 0.022149 | 0.019188 | −0.023994 | −0.015353 | 0.016431 | 0.031418 | −0.005452 | −0.013862 | 0.030572 | 0.012315 | −0.002222 |
| 294 | −0.008026 | −0.017471 | 0.003811 | 0.011217 | 0.012701 | −0.017234 | −0.051167 | 0.014277 | 0.034239 | −0.003912 | −0.040262 | 0.052144 | −0.005383 | −0.010834 |
| 295 | 0.0160081 | 0.012226 | 0.0079561 | 0.038422 | 0.035542 | 0.013811 | 0.003246 | 0.032327 | −0.030144 | −0.024973 | −0.038109 | 0.037166 | −0.015033 | 0.016981 |
| 296 | −0.003015 | −0.019184 | −0.009808 | 0.002838 | −0.001695 | −0.000675 | −0.048938 | −0.009523 | −0.018368 | −0.036601 | −0.026133 | 0.024629 | 0.020917 | 0.032244 |
| 297 | 0.013618 | 0.008079 | −0.003647 | 0.014223 | 0.018242 | 0.009487 | 0.035797 | 0.031618 | −0.058142 | −0.021375 | −0.039198 | 0.039011 | −0.009001 | 0.001754 |
| 298 | −0.002232 | 0.022338 | −0.007085 | 0.022809 | 0.030309 | 0.015216 | 0.040512 | 0.002473 | −0.002902 | 0.010838 | 0.028793 | 0.011113 | 0.035165 | −0.018678 |
| 299 | 0.005647 | 0.012373 | −0.007394 | 0.006032 | −0.005909 | −0.014461 | 0.003137 | 0.015062 | 0.022651 | 0.013037 | −0.05955 | −0.008383 | 0.009295 | 0.019054 |
| 300 | 0.024114 | 0.036486 | 0.004887 | 0.0183 | 0.029432 | 0.012425 | −0.022804 | 0.005154 | 0.045809 | −0.001108 | 0.011359 | −0.001002 | −0.009497 | −0.020778 |
| 301 | −0.003194 | −0.008179 | 0.004365 | 0.020461 | 0.009887 | −0.006961 | 0.004386 | −0.000799 | 0.012489 | 0.002728 | −0.021146 | −0.025901 | −0.003493 | −0.010529 |
| 302 | −0.015385 | −0.031097 | −0.003683 | −0.013799 | −0.016701 | −0.005515 | −0.034293 | −0.00108 | 0.033934 | −0.005183 | −0.003343 | 0.034879 | 0.012099 | 0.026111 |
| 303 | −0.007414 | −0.0060531 | −0.0199281 | −0.026046 | −0.049364 | −0.007601 | −0.019318 | −0.018122 | 0.006445 | 0.033583 | −0.012846 | −0.010235 | 0.001263 | 0.022631 |
| 304 | −0.0189541 | −0.012667 | −0.01711 | −0.041018 | −0.052455 | −0.018383 | −0.046667 | −0.033963 | 0.026377 | 0.025063 | −0.026973 | −0.013369 | 0.0302351 | 0.026879 |
| 305 | 0.012689 | 0.0143551 | −0.0184711 | 0.01965 | 0.01497 | 0.010783 | 0.003778 | −0.007394 | −0.019834 | −0.014858 | 0.045293 | 0.011888 | 0.013178 | −0.000559 |
| 306 | −0.020773 | −0.000008 | −0.015049 | −0.011449 | −0.00823 | 0.004369 | −0.00738 | 0.030409 | 0.045282 | 0.002981 | −0.017365 | −0.00271 | 0.023807 | −0.000838 |
| 307 | 0.037867 | 0.022577 | 0.000061 | −0.015825 | 0.007054 | 0.016375 | −0.021129 | −0.024961 | 0.03153 | −0.004176 | −0.019957 | −0.028227 | −0.020567 | 0.008219 |
| 308 | −0.012899 | −0.026477 | −0.00821 | −0.034903 | −0.023 | −0.001889 | 0.024445 | −0.010977 | 0.003906 | −0.010574 | −0.001861 | −0.038392 | 0.00581 | 0.000389 |
| 309 | −0.004469 | −0.014326 | −0.0116911 | 0.005856 | 0.012953 | −0.016062 | 0.005071 | −0.017884 | 0.011983 | −0.000567 | −0.014038 | 0.008979 | 0.008597 | −0.006934 |
| 310 | 0.003448 | −0.01297 | −0.01104 | −0.011275 | −0.002608 | 0.017439 | 0.003857 | 0.030213 | 0.026073 | 0.012252 | −0.017732 | −0.001511 | 0.042885 | 0.029606 |
| 311 | 0.012484 | 0.002128 | −0.000238 | 0.026848 | −0.000095 | −0.003686 | −0.000969 | −0.017866 | −0.06001 | −0.019512 | 0.048823 | 0.006144 | −0.020551 | 0.007213 |
| 312 | 0.017035 | −0.005015 | −0.040783 | −0.003535 | −0.003172 | −0.037392 | −0.00011 | 0.0162 | −0.036295 | −0.025441 | −0.04169 | −0.034118 | −0.043011 | −0.044026 |
| 313 | −0.000641 | 0.012419 | 0.004433 | 0.007421 | −0.000245 | −0.007673 | −0.014573 | −0.012212 | −0.017941 | 0.00138 | 0.010778 | 0.009334 | −0.01923 | −0.032563 |
| 314 | 0.025547 | 0.018112 | −0.020152 | 0.011908 | 0.038311 | 0.013272 | 0.004118 | 0.002609 | 0.012608 | 0.00688 | −0.027333 | 0.044516 | 0.06009 | 0.00042 |
| 315 | 0.009595 | 0.021938 | −0.003989 | −0.00086 | −0.002459 | −0.002563 | −0.017403 | −0.023087 | −0.009634 | 0.011173 | 0.001212 | −0.003921 | −0.008038 | −0.00483 |
| 316 | −0.04176 | 0.007369 | 0.011299 | −0.028591 | −0.031699 | 0.023702 | −0.024696 | −0.048786 | −0.002227 | −0.017611 | 0.051304 | 0.035406 | 0.012706 | −0.038256 |
| 317 | −0.007405 | 0.00316 | −0.0158 | 0.028167 | 0.034929 | −0.00045 | 0.015064 | −0.007812 | −0.014692 | −0.002305 | −0.013321 | 0.004426 | 0.03387 | −0.001863 |
| 318 | −0.017271 | −0.024568 | −0.04338 | 0.012171 | 0.020218 | 0.004282 | 0.003476 | −0.019983 | 0.012832 | 0.00789 | −0.001053 | −0.032595 | −0.011125 | 0.018255 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 319 | −0.016921 | −0.007686 | −0.02177 | −0.017806 | −0.023817 | 0.005291 | 0.00159 | 0.004367 | −0.008787 | 0.00858 | 0.007982 | −0.006192 | −0.000311 | 0.010498 |
| 320 | −0.017264 | −0.0206091 | −0.0259081 | −0.023815 | −0.020547 | −0.000205 | −0.003584 | 0.004534 | 0.031237 | −0.001808 | 0.043214 | 0.016251 | 0.012779 | −0.010801 |
| 321 | 0.034034 | 0.016467 | 0.029758 | −0.014935 | 0.007274 | −0.003972 | −0.03295 | −0.033787 | 0.018827 | 0.002207 | −0.002726 | 0.010676 | −0.008091 | −0.00333 |
| 322 | 0.037355 | 0.016506 | −0.007197 | 0.012479 | 0.006203 | −0.003416 | −0.00816 | −0.033051 | 0.061382 | 0.001887 | −0.04646 | 0.013477 | −0.006835 | 0.007264 |
| 323 | 0.029999 | 0.010996 | 0.004086 | −0.01863 | −0.008959 | −0.013585 | 0.01423 | 0.03968 | 0.025494 | 0.005439 | −0.058614 | 0.0293 | 0.004734 | −0.030128 |
| 724 | 0.002644 | 0.002771 | 0.007751 | −0.010302 | 0.018011 | −0.012842 | 0.023593 | −0.047013 | 0.050106 | 0.022342 | 0.033031 | −0.024766 | −0.014209 | −0.028721 |
| 325 | −0.007618 | −0.004439 | 0.005975 | −0.00163 | 0.015663 | −0.032132 | −0.01512 | −0.08099 | −0.012228 | −0.003691 | 0.005686 | 0.015065 | −0.004094 | −0.014809 |
| 326 | −0.012958 | 0.007812 | 0.035741 | 0.022402 | 0.029811 | −0.016294 | −0.032649 | −0.011234 | 0.027168 | −0.013857 | −0.009315 | 0.043879 | 0.007291 | 0.041906 |
| 327 | −0.006416 | −0.032377 | −0.022555 | −0.004042 | −0.001997 | 0.01218 | 0.026462 | −0.00225 | −0.019903 | 0.00978 | 0.011804 | −0.020435 | 0.013462 | 0.024358 |
| 328 | −0.000836 | 0.000382 | 0.037279 | 0.005451 | −0.010145 | 0.024251 | 0.045884 | −0.036501 | −0.014612 | −0.029789 | 0.040057 | 0.000693 | −0.023793 | −0.008446 |
| 329 | −0.014783 | −0.032604 | −0.006776 | 0.016599 | −0.001755 | 0.010782 | 0.031508 | 0.023154 | −0.01536 | 0.015334 | 0.013889 | −0.014076 | −0.015926 | 0.038704 |
| 330 | 0.027921 | 0.016288 | 0.024975 | −0.031936 | −0.013308 | 0.008622 | −0.003398 | 0.00791 | −0.007206 | −0.004485 | 0.052942 | 0.017478 | −0.001336 | 0.031449 |
| 331 | 0.007344 | −0.03024 | −0.008167 | 0.001855 | 0.004685 | −0.00408 | 0.004712 | −0.005641 | 0.002301 | 0.02479 | 0.027421 | 0.015583 | −0.008864 | 0.00307 |
| 332 | 0.000746 | 0.013815 | 0.030588 | −0.002885 | −0.013686 | 0.002884 | −0.005345 | 0.052746 | 0.026117 | 0.013711 | 0.02054 | 0.044059 | 0.004105 | 0.007131 |
| 333 | −0.001076 | −0.017605 | 0.012382 | −0.00332 | 0.013913 | −0.006115 | 0.004715 | −0.039808 | 0.002509 | 0.002106 | 0.005602 | −0.008798 | −0.020714 | −0.009915 |
| 334 | −0.010746 | −0.017129 | −0.001421 | 0.037519 | 0.042363 | −0.022413 | −0.028545 | −0.022972 | −0.00933 | −0.005812 | −0.0055 | 0.001883 | −0.026165 | −0.050663 |
| 335 | −0.008623 | −0.006508 | 0.000928 | −0.024428 | −0.007651 | −0.00151 | 0.006719 | 0.001697 | 0.008781 | −0.000647 | −0.000287 | −0.005496 | −0.016426 | 0.003512 |
| 336 | 0.008853 | 0.014616 | −0.002012 | 0.017916 | 0.018304 | −0.013926 | −0.005642 | −0.016456 | 0.004426 | −0.011653 | −0.020134 | −0.016847 | 0.024616 | 0.019084 |
| 337 | 0.018841 | 0.028745 | 0.016992 | 0 | −0.026229 | 0.011022 | 0.010039 | 0.019596 | −0.02632 | 0.008771 | −0.011827 | −0.015552 | 0.026534 | −0.019586 |
| 338 | −0.035176 | −0.013505 | −0.022814 | −0.000174 | −0.02012 | −0.001303 | 0.000372 | 0.079178 | −0.018375 | −0.021636 | −0.002507 | 0.01414r | −0.000845 | 0.026869 |
| 339 | −0.004857 | −0.030861 | −0.014212 | 0.01678 | −0.022885 | −0.017963 | −0.006444 | −0.027446 | −0.006816 | 0.028434 | 0.045837 | −0.065746 | 0.049783 | 0.027968 |
| 340 | −0.015623 | 0.031872 | 0.008973 | 0.043781 | 0.027705 | −0.016699 | 0.009377 | −0.024879 | 0.00324 | 0.001505 | 0.001866 | 0.030645 | −0.047444 | 0.00529 |

| | IB | IC | ID | IE | IF | IG | IH | II | IJ | IK | IL | IM | IN | IO |
|---|---|---|---|---|---|---|---|---|---|---|---|---|---|---|
| 1 | −0.0573681 | −0.0492941 | 0.002694 | −0.071042 | −0.086662 | 0.00051 | −0.058205 | −0.081367 | −0.054429 | 0.0087411 | −0.039139 | −0.013032 | 0.016451 | −0.002943 |
| 2 | 0.00424 | 0.024843 | 0.086424 | −0.005539 | −0.045435 | 0.026657 | 0.073867 | 0.0795 | 0.0452291 | 0.0037341 | 0.0504981 | 0.0793451 | 0.032371 | −0.016553 |
| 3 | −0.093629 | 0.030495 | 0.024276 | −0.006331 | 0.015695 | −0.003953 | 0.047815 | −0.009025 | 0.015977 | 0.048056 | 0.057643 | 0.005092 | 0.019047 | 0.005125 |
| 4 | −0.025723 | 0.016171 | 0.009961 | −0.068394 | −0.072392 | −0.006507 | −0.024332 | −0.011759 | 0.026056 | −0.001957 | 0.058453 | −0.056339 | −0.047002 | −0.004454 |
| 5 | 0.04876 | 0.019717 | −0.00874 | 0.057978 | 0.012999 | 0.00848 | −0.003012 | 0.017993 | 0.04706 | −0.003392 | −0.007641 | −0.021269 | 0.037006 | 0.103374 |
| 6 | 0.065512 | 0.053766 | 0.023494 | −0.004306 | −0.001681 | −0.007081 | 0.003949 | 0.070181 | 0.021527 | −0.053011 | −0.067879 | 0.038143 | 0.083433 | 0.044858 |
| 7 | −0.0150931 | 0.021755 | 0.0271081 | −0.042878 | −0.045453 | 0.012167 | 0.068489 | 0.0327 | 0.0387481 | 0.0138731 | −0.064654 | −0.068225 | −0.051999 | 0.018754 |
| 8 | 0.057297 | −0.008707 | −0.013119 | −0.026947 | −0.032108 | −0.002113 | 0.038136 | −0.011036 | −0.044682 | 0.011955 | 0.005397 | 0.004013 | 0.004842 | −0.02354 |
| 9 | −0.001666 | 0.0364641 | −0.034108 | −0.015809 | 0.021199 | 0.008822 | 0.014177 | 0.011916 | −0.057159 | −0.004928 | 0.038463 | 0.025394 | 0.053935 | 0.053554 |
| 10 | −0.005984 | −0.022607 | −0.005299 | 0.055884 | 0.089854 | −0.046314 | −0.030382 | 0.005666 | 0.037195 | −0.01391 | −0.022308 | −0.001813 | −0.019346 | −0.024202 |
| 11 | −0.012575 | −0.015391 | 0.000327 | −0.006898 | −0.021192 | 0.039501 | 0.008247 | 4.07974 | −0.041428 | −0.006829 | −0.008553 | 0.020811 | 0.008391 | −0.015724 |
| 12 | 0.0300881 | −0.027005 | 0.0407771 | −0.003817 | 0.004228 | −0.013064 | 0.018542 | 0.045239 | −0.003728 | 0.0287951 | −0.029409 | −0.041806 | −0.032702 | −0.048993 |
| 13 | 0.013477 | 0.030319 | 0.057851 | 0.020526 | −0.052063 | 0.030764 | −0.010338 | 0.01926 | 0.035666 | −0.008939 | −0.011819 | 0.021077 | 0.02334 | 0.027647 |
| 14 | 0.019745 | −0.000361 | −0.036939 | −0.010165 | 0.020962 | 0.050334 | 0.034233 | 0.013722 | −0.043421 | 0.048889 | 0.043253 | 0.04456 | −0.012152 | −0.011154 |
| 15 | 0.01055 | 0.034846 | −0.005905 | 0.018652 | 0.009275 | 0.03138 | 0.062322 | 0.020795 | 0.006094 | 0.002794 | 0.022846 | −0.039976 | −0.086167 | −0.039864 |
| 16 | −0.071243 | 0.026719 | −0.013948 | −0.00873 | −0.019243 | −0.009987 | −0.029847 | −0.004644 | −0.077131 | 0.035433 | 0.019934 | −0.017313 | 0.009611 | 0.027004 |
| 17 | −0.058717 | −0.022115 | −0.014277 | 0.036103 | 0.035269 | 0.024224 | −0.044869 | −0.032487 | 0.051403 | −0.015348 | −0.072426 | −0.025897 | 0.015955 | −0.006425 |
| 18 | −0.0332111 | −0.016919 | 0.040895 | −0.057485 | −0.00144 | −0.088868 | −0.055072 | 0.030593 | 0.027481 | 0.031099 | −0.025759 | −0.00987 | −0.005545 | −0.045668 |
| 19 | 0.0700441 | −0.087119 | −0.0564861 | −0.021791 | −0.008215 | 0.047437 | 0.008058 | 0.025494 | 0.108101 | 0.000047 | −0.059092 | 0.002961 | 0.003535 | 0.048625 |
| 20 | 0.073899 | 0.085767 | 0.00721 | −0.01335 | 0.019751 | −0.012683 | −0.009715 | 0.059798 | −0.052462 | 0.026245 | 0.014745 | −0.026251 | 0.003583 | 0.025183 |
| 21 | 0.040364 | −0.012495 | −0.043428 | 0.003735 | 0.028404 | −0.004346 | −0.049403 | 0.007021 | −0.000591 | 0.018584 | 0.026978 | 0.052232 | 0.018248 | 0.039796 |
| 22 | −0.011281 | −0.039425 | −0.061973 | −0.077199 | −0.041778 | 0.000088 | 0.019475 | −0.070752 | −0.097825 | 0.003691 | 0.0219441 | −0.013513 | −0.029616 | −0.041637 |
| 23 | 0.054252 | −0.05215 | −0.004553 | 0.092031 | 0.095865 | −0.021354 | −0.048734 | 0.00114 | 0.019802 | −0.098921 | −0.0851 | 0.004677 | 0.047587 | 0.031618 |
| 24 | −0.069314 | 0.027717 | 0.0132 | 0.007972 | 0.015102 | −0.055587 | −0.059941 | −0.023621 | −0.051734 | −0.014855 | −0.058748 | 0.001198 | 0.039796 | −0.012911 |
| 25 | 0.031555 | 0.019277 | 0.057254 | 0.046351 | 0.029787 | 0.025817 | −0.00294 | −0.018137 | −0.020836 | −0.026225 | −0.010735 | −0.032894 | −0.018028 | −0.03494 |
| 26 | −0.060117 | 0.031476 1 | −0.009446 | 0.000851 | −0.008236 | 0.006917 | −0.020575 | −0.077337 | −0.079805 | −0.08451 | 0.076135 | −0.000959 | 0.008563 | 0.059936 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 27 | 0.042028 | −0.115683 | 0.076949 | 0.031457 | −0.006517 | −0.013682 | −0.033204 | −0.01512 | 0.041091 | 0.008617 | −0.064489 | 0.054675 | −0.066322 | −0.066617 |
| 28 | −0.0336 | −0.07805 | 0.072286 | 0.061122 | 0.018238 | 0.078877 | 0.085417 | −0.025278 | −0.023818 | −0.024456 | −0.000379 | 0.030012 | −0.013647 | −0.047759 |
| 29 | 0.027607 | −0.036613 | −0.018069 | −0.005278 | 0.00369 | −0.021259 | −0.004708 | −0.031891 | −0.062585 | −0.028591 | −0.029675 | 0.011961 | 0.023553 | 0.016404 |
| 30 | −0.058607 | −0.004633 | 0.046426 | 0.010003 | −0.022466 | −0.092677 | −0.067626 | −0.05205 | −0.104087 | −0.03675 | −0.061146 | 0.044394 | 0.019643 | 0.017722 |
| 31 | 0.006074 | 0.002407 | 0.03144 | 0.001287 | −0.022279 | −0.04471 | −0.05131 | −0.011643 | −0.054592 | 0.008052 | −0.025542 | −0.008674 | −0.027244 | −0.029771 |
| 32 | 0.051329 | 0.03322 | 0.013075 | 0.015905 | −0.02292 | −0.043742 | −0.046832 | 0.031828 | 0.062899 | 0.023786 | −0.028724 | −0.050924 | −0.004743 | 0.037525 |
| 33 | 0.044886 | 0.103261 | −0.027332 | −0.020182 | −0.006541 | 0.003462 | −0.026979 | 0.100949 | 0.015635 | −0.041924 | 0.000047 | 0.003026 | 0.001846 | 0.017866 |
| 34 | 0.074721 | −0.05746 | 0.0448941 | −0.000925 | −0.010196 | 0.059515 | 0.051396 | −0.024204 | −0.039998 | 0.011815 | −0.025787 | 0.005719 | −0.017626 | −0.046504 |
| 35 | −0.01438 | −0.006764 | 0.027043 | 0.015721 | 0.005169 | −0.122916 | −0.077003 | 0.054463 | 0.084345 | 0.060416 | 0.054156 | −0.030715 | −0.074993 | −0.060557 |
| 36 | −0.052973 | −0.013625 | 0.028784 | −0.013625 | −0.028099 | 0.041902 | 0.009631 | −0.048334 | 0.051211 | 0.001529 | 0.006283 | −0.020015 | −0.028232 | −0.022807 |
| 37 | 0.055746 | −0.052765 | 0.068877 | 0.009882 | 0.006682 | 0.008414 | 0.03937 | −0.010907 | −0.04763 | 0.042858 | 0.087719 | 0.014071 | −0.026977 | −0.033529 |
| 38 | −0.080564 | 0.026688 | 0.037219 | 0.03705 | 0.019061 | 0.016558 | −0.025472 | 0.020615 | −0.032268 | −0.040809 | −0.026801 | 0.053667 | 0.035695 | 0.029049 |
| 39 | −0.00366 | 0.01136 | 0.032208 | −0.027866 | −0.004513 | −0.019401 | −0.019071 | −0.067851 | 0.045306 | 0.005564 | 0.069538 | 0.003132 | −0.008497 | −0.006566 |
| 40 | 0.037621 | −0.001214 | 0.052686 | 0.011927 | −0.041034 | −0.057228 | −0.018826 | −0.004845 | −0.035818 | −0.055561 | −0.002984 | 0.059681 | 0.0282091 | 0.005539 |
| 41 | −0.104515 | −0.003453 | −0.056665 | 0.020304 | 0.017945 | 0.061359L | −0.022859 | −0.029559 | −0.021418 | 0.026431 | −0.027758 | −0.049914 | −0.017745 | −0.044029 |
| 42 | 0.00431 | 0.01693 | −0.00192 | −0.007152 | 0.001008 | −0.004554 | −0.000469 | 0.011893 | −0.01317 | 0.001122 | 0.004309 | −0.005756 | 0.002277 | 0.005545 |
| 43 | −0.050546 | −0.09755 | −0.025588 | −0.017492 | −0.042088 | 0.010697 | 0.043462 | −0.009487 | −0.010216 | 0.009803 | 0.001886 | −0.044711 | −0.057238 | 0.020629 |
| 44 | 0.002706 | 0.055478 | −0.000433 | −0.011813 | −0.003869 | −0.039886 | −0.032927 | 0.049078 | −0.021682 | −0.02537 | −0.010003 | 0.057588 | 0.047143 | 0.020474 |
| 45 | 0.095698 | 0.020324 | −0.049771 | 0.032788 | 0.091745 | 0.053638 | 0.070862 | 0.038056 | 0.05247 | −0.008675 | 0.009452 | 0.029451 | 0.047709 | 0.080958 |
| 46 | 0.066037 | 0.0482 | −0.018829 | −0.011635 | −0.007639 | 0.002984 | −0.025313 | −0.020002 | 0.035443 | 0.081578 | 0.071412 | −0.02301 | 0.010198 | 0.028609 |
| 47 | 0.059745 | 0.002038 | −0.080267 | −0.084237 | −0.031633 | −0.024436 | −0.023248 | 0.061461 | 0.05669 | −0.000723 | −0.032383 | −0.01621 | 0.017703 | 0.038308 |
| 48 | 0.005289 | 0.000623 | 0.06587 | −0.007066 | −0.000421 | −0.014025 | 0.002171 | 0.03837 | −0.038322 | −0.004327 | −0.027644 | 0.020098 | −0.056014 | −0.052239 |
| 49 | 0.0114881 | −0.0060931 | −0.005656 | 0.007145 | 0.030406 | 0.07254 | 0.021097 | −0.039941 | −0.023315 | 0.023223 | −0.014012 | 0.016458 | 0.009654 | 0.017266 |
| 50 | −0.004674 | −0.054303 | −0.111881 | −0.015349 | 0.045592 | 0.01246 | 0.040284 | −0.043281 | −0.003194 | 0.045318 | 0.005269 | 0.000325 | 0.061481 | −0.024592 |
| 51 | −0.041177 | −0.021935 | 0.030497 | −0.094832 | −0.088765 | 0.07201 | 0.137304 | 0.000519 | −0.059863 | −0.055154 | −0.060598 | −0.011518 | −0.018676 | 0.002702 |
| 52 | −0.037877 | −0.029655 | −0.013059 | 0.072079 | 0.02769 | −0.031912 | 0.014565 | −0.045734 | 0.025537 | −0.044214 | −0.051192 | −0.005203 | 0.013864 | 0.052092 |
| 53 | 0.05044 | 0.123156 | 0.05434 | −0.062113 | −0.097338 | 0.031163 | 0.026311 | 0.001119 | −0.059893 | 0.013131 | −0.007391 | 0.066478 | 0.039895 | 0.105839 |
| 54 | 0.081898 | −0.059391 | −0.072006 | −0.077276 | −0.077689 | 0.032232 | −0.000337 | 0.09274 | −0.024115 | 0.053915 | −0.043436 | 0.02401 | −0.021786 | −0.035684 |
| 55 | −0.048333 | 0.039558 | 0.048585 | 0.027594 | −0.024007 | 0.036562 | 0.076881 | 0.039656 | 0.005069 | −0.017035 | −0.021691 | −0.007728 | 0.003239 | −0.021356 |
| 56 | −0.055491 | −0.013593 | −0.035548 | 0.005399 | 0.04818 | 0.018689 | 0.070665 | −0.028167 | 0.015914 | −0.053766 | 0.08966 | 0.071123 | 0.047294 | −0.000183 |
| 57 | −0.01339 | 0.003327 | −0.021752 | −0.026595 | −0.004267 | 0.020353 | 0.073902 | 0.001808 | −0.040424 | −0.12803 | −0.000042 | 0.073155 | 0.014282 | −0.00372 |
| 58 | 0.103829 | −0.020625 | −0.076252 | 0.033869 | 0.058569 | 0.061848 | −0.0203 | 0.000984 | 0.005418 | −0.048505 | −0.049523 | −0.029425 | −0.022298 | −0.055532 |
| 59 | −0.0881041 | 0.032657 | 0.078549 | 0.009738 | −0.051548 | −0.027643 | −0.003977 | −0.035573 | −0.011223 | −0.064616 | 0.029841 | 0.022476 | 0.024603 | 0.00503 |
| 60 | −0.129632 | −0.045715 | −0.056699 | 0.002969 | 0.02636 | 0.060962 | 0.033428 | −0.085439 | −0.057702 | 0.096451 | 0.026942 | −0.109193 | −0.05522 | 0.008045 |
| 61 | 0.007015 | −0.003868 | −0.020139 | 0.08041 | 0.05477 | 0.028636 | 0.012595 | −0.014556 | −0.012362 | 0.025275 | 0.039767 | −0.066442 | −0.012884 | −0.015903 |
| 62 | −0.044358 | 0.042083 | 0.024781 | 0.058768 | 0.048085 | −0.009373 | −0.046831 | −0.019034 | −0.03239 | 0.040841 | 0.026275 | −0.080929 | −0.104579 | −0.067511 |
| 63 | 0.099111 | −0.000888 | −0.039456 | 0.027208 | 0.011041 | 0.032259 | 0.054247 | 0.044323 | 0.127229 | 0.004431 | 0.010867 | −0.054325 | −0.047028 | −0.026778 |
| 64 | −0.035725 | −0.012814 | −0.010027 | −0.010169 | 0.003982 | −0.01054 | −0.025895 | 0.003399 | −0.009295 | 0.025893 | −0.082365 | −0.036445 | −0.005911 | −0.01344 |
| 65 | 0.04957 | 0.001959 | 0.014089 | 0.057744 | 0.037381 | −0.060007 | 0.043233 | 0.034226 | 0.046815 | −0.077397 | 0.020704 | 0.074168 | 0.014467 | −0.045578 |
| 66 | 0.047184 | 0.027165 | −0.000694 | 0.040389 | 0.058938 | −0.051045 | 0.013637 | −0.05793 | −0.038681 | −0.069563 | −0.060443 | −0.058172 | 0.028361 | 0.026398 |
| 67 | 0.000338 | −0.014945 | 0.03396 | −0.091175 | −0.073291 | −0.078974 | −0.044397 | 0.066358 | 0.012335 | 0.023645 | 0.023503 | −0.028425 | −0.016409 | −0.047389 |
| 68 | 0.001988 | −0.017008 | −0.026798 | 0.012565 | 0.04337 | 0.016047 | 0.030453 | 0.044863 | −0.005502 | −0.034051 | −0.028645 | 0.003339 | 0.026149 | −0.005621 |
| 69 | −0.086107 | 0.014482 | 0.003222 | −0.054973 | −0.05141 | −0.10981 | −0.069317 | 0.031469 | −0.031872 | −0.005492 | −0.021117 | 0.04592 | −0.029192 | −0.050437 |
| 70 | 0.034096 | −0.028893 | 0.069131 | 0.061041 | 0.010381 | −0.050449 | −0.017821 | 0.066211 | 0.012769 | 0.017122 | −0.028026 | 0.024802 | −0.039163 | 0.008386 |
| 71 | −0.025955 | 0.031769 | −0.038094 | 0.04971 | 0.042148 | −0.036828 | 0.066036 | 0.048509 | −0.002972 | −0.040621 | −0.040002 | −0.048371 | −0.006137 | 0.034465 |
| 72 | −0.018333 | 0.012269 | −0.029343 | −0.025105 | 0.01065 | 0.005903 | −0.031718 | 0.007568 | −0.047386 | 0.022991 | 0.025988 | −0.025579 | −0.058787 | −0.013391 |
| 73 | 0.062303 | 0.032334 | −0.011285 | −0.03096 | −0.006958 | 0.080959 | 0.067579 | 0.013393 | −0.035439 | 0.051969 | 0.145947 | 0.060712 | −0.00674 | −0.046414 |
| 74 | 0.0811741 | −0.007626 | 0.039404 | 0.013955 | 0.046902 | −0.067727 | −0.033508 | −0.024409 | 0.034878 | −0.011283 | 0.006627 | −0.019482 | −0.006149 | 0.055132 |
| 75 | 0.003239 | −0.01737 | 0.047419 | 0.043538 | 0.043192 | 0.057588 | −0.023587 | −0.155278 | 0.008532 | −0.015873 | −0.035352 | −0.077741 | −0.019557 | 0.00768 |
| 76 | −0.027893 | 0.016349 | 0.013623 | −0.032186 | −0.036317 | 0.104516 | 0.066745 | −0.090922 | −0.082397 | −0.036663 | 0.026587 | 0.007413 | 0.066877 | 0.052317 |
| 77 | 0.062419 | −0.008851 | −0.04818 | −0.069524 | −0.02702 | −0.007501 | −0.034166 | 0.088086 | 0.073039 | −0.015072 | 0.00761 | 0.044524 | −0.008658 | −0.021678 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 78 | 0.006438 | −0.051133 | −0.030553 | −0.048138 | −0.012309 | −0.030117 | −0.037522 | −0.041707 | 0.008228 | 0.03078 | 0.027101 | −0.030862 | −0.059151 | −0.002574 |
| 79 | −0.008539 | −0.02551 | −0.054377 | 0.052406 | 0.070833 | −0.001737 | 0.026897 | 0.00304 | −0.025418 | 0.017687 | 0.039052 | 0.004195 | 0.02094 | −0.029597 |
| 80 | −0.045539 | 0.0229 | −0.000193 | −0.037747 | −0.032576 | −0.015729 | 0.026085 | −0.040555 | −0.021641 | 0.027907 | 0.022397 | −0.002398 | 0.012113 | 0.001119 |
| 81 | 0.004927 | −0.002271 | −0.061881 | −0.014753 | 0.033437 | 0.009475 | 0.025427 | 0.05224 | 0.044519 | 0.073242 | 0.017798 | 0.008951 | 0.031248 | 0.013446 |
| 82 | 0.011719 | −0.013813 | −0.051061 | −0.033112 | −0.042954 | −0.041045 | −0.028182 | 0.054791 | 0.036309 | −0.012275 | 0.016572 | 0.047447 | −0.021494 | 0.011522 |
| 83 | 0.017705 | 0.012305 | 0.00414 | 0.004356 | 0.00287 | −0.005959 | 0.071398 | −0.02405 | −0.029285 | 0.042666 | 0.035784 | −0.077144 | 0.007409 | 0.011771 |
| 84 | −0.075924 | 0.011215 | −0.033871 | −0.023537 | −0.011744 | 0.007588 | −0.006184 | 0.032262 | 0.079697 | 0.031949 | 0.027602 | −0.007389 | 0.097003 | 0.00961 |
| 85 | −0.039364 | −0.082793 | 0.022234 | 0.04691 | 0.025191 | 0.01558 | −0.014391 | 0.001261 | 0.035284 | −0.059186 | −0.001231 | 0.038865 | −0.023705 | 0.009381 |
| 86 | 0.030602 | 0.042842 | 0.021233 | −0.01518 | −0.027991 | −0.052822 | −0.058224 | −0.045318 | 0.039971 | 0.004577 | −0.031918 | −0.001098 | 0.078412 | 0.069307 |
| 87 | 0.047147 | −0.023901 | −0.004499 | −0.022902 | −0.064214 | 0.042051 | −0.002889 | −0.043214 | −0.003251 | 0.002605 | 0.018458 | 0.022762 | −0.006233 | −0.017612 |
| 88 | −0.023933 | −0.09859 | 0.039086 | 0.01434 | 0.015014 | −0.005888 | −0.085973 | 0.02034 | 0.123821 | 0.038442 | −0.002892 | −0.061452 | −0.023805 | 0.035203 |
| 89 | −0.028126 | −0.00133 | −0.027954 | 0.054737 | 0.03439 | −0.082546 | −0.04086 | −0.013201 | −0.08703 | −0.009965 | 0.068446 | 0.075164 | 0.042555 | 0.069904 |
| 90 | −0.0002021 | 0.0158321 | −0.072461 | −0.040652 | 0.040751 | 0.097014 | 0.00601 | 0.011699 | 0.048632 | 0.050198 | −0.047922 | 0.019405 | −0.002089 | −0.040041 |
| 91 | −0.006567 | −0.028346 | −0.013504 | −0.042826 | −0.000808 | 0.013268 | 0.008749 | −0.032441 | −0.048799 | −0.017972 | 0.000832 | 0.014281 | −0.00256 | −0.083814 |
| 92 | −0.065874 | −0.019912 | −0.004113 | 0.006739 | −0.025933 | 0.015819 | −0.061926 | −0.072042 | −0.033644 | 0.001289 | −0.027877 | −0.006945 | −0.004189 | 0.034974 |
| 93 | −0.001079 | 0.083089 | −0.011503 | −0.005322 | 0.027055 | −0.029113 | 0.043987 | 0.050248 | 0.086189 | 0.006305 | −0.129064 | −0.004646 | 0.075622 | 0.0559 |
| 94 | −0.106465 | 0.053215 | 0.010241 | −0.005165 | 0.021647 | 0.034414 | 0.100237 | 0.02809 | 0.009665 | −0.02996 | −0.053274 | 0.0145621 | −0.007558 | −0.057806 |
| 95 | 0.05092 | −0.029247 | 0.011501 | 0.033493 | 0.021976 | −0.005408 | 0.093914 | 0.056912 | 0.019104 | −0.014101 | −0.012408 | −0.007829 | 0.037007 | 0.056196 |
| 96 | −0.002108 | −0.022344 | −0.035906 | −0.009258 | 0.027081 | −0.067703 | −0.066435 | 0.051508 | 0.03007 | 0.031156 | 0.03067 | 0.014751 | 0.024784 | 0.017012 |
| 97 | −0.025241 | 0.04261 | 0.072193 | 0.022916 | 0.027091 | 0.004431 | 0.041262 | 0.035812 | −0.020849 | 0.026228 | 0.035858 | 0.059975 | −0.019811 | −0.032915 |
| 98 | −0.032352 | −0.01991 | −0.077123 | −0.028447 | 0.009077 | 0.055747 | 0.056515 | −0.003505 | −0.030464 | −0.000541 | 0.043294 | −0.021497 | −0.060503 | −0.056057 |
| 99 | −0.041742 | 0.007054 | 0.039561 | 0.053804 | 0.094518 | −0.065939 | −0.049991 | 0.029156 | −0.008042 | 0.045573 | 0.036557 | 0.075597 | 0.075421 | 0.030199 |
| 100 | 0.003623 | 0.0361171 | 0.008085 | 0.034162 | 0.018928 | 0.01817 | 0.029332 | −0.014577 | −0.011228 | −0.007057 | −0.002717 | −0.014223 | 0.011926 | 0.028675 |
| 101 | 0.008789 | 0.012053 | −0.013821 | −0.021838 | −0.003932 | 0.005852 | 0.01638 | 0.017959 | −0.011457 | 0.010612 | 0.017017 | 0.004783 | −0.001044 | 0.002162 |
| 102 | −0.020912 | −0.026947 | 0.013198 | −0.021136 | −0.025532 | 0.023433 | 0.005856 | −0.038472 | −0.011561 | −0.010794 | −0.038112 | −0.005785 | −0.007197 | 0.014733 |
| 103 | −0.052315 | −0.030081 | 0.040017 | −0.010356 | −0.023771 | 0.01328 | 0.012352 | −0.05967 | −0.041585 | −0.029363 | −0.017858 | 0.000862 | 0.001608 | −0.001283 |
| 104 | −0.016657 | 0.030066 | −0.015923 | −0.019985 | −0.006334 | −0.015503 | 0.012198 | 0.029532 | 0.00872 | 0.000347 | −0.038379 | −0.018629 | 0.016653 | 0.020439 |
| 105 | 0.004495 | −0.003446 | 0.009862 | −0.000849 | 0.034298 | −0.018899 | 0.010803 | −0.048005 | 0.026269 | 0.001604 | −0.011731 | −0.026286 | 0.006576 | 0.026663 |
| 106 | −0.019517 | 0.008874 | 0.030328 | 0.030446 | −0.010615 | −0.012165 | −0.010748 | 0.017995 | −0.001286 | −0.013547 | −0.062704 | 0.026873 | −0.012977 | −0.003229 |
| 107 | −0.005228 | −0.013954 | 0.030465 | −0.023943 | −0.03121 | 0.015418 | −0.011932 | 0.019891 | −0.001793 | 0.016458 | −0.034368 | 0.007111 | −0.028464 | −0.034384 |
| 108 | 0.012324 | −0.054478 | −0.020469 | −0.01029 | 0.027458 | 0.027373 | 0.006537 | 0.001673 | 0.034559 | 0.029594 | −0.013783 | 0.035101 | 0.008367 | −0.035233 |
| 109 | −0.033233 | 0.020788 | −0.003098 | −0.012071 | −0.004894 | 0.013332 | −0.003291 | −0.000176 | −0.007177 | 0.041019 | 0.029009 | 0.006722 | 0.025236 | 0.01557 |
| 110 | 0.126078 | 0.044722 | 0.005906 | −0.001278 | −0.020136 | 0.004853 | −0.020128 | 0.070547 | 0.083152 | 0.011178 | −0.049174 | −0.017637 | 0.016977 | 0.025675 |
| 111 | 0.008289 | −0.02696 | 0.01306 | −0.009653 | −0.027229 | −0.027229 | −0.015751 | −0.018958 | 0.03971 | 0.004176 | −0.012825 | −0.021003 | −0.01979 | −0.034135 |
| 112 | 0.024539 | −0.01139 | 0.009342 | 0.015837 | 0.00675 | 0.024291 | 0.023583 | −0.010646 | −0.004687 | 0.019177 | 0.008779 | 0.034396 | 0.018412 | 0.01063 |
| 113 | 0.001111 | −0.04329 | −0.013716 | −0.001715 | −0.003976 | −0.022103 | −0.024921 | −0.033814 | 0.037153 | −0.007102 | −0.011068 | 0.003019 | −0.026784 | 0.005296 |
| 114 | −0.023105 | −0.01319 | −0.017366 | −0.0508 | −0.025775 | 0.004386 | −0.001661 | 0.028213 | −0.000569 | 0.001898 | −0.01738 | 0.039717 | −0.008184 | −0.025707 |
| 115 | 0.031743 | 0.0203291 | 0.047766 | −0.005958 | −0.015328 | −0.010409 | 0.006796 | 0.014102 | 0.021608 | −0.003163 | −0.003835 | 0.002362 | −0.00898 | −0.005222 |
| 116 | −0.047441 | −0.020273 | 0.014349 | −0.001197 | −0.019103 | −0.025107 | −0.033448 | 0.013 | −0.007329 | −0.015112 | −0.000734 | 0.0239 | −0.013537 | −0.030474 |
| 117 | −0.025528 | 0.013916 | −0.00349 | 0.023945 | 0.029822 | −0.015801 | 0.008017 | −0.017372 | 0.022809 | 0.002064 | −0.000516 | −0.015188 | 0.015456 | 0.015849 |
| 118 | 0.012827 | 0.013525 | −0.053865 | −0.029813 | 0.013765 | 0.042837 | 0.023203 | 0.005666 | 0.015728 | −0.000323 | 0.038379 | −0.003564 | 0.000532 | −0.016382 |
| 119 | −0.003252 | 0.040245 | 0.020955 | 0.012291 | 0.007573 | 0.008739 | 0.023047 | −0.025122 | −0.018726 | 0.017668 | 0.042866 | 0.005563 | 0.027484 | 0.009931 |
| 120 | −0.022612 | 0.004341 | 0.002201 | 0.014807 | 0.013179 | 0.010915 | 0.012169 | −0.015046 | −0.014365 | −0.004619 | 0.000176 | 0.009507 | −0.010086 | −0.003744 |
| 121 | 0.007395 | 0.00369 | 0.031185 | 0.019007 | 0.00121 | −0.018211 | −0.011082 | −0.022034 | 0.006025 | −0.008139 | −0.004345 | −0.022426 | −0.017998 | 0.011818 |
| 122 | 0.034347 | 0.006039 | −0.015042 | 0.0127 | 0.002948 | −0.001814 | −0.019106 | 0.005513 | −0.017004 | −0.003215 | 0.005477 | 0.009158 | −0.010709 | −0.014255 |
| 123 | 0.037222 | 0.01588 | 0.013534 | −0.001937 | −0.006845 | −0.03426 | −0.007361 | 0.028741 | 0.015795 | 0.001419 | 0.024416 | −0.003101 | −0.005312 | −0.013125 |
| 124 | 0.032398 | 0.009097 | 0.018128 | 0.018623 | 0.012004 | 0.013923 | 0.005473 | 0.004936 | −0.001935 | 0.012723 | 0.032426 | 0.001848 | 0.006563 | 0.020561 |
| 125 | −0.006545 | −0.034855 | −0.01729 | −0.002199 | 0.0067 | 0.025058 | 0.027636 | 0.010285 | 0.023678 | −0.0113 | 0.000892 | −0.019546 | −0.019116 | −0.024364 |
| 126 | 0.016327 | −0.002814 | 0.015602 | 0.006615 | −0.00911 | −0.040099 | −0.054433 | −0.008048 | 0.003514 | −0.017622 | 0.022475 | −0.012802 | −0.011189 | 0.019204 |
| 127 | 0.034633 | 0.017731 | 0.00855 | 0.005721 | −0.004291 | 0.003131 | 0.000368 | 0.004479 | −0.011867 | 0.000805 | 0.026007 | −0.006642 | 0.010428 | 0.023791 |
| 128 | −0.012546 | 0.013981 | 0.032797 | 0.018164 | −0.010482 | −0.005926 | 0.023544 | 0.017067 | 0.006435 | −0.027222 | −0.015904 | 0.015085 | 0.009681 | −0.012622 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 129 | 0.051302 | 0.016548 | −0.017443 | 0.03392 | 0.019116 | 0.017222 | 0.01828 | 0.034885 | 0.013246 | −0.017136 | −0.001637 | −0.009092 | −0.01316 | 0.000873 |
| 130 | −0.025998 | 0.020029 | −0.001534 | −0.004091 | −0.001738 | 0.039213 | 0.031211 | −0.022408 | −0.020769 | 0.006925 | 0.044405 | 0.008887 | 0.01218 | −0.020157 |
| 131 | 0.0009891 | −0.010111 | 0.0203961 | 0.012833 | 0.011271 | −0.044549 | −0.036168 | −0.008247 | −0.001052 | −0.008485 | 0.010959 | −0.023882 | −0.007027 | −0.00368 |
| 132 | −0.013292 | −0.030525 | 0.016879 | −0.02167 | −0.004518 | 0.021469 | 0.019074 | 0.007946 | 0.019595 | 0.024792 | −0.02806 | 0.006267 | −0.018113 | −0.062174 |
| 133 | −0.028884 | 0.007794 | 0.031394 | 0.003791 | −0.018693 | 0.026392 | 0.000295 | −0.02126 | 0.030917 | 0.001791 | −0.000487 | −0.018346 | 0.002631 | 0.021941 |
| 134 | 0.020617 | −0.013684 | −0.027613 | −0.037052 | −0.029259 | 0.025582 | −0.020289 | −0.035971 | 0.011251 | 0.002504 | 0.023149 | −0.003021 | 0.016361 | −0.013614 |
| 135 | −0.048503 | 0.000966 | 0.016011 | 0.026444 | 0.018595 | −0.015746 | −0.016771 | 0.000847 | −0.001793 | −0.000398 | −0.00966 | 0.007239 | 0.004495 | −0.008401 |
| 136 | −0.020592 | −0.005473 | −0.023815 | −0.004317 | −0.002958 | 0.011009 | −0.009743 | 0.010756 | 0.029152 | 0.015258 | 0.016896 | −0.030312 | −0.017206 | 0.00463 |
| 137 | 0.0081 | 0.01248 | 0.015009 | −0.016096 | −0.023466 | 0.011483 | 0.012049 | −0.015166 | −0.014381 | −0.039219 | −0.008406 | −0.0085 | −0.00238 | 0.011723 |
| 138 | −0.006181 | 0.000923 | −0.021779 | 0.004584 | 0.034559 | −0.016897 | −0.014393 | −0.002232 | −0.007937 | 0.000519 | −0.014934 | −0.004467 | 0.008682 | 0.0053 |
| 139 | −0.032496 | −0.002499 | −0.010092 | −0.019254 | −0.011131 | 0.029389 | −0.03231 | −0.07567 | −0.063101 | 0.054254 | 0.022472 | −0.034252 | −0.045246 | −0.001564 |
| 140 | −0.032822 | 0.023835 | −0.030058 | 0.00749 | 0.020614 | −0.005851 | −0.027403 | −0.021014 | 0.001512 | 0.016912 | −0.050492 | −0.032471 | 0.013054 | 0.000416 |
| 141 | −0.021745 | −0.001004 | −0.006476 | 0.019958 | 0.014995 | −0.015637 | 0.029966 | 0.001067 | −0.002544 | −0.000178 | −0.013221 | 0.005541 | 0.000575 | −0.020621 |
| 142 | −0.049384 | 0.012172 | 0.010904 | 0.015352 | 0.007648 | −0.023802 | 0.008769 | 0.029599 | 0.020781 | 0.007314 | −0.008159 | −0.009863 | 0.014772 | 0.026274 |
| 143 | 0.005718 | −0.022388 | 0.006712 | 0.015062 | 0.006483 | 0.026978 | −0.025234 | 0.010455 | 0.000094 | 0.00531 | −0.040102 | 0.020413 | −0.012751 | 0.005376 |
| 144 | 0.029276 | 0.001947 | 0.002643 | 0.02939 | 0.011677 | −0.01228 | −0.003745 | 0.010878 | 0.030927 | 0.014216 | −0.056349 | −0.024022 | 0.024756 | 0.039729 |
| 145 | −0.03269 | 0.03321 | −0.008199 | −0.031858 | −0.028971 | −0.030496 | −0.039247 | 0.033614 | 0.023789 | 0.018536 | 0.010706 | −0.007411 | −0.004596 | 0.009338 |
| 146 | −0.023214 | 0.002989 | 0.000954 | 0.003609 | 0.001922 | −0.01397 | −0.00372 | 0.003836 | −0.007465 | −0.00768 | −0.009868 | 0.006049 | 0.013553 | −0.007558 |
| 147 | 0.002896 | 0.015199 | −0.006572 | 0.017641 | 0.008197 | −0.021276 | 0.010988 | −0.000357 | 0.004344 | −0.011379 | −0.003456 | 0.030703 | 0.018246 | −0.000767 |
| 148 | 0.016593 | −0.004236 | 0.014106 | 0.014281 | 0.001877 | −0.048339 | −0.049577 | −0.009683 | −0.0023 | −0.02175 | −0.024636 | 0.008592 | 0.003733 | 0.015228 |
| 149 | 0.001804 | −0.01211 | −0.010668 | 0.011055 | 0.012031 | 0.000874 | 0.020669 | 0.015002 | 0.019056 | 0.001202 | 0.002086 | −0.008513 | −0.025056 | −0.009367 |
| 150 | 0.019004 | 0.017511 | −0.025993 | 0.001105 | 0.034106 | 0.042623 | 0.030164 | −0.003584 | −0.052894 | −0.002016 | 0.029069 | −0.009408 | −0.048306 | −0.038187 |
| 151 | 0.010868 | 0.04198 | −0.038817 | −0.033698 | −0.010994 | 0.003072 | 0.026683 | −0.006611 | −0.022533 | −0.001392 | −0.003285 | −0.026855 | −0.00562 | 0.005186 |
| 152 | 0.039121 | −0.009313 | 0.006963 | 0.004424 | 0.002423 | 0.008481 | 0.011343 | −0.023371 | −0.029223 | −0.010901 | 0.018006 | −0.000186 | 0.012401 | 0.029416 |
| 153 | 0.047619 | −0.003428 | −0.004352 | −0.020767 | −0.011165 | 0.012662 | 0.046212 | 0.02047 | −0.026424 | −0.028685 | −0.036372 | 0.02715 | 0.011351 | 0.000679 |
| 154 | 0.011567 | 0.026003 | 0.000445 | −0.002992 | 0.01524 | −0.022566 | 0.006149 | 0.005322 | 0.012121 | −0.015564 | −0.022366 | −0.030823 | 0.02834 | 0.017589 |
| 155 | 0.023995 | −0.011863 | −0.000278 | −0.01317 | 0.00569 | 0.00541 | 0.014578 | 0.018846 | −0.000412 | 0.007843 | −0.0353 | −0.022202 | −0.002165 | −0.009448 |
| 156 | −0.041604 | −0.010259 | 0.004574 | −0.014297 | −0.008711 | −0.053268 | −0.009748 | −0.010062 | −0.042693 | 0.007168 | −0.061117 | −0.004194 | 0.025849 | −0.016047 |
| 157 | −0.040242 | −0.004319 | 0.005969 | 0.013399 | −0.00598 | −0.006877 | −0.021797 | −0.024025 | −0.009235 | −0.003778 | 0.000003 | −0.036992 | −0.030911 | −0.025167 |
| 158 | 0.026644 | 0.002831 | −0.002192 | −0.000571 | 0.004878 | 0.033853 | 0.0319 | −0.038273 | −0.013095 | −0.009881 | 0.009174 | −0.022971 | −0.009721 | 0.021068 |
| 159 | −0.011689 | 0.03361 | −0.038021 | 0.010498 | 0.010541 | 0.004356 | 0.024624 | 0.043554 | 0.00289 | 0.017909 | 0.036355 | −0.030064 | 0.016203 | 0.023241 |
| 160 | 0.009678 | 0.017664 | 0.001997 | −0.035773 | 0.000337 | −0.004534 | 0.027817 | −0.00678 | −0.00697 | −0.009841 | −0.012317 | 0.00323 | −0.018255 | −0.012315 |
| 161 | −0.045743 | −0.019583 | 0.016534 | 0.00179 | −0.029897 | 0.001899 | −0.018932 | 0.013611 | −0.018232 | 0.02958 | 0.041596 | 0.016518 | −0.033174 | −0.001359 |
| 162 | −0.015374 | 0.00838 | −0.02327 | 0.019073 | 0.049346 | −0.023256 | 0.006535 | 0.011244 | 0.009514 | −0.011819 | 0.020285 | −0.014829 | 0.034322 | 0.024848 |
| 163 | −0.0334 | −0.009537 | 0.03606 | 0.040219 | 0.009368 | −0.012742 | −0.024057 | 0.012434 | −0.005345 | −0.010568 | −0.013759 | 0.009058 | −0.024743 | −0.025869 |
| 164 | −0.003177 | −0.039659 | −0.022926 | −0.007282 | 0.006887 | −0.002166 | 0.012265 | −0.010171 | 0.001447 | −0.015767 | −0.000897 | −0.028532 | −0.016007 | −0.005236 |
| 165 | −0.007937 | −0.033956 | 0.001441 | −0.028442 | −0.010885 | −0.00035 | −0.000973 | 0.025357 | 0.008675 | −0.037428 | −0.008372 | 0.018769 | −0.01443 | −0.032288 |
| 166 | −0.00003 | −0.054709 | −0.027105 | −0.006048 | 0.011429 | 0.001488 | 0.004281 | −0.018517 | 0.005931 | 0.002823 | 0.005633 | 0.003194 | −0.011891 | −0.015198 |
| 167 | 0.017244 | −0.029424 | −0.024215 | 0.009048 | 0.02404 | −0.005508 | −0.00296 | 0.012542 | 0.044297 | 0.009368 | −0.053944 | 0.015699 | −0.023079 | −0.030546 |
| 168 | −0.025109 | −0.001451 | 0.028183 | 0.031637 | 0.001613 | 0.020045 | −0.067188 | 0.009938 | 0.03595 | −0.021156 | −0.016544 | 0.011295 | −0.003082 | 0.019336 |
| 169 | −0.015147 | −0.01769 | −0.01181 | 0.021324 | 0.016167 | −0.014384 | −0.014122 | 0.002116 | 0.00277 | 0.015616 | 0.00067 | −0.005067 | −0.003043 | 0.013798 |
| 170 | 0.00643 | −0.011379 | −0.023796 | −0.004979 | 0.012258 | −0.014971 | −0.002164 | 0.011705 | −0.003301 | 0.023491 | 0.016597 | −0.006342 | 0.014766 | 0.017405 |
| 171 | −0.002232 | −0.005949 | −0.002752 | 0.024689 | 0.014879 | −0.011623 | −0.010022 | −0.005693 | 0.004135 | 0.013653 | −0.006621 | −0.004183 | −0.001626 | 0.008458 |
| 172 | −0.026995 | −0.003384 | 0.009908 | 0.040986 | 0.021118 | 0.005111 | 0.01855 | −0.014395 | 0.013364 | 0.001314 | −0.000304 | −0.001966 | −0.008843 | 0.010596 |
| 173 | −0.010015 | 0.032675 | 0.031756 | 0.036016 | 0.014724 | −0.004685 | 0.046239 | 0.000843 | 0.013623 | −0.010278 | 0.01131 | −0.007484 | 0.00513 | 0.007044 |
| 174 | −0.019059 | −0.001165 | 0.031702 | 0.015388 | −0.001167 | −0.009201 | −0.012394 | 0.000169 | 0.011627 | 0.024741 | −0.016968 | −0.000477 | −0.002087 | −0.004789 |
| 175 | 0.009755 | −0.021492 | −0.012247 | 0.005872 | 0.012603 | −0.004436 | −0.033992 | −0.049896 | −0.00692 | 0.061642 | 0.032397 | −0.022038 | −0.004199 | 0.025041 |
| 176 | 0.00896 | −0.063253 | −0.01469 | 0.013595 | 0.003172 | 0.018337 | −0.020955 | −0.026562 | 0.021007 | 0.003179 | −0.0086 | −0.019952 | −0.048422 | 0.00872 |
| 177 | −0.033419 | −0.022149 | −0.033675 | −0.024677 | 0.01785 | 0.017359 | −0.050466 | −0.010806 | −0.021954 | 0.003382 | 0.00616 | 0.002574 | −0.032303 | −0.039943 |
| 178 | −0.011808 | 0.023006 | 0.018675 | 0.009651 | −0.011115 | −0.000808 | −0.017458 | −0.00434 | −0.027802 | −0.012139 | −0.02187 | 0.001183 | −0.014272 | 0.023711 |
| 179 | −0.000446 | 0.005612 | 0.011409 | −0.0003 | −0.00221 | −0.008316 | −0.010823 | 0.015333 | 0.007718 | −0.007906 | −0.023497 | 0.01032 | 0.004706 | −0.003978 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 180 | 0.012839 | 0.005455 | −0.002399 | −0.007568 | −0.004707 | 0.00111 | 0.018079 | 0.004548 | 0.000259 | −0.014135 | −0.011768 | 0.000233 | −0.000532 | −0.001287 |
| 181 | 0.013536 | 0.013155 | −0.000081 | −0.01439 | −0.005136 | 0.011158 | 0.018809 | −0.000395 | −0.006419 | 0.002605 | −0.019518 | −0.005837 | 0.00317 | −0.001923 |
| 182 | 0.030385 | 0.018629 | −0.009691 | −0.004829 | 0.008342 | 0.032151 | 0.026225 | −0.022696 | 0.007832 | 0.013791 | −0.002645 | −0.031058 | 0.014382 | 0.02142 |
| 183 | 0.022423 | 0.003831 | 0.012375 | 0.009667 | −0.001741 | 0.009748 | 0.004629 | −0.008302 | 0.008432 | −0.017841 | −0.019608 | −0.006256 | −0.001812 | −0.018064 |
| 184 | −0.00307 | −0.013237 | 0.027984 | −0.00908 | −0.035867 | 0.015411 | 0.02589 | 0.017941 | −0.015078 | −0.02108 | −0.03209 | 0.024353 | −0.033898 | −0.059328 |
| 185 | −0.022143 | −0.004319 | 0.026567 | 0.021577 | 0.001411 | −0.009931 | −0.022916 | −0.032256 | −0.014443 | −0.015494 | −0.065492 | −0.023864 | −0.015421 | −0.000643 |
| 186 | 0.004381 | −0.000317 | 0.007151 | 0.005808 | −0.001601 | 0.00179 | −0.009683 | −0.032835 | −0.051215 | 0.002963 | 0.031721 | 0.003433 | −0.000895 | −0.001724 |
| 187 | −0.007301 | 0.0222 | −0.007241 | 0.008503 | 0.008717 | 0.011189 | 0.030445 | −0.005788 | 0.00508 | −0.038594 | 0.01568 | −0.004871 | 0.015931 | 0.015505 |
| 188 | −0.015281 | 0.010436 | −0.002805 | 0.000137 | 0.004556 | 0.006062 | 0.01061 | 0.005149 | −0.000115 | −0.011543 | −0.036426 | 0.003999 | 0.008908 | −0.003486 |
| 189 | 0.005514 | 0.0172 | −0.020797 | −0.007411 | 0.015441 | −0.003999 | −0.021687 | −0.009674 | −0.007493 | 0.025669 | −0.012321 | −0.001794 | 0.022691 | 0.002701 |
| 190 | 0.030807 | −0.034239 | −0.014846 | −0.015825 | −0.004011 | −0.002937 | 0.019156 | −0.000115 | 0.018858 | 0.006473 | 0.052199 | 0.001473 | −0.029658 | −0.01596 |
| 191 | −0.010006 | −0.002743 | 0.000201 | −0.012129 | 0.007355 | −0.01256 | 0.008155 | −0.009318 | −0.005099 | 0.007845 | 0.032351 | 0.002357 | 0.013835 | 0.001454 |
| 192 | −0.002678 | 0.044174 | −0.015336 | −0.003662 | 0.007187 | 0.016832 | −0.017016 | −0.003728 | 0.02832 | 0.033294 | −0.021198 | −0.02422 | 0.039492 | 0.041283 |
| 193 | −0.026261 | −0.004408 | 0.015953 | 0.013627 | 0.012641 | 0.017825 | 0.026084 | −0.019902 | 0.011971 | 0.010621 | −0.015611 | −0.000775 | 0.034166 | 0.005994 |
| 194 | 0.032166 | −0.021434 | 0.004392 | −0.008377 | 0.000746 | −0.012359 | 0.005028 | 0.020067 | −0.003168 | −0.015879 | −0.011114 | 0.030548 | −0.025145 | −0.019996 |
| 195 | 0.033773 | −0.014008 | 0.014579 | −0.017879 | −0.019073 | −0.008172 | −0.014524 | 0.037761 | 0.03326 | 0.009164 | 0.017983 | −0.003231 | −0.023156 | −0.03711 |
| 196 | 0.022845 | −0.017802 | −0.002738 | −0.002916 | −0.006136 | 0.009967 | −0.011781 | 0.016067 | 0.007331 | 0.029793 | 0.006259 | −0.000054 | −0.028661 | −0.025393 |
| 197 | 0.006968 | −0.024022 | −0.010052 | −0.01156 | −0.000975 | −0.000296 | 0.024516 | 0.002757 | 0.014899 | 0.01519 | 0.036045 | 0.003342 | 0.013273 | −0.000967 |
| 198 | 0.017436 | −0.005296 | −0.007938 | −0.011416 | −0.02908 | 0.012327 | −0.013728 | 0.01381 | −0.007841 | −0.026169 | 0.01862 | 0.046103 | −0.006448 | −0.008947 |
| 199 | 0.005565 | 0.001209 | −0.002472 | −0.02406 | −0.025216 | −0.028656 | 0.007331 | 0.003902 | 0.008079 | 0.030735 | 0.005338 | 0.006572 | 0.008076 | 0.013699 |
| 200 | −0.012527 | 0.003665 | 0.008132 | 0.015305 | 0.016199 | 0.036163 | 0.006557 | −0.017318 | 0.014051 | 0.003525 | −0.014046 | −0.007645 | −0.002016 | −0.005966 |
| 201 | 0.031558 | 0.013235 | −0.021302 | −0.033461 | −0.03846 | −0.001492 | −0.015008 | −0.016876 | −0.037123 | −0.015383 | 0.011831 | 0.011664 | −0.010791 | −0.012962 |
| 202 | 0.010488 | 0.030891 | 0.011567 | −0.004063 | −0.01058 | −0.036421 | −0.018616 | 0.004703 | −0.020638 | 0.01345 | 0.023669 | 0.03353 | 0.032526 | 0.019019 |
| 203 | 0.020155 | 0.008232 | −0.001699 | 0.619549 | −0.00497 | 0.010908 | 0.002536 | −0.020187 | −0.004014 | −0.046198 | −0.002129 | 0.004219 | −0.011772 | 0.005906 |
| 204 | 0.008557 | −0.012916 | 0.028162 | 0.009647 | 0.000428 | −0.038937 | −0.014512 | 0.009385 | −0.014169 | −0.017297 | 0.020079 | 0.028308 | −0.010034 | −0.038804 |
| 205 | 0.018026 | −0.025502 | 0.013953 | 0.005723 | 0.004656 | −0.001081 | 0.02405 | −0.029582 | 0.000833 | −0.001401 | 0.013775 | −0.01091 | −0.032251 | −0.020628 |
| 206 | −0.017444 | −0.017763 | −0.002173 | 0.005592 | 0.020003 | −0.017551 | 0.002801 | −0.005532 | 0.016311 | −0.01604 | 0.002639 | 0.001558 | 0.002787 | −0.003631 |
| 207 | 0.010386 | −0.022274 | 0.008277 | 0.007782 | −0.003699 | 0.00773 | 0.019115 | −0.012922 | −0.015729 | 0.020623 | −0.018245 | 0.002377 | 0.013878 | −0.012024 |
| 208 | −0.036459 | 0.005597 | −0.014677 | −0.005346 | −0.004324 | −0.019035 | 0.000895 | 0.008688 | 0.00431 | −0.006547 | 0.010637 | 0.012147 | 0.039726 | 0.03164 |
| 209 | −0.02454 | −0.01644 | −0.015125 | −0.005751 | −0.00743 | 0.016937 | 0.007413 | −0.015395 | 0.021562 | 0.022532 | −0.020095 | 0.001103 | 0.003861 | −0.006525 |
| 210 | 0.049645 | −0.050285 | 0.005597 | −0.000105 | −0.005221 | 0.025779 | 0.025221 | −0.008337 | −0.002577 | −0.007205 | 0.006856 | −0.011848 | −0.033248 | 0.001295 |
| 211 | −0.048976 | 0.012557 | 0.034672 | 0.016374 | −0.01664 | −0.005007 | 0.012187 | −0.006635 | −0.008942 | −0.023255 | −0.001794 | 0.022916 | 0.000157 | −0.013472 |
| 212 | 0.049714 | 0.006949 | −0.001216 | −0.006811 | −0.012047 | 0.032145 | 0.002807 | 0.001712 | 0.01293 | 0.023553 | 0.022942 | 0.005418 | −0.007431 | −0.004545 |
| 213 | −0.005626 | 0.010661 | −0.00732 | 0.004948 | −0.013158 | 0.004762 | −0.008495 | −0.030591 | −0.011895 | −0.001994 | −0.017678 | 0.014207 | −0.008137 | 0.003348 |
| 214 | 0.002745 | 0.025388 | 0.000935 | −0.007935 | −0.005226 | −0.004506 | 0.004839 | 0.042259 | 0.014703 | −0.004949 | −0.017364 | −0.000708 | −0.001278 | −0.005607 |
| 215 | −0.037905 | 0.029724 | 0.019949 | 0.016078 | 0.012816 | 0.030804 | 0.034724 | −0.008543 | −0.018628 | −0.003237 | −0.039722 | −0.015035 | −0.017759 | −0.032944 |
| 216 | 0.018624 | −0.014241 | 0.01593 | −0.001283 | −0.020225 | −0.001868 | −0.012068 | −0.019379 | −0.05083 | 0.018399 | 0.009948 | −0.003765 | −0.015939 | 0.000815 |
| 217 | 0.032626 | 0.021525 | −0.002538 | 0.024093 | 0.027876 | −0.007485 | 0.038565 | 0.013683 | −0.000332 | 0.015639 | 0.029448 | 0.018201 | 0.008344 | −0.013795 |
| 218 | 0.010071 | 0.010771 | 0.011498 | 0.009271 | 0.006373 | 0.006079 | −0.005235 | 0.002374 | −0.002243 | 0.03472 | −0.006192 | −0.011511 | −0.002952 | −0.012664 |
| 219 | −0.029744 | 0.005056 | 0.017481 | −0.048259 | −0.044782 | −0.013397 | −0.004338 | 0.013587 | −0.026367 | 0.043038 | 0.023375 | 0.003871 | −0.02352 | −0.050168 |
| 220 | 0.011767 | −0.004045 | 0.054369 | 0.024809 | 0.027858 | 0.019783 | 0.048745 | −0.015907 | −0.004815 | −0.00049 | 0.026053 | −0.020451 | −0.025984 | −0.059692 |
| 221 | −0.005505 | 0.007214 | 0.044921 | 0.038568 | 0.029707 | −0.007355 | 0.011451 | −0.007806 | −0.022048 | −0.057587 | −0.018023 | 0.010237 | −0.003405 | −0.015622 |
| 222 | 0.010191 | 0.036394 | 0.025374 | 0.018422 | 0.015819 | 0.031418 | 0.023049 | −0.00871 | −0.011156 | 0.016432 | 0.003731 | 0.010637 | 0.007576 | −0.014192 |
| 223 | 0.041042 | 0.002233 | 0.025879 | 0.014967 | 0.014348 | 0.043678 | 0.039397 | −0.003469 | 0.002954 | 0.005132 | 0.004361 | 0.015655 | −0.010017 | −0.01991 |
| 224 | −0.033551 | −0.003038 | 0.017306 | 0.005818 | −0.002806 | 0.001172 | 0.023972 | 0.001329 | −0.008029 | 0.021434 | −0.044273 | −0.017169 | −0.014454 | −0.006157 |
| 225 | −0.034665 | 0.008333 | −0.003462 | −0.004007 | −0.014783 | 0.017104 | 0.027476 | −0.007454 | −0.015042 | 0.002724 | −0.038383 | −0.027389 | −0.01834 | −0.009195 |
| 226 | 0.005229 | 0.017254 | 0.016403 | 0.020091 | 0.006991 | −0.00022 | −0.00684 | 0.017688 | 0.018998 | 0.015907 | 0.041098 | 0.027765 | 0.014313 | 0.002986 |
| 227 | −0.051979 | −0.02374 | 0.001622 | 0.025711 | 0.011751 | 0.009397 | 0.006365 | 0.001508 | 0.012783 | −0.005243 | −0.029663 | −0.007044 | 0.003868 | −0.006086 |
| 228 | −0.049201 | 0.000056 | 0.004286 | −0.001284 | −0.005476 | 0.021091 | −0.03594 | −0.039916 | −0.068651 | 0.030369 | 0.064936 | 0.007835 | 0.008202 | −0.015386 |
| 229 | 0.024545 | 0.02515 | 0.017135 | 0.014003 | 0.019168 | 0.029945 | 0.01177 | −0.005565 | 0.003359 | −0.00825 | 0.001819 | −0.015047 | 0.020436 | 0.005965 |
| 230 | −0.002166 | −0.027652 | 0.048305 | −0.020657 | −0.035843 | 0.020029 | 0.009875 | 0.01483 | −0.006607 | 0.000314 | −0.028211 | 0.0241 | −0.018427 | −0.028758 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 231 | −0.100701 | −0.041162 | 0.004662 | −0.013904 | −0.041627 | −0.022533 | 0.031688 | −0.000782 | 0.028655 | −0.017541 | 0.011883 | 0.029437 | −0.005281 | −0.023012 |
| 232 | 0.004795 | −0.067418 | −0.013216 | −0.004218 | 0.007589 | 0.003756 | −0.006565 | −0.011563 | −0.003131 | −0.019004 | 0.008317 | 0.035278 | 0.01619 | −0.102571 |
| 233 | −0.016925 | −0.001211 | −0.002089 | 0.002727 | −0.012826 | −0.067675 | −0.163994 | −0.069652 | −0.028921 | −0.005592 | −0.033131 | −0.039016 | −0.005918 | 0.009963 |
| 234 | −0.148718 | −0.009547 | 0.011525 | −0.031612 | −0.031451 | −0.04988 | −0.089563 | −0.042916 | −0.020331 | 0.024018 | 0.024565 | −0.026265 | −0.023212 | −0.004816 |
| 235 | 0.747787 | −0.005736 | 0.024214 | −0.00287 | −0.011859 | −0.04274 | −0.042219 | −0.073483 | −0.061806 | 0.007303 | 0.007296 | −0.020015 | −0.006982 | −0.016055 |
| 236 | −0.009361 | 0.841321 | −0.016223 | −0.002107 | −0.001636 | 0.016053 | −0.013181 | −0.052825 | 0.010566 | 0.01325 | −0.015144 | −0.006883 | −0.054497 | −0.054616 |
| 237 | 0.022813 | −0.01381 | 0.850168 | −0.032415 | 0.029376 | 0.037049 | 0.009906 | 0.000999 | 0.013137 | 0.019728 | 0.011538 | −0.030922 | 0.004204 | 0.014296 |
| 238 | −0.009569 | −0.000378 | −0.038906 | 0.866266 | −0.090741 | −0.01273 | −0.00156 | 0.016106 | −0.014006 | 0.029005 | 0.017747 | 0.013878 | −0.002393 | −0.02305 |
| 239 | −0.023563 | −0.001841 | 0.020934 | −0.099388 | 0.86785 | −0.021373 | −0.018104 | 0.004521 | −0.018997 | 0.0097 | 0.008423 | 0.021564 | −0.012517 | −0.01833 |
| 240 | −0.014388 | 0.008722 | 0.030281 | 0.023386 | 0.017376 | 0.814382 | −0.119754 | 0.036655 | 0.027389 | −0.022987 | −0.018033 | 0.026153 | 0.026723 | 0.021925 |
| 241 | −0.022783 | −0.01505 | 0.01165 | 0.012789 | 0.005959 | −0.115657 | 0.789139 | −0.029888 | 0.008902 | 0.013654 | −0.031506 | −0.010342 | 0.004723 | 0.020241 |
| 242 | −0.081967 | −0.02683 | 0.011022 | 0.012365 | 0.003683 | 0.030375 | −0.015336 | 0.809658 | −0.098021 | 0.004485 | 0.005184 | −0.052429 | −0.003375 | 0.010576 |
| 243 | −0.08245 | 0.020707 | 0.007023 | −0.015292 | −0.020306 | −0.003259 | −0.001114 | −0.094055 | 0.781866 | −0.004281 | 0.028333 | 0.017698 | 0.002118 | −0.011545 |
| 244 | −0.001716 | 0.001314 | 0.017913 | 0019599 | −0.000301 | 0.008051 | 0.019884 | −0.01224 | −0.021152 | 0.880052 | −0.053722 | 0.034256 | 0.021432 | 0.019578 |
| 245 | −0.004612 | −0.019146 | 0.015251 | 0.01207 | −0.006136 | −0.005783 | −0.017116 | 0.009461 | 0.020866 | −0.034647 | 0.817197 | −0.015598 | 0.011193 | 0.012834 |
| 246 | 0.002172 | −0.004356 | −0.010063 | 0.001571 | 0.005446 | 0.001289 | −0.006006 | −0.039892 | 0.019606 | 0.036983 | −0.032636 | 0.863868 | −0.050185 | −0.000538 |
| 247 | −0.000839 | −0.062532 | 0.01998 | −0.021434 | −0.02962 | 0.004898 | −0.012304 | −0.017474 | −0.005957 | 0.0293351 | 0.005182 | −0.049137 | 0.871921 | −0.088026 |
| 248 | −0.062092 | 0.014377 | | −0.030035 | −0.013816 | 0.002739 | 0.012504 | 0.002475 | −0.0184 | 0.015833 | 0.009543 | 0.006772 | −0.081193 | 0.849063 |
| 249 | −0.002184 | −0.014268 | 0.006027 | 0.002555 | 0.002087 | −0.091076 | −0.064298 | 0.033661 | 0.001808 | 0.03091 | 0.000436 | 0.012638 | 0.010518 | −0.039339 |
| 250 | −0.012299 | 0.000739 | 0.012554 | 0.012911 | 0.015049 | −0.12254 | −0.074459 | 0.030576 | 0.034446 | −0.004973 | 0.014402 | −0.001186 | 0.009728 | 0.030381 |
| 251 | −0.056326 | 0.023326 | 0.017987 | 0.010085 | 0.024466 | −0.117173 | −0.074033 | −0.003501 | −0.014754 | −0.036574 | −0.010885 | 0.027369 | 0.038753 | 0.027628 |
| 252 | −0.044706 | −0.017126 | 0.022822 | 0.013914 | −0.020285 | −0.026078 | −0.055187 | −0.056832 | −0.07884 | −0.01993 | −0.053596 | 0.032929 | 0.025373 | 0.008108 |
| 253 | −0.012751 | −0.01532 | 0.0111121 | 0.044134 | 0.034092 | 0.021774 | −0.005005 | −0.040178 | −0.086874 | −0.000153 | −0.014382 | 0.009244 | 0.0155411 | 0.015112 |
| 254 | 0.0064761 | −0.008714 | 0.013364 1 | −0.006359 | −0.010641 | 0.020505 | 0.012069 | −0.023228 | −0.014833 | −0.031938 | −0.015163 | 0.002106 | 0.004006 | 0.008415 |
| 255 | −0.024099 | 0.005743 | 0.037732 | 0.023264 | 0.018673 | −0.014063 | −0.007703 | −0.031202 | −0.039155 | −0.070774 | −0.0248 | −0.002483 | 0.003314 | 0.024318 |
| 256 | 0.001504 | −0.011428 | 0.046491 | 0.030428 | 0.025025 | 0.01261 | −0.016565 | 0.026235 | 0.007827 | −0.010432 | −0.100062 | −0.016532 | −0.010218 | −0.000559 |
| 257 | −0.005295 | −0.000646 | 0.031337 | 0.01813 | 0.011332 | 0.008087 | −0.004062 | 0.015312 | 0.030022 | 0.025461 | 0.027698 | 0.012582 | 0.00362 | 0.013376 |
| 258 | 0.001912 | −0.038866 | 0.007554 | 0.026895 | 0.020102 | 0.000529 | −0.029317 | 0.007883 | 0.007469 | 0.030821 | 0.010233 | 0.008407 | −0.042569 | −0.029113 |
| 259 | −0.009261 | 0.022471 | 0.001567 | 0.00279 | 0.00858 | −0.028845 | −0.008721 | −0.014248 | −0.045094 | 0.019966 | 0.019203 | 0.016514 | 0.019403 | −0.00291 |
| 260 | −0.031651 | 0.006445 | −0.022654 | 0.012758 | −0.010374 | −0.003162 | −0.002929 | 0.004068 | −0.04567 | −0.006532 | 0.025962 | 0.03687 | 0.010907 | −0.013666 |
| 261 | −0.027885 | 0.003941 | −0.016575 | 0.008049 | 0.013579 | −0.043771 | −0.021084 | 0.004545 | −0.012969 | 0.005957 | 0.008651 | 0.01135 | 0.016022 | −0.005072 |
| 262 | −0.0103951 | −0.040936 | −0.007626 | 0.010207 | −0.008179 | 0.032179 | 0.013495 | −0.033596 | 0.008699 | 0.014091 | −0.005748 | −0.010352 | −0.022718 | −0.012054 |
| 263 | −0.035628 | −0.027406 | 0.007326 | 0.009239 | −0.002433 | 0.033865 | 0.025716 | −0.046226 | −0.037721 | 0.0121251 | −0.013709 | 0.010491 | 0.0001041 | −0.01269 |
| 264 | −0.0128721 | 0.0344651 | 0.0054111 | 0.014719 | 0.011898 | −0.008148 | −0.000241 | 0.013939 | −0.011638 | 0.01154 | −0.001625 | 0.002201 | 0.009576 | 0.008292 |
| 265 | 0.021866 | 0.007961 | 0.015728 | −0.01117 | −0.030351 | 0.006779 | 0.005213 | 0.032196 | −0.006566 | 0.004038 | 0.014239 | −0.003132 | −0.022668 | −0.008783 |
| 266 | 0.010248 | −0.000616 | 0.015307 | −0.003261 | −0.017402 | 0.013184 | 0.007059 | 0.030312 | −0.013387 | −0.00617 | −0.010564 | 0.003182 | −0.0251 | −0.005924 |
| 267 | 0.026238 | 0.031079 | 0.021389 | 0.014327 | 0.000162 | −0.016412 | 0.027694 | 0.034442 | 0.020638 | 0.013672 | 0.044546 | 0.025982 | 0.032386 | 0.022628 |
| 268 | −0.001532 | 0.014239 | 0.0224 | 0.027197 | −0.007028 | −0.001653 | −0.009294 | 0.011372 | 0.013258 | 0.009374 | 0.043034 | 0.024431 | 0.006519 | 0.01764 |
| 269 | −0.009022 | 0.0232 | 0.014828 | 0.02947 | 0.029368 | 0.003796 | 0.001629 | 0.011201 | 0.015609 | 0.009337 | 0.051217 | 0.026428 | 0.022716 | 0.005293 |
| 270 | −0.001988 | 0.020009 | 0.018472 | 0.038582 | 0.035706 | −0.005763 | 0.00493 | 0.019446 | 0.013589 | 0.002419 | 0.030846 | 0.031544 | 0.036072 | 0.011184 |
| 271 | −0.020758 | −0.00591 | −0.014614 | 0.006024 | 0.025805 | 0.01492 | −0.001401 | −0.03558 | −0.008004 | 0.013128 | −0.031316 | −0.019357 | 0.012477 | 0.050049 |
| 272 | 0.007413 | 0.030954 | 0.023801 | −0.007833 | 0.0099 | −0.016768 | 0.002026 | 0.024281 | 0.022935 | 0.016894 | 0.029982 | 0.031449 | 0.027726 | 0.016678 |
| 273 | 0.014266 | 0.000195 | 0.040009 | 0.022638 | 0.009077 | −0.003241 | 0.001303 | 0.012054 | 0.005866 | 0.009031 | 0.023326 | 0.032918 | −0.004501 | −0.013647 |
| 274 | 0.010059 | 0.003771 | 0.033292 | 0.022643 | 0.020265 | −0.001177 | 0.000389 | 0.011128 | 0.00965 | 0.009193 | 0.030129 | 0.028003 | −0.000681 | −0.011565 |
| 275 | −0.009985 | −0.038372 | 0.038706 | 0.007327 | 0.007841 | 0.005485 | 0.043356 | 0.033516 | −0.009945 | −0.012278 | −0.026056 | 0.036425 | −0.016641 | −0.047495 |
| 276 | −0.008621 | −0.137412 | −0.004754 | 0.002818 | −0.002319 | 0.013983 | −0.022196 | −0.061378 | 0.008127 | 0.015153 | −0.010826 | −0.007292 | −0.0479 | −0.028149 |
| 277 | 0.000378 | −0.006325 | −0.061467 | 0.004072 | 0.001055 | 0.033932 | 0.015014 | −0.003917 | 0.007837 | 0.002088 | 0.008212 | 0.001198 | 0.004114 | 0.019844 |
| 278 | 0.012444 | 0.009154 | −0.056829 | 0.010254 | 0.001886 | 0.034188 | 0.036598 | 0.002406 | 0.0280121 | −0.011576 | −0.001496 | 0.0029571 | 0.033104 | 0.034354 |
| 279 | −0.023451 | 0.015431 | 0.012011 | −0.105209 | −0.112136 | −0.028214 | 0.003937 | 0.032885 | −0.014713 | 0.008553 | 0.01958 | 0.05154 | 0.022106 | −0.023344 |
| 280 | −0.037678 | 0.021298 | −0.019111 | 0.039451 | 0.036043 | 0.01703 | −0.022088 | −0.101809 | −0.192529 | 0.009423 | 0.001974 | −0.004309 | 0.025079 | 0.045867 |
| 281 | 0.025716 | 0.027427 | 0.022454 | 0.027275 | 0.016061 | −0.020403 | 0.002723 | −0.008487 | −0.014441 | 0.027614 | −0.016399 | −0.069244 | −0.03249 | −0.02433 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 282 | 0.032739 | 0.021734 | 0.047169 | 0.044004 | 0.021112 | −0.007107 | −0.003155 | −0.024751 | −0.021318 | 0.019599 | −0.016628 | −0.057271 | −0.021449 | 0.00297 |
| 283 | −0.012799 | −0.041811 | 0.024361 | −0.009731 | −0.014187 | −0.007373 | 0.010879 | 0.009468 | −0.023736 | 0.017096 | 0.019718 | −0.004289 | −0.086634 | −0.10639 |
| 284 | −0.015903 | 0.006726 | 0.028646 | 0.018426 | 0.013227 | 0.002116 | 0.006148 | 0.017933 | 0.030969 | 0.014818 | 0.02952 | 0.019087 | 0.020647 | 0.021016 |
| 285 | −0.000446 | 0.012665 | 0.031869 | −0.0208 | 0.006247 | 0.02726 | 0.028624 | 0.012841 | 0.02066 | 0.002006 | 0.037902 | 0.016363 | 0.014414 | 0.020778 |
| 286 | 0.036791 | 0.023304 | −0.005203 | 0.019639 | 0.01732 | 0.025927 | −0.005935 | 0.017805 | 0.014709 | 0.004176 | −0.006336 | 0.019818 | 0.013111 | 0.022219 |
| 287 | 0.0418811 | 0.030551 | 0.008651 | 0.036533 | 0.033943 | 0.008497 | −0.011251 | 0.020358 | −0.013013 | −0.000164 | 0.001036 | 0.042402 | 0.03343 | 0.029125 |
| 288 | −0.000937 | −0.027771 | −0.020092 | 0.026079 | 0.034122 | 0.00373 | 0.005785 | 0.015577 | 0.01511 | 0.0186351 | 0.0286541 | 0.0193781 | −0.033594 | −0.043522 |
| 289 | −0.00876 | −0.039606 | 0.001106 | 0.013089 | 0.004837 | 0.020335 | 0.01044 | −0.016022 | 0.012327 | 0.002914 | 0.013505 | −0.013822 | −0.025108 | −0.005845 |
| 290 | 0.009159 | 0.014438 | −0.023787 | −0.006063 | 0.025441 | −0.00504 | 0.026282 | −0.005239 | −0.019289 | 0.000669 | 0.012484 | 0.000847 | −0.007355 | −0.0063 |
| 291 | 0.013457 | 0.016292 | −0.025357 | −0.004331 | 0.024852 | −0.005448 | 0.026122 | −0.007999 | −0.015079 | 0.000969 | 0.011781 | −0.005093 | −0.007196 | 0.000779 |
| 292 | −0.017135 | 0.022442 | −0.023502 | −0.029655 | 0.015629 | −0.017646 | 0.007701 | −0.007102 | −0.015088 | 0.012818 | 0.006707 | −0.012162 | −0.00585 | −0.000891 |
| 293 | 0.017323 | −0.028007 | −0.009418 | 0.022528 | 0.006387 | −0.017292 | 0.018126 | −0.014483 | 0.022973 | 0.020052 | −0.005021 | −0.018949 | −0.013507 | 0.024203 |
| 294 | −0.027894 | −0.001156 | −0.007583 | 0.014881 | −0.002677 | 0.00356 | 0.000834 | −0.006221 | 0.000932 | 0.006239 | −0.006138 | −0.008479 | −0.012456 | 0.000204 |
| 295 | 0.014362 | −0.0072181 | −0.0055781 | −0.006717 | −0.016582 | 0.008837 | 0.025163 | −0.009396 | 0.021093 | 0.014849 | −0.005169 | −0.023784 | −0.012849 | 0.009752 |
| 296 | 0.011691 | 0.015964 | 0.013864 | 0.012121 | 0.01039 | 0.022044 | 0.036003 | 0.002681 | 0.004712 | −0.004209 | −0.008528 | −0.005313 | −0.007281 | −0.007135 |
| 297 | 0.007375 | 0.010479 | 0.017266 | 0.012738 | −0.007809 | −0.007713 | 0.004047 | −0.005571 | 0.031352 | 0.023565 | −0.008765 | −0.012713 | 0.004581 | 0.027708 |
| 298 | −0.021991 | 0.011269 | −0.0115 | 0.005422 | 0.029322 | 0.026126 | 0.012973 | 0.012669 | −0.005027 | 0.001503 | −0.001704 | 0.006651 | 0.02714 | −0.000315 |
| 299 | 0.008569 | −0.018333 | −0.003224 | −0.002757 | −0.019879 | −0.002088 | −0.003123 | 0.023231 | 0.002747 | 0.001319 | 0.004117 | 0.026875 | 0.002957 | 0.010268 |
| 300 | −0.041266 | 0.003367 | −0.026955 | 0.002122 | 0.014871 | 0.010199 | −0.006274 | 0.011424 | −0.024906 | −0.002219 | 0.012918 | 0.020071 | 0.01453 | 0.00371 |
| 301 | −0.015821 | −0.005233 | 0.009247 | 0.000035 | −0.02083 | 0.008978 | 0.026345 | −0.00322 | 0.005737 | 0.002035 | 0.010362 | −0.003281 | 0.009157 | 0.01299 |
| 302 | −0.003962 | 0.01571 | 0.010153 | −0.001725 | −0.018057 | 0.021627 | 0.02523 | 0.020314 | −0.00527f | 0.007448 | 0.008469 | −0.003373 | 0.002177 | 0.009272 |
| 303 | 0.018449 | 0.0009921 | −0.020365 | −0.007212 | −0.022442 | 0.017312 | 0.002571 | 0.0367 | −0.008238 | −0.026583 | −0.016735 | 0.026083 | −0.000558 | 0.016127 |
| 304 | 0.013658 | −0.0024841 | −0.012824 | −0.006403 | −0.011933 | 0.002982 | 0.015495 | 0.047118 | −0.020713 | −0.010691 | −0.020756 | 0.0341111 | −0.001838 | −0.015398 |
| 305 | 0.0286081 | 0.005716 | −0.0230271 | 0.00152 | 0.008207 | 0.028191 | 0.006922 | 0.006884 | 0.044618 | 0.010884 | −0.009015 | −0.032119 | 0.023629 | 0.048782 |
| 306 | 0.001502 | −0.008042 | 0.004922 | 0.012784 | 0.01356 | −0.037226 | −0.000198 | 0.013526 | 0.003852 | 0.006262 | 0.01645 | 0.000294 | −0.009539 | −0.008657 |
| 307 | 0.003842 | 0.015683 | −0.011564 | −0.012236 | 0.010622 | −0.018683 | −0.005178 | 0.004284 | −0.041735 | −0.009911 | −0.038801 | 0.042359 | 0.038911 | 0.027825 |
| 308 | −0.001337 | 0.013398 | 0.017314 | −0.001648 | 0.001149 | −0.003595 | 0.007686 | 0.007226 | −0.012066 | 0.009808 | 0.00968 | 0.016988 | 0.017884 | 0.001591 |
| 309 | −0.004648 | 0.001534 | 0.013551 | −0.007948 | −0.004385 | −0.01212 | 0.014721 | −0.001138 | −0.015845 | 0.016403 | 0.022857 | 0.0076571 | −0.000311 | −0.000324 |
| 310 | −0.012298 | −0.006638 | 0.0110951 | −0.006424 | −0.001517 | 0.001653 | 0.048263 | 0.014419 | 0.007072 | −0.007949 | 0.001965 | 0.000248 | −0.007107 | −0.016103 |
| 311 | 0.027503 | −0.005742 | −0.01383 | 0.013877 | 0.002913 | 0.011608 | −0.003384 | −0.018931 | −0.002427 | −0.006256 | 0.010438 | 0.001386 | −0.005323 | 0.003379 |
| 312 | −0.048004 | 0.033934 | 0.007797 | 0.017185 | 0.019419 | 0.00943 | −0.025089 | −0.023233 | 0.002842 | −0.00724 | −0.011685 | 0.027429 | 0.010602 | 0.013707 |
| 313 | −0.022269 | 0.012032 | 0.016393 | −0.005574 | 0.000133 | 0.018743 | −0.013454 | −0.026077 | −0.004595 | 0.002452 | 0.017024 | −0.003887 | 0.005144 | 0.001579 |
| 314 | 0.007589 | −0.019289 | −0.020447 | 0.001922 | 0.006757 | −0.002065 | −0.002981 | 0.001373 | 0.042864 | −0.001744 | −0.029553 | 0.001018 | 0.008755 | 0.020298 |
| 315 | 0.01546 | 0.004537 | −0.016384 | 0.000549 | 0.013629 | 0.006092 | −0.015454 | −0.006853 | 0.001044 | −0.002647 | 0.01694 | −0.005154 | 0.004503 | 0.020494 |
| 316 | 0.020214 | 0.006969 | 0.004074 | 0.011896 | 0.020863 | 0.035397 | 0.009444 | 0.015245 | −0.024806 | −0.01281 | 0.057711 | 0.014392 | −0.003462 | 0.027803 |
| 317 | −0.011058 | −0.004177 | 0.017834 | 0.008704 | 0.007228 | −0.005074 | 0.045802 | 0.004953 | 0.003235 | 0.004143 | 0.021057 | −0.001936 | 0.000802 | −0.002823 |
| 318 | 0.010551 | −0.029041 | −0.035698 | −0.006068 | 0.011928 | 0.013786 | 0.020099 | −0.003024 | 0.023275 | −0.006088 | 0.000366 | −0.004543 | −0.010618 | −0.017728 |
| 319 | 0.0002581 | 0.003534 | −0.003386 | 0.01066 | 0.012402 | 0.014014 | 0.009479 | −0.002169 | −0.007772 | −0.002616 | 0.0013931 | −0.008871 | −0.000401 | 0.014938 |
| 320 | −0.021684 | 0.0051891 | 0.0414261 | 0.00193 | −0.014229 | −0.006172 | −0.026729 | 0.013615 | −0.005979 | 0.027798 | 0.020938 | −0.002505 | −0.024272 | −0.002811 |
| 321 | 0.012209 | −0.002585 | 0.009137 | 0.019213 | 0.013062 | 0.001472 | −0.033268 | 0.008137 | 0.019553 | 0.013218 | −0.000052 | 0.005973 | 0.022631 | 0.03735 |
| 322 | −0.024238 | −0.013709 | −0.019116 | −0.031066 | −0.024923 | −0.004562 | −0.000156 | −0.017202 | −0.019885 | −0.006598 | 0.011712 | 0.041147 | 0.016404 | 0.017533 |
| 323 | −0.016817 | 0.020516 | −0.0132211 | −0.00018 | 0.010984 | −0.013774 | −0.006154 | 0.002909 | 0.005372 | 0.027449 | 0.004075 | −0.00275 | 0.025128 | 0.023036 |
| 324 | −0.006092 | 0.011244 | 0.044434 | −0.002975 | −0.011142 | −0.011767 | −0.003504 | −0.019287 | −0.019864 | −0.006604 | 0.014893 | 0.012594 | 0.000726 | −0.028803 |
| 325 | 0.012914 | 0.00529 | 0.024579 | 0.005405 | 0.014154 | 0.012523 | 0.008284 | −0.02194 | −0.009386 | 0.015876 | 0.013261 | −0.013716 | −0.005913 | −0.007074 |
| 326 | −0.000025 | −0.028067 | −0.001803 | −0.014062 | −0.002381 | −0.029712 | −0.041301 | 0.002934 | −0.033156 | 0.014474 | −0.010508 | 0.015823 | −0.008135 | −0.027194 |
| 327 | 0.005065 | 0.005449 | −0.004984 | −0.023154 | −0.001659 | 0.011422 | 0.026487 | −0.007594 | 0.000477 | 0.013478 | 0.026648 | −0.0056 | 0.008514 | 0.003387 |
| 328 | 0.012201 | 0.020092 | −0.026283 | 0.000825 | 0.006293 | 0.015905 | −0.0072 | 0.036574 | −0.027409 | 0.026528 | 0.002258 | −0.026624 | −0.008782 | 0.002588 |
| 329 | −0.000561 | 0.003134 | −0.0008091 | −0.013752 | −0.014483 | 0.018179 | 0.006332 | 0.005531 | 0.0016741 | −0.013032 | −0.007803 | 0.0009981 | −0.005141 | −0.002088 |
| 330 | 0.028047 | 0.008608 | −0.004528 | 0.034658 | 0.013642 | 0.000029 | −0.026449 | 0.000752 | 0.0331291 | 0.005061 | −0.022552 | −0.034393 | 0.0037851 | 0.022193 |
| 331 | 0.005381 | 0.006361 | −0.020487 | −0.005164 | 0.006875 | 0.003053 | −0.016824 | −0.020054 | −0.006543 | 0.022429 | 0.018676 | −0.010199 | −0.00092 | 0.015599 |
| 332 | −0.008043 | −0.011529 | 0.012881 | 0.00716 | 0.007046 | −0.012012 | −0.037562 | −0.010597 | −0.003325 | 0.019512 | −0.018331 | −0.017686 | −0.008723 | −0.009101 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 333 | −0.00124 | 0.001794 | 0.009968 | −0.008514 | 0.006858 | −0.00464 | 0.014639 | −0.036311 | −0.016001 | 0.020583 | 0.012006 | −0.019204 | 0.005986 | −0.003356 |
| 334 | −0.041586 | 0.014376 | 0.035335 | 0.001274 | −0.013683 | −0.021224 | −0.032075 | −0.015472 | 0.008266 | 0.00449 | −0.012772 | −0.009621 | −0.038689 | −0.014514 |
| 335 | −0.00469 | 0.003937 | 0.005908 | −0.006149 | 0.011064 | −0.001913 | 0.006876 | 0.004649 | −0.023714 | 0.011428 | 0.002045 | 0.006022 | 0.011886 | −0.00479 |
| 336 | 0.042869 | −0.048275 | −0.06037 | −0.014944 | 0.011593 | 0.007857 | 0.022783 | 0.012448 | −0.018073 | 0.024577 | 0.036808 | 0.002494 | −0.039364 | −0.034417 |
| 337 | −0.03206 | 0.014122 | −0.005724 | −0.019147 | 0.00527 | −0.02054 | 0.003831 | 0.020519 | −0.000019 | −0.017652 | 0.002901 | −0.010725 | −0.0103 | −0.003895 |
| 338 | 0.03821 | −0.03785 | −0.003186 | 0.003152 | 0.006574 | 0.002839 | −0.010914 | 0.014549 | 0.034557 | −0.017983 | −0.029565 | 0.020816 | −0.012342 | −0.005553 |
| 339 | 0.02947 | −0.014491 | −0.018401 | −0.008626 | −0.02367 | 0.000951 | −0.00151 | −0.009253 | 0.00493 | 0.009325 | 0.004609 | 0.008941 | 0.003873 | −0.008456 |
| 340 | 0.041727 | 0.005415 | −0.029255 | 0.008894 | 0.018893 | 0.012971 | −0.014196 | −0.017821 | −0.002827 | −0.007508 | 0.00374 | −0.031065 | −0.026377 | 0.010922 |

| | IP | IQ | IR | IS | IT | IU | IV | IW | IX | IY | IZ | JA | JB | JC |
|---|---|---|---|---|---|---|---|---|---|---|---|---|---|---|
| 1 | 0.0349431 | 0.047988 | −0.028858 | −0.038288 | −0.065809 | 0.072279 | 0.033102 | 0.068704 | 0.0335511 | −0.033961 | −0.002311 | 0.0458921 | −0.086927 | −0.024492 |
| 2 | 0.035856 | 0.011085 | 0.012528 | 0.021233 | 0.031818 | 0.012403 | 0.01281 | 0.00601 | −0.03947 | 0.008271 | 0.010399 | −0.05723 | −0.040926 | 0.010308 |
| 3 | −0.039865 | −0.020902 | −0.019087 | 0.028396 | −0.041048 | 0.01268 | 0.057703 | 0.042374 | −0.043091 | 0.044964 | −0.016103 | 0.017609 | 0.009931 | −0.016871 |
| 4 | 0.046801 | −0.019866 | −0.011695 | 0.082424 | 0.045028 | 0.039651 | −0.030999 | 0.058694 | −0.001276 | 0.015864 | 0.036009 | 0.104095 | 0.00025 | 0.00429 |
| 5 | −0.029959 | −0.036006 | 0.027426 | −0.020408 | −0.007772 | −0.026046 | 0.027026 | 0.03738 | −0.011442 | 0.017466 | −0.048415 | −0.073315 | 0.00827 | 0.010462 |
| 6 | 0.002151 | 0.027998 | 0.030007 | 0.024179 | 0.037206 | −0.032631 | −0.042445 | −0.128909 | 0.021173 | 0.089462 | 0.016988 | 0.083505 | 0.086999 | 0.100876 |
| 7 | 0.011817 | −0.008924 | 0.011157 | −0.004939 | 0.068955 | 0.010453 | 0.010528 | −0.072272 | −0.042168 | −0.019534 | 0.003462 | 0.0157941 | −0.050134 | −0.035859 |
| 8 | 0.0207481 | 0.025318 | −0.0281981 | −0.029877 | −0.015799 | 0.015823 | 0.00139 | 0.032379 | −0.000893 | −0.006784 | −0.02577 | 0.056885 | −0.007945 | −0.008972 |
| 9 | −0.00419 | 0.002514 | 0.008473 | −0.031482 | −0.051608 | 0.008558 | −0.017426 | −0.017953 | −0.003207 | 0.006652 | 0.015753 | 0.022968 | −0.010776 | −0.046797 |
| 10 | −0.05777 | −0.030753 | −0.035976 | 0.009249 | 0.053475 | −0.0261 | −0.025957 | 0.0291 | −0.006296 | −0.066573 | −0.052289 | −0.036325 | −0.020797 | −0.004614 |
| 11 | −0.012587 | 0.029008 | 0.024711 | −0.073285 | −0.022913 | −0.020445 | 0.001902 | −0.044012 | 0.012528 | −0.020325 | −0.023047 | −0.026618 | −0.043213 | −0.023974 |
| 12 | 0.0039721 | −0.029091 | 0.019526 | −0.007154 | 0.020211 | 0.034157 | −0.008351 | −0.115002 | −0.018623 | 0.0162821 | 0.0315171, | 0.0003441 | 0.0060921 | 0.00765 |
| 13 | −0.046353 | 0.006878 | 0.00528 | −0.008594 | 0.037271 | −0.054205 | 0.008058 | −0.043228 | −0.002319 | −0.040113 | 0.010413 | 0.024208 | 0.030655 | 0.014048 |
| 14 | 0.066594 | 0.007451 | 0.041914 | 0.06271 | 0.021349 | 0.034802 | 0.086653 | 0.111288 | 0.03692 | −0.030796 | −0.007677 | 0.00167 | 0.023422 | 0.009539 |
| 15 | 0.066841 | 0.027453 | 0.044356 | 0.013241 | 0.033867 | 0.038726 | 0.014556 | 0.005348 | 0.032483 | −0.009052 | 0.063128 | 0.005312 | −0.002319 | −0.030012 |
| 16 | −0.052956 | 0.012007 | 0.015693 | 0.029363 | −0.037449 | −0.000215 | 0.028673 | 0.040327 | 0.030613 | 0.02056 | −0.028358 | 0.034125 | −0.011963 | −0.005779 |
| 17 | 0.055071 | 0.037489 | −0.0012041 | −0.001833 | 0.039238 | 0.000895 | 0.026961 | −0.048882 | 0.032581 | −0.011856 | 0.0371141 | 0.0600981 | −0.004698 | 0.020498 |
| 18 | −0.0602281 | −0.027633 | −0.041761 | −0.048569 | −0.041502 | −0.003602 | −0.018597 | −0.101797 | −0.030221 | −0.04577 | 0.036132 | −0.009941 | −0.047518 | −0.003652 |
| 19 | 0.044044 | 0.019754 | −0.017486 | 0.000001 | 0.069645 | 0.053365 | 0.02922 | −0.018246 | −0.047529 | −0.041653 | 0.034756 | 0.01358 | 0.020464 | −0.01818 |
| 20 | 0.024438 | −0.04368 | 0.000495 | 0.061152 | −0.071956 | 0.016355 | −0.010048 | 0.052731 | −0.025352 | −0.022268 | 0.008775 | 0.056126 | 0.08432 | 0.131326 |
| 21 | −0.013751 | −0.004362 | 0.041019 | 0.05747 | −0.017937 | 0.021563 | 0.022362 | 0.056221 | 0.025834 | −0.008055 | 0.016129 | −0.002788 | 0.034625 | −0.019674 |
| 22 | 0.0167411 | −0.011091 | −0.0353281 | −0.039327 | −0.041649 | −0.063737 | −0.034236 | 0.03344 | 0.0475221 | −0.034585 | −0.009287 | −0.002916 | −0.032274 | −0.013496 |
| 23 | −0.075925 | −0.041117 | −0.02228 | −0.055742 | −0.022117 | −0.074713 | −0.041997 | −0.058092 | 0.021916 | 0.00185 | −0.012389 | −0.065575 | −0.007123 | −0.064452 |
| 24 | −0.005255 | −0.040907 | −0.109632 | −0.08742 | −0.013896 | 0.03484 | −0.016553 | 0.01167 | 0.017791 | 0.05875 | −0.041503 | −0.045331 | −0.041062 | −0.007644 |
| 25 | −0.06549 | −0.011549 | 0.03468 | −0.043246 | −0.071488 | −0.050891 | 0.002919 | −0.044383 | −0.006845 | 0.029468 | 0.002107 | −0.028073 | 0.054611 | 0.019445 |
| 26 | 0.04332 | 0.000041 | −0.08129 | −0.034455 | 0.071751 | −0.021493 | −0.087859 | 0.064881 | 0.035017 | 0.07487 | −0.006717 | −0.030401 | −0.030847 | −0.009816 |
| 27 | 0.00411 | 0.062777 | 0.010162 | −0.091464 | −0.008123 | 0.05027 | 0.019641 | −0.063813 | −0.039189 | −0.025813 | 0.029486 | −0.048021 | −0.011481 | −0.060494 |
| 28 | 0.039621 | 0.017105 | 0.026006 | −0.026382 | −0.046937 | 0.004956 | −0.016998 | 0.005358 | −0.105253 | −0.03743 | 0.030325 | −0.017149 | 0.071565 | 0.002328 |
| 29 | 0.000885 | −0.018308 | −0.039571 | −0.040078 | −0.005883 | 0.012185 | −0.011513 | 0.018398 | 0.018044 | 0.018953 | −0.014555 | −0.030148 | −0.013362 | 0.008413 |
| 30 | −0.171897 | −0.060712 | −0.063488 | −0.05569 | −0.006335 | −0.068442 | −0.036956 | −0.038511 | 0.048656 | 0.025244 | −0.163453 | −0.07145 | −0.004185 | 0.011447 |
| 3 1 | 0.012414 | −0.037344 | −0.047313 | −0.07372 | 0.028447 | 0.004047 | −0.008177 | 0.043435 | 0.00389 | −0.035917 | −0.070074 | −0.084374 | −0.076414 | −0.02645 |
| 32 | 0.0326511 | 0.016962 | 0.0599041 | 0.01809 | 0.06956 | 0.015314 | −0.019618 | −0.035024 | 0.022741 | −0.010796 | 0.0705361 | 0.093878 | 0.0505111 | 0.006063 |
| 33 | 0.0242171 | 0.0236821 | 0.0092661 | 0.032199 | −0.000394 | 0.001538 | −0.011292 | −0.004716 | 0.051272 | 0.036911 | 0.033579 | −0.018705 | 0.017043 | 0.058444 |
| 34 | 0.044038 | 0.098303 | 0.104006 | 0.059705 | 0.056353 | −0.00352 | −0.016082 | −0.028446 | 0.045196 | 0.025978 | 0.011932 | 0.064834 | 0.072351 | 0.038725 |
| 35 | −0.066177 | −0.074826 | −0.062514 | 0.125156 | 0.087155 | −0.007377 | −0.007449 | 0.085059 | 0.013257 | −0.022868 | −0.049747 | 0.055654 | 0.028474 | 0.011999 |
| 36 | 0.065979 | −0.032133 | 0.046265 | 0.002738 | 0.01854 | 0.016623 | 0.020147 | −0.055295 | −0.080646 | 0.008391 | 0.038201 | −0.011567 | −0.021199 | −0.044827 |
| 37 | −0.023107 | 0.00826 | 0.014357 | 0.051139 | −0.038292 | 0.022947 | 0.020033 | 0.039029 | 0.052088 | 0.03411 | 0.000015 | 0.062052 | 0.048275 | −0.015607 |
| 38 | 0.058357 | 0.00168 | −0.0143 | −0.06575 | 0.026153 | 0.028997 | −0.036226 | −0.004522 | 0.028481 | 0.039617 | 0.027669 | −0.026817 | 0.028632 | 0.05732 |
| 39 | −0.032985 | −0.016093 | −0.035614 | −0.029012 | −0.003747 | −0.029111 | 0.025869 | 0.147526 | −0.019656 | 0.039803 | −0.064988 | −0.038044 | −0.029896 | −0.011555 |
| 40 | −0.042173 | 0.029108 | −0.004725 | −0.013382 | 0.028871 | −0.028762 | 0.009912 | 0.081859 | −0.055439 | −0.08854 | −0.03317 | −0.047375 | −0.036589 | −0.002599 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 41 | 0.049154 | −0.003502 | −0.010632 | −0.040407 | 0.021 | 0.011099 | 0.031793 | −0.03782 | −0.004258 | −0.017689 | 0.028135 | −0.057384 | −0.005272 | 0.008964 |
| 42 | 0.0054161 | −0.004681 | −0.0097T | 0.000507 | −0.006561 | 0.010463 | −0.008521 | 0.003419 | −0.008803 | −0.019101 | 0.010364 | 0.01997 | −0.00147 | −0.002845 |
| 43 | 0.037497 | −0.083337 | −0.010867 | 0.037076 | 0.018434 | −0.119398 | −0.054015 | 0.07777 | 0.00708 | 0.017425 | −0.032868 | −0.0268 | 0.042515 | −0.004574 |
| 44 | 0.006753 | −0.02257 | −0.019969 | −0.029524 | −0.003999 | 0.065627 | −0.019935 | −0.083643 | −0.023011 | 0.032313 | 0.027589 | 0.053149 | 0.011635 | 0.01648 |
| 45 | 0.012834 | 0.040457 | 0.01385 | 0.01421 | −0.02532 | 0.038888 | −0.011426 | −0.06373 | −0.03189 | −0.007979 | −0.035735 | −0.003996 | 0.012261 | −0.060075 |
| 46 | 0.026541 | −0.023665 | 0.025164 | −0.022788 | 0.011256 | −0.028468 | 0.044087 | 0.000194 | −0.005244 | 0.069233 | −0.007725 | −0.122537 | −0.041907 | −0.009864 |
| 47 | −0.018116 | −0.039863 | −0.004482 | 0.053354 | 0.030148 | 0.011342 | −0.016087 | −0.084301 | 0.015105 | 0.086114 | 0.020928 | 0.004266 | 0.023486 | 0.045016 |
| 48 | −0.027585 | −0.043232 | −0.004471 | 0.017941 | −0.062888 | 0.02062 | 0.007303 | −0.062027 | −0.03388 | −0.021682 | −0.008297 | 0.038662 | −0.007912 | −0.004005 |
| 49 | 0.004475 | 0.041434 | 0.04322 | −0.002297 | −0.006483 | 0.000603 | 0.011807 | −0.072579 | −0.020402 | 0.009439 | −0.007907 | 0.006419 | 0.033904 | −0.017645 |
| 50 | −0.054593 | 0.064546 | 0.001155 | −0.016894 | 0.003537 | 0.004569 | 0.08646 | 0.041706 | 0.056644 | 0.048506 | −0.015885 | 0.04752 | 0.015062 | 0.00976 |
| 51 | 0.038579 | 0.08217 | 0.043361 | −0.013975 | 0.028468 | −0.08134 | −0.06967 | −0.011245 | 0.059599 | 0.002927k | 0.016161 | 0.045627 | 0.002848 | 0.020343 |
| 52 | 0.015484 | −0.055283 | 0.001731 | −0.0596 | 0.052244 | 0.07595 | 0.007875 | 0.009776 | −0.008711 | 0.028488 | 0.05562 | 0.016602 | 0.027541 | −0.065402 |
| 53 | 0.055912 | 0.044585 | 0.030667 | −0.007781 | −0.008602 | −0.004436 | 0.035003 | −0.005463 | −0.036847 | −0.019202 | 0.040637 | 0.070535 | 0.041244 | −0.034995 |
| 54 | 0.005897 | 0.027943 | 0.044942 | −0.108423 | 0.037829 | 0.02031 | 0.052969 | 0.021097 | 0.076449 | −0.014388 | 0.013529 | −0.14354 | −0.10059 | −0.061905 |
| 55 | −0.016543 | 0.063211 | 0.085773 | 0.03138 | −0.048433 | −0.03712 | 0.003905 | −0.040203 | −0.006709 | 0.015386 | −0.026645 | −0.038592 | 0.002878 | −0.042429 |
| 56 | 0.192037 | −0.002546 | −0.012514 | 0.087903 | 0.019151 | 0.00815 | −0.02209 | 0.047904 | −0.034605 | −0.039209 | 0.097584 | 0.055352 | 0.030103 | −0.005169 |
| 57 | 0.057195 | 0.015958 | 0.026695 | 0.011598 | 0.002127 | −0.022382 | −0.071363 | −0.008734 | 0.008942 | 0.017281 | 0.019795 | 0.054476 | 0.065712 | 0.016264 |
| 58 | 0.02966 | 0.060017 | 0.02653 | −0.034886 | −0.091195 | −0.018132 | −0.031671 | −0.072305 | −0.019167 | −0.069165 | 0.001345 | −0.001748 | −0.057268 | −0.034815 |
| 59 | 0.042166 | −0.028204 | −0.081141 | 0.03076 | −0.007882 | −0.117699 | −0.057119 | 0.053325 | 0.073297 | 0.008623 | −0.005038 | −0.001505 | −0.061403 | −0.007322 |
| 60 | 0.046925 | −0.017356 | 0.026591 | 0.02004 | −0.091846 | 0.001219 | 0.004613 | −0.009322 | −0.019092 | −0.048936 | 0.023967 | 0.013545 | 0.040173 | −0.018255 |
| 61 | −0.037502 | 0.057139 | 0.055658 | 0.035916 | −0.023556 | 0.01773 | 0.025742 | 0.046374 | −0.004328 | −0.013675 | 0.029434 | 0.078559 | 0.018441 | −0.065777 |
| 62 | 0.036275 | −0.022471 | −0.042357 | 0.024077 | 0.058095 | 0.018094 | −0.033645 | −0.03221 | −0.004128 | −0.041952 | −0.007804 | −0.046635 | −0.013066 | 0.054704 |
| 63 | −0.054066 | 0.07493 | 0.13558 | 0.106991 | 0.026373 | 0.012677 | 0.010592 | 0.026854 | 0.066226 | −0.028996 | 0.048489 | 0.027679 | 0.055601 | −0.026 |
| 64 | 0.01938 | 0.052007 | −0.00046 | −0.059772 | −0.080282 | 0.050029 | 0.015067 | −0.009378 | −0.019669 | −0.034186 | 0.038183 | −0.019563 | −0.031594 | 0.00685 |
| 65 | −0.027168 | −0.060812 | −0.070341 | −0.102262 | 0.009463 | −0.065161 | −0.108545 | 0.000437 | −0.017435 | −0.02519 | −0.045068 | −0.128031 | −0.137207 | −0.050431 |
| 66 | 0.072015 | −0.036928 | −0.04188 | 0.012941 | −0.030944 | −0.018998 | −0.077965 | −0.063882 | 0.048529 | 0.08599 | 0.051083 | 0.04262 | 0.016222 | 0.045974 |
| 67 | −0.114206 | −0.061563 | 0.001267 | 0.028921 | 0.004122 | −0.016824 | −0.00337 | −0.034123 | −0.013214 | −0.030653 | 0.006421 | 0.065196 | 0.014824 | 0.044922 |
| 68 | −0.052487 | 0.015657 | −0.017322 | −0.009772 | 0.090725 | −0.023417 | −0.032436 | −0.021257 | 0.01225 | 0.059787 | −0.045288 | −0.007701 | −0.011996 | 0.016313 |
| 69 | −0.089544 | −0.051724 | −0.071877 | −0.05008 | 0.056588 | 0.027551 | −0.002563 | −0.02088 | −0.016273 | 0.011002 | −0.023213 | −0.007653 | 0.052616 | 0.00658 |
| 70 | −0.043612 | −0.052665 | −0.035992 | −0.021558 | −0.090794 | 0.017313 | 0.0106 | −0.066361 | −0.019631 | −0.048053 | −0.022726 | 0.044626 | −0.018448 | −0.022352 |
| 71 | 0.07434 | −0.002145 | −0.031709 | 0.04829 | −0.046824 | 0.017532 | −0.017312 | 0.034455 | 0.008267 | 0.027732 | 0.043726 | −0.006228 | 0.003142 | 0.012704 |
| 72 | −0.01966 | −0.032638 | 0.030952 | 0.009939 | −0.028619 | 0.008419 | −0.000438 | −0.097465 | −0.008091 | −0.005613 | −0.021005 | −0.03727 | −0.036141 | −0.020096 |
| 73 | 0.019039 | 0.025437 | −0.002533 | −0.028839 | 0.02003 | −0.006158 | 0.039071 | 0.04759 | −0.007928 | 0.006543 | −0.026181 | −0.03273 | −0.002725 | 0.024519 |
| 74 | 0.057656 | −0.088593 | −0.060947 | 0.04588 | 0.118208 | −0.016573 | −0.033406 | 0.028797 | 0.020182 | 0.001222 | 0.020374 | 0.08905 | 0.023749 | 0.040543 |
| 75 | 0.100408 | 0.066503 | −0.034411 | −0.080778 | 0.030532 | −0.009232 | −0.100294 | −0.061004 | 0.013183 | 0.029864 | 0.036303 | 0.069088 | 0.000517 | −0.02376 |
| 76 | 0.058718 | 0.092392 | 0.055153 | −0.070901 | −0.057716 | −0.014993 | −0.014201 | 0.035988 | −0.060141 | 0.053746 | 0.017869 | −0.085118 | 0.017998 | −0.00559 |
| 77 | 0.046071 | 0.007562 | −0.05018 | 0.034943 | 0.081062 | −0.004523 | 0.024409 | 0.044734 | 0.012632 | −0.026427 | 0.035725 | 0.069353 | 0.010627 | −0.002038 |
| 78 | −0.06433 | −0.097208 | −0.00341 | 0.038448 | 0.002447 | 0.001071 | 0.01809 | 0.011863 | 0.003796 | 0.036204 | −0.061233 | −0.019346 | −0.049797 | 0.005639 |
| 79 | −0.092378 | 0.021708 | 0.072187 | 0.012696 | −0.035193 | 0.017741 | −0.013981 | −0.075964 | 0.00164 | −0.039969 | −0.022587 | −0.027821 | −0.079616 | −0.029067 |
| 80 | −0.041058 | −0.02213 | 0.006872 | −0.634663 | 0.034136 | 0.027149 | 0.01145 | 0.003352 | −0.026967 | 0.058656 | −0.024177 | 0.013969 | 0.022691 | −0.014816 |
| 81 | −0.086235 | −0.001154 | 0.041818 | 0.051413 | 0.035751 | −0.010478 | 0.036355 | −0.017157 | 0.00102 | 0.029002 | −0.040307 | −0.001913 | −0.016902 | −0.013134 |
| 82 | 0.051357 | 0.003121 | 0.021253 | 0.023922 | 0.013393 | 0.022379 | 0.024374 | −0.005447 | −0.024783 | −0.049343 | 0.054335 | 0.047388 | 0.080206 | 0.059326 |
| 83 | −0.076801 | −0.006382 | 0.00056 | 0.014813 | 0.068603 | 0.03181 | 0.013061 | 0.009584 | −0.012227 | −0.009938 | −0.080722 | 0.034496 | −0.008424 | −0.020593 |
| 84 | −0.084668 | −0.091051 | −0.045396 | 0.032085 | 0.113582 | 0.026252 | 0.036565 | 0.070169 | −0.055987 | 0.015077 | −0.034546 | −0.107209 | −0.041015 | 0.003344 |
| 85 | 0.025612 | 0.016714 | 0.038155 | 0.029333 | 0.012705 | −0.04573 | −0.072182 | −0.029571 | −0.000533 | −0.007066 | 0.044354 | 0.070605 | 0.028655 | −0.009599 |
| 86 | 0.040416 | −0.006704 | −0.040661 | −0.042996 | −0.021465 | 0.023824 | −0.04643 | −0.095637 | 0.012957 | 0.042656 | 0.035991 | 0.070804 | −0.015922 | −0.075553 |
| 87 | −0.066949 | 0.013435 | 0.075065 | −0.027539 | 0.021805 | −0.022147 | 0.087507 | 0.126203 | 0.029018 | 0.02509 | −0.030813 | −0.095201 | 0.033563 | 0.039311 |
| 88 | −0.015675 | −0.037307 | 0.042255 | 0.022049 | −0.075422 | −0.053584 | −0.012954 | −0.113988 | −0.021393 | −0.007292 | 0.049661 | 0.105856 | 0.053304 | −0.060449 |
| 89 | 0.004893 | −0.037101 | −0.075392 | −0.11051 | −0.073247 | 0.022165 | −0.043843 | −0.051022 | −0.007827 | −0.046636 | −0.007621 | −0.096599 | −0.116329 | 0.016278 |
| 90 | 0.014161 | 0.0687291 | 0.01931 | 0.042268 | −0.035355 | −0.069734 | −0.005359 | −0.011357 | −0.03498 | −0.004835 | −0.020144 | 0.071851 | −0.002034 | −0.000436 |
| 91 | −0.106318 | 0.037346 | 0.011852 | −0.030464 | 0.018713 | −0.03778 | 0.019452 | −0.019402 | 0.046661 | 0.049866 | 0.019483 | 0.088768 | 0.076847 | −0.017062 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 92 | 0.042405 | 0.00144 | −0.001192 | 0.007412 | −0.026999 | −0.008617 | 0.008378 | −0.005791 | −0.025049 | −0.016854 | 0.006158 | −0.009107 | 0.025247 | −0.020623 |
| 93 | −0.008519 | −0.027228 | −0.0515811 | −0.015412 | −0.028578 | −0.049788 | 0.038015 | −0.027684 | 0.054532 | 0.00656 | −0.013964 | −0.055786 | −0.125398 | 0.004639 |
| 94 | 0.050249 | 0.056628 | 0.023934 | 0.108991 | 0.055783 | 0.072163 | 0.003734 | −0.006551 | 0.050151 | 0.010712 | −0.001431 | 0.011512 | 0.019062 | 0.033844 |
| 95 | 0.030116 | −0.052643 | −0.004706 | 0.023328 | −0.084086 | 0.055757 | 0.056514 | −0.005437 | −0.03897 | 0.039978 | 0.030033 | −0.00885 | −0.036644 | −0.003045 |
| 96 | −0.017183 | −0.051217 | −0.040805 | −0.009734 | −0.037812 | 0.030169 | 0.015286 | −0.00532 | 0.006138 | −0.01544 | 0.037999 | 0.018737 | −0.027748 | 0.002111 |
| 97 | −0.014944 | −0.004869 | −0.032571 | −0.007145 | −0.024409 | 0.010608 | −0.008658 | −0.032041 | −0.040455 | −0.043588 | −0.042618 | −0.011926 | 0.00079 | 0.018013 |
| 98 | −0.022066 | 0.046961 | −0.012792 | 0.01738 | −0.008861 | −0.015872 | 0.002583 | −0.028683 | 0.001724 | −0.028542 | −0.013793 | −0.066599 | −0.03129 | −0.040637 |
| 99 | 0.065318 | 0.026905 | −0.065195 | 0.039416 | 0.007124 | 0.00663 | −0.047115 | 0.018467 | −0.113734 | −0.153354 | 0.001176 | 0.043876 | −0.056312 | 0.097246 |
| 100 | 0.017791 | 0.011646 | −0.000272 | −0.017925 | 0.00648 | 0.00295 | −0.017562 | 0.005466 | −0.004729 | 0.02522 | −0.012572 | −0.001639 | 0.003675 | −0.014596 |
| 101 | 0.005291 | 0.010442 | 0.008997 | −0.007223 | −0.018507 | −0.000391 | 0.004541 | 0.006913 | −0.00604 | −0.012668 | 0.013146 | 0.010218 | −0.000243 | −0.015894 |
| 102 | 0.025025 | 0.02565 | 0.002117 | 0.005409 | 0.015449 | −0.019967 | −0.002996 | 0.000263 | 0.012209 | 0.011214 | −0.016857 | 0.01819 | 0.019606 | 0.019292 |
| 103 | 0.033798 | 0.036361 | −0.009599 | −0.021495 | −0.001801 | −0.069324 | −0.037459 | 0.05165 | 0.019569 | 0.004014 | −0.006574 | 0.003884 | −0.009848 | 0.005354 |
| 104 | 0.009481 | 0.010861 | 0.005337 | 0.019295 | 0.028064 | −0.005903 | −0.006155 | −0.023524 | −0.00321 | 0.012989 | 0.016746 | 0.058487 | 0.031871 | −0.000943 |
| 105 | 0.02698 | 0.004755 | −0.019803 | −0.000647 | −0.04946 | −0.00489 | −0.030688 | −0.033562 | 0.015174 | 0.017165 | 0.006328 | 0.027492 | −0.02165 | −0.029156 |
| 106 | −0.018249 | 0.023194 | 0.006542 | −0.009119 | −0.001487 | −0.008198 | 0.018915 | −0.017931 | 0.023065 | −0.002981 | −0.009773 | −0.037002 | 0.001483 | −0.010026 |
| 107 | −0.02569 | 0.017663 | 0.03818 | 0.024105 | 0.022833 | −0.002271 | 0.020171 | −0.021678 | −0.038577 | −0.023273 | 0.033471 | 0.096354 | 0.055061 | 0.005819 |
| 108 | −0.011202 | −0.002016 | 0.03587 | 0.017611 | −0.018156 | 0.036012 | 0.027616 | 0.008368 | −0.03476 | −0.010569 | 0.003853 | 0.005978 | 0.00479 | −0.01216 |
| 109 | 0.033706 | 0.005587 | −0.042354 | −0.029025 | 0.021237 | 0.019287 | 0.018117 | −0.007337 | 0.015374 | 0.038099 | 0.015195 | −0.009721 | −0.050411 | −0.017263 |
| 110 | 0.020416 | 0.026796 | 0.028531 | 0.014537 | 0.02862 | −0.004924 | 0.00512 | −0.01301 | −0.045423 | −0.034514 | 0.000816 | 0.012339 | −0.016149 | 0.003702 |
| 111 | −0.005327 | −0.009734 | −0.002535 | 0.028552 | 0.031423 | 0.01648 | 0.030976 | 0.020861 | −0.007022 | −0.01497 | 0.00868 | 0.031958 | 0.009214 | −0.016013 |
| 112 | 0.018959 | 0.029607 | 0.019508 | −0.003885 | −0.068079 | 0.023555 | 0.018314 | −0.005919 | −0.029542 | 0.004217 | 0.011325 | 0.00744 | 0.013763 | −0.003945 |
| 113 | 0.003659 | 0.024108 | −0.005105 | 0.004719 | 0.028002 | 0.010403 | 0.002017 | 0.002885 | 0.001689 | 0.011301 | 0.027559 | 0.022944 | −0.0041 | −0.063125 |
| 114 | 0.013298 | 0.035202 | −0.01827 | −0.016717 | 0.034061 | 0.033592 | 0.008367 | −0.006542 | 0.003182 | 0.01624 | −0.014622 | 0.007591 | −0.008305 | −0.006417 |
| 115 | 0.024165 | −0.044793 | −0.016856 | −0.005398 | −0.015473 | −0.019843 | −0.015085 | −0.024639 | −0.031487 | 0.017236 | 0.036955 | 0.020417 | 0.023469 | 0.010644 |
| 116 | −0.015709 | 0.01814 | −0.036513 | −0.042041 | −0.039793 | 0.004169 | −0.014707 | 0.000867 | −0.006525 | −0.01265 | 0.016861 | −0.028317 | −0.048072 | −0.001068 |
| 117 | −0.016038 | −0.027024 | −0.031037 | −0.009015 | 0.034881 | −0.024835 | −0.002992 | 0.045971 | 0.000359 | 0.012286 | −0.022488 | −0.008488 | −0.003668 | 0.006166 |
| 118 | 0.069603 | −0.015861 | 0.012872 | 0.034042 | 0.029236 | −0.004064 | 0.00188 | −0.007584 | 0.00948 | 0.047175 | 0.029622 | 0.017285 | 0.039588 | 0.012918 |
| 119 | −0.011084 | 0.012761 | 0.0169 | −0.017792 | −0.009587 | 0.009974 | −0.002384 | −0.006096 | −0.018694 | 0.018371 | −0.010396 | −0.008009 | −0.007907 | −0.000734 |
| 120 | −0.010151 | −0.005398 | 0.014697 | 0.003902 | 0.01786 | −0.000611 | 0.00058 | 0.028255 | −0.00246 | 0.005286 | −0.013958 | −0.014758 | 0.006241 | 0.00475 |
| 121 | −0.011757 | 0.017687 | −0.000144 | −0 502513 | 0.012202 | −0.009873 | 0.00333 | 0.027447 | 0.013637 | −0.01148 | −0.008273 | 0.005702 | −0.000032 | −0.002436 |
| 122 | 0.013381 | −0.001652 | 0.010622 | −0.00644 | −0.01541 | 0.020035 | 0.03262 | 0.050093 | 0.004085 | 0.010686 | 0.019406 | −0.015396 | 0.012788 | 0.008528 |
| 123 | 0.001036 | −0.039888 | −0.006213 | 0.011256 | 0.013527 | 0.006199 | 0.022401 | 0.061319 | −0.004019 | 0.003237 | 0.006863 | −0.01012 | −0.018859 | 0.009117 |
| 124 | 0.0144491 | 0.020691 | 0.0196261 | 0.008949 | 0.012917 | 0.008327 | −0.012895 | 0.007372 | −0.016303 | 0.0112691 | 0.0092451 | 0.0165331 | 0.0204021 | −0.001381 |
| 125 | −0.000428 | −0.004042 | 0.014466 | 0.014065 | −0.003647 | 0.005254 | 0.013314 | −0.010383 | −0.00814 | −0.001451 | 0.021279 | −0.03143 | 0.001035 | −0.01798 |
| 126 | −0.007077 | −0.020404 | −0.005286 | 0.008871 | −0.001711 | −0.003656 | −0.015999 | 0.027512 | 0.006616 | 0.004448 | 0.005464 | 0.016396 | 0.015099 | −0.013548 |
| 127 | −0.037506 | −0.00968 | 0.007353 | −0.004646 | −0.033377 | −0.025575 | 0.014628 | 0.040044 | −0.000625 | 0.010287 | −0.02784 | −0.025104 | −0.002223 | −0.006327 |
| 128 | −0.021214 | 0.007929 | 0.003033 | −0.044207 | −0.011982 | 0.036001 | −0.010307 | −0.034179 | −0.0128 | 0.014196 | 0.014494 | −0.015678 | −0.01663 | −0.031532 |
| 129 | 0.016395 | 0.009595 | 0.023657 | 0.033099 | −0.007485 | −0.031838 | 0.007628 | 0.043599 | 0.021293 | 0.013053 | −0.002538 | −0.018558 | 0.025969 | 0.027574 |
| 130 | −0.003749 | 0.046016 | 0.019223 | 0.022165 | 0.018594 | −0.030222 | −0.030752 | 0.010201 | 0.006139 | −0.010276 | −0.006277 | −0.017912 | 0.014201 | 0.012573 |
| 131 | −0.040954 | −0.0255821 | 0.01283 | 0.026153 | 0.006585 | 0.021658 | −0.008608 | −0.024786 | 0.000346 | −0.007408 | 0.027835 | 0.031852 | 0.026402 | 0.03032 |
| 132 | −0.006186 | 0.013614 | 0.0100871 | −0.011372 | −0.019779 | 0.011057 | 0.024808 | −0.029538 | −0.003979 | −0.018914 | −0.009048 | 0.033014 | −0.047028 | −0.008275 |
| 133 | −0.000693 | 0.014963 | 0.008717 | −0.034894 | 0.015259 | −0.001659 | 0.019044 | 0.017111 | −0.008643 | 0.000094 | 0.006979 | −0.024566 | −0.010761 | −0.015619 |
| 134 | 0.003833 | 0.049957 | 0.018285 | 0.009185 | −0.003592 | 0.009038 | 0.00032 | 0.029125 | 0.018391 | 0.032944 | 0.028243 | 0.059212 | 0.017464 | −0.037643 |
| 135 | −0.015648 | −0.0052881 | −0.0039021 | −0.009327 | 0.001603 | 0.021438 | −0.006817 | −0.034968 | −0.001446 | 0.0004691 | 0.0036081 | 0.003299 | −0.007052 | −0.015232 |
| 136 | −0.022909 | −0.000496 | 0.018625 | 0.030174 | −0.005755 | −0.017835 | 0.00639 | −0.004795 | 0.005156 | 0.000215 | −0.013983 | −0.033072 | −0.02993 | −0.009141 |
| 137 | 0.039042 | 0.033592 | 0.009432 | −0.016618 | 0.01008 | −0.002705 | −0.018672 | 0.015694 | 0.010147 | 0.007871 | 0.021499 | −0.007588 | 0.003716 | −0.000748 |
| 138 | −0.068875 | −0.002927 | 0.002488 | 0.0427 | −0.036526 | 0.003722 | −0.006735 | −0.033957 | −0.002941 | 0.016236 | −0.015097 | 0.045259 | 0.033992 | 0.000647 |
| 139 | 0.036771 | 0.023826 | 0.0090231 | −0.003222 | −0.015925 | 0.008888 | 0.006007 | 0.022005 | −0.011887 | −0.045819 | −0.005933 | −0.014761 | −0.017496 | −0.034926 |
| 140 | −0.004221 | −0.005544 | −0.029411 | −0.032173 | −0.015012 | 0.042725 | 0.031001 | −0.019786 | −0.019707 | −0.0057 | −0.002238 | −0.000826 | 0.004426 | 0.02769 |
| 141 | −0.002452 | 0.01126 | −0.000911 | 0.036505 | 0.019645 | 0.008801 | −0.005792 | 0.036404 | 0.003581 | −0.011065 | −0.028832 | 0.026418 | 0.027751 | 0.028273 |
| 142 | 0.034543 | −0.022421 | −0.028191 | −0.004525 | 0.020434 | 0.017763 | 0.008627 | 0.005533 | 0.006895 | 0.002312 | 0.027322 | −0.0076 | −0.002099 | 0.009419 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 143 | 0.008816 | 0.018732 | 0.014753 | −0.043437 | −0.004999 | 0.013349 | 0.025051 | −0.007534 | −0.023526 | −0.016684 | 0.009486 | −0.000295 | 0.038455 | 0.004377 |
| 144 | −0.026028 | 0.015488 | 0.008357 | −0.006226 | 0.007761 | 0.008206 | −0.006428 | −0.033429 | 0.000416 | 0.006302 | −0.02845 | −0.004432 | −0.021286 | −0.014209 |
| 145 | −0.00296 | −0.021997 | −0.014347 | 0.002927 | 0.03718 | 0.004325 | 0.007325 | 0.022614 | 0.009285 | −0.005081 | 0.000057 | −0.002251 | −0.015065 | 0.008492 |
| 146 | −0.016803 | −0.008739 | −0.004445 | −0.011097 | −0.019267 | 0.021626 | 0.004017 | 0.020239 | 0.003429 | 0.00874 | 0.004219 | −0.019093 | −0.014784 | −0.003738 |
| 147 | −0.01822 | 0.004354 | −0.013912 | −0.02063 | 0.007124 | 0.023071 | −0.000159 | 0.011003 | 0.001431 | −0.000374 | 0.000411 | 0.005282 | −0.009677 | −0.026777 |
| 148 | −0.048226 | 0.015897 | −0.002147 | 0.014181 | −0.008292 | −0.034644 | −0.026408 | −0.044104 | 0.043751 | −0.012221 | −0.017907 | 0.073072 | 0.003426 | −0.020404 |
| 149 | 0.03296 | 0.013041 | 0.010765 | 0.0175 | −0.002157 | −0.007503 | −0.013521 | −0.028529 | 0.009485 | −0.030598 | 0.026512 | 0.028315 | −0.021118 | −0.022211 |
| 150 | 0.036517 | 0.011363 | 0.032203 | 0.02784 | 0.002246 | 0.017322 | −0.008695 | 0.036868 | 0.017611 | 0.003924 | 0.005857 | −0.023645 | 0.005488 | 0.018533 |
| 151 | 0.00957 | 0.054347 | 0.030474 | 0.031802 | 0.025334 | −0.029799 | −0.014132 | 0.041594 | 0.017456 | −0.008989 | 0.001692 | 0.038557 | 0.019472 | 0.004968 |
| 152 | −0.007255 | 0.043139 | 0.000128 | −0.019113 | −0.040513 | −0.042423 | −0.016317 | −0.016098 | −0.00017 | −0.002376 | 0.001874 | 0.038628 | 0.025882 | −0.003291 |
| 153 | 0.005035 | 0.024217 | 0.004004 | 0.008233 | 0.021765 | −0.033333 | −0.008499 | 0.021717 | 0.037954 | 0.031596 | −0.017921 | 0.022964 | 0.0242371 | 0.032858 |
| 154 | 0.012742 | 0.002679 | −0.04153 | 0.012613 | 0.022646 | 0.006445 | −0.038068 | −0.017969 | 0.038658 | 0.01678 | 0.00767 | 0.050937 | −0.017228 | 0.010368 |
| 155 | −0.002974 | 0.00095 | 0.000844 | 0.014731 | −0.036606 | −0.006606 | 0.005187 | −0.053232 | 0.010546 | 0.007942 | −0.014433 | 0.022953 | −0.001061 | 0.014257 |
| 156 | −0.052121 | −0.03999 | −0.0285651 | −0.051881 | −0.038935 | 0.040487 | 0.027529 | −0.006951 | 0.007729 | −0.015539 | 0.024655 | −0.016859 | −0.037782 | −0.005011 |
| 157 | 0.0025011 | −0.009263 | −0.0189361 | −0.021494 | 0.015714 | −0.001501 | −0.012548 | 0.005773 | −0.032556 | −0.010646 | 0.01369 | 0.006725 | 0.034233 | −0.010626 |
| 158 | 0.013168 | 0.002298 | 0.015566 | −0.005696 | −0.003722 | 0.01981 | −0.004129 | −0.003005 | 0.003851 | 0.031928 | −0.007134 | −0.000638 | 0.012699 | −0.03133 |
| 159 | 0.021031 | 0.017623 | 0.035372 | 0.018567 | 0.020655 | 0.040305 | 0.008632 | 0.008911 | 0.016728 | 0.022309 | 0.02862 | −0.007665 | −0.031095 | −0.004692 |
| 160 | −0.019819 | 0.029241 | 0.009342 | 0.023556 | 0.006165 | 0.017671 | 0.023087 | −0.019602 | −0.033519 | 0.024348 | −0.012618 | 0.025465 | −0.009756 | −0.035948 |
| 161 | −0.05993 | −0.020537 | 0.016373 | 0.024041 | 0.008364 | −0.034381 | 0.019916 | 0.001664 | −0.013624 | −0.033243 | −0.033513 | −0.011185 | 0.021378 | −0.015825 |
| 162 | −0.018911 | −0.042085 | −0.020129 | 0.030159 | 0.003135 | 0.004381 | −0.030718 | −0.01251 | 0.002355 | −0.001672 | 0.001023 | 0.012923 | 0.011765 | 0.001273 |
| 163 | −0.01808 | 0.023397 | 0.016772 | 0.006361 | −0.012815 | −0.012811 | −0.006177 | −0.009956 | 0.000896 | −0.046864 | 0.026310 | 0.038965 | 0.039492 | 0.005122 |
| 164 | 0.023559 | 0.003059 | −0.024358 | −0.002731 | 0.005132 | −0.002079 | −0.029847 | 0.007439 | 0.006151 | −0.025799 | 0.026117 | 0.014193 | −0.012433 | 0.019219 |
| 165 | −0.01852 | 0.020674 | −0.021389 | 0.011926 | 0.008446 | −0.027959 | −0.044736 | −0.063877 | −0.016367 | 0.004671 | −0.007948 | −0.002202 | 0.008524 | −0.01145 |
| 166 | 0.007749 | −0.002127 | 0.002904 | −0.009576 | 0.029111 | −0.019434 | −0.011836 | 0.009497 | 0.028373 | 0.01304 | 0.006629 | −0.035802 | −0.020584 | −0.013599 |
| 167 | −0.006638 | 0.00724 | 0.01302 | −0.008629 | −0.016386 | −0.005133 | 0.010633 | −0.013201 | −0.026822 | −0.034746 | −0.030259 | −0.055429 | −0.063118 | −0.008545 |
| 168 | 0.030547 | 0.011502 | 0.009044 | −0.010347 | −0.019922 | −0.032067 | −0.036278 | −0.030464 | −0.009751 | −0.026814 | 0.05563 | 0.015327 | 0.025203 | −0.000036 |
| 169 | −0.005925 | 0.002743 | 0.010453 | 0.013052 | −0.021488 | 0.006767 | 0.007084 | 0.026513 | 0.011454 | −0.022453 | 0.011378 | 0.017213 | 0.01051 | 0.010346 |
| 170 | −0.038603 | 0.005564 | 0.002831 | 0.0236 | −0.005588 | −0.000189 | 0.006923 | 0.032945 | 0.031133 | 0.007475 | −0.002554 | 0.021098 | −0.003792 | 0.015262 |
| 171 | 0.006895 | 0.006055 | 0.009056 | 0.015988 | −0.009742 | 0.000164 | 0.013312 | 0.044285 | 0.012807 | −0.01077 | 0.011739 | 0.016182 | 0.019125 | 0.019773 |
| 172 | 0.004585 | 0.019585 | 0.029869 | 0.019295 | 0.00473 | −0.004262 | −0.00557 | 0.007954 | −0.00094 | −0.010248 | −0.002582 | −0.009892 | 0.021503 | 0.001299 |
| 173 | −0.004971 | −0.024165 | −0.003955 | 0.036106 | 0.049704 | −0.011075 | −0.01185 | 0.019204 | 0.006108 | 0.012661 | −0.019014 | −0.028174 | 0.020969 | 0.024612 |
| 174 | 0.013352 | 0.018982 | −0.001516 | −0.00675 | 0.027397 | −0.01851 | −0.00583 | −0.048208 | 0.00578 | −0.021878 | 0.00981 | 0.026663 | 0.012355 | 0.009003 |
| 175 | 0.025452 | −0.045901 | −0.024237 | −0.017429 | 0.001139 | −0.039016 | −0.000154 | 0.016367 | 0.002217 | 0.006327 | −0.013647 | −0.002452 | 0.001124 | −0.026678 |
| 176 | 0.020288 | 0.008303 | 0.0323 | 0.018954 | −0.001448 | −0.02218 | −0.001687 | 0.015523 | −0.004477 | −0.031638 | 0.011954 | 0.008364 | 0.023923 | −0.008417 |
| 177 | −0.03168 | −0.009266 | 0.002889 | −0.008057 | 0.030552 | 0.00809 | −0.012211 | −0.042187 | 0.032125 | 0.001595 | 0.012659 | 0.008386 | 0.005874 | −0.010036 |
| 178 | 0.030856 | −0.003829 | −0.015006 | −0.031364 | −0.00029 | −0.018462 | −0.016519 | −0.015716 | −0.014424 | −0.024156 | −0.000567 | 0.000156 | 0.02835 | −0.014399 |
| 179 | 0.021451 | −0.001736 | −0.006544 | −0.026326 | −0.012222 | 0.003684 | 0.007312 | −0.006866 | −0.01485 | −0.011024 | 0.017135 | 0.003307 | −0.000624 | 0.010483 |
| 180 | −0.005772 | −0.009271 | 0.002099 | −0.012989 | 0.013433 | −0.007303 | 0.005468 | −0.01555 | 0.001402 | 0.011153 | −0.000206 | −0.010505 | 0.009297 | −0.00536 |
| 181 | 0.013704 | 0.003644 | −0.001743 | −0.023191 | −0.001755 | −0.004938 | 0.005115 | −0.010379 | −0.000563 | 0.007468 | −0.003539 | −0.007887 | −0.008141 | −0.003902 |
| 182 | 0.019461 | 0.003779 | 0.003792 | −0.016897 | 0.023875 | −0.002929 | −0.00473 | 0.004732 | 0.007681 | 0.026339 | −0.009808 | 0.002482 | −0.016686 | −0.006558 |
| 183 | 0.02954 | 0.005527 | −0.004469 | −0.014251 | −0.001265 | 0.01578 | 0.003981 | 0.033019 | 0.005715 | 0.027671 | 0.013012 | 0.008222 | −0.0035 | 0.004588 |
| 184 | 0.014273 | 0.0381 | 0.027148 | −0.021193 | −0.036385 | 0.019525 | 0.015243 | −0.000977 | 0.01398 | 0.014074 | 0.017091 | −0.014858 | −0.004814 | −0.015029 |
| 185 | 0.003849 | 0.007506 | −0.005023 | −0.081162 | −0.006017 | −0.035009 | −0.032939 | −0.088513 | 0.002914 | 0.020102 | 0.017199 | 0.00693 | 0.018648 | −0.009178 |
| 186 | −0.026508 | −0.014062 | −0.004478 | 0.011097 | 0.050796 | −0.033934 | −0.012654 | 0.013207 | 0.016785 | 0.022347 | −0.030015 | −0.011436 | 0.010349 | 0.049462 |
| 187 | 0.015493 | −0.012114 | −0.000515 | 0.044043 | 0.036665 | −0.000938 | −0.032055 | −0.00072 | 0.013183 | 0.029753 | −0.010648 | −0.011889 | 0.018088 | 0.02248 |
| 188 | 0.003659 | 0.012567 | 0.00867 | 0.018487 | 0.020023 | 0.00261 | −0.018583 | −0.056223 | 0.014762 | 0.013027 | −0.009961 | 0.012485 | 0.014811 | 0.015824 |
| 189 | 0.027801 | 0.024455 | 0.011197 | 0.031026 | 0.029231 | 0.026352 | −0.005325 | −0.005745 | 0.009781 | −0.00058 | −0.000418 | 0.041647 | 0.000704 | 0.012817 |
| 190 | −0.003988 | −0.005891 | 0.006329 | 0.023009 | 0.020401 | −0.004816 | 0.007929 | 0.040987 | −0.000776 | −0.012504 | 0.002954 | 0.010149 | −0.007941 | −0.02203 |
| 191 | 0.014575 | −0.010367 | −0.005897 | 0.010647 | −0.017729 | 0.001889 | 0.001669 | −0.004031 | −0.015071 | −0.002747 | 0.017725 | 0.037381 | 0.004593 | 0.019149 |
| 192 | −0.071547 | 0.002484 | 0.013998 | −0.000114 | 0.018692 | −0.02136 | 0.021507 | −0.002491 | −0.016609 | 0.02003 | −0.064648 | −0.01012 | 0.002935 | 0.014634 |
| 193 | −0.040571 | −0.011931 | −0.011903 | −0.016959 | 0.018702 | −0.04421 | 0.001594 | −0.022583 | −0.007507 | 0.016235 | −0.037868 | −0.019773 | −0.019449 | 0.006637 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 194 | 0.013138 | −0.035873 | 0.002634 | 0.019666 | −0.017672 | −0.019644 | −0.001381 | −0.032443 | −0.008515 | −0.017829 | 0.011421 | 0.018324 | 0.02341 | 0.010564 |
| 195 | 0.01517 | −0.014633 | 0.003747 | 0.003937 | 0.010458 | 0.016007 | 0.017538 | −0.018261 | −0.028134 | −0.037383 | 0.03102 | −0.016108 | −0.063974 | −0.007261 |
| 196 | 0.008744 | −0.002326 | 0.004985 | −0.028331 | −0.037575 | 0.01146 | 0.023796 | −0.01832 | −0.011205 | −0.040093 | 0.002171 | −0.028596 | −0.060239 | −0.040199 |
| 197 | −0.009894 | 0.000255 | 0.003894 | 0.000902 | 0.011952 | 0.034561 | 0.002916 | 0.004208 | −0.029956 | −0.004731 | 0.003983 | 0.037169 | −0.01937 | −0.001247 |
| 198 | 0.023992 | 0.036002 | 0.023668 | −0.014623 | 0.014577 | 0.015372 | −0.009899 | −0.011207 | 0.002951 | 0.012988 | 0.057765 | −0.014883 | 0.037305 | −0.03711 |
| 199 | −0.014869 | −0.02833 | −0.001712 | 0.009429 | 0.039811 | 0.014427 | 0.043519 | 0.053473 | −0.025188 | −0.032577 | 0.010641 | −0.030679 | 0.002667 | 0.00405 |
| 200 | 0.040212 | 0.029754 | 0.006942 | 0.014697 | 0.001517 | 0.010843 | 0.003461 | −0.041439 | −0.01365 | −0.020745 | 0.008863 | 0.025404 | 0.009264 | −0.035643 |
| 201 | −0.048579 | 0.004741 | 0.009853 | −0.01475 | 0.016231 | 0.019783 | 0.034313 | 0.014414 | 0.009802 | −0.006347 | −0.011453 | −0.010768 | −0.020043 | −0.000782 |
| 202 | −0.03718 | 0.023029 | −0.006569 | −0.016798 | 0.013054 | 0.017917 | 0.004476 | 0.011755 | −0.004324 | −0.009312 | 0.00874 | 0.017757 | −0.007475 | −0.02583 |
| 203 | 0.010298 | 0.025975 | 0.004168 | −0.009052 | −0.002548 | 0.006189 | −0.016953 | −0.038601 | 0.009805 | 0.012827 | 0.017518 | 0.002915 | 0.008664 | −0.019097 |
| 204 | −0.024533 | −0.013203 | −0.05067 | −0.066326 | −0.026227 | −0.001224 | −0.019649 | −0.027284 | 0.003782 | 0.03705 | −0.015424 | −0.020106 | −0.007484 | −0.025448 |
| 205 | −0.020256 | −0.016514 | 0.043608 | 0.03213 | −0.01321 | 0.038131 | 0.047009 | 0.034671 | −0.020153 | −0.008773 | −0.022606 | −0.056145 | −0.028131 | −0.027773 |
| 206 | −0.032851 | −0.02061 | −0.038649 | −0.000302 | 0.061535 | −0.020914 | −0.001738 | 0.016621 | −0.004879 | 0.027608 | −0.03158 | −0.010277 | −0.035292 | −0.023419 |
| 207 | 0.030733 | −0.006132 | −0.028385 | −0.051687 | 0.006495 | 0.011454 | 0.019761 | 0.018727 | −0.002668 | −0.002787 | −0.010181 | −0.053171 | −0.03385 | 0.005563 |
| 208 | −0.000973 | −0.016063 | −0.055781 | 0.030498 | 0.028068 | −0.000063 | −0.012063 | −0.031305 | −0.021456 | 0.009041 | −0.000524 | −0.005675 | 0.010539 | 0.054286 |
| 209 | −0.002737 | 0.023159 | −0.000015 | −0.013442 | 0.009287 | −0.010928 | 0.01905 | 0.017145 | 0.017701 | −0.005946 | −0.004953 | −0.015171 | 0.000376 | −0.020913 |
| 210 | 0.029493 | −0.012819 | 0.008958 | −0.008313 | 0.008497 | 0.007991 | −0.003892 | 0.004049 | −0.014947 | −0.063674 | 0.009891 | 0.008967 | −0.012809 | −0.026578 |
| 211 | −0.016228 | −0.012664 | 0.023342 | −0.007316 | 0.031021 | 0.025175 | −0.002615 | 0.009461 | −0.003375 | −0.017314 | −0.002527 | −0.018116 | 0.037446 | −0.011961 |
| 212 | −0.014819 | 0.049819 | 0.030456 | 0.008555 | 0.011014 | 0.000745 | 0.003833 | −0.01817 | −0.013782 | 0.001502 | 0.011459 | 0.057612 | 0.034344 | −0.006345 |
| 213 | 0.027705 | 0.022706 | 0.047995 | −0.012314 | −0.014442 | −0.033743 | −0.012375 | −0.030908 | 0.013184 | −0.020646 | 0.012691 | −0.019459 | −0.003121 | 0.023899 |
| 214 | −0.001525 | −0.012703 | 0.000789 | 0.002086 | 0.00037 | 0.00553 | 0.024907 | 0.01713 | 0.003212 | 0.014168 | 0.006295 | 0.002919 | 0.012772 | 0.005202 |
| 215 | 0.01786 | −0.001993 | −0.020883 | 0.00119 | 0.04495 | −0.006174 | 0.006227 | −0.050986 | −0.0107 | −0.010387 | −0.021954 | 0.016911 | 0.022036 | 0.009501 |
| 216 | 0.019914 | 0.008616 | 0.023004 | 0.003987 | −0.026856 | 0.01064 | −0.016271 | −0.027758 | 0.000266 | −0.014218 | 0.022036 | 0.042584 | 0.026215 | 0.000649 |
| 217 | −0.019588 | 0.018047 | 0.017838 | 0.016149 | −0.012406 | 0.022789 | 0.015286 | 0.016913 | 0.01672 | −0.010582 | −0.006247 | 0.006563 | −0.019789 | −0.022618 |
| 218 | −0.0238 | −0.002708 | 0.001238 | −0.002436 | 0.017424 | 0.011008 | 0.035066 | 0.006787 | 0.021491 | 0.011913 | −0.006735 | 0.012087 | 0.009133 | 0.016691 |
| 219 | −0.019828 | −0.00195 | −0.015428 | 0.021073 | 0.023536 | 0.0149 | 0.032181 | 0.046894 | 0.027694 | 0.009806 | −0.007598 | 0.014642 | −0.000539 | 0.026896 |
| 220 | −0.004988 | 0.020738 | 0.018246 | 0.001515 | −0.019285 | 0.002753 | −0.014885 | −0.020515 | 0.006343 | 0.030509 | 0.017421 | 0.002263 | 0.000692 | −0.018044 |
| 221 | 0.021588 | 0.010664 | −0.017131 | −0.009231 | −0.007034 | 0.001142 | −0.052585 | −0.047976 | −0.005526 | −0.007457 | 0.012102 | 0.029128 | 0.006582 | 0.000328 |
| 222 | −0.063934 | 0.019879 | 0.002675 | 0.008828 | −0.025325 | −0.040575 | 0.011948 | 0.002207 | −0.011846 | 0.000772 | −0.076255 | −0.014035 | 0.008438 | −0.003621 |
| 223 | 0.00037 | 0.00299 | 0.005209 | 0.006206 | −0.036868 | −0.086658 | −0.001453 | 0.008593 | −0.001481 | 0.004342 | −0.032154 | −0.015633 | 0.007933 | 0.002225 |
| 224 | 0.015737 | 0.023831 | 0.014203 | 0.009165 | 0.001351 | −0.010489 | 0.010187 | −0.010257 | 0.009795 | −0.053098 | −0.001756 | 0.005906 | −0.00281 | −0.025011 |
| 225 | 0.013679 | 0.033896 | 0.011007 | −0.002061 | −0.002436 | −0.024288 | 0.012014 | 0.014033 | 0.021161 | −0.045111 | −0.000933 | −0.024249 | −0.011545 | −0.026338 |
| 226 | −0.005261 | −0.003322 | 0.004716 | 0.00761 | −0.004788 | 0.030202 | 0.024951 | 0.039547 | −0.010234 | −0.009989 | 0.005353 | 0.001567 | 0.002677 | 0.004126 |
| 227 | 0.006172 | 0.01153 | 0.015758 | −0.003145 | 0.028858 | 0.003565 | 0.005529 | 0.028854 | −0.006523 | −0.037824 | 0.019819 | 0.018315 | 0.004062 | −0.017385 |
| 228 | −0.026381 | 0.033622 | 0.019011 | −0.004447 | −0.060208 | 0.004574 | 0.010712 | 0.026403 | 0.014088 | −0.014827 | −0.039497 | 0.00256 | −0.021589 | −0.014628 |
| 229 | 0.019038 | 0.035075 | 0.034289 | 0.013154 | −0.064787 | −0.025157 | −0.017352 | −0.063667 | 0.031763 | 0.041723 | 0.012261 | −0.00277 | −0.007861 | −0.000822 |
| 230 | 0.004378 | 0.023982 | 0.023104 | −0.005271 | 0.006716 | 0.023944 | −0.000982 | −0.038836 | −0.02017 | −0.00659 | 0.0108 | 0.02018 | 0.022747 | −0.012202 |
| 231 | 0.000149 | −0.025316 | 0.00006 | −0.012646 | 0.012162 | 0.020419 | −0.007898 | 0.041312 | 0.003499 | 0.004977 | 0.030751 | −0.015359 | −0.042795 | −0.029643 |
| 232 | −0.080998 | 0.044126 | 0.01879 | −0.039869 | −0.054817 | −0.013259 | 0.029291 | 0.008093 | 0.017832 | 0.008504 | 0.01317 | −0.003017 | 0.007043 | −0.026564 |
| 233 | −0.026392 | −0.01231 | −0.012066 | −0.015808 | −0.017885 | 0.002929 | −0.013923 | 0.000516 | 0.033411 | 0.028878 | 0.007256 | 0.027026 | 0.026086 | 0.026322 |
| 234 | −0.008844 | −0.071793 | −0.055015 | −0.005752 | −0.018665 | 0.026103 | 0.005034 | 0.013751 | −0.004419 | 0.006761 | −0.002915 | −0.014584 | −0.040479 | 0.000133 |
| 235 | −0.011208 | −0.060692 | −0.083288 | −0.021761 | −0.010893 | 0.000616 | −0.011877 | 0.030715 | −0.015118 | −0.008857 | −0.026831 | −0.023688 | −0.031079 | −0.004996 |
| 236 | −0.012282 | 0.007069 | 0.007447 | −0.032625 | −0.011174 | −0.000597 | 0.007064 | −0.000671 | −0.006412 | −0.034032 | 0.000867 | −0.006571 | −0.01609 | −0.062176 |
| 237 | 0.01753 | 0.021982 | 0.023664 | 0.033559 | 0.005881 | 0.008285 | 0.017169 | 0.024748 | 0.03524 | 0.011214 | 0.010065 | 0.000193 | −0.002175 | −0.002843 |
| 238 | −0.00686 | −0.002957 | −0.010872 | 0.020397 | 0.016248 | 0.013763 | 0.033925 | 0.035185 | 0.020654 | 0.025126 | 0.004296 | 0.042316 | −0.011114 | 0.013582 |
| 239 | −0.009031 | −0.002941 | −0.007032 | −0.010359 | 0.024691 | 0.006169 | 0.034889 | 0.052575 | 0.016333 | 0.009477 | 0.002315 | 0.007698 | −0.01307 | 0.003516 |
| 240 | −0.087983 | −0.118639 | −0.108845 | −0.01247 | 0.012969 | 0.001087 | −0.035153 | −0.015123 | 0.012961 | −0.013131 | −0.037612 | −0.005047 | −0.052135 | 0.019085 |
| 241 | −0.06226 | −0.071454 | −0.082114 | −0.050215 | −0.014747 | −0.004877 | −0.018548 | −0.036071 | 0.014171 | −0.022615 | −0.018018 | 0.00549 | −0.033836 | 0.006744 |
| 242 | 0.018124 | 0.018035 | −0.023258 | −0.069948 | −0.027172 | −0.018989 | −0.018067 | 0.024972 | 0.012429 | 0.033626 | −0.028483 | −0.006824 | −0.009918 | −0.037423 |
| 243 | −0.008393 | 0.014434 | −0.02895 | −0.069625 | −0.074262 | 0.001893 | −0.003506 | 0.039231 | 0.031415 | −0.003394 | −0.040822 | −0.018868 | −0.017474 | 0.015416 |
| 244 | 0.035126 | 0.027602 | −0.001452 | −0.036107 | 0.010201 | −0.025972 | −0.065986 | −0.039797 | 0.005861 | 0.016951 | 0.022373 | 0.00026 | 0.018759 | −0.003506 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 245 | 0.002559 | 0.029839 | 0.000333 | −0.062327 | 0.005659 | −0.003844 | −0.016559 | −0.116157 | 0.00678 | −0.00891 | 0.00342 | 0.001697 | −0.011742 | −0.004691 |
| 246 | −0.000999 | −0.022115 | 0.00612 | 0.034392 | 0.016906 | −0.0111 | −0.010087 | −0.017675 | 0.027805 | 0.032964 | −0.002423 | 0.02554 | 0.014561 | −0.002859 |
| 247 | 0.002121 | −0.006732 | 0.017207 | 0.022675 | 0.007673 | −0.002846 | 0.006742 | 0.007193 | 0.008115 | −0.033346 | −0.000257 | 0.008165 | 0.012369 | −0.023529 |
| 248 | −0.035903 | 0.013064 | −0.002231 | −0.008509 | 0.003139 | 0.008873 | 0.014208 | 0.013063 | 0.002715 | −0.031584 | −0.013417 | −0.013757 | −0.021914 | −0.017164 |
| 249 | 0.733507 | −0.072653 | −0.026248 | −0.026343 | −0.010486 | −0.034179 | 0.035675 | −0.009126 | 0.019993 | 0.023955 | −0.124895 | −0.063647 | −0.034547 | −0.015401 |
| 250 | −0.066478 | 0.827346 | −0.096774 | 0.003025 | 0.020668 | −0.012287 | −0.017708 | 0.014129 | −0.005478 | 0.01937 | −0.046976 | −0.053023 | −0.039232 | 0.016305 |
| 251 | −0.01858 | −0.101491 | 0.833477 | −0.061736 | 0.009084 | −0.013187 | −0.052169 | 0.004933 | −0.004137 | 0.002801 | −0.046591 | −0.047667 | −0.08178 | 0.013484 |
| 252 | −0.036698 | −0.00776 | −0.062278 | 0.784302 | −0.061933 | 0.011128 | −0.004317 | −0.053695 | −0.017163 | −0.009676 | −0.024704 | −0.122852 | −0.106091 | −0.052371 |
| 253 | 0.0005681 | 0.022787 | 0.023559 | −0.061957 | 0.782127 | −0.006893 | 0.004367 | −0.054187 | −0.012188 | −0.03681 | 0.0106861 | −0.021244 | −0.029851 | −0.031731 |
| 254 | −0.0166221 | 0.0002591 | −0.0007191 | −0.007207 | −0.003564 | 0.871805 | −0.051293 | −0.016872 | 0.026789 | 0.020595 | −0.035357 | −0.014552 | 0.006866 | 0.00439 |
| 255 | 0.039118 | 0.000703 | −0.029458 | −0.024672 | 0.002948 | −0.045267 | 0.884689 | −0.082556 | −0.002954 | 0.007225 | 0.00969 | 0.029509 | 0.01322 | 0.005186 |
| 256 | −0.014094 | 0.013257 | 0.032209 | −0.058066 | −0.049184 | 0.010007 | −0.046196 | 0.716057 | −0.041687 | −0.006337 | 0.041643 | 0.035504 | 0.015037 | −0.026679 |
| 257 | 0.000917 | −0.0218561 | 0.002194 | −0.015754 | −0.027176 | 0.030259 | 0.021614 | −0.022898 | 0.886886 | −0.047566 | 0.009232 | −0.022268 | 0.004301 | −0.005366 |
| 258 | 0.013174 | 0.013874 | 0.0019031 | −0.003587 | −0.028335 | 0.000185 | 0.013348 | 0.002156 | −0.043685 | 0.846441 | 0.0068931 | −0.005881 | −0.036901 | −0.016818 |
| 259 | −0.1189191 | −0.044435 | −0.04771 | −0.023707 | 0.001484 | −0.048802 | 0.005837 | 0.037382 | 0.011558 | 0.020485 | 0.861329 | −0.093456 | −0.058709 | 0.007148 |
| 260 | −0.059662 | −0.048528 | −0.030163 | −0.109306 | −0.021478 | −0.015939 | 0.022203 | 0.057527 | −0.000066 | −0.000757 | −0.079388 | 0.722 | −0.1394 | −0.025864 |
| 261 | −0.032193 | −0.041601 | −0.073146 | −0.079219 | −0.036713 | 0.001798 | −0.007454 | 0.000883 | −0.000467 | −0.036366 | −0.052638 | −0.139207 | 0.806926 | −0.051582 |
| 262 | −0.019338 | 0.024513 | 0.019136 | −0.058815 | −0.032701 | 0.009321 | 0.016331 | −0.018897 | −0.018344 | −0.013554 | −0.004244 | −0.03967 | −0.047672 | 0.880747 |
| 263 | −0.0240021 | 0.031087 | 0.004931 | −0.073667 | −0.052503 | 0.013393 | 0.013826 | −0.008061 | −0.027278 | −0.007194 | −0.025856 | −0.036794 | −0.034241 | −0.088486 |
| 264 | −0.081414 | −0.0163261 | 0.0060351 | 0.043119 | 0.000909 | −0.063884 | −0.021023 | −0.013827 | 0.011875 | 0.01459 | −0.088191 | −0.017119 | 0.021593 | 0.024001 |
| 265 | −0.026368 | −0.026891 | 0.017621 | 0.01242 | −0.014671 | −0.084974 | −0.016403 | −0.02661 | 0.015842 | −0.001326 | −0.03048 | −0.047915 | −0.029175 | −0.001478 |
| 266 | 0.04138 | −0.018385 | 0.008419 | −0.023862 | −0.043822 | −0.022304 | −0.028433 | −0.068496 | −0.005893 | −0.023748 | 0.027109 | −0.054282 | −0.072166 | −0.0211 |
| 267 | 0.005179 | −0.0155131 | 0.040126 | 0.045926 | −0.062837 | 0.005057 | 0.027674 | −0.001232 | 0.01833 | 0.002741 | 0.038301 | 0.01626 | 0.012349 | 0.009543 |
| 268 | −0.0034931 | −0.0089321 | 0.019343 | 0.007866 | −0.003274 | 0.028533 | 0.030272 | 0.040562 | −0.011588 | −0.000994 | 0.014915 | 0.0013751 | 0.030751 | 0.005663 |
| 269 | 0.0007461 | −0.011571 | 0.006746 | 0.009612 | −0.007855 | 0.026754 | 0.019064 | 0.027446 | −0.013135 | 0.015352 | 0.018778 | 0.00334 | 0.025517 | 0.006004 |
| 270 | 0.014218 | −0.008098 | −0.010494 | −0.002041 | 0.002296 | 0.023812 | 0.000634 | 0.036745 | −0.019328 | −0.009725 | 0.014834 | −0.003293 | −0.009341 | 0.003327 |
| 271 | 0.006766 | −0.014288 | −0.026113 | −0.007876 | −0.046431 | −0.029771 | −0.006162 | 0.018422 | 0.016208 | 0.031666 | −0.012937 | 0.016804 | 0.010545 | −0.011415 |
| 272 | 0.024021 | −0.001877 | −0.021791 | 0.025078 | −0.027715 | −0.009936 | −0.0022 | −0.012185 | 0.006244 | 0.007879 | −0.006412 | 0.019332 | −0.021465 | 0.020225 |
| 273 | −0.007621 | 0.004866 | −0.004156 | −0.012199 | 0.014656 | 0.01947 | 0.015906 | 0.023945 | −0.021833 | 0.0015771 | −0.015407 | −0.017147 | 0.0002091 | −0.002562 |
| 274 | −0.004467 | 0.002139 | −0.007671 | −0.004596 | 0.014982 | 0.015071 | 0.01038 | 0.023004 | −0.020408 | 0.005556 | −0.013533 | −0.018524 | −0.003117 | −0.000342 |
| 275 | 0.010312 | 0.008914 | −0.009131 | −0.002795 | 0.027917 | 0.020163 | −0.005567 | 0.002057 | −0.008016 | −0.021121 | 0.003738 | 0.01776 | 0.00047 | −0.013255 |
| 276 | −0.003261 | −0.00099 | 0.011894 | −0.034792 | −0.061054 | −0.014244 | 0.01009 | −0.01842 | 0.004772 | −0.026123 | −0.003131 | −0.012761 | −0.027421 | −0.06521 |
| 277 | 0.053741 | 0.030943 | 0.027415 | 0.025181 | 0.018533 | 0.006271 | 0.020377 | 0.053956 | 0.018396 | −0.012426 | 0.014787 | −0.023413 | 0.001168 | 0.007473 |
| 278 | 0.0661191 | 0.034965 | 0.028141 | 0.019589 | 0.02048 | 0.004973 | 0.0167 | 0.06546 | 0.0277251 | 0.011323 | 0.017819 | -.0342751 | −0.010566 | −0.004287 |
| 279 | 0.0031831 | −0.01497 | −0.0296551 | 0.006558 | 0.035305 | 0.015276 | 0.039989 | 0.070916 | 0.032131 | 0.028957 | −0.000675 | −0.007913 | −0.02763 | 0.020921 |
| 280 | 0.019449 | 0.038294 | 0.010481 | −0.016508 | −0.138111 | 0.006963 | −0.003266 | 0.012898 | 0.044821 | −0.022689 | −0.026584 | 0.035151 | 0.003306 | 0.020874 |
| 281 | −0.017263 | −0.011173 | −0.011284 | 0.039161 | 0.036873 | −0.003452 | −0.006046 | 0.01967 | 0.044112k | 0.001586 | −0.028534 | 0.003327 | −0.012448 | 0.027649 |
| 282 | 0.0042761 | −0.0084621 | −0.0164251 | −0.005782 | 0.01909 | −0.016082 | −0.007857 | 0.022639 | 0.027551 | −0.005198 | −0.018394 | 0.004755 | 0.007192 | 0.010128 |
| 283 | −0.009282 | −0.006396 | −0.00818 | 0.012515 | 0.017136 | −0.003203 | 0.010581 | 0.027685 | 0.032237 | −0.017479 | −0.00783 | −0.030788 | −0.019781 | −0.01623 |
| 284 | −0.010256 | −0.027924 | −0.00051 | −0.002021 | −0.014802 | 0.021685 | 0.023954 | −0.020603 | −0.080241 | −0.017836 | 0.003943 | −0.023863 | 0.010313 | 0.004367 |
| 285 | −0.017666 | −0.013871 | 0.003538 | −0.018336 | −0.018826 | 0.012068 | 0.026249 | −0.007813 | −0.080464 | −0.003106 | −0.006185 | −0.043407 | 0.019197 | −0.008066 |
| 286 | −0.008442 | 0.012984 | 0.011413 | −0.010316 | −0.019399 | −0.01521 | 0.021206 | −0.023741 | −0.020359 | −0.074714 | −0.000306 | −0.006871 | −0.003257 | −0.002956 |
| 287 | −0.002399 | 0.02805 | 0.001901 | −0.025862 | −0.033458 | −0.004381 | 0.009703 | −0.003272 | −0.029432 | −0.097035 | 0.000604 | −0.008986 | −0.01526 | 0.002165 |
| 288 | 0.011542 | 0.018218 | −0.00809 | 0.008357 | −0.006455 | 0.01216 | 0.012226 | 0.012441 | −0.010615 | −0.12019 | 0.006579 | −0.023074 | −0.036962 | −0.026075 |
| 289 | 0.006416 | 0.003012 | −0.000215 | −0.02011 | −0.001468 | 0.003594 | −0.002155 | −0.01581 | −0.025722 | −0.018067 | 0.015533 | −0.022959 | −0.022996 | −0.079608 |
| 290 | 0.002412 | −0.002354 | −0.012582 | 0.003333 | −0.0161 | −0.003311 | −0.008216 | −0.009497 | −0.002038 | −0.000154 | −0.007573 | 0.009319 | −0.021482 | 0.005946 |
| 291 | 0.001369 | −0.00824 | −0.011041 | 0.004319 | −0.013554 | −0.004948 | −0.008154 | −0.010939 | 0.000463 | 0.002186 | −0.008779 | 0.010166 | −0.019097 | 0.002974 |
| 292 | −0.003071 | −0.030822 | −0.032625 | 0.017573 | −0.019056 | −0.014358 | −0.003968 | −0.007521 | 0.002225 | 0.010356 | −0.012328 | 0.036717 | −0.009016 | 0.009342 |
| 293 | −0.004797 | −0.0389 | 0.009297 | 0.033326 | 0.019646 | −0.00566 | 0.005594 | −0.034808 | 0.0099 | 0.009158 | −0.008213 | 0.02662 | 0.016262 | 0.006671 |
| 294 | 0.000047 | −0.004467 | 0.012034 | 0.028281 | 0.037552 | 0.010234 | 0.01422 | 0.02837 | 0.02619 | 0.003688 | −0.002322 | 0.004559 | 0.009153 | 0.002169 |
| 295 | −0.02608 | −0.008249 | 0.030539 | 0.027999 | 0.029842 | 0.000199 | 0.021556 | 0.011875 | 0.007442 | 0.056351 | −0.006759 | 0.004651 | 0.023476 | −0.012062 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 296 | −0.006128 | 0.012737 | 0.014121 | 0.004979 | −0.011318 | −0.001131 | 0.004776 | 0.020206 | 0.021235 | 0.025663 | −0.002153 | −0.020156 | −0.014301 | −0.02643 |
| 297 | −0.023697 | −0.01005 | 0.019363 | 0.005493 | 0.007785 | 0.000038 | 0.016002 | −0.016235 | −0.006786 | 0.038031 | −0.004183 | −0.016906 | 0.001635 | −0.019744 |
| 298 | 0.02702 | 0.006434 | 0.002302 | 0.007411 | −0.016714 | −0.01954 | −0.012166 | 0.00685 | −0.001598 | −0.003933 | 0.004992 | −0.023011 | −0.013834 | −0.00692 |
| 299 | 0.007984 | 0.005397 | −0.009662 | −0.002006 | −0.004416 | −0.004145 | 0.009714 | 0.024055 | 0.012019 | −0.003191 | 0.011853 | −0.012336 | −0.012182 | 0.005456 |
| 300 | −0.00429 | 0.016443 | 0.0132891 | 0.020179 | −0.028126 | −0.02278 | −0.004047 | 0.007678 | 0.000103 | 0.006745 | 0.007271 | 0.015263 | −0.008923 | −0.04886 |
| 301 | −0.000071 | 0.000077 | 0.00402 | 0.007098 | 0.004362 | 0.014305 | 0.011106 | 0.011431 | −0.030001 | 0.025021 | 0.006744 | −0.009494 | 0.010009 | −0.004825 |
| 302 | 0.01316 | 0.005979 | −0.001061 | 0.025075 | 0.007174 | 0.017067 | 0.006329 | 0.02886 | −0.014037 | −0.002021 | 0.0006 | 0.006128 | −0.000935 | −0.016216 |
| 303 | 0.036998 | 0.018576 | 0.011794 | 0.010775 | −0.018927 | −0.014352 | 0.020637 | 0.03804 | 0.040127 | −0.023872 | 0.020937 | −0.015067 | −0.008617 | 0.009105 |
| 304 | 0.035225 | 0.017135 | −0.024142 | −0.009644 | −0.052982 | −0.00068 | 0.010164 | 0.024183 | 0.033873 | −0.044423 | 0.007916 | −0.007429 | −0.04516 | 0.003528 |
| 305 | 0.018511 | 0.0027851 | −0.0051461 | 0.040687 | 0.058411 | −0.029616 | 0.001875 | 0.003999 | 0.001848 | 0.041684 | 0.00536 | 0.039622 | 0.004285 | 0.010554 |
| 306 | 0.003269 | −0.029812 | −0.027359 | −0.000587 | 0.004303 | 0.013525 | 0.002955 | 0.018709 | −0.012015 | −0.017796 | 0.010734 | 0.009607 | −0.018399 | 0.00214 |
| 307 | −0.008748 | 0.001381 | 0.034463 | −0.040449 | −0.059905 | 0.011515 | 0.032058 | −0.012495 | −0.00022Y | −0.014954 | 0.027032 | 0.010144 | 0.025572 | 0.026983 |
| 308 | −0.010316 | 0.008478 | −0.02187 | −0.028458 | −0.032509 | 0.013259 | −0.0016 | 0.001054 | −0.009878 | −0.004299 | −0.007606 | −0.01703 | −0.022929 | −0.008904 |
| 309 | −0.0250441 | −0.0116851 | −0.0051371 | 0.001971 | 0.008748 | −0.005825 | −0.001125 | 0.019443 | −0.001313 | 0.0059341 | −0.013159 | 0.0119111 | 0.0096171 | 0.000588 |
| 310 | −0.015422 | −0.022232 | −0.005752 | 0.017709 | 0.038715 | −0.004918 | 0.009733 | 0.022651 | 0.015457 | 0.035013 | −0.003356 | 0.006583 | 0.027533 | 0.008998 |
| 311 | 0.013232 | 0.013997 | 0.014954 | −0.004607 | 0.005213 | −0.008206 | 0.008902 | 0.014597 | 0.008282 | 0.017535 | −0.011551 | −0.030434 | 0.001038 | −0.002183 |
| 312 | 0.058707 | 0.029502 | −0.012693 | −0.022889 | −0.007475 | −0.002208 | −0.024741 | −0.038451 | −0.021397 | −0.011288 | 0.037626 | 0.03988 | 0.038398 | 0.000205 |
| 313 | 0.021026 | 0.010398 | 0.007108 | −0.00228 | −0.009628 | −0.013112 | −0.018803 | −0.010767 | −0.029252 | −0.00302 | −0.001464 | 0.009376 | 0.002495 | 0.013277 |
| 314 | −0.021223 | −0.021222 | −0.000463 | −0.005117 | 0.00796 | −0.049102 | −0.019329 | −0.028714 | 0.010403 | 0.006411 | −0.023016 | 0.024414 | 0.017117 | −0.014568 |
| 315 | 0.016664 | 0.002689 | 0.007994 | 0.010408 | −0.000355 | −0.021385 | −0.015199 | 0.007317 | 0.004689 | −0.016182 | 0.017565 | 0.015645 | −0.000568 | 0.001301 |
| 316 | 0.006363 | 0.015852 | 0.042164 | 0.055197 | −0.064176 | −0.004916 | −0.019961 | 0.000231 | −0.014683 | −0.015269 | 0.00145 | 0.011059 | 0.011766 | 0.001073 |
| 317 | 0.003806 | −0.024982 | 0.004155 | 0.010168 | 0.01021 | −0.013245 | −0.005297 | 0.003859 | −0.028155 | 0.012502 | −0.000648 | −0.015978 | 0.005567 | 0.006387 |
| 318 | 0.007566 | 0.006328 | 0.003673 | 0.023372 | −0.007226 | −0.025592 | −0.004503 | 0.035237 | 0.00168 | 0.012108 | −0.014785 | −0.003069 | 0.010439 | −0.002985 |
| 319 | 0.011583 | 0.002479 | 0.019058 | 0.006924 | −0.026146 | −0.021181 | −0.005889 | −0.008772 | −0.001298 | −0.013498 | 0.016369 | −0.000769 | 0.015649 | −0.002676 |
| 320 | 0.052931 | −0.017079 | −0.0293461 | −0.011556 | −0.015535 | 0.002446 | −0.002717 | −0.013978 | −0.03199 | −0.056348 | 0.019072 | 0.007672 | 0.006323 | 0.016685 |
| 321 | 0.002863 | −0.002983 | −0.011947 | −0.034657 | −0.000324 | 0.02373 | 0.010533 | −0.015674 | −0.023597 | −0.014237 | 0.005321 | −0.004505 | −0.023321 | −0.020313 |
| 322 | 0.012522 | −0.020585 | −0.019875 | −0.025229 | −0.007729 | −0.012429 | −0.007824 | 0.04752 | 0.017123 | 0.01771 | −0.012295 | −0.001399 | 0.008131 | −0.002405 |
| 323 | −0.003881 | −0.048335 | −0.022985 | 0.002548 | 0.005991 | 0.015821 | 0.006836 | 0.022636 | −0.028971 | 0.008473 | −0.020961 | 0.018757 | 0.013944 | 0.029256 |
| 324 | −0.02594 | −0.01649 | −0.011965 | 0.009445 | 0.011999 | 0.000006 | −0.008844 | 0.016447 | 0.010626 | 0.027814 | −0.021227 | −0.026578 | −0.013502 | 0.012292 |
| 325 | −0.010281 | 0.005023 | 0.026665 | 0.005501 | 0.010413 | 0.010329 | 0.002906 | −0.010702 | 0.011557 | 0.006797 | −0.014231 | 0.003804 | −0.02308 | −0.007164 |
| 326 | −0.017694 | 0.004752 | −0.009064 | −0.004618 | 0.029751 | 0.029995 | 0.008812 | −0.005029 | 0.005101 | −0.032082 | −0.009494 | 0.008936 | −0.01567 | 0.026914 |
| 327 | 0.01663 | 0.010441 | −0.018109 | 0.0262531 | 0.014189 | −0.012764 | 0.005921 | 0.047286 | 0.009206 | 0.012319 | −0.011688 | 0.017555 | −0.003296 | 0.008863 |
| 328 | −0.070865 | −0.009751 | −0.004852 | −0.043839 | −0.037774 | 0.046771 | 0.016303 | −0.03379 | −0.010403 | 0.0292 | −0.012515 | −0.049509 | −0.016849 | −0.019431 |
| 329 | 0.003013 | 0.013656 | −0.011238 | 0.007716 | 0.024385 | −0.004965 | 0.008375 | 0.023182 | −0.014189 | 0.009288 | −0.01675 | 0.008765 | 0.020057 | 0.011248 |
| 330 | 0.008485 | −0.020749 | −0.007423 | −0.009996 | 0.058065 | 0.006486 | 0.00318 | 0.003602 | 0.026417 | 0.012521 | −0.015613 | −0.060817 | −0.034716 | 0.003665 |
| 331 | −0.005697 | −0.012789 | 0.01298 | 0.027418 | 0.018025 | −0.00762 | 0.011783 | 0.011869 | 0.018623 | −0.008199 | −0.012139 | 0.021851 | 0.016445 | 0.005122 |
| 332 | 0.024195 | 0.009595 | −0.018243 | −0.018759 | −0.021748 | 0.003189 | 0.005583 | −0.008057 | 0.006732 | −0.012195 | 0.015273 | −0.025846 | −0.021646 | 0.021634 |
| 333 | −0.025528 | −0.010344 | 0.016568 | 0.007152 | 0.01963 | 0.012957 | 0.003857 | −0.01157 | −0.012679 | 0.023747 | −0.021106 | 0.003589 | 0.003162 | 0.012721 |
| 334 | −0.060339 | −0.006927 | −0.004231 | −0.051578 | 0.031596 | 0.027389 | 0.013717 | −0.04058 | −0.029523 | −0.013049 | 0.006448 | 0.034904 | 0.001402 | −0.017396 |
| 335 | 0.000693 | −0.001223 | 0.001274 | 0.016582 | −0.007077 | 0.008137 | 0.003472 | −0.002235 | 0.005911 | 0.002931 | −0.012627 | 0.000955 | −0.002112 | 0.02952 |
| 336 | −0.000436 | 0.008639 | 0.02829 | 0.023254 | 0.032774 | −0.001662 | 0.005045 | −0.027168 | 0.016706 | −0.015252 | 0.009433 | 0.032138 | 0.035465 | −0.008715 |
| 337 | −0.017377 | −0.024135 | −0.0348 | 0.022626 | −0.003376 | −0.011954 | −0.011047 | −0.000589 | 0.016751 | 0.028088 | 0.018654 | −0.002759 | 0.007286 | 0.01987 |
| 338 | 0.005061 | 0.000475 | 0.000443 | −0.014661 | 0.000414 | 0.007518 | 0.013293 | 0.023531 | 0.010694k | −0.017327 | 0.022803 | 0.023172 | 0.022938 | −0.00391 |
| 339 | −0.040625 | 0.002728 | −0.017577 | −0.034291 | 0.022971 | −0.003698 | 0.042813 | 0.026353 | 0.020215 | −0.02815 | −0.024213 | 0.00194 | −0.035714 | −0.0121 |
| 340 | 0.020573 | 0.017292 | 0.021035 | −0.027575 | −0.004838 | 0.017418 | 0.003272 | −0.002505 | −0.010941 | −0.000393 | 0.013423 | −0.016611 | 0.005512 | 0.034268 |

| | JD | JE | JF | JG | JH | JI | JJ | JK | JL | JM | JN | JO | JP | JQ |
|---|---|---|---|---|---|---|---|---|---|---|---|---|---|---|
| 1 | −0.034191 | 0.111306 | 0.132335 | 0.067189 | 0.020914 | 0.025643 | 0.046964 | 0.016539 | 0.100106 | 0.034537 | 0.052792 | 0.06012 | 0.077998 | −0.098154 |
| 2 | 0.024062 | 0.009872 | −0.044457 | −0.016248 | −0.090294 | −0.019942 | −0.014156 | −0.044456 | 0.070019 | −0.089528 | −0.044908 | −0.046157 | −0.010585 | −0.000587 |
| 3 | −0.016237 | −0.015725 | 0.008219 | 0.04457 | −0.0766 | −0.058353 | −0.082296 | −0.084057 | −0.135443 | −0.10141 | −0.071614 | −0.084972 | −0.090922 | −0.010513 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 4 | 0.017191 | 0.03156 | 0.074646 | 0.054663 | −0.002292 | 0.00289 | 0.020619 | −0.017385 | −0.00319 | −0.055764 | −0.030617 | −0.031801 | −0.074111 | −0.019858 |
| 5 | 0.002331 | −0.034985 | −0.062106 | 0.03006 | −0.032453 | −0.064751 | −0.010126 | −0.010019 | −0.001204 | 0.006742 | −0.042569 | −0.020962 | 0.033644 | −0.002742 |
| 6 | 0.082338 | −0.024812 | 0.051551 | 0.063855 | 0.018512 | −0.015033 | −0.001129 | 0.00316 | 0.151294 | 0.078454 | −0.000528 | 0.013663 | −0.008903 | 0.075697 |
| 7 | −0.037376 | −0.030335 | −0.07998 | −0.049468 | 0.029314 | 0.036964 | 0.085434 | 0.064287 | 0.100666 | 0.033438 | 0.005012 | 0.012407 | 0.007079 | 0.000503 |
| 8 | −0.012885 | −0.025509 | −0.032694 | −0.031275 | 0.070041 | 0.035123 | 0.045128 | 0.02955 | 0.022957 | −0.015396 | −0.012169 | 0.004639 | 0.020675 | 0.009295 |
| 9 | −0.049814 | −0.037554 | −0.058125 | −0.025532 | 0.015255 | −0.024686 | −0.008319 | 0.002619 | 0.000355 | −0.026654 | −0.025705 | −0.023099 | −0.02494 | 0.04145 |
| 10 | −0.017757 | −0.061202 | −0.023313 | −0.018477 | 0.109471 | 0.011917 | −0.015215 | −0.053204 | −0.028729 | 0.085799 | 0.012593 | 0.001404 | −0.033254 | 0.01601 |
| 11 | −0.016951 | 0.064962 | 0.029638 | −0.039879 | −0.049757 | 0.010768 | 0.024926 | 0.024401 | −0.001565 | −0.021776 | 0.053845 | 0.063 | 0.016781 | 0.008352 |
| 12 | 0.003173 | 0.057876 | 0.022022 | −0.032469 | −0.103629 | 0.017826 | 0.006605 | 0.02073 | −0.041337 | −0.007399 | 0.060139 | 0.060285 | 0.012381 | −0.027197 |
| 13 | 0.036021 | −0.035771 | −0.11524 | −0.085357 | −0.013968 | −0.084573 | −0.049665 | −0.057031 | −0.026691 | 0.108243 | 0.052262 | 0.060197 | 0.035447 | 0.032733 |
| 14 | −0.012564 | −0.021067 | −0.004806 | −0.012976 | −0.041391 | 0.006842 | −0.010319 | 0.012998 | −0.130504 | −0.098518 | −0.049822 | −0.051966 | −0.054548 | −0.032977 |
| 15 | 0.017118 | 0.019856 | −0.010832 | −0.054821 | 0.002684 | −0.047566 | −0.029085 | −0.007774 | 0.053901 | 0.104033 | 0.002784 | 0.012176 | −0.00167 | 0.083062 |
| 16 | −0.027272 | −0.059671 | −0.044035 | −0.019632 | 0.028115 | −0.000593 | −0.006814 | 0.01205 | 0.076106 | 0.01325 | 0.019798 | 0.013655 | 0.015512 | 0.048156 |
| 17 | 0.01193 | 0.029554 | 0.016657 | 0.013276 | 0.071434 | 0.0452 | 0.037253 | 0.034977 | 0.093439 | 0.058371 | 0.049761 | 0.040202 | −0.024441 | −0.03938 |
| 18 | 0.027758 | 0.040292 | −0.008961 | −0.005687 | 0.004657 | 0.024808 | −0.029594 | −0.019068 | 0.072908 | 0.050375 | 0.055004 | 0.048312 | 0.000541 | 0.019191 |
| 19 | −0.01425 | 0.038725 | 0.044287 | −0.00146 | 0.093745 | 0.047882 | 0.074795 | 0.108301 | −0.04385 | 0.021207 | 0.008004 | 0.01057 | 0.04029 | −0.077379 |
| 20 | 0.083126 | 0.009267 | 0.031609 | 0.053045 | 0.019242 | 0.007509 | −0.003675 | −0.008543 | 0.043252 | 0.025869 | −0.013098 | −0.01667 | −0.008675 | 0.076765 |
| 21 | 0.000265 | −0.001242 | 0.028943 | 0.004471 | −0.008559 | 0.0054 | −0.011271 | −0.014154 | −0.005488 | 0.017625 | 0.022727 | 0.014409 | 0.019336 | −0.022734 |
| 22 | 0.012415 | 0.050163 | −0.013376 | −0.026893 | −0.057608 | 0.075113 | 0.046763 | 0.045334 | −0.003452 | −0.054062 | 0.061655 | 0.064114 | 0.020868 | −0.032743 |
| 23 | −0.041783 | 0.018012 | −0.001489 | −0.016169 | −0.053102 | −0.016354 | 0.003529 | 0.013332 | −0.085449 | −0.004781 | −0.016692 | −0.015142 | −0.01779 | −0.062218 |
| 24 | −0.047456 | 0.019677 | 0.053154 | 0.032094 | 0.041148 | −0.001886 | 0.014246 | −0.0415 | −0.068668 | 0.000782 | 0.000192 | 0.005925 | −0.031391 | 0.044262 |
| 25 | 0.025241 | −0.018413 | −0.042768 | 0.042689 | −0.071359 | 0.027222 | 0.014361 | 0.016297 | 0.088457 | −0.003201 | −0.011011 | −0.007604 | −0.028092 | 0.072067 |
| 26 | −0.004625 | −0.006653 | 0.039937 | −0.019266 | 0.136098 | 0.003535 | −0.022487 | 0.014517 | 0.01003 | 0.066135 | 0.074064 | 0.058071 | 0.022938 | 0.026807 |
| 27 | −0.040198 | 0.105451 | 0.050057 | −0.002597 | 0.086999 | 0.031216 | 0.018573 | 0.025662 | 0.111682 | −0.106065 | −0.196153 | −0.192481 | −0.12869 | −0.122816 |
| 28 | −0.035784 | 0.008883 | −0.006386 | −0.026883 | −0.020016 | −0.042691 | −0.037032 | −0.053924 | −0.046476 | 0.067924 | 0.025948 | 0.024907 | −0.073408 | −0.044434 |
| 29 | −0.009631 | 0.023635 | 0.009255 | 0.019756 | 0.018474 | 0.024696 | 0.017389 | −0.005427 | −0.042414 | 0.052494 | 0.019637 | 0.00817 | 0.022789 | −0.010191 |
| 30 | −0.033733 | −0.164481 | −0.035671 | 0.102358 | 0.006085 | 0.044267 | 0.071277 | 0.061236 | −0.073115 | −0.033214 | 0.019094 | 0.026499 | −0.044327 | −0.014945 |
| 31 | −0.0449 | −0.066028 | −0.055513 | −0.017422 | 0.110487 | 0.019641 | 0.016979 | −0.026174 | 0.12285 | 0.086924 | −0.041139 | −0.039251 | −0.092679 | 0.031986 |
| 32 | 0.034956 | 0.011644 | −0.007513 | 0.044274 | −0.059078 | −0.025914 | −0.003717 | −0.015557 | −0.020841 | 0.000075 | 0.015363 | 0.007333 | 0.038913 | 0.026944 |
| 33 | 0.05264 | 0.049573 | −0.037645 | −0.051495 | −0.023196 | −0.005167 | 0.005829 | 0.021854 | −0.149456 | −0.038797 | −0.032415 | −0.037682 | 0.049114 | 0.087565 |
| 34 | 0.003922 | −0.017975 | 0.002057 | −0.005092 | −0.032991 | −0.02465 | −0.011593 | −0.043788 | 0.001767 | −0.032039 | −0.037561 | −0.034062 | −0.123981 | −0.028492 |
| 35 | 0.042698 | −0.070101 | −0.021126 | 0.016242 | 0.042508 | −0.006739 | 0.020208 | 0.045566 | 0.088453 | −0.015232 | 0.025469 | 0.024653 | 0.008349 | −0.011102 |
| 36 | −0.02969 | 0.021511 | −0.014655 | −0.017071 | 0.004834 | −0.027635 | −0.036948 | −0.005333 | −0.018986 | 0.041235 | 0.043605 | 0.039303 | 0.084119 | 0.003599 |
| 37 | −0.043299 | 0.018976 | 0.007347 | −0.02121 | −0.039687 | −0.042998 | −0.055016 | −0.023387 | −0.034193 | 0.016074 | −0.028624 | −0.013701 | 0.01943 | −0.046439 |
| 38 | 0.030776 | 0.005073 | 0.045017 | 0.027581 | −0.019576 | −0.072324 | −0.08142 | −0.025887 | −0.030414 | −0.038384 | −0.014157 | −0.014255 | 0.064214 | 0.035497 |
| 39 | −0.030368 | 0.005811 | 0.073959 | 0..090388 | −0.055414 | −0.022297 | −0.045877 | −0.027266 | −0.008967 | 0.002478 | −0.028377 | −0.031293 | 0.009496 | −0.020945 |
| 40 | 0.013352 | 0.024424 | 0.00735 | −0.018718 | 0.05571 | 0.03946 | 0.036544 | 0.046239 | 0.026186 | 0.066305 | 0.025434 | 0.026023 | 0.034632 | 0.02821 |
| 41 | 0.010887 | 0.040355 | −0.007249 | −0.044072 | −0.009174 | 0.043472 | 0.0041 | 0.018517 | −0.015195 | −0.019154 | 0.017483 | 0.003904 | 0.019567 | −0.038108 |
| 42 | −0.000415 | 0.004894 | −0.008948 | −0.021323 | 0.033752 | −0.001111 | 0.004933 | 0.004601 | −0.002211 | 0.0143911 | −0.000852 | 0.0034071 | 0.0040381 | 0.026758 |
| 43 | −0.018754 | 0.005394 | −0.074388 | −0.000147 | 0.050348 | −0.011023 | 0.031329 | 0.021964 | −0.035977 | 0.017717 | 0.004652 | 0.015332 | 0.023684 | −0.06608 |
| 44 | 0.004289 | 0.003264 | 0.050387 | −0.01363 | 0.057492 | −0.022664 | −0.000573 | 0.015541 | 0.008238 | 0.003544 | −0.018779 | −0.007459 | 0.013593 | 0.035458 |
| 45 | −0.034648 | −0.01408 | 0.062768 | 0.069071 | −0.032007 | −0.02786 | −0.065759 | −0.060602 | 0.034853 | −0.04261 | −0.00097 | 0.000219 | 0.01966 | −0.013373 |
| 46 | 0.002231 | −0.037809 | −0.133418 | −0.103705 | −0.098202 | −0.041058 | −0.025698 | 0.036972 | −0.053986 | −0.091323 | 0.005066 | 0.013059 | 0.172822 | 0.00674 |
| 47 | 0.059693 | 0.011247 | 0.027172 | −0.009791 | −0.06595 | 0.006213 | 0.004869 | 0.034299 | 0.064322 | 0.026218 | 0.054369 | 0.047379 | −0.014881 | 0.016958 |
| 48 | −0.052208 | −0.04028 | −0.0261871 | −0.043291 | 0.017692 | −0.001082 | 0.015365 | 0.009914 | 0.00715 | −0.000317 | −0.02619 | −0.016433 | −0.059044 | −0.015457 |
| 49 | −0.052878 | 0.008571 | 0.0356271 | −0.006435 | 0.013502 | 0.025328 | 0.000439 | 0.014188 | 0.101148 | 0.049389 | 0.023553 | 0.01576 | 0.020213 | 0.017544 |
| 50 | −0.00077 | −0.00733 | 0.017766 | 0.149845 | −0.038983 | −0.004494 | −0.025503 | −0.001161 | −0.037606 | −0.04729 | −0.00547 | −0.002913 | 0.025439 | −0.056435 |
| 51 | 0.017078 | 0.023218 | −0.023682 | −0.063884 | 0.067391 | 0.066348 | 0.093646 | 0.053871 | −0.008583 | −0.01824 | −0.001973 | 0.015884 | −0.134201 | −0.045075 |
| 52 | −0.048499 | 0.049178 | 0.097735 | 0.075987 | −0.036811 | −0.080077 | −0.033453 | −0.037671 | 0.032807 | 0.075009 | −0.037721 | −0.009295 | −0.066769 | 0.002773 |
| 53 | −0.013405 | 0.029607 | −0.028927 | −0.014636 | −0.099205 | −0.025971 | −0.005451 | −0.015749 | −0.073932 | −0.034905 | 0.012948 | 0.012705 | 0.055105 | 0.080258 |
| 54 | −0.042405 | −0.017584 | −0.053444 | −0.075188 | 0.049625 | −0.00025 | 0.037276 | −0.047233 | −0.004535 | 0.07596 | 0.015217 | 0.023897 | −0.108601 | 0.011688 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 55 | −0.023383 | −0.093492 | −0.131045 | −0.053823 | −0.031531 | 0.027413 | 0.009197 | 0.025207 | 0.133562 | −0.022191 | 0.000486 | −0.00259 | 0.041938 | −0.032622 |
| 56 | −0.007596 | 0.111889 | 0.077474 | 0.066677 | −0.023306 | −0.009846 | −0.02284 | −0.046172 | 0.080581 | 0.019445 | 0.008525 | 0.003813 | −0.085129 | −0.011397 |
| 57 | −0.011985 | −0.0368951 | −0.030485 | −0.043307 | 0.016078 | 0.018184 | 0.014139 | 0.0489 | 0.007743 | −0.003933 | 0.03793 | 0.029114 | 0.030291 | −0.010966 |
| 58 | −0.020569 | 0.0651751 | −0.0091431 | −0.067857 | 0.048847 | 0.01917 | 0.013042 | 0.016655 | 0.117 | 0.044451 | 0.051819 | 0.0592051 | 0.0591231 | −0.009139 |
| 59 | 0.0295231 | −0.0169561 | −0.047866 | −0.008117 | −0.072053 | −0.017318 | −0.019995 | −0.020389 | 0.020944 | −0.064719 | −0.02138 | −0.022266 | 0.03533 | 0.010787 |
| 60 | −0.019993 | −0.027198 | −0.014533 | −0.043374 | 0.007032 | −0.010762 | −0.00503 | 0.029565 | −0.058712 | 0.069614 | 0.060153 | 0.061442 | 0.055741 | −0.0543 |
| 61 | −0.029911 | 0.026594 | −0.008073 | 0.010864 | 0.034414 | −0.018447 | −0.011153 | −0.01996 | 0.008208 | 0.051701 | −0.027946 | −0.021677 | −0.012012 | 0.008473 |
| 62 | 0.034823 | −0.00194 | −0.002709 | −0.012007 | 0.000004 | −0.020225 | −0.004521 | −0.030084 | 0.052164 | 0.019083 | 0.016732 | 0.022092 | 0.002477 | 0.064306 |
| 63 | −0.001367 | −0.079079 | 0.027576 | 0.059745 | −0.009721 | 0.006614 | 0.01971 | 0.033006 | 0.000987 | 0.033754 | 0.056828 | 0.048037 | 0.007704 | 0.02661 |
| 64 | −0.002718 | 0.041499 | 0.046981 | 0.004313 | −0.055299 | −0.027668 | −0.021138 | 0.00507 | −0.137805 | −0.121205 | 0.000131 | 0.002009 | 0.085368 | −0.073025 |
| 65 | −0.041794 | 0.021145 | 0.00421 | −0.025413 | 0.025907 | 0.02659 | 0.020831 | −0.035061 | 0.015714 | −0.008097 | −0.030975 | −0.029932 | 0.045417 | −0.038619 |
| 66 | 0.037164 | 0.001997 | 0.007848 | −0.049511 | −0.001177 | 0.063774 | 0.043736 | −0.025792 | 0.074312 | −0.008697 | 0.032356 | 0.023856 | −0.029253 | −0.008204 |
| 67 | 0.050944 | −0.066083 | −0.129728 | −0.041344 | −0.055786 | 0.012676 | 0.008168 | 0.0083 | 0.009436 | −0.011374 | 0.028922 | 0.019989 | −0.052148 | 0.012702 |
| 68 | 0.009937 | −0.070023 | −0.05613 | 0.001079 | 0.136076 | 0.035522 | −0.005395 | 0.006083 | −0.015553 | 0.03344 | −0.017356 | −0.024921 | −0.042407 | 0.029433 |
| 69 | −0.010369 | 0.020094 | 0.097484 | 0.084077 | 0.077234 | 0.025426 | 0.02253 | 0.013087 | 0.099689 | 0.045865 | −0.008553 | −0.006479 | 0.050943 | 0.038844 |
| 70 | −0.018138 | −0.015563 | 0.069718 | −0.000548 | −0.040271 | −0.052789 | −0.023408 | 0.017551 | −0.116934 | −0.03385 | −0.012525 | 0.005733 | −0.070321 | −0.092282 |
| 71 | 0.008703 | −0.000619 | 0.08139 | 0.079265 | −0.109992 | 0.056883 | 0.059538 | 0.029466 | −0.06203 | −0.043508 | 0.026515 | 0.023872 | −0.046608 | 0.01886 |
| 72 | 0.030183 | −0.004971 | −0.019776 | −0.017657 | 0.017123 | −0.006733 | 0.004211 | 0.043932 | −0.066104 | −0.057044 | −0.025653 | −0.020378 | 0.055699 | −0.029775 |
| 73 | 0.054352 | 0.030598 | 0.024815 | 0.020266 | 0.059878 | 0.003419 | −0.054708 | −0.039832 | 0.097741 | 0.0002 | −0.026207 | −0.047775 | −0.037766 | 0.004073 |
| 74 | 0.063009 | 0.042273 | 0.009156 | 0.00497 | 0.025381 | 0.022023 | 0.003997 | −0.00896 | −0.007663 | −0.014888 | −0.030124 | −0.031725 | 0.007571 | −0.024639 |
| 75 | −0.01208 | 0.08279 | 0.044849 | −0.018302 | 0.097434 | 0.058179 | 0.023997 | 0.015284 | −0.132025 | −0.04278 | −0.031732 | −0.053363 | 0.006768 | 0.010752 |
| 76 | −0.05827 | −0.026752 | 0.000267 | 0.0684 | 0.045894 | −0.005455 | 0.00572 | 0.00695 | 0.039465 | 0.067254 | 0.020046 | 0.023716 | 0.065718 | 0.014883 |
| 77 | 0.028518 | 0.083804 | −0.028774 | −0.024947 | −0.018248 | −0.013483 | −0.005056 | −0.0317 | 0.128924 | −0.05006 | −0.004365 | 0.007192 | −0.050199 | 0.038906 |
| 78 | 0.033509 | −0.032813 | −0.059477 | −0.044588 | −0.027371 | −0.005665 | 0.005691 | 0.013193 | −0.024695 | 0.032451 | 0.018827 | 0.013043 | 0.012809 | −0.038131 |
| 79 | −0.007511 | −0.047863 | −0.020716 | −0.017161 | −0.072639 | 0.009484 | −0.011691 | −0.026844 | 0.135983 | −0.00473 | −0.000797 | −0.007126 | 0.017119 | −0.045028 |
| 80 | −0.005795 | 0.007853 | 0.009228 | −0.629285 | −0.007767 | −0.027136 | −0.023781 | 0.02022 | −0.027829 | −0.01277 | 0.000162 | 0.008731 | 0.038267 | −0.008489 |
| 81 | −0.028886 | 0.073558 | 0.066137 | −0.038417 | 0.051558 | 0.005444 | −0.035825 | 0.004612 | 0.034582 | 0.003546 | −0.003232 | −0.008953 | 0.042046 | 0.011897 |
| 82 | 0.068255 | −0.053677 | 0.025343 | 0.078905 | −0.037703 | −0.041303 | 0.00385 | 0.046596 | 0.026574 | −0.050559 | 0.01386 | 0.034706 | 0.109486 | −0.044694 |
| 83 | −0.020275 | −0.000446 | 0.032777 | 0.083444 | −0.021504 | −0.044543 | 0.004653 | 0.013045 | 0.038946 | −0.024957 | −0.022354 | −0.005054 | 0.074195 | 0.029536 |
| 84 | 0.012713 | −0.017717 | 0.068223 | 0.072951 | 0.037141 | 0.052783 | 0.00828 | −0.028619 | 0.021181 | 0.001918 | −0.009031 | −0.020821 | −0.082923 | 0.057842 |
| 85 | −0.016893 | −0.013079 | −0.060781 | −0.049664 | 0.038093 | −0.01347 | 0.0266 | 0.017739 | −0.081174 | 0.04093 | 0.014502 | 0.022132 | 0.012374 | −0.067152 |
| 86 | −0.11259 | −0.051348 | −0.005104 | 0.007273 | −0.059649 | −0.031987 | −0.020845 | −0.041249 | −0.010247 | 0.011103 | 0.010524 | 0.028516 | −0.037352 | 0.071577 |
| 87 | 0.001124 | 0.038487 | 0.033955 | 0.051713 | −0.021042 | −0.06272 | −0.005281 | 0.005448 | 0.130895 | 0.035827 | −0.020637 | −0.010459 | 0.026964 | −0.014804 |
| 88 | −0.025599 | −0.020494 | −0.034995 | −0.016465 | 0.010643 | 0.055413 | 0.030134 | 0.034335 | −0.041375 | −0.030202 | 0.039272 | 0.012653 | 0.029767 | −0.164743 |
| 89 | 0.049528 | 0.023879 | −0.067537 | −0.117335 | −0.080483 | −0.044147 | −0.027762 | −0.041647 | 0.02216 | 0.003587 | 0.021181 | 0.019001 | −0.018041 | −0.021677 |
| 90 | −0.006648 | −0.107734 | −0.0352681 | −0.033789 | 0.02478 | 0.035073 | 0.02617 | −0.022101 | −0.152037 | −0.027685 | 0.010048 | 0.012518 | −0.009717 | 0.015442 |
| 91 | −0.063949 | 0.042594 | 0.039352 | 0.065579 | −0.048583 | −0.013537 | −0.070097 | −0.010283 | −0.034664 | 0.0416 | 0.051256 | 0.055101 | 0.026251 | −0.025242 |
| 92 | 0.008081 | −0.000525 | −0.033594 | −0.019295 | 0.057495 | −0.003583 | −0.000525 | 0.025876 | 0.0549 | 0.036475 | 0.001529 | 0.004344 | 0.083917 | 0.009471 |
| 93 | 0.01019 | 0.014559 | −0.04591 | −0.109322 | −0.020369 | 0.035362 | 0.014438 | −0.000576 | −0.011705 | −0.024569 | 0.072238 | 0.058502 | 0.011357 | 0.032879 |
| 94 | 0.042644 | −0.015116 | 0.019358 | 0.008458 | 0.014401 | 0.014572 | −0.029844 | 0.014185 | −0.031679 | −0.034345 | 0.007697 | −0.001641 | 0.001075 | 0.087066 |
| 95 | 0.005305 | 0.064401 | 0.011651 | −0.024748 | −0.035139 | −0.001893 | 0.00142 | −0.039229 | −0.081256 | 0.003673 | 0.046874 | 0.046441 | 0.034513 | −0.035301 |
| 96 | 0.032224 | 0.03991 | −0.006235 | −0.020085 | −0.052389 | −0.00842 | −0.048772 | −0.017577 | −0.006644 | −0.028115 | 0.009082 | −0.003596 | 0.038042 | −0.031353 |
| 97 | −0.047932 | −0.063193 | −0.025824 | 0.008377 | −0.081301 | −0.06134 | −0.037551 | 0.002695 | −0.007871 | −0.105847 | −0.05639 | −0.044703 | −0.001815 | −0.004798 |
| 98 | −0.035016 | −0.032642 | −0.002565 | 0.033899 | −0.008157 | 0.047823 | 0.075358 | 0.101596 | 0.002774 | −0.00111 | −0.000151 | −0.017771 | 0.027407 | −0.018954 |
| 99 | 0.028288 | 0.0019621 | 0.063051 | 0.025336 | −0.019083 | 0.022011 | −0.010974 | −0.082821 | 0.025944 | −0.0860611 | −0.048546 | −0.0733851 | −0.0401611 | 0.07476 |
| 100 | −0.0298381 | −0.047145 | −0.016474 | −0.006475 | 0.007972 | −0.015415 | −0.002756 | −0.007265 | −0.038876 | 0.003833 | −0.004231 | 0.000399 | 0.00236 | 0.039374 |
| 101 | −0.013038 | 0.010683 | 0.004789 | 0.007853 | −0.022932 | −0.005626 | −0.00452 | 0.004808 | 0.019965 | −0.016865 | −0.008006 | −0.007202 | −0.000633 | 0.006038 |
| 102 | −0.000069 | −0.010232 | 0.00806 | 0.019908 | 0.036948 | 0.003711 | 0.012669 | 0.02479 | −0.013831 | −0.011725 | 0.007432 | 0.005727 | 0.018314 | −0.034589 |
| 103 | −0.002207 | 0.020405 | −0.001761 | −0.027594 | 0.021405 | 0.020178 | 0.007649 | −0.001432 | 0.029824 | 0.001641 | 0.011607 | 0.012737 | −0.039457 | −0.066573 |
| 104 | −0.012839 | −0.040676 | −0.023214 | −0.002202 | 0.024151 | 0.001323 | 0.010476 | 0.015665 | −0.033876 | 0.012293 | 0.018745 | 0.0204321 | 0.013195 | 0.03012 |
| 105 | −0.037987 | −0.017201 | 0.022147 | 0.004115 | −0.041288 | −0.017625 | −0.033758 | −0.017907 | 0.004388 | 0.014708 | 0.042647 | 0.046218 | 0.036832 | 0.011258 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 106 | −0.005299 | −0.016768 | −0.004524 | 0.007617 | 0.027549 | 0.021652 | 0.021527 | 0.022045 | 0.017132 | 0.017285 | −0.007809 | −0.005216 | −0.018876 | 0.009548 |
| 107 | −0.005352 | 0.000764 | −0.024313 | 0.011 | 0.031544 | 0.009707 | 0.029655 | 0.015811 | −0.054469 | −0.003476 | −0.012205 | −0.00652 | −0.013143 | 0.018576 |
| 108 | −0.021221 | −0.014901 | 0.028578 | −0.005466 | −0.01531 | −0.00542 | −0.022919 | −0.02818 | −0.007259 | −0.008698 | −0.000455 | −0.00604 | −0.049869 | −0.034218 |
| 109 | −0.010534 | 0.00302 | 0.010887 | −0.022839 | 0.033996 | 0.001547 | −0.017074 | 0.011263 | −0.036551 | −0.008473 | 0.011392 | 0.000643 | −0.010103 | 0.017902 |
| 110 | 0.039918 | 0.036285 | 0.006997 | −0.02907 | 0.01313 | 0.019444 | 0.019225 | −0.021717 | 0.103864 | 0.01799 | 0.010639 | 0.015938 | 0.046713 | 0.058887 |
| 111 | −0.005609 | −0.001557 | −0.004668 | 0.021917 | −0.04255 | −0.015151 | −0.01003 | 0.017401 | −0.052738 | −0.003469 | −0.001929 | 0.001611 | 0.018481 | −0.006394 |
| 112 | −0.026114 | −0.004887 | 0.010513 | −0.013227 | −0.015403 | −0.036121 | −0.015606 | −0.033874 | 0.025436 | 0.027554 | 0.013531 | 0.012379 | 0.007373 | −0.011002 |
| 113 | −0.022835 | 0.005507 | 0.008191 | 0.015166 | 0.004038 | 0.024959 | 0.023352 | 0.030501 | −0.060912 | −0.002254 | 0.018168 | 0.015566 | 0.039473 | −0.046359 |
| 114 | −0.033664 | −0.042235 | −0.052841 | −0.039128 | 0.082167 | 0.007783 | 0.018639 | 0.039932 | −0.012145 | −0.041791 | −0.0160451 | −0.015641 | 0.038049 | −0.026524 |
| 115 | 0.012837 | 0.040652 | 0.00501 | −0.041518 | −0.030482 | −0.003282 | −0.004562 | 0.001821 | −0.078424 | 0.006121 | 0.008101 | 0.00724 | 0.007027 | 0.024307 |
| 116 | 0.006262 | −0.002868 | −0.009768 | −0.029906 | 0.015084 | −0.020606 | −0.000694 | 0.010696 | −0.099525 | 0.007878 | 0.003803 | 0.002254 | −0.005427 | 0.003685 |
| 117 | 0.007341 | −0.012789 | −0.000731 | 0.014855 | 0.025209 | 0.000283 | −0.013855 | −0.011088 | −0.004404 | −0.023633 | −0.01101 | −0.017487 | 0.002923 | 0.003552 |
| 118 | 0.01955 | −0.000023 | −0.002343 | −0.025094 | 0.021329 | 0.033537 | −0.004571 | 0.003255 | −0.016569 | −0.008884 | 0.046506 | 0.024032 | −0.008771 | 0.008532 |
| 119 | −0.013235 | 0.000905 | −0.017066 | −0.007166 | −0.020369 | −0.002427 | −0.010469 | −0.012927 | 0.046855 | −0.014781 | −0.011821 | −0.017403 | −0.00249 | 0.028288 |
| 120 | −0.011632 | −0.015554 | 0.000931 | −0.000423 | 0.039583 | −0.010384 | 0.008237 | 0.000236 | 0.018237 | 0.006886 | −0.024223 | −0.02217 | −0.015616 | 0.013759 |
| 121 | −0.011467 | −0.001661 | 0.016483 | 0.025507 | 0.015674 | −0.015303 | 0.009683 | 0.013147 | 0.042283 | 0.007285 | −0.005846 | −0.002061 | 0.017644 | −0.01003 |
| 122 | 0.009868 | 0.022457 | 0.023601 | 0.020261 | 0.001907 | −0.023445 | −0.019379 | −0.014913 | −0.040158 | 0.034853 | 0.012479 | 0.01097 | 0.021013 | −0.003762 |
| 123 | 0.026308 | 0.04081 | 0.013698 | 0.005634 | −0.003446 | −0.00329 | −0.0114 | −0.028922 | 0.023996 | 0.007506 | 0.014747 | 0.013303 | 0.003462 | 0.004406 |
| 124 | −0.004704 | 0.006152 | 0.001969 | 0.0034291 | −0.014707 | −0.01032 | −0.003169 | −0.027851 | 0.017038 | −0.015375 | −0.024051 | −0.02915 | −0.01802 | 0.018648 |
| 125 | −0.010156 | 0.000902 | 0.008504 | 0.015552 | 0.009303 | 0.017572 | 0.015368 | 0.021714 | 0.012386 | 0.026425 | 0.008997 | 0.002613 | −0.009529 | −0.019645 |
| 126 | 0.003777 | 0.009501 | 0.006839 | 0.010869 | 0.019265 | −0.002204 | 0.008997 | 0.014183 | −0.011812 | 0.01706 | 0.004322 | −0.000235 | 0.008464 | −0.007518 |
| 127 | 0.00415 | −0.665659 | −0.020497 | −0.66145 | 0.015419 | 0.000312 | 0.003742 | 0.004448 | 0.00381 | 0.0166 | 0.006008 | 0.003457 | 0.000194 | 0.007601 |
| 128 | −0.040699 | 0.038561 | 0.031486 | −0.005017 | −0.007012 | −0.021054 | −0.015489 | 3.018608 | −6.664597 | 0.019738 | 6.663313 | 0.010891 | 6.662652 | 6.633368 |
| 129 | 0.026561 | 0.011825 | −0.645048 | −0.029564 | −0.030614 | −0.037251 | −0.024977 | −0.027714 | −0.086189 | 0.024538 | 0.001789 | 0.008583 | 0.012077 | 6.628379 |
| 130 | −0.007515 | 0.001667 | 0.033277 | 0.034404 | −0.04369 | −0.006171 | 0.00922 | 0.011813 | 0.0681281 | 0.002907 | 0.002187 | 0.002768 | 0.029174 | 0.017946 |
| 131 | 0.03471 | 0.0137571 | −0.004817 | 0.624859 | −0.021186 | −0.050493 | −0.003538 | −0.002514 | −0.002112 | 0.064474 | −0.015801 | 0.003692 | −0.002984 | 0.016736 |
| 132 | −0.033884 | 0.062204 | −0.663979 | −0.662696 | 0.666932 | 0.000913 | −0.016534 | 0.028649 | −0.004896 | −0.005565 | −0.00115 | −0.009847 | −0.022625 | −0.016716 |
| 133 | −0.024468 | 0.61952 | 0.010204 | −0.666461 | 0.001691 | −0.030509 | −6.020386 | −6.660244 | 0.009542 | 0.017165 | 0.022145 | 0.024696 | 6.661826 | 0.015793 |
| 134 | −0.032907 | 0.016577 | 0.03846 | 0.022425 | −0.005492 | −0.666617 | −0.001672 | −0.00593 | −0.005169 | 0.002414 | −0.026162 | −0.026999 | −0.021277 | −0.000841 |
| 135 | −0.021161 | −0.009429 | 0.016469 | −0.002625 | 0.012036 | −0.000087 | −0.001505 | −0.011823 | 0.029517 | 0.005458 | −0.006646 | −0.00389 | −0.029067 | 0.004054 |
| 136 | 0.0044651 | −0.042288 | −0.021307 | 0.007385 | −0.03619 | 0.031151 | 0.030874 | 0.041269 | −0.004335 | −0.011641 | 0.009266 | 0.000908 | 0.033795 | −0.024604 |
| 137 | 0.006163 | 0.028344 | 0.01795 | 0.02505 | 0.006039 | 0.011528 | 0.010667 | 0.003181 | 0.031134 | −0.002014 | −0.008766 | −0.008483 | −0.011918 | 0.026019 |
| 138 | −0.006253 | −0.037435 | 0.00842 | 0.611475 | 0.000677 | 0.006684 | 0.007899 | 6.629663 | −6.030555 | 6.664064 | −6.606113 | −0.001516 | 6.611602 | −6.622758 |
| 139 | −0.653439 | 0.006437 4 | 0.626113 | −0.002795 | 0.039183 | 0.018089 | 0.032808 | 0.025354 | −0.017205 | −0.01519 | 0.002183 | −0.001411 | 0.004916 | −0.013211 |
| 140 | 0.014939 | 0.016909 | 0.040898 | 0.020318 | −0.003005 | 0.008554 | −0.01001 | −0.019912 | −0.039712 | 0.032499 | 0.020846 | 0.015319 | 0.005699 | 0.018177 |
| 141 | 0.011635 | −0.061563 | 0.005016 | 0.054442 | 0.024475 | −0.008486 | 0.005035 | −0.006018 | −0.048121 | −0.005899 | −0.010443 | −0.002735 | −0.011616 | 0.014601 |
| 142 | 0.6222381 | 0.629762 | −0.667648 | −0.031705 | 0.000218 | −0.012114 | −0.017748 | −0.01029 | −0.019643 | −0.033074 | −0.012974 | −0.022857 | −0.029294 | −0.005173 |
| 143 | −0.667136 | −0.014026 | −0.004768 | 0.024064 | 0.028391 | −0.043965 | −0.029415 | −6.61 4043 | −6.045367 | 6.666272 | −0.663993 | 0.002681 | 0.03 716 | −6.623555 |
| 144 | −0.661277 | −0.06951 | −0.664937 | −0.010187 | 0.048523 | 0.014565 | 0.024484 | −0.004516 | −0.007322 | 0.00606 | 0.00375 | 0.005542 | 0.003661 | 0.007374 |
| 145 | 0.012075 | −0.022834 | −0.014867 | 0.014337 | −0.016129 | −0.020171 | 0.008031 | 0.016898 | 0.022091 | −0.043694 | 0.010261 | 0.016649 | 0.039764 | −0.003855 |
| 146 | −0.027455 | 0.007791 | 0.622826 | 0.005705 | 0.005386 | 0.001168 | 0.007886 | −0.006636 | 0.024227 | 0.021324 | −0.0022491 | 0.001395 | −0.014377 | 0.01474 |
| 147 | −0.647562 | 0.669194 | 0.626515 | 0.01395S | −0.010135 | −0.612753 | −0.002553 | −0.001596 | 0.036347 | 0.013833 | −0.001309 | 0.003376 | 0.011976 | 0.025611 |
| 148 | −0.000368 | −6,631741 | 0.33645 | −0.669129 | 0.661535 | 0.61921 | 0.015204 | 6.664246 | −6.622998 | −0.01698 | 0.018231 | 0.013086 | −6.6149 | −6.625583 |
| 149 | 0.662682 | 0.612462 | 0.666711 | −0.029591 | 0.001676 | 0.010639 | 0.014251 | 0.012438 | −0.024869 | 0.002262 | 0.011961 | 0.01313 | 0.023367 | −0.030085 |
| 150 | 0.02297 | −0.001419 | 0.007193 | −0.014675 | 0.036537 | 0.020433 | 0.013996 | 0.009871 | −0.038836 | 0.005173 | −0.024323 | −0.03482 | −0.031336 | 0.014102 |
| 151 | 0.002252 | −0.022078 | 0.013825 | 0.062013 | −0.000259 | 0.016148 | 6.022315 | 6.628268 | 6.026022 | 6.61686 | 0.004378 | 0.004657 | 6.64648 | 6.017075 |
| 152 | −0.016735 | −0.013273 | −0.013587 | 0.017519 | −0.63381 | 0.006253 | 0.010375 | 0.008598 | −0.006619 | −0.001399 | 0.021486 | 0.021104 | 0.031133 | −0.014049 |
| 153 | 0.005901 | 0.614979 | 0.62933 | 0.66333 | 0.628358 | 0.667724 | 0.014745 | 6.662646 | 0.006404 | 6.03001 | 6.621639 | 0.032892 | −0.02881 | 0.015581 |
| 154 | 0.023541 | 0.035902 | 0.63615 | 0.005967 | −0.000754 | 0.632264 | 0.014423 | −0.002525 | 6.666196 | −0.026642 | −0.001535 | −0.00957 | 0.603595 | 0.022617 |
| 155 | 0.002826 | −0.005598 | 0.004544 | 0.003239 | −0.010361 | 0.621521 | 0.013292 | 0.01493 | −0.008153 | −0.02203 | 0.000458 | 0.000456 | 0.016782 | −0.005514 |
| 156 | −0.034568 | 0.019281 | 0.047605 | −0.019062 | −0.037984 | 0.028868 | 0.013588 | −0.002988 | −0.034036 | 0.001263 | 0.034 | 0.030114 | −0.016607 | −0.010767 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 157 | −0.616505 | −0.016586 | −0.015155 | 0.615259 | 0.062758 | 0.011911 | 0.024166 | 0.031974 | −6.055878 | 0.017768 | −0.018899 | −0.012946 | −0.020639 | 0.001134 |
| 158 | −0.012444 | −0.004899 | −0.010208 | 0.011931 | 0.011008 | −0.669332 | −0.014292 | −6.622922 | 0.026925 | 0.005819 | −0.002941 | −0.007045 | 6.614433 | −0.005282 |
| 159 | 0.025668 | −0.667453 | 0.031083 | 0.008035 | −0.045863 | −0.0098 | 0.001021 | −0.014848 | 0.042988 | −0.001035 | 0.005805 | 0.012979 | −0.04129 | 0.026816 |
| 160 | −0.034113 | 0.001751 | −0.011002 | −0.017266 | 0.021846 | 0.027688 | 0.023658 | 0.036512 | 0.058768 | 0.028176 | 0.020441 | 0.01949 | −0.015822 | 0.049021 |
| 161 | −0.001194 | −0.021517 | −0.055255 | −0.023801 | −0.025285 | −0.029453 | −0.008425 | 0.001128 | 0.006401 | −0.008097 | −0.001637 | −0.000721 | 0.014608 | −0.041867 |
| 162 | −0.661444 | −0.043057 | 0.661941 | 0.0234691 | 0.005542 | 0.027034 | 0.012196 | −0.003255 | −0.05726 | −0.038907 | 0.006548 | −0.001643 | −0.039465 | −0.0071 |
| 163 | 0.014685 | −0.051558 | 0.45452 | −0.004477 | −0.014579 | −0.612552 | −6.003634 | −0.010875 | −0.029116 | −0.013068 | .0.022505 | −0.623843 | −0.059421 | 0.00226 |
| 164 | 0.6241561 | 0.621681 | −0.633675 | −0.019217 | e.ei i 375 | 0.02591 | 0.031922 | 0.019864 | 0.009335 | 0.012102 | 0.024424 i | 0.01707: | −0.005214 | −0.017972 |
| 165 | 0.0068271 | 0.0037451 | 0.0189431 | 0.035515 | 0.075934 | 0.021455 | 0.008747 | 0.026158 | 0.020271 | 0.0160991 | −0.0197281 | −0.0114281 | 0.0038511 | −0.011428 |
| 166 | 0.001782 | 0.022865 | −0.005011 | −0.013724 | 0.035881 | −0.004164 | 0.000859 | 0.003673 | 0.0295251 | 0.0181361 | −0.022409 | −0.0226641 | 0.001511 | −0.055214 |
| 167 | −0.030947 | −0.047798 | −0.009484 | −0.008108 | 0.01596 | 0.03027 | 0.049271 | 0.027208 | −0.011267 | −0.011808 | 0.006124 | 0.006947 | −0.002649 | −0.045157 |
| 168 | 0.015946 | −0.034866 | −0.04356 | −0.028983 | 0.00159 | 0.014745 | 0.015729 | −0.00689 | −0.069879 | 0.02366 | 0.023856 | 0.016369 | −0.06605 | −0.001758 |
| 169 | 0.02204 | −0.002613 | 0.013026 | 0.029342 | −0.009043 | −0.004682 | 0.001635 | −0.009151 | 0.013522 | 0.01165 | 0.006552 | 0.007399 | −0.001619 | −0.011343 |
| 170 | 0.024091 | 0.021922 | 0.019872 | 0.033468 | −0.011452 | 0.013441 | 0.005924 | −0.006682 | 0.000973 | −0.001937 | 0.008811 | 0.004521 | 0.006389 | 0.000587 |
| 171 | 0.022908 | −0.008902 | 0.01244 | 0.025425 | −0.018222 | −0.00639 | −0.00099 | −0.016481 | −0.023661 | 0.022334 | 0.022973 | 0.025423 | 0.008416 | 0.004188 |
| 172 | 0.013933 | −0.028309 | −0.002804 | 0.013334 | −0.016617 | −0.015331 | −0.001173 | 0.005875 | 0.000048 | −0.010981 | −0.00742 | −0.00643 | 0.014095 | −0.001302 |
| 173 | 0.029361 | −0.020824 | 0.018618 | 0.020168 | −0.006584 | −0.012604 | −0.013005 | 0.001562 | 0.001981 | 0.014922 | −0.003072 | 0.001137 | −0.008486 | 0.045283 |
| 174 | 0.019264 | 0.029411 | −0.004719 | −0.009465 | −0.029961 | −0.00276 | −0.00011 | 0.003002 | 0.034232 | −0.017093 | −0.001464 | 0.002064 | 0.014585 | −0.005475 |
| 175 | −0.010248 | 0.006594 | −0.016185 | −0.006033 | −0.00483 | 0.000128 | −0.009544 | −0.017879 | −0.024649 | −0.014177 | −0.004918 | −0.004582 | 0.007776 | −0.041296 |
| 176 | 0.016827 | −0.013611 | −0.020653 | −0.002358 | −0.013361 | −0.002971 | 0.021289 | 0.017618 | −0.024529 | −0.001939 | 0.029587 | 0.031501 | 0.023635 | −0.072239 |
| 177 | 0.007291 | 0.030655 | 0.034395 | 0.035881 | 0.026001 | 0.030504 | −0.010404 | −0.000175 | 0.007584 | 0.024208 | 0.016664 | 0.003908 | −0.011521 | −0.017772 |
| 178 | −0.017509 | −0.010304 | 0.004643 | 0.023556 | 0.0264 | −0.001807 | 0.021051 | 0.008012 | 0.003723 | 0.000254 | −0.008722 | −0.002225 | −0.018115 | 0.015324 |
| 179 | 0.004419 | 0.01192 | −0.000533 | 0.004843 | 0.00896 | 0.009199 | −0.00108 | −0.00569 | 0.018421 | −0.007396 | −0.005133 | −0.007138 | −0.015133 | 0.007287 |
| 180 | −0.00688 | 0.000822 | 0.005308 | 0.015343 | 0.008694 | 0.012065 | 0.008453 | 0.01751 | 0.019138 | 0.012558 | 0.004517 | 0.002884 | −0.011963 | 0.003617 |
| 181 | −0.014706 | 0.010461 | 0.015786 | 0.010022 | 0.011656 | 0.018072 | 0.006354 | 0.01332 | 0.0173931 | −0.001854 | 0.0012411 | −0.00109 | −0.001195 | 0.009725 |
| 182 | −0.010955 | 0.014797 | 0.008064 | −0.000838 | 0.028983 | 0.021705 | 0.002319 | −0.005182 | −0.03422 | 0.009568 | 0.011188 | 0.001063 | 0.00172 | 0.031137 |
| 183 | −0.00483 | 0.008616 | 0.004658 | 0.005638 | 0.009928 | 0.001692 | −0.01249 | −0.026331 | −0.036461 | 0.027132 | 0.01059 | 0.011553 | −0.000046 | 0.026632 |
| 184 | −0.010195 | −0.017335 | −0.016465 | −0.027159 | −0.027581 | −0.012882 | −0.008667 | −0.015856 | −0.028262 | 0.024037 | 0.015669 | 0.023149 | −0.006718 | −0.019574 |
| 185 | 0.008051 | 0.012673 | 0.011626 | −0.018489 | 0.016711 | −0.011088 | −0.017368 | 0.007473 | −0.008699 | 0.019876 | 0.003802 | 0.00313 | 0.05482 | −0.019099 |
| 186 | 0.039886 | 0.003477 | 0.001989 | 0.001716 | −0.010625 | 0.00498 | 0.016465 | 0.029991 | −0.017055 | 0.014925 | −0.016022 | −0.017127 | 0.044406 | −0.003691 |
| 187 | 0.020772 | −0.027764 | −0.009304 | 0.006824 | −0.005571 | −0.002441 | −0.002596 | 0.004133 | 0.005027 | 0.013499 | 0.00497 | −0.000269 | −0.008429 | 0.032624 |
| 188 | 0.010036 | −0.01617 | −0.01548 | −0.018534 | −0.008038 | 0.003019 | 0.002246 | 0.008457 | 0.014677 | 0.001466 | 0.012074 | 0.011058 | 0.002274 | 0.013332 |
| 189 | 0.003595 | 0.002153 | −0.018896 | −0.032944 | −0.019171 | −0.018739 | −0.024027 | −0.028952 | 0.029655 | −0.009482 | 0.005627 | 0.007303 | 0.000857 | 0.030427 |
| 190 | −0.005804 | −0.008344 | −0.032805 | 0.002821 | −0.008815 | −0.009983 | −0.009333 | −0.003647 | −0.003868 | 0.005485 | −0.005298 | −0.005294 | −0.004773 | −0.021796 |
| 191 | 0.007711 | 0.007731 | −0.01609 | −0.00189 | −0.008899 | 0.002742 | −0.015758 | −0.005828 | 0.005858 | −0.002843 | −0.00824 | −0.014753 | 0.002477 | −0.004603 |
| 192 | 0.007662 | −0.068859 | −0.031816 | 0.018886 | 0.056614 | 0.01012 | 0.023619 | 0.010826 | −0.04347 | −0.001924 | −0.013601 | −0.017315 | 0.061372 | 0.042701 |
| 193 | 0.004232 | −0.014108 | −0.046822 | −0.020605 | 0.010297 | 0.014231 | 0.003216 | −0.018527 | −0.009296 | −0.007462 | −0.000899 | −0.005542 | −0.02103 | 0.023188 |
| 194 | 0.012332 | 0.009769 | −0.038351 | −0.026177 | −0.027817 | −0.005196 | −0.00419 | −0.010705 | 0.053346 | −0.000376 | 0.007776 | 0.013211 | −0.025097 | −0.027027 |
| 195 | 0.014223 | 0.037799 | −0.060732 | −0.09125 | −0.016458 | −0.005988 | −0.008712 | −0.004188 | 0.017354 | −0.038818 | −0.027972 | −0.03121 | 0.004283 | −0.004313 |
| 196 | −0.021417 | −0.003976 | −0.043349 | −0.059827 | 0.013155 | −0.010203 | 0.000145 | 0.00175 | −0.009271 | −0.000337 | −0.016679 | −0.017521 | −0.008734 | −0.027292 |
| 197 | −0.005757 | 0.012848 | 0.000555 | −0.012853 | 0.033747 | −0.009944 | −0.003747 | −0.018223 | 0.020986 | 0.022309 | −0.008746 | −0.005011 | 0.007832 | −0.008797 |
| 198 | −0.021541 | 0.038926 | 0.006794 | −0.032014 | −0.021622 | −0.034225 | −0.020964 | −0.022664 | −0.014092 | −0.000565 | −0.008212 | −0.001528 | −0.019586 | 0.00786 |
| 199 | 0.018672 | 0.033631 | −0.03129 | −0.012387 | −0.015182 | −0.012407 | 0.015409 | −0.001984 | 0.009259 | 0.021112 | −0.036026 | −0.02511 | −0.007155 | 0.015756 |
| 200 | −0.039057 | 0.021949 | −0.000133 | −0.019767 | −0.011126 | 0.000803 | −0.001664 | −0.000283 | 0.00073 | −0.026397 | −0.001289 | 0.000651 | −0.018134 | 0.022302 |
| 201 | −0.000137 | 0.021352 | −0.005265 | −0.024591 | −0.001499 | −0.002294 | 0.014357 | 0.023644 | −0.001221 | 0.032358 | 0.022975 | 0.02361 | 0.013784 | 0.023243 |
| 202 | −0.041159 | 0.016336 | 0.027861 | 0.012313 | −0.00417 | −0.021675 | −0.006067 | −0.01948 | −0.025626 | −0.002814 | −0.029292 | −0.019488 | 0.005961 | 0.056371 |
| 203 | −0.018327 | 0.018838 | −0.016873 | −0.001617 | −0.014517 | −0.019667 | 0.013808 | 0.010088 | 0.011696 | −0.013664 | −0.000297 | 0.010763 | 0.009815 | 0.006593 |
| 204 | −0.020311 | −0.008569 | −0.020751 | −0.029658 | −0.0076 | −0.008537 | −0.032053 | −0.011829 | 0.005412 | −0.006721 | −0.014072 | −0.014422 | −0.01412 | −0.003177 |
| 205 | 0.015247 | 0.02574 | 0.001498 | −0.01883 | 0.064522 | 0.022139 | 0.00331 | 0.023459 | 0.032856 | 0.041072 | −0.011309 | −0.018419 | −0.006765 | −0.017129 |
| 206 | −0.005828 | −0.025398 | −0.022575 | 0.005883 | 0.002828 | 0.026009 | 0.023416 | −0.005306 | −0.0229 | −0.016943 | −0.004399 | −0.01089 | −0.05049 | −0.02417 |
| 207 | −0.002039 | 0.019761 | 0.031045 | 0.031492 | −0.007492 | 0.010254 | 0.002216 | −0.006483 | 0.009662 | −0.015814 | −0.019858 | −0.013794 | −0.078595 | −0.015058 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 208 | 0.052959 | −0.006042 | 0.025567 | −0.004704 | −0.049402 | 0.013068 | 0.020704 | 0.030668 | 0.002403 | −0.036295 | 0.03552 | 0.039108 | 0.029199 | 0.000747 |
| 209 | −0.023195 | −0.029248 | 0.046521 | 0.034547 | 0.027633 | 0.008241 | 0.001344 | −0.023091 | 0.011478 | 0.034118 | 0.02296 | 0.030748 | 0.029769 | −0.024632 |
| 210 | −0.021637 | 0.02568 | 0.042848 | 0.03068 | 0.00556 | −0.005943 | 0.014324 | 0.000034 | −0.037907 | 0.045131 | 0.007501 | 0.018318 | −0.000622 | −0.040473 |
| 211 | −0.003837 | −0.01578 | 0.008906 | −0.013019 | 0.029073 | −0.017357 | −0.011116 | 0.017822 | −0.022709 | 0.022818 | −0.008091 | 0.001416 | 0.023459 | 0.013507 |
| 212 | 0.010658 | −0.024577 | 0.006018 | 0.01153 | 0.019479 | −0.022121 | −0.02832 | 0.003062 | 0.003307 | 0.000412 | −0.015767 | −0.013557 | 0.057138 | 0.010404 |
| 213 | 0.02274 | −0.044905 | −0.03325 | −0.000985 | −0.04949 | 0.005368 | 0.010859 | 0.027786 | −0.044985 | −0.028006 | 0.018054 | 0.008276 | 0.029944 | −0.003264 |
| 214 | 0.009613 | −0.012605 | −0.016707 | −0.008057 | 0.007104 | 0.002229 | −0.00385 | 0.004128 | −0.010718 | −0.002848 | −0.001661 | −0.000802 | −0.009885 | 0.012931 |
| 215 | 0.019298 | −0.018896 | −0.014932 | 0.0218 | 0.026471 | −0.003817 | −0.011464 | 0.015804 | 0.044444 | 0.016046 | −0.015532 | −0.008341 | −0.036668 | 0.055388 |
| 216 | −0.010954 | −0.011856 | 0.018564 | 0.006008 | −0.012194 | 0.005241 | 0.026922 | 0.011179 | 0.023539 | 0.058587 | 0.044073 | 0.051536 | −0.03867 | −0.007344 |
| 217 | −0.015946 | −0.016896 | −0.042754 | −0.034806 | −0.008219 | 0.017557 | −0.003892 | −0.00068 | 0.041085 | 0.013516 | 0.008591 | 0.0008 | 0.027836 | 0.031918 |
| 218 | 0.013913 | 0.020369 | 0.02579 | 0.013033 | 0.002611 | −0.002689 | −0.006415 | 0.004319 | 0.005349 | 0.00056 | 0.001812 | 0.008034 | 0.014747 | 0.011079 |
| 219 | 0.015914 | 0.006495 | 0.021799 | 0.013462 | 0.012995 | 0.01008 | 0.005154 | 0.011934 | 0.015966 | −0.003911 | 0.012249 | 0.014265 | 0.014272 | −0.003635 |
| 220 | −0.019183 | 0.017439 | −0.024436 | −0.035159 | −0.029261 | 0.009516 | −0.017905 | −0.012839 | 0.037419 | 0.016388 | 0.002383 | −0.004044 | 0.017706 | 0.013728 |
| 221 | −0.007248 | 0.008849 | 0.052466 | 0.019307 | 0.019714 | 0.009527 | 0.003431 | 0.009845 | 0.001953 | 0.018376 | 0.010551 | 0.01407 | −0.008361 | 0.013641 |
| 222 | −0.023016 | −0.106401 | −0.039015 | 0.010949 | 0.035584 | 0.004948 | 0.001515 | 0.019436 | −0.022356 | −0.002629 | −0.008977 | −0.002871 | 0.009991 | 0.027918 |
| 223 | −0.004582 | −0.035005 | −0.051915 | −0.031762 | −0.005356 | 0.005538 | −0.004712 | 0.001612 | −0.004576 | 0.000129 | 0.014947 | 0.018345 | 0.003762 | 0.003457 |
| 224 | −0.016896 | −0.03128 | −0.039945 | −0.023664 | 0.016705 | 0.019873 | 0.030247 | 0.01177 | 0.002917 | 0.000985 | 0.007081 | 0.006659 | −0.007634 | −0.005193 |
| 225 | −0.009067 | −0.010495 | −0.035615 | −0.014043 | 0.00657 | 0.017696 | 0.028902 | 0.024788 | −0.002289 | 0.008317 | 0.019909 | 0.022005 | 0.017362 | −0.001781 |
| 226 | 0.005965 | 0.018924 | 0.019955 | 0.016361 | −0.048252 | −0.090384 | −0.086625 | −0.080757 | −0.025981 | 0.000603 | −0.023194 | −0.018499 | 0.011319 | 0.016552 |
| 227 | −0.010258 | −0.003712 | 0.006893 | 0.043186 | 0.016979 | −0.035601 | −0.026234 | −0.098748 | 0.028195 | 0.087009 | 0.009158 | 0.010397 | −0.100381 | 0.017172 |
| 228 | −0.020353 | −0.013698 | −0.012628 | 0.012008 | 0.008218 | −0.012217 | −0.011447 | −0.008727 | −0.017 | −0.043628 | −0.017339 | −0.020527 | 0.029677 | −0.012589 |
| 229 | 0.018166 | 0.009074 | −0.000832 | −0.00352 | −0.129998 | 0.043404 | 0.022761 | 0.049597 | −0.071193 | −0.226054 | −0.063355 | −0.074442 | −0.013756 | −0.083437 |
| 230 | −0.019575 | 0.01658 | 0.044214 | 0.022429 | 0.032823 | 0.014075 | 0.016193 | 0.002597 | 0.044836 | −0.023568 | −0.07097 | −0.066105 | −0.141232 | −0.006564 |
| 231 | −0.016653 | 0.010124 | 0.021685 | −0.000961 | −0.042091 | −0.045025 | −0.041617 | −0.055403 | 0.011184 | 0.042156 | 0.008228 | 0.007238 | −0.028195 | −0.004148 |
| 232 | −0.036432 | 0.003749 | −0.00393 | 0.022035 | −0.003092 | 0.009313 | −0.014038 | 0.006513 | 0.045753 | 0.008497 | 0.003668 | 0.00428 | 0.014265 | −0.050731 |
| 233 | 0.023973 | 0.001206 | 0.038416 | 0.043582 | 0.004496 | 0.01473 | 0.023055 | 0.01768 | 0.027007 | 0.009995 | 0.005246 | 0.004571 | 0.039786 | 0.005391 |
| 234 | −0.000657 | 0.033936 | 0.026984 | 0.005634 | −0.027352 | −0.019341 | −0.010764 | −0.007279 | 0.033996 | −0.006834 | 0.021803 | 0.016967 | 0.018303 | −0.013848 |
| 235 | −0.01672 | −0.032879 | 0.001308 | 0.028932 | 0.008889 | 0.004962 | −0.003072 | 0.011302 | −0.031161 | −0.019543 | 0.010595 | 0.002507 | −0.003536 | −0.014084 |
| 236 | −0.054863 | 0.025369 | 0.011148 | −0.005377 | 0.043246 | 0.028555 | 0.026326 | 0.021957 | −0.013869 | 0.016273 | 0.006767 | 0.005419 | −0.02747 | −0.135326 |
| 237 | 0.010066 | 0.003394 | 0.018738 | 0.012447 | 0.014814 | 0.02969 | 0.025769 | 0.033285 | 0.011897 | 0.017 | 0.044122 | 0.041326 | 0.044033 | −0.010739 |
| 238 | 0.008981 | 0.010702 | 0.003844 | −0.000247 | 0.021889 | 0.029328 | 0.023088 | 0.031202 | 0.038449 | −0.006573 | 0.020736 | 0.020874 | 0.019269 | 0.001244 |
| 239 | 0.006452 | 0.002126 | −0.017443 | −0.002938 | 0.020997 | 0.002535 | 0.024211 | 0.02354 | 0.034689 | 0.013092 | 0.00998 | 0.017364 | 0.018874 | 0.001104 |
| 240 | 0.027897 | −0.019679 | 0.020263 | 0.02664 | −0.026654 | −0.008158 | −0.004908 | −0.016276 | 0.015208 | −0.012717 | −0.004733 | −0.003821 | −0.017097 | 0.013558 |
| 241 | 0.015101 | 0.003732 | 0.018882 | 0.009612 | 0.000621 | 0.002653 | 0.002903 | 0.002217 | −0.010738 | −0.001979 | 0.009675 | 0.004734 | 0.020844 | −0.005525 |
| 242 | −0.055538 | 0.02058 | 0.027967 | 0.022165 | 0.009224 | 0.015118 | 0.008092 | 0.016329 | −0.012403 | 0.012543 | 0.019092 | 0.017678 | 0.03193 | −0.021473 |
| 243 | −0.018636 | −0.004676 | 0.002853 | 0.002103 | −0.00349 | −0.000269 | 0.004955 | 0.005227 | 0.00296 | 0.011005 | 0.008133 | 0.01469 | 0.000622 | 0.026072 |
| 244 | −0.004649 | 0.01639 | 0.019284 | 0013041 | 0.030621 | 0.014591 | 0.022494 | 0.014944 | 0.008366 | 0.03858 | 0.016491 | 0.020877 | −0.02007 | 0.012321 |
| 245 | −0.013748 | −0.004218 | 0.001102 | −0.02065 | 0.047413 | 0.046446 | 0.063013 | 0.041584 | −0.024368 | 0.013086 | 0.026672 | 0.033946 | −0.004597 | −0.001156 |
| 246 | 0.008542 | −0.013217 | −0.01779 | −0.004019 | −0.002978 | 0.037446 | 0.042676 | 0.04345 | −0.02117 | 0.003751 | 0.0311581 | 0.028744 | 0.026217 | −0.007676 |
| 247 | −0.006352 | −0.009826 | −0.029654 | −0.033216 | 0.026656 | 0.019054 | 0.030425 | 0.044152 | −0.013766 | 0.000703 | −0.002059 | −0.001893 | −0.006212 | −0.059607 |
| 248 | −0.022998 | 0.001893 | −0.002326 | −0.018597 | 0.035191 | 0.03089 | 0.004822 | 0.009472 | 0.033344 | −0.004471 | −0.017964 | −0.020916 | −0.039888 | −0.041816 |
| 249 | −0.018142 | −0.099171 | −0.040416 | 0.023707 | 0.006726 | −0.00305 | −0.005015 | 0.018129 | 0.013441 | 0.013802 | −0.0167 | −0.011775 | 0.002366 | −0.007738 |
| 250 | 0.026813 | −0.019632 | −0.004599 | 0.006351 | −0.025392 | −0.017921 | −0.012396 | −0.020775 | −0.026402 | 0.002943 | 0.00031 | −0.000384 | −0.022982 | 0.00024 |
| 251 | 0.006177 | 0.01668 | 0.039277 | 0.013863 | 0.014272 | 0.010741 | −0.001823 | −0.017359 | −0.007064 | −0.016903 | −0.004095 | −0.006071 | 4.023249 | 0.022443 |
| 252 | −0.059477 | 0.034092 | 0.006719 | −0.026858 | 0.019651 | −0.017036 | −0.006925 | −0.01327 | 0.00136 | 0.020629 | −0.008751 | −0.000951 | 0.013346 | −0.011162 |
| 253 | −0.038271 | 0.000491 | −0.024752 | −0.033879 | −0.102003 | −0.014583 | −0.014474 | −0.012834 | −0.063765 | −0.031182 | 0.023603 | 0.023705 | 0.036465 | −0.048169 |
| 254 | 0.004778 | −0.0415211 | −0.079004 | −0.040284 | 0.004109 | 0.028887 | 0.030696 | 0.028751 | −0.017287 | 0.00066 | 0.028973 | 0.029165 | 0.014685 | −0.018864 |
| 255 | 0.000371 | −0.00077 | 0.003943 | −0.012587 | 0.01547 | 0.02025 | 0.024695 | 0.011788 | −0.006044 | 0.006301 | 0.012475 | 0.012132 | −0.016974 | 0.010921 |
| 256 | −0.011444 | 0.000502 | −0.041353 | −0.074655 | −0.046072 | 0.006506 | 0.011397 | 0.037812 | −0.015209 | −0.018162 | 0.028682 | 0.030625 | 0.02751 | −0.016277 |
| 257 | −0.00834 | 0.013639 | −0.001281 | 0.004244 | −0.009781 | −0.028383 | −0.023496 | −0.019793 | 0.008305 | 0.000506 | −0.025543 | −0.027791 | 0.009183 | −0.005872 |
| 258 | 0.000033 | 0.015309 | −0.021365 | −0.030112 | 0.004528 | 0.002084 | 0.008666 | −0.006927 | 0.024226 | 0.017337 | 0.008925 | 0.005969 | −0.007526 | −0.033647 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 259 | −0.010925 | −0.07814 | −0.035904 | 0.005595 | 0.040227 | 0.008443 | 0.007088 | 0.011291 | 0.026264 | −0.009378 | −0.022665 | −0.018485 | 0.007109 | 0.0166 |
| 260 | −0.017308 | −0.021078 | −0.042836 | −0.038302 | 0.006578 | −0.002552 | 0.000576 | −0.009383 | 0.032225 | 0.008157 | −0.023475 | −0.026297 | −0.00497 | 0.009451 |
| 261 | −0.030247 | 0.014879 | −0.022442 | −0.072815 | 0.007795 | 0.018513 | 0.010373 | −0.021677 | 0.041895 | −0.005513 | 0.00145 | −0.003848 | −0.012151 | −0.000536 |
| 262 | −0.095415 | −0.000164 | −0.021125 | −0.032767 | 0.023235 | −0.000039 | 0.007869 | 0.006547 | −0.008885 | 0.014296 | −0.006856 | −0.002489 | 0.003964 | −0.043462 |
| 263 | 0.881261 | −0.017143 | 0.000395 | −0.004241 | 0.027212 | −0.003597 | 0.006025 | 0.000591 | −0.013501 | 0.011032 | −0.015109 | −0.007792 | −0.006914 | −0.022595 |
| 264 | 0.005523 | 0.806022 | −0.109127 | −0.004554 | 0.014076 | 0.006039 | 0.021924 | 0.024739 | −0.047718 | −0.01537 | 0.000043 | 0.003551 | −0.002001 | 0.025571 |
| 265 | 0.021002 | −0.103148 | 0.775949 | −0.147203 | −0.017367 | −0.002731 | 0.014518 | 0.013126 | −0.042356 | −0.013232 | 0.017224 | 0.01643 | 0.020143 | 0.00318 |
| 266 | 0.007744 | 0.010638 | −0.131402 | 0.78961 | 0.000014 | 0.006521 | 0.010782 | 0.003067 | −0.034539 | 0.007765 | 0.037453 | 0.031268 | 0.010102 | −0.003209 |
| 267 | 0.019182 | 0.00838 | −0.01361 | 0.008627 | 0.725512 | −0.07693 | −0.06225 | −0.051839 | −0.088697 | −0.111783 | 0.01211 | 0.016596 | 0.022013 | −0.014592 |
| 268 | 0.0038681 | −0.0013951 | −0.0004661 | 0.021694 | −0.058345 | 0.889228 | −0.081761 | −0.063831 | −0.039306 | 0.0157181 | −0.020783 | −0.009216 | 0.019252 | 0.014176 |
| 269 | 0.006426 | 0.016167 | 0.021224 | 0.018353 | −0.055056 | −0.081322 | 0.895947 | −0.079662 | −0.031047 | −0.00028 | −0.02032 | −0.02197 | 0.003545 | 0.018152 |
| 270 | −0.003445 | 0.025808 | 0.032016 | 0.019826 | −0.026773 | −0.057744 | −0.075086 | 0.880094 | 0.000185 | 0.024192 | −0.026853 | −0.029556 | −0.065504 | 0.035362 |
| 271 | −0.018185 | −0.052023 | −0.030879 | −0.023327 | −0.058254 | −0.000675 | 0.007223 | 0.017415 | 0.542949 | −0.127758 | 0.001127 | −0.004755 | 0.018029 | −0.051308 |
| 272 | 0.029505 | 0.006257 | −0.009195 | −0.008685 | −0.122354 | −0.005401 | −0.012932 | 0.007795 | −0.097483 | 0.761459 | −0.077159 | −0.082228 | 0.001411 | −0.047917 |
| 273 | −0.007013 | 0.01557 | 0.019743 | 0.026997 | 0.008295 | −0.027662 | −0.023787 | −0.025795 | 0.003938 | −0.078127 | 0.868768 | −0.127175 | −0.069551 | −0.01142 |
| 274 | −0.002196 | 0.01535 | 0.018399 | 0.023064 | 0.008387 | −0.013102 | −0.023007 | −0.024813 | −0.001764 | −0.086009 | −0.126501 | 0.869071 | −0.073866 | −0.011752 |
| 275 | −0.027968 | 0.003394 | 0.040727 | 0.021712 | 0.050535 | 0.022425 | 0.011707 | −0.055309 | 0.021381 | 0.001749 | −0.072987 | −0.072329 | 0.740974 | −0.000108 |
| 276 | −0.047549 | 0.020383 | −0.002031 | −0.023422, | −0.01204 | 0.025734 | 0.03 | 0.045073 | −0.054523 | −0.054689 | 0.004354 | 0.002151 | 0.013658 | 0.806689 |
| 277 | 0.00596 | 0.002548 | −0.000667 | 0.001657 | 0.021975 | 0.022775 | 0.030974 | 0.023172 | 0.022728 | 0.00519 | 0.009441 | 0.007209 | 0.01458 | −0.004099 |
| 278 | 0.003418 | 0.023661 | 0.014882 | −0.007241 | 0.030497 | 0.041603 | 0.02775 | 0.010203 | 0.02732 | 0.007718 | 0.018729 | 0.011588 | −0.006046 | 0.010426 |
| 279 | 0.0086 | 0.011193 | 0.003119 | −0.010892 | 0.025991 | 0.02213 | 0.016338 | 0.0042 | 0.040894 | −0.00533 | 0.008339 | 0.009288 | −0.019191 | 0.015162 |
| 280 | −0.009446 | −0.016343 | −0.002578 | −0.000859 | −0.038979 | −0.021271 | 0.005659 | −0.005493 | −0.035617 | 0.005563 | 0.010428 | 0.02081 | 0.00978 | 0.015916 |
| 281 | 0.020836 | −0.011698 | −0.002814 | −0.011172 | 0.004205 | 0.025984 | 0.032279 | 0.017549 | 0.018204 | −0.014078 | −0.014673 | −0.012045 | −0.007683 | 0.028977 |
| 282 | 0.007155 | 0.001935 | 0.006951 | −0.003529 | 0.019989 | 0.027116 | 0.012794 | −0.004829 | −0.028577 | 0.004724 | −0.005024 | −0.007011 | −0.024855 | 0.014615 |
| 283 | −0.01515 | −0.006567 | 0.001327 | −0.034724 | 0.023033 | 0.037525 | 0.021969 | 0.014214 | 0.00677 | −0.013889 | −0.006337 | −0.01435 | −0.050985 | −0.048303 |
| 284 | 0.000882 | −0.003478 | −0.002488 | 0.015106 | −0.02222 | −0.028766 | −0.026027 | −0.01663 | −0.001586 | −0.005924 | −0.020427 | −0.022992 | 0.002565 | −0.009478 |
| 285 | −0.007901 | −0.002155 | −0.002692 | 0.024985 | −0.003277 | −0.023855 | −0.02349 | −0.006571 | −0.011995 | 0.015264 | −0.017552 | −0.021905 | 0.005965 | −0.00904 |
| 286 | 0.011749 | 0.00524 | −0.009086 | −0.013569 | 0.001576 | −0.001453 | −0.004097 | −0.000935 | 0.001544 | 0.040305 | 0.037056 | 0.034523 | 0.011391 | −0.000624 |
| 287 | −0.002257 | 0.019613 | 0.023894 | 0.000874 | 0.004183 | 0.000188 | −0.008983 | −0.029799 | 0.017251 | 0.036705 | 0.026334 | 0.021816 | −0.017221 | 0.018332 |
| 288 | −0.006091 | 0.0006441 | −0.0012751 | −0.025847 | 0.015826 | 0.011153 | 0.002054 | −0.011768 | 0.0303491 | 0.02008 | 0.018124 | 0.0130951 | −0.035862 | −0.028524 |
| 289 | −0.055834 | 0.01447 | −0.040772 | −0.054205 | 0.019748 | 0.005728 | 0.005965 | −0.005906 | −0.037514 | 0.008374 | −0.008877 | −0.011111 | −0.036103 | −0.031366 |
| 290 | 0.004199 | 0.002587 | 0.00197 | −0.011915 | 0.007397 | 0.00692 | 0.003901 | 0.003215 | 0.01636 | 0.002979 | −0.003754 | −0.001728 | −0.008678 | 0.02059 |
| 291 | 0.004459 | −0.000576 | 0.000704 | −0.011756 | 0.002972 | 0.005693 | 0.004292 | 0.004383 | 0.010426 | 0.004655 | 0.001048 | 0.003639 | −0.006173 | 0.017875 |
| 292 | 0.004575 | −0.019616 | −0.008539 | −0.014463 | 0.004842 | 0.013026 | 0.002244 | 0.011304 | −0.007637 | −0.005373 | 0.009697 | 0.009404 | −0.005885 | 0.014741 |
| 293 | 0.019156 | −0.014616 | 0.000266 | 0.007977 | 0.009861 | −0.035187 | −0.009701 | 0.005537 | 0.010948 | 0.016496 | 0.019853 | 0.029241 | 0.006603 | −0.011176 |
| 294 | 0.011877 | −0.031235 | −0.009946 | 0.002426 | 0.010661 | −0.021589 | −0.009563 | −0.026457 | −0.018072 | 0.024653 | −0.010895 | −0.00902 | −0.042538 | 0.017656 |
| 295 | 0.003026 | −0.0028631 | 0.002885 | 0.011763 | 0.025189 | 0.004695 | 0.013072 | 0.011492 | −0.00241 | −0.019515 | −0.054775 | −0.054994 | −0.023378 | −0.009067 |
| 296 | −0.032456 | −0.009528 | 0.003075 | 0.00595 | 0.002327 | 0.006261 | −0.003575 | −0.035716 | 0.003072 | −0.008399 | −0.056316 | −0.061147 | −0.089046 | 0.026802 |
| 297 | −0.007786 | 0.001413 | 0.009135 | −0.006933 | −0.007958 | 0.001366 | 0.004208 | 0.014209 | 0.026965 | −0.046354 | −0.047105 | −0.048121 | 0.008643 | −0.01269 |
| 298 | −0.019357 | 0.031688 | 0.021246 | −0.004893 | −0.004446 | 0.027098 | −0.005059 | −0.006764 | 0.033534 | −0.002342 | −0.012455 | −0.016981 | −0.001476 | 0.011712 |
| 299 | 0.01213 | 0.015523 | −0.011562 | −0.025572 | 0.004086 | −0.02151 | −0.007957 | −0.004903 | −0.002784 | −0.009207 | −0.007989 | −0.006685 | 0.03006 | −0.009405 |
| 300 | −0.035614 | 0.011392 | −0.008688 | −0.019072 | 0.019917 | 0.004765 | 0.005605 | −0.009348 | 0.028882 | 0.040969 | −0.009666 | −0.006597 | −0.021029 | 0.004615 |
| 301 | −0.001537 | −0.001438 | −0.002858 | 0.007668 | 0.016736 | −0.016783 | −0.003277 | −0.000328 | 0.012303 | 0.005377 | −0.01021 | −0.00597 | 0.015472 | 0.00632 |
| 302 | −0.015509 | −0.013029 | −0.009228 | 0.004011 | 0.021962 | −0.008361 | 0.007065 | −0.020575 | 0.006276 | 0.022846 | −0.012876 | −0.00927 | −0.032886 | 0.028573 |
| 303 | 0.0332561 | 0.008006 | −0.031115 | −0.035268 | −0.00757 | −0.004688 | −0.000132 | 0.008373 | −0.014416 | 0.0057 | 0.035693 | 0.035346 | 0.042226 | −0.009604 |
| 304 | 0.004898 | 0.017082 | −0.007349 | −0.02592 | −0.005696 | −0.005575 | 0.006832 | −0.018308 | 0.017601 | −0.000395 | 0.018175 | 0.022372 | 0.005816 | −0.008279 |
| 305 | 0.0043071 | 0.0036441 | 0.001167 | −0.010388 | 0.037734 | 0.021264 | 0.018136 | −0.000672 | −0.056071 | −0.008968 | 0.022407 | 0.00978 | −0.021227 | 0.025192 |
| 306 | −0.014116 | 0.005333 | −0.003363 | 0.017759 | −0.0251 | −0.013316 | 0.003233 | −0.011714 | 0.042236 | −0.003511 | −0.01327 | −0.007058 | −0.025535 | 0.023446 |
| 307 | 0.009189 | −0.000941 | 0.015847 | 0.012647 | 0.01454 | 0.010381 | 0.017574 | 0.010211 | −0.035762 | 0.010239 | −0.006734 | −0.011135 | −0.035269 | 0.028516 |
| 308 | −0.047798 | −0.000979 | 0.019035 | 0.019062 | −0.021649 | −0.007626 | 0.002413 | 0.00145 | 0.025127 | −0.011837 | −0.010612 | −0.008068 | 0.007921 | 0.020532 |
| 309 | −0.02091 | −0.001734 | 0.015368 | 0.017919 | −0.023614 | −0.013387 | −0.014515 | −0.015074 | −0.001403 | −0.001479 | 0.000386 | 0.002754 | −0.011676 | 0.003222 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 310 | −0.015088 | −0.024117 | −0.017734 | 0.025845 | −0.030921 | 0.001176 | −0.008806 | −0.000636 | −0.028061 | 0.00641 | 0.006829 | 0.004531 | −0.033243 | 0.019652 |
| 311 | 0.002605 | 0.014096 | −0.001677 | 0.001359 | 0.01619 | −0.014143 | −0.013141 | −0.005918 | 0.015797 | −0.011401 | −0.024571 | −0.021608 | −0.00111 | −0.016111 |
| 312 | 0.008392 | 0.036367 | 0.026995 | 0.001008 | 0.002429 | −0.008421 | −0.03535 | −0.0105 | 0.056594 | −0.052054 | −0.025157 | −0.03108 | 0.032463 | 0.018041 |
| 313 | −0.009389 | 0.007771 | −0.017137 | −0.014315 | 0.006994 | −0.005651 | −0.005288 | −0.007057 | 0.050068 | −0.017989 | −0.00644 | −0.005192 | 0.033197 | 0.002809 |
| 314 | −0.018379 | −0.023822 | −0.00211 | −0.005334 | 0.006758 | 0.019349 | 0.02448 | 0.016352 | −0.016625 | −0.006901 | 0.011072 | 0.013255 | 0.007252 | −0.011829 |
| 315 | 0.002795 | 0.02899 | −0.014623 | −0.027186 | 0.007353 | 0.001457 | −0.003912 | −0.006741 | 0.0054 | 0.009867 | 0.023145 | 0.015541 | 0.033035 | 0.004656 |
| 316 | 0.003284 | 0.018659 | 0.025582 | 0.009863 | −0.030527 | 0.002124 | −0.010009 | −0.020109 | 0.052169 | 0.031449 | 0.020465 | 0.015608 | −0.06036 | 0.002371 |
| 317 | −0.008543 | 0.005413 | −0.011044 | 0.002461 | −0.01522 | 0.000844 | −0.008456 | −0.009431 | −0.005624 | −0.00956 | −0.003609 | −0.007071 | −0.013656 | 0.001324 |
| 318 | −0.020618 | −0.000171 | 0.017249 | 0.009278 | 0.02982 | 0.00998 | 0.013825 | 0.013879 | −0.023071 | 0.017239 | 0.014584 | 0.013795 | 0.008703 | −0.02116 |
| 319 | −0.012042 | 0.000958 | −0.008171 | −0.017281 | −0.0042 | −0.003685 | −0.003336 | 0.009565 | 0.01269 | 0.026403 | 0.029808 | 0.027856 | 0.02237 | −0.006087 |
| 320 | 0.001469 | 0.017827 | −0.024421 | −0.01388 | 0.005774 | −0.022748 | −0.006627 | −0.008004 | 0.035455 | 0.000716 | −0.012675 | −0.010929 | −0.013774 | 0.011332 |
| 321 | −0.017309 | 0.017016 | 0.009884 | −0.005203 | 0.018394 | −0.01024 | 0.003374 | −0.021165 | 0.01705 | 0.007345 | −0.027565 | −0.02383 | −0.003769 | 0.003664 |
| 322 | −0.013677 | 0.001403 | 0.001961 | 0.028866 | 0.012497 | −0.005666 | −0.000858 | −0.009834 | −0.016286 | 0.023427 | 0.013475 | 0.011479 | 0.001874 | 0.00301 |
| 323 | 0.012164 | −0.006809 | 0.009884 | −0.006721 | −0.002975 | −0.01846 | −0.013533 | −0.003197 | 0.028207 | 0.002896 | −0.016474 | −0.012824 | 0.029921 | 0.011133 |
| 324 | −0.004731 | −0.014315 | −0.019605 | −0.029737 | 0.025246 | −0.002384 | −0.013634 | −0.035693 | −0.044606 | 0.013291 | −0.017955 | −0.017755 | −0.030511 | −0.000073 |
| 325 | 0.004059 | 0.007314 | −0.000876 | −0.019773 | 0.013804 | −0.00643 | −0.028377 | −0.029719 | 0.016308 | −0.007877 | −0.013006 | −0.015596 | −0.018811 | −0.005949 |
| 326 | 0.011667 | −0.009046 | 0.004789 | 0.004241 | 0.018028 | −0.004595 | −0.012123 | −0.030007 | −0.039411 | −0.013543 | −0.018638 | −0.020609 | −0.060326 | 0.013422 |
| 327 | −0.010579 | −0.010507 | 0.004507 | 0.022118 | −0.015638 | 0.010962 | 0.004502 | 0.005953 | −0.01565 | −0.027157 | −0.004972 | −0.010455 | 0.001763 | −0.001732 |
| 328 | −0.036657 | 0.008434 | 0.041374 | 0.018053 | 0.040639 | 0.024273 | 0.024909 | 0.014763 | −0.000682 | 0.054636 | −0.018839 | −0.021023 | 0.011182 | 0.02074 |
| 329 | 0.007466 | −0.0159511 | 0.0029461 | −0.002037 | 0.037559 | 0.003091 | 0.004214 | 0.019213 | −0.011865 | −0.011874 | −0.003761 | −0.002349 | 0.03318 | −0.012977 |
| 330 | 0.022623 | −0.020863 | 0.001147 | 0.023589 | −0.007422 | −0.003123 | 0.006035 | −0.00106 | 0.019487 | −0.011999 | −0.003724 | −0.000108 | −0.018864 | −0.002535 |
| 331 | 0.007997 | −0.026853 | −0.0157241 | −0.014998 | 0.010379 | −0.012873 | −0.015135 | −0.002691 | −0.019149 | 0.013131 | 0.025403 | 0.023164 | 0.01858 | −0.006306 |
| 332 | 0.015129 | 0.018513 | 0.014229 | 0.008537 | −0.033041 | −0.008851 | −0.020673 | −0.01902 | −0.038342 | −0.003137 | −0.005435 | −0.005914 | 0.002693 | −0.008218 |
| 333 | 0.011328 | −0.006117 | 0.008261 | −0.00834 | 0.028628 | −0.000432 | −0.017847 | −0.016647 | 0.002005 | 0.019083 | 0.002998 | 0.000568 | −0.003106 | −0.003166 |
| 334 | 0.0171 | 0.022615 | 0.030882 | 0.003385 | 0.010602 | −0.030175 | −0.013471 | 0.013398 | −0.029197 | −0.018736 | −0.010054 | 0.000443 | 0.00043 | −0.012242 |
| 335 | 0.017333 | −0.001985 | −0.000429 | −0.022683 | 0.021026 | 0.0016 | −0.014146 | −0.00833 | 0.0483161 | 0.0123341 | 0.0094561 | 0.0068171 | −0.007761 | 0.007791 |
| 336 | 0.009827 | 0.0131711 | 0.0132091 | 0.034451 | −0.031778 | 0.002228 | 0.000795 | −0.004167 | 0.006824 | 0.007555 | 0.012666 | 0.012817 | −0.00814 | −0.028191 |
| 337 | 0.029288 | 0.012032 | −0.028843 | −0.016789 | 0.000035 | 0.007581 | −0.004168 | 0.010004 | −0.060806 | −0.03017 | −0.002104 | −0.010674 | 0.002091 | 0.020931 |
| 338 | 0.004412 | 0.025711 | 0.059687 | 0.056919 | 0.000485 | −0.007017 | −0.01617 | −0.002432 | −0.021717 | −0.015914 | −0.042558 | −0.035404 | −0.027001 | −0.029751 |
| 339 | −0.003081 | 0.026344 | 0.019237 | 0.052199 | 0.036387 | −0.021713 | 0.004763 | 0.015289 | 0.046597 | 0.028783 | 0.007022 | 0.019747 | 0.025429 | −0.020898 |
| 340 | 0.04183 | 0.035362 | 0.0241711 | 0.001657 | 0.003048 | −0.01289 | −0.007304 | 0.017673 | 0.037412 | −0.022005 | −0.012045 | −0.014775 | 0.0098621 | 0.008099 |

| | JR | JS | JT | JU | JV | JW | JX | JY | JZ | KA | KB | KC | KD | KE |
|---|---|---|---|---|---|---|---|---|---|---|---|---|---|---|
| 1 | −0.019972 | −0.029919 | −0.06797 | −0.112135 | −0.048326 | −0.014185 | 0.043724 | 0.052211 | 0.037556 | −0.027509 | −0.006959 | 0.029641 | 0.028455 | 0.081909 |
| 2 | 0.005787 | −0.008194 | −0.079293 | 0.064965 | 0.033287 | 0.062406 | −0.011252 | −0.038567 | −0.022216 | 0.0133 | 0.017527 | 0.05573 | 0.007751 | 0.057427 |
| 3 | 0.070426 | 0.035073 | 0.006146 | 0.027162 | 0.038587 | 0.049711 | 0.00742 | −0.080276 | −0.082336 | −0.026279 | 0.024089 | 0.015266 | −0.007264 | 0.066423 |
| 4 | 0.018517 | 0.030807 | −0.060652 | 0.082726 | 0.019021 | 0.036128 | −0.024979 | 0.008486 | 0.013494 | 0.048651 | 0.047718 | −0.00023 | 0.041525 | −0.000846 |
| 5 | −0.065641 | −0.037534 | 0.054025 | −0.003912 | −0.028711 | 0.012405 | 0.127901 | −0.017333 | −0.020684 | −0.023859 | 0.029956 | 0.050714 | 0.007852 | −0.035681 |
| 6 | −0.008017 | 0.020206 | −0.009172 | −0.014318 | 0.058615 | 0.064382 | 0.055819 | −0.008787 | 0.010154 | 0.054493 | 0.049388 | 0.115869 | 0.136484 | 0.028995 |
| 7 | 0.032817 | 0.040997 | −0.024737 | −0.009565 | −0.038097 | −0.012301 | −0.02729 | −0.034784 | 0.003562 | −0.020075 | 0.004914 | 0.029432 | −0.056686 | −0.007419 |
| 8 | −0.033755 | −0.067592 | −0.06282 | −0.001786 | −0.014771 | −0.006877 | −0.001932 | 0.008546 | 0.011829 | 0.03014 | 0.02352 | −0.043559 | 0.007617 | −0.027165 |
| 9 | 0.060107 | 0.10273 | 0.053809 | −0.05007 | 0.031475 | 0.05158 | 0.08274 | −0.010747 | 0.026801 | 0.007486 | 0.034522 | 0.039185 | −0.028729 | −0.050746 |
| 10 | 0.018387 | 0.021461 | 0.086268 | 0.052416 | 0.015063 | −0.002602 | −0.016999 | 0.020173 | 0.033392 | −0.011457 | −0.044156 | −0.072426 | −0.047084 | −0.016008 |
| 11 | −0.036901 | −0.020123 | −0.000189 | 0.007554 | 0.022332 | 0.045914 | 0.018638 | 0.030466 | 0.035576 | −0.015378 | −0.008256 | −0.006781 | 0.002574 | −0.011421 |
| 12 | 0.023781 | −0.029454 | −0.030671 | 0.070431 | −0.052303 | −0.094119 | −0.052087 | −0.016406 | −0.024453 | 0.028462 | −0.000791 | 0.008657 | 0.0021 | −0.013678 |
| 13 | 0.040185 | 0.039284 | −0.017522 | 0.031113 | −0.049471 | −0.052117 | 0.036425 | −0.008018 | −0.027188 | −0.116584 | −0.059521 | −0.054354 | −0.037328 | 0.079902 |
| 14 | −0.018879 | −0.038315 | −0.034668 | −0.067172 | −0.019418 | −0.057591 | −0.062878 | 0.004243 | 0.025433 | −0.055065 | −0.058464 | −0.017564 | 0.01291 | 0.078129 |
| 15 | 0.00245 | 0.012516 | 0.020564 | 0.088873 | 0.003585 | 0.013076 | −0.057118 | 0.032054 | 0.036694 | 0.015482 | 0.066833 | −0.059811 | −0.020377 | −0.136171 |
| 16 | −0.060118 | −0.088816 | −0.034849 | −0.034874 | 0.002557 | 0.007425 | −0.022001 | 0.038056 | 0.043124 | 0.057268 | 0.01718 | −0.033474 | −0.01974 | 0.004904 |
| 17 | −0.028623 | −0.044857 | 0.012148 | 0.026079 | −0.050501 | −0.063277 | −0.031318 | −0.001585 | −0.009094 | −0.089015 | −0.046844 | −0.05952 | 0.010623 | 0.012458 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 18 | 0.106351 | 0.094346 | 0.00251 | 0.056115 | 0.059149 | 0.036133 | −0.001478 | −0.02824 | −0.015941 | −0.025113 | −0.045313 | −0.050593 | −0.000888 | −0.036709 |
| 19 | −0.047294 | −0.025582 | −0.009274 | 0.095141 | 0.004227 | 0.019342 | 0.040898 | −0.059769 | −0.066375 | −0.054462 | −0.017566 | −0.072601 | −0.033487 | −0.03373 |
| 20 | 0.082864 | 0.074781 | 0.033164 | −0.103691 | −0.082682 | −0.050918 | 0.052724 | 0.011195 | 0.002543 | −0.03019f | −0.070708 | 0.017015 | 0.08514 | −0.057459 |
| 21 | −0.078629 | −0.065585 | 0.004066 | −0.079711 | 0.008121 | 0.027096 | 0.038481 | 0.033921 | 0.041498 | −0.018069 | −0.036971 | −0.006502 | −0.025807 | 0.019934 |
| 22 | 0.024897 | 0.002884 | −0.027979 | −0.028529 | 0.0166 | 0.014076 | −0.004825 | 0.063941 | 0.086705 | 0.028341 | 0.021623 | −0.04027 | 0.035485 | −0.001943 |
| 23 | 0.030423 | −0.001955 | 0.060291 | −0.023857 | 0.044267 | 0.0097 | 0.00324 | −0.006864 | −0.007581 | −0.025221 | −0.02815 | −0.0429 | −0.080116 | 0.005704 |
| 24 | −0.003828 | −0.013083 | −0.040204 | 0.007893 | −0.02367 | −0.010521 | −0.018028 | 0.019976 | 0.000772 | 0.081714 | 0.048053 | −0.042311 | −0.031103 | −0.060735 |
| 25 | 0.031828 | 0.034783 | 0.063905 | 0.012697 | −0.063608 | −0.058526 | −0.007324 | −0.017914 | −0.029571 | −0.00757 | 0.023746 | 0.074285 | 0.052165 | 0.054106 |
| 26 | 0.017964 | −0.016458 | −0.021978 | −0.04323 | 0.005778 | −0.048118 | −0.057014 | 0.006003 | −0.033778 | −0.01338 | −0.035938 | 0.036242 | −0.021926 | 0.015379 |
| 27 | −0.002277 | −0.001985 | 0.026642 | 0.063483 | 0.016787 | 0.015598 | −0.052599 | −0.002097 | −0.003216 | 0.065083 | 0.029771 | 0.003216 | −0.060963 | −0.00129 |
| 28 | 0.039293 | 0.035322 | 0.01976 | 0.008916 | 0.049412 | −0.001663 | −0.02924 | −0.065039 | −0.102712 | 0.019497 | −0.014414 | 0.006663 | −0.045446 | −0.006031 |
| 29 | 0.016399 | 0.018851 | 0.000378 | −0.019351 | 0.006356 | 0.000915 | 0.011808 | 0.019598 | 0.005834 | 0.008635 | −0.010043 | 0.006752 | −0.004044 | −0.008898 |
| 30 | 0.03209 | 0.042811 | −0.030106 | −0.090328 | 0.018221 | −0.009652 | 0.006771 | 0.010081 | 0.009177 | −0.032526 | −0.022413 | 0.070931 | 0.067112 | 0.04414 |
| 31 | −0.043921 | −0.048151 | −0.012058 | −0.038634 | −0.081785 | −0.100848 | −0.011868 | 0.024948 | 0.019861 | −0.010533 | −0.02253 | −0.043643 | 0.032251 | 0.008807 |
| 32 | −0.034512 | −0.013887 | 0.016094 | 0.071903 | −0.093059 | −0.076846 | 0.01281 | 0.012713 | 0.012881 | −0.003378 | −0.00298 | 0.023322 | 0.007696 | −0.00639 |
| 33 | −0.052304 | −0.035945 | −0.029884 | −0.038005 | 0.022984 | 0.012579 | −0.001454 | 0.030149 | 0.015929 | 0.034896 | 0.031682 | 0.038958 | 0.012766 | 0.015214 |
| 34 | 0.039747 | 0.048981 | −0.028854 | −0.033341 | −0.037759 | 0.017724 | −0.075051 | 0.029779 | 0.062036 | 0.06191 | 0.041919 | 0.000282 | 0.001154 | 0.049013 |
| 35 | 0.019191 | 0.007946 | 0.014271 | 0.072662 | −0.056856 | −0.018554 | −0.06423 | 0.007842 | 0.026558 | −0.000709 | 0.009832 | −0.060159 | 0.02926 | 0.027564 |
| 36 | 0.027698 | 0.065571 | −0.004329 | 0.063723 | 0.043408 | 0.03938 | 0.0121 | −0.050392 | −0.047498 | 0.028828 | 0.063479 | 0.031762 | −0.021878 | 0.067434 |
| 37 | 0.046215 | 0.041709 | −0.061573 | −0.076286 | −0.0756 | −0.096029 | −0.114719 | 0.012562 | 0.011391 | 0.046219 | 0.008231 | −0.046088 | −0.031614 | −0.008888 |
| 38 | −0.01215 | 0.025043 | 0.0145 | −0.013724 | 0.021883 | 0.04577 | 0.023367 | 0.031863 | 0.029064 | 0.031818 | 0.021882 | 0.054576 | 0.052797 | 0.035678 |
| 39 | 0.05709 | 0.014852 | 0.002678 | 0.062189 | 0.039756 | −0.003937 | 0.016752 | −0.018974 | −0.048565 | 0.019795 | 0.018122 | 0.062119 | 0.036166 | −0.024383 |
| 40 | −0.073625 | −0.085834 | −0.039502 | 0.024848 | 0.048613 | 0.031217 | 0.035331 | −0.014016 | −0.028349 | −0.034756 | −0.077697 | −0.037604 | −0.024165 | −0.039872 |
| 41 | −0.032016 | −0.024498 | 0.006738 | 0.063076 | −0.036428 | −0.031329 | −0.073959 | −0.0028 | −0.003355 | −0.012796 | 0.005406 | −0.001957 | 0.001948 | −0.009939 |
| 42 | 0.010061 | 0.022685 | 0.012581 | −0.006049 | −0.002721 | 0.014298 | 0.014888 | 0.002398 | 0.008509 | 0.003229 | 0.000826 | −0.018867 | −0.010832 | −0.028745 |
| 43 | −0.014819 | 0.016541 | 0.009805 | −0.011364 | 0.012172 | 0.01997 | 0.017653 | 0.038145 | 0.027459 | 0.062578 | 0.071065 | 0.087704 | −0.002823 | 0.000334 |
| 44 | 0.004387 | 0.020421 | −0.011471 | −0.075812 | 0.112827 | 0.106893 | 0.072801 | −0.020617 | −0.016739 | 0.040944 | 0.024488 | −0.002825 | 0.020269 | −0.030275 |
| 45 | 0.016277 | 0.015254 | 0.096033 | 0.021038 | 0.063211 | 0.010512 | 0.058643 | −0.036548 | −0.045804 | −0.063482 | −0.082417 | −0.054092 | −0.012557 | 0.028617 |
| 46 | −0.032187 | −0.042707 | −0.017872 | 0.041695 | −0.033322 | 0.000352 | 0.00771 | −0.005907 | 0.01707 | 0.058964 | 0.037845 | 0.085832 | 0.000702 | 0.028821 |
| 47 | 0.023137 | 0.032876 | −0.037353 | 0.022244 | −0.009357 | 0.055549 | 0.056082 | 0.010587 | 0.032283 | 0.01426 | 0.063561 | 0.09851 | 0.040132 | −0.009295 |
| 48 | −0.007335 | 0.041878 | −0.013475 | −0.076218 | −0.094784 | −0.055695 | −0.072484 | −0.037729 | −0.018028 | −0.043053 | −0.016101 | 0.000283 | 0.016675 | 0.024463 |
| 49 | −0.00119 | −0.0023 | 0.027716 | 0.005617 | −0.034044 | 0.004057 | 0.003212 | −0.038273 | −0.042372 | −0.072667 | −0.015873 | −0.008799 | 0.003163 | 0.011147 |
| 50 | −0.049021 | −0.036648 | 0.005959 | −0.036658 | −0.014173 | 0.03639 | 0.029418 | 0.004593 | 0.023577 | −0.002955 | 0.042959 | −0.068529 | 0.008821 | −0.112532 |
| 51 | 0.015578 | 0.013377 | −0.095707 | −0.025647 | −0.025977 | −0.026433 | −0.017662 | 0.038061 | 0.036153 | −0.014465 | −0.030425 | −0.03206 | −0.01889 | −0.094161 |
| 52 | −0.047078 | −0.05345 | 0.071137 | 0.05157 | 0.067982 | 0.060444 | 0.069779 | 0.010854 | −0.001904 | 0.08964 | 0.0417 | 0.042475 | −0.021539 | 0.015119 |
| 53 | 0.025959 | 0.03366 | −0.071722 | −0.029049 | 0.077131 | 0.017382 | 0.000912 | −0.022553 | −0.054309 | −0.08242 | −0.12265 | −0.022395 | −0.009831 | −0.02708 |
| 54 | −0.019265 | −0.001264 | −0.086033 | 0.003294 | 0.027819 | 0.033868 | −0.062813 | 0.071347 | 0.105923 | 0.03878 | 0.01947 | −0.050892 | −0.047406 | 0.040611 |
| 55 | −0.030321 | −0.046938 | 0.003222 | −0.001611 | 0.021397 | 0.028857 | −0.000916 | −0.007751 | −0.019904 | 0.020601 | 0.049841 | 0.023099 | −0.021957 | 0.018637 |
| 56 | −0.086437 | −0.126969 | −0.028742 | −0.01324 | 0.078058 | 0.066372 | 0.023087 | −0.064089 | −0.043379 | −0.054129 | −0.03565 | −0.097334 | −0.056307 | −0.035033 |
| 57 | 0.014302 | 0.022033 | 0.011408 | −0.017148 | 0.076415 | 0.095139 | 0.038095 | 0.009622 | 0.016845 | −0.02641 | −0.000457 | 0.006474 | 0.013439 | −0.030308 |
| 58 | 0.037164 | 0.042989 | 0.109863 | −0.063368 | 0.046885 | 0.058677 | 0.047842 | 0.051731 | 0.050526 | −0.071819 | −0.064443 | −0.026265 | −0.043575 | −0.018835 |
| 59 | 0.020091 | 0.0233771 | −0.0511721 | 0.008277 | −0.02265 | −0.002219 | −0.018637 | 0.03441 | 0.044899 | 0.025321 | 0.046105 | 0.009678 | −0.029121 | −0.027963 |
| 60 | −0.098026 | −0.058728 | 0.056439 | −0.142431 | −0.014629 | −0.033203 | 0.015461 | −0.010662 | 0.005924 | 0.012211 | 0.049135 | 0.021954 | 0.007146 | 0.07645 |
| 61 | −0.017492 | 0.013506 | 0.078369 | −0.094683 | −0.144864 | −0.107317 | −0.022341 | −0.002964 | −0.01681 | −0.04732f | −0.031996 | 0.008189 | −0.031237 | −0.015556 |
| 62 | 0.053641 | 0.086163 | 0.042438 | 0.024786 | −0.061374 | −0.012628 | −0.103522 | −0.010394 | 0.027902 | 0.01094 | −0.004948 | −0.100682 | −0.005626 | −0.058417 |
| 63 | −0.030063 | −0.066955 | 0.019037 | 0.118396 | −0.034197 | −0.040482 | −0.052529 | 0.058116 | 0.018491 | −0.022161 | −0.033433 | −0.151771 | 0.010858 | −0.009487 |
| 64 | 0.030548 | 0.073198 | 0.045414 | 0.012016 | −0.024152 | 0.024733 | 0.0369 | −0.005206 | 0.028708 | 0.006617 | 0.022825 | −0.009971 | 0.056514 | 0.023009 |
| 65 | 0.030775 | 0.022185 | 0.019327 | 0.114824 | −0.005813 | −0.006113 | −0.069848 | −0.021738 | −0.028791 | −0.056519 | −0.040042 | −0.053246 | 0.01014 | 0.033732 |
| 66 | −0.029855 | −0.058177 | −0.014981 | −0.082449 | −0.072289 | −0.058667 | −0.085424 | 0.007234 | 0.018489 | 0.026349 | −0.009999 | −0.020293 | 0.011025 | −0.044695 |
| 67 | 0.047689 | 0.048925 | −0.073604 | 0.070066 | 0.068358 | 0.057426 | 0.026779 | −0.020418 | −0.013763 | −0.027316 | −0.004837 | 0.02801 | −0.010415 | 0.045534 |
| 68 | −0.008871 | −0.001396 | 0.041763 | 0.063265 | 0.025061 | 0.010439 | 0.020566 | 0.029362 | −0.008968 | 0.094727 | 0.078331 | 0.08057 | 0.004266 | 0.036889 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 69 | 0.016233 | 0.01365 | −0.064514 | 0.041578 | 0.051892 | 0.025429 | −0.045462 | −0.015414 | −0.003132 | −0.010197 | −0.006198 | 0.032464 | 0.013642 | 0.039201 |
| 70 | 0.072001 | 0.0487 | 0.027937 | −0.048951 | 0.000549 | −0.013031 | −0.05525 | −0.028254 | −0.044696 | −0.08817 | −0.099942 | −0.055756 | 0.020076 | 0.015916 |
| 71 | −0.059381 | −0.070999 | 0.059846 | −0.018134 | 0.008733 | −0.01507 | 0.005828 | 0.026957 | 0.020749 | 0.064978 | 0.062996 | 0.044197 | −0.010763 | 0.028774 |
| 72 | 0.043746 | 0.075654 | 0.042652 | −0.051608 | −0.060943 | −0.01308 | −0.024358 | −0.009263 | −0.015539 | 0.000053 | 0.035921 | 0.015104 | −0.014418 | −0.062671 |
| 73 | 0.007792 | −0.006637 | −0.047632 | 0.052188 | 0.051936 | −0.033469 | −0.058333 | −0.018741 | −0.081881 | −0.068023 | −0.052089 | −0.044811 | 0.021867 | −0.035465 |
| 74 | 0.021095 | 0.04301 | 0.051476 | 0.038705 | −0.047425 | −0.061646 | 0.030872 | 0.023347 | 0.01929 | −0.00873 | 0.012605 | 0.067705 | 0.009246 | 0.056879 |
| 75 | −0.032807 | −0.067364 | 0.059842 | −0.031162 | −0.0248 | −0.086999 | 0.050186 | 0.054559 | 0.04018 | 0.050601 | 0.053795 | 0.064649 | −0.044976 | −0.034346 |
| 76 | 0.013305 | 0.01715 | −0.031448 | 0.020021 | 0.062282 | 0.047209 | 0.074492 | −0.080339 | −0.086449 | 0.014464 | 0.000217 | 0.045803 | 0.025852 | 0.043423 |
| 77 | −0.040302 | −0.018419 | −0.048339 | 0.095922 | 0.018436 | 0.047101 | −0.004965 | 0.03489 | 0.024527 | 0.046984 | 0.021117 | 0.00825 | −0.003607 | 0.050523 |
| 78 | −0.01171 | 0.080269 | 0.032574 | −0.015669 | 0.026445 | 0.071557 | −0.006449 | 0.014381 | 0.020652 | 0.096437 | 0.118991 | 0.02794 | −0.027472 | −0.162892 |
| 79 | −0.014689 | −0.015835 | 0.061552 | −0.074359 | −0.021837 | 0.030265 | 0.001079 | −0.007635 | 0.027348 | 0.02836 | −0.008243 | −0.013691 | 0.013837 | −0.037121 |
| 80 | 0.03202 | 0.046995 | −0.007715 | 0.018979 | 0.011314 | 0.041504 | 0.060295 | −0.007885 | −0.00274 | 0.038905 | 0.077225 | 0.063533 | −0.022332 | 0.007184 |
| 81 | −0.018938 | −0.080661 | 0.000393 | 0.034801 | −0.009076 | 0.004027 | −0.013361 | 0.00699 | 0.031227 | −0.022555 | −0.009761 | 0.015739 | 0.001841 | −0.008976 |
| 82 | −0.077601 | −0.039184 | −0.045773 | −0.005389 | 0.003712 | 0.003809 | −0.022887 | −0.04161 | 0.000687 | −0.033975 | 0.003604 | −0.091195 | 0.042875 | −0.029166 |
| 83 | 0.096299 | 0.089552 | 0.056448 | −0.041886 | −0.041932 | 0.002429 | 0.055682 | −0.004308 | −0.015548 | 0.008254 | 0.026531 | 0.056372 | 0.001255 | 0.041361 |
| 84 | −0.043758 | −0.054748 | −0.069598 | 0.125628 | −0.026033 | 0.007665 | 0.027578 | −0.058375 | −0.048191 | −0.044839 | −0.024196 | −0.072321 | −0.033387 | 0.010033 |
| 85 | 0.006525 | 0.020484 | 0.047848 | −0.017755 | 0.060971 | 0.060532 | 0.013314 | −0.009709 | −0.000802 | 0.022649 | 0.030096 | 0.020416 | −0.019489 | 0.050102 |
| 86 | 0.046817 | 0.030747 | −0.023542 | −0.016593 | 0.004138 | 0.00863 | 0.081165 | 0.011891 | 0.03575 | 0.020491 | 0.003329 | 0.045795 | −0.043402 | 0.000747 |
| 87 | −0.06982 | −0.033351 | −0.044521 | −0.014794 | 0.043455 | 0.052178 | −0.012613 | 0.022913 | 0.01807 | 0.045802 | 0.011984 | 0.036912 | 0.053242 | −0.02617 |
| 88 | −0.005481 | −0.013558 | −0.00475 | 0.147314 | 0.094234 | 0.00483 | −0.005386 | −0.019608 | −0.041863 | 0.028023 | 0.034945 | 0.00773 | −0.066367 | 0.04175 |
| 89 | −0.028715 | −0.031505 | 0.050615 | −0.119382 | 0.076431 | 0.041727 | 0.059851 | −0.0115 | −0.026418 | −0.056541 | −0.04781 | −0.075478 | −0.026487 | 0.04008 |
| 90 | 0.029366 | 0.01052 | 0.043791 | −0.00624 | 0.019785 | 0.043258 | 0.030095 | −0.013039 | 0.008093 | −0.051348 | −0.030262 | 0.030139 | 0.041853 | −0.051166 |
| 91 | 0.010168 | 0.061463 | 0.014339 | 0.06149 | 0.063641 | 0.014695 | −0.002217 | 0.055419 | 0.048293 | 0.034839 | 0.00668 | 0.061656 | −0.003299 | −0.008536 |
| 92 | 0.019137 | 0.033611 | −0.008312 | −0.045999 | 0.005233 | 0.010335 | 0.032365 | −0.021361 | −0.023127 | −0.003461 | 0.024983 | −0.015906 | 0.002094 | −0.003537 |
| 93 | −0.011593 | −0.047609 | −0.050873 | 0.0624 | 0.00409 | 0.04135 | 0.021224 | 0.02089 | 0.021598 | −0.036383 | −0.043099 | −0.009163 | 0.047716 | −0.031602 |
| 94 | −0.022991 | −0.061017 | −0.020419 | 0.019627 | −0.024401 | −0.012322 | 0.005501 | 0.02984 | 0.039598 | 0.012287 | 0.011061 | −0.003676 | 0.030682 | 0.077907 |
| 95 | 0.001536 | −0.0322 | 0.020803 | 0.024106 | 0.01032 | −0.01371 | 0.01678 | −0.048517 | −0.052286 | 0.004362 | −0.013775 | 0.038014 | −0.02022 | −0.071008 |
| 96 | 0.016298 | −0.004608 | 0.024455 | −0.001677 | 0.032179 | 0.028163 | 0.010574 | 0.010653 | 0.030953 | 0.019785 | 0.009955 | −0.075755 | 0.024382 | −0.041223 |
| 97 | −0.038346 | 0.052154 | 0.000142 | −0.063104 | −0.019806 | −0.020334 | 0.009275 | −0.022101 | −0.021983 | −0.033829 | −0.025054 | −0.046433 | −0.018748 | −0.066411 |
| 98 | −0.02949 | 0.049579 | 0.038749 | 0.031451 | −0.023026 | 0.099772 | −0.093904 | 0.004162 | −0.068891 | 0.00735 | 0.005944 | −0.077643 | −0.021372 | 0.018832 |
| 99 | 0.017284 | 0.074029 | 0.091045 | −0.030122 | −0.048808 | −0.040883 | 0.012826 | −0.078201 | −0.020217 | −0.03161 | −0.164663 | −0.075425 | 0.032661 | −0.080314 |
| 100 | 0.006807 | −0.003449 | 0.023879 | −0.027191 | −0.025775 | −0.036086 | 0.010598 | −0.009021 | −0.011304 | −0.000025 | −0.003894 | 0.005967 | −0.012638 | −0.018541 |
| 101 | 0.006371 | 0.010876 | 0.002106 | −0.019125 | 0.014321 | 0.013862 | 0.010732 | −0.002547 | 0.004762 | −0.011442 | −0.010689 | 0.006296 | 0.009564 | 0.01317 |
| 102 | −0.000875 | 0.024777 | −0.000819 | 0.004038 | −0.022231 | −0.007806 | 0.010885 | 0.004466 | −0.00017e | 0.001417 | 0.008911 | 0.00318 | 0.015182 | 0.007135 |
| 103 | −0.005978 | −0.025796 | −0.018876 | −0.016064 | −0.014088 | −0.035653 | −0.005452 | 0.010627 | 0.019911 | −0.013833 | −0.021155 | 0.018142 | −0.004952 | −0.005261 |
| 104 | −0.010005 | −0.012128 | 0.007777 | 0.006058 | −0.000929 | −0.007103 | 0.040001 | −0.001152 | 0.000815 | 0.005881 | 0.008552 | 0.004496 | −0.005118 | 0.012229 |
| 105 | 0.029687 | 0.030703 | 0.024731 | 0.036339 | 0.003699 | 0.012975 | 0.02189 | 0.006805 | 0.01149 | 0.013261 | 0.015767 | −0.009194 | −0.00138 | −0.016241 |
| 106 | −0.020065 | −0.012944 | −0.00197 | 0.000281 | −0.012705 | −0.016204 | −0.019872 | 0.020274 | 0.006284 | 0.009907 | 0.003536 | 0.018264 | −0.002394 | 0.020768 |
| 107 | 0.015991 | 0.042063 | −0.004812 | 0.009404 | −0.012156 | 0.005733 | −0.005524 | −0.019528 | −0.009429 | −0.009885 | −0.00805 | 0.045047 | −0.009777 | 0.014195 |
| 108 | −0.011463 | −0.018045 | 0.006851 | −0.01438 | 0.041924 | 0.058632 | 0.004681 | −0.02642 | −0.00301 | −0.000796 | 0.003452 | −0.013141 | 0.020906 | 0.006526 |
| 109 | 0.006948 | −0.011313 | −0.017911 | 0.003859 | −0.018973 | −0.042341 | −0.042766 | −0.005395 | −0.018507 | −0.018599 | −0.017488 | 0.013359 | 0.011748 | 0.017674 |
| 110 | 0.016763 | −0.019724 | 0.00051 | 0.073315 | −0.027869 | −0.039742 | 0.035905 | −0.006857 | −0.009038 | −0.054818 | −0.055251 | 0.013481 | 0.030226 | 0.044031 |
| 111 | −0.01867 | −0.009793 | −0.011122 | 0.009806 | 0.018152 | 0.03278 | 0.030072 | 0.014598 | 0.034271 | 0.040718 | 0.06428 | 0.000371 | −0.048866 | −0.035845 |
| 112 | −0.017377 | 0.00044 | 0.008249 | −0.059005 | 0.002324 | 0.028722 | 0.007066 | −0.02238 | −0.036755 | 0.004735 | 0.001841 | 0.000396 | 0.002724 | 0.004327 |
| 113 | −0.016656 | −0.038797 | 0.005778 | 0.034433 | 0.013464 | 0.011191 | −0.020952 | −0.010092 | 0.002085 | −0.033894 | −0.007466 | −0.019085 | −0.034637 | 0.043153 |
| 114 | −0.010985 | 0.019774 | −0.038172 | −0.007896 | 0.048005 | 0.051523 | −0.012875 | −0.008429 | 0.003915 | 0.014495 | 0.019223 | 0.042303 | 0.018009 | 0.003598 |
| 115 | 0.033375 | 0.009497 | −0.019599 | 0.027421 | −0.003814 | −0.013075 | 0.006313 | −0.021185 | −0.031833 | −0.011952 | 0.004898 | 0.024492 | 0.018647 | 0.010386 |
| 116 | 0.0194711 | 0.012073 | −0.010855 | 0.005937 | 0.01018 | 0.030119 | 0.002301 | 0.001648 | −0.012337 | 0.004086 | 0.011841 | 0.004223 | −0.013192 | −0.019221 |
| 117 | −0.000455 | −0.007699 | 0.024783 | 0.032228 | −0.013575 | −0.016736 | 0.022893 | −0.005592 | −0.00311 | −0.006089 | −0.001542 | −0.003136 | 0.003608 | 0.002503 |
| 118 | −0.012041 | −0.036073 | −0.025645 | 0.05619 | 0.062281 | 0.017554 | −0.027106 | 0.004045 | −0.003502 | 0.006704 | 0.015212 | −0.00133 | −0.006916 | 0.007931 |
| 119 | −0.000005 | −0.018073 | −0.000416 | −0.021672 | 0.022485 | 0.011689 | 0.021325 | −0.017761 | −0.016009 | −0.002351 | 0.002033 | 0.007351 | −0.011961 | −0.005462 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 120 | −0.020202 | −0.009245 | 0.010246 | −0.02009 | −0.013523 | 0.01183 | −0.005247 | −0.004997 | −0.000983 | 0.013461 | −0.002222 | −0.005009 | 0.003219 | −0.019839 |
| 121 | −0.000581 | 0.013695 | −0.003619 | −0.600301 | −0.026043 | −0.029457 | −0.024874 | −0.001693 | −0.007765 | 0.003004 | −0.022356 | −0.021441 | 0.005856 | 0.001224 |
| 122 | −0.032338 | −0.016665 | 0.010878 | −0.001418 | −0.011349 | −0.003617 | −0.01955 | 0.009316 | −0.00764 | 0.003268 | 0.000745 | 0.009806 | 0.02481 | 0.01678 |
| 123 | 0.02032 | 0.002148 | −0.028944 | 0.057372 | 0.002143 | 0.003324 | −0.046489 | −0.008995 | −0.013887 | 0.005154 | −0.012829 | −0.005962 | 0.017689 | −0.002847 |
| 124 | 0.022305 | 0.024325 | 0.019853 | −0.000915 | 0.001642 | 0.000011 | −0.005398 | −0.007198 | −0.013299 | 0.027311 | 0.00205 | 0.013529 | −0.0299 | −0.012751 |
| 125 | 0.011316 | 0.009831 | 0.009748 | 0.060465 | 0.00711 | 0.043014 | −0.039726 | −0.0142 | −0.036362 | 0.013729 | 0.000552 | −0.029921 | −0.007631 | 0.005625 |
| 126 | 0.039053 | 0.017295 | 0.011288 | −0.000853 | 0.023944 | 0.011823 | −0.003202 | 0.008908 | −0.003304 | 0.014052 | −0.005494 | 0.022173 | −0.005105 | 0.021756 |
| 127 | 0.029623 | −0.001479 | 0.008433 | −0.019561 | 0.02144 | 0.001062 | 0.012633 | 0.000247 | −0.016602 | −0.004502 | −0.02071 | 0.028458 | 0.01071 | −0.005004 |
| 128 | 0.004223 | −0.011529 | 0.000569 | 0.024559 | 0.012137 | −0.004083 | 0.007171 | −0.003363 | −0.012908 | 0.003751 | −0.010117 | 0.00923 | −0.013382 | 0.014767 |
| 129 | −0.040785 | −0.020034 | 0.037483 | −0.003833 | −0.024903 | −0.014347 | 0.016352 | 0.0358 | 0.02164 | 0.020671 | 0.017978 | 0.049181 | 0.003082 | −0.017298 |
| 130 | −0.007681 | 0.013105 | −0.006848 | −0.028047 | −0.033851 | 0.003331 | −0.04416 | 0.001805 | −0.006332 | 0.017941 | −0.008052 | −0.032165 | 0.019245 | −0.007999 |
| 131 | 0.009409 | 0.034106 | 0.0164481 | 0.003466 | −0.04753 | −0.014327 | −0.023266 | −0.008646 | 0.017274 | −0.00698 | −0.002346 | 0.003799 | −0.022436 | 0.046682 |
| 132 | 0.012366 | −0.003878 | −0.010606 | 0.028023 | −0.001049 | 0.033388 | −0.012644 | 0.004121 | 0.008919 | 0.001272 | 0.007411 | 0.000023 | 0.010684 | −0.000077 |
| 133 | 0.025268 | 0.003545 | −0.0105 | 0.029767 | 0.019061 | −0.017454 | 0.028855 | −0.011707 | −0.019459 | −0.008059 | −0.011956 | 0.02618 | −0.011493 | 0.019576 |
| 134 | 0.014166 | −0.023537 | −0.034789 | −0.02542 | 0.003029 | 0.001046 | 0.011853 | 0.028006 | 0.019335 | 0.02213 | 0.023511 | 0.008375 | −0.013778 | −0.00444 |
| 135 | 0.006544 | 0.004377 | 0.009051 | −0.005524 | 0.002535 | 0.008601 | −0.010008 | −0.006133 | 0.0048831 | 0.0153091 | 0.0008271 | −0.020045 | −0.022974 | −0.008121 |
| 136 | −0.014332 | 0.003229 | 0.005637 | 0.03799 | −0.021375 | 0.025746 | −0.026157 | −0.010482 | −0.016839 | 0.003405 | 0.022185 | −0.012869 | 0.015413 | 0.03144 |
| 137 | −0.005862 | −0.040512 | −0.015408 | −0.001929 | 0.022433 | −0.005916 | 0.001423 | 0.010266 | 0.01546 | 0.01489 | −0.005812 | 0.002921 | −0.002057 | −0.008408 |
| 138 | −0.030737 | 0.001014 | 0.018435 | −0.05422 | 0.024614 | 0.037347 | 0.016421 | 0.005516 | 0.009813 | 0.024421 | 0.01815 | 0.018695 | −0.003308 | −0.008838 |
| 139 | −0.001728 | 0.015781 | 0.0066 | −0.032106 | 0.017492 | 0.008525 | −0.03273 | 0.002166 | 0.020632 | −0.019277 | −0.031243 | −0.040544 | −0.000291 | 0.013314 |
| 140 | −0.004327 | −0.00666 | 0.023542 | −0.020294 | −0.005292 | −0.018355 | 0.00575 | −0.021609 | −0.027476 | −0.025854 | −0.014051 | 0.012481 | 0.032547 | 0.048941 |
| 141 | −0.0131571 | −0.014727 | 0.0124371 | −0.018585 | −0.01077 | −0.008524 | −0.005401 | 0.003923 | −0.004085 | 0.03441 | 0.012181 | −0.013632 | 0.029789 | −0.004972 |
| 142 | −0.025041 | −0.039049 | −0.026166 | 0.034485 | 0.022582 | 0.015468 | −0.009789 | −0.008472 | −0.005403 | 0.016092 | 0.019978 | −0.014344 | −0.004148 | 0.029579 |
| 143 | −0.012808 | 0.053434 | 0.030398 | 0.012217 | 0.029513 | 0.010334 | 0.016542 | −0.010409 | −0.025436 | 0.017242 | 0.001281 | 0.013644 | 0.016771 | 0.020677 |
| 144 | 0.015398 | −0.00863 | 0.021458 | 0.002394 | −0.02302 | −0.002065 | 0.03747 | −0.002565 | 0.003273 | −0.007987 | −0.005017 | 0.004441 | −0.006056 | −0.011143 |
| 145 | 0.004529 | 0.027848 | −0.018996 | 0.015981 | 0.001049 | 0.03671 | 0.012043 | −0.00124 | 0.024178 | −0.004165 | 0.006408 | 0.003063 | 0.026208 | 0.019924 |
| 146 | 0.010113 | −0.012597 | −0.013112 | −0.021655 | 0.002355 | 0.02133 | −0.007179 | −0.000967 | 0.010976 | 0.01 | −0.011107 | −0.007972 | 0.007962 | −0.005636 |
| 147 | −0.00363 | 0.00017 | 0.010614 | 0.002091 | −0.004638 | 0.025553 | 0.004158 | 0.009694 | 0.005847 | −0.016437 | −0.032469 | 0.023733 | 0.017995 | 0.012079 |
| 148 | −0.005505 | −0.028697 | 0.006575 | −0.033163 | 0.03023 | 0.00725 | 0.015497 | 0.028282 | 0.042232 | −0.026878 | −0.028204 | 0.013397 | −0.006911 | 0.046526 |
| 149 | −0.016435 | −0.016883 | 0.01855 | −0.020122 | −0.030474 | −0.035923 | −0.015305 | 0.005684 | 0.012765 | −0.038123 | −0.018941 | −0.024279 | −0.018284 | 0.012227 |
| 150 | −0.021397 | −0.005982 | 0.030931 | −0.035571 | −0.01531 | 0.016829 | −0.04563 | 0.036831 | 0.011242 | 0.033604 | 0.010761 | −0.002568 | 0.004207 | −0.005059 |
| 151 | −0.005986 | −0.005248 | 0.016854 | −0.01006 | −0.022523 | 0.003935 | 0.024659 | 0.020872 | 0.007677 | −0.007823 | −0.007326 | 0.024652 | 0.043652 | 0.011036 |
| 152 | −0.017526 | −0.000294 | 0.015413 | −0.026211 | 0.024677 | 0.001691 | 0.015961 | 0.003745 | −0.007915 | 0.007493 | −0.010969 | 0.009966 | −0.004058 | −0.026089 |
| 153 | −0.014514 | −0.041164 | −0.042143 | −0.021022 | −0.000795 | −0.001757 | −0.019563 | 0.025205 | 0.023581 | −0.001785 | −0.012663 | 0.023686 | 0.04488 | −0.003172 |
| 154 | 0.002367 | −0.010058 | −0.001345 | 0.005798 | −0.038758 | −0.01016 | 0.01847 | 0.031967 | 0.030645 | 0.014322 | 0.01522 | 0.013028 | 0.007375 | 0.008165 |
| 155 | 0.028363 | 0.028796 | 0.001335 | −0.01193 | −0.00495 | 0.013683 | −0.000226 | 0.007642 | 0.017573 | 0.025913 | 0.021807 | 0.020286 | 0.013961 | −0.02111 |
| 156 | 0.032034 | 0.030004 | −0.025147 | −0.000948 | −0.066327 | −0.0291 | −0.043022 | −0.007263 | 0.025809 | −0.026858 | −0.046608 | −0.014107 | 0.020244 | 0.019399 |
| 157 | 0.006081 | 0.015103 | 0.013274 | 0.00978 | 0.000128 | 0.000563 | 0.000155 | −0.016447 | −0.020294 | 0.011301 | 0.010437 | −0.021074 | −0.053003 | −0.008288 |
| 158 | 0.006789 | −0.003311 | 0.004179 | −0.052239 | −0.021109 | −0.028296 | −0.006026 | 0.004332 | −0.018692 | 0.012598 | −0.000567 | 0.020699 | −0.005655 | −0.027278 |
| 159 | −0.023824 | −0.028463 | −0.002609 | 0.009818 | −0.024251 | −0.005888 | 0.012028 | 0.008371 | 0.023748 | 0.027818 | 0.022996 | 0.029556 | 0.004064 | −0.049037 |
| 160 | −0.015837 | −0.018372 | −0.012903 | −0.005823 | −0.025806 | −0.000997 | −0.02773 | −0.034879 | −0.042592 | 0.004604 | −0.002071 | 0.029781 | −0.019109 | −0.050405 |
| 161 | −0.008976 | 0.015298 | −0.022233 | 0.036695 | 0.016548 | 0.003507 | −0.036076 | −0.007908 | −0.033485 | −0.025183 | −0.012236 | −0.030179 | −0.019221 | 0.02991 |
| 162 | −0.003834 | 0.003854 | 0.025099 | −0.007653 | 0.007856 | −0.004801 | 0.027989 | −0.015573 | 0.004231 | −0.027475 | −0.00991 | −0.044831 | −0.032576 | 0.004046 |
| 163 | −0.012691 | 0.006588 | 0.026919 | −0.04105 | 0.008094 | −0.007487 | −0.011768 | 0.004123 | 0.016122 | 0.000477 | −0.002306 | −0.040055 | −0.021596 | 0.000529 |
| 164 | 0.015927 | 0.02004 | 0.028325 | −0.004337 | 0.007432 | 0.023313 | 0.021495 | 0.001185 | 0.012633 | −0.008612 | −0.00453 | 0.000462 | 0.005853 | 0.005183 |
| 165 | 0.045032 | 0.037723 | 0.000304 | −0.003526 | 0.009382 | 0.010538 | 0.026904 | −0.023401 | −0.02942 | −0.000087 | 0.016692 | 0.042821 | −0.011657 | 0.00225 |
| 166 | −0.014055 | 0.000416 | −0.002898 | 0.006486 | −0.015028 | 0.014433 | −0.032494 | 0.006749 | 0.026961 | 0.041207 | 0.050878 | 0.016573 | −0.019669 | 0.000581 |
| 167 | −0.015982 | −0.001479 | 0.032992 | 0.031748 | 0.02114 | 0.042816 | −0.010654 | −0.022935 | 0.004716 | −0.004676 | 0.000644 | −0.036854 | 0.025319 | −0.035427 |
| 168 | −0.003808 | −0.003958 | 0.007047 | 0.013166 | 0.011566 | −0.023939 | −0.013264 | −0.004208 | −0.01403 | −0.027218 | −0.039961 | −0.049011 | −0.027985 | 0.00066 |
| 169 | 0.003773 | 0.01 | 0.031551 | −0.042443 | 0.008098 | −0.006045 | 0.013079 | 0.010154 | 0.021441 | 0.001326 | −0.008066 | −0.010593 | 0.009731 | −0.016451 |
| 170 | 0.000429 | 0.001903 | 0.013906 | −0.038253 | −0.020813 | −0.018074 | 0.015043 | 0.024686 | 0.027919 | 0.008156 | −0.003966 | 0.027248 | 0.013904 | −0.017081 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 171 | 0.001099 | −0.004987 | 0.012644 | −0.023098 | −0.00004 | −0.022794 | −0.007684 | 0.00741 | 0.014495 | 0.000534 | −0.014222 | −0.005776 | 0.021394 | −0.014108 |
| 172 | 0.009934 | 0.006946 | 0.03985 | −0.015635 | 0.028742 | 0.009822 | 0.008575 | −0.002737 | −0.003225 | 0.009515 | −0.001035 | −0.00997 | −0.004333 | −0.010907 |
| 173 | 0.01865 | 0.005795 | 0.012098 | 0.008529 | −0.006154 | −0.032145 | 0.000153 | −0.004061 | −0.007414 | −0.004788 | −0.003661 | −0.004046 | 0.020824 | 0.009836 |
| 174 | 0.012615 | 0.008739 | −0.005465 | 0.024307 | −0.009281 | −0.028708 | −0.004854 | 0.010005 | 0.014153 | 0.014247 | 0.003874 | −0.011189 | 0.004051 | 0.012454 |
| 175 | −0.019739 | −0.016174 | 0.005873 | −0.020346 | −0.000505 | −0.031113 | 0.00964 | 0.023791 | 0.023123 | 0.020873 | 0.017779 | −0.001254 | −0.04231 | −0.017248 |
| 176 | 0.00002 | 0.008824 | 0.035403 | 0.001811 | 0.026777 | 0.012858 | −0.008988 | 0.009187 | 0.002623 | 0.021803 | 0.008419 | −0.009684 | −0.027133 | −0.011765 |
| 177 | 0.025197 | 0.066927 | 0.033787 | 0.018888 | −0.020211 | −0.010566 | −0.004193 | 0.037873 | 0.046261 | −0.027614 | 0.009565 | 0.007231 | −0.009608 | −0.055223 |
| 178 | 0.002481 | 0.015308 | −0.001649 | −0.015664 | 0.037489 | −0.005169 | −0.000634 | −0.003725 | −0.003928 | −0.013194 | −0.026692 | −0.007575 | −0.017043 | −0.013461 |
| 179 | −0.015003 | −0.018744 | −0.014476 | 0.016376 | 0.014644 | −0.002285 | 0.005846 | −0.010593 | 0.002334 | −0.007297 | −0.00496 | 0.003663 | 0.016228 | 0.000849 |
| 180 | −0.004006 | −0.005233 | −0.015069 | 0.02336 | 0.01323 | 0.003858 | −0.010362 | −0.006121 | −0.009897 | −0.011628 | −0.001738 | 0.006379 | 0.009317 | 0.011567 |
| 181 | −0.006559 | −0.014126 | −0.014914 | 0.010194 | −0.003629 | −0.010876 | 0.000464 | 0.002674 | 0.003696 | −0.008492 | 0.0001 | 0.023327 | 0.019297 | 0.014209 |
| 182 | −0.0177381 | −0.042772 | 0.001616 | 0.007441 | −0.01595 | −0.036695 | 0.026441 | 0.017448 | 0.008617 | −0.004194 | 0.006019 | 0.043532 | 0.004251 | 0.00171 |
| 183 | −0.016956 | −0.036504 | −0.007526 | 0.010976 | −0.014031 | −0.022113 | 0.001824 | 0.013103 | 0.014887 | 0.01017 | 0.019958 | 0.031886 | 0.013582 | −0.002014 |
| 184 | 0.001347 | −0.01518 | −0.042034 | 0.007589 | 0.015724 | 0.02049 | −0.058595 | 0.003364 | 0.005641 | 0.017497 | 0.021149 | −0.031642 | 0.006113 | −0.028156 |
| 185 | 0.046038 | 0.03567 | 0.027822 | 0.028811 | 0.039576 | 0.004103 | −0.006618 | 0.00574 | 0.008451 | 0.020754 | 0.022095 | 0.024693 | 0.004138 | −0.017382 |
| 186 | 0.006422 | 0.028276 | −0.003723 | −0.038752 | −0.033396 | −0.019268 | −0.038448 | −0.001846 | −0.020043 | 0.014418 | 0.017005 | 0.021258 | 0.033495 | 0.01027 |
| 187 | −0.006988 | −0.006927 | 0.015213 | 0.001912 | 0.015541 | 0.027101 | 0.027495 | 0.002078 | −0.010757 | 0.00648 | 0.023483 | −0.004543 | 0.009505 | 0.017498 |
| 188 | 0.003101 | 0.003431 | 0.007668 | −0.003396 | 0.003266 | 0.020369 | 0.015662 | 0.008864 | 0.012732 | 0.006857 | 0.013552 | −0.000352 | 0.017509 | 0.01123 |
| 189 | −0.000225 | −0.005973 | 0.009671 | −0.030606 | −0.024909 | 0.017261 | 0.030083 | 0.020681 | 0.050883 | 0.025935 | 0.009018 | −0.011039 | 0.012005 | 0.013425 |
| 190 | −0.005424 | 0.006394 | 0.001524 | 0.032057 | 0.016562 | −0.001444 | −0.010252 | 0.004134 | −0.00979 | 0.021851 | 0.01805 | −0.021212 | −0.034024 | 0.001176 |
| 191 | 0.006552 | 0.017705 | 0.001901 | −0.002718 | −0.007042 | −0.009847 | 0.018541 | −0.017828 | −0.018022 | 0.007536 | 0.011392 | −0.001418 | −0.005593 | 0.005788 |
| 192 | −0.006807 | −0.011017 | 0.011565 | 0.009086 | −0.023197 | 0.003355 | 0.053193 | −0.019406 | −0.017077 | −0.009291 | 0.022139 | 0.006647 | 0.022339 | −0.007811 |
| 193 | −0.017435 | −0.024216 | −0.005386 | 0.025895 | 0.010308 | 0.005294 | 0.015792 | −0.017127 | −0.014519 | 0.000109 | 0.007502 | −0.000541 | −0.008611 | −0.02588 |
| 194 | 0.000756 | 0.019699 | −0.001684 | −0.006092 | 0.018875 | 0.030362 | −0.014029 | −0.002981 | 0.008765 | −0.018602 | −0.007024 | −0.019835 | −0.002269 | −0.003028 |
| 195 | −0.003951 | 0.024999 | −0.016245 | 0.029397 | 0.000886 | 0.02448 | −0.011752 | −0.001998 | 0.016571 | 0.026321 | 0.036573 | 0.007347 | −0.051254 | 0.00021 |
| 196 | 0.000804 | 0.011166 | −0.004652 | −0.032266 | 0.005816 | 0.001927 | −0.014907 | 0.002496 | −0.000272 | −0.009407 | 0.003106 | −0.030528 | −0.035722 | −0.004771 |
| 197 | 0.0011781 | −0.008826 | −0.0071671 | −0.014468 | −0.018159 | −0.0217 | 0.029818 | −0.027223 | −0.027084 | 0.005248 | 0.007887 | −0.005622 | −0.016022 | −0.005439 |
| 198 | −0.003112 | −0.001487 | −0.027585 | −0.012667 | 0.060068 | 0.055157 | −0.01123 | 0.014256 | 0.014062 | 0.01243 | 0.003148 | 0.015933 | −0.075837 | 0.014704 |
| 199 | −0.011761 | 0.003832 | −0.012964 | 0.026543 | −0.018156 | 0.024151 | 0.060742 | −0.020853 | −0.000478 | −0.035956 | −0.014017 | 0.002136 | −0.015808 | −0.002825 |
| 200 | 0.012033 | −0.005851 | 0.000087 | 0.002587 | 0.010712 | −0.005134 | −0.002569 | −0.010263 | −0.008143 | −0.034049 | −0.020845 | −0.0022 | −0.042804 | 0.018872 |
| 201 | 0.018531 | 0.014237 | −0.01586 | −0.015553 | −0.027948 | 0.002311 | −0.019186 | 0.001282 | −0.00399 | −0.048586 | −0.036232 | 0.007256 | 0.012317 | −0.01439 |
| 202 | 0.008761 | 0.021117 | −0.012112 | −0.048303 | −0.012382 | −0.016482 | 0.010905 | −0.002585 | 0.006451 | 0.006316 | −0.032182 | 0.018196 | −0.028682 | −0.001367 |
| 203 | 0.012723 | 0.021328 | 0.019255 | 0.01197 | −0.002806 | 0.0262 | 0.037926 | 0.01155 | 0.018047 | −0.012285 | 0.019335 | 0.020894 | −0.040275 | −0.006274 |
| 204 | 0.014183 | −0.01225 | −0.004034 | 0.029331 | 0.030074 | −0.008174 | −0.017032 | 0.01103 | −0.020685 | 0.035721 | 0.020417 | 0.027954 | −0.016495 | −0.003541 |
| 205 | −0.010097 | −0.025934 | 0.020373 | −0.029931 | −0.010597 | −0.022506 | 0.007626 | 0.00272 | −0.017785 | 0.027068 | 0.042149 | 0.023639 | −0.019332 | 0.033133 |
| 206 | 0.002452 | 0.00362 | −0.001896 | 0.057149 | 0.011669 | 0.002782 | −0.036253 | −0.011381 | −0.024062 | 0.023079 | 0.012197 | −0.003225 | −0.050978 | 0.002372 |
| 207 | −0.008816 | −0.010236 | −0.021219 | −0.001172 | 0.000309 | −0.025088 | −0.002504 | −0.008415 | −0.005383 | 0.000999 | −0.018152 | −0.006025 | 0.025008 | −0.015077 |
| 208 | −0.00947 | −0.01536 | −0.020333 | 0.01332 | −0.008149 | 0.023613 | 0.029921 | −0.036293 | −0.024286 | −0.005491 | 0.004091 | 0.005291 | 0.005372 | 0.007298 |
| 209 | −0.018947 | −0.02439 | −0.041468 | 0.02726 | −0.024431 | −0.049875 | −0.026208 | 0.008743 | 0.023271 | −0.026739 | −0.022979 | −0.026993 | −0.005947 | −0.025452 |
| 210 | 0.011849 | 0.026092 | 0.021037 | 0.036104 | 0.000466 | −0.006456 | −0.000755 | 0.006965 | −0.006081 | −0.041924 | −0.053552 | −0.039394 | −0.022289 | 0.014917 |
| 211 | 0.012339 | 0.007323 | −0.018077 | 0.024393 | 0.009299 | −0.013687 | −0.009441 | −0.016814 | −0.011859 | −0.027169 | −0.039658 | −0.032813 | 0.011169 | 0.025566 |
| 212 | −0.002343 | 0.009638 | 0.000329 | 0.03171 | −0.012399 | −0.027497 | −0.000722 | −0.014175 | −0.026786 | −0.044113 | −0.026492 | 0.003163 | 0.005612 | 0.006962 |
| 213 | −0.011952 | −0.045889 | −0.013037 | −0.013626 | −0.01413 | 0.00108 | −0.017887 | 0.007674 | 0.019125 | −0.040306 | −0.020787 | −0.018733 | 0.054492 | 0.034362 |
| 214 | −0.005301 | −0.016873 | −0.027176 | 0.022709 | 0.005658 | 0.000726 | −0.019489 | −0.008361 | −0.003714 | 0.001138 | 0.006971 | 0.000735 | 0.019758 | 0.010198 |
| 215 | 0.010391 | 0.020572 | 0.015006 | 0.003304 | −0.01971 | 0.006223 | 0.007585 | −0.007561 | −0.02845 | −0.019477 | 0.014496 | −0.007694 | 0.004052 | 0.013764 |
| 216 | 0.030374 | 0.049614 | 0.005954 | −0.090988 | −0.014973 | −0.019902 | −0.011911 | 0.016399 | 0.014359 | −0.00586 | −0.020604 | −0.006952 | −0.011057 | 0.005685 |
| 217 | 0.00499 | 0.008441 | 0.037892 | −0.01525 | 0.028659 | 0.028309 | 0.01735 | 0.035807 | 0.024543 | 0.011078 | 0.007806 | −0.007581 | −0.025981 | 0.016434 |
| 218 | −0.002251 | −0.003184 | −0.005758 | 0.001868 | −0.034377 | −0.033659 | −0.014093 | 0.014265 | 0.016168 | −0.001296 | 0.003456 | 0.005976 | 0.023851 | 0.005099 |
| 219 | 0.028524 | 0.039006 | −0.066235 | −0.001945 | −0.016088 | −0.00093 | −0.058299 | 0.019774 | 0.029196 | 0.017803 | 0.016734 | 0.002139 | 0.029338 | 0.016134 |
| 220 | 0.070487 | 0.043483 | 0.023369 | 0.026172 | −0.025834 | −0.028093 | −0.040047 | 0.010181 | −0.003736 | 0.043006 | 0.032942 | 0.020814 | −0.031964 | −0.014238 |
| 221 | 0.036629 | 0.039073 | 0.029159 | −0.043469 | 0.013756 | −0.015531 | −0.01199 | −0.00022 | 0.002837 | −0.003309 | −0.012069 | 0.008344 | −0.00226 | 0.023231 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 222 | 0.023007 | 0.028098 | 0.017357 | −0.030355 | −0.00111 | −0.009683 | 0.01575 | −0.004595 | −0.01118 | −0.02124 | −0.013355 | 0.011209 | 0.018823 | 0.008064 |
| 223 | 0.020845 | 0.016629 | 0.014724 | 0.001446 | −0.000136 | −0.017958 | −0.019874 | 0.008381 | −0.004215 | −0.010523 | −0.016344 | 0.032339 | 0.023471 | 0.004555 |
| 224 | −0.008484 | −0.021112 | −0.00476 | −0.020055 | −0.027113 | −0.022937 | −0.01006 | 0.006524 | 0.016173 | −0.010261 | −0.007035 | −0.047941 | −0.012468 | 0.020623 |
| 225 | −0.010663 | −0.020151 | −0.000816 | −0.029314 | −0.022756 | −0.015489 | 0.003658 | 0.020487 | 0.026901 | −0.025287 | −0.001629 | −0.031575 | −0.015429 | 0.021879 |
| 226 | 0.032284 | 0.037945 | 0.019738 | 0.001265 | 0.003753 | 0.010982 | 0.012886 | −0.010608 | −0.014272 | −0.021226 | −0.020622 | −0.002986 | 0.007655 | 0.018234 |
| 227 | 0.026248 | 0.024068 | 0.038499 | 0.02981 | 0.02457 | 0.022772 | 0.013008 | −0.008048 | −0.002836 | −0.030048 | −0.023374 | −0.037584 | −0.007018 | 0.042159 |
| 228 | −0.016813 | −0.030399 | −0.017251 | −0.091703 | −0.007554 | −0.010815 | −0.005015 | 0.011433 | 0.007034 | 0.008696 | −0.008508 | −0.031131 | 0.00365 | 0.01807 |
| 229 | 0.012477 | −0.014238 | 0.000684 | −0.013997 | −0.022058 | −0.001642 | −0.010699 | 0.008711 | 0.011925 | 0.004299 | 0.018855 | 0.028702 | 0.011197 | 0.035033 |
| 230 | 0.040179 | 0.032248 | −0.023547 | −0.005981 | 0.001403 | −0.005829 | −0.024439 | −0.008794 | −0.010006 | 0.008502 | −0.015787 | 0.009908 | −0.001108 | 0.023054 |
| 231 | 0.003869 | −0.003485 | −0.002393 | 0.042797 | 0.042828 | 0.055182 | 0.007329 | 0.010905 | 0.022703 | 0.026502 | 0.043965 | 0.026976 | 0.000435 | 0.026803 |
| 232 | −0.020339 | −0.031142 | −0.029387 | 0.020814 | 0.024795 | 0.038298 | −0.020049 | 0.013771 | −0.00005 | 0.039931 | 0.012391 | −0.013597 | −0.002976 | −0.014452 |
| 233 | −0.012903 | −0.017268 | 0.004916 | −0.066067 | −0.042449 | −0.025376 | 0.005848 | 0.035468 | 0.050072 | 0.022036 | 0.017647 | 0.032965 | 0.034072 | 0.018896 |
| 234 | 0.01667 | 0.011428 | −0.031849 | −0.005627 | 0.001902 | 0.022739 | −0.021254 | −0.004021 | −0.000608 | 0.030481 | 0.030163 | 0.002122 | 0.001584 | −0.003615 |
| 235 | −0.002979 | 0.004271 | −0.013112 | −0.022199 | 0.012476 | 0.014627 | −0.001288 | −0.021252 | −0.012101 | 0.017628 | 0.037046 | −0.003614 | −0.014202 | 0.022289 |
| 236 | −0.008097 | −0.000257 | 0.010547 | 0.028689 | 0.020539 | 0.012839 | −0.040557 | 0.012661 | 0.008622 | 0.035672 | 0.027593 | −0.03554 | −0.061266 | 0.001825 |
| 237 | −0.068186 | −0.052317 | 0.032979 | −0.00222 | −0.006115 | 0.040784 | 0.026085 | 0.031935 | 0.043774 | 0.00537 | 0.031735 | −0.027464 | 0.01893 | −0.032921 |
| 238 | −0.004716 | 0.009854 | −0.100832 | 0.018226 | 0.022591 | 0.052727 | −0.001537 | 0.018241 | 0.035168 | 0.031627 | 0.039552 | 0.035645 | 0.036985 | −0.004312 |
| 239 | −0.005493 | 0.004611 | −0.121533 | 0.019444 | 0.025265 | 0.034247 | −0.010089 | 0.019324 | 0.02355 | 0.026839 | 0.031458 | 0.038299 | 0.01881 | 0.030379 |
| 240 | 0.024159 | 0.023096 | 0.010406 | 0.003842 | 0.014315 | 0.014005 | 0.019789 | 0.005523 | 0.023825 | 0.010868 | −0.006994 | −0.004846 | 0.015167 | −0.003856 |
| 241 | 0.018927 | 0.029042 | 0.018364 | −0.016127 | −0.010627 | −0.015506 | 0.020635 | 0.02381 | 0.032665 | −0.000196 | −0.010458 | −0.005312 | 0.002832 | 0.009516 |
| 242 | −0.004468 | −0.017989 | 0.017192 | −0.071302 | −0.02825 | −0.038276 | 0.011176 | 0.018335 | 0.009531 | 0.02893 | 0.029882 | 0.022026 | −0.025501 | −0.012453 |
| 243 | 0.012718 | 0.028131 | −0.014872 | −0.195688 | −0.02467 | −0.02553 | −0.021363 | 0.02711 | 0.034182 | 0.005976 | −0.017786 | 0.001869 | 0.016935 | −0.017233 |
| 244 | −0.008497 | −0.013152 | 0.003621 | −0.010046 | 0.063779 | 0.034001 | 0.026165 | 0.003888 | −0.009555 | 0.002922 | −0.004266 | 0.026851 | −0.01347 | 0.008878 |
| 245 | −0.006775 | −0.014243 | 0.006167 | 0.020325 | −0.007244 | 0.00091 | 0.028691 | 0.01271 | 0.030438 | 0.002036 | −0.000482 | 0.018047 | 0.011897 | 0.009239 |
| 246 | 0.005016 | −0.007053 | 0.02156 | 0.030275 | −0.087551 | −0.06198 | −0.017943 | 0.030697 | 0.030579 | 0.049476 | 0.064614 | 0.0189331 | −0.003088 | −0.017068 |
| 247 | 0.024602 | 0.037706 | −0.005613 | 0.022243 | −0.029316 | −0.029478 | −0.102447 | 0.028928 | 0.022902 | 0.033341 | 0.031612 | −0.02979 | −0.025828 | −0.000083 |
| 248 | 0.021932 | 0.023082 | −0.031073 | 0.037321 | −0.00942 | −0.000237 | −0.10854 | 0.020547 | 0.022738 | 0.03453 | 0.020519 | −0.044332 | −0.012832 | −0.001923 |
| 249 | 0.047433 | 0.053849 | 0.007315 | 0.008969 | 0.001544 | 0.029267 | −0.001249 | 0.007361 | 0.002405 | 0.006081 | 0.017071 | 0.023275 | 0.019326 | 0.00453 |
| 250 | 0.026158 | 0.03397 | 0.00794 | 0.034371 | 0.015493 | 0.018143 | 0.015531 | −0.008819 | −0.008651 | 0.01766 | 0.026179 | 0.019213 | 0.004353 | −0.007967 |
| 251 | 0.026532 | 0.020476 | 0.001223 | 0.001317 | 0.01739 | 0.004021 | 0.01926 | −0.007151 | −0.008235 | −0.006567 | −0.016695 | −0.004583 | 0.002733 | −0.021414 |
| 252 | 0.024971 | 0.025285 | 0.003725 | −0.033338 | 0.052816 | 0.0207 | 0.029244 | −0.001566 | −0.005415 | −0.00753 | −0.014837 | 0.008202 | −0.024252 | −0.00906 |
| 253 | 0.017621 | 0.013669 | 0.051767 | −0.145076 | 0.008342 | −0.001959 | 0.028954 | −0.008863 | −0.007874 | −0.036315 | −0.035414 | −0.026919 | −0.009153 | −0.025336 |
| 254 | 0.0095051 | 0.008537 | −0.011951 | 0.003268 | 0.014945 | 0.004405 | −0.002124 | 0.018535 | 0.011514 | 0.000529 | 0.006523 | 0.03626 | 0.004006 | −0.005217 |
| 255 | 0.035738 | 0.031826 | 0.027691 | −0.039711 | 0.022885 | −0.005741 | 0.015309 | 0.002428 | 0.00066 | 0.009722 | −0.006336 | 0.021196 | −0.016378 | −0.005394 |
| 256 | 0.067693 | 0.068159 | 0.041072 | −0.008527 | 0.020934 | 0.004733 | 0.008998 | −0.0396 | −0.030285 | −0.02221 | −0.007756 | 0.017571 | −0.039153 | 0.012629 |
| 257 | 0.037117 | 0.045844 | 0.03469 | 0.020754 | 0.030168 | 0.014519 | 0.034536 | −0.089389 | −0.09436 | −0.057366 | −0.048687 | −0.005756 | −0.021956 | 0.001743 |
| 258 | 0.022146 | 0.034985 | 0.04504 | −0.018336 | −0.016508 | −0.028449 | −0.018844 | −0.021564 | −0.012965 | −0.111696 | −0.113054 | −0.126402 | −0.03339 | 0.003028 |
| 259 | 0.019409 | 0.020588 | 0.002991 | −0.041754 | −0.014209 | 0.005256 | 0.007739 | 0.005886 | 0.001289 | −0.003402 | 0.00481 | 0.021108 | 0.033364 | −0.003377 |
| 260 | −0.019697 | −0.016194 | −0.015148 | 0.007392 | 0.033071 | 0.048053 | −0.020966 | 0.001397 | −0.004374 | 0.010521 | 0.011719 | −0.025465 | −0.006178 | 0.002464 |
| 261 | 0.011282 | −0.002475 | 0.003664 | −0.004865 | −0.001548 | 0.023874 | −0.013479 | 0.004409 | 0.015257 | −0.019643 | −0.018429 | −0.054426 | −0.024761 | −0.024459 |
| 262 | 0.005151 | −0.007421 | 0.011516 | 0.021417 | 0.029916 | 0.015637 | −0.009634 | −0.001651 | −0.012472 | −0.000664 | 0.008023 | −0.024314 | −0.077836 | 0.009365 |
| 263 | 0.007367 | 0.005621 | 0.006539 | −0.025882 | 0.021106 | 0.01012 | −0.001343 | −0.012909 | −0.016391 | −0.000042 | −0.008282 | −0.01031 | −0.052143 | −0.000455 |
| 264 | 0.007147 | 0.02537 | 0.008441 | −0.039106 | −0.014786 | 0.00238 | 0.008023 | −0.008218 | 0.000758 | −0.001682 | 0.014215 | 0.00097 | 0.029467 | 0.011378 |
| 265 | 0.007988 | 0.031593 | −0.019503 | −0.007872 | 0.002395 | 0.021786 | −0.006094 | 0.014314 | 0.021669 | 0.016422 | 0.03897 | 0.023627 | −0.03152 | 0.007673 |
| 266 | 0.013175 | 0.004264 | −0.018342 | −0.020046 | 0.010415 | 0.010619 | −0.031828 | 0.0088 | 0.019455 | −0.002213 | −0.004764 | −0.012848 | −0.053092 | −0.002761 |
| 267 | 0.007526 | 0.014837 | −0.003657 | −0.005722 | 0.013195 | 0.03436 | 0.018458 | −0.002547 | 0.013419 | 0.002241 | 0.001157 | 0.016846 | 0.011642 | 0.009481 |
| 268 | 0.01351 | 0.035917 | 0.015398 | −0.016112 | 0.023821 | 0.022573 | 0.03054 | −0.013314 | −0.018434 | −0.003038 | 0.00216 | 0.01388 | −0.004212 | 0.014769 |
| 269 | 0.019411 | 0.020927 | 0.02636 | 0.007963 | 0.026257 | 0.005927 | 0.020561 | −0.015123 | −0.023072 | −0.003966 | −0.005215 | 0.013666 | −0.000478 | 0.011835 |
| 270 | 0.022882 | 0.014253 | 0.024381 | 0.011324 | 0.01305 | −0.005586 | 0.010335 | −0.018894 | −0.018622 | −0.018128 | −0.037003 | −0.021194 | −0.010989 | −0.002457 |
| 271 | 0.015332 | 0.018758 | 0.02337 | −0.010403 | 0.001468 | −0.023159 | 0.030937 | 0.002452 | −0.00528 | 0.013961 | 0.026786 | 0.023945 | −0.026898 | −0.002342 |
| 272 | 0.013781 | 0.010802 | −0.01788 | 0.006613 | 0.000117 | 0.017889 | 0.00181 | −0.014628 | 0.007846 | 0.008863 | 0.008242 | 0.019357 | 0.019934 | 0.015433 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 273 | 0.016535 | 0.022869 | 0.006468 | −0.002389 | −0.002673 | −0.001214 | −0.016395 | −0.021409 | −0.021267 | 0.022516 | 0.011532 | 0.015346 | −0.008409 | 0.00338 |
| 274 | 0.015119 | 0.016254 | 0.010714 | 0.008197 | −0.002319 | −0.00431 | −0.021725 | −0.021458 | −0.025145 | 0.020831 | 0.009896 | 0.009635 | −0.010511 | 0.00402 |
| 275 | 0.023407 | 0.005156 | −0.021966 | 0.015573 | 0.022359 | −0.006057 | −0.066591 | −0.012258 | −0.011301 | 0.00688 | −0.028883 | −0.055538 | −0.027636 | −0.006934 |
| 276 | −0.00942 | −0.00875 | 0.000856 | −0.001293 | 0.017213 | 0.008797 | −0.038374 | 0.006128 | 0.002481 | 0.011062 | 0.021908 | −0.031144 | −0.05001 | 0.016414 |
| 277 | 0.854179 | −0.124563 | −0.013296 | 0.000519 | −0.007703 | 0.004684 | 0.006623 | 0.023227 | 0.026916 | 0.017135 | 0.018154 | −0.032562 | −0.000545 | −0.008409 |
| 278 | −0.145855 | 0.804982 | −0.037615 | 0.028606 | 0.004437 | −0.014226 | 0.012619 | 0.025696 | 0.022689 | 0.0085 | 0.004001 | −0.029437 | 0.003346 | 0.014779 |
| 279 | −0.035745 | −0.051783 | 0.827884 | 0.034092 | 0.023876 | 0.022422 | −0.041363 | 0.014734 | 0.023778 | 0.029284 | 0.016098 | 0.005471 | 0.025131 | 0.019371 |
| 280 | −0.020737 | −0.003045 | 0.049303 | 0.66156 | −0.073315 | −0.057222 | 0.033916 | 0.035029 | 0.056203 | −0.026451 | −0.036268 | −0.004497 | 0.015679 | −0.019262 |
| 281 | 0.005866 | −0.00763 | 0.002385 | −0.025591 | 0.802297 | −0.140765 | −0.07206 | 0.027148 | 0.03226 | −0.013372 | −0.012346 | −0.022769 | 0.022054 | −0.018305 |
| 282 | 0.011406 | −0.028162 | 0.003669 | −0.020823 | −0.136209 | 0.819164 | −0.058521 | 0.018095 | 0.002497 | −0.038794 | −0.053309 | −0.021486 | −0.000742 | −0.002066 |
| 283 | 0.015866 | −0.002345 | −0.059748 | 0.038432 | −0.046135 | −0.058073 | 0.811068 | 0.020319 | 0.011291 | 0.021311 | −0.014946 | −0.089414 | −0.017083 | 0.001504 |
| 284 | 0.029748 | 0.027503 | 0.008292 | 0.021237 | 0.020789 | 0.007127 | 0.017383 | 0.908521 | −0.09433 | −0.06014 | −0.040397 | −0.011421 | −0.009429 | 0.00972 |
| 285 | 0.026324 | 0.017382 | 0.007512 | 0.035174 | 0.033603 | −0.000785 | 0.012342 | −0.085151 | 0.874053 | −0.059083 | −0.042117 | −0.003982 | −0.015391 | 0.016679 |
| 286 | 0.03231 | 0.010473 | 0.018736 | −0.02419 | −0.026359 | −0.049623 | 0.010238 | −0.038973 | −0.047546 | 0.811931 | −0.141651 | −0.081867 | −0.000343 | 0.027809 |
| 287 | 0.034941 | 0.00661 | 0.02728 | −0.046006 | −0.014184 | −0.05997 | −0.002397 | −0.03797 | −0.046992 | −0.171855 | 0.80831 | −0.104742 | 0.00318 | 0.007937 |
| 288 | −0.003193 | −0.019919 | 0.006059 | 0.022015 | −0.016874 | −0.032194 | −0.073472 | −0.016943 | −0.014328 | −0.104587 | −0.109461 | 0.763071 | −0.051279 | −0.042124 |
| 289 | 0.005193 | −0.001896 | 0.008541 | 0.026387 | 0.029738 | 0.005731 | −0.015951 | −0.006605 | −0.018347 | 0.008238 | 0.005004 | −0.03797 | 0.879417 | −0.020688 |
| 290 | −0.002594 | 0.010621 | 0.015193 | −0.015683 | −0.006661 | 0.010418 | −0.012016 | −0.002469 | 0.009851 | 0.015732 | 0.004142 | −0.06012 | −0.016648 | 0.805184 |
| 291 | −0.003685 | 0.007555 | 0.01489 | −0.014948 | −0.006429 | 0.0059 | −0.009359 | −0.002221 | 0.009921 | 0.009535 | 0.004263 | −0.060343 | −0.018592 | −0.190378 |
| 292 | −0.001478 | 0.023905 | −0.001238 | −0.010039 | 0.000337 | 0.016194 | −0.007897 | −0.000548 | 0.012496 | 0.023343 | 0.01795 | −0.039198 | −0.007666 | −0.171089 |
| 293 | 0.003174 | 0.003873 | 0.011577 | −0.014849 | −0.017812 | 0.006604 | 0.006032 | −0.005107 | 0.008181 | −0.022016 | 0.007224 | −0.028468 | 0.013296 | −0.000739 |
| 294 | −0.000908 | 0.00867 | 0.004951 | −0.005989 | −0.010939 | −0.000997 | −0.016768 | 0.015003 | 0.021711 | 0.01556 | 0.027659 | −0.021611 | −0.007168 | 0.00576 |
| 295 | 0.00553 | −0.009203 | −0.00906 | 0.01876 | −0.007123 | 0.006351 | −0.016665 | −0.006028 | 0.000613 | 0.036441 | 0.05836 | 0.031589 | −0.001402 | 0.010838 |
| 296 | 0.002892 | −0.008213 | 0.00459 | 0.01547 | −0.001819 | −0.005354 | −0.02589 | 0.017816 | 0.019727 | 0.038612 | 0.032213 | −0.007911 | −0.01674 | −0.014065 |
| 297 | 0.003996 | −0.01818 | −0.003911 | 0.02131 | −0.023339 | −0.010641 | −0.00791 | −0.01465 | −0.004317 | 0.020738 | 0.027449 | 0.020995 | 0.000107 | 0.009712 |
| 298 | 0.004735 | −0.006102 | 0.002791 | −0.000657 | −0.017473 | −0.015595 | −0.001702 | −0.010064 | 0.008006 | −0.005918 | −0.012372 | 0.000538 | 0.006807 | −0.032765 |
| 299 | −0.006514 | 0.002524 | −0.006883 | −0.006533 | −0.014316 | 0.002964 | 0.00263 | 0.009783 | 0.014513 | 0.010228 | 0.012901 | 0.00616 | 0.01013 | 0.007657 |
| 300 | 0.012487 | 0.028906 | 0.012715 | −0.069106 | −0.013655 | 0.006792 | −0.006629 | −0.01433 | −0.007638 | −0.015408 | −0.014929 | 0.02871 | −0.020662 | −0.008107 |
| 301 | 0.007408 | −0.000632 | −0.011241 | 0.010184 | 0.010163 | 0.019568 | 0.014628 | −0.031609 | −0.029871 | 0.024951 | 0.031454 | 0.022387 | −0.004029 | 0.005342 |
| 302 | 0.003616 | 0.010646 | −0.006167 | −0.023665 | −0.000581 | 0.006041 | 0.011 | −0.004439 | −0.005241 | 0.010354 | 0.017199 | 0.010098 | −0.019617 | 0.003934 |
| 303 | −0.027089 | −0.034704 | −0.013424 | −0.019082 | 0.007863 | 0.00012 | 0.006129 | 0.031684 | 0.027409 | −0.027796 | −0.018757 | −0.000426 | 0.019081 | 0.031907 |
| 304 | −0.014369 | −0.007723 | −0.013675 | −0.046662 | −0.004671 | 0.00408 | −0.009379 | 0.03231 | 0.038285 | −0.026102 | −0.024554 | −0.038412 | 0.019067 | 0.003932 |
| 305 | 0.002129 | −0.008479 | −0.003393 | 0.044744 | −0.01601 | −0.018576 | −0.000039 | −0.004398 | −0.018129 | −0.001571 | −0.00833 | 0.027314 | −0.022328 | −0.008568 |
| 306 | 0.008118 | 0.029582 | 0.018781 | 0.003889 | −0.006947 | 0.011886 | 0.006466 | −0.001463 | 0.018754 | 0.032169 | 0.01879 | 0.018155 | −0.000336 | −0.055083 |
| 307 | −0.020354 | −0.034953 | −0.003797 | −0.030557 | 0.00958 | −0.021305 | 0.014875 | −0.019294 | −0.017185 | −0.034998 | −0.042821 | −0.009129 | 0.030348 | −0.030067 |
| 308 | −0.002918 | 0.012741 | −0.008382 | −0.015784 | 0.003579 | 0.015358 | 0.010207 | 0.000038 | −0.004407 | 0.019633 | −0.006168 | −0.007679 | 0.00997 | −0.025385 |
| 309 | 0.009023 | 0.009443 | −0.009063 | −0.003926 | 0.005036 | −0.00309 | −0.009624 | −0.00044 | 0.000411 | 0.007148 | −0.013486 | 0.011688 | 0.013385 | −0.00067 |
| 310 | −0.006263 | 0.002365 | −0.014331 | 0.05355 | 0.006363 | 0.003902 | −0.00924 | 0.008309 | −0.001393 | 0.032413 | 0.038527 | 0.041506 | 0.003864 | −0.019971 |
| 311 | −0.014292 | −0.026816 | −0.000993 | −0.005903 | 0.023139 | 0.010257 | −0.001127 | 0.009448 | 0.005557 | 0.005683 | 0.005296 | 0.008704 | −0.014319 | −0.003153 |
| 312 | 0.020207 | −0.013158 | 0.041875 | 0.039927 | 0.038682 | 0.011976 | 0.031129 | 0.001583 | 0.000247 | −0.003386 | −0.027964 | 0.013709 | −0.003115 | −0.004384 |
| 313 | 0.020205 | 0.021549 | 0.009448 | −0.007523 | −0.002101 | 0.010379 | 0.02711 | −0.024508 | −0.004794 | −0.004396 | −0.007264 | 0.040945 | 0.012774 | 0.018346 |
| 314 | 0.027099 | 0.010418 | 0.029046 | 0.059192 | −0.00603 | −0.00363 | 0.005969 | 0.001903 | −0.007567 | −0.002694 | −0.010017 | 0.029901 | 0.003737 | 0.003322 |
| 315 | −0.002242 | −0.003667 | 0.023964 | −0.000056 | −0.005918 | −0.007082 | 0.018044 | 0.013194 | 0.011402 | −0.01357 | −0.03095 | −0.000061 | −0.002771 | 0.010173 |
| 316 | −0.008294 | −0.032618 | 0.000826 | −0.061486 | 0.049933 | 0.01123 | 0.015195 | −0.021622 | −0.035888 | −0.018109 | −0.024994 | −0.018871 | −0.001056 | 0.007683 |
| 317 | −0.001478 | −0.009304 | −0.000182 | 0.036383 | 0.00369 | −0.007181 | −0.016592 | −0.02519 | −0.028135 | 0.01772 | 0.000801 | 0.01711 | 0.000653 | 0.000786 |
| 318 | −0.01286 | −0.010141 | 0.013332 | 0.030151 | 0.01465 | 0.033864 | −0.008962 | 0.015902 | 0.005453 | 0.027885 | 0.024143 | 0.013971 | 0.010768 | 0.017172 |
| 319 | −0.011573 | −0.009631 | 0.014758 | −0.022263 | 0.001211 | −0.011037 | −0.001178 | 0.000008 | −0.004493 | −0.017728 | −0.028962 | −0.002684 | 0.002739 | 0.015857 |
| 320 | 0.000958 | 0.030664 | −0.009051 | −0.003734 | 0.020823 | −0.00862 | 0.010822 | −0.010315 | −0.008532 | −0.008699 | −0.014216 | −0.021221 | −0.016554 | −0.010823 |
| 321 | 0.001537 | −0.006998 | 0.015826 | 0.028585 | −0.007251 | −0.008416 | 0.023417 | −0.026002 | −0.022318 | −0.012302 | −0.019865 | −0.019661 | −0.016831 | −0.014483 |
| 322 | −0.015181 | −0.016041 | −0.021172 | −0.041503 | 0.047889 | 0.018323 | 0.041674 | 0.017997 | 0.012395 | −0.008096 | 0.004579 | 0.032371 | −0.008251 | 0.014129 |
| 323 | 0.007953 | −0.003462 | 0.019383 | −0.010051 | −0.007597 | 0.011372 | 0.05638 | −0.024734 | −0.009723 | −0.0112 | 0.014304 | 0.057201 | 0.03242 | −0.013988 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 324 | 0.029974 | 0.006452 | −0.062784 | 0.005468 | −0.054961 | −0.031317 | −0.046328 | −0.014766 | −0.00887 | 0.009843 | 0.019999 | −0.015388 | −0.01187 | −0.016874 |
| 325 | 0.033322 | 0.001429 | 0.000606 | −0.014543 | −0.023213 | −0.024358 | −0.020396 | 0.000715 | 0.010899 | −0.005747 | −0.012861 | −0.007873 | 0.010624 | 0.010064 |
| 326 | 0.020142 | 0.036208 | −0.001569 | −0.619876 | −0.004766 | 0.007709 | −0.019903 | 0.002207 | 0.031903 | 0.002308 | −0.012672 | −0.005748 | 0.00794 | 0.024985 |
| 327 | −0.009439 | −0.004591 | −0.017626 | 0.015602 | −0.000749 | 0.001926 | 0.001094 | 0.005002 | 0.000428 | 0.014796 | 0.011445 | 0.007865 | 0.009141 | −0.007725 |
| 328 | 0.004173 | 0.0026291 | 0.009399 | −0.017505 | −0.019168 | −0.028337 | −0.003001 | −0.006328 | −0.034676 | −0.001631 | 0.003746 | 0.004231 | −0.024205 | −0.009819 |
| 329 | 0.00491 | 0.006166 | −0.00804 | 0.020048 | 0.004968 | −0.001561 | 0.007553 | −0.01558 | −0.015637 | −0.018637 | 0.003555 | 0.035464 | 0.00906 | 0.021343 |
| 330 | −0.023397 | −0.038462 | −0.002179 | 0.026465 | −0.036407 | −0.034517 | −0.008307 | 0.015004 | 0.000351 | 0.010542 | 0.00506 | 0.009827 | 0.010012 | 0.020505 |
| 331 | 0.002684 | 0.003941 | −0.002328 | −0.020332 | 0.005002 | −0.001734 | 0.007017 | 0.006117 | 0.013991 | −0.030274 | −0.019622 | −0.022599 | −0.001864 | 0.004567 |
| 332 | −0.018988 | −0.00099 | −0.015303 | −0.00827 | 0.018483 | −0.023908 | −0.014142 | 0.00419 | 0.012714 | 0.026804 | 0.011705 | 0.009568 | −0.001792 | 0.003051 |
| 333 | 0.021047 | 0.001058 | −0.006061 | −0.01249 | −0.004029 | −0.006931 | 0.007125 | −0.016658 | −0.009933 | 0.011069 | 0.010275 | 0.011647 | 0.005112 | −0.000261 |
| 334 | 0.06535 | 0.065269 | 0.03158 | 0.039477 | 0.016903 | −0.008552 | −0.00439 | −0.030666 | −0.031262 | −0.023496 | −0.015146 | −0.009517 | 0.020826 | 0.006818 |
| 335 | 0.005756 | −0.012078 | −0.016231 | −0.033712 | −0.003579 | 0.000377 | 0.002528 | −0.000826 | 0.004094 | −0.004691 | −0.003682 | −0.001957 | 0.021755 | 0.011984 |
| 336 | 0.030063 | 0.051919 | 0.039058 | 0.010747 | 0.003883 | 0.009968 | −0.051991 | 0.013792 | 0.009368 | −0.00157 | −0.003347 | −0.020767 | −0.004482 | 0.005946 |
| 337 | 0.018321 | 0.019795 | −0.005191 | 0.038382 | −0.015267 | 0.000177 | −0.002188 | 0.003928 | −0.003951 | 0.026838 | 0.04331 | 0.019276 | −0.012561 | −0.023612 |
| 338 | 0.034876 | 0.033284 | 0.016413 | 0.012754 | 0.026107 | −0.008174 | 0.011083 | 0.007411 | 0.018305 | −0.021769 | 0.001485 | 0.007128 | 0.016106 | 0.02578 |
| 339 | 0.00211 | 0.017195 | −0.014388 | 0.013461 | −0.013635 | −0.001638 | 0.011142 | 0.005626 | −0.007131 | −0.056647 | −0.02738 | −0.014819 | 0.015337 | −0.011633 |
| 340 | 0.004074 | 0.011612 | 0.044649 | −0.023626 | −0.012966 | 0.008579 | 0.004993 | −0.007075 | 0.005157 | −0.017206 | −0.000241 | 0.020247 | 0.049563 | 0.037993 |

| | KF | KG | KH | KI | KJ | KK | KL | KM | KN | KO | KP | KQ | KR | KS |
|---|---|---|---|---|---|---|---|---|---|---|---|---|---|---|
| 1 | 0.0809111 | 0.0613861 | −0.0171881 | −0.012392 | 0.010998 | −0.000757 | 0.028982 | −0.010747 | −0.021318 | 0.04112 | −0.010745 | −0.063054 | −0.064764 | −0.101638 |
| 2 | 0.065249 | 0.091031 | 0.013813 | 0.009598 | 0.012132 | 0.018248 | 0.013607 | 0.038356 | −0.030056 | 0.062181 | −0.058444 | −0.034142 | −0.066073 | −0.061367 |
| 3 | 0.052512 | 0.016686 | −0.10612 | −0.050615 | −0.140157 | −0.094441 | −0.090496 | 0.036848 | −0.03237 | 0.026888 | −0.072679 | −0.038894 | 0.02496 | 0.003985 |
| 4 | −0.006128 | −0.039458 | −0.073454 | −0.021128 | −0.062768 | −0.084305 | −0.029036 | 0.064675 | 0.038453 | 0.000712 | 0.004204 | −0.000741 | 0.113904 | 0.064121 |
| 5 | −0.030113 | −0.007985 | −0.031834 | −0.044685 | −0.021004 | 0.007148 | 0.001186 | 0.04549 | 0.022793 | −0.004098 | −0.011704 | −0.031853 | −0.003382 | −0.0102 |
| 6 | 0.028806 | 0.015861 | −0.033613 | −0.004932 | 0.018477 | 0.054711 | 0.014555 | −0.008198 | −0.026682 | −0.025231 | −0.009551 | 0.006937 | −0.011908 | −0.05513 |
| 7 | −0.0196791 | −0.0268791 | 0.003741 | 0.062693 | −0.032249 | 0.010712 | −0.012812 | 0.10017 | 0.0843061 | 0.0501171 | 0.043213 | 0.0004 | 0.0922251 | 0.092191 |
| 8 | −0.0331841 | −0.0304981 | 0.0142191 | 0.023205 | 0.001251 | 0.007039 | 0.028856 | −0.00917 | 0.022099 | 0.049953 | −0.007467 | 0.050056 | −0.026755 | −0.02649 |
| 9 | −0.050192 | −0.075606 | −0.047786 | −0.069114 | −0.053183 | −0.048718 | −0.031691 | −0.037481 | −0.054992 | −0.042673 | −0.057729 | −0.035444 | −0.056697 | −0.058934 |
| 10 | −0.00333 | −0.001291 | 0.094167 | −0.00687 | 0.074825 | −0.033185 | 0.084742 | −0.012061 | 0.073233 | 0.01093 | 0.061137 | 0.032104 | 0.068918 | 0.070631 |
| 11 | −0.01182 | 0.008217 | −0.050143 | 0.024372 | 0.024917 | 0.091834 | 0.029136 | 0.089789 | 0.025032 | −0.029759 | 0.034117 | 0.045141 | 0.067183 | 0.068434 |
| 12 | −0.012541 | −0.009157 | −0.006205 | 0.002419 | 0.021713 | 0.012139 | −0.012559 | −0.041203 | −0.045867 | 0.041033 | −0.031945 | 0.001333 | −0.068226 | −0.016477 |
| 13 | 0.075957 | 0.064198 | −0.044459 | −0.045461 | 0.033055 | 0.036608 | −0.003527 | 0.096078 | −0.065621 | 0.025365 | 0.007842 | 0.024269 | −0.031064 | −0.01084 |
| 14 | 0.068967 | 0.048023 | −0.035487 | −0.034713 | 0.005758 | 0.049529 | 0.036964 | 0.041532 | 0.039387 | −0.018104 | 0.067031 | 0.052538 | −0.016184 | 0.023064 |
| 15 | −0.147508 | −0.123667 | −0.098289 | −0.115249 | −0.05785 | −0.060857 | −0.016424 | −0.101536 | −0.022272 | −0.025622 | −0.023972 | −0.043595 | −0.056884 | −0.025344 |
| 16 | 0.008317 | 0.01503 | −0.014828 | −0.006004 | −0.004195 | −0.013894 | −0.017536 | −0.029436 | −0.004482 | 0.028538 | −0.042106 | −0.01922 | −0.018947 | −0.009867 |
| 17 | 0.012329 | 0.010002 | −0.003514 | −0.045642 | −0.00121 | −0.035243 | 0.009614 | 0.005316 | 0.038353 | 0.01172 | 0.032672 | 0.016608 | 0.007887 | −0.007364 |
| 18 | −0.036499 | −0.041269 | −0.068852 | 0.043537 | 0.020892 | 0.049678 | 0.030949 | −0.038253 | 0.02733 | 0.047972 | −0.023004 | 0.026021 | 0.047131 | 0.025059 |
| 19 | −0.03416 | −0.016012 | 0.001348 | 0.019354 | −0.009173 | 0.071309 | −0.009676 | −0.113303 | −0.071029 | −0.012505 | −0.071932 | −0.040024 | −0.012167 | −0.009639 |
| 20 | −0.047998 | −0.058402 | −0.016998 | 0.014562 | −0.014746 | −0.035681 | −0.034247 | −0.067217 | −0.047929 | −0.043416 | −0.01651 | −0.04209 | −0.056504 | −0.053958 |
| 21 | 0.022909 | −0.002471 | −0.004776 | −0.010156 | 0.023174 | −0.012828 | −0.036568 | −0.068663 | −0.027951 | −0.083499 | 0.030327 | −0.015317 | −0.070893 | −0.018183 |
| 22 | −0.004409 | −0.006957 | −0.017908 | 0.013798 | 0.043138 | 0.008845 | 0.032814 | −0.06728 | 0.014927 | −0.029411 | 0.014428 | 0.022052 | −0.012862 | −0.080171 |
| 23 | −0.003042 | 0.0154771 | 0.0304951 | 0.000744 | −0.067079 | −0.061052 | −0.015268 | −0.093619 | 0.000001 | −0.059839 | −0.019715 | −0.003979 | −0.03828 | 0.022645 |
| 24 | −0.055002 | −0.047141 | 0.00463 | 0.030724 | 0.044933 | 0.050531 | 0.057565 | 0.033554 | 0.04786 | 0.060681 | 0.008602 | 0.012599 | 0.103616 | 0.025736 |
| 25 | 0.052107 | 0.054119 | −0.003885 | −0.00441 | −0.018893 | −0.071928 | 0.005199 | −0.020958 | 0.002505 | 0.018869 | −0.012464 | 0.018608 | −0.031785 | 0.004711 |
| 26 | 0.012141 | −0.0111771 | 0.010697 | 0.007976 | 0.037988 | 0.075593 | 0.006068 | 0.086006 | −0.027228 | −0.031986 | −0.025113 | −0.038373 | −0.068128 | −0.001504 |
| 27 | 0.013917 | 0.034293 | 0.015159 | 0.006 | −0.126888 | −0.11649 | −0.149706 | 0.061974 | −0.044098 | 0.028034 | −0.014359 | 0.0242731 | 0.046539 | 0.03176 |
| 28 | −0.003401 | −0.013693 | 0.123617 | 0.023235 | 0.090744 | 0.049534 | 0.128819 | 0.031752 | 0.067185 | 0.065109 | −0.007349 | −0.057986 | 0.062493 | 0.037564 |
| 29 | −0.006142 | 0.04565 | 0.018596 | −0.000968 | 0.006112 | 0.045672 | 0.00175 | 0.016981 | −0.018076 | 0.001598 | 0.010462 | 0.010477 | −0.002109 | 0.007867 |
| 30 | 0.035174 | 0.028575 | −0.058725 | 0.004344 | −0.004067 | 0.007402 | −0.000317 | −0.008341 | −0.010562 | 0.02047 | −0.001158 | −0.026833 | −0.000639 | −0.000777 |
| 31 | 0.005991 | 0.003712 | 0.007615 | −0.006734 | 0.014859 | −0.056806 | 0.017689 | 0.043624 | −0.036892 | 0.05913 | 0.033547 | −0.021428 | −0.032647 | −0.047832 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 32 | −0.014172 | 0.00367 | −0.000819 | 0.017512 | 0.029713 | 0.040795 | 0.036577 | 0.034145 | 0.037182 | 0.033833 | 0.034243 | 0.0236 | 0.05575 | 0.041785 |
| 33 | 0.017094 | 0.027428 | 0.112318 | 0.006955 | 0.016465 | −0.020798 | 0.056669 | −0.053218 | 0.021738 | −0.003961 | 0.070939 | 0.033728 | −0.014645 | −0.041895 |
| 34 | 0.059532 | 0.055739 | −0.123856 | −0.074677 | −0.08713 | −0.020697 | −0.050643 | 0.042982 | −0.043542 | 0.013301 | −0.04076 | −0.033483 | 0.036955 | 0.011726 |
| 35 | 0.024533 | 0.024606 | −0.026198 | −0.02456 | 0.000363 | 0.019397 | −0.006069 | 0.005092 | −0.021135 | −0.017232 | −0.020979 | −0.038199 | −0.017512 | −0.043379 |
| 36 | 0.066353 | 0.047295 | −0.124725 | −0.062456 | −0.051089 | 0.006998 | −0.068236 | −0.022238 | −0.012241 | −0.027325 | −0.089305 | −0.01557 | 0.02711 | 0.044425 |
| 37 | −0.003608 | −0.005376 | −0.005524 | 0.014635 | 0.016165 | 0.011417 | −0.007208 | −0.056681 | −0.034616 | −0.024589 | −0.005518 | 0.018026 | 0.046248 | 0.001736 |
| 38 | 0.038148 | 0.017527 | 0.052253 | 0.006505 | 0.07663 | 0.028413 | 0.06326 | 0.015896 | 0.033982 | 0.066687 | 0.074149 | 0.057862 | 0.01638 | 0.05331 |
| 39 | −0.029325 | −0.034648 | 0.128952 | 0.054515 | 0.039666 | −0.004286 | −0.006743 | −0.058924 | 0.035268 | −0.047287 | 0.034175 | 0.086527 | −0.010465 | 0.028674 |
| 40 | −0.030663 | −0.036797 | −0.048308 | 0.032364 | 0.025477 | 0.055296 | −0.012542 | 0.029092 | 0.03534 | 0.035049 | −0.013459 | 0.023179 | 0.023434 | 0.083357 |
| 41 | −0.011752 | −0.004004 | 0.096352 | −0.044652 | 0.044274 | 0.028447 | 0.010528 | −0.074787 | 0.010201 | 0.048662 | −0.003122 | −0.000994 | −0.047784 | −0.018505 |
| 42 | −0.025731 | −0.036847 | −0.010558 | −0.003751 | −0.000408 | 0.000529 | 0.008891 | 0.000858 | −0.001305 | 0.000445 | −0.004509 | −0.00562 | 0.010029 | −0.000965 |
| 43 | 0.002033 | −0.016037 | −0.20026 | −0.000003 | −0.07267 | 0.053717 | −0.009125 | −0.072331 | −0.058836 | −0.055828 | −0.054179 | 0.014698 | −0.007463 | −0.015672 |
| 44 | −0.023289 | −0.031297 | −0.023265 | −0.003292 | −0.029005 | 0.022054 | −0.017556 | 0.050593 | −0.0052 | −0.035805 | −0.053958 | −0.032352 | 0.038094 | 0.011956 |
| 45 | 0.023521 | 0.038824 | −0.004506 | −0.020136 | 0.007162 | 0.00223 | −0.016997 | −0.00794 | 0.006534 | −0.03182 | −0.007459 | −0.002346 | −0.004449 | 0.002395 |
| 46 | 0.029425 | 0.029985 | −0.054229 | 0.04866 | −0.004628 | 0.068358 | −0.047626 | −0.026107 | 0.001814 | −0.012357 | −0.014825 | 0.062976 | 0.082905 | 0.127639 |
| 47 | −0.007389 | 0.003591 | 0.013931 | 0.072878 | 0.042564 | 0.053641 | 0.027264 | 0.003075 | 0.037408 | −0.063614 | 0.031304 | 0.035183 | 0.072849 | 0.059366 |
| 48 | 0.021601 | 0.015699 | −0.020281 | 0.040355 | 0.007621 | 0.030588 | 0.016709 | 0.00987 | −0.014595 | 0.014029 | −0.013798 | −0.025494 | −0.017102 | −0.054515 |
| 49 | 0.006851 | 0.01996 | −0.026598 | −0.016868 | −0.011406 | −0.04009 | −0.047967 | −0.086485 | 0.000991 | −0.011339 | 0.01659 | 0.02393 | 0.032744 | 0.07018 |
| 50 | −0.108474 | −0.113249 | −0.062552 | −0.004448 | −0.000768 | 0.029095 | 0.018048 | 0.05597 | 0.008927 | 0.038035 | −0.002451 | 0.054689 | 0.022985 | −0.010262 |
| 51 | −0.096133 | −0.087722 | −0.026347 | 0.006461 | −0.000989 | 0.003713 | 0.013921 | −0.006576 | 0.035418 | −0.007431 | 0.004073 | 0.032752 | 0.019633 | 0.019329 |
| 52 | 0.018104 | 0.03103 | −0.088185 | −0.02653 | 0.00724 | 0.022819 | −0.004472 | 0.078079 | 0.048609 | 0.0649 | −0.001254 | 0.02313 | 0.046061 | 0.042402 |
| 53 | −0.03527 | −0.052516 | 0.09171 | −0.007188 | −0.027817 | −0.051132 | −0.0143 | 0.008154 | −0.002467 | −0.017804 | −0.010216 | −0.083086 | −0.081448 | −0.062464 |
| 54 | 0.044085 | 0.049321 | 0.057958 | −0.080561 | −0.005846 | −0.08296 | −0.00862 | −0.002946 | −0.061154 | −0.092555 | 0.015248 | −0.051896 | −0.052241 | −0.119549 |
| 55 | 0.018163 | 0.014596 | 0.06828 | 0.015262 | 0.018708 | 0.029501 | −0.051085 | −0.123872 | 0.038351 | −0.07479 | −0.01024 | −0.025453 | −0.024741 | 0.010875 |
| 56 | −0.035129 | −0.010071 | 0.034911 | 0.064689 | 0.094444 | 0.021133 | 0.091414 | −0.091555 | 0.074962 | −0.110804 | 0.045788 | 0.01428 | 0.027275 | 0.003276 |
| 57 | −0.030027 | −0.050139 | −0.014998 | 0.018361 | 0.016545 | 0.030849 | 0.017364 | 0.021545 | 0.004747 | 0.052771 | 0.024032 | 0.05648 | −0.008466 | 0.027028 |
| 58 | −0.025914 | −0.015686 | −0.017824 | 0.069708 | 0.045376 | 0.05977 | 0.079346 | 0.048348 | 0.03154 | 0.060159 | 0.020431 | −0.022594 | −0.021564 | −0.083423 |
| 59 | −0.027039 | −0.035615 | 0.060586 | −0.031836 | −0.021419 | −0.071685 | −0.011043 | −0.018139 | −0.066976 | −0.048339 | −0.011854 | −0.084058 | −0.07275 | −0.071659 |
| 60 | 0.071273 | 0.007593 | −0.005646 | 0.028106 | −0.041831 | −0.029537 | −0.030261 | 0.075808 | −0.041778 | 0.043199 | −0.022542 | −0.048174 | −0.028167 | −0.044888 |
| 61 | −0.015821 | 0.00554 | 0.009044 | −0.001764 | 0.003702 | 0.030415 | 0.02369 | −0.108948 | 0.02966 | −0.321745 | 0.005772 | −0.015536 | 0.055717 | 0.038873 |
| 62 | −0.045639 | −0.031692 | −0.001132 | 0.009757 | 0.042148 | −0.009692 | 0.024035 | −0.03611 | 0.013002 | 0.050048 | 0.000553 | 0.026524 | 0.021773 | 0.007527 |
| 63 | −0.016467 | 0.041243 | −0.020932 | 0.016876 | −0.027308 | −0.054532 | −0.008063 | 0.162184 | 0.021643 | 0.250238 | 0.004396 | 0.011683 | 0.006698 | 0.013877 |
| 64 | 0.026857 | 0.016186 | 0.078959 | 0.037897 | 0.050959 | 0.019281 | −0.001874 | −0.036345 | −0.065843 | 0.027553 | 0.005776 | 0.014996 | −0.078822 | −0.056913 |
| 65 | 0.031329 | 0.066448 | 0.038016 | 0.043662 | −0.021361 | −0.03119 | −0.033947 | −0.050309 | −0.001717 | −0.029346 | 0.010429 | 0.022814 | 0.032066 | −0.045206 |
| 66 | −0.045974 | −0.040668 | −0.040455 | −0.016875 | −0.043111 | 0.012705 | −0.06059 | 0.026538 | 0.023647 | 0.005689 | −0.026859 | 0.040248 | −0.003367 | −0.043514 |
| 67 | 0.047907 | 0.006212 | 0.032636 | −0.003033 | 0.052364 | 0.057488 | 0.096867 | 0.039166 | 0.08543 | 0.055493 | 0.054014 | 0.032588 | 0.034212 | 0.035509 |
| 68 | 0.045357 | 0.038908 | 0.031487 | 0.006089 | 0.045375 | 0.00282 | 0.041602 | −0.057795 | 0.018927 | −0.032405 | −0.009018 | −0.002033 | −0.010084 | 0.031615 |
| 69 | 0.037257 | 0.02253 | −0.014464 | −0.000336 | −0.042778 | 0.01465 | −0.017403 | 0.001238 | 0.000171 | −0.087589 | −0.01006 | 0.014069 | 0.000454 | −0.034666 |
| 70 | 0.017832 | 0.012512 | −0.073035 | 0.057077 | 0.049821 | 0.05681 | 0.017194 | 0.001574 | 0.037076 | −0.011583 | 0.017164 | 0.042934 | −0.029864 | −0.04067 |
| 71 | 0.026922 | 0.030057 | 0.060173 | −0.023226 | −0.022044 | −0.038202 | −0.025495 | −0.022204 | 0.003796 | 0.009757 | −0.030061 | −0.037851 | −0.005808 | −0.020262 |
| 72 | −0.060164 | −0.066487 | 0.03151 | 0.00579 | 0.007182 | 0.059536 | −0.0085 | 0.013858 | 0.012474 | −0.044124 | 0.011532 | 0.039859 | −0.025412 | 0.002793 |
| 73 | −0.126324 | −0.027918 | −0.01681 | 0.029272 | −0.028756 | 0.015281 | 0.002971 | 0.067431 | 0.008859 | 0.028269 | 0.019666 | 0.038411 | 0.02665 | 0.023298 |
| 74 | 0.05168 | 0.036685 | 0.0316 | 0.02941 | 0.021033 | 0.040664 | 0.015253 | 0.044243 | 0.038096 | 0.023535 | 0.063626 | 0.039039 | 0.027296 | 0.06951 |
| 75 | −0.033362 | 0.011894 | −0.01285 | 0.025815 | −0.018905 | −0.068815 | −0.018324 | −0.013591 | −0.006379 | 0.161678 | −0.022157 | −0.023034 | 0.053594 | 0.035412 |
| 76 | 0.049019 | 0.056996 | 0.074606 | 0.052274 | −0.003537 | −0.024975 | 0.010574 | −0.056842 | 0.026942 | 0.006638 | −0.067295 | −0.011917 | 0.031981 | 0.046112 |
| 77 | 0.060268 | 0.021751 | 0.092373 | 0.043422 | 0.043665 | −0.015023 | 0.025174 | 0.006206 | −0.094781 | −0.02538 | −0.025808 | −0.059616 | −0.105685 | −0.119944 |
| 78 | −0.171127 | −0.189362 | 0.021665 | −0.076229 | −0.062868 | −0.096644 | 0.004015 | 0.03943 | 0.014847 | 0.019883 | 0.004275 | −0.066879 | 0.017201 | 0.021782 |
| 79 | −0.040695 | 0.000846 | −0.001622 | 0.012178 | 0.027047 | 0.003498 | −0.00136 | −0.082351 | 0.036346 | −0.040648 | 0.024246 | 0.042548 | 0.050306 | 0.044077 |
| 80 | 0.012045 | 0.009597 | −0.020542 | 0.013149 | −0.043501 | 0.01507 | −0.026694 | 0.07355 | −0.016801 | −0.001515 | −0.039763 | 0.000089 | 0.019462 | 0.035592 |
| 81 | −0.010255 | 0.008084 | −0.027404 | 0.025277 | −0.054826 | 0.017425 | −0.077256 | −0.06696 | −0.036942 | −0.032501 | −0.005919 | −0.000599 | 0.008181 | 0.050123 |
| 82 | −0.041332 | −0.01399 | −0.113095 | −0.025101 | 0.010552 | 0.060967 | −0.002009 | 0.046088 | −0.014637 | 0.136818 | −0.019867 | 0.051099 | −0.033298 | 0.031343 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 83 | 0.0393171 | 0.0700841 | 0.019931 | −0.015853 | 0.01539 | 0.040321 | 0.015447 | 0.019158 | 0.0101491 | 0.0547731 | −0.030286 | −0.083462 | 0.0056221 | −0.025793 |
| 84 | −0.002273 | −0.030354 | 0.0050581 | 0.001662 | −0.040254 | −0.012412 | −0.032897 | −0.064834 | 0.0334871 | 0.0199641 | −0.019486 | −0.063744 | 0.059744 | 0.056999 |
| 85 | 0.048516 | 0.072331 | −0.030527 | −0.055054 | −0.008363 | 0.001275 | 0.029165 | 0.037692 | −0.019333 | −0.037221 | −0.013602 | −0.01971 | −0.005329 | 0.051572 |
| 86 | −0.005996 | −0.025109 | 0.018822 | −0.018657 | 0.029462 | −0.101361 | −0.000053 | −0.020964 | 0.055701 | −0.040529 | 0.010951 | −0.039588 | 0.075336 | 0.040668 |
| 87 | −0.019454 | −0.01234 | 0.011795 | −0.004918 | −0.000931 | −0.027931 | −0.013186 | −0.054619 | −0.035794 | 0.017078 | −0.01508 | 0.043748 | −0.039609 | −0.030206 |
| 88 | 0.038112 | −0.025862 | 0.043886 | 0.073216 | 0.065706 | 0.041891 | 0.00561 | −0.005855 | 0.026713 | −0.03986 | 0.060523 | 0.013694 | −0.012063 | −0.032976 |
| 89 | 0.033343 | 0.088194 | −0.068249 | −0.027282 | 0.039962 | 0.035417 | 0.049124 | 0.069856 | −0.003017 | 0.004186 | 0.003292 | 0.033219 | −0.017466 | −0.020309 |
| 90 | −0.032015 | −0.0354881 | 0.041948 | 0.010205 | −0.013496 | −0.000373 | 0.016317 | 0.016662 | 0.000329 | −0.091811 | 0.005432 | −0.003328 | 0.029924 | −0.010389 |
| 91 | −0.009328 | −0.042403 | 0.103393 | 0.055348 | 0.044673 | 0.02989 | 0.043944 | 0.002109 | 0.060927 | −0.011353 | 0.056142 | 0.067731 | 0.028265 | 0.05443 |
| 92 | 0.003858 | 0.00642 | −0.026579 | 0.012534 | −0.009195 | 0.115859 | −0.025931 | 0.089027 | −0.033362 | −0..028307 | −0.038426 | 0.029301 | 0.008099 | 0.055582 |
| 93 | −0.035479 | −0.070025 | −0.114268 | −0.030443 | −0.002581 | −0.080822 | −0.025721 | −0.039176 | −0.012652 | −0.024044 | 0.011653 | 0.007654 | −0.034374 | −0.042892 |
| 94 | 0.089033 | 0.057366 | 0.045609 | 0.007909 | 0.0008 | 0.006063 | 0.058285 | −0.020817 | 0.064032 | −0.081538 | 0.020988 | 0.014314 | −0.040653 | −0.025721 |
| 95 | −0.072196 | −0.014554 | −0.026334 | 0.054879 | 0.029459 | 0.014373 | 0.032583 | 0.07116 | −0.032638 | 0.02443 | −0.029005 | −0.027337 | −0.054678 | −0.094589 |
| 96 | −0.031013 | −0.054201 | −0.021342 | 0.011287 | −0.006483 | 0.029011 | −0.034299 | −0.005846 | −0.050089 | −0.015977 | 0.01214 | −0.004579 | 0.010948 | 0.001366 |
| 97 | −0.064772 | −0.06549 | −0.03132 | 0.004081 | 0.068045 | −0.023369 | −0.005718 | 0.063996 | −0.02115 | 0.036078 | 0.040669 | −0.037 | 0.006682 | −0.115875 |
| 98 | 0.034332 | 0.003584 | −0.011509 | 0.018026 | 0.023783 | 0.007228 | 0.02553 | 0.063452 | −0.008816 | −0.069729 | 0.009077 | 0.017872 | 0.016602 | −0.003413 |
| 99 | −0.061963 | −0.070882 | −0.003952 | 0.012218 | 0.028722 | 0.033572 | −0.005288 | −0.09667 | −0.016239 | −0.050106 | 0.0021821 | 0.0487651 | 0.0623791 | 0.048122 |
| 100 | −0.021389 | −0.0107961 | 0.00652 | −0.005614 | 0.005752 | 0.006681 | −0.006905 | −0.039465 | 0.007233 | −0.051188 | −0.010142 | −0.009703 | 0.018296 | 0.0165 |
| 101 | 0.012331 | 0.008788 | 0.005672 | 0.0145 | −0.001624 | −0.002473 | −0.013204 | −0.029659 | −0.01552 | −0.06984 | 0.004067 | −0.008679 | −0.007474 | −0.018948 |
| 102 | 0.007931 | −0.012661 | −0.009164 | −0.010019 | −0.003273 | −0.004688 | −0.000555 | 0.005295 | −0.006754 | −0.01479 | 0.008619 | 0.024045 | −0.017924 | −0.002807 |
| 103 | −0.00434 | −0.018616 | 0.028463 | −0.005605 | 0.006507 | 0.011892 | −0.014485 | −0.088188 | 0.010413 | −0.086538 | 0.006814 | 0.01728 | −0.00631 | 0.023756 |
| 104 | 0.0093081 | −0.010044 | −0.0281331 | −0.005716 | −0.023491 | 0.004322 | −0.020786 | −0.036548 | −0.025261 | −0.026855 | −0.021369 | −0.009441 | −0.017951 | −0.001905 |
| 105 | −0.013707 | −0.045224 | −0.056615 | −0.003305 | 0.026398 | −0.009791 | −0.003385 | −0.026574 | 0 | 0.019676 | −0.010171 | 0.023421 | −0.002442 | −0.012586 |
| 106 | 0.025027 | 0.018604 | 0.025824 | −0.036944 | −0.00217 | −0.048051 | −0.048455 | −0.04579 | −0.032339 | −0.059097 | 0.002731 | −0.012176 | −0.055815 | −0.024367 |
| 107 | 0.018707 | 0.010613 | 0.001708 | 0.018123 | −0.021335 | 0.036888 | −0.004908 | −0.016096 | −0.015371 | −0.026073 | −0.032771 | −0.03067 | −0.006381 | −0.007168 |
| 108 | 0.004282 | 0.009256 | −0.025258 | 0.00138 | 0.005962 | 0.036784 | −0.002813 | −0.072357 | 0.005438 | 0.006909 | −0.004536 | −0.001826 | 0.022591 | 0.004238 |
| 109 | 0.019297 | 0.015719 | −0.003972 | 0.009438 | 0.018187 | −0.000379 | 0.00813 | −0.028832 | −0.003307 | 0.014647 | 0.006182 | −0.001534 | 0.001442 | −0.003546 |
| 110 | 0.043133 | 0.055138 | 0.005813 | 0.005917 | −0.024279 | 0.036364 | −0.036945 | 0.002296 | −0.017873 | 0.012681 | −0.010345 | −0.020436 | −0.018441 | −0.022742 |
| 111 | −0.038137 | −0.051389 | −0.02426 | −0.017875 | 0.006685 | 0.00705 | −0.015068 | −0.038446 | 0.016713 | 0.030474 | 0.001743 | −0.004042 | 0.022038 | 0.045732 |
| 112 | 0.00383 | 0.012662 | −0.016808 | −0.021628 | 0.005196 | −0.024872 | −0.006123 | 0.02331 | −0.035205 | 0.021939 | −0.030334 | −0.04154 | 0.003112 | −0.039815 |
| 113 | 0.037097 | 0.050922 | −0.044487 | −0.003853 | −0.046982 | −0.006628 | −0.04798 | 0.034998 | −0.007107 | −0.03498 | −0.022214 | 0.018704 | −0.016913 | 0.029324 |
| 114 | 0.006758 | −0.006879 | 0.047289 | 0.027931 | 0.017798 | 0.067625 | 0.042284 | 0.005594 | −0.005291 | 0.041528 | −0.016861 | 0.018533 | −0.012786 | −0.00676 |
| 115 | 0.010917 | 0.0005021 | −0.047077 | 0.032946 | −0.013879 | 0.009795 | −0.026744 | 0.004762 | −0.043339 | 0.003923 | −0.017582 | −0.008161 | −0.01456 | −0.041852 |
| 116 | −0.010959 | −0.00003 | −0.013612 | 0.00332 | 0.049771 | 0.020793 | 0.030918 | −0.012852 | −0.043582 | −0.007949 | −0.014813 | 0.023268 | −0.022684 | −0.015824 |
| 117 | −0.000041 | −0.002861 | −0.043475 | −0.001848 | −0.033538 | 0.002359 | −0.033123 | 0.020559 | −0.005766 | 0.023572 | −0.014636 | 0.019861 | 0.028954 | 0.033408 |
| 118 | 0.003771 | −0.001232 | −0.008053 | 0.017995 | 0.001094 | 0.008058 | 0.008037 | 0.039321 | −0.00013 | 0.038186 | 0.004226 | 0.004306 | −0.009656 | −0.017501 |
| 119 | −0.008097 | 0.0028391 | 0.0112221 | 0.031794 | −0.015428 | −0.000827 | −0.015108 | 0.024881 | 0.0516371 | 0.0459911 | 0.0158851 | −0.000514 | 0.0681571 | 0.035467 |
| 120 | −0.01586 | −0.009988 | −0.043679 | −0.006393 | −0.026689 | −0.004553 | −0.019847 | 0.023471 | −0.00053 | −0.008646 | −0.006961 | 0.022074 | 0.02707 | 0.021343 |
| 121 | 0.000677 | 0.001581 | −0.02533 | 0.004083 | 0.000424 | −0.009373 | −0.007344 | 0.018007 | 0.01723 | 0.000737 | 0.001628 | 0.032431 | 0.030673 | 0.031 |
| 122 | 0.020265 | 0.024712 | 0.045173 | 0.004511 | 0.023767 | −0.001067 | 0.031738 | 0.037745 | −0.003902 | −0.011443 | 0.022214 | −0.002397 | −0.023739 | −0.012813 |
| 123 | −0.000498 | −0.00917 | 0.040578 | 0.024199 | 0.025625 | 0.026368 | 0.026289 | −0.02068 | 0.035939 | −0.021717 | 0.018505 | 0.011466 | 0.004069 | 0.008334 |
| 124 | −0.010215 | 0.0010291 | 0.050854 | −0.002817 | −0.007799 | −0.006824 | −0.018974 | 0.012698 | −0.004027 | −0.015768 | 0.0026931 | −0.027074 | 0.0159641 | 0.001674 |
| 125 | 0.010593 | −0.000296 | −0.019546 | −0.005109 | −0.003326 | −0.011738 | 0.007855 | 0.003592 | 0.002736 | 0.007018 | −0.020637 | 0.002007 | −0.012033 | 0.006834 |
| 126 | 0.026674 | 0.01394 | 0.032605 | 0.01212 | 0.002051 | 0.007203 | 0.012234 | 0.010247 | 0.011696 | −0.036239 | 0.004816 | −0.00272 | −0.003061 | 0.026645 |
| 127 | −0.000856 | −0.002471 | 0.017718 | 0.018081 | −0.0161 | −0.013 | −0.006772 | 0.004876 | −0.017062 | −0.009742 | −0.01839 | −0.022192 | −0.027359 | −0.005523 |
| 128 | 0.012755 | 0.027595 | −0.022981 | 0.010458 | −0.021038 | 0.002868 | −0.013716 | −0.000248 | −0.018931 | 0.00955 | −0.027383 | −0.014474 | −0.006167 | −0.02208 |
| 129 | −0.018523 | −0.007091 | 0.01543 | 0.023076 | 0.043995 | −0.009627 | 0.071404 | −0.009251 | 0.036749 | −0.000752 | 0.058471 | 0.026334 | 0.025873 | 0.026288 |
| 130 | −0.003754 | −0.005258 | 0.040623 | 0.019534 | 0.00117 | −0.024169 | −0.02156 | −0.035281 | −0.00883 | 0.034683 | −0.004011 | −0.024539 | 0.036917 | 0.014353 |
| 131 | 0.049502 | 0.037743 | 0.022363 | −0.010619 | −0.001676 | 0.015169 | −0.021412 | 0.012698 | 0.016723 | 0.022645 | 0.008937 | 0.032948 | 0.015026 | 0.025701 |
| 132 | 0.008307 | 0.016245 | −0.011008 | 0.021643 | 0.005775 | 0.006451 | 0.016503 | −0.034154 | 0.011931 | 0.023356 | 0.002767 | 0.011176 | 0.013624 | −0.031619 |
| 133 | 0.021364 | 0.02534 | 0.01637 | 0.004659 | 0.040595 | −0.00413 | 0.001212 | 0.013056 | 0.00135 | 0,020992 | 0.005386 | 0.01118 | −0.003508 | 0.009777 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 134 | −0.002971 | 0.013449 | 0.012434 | −0.021409 | −0.025998 | −0.028534 | −0.025132 | 0.025581 | −0.018819 | −0.028644 | −0.011459 | −0.039273 | 0.03831 | 0.017514 |
| 135 | −0.007338 | −0.00794 | −0.000911 | −0.024483 | 0.007393 | 0.007656 | −0.009829 | 0.005283 | 0.003752 | −0.026368 | −0.002932 | −0.014512 | 0.006518 | −0.007866 |
| 136 | 0.032277 | 0.012131 | −0.015802 | −0.003089 | 0.001717 | 0.029342 | −0.036855 | −0.012115 | 0.002904 | −0.060899 | 0.021988 | 0.033905 | 0.01553 | 0.026775 |
| 137 | −0.014306 | 0.002446 | −0.007601 | −0.012402 | −0.033628 | −0.053783 | −0.015238 | −0.045404 | 0.00771 | 0.051384 | −0.015117 | −0.007156 | −0.012902 | 0.036629 |
| 138 | −0.009185 | −0.02703 | −0.011394 | −0.004819 | −0.037571 | −0.020623 | −0.031543 | 0.010118 | 0.008365 | −0.033208 | −0.012884 | −0.030497 | 0.029934 | 0.00934 |
| 139 | 0.011828 | 0.010162 | 0.013858 | −0.011867 | −0.013696 | 0.00589 | −0.015712 | 0.006232 | 0.026313 | −0.012446 | 0.034329 | −0.01084 | 0.050367 | 0.004737 |
| 140 | 0.042033 | 0.040115 | 0.0557921 | −0.050886 | −0.028491 | −0.050425 | −0.024805 | 0.017774 | 0.009436 | 0.062266 | −0.004589 | 0.003525 | −0.008989 | −0.002357 |
| 141 | −0.001615 | 0.000457 | 0.0018751 | −0.036457 | 0.011528 | 0.026104 | 0.038788 | −0.002752 | 0.006996 | 0.013555 | −0.026614 | −0.024902 | −0.010694 | −0.033111 |
| 142 | 0.03549 | 0.018205 | −0.001051 | 0.013821 | 0.023987 | 0.020579 | 0.006455 | 0.029996 | 0.012388 | 0.038264 | 0.018671 | 0.030525 | 0.029144 | 0.020628 |
| 143 | 0.021033 | 0.003518 | 0.034713 | −0.000221 | 0.047059 | 0.031771 | 0.024065 | 0.035561 | −0.033571 | −0.005962 | 0.01305 | 0.001369 | −0.037659 | −0.032612 |
| 144 | −0.012148 | 0.009691 | −0.027066 | 0.001711 | −0.013648 | 0.005331 | −0.018832 | 0.019808 | −0.000968 | −0.022764 | −0.000238 | −0.021111 | 0.030859 | 0.016161 |
| 145 | 0.02033 | −0.006189 | 0.006633 | −0.001576 | 0.014929 | 0.026753 | −0.01166 | 0.022052 | −0.016803 | −0.03489 | 0.009907 | −0.008392 | −0.034859 | −0.022967 |
| 146 | −0.001758 | 0.00282 | −0.014312 | −0.007739 | −0.009608 | −0.01661 | −0.013206 | −0.012259 | −0.005183 | −0.019828 | −0.007995 | −0.010763 | 0.01141 | −0.014969 |
| 147 | 0.014823 | 0.026296 | −0.039124 | −0.0033 | 0.020107 | −0.020379 | 0.002429 | −0.003051 | 0.004309 | −0.036276 | 0.00588 | −0.006228 | 0.02233 | −0.005394 |
| 148 | 0.040562 | 0.028225 | −0.033568 | 0.010678 | −0.021032 | −0.016148 | −0.02294 | 0.054395 | −0.012807 | 0.000304 | 0.029809 | 0.001527 | −0.007664 | −0.024363 |
| 149 | 0.005558, | 0.017969 | −0.03658 | −0.021688 | −0.01745 | 0.012276 | −0.017417 | −0.000915 | −0.041266 | −0.04451 | −0.006297 | −0.009938 | −0.034054 | −0.032557 |
| 150 | 0.001108 | −0.006773 | −0.001346 | 0.000743 | −0.017816 | −0.023544 | 0.012311 | 0.033272 | 0.022013 | 0.030079 | 0.013506 | 0.003033 | −0.011324 | −0.005506 |
| 151 | 0.0066 | 0.000153 | −0.000666 | 0.006661 | 0.005554 | 0.056577 | −0.003537 | −0.037522 | 0.002144 | −0.015086 | 0.008404 | −0.001964 | −0.022534 | −0.005464 |
| 152 | −0.026424 | −0.016927 | −0.007062 | 0.017783 | 0.022631 | 0.001854 | 0.004059 | 0.041378 | −0.011388 | 0.046045 | −0.004513 | 0.002173 | 0.006383 | 0.003509 |
| 153 | −0.002731 | 0.002698 | −0.067447 | −0.004684 | −0.0099 | 0.006587 | 0.009712 | 0.017738 | −0.020536 | 0.016562 | −0.003683 | 0.003554 | −0.01969 | −0.031208 |
| 154 | 0.013253 | −0.006522 | 0.008614 | 0.004991 | 0.000197 | −0.021938 | −0.009562 | 0.000386 | −0.008619 | −0.003188 | 0.017409 | −0.011662 | −0.003673 | −0.029715 |
| 155 | −0.013241 | −0.023945 | −0.015321 | 0.02019 | −0.009452 | −0.015134 | −0.006871 | −0.030435 | −0.008131 | −0.00317 | 0.001091 | 0.0165 | −0.008365 | −0.018035 |
| 156 | 0.021318 | −0.003502 | 0.0163731 | 0.004878 | 0.008147 | 0.007423 | −0.018874 | −0.032184 | −0.009627 | −0.020921 | 0.00905 | 0.034589 | −0.006461 | −0.018164 |
| 157 | −0.009144 | −0.029733 | 0.013584 | 0.010595 | −0.017879 | 0.006399 | −0.004183 | 0.016205 | 0.040531 | 0.015587 | −0.011137 | 0.010013 | 0.039607 | 0.051176 |
| 158 | −0.026921 | −0.00987 | −0.049624 | −0.019251 | −0.01915 | 0.0042 | 0.000766 | −0.018508 | 0.003473 | 0.015155 | −0.009912 | 0.007534 | 0.001284 | 0.025474 |
| 159 | −0.047355 | −0.043661 | 0.037969 | −0.005798 | 0.010614 | 0.018384 | 0.002268 | −0.018364 | 0.030717 | −0.042077 | 0.00428 | −0.015434 | 0.003214 | 0.033403 |
| 160 | −0.050263 | −0.066645 | 0.009855 | 0.01021 | 0.007772 | −0.02542 | −0.002724 | 0.042913 | 0.021136 | −0.027959 | 0.002363 | 0.010707 | −0.001132 | 0.00766 |
| 161 | 0.025241 | 0.016537 | −0.033659 | −0.000756 | −0.005189 | 0.045397 | 0.009683 | 0.014508 | −0.002607 | 0.007842 | 0.016362 | 0.027827 | 0.027078 | 0.038654 |
| 162 | −0.012948 | −0.00234 | 0.008091 | −0.001973 | 0.024563 | 0.008497 | 0.015831 | −0.040443 | 0.050641 | 0.007665 | 0.030272 | −0.003229 | 0.036101 | 0.022234 |
| 163 | 0.004399 | −0.002465 | 0.031446 | −0.040258 | 0.012744 | −0.004127 | 0.013755 | 0.013586 | 0.006397 | −0.00133 | 0.003213 | −0.003613 | −0.004161 | 0.013482 |
| 164 | 0.010002 | 0.021188 | 0.0180881 | 0.006603 | 0.01651 | 0.039012 | 0.040723 | −0.000722 | −0.033102 | 0.015862 | −0.018833 | −0.022505 | −0.048511 | −0.054701 |
| 165 | 0.0132421 | 0.020766 | −0.0119461 | 0.050251 | −0.026619 | 0.01546 | −0.00588 | −0.026041 | −0.032037 | −0.084607 | −0.039465 | −0.026165 | 0.000359 | 0.00411 |
| 166 | 0.000326 | 0.016027 | 0.036247 | 0.002024 | −0.011229 | −0.001889 | −0.01152 | 0.002984 | −0.014982 | 0.0089691 | 0.0169361 | 0.010611 | 0.0037651 | −0.021842 |
| 167 | −0.03387 | −0.00386 | −0.036515 | −0.010407 | −0.039259 | −0.02614 | −0.025069 | 0.015519 | −0.00578 | 0.028877 | −0.005289 | 0.008544 | 0.023482 | 0.014904 |
| 168 | −0.000865 | −0.017925 | 0.019094 | 0.002788 | 0.027325 | −0.00963 | 0.027744 | 0.010532 | 0.009314 | 0.007446 | 0.01458 | 0.003713 | 0.014321 | 0.046414 |
| 169 | −0.017886 | −0.007888 | −0.013452 | −0.02361 | −0.025091 | −0.019921 | −0.012864 | 0.005836 | −0.019406 | −0.016433 | −0.009326 | −0.01166 | −0.008436 | −0.005721 |
| 170 | −0.015489 | −0.004017 | −0.002428 | 0.001462 | −0.029109 | −0.015871 | −0.009872 | −0.004245 | −0.025986 | −0.037165 | −0.007636 | −0.015974 | 0.002271 | −0.000565 |
| 171 | −0.013416 | 0.001127 | −0.0062541 | −0.013865 | −0.003585 | 0.011439 | 0.007818 | −0.001277 | −0.000411 | −0.008418 | −0.009487 | 0.0057151 | 0.0115881 | 0.01204 |
| 172 | −0.014887 | −0.0070481 | −0.033827 | −0.043114 | −0.030609 | −0.005818 | −0.023387 | 0.005927 | 0.003741 | −0.009592 | −0.010279 | 0.008556 | −0.01512 | 0.008598 |
| 173 | 0.004079 | 0.012253 | −0.058422 | −0.04365 | −0.0383 | −0.022247 | −0.024127 | −0.001157 | 0.002867 | 0.015155 | −0.016735 | −0.002207 | 0.002709 | 0.018025 |
| 174 | 0.016304 | 0.01899 | −0.006446 | −0.009351 | 0.014476 | 0.004611 | −0.012633 | −0.004578 | −0.028221 | 0.001904 | −0.002377 | 0.02368 | −0.024464 | −0.023283 |
| 175 | −0.0216 | −0.032946 | −0.050028 | −0.003771 | −0.017881 | −0.033081 | −0.04553 | 0.005083 | −0.029322 | 0.019612 | −0.005931 | −0.009292 | −0.021459 | −0.036997 |
| 176 | −0.011469 | −0.0116421 | 0.009041 | −0.016565 | −0.004435 | 0.020019 | −0.010622 | 0.025824 | −0.003872 | 0.0081061 | −0.009526 | 0.0001641 | −0.016974 | 0.019046 |
| 177 | −0.057453 | −0.062348 | 0.005888 | −0.017031 | −0.00599 | 0.001783 | 0.005246 | 0.001478 | −0.023054 | −0.056845 | 0.046898 | −0.025835 | −0.012679 | −0.017687 |
| 178 | −0.016498 | −0.023558 | −0.015851 | −0.008023 | 0.008379 | 0.002185 | −0.005745 | −0.027252 | 0.008245 | −0.048221 | 0.006767 | −0.019246 | −0.008105 | −0.020955 |
| 179 | 0.002099 | 0.003315 | −0.014284 | 0.025661 | 0.00664 | 0.006301 | −0.001817 | −0.020213 | −0.001007 | 0.001202 | 0.000786 | 0.014021 | 0.00444 | 0.000424 |
| 180 | 0.007987 | 0.008418 | −0.025092 | 0.007105 | −0.007051 | −0.005136 | −0.006441 | −0.009632 | 0.017224 | −0.021427 | 0.008361 | 0.011193 | 0.019064 | 0.02404 |
| 181 | 0.012753 | 0.012262 | −0.024157 | 0.016196 | −0.007284 | −0.007859 | −0.015294 | −0.018947 | 0.0048691 | −0.003926 | 0.0069091 | 0.0044941 | 0.015731 | 0.008664 |
| 182 | −0.0007511 | 0.007196 | −0.008805 | 0.024315 | −0.008245 | −0.021089 | −0.006393 | −0.00761 | 0.004527 | 0.026786 | 0.008504 | −0.014244 | 0.017634 | 0.009575 |
| 183 | 0.000382 | 0.010737 | 0.016895 | 0.023985 | 0.009285 | 0.00512 | 0.019059 | −0.029082 | −0.002613 | 0.006234 | −0.012446 | −0.012241 | −0.005712 | −0.011592 |
| 184 | −0.021073 | −0.01224 | 0.052031 | −0.008009 | 0.009783 | 0.006139 | 0.018515 | −0.011131 | 0.008141 | −0.030076 | −0.007356 | 0.001586 | −0.005225 | −0.013669 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 185 | −0.022954 | −0.032352 | −0.007636 | −0.030728 | −0.029236 | −0.005701 | −0.035104 | −0.03263 | −0.002026 | −0.032713 | −0.006679 | 0.024434 | −0.019495 | 0.018151 |
| 186 | 0.011214 | 0.016472 | 0.031043 | −0.005488 | 0.006477 | 0.032868 | 0.017396 | −0.017709 | 0.029452 | −0.026246 | 0.037284 | 0.038118 | 0.055415 | 0.068067 |
| 187 | 0.016058 | 0.013263 | 0.015703 | −0.013365 | −0.006752 | −0.010783 | 0.02159 | 0.021891 | 0.020502 | 0.004109 | 0.012038 | −0.011296 | 0.005847 | 0.016727 |
| 188 | 0.015027 | 0.004503 | 0.027745 | −0.00933 | 0.005306 | −0.000933 | 0.011721 | −0.006383 | 0.007698 | −0.032043 | 0.014276 | 0.006301 | −0.014003 | −0.011449 |
| 189 | 0.022483 | 0.007743 | 0.046753 | −0.010756 | 0.014751 | 0.002287 | 0.006765 | −0.030288 | 0.003096 | −0.046571 | 0.006624 | −0.004462 | −0.001077 | 0.002714 |
| 190 | 0.00002 | −0.001359 | 0.019293 | −0.000817 | −0.009796 | −0.019473 | 0.001824 | 0.013277 | −0.011127 | −0.018454 | −0.006829 | −0.007903 | −0.011127 | −0.001286 |
| 191 | 0.007238 | −0.008312 | 0.006118 | 0.008937 | −0.002064 | −0.006727 | −0.002532 | 0.003556 | −0.005222 | −0.016839 | 0.008386 | 0.025288 | 0.016163 | 0.011419 |
| 192 | −0.006102 | −0.005075 | 0.012146 | 0.009223 | −0.025092 | −0.006234 | −0.030165 | 0.022504 | −0.033546 | 0.049876 | −0.020196 | −0.016834 | −0.006547 | −0.013377 |
| 193 | −0.024429 | −0.030795 | −0.026793 | −0.000669 | −0.009124 | 0.000491 | −0.003354 | −0.011947 | −0.005602 | 0.002288 | −0.012187 | 0.00061 | 0.013356 | −0.006179 |
| 194 | −0.005299 | −0.013923 | −0.037996 | 0.000517 | 0.001149 | −0.002268 | 0.013773 | 0.002929 | 0.012702 | −0.005022 | 0.015172 | 0.007487 | −0.014001 | −0.018864 |
| 195 | −0.000057 | −0.002563 | 0.024036 | −0.002864 | 0.009684 | −0.000428 | 0.017205 | 0.022072 | 0.00972 | 0.059865 | 0.014646 | −0.004792 | 0.010098 | 0.015042 |
| 196 | −0.005205 | −0.006814 | 0.01417 | −0.002959 | 0.009744 | −0.017443 | 0.005288 | 0.020704 | −0.004732 | −0.009577 | 0.020545 | −0.012157 | −0.007966 | −0.034553 |
| 197 | −0.00362 | 0.011671 | 0.001791 | 0.00275 | −0.013489 | 0.005898 | −0.004307 | 0.018203 | −0.031634 | −0.011326 | −0.0313 | −0.013579 | −0.002109 | −0.007802 |
| 198 | 0.018731 | 0.015362 | 0.05016 | −0.014733 | 0.01135 | 0.007372 | 0.012947 | −0.001615 | 0.00801 | −0.0634 | −0.002882 | −0.020224 | −0.007699 | 0.018766 |
| 199 | 0.003252 | 0.011512 | 0.013114 | 0.000649 | −0.020414 | −0.026617 | −0.00671 | −0.023305 | −0.004195 | −0.060132 | 0.0033 | 0.008388 | 0.018266 | 0.027396 |
| 200 | 0.011311 | 0.015842 | −0.03722 | −0.007562 | 0.025631 | 0.045843 | 0.038822 | −0.032934 | 0.028917 | 0.016454 | 0.003561 | −0.015152 | −0.006661 | −0.01185 |
| 201 | −0.021051 | 0.003212 | 0.010146 | −0.016037 | 0.005951 | 0.004557 | 0.018613 | −0.020809 | −0.00356 | −0.021256 | −0.004809 | −0.003803 | −0.023671 | −0.015301 |
| 202 | 0.000192 | −0.002425 | 0.019328 | 0.006429 | 0.022664 | 0.021678 | 0.008192 | −0.004931 | 0.018632 | −0.069258 | 0.014516 | 0.005321 | 0.027251 | 0.008744 |
| 203 | −0.007449 | 0.016292 | −0.025929 | −0.003503 | −0.017538 | −0.045873 | −0.007099 | 0.025962 | −0.051593 | 0.041705 | −0.038488 | −0.030645 | −0.056629 | −0.032076 |
| 204 | −0.004843 | −0.022972 | −0.00412 | 0.022242 | 0.008447 | 0.020442 | −0.004982 | 0.06377 | −0.009102 | −0.012948 | 0.010639 | 0.001646 | 0.015144 | 0.005996 |
| 205 | 0.037726 | 0.043479 | 0.025524 | −0.014279 | −0.030331 | −0.027028 | −0.02157 | 0.032624 | 0.018525 | −0.016008 | −0.0188 | −0.010764 | −0.017003 | 0.016959 |
| 206 | 0.004242 | −0.010658 | 0.042682 | −0.000357 | 0.013689 | 0.015053 | 0.029415 | 0.034495 | 0.033031 | −0.025324 | −0.003074 | −0.009866 | 0.0174211 | −0.001176 |
| 207 | −0.012534 | −0.012354 | −0.005832 | 0.005874 | 0.000414 | −0.008248 | −0.010867 | −0.039115 | −0.010871 | −0.004438 | −0.024125 | −0.030857 | −0.003799 | −0.04297 |
| 208 | 0.006016 | 0.007468 | −0.010725 | −0.00264 | 0.017758 | 0.031997 | 0.007201 | 0.002871 | −0.023778 | 0.055094 | −0.043437 | −0.024346 | −0.033825 | −0.007812 |
| 209 | −0.0283 | −0.022639 | −0.003751 | −0.01649 | 0.020738 | 0.021096 | −0.02212 | −0.007702 | 0.009659 | 0.019506 | 0.01303 | 0.027153 | 0.010309 | −0.00168 |
| 210 | 0.012579 | 0.014927 | −0.066306 | −0.004978 | 0.0231 | 0.018956 | 0.022218 | −0.009394 | −0.004961 | 0.039006 | 0.018929 | −0.0037 | −0.017607 | −0.001817 |
| 211 | 0.015567 | 0.012766 | −0.040393 | −0.032473 | −0.02524 | 0.035889 | −0.017572 | −0.021409 | 0.005254 | −0.050235 | −0.004667 | 0.00846 | −0.014299 | 0.007554 |
| 212 | 0.005127 | 0.024355 | −0.036789 | −0.01843 | −0.030487 | 0.001382 | −0.014373 | 0.005346 | −0.005836 | −0.030391 | −0.01872 | 0.006977 | 0.012158 | 0.013551 |
| 213 | 0.036969 | 0.064143 | −0.024918 | 0.002423 | 0.001852 | −0.004825 | −0.010426 | 0.035309 | 0.016328 | 0.053048 | 0.02562 | 0.052968 | −0.012029 | 0.016734 |
| 214 | 0.009971 | −0.00757 | 0.018743 | 0.014932 | 0.006283 | 0.012018 | 0.000253 | −0.032609 | 0.01209 | −0.045117 | 0.008928 | 0.009074 | −0.002873 | −0.001158 |
| 215 | 0.013588 | −0.001321 | −0.071858 | −0.024375 | 0.014369 | 0.025673 | 0.025584 | −0.003802 | 0.035531 | −0.004164 | −0.000852 | −0.014562 | 0.020736 | 0.020109 |
| 216 | 0.003652 | 0.006631 | −0.013474 | −0.000676 | 0.037312 | 0.032362 | 0.023654 | 0.044095 | 0.018894 | −0.009909 | 0.01347 | −0.014682 | 0.043661 | 0.025553 |
| 217 | 0.016611 | 0.010166 | 0.025234 | 0.000936 | −0.00436 | −0.041459 | −0.001765 | 0.007423 | 0.010297 | −0.007269 | 0.009954 | −0.03906 | −0.007753 | −0.022452 |
| 218 | 0.005425 | 0.005549 | −0.018498 | −0.022841 | 0.00092 | −0.003124 | −0.016126 | −0.004758 | −0.013049 | 0.014434 | 0.002184 | −0.001989 | −0.009014 | −0.017542 |
| 219 | 0.019529 | −0.000409 | 0.00564 | −0.004117 | 0.015682 | 0.025401 | 0.00066 | −0.004706 | −0.015156 | −0.000733 | 0.003548 | −0.001907 | 0.003421 | −0.025234 |
| 220 | −0.008644 | 0.004634 | 0.06818 | 0.015584 | 0.003494 | −0.040976 | −0.010278 | −0.022252 | −0.012975 | −0.009022 | −0.009699 | −0.023019 | −0.01376 | −0.005263 |
| 221 | 0.020296 | 0.017239 | −0.01849 | −0.014633 | 0.00518 | −0.008167 | −0.00107 | −0.00355 | 0.00517 | 0.005836 | −0.011896 | −0.015977 | −0.014276 | −0.01473 |
| 222 | 0.010306 | −0.001043 | −0.017756 | −0.008822 | −0.001581 | −0.018875 | −0.012551 | 0.009871 | −0.007661 | 0.013249 | −0.015852 | −0.022925 | −0.012048 | −0.017997 |
| 223 | 0.008564 | −0.00181 | −0.037959 | 0.00341 | 0.002725 | −0.014731 | −0.013912 | −0.022342 | −0.03932 | −0.021819 | −0.013537 | −0.003145 | −0.039221 | −0.040111 |
| 224 | 0.022072 | 0.022649 | −0.01095 | −0.003259 | 0.01378 | 0.006748 | −0.010576 | 0.022363 | −0.011758 | 0.023106 | 0.00065 | −0.010192 | −0.018324 | −0.026948 |
| 225 | 0.019894 | 0.024265 | 0.007254 | 0.000275 | 0.010263 | −0.01029 | −0.003422 | 0.00952 | −0.01369 | 0.028756 | −0.003537 | −0.012897 | −0.042244 | −0.029737 |
| 226 | 0.019914 | 0.017658 | 0.01016 | −0.027457 | 0.016662 | −0.00635 | 0.020969 | 0.015979 | −0.007546 | −0.009604 | 0.012089 | −0.001246 | −0.015372 | −0.015759 |
| 227 | 0.041401 | 0.046318 | −0.001115 | −0.042399 | 0.000696 | −0.022703 | 0.031523 | 0.039395 | 0.010154 | −0.009119 | −0.002244 | −0.025912 | −0.009403 | −0.02425 |
| 228 | 0.019923 | 0.017355 | 0.025056 | 0.021675 | 0.021599 | 0.003453 | 0.02435 | 0.002915 | 0.00652 | 0.019588 | 0.008076 | −0.003844 | −0.019917 | −0.032253 |
| 229 | 0.030897 | 0.032645 | 0.008465 | 0.027867 | −0.053793 | −0.010918 | −0.057184 | 0.007025 | 0.028359 | 0.034023 | 0.009277 | 0.030618 | 0.023651 | 0.041241 |
| 230 | 0.024217 | 0.017949 | −0.039048 | −0.006457 | −0.050457 | −0.025114 | −0.035925 | 0.015627 | −0.001323 | −0.018989 | −0.01236 | −0.005726 | 0.034701 | 0.024855 |
| 231 | 0.023361 | 0.033492 | −0.03992 | −0.058032 | −0.0377 | −0.02941 | −0.019616 | 0.053898 | −0.040893 | 0.014944 | −0.017319 | −0.019919 | −0.016596 | −0.014402 |
| 232 | −0.003814 | −0.018485 | 0.044521 | 0.064238 | 0.052145 | 0.022737 | 0.050821 | −0.022385 | 0.017051 | −0.012922 | 0.010849 | 0.052952 | 0.000984 | −0.004912 |
| 233 | 0.019651 | 0.018181 | 0.002537 | −0.016944 | −0.012718 | 0.012601 | −0.013501 | 0.010115 | 0.012723 | −0.018686 | 0.021075 | 0.032783 | 0.017307 | 0.04282 |
| 234 | −0.002297 | −0.013117 | −0.0043 | 0.000731 | 0.032771 | 0.038048 | 0.017048 | −0.005966 | 0.011501 | 0.011418 | 0.003514 | 0.023331 | 0.00865 | 0.019319 |
| 235 | 0.019029 | −0.016071 | −0.011721 | −0.011468 | 0.008811 | 0.021127 | 0.012254 | 0.008271 | 0.025094 | 0.009384 | −0.004358 | 0.002034 | 0.013046 | 0.029316 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 236 | 0.004459 | 0.005717 | −0.010708 | 0.014762 | 0.001452 | 0.020383 | 0.001975 | 0.014897 | −0.014269 | 0.016625 | −0.009608 | 0.008549 | 0.02083 | 0.018179 |
| 237 | −0.033858 | −0.022312 | 0.01819 | 0.005247 | 0.008734 | 0.017581 | 0.0125 | −0.021362 | −0.002669 | −0.036807 | 0.010187 | 0.007938 | −0.003032 | −0.014102 |
| 238 | −0.003834 | −0.035965 | −0.004311 | 0.018252 | −0.002765 | 0.0144 | 0.000452 | 0.006036 | −0.023048 | −0.011253 | −0.002378 | 0.00188 | −0.006961 | −0.032991 |
| 239 | 0.028928 | 0.005436 | −0.016977 | −0.003812 | −0.004872 | 0.00921 | −0.002519 | 0.034533 | −0.027388 | 0.01785 | −0.012651 | −0.010618 | −0.018654 | −0.026498 |
| 240 | −0.006366 | −0.015663 | −0.022454 | −0.000702 | 0.018127 | 0.004282 | 0.004455 | 0.003399 | 0.008346 | −0.00939 | 0.02585 | 0.017654 | 0.014048 | 0.003586 |
| 241 | 0.010309 | −0.004843 | 0.023739 | 0.005355 | 0.028266 | 0.01642 | 0.001823 | 0.016093 | −0.011601 | −0.001213 | 0.038384 | 0.020994 | 0.011583 | 0.026806 |
| 242 | −0.015064 | −0.009014 | −0.021824 | −0.003669 | −0.022237 | −0.018742 | −0.027133 | 0.022165 | 0.014568 | 0.042437 | −0.01972 | 0.006868 | 0.035315 | 0.054932 |
| 243 | −0.016714 | −0.019264 | −0.004085 | −0.01598 | 0.01055 | 0.009543 | 0.020613 | −0.003635 | −0.004286 | −0.024321 | −0.002313 | 0.0042081 | −0.031612 | −0.032365 |
| 244 | 0.005934 | 0.014429 | 0.01768 | 0.010146 | 0.021207 | 0.008328 | 0.038814 | −0.001618 | 0.032009 | −0.005182 | 0.000199 | 0.006136 | −0.013293 | 0.014293 |
| 245 | 0.008991 | 0.016149 | −0.010896 | −0.004887 | −0.005515 | −0.002541 | −0.008416 | −0.011261 | −0.011706 | 0.02879 | −0.013404 | −0.005156 | −0.025424 | −0.016513 |
| 246 | −0.020481 | −0.020347 | −0.007204 | 0.001831 | −0.019875 | −0.008437 | −0.025986 | −0.006672 | 0.0052531 | 0.042819 | −0.010668 | −0.014419 | 0.014094 | 0.017045 |
| 247 | 0.0006511 | −0.0072771 | −0.0103931 | −0.002538 | −0.016457 | −0.002348 | −0.010509 | 0.032935 | −0.012557 | 0.0278381 | 0.0021931 | 0.008769 | −0.010583 | −0.001745 |
| 248 | 0.00418 | −0.007943 | 0.031595 | 0.02106 | 0.00718 | 0.001496 | 0.014849 | −0.005756 | 0.007953 | 0.016487 | 0.010717 | 0.022821 | 0.008864 | −0.014917 |
| 249 | 0.00302 | −0.008117 | −0.00456 | 0.005007 | −0.015115 | 0.003457 | −0.016125 | −0.007718 | 0.007774 | −0.027229 | 0.009953 | 0.006707 | 0.030655 | 0.022092 |
| 250 | −0.01228 | −0.024222 | −0.038203 | −0.001924 | 0.004158 | 0.008784 | 0.005735 | 0.00625 | 0.001335 | −0.000909 | 0.01293 | −0.004345 | 0.01657 | 0.002647 |
| 251 | −0.021312 | −0.031459 | −0.00011 | 0.019433 | 0.026943 | −0.004193 | 0.017246 | −0.007507 | −0.008236 | 0.001049 | 0.007229 | −0.003453 | 0.001217 | −0.022566 |
| 252 | −0.009601 | 0.007889 | 0.009793 | 0.005524 | 0.008913 | −0.023471 | −0.002964 | 0.02048 | −0.011127 | 0.044025 | −0.00639 | 0.011878 | −0.008364 | −0.009897 |
| 253 | −0.026363 | −0.011853 | −0.005603 | 0.015471 | 0.005826 | −0.021436 | 0.001137 | −0.00824 | −0.024333 | −0.008553 | −0.0091 | −0.006346 | −0.05154 | −0.060897 |
| 254 | −0.00651 | −0.015049 | −0.019922 | 0.015072 | 0.000318 | 0.010042 | −0.000896 | −0.025714 | −0.011992 | −0.029394 | −0.000132 | 0.013281 | −0.007416 | 0.00869 |
| 255 | −0.006627 | −0.002068 | −0.006795 | 0.012434 | 0.007349 | 0.00973 | 0.014038 | −0.005114 | 0.01693 | −0.004123 | −0.000947 | −0.00115 | 0.017912 | 0.026005 |
| 256 | 0.008793 | 0.014754 | −0.029614 | 0.008116 | −0.00108 | 0.029659 | −0.010323 | 0.031711 | 0.00643 | 0.02634 | −0.012765 | 0.001011 | 0.004859 | 0.022056 |
| 257 | 0.002204 | 0.002388 | −0.008131 | 0.019712 | −0.008941 | 0.022361 | −0.007378 | 0.007323 | 0.010802 | 0.015973 | −0.025013 | −0.006837 | 0.022866 | 0.034363 |
| 258 | 0.003249 | 0.008559 | −0.001308 | 0.000943 | 0.025712 | 0.011052 | 0.026658 | 0.013348 | 0.000343 | 0.025186 | 0.02494 | 0.0049 | −0.022304 | −0.015032 |
| 259 | −0.002644 | −0.002819 | −0.022886 | 0.001578 | −0.019687 | −0.003146 | −0.0174 | −0.012656 | −0.007012 | −0.010029 | −0.006054 | −0.006596 | 0.010892 | −0.002074 |
| 260 | 0.004698 | 0.02926 | 0.022707 | −0.007792 | −0.015249 | −0.040229 | −0.017129 | −0.025846 | −0.008806 | 0.010553 | −0.004235 | 0.0019 | −0.003244 | 0.00284 |
| 261 | −0.025315 | −0.005378 | −0.003149 | 0.003127 | −0.003507 | −0.044047 | −0.009328 | −0.011039 | −0.007449 | 0.003313 | 0.002468 | −0.019085 | 0.002754 | −0.025237 |
| 262 | 0.004969 | 0.011697 | 0.000798 | 0.000437 | −0.025885 | −0.026962 | −0.031629 | 0.01255 | −0.000105 | −0.023847 | −0.018175 | −0.031221 | 0.01143 | 0.005972 |
| 263 | −0.002224 | 0.001405 | 0.000775 | 0.007165 | −0.011842 | −0.027225 | −0.021646 | −0.009147 | 0.002297 | −0.011766 | −0.017889 | −0.025139 | 0.023259 | −0.002751 |
| 264 | 0.008668 | −0.003359 | −0.026387 | −0.023801 | −0.004451 | 0.012302 | −0.002694 | 0.022406 | 0.009765 | 0.005353 | −0.001271 | −0.003583 | 0.017124 | 0.021412 |
| 265 | 0.007131 | −0.00219 | −0.005912 | −0.012266 | 0.011539 | 0.012242 | 0.025918 | 0.027956 | −0.015406 | 0.000396 | 0.003843 | −0.007189 | −0.018745 | −0.003015 |
| 266 | −0.001977 | 0.003003 | −0.003615 | −0.003426 | 0.005727 | 0.006039 | 0.009495 | 0.022126 | −0.023661 | −0.004618 | 0.000169 | −0.007628 | −0.023227 | −0.008683 |
| 267 | 0.004178 | 0.0063331 | 0.009917 | −0.022251 | 0.029399 | −0.007985 | 0.020155 | 0.00315 | 0.00963 | 0.002984 | 0.024474 | 0.006397 | −0.015836 | −0.017287 |
| 268 | 0.0153741 | 0.0166191 | −0.005821 | −0.037007 | 0.013511 | −0.001246 | 0.020619 | 0.03328 | −0.011531 | 0.001039 | −0.002455 | −0.009694 | −0.015284 | −0.004292 |
| 269 | 0.013356 | 0.006905 | 0.021574 | −0.015453 | 0.015981 | −0.002576 | 0.012003 | 0.005245 | 0.006785 | −0.014031 | 0.011894 | 0.005182 | −0.00042 | 0.011036 |
| 270 | 0.00046 | 0.007908 | 0.026753 | −0.026212 | 0.009092 | −0.033726 | 0.01458 | −0.003785 | 0.005132 | −0.017929 | 0.009692 | −0.014759 | 0.009675 | −0.013694 |
| 271 | −0.004258 | −0.012138 | 0.008218 | −0.000146 | −0.001887 | 0.010944 | 0.026047 | 0.04064 | −0.008242 | 0.00859 | 0.00946 | 0.011688 | 0.018479 | 0.02915 |
| 272 | 0.015659 | 0.002474 | −0.01466 | 0.013283 | −0.039445 | −0.008196 | −0.044694 | 0.011766 | −0.020556 | 0.02213 | 0.000235 | 0.024859 | −0.007356 | −0.01102 |
| 273 | 0.008647 | 0.011241 | −0.005568 | −0.017218 | −0.069195 | −0.050271 | −0.055916 | −0.004433 | −0.012268 | −0.017419 | −0.009445 | 0.005738 | 0.025274 | 0.014784 |
| 274 | 0.00936 | 0.009074 | 0.004221 | −0.011075 | −0.068992 | −0.052186 | −0.057462 | −0.004816 | −0.006775 | −0.014777 | −0.002237 | 0.009823 | 0.031117 | 0.022755 |
| 275 | −0.004899 | −0.012989 | −0.023281 | −0.025837 | −0.039023 | −0.071059 | −0.001187 | 0.00896 | 0.02798 | −0.013934 | 0.002001 | −0.021261 | 0.045279 | −0.008073 |
| 276 | 0.015546 | 0.013667 | −0.01189 | 0.02847 | −0.003635 | 0.029783 | −0.020963 | 0.031478 | −0.01352 | 0.021392 | 0.0014 | 0.027353 | 0.004491 | 0.012332 |
| 277 | −0.008384 | 0.006085 | 0.004474 | 0.002979 | 0.018722 | −0.000392 | 0.009774 | −0.003808 | 0.012005 | 0.01957 | 0.01702 | 0.010708 | 0.00458 | −0.005831 |
| 278 | 0.0131271 | 0.040308 | 0.0000741 | 0.015606 | 0.007754 | −0.010739 | −0.000826 | −0.020066 | 0.0234641 | 0.034111 | 0.0093331 | 0.0104661 | 0.0009831 | 0.000285 |
| 279 | 0.019539 | −0.005172 | −0.009985 | 0.013037 | 0.011907 | 0.01035 | 0.005778 | 0.006085 | −0.011905 | 0.016654 | 0.000555 | 0.004185 | −0.002388 | −0.035804 |
| 280 | −0.020978 | −0.004165 | −0.028613 | −0.032372 | −0.003136 | −0.007761 | 0.013458 | −0.001449 | −0.022337 | −0.047445 | −0.003304 | −0.024512 | −0.042844 | −0.052264 |
| 281 | −0.017944 | 0.000246 | −0.004915 | −0.013611 | −0.015807 | −0.015594 | −0.029903 | −0.034801 | −0.021865 | −0.001987 | 0.004529 | 0.001244 | −0.007633 | −0.00867 |
| 282 | −0.006401 | 0.012439 | 0.014301 | −0.002624 | −0.004215 | −0.013453 | −0.018875 | −0.016939 | −0.004536 | 0.024276 | 0.013381 | 0.00422 | −0.014822 | −0.004754 |
| 283 | 0.002264 | −0.005022 | 0.017701 | 0.000208 | −0.003706 | −0.003529 | −0.013562 | 0.001268 | 0.00126 | 0.012904 | 0.016121 | 0.03108 | 0.001558 | −0.01236 |
| 284 | 0.007113 | 0.007539 | −0.013464 | 0.008397 | −0.010799 | 0.022062 | −0.007707 | −0.002045 | 0.013276 | 0.004937 | −0.021877 | 0.004113 | 0.018506 | 0.032349 |
| 285 | 0.014968 | 0.015872 | 0.002921 | 0.021952 | −0.001216 | 0.022873 | 0.005044 | 0.015881 | 0.022395 | 0.013999 , | −0.02222 | −0.00101 | 0.015064 | 0.031544 |
| 286 | 0.019426 | 0.032418 | −0.021096 | 0.003058 | 0.013015 | 0.026254 | 0.021306 | 0.014543 | 0.010424 | −0.002559 | 0.026222 | 0.010274 | −0.03245 | −0.008921 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 287 | 0.0047341 | 0.017805 | 0.002353 | 0.014787 | 0.031996 | 0.020845 | 0.029142 | −0.004591 | 0.023618 | −0.015065 | 0.033803 | 0.01909 | −0.018889 | −0.009281 |
| 288 | −0.043837 | −0.028594 | −0.014271 | −0.005714 | 0.016015 | −0.006114 | 0.014959 | 0.026518 | 0.019723 | 0.050178 | 0.02417 | 0.021001 | 0.007008 | −0.001327 |
| 289 | −0.022278 | −0.021642 | 0.023558 | 0.00127 | −0.006853 | −0.016629 | −0.000413 | 0.022541 | 0.023843 | −0.002142 | −0.004699 | −0.027974 | 0.031825 | 0.037444 |
| 290 | −0.193465 | −0.176266 | −0.021998 | −0.006108 | −0.008677 | −0.030298 | 0.000977 | −0.041012 | 0.017193 | 0.000504 | −0.002142 | 0.001277 | 0.028724 | 0.013985 |
| 291 | 0.807084 | −0.174026 | −0.030272 | −0.011177 | −0.012409 | −0.032169 | −0.001172 | −0.038486 | 0.020404 | 0.009126 | −0.000848 | −0.001415 | 0.028699 | 0.015795 |
| 292 | −0.173056 | 0.802698 | −0.025162 | −0.002545 | −0.00717 | −0.025083 | −0.003319 | −0.032238 | 0.016119 | −0.015155 | 0.008001 | 0.000886 | 0.02262 | 0.005133 |
| 293 | −0.008757 | −0.001197 | 0.704588 | −0.06677 | −0.095295 | −0.000939 | −0.073737 | 0.049445 | −0.054989 | 0.036135 | −0.068982 | 0.002369 | 0.013648 | 0.00874 |
| 294 | 0.003118 | 0.00155 | −0.048794 | 0.885125 | −0.056371 | −0.063956 | −0.037172 | 0.002945 | −0.033174 | −0.014225 | −0.030214 | −0.042703 | −0.029034 | −0.020039 |
| 295 | 0.006446 | 0.010852 | −0.099473 | −0.065175 | 0.831364 | −0.086977 | −0.129085 | 0.011227 | −0.061587 | −0.008428 | −0.077331 | −0.037424 | −0.004742 | 0.007985 |
| 296 | −0.014731 | −0.009507 | 0.005144 | −0.066291 | −0.100405 | 0.803002 | −0.082354 | −0.029556 | −0.041362 | 0.004706 | −0.028612 | −0.064904 | −0.025634 | −0.046986 |
| 297 | 0.007554 | 0.011455 | −0.08172 | −0.046668 | −0.127303 | −0.071559 | 0.843248 | −0.013536 | −0.075402 | −0.021628 | −0.065834 | −0.02425 | −0.0162 | 0.006005 |
| 298 | −0.032676 | −0.035104 | 0.055838 | −0.005655 | 0.009497 | −0.022881 | −0.017864 | 0.724601 | −0.004143 | −0.156262 | −0.006125 | −0.010456 | −0.017073 | −0.012633 |
| 299 | 0.011124 | 0.017116 | −0.046103 | −0.044875 | −0.046709 | −0.041121 | −0.064543 | −0.012151 | 0.854765 | −0.020451 | −0.065643 | −0.054002 | −0.112521 | −0.098471 |
| 300 | −0.004685 | −0.024053 | 0.055947 | −0.012997 | −0.000027 | 0.018216 | −0.007593 | −0.151088 | −0.005398 | 0.644159 | 0.004378 | −0.021495 | 0.000106 | −0.01288 |
| 301 | 0.005486 | 0.012437 | −0.064043 | −0.034901 | −0.067987 | −0.024216 | −0.057637 | −0.019005 | −0.066864 | 0.009344 | 0.900729 | −0.055503 | −0.042259 | −0.027206 |
| 302 | 0.002627 | 0.001923 | 0.006266 | −0.046934 | −0.038901 | −0.064921 | −0.023121 | −0.015325 | −0.058929 | −0.013195 | −0.055865 | 0.87484 | −0.055175 | −0.082118 |
| 303 | 0.03009 | 0.029571 | 0.023452 | −0.04195 | 0.015512 | −0.024375 | −0.00051 | −0.03799 | −0.103245 | −0.021323 | −0.028731 | −0.049099 | 0.80051 | −0.147349 |
| 304 | 0.006115 | 0.010197 | 0.014782 | −0.028483 | 0.022182 | −0.048791 | 0.006298 | −0.025806 | −0.115296 | −0.016812 | −0.027534 | −0.07578 | −0.174799 | 0.77426 |
| 305 | −0.011853 | −0.033253 | −0.079517 | −0.014171 | −0.02912 | 0.009372 | −0.023778 | −0.00473 | −0.014869 | −0.013009 | −0.02545 | −0.000327 | −0.002082 | 0.018949 |
| 306 | −0.051481 | −0.04229 | −0.033785 | −0.024175 | 0.010453 | −0.039223 | −0.006689 | −0.011989 | −0.033753 | −0.009066 | −0.016738 | −0.036006 | −0.003264 | −0.035976 |
| 307 | −0.024477 | −0.01851 | 0.001617 | −0.01176 | −0.017081 | −0.024996 | 0.001223 | 0.027832 | −0.003172 | 0.014895 | 0.020625 | 0.038955 | −0.046521 | −0.029519 |
| 308 | −0.018658 | −0.01847 | 0.000847 | 0.016163 | 0.033569 | −0.02899 | −0.00769 | 0.007866 | −0.031732 | 0.005781 | 0.003682 | −0.028745 | 0.007068 | −0.058853 |
| 309 | −0.001609 | −0.006709 | −0.018341 | −0.00559 | 0.003905 | −0.016783 | −0.010873 | −0.011883 | −0.004581 | −0.0058 | −0.001754 | −0.015918 | 0.006657 | −0.02166 |
| 310 | −0.022273 | −0.020946 | 0.000636 | −0.025716 | 0.018278 | −0.043787 | 0.015692 | −0.016806 | −0.009799 | 0.022966 | −0.000392 | −0.040536 | −0.019902 | −0.036619 |
| 311 | −0.003717 | 0.009369 | −0.041241 | −0.006524 | −0.037333 | −0.010061 | −0.025582 | −0.01576 | 0.008763 | 0.011862 | −0.0205 | 0.01687 | 0.001585 | 0.024336 |
| 312 | 0.004595 | −0.000223 | 0.045817 | 0.007427 | 0.020691 | 0.001493 | −0.030761 | −0.001209 | −0.006919 | 0.025811 | 0.021047 | 0.038035 | −0.048454 | 0.005683 |
| 313 | 0.018628 | 0.018047 | −0.002881 | 0.014808 | −0.006462 | 0.002114 | −0.021177 | −0.036141 | −0.012591 | −0.014879 | −0.022931 | 0.00382 | −0.0093 | −0.004731 |
| 314 | −0.001759 | 0.001683 | 0.022903 | −0.018244 | 0.000792 | 0.001783 | −0.026577 | −0.055313 | −0.005685 | −0.029144 | 0.003571 | 0.006952 | −0.029032 | −0.011158 |
| 315 | 0.011602 | 0.010164 | 0.001644 | 0.00753 | 0.002775 | −0.013222 | −0.012886 | −0.008706 | −0.033969 | −0.020788 | −0.000277 | −0.00702 | −0.035125 | −0.023894 |
| 316 | 0.002251 | 0.027537 | −0.014649 | −0.005654 | −0.007513 | −0.030325 | 0.013338 | −0.049807 | 0.030128 | −0.008086 | −0.020377 | −0.029832 | −0.002812 | 0.01841 |
| 317 | −0.001067 | 0.004827 | −0.034294 | −0.003801 | −0.018896 | −0.013486 | −0.015643 | −0.031285 | 0.01489r | 0.015677 | −0.027011 | −0.000442 | 0.024161 | 0.015815 |
| 318 | 0.022471 | 0.010343 | −0.007558 | −0.003279 | −0.012471 | −0.019837 | −0.009399 | −0.020667 | −0.015729 | −0.045309 | −0.019197 | −0.018171 | −0.010655 | −0.041268 |
| 319 | 0.01241 | 0.005653 | −0.006994 | −0.000145 | 0.006984 | −0.014163 | −0.012085 | −0.011227 | −0.013277 | −0.005851 | −0.002559 | −0.011823 | −0.029413 | −0.025682 |
| 320 | −0.007379 | −0.01605 | −0.0247631 | −0.011549 | 0.022251 | −0.035428 | 0.013052 | −0.000411 | −0.01694 | 0.039292 | 0.004828 | −0.027252 | −0.003408 | −0.040226 |
| 321 | −0.009026 | 0.003833 | 0.014274 | −0.022546 | −0.03174 | −0.04115 | −0.047513 | −0.004533 | −0.064069 | −0.00166 | −0.037388 | −0.045071 | −0.044533 | −0.033802 |
| 322 | 0.013113 | 0.013674 | −0.024854 | −0.006506 | 0.010254 | −0.000026 | 0.046474 | −0.012886 | 0.012503 | 0.00001 | 0.006328 | −0.00571 | 0.006021 | −0.020525 |
| 323 | −0.011635 | −0.009084 | 0.023556 | 0.005648 | −0.011999 | 0.031886 | −0.010891 | −0.053203 | −0.009805 | 0.024486 | −0.016077 | −0.004188 | −0.004179 | 0.005171 |
| 324 | −0.015729 | −0.000033 | −0.012406 | −0.01908 | 0.008306 | −0.018713 | −0.000526 | −0.036193 | 0.001439 | 0.015872 | −0.006724 | −0.019458 | 0.031167 | 0.02686 |
| 325 | 0.008723 | 0.01436 | −0.016231 | −0.024246 | −0.0188 | −0.04783 | −0.026956 | −0.012044 | 0.011658 | 0.019029 | −0.006741 | −0.011433 | −0.00802 | 0.001842 |
| 326 | 0.025858 | 0.019687 | 0.002792 | −0.037708 | −0.006922 | −0.013184 | 0.021587 | 0.018987 | −0.008636 | 0.036488 | 0.004641 | −0.009467 | −0.003891 | 0.01209 |
| 327 | −0.006585 | −0.018494 | 0.013036 | −0.000821 | −0.005731 | −0.042995 | −0.005643 | −0.01153 | −0.026702 | 0.017865 | −0.008907 | −0.033359 | −0.023317 | −0.041107 |
| 328 | −0.006683 | −0.00101 | 0.0563 | −0.00956 | −0.020737 | −0.068972 | −0.018693 | −0.05118 | 0.024478 | −0.028924 | 0.016112 | −0.013268 | 0.039189 | 0.004946 |
| 329 | 0.018219 | 0.01344 | 0.038027 | −0.003822 | −0.016767 | 0.008285 | −0.008591 | 0.002973 | −0.037498 | 0.021003 | −0.031291 | −0.02909 | −0.061678 | −0.028216 |
| 330 | 0.014138 | 0.029393 | 0.010609 | −0.021136 | 0.014959 | 0.013553 | 0.012986 | −0.02404 | 0.009915 | 0.034198 | −0.008946 | −0.034281 | −0.032024 | −0.0214 |
| 331 | 0.001158 | −0.009985 | −0.026422 | −0.030638 | 0.001174 | 0.00296 | −0.003181 | 0.00655 | −0.001592 | 0.000338 | 0.008604 | −0.001093 | −0.015616 | 0.003956 |
| 332 | 0.001274 | 0.004954 | 0.026916 | −0.008952 | 0.00748 | −0.009861 | 0.006081 | −0.02881 | −0.009071 | −0.01587 | −0.003525 | −0.016744 | −0.033748 | −0.03974 |
| 333 | 0.000023 | 0.002246 | −0.029992 | −0.018636 | −0.029884 | −0.012412 | −0.023135 | 0.011964 | 0.025337 | 0.026188 | −0.024412 | −0.00004 | 0.035422 | 0.040841 |
| 334 | 0.003088 | 0.003304 | −0.010177 | −0.030173 | −0.01375 | −0.003481 | −0.017838 | 0.04385 | 0.008615 | 0.011271 | −0.022033 | −0.007449 | −0.014915 | 0.015815 |
| 335 | 0.015001 | 0.011222 | −0.023649 | −0.015769 | 0.001426 | 0.000546 | −0.001684 | 0.018641 | −0.017066 | 0.026012 | −0.008403 | −0.018356 | −0.020864 | −0.028654 |
| 336 | 0.007009 | 0.009508 | 0.00975 | −0.034105 | −0.00005 | 0.017157 | 0.014296 | −0.020976 | −0.017397 | −0.047403 | −0.004026 | 0.001792 | −0.021616 | −0.025774 |
| 337 | −0.01982 | −0.030831 | 0.001038 | −0.005949 | −0.029706 | −0.036651 | −0.011687 | −0.013174 | −0.053056 | 0.021848 | −0.041607 | −0.009621 | −0.050415 | −0.019711 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 338 | 0.021478 | 0.031571 | 0.009073 | −0.000986 | −0.016692 | −0.055238 | 0.011606 | −0.071603 | 0.000877 | 0,041246 | 0.01397 | −0.004598 | −0.001239 | −0.002401 |
| 339 | −0.013 | −0.005832 | −0.019708 | 0.021915 | 0.013578 | 0.008979 | 0.033763 | 0.021108 | 0.005418 | 0.047437 | −0.003576 | −0.004761 | −0.021276 | −0.036308 |
| 340 | 0.027627 | 0.022981 | −0.052707 | 0.02878 | −0.019515 | −0.009336 | −0.031084 | 0.0016 | −0.034229 | 0.017287 | 0.002872 | 0.034822 | −0.045316 | −0.026432 |
| | KT | KU | KV | KW | KX | KY | KZ | LA | LB | LC | LD | LE | LF | LG |
| 1 | −0.035368 | 0.042225 | 0.001638 | −0.015791 | 0.013671 | 0.050526 | 0.001833 | 0.021435 | −0.019119 | 0.061629 | −0.027657 | −0.026601 | 0.069931 | −0.047991 |
| 2 | −0.013544 | −0.036911 | 0.095897 | −0.02881 | 0.002713 | −0.015492 | −0.035461 | 0.032318 | −0.054649 | 0.134739 | 0.023155 | −0.044938 | −0.054382 | 0.00341 |
| 3 | −0.041404 | 0.082967 | 0.052005 | 0.048581 | −0.073475 | −0.031763 | −0.088679 | −0.013327 | −0.062147 | −0.022398 | −0.062394 | −0.000921 | −0.100807 | −0.086955 |
| 4 | −0.027783 | −0.024337 | 0.189315 | −0.017326 | 0.003642 | 0.043726 | 0.037125 | 0.147341 | −0.006856 | 0.15689 | 0.023146 | −0.074839 | 0.04304 | 0.049956 |
| 5 | −0.014194 | −0.022212 | 0.08473 | 0.00851 | −0.025803 | −0.056949 | −0.042781 | 0.038032 | −0.05416 | 0.015467 | 0.029823 | 0.015898 | −0.016611 | −0.001335 |
| 6 | 0.01333 | 0.013881 | 0.017446 | −0.022781 | 0.032602 | 0.060202 | 0.047686 | −0.00441 | 0.02648 | 0.011845 | 0.05983 | 0.113381 | 0.046869 | 0.045874 |
| 7 | −0.028022 | −0.050766 | 0.021403 | 0.022671 | 0.02724 | 0.016402 | 0.033636 | 0.017087 | −0.001315 | 0.022874 | 0.059244 | 0.045527 | 0.031553 | 0.097266 |
| 8 | 0.004712 | 0.048132 | 0.008252 | 0.053589 | 0.002038 | 0.025768 | −0.050111 | −0.051656 | −0.022102 | −0.045326 | −0.013426 | 0.006026 | −0.028496 | −0.037502 |
| 9 | −0.070432 | −0.055054 | −0.145445 | −0.00829 | 0.046855 | 0.043784 | 0.030003 | −0.127275 | −0.029647 | −0.041338 | 0.010263 | −0.006131 | 0.060547 | 0.054366 |
| 10 | 0.091772 | 0.038247 | −0.014897 | 0.031814 | −0.012097 | 0.032238 | −0.038965 | −0.027302 | 0.000068 | 0.018921 | −0.042348 | 0.096269 | −0.040305 | −0.044354 |
| 11 | 0.019133 | −0.019259 | −0.068041 | 0.002808 | 0.013417 | 0.021222 | 0.024596 | −0.031897 | 0.019542 | −0.019196 | 0.013074 | 0.010259 | 0.017572 | 0.012295 |
| 12 | 0.017653 | 0.01646 | 0.023156 | −0.023841 | −0.056297 | −0.036298 | 0.047192 | −0.020267 | 0.013692 | 0.073749 | −0.014377 | −0.044497 | −0.049822 | 0.036172 |
| 13 | −0.015293 | 0.024476 | 0.015849 | 0.012085 | 0.043755 | 0.031943 | 0.070214 | −0.046257 | 0.017698 | −0.00593 | −0.016615 | 0.07904 | 0.066613 | 0.024529 |
| 14 | −0.016087 | −0.043869 | −0.039692 | 0.006146 | 0.02707 | −0.015957 | 0.020006 | 0.098494 | −0.008377 | −0.050991 | 0.019752 | 0.041428 | 0.043585 | 0.010765 |
| 15 | 0.034789 | −0.083403 | −0.075504 | 0.041912 | 0.002276 | −0.076836 | −0.088367 | 0.049858 | 0.029548 | −0.010746 | 0.02688 | 0.015645 | −0.008296 | −0.048479 |
| 16 | −0.04301 | −0.007342 | −0.04858 | −0.013578 | 0.005347 | 0.034406 | 0.026294 | −0.040181 | 0.027985 | 0.000157 | 0.024306 | −0.074212 | −0.010663 | −0.018766 |
| 17 | 0.02905 | −0.013087 | −0.148282 | 0.009316 | 0.01516 | −0.038128 | −0.082298 | 0.062601 | −0.011472 | −0.014012 | −0.031068 | 0.078566 | −0.056433 | −0.073795 |
| 18 | 0.128321 | 0.041331 | 0.02732 | 0.000331 | −0.019731 | −0.013744 | 0.053309 | 0.086713 | 0.012751 | 0.105231 | −0.001924 | −0.026663 | −0.042001 | 0.035939 |
| 19 | 0.0142924 | 0.023945 | 0.088552 | −0.039543 | 0.024879 | −0.004164 | 0.048624 | 0.137358 | 0.00378 | 0.017557 | 0.018825 | 0.011922 | 0.01749 | 0.021841 |
| 20 | 0.066682 | −0.073076 | −0.041848 | −0.018294 | −0.000179 | −0.008557 | −0.022844 | −0.119769 | −0.069215 | −0.028057 | −0.080772 | −0.019326 | −0.008674 | −0.05261 |
| 21 | −0.049183 | 0.023602 | −0.017974 | −0.001891 | −0.00521 | 0.008931 | 0.020748 | −0.023985 | 0.047794 | −0.07379 | −0.034103 | −0.094614 | 0.055668 | 0.057256 |
| 22 | 0.058348 | −0.048496 | 0.095706 | −0.030831 | −0.045923 | 0.01824 | 0.058922 | −0.067984 | −0.071118 | −0.066738 | −0.021275 | −0.053766 | −0.032852 | −0.065142 |
| 23 | −0.05567 | 0.008398 | −0.041536 | 0.027347 | 0.034952 | −0.011404 | −0.057887 | 0.095415 | 0.026996 | 0.027022 | −0.017409 | −0.04121 | 0.022461 | −0.053385 |
| 24 | 0.015111 | 0.032152 | −0.072871 | −0.021787 | 0.034733 | 0.04273 | −0.027355 | −0.061813 | −0.029255 | −0.076015 | 0.029215 | 0.005453 | 0.001127 | 0.004329 |
| 25 | −0.042895 | −0.016203 | −0.129884 | 0.015789 | −0.016702 | −0.063897 | 0.023841 | 0.128304 | 0.015205 | −0.082998 | 0.020318 | −0.056036 | −0.029335 | 0.070058 |
| 26 | −0.079529 | 0.025393 | 0.011266 | −0.017411 | −0.04884 | 0.015174 | −0.031521 | −0.038919 | −0.036584 | 0.041777 | −0.042577 | −0.051945 | 0.015683 | 0.01253 |
| 27 | 0.095823 | −0.0548 | −0.053998 | −0.027249 | 0.026769 | 0.033394 | −0.046766 | −0.191074 | −0.017018 | −0.027334 | 0.024056 | 0.084722 | −0.008344 | 0.014738 |
| 28 | −0.032294 | −0.031968 | −0.031102 | −0.013968 | −0.011969 | −0.028235 | 0.096827 | 0.011411 | 0.087433 | 0.08253 | 0.054341 | −0.006016 | −0.037987 | −0.056994 |
| 29 | −0.015684 | 0.019368 | −0.014348 | −0.000531 | −0.025045 | −0.009566 | −0.026804 | −0.014481 | 0.041452 | −0.04614 | −0.05788 | 0.012758 | −0.027705 | 0.018926 |
| 30 | 0.035927 | −0.067704 | 0.030421 | −0.00965 | −0.023247 | −0.112508 | 0.003465 | 0.076898 | 0.004051 | −0.066986 | 0.039959 | 0.002715 | 0.001376 | 0.009114 |
| 31 | 0.046464 | 0.03033 | 0.034734 | −0.026697 | −0.001451 | −0.012344 | 0.033518 | 0.026243 | 0.004452 | 0.139904 | −0.008182 | 0.027887 | −0.015621 | 0.038226 |
| 32 | −0.02698 | −0.014771 | 0.016678 | 0.018963 | 0.006535 | −0.006001 | 0.030557 | 0.04633 | −0.00907 | −0.079408 | −0.005856 | −0.054939 | 0.002757 | 0.091415 |
| 33 | 0.018879 | 0.073002 | −0.010624 | −0.043803 | 0.011734 | −0.003152 | 0.02774 | −0.028578 | 0.056655 | −0.023324 | 0.006371 | −0.133838 | 0.022629 | −0.059703 |
| 34 | −0.079104 | 0.03817 | −0.061555 | 0.016074 | −0.010566 | 0.005744 | −0.031163 | 0.071094 | 0.00366 | 0.022129 | 0.046655 | 0.008142 | 0.010722 | −0.096493 |
| 35 | 0.009878 | −0.015555 | 0.09957 | 0.026406 | −0.012363 | 0.002257 | 0.011935 | −0.111111 | 0.015509 | −0.051528 | −0.003794 | 0.022605 | −0.013027 | −0.072771 |
| 36 | −0.110923 | −0.008699 | 0.166879 | 0.012802 | 0.003574 | −0.003065 | −0.014717 | 0.039807 | −0.046963 | −0.021145 | −0.033278 | −0.005231 | −0.085355 | −0.038601 |
| 37 | 0.05915 | −0.005708 | 0.119441 | −0.031854 | −0.026899 | 0.002042 | −0.014409 | 0.008692 | −0.005317 | 0.074663 | 0.021467 | 0.093923 | 0.013843 | 0.102268 |
| 38 | 0.064373 | 0.013037 | 0.090532 | −0.043393 | −0.009368 | −0.058787 | 0.035118 | 0.017785 | 0.004384 | 0.014744 | −0.007583 | 0.097269 | −0.013588 | −0.00881 |
| 39 | 0.008093 | −0.030699 | −0.015429 | −0.038692 | −0.000436 | −0.040944 | −0.008022 | 0.006104 | −0.060368 | −0.098482 | 0.038771 | −0.103051 | 0.023512 | −0.004911 |
| 40 | −0.024168 | −0.003262 | −0.04536 | 0.017057 | −0.021179 | 0.046579 | −0.037617 | 0.055106 | 0.024375 | 0.079859 | −0.024038 | −0.031594 | −0.023482 | −0.041575 |
| 41 | 0.078315 | 0.012296 | 0.040113 | 0.044035 | 0.009408 | −0.083426 | 0.019124 | −0.18839 | −0.01221 | −0.146728 | 0.020876 | 0.043287 | −0.021324 | 0.027394 |
| 42 | 0.005285 | −0.000681 | −0.023767 | 0.000717 | 0.01522 | 0.031365 | 0.007819 | −0.047893 | −0.009194 | 0.0040091 | −0.004851 | 0.004581 | 0.0157481 | 0.001982 |
| 43 | −0.147429 | 0.008277 | 0.038863 | 0.032508 | −0.020767 | 0.020307 | −0.084484 | 0.022494 | 0.016335 | 0.000937 | −0.029496 | 0.069884 | −0.064327 | −0.043401 |
| 44 | −0.017188 | −0.018433 | −0.044634 | −0.026228 | 0.006554 | 0.083669 | −0.028512 | 0.028123 | −0.033876 | 0.051057 | −0.030441 | −0.080806 | 0.003262 | 0.026453 |
| 45 | 0.119186 | 0.062465 | 0.034578 | −0.001439 | −0.006473 | 0.079371 | 0.009825 | −0.119914 | −0.012369 | 0.020207 | −0.005062 | −0.134137 | 0.021181 | −0.000913 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 46 | 0.047167 | −0.014144 | −0.028913 | 0.008134 | 0.000108 | 0.084878 | −0.047806 | 0.010698 | −0.06355 | 0.029147 | −0.068155 | 0.153209 | −0.06572 | −0.033891 |
| 47 | 0.003615 | −0.014566 | −0.037067 | 0.003861 | −0.003584 | −0.023271 | −0.010811 | 0.005049 | 0.010071 | 0.061635 | −0.013452 | −0.015179 | −0.008337 | −0.056449 |
| 48 | 0.053401 | 0.012251 | −0.060531 | 0.039492 | −0.000604 | 0.01464 | −0.002152 | 0.02948 | −0.033827 | −0.01724 | −0.003007 | −0.139729 | −0.012733 | 0.044345 |
| 49 | −0.01991 | 0.00739 | 0.048526 | −0.009926 | −0.032349 | −0.082524 | 0.037259 | −0.045601 | −0.033624 | −0.101448 | 0.000398 | −0.089927 | −0.033822 | 0.030533 |
| 50 | −0.052797 | −0.034669 | 0.138086 | 0.005026 | 0.002933 | −0.031707 | 0.003472 | 0.008537 | 0.061407 | 0.108056 | 0.056598 | 0.027859 | 0.010246 | 0.015093 |
| 51 | 0.01809 | 0.02452 | −0.024117 | 0.014892 | −0.047337 | −0.006095 | −0.015592 | 0.069999 | 0.003519 | −0.09815 | −0.008159 | −0.003158 | −0.059938 | 0.01047 |
| 52 | −0.008437 | −0.058341 | −0.054319 | −0.015099 | −0.03489 | −0.005122 | −0.042603 | −0.218268 | 0.011861 | −0.04371 | −0.019103 | 0.078239 | −0.009012 | −0.006808 |
| 53 | 0.003525 | 0.04482 | −0.073828 | −0.015305 | −0.063964 | −0.028136 | 0.013122 | −0.068059 | 0.036199 | 0.092373 | −0.049972 | 0.124604 | −0.037583 | 0.058354 |
| 54 | −0.072714 | −0.014546 | 0.050688 | −0.007388 | −0.006291 | 0.005967 | 0.031717 | 0.039197 | 0.039875 | −0.034937 | −0.021165 | 0.062944 | 0.045138 | −0.013193 |
| 55 | 0.033327 | 0.116128 | 0.155077 | 0.080571 | 0.080334 | 0.099617 | −0.039397 | −0.071897 | −0.043944 | −0.027004 | 0.033827 | 0.043169 | 0.035577 | 0.042327 |
| 56 | 0.092752 | −0.022493 | −0.127615 | −0.001722 | 0.003879 | −0.02181 | −0.004299 | −0.020044 | −0.02304 | 0.052861 | −0.005639 | −0.030549 | −0.030519 | 0.026733 |
| 57 | 0.007752 | −0.024642 | −0.029247 | 0.007177 | 0.022284 | −0.047982 | 0.019415 | 0.012059 | −0.015584 | 0.034426 | −0.009793 | 0.050234 | 0.038423 | −0.030726 |
| 58 | −0.033632 | 0.036498 | 0.240998 | 0.013277 | 0.033764 | 0.076118 | −0.081177 | −0.075001 | −0.07202 | 0.062403 | −0.018327 | 0.036522 | 0.045044 | −0.010044 |
| 59 | 0.028887 | −0.007397 | 0.113584 | 0.016132 | 0.028561 | −0.014236 | 0.04496 | −0.103865 | 0.014919 | −0.05161 | −0.005666 | −0.024425 | 0.030001 | 0.065954 |
| 60 | 0.132739 | 0.001223 | −0.093296 | −0.00626 | −0.037411 | −0.0013 | 0.026988 | 0.05986 | −0.069378 | 0.003326 | −0.046397 | 0.008025 | −0.033516 | −0.056167 |
| 61 | 0.018453 | −0.006195 | 0.082265 | 0.022061 | 0.024121 | 0.001698 | 0.014479 | 0.132381 | 0.032699 | 0.071219 | 0.036486 | 0.041808 | 0.001852 | −0.046844 |
| 62 | −0.051682 | −0.05762 | 0.150947 | −0.031428 | 0.000794 | 0.006308 | −0.000527 | −0.09132 | −0.059196 | 0.078517 | −0.015887 | −0.03993 | 0.040227 | 0.030782 |
| 63 | −0.000271 | 0.077834 | −0.03897 | −0.02516 | −0.007624 | −0.016896 | 0.010232 | −0.020427 | 0.041726 | −0.060133 | −0.028654 | −0.023285 | 0.002299 | 0.024538 |
| 64 | 0.036017 | 0.024719 | −0.08675 | 0.013421 | 0.029243 | 0.065712 | −0.005039 | −0.049948 | 0.013807 | 0.146232 | 0.006325 | 0.155288 | 0.08194 | 0.081834 |
| 65 | 0.100858 | 0.021151 | −0.07076 | −0.011358 | −0.029666 | 0.040787 | −0.036511 | 0.050273 | 0.004602 | −0.016903 | −0.016389 | 0.107066 | −0.054899 | −0.104686 |
| 66 | −0.07297 | 0.031427 | −0.032627 | −0.004377 | −0.004862 | 0.02695 | −0.018481 | 0.018883 | −0.016748 | −0.014333 | −0.00322 | 0.082097 | −0.03707 | 0.023251 |
| 67 | −0.027354 | −0.02638 | −0.027284 | 0.01051 | 0.007307 | −0.053584 | −0.01165 | −0.075494 | 0.003745 | −0.064914 | 0.036582 | 0.030987 | 0.004851 | 0.09337 |
| 68 | −0.045003 | −0.040932 | 0.01308 | −0.018776 | −0.035917 | −0.090913 | −0.017124 | −0.030625 | −0.046588 | 0.063953 | −0.012774 | −0.019143 | −0.055033 | −0.026134 |
| 69 | 0.020384 | −0.001382 | −0.043434 | −0.005884 | −0.009597 | 0.025693 | 0.011649 | 0.024872 | −0.013036 | 0.074277 | 0.034135 | 0.112718 | 0.041947 | −0.008575 |
| 70 | −0.037277 | 0.100722 | 0.019406 | 0.020087 | −0.007939 | 0.072587 | −0.026384 | 0.033784 | 0.05818 | −0.024832 | 0.065338 | −0.041993 | 0.011358 | −0.015111 |
| 71 | 0.037975 | −0.048586 | 0.037445 | 0.001224 | −0.008385 | −0.045883 | 0.01744 | 0.068103 | 0.068879 | 0.084329 | 0.058047 | −0.049889 | −0.060194 | −0.027101 |
| 72 | 0.03053 | 0.018726 | −0.080559 | 0.064579 | 0.040026 | 0.07111 | 0.007797 | 0.059451 | −0.008368 | −0.01675 | −0.003782 | 0.068257 | −0.002423 | 0.003603 |
| 73 | −0.021228 | 0.024041 | −0.072711 | 0.053084 | 0.035671 | 0.027012 | −0.029794 | −0.061037 | 0.054467 | 0.065105 | 0.029813 | −0.052197 | 0.048399 | 0.069224 |
| 74 | −0.053877 | 0.033328 | 0.040216 | 0.013286 | −0.005445 | −0.009996 | 0.035508 | −0.09917 | 0.014647 | 0.018232 | −0.013036 | 0.003492 | 0.017047 | 0.009052 |
| 75 | −0.087753 | −0.008777 | 0.043731 | −0.006044 | 0.004196 | −0.00748 | −0.028119 | −0.084193 | 0.010738 | 0.058834 | −0.025286 | 0.096774 | 0.000665 | 0.045668 |
| 76 | 0.048963 | 0.00615 | 0.041555 | −0.037514 | 0.026996 | −0.02512 | 0.015687 | −0.037698 | −0.062897 | 0.020698 | 0.029196 | −0.140843 | −0.025175 | 0.003927 |
| 77 | 0.043622 | −0.070639 | 0.044284 | −0.025445 | −0.02521 | −0.029371 | −0.020483 | 0.042321 | −0.076287 | −0.086258 | −0.086549 | −0.009245 | 0.003747 | −0.058146 |
| 78 | 0.034292 | 0.013731 | −0.004789 | 0.033965 | 0.01652 | −0.0378 | 0.034081 | 0.112102 | 0.051934 | −0.030829 | 0.040656 | −0.013652 | 0.021727 | −0.027898 |
| 79 | 0.034266 | −0.033401 | 0.037912 | −0.002526 | −0.069836 | 0.010746 | −0.042801 | −0.030355 | −0.049327 | 0.034005 | −0.067007 | −0.097701 | −0.035985 | 0.111965 |
| 80 | 0.056878 | 0.052722 | −0.055234 | 0.639071 | 0.023435 | −0.011409 | 0.009347 | −0.067996 | 0.024584 | 0.039578 | 0.043896 | 0.122224 | 0.028707 | 0.009879 |
| 81 | −0.068932 | 0.010058 | 0.00779 | 0.001168 | −0.033693 | −0.006429 | −0.016042 | −0.041255 | 0.014273 | −0.028186 | −0.03779 | −0.071513 | −0.06831 | −0.039099 |
| 82 | 0.0325 | −0.022137 | −0.099759 | 0.074335 | 0.039833 | 0.040694 | −0.044897 | −0.080441 | 0.015498 | −0.037547 | 0.053688 | 0.008955 | 0.002781 | −0.001605 |
| 83 | 0.067256 | −0.082191 | 0.01156 | −0.047942 | −0.033168 | −0.057883 | 0.051573 | 0.124767 | 0.055935 | −0.065989 | 0.035839 | 0.063308 | −0.000371 | −0.019359 |
| 84 | −0.055984 | 0.053928 | 0.04906 | −0.00232 | −0.005259 | 0.013843 | 0.028287 | 0.065587 | 0.019538 | 0.061752 | 0.037706 | 0.060572 | 0.011859 | 0.0339 |
| 85 | −0.035543 | −0.052119 | 0.038214 | 0.018818 | −0.011703 | −0.060486 | 0.024862 | 0.001821 | −0.067367 | −0.013646 | −0.048636 | −0.098635 | −0.025588 | −0.005643 |
| 86 | 0.025214 | −0.035748 | 0.019388 | −0.058156 | −0.044098 | −0.030204 | −0.004755 | −0.016647 | −0.018575 | −0.104479 | 0.018661 | 0.015046 | −0.011321 | −0.040494 |
| 87 | 0.002553 | 0.039179 | 0.011055 | −0.026298 | −0.026178 | 0.02082 | −0.07851 | −0.017003 | −0.100622 | 0.013231 | −0.040784 | 0.050893 | −0.005548 | −0.019774 |
| 88 | −0.061259 | 0.002204 | −0.097952 | −0.057571 | −0.022956 | −0.051079 | 0.035201 | −0.036603 | −0.015548 | −0.06086 | −0.053853 | −0.013226 | 0.00618 | −0.089857 |
| 89 | 0.030803 | 0.056027 | 0.110542 | 0.07094 | 0.028475 | 0.070996 | −0.04177 | 0.113099 | 0.049424 | 0.041713 | 0.029385 | −0.127585 | 0.020325 | 0.077884 |
| 90 | 0.008815 | 0.026934 | −0.042534 | 0.01273 | 0.027784 | 0.065565 | 0.041569 | −0.071315 | −0.042148 | −0.062337 | 0.030471 | 0.029009 | 0.075167 | −0.013787 |
| 91 | −0.022204 | 0.029932 | 0.05462 | 0.024399 | −0.073167 | −0.040551 | −0.008487 | 0.078533 | −0.043547 | −0.041088 | −0.049786 | 0.017819 | −0.067497 | −0.016778 |
| 92 | 0.016387 | 0.000326 | 0.046863 | −0.016021 | 0.022774 | −0.009186 | −0.021147 | −0.073969 | 0.026867 | 0.046077 | 0.01826 | −0.009942 | 0.035812 | 0.072996 |
| 93 | −0.12582 | −0.050993 | −0.055599 | −0.024928 | 0.020957 | 0.001789 | 0.028926 | −0.001311 | 0.031849 | −0.000131 | −0.01574 | −0.043213 | 0.013064 | 0.013803 |
| 94 | −0.013606 | 0.106329 | −0.047262 | 0.095819 | 0.024629 | 0.01057 | 0.005001 | −0.056218 | −0.006008 | 0.05986 | −0.004838 | 0.044986 | −0.001392 | −0.031289 |
| 95 | −0.046174 | −0.067265 | −0.026939 | −0.036641 | 0.019915 | −0.076147 | 0.028946 | 0.000894 | 0.015253 | −0.021783 | 0.000895 | 0.141742 | −0.020334 | 0.012991 |
| 96 | 0.071561 | −0.041822 | 0.048083 | −0.056268 | −0.034482 | −0.028929 | 0.099862 | −0.018612 | 0.059668 | −0.040906 | −0.027627 | 0.069378 | 0.001551 | 0.004637 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 97 | 0.043332 | −0.100402 | −0.00388 | −0.205479 | −0.097479 | −0.146928 | 0.000629 | 0.022904 | −0.028522 | 0.131933 | −0.017244 | 0.058287 | −0.018018 | −0.005177 |
| 98 | −0.034042 | 0.015465 | 0.043751 | −0.099134 | 0.013211 | 0.001539 | 0.039232 | −0.020917 | 0.060335 | −0.016203 | −0.005305 | 0.115969 | 0.012086 | −0.092244 |
| 99 | −0.237151 | −0.040259 | 0.011625 | 0.031826 | 0.004607 | 0.048058 | 0.021414 | −0.045784 | −0.076913 | −0.124151 | −0.057305 | 0.017255 | −0.070073 | −0.017108 |
| 100 | −0.015377 | −0.000063 | 0.035525 | −0.002362 | −0.006911 | −0.006033 | −0.007613 | −0.00403 | −0.019948 | 0.005195 | 0.005738 | 0.021129 | −0.000781 | 0.015357 |
| 101 | 0.023476 | −0.026971 | −0.001841 | −0.028002 | −0.022498 | −0.007875 | 0.010863 | −0.003979 | −0.009472 | 0.018007 | −0.015061 | −0.000362 | −0.002483 | 0.001684 |
| 102 | −0.056915 | 0.045796 | 0.004731 | 0.014739 | 0.011241 | −0.003958 | −0.001541 | −0.020982 | −0.018418 | −0.021875 | −0.01267 | 0.033118 | −0.002355 | −0.015453 |
| 103 | 0.032682 | 0.048885 | −0.01462 | 0.047352 | −0.002905 | 0.042191 | −0.013494 | 0.018117 | −0.018011 | −0.013685 | 0.011578 | −0.019117 | −0.003608 | 0.000793 |
| 104 | −0.053422 | 0.036654 | 0.036905 | 0.025016 | 0.024403 | 0.036613 | 0.005604 | 0.011741 | 0.007339 | −0.027682 | −0.002883 | 0.041266 | 0.008508 | 0.013067 |
| 105 | −0.021969 | −0.002238 | −0.022229 | −0.038914 | −0.001635 | −0.001041 | −0.007339 | −0.021088 | −0.008999 | 0.016813 | 0.004053 | 0.029307 | 0.006133 | −0.022546 |
| 106 | 0.005801 | −0.018263 | −0.026963 | −0.006708 | 0.009671 | −0.027665 | 0.017459 | −0.075044 | 0.020003 | −0.061341 | 0.006086 | −0.005949 | −0.001158 | −0.004932 |
| 107 | −0.044543 | −0.032517 | −0.035459 | 0.023658 | −0.019512 | −0.024222 | −0.003043 | 0.032603 | −0.061979 | −0.038826 | −0.038876 | 0.069022 | −0.036761 | 0.015046 |
| 108 | 0.016075 | 0.018612 | −0.040654 | −0.004276 | −0.011811 | 0.015746 | 0.008689 | 0.00908 | −0.023142 | −0.040006 | 0.019939 | −0.072328 | 0.013917 | 0.012953 |
| 109 | −0.039029 | 0.03567 | 0.029389 | 0.010677 | 0.013403 | 0.006818 | 0.001897 | −0.03247 | 0.031354 | 0.00154 | 0.007962 | 0.07321 | −0.01426 | 0.000854 |
| 110 | −0.047328 | 0.03906 | 0.030999 | 0.01664 | −0.007166 | 0.03017 | −0.001712 | −0.073059 | 0.005817 | −0.036832 | −0.020012 | −0.025587 | 0.006813 | −0.03735 |
| 111 | −0.025217 | −0.027837 | 0.062261 | 0.028372 | 0.026135 | 0.004421 | −0.038522 | −0.02753 | −0.001175 | 0.023546 | 0.019074 | 0.002259 | 0.016357 | 0.002991 |
| 112 | 0.009711 | 0.026651 | −0.009053 | −0.028902 | 0.003722 | 0.026268 | 0.029397 | −0.009146 | 0.003061 | −0.047932 | 0.00374 | −0.032041 | −0.006824 | −0.031918 |
| 113 | −0.021302 | −0.017811 | 0.070014 | 0.021915 | 0.008132 | 0.003805 | −0.017398 | 0.033946 | −0.009835 | −0.005202 | 0.001971 | 0.032277 | −0.000623 | 0.015962 |
| 114 | 0.003461 | 0.013527 | 0.00682 | 0.013606 | 0.029077 | 0.023062 | −0.027227 | 0.093782 | −0.015298 | −0.00837 | 0.031254 | 0.065491 | 0.016617 | 0.044174 |
| 115 | −0.033757 | −0.011133 | −0.070129 | −0.046338 | −0.049331 | −0.040544 | 0.043422 | 0.050635 | 0.009342 | 0.040053 | −0.025504 | 0.005849 | −0.041455 | −0.022791 |
| 116 | 0.020729 | −0.046701 | −0.04456 | −0.019046 | 0.019171 | −0.033856 | −0.027409 | −0.036286 | 0.008075 | 0.030095 | 0.012773 | −0.000618 | −0.005183 | −0.023886 |
| 117 | −0.017693 | −0.004332 | 0.047271 | 0.025459 | 0.003679 | 0.003328 | 0.010502 | −0.003342 | −0.006852 | 0.001105 | −0.009879 | −0.031465 | −0.010407 | 0.027208 |
| 118 | −0.058975 | 0.00892 | 0.010646 | 0.024445 | 0.025968 | −0.044476 | 0.01287 | −0.009222 | 0.008055 | −0.052283 | −0.00656 | 0.003767 | 0.008063 | 0.00759 |
| 119 | 0.005655 | 0.01994 | −0.01509 | −0.005804 | −0.019311 | 0.003863 | −0.030519 | −0.011004 | −0.027997 | 0.005948 | −0.001921 | −0.016046 | −0.024271 | −0.003264 |
| 120 | −0.009428 | −0.014355 | −0.036427 | −0.004645 | −0.010974 | 0.015522 | −0.02335 | −0.019559 | −0.043867 | 0.006562 | −0.035716 | −0.021076 | −0.015679 | −0.000262 |
| 121 | −0.018157 | −0.006751 | −0.004228 | −0.011443 | −0.011823 | 0.018523 | −0.035425 | 0.049013 | −0.015215 | 0.035977 | −0.027854 | −0.049982 | −0.016481 | −0.026674 |
| 122 | 0.025174 | −0.000189 | −0.077776 | 0.010112 | 0.013694 | −0.012046 | 0.010956 | 0.016526 | 0.046017 | 0.037805 | −0.007048 | 0.015325 | 0.005881 | −0.008755 |
| 123 | 0.010325 | −0.0071 | −0.064119 | 0.023501 | −0.004728 | 0.01267 | −0.017177 | 0.036063 | 0.017584 | 0.019726 | −0.002878 | −0.007501 | −0.015687 | −0.013122 |
| 124 | −0.032777 | −0.007973 | −0.013947 | −0.023409 | −0.011813 | −0.008204 | 0.00147 | −0.020114 | −0.015517 | −0.030986 | −0.00903 | 0.001794 | −0.003261 | −0.014805 |
| 125 | −0.004268 | −0.011462 | 0.014213 | −0.025048 | 0.000455 | −0.032884 | 0.023616 | −0.01907 | 0.003494 | −0.047177 | −0.000562 | 0.005576 | −0.016139 | −0.028518 |
| 126 | 0.013599 | −0.0228761 | −0.044689 | 0.008873 | 0.018109 | 0.012699 | 0.01185 | 0.0233 | 0.016805 | −0.012875 | −0.004697 | −0.001619 | 0.018172 | −0.03218 |
| 127 | 0.018394 | −0.026352 | −0.034176 | 0.007147 | 0.011171 | 0.002792 | 0.01359 | 0.038213 | 0.004345 | −0.012788 | −0.008328 | −0.028159 | 0.009128 | −0.00443 |
| 128 | −0.010124 | 0.007821 | 0.034051 | −0.014358 | −0.014965 | −0.017141 | 0.013652 | 0.037525 | −0.000822 | −0.007684 | 0.001369 | −0.001924 | −0.016107 | 0.016544 |
| 129 | 0.001481 | 0.034747 | 0.061588 | 0.051124 | −0.001197 | −0.000518 | −0.058717 | 0.013314 | −0.019365 | −0.049126 | −0.013354 | 0.060507 | −0.017918 | −0.012531 |
| 130 | 0.058039 | 0.031343 | 0.000583 | −0.017527 | −0.029141 | 0.043774 | −0.001602 | −0.042108 | −0.005314 | −0.050204 | −0.022766 | 0.02171 | −0.023324 | −0.033373 |
| 131 | −0.012941 | 0.0106431 | −0.058974 | 0.056709 | 0.025605 | 0.026993 | −0.020014 | −0.039543 | −0.029315 | −0.025739 | −0.004235 | 0.074437 | 0.023004 | 0.044756 |
| 132 | −0.039381 | −0.00017 | 0.047385 | −0.003035 | −0.002097 | −0.009441 | 0.011174 | −0.024922 | −0.02011 | −0.09518 | −0.001337 | −0.081225 | −0.015789 | −0.034829 |
| 133 | 0.009886 | −0.060606 | 0.013309 | −0.076444 | −0.036725 | −0.080296 | 0.038801 | 0.022003 | −0.0212 | −0.022501 | −0.002411 | −0.046563 | −0.001223 | 0.026746 |
| 134 | 0.048535 | −0.031973 | −0.018467 | −0.039075 | −0.007199 | −0.01539 | −0.018621 | 0.007217 | 0.015339 | 0.039091 | 0.019344 | 0.00558 | 0.02892 | 0.017068 |
| 135 | 0.01697 | −0.011709 | 0.028514 | −0.024383 | −0.013343 | −0.009283 | 0.017357 | −0.048787 | −0.0197 | −0.021924 | 0.005728 | −0.029095 | −0.002791 | 0.01231 |
| 136 | 0.006577 | 0.019993 | 0.069904 | −0.037811 | −0.011908 | −0.012627 | 0.019138 | 0.01604 | −0.019153 | −0.032409 | 0.002981 | −0.066012 | −0.002971 | −0.030341 |
| 137 | −0.005814 | −0.018888 | 0.01409 | 0.031849 | 0.002878 | 0.003678 | −0.023186 | −0.039164 | −0.015501 | −0.012115 | −0.000523 | −0.033424 | −0.019073 | 0.049832 |
| 138 | 0.068785 | −0.017649 | 0.015496 | −0.014887 | −0.012712 | −0.004199 | −0.006105 | 0.057753 | 0.001263 | 0.032152 | −0.011509 | −0.083071 | −0.020192 | −0.071381 |
| 139 | 0.013582 | −0.0321951 | −0.065706 | −0.068676 | −0.056706 | −0.00953 | −0.019678 | −0.055014 | −0.00966 | 0.007321 | −0.032068 | 0.053837 | −0.000303 | −0.029365 |
| 140 | 0.057823 | 0.01504 | 0.00519 | 0.02563 | 0.016128 | −0.021049 | 0.032315 | 0.013341 | −0.003753 | −0.071101 | 0.0348811 | −0.050661 | −0.003738 | 0.005849 |
| 141 | 0.032951 | −0.007478 | −0.059843 | −0.006009 | −0.013579 | −0.019872 | 0.015335 | −0.020875 | 0.038806 | 0.000576 | 0.027664 | 0.021665 | −0.02633 | −0.063494 |
| 142 | 0.009982 | −0.008288 | −0.043313 | −0.003526 | 0.002837 | 0.008543 | −0.009006 | −0.011363 | 0.062311 | 0.040769 | 0.008869 | 0.046226 | −0.011084 | 0.003027 |
| 143 | −0.008908 | −0.016088 | −0.028407 | −0.036865 | −0.016911 | −0.010882 | −0.009318 | −0.027701 | −0.023385 | 0.053022 | −0.02894 | 0.049387 | 0.022431 | 0.031782 |
| 144 | −0.004316 | 0.001363 | −0.016265 | −0.010761 | −0.00489 | 0.022353 | −0.024385 | −0.00753 | −0.01026 | 0.035937 | −0.004066 | 0.022503 | 0.006281 | 0.005481 |
| 145 | 0.019968 | −0.0334541 | −0.014165 | −0.031013 | −0.015668 | 0.014453 | 0.005774 | 0.046158 | −0.047559 | 0.0206921 | −0.023884 | 0.009428 | 0.027623 | 0.018811 |
| 146 | 0.040109 | −0.0565 | −0.01252 | −0.065309 | −0.02472 | −0.035623 | 0.018686 | −0.006411 | −0.02398 | −0.017298 | −0.003415 | −0.002192 | −0.008181 | −0.015717 |
| 147 | 0.012866 | −0.089923 | 0.016812 | −0.054925 | −0.018523 | −0.052221 | 0.001058 | −0.047289 | −0.00405 | −0.04977 | 0.001628 | 0.08024 | −0.010001 | −0.039386 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 148 | 0.0001 | −0.013117 | 0.05111 | 0.000465 | −0.021106 | −0.017833 | 0.006722 | −0.040196 | −0.023627 | −0.053876 | −0.037206 | −0.063044 | 0.013205 | 0.030513 |
| 149 | −0.01158 | 0.009374 | 0.000497 | 0.022539 | 0.009936 | 0.020779 | 0.021811 | 0.043892 | 0.05042 | 0.073408 | −0.003628 | 0.007536 | 0.013088 | 0.039061 |
| 150 | −0.005479 | 0.034897 | −0.023529 | 0.024985 | 0.007473 | 0.028493 | −0.030613 | −0.045112 | −0.01435 | −0.025794 | −0.02939 | −0.023274 | 0.000937 | −0.025139 |
| 151 | −0.010477 | −0.0001 | −0.022791 | 0.02052 | −0.010946 | 0.028017 | −0.029005 | −0.051895 | −0.012635 | −0.020887 | −0.026844 | 0.029847 | 0.004415 | 0.034061 |
| 152 | −0.016814 | −0.037787 | 0.009392 | −0.035421 | −0.03271 | −0.02111 | −0.007033 | 0.043813 | −0.002479 | 0.000233 | −0.021166 | −0.016385 | −0.027472 | −0.012152 |
| 153 | −0.034637 | −0.017762 | −0.045545 | −0.019089 | −0.042217 | −0.024614 | −0.029931 | 0.023113 | −0.004469 | 0.019975 | −0.012873 | −0.008722 | −0.032763 | −0.058334 |
| 154 | −0.024319 | −0.00847 | 0.002435 | −0.019023 | 0.002292 | 0.017933 | 0.004821 | −0.043452 | 0.016234 | 0.028837 | −0.017037 | 0.04176 | 0.026884 | −0.010255 |
| 155 | −0.015333 | 0.00214 | −0.002826 | 0.0005 | 0.011475 | 0.00104 | −0.015082 | 0.009808 | −0.000284 | −0.038499 | 0.009832 | −0.015841 | 0.006628 | −0.020037 |
| 156 | −0.010205 | 0.003713 | −0.0760551 | 0.005118 | −0.016157 | −0.002166 | 0.046875 | −0.007526 | 0.021983 | −0.014676 | 0.005696 | 0.091137 | −0.002848 | 0.024398 |
| 157 | −0.003893 | 0.006876 | 0.051149 | 0.017462 | 0.010537 | 0.024526 | −0.014402 | 0.003276 | −0.003002 | −0.032984 | 0.014544 | 0.01463 | −0.019253 | −0.026407 |
| 158 | −0.015901 | −0.002454 | −0.044569 | 0.005237 | 0.013307 | 0.003314 | −0.007075 | −0.053055 | 0.039294 | 0.082077 | 0.008546 | −0.035491 | 0.013066 | 0.023659 |
| 159 | −0.024524 | −0.031054 | −0.002625 | 0.035039 | −0.008961 | −0.010364 | −0.047818 | −0.006389 | 0.012741 | 0.000531 | 0.00177 | −0.069553 | −0.011514 | 0.000993 |
| 160 | −0.042591 | 0.010059 | −0.005381 | −0.029787 | −0.012928 | −0.033197 | 0.037082 | −0.010486 | 0.045202 | 0.005245 | 0.0256211 | 0.032163 | −0.011726 | 0.01567 |
| 161 | 0.010458 | 0.03744 | 0.036686 | 0.035986 | 0.002787 | 0.031769 | −0.043751 | −0.038401 | 0.020586 | 0.046745 | 0.000132 | −0.026881 | −0.006493 | 0.021642 |
| 162 | 0.013467 | 0.02303 | −0.011677 | 0.021705 | 0.013157 | 0.030509 | −0.00712 | −0.01137 | 0.007726 | −0.034802 | 0.015505 | −0.008572 | 0.011474 | 0.035683 |
| 163 | −0.001295 | 0.016362 | 0.012773 | 0.046353 | 0.019493 | 0.041077 | 0.020428 | −0.005229 | 0.045323 | 0.027492 | 0.029619 | −0.008131 | 0.024707 | 0.056562 |
| 164 | 0.001846 | −0.059831 | 0.00733 | −0.013283 | −0.001042 | −0.04582 | 0.030674 | 0.039609 | −0.002598 | −0.006276 | −0.016426 | 0.035306 | 0.00941 | 0.035562 |
| 165 | 0.0216 | 0.019836 | 0.046085 | 0.024019 | 0.022304 | 0.031279 | −0.011356 | −0.018632 | −0.004205 | 0.029522 | 0.004507 | −0.068337 | 0.050676 | 0.051311 |
| 166 | 0.06088 | 0.026967 | −0.003894 | −0.004904 | −0.00747 | 0.001916 | 0.021183 | −0.062035 | 0.00616 | −0.072432 | −0.00402 | 0.00345 | −0.014797 | −0.042096 |
| 167 | −0.015296 | −0.028202 | −0.057425 | −0.007008 | 0.024827 | 0.016434 | −0.002188 | 0.010421 | −0.035894 | 0.02405 | 0.01675 | −0.077597 | −0.00201 | −0.020896 |
| 168 | −0.025831 | 0.0225 | −0.019365 | 0.016695 | 0.01536 | 0.032741 | 0.010977 | −0.028841 | −0.002669 | 0.033426 | −0.019599 | −0.007621 | 0.022081 | 0.045122 |
| 169 | 0.015217 | −0.021477 | 0.00552 | 0.010656 | 0.003309 | −0.00291 | 0.001174 | −0.016181 | 0.011019 | −0.004866 | −0.001865 | −0.015561 | 0.015968 | 0.017488 |
| 170 | −0.018122 | −0.023518 | 0.008138 | 0.001294 | −0.014147 | −0.017601 | 0.010351 | 0.006108 | 0.020467 | 0.002748 | −0.018362 | −0.017578 | 0.000335 | 0.012429 |
| 171 | 0.010959 | −0.012198 | −0.020102 | 0.013291 | −0.000634 | 0.000308 | −0.008349 | 0.009963 | 0.018604 | 0.019907 | 0.00956 | 0.005461 | 0.005125 | 0.007919 |
| 172 | −0.021936 | 0.007906 | −0.018751 | 0.008162 | 0.00761 | 0.004386 | −0.021305 | −0.013538 | 0.003623 | −0.028288 | 0.014511 | 0.008412 | 0.006569 | 0.003694 |
| 173 | 0.009011 | 0.002953 | −0.003407 | −0.002785 | −0.010859 | −0.0169 | −0.00245 | 0.029392 | 0.026544 | 0.023914 | 0.0249 | 0.01557 | −0.017788 | 0.025482 |
| 174 | 0.00068 | −0.024724 | −0.000514 | −0.017901 | −0.004777 | −0.018098 | 0.008333 | −0.064296 | 0.010253 | 0.00632 | −0.001279 | 0.011079 | −0.010715 | 0.021247 |
| 175 | −0.035868 | −0.008896 | 0.02129 | −0.007769 | −0.006592 | 0.009333 | −0.022624 | −0.034654 | 0.018015 | 0.001923 | −0.009375 | 0.059478 | 0.002069 | 0.031188 |
| 176 | −0.026747 | −0.01797 | 0.000496 | 0.021437 | 0.002388 | 0.010004 | −0.010794 | −0.005566 | −0.021971 | −0.028889 | −0.028103 | −0.027576 | 0.001559 | −0.024799 |
| 177 | 0.0255 | −0.041929 | −0.017556 | −0.010273 | 0.013931 | −0.054232 | 0.082161 | −0.053041 | 0.000231 | 0.061547 | −0.004348 | 0.016359 | 0.063143 | 0.006734 |
| 178 | −0.010145 | −0.032309 | −0.034429 | −0.017026 | −0.004997 | 0.008125 | −0.021028 | −0.049223 | −0.016359 | −0.003246 | −0.003298 | 0.041242 | 0.014787 | −0.001032 |
| 179 | −0.003542 | −0.02002 | −0.004243 | 0.007992 | 0.003925 | −0.012542 | −0.014474 | −0.019416 | −0.0156 | 0.016364 | −0.003705 | −0.003036 | −0.008195 | 0.00905 |
| 180 | 0.006821 | −0.012158 | −0.014812 | −0.004662 | −0.01081 | −0.027732 | −0.003847 | 0.004653 | 0.013606 | −0.000121 | 0.004197 | 0.00023 | −0.017844 | −0.012092 |
| 181 | −0.00976 | −0.01604 | −0.006856 | −0.012279 | −0.008403 | −0.020713 | 0.003474 | −0.021953 | 0.003609 | 0.002898 | 0.001664 | −0.008525 | −0.015344 | −0.011197 |
| 182 | −0.0509981 | −0.007703 | −0.00121 | −0.013979 | −0.022781 | −0.036828 | 0.006035 | 0.004406 | 0.009214 | 0.006936 | −0.021042 | 0.004655 | −0.018112 | −0.007568 |
| 183 | −0.002207 | −0.001377 | 0.042236 | 0.013837 | −0.000286 | −0.030209 | −0.019118 | 0.024603 | −0.020965 | 0.046209 | 0.004972 | 0.017805 | −0.003145 | −0.002066 |
| 184 | 0.079582 | 0.04205 | 0.025316 | 0.024471 | 0.008784 | 0.018251 | −0.009556 | 0.017944 | 0.00992 | 0.053146 | 0.039868 | 0.013643 | 0.018815 | 0.021904 |
| 185 | −0.011871 | 0.023773 | −0.008243 | 0.043186 | −0.011418 | 0.005495 | −0.006594 | −0.047921 | 0.023305 | −0.047294 | −0.007407 | 0.008066 | −0.026146 | −0.020493 |
| 186 | 0.007104 | 0.027906 | −0.0102141 | −0.015976 | −0.024005 | 0.001951 | −0.001511 | −0.010293 | 0.0278281 | −0.016219 | 0.0012621 | 0.0072631 | −0.013797 | −0.013035 |
| 187 | 0.034402 | 0.034276 | 0.010335 | −0.010578 | 0.001152 | −0.027663 | 0.012698 | 0.028061 | 0.00984 | 0.012897 | 0.008687 | −0.009595 | 0.004382 | −0.001792 |
| 188 | 0.027985 | 0.030158 | −0.012522 | 0.003236 | −0.00005 | −0.015729 | 0.010992 | −0.028707 | −0.004517 | −0.008532 | −0.000336 | 0.008111 | 0.000378 | −0.012 |
| 189 | 0.019137 | 0.009301 | 0.017165 | 0.017029 | −0.001343 | 0.013448 | 0.005335 | −0.058455 | −0.021074 | 0.003742 | −0.021987 | −0.006853 | −0.003134 | −0.019438 |
| 190 | −0.010738 | −0.022977 | −0.010129 | −0.000995 | −0.017238 | −0.017966 | −0.023726 | 0.046297 | 0.007456 | 0.01335 | −0.013552 | −0.02234 | −0.016097 | −0.012786 |
| 191 | −0.015739 | 0.002141 | −0.002773 | −0.003767 | 0.00958 | −0.012367 | 0.020802 | −0.018633 | 0.012801 | 0.010146 | 0.004266 | −0.020763 | −0.011125 | 0.000869 |
| 192 | −0.009313 | 0.014264 | −0.05862 | −0.030401 | 0.01279 | −0.00226 | 0.025306 | −0.011123 | −0.01381 | −0.002331 | −0.013323 | 0.064431 | 0.022726 | −0.01348 |
| 193 | −0.051181 | −0.000108 | −0.007102 | −0.008768 | −0.009882 | −0.018436 | 0.001997 | 0.03889 | 0.003402 | 0.000106 | 0.002145 | 0.063131 | −0.021432 | 0.022717 |
| 194 | 0.024488 | 0.003108 | −0.02618 | 0.027909 | −0.016196 | −0.01013 | −0.028651 | 0.008128 | −0.009826 | 0.002857 | −0.024711 | −0.0212 | −0.029708 | −0.018946 |
| 195 | −0.037539 | −0.018442 | 0.01925 | 0.011045 | 0.020639 | 0.005482 | −0.008775 | 0.001305 | 0.012845 | 0.017914 | 0.007787 | −0.026423 | −0.00868 | 0.01601 |
| 196 | −0.000757 | −0.006773 | −0.027217 | −0.016715 | 0.015423 | 0.019337 | −0.004321 | 0.006586 | 0.031083 | 0.022363 | 0.009899 | −0.011934 | 0.021536 | 0.007825 |
| 197 | −0.035776 | −0.023977 | −0.034382 | −0.01116 | −0.009132 | −0.008486 | 0.004445 | 0.041988 | 0.000694 | 0.028799 | −0.009485 | −0.040415 | −0.004332 | 0.021575 |
| 198 | −0.003607 | 0.009969 | 0.003169 | 0.008182 | 0.007318 | 0.029209 | −0.021122 | −0.01217 | 0.013318 | 0.008463 | 0.012989 | −0.014922 | 0.02286 | −0.016791 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 199 | 0.062103 | −0.05734 | −0.041185 | −0.001422 | 0.011298 | −0.025543 | 0.021516 | 0.030334 | 0.051285 | 0.087249 | 0.00389 | 0.126035 | 0.009856 | 0.030295 |
| 200 | −0.039659 | 0.007057 | 0.033606 | 0.000063 | 0.009501 | −0.025107 | −0.019029 | −0.008734 | −0.026422 | −0.037622 | 0.026735 | −0.015939 | 0.00829 | 0.000357 |
| 201 | 0.002912 | −0.010483 | 0.02072 | 0.012067 | −0.010771 | −0.041062 | −0.013464 | 0.038011 | −0.039032 | −0.051356 | −0.031252 | 0.019793 | −0.019288 | −0.034023 |
| 202 | −0.060266 | −0.016024 | −0.041386 | −0.04189 | −0.030466 | 0.027658 | 0.003635 | 0.029821 | −0.01261 | −0.051657 | −0.01462 | 0.017094 | −0.006242 | 0.003286 |
| 203 | −0.030936 | −0.042129 | 0.001985 | 0.013365 | 0.014535 | −0.035184 | −0.045499 | −0.02166 | −0.012186 | 0.064447 | −0.017118 | 0.006251 | 0.0298 | 0.019602 |
| 204 | 0.004308 | −0.035752 | 0.028442 | −0.020916 | −0.010874 | −0.015889 | −0.023693 | −0.013486 | −0.014313 | −0.080568 | −0.007017 | −0.008859 | −0.001615 | −0.032801 |
| 205 | −0.008268 | 0.0036 | −0.070428 | 0.052053 | 0.037829 | 0.025517 | −0.006087 | 0.034083 | 0.035284 | 0.033085 | −0.001516 | 0.001231 | −0.02261 | −0.036048 |
| 206 | −0.067531 | −0.000686 | −0.050876 | 0.000883 | −0.006335 | 0.000473 | −0.00461 | 0.048908 | 0.019014 | 0.045727 | 0.024432 | 0.021015 | 0.004309 | −0.010789 |
| 207 | −0.026629 | −0.032789 | 0.037643 | −0.010106 | 0.016852 | −0.030608 | 0.026488 | −0.00286 | 0.056351 | −0.019533 | 0.058968 | 0.007965 | 0.020319 | 0.011478 |
| 208 | −0.05553 | 0.00738 | 0.014941 | 0.022274 | −0.02074 | −0.01657 | 0.004001 | 0.016817 | −0.015631 | −0.013612 | 0.00045 | −0.03683 | −0.015051 | −0.008683 |
| 209 | −0.00181 | 0.005696 | 0.018492 | 0.005658 | −0.008431 | −0.00899 | −0.003489 | −0.054766 | 0.023971 | −0.079253 | 0.026594 | 0.007161 | 0.006568 | −0.018542 |
| 210 | 0.027897 | 0.010109 | 0.047589 | −0.00181 | 0.016563 | 0.025022 | 0.006134 | 0.040891 | 0.017612 | −0.058587 | −0.00118 | 0.029608 | 0.024658 | 0.004007 |
| 211 | 0.085396 | 0.047289 | −0.047694 | 0.02468 | 0.005182 | 0.010669 | −0.005165 | 0.045866 | −0.051841 | −0.050464 | −0.004225 | 0.092173 | 0.003721 | −0.001501 |
| 212 | 0.003579 | 0.029329 | 0.038194 | −0.000621 | −0.013747 | −0.013365 | −0.014252 | −0.043408 | −0.003491 | −0.006646 | 0.017267 | −0.009287 | −0.008129 | −0.010221 |
| 213 | 0.014794 | 0.002564 | −0.085327 | −0.011474 | −0.008395 | −0.027343 | −0.000158 | −0.044438 | 0.021553 | 0.004355 | 0.001215 | 0.006224 | −0.022319 | −0.004971 |
| 214 | 0.034691 | 0.001587 | −0.004875 | 0.006369 | 0.001702 | −0.004819 | 0.006303 | 0.008531 | −0.008759 | −0.002243 | 0.006601 | 0.002819 | 0.001429 | −0.011249 |
| 215 | 0.000266 | 0.006282 | 0.09697 | 0.024332 | 0.01175 | −0.01902 | −0.005746 | −0.027322 | 0.015897 | −0.002745 | 0.034368 | 0.016328 | 0.001785 | 0.038242 |
| 216 | 0.009435 | −0.016115 | 0.001352 | −0.022415 | −0.002273 | 0.017259 | 0.033265 | 0.011953 | 0.035486 | 0.029203 | 0.01474 | −0.008118 | 0.007353 | 0.021565 |
| 217 | −0.000199 | −0.014003 | 0.056857 | −0.01049 | −0.000015 | −0.035672 | 0.007005 | 0.012868 | 0.001194 | −0.001914 | −0.018557 | 0.030802 | 0.011931 | −0.015503 |
| 218 | −0.007001 | −0.021105 | 0.008225 | −0.025018 | −0.0237 | −0.018507 | 0.010593 | −0.000499 | 0.00466 | −0.011725 | −0.003451 | 0.006779 | −0.008035 | 0.021153 |
| 219 | 0.021464 | −0.017614 | 0.030278 | −0.036179 | −0.013122 | −0.007114 | 0.027608 | −0.007464 | 0.016717 | 0.032499 | 0.013846 | 0.034304 | 0.009702 | 0.00418 |
| 220 | 0.024988 | −0.020435 | 0.028151 | −0.022955 | −0.003991 | −0.069489 | 0.030963 | −0.054619 | −0.009296 | −0.02504 | −0.003845 | −0.002958 | −0.002704 | 0.002686 |
| 221 | −0.025882 | −0.012734 | 0.02177 | −0.007341 | 0.000488 | 0.009329 | 0.005608 | 0.018149 | 0.010963 | 0.028157 | 0.011023 | −0.025132 | 0.003369 | −0.008963 |
| 222 | 0.002619 | 0.003197 | 0.003398 | −0.022281 | 0.003102 | 0.001955 | 0.003438 | −0.032033 | −0.008676 | 0.025831 | 0.019236 | 0.020234 | 0.014562 | −0.016571 |
| 223 | −0.021079 | −0.014331 | −0.018872 | −0.012333 | −0.004854 | −0.004689 | 0.00824 | −0.029069 | −0.005932 | −0.024978 | −0.010087 | 0.030723 | −0.01706 | −0.036531 |
| 224 | −0.00035 | −0.021099 | −0.034647 | −0.016461 | 0.009991 | −0.000821 | 0.031604 | −0.02079 | −0.003991 | −0.017883 | −0.019912 | −0.007909 | 0.004755 | 0.005085 |
| 225 | 0.022646 | −0.011864 | 0.009463 | −0.002773 | 0.017122 | 0.003875 | 0.014396 | 0.004417 | −0.002049 | 0.024914 | −0.013605 | −0.017719 | 0.014771 | 0.012005 |
| 226 | 0.005223 | 0.026493 | 0.013887 | 0.007668 | −0.00785 | 0.014885 | −0.016413 | −0.028809 | −0.005153 | 0.016377 | −0.011331 | 0.026437 | 0.01383 | −0.018758 |
| 227 | −0.036887 | 0.013225 | 0.024999 | 0.034831 | −0.002714 | −0.007847 | −0.01782 | 0.014062 | −0.019503 | −0.027737 | −0.015341 | −0.012198 | 0.006395 | −0.003396 |
| 228 | −0.053881 | 0.033662 | −0.028011 | −0.012906 | −0.01212 | 0.026784 | −0.005208 | 0.006929 | −0.013702 | −0.004053 | −0.041208 | −0.018671 | −0.000406 | −0.026612 |
| 229 | −0.01683 | 0.045622 | 0.040203 | 0.019512 | 0.033936 | 0.051814 | −0.021587 | −0.045835 | −0.001929 | 0.029433 | 0.013541 | −0.023278 | 0.015462 | 0.030078 |
| 230 | −0.0287491 | 0.0002961 | −0.01156 | 0.00014 | 0.007344 | 0.021316 | −0.010821 | −0.034577 | −0.007956 | −0.014578 | 0.017077 | 0.00696 | −0.007465 | 0.017809 |
| 231 | 0.007444 | −0.007344 | −0.014837 | 0.018588 | −0.020094 | −0.042399 | 0.025596 | −0.004324 | 0.036877 | −0.042519 | 0.006153k | 0.033438 | −0.013535 | 0.002166 |
| 232 | −0.025917 | −0.003084 | −0.023706 | −0.034157 | 0.000417 | −0.018129 | 0.002525 | −0.042977 | −0.005298 | 0.028484 | −0.015353 | 0.025332 | 0.003511 | −0.025682 |
| 233 | −0.0163661 | 0.014897 | −0.011376 | 0.001029 | 0.020164 | 0.026308 | −0.008011 | −0.042638 | −0.00991 | 0.008948 | −0.004497 | 0.000875 | 0.036374 | −0.00167 |
| 234 | −0.004756 | 0.007404 | −0.019438 | −0.007121 | −0.004097 | 0.006062 | 0.007173 | −0.030303 | −0.003834 | −0.031429 | −0.011897 | −0.015861 | −0.000336 | 0.014964 |
| 235 | 0.017671 | −0.002842 | −0.025573 | 0.02157 | 0.004374 | −0.024559 | 0.015677 | −0.014115 | −0.004607 | −0.008225 | 0.013844 | 0.012355 | −0.013455 | 0.014367 |
| 236 | −0.018177 | −0.006264 | 0.023861 | −0.000302 | −0.005916 | −0.007004 | −0.00273 | 0.027413 | 0.009941 | −0.012537 | −0.000389 | 0.012431 | −0.008148 | −0.021148 |
| 237 | 0.030445 | −0.002547 | 0.019872 | 0.003877 | 0.006918 | 0.021006 | 0.01029 | 0.018551 | −0.004612 | −0.02169 | −0.012073 | −0.016771 | 0.016783 | −0.024575 |
| 238 | 0.015568 | −0.018484 | −0.013389 | −0.020179 | 0.00051 | 0.006335 | 0.032789 | 0.022246 | −0.007199 | −0.003175 | −0.000677 | 0.025968 | 0.018656 | 0.003172 |
| 239 | 0.003776 | −0.012684 | 0.009305 | −0.012819 | 0.006905 | 0.007262 | 0.014229 | 0.02263 | 0.007313 | 0.015593 | 0.011013 | 0.043327 | 0.022025 | 0.016416 |
| 240 | 0.003014 | −0.023249 | −0.029371 | 0.008616 | −0.003122 | 0.010188 | −0.007218 | 0.018612 | 0.034815 | −0.004166 | 0.000942 , | 0.015848 | 0.007797 | 0.007494 |
| 241 | −0.004343 | −0.010504 | −0.00769 | −0.007019 | 0.015007 | 0.015728 | 0.005355 | −0.034503 | −0.005421 | −0.039038 | −0.024874 | −0.022521 | 0.041623 | 0.016672 |
| 242 | −0.009201 | −0.006292 | −0.00619 | −0.008126 | −0.014743 | −0.021686 | −0.008157 | −0.031431 | −0.012491 | −0.012298 | 0.000255 | 0.00054 | −0.016417 | 0.005591 |
| 243 | 0.014693 | −0.014317 | −0.023902 | 0.00888 | −0.009083 | 0.004782 | 0.000213 | 0.004932 | 0.00191 | 0.003096 | 0.003481 | −0.002874 | 0.001053 | 0.021589 |
| 244 | −0.006358 | 0.006279 | −0.004969 | 0.012394 | 0.010216 | −0.006061 | −0.018364 | 0.025723 | −0.002535 | 0.02306 | 0.009708 | −0.031768 | 0.004169 | 0.003167 |
| 245 | −0.0263351 | −0.0008851 | −0.029842 | 0.011595 | 0.018365 | −0.003989 | 0.009238 | −0.028366 | −0.000438 | −0.027171 | 0.007925 | 0.035713 | 0.00395 | 0.014366 |
| 246 | −0.007862 | −0.000357 | 0.044152 | −0.000813 | −0.005051 | −0.015267 | 0.01375 | −0.004696 | 0.011152 | −0.017116 | 0.000831 | 0.013636 | −0.009085 | 0.003238 |
| 247 | 0.020299 | 0.002492 | 0.01957 | 0.015355 | 0.002503 | 0.006669 | −0.009231 | −0.006754 | 0.002955 | −0.007116 | −0.002836 | 0.027894 | 0.002982 | −0.015258 |
| 248 | 0.028295 | 0.017396 | 0.023895 | 0.015595 | 0.000191 | 0.005773 | −0.006708 | −0.016275 | −0.009384 | −0.005485 | 0.009192 | 0.030676 | −0.006651 | −0.022014 |
| 249 | 0.014959 | 0.008376 | 0.011251 | −0.007333 | −0.026311 | −0.013366 | −0.001895 | 0.049243 | 0.014836 | −0.021338 | 0.013651 | 0.001106 | 0.00583 | −0.007031 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 250 | 0.006851 | −0.018107 | −0.028918 | −0.004296 | −0.008321 | −0.017773 | 0.009171 | 0.039426 | 0.034517 | 0.003013 | 0.002047 | 0.020495 | −0.002062 | −0.005542 |
| 251 | 0.007177 | −0.028281 | −0.001992 | −0.021077 | −0.002833 | −0.008064 | 0.002548 | 0.000065 | 0.022893 | 0.025929 | 0.006768 | 0.012722 | 0.006844 | 0.000623 |
| 252 | 0.014001 | −0.022931 | −0.023158 | −0.021905 | −0.002437 | −0.006934 | −0.019046 | −0.018516 | 0.008321 | 0.014731 | 0.009023 | 0.027216 | 0.005652 | 0.025492 |
| 253 | 0.029012 | 0.005268 | −0.048127 | −0.000231 | 0.016968 | 0.008852 | 0.006162 | −0.001663 | 0.002699 | −0.012283 | −0.005941 | −0.073301 | 0.015591 | 0.02127 |
| 254 | −0.024476 | 0.007034 | 0.018708 | 0.009487 | −0.003858 | 0.000053 | −0.001024 | 0.009759 | −0.007943 | −0.03761 | −0.010667 | −0.014359 | −0.016039 | −0.017161 |
| 255 | −0.01749f | 0.004974 | 0.009585 | 0.005969 | −0.005033 | 0.012117 | −0.003021 | −0.023249 | −0.001529 | 0.007047 | −0.003287 | −0.033627 | −0.004952 | 0.011364 |
| 256 | −0.015681 | 0.01219 | 0.009368 | 0.011563 | 0.009471 | 0.002606 | 0.024406 | −0.06066 | 0.009166 | −0.012282 | 0.009307 | −0.015493 | −0.004405 | 0.055624 |
| 257 | −0.009284 | 0.002026 | −0.019565 | 0.003249 | 0.004728 | 0.005113 | −0.007697 | −0.005521 | −0.016541 | 0.039015 | 0.007042 | −0.001728 | −0.016669 | 0.006528 |
| 258 | 0.012792 | 0.004835 | −0.00425 | 0.028143 | 0.011035 | 0.030477 | −0.006909 | −0.004659 | −0.002887 | −0.011191 | −0.026993 | −0.012398 | 0.012852 | 0.006467 |
| 259 | 0.004975 | 0.011994 | 0.024759 | −0.004103 | −0.005059 | 0.007555 | −0.012931 | 0.02301 | −0.005439 | 0.007499 | 0.015393 | −0.011782 | 0.000208 | −0.025836 |
| 260 | 0.044059 | 0.018111 | 0.006387 | −0.009512 | 0.013995 | 0.014892 | −0.014839 | 0.032563 | 0.022409 | 0.055878 | 0.015919 | −0.006381 | −0.003573 | −0.012961 |
| 261 | −0.006807 | −0.004496 | 0.03624 | −0.004442 | 0.00991 | 0.028923 | −0.006908 | 0.030232 | 0.022641 | 0.033658 | −0.002144 | −0.03839 | 0.004361 | 0.005109 |
| 262 | 0.012076 | 0.000467 | 0.017669 | −0.015571 | −0.004916 | 0.008174 | −0.00876 | −0.000731 | 0.003245 | 0.005245 | 0.00077 | 0.008608 | 0.006014 | −0.003846 |
| 263 | 0.002813 | −0.014918 | −0.006422 | −0.042458 | −0.021649 | −0.01566 | −0.009805 | 0.002791 | −0.025881 | −0.0107 | 0.002231 | 0.007913 | −0.013729 | −0.013141 |
| 264 | 0.004691 | 0.017765 | 0.002807 | 0.013628 | 0.01373 | 0.009225 | 0.006532 | 0.012511 | −0.014982 | −0.025536 | 0.029192 | −0.015122 | 0.01544 | 0.005834 |
| 265 | −0.007173 | −0.000737 | 0.044601 | 0.03446 | 0.030722 | 0.00283 | 0.008177 | 0.018315 | 0.001615 | −0.012471 | −0.001331 | 0.017065 | 0.006261 | 0.021856 |
| 266 | −0.007646 | 0.019538 | −0.011492 | 0.034606 | 0.027814 | 0.03695 | 0.007563 | −0.008691 | 0.010276 | −0.006422 | −0.023684 | 0.005476 | −0.001535 | 0.010666 |
| 267 | 0.024837 | −0.011118 | 0.011758 | −0.0039 | −0.021846 | −0.027067 | 0.023882 | 0.0359 | 0.025567 | −0.019484 | 0.007501 | −0.021197 | −0.000034 | 0.019471 |
| 268 | 0.01739 | 0.000161 | 0.006194 | 0.000527 | −0.008295 | −0.007731 | −0.02898 | 0.004086 | −0.002578 | 0.028983 | −0.00409 | 0.013054 | 0.009254 | −0.005944 |
| 269 | 0.021266 | 0.021689 | 0.01344 | 0.008702 | −0.014921 | −0.011584 | −0.012096 | −0.026849 | −0.005437 | 0.021385 | −0.008906 | −0.011622 | −0.004655 | −0.003305 |
| 270 | −0.015881 | 0.015474 | 0.004645 | 0.007514 | −0.01748 | −0.004282 | −0.012792 | −0.020181 | −0.003732 | 0.004485 | −0.008814 | −0.024791 | −0.005466 | 0.001421 |
| 271 | −0.023555 | 0.013288 | −0.093048 | 0.007567 | 0.009985 | −0.021509 | 0.042588 | 0.080369 | 0.051501 | −0.014336 | 0.01537 | 0.062734 | 0.020643 | −0.009218 |
| 272 | −0.025369 | −0.005368 | −0.01753 | 0.008096 | 0.019661 | 0.03184 | −0.006307 | −0.035382 | −0.009143 | −0.006204 | 0.007662 | 0.015228 | 0.017483 | 0.010921 |
| 273 | −0.007006 | −0.010026 | −0.014574 | −0.000302 | 0.010152 | 0.015434 | −0.046355 | −0.040517 | −0.009761 | 0.009173 | 0.020106 | 0.023619 | 0.001355 | −0.005306 |
| 274 | −0.01651 | −0.003554 | −0.020658 | 0.000275 | 0.011943 | 0.011779 | −0.037878 | −0.047484 | −0.005127 | 0.004226 | 0.015385 | 0.015153 | −0.000691 | −0.006025 |
| 275 | −0.03704 | −0.004489 | −0.031873 | 0.012026 | −0.011776 | −0.009951 | −0.018736 | 0.028662 | 0.013674 | −0.030441 | 0.042191 | −0.041778 | −0.01761 | −0.002202 |
| 276 | 0.017209 | 0.014897 | −0.003119 | 0.004462 | 0.013467 | 0.026731 | −0.006974 | 0.018112 | 0.007971 | 0.014712 | 0.000483 | −0.004578 | 0.014236 | −0.007665 |
| 277 | 0.000108 | 0.00189 | −0.014484 | −0.00348 | 0.004296 | 0.016116 | −0.013338 | 0.026577 | −0.008744 | 0.008773 | −0.01069 | −0.009574 | −0.015221 | −0.009345 |
| 278 | −0.003743 | 0.017898 | −0.0291671 | 0.00479 | −0.000839 | 0.014623 | −0.015585 | 0.006556 | −0.00112 | −0.003751 | −0.011715 | −0.049188 | −0.032201 | −0.014756 |
| 279 | 0.00257 | −0.008054 | −0.027254 | −0.029361 | −0.001424 | 0.002609 | 0.015489 | 0.030585 | 0.012604 | 0.023394 | 0.014556 | 0.017217 | 0.005748 | 0.010171 |
| 280 | 0.006754 | −0.00923 | −0.014138 | 0.015429 | 0.01422 | 0.034724 | −0.001622 | 0.04689 | 0.006181 | 0.017748 | −0.002866 | −0.069222 | 0.030092 | 0.036372 |
| 281 | −0.002135 | 0.014114 | 0.008579 | 0.016462 | −0.001086 | −0.003423 | 0.011546 | −0.013758 | 0.016046 | −0.027407 | 0.002413 | 0.029603 | −0.00974 | 0.008368 |
| 282 | −0.003133 | 0.024233 | −0.016803 | 0.015703 | −0.012804 | −0.015719 | 0.00787 | −0.0056 | 0.023698 | −0.02171 | 0.000781 | 0.003304 | −0.018158 | 0.023235 |
| 283 | 0.018746 | 0.03355 | −0.011197 | 0.005993 | −0.007706 | 0.021134 | −0.003681 | −0.001678 | 0.020211 | −0.035538 | 0.007527 | 0.035649 | −0.020026 | −0.029407 |
| 284 | 0.001436 | 0.011703 | −0.027025 | 0.005272 | 0.004746 | −0.005911 | −0.003896 | 0.020432 | −0.006935 | 0.026429 | 0.020344 | −0.020403 | −0.014481 | 0.016429 |
| 285 | 0.008727 | 0.026941 | −0.021563 | −0.013093 | −0.002157 | −0.018654 | −0.006473 | 0.028439 | 0.005502 | 0.042214 | 0.020478 | −0.023351 | −0.020293 | 0.004017 |
| 286 | 0.025089 | 0.043531 | −0.009059 | 0.030191 | 0.013671 | 0.007051 | −0.000851 | 0.034983 | 0.011146 | 0.008715 | −0.002586 | −0.025903 | 0.026199 | 0.028318 |
| 287 | 0.002394 | 0.035224 | −0.028865 | 0.011541 | −0.005614 | 0.029833 | −0.004663 | 0.011004 | −0.005899 | −0.014069 | −0.026634 | −0.024047 | 0.005185 | 0.016971 |
| 288 | 0.044779 | 0.043758 | −0.002148 | 0.022449 | 0.009508 | 0.04926 | −0.009163 | −0.014724 | 0.021631 | 0.010518 | −0.007435 | −0.023138 | 0.011424 | 0.00785 |
| 289 | −0.016524 | −0.000152 | 0.016602 | 0.00474 | 0.00756 | 0.005092 | −0.00991 | −0.005946 | 0.018861 | 0.013993 | 0.008599 | 0.005541 | 0.002802 | 0.008655 |
| 290 | 0.012608 | −0.03997 | −0.033318 | 0.007052 | 0.002764 | −0.005548 | −0.014123 | −0.023125 | 0.007503 | 0.008313 | 0.016791 | 0.01022 | −0.006372 | 0.01756 |
| 291 | 0.015202 | −0.036268 | −0.028055 | 0.010198 | 0.00141 | −0.006396 | −0.015498 | −0.009884 | 0.010535 | 0.006454 | 0.018942 | 0.00344 | −0.00581 | 0.019719 |
| 292 | 0.008078 | −0.036859 | −0.039967 | 0.001213 | 0.001406 | −0.003599 | 0.002328 | −0.002905 | −0.003397 | −0.001942 | 0.010015 | 0.025358 | 0.003268 | 0.005206 |
| 293 | −0.116193 | −0.02167 | 0.054599 | 0.025516 | 0.000932 | 0.026069 | −0.051061 | 0.025471 | 0.019577 | 0.019005 | 0.001849 | 0.010507 | −0.011073 | −0.006085 |
| 294 | −0.023325 | −0.008523 | 0.015371 | 0.022796 | 0.000315 | −0.01487 | −0.008329 | −0.002677 | 0.016089 | −0.037117 | 0.010121 | −0.000428 | 0.004363 | −0.0124 |
| 295 | −0.053407 | 0.000805 | −0.003182 | 0.030056 | 0.00422 | 0.008259 | −0.034707 | 0.001425 | 0.005456 | −0.009693 | 0.005701 | 0.003475 | −0.012776 | −0.019956 |
| 296 | −0.009557 | −0.030075 | −0.024259 | −0.024234 | −0.023299 | −0.051458 | −0.014092 | −0.015051 | 0.000138 | −0.021986 | −0.014338 | −0.028906 | −0.020163 | −0.032392 |
| 297 | −0.030664 | −0.014154 | −0.007594 | −0.003807 | −0.009139 | 0.011839 | −0.019905 | −0.054361 | −0.014305 | −0.027745 | −0.017055 | 0.005902 | −0.017284 | −0.010897 |
| 298 | 0.02286 | 0.016759 | 0.034643 | 0.018867 | −0.000825 | 0.009859 | −0.002141 | 0.008178 | −0.03364 | −0.050133 | −0.010983 | −0.049748 | −0.028962 | −0.02551 |
| 299 | −0.019363 | −0.042687 | 0.003079 | −0.02538 | −0.005558 | −0.026528 | 0.01103 | −0.014274 | −0.001947 | 0.008692 | −0.037635 | 0.025884 | 0.014409 | −0.007132 |
| 300 | 0.024898 | −0.008761 | 0.012007 | 0.00921 | 0.011936 | 0.028614 | 0.020527 | 0.080101 | −0.017741 | −0.004096 | 0.003126 | −0.006297 | 0.018119 | −0.032994 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 301 | −0.040365 | −0.011039 | 0.032096 | 0.006029 | −0.001337 | −0.001107 | −0.01488 | 0.008634 | −0.010836 | 0.032508 | 0.001768 | −0.007311 | −0.019803 | −0.004079 |
| 302 | 0.000023 | −0.033103 | 0.026569 | −0.027041 | −0.016382 | −0.035566 | 0.016054 | 0.026134 | −0.001174 | 0.033546 | −0.005416 | −0.008825 | 0.006485 | −0.012667 |
| 303 | −0.000802 | −0.010058 | −0.0153 | 0.004863 | 0.003725 | −0.034562 | cioos 1 89 | 0.003081 | −0.011039 | −0.01475 | −0.045756 | −0.004877 | 0.025564 | −0.009026 |
| 304 | 0.010016 | −0.030846 | −0.002069 | −0.047948 | −0.010433 | −0.033374 | 0.013573 | 0.005905 | −0.009074 | 0.003263 | −0.036195 | 0.033245 | 0.031532 | −0.025104 |
| 305 | 0.696026 | −0.002764 | 0.065111 | 0.012854 | 0.007119 | 0.003799 | −0.017027 | 0.000825 | 0.00463 | −0.039311 | −0.014706 | −0.011404 | −0.001221 | 0.000424 |
| 306 | −0.00255 | 0.8216 | −0.033866 | −0.072074 | −0.034649 | −0.100716 | 0.011239 | 0.021137 | −0.01258 | −0.012447 | −0.008892 | 0.020228 | −0.023223 | −0.009295 |
| 307 | 0.035515 | −0.046823 | 0.475387 | −0.001029 | −0.00429 | −0.035463 | −0.02807 | −0.021032 | 0.025335 | −0.084116 | −0.022535 | 0.076021 | −0.019009 | −0.038676 |
| 308 | 0.026396 | −0.090809 | −0.016121 | 0.848314 | −0.056126 | −0.079681 | 0.041042 | 0.003463 | −0.011531 | 0.030707 | −0.019825 | 0.025956 | −0.011775 | −0.023537 |
| 309 | 0.005791 | −0.024156 | 0.001731 | −0.050852 | 0.913625 | −0.05026 | −0.013437 | 0.022909 | −0.024754 | −0.00696 | −0.044605 | 0.004521 | −0.06211 | −0.039992 |
| 310 | 0.020647 | −0.096289 | −0.003739 | −0.073138 | −0.075113 | 0.809117 | 0.026129 | 0.046605 | 0.004411 | −0.034577 | −0.00622 | 0.015629 | −0.060447 | −0.032591 |
| 311 | −0.028661 | 0.027778 | 0.012654 | 0.048251 | 0.001592 | 0.043756 | 0.864467 | −0.023773 | −0.043478 | 0.019561 | −0.02593 | 0.001479 | −0.033092 | −0.027804 |
| 312 | −0.007901 | 0.00154 | −0.057993 | 0.024413 | 0.018514 | 0.026253 | −0.027786 | 0.483825 | −0.061219 | −0.12081L | −0.044432 | 0.041499 | 0.018981 | 0.017479 |
| 313 | −0.000565 | −0.012488 | 0.042271 | −0.003033 | −0.019605 | 0.005048 | −0.047536 | −0.040827 | 0.854632 | −0.043127 | −0.062537 | −0.039521 | −0.039506 | −0.023835 |
| 314 | −0.013044 | 0.013116 | −0.024088 | 0.031325 | −0.013743 | −0.021642 | −0.003314 | −0.108342 | −0.058439 | 0.599337 | −0.033668 | −0.039159 | −0.038638 | −0.069614 |
| 315 | −0.024653 | −0.012737 | −0.016818 | −0.01416 | −0.042664 | −0.007946 | −0.026581 | −0.033461 | −0.059257 | −0.027279 | 0.890341 | 0.002181 | −0.042287 | −0.041813 |
| 316 | −0.025666 | 0.023651 | 0.077536 | 0.010336 | −0.026363 | −0.003408 | −0.005759 | 0.045857 | −0.021872 | −0.01943 | −0.006175 | 0.528492 | −0.030122 | 0.006554 |
| 317 | −0.015446 | −0.00066 | 0.002461 | 0.000587 | −0.061036 | −0.037678 | −0.033851 | 0.031227 | −0.021211 | −0.028693 | −0.038427 | 0.002222 | 0.879328 | −0.060207 |
| 318 | −0.00056 | −0.002179 | −0.041422 | −0.030088 | −0.034471 | −0.023564 | −0.026809 | 0.034485 | −0.027214 | −0.044542 | −0.04423 | 0.023137 | −0.063536 | 0.801552 |
| 319 | 0.023106 | −0.00462 | −0.030789 | −0.028359 | −0.052776 | −0.021003 | −0.020813 | 0.020382 | −0.038017 | −0.005037 | −0.073876 | −0.018758 | −0.060848 | −0.052607 |
| 320 | 0.014971 | −0.062763 | −0.016065 | −0.041363 | −0.011538 | −0.027843 | −0.026802 | −0.020486 | −0.012779 | 0.02547 | −0.026073 | −0.008825 | −0.021159 | −0.029295 |
| 321 | 0.026562 | −0.041656 | −0.070515 | −0.034919 | −0.015217 | −0.023648 | 0.000562 | −0.007653 | −0.041716 | −0.046439 | −0.040992 | −0.006423 | −0.000581 | −0.014261 |
| 322 | −0.047488 | 0.041866 | 0.00456 | 0.020161 | 0.014114 | 0.005769 | 0.015297 | −0.045537 | 0.053015 | −0.019528 | 0.028203 | −0.028918 | 0.012822 | −0.004695 |
| 323 | 0.027647 | 0.001166 | −0.03742 | 0.025185 | 0.007792 | 0.008926 | −0.022042 | −0.081872 | −0.041862 | −0.062606 | −0.006854 | −0.000151 | −0.004512 | −0.001599 |
| 324 | 0.010527 | −0.005918 | −0.05579 | 0.002764 | 0.004833 | −0.027803 | 0.010538 | −0.050637 | 0.019858 | 0.000716 | 0.034294 | −0.070273 | 0.020962 | 0.017563 |
| 325 | 0.007107 | 0.019733 | 0.027947 | 0.011342 | −0.046336 | −0.005794 | −0.020772 | −0.006757 | −0.031533 | −0.004877 | −0.042014 | −0.039599 | −0.044558 | −0.015577 |
| 326 | −0.020258 | −0.005263 | −0.002166 | 0.046842 | −0.013487 | −0.006832 | −0.0397 | −0.004191 | −0.026088 | −0.02929 | −0.013674 | 0.005851 | −0.026844 | −0.000142 |
| 327 | −0.021479 | −0.037933 | −0.007285 | −0.05606 | −0.039926 | −0.064234 | −0.008079 | 0.010061 | −0.012117 | 0.02638 | −0.028901 | 0.007543 | −0.026685 | −0.044123 |
| 328 | −0.072043 | −0.013853 | −0.00348 | −0.045761 | −0.010556 | 0.011853 | −0.007636 | −0.031272 | 0.016648 | −0.006517 | −0.003829 | −0.01185 | 0.009947 | 0.065414 |
| 329 | −0.0025081 | 0.023055 | 0.027521 | 0.022514 | −0.003791 | −0.014558 | −0.035747 | −0.02439 | −0.046612 | 0.0180521 | −0.020531 | 0.001691 | −0.007134 | −0.017159 |
| 330 | −0.013006 | 0.000932 | 0.093595 | −0.000302 | 0.001709 | −0.008079 | −0.010219 | 0.085193 | −0.002375 | 0.006882 | 0.008639 | −0.032874 | −0.020225 | 0.015377 |
| 331 | −0.003774 | 0.004768 | −0.019531 | 0.006748 | −0.023263 | −0.000064 | −0.035601 | −0.031605 | −0.020504 | 0.002044 | −0.042324 | −0.00758 | −0.001 | −0.010297 |
| 332 | 0.016719 | 0.008836 | −0.007457 | 0.012892 | −0.005433 | 0.002997 | −0.063978 | 0.041899 | −0.006744 | 0.000705 | 0.009428 | −0.040302 | −0.009382 | 0.016527 |
| 333 | −0.002615 | 0.031361 | −0.019708 | 0.022051 | −0.038285 | 0.009896 | −0.034059 | 0.008898 | −0.015317 | 0.04065 | −0.026967 | −0.014828 | −0.056146 | −0.03059 |
| 334 | 0.006915 | 0.031966 | 0.039309 | 0.044762 | −0.023509 | 0.035089 | −0.005136 | −0.063959 | −0.025339 | −0.035028 | −0.026839 | 0.017579 | −0.006537 | 0.010106 |
| 335 | 0.025908 | −0.017779 | −0.029151 | −0.034897 | −0.036595 | −0.040199 | −0.012486 | −0.020075 | −0.020492 | 0.033912 | −0.028489 | −0.043177 | −0.031774 | −0.025083 |
| 336 | −0.009481 | 0.003705 | 0.039058 | 0.023948 | −0.024824 | 0.000323 | 0.008905 | −0.004765 | 0.039232 | −0.059228 | −0.00201 | 0.071451 | −0.026466 | −0.024332 |
| 337 | −0.027827 | −0.024611 | −0.048389 | 0.02187 | 0.010005 | −0.026971 | −0.004889 | −0.037139 | 0.0247 | 0.009386 | −0.017671 | −0.037011 | −0.00762 | 0.001104 |
| 338 | 0.045308 | −0.000691 | −0.029187 | 0.021508 | −0.000264 | −0.020116 | −0.02433 | 0.017913 | 0.040812 | 0.007136 | 0.020529 | −0.032545 | 0.023281 | 0.026149 |
| 339 | −0.01844 | 0.000535 | −0.006495 | 0.011304 | −0.012623 | 0.014972 | −0.071591 | −0.024197 | −0.014186 | 0.007766 | −0.025918 | 0.007654 | −0.004128 | −0.018179 |
| 340 | −0.044047 | 0.002851 | 0.027765 | −0.00557 | −0.001623 | 0.009395 | 0.002174 | 0.06718 | 0.004684 | −0.001477 | −0.012926 | 0.005549 | 0.022651 | −0.064033 |

| | LH | LI | LJ | LK | LL | LM | LN | LO | LP | LQ | LR | LS | LT | LU |
|---|---|---|---|---|---|---|---|---|---|---|---|---|---|---|
| 1 | −0.008108 | 0.013247 | −0.041658 | −0.028413 | −0.041864 | −0.040583 | 0.006903 | 0.040482 | −0.04838 | −0.156468 | −0.021941 | 0.034611 | −0.006361 | 0.085873 |
| 2 | 0.031639 | −0.013449 | −0.020384 | −0.072902 | −0.017176 | −0.052001 | −0.013493 | 0.006029 | −0.04112 | 0.109851 | −0.011861 | −0.062106 | 0.044585 | −0.018424 |
| 3 | −0.061289 | 0.045612 | 0.012466 | −0.023909 | −0.07213 | −0.117646 | −0.08931 | −0.070572 | −0.067147 | 0.05182 | −0.132849 | 0.06488 | −0.06813 | 0.035735 |
| 4 | 0.027058 | −0.066176 | 0.040007 | 0.122236 | 0.074662 | −0.01103 | −0.038982 | 0.038046 | 0.011627 | −0.024845 | 0.024658 | 0.027283 | 0.036691 | −0.040081 |
| 5 | 0.010043 | 0.00491 | 0.030861 | 0.067245 | 0.041614 | −0.032724 | −0.04478 | −0.054069 | 0.016894 | 0.024073 | −0.001153 | 0.045769 | 0.011385 | 0.054735 |
| 6 | 0.029082 | 0.035039 | −0.011712 | 0.063953 | 0.017299 | −0.002242 | 0.024227 | 0.018409 | 0.031825 | 0.049024 | 0.019451 | 0.007768 | 0.055072 | −0.024077 |
| 7 | 0.031733 | 0.030203 | 0.050971 | −0.043822 | −0.003918 | 0.021402 | 0.024713 | −0.002376 | 0.036304 | −0.034538 | 0.021071 | −0.01214 | 0.064734 | 0.050233 |
| 8 | 0.007084 | −0.009009 | 0.035951 | 0.11129 | −0.063966 | 0.068574 | 0.033116 | 0.02159 | −0.016728 | 0.022274 | −0.014043 | 0.104296 | 0.001221 | 0.027301 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 9 | 0.003402 | −0.013892 | −0.044814 | −0.06914 | −0.118017 | 0.077748 | 0.041395 | 0.031431 | 0.020319 | −0.05614 | −0.017223 | −0.012789 | −0.022845 | −0.007257 |
| 10 | −0.028948 | −0.00324 | 0.002529 | −0.061275 | 0.038289 | −0.02452 | −0.054239 | −0.089954 | 0.016979 | 0.030404 | −0.015386 | 0.052093 | −0.049612 | 0.02561 |
| 11 | 0.022799 | 0.022925 | −0.002597 | −0.009152 | 0.056278 | 0.064735 | 0.053409 | −0.074964 | 0.057638 | 0.031284 | 0.012544 | −0.000471 | −0.007665 | −0.090873 |
| 12 | −0.012965 | 0.002652 | −0.041527 | −0.060372 | −0.004434 | 0.049706 | −0.069401 | −0.01089 | −0.016535 | 0.061253 | −0.012801 | 0.070858 | −0.032851 | 0.018379 |
| 13 | 0.000017 | −0.006048 | 0.010793 | 0.065904 | 0.018431 | −0.111366 | 0.060544 | 0.064392 | 0.071898 | −0.0247 | 0.058343 | 0.081389 | 0.012846 | 0.078413 |
| 14 | 0.011105 | 0.053132 | 0.043694 | 0.035166 | −0.030425 | 0.04087 | 0.0054 | −0.044701 | 0.008447 | 0.09171 | 0.011252 | −0.04008 | −0.058374 | 0.012032 |
| 15 | −0.005292 | −0.069969 | −0.065894 | 0.136601 | −0.013613 | −0.004818 | −0.020265 | −0.050917 | −0.02846 | −0.019082 | −0.03977 | 0.024097 | −0.058382 | −0.132671 |
| 16 | 0.018143 | 0.025484 | −0.050417 | 0.002067 | −0.037598 | 0.010949 | −0.014546 | 0.015791 | 0.012922 | −0.055143 | 0.004319 | 0.031856 | 0.023229 | 0.040258 |
| 17 | −0.059261 | −0.077375 | −0.030444 | 0.001887 | −0.016507 | 0.050143 | −0.045938 | 0.031093 | −0.049849 | 0.034353 | −0.037554 | −0.072055 | −0.02814 | −0.008808 |
| 18 | −0.051209 | −0.001332 | 0.105755 | 0.034764 | 0.097301 | 0.036872 | −0.054139 | −0.014017 | 0.055982 | 0.19123 | 0.115403 | 0.019503 | 0.05701 | 0.024153 |
| 19 | 0.002827 | −0.026262 | −0.069299 | −0.053452 | −0.097963 | 0.004875 | 0.073987 | 0.010959 | −0.037483 | −0.020193 | −0.08157 | −0.131718 | 0.002955 | −0.033657 |
| 20 | −0.036531 | −0.054086 | −0.032942 | −0.069112 | −0.078577 | −0.058655 | −0.009043 | −0.007962 | −0.002647 | −0.017997 | 0.043164 | −0.054907 | −0.01604 | −0.036628 |
| 21 | −0.00723 | 0.082941 | 0.018576 | −0.060229 | 0.02443 | −0.076494 | −0.041644 | 0.010858 | 0.029653 | −0.033629 | 0.040586 | 0.070825 | −0.036687 | 0.083857 |
| 22 | 0.00303 | −0.0299 | 0.083287 | 0.001981 | 0.034484 | 0.016119 | −0.051975 | −0.000015 | −0.014592 | 0.063322 | 0.0199 | 0.036965 | 0.013953 | 0.074797 |
| 29 | −0.024635 | 0.040862 | −0.046651 | 0.070721 | −0.046931 | −0.009599 | 0.059814 | 0.036275 | −0.03984 | −0.004931 | −0.031841 | −0.077996 | −0.025057 | −0.023588 |
| 24 | 0.072304 | −0.011272 | −0.017325 | −0.037478 | 0.012046 | −0.068206 | 0.084658 | −0.01017 | 0.025513 | 0.006413 | −0.002604 | 0.133502 | 0.058105 | −0.004255 |
| 25 | 0.0037 | −0.001586 | −0.020483 | −0.075167 | 0.042296 | 0.08714 | −0.020123 | 0.026694 | 0.01288 | −0.097182 | 0.009439 | 0.043108 | 0.05079 | 0.006673 |
| 26 | −0.0591 | 0.072502 | 0.034247 | 0.072229 | 0.053467 | 0.000932 | −0.017777 | −0.040329 | −0.007033 | 0.073072 | −0.048868 | −0.040449 | −0.044986 | −0.075422 |
| 27 | 0.032432 | −0.008084 | −0.041085 | 0.166054 | 0.057878 | 0.088874 | −0.007151 | −0.03886 | 0.043646 | −0.018938 | 0.023959 | 0.120361 | 0.081599 | 0.055567 |
| 28 | −0.016591 | −0.019047 | 0.091966 | −0.04077 | −0.061393 | −0.068871 | 0.032146 | 0.007729 | −0.019795 | −0.003337 | −0.034548 | −0.045664 | 0.031631 | 0.044755 |
| 29 | 0.004968 | 0.047134 | −0.021778 | 0.020467 | −0.001273 | −0.015333 | 0.011402 | −0.028783 | −0.001342 | −0.021541 | −0.025302 | 0.020539 | −0.011486 | −0.0204 |
| 30 | 0.03514 | 0.011813 | −0.00368 | −0.016283 | 0.011963 | −0.010152 | −0.00091 | −0.064557 | −0.011941 | 0.096066 | 0.009358 | −0.040829 | −0.011161 | 0.053283 |
| 31 | −0.011362 | −0.029466 | −0.058517 | −0.032303 | −0.02076 | 0.04679 | −0.016507 | −0.130869 | −0.043629 | −0.007322 | −0.085964 | −0.124538 | 0.005525 | 0.039781 |
| 32 | 0.026727 | 0.028148 | 0.01309 | 0.005257 | −0.045953 | −0.04437 | 0.016261 | 0.059957 | −0.001504 | −0.014184 | 0.038142 | 0.056175 | −0.024745 | 0.10375 |
| 33 | 0.004601 | −0.048648 | 0.032522 | −0.148538 | 0.068874 | −0.023244 | 0.047895 | 0.032794 | −0.007729 | −0.063821 | 0.045437 | 0.098836 | 0.016239 | −0.066143 |
| 34 | 0 061759 | 0.010681 | −0.001928 | −0.06651 | 0.075435 | −0.117971 | −0.013221 | −0.13523 | −0.012162 | 0.204128 | 0.059309 | 0.011074 | −0.003264 | −0.033074 |
| 35 | −0.017261 | −0.08076 | 0.0549 | −0.084867 | 0.003858 | 0.021792 | 0.014048 | 0.004558 | −0.014509 | 0.013842 | −0.015308 | −0.031102 | −0.039507 | 0.054498 |
| 36 | −0.005461 | −0.000775 | 0.04522 | 0.008972 | 0.064229 | 0.073887 | −0.013869 | 0.002655 | 0.016428 | 0.004286 | 0.024067 | 0.048948 | −0.037052 | −0.053268 |
| 37 | 0.016012 | 0.040157 | 0.001357 | 0.025741 | −0.037101 | −0.06066 | −0.009369 | 0.01721 | 0.010032 | −0.155631 | 0.014803 | 0.059881 | 0.001221 | 0.009271 |
| 38 | −0.040814 | −0.043424 | 0.034538 | 0.090546 | −0.048851 | 0.143039 | −0.019871 | −0.038122 | 0.005508 | −0.01998 | −0.00754 | −0.144325 | −0.000306 | 0.080349 |
| 39 | 0.019845 | 0.072849 | 0.031512 | 0.023436 | −0.032247 | −0.024534 | −0.005928 | 0.100654 | −0.048406 | 0.064622 | 0.003362 | −0.108079 | 0.039132 | −0.09233 |
| 40 | −0.032732 | −0.032842 | −0.014352 | 0.024491 | 0.016268 | −0.010551 | −0.039464 | −0.014331 | 0.006527 | −0.003916 | −0.017866 | 0.044051 | −0.023432 | −0.060399 |
| 41 | 0.002754 | 0.011306 | −0.01585 | −0.025061 | −0.06607 | −0.081418 | −0.009784 | −0.015311 | 0.04644 | 0.01972 | −0.042475 | −0.049624 | 0.012567 | −0.067061 |
| 42 | −0.004173 | −0.025051 | −0.006714 | −0.021199 | −0.018937 | 0.013193 | 0.015933 | 0.00008 | 0.016423 | −0.032947 | −0.000623 | 0.029509 | −0.006101 | −0.003776 |
| 43 | −0.002775 | −0.037122 | 0.106546 | −0.159042 | −0.01293 | 0.112779 | 0.105732 | 0.063679 | 0.012466 | −0.051668 | 0.038294 | −0.041111 | 0.016506 | −0.016308 |
| 44 | −0.014106 | −0.011967 | −0.047682 | 0.008859 | −0.048868 | 0.091379 | −0.013433 | −0.031737 | 0.012618 | −0.158436 | −0.018728 | 0.060599 | −0.034413 | 0.039919 |
| 45 | −0.013531 | 0.022653 | −0.107535 | −0.030422 | 0.013363 | 0.11688 | −0.060599 | 0.005841 | 0.016376 | 0.006424 | −0.037979 | 0.074677 | −0.049344 | 0.052333 |
| 46 | −0.050637 | −0.008818 | −0.084114 | −0.027038 | −0.014058 | 0.003297 | −0.003859 | 0.034156 | 0.008227 | 0.045101 | 0.047807 | −0.022373 | −0.004384 | 0.043123 |
| 47 | −0.022405 | 0.021974 | 0.083781 | −0.07419 | −0.046878 | 0.093874 | 0.037549 | −0.008521 | 0.010164 | −0.021733 | −0.032704 | 0.031376 | 0.007071 | −0.016004 |
| 48 | −0.057409 | −0.035751 | 0.024595 | 0.054214 | 0.017384 | −0.091181 | −0.001963 | −0.057645 | 0.011306 | 0.120364 | −0.034848 | −0.01558 | −0.006719 | −0.10779 |
| 49 | −0.017871 | 0.022303 | −0.029431 | −0.123852 | −0.058889 | −0.027142 | −0.042487 | −0.003566 | 0.000405 | −0.169772 | −0.023955 | −0.04738 | −0.012925 | 0.109421 |
| 50 | 0.044319 | 0.054086 | 0.035699 | −0.08497 | 0.066742 | 0.037056 | −0.028182 | −0.058049 | −0.025468 | −0.000689 | 0.01769 | −0.074117 | −0.009107 | −0.059581 |
| 51 | −0.025265 | 0.013199 | −0.021782 | −0.074386 | 0.042931 | −0.043711 | −0.094654 | 0.017882 | −0.013226 | −0.005801 | 0.010426 | 0.024368 | −0.030488 | 0.026564 |
| 52 | −0.007382 | −0.012462 | −0.027056 | −0.087697 | −0.078945 | 0.051013 | 0.01483 | 0.061652 | 0.025761 | −0.017065 | 0.072082 | −0.088544 | −0.005438 | 0.038951 |
| 53 | −0.044849 | 0.003922 | 0.000087 | 0.013205 | 0.071936 | 0.06349 | −0.046881 | −0.010111 | −0.064222 | 0.03297 | −0.021135 | −0.002916 | −0.044434 | 0.016843 |
| 54 | −0.011099 | −0.025491 | −0.039062 | −0.070447 | 0.070937 | 0.017746 | −0.044909 | −0.038888 | −0.005006 | −0.050212 | −0.007877 | 0.081599 | −0.040461 | 0.058374 |
| 55 | 0.020765 | −0.006839 | 0.060873 | 0.000674 | −0.08126 | −0.016034 | 0.018553 | 0.093763 | 0.075968 | 0.014167 | −0.002015 | −0.057707 | 0.041314 | −0.023832 |
| 56 | −0.01341 | −0.062982 | −0.011394 | −0.021763 | 0.012117 | −0.016834 | −0.000874 | 0.030004 | 0.001745 | 0.097269 | 0.100344 | 0.107822 | −0.001165 | 0.039603 |
| 57 | 0.00825 | 0.038811 | 0.020465 | 0.028389 | −0.06023 | 0.058593 | 0.035278 | 0.083005 | −0.01394 | 0.181001 | −0.052749 | 0.332125 | −0.048563 | 0.434984 |
| 58 | −0.019821 | 0.033972 | 0.085079 | −0.033031 | 0.008508 | 0.101635 | −0.009733 | −0.006817 | 0.0043481 | 0.042963 | −0.062116 | −0.033387 | −0.011398 | −0.058867 |
| 59 | −0.002758 | 0.006591 | −0.013266 | −0.014205 | 0.005436 | 0.024918 | 0.004253 | −0.001109 | −0.076443 | 0.13834 | −0.100449 | 0.010165 | −0.022949 | −0.013739 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 60 | −0.112478 | −0.087016 | −0.068333 | 0.066764 | −0.088881 | 0.161781 | 0.009418 | −0.00863 | −0.047868 | 0.069856 | −0.036452 | 0.138224 | −0.041749 | −0.092744 |
| 61 | 0.048307 | 0.0395 | 0.033284 | 0.000202 | 0.067532 | −0.019166 | 0.033179 | 0.072267 | 0.024379 | 0.122866 | 0.00802 | 0.032533 | 0.0475 | 0.066956 |
| 62 | 0.045182 | −0.045151 | −0.05885 | 0.096834 | −0.05376 | −0.085214 | −0.020222 | 0.002771 | −0.028452 | −0.017521 | −0.017493 | 0.040532 | −0.056027 | 0.067324 |
| 63 | −0.029636 | 0.071921 | 0.036242 | 0.041036 | 0.092511 | 0.069455 | 0.008813 | 0.03013 | −0.012562 | 0.006342 | 0.009332 | −0.026251 | 0.00728 | 0.005444 |
| 64 | 0.023537 | 0.003862 | 0.026625 | 0.126877 | 0.05301 | −0.023331 | 0.009222 | −0.086211 | −0.026748 | −0.022404 | −0.036531 | 0.076447 | −0.011667 | −0.10766 |
| 65 | 0.003749 | 0.072744 | −0.019249 | −0.136259 | −0.052759 | −0.061151 | −0.017418 | 0.024341 | 0.029959 | −0.068811 | 0.023266 | 0.002658 | 0.036458 | −0.053042 |
| 66 | −0.018473 | 0.119556 | −0.017897 | 0.052025 | −0.006025 | −0.00476 | −0.035451 | 0.072134 | 0.040666 | −0.075555 | 0.023952 | −0.155836 | −0.003627 | −0.0218 |
| 67 | 0.070141 | −0.017124 | 0.057433 | −0.048595 | −0.106829 | 0.00549 | 0.044643 | −0.178012 | −0.039684 | −0.152073 | −0.0227 | −0.028164 | −0.059202 | −0.082535 |
| 68 | −0.044159 | 0.011994 | 0.002329 | 0.081316 | 0.044748 | −0.036167 | −0.070193 | −0.016352 | −0.026105 | −0.002056 | −0.01143 | −0.028931 | 0.011402 | −0.019797 |
| 69 | 0.021429 | −0.034806 | 0.002136 | −0.117359 | −0.016757 | 0.070885 | 0.072926 | 0.038845 | 0.00544 | −0.063665 | −0.022376 | 0.117312 | −0.011794 | −0.035042 |
| 70 | 0.008338 | 0.052702 | −0.019265 | −0.044846 | −0.013026 | 0.074094 | −0.038697 | 0.00909 | 0.037197 | −0.009664 | −0.00646 | 0.017481 | −0.003896 | 0.040139 |
| 71 | −0.00965 | 0.025311 | 0.050062 | 0.03919 | −0.020664 | 0.167473 | 0.137863 | 0.031557 | −0.017183 | −0.029964 | −0.024654 | −0.007014 | 0.080466 | 0.015798 |
| 72 | 0.014929 | 0.037879 | −0.046941 | 0.099164 | 0.000742 | 0.032074 | −0.078155 | −0.014772 | 0.078202 | 0.018372 | 0.009998 | −0.145554 | 0.006109 | 0.105695 |
| 73 | 0.04203 | −0.031614 | 0.002619 | −0.011818 | −0.013745 | −0.028122 | 0.038764 | 0.076037 | −0.005659 | −0.108739 | 0.010559 | −0.000748 | −0.022456 | −0.047333 |
| 74 | 0.001486 | −0.010249 | 0.006276 | 0.015303 | −0.047695 | 0.017114 | −0.019024 | −0.0097 | −0.038142 | 0.081523 | −0.040059 | 0.028256 | −0.033114 | 0.020153 |
| 75 | 0.049978 | −0.049761 | −0.00909 | −0.123951 | −0.01299 | −0.040223 | −0.063672 | −0.001489 | −0.03495 | −0.020234 | 0.011662 | 0.035654 | 0.014917 | 0.031356 |
| 76 | 0.021955 | −0.026843 | −0.01178 | −0.084621 | 0.022977 | −0.09029 | 0.000856 | 0.022583 | −0.037947 | −0.062732 | −0.04331 | −0.050202 | 0.031522 | −0.034264 |
| 77 | −0.016378 | −0.039945 | −0.123925 | 0.114436 | −0.002902 | 0.093682 | 0.016599 | −0.051838 | −0.022735 | 0.120954 | −0.060325 | −0.100429 | 0.037025 | −0.000699 |
| 78 | 0.043448 | 0.037938 | −0.00702 | −0.04486 | −0.01434 | −0.057967 | −0.007285 | −0.002803 | −0.025888 | 0.021482 | 0.029923 | 0.077796 | −0.000627 | 0.016112 |
| 79 | −0.052594 | 0.018198 | 0.05413 | 0.127912 | −0.039812 | −0.020092 | −0.103291 | −0.038012 | 0.001509 | −0.085625 | 0.029189 | −0.036752 | −0.088221 | −0.014837 |
| 80 | 0.045602 | 0.036354 | −0.021256 | 0.015232 | −0.074178 | −0.065214 | 0.021827 | 0.027661 | −0.01975 | 0.058574 | −0.04697 | −0.011118 | −0.03209 | −0.030334 |
| 81 | −0.059889 | 0.017169 | 0.062528 | 0.06871 | −0.069385 | 0.001745 | 0.007505 | −0.057611 | 0.006059 | −0.036772 | −0.02686 | 0.040966 | −0.004847 | 0.074498 |
| 82 | 0.022481 | −0.01284 | 0.04004 | −0.065922 | 0.012133 | −0.125622 | −0.005725 | −0.051096 | 0.030691 | 0.097836 | −0.061415 | −0.035453 | −0.02027 | −0.007942 |
| 83 | 0.011322 | −0.0122231 | −0.0493831 | 0.012276 | −0.069819 | −0.01559 | −0.078352 | 0.016443 | −0.030989 | 0.0258721 | −0.031329 | −0.028511 | −0.008652 | 0.05135 |
| 84 | 0.038158 | 0.069915 | −0.053964 | 0.078804 | 0.013342 | −0.018518 | 0.011069 | 0.042172 | −0.013892 | −0.047113 | 0.014169 | −0.014423 | 0.002692 | 0.115801 |
| 85 | −0.007326 | −0.001078 | −0.053146 | −0.021823 | 0.069241 | −0.089084 | −0.034293 | −0.076849 | 0.007002 | −0.103739 | −0.016264 | 0.034926 | −0.009481 | −0.01952 |
| 86 | −0.030046 | −0.094754 | −0.003868 | 0.038936 | 0.044278 | −0.065672 | −0.027057 | −0.072668 | −0.013897 | 0.012382 | 0.070459 | −0.00696 | −0.034093 | −0.078307 |
| 87 | −0.025261 | 0.006534 | 0.000396 | −0.038825 | −0.038851 | 0.136155 | −0.008322 | −0.019602 | −0.01565 | 0.112147 | −0.032304 | 0.045376 | −0.044172 | 0.010937 |
| 88 | −0.058809 | −0.092761 | −0.086887 | 0.000332 | 0.062421 | 0.00931 | −0.002712 | 0.077473 | −0.049907 | −0.007766 | 0.01106 | −0.022944 | −0.037429 | −0.04449 |
| 89 | 0.048327 | −0.024024 | 0.024265 | −0.142337 | 0.044959 | 0.056001 | 0.004933 | 0.019187 | 0.0605121 | −0.015822 | 0.068381 | −0.085772 | 0.0308691 | −0.060661 |
| 90 | 0.073248 | 0.0629981 | −0.067836 | −0.012912 | −0.149675 | 0.03071 | 0.01895 | 0.048795 | 0.003291 | −0.010879 | −0.047039 | 0.063107 | 0.031564 | 0.045605 |
| 91 | −0.059381 | 0.0268991 | 0.024193 | 0.041506 | 0.001359 | 0.075019 | 0.014319 | −0.013358 | −0.000515 | −0.037238 | −0.037788 | 0.004819 | 0.002191 | −0.036689 |
| 92 | 0.013843 | 0.038147 | −0.016997 | −0.023342 | −0.015848 | −0.07447 | 0.037833 | 0.049775 | 0.021217 | 0.200536 | −0.003568 | 0.095885 | −0.016117 | −0.025438 |
| 93 | −0.011635 | −0.036286 | 0.052264 | 0.047449 | 0.037955 | −0.096038 | −0.012966 | 0.06079 | −0.007651 | −0.026405 | 0.080732 | 0.046017 | −0.034454 | 0.025098 |
| 94 | 0.019375 | 0.084861 | 0.078554 | −0.125359 | 0.050845 | 0.024442 | −0.060066 | 0.007753 | 0.000855 | −0.016728 | −0.012764 | −0.038757 | 0.036506 | −0.121141 |
| 95 | 0.018245 | 0.029711 | 0.018186 | 0.05814 | 0.10225 | −0.046886 | −0.004018 | −0.008695 | 0.019844 | −0.004605 | 0.007934 | 0.004916 | 0.053813 | −0.000517 |
| 96 | 0.022458 | 0.060167 | −0.07705 | −0.03097 | −0.013433 | 0.004135 | −0.010385 | 0.084134 | 0.007312 | 0.064797 | 0.083208 | 0.009242 | 0.03565 | 0.013636 |
| 97 | −0.045662 | −0.129479 | 0.019704 | −0.053845 | 0.033208 | −0.017633 | 0.027238 | 0.106013 | −0.077465 | −0.076781 | −0.012656 | −0.042113 | −0.023204 | −0.060267 |
| 98 | −0.0219231 | 0.025804 | 0.050978 | 0.070602 | 0.120548 | 0.049268 | 0.084089 | 0.047742 | −0.067092 | −0.072796 | 0.040081 | 0.070824 | 0.039035 | 0.065771 |
| 99 | 0.0006 | −0.038774 | −0.027889 | 0.018352 | −0.002677 | 0.132898 | 0.043717 | −0.115141 | −0.038996 | 0.046378 | 0.000311 | 0.100437 | 0.042254 | −0.022042 |
| 100 | −0.003726 | 0.006666 | 0.011412 | −0.005289 | −0.017103 | 0.015024 | 0.001874 | −0.003488 | 0.005498 | −0.000245 | −0.020518 | −0.041234 | −0.012287 | −0.007093 |
| 101 | −0.023245 | −0.016439 | 0.004204 | 0.002469 | −0.003735 | 0.038132 | −0.001989 | 0.012497 | −0.014767 | 0.015303 | −0.000438 | 0.01052 | −0.007903 | −0.004806 |
| 102 | −0.011771 | 0.01301 | 0.041814 | −0.00548 | 0.080056 | 0.005301 | 0.00475 | −0.041075 | −0.015797 | −0.041537 | −0.033207 | −0.014622 | −0.00727 | −0.006647 |
| 103 | −0.009989 | 0.002798 | −0.00008 | −0.028533 | −0.018598 | −0.040077 | −0.010495 | 0.008132 | 0.008896 | 0.042297 | −0.001313 | −0.004528 | −0.00592 | −0.007633 |
| 104 | 0.001741 | −0.019497 | 0.025448 | 0.01634 | −0.020802 | 0.029379 | 0.075556 | 0.011511 | −0.008539 | 0.005629 | 0.005791 | −0.028156 | −0.000797 | 0.038158 |
| 105 | −0.003101 | 0.043805 | −0.026712 | −0.00613 | −0.046597 | −0.009023 | −0.00351 | 0.038209 | −0.030901 | −0.035089 | −0.009949 | −0.032293 | −0.007966 | 0.000336 |
| 106 | −0.003872 | −0.005711 | 0.003668 | 0.017364 | 0.03555 | −0.00799 | 0.012002 | −0.006317 | 0.028008 | −0.040963 | 0.017321 | −0.008197 | 0.016842 | 0.008726 |
| 107 | −0.007246 | 0.022105 | −0.034048 | 0.016819 | −0.04198 | 0.038549 | 0.005601 | −0.047407 | 0.019458 | −0.005660 | −0.010677 | 0.008077 | 0.011114 | 0.005976 |
| 108 | 0.012126 | 0.025241 | 0.0074 | 0.011199 | −0.066502 | 0.002545 | −0.013776 | −0.009579 | 0.022554 | 0.0278 | 0.020016 | −0.018215 | −0.015148 | 0.019167 |
| 109 | −0.02303 | −0.061459 | 0.023397 | 0.012355 | 0.009053 | 0.105837 | 0.012063 | 0.025584 | −0.018369 | 0.0299 | 0.010389 | −0.02297 | 0.012198 | 0.075554 |
| 110 | −0.002781 | −0.012028 | −0.02559 | −0.008426 | −0.038214 | 0.014656 | −0.000749 | 0.040614 | −0.003117 | −0.001732 | −0.037139 | −0.003572 | −0.006939 | −0.020519 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 111 | 0.019353 | −0.036898 | 0.042577 | −0.014 | −0.024586 | −0.015051 | 0.037448 | −0.046947 | 0.003896 , | 0.000591 , | 0.00143. | −0.002542 | −0.017661 | −0.056775 |
| 112 | −0.011197 | −0.009394 | 0.019951 | −0.008714 | −0.011078 | −0.056901 | 0.023928 | 0.018626 | 0.004782 | −0.034345 | −0.004076 | 0.039282 | 0.025459 | 0.041604 |
| 113 | 0.021911 | 0.068116 | −0.017303 | 0.006231 | 0.04965 | 0.017355 | −0.025636 | −0.008683 | −0.002089 | −0.055262 | −0.00627 | −0.044094 | 0.004637 | −0.042239 |
| 114 | 0.0214211 | 0.0165641 | 0.005088 | −0.004899 | −0.074394 | 0.046077 | 0.010485 | −0.032593 | 0.0095961 | 0.0202731 | −0.052675 | −0.022069 | 0.0056021 | −0.027695 |
| 115 | −0.033748 | 0.010026 | 0.001826 | −0.055096 | 0.009416 | 0.00489 | −0.025748 | 0.043951 | −0.023704 | 0.017452 | −0.001779 | 0.021741 | 0.017252 | 0.031378 |
| 116 | 0.021408 | −0.014705 | −0.008282 | −0.023906 | 0.019388 | −0.045361 | 0.020149 | −0.043488 | −0.005338 | 0.01222 | −0.008477 | 0.017781 | 0.025003 | −0.008582 |
| 117 | −0.001189 | 0.026593 | −0.010269 | −0.058914 | −0.033391 | 0.04424 | 0.000887 | 0.016954 | 0.012849 | 0.027885 | −0.026447 | −0.021131 | −0.010886 | 0.053803 |
| 118 | 0.014618 | −0.000265 | 0.017546 | −0.065946 | −0.010012 | 0.016742 | 0.021169 | 0.05426 | −0.000516 | 0.05651 | −0.018896 | −0.015807 | −0.011502 | 0.033563 |
| 119 | 0.000041 | −0.030781 | 0.0173521 | −0.051532 | −0.050012 | 0.005198 | −0.00425 | 0.029238 | −0.004723 | 0.0152441 | 0.0252621 | 0.0187151 | 0.0100651 | −0.007464 |
| 120 | −0.027319 | −0.000191 | −0.017228 | −0.016136 | −0.01861 | 0.04785 | −0.014743 | −0.015092 | 0.014708 | −0.00501 | 0.001673 | 0.002511 | −0.022686 | 0.049826 |
| 121 | −0.04401 | −0.039612 | 0.003809 | −0.003881 | 0.041459 | 0.042231 | −0.015065 | −0.020412 | −0.012217 | 0.001606 | −0.017678 | 0.011365 | −0.026253 | −0.016208 |
| 122 | −0.004044 | 0.023851 | 0.020621 | 0.016861 | 0.03039 | −0.047974 | 0.026404 | 0.002525 | 0.00272 | −0.019723 | 0.001142 | 0.033066 | 0.008736 | 0.011669 |
| 123 | 0.006391 | 0.013317 | 0.004632 | 0.029382 | −0.003269 | −0.022922 | −0.018703 | −0.016266 | 0.012108 | 0.01376 | 0.021821 | 0.000442 | −0.012704 | 0.000425 |
| 124 | 0.010122 | −0.004831 | −0.034547 | −0.025688 | −0.02231 | 0.012529 | 0.016374 | 0.008581 | −0.01178 | −0.012051 | −0.004858 | −0.007163 | 0.017076 | 0.021969 |
| 125 | −0.014478 | 0.027705 | −0.018709 | 0.049784 | 0.056576 | −0.020037 | −0.015429 | 0.002354 | −0.01705 | −0.013904 | 0.024734 | 0.010764 | 0.002409 | 0.046647 |
| 126 | 0.004322 | 0.00493 | −0.032633 | 0.021158 | 0.016933 | 0.019264 | 0.00461 | −0.013813 | 0.002493 | 0.031401 | 0.026531 | 0.009172 | −0.003214 | 0.024035 |
| 127 | −0.007708 | −0.000275 | −0.038182 | 0.03973 | −0.003949 | 0.01761 | −0.002909 | 0.009338 | 0.004543 | 0.024183 | 0.010244 | −0.014215 | 0.006242 | 0.02319 |
| 128 | 0.002702 | 0.021368 | −0.020358 | −0.007585 | 0.032092 | 0.006418 | 0.0197 | 0.036956 | 0.016099 | −0.003629 | 0.023804 | −0.021358 | 0.036857 | −0.007392 |
| 129 | 0.00434 | −0.000662 | 0.037253 | 0.001352 | 0.014705 | −0.049884 | −0.001485 | −0.029755 | 0.012507 | −0.050702 | −0.026852 | 0.041238 | 0.008313 | 0.008649 |
| 130 | −0.045435 | −0.03333 | 0.026092 | −0.015382 | 0.003194 | −0.00554 | −0.017233 | 0.011005 | −0.02471 | 0.048743 | 0.033162 | −0.007789 | 0.027113 | −0.047436 |
| 131 | 0.0052641 | 0.030854 | −0.008803 | 0.002605 | −0.055842 | −0.019591 | −0.004281 | −0.024504 | 0.030926 | −0.044969 | −0.016863 | 0.033544 | −0.014022 | 0.0013 |
| 132 | 0.020614 | −0.002285 | −0.022591 | −0.083365 | −0.045114 | −0.058044 | −0.032133 | 0.017861 | 0.002313 | −0.023385 | 0.027447 | 0.016405 | 0.028176 | 0.062992 |
| 133 | −0.016277 | −0.032929 | −0.026081 | 0.016572 | 0.025823 | 0.008747 | −0.017821 | 0.064596 | 0.003024 | 0.047626 | 0.044025 | 0.010758 | −0.002426 | 0.029146 |
| 134 | 0.023568 | 0.021699 | −0.020426 | −0.071509 | 0.024459 | −0.040748 | 0.018562 | −0.010931 | −0.00865 | −0.035918 | 0.014453 | 0.037856 | 0.029341 | −0.024534 |
| 135 | 0.001465 | 0.001529 | −0.027057 | −0.015537 | 0.011868 | −0.03614 | −0.012633 | 0.004229 | 0.012578 | 0.01513 | 0.017846 | −0.038293 | −0.002492 | 0.008966 |
| 136 | −0.004465 | 0.040716 | −0.014093 | −0.03936 | 0.027712 | −0.003865 | 0.000462 | 0.035569 | −0.009674 | 0.01498 | 0.013154 | −0.002075 | 0.018037 | −0.011581 |
| 137 | 0.003341 | 0.004681 | −0.014881 | 0.003687 | 0.02468 | −0.034338 | −0.051785 | −0.033807 | −0.012499 | −0.014164 | −0.005818 | 0.015444 | 0.002244 | 0.009102 |
| 138 | −0.048903 | −0.043917 | −0.0141 | 0.041759 | −0.01036 | 0.047585 | 0.016611 | 0.035151 | −0.010021 | 0.018707 | 0.01306 | 0.02691 | −0.006144 | −0.073811 |
| 139 | −0.0184411 | −0.044237 | −0.022581 | 0.036165 | −0.007023 | 0.021601 | 0.017556 | 0.00517 | −0.062078 | −0.017734 | −0.005701 | 0.105778 | −0.043622 | −0.00378 |
| 140 | 0.021249 | 0.032525 | −0.033855 | 0.050741 | −0.031263 | 0.006637 | 0.003114 | −0.026839 | 0.0331431 | −0.074681 | −0.019884 | 0.0407231 | 0.0224741 | 0.030685 |
| 141 | 0.002511 | 0.0152051 | 0.0218341 | −0.039449 | −0.014426 | −0.076509 | −0.002893 | −0.001754 | −0.020973 | 0.073189 | 0.01556 | −0.061067 | −0.003863 | −0.045717 |
| 142 | 0.011578 | −0.047617 | −0.00102 | −0.045041 | −0.031732 | −0.00219 | 0.0081 | 0.00463 | −0.001423 | 0.031835 | 0.013684 | −0.009265 | −0.008461 | −0.011245 |
| 143 | −0.019762 | −0.024145 | −0.012347 | 0.056135 | 0.039753 | 0.013882 | 0.016337 | −0.009709 | −0.016809 | −0.022651 | −0.031669 | 0.011006 | −0.035248 | −0.007433 |
| 144 | 0.016681 | 0.005171 | −0.017963 | −0.011296 | 0.011474 | −0.033053 | −0.024323 | −0.035054 | 0.001522 | −0.022343 | −0.003309 | 0.041342 | −0.020452 | 0.02855 |
| 145 | −0.009178 | −0.018526 | −0.071818 | 0.007505 | −0.001636 | 0.031693 | −0.006688 | 0.018298 | −0.014904 | 0.008163 | −0.000079 | −0.029343 | −0.037822 | −0.008659 |
| 146 | −0.0039 | 0.014326 | −0.031861 | −0.000663 | −0.003186 | −0.032786 | −0.009278 | 0.012725 | −0.002186 | −0.019004 | 0.034305 | −0.009619 | 0.006471 | 0.013304 |
| 147 | 0.008735 | −0.003172 | 0.027982 | −0.037019 | 0.005381 | −0.015342 | −0.00005 | −0.019705 | 0.000965 | −0.037717 | 0.019582 | −0.010727 | 0.010974 | 0.020225 |
| 148 | −0.008394 | 0.01516 | 0.00611 | 0.044008 | 0.039157 | −0.023109 | −0.028659 | −0.032093 | −0.011892 | 0.070012 | −0.016232 | 0.033678 | −0.034584 | 0.015244 |
| 149 | −0.020044 | 0.008488 | 0.005335 | −0.020696 | 0.016812 | −0.012723 | 0.01264 | 0.021859 | −0.002161 | −0.022692 | −0.013684 | 0.009138 | −0.013771 | 0.008054 |
| 150 | −0.009303 | 0.024833 | 0.009278 | 0.032063 | 0.013391 | −0.03159 | −0.032633 | −0.00123 | −0.015501 | −0.017643 | 0.027945 | −0.027867 | 0.002962 | −0.011329 |
| 151 | −0.018969 | 0.03607 | 0.065315 | 0.048212 | −0.008102 | 0.013848 | 0.02023 | −0.058818 | −0.0152 | −0.038545 | −0.007493 | −0.048315 | −0.023847 | −0.05449 |
| 152 | −0.030132 | −0.044148 | −0.021659 | 0.018978 | 0.026058 | −0.001676 | 0.002924 | −0.008419 | −0.035488 | −0.009363 | −0.031542 | 0.015737 | 0.000286 | −0.015884 |
| 153 | −0.016962 | −0.001674 | 0.019092 | −0.022336 | −0.005589 | −0.035762 | −0.016775 | −0.022542 | −0.027644 | −0.002597 | −0.031931 | −0.030538 | −0.014203 | 0.007697 |
| 154 | 0.018694 | −0.009258 | −0.0147 | −0.01457 | −0.019154 | −0.014817 | −0.00654 | −0.008124 | −0.035406 | −0.070077 | −0.001916 | −0.020362 | −0.001715 | −0.026303 |
| 155 | 0.010064 | −0.021231 | −0.02165 | 0.017954 | −0.013746 | 0.015299 | −0.005108 | −0.004586 | −0.024441 | 0.028682 | −0.009208 | 0.052326 | −0.003331 | −0.003291 |
| 156 | −0.02678 | 0.025786 | 0.042931 | 0.044304 | −0.022002 | 0.011931 | 0.027375 | −0.074732 | 0.014442 | 0.003285 | 0.019666 | −0.024493 | −0.011615 | −0.044377 |
| 157 | 0.006793 | −0.015852 | −0.008999 | 0.0168 | −0.013441 | −0.005871 | 0.030053 | 0.005418 | 0.009938 | −0.015178 | 0.010255 | −0.023776 | −0.001183 | 0.02309 |
| 158 | 0.011377 | −0.007778 | 0.019941 | −0.002754 | 0.02436 | −0.025001 | −0.007826 | 0.00991 | 0.007469 | −0.014931 | 0.039956 | −0.068271 | −0.021852 | 0.085187 |
| 159 | 0.000337 | −0.00023 | −0.069469 | 0.050906 | −0.049645 | 0.048291 | 0.006685 | −0.033419 | −0.028649 | −0.027796 | −0.049058 | −0.058667 | −0.026835 | −0.002466 |
| 160 | −0.005357 | 0.022281 | 0.04043 | −0.032127 | 0.003639 | 0.019142 | 0.011552 | −0.005287 | 0.010677 | −0.056181 | 0.0123891 | −0.0122 | 0.028028 | −0.007152 |
| 161 | 0.003639 | −0.059608 | 0.018636 | 0.044438 | 0.005854 | 0.020862 | 0.046936 | 0.022651 | −0.00678 | 0.034031 | −0.035976 | 0.021537 | −0.027306 | 0.043019 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 162 | 0.008384 | −0.024541 | 0.013179 | −0.024584 | 0.00401 | −0.062529 | −0.00535 | −0.001261 | 0.018158 | −0.011092 | −0.001732 | 0.009941 | −0.040792 | −0.027759 |
| 163 | 0.026995 | −0.007873 | −0.003892 | −0.057801 | −0.01515 | −0.005228 | 0.010806 | −0.031242 | 0.020455 | 0.037155 4 | −0.013248 | −0.020442 | 0.001019 | −0.042221 |
| 164 | 0.022306 | 0.029602 | −0.037283 | −0.012684 | −0.037006 | −0.011134 | 0.017495 | −0.038858 | −0.031545 | −0.0036 | −0.01538 | −0.048357 | 0.001589 | −0.039131 |
| 165 | 0.017094 | 0.006555 | 0.004977 | 0.018984 | 0.020909 | −0.057178 | 0.014112 | 0.027184 | 0.00963 | −0.05191 | −0.037628 | 0.02189 | 0.018203 | −0.055261 |
| 166 | −0.016618 | 0.006773 | −0.000372 | −0.061733 | −0.046462 | −0.005608 | −0.008976 | 0.003667 | 0.012625 | 0.054061 | 0.008028 | −0.045469 | 0.003712 | −0.009902 |
| 167 | 0.011859 | −0.00964 | 0.003783 | 0.00482 | −0.02405 | −0.038185 | 0.039629 | −0.022237 | −0.013968 | −0.004217 | −0.000735 | −0.021733 | 0.017732 | −0.01469 |
| 168 | −0.002176 | 0.00267 | −0.038002 | 0.013549 | 0.040708 | 0.010829 | 0.022855 | −0.004711 | 0.016636 | −0.010026 | 0.039766 | −0.004676 | −0.001061 | 0.002947 |
| 169 | 0.002762 | 0.001362 | 0.003745 | −0.021453 | −0.011628 | 0.031029 | 0.005195 | 0.013957 | 0.008394 | 0.022465 | 0.014803 | 0.015936 | 0.000996 | 0.009659 |
| 170 | −0.000544 | 0.025208 | 0.012632 | −0.038071 | 0.003187 | 0.015859 | −0.001559 | 0.005093 | −0.006515 | −0.007716 | 0.021152 | 0.032786 | 0.014726 | 0.023954 |
| 171 | 0.011373 | 0.017934 | 0.006226 | −0.033985 | −0.028335 | 0.020323 | 0.012429 | 0.01219 | 0.013322 | 0.034754 | 0.010058 | 0.017518 | 0.002153 | −0.005674 |
| 172 | 0.0091631 | 0.0137711 | 0.032381 | −0.002391 | 0.01857 | 0.067811 | 0.002547 | 0.020137 | 0.009119 | 0.014141 | 0.010969 | −0.011179 | −0.003719 | −0.019973 |
| 173 | −0.003026 | 0.009011 | 0.038044 | 0.039125 | 0.032728 | 0.047309 | −0.002761 | 0.034031 | 0.003184 | −0.002285 | 0.00831 | 0.01792 | −0.007904 | −0.021177 |
| 174 | 0.003163 | −0.04301 | −0.005391 | 0.012044 | 0.02964 | 0.032087 | 0.000267 | 0.013622 | −0.006802 | 0.019595 | 0.01571 | −0.007211 | 0.006082 | −0.047036 |
| 175 | −0.001922 | −0.025907 | −0.021463 | −0.000656 | −0.006189 | 0.013377 | −0.014368 | 0.049933 | −0.006199 | −0.017067 | 0.027649 | −0.059575 | −0.014698 | −0.014197 |
| 176 | −0.016028 | 0.018577 | −0.007168 | 0.020818 | −0.014793 | 0.035125 | −0.004409 | 0.003759 | 0.017667 | −0.007915 | −0.012339 | −0.08416 | −0.004865 | 0.021408 |
| 177 | 0.027446 | 0.005443 | −0.014789 | −0.043297 | 0.058087 | −0.037676 | 0.012766 | −0.016466 | 0.007139 | 0.059915 | 0.018166 | −0.059405 | 0.012782 | 0.032659 |
| 178 | −0.005627 | −0.063733 | −0.0115 | 0.007431 | 0.012295 | 0.015153 | 0.02095 | 0.027224 | 0.00619 | 0.019333 | 0.003076 | 0.016497 | −0.022178 | −0.014215 |
| 179 | 0.005499 | −0.013013 | 0.000202 | −0.018564 | −0.010189 | −0.002393 | 0.000726 | −0.012055 | 0.009397 | 0.048108 | 0.000852 | −0.012333 | 0.01021 | −0.031992 |
| 180 | −0.010074 | −0.004424 | 0.026097 | −0.011601 | 0.02026 | −0.016766 | −0.005302 | 0.015654 | 0.001782 | 0.024007 | 0.011119 | 0.013823 | −0.006331 | −0.001209 |
| 181 | −0.011771 | −0.015139 | 0.025771 | −0.014589 | −0.008101 | −0.005434 | −0.00161 | 0.010841 | −0.006762 | 0.011206 | 0.001201 | 0.016203 | 0.00253 | 0.002448 |
| 182 | −0.0086661 | −0.0002521 | 0.0110371 | −0.015174 | −0.009395 | 0.007068 | −0.031317 | −0.003161 | −0.024098 | 0.004606 | 0.004165 | 0.014853 | −0.005993 | 0.008446 |
| 183 | 0.023158 | 0.045508 | −0.006555 | −0.006063 | −0.020747 | −0.010983 | −0.007945 | −0.037099 | 0.000931 | 0.026703 | −0.019106 | −0.025927 | 0.021433 | −0.031246 |
| 184 | 0.033613 | 0.053424 | −0.010751 | 0.010531 | −0.001809 | 0.003677 | −0.017255 | −0.038774 | 0.026699 | −0.029442 | −0.024156 | 0.037485 | 0.001905 | −0.008465 |
| 185 | −0.029439 | −0.014757 | 0.007403 | −0.049607 | −0.006685 | 0.014504 | −0.039472 | 0.018597 | −0.003607 | 0.005281 | −0.028592 | −0.015936 | −0.036474 | −0.085238 |
| 186 | 0.002115 | 0.026077 | 0.0432221 | −0.010523 | −0.019499 | 0.010625 | −0.003993 | 0.008859 | −0.033018 | −0.01738 | 0.003466 | 0.100451 | −0.024399 | 0.019792 |
| 187 | 0.004308 | 0.038586 | 0.019268 | 0.03391 | 0.040167 | 0.019494 | 0.004105 | −0.003159 | −0.014604 | −0.00614 | 0.002422 | 0.01646 | 0.002119 | −0.00069 |
| 188 | 0.002237 | 0.020983 | 0.01437 | 0.01464 | 0.021166 | 0.025022 | −0.011063 | −0.022566 | −0.000343 | −0.010547 | −0.00281 | 0.006584 | −0.000673 | −0.023882 |
| 189 | 0.005748 | 0.023592 | −0.00617 | 0.028383 | −0.021108 | −0.011634 | −0.040703 | −0.068116 | 0.003055 | 0.019957 | −0.002095 | −0.043776 | −0.006188 | −0.013767 |
| 190 | −0.004098 | 0.005405 | −0.007733 | 0.011945 | 0.020376 | 0.012933 | −0.002771 | −0.006338 | −0.032364 | 0.001262 | 0.003066 | −0.00871 | −0.011108 | −0.019842 |
| 191 | 0.00254 | −0.011221 | 0.014514 | −0.039432 | −0.002166 | −0.013181 | 0.027152 | 0.008274 | −0.015836 | 0.013818 | 0.023437 | 0.012232 | 0.006937 | 0.01712 |
| 192 | 0.015405 | 0.032925 | −0.074236 | 0.030398 | −0.041764 | −0.028296 | −0.007389 | 0.009759 | −0.025795 | 0.008285 | −0.020548 | 0.042265 | −0.000306 | 0.049951 |
| 193 | 0.023284 | 0.019565 | −0.024857 | −0.018715 | 0.00024 | 0.031489 | −0.006114 | −0.007842 | 0.000536 | −0.011246 | 0.025377 | 0.012598 | 0.011747 | −0.006009 |
| 194 | −0.018667 | 0.015238 | 0.019387 | −0.031058 | 0.024329 | −0.01146 | −0.012757 | −0.011746 | 0.025349 | −0.002888 | 0.017464 | −0.003735 | −0.002175 | 0.030807 |
| 195 | 0.006099 | −0.016443 | 0.032564 | 0.047903 | 0.010922 | −0.031053 | 0.001538 | −0.0561 | −0.006391 | 0.037625 | −0.007161 | 0.0228 | 0.001518 | −0.014629 |
| 196 | 0.00003 | −0.023813 | 0.012199 | 0.009363 | 0.01765 | 0.010502 | −0.004496 | −0.002554 | −0.005438 | −0.000457 | 0.009852 | 0.029231 | −0.009851 | −0.002145 |
| 197 | 0.006311 | 0.01125 | −0.02343 | −0.000448 | −0.027798 | −0.037156 | −0.004379 | −0.001101 | −0.020172 | −0.048859 | −0.001413 | 0.018184 | −0.004101 | 0.016882 |
| 198 | 0.009764 | 0.011561 | 0.007368 | −0.01868 | 0.023244 | −0.015919 | 0.024871 | −0.032262 | 0.021648 | 0.029016 | −0.002655 | −0.003008 | −0.011359 | 0.011926 |
| 199 | 0.01812 | −0.003985 | −0.035149 | −0.04085 | −0.049138 | −0.02429 | −0.014805 | 0.009678 | −0.014947 | −0.045358 | −0.007609 | −0.012781 | −0.013 | 0.052766 |
| 200 | 0.01589 | −0.014554 | 0.018709 | 0.009764 | −0.000359 | −0.012682 | 0.020647 | −0.011191 | −0.000149 | 0.1051 | −0.00879 | −0.022866 | 0.000195 | −0.004464 |
| 201 | −0.01179 | 0.056954 | 0.021783 | −0.014489 | −0.024684 | −0.112083 | −0.028329 | 0.002855 | 0.01104 | −0.009548 | −0.039667 | −0.068978 | −0.001825 | 0.075311 |
| 202 | −0.015945 | 0.021297 | 0.020173 | 0.010728 | 0.025447 | 0.018432 | 0.018358 | −0.010263 | 0.006766 | −0.024807 | 0.030368 | 0.048525 | 0.006173 | −0.016501 |
| 203 | 0.018866 | −0.0004 | −0.035302 | −0.012306 | 0.030955 | −0.066191 | 0.012407 | −0.031228 | 0.001233 | −0.012922 | −0.033252 | −0.009929 | −0.005206 | 0.058775 |
| 204 | −0.012575 | −0.009672 | −0.015043 | 0.038131 | −0.011822 | −0.002886 | 0.016548 | −0.003043 | −0.01092 | −0.056604 | −0.044754 | 0.003813 | 0.010983 | 0.00794 |
| 205 | 0.017582 | 0.04082 | 0.050332 | 0.043308 | 0.070002 | 0.000739 | −0.043308 | 0.021694 | 0.017949 | 0.065036 | 0.022603 | −0.0101 | 0.017253 | 0.05925 |
| 206 | 0.028383 | 0.027554 | −0.0096 | 0.017155 | 0.027355 | −0.010483 | 0.007521 | 0.029414 | −0.039382 | −0.018894 | −0.00937 | −0.02038 | 0.008292 | 0.026273 |
| 207 | 0.04901 | −0.023163 | 0.002157 | 0.012414 | −0.028694 | −0.015109 | 0.010696 | 0.002816 | −0.021853 | 0.054363 | 0.00222 | 0.03428 | 0.029764 | −0.025234 |
| 208 | −0.018442 | −0.020917 | −0.013853 | 0.017663 | −0.004997 | −0.058827 | 0.009036 | 0.008774 | −0.030733 | −0.036456 | −0.037093 | −0.037456 | 0.00707 | 0.060754 |
| 209 | 0.005118 | 0.021958 | −0.011731 | −0.058693 | 0.00898 | −0.015979 | −0.009714 | 0.042725 | 0.019231 | −0.012864 | −0.022843 | 0.054127 | −0.009378 | 0.014503 |
| 210 | 0.017077 | −0.036395 | −0.076476 | 0.040655 | −0.012392 | 0.001857 | 0.014597 | −0.037683 | 0.003962 | −0.025607 | 0.015998 | −0.055542 | −0.011839 | −0.023448 |
| 211 | 0.003046 | 0.01264 | −0.031551 | 0.048483 | 0.00735 | −0.009308 | −0.005106 | 0.008994 | 0.04245 | 0.028042 | −0.005513 | −0.022519 | −0.010257 | −0.022263 |
| 212 | 0.019347 | 0.014945 | 0.027423 | −0.018355 | −0.036827 | 0.01894 | −0.001174 | −0.01815 | −0.022863 | −0.018243 | −0.068108 | 0.001152 | −0.017135 | 0.009064 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 213 | 0.006411 | 0.012361 | 0.057266 | 0.00875 | 0.015687 | −0.001876 | −0.018644 | −0.023406 | 0.0001 | 0.066975 | 0.040802 | −0.013408 | −0.012814 | 0.005179 |
| 214 | −0.00075 | 0.015479 | −0.003651 | 0.014037 | −0.018809 | −0.008267 | −0.009015 | 0.012504 | 0.016389 | 0.039889 | −0.007627 | −0.013193 | 0.00351 | −0.002066 |
| 215 | 0.02421 | −0.020924 | 0.029705 | −0.010065 | −0.026836 | −0.007734 | −0.0069 | 0.017631 | 0.014946 | −0.008135 | 0.01361 | −0.055453 | −0.002793 | 0.030121 |
| 216 | −0.012977 | −0.012035 | 0.028001 | −0.024948 | 0.008892 | 0.030888 | 0.039307 | 0.00602 | 0.015824 | −0.026757 | 0.035886 | 0.009131 | −0.009621 | 0.036811 |
| 217 | −0.007925 | 0.000393 | 0.024221 | −0.025298 | 0.016192 | 0.03391 | 0.004558 | 0.035814 | −0.02193 | −0.011992 | 0.019702 | 0.032264 | 0.001034 | −0.002072 |
| 218 | −0.004725 | −0.012319 | −0.011994 | 0.004839 | −0.007594 | 0.003686 | −0.027924 | 0.02462 | 0.000671 | −0.050147 | −0.00063 | 0.017896 | −0.013622 | 0.034461 |
| 219 | 0.003235 | −0.010203 | 0.027081 | −0.020148 | −0.004986 | −0.024826 | 0.00321 | 0.015891 | −0.011536 | −0.006491 | −0.002205 | 0.021915 | −0.010593 | 0.006887 |
| 220 | 0.006233 | 0.008478 | −0.01225 | −0.050413 | 0.010017 | −0.040389 | −0.021246 | 0.033123 | −0.01975 | 0.006617 | −0.000643 | 0.015862 | 0.025586 | −0.007021 |
| 221 | −0.014438 | −0.014326 | 0.020557 | 0.02624 | 0.036614 | 0.017762 | −0.002312 | 0.00402 | 0.004664 | −0.021318 | −0.003706 | 0.011089 | −0.001199 | −0.046267 |
| 222 | −0.005917 | −0.017802 | 0.002714 | 0.037372 | 0.001695 | −0.017958 | 0.006937 | 0.01176 | −0.01579 | −0.002778 | −0.026222 | 0.007028 | −0.006649 | −0.010407 |
| 223 | −0.021926 | −0.015161 | 0.00386 | 0.002548 | 0.006411 | 0.021048 | 0.012872 | 0.03365 | −0.000343 | 0.028151 | 0.000266 | −0.005606 | 0.01423 | 0.007218 |
| 224 | −0.021157 | −0.033303 | −0.012634 | −0.0052 | −0.028792 | −0.010603 | 0.002339 | 0.022942 | −0.001136 | 0.029646 | 0.004477 | −0.000829 | −0.006471 | 0.046219 |
| 225 | −0.02257 | −0.021189 | 0.004349 | −0.009252 | −0.020572 | 0.003925 | 0.006466 | 0.032733 | −0.003723 | 0.02575 | −0.009951 | −0.011192 | −0.006073 | 0.034439 |
| 226 | −0.005623 | −0.000156 | 0.009191 | 0.023044 | −0.006151 | −0.027675 | −0.029063 | −0.026494 | 0.00051 | 0.019928 | −0.006557 | 0.009711 | −0.023106 | −0.013022 |
| 227 | 0.009341 | 0.004861 | −0.02048 | −0.004913 | 0.000052 | −0.025805 | −0.020957 | −0.033097 | 0.008394 | 0.024974 | 0.000111 | −0.009194 | −0.006321 | 0.005982 |
| 228 | −0.009711 | 0.003548 | −0.040719 | −0.013618 | 0.009906 | −0.039607 | −0.063949 | 0.004789 | −0.022897 | −0.050862 | −0.004165 | 0.030301 | −0.006761 | 0.063017 |
| 229 | 0.015676 | 0.048206 | 0.021961 | 0.036536 | 0.008129 | 0.025596 | 0.000748 | 0.028855 | −0.001943 | −0.01317 | 0.007298 | −0.04567 | 0.008484 | 0.029376 |
| 230 | 0.011655 | 0.005787 | −0.002668 | −0.007583 | 0.011539 | 0.030193 | 0.011542 | −0.025052 | 0.014329 | −0.016847 | 0.012708 | −0.028598 | 0.030565 | 0.01442 |
| 231 | −0.00238 | 0.043022 | 0.026091 | −0.040167 | −0.006513 | 0.03253 | 0.001907 | −0.018202 | 0.009626 | 0.022122 | 0.002634 | 0.017832 | 0.022025 | −0.018366 |
| 232 | −0.012125 | 0.024927 | 0.032052 | 0.006253 | 0.003738 | −0.041142 | 0.019488 | 0.017321 | −0.024048 | −0.047359 | −0.006828 | −0.049962 | 0.007412 | −0.028553 |
| 233 | 0.016079 | 0.029201 | −0.001753 | 0.005589 | 0.013492 | 0.000229 | 0.016493 | −0.021371 | 0.006108 | −0.000869 | 0.001855 | −0.018762 | −0.003078 | −0.000171 |
| 234 | 0.001861 | −0.013666 | −0.011181 | −0.007577 | −0.023214 | 0.000064 | −0.001576 | 0.035315 | 0.012929 | 0.025501 | 0.03691 | 0.009386 | 0.013124 | 0.022047 |
| 235 | −0.000466 | −0.028649 | 0.00087 | −0.009913 | −0.022557 | 0.010606 | 0.016358 | 0.021828 | −0.00914 | 0.04493 | −0.002791 | 0.00124 | 0.009127 | −0.015095 |
| 236 | 0.006084 | 0.01874 | −0.009443 | −0.016805 | 0.015947 | 0.006753 | 0.006598 | −0.028697 | −0.003935 | −0.000208 | −0.010485 | −0.01008 | 0.008035 | 0.012514 |
| 237 | −0.006142 | 0.030935 | −0.004404 | 0.018583 | −0.023679 | 0.042612 | 0.012652 | 0.021214 | 0.005344 | −0.016514 | −0.011068 | 0.003768 | −0.003687 | 0.033776 |
| 238 | 0.001068 | 0.001663 | 0.012885 | −0.005624 | −0.01158 | −0.003088 | 0.011351 | −0.001573 | −0.014735 | 0.004027 | −0.004734 | 0.026282 | 0.003509 | 0.01158 |
| 239 | 0.012932 | −0.009407 | 0.019222 | −0.01031 | 0.019185 | −0.026407 | 0.018396 | −0.006825 | −0.005545 | 0.008814 | −0.005945, | 0.018101 | 0.003958 | 0.001247 |
| 240 | 0.004733 | −0.006445 | 0.005412 | 0.008433 | 0.004829 | 0.019702 | 0.018481 | −0.042398 | 0.011018 | 0.00985 | 0.033631 | −0.010971 | −0.005872 | −0.029913 |
| 241 | 0.006493 | −0.015923 | −0.054587 | 0.035388 | −0.000637 | 0.027423 | 0.026712 | −0.051716 | 0.002693 | 0.016815 | 0.00687 | −0.0078 | −0.011032 | −0.013631 |
| 242 | 0.006002 | 0.010805 | −0.012098 | 0.000258 | −0.008722 | 0.001264 | −0.020858 | 0.004166 | −0.021856 | 0.017206 | −0.005098 | 0.002814 | −0.006774 | 0.005688 |
| 243 | 0.001974 | 0.003916 | 0.008192 | 0.001464 | −0.016383 | 0.02223 | −0.013222 | −0.028469 | −0.004681 | 0.010674 | −0.014987 | 0.015544 | −0.019461 | 0.008284 |
| 244 | 0.003655 | 0.021177 | 0.017613 | −D.006914 | 0.042289 | −0.010252 | 0.005543 | −0.000171 | 0.015812 | 0.002119 | −0.000973 | −0.028365 | 0.010245 | −0.022647 |
| 245 | 0.0116 | 0.007853 | −0.012445 | −0.002407 | 0.009179 | 0.011344 | 0.006154 | −0.048033 | 0.019669 | −0.02432 | −0.007602 | −0.010199 | 0.010126 | −0.005533 |
| 246 | 0.001559 | −0.001575 | −0.006895 | 0.017523 | −0.009447 | 0.001912 | −0.003541 | 0.017118 | −0.014175 | −0.007828 | −0.001568 | −0.015659 | −0.00163 | −0.006339 |
| 247 | 0.004114 | −0.000134 | 0.005646 | −0.006291 | 0.017013 | 0.015307 | −0.00261 | −0.012518 | −0.002424 | 0.02984 | −0.020514 | 0.007292 | −0.007659 | −0.00687 |
| 248 | 0.014099 | 0.01854 | 0.027007 | −0.021404 | −0.003805 | −0.01152 | −0.004057 | −0.020989 | −0.001509 | 0.014043 | −0.019395 | 0.004118 | 0.018418 | −0.032544 |
| 249 | −0.004117 | 0.043432 | 0.022655 | 0.009814 | −0.01712 | −0.02294 | −0.0038 | −0.021544 | 0.009068 | −0.057883 | −0.010883 | −0.016627 | −0.005792 | 0.012844 |
| 250 | 0.001219 | −0.006172 | −0.009346 | −0.005646 | −0.02084 | 0.004426 | 0.023618 | 0.01187 | 0.010502 | 0.022914 | 0.034106 | −0.028098 | −0.008174 | 0.011359 |
| 251 | 0.00459 | −0.025688 | −0.021277 | 0.000282 | −0.009402 | 0.008054 | 0.030366 | −0.000388 | −0.01728 | −0.006234 | 0.000352 | −0.025079 | 0.017564 | −0.028382 |
| 252 | 0.008702 | −0.016369 | −0.04046 | −0.019626 | −0.001872 | 0.027065 | −0.011436 | −0.033789 | 0.004087 | −0.050449 | −0.014066 | −0.028052 | 0.001264 | −0.026261 |
| 253 | −0.011427 | 0.005646 | −0.004406 | 0.015479 | 0.006034 | 0.010933 | 0.005199 | 0.010873 | 0.011944 | −0.018359 | 0.011184 | 0.023978 | 0.00715 | −0.032831 |
| 254 | −0.009529 | −0.003369 | 0.011819 | −0.0311 | 0.009233 | −0.006753 | 0.010353 | 0.019192 | −0.004318 | 0.036764 | −0.001953 | −0.009459 | −0.002555 | 0.007994 |
| 255 | 0.002535 | −0.016196 | −0.002235 | −0.038544 | 0.012682 | 0.014007 | 0.003161 | −0.003266 | 0.000713 | −0.008548 | 0.010453 | −0.002325 | 0.00106 | −0.021839 |
| 256 | −0.00144 | −0.019621 | −0.016167 | −0.026317 | 0.016474 | 0.03507 | −0.016684 | −0.027155 | 0.037842 | −0.047688 | 0.013811 | 0.002099 | −0.008312 | −0.007535 |
| 257 | −0.00204 | −0.027967 | −0.00975 | −0.004958 | −0.029751 | −0.000886 | 0.01206 | 0.002032 | 0.000525 | 0.000738 | −0.005525 | 0.010959 | 0.008808 | −0.007715 |
| 258 | −0.012306 | −0.038456 | −0.013455 | 0.015608 | −0.000039 | 0.022402 | −0.009055 | −0.046225 | −0.007012 | 0.037168 | −0.007688 | 0.03203 | −0.029431 | −0.004111 |
| 259 | 0.006353 | 0.014784 | 0.007107 | −0.000084 | −0.024126 | −0.017024 | −0.007843 | −0.003456 | −0.005594 | −0.005714 | −0.021411 | −0.018604 | 0.004333 | 0.025599 |
| 260 | 0.008841 | 0.02063 | 0.000386 | −0.018533 | 0.03671 | −0.010741 | −0.005728 | 0.009579 | 0.019834 | −0.007795 | 0.01699 | −0.051047 | 0.030017 | −0.002892 |
| 261 | 0.004433 | 0.003206 | −0.006612 | 0.020579 | 0.024314 | −0.01056 | −0.022389 | −0.022042 | 0.001467 | −0.03697 | 0.017747 | −0.019989 | 0.021018 | −0.020991 |
| 262 | −0.008352 | 0.001532 | −0.022435 | 0.014394 | 0.015776 | 0.01169 | 0.001146 | 0.019865 | 0.005846 | −0.025675 | −0.00838 | 0.007437 | −0.000716 | 0.012127 |
| 263 | −0.01736 | −0.015169 | −0.014725 | 0.000053 | −0.007557 | 0.00661 | 0.013933 | 0.000609 | −0.006285 | −0.045029 | −0.01583 | 0.017878 | 0.004277 | 0.010557 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 264 | 0.009733 | 0.008252 | 0.011476 | 0.017967 | −0.021088 | −0.033977 | 0.01541 | −0.009266 | 0.005802 | 0.015209 | −0.016838 | −0.025199 | −0.012202 | 0.013693 |
| 265 | 0.0164441 | −0.008577 | 0.01912 | −0.019551 | 0.007207 | −0.063211 | 0.00822 | −0.017052 | 0.022282 | 0.047141 | 0.009267 | −0.019674 | −0.004308 | 0.013035 |
| 266 | −0.00506 | −0.00804 | −0.000016 | −0.010685 | 0.008163 | −0.027622 | −0.001221 | −0.018539 | 0.038435 | 0.016281 | 0.017459 | 0.033118 | −0.005919 | 0.009683 |
| 267 | 0.001399 | 0.0076 | 0.028296 | 0.001845 | 0.003525 | 0.007266 | −0.00531 | 0.00321 | −0.009066 | 0.041287 | 0.032178 | −0.022298 | −0.018623 | −0.027065 |
| 268 | −0.00718 | −0.015889 | −0.00185 | 0.013908 | −0.007334 | −0.019448 | −0.009157 | −0.021725 | −0.000653 | 0.025867 | −0.01124 | −0.002279 | −0.03159 | −0.018192 |
| 269 | −0.015188 | 0.001002 | 0.008065 | 0.016984 | −0.013753 | −0.012744 | −0.025088 | −0.00514 | 0.003208 | 0.029146 | −0.005413 | −0.013588 | −0.019559 | −0.029518 |
| 270 | 0.005223 | −0.000786 | −0.013302 | −0.000758 | −0.006619 | −0.046418 | −0.026958 | −0.024024 | 0.003113 | 0.005128 | 0.008154 | 0.009531 | −0.005382 | −0.016375 |
| 271 | 0.036639 | 0.047684 | −0.011894 | 0.015784 | 0.031449 | −0.081794 | 0.025997 | −0.015053 | −0.020899 | 0.029671 | 0.001236 | 0.060373 | −0.016914 | −0.013343 |
| 272 | 0.026449 | 0.003379 | −0.014323 | 0.033076 | −0.00974 | 0.019852 | −0.002731 | −0.002261 | −0.019613 | 0.05259 | −0.00203 | −0.016255 | 0.000714 | −0.013436 |
| 273 | 0.026359 | −0.003839 | −0.028457 | 0.013553 | −0.020278 | −0.004828 | −0.0044 | −0.016077 | −0.008226 | −0.00064 | −0.008357 | −0.00294 | 0.018528 | −0.016372 |
| 274 | 0.024808 | 0.002002 | −0.023886 | 0.012724 | −0.016091 | −0.004912 | −0.002821 | −0.007294 | −0.012464 | 0.002186 | −0.002606 | 0.001053 | 0.021482 | −0.012384 |
| 275 | 0.031112 | −0.011454 | −0.01447 | −0.009246 | 0.021242 | −0.019169 | −0.009025 | −0.050843 | 0.005111 | 0.007513 | 0.024401 | −0.015447 | 0.027791 | −0.001934 |
| 276 | −0.000519 | 0.020306 | −0.012387 | 0.000696 | 0.007761 | −0.006452 | 0.000848 | 0.005472 | 0.003006 | 0.011168 | −0.006602 | −0.030988 | −0.008204 | 0.011473 |
| 277 | −0.008685 | −0.022065 | 0.001406 | 0.0234 | 0.021394 | 0.027542 | 0.020155 | 0.018751 | 0.005743 | −0.029055 | 0.00915 | 0.010358 | 0.017492 | 0.007556 |
| 278 | −0.008441 | −0.003501 | 0.005736 | −0.000209 | 0.01247 | 0.005703 | −0.0028 | 0.033851 | 0.013727 | −0.032278 | 0.022619 | −0.0049 | 0.026922 | 0.017312 |
| 279 | 0.011978 | −0.009512 | 0.020044 | −0.021809 | 0.014894 | −0.059432 | 0.015987 | 0.010384 | −0.004849 | −0.001877 | 0.017229 | 0.011181 | 0.011149 | −0.006359 |
| 280 | −0.002787 | 0.012715 | 0.007423 | −0.000347 | −0.021247 | 0.033865 | −0.009864 | −0.025461 | 0.01176 | 0.024667 | 0.015233 | 0.019649 | −0.020528 | 0.026867 |
| 281 | 0.005207 | 0.026503 | 0.008144 | 0.004355 | −0.008051 | −0.040414 | −0.012123 | −0.01485 | 0.001519 | 0.003955 | −0.004713 | −0.023221 | 0.004391 | 0.040824 |
| 282 | −0.005465 | 0.004193 | −0.006315 | −0.012041 | 0.001071 | −0.008759 | −0.016278 | 0.005989 | −0.001049 | 0.013516 | −0.009728 | −0.033579 | −0.005572 | 0.00344 |
| 283 | −0.00058 | 0.028851 | 0.015322 | 0.000971 | 0.032938 | −0.006373 | −0.003211 | 0.001432 | 0.009017 | 0.033476 | 0.003512 | −0.000389 | 0.006477 | −0.004913 |
| 284 | 0.001018 | −0.011043 | −0.006421 | −0.014669 | −0.02679 | −0.027052 | 0.001272 | 0.00977 | 0.002066 | 0.003748 | −0.001513 | −0.004192 | −0.000995 | −0.004719 |
| 285 | −0.006672 | −0.004767 | 0.00457 | −0.609731 | −0.002892 | −0.031481 | 0.006427 | 0.044171 | −0.0066 | −0.024876 | −0.004341 | −0.017485 | 0.01121 | 0.000216 |
| 286 | −0.012342 | 0.010395 | 0.007297 | −0.022085 | −0.010726 | −0.013744 | −0.016695 | −0.005572 | 0.008853 | 0.011888 | −0.01913 | −0.007623 | −0.043049 | 0.041155 |
| 287 | −0.026062 | 0.001732 | −0.003379 | 0.002551 | 0.007959 | 0.021563 | −0.022848 | −0.026241 | 0.007362 | 0.002421 | 0.004959 | 0.004643 | −0.036632 | 0.029774 |
| 288 | 0.001937 | −0.001805 | −0.016458 | 0.009976 | 0.035941 | −0.015617 | −0.019122 | −0.010918 | 0.005985 | 0.006694 | 0.010234 | 0.045143 | −0.026344 | 0.022815 |
| 289 | 0.008505 | −0.006348 | −0.018381 | −0.008807 | 0.018073 | −0.027021 | 0.017159 | 0.007275 | 0.007659 | −0.021994 | 0.007532 | 0.014732 | 0.000771 | 0.020847 |
| 290 | 0.018805 | −0.009396 | −0.008201 | 0.0114 | −0.011859 | −0.014658 | −0.012933 | −0.008904 | 0.002915 | −0.013483 | 0.014745 | 0.033252 | −0.006012 | 0.013792 |
| 291 | 0.016474 | −0.011479 | −0.004387 | 0.013823 | −0.011235 | −0.017528 | −0.015164 | −0.006227 | 0.004485 | −0.013752 | 0.0142 | 0.025946 | −0.012709 | 0.014303 |
| 292 | 0.000155 | −0.021666 | −0.0124 | 0.047353 | −0.024455 | 0.007843 | 0.004168 | 0.00499 | −0.008972 | 0.003507 | 0.01268 | 0.033386 | −0.019089 | 0.002913 |
| 293 | 0.015596 | −0.00561 | 0.033209 | −0.03902 | 0.040034 | 0.00072 | −0.004922 | 0.002227 | 0.028318 | −0.006904 | 0.045708 | 0.024371 | −0.038279 | 0.031346 |
| 294 | 0.017518 | 0.004481 | −0.016979 | −0.004502 | 0.008604 | −0.036035 | −0.02288 | −0.026943 | 0.003109 | −0.014463 | −0.007192 | 0.012547 | −0.032519 | 0.006248 |
| 295 | 0.017332 | 0.038656 | −0.022732 | −0.00189 | −0.008768 | 0.004102 | −0.003237 | 0.012346 | −0.002853 | −0.02237 | −0.010422 | 0.036822 | −0.000942 | 0.007257 |
| 296 | −0.008831 | −0.023716 | −0.04064 | 0.018189 | 0.027135 | −0.030238 | −0.045043 | −0.004175 | −0.03895 | −0.071556 | −0.008808 | 0.045705 | 0.000469 | 0.003198 |
| 297 | −0.009774 | 0.014028 | −0.0472 | 0.014278 | −0.012097 | 0.021893 | −0.012463 | 0.029466 | 0.009703 | −0.017307 | 0.001534 | 0.024099 | −0.003857 | 0.016949 |
| 298 | −0.015377 | −0.036876 | −0.024556 | −0.052292 | −0.073161 | −0.001079 | −0.013988 | 0.028244 | −0.000649 | −0.024608 | −0.000059 | −0.046956 | −0.001125 | −0.015167 |
| 299 | −0.013821 | −0.003146 | −0.059506 | 0.012439 | 0.01381 | −0.009021 | 0.007419 | −0.007511 | −0.022787 | 0.024995 | −0.030698 | 0.008618 | −0.009233 | −0.000706 |
| 300 | −0.002891 | 0.016001 | −0.01779 | −0.021478 | 0.012799 | 0.03143 | 0.029918 | 0.049661 | 0.029003 | 0.017946 | 0.023492 | 0.009631 | 0.012279 | −0.023207 |
| 301 | 0.002504 | 0.006139 | −0.023737 | −0.011488 | −0.009855 | −0.023961 | −0.005065 | 0.006779 | −0.006191 | −0.002958 | −0.022333 | −0.012905 | 0.006225 | −0.015421 |
| 302 | −0.008714 | −0.033028 | −0.038481 | 0.004867 | 0.005961 | −0.054224 | −0.007472 | −0.005353 | −0.03521 | −0.0079f | −0.029302 | −0.003588 | −0.000259 | −0.010493 |
| 303 | −0.033653 | 0.008029 | −0.043084 | 0.038574 | 0.02149 | −0.003604 | −0.031504 | −0.016865 | −0.023976 | 0.040724 | −0.045254 | −0.073611 | −0.038194 | −0.033357 |
| 304 | −0.023237 | −0.021242 | −0.042423 | 0.002286 | 0.022162 | −0.00587 | −0.01634 | 0.008423 | −0.040516 | 0.013032 | −0.036452 | −0.031372 | −0.012351 | −0.04421 |
| 305 | 0.011341 | 0.024073 | 0.043965 | −0.011875 | 0.022395 | 0.002076 | 0.04282 | 0.004981 | −0.025799 | −0.10737 | −0.005244 | −0.006867 | −0.014916 | 0.033551 |
| 306 | −0.002543 | −0.058819 | −0.03982 | 0.035162 | −0.005179 | −0.00907 | 0.002283 | −0.014618 | −0.028398 | −0.004419 | 0.016936 | 0.00236 | −0.003425 | 0.002794 |
| 307 | −0.025088 | −0.006296 | −0.082502 | 0.024468 | −0.025346 | 0.020612 | 0.003519 | −0.0263 | −0.008959 | 0.003855 | 0.041789 | 0.098393 | −0.033104 | −0.024243 |
| 308 | −0.029586 | −0.048961 | −0.027678 | 0.013221 | 0.029606 | 0.004035 | 0.012041 | 0.045066 | −0.049284 | −0.035093 | 0.024566 | 0.027416 | 0.013849 | 0.00513 |
| 309 | −0.055129 | −0.026534 | 0.000323 | −0.018179 | 0.0069 | 0.014234 | −0.051598 | −0.014848 | −0.036867 | −0.008944 | −0.010269 | 0.012187 | −0.03575 | −0.006156 |
| 310 | −0.026567 | −0.024427 | 0.007478 | −0.018712 | 0.022859 | −0.059866 | −0.028149 | −0.000116 | −0.055874 | 0.015268 | −0.009927 | −0.034541 | −0.01024 | 0.005133 |
| 311 | −0.008534 | −0.00233 | 0.002646 | 0.003369 | −0.015132 | 0.010478 | −0.023184 | −0.048356 | −0.00077 | −0.018001 | −0.032936 | −0.030013 | −0.035292 | −0.053609 |
| 312 | −0.005549 | −0.028672 | −0.010638 | −0.049903 | −0.076855 | 0.025698 | 0.003514 | −0.032011 | 0.001022 | −0.022365 | −0.038639 | 0.042025 | −0.036048 | −0.006198 |
| 313 | −0.037583 | −0.033555 | −0.033885 | 0.02935 | −0.041824 | 0.012659 | −0.037744 | −0.035187 | −0.008876 | 0.022009 | −0.038338 | −0.002603 | −0.020821 | −0.010999 |
| 314 | −0.015838 | 0.016347 | −0.046384 | −0.034128 | −0.075138 | 0.003495 | −0.012299 | −0.005685 | 0.021381 | −0.000356 | −0.022454 | 0.010886 | −0.017523 | 0.047376 |

APPENDIX B2-continued

PCA Transformation Matrix (340 × 340; Benign/Malignant)

| | | | | | | | | | | | | | | |
|---|---|---|---|---|---|---|---|---|---|---|---|---|---|---|
| 315 | −0.071969 | −0.023317 | −0.030288 | 0.024519 | 0.007736 | 0.033237 | −0.039207 | −0.021664 | −0.027804 | 0.001342 | −0.017435 | 0.024941 | −0.049992 | 0.015272 |
| 717 | −0.029528 | −0.052988 | 0.020611 | −0.052022 | 0.020761 | −0.045637 | −0.039042 | 0.009871 | −0.001702 | −0.054978 | 0.003768 | −0.009012 | −0.008066 | −0.032912 |
| 317 | −0.051043 | −0.021332 | 0.025927 | −0.037385 | 0.009703 | 0.021446 | −0.045196 | −0.021971 | −0.013075 | 0.007338 | −0.001681 | −0.015525 | −0.006438 | −0.007469 |
| 318 | −0.051482 | −0.017322 | −0.011011 | −0.024117 | 0.016034 | 0.006353 | −0.002354 | 0.014329 | −0.037555 | 0.056295 | −0.019791 | 0.026179 | 0.003036 | −0.00055 |
| 319 | 0.897542 | −0.048816 | 0.000772 | 0.03797 | 0.014693 | 0.053212 | −0.034294 | −0.005159 | −0.022278 | 0.013307 | −0.012729 | −0.008441 | −0.045498 | −0.018249 |
| 320 | −0.030185 | 0.820053 | −0.029406 | −0.007795 | 0.006061 | 0.025426 | 0.016694 | −0.010045 | −0.039843 | −0.002146 | 0.000858 | 0.023805 | −0.026216 | −0.047456 |
| 321 | −0.007427 | −0.018694 | 0.798675 | 0.035169 | −0.048353 | −0.000347 | −0.03348 | −0.01005 | −0.028529 | −0.027342 | −0.037085 | 0.019356 | −0.01898 | 0.027799 |
| 322 | 0.040008 | 0.005014 | 0.02797 | 0.575622 | −0.054652 | −0.012492 | 0.020806 | 0.045553 | −0.004066 | −0.064286 | −0.000472 | −0.060463 | 0.0086 | −0.008103 |
| 323 | −0.002183 | −0.010706 | −0.059933 | −0.039543 | 0.739536 | 0.033637 | 0.027775 | 0.013563 | −0.018828 | −0.032332 | −0.08051 | −0.029552 | −0.032119 | 0.044442 |
| 324 | 0.045719 | 0.016686 | 0.012683 | −0.078281 | 0.017064 | 0.603359 | −0.053327 | −0.014281 | 0.013799 | −0.022261 | 0.03097 | −0.018041 | 0.000578 | −0.018928 |
| 325 | −0.035065 | 0.01203 | −0.019989 | −0.00437 | 0.019342 | −0.052189 | 0.835358 | −0.056206 | −0.006522 | 0.01788 | −0.014095 | −0.019687 | −0.051925 | 0.015754 |
| 326 | 0.003473 | 0.001065 | 0.000697 | 0.045493 | 0.014704 | −0.009521 | −0.045921 | 0.753327 | −0.01328 | 0.014187 | −0.051786 | −0.023162 | −0.04357 | −0.075633 |
| 327 | −0.032194 | −0.035254 | −0.020367 | 0.017718 | −0.005304 | −0.011152 | −0.008778 | −0.002697 | 0.902801 | −0.00028 | −0.047677 | 0.008608 | −0.029348 | −0.017713 |
| 328 | 0.006418 | −0.000307 | −0.019293 | −0.065266 | −0.067696 | 0.000254 | 0.026747 | 0.031335 | −0.004457 | 0.458536 | −0.029217 | −0.039711 | 0.001385 | −0.011378 |
| 329 | −0.027722 | 0.007008 | −0.030626 | 0.024681 | −0.066327 | 0.004361 | −0.009555 | −0.051268 | −0.048801 | 0.007825 | 0.847177 | −0.026436 | −0.044724 | −0.015259 |
| 330 | −0.006175 | −0.004148 | −0.0196 | −0.017895 | −0.018919 | −0.026291 | −0.039462 | −0.045382 | 0.005505 | −0.077728 | −0.005091 | 0.481786 | 0.013308 | −0.171973 |
| 331 | −0.034309 | −0.021017 | −0.022293 | 0.018623 | −0.032791 | −0.005899 | −0.043383 | −0.044192 | −0.030834 | 0.010671 | −0.036316 | 0.03015 | 0.89269 | 0.010512 |
| 332 | −0.009515 | −0.059355 | −0.001755 | −0.028115 | 0.043731 | −0.010234 | −0.004099 | −0.099875 | −0.018091 | −0.057055 | −0.00431 | −0.219978 | −0.000723 | 0.546751 |
| 333 | −0.034198 | 0.004467 | 0.004242 | −0.017215 | −0.017627 | −0.045913 | −0.10313 | −0.0425 | −0.014329 | −0.00057 | −0.021987 | 0.014448 | −0.059833 | 0.00529 |
| 334 | −0.006898 | 0.011592 | −0.000105 | −0.040301 | 0.005136 | 0.008812 | −0.099801 | −0.034668 | 0.017702 | 0.012298 | −0.061854 | −0.009607 | −0.031029 | 0.014616 |
| 335 | −0.045185 | −0.023591 | −0.007713 | 0.02241 | −0.019442 | −0.024805 | −0.056443 | −0.037709 | −0.040007 | 0.021201 | −0.031675 | −0.002189 | −0.050869 | −0.006523 |
| 336 | 0.005466 | 0.040414 | −0.015306 | −0.061498 | −0.012834 | 0.062537 | −0.023069 | −0.033517 | −0.014812 | 0.006601 | −0.018189 | 0.024817 | −0.040397 | 0.051874 |
| 337 | −0.006037 | 0.00069 | 0.00119 | −0.030471 | −0.00009 | −0.047467 | 0.007027 | −0.004116 | −0.014309 | −0.007961 | −0.008761 | −0.001139 | 0.00273 | −0.020976 |
| 338 | 0.009473 | −0.00995 | −0.001569 | −0.074276 | −0.052218 | −0.020244 | 0.002311 | 0.01234 | −0.037621 | −0.038061 | −0.035399 | −0.024527 | −0.0068 | −0.042362 |
| 339 | −0.019996 | −0.020496 | −0.006771 | −0.007321 | −0.052138 | 0.052582 | −0.018974 | −0.04267 | −0.030338 | −0.038262 | −0.051549 | 0.010934 | −0.049902 | −0.007367 |
| 340 | −0.014848 | 0.020241 | −0.017773 | 0.018899 | 0.033565 | 0.037034 | −0.044515 | −0.00936 | −0.010229 | 0.0811081 | −0.009588 | −0.071901 | −0.006101 | −0.069568 |

| | LV | LW | LX | LY | LZ | MA | MB | MC |
|---|---|---|---|---|---|---|---|---|
| 1 | −0.009882 | 0.060475 | −0.036914 | 0.05097 | 0.033586 | −0.019875 | −0.134637 | 0.044609 |
| 2 | 0.0053581 | 0.0929971 | −0.010181 | −0.011966 | −0.033643 | 0.049716 | 0.005788 | 0.137525 |
| 3 | −0.130021 | −0.116156 | −0.067848 | −0.007242 | −0.089861 | 0.035996 | −0.013815 | −0.176878 |
| 4 | 0.007573 | −0.083026 | 0.039613 | 0.093886 | 0.016521 | 0.016362 | 0.054071 | −0.068765 |
| 5 | −0.024388 | −0.038988 | −0.019864 | 0.029372 | 0.034478 | 0.108416 | −0.018188 | 0.169976 |
| 6 | 0.043879 | −0.014521 | 0.000906 | 0.003825 | 0.0995 | 0.066994 | 0.037579 | −0.077458 |
| 7 | 0.0788651 | 0.018292 | 0.090317 | 0.129407 | 0.024989 | 0.055189 | −0.057464 | −0.094437 |
| 8 | −0.011415 | 0.0077151 | 0.0245041 | 0.030802 | 0.001538 | −0.11172 | −0.014674 | −0.079279 |
| 9 | 0.057385 | −0.014388 | 0.019605 | −0.038296 | −0.088348 | −0.001822 | −0.114895 | 0.011119 |
| 10 | −0.080422 | −0.04965 | −0.016895 | −0.042975 | −0.033543 | −0.086651 | 0.096568 | 0.08227 |
| 11 | 0.017059 | −0.032009 | 0.030212 | −0.02969 | 0.050764 | 0.163373 | −0.032985 | −0.055541 |
| 12 | −0.059983 | −0.130021 | −0.048195 | −0.046791 | −0.018816 | 0.152153 | 0.025703 | 0.014363 |
| 13 | 0.032998 | −0.000148 | 0.025338 | 0.07379 | −0.089859 | 0.098852 | 0.012591 | 0.00902 |
| 14 | 0.020039 | −0.045683 | −0.066512 | 0.059587 | 0.075144 | 0.028717 | 0.060126 | −0.032701 |
| 15 | −0.016671 | 0.031067 | −0.035314 | −0.034271 | −0.052252 | −0.013058 | −0.028232 | −0.088878 |
| 16 | 0.025782 | 0.036172 | −0.005439 | 0.019242 | −0.010396 | 0.011666 | 0.028182 | −0.093942 |
| 17 | −0.052576 | −0.05261 | −0.081507 | −0.006257 | −0.007678 | −0.032289 | −0.072732 | 0.120719 |
| 18 | −0.0518 | −0.081642 | −0.030652 | 0.018345 | −0.054117 | −0.021891 | 0.063261 | 0.08809 |
| 19 | 0.016193 | 0.011187 | −0.009396 | −0.012658 | −0.005018 | −0.051003 | 0.008789 | −0.028595 |
| 20 | −0.019524 | 0.060731 | −0.026498 | 0.009274 | −0.093354 | 0.043832 | −0.010433 | −0.039706 |
| 21 | 0.005887 | −0.030135 | 0.010292 | −0.018775 | −0.010461 | −0.011746 | 0.106481 | −0.056284 |
| 22 | −0.017588 | −0.184237 | −0.019525 | −0.046238 | 0.017478 | −0.118726 | −0.019734 | −0.122034 |

APPENDIX B2-continued

PCA Transformation Matrix (340 × 340; Benign/Malignant)

| | | | | | | | | |
|---|---|---|---|---|---|---|---|---|
| 23 | 0.032255 | 0.089349 | 0.024822 | 0.007495 | −0.015916 | −0.089784 | −0.024411 | 0.09209 |
| 24 | 0.039993 | 0.052699 | 0.000851 | 0.030407 | 0.00446 | 0.09975 | −0.025631 | 0.237196 |
| 25 | 0.039511 | 0.017696 | 0.035336 | −0.05537 | −0.034885 | −0.108684 | 0.052385 | −0.09595 |
| 26 | 0.002653 | −0.0508 | −0.043809 | 0.06315 | −0.024564 | −0.003466 | −0.02122 | −0.087743 |
| 27 | 0.029581 | 0.033431 | 0.002536 | 0.001088 | −0.008001 | −0.02628 | 0.01771 | −0.053578 |
| 28 | −0.045335 | 0.013654 | −0.052597 | −0.033412 | −0.02157 | 0.019965 | 0.032946 | −0.101348 |
| 29 | 0.001445 | 0.01956 | 0.009972 | −0.022254 | 0.036355 | 0.032501 | 0.007011 | −0.03201 |
| 30 | 0.017754 | −0.035623 | 0.009665 | −0.050125 | −0.038497 | −0.003384 | −0.091303 | −0.096902 |
| 31 | −0.000988 | 0.010565 | −0.019844 | 0.004201 | 0.117996 | −0.006144 | 0.035984 | −0.091472 |
| 32 | 0.011249 | 0.035747 | 0.0382461 | −0.06681 | 0.007822 | −0.027912 | −0.081524 | 0.021649 |
| 33 | 0.043952 | −0.005065 | 0.0280991 | −0.014409 | −0.077817 | −0.07931 | 0.072309 | −0.160553 |
| 34 | −0.041116 | 0.131869 | −0.017837 | −0.107537 | 0.024791 | 0.044365 | 0.047015 | −0.0162 |
| 35 | 0.019906 | −0.029535 | −0.004971 | −0.013597 | 0.014508 | 0.10981 | 0.004285 | 0.071752 |
| 36 | −0.065601 | −0.086514 | 0.042024 | −0.085032 | 0.006038 | −0.027641 | −0.025906 | −0.002262 |
| 37 | 0.011709 | 0.0798891 | 0.0054071 | −0.029981 | −0.003597 | −0.085811 | 0.012986 | 0.158557 |
| 38 | 0.005185 | 0.054755 | −0.058291 | 0.082487 | 0.037461 | −0.006064 | 0.048421 | −0.028126 |
| 39 | 0.003291 | 0.10733 | 0.019127 | 0.650137 | 0.020729 | 0.049462 | 0.146949 | −0.039828 |
| 40 | −0.070623 | −0.027438 | −0.015528 | 0.123675 | 0.039956 | 0.056963 | −0.063679 | −0.050144 |
| 42 | 0.005577 | −0.011587 | 0.002809 | 0.012035 | −0.028963 | 0.006678 | −0.033793 | 0.009745 |
| 43 | 0.076305 | 0.176734 | 0.071593 | −0.054074 | −0.06834 | −0.015242 | −0.027944 | 0.006286 |
| 44 | −0.068288 | −0.144196 | −0.0247 | 0.024986 | −0.037379 | 0.008283 | −0.08409 | 0.077735 |
| 45 | −0.035641 | −0.04594 | −0.023683 | −0.081381 | 0.009012 | 0.075841 | −0.016691 | 0.006023 |
| 46 | −0.035236 | 0.099454 | 0.024815 | −0.035734 | 0.012946 | −0.050624 | 0.013281 | −0.071754 |
| 47 | −0.030134 | 0.030381 | −0.005697 | −0.03635 | −0.008932 | −0.019668 | −0.033489 | −0.051098 |
| 48 | 0.013769 | 0.01512 | −0.026312 | 0.088839 | −0.081983 | −0.088335 | −0.00881 | 0.0146 |
| 49 | −0.010869 | 0.046993 | −0.064542 | −0.022791 | −0.00653 | −0.081849 | 0.060567 | 0.047957 |
| 50 | −0.001475 | 0.064641 | −0.012982 | −0.061126 | −0.057654 | −0.006818 | −0.078876 | −0.106121 |
| 51 | −0.089667 | −0.085033 | −0.047268 | −0.053764 | −0.024566 | −0.049988 | −0.017405 | −0.047299 |
| 52 | 0.001268 | −0.213366 | 0.044884 | −0.018189 | 0.059779 | −0.101564 | −0.031362 | 0.0138 |
| 53 | −0.010487 | −0.033952 | 0.012509 | −0.092285 | 0.062085 | 0.026808 | 0.012324 | 0.110985 |
| 54 | −0.02719 | 0.019169 | −0.011485 | −0.086513 | 0.048949 | 0.098908 | 0.044716 | 0.054964 |
| 55 | 0.022204 | −0.066627 | 0.062995 | 0.069568 | 0.067433 | 0.072449 | 0.072987 | 0.013449 |
| 56 | 0.014437 | 0.157061 | −0.003056 | −0.032298 | 0.056394 | 0.004827 | −0.057531 | 0.005716 |
| 57 | 0.015932 | 0.088606 | 0.002083 | 0.003173 | 0.030312 | 0.012363 | 0.092316 | −0.019691 |
| 58 | 0.018195 | 0.081017 | −0.059538 | −0.054557 | 0.074106 | −0.038287 | 0.003244 | −0.151524 |
| 59 | 0.03364 | 0.00383 | −0.032659 | 0.057601 | −0.02294 | −0.010953 | −0.038166 | 0.138931 |
| 60 | −0.0366 | 0.144701 | −0.047732 | −0.023552 | 0.006405 | 0.106602 | 0.03098 | 0.010187 |
| 61 | 0.051061 | −0.086829 | 0.079869 | 0.036975 | 0.05297 | 0.012539 | 0.011921 | −0.027055 |
| 62 | −0.004393 | −0.05439 | 0.000047 | −0.069203 | −0.025366 | 0.031412 | 0.022341 | −0.103384 |
| 63 | 0.016028 | −0.068297 | 0.019997 | 0.054085 | −0.016191 | −0.05862 | −0.087041 | −0.00544 |
| 64 | 0.025276 | −0.136198 | 0.01143 | 0.077008 | −0.073757 | −0.106526 | 0.013697 | −0.14904 |
| 65 | 0.007597 | −0.041292 | 0.053685 | −0.042632 | −0.006109 | −0.045766 | −0.119073 | −0.061061 |
| 66 | −0.072017 | −0.000468 | −0.041027 | −0.002677 | 0.004256 | 0.233334 | 0.095589 | −0.043678 |
| 67 | 0.005163 | 0.050805 | −0.060923 | −0.062487 | 0.002071 | −0.018636 | −0.012355 | 0.106858 |
| 68 | −0.062687 | −0.005832 | −0.063215 | −0.046641 | 0.00535 | −0.009789 | −0.006834 | −0.038989 |
| 69 | −0.019544 | 0.095872 | −0.018684 | −0.082028 | 0.012479 | −0.036327 | 0.039329 | −0.041784 |
| 70 | 0.015728 | 0.002707 | 0.044483 | −0.05476 | 0.141592 | −0.064177 | −0.127095 | 0.003543 |
| 71 | 0.075315 | 0.09024 | 0.030631 | −0.050637 | −0.039856 | −0.091271 | 0.098705 | 0.071872 |
| 72 | −0.035681 | −0.049507 | 0.00227 | −0.03085 | −0.090808 | 0.225472 | −0.030252 | −0.040512 |
| 73 | 0.002791 | −0.033057 | −0.011158 | −0.035235 | −0.01034 | −0.046084 | −0.036713 | −0.014214 |
| 74 | −0.020214 | 0.001391 | −0.022986 | −0.031773 | −0.030533 | −0.002961 | −0.106015 | −0.031193 |

APPENDIX B2-continued

PCA Transformation Matrix (340 × 340; Benign/Malignant)

| | | | | | | | | |
|---|---|---|---|---|---|---|---|---|
| 75 | −0.049605 | −0.103639 | 0.047631 | 0.05437 | −0.059551 | 0.021714 | 0.030065 | 0.033121 |
| 76 | 0.001619 | −0.001259 | −0.000829 | 0.132441 | −0.04173 | 0.037153 | 0.014865 | 0.003607 |
| 77 | 0.078654 | −0.066436 | 0.013388 | −0.019969 | −0.082162 | 0.037938 | −0.062259 | −0.072247 |
| 78 | −0.024013 | −0.08259 | 0.033396 | −0.012762 | 0.030265 | −0.024921 | 0.028831 | 0.062725 |
| 79 | −0.099711 | 0.087781 | −0.057895 | −0.058519 | 0.053427 | 0.002995 | −0.021965 | 0.02474 |
| 80 | −0.080414 | −0.028231 | −0.051391 | 0.007672 | 0.058227 | −0.011954 | 0.082223 | −0.060235 |
| 81 | 0.013781 | −0.043148 | −0.061561 | −0.008632 | −0.026057 | 0.004149 | 0.05752 | 0.015606 |
| 82 | −0.015488 | −0.054449 | 0.02106 | −0.050435 | −0.00644 | −0.028127 | −0.005361 | 0.020557 |
| 83 | −0.061717 | −0.0399341 | −0.040279 | −0.099301 | 0.062307 | −0.105365 | −0.035538 | 0.002848 |
| 84 | −0.002017 | 0.072421 | 0.016421 | 0.053739 | 0.022619 | −0.011993 | 0.028789 | −0.014121 |
| 85 | 0.024829 | −0.068096 | −0.00972 | 0.028448 | 0.051326 | −0.06009 | 0.099309 | 0.010354 |
| 86 | −0.009708 | 0.070793 | 0.019108 | 0.050939 | 0.018111 | 0.052815 | −0.00019 | −0.010044 |
| 87 | 0.00707 | −0.051255 | 0.020075 | 0.037742 | 0.035708 | 0.036831 | −0.154107 | −0.069362 |
| 88 | 0.00924 | 0.031499 | −0.029327 | 0.07193 | 0.034112 | 0.014769 | 0.035857 | −0.032254 |
| 89 | −0.004328 | −0.104888 | 0.0261881 | −0.039211 | −0.021828 | 0.044552 | 0.027225 | −0.037214 |
| 90 | 0.018216 | −0.0768641 | 0.0147981 | 0.0408 | 0.014198 | −0.029979 | 0.031449 | 0.110644 |
| 91 | −0.03528 | −0.062713 | 0.074362 | −0.032462 | 0.002848 | 0.132801 | −0.076458 | 0.162048 |
| 92 | 0.020592 | 0.082702 | −0.058026 | 0.014245 | −0.053555 | −0.006604 | −0.025222 | 0.012328 |
| 93 | 0.009993 | 0.0523581 | −0.020287 | 0.123331 | −0.081907 | 0.048148 | −0.062784 | 0.059019 |
| 94 | −0.017642 | 0.007014 | 0.0105391 | 0.049502 | −0.045122 | 0.012507 | 0.014974 | −0.000606 |
| 95 | 0.019733 | 0.0338391 | 0.022011 | −0.028123 | −0.011286 | 0.003573 | 0.014068 | −0.031592 |
| 96 | 0.048015 | −0.052817 | 0.021521 | −0.032703 | 0.015043 | −0.047212 | 0.045458 | −0.021534 |
| 97 | 0.031614 | 0.012495 | −0.046936 | 0.11309 | 0.052126 | 0.005376 | 0.035472 | 0.03534 |
| 98 | 0.067833 | 0.020637 | 0.042448 | −0.145243 | −0.044957 | 0.196762 | −0.000047 | 0.030737 |
| 99 | 0.029271 | 0.0447271 | 0.0575681 | −0.056039 | 0.011596 | 0.06442 | 0.065475 | −0.049263 |
| 100 | −0.003586 | −0.006644 | 0.009211 | 0.0202 | 0.023749 | 0.0273 | 0.028202 | −0.012293 |
| 101 | 0.008669 | −0.000384 | −0.004974 | −0.016615 | 0.015913 | 0.003709 | 0.005666 | −0.031142 |
| 102 | 0.002318 | 0.006979 | −0.000031 | 0.026213 | 0.007122 | 0.018801 | 0.002063 | 0.009933 |
| 103 | −0.019854 | 0.00569 | −0.009218 | 0.035683 | 0.035861 | −0.004602 | 0.022681 | 0.049379 |
| 104 | 0.0208121 | −0.039197 | 0.036023 | −0.000864 | −0.02888 | −0.014574 | 0.03341 | 0.00491 |
| 105 | −0.001814 | −0.002477 | −0.022349 | 0.005011 | −0.024342 | −0.024003 | 0.02837 | 0.027863 |
| 106 | 0.029899 | −0.028639 | 0.012724 | −0.006144 | −0.016411 | 0.003781 | −0.005059 | 0.006689 |
| 107 | 0.002129 | −0.037555 | 0.02128 | −0.026784 | −0.017582 | −0.030183 | −0.05583 | 0.001281 |
| 108 | −0.005802 | 0.022827 | −0.018426 | 0.045814 | 0.052963 | −0.015033 | 0.017699 | −0.030001 |
| 109 | 0.032856 | −0.090067 | 0.012465 | 0.024689 | 0.014411 | −0.018959 | −0.045995 | 0.078512 |
| 110 | −0.01569 | 0.005456 | −0.041202 | −0.000013 | 0.04991 | 0.011395 | 0.013076 | −0.013882 |
| 111 | 0.002892 | 0.041665 | 0.05043 | 0.051026 | 0.012943 | −0.01906 | −0.011458 | 0.052957 |
| 112 | 0.001981 | −0.012854 | −0.010843 | 0.021066 | 0.002856 | −0.005467 | −0.01131 | −0.000639 |
| 113 | 0.0044 | −0.007479 | 0.023008 | −0.022417 | 0.009918 | 0.029055 | 0.059662 | −0.013998 |
| 114 | 0.017679 | 0.055161 | 0.0135481 | −0.011306 | −0.040632 | 0.029454 | −0.020558 | 0.021103 |
| 115 | −0.034915 | −0.034395 | −0.026421 | 0.011551 | −0.022233 | −0.029266 | 0.041369 | −0.094354 |
| 116 | 0.032964 | 0.080627 | −0.017014 | 0.044886 | −0.085338 | −0.014997 | 0.006429 | 0.013836 |
| 117 | −0.016243 | −0.005028 | 0.003111 | 0.048042 | −0.019589 | −0.017929 | −0.018919 | −0.000055 |
| 118 | 0.007685 | 0.017396 | 0.025668 | −0.021334 | 0.011659 | 0.031592 | 0.063298 | −0.013799 |
| 119 | −0.022061 | −0.017742 | −0.004974 | 0.04114 | 0.019907 | 0.020707 | −0.035967 | −0.041322 |
| 120 | −0.024367 | −0.008322 | −0.017927 | 0.03837 | −0.018426 | 0.016673 | −0.040744 | −0.011467 |
| 121 | −0.029867 | −0.026527 | −0.003706 | 0.053691 | −0.014493 | 0.006586 | −0.092425 | 0.013929 |
| 122 | 0.010477 | −0.039977 | 0.025149 | −0.008676 | 0.012803 | −0.037525 | 0.005936 | 0.023501 |
| 123 | −0.014241 | −0.007736 | 0.001654 | −0.01658 | 0.005377 | −0.032725 | −0.048268 | −0.005734 |
| 124 | 0.00853 | −0.004581 | 0.0063311 | −0.015926 | 0.022111 | 0.037732 | 0.026454 | −0.011766 |
| 125 | 0.00401 | 0.0605471 | −0.000988 | −0.056051 | −0.009162 | 0.026252 | 0.004175 | 0.027069 |

APPENDIX B2-continued

PCA Transformation Matrix (340 × 340; Benign/Malignant)

| | | | | | | | | |
|---|---|---|---|---|---|---|---|---|
| 126 | 0.013047 | 0.021147 | 0.0133721 | −0.020001 | 0.011109 | −0.014711 | 0.006071 | −0.014335 |
| 127 | 0.008023 | 0.005567 | 0.004346 | 0.009113 | −0.000033 | −0.015094 | −0.000233 | −0.002817 |
| 128 | 0.023181 | 0.024836 | 0.025756 | −0.002493 | 0.00421 | 0.010726 | 0.036634 | −0.023473 |
| 129 | 0.004267 | 0.004984 | 0.041134 | −0.018897 | 0.027231 | 0.002438 | −0.046706 | −0.06275 |
| 130 | 0.0059221 | −0.059055 | 0.009231 | −0.031483 | −0.025791 | −0.01901 | 0.002551 | −0.028387 |
| 131 | −0.013899 | 0.01186 | 0.000715 | −0.022609 | −0.014367 | 0.012452 | 0.027291 | 0.033339 |
| 132 | 0.008266 | −0.023636 | 0.000066 | 0.01632 | −0.02189 | 0.05665 | −0.055276 | 0.032805 |
| 133 | 0.019842 | −0.014312 | −0.012302 | 0.077284 | 0.019379 | −0.035369 | −0.020819 | −0.040648 |
| 134 | 0.022218 | −0.001505 | 0.013884 | 0.029361 | 0.018183 | −0.112044 | 0.008827 | 0.101699 |
| 135 | 0.0010511 | −0.035027 | −0.021584 | 0.013788 | 0.010753 | 0.01229 | 0.036982 | 0.025554 |
| 136 | 0.034021 | 0.000479 | 0.010362 | 0.014221 | 0.028533 | 0.046143 | 0.041489 | −0.015546 |
| 137 | −0.013896 | 0.040464 | 0.007239 | −0.055031 | 0.012165 | −0.033324 | 0.044646 | 0.002733 |
| 138 | −0.02662 | −0.007835 | −0.014488 | 0.029198 | −0.032956 | 0.033047 | −0.000591 | −0.00042 |
| 139 | 0.0160071 | −0.013171 | −0.014598 | 0.006268 | 0.066318 | 0.045612 | 0.012542 | 0.036832 |
| 140 | −0.000278 | 0.02338 | 0.0332111 | −0.033342 | 0.02942 | 0.050948 | 0.045502 | 0.014734 |
| 141 | −0.036318 | 0.012686 | −0.028355 | −0.071723 | −0.010633 | −0.009336 | −0.000362 | −0.00642 |
| 142 | 0.011403 | 0.007273 | −0.005642 | 0.017175 | −0.046313 | −0.036921 | −0.006968 | −0.001165 |
| 143 | 0.007471 | −0.040647 | −0.006768 | 0.002557 | −0.001656 | 0.003608 | −0.035906 | −0.017371 |
| 144 | −0.035089 | 0.010817 | −0.037784 | −0.007354 | 0.021387 | −0.001062 | −0.02176 | −0.003198 |
| 145 | 0.0198131 | −0.001003 | −0.002726 | 0.022636 | 0.033348 | 0.037728 | −0.026861 | 0.017314 |
| 146 | 0.015766 | 0.047562 | −0.029091 | 0.029468 | 0.018019 | −0.021073 | 0.035159 | −0.012421 |
| 147 | 0.034893 | −0.041976 | 0.027318 | −0.007708 | 0.014135 | −0.012318 | −0.019371 | −0.035778 |
| 148 | 0.005143 | 0.062904 | −0.016322 | −0.044892 | 0.03728 | −0.037204 | 0.0639 | −0.068108 |
| 149 | −0.006231 | 0.029694 | 0.005356 | −0.041541 | 0.003809 | −0.016669 | 0.045407 | 0.026249 |
| 150 | −0.009783 | 0.006195 | −0.005878 | −0.02308 | −0.031674 | −0.025303 | 0.013617 | −0.031276 |
| 151 | −0.003764 | −0.015287 | −0.008824 | −0.023675 | −0.011341 | 0.060436 | −0.013473 | −0.028054 |
| 152 | −0.0172 | −0.000163 | 0.003748 | −0.012097 | 0.000857 | 0.063916 | −0.00008 | 0.048453 |
| 153 | −0.023021 | 0.016451 | −0.058631 | −0.006343 | 0.006083 | 0.015035 | 0.000433 | 0.017074 |
| 154 | 0.008138 | −0.014796 | −0.009228 | 0.017003 | −0.03847 | 0.01022 | 0.002523 | 0.020501 |
| 155 | −0.006153 | 0.076178 | −0.005872 | −0.011004 | −0.013706 | −0.016432 | −0.017471 | 0.031778 |
| 156 | 0.004935 | 0.038392 | −0.000571 | 0.022851 | −0.05135 | −0.031213 | −0.021949 | −0.011595 |
| 157 | −0.010243 | 0.029944 | 0.029688 | −0.005354 | −0.013167 | 0.036295 | 0.014989 | −0.035068 |
| 158 | −0.031611 | 0.002987 | 0.005007 | −0.024477 | −0.032827 | 0.032197 | 0.023188 | 0.016537 |
| 159 | −0.002909 | −0.00514 | −0.001628 | −0.047017 | 0.025017 | −0.053013 | −0.07496 | 0.058132 |
| 160 | 0.018944 | 0.005552 | 0.0061881 | 0.003338 | 0.015534 | 0.01524 | 0.012653 | −0.087467 |
| 161 | 0.019463 | 0.041311 | −0.017324 | −0.032152 | −0.053782 | 0.012346 | −0.01471 | 0.019893 |
| 162 | −0.018859 | 0.016051 | 0.009768 | −0.001772 | −0.009474 | 0.024356 | −0.00097 | 0.016843 |
| 163 | 0.014132 | −0.055969 | 0.03594 | 0.006685 | −0.018106 | −0.033143 | 0.00597 | 0.042399 |
| 164 | 0.027075 | 0.015554 | 0.000389 | −0.049114 | −0.001238 | −0.002143 | 0.009691 | −0.028513 |
| 165 | −0.003077 | −0.020609 | 0.0053831 | 0.018174 | −0.055679 | −0.097316 | −0.044701 | −0.009814 |
| 166 | −0.009561 | 0.011712 | −0.017158 | −0.012726 | 0.003816 | 0.008707 | −0.05496 | −0.048757 |
| 167 | 0.015316 | −0.047945 | 0.005615 | 0.028959 | 0.031211 | −0.023186 | −0.01511 | 0.039018 |
| 168 | 0.039199 | 0.010306 | 0.035444 | 0.012544 | −0.026008 | 0.021121 | 0.008627 | −0.030875 |
| 169 | 0.013618 | −0.012598 | 0.011561 | 0.000213 | −0.014716 | 0.001179 | −0.027277 | 0.022798 |
| 170 | 0.006868 | −0.000779 | 0.007005 | −0.023303 | −0.053822 | 0.023655 | −0.04033 | 0.031783 |
| 171 | 0.001439 | 0.0077641 | 0.01451 | −0.009891 | −0.013835 | −0.005208 | −0.046158 | 0.041591 |
| 172 | 0.006137 | −0.009641 | 0.005126 | 0.013099 | 0.019843 | 0.03358 | 0.016757 | −0.007618 |
| 173 | −0.012776 | 0.005016 | −0.005448 | 0.004844 | 0.025509 | −0.023192 | 0.010154 | 0.031878 |
| 174 | 0.009154 | −0.005102 | −0.011161 | −0.01639 | −0.009344 | 0.036794 | 0.004118 | 0.027734 |
| 175 | −0.011341 | 0.058033 | 0.004396 | −0.011596 | 0.020232 | 0.057194 | 0.030574 | 0.020491 |
| 176 | −0.009558 | −0.035961 | 0.0078241 | −0.010428 | −0.005122 | 0.063249 | −0.010358 | 0.018227 |

APPENDIX B2-continued

PCA Transformation Matrix (340 × 340; Benign/Malignant)

| | | | | | | | | |
|---|---|---|---|---|---|---|---|---|
| 177 | 0.032636 | −0.045958 | 0.004461 | −0.01386 | −0.03825 | 0.012411 | 0.035235 | −0.024234 |
| 178 | 0.018571 | −0.022502 | 0.021538 | −0.024571 | 0.036411 | 0.015282 | −0.020295 | 0.000234 |
| 179 | 0.010949 | −0.001542 | 0.01561 | 0.020314 | −0.009367 | −0.030923 | −0.025704 | −0.045573 |
| 180 | −0.006686 | −0.010221 | 0.010261 | −0.016997 | 0.007654 | −0.011431 | −0.026543 | −0.009304 |
| 181 | −0.002448 | 0.0030421 | −0.002134 | 0.006446 | 0.007393 | −0.00997 | −0.021529 | −0.012726 |
| 182 | −0.022108 | 0.0068641 | −0.001995 | 0.006316 | −0.004154 | 0.003947 | −0.019014 | −0.056068 |
| 183 | 0.005402 | 0.03772 | 0.019789 | 0.023174 | −0.007722 | −0.024101 | −0.018848 | −0.02697 |
| 184 | −0.017089 | 0.027276 | 0.003729 | −0.001833 | 0.02057 | 0.051455 | −0.017035 | 0.075729 |
| 185 | −0.05981 | −0.017568 | −0.015118 | −0.024177 | 0.006707 | −0.020724 | 0.035559 | 0.003821 |
| 186 | −0.027133 | −0.050631 | −0.028935 | −0.067229 | 0.015283 | −0.064268 | −0.061786 | 0.015819 |
| 187 | 0.003674 | 0.010003 | −0.008288 | 0.002615 | 0.019441 | −0.00033 | 0.027756 | 0.008735 |
| 188 | −0.001177 | −0.003565 | −0.013038 | −0.001576 | 0.009658 | 0.044474 | 0.018705 | 0.021433 |
| 189 | −0.01638 | −0.023856 | −0.019262 | 0.012272 | 0.01016 | 0.084404 | 0.04371 | 0.017098 |
| 190 | −0.015852 | 0.023607 | 0.008125 | −0.051779 | −0.033803 | 0.029333 | −0.032984 | 0.004068 |
| 191 | −0.00304 | 0.035604 | 0.000564 | −0.012811 | −0.039685 | 0.013038 | 0.007906 | −0.039359 |
| 192 | −0.011164 | −0.005942 | −0.021858 | 0.028479 | −0.02536 | −0.019389 | −0.002738 | −0.056506 |
| 193 | 0.000863 | 0.011237 | 0.004873 | −0.002358 | −0.017336 | 0.016512 | −0.016275 | −0.005123 |
| 194 | 0.001188 | −0.02456 | 0.006214 | −0.021398 | −0.012518 | −0.06324 | −0.03856 | 0.001184 |
| 195 | −0.000945 | 0.01572 | −0.017223 | 0.021909 | −0.019323 | −0.067996 | −0.005265 | −0.004479 |
| 196 | 0.0048921 | 0.021704 | −0.011297 | 0.02011 | 0.009736 | −0.011775 | −0.032352 | 0.00528 |
| 197 | −0.038303 | −0.011369 | −0.022665 | −0.011768 | −0.030509 | −0.005063 | −0.00963 | −0.014642 |
| 198 | 0.003115 | 0.015913 | −0.005378 | −0.049853 | −0.028077 | −0.00819 | 0.045003 | 0.000247 |
| 199 | −0.038447 | −0.017609 | −0.008959 | −0.036039 | −0.03786 | 0.021033 | 0.017948 | −0.036759 |
| 200 | 0.0371 | 0.014697 | −0.023728 | 0.009672 | 0.034926 | −0.032041 | 0.012107 | 0.004139 |
| 201 | −0.013934 | −0.119708 | 0.0290791 | −0.003168 | −0.016355 | −0.022568 | −0.028943 | −0.052191 |
| 202 | 0.002698 | −0.080732 | 0.010383 | 0.001311 | 0.003281 | −0.033207 | −0.046449 | −0.026787 |
| 203 | 0.027064 | −0.004032 | 0.035966 | 10.012636 | −0.098936 | −0.002885 | −0.054994 | −0.046004 |
| 204 | −0.003405 | −0.03942 | −0.026791 | 0.032478 | −0.011828 | 0.11618 | 0.016241 | −0.076293 |
| 205 | −0.051016 | −0.055276 | −0.007323 | 0.009695 | −0.036376 | 0.050134 | 0.017460 | 0.014336 |
| 206 | −0.003471 | −0.024941 | 0.003019 | −0.025576 | −0.000615 | 0.002747 | 0.007627 | 0.014724 |
| 207 | 0.025969 | −0.049009 | 0.042086 | 0.005027 | 0.030147 | −0.005174 | −0.067553 | −0.085585 |
| 208 | −0.030696 | −0.012366 | −0.021532 | −0.005871 | −0.03805 | −0.011468 | 0.005278 | 0.060667 |
| 209 | −0.0156 | −0.02733 | 0.005576 | 0.03593 | −0.034785 | −0.000233 | −0.030078 | 0.035014 |
| 210 | 0.022781 | 0.006848 | 0.039671 | −0.044486 | 0.057743 | −0.044973 | −0.053411 | 0.025427 |
| 211 | 0.001721 | −0.036254 | 0.032502 | 0.051845 | 0.103747 | −0.010382 | 0.033122 | −0.000206 |
| 212 | −0.009992 | −0.028975 | −0.012095 | 0.015134 | 0.029141 | 0.005953 | −0.060849 | 0.091669 |
| 213 | −0.000629 | 0.026405 | 0.007598 | −0.019603 | 0.033916 | 0.009703 | −0.042314 | −0.040685 |
| 214 | 0.009201 | −0.010842 | 0.007492 | 0.024171 | 0.011874 | −0.019769 | −0.005155 | −0.023786 |
| 215 | −0.00719 | −0.03429 | −0.006155 | −0.030747 | 0.023515 | −0.043681 | −0.048693 | 0.042238 |
| 216 | −0.000916 | 0.006294 | −0.003587 | −0.061917 | 0.057394 | 0.019065 | −0.004263 | 0.011917 |
| 217 | 0.009826 | 0.014616 | 0.000121 | 0.003278 | 0.020318 | −0.026251 | 0.027447 | −0.012671 |
| 218 | −0.010498 | −0.052431 | −0.0251 | 0.0004 | 0.008084 | −0.012383 | −0.015258 | 0.058822 |
| 219 | −0.000597 | 0.002595 | −0.032536 | −0.000928 | −0.004316 | −0.005431 | −0.000635 | 0.02664 |
| 220 | 0.002047 | 0.007868 | −0.008694 | 0.026764 | −0.024837 | 0.013752 | 0.067274 | 0.020763 |
| 221 | 0.001154 | −0.020084 | 0.001922 | 0.011572 | 0.020475 | −0.042799 | 0.016016 | −0.023168 |
| 222 | −0.000407 | −0.012092 | −0.009821 | 0.04514 | 0.028325 | −0.024785 | 0.007951 | 0.024521 |
| 223 | 0.026798 | 0.001927 | 0.008248 | 0.01046 | 0.011543 | −0.002245 | 0.009506 | −0.005813 |
| 224 | −0.004152 | −0.009899 | −0.009226 | 0.007494 | −0.011231 | −0.008126 | −0.025297 | 0.04231 |
| 225 | 0.005788 | 0.011033 | 0.004235 | 0.005689 | −0.030238 | −0.033881 | −0.03806 | 0.032098 |
| 226 | −0.019793 | −0.006129 | −0.016145 | −0.003855 | 0.001441 | 0.02314 | −0.016032 | 0.019074 |
| 227 | −0.013179 | −0.032709 | 0.014668 | −0.04052 | 0.001164 | 0.028617 | −0.028639 | 0.049448 |

APPENDIX B2-continued

PCA Transformation Matrix (340 × 340; Benign/Malignant)

| | | | | | | | | |
|---|---|---|---|---|---|---|---|---|
| 228 | −0.022138 | −0.022219 | −0.005874 | −0.005112 | 0.028908 | 0.063891 | −0.040534 | −0.033427 |
| 229 | 0.011053 | −0.03019 | 0.01048 | 0.019379 | −0.016501 | 0.001224 | −0.024589 | 0.024858 |
| 230 | 0.01548 | −0.005725 | 0.013324 | −0.033396 | 0.027673 | −0.021448 | −0.005872 | −0.023671 |
| 231 | 0.011403 | 0.017695 | 0.014138 | 0.011795 | 0.012552 | −0.007599 | 0.045436 | 0.005391 |
| 232 | −0.004276 | 0.06364 | −0.008306 | 0.008511 | 0.00773 | −0.012885 | −0.028587 | 0.011714 |
| 233 | 0.004809 | −0.025042 | −0.013537 | 0.020944 | 0.028897 | −0.004238 | 0.058596 | −0.014827 |
| 234 | 0.022953 | −0.00611 | 0.00244 | 0.014325 | −0.022941 | 0.012087 | 0.002359 | 0.041818 |
| 235 | 0.016716 | 0.030441 | −0.003473 | 0.061488 | −0.015371 | −0.002375 | 0.033194 | 0.040092 |
| 236 | −0.00225 | 0.04831 | 0.00502 | −0.042292 | 0.019421 | −0.013181 | −0.003752 | 0.017875 |
| 237 | 0.00884 | −0.013953 | 0.005288 | −0.0541 | −0.004862 | 0.020834 | −0.003286 | −0.024936 |
| 238 | 0.00156 | 0.015048 | −0.010917 | 0.009777 | −0.012955 | 0.01291 | −0.007633 | −0.023153 |
| 239 | 0.011065 | 0.018829 | 0.006176 | 0.034619 | 0.010527 | −0.006521 | −0.027349 | −0.015172 |
| 240 | 0.006422 | 0.010035 | 0.009671 | −0.009193 | −0.002365 | −0.03749 | −0.026573 | 0.008013 |
| 241 | 0.028127 | −0.014491 | −0.004225 | 0.019895 | −0.001385 | −0.006961 | −0.009686 | 0.028379 |
| 242 | −0.030068 | −0.020514 | −0.008279 | 0.031476 | 0.011838 | 0.031524 | 0.011666 | −0.013865 |
| 243 | −0.014844 | −0.012501 | −0.023279 | −0.027809 | 0.006905 | 0.019333 | −0.002266 | −0.057611 |
| 244 | 0.006391 | 0.001314 | 0.015306 | 0.00943 | 0.007782 | −0.028856 | 0.002648 | −0.03411 |
| 245 | 0.006574 | −0.009424 | 0.007617 | 0.015034 | −0.004948 | −0.004953 | −0.027867 | 0.023994 |
| 246 | −0.010767 | −0.012893 | 0.010493 | −0.004676 | −0.014558 | 0.025404 | 0.018282 | 0.012059 |
| 247 | 0.0017681 | −0.008635 | 0.0146761 | −0.032529 | 0.001612 | 0.002244 | 0.016363 | −0.017031 |
| 248 | −0.002746 | 0.01149 | 0.0072691 | −0.012891 | 0.008856 | −0.021476 | 0.014725 | −0.011432 |
| 249 | −0.017229 | −0.033373 | −0.013474 | 0.001605 | 0.001744 | −0.044186 | −0.038981 | 0.028177 |
| 250 | 0.004763 | 0.026503 | 0.008182 | −0.015981 | −0.006732 | −0.032619 | −0.016678 | 0.01744 |
| 251 | 0.023221 | 0.0135 | −0.001023 | 0.017822 | −0.028172 | −0.03665 | −0.009124 | 0.007783 |
| 252 | −0.007653 | −0.030042 | −0.003026 | 0.020419 | 0.007459 | −0.035578 | −0.046269 | −0.039205 |
| 253 | 0.02309 | 0.049634 | −0.004104 | 0.027822 | −0.018181 | −0.002441 | 0.006814 | 0.007078 |
| 254 | 0.0098621 | 0.018293 | 0.0053921 | 0.006258 | −0.012676 | 0.021706 | 0.000315 | 0.005958 |
| 255 | −0.000777 | −0.013241 | 0.005308 | −0.012633 | −0.004826 | 0.001822 | 0.031171 | −0.021808 |
| 256 | −0.013071 | −0.042507 | −0.008382 | −0.0459 | −0.024344 | 0.045024 | −0.007348 | 0.027142 |
| 257 | −0.006912 | 0.0172031 | 0.000025 | 0.002534 | 0.003949 | −0.021892 | 0.008953 | −0.025891 |
| 258 | 0.0089361 | 0.0065411 | −0.005581 | −0.027319 | 0.010089 | −0.019207 | −0.039623 | 0.01435 |
| 259 | −0.009526 | −0.008444 | −0.017798 | 0.016249 | 0.017085 | −0.003089 | −0.016958 | −0.009541 |
| 260 | 0.014651 | 0.018839 | 0.013987 | 0.018912 | −0.0053 | −0.020985 | −0.001619 | −0.05066 |
| 261 | 0.016897 | −0.014823 | 0.004697 | 0.039067 | −0.007751 | −0.024284 | −0.035333 | −0.010532 |
| 262 | 0.009399 | −0.010356 | 0.015384 | 0.017138 | 0.030717 | −0.009358 | −0.006768 | 0.025168 |
| 263 | 0.0137321 | 0.020606 | 0.0058611 | 0.035242 | 0.034781 | −0.014575 | −0.000389 | 0.01932 |
| 264 | 0.0003311 | 0.015791 | 0.0001561 | 0.033554 | 0.015211 | 0.027522 | 0.026834 | 0.042512 |
| 265 | 0.017868 | 0.027292 | 0.017779 | 0.013531 | −0.032727 | 0.037355 | 0.03146 | −0.003394 |
| 266 | 0.006252 | −0.009504 | −0.000279 | 0.023857 | −0.025503 | 0.018495 | 0.046187 | −0.018193 |
| 267 | 0.004781 | 0.026132 | 0.017251 | −0.028729 | 0.008523 | 0.050406 | 0.006371 | 0.070102 |
| 268 | −0.017137 | −0.000291 | −0.008372 | 0.000656 | 0.002542 | 0.007648 | −0.025419 | 0.032295 |
| 269 | −0.028672 | −0.008246 | −0.017702 | 0.010385 | −0.003492 | 0.004895 | 0.014924 | 0.022137 |
| 270 | −0.023081 | −0.003545 | −0.008902 | −0.011193 | −0.007173 | 0.014575 | 0.015115 | 0.025496 |
| 271 | −0.017606 | −0.037618 | 0.029669 | 0.013964 | −0.061266 | −0.020464 | 0.045986 | 0.046052 |
| 272 | 0.018023 | −0.00556 | 0.004437 | 0.022014 | −0.035952 | 0.011239 | −0.010114 | −0.024207 |
| 273 | 0.005127 | 0.00044 | 0.004673 | 0.001432 | −0.003629 | −0.045923 | −0.010887 | −0.036705 |
| 274 | 0.007452 | 0.003633 | 0.004337 | 0.002952 | −0.011441 | −0.039261 | 0.005101 | −0.039389 |
| 275 | 0.004605 | −0.001846 | 0.009243 | −0.042346 | 0.021864 | −0.029001 | −0.002147 | −0.019475 |
| 276 | −0.003859 | 0.034281 | −0.002746 | 0.002507 | 0.016006 | 0.016269 | −0.01825 | 0.0386 |
| 277 | 0.022061 | 0.021516 | 0.024963 | 0.016822 | 0.026494 | 0.025021 | 0.006679 | −0.003187 |
| 278 | 0.0097771 | 0.0217721 | 0.0110381 | 0.037132 | 0.033822 | −0.006215 | 0.018246 | −0.012512 |

APPENDIX B2-continued

PCA Transformation Matrix (340 × 340; Benign/Malignant)

| | | | | | | | | |
|---|---|---|---|---|---|---|---|---|
| 279 | 0.0101221 | 0.0538871 | −0.010851 | 0.055754 | −0.000813 | −0.012578 | −0.019721 | 0.001797 |
| 280 | 0.00146 | 0.01932 | −0.020915 | −0.011058 | 0.006767 | 0.026692 | 0.000764 | −0.020667 |
| 281 | 0.001704 | −0.019718 | 0.000909 | 0.006232 | −0.035487 | 0.019579 | −0.01266 | 0.009892 |
| 282 | −0.012353 | −0.032906 | −0.005273 | 0.016746 | −0.009597 | −0.003621 | −0.00359 | 0.017671 |
| 283 | 0.0125371 | 0.006314 | 0.011988 | −0.031351 | 0.006547 | 0.017464 | 0.014159 | 0.007083 |
| 284 | −0.010467 | 0.022102 | −0.010354 | 0.008949 | −0.007745 | −0.0149 | −0.003205 | −0.00271 |
| 285 | −0.012134 | 0.002842 | −0.011525 | 0.006877 | −0.005509 | −0.012263 | −0.007293 | −0.000437 |
| 286 | −0.001958 | −0.012756 | −0.032228 | 0.000801 | 0.002644 | −0.013078 | −0.046328 | 0.025996 |
| 287 | −0.002907 | −0.02122 | −0.021965 | −0.014916 | 0.026433 | 0.005451 | −0.047101 | 0.008862 |
| 288 | −0.001694 | −0.024084 | −0.005032 | −0.023524 | 0.004253 | 0.001161 | −0.026038 | 0.059248 |
| 289 | 0.003001 | 0.024939 | 0.013358 | −0.01293 | −0.006191 | −0.000668 | 0.028389 | 0.044807 |
| 290 | −0.010947 | −0.018364 | 0.01203 | −0.004848 | −0.021236 | 0.004662 | −0.027275 | 0.02294 |
| 291 | −0.015038 | −0.018596 | 0.011232 | −0.00208 | −0.016054 | 0.002877 | −0.02726 | 0.020382 |
| 292 | −0.006807 | 0.010009 | 0.00454 | 0.020116 | −0.020541 | 0.033688 | −0.012108 | 0.017443 |
| 293 | −0.018903 | 0.00571 | 0.009185 | −0.048548 | −0.027146 | −0.006911 | −0.077082 | −0.038861 |
| 294 | −0.021455 | −0.050476 | −0.006243 | −0.030199 | −0.009434 | 0.014925 | 0.012447 | 0.061536 |
| 295 | −0.018527 | −0.009903 | 0.012697 | −0.021395 | −0.037822 | −0.00313 | −0.000965 | −0.022037 |
| 296 | −0.010291 | −0.020582 | 0.007271 | 0.012572 | −0.033157 | −0.034021 | 0.029455 | 0.006471 |
| 297 | −0.008388 | −0.028338 | 0.009547 | 0.022893 | −0.027534 | 0.02582 | 0.006492 | −0.025237 |
| 298 | 0.009157 | 0.028717 | 0.015438 | −0.007908 | −0.006901 | −0.068828 | 0.025617 | 0.008013 |
| 299 | 0.022462 | 0.010704 | −0.009488 | −0.004312 | −0.060785 | 0.009972 | 0.00906 | −0.031572 |
| 300 | 0.036996 | 0.018801 | 0.025242 | −0.006716 | 0.029352 | 0.055056 | 0.036574 | −0.001324 |
| 301 | −0.016609 | −0.002426 | 0.002917 | −0.011408 | −0.043987 | −0.005795 | −0.005628 | −0.011653 |
| 302 | 0.002498 | −0.015855 | −0.012366 | 0.002291 | −0.004195 | −0.017587 | 0.016857 | 0.025619 |
| 303 | 0.013186 | 0.007881 | −0.027074 | −0.005061 | −0.026722 | 0.018428 | 0.008137 | −0.018901 |
| 304 | 0.030488 | 0.02055 | −0.027601 | −0.006265 | −0.01698 | 0.012514 | −0.00864 | −0.021043 |
| 305 | 0.022665 | 0.015515 | 0.026058 | −0.02762 | −0.042709 | 0.053431 | −0.018511 | −0.041826 |
| 306 | 0.026037 | 0.039249 | −0.00449 | −0.016603 | −0.020972 | −0.031811 | −0.012044 | −0.026105 |
| 307 | −0.021635 | 0.052078 | −0.045694 | −0.028764 | −0.042898 | −0.047606 | −0.087337 | 0.017865 |
| 308 | 0.0324 | 0.025534 | −0.028513 | 0.03896 | 0.023887 | −0.007405 | 0.017019 | −0.012905 |
| 309 | −0.048413 | −0.022678 | −0.036751 | −0.026683 | 0.022518 | −0.006455 | −0.007846 | −0.016592 |
| 310 | −0.008244 | 0.035063 | −0.027262 | −0.013108 | 0.004817 | −0.048273 | 0.045906 | 0.012501 |
| 311 | −0.041865 | 0.021039 | −0.007228 | −0.038081 | −0.016698 | −0.013285 | −0.067618 | 0.004003 |
| 312 | 0.032361 | −0.088435 | −0.01774 | −0.017812 | −0.031096 | −0.001812 | −0.025459 | −0.021142 |
| 313 | −0.027092 | 0.001759 | −0.025436 | 0.030268 | 0.001165 | 0.043643 | −0.009529 | −0.027584 |
| 314 | 0.007533 | −0.060416 | 0.024082 | −0.057619 | 0.012594 | 0.028178 | −0.045264 | 0.034862 |
| 315 | −0.03742 | −0.035406 | −0.02803 | −0.020136 | −0.027257 | 0.037115 | −0.022394 | −0.030031 |
| 316 | −0.011956 | −0.028406 | −0.033032 | 0.019283 | −0.032203 | −0.068357 | −0.004962 | 0.022654 |
| 317 | −0.057114 | −0.004508 | −0.010056 | −0.052215 | −0.006716 | −0.000173 | −0.009032 | −0.010722 |
| 318 | −0.030434 | 0.00247 | −0.014902 | −0.031206 | 0.001996 | 0.030779 | 0.001469 | −0.041597 |
| 319 | −0.043119 | 0.005142 | −0.047435 | 0.000836 | 0.000016 | 0.020313 | −0.009919 | −0.008055 |
| 320 | 0.006925 | 0.034294 | −0.022051 | 0.015257 | −0.019325 | −0.021918 | −0.027331 | 0.029839 |
| 321 | −0.011275 | −0.004915 | −0.023392 | −0.013812 | 0.005038 | 0.026044 | −0.029976 | 0.034032 |
| 322 | 0.017758 | 0.013164 | 0.028065 | −0.053893 | −0.013116 | −0.089715 | −0.01956 | 0.018308 |
| 323 | −0.019042 | 0.018398 | −0.036742 | −0.007813 | 0.011912 | −0.042244 | −0.052287 | 0.043431 |
| 324 | −0.036884 | −0.037137 | −0.020739 | 0.05669 | −0.068204 | −0.072742 | 0.047275 | 0.008428 |
| 325 | −0.108766 | −0.10316 | −0.061314 | −0.003976 | 0.008712 | 0.025086 | −0.009646 | −0.039417 |
| 326 | −0.044356 | −0.010859 | −0.037098 | −0.069968 | −0.020253 | 0.000369 | −0.032618 | −0.036468 |
| 327 | −0.019264 | 0.038995 | −0.044278 | −0.007857 | −0.001305 | −0.013069 | 0.011654 | 0.010094 |
| 328 | 0.008997 | −0.028289 | 0.002318 | −0.032659 | −0.022251 | −0.072395 | −0.020927 | 0.064311 |
| 329 | −0.037141 | −0.012115 | −0.052205 | 0.010458 | 0.003802 | 0.00132 | −0.003666 | 0.00074 |

APPENDIX B2-continued

| PCA Transformation Matrix (340 × 340; Benign/Malignant) | | | | | | | | |
|---|---|---|---|---|---|---|---|---|
| 330 | −0.01367 | −0.03067 | −0.020188 | 0.030865 | 0.005569 | 0.035331 | −0.012419 | −0.024858 |
| 331 | −0.068483 | −0.011381 | −0.064231 | −0.029389 | 0.005656 | 0.022673 | −0.037804 | 0.020616 |
| 332 | −0.007716 | 0.061935 | −0.008346 | 0.024297 | −0.023445 | −0.04651 | −0.004522 | −0.032382 |
| 333 | 0.853252 | −0.066705 | −0.073113 | −0.032521 | −0.004942 | 0.034898 | −0.007397 | −0.006191 |
| 334 | −0.071031 | 0.515176 | 0.008838 | 0.036236 | −0.008557 | −0.032918 | −0.080989 | −0.065568 |
| 335 | −0.067818 | 0.018858 | 0.8751091 | 0.003192 | −0.002379 | 0.00321 | 0.017952 | 0.000673 |
| 336 | −0.038871 | 0.012459 | −0.000655 | 0.71138 | 0.011806 | 0.029545 | −0.017406 | −0.011998 |
| 337 | 0.000499 | −0.012556 | −0.006356 | −0.005809 | 0.784688 | −0.009656 | −0.024439 | −0.025345 |
| 338 | 0.019725 | 0.000932 | 0.00052 | −0.036785 | 0.000405 | 0.516104 | −0.044269 | −0.039149 |
| 339 | −0.017088 | −0.05005 | −0.005455 | −0.032248 | −0.035583 | −0.04094 | 0.674859 | 0.028835 |
| 340 | −0.003359 | −0.037041 | −0.002109 | 0.006806 | −0.010954 | −0.050728 | 0.038259 | 0.421013 |

APPENDIX B3

PCA Transformation
Matrix (340 × 340 Early/Late)

| | A | B | C | D | E | F | G | H | I | J | K |
|---|---|---|---|---|---|---|---|---|---|---|---|
| 1 | 409.4/255.3 > GPA.Lyso 16.0 | −0.084549 | −0.000648 | 0.081762 | 0.080819 | 0.038706 | 0.010787 | −0.045519 | 0.035218 | −0.046088 | −0.016411 |
| 2 | 433.4/279.3 > GPA:Lyso 18:2 | −0.074727 | 0.047237 | 0.029063 | 0.11057 | 0.01461 | 0.006678 | 0.044697 | 0.055951 | −0.020971 | −0.088282 |
| 3 | 435.4/281.3 > GPA:Lyso 18:1 | −0.088986 | 0.039208 | 0.056817 | 0.079403 | 0.003212 | 0.022162 | −0.003429 | 0.074578 | −0.013487 | −0.043968 |
| 4 | 437.4/283.3 > GPA:Lyso 18:0 | 0.008577 | −0.075046 | 0.106548 | 0.082045 | 0.012322 | −0.022934 | −0.029038 | −0.010448 | 0.026385 | −0.048348 |
| 5 | 451.4/283.3 > GPA:Lyso 18:0 | −0.039483 | 0.007818 | 0.055426 | 0.068624 | 0.042155 | 0.042458 | −0.076885 | −0.018428 | −0.116266 | −0.04669 |
| 6 | 459.6/305.5 > GPA:Lyso 20:3 | −0.065711 | 0.024051 | −0.021933 | 0.093235 | 0.000983 | 0.043241 | −0.025647 | 0.027906 | 0.058762 | 0.057287 |
| 7 | 461.6/307.5 > GPA:Lyso 20:2 | −0.045924 | 0.065727 | 0.059163 | 0.081275 | −0.038754 | 0.056616 | 0.021197 | −0.004018 | 0.022231 | 0.008291 |
| 8 | 463.7/309.5 > GPA:Lyso 20:1 | −0.020674 | −0.002813 | 0.085687 | 0.034615 | −0.040521 | 0.060833 | 0.039675 | −0.032529 | −0.06427 | −0.011393 |
| 9 | 465.7/311.5 > GPA:Lyso 20:0 | 0.008414 | −0.10711 | 0.053022 | 0.055033 | 0.02517 | −0.01043 | −0.051646 | −0.041891 | 0.01234 | −0.062678 |
| 10 | 481.4/327.3 > GPA:Lyso 22:6 | −0.061688 | 0.063678 | 0.014834 | 0.079968 | 0.061715 | −0.033865 | 0.031208 | −0.030259 | 0.08316 | −0.006904 |
| 11 | 483.4/329.3 > GPA:Lyso 22:5 | −0.035269 | −0.014568 | 0.000043 | 0.101294 | 0.014047 | 0.032856 | −0.072654 | −0.03499 | −0.046341 | 0.000795 |
| 12 | 641.8/251.3 > GPA:16:1/16:2 | −0.000351 | −0.011831 | 0.035237 | −0.00862 | −0.010556 | 0.022016 | 0.051198 | 0.031248 | −0.08175 | −0.039489 |
| 13 | 643.8/253.3 > GPA:16:1/16:1 | 0.027797 | −0.000013 | 0.014108 | −0.053528 | −0.01869 | −0.11933 | −0.016316 | 0.181048 | −0.049332 | 0.031493 |
| 14 | 645.8/255.3 > GPA:16:1/16:0 | 0.008807 | −0.020653 | 0.017412 | −0.038791 | −0.016934 | −0.096273 | −0.034201 | 0.192294 | −0.064717 | 0.023281 |
| 15 | 647.8/255.3 > GPA:16:0/16:0 | −0.090392 | 0.026209 | 0.061768 | 0.051539 | −0.017056 | −0.049419 | −0.060098 | 0.075181 | −0.034656 | 0.018098 |
| 16 | 667.8/279.3 > GPA:34:4 | 0.009559 | 0.000391 | 0.044239 | 0.04565 | 0.043263 | 0.041421 | 0.005554 | −0.045043 | −0.081576 | −0.052005 |
| 17 | 669.8/279.3 > GPA:34:3 | −0.054256 | −0.030403 | −0.011201 | 0.108873 | −0.013784 | −0.006764 | 0.033962 | 0.140091 | −0.006833 | 0.001443 |
| 18 | 669.8/281.3 > GPA:34:4 | −0.060664 | −0.033022 | 0.015472 | 0.075757 | 0.073943 | −0.018497 | −0.057347 | 0.006092 | −0.073785 | 0.019968 |
| 19 | 671.8/279.3 > GPA:18:2/16:0 | −0.046403 | −0.006511 | 0.031314 | 0.136441 | 0.029596 | −0.033683 | −0.014686 | 0.045534 | −0.093366 | −0.030186 |
| 20 | 673.8/281.3 > GPA:18:1/16:0 | −0.040705 | 0.002721 | 0.04104 | 0.021149 | −0.165263 | −0.088407 | −0.058469 | 0.019035 | −0.01501 | 0.050669 |
| 21 | 695.8/279.3 > GPA:36:4 | −0.056722 | 0.044629 | 0.02137 | 0.098011 | −0.001177 | 0.010527 | 0.096371 | 0.052944 | −0.038472 | −0.094251 |
| 22 | 695.8/303.3 > GPA:36:4 | −0.0654 | 0.030245 | 0.062724 | 0.086903 | 0.019367 | −0.061297 | −0.060302 | −0.005814 | −0.006665 | −0.034821 |
| 23 | 697.8/281.3 > GPA:20:3/16:0 | −0.067288 | 0.043764 | 0.054932 | 0.038512 | −0.022704 | −0.007269 | −0.042753 | 0.031164 | −0.068748 | 0.046753 |
| 24 | 697.8/305.3 > GPA:18:1/18:2 | −0.067993 | 0.033445 | 0.05299 | 0.088708 | −0.033984 | 0.004531 | 0.010651 | 0.064795 | −0.056643 | −0.048085 |
| 25 | 699.8/279.3 > GPA:36:2 | −0.065045 | 0.019918 | 0.029264 | 0.105708 | −0.055765 | −0.006488 | 0.062411 | 0.062399 | −0.006 | −0.023989 |
| 26 | 699.8/281.3 > GPA:36:2 | −0.040531 | 0.008199 | 0.047452 | 0.004505 | −0.174347 | −0.068453 | −0.059723 | −0.006733 | 0.000731 | 0.052999 |
| 27 | 701.8/283.3 > GPA:36:1 | −0.036393 | 0.001462 | 0.035516 | 0.024618 | −0.174531 | −0.080064 | −0.049263 | −0.04176 | 0.010152 | 0.036652 |
| 28 | 703.8/283.3 > GPA:36:0 | −0.053272 | −0.050884 | 0.080113 | 0.063909 | −0.079948 | −0.061026 | −0.046663 | −0.032321 | 0.013727 | −0.028009 |
| 29 | 721.8/255.3 > GPA:18:1/20:4 | −0.040826 | 0.008236 | 0.065408 | 0.031371 | −0.092165 | −0.108316 | 0.002741 | −0.039586 | 0.001623 | −0.044451 |
| 30 | 721.8/281.3 > GPA:16:0/22:5 | −0.053233 | −0.065222 | 0.112649 | 0.028282 | −0.000769 | 0.024667 | −0.002301 | 0.008927 | 0.056135 | −0.002042 |
| 31 | 723.8/283.3 > GPA:18:0/20:4 | −0.035654 | 0.012715 | 0.040483 | 0.027431 | −0.145995 | −0.092225 | −0.05961 | −0.103997 | 0.007762 | −0.00277 |
| 32 | 725.8/305.3 > GPA:20:3/18:0 | −0.038534 | 0.01596 | 0.023725 | 0.031475 | −0.097113 | −0.002468 | −0.050103 | −0.045813 | 0.057531 | 0.059859 |
| 33 | 729.8/281.3 > GPA:38:1 | −0.058607 | −0.003398 | 0.007166 | 0.092136 | −0.104572 | −0.049391 | −0.009764 | 0.011201 | −0.049996 | 0.0525 |
| 34 | 731.8/283.3 > GPA:38:0 | −0.051736 | −0.040539 | 0.099232 | 0.062281 | −0.057345 | −0.046225 | −0.032547 | −0.00396 | 0.062121 | −0.029227 |
| 35 | 751.8/303.3 > GPA:40:4 | −0.02126 | 0.094516 | −0.005654 | 0.085443 | 0.010083 | −0.013756 | 0.075194 | −0.029842 | −0.033062 | 0.021068 |
| 36 | 757.8/281.3 > GPA:40:1 | −0.08045 | −0.005904 | 0.047669 | −0.048821 | −0.087218 | −0.006379 | 0.045608 | −0.028216 | −0.022902 | 0.022434 |
| 37 | 759.8/283.3 > GPA:40:0 | −0.056693 | −0.038662 | 0.002662 | 0.048179 | −0.141134 | −0.061963 | −0.061544 | −0.037445 | 0.007856 | 0.064876 |
| 38 | 777.8/329.3 > GPA:42:5 | −0.018089 | −0.020002 | 0.071834 | 0.030203 | 0.04085 | 0.042476 | −0.01206 | 0.098592 | −0.089013 | 0.012458 |
| 39 | 481.4/253.3 > GPGro:Lyso 16:1 | 0.006199 | −0.044947 | 0.098709 | 0.10218 | −0.00499 | −0.004916 | −0.087745 | 0.081685 | 0.004316 | 0.013494 |
| 40 | 483.4/255.3 > GPGro:Lyso 16:0 | −0.042684 | −0.049177 | 0.082744 | 0.084666 | 0.061793 | −0.059203 | −0.043531 | 0.070765 | 0.030787 | −0.020373 |
| 41 | 507.4/279.3 > GPGro:Lyso 18:2 | −0.025813 | −0.037471 | 0.069511 | 0.113698 | 0.052515 | −0.058452 | −0.006876 | 0.087861 | 0.029405 | −0.057712 |
| 42 | 509.4/281.3 > GPGro:Lyso 18:1 | −0.000845 | −0.04825 | 0.089478 | 0.107019 | 0.046348 | −0.02644 | −0.081365 | 0.04703 | −0.025707 | −0.03292 |
| 43 | 511.4/283.3 > GPGro:Lyso 18:0 | −0.017174 | −0.061846 | 0.093997 | 0.083375 | 0.046248 | −0.066654 | −0.0162 | 0.062736 | 0.055472 | −0.025254 |
| 44 | 531.4/303.3 > GPGro:Lyso 20:4 | −0.037975 | 0.010137 | 0.074432 | 0.107926 | 0.0662 | −0.084627 | −0.059156 | 0.06559 | 0.036588 | −0.000588 |
| 45 | 555.4/327.3 > GPGro:Lyso 22:6 | −0.026348 | −0.008115 | 0.074704 | 0.107263 | −0.070699 | −0.077981 | −0.016658 | 0.028502 | 0.077939 | −0.040795 |
| 46 | 557.4/329.3 > GPGro:Lyso 22:5 | −0.018474 | 0.004355 | 0.024108 | 0.141341 | 0.082304 | −0.069596 | −0.056616 | 0.056796 | 0.06634 | −0.012589 |

APPENDIX B3-continued

| | PCA Transformation Matrix (340 × 340 Early/Late) | | | | | | | | | | |
|---|---|---|---|---|---|---|---|---|---|---|---|
| 47 | 717.8/253.3 > GPGro:16:1/16:1 | 0.004054 | 0.007536 | 0.010303 | −0.042743 | −0.09226 | 0.090127 | −0.109775 | 0.104198 | 0.097442 | −0.015229 |
| 48 | 719.8/253.3 > GPGro:16:1/16:0 | 0.043423 | −0.053495 | 0.010354 | 0.094452 | −0.038393 | 0.029779 | −0.1032 | 0.095175 | 0.018852 | 0.030901 |
| 49 | 721.8/255.3 > GPGro:16:0/16:0 | −0.047187 | −0.071574 | 0.1111 | 0.020537 | −0.008129 | 0.019358 | 0.014468 | 0.019844 | 0.044876 | −0.002464 |
| 50 | 743.8/279.3 > GPGro:18:2/16:1 | 0.004285 | 0.046731 | −0.094733 | −0.075074 | −0.034786 | −0.028194 | 0.09541 | 0.013859 | −0.122187 | −0.053639 |
| 51 | 743.8/281.3 > GPGro:18:1/16:2 | −0.004687 | 0.030989 | −0.019131 | −0.123175 | −0.042903 | 0.066212 | −0.085299 | 0.034942 | 0.028506 | 0.009421 |
| 52 | 745.8/279.3 > GPGro:18:2/16:0 | 0.025255 | 0.045091 | −0.091681 | −0.045301 | −0.01917 | −0.019715 | 0.092687 | 0.016148 | −0.097698 | −0.044368 |
| 53 | 745.8/281.3 > GPGro:18:1/16:1 | −0.027 | 0.016733 | −0.034116 | −0.131221 | −0.056487 | 0.047472 | −0.108873 | 0.007485 | −0.006212 | 0.02956 |
| 54 | 747.8/255.2 > GPGro:16:0/18:1 | 0.065478 | −0.042605 | 0.017213 | 0.052776 | 0.003308 | −0.022384 | −0.118119 | 0.061278 | −0.074399 | 0.029233 |
| 55 | 747.8/281.1 > GPGro:16:0/18:1 | −0.067611 | 0.047243 | 0.051053 | −0.088939 | −0.072993 | 0.040362 | −0.056879 | −0.041575 | −0.007982 | 0.027204 |
| 56 | 749.8/283.3 > GPGro:18:0/16:0 | −0.045149 | −0.062768 | 0.116813 | 0.02112 | −0.002911 | 0.006957 | 0.029342 | 0.017736 | 0.060031 | 0.013011 |
| 57 | 767.8/303.3 > GPGro:20:4/16:1 | 0.013695 | 0.114597 | −0.029001 | −0.01905 | 0.040117 | −0.018865 | −0.086056 | −0.059127 | −0.067659 | 0.058396 |
| 58 | 769.8/279.3 > GPGro:18:2/18:2 | 0.019555 | −0.020959 | −0.123052 | 0.066521 | −0.025737 | −0.010895 | 0.085252 | 0.061169 | −0.007568 | 0.026067 |
| 59 | 769.8/303.3 > GPGro:20:4/16:0 | 0.028888 | 0.046295 | 0.016803 | 0.057864 | 0.045378 | −0.083128 | −0.09438 | 0.02581 | −0.008519 | 0.043544 |
| 60 | 771.8/279.3 > GPGro:18:2/18:1 | −0.008161 | 0.048099 | −0.012533 | −0.041112 | −0.061121 | 0.073609 | 0.175419 | −0.019117 | 0.024729 | 0.027336 |
| 61 | 773.8/279.3 > GPGro:18:2/18:0 | 0.048004 | −0.037688 | 0.065179 | 0.048431 | −0.024802 | −0.047157 | 0.087546 | 0.100672 | 0.029401 | 0.012611 |
| 62 | 773.8/281.3 > GPGro:18:1/18:1 | −0.001946 | 0.00455 | −0.003781 | −0.042075 | −0.099065 | 0.12233 | 0.004614 | 0.056256 | 0.118603 | 0.137306 |
| 63 | 775.8/281.3 > GPGro:18:1/18:0 | 0.050552 | −0.047445 | 0.106024 | 0.054126 | 0.000194 | −0.012335 | −0.054181 | 0.084598 | 0.019316 | 0.022737 |
| 64 | 777.8/283.3 > GPGro:18:0/18:0 | −0.038258 | −0.081888 | 0.096334 | 0.045057 | 0.013431 | 0.025969 | 0.037751 | 0.016881 | 0.093892 | 0.02844 |
| 65 | 795.8/303.3 > GPGro:20:4/18:1 | 0.005782 | 0.118824 | −0.003598 | −0.004992 | 0.02126 | 0.020382 | −0.025873 | −0.079243 | 0.001648 | 0.128232 |
| 66 | 797.8/303.3 > GPGro:20:4/18:0 | 0.034026 | 0.013611 | 0.07246 | 0.040429 | 0.069268 | −0.11144 | −0.025717 | 0.01286 | 0.047678 | 0.107402 |
| 67 | 821.8/327.3 > GPGro:22:6/18:0 | 0.002875 | 0.027968 | 0.08069 | 0.044932 | 0.079571 | −0.100455 | 0.000445 | 0.011828 | 0.097542 | 0.058624 |
| 68 | 823.8/329.3 > GPGro:22:5/18:0 | 0.014123 | 0.065213 | 0.073335 | 0.053529 | 0.056982 | 0.007148 | −0.071809 | 0.023796 | −0.051303 | 0.090297 |
| 69 | 494.4/407.4 > Lyso GPSer:16:1 | 0.032041 | −0.002521 | 0.014846 | −0.053979 | −0.007764 | −0.098737 | −0.020352 | 0.169957 | −0.089281 | 0.08302 |
| 70 | 496.4/409.4 > Lyso GPSer:16:0 | 0.022628 | −0.00139 | 0.029286 | −0.053785 | 0.0108 | −0.10349 | −0.018332 | 0.174008 | −0.070657 | 0.012724 |
| 71 | 522.4/435.4 > Lyso GPSer:18:1 | −0.028667 | −0.023862 | −0.002593 | 0.011638 | −0.129383 | −0.121268 | −0.059676 | 0.022588 | −0.035898 | −0.052957 |
| 72 | 524.4/437.4 > Lyso GPSer:18:0 | −0.034209 | −0.053233 | 0.027685 | 0.013594 | −0.089544 | −0.052122 | −0.029739 | −0.103253 | −0.036093 | −0.071726 |
| 73 | 544.4/457.4 > Lyso GPSer:20:4 | −0.023919 | 0.019658 | 0.053441 | 0.024052 | −0.027773 | −0.023933 | −0.006324 | −0.057467 | −0.026265 | −0.071636 |
| 74 | 570.4/483.4 > Lyso GPSer:22:5 | 0.008746 | −0.049239 | −0.104821 | 0.063343 | 0.012182 | −0.010863 | −0.031769 | −0.046053 | −0.067034 | −0.048477 |
| 75 | 732.6/645.6 > GPSer:32:1 | 0.031689 | 0.000525 | 0.0012 | −0.060933 | 0.006022 | −0.099352 | −0.026523 | 0.192076 | −0.063473 | 0.024214 |
| 76 | 734.6/647.6 > GPSer:32:0 | 0.01653 | −0.030955 | −0.06031 | −0.045489 | 0.014869 | −0.095341 | −0.034267 | 0.157204 | −0.055697 | 0.013048 |
| 77 | 758.6/671.6 > GPSer:34:2 | 0.034484 | −0.006673 | −0.003947 | −0.049995 | 0.008486 | −0.101849 | −0.029111 | 0.191043 | −0.063393 | 0.028305 |
| 78 | 760.8/673.8 > GPSer:34:1 | 0.030186 | 0.000951 | 0.00812 | −0.053757 | −0.013711 | −0.108481 | −0.031501 | 0.186411 | −0.068593 | 0.029855 |
| 79 | 762.8/675.7 > GPSer:34:0 | 0.016927 | −0.001459 | 0.013311 | −0.069704 | −0.012528 | −0.113083 | −0.033793 | 0.173339 | −0.068991 | 0.020791 |
| 80 | 782.6/695.7 > GPSer:36:4 | 0.032913 | −0.067394 | 0.032521 | −0.017855 | 0.026368 | −0.088863 | 0.029868 | −0.021503 | 0.077209 | 0.00983 |
| 81 | 784.8/697.8 > GPSer:36:3 | −0.002168 | −0.064684 | −0.083452 | −0.017058 | −0.00817 | −0.100834 | −0.029912 | 0.092668 | −0.000227 | 0.02684 |
| 82 | 786.8/699.8 > GPSer:36:2 | −0.024196 | −0.027211 | −0.010013 | 0.01964 | −0.161361 | −0.124781 | −0.044766 | −0.012128 | −0.003982 | 0.048354 |
| 83 | 788.8/701.8 > GPSer:36:1 | −0.032375 | −0.003494 | 0.021632 | 0.026526 | −0.173853 | −0.090294 | −0.051523 | −0.049743 | 0.006439 | 0.024164 |
| 84 | 790.8/703.8 > GPSer:36:0 | −0.029209 | −0.010194 | 0.02306 | 0.025273 | −0.177052 | −0.078422 | −0.057128 | −0.052955 | 0.002702 | 0.007574 |
| 85 | 808.6/721.6 > GPSer:38:6 | 0.00143 | −0.037705 | 0.037028 | −0.057288 | −0.064464 | −0.107713 | 0.044948 | −0.067507 | −0.002647 | −0.026265 |
| 86 | 810.8/723.8 > GPSer:38:5 | 0.000045 | −0.015457 | −0.03545 | 0.013951 | −0.108191 | −0.130539 | −0.019941 | −0.090007 | −0.006372 | −0.025489 |
| 87 | 812.8/725.8 > GPSer:38:4 | −0.014427 | 0.014617 | 0.02084 | 0.017761 | −0.158016 | −0.097905 | −0.054625 | −0.067219 | 0.025207 | −0.051129 |
| 88 | 814.6/727.6 > GPSer:38:3 | −0.026693 | −0.002894 | 0.034968 | 0.02028 | −0.169304 | −0.100086 | −0.042911 | −0.050962 | 0.010955 | 0.032863 |
| 89 | 816.8/729.8 > GPSer:38:2 | −0.032503 | 0.004308 | 0.030785 | 0.02793 | −0.173226 | −0.08259 | −0.050453 | −0.038855 | 0.014879 | 0.027183 |
| 90 | 818.8/731.8 > GPSer:38:1 | −0.031289 | 0.002822 | 0.035176 | 0.019647 | −0.173992 | −0.083062 | −0.047926 | −0.041807 | 0.011733 | 0.012501 |
| 91 | 834.8/747.8 > GPSer:40:6 | −0.027814 | −0.009429 | 0.024609 | 0.025555 | −0.171681 | −0.101053 | −0.044643 | −0.056653 | 0.002619 | 0.03593 |
| 92 | 836.8/749.8 > GPSer:40:5 | −0.003147 | −0.014157 | −0.029707 | −0.008663 | −0.125178 | −0.109411 | −0.039564 | −0.081294 | −0.034196 | −0.033837 |
| 93 | 838.8/751.8 > GPSer:40:4 | −0.009958 | −0.003487 | 0.047537 | −0.000965 | −0.163477 | −0.105056 | −0.034437 | −0.055336 | 0.005125 | 0.013906 |
| 94 | 840.6/753.7 > GPSer:40:3 | −0.005615 | −0.049527 | −0.01051 | −0.008841 | −0.124343 | −0.140605 | 0.008145 | −0.079119 | −0.003684 | 0.041957 |
| 95 | 778.9/97 > Sulfatide:16:0 | 0.016302 | −0.02748 | 0.014347 | 0.104261 | 0.039018 | −0.085663 | −0.002487 | −0.015885 | −0.083921 | −0.01057 |
| 96 | 806.9/9 > Sulfatide:18:0 | −0.001141 | −0.045679 | 0.107606 | 0.025323 | 0.071201 | 0.005948 | −0.046757 | 0.012123 | −0.066544 | −0.030522 |

APPENDIX B3-continued

| | | PCA Transformation Matrix (340 × 340 Early/Late) | | | | | | | | | |
|---|---|---|---|---|---|---|---|---|---|---|---|
| 97 | 822.9/97 > Sulfatide:18:0 (OH) | −0.095525 | −0.016243 | −0.049308 | 0.012494 | 0.051875 | −0.026813 | 0.015329 | −0.002007 | −0.045387 | 0.104611 |
| 98 | 834.9/97 > Sulfatide:20:0 | 0.056747 | −0.092537 | 0.007494 | −0.001845 | 0.071282 | −0.100236 | 0.005516 | −0.03928 | 0.079077 | 0.000075 |
| 99 | 850.9/97 > Sulfatide:20:0 (OH) | −0.105862 | 0.020285 | 0.003933 | −0.017896 | 0.05559 | −0.03305 | −0.003986 | −0.004763 | −0.071157 | 0.070435 |
| 100 | 862.9/97 > Sulfatide:22:1 | 0.066278 | −0.093063 | −0.012856 | 0.041081 | 0.074072 | −0.049712 | −0.025872 | −0.022339 | 0.001262 | 0.023132 |
| 101 | 878.9/97 > Sulfatide: 22:1 (OH) | 0.040056 | −0.087532 | −0.01523 | −0.022099 | 0.074618 | −0.104641 | 0.026327 | −0.030252 | 0.116304 | 0.018055 |
| 102 | 888.9/97 > Sulfatide:24:1 | 0.032839 | 0.013001 | 0.015621 | 0.083783 | 0.047994 | −0.003923 | −0.053536 | 0.049116 | −0.079343 | 0.011132 |
| 103 | 890.9/97 > Sulfatide:24:0 | −0.00573 | −0.080516 | −0.036305 | 0.059671 | 0.073797 | −0.024767 | −0.027251 | 0.034688 | −0.03698 | 0.003532 |
| 104 | 906.7/97 > Sulfatide:24:0 (OH) | −0.034241 | −0.019549 | −0.094248 | 0.090856 | 0.056081 | −0.013166 | −0.036807 | −0.003955 | −0.008282 | 0.130685 |
| 105 | 1147/281.3 > CardioliGPInsn:52:3 | 0.004792 | −0.034616 | 0.09377 | 0.015228 | 0.005839 | 0.064483 | 0.005191 | −0.041394 | −0.023954 | −0.048371 |
| 106 | 1376/281.3 > CardioliGPInsn:66:2 | −0.080159 | 0.025333 | 0.040025 | −0.055358 | −0.017126 | 0.099668 | 0.036971 | 0.005636 | 0.04007 | 0.004299 |
| 107 | 1400/281.3 > CardioliGPInsn:68:4 | −0.078227 | 0.009138 | 0.053104 | −0.060849 | −0.039646 | 0.070954 | 0.016315 | 0.030699 | 0.021724 | −0.003607 |
| 108 | 1402/281.3 > CardioliGPInsn:68:3 | −0.063864 | −0.000224 | 0.078253 | −0.031912 | −0.019391 | 0.084728 | −0.007399 | 0.060129 | −0.029703 | −0.013253 |
| 109 | 1404/281.3 > CardioliGPInsn:68:2 | −0.057349 | 0.019329 | 0.055606 | −0.031995 | −0.02247 | 0.028549 | −0.031621 | 0.022098 | −0.03548 | 0.053402 |
| 110 | 1406/281.3 > CardioliGPInsn:68:1 | 0.005151 | −0.012337 | 0.073345 | −0.080439 | 0.023458 | 0.003997 | 0.034183 | −0.023955 | 0.032633 | 0.044503 |
| 111 | 1426/281.3 > CardioliGPInsn:70:5 | −0.075517 | −0.006845 | 0.078642 | −0.010095 | −0.010243 | 0.066509 | −0.025296 | 0.045127 | 0.019599 | 0.033546 |
| 112 | 1428/281.3 > CardioliGPInsn:70:4 | −0.071999 | −0.012942 | 0.0793 | −0.019723 | 0.015625 | 0.056832 | −0.036894 | 0.026784 | −0.036305 | −0.071137 |
| 113 | 1430/281.3 > CardioliGPInsn:70:3 | −0.078636 | 0.010763 | 0.066727 | −0.029946 | −0.010235 | 0.069271 | 0.00853 | 0.04071 | −0.059914 | 0.020663 |
| 114 | 1432/281.3 > CardioliGPInsn:70:2 | −0.032424 | −0.032762 | 0.098035 | −0.004864 | −0.03155 | 0.054002 | −0.017101 | −0.003551 | −0.002296 | −0.110952 |
| 115 | 1434/281.3 > CardioliGPInsn:70:1 | −0.075067 | −0.03004 | 0.06438 | 0.02519 | −0.006941 | 0.040241 | −0.020943 | 0.013788 | −0.038919 | −0.004946 |
| 116 | 1436/281.3 > CardioliGPInsn:70:0 | −0.035984 | −0.013238 | 0.079785 | −0.052141 | −0.052649 | 0.032015 | −0.00327 | 0.008147 | 0.08373 | 0.003808 |
| 117 | 436.6/196.1 > Lyso GPEtn:Lyso16:1e/16:0p | 0.027003 | −0.044346 | −0.002865 | 0.04906 | −0.005151 | 0.024777 | 0.015393 | −0.038993 | −0.154355 | −0.042651 |
| 118 | 450.4/196.1 > Lyso GPEtn:Lyso 16:1 | 0.01055 | −0.048231 | −0.029237 | 0.064732 | −0.081221 | 0.078468 | −0.068711 | 0.03606 | 0.001529 | −0.018067 |
| 119 | 452.4/196.1 > Lyso GPEtn:Lyso 16:0 | −0.043425 | −0.05576 | −0.027445 | 0.016705 | −0.042823 | 0.085224 | −0.093434 | −0.047068 | −0.108081 | −0.035978 |
| 120 | 462.4/196.1 > Lyso GPEtn:Lyso18:2e/18:1p | 0.000954 | −0.088589 | −0.077553 | 0.075157 | 0.003903 | 0.029796 | −0.028723 | −0.010335 | −0.100579 | −0.057605 |
| 121 | 464.5/196.1 > Lyso GPEtn:Lyso18:1e/18:0p | 0.01383 | −0.017369 | 0.031265 | 0.072606 | 0.021444 | −0.018613 | 0.047841 | −0.042136 | −0.094894 | 0.066243 |
| 122 | 476.6/196.1 > Lyso GPEtn:Lyso18:2a | −0.000793 | 0.020576 | −0.002273 | 0.093848 | −0.075986 | 0.06667 | 0.117166 | 0.084371 | −0.031725 | −0.089328 |
| 123 | 478.4/196.1 > Lyso GPEtn:Lyso 18:1 | −0.001358 | −0.019347 | −0.022122 | 0.090486 | −0.091522 | 0.079161 | 0.049984 | 0.051724 | −0.037898 | −0.057294 |
| 124 | 480.4/196.1 > Lyso GPEtn:Lyso 18:0 | −0.060562 | −0.037252 | −0.044653 | 0.025804 | −0.067677 | 0.085649 | −0.080128 | 0.00363 | −0.03193 | −0.033417 |
| 125 | 492.5/196.1 > Lyso GPEtn:Lyso20:1e/20:0p | −0.047888 | −0.064031 | −0.093098 | 0.069101 | 0.021004 | −0.036178 | −0.062649 | 0.028834 | −0.049858 | 0.028707 |
| 126 | 500.4/196.1 > Lyso GPEtn:Lyso 20:4 | 0.020723 | 0.076962 | −0.012834 | 0.109091 | −0.039611 | 0.027262 | 0.052285 | −0.019313 | −0.030955 | −0.043281 |
| 127 | 524.4/196.1 > Lyso GPEtn:Lyso 22:6 | 0.003991 | 0.091634 | −0.03043 | 0.1155 | −0.010565 | 0.030774 | −0.010851 | −0.072268 | −0.012612 | −0.02654 |
| 128 | 688.6/196.1 > GPEtn:16:0/16:1 | 0.021153 | −0.08701 | −0.100149 | 0.051485 | 0.014413 | −0.004686 | −0.075514 | −0.04118 | −0.03138 | −0.014723 |
| 129 | 690.7/196.1 > GPEtn:16:0/16:0 | −0.025238 | −0.024906 | −0.045285 | 0.000753 | −0.007165 | 0.003057 | 0.004246 | −0.04489 | −0.059303 | −0.044157 |
| 130 | 698.6/196.1 > GPEtn:34:2p, 34:3e | 0.000372 | −0.065132 | −0.078682 | 0.035437 | 0.032206 | −0.035559 | −0.00101 | −0.018237 | 0.016707 | −0.01799 |
| 131 | 700.6/196.1 > GPEtn:34:1p, 34:2e | −0.006628 | −0.015053 | 0.04484 | −0.007066 | 0.06359 | 0.052243 | 0.079492 | −0.066613 | −0.018936 | −0.042619 |
| 132 | 702.6/196.1 > GPEtn:34:0p, 34:1e | 0.000398 | −0.080922 | −0.120314 | 0.049086 | −0.008436 | 0.00408 | −0.029451 | −0.017746 | −0.006896 | 0.018238 |
| 133 | 710.8/196.1 > GPEtn:18:1/16:1 | 0.016904 | −0.073806 | −0.063669 | −0.022414 | 0.042658 | −0.04555 | −0.032598 | −0.07076 | −0.024178 | 0.05596 |
| 134 | 712.8/196.1 > GPEtn:18:2/16:1 | 0.000692 | −0.045326 | −0.007423 | −0.043036 | −0.015561 | −0.006971 | −0.047196 | 0.025023 | 0.087099 | −0.044707 |
| 135 | 714.7/196.1 > GPEtn:18:1/16:1 | −0.013933 | −0.047755 | −0.150292 | 0.050693 | −0.027286 | 0.00421 | −0.04158 | 0.029885 | −0.000204 | −0.007915 |
| 136 | 716.7/196.1 > GPEtn:18:1/16:0 | −0.001556 | −0.012326 | −0.111754 | −0.0094 | −0.044461 | 0.05282 | −0.074497 | 0.005064 | −0.010574 | −0.074308 |
| 137 | 718.6/196.1 > GPEtn:18:0/16:0 | 0.009111 | −0.070138 | −0.110959 | 0.056328 | 0.005624 | −0.025039 | −0.064341 | −0.046408 | −0.00864 | −0.009007 |
| 138 | 722.6/196.1 > GPEtn:36:4p | −0.024942 | −0.011216 | 0.052646 | −0.00338 | 0.051653 | 0.06441 | −0.004648 | −0.018601 | −0.011105 | −0.04719 |
| 139 | 724.6/196.1 > GPEtn:36:3p, 36:4e | −0.000101 | −0.044089 | −0.036587 | 0.048369 | 0.040753 | 0.009108 | 0.009815 | −0.054071 | −0.002608 | 0.011174 |
| 140 | 726.6/196.1 > GPEtn:36:2p, 36:3e | −0.00723 | −0.03557 | −0.072439 | 0.025785 | 0.000232 | −0.091707 | 0.002925 | −0.033864 | −0.011805 | 0.087966 |
| 141 | 728.6/196.1 > GPEtn:36:1p, 36:2e | −0.019188 | −0.066121 | −0.129887 | 0.056958 | −0.007375 | −0.01108 | −0.032861 | 0.00145 | 0.033287 | −0.012389 |
| 142 | 738.8/196.1 > GPEtn:20:4/16:0 | 0.00551 | 0.086009 | −0.072768 | −0.026068 | −0.009861 | 0.0095 | −0.073904 | 0.032592 | −0.044446 | −0.079377 |
| 143 | 740.8/196.1 > GPEtn:18:2/18:1 | −0.006288 | −0.022264 | −0.138524 | 0.065468 | −0.020208 | 0.016235 | 0.010982 | 0.061724 | 0.013666 | −0.010482 |
| 144 | 742.8/196.1 > GPEtn:18:1/18:1 | −0.003718 | 0.007326 | −0.078945 | 0.0263 | −0.085095 | 0.091663 | 0.006769 | 0.083291 | 0.013552 | −0.066132 |
| 145 | 744.6/196.1 > GPEtn:18:0/18:1 | −0.019707 | −0.029996 | −0.12232 | 0.051886 | −0.041233 | 0.039054 | −0.006893 | 0.060162 | 0.052155 | −0.057903 |
| 146 | 746.8/196.1 > GPEtn:18:0/18:0 | −0.010086 | −0.06672 | −0.140959 | 0.038711 | −0.001138 | −0.023437 | −0.047928 | 0.021782 | 0.00823 | 0.020136 |

APPENDIX B3-continued

PCA Transformation
Matrix (340 × 340 Early/Late)

| | | | | | | | | | | | |
|---|---|---|---|---|---|---|---|---|---|---|---|
| 147 | 748.6/196.1 > GPEtn:38:5p, 38:6e | −0.012991 | 0.044489 | 0.044715 | −0.006636 | 0.023534 | −0.036738 | −0.003558 | 0.016351 | −0.073345 | −0.014 |
| 148 | 750.6/196.1 > GPEtn:38:4p, 38:5e | −0.00139 | −0.034584 | −0.050851 | 0.089475 | −0.00669 | −0.021332 | −0.025865 | −0.048542 | −0.011793 | −0.057135 |
| 149 | 752.6/196.1 > GPEtn:38:3p, 38:4e | −0.01342 | −0.056876 | −0.138535 | 0.068495 | −0.005938 | 0.005644 | −0.038806 | 0.007199 | 0.01257 | 0.001665 |
| 150 | 754.6/196.1 > GPEtn:38:2p, 38:3e | −0.020592 | −0.067047 | −0.116811 | 0.064341 | 0.021704 | −0.005198 | −0.069572 | 0.002806 | −0.01974 | −0.01503 |
| 151 | 756.6/196.1 > GPEtn:38:1p, 38:2e | −0.015684 | −0.003457 | 0.052487 | −0.039485 | 0.016324 | −0.0083 | −0.024896 | −0.02806 | −0.031526 | −0.012381 |
| 152 | 762.8/196.1 > GPEtn:20:4/18:2 | 0.003444 | 0.098505 | −0.060274 | 0.034323 | −0.025266 | 0.041977 | −0.076607 | −0.066104 | −0.035241 | −0.04224 |
| 153 | 764.8/196.1 > GPEtn:20:4/18:1 | 0.016712 | 0.069378 | −0.092028 | 0.040057 | −0.039176 | 0.065154 | −0.03915 | 0.003943 | 0.02344 | −0.037251 |
| 154 | 766.8/196.1 > GPEtn:20:4/18:0 | 0.019108 | 0.082563 | −0.08176 | −0.001187 | −0.045848 | 0.023193 | −0.039604 | 0.022601 | 0.007988 | −0.039986 |
| 155 | 768.8/196.1 > GPEtn:20:3/18:0 | 0.009958 | 0.033262 | −0.096018 | 0.058178 | −0.054627 | 0.086563 | −0.050388 | 0.03342 | 0.018609 | 0.03335 |
| 156 | 770.6/196.1 > GPEtn:20:2/18:0 | −0.000716 | −0.07393 | −0.10785 | 0.064947 | 0.000011 | 0.010625 | −0.012872 | −0.02617 | −0.037238 | 0.021432 |
| 157 | 772.6/196.1 > GPEtn:20:1/18:0 | −0.016348 | −0.094973 | −0.116287 | 0.027383 | −0.007407 | 0.003796 | −0.029571 | 0.022482 | −0.013298 | 0.031942 |
| 158 | 776.6/196.1 > GPEtn:40:5p, 40:6e | −0.028587 | −0.025178 | −0.013457 | 0.040329 | 0.01597 | 0.072199 | 0.028504 | −0.026412 | −0.010888 | 0.082413 |
| 159 | 778.6/196.1 > GPEtn:40:4p, 40:5e | −0.04143 | −0.017382 | −0.017183 | 0.006732 | 0.056084 | 0.029726 | −0.083407 | −0.056984 | −0.011959 | −0.050934 |
| 160 | 780.6/196.1 > GPEtn:40:3p, 40:4e | −0.002433 | −0.042528 | −0.033855 | 0.027789 | 0.024888 | −0.024957 | −0.03365 | −0.065454 | −0.018743 | 0.016346 |
| 161 | 784.6/196.1 > GPEtn:40:1p, 40:2e | −0.000706 | −0.068301 | −0.085359 | 0.071013 | −0.01553 | 0.035658 | −0.040788 | −0.024347 | −0.020544 | −0.040446 |
| 162 | 788.8/196.1 > GPEtn:22:4/18:3 | −0.020488 | −0.010579 | −0.118012 | 0.063746 | −0.032722 | 0.018029 | −0.073891 | 0.037982 | −0.02204 | −0.045992 |
| 163 | 790.8/196.1 > GPEtn:22:4/18:2 | −0.007692 | 0.023673 | −0.132567 | 0.057756 | −0.023583 | 0.015421 | −0.105565 | −0.023931 | −0.014543 | −0.006126 |
| 164 | 792.6/196.1 > GPEtn:40:5a | 0.012352 | 0.057564 | −0.019572 | −0.035409 | −0.03084 | 0.076536 | −0.077179 | −0.024271 | −0.051479 | 0.043563 |
| 165 | 794.6/196.1 > GPEtn:40:4a | 0.023632 | 0.00047 | −0.093829 | 0.002491 | 0.033858 | 0.064321 | −0.071914 | −0.033977 | −0.025098 | 0.034866 |
| 166 | 796.8/196.1 > GPEtn:40:3a | 0.004724 | −0.03411 | 0.046623 | −0.077236 | −0.009076 | 0.0369821 | 0.0022 | −0.033917 | −0.037324 | 0.006183 |
| 167 | 798.6/196.1 > GPEtn:40:2a | −0.015899 | −0.088991 | −0.107581 | 0.042079 | −0.0069 | 0.014571 | −0.01777 | −0.006686 | −0.00361 | 0.053042 |
| 168 | 569.4/241.1 > GPIns:Lyso 16:1 | 0.005691 | −0.002609 | 0.048055 | 0.108524 | −0.004069 | 0.10043 | −0.090057 | 0.050485 | 0.066147 | −0.059793 |
| 169 | 571.3/241.1 > GPIns:Lyso 16:0 | −0.00654 | −0.114989 | −0.008757 | 0.05048 | 0.021924 | −0.00552 | 0.031334 | −0.025679 | 0.118307 | −0.044851 |
| 170 | 595.4/241.1 > GPIns:Lyso 18:2 | −0.001679 | −0.09318 | 0.00615 | 0.03574 | 0.032658 | −0.035652 | 0.079262 | −0.035539 | 0.133749 | −0.074269 |
| 171 | 597.4/241.1 > GPIns:Lyso 18:1 | 0.000717 | −0.098935 | −0.008108 | 0.096938 | 0.00737 | 0.004974 | 0.042012 | −0.00635 | 0.101186 | −0.070285 |
| 172 | 599.4/241.1 > GPIns:Lyso 18:0 | −0.043449 | −0.096164 | 0.006418 | 0.066658 | 0.030564 | 0.087123 | −0.039445 | −0.021416 | −0.04762 | −0.027156 |
| 173 | 619.5/241.1 > GPIns:Lyso 20:4 | −0.022577 | 0.062609 | 0.006684 | 0.138054 | 0.05399 | 0.038713 | −0.069492 | 0.030971 | −0.004957 | −0.02052 |
| 174 | 621.5/241.1 > GPIns:Lyso 20:3 | 0.007079 | 0.048 | 0.003328 | 0.126189 | −0.029134 | 0.07296 | −0.034534 | 0.080597 | 0.029925 | 0.026019 |
| 175 | 623.5/241.1 > GPIns:Lyso 20:2 | −0.007281 | −0.029491 | −0.047023 | 0.112011 | −0.011159 | 0.072904 | 0.013095 | 0.055725 | −0.04913 | −0.024717 |
| 176 | 625.5/241.1 > GPIns:Lyso 20:1 | −0.005786 | −0.123548 | −0.04109 | 0.036235 | 0.003729 | 0.036055 | −0.004658 | −0.024228 | −0.042881 | 0.019871 |
| 177 | 627.5/241.1 > GPIns:Lyso 20:0 | −0.003214 | −0.058599 | 0.101788 | 0.030847 | 0.049016 | 0.04451 | 0.017524 | −0.017329 | −0.015801 | −0.016417 |
| 178 | 679.5/241.1 > GPIns:Lyso 24:2 | 0.056996 | −0.086644 | 0.010374 | 0.040215 | 0.079336 | −0.057694 | −0.025929 | −0.045465 | 0.053391 | −0.013045 |
| 179 | 835.7/241.1 > GPIns:34:1 | 0.077005 | −0.074051 | 0.041124 | −0.009189 | 0.067922 | −0.052187 | −0.000696 | −0.031136 | 0.083654 | −0.006183 |
| 180 | 857.7/241.1 > GPIns:36:4 | 0.080572 | −0.06006 | 0.047252 | −0.008094 | 0.071186 | −0.061142 | −0.000926 | −0.01976 | 0.090491 | 0.000751 |
| 181 | 859.8/241.1 > GPIns:36:3 | 0.072302 | −0.07602 | 0.047642 | −0.017482 | 0.061023 | −0.064147 | 0.025576 | −0.025008 | 0.090429 | −0.004982 |
| 182 | 861.8/241.1 > GPIns:36:2 | 0.082727 | −0.062041 | 0.03581 | −0.022113 | 0.07497 | −0.038109 | 0.028087 | −0.048102 | 0.053414 | −0.016691 |
| 183 | 863.7/241.1 > GPIns:36:1 | 0.083189 | −0.066432 | 0.036195 | 0.005867 | 0.042271 | −0.003847 | 0.016039 | −0.041972 | 0.03903 | −0.013846 |
| 184 | 865.8/241.1 > GPIns:36:0 | 0.065671 | −0.087083 | 0.003756 | 0.048973 | 0.027836 | −0.007256 | −0.049115 | 0.018876 | 0.003167 | 0.010049 |
| 185 | 873.8/241.1 > GPIns:37:3 | 0.066631 | −0.027827 | 0.072841 | 0.0332 | 0.009919 | 0.086372 | −0.024594 | 0.025541 | 0.019418 | 0.050255 |
| 186 | 883.8/241.1 > GPIns:38:5 | 0.050139 | −0.020423 | 0.089897 | 0.00908 | −0.001161 | 0.081096 | −0.005027 | 0.034063 | −0.052217 | 0.06982 |
| 187 | 885.8/241.1 > GPIns:38:4 | 0.072274 | 0.078675 | 0.008807 | 0.045357 | 0.050363 | 0.023782 | −0.072001 | −0.023816 | −0.041761 | 0.018736 |
| 188 | 887.8/241.1 > GPIns:38:3 | 0.072377 | 0.067785 | 0.013296 | 0.048464 | 0.002906 | 0.051694 | −0.049978 | 0.029751 | −0.023551 | 0.044971 |
| 189 | 889.8/241.1 > GPIns:38:2 | 0.078126 | −0.020754 | −0.000074 | 0.061042 | 0.018525 | 0.019533 | −0.00608 | 0.070187 | −0.025228 | 0.038956 |
| 190 | 891.8/241.1 > GPIns:38:1 | 0.008453 | −0.122925 | −0.063806 | −0.028512 | 0.033981 | −0.000809 | 0.010687 | −0.041913 | 0.042887 | 0.077149 |
| 191 | 893.8/241.1 > GPIns:38:0 | −0.000089 | −0.105082 | −0.09351 | −0.000936 | 0.034241 | −0.026268 | −0.015735 | −0.042213 | 0.085692 | 0.054784 |
| 192 | 909.8/241.1 > GPIns:40:6 | 0.035701 | 0.086899 | 0.00844 | 0.084025 | 0.042228 | 0.019185 | −0.053003 | −0.096606 | 0.030824 | −0.003161 |
| 193 | 911.8/241.1 > GPIns:40:5 | 0.058632 | 0.088916 | 0.025351 | 0.067845 | 0.033602 | 0.054252 | −0.054246 | −0.057244 | 0.007026 | 0.006947 |
| 194 | 913.8/241.1 > GPIns:40:4 | 0.064306 | −0.005091 | 0.045356 | 0.039569 | 0.019225 | 0.109479 | −0.071708 | 0.017276 | −0.041135 | 0.084563 |
| 195 | 915.8/241.1 > GPIns:40:3 | 0.03206 | −0.087163 | 0.02962 | −0.071651 | 0.024926 | 0.038269 | −0.033573 | 0.008479 | −0.090649 | 0.099909 |
| 196 | 917.8/241.1 > GPIns:40:2 | 0.039019 | −0.114853 | 0.042743 | −0.02576 | 0.043447 | 0.006927 | 0.011395 | 0.013432 | −0.023375 | 0.089913 |

APPENDIX B3-continued

PCA Transformation
Matrix (340 × 340 Early/Late)

| | | | | | | | | | | | |
|---|---|---|---|---|---|---|---|---|---|---|---|
| 197 | 919.8/241.1 > GPIns:40:1 | −0.001128 | −0.121667 | −0.060663 | −0.017058 | 0.036356 | 0.009346 | 0.012027 | −0.03119 | 0.050038 | 0.064834 |
| 198 | 963.9/241.1 > GPInsP:38:5 | −0.029028 | −0.077994 | 0.013054 | −0.059181 | 0.001377 | 0.106067 | −0.013351 | −0.042198 | −0.094853 | −0.001856 |
| 199 | 963.9/321.1 > GPInsP:38:5 | −0.019557 | −0.056263 | −0.065638 | 0.046913 | 0.034562 | 0.040672 | −0.058994 | 0.016854 | −0.097463 | −0.026454 |
| 200 | 965.9/241.1 > GPInsP:38:4 | −0.026079 | −0.072007 | 0.066459 | −0.041668 | −0.020127 | 0.076952 | −0.010088 | −0.074775 | −0.119431 | 0.006507 |
| 201 | 965.9/321.1 > GPInsP:38:4 | −0.036168 | −0.022521 | −0.066314 | 0.041128 | −0.070518 | 0.010002 | −0.058426 | −0.050135 | 0.079501 | 0.036029 |
| 202 | 967.9/241.1 > GPInsP:38:3 | −0.016991 | −0.063442 | 0.057594 | −0.062069 | 0.000398 | 0.099917 | −0.009541 | −0.046534 | −0.100549 | −0.014527 |
| 203 | 967.9/321.1 > GPInsP. 38.3 | −0.033722 | −0.073837 | 0.03056 | 0.02021 | 0.027859 | 0.080559 | −0.021446 | −0.104458 | 0.055845 | −0.058877 |
| 204 | 1045.9/241.1 > GPInsP2:38:4 | −0.032455 | −0.083373 | −0.050409 | 0.011765 | 0.008161 | 0.030833 | −0.018337 | −0.022842 | −0.026804 | 0.028536 |
| 205 | 1045.9/321.1 > GPInsP2:38:4 | −0.015299 | 0.012476 | 0.031949 | 0.010473 | 0.027142 | 0.033378 | −0.048625 | 0.00361 | −0.0694 | 0.061239 |
| 206 | 1045.9/401.1 > GPInsP2:38:4 | −0.042761 | −0.00529 | 0.033538 | 0.000496 | 0.021735 | 0.021228 | 0.052067 | −0.0312 | 0.020905 | 0.038444 |
| 207 | 1047.9/321.1 > GPInsP2:38:3 | −0.026117 | −0.006704 | 0.039858 | 0.011429 | 0.050742 | 0.028666 | −0.011795 | −0.049146 | −0.061623 | −0.068444 |
| 208 | 1047.9/401.1 > GPInsP2:38:3 | −0.037761 | −0.020492 | 0.042456 | −0.034145 | 0.010017 | 0.057065 | 0.033871 | −0.121058 | 0.027685 | 0.020651 |
| 209 | 1047.9/241.1 > GPInsP2:38:3 | 0.012455 | −0.038994 | 0.07315 | 0.006999 | 0.012219 | 0.082442 | −0.007033 | −0.03373 | −0.066529 | −0.030933 |
| 210 | 1125.9/241.1 > GPInsP3:38:4 | −0.005413 | −0.059839 | −0.008791 | −0.006041 | 0.024033 | 0.060861 | −0.044803 | 0.000974 | 0.046819 | −0.018649 |
| 211 | 1125.9/321.1 > GPInsP3:38:4 | −0.00635 | −0.069047 | −0.092383 | 0.070708 | 0.01372 | −0.019139 | −0.014139 | −0.018149 | 0.001743 | −0.051473 |
| 212 | 1125.9/401.1 > GPInsP3:38:4 | 0.012136 | −0.024386 | 0.045614 | −0.020987 | −0.007407 | −0.010389 | 0.02524 | −0.055349 | −0.059931 | 0.071279 |
| 213 | 1125.9/481.1 > GPInsP3:38:4 | 0.018492 | −0.007865 | 0.042138 | −0.017033 | 0.045291 | −0.037292 | −0.052933 | 0.07559 | −0.045487 | 0.104078 |
| 214 | 835.7/281.1 > GPIns:34:1 | 0.080851 | −0.079852 | 0.021475 | 0.011285 | 0.059856 | −0.068013 | −0.020571 | −0.004856 | 0.050809 | −0.010966 |
| 215 | 821.8/241.1 > GPIns:34:1 | 0.053186 | −0.071114 | 0.063016 | 0.009654 | 0.043929 | −0.028999 | −0.036187 | −0.017456 | 0.067714 | 0.037515 |
| 216 | 494.4/184.1 > GPCho:Lyso 16:1 | −0.005795 | −0.016357 | 0.054908 | 0.053132 | −0.091378 | 0.116537 | −0.050696 | 0.103012 | 0.081978 | −0.020233 |
| 217 | 496.4/184.1 > GPCho:Lyso 16:0 | −0.048509 | −0.031182 | 0.048053 | 0.018781 | −0.05267 | 0.12526 | −0.061686 | −0.003704 | −0.086254 | 0.056238 |
| 218 | 520.4/184.1 > GPCho:Lyso 18:2 | −0.060352 | 0.014174 | −0.031047 | 0.09692 | −0.037882 | 0.048037 | 0.11773 | 0.062813 | 0.046749 | −0.109061 |
| 219 | 522.4/184.1 > GPCho:Lyso 18:1 | −0.066258 | −0.005735 | 0.034078 | 0.030452 | −0.072012 | 0.087377 | −0.01696 | 0.082058 | 0.09602 | −0.044855 |
| 220 | 524.4/184.1 > GPCho:Lyso 18:0 | −0.041353 | −0.043906 | 0.011382 | 0.045684 | −0.080347 | 0.129634 | 0.030623 | 0.00678 | 0.056096 | 0.130175 |
| 221 | 544.4/184.1 > GPCho:Lyso 20:4 | −0.04198 | 0.103403 | −0.005946 | 0.087444 | 0.041073 | 0.011495 | −0.053374 | −0.00154 | 0.024918 | 0.046553 |
| 222 | 568.4/184.1 > GPCho:Lyso 22:6 | −0.041727 | 0.092639 | −0.002116 | 0.098961 | 0.034234 | 0.000945 | −0.013906 | −0.038307 | 0.04375− | 0.022119 |
| 223 | 570.4/184.1 > GPCho:Lyso 22:5 | −0.025671 | 0.101408 | 0.00164 | 0.106563 | 0.010895 | 0.026774 | −0.001123 | −0.004564 | 0.06595 | 0.036317 |
| 224 | 678.5/184.1 > GPCho:28:0 | −0.028584 | −0.098419 | 0.041228 | 0.00057 | −0.057535 | 0.087313 | 0.000809 | −0.004889 | −0.020455 | 0.071131 |
| 225 | 678.5/184.1 > GPCho:28:0a | −0.034523 | −0.093865 | 0.034929 | 0.010307 | −0.060213 | 0.087337 | −0.000018 | −0.016379 | −0.007507 | 0.076963 |
| 226 | 704.6/184.1 > GPCho:30:1a | −0.10192 | 0.010698 | −0.003209 | −0.048243 | 0.041671 | −0.050725 | 0.014543 | −0.018338 | −0.058585 | −0.026207 |
| 227 | 706.6/184.1 > GPCho:30:0a | −0.087359 | 0.009767 | −0.000924 | −0.027691 | 0.022165 | −0.007593 | −0.019638 | −0.009513 | −0.014133 | 0.016422 |
| 228 | 718.6/184.1 > GPCho:32:0p, 32:1e | −0.067843 | −0.065777 | 0.006874 | 0.027866 | −0.018833 | −0.010551 | 0.06337 | −0.095896 | −0.044692 | −0.010116 |
| 229 | 730.8/184.1 > GPCho:32:2 | −0.07635 | −0.009558 | 0.000637 | −0.005263 | 0.019405 | −0.029863 | −0.038261 | 0.016669 | −0.025104 | −0.065593 |
| 230 | 732.6/184.1 > GPCho:32:1a | −0.029325 | −0.030554 | 0.024848 | −0.064754 | −0.013288 | 0.042906 | −0.159253 | 0.071117 | 0.094718 | −0.052876 |
| 231 | 734.6/184.1 > GPCho:32:0a | 0.000684 | −0.030006 | 0.025725 | −0.12331 | 0.013337 | −0.009917 | −0.106763 | −0.086105 | −0.008802 | −0.057042 |
| 232 | 742.6/184.1 > GPCho:34:2p, 34:3e | −0.020246 | −0.089869 | 0.064312 | 0.023449 | −0.065453 | 0.010869 | 0.089223 | −0.01293 | −0.066809 | 0.024024 |
| 233 | 744.6/184.1 > GPCho:34:1p, 34:2e | 0.028072 | −0.002187 | 0.016777 | 0.083407 | −0.0475 | −0.010582 | 0.17775 | 0.027789 | −0.030956 | −0.03958 |
| 234 | 746.6/184.1 > GPCho:34:0p, 34:1e | 0.003469 | −0.064832 | 0.063424 | −0.008267 | −0.032195 | −0.034503 | 0.068794 | −0.027396 | −0.034966 | −0.049383 |
| 235 | 748.6/184.1 > GPCho:34:0e | −0.016793 | −0.092704 | 0.023249 | −0.031127 | −0.033206 | −0.02449 | 0.05935 | −0.067999 | −0.050944 | −0.001668 |
| 236 | 756.6/184.1 > GPCho:34:3a | 0.012385 | −0.12025 | 0.044316 | −0.035952 | −0.037836 | 0.031711 | 0.0364 | 0.056381 | −0.025816 | −0.00428 |
| 237 | 758.7/184.1 > GPCho:34:2a | 0.086272 | −0.035641 | −0.012222 | −0.025642 | −0.008187 | −0.046123 | 0.062962 | 0.023671 | −0.014691 | −0.10843 |
| 238 | 760.6/184.1 > GPCho:34:1a | 0.066533 | −0.037267 | 0.048426 | −0.079759 | −0.035272 | 0.022149 | −0.107832 | 0.027587 | 0.06492 | −0.05688 |
| 239 | 762.6/184.1 > GPCho:34:0a | 0.056514 | −0.024788 | 0.051318 | −0.083963 | −0.042533 | 0.049531 | −0.117837 | 0.007188 | 0.062786 | −0.045906 |
| 240 | 768.6/184.1 > GPCho:36:3p, 36:4e | 0.032528 | 0.087727 | 0.029009 | 0.091025 | 0.012152 | −0.048969 | 0.024311 | −0.057418 | −0.027432 | 0.063808 |
| 241 | 770.6/184.1 > GPCho:36:2p, 36:3e | 0.035623 | 0.01459 | 0.047115 | 0.100078 | −0.045498 | −0.035729 | 0.146087 | 0.019147 | −0.030509 | 0.040849 |
| 242 | 772.6/184.1 > GPCho:36:1p, 36:2e | 0.025754 | −0.102046 | 0.02804 | 0.019113 | −0.038052 | 0.011928 | 0.123692 | −0.029729 | −0.048124 | −0.031253 |
| 243 | 774.6/184.1 > GPCho:36:0p, 36:1e | 0.011153 | −0.094705 | 0.030156 | 0.048482 | −0.05475 | 0.031121 | 0.062977 | −0.057145 | −0.028695 | 0.046557 |
| 244 | 782.6/184.1 > GPCho:36:4a | 0.067495 | 0.096807 | −0.006861 | 0.012034 | 0.032179 | −0.022187 | −0.078996 | −0.048847 | −0.009936 | 0.036592 |
| 245 | 784.6/184.1 > GPCho:36:3a | 0.088945 | 0.048543 | 0.006732 | 0.052629 | −0.049067 | 0.043749 | 0.002847 | 0.042517 | 0.040309 | 0.069957 |
| 246 | 786.6/184.1 > GPCho:36:2a | 0.078517 | −0.033837 | −0.022561 | 0.047682 | −0.040023 | 0.033502 | 0.107156 | 0.032527 | 0.07634 | 0.001723 |

APPENDIX B3-continued

PCA Transformation
Matrix (340 × 340 Early/Late)

| | | | | | | | | | | | |
|---|---|---|---|---|---|---|---|---|---|---|---|
| 247 | 788.6/184.1 > GPCho:36:1a | 0.034885 | −0.109774 | −0.002163 | −0.017497 | −0.048221 | 0.080703 | 0.018132 | 0.074716 | 0.060122 | 0.080084 |
| 248 | 790.8/184.1 > GPCho:36:0 | 0.020303 | −0.111787 | 0.022599 | −0.019002 | −0.057991 | 0.075748 | 0.001885 | 0.060812 | 0.048906 | 0.11137 |
| 249 | 792.6/184.1 > GPCho:38:5p, 38:6e | 0.008351 | 0.057642 | 0.047608 | 0.092898 | −0.007852 | −0.015746 | 0.038707 | −0.109495 | −0.005171 | 0.071093 |
| 250 | 794.6/184.1 > GPCho:38:4p, 38:5e | 0.027833 | 0.090974 | 0.031767 | 0.090063 | 0.03876 | −0.071289 | 0.025686 | −0.049751 | −0.02214 | 0.028808 |
| 251 | 796.6/184.1 > GPCho:38:3p, 38:4e | 0.03397 | 0.076821 | 0.044191 | 0.076359 | 0.021994 | −0.070364 | 0.028575 | −0.065527 | −0.050462 | 0.078749 |
| 252 | 798.6/184.1 > GPCho:38:2p, 38:3e | 0.049116 | −0.056102 | 0.075475 | 0.032838 | −0.006309 | −0.009921 | 0.009593 | −0.069722 | −0.114886 | 0.112124 |
| 253 | 800.6/184.1 > GPCho:38:1p, 38:2e | −0.037031 | −0.090172 | 0.043776 | 0.037444 | −0.030657 | −0.006731 | 0.105679 | −0.055439 | −0.07843 | 0.021915 |
| 254 | 808.6/184.1 > GPCho:38:5a | 0.059323 | 0.102063 | 0.002045 | 0.073172 | 0.009897 | 0.007705 | −0.021404 | −0.046226 | 0.045091 | 0.081339 |
| 255 | 810.6/184.1 > GPCho:38:4a | 0.071279 | 0.089701 | −0.008048 | 0.040233 | 0.022309 | 0.00248 | −0.046829 | −0.040764 | 0.035134 | 0.106113 |
| 256 | 812.6/184.1 > GPCho:38:3a | 0.040752 | 0.042488 | 0.01149 | 0.037184 | −0.012103 | 0.056388 | −0.050787 | 0.008779 | 0.034757 | 0.211919 |
| 257 | 814.6/184.1 > GPCho:38:2a | −0.101215 | −0.02696 | 0.005051 | −0.048896 | 0.059851 | −0.021255 | −0.020352 | −0.029672 | −0.042583 | 0.050552 |
| 258 | 816.6/184.1 > GPCho:38:1a | −0.05705 | −0.095747 | −0.023054 | −0.004616 | 0.013234 | 0.014425 | 0.064777 | 0.02605 | −0.06046 | 0.145845 |
| 259 | 820.6/184.1 > GPCho:40:5p, 40:6e | 0.023947 | 0.078142 | 0.021214 | 0.097958 | 0.024527 | −0.027127 | 0.033937 | −0.111574 | −0.004866 | 0.048983 |
| 260 | 822.6/184.1 > GPCho:40:4p, 40:5e | 0.044762 | −0.005182 | 0.050869 | 0.044365 | 0.05637 | −0.034361 | −0.013686 | −0.134507 | −0.088897 | 0.081665 |
| 261 | 824.6/184.1 > GPCho:40:3p, 40:4e | 0.052974 | −0.046883 | 0.068826 | 0.014327 | 0.036215 | −0.033089 | −0.017867 | −0.083761 | −0.105818 | 0.11952 |
| 262 | 826.6/184.1 > GPCho:40:2p, 40:3e | 0.010001 | −0.12956 | 0.044847 | −0.040108 | −0.001773 | 0.026732 | −0.007872 | −0.025733 | −0.085101 | 0.016391 |
| 263 | 828.6/184.1 > GPCho:40:1p, 40:2e | −0.015141 | −0.132902 | 0.032242 | −0.029576 | −0.012996 | 0.018583 | 0.007025 | −0.040015 | −0.06731 | 0.014214 |
| 264 | 834.6/184.1 > GPCho:40:6a | 0.040614 | 0.095 | −0.004745 | 0.079754 | 0.005645 | 0.014455 | −0.025571 | −0.093364 | 0.060107 | 0.060799 |
| 265 | 836.6/184.1 > GPCho:40:5a | 0.068856 | 0.042146 | −0.000522 | 0.040172 | 0.009759 | 0.058588 | −0.046164 | −0.081015 | −0.004006 | 0.1548 |
| 266 | 838.6/184.1 > GPCho:40:4a | 0.077603 | −0.026438 | 0.022522 | −0.004386 | −0.006712 | 0.066404 | −0.06019 | 0.003269 | −0.044381 | 0.200587 |
| 267 | 701.5/184.1 > SM:18/16:1 | −0.089848 | 0.002181 | 0.002716 | −0.016799 | 0.022837 | −0.030978 | 0.027065 | −0.00854 | −0.057702 | −0.071381 |
| 268 | 703.5/184.1 > SM:18/16:0 | −0.105221 | 0.004473 | −0.0134 | −0.036002 | 0.049374 | −0.04447 | 0.005814 | −0.020747 | −0.056549 | −0.033373 |
| 269 | 703.8/184.4 > SM:d18:1/16:0 | −0.103167 | 0.012292 | −0.000974 | −0.043748 | 0.048261 | −0.068015 | 0.016252 | −0.011723 | −0.059058 | −0.009879 |
| 270 | 705.8/184.4 > SM:d18:0/16:0 | −0.10111 | 0.019274 | −0.015837 | −0.041166 | 0.051 | −0.048808 | −0.005407 | −0.018521 | −0.050686 | −0.007906 |
| 271 | 727.6/184.1 > SM:18/18:2 | −0.05848 | −0.061412 | −0.047297 | 0.003062 | 0.012162 | −0.037409 | 0.054503 | 0.014715 | −0.08799 | −0.061328 |
| 272 | 729.6/184.1 > SM:18/18:1 | −0.082035 | −0.011438 | −0.015516 | −0.027227 | 0.037531 | −0.040702 | −0.042407 | −0.0276 | −0.036516 | −0.075854 |
| 273 | 731.6/184.1 > SM:18/18:0 | −0.088671 | −0.010116 | −0.031646 | −0.06492 | 0.057198 | −0.030793 | −0.082206 | −0.032731 | −0.013565 | −0.038131 |
| 274 | 731.8/184.4 > SM:d18:1/18:0 | −0.089501 | −0.007174 | −0.024596 | −0.069701 | 0.056663 | −0.038676 | −0.078685 | −0.030703 | −0.015452 | −0.031022 |
| 275 | 733.8/184.4 > SM:d18:0/18:0 | −0.048642 | −0.025332 | −0.013933 | −0.065977 | 0.021671 | 0.019558 | −0.166252 | 0.035629 | 0.055576 | −0.023618 |
| 276 | 757.6/184.1 > SM:18/20:1 | −0.016991 | −0.117175 | 0.036875 | −0.024353 | −0.036201 | 0.008701 | 0.049008 | 0.056958 | −0.041343 | −0.026955 |
| 277 | 759.6/184.1 > SM:18/20:0 | 0.089742 | −0.003793 | −0.028993 | −0.014657 | −0.008988 | −0.034712 | 0.071292 | 0.02206 | −0.051126 | −0.141294 |
| 278 | 759.8/184.4 > SM:d18:1/20:0 | 0.085843 | 0.002176 | −0.026012 | −0.018627 | −0.021856 | −0.043389 | 0.071158 | 0.023403 | −0.05513 | −0.135114 |
| 279 | 761.8/184.4 > SM:d18:0/20:0 | 0.060668 | −0.017256 | 0.058344 | −0.077215 | −0.054004 | 0.029398 | −0.119415 | 0.025738 | 0.058429 | −0.05184 |
| 280 | 773.6/184.1 > SM:18/21:0 | −0.032084 | −0.045648 | −0.016927 | 0.052526 | −0.05981 | 0.018418 | 0.154423 | −0.031955 | −0.050753 | 0.02903 |
| 281 | 787.6/184.1 > SM:18/22:0 | 0.021598 | −0.037127 | −0.052645 | 0.063258 | −0.052025 | 0.047722 | 0.149756 | 0.048275 | 0.071647 | 0.049915 |
| 282 | 787.9/184.4 > SM:d18:1/22:0 | −0.002484 | −0.032344 | −0.063978 | 0.060078 | −0.055733 | 0.022289 | 0.15537 | 0.048622 | 0.051344 | 0.100949 |
| 283 | 789.9/184.4 > SM:d18:0/22:0 | 0.028444 | −0.097828 | 0.009246 | −0.013179 | −0.068929 | 0.070087 | −0.00716 | 0.092682 | 0.067136 | 0.114144 |
| 284 | 813.6/184.1 > SM:18/24:1 | −0.107755 | 0.001391 | −0.005732 | −0.035175 | 0.057598 | −0.034166 | −0.021359 | −0.034773 | −0.027296 | 0.032511 |
| 285 | 813.9/184.4 > SM:d18:1/24:1 | −0.105613 | 0.00315 | −0.00194 | −0.037619 | 0.045735 | −0.048089 | −0.018551 | −0.044849 | −0.03301 | 0.031363 |
| 286 | 815.6/184.1 > SM:18/24:0 | −0.093163 | 0.00752 | −0.018626 | 0.011499 | 0.034274 | −0.017384 | 0.069419 | 0.004054 | −0.042508 | 0.119719 |
| 287 | 815.9/184.4 > SM:d18:0/24:1 | −0.08677 | −0.001985 | −0.048429 | 0.019049 | 0.023715 | −0.035214 | 0.058698 | 0.011744 | −0.050553 | 0.129608 |
| 288 | 817.9/184.4 > SM:d18:0/24:0 | −0.006997 | −0.113491 | −0.025628 | 0.024044 | −0.004947 | 0.002876 | 0.038844 | 0.045192 | −0.092539 | 0.128288 |
| 289 | 841.9/184.4 > SM:d18:1/26:1 | −0.007211 | −0.12501 | −0.00499 | −0.05424 | −0.000959 | 0.04198 | −0.022305 | −0.013866 | −0.099513 | 0.069307 |
| 290 | 843.9/184.4 > SM:d18:0/26:1 | 0.06532 | −0.06494 | 0.025238 | 0.041842 | 0.019385 | 0.00848 | −0.068973 | −0.01133 | −0.088713 | −0.001669 |
| 291 | 843.9/184.4 > SM:d18:1/26:0 | 0.065454 | −0.064564 | 0.025197 | 0.042653 | 0.01994 | 0.008708 | −0.069316 | −0.010785 | −0.090238 | −0.000209 |
| 292 | 845.9/184.4 > SM:d18:0/26:0 | 0.068076 | −0.052995 | 0.045274 | 0.043158 | 0.013142 | 0.011058 | −0.089395 | −0.009437 | −0.072677 | −0.01572 |
| 293 | 538.7/264.4 > Cer:d18:1/16:0 | −0.081016 | −0.010525 | 0.0435 | 0.044477 | 0.089691 | −0.013367 | −0.044382 | −0.00268 | 0.013564 | −0.050076 |
| 294 | 540.7/266.4 > Cer:d18:0/16:0 | −0.112485 | −0.000564 | −0.014432 | 0.002156 | 0.061077 | −0.020032 | −0.025314 | 0.00438 | 0.018586 | −0.017536 |
| 295 | 566.7/264.4 > Cer:d18:1/18:0 | −0.089215 | −0.025665 | −0.011344 | −0.031944 | 0.075444 | −0.011666 | −0.0892 | −0.025136 | 0.034673 | −0.048529 |
| 296 | 568.7/266.4 > Cer:d18:0/18:0 | −0.094687 | −0.004748 | −0.017403 | −0.046974 | 0.063428 | −0.012101 | −0.05485 | −0.01445 | 0.027952 | 0.029321 |

APPENDIX B3-continued

PCA Transformation
Matrix (340 × 340 Early/Late)

| | | | | | | | | | | | |
|---|---|---|---|---|---|---|---|---|---|---|---|
| 297 | 594.7/264.4 > Cer:d18:1/20:0 | −0.099301 | −0.02082 | −0.005265 | −0.034713 | 0.051093 | −0.000802 | −0.062113 | −0.020425 | 0.045725 | −0.027313 |
| 298 | 596.7/266.4 > Cer:d18:0/20:0 | −0.081588 | −0.005223 | 0.051759 | 0.023963 | 0.071202 | −0.006757 | 0.005869 | 0.051774 | 0.074221 | 0.040393 |
| 299 | 622.8/264.4 > Cer:d18:1/22:0 | −0.107359 | −0.00684 | −0.00577 | −0.006929 | 0.026546 | 0.011512 | −0.01012 | −0.00928 | 0.078934 | 0.00713 |
| 300 | 624.8/266.4 > Cer:d18:0/22:0 | 0.005601 | −0.054356 | 0.02156 | 0.011075 | 0.073113 | −0.107223 | −0.018159 | 0.017867 | 0.138786 | 0.009036 |
| 301 | 648.9/264.4 > Cer:d18:1/24:1 | −0.105272 | −0.013146 | 0.017687 | −0.017929 | 0.057117 | −0.008987 | −0.050342 | −0.020318 | 0.041278 | −0.028525 |
| 302 | 650.9/266.4 > Cer:d18:0/24:1 | −0.11178 | 0.005341 | −0.011021 | −0.027064 | 0.031315 | 0.018727 | −0.046266 | −0.022087 | 0.04713 | 0.002543 |
| 303 | 650.9/264.4 > Cer:d18:1/24:0 | −0.096524 | 0.030924 | −0.015339 | −0.00021 | −0.012711 | 0.015442 | 0.056123 | 0.001602 | 0.029288 | 0.069864 |
| 304 | 652.9/266.4 > Cer:d18:0/24:0 | −0.0979 | 0.031959 | −0.018338 | 0.010057 | −0.018645 | 0.022537 | 0.038292 | 0.004512 | 0.041248 | 0.077308 |
| 305 | 676.9/264.4 > Cer:d18:1/26:1 | −0.094591 | −0.007914 | 0.030002 | −0.044384 | 0.042528 | 0.011061 | −0.037918 | −0.053122 | −0.015123 | −0.007082 |
| 306 | 678.9/266.4 > Cer:d18:0/26:1 | −0.063488 | −0.041391 | 0.023797 | 0.01491 | 0.03028 | 0.038374 | −0.045161 | −0.013405 | 0.054411 | −0.032798 |
| 307 | 678.9/264.4 > Cer:d18:1/26:0 | −0.039672 | −0.043235 | 0.041707 | 0.065748 | −0.028546 | 0.02705 | 0.046157 | −0.017714 | 0.01747 | −0.046229 |
| 308 | 680.9/266.4 > Cer:d18:0/26:0 | −0.007076 | −0.062418 | 0.006679 | 0.051488 | 0.019419 | −0.026283 | −0.022358 | −0.036038 | 0.038794 | −0.064387 |
| 309 | 700.7/264.4 > MonoHexCer:d18:1/16:0 | −0.112008 | 0.009775 | −0.025024 | −0.032283 | 0.019932 | −0.024793 | 0.019286 | 0.00942 | 0.00843 | 0.010868 |
| 310 | 702.7/266.4 > MonoHexCer:d18:0/16:0 | −0.101652 | −0.0035 | 0.014003 | −0.052051 | 0.021878 | 0.023011 | 0.029614 | −0.022705 | 0.010232 | 0.042833 |
| 311 | 728.7/264.4 > MonoHexCer:d18:1/18:0 | −0.11268 | 0.011339 | −0.004475 | −0.01753 | 0.035311 | −0.020173 | −0.003757 | 0.019504 | 0.00322 | 0.000046 |
| 312 | 730.7/266.4 > MonoHexCer:d18:0/18:0 | −0.064829 | −0.049433 | −0.068011 | −0.000205 | −0.021072 | 0.007282 | 0.014183 | −0.031964 | 0.039015 | 0.050009 |
| 313 | 756.7/264.4 > MonoHexCer:d18:1/20:0 | −0.111871 | 0.021529 | −0.006646 | −0.019463 | 0.002738 | −0.020212 | 0.020009 | 0.0149981 | 0.024961 | 0.035352 |
| 314 | 758.7/266.4 > MonoHexCer:d18:0/20:0 | −0.074925 | −0.027204 | −0.007913 | −0.017198 | −0.052128 | 0.017976 | 0.045622 | 0.0229 | 0.030301 | 0.018782 |
| 315 | 784.8/264.4 > MonoHexCer:d18:1/22:0 | −0.105203 | 0.015772 | −0.031269 | −0.004289 | 0.020606 | −0.015912 | 0.069754 | 0.033202 | −0.002453 | 0.05733 |
| 316 | 786.8/266.4 > MonoHexCer:d18:0/22:0 | −0.064289 | −0.06386 | −0.037273 | −0.004763 | −0.00237 | −0.022515 | 0.036404 | −0.00914 | −0.01623 | −0.022777 |
| 317 | 810.9/264.4 > MonoHexCer:d18:1/24:1 | −0.106991 | 0.016607 | −0.017266 | −0.014919 | 0.044607 | −0.030925 | 0.009093 | 0.015308 | 0.004225 | 0.021383 |
| 318 | 812.9/266.4 > MonoHexCer:d18:0/24:1 | −0.096559 | 0.033608 | 0.005667 | −0.018894 | 0.036743 | −0.023477 | 0.043847 | 0.010492 | −0.002766 | 0.000474 |
| 319 | 812.9/264.4 > MonoHexCer:d18:1/24:0 | −0.102008 | 0.016485 | −0.035639 | 0.011794 | 0.035872 | −0.011865 | 0.063975 | 0.029624 | 0.000328 | 0.067694 |
| 320 | 814.9/266.4 > MonoHexCer:d18:0/24:0 | −0.099983 | 0.003935 | −0.049061 | 0.009426 | 0.040071 | 0.007889 | 0.034255 | 0.031468 | 0.021017 | 0.062764 |
| 321 | 838.9/264.4 > MonoHexCer:d18:1/26:1 | −0.102111 | −0.001734 | −0.026483 | 0.029993 | 0.005824 | −0.016945 | 0.012547 | −0.023989 | 0.031495 | −0.023884 |
| 322 | 840.9/266.4 > MonoHexCer:d18:0/26:1 | −0.041806 | −0.033011 | −0.033784 | −0.002945 | −0.019284 | 0.017952 | −0.001866 | 0.039045 | 0.083205 | −0.020896 |
| 323 | 840.9/264.4 > MonoHexCer:d18:1/26:0 | −0.096049 | 0.000741 | 0.026923 | −0.022177 | −0.019367 | 0.003254 | 0.01334 | 0.007626 | 0.036832 | −0.037079 |
| 324 | 842.9/266.4 > MonoHexCer:d18:0/26:0 | −0.047144 | −0.066416 | −0.100332 | −0.00996 | −0.013143 | 0.010247 | −0.045386 | −0.050684 | 0.063429 | 0.040054 |
| 325 | 862.7/264.4 > DiHexCer:d18:1/16:0 | −0.107527 | 0.012342 | −0.024305 | −0.023702 | 0.036937 | −0.031428 | 0.016616 | 0.02813 | −0.00979 | 0.052736 |
| 326 | 864.7/266.4 > DiHexCer:d18:0/16:0 | −0.094513 | 0.007059 | −0.010365 | −0.014959 | 0.03917 | −0.039561 | 0.010417 | 0.019568 | 0.018782 | 0.077485 |
| 327 | 890.7/264.4 > DiHexCer:d18:1/18:0 | −0.11493 | 0.003269 | −0.028963 | −0.01662 | 0.025012 | −0.006018 | 0.006738 | 0.008245 | 0.017552 | 0.025609 |
| 328 | 892.7/266.4 > DiHexCer:d18:0/18:0 | −0.059357 | −0.02586 | 0.028377 | −0.018225 | 0.039848 | −0.013563 | 0.033087 | −0.010374 | 0.087077 | 0.0352 |
| 329 | 918.7/264.4 > DiHexCer:d18:1/20:0 | −0.112016 | 0.024726 | −0.013977 | −0.00528 | −0.000369 | −0.006728 | 0.000889 | 0.00523 | 0.029157 | 0.025759 |
| 330 | 920.7/266.4 > DiHexCer:d18:0/20:0 | 0.009265 | −0.046859 | −0.068153 | 0.024459 | 0.030085 | −0.060962 | −0.004424 | −0.022557 | 0.125026 | 0.059924 |
| 331 | 946.8/264.4 > DiHexCer:d18:1/22:0 | −0.109722 | 0.008637 | −0.033221 | 0.006162 | 0.024736 | −0.010614 | 0.042134 | 0.046191 | 0.001941 | 0.055494 |
| 332 | 948.8/266.4 > DiHexCer:d18:0/22:0 | −0.011444 | −0.019112 | −0.012358 | −0.015384 | 0.030834 | −0.08189 | 0.031404 | 0.020608 | 0.120842 | 0.063106 |
| 333 | 972.9/264.4 > DiHexCer:d18:1/24:1 | −0.109056 | 0.011909 | −0.017663 | −0.013614 | 0.040719 | −0.023242 | 0.004811 | 0.038258 | −0.005116 | 0.043349 |
| 334 | 974.9/266.4 > DiHexCer:d18:0/24:1 | −0.089705 | 0.017069 | −0.021334 | −0.010862 | 0.051061 | 0.001758 | 0.004795 | 0.044162 | −0.034613 | 0.051217 |
| 335 | 974.9/264.4 > DiHexCer:d18:1/24:0 | −0.108153 | 0.016433 | −0.023225 | 0.002779 | 0.021313 | −0.012301 | 0.04733 | 0.04248 | −0.005092 | 0.062686 |
| 336 | 976.9/266.4 > DiHexCer:d18:0/24:0 | −0.099182 | −0.019931 | −0.051806 | −0.0043 | 0.028215 | 0.033159 | 0.003167 | 0.032785 | 0.083085 | 0.002845 |
| 337 | 1000.9/264.4 > DiHexCer:d18:1/26:1 | −0.082127 | −0.067 | −0.012875 | 0.037777 | 0.017597 | 0.004952 | −0.022668 | −0.037941 | 0.045362 | 0.003632 |
| 338 | 1002.9/266.4 > DiHexCer:d18:0/26:1 | −0.05587 | 0.003063 | 0.051329 | −0.049613 | 0.004006 | 0.068315 | −0.032402 | −0.005886 | 0.067684 | 0.006934 |
| 339 | 1002.9/264.4 > DiHexCer:d18:1/26:0 | −0.082571 | −0.044316 | 0.083001 | 0.012823 | 0.024042 | 0.015701 | −0.010005 | −0.027026 | −0.000071 | −0.034297 |
| 340 | 1004.9/266.4 > DiHexCer:d18:0/26:0 | 0.003676 | −0.015741 | 0.041908 | −0.024183 | 0.01341 | 0.015879 | −0.052165 | −0.10076 | 0.08486 | 0.015338 |

| | L | M | N | O | P | Q | R | S | T | U | V | W | X | Y |
|---|---|---|---|---|---|---|---|---|---|---|---|---|---|---|
| 1 | 0.003308 | −0.002547 | −0.000245 | −0.045864 | −0.039148 | 0.015397 | 0.023182 | −0.02994 | −0.009594 | −0.033865 | 0.038044 | −0.023224 | −0.012023 | −0.011814 |
| 2 | −0.017174 | 0.009017 | 0.03653 | −0.047416 | −0.039431 | 0.003237 | 0.025664 | 0.012168 | 0.007093 | −0.006893 | −0.023417 | −0.025518 | −0.037855 | 0.007129 |
| 3 | −0.042881 | 0.020851 | −0.006094 | −0.013522 | −0.01499 | 0.019489 | −0.014257 | 0.034317 | −0.042837 | 0.010513 | 0.004933 | −0.052769 | 0.003813 | −0.034184 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 4 | 0.014622 | 0.015145 | 0.033357 | −0.003942 | −0.090206 | 0.00736 | 0.010926 | −0.101813 | −0.009655 | −0.032179 | 0.011928 | 0.007851 | 0.036622 | 0.029081 |
| 5 | −0.060231 | 0.085379 | 0.07655 | −0.03839 | 0.074284 | −0.001642 | 0.029776 | 0.073005 | 0.024989 | 0.051167 | −0.028836 | −0.017129 | 0.04343 | 0.022396 |
| 6 | 0.032693 | −0.023152 | 0.058503 | 0.023848 | −0.113688 | −0.03482 | 0.049725 | 0.032073 | −0.098307 | 0.050211 | 0.059924 | −0.119045 | −0.105522 | 0.041872 |
| 7 | −0.000946 | 0.008336 | 0.026256 | 0.092305 | −0.081848 | −0.039156 | 0.043075 | 0.141695 | 0.007783 | 0.060593 | 0.011785 | −0.114688 | −0.021909 | −0.013845 |
| 8 | 0.015046 | 0.056726 | −0.016366 | −0.052085 | −0.095767 | 0.006883 | 0.059031 | 0.099337 | 0.126651 | 0.024796 | −0.033839 | −0.060542 | 0.211893 | 0.005163 |
| 9 | 0.04308 | 0.080413 | 0.047881 | −0.012462 | −0.017033 | 0.010319 | −0.017326 | −0.077634 | 0.023722 | −0.004736 | 0.031624 | 0.012482 | 0.02895 | 0.020689 |
| 10 | −0.060689 | 0.040633 | 0.02881 | 0.008355 | −0.050685 | −0.049266 | 0.067202 | 0.075555 | 0.088087 | 0.042362 | 0.093365 | −0.029775 | 0.004669 | 0.034654 |
| 11 | −0.078203 | 0.125106 | −0.014687 | −0.06268 | 0.038569 | −0.112268 | −0.059175 | 0.035644 | −0.002634 | 0.051332 | 0.005161 | −0.147368 | −0.11236 | 0.08078 |
| 12 | 0.06629 | −0.096071 | −0.000105 | −0.031152 | 0.019182 | 0.051847 | 0.129659 | 0.223234 | −0.106103 | 0.021089 | −0.033977 | 0.205273 | 0.048401 | 0.022055 |
| 13 | 0.017485 | 0.081878 | 0.036794 | 0.10099 | −0.047726 | −0.088858 | −0.006914 | 0.044464 | 0.040196 | 0.00422 | 0.002245 | 0.003606 | −0.013486 | 0.033594 |
| 14 | 0.017979 | 0.086512 | 0.031937 | 0.095533 | −0.060846 | −0.097134 | 0.036216 | 0.051185 | 0.016495 | −0.036025 | −0.004438 | 0.006091 | −0.031079 | 0.060278 |
| 15 | −0.002737 | 0.006442 | 0.026742 | −0.045852 | 0.008673 | 0.02537 | 0.020723 | −0.030536 | 0.012416 | −0.002456 | 0.0375 | −0.014215 | −0.04501 | 0.000939 |
| 16 | 0.107871 | 0.102279 | 0.070995 | −0.10798 | 0.036714 | −0.138884 | −0.070834 | 0.045317 | −0.041635 | −0.171093 | 0.017936 | −0.023604 | −0.02811 | 0.036118 |
| 17 | 0.005446 | 0.027761 | 0.000261 | −0.028609 | 0.005579 | 0.032463 | 0.017211 | −0.01369 | −0.006549 | −0.030267 | −0.083211 | −0.004329 | −0.039143 | 0.109518 |
| 18 | −0.007093 | 0.033824 | 0.00515 | −0.044609 | 0.083026 | −0.012931 | −0.048778 | 0.053336 | −0.123124 | −0.114258 | −0.063334 | −0.012668 | 0.041316 | −0.03936 |
| 19 | 0.078021 | 0.054144 | −0.08041 | −0.039264 | 0.018281 | −0.026898 | −0.013635 | −0.026317 | −0.020085 | 0.003626 | 0.026584 | −0.075554 | 0.012031 | −0.063392 |
| 20 | 0.039065 | 0.000607 | 0.039046 | 0.023436 | 0.052145 | −0.010584 | 0.017516 | −0.012355 | 0.035693 | 0.031124 | −0.009936 | −0.010861 | −0.010795 | 0.003198 |
| 21 | 0.015722 | 0.025598 | 0.015722 | −0.026026 | −0.070326 | −0.0123 | 0.016366 | −0.020489 | −0.049519 | 0.044219 | 0.03157 | −0.006464 | 0.011802 | 0.02226 |
| 22 | 0.012327 | 0.011967 | 0.009074 | −0.010817 | 0.014924 | 0.013214 | 0.063079 | −0.085584 | 0.002391 | 0.044474 | −0.000573 | −0.007706 | −0.159758 | 0.046317 |
| 23 | 0.041839 | 0.025381 | 0.044453 | −0.035995 | −0.066355 | 0.060013 | −0.008616 | 0.009413 | −0.126928 | 0.029337 | 0.044089 | −0.072985 | −0.148395 | −0.061958 |
| 24 | −0.000089 | 0.071841 | −0.045536 | −0.061079 | 0.002561 | −0.022631 | 0.03339 | −0.067744 | −0.01955 | 0.048086 | −0.014966 | −0.034577 | 0.016912 | −0.036131 |
| 25 | 0.056305 | 0.0691 | 0.001648 | −0.003857 | −0.008275 | −0.045277 | 0.016151 | 0.002672 | −0.025499 | 0.063119 | 0.045161 | −0.068719 | −0.0588 | −0.078089 |
| 26 | 0.023613 | −0.000763 | 0.020617 | 0.012379 | 0.066641 | −0.010149 | 0.002873 | −0.003946 | 0.02772 | 0.031104 | −0.005749 | −0.012125 | −0.00819 | −0.013005 |
| 27 | 0.035401 | −0.027009 | 0.042343 | 0.006519 | 0.072629 | 0.006151 | −0.005193 | −0.007541 | 0.038386 | 0.029513 | −0.013056 | −0.007818 | 0.006682 | 0.007751 |
| 28 | 0.060086 | 0.02327 | 0.032898 | 0.006727 | −0.059467 | 0.003497 | 0.017859 | −0.05674 | 0.015923 | −0.013102 | 0.025792 | −0.025011 | −0.009234 | 0.009669 |
| 29 | 0.022413 | −0.017389 | −0.023005 | −0.031194 | −0.014777 | 0.035674 | 0.048655 | 0.085831 | −0.022275 | 0.081309 | −0.048929 | −0.046948 | −0.092529 | 0.032255 |
| 30 | −0.01465 | −0.047887 | −0.003856 | 0.03123 | −0.063689 | 0.014348 | −0.002887 | −0.056908 | 0.026805 | −0.031513 | 0.076314 | −0.036866 | 0.068327 | 0.012971 |
| 31 | 0.028018 | 0.004869 | 0.055989 | −0.023565 | −0.042318 | 0.01935 | −0.010525 | 0.021875 | −0.036542 | 0.026651 | −0.008213 | 0.021851 | −0.021893 | 0.029953 |
| 32 | 0.123282 | −0.007899 | 0.140569 | −0.004687 | 0.01158 | −0.052698 | 0.075854 | −0.101376 | −0.054635 | −0.103275 | −0.097689 | −0.001782 | −0.100511 | −0.011694 |
| 33 | −0.015278 | −0.028588 | −0.004606 | −0.053081 | 0.144102 | −0.066225 | 0.014665 | −0.008538 | −0.013358 | 0.057384 | 0.050338 | −0.005316 | −0.063036 | 0.014238 |
| 34 | 0.07753 | −0.030242 | −0.03082 | 0.074371 | 0.056984 | −0.010306 | 0.018444 | −0.022853 | 0.021447 | −0.0168 | −0.014323 | 0.012368 | 0.008014 | 0.023704 |
| 35 | −0.104207 | 0.042612 | 0.013367 | 0.037786 | 0.054618 | −0.077934 | −0.00581 | 0.030691 | −0.022732 | −0.00554 | 0.101441 | 0.081474 | 0.024351 | 0.019595 |
| 36 | −0.07358 | 0.057679 | −0.032351 | 0.007542 | 0.045043 | 0.062737 | 0.024934 | −0.067862 | 0.022896 | −0.005023 | −0.044631 | −0.001653 | −0.050971 | 0.007965 |
| 37 | 0.028742 | −0.010463 | 0.008003 | 0.005519 | 0.02002 | 0.016912 | 0.014862 | −0.059793 | −0.006436 | 0.053059 | −0.024665 | −0.014359 | −0.030917 | 0.05026 |
| 38 | −0.030731 | −0.053025 | 0.067837 | 0.003763 | −0.020225 | 0.133939 | 0.001066 | −0.035827 | 0.103361 | 0.136392 | −0.040819 | 0.042525 | 0.178894 | 0.140018 |
| 39 | −0.009473 | −0.02129 | −0.088437 | 0.012204 | 0.0061 | 0.008269 | −0.039347 | 0.031317 | 0.054324 | 0.038876 | −0.000175 | 0.038021 | 0.027478 | −0.007861 |
| 40 | 0.054654 | −0.058261 | −0.069599 | 0.017075 | 0.051317 | 0.043654 | 0.050248 | 0.010226 | −0.007945 | −0.041251 | −0.040549 | 0.019691 | −0.00489 | 0.01862 |
| 41 | 0.09642 | −0.03649 | −0.078825 | 0.051992 | 0.048017 | 0.025377 | 0.012377 | 0.038071 | 0.007521 | 0.006488 | −0.053838 | −0.006316 | 0.015296 | −0.033198 |
| 42 | 0.074808 | 0.006091 | −0.105982 | 0.00796 | 0.051179 | −0.031275 | 0.002318 | −0.006734 | −0.016524 | 0.020512 | −0.039091 | −0.049275 | 0.043679 | −0.025206 |
| 43 | 0.064548 | −0.042657 | −0.079552 | 0.063795 | 0.01633 | 0.040755 | 0.02532 | 0.057423 | −0.011243 | −0.025691 | −0.057959 | 0.011398 | 0.015011 | −0.009269 |
| 44 | 0.037001 | −0.031329 | −0.036114 | 0.043786 | 0.03015 | 0.040426 | 0.052976 | 0.00095 | −0.043113 | 0.02878 | −0.050554 | 0.00436 | 0.02482 | −0.035186 |
| 45 | 0.039805 | −0.027577 | −0.072903 | 0.070101 | 0.022451 | −0.01397 | 0.052163 | 0.114592 | 0.017492 | −0.006575 | −0.070351 | −0.006485 | −0.013774 | −0.071801 |
| 46 | −0.008315 | 0.010683 | −0.049706 | 0.001014 | 0.027971 | −0.005667 | 0.010061 | −0.046422 | 0.054045 | −0.016671 | −0.027708 | −0.045578 | −0.032743 | −0.041332 |
| 47 | −0.103018 | −0.001198 | −0.054415 | −0.013364 | −0.026457 | 0.035717 | −0.053813 | 0.025727 | −0.010189 | −0.028158 | 0.02308 | 0.068273 | −0.066942 | −0.033349 |
| 48 | −0.044841 | −0.033593 | −0.008296 | 0.024817 | −0.025576 | 0.070173 | −0.083334 | 0.045657 | 0.060313 | −0.005708 | 0.029436 | 0.03841 | 0.00011 | 0.064239 |
| 49 | −0.009426 | −0.040931 | −0.010076 | 0.056936 | −0.076021 | 0.029376 | −0.036694 | −0.046189 | 0.033724 | −0.050386 | 0.070951 | −0.048343 | 0.099493 | 0.002574 |
| 50 | 0.072162 | −0.005281 | −0.055028 | −0.019648 | 0.003709 | −0.040555 | 0.005519 | −0.036102 | 0.040195 | 0.001522 | 0.095643 | −0.050163 | −0.030476 | −0.01734 |
| 51 | −0.159249 | −0.012333 | −0.090223 | −0.050252 | 0.066331 | −0.030642 | 0.026773 | 0.024712 | −0.00518 | 0.008237 | 0.04259 | 0.011431 | −0.01065 | −0.005217 |
| 52 | 0.105184 | −0.066636 | −0.084086 | −0.067401 | −0.013218 | −0.005212 | 0.00244 | −0.080005 | 0.112725 | −0.015437 | 0.039451 | 0.029019 | −0.040957 | 0.004658 |
| 53 | −0.101473 | −0.046866 | −0.068374 | −0.018699 | 0.058111 | −0.044101 | 0.012929 | 0.005455 | 0.015517 | −0.025329 | 0.022695 | 0.005983 | 0.041862 | −0.074153 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 54 | 0.033327 | 0.014921 | −0.118712 | 0.02033 | 0.015652 | 0.054817 | −0.014636 | −0.047357 | 0.035274 | 0.049464 | 0.018723 | −0.056481 | 0.154308 | −0.033034 |
| 55 | −0.054947 | −0.025515 | −0.024461 | −0.020419 | −0.014491 | −0.068953 | 0.01223 | −0.037632 | 0.055274 | −0.035258 | 0.037843 | −0.001296 | 0.005116 | 0.003047 |
| 56 | 0.009586 | −0.030106 | −0.007905 | 0.076017 | −0.076118 | 0.069128 | −0.044164 | −0.012091 | 0.020528 | −0.048782 | 0.077231 | −0.025985 | 0.099593 | −0.011228 |
| 57 | 0.025978 | −0.019721 | −0.010562 | 0.04442 | −0.031424 | 0.002931 | −0.013918 | −0.01326 | −0.090679 | 0.013291 | −0.005426 | 0.034182 | −0.050319 | 0.040604 |
| 58 | −0.005846 | 0.018008 | −0.052461 | −0.059726 | 0.066385 | 0.04604 | −0.010641 | −0.037605 | −0.034561 | 0.09205 | 0.023697 | 0.053058 | 0.016969 | 0.04865 |
| 59 | 0.03795 | 0.014276 | −0.011574 | 0.105004 | −0.069442 | 0.109909 | 0.058271 | −0.049262 | −0.096016 | 0.082523 | −0.025539 | −0.013341 | 0.069418 | −0.060175 |
| 60 | 0.093942 | 0.074555 | 0.01958 | −0.032295 | −0.034062 | −0.01283 | 0.019749 | −0.067956 | 0.023352 | 0.009908 | −0.012326 | 0.009252 | −0.026324 | 0.056961 |
| 61 | 0.135459 | 0.051089 | −0.04122 | 0.009483 | −0.057779 | 0.096977 | −0.006202 | −0.033885 | 0.045814 | 0.023956 | −0.029743 | 0.006336 | 0.076463 | 0.016237 |
| 62 | −0.057545 | 0.06158 | −0.019796 | 0.00584 | −0.021007 | 0.005818 | −0.016651 | −0.04107 | −0.109873 | 0.043229 | −0.009474 | 0.003267 | 0.037204 | −0.005531 |
| 63 | 0.070035 | 0.0184 | −0.056568 | 0.026179 | −0.040158 | 0.070584 | −0.057173 | −0.019735 | 0.021697 | 0.001471 | 0.004149 | 0.001107 | 0.102003 | −0.022179 |
| 64 | 0.009092 | 0.008976 | −0.008655 | 0.040704 | −0.090031 | 0.033806 | −0.02536 | −0.010299 | −0.014634 | −0.034076 | 0.035142 | −0.013937 | 0.086724 | 0.010794 |
| 65 | 0.021491 | 0.025254 | 0.022395 | 0.061301 | −0.068497 | −0.011285 | 0.019394 | 0.005377 | −0.110015 | 0.040322 | −0.02895 | 0.04435 | −0.017975 | 0.071365 |
| 66 | 0.035385 | 0.006245 | 0.024418 | 0.087431 | −0.053089 | 0.060868 | −0.008595 | −0.07436 | −0.097023 | 0.064818 | −0.00676 | 0.027675 | 0.058086 | −0.015482 |
| 67 | 0.009006 | 0.011803 | −0.041554 | 0.02721 | −0.060226 | 0.089073 | 0.084409 | 0.084185 | 0.106621 | −0.008915 | 0.004413 | 0.105331 | −0.013243 | −0.078808 |
| 68 | 0.017152 | 0.031098 | −0.10899 | 0.029347 | 0.026051 | 0.024679 | 0.037786 | 0.009575 | 0.050324 | 0.062461 | −0.013123 | −0.047191 | −0.019056 | −0.043173 |
| 69 | −0.026977 | 0.056834 | 0.078454 | 0.053582 | −0.037554 | −0.07217 | 0.011894 | 0.010022 | 0.115211 | −0.055173 | 0.043267 | −0.004759 | 0.006181 | −0.004637 |
| 70 | −0.046641 | 0.057634 | 0.093013 | 0.077785 | −0.06523 | −0.074312 | −0.007195 | 0.037934 | 0.037228 | −0.062304 | 0.109096 | −0.01438 | −0.01033 | −0.034745 |
| 71 | −0.036061 | 0.012223 | 0.068868 | −0.020123 | −0.100658 | −0.087083 | −0.022678 | 0.049805 | 0.005943 | −0.021443 | −0.024361 | −0.004716 | 0.019936 | 0.104676 |
| 72 | −0.034193 | 0.014122 | −0.00633 | −0.132359 | −0.183645 | −0.016499 | −0.034954 | 0.019917 | −0.058542 | −0.058055 | −0.005455 | 0.029155 | 0.064683 | 0.031577 |
| 73 | −0.069227 | 0.003612 | 0.018914 | −0.204365 | −0.178189 | −0.05425 | −0.038834 | 0.064363 | −0.087593 | −0.04283 | −0.034057 | −0.020471 | −0.040156 | 0.134019 |
| 74 | −0.001246 | 0.037864 | −0.068349 | −0.036533 | 0.013134 | −0.089425 | −0.022112 | −0.05956 | −0.140986 | 0.079977 | 0.07358 | −0.071196 | 0.064103 | −0.046949 |
| 75 | −0.029212 | 0.07874 | 0.063506 | 0.083301 | −0.061216 | −0.108631 | 0.013267 | 0.018176 | 0.026683 | −0.041695 | 0.017561 | 0.004715 | −0.024054 | 0.032843 |
| 76 | −0.062974 | 0.075037 | 0.065144 | 0.072529 | −0.026383 | −0.131951 | 0.047837 | 0.065056 | −0.027018 | −0.070349 | −0.011773 | 0.02893 | −0.025909 | −0.009789 |
| 77 | −0.032246 | 0.064903 | 0.07154 | 0.081135 | −0.056491 | −0.116073 | 0.011661 | 0.015424 | 0.045146 | −0.051149 | 0.022189 | −0.008769 | −0.015274 | 0.018349 |
| 78 | −0.027583 | 0.060025 | 0.075007 | 0.083029 | −0.058029 | −0.107338 | 0.008334 | 0.016862 | 0.040747 | −0.042515 | 0.017481 | −0.010599 | −0.029756 | 0.020029 |
| 79 | −0.010826 | 0.08886 | 0.074856 | 0.059296 | −0.047459 | −0.119408 | 0.015127 | −0.018748 | 0.05302 | −0.074917 | 0.008027 | −0.006834 | −0.008272 | 0.029383 |
| 80 | −0.072736 | 0.07573 | 0.077836 | −0.039813 | 0.050022 | 0.054018 | −0.096433 | 0.06945 | −0.034745 | 0.0502 | 0.098336 | −0.095435 | −0.10789 | 0.001687 |
| 81 | −0.046559 | −0.018227 | −0.008894 | −0.025929 | −0.051715 | −0.096504 | 0.044787 | −0.020998 | 0.007707 | 0.020919 | 0.039015 | −0.024355 | 0.003805 | −0.069215 |
| 82 | 0.015539 | −0.039516 | 0.036335 | −0.008217 | 0.0658 | −0.023888 | 0.020486 | 0.006539 | 0.010635 | −0.008652 | 0.001223 | −0.034752 | 0.009275 | −0.011977 |
| 83 | 0.02289 | −0.044516 | 0.048308 | −0.004222 | 0.073798 | 0.008905 | 0.001123 | 0.003523 | 0.023168 | 0.016433 | −0.013305 | −0.007428 | 0.016473 | 0.013037 |
| 84 | 0.026397 | −0.036459 | 0.061722 | 0.000013 | 0.069253 | 0.021453 | 0.00202 | 0.003495 | 0.024009 | 0.026368 | −0.019737 | 0.024757 | 0.043048 | 0.010793 |
| 85 | −0.038749 | 0.014261 | −0.014204 | −0.147655 | −0.092778 | 0.119318 | −0.025426 | 0.050137 | −0.056433 | −0.057107 | 0.019474 | 0.072064 | 0.07421 | 0.027529 |
| 86 | −0.018279 | −0.012998 | −0.013524 | −0.142559 | −0.081151 | 0.034442 | −0.05062 | 0.078047 | −0.010114 | −0.079603 | −0.006676 | 0.040001 | 0.035901 | 0.055928 |
| 87 | −0.010434 | −0.034664 | 0.026701 | −0.054115 | −0.040116 | 0.042999 | 0.025725 | 0.040013 | −0.001162 | −0.05084 | −0.003268 | 0.031574 | 0.009395 | 0.052443 |
| 88 | 0.027579 | −0.027152 | 0.048388 | −0.024272 | 0.070923 | −0.003702 | −0.01201 | 0.031795 | 0.020541 | 0.01567 | −0.015465 | −0.017719 | 0.015434 | 0.014635 |
| 89 | 0.034423 | −0.037488 | 0.048205 | 0.002797 | 0.090855 | 0.011037 | 0.004555 | 0.004226 | 0.037401 | 0.032039 | −0.01244 | 0.001007 | 0.012894 | 0.007945 |
| 90 | 0.03972 | −0.016443 | 0.043132 | 0.004012 | 0.063756 | 0.04114 | 0.00899 | −0.006671 | 0.033514 | 0.029457 | −0.013391 | −0.008317 | 0.040138 | 0.04598 |
| 91 | 0.015342 | 0.002832 | −0.003288 | 0.006007 | 0.010033 | 0.028887 | −0.014135 | 0.000436 | 0.023509 | −0.028404 | 0.010841 | 0.005463 | 0.008117 | −0.054761 |
| 92 | −0.005078 | 0.031465 | 0.010352 | −0.030872 | −0.097701 | 0.020618 | 0.047366 | −0.041607 | −0.030026 | −0.094868 | 0.044587 | 0.094475 | −0.038904 | −0.078756 |
| 93 | 0.055264 | −0.003104 | 0.030411 | −0.0617 | 0.035799 | 0.020544 | −0.045303 | −0.004919 | 0.018546 | −0.012361 | 0.026951 | 0.028727 | −0.016975 | 0.011175 |
| 94 | 0.025747 | 0.058091 | 0.058151 | −0.010863 | 0.00578 | 0.034527 | 0.003438 | 0.023465 | −0.000183 | 0.033013 | 0.026619 | −0.045578 | −0.045687 | −0.04514 |
| 95 | −0.093182 | −0.130345 | 0.1029 | −0.051587 | 0.052738 | 0.012142 | −0.028551 | −0.05858 | 0.065288 | 0.01953 | 0.077392 | −0.042845 | 0.020447 | −0.047366 |
| 96 | −0.008602 | 0.010382 | −0.033474 | −0.047277 | −0.040894 | 0.128133 | −0.000571 | −0.009867 | 0.043293 | 0.009782 | 0.131161 | −0.063362 | −0.019585 | 0.103118 |
| 97 | 0.00378 | −0.051979 | 0.019427 | −0.030699 | −0.032659 | 0.046623 | −0.015486 | −0.005901 | −0.053828 | 0.016287 | 0.047346 | −0.038669 | 0.008852 | 0.030576 |
| 98 | −0.050227 | 0.016218 | 0.016651 | −0.008387 | −0.026681 | 0.015879 | 0.015182 | 0.032084 | −0.012784 | 0.015899 | −0.034406 | 0.017183 | −0.049207 | 0.024514 |
| 99 | −0.006002 | −0.002116 | 0.019785 | −0.0614 | −0.004259 | 0.030702 | −0.013637 | −0.047485 | −0.016891 | −0.044783 | 0.015691 | −0.01094 | 0.022087 | 0.008851 |
| 100 | −0.000504 | 0.046895 | −0.017756 | −0.05651 | −0.010073 | 0.004397 | −0.061277 | −0.040784 | 0.031474 | −0.010924 | −0.006241 | −0.053738 | −0.015065 | 0.001623 |
| 101 | −0.047125 | 0.038393 | 0.013269 | −0.024264 | −0.014894 | −0.001625 | 0.006928 | 0.057459 | −0.024491 | 0.074202 | −0.007299 | 0.004444 | −0.00185 | −0.009553 |
| 102 | −0.018475 | −0.147461 | 0.02019 | −0.139109 | 0.079541 | 0.098901 | −0.065051 | −0.041693 | 0.109475 | −0.08018 | 0.087806 | 0.016041 | −0.088025 | 0.049756 |
| 103 | −0.005846 | −0.094542 | 0.063276 | −0.000577 | 0.08384 | 0.03697 | 0.071644 | −0.009052 | 0.061043 | −0.069604 | 0.070775 | −0.017359 | −0.015588 | 0.076852 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 104 | 0.00997 | −0.07723 | 0.043708 | −0.044006 | 0.042076 | −0.000476 | 0.036004 | −0.042129 | −0.07933 | −0.015462 | 0.069451 | 0.01647 | 0.013989 | 0.044998 |
| 105 | 0.016812 | 0.065587 | 0.026616 | 0.069501 | 0.065227 | −0.030396 | −0.040404 | 0.088367 | −0.079702 | 0.000077 | −0.17441 | 0.038717 | −0.103434 | 0.218324 |
| 106 | −0.064143 | −0.025834 | 0.039479 | 0.005299 | 0.018919 | −0.039209 | 0.040703 | −0.026402 | 0.029722 | −0.041993 | 0.021235 | 0.024691 | −0.008093 | −0.092667 |
| 107 | −0.095551 | −0.003953 | 0.015689 | −0.098643 | −0.02159 | −0.015009 | 0.02631 | −0.064322 | −0.058457 | 0.021402 | −0.017321 | −0.070065 | 0.059086 | 0.002565 |
| 108 | −0.039326 | 0.025007 | −0.032646 | −0.01792 | 0.015007 | 0.022446 | 0.069502 | 0.015038 | −0.136029 | 0.03092 | 0.044485 | −0.032984 | −0.13733 | −0.089836 |
| 109 | −0.054256 | 0.092215 | 0.042699 | 0.037581 | 0.132867 | 0.087968 | −0.029788 | −0.124624 | 0.020052 | 0.017497 | 0.008482 | −0.085607 | 0.020305 | −0.087246 |
| 110 | −0.058227 | 0.047563 | 0.074466 | −0.008956 | 0.022766 | 0.053867 | −0.12182 | −0.084037 | 0.042535 | −0.098541 | 0.03259 | −0.023971 | 0.035246 | −0.057242 |
| 111 | −0.000143 | −0.011331 | −0.040898 | −0.040843 | 0.011743 | −0.021798 | 0.023434 | −0.049689 | −0.082331 | 0.043722 | 0.009979 | 0.047252 | −0.062921 | 0.015042 |
| 112 | −0.042376 | −0.001892 | 0.033669 | 0.036262 | 0.010352 | 0.09714 | 0.033385 | 0.002392 | −0.008421 | −0.091906 | −0.031885 | 0.00688 | −0.088354 | 0.016781 |
| 113 | −0.032879 | −0.00386 | 0.040923 | 0.005339 | 0.001722 | 0.099153 | 0.060057 | −0.035888 | −0.075285 | −0.039517 | 0.117111 | 0.013151 | −0.043393 | 0.009151 |
| 114 | 0.040198 | −0.035486 | 0.046232 | 0.053256 | 0.059736 | 0.0077 | 0.003176 | 0.123407 | −0.045818 | −0.026932 | −0.018929 | −0.05294 | 0.071933 | −0.08505 |
| 115 | 0.012585 | 0.055979 | 0.027995 | −0.013712 | 0.017072 | −0.025387 | −0.057861 | −0.037558 | −0.065361 | −0.101332 | −0.046231 | 0.12092 | 0.068677 | −0.115862 |
| 116 | −0.073635 | 0.084734 | 0.001067 | 0.013099 | −0.043377 | −0.089918 | −0.031906 | −0.025012 | −0.088443 | −0.012651 | −0.132989 | 0.056429 | 0.063345 | −0.048792 |
| 117 | −0.045205 | −0.012051 | −0.089051 | 0.044717 | 0.182913 | −0.037871 | −0.03985 | 0.090289 | −0.008694 | −0.053033 | 0.0481 | −0.010921 | 0.030983 | 0.240147 |
| 118 | −0.134606 | 0.055223 | 0.022112 | 0.016725 | 0.014155 | 0.106655 | −0.037479 | −0.014051 | −0.013307 | −0.080397 | 0.060454 | 0.043882 | 0.065382 | 0.031126 |
| 119 | −0.013651 | 0.155673 | 0.014774 | 0.020818 | −0.017116 | 0.064659 | −0.056587 | 0.007273 | 0.072565 | 0.002329 | 0.027663 | −0.040567 | 0.070428 | −0.057418 |
| 120 | −0.021909 | −0.015724 | −0.03433 | 0.035394 | 0.059246 | −0.042471 | −0.060249 | 0.033309 | 0.032453 | 0.026479 | −0.026795 | 0.021191 | 0.03952 | 0.060908 |
| 121 | −0.048285 | 0.06475 | 0.022379 | −0.005853 | 0.192262 | 0.00429 | −0.199941 | 0.016276 | −0.013294 | −0.066392 | 0.016821 | 0.076185 | 0.065182 | 0.109355 |
| 122 | −0.051372 | 0.048651 | 0.113746 | 0.00874 | 0.018834 | 0.037346 | −0.031287 | −0.031316 | 0.023968 | 0.022915 | −0.000798 | 0.069508 | 0.046126 | 0.006979 |
| 123 | −0.082122 | 0.140561 | 0.066997 | −0.012772 | 0.04421 | 0.025787 | −0.05525 | −0.040929 | 0.013101 | 0.037324 | −0.068148 | 0.006797 | 0.086567 | −0.02355 |
| 124 | 0.035092 | 0.154127 | 0.036452 | 0.035274 | −0.031727 | 0.058614 | −0.048972 | 0.033172 | 0.008309 | 0.043672 | 0.011955 | −0.074703 | 0.046257 | −0.031442 |
| 125 | 0.003876 | −0.051305 | 0.01478 | −0.01618 | 0.008798 | 0.02867 | 0.00753 | −0.030274 | −0.001367 | −0.094276 | −0.038447 | 0.04501 | −0.043777 | 0.04414 |
| 126 | −0.075177 | 0.020436 | 0.107972 | 0.04186 | 0.067603 | −0.057268 | −0.000455 | −0.015468 | −0.029458 | −0.014727 | 0.054916 | 0.085321 | 0.083572 | 0.080802 |
| 127 | −0.076451 | 0.027187 | 0.015781 | 0.028503 | −0.011412 | −0.068781 | 0.051621 | 0.001446 | 0.111723 | −0.036339 | 0.052465 | 0.037276 | 0.049115 | 0.016088 |
| 128 | −0.043794 | −0.007108 | 0.026699 | 0.031761 | −0.032723 | −0.002789 | 0.013292 | −0.080725 | −0.014074 | −0.029453 | 0.030967 | −0.066353 | −0.03073 | −0.033678 |
| 129 | 0.041214 | 0.120147 | 0.096819 | 0.086685 | 0.01112 | 0.133204 | −0.057316 | −0.026428 | 0.045344 | 0.066219 | 0.084801 | 0.079302 | −0.079078 | −0.006786 |
| 130 | −0.082098 | 0.0409 | 0.103926 | 0.070167 | −0.053161 | 0.091921 | 0.055442 | 0.043999 | −0.078288 | −0.070368 | 0.016172 | −0.023754 | −0.011101 | −0.057012 |
| 131 | 0.020617 | 0.040091 | 0.091551 | 0.131792 | 0.059956 | 0.045356 | 0.042704 | 0.047592 | −0.05712 | −0.084343 | 0.056218 | −0.092454 | 0.018434 | 0.197198 |
| 132 | −0.051534 | −0.051722 | −0.008209 | −0.013098 | 0.006332 | −0.004144 | 0.010507 | −0.011403 | −0.045554 | 0.002479 | 0.053844 | −0.087561 | −0.041178 | 0.021004 |
| 133 | −0.013744 | −0.004966 | 0.09893 | 0.032827 | 0.050779 | 0.102423 | 0.09019 | −0.111527 | 0.059348 | 0.004771 | −0.095782 | −0.151231 | −0.012455 | 0.000933 |
| 134 | 0.026611 | 0.046998 | −0.00808 | −0.030961 | 0.119544 | 0.004233 | 0.041114 | 0.007226 | −0.044058 | 0.073751 | 0.096866 | 0.276584 | 0.035842 | 0.063823 |
| 135 | 0.004309 | −0.000773 | 0.005389 | 0.015697 | 0.003071 | 0.003346 | −0.009875 | 0.022459 | 0.014313 | −0.004988 | −0.035876 | −0.015454 | −0.017763 | 0.003628 |
| 136 | 0.010006 | 0.147347 | −0.004968 | −0.018146 | −0.023913 | 0.080185 | 0.033971 | 0.079257 | 0.023991 | −0.060572 | −0.085438 | 0.009224 | 0.021575 | −0.041047 |
| 137 | −0.074224 | 0.036996 | 0.042528 | 0.012438 | −0.046138 | 0.036939 | 0.064469 | −0.038449 | −0.003813 | 0.010814 | 0.022905 | 0.029329 | −0.032737 | −0.034121 |
| 138 | −0.019009 | 0.112732 | 0.069748 | −0.050374 | 0.019335 | 0.069792 | 0.240202 | −0.06644 | −0.107054 | 0.057645 | 0.128452 | 0.062004 | 0.078173 | −0.051132 |
| 139 | 0.012076 | 0.007826 | −0.03826 | −0.026425 | −0.088166 | 0.000573 | −0.095612 | 0.156778 | 0.136774 | 0.170132 | 0.021445 | −0.019832 | −0.06176 | 0.061138 |
| 140 | −0.054233 | 0.023285 | −0.06401 | −0.0044 | 0.053669 | 0.063355 | 0.14745 | 0.044104 | −0.10637 | −0.096419 | −0.067553 | −0.039845 | 0.010221 | −0.049439 |
| 141 | −0.024524 | −0.050734 | −0.00317 | −0.000188 | 0.027475 | −0.020371 | −0.00188 | −0.017604 | 0.060311 | −0.021152 | −0.013981 | 0.021325 | −0.0092 | −0.050764 |
| 142 | 0.029365 | 0.105479 | −0.05169 | 0.073979 | −0.043823 | 0.124183 | −0.057096 | 0.07088 | −0.058341 | −0.017437 | −0.012606 | 0.024409 | −0.031188 | 0.083303 |
| 143 | −0.012304 | 0.038927 | 0.002122 | 0.011099 | −0.008392 | 0.062737 | −0.003071 | −0.057955 | −0.023711 | 0.031082 | −0.033667 | 0.020759 | −0.036888 | −0.02723 |
| 144 | 0.063068 | 0.156644 | −0.022205 | −0.007265 | −0.008393 | 0.102989 | −0.058701 | −0.002852 | 0.049847 | 0.003805 | −0.040363 | 0.041889 | 0.048319 | −0.044489 |
| 145 | −0.017408 | 0.070793 | 0.023857 | 0.009675 | 0.001731 | 0.075591 | −0.028976 | −0.006469 | 0.055546 | 0.007074 | 0.014836 | −0.066495 | −0.050134 | 0.018625 |
| 146 | −0.027173 | −0.031334 | −0.029217 | 0.031308 | −0.009338 | 0.002865 | 0.010873 | 0.024943 | −0.012865 | −0.002185 | 0.002338 | −0.010078 | 0.002615 | 0.020282 |
| 147 | −0.019027 | 0.044328 | 0.102664 | 0.046876 | 0.142381 | −0.025679 | 0.135068 | 0.103944 | −0.124608 | 0.016366 | 0.067073 | 0.220584 | −0.040394 | 0.145906 |
| 148 | −0.02854 | −0.045036 | 0.104744 | 0.061796 | −0.00842 | 0.046375 | 0.153344 | −0.021646 | 0.003178 | −0.055244 | −0.041869 | 0.01142 | 0.109584 | −0.017738 |
| 149 | −0.029213 | −0.023526 | 0.016417 | −0.011802 | 0.010285 | −0.047215 | −0.004363 | −0.005474 | 0.001491 | −0.020081 | 0.023958 | −0.014662 | 0.043174 | −0.016997 |
| 150 | −0.007137 | −0.006061 | −0.011568 | −0.000967 | −0.023809 | 0.038486 | 0.022837 | 0.014599 | −0.032471 | −0.020718 | −0.029286 | 0.013603 | −0.03638 | 0.001489 |
| 151 | −0.014831 | 0.074224 | 0.085011 | −0.24256 | 0.014321 | −0.105377 | −0.024711 | 0.1384 | −0.053098 | 0.037141 | −0.00399 | 0.089077 | 0.045155 | −0.114454 |
| 152 | 0.027939 | 0.083267 | −0.052026 | 0.059675 | −0.04934 | 0.048498 | 0.001356 | 0.047806 | 0.096247 | −0.071876 | −0.020503 | 0.02642 | −0.01786 | 0.008092 |
| 153 | 0.030824 | 0.077647 | −0.032202 | 0.049232 | −0.075442 | 0.119455 | −0.107832 | 0.035085 | 0.009714 | −0.004424 | −0.036266 | 0.065455 | 0.051533 | 0.041193 |

APPENDIX B3-continued

PCA Transformation
Matrix (340 × 340 Early/Late)

| | | | | | | | | | | | | | |
|---|---|---|---|---|---|---|---|---|---|---|---|---|---|
| 154 | 0.112458 | 0.091017 | −0.007953 | 0.051653 | −0.069773 | 0.087018 | −0.041893 | 0.082449 | −0.075712 | −0.063121 | −0.033803 | 0.068935 | −0.018653 | 0.07391 |
| 155 | 0.063923 | 0.05654 | 0.04502 | 0.056849 | −0.090157 | 0.104071 | 0.022404 | 0.025178 | 0.05377 | −0.019096 | −0.008454 | 0.001691 | −0.000774 | 0.00724 |
| 156 | 0.022564 | 0.03908 | −0.04821 | 0.017377 | −0.028194 | 0.011161 | 0.029866 | −0.051036 | −0.011565 | −0.03619 | 0.095149 | −0.025976 | 0.019379 | −0.009273 |
| 157 | 0.000563 | −0.015189 | −0.005782 | −0.009392 | −0.004513 | −0.008312 | 0.02422 | −0.007035 | 0.040835 | −0.034168 | −0.019239 | −0.012235 | 0.072866 | 0.000162 |
| 158 | 0.007555 | 0.113588 | 0.122246 | 0.026377 | 0.039991 | −0.028382 | 0.069642 | −0.084888 | 0.011659 | 0.045052 | −0.138885 | 0.068205 | −0.094985 | −0.228837 |
| 159 | 0.063272 | 0.157986 | 0.024208 | 0.057114 | −0.009614 | 0.056769 | −0.032307 | −0.014821 | 0.063667 | 0.138115 | −0.043616 | 0.000282 | −0.172798 | 0.001613 |
| 160 | −0.026772 | 0.12848 | 0.147288 | 0.115491 | 0.051042 | 0.041272 | −0.021048 | 0.036073 | −0.014952 | −0.061174 | 0.087958 | 0.004134 | 0.066757 | −0.052844 |
| 161 | −0.002831 | 0.024234 | 0.051642 | 0.020138 | −0.013124 | −0.03177 | 0.062043 | −0.121446 | −0.013066 | 0.070625 | −0.034395 | 0.040334 | 0.028521 | −0.044039 |
| 162 | −0.033187 | 0.092459 | −0.054449 | −0.004454 | 0.024567 | 0.035931 | 0.021761 | 0.076929 | 0.012545 | 0.091837 | 0.028621 | 0.036741 | 0.033342 | −0.086363 |
| 163 | 0.028732 | −0.001589 | −0.03367 | 0.033264 | −0.044232 | 0.02997 | 0.011135 | 0.052619 | 0.039714 | −0.07017 | 0.038826 | 0.035272 | −0.043505 | 0.045695 |
| 164 | 0.100389 | 0.126722 | −0.011183 | −0.044752 | −0.024063 | 0.089316 | 0.074125 | 0.180494 | 0.093427 | −0.111082 | 0.042142 | −0.082017 | −0.025644 | −0.013943 |
| 165 | 0.070782 | 0.025479 | 0.089154 | 0.022628 | 0.044024 | 0.083284 | 0.016993 | −0.001931 | −0.056906 | −0.063042 | −0.023268 | 0.043463 | 0.036691 | 0.012838 |
| 166 | 0.079342 | 0.165102 | 0.076139 | 0.03714 | 0.032084 | 0.09202 | 0.097672 | 0.112755 | −0.08266 | 0.104622 | 0.056935 | −0.139225 | 0.042002 | −0.068429 |
| 167 | 0.017455 | 0.039886 | −0.044817 | 0.014319 | −0.012229 | 0.066116 | 0.018717 | −0.013782 | −0.007901 | −0.032897 | 0.055965 | 0.024623 | −0.036967 | −0.022169 |
| 168 | −0.049187 | 0.004963 | −0.006386 | −0.01027 | −0.083712 | −0.004646 | −0.098249 | −0.018705 | 0.044974 | −0.097518 | 0.00799 | −0.020343 | −0.043656 | −0.017605 |
| 169 | −0.068743 | −0.03886 | 0.027597 | 0.080841 | 0.002251 | −0.005826 | −0.016136 | 0.098269 | −0.010597 | 0.005503 | −0.011615 | −0.067987 | 0.037307 | 0.036451 |
| 170 | −0.051415 | −0.016028 | 0.04435 | 0.097021 | −0.000466 | 0.007321 | −0.006968 | 0.139797 | −0.005111 | 0.021691 | −0.015181 | −0.082551 | 0.046978 | −0.016269 |
| 171 | −0.080528 | 0.011362 | 0.033439 | 0.064322 | 0.034089 | −0.043406 | −0.048599 | 0.050232 | −0.030621 | −0.000763 | −0.039274 | −0.075666 | −0.008077 | 0.019291 |
| 172 | −0.021433 | −0.070171 | 0.079553 | −0.012308 | −0.019285 | −0.032921 | −0.020088 | 0.092679 | −0.010376 | 0.012205 | −0.024484 | −0.025323 | −0.036066 | −0.05339 |
| 173 | −0.020804 | −0.052976 | 0.096186 | −0.044836 | −0.016222 | −0.019693 | −0.000748 | 0.006817 | −0.006315 | 0.016878 | −0.050597 | 0.015927 | −0.042401 | −0.012449 |
| 174 | 0.013434 | −0.109402 | 0.103469 | −0.057606 | −0.040991 | −0.01995 | −0.033423 | 0.030037 | −0.034107 | −0.032994 | −0.001149 | 0.002949 | −0.106432 | −0.080782 |
| 175 | −0.072815 | −0.090214 | 0.115026 | −0.000349 | −0.00042 | −0.010801 | 0.037163 | 0.111139 | 0.032538 | −0.060634 | 0.020562 | 0.002909 | −0.073312 | −0.039038 |
| 176 | −0.036637 | −0.046606 | 0.000712 | −0.01737 | 0.008447 | 0.000229 | 0.050734 | −0.011674 | 0.005099 | 0.004356 | −0.010833 | −0.105856 | −0.033386 | 0.036836 |
| 177 | 0.073625 | 0.020345 | 0.021925 | −0.045202 | 0.071472 | −0.101616 | −0.03439 | 0.072445 | −0.029383 | −0.00412 | 0.015639 | −0.014316 | 0.025565 | −0.062962 |
| 178 | −0.039183 | 0.004463 | 0.088265 | −0.007394 | −0.002522 | −0.009154 | 0.021728 | −0.040099 | 0.020664 | 0.066945 | −0.065384 | 0.03244 | −0.047175 | 0.011439 |
| 179 | −0.038283 | 0.044273 | 0.059815 | −0.017077 | −0.001364 | 0.024743 | −0.011884 | 0.025792 | 0.019663 | −0.005479 | −0.048407 | 0.023433 | −0.014105 | 0.040752 |
| 180 | −0.034493 | 0.028111 | 0.070654 | −0.002449 | −0.006093 | 0.04853 | 0.009061 | 0.018171 | 0.008842 | 0.037319 | −0.05591 | 0.052138 | 0.003113 | 0.03925 |
| 181 | −0.028963 | 0.041511 | 0.068203 | −0.019163 | −0.004966 | 0.029434 | 0.008674 | 0.023176 | 0.006731 | 0.034572 | −0.047388 | 0.038516 | −0.017014 | 0.030601 |
| 182 | 0.003037 | 0.048103 | 0.077833 | −0.051453 | −0.011832 | 0.03171 | −0.007026 | 0.015846 | 0.040766 | −0.0073 | −0.078101 | 0.005977 | −0.027369 | −0.001945 |
| 183 | −0.024979 | 0.071822 | 0.074582 | −0.049779 | 0.005924 | −0.022871 | −0.067077 | −0.045058 | 0.027796 | −0.062397 | −0.057643 | −0.00436 | −0.044968 | 0.030615 |
| 184 | −0.008903 | 0.034435 | 0.054071 | −0.063506 | 0.008563 | −0.022071 | −0.078828 | −0.096836 | −0.027717 | −0.008114 | 0.001005 | −0.01928 | −0.073025 | −0.031555 |
| 185 | −0.026167 | 0.006612 | 0.010508 | −0.082065 | −0.081366 | 0.025743 | −0.124747 | −0.05196 | 0.014253 | −0.016688 | 0.06867 | 0.005007 | −0.042781 | 0.081963 |
| 186 | 0.039262 | −0.044163 | 0.104635 | 0.0143 | 0.033466 | 0.087916 | −0.048508 | 0.004101 | 0.001224 | 0.070586 | 0.001337 | 0.079031 | 0.04691 | −0.067823 |
| 187 | 0.043645 | −0.072727 | 0.060409 | −0.031422 | 0.026739 | 0.038187 | −0.076233 | −0.004881 | 0.030539 | 0.010981 | −0.050364 | 0.063263 | 0.001789 | −0.026803 |
| 188 | 0.062191 | −0.09273 | 0.067559 | −0.057495 | −0.008067 | 0.05064 | −0.092922 | 0.015114 | 0.01879 | −0.049248 | −0.026009 | 0.054309 | −0.047829 | −0.061855 |
| 189 | 0.027374 | −0.074455 | 0.075276 | −0.067472 | 0.034002 | 0.073632 | −0.078786 | 0.089644 | 0.036707 | −0.075266 | −0.034399 | 0.042178 | −0.077614 | −0.039635 |
| 190 | 0.025191 | 0.033992 | 0.020225 | −0.028849 | 0.030446 | −0.033011 | 0.044838 | 0.010276 | 0.027099 | 0.013366 | 0.007424 | 0.005497 | 0.030667 | 0.01279 |
| 191 | 0.014344 | −0.003276 | 0.003607 | 0.003297 | 0.066383 | −0.031084 | 0.02801 | 0.01919 | 0.018935 | 0.016089 | 0.007419 | 0.001187 | 0.072215 | 0.009245 |
| 192 | −0.020836 | −0.010004 | 0.018375 | 0.000428 | −0.049726 | −0.05727 | −0.035499 | −0.044308 | 0.100634 | −0.080606 | 0.003162 | 0.006385 | −0.025292 | −0.049596 |
| 193 | 0.007345 | −0.042982 | 0.032035 | −0.012452 | −0.020062 | −0.028821 | −0.032648 | −0.020021 | 0.118018 | −0.026035 | −0.015691 | 0.012348 | −0.048169 | −0.020344 |
| 194 | −0.002499 | −0.068459 | 0.089609 | −0.025738 | 0.028125 | −0.001341 | −0.003356 | 0.032516 | 0.106786 | −0.02902 | −0.086087 | 0.074931 | −0.001346 | 0.023117 |
| 195 | 0.030729 | −0.000782 | 0.097407 | −0.014156 | 0.016378 | −0.014009 | 0.018569 | 0.099927 | 0.063964 | 0.079617 | −0.058564 | −0.013589 | −0.001975 | −0.016491 |
| 196 | 0.014076 | 0.010255 | 0.068576 | −0.027834 | 0.000483 | −0.001872 | 0.015839 | 0.089685 | 0.043994 | 0.040654 | −0.026168 | 0.035404 | 0.009907 | −0.047228 |
| 197 | 0.053704 | −0.018363 | 0.024449 | 0.005889 | 0.009604 | 0.005521 | 0.047102 | 0.004696 | 0.049097 | −0.015069 | −0.003238 | −0.01427 | 0.057706 | 0.005752 |
| 198 | 0.016056 | −0.081736 | 0.112747 | 0.040019 | 0.040981 | −0.027602 | −0.020019 | 0.079918 | 0.009674 | 0.062285 | −0.009665 | −0.022224 | −0.038203 | −0.03106 |
| 199 | −0.030934 | −0.039036 | −0.018111 | −0.005515 | 0.057425 | −0.045571 | 0.062146 | 0.100582 | −0.083321 | 0.027628 | 0.084877 | 0.043716 | 0.081232 | −0.030062 |
| 200 | 0.045823 | −0.022403 | 0.090491 | 0.004378 | −0.021453 | 0.048072 | −0.015353 | 0.067578 | 0.003746 | 0.049807 | −0.061563 | −0.014645 | −0.058361 | −0.072241 |
| 201 | 0.031842 | −0.002926 | 0.008964 | −0.00149 | 0.051612 | −0.052274 | −0.057254 | −0.038159 | 0.044537 | 0.04376 | −0.062148 | 0.030647 | 0.062574 | 0.119783 |
| 202 | 0.051365 | −0.065208 | 0.103012 | 0.048386 | 0.043119 | −0.009112 | −0.034975 | 0.102275 | 0.044536 | 0.073733 | −0.048407 | 0.032948 | −0.059718 | −0.052064 |
| 203 | 0.058659 | −0.019707 | 0.059066 | 0.100843 | −0.032697 | −0.119544 | 0.028497 | −0.001497 | 0.063905 | −0.012851 | 0.003738 | −0.008912 | 0.068143 | 0.082105 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 204 | 0.051541 | 0.054166 | −0.001326 | 0.069183 | −0.077907 | −0.125477 | −0.058044 | −0.037879 | −0.009561 | 0.014151 | 0.028906 | 0.154955 | −0.070884 | 0.03941 |
| 205 | −0.018717 | 0.023905 | −0.058687 | −0.148639 | 0.021763 | 0.143814 | 0.239192 | 0.026434 | 0.10787 | −0.016702 | −0.011311 | 0.061618 | −0.088151 | 0.107131 |
| 206 | 0.1514 | 0.004726 | −0.030991 | 0.138086 | 0.073526 | 0.036251 | −0.013944 | −0.091364 | −0.05495 | −0.143672 | 0.026281 | 0.019773 | −0.139485 | 0.061155 |
| 207 | −0.00346 | 0.026099 | 0.072549 | −0.007088 | −0.085876 | 0.045727 | −0.008416 | −0.015094 | 0.015228 | −0.196411 | 0.154428 | 0.192717 | 0.06371 | −0.152975 |
| 208 | 0.095942 | −0.022422 | 0.056337 | 0.139527 | 0.030706 | 0.061073 | 0.000582 | −0.022446 | 0.148533 | −0.094202 | 0.13951 | −0.094885 | 0.0478 | 0.029541 |
| 209 | 0.017437 | 0.047005 | 0.169426 | −0.06198 | 0.003546 | −0.037719 | 0.129553 | −0.034282 | −0.019927 | 0.052918 | −0.08006 | 0.062998 | −0.013306 | −0.036275 |
| 210 | −0.020806 | 0.006753 | 0.123258 | −0.069148 | 0.0444 | −0.038654 | 0.182054 | −0.019125 | −0.029611 | 0.088916 | 0.081093 | −0.040433 | 0.025533 | 0.118628 |
| 211 | 0.000553 | −0.01067 | −0.056983 | −0.0568 | −0.067269 | −0.000432 | 0.059716 | −0.029695 | −0.111253 | −0.061029 | −0.002515 | 0.043836 | 0.015594 | −0.011149 |
| 212 | −0.012827 | −0.054928 | −0.059114 | 0.00239 | −0.155453 | 0.139116 | −0.052471 | 0.176935 | −0.11169 | −0.171557 | −0.00718 | −0.108339 | 0.037292 | 0.113822 |
| 213 | 0.014291 | 0.071197 | 0.064804 | −0.017219 | 0.052073 | 0.050441 | 0.136267 | −0.140874 | 0.09518 | 0.064553 | 0.014602 | 0.022801 | −0.043692 | −0.013809 |
| 214 | −0.027051 | 0.042815 | 0.047306 | −0.000711 | 0.011703 | 0.027803 | −0.039076 | 0.018881 | 0.011305 | −0.008165 | −0.042405 | 0.00845 | 0.001966 | 0.001775 |
| 215 | −0.08832 | 0.056327 | 0.07875 | −0.052278 | −0.013083 | 0.064992 | −0.052012 | −0.046476 | 0.038621 | −0.023044 | 0.012241 | 0.029169 | −0.053855 | 0.10805 |
| 216 | −0.138701 | −0.009814 | −0.045027 | −0.006968 | 0.015076 | 0.018784 | −0.036712 | 0.022328 | −0.000152 | 0.001039 | −0.011321 | 0.006127 | −0.055343 | −0.009532 |
| 217 | −0.037993 | −0.021456 | −0.094906 | −0.046863 | 0.076301 | −0.077122 | −0.006304 | 0.038267 | 0.025623 | 0.006351 | 0.103324 | −0.102722 | 0.032045 | 0.025976 |
| 218 | −0.022474 | −0.017247 | 0.015442 | −0.029662 | 0.006254 | −0.011734 | 0.021046 | 0.008897 | 0.012116 | 0.010425 | −0.003788 | −0.068594 | −0.0104 | 0.018088 |
| 219 | −0.144444 | −0.009955 | −0.02715 | −0.016514 | 0.054733 | −0.011218 | 0.011228 | 0.026067 | −0.030453 | 0.017186 | −0.018812 | −0.069266 | 0.015912 | −0.031675 |
| 220 | −0.009402 | 0.052748 | −0.043405 | 0.002087 | −0.021599 | −0.054853 | −0.027668 | 0.014456 | −0.088432 | 0.050109 | 0.030839 | −0.087284 | 0.031165 | 0.032341 |
| 221 | −0.035846 | −0.010663 | 0.034983 | 0.00034 | −0.032666 | −0.005359 | 0.04401 | −0.015167 | −0.086708 | 0.021385 | −0.011354 | −0.006245 | −0.049596 | 0.054714 |
| 222 | −0.070355 | 0.012723 | −0.011154 | −0.009367 | −0.052709 | −0.049376 | 0.10334 | 0.033046 | 0.113767 | −0.025096 | 0.002925 | 0.023333 | −0.024056 | 0.004458 |
| 223 | −0.079582 | 0.003409 | −0.008729 | −0.008885 | −0.041019 | −0.057336 | 0.081522 | 0.007182 | 0.081274 | −0.008063 | −0.020598 | 0.003687 | −0.04835 | 0.012393 |
| 224 | −0.002213 | −0.059277 | −0.023722 | 0.076739 | −0.012681 | −0.047892 | −0.055054 | −0.019177 | 0.029176 | −0.01412 | 0.012862 | 0.065274 | −0.092319 | 0.005578 |
| 225 | −0.010441 | −0.061093 | −0.021132 | 0.095886 | −0.002046 | −0.049587 | −0.051956 | −0.010625 | 0.036731 | −0.011602 | 0.008148 | 0.054351 | −0.09281 | 0.007001 |
| 226 | −0.063849 | −0.00631 | 0.03526 | 0.035676 | −0.022105 | 0.014564 | −0.092394 | −0.038768 | 0.017163 | 0.037866 | −0.047886 | −0.042688 | −0.002599 | −0.005443 |
| 227 | −0.105298 | 0.012574 | −0.004245 | 0.086084 | 0.009742 | −0.019908 | −0.166379 | −0.05555 | 0.035295 | 0.007809 | −0.079887 | 0.004763 | −0.092746 | 0.082861 |
| 228 | −0.080882 | −0.032697 | −0.04235 | 0.098587 | −0.070435 | 0.025209 | −0.005325 | −0.01054 | 0.108494 | −0.05048 | 0.049331 | 0.091781 | −0.054488 | −0.094887 |
| 229 | −0.01239 | −0.132399 | 0.015616 | 0.052164 | −0.082995 | 0.037829 | −0.061784 | 0.017007 | 0.041263 | 0.196321 | 0.114447 | 0.118086 | −0.009236 | 0.017493 |
| 230 | −0.076358 | −0.024934 | −0.034008 | 0.014037 | −0.061507 | 0.030314 | −0.047438 | 0.016433 | 0.036376 | 0.033695 | 0.050238 | 0.121935 | −0.029304 | 0.034271 |
| 231 | −0.111749 | 0.05218 | −0.050673 | 0.012708 | −0.000714 | −0.019698 | −0.012659 | −0.055324 | −0.017151 | −0.001238 | −0.062684 | −0.052861 | −0.074409 | 0.031908 |
| 232 | −0.012394 | −0.042468 | −0.026629 | 0.089026 | −0.043245 | 0.013284 | −0.010929 | 0.006755 | −0.004018 | −0.051581 | 0.050113 | 0.120155 | −0.033532 | −0.072234 |
| 233 | −0.0914 | 0.006217 | 0.046525 | 0.015803 | 0.066004 | 0.011325 | −0.04191 | −0.03839 | 0.013324 | −0.005301 | 0.023815 | 0.111221 | −0.002252 | 0.000483 |
| 234 | −0.183285 | 0.05541 | −0.088194 | 0.043662 | 0.003683 | 0.082024 | 0.013671 | −0.10971 | −0.02945 | −0.05715 | −0.074086 | −0.031679 | −0.074086 | −0.03605 |
| 235 | −0.143295 | 0.032098 | −0.100728 | 0.059693 | −0.02447 | 0.042014 | 0.024947 | −0.085946 | −0.017706 | −0.054935 | −0.045026 | 0.01706 | −0.08255 | −0.000606 |
| 236 | 0.038087 | −0.021433 | −0.065306 | −0.000364 | −0.001865 | 0.052428 | 0.103711 | 0.001431 | −0.006538 | −0.035316 | 0.043737 | 0.004658 | −0.03006 | 0.059363 |
| 237 | 0.113711 | 0.046141 | −0.060486 | −0.054939 | 0.077032 | −0.010929 | −0.032282 | 0.030304 | 0.076996 | −0.001863 | 0.032868 | −0.02804 | −0.021225 | −0.03101 |
| 238 | −0.065492 | −0.00507 | −0.05359 | −0.030157 | 0.080612 | −0.020412 | 0.055148 | 0.048381 | 0.020385 | −0.044033 | −0.004644 | 0.009446 | 0.022938 | −0.045211 |
| 239 | −0.100239 | −0.042209 | −0.013618 | −0.003305 | 0.043758 | −0.020431 | 0.06027 | −0.004672 | 0.046291 | −0.060306 | −0.030809 | 0.020527 | 0.005187 | −0.020766 |
| 240 | −0.082822 | 0.042926 | −0.003965 | 0.070891 | 0.071371 | −0.021076 | −0.021535 | −0.018788 | −0.087498 | −0.009718 | 0.065428 | 0.053206 | 0.092404 | 0.009742 |
| 241 | −0.082434 | 0.049748 | −0.000062 | 0.032178 | 0.056281 | 0.013808 | −0.029295 | −0.03102 | −0.052075 | −0.026016 | 0.050981 | 0.064311 | 0.035987 | −0.011236 |
| 242 | −0.035819 | 0.044721 | −0.060801 | −0.003833 | −0.049557 | 0.015445 | 0.07148 | −0.059799 | 0.00795 | 0.002314 | −0.023427 | 0.059303 | −0.106424 | 0.051303 |
| 243 | −0.076798 | 0.017513 | −0.086826 | 0.025176 | −0.114411 | −0.063055 | 0.056594 | 0.012511 | 0.046049 | 0.043588 | −0.012736 | 0.099695 | −0.072486 | −0.036009 |
| 244 | 0.03117 | −0.030378 | 0.018737 | 6.067324 | −0.015933 | 0.013571 | −0.007288 | −0.036946 | −0.081959 | 0.03497 | −0.000865 | 0.028269 | −0.0191851 | 0.024775 |
| 245 | 0.066811 | −0.039187 | 0.011158 | −0.024753 | −0.001994 | 0.041458 | −0.019595 | −0.027122 | −0.058896 | −0.016743 | 0.0712 | 0.019598 | −0.067955 | 0.018079 |
| 246 | 0.065419 | 0.090341 | 0.005978 | −0.074289 | 0.003295 | 0.022293 | 0.019015 | −0.025095 | 0.010695 | 0.001561 | −0.020631 | 0.009962 | −0.032684 | 0.049694 |
| 247 | −0.022909 | 0.031592 | −0.003414 | −0.048928 | −0.022245 | −0.024346 | 0.057738 | −0.007578 | −0.007141 | 0.001727 | −0.01237 | 0.028187 | 0.005419 | 0.074656 |
| 248 | −0.040752 | 0.023022 | −0.046927 | −0.010405 | −0.034335 | 0.002515 | 0.048952 | 0.003871 | −0.021551 | −0.002889 | 0.002075 | 0.047023 | 0.013613 | 0.048113 |
| 249 | −0.080858 | 0.085313 | −0.082894 | 0.080129 | 0.019626 | −0.071038 | 0.071545 | 0.046882 | 0.057337 | −0.043778 | 0.10037 | 0.063964 | 0.049344 | −0.042107 |
| 250 | −0.081684 | 0.075918 | −0.047193 | 0.045907 | 0.05335 | −0.008571 | 0.007905 | −0.037631 | −0.057047 | 0.01442 | 0.01735 | 0.014004 | 0.053001 | 0.006897 |
| 251 | −0.059992 | 0.072793 | −0.056591 | 0.093592 | 0.04393 | −0.011748 | −0.034515 | −0.0267 | −0.075676 | 0.00618 | 0.04783 | 0.015584 | 0.065846 | 0.013485 |
| 252 | −0.037993 | 0.060247 | −0.091251 | 0.028738 | −0.024619 | −0.030919 | −0.027177 | 0.010989 | −0.008618 | 0.03981 | 0.011591 | 0.015251 | −0.089654 | 0.021085 |
| 253 | −0.044037 | −0.018545 | −0.052096 | 0.015342 | −0.127802 | −0.016862 | 0.00739 | 0.015042 | 0.008908 | 0.012793 | 0.017249 | 0.061294 | −0.069642 | −0.040317 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 254 | −0.01715 | −0.01219 | −0.014929 | 0.034844 | −0.034427 | −0.009469 | 0.05323 | −0.00125 | 0.024431 | 0.010001 | 0.001531 | 0.045307 | −0.014789 | −0.008038 |
| 255 | 0.023923 | 0.014313 | 0.018906 | 0.052081 | −0.04293 | 0.026958 | −0.005221 | −0.010834 | −0.110217 | 0.038384 | −0.016134 | 0.034877 | −0.002199 | 0.034175 |
| 256 | 0.058405 | −0.048779 | 0.072561 | −0.00552 | −0.102351 | 0.050211 | −0.039342 | 0.0381 | −0.139294 | −0.000601 | 0.019288 | −0.003264 | −0.067541 | 0.003628 |
| 257 | −0.036455 | −0.008196 | 0.013544 | −0.008711 | −0.013282 | 0.02082 | −0.013381 | 0.015219 | −0.026345 | −0.064297 | −0.051129 | −0.040596 | 0.0376 | −0.008644 |
| 258 | −0.000367 | −0.048109 | −0.004814 | −0.027178 | −0.030158 | −0.017588 | 0.005984 | 0.041801 | 0.013354 | −0.047425 | −0.024689 | −0.02894 | 0.05314 | 0.024306 |
| 259 | −0.087154 | 0.064987 | −0.0848 | 0.042542 | −0.016451 | −0.051456 | 0.070995 | 0.033258 | 0.111253 | −0.002978 | 0.041331 | 0.045352 | 0.004281 | −0.021087 |
| 260 | −0.05931 | 0.083497 | −0.115797 | 0.019989 | 0.016923 | −0.027638 | 0.028953 | 0.040263 | 0.088254 | 0.046039 | −0.007872 | 0.008332 | −0.066214 | −0.049669 |
| 261 | −0.049654 | 0.102434 | −0.09743 | −0.000965 | 0.013184 | −0.011372 | 0.001039 | 0.022567 | 0.035421 | 0.021813 | 0.02018 | −0.011885 | −0.009172 | 0.005684 |
| 262 | 0.016067 | 0.020598 | −0.051791 | 0.002883 | −0.028221 | −0.002831 | 0.042405 | −0.003765 | 0.00004 | 0.002676 | 0.004607 | 0.017724 | −0.053339 | 0.015858 |
| 263 | 0.003971 | 0.007842 | −0.079786 | 0.01801 | −0.042345 | 0.002696 | 0.032514 | 0.002153 | 0.010899 | −0.009801 | 0.000393 | 0.025496 | −0.046562 | 0.014562 |
| 264 | −0.031624 | 0.027705 | −0.035566 | 0.051607 | −0.059924 | −0.020019 | 0.065886 | 0.021094 | 0.106825 | −0.033649 | −0.003343 | 0.039606 | 0.020564 | −0.024155 |
| 265 | 0.002838 | 0.013663 | −0.040816 | 0.020868 | −0.034446 | −0.039078 | 0.07951 | 0.068502 | 0.120858 | 0.000538 | −0.05425 | −0.002143 | 0.001507 | −0.046267 |
| 266 | 0.02646 | 0.017367 | −0.039748 | −0.019147 | −0.021369 | −0.006524 | 0.025328 | 0.044135 | 0.02777 | 0.041823 | −0.033234 | −0.012813 | −0.009205 | 0.005608 |
| 267 | −0.044879 | −0.094848 | 0.079418 | 0.072829 | −0.083288 | 0.018138 | −0.076606 | 0.012935 | −0.038126 | 0.10687 | 0.045048 | −0.006499 | −0.097962 | −0.034996 |
| 268 | −0.057424 | −0.010902 | 0.057313 | 0.032679 | −0.013814 | 0.003773 | −0.067183 | −0.026036 | −0.003045 | 0.0325 | −0.053914 | −0.028277 | −0.02132 | −0.000925 |
| 269 | −0.044022 | 0.003584 | 0.032137 | 0.021985 | −0.000025 | 0.013503 | −0.079243 | −0.017043 | −0.02102 | 0.029423 | −0.056195 | −0.01656 | −0.016873 | −0.01358 |
| 270 | −0.035976 | 0.014079 | 0.030359 | 0.048031 | −0.005075 | −0.000161 | −0.108303 | −0.028805 | −0.004777 | 0.017501 | −0.073502 | −0.021521 | 0.000606 | −0.007938 |
| 271 | 0.011184 | −0.086057 | −0.050656 | 0.019723 | −0.025437 | 0.05614 | −0.019547 | −0.063689 | −0.029751 | 0.164167 | 0.059496 | 0.080313 | −0.012678 | −0.052113 |
| 272 | −0.008347 | −0.108007 | 0.021554 | 0.061435 | −0.082785 | 0.020577 | −0.026127 | 0.005242 | 0.01762 | 0.162955 | 0.115844 | 0.040988 | 0.043543 | −0.0223 |
| 273 | 0.023645 | −0.022854 | 0.006273 | 0.024126 | −0.050678 | −0.024165 | −0.025123 | 0.006649 | 0.00621 | 0.099619 | 0.058513 | 0.041805 | 0.057338 | 0.008181 |
| 274 | 0.027289 | −0.01581 | 0.001443 | 0.023374 | −0.047375 | −0.015792 | −0.029609 | 0.007698 | 0.001505 | 0.093553 | 0.053885 | 0.044763 | 0.059289 | 0.004594 |
| 275 | 0.004786 | 0.001166 | −0.042725 | 0.05196 | −0.041868 | 0.002394 | −0.098904 | −0.005095 | 0.023015 | 0.023258 | 0.044703 | 0.088742 | 0.026615 | 0.038555 |
| 276 | 0.016931 | −0.079849 | −0.046817 | 0.014929 | −0.03779 | 0.066621 | 0.109228 | 0.010545 | −0.01895 | 0.017336 | 0.083147 | 0.020405 | −0.014701 | 0.048922 |
| 277 | 0.097283 | −0.017989 | 0.011503 | −0.043274 | 0.027823 | −0.000574 | 0.062561 | −0.006064 | 0.089349 | −0.037085 | 0.018553 | −0.02508 | −0.039998 | −0.017849 |
| 278 | 0.10879 | −0.027945 | 0.014469 | −0.034466 | 0.028762 | 0.003474 | 0.043686 | −0.017859 | 0.101041 | −0.051717 | 0.015641 | 0.015186 | −0.040198 | −0.025709 |
| 279 | −0.071861 | −0.04355 | −0.015726 | 0.015943 | 0.043486 | 0.007181 | 0.049108 | 0.003575 | 0.023214 | −0.059438 | −0.022355 | 0.039345 | 0.03248 | −0.063109 |
| 280 | −0.056993 | −0.034886 | −0.011315 | 0.036858 | −0.13503 | −0.02136 | 0.044089 | 0.038803 | 0.053784 | 0.047925 | 0.04816 | 0.082425 | −0.082132 | −0.076703 |
| 281 | 0.095182 | 0.057077 | 0.072939 | −0.024704 | −0.044799 | −0.017551 | −0.009234 | −0.053215 | 0.013225 | 0.015841 | 0.009394 | 0.020793 | 0.056403 | 0.037357 |
| 282 | 0.083656 | 0.003756 | 0.076182 | −0.030944 | −0.043236 | −0.024156 | −0.028277 | −0.037099 | −0.009348 | 0.003111 | −0.024679 | 0.043289 | 0.035755 | 0.022396 |
| 283 | −0.021675 | 0.017069 | −0.006708 | 0.002667 | −0.050098 | 0.002631 | 0.024788 | −0.045544 | −0.028373 | 0.014929 | −0.011066 | 0.033948 | 0.042471 | 0.044376 |
| 284 | −0.01451 | −0.013543 | 0.024856 | 0.025268 | −0.023624 | 0.034405 | −0.030918 | 0.010928 | −0.042029 | −0.063943 | −0.03037 | −0.036176 | 0.050982 | −0.034741 |
| 285 | −0.016906 | −0.02151 | 0.020873 | 10.01948 | −0.016423 | 0.031919 | −0.039774 | 0.001375 | −0.041087 | −0.074565 | −0.063248 | −0.014255 | 0.041845 | −0.038573 |
| 286 | −0.011833 | −0.063264 | 0.046966 | 0.010214 | −0.016953 | −0.001735 | −0.072433 | 0.044089 | −0.01596 | −0.058197 | −0.019483 | −0.030018 | 0.093229 | −0.019081 |
| 287 | −0.01933 | −0.081929 | 0.03818 | 0.011879 | −0.011096 | −0.000652 | −0.077641 | 0.039234 | −0.014225 | −0.050831 | −0.034483 | −0.002807 | 0.088286 | −0.030273 |
| 288 | 0.039609 | −0.047662 | −0.068779 | −0.041039 | −0.027132 | −0.005671 | −0.036623 | −0.024101 | −0.019681 | −0.058184 | −0.013556 | 0.001324 | 0.07095 | 0.027421 |
| 289 | 0.05487 | −0.018733 | −0.041972 | 0.025563 | −0.000484 | −0.00619 | 0.017819 | 0.017286 | −0.023066 | 0.020976 | −0.012217 | −0.022653 | −0.012869 | 0.020507 |
| 290 | 0.108601 | 0.048711 | −0.089362 | −0.093324 | −0.023504 | −0.094129 | −0.067757 | −0.064178 | −0.05301 | 0.003071 | 0.000274 | 0.008553 | 0.034879 | −0.036102 |
| 291 | 0.104852 | 0.046278 | −0.084646 | −0.096211 | −0.02555 | −0.099695 | −0.066342 | −0.065387 | −0.054058 | 0.005486 | 0.005767 | 0.006471 | 0.036849 | −0.041244 |
| 292 | 0.071729 | 0.045463 | −0.092697 | −0.089835 | −0.026809 | −0.091542 | −0.063612 | −0.073235 | −0.057135 | −0.010926 | 0.007371 | 0.034244 | 0.051002 | −0.026826 |
| 293 | −0.023657 | −0.010376 | 0.007876 | −0.061834 | −0.009543 | −0.001596 | 0.06686 | −0.099529 | −0.016781 | −0.08896 | −0.038881 | 0.058718 | −0.04165 | 0.089352 |
| 294 | 0.019953 | −0.013749 | −0.004023 | −0.043184 | 0.017938 | −0.011107 | 0.022155 | −0.023862 | 0.029983 | −0.006824 | −0.03028 | 0.022673 | −0.034494 | 0.053002 |
| 295 | 0.032763 | 0.007464 | −0.008468 | −0.045582 | −0.038441 | −0.022826 | 0.058353 | −0.038539 | −0.014204 | −0.00396 | 0.040329 | 0.040015 | 0.025037 | 0.050768 |
| 296 | 0.045305 | 0.029383 | −0.00071 | 0.000193 | −0.036005 | −0.061099 | −0.002915 | −0.024565 | 0.039399 | 0.002217 | 0.055224 | 0.074347 | 0.033602 | 0.079996 |
| 297 | −0.005659 | 0.001844 | −0.051864 | −0.041357 | −0.029826 | 0.070864 | −0.052203 | −0.052203 | −0.015544 | −0.00788 | 0.041878 | 0.041637 | 0.03007 | 0.063528 |
| 298 | 0.08236 | 0.024329 | −0.024616 | −0.069121 | 0.058124 | −0.023071 | 0.012346 | −0.004972 | −0.037423 | −0.046202 | 0.072849 | −0.003934 | −0.014651 | −0.108173 |
| 299 | 0.040212 | −0.02948 | 0.031287 | −0.019203 | −0.026529 | −0.080427 | 0.064456 | −0.020544 | 0.000994 | −0.046893 | 0.032826 | −0.003529 | 0.044051 | 0.031735 |
| 300 | 0.009609 | 0.030633 | 0.005556 | −0.11574 | 0.047142 | 0.056808 | −0.055239 | 0.03697 | −0.023596 | 0.06184 | 0.127944 | 0.048811 | −0.003845 | −0.14205 |
| 301 | 0.016978 | −0.00012 | −0.010502 | −0.022496 | −0.005024 | −0.023142 | 0.066847 | −0.031465 | −0.008217 | −0.10734 | −0.020196 | 0.000331 | −0.013398 | 0.017381 |
| 302 | 0.026348 | 0.017292 | 0.024366 | −0.01502 | 0.021282 | −0.029115 | 0.018383 | 0.007589 | 0.036229 | −0.054721 | 0.022678 | −0.024024 | 0.006014 | −0.003538 |
| 303 | 0.042334 | −0.070475 | 0.069392 | −0.030744 | −0.013627 | −0.080157 | 0.026997 | 0.054254 | 0.06006 | −0.029401 | 0.033467 | −0.008157 | 0.00927 | −0.033894 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 304 | 0.043952 | −0.046107 | 0.064142 | −0.016501 | 0.000531 | −0.086261 | −0.000199 | 0.047254 | 0.070097 | −0.042115 | 0.061626 | −0.024943 | 0.02411 | −0.016254 |
| 305 | 0.047865 | −0.011891 | 0.020605 | −0.001357 | −0.006701 | 0.032461 | −0.066943 | −0.101429 | 0.042511 | −0.067739 | 0.05796 | 0.032814 | −0.059795 | −0.004091 |
| 306 | 0.083108 | 0.092505 | −0.002748 | −0.024382 | −0.053997 | −0.18755 | 0.063937 | −0.062055 | 0.065975 | 0.000514 | −0.022763 | 0.036183 | −0.019666 | 0.146526 |
| 307 | 0.097526 | 0.010961 | −0.0388 | 0.003582 | −0.027795 | −0.086296 | −0.10626 | 0.048059 | 0.02479 | 0.013501 | −0.079588 | 0.075027 | −0.026978 | −0.069879 |
| 308 | 0.060587 | −0.077671 | −0.091252 | 0.119607 | 0.092604 | −0.10323 | −0.019265 | 0.095124 | −0.024131 | 0.008823 | −0.198962 | 0.086425 | −0.004188 | −0.037319 |
| 309 | −0.021376 | 0.037585 | −0.017382 | −0.032557 | 0.031102 | 0.046194 | −0.011797 | 0.020996 | 0.059217 | −0.018713 | −0.059562 | 0.017465 | 0.023445 | 0.004777 |
| 310 | 0.015074 | 0.049211 | 0.024746 | −0.012791 | 0.020413 | 0.001222 | −0.043217 | −0.001442 | 0.044992 | −0.051878 | −0.035523 | −0.026655 | 0.057693 | 0.003993 |
| 311 | 0.003553 | 0.04465 | −0.019524 | −0.030864 | −0.002171 | 0.031745 | −0.023335 | 0.008049 | 0.061545 | 0.042944 | −0.057953 | 0.073503 | −0.027376 | 0.032035 |
| 312 | 0.008105 | −0.002734 | −0.042199 | 0.058826 | −0.005146 | −0.029872 | −0.037697 | 0.011459 | −0.028968 | 0.152439 | −0.056612 | 0.094793 | −0.045626 | −0.022701 |
| 313 | −0.004092 | 0.0342 | −0.031589 | −0.031315 | −0.022506 | 0.044288 | 0.008877 | −0.003219 | 0.061473 | −0.007497 | −0.098796 | −0.018966 | 0.015919 | 0.037069 |
| 314 | 0.038106 | 0.011446 | −0.032154 | 0.016146 | 0.056899 | 0.023513 | 0.071777 | −0.013335 | 0.109453 | 0.048683 | 0.055653 | −0.049699 | −0.061366 | 0.004116 |
| 315 | −0.000325 | 0.022466 | −0.033703 | −0.05853 | 0.012091 | 0.028114 | −0.008535 | −0.003544 | 0.06232 | 0.003245 | −0.082604 | 0.020707 | 0.030955 | 0.026342 |
| 316 | 0.046224 | 0.035315 | −0.022686 | 0.005758 | 0.025884 | −0.010754 | 0.05023 | 0.03986 | −0.053857 | −0.154594 | −0.071059 | 0.065793 | −0.095831 | −0.176557 |
| 317 | −0.02776 | 0.038194 | −0.045433 | −0.076357 | 0.023383 | 0.072306 | 0.022346 | −0.001721 | 0.053544 | −0.033061 | −0.097723 | 0.014428 | 0.000765 | 0.002971 |
| 318 | −0.008614 | 0.065607 | −0.051537 | −0.077563 | 0.078519 | 0.028792 | 0.023344 | −0.01567 | 0.102647 | 0.015642 | −0.04717 | 0.036059 | −0.000806 | 0.069059 |
| 319 | −0.027219 | 0.012696 | −0.028966 | −0.066883 | 0.026691 | 0.03722 | −0.015533 | 0.009714 | 0.054296 | −0.015445 | −0.081592 | −0.000598 | 0.033532 | −0.015266 |
| 320 | −0.025831 | 0.03993 | −0.017273 | −0.061317 | 0.036885 | −0.009779 | −0.016976 | −0.027654 | 0.045806 | −0.050668 | −0.04093 | −0.00223 | 0.029963 | −0.009263 |
| 321 | 0.112526 | 0.048442 | −0.024498 | −0.000716 | −0.039429 | −0.045687 | −0.007757 | 0.003408 | 0.005439 | −0.009049 | 0.028128 | −0.05053 | 0.008347 | 0.053458 |
| 322 | 0.002734 | 0.034259 | −0.112483 | 0.124618 | 0.207122 | −0.022025 | −0.006289 | 0.130415 | −0.070876 | −0.102948 | 0.124771 | 0.028836 | −0.10467 | −0.036 |
| 323 | 0.086322 | 0.105587 | −0.03896 | 0.095795 | −0.045001 | −0.011104 | −0.006468 | 0.041869 | −0.032749 | −0.011602 | 0.030884 | −0.046813 | −0.017683 | 0.025446 |
| 324 | 0.01809 | −0.000809 | 0.02019 | 0.074913 | 0.024301 | −0.037408 | −0.000225 | −0.02156 | −0.020867 | −0.089194 | 0.004232 | 0.067091 | −0.001057 | −0.030964 |
| 325 | −0.033627 | 0.019832 | −0.000801 | −0.059444 | 0.023116 | 0.043183 | −0.002284 | 0.037932 | 0.047322 | −0.009163 | −0.055396 | 0.047969 | 0.029767 | 0.011922 |
| 326 | −0.028769 | 0.06313 | −0.019388 | −0.063227 | −0.01311 | 0.016225 | −0.042075 | 0.126014 | 0.060304 | 0.045705 | −0.003586 | 0.069992 | 0.028342 | −0.010376 |
| 327 | 0.037985 | 0.03801 | −0.011897 | −0.00418 | −0.010329 | 0.042856 | −0.017396 | 0.019366 | 0.036335 | −0.006353 | 0.021333 | 0.038481 | 0.016738 | −0.001836 |
| 328 | 0.125244 | 0.040764 | −0.059758 | 0.003903 | 0.0450871 | −0.017114 | −0.079998 | 0.041025 | −0.017704 | −0.081298 | 0.151247 | 0.058958 | −0.126999 | 0.02626 |
| 329 | 0.046166 | 0.055439 | −0.015399 | 0.015063 | −0.029341 | 0.028883 | −0.003737 | 0.053003 | 0.005057 | 0.016299 | 0.007383 | 0.009964 | 0.027637 | 0.030083 |
| 330 | −0.001238 | 0.029404 | 0.023026 | −0.049219 | 0.080212 | 0.049418 | −0.111511 | 0.112353 | 0.039716 | −0.023522 | 0.188677 | −0.061095 | −0.109337 | −0.001265 |
| 331 | 0.000666 | 0.017511 | −0.017596 | −0.039785 | 0.00453 | 0.019276 | −0.008818 | 0.020787 | 0.025002 | 0.02354 | −0.048323 | 0.055677 | 0.007232 | 0.002546 |
| 332 | −0.014124 | 0.101866 | −0.018435 | −0.182033 | 0.053112 | 0.072805 | −0.109372 | 0.152679 | −0.023141 | 0.020904 | 0.136461 | 0.004341 | −0.121893 | −0.071873 |
| 333 | −0.029764 | 0.038887 | −0.028914 | −0.057856 | 0.055259 | 0.050909 | −0.000982 | 0.015801 | 0.037797 | −0.010666 | −0.073084 | 0.055507 | 0.014683 | 0.005085 |
| 334 | −0.027885 | 0.032846 | 0.01683 | −0.046796 | 0.067538 | 0.024562 | −0.015127 | 0.018463 | −0.022487 | 0.064489 | −0.004962 | 0.109331 | 0.001893 | 0.115796 |
| 335 | −0.012236 | 0.027887 | −0.014346 | −0.037286 | 0.003295 | 0.044282 | −0.033579 | 0.061845 | 0.022749 | −0.000748 | −0.068119 | 0.03764 | 0.028736 | −0.030262 |
| 336 | 0.01391 | −0.007695 | −0.009804 | −0.014838 | 0.072558 | −0.013442 | 0.019925 | −0.015916 | 0.035632 | 0.019639 | 0.011821 | 0.001006 | −0.046788 | −0.022694 |
| 337 | 0.089773 | 0.028577 | −0.000465 | 0.030122 | 0.011279 | −0.128696 | −0.00867 | −0.011466 | −0.055452 | −0.022364 | −0.038377 | 0.063992 | 0.063264 | −0.02579 |
| 338 | 0.080626 | 0.011568 | −0.001557 | 0.077411 | 0.157321 | 0.025016 | −0.024801 | −0.092794 | 0.025608 | −0.019038 | 0.122164 | 0.039434 | 0.003949 | 0.035173 |
| 339 | 0.073387 | 0.076029 | −0.008279 | 0.048122 | 0.019051 | 0.036759 | −0.03714 | −0.026826 | 0.047811 | −0.012045 | −0.029742 | 0.032678 | −0.024707 | −0.018325 |
| 340 | 0.00827 | 0.120462 | 0.090222 | −0.120626 | −0.037126 | −0.136588 | −0.000582 | 0.012281 | 0.056724 | 0.064747 | 0.167571 | 0.023043 | 0.058747 | −0.004185 |

| | Z | AA | AB | AC | AD | AE | AF | AG | AH | AI | AJ | AK | AL | AM |
|---|---|---|---|---|---|---|---|---|---|---|---|---|---|---|
| 1 | −0.025438 | −0.001181 | 0.030663 | 0.020583 | −0.003984 | −0.032363 | 0.026843 | 0.033794 | 0.033567 | −0.000425 | −0.019503 | 0.015899 | 0.020712 | −0.014331 |
| 2 | −0.015891 | 0.031646 | −0.0397 | 0.012492 | −0.005111 | −0.004683 | 0.064029 | −0.022883 | 0.057345 | −0.04041 | −0.075693 | −0.023128 | 0.012371 | −0.033377 |
| 3 | −0.019822 | −0.004761 | −0.013238 | 0.008571 | 0.034577 | 0.011753 | 0.00843 | 0.016806 | 0.023266 | −0.015577 | −0.037728 | 0.011799 | −0.011714 | 0.011507 |
| 4 | −0.015385 | −0.046192 | 0.063752 | 0.02753 | −0.027359 | −0.026015 | 0.066585 | −0.013756 | 0.020016 | 0.008976 | 0.085835 | −0.051784 | 0.094077 | −0.066302 |
| 5 | 0.06859 | −0.046748 | 0.044942 | 0.020115 | 0.102943 | 0.068336 | 0.038454 | −0.100105 | 0.004458 | 0.108608 | 0.034782 | 0.046808 | 0.01226 | 0.121546 |
| 6 | −0.018037 | −0.011324 | 0.062248 | −0.012072 | 0.014954 | 0.056542 | −0.020117 | −0.100815 | 0.024707 | −0.088129 | −0.017873 | 0.093286 | 0.000988 | −0.036486 |
| 7 | −0.007408 | 0.010194 | 0.041898 | 0.011574 | 0.002878 | −0.003863 | −0.023462 | 0.039425 | 0.064737 | −0.106122 | −0.125555 | 0.051972 | −0.029474 | 0.018254 |
| 8 | −0.128398 | 0.074753 | 0.083717 | −0.135865 | 0.024778 | −0.038923 | −0.016499 | −0.07169 | −0.12916 | −0.068616 | −0.086173 | 0.049066 | −0.007814 | −0.025897 |
| 9 | 0.057106 | −0.057294 | 0.003998 | −0.062445 | −0.045733 | −0.067425 | −0.001287 | −0.004421 | 0.000151 | −0.062853 | −0.006356 | 0.013414 | 0.009819 | −0.152004 |
| 10 | 0.052379 | 0.079234 | 0.049295 | 0.042165 | 0.012823 | −0.01139 | 0.031692 | −0.00254 | −0.033549 | −0.008871 | −0.05345 | −0.049823 | 0.025753 | 0.001968 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 11 | 0.056589 | 0.123045 | −0.028761 | 0.015238 | 0.013753 | −0.021844 | 0.001461 | 0.121934 | −0.003275 | −0.0186561 | 0.036307 | 0.0688711 | 0.125124 | 0.010557 |
| 12 | −0.057434 | 0.081054 | −0.142379 | 0.131097 | −0.086845 | −0.035589 | −0.0348 | 0.055894 | −0.156455 | −0.080091 | −0.071501 | 0.1266681 | 0.016571 | −0.157436 |
| 13 | 0.006217 | 0.010015 | 0.023916 | −0.018207 | −0.003436 | 0.036559 | 0.071173 | 0.006771 | −0.07831 | 0.002651 | −0.0239 | 0.003171 | −0.044007 | 0.029066 |
| 14 | 0.036115 | 0.046645 | 0.005233 | −0.01251 | −0.000406 | 0.018319 | 0.092265 | 0.046785 | −0.07196 | −0.038752 | 0.020432 | −0.047655 | −0.010055 | 0.001182 |
| 15 | 0.024074 | 0.002563 | 0.017559 | −0.017185 | 0.022309 | −0.040966 | −0.001382 | 0.04433 | 0.029781 | 0.052585 | −0.008445 | 0.002495 | 0.013409 | −0.005105 |
| 16 | 0.094066 | 0.09989 | 0.018409 | −0.025102 | 0.064857 | 0.087271 | 0.012313 | 0.133662 | −0.099904 | 0.076513 | 0.067026 | 0.094226 | 0.046865 | −0.085305 |
| 17 | 0.016594 | −0.013913 | −0.114874 | −0.064248 | −0.043774 | 0.0001 | 0.024797 | −0.099054 | 0.013777 | −0.041012 | −0.060065 | 0.065732 | −0.020393 | 0.095535 |
| 18 | 0.052548 | −0.105065 | 0.000443 | −0.044067 | 0.021076 | 0.034888 | −0.044349 | 0.141074 | 0.011776 | −0.028644 | 0.000425 | −0.104903 | −0.014532 | −0.033985 |
| 19 | 0.000223 | −0.021161 | −0.012249 | −0.059358 | 0.067696 | −0.004544 | 0.24805 | 0.028504 | 0.092443 | 0.002791 | 0.015574 | 0.030272 | 0.018046 | 0.070666 |
| 20 | −0.003132 | 0.026144 | 0.046275 | −0.002249 | −0.016062 | −0.020923 | −0.029314 | 0.015465 | −0.021081 | 0.000594 | −0.040367 | −0.006005 | −0.040367 | −0.006005 |
| 21 | −0.048329 | 0.0501 | −0.129867 | −0.014377 | −0.086857 | 0.012914 | 0.03869 | −0.028934 | 0.044904 | −0.01074 | −0.054939 | −0.114281 | −0.010267 | 0.076917 |
| 22 | 0.05419 | 0.023745 | 0.016327 | −0.008801 | 0.074293 | 0.041217 | −0.091127 | −0.050532 | −0.060091 | −0.010492 | −0.024569 | 0.041439 | 0.023374 | 0.030373 |
| 23 | 0.044918 | 0.077837 | −0.002282 | −0.078255 | −0.069739 | −0.000288 | 0.012491 | 0.03878 | −0.094284 | 0.106591 | 0.014145 | 0.050187 | −0.138233 | −0.013786 |
| 24 | 0.106601 | −0.028131 | −0.091183 | 0.09028 | −0.093412 | −0.063339 | 0.049089 | −0.012239 | 0.02881 | 0.039685 | −0.058014 | −0.080251 | −0.082176 | 0.028428 |
| 25 | 0.083748 | −0.018286 | −0.080251 | −0.082176 | 0.028428 | 0.083748 | −0.018286 | −0.036782 | 0.013683 | −0.029495 | −0.038883 | 0.002034 | −0.049365 | −0.110978 |
| 26 | 0.008141 | 0.018902 | 0.027443 | 0.003027 | −0.000431 | 0.003168 | −0.013496 | −0.016251 | 0.009594 | 0.011237 | −0.00743 | −0.02729 | −0.029966 | −0.00716 |
| 27 | 0.008544 | 0.004639 | 0.036823 | 0.021903 | −0.005177 | −0.000435 | −0.013817 | −0.011209 | −0.01541 | 0.006353 | −0.006291 | −0.00893 | −0.019624 | −0.002792 |
| 28 | −0.050962 | −0.017579 | 0.057217 | 0.05037 | −0.006032 | −0.041951 | 0.01979 | −0.027506 | 0.057137 | −0.01007 | 0.044642 | −0.001961 | 0.061857 | −0.029874 |
| 29 | 0.025998 | −0.061409 | 0.045164 | 0.075311 | 0.103481 | 0.043093 | 0.062549 | −0.062161 | 0.08587 | 0.077341 | 0.13044 | −0.051964 | −0.04202 | 0.003114 |
| 30 | −0.011562 | 0.056662 | 0.038822 | 0.081751 | −0.019548 | 0.039954 | −0.032791 | 0.010384 | −0.068091 | −0.014012 | 0.024439 | −0.045829 | 0.009377 | −0.012712 |
| 31 | −0.009188 | −0.018985 | −0.043111 | −0.00685 | −0.001664 | 0.023739 | −0.012091 | −0.002074 | 0.044344 | 0.008913 | 0.007269 | 0.057446 | −0.023303 | 0.050946 |
| 32 | 0.045235 | 0.011644 | −0.070011 | −0.048393 | 0.063801 | 0.07581 | −0.106551 | 0.104655 | −0.084293 | 0.033128 | −0.09131 | −0.102213 | 0.052104 | −0.09137 |
| 33 | −0.00726 | 0.033625 | 0.014322 | −0.073979 | −0.073145 | −0.037736 | 0.103806 | −0.012433 | −0.043954 | 0.059679 | 0.048444 | −0.02064 | 0.004433 | 0.013016 |
| 34 | 0.100377 | −0.019705 | −0.011323 | −0.00453 | −0.002235 | −0.070106 | −0.031233 | 0.004873 | 0.004048 | −0.069397 | 0.090885 | 0.041619 | −0.038159 | 0.00436 |
| 35 | 0.086835 | 0.020836 | 0.001709 | 0.047287 | −0.049386 | 0.0628 | −0.055954 | −0.008461 | 0.011116 | 0.055894 | 0.025681 | 0.007177 | −0.010014 | −0.03184 |
| 36 | 0.051385 | 0.053077 | −0.026086 | 0.099996 | −0.051167 | −0.030934 | −0.045343 | −0.007054 | −0.110381 | 0.002375 | −0.008316 | −0.02262 | −0.058733 | 0.068633 |
| 37 | −0.007231 | 0.053305 | 0.007986 | 0.02327 | −0.001125 | −0.002491 | −0.035275 | −0.00598 | −0.034016 | 0.023697 | 0.006419 | −0.006104 | −0.054024 | 0.015218 |
| 38 | −0.028533 | 0.10334 | −0.003512 | −0.047484 | 0.057797 | −0.042972 | −0.071495 | −0.054988 | −0.086557 | 0.049613 | 0.077128 | 0.039927 | −0.058046 | −0.042365 |
| 39 | −0.00226 | 0.003918 | −0.071964 | 0.043748 | −0.036042 | −0.008187 | 0.068118 | 0.007952 | −0.049481 | 0.05044 | −0.031537 | 0.047674 | 0.005314 | −0.022407 |
| 40 | 0.020433 | 0.048805 | −0.020143 | 0.005681 | −0.0296 | −0.043066 | −0.012544 | 0.013114 | −0.005257 | −0.02954 | 0.049945 | 0.038971 | 0.010306 | −0.016836 |
| 41 | −0.017988 | 0.030998 | −0.076052 | 0.002518 | −0.010567 | −0.016423 | −0.000799 | 0.035221 | −0.014507 | −0.031124 | 0.013651 | 0.048465 | 0.006866 | −0.028775 |
| 42 | 0.019927 | −0.023415 | −0.035465 | 0.028668 | −0.009598 | 0.00805 | −0.018271 | 0.02344 | −0.036772 | −0.005987 | 0.009011 | 0.034777 | −0.001513 | 0.005118 |
| 43 | 0.022457 | 0.029626 | −0.015207 | 0.005056 | −0.003694 | −0.01069 | −0.031499 | 0.010974 | −0.004726 | −0.045716 | 0.040817 | 0.037699 | 0.000911 | −0.013705 |
| 44 | 0.017328 | 0.068872 | −0.030459 | 0.001414 | −0.006506 | −0.015255 | 0.015276 | 0.004415 | 0.006967 | 0.039366 | −0.010872 | 0.008104 | 0.046305 | −0.045913 |
| 45 | 0.036116 | 0.038987 | 0.009059 | 0.008089 | −0.011777 | −0.024396 | −0.056871 | 0.048514 | −0.045504 | 0.003895 | 0.023504 | 0.066679 | −0.03989 | 0.010914 |
| 46 | 0.000703 | −0.022929 | −0.079317 | −0.04009 | 0.012882 | −0.025186 | 0.021655 | 0.032845 | 0.059961 | −0.053504 | −0.024822 | 0.02833 | −0.008037 | −0.052077 |
| 47 | −0.039193 | −0.048135 | 0.053712 | 0.022063 | −0.026143 | −0.092588 | 0.087652 | 0.042782 | −0.072384 | 0.106373 | −0.021816 | 0.0177 | −0.090037 | 0.046673 |
| 48 | 0.031125 | −0.023152 | −0.04088 | −0.009251 | 0.008659 | −0.020209 | 0.068578 | 0.01737 | −0.023728 | 0.048011 | −0.006879 | 0.039884 | −0.051392 | −0.105752 |
| 49 | −0.017641 | 0.020241 | 0.059495 | 0.055853 | −0.001404 | 0.057275 | −0.029849 | 0.017592 | −0.024806 | −0.027715 | 0.021941 | −0.054348 | 0.033519 | −0.001978 |
| 50 | −0.009088 | −0.036285 | 0.020966 | 0.009507 | 0.027685 | 0.016668 | −0.049489 | 0.017712 | −0.008969 | 0.033518 | −0.042531 | 0.052644 | 0.002157 | −0.078523 |
| 51 | 0.002627 | −0.046476 | −0.030082 | 0.028086 | −0.064932 | 0.025225 | −0.024392 | −0.031632 | −0.029351 | 0.042699 | 0.078774 | −0.003724 | −0.005251 | 0.024771 |
| 52 | −0.073032 | 0.017896 | −0.030063 | −0.042542 | 0.026939 | −0.023364 | 0.024499 | 0.002103 | 0.000959 | 0.021084 | 0.040446 | 0.013935 | 0.068178 | −0.052638 |
| 53 | −0.017835 | 0.005164 | −0.070443 | −0.041284 | −0.013687 | 0.016978 | −0.023958 | 0.025105 | 0.003874 | −0.007758 | 0.037864 | 0.033169 | 0.04313 | −0.017198 |
| 54 | 0.023452 | −0.039803 | −0.017814 | 0.025778 | −0.025723 | 0.024148 | −0.018995 | −0.013388 | −0.083545 | −0.037015 | −0.025394 | −0.003845 | −0.036542 | −0.042248 |
| 55 | −0.047069 | 0.020392 | −0.016411 | −0.033493 | −0.01797 | −0.03648 | −0.010406 | −0.014538 | 0.027284 | −0.007915 | 0.090636 | 0.043778 | 0.001576 | 0.021493 |
| 56 | −0.032358 | 0.001765 | 0.055585 | 0.030023 | 0.008774 | 0.060977 | −0.0241 | −0.023132 | 0.016402 | −0.008894 | 0.028127 | −0.008354 | 0.090369 | −0.008308 |
| 57 | −0.054495 | 0.074636 | −0.012707 | −0.023299 | −0.058434 | −0.038598 | 0.041719 | −0.027936 | 0.005445 | −0.015977 | 0.047521 | −0.019755 | −0.014523 | −0.049052 |
| 58 | 0.067477 | −0.008218 | 0.015027 | 0.03436 | 0.036516 | 0.031056 | −0.003917 | 0.059563 | −0.084016 | −0.027253 | 0.0649 | −0.030316 | 0.005892 | 0.000803 |
| 59 | −0.046913 | 0.208478 | 0.008315 | 0.005222 | −0.000416 | 0.012364 | 0.03761 | 0.009056 | 0.076908 | 0.005179 | −0.02339 | −0.06328 | 0.1648 | −0.089471 |
| 60 | 0.068543 | −0.075117 | −0.020136 | 0.019676 | 0.02196 | −0.02449 | 0.087633 | −0.020896 | 0.010452 | 0.013158 | −0.058679 | −0.008483 | 0.014245 | 0.054423 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 61 | −0.004932 | −0.03249 | −0.007219 | 0.04733 | 0.035273 | 0.053934 | 0.048983 | 0.015597 | 0.008316 | −0.034476 | −0.025001 | 0.051243 | 0.052637 | −0.053489 |
| 62 | 0.078436 | −0.066824 | −0.080722 | −0.050143 | 0.0995 | −0.021453 | 0.007165 | −0.010481 | 0.006539 | 0.004278 | −0.039453 | −0.027117 | 0.008261 | 0.041056 |
| 63 | −0.000455 | −0.008857 | 0.015555 | 0.061686 | −0.003618 | 0.033446 | −0.010979 | 0.009349 | −0.02581 | −0.008564 | 0.032345 | −0.023485 | 0.024622 | 0.016915 |
| 64 | 0.004075 | 0.003384 | 0.031636 | 0.05914 | −0.013398 | 0.042209 | −0.026198 | −0.003742 | −0.048071 | −0.050141 | 0.008412 | −0.022488 | 0.052721 | 0.031016 |
| 65 | −0.009573 | −0.008269 | −0.021717 | −0.010173 | −0.011339 | −0.027612 | 0.053017 | −0.053977 | 0.027865 | −0.083721 | 0.031487 | −0.043545 | −0.001258 | −0.00162 |
| 66 | −0.114682 | 0.089086 | −0.060055 | 0.035349 | 0.020826 | 0.009166 | 0.10524 | −0.011718 | 0.009983 | −0.005141 | 0.001471 | −0.078808 | 0.067184 | 0.004985 |
| 67 | −0.060602 | 0.026447 | −0.016766 | 0.074265 | 0.106589 | 0.056801 | 0.079918 | −0.035708 | −0.010743 | 0.045454 | 0.053099 | −0.018355 | −0.025577 | 0.029483 |
| 68 | −0.133572 | −0.128848 | −0.00426 | −0.0968 | 0.00852 | 0.010223 | 0.020105 | 0.079099 | −0.047169 | −0.013814 | −0.045887 | −0.004546 | 0.085445 | −0.019383 |
| 69 | −0.026539 | −0.036718 | −0.053408 | −0.026472 | −0.01319 | 0.010076 | −0.057029 | 0.063002 | 0.021992 | −0.001573 | −0.003723 | 0.039326 | 0.063341 | 0.040899 |
| 70 | −0.001067 | −0.013037 | −0.008261 | −0.034044 | −0.041393 | −0.023 | 0.014609 | −0.053853 | 0.078699 | −0.0365 | 0.024009 | −0.042701 | −0.040051 | 0.068577 |
| 71 | −0.027331 | −0.007276 | −0.09109 | 0.014038 | −0.022012 | 0.092586 | −0.016045 | 0.047038 | −0.093883 | 0.015079 | −0.038988 | 0.040994 | 0.019187 | 0.078559 |
| 72 | 0.019379 | −0.044213 | −0.096196 | 0.003885 | −0.060524 | 0.056921 | −0.001411 | −0.004087 | −0.035286 | −0.054092 | −0.006444 | 0.036894 | 0.02653 | 0.094558 |
| 73 | −0.192528 | 0.016371 | −0.122267 | −0.061984 | 0.022152 | −0.005927 | 0.026973 | 0.086854 | −0.015546 | 0.004741 | −0.03662 | 0.072535 | −0.0509 | 0.005409 |
| 74 | −0.009528 | 0.009628 | 0.054917 | 0.049819 | −0.009345 | 0.074373 | −0.033816 | −0.117641 | 0.039883 | 0.089219 | −0.067891 | 0.085341 | −0.050745 | 0.035713 |
| 75 | 0.007609 | −0.016403 | −0.001233 | −0.011626 | −0.01323 | 0.018705 | 0.015473 | −0.020289 | −0.003686 | 0.034003 | 0.005697 | −0.012204 | 0.022687 | 0.027461 |
| 76 | 0.027461 | −0.008075 | 0.015348 | −0.009748 | −0.003665 | 0.000961 | −0.09419 | −0.046306 | 0.003659 | −0.010876 | 0.007433 | 0.029924 | −0.013679 | 0.056142 |
| 77 | 0.000262 | −0.020569 | −0.020371 | 0.00327 | −0.024667 | 0.024948 | 0.010928 | 0.009268 | 0.016269 | 0.007155 | 0.039818 | 0.015086 | −0.006742 | 0.024832 |
| 78 | 0.005121 | −0.024347 | −0.003734 | −0.013369 | −0.023531 | 0.017364 | 0.025306 | 0.00376 | 0.002226 | 0.004524 | 0.042298 | 0.017482 | −0.027016 | 0.018841 |
| 79 | 0.011081 | 0.000242 | 0.020312 | −0.02921 | 0.004258 | −0.004569 | 0.020789 | −0.024632 | −0.030486 | −0.006087 | −0.047949 | 0.000284 | 0.009515 | −0.003714 |
| 80 | 0.041539 | 0.035616 | −0.010885 | −0.056309 | −0.161413 | 0.045267 | 0.079411 | 0.068774 | −0.028249 | 0.073085 | 0.091588 | −0.078174 | 0.071854 | −0.057887 |
| 81 | −0.027766 | 0.03232 | 0.062203 | 0.043428 | 0.097014 | −0.066615 | −0.137544 | 0.041289 | 0.095523 | −0.045444 | 0.059055 | −0.137083 | 0.02667 | 0.013972 |
| 82 | 0.040935 | −0.020411 | 0.049232 | 0.010954 | −0.025601 | −0.008005 | 0.00693 | −0.038349 | 0.043442 | −0.022846 | 0.010476 | −0.060783 | 0.022482 | 0.010672 |
| 83 | 0.008486 | −0.029398 | 0.037955 | 0.009382 | −0.00211 | −0.001791 | 0.000992 | −0.015179 | −0.019205 | −0.033395 | 0.005256 | −0.01154 | 0.026052 | −0.007914 |
| 84 | 0.018142 | −0.001026 | 0.027577 | −0.009919 | −0.012675 | −0.004717 | 0.00798 | −0.037284 | −0.002145 | −0.007841 | 0.029804 | 0.034074 | 0.011695 | −0.006435 |
| 85 | 0.000284 | −0.010219 | 0.027736 | −0.047431 | 0.042973 | −0.008156 | −0.034324 | 0.022078 | 0.017976 | −0.11994 | −0.146978 | 0.06795 | 0.108222 | 0.02226 |
| 86 | −0.039701 | 0.019853 | −0.117279 | −0.019308 | 0.059145 | 0.000369 | −0.014901 | 0.091476 | 0.006535 | −0.0535 | −0.021672 | 0.077066 | 0.035859 | 0.113997 |
| 87 | −0.093236 | −0.016324 | −0.079988 | 0.020913 | −0.081406 | 0.027098 | −0.002468 | 0.02782 | 0.001382 | 0.038388 | −0.030962 | −0.029751 | 0.032798 | 0.076729 |
| 88 | −0.000316 | −0.007483 | 0.079339 | 0.033777 | −0.024511 | 0.00406 | 0.025686 | 0.000078 | −0.00429 | 0.028115 | 0.034134 | −0.033943 | −0.001384 | 0.00296 |
| 89 | −0.012445 | −0.027153 | 0.050636 | 0.009035 | 0.008723 | −0.012081 | −0.002324 | −0.029252 | −0.009469 | −0.003153 | −0.009871 | 0.016133 | 0.015025 | −0.018724 |
| 90 | −0.019425 | −0.049562 | 0.033657 | 0.00448 | 0.052964 | −0.000417 | −0.004623 | −0.045305 | 0.002938 | −0.002864 | −0.024243 | 0.031035 | 0.051005 | 0.009509 |
| 91 | 0.014904 | 0.020421 | 0.049845 | −0.031432 | 0.020578 | −0.030975 | 0.042121 | −0.075598 | 0.048411 | −0.062761 | 0.051744 | 0.010342 | −0.001393 | −0.005758 |
| 92 | −0.017235 | −0.017082 | 0.001144 | −0.026471 | 0.060521 | −0.084992 | −0.022481 | −0.057503 | 0.003061 | −0.045875 | 0.095531 | −0.08766 | −0.141472 | −0.09304 |
| 93 | 0.018541 | −0.088286 | 0.031126 | 0.009956 | 0.096005 | 0.021023 | −0.039992 | 0.002235 | 0.011889 | 0.001423 | 0.030018 | −0.057118 | 0.019637 | 0.006106 |
| 94 | 0.01561 | 0.044341 | 0.09191 | −0.039441 | −0.020021 | 0.001037 | 0.022107 | 0.026377 | −0.026197 | 0.008721 | −0.116912 | −0.002705 | 0.007399 | 0.069136 |
| 95 | −0.035035 | 0.046896 | −0.012275 | −0.046151 | 0.078727 | 0.045818 | −0.026436 | 0.151371 | 0.001773 | −0.01994 | −0.046069 | 0.059746 | 0.019599 | −0.077111 |
| 96 | −0.016194 | −0.008688 | 0.021097 | 0.068363 | −0.056273 | −0.012163 | 0.04638 | −0.034698 | −0.048917 | −0.042294 | −0.039813 | 0.078932 | −0.146029 | 0.090344 |
| 97 | 0.006218 | −0.041903 | 0.021372 | 0.05535 | −0.079964 | −0.059537 | −0.026864 | 0.076321 | 0.006129 | 0.013959 | −0.068726 | −0.014974 | −0.043536 | 0.022145 |
| 98 | 0.025787 | 0.050677 | 0.00582 | 0.013788 | −0.006703 | 0.013714 | −0.024316 | 0.000485 | −0.019676 | 0.057702 | −0.040945 | −0.025277 | −0.007303 | 0.013373 |
| 99 | −0.032029 | 0.020006 | 0.01749 | 0.037953 | −0.019599 | −0.021298 | 0.013725 | 0.013035 | 0.014349 | 0.019426 | −0.034239 | 0.027381 | −0.051997 | 0.029631 |
| 100 | 0.008122 | 0.033353 | −0.031342 | 0.041332 | −0.016405 | −0.004976 | −0.060928 | −0.039016 | −0.01112 | −0.00988 | −0.039847 | −0.027589 | −0.057783 | 0.027868 |
| 101 | 0.000455 | 0.037414 | 0.027054 | 0.002723 | −0.011783 | 0.059468 | −0.046716 | 0.010231 | −0.012131 | 0.078455 | −0.022283 | −0.001275 | −0.02552 | 0.021948 |
| 102 | −0.034479 | −0.090766 | 0.04356 | 0.021951 | −0.074859 | 0.051922 | −0.087906 | 0.031667 | 0.059128 | −0.070627 | −0.004339 | −0.034498 | −0.032419 | 0.070342 |
| 103 | −0.055349 | −0.108108 | −0.039825 | −0.004001 | −0.062405 | 0.134046 | 0.108319 | 0.149594 | 0.011658 | −0.03297 | 0.064489 | −0.103784 | −0.056039 | −0.024484 |
| 104 | −0.017883 | −0.003732 | −0.069043 | 0.014398 | 0.03689 | 0.050454 | 0.075624 | 0.006872 | −0.060121 | −0.00054 | 0.100505 | 0.054724 | −0.0572 | −0.042384 |
| 105 | −0.062709 | −0.074054 | −0.068493 | −0.027046 | −0.073095 | −0.014761 | −0.034363 | −0.017582 | −0.073007 | 0.064572 | 0.003378 | −0.108761 | −0.056567 | 0.029189 |
| 106 | 0.00965 | −0.017372 | −0.052968 | 0.043132 | −0.013871 | −0.01567 | 0.016508 | −0.036579 | −0.027161 | 0.043832 | 0.060041 | −0.100366 | 0.082591 | 0.023843 |
| 107 | 0.000502 | 0.097611 | −0.018596 | 0.01853 | −0.054936 | −0.045538 | −0.037235 | 0.05072 | 0.027593 | 0.083611 | 0.029534 | −0.028104 | 0.056203 | 0.060118 |
| 108 | −0.015179 | 0.038197 | 0.053063 | 0.005769 | −0.007305 | 0.161727 | −0.080416 | 0.044954 | 0.008628 | 0.11516 | 0.047516 | 0.024549 | −0.039912 | 0.004441 |
| 109 | −0.046266 | −0.128504 | 0.035807 | −0.218939 | −0.030554 | 0.068502 | −0.038329 | 0.019874 | −0.068148 | −0.054204 | −0.001096 | 0.00318 | −0.028873 | −0.046527 |
| 110 | 0.192702 | −0.062094 | −0.124112 | 0.075529 | −0.196431 | 0.050222 | 0.04411 | −0.02079 | −0.112428 | −0.024739 | 0.088965 | 0.167611 | −0.005376 | −0.09896 |

APPENDIX B3-continued

PCA Transformation
Matrix (340 × 340 Early/Late)

| | | | | | | | | | | | | | |
|---|---|---|---|---|---|---|---|---|---|---|---|---|---|
| 111 | −0.021826 | 0.111096 | −0.01578 | 0.024199 | −0.060379 | 0.06093 | −0.126089 | −0.078494 | 0.072083 | 0.0645 | 0.097318 | 0.143976 | 0.034525 | 0.081928 |
| 112 | −0.027912 | −0.014423 | −0.060701 | 0.094988 | 0.044398 | 0.148222 | −0.079819 | 0.029399 | −0.018785 | 0.016213 | 0.031519 | 0.065436 | −0.016743 | −0.027693 |
| 113 | −0.072826 | −0.009952 | 0.0192 | −0.03405 | 0.035505 | −0.022246 | −0.110675 | −0.045156 | 0.007261 | 0.071522 | −0.095716 | −0.059957 | 0.066488 | −0.08709 |
| 114 | −0.033668 | −0.016158 | −0.081199 | −0.016045 | 0.100052 | −0.002044 | −0.073142 | −0.092661 | −0.049799 | 0.053133 | −0.067726 | −0.011351 | −0.065811 | −0.10344 |
| 115 | 0.036403 | 0.055138 | −0.042067 | 0.031281 | 0.140298 | 0.062256 | 0.107444 | −0.076642 | 0.0544 | −0.013905 | 0.090868 | 0.076849 | −0.045736 | 0.18268 |
| 116 | −0.083908 | −0.131815 | −0.027259 | −0.016025 | −0.097454 | 0.206669 | −0.173503 | 0.008068 | 0.006586 | −0.020088 | −0.017747 | −0.032326 | −0.0609 | −0.097833 |
| 117 | −0.091542 | 0.014976 | 0.068987 | 0.045565 | −0.036403 | 0.060912 | 0.057271 | −0.020211 | 0.012384 | −0.064354 | −0.029106 | −0.019206 | −0.119632 | 0.004589 |
| 118 | 0.027335 | 0.071331 | −0.045542 | −0.014476 | 0.015115 | −0.071433 | 0.041947 | −0.041736 | 0.082263 | 0.081356 | −0.109589 | −0.104826 | −0.129858 | −0.002848 |
| 119 | 0.003516 | 0.036508 | 0.005626 | −0.029965 | −0.049663 | −0.019796 | 0.004065 | 0.024097 | 0.05504 | −0.011418 | 0.016447 | 0.054894 | −0.008882 | 0.096571 |
| 120 | −0.055514 | 0.016345 | 0.03868 | −0.07639 | 0.031396 | −0.063047 | −0.00724 | −0.09483 | 0.011349 | −0.044817 | 0.017745 | −0.049009 | −0.04464 | −0.025981 |
| 121 | 0.121784 | 0.006042 | 0.105732 | −0.103032 | −0.012271 | −0.054852 | −0.024844 | −0.091842 | 0.000588 | 0.011444 | −0.010018 | −0.027496 | 0.04847 | 0.048572 |
| 122 | −0.00961 | 0.100569 | −0.065095 | 0.007263 | 0.043726 | −0.013917 | −0.024069 | 0.043733 | 0.047838 | −0.023066 | −0.038601 | −0.008447 | 0.025409 | −0.07896 |
| 123 | 0.042144 | 0.15113 | −0.046573 | −0.005105 | 0.0339291 | 0.019109 | −0.085732 | 0.0155861 | 0.08315 | −0.025429 | 0.020293 | −0.056106 | 0.079183 | −0.027685 |
| 124 | 0.028448 | 0.081156 | −0.011365 | −0.00498 | −0.021573 | 0.006359 | −0.014678 | 0.019281 | 0.07634 | −0.012236 | −0.034247 | 0.028728 | −0.030049 | 0.03401 |
| 125 | 0.072522 | 0.044548 | 0.018926 | 0.006903 | −0.024449 | 0.029409 | 0.001119 | −0.013552 | −0.054647 | 0.0282 | −0.061736 | −0.040998 | 0.017144 | −0.042583 |
| 126 | 0.069025 | 0.085709 | 0.017422 | −0.02497 | 0.014686 | −0.018995 | −0.006947 | −0.018534 | 0.095186 | 0.098401 | −0.019209 | −0.042265 | −0.04042 | −0.036844 |
| 127 | 0.052301 | 0.068385 | 0.009745 | 0.027088 | −0.028636 | 0.017234 | 0.033794 | −0.005598 | −0.018523 | 0.050012 | −0.028081 | 0.025018 | −0.008603 | 0.006231 |
| 128 | 0.030289 | −0.032519 | −0.066337 | 0.01743 | −0.014811 | −0.045728 | 0.076394 | −0.019332 | −0.005799 | −0.034396 | 0.047223 | 0.018488 | −0.031567 | −0.029837 |
| 129 | −0.091305 | −0.189865 | −0.070752 | 0.268193 | 0.102521 | 0.073038 | −0.037215 | 0.134251 | −0.004821 | 0.043131 | 0.031364 | 0.0629 | 0.146595 | 0.130617 |
| 130 | −0.098302 | −0.117511 | 0.102946 | −0.106337 | 0.182548 | −0.003467 | 0.128157 | 0.055486 | 0.035736 | −0.126135 | 0.083275 | 0.059375 | −0.074854 | 0.086225 |
| 131 | −0.02477 | −0.124503 | 0.018247 | −0.050184 | −0.202437 | 0.0148 | −0.088555 | 0.133777 | 0.107827 | 0.092545 | −0.046443 | −0.025186 | 0.035517 | 0.099732 |
| 132 | 0.01099 | 0.044412 | −0.071659 | −0.049537 | 0.00332 | 0.045208 | 0.024608 | −0.000032 | −0.060949 | −0.045015 | 0.037597 | 0.039288 | 0.02933 | 0.085166 |
| 133 | 0.04489 | 0.019553 | −0.006373 | 0.005337 | −0.060463 | −0.033253 | 0.101145 | 0.108132 | −0.13643 | 0.01142 | −0.04148 | −0.047652 | 0.065699 | 0.055207 |
| 134 | 0.021529 | −0.00493 | 0.112568 | 0.024301 | −0.127307 | 0.15386 | 0.038881 | 0.070819 | 0.223073 | −0.188523 | −0.050556 | 0.162122 | −0.06809 | 0.012891 |
| 135 | −0.002602 | 0.039862 | −0.004308 | 0.006188 | −0.009167 | 0.02903 | 0.032327 | 0.004477 | −0.053882 | −0.030706 | 0.009759 | −0.013211 | −0.02038 | −0.046618 |
| 136 | −0.013805 | 0.015345 | −0.100947 | −0.025936 | −0.109933 | 0.003369 | 0.00449 | −0.052715 | 0.022286 | −0.10274 | −0.025472 | 0.014972 | −0.035596 | 0.1032 |
| 137 | −0.019718 | −0.094743 | −0.030671 | 0.004607 | −0.021628 | 0.018838 | 0.039057 | −0.036774 | 0.008814 | 0.103008 | −0.130321 | −0.030489 | 0.097506 | −0.017231 |
| 138 | −0.077451 | −0.053336 | 0.121762 | −0.038481 | −0.007056 | −0.125169 | −0.071476 | 0.063842 | −0.07403 | 0.024685 | −0.025247 | 0.070211 | −0.132316 | 0.018319 |
| 139 | 0.07055 | −0.139661 | 0.060622 | −0.209906 | 0.004923 | 0.174743 | 0.024846 | −0.057217 | 0.054173 | 0.186758 | 0.147104 | 0.05294 | 0.091911 | −0.035726 |
| 140 | 0.050295 | −0.113994 | −0.091452 | 0.031487 | 0.050311 | −0.105073 | 0.036878 | 0.063151 | 0.152254 | 0.034441 | 0.019299 | 0.202098 | 0.043805 | −0.01322 |
| 141 | 0.005529 | 0.034842 | −0.005405 | −0.007615 | −0.005982 | −0.025864 | 0.034709 | 0.075519 | −0.095565 | −0.012124 | 0.028837 | 0.005262 | −0.083568 | −0.075726 |
| 142 | −0.024014 | 0.037723 | 0.057052 | −0.033193 | 0.069037 | −0.03119 | −0.053589 | 0.074095 | −0.044575 | −0.011854 | 0.016195 | 0.005235 | −0.028491 | −0.064452 |
| 143 | 0.004312 | 0.081989 | 0.019353 | 0.031042 | 0.049344 | −0.000469 | −0.083556 | 0.108143 | −0.058178 | −0.040898 | 0.090984 | −0.044961 | 0.019638 | −0.087183 |
| 144 | −0.012115 | 0.032569 | −0.000364 | 0.079204 | 0.024803 | 0.012545 | −0.033911 | 0.150623 | 0.035825 | −0.007105 | 0.080694 | −0.025083 | 0.046277 | −0.008672 |
| 145 | 0.005223 | 0.034344 | −0.08295 | 0.088347 | −0.018405 | −0.014301 | −0.01265 | 0.037496 | 0.026287 | −0.094155 | −0.005777 | −0.087259 | 0.042271 | −0.021208 |
| 146 | −0.01362 | 0.020315 | 0.035898 | −0.035049 | −0.00452 | 0.021579 | 0.021285 | 0.002545 | 0.012488 | −0.016124 | −0.003615 | −0.026182 | 0.037399 | −0.024523 |
| 147 | −0.056451 | −0.008451 | 0.155318 | 0.008516 | 0.092452 | −0.079669 | −0.055965 | 0.025477 | −0.047235 | −0.030142 | 0.076399 | −0.058148 | 0.042934 | −0.058295 |
| 148 | −0.110534 | −0.126612 | −0.142992 | −0.004018 | 0.073774 | −0.028409 | 0.002878 | 0.048531 | 0.165035 | 0.179014 | −0.029315 | 0.048566 | −0.093451 | −0.103166 |
| 149 | −0.026849 | 0.020295 | −0.052711 | 0.00125 | −0.05201 | −0.003196 | 0.045884 | −0.001286 | −0.029516 | −0.002224 | −0.003952 | −0.001756 | 0.009538 | −0.008193 |
| 150 | −0.010474 | −0.021723 | 0.013504 | 0.007443 | 0.077763 | 0.079394 | −0.037054 | −0.032151 | 0.028485 | −0.026648 | −0.033009 | −0.071031 | −0.057118 | −0.137832 |
| 151 | 0.04152 | 0.028286 | 0.024259 | 0.153918 | −0.021775 | 0.102571 | 0.159125 | 0.10133 | 0.027109 | −0.080375 | 0.092425 | −0.086708 | 0.036036 | −0.088921 |
| 152 | −0.031409 | 0.052258 | 0.000905 | 0.007656 | −0.073212 | 0.010666 | −0.015886 | 0.001729 | 0.006318 | −0.005081 | 0.070884 | 0.078226 | 0.053502 | 0.009434 |
| 153 | 0.018519 | 0.004545 | 0.029906 | −0.093842 | −0.062673 | 0.035573 | 0.046668 | 0.035617 | −0.011829 | −0.067202 | 0.079118 | 0.022154 | −0.005576 | −0.053126 |
| 154 | −0.032793 | 0.015595 | 0.051969 | −0.048212 | −0.054901 | 0.006799 | −0.056006 | −0.004466 | 0.00643 | −0.083471 | 0.067243 | 0.009671 | −0.010283 | 0.001811 |
| 155 | −0.021703 | 0.04217 | −0.016166 | −0.099783 | −0.050142 | −0.019641 | −0.032733 | −0.058926 | 0.049096 | −0.026314 | 0.129617 | −0.001356 | 0.101234 | 0.157574 |
| 156 | −0.040255 | 0.082779 | 0.161813 | 0.003026 | −0.07424 | −0.010791 | −0.102434 | 0.043563 | 0.001184 | −0.072786 | 0.13935 | −0.010417 | −0.028303 | 0.014292 |
| 157 | 0.079332 | 0.062409 | −0.016684 | 0.022519 | 0.069276 | −0.042558 | 0.006953 | −0.072886 | −0.020253 | 0.001863 | 0.033965 | 0.00543 | 0.010491 | −0.054835 |
| 158 | −0.020406 | 0.125 | 0.134822 | −0.077041 | −0.134131 | 0.033403 | 0.013625 | −0.08701 | −0.098808 | −0.018543 | −0.003117 | 0.143532 | −0.010991 | 0.054805 |
| 159 | 0.011075 | −0.167164 | −0.042451 | 0.131225 | −0.005213 | −0.037692 | 0.016641 | −0.171408 | −0.040462 | −0.023377 | 0.076449 | −0.061579 | −0.084318 | −0.134954 |
| 160 | 0.098665 | −0.103418 | 0.017772 | 0.100778 | −0.191224 | −0.14609 | −0.087293 | −0.060094 | −0.019344 | 0.004582 | −0.10408 | 0.068577 | 0.061924 | −0.218558 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 161 | −0.126116 | −0.172397 | −0.01653 | −0.078368 | −0.024138 | 0.036202 | −0.059487 | −0.006044 | −0.060702 | 0.005684 | 0.05346 | 0.185247 | 0.057782 | −0.029012 |
| 162 | 0.005534 | −0.028729 | 0.029071 | −0.050178 | −0.096421 | 0.09025 | −0.058207 | 0.035261 | −0.068877 | 0.058174 | −0.0787 | −0.065327 | 0.02532 | −0.006997 |
| 163 | −0.008823 | 0.058162 | 0.013775 | 0.051419 | −0.028643 | −0.026423 | −0.040728 | −0.000328 | −0.060633 | 0.006861 | −0.00452 | 0.061791 | 0.058038 | −0.040966 |
| 164 | −0.022378 | 0.008426 | 0.018315 | 0.0511 | −0.02044 | −0.046732 | 0.053378 | −0.001844 | −0.047121 | 0.116869 | 0.015147 | −0.14542 | −0.002903 | 0.0055 |
| 165 | −0.021106 | 0.080251 | −0.089566 | −0.059705 | −0.004349 | −0.058747 | 0.064775 | 0.066269 | −0.02064 | 0.037515 | 0.041639 | −0.128918 | 0.166052 | 0.170792 |
| 166 | 0.012473 | −0.003688 | 0.027168 | −0.042789 | 0.031708 | −0.006532 | 0.033481 | 0.111455 | −0.014761 | 0.020724 | −0.08293 | −0.040515 | −0.140362 | −0.039255 |
| 167 | −0.010539 | 0.027721 | −0.026112 | −0.054416 | 0.085987 | 0.021333 | 0.032944 | 0.007295 | −0.018829 | 0.083736 | 0.043038 | 0.010054 | 0.04177 | 0.02252 |
| 168 | −0.054425 | −0.013559 | 0.047884 | 0.044912 | 0.027405 | −0.146231 | 0.054785 | 0.095626 | −0.024719 | 0.009154 | −0.112146 | 0.011897 | −0.005165 | 0.041036 |
| 169 | −0.036689 | −0.01481 | 0.068306 | −0.022818 | 0.032134 | 0.042195 | −0.023889 | 0.006491 | −0.057766 | −0.003368 | 0.020865 | −0.016637 | −0.016018 | 0.041568 |
| 170 | −0.016705 | −0.03603 | 0.063748 | −0.009945 | 0.035392 | 0.038765 | −0.032319 | 0.023188 | −0.040889 | −0.027749 | 0.017996 | −0.021017 | −0.048226 | 0.098278 |
| 171 | −0.020709 | 0.026891 | 0.058424 | −0.045283 | 0.045406 | −0.003306 | −0.041264 | 0.031995 | −0.007054 | 0.026321 | 0.047017 | 0.011656 | −0.027834 | 0.051076 |
| 172 | 0.005604 | −0.029005 | 0.047779 | −0.030935 | 0.019734 | 0.046743 | 0.024489 | −0.014186 | 0.040389 | −0.073919 | 0.002045 | −0.041736 | 0.026786 | 0.00929 |
| 173 | 0.020285 | −0.053937 | 0.029979 | −0.027546 | 0.013198 | 0.053408 | 0.046402 | −0.043856 | 0.011978 | −0.0047 | −0.045095 | −0.009907 | 0.069723 | 0.044945 |
| 174 | −0.018178 | −0.119554 | 0.051017 | −0.053694 | −0.018424 | 0.002392 | 0.021911 | −0.029129 | −0.029593 | −0.030275 | −0.03988 | 0.046944 | 0.062745 | 0.02104 |
| 175 | −0.06364 | −0.082909 | 0.023528 | −0.049154 | −0.012701 | 0.055359 | −0.011393 | −0.147748 | 0.057087 | −0.086092 | −0.106264 | −0.099849 | 0.095524 | −0.030119 |
| 176 | −0.064347 | 0.05566 | 0.062949 | −0.060938 | 0.013768 | 0.025109 | −0.055697 | −0.064116 | −0.031102 | −0.002775 | −0.009447 | −0.058484 | −0.025114 | 0.104414 |
| 177 | −0.049331 | −0.100705 | 0.038532 | −0.04075 | 0.00113 | −0.075138 | 0.157147 | 0.003548 | 0.022518 | −0.036035 | 0.146566 | 0.111711 | −0.102326 | 0.012485 |
| 178 | −0.023621 | 0.010549 | −0.031772 | 0.041135 | −0.011917 | 0.00883 | 0.045505 | −0.025715 | 0.014322 | 0.132058 | 0.008582 | −0.040333 | 0.058256 | 0.015536 |
| 179 | −0.008494 | 0.067512 | 0.014077 | −0.002355 | 0.004358 | −0.058225 | −0.035367 | 0.005769 | 0.008793 | 0.066586 | 0.008931 | −0.004108 | −0.034783 | 0.017416 |
| 180 | −0.006184 | 0.02388 | 0.007241 | −0.00267 | −0.003723 | −0.009777 | −0.002206 | −0.006633 | 0.004322 | 0.0678 | −0.025372 | 0.001474 | −0.041383 | 0.030654 |
| 181 | 0.021453 | 0.04264 | −0.000155 | −0.018311 | −0.005767 | 0.000798 | −0.01612 | −0.013173 | −0.001755 | 0.049672 | 0.002249 | 0.004329 | −0.024278 | 0.036691 |
| 182 | −0.021914 | 0.042725 | −0.015526 | 0.015697 | 0.007984 | −0.033645 | −0.026152 | −0.037216 | 0.026042 | 0.003609 | −0.018006 | −0.001674 | −0.062371 | 0.042459 |
| 183 | 0.004023 | 0.101467 | −0.006268 | 0.009796 | 0.000368 | −0.055005 | −0.122567 | −0.03187 | 0.06322 | 0.030582 | 0.024974 | −0.01781 | −0.074243 | 0.020167 |
| 184 | 0.021969 | 0.046026 | 0.011334 | 0.054777 | 0.001329 | −0.023254 | −0.199224 | 0.010732 | 0.074063 | 0.033879 | 0.066189 | −0.001399 | −0.005267 | 0.023585 |
| 185 | −0.055744 | 0.032113 | −0.080098 | −0.035739 | 0.064518 | −0.03295 | 0.016566 | −0.036592 | 0.003577 | −0.143926 | 0.000072 | −0.00385 | −0.063951 | −0.117408 |
| 186 | 0.004999 | −0.069175 | −0.092791 | −0.169576 | 0.098551 | −0.048518 | 0.080872 | 0.02931 | 0.079061 | −0.089984 | 0.039265 | 0.030891 | −0.015043 | −0.007338 |
| 187 | −0.014504 | −0.021225 | −0.001081 | 0.032383 | −0.026182 | 0.038092 | −0.016442 | −0.044659 | 0.024585 | −0.007549 | −0.050545 | −0.060634 | −0.049904 | 0.053745 |
| 188 | −0.027741 | −0.089317 | 0.042755 | 0.013081 | −0.060418 | 0.013162 | −0.069594 | −0.040458 | −0.004353 | −0.02709 | −0.033035 | −0.041092 | −0.048425 | 0.069306 |
| 189 | 0.007845 | −0.11287 | 0.070929 | −0.00306 | −0.053477 | 0.032567 | −0.19813 | −0.081903 | −0.020209 | −0.029716 | −0.060629 | −0.041537 | −0.088024 | 0.020207 |
| 190 | 0.025113 | 0.023976 | 0.011706 | −0.038351 | −0.019657 | 0.017859 | −0.016454 | −0.01918 | 0.027737 | 0.0083 | −0.047082 | −0.026409 | −0.050535 | 0.011632 |
| 191 | 0.017788 | 0.019774 | 0.011466 | −0.019298 | −0.016573 | −0.035677 | 0.008458 | 0.00581 | 0.035422 | −0.026186 | 0.031461 | 0.06429 | −0.066615 | 0.036239 |
| 192 | −0.021124 | 0.070008 | 0.038187 | 0.086468 | −0.066954 | −0.043778 | −0.031117 | 0.058726 | 0.038826 | 0.016988 | −0.011875 | 0.045128 | −0.041141 | −0.038033 |
| 193 | −0.028308 | 0.029244 | 0.025373 | 0.025308 | −0.045716 | −0.031152 | −0.045895 | 0.009768 | 0.058378 | −0.060963 | −0.027425 | −0.028008 | −0.001952 | 0.007641 |
| 194 | −0.038312 | 0.034392 | 0.099086 | 0.026486 | −0.00366 | 0.035097 | −0.060277 | 0.033662 | 0.046015 | −0.072783 | −0.078391 | −0.104699 | −0.031777 | 0.070671 |
| 195 | 0.0882 | 0.041025 | −0.096589 | −0.073827 | 0.007788 | 0.049675 | −0.037166 | 0.017907 | 0.045789 | −0.000665 | 0.002475 | 0.072752 | 0.054354 | −0.056733 |
| 196 | 0.025064 | 0.013082 | −0.039242 | −0.037829 | 0.007279 | 0.083482 | −0.013327 | −0.03999 | 0.052366 | −0.016867 | −0.028944 | 0.060716 | 0.018086 | −0.027091 |
| 197 | 0.001961 | 0.06098 | 0.000073 | 0.010962 | −0.01233 | −0.006875 | 0.065348 | −0.060123 | 0.000726 | −0.072425 | 0.007236 | 0.027493 | −0.021784 | 0.003086 |
| 198 | −0.006972 | 0.047247 | −0.09303 | 0.009568 | 0.094013 | −0.029267 | −0.005945 | −0.032779 | 0.12249 | 0.001707 | 0.035264 | −0.043662 | 0.006876 | −0.042724 |
| 199 | −0.11829 | −0.0891 | 0.028529 | 0.076641 | 0.018319 | −0.125228 | 0.044528 | 0.031972 | −0.189994 | 0.111581 | −0.011289 | −0.018097 | 0.127495 | 0.099188 |
| 200 | 0.060288 | −0.02936 | −0.02671 | 0.007931 | −0.034413 | 0.024924 | 0.110872 | 0.030386 | 0.000128 | 0.058569 | 0.026041 | −0.021495 | 0.065397 | −0.049653 |
| 201 | −0.179365 | 0.086452 | −0.132792 | −0.110226 | −0.112493 | 0.102571 | −0.077029 | 0.033097 | −0.068729 | 0.163929 | −0.080303 | 0.112319 | −0.118784 | 0.027751 |
| 202 | −0.005193 | 0.087845 | −0.07472 | 0.049739 | 0.0531 | 0.015078 | 0.093661 | 0.012215 | 0.073221 | −0.03196 | −0.004014 | −0.016099 | 0.05343 | −0.003853 |
| 203 | 0.030235 | −0.092832 | −0.052037 | 0.104357 | 0.016179 | −0.074852 | −0.022765 | 0.019036 | −0.008897 | −0.038588 | 0.045789 | −0.078033 | 0.00387 | 0.060175 |
| 204 | −0.080526 | 0.001312 | −0.077744 | 0.064503 | 0.143759 | 0.11608 | −0.043812 | −0.027319 | 0.050903 | −0.023031 | 0.082545 | 0.007544 | −0.073391 | 0.003519 |
| 205 | 0.164307 | 0.05408 | 0.104833 | −0.019546 | −0.035272 | 0.042631 | 0.120673 | 0.04954 | 0.02159 | 0.044899 | −0.052891 | 0.041325 | 0.031628 | −0.053845 |
| 206 | −0.028519 | 0.064443 | −0.009584 | −0.090391 | 0.013816 | 0.214244 | 0.002254 | 0.167339 | 0.089753 | 0.050526 | −0.107266 | 0.121892 | −0.009189 | 0.00757 |
| 207 | 0.088745 | 0.047066 | −0.04384 | −0.130145 | 0.037478 | 0.062347 | 0.037114 | −0.185338 | −0.114702 | 0.134675 | 0.066704 | −0.109546 | −0.006972 | 0.087586 |
| 208 | 0.007984 | −0.0076 | 0.000373 | 0.011729 | 0.054764 | 0.121848 | 0.050536 | 0.047925 | −0.050036 | −0.092032 | 0.146331 | 0.026791 | −0.029616 | 0.070139 |
| 209 | −0.063516 | 0.090345 | 0.115909 | 0.119356 | −0.029654 | 0.075148 | 0.071232 | 0.025532 | −0.142988 | −0.166706 | −0.058458 | −0.024119 | −0.028322 | 0.040361 |
| 210 | −0.171403 | −0.013339 | −0.093892 | 0.135101 | −0.166641 | −0.000544 | 0.030247 | −0.225954 | 0.069338 | −0.081036 | 0.097706 | 0.016927 | 0.078738 | −0.04576 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 211 | −0.03897 | 0.01651 | 0.026644 | 0.024972 | −0.107258 | 0.111492 | 0.050711 | −0.024107 | 0.147948 | 0.062168 | 0.11018 | 0.005592 | −0.101027 | −0.042746 |
| 212 | 0.126763 | −0.041372 | 0.002168 | −0.045003 | −0.021974 | 0.003558 | −0.08532 | 0.015675 | 0.059903 | 0.099077 | 0.136431 | −0.103184 | −0.007154 | −0.133427 |
| 213 | −0.080845 | −0.040174 | −0.091878 | 0.031912 | −0.064383 | −0.202139 | −0.161282 | 0.071274 | 0.182498 | 0.00992 | 0.081276 | 0.024414 | −0.025448 | 0.117278 |
| 214 | 0.035591 | 0.049689 | 0.002959 | −0.002113 | 0.008243 | 0.008031 | −0.075066 | −0.02216 | 0.013031 | 0.073533 | −0.022829 | 0.017549 | −0.054166 | 0.005599 |
| 215 | 0.011346 | 0.096203 | 0.014771 | 0.021064 | 0.028121 | −0.054934 | 0.069775 | 0.02846 | −0.054975 | 0.043878 | 0.073411 | 0.028208 | 0.030477 | −0.07355 |
| 216 | −0.014582 | −0.009828 | 0.015565 | 0.053693 | 0.017261 | −0.0498 | 0.059455 | 0.019325 | −0.035537 | 0.05973 | 0.009776 | 0.000538 | 0.00291 | 0.025432 |
| 217 | 0.008725 | 0.020651 | −0.000485 | 0.036891 | 0.013974 | −0.030802 | −0.041325 | 0.026357 | 0.066388 | −0.027512 | 0.016531 | −0.02136 | 0.01564 | 0.021901 |
| 218 | 0.031976 | −0.010729 | −0.017781 | −0.035912 | 0.049204 | 0.046804 | −0.001136 | −0.025575 | −0.010125 | −0.033446 | 0.014117 | 0.03025 | 0.072115 | −0.027207 |
| 219 | 0.022777 | −0.007889 | −0.014351 | −0.024469 | 0.067146 | 0.054699 | −0.056313 | 0.007564 | −0.030728 | 0.00244 | 0.055023 | −0.003824 | 0.068423 | −0.012074 |
| 220 | 0.09044 | −0.013615 | 0.009206 | 0.029432 | 0.043651 | 0.01251 | −0.002966 | −0.020382 | 0.06113 | −0.070827 | −0.04476 | −0.008848 | 0.025738 | 0.056362 |
| 221 | 0.042965 | 0.064789 | 0.026259 | −0.060193 | 0.012 | 0.000982 | −0.004742 | −0.042434 | 0.019865 | −0.018557 | 0.015259 | −0.007932 | 0.032536 | −0.029134 |
| 222 | 0.062301 | 0.027984 | 0.078306 | 0.027999 | −0.031426 | 0.029282 | −0.027069 | −0.003636 | −0.021885 | 0.009105 | 0.025461 | 0.059801 | 0.044497 | −0.020852 |
| 223 | 0.044659 | 0.016877 | 0.032361 | −0.035966 | 0.008687 | 0.055508 | −0.003909 | 0.000636 | 0.009395 | −0.032672 | 0.012561 | 0.000749 | 0.044522 | 0.036772 |
| 224 | −0.078248 | 0.053506 | 0.043066 | 0.04282 | 0.055852 | −0.037903 | 0.061619 | 0.016226 | 0.014089 | 0.139455 | −0.0196 | 0.080082 | −0.07173 | −0.017678 |
| 225 | −0.074271 | 0.042734 | 0.019589 | 0.035142 | 0.051339 | −0.06591 | 0.042492 | 0.036807 | −0.001172 | 0.121207 | −0.024739 | 0.069691 | −0.034163 | −0.010901 |
| 226 | −0.01102 | −0.014376 | 0.025369 | 0.021706 | −0.00043 | −0.00073 | −0.046024 | 0.018572 | 0.003369 | −0.070983 | 0.00152 | 0.027031 | 0.003412 | −0.05333 |
| 227 | −0.125749 | −0.017969 | 0.084005 | 0.085627 | 0.05598 | −0.00476 | 0.091558 | 0.006576 | 0.028188 | 0.038974 | −0.068267 | 0.085992 | −0.043128 | −0.094308 |
| 228 | 0.047839 | −0.01919 | −0.028351 | 0.020149 | −0.032058 | −0.012752 | −0.022278 | −0.006682 | −0.013655 | −0.032698 | −0.039111 | −0.022934 | 0.011118 | −0.00849 |
| 229 | 0.16117 | −0.01272 | −0.076569 | −0.075207 | −0.035023 | −0.026861 | −0.061754 | 0.071443 | −0.084104 | 0.009387 | −0.009732 | −0.031759 | −0.048964 | 0.078912 |
| 230 | 0.035847 | −0.045764 | 0.045671 | −0.010331 | −0.039634 | −0.043631 | 0.108597 | −0.003852 | −0.024044 | 0.079654 | −0.076987 | 0.02686 | −0.019022 | −0.001205 |
| 231 | −0.081758 | 0.016779 | 0.056988 | −0.01831 | −0.043754 | 0.025559 | 0.064244 | 0.033934 | 0.014282 | −0.1592621 | −0.014863 | −0.0486721 | −0.026261 | −0.031358 |
| 232 | 0.031074 | 0.020869 | 0.004372 | −0.01839 | −0.051392 | −0.054135 | −0.021944 | −0.046986 | −0.00587 | −0.005527 | 0.01492 | 0.051122 | 0.029331 | −0.07908 |
| 233 | 0.009788 | −0.071095 | −0.092238 | −0.075493 | −0.047263 | −0.070723 | 0.0411 | 0.003131 | 0.013826 | 0.029577 | 0.039062 | 0.05522 | 0.056367 | −0.047734 |
| 234 | −0.021969 | −0.067756 | −0.034878 | −0.052552 | −0.027107 | 0.018104 | 0.092254 | −0.006842 | −0.114192 | −0.06401 | −0.053484 | −0.076349 | 0.066492 | −0.01117 |
| 235 | −0.067686 | −0.035467 | 0.060973 | −0.051405 | −0.004426 | −0.000336 | 0.0714541 | 0.033945 | −0.034796 | −0.091561 | −0.018705 | −0.08407 | 0.066788 | −0.027859 |
| 236 | −0.028216 | 0.003589 | 0.059722 | −0.009621 | 0.007364 | 0.017655 | −0.011128 | −0.020093 | 0.032109 | −0.005342 | 0.003165 | −0.013112 | −0.004939 | 0.012529 |
| 237 | −0.060192 | −0.044528 | 0.017056 | −0.020319 | 0.01988 | 0.000154 | −0.019359 | −0.007701 | −0.045119 | 0.02591 | 0.008613 | −0.02557 | −0.038862 | −0.003825 |
| 238 | −0.01996 | −0.016038 | −0.0235 | −0.035383 | −0.035116 | 0.033401 | −0.011021 | 0.02575 | −0.007996 | 0.003956 | 0.052748 | −0.014173 | 0.01011 | −0.00564 |
| 239 | −0.018152 | 0.022049 | −0.07636 | −0.02507 | −0.03444f | 0.024353 | −0.006239 | 0.014649 | 0.012636 | −0.023154 | 0.078896 | 0.011432 | 0.060493 | −0.021426 |
| 240 | −0.04157 | −0.028323 | −0.060764 | 0.024853 | −0.011943 | 0.053135 | 0.004277 | 0.03124 | 0.007063 | 0.020896 | 0.006102 | −0.07142 | −0.001658 | −0.024353 |
| 241 | −0.026029 | −0.060539 | −0.106986 | −0.025002 | −0.03046 | −0.01141 | 0.008254 | −0.007232 | 0.008131 | 0.042999 | 0.039618 | −0.023754 | −0.000671 | −0.018897 |
| 242 | −0.011399 | 0.000012 | 0.040995 | −0.059831 | −0.015831 | −0.031588 | 0.035534 | −0.016853 | 0.04156 | −0.022802 | 0.024978 | −0.024135 | 0.014245 | 0.021159 |
| 243 | −0.066157 | 0.007011 | 0.002016 | −0.073932 | −0.025282 | −0.055274 | 0.003514 | 0.032053 | 0.01195 | −0.025547 | 0.035889 | −0.022618 | −0.009459 | −0.067829 |
| 244 | −0.043419 | 0.088514 | −0.016079 | −0.015588 | −0.030863 | −0.018363 | 0.040236 | −0.010259 | 0.032791 | 0.012918 | 0.02211 | −0.043116 | −0.016827 | −0.012007 |
| 245 | 0.008367 | 0.00649 | −0.00417 | 0.020875 | −0.019206 | −0.04128 | −0.006882 | 0.056465 | −0.046758 | 0.032253 | 0.083457 | −0.007006 | −0.017793 | 0.02441 |
| 246 | 0.089087 | −0.083417 | −0.002186 | 0.033545 | 0.046276 | −0.012815 | 0.028243 | −0.018264 | −0.073239 | 0.016374 | −0.011917 | 0.023762 | 0.0144 | 0.029579 |
| 247 | 0.046078 | −0.040553 | −0.01466 | 0.012522 | 0.036737 | 0.00172 | −0.000983 | −0.011044 | −0.001302 | 0.029987 | −0.032701 | −0.002175 | 0.045126 | −0.006173 |
| 248 | 0.037941 | 0.009286 | 0.001948 | 0.006607 | 0.028971 | 0.027355 | −0.017584 | 0.005148 | 0.03643 | −0.017333 | −0.024819 | 0.018161 | 0.053412 | −0.048581 |
| 249 | 0.015459 | −0.049071 | 0.024088 | 0.054002 | −0.01548 | 0.049514 | −0.038952 | 0.071913 | −0.002032 | −0.012367 | 0.021259 | 0.044088 | 0.015197 | 0.005589 |
| 250 | −0.019298 | −0.003269 | −0.055918 | 0.013775 | 0.023004 | 0.058822 | 0.0486 | −0.041809 | −0.017065 | −0.0015 | −0.033818 | −0.053888 | −0.028565 | 0.041859 |
| 251 | −0.075387 | −0.004733 | −0.049436 | −0.036391 | 0.029996 | 0.073417 | 0.041468 | −0.039634 | −0.018207 | −0.013607 | −0.016177 | −0.069309 | 0.003055 | −0.001467 |
| 252 | −0.070359 | 0.039029 | −0.110604 | −0.055033 | −0.031994 | −0.050113 | −0.004128 | −0.012482 | 0.012852 | −0.078663 | 0.039692 | −0.000139 | 0.021786 | −0.034382 |
| 253 | 0.021184 | 0.01903 | 0.010498 | 0.001943 | −0.050444 | −0.0543 | −0.0564 | 0.056052 | 0.001682 | −0.010255 | 0.014283 | −0.02024 | −0.023152 | 0.053279 |
| 254 | 0.000002 | −0.007243 | −0.01801 | −0.008058 | 0.03506 | 0.039865 | 0.013708 | 0.016974 | 0.018879 | −0.015951 | 0.029303 | −0.040652 | −0.034624 | 0.056454 |
| 255 | −0.005886 | −0.02339 | −0.001011 | 0.000519 | 0.02207 | −0.012042 | 0.050232 | −0.02823 | −0.001681 | −0.02868 | 0.000896 | −0.071125 | −0.044777 | 0.024004 |
| 256 | 0.078875 | −0.086426 | −0.043757 | 0.011536 | −0.014435 | −0.130742 | −0.020789 | 0.033501 | −0.061377 | −0.045493 | 0.047044 | 0.0291 | −0.049167 | 0.073631 |
| 257 | 0.030686 | 0.021639 | 0.028254 | 0.058429 | −0.017915 | −0.031237 | 0.010286 | −0.044848 | 0.018104 | 0.00604 | −0.001539 | 0.082401 | 0.05167 | 0.012485 |
| 258 | −0.057685 | 0.009558 | 0.067563 | 0.069297 | −0.042643 | −0.007424 | 0.021671 | 0.00098 | 0.00878 | 0.067895 | 0.011784 | 0.029792 | 0.048625 | −0.001858 |
| 259 | 0.014333 | −0.022778 | −0.004326 | 0.006941 | 0.003526 | 0.065195 | −0.018004 | −0.005268 | −0.011567 | −0.000054 | −0.007887 | 0.015271 | −0.016171 | 0.027176 |
| 260 | −0.008295 | 0.008541 | −0.150639 | −0.027962 | 0.034303 | 0.026376 | −0.040897 | −0.014622 | −0.015248 | −0.048202 | −0.080965 | −0.036064 | 0.012993 | 0.035715 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 261 | −0.025799 | −0.017672 | −0.114726 | −0.043982 | −0.005561 | 0.070464 | −0.030851 | 0.00441 | −0.024233 | −0.067021 | −0.067436 | −0.03576 | 0.030011 | −0.008713 |
| 262 | 0.024202 | 0.028639 | −0.020923 | 0.002497 | −0.030785 | 0.020572 | −0.00807 | −0.019501 | 0.018579 | −0.019353 | −0.03907 | 0.006603 | 0.047821 | −0.030336 |
| 263 | 0.013137 | 0.041145 | 0.009558 | 0.014831 | −0.026387 | 0.000235 | −0.011289 | −0.017477 | 0.04425 | −0.027301 | −0.022672 | 0.006921 | 0.042364 | −0.004039 |
| 264 | 0.023408 | −0.026245 | 0.047112 | 0.061625 | 0.025862 | 0.037403 | −0.054206 | 0.015941 | −0.015918 | 0.027315 | −0.034005 | 0.007911 | −0.074142 | −0.007258 |
| 265 | 0.049021 | −0.04494 | −0.064714 | 0.028522 | 0.062757 | 0.010136 | −0.082317 | 0.056257 | −0.023549 | 0.019543 | −0.050924 | 0.037138 | −0.066859 | 0.003675 |
| 266 | 0.04035 | −0.033595 | −0.103463 | −0.020882 | 0.030837 | 0.021152 | −0.044873 | 0.057316 | −0.019145 | −0.020707 | −0.011023 | −0.010908 | −0.065945 | 0.004251 |
| 267 | 0.031847 | −0.017551 | −0.07846 | 0.032487 | −0.02237 | −0.031101 | −0.060895 | 0.081395 | −0.048827 | −0.034666 | 0.021075 | 0.034116 | −0.032936 | 0.096687 |
| 268 | −0.017488 | −0.003926 | −0.005753 | 0.026653 | 0.011742 | −0.024263 | −0.026084 | 0.004005 | −0.001867 | −0.043414 | 0.021405 | 0.017564 | −0.002678 | −0.028572 |
| 269 | −0.016665 | 0.014498 | 0.021654 | 0.005507 | 0.022158 | −0.017174 | −0.028642 | 0.001058 | 0.012594 | −0.048891 | 0.001937 | 0.004814 | −0.028077 | −0.03123 |
| 270 | −0.050344 | 0.007107 | 0.017303 | 0.066184 | 0.034197 | 0.017558 | 0.020645 | −0.00775 | 0.041478 | −0.04045 | −0.057334 | 0.01768 | −0.00459 | −0.042104 |
| 271 | 0.064708 | 0.056418 | −0.053328 | 0.047585 | 0.054978 | 0.015118 | −0.063847 | 0.134049 | −0.0344 | 0.005764 | 0.025487 | −0.060192 | −0.077387 | 0.104362 |
| 272 | 0.134245 | 0.006814 | −0.068873 | −0.086625 | −0.028546 | 0.010031 | −0.090245 | 0.082444 | −0.059011 | −0.014068 | −0.009057 | −0.059728 | −0.02461 | 0.058132 |
| 273 | 0.061176 | 0.000835 | 0.00686 | −0.062385 | −0.001143 | −0.001251 | 0.016806 | −0.027139 | 0.047907 | 0.013895 | −0.076577 | 0.018099 | 0.038163 | −0.017528 |
| 274 | 0.059584 | 0.000561 | 0.011655 | −0.069314 | −0.000213 | 0.001682 | 0.014798 | −0.017629 | 0.056454 | 0.022599 | −0.093486 | 0.012302 | 0.01929 | −0.015258 |
| 275 | −0.002354 | −0.03966 | 0.079262 | 0.02551 | 0.027623 | 0.048894 | 0.11945 | −0.005776 | 0.057599 | 0.101738 | −0.146532 | 0.013777 | −0.003802 | −0.042516 |
| 276 | −0.016281 | 0.008634 | 0.027299 | −0.038081 | −0.019683 | 0.030983 | −0.026442 | −0.008804 | 0.007959 | −0.015832 | 0.01052 | −0.033497 | −0.015652 | 0.056298 |
| 277 | −0.063528 | 0.019214 | −0.015091 | −0.024665 | −0.010254 | 0.002154 | −0.017285 | −0.000361 | 0.008491 | 0.050847 | −0.013126 | 0.015903 | 0.026118 | −0.016684 |
| 278 | −0.059081 | 0.057914 | −0.026962 | −0.033937 | −0.02068 | 0.0257 | −0.001611 | −0.003006 | 0.017187 | 0.0391 | −0.044449 | 0.011343 | 0.012791 | −0.018308 |
| 279 | −0.02256 | 0.053272 | −0.066244 | −0.050455 | −0.027279 | 0.045526 | −0.018668 | 0.019024 | 0.023506 | −0.019638 | 0.030869 | −0.021893 | 0.026771 | −0.028342 |
| 280 | −0.044723 | 0.005296 | 0.067146 | −0.04481 | −0.047904 | −0.084172 | 0.023822 | 0.037922 | 0.007704 | 0.016021 | −0.021942 | 0.009227 | −0.064113 | 0.023139 |
| 281 | 0.067909 | −0.073633 | −0.002152 | 0.05112 | −0.022856 | 0.010909 | 0.024289 | 0.03229 | −0.052435 | −0.016929 | −0.051426 | 0.021742 | −0.03407 | 0.022729 |
| 282 | 0.03213 | −0.018637 | 0.007321 | 0.042009 | −0.038042 | 0.006063 | 0.085827 | 0.007681 | −0.026174 | −0.002677 | −0.077036 | 0.041371 | −0.029117 | 0.00766 |
| 283 | 0.037271 | −0.00352 | −0.034327 | −0.045189 | 0.033694 | 0.043499 | −0.016207 | 0.020388 | 0.056647 | −0.025493 | −0.087007 | −0.025418 | 0.00631 | −0.057435 |
| 284 | 0.019027 | 0.02303 | 0.024136 | 0.025787 | −0.011748 | −0.021535 | 0.006833 | −0.022208 | 0.016551 | 0.006397 | −0.023617 | 0.037134 | 0.015524 | 0.017041 |
| 285 | 0.007132 | 0.038204 | 0.00855 | 0.035097 | −0.009602 | −0.005318 | 0.031708 | −0.042987 | 0.020145 | 0.003226 | −0.026145 | 0.063519 | 0.021364 | 0.010408 |
| 286 | −0.089379 | 0.017901 | 0.050196 | 0.075612 | −0.074659 | −0.018887 | 0.035859 | 0.003184 | 0.016554 | 0.067672 | 0.033219 | 0.028082 | −0.012239 | 0.036091 |
| 287 | −0.092712 | 0.036229 | 0.048119 | 0.068151 | −0.071719 | −0.007193 | 0.038461 | −0.001531 | 0.02967 | 0.05372 | 0.015877 | 0.01321 | −0.010334 | 0.001574 |
| 288 | −0.033529 | 0.004827 | 0.094775 | 0.048889 | −0.034631 | 0.026489 | −0.003745 | −0.014011 | 0.007927 | 0.058158 | −0.050386 | −0.0120981 | −0.00621 | −0.00292 |
| 289 | 0.034241 | 0.023927 | −0.010786 | 0.038832 | −0.011135 | 0.011138 | 0.017792 | 0.000012 | 0.032235 | 0.018056 | −0.074673 | −0.004235 | 0.043913 | 0.000361 |
| 290 | −0.033648 | −0.058309 | 0.041841 | 0.035057 | −0.014177 | 0.01052 | −0.01385 | −0.015722 | −0.024932 | 0.032622 | 0.011719 | −0.056104 | 0.00841 | 0.005813 |
| 291 | −0.03575 | −0.058643 | 0.037967 | 0.038825 | −0.010999 | 0.016383 | −0.008033 | −0.011591 | −0.027644 | 0.033131 | 0.010776 | −0.051167 | 0.00468 | −0.000246 |
| 292 | −0.033133 | −0.065764 | 0.045847 | 0.03383 | −0.023349 | 0.022692 | −0.008884 | −0.027178 | −0.031385 | 0.015777 | 0.033888 | −0.062027 | −0.009905 | −0.007926 |
| 293 | 0.069537 | −0.063654 | 0.0371 | −0.029176 | 0.017603 | −0.032789 | −0.000103 | 0.026845 | −0.020817 | −0.044462 | 0.065075 | −0.043297 | −0.044301 | 0.00165 |
| 294 | 0.02121 | −0.042796 | −0.004757 | −0.013789 | −0.01156 | 0.017499 | 0.016201 | 0.00479 | −0.014486 | −0.035359 | −0.0194 | 0.003539 | −0.001079 | −0.058591 |
| 295 | 0.122685 | −0.035679 | −0.003333 | −0.10157 | 0.002643 | −0.040683 | 0.016314 | −0.001565 | 0.04226 | −0.014218 | −0.028851 | 0.003937 | −0.016737 | 0.015862 |
| 296 | 0.039419 | −0.070763 | 0.00222 | −0.071113 | 0.001987 | −0.025774 | −0.016056 | 0.011911 | 0.046788 | −0.001886 | −0.152219 | −0.016244 | 0.065904 | 0.029611 |
| 297 | 0.106112 | −4.03705 | −4.036498 | −4.077023 | −4.043844 | −4.024718 | −0.009473 | −4.016401 | 0.016819 | −4.047302 | −0.001448 | −4.025388 | −4.029116 | 0.038576 |
| 298 | −0.069656 | 0.020407 | −0.060303 | −0.079259 | −0.040872 | 0.062157 | −0.034297 | −0.069506 | −0.061563 | 0.02308 | −0.00562 | −0.059082 | 0.025502 | 0.073559 |
| 299 | 0.010414 | −0.017226 | −0.075192 | −0.057351 | −0.034708 | −0.003635 | −0.032303 | 0.039255 | −0.03086 | −0.072299 | 0.057222 | −0.053322 | −0.071919 | −0.038344 |
| 300 | −0.08266 | 0.034602 | −0.03058 | −0.028686 | −0.066112 | 0.088435 | 0.054536 | −0.029621 | 0.049508 | 0.034469 | −0.095107 | −0.091703 | 0.04288 | 0.041555 |
| 301 | 0.081016 | 0.015312 | −0.036711 | −0.045394 | 0.007269 | −0.019344 | −0.024548 | −0.011241 | −0.035209 | −0.043941 | 0.017086 | −0.013382 | −0.013472 | −0.026617 |
| 302 | 0.039566 | 0.01124 | −0.015339 | 0.027262 | 0.026465 | 0.031282 | 0.018835 | −0.003339 | 0.011664 | −0.009123 | −0.000643 | 0.015685 | 0.024271 | −0.024147 |
| 303 | −0.065506 | 0.050353 | −0.091079 | −0.048306 | −0.091554 | −0.002953 | −0.022127 | 0.01477 | −0.053168 | −0.035471 | 0.040166 | −0.080803 | −0.043308 | −0.088872 |
| 304 | −0.066893 | 0.024537 | −0.067621 | −0.044475 | −0.073966 | 0.049551 | −0.008229 | 0.037799 | −0.041747 | −0.025389 | 0.015522 | −0.064574 | −0.034655 | −0.069789 |
| 305 | 0.10155 | 0.028515 | −0.04155 | 0.000568 | 0.056154 | −0.021098 | 0.007458 | −0.057157 | −0.015531 | −0.044486 | −0.014128 | −0.015844 | −0.005917 | −0.015943 |
| 306 | −0.017168 | −0.039906 | 0.049418 | −0.017429 | 0.092018 | −0.062644 | −0.006871 | 0.064776 | −0.046313 | 0.082995 | −0.055487 | −0.095525 | 0.116844 | −0.070727 |
| 307 | −0.004033 | 0.017156 | 0.091365 | −0.103033 | −0.228199 | −0.022906 | 0.134609 | 0.217929 | 0.186869 | 0.035198 | 0.004067 | −0.104833 | −0.029988 | −0.016373 |
| 308 | 0.051726 | −0.040267 | −0.062116 | −0.057926 | −0.08923 | −0.22015 | 0.005869 | 0.04143 | 0.024513 | −0.017116 | 0.042204 | −0.025739 | 0.172383 | 0.139523 |
| 309 | −0.046459 | −0.031754 | 0.018997 | 0.029672 | 0.039362 | 0.00602 | 0.007193 | 0.014377 | 0.024336 | −0.048646 | 0.013497 | −0.017978 | −0.014476 | 0.017786 |
| 310 | −0.075384 | −0.022039 | 0.025614 | 0.040528 | 0.018163 | −0.0396 | 0.021619 | 0.097551 | −0.000889 | 0.054566 | −0.047253 | −0.064484 | −0.081628 | 0.016253 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 311 | −0.027687 | −0.025701 | −0.026439 | −0.048322 | −0.004357 | −0.007196 | −0.050403 | −0.039273 | 0.062653 | 0.023408 | 0.014983 | −0.048928 | 0.011646 | −0.00467 |
| 312 | 0.017971 | −0.05185 | 0.079647 | −0.039113 | −0.114165 | 0.029198 | −0.062863 | −0.042525 | −0.106762 | −0.018517 | 0.060076 | −0.048999 | 0.037955 | −0.077677 |
| 313 | −0.017253 | −0.016085 | −0.039262 | −0.000188 | 0.004647 | 0.013765 | −0.032368 | −0.035914 | 0.032586 | 0.040963 | −0.010997 | −0.022801 | 0.001176 | 0.040528 |
| 314 | 0.020031 | 0.021718 | −0.123363 | 0.090747 | −0.013442 | 0.149011 | 0.13851 | −0.057361 | 0.055731 | 0.00479 | 0.008757 | −0.180931 | −0.167537 | 0.016503 |
| 315 | −0.070615 | −0.007459 | −0.018954 | −0.009391 | −0.011478 | −0.02706 | 0.000094 | 0.005682 | 0.001049 | 0.000946 | 0.012639 | −0.061838 | −0.0562 | 0.017394 |
| 316 | 0.068494 | 0.055116 | −0.053771 | −0.03544 | 0.122713 | −0.041192 | −0.003437 | −0.098153 | −0.023317 | 0.08462 | −0.119903 | 0.016772 | −0.070061 | 0.014703 |
| 317 | −0.000122 | −0.013614 | −0.007285 | −0.000415 | 0.046863 | −0.004154 | −0.017285 | −0.013188 | 0.022492 | −0.030068 | −0.041474 | 0.00095 | −0.034522 | 0.027355 |
| 318 | 0.034643 | −0.005555 | 0.027812 | −0.076435 | −0.006717 | 0.016893 | 0.018996 | 0.001066 | 0.031784 | −0.005387 | 0.048361 | 0.024799 | −0.127676 | 0.056513 |
| 319 | −0.081434 | −0.005329 | 0.026689 | −0.041745 | −0.000718 | −0.033143 | 0.0044 | 0.02018 | −0.002857 | −0.014614 | 0.020385 | −0.033906 | −0.048937 | 0.004404 |
| 320 | −0.029332 | −0.098802 | 0.038034 | −0.061924 | 0.019185 | −0.037207 | −0.005568 | −0.051289 | −0.02825 | 0.044906 | 0.062673 | 0.083162 | 0.089285 | 0.001395 |
| 321 | −0.031639 | −0.032711 | −0.095623 | −0.010814 | −0.111546 | −0.04834 | 0.067527 | −0.058811 | 0.028543 | 0.006734 | −0.013005 | −0.006513 | −0.008586 | −0.030095 |
| 322 | −0.018558 | 0.065757 | −0.032113 | 0.04903 | −0.063521 | −0.066999 | 0.066234 | 0.007781 | −0.00169 | −0.149867 | −0.093872 | 0.019128 | −0.075052 | 0.075612 |
| 323 | −0.10804 | 0.036126 | −0.034246 | −0.035808 | −0.034206 | −0.023352 | 0.011177 | −0.115225 | −0.051545 | 0.080647 | 0.064701 | 0.004562 | −0.035529 | −0.009959 |
| 324 | 0.031298 | 0.005238 | −0.048066 | 0.066024 | 0.085698 | 0.121413 | 0.005359 | 0.088412 | 0.052561 | −0.01906 | −0.020158 | −0.054143 | −0.005964 | 0.000893 |
| 325 | −0.020137 | −0.03699 | 0.006869 | −0.003895 | 0.026561 | 0.004302 | −0.033502 | −0.004584 | −0.011807 | −0.056592 | −0.068679 | −0.045614 | 0.00722 | 0.00162 |
| 326 | −0.017513 | −0.021795 | 0.013476 | 0.105785 | 0.052872 | −0.02067 | −0.13097 | 0.034082 | 0.109929 | 0.021525 | 0.085316 | −0.029409 | 0.010603 | −0.04207 |
| 327 | −0.031227 | −0.017228 | −0.002817 | −0.061981 | 0.004147 | 0.0109961 | −0.00146 | −0.013299 | 0.006714 | 0.037583 | 0.01549 | −0.005506 | 0.005608 | −0.011818 |
| 328 | −0.055517 | −0.000028 | −0.012976 | 0.087902 | 0.021131 | −0.019679 | −0.105537 | −0.111522 | −0.028972 | −0.034505 | −0.123574 | 0.019071 | 0.236987 | 0.077935 |
| 329 | −0.045458 | 0.01865 | −0.0588 | 0.019314 | −0.009818 | 0.011117 | −0.053865 | −0.060569 | 0.004629 | 0.049677 | 0.059647 | 0.008915 | 0.031416 | −0.038061 |
| 330 | −0.138368 | 0.059537 | −0.096943 | −0.036088 | 0.042468 | −0.028202 | −0.035826 | −0.105446 | −0.099882 | −0.055458 | −0.002502 | 0.050099 | −0.0340821 | −0.069475 |
| 331 | −0.047042 | 0.006128 | −0.007896 | 0.011738 | −0.029868 | −0.025847 | −0.029223 | 0.012366 | −0.024605 | 0.045797 | 0.071751 | −0.070613 | −0.008289 | −0.037153 |
| 332 | −0.027121 | 0.022898 | −0.005193 | −0.034075 | 0.028361 | −0.127792 | −0.042045 | 0.027816 | 0.060052 | −0.05379 | −0.001843 | −0.02117 | 0.049951 | −0.05535 |
| 333 | −0.013165 | −0.000378 | 0.015987 | 0.012888 | 0.01773 | −0.020467 | 0.012848 | 0.007364 | −0.018286 | −0.007274 | 0.023766 | −0.006619 | −0.002595 | 0.017971 |
| 334 | −0.025154 | 0.034542 | −0.019027 | 0.013763 | 0.061693 | 0.085963 | 0.077064 | −0.010771 | −0.185227 | −0.097862 | 0.047947 | 0.018775 | 0.082007 | 0.064636 |
| 335 | −0.033466 | −0.033621 | 0.033798 | −0.025224 | 0.003 | 0.00569 | −0.006182 | 0.039759 | −0.020799 | 0.015059 | 0.058584 | −0.054859 | −0.010747 | −0.065597 |
| 336 | −0.0262 | −0.085204 | −0.073143 | 0.046459 | 0.02726 | −0.093092 | 0.033564 | −0.008085 | 0.008449 | 0.04916 | −0.018251 | −0.016853 | −0.036082 | −0.045793 |
| 337 | 0.029206 | −0.011629 | 0.009638 | −0.039086 | 0.062418 | −0.036245 | −0.061512 | 0.087015 | −0.133448 | −0.056328 | −0.038666 | −0.077751 | −0.078952 | 0.030219 |
| 338 | −0.099583 | 0.094521 | 0.045333 | −0.171412 | 0.047541 | −0.00815 | 0.008569 | 0.042561 | 0.057597 | 0.029685 | −0.042413 | −0.043698 | 0.068288 | −0.047529 |
| 339 | −0.051328 | 0.028733 | 0.029852 | −0.004748 | −0.041866 | −0.025941 | −0.076018 | −0.037329 | −0.014561 | 0.01133 | 0.097844 | −0.043315 | 0.023477 | 0.029147 |
| 340 | −0.081292 | 0.027889 | −0.050772 | −0.07073 | 0.135028 | −0.162046 | 0.00882 | 0.119116 | −0.04801 | −0.010333 | 0.014277 | 0.0486671 | −0.0188831 | −0.030871 |

| | AN | AO | AP | AQ | AR | AS | AT | AU | AV | AW | AX | AY | AZ | BA |
|---|---|---|---|---|---|---|---|---|---|---|---|---|---|---|
| 1 | −0.014117 | 0.007752 | −0.006572 | 0.023947 | 0.00987 | −0.00578 | 0.021539 | −0.047136 | −0.002522 | 0.019393 | −0.003808 | −0.030736 | 0.027639 | 0.030827 |
| 2 | 0.002377 | 0.007337 | 0.003252 | 0.01387 | −0.009573 | −0.023358 | 0.049448 | 0.005846 | 0.019571 | 0.043814 | 0.019208 | 0.005111 | −0.004766 | 0.009652 |
| 3 | −0.033576 | −0.005446 | 0.016466 | 0.02818 | −0.045699 | 0.05278 | 0.021933 | −0.051306 | 0.018177 | −0.011719 | 0.008568 | −0.059111 | 0.009881 | 0.004426 |
| 4 | −0.036764 | −0.001359 | 0.018777 | −0.05822 | 0.01423 | −0.081212 | −0.06017 | −0.066376 | −0.016736 | 0.025928 | 0.008029 | −0.050284 | 0.041454 | 0.016824 |
| 5 | −0.005499 | 0.077926 | −0.176658 | 0.037268 | −0.066731 | 0.009909 | 0.189314 | 0.084334 | −0.069425 | 0.091744 | −0.034335 | 0.089053 | −0.03969 | 0.003247 |
| 6 | −0.107433 | −0.043788 | 0.070389 | −0.035422 | −0.02826 | 0.061094 | −0.10537 | 0.115823 | −0.03025 | −0.042632 | 0.020849 | −0.118552 | 0.03146 | −0.046692 |
| 7 | −0.015299 | 0.038441 | −0.002508 | −0.02361 | −0.025156 | 0.018616 | −0.05077 | 0.027918 | 0.055279 | 0.02739 | −0.008421 | −0.037694 | 0.003546 | 0.065656 |
| 8 | 0.098996 | 0.038362 | 0.012476 | −0.025459 | −0.026189 | −0.054109 | 0.052944 | 0.131232 | 0.004385 | 0.068773 | 0.060385 | −0.124261 | −0.049085 | −0.010957 |
| 9 | 0.011029 | 0.089774 | −0.017078 | −0.041019 | 0.079464 | −0.105468 | 0.022335 | −0.020691 | 0.045022 | 0.138928 | −0.027367 | −0.061745 | −0.003394 | −0.123098 |
| 10 | −0.005002 | −0.000697 | 0.005099 | −0.034968 | −0.062704 | 0.096351 | −0.037712 | −0.010647 | −0.008017 | −0.022226 | −0.029527 | 0.041024 | −0.020542 | −0.023671 |
| 11 | 0.04049 | −0.003781 | 0.034242 | 0.01294 | −0.016067 | −0.06834 | 0.09381 | −0.063598 | 0.008705 | −0.061288 | 0.15743 | 0.197265 | 0.011232 | 0.021309 |
| 12 | −0.043547 | 0.127102 | −0.055687 | 0.03516 | −0.042325 | 0.036566 | −0.025904 | −0.161341 | 0.042394 | −0.135589 | −0.049677 | 0.025787 | 0.068426 | −0.027201 |
| 13 | −0.025549 | −0.028942 | −0.005999 | 0.055768 | 0.060001 | −0.074983 | 0.016649 | −0.064008 | −0.078015 | 0.010784 | 0.038137 | −0.026079 | 0.043772 | −0.001826 |
| 14 | −0.013814 | −0.105014 | −0.000278 | 0.032255 | 0.059566 | −0.053894 | 0.041138 | −0.027742 | −0.096934 | 0.011432 | −0.091533 | −0.114834 | 0.005255 | −0.151209 |
| 15 | −0.007823 | −0.001428 | 0.043445 | 0.033046 | 0.055421 | 0.001734 | 0.014552 | −0.049943 | −0.032379 | −0.027327 | 0.000654 | 0.01807 | 0.012382 | −0.048994 |
| 16 | −0.039201 | 0.128124 | 0.023731 | 0.151942 | −0.05885 | 0.015724 | 0.049679 | 0.097447 | −0.172525 | −0.009611 | 0.024587 | 0.066184 | −0.042693 | −0.001249 |
| 17 | −0.122702 | −0.04865 | 0.063796 | −0.017752 | −0.003941 | 0.079644 | −0.053084 | 0.028797 | −0.112106 | 0.016547 | −0.108213 | 0.115798 | 0.055533 | −0.090418 |

APPENDIX B3-continued

PCA Transformation Matrix (340 × 340 Early/Late)

| | | | | | | | | | | | | | | |
|---|---|---|---|---|---|---|---|---|---|---|---|---|---|---|
| 18 | 0.099075 | −0.03748 | −0.05908 | −0.012552 | 0.064555 | −0.027201 | 0.122584 | 0.16091 | −0.023917 | −0.013797 | −0.107761 | −0.047814 | −0.003685 | −0.077728 |
| 19 | −0.068431 | 0.004269 | 0.080388 | 0.016629 | 0.017525 | 0.024944 | 0.022496 | 0.017091 | −0.061615 | −0.101571 | 0.071088 | 0.049684 | −0.046038 | 0.028946 |
| 20 | −0.047059 | 0.002174 | −0.029327 | 0.006227 | −0.024544 | −0.036014 | 0.026787 | 0.032546 | −0.009807 | −0.05498 | −0.003445 | −0.001342 | 0.004799 | −0.021042 |
| 21 | −0.025706 | 0.036369 | −0.045817 | −0.133687 | 0.039283 | 0.047154 | −0.098922 | −0.03103 | −0.074953 | −0.006389 | −0.025751 | 0.049073 | 0.04477 | 0.067224 |
| 22 | −0.063932 | 0.092828 | 0.064715 | −0.041779 | −0.046527 | −0.080688 | −0.069272 | −0.031435 | 0.002461 | 0.043286 | 0.054983 | 0.00717 | −0.135256 | 0.017411 |
| 23 | −0.087425 | 0.056054 | 0.006438 | −0.01358 | 0.040164 | −0.0258 | −0.005376 | 0.032127 | −0.034526 | −0.048194 | 0.166876 | −0.040957 | 0.030422 | 0.02907 |
| 24 | −0.019529 | −0.046618 | −0.058528 | −0.034177 | −0.009447 | −0.021016 | 0.020661 | 0.023024 | 0.016166 | −0.008499 | 0.026879 | −0.110063 | −0.060484 | 0.008095 |
| 25 | 0.01453 | 0.01467 | −0.095024 | −0.066123 | 0.01611 | −0.076884 | 0.097747 | 0.024958 | −0.084721 | −0.00821 | −0.05391 | 0.039317 | −0.028881 | −0.075203 |
| 26 | −0.012354 | −0.005616 | −0.035528 | 0.012619 | −0.024406 | −0.018907 | 0.024176 | 0.014103 | −0.034738 | −0.044881 | −0.013605 | −0.0007121 | 0.016972 | 0.016286 |
| 27 | −0.016882 | −0.01721 | −0.013464 | −0.001753 | −0.014245 | −0.004358 | 0.007722 | 0.023278 | −0.021063 | −0.035279 | 0.019372 | 0.016868 | 0.048509 | −0.011385 |
| 28 | −0.038896 | 0.022348 | 0.019024 | −0.035709 | −0.026243 | 0.03568 | −0.076895 | −0.103412 | −0.068021 | 0.064417 | −0.047647 | −0.03937 | 0.024884 | 0.066895 |
| 29 | 0.114037 | −0.022704 | 0.047054 | 0.014093 | −0.062746 | 0.077753 | −0.056839 | −0.074384 | 0.064692 | 0.104592 | −0.008537 | −0.096202 | 0.19324 | 0.048395 |
| 30 | 0.077007 | 0.008445 | −0.011048 | −0.003123 | 0.098774 | 0.054067 | −0.026078 | 0.004593 | 0.01689 | −0.004345 | 0.008982 | 0.024847 | −0.013344 | −0.104054 |
| 31 | 0.050648 | −0.033371 | −0.038472 | −0.013359 | 0.050555 | 0.044863 | 0.019605 | −0.003046 | −0.030302 | 0.030363 | 0.009442 | 0.050565 | −0.061103 | −0.074768 |
| 32 | −0.056602 | −0.061444 | 0.020308 | −0.004279 | −0.010178 | 0.038663 | −0.012594 | −0.0148 | 0.063107 | −0.018121 | 0.007825 | 0.00622 | −0.128485 | −0.012435 |
| 33 | 0.100642 | −0.003802 | 0.014595 | −0.021352 | 0.136386 | 0.008814 | 0.055898 | 0.004472 | −0.04648 | 0.045159 | 0.015238 | −0.024237 | 0.001622 | 0.005631 |
| 34 | 0.02719 | −0.005045 | −0.012874 | 0.036114 | 0.010011 | −0.032662 | −0.032537 | −0.035667 | −0.009766 | 0.053387 | 0.043774 | 0.059432 | −0.037634 | 0.023665 |
| 35 | 0.033942 | −0.007913 | 0.071286 | −0.019862 | −0.01909 | −0.043243 | 0.037109 | 0.001358 | 0.002488 | −0.003486 | 0.117391 | −0.153038 | −0.060973 | −0.039413 |
| 36 | −0.028865 | −0.011249 | −0.055464 | −0.034728 | −0.0475 | 0.048814 | 0.015514 | 0.093215 | −0.051203 | 0.002568 | 0.110894 | −0.040465 | −0.011775 | 0.07186 |
| 37 | 0.008672 | −0.057886 | −0.004879 | 0.038366 | −0.04292 | 0.101581 | 0.074651 | 0.087904 | −0.004656 | 0.084264 | 0.006183 | 0.026336 | 0.050252 | −0.021765 |
| 38 | −0.022409 | 0.046538 | 0.020795 | −0.04734 | 0.112211 | −0.083387 | 0.062397 | 0.084953 | −0.027341 | −0.068901 | 0.110054 | 0.029342 | −0.016969 | 0.163455 |
| 39 | −0.03147 | 0.080146 | −0.038954 | −0.032551 | 0.014752 | −0.005122 | 0.043399 | 0.039886 | 0.061617 | −0.045861 | 0.003226 | −0.02982 | −0.008112 | −0.005138 |
| 40 | 0.043378 | −0.005801 | −0.048502 | 0.039247 | 0.017084 | 0.000518 | 0.014687 | −0.017587 | 0.035948 | 0.028959 | −0.044362 | 0.000443 | 0.039251 | 0.004531 |
| 41 | 0.022673 | 0.007481 | −0.03168 | 0.029539 | −0.027864 | 0.010091 | −0.004083 | 0.002202 | 0.030323 | 0.027064 | −0.029065 | −0.004903 | 0.047017 | 0.038335 |
| 42 | 0.026107 | 0.073244 | −0.040797 | 0.037064 | 0.017162 | −0.024957 | −0.012929 | 0.013663 | 0.03945 | −0.003743 | −0.007672 | 0.0016 | 0.030265 | 0.040842 |
| 43 | 0.032392 | −0.015738 | −0.03679 | 0.043681 | 0.005256 | 0.002191 | 0.015936 | −0.022213 | 0.020754 | 0.042253 | −0.029069 | −0.013404 | 0.029567 | 0.047268 |
| 44 | 0.062372 | 0.025752 | 0.031194 | 0.044223 | −0.02735 | −0.001177 | −0.052481 | −0.04507 | −0.025461 | 0.054624 | 0.018987 | −0.014624 | −0.04389 | −0.034617 |
| 45 | −0.01496 | −0.044921 | 0.012583 | −0.002551 | −0.023693 | 0.049179 | −0.005552 | −0.07229 | 0.025504 | 0.03682 | −0.009854 | −0.032758 | −0.048956 | −0.025047 |
| 46 | −0.054713 | −0.066459 | 0.092598 | −0.004601 | 0.03479 | −0.036758 | −0.057793 | 0.003944 | −0.076798 | 0.021849 | 0.053204 | −0.06627 | 0.042342 | −0.076507 |
| 47 | 0.021317 | −0.028094 | 0.029031 | 0.021682 | −0.086777 | 0.020861 | −0.032386 | −0.020667 | −0.068773 | 0.012899 | 0.013868 | 0.006717 | 0.011205 | −0.061487 |
| 48 | −0.065129 | −0.035578 | −0.026862 | −0.011747 | −0.012335 | 0.032588 | 0.0881 | 0.102899 | 0.197046 | 0.071225 | 0.018307 | 0.007638 | 0.065319 | 0.087431 |
| 49 | 0.035271 | 0.032757 | 0.014723 | −0.013179 | 0.072794 | 0.03921 | −0.041715 | 0.014727 | 0.006321 | −0.04615 | 0.005753 | 0.082751 | 0.002214 | −0.104915 |
| 50 | −0.00715 | −0.019596 | 0.039818 | 0.018128 | 0.005186 | 0.014465 | −0.023339 | 0.026574 | −0.050068 | 0.011997 | −0.010979 | −0.018397 | 0.018863 | −0.043889 |
| 51 | −0.022079 | −0.018614 | −0.046252 | −0.09678 | 0.067869 | 0.002742 | 0.006437 | 0.05268 | −0.039761 | 0.024795 | 0.026293 | 0.046407 | −0.01347 | −0.022236 |
| 52 | 0.033307 | −0.045998 | −0.049537 | −0.078807 | −0.004213 | −0.047073 | −0.023778 | 0.016813 | 0.030186 | −0.006013 | 0.023222 | 0.047576 | 0.013299 | −0.058921 |
| 53 | −0.054468 | 0.001336 | 0.051242 | −0.012483 | 0.012265 | 0.031338 | 0.031793 | 0.02173 | −0.008462 | 0.026116 | 0.022139 | 0.003075 | −0.031417 | 0.013962 |
| 54 | 0.045602 | 0.018634 | 0.004519 | 0.006306 | 0.023887 | −0.033654 | −0.016358 | 0.051898 | −0.023541 | −0.017595 | −0.01588 | −0.055493 | −0.024524 | 0.047705 |
| 55 | −0.063255 | −0.00902 | −0.022839 | −0.038353 | 0.014921 | −0.014152 | −0.016359 | −0.038413 | −0.018424 | 0.017924 | 0.035563 | 0.008371 | −0.024589 | −0.00352 |
| 56 | 0.009322 | −0.053747 | −0.019811 | 0.031006 | 0.042154 | 0.010264 | 0.025944 | 0.004508 | −0.037354 | 0.010031 | 0.027176 | 0.028022 | −0.047492 | −0.050194 |
| 57 | 0.058013 | 0.027539 | −0.016822 | 0.00087 | 0.061266 | 0.00462 | −0.007924 | 0.004275 | 0.002408 | −0.040959 | −0.01866 | 0.002233 | 0.089897 | 0.010878 |
| 58 | −0.000289 | 0.013522 | −0.072558 | −0.064959 | −0.07227 | 0.041716 | −0.003279 | 0.079515 | −0.039736 | 0.015328 | −0.020033 | −0.044043 | −0.0229 | 0.018386 |
| 59 | 0.038771 | 0.03613 | 0.012436 | 0.046829 | −0.035347 | 0.064911 | −0.148728 | −0.012003 | −0.02315 | −0.053999 | 0.052819 | 0.092493 | 0.034399 | −0.062578 |
| 60 | 0.014035 | −0.021756 | −0.054823 | −0.026272 | −0.113699 | −0.073805 | 0.02092 | −0.027398 | 0.014024 | 0.013083 | 0.060361 | −0.027357 | −0.055124 | −0.005487 |
| 61 | 0.037648 | −0.025058 | −0.054003 | −0.057778 | −0.05772 | −0.004056 | 0.01551 | −0.002473 | 0.027866 | −0.000386 | −0.002409 | −0.025582 | −0.018945 | 0.093029 |
| 62 | 0.026201 | 0.058996 | 0.046378 | 0.047705 | −0.071467 | 0.071924 | −0.019838 | −0.069446 | −0.062712 | 0.024472 | 0.050313 | −0.084803 | −0.028209 | −0.02705 |
| 63 | 0.041541 | 0.007951 | 0.014761 | 0.003657 | −0.032639 | 0.007645 | 0.037051 | −0.003313 | −0.025081 | 0.016879 | −0.004479 | 0.043117 | −0.003709 | 0.128031 |
| 64 | 0.048816 | −0.002406 | −0.046817 | 0.009219 | 0.081482 | 0.05649 | 0.008304 | 0.027085 | −0.026121 | −0.076795 | −0.034328 | 0.016276 | −0.036553 | −0.097112 |
| 65 | 0.025643 | 0.051016 | −0.036985 | −0.006825 | −0.03642 | −0.037582 | −0.008828 | −0.024931 | 0.023996 | −0.010892 | −0.004618 | 0.012194 | 0.04361 | 0.021293 |
| 66 | 0.069682 | −0.065442 | −0.041615 | 0.017246 | −0.009659 | −0.101978 | 0.006736 | 0.033284 | 0.030918 | −0.025146 | 0.095328 | 0.082279 | −0.068089 | 0.028658 |
| 67 | 0.018548 | 0.025502 | −0.014932 | −0.01849 | −0.012215 | −0.089723 | 0.039065 | −0.002724 | −0.103578 | 0.031301 | −0.018945 | 0.014459 | −0.065319 | 0.058106 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 68 | −0.06576 | 0.052773 | −0.079751 | −0.070445 | −0.066638 | −0.129149 | 0.011312 | −0.121454 | −0.040682 | −0.047306 | −0.017299 | −0.067787 | 0.087764 | 0.049225 |
| 69 | −0.053746 | 0.01283 | 0.071903 | 0.004703 | −0.040779 | 0.026894 | −0.038032 | −0.012532 | −0.003212 | −0.051984 | −0.107124 | 0.013355 | −0.023852 | −0.017221 |
| 70 | 0.09708 | 0.026946 | 0.006158 | −0.056557 | −0.073984 | 0.022016 | −0.022446 | −0.050296 | 0.058944 | −0.000086 | 0.072489 | 0.00125 | −0.036764 | 0.072824 |
| 71 | 0.059204 | −0.021909 | 0.009682 | 0.012733 | −0.018051 | 0.025076 | 0.006608 | −0.006926 | 0.060682 | −0.047891 | −0.052086 | 0.039693 | 0.021469 | −0.006802 |
| 72 | −0.035867 | 0.013655 | 0.082526 | −0.005752 | −0.007058 | 0.005503 | −0.057229 | −0.054842 | −0.004417 | −0.008797 | −0.047691 | 0.014646 | −0.021224 | −0.032596 |
| 73 | 0.032975 | 0.016266 | 0.002703 | 0.084233 | 0.062955 | −0.032512 | −0.013784 | −0.022809 | 0.07547 | 0.081423 | 0.062033 | −0.067176 | −0.14061 | 0.116098 |
| 74 | 0.040299 | 0.006786 | −0.03874 | −0.012099 | −0.043051 | 0.052258 | 0.037369 | −0.055506 | −0.037068 | 0.035504 | 0.027121 | 0.103141 | −0.001282 | −0.048028 |
| 75 | 0.046893 | −0.006423 | 0.01138 | −0.0396 | 0.006848 | 0.014351 | 0.028991 | −0.02276 | 0.006115 | 0.016586 | 0.016236 | 0.020456 | −0.002651 | 0.053323 |
| 76 | 0.067133 | −0.008884 | −0.003793 | −0.04577 | −0.048593 | 0.0114 | −0.025172 | 0.016475 | 0.010563 | 0.039353 | −0.066295 | 0.070873 | −0.021313 | 0.034346 |
| 77 | 0.048011 | 0.002467 | 0.031209 | −0.039213 | −0.022235 | 0.031043 | 0.02997 | −0.007872 | 0.049492 | 0.000583 | 0.006509 | 0.037245 | 0.012801 | 0.067565 |
| 78 | 0.037737 | 0.023584 | 0.001971 | −0.064158 | −0.001952 | 0.043014 | 0.050525 | 0.012439 | 0.040676 | −0.000596 | 0.040763 | 0.036642 | −0.015246 | 0.089561 |
| 79 | 0.086355 | −0.031587 | −0.048054 | 0.028676 | 0.054809 | −0.018976 | −0.019255 | −0.000904 | −0.040558 | 0.019602 | 0.026206 | 0.011528 | 0.013074 | −0.037757 |
| 80 | 0.138599 | −0.069991 | −0.097642 | −0.045903 | −0.013121 | 0.000402 | 0.009527 | 0.025152 | −0.030928 | −0.075791 | −0.063127 | 0.017374 | −0.023063 | 0.02556 |
| 81 | −0.076935 | 0.123602 | 0.025469 | −0.002573 | −0.097404 | −0.011784 | 0.081378 | 0.028951 | 0.009971 | 0.156562 | −0.046897 | −0.005086 | 0.049816 | −0.041775 |
| 82 | −0.018233 | −0.02089 | −0.016293 | −0.041239 | 0.032753 | −0.05967 | −0.041462 | −0.050299 | 0.017154 | −0.001307 | −0.005432 | −0.012365 | 0.040025 | −0.01784 |
| 83 | −0.017099 | −0.021793 | −0.011121 | −0.047258 | 0.005272 | −0.020491 | −0.014238 | −0.019847 | −0.025251 | −0.053642 | 0.028124 | 0.003104 | 0.051171 | 0.00442 |
| 84 | 0.019748 | 0.01142 | 0.006897 | 0.014059 | −0.019937 | −0.003684 | −0.034934 | 0.053591 | 0.029733 | −0.024849 | 0.013926 | −0.044006 | 0.044025 | 0.003173 |
| 85 | 0.069947 | 0.092118 | 0.032499 | −0.00426 | 0.151415 | −0.026443 | 0.052398 | 0.033685 | −0.072028 | 0.132535 | −0.011236 | 0.0457 | 0.066897 | −0.114668 |
| 86 | 0.027275 | −0.058951 | −0.010599 | 0.031589 | 0.015553 | 0.069909 | 0.027561 | −0.02328 | 0.040197 | −0.056233 | 0.015594 | 0.010029 | −0.028097 | −0.006214 |
| 87 | 0.07456 | −0.043055 | −0.065574 | −0.005782 | −0.036501 | 0.041847 | 0.015655 | −0.013094 | −0.130772 | −0.029644 | −0.01587 | −0.06172 | −0.087351 | −0.048009 |
| 88 | −0.04711 | −0.016818 | −0.006283 | −0.010258 | −0.011359 | −0.00937 | 0.029719 | 0.056958 | −0.005751 | −0.027052 | 0.028713 | −0.012375 | 0.051698 | −0.025068 |
| 89 | −0.034303 | 0.004904 | −0.025551 | −0.031551 | −0.011003 | −0.015798 | −0.00708 | 0.016029 | −0.026897 | −0.075536 | 0.013386 | −0.001351 | 0.01975 | −0.012771 |
| 90 | −0.033213 | −0.003315 | −0.047474 | −0.021452 | −0.036536 | −0.015135 | −0.017833 | 0.000121 | −0.060094 | −0.058787 | −0.02699 | 0.0187 | −0.035289 | 0.00543 |
| 91 | −0.010062 | 0.005503 | 0.003071 | −0.000348 | 0.064329 | −0.001768 | −0.014593 | −0.004639 | 0.049667 | −0.034649 | −0.002461 | 0.007171 | −0.014772 | −0.035577 |
| 92 | −0.100051 | 0.181535 | −0.009143 | 0.004324 | 0.067348 | −0.028942 | 0.070985 | 0.019251 | 0.176152 | −0.00405 | −0.024783 | −0.058772 | 0.002129 | 0.055124 |
| 93 | 0.04609 | −0.003307 | 0.010215 | −0.05661 | −0.005062 | −0.039892 | −0.055988 | 0.054698 | −0.001281 | −0.028305 | 0.021939 | 0.035463 | 0.011708 | 0.078147 |
| 94 | −0.050352 | 0.075252 | 0.016917 | 0.069639 | −0.005944 | 0.005287 | −0.004699 | −0.031795 | 0.082331 | 0.051575 | 0.082298 | 0.040513 | −0.007907 | 0.070938 |
| 95 | −0.034063 | −0.012985 | −0.056163 | 0.066541 | −0.085017 | −0.08202 | −0.084088 | −0.122316 | −0.086976 | 0.030899 | −0.004701 | −0.126695 | −0.086519 | −0.038142 |
| 96 | 0.134995 | −0.119093 | 0.010678 | 0.00794 | −0.072751 | −0.029328 | 0.073703 | −0.001977 | 0.065213 | 0.122401 | −0.018044 | 0.04618 | 0.033108 | −0.03865 |
| 97 | 0.025582 | 0.027579 | −0.052308 | −0.005155 | 0.011535 | −0.049288 | −0.020257 | −0.009947 | −0.024812 | 0.023219 | 0.008254 | 0.037985 | −0.041218 | 0.0683 |
| 98 | −0.040958 | 0.003861 | 0.000666 | −0.000476 | 0.021967 | 0.023772 | −0.006852 | 0.006727 | 0.003463 | 0.021126 | −0.031108 | −0.040381 | −0.03685 | −0.023532 |
| 99 | −0.025285 | 0.012743 | −0.005316 | −0.022996 | −0.001671 | −0.015421 | 0.00704 | −0.029901 | 0.014305 | 0.04032 | −0.047565 | 0.035668 | 0.028336 | −0.002697 |
| 100 | −0.002027 | 0.026707 | −0.008619 | −0.028228 | 0.009776 | 0.048948 | −0.038167 | −0.029571 | −0.080747 | 0.053466 | −0.004443 | −0.021817 | 0.033936 | 0.036873 |
| 101 | 0.009676 | 0.062607 | −0.018925 | −0.017839 | −0.019561 | 0.000524 | −0.029993 | 0.05478 | 0.028577 | 0.012788 | 0.015427 | 0.000148 | −0.057288 | −0.026665 |
| 102 | 0.080638 | −0.002717 | 0.008621 | 0.056816 | −0.044009 | 0.071272 | −0.018736 | −0.048209 | −0.035777 | 0.132124 | 0.000234 | −0.026543 | −0.0219 | 0.072628 |
| 103 | −0.118366 | 0.112766 | −0.048945 | 0.077307 | −0.026898 | 0.069615 | −0.021391 | −0.041857 | −0.103115 | −0.077866 | 0.149287 | −0.026824 | 0.019986 | −0.008897 |
| 104 | 0.041942 | 0.032961 | −0.034071 | −0.028835 | −0.06116 | 0.062907 | −0.021644 | 0.062072 | −0.031461 | 0.060102 | −0.016602 | 0.011433 | −0.07173 | −0.005902 |
| 105 | 0.023221 | 0.083141 | 0.073602 | −0.1666 | −0.05863 | 0.072414 | 0.105129 | 0.0748 | −0.00037 | 0.063146 | 0.050966 | −0.121313 | 0.056705 | −0.078493 |
| 106 | 0.01302 | −0.132337 | −0.023274 | 0.147338 | 0.113253 | 0.108165 | −0.001251 | 0.02008 | 0.033226 | −0.019401 | 0.092932 | 0.038621 | 0.01972 | 0.085715 |
| 107 | −0.042854 | −0.005738 | −0.040768 | −0.006352 | −0.02426 | −0.073658 | 0.004564 | 0.073965 | 0.03152 | 0.015525 | −0.020833 | 0.114812 | 0.027316 | 0.155148 |
| 108 | 0.117503 | −0.033945 | −0.066172 | −0.010022 | 0.016256 | −0.0026 | −0.097185 | 0.007639 | 0.029767 | −0.019763 | −0.057007 | −0.042183 | 0.111257 | −0.079122 |
| 109 | −0.043971 | 0.057544 | 0.107811 | −0.034371 | 0.004157 | 0.113567 | 0.029986 | −0.087485 | 0.056825 | 0.154945 | −0.156762 | 0.009265 | −0.113444 | −0.050572 |
| 110 | 0.016564 | −0.004332 | −0.080524 | 0.00933 | 0.177381 | −0.132897 | −0.023625 | −0.026601 | 0.151548 | −0.03764 | 0.043292 | −0.022369 | 0.101458 | 0.034173 |
| 111 | 0.108488 | −0.025363 | −0.078003 | 0.116008 | 0.038875 | −0.094512 | −0.033632 | −0.109566 | 0.057522 | 0.024399 | 0.006632 | −0.131197 | −0.033651 | −0.069757 |
| 112 | −0.01983 | −0.068945 | 0.122268 | 0.104566 | −0.122782 | 0.082789 | −0.025059 | 0.171502 | −0.008814 | −0.064052 | 0.012645 | −0.04364 | 0.095091 | 0.055005 |
| 113 | −0.074178 | −0.012111 | −0.057619 | 0.067012 | 0.082461 | −0.011926 | −0.010139 | −0.07417 | 0.155922 | 0.082929 | −0.056731 | −0.022547 | −0.073246 | 0.017728 |
| 114 | −0.111157 | −0.070185 | −0.035995 | −0.164662 | 0.045486 | 0.156554 | 0.069133 | −0.028918 | 0.048679 | 0.077467 | −0.02355 | 0.256715 | 0.041627 | −0.067241 |
| 115 | 0.047208 | 0.093722 | −0.048582 | −0.066623 | −0.001916 | 0.023985 | −0.068866 | 0.037725 | 0.088556 | 0.019265 | 0.135375 | −0.023578 | −0.004646 | −0.047251 |
| 116 | −0.029623 | −0.072081 | 0.040129 | 0.003344 | −0.009327 | −0.13048 | −0.045229 | −0.083769 | −0.098187 | −0.008205 | −0.02988 | −0.058227 | 0.026582 | 0.062291 |
| 117 | 0.011853 | −0.048559 | 0.001262 | 0.160365 | −0.045591 | −0.014024 | −0.116047 | 0.041739 | 0.028684 | 0.066031 | 0.014853 | 0.020861 | −0.010002 | −0.054045 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 118 | 0.138824 | 0.090886 | −0.00655 | −0.035025 | −0.063968 | −0.039899 | −0.133943 | −0.084309 | −0.06607 | 0.003963 | −0.079655 | 0.036036 | −0.065236 | −0.074274 |
| 119 | −0.047368 | −0.0222 | −0.018613 | 0.070801 | −0.015285 | −0.024693 | −0.080338 | 0.051682 | −0.006366 | −0.037295 | −0.048965 | 0.031711 | −0.045121 | 0.033102 |
| 120 | 0.010268 | −0.018939 | −0.051364 | 0.141201 | 0.081905 | −0.027514 | −0.087327 | 0.018115 | −0.021414 | −0.057515 | 0.02749 | 0.03273 | −0.013183 | −0.060997 |
| 121 | −0.091084 | −0.036635 | 0.089558 | 0.027524 | 0.075059 | 0.087592 | 0.051228 | −0.193238 | −0.035038 | −0.06689 | 0.121929 | 0.031271 | 0.072733 | 0.011526 |
| 122 | 0.02507 | −0.013879 | 0.009868 | −0.060553 | −0.027147 | 0.024218 | −0.070103 | 0.048506 | 0.072039 | 0.037259 | 0.046818 | −0.076421 | 0.029444 | 0.018566 |
| 123 | 0.001815 | 0.052393 | −0.05176 | −0.062447 | 0.021891 | −0.03353 | −0.058086 | 0.023038 | 0.049542 | −0.011242 | 0.070309 | −0.029807 | 0.029122 | 0.014821 |
| 124 | −0.048939 | 0.008927 | −0.048446 | 0.07318 | −0.049324 | 0.000325 | −0.04754 | 0.088558 | −0.033168 | −0.034146 | −0.007592 | −0.017034 | 0.00154 | 0.086112 |
| 125 | 0.039641 | 0.014458 | 0.019826 | −0.000798 | 0.006966 | −0.025917 | 0.103764 | 0.062826 | 0.00339 | −0.060766 | −0.106049 | −0.055297 | −0.0052 | −0.101025 |
| 126 | −0.010575 | 0.036203 | 0.028901 | −0.000207 | −0.018696 | 0.018154 | 0.000039 | −0.100056 | 0.055992 | −0.013487 | −0.025696 | 0.017385 | −0.05264 | 0.023584 |
| 127 | −0.030779 | 0.031922 | −0.011511 | −0.002209 | −0.024482 | 0.005006 | 0.045703 | −0.015855 | 0.045717 | −0.037904 | −0.055756 | 0.001211 | −0.024273 | 0.052989 |
| 128 | 0.047278 | −0.040304 | 0.029458 | −0.082721 | 0.011097 | −0.030798 | 0.028265 | −0.04221 | 0.008594 | 0.019747 | 0.01226 | 0.014222 | −0.004816 | 0.049781 |
| 129 | 0.064936 | 0.087827 | 0.069292 | 0.083861 | 0.109224 | 0.01194 | 0.107547 | 0.034047 | 0.043321 | 0.006101 | 0.043949 | −0.062143 | 0.070731 | −0.093597 |
| 130 | −0.001971 | 0.022106 | 0.03408 | −0.040006 | 0.033953 | 0.042525 | 0.026094 | −0.025465 | 0.01477 | −0.022266 | 0.115767 | −0.04825 | −0.013335 | 0.096224 |
| 131 | −0.030078 | 0.078007 | −0.013558 | −0.061839 | 0.059293 | −0.154739 | −0.065168 | 0.062509 | −0.121718 | 0.011887 | 0.036878 | −0.048514 | 0.030829 | 0.066924 |
| 132 | 0.008309 | −0.008713 | 0.020222 | −0.010168 | 0.084192 | −0.059892 | −0.112766 | 0.032342 | 0.008714 | −0.069046 | −0.019295 | −0.024633 | −0.011356 | −0.021238 |
| 133 | −0.033415 | 0.025563 | −0.023223 | 0.085492 | 0.057017 | 0.000968 | −0.021692 | −0.073153 | −0.070369 | 0.100529 | −0.041546 | −0.000051 | 0.005014 | 0.028749 |
| 134 | −0.09229 | 0.111913 | 0.007177 | −0.095609 | −0.132709 | −0.066032 | 0.065594 | 0.046864 | −0.025854 | −0.02192 | 0.011179 | 0.000467 | −0.113122 | 0.017195 |
| 135 | 0.014966 | −0.070493 | −0.010848 | 0.026226 | −0.005218 | 0.045342 | 0.011901 | 0.030036 | −0.030962 | −0.021601 | −0.046745 | 0.043956 | −0.053027 | 0.005837 |
| 136 | −0.036015 | 0.011947 | −0.116051 | −0.004978 | 0.148834 | −0.062333 | −0.01802 | −0.095606 | 0.01146 | 0.079659 | −0.042967 | −0.071473 | −0.035019 | −0.022603 |
| 137 | −0.000282 | 0.058481 | 0.027914 | −0.047089 | 0.010351 | 0.018228 | 0.007634 | 0.018455 | −0.076891 | −0.019217 | 0.058467 | 0.010887 | −0.029426 | 0.063348 |
| 138 | −0.016717 | −0.094571 | 0.111382 | −0.031061 | 0.016328 | −0.095737 | 0.01776 | −0.049935 | 0.019863 | −0.1702 | −0.071703 | 0.021837 | −0.025956 | 0.096946 |
| 139 | 0.097221 | 0.044594 | −0.031597 | −0.010355 | 0.03256 | 0.017988 | −0.154701 | −0.087248 | 0.18508 | 0.076865 | 0.024929 | 0.072578 | 0.118053 | 0.054487 |
| 140 | 0.064214 | −0.107846 | 0.191676 | −0.057318 | 0.1468 | −0.008023 | −0.10163 | 0.083135 | 0.073055 | 0.032165 | 0.007639 | −0.07117 | −0.025713 | 0.051026 |
| 141 | −0.013549 | −0.064111 | 0.06598 | −0.052903 | −0.048981 | −0.033009 | 0.018863 | −0.048939 | −0.001393 | −0.036347 | 0.064441 | −0.022844 | 0.06369 | 0.018393 |
| 142 | 0.011506 | −0.004683 | −0.027774 | 0.024656 | 0.050504 | 0.067969 | −0.011594 | 0.004117 | 0.002254 | 0.029533 | 0.117695 | 0.005346 | −0.003141 | −0.017588 |
| 143 | 0.004562 | −0.03724 | −0.018449 | −0.128223 | −0.004375 | 0.062738 | −0.011145 | 0.142228 | 0.051895 | 0.10032 | 0.012263 | −0.024625 | 0.062059 | 0.010066 |
| 144 | −0.078245 | −0.12977 | −0.102084 | 0.00777 | −0.039511 | −0.029634 | −0.033619 | −0.007778 | −0.000976 | −0.006191 | 0.032496 | −0.008698 | −0.058621 | 0.016042 |
| 145 | −0.043894 | 0.030338 | −0.093302 | −0.057716 | 0.040299 | 0.006334 | −0.073818 | −0.088748 | 0.099668 | 0.059834 | −0.057672 | 0.0411 | −0.216294 | −0.004649 |
| 146 | 0.021066 | −0.060625 | −0.006149 | 0.066137 | 0.069999 | −0.046321 | 0.005549 | 0.009534 | −0.064175 | −0.008943 | −0.073205 | 0.003892 | −0.015608 | 0.025426 |
| 147 | −0.086705 | −0.002036 | −0.085743 | 0.001849 | 0.160618 | −0.04951 | −0.116988 | 0.036505 | −0.006747 | 0.047572 | 0.004963 | 0.11845 | −0.03459 | 0.092025 |
| 148 | 0.176894 | −0.171569 | −0.107036 | 0.021075 | 0.000906 | −0.014755 | −0.052233 | −0.009332 | −0.073263 | 0.071646 | 0.072601 | 0.100417 | −0.056836 | 0.049088 |
| 149 | 0.004013 | 0.022014 | 0.018301 | −0.077911 | −0.060827 | 0.015618 | 0.024029 | 0.009661 | 0.029278 | 0.074912 | 0.131299 | 0.029814 | 0.038664 | −0.09351 |
| 150 | 0.012202 | 0.066622 | −0.019418 | 0.006961 | 0.105231 | 0.030666 | 0.049405 | 0.08701 | 0.012803 | −0.090342 | −0.128845 | −0.077547 | 0.020375 | 0.131676 |
| 151 | 0.022491 | −0.021945 | −0.058071 | −0.074951 | −0.057117 | −0.015513 | −0.107289 | 0.108095 | 0.049142 | 0.115679 | −0.031995 | 0.047865 | 0.03079 | −0.026794 |
| 152 | −0.055913 | 0.022115 | 0.030132 | 0.02237 | −0.025547 | −0.031123 | 0.038535 | −0.006043 | 0.044576 | −0.101556 | −0.021052 | 0.02344 | 0.085689 | −0.037186 |
| 153 | 0.012451 | 0.050318 | −0.050745 | 0.053898 | −0.009305 | −0.047688 | 0.023802 | −0.034442 | −0.004587 | −0.051453 | −0.014014 | 0.012462 | 0.144693 | −0.067008 |
| 154 | 0.037137 | 0.011555 | −0.016811 | 0.015997 | 0.070004 | −0.028679 | −0.007019 | −0.028928 | −0.010248 | 0.049718 | 0.050891 | −0.083385 | −0.105425 | 0.052636 |
| 155 | 0.077341 | −0.020707 | −0.033146 | 0.004601 | 0.041614 | 0.005335 | 0.073105 | −0.017585 | 0.007668 | −0.115628 | −0.06902 | −0.057133 | −0.053206 | −0.056528 |
| 156 | 0.028725 | −0.01146 | −0.058141 | −0.051706 | −0.033276 | 0.000292 | 0.034989 | −0.091361 | −0.030085 | 0.083909 | −0.026936 | −0.002886 | 0.01993 | 0.075826 |
| 157 | 0.005214 | −0.053544 | 0.039281 | 0.086028 | 0.069158 | 0.001015 | −0.016145 | 0.039061 | 0.015165 | −0.00583 | −0.02602 | −0.026287 | −0.015714 | 0.029795 |
| 158 | 0.14309 | −0.069425 | −0.163728 | −0.0652 | 0.042272 | 0.051168 | 0.019848 | −0.013869 | −0.056516 | 0.071735 | 0.036814 | 0.029566 | −0.008901 | −0.004337 |
| 159 | 0.011283 | 0.060118 | 0.078407 | −0.127315 | 0.049079 | 0.056586 | 0.010715 | −0.047225 | −0.018383 | −0.065581 | 0.0058 | 0.042233 | −0.098205 | 0.048111 |
| 160 | 0.079224 | 0.08886 | 0.090639 | 0.141664 | −0.12011 | 0.036238 | −0.019673 | −0.066738 | 0.074658 | 0.090893 | −0.017464 | 0.10684 | 0.160626 | −0.046318 |
| 161 | 0.018134 | −0.032269 | −0.033768 | −0.03168 | −0.121218 | −0.063191 | 0.020359 | 0.076314 | −0.009085 | −0.019592 | 0.023472 | 0.15878 | 0.093414 | 0.022078 |
| 162 | −0.012332 | −0.013273 | 0.086694 | 0.075251 | −0.006405 | −0.055756 | −0.1057 | −0.014672 | −0.044826 | −0.023457 | −0.008976 | −0.047682 | 0.046299 | 0.012989 |
| 163 | −0.022864 | 0.014132 | 0.031655 | 0.039904 | −0.062053 | 0.046943 | −0.002564 | 0.036305 | −0.047248 | −0.050872 | 0.037114 | 0.016597 | 0.019576 | 0.036741 |
| 164 | −0.058138 | 0.04856 | 0.028411 | −0.050801 | −0.016482 | 0.014049 | −0.047913 | 0.038669 | −0.033377 | 0.154016 | −0.004463 | −0.080178 | −0.022408 | −0.014759 |
| 165 | 0.111624 | −0.136622 | 0.086 | 0.056355 | −0.253509 | −0.108163 | 0.171276 | −0.069487 | 0.114951 | 0.039346 | −0.087359 | 0.005415 | 0.059156 | −0.084031 |
| 166 | 0.02863 | −0.135518 | 0.049397 | 0.205525 | −0.008783 | 0.077503 | 0.068054 | 0.014554 | 0.044327 | 0.040867 | 0.100709 | −0.058287 | −0.047741 | −0.132796 |
| 167 | −0.119043 | −0.06203 | −0.110138 | −0.089961 | 0.048963 | 0.027961 | −0.06817 | −0.116392 | 0.072631 | 0.019451 | −0.034013 | −0.096635 | −0.115563 | −0.068508 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 168 | −0.034667 | 0.017373 | 0.068286 | −0.057663 | 0.011859 | 0.0047 | −0.029944 | −0.00582 | −0.103537 | 0.061509 | 0.003159 | 0.023639 | 0.106063 | 0.073793 |
| 169 | −0.018047 | −0.00982 | −0.006075 | 0.028781 | 0.026748 | −0.020888 | 0.022775 | 0.058559 | 0.065753 | −0.039483 | −0.044726 | 0.014762 | −0.004928 | −0.014009 |
| 170 | −0.033897 | −0.005563 | −0.000447 | 0.023384 | −0.011836 | −0.073428 | 0.041552 | 0.026281 | 0.054626 | −0.02548 | −0.02262 | 0.067462 | 0.017228 | 0.046394 |
| 171 | −0.053588 | 0.012196 | 0.041461 | −0.025087 | −0.002215 | −0.04111 | 0.045748 | −0.024142 | 0.048601 | −0.061184 | 0.012997 | 0.02809 | 0.080651 | −0.013852 |
| 172 | −0.006657 | −0.016208 | −0.011858 | 0.021215 | 0.021476 | −0.01589 | −0.000862 | −0.006313 | 0.002234 | 0.00179 | −0.06573 | 0.05822 | −0.015655 | −0.033369 |
| 173 | 0.02699 | 0.019579 | 0.042114 | 0.032907 | 0.013178 | −0.020245 | 0.075089 | −0.069126 | 0.032294 | 0.045918 | 0.027628 | 0.050238 | −0.006877 | −0.061192 |
| 174 | −0.016339 | −0.038378 | −0.020349 | 0.02438 | 0.012087 | −0.036998 | 0.035801 | −0.006346 | 0.061485 | −0.004569 | 0.029762 | 0.016112 | −0.051245 | −0.027099 |
| 175 | −0.008032 | −0.003876 | −0.078199 | 0.027077 | −0.086274 | −0.080366 | 0.04595 | 0.115694 | 0.133811 | −0.03487 | 0.013093 | −0.073746 | 0.041795 | 0.009746 |
| 176 | −0.033488 | −0.057863 | −0.034875 | −0.036182 | −0.060964 | −0.149935 | −0.052213 | −0.060101 | −0.033117 | −0.008235 | −0.000858 | 0.006378 | 0.116052 | 0.071322 |
| 177 | −0.065341 | −0.013197 | −0.144431 | 0.117306 | −0.063191 | 0.097005 | −0.091722 | −0.047633 | −0.078603 | −0.035878 | −0.123225 | −0.066172 | −0.104512 | 0.05612 |
| 178 | −0.051088 | 0.032089 | −0.017913 | 0.068354 | −0.018317 | 0.013101 | 0.003303 | 0.010823 | 0.052873 | −0.056627 | −0.000753 | −0.032958 | −0.026144 | 0.118203 |
| 179 | −0.031058 | −0.015215 | −0.001498 | −0.016712 | 0.032885 | 0.02984 | −0.009483 | 0.006381 | 0.020292 | −0.0415 | −0.03516 | −0.042995 | −0.021517 | −0.011554 |
| 180 | −0.023669 | −0.008231 | 0.011426 | 0.012525 | 0.03313 | 0.018858 | −0.020032 | −0.005132 | 0.048438 | −0.036917 | −0.001956 | −0.007552 | 0.006007 | −0.015293 |
| 181 | −0.050391 | 0.007353 | 0.001933 | 0.018912 | 0.018204 | 0.008864 | −0.022361 | 0.003683 | 0.025707 | −0.020837 | −0.011616 | −0.016952 | 0.000609 | −0.013569 |
| 182 | −0.026201 | 0.000896 | −0.005996 | 0.00505 | 0.00885f | 0.026014 | −0.053597 | −0.030397 | −0.026712 | 0.002601 | 0.016956 | 0.003297 | 0.035186 | 0.037624 |
| 183 | −0.003966 | −0.007099 | 0.019451 | −0.067136 | 0.017816 | 0.04873 | 0.020894 | −0.061028 | −0.032906 | −0.034187 | −0.01715 | −0.066165 | −0.001247 | 0.00319 |
| 184 | 0.025883 | −0.048269 | 0.084479 | −0.045385 | 0.006541 | 0.045081 | 0.008668 | −0.073949 | −0.032881 | −0.112733 | 0.086742 | 0.066897 | −0.039 | −0.086697 |
| 185 | 0.046916 | −0.086849 | 0.056799 | −0.002348 | −0.065761 | −0.018007 | 0.014044 | 0.071591 | 0.032216 | −0.082086 | 0.028772 | 0.018655 | −0.003237 | 0.058239 |
| 186 | −0.014466 | 0.030185 | 0.110583 | −0.011868 | 0.092814 | −0.054004 | −0.024635 | 0.031744 | −0.065632 | 0.038195 | 0.072343 | 0.029143 | 0.038473 | −0.072093 |
| 187 | 0.057917 | −0.021714 | 0.00749 | 0.007038 | 0.01802 | 0.050864 | −0.026326 | −0.034173 | −0.038695 | 0.016505 | 0.009308 | 0.028118 | −0.067737 | −0.055431 |
| 188 | 0.054443 | −0.08855 | −0.006145 | 0.008449 | 0.019236 | 0.031679 | −0.047738 | −0.036093 | 0.009303 | −0.002015 | 0.003116 | 0.042243 | −0.055155 | −0.002398 |
| 189 | 0.071987 | −0.04917 | −0.056744 | −0.040513 | 0.02628 | 0.050322 | −0.11268 | 0.005561 | 0.019598 | −0.02965 | 0.015217 | −0.044872 | 0.014016 | 0.003554 |
| 190 | −0.01422 | 0.006284 | −0.004233 | −0.083309 | −0.022063 | −0.02669 | −0.036207 | 0.028561 | 0.023329 | −0.008508 | 0.094656 | 0.021259 | −0.005051 | −0.045999 |
| 191 | 0.035439 | 0.022567 | 0.034737 | −0.028451 | −0.00841 | 0.009757 | −0.046725 | 0.079341 | −0.025862 | 0.024927 | 0.037456 | −0.00858 | −0.044889 | −0.104206 |
| 192 | −0.038763 | −0.110529 | 0.070703 | −0.058557 | 0.028804 | 0.067781 | 0.010744 | 0.034741 | −0.067545 | 0.051394 | −0.016293 | −0.068735 | −0.056744 | 0.095867 |
| 193 | −0.04856 | −0.054907 | −0.011696 | −0.00582 | −0.008378 | −0.059832 | 0.000261 | 0.025276 | −0.089264 | 0.036819 | 0.061431 | 0.042694 | −0.0106 | −0.031649 |
| 194 | 0.057892 | −0.015147 | 0.027567 | −0.042918 | 0.024821 | −0.020477 | −0.027847 | 0.076884 | 0.105889 | −0.043378 | −0.053556 | −0.04985 | −0.004323 | −0.012181 |
| 195 | 0.009713 | 0.007177 | −0.005297 | −0.079096 | 0.023158 | −0.056375 | −0.007971 | 0.004606 | −0.068252 | 0.024035 | 0.033132 | 0.010535 | −0.030199 | −0.035705 |
| 196 | −0.024764 | −0.042572 | 0.010396 | −0.048352 | −0.010524 | 0.00366 | −0.071277 | 0.062513 | 0.003252 | 0.014714 | 0.068781 | 0.004189 | −0.037404 | −0.029271 |
| 197 | −0.004624 | −0.017022 | 0.017702 | −0.133161 | −0.046465 | −0.045836 | −0.066827 | 0.045959 | −0.053411 | 0.039313 | 0.105106 | 0.022305 | −0.014888 | −0.055207 |
| 198 | 0.045971 | −0.017067 | 0.033606 | −0.002079 | −0.094846 | −0.062919 | −0.000671 | −0.068217 | −0.130067 | −0.097679 | −0.016183 | −0.005172 | −0.020538 | 0.108309 |
| 199 | −0.046376 | 0.012659 | 0.008988 | −0.11376 | 0.075642 | 0.046316 | −0.050583 | 0.036084 | 0.079525 | −0.053673 | 0.181772 | −0.048689 | −0.027729 | −0.09017 |
| 200 | −0.051502 | 0.060266 | 0.03981 | −0.031197 | −0.034256 | 0.03087 | 0.06491 | −0.068883 | −0.065572 | −0.00629 | −0.169375 | −0.05017 | −0.000763 | −0.008502 |
| 201 | 0.064624 | 0.000782 | 0.082867 | −0.03187 | −0.072443 | −0.085702 | −0.014703 | −0.020328 | 0.018523 | 0.091946 | −0.101659 | 0.025681 | 0.082702 | 0.094293 |
| 202 | −0.005285 | −0.007081 | 0.105165 | −0.002502 | −0.0178 | −0.049325 | 0.090515 | −0.049657 | 0.026326 | 0.085431 | −0.038169 | 0.00201 | −0.036772 | 0.05975 |
| 203 | 0.088613 | −0.011767 | −0.059776 | −0.063382 | −0.00886 | 0.140832 | −0.076721 | −0.05219 | 0.042646 | −0.068549 | 0.021401 | −0.024833 | −0.012528 | −0.005757 |
| 204 | −0.166808 | −0.062652 | 0.185139 | 0.076336 | 0.008979 | −0.109436 | −0.048212 | −0.007329 | −0.023113 | 0.069048 | −0.116774 | 0.054252 | 0.056703 | −0.118638 |
| 205 | 0.088036 | −0.047572 | 0.181521 | −0.143193 | −0.023722 | 0.020466 | −0.122741 | −0.000623 | 0.087566 | −0.089114 | −0.067705 | −0.021416 | −0.03597 | −0.015437 |
| 206 | −0.05238 | 0.044278 | −0.171066 | −0.037272 | 0.029478 | 0.177284 | −0.090245 | 0.072467 | 0.022584 | 0.017478 | −0.022878 | 0.105116 | 0.047144 | −0.012468 |
| 207 | −0.159918 | −0.064149 | −0.073463 | 0.03125 | −0.034636 | 0.033957 | −0.103773 | 0.103942 | −0.115433 | 0.045018 | 0.044454 | −0.061505 | 0.140107 | 0.013799 |
| 208 | 0.095257 | 0.050276 | 0.069183 | −0.02846 | −0.059011 | −0.014783 | −0.011091 | −0.058376 | 0.042357 | −0.123395 | −0.078058 | −0.007772 | −0.068908 | −0.021187 |
| 209 | −0.015342 | −0.15527 | 0.101013 | 0.016889 | 0.094885 | 0.023536 | 0.069003 | −0.083539 | −0.023008 | −0.021962 | 0.045646 | 0.055915 | −0.028437 | 0.067841 |
| 210 | −0.054537 | 0.059394 | −0.070746 | 0.037397 | 0.083321 | 0.023282 | 0.115869 | −0.029654 | −0.139374 | −0.047268 | −0.011781 | −0.125678 | 0.105761 | −0.06193 |
| 211 | 0.000192 | 0.067822 | 0.076065 | −0.006887 | 0.135519 | 0.06658 | 0.246074 | −0.020949 | −0.015931 | 0.105137 | −0.006799 | 0.046711 | −0.063627 | −0.030437 |
| 212 | −0.009391 | 0.019233 | 0.002044 | −0.035657 | −0.108703 | −0.096673 | 0.063745 | −0.046401 | −0.150503 | −0.007418 | 0.140068 | 0.05878 | −0.139739 | 0.076368 |
| 213 | −0.096863 | 0.168116 | −0.070665 | 0.167101 | −0.069285 | 0.097073 | −0.058448 | 0.167749 | 0.117956 | −0.0367 | −0.044543 | 0.033596 | 0.010057 | −0.048835 |
| 214 | −0.008318 | 0.020315 | 0.053771 | −0.003943 | 0.08172 | 0.055907 | 0.001765 | 0.008418 | −0.00569 | −0.005576 | −0.012285 | −0.0441 | −0.005521 | 0.019434 |
| 215 | 0.019302 | 0.055056 | 0.008749 | 0.047125 | 0.022852 | −0.032391 | 0.026959 | 0.184851 | −0.042416 | −0.067847 | −0.085472 | −0.008806 | −0.078156 | −0.112537 |
| 216 | −0.007685 | 0.023055 | −0.006834 | 0.010067 | −0.012554 | −0.030131 | −0.057091 | −0.004717 | −0.015315 | 0.014747 | 0.028826 | 0.005039 | 0.056586 | −0.0308 |
| 217 | 0.065829 | 0.051136 | 0.022174 | −0.040918 | 0.101738 | 0.018832 | −0.01 | 0.037246 | 0.063845 | −0.055679 | −0.108448 | 0.014227 | −0.03002 | 0.059784 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 218 | 0.013716 | 0.003985 | 0.024691 | −0.008191 | 0.08056 | −0.017554 | 0.000367 | 0.029202 | −0.02557 | 0.025009 | −0.005518 | 0.048216 | −0.011879 | 0.003945 |
| 219 | 0.012691 | 0.030416 | 0.004496 | 0.050447 | 0.049441 | 0.024763 | 0.003741 | −0.04562 | −0.024018 | 0.027361 | 0.023661 | 0.01467 | −0.001504 | 0.03775 |
| 220 | 0.032332 | 0.066182 | 0.023091 | 0.023877 | 0.01383 | 0.044799 | −0.025349 | 0.009834 | −0.035314 | −0.070964 | −0.057224 | −0.036647 | −0.015425 | 0.004199 |
| 221 | 0.052645 | 0.049168 | 0.070328 | 0.038508 | 0.049358 | 0.020434 | −0.003718 | −0.07252 | 0.003839 | 0.020169 | −0.0265 | −0.012112 | 0.066875 | −0.002683 |
| 222 | 0.01316 | −0.000521 | 0.031241 | 0.012671 | 0.016725 | 0.081497 | 0.050533 | −0.041227 | −0.028032 | 0.012795 | −0.006941 | −0.022328 | −0.021782 | 0.030542 |
| 223 | −0.023219 | 0.078597 | 0.002446 | 0.052792 | 0.003598 | 0.010299 | 0.029425 | 0.012654 | 0.003592 | 0.040573 | 0.046093 | −0.04837 | 0.066668 | −0.04388 |
| 224 | −0.014523 | 0.015675 | −0.009304 | 0.020813 | −0.009388 | −0.060099 | 0.067053 | −0.076744 | 0.062645 | 0.027868 | 0.0393121 | −0.032355 | −0.106047 | −0.060818 |
| 225 | 0.002821 | 0.057083 | −0.009141 | 0.026041 | −0.002538 | −0.054561 | 0.077862 | −0.100915 | 0.084698 | 0.03003 | 0.02267 | −0.061998 | −0.128463 | −0.051102 |
| 226 | 0.016024 | −0.014026 | 0.007174 | −0.011727 | −0.038791 | −0.018404 | 0.008595 | 0.00097 | −0.032502 | 0.015682 | 0.044488 | −0.097614 | −0.006093 | −0.011801 |
| 227 | 0.0088 | −0.016671 | −0.132523 | −0.018097 | −0.010535 | −0.030676 | −0.025376 | 0.022367 | 0.044841 | −0.03505 | 0.005418 | −0.071569 | −0.061847 | −0.033221 |
| 228 | 0.032743 | 0.0705 | 0.074668 | −0.007802 | 0.016044 | 0.04722 | −0.022706 | −0.001341 | −0.029483 | −0.010069 | 0.10697 | 0.018149 | −0.003224 | −0.014531 |
| 229 | −0.066658 | 0.026088 | 0.008469 | −0.007215 | 0.011554 | 0.011208 | 0.018652 | 0.019875 | −0.027373 | −0.018801 | −0.084615 | 0.03169 | −0.076102 | −0.028176 |
| 230 | −0.046694 | −0.032745 | −0.007929 | 0.000575 | −0.033566 | 0.009015 | 0.040004 | 0.032476 | −0.028833 | 0.024564 | −0.013167 | 0.006363 | −0.006607 | 0.003135 |
| 231 | 0.019364 | −0.025844 | −0.051297 | 0.005058 | −0.024283 | −0.0119 | −0.023962 | −0.008699 | 0.019894 | 0.053247 | 0.102311 | 0.077938 | 0.004031 | −0.113816 |
| 232 | 0.09326 | −0.062952 | 0.079122 | −0.029405 | −0.064281 | −0.047823 | 0.029136 | −0.007776 | −0.097396 | −0.016749 | 0.053855 | −0.073661 | −0.006494 | −0.093823 |
| 233 | 0.023978 | −0.036837 | −0.00557 | 0.005299 | −0.036094 | 0.001621 | 0.008996 | 0.022753 | −0.072418 | −0.000948 | −0.101046 | 0.012045 | −0.030701 | 0.019246 |
| 234 | −0.027698 | 0.060155 | −0.015493 | 0.006941 | −0.071132 | 0.045513 | −0.021643 | 0.048683 | −0.040325 | −0.030113 | −0.005716 | 0.038686 | −0.003242 | 0.041074 |
| 235 | −0.041586 | 0.024999 | 0.01819 | 0.070553 | −0.043923 | 0.072454 | −0.024086 | −0.019125 | 0.000282 | −0.016281 | −0.045612 | 0.104856 | −0.067021 | 0.016043 |
| 236 | −0.015238 | −0.080195 | −0.05743 | −0.019506 | −0.071136 | −0.003514 | 0.037223 | −0.031207 | −0.015865 | 0.000655 | 0.035907 | −0.015423 | 0.112936 | −0.067907 |
| 237 | 0.042601 | 0.006949 | 0.029309 | −0.02431 | −0.020732 | −0.036307 | −0.05704 | −0.003382 | 0.020397 | 0.017622 | −0.033871 | −0.04167 | −0.022867 | −0.043581 |
| 238 | 0.018614 | 0.048568 | 0.046473 | −0.030413 | −0.015203 | −0.015486 | −0.020101 | −0.020052 | 0.013404 | 0.030668 | −0.009062 | 0.018188 | −0.058122 | −0.007437 |
| 239 | −0.008343 | 0.022066 | 0.008586 | 0.008344 | 0.001108 | −0.009478 | 0.01187 | −0.026293 | 0.006844 | 0.026554 | 0.050903 | 0.045575 | −0.043795 | 0.034314 |
| 240 | 0.019809 | −0.102547 | 0.013298 | −0.024584 | −0.025859 | −0.041695 | −0.002899 | −0.011587 | 0.09235 | −0.012306 | −0.003396 | 0.004717 | −0.031396 | −0.059174 |
| 241 | −0.0454 | −0.106519 | 0.002766 | −0.015599 | −0.018265 | −0.009091 | 0.004425 | 0.03896 | −0.003506 | 0.009823 | −0.067165 | 0.00156 | −0.019756 | 0.023192 |
| 242 | 0.027821 | −0.000956 | −0.036253 | 0.043734 | −0.046311 | 0.082625 | −0.009047 | −0.000369 | −0.035016 | −0.009126 | 0.011336 | 0.053122 | 0.025035 | 0.015595 |
| 243 | 0.088457 | 0.100498 | 0.014722 | 0.074025 | 0.008729 | 0.051262 | −0.005696 | 0.015419 | −0.051126 | −0.027207 | −0.046606 | 0.08463 | 0.012594 | 0.027196 |
| 244 | 0.058134 | 0.033838 | −0.001904 | 0.009277 | 0.04535 | 0.018589 | −0.017576 | −0.01371 | −0.018766 | −0.044057 | −0.007768 | 0.04366f | 0.061718 | 0.008278 |
| 245 | −0.038706 | −0.105936 | −0.046096 | −0.017805 | 0.054313 | 0.049428 | −0.011678 | 0.02889 | 0.042892 | −0.02147 | −0.023329 | 0.052057 | 0.035309 | 0.043004 |
| 246 | 0.00433 | 0.017156 | −0.043156 | −0.007299 | −0.042349 | −0.008867 | 0.014787 | −0.021834 | −0.010553 | 0.01106 | 0.00244 | −0.024294 | −0.022404 | 0.035376 |
| 247 | 0.005372 | 0.018002 | −0.023636 | 0.014633 | −0.015819 | 0.029374 | 0.035594 | −0.060935 | 0.01178 | 0.006287 | 0.015947 | −0.01115 | 0.016108 | 0.017968 |
| 248 | 0.020703 | −0.018783 | 0.02359 | 0.021165 | −0.002391 | 0.026499 | 0.018289 | −0.057705 | −0.028646 | −0.032018 | 0.003741 | −0.049394 | −0.006544 | −0.021331 |
| 249 | 0.002547 | −0.144429 | 0.007475 | −0.072345 | −0.021784 | −0.087986 | 0.06322 | 0.015906 | −0.032861 | 0.011743 | −0.06341 | 0.030299 | 0.004832 | 0.031138 |
| 250 | 0.003232 | −0.024938 | −0.043157 | −0.029981 | −0.042191 | −0.065168 | −0.004033 | 0.010634 | 0.059472 | −0.006918 | 0.015209 | −0.048255 | 0.007096 | −0.055019 |
| 251 | −0.014775 | −0.03834 | 0.031215 | 0.018299 | −0.051542 | 0.030644 | 0.004718 | −0.04289 | 0.081272 | 0.010999 | −0.009086 | −0.033149 | −0.023288 | 0.004656 |
| 252 | −0.054474 | −0.1185 | −0.027294 | −0.039287 | 0.033224 | 0.061964 | 0.001069 | 0.073352 | −0.003585 | 0.002665 | −0.034852 | 0.025703 | 0.023329 | 0.043208 |
| 253 | 0.037364 | 0.018443 | 0.019174 | −0.027935 | −0.030235 | −0.035874 | 0.019812 | 0.100024 | 0.012755 | −0.050526 | −0.038577 | −0.022935 | 0.027863 | −0.007047 |
| 254 | −0.033515 | 0.080528 | −0.056243 | 0.065794 | 0.002507 | −0.047705 | 0.043018 | 0.031253 | −0.020425 | 0.001186 | 0.059002 | 0.055093 | 0.041463 | −0.042246 |
| 255 | 0.035469 | 0.057173 | −0.02846 | 0.024146 | −0.009513 | −0.022741 | −0.009367 | −0.010094 | −0.019883 | −0.020838 | 0.010728 | 0.05919 | 0.029529 | 0.013571 |
| 256 | −0.042874 | −0.083613 | 0.026064 | −0.037434 | −0.03417 | −0.050123 | −0.064026 | 0.069451 | −0.013306 | −0.018301 | −0.0797 | 0.112871 | 0.007971 | −0.023321 |
| 257 | −0.07036 | −0.016952 | −0.009146 | −0.059659 | −0.061681 | −0.030582 | −0.046382 | 0.032225 | 0.052895 | 0.004012 | −0.066292 | −0.046591 | 0.03427 | 0.022156 |
| 258 | −0.060748 | 0.008719 | −0.031403 | −0.007187 | 0.030763 | −0.012739 | −0.000166 | −0.020648 | 0.058196 | 0.019331 | 0.013455 | −0.024912 | 0.003314 | −0.007155 |
| 259 | −0.020951 | −0.04262 | −0.044099 | 0.014986 | 0.007953 | 0.035293 | 0.051304 | −0.029212 | 0.012386 | 0.00917 | −0.008831 | 0.006242 | 0.003434 | −0.007165 |
| 260 | −0.063529 | −0.059197 | −0.081546 | 0.028719 | 0.068128 | 0.074007 | 0.048463 | −0.023204 | 0.03238 | −0.045302 | −0.001251 | −0.083419 | 0.048653 | −0.007739 |
| 261 | −0.034133 | −0.028557 | −0.074739 | −0.040816 | 0.018799 | 0.039866 | −0.013276 | −0.041419 | 0.061382 | 0.017113 | 0.041083 | −0.018751 | −0.01312 | −0.010943 |
| 262 | −0.014922 | −0.04733 | −0.038039 | −0.033694 | −0.03195 | 0.034151 | 0.033668 | −0.020191 | 0.05814 | 0.021853 | 0.02947 | 0.009565 | 0.007992 | 0.018688 |
| 263 | −0.009135 | −0.043005 | −0.029652 | −0.016687 | −0.016314 | 0.068185 | 0.034897 | −0.003341 | 0.024055 | 0.023209 | −0.012304 | 0.019082 | 0.03645 | 0.020594 |
| 264 | −0.031465 | −0.028036 | −0.039217 | −0.013726 | 0.03349 | −0.009461 | 0.028922 | −0.016616 | −0.046453 | 0.021647 | −0.022701 | 0.044299 | −0.029938 | −0.025056 |
| 265 | −0.043313 | 0.061491 | −0.093594 | −0.014862 | 0.055188 | −0.072632 | 0.039401 | 0.041591 | −0.051592 | 0.068859 | 0.075068 | 0.05815 | 0.000265 | −0.062308 |
| 266 | −0.00359 | 0.088344 | −0.029487 | −0.015463 | 0.036359 | −0.0514 | 0.004987 | −0.003694 | −0.04165 | 0.045408 | 0.105977 | 0.054349 | 0.046115 | −0.003754 |
| 267 | 0.049034 | 0.067693 | −0.021505 | −0.036345 | 0.014897 | −0.075407 | −0.030942 | 0.006142 | −0.003497 | −0.086473 | 0.026391 | −0.004585 | −0.027232 | −0.092216 |

APPENDIX B3-continued

PCA Transformation
Matrix (340 × 340 Early/Late)

| | | | | | | | | | | | | | |
|---|---|---|---|---|---|---|---|---|---|---|---|---|---|
| 268 | 0.022806 | −0.024486 | −0.00301 | −0.034149 | −0.028015 | −0.008742 | 0.018057 | 0.028214 | −0.036234 | −0.002214 | 0.056888 | −0.052279 | −0.01298 | −0.022778 |
| 269 | 0.033534 | −0.010394 | 0.015141 | −0.002938 | −0.038118 | 0.003043 | 0.017556 | 0.031515 | −0.037445 | −0.011039 | 0.015266 | −0.063526 | −0.008481 | −0.026412 |
| 270 | 0.030992 | −0.040033 | −0.052088 | −0.008045 | −0.018804 | 0.000591 | −0.009092 | 0.026709 | −0.029072 | −0.044359 | 0.050695 | −0.073147 | 0.001822 | 0.013388 |
| 271 | −0.002574 | 0.00679 | 0.010586 | −0.083131 | 0.059468 | −0.013285 | 0.088197 | −0.146684 | −0.013274 | 0.078246 | 0.002231 | −0.060722 | 0.115918 | 0.074953 |
| 272 | −0.036945 | −0.006129 | −0.02105 | −0.013507 | 0.019996 | −0.005097 | 0.010091 | −0.034809 | −0.00124 | 0.012287 | −0.016666 | 0.019475 | −0.069309 | −0.020869 |
| 273 | −0.034284 | −0.091107 | −0.019575 | −0.001854 | 0.029961 | 0.042069 | 0.066431 | 0.050393 | −0.007031 | 0.00121 | 0.001459 | −0.035786 | −0.025149 | 0.008631 |
| 274 | −0.038601 | −0.080494 | −0.018977 | 0.010655 | 0.028286 | 0.044808 | 0.048631 | 0.04826 | −0.008331 | 0.005518 | −0.010944 | −0.036433 | −0.021876 | 0.018632 |
| 275 | 0.001211 | −0.067312 | −0.095134 | 0.028727 | 0.017357 | 0.044773 | −0.007406 | −0.014524 | −0.05804 | −0.08215 | −0.013252 | −0.010269 | 0.032248 | 0.029401 |
| 276 | −0.05215 | −0.089363 | −0.066545 | −0.033379 | −0.059692 | 0.01427 | 0.010569 | −0.038233 | −0.001385 | 0.000937 | 0.046094 | −0.00718 | 0.072419 | −0.069747 |
| 277 | 0.018851 | −0.013014 | −0.004382 | 0.04321 | 0.032589 | 0.004229 | 0.001621 | 0.002172 | 0.009756 | −0.029442 | 0.07445 | 0.043941 | −0.01415 | −0.012187 |
| 278 | 0.00462 | −0.000482 | 0.011329 | 0.093824 | 0.01743 | −0.007915 | −0.004492 | −0.022038 | 0.005782 | −0.040215 | 0.073413 | 0.039085 | −0.010145 | −0.013533 |
| 279 | −0.016648 | 0.025397 | 0.044213 | 0.046401 | 0.020922 | 0.002354 | 0.02454 | −0.041783 | −0.016354 | −0.003214 | 0.076315 | 0.03133 | −0.032753 | 0.028091 |
| 280 | 0.121303 | 0.044991 | 0.002543 | 0.027811 | −0.007262 | 0.019285 | −0.000439 | 0.077339 | −0.049325 | −0.006158 | −0.035919 | 0.067297 | 0.006208 | 0.004186 |
| 281 | −0.03191 | 0.016661 | −0.01464 | 0.051958 | 0.008265 | 0.039896 | 0.050483 | −0.035353 | −0.000627 | 0.056644 | 0.038892 | 0.000285 | −0.003112 | 0.029989 |
| 282 | −0.078498 | 0.011003 | 0.009765 | 0.069867 | 0.006285 | 0.046651 | 0.086686 | −0.055377 | −0.004004 | 0.063884 | 0.019518 | 0.025712 | 0.034628 | 0.063538 |
| 283 | −0.036944 | 0.005306 | 0.026434 | 0.082779 | 0.007784 | 0.07045 | 0.047671 | −0.082887 | −0.010255 | 0.006375 | 0.040853 | −0.008733 | 0.052111 | 0.037388 |
| 284 | −0.074245 | −0.026488 | 0.017196 | −0.038922 | −0.035305 | −0.012545 | −0.038064 | 0.019087 | 0.026812 | 0.021094 | −0.050731 | −0.024431 | 0.01358 | −0.020131 |
| 285 | −0.088744 | −0.016595 | 0.037331 | −0.040075 | −0.046132 | −0.018118 | −0.015493 | 0.026709 | 0.025131 | 0.017441 | −0.058648 | −0.02332 | 0.04715 | 0.033048 |
| 286 | −0.110663 | 0.038721 | 0.003428 | 0.007765 | 0.038757 | −0.001007 | −0.042255 | −0.000762 | 0.028503 | 0.075484 | −0.050533 | 0.013085 | −0.008615 | 0.006847 |
| 287 | −0.089143 | 0.022953 | 0.011406 | 0.025274 | 0.038283 | 0.007902 | −0.02728 | −0.001078 | 0.014374 | 0.052923 | −0.045093 | 0.016833 | 0.023746 | 0.047053 |
| 288 | −0.036191 | −0.003836 | 0.005669 | 0.047822 | 0.028463 | 0.038593 | −0.003032 | −0.032869 | 0.026889 | 0.00046 | 0.070169 | −0.059456 | −0.020987 | 0.00826 |
| 289 | −0.01769 | −0.021918 | −0.037315 | 0.015507 | −0.045984 | −0.010162 | 0.028513 | −0.026089 | −0.018313 | −0.016546 | 0.042276 | −0.000853 | 0.039042 | 0.055317 |
| 290 | 0.042497 | 0.031985 | 0.024863 | 0.012311 | −0.039677 | 0.013927 | 0.000977 | 0.006905 | 0.017023 | −0.078499 | −0.003043 | 0.001531 | −0.046413 | 0.02564 |
| 291 | 0.04145 | 0.032795 | 0.024851 | 0.011609 | −0.03238 | 0.010181 | −0.01323 | 0.006084 | 0.018431 | −0.073594 | −0.006572 | 0.004636 | −0.038608 | 0.021913 |
| 292 | 0.038356 | 0.052485 | 0.045261 | −0.001462 | −0.039868 | 0.010683 | −0.00775 | 0.021028 | 0.015971 | −0.051039 | −0.018843 | 0.003737 | −0.057797 | 0.02773 |
| 293 | 0.010439 | −0.036127 | −0.135594 | 0.053113 | −0.033614 | −0.107822 | 0.031371 | −0.013143 | 0.02014 | 0.051375 | 0.011104 | −0.004845 | 0.047994 | −0.092643 |
| 294 | 0.025718 | −0.023009 | −0.029914 | 0.020376 | 0.050451 | 0.002285 | 0.013038 | −0.011383 | −0.034856 | −0.021602 | 0.037264 | 0.02856 | −0.000337 | 0.004385 |
| 295 | 0.005638 | −0.071046 | −0.048805 | 0.025743 | −0.016233 | −0.00057 | 0.035804 | 0.028323 | 0.069485 | 0.002295 | 0.020552 | 0.031264 | −0.009952 | 0.029994 |
| 296 | 0.101032 | −0.026438 | −0.01756 | 0.021967 | 0.052129 | 0.100405 | 0.015169 | 0.038902 | 0.017673 | −0.098981 | 0.057816 | −0.00683 | −0.04107 | 0.081242 |
| 297 | −0.016114 | −0.084733 | −0.050399 | 0.070593 | −0.016375 | 0.007661 | 0.004259 | 0.028375 | 0.089552 | 0.000305 | 0.038134 | 0.023557 | −0.003347 | 0.028667 |
| 298 | 0.047831 | 0.089669 | 0.058267 | −0.001337 | 0.045289 | 0.050884 | 0.04414 | 0.048017 | −0.044035 | −0.070304 | 0.00854 | −0.063309 | 0.036222 | −0.007726 |
| 299 | 0.024144 | −0.018345 | −0.040843 | 0.022756 | −0.06739 | 0.031388 | 0.03744 | −0.007197 | 0.064382 | 0.028342 | 0.074635 | −0.019077 | 0.031659 | −0.033559 |
| 300 | −0.053882 | 0.094365 | 0.075231 | 0.014409 | −0.114013 | −0.075069 | −0.032621 | 0.051529 | 0.045814 | −0.03804 | 0.065736 | 0.02911 | −0.034114 | −0.038992 |
| 301 | 0.004891 | −0.009648 | −0.020127 | −0.01912 | −0.103224 | −0.003674 | 0.030598 | −0.008601 | 0.045756 | −0.027734 | 0.009648 | 0.001216 | 0.016984 | 0.021522 |
| 302 | 0.027418 | 0.018317 | −0.024143 | −0.027545 | −0.082716 | 0.044295 | 0.004489 | −0.019142 | 0.040323 | −0.062911 | 0.012671 | 0.010666 | −0.014434 | 0.095959 |
| 303 | 0.040709 | 0.093163 | −0.007207 | 0.014915 | −0.009993 | 0.05741 | 0.013818 | −0.014981 | 0.055078 | −0.014913 | 0.020497 | −0.0111 | −0.014535 | −0.008548 |
| 304 | 0.067515 | 0.04314 | −0.001075 | 0.015052 | −0.054388 | 0.058759 | −0.004813 | 0.021136 | 0.077653 | −0.028554 | 0.07038 | −0.056585 | −0.06902 | 0.01389 |
| 305 | 0.013265 | 0.096355 | −0.0998 | 0.011094 | −0.050818 | −0.103164 | −0.077966 | −0.028297 | −0.050572 | 0.158271 | −0.004514 | 0.009771 | 0.071991 | 0.084181 |
| 306 | −0.051073 | −0.019751 | −0.074969 | −0.051809 | 0.050898 | −0.182411 | −0.117353 | −0.026618 | 0.060848 | −0.026973 | −0.054732 | 0.022712 | 0.005632 | −0.121638 |
| 307 | −0.092231 | −0.059795 | 0.073452 | −0.052554 | 0.094736 | −0.026889 | −0.063829 | 0.021187 | 0.077378 | −0.028268 | 0.034284 | 0.057435 | 0.051236 | −0.025224 |
| 308 | 0.011469 | −0.019763 | −0.00385 | 0.019889 | −0.002069 | 0.072918 | 0.023337 | 0.069507 | −0.081742 | 0.094759 | −0.014109 | −0.127242 | −0.041538 | 0.084961 |
| 309 | 0.076666 | 0.019816 | −0.007215 | 0.00769 | −0.022642 | −0.003003 | 0.020125 | −0.030182 | 0.024725 | −0.025941 | 0.027748 | 0.082784 | 0.052664 | 0.00607 |
| 310 | 0.116684 | 0.081281 | −0.061168 | −0.023786 | 0.096198 | 0.012676 | 0.054645 | −0.028531 | −0.012561 | −0.0763 | −0.090136 | 0.116571 | 0.078152 | −0.012588 |
| 311 | −0.018472 | −0.052337 | −0.030471 | 0.008981 | −0.015244 | −0.006247 | 0.058687 | 0.013925 | 0.010625 | −0.032767 | 0.009227 | 0.000413 | 0.007756 | 0.002282 |
| 312 | 0.084708 | −0.039699 | 0.019235 | 0.277894 | −0.066908 | −0.017669 | −0.133321 | 0.110058 | −0.011676 | 0.122477 | 0.047039 | −0.040219 | −0.165787 | 0.100898 |
| 313 | −0.028237 | 0.007993 | −0.028732 | 0.042605 | −0.010025 | −0.034736 | 0.007768 | 0.017571 | −0.04239 | 0.004777 | −0.083511 | 0.005036 | −0.105904 | −0.020232 |
| 314 | −0.000247 | −0.082113 | 0.158284 | 0.167797 | 0.191534 | −0.165719 | −0.006929 | 0.110752 | −0.008783 | 0.0539 | −0.055115 | 0.099567 | 0.016654 | 0.066676 |
| 315 | 0.046903 | 0.024474 | 0.023314 | 0.028639 | −0.007192 | −0.022204 | −0.028119 | 0.004231 | 0.027234 | 0.042026 | 0.041676 | 0.02084 | 0.016807 | −0.004119 |
| 316 | 0.158359 | 0.114843 | −0.048179 | 0.022106 | 0.030629 | −0.141347 | −0.008876 | −0.045437 | 0.003025 | −0.170813 | −0.108081 | 0.034865 | −0.000371 | 0.063411 |
| 317 | −0.002401 | 0.004701 | 0.029691 | 0.019744 | −0.020161 | −0.020123 | 0.025281 | 0.001084 | 0.026904 | −0.029623 | 0.021453 | 0.078156 | 0.05438 | −0.024518 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 318 | −0.003141 | −0.015161 | 0.098866 | 0.052409 | −0.006804 | −0.001108 | −0.008195 | −0.088437 | 0.023659 | −0.096778 | 0.036095 | −0.084479 | 0.072702 | 0.014761 |
| 319 | 0.004098 | 0.033559 | 0.069172 | 0.026011 | −0.018982 | −0.01213 | 0.021921 | −0.004341 | 0.042761 | −0.011884 | 0.010156 | 0.042827 | 0.052555 | −0.042874 |
| 320 | −0.046475 | 0.018859 | 0.013012 | 0.0685 | 0.028361 | −0.041861 | 0.026954 | −0.001695 | −0.00103 | −0.077817 | 0.002378 | 0.003518 | −0.074016 | −0.018207 |
| 321 | −0.067322 | −0.084321 | 0.044906 | −0.036883 | 0.05156 | 0.065037 | 0.003783 | −0.013243 | 0.029954 | −0.078269 | 0.052709 | 0.016087 | −0.022025 | −0.012617 |
| 322 | 0.045898 | 0.085859 | −0.016249 | 0.026596 | 0.015216 | −0.047087 | −0.067246 | −0.032298 | −0.015565 | 0.005802 | 0.051965 | 0.059434 | −0.040888 | 0.045253 |
| 323 | −0.040613 | 0.017292 | 0.079863 | −0.026451 | −0.02301 | −0.049107 | −0.034705 | 0.062946 | −0.021687 | 0.021323 | 0.018848 | 0.003746 | −0.066475 | −0.053928 |
| 324 | 0.024786 | 0.00377 | −0.054674 | −0.016041 | 0.058128 | −0.016982 | 0.003506 | −0.060855 | −0.051455 | −0.04311 | 0.060109 | −0.162625 | 0.129358 | 0.130772 |
| 325 | 0.042622 | 0.003022 | −0.0245 | −0.028553 | 0.044165 | 0.067939 | −0.03689 | −0.038942 | −0.052898 | −0.068115 | 0.025174 | 0.04354 | 0.016581 | −0.011516 |
| 326 | 0.010155 | −0.092215 | −0.070668 | 0.000734 | 0.003488 | 0.0628 | 0.02553 | −0.084197 | −0.119096 | 0.027243 | −0.011981 | 0.06237 | 0.007201 | −0.044619 |
| 327 | 0.02301 | 0.056889 | 0.022343 | −0.050677 | −0.027832 | 0.077415 | −0.00719 | −0.029794 | −0.00424 | −0.00956 | 0.029804 | 0.002429 | −0.037204 | −0.003933 |
| 328 | 0.073967 | −0.034434 | 0.113337 | −0.007464 | 0.08804 | −0.157886 | 0.005227 | 0.088372 | −0.045373 | 0.153173 | 0.055 | 0.068216 | −0.009126 | 0.116983 |
| 329 | 0.005699 | 0.016166 | 0.075113 | −0.031465 | −0.076657 | 0.081031 | −0.004647 | −0.080191 | −0.024322 | 0.023688 | 0.001266 | 0.05256 | −0.016302 | 0.004767 |
| 330 | −0.07082 | −0.067843 | −0.098966 | −0.032371 | −0.028724 | −0.004758 | 0.063905 | −0.041236 | −0.044066 | −0.038151 | −0.064007 | 0.014214 | −0.001855 | 0.021143 |
| 331 | 0.04929 | 0.003901 | 0.00056 | 0.003814 | 0.017792 | 0.004045 | −0.037728 | −0.038155 | −0.043037 | 0.00916 | 0.057083 | 0.035032 | −0.018713 | −0.046255 |
| 332 | −0.060146 | −0.098419 | −0.079211 | 0.046641 | −0.037213 | −0.056777 | 0.183216 | −0.070148 | 0.038552 | −0.060815 | 0.014857 | −0.02774 | 0.039594 | 0.069893 |
| 333 | 0.030734 | −0.048402 | 0.020172 | −0.046068 | −0.026369 | 0.000569 | −0.034555 | −0.048251 | −0.045683 | −0.088173 | 0.050077 | 0.037635 | 0.01865 | −0.031384 |
| 334 | 0.015227 | 0.015739 | 0.073516 | −0.095679 | 0.005777 | 0.088444 | −0.106648 | −0.075927 | −0.032646 | 0.098106 | −0.102828 | 0.056472 | −0.091935 | 0.110499 |
| 335 | −0.019947 | −0.003681 | 0.022544 | 0.000292 | −0.020188 | −0.015254 | −0.014419 | −0.009871 | −0.083921 | −0.061615 | −0.022981 | 0.047343 | 0.003136 | −0.07077 |
| 336 | 0.024303 | −0.003614 | 0.032265 | −0.058493 | −0.046302 | −0.018982 | −0.035636 | 0.007412 | −0.010824 | 0.000127 | 0.086555 | 0.036404 | 0.01707 | −0.095933 |
| 337 | 0.000891 | 0.006944 | 0.034298 | −0.011801 | −0.034783 | −0.042494 | 0.017774 | −0.02437 | 0.040934 | −0.011678 | −0.02044 | 0.011227 | 0.028994 | 0.060127 |
| 338 | 0.113519 | 0.017598 | 0.044096 | −0.144905 | 0.057116 | 0.081976 | 0.176627 | 0.111496 | −0.060694 | 0.074825 | −0.061085 | −0.098613 | 0.038532 | 0.079952 |
| 339 | −0.095908 | −0.068709 | 0.071401 | 0.030595 | −0.045302 | −0.011024 | −0.004054 | −0.034066 | 0.089275 | 0.049663 | 0.059042 | 0.040669 | −0.092975 | −0.015455 |
| 340 | 0.113488 | −0.010944 | 0.000186 | 0.073126 | 0.027947 | 0.101568 | −0.17423 | −0.02718 | −0.104091 | 0.092499 | −0.055888 | −0.129007 | 0.200205 | 0.004049 |

| | BB | BC | BD | BE | BF | BG | BH | BI | BJ | BK | BL | BM | BN | BO |
|---|---|---|---|---|---|---|---|---|---|---|---|---|---|---|
| 1 | −0.054715 | 0.011905 | 0.014341 | −0.020284 | 0.07073 | −0.124344 | 0.164221 | 0.002368 | −0.058005 | 0.080075 | 0.000044 | −0.025475 | 0.039348 | −0.005293 |
| 2 | −0.007568 | −0.013698 | −0.002308 | 0.026203 | 0.211189 | −0.092968 | −0.211613 | −0.04018 | 0.049116 | −0.057183 | 0.060286 | 0.031191 | −0.032572 | 0.07929 |
| 3 | −0.015209 | −0.007974 | 0.057555 | −0.007441 | −0.036383 | 0.034811 | 0.098329 | 0.028042 | 0.000101 | −0.025347 | −0.000176 | −0.00543 | 0.008302 | 0.01695 |
| 4 | −0.008358 | 0.01097 | −0.003389 | −0.018954 | 0.015222 | −0.035402 | −0.072999 | 0.040577 | −0.034974 | 0.00482 | −0.040571 | −0.006765 | 0.016198 | −0.0292 |
| 5 | −0.032719 | 0.021704 | −0.123165 | −0.053327 | 0.065541 | −0.046124 | −0.014063 | −0.039702 | 0.012219 | 0.182219 | 0.015825 | 0.002181 | 0.034799 | 0.009931 |
| 6 | 0.038688 | 0.059239 | −0.077204 | −0.096328 | 0.061341 | −0.020443 | 0.123992 | 0.064995 | 0.061984 | −0.031137 | 0.058867 | 0.060366 | −0.045772 | 0.032428 |
| 7 | −0.088479 | −0.024757 | 0.160743 | −0.02549 | −0.158814 | 0.116544 | 0.085552 | 0.040744 | −0.043097 | −0.010667 | −0.033164 | −0.060809 | −0.036919 | −0.051392 |
| 8 | 0.08561 | −0.148607 | −0.075453 | 0.01636 | 0.019172 | −0.008706 | −0.148106 | 0.028049 | −0.079716 | 0.003662 | −0.080863 | −0.09816 | 0.059363 | −0.024446 |
| 9 | −0.082826 | 0.04032 | −0.012 | 0.039487 | −0.181825 | −0.044366 | 0.047693 | 0.053796 | −0.012139 | 0.089867 | −0.018913 | −0.034123 | 0.011312 | −0.020567 |
| 10 | −0.023697 | −0.027095 | 0.01852 | 0.079126 | −0.074336 | −0.009677 | 0.049861 | 0.023689 | −0.09058 | 0.05754 | −0.020381 | −0.019758 | −0.024083 | −0.059089 |
| 11 | 0.052119 | −0.10629 | −0.063371 | 0.030322 | 0.134048 | −0.096645 | 0.0084 | 0.010514 | 0.088568 | 0.006195 | 0.001937 | 0.079756 | 0.018288 | 0.004282 |
| 12 | −0.134065 | −0.02872 | −0.00253 | −0.042346 | −0.044533 | −0.001227 | −0.01368 | −0.075784 | −0.06339 | −0.092348 | 0.001731 | −0.029521 | −0.082719 | −0.020956 |
| 13 | 0.090733 | −0.002702 | 0.017672 | 0.004231 | 0.165934 | −0.134662 | −0.037596 | 0.002932 | −0.03278 | −0.033554 | −0.017022 | −0.013644 | −0.002949 | −0.00551 |
| 14 | −0.016982 | 0.022391 | −0.028746 | −0.060032 | −0.023311 | −0.010395 | 0.005524 | 0.058602 | 0.01883 | 0.037729 | 0.023231 | 0.018776 | 0.062719 | 0.020787 |
| 15 | 0.031841 | 0.01278 | 0.0667 | −0.078753 | 0.129094 | −0.004429 | −0.013298 | −0.012413 | 0.04014 | −0.040022 | 0.024723 | −0.049579 | −0.002882 | 0.042107 |
| 16 | 0.08112 | 0.191659 | 0.08272 | 0.029995 | −0.06434 | 0.051898 | −0.051333 | 0.031676 | 0.028048 | 0.036475 | 0.018284 | 0.027248 | 0.027322 | 0.04947 |
| 17 | 0.036687 | 0.081759 | 0.080453 | 0.012609 | 0.050791 | −0.087999 | −0.102394 | 0.026681 | −0.027319 | 0.02243 | −0.01499 | −0.027496 | 0.058815 | 0.014644 |
| 18 | −0.034623 | 0.080695 | −0.064681 | 0.079008 | −0.055734 | 0.033785 | −0.006928 | 0.065629 | 0.056702 | −0.040164 | −0.010527 | −0.001633 | 0.010493 | 0.022537 |
| 19 | 0.022564 | 0.083455 | −0.05068 | 0.04149 | −0.032792 | −0.058129 | 0.041325 | −0.011584 | −0.082944 | −0.002268 | −0.099736 | −0.035149 | 0.093579 | −0.021026 |
| 20 | 0.003436 | −0.039131 | −0.00875 | −0.02895 | 0.01474 | −0.070815 | −0.000936 | 0.046141 | −0.01493 | 0.0261 | −0.045593 | −0.043065 | 0.014213 | −0.005101 |
| 21 | 0.063819 | −0.015726 | −0.064181 | 0.131667 | −0.099203 | 0.090447 | 0.109607 | 0.014819 | 0.084996 | 0.073649 | 0.052489 | 0.014821 | −0.021056 | 0.038946 |
| 22 | 0.03779 | −0.158435 | 0.007588 | 0.069041 | −0.011088 | 0.003785 | −0.090779 | 0.003569 | 0.043603 | −0.029007 | −0.005431 | 0.0491461 | −0.009631 | 0.033887 |
| 23 | −0.187901 | −0.054924 | −0.018825 | −0.128927 | 0.126611 | −0.113603 | −0.057046 | 0.011724 | 0.018287 | −0.011185 | 0.015213 | 0.022159 | −0.101231 | −0.070563 |
| 24 | 0.045377 | −0.111325 | −0.009913 | 0.046365 | 0.031424 | −0.048081 | 0.027582 | −0.024493 | −0.141063 | −0.03133 | −0.103014 | 0.018034 | 0.023253 | −0.057112 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 25 | −0.05151 | 0.020848 | 0.133052 | 0.133973 | −0.12656 | 0.119382 | −0.003962 | −0.150277 | −0.042876 | −0.002814 | 0.016697 | −0.059433 | −0.021084 | 0.043721 |
| 26 | 0.029491 | 0.002125 | −0.021843 | −0.06214 | 0.057775 | −0.059631 | 0.16764 | −0.024866 | 0.000043 | −0.052977 | −0.054115 | 0.078084 | −0.105808 | −0.034277 |
| 27 | 0.002353 | 0.008792 | −0.016402 | −0.000607 | −0.075919 | 0.0891341 | 0.083401 | −0.051005 | 0.009968 | −0.011766 | 0.0076271 | −0.002239 | 0.045398 | 0.029651 |
| 28 | −0.105535 | 0.019113 | 0.086319 | 0.110932 | 0.055139 | 0.002892 | 0.084024 | 0.003462 | −0.030384 | −0.009531 | −0.054953 | 0.052726 | 0.034491 | 0.040115 |
| 29 | 0.014249 | 0.240109 | 0.096676 | −0.021346 | −0.188837 | 0.043935 | −0.731307 | 0.007217 | −0.010346 | 0.004727 | −0.021788 | 0.02508 | −0.021623 | −0.021333 |
| 30 | −0.005242 | 0.005255 | −0.052702 | −0.034194 | 0.08804 | −0.044768 | −0.028347 | 0.042471 | 0.014666 | 0.004499 | −0.035793 | −0.097731 | 0.004002 | −0.121602 |
| 31 | 0.005698 | −0.037636 | −0.004362 | 0.063646 | 0.022786 | −0.017631 | 0.002646 | −0.038609 | −0.052517 | −0.030026 | 0.005436 | 0.015318 | 0.006104 | 0.01813 |
| 32 | −0.055089 | 0.040575 | 0.036773 | 0.004569 | 0.078676 | −0.095758 | −0.039975 | −0.028582 | −0.049184 | 0.048295 | 0.006181 | 0.036514 | 0.068142 | −0.060007 |
| 33 | −0.040454 | −0.010288 | 0.04715 | −0.038748 | −0.085286 | 0.045947 | 0.041567 | 0.061989 | 0.026453 | −0.027107 | 0.011246 | 0.050072 | 0.006175 | −0.038167 |
| 34 | −0.004058 | −0.033006 | −0.010391 | −0.093737 | −0.051238 | −0.02443 | 0.015016 | −0.004625 | −0.025775 | −0.04096 | 0.007671 | −0.062006 | 0.010593 | 0.024944 |
| 35 | −0.091551 | −0.123801 | 0.068676 | −0.001034 | −0.17418 | 0.155086 | 0.007831 | −0.010182 | −0.01561 | −0.013426 | 0.011084 | −0.039751 | 0.073317 | 0.009106 |
| 36 | 0.045079 | −0.029686 | −0.019066 | −0.15553 | −0.173147 | 0.046686 | 0.010538 | 0.027193 | 0.088794 | −0.04292 | 0.057356 | −0.006177 | −0.020492 | −0.026133 |
| 37 | −0.014484 | −0.032335 | −0.043202 | 0.033773 | 0.056549 | −0.03858 | 0.014448 | 0.007218 | 0.041869 | −0.103717 | −0.01509 | −0.052954 | 0.039181 | −0.025719 |
| 38 | −0.033847 | −0.03113 | 0.157107 | 0.01775 | 0.008325 | −0.009661 | −0.035496 | −0.061846 | −0.098694 | 0.039759 | −0.027557 | 0.099499 | 0.00859 | −0.055552 |
| 39 | 0.141356 | −0.004147 | 0.025729 | −0.035468 | −0.070295 | −0.090868 | −0.010966 | 0.107855 | 0.034678 | 0.109939 | −0.043054 | −0.065517 | −0.027565 | −0.038188 |
| 40 | 0.016488 | 0.032012 | 0.033443 | −0.012665 | 0.535203 | 0.748207 | −0.017847 | 0.014449 | −0.020871 | 0.03339 | −0.026141 | −0.01683 | −0.000724 | −0.036829 |
| 41 | 0.00377 | 0.015913 | −0.014066 | 0.040083 | −0.148381 | 0.039722 | 0.060163 | 0.099032 | 0.037418 | 0.001971 | −0.052562 | −0.02253 | 0.084298 | 0.026459 |
| 42 | 0.012731 | 0.038294 | 0.012149 | −0.014611 | 0.020433 | −0.075285 | 0.011846 | −0.037578 | −0.060808 | −0.014239 | −0.030181 | 0.060832 | 0.021983 | 0.070805 |
| 43 | 0.018529 | 0.006643 | 0.037871 | −0.002981 | −0.026118 | −0.070314 | 0.049407 | 0.152554 | −0.002269 | 0.061775 | 0.006594 | −0.045666 | 0.058141 | 0.022013 |
| 44 | 0.025308 | 0.032692 | 0.010139 | 0.012693 | −0.091225 | 0.015105 | 0.052309 | 0.003824 | −0.064057 | −0.030556 | −0.106299 | −0.065039 | −0.020906 | −0.144054 |
| 45 | 0.049124 | −0.012652 | −0.035355 | 0.036132 | −0.003911 | −0.056627 | 0.015199 | 0.011724 | −0.000432 | 0.051604 | 0.053837 | 0.045824 | 0.04224 | 0.064241 |
| 46 | −0.020379 | 0.038704 | −0.075424 | −0.010989 | 0.074974 | −0.080185 | −0.021866 | −0.051215 | −0.004915 | −0.005533 | 0.033216 | 0.001971 | −0.036611 | −0.104989 |
| 47 | 0.043296 | −0.023712 | −0.009266 | 0.088258 | 0.033215 | −0.004633 | −0.01036 | −0.056647 | 0.050615 | −0.058382 | 0.040639 | −0.032364 | 0.019273 | 0.07564 |
| 48 | 0.015963 | 0.006931 | −0.0578 | −0.058784 | −0.075083 | 0.031473 | 0.04172 | 0.044759 | −0.04175 | 0.053135 | −0.047654 | 0.054908 | −0.027107 | 0.098993 |
| 49 | −0.022393 | 0.032501 | −0.055951 | −0.047654 | 0.045852 | −0.049503 | −0.036987 | 0.05087 | 0.008609 | −0.011641 | −0.035815 | −0.095372 | −0.014039 | 0.0752 |
| 50 | −0.015233 | −0.00287 | −0.08047 | −0.021912 | 0.062326 | −0.023163 | −0.028294 | 0.048534 | 0.025074 | 0.102743 | 0.066275 | 0.029652 | 0.015486 | 0.074489 |
| 51 | −0.047764 | 0.010243 | 0.054411 | 0.017407 | −0.012634 | 0.028932 | −0.024557 | 0.060894 | 0.049526 | −0.001549 | −0.039443 | −0.012684 | 0.026815 | 0.02988 |
| 52 | −0.015718 | 0.009526 | −0.033768 | −0.008955 | −0.073755 | 0.065808 | 0.021957 | −0.053765 | −0.034831 | −0.001911 | 0.018689 | −0.003015 | 0.006776 | −0.014017 |
| 53 | −0.041929 | 0.043753 | −0.044929 | −0.032214 | 0.055673 | −0.029158 | −0.050153 | 0.064112 | 0.131777 | −0.037895 | 0.049816 | 0.059448 | 0.048949 | 0.026799 |
| 54 | 0.014536 | 0.117108 | 0.011026 | −0.072048 | 0.028776 | −0.038725 | 0.003816 | 0.013575 | −0.090598 | 0.018505 | −0.089785 | −0.03933 | 0.012256 | −0.038328 |
| 55 | 0.020371 | 0.039394 | 0.040174 | 0.026452 | 0.01749 | 0.003758 | −0.008617 | 0.004016 | 0.004699 | 0.001458 | −0.01427 | −0.02452 | −0.036338 | −0.04243 |
| 56 | 0.004681 | −0.037493 | −0.041321 | −0.009986 | 0.013778 | −0.026418 | −0.042568 | −0.026949 | 0.003659 | −0.026464 | −0.062209 | −0.053988 | −0.057229 | −0.143641 |
| 57 | 0.06478 | 0.010423 | −0.004504 | −0.008576 | 0.056075 | −0.068442 | −0.006992 | 0.044428 | −0.001541 | 0.121271 | −0.039369 | −0.026652 | −0.043665 | −0.114382 |
| 58 | 0.054073 | −0.008855 | 0.051965 | −0.001477 | −0.010587 | 0.002347 | 0.008435 | −0.029736 | −0.009728 | −0.036761 | 0.07647 | 0.040024 | −0.034786 | −0.05222 |
| 59 | −0.075171 | 0.068951 | −0.005651 | 0.065349 | −0.053365 | 0.000926 | 0.015531 | 0.078931 | −0.014887 | 0.066999 | 0.024655 | 0.005126 | −0.03812 | −0.122251 |
| 60 | −0.028286 | 0.002983 | 0.013119 | 0.056597 | 0.069227 | 0.02117 | −0.002727 | 0.86511 | −0.044586 | −0.046133 | 0.008383 | 0.016733 | −0.030682 | −0.004154 |
| 61 | −0.104571 | −0.008872 | 0.128385 | 0.029158 | 0.01244 | −0.033626 | 0.02626 | −0.045525 | 0.867553 | 0.016024 | −0.065926 | −0.020015 | 0.009693 | −0.047619 |
| 62 | −0.01878 | −0.045649 | −0.043413 | −0.031855 | 0.025766 | 0.035967 | −0.020751 | −0.049115 | −0.001372 | 0.835211 | −0.00244 | −0.005734 | −0.028309 | 0.010967 |
| 63 | −0.013733 | 0.003553 | 0.013442 | 0.061946 | 0.002615 | −0.027335 | −0.001917 | 0.010082 | −0.064707 | −0.007231 | 0.905289 | −0.038905 | 0.006752 | −0.049671 |
| 64 | 0.059009 | −0.015099 | 0.025135 | 0.010758 | −0.048253 | 0.022229 | −0.024159 | 0.001101 | −0.020873 | −0.007844 | −0.025042 | 0.893509 | 0.005219 | −0.020363 |
| 65 | 0.053161 | −0.047232 | 0.024331 | −0.030358 | 0.018679 | 0.002486 | −0.002438 | −0.021577 | 0.012087 | −0.02922 | 0.01354 | 0.007317 | 0.897772 | −0.036785 |
| 66 | −0.04611 | 0.012042 | −0.008708 | −0.061349 | −0.023959 | 0.007852 | −0.020319 | −0.002454 | −0.039757 | −0.001038 | −0.035944 | −0.031757 | −0.040304 | 0.835579 |
| 67 | −0.041185 | −0.006127 | −0.05533 | −0.038305 | −0.003354 | −0.021421 | 0.040965 | 0.007118 | −0.03322 | 0.003377 | −0.041792 | −0.005442 | −0.000883 | −0.068187 |
| 68 | 0.119316 | −0.087116 | −0.086497 | 0.039397 | −0.06638 | 0.039459 | −0.037415 | −0.001795 | −0.003023 | −0.012875 | −0.006329 | 0.024078 | −0.039562 | −0.016659 |
| 69 | −0.066947 | −0.088643 | 0.052785 | −0.096556 | −0.045727 | 0.04355 | −0.04379 | 0.019298 | −0.016807 | 0.001771 | −0.001714 | 0.003988 | 0.013022 | 0.003202 |
| 70 | −0.005943 | 0.019564 | 0.024313 | −0.045885 | −0.025595 | 0.029433 | 0.021949 | −0.012002 | −0.00951 | −0.005383 | −0.009034 | 0.019715 | −0.01062 | −0.03179 |
| 71 | −0.005616 | −0.128581 | −0.0706 | 0.076659 | −0.036848 | 0.04067 | −0.021074 | 0.008061 | 0.002755 | 0.018074 | 0.000319 | −0.019294 | −0.003458 | −0.003486 |
| 72 | −0.014967 | −0.057921 | −0.012348 | 0.066882 | −0.040564 | 0.050012 | −0.006922 | −0.002657 | 0.008721 | 0.002455 | 0.002912 | −0.022504 | −0.00663 | 0.023889 |
| 73 | 0.017571 | −0.017688 | −0.065846 | −0.118333 | −0.031708 | 0.038902 | 0.01213 | 0.001781 | 0.024126 | −0.00146 | 0.033687 | 0.019625 | −0.008645 | −0.02511 |
| 74 | 0.100794 | −0.001051 | 0.049417 | 0.076587 | −0.024297 | 0.033738 | 0.013248 | 0.009639 | 0.021606 | −0.013075 | 0.000132 | −0.006224 | −0.005903 | 0.006551 |

APPENDIX B3-continued

PCA Transformation Matrix (340 × 340 Early/Late)

| | | | | | | | | | | | | | | |
|---|---|---|---|---|---|---|---|---|---|---|---|---|---|---|
| 75 | 0.01329 | −0.009879 | −0.021428 | 0.027547 | −0.021182 | 0.025971 | 0.002711 | −0.009606 | −0.01387 | −0.005754 | −0.018879 | 0.00231 | −0.012396 | −0.024824 |
| 76 | −0.077355 | 0.033756 | 0.00936 | 0.012269 | 0.040112 | −0.046996 | −0.006234 | 0.011651 | −0.00414 | −0.000722 | −0.013995 | 0.013012 | −0.003635 | −0.001293 |
| 77 | 0.011862 | −0.035979 | −0.024003 | 0.026035 | −0.031053 | 0.03418 | −0.003182 | −0.0007 | −0.014716 | 0.002256 | −0.02095 | 0.0062 | −0.009297 | −0.024041 |
| 78 | 0.003812 | 0.000748 | −0.044879 | 0.038482 | −0.08531 | 0.07569 | 0.014749 | −0.000657 | −0.013671 | 0.00572 | −0.015621 | 0.008786 | −0.007825 | −0.026457 |
| 79 | 0.050739 | 0.026672 | 0.001151 | −0.072291 | −0.031643 | 0.031568 | 0.013211 | −0.0129 | 0.003509 | −0.006142 | 0.008804 | −0.009746 | −0.005786 | −0.022273 |
| 80 | 0.067098 | 0.009945 | 0.152968 | −0.049695 | 0.026808 | −0.040321 | 0.019697 | 0.003225 | −0.027652 | 0.029017 | −0.007346 | −0.0431 | 0.003636 | −0.029636 |
| 81 | −0.037188 | −0.064204 | 0.134638 | 0.152435 | 0.033454 | −0.026918 | 0.026388 | 0.010456 | −0.009024 | −0.006548 | −0.015534 | 0.01604 | −0.008728 | 0.021574 |
| 82 | −0.022942 | 0.051689 | −0.036019 | −0.024823 | 0.027803 | −0.024697 | 0.029225 | −0.0028 | 0.005724 | 0.018684 | 0.018073 | 0.01051 | 0.002304 | 0.004013 |
| 83 | 0.00325 | 0.068667 | 0.014513 | 0.022636 | 0.023371 | −0.013247 | 0.036276 | 0.004183 | −0.006918 | 0.025243 | 0.004811 | −0.001892 | 0.00298 | 0.009144 |
| 84 | 0.009829 | 0.005753 | −4.004708 | 0.060156 | 0.003395 | 0.001418 | 0.045003 | 0.005877 | −0.000096 | 0.018917 | 0.009701 | 0.007657 | −0.001952 | 0.013966 |
| 85 | −0.040995 | −0.067886 | 0.036793 | −0.039792 | 0.011054 | −0.01444 | 0.000625 | 0.017582 | −0.012562 | 0.000258 | 0.011023 | −0.020841 | 0.008207 | 0.012921 |
| 86 | −0.05498 | −0.063342 | −0.016368 | 0.048858 | −0.019527 | 0.005194 | −0.008231 | 0.015412 | −0.011374 | 0.019705 | 0.00238 | −0.008009 | 0.007945 | −0.005036 |
| 87 | −0.046332 | −0.00145 | 0.045584 | 0.015097 | 0.057449 | −0.046708 | −0.011853 | −0.005699 | −0.011922 | 0.010291 | 0.000588 | −0.014584 | 0.008617 | 0.002213 |
| 88 | −0.016213 | 0.045584 | −0.013025 | −0.024683 | 0.021234 | −0.003312 | 0.041892 | 0.001916 | 0.002528 | 0.023602 | 0.010448 | 0.000744 | 0.009785 | 0.00473 |
| 89 | 0.00368 | 0.012919 | −0.03055 | 0.022551 | −0.049582 | 0.057691 | 0.024758 | 0.008485 | 0.001388 | 0.02409 | 0.016228 | 0.003579 | 0.004627 | 0.006763 |
| 90 | 0.026011 | −0.016124 | 0.030376 | 0.006947 | −0.025795 | 0.037637 | 0.014856 | −0.003724 | −0.017372 | 0.007356 | 0.003368 | −0.009753 | −0.00671 | −0.000288 |
| 91 | 0.087969 | −0.005612 | −0.027481 | 0.04589 | −0.020456 | 0.016281 | 0.022993 | 0.007159 | 0.015026 | 0.015713 | 0.018502 | −0.010555 | −0.013821 | 0.001478 |
| 92 | −0.002587 | 0.105976 | 0.00785 | 0.060152 | 0.005054 | 0.008677 | 0.031387 | 0.022383 | 0.0240891 | 0.03321 | 0.022944 | 0.034701 | −0.011374 | 0.017196 |
| 93 | 0.088337 | −0.069971 | 0.016992 | 0.00409 | 0.043823 | 0.001865 | 0.028349 | −0.009861 | −0.015899 | 0.00919 | −0.012435 | −0.008339 | −0.012777 | −0.002839 |
| 94 | 0.038874 | 0.073438 | −0.020221 | −0.037974 | −0.027119 | 0.06471 | 0.040638 | −0.014894 | 0.007068 | 0.005589 | 0.011457 | 0.0178811 | 0.006308 | −0.011914 |
| 95 | −0.009287 | −0.039843 | −0.061719 | 0.009389 | −0.0187 | 0.018243 | −0.056611 | 0.023247 | 0.016401 | 0.008218 | 0.016193 | 0.016663 | 0.040167 | 0.00483 |
| 96 | −0.008627 | 0.068151 | −0.040407 | −0.104366 | −0.063017 | 0.006759 | 0.066674 | −0.010122 | −0.009862 | 0.030293 | −0.0139 | 0.005855 | 0.015356 | −0.030202 |
| 97 | 0.024133 | 0.067229 | 0.154916 | 0.000191 | 0.002939 | −0.020749 | −0.000185 | −0.001268 | −0.010607 | 0.02459 | −0.006318 | −0.007902 | −0.008877 | −0.009457 |
| 98 | 0.019678 | 0.037736 | 0.01156 | 0.028266 | −0.000434 | −0.00731 | 0.025535 | 0.009701 | 0.004212 | 0.006111 | 0.001559 | −0.017899 | 0.012285 | −0.00465 |
| 99 | −0.002012 | 0.017216 | 0.075055 | −0.035348 | −0.002978 | −0.012208 | 0.005084 | 0.006145 | 0.001912 | 0.020376 | 0.006457 | 0.006855 | −0.005362 | −0.000262 |
| 100 | −0.104336 | 0.040932 | −0.025964 | −0.021902 | −0.014547 | −0.00123 | 0.008425 | 0.014573 | −0.010737 | −0.007039 | −0.021808 | −0.001196 | 0.023012 | 0.005459 |
| 101 | 0.057797 | 0.004131 | 0.003545 | 0.05893 | 0.021824 | −0.007745 | 0.014406 | 0.006472 | 0.003719 | −0.003965 | −0.002615 | −0.021476 | 0.009882 | −0.01301 |
| 102 | −0.042189 | −0.042379 | 0.085304 | 0.079714 | −0.01917 | −0.02464 | 0.06582 | 0.020154 | −0.020292 | 0.039093 | −0.032027 | 0.022411 | 0.021694 | 0.037662 |
| 103 | 0.054206 | −0.029632 | 0.065986 | 0.111921 | −0.011078 | −0.012572 | −0.031232 | 0.016961 | −0.000119 | 0.017524 | −0.014583 | −0.020887 | 0.014787 | 0.015502 |
| 104 | −0.007318 | −0.06945 | 0.089865 | −0.062637 | −0.023991 | 0.000552 | −0.013847 | 0.016557 | −0.009462 | −0.012799 | 0.001727 | −0.008267 | −0.025468 | −0.018719 |
| 105 | −0.056824 | −0.035786 | −0.12354 | −0.014141 | 0.02452 | 0.020167 | 0.02567 | −0.029647 | 0.022513 | −0.032854 | 0.023723 | 0.017855 | −0.034238 | 0.026429 |
| 106 | 0.045701 | 0.029443 | −0.089073 | 0.077673 | 0.000734 | −0.002816 | −0.002708 | −0.003853 | 0.029081 | −0.018054 | −0.008648 | −0.027208 | 0.016903 | −0.008263 |
| 107 | −0.051071 | 0.032208 | −0.048477 | 0.002234 | −0.025243 | 0.02804 | −0.023725 | 0.001252 | 0.001384 | −0.005895 | −0.018622 | −0.00112 | 0.013427 | −0.02587 |
| 108 | 0.067633 | −0.089441 | 0.036342 | 0.015315 | 0.015119 | −0.024214 | 0.036069 | 0.017031 | 0.007152 | 0.000674 | 0.014885 | −0.01599 | 0.013682 | 0.035305 |
| 109 | −0.139813 | 0.113425 | −0.026434 | 0.037187 | 0.026288 | 0.007534 | 0.007503 | 0.0055 | −0.004665 | −0.057191 | 0.001696 | 0.020394 | 0.023473 | 0.042246 |
| 110 | 0.015431 | −0.024305 | 0.061269 | 0.139026 | 0.044912 | −0.055015 | −0.053888 | −0.006002 | −0.024668 | 0.04208 | −0.010481 | −0.027866 | 0.016114 | 0.010278 |
| 111 | −0.011423 | 0.152506 | 0.018105 | 0.026234 | −0.024457 | −0.028299 | 0.057183 | −0.001583 | 0.006653 | −0.005565 | 0.011138 | −0.01057 | 0.000561 | −0.001134 |
| 112 | 0.070955 | −0.088 | 0.02106 | −0.057393 | −0.045079 | 0.018459 | 0.041221 | 0.031793 | −0.01202 | 0.012911 | −0.018604 | −0.015759 | 0.024583 | 0.022518 |
| 113 | 0.056676 | 0.003206 | −0.096222 | −0.007942 | −0.059477 | 0.037688 | −0.017578 | 0.009233 | 0.029188 | −0.009993 | 0.027546 | 0.001917 | 0.012168 | −0.001675 |
| 114 | 0.098861 | −0.139017 | 0.140248 | −0.128835 | −0.023103 | 0.003229 | −0.027943 | 0.067257 | 0.002604 | 0.030566 | 0.005297 | −0.01663 | 0.022322 | 0.010935 |
| 115 | 0.041503 | 0.024318 | −0.05195 | 0.108578 | 0.048956 | −0.054422 | 0.028361 | −0.028834 | −0.000672 | −0.053877 | −0.015439 | −0.022432 | −0.015661 | −0.022828 |
| 116 | 0.036509 | 0.022232 | 0.09555 | 0.051607 | −0.025873 | 0.019517 | 0.022194 | 0.010792 | −0.016815 | −0.00577 | −0.012174 | −0.010565 | −0.015564 | 0.014478 |
| 117 | −0.030441 | −0.019355 | 0.108514 | 0.040115 | 0.035603 | −0.057864 | 0.022604 | 0.001947 | 0.023584 | 0.020626 | 0.015237 | 0.022103 | −0.013631 | 0.025001 |
| 118 | 0.050417 | −0.012628 | 0.065421 | −0.132637 | −0.019085 | 0.030543 | 0.008914 | 0.01389 | 0.029428 | −0.058348 | 0.0156 | 0.006758 | −0.002008 | −0.001912 |
| 119 | −0.022734 | −0.032711 | −0.028477 | −0.041677 | −0.022491 | 0.050949 | −0.056606 | 0.012016 | 0.019513 | −0.010217 | −0.001851 | −0.003172 | 0.011996 | 0.007302 |
| 120 | 0.041642 | −0.036513 | 0.016239 | −0.009935 | −0.036323 | 0.019559 | −0.011832 | 0.042086 | 0.050755 | 0.023904 | 0.028317 | −0.004923 | −0.005047 | 0.001667 |
| 121 | 0.096512 | 0.021046 | 0.065046 | −0.073568 | −0.025275 | 0.023395 | 0.013763 | 0.022993 | 0.039463 | −0.021114 | 0.002316 | −0.016669 | −0.015521 | 0.029603 |
| 122 | 0.029268 | 0.056463 | 0.010597 | 0.059294 | 0.056507 | −0.03569 | 0.014895 | −0.025157 | −0.029549 | −0.004169 | −0.001155 | 0.004035 | 0.021975 | 0.009783 |
| 123 | −0.027822 | −0.053776 | −0.091467 | 0.023446 | −0.003472 | 0.038045 | −0.057111 | −0.002762 | −0.004122 | −0.032883 | 0.000086 | −0.01218 | 0.009299 | −0.001557 |
| 124 | −0.030286 | 0.021941 | −0.002963 | −0.003143 | −0.007553 | 0.03577 | −0.025612 | −0.00391 | −0.007753 | −0.030904 | −0.014013 | −0.005999 | 0.007556 | 0.005649 |

APPENDIX B3-continued

PCA Transformation
Matrix (340 × 340 Early/Late)

| | | | | | | | | | | | | | |
|---|---|---|---|---|---|---|---|---|---|---|---|---|---|
| 125 | 0.032884 | −0.085056 | −0.048376 | 0.024919 | 0.020947 | −0.036409 | −0.074758 | 0.012659 | 0.024872 | 0.008489 | 0.011958 | −0.025477 | 0.001475 | 0.016207 |
| 126 | −0.048099 | −0.012595 | −0.003765 | −0.042434 | 0.020547 | 0.005254 | −0.008519 | 0.003384 | 0.030204 | −0.018565 | 0.022027 | 0.021409 | −0.012023 | 0.007901 |
| 127 | −0.00087 | 0.050133 | −0.01129 | 0.00729 | 0.019581 | −0.004883 | −0.017375 | −0.002594 | 0.02361 | 0.010484 | 0.009392 | 0.007636 | −0.002659 | 0.021275 |
| 128 | −0.02547 | −0.079084 | 0.000348 | 0.005395 | 0.00767 | 0.006659 | −0.028286 | 0.002991 | 0.002333 | 0.003146 | 0.004072 | 0.012767 | −0.009622 | −0.013718 |
| 129 | 0.015195 | −0.049149 | 0.121745 | −0.009541 | 0.00534 | 0.023935 | 0.048501 | −0.001656 | −0.038731 | 0.005684 | −0.016253 | −0.034514 | 0.009152 | −0.012899 |
| 130 | 0.019002 | 0.052403 | −0.089043 | 0.011991 | 0.02193 | 0.003539 | −0.016176 | −0.000761 | 0.003315 | −0.03818 | −0.003994 | −0.001037 | −0.013471 | −0.024975 |
| 131 | 0.08448 | 0.072928 | −0.060486 | −0.009669 | −0.006304 | 0.044666 | −0.013425 | −0.03447 | 0.027504 | 0.013381 | 0.015629 | −0.013124 | −0.016093 | 0.015817 |
| 132 | −0.120987 | −0.05346 | 0.074858 | −0.048673 | −0.027815 | 0.047184 | −0.03663 | 0.020907 | 0.006219 | 0.011973 | 0.029208 | −0.011539 | 0.011877 | 0.001373 |
| 133 | 0.101192 | 0.000967 | 0.008588 | −0.01396 | −0.066453 | 0.040258 | 0.007882 | −0.004381 | 0.016719 | −0.002816 | 0.001765 | −0.011792 | −0.007165 | −0.004565 |
| 134 | 0.123848 | 0.047056 | −0.01089 | −0.080974 | 0.033322 | −0.019236 | −0.048257 | −0.004604 | −0.01818 | 0.012836 | −0.005025 | 0.015487 | −0.014061 | 0.002069 |
| 135 | 0.000138 | 0.011968 | −0.058735 | −0.044345 | −0.088253 | 0.059854 | 0.003346 | 0.022589 | 0.005679 | 0.014367 | 0.003257 | −0.005288 | 0.011087 | −0.008952 |
| 136 | 0.000874 | 0.117185 | −0.075802 | 0.008102 | −0.001672 | −0.00567 | −0.002459 | −0.003686 | 0.019296 | −0.001948 | 0.019808 | 0.017592 | −0.003327 | 0.020632 |
| 137 | 0.037553 | −0.016235 | −0.053 | 0.065169 | −0.021034 | 0.057438 | −0.028741 | −0.00133 | 0.014182 | −0.031371 | 0.004003 | 0.001792 | 0.003976 | −0.008121 |
| 138 | 0.07993 | 0.044853 | 0.080561 | 0.009026 | 0.014235 | −0.019706 | −0.037409 | 0.025191 | 0.028465 | 0.032923 | 0.005621 | −0.001321 | 0.007415 | 0.014003 |
| 139 | −0.11761 | −0.016513 | 0.000266 | −0.086807 | 0.041954 | −0.017365 | 0.129425 | 0.00192 | −0.029264 | −0.006161 | 0.004408 | 0.030877 | 0.005865 | 0.016287 |
| 140 | 0.012711 | −0.144267 | 0.019733 | −0.010484 | −0.000753 | −0.010808 | 0.026843 | 0.013472 | −0.005648 | 0.003367 | 0.035973 | 0.032452 | −0.00729 | 0.007513 |
| 141 | −0.13155 | −0.081762 | −0.032744 | 0.016036 | −0.01715 | 0.044097 | −0.016028 | 0.020241 | −0.002246 | 0.032152 | 0.006345 | 0.038245 | 0.033271 | 0.009953 |
| 142 | −0.032367 | 0.037294 | 0.101185 | 0.011775 | 0.024406 | −0.037362 | 0.031991 | 0.024255 | −0.017235 | 0.00199 | −0.012908 | 0.002634 | 0.00102 | 0.006659 |
| 143 | 0.076423 | −0.008839 | −0.017342 | 0.010901 | 0.035124 | −0.033682 | 0.004279 | 0.008352 | −0.024154 | 0.008626 | −0.015857 | −0.013818 | 0.010949 | 0.009705 |
| 144 | 0.001249 | −0.016666 | −0.008974 | 0.026042 | −0.02997 | 0.031539 | −0.026932 | −0.024409 | −0.05287 | 0.000736 | −0.036407 | −0.013513 | 0.02448 | −0.016724 |
| 145 | 0.106458 | 0.015092 | 0.085525 | −0.068602 | 0.042685 | −0.04222 | −0.045577 | −0.01665 | −0.021891 | 0.00163 | 0.000574 | −0.029189 | 0.005502 | −0.005363 |
| 146 | −0.050297 | −0.066653 | 0.034801 | −0.088418 | −0.033963 | 0.007629 | −0.023847 | 0.034206 | 0.003094 | 0.01258 | 0.007297 | −0.005632 | 0.000766 | −0.014712 |
| 147 | −0.073448 | −0.147684 | −0.019546 | −0.01597 | 0.000462 | −0.028511 | −0.060526 | 0.054968 | 0.029908 | 0.054764 | 0.014013 | 0.007797 | −0.030349 | −0.018074 |
| 148 | −0.029773 | 0.119007 | −0.062464 | 0.016792 | 0.031563 | −0.052192 | 0.051666 | 0.009942 | −0.008694 | 0.003612 | −0.002995 | 0.029676 | 0.018651 | −0.061731 |
| 149 | 0.086345 | 0.007674 | 0.022199 | −0.018022 | −0.00693 | 0.00602 | −0.009367 | −0.001077 | 0.019395 | −0.005699 | 0.018066 | 0.006084 | 0.000821 | −0.001988 |
| 150 | 0.09893 | 0.009332 | 0.019665 | −0.041137 | 0.008974 | −0.009293 | 0.028978 | 0.051475 | 0.002637 | 0.015055 | −0.000898 | −0.016875 | −0.005414 | 0.017878 |
| 151 | −0.060396 | 0.012144 | −0.007674 | −0.079553 | 0.027458 | −0.006793 | 0.05498 | −0.002016 | −0.01804 | 0.029707 | −0.000109 | 0.013176 | −0.000127 | −0.021105 |
| 152 | 0.034244 | 0.07284 | −0.021942 | −0.011779 | −0.018998 | 0.005657 | 0.009632 | 0.020021 | 0.01442 | 0.039174 | 0.002718 | 0.007981 | −0.010796 | 0.016492 |
| 155 | −0.120514 | −0.099782 | 0.012706 | −0.021162 | 0.015799 | −0.033088 | −0.026774 | 0.01463 | −0.024173 | −0.006436 | −0.012768 | 0.004131 | −0.02109 | 0.002491 |
| 154 | −0.015156 | 0.033894 | −0.022819 | 0.030653 | −0.005897 | −0.000421 | 0.000089 | −0.009099 | −0.011802 | 0.002908 | −0.012899 | 0.002867 | −0.032278 | −0.002295 |
| 155 | 0.014489 | −0.030548 | 0.106087 | −0.072324 | −0.019024 | −0.019685 | −0.022667 | −0.00228 | −0.006876 | −0.016063 | 0.003909 | −0.041126 | −0.03602 | −0.003238 |
| 156 | 0.05673 | −0.077967 | −0.114327 | 0.057596 | 0.000842 | 0.001741 | −0.046962 | 0.010539 | 0.009562 | 0.024756 | −0.02864 | −0.009113 | −0.012414 | 0.018711 |
| 157 | −0.054547 | −0.005638 | 0.059471 | 0.01696 | −0.006859 | 0.010465 | 0.009552 | 0.01823 | −0.003062 | 0.001714 | −0.002525 | −0.008819 | 0.014667 | 0.006354 |
| 158 | −0.049831 | −0.101461 | 0.056924 | 0.059987 | −0.007106 | 0.011194 | −0.040176 | −0.013354 | −0.008361 | 0.016493 | 0.013803 | −0.002499 | −0.016717 | 0.002749 |
| 159 | 0.066725 | 0.089628 | 0.014005 | −0.016708 | 0.001197 | 0.034797 | 0.059885 | −0.001782 | −0.000173 | 0.004042 | −0.001839 | −0.002118 | −0.022632 | 0.008698 |
| 160 | 0.086828 | −0.066347 | −0.176672 | 0.081143 | 0.028402 | −0.028947 | −0.035661 | 0.019543 | 0.044313 | −0.010766 | −0.00791 | 0.020442 | −0.01094 | 0.025624 |
| 161 | −0.1056 | −0.043744 | 0.077766 | −0.056608 | −0.020602 | 0.027243 | −0.014582 | 0.018139 | −0.037497 | 0.024203 | −0.006493 | 0.019279 | −0.001265 | −0.025615 |
| 162 | 0.084969 | −0.072752 | 0.012653 | −0.066424 | 0.038329 | −0.008206 | −0.038235 | 0.031458 | 0.025391 | −0.004271 | −0.006021 | 0.007538 | 0.023949 | 0.031318 |
| 163 | 0.002566 | 0.092992 | 0.004203 | 0.025569 | 0.03088 | −0.015059 | 0.003203 | 0.02231 | 0.002177 | 0.018748 | −0.019533 | 0.000551 | 0.010817 | 0.020191 |
| 164 | −0.060228 | −0.059827 | 0.020782 | −0.017527 | 0.064213 | −0.007718 | 0.005183 | −0.031079 | 0.006432 | −0.02125 | 0.002164 | 0.03338 | 0.003756 | 0.044758 |
| 165 | 0.043603 | 0.082675 | 0.093796 | −0.056459 | −0.025298 | −0.021963 | 0.063321 | −0.036458 | −0.004802 | −0.019769 | −0.014832 | 0.020342 | −0.062469 | −0.074572 |
| 166 | −0.058952 | 0.01516 | −0.026505 | 0.05182 | 0.006663 | 0.040007 | 0.02323 | −0.025341 | 0.019159 | −0.0469 | 0.022982 | 0.008187 | 0.018752 | −0.0033 |
| 167 | 0.019779 | −0.100256 | 0.001689 | 0.017917 | −0.011799 | 0.01982 | −0.032151 | −0.01526 | −0.007254 | −0.021399 | 0.025564 | −0.010375 | 0.009194 | 0.009437 |
| 168 | −0.017823 | 0.033136 | −0.031522 | 0.023401 | −0.003974 | 0.003043 | −0.00785 | 0.000372 | −0.004662 | −0.023568 | −0.034022 | −0.003525 | 0.02728 | 0.010686 |
| 169 | 0.008077 | −0.008911 | 0.026644 | 0.031055 | 0.006143 | −0.018732 | −0.017708 | 0.021419 | 0.00408 | 0.017281 | −0.004207 | −0.046083 | 0.014647 | −0.007965 |
| 171 | 0.021939 | −0.018456 | 0.011463 | 0.026908 | 0.03839 | −0.036903 | −0.003509 | 0.009443 | −0.003551 | 0.022346 | −0.019577 | −0.032329 | 0.009232 | −0.019389 |
| 171 | −0.054947 | −0.024069 | −0.01214 | −0.031016 | −0.042062 | 0.024394 | 0.0272 | 0.023758 | 0.008854 | 0.007372 | 0.009185 | −0.016267 | 0.018511 | −0.001159 |
| 172 | −0.00058 | −0.047688 | 0.074348 | 0.060027 | −0.055535 | 0.023839 | 0.00452 | 0.023908 | 0.014628 | 0.020738 | 0.010398 | −0.02168 | −0.008175 | 0.00936 |
| 173 | 0.038437 | −0.048962 | 0.020677 | 0.042546 | −0.00507 | −0.004693 | −0.003959 | −0.002702 | 0.0213 | −0.021539 | 0.004833 | −0.010537 | −0.028927 | −0.011237 |
| 174 | 0.014385 | −0.031208 | −0.007189 | 0.013038 | 0.008109 | −0.016832 | −0.036718 | −0.013709 | 0.005466 | −0.010775 | 0.010166 | −0.008931 | −0.001882 | −0.005453 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 175 | −0.012914 | 0.046468 | 0.019488 | −0.030854 | 0.050237 | −0.033052 | 0.005235 | −0.017371 | 0.003327 | 0.017384 | 0.032687 | 0.016661 | −0.003213 | −0.002724 |
| 176 | −0.049431 | 0.093555 | −0.041361 | 0.091288 | −0.010579 | 0.003066 | 0.036845 | −0.006919 | 0.009365 | 0.021067 | −0.003231 | 0.013114 | 0.005925 | 0.001443 |
| 177 | 0.015315 | −0.095105 | −0.103107 | −0.001676 | −0.031046 | 0.010659 | −0.015593 | −0.005885 | 0.011131 | −0.015028 | −0.001119 | 0.00437 | −0.010291 | 0.015748 |
| 178 | −0.078081 | −0.010877 | −0.011684 | −0.000036 | 0.031059 | −0.01015 | 0.006834 | 0.007477 | −0.010771 | −0.000463 | −0.015371 | 0.000782 | 0.006599 | −0.042892 |
| 179 | −0.015546 | 0.007778 | 0.015681 | 0.010112 | 0.031517 | −0.034753 | −0.000292 | 0.017564 | 0.004356 | 0.008342 | −0.000751 | −0.01718 | 0.01458 | −0.002449 |
| 180 | 0.018495 | −0.007313 | −0.008548 | 0.025644 | −0.00993 | −0.000791 | 0.011113 | 0.016215 | 0.004924 | 0.00493 | −0.002209 | −0.01354 | 0.004697 | −0.020983 |
| 181 | 0.005435 | −0.009662 | 0.011228 | 0.042041 | 0.019635 | −0.022262 | 0.003381 | 0.006034 | 0.000488 | 0.0008 | −0.003506 | −0.01653 | 0.006281 | −0.006824 |
| 182 | −0.001528 | −0.008796 | 0.027932 | 0.024805 | −0.00735 | 0.009235 | 0.028312 | 0.005898 | −0.004499 | 0.014662 | −0.007179 | 0.002962 | 0.002092 | −0.002016 |
| 183 | −0.086342 | −0.023794 | −0.014783 | −0.035883 | −0.022656 | 0.024471 | −0.011136 | 0.013867 | 0.009686 | −0.000079 | 0.007088 | −0.002509 | 0.013495 | 0.022079 |
| 184 | −0.06815 | 0.019286 | −0.065517 | −0.062771 | −0.045769 | 0.027488 | −0.043109 | 0.039921 | 0.020537 | −0.007398 | −0.00827 | −0.03241 | 0.037122 | −0.004708 |
| 185 | 0.057664 | −0.007244 | 0.064337 | 0.13898 | 0.007511 | −0.00047 | −0.024856 | −0.011519 | −0.028333 | −0.008132 | −0.027861 | −0.025275 | −0.021402 | −0.02867 |
| 186 | −0.059628 | 0.016556 | −0.072082 | −0.072638 | −0.042412 | 0.039548 | 0.001753 | 0.019936 | 0.011413 | −0.051739 | 0.009627 | 0.017104 | −0.004523 | −0.030471 |
| 187 | 0.008307 | −0.018855 | 0.037471 | 0.008932 | 0.016704 | −0.000609 | −0.023317 | 0.018028 | 0.016835 | 0.00295 | −0.010496 | 0.000674 | −0.014141 | −0.010957 |
| 188 | −0.000561 | −0.038031 | 0.028249 | 0.018856 | 0.010011 | 0.009423 | −0.021599 | 0.009563 | 0.002032 | 0.018788 | −0.018452 | −0.000371 | −0.00329 | −0.003554 |
| 189 | −0.037521 | 0.06621 | 0.019303 | 0.019445 | 0.02873 | −0.025623 | 0.024798 | 0.023535 | −0.006897 | 0.033638 | −0.011558 | 0.000134 | 0.033069 | 0.041612 |
| 190 | 0.017339 | −0.024749 | −0.057416 | −0.027338 | 0.015449 | 0.016371 | −0.043281 | −0.016732 | 0.019136 | −0.01318 | 0.023133 | 0.000724 | 0.002971 | −0.000083 |
| 191 | −0.019361 | −0.0137 | −0.009491 | −0.016523 | −0.015681 | 0.001125 | −0.018978 | 0.007451 | 0.020823 | −0.008286 | 0.023661 | −0.002739 | 0.006182 | 0.008425 |
| 192 | −0.004607 | −0.025903 | 0.077462 | −0.084218 | 0.005233 | −0.003857 | −0.032214 | 0.016899 | 0.006507 | 0.038191 | 0.001318 | 0.007394 | 0.01142 | 0.024207 |
| 193 | −0.089352 | −0.028742 | −0.06564 | 0.032867 | −0.001747 | 0.021288 | −0.067546 | −0.001952 | 0.021149 | 0.018901 | 0.002843 | 0.014539 | −0.001949 | −0.005538 |
| 194 | −0.052892 | −0.015697 | 0.016397 | 0.053887 | −0.001144 | −0.001746 | −0.00334 | 0.01369 | 0.008109 | 0.028881 | 0.002416 | −0.004506 | −0.007221 | 0.006407 |
| 195 | 0.088433 | 0.044057 | 0.058025 | 0.064351 | 0.010681 | 0.001705 | −0.010012 | 0.008248 | 0.003157 | −0.010254 | 0.005857 | −0.00393 | −0.006994 | 0.015022 |
| 196 | 0.06016 | 0.03925 | 0.047908 | −0.023155 | 0.006207 | 0.006996 | 0.011032 | 0.001878 | −0.012251 | −0.00267 | 0.004465 | −0.011158 | 0.010225 | −0.006597 |
| 197 | 0.074732 | −0.070887 | −0.002711 | −0.076588 | −0.024529 | 0.04011 | −0.035977 | −0.019656 | −0.000042 | 0.005387 | 0.015061 | −0.009217 | −0.008963 | −0.015214 |
| 198 | 0.006456 | −0.031039 | 0.026551 | 0.063894 | 0.046926 | −0.024954 | −0.010736 | 0.012898 | 0.010873 | −0.009911 | −0.008587 | 0.020789 | −0.014147 | 0.001348 |
| 199 | −0.072043 | 0.168819 | 0.090209 | 0.133803 | 0.018334 | −0.001879 | 0.021692 | 0.017864 | 0.017456 | 0.023867 | 0.011255 | −0.008203 | 0.04364 | 0.001415 |
| 200 | −0.145907 | −0.087334 | −0.004429 | −0.041927 | −0.008212 | 0.017416 | 0.006789 | 0.005741 | −0.011964 | −0.008192 | 0.005003 | 0.0179 | 0.006505 | 0.030847 |
| 201 | −0.010814 | 0.063907 | −0.021999 | 0.011404 | 0.006884 | −0.012906 | −0.011978 | 0.022623 | 0.003789 | 0.015277 | −0.008617 | 0.044446 | 0.00314 | −0.004013 |
| 202 | 0.031236 | −0.019912 | −0.060127 | −0.021826 | −0.001549 | 0.005047 | 0.011003 | 0.004649 | 0.011134 | 0.007434 | −0.001691 | 0.032417 | −0.010193 | −0.020398 |
| 203 | 0.008795 | −0.027789 | 0.023481 | −0.03326 | 0.042359 | −0.039722 | 0.008805 | −0.023559 | 0.000836 | −0.00486 | 0.0008 | −0.044343 | −0.019198 | 0.017398 |
| 204 | 0.021079 | 0.075214 | 0.031322 | 0.041709 | 0.002087 | 0.02842 | 0.056475 | 0.004128 | 0.015283 | −0.000056 | 0.003144 | −0.003515 | −0.021202 | −0.006414 |
| 205 | −0.022875 | 0.087135 | −0.048827 | 0.08384 | −0.020789 | −0.006487 | 0.054689 | −0.022833 | −0.009227 | 0.02634 | 0.016002 | 0.019477 | 0.019474 | 0.052299 |
| 206 | 0.045916 | −0.018336 | −0.030908 | −0.042939 | −0.026307 | −0.014306 | −0.045967 | −0.011119 | −0.043547 | 0.009777 | −0.00522 | −0.034738 | 0.009021 | −0.003625 |
| 207 | 0.035418 | 0.014292 | 0.008256 | 0.028977 | −0.029359 | 0.056899 | 0.030925 | −0.003365 | 0.03522 | −0.021649 | −0.007234 | −0.008483 | 0.01541 | 0.020659 |
| 208 | 0.061119 | −0.026538 | −0.062467 | 0.005337 | 0.006854 | 0.003565 | −0.004978 | −0.023708 | −0.006815 | 0.010623 | −0.015527 | −0.04948 | −0.00854 | 0.00547 |
| 209 | 0.00711 | 0.042196 | 0.086609 | −0.085558 | −0.037001 | 0.039207 | 0.007826 | 0.01206 | 0.000122 | 0.056593 | −0.005456 | −0.028045 | −0.002294 | −0.020104 |
| 210 | 0.00176 | −0.032443 | −0.044838 | −0.013899 | −0.005805 | −0.009833 | 0.001912 | 0.02062 | 0.028613 | 0.005448 | 0.036118 | −0.021072 | −0.021777 | 0.019447 |
| 211 | 0.070781 | −0.07565 | −0.002469 | 0.036156 | 0.021059 | −0.005591 | 0.009118 | 0.031936 | 0.018845 | 0.011116 | −0.004974 | −0.014855 | −0.008498 | 0.00314 |
| 212 | −0.020496 | −0.080401 | 0.016926 | 0.12907 | 0.001424 | 0.006075 | 0.022799 | −0.009611 | −0.012788 | −0.019935 | −0.036027 | −0.017434 | −0.025472 | −0.002221 |
| 213 | −0.037838 | −0.058868 | −0.024179 | 0.020636 | −0.026481 | −0.012154 | −0.054635 | 0.025219 | 0.021227 | −0.007377 | 0.008055 | 0.018458 | −0.005613 | −0.000551 |
| 214 | −0.02769 | 0.023052 | −0.018909 | 0.000853 | −0.050764 | 0.034278 | 0.025424 | 0.039478 | 0.007784 | 0.001585 | −0.006869 | −0.011163 | 0.02765 | 0.005477 |
| 215 | −0.072544 | 0.095074 | −0.089939 | 0.026012 | −0.051853 | 0.047186 | 0.00677 | 0.001629 | 0.003482 | −0.006361 | 0.004987 | −0.049006 | 0.024017 | −0.030068 |
| 216 | 0.042565 | 0.04015 | −0.023217 | −0.020626 | −0.053223 | 0.046314 | 0.040315 | 0.005375 | 0.008715 | −0.038025 | −0.00402 | −0.004107 | 0.023405 | 0.003242 |
| 217 | −0.036089 | 0.051682 | −0.022564 | −0.043239 | 0.0628 | −0.051579 | −0.026602 | 0.028597 | 0.021592 | −0.007249 | 0.001054 | −0.016225 | 0.017316 | 0.034491 |
| 218 | 0.026559 | 0.044928 | −0.068437 | 0.01409 | −0.036709 | 0.029306 | 0.019339 | −0.016596 | −0.005658 | −0.003596 | 0.007145 | −0.025129 | 0.02266 | 0.016256 |
| 219 | −0.004403 | 0.005178 | −0.008886 | −0.059502 | −0.034344 | 0.013383 | 0.019387 | 0.030888 | 0.005918 | −0.052356 | −0.007183 | −0.02346 | 0.0267 | 0.018953 |
| 220 | −0.024866 | 0.056538 | −0.014921 | 0.013558 | 0.015665 | 0.009158 | −0.006339 | −0.036842 | −0.007623 | −0.092137 | −0.005327 | −0.048689 | −0.022066 | 0.021631 |
| 221 | 0.096476 | −0.028485 | −0.029007 | −0.031184 | −0.051873 | 0.01689 | 0.032573 | 0.019469 | 0.04245 | −0.031728 | 0.021144 | −0.008395 | −0.054404 | 0.006252 |
| 222 | 0.023627 | 0.016406 | −0.010589 | −0.014186 | −0.006185 | −0.015261 | 0.008409 | 0.00665 | 0.017176 | 0.003217 | 0.004754 | −0.013005 | −0.002826 | 0.042499 |
| 223 | −0.02556 | 0.003499 | −0.009634 | 0.075448 | −0.012184 | 0.010508 | 0.016878 | −0.01888 | 0.017169 | −0.028911 | 0.017414 | −0.002967 | −0.021315 | 0.031514 |
| 224 | 0.050497 | 0.02995 | 0.01101 | 0.040251 | −0.027484 | 0.025884 | 0.005298 | −0.015576 | 0.012519 | −0.004773 | 0.017195 | 0.008837 | 0.013159 | −0.012446 |

APPENDIX B3-continued

PCA Transformation
Matrix (340 × 340 Early/Late)

| | | | | | | | | | | | | | |
|---|---|---|---|---|---|---|---|---|---|---|---|---|---|
| 225 | 0.0941 | 0.002143 | 0.049282 | 0.070217 | −0.056814 | 0.045705 | 0.02114 | −0.014968 | 0.014728 | −0.005497 | 0.02278 | 0.005579 | −0.000668 | −0.004883 |
| 226 | −0.015239 | 0.004634 | 0.003442 | −0.009352 | 0.036181 | −0.017322 | −0.005845 | −0.003008 | 0.000065 | 0.005897 | 0.012017 | 0.005059 | 0.00459 | 0.012963 |
| 227 | 0.009123 | −0.041803 | 0.033483 | −0.002195 | 0.058787 | −0.036112 | −0.027756 | −0.01633 | −0.011823 | 0.009305 | 0.02784 | 0.002121 | −0.003137 | −0.018847 |
| 228 | 0.009486 | 0.00193 | 0.01402 | −0.074651 | 0.014866 | 0.01195 | −0.012117 | 0.007594 | 0.015845 | 0.011762 | 0.011004 | −0.004947 | 0.023889 | 0.021484 |
| 229 | 0.051595 | 0.008766 | −0.033053 | 0.032833 | 0.027626 | −0.014674 | −0.048739 | 0.026262 | 0.037467 | −0.003602 | −0.005812 | −0.017188 | 0.019324 | 0.023109 |
| 230 | 0.023751 | −0.022215 | 0.003987 | 0.096805 | −0.04227 | 0.041346 | −0.015686 | 0.004402 | 0.005528 | −0.023147 | −0.012806 | 0.006673 | 0.016124 | 0.001403 |
| 231 | 0.021695 | 0.017639 | 0.098607 | 0.112547 | −0.005758 | 0.01952 | 0.005675 | −0.002464 | 0.012835 | 0.02391 | 0.022318 | 0.003568 | −0.026649 | −0.013464 |
| 232 | −0.017794 | 0.006031 | −0.006789 | 0.070641 | 0.037852 | −0.039089 | −0.018722 | −0.017453 | −0.006473 | 0.007776 | −0.000327 | −0.003846 | 0.016045 | 0.013141 |
| 233 | −0.031239 | 0.04708 | 0.047598 | 0.016111 | 0.044517 | −0.050081 | −0.004681 | −0.018117 | −0.027366 | 0.002823 | −0.003909 | 0.010594 | 0.01172 | 0.003831 |
| 234 | 0.029985 | −0.043063 | 0.075865 | −0.081638 | 0.008551 | 0.014451 | −0.00718 | −0.012914 | −0.02422 | −0.019069 | −0.005596 | −0.014033 | −0.000025 | −0.011658 |
| 235 | −0.049095 | 0.012986 | 0.109986 | −0.010933 | −0.001997 | −0.00636 | 0.008018 | 0.000325 | −0.022933 | 0.008187 | −0.005209 | −0.013059 | −0.003086 | −0.012014 |
| 236 | −0.023636 | −0.023259 | −0.0194 | 0.03477 | −0.014508 | −0.01121 | 0.022282 | −0.021923 | −0.028234 | 0.012707 | −0.006464 | −0.001565 | 0.01739 | 0.009425 |
| 237 | 0.064634 | −0.062219 | −0.024277 | −0.038756 | 0.001887 | −0.007968 | 0.013313 | −0.013639 | −0.0036 | 0.035434 | 0.008412 | 0.025864 | 0.02714 | 0.024158 |
| 238 | 0.026382 | −0.008794 | 0.000127 | −0.021532 | −0.030781 | 0.020155 | 0.005917 | 0.037114 | 0.015291 | −0.00267 | −0.00439 | 0.015821 | 0.01868 | 0.010863 |
| 239 | −0.022947 | 0.05773 | 0.029299 | 0.001583 | −0.022522 | −0.00194 | 0.005806 | 0.037711 | 0.004387 | 0.000398 | −0.010972 | 0.01073 | 0.016 | −0.005522 |
| 240 | −0.026509 | 0.007504 | −0.029291 | −0.017334 | 0.074863 | −0.036613 | −0.030949 | −0.003745 | 0.008659 | −0.007549 | 0.005544 | −0.001833 | −0.026495 | −0.05401 |
| 241 | 0.006326 | 0.0772 | −0.016877 | −0.022928 | −0.007842 | 0.013345 | 0.017171 | −0.016099 | −0.016594 | −0.00391 | −0.00378 | 0.000898 | 0.000241 | −0.029953 |
| 242 | −0.021119 | 0.026285 | −0.039518 | 0.009789 | 0.045382 | −0.033137 | 0.03585 | −0.035736 | −0.018502 | −0.006074 | −0.005773 | −0.003497 | −0.000749 | 0.006795 |
| 243 | −0.014591 | 0.050532 | −0.021109 | −0.095463 | 0.059519 | −0.05892 | 0.01166 | 0.02207 | 0.009137 | −0.008303 | −0.002739 | −0.004329 | −0.003155 | 0.002791 |
| 244 | 0.039655 | −0.041197 | −0.013495 | −0.029408 | −0.073596 | 0.05084 | 0.007692 | 0.0362 | 0.025831 | 0.012668 | 0.002208 | 0.004799 | −0.051509 | −0.042044 |
| 245 | 0.014408 | −0.058043 | 0.015958 | 0.087328 | −0.033371 | 0.004639 | −0.020756 | 0.002221 | −0.019559 | 0.018547 | −0.024512 | −0.018865 | −0.005165 | −0.012478 |
| 246 | −0.03289 | 0.012118 | 0.023338 | 0.017755 | 0.066081 | −0.032955 | 0.012663 | −0.072217 | −0.053937 | −0.041639 | −0.02498 | −0.009895 | 0.00149 | 0.011614 |
| 247 | −0.021039 | −0.014488 | 0.0254 | 0.001764 | 0.026434 | −0.017879 | −0.001835 | −0.029099 | −0.02939 | −0.059202 | −0.014991 | −0.016119 | 0.000701 | 0.009852 |
| 248 | −0.008906 | −0.056298 | 0.015506 | 0.001358 | −0.036116 | 0.010914 | −0.023861 | −0.005752 | −0.022657 | −0.050785 | −0.008251 | −0.02734 | −0.00033 | 0.009291 |
| 249 | −0.03076 | 0.031759 | −0.034545 | 0.025121 | 0.043247 | −0.027145 | −0.032405 | −0.012133 | −0.005343 | 0.023347 | −0.010358 | −0.00244 | −0.010731 | −0.00694 |
| 250 | −0.0692 | −0.011302 | −0.002132 | −0.003393 | 0.023036 | −0.000157 | −0.001752 | −0.022737 | −0.001039 | −0.014984 | 0.015616 | 0.011169 | −0.032464 | −0.045284 |
| 251 | −0.018138 | −0.04774 | −0.00132 | −0.011863 | −0.017682 | 0.025313 | −0.000945 | −0.004672 | −0.001319 | −0.022879 | 0.003013 | 0.007044 | −0.04535 | −0.049502 |
| 252 | 0.027416 | −0.012257 | −0.009583 | 0.061267 | −0.00388 | 0.008025 | −0.025714 | 0.009644 | −0.002846 | 0.018853 | 0.000442 | −0.004527 | −0.029794 | −0.019105 |
| 253 | 0.027272 | 0.020928 | −0.006607 | −0.001299 | −0.043771 | 0.041491 | 0.005643 | −0.008435 | 0.009254 | 0.034082 | 0.011675 | −0.011202 | 0.001214 | 0.010501 |
| 254 | −0.035247 | −0.001063 | 0.032388 | 0.039348 | 0.011162 | 0.000005 | −0.004712 | −0.002765 | 0.009454 | −0.020802 | −0.002629 | −0.000574 | −0.038604 | −0.025871 |
| 255 | 0.008046 | −0.05689 | 0.006904 | 0.00425 | 0.004923 | 0.002248 | −0.011989 | −0.002723 | 0.006509 | −0.038797 | −0.011871 | −0.004938 | −0.071345 | −0.050484 |
| 256 | 0.059155 | −0.019225 | −0.085258 | 0.003484 | −0.040093 | 0.027801 | −0.051572 | −0.009577 | 0.021114 | −0.037097 | −0.010377 | −0.022791 | −0.051794 | −0.029455 |
| 257 | −0.00022 | −0.023458 | 0.049471 | 0.043602 | 0.034687 | −0.040377 | −0.010428 | −0.004901 | −0.008324 | 0.016768 | 0.003881 | 0.000558 | −0.007711 | 0.015573 |
| 258 | 0.019295 | 0.019758 | 0.034745 | 0.007538 | −0.018764 | −0.007338 | 0.002643 | −0.004143 | −0.009916 | 0.021988 | 0.003879 | −0.015693 | 0.010253 | 0.00148 |
| 259 | −0.035155 | −0.022341 | 0.017714 | −0.033662 | 0.001865 | 0.010119 | −0.005178 | −0.00221 | 0.007994 | 0.007466 | 0.013792 | 0.005185 | −0.014553 | 0.009656 |
| 260 | 0.010503 | 0.016792 | 0.021195 | 0.06998 | −0.00716 | 0.018074 | −0.006296 | 0.00915 | 0.015136 | 0.003539 | 0.021439 | 0.005557 | −0.017757 | 0.010146 |
| 261 | 0.060781 | 0.003835 | −0.010002 | −0.007902 | 0.021352 | 0.003889 | −0.030119 | −0.00333 | 0.001066 | −0.013948 | 0.007413 | −0.006697 | −0.022246 | −0.012472 |
| 262 | −0.015705 | 0.001199 | −0.029329 | 0.047389 | 0.023259 | −0.01675 | −0.014989 | −0.01498 | −0.019097 | 0.008844 | −0.008472 | 0.00031 | 0.006396 | −0.000685 |
| 263 | −0.044534 | −0.05192 | 0.007932 | 0.002396 | 0.001381 | −0.013894 | −0.004561 | −0.000925 | −0.021976 | 0.017602 | −0.007328 | −0.004071 | 0.006534 | 0.007815 |
| 264 | −0.033588 | 0.059123 | 0.010395 | −0.068756 | −0.007851 | 0.021051 | −0.000595 | 0.005687 | 0.01016 | 0.003241 | 0.004421 | −0.003709 | −0.004439 | 0.006304 |
| 265 | −0.029751 | 0.117085 | 0.059696 | −0.007801 | −0.003702 | 0.022442 | 0.007817 | 0.001855 | 0.010782 | −0.016849 | 0.010173 | 0.009808 | −0.009411 | 0.008029 |
| 266 | 0.076917 | 0.036356 | 0.062786 | 0.009624 | 0.008146 | 0.006261 | −0.001096 | 0.004558 | 0.003906 | −0.04423 | −0.013038 | −0.000626 | −0.031825 | −0.003936 |
| 267 | −0.037707 | 0.066639 | −0.09535 | 0.012898 | 0.002646 | 0.021367 | −0.023067 | 0.009441 | 0.03361 | 0.018133 | 0.022178 | −0.010513 | 0.018806 | −0.005405 |
| 268 | −0.027455 | 0.058987 | 0.040914 | −0.035615 | 0.009181 | −0.000309 | 0.019519 | 0.002728 | 0.002978 | 0.01466 | 0.017766 | 0.003149 | 0.002749 | −0.001399 |
| 269 | 0.013545 | 0.037338 | −0.002792 | −0.000326 | −0.005005 | 0.012591 | 0.022456 | 0.004756 | 0.010759 | 0.007453 | 0.014932 | 0.003873 | −0.004674 | 0.001092 |
| 270 | −0.017627 | −0.008157 | −0.000692 | −0.015255 | 0.024934 | −0.009625 | −0.009505 | −0.004077 | −0.008759 | 0.007128 | 0.009848 | 0.000236 | −0.004046 | −0.018804 |
| 271 | −0.042619 | −0.006192 | −0.043158 | −0.037899 | 0.023662 | −0.040115 | 0.020999 | 0.023647 | −0.009021 | 0.014612 | −0.024117 | 0.023766 | 0.029193 | 0.008997 |
| 272 | −0.001439 | −0.008022 | −0.027458 | 0.00602 | 0.027027 | −0.00971 | −0.053151 | 0.024992 | 0.034127 | 0.000898 | 0.002049 | −0.011373 | 0.017851 | 0.011103 |
| 273 | −0.047197 | 0.029026 | 0.04358 | 0.020352 | −0.032177 | 0.028743 | −0.010319 | 0.007336 | 0.005553 | 0.002885 | 0.015958 | 0.002703 | 0.004375 | −0.002198 |
| 274 | −0.037015 | 0.031225 | 0.043427 | 0.021232 | −0.02506 | 0.034136 | −0.004063 | 0.006804 | 0.005513 | 0.000183 | 0.013874 | 0.005859 | 0.003647 | −0.001097 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 275 | −0.065739 | −0.06243 | −0.03622 | 0.045074 | 0.001772 | 0.01239 | −0.041436 | 0.009132 | −0.015495 | −0.025663 | −0.018574 | −0.006703 | 0.017753 | −0.020979 |
| 276 | 0.005015 | 0.004948 | −0.023718 | 0.001435 | 0.016187 | −0.03886 | 0.008274 | −0.013176 | −0.015058 | 0.01709 | −0.002545 | −0.009997 | 0.026027 | 0.008806 |
| 277 | 0.033642 | 0.006671 | 0.010045 | 0.007169 | −0.007608 | −0.005944 | 0.010141 | −0.000695 | −0.005937 | 0.05942 | 0.005148 | 0.016463 | 0.040192 | 0.005662 |
| 278 | 0.0112 | −0.025106 | −0.017618 | 0.037978 | −0.050698 | 0.03116 | −0.008223 | 0.001671 | −0.002208 | 0.061742 | 0.005081 | 0.025324 | 0.038549 | −0.000158 |
| 279 | −0.032157 | 0.025172 | −0.006766 | −0.064016 | 0.015031 | −0.028421 | −0.028343 | 0.052559 | 0.012595 | −0.012572 | −0.015907 | 0.00948 | 0.027551 | −0.01164 |
| 280 | 0.012538 | 0.095393 | 0.0306 | −0.148489 | 0.034259 | −0.023637 | 0.016286 | −0.005358 | 0.010783 | 0.020379 | 0.017337 | 0.006052 | 0.012644 | 0.006274 |
| 281 | −0.048901 | 0.027524 | 0.018704 | −0.000913 | 0.023346 | −0.002828 | −0.006771 | −0.066028 | −0.048165 | −0.037358 | −0.022891 | −0.020435 | 0.006242 | 0.00598 |
| 282 | −0.063259 | 0.023148 | −0.007655 | 0.015777 | 0.007943 | 0.004599 | −0.003865 | −0.05266 | −0.043544 | −0.025703 | −0.021119 | −0.002085 | 0.001171 | −0.006562 |
| 283 | −0.06673 | −0.040631 | −0.044228 | −0.065388 | 0.002156 | 0.004125 | −0.029868 | −0.003955 | −0.025403 | −0.082678 | −0.019422 | −0.01218 | 0.005145 | −0.006063 |
| 284 | −0.026358 | −0.005757 | 0.003634 | −0.01059 | 0.004022 | −0.008616 | −0.011647 | 0.003228 | 0.006433 | 0.007937 | 0.010588 | 0.000692 | −0.001303 | 0.003356 |
| 285 | −0.033032 | −0.005419 | −0.005998 | 0.015692 | 0.002122 | −0.006704 | −0.000866 | 0.006002 | −0.002585 | 0.016247 | 0.002292 | 0.011736 | −0.004799 | −0.001016 |
| 286 | 0.017607 | 0.00713 | 0.018714 | −0.023123 | 0.00797 | −0.018123 | −0.007942 | 0.013868 | 0.010022 | 0.023851 | 0.000905 | −0.006841 | 0.002815 | −0.004315 |
| 287 | 0.009629 | −0.011995 | −0.017735 | −0.022433 | −0.000259 | −0.00624 | −0.01591 | 0.027147 | 0.009331 | 0.028152 | −0.004755 | 0.001859 | 0.002595 | −0.012797 |
| 288 | 0.004304 | −0.003458 | −0.05919 | −0.082246 | −0.031661 | 0.027924 | −0.011217 | −0.000497 | −0.003025 | −0.006125 | −0.007041 | −0.013508 | 0.023013 | −0.004794 |
| 289 | −0.036127 | 0.041732 | −0.004195 | 0.018656 | 0.021235 | −0.024673 | −0.004155 | −0.012639 | −0.019314 | −0.006698 | −0.017144 | 0.005866 | 0.004228 | −0.009082 |
| 290 | −0.042773 | −0.013098 | −0.032731 | −0.047829 | −0.033486 | 0.038787 | −0.015411 | 0.004062 | −0.00583 | −0.004471 | −0.026093 | −0.009377 | −0.00064 | −0.02171 |
| 291 | −0.040467 | −0.0222 | −0.03438 | −0.05029 | −0.0139 | 0.02586 | −0.007416 | 0.004718 | −0.005508 | −0.005456 | −0.025055 | −0.009539 | 0.000608 | −0.020537 |
| 292 | −0.037835 | −0.016051 | −0.035854 | −0.061482 | 0.025839 | −0.008432 | −0.019287 | 0.009083 | −0.002233 | −0.013132 | −0.031736 | −0.011711 | −0.001646 | −0.016651 |
| 293 | −0.013049 | −0.030802 | 0.010916 | −0.136569 | −0.014996 | −0.041671 | 0.01835 | −0.017103 | 0.014563 | 0.006589 | 0.025238 | −0.005991 | −0.024422 | −0.010714 |
| 294 | −0.037324 | 0.033123 | −0.025124 | −0.049928 | −0.031928 | 0.012645 | 0.006986 | 0.004041 | 0.001768 | 0.016352 | 0.012338 | −0.004715 | 0.004918 | −0.001842 |
| 295 | −0.047197 | −0.00453 | 0.031473 | −0.029271 | −0.001513 | −0.013022 | −0.005506 | −0.014766 | 0.005232 | −0.007544 | 0.013321 | 0.005297 | −0.012558 | −0.006061 |
| 296 | −0.028896 | −0.011104 | 0.000252 | 0.059836 | 0.002409 | 0.006671 | −0.059079 | −0.01964 | −0.001255 | −0.023988 | 0.000248 | −0.02198 | −0.012486 | −0.004798 |
| 297 | 0.032867 | 0.044167 | 0.001289 | 0.003699 | −0.043667 | 0.018374 | 0.020555 | −0.019443 | 0.019293 | −0.002495 | 0.016713 | −0.005054 | −0.019316 | −0.004005 |
| 298 | −0.086157 | −0.074917 | 0.018359 | 0.032221 | −0.021525 | 0.001473 | −0.044728 | 0.013798 | −0.000314 | −0.017523 | −0.008697 | −0.02642 | 0.012838 | 0.003947 |
| 299 | 0.041871 | 0.038138 | 0.036337 | −0.029217 | −0.04778 | 0.011514 | 0.029679 | −0.014565 | 0.01127 | 0.002298 | 0.020886 | −0.005325 | −0.020061 | 0.005265 |
| 300 | −0.022011 | 0.010952 | 0.054592 | −0.072567 | 0.067154 | −0.032165 | −0.031164 | 0.005121 | −0.013542 | −0.010027 | −0.01357 | 0.001296 | 0.029333 | −0.059636 |
| 301 | −0.026174 | −0.001949 | −0.001135 | −0.020251 | −0.061168 | 0.016301 | 0.016821 | −0.008122 | 0.001567 | 0.006228 | 0.009117 | 0.004021 | −0.012637 | 0.006075 |
| 302 | −0.062587 | 0.054529 | 0.003052 | −0.003051 | 0.003654 | 0.001539 | 0.01498 | −0.011364 | −0.020833 | −0.00306 | −0.010407 | 0.000315 | 0.003438 | 0.001296 |
| 303 | 0.066901 | 0.024599 | −0.010328 | 0.00617 | 0.034116 | −0.033064 | −0.021975 | 0.005486 | 0.026923 | 0.016721 | 0.019563 | −0.003186 | −0.005896 | 0.020489 |
| 304 | 0.021086 | −0.031879 | 0.00897 | −0.067501 | −0.016167 | 0.02541 | −0.025073 | −0.009309 | 0.010844 | 0.006849 | 0.025189 | −0.001592 | −0.002049 | 0.005957 |
| 305 | −0.008773 | −0.035278 | 0.042841 | −0.100637 | −0.033872 | 0.014645 | 0.029941 | −0.02015 | −0.009767 | −0.008959 | −0.00303 | 0.024626 | −0.021978 | −0.002033 |
| 306 | −0.030877 | 0.008524 | −0.00908 | −0.04706 | −0.009026 | 0.0202 | −0.020143 | −0.050297 | 0.009867 | 0.005429 | 0.043459 | −0.021775 | −0.01565 | −0.01124 |
| 307 | 0.042146 | −0.040141 | 0.037431 | 0.050263 | 0.000628 | 0.000352 | −0.027827 | −0.013631 | 0.003004 | 0.06691 | 0.014081 | 0.005027 | 0.004449 | −0.002752 |
| 308 | 0.037103 | −0.024494 | 0.042436 | −0.047566 | 0.021652 | −0.080069 | −0.000786 | −0.0003061 | 0.0049731 | −0.003118 | −0.01124 | 0.014329 | −0.030703 | 0.003701 |
| 309 | −0.019351 | −0.028566 | −0.049854 | 0.025926 | −0.044079 | 0.025014 | 0.022653 | 0.005218 | −0.007669 | 0.013792 | −0.00656 | 0.005907 | −0.006332 | −0.014472 |
| 310 | −0.144474 | −0.00961 | −0.01082 | 0.117576 | −0.049093 | 0.031597 | −0.01159 | 0.015377 | −0.007701 | 0.022254 | −0.009448 | −0.014179 | 0.007742 | −0.007968 |
| 311 | 0.01765 | −0.013063 | 0.040254 | −0.068624 | −0.03134 | 0.015938 | 0.01081 | 0.002526 | −0.001127 | 0.009411 | 0.013117 | 0.006261 | −0.0114 | −0.008423 |
| 312 | −0.016651 | −0.005127 | −0.084379 | 0.14429 | −0.011854 | 0.014616 | 0.004648 | −0.016144 | 0.013245 | −0.018649 | −0.019508 | 0.006908 | −0.016292 | −0.013264 |
| 313 | 0.060357 | −0.080358 | −0.001344 | −0.035848 | −0.005361 | 0.002165 | −0.027531 | −0.015761 | 0.005963 | −0.019855 | 0.008631 | −0.015891 | −0.014446 | 0.001644 |
| 314 | −0.039318 | −0.103098 | −0.027144 | 0.073351 | 0.007562 | −0.017014 | −0.002896 | −0.012111 | 0.012439 | 0.023857 | −0.001923 | 0.003481 | 0.008651 | −0.031414 |
| 315 | 0.073089 | 0.02679 | 0.006681 | 0.010832 | 0.012707 | −0.016275 | 0.02065 | −0.015371 | 0.004764 | 0.003065 | 0.00114 | 0.008394 | −0.012422 | −0.005908 |
| 316 | 0.100097 | −0.035842 | −0.020525 | 0.0162 | 0.023809 | −0.050139 | −0.007402 | 0.00747 | 0.024309 | 0.003194 | 0.010505 | 0.008077 | −0.007463 | −0.001813 |
| 317 | −0.054955 | −0.060574 | −0.009711 | 0.08107 | 0.010341 | −0.021807 | −0.014103 | 0.000619 | −0.00514 | 0.0042 | −0.002957 | 0.009724 | 0.000525 | 0.003483 |
| 318 | −0.047347 | −0.132353 | 0.082668 | 0.030701 | 0.030068 | −0.017275 | 0.004644 | −0.010378 | 0.002929 | 0.008169 | 0.017993 | 0.030143 | −0.004732 | 0.052162 |
| 319 | 0.070913 | 0.022854 | 0.015002 | 0.076125 | −0.015597 | 0.000377 | 0.034241 | 0.003217 | 0.012044 | 0.011844 | 0.004987 | 0.005445 | −0.007408 | 0.006725 |
| 320 | −0.025454 | −0.004432 | 0.135251 | −0.001956 | −0.010185 | −0.004782 | −0.041485 | −0.003282 | −0.005976 | −0.008567 | 0.010518 | −0.016657 | 0.002407 | 0.012532 |
| 321 | 0.003021 | 0.068678 | −0.006439 | −0.051938 | −0.003624 | 0.006468 | −0.005039 | −0.025845 | −0.000157 | 0.019159 | 0.022699 | −0.012213 | 0.001346 | −0.006223 |
| 322 | −0.243054 | 0.020135 | 0.060037 | 0.049799 | −0.018925 | −0.023747 | −0.058996 | 0.012095 | −0.017229 | 0.0300841 | −0.005019 | 0.038361 | 0.018585 | −0.014285 |
| 323 | −0.085883 | −0.009092 | 0.103659 | 0.033268 | 0.006499 | 0.000292 | 0.023036 | −0.020914 | −0.012447 | 0.005599 | 0.009216 | −0.003854 | −0.002987 | −0.008346 |
| 324 | −0.030051 | 0.058912 | −0.040645 | −0.090227 | −0.011374 | −0.000251 | 0.049531 | 0.004185 | −0.016024 | −0.019813 | −0.00316 | 0.002782 | −0.000017 | −0.002899 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 325 | 0.044718 | 0.083094 | −0.099451 | 0.023911 | −0.024401 | 0.019914 | 0.004467 | 0.012317 | 0.013648 | −0.005441 | 0.00024 | −0.016844 | 0.00564 | 0.007573 |
| 326 | 0.006274 | −0.042554 | −0.110237 | −0.006216 | 0.008538 | −0.019363 | −0.014286 | 0.029448 | 0.006623 | −0.009899 | −0.018889 | −0.015747 | 0.006528 | 0.004855 |
| 327 | −0.043393 | 0.015499 | 0.043682 | −0.014567 | 0.025325 | −0.01882 | 0.002801 | −0.003309 | −0.015414 | −0.01555 | −0.00341 | −0.001533 | 0.006412 | 0.011826 |
| 328 | 0.018594 | −0.030378 | −0.006933 | −0.05224 | −0.060209 | 0.028872 | −0.026941 | −0.025365 | −0.023394 | 0.021136 | −0.024996 | −0.017614 | −0.007783 | −0.050692 |
| 329 | −0.002882 | 0.028009 | 0.084903 | 0.047828 | 0.031213 | −0.032991 | 0.031134 | 0.002356 | −0.023838 | −0.009362 | −0.024221 | −0.00771 | −0.009708 | 0.009212 |
| 330 | −0.110447 | 0.061321 | −0.08409 | 0.080018 | 0.045337 | −0.036709 | −0.045714 | 0.022816 | −0.01201 | 0.018354 | −0.006917 | 0.003425 | 0.035393 | −0.0112 |
| 331 | 0.014213 | 0.038836 | −0.009942 | −0.086299 | 0.008301 | −0.025008 | 0.012869 | 0.010591 | 0.009444 | 0.000336 | 0.001839 | −0.006862 | 0.005273 | −0.008877 |
| 332 | 0.097166 | 0.037476 | −0.03102 | −0.083765 | −0.051524 | 0.028996 | 0.010722 | 0.009178 | −0.003121 | 0.008556 | 0.00555 | 0.014934 | 0.005107 | −0.027677 |
| 333 | 0.036923 | 0.035689 | −0.049665 | −0.001379 | −0.012891 | 0.003902 | 0.004675 | 0.004962 | 0.006162 | 0.002625 | −0.002914 | −0.005278 | 0.003244 | −0.004507 |
| 334 | 0.018324 | 0.080687 | −0.168868 | 0.124254 | 0.000464 | −0.005427 | 0.022751 | −0.003116 | −0.01012 | −0.024209 | −0.042984 | −0.016629 | −0.016587 | −0.0052 |
| 335 | 0.018895 | 0.036982 | 0.002728 | −0.006783 | −0.065019 | 0.051448 | 0.0337 | 0.017023 | 0.003404 | 0.007499 | 0.002329 | −0.011217 | 0.003046 | 0.002294 |
| 336 | −0.07037 | −0.090707 | −0.150681 | −0.043001 | −0.048527 | 0.0543 | −0.035796 | −0.016083 | 0.021037 | −0.023085 | 0.032767 | 0.030996 | 0.019693 | −0.006215 |
| 337 | 0.012281 | −0.01621 | 0.019435 | 0.026682 | 0.021902 | −0.025749 | −0.025178 | −0.004974 | 0.00833 | −0.003648 | −0.01489 | −0.011642 | −0.022493 | −0.000407 |
| 338 | 0.000206 | −0.023061 | 0.019001 | 0.08241 | 0.027556 | −0.035165 | −0.019288 | −0.001777 | −0.020731 | −0.01982 | −0.012154 | −0.004248 | −0.001844 | 0.008193 |
| 339 | −0.020307 | −0.019421 | −0.03771 | −0.05173 | 0.004841 | −0.014778 | −0.020623 | −0.005525 | 0.003323 | 0.017058 | −0.012598 | −0.009977 | 0.009096 | −0.021392 |
| 340 | 0.14654 | −0.075606 | 0.146172 | 0.024242 | 0.057099 | −0.034928 | 0.053253 | 0.003671 | 0.024747 | −0.039543 | 0.019827 | −0.001083 | −0.024685 | 0.060453 |

| | BP | BQ | BR | BS | BT | BU | BV | BW | BX | BY | BZ | CA | CB | CC |
|---|---|---|---|---|---|---|---|---|---|---|---|---|---|---|
| 1 | −0.000522 | −0.012269 | 0.001736 | −0.017976 | −0.079141 | −0.075484 | −0.042734 | 0.090379 | 0.033455 | 0.084822 | 0.038747 | 0.02253 | 0.001446 | −0.156524 |
| 2 | 0.063464 | −0.063413 | 0.018892 | 0.018081 | −0.027699 | 0.037345 | −0.043809 | −0.012525 | 0.023955 | 0.009337 | 0.029219 | 0.011625 | 0.030384 | 0.084847 |
| 3 | −0.019109 | 0.021646 | −0.019841 | 0.00479 | −0.179469 | −0.161725 | −0.185124 | −0.010748 | 0.006108 | −0.012111 | −0.002176 | 0.011988 | 0.021656 | −0.002142 |
| 4 | 0.003982 | −0.123909 | −0.034148 | −0.04774 | −0.033524 | −0.103995 | −0.078211 | −0.052493 | −0.031053 | −0.05478 | −0.020137 | −0.005948 | −0.06583 | 0.075439 |
| 5 | −0.068853 | 0.065538 | −0.001561 | 0.020031 | −0.059173 | −0.042753 | 0.031929 | −0.06712 | −0.026151 | −0.038864 | −0.019459 | −0.040569 | −0.034559 | 0.040051 |
| 6 | −0.053345 | 0.02987 | 0.017776 | 0.031716 | 0.048529 | 0.005508 | −0.043114 | 0.086272 | 0.047566 | 0.040497 | 0.042456 | 0.054921 | 0.05419 | 0.010235 |
| 7 | 0.021606 | 0.009431 | −0.066338 | −0.050243 | −0.042581 | −0.031521 | −0.056152 | −0.032166 | −0.018789 | −0.054351 | −0.019286 | −0.025996 | −0.058747 | −0.035918 |
| 8 | −0.005598 | −0.009743 | −0.015155 | 0.034778 | −0.078571 | −0.067813 | −0.086889 | 0.048958 | 0.027292 | 0.069337 | 0.025249 | 0.033089 | −0.016832 | 0.030096 |
| 9 | −0.044829 | −0.091375 | 0.086816 | 0.053107 | 0.071572 | 0.059864 | 0.029954 | −0.003492 | 0.071112 | 0.048449 | 0.080526 | 0.068645 | 0.028163 | 0.009752 |
| 10 | −0.032176 | −0.031508 | −0.023663 | 0.050596 | −0.007208 | 0.133655 | 0.028947 | −0.035078 | −0.011103 | −0.031791 | −0.009493 | 0.004229 | −0.008211 | −0.006031 |
| 11 | 0.050198 | −0.011811 | 0.06941 | −0.006795 | −0.07306 | −0.027636 | −0.103652 | −0.115135 | −0.009052 | −0.009094 | −0.018908 | 0.000026 | 0.035495 | −0.060974 |
| 12 | 0.006432 | −0.028703 | 0.003684 | 0.064866 | −0.09508 | −0.125332 | −0.050368 | 0.037381 | 0.028747 | −0.001273 | 0.034254 | 0.042979 | 0.047475 | 0.092448 |
| 13 | −0.025919 | 0.026995 | −0.080485 | −0.067735 | −0.063314 | 0.062532 | 0.190709 | 0.034945 | −0.117409 | −0.123572 | −0.099636 | −0.074771 | −0.102977 | −0.164738 |
| 14 | −0.055291 | 0.019341 | −0.101996 | −0.064017 | 0.006964 | 0.01426 | −0.087397 | 0.109121 | −0.084014 | −0.042562 | −0.056381 | −0.062253 | −0.103934 | 0.053114 |
| 17 | 0.07257 | −0.024199 | −0.030983 | 0.024032 | −0.009561 | −0.077133 | −0.105206 | −0.084935 | 0.003145 | 0.030491 | 0.001306 | 0.006231 | −0.029515 | −0.06049 |
| 16 | 0.051162 | 0.055849 | −0.053966 | 0.002934 | −0.021339 | −0.012488 | −0.080024 | 0.02634 | −0.029237 | −0.052661 | −0.017867 | −0.033538 | −0.070884 | −0.051385 |
| 17 | 0.040733 | −0.051323 | −0.08748 | 0.020948 | 0.058537 | 0.023949 | 0.067452 | 0.040934 | 0.019262 | −0.000101 | 0.017424 | 0.037464 | −0.00821 | 0.013977 |
| 18 | 0.012825 | −0.112922 | 0.02806 | 0.046619 | −0.046 | 0.000628 | 0.01911 | 0.002038 | −0.013113 | −0.02847 | −0.00766 | −0.022992 | 0.028746 | −0.045122 |
| 19 | −0.073732 | −0.02532 | 0.068942 | 0.000971 | 0.060096 | −0.007517 | −0.001965 | −0.107446 | 0.029869 | 0.03845 | 0.032103 | 0.029843 | 0.052247 | 0.001169 |
| 20 | −0.056355 | 0.021164 | −0.058417 | −0.057451 | −0.026781 | 0.007094 | −0.010689 | 0.102715 | −0.032961 | −0.051658 | −0.044898 | −0.048971 | −0.046743 | 0.019486 |
| 21 | 0.002614 | 0.031614 | 0.053923 | −0.101107 | 0.001108 | 0.01654 | −0.036441 | −0.058745 | −0.040228 | −0.057091 | −0.039705 | −0.056479 | −0.045157 | −0.000913 |
| 22 | −0.135259 | −0.155232 | −0.031218 | 0.05585 | −0.079877 | −0.02945 | −0.049098 | 0.017695 | −0.012855 | −0.017471 | −0.012775 | −0.020632 | 0.023398 | 0.120118 |
| 23 | 0.012479 | −0.028402 | −0.021324 | −0.041023 | 0.024978 | 0.013535 | −0.010844 | −0.040742 | −0.011002 | −0.022029 | 0.000878 | 0.0101 | 0.004884 | −0.051225 |
| 24 | −0.043966 | −0.006797 | −0.037661 | −0.017584 | 0.040423 | −0.013942 | 0.023087 | −0.003084 | −0.013322 | −0.022113 | −0.012524 | 0.001211 | 0.00549 | 0.02342 |
| 25 | −0.012795 | 0.01441 | 0.030114 | 0.035338 | −0.005419 | −0.082612 | 0.1019 | −0.023933 | 0.018203 | 0.020096 | 0.022293 | 0.018249 | 0.011624 | −0.013744 |
| 26 | −0.03249 | −0.043017 | 0.052599 | −0.007662 | 0.025403 | 0.028603 | 0.013398 | −0.010461 | 0.01149 | −0.003944 | 0.017948 | 0.038346 | −0.035926 | 0.038598 |
| 27 | 0.138527 | 0.008182 | 0.047526 | 0.064193 | −0.055938 | −0.013456 | 0.096713 | −0.075413 | 0.028497 | 0.034 | 0.0212 | 0.008981 | 0.002165 | 0.050653 |
| 28 | −0.022381 | −0.01215 | −0.018422 | 0.015689 | 0.061859 | 0.047527 | 0.205425 | 0.03715 | 0.005161 | −0.029291 | 0.004152 | 0.009632 | 0.034553 | 0.156684 |
| 29 | −0.0124 | 0.024981 | 0.041692 | −0.016549 | −0.003888 | −0.008876 | −0.008299 | −0.003464 | 0.006941 | 0.00818 | 0.001356 | 0.009296 | 0.01838 | −0.044861 |
| 30 | −0.173397 | 0.00448 | 0.020092 | 0.076279 | −0.010169 | 0.016035 | 0.01648 | 0.070017 | 0.043169 | 0.017953 | 0.051023 | 0.062766 | 0.036546 | −0.013134 |
| 31 | −0.051738 | 0.075494 | 0.032342 | −0.021144 | −0.009834 | −0.034511 | 0.006094 | −0.106958 | 0.000406 | −0.01494 | −0.000419 | −0.016258 | 0.002035 | 0.050551 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 32 | 0.047587 | 0.163053 | −0.008149 | 0.07551 | −0.048314 | 0.011021 | −0.080387 | 0.05842 | 0.020034 | −0.011797 | 0.016997 | 0.027306 | 0.004862 | −0.019383 |
| 33 | 0.008293 | 0.032981 | 0.004374 | 0.004199 | 0.037482 | 0.045572 | 0.006436 | −0.050275 | 0.004498 | 0.002761 | 0.018646 | 0.006445 | −0.03322 | 0.02864 |
| 34 | −0.021514 | 0.002635 | 0.007484 | −0.04405 | 0.043015 | 0.077599 | 0.027692 | 0.055423 | 0.002678 | 0.056151 | 0.009107 | −0.018309 | −0.030462 | −0.088295 |
| 35 | 0.009941 | 0.026854 | −0.033966 | −0.065047 | −0.036229 | −0.009607 | 0.00563 | −0.05331 | −0.033751 | −0.02597 | −0.036448 | −0.046868 | −0.041576 | −0.044059 |
| 36 | −0.006884 | 0.044869 | 0.029255 | 0.038972 | 0.058053 | 0.028182 | −0.035897 | 0.055684 | 0.037663 | 0.041708 | 0.045795 | 0.028927 | −0.016363 | −0.010764 |
| 37 | 0.010225 | 0.036243 | 0.055258 | 0.006438 | −0.016303 | 0.079788 | 0.026777 | −0.029288 | −0.005017 | −0.024347 | −0.000388 | −0.021698 | −0.05213 | 0.069666 |
| 38 | −0.074442 | −0.000308 | 0.031326 | −0.010141 | 0.049369 | 0.058066 | −0.042751 | 0.084619 | 0.006865 | 0.041172 | 0.007992 | −0.001899 | 0.040496 | 0.055575 |
| 39 | 0.032582 | −0.030724 | 0.071826 | 0.07343 | 0.009833 | 0.013189 | 0.010188 | −0.010155 | 0.024867 | 0.076933 | 0.026922 | 0.036921 | −0.000381 | 0.044898 |
| 40 | −0.021861 | 0.006329 | 0.017578 | 0.006753 | 0.022143 | 0.031794 | 0.00178 | 0.011618 | 0.007485 | 0.017683 | 0.006788 | 0.014724 | −0.009495 | −0.004941 |
| 41 | −0.019252 | −0.053769 | −0.008027 | 0.025583 | −0.004554 | −0.017142 | −0.032285 | −0.002951 | −0.002682 | 0.056251 | −0.002388 | −0.018937 | 0.028449 | 0.000288 |
| 42 | 0.054987 | −0.119616 | −0.018633 | 0.058878 | 0.069685 | 0.067336 | 0.046713 | 0.070604 | 0.040483 | 0.063655 | 0.033518 | 0.050103 | 0.051682 | 0.029208 |
| 43 | −0.031988 | 0.107948 | 0.0905 | 0.162393 | 0.030704 | −0.016164 | 0.065145 | −0.035249 | 0.119232 | 0.033557 | 0.113089 | 0.132081 | 0.114053 | 0.007156 |
| 44 | −0.114788 | −0.096614 | −0.120125 | −0.139806 | −0.08138 | 0.02144 | 0.027611 | 0.009066 | −0.154806 | −0.036542 | −0.175545 | −0.171788 | −0.136762 | −0.000716 |
| 45 | 0.02006 | 0.050334 | −0.179953 | −0.154387 | −0.039331 | −0.000468 | 0.043697 | 0.044033 | −0.08032 | −0.203046 | −0.121443 | −0.084398 | −0.079655 | 0.033962 |
| 46 | 0.033074 | 0.051152 | 0.106739 | −0.013136 | −0.010573 | 0.020843 | −0.079439 | 0.042706 | −0.091368 | −0.049176 | −0.043373 | −0.058351 | −0.121004 | 0.019184 |
| 47 | −0.045166 | −0.0674 | −0.024575 | 0.053363 | −0.028216 | −0.042558 | −0.001023 | 0.006576 | −0.029141 | 0.042199 | 0.017677 | 0.034462 | −0.081628 | 0.031178 |
| 48 | 0.017701 | −0.05895 | −0.044326 | −0.045891 | −0.079401 | −0.005128 | −0.082687 | 0.028013 | −0.113877 | −0.055587 | −0.124183 | −0.17226 | −0.02217 | 0.032622 |
| 49 | 0.107968 | 0.115962 | −0.02216 | −0.00911 | −0.017716 | −0.082724 | 0.088841 | −0.088485 | −0.009764 | −0.054454 | −0.011512 | 0.00398 | −0.018754 | 0.10465 |
| 50 | 0.064726 | −0.06834 | −0.030961 | 0.068872 | −0.059294 | 0.025858 | 0.026105 | −0.083157 | 0.004 | 0.016306 | −0.017056 | 0.022752 | −0.06324 | 0.01524 |
| 51 | 0.079407 | 0.004221 | −0.055484 | −0.010583 | −0.104162 | −0.024469 | 0.147113 | −0.000982 | −0.036344 | −0.031964 | −0.050423 | −0.043313 | −0.00817 | −0.112401 |
| 52 | −0.003695 | −0.031143 | −0.054192 | −0.005325 | −0.011172 | 0.041538 | −0.052979 | 0.084232 | −0.017486 | 0.008102 | −0.002519 | −0.019279 | −0.081369 | 0.005617 |
| 53 | −0.007984 | 0.031756 | −0.074493 | −0.014915 | −0.003457 | −0.015811 | −0.032414 | −0.013849 | 0.008622 | −0.064928 | −0.002999 | −0.002465 | −0.043149 | 0.139671 |
| 54 | −0.066683 | 0.041477 | 0.02989 | −0.009658 | 0.054931 | 0.087159 | 0.068658 | −0.100632 | −0.011521 | −0.078017 | 0.005272 | 0.004695 | −0.054825 | −0.16413 |
| 55 | −0.041792 | −0.009777 | 0.009449 | 0.058756 | 0.061563 | −0.01659 | 0.011226 | 0.023423 | 0.014229 | −0.021825 | 0.029677 | 0.024985 | 0.027301 | −0.086758 |
| 56 | 0.000461 | 0.006186 | −0.031937 | −0.048111 | −0.012614 | 0.019709 | −0.045283 | 0.015406 | −0.020889 | 0.030534 | −0.036163 | −0.009283 | 0.000666 | −0.009591 |
| 57 | −0.053524 | −0.123667 | 0.018826 | −0.00957 | −0.001859 | 0.022434 | 0.021903 | 0.072832 | 0.008987 | −0.007704 | 0.00489 | 0.025498 | −0.019423 | −0.052287 |
| 58 | 0.00046 | −0.137914 | −0.043958 | 0.027041 | 0.039522 | 0.06898 | 0.023517 | −0.045947 | 0.017098 | 0.036603 | 0.016235 | 0.016838 | −0.003577 | −0.004362 |
| 59 | 0.004342 | −0.047388 | −0.06016 | −0.033723 | −0.027993 | −0.042989 | 0.047927 | −0.055468 | −0.006428 | 0.056725 | −0.014996 | −0.071828 | −0.007117 | −0.01558 |
| 60 | 0.007569 | −0.003763 | 0.015386 | −0.01269 | −0.00466 | −0.016128 | 0.005718 | 0.002923 | −0.009452 | 0.007433 | −0.004731 | −0.009654 | 0.004179 | 0.008638 |
| 61 | −0.038019 | −0.003619 | −0.014461 | −0.016895 | 0.004901 | 0.009396 | 0.017563 | 0.013487 | −0.013551 | −0.004948 | −0.01197 | −0.008486 | −0.0073 | −0.032825 |
| 62 | 0.018884 | −0.018827 | −0.000665 | −0.003003 | 0.006051 | −0.008422 | −0.001496 | 0.011458 | 0.007491 | 0.007837 | 0.010193 | 0.009551 | 0.016224 | 0.035643 |
| 63 | −0.039113 | −0.020165 | 0.002091 | −0.014056 | −0.004166 | −0.00137 | 0.013898 | 0.003532 | −0.011902 | −0.000997 | −0.013583 | −0.009989 | −0.001659 | −0.013064 |
| 64 | −0.005745 | 0.003631 | 0.00453 | 0.006774 | −0.020585 | −0.028421 | 0.02128 | −0.006643 | 0.004146 | 0.019797 | 0.008911 | 0.006668 | −0.022888 | −0.042528 |
| 65 | 0.006335 | −0.025335 | 0.010591 | −0.004533 | 0.002228 | 0.001762 | −0.012568 | 0.001993 | −0.008121 | −0.000711 | −0.003651 | 0.000229 | −0.004089 | 0.000057 |
| 66 | −0.062101 | −0.00879 | 0.008181 | −0.004807 | 0.013215 | 0.031618 | −0.017035 | 0.024489 | 0.000824 | 0.009642 | 0.007022 | 0.01572 | −0.022159 | −0.041409 |
| 67 | 0.829351 | −0.042757 | 0.012442 | −0.000704 | 0.03292 | 0.028586 | −0.012169 | 0.04122 | 0.005006 | 0.006354 | 0.012545 | 0.010296 | 0.009968 | −0.00285 |
| 68 | −0.02741 | 0.772923 | −0.024511 | 0.013177 | 0.011901 | 0.030382 | 0.009347 | 0.006107 | 0.000204 | 0.048341 | 0.000852 | −0.004236 | 0.012006 | 0.021157 |
| 69 | −0.010274 | −0.035724 | 0.835537 | −0.083298 | −0.053737 | −0.013662 | 0.014759 | 0.039533 | −0.07332 | −0.072624 | −0.088753 | −0.078681 | −0.069567 | 0.00772 |
| 70 | −0.001999 | 0.001053 | −0.080012 | 0.841012 | −0.027393 | 0.004351 | −0.019296 | 0.006088 | −0.097041 | −0.084297 | −0.107092 | −0.113636 | −0.084059 | −0.016594 |
| 71 | 0.02002 | −0.017619 | −0.055671 | −0.024469 | 0.834609 | −0.103575 | −0.075421 | −0.008638 | −0.051131 | −0.032743 | −0.060262 | −0.05872 | −0.035706 | −0.027069 |
| 72 | 0.025267 | 0.015353 | −0.022294 | 0.005663 | −0.108347 | 0.829123 | −0.092405 | −0.017836 | −0.000088 | 0.008087 | −0.004628 | −0.002616 | 0.015636 | 0.000631 |
| 73 | 0.0017 | −0.010168 | 0.000555 | −0.008889 | −0.056972 | −0.069466 | 0.735969 | 0.021052 | −0.007482 | 0.026829 | −0.004563 | −0.015146 | −0.012881 | 0.01917 |
| 74 | 0.056974 | 0.022251 | 0.046016 | 0.005897 | −0.01467 | −0.029912 | 0.006991 | 0.823437 | 0.007385 | −0.014587 | 0.004818 | 0.003238 | 0.0088 | 0.003099 |
| 75 | −0.007159 | −0.016086 | −0.067673 | −0.09476 | −0.055781 | 0.000057 | −0.013985 | 0.002032 | 0.895386 | −0.075135 | −0.105139 | −0.1116 | −0.088511 | −0.002286 |
| 76 | −4.004988 | 0.038266 | −0.062827 | −4.088743 | −4.039423 | 0.000626 | 0.007054 | −4.019776 | −4.082674 | 0.859512 | −4.08663 | −4.079459 | −4.076463 | 0.010332 |
| 77 | −0.003377 | −0.015248 | −0.085668 | −0.104755 | −0.064635 | −0.002398 | −0.00573 | 0.000327 | −0.104398 | −0.081729 | 0.885001 | −0.117044 | −0.082353 | −0.000836 |
| 78 | −0.001973 | −0.018857 | −0.077662 | −0.110831 | −0.066326 | −0.001847 | −0.018238 | 0.000581 | −0.110034 | −0.073535 | −0.117602 | 0.863587 | −0.082053 | 0.000885 |
| 79 | 0.0052 | −0.010564 | −0.067321 | −0.084973 | −0.043618 | 0.010019 | −0.015597 | −0.007813 | −0.088055 | −0.068348 | −0.081965 | −0.086461 | 0.872489 | 0.005545 |
| 80 | 0.00104 | 0.02728 | −0.000384 | −4.025604 | −0.007004 | 0.017892 | 0.001169 | 0.020766 | −0.012419 | 0.004114 | −0.007443 | −0.005723 | −0.017637 | 0.748459 |
| 81 | 0.007466 | 0.023652 | −0.036063 | −0.040484 | 0.010172 | −0.004996 | 0.040749 | −0.027471 | −0.025798 | −0.060869 | −0.036102 | −0.021781 | 0.001061 | 0.015899 |

APPENDIX B3-continued

PCA Transformation Matrix (340 × 340 Early/Late)

| | | | | | | | | | | | | | |
|---|---|---|---|---|---|---|---|---|---|---|---|---|---|
| 82 | 0.011209 | −0.001657 | −0.012573 | −0.012609 | −0.02949 | −0.020225 | 0.011441 | 0.019585 | −0.001516 | −0.005205 | −0.00098 | −0.002888 | −0.012672 | −0.025 |
| 83 | 0.01245 | −0.012152 | 0.002781 | 0.0065621 | −0.032198 | −0.017572 | 0.015625 | 0.0146651 | 0.007761 | 0.01491 | 0.010786 | 0.002151 | 0.0035161 | −0.031719 |
| 84 | 0.023316 | 0.008266 | 0.005844 | 0.005337 | −0.046809 | −0.025737 | 0.003994 | 0.008968 | 0.010028 | 0.012705 | 0.007096 | 0.000354 | 0.012185 | −0.024755 |
| 85 | −0.009092 | 0.037187 | −0.011401 | 0.023128 | −0.023306 | −0.074056 | −0.069024 | 0.011949 | 0.011325 | −0.006109 | 0.022224 | 0.029041 | −0.026913 | 0.00644 |
| 86 | −0.008976 | 0.014453 | −0.025468 | 0.009646 | −0.099835 | −0.101961 | −0.100455 | 0.020685 | 0.003687 | 0.002674 | −0.000987 | 0.002024 | 0.012605 | −0.006038 |
| 87 | −0.019662 | 0.007073 | 0.001232 | 0.004605 | −0.070932 | −0.068157 | −0.074114 | 0.012895 | 0.012768 | 0.005739 | 0.017848 | 0.018492 | 0.011354 | −0.073787 |
| 88 | 0.000724 | 0.002955 | 0.003454 | 0.010718 | −0.028485 | −0.003477 | 0.007191 | 0.021409 | 0.010963 | 0.022317 | 0.011149 | 0.000317 | 0.008484 | −0.03699 |
| 89 | 0.008288 | −0.032355 | −0.011454 | 0.006637 | −0.039674 | −0.010534 | 0.017756 | 0.007139 | 0.008958 | 0.022979 | 0.007737 | −0.00992 | 0.008505 | −0.020915 |
| 90 | 0.003233 | −0.034681 | −0.020439 | 0.005983 | −0.047032 | −0.026369 | 0.005154 | −0.005718 | 0.00851 | 0.013445 | 0.009853 | −0.000949 | 0.002363 | −0.029087 |
| 91 | 0.011333 | −0.004278 | 0.002919 | −0.006634 | −0.034706 | −0.038476 | −0.001404 | 0.001031 | 0.003032 | 0.020946 | 0.00286 | −0.007079 | −0.002657 | −0.017019 |
| 92 | 0.003337 | 0.040847 | 0.005976 | −0.038349 | −0.005657 | −0.031286 | −0.053002 | 0.020991 | −0.014977 | −0.004884 | −0.018444 | −0.036282 | 0.003393 | 0.034366 |
| 93 | −0.001995 | −0.016251 | −0.01465 | −0.014713 | −0.054173 | −0.040103 | −0.017122 | 0.019622 | −0.004581 | 0.007519 | −0.008409 | −0.013011 | −0.003341 | −0.040409 |
| 94 | 0.008244 | −0.011365 | −0.001674 | −0.023478 | −0.021526 | −0.017525 | −0.034012 | −0.004486 | −0.004456 | 0.011915 | −0.00114 | −0.017825 | −0.01118 | −0.016349 |
| 95 | −0.004319 | −0.059259 | −0.026109 | 0.016527 | 0.01786f | 0.004629 | −0.016724 | 0.013303 | 0.033071 | 0.041748 | 0.034939 | 0.043701 | 0.014935 | −0.007443 |
| 96 | −0.010554 | 0.020007 | 0.012489 | −0.043354 | −0.014462 | −0.00877 | −0.0535 | −0.027856 | −0.007659 | −0.000502 | −0.00991 | −0.013457 | −0.017934 | −0.011302 |
| 97 | 0.018374 | 0.019649 | 0.001964 | −0.016152 | 0.020195 | 0.005484 | −0.02331 | −0.020791 | 0.000482 | −0.007639 | 0.004104 | 0.000098 | −0.004604 | −0.033624 |
| 98 | −0.021767 | 0.025984 | 0.017734 | 0.017025 | −0.004589 | −0.016997 | −0.011145 | −0.006726 | 0.010212 | −0.002234 | 0.01529 | 0.015846 | 0.003338 | −0.04409 |
| 99 | 0.002555 | 0.012234 | −0.016865 | −0.009921 | 0.008767 | −0.00273 | −0.015974 | −0.01843 | −0.0022 | −0.007536 | −0.003851 | −0.00008 | −0.008391 | 0.004767 |
| 100 | −0.007058 | 0.024007 | −0.008702 | −0.002516 | −0.001088 | −0.02729 | −0.012778 | −0.013953 | 0.005873 | −0.011591 | 0.003894 | 0.005125 | −0.000332 | 0.000589 |
| 101 | −0.024081 | 0.016097 | 0.026683 | 0.006146 | −0.007564 | −0.009348 | −0.012265 | −0.030713 | 0.006931 | −0.011639 | 0.008523 | 0.007237 | 0.00883 | −0.053065 |
| 102 | 0.007931 | 0.016906 | −0.018982 | −0.037185 | 0.00194 | −0.022244 | −0.031701 | 0.005896 | 0.005242 | −0.003014 | −0.005751 | −0.001391 | 0.021432 | −0.016015 |
| 103 | −0.005398 | −0.03787 | −0.007226 | −0.001022 | 0.004121 | 0.003228 | 0.025817 | 0.016324 | −0.003232 | 0.051595 | −0.004575 | −0.005721 | 0.01448 | −0.028628 |
| 104 | −0.007134 | 0.039928 | −0.002589 | 0.002328 | −0.000064 | 0.001698 | −0.012342 | −0.030696 | 0.004287 | −0.005188 | 0.002682 | 0.004493 | 0.017097 | −0.036395 |
| 105 | 0.031188 | −0.01569 | 0.021704 | 0.008686 | −0.044856 | −0.008427 | −0.037573 | 0.032484 | −0.01275 | 0.001637 | −0.011481 | −0.025512 | 0.017954 | −0.008006 |
| 106 | −0.005132 | 0.012804 | 0.031049 | 0.004423 | −0.000978 | 0.012554 | 0.005431 | 0.035703 | −0.002928 | 0.018339 | −0.005134 | −0.006454 | −0.005585 | 0.005316 |
| 107 | 0.010726 | 0.013119 | −0.003017 | 0.000122 | −0.01336 | −0.004318 | −0.039163 | 0.019149 | −0.003615 | −0.012533 | −0.012462 | −0.014923 | 0.011717 | −0.016967 |
| 108 | 0.021939 | −0.014651 | 0.028356 | 0.006708 | 0.004987 | 0.034523 | 0.013536 | −0.038902 | 0.006179 | −0.006997 | 0.006348 | 0.010884 | 0.001679 | −0.062523 |
| 109 | 0.040955 | −0.022398 | −0.041237 | −0.013055 | 0.030796 | −0.001881 | 0.016406 | 0.024354 | −0.003183 | −0.018081 | 0.00024 | −0.00477 | 0.01286 | 0.008629 |
| 110 | 0.038057 | 0.027636 | 0.000052 | −0.001262 | −0.026834 | −0.027759 | 0.011287 | 0.033892 | −0.020955 | 0.024 | −0.025854 | −0.023402 | −0.025825 | −0.065106 |
| 111 | 0.019705 | 0.027576 | 0.041184 | 0.003063 | 0.022811 | 0.016397 | −0.04446 | −0.03734 | 0.01653 | −0.00837 | 0.022839 | 0.02441 | −0.007746 | −0.002693 |
| 112 | −0.008944 | 0.00559 | −0.021705 | 0.008389 | −0.016597 | 0.009947 | 0.02067 | 0.015302 | 0.010319 | 0.008632 | −0.006278 | 0.001146 | 0.014426 | 0.013191 |
| 113 | 0.028522 | −0.031589 | −0.003184 | −0.007839 | 0.028204 | 0.029143 | −0.035685 | 0.00601 | 0.009761 | 0.011069 | 0.010366 | 0.007012 | −0.011005 | 0.022089 |
| 114 | 0.008263 | −0.005329 | −0.005185 | 0.001812 | 0.000768 | 0.026412 | 0.032128 | −0.0592 | 0.011064 | −0.00214 | 0.004891 | 0.004848 | −0.003107 | −0.023156 |
| 115 | −0.016249 | 0.040125 | 0.052241 | −0.025514 | −0.00462 | −0.025419 | −0.004025 | −0.028685 | −0.00577 | −0.014114 | −0.006008 | −0.006729 | −0.00073 | 0.061194 |
| 116 | 0.009693 | −0.061921 | −0.013683 | 0.009766 | −0.026409 | −0.05095 | −0.039305 | −0.025021 | −0.008346 | −0.00941 | −0.007089 | −0.007315 | −0.009873 | 0.00423 |
| 117 | 0.0521 | 0.084825 | 0.022339 | 0.003045 | −0.00649 | −0.002213 | −0.000356 | −0.037956 | 0.015252 | −0.019317 | 0.017283 | 0.031947 | −0.003278 | 0.028617 |
| 118 | 0.002948 | 0.043307 | −0.011294 | −0.047902 | 0.003546 | −0.009471 | −0.01935 | −0.020046 | 0.014743 | −0.015409 | 0.011975 | 0.020946 | −0.012384 | −0.044466 |
| 119 | 0.023675 | −0.010336 | −0.044956 | −0.011146 | −0.021434 | −0.031342 | −0.008158 | 0.00224 | 0.004247 | −0.003964 | −0.00396 | −0.001144 | −0.000662 | 0.013156 |
| 120 | 0.042998 | 0.014018 | 0.004116 | 0.012321 | −0.00815 | 0.004449 | −0.008213 | −0.032671 | 0.010174 | −0.002325 | 0.013231 | 0.015939 | −0.026344 | 0.026618 |
| 121 | 0.057147 | 0.004013 | −0.013879 | −0.001765 | 0.021583 | 0.004658 | 0.05254 | −0.015609 | 0.001005 | 0.028153 | 0.006399 | 0.00392 | −0.019564 | −0.005881 |
| 122 | 0.033495 | 0.048524 | 0.013401 | −0.012066 | 0.011912 | 0.017205 | 0.013873 | 0.019378 | 0.002696 | −0.001802 | −0.000592 | 0.008198 | 0.004575 | −0.009847 |
| 123 | 0.040665 | 0.010396 | −0.010024 | 0.000514 | −0.00983 | 0.001489 | 0.025627 | 0.024943 | 0.003871 | 0.00048 | −0.003421 | 0.002531 | 0.000805 | −0.004518 |
| 124 | 0.028052 | 0.006723 | −0.010423 | −0.006462 | −0.002935 | 0.001088 | 0.006028 | −0.008114 | 0.007638 | −0.001817 | 0.003298 | 0.000709 | 0.004032 | 0.002407 |
| 125 | 0.012396 | 0.019607 | −0.00391 | 0.02958 | −0.032371 | −0.006128 | 0.049054 | −0.002902 | 0.005152 | −0.008671 | 0.003291 | 0.015463 | −0.010799 | −0.019684 |
| 126 | 0.02088 | 0.054838 | −0.009732 | −0.016484 | 0.009821 | 0.016003 | 0.007563 | −0.001182 | 0.002801 | −0.008184 | −0.001727 | 0.005904 | 0.008168 | −0.004614 |
| 127 | −0.017023 | 0.001831 | 0.001222 | −0.002302 | −0.003192 | −0.000095 | 0.011928 | −0.004071 | 0.00336 | 0.005847 | −0.00161 | −0.000958 | 0.014141 | 0.00935 |
| 128 | 0.02011 | 0.013127 | −0.010513 | −0.017902 | −0.022218 | −0.029031 | −0.007315 | −0.010781 | −0.01588 | −0.006993 | −0.022864 | −0.017813 | 0.002294 | −0.021357 |
| 129 | −0.024069 | 0.006854 | −0.05051 | 0.004462 | −0.025101 | 0.002495 | 0.013464 | 0.01819 | −0.007386 | 0.019877 | −0.014237 | −0.003089 | −0.004578 | −0.007575 |
| 130 | −0.029942 | −0.028519 | 0.013057 | −0.039538 | 0.016286 | 0.010373 | −0.033981 | 0.026324 | −0.030929 | −0.015347 | −0.024437 | −0.035887 | −0.010036 | 0.045578 |
| 131 | 0.034421 | −0.0556 | −0.01477 | −0.006096 | −0.000296 | −0.006289 | −0.025702 | 0.025274 | −0.010449 | 0.011629 | −0.007857 | −0.017834 | −0.016866 | −0.019359 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 132 | 0.031439 | 0.029298 | −0.036199 | 0.00615 | −0.036342 | −0.041332 | −0.015943 | 0.009467 | 0.004179 | −0.00949 | 0.002427 | 0.005619 | 0.00265 | −0.025484 |
| 133 | 0.011617 | −0.041834 | −0.000962 | 0.0402 | −0.014731 | −0.013403 | 0.009167 | 0.010409 | 0.004535 | 0.0392394 | 0.015598 | 0.015998 | −0.014533 | −0.038904 |
| 134 | −0.019223 | 0.007883 | 0.000026 | −0.024507 | 0.031174 | 0.004744 | 0.010393 | −0.030679 | −0.001762 | −0.009852 | −0.002795 | −0.008007 | 0.023415 | 0.009678 |
| 135 | −0.001819 | 0.017033 | −0.00435 | 0.010543 | −0.029079 | −0.005864 | 0.004976 | −0.014231 | −0.005465 | −0.010296 | −0.005248 | −0.011869 | −0.005706 | −0.009757 |
| 136 | −0.000079 | −0.014528 | 0.017469 | −0.002142 | −0.01841 | −0.044905 | −0.065423 | 0.000042 | −0.0067 | −0.016505 | 0.004106 | −0.001133 | −0.021191 | 0.040162 |
| 137 | −0.00564 | −0.024503 | −0.002687 | 0.002121 | −0.021479 | −0.03358 | 0.000137 | −0.0283 | −0.000453 | 0.001208 | −0.004716 | −0.008349 | 0.009135 | −0.014394 |
| 138 | 0.016504 | −0.025937 | −0.000282 | −0.001393 | 0.036928 | 0.023196 | 0.003958 | −0.027195 | 0.000971 | −0.008001 | 0.004754 | 0.002545 | 0.010109 | 0.011818 |
| 139 | −0.014965 | −0.002237 | −0.009169 | −0.015796 | −0.007245 | −0.001401 | −0.033968 | 0.021268 | −0.002308 | −0.013006 | −0.009712 | −0.001189 | 0.005582 | −0.067076 |
| 140 | 0.001704 | 0.020418 | −0.030804 | 0.020484 | −0.000428 | −0.024033 | −0.033684 | 0.026083 | 0.009264 | −0.012474 | −0.002459 | 0.010297 | 0.020679 | 0.031431 |
| 141 | −0.010505 | −0.003395 | −0.007162 | 0.010765 | −0.010826 | 0.003519 | 0.023229 | 0.026522 | 0.002945 | 0.01142 | −0.003344 | −0.004401 | 0.03065 | 0.01076 |
| 142 | 0.019222 | 0.039706 | 0.035763 | 0.009069 | 0.035595 | 0.040326 | −0.014778 | 0.004767 | −0.002674 | −0.007704 | 0.01329 | 0.008721 | −0.01076 | 0.017608 |
| 143 | 0.022944 | 0.036707 | 0.030356 | 0.024707 | 0.00967 | 0.023951 | 0.041448 | 0.005154 | 0.002141 | −0.010353 | 0.001554 | 0.00558 | 0.017254 | −0.021306 |
| 144 | −0.010917 | −0.015454 | −0.000825 | 0.021342 | 0.004407 | 0.007933 | 0.021658 | 0.025045 | 0.009235 | 0.019717 | 0.010164 | 0.011833 | 0.018549 | −0.003293 |
| 145 | 0.018754 | 0.028277 | −0.005374 | −0.020197 | 0.006858 | −0.009102 | −0.017979 | 0.007689 | 0.004889 | −0.000995 | 0.006914 | 0.015705 | −0.002927 | −0.063279 |
| 146 | −0.008868 | 0.010196 | −0.024476 | 0.016042 | −0.009441 | 0.004087 | −0.003185 | 0.002758 | −0.000602 | −0.01731 | 0.002087 | 0.010528 | −0.016469 | −0.018107 |
| 147 | −0.017472 | 0.019918 | −0.01091 | 0.009941 | 0.014561 | 0.050942 | −0.016001 | 0.047657 | −0.027218 | −0.049197 | −0.010817 | −0.012798 | −0.028225 | 0.000492 |
| 148 | −0.051638 | 0.022817 | 0.033277 | 0.003504 | 0.008514 | 0.027648 | −0.061391 | −0.017689 | 0.016844 | −0.025748 | 0.013929 | 0.025466 | −0.010098 | 0.010732 |
| 149 | 0.027206 | 0.012782 | 0.017556 | −0.009255 | −0.00795 | −0.012793 | 0.011081 | −0.046191 | 0.002084 | 0.004495 | −0.004198 | −0.00048 | 0.005422 | −0.00406 |
| 150 | −0.003168 | 0.003148 | 0.005384 | 0.010799 | 0.006255 | 0.024518 | −0.006475 | −0.012619 | −0.00019 | −0.006069 | −0.001716 | −0.003651 | −0.011822 | −0.002959 |
| 151 | −0.043994 | 0.059917 | 0.015726 | −0.009786 | 0.017336 | −0.015061 | −0.032135 | 0.031298 | 0.000148 | −0.009572 | 0.001213 | 0.009124 | 0.002726 | −0.071305 |
| 152 | −0.013653 | −0.026091 | −0.009247 | 0.01742 | −0.000191 | 0.000012 | 0.029088 | 0.010569 | 0.008187 | 0.011047 | 0.001971 | 0.006488 | 0.010701 | 0.029913 |
| 153 | 0.000455 | 0.001629 | −0.000412 | 0.032177 | −0.003665 | 0.002789 | 0.024776 | 0.036411 | 0.010938 | 0.010895 | 0.013025 | 0.025889 | 0.011336 | −0.005073 |
| 154 | 0.00817 | 0.015272 | 0.030036 | −0.006444 | 0.002074 | −0.012596 | −0.05643 | 0.016235 | −0.016957 | −0.013414 | −0.00187 | −0.013251 | −0.011206 | 0.026284 |
| 155 | 0.007076 | −0.001567 | −0.040792 | −0.020152 | −0.02157 | −0.007321 | 0.021871 | 0.021838 | −0.010621 | −0.018634 | −0.012342 | −0.005199 | −0.016775 | −0.040748 |
| 156 | 0.018149 | −0.029222 | 0.017755 | −0.009762 | −0.007954 | −0.014545 | 0.008113 | −0.039263 | −0.018476 | −0.014002 | −0.018974 | −0.018719 | 0.009748 | −0.003906 |
| 157 | 0.008302 | 0.061767 | −0.008353 | 0.009824 | −0.00119 | −0.003448 | 0.021796 | −0.003403 | 0.000182 | −0.017838 | −0.001061 | 0.006575 | −0.01445 | 0.02142 |
| 158 | 0.008295 | −0.006972 | 0.031813 | −0.000294 | 0.008724 | 0.035704 | 0.038237 | −0.052952 | −0.019448 | −0.04006 | −0.009009 | −0.020698 | −0.022811 | −0.054695 |
| 159 | −0.00205 | 0.012869 | 0.016387 | −0.019557 | 0.020453 | 0.001639 | 0.018449 | −0.01652 | −0.011997 | 0.011187 | −0.009448 | −0.028964 | 0.007102 | −0.036747 |
| 160 | 0.047106 | 0.01237 | −0.003304 | −0.012629 | 0.005748 | 0.009573 | 0.081817 | −0.028864 | 0.00331 | −0.028302 | −0.014126 | 0.012904 | −0.013289 | −0.010403 |
| 161 | 0.015444 | −0.024263 | −0.047405 | 0.005014 | −0.028252 | −0.005058 | 0.010009 | −0.043026 | −0.007615 | −0.04866 | −0.021784 | −0.014355 | −0.0001 | 0.008794 |
| 162 | 0.002708 | −0.037906 | −0.002934 | 0.024954 | −0.004823 | −0.005491 | 0.02707 | −0.021941 | 0.023029 | 0.010976 | 0.021426 | 0.036355 | 0.016388 | −0.007186 |
| 163 | −0.007818 | 0.022171 | 0.015922 | 0.014129 | 0.009852 | 0.008063 | 0.022245 | −0.009633 | 0.009594 | −0.010861 | 0.00949 | 0.011619 | 0.012272 | 0.02069 |
| 164 | −0.040205 | −0.017206 | 0.001942 | −0.009876 | 0.032658 | 0.00942 | −0.00957 | 0.043661 | 0.004853 | 0.011833 | 0.008379 | 0.007447 | 0.018877 | −0.00303 |
| 165 | −0.009914 | −0.001759 | −0.00536 | −0.006574 | 0.001904 | 0.014159 | 0.052899 | 0.014725 | 0.00995 | −0.020534 | 0.005625 | 0.041066 | 0.00562 | −0.0467 |
| 166 | 0.028331 | 0.005744 | 0.033504 | 0.012573 | 0.039517 | 0.051204 | 0.007439 | −0.000197 | 0.016876 | 0.034106 | 0.02917 | 0.023243 | −0.000155 | 0.007196 |
| 167 | 0.000312 | −0.031596 | −0.002863 | 0.019748 | −0.005432 | −0.021091 | −0.001945 | −0.013256 | 0.014392 | 0.02151 | 0.019527 | 0.019583 | 0.023973 | −0.018351 |
| 168 | −0.013375 | −0.020565 | 0.008818 | 0.00444 | 0.015504 | −0.006204 | −0.020851 | 0.021925 | 0.008541 | 0.018597 | 0.006117 | 0.005998 | 0.010993 | 0.031657 |
| 169 | −0.006087 | 0.004859 | 0.016565 | 0.015067 | −0.020859 | 0.003229 | 0.00834 | 0.000279 | 0.008777 | −0.006047 | 0.008398 | 0.010243 | 0.0048 | −0.037369 |
| 170 | −0.034915 | −0.015433 | 0.019692 | 0.002492 | −0.014788 | 0.006517 | 0.010084 | 0.004583 | 0.003321 | −0.012957 | 0.002556 | 0.005121 | 0.008827 | −0.02817 |
| 171 | 0.003497 | −0.003067 | −0.003543 | 0.010336 | −0.007603 | 0.014237 | 0.015198 | 0.004955 | 0.007761 | 0.000379 | 0.001432 | 0.000057 | 0.013317 | −0.016723 |
| 172 | 0.016565 | 0.002356 | −0.00251 | 0.001969 | −0.000155 | −0.014334 | 0.01764 | −0.014734 | 0.007639 | −0.005157 | 0.005892 | 0.008851 | 0.00262 | −0.028353 |
| 173 | 0.00566 | −0.012687 | 0.01604 | 0.009423 | 0.003675 | −0.001817 | 0.011072 | −0.018466 | 0.009211 | 0.010355 | 0.00858 | 0.018555 | −0.000927 | 0.000241 |
| 174 | 0.013408 | −0.025426 | 0.003647 | −0.003358 | 0.007715 | 0.01227 | −0.007266 | 0.007717 | 0.007757 | 0.003631 | 0.005036 | 0.002942 | 0.000514 | 0.000097 |
| 175 | 0.008869 | −0.015651 | −0.009853 | −0.050827 | 0.025006 | 0.047148 | 0.023978 | 0.019694 | 0.001507 | −0.036833 | −0.010542 | −0.003245 | −0.020014 | −0.003399 |
| 176 | 0.011532 | −0.03993 | 0.019311 | 0.003445 | −0.012525 | −0.01392 | 0.006942 | −0.026659 | 0.002966 | −0.020611 | 0.003922 | 0.003334 | 0.005766 | 0.012643 |
| 177 | −0.015305 | −0.051236 | 0.000971 | −0.002682 | 0.004815 | 0.001039 | −0.04997 | −0.013569 | 0.000253 | 0.018388 | 0.002774 | −0.008266 | 0.014307 | −0.008454 |
| 178 | −0.03427 | 0.015112 | −0.004103 | 0.011829 | −0.005503 | 0.011474 | −0.018078 | 0.025599 | 0.008976 | 0.003016 | 0.002221 | 0.010938 | 0.015198 | −0.047926 |
| 179 | −0.016663 | 0.030924 | 0.001017 | 0.011249 | 0.000839 | 0.003821 | −0.010555 | 0.020313 | 0.007836 | −0.005836 | 0.008441 | 0.013522 | 0.000903 | −0.042066 |
| 180 | −0.020665 | 0.013518 | 0.005261 | 0.012074 | −0.013816 | −0.003754 | −0.008643 | 0.008541 | 0.006037 | 0.003426 | 0.005427 | 0.008799 | 0.000157 | −0.029635 |
| 181 | −0.016896 | 0.022913 | 0.005982 | 0.014718 | −0.010751 | −0.011851 | −0.002929 | 0.009176 | 0.006175 | −0.002152 | 0.007409 | 0.012279 | 0.002956 | −0.039757 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 182 | −0.020191 | 0.014857 | 0.000901 | −0.000916 | −0.002992 | −0.016214 | −0.018803 | −0.00038 | 0.002994 | −0.004107 | 0.001505 | 0.003759 | −0.002366 | −0.013452 |
| 183 | 0.010572 | 0.037851 | −0.028612 | −0.011569 | −0.007177 | −0.014608 | −0.012192 | 0.013577 | −0.00196 | −0.011511 | −0.009139 | −0.00905 | −0.0026 | −0.016509 |
| 184 | 0.029138 | 0.048528 | −0.037939 | −0.006096 | 0.001577 | −0.008779 | 0.033126 | −0.00561 | 0.008586 | −0.014053 | −0.003632 | 0.001267 | −0.002018 | −0.007282 |
| 185 | 0.030674 | 0.015339 | 0.000264 | −0.018559 | −0.010246 | −0.020955 | −0.02078 | 0.006193 | −0.006811 | 0.014685 | −0.014423 | −0.010242 | 0.001672 | −0.02471 |
| 186 | −0.013111 | −0.013665 | −0.036291 | 0.00562 | 0.042116 | 0.016994 | 0.008489 | 0.069566 | 0.010517 | 0.025694 | 0.012776 | 0.010711 | −0.001372 | 0.057439 |
| 187 | −0.003128 | 0.014281 | 0.008311 | 0.004442 | 0.003177 | −0.007071 | 0.005526 | −0.012919 | 0.018746 | 0.00763 | 0.018676 | 0.024776 | 0.007697 | 0.006719 |
| 188 | 0.005587 | −0.001239 | −0.007631 | −0.017599 | −0.010033 | −0.012684 | −0.007011 | 0.002724 | 0.00482 | −0.008757 | 0.000085 | 0.00095 | 0.000463 | 0.005512 |
| 189 | 0.014421 | 0.017141 | −0.003394 | −0.036396 | 0.005635 | 0.010467 | 0.012974 | 0.006182 | 0.002648 | −0.043858 | −0.001894 | −0.00764 | −0.015207 | −0.000345 |
| 190 | 0.007544 | −0.000658 | −0.001159 | −0.00553 | −0.003452 | −0.006648 | 0.019903 | −0.012815 | 0.002416 | −0.006701 | −0.001431 | −0.001946 | −0.002449 | 0.007213 |
| 191 | 0.004443 | 0.04212 | 0.00237 | 0.008783 | 0.00042 | −0.011274 | 0.018036 | −0.017387 | 0.01482 | −0.011165 | 0.012082 | 0.012997 | 0.012285 | 0.007671 |
| 192 | −0.013152 | 0.020292 | −0.01126 | 0.010837 | 0.027786 | −0.002101 | −0.01786 | 0.015195 | 0.019117 | 0.028589 | 0.012297 | 0.013516 | 0.025617 | 0.000318 |
| 193 | −0.016979 | −0.017088 | −0.004686 | 0.01961 | 0.021133 | 0.000378 | 0.015625 | 0.031961 | 0.023876 | 0.020105 | 0.019579 | 0.022125 | 0.019489 | 0.037919 |
| 194 | 0.005202 | −0.002762 | −0.026134 | −0.015334 | −0.005954 | 0.016563 | 0.022221 | 0.048934 | −0.000548 | −0.01924 | −0.00961 | −0.004039 | −0.004621 | 0.028338 |
| 195 | 0.010365 | −0.024193 | −0.023062 | −0.003821 | 0.009752 | 0.009915 | 0.028185 | −0.005034 | −0.017731 | −0.014725 | −0.013061 | −0.013985 | −0.026798 | −0.024512 |
| 196 | −0.01181 | 0.000816 | −0.017698 | −0.016623 | 0.017577 | 0.004501 | 0.015455 | −0.008337 | −0.003158 | −0.014776 | −0.004325 | −0.003916 | −0.018674 | −0.011297 |
| 197 | −0.008512 | −0.002468 | 0.001734 | −0.008119 | 0.00161 | −0.015922 | 0.027396 | −0.019749 | 0.00152 | 0.007272 | 0.000558 | −0.000823 | −0.004596 | 0.001197 |
| 198 | −0.006882 | −0.013589 | −0.011058 | −0.012801 | 0.020698 | 0.030614 | 0.027188 | 0.008725 | 0.000023 | −0.010227 | −0.004041 | 0.005358 | 0.015217 | −0.0198 |
| 199 | 0.025136 | 0.011308 | 0.039861 | −0.000604 | 0.025838 | 0.015676 | 0.006086 | −0.024877 | 0.003512 | −0.006085 | 0.013003 | −0.001008 | 0.018278 | 0.025284 |
| 200 | −0.017206 | −0.013727 | −0.036736 | 0.022969 | 0.004875 | −0.006284 | 0.022359 | 0.046764 | 0.009431 | 0.019979 | 0.009462 | 0.010952 | 0.032878 | −0.051352 |
| 201 | 0.004411 | −0.024726 | −0.005948 | 0.033208 | −0.084889 | −0.038537 | −0.081073 | −0.039889 | 0.008067 | −0.012925 | −0.002698 | 0.007443 | 0.025889 | −0.003579 |
| 202 | −0.029638 | −0.013513 | −0.004253 | 0.000751 | 0.016688 | 0.02605 | −0.001847 | 0.033781 | −0.001999 | 0.015933 | −0.003596 | 0.002651 | 0.014868 | 0.007151 |
| 203 | 0.025336 | 0.015879 | 0.001744 | −0.024967 | −0.033355 | −0.02703 | 0.006973 | 0.013777 | −0.004379 | −0.000188 | −0.009249 | −0.002706 | −0.007172 | −0.011206 |
| 204 | −0.021211 | 0.03819 | −0.034498 | 0.031829 | −0.020781 | −0.059187 | 0.009256 | −0.036949 | −0.002877 | −0.019903 | −0.005042 | 0.01504 | −0.00155 | 0.084918 |
| 205 | −0.012172 | 0.029609 | 0.014162 | 0.014654 | 0.018962 | −0.015782 | 0.052934 | 0.04718 | 0.012722 | 0.007161 | 0.014051 | 0.015589 | 0.032411 | −0.026264 |
| 206 | 0.004523 | −0.010513 | 0.000656 | 0.034318 | 0.000246 | 0.032786 | 0.032086 | −0.014829 | 0.012127 | 0.011762 | 0.012276 | 0.012208 | −0.004992 | −0.010874 |
| 207 | −0.03795 | 0.02164 | 0.020415 | −0.016158 | 0.002806 | −0.05553 | 0.041586 | −0.017411 | 0.007378 | 0.007774 | 0.010213 | 0.004774 | −0.004699 | 0.018961 |
| 208 | −0.030029 | −0.03874 | −0.026317 | −0.024298 | −0.024725 | −0.019205 | 0.048942 | 0.039664 | −0.008362 | 0.030698 | −0.013292 | −0.011186 | 0.006893 | −0.01404 |
| 209 | −0.001695 | 0.013885 | 0.007804 | 0.007892 | 0.002308 | 0.000222 | −0.014351 | −0.001527 | −0.020588 | 0.012182 | −0.005301 | −0.011637 | −0.032218 | 0.00655 |
| 210 | 0.017231 | −0.007235 | −0.004426 | 0.009993 | −0.009781 | −0.002559 | −0.022211 | −0.034982 | −0.005722 | 0.017098 | −0.008461 | −0.00548 | −0.009239 | −0.033961 |
| 211 | −0.010644 | 0.061609 | 0.04166 | 0.020741 | −0.002285 | −0.03212 | −0.054004 | −0.068533 | −0.00704 | 0.014161 | −0.009556 | −0.009695 | 0.020413 | −0.007734 |
| 212 | −0.030587 | −0.008164 | 0.033988 | −0.003525 | 0.026746 | −0.024669 | −0.025513 | 0.021901 | 0.000204 | 0.010099 | 0.007286 | −0.005536 | 0.027608 | −0.036492 |
| 213 | 0.025119 | 0.007954 | −0.099561 | −0.035585 | −0.001551 | 0.029158 | 0.021425 | 0.038019 | −0.002109 | −0.039989 | −0.032516 | −0.019125 | 0.004028 | 0.038849 |
| 214 | −0.010099 | 0.032746 | −0.010645 | 0.001839 | −0.007395 | −0.006899 | −0.006655 | −0.001074 | −0.00024 | −0.006936 | −4.002622 | −0.007518 | −0.006913 | −0.010278 |
| 215 | −0.032544 | 0.073236 | −0.005961 | 0.029449 | 0.000673 | 0.003071 | −0.002889 | 0.054991 | 0.008156 | 0.009661 | 0.012778 | 0.005498 | −0.008913 | −0.067105 |
| 216 | −0.009612 | −0.018025 | 0.022654 | −0.000531 | 0.007607 | 0.020014 | −0.011524 | 0.010908 | 0.011367 | 0.021883 | 0.010164 | 0.000909 | 0.013043 | −0.01192 |
| 217 | 0.031351 | 0.006039 | −0.023584 | −0.016171 | 0.01286 | 0.019975 | −0.013743 | 0.020824 | 0.001274 | −0.010576 | −0.006696 | −0.003959 | 0.002583 | 0.00729 |
| 218 | 0.007592 | 0.015043 | 0.019625 | 0.01976 | −0.003835 | −0.010967 | 0.002035 | −0.002939 | 0.004513 | 0.009066 | 0.007475 | 0.00118 | −0.001966 | 0.00097 |
| 219 | −0.000297 | −0.013184 | 0.01045 | 0.007824 | 0.015135 | 0.022368 | −0.012155 | 0.015781 | 0.010602 | 0.008228 | 0.011842 | 0.007609 | 0.005555 | −0.008293 |
| 220 | 0.037069 | 0.010171 | 0.003196 | 0.004835 | 0.004987 | −0.013808 | 0.022587 | −0.009368 | 0.010323 | 0.000758 | 0.011689 | 0.008593 | 0.008866 | 0.00889 |
| 221 | 0.023147 | −0.004876 | 0.020871 | 0.016603 | 0.01217 | 0.005296 | −0.000033 | −0.012117 | 0.007594 | 0.015879 | 0.011208 | 0.0163 | −0.004331 | −0.002575 |
| 222 | −0.030981 | −0.006741 | 0.010626 | 0.008545 | 0.017471 | 0.005427 | 0.014369 | 0.004739 | 0.003523 | 0.0082 | 0.004459 | 0.002376 | 0.008026 | 0.00301 |
| 223 | −0.011685 | −0.019906 | 0.01412 | 0.012822 | 0.011949 | 0.000405 | 0.021993 | 0.016348 | 0.008749 | 0.015145 | 0.008019 | 0.007262 | 0.013066 | 0.027755 |
| 224 | −0.010423 | −0.011286 | 0.020464 | −0.001646 | 0.015828 | 0.037002 | −0.029313 | −0.02587 | 0.001943 | 0.025724 | 0.003542 | −4.008813 | 0.008459 | 0.017804 |
| 225 | 0.000427 | −0.030556 | 0.014438 | −0.006647 | 0.009411 | 0.030961 | −0.033348 | −0.024488 | 0.000064 | 0.032469 | 0.001117 | −0.013439 | 0.010882 | 0.006139 |
| 226 | 0.025277 | −0.001926 | −0.004441 | −0.007409 | 0.010969 | 0.005304 | −0.003447 | 0.010998 | −0.002286 | 0.001404 | 0.000283 | 0.000144 | −0.008108 | 0.005592 |
| 227 | 0.008314 | −0.011687 | 0.009834 | 0.003928 | 0.004519 | 0.050705 | −0.035531 | −0.005672 | −0.001721 | 0.007056 | 0.001281 | −0.000597 | −0.015637 | −0.018906 |
| 228 | −0.021666 | 0.016502 | −0.011341 | −0.024315 | 0.013501 | −0.020599 | 0.019126 | 0.028384 | 0.008636 | 0.01342 | 0.00455 | 0.001412 | 0.00567 | 0.012315 |
| 229 | 0.013111 | 0.017306 | −0.004298 | 0.008246 | −0.038903 | −0.042895 | 0.013655 | 0.011249 | 0.006302 | 0.009921 | 0.011222 | 0.004971 | 0.025854 | −0.020089 |
| 230 | −0.009832 | −0.003729 | 0.016594 | −0.007416 | −0.022905 | −0.013942 | −0.007333 | −0.008034 | −0.008604 | 0.008044 | −0.007962 | −0.018288 | 0.010758 | −0.019889 |
| 231 | 0.046508 | 0.002156 | 0.032016 | −0.006875 | −0.002991 | −0.023369 | −0.022317 | −0.02189 | −0.007701 | 0.00256 | 0.000333 | −0.000667 | −0.015964 | −0.025046 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 232 | −0.003893 | 0.019959 | 0.013396 | −0.006827 | 0.017996 | −0.005897 | 0.04619 | 0.004703 | 0.003948 | −0.004734 | 0.007715 | 0.009549 | 0.005684 | −0.014561 |
| 233 | −0.005644 | 0.037207 | −0.023839 | −0.001482 | −0.000314 | −0.005466 | 0.008322 | 0.0218 | −0.002898 | −0.021853 | −0.003841 | 0.003616 | 0.007673 | −0.062698 |
| 234 | 0.001385 | −0.028897 | −0.012836 | −0.008193 | −0.00801 | −0.022724 | −0.006218 | 0.020112 | −0.001868 | 0.006425 | 0.000673 | −0.001593 | −0.004381 | −0.052715 |
| 235 | 0.000626 | 0.012444 | −0.016063 | −0.001367 | 0.008529 | −0.023912 | −0.005224 | 0.020268 | −0.000726 | −0.012046 | 0.004318 | 0.008061 | 0.001696 | −0.032882 |
| 236 | 0.000765 | −0.019879 | 0.008613 | −0.006401 | −0.001591 | 0.010648 | 0.033929 | −0.013924 | −0.006027 | −0.005911 | −0.005618 | −0.004559 | −0.004918 | 0.001649 |
| 237 | −0.008981 | −0.028946 | −0.009438 | −0.010278 | −0.010605 | −0.00426 | −0.005998 | −0.016044 | −0.003239 | 0.000661 | −0.004912 | −0.003673 | −0.005014 | −0.000917 |
| 238 | −0.017573 | −0.023889 | −0.010827 | −0.020455 | −0.001172 | −0.00592 | −0.022387 | 0.013933 | −0.006041 | −0.008458 | −0.009899 | −0.012079 | 0.00485 | −0.010925 |
| 239 | −0.017525 | −0.000369 | −0.007074 | −0.014764 | 0.007739 | 0.001305 | −0.024876 | 0.033906 | −0.006256 | −0.007893 | −0.009633 | −0.00966 | 0.000551 | −0.003939 |
| 240 | −0.007958 | −0.005577 | −0.00008 | 0.005925 | 0.00278 | 0.007232 | 0.006509 | 0.012913 | 0.013893 | 0.004159 | 0.012084 | 0.028879 | 0.012457 | −0.016688 |
| 241 | −0.01368 | 0.003474 | −0.021838 | −0.005964 | −0.007196 | −0.011702 | −0.005134 | 0.011917 | −0.001409 | −0.0033081 | −0.004638 | −0.005115 | 0.008106 | −0.033782 |
| 242 | −0.000508 | 0.027148 | 0.015903 | −0.002517 | −0.002772 | −0.015207 | −0.009576 | 0.003171 | −0.006901 | −0.016702 | −0.003426 | −0.002082 | −0.001773 | −0.018935 |
| 243 | −0.035261 | 0.010152 | −0.007207 | −0.002929 | 0.015146 | 0.007162 | −0.03876 | 0.026313 | −0.002461 | −0.021053 | −0.001084 | 0.003619 | −0.007309 | −0.011392 |
| 244 | 0.006865 | −0.005085 | 0.011348 | 0.011347 | −0.010703 | 0.006007 | 0.000348 | −0.013972 | −0.001488 | 0.015661 | −0.000727 | −0.000974 | 0.000952 | −0.016405 |
| 245 | 0.014397 | 0.011172 | 0.006629 | 0.019152 | −0.023607 | −0.00252 | 0.011995 | 0.009986 | −0.001522 | 0.01586 | −0.004578 | −0.008842 | 0.023384 | −0.039414 |
| 246 | −0.011106 | 0.015386 | 0.017804 | 0.008562 | −0.001544 | −0.007818 | 0.008042 | 0.001082 | −0.001748 | −0.005178 | 0.004045 | 0.002998 | 0.004456 | −0.016338 |
| 247 | 0.003925 | 0.001795 | −0.010021 | −0.008431 | −0.007588 | 0.003187 | −0.000627 | 0.001159 | −0.015769 | −0.0182 | −0.016141 | −0.011597 | −0.01421 | −0.003329 |
| 248 | 0.00338 | −0.009404 | −0.019508 | 0.002624 | −0.003253 | −0.003702 | 0.014791 | 0.006171 | −0.005246 | −0.001613 | −0.005354 | −0.001429 | −0.006016 | −0.003254 |
| 249 | −0.058401 | −0.04863 | −0.010724 | 0.00931 | 0.005544 | −0.002975 | 0.032152 | 0.013315 | 0.000467 | −0.008732 | −0.000433 | 0.004341 | 0.016973 | 0.00201 |
| 250 | −0.015692 | −0.020476 | 0.008846 | 0.001275 | −0.000408 | −0.000496 | 0.003921 | −0.005768 | 0.012538 | 0.00713 | 0.01377 | 0.019395 | 0.010739 | 0.000165 |
| 251 | −0.004645 | −0.040113 | −0.012603 | −0.006704 | −0.008707 | −0.009581 | −0.007275 | −0.009539 | 0.002659 | 0.014392 | 0.001341 | 0.007776 | 0.012181 | 0.0004 |
| 252 | 0.01716 | −0.031055 | −0.021738 | 0.007301 | −0.024923 | −0.02625 | −0.022899 | 0.005611 | −0.011703 | 0.000914 | −0.01342 | −0.015204 | 0.003881 | −0.029437 |
| 253 | 0.001894 | 0.004364 | −0.01557 | −0.017986 | −0.026256 | −0.035521 | −0.008156 | 0.010804 | −0.006917 | −0.006135 | −0.012648 | −0.022775 | 0.005916 | −0.016135 |
| 254 | −0.041788 | −0.019122 | 0.011863 | 0.016526 | 0.017914 | 0.016432 | 0.015897 | 0.012318 | 0.013202 | 0.013928 | 0.01431 | 0.014981 | 0.014347 | 0.028728 |
| 255 | −0.012405 | −0.012908 | 0.018227 | 0.009275 | 0.001156 | 0.006464 | 0.000609 | −0.004279 | 0.00253 | 0.003145 | 0.007013 | 0.010158 | 0.004052 | −0.000476 |
| 256 | 0.010313 | −0.011297 | −0.014395 | 0.014931 | −0.028271 | −0.033506 | 0.010607 | 0.018773 | 0.003065 | −0.009988 | 0.000331 | −0.002987 | 0.014342 | 0.001713 |
| 257 | 0.012649 | 0.005443 | −0.005349 | 0.002054 | 0.004603 | −0.011726 | 0.020686 | −0.009075 | 0.004541 | −0.020148 | −0.000674 | 0.00895 | 0.007683 | −0.001149 |
| 258 | −0.000154 | −0.008893 | −0.011372 | −0.001058 | 0.006583 | 0.009938 | −0.007969 | −0.012672 | −0.008841 | −0.002052 | −0.01112 | −0.012237 | −0.010397 | 0.006663 |
| 259 | −0.04559 | −0.039308 | −0.011552 | 0.0039 | 0.001675 | −0.003558 | 0.006097 | 0.000815 | 0.007527 | 0.010481 | 0.005712 | 0.005514 | 0.012531 | 0.012075 |
| 260 | −0.009637 | −0.075363 | −0.010919 | 0.018807 | −0.007175 | −0.011183 | 0.002088 | 0.001307 | 0.014256 | 0.02895 | 0.014554 | 0.012796 | 0.010601 | 0.011483 |
| 261 | 0.005991 | −0.077206 | −0.020397 | −0.008395 | −0.010581 | −0.019961 | −0.023795 | −0.003751 | 0.014022 | −0.002216 | −0.001054 | −0.001054 | −0.012437 | −0.004693 |
| 262 | 0.016583 | −0.005203 | 0.00451 | −0.007877 | −0.005869 | −0.008962 | 0.004813 | −0.009131 | −0.009899 | −0.010449 | −0.010952 | −0.008626 | −0.004147 | −0.007039 |
| 263 | 0.007976 | 0.008788 | −0.007645 | −0.00373 | −0.010377 | −0.014291 | 0.006154 | −0.005734 | −0.005149 | −0.012749 | −0.008579 | −0.004409 | 0.001232 | −0.010126 |
| 264 | −0.059365 | −0.019469 | 0.00255 | 0.018048 | 0.023361 | 0.011347 | 0.011658 | 0.003208 | 0.018356 | 0.009304 | 0.021235 | 0.015394 | 0.007346 | 0.039339 |
| 265 | −0.048628 | −0.042305 | 0.000592 | 0.020322 | 0.041737 | 0.032848 | 0.009166 | 0.003693 | 0.015517 | 0.004653 | 0.020203 | 0.007897 | −0.00251 | 0.070272 |
| 267 | −0.006987 | −0.053665 | −0.007784 | −0.000847 | 0.014855 | 0.015364 | −0.006564 | −0.008973 | 0.007803 | −0.005998 | −0.012383 | −0.012383 | −0.013247 | 0.034575 |
| 268 | 0.017514 | 0.021804 | −0.00157 | −0.012757 | 0.013309 | 0.011569 | −0.004793 | 0.006398 | −0.004425 | −0.00773 | −0.001107 | −0.013642 | 0.000629 | −0.007057 |
| 269 | 0.015497 | 0.008827 | 0.001874 | −0.009353 | 0.008604 | 0.008939 | −0.000126 | −0.002491 | −0.003952 | −0.005716 | −0.000499 | −0.005641 | −0.011229 | 0.000611 |
| 270 | 0.007222 | −0.003895 | 0.002218 | −0.004435 | 0.005699 | 0.021862 | −0.004568 | −0.001087 | −0.001917 | 0.000236 | 0.000051 | 0.000354 | −0.017076 | 0.006508 |
| 271 | −0.012245 | 0.000242 | 0.015929 | 0.012436 | −0.0064 | −0.004051 | −0.002331 | 0.005064 | −0.000146 | 0.017294 | 0.00526 | 0.005559 | 0.033079 | 0.020796 |
| 272 | 0.021188 | 0.005593 | −0.002803 | −0.000167 | −0.024055 | −0.036719 | 0.005895 | 0.010206 | 0.007177 | 0.009533 | 0.012694 | 0.010828 | 0.01566 | −0.010823 |
| 273 | 0.023169 | 0.022228 | −0.00218 | 0.00021 | −0.000997 | −0.008896 | 0.010694 | −0.018446 | 0.000161 | 0.000929 | 0.003905 | −0.001187 | −0.004481 | 0.000846 |
| 274 | 0.021161 | 0.018169 | −0.00283 | −0.001204 | 0.000358 | −0.008335 | 0.006091 | −0.019012 | 0.001053 | 0.00081 | 0.004647 | −0.000417 | −0.005607 | 0.004071 |
| 275 | −0.018676 | −0.016478 | 0.00592 | 0.007544 | −0.016268 | 0.016063 | 0.009452 | −0.013494 | −0.001826 | 0.007972 | 0.000042 | 0.001338 | −0.010765 | −0.002754 |
| 276 | 0.005849 | −0.011224 | 0.013387 | −0.009715 | −0.008583 | −0.004749 | 0.020872 | −0.011821 | −0.001241 | −.002879 | 0.001718 | 0.002216 | 0.002103 | −0.004905 |
| 277 | −0.001757 | 0.008433 | −0.004816 | −0.005717 | −0.001832 | 0.010951 | −0.006457 | −0.013048 | −0.006528 | 0.002232 | −0.009002 | −0.00838 | −0.01839 | 0.005466 |
| 278 | −0.005965 | 0.003077 | −0.013364 | −0.003854 | −0.01503 | −0.001199 | −0.002594 | −0.009103 | −0.005486 | 0.010665 | −0.009742 | −0.009162 | −0.015097 | 0.019325 |
| 279 | −0.027448 | −0.004116 | −0.007944 | −0.007836 | 0.020527 | 0.018198 | −0.017027 | 0.044368 | 0.003948 | 0.00167 | 0.002241 | 0.007418 | −0.001665 | 0.015377 |
| 280 | −0.031591 | 0.03634 | −0.006675 | −0.032797 | 0.016513 | 0.019384 | −0.026058 | 0.009224 | −0.00893 | −0.029131 | −0.007447 | −0.014074 | −0.015404 | −0.021898 |
| 281 | 0.0077 | 0.03279 | −0.000017 | 0.002675 | −0.011487 | −0.016076 | 0.003558 | −0.005075 | −0.011043 | 0.004607 | −0.008153 | −0.011565 | −0.006374 | 0.017558 |
| 282 | −0.006429 | 0.029462 | 0.000795 | 0.01309 | −0.011127 | −0.009497 | −0.001669 | −0.007212 | −0.011224 | 0.006334 | −0.009664 | −0.012717 | 0.001372 | 0.024971 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 283 | 0.005743 | −0.009454 | −0.030243 | −0.000582 | 0.000282 | 0.009956 | 0.0003 | 0.024315 | −0.007242 | 0.000057 | −0.009883 | −0.002142 | −0.014599 | 0.035965 |
| 284 | 0.004717 | 0.009203 | −0.006107 | 0.005783 | 0.01 | −0.011918 | 0.017702 | −0.001377 | 0.012477 | −0.008383 | 0.010143 | 0.016286 | 0.007215 | 0.015619 |
| 285 | −0.005464 | 0.006235 | −0.004768 | 0.010941 | 0.001359 | −0.017017 | 0.013182 | −0.001549 | 0.009295 | −0.008668 | 0.004723 | 0.01058 | 0.013604 | 0.022625 |
| 286 | −0.012618 | 0.007699 | −0.012473 | 0.005071 | 0.009165 | −0.000097 | −0.023562 | −0.007502 | 0.002097 | 0.000826 | −0.001366 | 0.001112 | 0.005949 | 0.014226 |
| 287 | −0.018226 | 0.002559 | −0.015208 | 0.007112 | 0.002206 | 0.005697 | −0.018193 | −0.003327 | −0.00078 | −0.001508 | −0.006258 | −0.002326 | 0.004547 | 0.017805 |
| 288 | 0.01153 | −0.008466 | −0.010072 | −0.001883 | 0.003576 | 0.002737 | −0.020986 | −0.020466 | −0.001571 | 0.01278 | −0.003408 | −0.008082 | −0.015475 | 0.051735 |
| 289 | 0.009144 | −0.011771 | 0.004722 | 0.002911 | 0.011179 | 0.018151 | 0.021465 | −0.013981 | −0.002821 | −0.008042 | −0.001373 | 0.001288 | −0.004791 | 0.013481 |
| 290 | 0.017367 | −0.010926 | −0.016495 | −0.008937 | −0.012876 | −0.025322 | −0.01971 | −0.032205 | −0.002887 | 0.000013 | −0.008984 | −0.010357 | −0.004673 | 0.02018 |
| 291 | 0.015364 | −0.010559 | −0.015501 | −0.006621 | −0.011386 | −0.023676 | −0.023076 | −0.032449 | −0.002548 | 0.000174 | −0.008362 | −0.007808 | −0.00542 | 0.021156 |
| 292 | 0.010845 | 0.002114 | −0.008777 | −0.008842 | −0.007187 | −0.028806 | −0.02907 | −0.023445 | −0.001299 | −0.005417 | −0.006377 | −0.002736 | −0.001447 | 0.021339 |
| 293 | −0.003029 | 0.009878 | 0.01582 | 0.007355 | 0.017819 | 0.010829 | −0.01568 | 0.023274 | 0.012394 | 0.003371 | 0.01827 | 0.026076 | −0.02855 | 0.001471 |
| 294 | −0.006992 | 0.005348 | 0.005879 | 0.010524 | 0.00703 | 0.008003 | −0.009885 | 0.015841 | 0.00215 | 0.008181 | 0.00726 | 0.002426 | −0.017381 | 0.003173 |
| 295 | 0.021699 | 0.03354 | 0.006242 | −0.012307 | 0.00149 | −0.011973 | −0.007535 | 0.002919 | 0.001048 | −0.012501 | 0.000752 | 0.004029 | −0.012 | 0.004813 |
| 296 | 0.026153 | 0.002044 | −0.020707 | −0.027337 | −0.028844 | −0.014919 | −0.004353 | 0.009826 | −0.021303 | −0.018325 | −0.023024 | −0.023888 | −0.032092 | 0.010548 |
| 297 | 0.034832 | 0.026397 | 0.013856 | −0.015583 | −0.018547 | −0.034937 | −0.019446 | −0.004381 | −0.001592 | −0.001617 | −0.003129 | −0.005687 | −0.01285 | 0.011593 |
| 298 | −0.017813 | −0.017768 | −0.013479 | −0.006528 | 0.003595 | −0.000684 | 0.021772 | 0.005054 | 0.005151 | 0.005113 | 0.000477 | −0.000413 | 0.00896 | −0.019347 |
| 299 | 0.022464 | 0.003855 | 0.011091 | −0.025508 | −0.00541 | −0.007774 | −0.014789 | 0.001758 | −0.005258 | 0.009813 | −0.008035 | −0.012116 | −0.010596 | 0.002245 |
| 300 | −0.056856 | 0.00738 | −0.002822 | −0.016012 | 0.045873 | 0.008537 | 0.012279 | 0.007207 | 0.041741 | 0.017146 | 0.033284 | 0.049703 | 0.033401 | −0.068378 |
| 301 | 0.002656 | 0.001 | 0.003488 | −0.015966 | 0.001055 | −0.008277 | 0.014319 | 0.011428 | 0.00033 | −0.00757 | −0.00343 | −0.00558 | −0.002338 | 0.005724 |
| 302 | −0.015837 | 0.006716 | −0.000673 | −0.026527 | 0.0127 | 0.015933 | 0.016514 | 0.014772 | −0.004186 | −0.011096 | −0.00937 | −0.011073 | 0.003032 | −0.008136 |
| 303 | 0.003322 | −0.00664 | 0.001536 | −0.024043 | −0.001606 | 0.011485 | −0.019021 | 0.022939 | −0.008022 | 0.009748 | −0.012011 | −0.013904 | −0.003837 | −0.02215 |
| 304 | 0.005916 | −0.016248 | −0.02274 | −0.044049 | −0.010358 | 0.012759 | −0.028706 | 0.03042 | −0.010777 | 0.016058 | −0.019359 | −0.026191 | −0.006242 | −0.02298 |
| 305 | −0.011497 | 0.008756 | 0.000579 | −0.023008 | 0.024705 | −0.005374 | −0.007757 | 0.008237 | 0.005824 | 0.004028 | 0.008162 | 0.009287 | −0.017086 | 0.005193 |
| 306 | 0.013052 | −0.034697 | −0.022892 | 0.028154 | −0.010645 | −0.008026 | −0.002173 | 0.024795 | 0.000974 | 0.001931 | 0.008958 | 0.019768 | −0.046783 | 0.00884 |
| 307 | 0.030994 | 0.001444 | 0.006091 | 0.025571 | 0.004661 | −0.021343 | 0.007293 | 0.045212 | −0.014713 | 0.056654 | 0.009095 | 0.013063 | 0.029545 | −0.053712 |
| 308 | 0.000505 | −0.012624 | 0.024827 | 0.027906 | 0.01023 | 0.004557 | −0.000328 | 0.037345 | 0.019153 | −0.007684 | 0.024708 | 0.030024 | 0.023252 | −0.009315 |
| 309 | −0.029607 | −0.018305 | −0.006461 | −0.012729 | −0.016023 | 0.002991 | 0.001651 | 0.014538 | −0.01028 | −0.010961 | −0.015198 | −0.015038 | −0.006132 | 0.014223 |
| 310 | −0.022877 | −0.002811 | −0.01983 | −0.001275 | −0.029222 | 0.008727 | 0.001008 | 0.02101 | −0.018888 | −0.014712 | −0.021545 | −0.026282 | −0.015168 | −0.012249 |
| 311 | −0.011022 | −0.013956 | −0.020337 | −0.006329 | −0.000916 | 0.011423 | −0.002339 | 0.01438 | 0.001358 | −0.000122 | −0.002374 | −0.002481 | −0.00683 | −0.013303 |
| 312 | 0.01864 | 0.029574 | 0.06197 | 0.033438 | −0.006477 | −0.017872 | −0.025247 | −0.003686 | 0.018148 | −0.008359 | 0.027457 | 0.02206 | 0.027116 | −0.007075 |
| 313 | −0.022908 | −0.027112 | −0.019435 | 0.016357 | −0.024336 | −0.022347 | −0.023692 | 0.002066 | 0.009231 | 0.002987 | 0.008351 | 0.011359 | −0.001573 | 0.000594 |
| 314 | −0.049842 | 0.044427 | −0.001841 | 0.02971 | −0.040694 | −0.026107 | −0.002316 | 0.03925 | 0.001109 | 0.032766 | −0.004363 | 0.00623 | 0.00962 | −0.000698 |
| 315 | −0.010866 | −0.006661 | 0.011915 | −0.002977 | −0.002204 | −0.000135 | −0.024255 | 0.00509 | −0.000888 | 0.002097 | −0.001602 | 0.001244 | −0.004525 | 0.016677 |
| 316 | −0.050043 | −0.016233 | 0.020399 | −0.010736 | 0.001237 | 0.026606 | 0.014942 | −0.029061 | −0.002244 | −0.044089 | −0.000633 | 0.002875 | −0.032566 | 0.009341 |
| 317 | −0.021082 | −0.003759 | −0.00131 | 0.016984 | −0.005731 | −0.006141 | 0.019973 | 0.012382 | 0.01036 | −0.009933 | 0.004831 | 0.013753 | 0.011679 | 0.035332 |
| 318 | 0.009039 | −0.010489 | −0.021513 | −0.000383 | −0.011956 | −0.008279 | 0.008554 | 0.024225 | −0.001555 | 0.019201 | −0.00644 | −0.000471 | 0.017707 | 0.014974 |
| 319 | −0.00671 | −0.019363 | 0.006598 | 0.008241 | 0.00793 | 0.004927 | 0.007866 | −0.001401 | 0.0048 | 0.00723 | 0.000844 | 0.002895 | 0.009694 | 0.02062 |
| 320 | 0.002467 | −0.006531 | −0.03397 | 0.008274 | 0.021725 | 0.010105 | 0.014605 | 0.00122 | 0.002404 | −0.00856 | 0.001024 | 0.00292 | −0.008851 | 0.004111 |
| 321 | 0.026163 | 0.016754 | −0.001363 | 0.000392 | −0.013795 | −0.031166 | −0.018231 | −0.004321 | 0.003785 | 0.02906 | 0.001519 | −0.002834 | −0.000365 | −0.010023 |
| 322 | −0.027303 | 0.042635 | 0.011486 | −0.038638 | 0.03983 | 0.04275 | 0.01848 | 0.02554 | −0.001411 | −0.041614 | 0.00308 | −0.002677 | 0.016341 | −0.00063 |
| 323 | −0.002465 | 0.028983 | 0.004044 | −0.00789 | 0.002259 | −0.012944 | −0.014222 | −0.018286 | −0.003718 | −0.009673 | 0.000289 | −0.005547 | 0.006502 | −0.015508 |
| 324 | −0.03746 | −0.020761 | 0.004707 | 0.001173 | 0.009574 | 0.021855 | 0.004248 | 0.034976 | −0.001213 | 0.01386 | 0.000836 | −0.000072 | −0.008911 | 0.031743 |
| 325 | −0.018019 | −0.026377 | 0.002117 | −0.002733 | −0.007728 | −0.005193 | 0.006584 | 0.009875 | −0.005502 | −0.009136 | −0.000517 | −0.00735 | −0.02046 | 0.022723 |
| 326 | −0.060795 | −0.017489 | −0.009665 | 0.011656 | 0.008451 | 0.01355 | 0.009596 | 0.00914 | 0.004276 | −0.013411 | 0.003803 | 0.011264 | 0.002917 | −0.008657 |
| 327 | −0.013871 | 0.009866 | −0.005654 | −0.016782 | 0.016781 | 0.004143 | 0.005804 | 0.007687 | 0.000094 | −0.006791 | 0.000522 | −0.000352 | 0.00836 | −0.011091 |
| 328 | −0.039179 | −0.001558 | −0.011742 | −0.008727 | 0.006588 | −0.013797 | −0.014002 | 0.00444 | −0.002395 | −0.018098 | −0.002031 | 0.001758 | −0.024603 | 0.004737 |
| 329 | −0.013289 | 0.019557 | 0.004772 | −0.00533 | 0.005035 | −0.012818 | 0.012397 | −0.023074 | 0.001512 | −0.013508 | 0.0003061 | 0.0083061 | 0.019721 | −0.024522 |
| 330 | −0.048833 | −0.016935 | 0.003139 | 0.004355 | 0.00486 | 0.021213 | −0.007567 | 0.004448 | 0.012786 | −0.009398 | 0.013985 | 0.010741 | 0.022634 | −0.061727 |
| 331 | −0.026046 | 0.011616 | 0.009011 | 0.004819 | 0.021734 | 0.02159 | −0.009259 | 0.017676 | 0.005345 | 0.000174 | 0.010518 | 0.012063 | −0.007171 | −0.013143 |
| 332 | −0.041591 | −0.05387 | −0.004227 | −0.01893 | 0.049524 | 0.056525 | −0.021324 | 0.029192 | 0.01204 | 0.028184 | 0.010319 | 0.002245 | 0.006031 | −0.080954 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 333 | −0.026067 | −0.02103 | 0.005986 | 0.005607 | 0.004126 | 0.007638 | 0.024373 | 0.011982 | 0.001595 | −0.000442 | 0.00448 | 0.00385 | −0.001869 | 0.004735 |
| 334 | −0.029267 | −0.003614 | 0.024514 | 0.014876 | −0.043608 | −0.056049 | −0.029035 | 0.003136 | −0.029395 | −0.029023 | −0.012738 | −0.016863 | 0.011011 | 0.005701 |
| 335 | −0.031632 | −0.022745 | −0.010584 | 0.014839 | 0.016824 | 0.009157 | 0.026338 | 0.014032 | 0.005557 | 0.007546 | 0.009617 | 0.002887 | 0.001763 | −0.0104 |
| 336 | −0.015991 | −0.013858 | −0.004946 | 0.004931 | 0.004841 | 0.018237 | 0.022116 | 0.020599 | 0.017754 | 0.015383 | 0.007247 | 0.005299 | 0.025106 | 0.025096 |
| 337 | 0.011421 | −0.019882 | 0.013776 | 0.009805 | −0.018619 | −0.01452 | 0.010439 | −0.00449 | −0.00285 | −0.011331 | 0.001161 | 0.004026 | −0.001858 | 0.037041 |
| 338 | 0.010867 | −0.01501 | 0.011255 | 0.003156 | 0.034493 | 0.062505 | 0.042285 | 0.022347 | −0.005328 | 0.013632 | −0.002461 | −0.00539 | 0.010927 | −0.043419 |
| 339 | −0.005496 | 0.001887 | −0.000364 | 0.00491 | 0.018672 | −0.001972 | 0.007453 | 0.027423 | 0.018509 | 0.015587 | 0.015518 | 0.021054 | 0.017989 | 0.009717 |
| 340 | 0.027683 | −0.015515 | −0.007478 | −0.000746 | −0.010228 | −0.027034 | −0.059204 | −0.016578 | 0.001564 | 0.020836 | 0.006021 | 0.024531 | −0.020487 | −0.042121 |

| | CD | CE | CF | CG | CH | CI | CJ | CK | CL | CM | CN | CO | CP | CQ |
|---|---|---|---|---|---|---|---|---|---|---|---|---|---|---|
| 1 | 0.066818 | −0.210412 | −0.217454 | −0.174249 | −0.096732 | −0.086756 | −0.186418 | −0.201214 | −0.180807 | −0.17117 | −0.169824 | −0.050161 | −0.180162 | −0.131196 |
| 2 | 0.026226 | 0.007784 | −0.031672 | −0.007383 | 0.118568 | 0.027493 | −0.036946 | 0.001103 | −0.04509 | −0.064564 | −0.033201 | −0.049424 | 0.016612 | −0.03759 |
| 3 | −0.007067 | 0.067203 | 0.025445 | −0.01962 | −0.10449 | −0.176888 | −0.111812 | 0.016777 | 0.025765 | −0.008044 | 0.035135 | 0.022507 | −0.018592 | 0.001181 |
| 4 | −0.071011 | −0.024685 | −0.015477 | 0.029021 | −0.181552 | −0.071092 | −0.055954 | 0.071784 | 0.011214 | −0.049055 | 0.01787 | −0.047051 | −0.031536 | 0.025153 |
| 5 | 0.039677 | −0.012742 | −0.014193 | −0.00336 | −0.006065 | −0.033136 | −0.011012 | −0.052147 | −0.02681 | −0.046194 | −0.000454 | 0.002415 | −0.003862 | −0.039346 |
| 6 | 0.058812 | 0.0183 | 0.013233 | −0.011302 | 0.003909 | 0.020924 | 0.006997 | −0.016163 | 0.015934 | 0.026273 | 0.021894 | −0.002215 | −0.009695 | 0.080101 |
| 7 | 0.021064 | −0.04676 | −0.017496 | −0.016814 | −0.048999 | −0.039901 | −0.005272 | −0.021013 | −0.01994 | −0.060979 | −0.039677 | 0.061395 | −0.010279 | −0.150413 |
| 8 | 0.013002 | 0.062974 | 0.020849 | −0.042301 | −0.167557 | −0.067033 | −0.047293 | 0.010035 | −0.001244 | −0.011057 | −0.018367 | 0.045443 | −0.002137 | 0.047844 |
| 9 | 0.012308 | 0.034621 | 0.034886 | 0.023245 | 0.032216 | 0.136267 | 0.059792 | 0.022139 | −0.002567 | 0.014115 | 0.028259 | 0.013469 | 0.036514 | 0.030503 |
| 10 | −0.042682 | 0.037947 | −0.009105 | 0.032921 | −0.000789 | −0.007177 | −0.021744 | 0.007354 | −0.015609 | −0.035146 | 0.091766 | 0.220504 | 0.042893 | 0.088278 |
| 11 | −0.048703 | 0.00267 | 0.01622 | 0.011495 | 0.059116 | −0.045702 | 0.012002 | 0.007364 | 0.031251 | 0.040496 | 0.01595 | 0.089012 | −0.006325 | −0.020433 |
| 12 | 0.106786 | 0.012114 | −0.007915 | −0.007718 | −0.056268 | −0.082927 | −0.02962 | 0.023147 | −0.013561 | −0.015471 | 0.043267 | 0.046123 | 0.039179 | 0.042022 |
| 13 | −0.017626 | −0.045031 | −0.027875 | −0.021177 | −0.012662 | 0.022819 | −0.009298 | −0.016651 | −0.009989 | −0.030766 | −0.031457 | 0.015095 | −0.051848 | 0.001202 |
| 14 | −0.083866 | −0.017964 | 0.044515 | 0.070609 | −0.104138 | 0.026796 | 0.039735 | 0.013075 | 0.052715 | 0.081276 | 0.042193 | −0.023928 | 0.107646 | −0.01201 |
| 15 | 0.018617 | −0.008374 | −0.007583 | 0.038636 | 0.027199 | 0.041551 | 0.047113 | −0.018084 | −0.001884 | 0.002728 | 0.00076 | −0.01296 | −0.042902 | 0.005664 |
| 16 | 0.037963 | 0.052362 | −0.003026 | 0.008997 | −0.02819 | −0.060569 | −0.029683 | −0.01409 | 0.001705 | 0.00185 | 0.045503 | −0.008003 | −0.021797 | −0.066566 |
| 17 | 0.053201 | 0.014558 | 0.001202 | 0.021872 | −0.029346 | 0.022486 | 0.035556 | 0.020683 | 0.007069 | −0.023732 | 0.001982 | 0.123513 | 0.031446 | 0.02001 |
| 18 | −0.04003 | −0.023731 | −0.014535 | −0.011728 | 0.016302 | −0.047541 | −0.028496 | −0.045448 | −0.027131 | −0.001799 | −0.008676 | 0.006476 | 0.002313 | 0.060198 |
| 19 | −0.027084 | 0.032377 | 0.041477 | 0.058535 | 0.019426 | 0.004143 | 0.003501 | 0.0296 | 0.048268 | 0.037263 | 0.033002 | 0.040109 | 0.041462 | 0.028354 |
| 20 | −0.138405 | −0.072872 | −0.045173 | −0.076353 | 0.056813 | 0.004551 | −0.026795 | −0.090219 | −0.066421 | −0.038997 | −0.059157 | −0.135956 | −0.059168 | −0.015852 |
| 21 | −0.01494 | 0.00224 | 0.006252 | −0.005275 | 0.055151 | 0.082025 | −0.023896 | 0.017964 | −0.000149 | 0.020043 | 0.023218 | −0.059262 | 0.016125 | 0.036577 |
| 22 | −0.02746 | −0.001569 | 0.010673 | −0.046407 | −0.017899 | −0.031204 | −0.023958 | 0.011166 | −0.047336 | −0.061812 | −0.049971 | −0.02653 | −0.086244 | −0.009925 |
| 23 | −0.039609 | 0.001915 | 0.015878 | 0.021507 | 0.019826 | 0.019518 | −0.031122 | 0.008992 | 0.041783 | 0.040412 | 0.035196 | −0.019202 | 0.042366 | −0.015284 |
| 24 | 0.026114 | 0.010487 | 0.036083 | 0.066463 | 0.029036 | 0.009244 | −0.017864 | 0.036589 | 0.054357 | 0.02715 | 0.052206 | 0.060479 | −0.011135 | 0.071761 |
| 25 | −0.056147 | −0.020775 | 0.002915 | 0.013317 | −0.125812 | −0.01209 | 0.001092 | 0.026867 | −0.00434 | −0.00923 | −0.043364 | −0.028 | 0.002059 | 0.012383 |
| 26 | −0.030918 | −0.093914 | −0.057209 | −0.041902 | 0.041732 | 0.051907 | 0.013448 | −0.04752 | −0.021622 | −0.046304 | −0.048004 | −0.031176 | −0.057983 | −0.087721 |
| 27 | −0.024912 | −0.05413 | −0.074996 | −0.099931 | 0.069309 | −0.010199 | −0.002575 | −0.06798 | −0.090711 | −0.096505 | −0.062509 | 0.03059 | −0.075396 | −0.016359 |
| 28 | −0.114031 | −0.030089 | −0.074628 | −0.05331 | 0.067184 | 0.059534 | 0.113257 | −0.048643 | −0.060168 | −0.031384 | −0.020008 | −0.038384 | −0.049414 | −0.012391 |
| 29 | −0.001146 | −0.055104 | −0.03372 | −0.02997 | 0.031825 | 0.007269 | −0.028897 | −0.046833 | −0.013998 | −0.008735 | −0.017073 | −0.029384 | −0.036682 | −0.014191 |
| 30 | 0.09664 | 0.007063 | 0.002157 | 0.03326 | 0.026734 | 0.005027 | −0.035208 | −0.012599 | 0.006009 | 0.001624 | 0.016726 | −0.000093 | 0.007737 | 0.000669 |
| 31 | −0.018432 | −0.013945 | −0.029594 | −0.057932 | −0.060192 | −0.092519 | −0.134924 | −0.04405 | −0.050207 | −0.0468 | −0.072062 | −0.087883 | −0.011603 | −0.006066 |
| 32 | −0.02909 | −0.014083 | −0.01679 | −0.015276 | 0.00395 | −0.041083 | −0.067149 | −0.024023 | −0.003299 | −0.013537 | 0.038787 | −0.075509 | −0.043973 | 0.004653 |
| 33 | 0.008382 | −0.021258 | −0.032317 | −0.045151 | −0.101871 | −0.042185 | 0.025429 | −0.003906 | −0.029858 | −0.018977 | −0.058888 | 0.000326 | −0.034119 | −0.044527 |
| 34 | 0.09602 | −0.018296 | −0.027845 | −0.020477 | 0.046781 | −0.015565 | −0.02937 | −0.036004 | −0.054861 | −0.046855 | −0.031018 | 0.019411 | −0.024863 | 0.057034 |
| 35 | 0.007486 | −0.008201 | 0.011487 | 0.009263 | 0.032507 | 0.029255 | 0.052569 | 0.014199 | −0.008851 | 0.014979 | 0.011215 | −0.020539 | 0.01016 | −0.051818 |
| 36 | 0.042926 | 0.028691 | 0.030013 | 0.015866 | −0.067504 | 0.025401 | 0.043339 | 0.018827 | 0.005558 | 0.010111 | −0.012422 | −0.000201 | 0.007931 | −0.014515 |
| 37 | 0.024801 | −0.052731 | −0.047702 | −0.031649 | −0.104774 | 0.033153 | −0.016824 | −0.099872 | −0.052677 | −0.016024 | 0.017236 | 0.059054 | −0.018934 | −0.106253 |
| 38 | 0.111213 | −0.001864 | −0.012903 | −0.015345 | 0.069326 | 0.034808 | 0.030968 | −0.017296 | −0.007473 | −0.003309 | 0.054853 | 0.03927 | −0.004967 | 0.008104 |
| 39 | 0.055463 | 0.005804 | −0.026658 | −0.033403 | 0.002948 | −0.017971 | 0.068267 | −0.013748 | 0.002084 | 0.029109 | −0.065553 | −0.125198 | 0.028786 | 0.024909 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 40 | −0.009607 | 0.00283 | 0.00466 | −0.003715 | −0.016473 | 0.017075 | 0.005583 | −0.001253 | −0.002716 | 0.000237 | 0.00036 | −0.001567 | −0.003209 | −0.000592 |
| 41 | 0.1557 | −0.008093 | −0.016099 | −0.01727 | 0.117553 | 0.005948 | 0.004391 | −0.004496 | −0.041109 | −0.01957 | −0.02769 | 0.068119 | −0.007816 | −0.048639 |
| 42 | −0.059033 | 0.019916 | 0.026206 | 0.001703 | 0.009118 | 0.083169 | 0.001735 | 0.010648 | 0.028753 | 0.045675 | 0.097355 | −0.01031 | 0.098744 | −0.009589 |
| 43 | −0.096408 | −0.021676 | −0.008216 | 0.002605 | −0.047248 | −0.057656 | −0.016546 | 0.015999 | 0.027718 | 0.023922 | −0.018194 | −0.020945 | 0.064992 | 0.066625 |
| 44 | −0.07185 | 0.03751 | 0.024131 | 0.034486 | 0.073914 | 0.045261 | 0.019901 | 0.033898 | 0.026194 | 0.007926 | 0.009106 | 0.080701 | −0.018712 | −0.005422 |
| 45 | −0.084671 | −0.039029 | 0.02545 | 0.002297 | 0.090907 | −0.013415 | 0.003119 | 0.027572 | 0.030595 | 0.039492 | 0.007281 | 0.007623 | 0.057902 | 0.055445 |
| 46 | 0.145138 | −0.026718 | 0.00081 | −0.006232 | 0.043008 | 0.039559 | 0.030801 | 0.014366 | 0.040264 | 0.07542 | −0.015519 | 0.033586 | 0.080158 | 0.017987 |
| 47 | 0.02474 | 0.00956 | −0.009148 | 0.023122 | 0.01877 | 0.001831 | −0.110555 | −0.015636 | −0.008879 | −0.03138 | 0.009342 | 0.110844 | 0.026231 | 0.043753 |
| 48 | −0.024954 | 0.033139 | 0.000508 | −0.010266 | −0.002489 | −0.012301 | 0.092492 | −0.004297 | −0.02812 | −0.008996 | −0.017042 | −0.149643 | −0.043484 | 0.020606 |
| 49 | −0.077468 | −0.022706 | 0.002812 | −0.007146 | −0.069505 | 0.049564 | 0.000355 | 0.01308 | 0.029833 | 0.010224 | −0.020808 | −0.004328 | −0.034109 | 0.079019 |
| 50 | 0.082791 | −0.014138 | 0.015076 | −0.008223 | −0.056468 | 0.035361 | 0.062306 | −0.001378 | −0.012022 | 0.000961 | −0.006176 | 0.103014 | −0.012139 | 0.011073 |
| 07 | 0.043634 | −0.021423 | −0.036239 | −0.03218 | 0.109228 | 0.02506 | −0.067982 | −0.024206 | −0.034901 | −0.013488 | 0.058055 | 0.130706 | 0.000978 | 0.094135 |
| 52 | 0.047765 | −0.023472 | −0.013973 | 0.008443 | 0.057174 | −0.03419 | −0.064598 | −0.004124 | −0.020161 | −0.044098 | 0.010279 | 0.002341 | −0.042423 | 0.072109 |
| 53 | 0.105336 | −0.046167 | −0.012018 | 0.017795 | −0.018879 | −0.022428 | −0.019064 | −0.008035 | −0.024327 | −0.011354 | −0.004907 | 0.011785 | 0.058985 | 0.010013 |
| 54 | 0.058289 | 0.034037 | −0.009467 | −0.023416 | 0.050488 | 0.119198 | −0.02986 | 0.002095 | −0.000336 | −0.042409 | 0.02623 | 0.054487 | 0.006812 | 0.026346 |
| 55 | −0.073822 | −0.015786 | −0.025179 | −0.00527 | −0.064735 | 0.052672 | −0.046557 | −0.026221 | −0.011726 | −0.036232 | 0.001992 | 0.069715 | −0.007262 | 0.06085 |
| 56 | 0.028343 | 0.036279 | 0.058249 | 0.025426 | 0.029881 | −0.018425 | 0.031148 | 0.020166 | 0.031852 | 0.003733 | −0.017556 | 0.078448 | −0.011651 | 0.033786 |
| 57 | 0.056917 | −0.029217 | −0.019612 | 0.031002 | −0.042572 | −0.047138 | −0.028694 | 0.012916 | 0.016089 | 0.040577 | −0.02048 | 0.023519 | −0.063936 | 0.018904 |
| 58 | −0.059107 | −0.028447 | −0.012867 | −0.006966 | 0.047989 | 0.053434 | 0.063606 | −0.031942 | −0.03605 | −0.039175 | −0.004671 | −0.013285 | −0.018364 | 0.006874 |
| 59 | −0.006308 | −0.022391 | −0.026422 | −0.053469 | 0.026256 | 0.007227 | −0.007471 | −0.044799 | −0.111854 | −0.070147 | −0.068045 | −0.082259 | 0.069809 | −0.063058 |
| 60 | 0.027331 | −0.000321 | −0.003179 | −0.001247 | 0.032464 | 0.001956 | −0.013252 | 0.000067 | −0.002366 | −0.00984 | 0.013047 | 0.011041 | −0.00126 | −0.007159 |
| 61 | −0.0127 | 0.009995 | 0.000546 | 0.003901 | −0.025448 | −0.008613 | −0.02547 | 0.005778 | 0.00951 | −0.009412 | 0.020154 | 0.029431 | −0.011297 | 0.018352 |
| 62 | 0.004333 | 0.002273 | 0.003458 | −0.000985 | 0.008472 | −0.005298 | −0.004455 | 0.014403 | −0.001206 | −0.00799 | 0.006032 | 0.023382 | −0.004867 | −0.001968 |
| 63 | −0.015539 | 0.010065 | 0.004008 | 0.00334 | −0.01518 | 0.001587 | −0.001332 | 0.007651 | 0.011614 | 0.000189 | 0.005465 | 0.030633 | −0.027805 | 0.007319 |
| 64 | 0.024358 | 0.001268 | −0.004284 | 0.002429 | −0.039587 | −0.008108 | −0.022162 | 0.001042 | −0.006384 | −0.012126 | −0.020869 | 0.031577 | −0.005449 | 0.004986 |
| 65 | 0.018645 | 0.004548 | 0.005368 | 0.002589 | 0.016175 | 0.0215 | 0.012954 | 0.007909 | 0.010343 | 0.002888 | −0.001882 | −0.008721 | 0.003151 | 0.010559 |
| 66 | 0.040988 | −0.001211 | 0.003173 | 0.013047 | −4.012807 | 0.000587 | −4.008308 | −4.000488 | 0.013312 | 0.003227 | 0.0081 | 0.062506 | −4.004152 | −4.008978 |
| 67 | 0.003004 | 0.014186 | 0.016703 | 0.020324 | −0.015568 | 0.0115 | −0.021162 | 0.003628 | 0.007596 | −0.000723 | 0.007533 | 0.001511 | −0.014413 | 0.005522 |
| 68 | 0.004963 | 0.005134 | −0.004183 | 0.019366 | 0.030876 | 0.033899 | 0.026605 | 0.008019 | −0.026979 | −0.025506 | 0.008547 | 0.030189 | −0.013253 | −0.003366 |
| 69 | −0.039469 | −0.001626 | 0.008405 | 0.011721 | 0.015604 | −0.019751 | −0.019494 | 0.006738 | −0.004917 | −0.015756 | 0.011574 | 0.023909 | 0.001749 | 0.007985 |
| 70 | −0.019998 | −0.01541 | 0.008594 | 0.005417 | 0.047807 | 0.006932 | −0.001593 | 0.006575 | 0.008774 | 0.015362 | −0.004548 | −0.023506 | −0.001521 | −0.023323 |
| 71 | 0.019888 | −0.01049 | −0.020065 | −0.029802 | −0.018995 | −0.095999 | −0.065904 | −0.014154 | −0.026434 | −0.033438 | −0.016577 | 0.017386 | −0.033437 | −0.019181 |
| 72 | 0.008092 | −0.013266 | −0.009331 | −0.014674 | −0.074248 | −0.106565 | −0.057612 | −0.001198 | −0.002357 | −0.012569 | −0.029343 | −0.039104 | −0.018121 | −0.021475 |
| 73 | 0.049177 | 0.033003 | 0.040167 | 0.031587 | −0.039449 | −0.078088 | −0.022441 | 0.024468 | 0.030662 | 0.023815 | 0.019047 | −0.03167 | 0.013174 | −0.029309 |
| 74 | −0.026925 | 0.005068 | 0.005857 | 0.006565 | 0.003827 | 0.006447 | 0.009055 | 0.015532 | 0.003702 | −0.008084 | −0.006599 | 0.011658 | 0.008841 | −0.009482 |
| 75 | −0.011028 | 0.000359 | 0.007966 | 0.005774 | 0.040962 | 0.005679 | 0.004374 | 0.007317 | 0.005556 | 0.006571 | 0.002106 | 0.00587 | −0.001484 | −0.001337 |
| 76 | −0.050107 | −0.005508 | 0.01268 | 0.012034 | 0.014064 | 0.002794 | −0.00129 | 0.022879 | 0.025191 | −0.015803 | 0.018877 | −0.002119 | 0.001433 | 0.015183 |
| 77 | −0.025969 | 0.000563 | 0.011112 | 0.003271 | 0.047002 | 0.000699 | 0.009427 | 0.008056 | 0.004948 | 0.007747 | 0.002039 | 0.003299 | −0.004636 | −0.000243 |
| 78 | −0.014605 | −0.004463 | −0.000102 | −0.00603 | 0.05667 | 0.00127 | 0.006431 | −0.004845 | −0.01527 | −0.004787 | −0.011267 | −0.023995 | −0.004239 | −0.016925 |
| 79 | 0.017985 | −0.02021 | −0.007957 | −0.001507 | 0.008842 | 0.010719 | −0.009133 | −0.003918 | −0.00953 | −0.011884 | −0.008565 | 0.02624 | −0.006328 | −0.015646 |
| 80 | 0.066746 | −0.004889 | −0.009682 | −0.005568 | 0.018936 | 0.011986 | −0.053952 | −0.021695 | 0.00389 | −0.004819 | 0.003806 | 0.060037 | −0.02232 | 0.000195 |
| 81 | 0.757605 | −0.005387 | 0.016063 | 0.007305 | −0.030202 | 0.002131 | 0.007509 | 0.010128 | 0.029921 | 0.020518 | 0.001463 | −0.087991 | −0.008206 | 0.010572 |
| 82 | 0.016124 | 0.911836 | −0.070472 | −0.050945 | −0.004909 | −0.025054 | −0.04379 | −0.064414 | −0.056442 | −0.047413 | −0.052974 | −0.01729 | −0.045151 | −0.051007 |
| 83 | 0.027992 | −0.063131 | 0.920357 | −0.058471 | −0.004272 | −0.028929 | −0.052657 | −0.064569 | −0.068168 | −0.063468 | −0.050053 | −0.014141 | −0.052 | −0.041801 |
| 84 | 0.014963 | −0.050406 | −0.063952 | 0.922271 | −0.003632 | −0.032008 | −0.048536 | −0.059779 | −0.064788 | −0.058939 | −0.057194 | −0.028823 | −0.050216 | −0.038724 |
| 85 | −0.044307 | −0.012011 | −0.002608 | 0.001304 | 0.744061 | −0.088447 | −0.042343 | 0.00343 | 0.015459 | −0.00292 | −0.01401 | −0.022811 | −0.024264 | −0.031503 |
| 86 | 0.009941 | −0.004398 | −0.016047 | −0.019519 | −0.095225 | 0.839201 | −0.077619 | −0.006047 | −0.010653 | −0.026233 | −0.0283 | −0.020796 | −0.036106 | −0.024529 |
| 87 | 0.032957 | −0.021019 | −0.034868 | −0.028839 | −0.038345 | −0.089265 | 0.844395 | −0.029188 | −0.023397 | −0.04411 | −0.007974 | 0.020262 | −0.03111 | 0.000581 |
| 88 | 0.025088 | −0.059573 | −0.069632 | −0.061094 | 0.011721 | −0.018395 | −0.051363 | 0.917299 | −0.070009 | −0.057567 | −0.046573 | −0.013918 | −0.0463 | −0.046822 |
| 89 | 0.029893 | −0.056622 | −0.075946 | −0.065351 | 0.011332 | −0.021783 | −0.050966 | −0.070113 | 0.909676 | −0.080705 | −0.056903 | −0.021214 | −0.048388 | −0.045562 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 90 | 0.025956 | −0.046396 | −0.067482 | −0.05405 | −0.006741 | −0.032024 | −0.068552 | −0.051798 | −0.076307 | 0.907912 | −0.04826 | 0.002454 | −0.05671 | −0.035222 |
| 91 | 0.02274 | −0.060286 | −0.05773 | −0.05981 | −0.018168 | −0.039866 | −0.024963 | −0.049493 | −0.059473 | −0.054812 | 0.904332 | −0.060402 | −0.053125 | −0.059958 |
| 92 | −0.067148 | −0.036084 | −0.021045 | −0.03748 | −0.001177 | −0.024142 | 0.008127 | −0.029884 | −0.019018 | 0.001788 | −0.071907 | 0.758085 | −0.020924 | −0.055422 |
| 93 | 0.015572 | −0.046063 | −0.059954 | −0.051276 | −0.026503 | −0.043863 | −0.03857 | −0.047705 | −0.055516 | −0.06623 | −0.053233 | −0.016565 | 0.887683 | −0.042517 |
| 94 | 0.030664 | −0.046421 | −0.042188 | −0.030086 | −0.017026 | −0.019696 | −0.004618 | −0.045016 | −0.041254 | −0.032434 | −0.040276 | −0.036807 | −0.02214 | 0.86076 |
| 95 | −0.013494 | −0.00918 | −0.006677 | 0.00333 | −0.00532 | −0.012562 | −0.0202 | 0.008297 | −0.008731 | −0.012738 | 0.014949 | 0.047879 | 0.009256 | 0.001769 |
| 96 | 0.042102 | 0.011404 | 0.021227 | 0.014058 | −0.014529 | −0.007422 | −0.001354 | 0.005815 | 0.017548 | 0.02255 | 0.021541 | 0.023299 | 0.02627 | −0.016954 |
| 97 | −0.023257 | 0.004982 | 0.004388 | 0.018366 | −0.011464 | 0.008311 | −0.011562 | 0.009673 | 0.016229 | 0.008255 | 0.025147 | −0.003965 | 0.010241 | −0.010996 |
| 98 | −0.005357 | −0.001748 | 0.00487 | 0.004123 | −0.01705 | −0.009555 | −0.019618 | −0.001547 | 0.008138 | 0.004325 | 0.003743 | −0.003416 | 0.005454 | −0.024284 |
| 99 | −0.017387 | 0.00541 | 0.012331 | 0.015716 | −0.016521 | 0.000596 | 0.00694 | 0.00737 | 0.015942 | 0.011025 | 0.011682 | −0.010731 | 0.018564 | −0.000655 |
| 100 | −0.017432 | −0.006773 | 0.007144 | 0.018397 | −0.019014 | −0.020092 | −0.010488 | 0.007474 | 0.014126 | 0.015627 | 0.020084 | 0.002634 | 0.011327 | −0.004664 |
| 101 | −0.022567 | 0.004605 | 0.007689 | 0.000422 | −0.021317 | −0.003929 | −0.005505 | 0.000206 | 0.006349 | 0.003139 | 0.001613 | 0.000122 | −0.012911 | −0.035162 |
| 102 | −0.062517 | 0.008957 | 0.014624 | 0.005234 | −0.036772 | −0.031932 | −0.040268 | 0.019392 | 0.021932 | 0.014764 | 0.023161 | 0.002027 | −0.009407 | 0.01758 |
| 103 | −0.023631 | 0.009923 | −0.006703 | 0.001477 | 0.04048 | 0.003756 | −0.026588 | −0.005628 | −0.00382 | −0.001078 | 0.014699 | 0.00816 | 0.001987 | 0.014311 |
| 104 | −0.016044 | 0.018459 | 0.01334 | 0.000028 | 0.024739 | 0.001784 | −0.017606 | 0.009606 | 0.010014 | −0.00319 | 0.014077 | 0.01355 | 0.004201 | 0.039024 |
| 105 | 0.034349 | 0.013246 | −0.001897 | −0.011179 | 0.031111 | 0.019661 | −0.036506 | −0.028129 | −0.016499 | 0.00103 | 0.037367 | 0.013483 | 0.003596 | 0.028905 |
| 106 | 0.036173 | 0.004466 | 0.003116 | −0.006004 | 0.045111 | −0.001046 | 0.016946 | 0.00476 | 0.007784 | 0.021408 | −0.01496 | 0.0049 | −0.001318 | −0.005025 |
| 107 | −0.022209 | 0.007694 | 0.014596 | 0.010021 | 0.008687 | 0.00007 | 0.023661 | 0.00171 | 0.013342 | 0.016071 | 0.018881 | −0.001404 | 0.008859 | −0.008155 |
| 108 | 0.020749 | 0.021998 | 0.018981 | 0.006494 | 0.028874 | 0.045558 | 0.015813 | 0.014891 | 0.014978 | 0.021474 | 0.014917 | 0.039159 | −0.006045 | 0.02876 |
| 109 | −0.012889 | −0.0157 | −0.004733 | 0.004033 | −0.010924 | 0.023938 | 0.018446 | 0.014824 | 0.00595 | 0.00291 | −0.007236 | −0.042207 | 0.026761 | −0.024688 |
| 110 | 0.063871 | −0.00749 | −0.009937 | −0.028892 | −0.028847 | −0.008329 | 0.035731 | −0.003573 | 0.004892 | 0.024133 | −0.026683 | −0.0275 | −0.002734 | 0.010384 |
| 111 | 0.027576 | −0.000274 | 0.008569 | −0.009619 | 0.019683 | 0.015058 | −0.010859 | 0.014232 | 0.013181 | 0.014904 | 0.001005 | 0.01417 | 0.041832 | 0.020224 |
| 112 | 0.016002 | 0.05062 | 0.014349 | −0.007334 | 0.046372 | 0.015604 | 0.006701 | 0.005595 | −0.00164 | −0.004341 | 0.026694 | 0.038879 | −0.015895 | 0.034237 |
| 113 | 0.001855 | −0.004324 | 0.021116 | 0.019834 | −0.004649 | 0.02976 | 0.03197 | 0.024114 | 0.010821 | 0.01198 | −0.004309 | −0.044105 | 0.025979 | −0.036094 |
| 114 | −0.010147 | 0.016158 | −0.001892 | 0.024549 | −0.030403 | 0.025704 | 0.022186 | 0.003548 | −0.007426 | −0.021164 | −0.002562 | 0.014307 | −0.018708 | 0.007908 |
| 115 | 0.00957 | 0.001325 | 0.004862 | −0.023785 | −0.012919 | −0.023844 | 0.03317 | 0.012371 | 0.012005 | 0.012788 | −4.040929 | −4.023491 | −0.028911 | 0.001061 |
| 116 | −0.000289 | −0.00619 | −0.02019 | −0.001785 | 0.01477 | 0.016827 | −0.030968 | −0.003466 | −0.014962 | −0.017019 | 0.010353 | −0.009392 | −0.017761 | 0.029198 |
| 117 | −0.016179 | 0.000989 | 0.002966 | −0.016842 | 0.007231 | −0.006554 | −0.004847 | 0.003786 | 0.012226 | −0.003992 | 0.006168 | 0.014269 | 0.000135 | 0.038085 |
| 118 | 0.017643 | −0.014971 | 0.011244 | −0.000735 | −0.020531 | 0.002715 | −0.047029 | 0.013422 | 0.006387 | −0.006656 | −0.006071 | −0.008699 | −0.004985 | 0.001435 |
| 119 | 0.0293 | 0.002085 | 0.007588 | −0.007036 | 0.016714 | −0.020719 | 0.0056 | 0.005322 | −0.004944 | −0.013376 | −0.018786 | 0.006616 | −0.000381 | −0.019626 |
| 120 | 0.000988 | −0.009465 | −0.005594 | −0.013656 | 0.001528 | −0.001645 | 0.010258 | −0.00022 | −0.014257 | −0.017076 | −0.026337 | −0.004592 | −0.002801 | 0.010273 |
| 121 | 0.06843 | −0.026494 | −0.037436 | −0.015655 | −0.017054 | 0.001766 | 0.024836 | −0.030365 | −0.031847 | −0.030923 | −0.033329 | 0.034852 | −0.011173 | −0.030632 |
| 122 | −0.026979 | 0.006914 | 0.000615 | −0.014413 | −0.001855 | 0.002468 | 0.001515 | 0.009005 | 0.014817 | 0.019251 | 0.007111 | −0.003633 | 0.00248 | 0.015175 |
| 123 | −0.020909 | −0.013821 | −0.006782 | −0.015538 | −0.016897 | −0.007573 | 0.017404 | −0.002207 | −0.005726 | 0.001768 | −0.013626 | 0.008663 | −0.010517 | 0.006002 |
| 124 | 0.010562 | 0.007146 | 0.002042 | −0.009544 | 0.038075 | 0.004478 | 0.004767 | 0.001023 | −0.006495 | −0.011892 | −0.002442 | 0.007377 | 0.005062 | −0.015868 |
| 125 | −0.002906 | −0.007018 | −0.000663 | −0.011227 | −0.015851 | −0.003758 | −0.022363 | −0.002659 | −0.003741 | −0.004423 | −0.003246 | 0.022117 | −0.002786 | 0.027629 |
| 126 | 0.012846 | −0.006582 | 0.007104 | −0.005259 | 0.028642 | 0.019657 | −0.000813 | −0.000685 | 0.006009 | 0.006045 | 0.003067 | −0.013915 | 0.022923 | 0.013539 |
| 127 | 0.012791 | 0.005511 | 0.005927 | −0.001509 | 0.046391 | 0.011344 | −0.000938 | 0.000516 | 0.002366 | 0.00697 | −0.003062 | −0.027792 | 0.025993 | 0.001229 |
| 128 | −0.002759 | −0.007765 | 0.003599 | 0.004024 | 0.016251 | −0.014762 | 0.004372 | 0.011982 | 0.011971 | 0.011948 | −0.005582 | −0.013195 | 0.000419 | 0.011689 |
| 129 | −0.029836 | 0.03193 | 0.004737 | −0.006148 | −0.064757 | −0.030268 | −0.034512 | 0.000578 | 0.003143 | −0.011899 | 0.021221 | 0.008318 | −0.023173 | 0.011011 |
| 130 | 0.022485 | −0.003831 | −0.003661 | 0.005492 | 0.000942 | −0.017836 | 0.036455 | 0.010609 | 0.003882 | 0.0066 | −0.019335 | −0.044206 | −0.011575 | −0.036648 |
| 131 | 0.062422 | −0.011646 | −0.007503 | 0.005952 | −0.001251 | 0.041675 | −0.021833 | −0.012664 | −0.012007 | −0.012123 | 0.035524 | 0.047371 | 0.000242 | −0.014206 |
| 132 | 0.01171 | −0.012602 | −0.006424 | −0.000552 | −0.007775 | −0.040933 | −0.013684 | 0.002297 | −0.002571 | −0.003663 | 0.000071 | 0.014059 | 0.008582 | 0.007274 |
| 133 | 0.028958 | −0.018159 | −0.013358 | −0.002799 | 0.000541 | 0.00987 | −0.01162 | −0.00445 | −0.005723 | −0.017438 | 0.001396 | 0.044247 | 0.015985 | −0.056569 |
| 134 | −0.004333 | −0.002439 | −0.009987 | −0.016899 | −0.034895 | 0.014466 | −0.013175 | −0.014852 | −0.021709 | −0.026289 | −0.010317 | −0.012226 | −0.016918 | −0.023605 |
| 135 | 0.023014 | −0.007273 | −0.008363 | −0.006908 | 0.035039 | −0.013615 | −0.014845 | −0.007682 | −0.019138 | −0.016098 | −0.010648 | 0.00755 | 0.00852 | −0.004275 |
| 136 | 0.031241 | −0.026698 | 0.001025 | 0.002539 | −0.037013 | −0.042615 | −0.030829 | 0.012838 | 0.009014 | 0.008386 | −0.021031 | −0.053289 | 0.027935 | −0.02401 |
| 137 | 0.000508 | −0.005141 | −0.003146 | 0.00031 | −0.013924 | −0.009551 | −0.028777 | 0.007238 | −0.0075 | −0.012216 | 0.002926 | −0.001814 | −0.008694 | −0.028908 |
| 138 | 0.019619 | 0.027166 | 0.004828 | 0.015202 | 0.032426 | 0.035847 | 0.034468 | 0.018675 | 0.000812 | 0.000661 | 0.006981 | −0.055642 | 0.007522 | −0.006877 |
| 139 | 0.0441 | −0.010719 | 0.017828 | 0.001447 | −0.01282 | 0.009622 | 0.052256 | 0.005743 | 0.02985 | 0.030829 | 0.013804 | 0.032263 | −0.010008 | −0.021729 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 140 | 0.008808 | −0.011294 | 0.004674 | −0.017258 | −0.062096 | −0.056625 | 0.006716 | 0.007274 | 0.002362 | −0.006088 | −0.024487 | 0.001704 | −0.037348 | 0.007774 |
| 141 | −0.015656 | −0.0027 | −0.010836 | −0.008495 | 0.03229 | −0.018845 | 0.005524 | −0.016163 | −0.016078 | 0.010342 | 0.006388 | −0.020593 | 0.00938 | 0.005984 |
| 142 | −0.007043 | 0.03723 | 0.012902 | 0.015868 | −0.031518 | −0.006534 | 0.009265 | 0.020095 | 0.029444 | 0.018348 | 0.012716 | −0.022431 | 0.008505 | 0.007684 |
| 143 | −0.063889 | 0.008912 | 0.00051 | −0.004388 | 0.00298 | 0.004524 | 0.023294 | 0.002134 | 0.015717 | 0.020371 | 0.000764 | −0.011545 | −0.0215 | 0.007967 |
| 144 | −0.000429 | 0.010036 | −0.00086 | −0.000389 | 0.029847 | −0.025329 | −0.013461 | −0.001514 | −0.00477 | −0.012722 | −0.003256 | 0.019112 | −0.015144 | 0.011482 |
| 145 | −0.013142 | −0.012156 | 0.008244 | 0.02845 | 0.005334 | −0.00852 | −0.01729 | 0.027185 | 0.027017 | 0.002446 | −0.00797 | −0.002317 | −0.001396 | −0.019908 |
| 146 | −0.005239 | −0.010544 | 0.003483 | 0.007096 | −0.015951 | −0.009591 | −0.020512 | 0.001775 | 0.003167 | −0.006754 | 0.005467 | 0.027319 | 0.007315 | 0.014774 |
| 147 | −0.009378 | 0.003945 | 0.000948 | 0.003662 | −0.034935 | 0.032473 | 0.021273 | −0.002824 | −0.000742 | −0.010088 | 0.006562 | −0.019904 | −0.024385 | 0.016326 |
| 148 | 0.04038 | −0.004114 | 0.0022 | −0.001841 | −0.004338 | −0.026942 | −0.054843 | 0.021567 | 0.016875 | −0.001914 | 0.023981 | 0.029237 | −0.011289 | 0.032913 |
| 149 | −0.034733 | −0.011476 | −0.00745 | −0.006624 | −0.000514 | −0.007713 | −0.001416 | −0.009229 | 0.000359 | 0.009997 | −0.005497 | 0.004145 | 0.006913 | −0.016623 |
| 150 | −0.01826 | 0.003563 | 0.005618 | 0.002349 | 0.009264 | 0.020458 | 0.013058 | 0.010003 | −0.000093 | −0.004464 | −0.008596 | −0.060491 | −0.019642 | 0.016177 |
| 151 | −0.016786 | −0.017648 | 0.007623 | −0.007369 | −0.030789 | 0.00588 | 0.009211 | −0.029544 | 0.019324 | 0.033932 | 0.004353 | −0.007114 | −0.023609 | 0.013781 |
| 152 | 0.027354 | 0.007751 | −0.004035 | −0.007785 | 0.018533 | −0.005749 | 0.010411 | −0.006927 | −0.006067 | −0.000106 | −0.019706 | −0.029959 | 0.018598 | −0.000269 |
| 153 | 0.010667 | 0.01656 | 0.011791 | −0.003587 | −0.048882 | −0.015727 | 0.002663 | 0.004304 | 0.016648 | 0.017598 | 0.006662 | −0.002151 | 0.019215 | 0.038734 |
| 154 | 0.030549 | 0.003435 | 0.002522 | −0.002866 | −0.015685 | −0.014983 | −0.02082 | 0.008742 | 0.009413 | 0.003826 | −0.011861 | −0.035043 | 0.00308 | −0.003334 |
| 155 | 0.021583 | 0.000559 | 0.000571 | −0.006235 | 0.011778 | −0.025725 | −0.049686 | 0.00877 | 0.002011 | −0.017807 | −0.021138 | 0.01764 | 0.010427 | 0.027139 |
| 156 | −0.042431 | −0.009437 | 0.006364 | 0.007328 | 0.017057 | 0.001062 | 0.015074 | 0.009163 | 0.012387 | 0.016078 | −0.017446 | −0.021983 | −0.000104 | −0.015561 |
| 157 | −0.033059 | −0.009991 | −0.000289 | −0.014985 | 0.000958 | −0.012201 | 0.008537 | 0.002661 | 0.003887 | −0.000977 | −0.016366 | −0.020441 | 0.004537 | 0.015889 |
| 158 | 0.045957 | 0.02016 | 0.005555 | −0.003458 | 0.023261 | 0.048599 | 0.001125 | 0.014136 | 0.000366 | 0.008446 | −0.001244 | 0.047157 | 0.036894 | −0.003464 |
| 159 | 0.047735 | 0.001692 | −0.015371 | 0.003378 | 0.078922 | 0.059912 | 0.018062 | −0.002463 | −0.019525 | −0.016796 | −0.018905 | −0.061813 | −0.015868 | 0.00034 |
| 160 | −0.007638 | −0.017815 | 0.003936 | −0.025763 | −0.044113 | 0.048651 | 0.048021 | 0.006487 | 0.009792 | 0.025231 | −0.005499 | −0.004433 | 0.01084 | −0.038036 |
| 161 | −0.022352 | 0.020918 | −0.005187 | −0.003212 | −0.007127 | 0.000343 | 0.004662 | 0.007952 | −0.008015 | −0.019232 | 0.03119 | 0.016669 | −0.000898 | 0.027022 |
| 162 | 0.003851 | −0.005334 | −0.003136 | −4.001179 | 0.009095 | 0.018407 | −0.010997 | −0.0059 | −0.002694 | −0.00017 | 0.015498 | 0.044319 | −0.019177 | −0.017759 |
| 163 | −0.002713 | 0.013874 | −0.005242 | −0.003145 | 0.016293 | −0.007642 | −0.010249 | 0.003245 | 0.004018 | 0.001871 | 0.003674 | −0.01006 | 0.010402 | −0.004251 |
| 164 | −0.022561 | −0.002263 | 0.018699 | 0.011747 | 0.023634 | 0.024326 | −0.022285 | −0.012418 | 0.017423 | 0.017733 | 0.011351 | −0.024005 | −0.001091 | −0.009666 |
| 165 | −0.010146 | 0.001745 | 0.011258 | −0.004902 | 0.019452 | −0.009315 | −0.025178 | 0.007715 | 0.034526 | 0.013322 | 0.028264 | 0.053571 | 0.02019 | 0.018628 |
| 166 | 0.03513 | 0.014278 | 0.006592 | −0.003739 | 0.0275271 | 0.019286 | 0.0153491 | −0.007449 | 0.000543 | 0.01196 | 0.005906 | 0.013457 | 0.0292 | −0.039483 |
| 167 | 0.01059 | −0.00879 | 0.007318 | 0.009587 | 0.026553 | −0.033873 | −0.015309 | 0.014119 | 0.00113 | −0.012406 | −0.024289 | −0.00862 | 0.004386 | −0.012605 |
| 168 | −0.0105 | 0.019079 | 0.016984 | 0.027576 | −0.018217 | 0.005292 | 0.020139 | 0.015661 | 0.017025 | 0.02595 | 0.024553 | 0.014014 | 0.007941 | −0.000304 |
| 169 | −0.006105 | −0.00315 | −0.005562 | −0.004115 | 0.000246 | 0.00395 | 0.003681 | −0.008987 | −0.006054 | −0.006391 | −0.001924 | 0.010203 | −0.004254 | −0.007052 |
| 170 | −0.009656 | −0.001671 | −0.004846 | 0.00542 | −0.005755 | 0.007708 | 0.018109 | −0.006863 | −0.001244 | −0.00327 | 0.005154 | 0.010203 | −0.016441 | −0.024538 |
| 171 | −0.003686 | −0.004537 | −0.007245 | 0.002102 | 0.014548 | 0.009624 | 0.030047 | −0.017354 | −0.015887 | −0.002167 | 0.002229 | 0.002742 | 0.0101 | −0.007655 |
| 172 | −0.025346 | 0.000237 | 0.005862 | 0.006046 | −0.005734 | 0.020226 | 0.01601 | 0.01168 | 0.004916 | 0.002463 | −0.004499 | 0.007701 | 0.009399 | 0.022197 |
| 173 | −0.000534 | 0.007636 | 0.011761 | 0.011808 | −0.019985 | 0.025627 | 0.019216 | 0.017932 | 0.016181 | 0.011479 | 0.010714 | 0.04792 | 0.013145 | 0.016351 |
| 174 | 0.026248 | −0.004053 | −0.00274 | 0.005361 | 0.009998 | 0.016665 | 0.014896 | 0.003298 | −0.00684 | 0.000589 | −0.000113 | 0.030024 | 0.002185 | −0.001535 |
| 175 | −0.033393 | −0.023233 | −0.003204 | −0.003586 | 0.024335 | 0.042064 | 0.003713 | −0.006436 | −0.001012 | 0.011224 | 0.014257 | −0.015508 | 0.011678 | 0.006408 |
| 176 | −0.018778 | −0.030676 | −0.021811 | 0.001608 | 0.035882 | 0.004849 | 0.011979 | −0.00577 | −0.008702 | −0.002324 | 0.007913 | 0.001284 | 0.008777 | −0.019948 |
| 177 | 0.061892 | 0.015152 | 0.02095 | −0.004974 | 0.090783 | 0.018023 | 0.008035 | 0.004281 | −0.016723 | −0.02072 | −0.014585 | 0.007727 | 0.005543 | 0.024006 |
| 178 | 0.011545 | 0.009709 | 0.016532 | 0.002778 | 0.038513 | 0.007062 | −0.008488 | −0.000102 | 0.013615 | 0.009133 | 0.027142 | 0.015903 | 0.010576 | −0.005674 |
| 179 | 0.00638 | 0.006314 | 0.008536 | 0.002473 | −0.006858 | −0.013191 | −0.012557 | −0.000958 | 0.008958 | 0.005647 | 0.003938 | −0.000706 | 0.003329 | −0.001751 |
| 180 | 0.020324 | 0.004316 | 0.005211 | −0.004907 | −0.013592 | −0.011865 | −0.005385 | −0.003009 | 0.000226 | 0.000266 | 0.001214 | 0.007569 | 0.000179 | −0.017888 |
| 181 | 0.005443 | 0.004302 | 0.005094 | −0.003785 | −0.014903 | −0.01021 | −0.005817 | −0.001464 | 0.005836 | 0.001878 | 0.001738 | 0.004964 | −0.000897 | −0.015011 |
| 182 | −0.00011 | 0.007782 | 0.008458 | 0.006614 | −0.014866 | −0.014105 | −0.001965 | 0.006686 | 0.00844 | 0.005251 | 0.00707 | −0.005302 | 0.000785 | −0.013244 |
| 183 | 0.001458 | 0.00011 | 0.006719 | 0.00841 | 0.008576 | −0.018548 | −0.0143 | −0.00085 | 0.000723 | 0.006729 | 0.005621 | −0.013734 | 0.013283 | 0.015618 |
| 184 | 0.012384 | −0.011616 | −0.011788 | 0.012248 | 0.003623 | −0.022935 | 0.007504 | −0.003415 | −0.008744 | 0.001653 | −0.00283 | 0.033307 | −0.005338 | 0.006482 |
| 185 | −0.016806 | 0.033894 | 0.010927 | 0.003937 | 0.010328 | −0.023186 | 0.024596 | 0.028167 | 0.015855 | 0.011831 | −0.010093 | −0.017917 | −0.017956 | 0.036971 |
| 186 | 0.017758 | −0.007639 | −0.007913 | −0.009824 | −0.065745 | 0.00159 | 0.03996 | −0.001511 | −0.012688 | −0.002999 | −0.013139 | 0.008215 | −0.008902 | 0.008683 |
| 187 | 0.020119 | 0.00409 | 0.002614 | 0.003167 | −0.013157 | −0.006572 | −0.026229 | 0.009103 | 0.0062 | −0.00016 | 0.00791 | 0.040474 | −0.007474 | 0.0206 |
| 188 | 0.031388 | −0.003103 | −0.003141 | 0.001937 | −0.000626 | −0.015926 | −0.019284 | 0.005394 | −0.002788 | −0.00151 | 0.000961 | 0.027919 | −0.020665 | 0.00618 |
| 189 | 0.016398 | −0.022142 | −0.019569 | −0.008059 | −0.005726 | −0.00475 | −0.020024 | −0.005609 | −0.01434 | −0.000049 | 0.007529 | −0.00156 | −0.025344 | 0.000239 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 190 | 0.002893 | −0.023116 | −0.011356 | −0.003841 | −0.001144 | −0.004906 | 0.013234 | −0.012467 | −0.013032 | −0.003041 | −0.007956 | 0.010062 | −0.011765 | −0.035378 |
| 191 | −0.019431 | −0.016933 | −0.009582 | −0.021149 | −0.01902 | −0.018992 | −0.009857 | −0.013734 | −0.014904 | −0.010542 | −0.016355 | 0.003746 | −0.003674 | −0.008468 |
| 192 | 0.010213 | 0.019833 | 0.013809 | 0.017189 | 0.040461 | 0.005869 | −0.017595 | −0.000182 | 0.011856 | 0.015666 | 0.012169 | 0.009972 | 0.015847 | 0.020497 |
| 193 | −0.007815 | 0.000939 | 0.00059 | 0.012763 | −0.001611 | 0.001549 | −0.001361 | −0.001172 | −0.001314 | 0.008942 | 0.010305 | 0.025903 | 0.010947 | 0.019108 |
| 194 | −0.024434 | −0.007622 | −0.000686 | −0.009432 | 0.001743 | 0.00238 | 0.002439 | −0.003171 | −0.004077 | 0.009386 | 0.002898 | 0.002713 | −0.005905 | 0.017756 |
| 195 | −0.009584 | 0.000028 | −0.01213 | −0.006112 | −0.014811 | 0.019151 | 0.011932 | 0.009384 | −0.004547 | −0.014313 | −0.003032 | 0.042577 | −0.009953 | 0.012156 |
| 196 | 0.007614 | −0.00488 | −0.006359 | −0.003611 | −0.009393 | 0.010411 | 0.011743 | −0.000503 | −0.004281 | −0.006746 | −0.004812 | 0.03677 | −0.01157 | −0.014114 |
| 197 | 0.004596 | −0.021007 | −0.015913 | −0.00771 | −0.006381 | 0.004474 | 0.00315 | −0.015153 | −0.018917 | −0.016362 | −0.016917 | 0.034518 | −0.012973 | −0.021639 |
| 198 | −0.016223 | 0.013346 | −0.000026 | 0.003468 | 0.054647 | 0.028351 | 0.00262 | 0.020403 | 0.004227 | −0.008673 | 0.017644 | 0.030503 | −0.009589 | 0.053936 |
| 199 | −0.035894 | 0.000352 | −0.015332 | −0.004513 | 0.005909 | −0.010329 | −0.007904 | −0.014103 | −0.004438 | 0.0136 | 0.00886 | −0.038853 | 0.019507 | −0.008563 |
| 200 | 0.018407 | 0.005436 | 0.010362 | 0.00316 | 0.012209 | 0.027949 | −0.018815 | −0.006918 | 0.00074 | 0.000084 | 0.020977 | 0.011341 | 0.029576 | 0.031053 |
| 201 | 0.023828 | 0.005433 | −0.006069 | −0.019069 | 0.018161 | −0.034283 | −0.043108 | −0.002397 | −0.006994 | −0.010316 | 0.032024 | 0.032827 | 0.004476 | −0.009847 |
| 202 | 0.002905 | 0.008898 | 0.013296 | 0.00527 | 0.015201 | 0.031235 | 0.029214 | 0.007884 | 0.011424 | 0.012213 | 0.009592 | 0.028347 | 0.011687 | 0.004665 |
| 203 | 0.02564 | −0.005182 | −0.007398 | −0.003133 | 0.043934 | −0.012731 | −0.025248 | 0.005852 | 0.004104 | −0.001191 | 0.003483 | 0.016519 | −0.01364 | 0.023069 |
| 204 | −0.056382 | 0.004796 | 0.007646 | 0.006894 | 0.021749 | −0.001286 | 0.030064 | 0.012818 | 0.015096 | 0.004491 | −0.008683 | −0.036685 | 0.00211 | 0.029671 |
| 205 | 0.059633 | −0.013149 | −0.006266 | −0.016726 | −0.000453 | 0.002059 | 0.010492 | −0.00028 | 0.001526 | 0.012732 | −0.013239 | 0.005216 | 0.003682 | −0.009466 |
| 206 | 0.084842 | 0.02922 | 0.015126 | 0.022792 | −0.005084 | 0.003996 | 0.01539 | 0.026251 | 0.011371 | −0.002561 | 0.018486 | 0.079218 | 0.003004 | −0.017372 |
| 207 | 0.011754 | 0.003813 | 0.006981 | −0.020329 | 0.028082 | 0.005643 | −0.009041 | −0.00628 | 0.003018 | 0.008231 | −0.022467 | −0.058624 | −0.008846 | −0.00312 |
| 208 | 0.06566 | −0.008395 | −0.01817 | −0.014853 | 0.044339 | −0.002894 | 0.007296 | −0.000092 | −0.018092 | −0.022825 | −0.036232 | 0.007867 | −0.024448 | −0.006062 |
| 209 | 0.062491 | 0.009863 | −0.013569 | 0.017689 | 0.019928 | 0.029059 | 0.010111 | −0.008222 | −0.001103 | 0.006957 | 0.011543 | 0.03176 | 0.031657 | −0.019866 |
| 210 | −0.026547 | −0.011905 | −0.003608 | −0.009248 | 0.011946 | 0.022605 | −0.05978 | −0.017143 | −0.014189 | −0.010449 | 0.005104 | −0.008202 | 0.056005 | 0.053622 |
| 211 | −0.043915 | 0.019245 | 0.039382 | 0.017453 | −0.044779 | −0.005622 | −0.009579 | 0.011584 | 0.037712 | 0.035482 | −0.016244 | −0.055697 | 0.021879 | 0.020137 |
| 212 | −0.018224 | 0.01215 | 0.006375 | 0.017849 | −0.015566 | 0.001555 | −0.02208 | 0.005354 | 0.016203 | −0.000728 | 0.00043 | −0.025352 | −0.021135 | 0.025497 |
| 213 | −0.111935 | 0.020817 | 0.032229 | −0.010429 | 0.021159 | −0.015364 | 0.010759 | 0.01555 | 0.006216 | 0.00248 | 0.002917 | −0.055702 | 0.007448 | −0.005035 |
| 214 | 0.006365 | −0.001032 | 0.002852 | −0.004711 | −0.017717 | −0.010389 | −0.002791 | −0.004752 | −0.006163 | −0.000529 | −0.003042 | −0.011349 | 0.002443 | −0.014329 |
| 215 | 0.024062 | 0.009591 | 0.005161 | −0.017434 | −0.02292 | −0.003888 | −0.013555 | −0.01762 | −0.011346 | −0.005955 | −0.012726 | −0.016325 | 0.014884 | 0.012556 |
| 216 | 0.012847 | −0.000833 | −0.003612 | −0.009147 | 0.026003 | 0.022773 | 0.005247 | −0.014907 | −0.019307 | −0.00351 | −0.004251 | 0.006079 | 0.000059 | −0.006388 |
| 217 | −0.010833 | −0.01192 | 0.003654 | 0.009346 | 0.00482 | 0.002947 | 0.027164 | 0.007047 | 0.008135 | 0.011713 | −0.009194 | −0.010366 | −0.01004 | 0.019098 |
| 218 | 0.010732 | −0.005683 | −0.006308 | 0.002782 | −0.021081 | 0.010078 | 0.018847 | 0.005168 | −0.006405 | −0.004535 | −0.006059 | 0.015119 | 0.002483 | 0.004858 |
| 219 | −0.005883 | 0.000941 | −0.002552 | 0.005577 | −0.005959 | 0.01845 | 0.015393 | 0.004186 | −0.003572 | −0.002773 | 0.002295 | 0.017318 | −0.000935 | 0.007108 |
| 220 | 0.010617 | −0.014608 | −0.009541 | −0.001713 | 0.012743 | 0.008648 | 0.010924 | 0.003199 | −0.008491 | −0.010458 | −0.010692 | 0.018588 | 0.001348 | 0.002319 |
| 221 | 0.017624 | 0.002612 | 0.009426 | 0.004136 | −0.002068 | 0.034515 | 0.034049 | 0.015061 | 0.011444 | 0.012668 | −0.007261 | 0.012598 | 0.018908 | 0.004619 |
| 222 | 0.008567 | 0.011751 | 0.007208 | 0.008661 | 0.020237 | 0.021234 | 0.000867 | 0.005576 | 0.007443 | 0.011442 | −0.000405 | 0.004089 | 0.024452 | 0.004308 |
| 223 | −0.035659 | 0.00594 | 0.005829 | −0.001262 | 0.004327 | 0.017767 | 0.014144 | 0.002602 | 0.005034 | 0.016178 | −0.000159 | −0.01203 | 0.024524 | 0.005972 |
| 224 | 0.013484 | 0.012703 | 0.008539 | −0.001467 | 0.059578 | 0.027642 | 0.010039 | −0.002593 | −0.012298 | −0.00294 | −0.0124 | −0.018915 | 0.025057 | −0.016304 |
| 225 | −0.003093 | 0.015426 | 0.008353 | −0.005335 | 0.055875 | 0.025341 | 0.004633 | 0.002216 | −0.016258 | −0.010144 | −0.019517 | −0.034599 | 0.02321 | −0.02104 |
| 226 | −0.015544 | 0.002993 | −0.005579 | 0.000664 | −0.003362 | 0.006685 | 0.000607 | 0.000546 | 0.002556 | 0.003891 | 0.011518 | 0.009315 | 0.007675 | 0.01071 |
| 227 | 0.03214 | 0.019171 | 0.008887 | 0.006022 | 0.03978 | 0.019346 | −0.002449 | 0.003018 | −0.003067 | −0.008735 | 0.011349 | 0.0283 | 0.010636 | 0.021662 |
| 228 | 0.00441 | −0.000841 | −0.004943 | 0.002492 | −0.031705 | −0.005839 | −0.007115 | 0.000101 | 0.002165 | 0.015178 | −0.012151 | −0.033591 | −0.003773 | −0.033563 |
| 229 | −0.014685 | 0.015659 | 0.000142 | −0.003754 | −0.009428 | −0.02154 | −0.014955 | 0.011832 | 0.00021 | −0.0039561 | 0.0024761 | −0.007589 | −0.009182 | −0.010325 |
| 230 | −0.005472 | 0.01988 | 0.011552 | −0.012127 | 0.007501 | −0.000946 | −0.018663 | 0.000385 | −0.007824 | −0.005225 | −0.000625 | −0.009333 | 0.003726 | −0.003963 |
| 231 | −0.025915 | 0.001454 | −0.005592 | 0.002536 | −0.028751 | −0.010522 | 0.002416 | 0.005561 | 0.013457 | 0.011326 | −0.016355 | −0.023644 | 0.006591 | −0.014546 |
| 232 | 0.004899 | −0.005052 | −0.01554 | −0.021136 | −0.014867 | 0.007353 | −0.03259 | −0.007724 | −0.007118 | 0.003621 | −0.014268 | 0.002619 | 0.000416 | 0.02189 |
| 233 | 0.007543 | 0.008538 | 0.001257 | −0.011494 | −0.011344 | −0.008542 | −0.044653 | 0.005355 | 0.005971 | −0.006502 | 0.011732 | 0.00498 | 0.0027 | 0.042936 |
| 234 | 0.017573 | 0.011639 | 0.001044 | 0.012994 | −0.018113 | 0.002934 | −0.01863 | 0.005409 | 0.00573 | −0.007107 | 0.0059941 | −0.003456 | −0.010397 | −0.022137 |
| 235 | −0.01662 | 0.008447 | 0.007178 | 0.020239 | −0.026039 | −0.010291 | −0.010993 | 0.015738 | 0.023631 | 0.006536 | −0.003961 | −0.034529 | 0.011348 | −0.022736 |
| 236 | −0.019104 | −0.008768 | −0.006873 | −0.002608 | −0.00142 | −0.00196 | −0.01386 | −0.009597 | −0.006528 | −0.00272 | 0.004113 | 0.011911 | 0.005141 | 0.003547 |
| 237 | −0.003412 | −0.011934 | −0.003037 | −0.004376 | 0.002307 | −0.002308 | −0.00656 | −0.00893 | −0.013782 | −0.013218 | −0.0076 | −0.007554 | −0.033761 | −0.016009 |
| 238 | −0.015495 | −0.007839 | −0.001066 | −0.007371 | −0.012211 | −0.002147 | −0.008844 | −0.004342 | −0.006813 | −0.004497 | −0.013136 | −0.023139 | −0.019395 | −0.006661 |
| 239 | −0.016885 | −0.000129 | −0.00187 | −0.004227 | −0.009554 | −0.009297 | −0.00946 | 0.003896 | 0.006133 | 0.0052151 | −0.006808 | −0.024301 | 0.0018151 | 0.005921 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 240 | 0.031276 | −0.013011 | −0.00534 | −0.001118 | 0.010418 | −0.010145 | −0.015112 | −0.008116 | 0.008393 | 0.007953 | 0.002704 | 0.023231 | −0.009844 | 0.020096 |
| 241 | 0.026752 | −0.011213 | −0.00962 | −0.01092 | 0.025888 | −0.011502 | −0.031851 | −0.015875 | −0.012574 | −0.013139 | −0.00597 | −0.009323 | −0.007922 | 0.011764 |
| 242 | 0.009998 | 0.008688 | 0.010583 | 0.007641 | −0.008015 | −0.010869 | −0.009686 | 0.011886 | 0.020775 | 0.014411 | 0.00199 | −0.008216 | 0.006452 | −0.01285 |
| 243 | −0.007294 | 0.016389 | 0.019925 | 0.018342 | −0.023499 | 0.006476 | 0.002723 | 0.017682 | 0.028696 | 0.029888 | 0.002329 | −0.036177 | 0.00772 | −0.006551 |
| 244 | 0.021836 | 0.007789 | 0.004129 | −0.006668 | 0.0075 | 0.00518 | 0.002306 | 0.002792 | −0.0016 | 0.0014861 | −0.011166 | −0.002319 | 0.006678 | 0.00832 |
| 245 | 0.016538 | 0.008466 | −0.003868 | −0.008492 | 0.034136 | −0.022282 | −0.002094 | −0.006539 | −0.00791 | −0.003593 | −0.011995 | 0.001626 | −0.016982 | 0.009659 |
| 246 | 0.016642 | 0.00205 | −0.002465 | 0.001486 | 0.002284 | −0.002211 | −0.010843 | 0.001909 | 0.002539 | −0.008889 | 0.016123 | 0.012359 | −0.013786 | −0.001238 |
| 247 | −0.017761 | 0.001891 | 0.007305 | 0.007502 | −0.005215 | −0.00186 | −0.003711 | 0.011012 | 0.010767 | 0.003053 | 0.016459 | 0.016152 | 0.004531 | 0.005375 |
| 248 | −0.010081 | 0.000292 | 0.00187 | 0.000677 | −0.014125 | −0.007714 | −0.011884 | 0.007726 | −0.001673 | −0.005702 | −0.001588 | 0.023168 | 0.005285 | 0.014072 |
| 249 | 0.013918 | −0.006477 | −0.011916 | 0.003157 | 0.012714 | −0.002095 | −0.013922 | −0.01043 | −0.006048 | −0.004291 | −0.00284 | 0.006472 | −0.015185 | 0.019251 |
| 250 | 0.014672 | −0.007376 | −0.001026 | −0.000422 | 0.010746 | −0.004366 | −0.01425 | −0.007435 | 0.00033 | 0.001096 | 0.006216 | 0.003435 | 0.003575 | 0.013769 |
| 251 | 0.017712 | −0.001361 | 0.003425 | 0.00213 | 0.024362 | −0.007918 | −0.0059 | 0.000039 | 0.002511 | −0.002728 | −0.005715 | 0.001867 | 0.002719 | −0.002088 |
| 252 | 0.003751 | 0.011585 | 0.001193 | 0.003639 | 0.017796 | −0.031178 | −0.003417 | 0.006164 | 0.002408 | −0.001174 | −0.01859 | −0.006624 | −0.007715 | 0.008472 |
| 253 | −0.017496 | 0.003872 | 0.00061 | −0.007742 | 0.002521 | −0.012216 | −0.009813 | −0.010818 | −0.009087 | 0.007174 | −0.010962 | −0.048656 | −0.004246 | −0.01562 |
| 254 | −0.026623 | 0.011412 | 0.004673 | 0.004581 | −0.004491 | 0.006718 | 0.005075 | 0.000595 | 0.00492 | 0.00579 | 0.001927 | −0.019649 | 0.00368 | 0.009012 |
| 255 | 0.016052 | 0.006742 | 0.005405 | 0.004848 | −0.00014 | 0.011704 | 0.007126 | 0.007227 | 0.007326 | 0.000359 | 0.002895 | 0.005453 | −0.008241 | 0.00728 |
| 256 | 0.043703 | −0.00738 | −0.011232 | −0.004776 | 0.023621 | −0.012264 | 0.020852 | −0.003688 | −0.017834 | −0.015488 | −0.013574 | 0.022058 | −0.025567 | −0.005209 |
| 257 | −0.023389 | −0.001801 | 0.005741 | −0.002772 | 0.001281 | 0.005723 | 0.015607 | 0.004419 | 0.011324 | 0.003843 | 0.002181 | 0.003116 | 0.009059 | 0.011782 |
| 258 | −0.022099 | −0.011296 | 0.003303 | 0.0045 | 0.009142 | 0.008175 | 0.008541 | −0.010943 | 0.000871 | 0.006503 | −0.001012 | 0.00256 | 0.024091 | −0.012272 |
| 259 | 0.00913 | 0.008872 | 0.006216 | 0.011936 | 0.013132 | −0.007989 | −0.012478 | 0.00055 | 0.001299 | 0.00231 | −0.000317 | −0.0114 | 0.011701 | 0.00208 |
| 260 | 0.000879 | 0.011413 | 0.000355 | 0.010019 | 0.010886 | −0.036588 | −0.010205 | 0.0114 | −0.002309 | −0.001437 | −0.008635 | −0.023184 | 0.006794 | −0.003609 |
| 261 | 0.01836 | −0.00325 | −0.001654 | 0.016913 | −0.011169 | −0.027848 | 0.000532 | 0.011754 | 0.005914 | −0.000212 | −0.008061 | 0.008544 | −0.011576 | −0.02501 |
| 262 | −0.002543 | 0.002317 | 0.006708 | 0.008405 | −0.002226 | −0.006408 | 0.008117 | 0.011967 | 0.015931 | 0.015171 | 0.003759 | 0.004902 | 0.00836 | −0.010643 |
| 263 | −0.017596 | 0.005709 | 0.01122 | 0.008868 | −0.017928 | −0.015834 | −0.004217 | 0.009156 | 0.015897 | 0.012191 | 0.002571 | 0.001628 | 0.00961 | −0.002968 |
| 264 | 0.017353 | −0.001197 | −0.004418 | 0.013641 | 0.01128 | 0.011744 | −0.011399 | −0.006838 | −0.008644 | −0.005942 | 0.00069 | −0.017329 | 0.009379 | −0.001883 |
| 265 | −0.026905 | 0.005688 | −0.00655 | 0.014146 | −0.01118 | 0.015711 | 0.012991 | −0.00058 | −0.00864 | −0.004116 | 0.008335 | −0.028584 | 0.006216 | −0.002875 |
| 266 | −0.023336 | 0.008179 | −0.004127 | 0.010744 | −0.010784 | 0.00955 | 0.02753 | 0.008221 | 0.000502 | 0.000045 | 0.003311 | −0.001395 | −0.01864 | −0.008228 |
| 267 | 0.021626 | 0.004081 | −0.00765 | 0.001885 | −0.004396 | −0.016781 | −0.003747 | 0.003778 | −0.007259 | 0.009273 | 0.010029 | −0.007134 | 0.0098 | −0.006911 |
| 268 | −0.007212 | 0.004828 | −0.0079 | 0.000435 | 0.007573 | 0.008125 | −0.005705 | −0.003913 | −0.000613 | 0.001047 | 0.012529 | 0.001297 | 0.012293 | 0.015058 |
| 269 | −0.008465 | 0.003544 | −0.006471 | −0.005706 | 0.003631 | 0.007053 | 0.000421 | −0.00396 | −0.006639 | −0.00391 | 0.00017 | −0.005145 | 0.003412 | 0.006026 |
| 270 | 0.015241 | 0.006038 | −0.002996 | 0.002538 | 0.009852 | 0.002213 | −0.003866 | 0.000537 | −0.002215 | −0.003553 | 0.012022 | 0.029849 | 0.003397 | 0.015934 |
| 271 | −0.048714 | 0.00775 | 0.007339 | 0.019797 | −0.025674 | −0.02566 | 0.005692 | 0.010912 | 0.023881 | 0.033675 | 0.032324 | −0.017386 | 0.005672 | −0.003988 |
| 272 | −0.018327 | 0.004662 | 0.000373 | 0.00745 | −0.019451 | −0.0231 | −0.007258 | 0.015885 | 0.011848 | 0.008735 | 0.00749 | −0.002592 | −0.000514 | −0.015599 |
| 273 | −0.01127 | 0.004867 | 0.001147 | −0.004965 | −0.007979 | −0.010325 | −0.009572 | 0.002366 | −0.000815 | −0.005128 | 0.002224 | −0.000478 | 0.017914 | 0.003441 |
| 274 | −0.009388 | 0.005258 | 0.002927 | −0.004572 | −0.009318 | −0.009079 | −0.008055 | 0.003485 | −0.000185 | −0.005452 | 0.002375 | −0.002951 | 0.014654 | −0.002943 |
| 275 | 0.040546 | 0.012169 | 0.010577 | 0.001611 | 0.005177 | −0.008123 | −0.018386 | 0.006893 | −0.003816 | −0.008927 | 0.013527 | 0.048556 | 0.000432 | 0.016389 |
| 276 | −0.012943 | −0.011631 | −0.009562 | 0.00186 | −0.000926 | −0.013406 | −0.022688 | −0.007097 | −0.000201 | 0.002005 | 0.004751 | 0.014071 | 0.006256 | −0.011704 |
| 277 | 0.003726 | 0.00523 | 0.001303 | 0.004125 | −0.010193 | −0.01235 | −0.005806 | 0.002389 | 0.00086 | 0.000277 | 0.000778 | −0.000016 | −0.003124 | −0.013759 |
| 278 | 0.007259 | 0.004697 | 0.001499 | −0.003022 | −0.010673 | −0.020997 | −0.009532 | 0.001244 | −0.006652 | −0.002639 | −0.004476 | −0.004301 | 0.003305 | −0.019546 |
| 279 | −0.000176 | −0.00182 | −0.00156 | 0.001977 | −0.024132 | −0.007822 | −0.007382 | 0.001978 | 0.008287 | 0.010038 | −0.003024 | −0.005323 | −0.001969 | −0.0032 |
| 280 | 0.008969 | 0.009897 | 0.012128 | 0.01129 | −0.00505 | 0.017394 | −0.012452 | −0.000032 | 0.012763 | 0.0235 | 0.009209 | −0.027503 | 0.015565 | −0.027033 |
| 281 | 0.005686 | −0.000204 | −0.001222 | 0.002943 | 0.000857 | −0.003839 | −0.005932 | −0.002718 | 0.002846 | 0.003635 | 0.018266 | 0.008377 | 0.016002 | −0.017699 |
| 282 | 0.004704 | −0.000934 | 0.001336 | 0.002812 | 0.001578 | −0.004673 | 0.000846 | −0.007356 | 0.001705 | 0.00744 | 0.016265 | 0.007216 | 0.032122 | −0.024716 |
| 283 | −0.008 | −0.001437 | 0.008076 | 0.013459 | −0.020237 | −0.008738 | 0.009052 | 0.012095 | 0.010415 | 0.009895 | 0.016307 | 0.026999 | 0.01538 | −0.007951 |
| 284 | −0.005503 | −0.007468 | 0.003474 | 0.002099 | −0.006341 | 0.002643 | 0.011615 | −0.000272 | 0.006553 | 0.004669 | 0.000549 | 0.00314 | 0.015135 | −0.001551 |
| 285 | −0.007038 | −0.00487 | 0.001681 | 0.00405 | −0.006663 | −0.002148 | 0.013124 | −0.002867 | 0.003483 | 0.002367 | −0.000915 | −0.00557 | 0.01312 | −0.000806 |
| 286 | −0.017903 | −0.006361 | 0.012273 | 0.008072 | 0.005344 | 0.011876 | 0.009263 | −0.009561 | 0.00949 | 0.012313 | 0.001466 | −0.000545 | 0.026518 | −0.011245 |
| 287 | −0.017057 | −0.009038 | 0.00895 | 0.003402 | 0.0035 | 0.005327 | 0.008822 | −0.011561 | 0.004749 | 0.011448 | 0.000434 | 0.002703 | 0.021324 | −0.010958 |
| 288 | 0.01426 | −0.017854 | 0.001312 | 0.005379 | 0.006268 | −0.004447 | 0.007138 | −0.015024 | −0.008064 | 0.00324 | −0.002252 | 0.018609 | 0.012624 | −0.031325 |
| 289 | 0.000447 | −0.00248 | −0.001213 | 0.008178 | 0.013821 | 0.008565 | 0.007874 | 0.004164 | 0.007664 | 0.005023 | 0.019791 | 0.032332 | 0.012332 | −0.006098 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 290 | 0.011416 | −0.001871 | 0.006119 | 0.006275 | 0.021477 | −0.003954 | 0.009872 | −0.003815 | −0.004046 | −0.000634 | 0.00006 | −0.002498 | −0.017985 | 0.004012 |
| 291 | 0.009521 | −0.000584 | 0.00828 | 0.008683 | 0.016959 | −0.003497 | 0.013304 | −0.001744 | 0.000041 | 0.00279 | 0.001139 | −0.001419 | −0.018598 | 0.005073 |
| 292 | 0.005011 | −0.000818 | 0.010362 | 0.008056 | 0.009313 | 0.000162 | 0.009697 | 0.000006 | 0.008534 | 0.008375 | 0.000418 | −0.009096 | −0.024101 | 0.011147 |
| 293 | 0.010529 | −0.001808 | 0.011179 | 0.010794 | −0.014906 | 0.018781 | 0.007667 | 0.001457 | 0.015477 | 0.012124 | 0.017785 | 0.000918 | 0.00751 | 0.029814 |
| 294 | 0.033057 | 0.000271 | −0.003929 | 0.007387 | −0.011561 | 0.003949 | 0.002863 | 0.000926 | −0.003999 | −0.000281 | 0.01006 | 0.012295 | 0.008495 | 0.008338 |
| 295 | 0.00446 | 0.005811 | 0.013925 | 0.004544 | −0.011797 | −0.012352 | 0.016822 | 0.016049 | 0.019397 | 0.012007 | 0.006888 | −0.010991 | 0.00455 | 0.001102 |
| 296 | 0.022084 | 0.012324 | 0.005865 | 0.003053 | −0.022316 | −0.035039 | −0.011436 | 0.024057 | 0.006448 | −0.001515 | 0.008426 | 0.022211 | −0.011074 | −0.003757 |
| 297 | 0.011041 | −0.004151 | 0.002084 | −0.009146 | 0.012124 | −0.019554 | 0.01156 | 0.006593 | 0.005148 | 0.005227 | −0.010735 | −0.029974 | 0.003198 | −0.018004 |
| 298 | −0.01459 | 0.015944 | 0.013415 | 0.010293 | −0.012595 | 0.004547 | −0.007783 | 0.007532 | 0.002961 | 0.013723 | 0.011225 | 0.004889 | 0.002597 | 0.0196 |
| 299 | −0.017552 | −0.00113 | −0.003905 | −0.006681 | 0.033947 | 0.000689 | 0.00186 | −0.004014 | −0.000499 | 0.011253 | −0.002807 | −0.039382 | 0.01124 | −0.000433 |
| 300 | −0.02345 | −0.007886 | 0.009062 | 0.013688 | −0.045275 | 0.002848 | −0.005617 | −0.010168 | 0.014662 | 0.01723 | 0.014764 | 0.019518 | −0.016629 | −0.048782 |
| 301 | −0.000249 | 0.003513 | 0.002067 | 0.00053 | 0.021733 | 0.004755 | 0.015036 | 0.006045 | 0.000515 | 0.004498 | 0.001321 | −0.03009 | 0.007988 | 0.007151 |
| 302 | 0.013928 | 0.003426 | −0.000639 | 0.002534 | 0.037437 | 0.008366 | 0.012213 | 0.006087 | 0.002447 | 0.003256 | 0.008051 | −0.007766 | 0.004749 | 0.002084 |
| 303 | −0.015383 | −0.000535 | −0.000158 | −0.001951 | 0.033077 | 0.011809 | −0.00143 | −0.001509 | 0.003971 | 0.021769 | −0.007759 | −0.040377 | 0.011898 | −0.008337 |
| 304 | 0.01061 | −0.000113 | −0.001757 | −0.005814 | 0.057087 | 0.005903 | −0.01255 | −0.011004 | −0.011129 | 0.007255 | −0.002171 | −0.012429 | 0.005361 | −0.012928 |
| 305 | −0.013989 | −0.002589 | 0.01068 | 0.006534 | −0.025939 | 0.03035 | 0.024248 | 0.015751 | 0.015537 | 0.006342 | 0.011135 | −0.021829 | −0.006826 | −0.007936 |
| 306 | 0.011669 | −0.024692 | −0.006451 | 0.014831 | 0.008774 | 0.027478 | 0.021056 | −0.003996 | −0.005358 | −0.010227 | 0.00853 | 0.017788 | −0.005483 | 0.009367 |
| 307 | 0.032778 | −0.015897 | −0.00185 | −0.00801 | 0.009989 | 0.004626 | 0.019848 | −0.032358 | −0.001006 | 0.027802 | −0.023398 | 0.013301 | −0.008144 | −0.023894 |
| 308 | −0.011789 | −0.000347 | −0.001634 | −0.018467 | −0.001583 | −0.003264 | −0.047133 | −0.006922 | 0.001872 | −0.011866 | 0.011946 | 0.052697 | −0.016615 | 0.021034 |
| 309 | −0.011013 | 0.000909 | −0.001387 | −0.002074 | −0.030633 | −0.022098 | 0.009998 | 0.001052 | −0.006246 | −0.002656 | −0.005347 | −0.010902 | −0.012691 | −0.003384 |
| 310 | −0.012354 | 0.010498 | 0.008868 | 0.00873 | −0.039158 | −0.020523 | −0.004362 | 0.005506 | −0.000765 | 0.008506 | 0.009408 | −0.033212 | 0.009041 | 0.022756 |
| 311 | −0.003441 | 0.007815 | 0.00211 | 0.001509 | 0.007526 | −0.003097 | −0.012511 | −0.004202 | −0.007406 | −0.012358 | 0.004187 | 0.000022 | −0.005004 | 0.011587 |
| 312 | −0.000066 | 0.00377 | 0.001434 | −0.03526 | 0.045368 | 0.026154 | −0.003161 | 0.002484 | 0.000331 | 0.002546 | −0.004618 | 0.005895 | −0.009793 | −0.028755 |
| 313 | −0.000104 | 0.00531 | 0.009075 | 0.007016 | −0.00381 | −0.011577 | −0.029489 | 0.007661 | −0.004631 | −0.027049 | −0.002643 | 0.023061 | −0.011635 | 0.006446 |
| 314 | 0.003459 | −0.016426 | 0.00339 | −0.008846 | 0.02076 | 0.001979 | 0.005297 | −0.012842 | 0.002153 | 0.009385 | −0.015643 | −0.001561 | −0.026068 | 0.005073 |
| 315 | −0.019695 | 0.00167 | 0.00437 | −0.000328 | −0.007813 | −0.006152 | 0.005623 | 0.001911 | 0.007451 | 0.008975 | −0.000331 | −0.009085 | −0.009411 | −0.010258 |
| 316 | 0.042315 | 0.003081 | 0.009219 | 0.005014 | −0.01247 | 0.016948 | 0.027101 | 0.031624 | −0.000612 | −0.00616 | −0.018437 | −0.041167 | −0.03289 | −0.004456 |
| 317 | −0.032786 | 0.012354 | 0.008063 | 0.007303 | −0.047649 | −0.027954 | 0.018194 | 0.013973 | 0.009202 | 0.006378 | 0.004551 | −0.006094 | −0.00641 | 0.009058 |
| 318 | 0.003508 | 0.016158 | 0.004252 | −0.009939 | 0.019194 | −0.018183 | 0.00707 | −0.001644 | −0.003585 | 0.000388 | 0.001053 | −0.006189 | −0.002026 | 0.019246 |
| 319 | −0.040914 | 0.006194 | 0.002733 | −0.001766 | −0.012798 | −0.003511 | 0.02709 | 0.000465 | 0.000313 | 0.008199 | −0.012457 | −0.030604 | 0.000613 | −0.00851 |
| 320 | −0.012332 | 0.010471 | 0.002512 | 0.003939 | −0.000043 | 0.006947 | 0.009296 | 0.006152 | −0.004357 | −0.01749 | −0.003084 | −0.002279 | 0.008283 | 0.023515 |
| 321 | 0.064938 | −0.014178 | −0.013162 | 0.002461 | 0.039957 | −0.017941 | −0.014044 | −0.01572 | −0.011365 | −0.004183 | −0.013999 | 0.001707 | 0.015987 | −0.014358 |
| 322 | −0.006111 | 0.000313 | 0.005722 | 0.012941 | −0.015322 | 0.002775 | −0.006581 | 0.010008 | 0.007524 | 0.023168 | 0.018675 | −0.027479 | 0.029284 | −0.002234 |
| 323 | −0.007865 | 0.015282 | 0.007331 | 0.002569 | 0.036098 | 0.025422 | −0.014573 | −0.003757 | 0.003361 | −0.002306 | −0.001894 | −0.026142 | 0.017162 | 0.01004 |
| 324 | 0.027389 | −0.023674 | −0.020314 | −0.00721 | 0.021852 | −0.010272 | −0.01242 | −0.01372 | −0.012081 | 0.000237 | 0.007939 | −0.01131 | −0.01174 | −0.000587 |
| 325 | 0.022183 | −0.012345 | −0.017556 | 0.001394 | −0.035858 | −0.025279 | −0.004729 | 0.002208 | −0.01584 | −0.011361 | −0.010374 | 0.003609 | −0.013356 | −0.01657 |
| 326 | −0.027784 | 0.001945 | 0.005024 | 0.015916 | −0.028886 | −0.025368 | −0.018929 | 0.002887 | 0.002793 | −0.004015 | 0.003261 | 0.033005 | −0.019386 | 0.0295 |
| 327 | −0.005822 | 0.010866 | 0.006976 | 0.008064 | −0.007877 | −0.002742 | −0.008542 | 0.010252 | 0.011495 | 0.006302 | 0.005876 | −0.009709 | 0.004256 | −0.000074 |
| 328 | −0.000289 | −0.004961 | 0.002163 | 0.020553 | −0.092326 | 0.00297 | 0.009271 | 0.010069 | 0.005364 | −0.005448 | 0.013654 | 0.053773 | −0.036931 | −0.030633 |
| 329 | −0.02702 | 0.016703 | 0.005015 | 0.00744 | 0.006282 | 0.000979 | −0.017118 | 0.014898 | 0.019367 | 0.00307 | 0.007519 | 0.001641 | 0.006282 | 0.015714 |
| 330 | 0.001421 | −0.002569 | −0.010188 | 0.013991 | 0.007524 | −0.038489 | −0.021 | 0.001655 | −0.01049 | −0.008458 | −0.000395 | −0.023383 | 0.009533 | −0.00406 |
| 331 | 0.008224 | −0.000705 | 0.000942 | 0.009599 | −0.001541 | 0.009731 | −0.007318 | −0.004228 | 0.006831 | 0.010919 | 0.008452 | 0.014797 | 0.000989 | 0.00579 |
| 332 | 0.000158 | −0.005103 | −0.003981 | 0.013117 | −0.011675 | −0.019391 | 0.015974 | −0.019774 | −0.020544 | −0.009282 | −0.015291 | −0.034711 | −0.015504 | −0.044562 |
| 333 | 0.030733 | −0.003734 | −0.015089 | −0.002783 | −0.000665 | −0.012737 | 0.001097 | −0.006192 | −0.015179 | −0.011355 | −0.007088 | 0.025378 | −0.014272 | 0.002688 |
| 334 | 0.026538 | 0.008669 | 0.00209 | 0.006342 | −0.013346 | −0.024874 | 0.008625 | 0.031638 | 0.018095 | 0.002432 | 0.002678 | 0.026369 | −0.00544 | −0.007369 |
| 335 | −0.00176 | −0.000453 | −0.010456 | −0.001306 | 0.001064 | 0.011405 | −0.001419 | −0.014713 | −0.021005 | −0.015029 | −0.008942 | −0.008426 | −0.00296 | 0.011214 |
| 336 | 0.005835 | −0.007039 | 0.000061 | 0.000422 | 0.018234 | 0.004155 | 0.01202 | −0.009196 | −0.023028 | −0.000923 | 0.010653 | 0.014737 | −0.001605 | 0.006964 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 337 | −0.018437 | 0.00148 | −0.00906 | 0.000952 | 0.015971 | 0.00425 | 0.029354 | 0.004219 | −0.000903 | 0.002129 | 0.00437 | −0.023251 | −0.023898 | −0.008276 |
| 338 | −0.036141 | 0.020061 | 0.004631 | −0.008918 | −0.024769 | 0.027042 | −0.01063 | 0.008006 | 0.003598 | −0.001768 | 0.003045 | 0.006957 | −0.012038 | 0.0304 |
| 339 | 0.01945 | −0.000259 | 0.002496 | 0.006366 | 0.031663 | 0.01585 | 0.021776 | −0.005822 | 0.005298 | 0.005221 | −0.009403 | 0.010463 | 0.000195 | −0.024349 |
| 340 | −0.048156 | 0.02531 | 0.013637 | −0.011819 | −0.030839 | −0.026547 | −0.006599 | 0.022917 | 0.023275 | 0.008062 | −0.002756 | −0.010713 | −0.030164 | 0.009031 |

| | CR | CS | CT | CU | CV | CW | CX | CY | CZ | DA | DB | DC | DD | DE |
|---|---|---|---|---|---|---|---|---|---|---|---|---|---|---|
| 1 | −0.063541 | −0.066896 | −0.018596 | 0.012904 | −0.013668 | 0.034279 | 0.052207 | −0.113455 | −0.060846 | 0.012057 | −0.027344 | 0.014357 | 0.024303 | −0.032834 |
| 2 | −0.031712 | 0.119365 | −0.008381 | 0.072252 | 0.003514 | 0.097712 | 0.059483 | 0.112097 | 0.042507 | 0.024264 | 0.03955 | −0.023483 | −0.044921 | −0.016026 |
| 3 | 0.011909 | −0.079622 | −0.039148 | 0.008872 | −0.069688 | 0.010554 | −0.011569 | −0.006864 | 0.037947 | −0.000118 | −0.08079 | 0.005832 | −0.058419 | −0.073527 |
| 4 | −0.141534 | 0.009463 | −0.02303 | −0.032974 | −0.015103 | −0.055616 | −0.012946 | −0.038035 | −0.018334 | 0.044546 | 0.0932 | 0.090273 | 0.003323 | 0.12321 |
| 5 | −0.017848 | −0.102935 | −0.01519 | −0.020426 | −0.043595 | −0.026367 | −0.013848 | 0.015566 | −0.032569 | −0.025663 | −0.00861 | 0.042188 | 0.028861 | 0.116588 |
| 6 | −0.005383 | 0.024559 | 0.094896 | 0.004441 | 0.0558 | 0.04156 | 0.014753 | 0.007169 | −0.006784 | −0.057558 | −0.051782 | 0.022124 | 0.081867 | −0.006603 |
| 7 | 0.035768 | −0.065363 | −0.052357 | −0.044619 | −0.015872 | −0.043355 | −0.031944 | 0.006064 | 0.068529 | −0.006503 | 0.091157 | 0.049596 | −0.019011 | −0.033258 |
| 8 | −0.120913 | −0.079138 | 0.084342 | 0.012473 | 0.050335 | −0.039128 | −0.00561 | −0.005499 | 0.035431 | 0.027993 | −0.046993 | 0.049783 | 0.0227 | 0.045745 |
| 9 | 0.009666 | −0.064648 | 0.00493 | −0.047241 | 0.029876 | −0.024361 | −0.041687 | 0.017282 | 0.030879 | 0.031445 | −0.187455 | 0.116654 | 0.111435 | −0.013895 |
| 10 | −0.026031 | −0.01644 | −0.053283 | −0.007139 | −0.028193 | −0.009044 | −0.016788 | −0.075949 | −0.02098 | −0.040877 | −0.027765 | 0.075488 | 0.0268 | 0.000049 |
| 11 | −0.03509 | −0.072499 | 0.00103 | −0.011069 | 0.036446 | −0.021967 | −0.046611 | −0.036935 | 0.017073 | 0.024611 | −0.020244 | −0.004166 | −0.08501 | −0.023422 |
| 12 | 0.028634 | 0.034598 | 0.015499 | 0.028316 | 0.017598 | 0.016922 | 0.030212 | 0.09575 | 0.01666 | −0.043076 | −0.084954 | 0.037726 | 0.014585 | 0.019596 |
| 13 | 0.140029 | 0.07769 | 0.059866 | −0.046338 | 0.057573 | 0.028866 | −0.058309 | 0.14778 | −0.006013 | 0.045165 | −0.077233 | 0.014992 | 0.085456 | −0.047007 |
| 14 | −0.115786 | −0.056799 | −0.00377 | −0.005913 | −0.041913 | −0.002336 | 0.040055 | −0.027551 | 0.006791 | 0.041776 | 0.078054 | 0.002642 | −0.019434 | 0.008711 |
| 15 | 0.010756 | 0.034447 | 0.006758 | 0.007334 | −0.031727 | −0.051248 | 0.01125 | 0.059097 | 0.017832 | −0.0194 | −0.05859 | 0.005317 | 0.003319 | −0.040399 |
| 16 | 0.000583 | 0.106294 | 0.004369 | 0.002713 | 0.030915 | 0.005896 | 0.007707 | 0.032226 | −0.094127 | −0.021964 | 0.018776 | −0.01517 | −0.02811 | 0.024912 |
| 17 | −0.043609 | 0.005033 | −0.027311 | 0.028751 | −0.049442 | 0.001287 | 0.048834 | −0.098821 | −0.102152 | −0.010462 | 0.035153 | 0.011095 | 0.026057 | 0.070376 |
| 18 | −0.02381 | 0.077468 | 0.029389 | −0.019761 | −0.002874 | 0.015087 | −0.015258 | 0.023534 | −0.003518 | −0.012739 | −0.154107 | 0.018745 | −0.042212 | −0.061936 |
| 19 | 0.033047 | −0.108729 | 0.007054 | 0.026185 | −0.038351 | −0.064501 | −0.006262 | −0.023062 | −0.012332 | −0.029636 | 0.077056 | −0.014027 | −0.085714 | −0.086155 |
| 20 | 0.07597 | 0.07326 | −0.052935 | −0.019835 | −0.007847 | −0.0193241 | −0.049507 | 0.002223 | 0.004955 | 0.013879 | 0.064323 | −0.02549 | −0.070102 | 0.071321 |
| 21 | 0.015981 | −0.016377 | −0.038294 | 0.030412 | −0.007458 | 0.0213 | 0.0337231 | −0.0429431 | −0.099506 | −0.01507 | −0.082447 | −0.091825 | −0.039094 | −0.085422 |
| 22 | −0.089897 | 0.078826 | 0.099293 | 0.011891 | 0.045877 | 0.04612 | −0.030429 | −0.081732 | −0.039719 | −0.04716 | −0.020874 | 0.026391 | 0.026504 | −0.097029 |
| 23 | −0.070864 | −0.02546 | −0.140429 | −0.040723 | −0.078061 | −0.043364 | −0.016785 | −0.033676 | −0.056074 | −0.102092 | −0.040804 | 0.100836 | 0.03959 | −0.032281 |
| 24 | 0.032297 | 0.011675 | 0.00515 | 0.033069 | 0.02815 | −0.042251 | 0.084316 | −0.051388 | 0.030524 | 0.060922 | 0.047538 | −0.01959 | −0.01441 | −0.054048 |
| 25 | 0.055086 | 0.0107 | −0.014804 | −0.001556 | −0.004557 | 0.000879 | 0.012591 | 0.055787 | 0.107419 | 0.07212 | 0.053754 | 0.063834 | −0.03538 | 0.074609 |
| 26 | −0.054972 | −0.006828 | 0.018492 | 0.009854 | −0.023867 | −0.062972 | 0.032273 | −0.034142 | 0.012068 | 0.013766 | 0.002307 | 0.03298 | 0.012775 | 0.088424 |
| 27 | 0.02473 | 0.021984 | 0.023386 | 0.02168 | 0.051063 | 0.105355 | 0.016755 | 0.017989 | 0.029952 | 0.068044 | 0.085011 | −0.152226 | −0.05981 | −0.026852 |
| 28 | −0.060452 | 0.028241 | 0.031316 | 0.035621 | −0.014396 | −0.050419 | 0.061002 | 0.004406 | −0.002688 | 0.030693 | 0.042442 | 0.025615 | 0.015051 | 0.003121 |
| 29 | 0.009097 | −0.058912 | −0.004289 | −0.00233 | −0.003194 | −0.018519 | 0.014928 | −0.011387 | −0.011255 | −0.014592 | −0.036762 | −0.00996 | −0.003058 | −0.037418 |
| 30 | 0.025563 | −0.001462 | 0.052171 | −0.055721 | 0.014097 | −0.015445 | −0.042904 | 0.127545 | 0.071102 | 0.039694 | 0.046036 | −0.15779 | −0.076644 | −0.036175 |
| 31 | 0.049582 | 0.008897 | 0.017201 | −0.025076 | −0.018861 | −0.021417 | −0.034194 | −0.057192 | −0.02197 | −0.083666 | −0.036102 | 0.002501 | 0.130186 | 0.053013 |
| 32 | −0.071839 | 0.023971 | −0.0492 | −0.039116 | −0.030042 | −0.007684 | −0.007734 | −0.02001 | −0.023002 | −0.056737 | −0.031748 | 0.036985 | −0.037292 | −0.002086 |
| 33 | −0.027775 | 0.056603 | −0.021796 | 0.076417 | −0.00857 | 0.026657 | 0.059193 | 0.019452 | 0.120977 | −0.049614 | 0.136362 | −0.023672 | 0.046778 | 0.027373 |
| 34 | −0.086047 | −0.037043 | −0.018693 | 0.042517 | 0.013412 | 0.00536 | 0.033121 | −0.01557 | −0.136451 | −0.023551 | 0.053878 | 0.025659 | 0.031984 | −0.069116 |
| 35 | −0.146939 | −0.035256 | −0.052588 | −0.003549 | −0.005376 | 0.005439 | −0.043189 | −0.073089 | −0.095858 | −0.069638 | 0.103675 | −0.000856 | 0.049614 | −0.044014 |
| 36 | 0.044179 | −0.104259 | −0.016608 | −0.033804 | −0.075102 | −0.022883 | 0.005026 | −0.008575 | 0.077311 | −0.05372 | −0.060412 | −0.052742 | −0.104266 | −0.056658 |
| 37 | 0.082133 | −0.061304 | 0.043744 | 0.006139 | 0.047782 | −0.007725 | −0.022298 | 0.082317 | 0.085578 | 0.057706 | −0.20643 | −0.007355 | −0.027312 | −0.031098 |
| 38 | 0.043239 | −0.00763 | −0.019294 | 0.030077 | −0.024234 | 0.038541 | 0.023021 | 0.04489 | 0.035054 | −0.007114 | −0.032522 | 0.041795 | −0.085571 | 0.077508 |
| 39 | 0.022746 | 0.023057 | 0.017392 | −0.006415 | −0.02126 | 0.073721 | 0.023655 | 0.05283 | −0.055438 | 0.064563 | 0.080217 | −0.060645 | 0.015337 | −0.048048 |
| 40 | −0.006915 | −0.036953 | −0.012462 | −0.014605 | −0.011358 | −0.000056 | −0.009093 | −0.034923 | −0.003673 | −0.008716 | −0.017761 | 0.023985 | 0.007375 | −0.017446 |
| 41 | −0.10344 | 0.016851 | −0.007304 | −0.064519 | 0.034831 | −0.052097 | −0.054839 | 0.036178 | −0.020859 | 0.027958 | −0.016955 | −0.002402 | 0.035143 | 0.057819 |
| 42 | −0.04359 | −0.026838 | −0.058652 | 0.03225 | −0.020993 | −0.028112 | 0.054428 | −0.107171 | −0.135102 | 0.023872 | −0.058284 | −0.017913 | −0.005871 | 0.020336 |
| 43 | −0.041333 | 0.059012 | −0.00375 | −0.055854 | 0.020979 | −0.057821 | −0.005451 | −0.033542 | −0.080785 | −0.125404 | 0.132143 | −0.017261 | 0.054609 | 0.048404 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 44 | 0.015488 | 0.047643 | −0.018538 | −0.011252 | 0.003095 | 0.017056 | −0.033989 | 0.019392 | −0.148433 | −0.028588 | 0.025392 | −0.068834 | 0.004791 | 0.051054 |
| 45 | −0.038431 | −0.045938 | 0.076471 | −0.006025 | −0.00156 | 0.007796 | 0.016762 | 0.004033 | 0.176738 | 0.035601 | −0.014594 | 0.038408 | 0.015731 | −0.054002 |
| 46 | 0.024399 | −0.032839 | 0.055085 | −0.007138 | 0.038673 | −0.021732 | 0.015213 | 0.115924 | 0.013343 | 0.001648 | −0.065708 | −0.073152 | 0.029844 | 0.016439 |
| 47 | −0.038673 | −0.086578 | 0.009067 | −0.011089 | −0.000142 | 0.050005 | 0.045602 | 0.002822 | −0.064818 | 0.000629 | −0.017853 | 0.033305 | 0.120718 | −0.04052 |
| 48 | 0.13956 | −0.125329 | 0.000564 | 0.054564 | −0.011511 | 0.006428 | 0.074852 | −0.06556 | 0.038278 | −0.061405 | −0.117097 | 0.042332 | −0.029372 | 0.045463 |
| 49 | 0.108143 | −0.001281 | −0.051657 | 0.049168 | −0.035736 | −0.004312 | 0.01258 | −0.038568 | −0.022789 | −0.061198 | −0.026447 | 0.076909 | 0.024103 | −0.079778 |
| 50 | −0.02541 | 0.034771 | 0.030557 | 0.023561 | −0.045139 | 0.026996 | 0.019048 | 0.076796 | 0.074933 | 0.038707 | 0.080376 | 0.018296 | 0.005052 | −0.155282 |
| 51 | −0.058086 | 0.006901 | 0.032181 | 0.029202 | 0.015422 | −0.058196 | 0.040286 | −0.084862 | −0.106262 | −0.089426 | −0.061156 | −0.054441 | −0.060565 | −0.035987 |
| 52 | −0.015952 | 0.031948 | 0.013515 | 0.040648 | 0.023285 | −0.041274 | 0.098076 | −0.02576 | 0.045431 | −0.037993 | −0.072374 | −0.027226 | 0.045093 | 0.064001 |
| 53 | 0.03608 | −0.067125 | 0.011165 | 0.040014 | −0.016705 | −0.04279 | 0.068499 | 0.034472 | 0.044714 | 0.048978 | 0.027846 | −0.012953 | −0.030244 | 0.098388 |
| 54 | 0.007365 | −0.129495 | −0.075075 | −0.008796 | −0.018962 | 0.010532 | −0.035665 | −0.021348 | 0.113827 | −0.091799 | 0.111137 | 0.078103 | 0.003153 | −0.081087 |
| 55 | −0.012932 | 0.152099 | −0.07251 | 0.001908 | −0.007629 | 0.048345 | −0.031899 | 0.071048 | 0.021118 | −0.006728 | 0.025498 | −0.027392 | −0.12433 | −0.018099 |
| 56 | −0.024748 | −0.057763 | 0.020561 | 0.091283 | −0.004136 | 0.101932 | 0.090099 | 0.015523 | 0.010057 | −0.073914 | 0.053172 | −0.068015 | −0.036157 | 0.090804 |
| 57 | 0.008659 | −0.087762 | −0.064402 | 0.049916 | −0.021452 | 0.020692 | 0.018733 | −0.046399 | 0.002863 | 0.024014 | 0.10167 | −0.021704 | 0.027305 | −0.058136 |
| 58 | −0.089833 | 0.006972 | −0.005336 | 0.033295 | −0.011647 | 0.035607 | −0.022851 | 0.153212 | −0.056523 | −0.133488 | 0.024278 | 0.116294 | 0.002041 | −0.019028 |
| 59 | −0.008853 | 0.006358 | 0.048532 | 0.005447 | 0.006436 | −0.011481 | 0.02685 | 0.074668 | 0.027693 | 0.010145 | 0.011033 | 0.102328 | −0.023761 | 0.016594 |
| 60 | 0.037114 | −0.010455 | −0.009031 | 0.022659 | 0.000429 | 0.021633 | 0.014345 | 0.027431 | 0.014677 | 0.005071 | −0.029565 | −0.002889 | −0.013025 | 0.036288 |
| 61 | 0.006389 | −0.019943 | −0.021595 | 0.002904 | −0.001681 | −0.015552 | −0.004398 | −0.039759 | −0.001921 | −0.004107 | 0.025429 | 0.033738 | 0.017446 | 0.011335 |
| 62 | 0.014709 | 0.059099 | 0.018811 | 0.015311 | 0.029885 | −0.000429 | 0.00628 | 0.03877 | 0.027278 | −0.008041 | −0.035368 | −0.024668 | −0.007994 | 0.000799 |
| 63 | 0.006826 | −0.017158 | −0.014688 | −0.000259 | 0.005679 | −0.027615 | −0.011111 | −0.052171 | 0.001072 | 0.010273 | 0.01982 | −0.010363 | −0.007817 | 0.008734 |
| 64 | 0.016357 | −0.016804 | −0.01796 | −0.017524 | 0.0059 | −0.00914 | −0.023135 | 0.011468 | −0.002155 | 0.009529 | 0.01764 | −0.015582 | 0.02201 | −0.022548 |
| 65 | 0.046693 | 0.016552 | −0.011564 | 0.015785 | −0.014443 | 0.020554 | 0.017859 | 0.046658 | 0.021257 | −0.029442 | −0.033011 | 0.013764 | −0.001623 | −0.001725 |
| 66 | −0.014905 | −0.010364 | −0.013995 | −0.010684 | −0.003848 | −0.002976 | −0.018171 | 0.041621 | 0.016774 | −0.017698 | 0.031448 | −0.018244 | −0.017185 | 0.01107 |
| 67 | −0.006071 | −0.020324 | 0.008447 | −0.024617 | 0.003759 | −0.01373 | −0.034623 | −0.001675 | 0.012386 | −0.007039 | 0.015141 | 0.007019 | 0.008339 | −0.002816 |
| 68 | −0.055982 | 0.029805 | −0.002966 | 0.027744 | −0.004421 | 0.018757 | 0.014347 | 0.005236 | −0.055162 | 0.010351 | −0.021555 | 0.047122 | 0.01442 | −0.009977 |
| 69 | −0.035823 | 0.011087 | 0.008888 | 0.011663 | −0.008624 | 0.000415 | 0.021926 | −0.010535 | −0.015374 | −0.007009 | 0.016597 | 0.034115 | 0.016219 | 0.01488 |
| 70 | 0.009485 | −0.029961 | −0.002628 | 0.014646 | −0.000635 | −0.00467 | 0.004157 | −0.014371 | −0.006777 | 0.005148 | −0.01038 | 0.005697 | 0.00101 | 0.018413 |
| 71 | −0.013551 | −0.010997 | 0.020781 | −0.003555 | 0.005999 | 0.010853 | −0.008521 | 0.015415 | −0.002335 | −0.002986 | −0.037673 | 0.015457 | −0.01206 | −0.014853 |
| 72 | 0.003204 | −0.014756 | 0.001878 | −0.011766 | −0.012328 | −0.013699 | −0.002072 | 0.008574 | 0.017973 | 0.007676 | 0.000915 | 0.025624 | −0.019924 | 0.024766 |
| 73 | −0.041501 | −0.039627 | −0.005356 | −0.001867 | −0.016124 | 0.002756 | 0.001773 | 0.006388 | 0.020878 | −0.009433 | −0.030736 | 0.008045 | −0.047398 | 0.025035 |
| 74 | 0.007953 | −0.020888 | −0.030136 | −0.005316 | −0.019485 | −0.01858 | −0.028893 | 0.008735 | 0.022871 | −0.036446 | 0.029299 | 0.034553 | −0.000128 | −0.033301 |
| 75 | 0.016028 | −0.012874 | 0.007648 | 0.004546 | 0.004166 | 0.002876 | 0.001644 | 0.007002 | −0.013754 | −0.005009 | −0.025731 | −0.001746 | 0.005968 | 0.006397 |
| 76 | 0.031145 | −0.006213 | −0.007038 | −0.00509 | −0.001978 | −0.013157 | −0.01075 | −0.001099 | 0.050406 | −0.007571 | −0.002488 | 0.005509 | −0.008904 | −0.016851 |
| 77 | 0.014812 | −0.007523 | 0.011906 | 0.007281 | 0.002689 | 0.00388 | −0.000254 | 0.001992 | −0.012237 | −0.005932 | −0.019852 | −0.000639 | −0.000848 | 0.005921 |
| 78 | 0.021627 | −0.004856 | 0.016142 | 0.009911 | 0.009517 | 0.004603 | 0.002278 | 0.011762 | −0.01769 | −0.003615 | −0.036987 | 0.002493 | −0.004138 | 0.017817 |
| 79 | −0.004034 | −0.034057 | 0.000187 | 0.008038 | −0.003795 | −0.002085 | 0.013052 | 0.012972 | 0.004252 | 0.002412 | 0.000941 | 0.00031 | 0.024821 | −0.004085 |
| 80 | 0.009747 | −0.027712 | −0.031537 | −0.033978 | 0.007558 | 0.001158 | −0.045417 | −0.008939 | −0.024247 | −0.028864 | −0.006202 | −0.00346 | −0.011603 | −0.075777 |
| 81 | −0.006867 | 0.042139 | −0.038554 | −0.018336 | −0.024354 | −0.011798 | −0.02841 | −0.065135 | −0.026739 | −0.027303 | 0.037031 | 0.024021 | −0.012373 | 0.000452 |
| 82 | −0.01331 | 0.004472 | −0.002241 | 0.000292 | −0.000467 | 0.001114 | 0.011287 | −0.001518 | −0.006162 | 0.011493 | 0.004137 | 0.009571 | 0.00129 | 0.000182 |
| 83 | −0.012106 | 0.010788 | −0.004825 | 0.005415 | 0.003967 | 0.010182 | 0.01369 | −0.007029 | −0.022731 | 0.010313 | −0.005086 | 0.007909 | 0.011585 | 0.001808 |
| 84 | −0.007126 | 0.014525 | 0.011557 | 0.005923 | 0.008591 | 0.020797 | 0.002178 | −0.007161 | −0.007436 | −0.002467 | −0.016775 | 0.007375 | 0.003287 | −0.012974 |
| 85 | −0.004705 | −0.037201 | −0.022903 | −0.012872 | −0.03148 | −0.012296 | −0.004942 | −0.035832 | 0.043868 | 0.018939 | 0.035004 | 0.044781 | 0.001035 | 0.000634 |
| 86 | −0.030264 | −0.003306 | 0.00752 | −0.009449 | −0.003133 | 0.004065 | −0.000765 | −0.019983 | 0.000602 | −0.000221 | 0.031142 | 0.013265 | 0.001978 | 0.029937 |
| 87 | −0.017455 | −0.013332 | −0.015094 | −0.016156 | 0.008052 | −0.002413 | −0.010521 | −0.045725 | −0.02911 | −0.009078 | −0.037638 | 0.013102 | 0.004588 | −0.015512 |
| 88 | 0.002006 | 0.004911 | 0.009925 | 0.002137 | 0.006745 | 0.014203 | 0.003748 | 0.007147 | −0.021156 | 0.006683 | −0.035605 | 0.00414 | −0.00122 | −0.00986 |
| 89 | −0.01706 | 0.019514 | 0.012222 | 0.010812 | 0.010236 | 0.018037 | 0.011711 | 0.01086 | −0.01824 | 0.007112 | −0.021952 | 0.023853 | 0.008919 | 0.000883 |
| 90 | −0.018952 | 0.013707 | −0.004507 | 0.007901 | 0.004103 | 0.018758 | 0.010448 | 0.002341 | −0.005793 | −0.003714 | −0.003304 | 0.033439 | 0.010167 | 0.002857 |
| 91 | 0.001476 | 0.013387 | 0.013769 | 0.001822 | 0.002688 | 0.025521 | 0.004647 | 0.02028 | 0.006736 | 0.007259 | 0.02924 | 0.004205 | 0.022319 | 0.001936 |
| 92 | 0.018485 | 0.025474 | 0.015505 | −0.005398 | −0.008401 | 0.007224 | 0.005032 | 0.016279 | −0.018595 | 0.000197 | 0.017791 | −0.002298 | 0.00278 | 0.0345 |
| 93 | 0.006816 | 0.016734 | −0.006609 | 0.01153 | 0.006544 | 0.021045 | 0.000749 | −0.018754 | 0.000373 | −0.000663 | −0.003973 | 0.007077 | 0.005439 | −0.012717 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 94 | −0.018604 | −0.005556 | −0.017671 | −0.012757 | −0.007462 | −0.001182 | −0.014672 | 0.022763 | 0.000542 | 0.033688 | 0.021666 | 0.006365 | −0.012378 | 0.028139 |
| 95 | 0.779459 | −0.004755 | −0.018566 | −0.002519 | −0.012454 | −0.019661 | 0.009224 | −0.088586 | −0.082649 | −0.032939 | 0.075285 | 0.031505 | 0.0263 | 0.009821 |
| 96 | 0.003831 | 0.790176 | −0.020184 | 0.005332 | −0.033361 | −0.034043 | 0.00857 | −0.063786 | 0.035935 | −0.009144 | −0.020779 | 0.038654 | −0.014581 | −0.014585 |
| 97 | −0.009937 | −0.032544 | 0.888836 | −0.003592 | −0.049165 | −0.014361 | −0.007952 | −0.053383 | −0.033092 | −0.033436 | 0.038956 | 0.018168 | −0.019758 | 0.011035 |
| 98 | −0.006744 | −0.002683 | −0.012075 | 0.934877 | 0.002664 | −0.034273 | −0.058848 | 0.008977 | 0.00846 | 0.007758 | −0.012133 | 0.01318 | 0.006678 | 0.00037 |
| 99 | −0.007435 | −0.045559 | −0.046903 | 0.003021 | 0.941392 | −0.01129 | 0.008778 | −0.027224 | −0.00021 | −0.028371 | 0.026516 | 0.02162 | −0.019857 | −0.007144 |
| 100 | −0.015229 | −0.024305 | −0.007355 | −0.026886 | −0.007364 | 0.908313 | −0.012803 | −0.039869 | 0.003706 | −0.002011 | −0.012102 | 0.023799 | −0.000036 | 0.03495 |
| 101 | −0.001768 | 0.016177 | −0.022206 | −0.057516 | 0.004918 | −0.018335 | 0.909893 | 0.022977 | 0.006528 | −0.002236 | −0.0001 | 0.018257 | −0.005478 | −0.021218 |
| 102 | −0.051312 | −0.079664 | −0.051128 | 0.00153 | −0.028686 | −0.042516 | 0.015464 | 0.766209 | −0.075036 | −0.031987 | 0.01481 | 0.016487 | 0.01342 | 0.004577 |
| 103 | −0.079321 | 0.023174 | −0.032124 | −0.008922 | 0.000754 | −0.010833 | −0.007712 | −0.107035 | 0.748616 | −0.055899 | −0.000256 | −0.013526 | 0.054137 | 0.019891 |
| 104 | −0.019946 | −0.018105 | −0.030815 | 0.00332 | −0.023528 | −0.008968 | −0.002923 | −0.044133 | −0.047619 | 0.862527 | −0.00058 | 0.028961 | 0.015711 | −0.016541 |
| 105 | 0.097715 | −0.007917 | 0.054311 | −0.01134 | 0.029244 | −0.018648 | −0.004463 | 0.035927 | 0.006746 | 0.011508 | 0.689511 | 0.043837 | 0.010148 | −0.00423 |
| 106 | 0.029408 | 0.039095 | 0.026917 | 0.005906 | 0.028895 | 0.029048 | 0.008718 | 0.007254 | −0.016825 | 0.03636 | 0.048101 | 0.829341 | −0.038109 | −0.012689 |
| 107 | 0.022901 | 0.015617 | −0.007242 | 0.009363 | −0.012871 | 0.011039 | −0.005572 | 0.0403 | 0.049081 | 0.025911 | 0.032777 | −0.05528 | 0.857381 | −0.021998 |
| 108 | 0.018013 | −0.019775 | 0.003639 | 0.007038 | −0.000611 | 0.028971 | −0.022017 | 0.001119 | 0.018669 | 0.002926 | −0.008386 | −0.011189 | −0.019406 | 0.7927 |
| 109 | −0.029308 | −0.016286 | 0.011799 | 0.013951 | −0.012277 | −0.013218 | 0.023684 | −0.055658 | 0.003652 | −0.004229 | −0.003666 | 0.000092 | 0.011163 | 0.007582 |
| 110 | 0.002825 | −0.014886 | −0.00514 | 0.009332 | −0.018267 | 0.002731 | 0.001592 | −0.001418 | −0.021618 | 0.005053 | 0.063302 | −0.055639 | −0.017021 | −0.019792 |
| 111 | −0.002915 | −0.055303 | −0.008276 | −0.004724 | −0.012762 | 0.005147 | −0.0061 | −0.024565 | 0.073345 | 0.016959 | 0.014859 | −0.011172 | −0.028418 | −0.107988 |
| 112 | 0.005942 | −0.016486 | 0.028563 | 0.01054 | 0.012102 | 0.014832 | 0.012054 | −0.021396 | −0.024909 | 0.000125 | −0.036082 | −0.026034 | 0.009359 | −0.073412 |
| 113 | −0.039317 | −0.014176 | −0.008349 | −0.002792 | −0.0153 | 0.022213 | 0.009491 | −0.005418 | 0.020272 | 0.028038 | 0.038708 | −0.054693 | −0.03264 | −0.039961 |
| 114 | 0.040566 | −0.003262 | 0.020472 | 0.007481 | −0.009358 | 0.022608 | 0.001704 | 0.051126 | 0.032958 | −0.010914 | −0.012295 | 0.00755 | 0.01653 | −0.050292 |
| 115 | 0.029066 | 0.017058 | 0.03073 | 0.009596 | −0.004891 | 0.008256 | −0.018546 | 0.0256 | 0.028918 | −0.017927 | −0.00198 | −0.03163 | 0.001244 | −0.032417 |
| 116 | 0.008398 | 0.045778 | −0.012138 | 0.005015 | 0.001575 | −0.003086 | −0.00363 | 0.006922 | 0.002932 | 0.033389 | −0.024515 | 0.012561 | −0.003136 | −0.048982 |
| 117 | −0.00509 | −0.065393 | −0.011891 | 0.000693 | −0.010503 | −0.016094 | 0.021704 | −0.064557 | −0.023189 | −0.03575 | −0.044544 | 0.027866 | 0.041177 | 0.018152 |
| 118 | −0.02255 | −0.034876 | −0.01816 | −0.00584 | −0.013778 | −0.026405 | −0.007308 | −0.00862 | 0.027399 | −0.026642 | −0.008168 | 0.05719 | −0.008584 | −0.019693 |
| 119 | −0.013944 | 0.001609 | 0.009942 | 0.027686 | −0.000592 | −0.00177 | 0.022254 | 0.028698 | 0.016927 | 0.01936 | 0.039735 | −0.00706 | −0.028588 | 0.006755 |
| 120 | −0.022644 | 0.010862 | 0.004023 | 0.005917 | 0.008967 | −0.002938 | 0.013771 | −0.007203 | −0.028034 | −0.006858 | 0.007972 | 0.001886 | 0.037152 | 0.015579 |
| 121 | 0.006895 | 0.014407 | 0.009748 | −0.003049 | −0.010972 | −0.016512 | 0.041152 | −0.018523 | −0.012904 | 0.029102 | −0.049194 | −0.004509 | 0.050679 | 0.063237 |
| 122 | −0.036003 | 0.022947 | 0.006285 | −0.002214 | 0.009415 | 0.002064 | −0.005502 | −0.016724 | 0.000308 | 0.013486 | −0.002605 | −0.019488 | −0.005222 | −0.000014 |
| 123 | −0.023145 | 0.079058 | 0.045138 | 0.012839 | 0.02518 | −0.007963 | 0.003009 | 0.041132 | 0.02043 | 0.035673 | −0.01801 | −0.02091 | −0.037506 | −0.007547 |
| 124 | −0.001341 | 0.022474 | −0.002922 | 0.020624 | 0.009774 | −0.012278 | 0.009313 | 0.035897 | 0.009369 | 0.019724 | 0.021866 | −0.008494 | −0.029867 | −0.004678 |
| 125 | −0.017647 | −0.006027 | −0.005341 | −0.018396 | −0.008374 | −0.004586 | −0.003735 | −0.020037 | −0.023288 | −0.03919 | −0.029604 | 0.016547 | 0.033993 | −0.016526 |
| 126 | −0.023479 | 0.026282 | 0.02471 | 0.000284 | 0.001076 | 0.010817 | 0.017007 | 0.016356 | 0.017533 | −0.006017 | −0.023966 | −0.000731 | −0.01352 | 0.020163 |
| 127 | −0.01208 | 0.009061 | 0.015703 | −0.001985 | 0.000479 | 0.007799 | 0.006532 | 0.019786 | 0.00166 | −0.001535 | 0.012474 | −0.010583 | −0.007292 | 0.034006 |
| 128 | −0.005069 | −0.012026 | −0.002334 | 0.007803 | −0.003783 | −0.015919 | 0.018535 | 0.00277 | −0.016899 | −0.044192 | 0.007394 | 0.00315 | −0.001289 | 0.027346 |
| 129 | 0.009011 | −0.021786 | −0.01572 | 0.010757 | −0.002899 | 0.018054 | 0.0129 | −0.049982 | −0.0454 | −0.001693 | −0.026252 | −0.007183 | 0.057362 | −0.029585 |
| 130 | −0.025491 | 0.013357 | 0.005104 | 0.009947 | 0.01343 | 0.007657 | 0.008289 | 0.011026 | −0.059332 | −0.009558 | 0.019534 | −0.025476 | 0.025856 | 0.032156 |
| 131 | 0.014252 | −0.015998 | −0.052457 | 0.000591 | −0.003612 | −0.001629 | −0.002218 | 0.007668 | −0.052854 | 0.047008 | −0.112306 | 0.03049 | −0.03835 | 0.007289 |
| 132 | −0.012238 | 0.00858 | −0.002346 | 0.00018 | 0.003649 | −0.016166 | 0.010893 | 0.013083 | −0.013518 | −0.033016 | 0.018802 | 0.024464 | −0.005574 | −0.011167 |
| 133 | −0.051253 | −0.014776 | −0.040438 | −0.024475 | −0.021535 | −0.024355 | 0.001689 | −0.017604 | −0.062748 | −0.025964 | 0.026933 | −0.011845 | −0.006141 | 0.030255 |
| 134 | −0.004516 | −0.017692 | −0.014663 | −0.002926 | −0.007199 | 0.03159 | −0.033423 | −0.015075 | −0.02675 | −0.015951 | −0.000966 | 0.099934 | 0.01481 | 0.016988 |
| 135 | −0.007196 | −0.000461 | 0.010746 | −0.000285 | 0.015594 | −0.00808 | 0.007178 | 0.01115 | −0.008037 | −0.028445 | 0.010599 | 0.004562 | 0.014549 | 0.017781 |
| 136 | 0.025255 | −0.015371 | 0.007996 | −0.004543 | 0.000513 | −0.023545 | 0.004892 | 0.018291 | 0.025763 | 0.038625 | 0.002561 | 0.00854 | −0.002183 | 0.019538 |
| 137 | −0.010785 | 0.049042 | −0.015042 | −0.025005 | 0.013821 | −0.017828 | −0.027253 | 0.013795 | −0.038511 | −0.007968 | −0.004822 | −0.017622 | −0.006921 | 0.031467 |
| 138 | 0.011349 | −0.034357 | −0.044473 | 0.008893 | −0.02663 | 0.036336 | 0.004027 | 0.036901 | 0.006722 | 0.013825 | 0.060378 | −0.01178 | −0.029412 | −0.026363 |
| 139 | 0.026161 | −0.002621 | 0.032416 | −0.001608 | 0.019193 | 0.004668 | −0.027264 | −0.004719 | 0.037728 | 0.01638 | 0.006279 | −0.003551 | −0.017683 | −0.074147 |
| 140 | 0.032648 | 0.029253 | −0.017832 | −0.003196 | −0.010911 | 0.03358 | 0.000724 | 0.029058 | 0.0465 | −0.030961 | 0.013466 | 0.014234 | 0.007489 | −0.002528 |
| 141 | −0.032038 | 0.019021 | 0.024854 | 0.01288 | 0.006986 | −0.010201 | 0.01683 | −0.003277 | −0.046238 | −0.017604 | −0.005107 | 0.010576 | 0.007328 | 0.029964 |
| 142 | 0.026817 | 0.008424 | −0.010882 | 0.007329 | 0.007075 | 0.00659 | 0.012012 | −0.009799 | −0.006179 | 0.018374 | −0.001721 | −0.00197 | 0.036689 | −0.009254 |
| 143 | 0.012852 | 0.031839 | −0.005942 | −0.011079 | 0.010061 | −0.005876 | −0.023454 | −0.007163 | 0.000853 | −0.027412 | −0.001349 | −0.011422 | −0.002132 | −0.027914 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 144 | −0.011821 | 0.035651 | 0.011475 | 0.021192 | 0.021824 | 0.017076 | 0.010855 | 0.004976 | −0.00824 | 0.0271 | 0.04683 | −0.022962 | −0.009976 | −0.0013 |
| 145 | −0.016792 | 0.004811 | −0.045595 | −0.021004 | −0.003772 | −0.00706 | −0.018927 | −0.014828 | −0.009377 | −0.015245 | 0.057125 | 0.008591 | 0.013152 | 0.036275 |
| 146 | −0.012858 | 0.012246 | −0.010816 | −0.002797 | 0.003453 | −0.005114 | 0.0121 | −0.005783 | −0.008547 | −0.026381 | 0.033479 | 0.010531 | 0.007355 | −0.002787 |
| 147 | 0.020724 | 0.04017 | 0.003466 | 0.002614 | −0.000823 | 0.036848 | 0.016661 | 0.003758 | −0.007623 | −0.015034 | −0.023529 | −0.036977 | −0.022843 | −0.033815 |
| 148 | −0.065681 | −0.032877 | −0.028315 | 0.002606 | 0.002588 | 0.002935 | −0.007661 | −0.03052 | −0.015926 | −0.034047 | 0.060243 | −0.047528 | −0.015566 | −0.016132 |
| 149 | −0.004165 | 0.000601 | −0.010466 | −0.00196 | −0.007792 | −0.002563 | −0.016935 | 0.004144 | −0.040708 | −0.046064 | −0.011168 | 0.014584 | 0.011623 | 0.023443 |
| 150 | 0.003385 | 0.036767 | −0.015756 | −0.016828 | 0.005703 | −0.012864 | −0.00894 | −0.006737 | −0.028373 | −0.023772 | 0.010627 | 0.009964 | 0.036235 | −0.018817 |
| 151 | 0.009103 | −0.013899 | 0.01531 | 0.005771 | −0.015487 | 0.0088 | −0.018933 | 0.001655 | 0.016223 | −0.040624 | 0.0209 | −0.013817 | −0.040641 | −0.052609 |
| 152 | 0.027402 | 0.003957 | 0.03322 | 0.017005 | 0.000797 | 0.023595 | 0.026233 | 0.039023 | 0.011721 | 0.036317 | 0.012891 | 0.010857 | 0.013466 | 0.006094 |
| 153 | 0.016957 | 0.020151 | 0.036528 | 0.034022 | 0.009362 | 0.009049 | 0.032848 | 0.006745 | −0.011859 | 0.006212 | 0.004133 | 0.023081 | 0.011755 | −0.01775 |
| 154 | 0.044242 | 0.008516 | −0.002936 | 0.013699 | 0.014897 | 0.005717 | 0.018999 | −0.011094 | 0.021368 | 0.019864 | −0.034528 | 0.011199 | 0.022741 | 0.019116 |
| 155 | 0.054768 | 0.013556 | 0.008209 | 0.014994 | 0.015583 | 0.026184 | 0.025771 | 0.012978 | 0.022579 | −0.005384 | 0.00149 | 0.003873 | 0.020765 | −0.022761 |
| 156 | −0.011304 | −0.016335 | −0.015756 | 0.010864 | −0.011968 | −0.01917 | 0.004047 | −0.042335 | −0.01786 | −0.014264 | 0.022526 | 0.005422 | −0.017401 | −0.01276 |
| 157 | 0.00027 | 0.017954 | −0.002731 | −0.006845 | 0.000536 | −0.012796 | 0.008888 | −0.002365 | 0.006846 | −0.02539 | 0.054269 | −0.025714 | 0.011004 | 0.024249 |
| 158 | 0.041031 | 0.009455 | 0.006316 | 0.014589 | −0.009543 | −0.000345 | −0.002963 | 0.013456 | 0.050168 | −0.026306 | −0.004275 | −0.028393 | −0.012206 | −0.094476 |
| 159 | 0.085597 | −0.011902 | −0.002728 | −0.008662 | 0.014844 | −0.029239 | 0.000404 | 0.03418 | 0.00696 | −0.001215 | −0.078779 | 0.007723 | 0.054514 | 0.043919 |
| 160 | −0.02574 | −0.020546 | −0.009752 | 0.008358 | −0.016849 | −0.010352 | −0.001809 | −0.009247 | 0.017855 | 0.009982 | 0.024853 | −0.038633 | 0.004304 | 0.018018 |
| 161 | 0.007025 | 0.000168 | 0.005308 | 0.043103 | −0.003564 | 0.017989 | 0.022242 | 0.010864 | 0.008566 | −0.043418 | 0.025448 | 0.022419 | −0.029313 | −0.02753 |
| 162 | −0.013672 | 0.035788 | −0.013347 | −0.002395 | 0.015118 | −0.002644 | −0.019472 | −0.001428 | −0.021131 | 0.021253 | 0.010218 | −0.000441 | 0.013716 | −0.03282 |
| 163 | 0.003104 | 0.009617 | −0.013501 | −0.002839 | 0.004384 | −0.008102 | 0.006302 | −0.015119 | −0.013476 | −0.001072 | 0.028231 | −0.009418 | 0.017475 | 0.025124 |
| 164 | 0.053195 | −0.000033 | 0.003259 | 0.006744 | −0.004165 | −0.009595 | 0.004743 | −0.009576 | −0.01972 | −0.004629 | −0.064841 | −0.010331 | −0.002999 | −0.007865 |
| 165 | 0.022674 | −0.062962 | −0.000092 | 0.010555 | −0.022497 | 0.042842 | 0.031332 | −0.006589 | 0.048624 | −0.031833 | −0.011851 | 0.003815 | −0.011897 | −0.008386 |
| 166 | −0.020467 | −0.039268 | 0.006611 | 0.013704 | 0.020301 | 0.024517 | 0.002181 | 0.033437 | −0.037989 | 0.023414 | −0.005446 | −0.051959 | 0.036823 | −0.034713 |
| 167 | −0.03072 | 0.035909 | 0.006548 | −0.024497 | 0.001396 | 0.003254 | −0.017942 | 0.026979 | −0.015953 | −0.031708 | 0.02829 | 0.009191 | 0.02566 | −0.022352 |
| 168 | −0.00752 | −0.01781 | −0.015087 | 0.001904 | −0.009619 | −0.042087 | 0.015453 | −0.030217 | 0.012662 | 0.030547 | −0.000793 | −0.006721 | −0.033696 | 0.039246 |
| 169 | 0.002267 | 0.005541 | −0.005494 | −0.027143 | 0.016675 | 0.003221 | −0.03827 | 0.020918 | −0.011383 | 0.008597 | −0.007644 | −0.005205 | 0.003109 | −0.015693 |
| 170 | 0.008856 | 0.001371 | −0.011359 | −0.020384 | 0.015546 | 0.007797 | −0.041658 | 0.03136 | −0.000768 | 0.03198 | 0.003461 | −0.003015 | −0.009031 | −0.002944 |
| 171 | 0.005895 | 0.017852 | 0.029388 | −0.01032 | 0.016424 | −0.004704 | −0.009671 | 0.052001 | 0.010946 | 0.027234 | −0.042486 | 0.020272 | −0.012602 | −0.008927 |
| 172 | −0.01269 | −0.000471 | −0.01426 | 0.002986 | −0.004876 | 0.009604 | 0.009925 | −0.025985 | −0.020023 | −0.015824 | 0.020274 | −0.002655 | 0.00963 | −0.030586 |
| 173 | −0.010554 | −0.01151 | −0.005412 | 0.00193 | −0.008759 | 0.014728 | 0.009347 | −0.036698 | −0.004233 | −0.016071 | −0.0053 | −0.012061 | 0.013281 | −0.00918 |
| 174 | −0.019531 | 0.000954 | −0.009344 | 0.018863 | 0.007696 | 0.028663 | 0.017998 | −0.033128 | −0.002372 | −0.009974 | 0.023864 | −0.029018 | 0.005621 | −0.015093 |
| 175 | −0.013858 | 0.005615 | 0.000001 | 0.010985 | 0.014638 | 0.020169 | 0.009984 | −0.032028 | −0.029574 | 0.008785 | −0.009754 | −0.025465 | 0.009356 | −0.015779 |
| 176 | −0.020171 | −0.026472 | −0.018797 | −0.007873 | −0.011682 | −0.03802 | −0.000491 | −0.011908 | −0.010845 | 0.024141 | 0.007089 | 0.007466 | −0.045603 | −0.019099 |
| 177 | −0.037738 | −0.005188 | 0.025434 | 0.022445 | 0.00827 | 0.007442 | 0.012847 | −0.005171 | −0.025367 | −0.048138 | −0.001564 | −0.002544 | 0.008136 | −0.008405 |
| 178 | −0.014204 | 0.037707 | 0.013283 | −0.044293 | 0.014079 | −0.024494 | −0.038288 | 0.01289 | −0.012456 | 0.00039 | −0.011864 | −0.036393 | −0.032462 | 0.010921 |
| 179 | −0.001116 | 0.005747 | 0.004551 | −0.050248 | 0.002716 | −0.028236 | −0.043469 | 0.014455 | 0.016254 | 0.014823 | −0.016231 | 0.002367 | −0.002388 | 0.000303 |
| 180 | −0.002 | −0.00094 | 0.006606 | −0.048542 | 0.004253 | −0.019319 | −0.049452 | 0.017953 | 0.006392 | 0.016828 | −0.012507 | 0.001921 | −0.002237 | −0.002626 |
| 181 | −0.000069 | 0.007046 | 0.005941 | −0.050482 | 0.005311 | −0.022085 | −0.050889 | 0.016513 | 0.006558 | 0.014708 | −0.009205 | 0.000161 | −0.005283 | −0.006567 |
| 182 | 0.001869 | −0.00587 | −0.00011 | −0.033633 | −0.007738 | −0.043319 | −0.028014 | −0.00722 | 0.007168 | 0.017326 | −0.002305 | 0.008779 | −0.004783 | 0.013728 |
| 183 | 0.001492 | 0.003772 | 0.031341 | −0.023441 | 0.001063 | −0.057581 | 0.000392 | 0.000845 | 0.032879 | 0.019455 | −0.056105 | 0.021234 | −0.004723 | 0.015968 |
| 184 | −0.022275 | 0.00291 | 0.020368 | −0.007969 | 0.012942 | −0.046021 | 0.006606 | −0.005541 | 0.022887 | 0.022708 | 0.002629 | −0.00524 | 0.005279 | 0.002213 |
| 185 | −0.014925 | −0.027686 | −0.011219 | 0.00456 | −0.002899 | −0.012697 | 0.006358 | −0.040547 | −0.019479 | −0.023665 | 0.032665 | −0.010529 | 0.010574 | 0.027607 |
| 186 | −0.040645 | 0.006943 | 0.036088 | 0.032949 | 0.01331 | 0.007004 | 0.041616 | 0.00137 | −0.009392 | −0.004627 | −0.00242 | 0.002676 | 0.018298 | 0.026122 |
| 187 | −0.017702 | −0.014926 | −0.011681 | −0.002126 | −0.006048 | −0.021201 | 0.003622 | −0.071918 | −0.007887 | −0.014081 | −0.007977 | 0.006596 | 0.034732 | 0.010036 |
| 188 | −0.001991 | −0.024018 | −0.019146 | 0.01329 | −0.003311 | −0.01037 | 0.015127 | −0.088424 | 0.004776 | 0.004329 | 0.01269 | −0.011724 | 0.018521 | −0.005503 |
| 189 | −0.004343 | −0.02512 | −0.026973 | −0.007552 | 0.007456 | −0.047974 | −0.00922 | −0.109633 | −0.002655 | 0.027416 | −0.015692 | 0.003845 | 0.03694 | −0.02859 |
| 190 | 0.004439 | 0.014789 | −0.002032 | −0.013046 | 0.000624 | −0.015286 | −0.032002 | 0.041007 | −0.018146 | −0.008536 | −0.012994 | 0.012404 | 0.000743 | 0.017037 |
| 191 | 0.002431 | 0.001592 | −0.007509 | −0.012653 | −0.00009 | −0.01363 | −0.030244 | 0.012665 | −0.007833 | −0.042838 | −0.005899 | 0.035821 | 0.017889 | 0.02367 |
| 192 | −0.01032 | 0.002998 | −0.008373 | −0.004409 | −0.011671 | −0.024239 | 0.020583 | −0.028144 | 0.013611 | −0.010268 | 0.004205 | −0.00189 | 0.006977 | 0.044821 |
| 193 | −0.031864 | 0.002139 | 0.012359 | 0.014466 | 0.003304 | −0.020357 | 0.026784 | −0.034731 | −0.009761 | 0.019791 | 0.005309 | −0.009983 | −0.006281 | 0.044391 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 194 | −0.00262 | 0.002351 | −0.002738 | 0.000382 | −0.003905 | −0.003747 | 0.004898 | −0.059232 | −0.009222 | 0.015988 | −0.026195 | 0.002892 | 0.009823 | −0.009692 |
| 195 | −0.033819 | 0.020725 | −0.019975 | −0.006575 | −0.001808 | 0.007099 | −0.013612 | 0.006839 | −0.014454 | −0.0143 | 0.006317 | 0.016936 | 0.021249 | −0.023313 |
| 196 | −0.017091 | 0.005261 | −0.009827 | −0.019482 | 0.002517 | −0.006414 | −0.033051 | 0.009115 | −0.003697 | −0.007067 | 0.017144 | 0.007228 | 0.024703 | −0.016277 |
| 197 | 0.007217 | −0.009624 | −0.009173 | −0.002801 | −0.009411 | −0.013475 | −0.01744 | 0.035515 | −0.016579 | −0.038849 | −0.008817 | 0.040165 | 0.01428 | 0.030355 |
| 198 | −0.045199 | 0.041127 | −0.005733 | 0.01987 | 0.00736 | 0.010694 | 0.026744 | −0.007557 | −0.023803 | −0.00962 | 0.002759 | −0.016674 | −0.002614 | −0.013216 |
| 199 | 0.024934 | 0.032199 | −0.03397 | −0.01391 | 0.004992 | 0.013839 | −0.025471 | 0.009865 | −0.053138 | 0.000347 | −0.026632 | −0.042466 | 0.00881 | 0.018082 |
| 200 | −0.012875 | 0.01573 | 0.030601 | 0.010038 | 0.001135 | 0.00231 | 0.035445 | 0.011096 | −0.006767 | −0.011378 | −0.055733 | 0.013086 | −0.004601 | −0.031651 |
| 201 | −0.018386 | −0.032203 | −0.006733 | −0.008439 | −0.027888 | −0.027911 | −0.025442 | −0.011387 | 0.035909 | −0.029896 | −0.054865 | 0.061725 | −0.052777 | −0.018045 |
| 202 | −0.02639 | −0.006419 | 0.026189 | 0.010999 | 0.000337 | 0.024995 | 0.026339 | 0.007488 | 0.017495 | 0.004844 | −0.029212 | −0.011724 | −0.00252 | 0.006458 |
| 203 | 0.036855 | 0.006213 | −0.002607 | 0.003033 | 0.016999 | −0.005955 | 0.00705 | 0.015268 | −0.017097 | −0.003323 | −0.044671 | −0.031588 | 0.028653 | 0.030769 |
| 204 | −0.000213 | −0.020144 | 0.01248 | −0.016599 | −0.020571 | −0.013408 | 0.008975 | 0.019864 | 0.025207 | −0.018481 | 0.021295 | 0.027078 | 0.038358 | −0.002701 |
| 205 | 0.023401 | −0.053309 | −0.002903 | −0.028318 | −0.011783 | 0.013135 | −0.012854 | −0.020825 | 0.00359 | 0.008172 | 0.007561 | 0.01614 | −0.000772 | −0.025375 |
| 206 | −0.016778 | −0.001184 | 0.001395 | −0.002647 | −0.011029 | 0.000323 | −0.006833 | −0.00254 | −0.037151 | −0.02054 | 0.017457 | 0.016814 | 0.02186 | −0.078682 |
| 207 | 0.017326 | 0.014516 | 0.051728 | −0.012877 | 0.009379 | −0.024454 | −0.00232 | 0.012132 | −0.010553 | 0.000812 | 0.019707 | −0.076782 | −0.012708 | −0.028151 |
| 208 | −0.028024 | −0.040351 | 0.019655 | 0.030244 | 0.004537 | 0.025178. | 0.02524 | −0.001095 | −0.049441 | −0.014951 | 0.02201 | 0.007747 | 0.053226 | 0.010617 |
| 209 | 0.014161 | −0.048704 | −0.002761 | 0.005784 | −0.015048 | 0.001024 | 0.041618 | 0.004188 | −0.015566 | 0.012958 | 0.006922 | −0.04165 | 0.012153 | 0.00563 |
| 210 | 0.025415 | −0.01375 | 0.019851 | −0.01094 | −0.00069 | −0.022607 | 0.004211 | 0.000693 | −0.074949 | −0.036287 | −0.061222 | −0.015723 | −0.012923 | −0.024708 |
| 211 | 0.053249 | −0.014936 | −0.000714 | −0.023128 | −0.014529 | 0.005852 | −0.025864 | −0.022638 | −0.034488 | −0.046842 | −0.026457 | 0.00862 | 0.004206 | −0.022394 |
| 212 | 0.01668 | 0.029395 | −0.040118 | 0.000484 | 0.011278 | 0.015588 | −0.003414 | −0.005894 | −0.050578 | −0.000168 | −0.03367 | −0.004319 | −0.016746 | 0.003622 |
| 213 | −0.011126 | 0.019207 | −0.012093 | −0.000574 | −0.01676 | −0.003749 | −0.018274 | −0.042125 | −0.037003 | −0.017146 | 0.030816 | −0.015034 | −0.045619 | 0.000961 |
| 214 | −0.003832 | 0.005471 | 0.015629 | −0.042397 | 0.010171 | −0.046877 | −0.033089 | 0.002443 | 0.020969 | 0.019616 | −0.026488 | 0.014191 | 0.009604 | 0.009096 |
| 215 | −0.022299 | −0.029051 | 0.023042 | −0.04211 | 0.010396 | −0.02321 | −0.031985 | 0.023274 | 0.012447 | −0.018881 | −0.01598 | −0.002013 | −0.015673 | 0.008608 |
| 216 | 0.009229 | −0.007191 | 0.016768 | 0.000587 | 0.018144 | 0.005803 | −0.008019 | 0.009018 | 0.014546 | 0.020649 | −0.025702 | −0.012834 | −0.037379 | −0.041429 |
| 217 | 0.011796 | −0.003639 | −0.009352 | 0.024532 | −0.003306 | 0.004495 | 0.023741 | −0.012357 | 0.017777 | 0.004764 | 0.011647 | −0.019428 | −0.025356 | −0.017836 |
| 218 | 0.002185 | −0.00009 | 0.012511 | 0.004813 | 0.019425 | 0.008604 | 0.005901 | 0.010622 | 0.015926 | 0.014415 | 0.009484 | −0.016744 | −0.010659 | 0.005379 |
| 219 | −0.002034 | 0.035246 | 0.025159 | 0.010588 | 0.028475 | 0.013209 | 0.005859 | 0.006281 | 0.015136 | 0.018641 | 0.00635 | −0.044283 | −0.030044 | −0.04282 |
| 220 | 0.032264 | 0.029837 | −0.015853 | 0.009714 | 0.014749 | −0.01289 | 0.007939 | 0.036398 | 0.029751 | 0.003936 | −0.007099 | −0.008426 | −0.005593 | −0.003087 |
| 221 | 0.010382 | 0.002095 | 0.000865 | −0.003742 | −0.01095 | 0.006571 | 0.013828 | 0.012906 | 0.02905 | −0.015799 | −0.012632 | 0.000146 | 0.00161 | −0.027622 |
| 222 | 0.007126 | 0.003491 | 0.003875 | −0.009967 | 0.002594 | 0.00393 | 0.002091 | −0.010796 | 0.004979 | 0.001476 | 0.009379 | −0.024949 | 0.013183 | 0.007621 |
| 223 | 0.00638 | 0.025071 | 0.017029 | −0.002633 | 0.008372 | 0.005236 | 0.000554 | −0.010892 | −0.020357 | 0.005717 | −0.013257 | −0.017949 | 0.00274 | −0.00334 |
| 224 | −0.031958 | −0.020601 | −0.005623 | −0.003737 | −0.010502 | 0.02453 | −0.004989 | 0.011952 | −0.00276 | −0.013264 | −0.01816 | 0.007921 | 0.010071 | −0.020864 |
| 225 | −0.030702 | −0.00574 | −0.015734 | −0.005438 | −0.01095 | 0.034633 | −0.006213 | 0.007423 | −0.007156 | −0.016638 | −0.026221 | 0.017455 | 0.019235 | −0.011819 |
| 226 | −0.042082 | 0.000437 | −0.019453 | 0.009334 | −0.012472 | −0.008017 | 0.012113 | −0.016258 | −0.010653 | 0.008526 | −0.013315 | 0.007502 | 0.015386 | 0.014728 |
| 227 | −0.041165 | 0.002238 | −0.020611 | −0.001755 | −0.020372 | 0.008766 | −0.008059 | 0.00887 | −0.010302 | −0.018399 | −0.020508 | 0.018481 | 0.017883 | −0.019192 |
| 228 | −0.00521 | 0.009554 | −0.00198 | −0.001289 | 0.008124 | −0.008318 | 0.006205 | −0.004534 | −0.023132 | 0.026228 | −0.000459 | −0.01903 | 0.033405 | 0.036613 |
| 229 | −0.03733 | −0.008607 | −0.026143 | −0.025874 | 0.014631 | 0.004009 | −0.029136 | −0.0108 | −0.007253 | 0.007937 | 0.009576 | 0.004965 | −0.001886 | 0.023272 |
| 230 | 0.017049 | −0.015537 | 0.001323 | −0.019711 | 0.009091 | 0.011138 | −0.028804 | −0.005027 | −0.001491 | 0.007221 | −0.005079 | −0.009962 | −0.028669 | −0.003962 |
| 231 | 0.009277 | −0.025097 | −0.012337 | −0.002995 | −0.016397 | 0.008081 | −0.005564 | −0.00845 | −0.040552 | 0.007392 | 0.011082 | 0.004955 | 0.006963 | −0.011248 |
| 232 | −0.014855 | −0.014167 | 0.002794 | 0.004527 | 0.011723 | 0.00801 | 0.011783 | −0.015279 | 0.007124 | 0.009227 | −0.027213 | −0.003307 | 0.037475 | −0.016543 |
| 233 | −0.020109 | −0.001373 | 0.001175 | −0.004981 | 0.008368 | 0.007067 | 0.007606 | −0.035939 | 0.007682 | −0.022081 | −0.008415 | −0.002517 | −0.005056 | 0.016035 |
| 234 | 0.014683 | 0.014081 | 0.005445 | −0.010054 | 0.009983 | −0.005871 | −0.001644 | 0.015002 | −0.026218 | 0.00619 | −0.029237 | −0.003068 | −0.005113 | 0.005762 |
| 235 | 0.008212 | 0.010891 | −0.013244 | −0.015004 | −0.005638 | 0.003086 | 0.007567 | −0.012416 | −0.029188 | 0.005197 | 0.03226 | −0.015356 | 0.003698 | 0.017915 |
| 236 | 0.010557 | −0.048525 | 0.010382 | 0.000468 | 0.002027 | 0.000017 | 0.00287 | −0.022028 | −0.032235 | 0.016408 | −0.016241 | 0.006664 | −0.000144 | −0.053332 |
| 237 | −0.002011 | −0.027106 | 0.020838 | 0.002125 | 0.011086 | 0.000433 | −0.013027 | −0.016414 | −0.003993 | 0.004938 | −0.021481 | 0.045793 | 0.036183 | −0.003443 |
| 238 | 0.009358 | 0.010083 | 0.032204 | −0.001625 | 0.018697 | 0.017761 | −0.016253 | −0.004831 | 0.000953 | 0.007838 | −0.009915 | 0.009866 | −0.01172 | −0.019529 |
| 239 | 0.00005 | 0.020322 | 0.032556 | 0.000017 | 0.018571 | 0.016645 | 0.002036 | −0.010293 | −0.010241 | 0.011483 | 0.022873 | −0.031637 | −0.027483 | −0.00194 |
| 240 | −0.022556 | 0.001271 | 0.008526 | 0.00048 | 0.000587 | 0.015662 | −0.000561 | 0.017099 | 0.004231 | −0.014563 | −0.017349 | −0.013399 | 0.01377 | −0.001278 |
| 241 | −0.004741 | −0.009786 | 0.009241 | −0.008037 | 0.008786 | −0.000704 | 0.001776 | 0.00487 | 0.014575 | −0.009942 | −0.026307 | −0.007571 | −0.008537 | 0.012723 |
| 242 | 0.028415 | −0.019293 | 0.010766 | −0.015389 | 0.012758 | −0.00956 | −0.005062 | −0.008554 | −0.003839 | 0.018927 | −0.013822 | −0.022526 | −0.011042 | −0.009119 |
| 243 | 0.010503 | 0.011525 | 0.003473 | −0.005478 | 0.012959 | −0.002387 | −0.005433 | 0.01122 | 0.009031 | 0.004232 | 0.012085 | −0.019392 | −0.002831 | −0.011704 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 244 | 0.011138 | 0.014096 | 0.009616 | −0.000722 | −0.003514 | 0.001728 | 0.006063 | 0.018573 | 0.000827 | −0.016861 | −0.010287 | 0.011816 | −0.002062 | −0.014932 |
| 245 | 0.025474 | −0.000182 | −0.000807 | 0.000231 | 0.008333 | 0.00803 | 0.004242 | −0.023286 | −0.009866 | −0.019635 | 0.019083 | −0.031104 | −0.019885 | −0.028585 |
| 246 | 0.032029 | −0.008513 | −0.002797 | −0.006823 | 0.015666 | −0.01724 | −0.008386 | −0.006808 | 0.014221 | −0.005949 | −0.018628 | 0.001778 | 0.003829 | 0.019637 |
| 247 | 0.01989 | 0.011733 | −0.001525 | −0.009277 | 0.009356 | −0.006257 | −0.008766 | −0.0012 | −0.004793 | −0.006392 | −0.006238 | −0.020458 | −0.012912 | −0.011866 |
| 248 | 0.000467 | 0.02126 | 0.005988 | −0.006013 | 0.01342 | −0.000032 | −0.000004 | 0.00402 | −0.006163 | −0.00401 | 0.002706 | −0.005984 | 0.008841 | −0.023348 |
| 249 | 0.002241 | −0.014797 | 0.003725 | 0.010682 | 0.003419 | 0.017749 | 0.011742 | 0.016339 | 0.023805 | 0.008788 | 0.008122 | −0.007531 | 0.005222 | 0.002125 |
| 250 | −0.003254 | −0.005295 | 0.017649 | −0.002767 | −0.000722 | −0.006248 | −0.004761 | 0.029842 | 0.009072 | −0.011774 | −0.044264 | 0.021586 | 0.01077 | 0.002879 |
| 251 | −0.011546 | 0.010787 | 0.022799 | 0.000279 | 0.000046 | 0.001128 | 0.007531 | 0.01992 | −0.000295 | −0.019231 | −0.037167 | 0.009916 | 0.028065 | 0.01781 |
| 252 | 0.015303 | 0.001726 | 0.006823 | −0.011837 | 0.003102 | −0.012253 | 0.004383 | 0.015064 | 0.004074 | −0.008057 | −0.027004 | −0.009138 | 0.003784 | 0.003058 |
| 253 | 0.018432 | −0.018154 | −0.014757 | −0.006052 | 0.000352 | 0.002891 | −0.00817 | 0.018495 | 0.017572 | 0.01974 | −0.034346 | 0.018592 | −0.014261 | −0.011101 |
| 254 | 0.005883 | 0.022999 | 0.005018 | 0.00487 | 0.00585 | 0.00748 | −0.000401 | −0.000264 | −0.031614 | −0.012555 | 0.009133 | −0.006179 | 0.005989 | 0.001205 |
| 255 | 0.027977 | 0.017995 | −0.008991 | 0.005199 | −0.000564 | −0.002126 | 0.002184 | 0.021119 | 0.003765 | −0.028213 | −0.015855 | 0.006936 | 0.002012 | 0.000099 |
| 256 | 0.027107 | −0.021171 | −0.032529 | 0.010432 | −0.006367 | 0.00251 | 0.01066 | 0.03429 | 0.05311 | −0.033146 | 0.007636 | −0.000076 | −0.029289 | −0.000058 |
| 257 | 0.006355 | 0.003451 | −0.030333 | −0.007971 | −0.039058 | 0.000039 | −0.007945 | 0.014112 | 0.02862 | −0.010547 | 0.019326 | 0.008774 | −0.026455 | −0.014021 |
| 258 | −0.006736 | 0.002181 | −0.040515 | −0.009331 | −0.032423 | 0.000775 | −0.011727 | −0.005992 | −0.029431 | −0.016693 | 0.016216 | −0.006149 | −0.013004 | −0.007783 |
| 259 | 0.00322 | −0.001976 | 0.02089 | −0.002094 | 0.006359 | 0.001499 | 0.00472 | 0.009013 | −0.0008 | 0.00371 | −0.00374 | −0.002539 | 0.026066 | 0.010547 |
| 260 | −0.014237 | 0.021066 | 0.01753 | −0.021739 | 0.009639 | −0.021371 | −0.00184 | 0.011213 | −0.024358 | 0.02236 | −0.016746 | −0.011039 | 0.049494 | 0.013669 |
| 261 | −0.023263 | 0.000332 | −0.000449 | −0.012636 | −0.001329 | −0.019134 | −0.010185 | 0.008634 | −0.024664 | 0.004104 | −0.015304 | 0.005095 | 0.036415 | 0.010239 |
| 262 | 0.006764 | −0.01699 | 0.004454 | −0.009754 | 0.001219 | −0.006813 | −0.004039 | 0.001804 | −0.001979 | 0.015284 | −0.005732 | −0.016899 | −0.004508 | −0.013561 |
| 263 | 0.022836 | −0.014952 | 0.00465 | −0.008456 | −0.003151 | −0.009735 | 0.002308 | −0.003645 | 0.007344 | 0.011296 | −0.005504 | −0.00621 | −0.006348 | −0.018177 |
| 264 | 0.001909 | −0.006003 | 0.000883 | −0.001974 | 0.002456 | −0.010133 | 0.005569 | 0.014858 | 0.017445 | 0.008134 | 0.018283 | 0.00649 | 0.021129 | 0.019021 |
| 265 | −0.005105 | 0.011229 | −0.020017 | 0.007626 | −0.001101 | −0.009929 | 0.001388 | 0.013318 | −0.008391 | −0.004549 | 0.012041 | 0.014132 | 0.022933 | 0.016693 |
| 266 | 0.002418 | 0.012688 | −0.03071 | 0.010017 | −0.005006 | −0.011227 | −0.003017 | −0.005733 | −0.038834 | −0.021772 | −0.007517 | 0.014636 | 0.017112 | −0.00348 |
| 267 | −0.044301 | −0.021785 | −0.017368 | 0.004155 | 0.007644 | 0.000674 | −0.004404 | 0.020986 | 0.00147 | 0.027559 | −0.017757 | 0.011529 | −0.007623 | −0.007112 |
| 268 | −0.017924 | −0.008245 | −0.019665 | 0.005709 | −0.012409 | −0.006052 | 0.011904 | −0.000591 | −0.002492 | −0.002299 | −0.023222 | 0.006072 | 0.009876 | 0.012381 |
| 269 | −0.021747 | −0.006573 | −0.016593 | 0.002224 | −0.013979 | −0.004835 | 0.004072 | −0.002899 | 0.003959 | 0.001065 | −0.022708 | 0.014638 | 0.016429 | 0.0049 |
| 270 | −0.03059 | 0.013126 | −0.015334 | 0.008919 | −0.012614 | −0.008398 | 0.008426 | 0.007131 | −0.007683 | 0.003015 | −0.006893 | 0.000321 | 0.017045 | 0.006965 |
| 271 | −0.035339 | −0.021412 | −0.011182 | −0.005521 | −0.007031 | −0.029235 | 0.005778 | −0.037066 | −0.013122 | 0.016249 | −0.010888 | 0.013721 | −0.013578 | −0.008414 |
| 272 | −0.050988 | 0.000089 | −0.022556 | −0.011257 | 0.010679 | 0.003159 | −0.015118 | −0.001764 | −0.013785 | 0.015607 | 0.03165 | −0.008541 | −0.003968 | 0.019481 |
| 273 | −0.000951 | 0.004298 | −0.010307 | −0.007101 | −0.00128 | 0.006631 | −0.000743 | 0.018186 | 0.009423 | 0.002795 | 0.0244 | −0.010655 | 0.001687 | 0.023599 |
| 274 | −0.00355 | 0.003834 | −0.014883 | −0.008875 | −0.004809 | 0.004631 | −0.004303 | 0.01492 | 0.010347 | 0.006468 | 0.026422 | −0.006699 | 0.000856 | 0.020494 |
| 275 | −0.016373 | 0.014525 | 0.006519 | −0.00416 | 0.007701 | −0.006017 | −0.010026 | 0.005044 | −0.017356 | 0.012092 | 0.032119 | −0.02051 | −0.000937 | −0.018502 |
| 276 | −0.006961 | −0.049032 | −0.003613 | −0.010393 | 0.0049 | 0.001753 | −0.00998 | −0.020414 | −0.042517 | 0.019064 | −0.001377 | −0.002691 | −0.003417 | −0.046583 |
| 277 | −0.017646 | −0.013227 | 0.015379 | 0.001448 | 0.010863 | 0.010346 | 0.000755 | −0.024361 | −0.034241 | 0.021329 | 0.032185 | −0.0063 | 0.019268 | 0.009933 |
| 278 | −0.036654 | −0.007702 | 0.028354 | 0.004406 | 0.010392 | 0.008338 | 0.008242 | −0.029733 | −0.043523 | 0.025404 | 0.03711 | −0.002036 | 0.021329 | 0.019403 |
| 279 | −0.018392 | 0.034053 | 0.043135 | 0.003259 | 0.026013 | 0.012309 | 0.006066 | −0.003853 | −0.017506 | 0.027727 | 0.027625 | −0.038673 | −0.01174 | −0.003024 |
| 280 | 0.012714 | −0.036345 | −0.030064 | 0.003525 | −0.001915 | 0.007309 | −0.004047 | 0.004343 | 0.021921 | 0.001749 | 0.011835 | −0.000095 | −0.00996 | −0.015324 |
| 281 | 0.013013 | −0.008829 | −0.019866 | 0.004575 | 0.00231 | −0.021787 | 0.005571 | −0.014237 | −0.0205 | −0.011772 | 0.002505 | −0.0154 | 0.004755 | 0.051532 |
| 282 | 0.004756 | −0.00109 | −0.017308 | −0.000139 | −0.012224 | −0.020244 | 0.009446 | −0.011387 | −0.019667 | −0.017278 | 0.010419 | −0.016872 | −0.009865 | 0.054354 |
| 283 | −0.01673 | 0.032005 | 0.017818 | 0.001297 | 0.016601 | −0.017908 | 0.011945 | 0.003834 | −0.018996 | 0.01066 | 0.015225 | −0.030348 | −0.00586 | 0.00573 |
| 284 | −0.004777 | −0.000976 | −0.019569 | −0.003911 | −0.031819 | −0.004492 | 0.000815 | 0.023028 | 0.028075 | −0.002315 | 0.016883 | 0.007947 | −0.015131 | 0.00134 |
| 285 | −0.000203 | 0.005937 | −0.010305 | −0.004414 | −0.034307 | −0.005923 | 0.003445 | 0.023173 | 0.03211 | −0.001875 | 0.012021 | 0.00971 | −0.023147 | 0.006662 |
| 286 | −0.013491 | 0.004127 | −0.044926 | −0.006861 | −0.04706 | −0.005132 | −0.011194 | −0.008981 | −0.010662 | −0.024292 | 0.019451 | −0.00147 | −0.02803 | 0.007117 |
| 287 | −0.02353 | 0.01696 | −0.035987 | −0.004646 | −0.04114 | −0.00839 | −0.006492 | −0.014727 | −0.017341 | −0.022991 | 0.025092 | −0.007315 | −0.026774 | 0.010238 |
| 288 | −0.022717 | −0.004076 | −0.017797 | −0.001362 | −0.013287 | −0.023952 | 0.002608 | −0.019212 | −0.03001 | −0.001865 | −0.002982 | −0.002649 | 0.009438 | 0.016715 |
| 289 | −0.006149 | −0.001083 | −0.019265 | 0.001713 | −0.004092 | −0.012584 | 0.008268 | 0.002486 | −0.018977 | 0.008247 | 0.004244 | −0.011874 | −0.006801 | −0.003619 |
| 290 | 0.015001 | 0.000571 | 0.013159 | 0.017202 | 0.005977 | −0.022383 | 0.012462 | −0.001681 | 0.012206 | −0.007295 | −0.020832 | 0.014051 | 0.007524 | 0.016696 |
| 291 | 0.012064 | 0.000584 | 0.01233 | 0.016834 | 0.004216 | −0.021078 | 0.010594 | −0.000551 | 0.01161 | −0.009184 | −0.014944 | 0.012258 | 0.007804 | 0.0116 |
| 292 | 0.019593 | −0.000515 | 0.015074 | 0.012956 | 0.006023 | −0.022423 | 0.005993 | −0.008409 | 0.016038 | −0.0114 | −0.023042 | 0.009158 | 0.004658 | 0.013824 |
| 293 | −0.000613 | −0.071106 | −0.003477 | 0.009704 | −0.022728 | 0.005266 | 0.026289 | −0.021139 | −0.003529 | −0.027324 | −0.014381 | 0.005549 | −0.005207 | −0.025824 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 294 | 0.000639 | −0.021852 | −0.008192 | 0.00574 | −0.008043 | −0.004542 | 0.01566 | −0.011452 | −0.019034 | −0.005454 | 0.001809 | −0.010405 | 0.008271 | 0.013211 |
| 295 | 0.027261 | −0.02783 | −0.009297 | 0.003428 | −0.009244 | 0.013445 | 0.006625 | 0.012576 | 0.018757 | −0.007847 | 0.032549 | −0.01943 | −0.02038 | 0.015391 |
| 296 | 0.021402 | 0.023694 | −0.025197 | 0.001849 | 0.003062 | 0.00396 | −0.000254 | −0.006304 | −0.012023 | 0.011764 | 0.014672 | −0.043811 | 0.008994 | 0.045532 |
| 297 | 0.030589 | −0.033405 | −0.012993 | −0.001311 | −0.007028 | 0.015039 | 0.000839 | 0.010462 | 0.004019 | −0.001157 | 0.032671 | −0.036357 | −0.025116 | 0.02053 |
| 298 | 0.039195 | 0.024766 | 0.016098 | 0.003102 | 0.002189 | −0.020261 | −0.009918 | −0.016236 | −0.02124 | −0.012301 | −0.038803 | −0.016545 | 0.006121 | −0.032311 |
| 299 | 0.012554 | −0.023734 | −0.008421 | 0.014967 | −0.009129 | 0.015407 | 0.008634 | −0.001195 | −0.039613 | −0.03104 | −0.007552 | −0.013906 | 0.007238 | 0.009498 |
| 300 | −0.02521 | 0.008401 | −0.014746 | −0.034954 | −0.007035 | −0.018382 | −0.070734 | −0.006763 | −0.019911 | 0.00206 | 0.046001 | 0.01675 | −0.011355 | −0.000465 |
| 301 | 0.022241 | −0.016643 | 0.010024 | 0.009718 | −0.009686 | 0.006043 | 0.016998 | 0.017645 | 0.010106 | −0.010164 | −0.007612 | −0.000016 | −0.008663 | 0.008138 |
| 302 | 0.010013 | 0.006691 | −0.000417 | 0.013984 | −0.005975 | 0.003398 | 0.009883 | 0.007559 | −0.00127 | −0.005506 | 0.024003 | −0.023123 | −0.012695 | 0.01003 |
| 303 | −0.012821 | 0.020995 | −0.013211 | 0.008385 | −0.009206 | 0.016077 | −0.006757 | −0.012433 | −0.058753 | −0.027984 | −0.00111 | −0.030657 | 0.010603 | 0.005807 |
| 304 | −0.017046 | 0.019155 | −0.002501 | 0.024755 | 0.001345 | 0.022351 | 0.005036 | −0.007828 | −0.059783 | −0.035291 | −0.019977 | −0.018665 | 0.017525 | 0.012152 |
| 305 | −0.014267 | −0.043082 | −0.015938 | 0.021669 | −0.03525 | −0.030261 | 0.033396 | −0.034445 | 0.028286 | −0.026649 | 0.023911 | 0.019264 | −0.024035 | 0.003636 |
| 306 | 0.00412 | 0.008448 | 0.000641 | −0.003911 | −0.010918 | 0.015531 | 0.007225 | 0.081391 | 0.030755 | 0.01559 | −0.003013 | 0.009438 | −0.009916 | 0.001352 |
| 307 | 0.032916 | 0.042342 | −0.007814 | −0.003277 | −0.004405 | 0.035767 | −0.010626 | 0.022541 | −0.04433 | 0.046585 | −0.016196 | 0.000907 | −0.013117 | 0.00522 |
| 308 | 0.062186 | 0.063384 | −0.003557 | −0.016493 | 0.032323 | 0.011602 | −0.000048 | −0.004427 | 0.049353 | 0.007684 | −0.109408 | −0.002687 | 0.010153 | 0.054484 |
| 309 | 0.01383 | −0.011365 | 0.000215 | 0.018216 | −0.015955 | 0.008937 | 0.005198 | −0.01329 | −0.007204 | 0.008255 | 0.00857 | −0.003385 | −0.008258 | 0.002593 |
| 310 | 0.020481 | −0.006114 | −0.015026 | 0.017897 | −0.030256 | −0.009833 | 0.008617 | −0.008788 | −0.020641 | 0.004814 | 0.001293 | −0.007912 | −0.028367 | −0.01449 |
| 311 | 0.027793 | 0.001288 | 0.000231 | 0.000717 | −0.00673 | 0.011711 | 0.002258 | 0.004333 | 0.009128 | 0.009865 | −0.025249 | 0.001307 | −0.001253 | −0.002815 |
| 312 | 0.002132 | 0.040168 | −0.021799 | −0.007679 | 0.038486 | 0.007089 | −0.031883 | −0.038076 | 0.012823 | −0.007508 | 0.003047 | −0.073641 | −0.012211 | 0.005925 |
| 313 | 0.008346 | 0.007996 | −0.018232 | −0.007458 | −0.013609 | 0.00807 | −0.013418 | 0.011314 | 0.017861 | −0.007844 | −0.008319 | 0.013448 | −0.009198 | 0.001347 |
| 314 | 0.038927 | −0.033216 | 0.009715 | −0.000591 | 0.005154 | −0.000624 | 0.003084 | −0.010727 | −0.05247 | −0.008261 | 0.018046 | −0.057977 | −0.018884 | −0.00557 |
| 315 | 0.015629 | −0.012609 | −0.031049 | 0.000678 | −0.025924 | 0.000812 | −0.014646 | −0.024911 | −0.015069 | −0.006986 | −0.009229 | −0.003317 | −0.006294 | 0.013241 |
| 316 | 0.015203 | 0.025045 | −0.003062 | 0.002687 | −0.008475 | 0.016517 | −0.008517 | 0.06093 | 0.067893 | 0.006677 | 0.039991 | 0.009883 | 0.01466 | −0.054063 |
| 317 | 0.015539 | −0.001339 | −0.006316 | 0.002977 | −0.023729 | −0.000603 | −0.003326 | −0.015665 | −0.003204 | 0.010648 | 0.018676 | −0.003809 | −0.009301 | 0.004931 |
| 318 | 0.020682 | −0.002058 | 0.01314 | 0.01254 | −0.017409 | 0.009338 | 0.015832 | −0.028678 | −0.042749 | 0.007069 | −0.034721 | 0.019165 | 0.019096 | −0.001904 |
| 319 | 0.009199 | −0.000365 | −0.024511 | 0.000636 | −0.030835 | 0.011751 | −0.01303 | −0.020312 | −0.02516 | −0.003147 | 0.010582 | 0.003564 | 0.001396 | 0.009608 |
| 320 | 0.012331 | 0.034569 | −0.021313 | 0.012845 | −0.018046 | 0.023365 | 0.013114 | −0.004015 | −0.00922 | −0.02336 | 0.038558 | −0.013563 | 0.007103 | 0.017219 |
| 321 | 0.048592 | −0.01277 | −0.004538 | −0.001248 | −0.003719 | −0.003502 | 0.010382 | 0.054276 | −0.011679 | 0.007647 | −0.020564 | −0.012043 | 0.013402 | 0.057656 |
| 722 | 0.036311 | −0.014272 | −0.007852 | 0.019427 | 0.003592 | −0.018361 | 0.018723 | −0.028431 | −0.011378 | 0.004205 | −0.014019 | 0.02186 | 0.004101 | 0.023647 |
| 323 | 0.076036 | −0.003387 | 0.001861 | 0.000606 | −0.003406 | 0.004494 | −0.009318 | 0.059351 | 0.029184 | −0.004762 | −0.060112 | 0.018886 | −0.001134 | −0.010651 |
| 324 | −0.020025 | 0.049235 | 0.013918 | 0.007962 | 0.01423 | −0.020995 | 0.024306 | 0.010819 | −0.043617 | 0.00258 | −0.001862 | −0.018157 | 0.023814 | −0.003472 |
| 325 | −0.00825 | 0.005955 | −0.017926 | −0.005959 | −0.008469 | −0.014569 | −0.008622 | −0.013017 | −0.016823 | 0.022817 | 0.014253 | −0.017968 | 0.014031 | 0.019838 |
| 326 | −0.017867 | 0.007717 | −0.007829 | −0.005934 | −0.004632 | −0.012037 | −0.014448 | −0.025583 | 0.011526 | 0.010061 | 0.023503 | −0.025922 | 0.001424 | −0.022977 |
| 327 | 0.018797 | 0.012883 | −0.011988 | 0.001848 | −0.010453 | −0.001354 | −0.007639 | −0.010034 | −0.011807 | −0.011252 | −0.005465 | 0.000425 | 0.01219 | 0.00461 |
| 328 | 0.063557 | −0.042727 | −0.029197 | 0.002777 | −0.013055 | −0.0165091 | 0.0100881 | −0.0212681 | 0.0991291 | 0.0247261 | −0.006719 | −0.008164 | −0.018388 | 0.030688 |
| 329 | 0.037157 | 0.004765 | −0.020841 | −0.007103 | −0.01682 | −0.003219 | −0.012366 | −0.008407 | 0.01348 | −0.012319 | −0.004065 | −0.001032 | 0.004958 | −0.006327 |
| 330 | −0.051052 | −0.026501 | 0.006662 | −0.02275 | 0.001203 | −0.051058 | −0.02036 | −0.022613 | −0.013146 | −0.019873 | 0.041151 | 0.000491 | 0.010717 | 0.018034 |
| 331 | 0.010239 | 0.001026 | −0.018555 | −0.000538 | −0.010302 | −0.00282 | −0.008058 | −0.007249 | −0.007519 | −0.008824 | −0.010839 | −0.017039 | 0.000604 | −0.009279 |
| 332 | −0.019029 | −0.019463 | −0.007108 | −0.008354 | −0.004042 | 0.009588 | −0.009162 | 0.003787 | 0.018705 | 0.026163 | 0.04844 | −0.003544 | −0.008728 | 0.009146 |
| 333 | 0.005618 | −0.002278 | −0.006628 | 0.001664 | −0.012044 | 0.00251 | −0.003289 | 0.003721 | −0.006039 | 0.008826 | −0.000234 | −0.005197 | 0.005708 | 0.001697 |
| 334 | 0.001577 | −0.016756 | −0.004755 | −0.024987 | −0.009875 | −0.024653 | −0.018922 | −0.031629 | 0.024647 | −0.02947 | −0.014091 | −0.017305 | −0.01569 | 0.028616 |
| 335 | −0.000063 | 0.016562 | −0.012269 | 0.004856 | −0.010137 | 0.01029 | −0.001299 | 0.005825 | −0.020184 | −0.002221 | 0.001395 | 0.011503 | 0.013534 | −0.00826 |
| 336 | 0.003713 | 0.002328 | 0.026124 | 0.019605 | 0.008562 | 0.000486 | 0.003068 | 0.03123 | −0.007213 | −0.014736 | −0.04336 | −0.003512 | −0.010799 | 0.018164 |
| 337 | 0.016824 | 0.022508 | −0.01672 | 0.010272 | −0.008013 | 0.000859 | 0.006556 | 0.026148 | 0.009134 | −0.008104 | −0.017688 | 0.001156 | 0.012821 | 0.02742 |
| 338 | 0.026725 | 0.015895 | 0.013819 | 0.007906 | 0.000974 | 0.013563 | 0.008352 | −0.041195 | −0.008874 | −0.020732 | −0.06058 | −0.00762 | 0.003067 | −0.023011 |
| 339 | 0.022538 | −0.013246 | 0.020733 | 0.000778 | −0.000189 | 0.004715 | 0.006763 | 0.013619 | 0.029477 | 0.034225 | −0.022994 | −0.032343 | −0.004358 | 0.017919 |
| 340 | −0.039217 | −0.005554 | −0.025004 | −0.003148 | −0.028146 | −0.01304 | −0.009686 | −0.030437 | −0.00622 | −0.049902 | 0.054791 | −0.010339 | 0.014944 | −0.039706 |

APPENDIX B3-continued

PCA Transformation
Matrix (340 × 340 Early/Late)

| | DF | DG | DH | DI | DJ | DK | DL | DM | DN | DO | DP | DQ | DR | DS |
|---|---|---|---|---|---|---|---|---|---|---|---|---|---|---|
| 1 | −0.064118 | −0.083274 | −0.023388 | 0.000836 | 0.012589 | −0.031041 | 0.046117 | −0.009486 | −0.027035 | 0.011334 | 0.074871 | 0.048013 | −0.073623 | 0.001608 |
| 2 | −0.064697 | 0.058843 | 0.038761 | 0.004794 | −0.104332 | −0.154301 | 0.017825 | 0.037827 | 0.068333 | −0.012234 | −0.040054 | 0.037146 | 0.091929 | −0.056487 |
| 3 | 0.001054 | 0.047588 | −0.034857 | −0.163239 | 0.01488 | −0.001919 | −0.075607 | −0.074957 | −0.05857 | −0.071884 | −0.10508 | 0.001632 | 0.076243 | −0.020814 |
| 4 | −0.01454 | −0.007606 | 0.02831 | 0.116767 | −0.075935 | 0.000798 | 0.018099 | −0.083956 | 0.07073 | −0.061709 | 0.033928 | −0.002472 | −0.02964 | 0.00277 |
| 5 | 0.047706 | −0.010224 | 0.08063 | −0.008581 | 0.077045 | −0.009276 | −0.046822 | 0.13336 | −0.049616 | 0.144311 | −0.070395 | −0.014332 | −0.000279 | 0.088461 |
| 6 | 0.023932 | 0.065692 | 0.066706 | −0.121143 | 0.041308 | −0.001917 | 0.009015 | 0.069811 | 0.018003 | 0.008878 | 0.052282 | 0.054829 | 0.06531 | −0.022807 |
| 7 | 0.02233 | 0.039826 | −0.03717 | 0.024361 | −0.055926 | −0.070579 | −0.019379 | 0.069619 | −0.035367 | −0.056407 | −0.134706 | −0.011927 | 0.023759 | 0.058317 |
| 8 | 0.002555 | −0.046623 | 0.06332 | −0.047124 | 0.023427 | −0.029056 | 0.000363 | 0.0024 | −0.052467 | −0.03711 | −0.088312 | −0.076687 | 0.04648 | −0.136115 |
| 9 | 0.008684 | 0.027447 | −0.012984 | 0.00896 | −0.0259 | −0.187388 | 0.040703 | −0.044774 | −0.108426 | −0.017322 | 0.03801 | −0.096225 | 0.014449 | 0.059489 |
| 10 | 0.051231 | 0.168378 | −0.03405 | 0.007059 | 0.065173 | −0.022808 | 0.149473 | −0.007361 | −0.118622 | 0.094217 | 0.141125 | −0.007997 | −0.02969 | −0.009158 |
| 11 | 0.152543 | 0.024023 | −0.019564 | 0.074069 | 0.080058 | 0.015468 | −0.018024 | 0.133706 | −0.08484 | −0.057915 | −0.028106 | −0.074652 | −0.020206 | −0.027386 |
| 12 | 0.089001 | −0.050898 | −0.014491 | 0.004672 | 0.038507 | −0.047947 | −0.027608 | −0.034694 | −0.000576 | 0.052087 | 0.071115 | 0.027167 | 0.040359 | 0.009567 |
| 13 | −0.001027 | −0.055333 | 0.084128 | 0.032502 | 0.026888 | −0.090988 | 0.012184 | 0.065142 | −0.075984 | −0.0647 | 0.001901 | −0.030737 | −0.080862 | −0.000144 |
| 14 | −0.056871 | 0.073898 | −0.029998 | 0.113428 | −0.096865 | 0.022587 | 0.068967 | 0.089714 | 0.041315 | 0.022147 | 0.058611 | 0.017725 | 0.069598 | 0.001187 |
| 15 | −0.074728 | 0.006685 | −0.041166 | 0.007551 | −0.011364 | −0.032101 | −0.002202 | −0.135951 | 0.131864 | 0.041937 | −0.028778 | 0.001877 | −0.108462 | 0.041621 |
| 16 | 0.076157 | 0.073663 | 0.070445 | −0.096357 | 0.082095 | −0.00201 | 0.04864 | −0.019468 | −0.061893 | 0.04751 | −0.021562 | −0.025797 | −0.082959 | 0.011942 |
| 17 | −0.173419 | 0.023254 | 0.06433 | −0.02069 | −0.023772 | −0.084888 | −0.018092 | 0.009477 | −0.028294 | −0.046927 | −0.096498 | −0.104993 | −0.193323 | −0.06675 |
| 18 | −0.078815 | 0.057638 | 0.072897 | 0.036657 | 0.025065 | −0.024167 | −0.075838 | −0.032128 | 0.05456 | −0.034259 | 0.014988 | 0.013211 | −0.037236 | 0.035264 |
| 19 | −0.050841 | 0.007973 | −0.085359 | 0.008584 | −0.02604 | −0.107159 | −0.094758 | 0.042608 | 0.047475 | 0.052349 | 0.003816 | 0.093249 | 0.085342 | 0.040256 |
| 20 | 0.142761 | −0.020321 | 0.015713 | 0.003222 | 0.069142 | 0.161954 | 0.01056 | −0.058193 | 0.029172 | 0.0188 | −0.028993 | −0.052594 | 0.101529 | 0.016434 |
| 21 | 0.122195 | 0.096004 | −0.020621 | −0.047316 | −0.081517 | −0.060951 | −0.060211 | −0.036255 | −0.081511 | −0.131314 | −0.002912 | −0.092783 | 0.030235 | −0.117594 |
| 22 | −0.071143 | 0.105507 | −0.087754 | −0.027594 | −0.060141 | 0.151702 | −0.086611 | −0.020838 | 0.050455 | 0.058921 | −0.014636 | −0.011072 | 0.114418 | 0.096071 |
| 23 | 0.035905 | 0.027708 | −0.03726 | 0.045543 | −0.019366 | 0.090434 | 0.042512 | 0.050252 | −0.050911 | −0.017754 | 0.028735 | 0.007211 | −0.085784 | 0.027195 |
| 24 | 0.079286 | 0.011445 | 0.004847 | −0.107323 | 0.027463 | 0.01737 | 0.011204 | −0.117685 | −0.040639 | 0.007553 | −0.044439 | 0.022017 | 0.006085 | −0.02746 |
| 25 | 0.028422 | −0.046176 | 0.038387 | 0.178784 | 0.047354 | 0.107636 | 0.006263 | 0.058541 | 0.062265 | −0.085769 | −0.002755 | 0.078276 | 0.04685 | −0.057312 |
| 26 | −0.072776 | 0.079122 | 0.024069 | 0.059892 | −0.006116 | −0.019291 | 0.00802 | −0.086832 | −0.127749 | −0.122175 | −0.003815 | −0.039451 | −0.137007 | −0.017911 |
| 27 | −0.02113 | 0.067545 | −0.011603 | −0.014637 | −0.103613 | −0.056893 | 0.060034 | −0.012942 | −0.027966 | 0.128909 | 0.005252 | −0.057779 | 0.020953 | −0.003454 |
| 28 | −0.009298 | 0.014791 | 0.064233 | −0.096257 | 0.07887 | 0.033371 | −0.104453 | 0.071998 | −0.056338 | 0.059722 | −0.019103 | 0.020755 | −0.033856 | −0.045162 |
| 29 | 0.048576 | 0.012336 | −0.044341 | −0.01801 | 0.021446 | −0.005518 | 0.008849 | −0.003842 | −0.070372 | −0.013725 | 0.030656 | 0.006794 | 0.00074 | 0.003026 |
| 30 | −0.026415 | −0.013698 | 0.034514 | 0.022373 | −0.078794 | −0.131747 | 0.015421 | −0.032279 | 0.116819 | 0.000152 | −0.009652 | 0.042284 | 0.055156 | 0.027664 |
| 31 | 0.014404 | 0.011003 | 0.003354 | 0.080718 | 0.016646 | −0.085799 | −0.144389 | 0.072684 | −0.034784 | −0.069283 | 0.055664 | 0.022753 | −0.00629 | −0.02759 |
| 32 | −0.037372 | −0.062006 | −0.008496 | −0.061238 | −0.069833 | −0.061436 | 0.018445 | −0.037194 | −0.032309 | −0.045037 | 0.039579 | 0.052987 | 0.148449 | −0.107462 |
| 33 | −0.075209 | −0.045253 | −0.02303 | 0.104099 | 0.065738 | −0.081719 | −0.062597 | 0.027675 | 0.047183 | 0.028729 | −0.030194 | −0.04692 | −0.079574 | 0.009786 |
| 34 | 0.098323 | −0.069902 | −0.053907 | −0.014303 | 0.068947 | 0.010992 | −0.044814 | 0.03264 | 0.015308 | −0.092984 | −0.055731 | −0.046405 | −0.014195 | 0.028641 |
| 35 | −0.090406 | −0.13612 | −0.00927 | −0.007189 | −0.112382 | 0.033073 | 0.046754 | −0.067501 | −0.059151 | −0.082316 | 0.015022 | −0.02047 | −0.07179 | −0.03554 |
| 36 | −0.009969 | −0.016623 | −0.042476 | −0.096492 | −0.10745 | −0.062736 | −0.032348 | 0.144451 | −0.009945 | −0.090345 | 0.013049 | 0.032742 | −0.04716 | 0.00557 |
| 37 | 0.015299 | 0.146767 | −0.051147 | −0.05974 | −0.036404 | 0.011556 | −0.032336 | 0.029228 | 0.103494 | 0.026746 | 0.039544 | 0.056549 | −0.053282 | −0.017317 |
| 38 | 0.102588 | 0.004779 | 0.020402 | 0.046325 | 0.047147 | −0.020988 | −0.038407 | 0.034329 | 0.021091 | −0.055027 | 0.00337 | 0.035761 | −0.036002 | −0.059739 |
| 39 | 0.107447 | −0.243812 | −0.21799 | −0.023484 | −0.072556 | 0.040751 | −0.162312 | 0.004845 | −0.096377 | 0.066268 | 0.015455 | −0.069403 | −0.156419 | −0.04368 |
| 40 | 0.020825 | −0.017705 | −0.04594 | −0.007477 | −0.010961 | −0.017029 | 0.017804 | 0.030697 | −0.057617 | −0.013642 | 0.018151 | −0.024991 | −0.005712 | 0.006732 |
| 41 | −0.007299 | 0.051721 | 0.022102 | −0.031781 | −0.028797 | 0.067979 | 0.05927 | 0.00587 | 0.030747 | −0.017299 | −0.041403 | 0.012719 | −0.073954 | −0.039388 |
| 42 | −0.161723 | −0.095185 | −0.000447 | 0.013945 | −0.060868 | 0.141974 | 0.139963 | 0.03181 | 0.017804 | 0.066305 | −0.034379 | 0.059423 | 0.087507 | 0.00175 |
| 43 | 0.077796 | 0.058453 | 0.021864 | −0.020852 | 0.035627 | −0.062783 | 0.064497 | 0.058173 | −0.050748 | 0.019029 | 0.050639 | −0.08173 | 0.04213 | 0.021632 |
| 44 | 0.096578 | −0.039301 | 0.118527 | −0.073377 | 0.084033 | −0.095183 | −0.063183 | −0.004475 | 0.120658 | 0.030318 | 0.08476 | 0.067868 | 0.055953 | 0.022904 |
| 45 | −0.062196 | 0.015953 | −0.157545 | −0.039925 | −0.017202 | −0.037523 | −0.019716 | −0.046032 | 0.004746 | 0.023123 | −0.016595 | 0.065072 | 0.046061 | −0.058504 |
| 46 | −0.031333 | −0.141105 | −0.079664 | 0.066692 | 0.061442 | 0.223835 | −0.126903 | −0.015191 | −0.044269 | 0.116668 | 0.021242 | −0.03669 | 0.077619 | −0.040625 |
| 47 | 0.084483 | 0.093038 | −0.02097 | −0.054204 | 0.059694 | 0.021417 | 0.076922 | −0.098638 | −0.027683 | −0.082811 | 0.006211 | −0.000623 | −0.000128 | 0.072543 |
| 48 | −0.072588 | −0.091379 | 0.129206 | −0.052401 | −0.044043 | −0.1631 | 0.111101 | −0.033442 | 0.00255 | 0.073927 | 0.015665 | 0.025055 | 0.001755 | 0.024802 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 49 | −0.075433 | 0.031169 | 0.017717 | 0.031163 | 0.059288 | −0.078185 | −0.079188 | −0.026163 | −0.102905 | −0.105804 | −0.015135 | −0.049183 | 0.031873 | 0.014438 |
| 50 | 0.174194 | −0.126914 | 0.034585 | −0.088784 | −0.036707 | −0.121381 | 0.069561 | −0.016449 | 0.02511 | 0.020865 | 0.00649 | −0.023742 | −0.002918 | 0.02297 |
| 51 | −0.013572 | −0.160764 | −0.00612 | −0.044608 | 0.075682 | −0.009381 | −0.002669 | −0.016237 | −0.018042 | −0.012852 | −0.034846 | 0.044047 | −0.010705 | −0.004582 |
| 52 | 0.040694 | 0.085538 | −0.02485 | 0.064863 | −0.045906 | 0.070604 | 0.04884 | 0.12815 | −0.046185 | −0.020292 | 0.009745 | −0.089829 | −0.030198 | −0.001113 |
| 53 | −0.072597 | 0.033226 | −0.007055 | 0.022296 | −0.004707 | −0.007272 | 0.057478 | −0.002178 | −0.133848 | −0.118267 | −0.081029 | −0.082824 | −0.018549 | 0.141936 |
| 54 | −0.053624 | 0.013655 | −0.133379 | −0.027821 | 0.055694 | 0.063116 | 0.017059 | −0.016089 | 0.004195 | −0.116161 | 0.011905 | 0.007185 | 0.096504 | 0.005636 |
| 55 | 0.016074 | −0.118201 | −0.091134 | 0.035984 | −0.017939 | −0.0074 | 0.043891 | −0.168014 | 0.064302 | 0.084673 | −0.01236 | 0.046825 | 0.038305 | 0.019969 |
| 56 | 0.077473 | 0.049658 | 0.056776 | −0.026965 | −0.06894 | 0.012124 | −0.032083 | 0.170227 | −0.087085 | −0.019551 | −0.062325 | −0.036922 | −0.071891 | 0.042322 |
| 57 | 0.05663 | −0.009351 | 0.057138 | 0.018595 | −0.019663 | 0.025489 | 0.042201 | 0.029899 | 0.117542 | 0.026515 | −0.013777 | 0.023454 | 0.160109 | 0.036203 |
| 58 | 0.00795 | 0.056638 | 0.076939 | 0.010461 | 0.019747 | −0.043275 | −0.011718 | 0.02398 | −0.071616 | −0.031504 | −0.033742 | −0.029977 | 0.116195 | −0.043295 |
| 59 | −0.023861 | 0.110177 | −0.018343 | 0.025948 | −0.015856 | 0.022499 | 0.126395 | −0.026248 | 0.103071 | −0.067794 | −0.074573 | −0.053728 | 0.01619 | 0.026335 |
| 60 | −0.001393 | −0.022041 | −0.000287 | 0.051296 | 0.025728 | 0.051207 | −0.019493 | −0.002239 | 0.023183 | 0.014195 | 0.01308 | 0.049021 | 0.020781 | −0.004896 |
| 61 | 0.00089 | −0.041203 | 0.006295 | 0.012671 | 0.036317 | −0.002241 | 0.013251 | −0.033847 | 0.007055 | 0.031721 | 0.023343 | 0.032134 | 0.033963 | −0.022459 |
| 62 | −0.033122 | 0.039466 | −0.004411 | 0.019212 | −0.006823 | 0.019743 | −0.028467 | −0.017209 | 0.035972 | −0.045858 | 0.009406 | 0.028987 | −0.015962 | −0.008375 |
| 63 | −0.001826 | −0.035578 | 0.007381 | −0.002891 | 0.009305 | 0.000307 | −0.019385 | −0.02823 | 0.005164 | 0.011213 | 0.000487 | 0.013699 | −0.001706 | −0.001465 |
| 64 | 0.028303 | −0.05201 | −0.026037 | −0.00286 | −0.003537 | −0.000295 | 0.000065 | −0.031017 | 0.027135 | 0.002463 | 0.000342 | −0.008824 | −0.001562 | 0.018425 |
| 65 | 0.033221 | −0.007524 | −0.003057 | 0.016153 | 0.008609 | 0.007151 | −0.008411 | −0.00814 | −0.016091 | −0.007475 | 0.014948 | 0.002081 | −0.017739 | 0.021423 |
| 66 | 0.050556 | −0.012646 | −0.014774 | 0.005533 | 0.003396 | 0.01561 | −0.025336 | 0.002927 | 0.000078 | 0.010288 | 0.009971 | 0.000785 | 0.008683 | 0.00042 |
| 67 | 0.039025 | 0.045351 | 0.009589 | −0.003972 | 0.013034 | 0.003017 | −0.023707 | −0.000913 | 0.048135 | −0.026047 | 0.016574 | 0.030544 | 0.067019 | 0.028039 |
| 68 | −0.024294 | 0.041409 | 0.062746 | 0.0222 | −0.027662 | −0.016894 | 0.051637 | −0.040998 | 0.082765 | 0.022897 | 0.006296 | 0.011937 | −0.010009 | 0.045388 |
| 69 | −0.023265 | 0.029494 | 0.039444 | −0.045988 | 0.012935 | −0.012712 | 0.047495 | −0.018519 | 0.025039 | −0.005677 | −0.035299 | 0.021771 | 0.010812 | 0.011113 |
| 70 | 0.003644 | 0.010769 | 0.007725 | 0.010763 | 0.015263 | 0.022085 | −0.03841 | 0.002971 | 0.020894 | −0.036488 | −0.008614 | 0.014286 | −0.002639 | −0.015855 |
| 71 | 0.021769 | −0.02853 | 0.02517 | −0.037026 | 0.026264 | −0.005848 | 0.009372 | −0.028619 | 0.012622 | 0.016681 | −0.014612 | 0.017398 | 0.043326 | 0.021383 |
| 72 | 0.002277 | −0.044696 | 0.010865 | 0.009072 | 0.023792 | 0.016927 | −0.00202 | −0.043934 | 0.030795 | −0.001816 | −0.037053 | 0.023909 | 0.015505 | 0.029648 |
| 73 | 0.015903 | 0.054648 | −0.02804 | −0.006901 | −0.051778 | 0.03906 | 0.013322 | −0.022446 | 0.020978 | −0.003037 | −0.009923 | −0.007006 | 0.041395 | −0.002557 |
| 74 | −0.004008 | 0.024041 | −0.034378 | 0.042694 | −0.001482 | −0.062715 | −0.024809 | −0.021731 | −0.028128 | −0.035391 | −0.000675 | −0.027262 | −0.028637 | 0.028505 |
| 75 | 0.00449 | −0.013967 | 0.010655 | −0.011998 | 0.022754 | 0.029429 | −0.024002 | −0.022828 | 0.018338 | 0.015914 | 0.007667 | 0.019128 | 0.011159 | 0.002376 |
| 76 | −0.00649 | 0.011839 | −0.027394 | −0.005691 | 0.009884 | 0.001493 | −0.030352 | −0.036944 | −0.025705 | −0.010106 | 0.001963 | 0.008275 | 0.027346 | −0.002952 |
| 77 | 0.008509 | −0.012971 | 0.02019 | −0.02414 | 0.022777 | 0.013704 | −0.022092 | −0.017544 | 0.023322 | 0.015787 | 0.002497 | 0.0228 | 0.016987 | −0.000993 |
| 78 | −0.008486 | −0.002453 | 0.025377 | −0.012577 | 0.020154 | 0.016598 | −0.018115 | −0.015867 | 0.046366 | 0.02449 | 0.001588 | 0.020293 | 0.021871 | 0.003452 |
| 79 | 0.022736 | −0.007998 | −0.024672 | −0.013146 | 0.007328 | 0.03081 | −0.014866 | −0.030726 | −0.009747 | −0.01535 | −0.000595 | −0.01217 | −0.008234 | 0.005075 |
| 80 | 0.00858 | −0.097062 | −0.02215 | −4.02136 | 0.027775 | 0.013874 | 0.0575 | −0.014721 | 0.022307 | −0.028472 | −0.003047 | 0.023396 | −0.004205 | 0.007924 |
| 81 | −0.018126 | 0.052526 | 0.013599 | 0.031656 | −0.000827 | −0.002403 | 0.005318 | −0.005316 | 0.000993 | 0.01435 | 0.03973 | 0.014481 | 0.050972 | −0.008886 |
| 82 | 0.000037 | −0.015343 | −0.010506 | 0.032404 | 0.008057 | 0.018675 | 0.010587 | 0.001881 | −0.007689 | −0.004554 | 0.00237 | 0.005258 | −0.026347 | 0.007021 |
| 83 | −0.008074 | −0.019721 | 0.004421 | 0.004446 | 0.021678 | −0.006942 | 0.015518 | −0.012414 | −0.002054 | 0.014688 | 0.009238 | 0.004853 | −0.032068 | −0.000053 |
| 84 | −0.00892 | −0.02406 | −0.010387 | −0.00969 | 0.017226 | 0.012622 | −0.01323 | 0.007129 | −0.016337 | 0.00415 | −0.008283 | −0.007351 | −0.003754 | −0.015188 |
| 85 | −0.01426 | −0.018175 | −0.006246 | 0.017849 | −0.023441 | 0.007264 | 0.016707 | −0.005422 | 0.011946 | −0.010232 | 0.013878 | 0.024662 | −0.00165 | 0.001455 |
| 86 | 0.033352 | 0.001468 | 0.018114 | −0.007804 | 0.023737 | 0.01141 | −0.010607 | 0.026083 | 0.003529 | 0.018039 | −0.020961 | 0.010274 | 0.006776 | 0.013828 |
| 87 | 0.017777 | 0.022583 | −0.02211 | 0.000327 | 0.031206 | 0.023288 | 0.031222 | −0.021449 | 0.007514 | −0.029839 | 0.000641 | 0.024799 | 0.053455 | 0.018757 |
| 88 | 0.002478 | 0.005038 | 0.002939 | −0.014151 | 0.025089 | 0.002063 | 0.006655 | 0.004811 | 0.002413 | 0.017126 | −0.002161 | 0.006892 | −0.011842 | 0.005847 |
| 89 | −0.015456 | 0.012411 | 0.017872 | 0.000207 | 0.010432 | −0.02126 | 0.030367 | −0.004088 | 0.018378 | 0.004358 | −0.005777 | −0.004873 | −0.013478 | 0.010894 |
| 90 | 0.023181 | 0.017134 | 0.001467 | 0.003549 | −0.04138 | 0.038663 | −0.018311 | 0.002992 | −0.015271 | −0.008953 | −0.003783 | −0.013035 | 0.018346 | −0.008316 |
| 91 | −0.028582 | 0.004698 | 0.021222 | −0.001989 | −0.004609 | −0.02629 | 0.022381 | 0.006676 | −0.006519 | −0.016051 | −0.016172 | −0.028988 | 0.008992 | −0.044838 |
| 92 | −0.044838 | −0.03138 | 0.00487 | 0.035379 | −0.049341 | 0.02745 | −0.044817 | 0.029171 | 0.02684 | −0.006928 | −0.006482 | −0.01099 | 0.024157 | −0.023813 |
| 93 | 0.017499 | −0.006602 | 0.043545 | −0.025169 | 0.011728 | −0.031389 | −0.004626 | −0.017329 | 0.010915 | 0.002876 | 0.004266 | 0.011416 | −0.020314 | 0.004016 |
| 94 | −0.038287 | 0.007009 | 0.021132 | 0.032154 | −0.021791 | 0.016105 | 0.006657 | 0.022125 | 0.031553 | 0.001085 | −0.026329 | 0.019345 | −0.043837 | 0.007736 |
| 95 | −0.039724 | 0.010512 | −0.009955 | 0.002337 | −0.033679 | 0.049082 | 0.036448 | 0.003114 | −0.010092 | −0.02935 | −0.016808 | −0.01230f | −0.022709 | −0.035299 |
| 96 | −0.010275 | 0.004174 | −0.038294 | −0.023373 | −0.01554 | 0.014078 | 0.012279 | 0.044148 | −0.058513 | −0.058807 | −0.025418 | 0.006851 | 0.037029 | 0.013501 |
| 97 | 0.009032 | −0.025607 | −0.010332 | 0.026976 | −0.012724 | 0.01476 | 0.047316 | −0.010234 | −0.023952 | −0.019562 | 0.005634 | −0.003895 | 0.000632 | 0.01514 |
| 98 | 0.021893 | −0.006738 | −0.009441 | 0.014121 | 0.000844 | 0.015867 | 0.016919 | −0.004261 | 0.000464 | −0.014468 | 0.013224 | 0.007471 | −0.000453 | 0.011285 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 99 | −0.017275 | −0.015666 | −0.014856 | −0.000429 | −0.018758 | −0.014556 | −0.00409 | 0.008973 | −0.016511 | −0.026755 | −0.006535 | 0.012388 | −0.007045 | 0.009506 |
| 100 | −0.0089 | −0.005405 | 0.004321 | 0.024766 | 0.027554 | 0.020961 | 0.014841 | −0.008265 | −0.012763 | −0.021949 | −0.015331 | −0.000866 | −0.01491 | 0.012262 |
| 101 | 0.016664 | −0.005439 | −0.005518 | 0.022284 | 0.006853 | 0.00703 | −0.0118 | −0.014207 | 0.025893 | −0.005805 | 0.015177 | 0.011973 | 0.025539 | 0.010235 |
| 102 | −0.040323 | 0.012001 | −0.015285 | −0.011452 | −0.017515 | 0.04748 | 0.043636 | 0.015811 | −0.055844 | −0.030731 | 0.016064 | −0.004783 | −0.013491 | −0.002496 |
| 103 | 0.015215 | −0.028684 | 0.055955 | −0.045152 | 0.029915 | 0.034468 | 0.00523 | 0.002625 | −0.037075 | 0.006163 | 0.015451 | −0.024248 | −0.026429 | 0.009344 |
| 104 | −0.002584 | 0.016116 | −0.000938 | −0.024298 | 0.018103 | −0.026005 | −0.009511 | 0.034721 | −0.045296 | −0.035653 | 0.016237 | −0.006148 | 0.025053 | 0.012554 |
| 105 | −0.022636 | 0.067317 | 0.023454 | −0.033091 | 0.033327 | −0.017748 | 0.00867 | −0.02593 | −0.014487 | 0.001028 | 0.03859 | 0.018174 | −0.010708 | 0.000081 |
| 106 | 0.022288 | −0.051656 | −0.022628 | −0.025993 | −0.050532 | 0.021426 | −0.047688 | 0.013722 | 0.03204 | 0.060705 | 0.000813 | −0.006657 | −0.001938 | −0.017317 |
| 107 | −0.006648 | −0.021602 | −0.02051 | −0.00591 | −0.040219 | 0.002072 | −0.005085 | −0.009277 | 0.055761 | 0.018358 | −0.025088 | 0.038423 | 0.055556 | −0.018948 |
| 108 | 0.009646 | −0.02999 | −0.098191 | −0.080471 | −0.038439 | −0.0397351 | −0.033881 | −0.050805 | 0.0068161 | −0.010709 | 0.007352 | 0.012864 | 0.061273 | −0.01021 |
| 109 | 0.701548 | −0.003068 | −0.010382 | 0.044557 | −0.085798 | 0.000903 | 0.030922 | −0.033216 | 0.042204 | −0.002354 | −0.017583 | 0.036806 | −0.022787 | −0.013428 |
| 110 | −0.004842 | 0.659241 | −0.042502 | −0.018569 | 0.004807 | 0.028523 | −0.058353 | −0.035855 | 0.011934 | 0.06535 | −0.014216 | 0.034329 | −0.011328 | −0.02395 |
| 111 | 0.007184 | −0.045493 | 0.745116 | 0.001833 | −0.057629 | 0.094493 | −0.05884 | −0.048625 | −0.036607 | −0.002952 | 0.002887 | −0.01154 | 0.006469 | −0.020549 |
| 112 | 0.04837 | 0.012111 | 0.006457 | 0.793148 | 0.006467 | −0.053672 | −0.007356 | −0.052818 | −0.030837 | 0.019517 | −0.019613 | 0.005252 | 0.034781 | −0.027011 |
| 113 | −0.073776 | 0.011254 | −0.055149 | 0.013965 | 0.806559 | −0.023358 | 0.034803 | 0.016241 | 0.017897 | −0.023303 | −0.007529 | −0.005881 | −0.009698 | −0.032804 |
| 114 | −0.033007 | 0.036257 | 0.109872 | −0.030287 | −0.046039 | 0.630254 | 0.036304 | −0.013169 | −0.003604 | −0.03692 | 0.035977 | −0.00892 | −0.02552 | 0.01218 |
| 115 | 0.026273 | −0.05308 | −0.060143 | 0.00307 | 0.023757 | 0.009845 | 0.746273 | 0.035653 | −0.009086 | −0.02477 | −0.010673 | 0.001648 | −0.012252 | −0.051367 |
| 116 | −0.028235 | −0.037832 | −0.052599 | −0.033206 | 0.007239 | −0.012747 | 0.05672 | 0.730992 | 0.057234 | 0.033957 | 0.015409 | 0.007062 | 0.007604 | 0.014407 |
| 117 | 0.044643 | 0.009902 | −0.020873 | −0.031772 | 0.008633 | −0.011767 | −0.015403 | 0.031602 | 0.708533 | −0.077773 | −0.008505 | −0.105852 | −0.074588 | −0.020154 |
| 118 | 0.002254 | 0.048833 | 0.008469 | 0.029418 | −0.022644 | −0.027254 | −0.007671 | 0.03252 | −0.058999 | 0.743028 | −0.045637 | −0.03512 | −0.011724 | −0.040138 |
| 119 | −0.032799 | −0.00594 | 0.012009 | −0.021492 | −0.008274 | 0.009295 | −0.025588 | 0.002773 | −0.001598 | −0.042849 | 0.864986 | −0.038113 | 0.002765 | −0.006661 |
| 120 | 0.034786 | 0.038967 | −0.005579 | 0.00542 | −0.009148 | −0.005597 | 0.005909 | 0.008473 | −0.120599 | −0.045093 | −0.036578 | 0.8596 | −0.064985 | 0.005256 |
| 121 | −0.007326 | −0.017054 | 0.010109 | 8.008996 | −0.005931 | −0.032838 | −0.00183 | 0.008448 | −0.081553 | −0.039526 | −0.006533 | −0.056542 | 0.698361 | −0.000357 |
| 122 | −0.000216 | −0.027004 | −0.009985 | −0.006655 | −0.006936 | 0.019288 | −0.042341 | 0.008391 | −0.017089 | −0.021701 | 0.009011 | 0.006425 | −0.004736 | 0.866642 |
| 123 | −0.004581 | −0.035466 | −0.00318 | 0.001828 | −0.007671 | 0.006787 | −0.051183 | −0.013633 | 0.019892 | −0.019061 | −0.043276 | −0.011054 | −0.036593 | −0.097056 |
| 124 | −0.010258 | −0.005185 | −0.005402 | −0.028164 | 0.003207 | 0.009442 | −0.018831 | −0.02279 | −0.003997 | −0.025059 | −0.096824 | −0.02424 | 0.021142 | −0.027946 |
| 125 | 0.032153 | −0.02025 | 0.003155 | −0.037757 | −0.003564 | 0.028039 | 0.007595 | 0.036086 | −0.033274 | −0.029872 | 0.0042 | −0.0129031 | −0.006163 | 0.014482 |
| 126 | −0.018377 | 0.023586 | −0.008115 | 0.029349 | −0.032476 | −0.009567 | −0.003317 | 0.033863 | −0.047654 | −0.091464 | −0.008343 | −0.013132 | −0.082801 | −0.057391 |
| 127 | 0.002345 | −0.001562 | 0.016424 | 0.019099 | 0.000958 | 0.021427 | −0.009218 | 0.035848 | 0.003848 | −0.03672 | −0.021586 | 0.00997 | −0.010613 | −0.02009 |
| 128 | 0.001037 | −0.044197 | 0.050234 | 0.00552 | 0.026312 | −0.012349 | 0.006664 | 0.02369 | 0.008534 | −0.014909 | −0.017383 | 0.001728 | 0.013833 | 0.010417 |
| 129 | 0.017787 | −0.034079 | −0.030204 | −0.095896 | −0.002953 | 0.030994 | −0.016135 | 0.003235 | 0.019724 | 0.026781 | −0.023591 | 0.019763 | 0.018939 | −0.033191 |
| 130 | −0.024696 | 0.030555 | 0.039732 | −0.005403 | −0.000603 | 0.055613 | −0.082768 | 0.016679 | 0.054244 | 0.016696 | −0.01544 | −0.008769 | −0.02269 | −0.014733 |
| 131 | 0.008997 | −0.019851 | −0.023544 | −0.009755 | −0.022247 | 0.081427 | 0.064951 | −0.079605 | 0.008768 | −0.003468 | −0.030569 | 0.015437 | −0.024113 | 0.005832 |
| 132 | 0.01974 | −0.02315 | −0.004499 | −0.01636 | 0.034787 | 0.019301 | 0.022554 | 0.012727 | −0.032282 | 0.002253 | −0.030932 | −0.027833 | 0.013486 | 0.01928 |
| 133 | −0.038204 | −0.047984 | 0.038187 | 0.01717 | −0.007265 | 0.034336 | 0.058278 | 0.026031 | 0.009804 | −0.014023 | −0.023446 | 0.009367 | −0.017303 | 0.039291 |
| 134 | 0.013663 | 0.055751 | −0.014974 | −0.001866 | 0.027768 | 0.033927 | −0.031534 | −0.039741 | 0.019565 | −0.03874 | −0.016491 | 0.03483 | −0.006258 | −0.024582 |
| 135 | 0.00419 | 0.040738 | 0.022103 | −0.01297 | 0.014671 | 0.00255 | 0.0359 | 0.004762 | −0.001854 | −0.016124 | −0.028876 | −0.034093 | 0.01847 | 0.013611 |
| 136 | −0.022558 | −0.034971 | −0.055372 | 0.072337 | −0.021465 | 0.045722 | −0.032045 | −0.030986 | 0.016046 | −0.035854 | −0.058034 | −0.017141 | 0.02744 | −0.000045 |
| 137 | 0.002267 | 0.020724 | 0.060412 | 0.014597 | −0.016332 | 0.019523 | 0.024113 | 0.004486 | 0.071932 | −0.031741 | −0.01394 | 0.013739 | 0.01179 | 0.003873 |
| 138 | −0.035206 | 0.013557 | 0.010117 | −0.012361 | −0.064048 | −0.030537 | 0.051014 | −0.026472 | 0.034751 | −0.00972 | −0.031256 | −0.005971 | −0.014226 | 0.004976 |
| 139 | −0.045477 | −0.024936 | −0.048927 | 0.024146 | −0.015179 | 0.012116 | −0.012127 | 0.01449 | 0.02212 | 0.000602 | −0.015002 | −0.010644 | −0.017206 | −0.005762 |
| 140 | 0.049814 | −0.008272 | 0.039915 | −0.043188 | 0.011774 | −0.014252 | 0.00622 | 0.026182 | −0.025465 | 0.01405 | −0.003823 | 0.01187 | 0.016702 | 0.004201 |
| 141 | 0.002137 | −0.001778 | 0.074229 | −0.012535 | 0.053667 | −0.006339 | 0.024096 | 0.017201 | 0.023791 | 0.015677 | −0.007584 | −0.002011 | 0.0103 | −0.001857 |
| 142 | −0.013117 | 0.010417 | −0.006815 | −0.027464 | −0.014929 | −0.019156 | −0.014447 | 0.008253 | −0.058361 | 0.005328 | −0.006101 | −0.034375 | −0.032636 | −0.03696 |
| 143 | 0.007823 | −0.003082 | 0.028758 | −0.030432 | 0.012625 | −0.009279 | −0.018946 | 0.017034 | 0.0253511 | 0.037875 | 0.014422 | 0.015864 | 0.033899 | −0.06821 |
| 144 | 0.010969 | −0.006964 | 0.003871 | −0.011758 | 0.002422 | 0.0069421 | −0.014715 | −0.031488 | 0.039865 | 0.0131851 | −0.065435 | −0.002574 | 0.022539 | −0.048416 |
| 145 | −0.01272 | −0.0229 | 0.026743 | 0.055566 | −0.035456 | −0.044009 | 0.031964 | 0.024914 | −0.008075 | −0.0673451 | −0.016424 | −0.001838 | 0.006351 | −0.035045 |
| 146 | 0.031876 | 0.037197 | 0.001862 | −0.011031 | 0.004147 | 0.019135 | 0.063612 | −0.01303 | −0.0263 | −0.018387 | −0.021086 | −0.04602 | 0.004654 | 0.029654 |
| 147 | 0.009348 | 0.030706 | 0.013368 | −0.01888 | −0.090785 | −0.055542 | 0.02431 | 0.013838 | −0.085817 | 0.017732 | 0.0037 | −0.054264 | −0.049938 | −0.014256 |
| 148 | 0.007514 | 0.0333 | −0.041814 | 0.001591 | −0.039568 | −0.015729 | −0.011681 | −0.022496 | −0.029674 | −0.073539 | −0.002341 | −0.027651 | 0.082888 | −0.042468 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 149 | 0.024272 | 0.011016 | 0.032894 | 0.016932 | 0.034068 | −0.028306 | −0.031983 | 0.033206 | 0.007985 | −0.023716 | 0.013974 | 0.002183 | −0.007777 | −0.017006 |
| 150 | 0.033077 | 0.02863 | 0.016457 | −0.041447 | −0.030342 | −0.001789 | 0.032769 | −0.029938 | −0.008531 | −0.024121 | 0.003973 | −0.05129 | 0.009021 | −0.003936 |
| 151 | 0.0252 | −0.026611 | −0.008254 | −0.005929 | 0.026825 | 0.018005 | −0.080451 | −0.003157 | 0.022164 | −0.006744 | −0.01967 | 0.039617 | 0.073272 | −0.042654 |
| 152 | 0.017709 | −0.017144 | −0.014617 | −0.036538 | 0.014527 | 0.020458 | −0.018962 | 0.013958 | 0.013549 | 0.007054 | −0.050531 | −0.000354 | −0.01241 | −0.004097 |
| 153 | −0.006159 | −0.059077 | 0.002063 | −0.015195 | 0.037126 | 0.026426 | −0.007905 | −0.005229 | −0.005219 | −0.011986 | −0.040139 | −0.02233 | −0.005739 | −0.012162 |
| 154 | −0.010859 | −0.002834 | −0.054802 | 0.02355 | −0.012907 | 0.070449 | −0.010314 | −0.03951 | −0.005245 | 0.022383 | −0.019637 | −0.018616 | −0.015795 | −0.007323 |
| 155 | 0.02187 | 0.013545 | −0.054334 | −0.003211 | 0.019734 | 0.025373 | 0.007012 | 0.015921 | 0.036806 | −0.020745 | −0.044073 | −0.020659 | −0.004976 | 0.018762 |
| 156 | −0.021557 | −0.002791 | −0.012105 | 0.03825 | −0.018167 | 0.049351 | 0.002533 | −0.001375 | 0.030614 | 0.020633 | −0.033042 | 0.000016 | −0.015512 | 0.014744 |
| 157 | 0.027471 | −0.019595 | −0.012595 | −0.006785 | 0.001928 | 0.018325 | −0.003636 | 0.020475 | −0.06185 | −0.007187 | −0.018996 | −0.050359 | −0.010202 | −0.006695 |
| 158 | −0.060606 | −0.065645 | −0.053694 | 0.02632 | 0.027567 | −0.039516 | −0.045227 | −0.043589 | 0.08049 | 0.035033 | −0.017778 | 0.007581 | 0.0234 | 0.017692 |
| 159 | −0.047545 | −0.017198 | 0.049461 | 0.002859 | 0.010635 | −0.057574 | 0.042458 | −0.020871 | 0.025295 | −0.020082 | −0.006873 | −0.015742 | −0.019322 | 0.01883 |
| 160 | −0.052581 | −0.132397 | 0.024034 | −0.002032 | −0.077212 | −0.002601 | 0.013753 | 0.032767 | −0.033285 | −0.058045 | −0.037387 | 0.011608 | −0.056001 | −0.040246 |
| 161 | −0.046813 | 0.009011 | 0.007772 | −0.04927 | 0.023734 | −0.070351 | 0.029991 | −0.068776 | 0.047466 | 0.041633 | −0.024076 | −0.006545 | 0.057729 | 0.006226 |
| 162 | 0.037233 | 0.025946 | 0.036995 | −0.032334 | 0.006064 | −0.0032 | 0.041496 | −0.044021 | −0.003417 | −0.035262 | −0.042231 | −0.023146 | −0.015303 | −0.004511 |
| 163 | 0.03338 | 0.011131 | −0.004023 | −0.032715 | 0.007397 | 0.030774 | −0.003385 | 0.034299 | −0.026797 | 0.0015 | −0.019759 | −0.005791 | −0.007429 | −0.013409 |
| 164 | −0.025083 | 0.042319 | 0.05192 | 0.010674 | −0.020772 | −0.014836 | −0.004799 | 0.053846 | 0.00699 | −0.041047 | −0.036826 | 0.035819 | 0.05338 | 0.011629 |
| 165 | 0.013262 | 0.046799 | −0.063811 | −0.016424 | −0.00331 | 0.046797 | −0.028913 | 0.048314 | −0.029466 | −0.06525 | −0.017337 | 0.028028 | −0.029771 | −0.011044 |
| 166 | −0.079499 | 0.018938 | −0.01351 | −0.026 | −0.046364 | 0.001248 | 0.010931 | 0.003156 | −0.04028 | 0.025123 | −0.043999 | −0.02289 | 0.012511 | −0.002217 |
| 167 | −0.014803 | 0.010249 | 0.002348 | 0.04743 | −0.046873 | −0.031452 | −0.017846 | 0.043661 | 0.031823 | −0.027017 | −0.028296 | −0.004691 | −0.007801 | 0.007086 |
| 168 | 0.013695 | 0.008845 | 0.062815 | 0.0059 | 0.010204 | 0.005562 | −0.003875 | 0.021505 | 0.043647 | −0.04826 | −0.011493 | 0.023612 | 0.009155 | −0.024628 |
| 169 | 0.016354 | −0.008928 | 0.007783 | −0.011275 | 0.00008 | −0.019527 | 0.015729 | −0.025097 | −0.013591 | 0.011385 | 0.006367 | −0.032355 | 0.007682 | 0.012768 |
| 170 | 0.023794 | −0.011967 | 0.036365 | −0.00467 | 0.015762 | −0.044451 | 0.010561 | −0.042051 | 0.004978 | 0.023787 | 0.007519 | −0.013034 | 0.00825 | 0.020715 |
| 171 | 0.008788 | 0.014526 | 0.015156 | −0.019037 | 0.020701 | −0.040851 | 0.015473 | −0.022741 | 0.015285 | −0.000284 | −0.001567 | −0.020286 | −0.03763 | −0.000398 |
| 172 | −0.008359 | 0.000228 | −0.003382 | −0.006684 | −0.015274 | −0.040576 | 0.016345 | −0.027263 | −0.013233 | −0.013538 | −0.013394 | −0.044303 | 0.00114 | 0.015023 |
| 173 | −0.004062 | −0.005848 | −0.01223 | 0.003005 | −0.017456 | −0.021359 | −0.011151 | 0.006503 | 0.0024 | −0.01803 | 0.030319 | −0.003246 | −0.043016 | 0.00477 |
| 174 | −0.003399 | −0.012377 | −0.009239 | 0.002204 | −0.03378 | −0.019215 | 0.002569 | 0.006286 | 0.048175 | 0.023863 | 0.023582 | 0.000996 | 0.000663 | 0.005066 |
| 175 | 0.037563 | 0.036815 | −0.014443 | −0.022304 | −0.045619 | 0.013981 | 0.002364 | −0.005434 | −0.011564 | −0.009001 | 0.017438 | −0.033696 | 0.024085 | −0.044356 |
| 176 | 0.002804 | 0.01116 | −0.037272 | 0.020891 | −0.005674 | 0.041876 | 0.010199 | −0.040857 | −0.01857 | 0.007656 | −0.010643 | −0.020766 | −0.002496 | 0.01633 |
| 177 | −0.027533 | 0.023928 | −0.005666 | 0.026079 | −0.005376 | 0.001279 | −0.032794 | 0.010959 | −0.011846 | −0.018603 | −0.053995 | −0.052122 | 0.013532 | 0.047194 |
| 178 | 0.030008 | −0.012327 | −0.001098 | −0.008019 | −0.004264 | 0.031107 | 0.000453 | 0.01933 | 0.016724 | −0.000972 | −0.008589 | 0.00061 | 0.007367 | −0.004395 |
| 179 | 0.021427 | −0.016535 | −0.00597 | 0.004421 | 0.003139 | 0.002782 | 0.001246 | 0.013555 | −0.002161 | −0.020773 | −0.004302 | −0.002888 | −0.013987 | −0.00403 |
| 180 | 0.026243 | −0.021092 | 0.002988 | 0.003093 | 0.000553 | −0.001707 | −0.001085 | 0.006981 | 0.004534 | −0.021472 | 0.001649 | −0.003485 | −0.012668 | 0.001236 |
| 181 | 0.019115 | −0.036384 | −0.007482 | 0.002532 | 0.007838 | 0.002426 | −0.005785 | −0.003139 | −0.00021 | −0.005745 | 0.002298 | 0.003783 | −0.011674 | 0.001673 |
| 182 | 0.024358 | −0.020616 | 0.011153 | 0.007827 | 0.022673 | −0.016632 | −0.001856 | −0.013835 | 0.000057 | −0.01663 | −0.006011 | −0.003478 | −0.013293 | 0.006313 |
| 183 | −0.000904 | −0.002533 | −0.014078 | 0.001498 | 0.019928 | −0.003419 | 0.01439 | −0.01569 | 0.016686 | −0.029026 | −0.018922 | 0.002799 | −0.045183 | −0.004724 |
| 184 | 0.002301 | 0.000886 | −0.032679 | −0.031401 | 0.009699 | −0.014364 | 0.006874 | −0.005844 | 0.026718 | −0.002011 | −0.026149 | −0.004198 | −0.076511 | −0.003912 |
| 185 | 0.016824 | −0.058565 | 0.022912 | −0.037661 | 0.008806 | 0.011995 | −0.003976 | −0.015053 | −0.036755 | 0.007083 | 0.009467 | −0.018432 | −0.005013 | −0.034009 |
| 186 | −0.057941 | 0.01923 | 0.015706 | −0.010955 | −0.003977 | −0.006944 | −0.030323 | 0.019405 | 0.013912 | −0.010542 | −0.018731 | −0.021841 | −0.032438 | −0.033934 |
| 187 | 0.000882 | 0.014208 | 0.003915 | 0.015478 | 0.013149 | −0.021856 | −0.008598 | 0.00922 | −0.033129 | −0.041283 | 0.004034 | −0.021638 | −0.033365 | 0.009515 |
| 188 | −0.000317 | −0.006147 | 0.002732 | 0.008473 | −0.006305 | −0.024547 | 0.007724 | −0.009637 | 0.000814 | −0.010638 | −0.000426 | −0.014894 | −0.019823 | 0.017894 |
| 189 | 0.002295 | −0.013004 | −0.028708 | 0.000315 | −0.012662 | −0.004987 | 0.012516 | −0.036329 | −0.022732 | −0.015431 | 0.012724 | −0.032335 | −0.027505 | −0.011201 |
| 190 | 0.019366 | 0.013517 | 0.032691 | 0.025111 | 0.017744 | −0.0090041 | −0.017726 | 0.00941 | 0.017177 | −0.007149 | −0.012111 | −0.00002 | −0.012362 | 0.012512 |
| 191 | 0.008786 | 0.025566 | 0.00695 | 0.022539 | 0.048398 | 0.017136 | −0.018225 | 0.029364 | −0.02132 | −0.022052 | −0.016153 | −0.020524 | 0.013779 | 0.016151 |
| 192 | 0.026714 | 0.017831 | 0.045647 | −0.019603 | 0.040431 | −0.015627 | 0.04638 | −0.005778 | 0.034456 | 0.005567 | −0.019484 | 0.023361 | −0.004005 | −0.002789 |
| 193 | 0.008407 | 0.007593 | 0.027958 | 0.007898 | 0.021743 | 0.011299 | 0.022791 | 0.00039 | 0.01433 | 0.021068 | −0.018602 | 0.001709 | 0.006448 | 0.005504 |
| 194 | 0.013906 | 0.029429 | 0.004618 | −0.00766 | −0.003556 | 0.038967 | −0.009655 | 0.005636 | −0.015698 | −0.014874 | −0.008489 | −0.022865 | 0.010129 | −0.021691 |
| 195 | −0.014724 | −0.037936 | −0.028487 | −0.009504 | 0.005539 | −0.032357 | −0.007711 | −0.041752 | 0.001903 | 0.015782 | −0.000773 | 0.004032 | −0.011972 | −0.009855 |
| 196 | 0.01698 | −0.00316 | −0.012561 | −0.019419 | 0.009578 | −0.034753 | −0.026688 | −0.03461 | 0.002189 | 0.007701 | −0.005156 | −0.003829 | −0.008131 | −0.014844 |
| 197 | 0.051395 | 0.013182 | 0.053905 | 0.012642 | 0.057073 | −0.039696 | −0.017001 | 0.014123 | 0.011627 | −0.015363 | −0.007294 | 0.001492 | 0.002384 | 0.018354 |
| 198 | 0.020793 | 0.025226 | −0.004673 | −0.034203 | 0.002562 | −0.031485 | 0.003048 | −0.023581 | −0.030988 | −0.022819 | −0.010837 | −0.025809 | −0.006982 | −0.014868 |

APPENDIX B3-continued

PCA Transformation
Matrix (340 × 340 Early/Late)

| | | | | | | | | | | | | | |
|---|---|---|---|---|---|---|---|---|---|---|---|---|---|
| 199 | 0.008489 | 0.035021 | 0.000552 | 0.054066 | −0.024236 | 0.011938 | −0.062735 | 0.080139 | −0.00511 | 0.037865 | 0.01845 | −0.02745 | −0.011441 | −0.029653 |
| 200 | −0.072393 | −0.002288 | 0.017288 | −0.018746 | −0.007202 | −0.024512 | 0.043248 | 0.008081 | 0.048419 | −0.015043 | −0.036724 | 0.031807 | 0.032688 | 0.018427 |
| 201 | −0.051311 | 0.014551 | −0.041258 | −0.001012 | 0.017048 | −0.001855 | 0.030063 | −0.071493 | −0.00766 | −0.037796 | −0.006709 | 0.022665 | 0.043313 | −0.003523 |
| 202 | −0.010119 | 0.032101 | 0.002818 | −0.022821 | −0.022017 | −0.030007 | −0.017692 | 0.021603 | −0.001309 | −0.00098 | −0.011226 | 0.011275 | 0.002593 | −0.024107 |
| 203 | 0.050351 | −0.005285 | 0.030208 | −0.02326 | 0.034906 | −0.025711 | −0.015072 | 0.022175 | −0.012557 | −0.01276 | −0.000622 | −0.014958 | −0.007167 | 0.003613 |
| 204 | 0.011362 | 0.021539 | −0.065266 | −0.054263 | 0.008429 | 0.012873 | −0.030046 | −0.089572 | −0.067444 | 0.002754 | −0.018753 | −0.026675 | 0.000873 | −0.004748 |
| 205 | −0.017631 | −0.008877 | 0.005435 | −0.013292 | −0.007188 | 0.096132 | 0.005363 | 0.09428 | −0.01593 | −0.046908 | −0.008845 | 0.053689 | 0.006767 | −0.02177 |
| 206 | −0.0235 | −0.023929 | −0.019021 | −0.061328 | −0.022959 | −0.062052 | −0.046082 | 0.004702 | −0.010333 | 0.010976 | −0.004188 | 0.03613 | 0.004427 | −0.008918 |
| 207 | 0.033254 | −0.035244 | −0.009128 | −0.035303 | −0.012318 | −0.014444 | −0.123397 | 0.000647 | 0.027252 | −0.039473 | −0.053806 | −0.010876 | −0.024216 | −0.018677 |
| 208 | −0.045029 | −0.051788 | 0.013495 | −0.031282 | 0.017722 | 0.037949 | −0.037425 | 0.027049 | 0.017592 | 0.001699 | −0.038436 | 0.023887 | −0.003943 | 0.020073 |
| 209 | 0.004133 | 0.001715 | 0.005117 | −0.039104 | 0.011791 | −0.028103 | 0.029504 | −0.059137 | 0.012141 | 0.053313 | −0.005703 | −0.003489 | −0.049468 | 0.007598 |
| 210 | 0.043371 | −0.011628 | −0.084045 | −0.006193 | −0.016176 | 0.031905 | 0.058452 | −0.021439 | 0.01022 | 0.020319 | 0.017382 | −0.014068 | 0.042439 | 0.024206 |
| 211 | −0.003388 | 0.00708 | −0.029318 | 0.004159 | −0.008968 | −0.010768 | −0.015062 | −0.012508 | 0.024508 | −0.005569 | 0.025047 | 0.00363 | 0.016119 | 0.031957 |
| 212 | 0.014604 | −0.018701 | 0.019233 | −0.018906 | −0.024959 | −0.019125 | 0.043518 | −0.058449 | −0.007705 | 0.006179 | 0.016534 | 0.013787 | −0.013377 | 0.044277 |
| 213 | −0.024668 | 0.023001 | −0.005025 | −0.032096 | −0.040149 | 0.018312 | −0.006629 | 0.093629 | −0.01992 | −0.01037 | −0.0609 | −0.016104 | 0.074788 | −0.014912 |
| 214 | −0.001777 | −0.007243 | −0.00685 | −0.005629 | 0.00249f | −0.000199 | 0.009564 | −0.011367 | 0.006834 | −0.021212 | −0.010609 | −0.009968 | −0.031108 | −0.001568 |
| 215 | −0.015576 | −0.04443 | −0.047849 | −0.032615 | −0.008258 | 0.119808 | −0.006621 | 0.050485 | −0.000468 | −0.029642 | −0.028716 | −0.001752 | 0.039734 | −0.025453 |
| 216 | 0.023402 | 0.015931 | −0.011433 | −0.01556 | −0.01114 | −0.003757 | −0.021857 | 0.009637 | 0.017852 | −0.07156 | −0.000856 | −0.002973 | 0.024585 | −0.029319 |
| 217 | −0.02492 | 0.019797 | −0.020101 | 0.005265 | −0.043793 | 0.010724 | −0.006006 | 0.04265 | −0.040522 | −0.016848 | −0.023948 | −0.01795 | −0.000996 | −0.011189 |
| 218 | −0.014174 | −0.00654 | −0.013286 | 0.001103 | −0.011376 | 0.002305 | 0.019942 | −0.016687 | 0.018913 | 0.021993 | 0.022169 | −0.00254 | 0.003014 | −0.025643 |
| 219 | −0.031171 | 0.016853 | −0.029595 | −0.027442 | −0.038142 | −0.03865 | 0.007346 | −0.041669 | 0.026514 | −0.010722 | 0.016351 | −0.003873 | −0.011888 | −0.020332 |
| 220 | −0.005257 | 0.003466 | −0.036878 | 0.023637 | 0.004019 | 0.053751 | −0.008351 | −0.023031 | −0.007287 | −0.015057 | −0.009556 | −0.000453 | −0.018429 | 0.002516 |
| 221 | 0.010353 | 0.00247 | −0.036645 | −0.008136 | −0.027245 | 0.012293 | 0.014662 | 0.009257 | −0.011056 | −0.029236 | 0.025896 | −0.005487 | −0.061888 | 0.002741 |
| 222 | 0.005829 | 0.00983 | −0.006705 | −0.004816 | 0.003994 | 0.023711 | 0.022324 | 0.007807 | 0.03471 | 0.011237 | 0.01194 | 0.024042 | −0.019237 | 0.008947 |
| 223 | 0.002439 | −0.003006 | −0.018574 | 0.000706 | 0.015511 | 0.05476 | −0.013574 | −0.00027 | 0.019762 | 0.021768 | 0.025297 | 0.017111 | 0.002124 | −0.004852 |
| 224 | −0.005279 | 0.027084 | −0.052634 | 0.012036 | −0.043863 | −0.000443 | −0.03808 | 0.025302 | −0.001895 | −0.0422 | 0.00194 | −0.01562 | 0.011412 | −0.007903 |
| 225 | −0.012736 | 0.026858 | −0.04294 | 0.025703 | −0.051394 | −0.003757 | −0.017538 | 0.024801 | 0.007137 | −0.046387 | 0.009162 | −0.01754 | 0.004408 | −0.003603 |
| 226 | −0.021708 | −0.019507 | −0.007836 | −0.022997 | 0.013939 | 0.03213 | 0.008013 | −0.038119 | 0.003161 | 0.036236 | −0.001989 | −0.002257 | −0.011504 | −0.020614 |
| 227 | 0.014818 | −0.014488 | −0.009602 | −0.018466 | −0.007733 | 0.011444 | −0.022697 | −0.004831 | −0.029114 | −0.024854 | −0.000756 | −0.029951 | 0.020565 | −0.021902 |
| 228 | 0.012629 | −0.00386 | 0.052591 | −0.019498 | 0.021555 | −0.004622 | −0.00541 | 0.018461 | 0.022669 | −0.018072 | −0.011842 | 0.001656 | −0.02341 | −0.015761 |
| 229 | −0.017227 | −0.002161 | 0.036435 | 0.016987 | −0.002987 | −0.015015 | 0.037611 | 0.042881 | 0.011251 | −0.00496 | −0.012019 | −0.003381 | 0.012801 | 0.004698 |
| 230 | 0.006876 | 0.001681 | 0.028362 | 0.003448 | −0.01233 | 0.001167 | −0.000737 | 0.022095 | 0.037772 | −0.049848 | −0.012559 | 0.010232 | 0.053475 | 0.007481 |
| 231 | −0.031756 | −0.039021 | 0.003944 | 0.003525 | 0.016792 | 0.003914 | −0.017548 | −0.037144 | −0.037413 | 0.011448 | 0.000065 | −0.016788 | 0.013762 | 0.012067 |
| 232 | 0.008827 | −0.029097 | −0.0388 | −0.017542 | 0.019542 | 0.039005 | −0.013892 | −0.016933 | −0.010325 | 0.004353 | 0.011081 | 0.003975 | −0.009296 | −0.026622 |
| 233 | −0.035745 | −0.026597 | −0.012295 | 0.005425 | 0.010441 | 0.028642 | 0.028457 | −0.00586 | −0.022748 | −0.032018 | 0.008879 | 0.002296 | −0.007496 | −0.048505 |
| 234 | −0.028938 | −0.005562 | 0.085065 | −0.03945 | 0.015893 | −0.030245 | 0.025609 | −0.026153 | 0.008371 | −0.02622 | 0.002347 | 0.008716 | −0.003355 | 0.005602 |
| 235 | −0.059288 | 0.017292 | 0.042562 | −0.008528 | −0.014505 | 0.0098191 | 0.035813 | −0.0135481 | −0.025517 | −0.012548 | −0.007329 | −0.013615 | −0.012631 | 0.011459 |
| 236 | 0.025062 | 0.020864 | −0.029204 | −0.019903 | −0.009783 | −0.003671 | 0.003073 | −0.0017091 | −0.019843 | 0.009795 | 0.0134081 | 0.003643 | 0.020339 | 0.006955 |
| 237 | −0.003373 | 0.048669 | 0.034907 | 0.014788 | 0.011291 | −0.02065 | 0.019454 | 0.013644 | −0.007472 | −0.009899 | 0.00166 | −0.011093 | 0.018088 | 0.015308 |
| 238 | −0.031795 | 0.029265 | 0.01015 | −0.002052 | −0.012804 | −0.032043 | −0.006958 | −0.014615 | 0.025947 | −0.034899 | −0.001289 | 0.012552 | 0.008341 | 0.027298 |
| 239 | −0.023964 | −0.009783 | −0.019804 | −0.015783 | −0.014594 | −0.015128 | −0.018783 | −0.016229 | 0.020431 | −0.005067 | 0.002746 | 0.015077 | 0.025553 | −0.012658 |
| 240 | −0.004701 | −0.013136 | −0.002993 | 0.00263 | −0.013912 | 0.007692 | −0.018709 | −0.010477 | −0.045295 | −0.012327 | 0.006581 | 0.005005 | −0.040375 | −0.028713 |
| 241 | −0.019187 | −0.00224 | −0.006438 | −0.001875 | −0.008335 | 0.0105061 | 0.0202121 | −0.032286 | −0.012033 | −0.016461 | −0.000103 | 0.0052691 | −0.017761 | −0.031968 |
| 242 | −0.000145 | 0.020151 | −0.013157 | 0.001207 | 0.006106 | 0.049645 | −0.007458 | 0.017522 | −0.020572 | −0.003256 | −0.000339 | −0.006461 | 0.000579 | −0.008002 |
| 243 | −0.00529 | 0.048304 | −0.004176 | −0.000271 | 0.000474 | 0.036591 | 0.012614 | 0.003134 | 0.005865 | −0.026217 | −0.004265 | −0.023446 | 0.028858 | −0.00452 |
| 244 | 0.027904 | −0.003344 | −0.000023 | −0.0036 | 0.0082361 | 0.00183 | 0.003411 | 0.0252 | −0.012114 | −0.019962 | 0.002326 | −0.017306 | 0.014455 | 0.014699 |
| 245 | 0.023273 | −0.049898 | 0.01146 | −0.008529 | −0.004691 | −0.023587 | 0.013306 | 0.034802 | 0.007332 | 0.036842 | 0.007782 | 0.012626 | 0.010122 | 0.005053 |
| 246 | 0.002993 | −0.030681 | 0.000541 | 0.029312 | 0.022747 | 0.02573 | −0.004208 | −0.000409 | 0.00451 | −0.00069 | 0.019393 | 0.029441 | −0.001887 | −0.004045 |
| 247 | 0.011673 | −0.001616 | −0.020807 | 0.010197 | −0.01818 | 0.009499 | 0.000072 | −0.010156 | 0.0071 | −0.017283 | 0.021726 | 0.016243 | −0.001921 | −0.005373 |
| 248 | 0.018206 | 0.007976 | −0.024692 | −0.012812 | −0.013193 | 0.017953 | 0.01899 | −0.029417 | 0.007923 | −0.015192 | 0.006731 | 0.004561 | −0.009418 | −0.000601 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 249 | 0.000294 | −0.005206 | 0.01119 | −0.005464 | 0.014914 | 0.018433 | 0.016997 | −0.05259 | 0.015568 | 0.031568 | −0.014181 | 0.037105 | 0.005976 | 0.00872 |
| 250 | 0.005971 | 0.00003 | 0.005096 | 0.015489 | 0.019074 | 0.011684 | −0.026761 | −0.008502 | −0.041184 | −0.019479 | 0.007549 | 0.000586 | −0.015098 | −0.007021 |
| 251 | −0.030565 | 0.027643 | 0.024015 | 0.008502 | −0.009724 | −0.006013 | −0.002253 | −0.015505 | −0.039413 | −0.00849 | 0.003309 | −0.007341 | −0.05874 | 0.000639 |
| 252 | 0.000837 | −0.008554 | 0.023684 | −0.015558 | 0.006198 | −0.019068 | 0.024811 | −0.012844 | −0.031376 | 0.052203 | −0.01553 | −0.01681 | −0.007054 | 0.010007 |
| 253 | 0.037915 | 0.013356 | 0.002563 | −0.017094 | 0.024947 | 0.044834 | 0.015902 | −0.00706 | 0.031134 | 0.010525 | −0.020097 | −0.000822 | 0.039907 | 0.001868 |
| 254 | 0.022196 | 0.002651 | 0.001957 | 0.003101 | 0.022682 | 0.010667 | −0.024284 | 0.002825 | −0.006477 | 0.004062 | 0.01546 | −0.001717 | 0.013931 | 0.015568 |
| 255 | 0.026803 | −0.002153 | 0.019397 | 0.016835 | 0.01344 | −0.001896 | −0.009758 | 0.003386 | −0.019124 | −0.026158 | 0.012944 | −0.008963 | −0.014739 | 0.025924 |
| 256 | 0.026651 | −0.034217 | 0.026267 | −0.008099 | 0.000963 | −0.020694 | 0.015593 | 0.017945 | 0.019941 | 0.004044 | −0.018857 | 0.021544 | 0.020533 | 0.043451 |
| 257 | 0.015024 | −0.053477 | −0.010829 | −0.012521 | −0.005283 | −0.009767 | −0.03276 | 0.000533 | −0.012038 | 0.009483 | −0.014363 | 0.01961 | 0.008189 | 0.000165 |
| 258 | 0.024016 | −0.010985 | −0.032427 | 0.017697 | −0.02707 | 0.023261 | −0.008435 | 0.005765 | 0.004388 | 0.019225 | 0.003313 | −0.005469 | −0.00349 | 0.007879 |
| 259 | 0.002191 | 0.023664 | 0.024326 | 0.006292 | 0.016058 | −0.013093 | 0.021046 | −0.011478 | 0.00421 | 0.00497 | −0.005774 | 0.005545 | −0.012688 | 0.023049 |
| 260 | 0.007725 | 0.002 | 0.024015 | 0.005253 | 0.003116 | −0.01783 | 0.016844 | −0.011092 | −0.021528 | 0.037215 | −0.008213 | −0.020868 | −0.03225 | 0.023952 |
| 261 | −0.017958 | −0.008192 | 0.026224 | 0.014393 | −0.018788 | −0.024661 | −0.000284 | −0.023472 | −0.017567 | 0.016859 | −0.009182 | −0.002294 | −0.046815 | 0.011721 |
| 262 | −0.003166 | −0.020643 | −0.010904 | −0.00226 | −0.02386 | −0.007984 | −0.012237 | 0.003958 | −0.010402 | 0.028753 | −0.005929 | 0.011872 | 0.002873 | −0.004606 |
| 263 | 0.01126 | 0.003413 | 0.000774 | −0.012078 | −0.006738 | −0.019921 | 0.006795 | 0.007843 | −0.014109 | 0.016826 | −0.012589 | 0.00259 | 0.009626 | 0.008579 |
| 264 | 0.0033 | 0.032781 | 0.015695 | 0.015996 | 0.008508 | −0.019751 | 0.029895 | −0.02559 | 0.026407 | −0.021591 | −0.007435 | 0.009174 | 0.012639 | 0.02429 |
| 265 | −0.002812 | 0.017435 | 0.001614 | 0.019852 | 0.010856 | −0.035465 | −0.000253 | −0.029519 | 0.008661 | 0.00443 | 0.004802 | 0.00082 | 0.033043 | 0.021695 |
| 266 | 0.008726 | −0.00965 | 0.011639 | −0.000094 | 0.013338 | −0.032814 | −0.014325 | −0.031705 | −0.012585 | 0.000805 | 0.015135 | −0.002548 | −0.010891 | 0.018431 |
| 267 | 0.002282 | −0.036937 | −0.025398 | −0.008733 | 0.013016 | 0.039096 | −0.010279 | 0.016902 | 0.031935 | 0.021008 | −0.015149 | 0.003582 | 0.043487 | −0.013029 |
| 268 | −0.008409 | −0.003648 | −0.016815 | −0.027171 | 0.021314 | 0.012084 | 0.001835 | −0.026214 | −0.002759 | 0.02261 | 0.000573 | −0.008923 | −0.005371 | −0.01856 |
| 269 | −0.014448 | 0.007125 | −0.015895 | −0.024184 | 0.012781 | 0.025561 | −0.003115 | −0.026366 | −0.007968 | 0.014158 | −0.000517 | −0.013952 | −0.013559 | −0.010726 |
| 270 | 0.022626 | −0.00803 | −0.001198 | −0.026876 | 0.020563 | 0.017574 | −0.018829 | −0.029584 | −0.008538 | 0.018397 | −0.007648 | −0.017587 | −0.005566 | −0.015839 |
| 271 | 0.004912 | 0.017353 | 0.006529 | 0.017542 | 0.013976 | 0.000769 | 0.006466 | 0.020732 | 0.025234 | 0.024644 | 0.01783 | 0.024416 | −0.007395 | −0.021289 |
| 272 | −0.030147 | −0.008687 | 0.026594 | 0.028215 | −0.013849 | −0.021023 | 0.033771 | 0.019545 | 0.021465 | 0.018092 | −0.016943 | −0.001015 | 0.003703 | 0.004494 |
| 273 | −0.007448 | 0.017733 | −0.003942 | 0.014635 | −0.00773 | 0.000679 | 0.02368 | 0.003493 | 0.014002 | 0.028591 | −0.018184 | −0.013059 | 0.003186 | 0.008748 |
| 274 | −0.011135 | 0.019958 | −0.002882 | 0.015793 | −0.012171 | 0.002017 | 0.021868 | −0.000776 | 0.009537 | 0.019276 | −0.020481 | −0.013498 | 0.001292 | 0.00874 |
| 275 | 0.033996 | 0.002282 | 0.014408 | −0.002055 | −0.011535 | 0.013117 | −0.016455 | 0.008067 | 0.014378 | −0.040396 | −0.030305 | −0.016467 | 0.023285 | 0.012892 |
| 276 | 0.027085 | 0.026259 | −0.02224 | −0.009218 | −0.013876 | −0.015332 | 0.005096 | 0.010498 | −0.014338 | 0.016152 | 0.014733 | 0.003287 | 0.019071 | 0.001385 |
| 277 | 0.017722 | 0.013247 | 0.008083 | −0.007082 | −0.000671 | −0.017192 | 0.012036 | 0.030268 | −0.007045 | 0.025759 | 0.006883 | −0.0148 | 0.006372 | −0.007663 |
| 278 | 0.016295 | 0.007313 | 0.010399 | −0.009479 | 0.000796 | −0.002189 | 0.010944 | 0.027938 | −0.011671 | 0.018152 | −0.004331 | −0.018911 | 0.00091 | −0.006157 |
| 279 | −0.015364 | 0.009473 | −0.004312 | −0.029709 | −0.016757 | −0.029893 | −0.022595 | −0.013958 | 0.016961 | −0.010056 | −0.000827 | 0.00754 | −0.001056 | −0.015752 |
| 280 | 0.018331 | 0.065448 | −0.003714 | 0.005065 | 0.019784 | 0.040184 | 0.020986 | 0.027411 | 0.024643 | −0.040472 | −0.009118 | −0.01172 | 0.054047 | −0.011129 |
| 281 | −0.012176 | −0.040618 | 0.003107 | 0.038824 | 0.022055 | 0.036499 | 0.011241 | −0.017756 | 0.020548 | 0.023869 | 0.011478 | 0.02482 | −0.00876 | −0.011305 |
| 282 | −0.007562 | −0.032529 | 0.005242 | 0.038735 | 0.017184 | 0.034405 | 0.009788 | −0.004867 | 0.021307 | 0.029137 | 0.01959 | 0.028536 | −0.015177 | −0.004125 |
| 283 | −0.007758 | 0.016258 | −0.000168 | −0.009702 | −0.026055 | 0.006066 | 0.01964 | −0.028282 | 0.01594 | −0.008917 | 0.007427 | 0.009577 | −0.025771 | −0.013032 |
| 284 | −0.005203 | −0.02247 | −0.000076 | −0.006155 | −0.010049 | −0.014949 | −0.020175 | 0.002449 | 0.000483 | −0.000711 | −0.021892 | 0.013939 | −0.000431 | 0.004518 |
| 285 | −0.000709 | −0.030705 | 0.004049 | −4.016793 | 0.000027 | −0.012318 | −0.029435 | −0.004806 | 0.00337 | 0.010937 | −0.016853 | 0.02219 | 0.002067 | 0.002251 |
| 286 | −0.00213 | −0.015655 | −0.012663 | 0.021356 | −0.022258 | 0.000008 | −0.017984 | 0.007216 | 0.000733 | −0.000274 | −0.00937 | 0.000486 | −0.001679 | 0.005336 |
| 287 | 0.011113 | −0.007467 | −0.000869 | 0.011599 | −0.017066 | 0.008781 | −0.010506 | 0.005727 | 0.000725 | 0.003532 | −0.00837 | −0.007439 | −0.007366 | 0.002971 |
| 288 | 0.029245 | 0.038319 | −0.017129 | 0.010152 | −0.025413 | 0.043428 | −0.009087 | 0.008663 | −0.01065 | 0.003731 | −0.010862 | −0.028132 | −0.049168 | 0.013101 |
| 289 | 0.023494 | 0.001435 | −0.018152 | −0.005287 | −0.00761 | 0.01246 | −0.008218 | −0.000659 | −0.031593 | 0.018246 | −0.010404 | −0.003112 | −0.008065 | 0.00692 |
| 290 | 0.002132 | 0.039352 | 0.002606 | 0.011109 | 0.008431 | 0.022254 | −0.01564 | −0.00761 | 0.00669 | 0.003833 | −0.029484 | −0.026515 | −0.023762 | 0.031408 |
| 291 | 0.002787 | 0.035258 | 0.003567 | 0.009549 | 0.006879 | 0.018458 | −0.019563 | −0.006589 | 0.00647 | 0.005047 | −0.026783 | −0.024635 | −0.019579 | 0.029483 |
| 292 | −0.005684 | 0.031845 | 0.004955 | 0.007147 | 0.005951 | 0.021402 | −0.031599 | −0.009226 | −0.00223 | −0.006811 | −0.022364 | −0.01937 | −0.018379 | 0.021092 |
| 293 | 0.034106 | −0.015906 | −0.047629 | −0.028 | −0.015505 | 0.010615 | −0.007134 | −0.003232 | −0.043474 | −0.034834 | 0.006952 | −0.022132 | −0.008084 | 0.016857 |
| 294 | 0.000422 | −0.007461 | −0.011115 | −0.01406 | −0.003721 | 0.011148 | 0.25788 | −0.011503 | −0.005091 | 0.013697 | 0.008394 | −0.013617 | −0.011493 | 0.016595 |
| 295 | 0.006953 | −0.009759 | −0.004716 | 0.005865 | −0.014509 | −0.004855 | −0.005704 | 0.023583 | −0.014117 | −0.000935 | −0.01561 | −0.007581 | −0.002118 | 0.01744 |
| 296 | 0.01449 | 0.002337 | 0.018919 | 0.016545 | −0.011105 | 0.048843 | 0.004498 | 0.014762 | 0.013937 | 0.023196 | −0.006335 | −0.008447 | −0.027839 | 0.013569 |
| 297 | 0.017375 | −0.02309 | −0.02244 | 0.005335 | −0.02061 | 0.019343 | −0.006191 | 0.004282 | −0.012847 | 0.011203 | −0.013859 | −0.013499 | −0.003069 | 0.016744 |
| 298 | −0.021981 | −0.0038 | −0.010041 | −0.01754 | 0.008818 | −0.010059 | −0.014709 | −0.011257 | 0.046936 | 0.034277 | 0.020659 | 0.016204 | 0.002077 | 0.035065 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 299 | 0.002478 | −0.006265 | −0.015202 | −0.003506 | 0.006126 | −0.008986 | −0.000629 | −0.019883 | 0.007387 | 0.017276 | 0.023421 | 0.000539 | 0.012011 | 0.005426 |
| 300 | 0.012015 | 0.014674 | 0.023305 | 0.008602 | 0.00621 | −0.007787 | −0.026227 | 0.019927 | 0.041008 | −0.038925 | 0.000137 | 0.034553 | 0.003605 | −0.007366 |
| 301 | −0.000012 | −0.010918 | 0.002749 | −0.022633 | −0.001556 | −0.023013 | −0.006068 | −0.002814 | 0.005485 | −0.001912 | 0.002706 | 0.013418 | −0.000534 | 0.016432 |
| 302 | −0.01275 | −0.014631 | −0.004694 | −0.010982 | −0.003293 | 0.001406 | −0.027873 | 0.008307 | 0.022251 | 0.00188 | −0.00811 | 0.02672 | 0.005755 | −0.006416 |
| 303 | −0.017753 | −0.018492 | 0.002933 | 0.015832 | −0.011631 | −0.003004 | 0.000738 | 0.013616 | 0.02698 | 0.019195 | 0.033263 | 0.0073 | 0.018941 | −0.0085 |
| 304 | −0.010898 | 0.016153 | 0.019034 | −0.007967 | 0.002305 | 0.00124 | 0.011039 | 0.002362 | 0.037084 | 0.015708 | 0.010634 | 0.005872 | 0.018709 | −0.005577 |
| 305 | −0.007516 | −0.046437 | −0.016001 | −0.000535 | −0.018411 | −0.014939 | −0.024005 | 0.002811 | −0.021678 | −0.059537 | −0.017107 | 0.010208 | −0.002455 | −0.005663 |
| 306 | 0.028052 | 0.006733 | −0.019299 | 0.041356 | −0.038284 | 0.019469 | 0.029638 | −0.018093 | 0.006221 | −0.011637 | −0.005953 | −0.14765 | −0.005999 | 0.008362 |
| 307 | 0.032363 | −0.040111 | 0.060457 | 0.030237 | 0.058408 | 0.014402 | 0.006897 | −0.01036 | 0.042006 | 0.028644 | −0.028143 | −0.00668 | −0.024832 | −0.007257 |
| 308 | 0.067939 | 0.077364 | 0.019535 | 0.033779 | 0.06499 | −0.000537 | 0.011094 | 0.017056 | −0.032255 | 0.025359 | 0.021081 | −0.0287 | −0.031889 | 0.024616 |
| 309 | −0.006846 | 0.004189 | 0.01678 | −0.009749 | 0.003289 | 0.003148 | −0.017534 | −0.001453 | 0.010944 | −0.005034 | −0.003813 | −0.004583 | 0.004045 | 0.006871 |
| 310 | −0.051788 | −0.040209 | 0.013111 | 0.026475 | −0.009207 | 0.010631 | 0.001991 | 0.000921 | 0.028298 | −0.021089 | −0.012586 | −0.000785 | 0.044189 | 0.002223 |
| 311 | 0.014338 | 0.038374 | −0.006721 | −0.024475 | −0.004437 | −0.026645 | 0.029854 | −0.026552 | 0.012588 | −0.002161 | −0.005919 | −0.019186 | −0.015461 | 0.009646 |
| 312 | −0.039763 | −0.005806 | −0.058158 | 0.011378 | −0.025017 | 0.131184 | 0.021238 | −0.061216 | −0.044229 | 0.062166 | −0.021044 | −0.060371 | 0.032631 | 0.005743 |
| 313 | 0.002297 | 0.030465 | 0.004372 | −0.006502 | −0.011364 | −0.021907 | 0.030164 | −0.030438 | 0.007557 | −0.026182 | −0.01266 | −0.005597 | 0.025074 | 0.038469 |
| 314 | 0.032087 | −0.055755 | 0.037157 | −0.058551 | 0.022275 | 0.018849 | 0.032621 | −0.024349 | −0.081908 | 0.012092 | −0.013575 | −0.02463 | 0.08075 | 0.031937 |
| 315 | 0.005121 | 0.010786 | 0.00668 | 0.010558 | 0.006476 | 0.023936 | −0.016893 | −0.005704 | −0.019162 | −0.011591 | 0.015683 | −0.014391 | −0.003274 | −0.004349 |
| 316 | 0.57766 | −0.023769 | −0.014394 | −0.00528 | −0.02473 | −0.046136 | −0.069813 | 0.002329 | −0.007909 | −0.089075 | 0.001628 | −0.028507 | 0.004644 | 0.023664 |
| 317 | −0.005166 | −0.015422 | 0.029743 | −0.020602 | 0.006025 | −0.021612 | −0.016611 | 0.003659 | −0.018258 | 0.005796 | 0.004512 | 0.000484 | 0.000269 | 0.012506 |
| 318 | 0.00128 | −0.015259 | 0.022067 | −0.034315 | 0.052388 | 0.013057 | 0.004529 | −0.006252 | −0.04568 | 0.003809 | −0.00549 | −0.17187 | −0.060848 | 0.019854 |
| 319 | −0.020166 | 0.007424 | 0.01453 | 0.004335 | 0.001818 | 0.01236 | −0.011831 | −0.000229 | −0.000059 | 0.000754 | 0.016433 | −0.015002 | −0.017304 | 0.002605 |
| 320 | −0.027878 | −0.018047 | −0.025109 | −0.005994 | −0.012487 | 0.00511 | 0.008899 | −0.021084 | 0.007377 | 0.01939 | −0.005868 | −0.026519 | −0.041887 | 0.025684 |
| 321 | 0.018782 | −0.014182 | 0.021528 | 0.01738 | 0.022791 | −0.019781 | 0.0306 | 0.009721 | 0.007578 | 0.030677 | −0.009124 | −0.002861 | −0.024108 | 0.022301 |
| 322 | −0.010826 | −0.011561 | 0.008715 | 0.030089 | 0.023174 | −0.002592 | −0.013127 | 0.030809 | −0.103373 | −0.040504 | −0.006247 | −0.016314 | 0.011555 | 0.003504 |
| 323 | −0.033312 | 0.005535 | −0.01701 | −0.008685 | 0.013912 | −0.044873 | 0.002413 | −0.034845 | −0.018024 | 0.010713 | −0.008262 | −0.005396 | 0.041773 | 0.018078 |
| 324 | 0.068652 | 0.003462 | −0.025829 | −0.030974 | 0.025123 | 0.06854 | −0.038172 | −0.050409 | 0.037935 | 0.002604 | −0.00377 | 0.009374 | −0.01581 | −0.019931 |
| 325 | −0.006283 | 0.016169 | 0.010363 | 0.015422 | −0.014955 | 0.022963 | −0.006189 | −0.007732 | 0.020225 | −0.007437 | 0.006417 | −0.010559 | −0.035185 | 0.002354 |
| 326 | 0.022104 | 0.035615 | −0.020869 | −0.002757 | −0.020717 | −0.020927 | 0.014963 | −0.026018 | 0.023294 | −0.003055 | −0.009194 | −0.000888 | −0.010548 | 0.010028 |
| 327 | −0.044109 | 0.018385 | 0.003039 | 0.010509 | −0.0035 | −0.010646 | −0.014779 | 0.012103 | 0.025019 | −0.01295 | 0.000773 | 0.0123 | −0.011183 | −0.004264 |
| 328 | 0.051892 | 0.002982 | −0.027689 | −0.016375 | −0.040143 | 0.002441 | 0.033987 | −0.028723 | 0.003169 | 0.046105 | 0.017773 | 0.032783 | −0.027769 | 0.022042 |
| 329 | −0.032229 | −0.000122 | −0.021041 | −0.001471 | −0.001566 | −0.047812 | 0.003042 | −0.022394 | 0.007135 | −0.006211 | 0.016855 | 0.023746 | −0.014041 | −0.003789 |
| 330 | −0.046661 | −0.029199 | −0.003719 | 0.024527 | −0.033073 | −0.022175 | 0.036786 | 0.023404 | 0.004992 | 0.016026 | 0.000738 | 0.007438 | 0.014699 | 0.013799 |
| 331 | 0.007483 | 0.022241 | −0.023767 | 0.001062 | −0.002079 | 0.006626 | 0.000378 | −0.004358 | 0.001437 | −0.016291 | 0.010787 | −0.014732 | −0.017078 | −0.004076 |
| 332 | 0.033928 | 0.019597 | −0.004618 | 0.006968 | −0.053242 | −0.008962 | 0.058778 | 0.017132 | 0.069847 | 0.007258 | −0.002956 | 0.011402 | −0.057392 | 0.011881 |
| 333 | 0.016998 | 0.009457 | 0.006503 | −0.012957 | 0.017657 | 0.007927 | −0.024794 | 0.001579 | 0.005089 | −0.012856 | −0.001549 | −0.004892 | −0.040677 | 0.003877 |
| 334 | −0.081545 | −0.00005 | −0.008436 | 0.036945 | −0.02832 | 0.065952 | −0.045992 | 0.015463 | −0.008585 | 0.014548 | 0.013534 | 0.034536 | −0.024706 | −0.015105 |
| 335 | −0.019192 | 0.026768 | 0.005315 | −0.013091 | 0.005034 | 0.000139 | 0.025236 | −0.040489 | 0.027073 | −0.01116 | −0.004734 | −0.018479 | −0.013203 | 0.013562 |
| 336 | 0.003149 | 0.040416 | 0.058336 | 0.00059 | 0.005789 | −0.03648 | 0.009776 | 0.050532 | 0.034879 | −0.024909 | 0.001609 | 0.008204 | 0.042911 | 0.006931 |
| 337 | −0.001525 | 0.003845 | 0.039632 | 0.014861 | 0.016553 | −0.030424 | −0.015318 | −0.043514 | −0.007534 | 0.02178 | 0.009756 | −0.013321 | −0.035263 | 0.017907 |
| 338 | −0.090544 | 0.043189 | −0.001168 | −0.001669 | −0.032735 | 0.011429 | 0.003842 | 0.026015 | 0.042348 | 0.016964 | 0.033695 | 0.036251 | −0.002613 | −0.032951 |
| 339 | −0.040055 | 0.003033 | −0.009047 | −0.018748 | −0.031939 | −0.04217 | −0.013008 | −0.006408 | −0.001384 | 0.030139 | −0.035532 | −0.00622 | −0.048245 | −0.000344 |
| 340 | 0.019583 | −0.01172 | −0.005469 | 0.009429 | 0.012681 | 0.015671 | −0.012724 | 0.011278 | −0.011792 | −0.045325 | −0.008932 | −0.0092 | 0.000021 | −0.027191 |
| | DT | DU | DV | DW | DX | DY | DZ | EA | EB | EC | ED | EE | EF | EG |
| 1 | 0.057072 | 0.098056 | 0.018633 | 0.015397 | 0.017317 | 0.010887 | 0.011164 | 0.028164 | −0.039851 | −0.053264 | −0.048275 | 0.012191 | 0.056079 | 0.057586 |
| 2 | −0.064457 | −0.097709 | −0.018875 | −0.054905 | −0.111531 | 0.009391 | 0.137688 | 0.012079 | 0.099505 | 0.033557 | 0.015591 | 0.007063 | −0.016329 | −0.042138 |
| 3 | −0.009663 | −0.105045 | 0.004613 | 0.027758 | 0.004129 | 0.024537 | −0.173021 | 0.001295 | 0.017164 | −0.013735 | 0.055168 | 0.05229 | −0.004565 | −0.015405 |
| 4 | −0.009037 | 0.068598 | 0.004971 | 0.002233 | 0.027089 | −0.058943 | 0.016425 | −0.099968 | −0.074755 | 0.01053 | −0.041034 | −0.095389 | 0.059857 | −0.086692 |
| 5 | 0.052042 | −0.026851 | −0.06671 | 0.028245 | −0.056437 | −0.016167 | −0.114122 | −0.046122 | −0.050048 | 0.018419 | −0.091749 | −0.024165 | −0.050045 | −0.052759 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 6 | 0.047335 | 0.021547 | 0.007661 | −0.037201 | −0.035944 | 0.01167 | −0.033079 | −0.067312 | 0.006663 | −0.009966 | 0.094079 | −0.007628 | 0.010441 | 0.051009 |
| 7 | 0.002286 | −0.136826 | 0.063883 | 0.044011 | 0.009951 | 0.002913 | −0.040126 | −0.045367 | −0.041561 | −0.098601 | −0.117911 | 0.017165 | −0.025088 | −0.115405 |
| 8 | −0.167402 | −0.079525 | −0.05671 | 0.02305 | −0.003932 | 0.01056 | 0.039079 | 0.036155 | 0.038761 | 0.00278 | 0.030201 | 0.072729 | 0.011572 | −0.001142 |
| 9 | 0.052421 | 0.021364 | −0.030586 | 0.046659 | 0.048916 | 0.028503 | 0.060659 | 0.14572 | −0.043361 | 0.039109 | 0.048936 | −0.013733 | 0.020551 | −0.001289 |
| 10 | 0.039277 | 0.065422 | 0.012175 | −0.032518 | 0.001565 | 0.098594 | −0.00913 | 0.094238 | 0.012824 | 0.028603 | 0.063664 | −0.039919 | 0.004581 | 0.132362 |
| 11 | −0.068361 | −0.000221 | 0.046925 | −0.031425 | −0.012746 | −0.074925 | 0.01729 | 0.023266 | 0.042931 | −0.027956 | −0.007056 | 0.08548 | −0.000407 | 0.026619 |
| 12 | 0.011594 | 0.041986 | −0.003265 | 0.026128 | 0.058376 | 0.034368 | 0.035981 | 0.044342 | 0.062356 | −0.03188 | 0.039868 | 0.005237 | −0.005982 | −0.03959 |
| 13 | −0.041135 | −0.019962 | −0.085392 | −0.020549 | 0.041136 | −0.007776 | −0.073426 | 0.012659 | 0.015724 | −0.013391 | −0.00695 | 0.030376 | −0.006982 | −0.036727 |
| 14 | 0.05546 | 0.070031 | 0.004958 | 0.000082 | 0.013412 | 0.074201 | 0.077087 | 0.050987 | 0.114167 | 0.033562 | 0.005 | 0.007874 | 0.000724 | −0.014704 |
| 15 | −0.031157 | −0.017121 | −0.029887 | −0.007414 | 0.004177 | −0.034621 | −0.063205 | 0.020653 | 0.043724 | −0.003806 | 0.04077 | 0.003287 | 0.000681 | 0.045895 |
| 16 | 0.016608 | −0.043781 | 0.026473 | −0.018496 | −0.042728 | 0.077571 | 0.080679 | 0.022906 | −0.055382 | −0.002801 | 0.004104 | −0.066833 | −0.029956 | 0.075573 |
| 17 | −0.033018 | −0.036376 | −0.017826 | 0.000834 | 0.032732 | 0.039322 | 0.009161 | −0.070105 | −0.075618 | −0.019292 | −0.038503 | −0.036382 | −0.020469 | −0.043322 |
| 18 | −0.051712 | 0.030746 | −0.115776 | −0.008068 | 0.006409 | −0.008798 | 0.113893 | −0.083852 | 0.009949 | 0.014232 | −0.032286 | 0.12701 | −0.031179 | −0.015286 |
| 19 | 0.031341 | −0.042903 | 0.078172 | 0.094772 | 0.057967 | 0.021111 | 0.115495 | 0.019036 | 0.028021 | −0.008513 | 0.054525 | 0.082719 | 0.033725 | −0.041722 |
| 20 | −0.004914 | −0.063139 | −0.023502 | 0.0706 | −0.006742 | 0.045419 | 0.062578 | 0.025982 | 0.029378 | −0.02875 | 0.043772 | −0.017528 | −0.018665 | −0.035007 |
| 21 | −0.067134 | −0.037097 | 0.009951 | −0.093405 | −0.035011 | −0.014718 | −0.003529 | −0.057986 | −0.165332 | 0.022264 | 0.026697 | −0.000098 | −0.018312 | −0.072467 |
| 22 | 0.006309 | 0.041195 | −0.071024 | 0.029198 | 0.0076 | 0.033089 | −0.026436 | −0.047598 | 0.004126 | −0.018159 | −0.002232 | −0.121252 | 0.001196 | −0.006674 |
| 23 | 0.079175 | −0.008468 | −0.087038 | −0.062792 | −0.022388 | −0.032899 | 0.075946 | −0.005704 | −0.097696 | −0.06536 | 0.007068 | 0.045634 | 0.062774 | 0.088654 |
| 24 | −0.068347 | −0.067847 | 0.020139 | 0.008463 | 0.031732 | −0.014173 | −0.049555 | 0.070922 | 0.058602 | 0.000442 | 0.101031 | −0.031021 | 0.000269 | −0.022827 |
| 25 | −0.065515 | −0.012289 | −0.052826 | −0.072469 | −0.105158 | −0.019947 | 0.014972 | 0.088599 | −0.09161 | 0.016301 | 0.020487 | −0.050078 | 0.020169 | −0.048249 |
| 26 | −0.055801 | −0.045849 | 0.026326 | −0.0102636 | −0.03581 | 0.032956 | 0.210398 | 0.054306 | 0.024646 | 0.136978 | −0.101122 | 0.021656 | −0.013269 | −0.063499 |
| 27 | 0.043513 | −0.013941 | 0.001473 | 0.021015 | 0.029937 | 0.051018 | 0.105148 | 0.091414 | 0.054146 | 0.055212 | 0.023688 | 0.089018 | −0.009981 | 0.10587 |
| 28 | −0.022063 | −0.040354 | 0.025205 | 0.035611 | 0.011184 | −0.022805 | −0.036846 | −0.078978 | 0.134312 | 0.001049 | 0.029872 | 0.106113 | 0.043326 | 0.160103 |
| 29 | 0.010021 | 0.010129 | 0.019876 | −0.007729 | 0.017895 | −0.005957 | −0.009436 | −0.023691 | 0.009453 | 0.001182 | 0.009047 | 0.056076 | 0.015394 | 0.022272 |
| 30 | 0.011893 | 0.039411 | 0.08219 | −0.051323 | −0.077122 | 0.030718 | −0.01876 | −0.026128 | 0.018579 | 0.028585 | −0.029802 | 0.15961 | 0.024606 | 0.0146 |
| 31 | 0.054418 | 0.055985 | −0.003725 | −0.032378 | −0.03071 | 0.010008 | −0.026302 | 0.046516 | 0.206422 | 0.120361 | 0.125916 | −0.124661 | 0.009283 | −0.03027 |
| 32 | −0.026604 | −0.010428 | −0.083025 | −0.041895 | 0.046609 | −0.024411 | −0.11033 | 0.07168 | −0.028111 | −0.01749 | −0.047475 | 0.031286 | −0.027487 | 0.003097 |
| 33 | −0.014329 | −0.003934 | 0.062439 | −0.0034 | 0.043184 | −0.044761 | −0.119518 | −0.04877 | 0.119581 | −0.057292 | −0.046268 | 0.073517 | −0.013545 | −0.046228 |
| 34 | −0.025619 | −0.083538 | 0.02843 | −0.016501 | 0.041983 | −0.004535 | 0.00582 | −0.095747 | −0.068138 | 0.004972 | 0.052572 | −0.096297 | −0.004047 | 0.001384 |
| 35 | −0.047818 | 0.026558 | −0.038168 | −0.099373 | −0.049032 | −0.021581 | −0.023672 | −0.013613 | 0.015153 | −0.053014 | 0.006351 | 0.060455 | −0.047914 | 0.05894 |
| 36 | −0.040103 | 0.035703 | −0.058792 | 0.021986 | 0.043878 | −0.002003 | 0.055614 | 0.082619 | 0.072779 | 0.005254 | −0.125786 | 0.056933 | 0.008186 | 0.02078 |
| 37 | −0.080605 | −0.02912 | −0.058435 | 0.016048 | 0.032526 | 0.066764 | −0.135037 | −0.058566 | −0.013269 | 0.052486 | 0.04086 | −0.089656 | −0.022149 | 0.009515 |
| 38 | −0.049797 | 0.009062 | 0.038711 | −0.100916 | −0.069881 | −0.006968 | 0.103285 | 0.019371 | −0.010119 | 0.005166 | 0.035555 | −0.091774 | 0.024528 | 0.020239 |
| 39 | −0.045159 | 0.022959 | −0.037009 | −0.026225 | −0.067589 | 0.090799 | −0.14352 | 0.064249 | 0.010323 | 0.038944 | 0.053503 | −0.023937 | 0.072339 | −0.060199 |
| 40 | 0.006544 | 0.011105 | −0.013858 | 0.01213 | 0.024133 | 0.016148 | −0.000612 | 0.046745 | −0.026946 | −0.016931 | 0.003403 | −0.011327 | 0.016852 | −0.007209 |
| 41 | −0.008409 | −0.046763 | 0.00548 | −0.014381 | −0.017708 | 0.027239 | 0.065215 | 0.011139 | −0.131057 | 0.048525 | −0.066515 | −0.080569 | −0.059712 | −0.011275 |
| 42 | 0.015431 | −0.03886 | 0.003638 | 0.020564 | −0.023167 | −0.013474 | −0.193756 | 0.052218 | −0.126718 | 0.053085 | −0.171342 | 0.075275 | 0.058446 | −0.056137 |
| 43 | 0.010193 | 0.023925 | −0.146463 | 0.024929 | −0.027707 | −0.098775 | 0.060688 | 0.008016 | 0.206364 | −0.107649 | −0.070764 | 0.060239 | −0.131054 | −0.011587 |
| 44 | 0.04253 | 0.05379 | −0.008091 | 0.07477 | 0.006048 | −0.041532 | −0.048121 | −0.006983 | 0.020133 | 0.052957 | −0.110382 | 0.155058 | 0.0298 | 0.128613 |
| 45 | −0.036633 | 0.028414 | 0.003291 | −0.070488 | −0.049383 | −0.006483 | 0.076122 | 0.064023 | 0.035968 | 0.011107 | 0.115883 | −0.018456 | 0.01825 | −0.043247 |
| 46 | −0.02357 | −0.005893 | −0.003454 | 0.068349 | 0.030347 | −0.069796 | 0.153239 | −0.139313 | −0.016059 | −0.052857 | −0.049174 | 0.050542 | −0.03395 | −0.118603 |
| 47 | 0.148566 | 0.036158 | −0.048681 | 0.067486 | 0.005777 | −0.000877 | −0.064202 | 0.013549 | −0.024467 | 0.012233 | −0.114533 | −0.020589 | −0.04336 | −0.065945 |
| 48 | 0.053144 | 0.010542 | 0.027059 | 0.026036 | −0.004727 | −0.084957 | 0.006953 | −0.058274 | 0.006991 | 0.030485 | 0.059685 | −0.013777 | −0.058772 | −0.00399 |
| 49 | −0.00434 | 0.02828 | −0.006278 | −0.015004 | 0.04002 | 0.003261 | 0.01647 | 0.062535 | −0.059834 | −0.038402 | 0.026984 | −0.014805 | 0.028312 | 0.015283 |
| 50 | 0.007369 | 0.022655 | −0.081913 | 0.012174 | 0.010109 | −0.013116 | 0.021265 | 0.107204 | −0.024551 | 0.009658 | −0.031028 | 0.073127 | 0.004572 | 0.061074 |
| 51 | −0.076299 | −0.031357 | −0.081891 | −0.015379 | −0.054105 | −0.045685 | 0.007775 | 0.161563 | −0.00012 | −0.081264 | −0.033103 | −0.052611 | −0.039981 | 0.013164 |
| 52 | −0.023122 | 0.040244 | −0.022959 | 0.006073 | 0.005902 | −0.005674 | −0.070639 | 0.069576 | −0.000531 | −0.068069 | −0.027408 | 0.354232 | −0.046854 | −0.009972 |
| 53 | 0.085954 | −0.026237 | −0.010943 | −0.015 | −0.037391 | −0.021055 | 0.112326 | 0.027458 | −0.04018 | −0.071068 | 0.051566 | 0.038618 | −0.027042 | −0.078556 |
| 54 | 0.121656 | −0.017373 | −0.026796 | 0.039623 | −0.019837 | 0.027583 | 0.013604 | 0.054028 | 0.08267 | 0.037027 | −0.007873 | −0.053647 | −0.043181 | 0.063917 |
| 55 | −0.05054 | −0.022543 | 0.06684 | 0.037784 | 0.053354 | 0.023668 | 0.022138 | 0.080012 | −0.164788 | 0.026039 | 0.007058 | −0.009945 | 0.051008 | −0.001053 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 56 | 0.017044 | −0.000998 | −0.057601 | −0.075562 | −0.012955 | −0.051533 | −0.034495 | −0.046375 | 0.017002 | 0.027799 | 0.033074 | −0.067451 | −0.016752 | 0.149187 |
| 57 | 0.049418 | 0.024245 | −0.058701 | 0.159332 | 0.054888 | −0.018808 | 0.015654 | −0.012348 | 0.012618 | 0.032329 | 0.02037 | −0.0127 | −0.035044 | −0.047495 |
| 58 | −0.058621 | −0.032336 | 0.027287 | 0.02978 | −0.000119 | −0.026606 | −0.030381 | −0.007768 | −0.000504 | −0.072206 | −0.001045 | −0.150338 | −0.021718 | 0.031265 |
| 59 | −0.08435 | −0.071569 | 0.031494 | −0.051358 | 0.002217 | −0.010025 | 0.03429 | 0.07978 | 0.045716 | −0.055958 | −0.027744 | −0.007965 | −0.103119 | −0.025938 |
| 60 | 0.012774 | 0.007763 | 0.023942 | −0.011418 | −0.011006 | −0.006585 | 0.007667 | 0.004913 | −0.017756 | 0.027216 | −0.000183 | −0.012251 | 0.017315 | −0.002299 |
| 61 | 0.002633 | 0.001907 | 0.021558 | 0.027327 | 0.02464 | 0.010155 | −0.01873 | 0.028048 | 0.02926 | 0.016675 | 0.02687 | 0.000195 | 0.01991 | 0.012578 |
| 62 | −0.034198 | −0.011835 | 0.026598 | −0.014569 | 0.022089 | 0.004152 | 0.021412 | −0.021463 | 0.029035 | −0.001221 | 0.005906 | 0.026946 | 0.008811 | 0.006334 |
| 63 | −0.008067 | −0.012386 | 0.011216 | 0.032099 | 0.023005 | 0.012633 | −0.010168 | 0.019709 | 0.009681 | 0.025054 | 0.01106 | 0.029812 | 0.018428 | 0.015927 |
| 64 | 0.00467 | −0.005062 | −0.025401 | 0.053563 | 0.024949 | 0.015167 | −0.028634 | 0.017246 | −0.023248 | −0.01743 | −0.009962 | 0.030225 | −0.006082 | −0.011606 |
| 65 | 0.015255 | 0.007247 | 0.006849 | −0.023546 | −0.010047 | −0.006728 | 0.029172 | 0.002456 | −0.014907 | 0.003801 | −0.002701 | −0.00223 | 0.018438 | 0.010462 |
| 66 | −0.011458 | 0.002784 | 0.010602 | 0.017784 | 0.027297 | 0.007867 | −0.001701 | −0.000698 | 0.002738 | −0.014551 | −0.011775 | 0.026021 | 0.012636 | 0.029949 |
| 67 | 0.029804 | 0.016068 | 0.018757 | 0.026982 | −0.002479 | 0.018475 | −0.015572 | −0.028327 | 0.020272 | 0.026938 | 0.016928 | −0.003937 | 0.011281 | −0.002727 |
| 68 | 0.013457 | 0.021154 | 0.01126 | 0.03553 | 0.00835 | 0.002531 | 0.014462 | −0.02285 | −0.050814 | 0.026387 | −0.029999 | −0.021963 | 0.019633 | 0.021301 |
| 69 | 0.005176 | −0.00647 | −0.006772 | −0.004937 | −0.012005 | −0.005706 | −0.043075 | 0.013907 | −0.007214 | −0.019188 | −0.002475 | −0.006485 | −0.006757 | 0.020479 |
| 70 | −0.005385 | −0.003807 | 0.033057 | −0.022061 | −0.002453 | −0.022356 | 0.031596 | −0.048817 | −0.021223 | 0.008805 | 0.035608 | −0.021098 | 0.007147 | −0.002994 |
| 71 | 0.000194 | −0.002585 | −0.036597 | 0.008123 | −0.018784 | −0.027954 | −0.015704 | 0.013145 | −0.001567 | −0.042638 | −0.015316 | 0.041436 | −0.02216 | 0.008328 |
| 72 | 0.002918 | −0.00645 | −0.012588 | 0.009709 | −0.013504 | −0.033391 | 0.001769 | 0.014743 | 0.006094 | −0.043997 | −0.01395 | 0.008868 | −0.007612 | −0.048047 |
| 73 | 0.000176 | −0.000692 | 0.033335 | −0.008952 | −0.000272 | 0.003406 | 0.018028 | −0.051905 | −0.026231 | −0.016015 | 0.004711 | 0.004262 | −0.013599 | −0.033548 |
| 74 | 0.011949 | −0.009427 | −0.003086 | −0.021434 | 0.004172 | −0.032878 | 0.028208 | 0.016325 | 0.033211 | −0.006294 | 0.014425 | −0.022684 | −0.011885 | 0.011519 |
| 75 | 0.008641 | 0.005127 | 0.003282 | 0.00577 | 0.00104 | −0.020191 | 0.001413 | −0.03757 | −0.018773 | 0.010666 | −0.001629 | 0.003924 | −0.007231 | 0.005007 |
| 76 | 0.002817 | −0.00176 | −0.001054 | −0.011371 | −0.004309 | −0.012214 | 0.027533 | −0.014507 | 0.002887 | −0.001368 | 0.042317 | 0.001104 | −0.002952 | −0.01416 |
| 77 | 0.000817 | 0.003186 | −0.000516 | −0.001909 | −0.004282 | −0.023185 | −0.001301 | −0.02583 | −0.009906 | 0.010928 | 0.010136 | 0.000724 | −0.005684 | 0.019866 |
| 78 | −0.002361 | −0.001829 | 0.011124 | 0.000846 | −0.002621 | −0.025885 | 0.008502 | −0.045969 | −0.010483 | 0.009522 | 0.010361 | −0.004904 | −0.018502 | 0.011873 |
| 79 | 0.011203 | 0.001003 | −0.004626 | 0.016892 | 0.007765 | −0.004113 | −0.005358 | −0.014101 | −0.03455 | −0.001239 | −0.020618 | 0.011851 | −0.012671 | −0.019105 |
| 80 | 0.016746 | −0.012766 | −0.012086 | 0.021797 | 0.020483 | −0.011752 | −0.00398 | 0.029033 | −0.063783 | −0.035206 | −0.034891 | 0.021502 | −0.010993 | 0.022779 |
| 81 | 0.004502 | 0.020151 | −0.009937 | 0.004335 | 0.023673 | −0.013332 | −0.016328 | 0.005345 | 0.064091 | 0.018958 | 0.008538 | 0.025642 | 0.030379 | 0.036879 |
| 82 | −0.006543 | 0.012168 | −0.006281 | −0.008989 | −0.009228 | −0.010594 | 0.024563 | 0.005881 | −0.021668 | −0.033268 | −0.024605 | −0.006136 | −0.002988 | −0.023769 |
| 83 | 0.004926 | 0.008942 | 0.004154 | 0.004496 | −0.00908 | −0.002198 | −0.004507 | −0.003194 | −0.011625 | −0.020573 | −0.018304 | −0.003138 | −0.000188 | 0.002205 |
| 84 | −0.010987 | −0.00674 | −0.003499 | −0.007862 | −0.008945 | −0.001809 | −0.005276 | 0.002777 | −0.000728 | −0.022906 | −0.008919 | −0.005692 | 0.002386 | 0.007123 |
| 85 | 0.000975 | 0.023192 | −0.014765 | 0.034017 | 0.044036 | 0.01824 | −0.086987 | −0.019611 | −0.027674 | −0.014369 | −0.009104 | −0.034752 | 0.030251 | −0.049217 |
| 86 | 0.003743 | 0.00083 | −0.014546 | 0.00697 | −0.009379 | −0.009396 | −0.041653 | −0.035709 | 0.036384 | −0.038995 | 0.005669 | 0.005264 | −0.008951 | −0.02358 |
| 87 | 0.034777 | 0.005203 | −0.007379 | 0.012565 | −0.008209 | −0.002279 | −0.013493 | 0.019798 | −0.046136 | −0.024883 | −0.00957 | 0.005369 | 0.001831 | −0.034683 |
| 88 | 0.002221 | −0.004514 | 0.000767 | 0.003145 | −0.007813 | 0.010574 | −0.015844 | −0.000514 | −0.018153 | −0.01242 | −0.008563 | −0.009223 | −0.005511 | 0.014125 |
| 89 | −0.002696 | −0.001721 | 0.002063 | −0.002877 | −0.00825 | −0.000955 | −0.001456 | 0.001113 | −0.00716 | −0.019309 | −0.008948 | −0.020144 | −0.01363 | 0.01391 |
| 90 | 0.011228 | −0.00354 | 0.006299 | −0.002167 | −0.003358 | −0.001278 | −0.005319 | 0.006813 | −0.013102 | −0.021222 | −0.019659 | −0.008124 | −0.007019 | 0.01217 |
| 91 | −0.002688 | 0.003044 | −0.010119 | 0.002866 | −0.005924 | −0.016043 | 0.017899 | −0.030256 | 0.0265 | −0.023828 | −0.019523 | −0.008524 | −0.007477 | −0.018431 |
| 92 | −0.018614 | −0.000332 | −0.001816 | −0.03792 | −0.03458 | −0.027307 | −0.013387 | −0.073692 | 0.063385 | 0.004132 | 0.017727 | −0.006997 | 0.002156 | −0.051932 |
| 93 | 0.00416 | 0.01217 | 0.009524 | 0.012734 | 0.017467 | −0.003371 | −0.03347 | −0.013367 | −0.017163 | −0.01226 | 0.005097 | 0.002812 | 0.011044 | 0.04429 |
| 94 | −0.004277 | −0.024427 | 0.026764 | −0.010901 | −0.021885 | 0.007227 | −0.003396 | −0.0436 | −0.02307 | −0.005676 | −0.067989 | −0.016609 | −0.007438 | −0.020845 |
| 95 | −0.029068 | 0.003723 | −0.019589 | −0.02809 | −0.012273 | −0.011126 | −0.001142 | −0.012937 | −0.014878 | −0.020222 | −0.058599 | −0.022651 | −0.002807 | 0.018269 |
| 96 | 0.042512 | −0.010808 | 0.011139 | 0.020882 | 0.009269 | −0.02067 | −0.004385 | 0.005189 | −0.0123 | −0.006028 | 0.003074 | −0.014708 | −0.011997 | −0.019503 |
| 97 | 0.044625 | −0.004857 | 0.00494 | 0.009481 | 0.011935 | −0.00441 | −0.009446 | 0.017334 | −0.054625 | −0.009067 | −0.029841 | 0.007769 | 0.004727 | 0.004479 |
| 98 | 0.012935 | 0.004575 | −0.016745 | 0.005664 | −0.000746 | 0.005515 | 0.013058 | 0.013687 | −0.014631 | −0.005113 | −0.035828 | 0.01928 | 0.000446 | −0.013506 |
| 99 | 0.02512 | 0.001565 | −0.005931 | −0.0075 | −0.004354 | −0.002368 | −0.00543 | 0.01433 | 0.001371 | 0.00219 | −0.016761 | −0.001287 | 0.009223 | −0.001382 |
| 100 | −0.019863 | −0.019268 | 0.00245 | 0.009648 | 0.006175 | −0.019474 | 0.015011 | 0.02634 | 0.009167 | −0.022625 | −0.018585 | 0.04111 | −0.011907 | −0.037437 |
| 101 | 0.004447 | −0.000012 | −0.000486 | 0.018107 | 0.015664 | 0.015424 | 0.012598 | −0.007891 | −0.018007 | 0.000923 | −0.01031 | −0.012377 | 0.008619 | 0.007723 |
| 102 | 0.038879 | 0.03111 | −0.003241 | −0.005677 | 0.013412 | −0.003507 | −0.017567 | 0.031108 | −0.008273 | 0.001889 | −0.0004 | −0.007209 | 0.012941 | 0.008245 |
| 103 | 0.02669 | 0.008835 | −0.025315 | 0.014741 | 0.0027161 | −0.012534 | −0.055385 | −0.04247 | −0.066567 | −0.006811 | −0.06656 | −0.038151 | −0.002977 | 0.025662 |
| 104 | 0.029807 | 0.012503 | −0.026634 | −0.011119 | 0.005354 | −0.039037 | 0.00653 | 0.002161 | 0.046823 | −0.049583 | −0.01165 | −0.007195 | −0.029466 | 0.045412 |
| 105 | −0.016975 | 0.01859 | −0.013545 | −0.011587 | 0.022567 | 0.004963 | −0.018909 | 0.023547 | −0.10505 | 0.022427 | 0.031266 | 0.014863 | 0.007128 | 0.007686 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 106 | −0.011274 | 0.002582 | 0.019501 | 0.019764 | −0.010076 | 0.019083 | −0.006379 | −0.014595 | 0.025634 | 0.023755 | −0.018629 | 0.09091 | −0.001551 | −0.004805 |
| 107 | −0.053146 | −0.034916 | 0.030759 | −0.004293 | −0.005112 | 0.016219 | 0.055033 | 0.024672 | −0.011337 | 0.002236 | 0.001906 | 0.034849 | 0.008253 | 0.013077 |
| 108 | −0.009441 | −0.008747 | 0.007688 | 0.032281 | 0.042191 | 0.025826 | −0.009471 | 0.02553 | −0.010675 | −0.012735 | 0.043903 | 0.013824 | 0.02168 | 0.024628 |
| 109 | −0.007009 | 0.009488 | 0.027914 | −0.015454 | 0.0071131 | −0.001272 | 0.013883 | −0.044384 | 0.026113 | 0.00132 | −0.040761 | 0.012085 | 0.000126 | −0.053455 |
| 110 | −0.030736 | 0.00081 | −0.001666 | 0.039436 | −0.00137 | −0.034325 | −0.069235 | 0.027358 | −0.017773 | −0.026715 | −0.038589 | 0.045425 | 0.033594 | −0.047542 |
| 111 | −0.018002 | −0.00795 | 0.022293 | −0.003562 | 0.011181 | 0.04668 | −0.008675 | 0.060299 | −0.009831 | −0.014903 | 0.048557 | −0.030106 | 0.031591 | −0.063393 |
| 112 | −0.002259 | −0.039423 | −0.00726 | 0.037718 | 0.016598 | 0.018551 | −0.092345 | 0.012142 | −0.001409 | 0.010481 | 0.030348 | 0.001282 | −0.008692 | 0.0646 |
| 113 | −0.02844 | −0.000866 | −0.001245 | −0.034255 | −0.001427 | 0.026131 | 0.014552 | 0.004343 | −0.021426 | 0.023225 | −0.016724 | 0.028023 | 0.006954 | −0.03365 |
| 114 | 0.021716 | 0.035766 | 0.030576 | −0.000856 | 0.031413 | −0.004736 | 0.040049 | 0.036896 | 0.084 | 0.028453 | 0.024184 | 0.068934 | −0.002293 | 0.047851 |
| 115 | −0.061887 | −0.010138 | 0.008731 | −0.001045 | 0.011426 | 0.001367 | −0.02306 | −0.076979 | 0.061113 | 0.002367 | 0.051767 | −0.025806 | 0.036263 | −0.027389 |
| 116 | 0.00237 | 0.003508 | 0.046017 | 0.025014 | 0.026309 | 0.0177 | 0.009084 | 0.035131 | −0.056943 | 0.017946 | 0.038126 | −0.029144 | 0.009606 | −0.034005 |
| 117 | 0.011022 | −0.005209 | −0.014222 | −0.060109 | −0.011813 | 0.000486 | 0.014029 | 0.065412 | −0.015382 | −0.029746 | 0.032463 | 0.014897 | 0.006987 | 0.017128 |
| 118 | −0.051259 | −0.034 | −0.023931 | −0.090414 | −0.020302 | −0.027417 | 0.06033 | 0.025807 | −0.022009 | −0.026496 | 0.004066 | −0.002843 | −0.013652 | −0.031226 |
| 119 | −0.06235 | −0.101707 | 0.010161 | −0.004876 | −0.01677 | −0.017808 | −0.030001 | −0.02592 | −0.02701 | −0.035022 | −0.018227 | −0.010176 | −0.026479 | −0.061668 |
| 120 | −0.017738 | −0.016701 | −0.025422 | −0.018202 | 0.01204 | −0.003923 | 0.014172 | −0.000758 | −0.000037 | −0.04001 | 0.002026 | 0.026034 | −0.031166 | −0.012928 |
| 121 | −0.023439 | 0.015394 | −0.015703 | −0.084532 | −0.023617 | 0.021928 | −0.017645 | 0.005741 | −0.048244 | 0.016422 | −0.019983 | −0.002767 | 0.009371 | 0.016642 |
| 122 | −0.088981 | −0.016411 | 0.000186 | −0.045087 | −0.014465 | 0.01272 | −0.010288 | 0.00788 | 0.005742 | 0.026193 | 0.026088 | −0.008944 | 0.015879 | 0.000117 |
| 123 | 0.833411 | −0.054253 | −0.008637 | −0.042659 | −0.004894 | 0.002955 | −0.009639 | 0.008955 | −0.006716 | −0.008617 | 0.013878 | 0.003967 | 0.000295 | −0.032649 |
| 124 | −0.069336 | 0.882821 | 0.018042 | 0.001515 | −0.003713 | −0.002035 | −0.011694 | −0.008991 | −0.021835 | −0.017222 | 0.000647 | −0.005897 | −0.022357 | −0.048304 |
| 125 | 0.003449 | 0.004174 | 0.869281 | 0.00246 | −0.009354 | −0.027187 | −0.015027 | 0.037915 | −0.001312 | −0.026882 | −0.031948 | 0.000595 | −0.028276 | 0.011863 |
| 126 | −0.059017 | −0.002658 | −0.014932 | 0.853343 | −0.07186 | 0.000179 | 0.040284 | 0.02502 | −0.017478 | 0.015399 | 0.026282 | −0.01862 | 0.008795 | 0.018127 |
| 127 | −0.015876 | −0.01319 | −0.023196 | −0.068775 | 0.901746 | −0.011672 | 0.025209 | 0.00845 | 0.005347 | 0.011663 | 0.000586 | −0.015026 | −0.005917 | −0.00595 |
| 128 | −0.00492 | 0.00037 | −0.022857 | −0.002184 | −0.003954 | 0.908268 | 0.004799 | −0.035105 | 0.019889 | −0.048367 | −0.041737 | 0.037387 | −0.026135 | −0.003359 |
| 129 | −0.009047 | −0.017628 | −0.001656 | 0.028831 | 0.021419 | −0.000333 | 0.618375 | −0.035055 | −0.058075 | −0.009815 | −0.0167 | −0.002906 | 0.021653 | −0.005423 |
| 710 | −0.011519 | −0.013577 | 0.024125 | 0.00768 | 0.013838 | −0.033462 | −0.044218 | 0.766094 | −0.03209 | −0.011968 | −0.021247 | −0.02713 | −0.014117 | −0.029643 |
| 131 | −0.007198 | −0.035839 | 0.024582 | −0.006314 | 0.007023 | 0.024498 | −0.060051 | −0.005825 | 0.663565 | 0.000499 | −0.043879 | −0.061599 | 0.027662 | −0.04977 |
| 132 | −0.015048 | −0.016371 | −0.018649 | 0.017474 | 0.007206 | −0.041539 | −0.009748 | −0.005452 | −0.000315 | 0.875294 | −0.0194 | 0.039269 | −0.030664 | −0.016065 |
| 133 | 0.021911 | −0.006578 | −0.026356 | 0.026669 | −0.011308 | −0.037248 | −0.021097 | −0.004896 | −0.061901 | −0.03526 | 0.784213 | 0.094883 | −0.030439 | −0.044587 |
| 134 | −0.004818 | −0.023266 | 0.002777 | −0.042697 | −0.016479 | 0.022471 | −0.014538 | −0.034573 | −0.063084 | 0.049071 | 0.078444 | 0.605623 | 0.009975 | −0.011064 |
| 135 | −0.007832 | −0.028997 | −0.036944 | 0.003235 | −0.009485 | −0.029068 | 0.02012 | −0.007682 | 0.038141 | −0.033037 | −0.022857 | −0.002176 | 0.923682 | −0.023619 |
| 136 | −0.042752 | −0.044624 | 0.011789 | 0.010839 | −0.011799 | −0.01328 | 0.002988 | −0.033225 | −0.043091 | −0.022093 | −0.036624 | −0.030327 | −0.022273 | 0.795687 |
| 137 | −0.015435 | −0.014783 | −0.03081 | −0.006882 | −0.017126 | −0.044915 | −0.025226 | −0.032191 | −0.03912 | −0.011679 | −0.049041 | 0.005399 | −0.019275 | −0.005636 |
| 136 | 0.03998 | −0.008213 | 0.021765 | −0.025161 | −0.021427 | −0.009582 | −0.005615 | −0.076548 | −0.048437 | 0.01633 | −0.004559 | −0.045568 | 0.013037 | 0.015113 |
| 139 | −0.030091 | −0.000631 | 0.046511 | −0.025663 | 0.000401 | 0.025839 | 0.010724 | 0.003947 | 0.013295 | −0.028168 | 0.048103 | 0.054789 | 0.014266 | 0.008137 |
| 140 | 0.01739 | 0.02634 | −0.002035 | 0.005436 | 0.028387 | −0.042787 | −0.05096 | −0.049548 | −0.040982 | −0.046385 | −0.010524 | 0.000938 | 0.011336 | 0.013817 |
| 141 | −0.015236 | 0.00321 | −0.019504 | −0.00601 | −0.015572 | −0.048695 | 0.014752 | −0.027756 | 0.060524 | −0.026655 | −0.002089 | 0.010173 | −0.036594 | 0.023285 |
| 142 | −0.016919 | −0.032801 | 0.025446 | 0.004362 | 0.022415 | 0.025484 | −0.061715 | −0.051364 | 0.005815 | 0.019216 | 0.024813 | 0.031763 | 0.00199 | −0.027371 |
| 143 | −0.055965 | −0.013943 | −0.024493 | 0.030487 | 0.02121 | −0.011787 | −0.022515 | −0.017557 | 0.039665 | 0.001386 | −0.011611 | 0.014079 | −0.025472 | 0.011247 |
| 144 | −0.076216 | −0.066116 | 0.021245 | 0.011344 | 0.007917 | 0.012458 | −0.058064 | −0.009889 | 0.013312 | 0.020686 | 0.007772 | −0.023824 | −0.02824 | −0.053433 |
| 145 | −0.033199 | −0.01395 | −0.01113 | −0.009905 | −0.010831 | −0.027749 | 0.006204 | 0.017323 | 0.012888 | −0.021289 | −0.057929 | −0.00475 | −0.030135 | −0.071986 |
| 146 | 0.006415 | −0.015867 | −0.038876 | 0.001729 | 0.005279 | −0.021212 | −0.000134 | 0.00124 | −0.009192 | −0.055722 | −0.021539 | 0.007867 | −0.043304 | −0.014143 |
| 147 | −0.018691 | 0.018784 | 0.018609 | −0.060072 | 0.000559 | 0.029752 | −0.024358 | −0.027541 | −0.061911 | 0.003644 | 0.020737 | −0.018328 | 0.014923 | 0.027124 |
| 148 | 0.00102 | 0.000386 | 0.032816 | −0.036655 | 0.00033 | −0.02025 | 0.000072 | −0.046221 | −0.048295 | 0.018935 | 0.002585 | 0.039741 | −0.003599 | −0.024194 |
| 149 | −0.010905 | 0.010662 | −0.024476 | 0.001405 | −0.005518 | −0.037952 | 0.006231 | −0.013624 | 0.019831 | −0.01428 | −0.021036 | −0.026653 | −0.021001 | 0.002396 |
| 150 | −0.007274 | −0.024016 | −0.058526 | 0.00059 | 0.001284 | −0.012243 | −0.021137 | −0.025222 | 0.002544 | −0.013717 | 0.006139 | −0.010835 | −0.036514 | −0.009874 |
| 151 | −0.045027 | −0.015323 | 0.018072 | −0.001791 | 0.003955 | 0.012102 | −0.009682 | 0.014676 | 0.058826 | 0.019276 | 0.048888 | −0.097276 | −0.004898 | −0.012229 |
| 152 | −0.018147 | −0.038188 | −0.016713 | −0.007798 | −0.055743 | 0.00846 | −0.054848 | −0.005028 | −0.005952 | 0.012078 | 0.014236 | −0.03772 | −0.008295 | −0.045387 |
| 153 | −0.050113 | −0.04123 | −0.019846 | −0.011305 | −0.001372 | 0.001968 | −0.040043 | −0.007259 | 0.017678 | −0.013593 | 0.0287 | −0.006539 | −0.005571 | −0.037143 |
| 154 | −0.018028 | −0.031502 | 0.015595 | −0.001248 | 0.012107 | 0.013299 | −0.016152 | −0.042655 | −0.059884 | 0.005968 | 0.019984 | −0.035317 | −0.012492 | −0.097448 |
| 155 | −0.009384 | −0.032317 | −0.033867 | 0.007066 | −0.007567 | −0.010959 | −0.041424 | −0.013695 | −0.018966 | −0.053568 | −0.010552 | 0.027457 | −0.020376 | −0.06324 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 156 | −0.02257 | −0.020633 | −0.016402 | 0.00097 | −0.009024 | −0.035496 | 0.037986 | −0.0409 | −0.03326 | 0.003199 | −0.031672 | −0.028557 | −0.023215 | −0.036214 |
| 157 | −0.0132 | −0.019602 | −0.035117 | −0.004334 | −0.004912 | −0.022736 | −0.000822 | 0.010628 | 0.055731 | −0.040137 | −0.017843 | 0.0649 | −0.027976 | −0.014918 |
| 158 | −0.010169 | −0.007338 | 0.012328 | 0.030527 | 0.005042 | −0.029367 | 0.054946 | −0.014455 | 0.052386 | −0.009743 | −0.040873 | 0.026586 | −0.015261 | −0.038052 |
| 159 | 0.015643 | −0.009568 | 0.017773 | 0.011443 | 0.006424 | −0.053094 | −0.053584 | −0.005817 | 0.029147 | 0.015885 | −0.007838 | 0.019665 | −0.034901 | −0.024306 |
| 160 | −0.039304 | −0.027301 | −0.042918 | −0.056597 | −0.034934 | −0.028611 | −0.045081 | 0.043893 | −0.044844 | 0.069673 | −0.048748 | 0.002405 | 0.013921 | −0.005344 |
| 161 | −0.001795 | −0.006948 | 0.026771 | 0.017208 | 0.011562 | −0.03602 | −0.057693 | −0.021687 | 0.034183 | −0.031705 | 0.032292 | −0.022585 | −0.01577 | 0.040928 |
| 162 | −0.025423 | −0.038406 | −0.016782 | −0.0039 | −0.010302 | 0.008243 | −0.03956 | 0.034022 | −0.037169 | −0.010417 | −0.014938 | −0.024538 | −0.016502 | −0.015784 |
| 163 | 0.004825 | −0.036708 | −0.025261 | 0.002632 | −0.039959 | 0.000975 | −0.027406 | −0.002587 | 0.012343 | 0.006206 | 0.00739 | −0.009308 | −0.020206 | −0.010582 |
| 164 | 0.004457 | −0.034159 | 0.014975 | 0.011794 | −0.010676 | 0.000128 | −0.008756 | −0.000392 | −0.041566 | 0.017941 | −0.027718 | 0.071691 | 0.004569 | −0.059112 |
| 165 | 0.013369 | −0.003071 | −0.058466 | −0.045931 | −0.028171 | −0.008744 | −0.058052 | 0.022575 | −4.003417 | 0.002786 | −0.043535 | 0.007802 | 0.000545 | −0.010541 |
| 166 | 0.007243 | −0.056931 | 0.038924 | 0.01831 | 0.038708 | 0.018083 | −0.057137 | −0.069085 | −0.021321 | 0.021942 | −0.036347 | 0.038321 | −0.00551 | −0.026646 |
| 167 | −0.01749 | −0.004199 | −0.021258 | −0.007608 | −0.004601 | −0.031099 | 0.021787 | −0.030773 | 0.034793 | −0.045375 | −0.040412 | 0.027754 | −0.023113 | −0.046834 |
| 168 | −0.012084 | −0.019974 | 0.006582 | 0.011087 | −0.010247 | −0.014488 | 0.008158 | −0.01514 | −0.008079 | 0.019428 | −0.006864 | 0.049829 | 0.003093 | 0.007517 |
| 169 | 0.007871 | −0.002897 | −0.017142 | 0.020308 | 0.00906 | 0.006157 | −0.003694 | −0.029517 | −0.032043 | −0.031352 | −0.003931 | 0.039417 | −0.011589 | 0.011294 |
| 170 | 0.014876 | −0.001761 | 0.014839 | 0.023826 | 0.011121 | 0.010257 | −0.007622 | −0.051346 | −0.049265 | −0.007795 | −0.002555 | 0.028921 | 0.003989 | 0.010784 |
| 171 | −0.035494 | −0.00743 | −0.001468 | −0.017495 | 0.000706 | −0.004586 | −0.007059 | −0.03321 | −0.018149 | −0.028402 | 0.016373 | 0.029325 | −0.012762 | 0.024154 |
| 172 | 0.005388 | −0.006079 | −0.027011 | 0.006528 | 0.015635 | −0.02026 | 0.00566 | 0.00063 | 0.016494 | −0.028248 | −0.005283 | 0.018039 | −0.019136 | 0.000329 |
| 173 | 0.006819 | 0.031872 | −0.038639 | −0.020582 | −0.005804 | −0.008249 | −0.008411 | 0.013098 | 0.018606 | 0.005615 | −0.019534 | 0.020875 | 0.010324 | 0.020406 |
| 174 | 0.018523 | 0.026386 | −0.018604 | 0.015223 | 0.010355 | −0.005427 | 0.016071 | −0.017807 | 0.028361 | −0.008725 | 0.01195 | 0.011753 | −0.006371 | 0.019724 |
| 175 | −0.020516 | −0.000532 | −0.036492 | −0.008376 | −0.010867 | 0.006267 | 0.014988 | −0.015153 | −0.014728 | −0.003627 | 0.057479 | −0.026257 | −0.001181 | −0.003764 |
| 176 | −0.009392 | −0.015367 | 0.003058 | 0.018398 | 0.000464 | −0.015925 | 0.073824 | −0.016537 | −0.037227 | −0.04184 | −0.026211 | 0.054404 | −0.007889 | −0.027549 |
| 177 | 0.031934 | −0.022298 | 0.035348 | −0.012941 | 0.005771 | −0.005605 | 0.071841 | −0.039138 | 0.0137 | 0.010435 | 0.007222 | −0.034362 | −0.021825 | −0.006704 |
| 178 | −0.02159 | −0.01208 | −0.009432 | −0.029127 | −0.023503 | −0.001354 | −0.011501 | 0.015602 | 0.002588 | −0.005656 | −0.030847 | 0.047631 | 0.007461 | 0.02326 |
| 179 | −0.00694 | −0.004487 | −0.010077 | −0.009939 | −0.003115 | 0.009938 | 0.007941 | 0.000935 | −0.014198 | 0.000235 | −0.015865 | 0.032881 | 0.010336 | −0.006788 |
| 180 | −0.003134 | 0.002687 | −0.005391 | −0.010903 | −0.000052 | 0.012466 | 0.003553 | 0.000399 | −0.014603 | 0.003473 | −0.024457 | 0.019698 | 0.011353 | 0.000882 |
| 181 | −0.003871 | −0.000467 | −0.003153 | −0.00252 | 0.002686 | 0.012793 | 0.007031 | 0.007251 | −0.011644 | −0.000931 | −0.025975 | 0.021336 | 0.016055 | −0.003237 |
| 182 | −0.002018 | −0.005261 | 0.021088 | 0.00053 | 0.006103 | 0.001058 | 0.013361 | 0.002692 | −0.002041 | 0.008122 | −0.027249 | 0.035103 | 0.010523 | −0.021073 |
| 183 | −0.04467 | −0.013871 | −0.006146 | −0.035523 | −0.008084 | −0.014837 | 0.012734 | 0.019589 | −0.005118 | −0.007175 | 0.00597 | 0.029904 | −0.004962 | −0.02347 |
| 184 | −0.059539 | −0.014116 | −0.018333 | −0.009857 | 0.017611 | −0.014979 | −0.042675 | 0.014489 | 0.02303 | −0.022817 | 0.022235 | 0.005671 | −0.019761 | 0.013804 |
| 185 | 0.000285 | −0.006763 | −0.015097 | 0.025854 | 0.022813 | −0.027161 | 0.033409 | −0.004529 | 0.06952 | −0.001848 | 0.040717 | 0.022018 | 0.000611 | 0.056969 |
| 186 | −0.043273 | −0.000136 | 0.027935 | 0.000911 | 0.051776 | 0.004693 | −0.054323 | −0.06037 | −0.000202 | −0.018347 | 0.006884 | −0.028128 | 0.010656 | −0.000516 |
| 187 | 0.014053 | 0.01737 | −0.011582 | −0.016699 | 0.003487 | 0.005145 | −0.000748 | 0.036481 | 0.014433 | 0.006587 | −0.002158 | 0.009246 | 0.005745 | −0.004275 |
| 188 | 0.025668 | 0.019611 | 0.003198 | 0.006642 | 0.01641 | 0.006435 | 0.015315 | 0.022095 | 0.014279 | 0.003557 | 0.018356 | 0.025777 | −0.000335 | −0.00583 |
| 189 | 0.000321 | 0.009411 | 0.003917 | 0.01754 | 0.029223 | 0.027248 | 0.019201 | 0.017521 | −0.017311 | −0.000296 | 0.053908 | 0.023322 | 0.000131 | −0.033879 |
| 190 | −0.018095 | −0.00786 | −0.011659 | 0.0071 | 0.005889 | −0.014938 | 0.036793 | −0.020707 | −0.023072 | −0.016292 | −0.013368 | −0.047089 | −0.011681 | −0.006335 |
| 191 | 0.003651 | −0.007339 | −0.013799 | 0.007492 | 0.01248 | −0.020398 | 0.006995 | −0.02243 | −0.008547 | −0.03967 | −0.007946 | −0.053971 | −0.020587 | −0.009999 |
| 192 | 0.01895 | −0.008152 | 0.005388 | −0.016868 | −0.049347 | −0.02408 | 0.013391 | 0.025185 | −0.000571 | 0.012235 | −0.009596 | 0.00251 | −0.013389 | 0.010859 |
| 193 | −0.014479 | −0.0052 | 0.004074 | 0.003666 | −0.016467 | −0.006248 | 0.016391 | 0.02425 | −0.006229 | 0.009432 | 0.003976 | −0.001898 | 0.001818 | −0.004573 |
| 194 | −0.022153 | 0.000937 | −0.039943 | −0.010287 | −0.011976 | 0.017041 | 0.003437 | 0.009402 | −0.010317 | −0.005305 | 0.022408 | −0.009905 | 0.005596 | 0.001279 |
| 195 | −0.010454 | −0.008889 | −0.001693 | 0.031954 | 0.029493 | −0.001145 | −0.015361 | 0.010131 | −0.027947 | −0.000634 | −0.0314 | −0.018963 | 0.010597 | −0.009947 |
| 196 | −0.005987 | −0.008673 | 0.013877 | 0.03136 | 0.02706 | 0.013747 | 0.005812 | −0.003525 | −0.00106 | −0.00115 | 0.00681 | −0.045296 | 0.003744 | −0.001937 |
| 197 | 0.002585 | 0.000289 | −0.007234 | 0.03474 | 0.01981 | −0.03702 | 0.043395 | −0.01697 | −0.014105 | −0.028926 | −0.036109 | −0.050402 | −0.023653 | −0.002928 |
| 198 | −0.011128 | −0.021824 | 0.000858 | −0.021704 | 0.012056 | −0.021641 | −0.002083 | −0.003268 | −0.005426 | 0.006337 | 0.013274 | 0.016327 | 0.006656 | 0.039551 |
| 199 | 0.007766 | 0.022632 | 0.014649 | 0.0161 | −0.000975 | 0.008549 | −0.079106 | −0.068615 | −0.008843 | −0.018363 | 0.025134 | 0.04293 | 0.014666 | −0.005058 |
| 200 | −0.006813 | −0.021067 | −0.023643 | −0.017359 | −0.005209 | −0.024233 | −0.039107 | 0.028626 | 0.010951 | −0.007181 | −0.03338 | 0.027664 | −0.011611 | −0.005397 |
| 201 | 0.004139 | −0.011582 | −0.002495 | −0.030796 | −0.035988 | −0.00024 | 0.050673 | 0.071418 | −0.032394 | −0.02548 | −0.004696 | −0.01128 | −0.01029 | −0.007746 |
| 202 | −0.015524 | −0.005381 | −0.006903 | −0.020655 | −0.00307 | −0.010125 | −0.041059 | −0.000225 | 0.011572 | 0.025514 | −0.020587 | −0.032647 | −0.001666 | 0.004921 |
| 203 | 0.010872 | 0.00885 | 0.006071 | −0.010288 | −0.024597 | −0.024817 | −0.012374 | 0.006214 | −0.026351 | −0.007188 | −0.008079 | 0.051594 | 0.001545 | −0.000193 |
| 204 | 0.019448 | −0.009725 | −0.010632 | −0.005709 | −0.003963 | −0.006523 | −0.089191 | 0.030725 | 0.047697 | −0.017668 | 0.031258 | −0.030986 | −0.011453 | −0.008638 |
| 205 | 0.008568 | 0.009856 | −0.063087 | −0.026041 | −0.05328 | −0.00465 | 0.067283 | 0.014523 | 0.002462 | −0.001461 | −0.020294 | −0.066721 | −0.003516 | 0.005362 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 206 | −0.000667 | −0.024089 | −0.008074 | 0.010748 | 0.000721 | 0.038551 | −0.008386 | 0.016607 | −0.045148 | 0.00067 | −0.007875 | −0.079968 | 0.000391 | 0.015299 |
| 207 | −0.022398 | −0.042968 | 0.009853 | −0.004412 | −0.026541 | 0.005782 | 0.032681 | −0.007117 | 0.017798 | −0.001144 | 0.008812 | 0.072214 | 0.006649 | −0.045231 |
| 208 | 0.02033 | −0.007954 | −0.019436 | 0.014363 | −0.031348 | −0.026034 | −0.06597 | −0.067278 | −0.04758 | −0.029497 | −0.038021 | −0.022971 | −0.011764 | −0.004548 |
| 209 | 0.022609 | 0.005322 | 0.009025 | 0.010528 | −0.022748 | −0.011875 | −0.032984 | −0.031279 | 0.020235 | 0.003205 | −0.066321 | −0.019121 | −0.032218 | −0.021559 |
| 210 | 0.004402 | −0.000715 | −0.015132 | 0.01271 | 0.004299 | −0.026777 | −0.036979 | 0.03192 | −0.058072 | −0.023727 | −0.025801 | −0.038744 | −0.004328 | −0.06101 |
| 211 | 0.02311 | 0.023379 | −0.046547 | −0.017188 | 0.011073 | −0.03324 | −0.022825 | −0.023947 | −0.004142 | 0.017765 | 0.002098 | −0.067484 | −0.012808 | −0.02464 |
| 212 | 0.016842 | −0.003572 | 0.007834 | 0.013173 | 0.038908 | −0.007234 | 0.054203 | −0.028539 | −0.097964 | 0.031027 | 0.010712 | 0.074447 | 0.015694 | 0.018523 |
| 213 | −0.031011 | −0.039156 | 0.012294 | −0.009815 | 0.004444 | 0.020888 | −0.066301 | 0.031139 | 0.009441 | 0.007819 | −0.012294 | −0.010012 | 0.03488 | 0.022482 |
| 214 | −0.025204 | −0.015407 | −0.007205 | −0.012944 | 0.004194 | 0.004065 | −0.012822 | 0.004214 | −0.014546 | −0.008791 | −0.010317 | 0.026123 | −0.00688 | −0.019973 |
| 215 | −0.034432 | −0.03166 | −0.054211 | 0.006453 | −0.002393 | 0.006877 | −0.052221 | −0.002238 | −0.009228 | −0.026182 | −0.017067 | 0.010717 | −0.026309 | 0.004338 |
| 216 | −0.03331 | −0.010161 | 0.01937 | 0.0015 | 0.004412 | 0.011455 | 0.012714 | 0.003018 | 0.015229 | −0.000575 | 0.020421 | 0.020614 | −0.005582 | 0.010522 |
| 217 | −0.024972 | −0.015745 | −0.009811 | −0.008821 | −0.012931 | 0.004654 | 0.000773 | 0.006759 | −0.011877 | −0.028664 | 0.045692 | −0.007442 | 0.004941 | 0.003917 |
| 218 | −0.027057 | 0.007965 | −0.006225 | 0.008012 | 0.005755 | 0.003297 | 0.003862 | −0.000468 | −0.009322 | −0.013549 | 0.001018 | 0.010218 | −0.022999 | −0.012039 |
| 219 | −0.045921 | −0.000663 | 0.026977 | 0.002793 | 0.014718 | 0.021332 | 0.002588 | −0.01169 | 0.02172 | −0.011051 | 0.01456 | 0.037998 | −0.006457 | 0.001199 |
| 220 | −0.026388 | −0.03698 | −0.004793 | 0.001527 | 0.004316 | 0.00565 | 0.015578 | 0.007435 | −0.009948 | −0.029892 | 0.021839 | 0.001972 | −0.005454 | −0.005994 |
| 221 | −0.005416 | 0.012997 | −0.030644 | −0.037087 | −0.01552 | −0.000378 | 0.038604 | 0.020406 | −0.004003 | −0.005447 | −0.029441 | 0.024825 | 0.001224 | 0.013719 |
| 222 | 0.018217 | 0.012223 | −0.015307 | −0.017368 | −0.06161 | 0.003652 | 0.017702 | 0.005371 | 0.010204 | 0.025051 | −0.012546 | −0.001645 | −0.006545 | 0.000922 |
| 223 | −0.009722 | 0.011633 | −0.00919 | −0.005959 | −0.035788 | 0.012641 | 0.008626 | 0.003104 | 0.00999 | 0.005255 | −0.002503 | 0.013304 | 0.015927 | 0.00194 |
| 224 | 0.01712 | 0.007964 | −0.007945 | −0.021555 | −0.011434 | −0.00648 | −0.011085 | −0.016413 | 0.025169 | 0.015482 | 0.009319 | −0.014213 | −0.004544 | 0.024958 |
| 225 | 0.02308 | 0.017154 | −0.011665 | −0.025248 | −0.01458 | −0.011788 | −0.021502 | −0.01337 | 0.015737 | 0.013475 | −0.009133 | −0.002661 | −0.002193 | 0.024039 |
| 226 | −0.010393 | −0.008202 | 0.004456 | 0.022256 | 0.020337 | −0.004575 | −0.037411 | −0.020378 | −0.017316 | 0.00824 | −0.007088 | −0.001176 | 0.003813 | 0.001171 |
| 227 | 0.001658 | −0.007064 | −0.012457 | 0.000055 | 0.00392 | −0.00471 | −0.020782 | −0.022746 | 0.005926 | 0.00742 | 0.016846 | −0.005355 | −0.002499 | 0.033178 |
| 228 | −0.003986 | 0.007639 | −0.000252 | 0.006146 | −0.023135 | −0.015176 | −0.050336 | −0.017785 | −0.001004 | 0.001576 | −0.001123 | −0.009674 | 0.000536 | 0.004836 |
| 229 | 0.021771 | −0.006257 | −0.019505 | 0.005179 | −0.003489 | 0.0002 | 0.002795 | 0.032269 | 0.007116 | −0.014484 | −0.016921 | −0.005087 | −0.003668 | 0.021896 |
| 230 | 0.025128 | −0.017858 | −0.007841 | 0.006879 | −0.002092 | −0.010673 | 0.034016 | 0.003074 | 0.027332 | 0.019 | 0.011076 | −0.023316 | −0.005483 | 0.015936 |
| 231 | 0.017903 | 0.006942 | 0.020663 | 0.041488 | 0.025216 | −0.022433 | 0.014967 | −0.036593 | 0.016087 | −0.003752 | −0.030225 | −0.018181 | 0.007934 | −0.019235 |
| 232 | 0.008799 | 0.01778 | −0.023732 | 0.013172 | 0.011019 | −0.013407 | −0.013203 | 0.010125 | −0.008765 | 0.013045 | 0.038793 | −0.021078 | 0.01354 | 0.018975 |
| 233 | −0.001476 | 0.022774 | −0.004251 | −0.04728 | −0.01764 | −0.003818 | −0.011908 | 0.029594 | −0.013687 | 0.007421 | 0.020747 | −0.012429 | 0.006825 | 0.019309 |
| 234 | 0.003292 | 0.013069 | 0.004288 | 0.028997 | 0.00736 | −0.017046 | 0.010154 | −0.018067 | 0.004323 | −0.012829 | −0.045237 | 0.036347 | −0.00311 | 0.024768 |
| 235 | 0.025835 | 0.014993 | −0.000601 | 0.004111 | −0.008561 | −0.009312 | 0.008414 | −0.028483 | 0.035079 | −0.008399 | −0.035212 | 0.01864 | −0.009061 | 0.014004 |
| 236 | 0.013662 | 0.006667 | −0.003228 | 0.028011 | 0.026484 | 0.005804 | 0.01775 | 0.00021 | −0.010243 | 0.009045 | 0.018003 | −0.019555 | 0.008031 | 0.003292 |
| 237 | 0.02152 | 0.024454 | 0.003811 | 0.013311 | 0.015434 | −0.001196 | −0.006524 | 0.00241 | −0.011016 | 0.003303 | 0.004029 | −0.029842 | −0.007489 | −0.006329 |
| 238 | −0.005133 | 0.016169 | 0.020152 | 0.00162 | 0.005095 | 0.002786 | 0.021738 | −0.013574 | 0.002347 | 0.002178 | 0.014457 | −0.049684 | 0.00357 | −0.015424 |
| 239 | −0.016984 | 0.010861 | 0.028362 | 0.001912 | −0.008965 | 0.000544 | 0.01034 | −0.014482 | 0.023202 | 0.001525 | 0.003789 | −0.021173 | 0.008779 | −0.02216 |
| 240 | −0.01875 | 0.023182 | −0.004831 | −0.050337 | −0.025974 | 0.005425 | −0.014561 | 0.007436 | −0.027706 | 0.001219 | 0.033034 | −0.011898 | 0.022787 | 0.021615 |
| 241 | −0.010622 | 0.012 | 0.01473 | −0.035418 | −0.013411 | 0.004199 | 0.002371 | 0.021087 | −0.027417 | 0.002782 | 0.026557 | −0.002424 | −0.002103 | 0.006145 |
| 242 | 0.003303 | 0.004552 | 0.003435 | −0.002697 | −0.004 | 0.002525 | 0.028259 | −0.014667 | 0.004026 | 0.014722 | −0.001887 | −0.001747 | 0.002094 | 0.004249 |
| 243 | 0.006062 | 0.005377 | 0.001826 | −0.001486 | −0.018017 | 0.00923 | 0.012199 | −0.016155 | 0.029396 | 0.010862 | 0.022569 | −0.007547 | −0.00443 | 0.016428 |
| 244 | −0.001564 | −0.00032 | −0.011322 | −0.027998 | −0.007292 | −0.009083 | 0.019524 | 0.018388 | −0.004305 | −0.010705 | −0.016736 | 0.019178 | 0.000577 | 0.0181 |
| 245 | 0.011912 | 0.006351 | 0.000329 | 0.008784 | 0.005633 | −0.007367 | 0.014943 | 0.021833 | 0.028573 | −0.01619 | −0.001883 | 0.056131 | −0.007087 | 0.032601 |
| 246 | 0.001299 | 0.005998 | 0.005951 | −0.000071 | −0.002011 | −0.003482 | −0.012857 | 0.005705 | 0.00804 | 0.007684 | −0.006542 | 0.017949 | 0.003257 | −0.008681 |
| 247 | −0.009743 | 0.005967 | −0.006913 | −0.004939 | 0.004023 | 0.001241 | 0.006859 | 0.007688 | 0.016844 | 0.005413 | −0.000611 | 0.012621 | 0.005411 | 0.004827 |
| 248 | −0.015339 | −0.002692 | −0.020584 | 0.004005 | 0.011561 | −0.000592 | 0.005555 | 0.011167 | 0.016261 | −0.007162 | 0.007996 | −0.017122 | −0.005433 | 0.007896 |
| 249 | 0.017688 | 0.009111 | 0.011546 | −0.009026 | −0.053739 | −0.006602 | −0.025596 | −0.009704 | −0.046962 | 0.017253 | 0.039953 | −0.050038 | 0.011223 | 0.005617 |
| 250 | −0.01858 | 0.013814 | 0.004594 | −0.03284 | −0.020912 | −0.003474 | 0.005756 | 0.007526 | −0.007269 | −0.015461 | 0.026445 | 0.003368 | 0.02219 | 0.004807 |
| 251 | −0.005192 | 0.017151 | 0.007117 | −0.046291 | −0.023867 | −0.002362 | 0.01419 | −0.00059 | 0.006901 | −0.004823 | 0.012215 | 0.013281 | 0.011255 | 0.023989 |
| 252 | 0.009348 | −0.002755 | 0.008464 | 0.032933 | 0.009063 | −0.018346 | 0.03049 | 0.017718 | 0.017745 | −0.015012 | 0.002157 | 0.030266 | −0.003074 | 0.015119 |
| 253 | 0.003986 | −0.009795 | −0.015225 | 0.020688 | −0.004705 | −0.006536 | −0.015744 | 0.007093 | −0.025621 | −0.009862 | 0.023838 | −0.014046 | −0.007518 | 0.018215 |
| 254 | 0.0055 | 0.008358 | 0.011139 | −0.005094 | −0.017823 | 0.012586 | −0.021676 | −0.009407 | 0.011628 | 0.001457 | 0.009199 | 0.010175 | 0.022785 | 0.013489 |
| 255 | 0.007715 | 0.003129 | 0.001169 | −0.018432 | 0.00313 | −0.006418 | 0.015891 | −0.004924 | −0.000834 | −0.005395 | −0.006316 | 0.02937 | 0.011145 | 0.021615 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 256 | 0.030454 | −0.011803 | −0.007136 | 0.033834 | 0.024373 | −0.02277− | 0.037453 | 0.008809 | −0.000616 | −0.031365 | −0.018419 | 0.049356 | −0.019744 | 0.025425 |
| 257 | 0.005933 | −0.012901 | −0.016221 | 0.012376 | −0.00296 | −0.007368 | 0.020384 | 0.014507 | −0.001476 | −0.001666 | −0.008874 | 0.013682 | 0.018646 | −0.000315 |
| 258 | 0.011445 | 0.005997 | −0.017308 | 0.013939 | 0.000671 | 0.010506 | −0.00299 | 0.002315 | −0.020194 | 0.000702 | −0.020215 | 0.011838 | −0.003275 | −0.004619 |
| 259 | 0.017205 | 0.014868 | 0.014378 | −0.022552 | −0.057845 | 0.000103 | −0.005383 | 0.002084 | 0.011713 | 0.00803 | 0.016157 | −0.002926 | 0.005106 | −0.001601 |
| 260 | 0.009418 | 0.004123 | 0.005496 | 0.020213 | −0.024985 | −0.001345 | −0.021342 | 0.012998 | 0.027423 | −0.006555 | −0.013026 | 0.041712 | 0.013643 | −0.024743 |
| 261 | −0.007119 | 0.007681 | 0.011863 | 0.023091 | −0.003431 | −0.001547 | 0.003655 | −0.00087 | −0.007415 | −0.003279 | −0.018913 | −0.002677 | 0.013766 | −0.022229 |
| 262 | −0.007057 | −0.004984 | −0.007772 | 0.017618 | 0.003908 | −0.010952 | 0.018106 | 0.011213 | 0.014495 | 0.011326 | −0.001063 | −0.012759 | 0.006712 | −0.00696 |
| 263 | 0.001918 | −0.007596 | −0.009561 | 0.015706 | 0.003786 | −0.011231 | 0.011311 | 0.019427 | 0.022106 | 0.00069 | 0.005515 | −0.004001 | 0.000275 | 0.000495 |
| 264 | 0.018836 | 0.000765 | 0.016451 | −0.014801 | −0.051345 | 0.005929 | −0.002691 | 0.000512 | 0.002028 | 0.015191 | 0.007625 | 0.000794 | −0.009501 | −0.023638 |
| 265 | 0.01166 | −0.000853 | 0.035719 | 0.027023 | −0.01534 | 0.012937 | −0.041578 | −0.006726 | 0.000934 | 0.009177 | 0.000959 | 0.016624 | 0.009765 | −0.029445 |
| 266 | 0.004542 | 0.002296 | 0.025648 | 0.039221 | 0.025726 | 0.004201 | −0.022628 | −0.005497 | −0.006816 | 0.00069 | −0.017777 | 0.015797 | 0.017413 | 0.003161 |
| 267 | −0.016721 | −0.012677 | 0.003808 | 0.027682 | 0.018055 | −0.008158 | −0.069543 | −0.024916 | −0.036703 | −0.034834 | 0.008921 | 0.000886 | −0.001571 | −0.007617 |
| 268 | −0.003747 | −0.007829 | 0.008522 | 0.017096 | 0.01825 | −0.007174 | −0.042085 | −0.020092 | −0.009199 | −0.001631 | 0.001153 | 0.006522 | −0.004848 | 0.001211 |
| 269 | −0.000276 | −0.008958 | −0.002986 | 0.01432 | 0.022598 | 0.002804 | −0.024665 | −0.01879 | −0.00663 | 0.009861 | 0.00294 | −0.007069 | −0.004463 | 0.006206 |
| 270 | −0.013596 | −0.020478 | −0.001829 | 0.016579 | 0.016923 | −0.00114 | −0.03197 | −0.020223 | −0.00577 | 0.007016 | 0.008885 | −0.003824 | −0.002846 | 0.005977 |
| 271 | −0.021919 | 0.013342 | 0.00993 | −0.006923 | 0.010023 | −0.012591 | −0.060322 | −0.006838 | 0.018291 | −0.00354 | −0.0145 | 0.001841 | 0.008998 | −0.002774 |
| 272 | 0.00249 | −0.008212 | −0.000306 | 0.006061 | 0.000713 | −0.006402 | 0.004837 | 0.009211 | −0.005544 | −0.020696 | −0.025692 | 0.008897 | 0.000953 | −0.002802 |
| 273 | 0.017065 | −0.025375 | −0.004533 | 0.00188 | 0.000725 | −0.005281 | 0.003854 | 0.005726 | 0.01349 | −0.005739 | 0.008706 | −0.022813 | −0.008627 | −0.004293 |
| 274 | 0.01886 | −0.028068 | −0.000249 | −0.001105 | 0.001751 | 0.001823 | 0.009113 | 0.007139 | 0.006701 | −0.000028 | 0.007685 | −0.024793 | −0.004304 | −0.005351 |
| 275 | 0.002189 | −0.04173 | −0.019413 | −0.002753 | −0.00117 | 0.001874 | 0.009218 | −0.000737 | 0.017281 | 0.009842 | 0.02975 | −0.020735 | −0.007576 | 0.012661 |
| 276 | 0.019248 | 0.010936 | 0.003655 | 0.031257 | 0.023473 | 0.009731 | 0.034761 | −0.005684 | −0.01444 | −0.001833 | 0.007491 | −0.02019 | 0.007944 | −0.001202 |
| 277 | 0.011796 | 0.017157 | 0.003143 | 0.00596 | −0.001161 | 0.006938 | −0.028306 | −0.002963 | −0.005842 | 0.012778 | −0.008163 | −0.007699 | −0.002838 | −0.003644 |
| 278 | 0.002491 | 0.010152 | −0.007033 | −0.007761 | −0.010626 | 0.006831 | −0.020651 | 0.011897 | 0.006575 | 0.011773 | −0.010943 | −0.021286 | −0.007294 | −0.006115 |
| 279 | −0.028344 | 0.004027 | 0.022039 | −0.001873 | −0.002696 | 0.01563 | 0.006727 | −0.021976 | 0.021132 | 0.008149 | 0.009467 | −0.030261 | 0.012638 | −0.018167 |
| 280 | 0.031308 | −0.001664 | 0.00968 | −0.001922 | −0.020502 | 0.007655 | 0.000581 | −0.025711 | −0.007903 | 0.004794 | 0.025331 | −0.024523 | −0.016388 | 0.018176 |
| 281 | −0.000802 | −0.005363 | 0.008675 | −0.00833 | −0.010552 | −0.002769 | −0.029844 | 0.007641 | −0.000641 | 0.011235 | −0.025312 | 0.004758 | −0.011805 | −0.019222 |
| 282 | 0.009142 | 0.000985 | −0.003433 | −0.020075 | −0.019109 | −0.001176 | 0.000792 | 0.012448 | 0.025224 | 0.019179 | −0.029836 | 0.000315 | −0.015107 | −0.00534 |
| 283 | −0.036592 | −0.013421 | −0.003018 | −0.011997 | 0.00994 | 0.010021 | 0.019187 | 0.001387 | 0.03036 | 0.006275 | −0.002758 | −0.001699 | −0.00244 | 0.005345 |
| 284 | 0.002266 | −0.016868 | −0.011065 | 0.004948 | −0.000907 | −0.00297 | 0.015721 | 0.003794 | −0.006058 | −0.004606 | −0.012302 | 0.012131 | 0.004804 | −0.013547 |
| 285 | 0.001386 | −0.01515 | −0.01265 | −0.00202 | −0.007678 | −0.005427 | 0.016792 | 0.005598 | 0.007799 | 0.001373 | −0.008128 | 0.005449 | 0.007203 | −0.006694 |
| 286 | 0.014842 | −0.000117 | 0.000985 | −0.006009 | −0.006681 | 0.017782 | 0.004628 | 0.008449 | −0.030254 | 0.005928 | −0.024081 | 0.020486 | 0.002928 | −0.010133 |
| 287 | 0.00529 | −0.002156 | −0.010902 | −0.01054 | −0.007991 | 0.014619 | 0.01224 | 0.008451 | −0.016274 | 0.007265 | −0.019851 | 0.012907 | −0.005938 | −0.000322 |
| 288 | −0.007985 | −0.004974 | −0.02405 | 0.003055 | 0.008759 | 0.015763 | 0.00942 | −0.000481 | −0.015919 | 0.000772 | −0.006823 | −0.013414 | −0.019739 | −0.003676 |
| 289 | −0.000651 | −0.024183 | −0.007459 | 0.015849 | 0.007828 | −0.002001 | −0.002303 | 0.011903 | −0.010713 | 0.004269 | −0.009842 | −0.00583 | 0.002435 | 0.000379 |
| 290 | −0.010965 | −0.011738 | −0.014476 | −0.000453 | 0.008242 | −0.007763 | −0.009636 | 0.019366 | 0.027611 | −0.005845 | 0.038825 | −0.016686 | −0.015728 | 0.016703 |
| 291 | −0.009439 | −0.009101 | −0.014014 | 0.001599 | 0.009232 | −0.008093 | −0.011998 | 0.01594 | 0.030403 | −0.005476 | 0.03818 | −0.014136 | −0.012665 | 0.0189 |
| 292 | −0.011 | −0.004078 | −0.013962 | −0.00342 | 0.005369 | −0.006155 | 0.000071 | 0.013378 | 0.028155 | −0.000213 | 0.046379 | −0.02471 | −0.00459 | 0.017141 |
| 293 | 0.011889 | 0.02034 | −0.024266 | −0.003905 | 0.006384 | −0.003979 | 0.000154 | 0.013309 | −0.013692 | −0.005546 | −0.010934 | −0.007116 | 0.002912 | −0.008788 |
| 294 | 0.014722 | 0.006602 | −0.010945 | 0.013454 | 0.004948 | 0.002446 | −0.005335 | 0.007573 | −0.001789 | −0.002665 | −0.004881 | −0.019736 | −0.018095 | −0.009191 |
| 295 | 0.018369 | −0.011819 | −0.006005 | −0.009691 | −0.004229 | −0.012042 | 0.03989 | −0.001936 | 0.01572 | −0.007107 | 0.008245 | −0.019839 | 0.002431 | −0.001807 |
| 296 | 0.018251 | −0.010592 | −0.021542 | 0.000187 | −0.009462 | 0.00444 | −0.005153 | −0.009149 | −0.026848 | 0.004222 | 0.013841 | −0.0163 | 0.005514 | 0.015006 |
| 297 | 0.021087 | −0.010229 | 0.001451 | 0.000018 | −0.008803 | −0.005489 | 0.051133 | 0.006285 | 0.00542 | −0.006716 | −0.008155 | −0.018408 | −0.006223 | −0.01922 |
| 298 | −0.010436 | 0.011201 | −0.016956 | 0.04053 | 0.029337 | 0.014301 | −0.011756 | 0.02292 | 0.012491 | −0.02506 | 0.034343 | 0.020256 | 0.014281 | 0.012565 |
| 299 | 0.024925 | 0.013686 | 0.007626 | 0.008168 | −0.003472 | −0.006233 | 0.03304 | 0.000072 | 0.013836 | 0.005571 | 0.001157 | −0.013978 | −0.009561 | −0.003265 |
| 300 | −0.007259 | −0.005364 | 0.003882 | 0.01068 | 0.019161 | 0.031102 | −0.006281 | 0.015514 | 0.019506 | −0.001677 | 0.034844 | −0.093827 | 0.03121 | 0.028412 |
| 301 | 0.008331 | 0.000837 | −0.015072 | −0.001824 | −0.013617 | −0.01539 | 0.048504 | 0.008625 | 0.029487 | 0.002622 | 0.007037 | −0.005088 | −0.00849 | 0.002138 |
| 302 | −0.006128 | −0.020874 | 0.004726 | −0.010962 | −0.02741 | −0.002395 | 0.013268 | −0.011246 | 0.027756 | 0.011057 | 0.022658 | −0.019795 | −0.004217 | 0.002347 |
| 303 | 0.017693 | 0.024783 | −0.013146 | 0.004625 | −0.01831 | 0.009162 | 0.042088 | 0.011136 | 0.017164 | 0.017673 | −0.006843 | 0.003499 | −0.004344 | 0.00327 |
| 304 | 0.007611 | 0.006892 | −0.002534 | −0.000622 | −0.017629 | 0.003515 | 0.027846 | −0.000635 | 0.004117 | −0.001695 | 0.012431 | −0.01976 | −0.020298 | 0.018948 |
| 305 | −0.01329 | −0.017306 | 0.018784 | −0.008105 | 0.001555 | −0.019909 | 0.004646 | 0.040655 | 0.010115 | −0.008075 | −0.025888 | 0.012356 | 0.01093 | −0.019704 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 306 | −0.010595 | 0.010698 | −0.02949 | −0.009506 | −0.021959 | 0.00624 | 0.005036 | 0.055719 | −0.037382 | −0.017098 | −0.015137 | 0.022983 | −0.000322 | −0.003421 |
| 307 | −0.00732 | −0.004561 | −0.008612 | −0.007972 | 0.000539 | 0.013303 | 0.041616 | 0.035592 | −0.060567 | 0.019889 | 0.002793 | −0.077302 | 0.006736 | 0.016361 |
| 308 | 0.034524 | 0.027161 | 0.000779 | 0.009771 | 0.014081 | 0.014113 | 0.017563 | 0.04877 | −0.056258 | 0.011809 | −0.018857 | 0.010069 | 0.014852 | −0.001103 |
| 309 | −0.008732 | 0.003455 | −0.000267 | 0.007683 | 0.008894 | 0.006408 | −0.029913 | −0.028437 | 0.019086 | 0.017945 | 0.013801 | −0.012874 | −0.005487 | −0.002137 |
| 310 | −0.003045 | −0.007079 | −0.014698 | −0.002275 | 0.001077 | 0.000617 | −0.047787 | −0.010002 | −0.008314 | 0.004149 | 0.006053 | 0.055912 | −0.001405 | −0.010415 |
| 311 | 0.003025 | −0.004557 | −0.001121 | 0.002128 | 0.011323 | 0.01904 | −0.01323 | 0.026019 | 0.006587 | 0.015962 | 0.025115 | −0.016184 | −0.004681 | 0.002623 |
| 312 | 0.005826 | −0.027338 | 0.014735 | 0.025963 | 0.022508 | 0.020551 | 0.039927 | 0.030143 | 0.006394 | −0.000157 | −0.016217 | 0.02675 | −0.029809 | −0.002474 |
| 313 | 0.018196 | −0.004416 | −0.017398 | 0.01797 | 0.0098 | 0.011334 | 0.013981 | 0.034671 | −0.01507 | 0.000435 | −0.026679 | 0.018745 | −0.009418 | −0.014735 |
| 314 | 0.024469 | −0.008618 | −0.018779 | 0.032751 | 0.012551 | −0.030447 | −0.029023 | 0.049341 | −0.00518 | −0.056466 | −0.039607 | 0.057328 | −0.022548 | −0.000928 |
| 315 | 0.010901 | 0.01709 | 0.001371 | 0.013019 | 0.012853 | 0.020752 | 0.006838 | 0.004877 | −0.002894 | 0.022292 | −0.010665 | 0.009428 | 0.00465 | −0.00375 |
| 316 | 0.006114 | 0.003945 | −0.056214 | −0.012779 | −0.008745 | −0.013498 | 0.018919 | −0.016637 | 0.027676 | −0.00277 | 0.021914 | 0.016837 | 0.000985 | −0.010256 |
| 317 | 0.000738 | 0.008793 | −0.01766 | 0.016813 | 0.011899 | 0.007065 | −0.007635 | −0.002446 | 0.044387 | 0.013595 | 0.008872 | 0.015778 | 0.012966 | 0.009062 |
| 318 | 0.018192 | 0.012455 | 0.000128 | −0.021541 | −0.00788 | 0.00499 | −0.000689 | 0.000491 | 0.009093 | −0.001863 | 0.010716 | −0.009623 | 0.021844 | 0.025504 |
| 319 | 0.016605 | 0.021357 | −0.014418 | 0.013232 | 0.010046 | 0.018408 | 0.002164 | −0.017506 | 0.022159 | 0.025708 | −0.007309 | 0.00709 | 0.002932 | 0.012635 |
| 320 | 0.022512 | 0.010868 | −0.011647 | 0.008682 | 0.003538 | 0.008798 | −0.042115 | −0.009837 | 0.016447 | −0.014586 | 0.003346 | 0.017903 | −0.001237 | 0.009395 |
| 321 | 0.029231 | −0.006741 | 0.001839 | 0.010881 | −0.011362 | −0.015357 | 0.027811 | 0.024679 | −0.012738 | −0.011197 | −0.001897 | −0.004043 | −0.022704 | −0.024209 |
| 322 | 0.002917 | −0.012774 | 0.033142 | −0.019373 | −0.004457 | −0.009294 | 0.009547 | −0.004375 | −0.003192 | −0.036805 | 0.071435 | −0.074676 | 0.003871 | −0.036184 |
| 323 | 0.027794 | −0.017371 | 0.031527 | 0.024966 | 0.021247 | −0.00359 | 0.008491 | 0.019186 | −0.006569 | −0.020042 | 0.034722 | 0.053316 | 0.003331 | −0.007385 |
| 324 | −0.040676 | −0.029281 | −0.003695 | −0.009139 | −0.019329 | −0.007953 | −0.072682 | −0.051931 | −0.04096 | −0.018093 | 0.001157 | −0.044801 | −0.016546 | −0.045527 |
| 325 | −0.005362 | 0.005697 | −0.011301 | 0.018665 | 0.005978 | 0.02589 | 0.004248 | −0.024909 | −0.00534 | 0.022145 | −0.004759 | −0.016964 | −0.012875 | −0.029873 |
| 326 | −0.014154 | −0.007446 | 0.009479 | 0.008956 | 0.020783 | 0.03061 | −0.034943 | 0.012136 | 0.01206 | 0.051906 | 0.035652 | −0.010112 | −0.004171 | −0.011525 |
| 327 | 0.00575 | −0.002112 | 0.005696 | −0.002532 | 0.002487 | 0.010905 | −0.005444 | −0.014561 | 0.016313 | 0.011446 | 0.020343 | −0.009365 | 0.004208 | −0.00326 |
| 328 | 0.02417 | 0.013066 | 0.00676 | 0.051597 | 0.033233 | 0.012925 | −0.088021 | 0.058851 | −0.071721 | −0.012649 | 0.026125 | −0.026452 | 0.011405 | 0.000528 |
| 329 | 0.019561 | 0.001992 | 0.016216 | −0.00507 | −0.001714 | 0.011022 | 0.000851 | 0.036853 | 0.031906 | 0.02725 | 0.019845 | 0.027157 | 0.013327 | 0.004705 |
| 330 | 0.014719 | −0.013583 | 0.000749 | 0.028946 | 0.001289 | −0.01658 | 0.026404 | −0.025539 | 0.058975 | −0.026718 | 0.027245 | 0.022333 | −0.025557 | −0.030494 |
| 331 | −0.003483 | 0.012197 | 0.002016 | 0.007791 | 0.015227 | 0.025592 | −0.008407 | 0.014957 | 0.002293 | 0.014871 | 0.003782 | 0.00974 | −0.009722 | −0.006566 |
| 332 | 0.001785 | −0.014249 | 0.012555 | 0.00977 | 0.020098 | 0.022975 | −0.02124 | −0.033143 | 0.024322 | 0.039367 | 0.034434 | −0.071623 | −0.011456 | −0.003335 |
| 333 | −0.002978 | 0.007007 | −0.009893 | 0.013387 | 0.006695 | 0.015502 | 0.00091 | −0.016366 | 0.009442 | 0.016803 | 0.004481 | −0.021495 | −0.007821 | 0.00071 |
| 334 | −0.003103 | 0.017788 | −0.00867 | −0.001271 | −0.01624 | 0.004199 | 0.035985 | −0.023281 | 0.029646 | 0.000677 | −0.040521 | −0.010994 | −0.021557 | −0.031688 |
| 335 | 0.005698 | −0.001311 | −0.007327 | 0.015572 | 0.018392 | 0.026001 | −0.01231 | −0.001705 | 0.005611 | 0.017845 | 0.010706 | −0.007649 | −0.023062 | 0.001541 |
| 336 | −0.015506 | 0.012115 | −0.002116 | 0.003066 | 0.019351 | −0.026261 | −0.000754 | 0.002746 | 0.026329 | −0.00422 | 0.020134 | −0.009461 | −0.02195 | 0.028157 |
| 337 | 0.014803 | 0.007617 | −0.014388 | −0.000079 | −0.007313 | −0.007915 | 0.014621 | −0.008149 | 0.014812 | 0.003145 | −0.001887 | 0.013656 | −0.003263 | 0.01902 |
| 338 | 0.001952 | 0.007645 | −0.025648 | −0.002159 | 0.017206 | 0.005999 | −0.016755 | −0.021119 | −0.04502 | 0.021546 | 0.013589 | −0.039562 | 0.02284 | 0.038011 |
| 339 | −0.016433 | −0.010274 | 0.01888 | 0.005418 | 0.0046441 | 0.015539 | −0.009085 | 0.016885 | 0.008191 | 0.019891 | −0.003787 | 0.014113 | 0.002851 | −0.011433 |
| 340 | 0.031499 | −0.007455 | 0.040027 | 0.001754 | −0.00328 | −0.006347 | −0.02871 | −0.010791 | 0.013202 | −0.001926 | −0.041795 | 0.06528 | 0.034558 | 0.022223 |

| | EH | EI | EJ | EK | EL | EM | EN | EO | EP | EQ | ER | ES | ET | EU |
|---|---|---|---|---|---|---|---|---|---|---|---|---|---|---|
| 1 | 0.04727 | 0.031264 | −0.031621 | −0.067029 | −0.000657 | 0.090089 | 0.074888 | 0.106287 | −0.00835 | 0.020302 | 0.00921 | 0.036042 | 0.015388 | 0.05993 |
| 2 | −0.012538 | −0.056183 | 0.164834 | 0.118707 | 0.010096 | −0.065741 | −0.026839 | −0.036819 | −0.1739 | 0.045486 | 0.00764 | 0.07174 | −0.003677 | −0.034206 |
| 3 | −0.012607 | 0.055396 | −0.11147 | −0.030569 | −0.010465 | −0.094676 | 0.014894 | −0.038308 | 0.039345 | −0.007622 | 0.068712 | −0.066588 | 0.010415 | −0.00925 |
| 4 | −0.118605 | −0.125299 | 0.10067 | −0.022147 | 0.032735 | 0.003579 | 0.041574 | 0.02965 | −0.052772 | −0.013768 | −0.070481 | −0.110725 | −0.013932 | −0.029821 |
| 5 | −0.016498 | 0.028893 | 0.040423 | 0.064569 | 0.039244 | 0.032301 | 0.038393 | −0.001657 | 0.011441 | 0.009704 | −0.034286 | −0.022572 | 0.011177 | 0.004157 |
| 6 | −0.014553 | 0.05141 | −0.13633 | −0.11685 | 0.016717 | −0.048944 | −0.023143 | 0.060159 | 0.045983 | 0.010905 | −0.010793 | −0.032171 | −0.009598 | −0.051487 |
| 7 | −0.009098 | 0.043455 | −0.097483 | −0.049218 | 0.104027 | −0.039787 | 0.036888 | −0.029928 | −0.123632 | −0.054015 | −0.049621 | 0.043112 | 0.016901 | −0.004097 |
| 8 | 0.021972 | 0.017442 | 0.084813 | 0.059611 | −0.009428 | 0.000398 | −0.040362 | −0.025515 | 0.054882 | 0.014443 | 0.077557 | 0.010592 | −0.009144 | 0.01009 |
| 9 | 0.047582 | 0.063334 | −0.024799 | 0.086442 | −0.002856 | −0.021516 | 0.043434 | 0.056749 | −0.018432 | 0.014623 | −0.051031 | 0.067525 | −0.004881 | −0.004511 |
| 10 | 0.086604 | −0.029294 | 0.081715 | 0.018173 | 0.027591 | −0.050333 | 0.018144 | 0.039149 | 0.034018 | −0.024669 | −0.131648 | −0.01923 | 0.060438 | −0.001198 |
| 11 | −0.025741 | 0.052915 | −0.151309 | −0.005351 | −0.045202 | −0.004981 | −0.036966 | −0.022485 | −0.06625 | 0.016215 | 0.011485 | −0.043674 | −0.094436 | 0.113862 |
| 12 | 0.048788 | 0.010363 | 0.038394 | 0.01227 | −0.022815 | 0.046763 | 0.065748 | 0.017682 | 0.048063 | 0.03176 | −0.041358 | 0.054496 | 0.010613 | 0.066939 |

APPENDIX B3-continued

PCA Transformation
Matrix (340 × 340 Early/Late)

| | | | | | | | | | | | | | |
|---|---|---|---|---|---|---|---|---|---|---|---|---|---|
| 13 | −0.029535 | −0.026254 | −0.061103 | −0.03646 | 0.017552 | −0.091869 | −0.014294 | −0.012931 | −0.065061 | −0.037244 | −0.14909 | 0.065281 | 0.026773 | −0.043599 |
| 14 | 0.093609 | 0.114506 | −0.060414 | 0.162547 | 0.002853 | 0.010042 | 0.039638 | 0.041272 | 0.004506 | −0.026522 | −0.061318 | 0.093852 | 0.037226 | 0.043302 |
| 15 | −0.043148 | −0.093543 | −0.079599 | 0.055875 | 0.023067 | 0.09028 | 0.03499 | 0.027617 | −0.009556 | 0.01406 | 0.060108 | 0.090702 | −0.008904 | −0.07664 |
| 16 | 0.00958 | −0.030486 | 0.063957 | 0.066101 | −0.001726 | −0.098498 | 0.002714 | −0.014184 | 0.08031 | −0.007561 | −0.127392 | 0.0304 | 0.00839 | −0.005965 |
| 17 | −0.008553 | −0.000278 | −0.060281 | 0.004121 | 0.024729 | −0.016723 | −0.016944 | −0.066431 | −0.070253 | −0.032807 | −0.019126 | −0.019777 | −0.037309 | 0.035803 |
| 18 | −0.015166 | 0.015383 | 0.079807 | −0.075486 | −0.041623 | 0.022423 | −0.036988 | −0.012743 | 0.093635 | −0.013407 | 0.014798 | −0.020095 | −0.00096 | −0.055632 |
| 19 | 0.071989 | −0.026291 | 0.019192 | 0.066725 | 0.020106 | 0.001861 | 0.010786 | −0.041359 | 0.018127 | 0.058642 | 0.139199 | 0.007413 | −0.016156 | 0.076914 |
| 20 | 0.040166 | −0.039343 | 0.150667 | −0.003556 | −0.037478 | 0.058357 | −0.033269 | −0.035821 | −0.016045 | −0.050462 | −0.026712 | 0.138787 | 0.014343 | −0.089263 |
| 21 | −0.078365 | −0.112717 | 0.098476 | 0.054519 | 0.035514 | 0.045232 | 0.009002 | 0.041184 | 0.012927 | 0.004188 | −0.152384 | −0.176124 | −0.032669 | −0.094619 |
| 22 | −0.051042 | 0.020175 | −0.092357 | −0.029535 | 0.018999 | 0.080312 | 0.038377 | 0.02359 | 0.078763 | −0.025191 | −0.157796 | 0.033043 | 0.082744 | −0.030087 |
| 23 | −0.024209 | −0.083597 | 0.023592 | −0.009777 | 0.002002 | −0.022953 | 0.025768 | 0.147 | 0.099709 | −0.031058 | −0.031005 | 0.037216 | 0.003856 | −0.022915 |
| 24 | −0.008673 | 0.038081 | 0.062649 | −0.08943 | 0.02023 | −0.036434 | −0.008554 | −0.143651 | −0.036999 | −0.041907 | 0.003599 | −0.007487 | 0.099354 | −0.057441 |
| 25 | −0.057225 | 0.022682 | 0.046129 | −0.010675 | 0.036285 | 0.094031 | 0.016126 | −0.008833 | −0.039057 | 0.019002 | 0.107417 | 0.02225 | 0.003025 | 0.039016 |
| 26 | 0.070808 | 0.146851 | −0.050805 | 0.169402 | 0.039992 | 0.002744 | 0.015465 | −0.010874 | −0.048252 | 0.007318 | 0.028166 | −0.070164 | 0.004065 | −0.015624 |
| 27 | −0.03064 | −0.067834 | −0.063317 | 0.009187 | 0.047658 | 0.04338 | 0.014283 | −0.015883 | 0.107018 | 0.013755 | 0.004298 | −0.118869 | 0.028391 | 0.022193 |
| 28 | 0.029084 | −0.047126 | 0.066048 | 0.014937 | −0.114924 | −0.044952 | −0.052011 | −0.007181 | 0.134155 | 0.070475 | −0.045131 | 0.086698 | 0.031856 | 0.056457 |
| 29 | 0.026883 | 0.046683 | −0.076429 | −0.006436 | 0.019672 | 0.022079 | 0.013656 | 0.023607 | 0.021269 | 0.002507 | 0.000876 | −0.043731 | 0.003402 | 0.014636 |
| 30 | −0.007807 | −0.134268 | −0.048413 | 0.062797 | 0.002016 | 0.046197 | 0.013653 | −0.018503 | 0.025679 | 0.005401 | −0.165409 | −0.15193 | 0.086357 | 0.044048 |
| 31 | −0.075519 | 0.115706 | 0.034791 | −0.03841 | 0.006646 | −0.028157 | 0.022833 | 0.002758 | −0.001818 | 0.072221 | 0.005596 | −0.120325 | −0.081561 | 0.048437 |
| 32 | 0.015112 | −0.007091 | 0.174183 | −0.030346 | −0.021861 | −0.041255 | −0.086269 | −0.083824 | −0.122861 | 0.004727 | −0.031216 | −0.179524 | 0.007878 | −0.044072 |
| 33 | 0.039788 | −0.056835 | 0.04208 | −0.163498 | −0.042896 | −0.047528 | −0.003738 | 0.002974 | 0.041349 | −0.047592 | −0.050269 | −0.059329 | −0.016487 | 0.030291 |
| 34 | 0.086822 | 0.015411 | −0.048153 | 0.041247 | −0.021315 | −0.035759 | 0.05864 | −0.079829 | 0.018251 | −0.008837 | 0.018161 | −0.131974 | 0.060081 | −0.017261 |
| 35 | −0.045689 | −0.048706 | −0.088346 | 0.009599 | −0.103794 | −0.043569 | −0.004389 | −0.044412 | −0.05765 | −0.022605 | −0.053485 | −0.019072 | −0.050394 | 0.019145 |
| 36 | 0.005917 | −0.060668 | 0.177693 | −0.095474 | 0.038491 | −0.000802 | −0.062656 | 0.05281 | −0.036002 | 0.047001 | −0.089709 | 0.085309 | 0.006254 | 0.029065 |
| 37 | −0.054177 | 0.101039 | −0.000715 | 0.087918 | 0.01841 | −0.04464 | −0.096861 | 0.005282 | 0.086432 | −0.003559 | 0.035877 | 0.013173 | −0.080352 | −0.000665 |
| 38 | −0.001691 | −0.088043 | −0.143298 | −0.048932 | −0.096881 | −0.009893 | 0.013394 | −0.042435 | 0.023605 | 0.002666 | −0.066617 | −0.077165 | −0.024951 | 0.036808 |
| 39 | 0.097088 | 0.004176 | 0.019397 | 9.079767 | 0.100854 | −0.085163 | 0.022986 | −0.012497 | 0.016028 | 0.066548 | −0.016262 | 0.08657 | 0.004194 | −0.04487 |
| 40 | 0.042481 | 0.02818 | 0.020405 | −0.012087 | −0.004316 | −0.007437 | 0.002668 | 0.011841 | −0.001964 | −0.001293 | −0.016911 | 0.015505 | 0.012582 | −0.013172 |
| 41 | −0.06057 | −0.052151 | 0.09389 | −0.109523 | 0.00605 | 0.03385 | −0.029693 | −0.039877 | −0.048103 | 0.026201 | 0.050386 | −0.027069 | 0.023014 | −0.049499 |
| 42 | −0.050932 | −0.066501 | −0.023779 | −0.04424 | −0.020863 | −0.011161 | 0.025947 | −0.022002 | 0.014602 | 0.019744 | 0.017431 | −0.055287 | 0.018474 | 0.023299 |
| 43 | −0.053677 | 0.088676 | −0.011944 | −0.075129 | −0.11033 | −0.007032 | −0.120904 | 0.010306 | −0.094316 | −0.165709 | 0.021295 | −0.064518 | −0.091297 | −0.161608 |
| 44 | −0.095297 | 0.148973 | 0.028762 | −0.014237 | 0.027099 | 0.073611 | 0.026147 | 0.083925 | 0.004005 | 0.040883 | 0.180394 | −0.065172 | −0.080661 | 0.021593 |
| 45 | 0.117467 | −0.034531 | −0.027704 | −0.120422 | −0.021301 | 0.071099 | −0.018734 | −0.01766 | −0.0124 | 0.030854 | 0.047602 | −0.062948 | −0.006775 | 0.100753 |
| 46 | 0.013804 | 0.074381 | 0.017874 | −0.078894 | −0.03465 | −0.039447 | −0.045216 | 0.020924 | 0.040047 | −0.012325 | −0.014835 | −0.087093 | −0.021473 | 0.039412 |
| 47 | 0.018681 | −0.116421 | 0.239082 | 0.003228 | −0.055047 | −0.03815 | 0.030589 | −0.093754 | −0.006294 | −0.040274 | 0.061899 | 0.014187 | −0.045132 | 0.078086 |
| 48 | 0.019379 | −0.047296 | −0.063199 | −0.053365 | −0.076221 | −0.062313 | −0.092429 | −0.005804 | 0.037783 | −0.012647 | −0.126984 | 0.024275 | 0.001772 | −0.093818 |
| 49 | 0.071408 | −0.006184 | −0.012586 | −0.047948 | 0.065674 | −0.05196 | −0.059718 | 0.039561 | −0.046664 | 0.011101 | −0.042251 | 0.027539 | −0.025084 | 0.005403 |
| 50 | −0.013897 | 0.014372 | −0.061494 | −0.141588 | −0.032405 | 0.051343 | −0.000839 | 0.044764 | 0.104248 | −0.052115 | −0.022717 | −0.009559 | −0.001176 | −0.052552 |
| 51 | −0.024605 | 0.152105 | 0.035926 | 0.198809 | −0.059433 | 0.092548 | −0.035701 | −0.01546 | −0.011213 | −0.007361 | −0.000863 | 0.114441 | −0.056167 | 0.054834 |
| 52 | 0.002703 | 0.17763 | −0.114401 | 0.038408 | 0.011746 | −0.07133 | −0.031727 | −0.057834 | −0.049893 | −0.044959 | −0.025766 | −0.058392 | 0.023983 | −0.010618 |
| 53 | −0.03886 | −0.017244 | 0.05494 | −0.093021 | −0.005466 | 0.071763 | 0.228445 | 0.144428 | 0.090154 | −0.055078 | 0.074115 | −0.144596 | 0.024024 | 0.00838 |
| 54 | 0.011231 | −0.083389 | −0.03781 | 0.111157 | 0.09188 | 0.00628 | −0.000363 | 0.054402 | 0.008008 | −0.020542 | 0.117977 | −0.09238 | 0.034148 | −0.07432 |
| 55 | −0.011097 | 0.048611 | −0.01279 | −0.07112 | 0.065444 | −0.029081 | −0.013869 | −0.070122 | −0.011449 | −0.010548 | −0.141396 | −0.062619 | 0.014741 | 0.092144 |
| 56 | 0.034701 | −0.010291 | 0.138149 | −0.043023 | 0.016082 | 0.05195 | 0.063 | −0.027304 | −0.013404 | −0.048778 | −0.115968 | 0.037431 | −0.006331 | 0.063808 |
| 57 | −0.003173 | −0.057721 | 0.010705 | −0.015544 | −0.023714 | −0.043685 | −0.093528 | −0.069112 | −0.056028 | −0.011259 | −0.002096 | −0.105738 | −0.027121 | −0.029229 |
| 58 | 0.001804 | −0.001077 | 0.036149 | −0.062373 | −0.017621 | 0.064446 | −0.102138 | −0.045451 | −0.065461 | −0.017551 | −0.008983 | −0.014271 | −0.104979 | −0.03085 |
| 59 | −0.042834 | 0.002869 | 0.029155 | 0.086178 | −0.077889 | −0.039487 | 0.019918 | −0.073111 | 0.056221 | −0.058603 | −0.002418 | 0.062292 | −0.005361 | 0.024845 |
| 60 | −0.00329 | −0.01549 | −0.008054 | 0.020859 | −0.001714 | 0.034732 | 0.035514 | −0.018398 | 0.008766 | 0.039311 | 0.04916 | −0.020752 | −0.003042 | 0.07031 |
| 61 | 0.024497 | 0.015524 | −0.022991 | 0.008444 | 0.004022 | −0.020594 | −0.002863 | −0.041006 | −0.00847 | 0.004813 | 0.023312 | −0.017954 | 0.023356 | 0.015765 |
| 62 | −0.018972 | 0.020049 | −0.002719 | −0.024122 | −0.002816 | 0.007854 | 0.004309 | −0.009091 | 0.001231 | 0.012679 | 0.037464 | 0.014466 | −0.001744 | 0.025248 |

APPENDIX B3-continued

PCA Transformation
Matrix (340 × 340 Early/Late)

| | | | | | | | | | | | | | |
|---|---|---|---|---|---|---|---|---|---|---|---|---|---|
| 63 | 0.006972 | 0.038896 | −0.010136 | 0.029597 | 0.024422 | −0.007692 | −0.002566 | −0.019742 | −0.000746 | 0.009248 | 0.020077 | 0.010376 | 0.021799 | 0.001257 |
| 64 | 0.001469 | 0.021653 | 0.02834 | 0.033273 | 0.032146 | 0.01264 | 0.005283 | −0.002364 | −0.017028 | −0.008503 | 0.053176 | 0.04387 | 0.003564 | −0.00963 |
| 65 | 0.018362 | −0.00184 | 0.000937 | −0.000104 | 0.026885 | −0.002471 | 0.016175 | 0.040177 | 0.016881 | 0.000793 | −0.042067 | 0.03095 | 0.007421 | −0.001638 |
| 66 | 0.007072 | 0.030287 | 0.020935 | −0.002512 | 0.025335 | 0.001504 | 0.00819 | −0.001402 | 0.002115 | −0.014908 | −0.027863 | −0.037157 | 0.004327 | 0.031828 |
| 67 | −0.017059 | 0.011657 | −0.022947 | 0.000113 | 0.00292 | 0.0088 | 0.015634 | −0.006118 | 0.01432 | −0.005975 | −0.024369 | −0.049241 | 0.027625 | −0.004487 |
| 68 | −0.03847 | −0.035181 | −0.008498 | 0.017202 | −0.019079 | 0.021211 | 0.013764 | −0.009194 | 0.023954 | 0.005546 | −0.018069 | 0.034389 | −0.005002 | 0.002723 |
| 69 | −0.001885 | −0.009977 | 0.038148 | −0.035488 | −0.011145 | 0.020499 | 0.017338 | −0.013686 | −0.004883 | −0.016805 | 0.001654 | 0.018849 | 0.006695 | 0.020312 |
| 70 | −0.003008 | 0.009708 | −0.005275 | 0.005995 | −0.000023 | 0.014183 | 0.021121 | 0.016534 | −0.001697 | 0.017974 | 0.029709 | −0.019099 | −0.024963 | 0.033186 |
| 71 | −0.02281 | 0.030761 | −0.015891 | −0.005917 | −0.023715 | 0.021949 | 0.02236 | 0.019878 | 0.013113 | −0.008903 | 0.026137 | 0.014668 | −0.006668 | 0.009796 |
| 72 | −0.022316 | 0.004125 | −0.019076 | −0.026998 | −0.009456 | 0.033452 | 0.034494 | 0.008157 | −0.006824 | −0.002011 | 0.065997 | 0.042467 | −0.008345 | 0.015604 |
| 73 | 0.003753 | 0.000614 | −0.021792 | −0.023034 | 0.013283 | −0.005881 | 0.027066 | 0.002788 | −0.022768 | −0.009779 | 0.000538 | −0.03257 | 0.001976 | −0.013765 |
| 74 | −0.033915 | −0.026222 | 0.000165 | 0.012652 | 0.018363 | 0.006935 | 0.013465 | 0.035326 | −0.001298 | −0.003893 | 0.042117 | −0.028162 | −0.039342 | −0.013345 |
| 75 | −0.009215 | 0.014769 | 0.019365 | −0.009995 | 0.000297 | 0.001411 | 0.001201 | 0.00589 | 0.01686 | 0.00687 | 0.003587 | −0.010938 | −0.008414 | 0.0143 |
| 76 | 0.001879 | −0.014501 | 0.005427 | −0.030412 | 0.013603 | −0.011802 | −0.009662 | 0.017579 | 0.003589 | −0.007218 | −0.04554 | −0.047265 | 0.004753 | −0.00177 |
| 77 | −0.01097 | 0.018679 | 0.009943 | −0.018078 | −0.004875 | 0.016166 | 0.000627 | 0.009299 | 0.01814 | 0.008409 | 0.011951 | −0.01059 | −0.012993 | 0.01248 |
| 78 | −0.019515 | 0.021141 | 0.011501 | 0.001715 | −0.012969 | 0.007689 | 0.000695 | 0.006801 | 0.02079 | 0.011389 | 0.009964 | −0.005838 | −0.012512 | 0.009228 |
| 79 | −0.003539 | 0.017582 | 0.043938 | −0.00347 | 0.019199 | 0.001271 | 0.016433 | 0.011826 | 0.013408 | −0.00664 | 0.014422 | −0.029956 | −0.015789 | 0.015493 |
| 80 | 0.004358 | 0.012674 | −0.085349 | 6.015414 | 0.026336 | 0.003209 | −0.004638 | 0.000036 | −0.038968 | −0.023406 | 0.034651 | 0.007633 | 0.012241 | −0.014708 |
| 81 | 0.008914 | 0.004335 | 0.035731 | 0.004506 | −0.000079 | −0.007809 | −0.05732 | 0.006667 | −0.020389 | −0.00222 | −0.013005 | 0.027966 | −0.023468 | −0.011706 |
| 82 | 0.004176 | 0.015294 | −0.019652 | −0.02358 | −0.013935 | 0.031863 | 0.0121621 | 0.0124891 | −0.017516 | −0.010639 | −0.005929 | 0.007436 | −0.008757 | 0.013935 |
| 83 | 0.000801 | −0.002724 | 0.000371 | 0.005555 | −0.012392 | 0.006306 | 0.010288 | 0.013593 | −0.003008 | 0.003956 | −0.003771 | 0.013283 | 0.000366 | 0.004002 |
| 84 | 0.001755 | 0.005918 | −0.019459 | −0.013732 | −0.008506 | 0.010834 | 0.004326 | 0.019209 | 0.013754 | 0.006958 | −0.009906 | 0.013833 | 0.000303 | 0.005761 |
| 85 | −0.008554 | 0.011278 | −0.001284 | −0.072395 | 0.044014 | −0.038274 | −0.000554 | 0.028476 | 0.017065 | −0.027094 | −0.033696 | 0.004834 | 0.009406 | −0.004947 |
| 86 | −0.003955 | 0.011087 | −0.005411 | −0.058868 | −0.013245 | −0.018969 | 0.021765 | −0.012733 | −0.001406 | −0.016263 | 0.003087 | −0.013885 | 0.012282 | 0.001744 |
| 87 | −0.021407 | 0.012898 | 0.005057 | −0.003534 | 0.012026 | −0.00466 | 0.034934 | 0.004461 | −0.019794 | −0.010389 | 0.029421 | −0.058481 | 0.008412 | 0.014789 |
| 88 | 0.007136 | 0.019035 | −0.011513 | 0.012443 | −0.011775 | 0.013964 | 0.007789 | 0.004309 | 0.014241 | 0.003814 | −0.000234 | 0.018388 | −0.001485 | 0.009293 |
| 89 | −0.012473 | −0.00978 | 0.011501 | 0.015169 | −0.024742 | 0.014284 | 0.01872 | 0.007401 | 0.008405 | 0.000669 | −0.018336 | 0.020717 | 0.002986 | 0.006048 |
| 90 | −0.014447 | −0.017246 | 0.012724 | 0.00627 | 0.004516 | 0.008231 | 0.030292 | 0.00643 | −0.01493 | −0.007532 | −0.019599 | 0.004162 | 0.014497 | 0.004452 |
| 91 | −0.001158 | 0.004309 | 0.000279 | −0.035987 | 0.002521 | 0.019604 | 0.010689 | 0.018162 | −0.019194 | −0.000418 | 0.008354 | 0.037114 | −0.004801 | −0.004716 |
| 92 | −0.005959 | −0.035896 | 0.003619 | 0.014376 | −0.014293 | −0.021443 | −0.024777 | 0.009906 | −0.02926 | 0.017561 | −0.028402 | 0.01437 | −0.005705 | −0.062414 |
| 93 | −0.008026 | −0.001118 | −0.036722 | −0.029082 | 0.011083 | 0.009073 | −0.002112 | 0.007907 | −0.009102 | 0.009195 | −0.033787 | 0.018075 | 0.014276 | −0.008798 |
| 94 | −0.028973 | −0.000963 | −0.027741 | 0.023673 | −0.002462 | 0.004394 | 0.025614 | 0.010005 | −0.020177 | 0.007493 | 0.014122 | 0.037375 | −0.010202 | 0.020938 |
| 95 | −0.00849 | 0.002231 | 0.037455 | 0.025003 | −0.035994 | 0.029669 | 0.000051 | −0.02513 | −0.028848 | −0.01479 | 0.006471 | −0.03541 | −0.01016 | 0.019381 |
| 96 | 0.029421 | −0.027663 | −0.005865 | 0.029044 | −0.005601 | 0.004294 | 0.024793 | 0.017471 | 0.014725 | 0.009693 | 0.066077 | −0.036635 | −0.015598 | 0.042048 |
| 97 | 0.00111 | −0.034922 | 0.027686 | 0.003038 | 0.013888 | −0.021622 | 0.007618 | 0.015008 | −0.031485 | −0.013216 | −0.005173 | −0.025533 | −0.002223 | −0.012017 |
| 98 | −0.022929 | 0.007056 | −0.008072 | −0.002829 | 0.011855 | 0.005211 | 0.00021 | 0.017362 | −0.013377 | −0.004501 | 0.013124 | 0.002298 | 0.006364 | −0.013263 |
| 99 | 0.019425 | −0.024773 | 0.026621 | −0.004941 | 0.008335 | 0.000858 | 0.010064 | 0.016337 | −0.004144 | 0.001935 | 0.006621 | −0.004327 | −0.002739 | 0.001841 |
| 100 | −0.009366 | 0.050634 | −0.00662 | 0.022871 | −0.018902 | 0.008075 | −0.000487 | −0.001773 | −0.014125 | −0.008828 | 0.045273 | 0.004346 | −0.001903 | −0.004982 |
| 101 | −0.027591 | −0.000335 | −0.040524 | −0.001629 | 0.018065 | 0.004627 | −0.011795 | 0.018481 | −0.011952 | 0.006919 | 0.006527 | −0.001232 | −0.006502 | −0.009282 |
| 102 | 0.008598 | 0.030075 | −0.034824 | 0.02074 | 0.004281 | −0.005796 | 0.013037 | 0.017294 | −0.017077 | −0.003227 | 0.000822 | −0.009413 | 0.010923 | 0.003873 |
| 103 | −0.039525 | 0.044667 | 0.021841 | 0.047595 | −0.022493 | 0.002564 | 0.012261 | −0.003058 | −0.020071 | −0.000745 | 0.010178 | −0.014759 | −0.035231 | −0.023782 |
| 104 | 0.004732 | 0.013993 | 0.007555 | −0.020572 | −0.019225 | 0.002344 | −0.029556 | 0.024239 | −0.025138 | −0.027955 | −0.029468 | −0.011009 | −0.031958 | −0.021813 |
| 105 | −0.009676 | 0.065995 | −0.026798 | 0.03578 | −0.009169 | −0.012198 | −0.007773 | 0.040534 | 0.053366 | 0.039151 | −0.010962 | 0.04054 | −0.012462 | 0.017365 |
| 106 | −0.020555 | 0.022214 | −0.024567 | 0.000013 | 0.01828 | 0.028782 | −0.000194 | −0.01631 | 0.014105 | 0.015468 | −0.003959 | −0.03584 | 0.010403 | 0.004839 |
| 107 | 0.012668 | −0.014866 | −0.009602 | 0.017001 | 0.013494 | 0.026597 | −0.017866 | −0.026894 | 0.001869 | 0.009253 | −0.007909 | −0.00236 | 0.019586 | 0.017362 |
| 108 | 0.038272 | −0.043893 | −0.060881 | −0.009944 | 0.023269 | −0.024968 | −0.032682 | −0.008192 | 0.021028 | 0.016842 | −0.012994 | 0.009686 | 0.026924 | −0.01608 |
| 109 | 0.004632 | −0.041923 | −0.059756 | 0.007266 | 0.010228 | −0.010646 | −0.010648 | 0.002371 | −0.048654 | 0.017026 | 0.017658 | 0.007893 | 0.018236 | 0.016282 |
| 110 | 0.028367 | 0.033954 | −0.03136 | −0.051174 | −0.006455 | 0.021659 | 0.001731 | −0.005126 | 0.001655 | 0.034551 | 0.05481 | 0.030091 | −0.006552 | 0.022254 |
| 111 | 0.070395 | −0.022316 | −0.022558 | 0.020678 | 0.061683 | −0.007888 | 0.025171 | −0.00359 | 0.004659 | 0.016803 | 0.021179 | 0.002313 | 0.032181 | 0.025437 |
| 112 | 0.006167 | −0.003505 | 0.049596 | −0.014557 | −0.004516 | −0.016133 | −0.02803 | −0.025341 | 0.036992 | 0.01347 | 0.023859 | 0.009823 | 0.018916 | −0.041575 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 113 | −0.021336 | −0.050745 | −0.011389 | 0.015828 | 0.040491 | −0.013283 | −0.009204 | −0.016996 | −0.051351 | 0.002069 | −0.068371 | −0.020625 | 0.014448 | −0.013562 |
| 114 | 0.019033 | −0.013685 | −0.004089 | 0.02108 | 0.000915 | −0.035138 | −0.016223 | 0.027396 | −0.036888 | 0.010353 | −0.048447 | −0.019668 | −0.033792 | −0.011369 |
| 115 | 0.012822 | 0.060486 | −0.021232 | −0.032623 | 0.034315 | 0.016291 | −0.013569 | 0.003399 | 0.008362 | 0.059288 | 0.02808 | −0.002626 | −0.026951 | 0.02212 |
| 116 | 0.00705 | −0.062155 | 0.011442 | 0.013355 | −0.003823 | 0.008298 | 0.014695 | −0.028122 | 0.030442 | −0.005081 | 0.020173 | −0.023684 | 0.022802 | −0.028434 |
| 117 | 0.057146 | 0.04096 | 0.044065 | −0.008448 | 0.022942 | −0.036619 | 0.041133 | 0.042584 | −0.003076 | −0.009148 | −0.070562 | −0.010216 | 0.002544 | 0.006146 |
| 118 | −0.031396 | −0.003452 | −0.000106 | −0.009925 | −0.00289 | −0.008131 | 0.012993 | 0.007005 | −0.068811 | −0.02374 | 0.023721 | −0.074773 | −0.02925 | −0.012426 |
| 119 | −0.013841 | −0.018734 | −0.008866 | −0.017034 | −0.001216 | −0.002326 | 0.005346 | −0.069967 | −0.037874 | −0.020844 | 0.013433 | −0.006911 | 0.005875 | 0.000674 |
| 120 | 0.002397 | 0.015478 | 0.006333 | 0.014518 | 0.002264 | −0.022088 | 0.017712 | 0.010671 | −0.006774 | −0.047761 | −0.066372 | −0.013926 | −0.007708 | −0.03459 |
| 121 | 0.004383 | 0.023196 | 0.00894 | 0.02313 | 0.024481 | −0.014626 | 0.053301 | 0.030884 | 0.031038 | −0.001232 | −0.031711 | 0.092461 | 0.001705 | 0.008808 |
| 122 | 0.006917 | 0.012609 | 0.019241 | 0.009903 | 0.001639 | −0.012822 | −0.069419 | −0.041668 | −0.035948 | 0.034045 | 0.01791 | −0.030921 | −0.021362 | 0.004698 |
| 123 | −0.002234 | 0.054572 | −0.001487 | 0.01 | −0.008366 | −0.006407 | −0.06848 | −0.075406 | −0.043386 | 0.007047 | −0.008755 | 0.027404 | −0.015749 | 0.001003 |
| 124 | −0.00503 | 0.004436 | 0.012208 | 0.023301 | 0.002065 | −0.021974 | −0.010613 | −0.069646 | −0.03466 | −0.010328 | 0.035616 | −0.004747 | 0.009977 | −0.020351 |
| 125 | −0.035043 | 0.027544 | 0.05566 | −0.015191 | −0.017287 | 0.020084 | −0.018877 | 0.028446 | −0.001096 | −0.03583 | 0.011105 | 0.026922 | −0.018116 | −0.04967 |
| 126 | −0.000243 | −0.013771 | −0.014051 | 0.01574 | 0.004362 | 0.007323 | 0.017861 | 0.014631 | −0.008942 | −0.000679 | −0.049962 | −0.030227 | 0.00291 | 0.004681 |
| 127 | −0.027882 | −0.008954 | −0.001268 | 0.03117 | −0.011909 | 0.02995 | 0.012052 | 0.011884 | −0.008071 | 0.003875 | 0.028419 | −0.003997 | −0.013545 | −0.014314 |
| 128 | −0.034121 | −0.005129 | 0.002447 | −0.066651 | −0.054568 | 0.023311 | −0.019403 | 0.007774 | −0.025278 | −0.027188 | 0.024814 | −0.03124 | −0.03831 | −0.011264 |
| 129 | −0.039446 | −0.000317 | −0.003968 | −0.051789 | 0.034328 | −0.054109 | −0.022279 | −0.054576 | −0.020128 | −0.002382 | −0.009118 | −0.023381 | 0.005756 | −0.021078 |
| 130 | −0.042538 | −0.046837 | −0.009707 | −0.060147 | −0.016765 | −0.016371 | −0.019326 | −0.013723 | 0.007532 | −0.01003 | −0.033836 | −0.067999 | −0.005952 | −0.038129 |
| 131 | −0.033429 | −0.03212 | 0.005458 | −0.014348 | 0.057492 | 0.014637 | 0.034361 | −0.002257 | 0.01793 | 0.006567 | −0.014501 | −0.045964 | 0.011847 | 0.017409 |
| 132 | 0.004958 | 0.002385 | −0.00104 | −0.048529 | −0.043044 | 0.003154 | −0.003866 | 0.002892 | −0.023387 | −0.050967 | −0.001918 | 0.050633 | −0.008829 | −0.008857 |
| 133 | −0.042025 | 0.011899 | 0.032873 | −0.011252 | −0.007092 | 0.022799 | 0.000569 | 0.002327 | −0.04887 | −0.02953 | 0.032793 | 0.003575 | −0.017735 | 0.007398 |
| 134 | −0.011608 | −0.084236 | 0.073745 | 0.008839 | 0.018821 | 0.013809 | −0.00537 | −0.025184 | −0.026579 | 0.007314 | −0.056524 | 0.028336 | −0.016855 | −0.017648 |
| 135 | −0.024045 | 0.014822 | 0.01756 | 0.012115 | −0.045596 | −0.008659 | −0.025053 | −0.036343 | −0.032117 | −0.049606 | 0.00362 | −0.016454 | −0.017204 | −0.038315 |
| 136 | −0.01117 | −0.004422 | 0.00394 | −0.022001 | 0.009407 | −0.025808 | 0.001274 | −0.05892 | −0.072567 | −0.016967 | 0.014458 | −0.039603 | −0.013515 | −0.012417 |
| 137 | 0.862908 | −0.001634 | −0.026195 | −0.043341 | −0.014712 | 0.025752 | −0.0052 | 0.012243 | −0.015508 | −0.022616 | 0.016067 | −0.063488 | −0.033291 | −0.035625 |
| 138 | −0.014553 | 0.691472 | 0.109438 | −0.043959 | −0.005357 | −0.019226 | 0.004439 | −0.000999 | 0.021461 | 0.00729 | −0.103244 | −0.043952 | 0.032894 | −0.030904 |
| 139 | 0.005793 | 0.098453 | 0.586316 | −0.002638 | 0.015126 | −0.011845 | 0.009298 | 0.010495 | 0.016267 | −0.017333 | −0.003366 | −0.022971 | 0.016264 | 0.005681 |
| 140 | −0.023416 | −0.082764 | 0.017932 | 0.674433 | −0.012287 | 0.002223 | −0.021736 | 0.012972 | 0.015661 | −0.030829 | −0.07597 | −0.07764 | 0.007107 | −0.018412 |
| 141 | −0.011682 | −0.012204 | 0.006601 | −0.008699 | 0.874254 | −0.007511 | −0.032999 | −0.032584 | 0.023478 | −0.021864 | −0.004964 | −0.001168 | −0.034425 | 0.004926 |
| 142 | 0.026279 | 0.002903 | −0.000623 | 0.004769 | 0.021284 | 0.835937 | −0.050756 | −0.056131 | −0.030615 | 0.000297 | −0.06234 | −0.01832 | 0.015834 | −0.026603 |
| 143 | 0.003928 | 0.020722 | 0.012146 | −0.011769 | −0.025724 | −0.051118 | 0.850201 | −0.06751 | −0.055748 | 0.000359 | −0.013101 | 0.021059 | −0.035396 | −0.036986 |
| 144 | 0.01128 | −0.007604 | 0.013116 | 0.013214 | −0.020985 | −0.058997 | −0.063767 | 0.829415 | −0.070275 | −0.005429 | −0.01213 | −0.03055 | 0.004171 | 0.012176 |
| 145 | −0.006923 | 0.023038 | 0.019098 | 0.006328 | 0.014245 | −0.022613 | −0.048875 | −0.063501 | 0.799048 | −0.01831 | 0.02249 | 0.01388 | −0.037975 | −0.019507 |
| 146 | −0.015046 | 0.00346 | −0.000189 | −0.03694 | −0.023016 | −0.01017 | −0.005803 | −0.013469 | −0.011662 | 0.916438 | −0.043445 | −0.019106 | 0.004781 | −0.046289 |
| 147 | 0.015541 | −0.078505 | 0.004931 | −0.023958 | 0.03468 | −0.08477 | −0.029024 | −0.008379 | −0.001151 | −0.030598 | 0.655728 | −0.004097 | 0.059665 | −0.0186 |
| 148 | −0.04814 | −0.047566 | −0.067743 | −0.103233 | 0.01387 | −0.00855 | 0.006651 | −0.013779 | 0.00175 | −0.018772 | −0.036068 | 0.653896 | −0.003191 | −0.011058 |
| 149 | −0.035584 | 0.03943 | 0.005462 | −0.007069 | −0.04095 | 0.013984 | −0.043304 | 0.006558 | −0.027674 | −0.001203 | 0.060071 | −0.007725 | 0.899874 | 0.012776 |
| 150 | −0.036911 | −0.014662 | 0.01687 | −0.01227 | 0.007222 | −0.01861 | −0.038847 | 0.00762 | −0.030409 | −0.051626 | −0.02806 | −0.009478 | 0.017622 | 0.847138 |
| 151 | 0.033704 | 0.03815 | −0.087584 | −0.007251 | −0.000166 | 0.023963 | −0.050886 | −0.059175 | −0.01832 | 0.006846 | −0.053607 | −0.005868 | −0.01825 | 0.003052 |
| 152 | 0.001155 | −0.005292 | −0.003538 | 0.010244 | 0.000014 | −0.029817 | −0.002927 | −0.036056 | 0.001027 | 0.003442 | 0.034837 | 0.024147 | −0.004145 | −0.01725 |
| 153 | 0.030346 | 0.047359 | −0.074541 | 0.02629 | −0.028083 | −0.071097 | −0.019162 | −0.054575 | 0.020235 | −0.032115 | −0.017355 | 0.016976 | 0.009598 | −0.008265 |
| 154 | 0.019913 | 0.000861 | 0.003337 | 0.002304 | 0.024593 | −0.09069 | −0.017039 | −0.055913 | −0.03146 | −0.012742 | −0.0542 | 0.007918 | 0.022224 | −0.01382 |
| 155 | 0.009207 | −0.016824 | −0.009892 | −0.011466 | 0.024732 | −0.018924 | 0.001245 | −0.026715 | −0.035521 | −0.043739 | 0.032599 | 0.027486 | 0.00741 | −0.018042 |
| 156 | 0.001985 | −0.024346 | 0.00052 | 0.028708 | −0.024269 | −0.006628 | −0.055659 | −0.044443 | −0.026076 | −0.019499 | −0.02478 | 0.031464 | −0.016068 | −0.009132 |
| 157 | −0.000364 | 0.007969 | 0.02027 | −0.048676 | −0.018272 | −0.006213 | −0.013899 | −0.008172 | −0.010431 | −0.041867 | −0.009519 | −0.013717 | −0.002396 | −0.037895 |
| 158 | −0.001175 | −0.03893 | −0.023929 | 0.019813 | −0.025162 | 0.003503 | −0.019833 | 0.004406 | 0.032131 | −0.003543 | −0.029773 | −0.002231 | −0.003166 | 0.032483 |
| 159 | −0.04873 | −0.025535 | −0.025552 | 0.023126 | −0.004798 | −0.023645 | −0.006862 | 0.005388 | −0.079067 | 0.017215 | 0.017981 | 0.014036 | −0.001626 | −0.058038 |
| 160 | −0.064007 | 0.004752 | −0.032593 | −0.039108 | 0.002483 | 0.018529 | −0.005238 | 0.028824 | 0.004499 | 0.018298 | −0.020311 | −0.059295 | −0.04396 | 0.017044 |
| 161 | −0.024477 | −0.07593 | −0.061437 | −0.015209 | −0.039777 | −0.004128 | −0.023558 | −0.014285 | 0.039469 | −0.027403 | −0.0444 | −0.082291 | −0.020994 | 0.003688 |
| 162 | −0.048752 | −0.028634 | −0.011162 | −9.016349 | −0.02669 | −0.017718 | −0.028258 | −0.046423 | −0.028839 | −0.030238 | −0.016654 | 0.022667 | −0.023566 | −0.027711 |

APPENDIX B3-continued

PCA Transformation Matrix (340 × 340 Early/Late)

| | | | | | | | | | | | | | | |
|---|---|---|---|---|---|---|---|---|---|---|---|---|---|---|
| 163 | −0.0285 | 0.011807 | 0.023828 | 0.015959 | −0.006516 | −0.051848 | −0.023672 | −0.019726 | −0.019448 | −0.006823 | 0.010756 | −0.0017 | −0.011864 | −0.034194 |
| 164 | −0.019599 | 0.032161 | −0.052298 | −0.020881 | −0.001662 | −0.034875 | −0.016054 | −0.044139 | −0.040423 | 0.013197 | −0.003666 | −0.001817 | −0.017792 | 0.016255 |
| 165 | 0.015974 | −0.043094 | 0.003997 | −0.00113 | 0.015323 | 0.008918 | 0.003021 | −0.019534 | 0.013305 | −0.020985 | 0.032466 | −0.039138 | −0.0293 | 0.038487 |
| 166 | 0.015127 | −0.085811 | 0.027411 | −0.018937 | −0.000342 | −0.06037 | 0.019549 | −0.043957 | 0.025892 | 0.015607 | −0.006475 | −0.076047 | 0.014545 | 0.029632 |
| 167 | −0.029853 | −0.009523 | −0.04432 | −0.042819 | −0.026685 | −0.01351 | −0.031491 | −0.05965 | −0.079873 | −0.022611 | −0.013257 | 0.00523 | −0.021444 | −0.000321 |
| 168 | −0.034847 | 0.027522 | 0.021535 | 0.00854 | −0.028316 | 0.00749 | −0.013396 | −0.013383 | −0.000985 | 0.011136 | 0.058691 | −0.008308 | −0.014496 | 0.006215 |
| 169 | −0.001653 | 0.002424 | −0.026525 | 0.019808 | −0.002655 | 0.009158 | −0.000059 | 0.016889 | −0.001139 | −0.025943 | −0.005775 | 0.008223 | 0.001109 | −0.028582 |
| 170 | 0.006094 | −0.018252 | −0.027283 | 0.022893 | −0.002839 | 0.013365 | 0.012575 | 0.012184 | 0.00792 | −0.012016 | −0.012718 | −0.003509 | 0.008731 | −0.010444 |
| 171 | 0.009854 | −0.003365 | −0.024722 | 0.016852 | −0.040173 | 0.006841 | −0.003164 | −0.00094 | 0.021385 | −0.017683 | 0.003433 | 0.028033 | −0.004816 | −0.008572 |
| 172 | −0.004761 | 0.001478 | −0.031793 | 0.017592 | −0.000708 | 0.022373 | 0.013872 | 0.015967 | −0.009742 | −0.035061 | −0.014113 | 0.006172 | −0.000038 | −0.033343 |
| 173 | −0.022225 | 0.022881 | −0.02948 | 0.009098 | 0.018545 | 0.027648 | 0.023045 | 0.047275 | 0.003413 | −0.004243 | 0.010722 | 0.009288 | −0.02004 | 0.004535 |
| 174 | −0.016446 | 0.000962 | −0.022866 | 0.005391 | −0.005315 | 0.032623 | 0.012425 | 0.016046 | −0.005784 | −0.0043 | 0.002928 | 0.005342 | −0.015239 | 0.009723 |
| 175 | −0.034987 | 0.021406 | −0.032378 | 0.040872 | 0.001196 | 0.046072 | 0.00099 | 0.024807 | 0.002057 | −0.019208 | 0.000422 | −0.033686 | −0.033705 | −0.041557 |
| 176 | −0.003524 | −0.029 | −0.020036 | 0.0504 | −0.02855 | 0.03049 | 0.010679 | 0.008829 | 0.024239 | −0.012896 | 0.019787 | −0.009186 | 0.000217 | 0.001072 |
| 177 | 0.027916 | −0.022834 | −0.028935 | 0.015956 | 0.003471 | 0.054706 | 0.062834 | −0.017193 | 0.01087 | −0.002501 | −0.054792 | −0.020375 | 0.0382 | 0.009891 |
| 178 | −0.041731 | 0.026467 | −0.065265 | 0.006496 | 0.005935 | 0.036489 | 0.019831 | 0.010021 | 0.000233 | −0.01047 | −0.017205 | −0.028312 | 0.021877 | −0.015464 |
| 179 | −0.000044 | −0.012565 | −0.004803 | −0.012616 | 0.012471 | −0.002108 | 0.001935 | 0.005805 | −0.004779 | 0.00223 | −0.010291 | −0.009361 | 0.021411 | −0.009058 |
| 180 | −0.015135 | −0.013282 | −0.022254 | −0.010804 | 0.009966 | 0.007067 | 0.014423 | 0.016665 | 0.01266 | 0.005077 | −0.014091 | −0.016747 | 0.014805 | 0.000908 |
| 181 | −0.004265 | −0.005662 | −0.021294 | −0.002364 | 0.015773 | 0.010841 | 0.011 | 0.014496 | 0.005712 | 0.008488 | −0.007442 | 0.005352 | 0.01841 | 0.004758 |
| 182 | 0.000838 | −0.003849 | −0.00602 | 0.004987 | 0.003458 | 0.008028 | 0.02045 | 0.007467 | 0.007034 | 0.010777 | 0.003327 | −0.01497 | 0.01611 | 0.004921 |
| 183 | 0.014132 | 0.005841 | 0.021554 | 0.014729 | −0.01928 | 0.011037 | 0.005445 | −0.008979 | 0.002141 | 0.002067 | 0.023393 | 0.016987 | 0.017636 | −0.001937 |
| 184 | 0.001809 | −0.003042 | 0.030504 | 0.000268 | −0.019324 | −0.001065 | −0.015746 | −0.032059 | −0.020925 | −0.000754 | 0.027371 | 0.017735 | −0.000432 | 0.007565 |
| 185 | 0.01444 | −0.007846 | 0.056255 | 0.019071 | −0.004414 | 0.008778 | −0.00998 | 0.012625 | 0.000722 | 0.017732 | 0.056442 | 0.021345 | 0.001542 | −0.025362 |
| 186 | 0.010945 | 0.005614 | −0.013339 | −0.05093 | −0.00204 | 0.005497 | −0.001342 | −0.001668 | 0.038872 | −0.001071 | −0.039304 | −0.028489 | 0.005017 | 0.024341 |
| 187 | −0.000381 | 0.032061 | −0.000023 | 0.023377 | 0.01911 | −0.002511 | 0.026409 | 0.022171 | −0.008149 | 0.003362 | −0.005143 | −0.016368 | 0.003233 | 0.010076 |
| 188 | 0.008525 | 0.003302 | −0.018921 | 0.01764 | 0.004331 | −0.000739 | 0.025439 | 0.002153 | −0.002754 | 0.004113 | −0.015493 | −0.011149 | 0.014244 | 0.018585 |
| 189 | 0.008599 | 0.007053 | −0.046115 | 0.034303 | −0.000268 | −0.024459 | 0.000822 | 0.001899 | −0.000746 | 0.010019 | −0.021756 | −0.022766 | 0.018668 | −0.016868 |
| 190 | −0.030505 | −0.005735 | −0.013611 | −0.016434 | −0.030956 | 0.031077 | −0.009805 | 0.003594 | −0.002946 | −0.001877 | 0.005226 | −0.003461 | −0.043489 | 0.010743 |
| 191 | −0.007405 | −0.005626 | 0.010719 | −0.055698 | −0.029066 | 0.015464 | −0.013362 | 0.011364 | −0.00292 | −0.020067 | −0.002034 | −0.014131 | −0.037884 | 0.009282 |
| 192 | −0.002543 | −0.005668 | 0.054721 | −0.023756 | −0.031567 | 0.016769 | −0.017082 | −0.016993 | −0.013765 | −0.008153 | 0.043994 | 0.002382 | −0.007597 | −0.009184 |
| 193 | −0.00186 | 0.033972 | 0.027643 | 0.0315 | −0.024431 | 0.020652 | 0.008429 | −0.016503 | 0.010966 | 0.003113 | 0.005233 | −0.005926 | −0.004024 | 0.037468 |
| 194 | 0.006729 | −0.004474 | 0.007691 | 0.010385 | −0.005581 | 0.017361 | −0.004634 | 0.010369 | 0.014631 | −0.005295 | −0.031782 | 0.017984 | 0.013748 | −0.023081 |
| 195 | −0.003837 | 0.002965 | −0.001523 | −0.028041 | 0.030691 | 0.003803 | −0.007605 | 0.010124 | −0.007089 | 0.009366 | 0.012426 | −0.015256 | −0.006483 | −0.007088 |
| 196 | −0.008877 | 0.003986 | −0.020154 | −0.028111 | 0.017692 | 0.020819 | −0.004765 | 0.001555 | −0.002865 | 0.008272 | 0.015399 | −0.017207 | −0.016497 | 0.000157 |
| 197 | −0.016744 | 0.012339 | 0.035403 | −0.027 | −0.042616 | 0.038564 | −0.020661 | 0.002296 | −0.014981 | −0.009952 | 0.027254 | 0.017413 | −0.067355 | 0.02677 |
| 198 | −0.001547 | −0.017188 | 0.019327 | 0.007544 | 0.002414 | 0.020938 | 0.027167 | 0.011706 | 0.009363 | −0.008848 | −0.022032 | −0.053047 | 0.030146 | −0.032409 |
| 199 | −0.05764 | −0.051485 | −0.001043 | −0.023612 | −0.007558 | −0.061806 | −0.030701 | −0.004311 | −0.003604 | 0.023315 | −0.065235 | −0.024472 | −0.052982 | 0.012917 |
| 200 | −0.011864 | 0.02208 | −0.067394 | 0.008149 | −0.020006 | 0.025198 | 0.024268 | −0.009236 | 0.009574 | −0.020882 | 0.001629 | 0.014323 | 0.035474 | −0.01134 |
| 201 | 0.000158 | −0.00543 | −0.058971 | 0.028153 | −0.03223 | 0.029407 | 0.009056 | 0.033271 | 0.024372 | −0.006604 | 0.048423 | −0.04672 | −0.016866 | 0.006961 |
| 202 | 0.003023 | 0.028511 | −0.000822 | 0.001347 | 0.003531 | 0.036101 | 0.009111 | 0.001762 | −0.004827 | −0.001905 | −0.01324 | −0.000551 | 0.004432 | −0.002867 |
| 203 | −0.002428 | 0.016794 | −0.034737 | 0.015991 | −0.004077 | 0.021759 | 0.011954 | 0.014324 | −0.032898 | 0.010706 | 0.019402 | −0.017163 | −0.020573 | 0.005332 |
| 204 | 0.024554 | −0.0206 | 0.034923 | −0.003813 | 0.006019 | 0.021234 | −0.003033 | −0.016901 | 0.003639 | −0.009937 | 0.016429 | 0.002553 | 0.004605 | −0.019794 |
| 205 | −0.035563 | −0.086817 | −0.053504 | −0.098942 | −0.015697 | 0.008198 | −0.010807 | 0.016998 | −0.000645 | 0.017247 | 0.001552 | 0.013694 | 0.018457 | −0.010034 |
| 206 | 0.016328 | 0.071855 | −0.039642 | 0.027823 | 0.040115 | −0.023858 | −0.014691 | −0.01733 | −0.02239 | 0.014272 | 0.003529 | −0.006712 | 0.019704 | −0.00739 |
| 207 | −0.038817 | 0.033579 | −0.047779 | 0.075084 | 0.002067 | 0.023336 | −0.003696 | −0.021956 | 0.063918 | 0.025734 | 0.034008 | −0.005777 | −0.020685 | 0.017861 |
| 208 | 0.017533 | −0.010523 | −0.00845 | 0.024996 | −0.008215 | 0.042607 | 0.027053 | 0.001178 | −0.024887 | 0.01179 | 0.075566 | 0.044252 | 0.002553 | 0.002733 |
| 209 | 0.012235 | −0.107203 | 0.118288 | 0.046594 | −0.020661 | 0.00254 | 0.01058 | −0.010692 | 0.004306 | −0.013115 | −0.041562 | 0.039642 | 0.006929 | −0.010948 |
| 210 | −0.02606 | −0.019896 | 0.068202 | 0.018805 | 0.021137 | 0.061338 | 0.025368 | 0.038433 | 0.004653 | −0.025861 | −0.002563 | −0.002355 | −0.022911 | −0.033837 |
| 211 | −0.024423 | 0.005924 | −0.003173 | −0.056144 | 0.022361 | 0.005205 | −0.013347 | 0.025343 | −0.004645 | −0.027943 | 0.017122 | −0.034281 | −0.023566 | −0.060788 |
| 212 | −0.011015 | 0.016658 | −0.029011 | −0.032571 | 0.022468 | −0.063724 | 0.018663 | −0.011479 | 0.014331 | −0.001039 | −0.018312 | −0.055863 | 0.027959 | −0.011023 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 213 | 0.011373 | −0.038192 | 0.043995 | −0.035589 | 0.039434 | 0.013934 | −0.012499 | −0.008845 | −0.028515 | 0.030209 | −0.062194 | −0.014565 | 0.020131 | 0.024916 |
| 214 | −0.016102 | 0.011373 | −0.006006 | −0.013817 | 0.0004 | −0.005863 | 0.001962 | 0.006704 | 0.009148 | −0.006482 | 0.006927 | −0.000655 | 0.017239 | −0.024146 |
| 215 | −0.013131 | 0.028474 | 0.023069 | 0.012972 | 0.019168 | 0.01416 | −0.014734 | −0.008249 | 0.002003 | −0.007911 | 0.018262 | 0.000926 | 0.02798 | −0.016765 |
| 216 | −0.012301 | 0.027099 | −0.019857 | 0.017016 | −0.017321 | 0.002472 | −0.013994 | −0.022196 | −0.008889 | 0.01221 | 0.027062 | 0.006218 | −0.016158 | 0.013097 |
| 217 | 0.021955 | −0.00556 | −0.009275 | −0.032014 | 0.029388 | 0.017388 | −0.002926 | 0.018543 | −0.037361 | −0.008833 | −0.012404 | 0.034268 | 0.018898 | −0.047448 |
| 218 | −0.006072 | 0.017057 | −0.010657 | 0.009203 | 0.004614 | 0.020007 | −0.018919 | −0.006213 | −0.021728 | −0.007859 | 0.026139 | 0.006944 | −0.005937 | −0.010951 |
| 219 | 0.006635 | 0.021849 | −0.030743 | 0.008877 | 0.003652 | −0.012981 | −0.021566 | −0.018083 | −0.02486 | −0.011988 | −0.004435 | 0.021125 | 0.005266 | −0.020456 |
| 220 | 0.001779 | 0.015115 | 0.014256 | −0.002512 | 0.024215 | 0.032948 | 0.01792 | 0.010373 | −0.013488 | −0.006579 | 0.055267 | 0.056924 | 0.019405 | −0.023994 |
| 221 | 0.006255 | 0.000845 | −0.001584 | −0.008626 | 0.02273 | 0.003099 | −0.002483 | 0.053395 | 0.008998 | −0.011624 | −0.007685 | 0.056901 | 0.002268 | −0.025485 |
| 222 | −0.019461 | −0.004626 | −0.014334 | 0.00509 | −0.002636 | 0.012316 | −0.002001 | 0.01745 | 0.002309 | −0.001713 | 0.024309 | 0.023117 | −0.001988 | −0.017004 |
| 223 | −0.006929 | 0.038743 | −0.023197 | 0.022788 | −0.003614 | 0.020421 | −0.000957 | 0.025077 | 0.026677 | 0.012142 | 0.037625 | 0.04697 | −0.011053 | 0.006671 |
| 224 | −0.01047 | 0.000568 | 0.004549 | 0.022239 | −0.013571 | 0.010873 | 0.022189 | 0.005567 | −0.002932 | 0.011982 | 0.027737 | −0.030235 | −0.016646 | 0.011385 |
| 225 | −0.017573 | −0.00729 | 0.013516 | 0.016231 | −0.011234 | 0.008008 | 0.023327 | 0.014674 | −0.01723 | 0.009308 | 0.026159 | −0.007612 | −0.02016 | 0.004596 |
| 226 | 0.013358 | 0.017868 | 0.030835 | 0.01007 | −0.010429 | −0.016824 | −0.019893 | −0.010864 | −0.000421 | 0.004911 | 0.031096 | 0.007651 | −0.00341 | 0.00038 |
| 227 | −0.004041 | 0.044229 | −0.000822 | 0.004877 | −0.002546 | −0.018264 | −0.000231 | −0.004619 | −0.021126 | −0.004003 | 0.002339 | −0.041161 | 0.002018 | −0.019718 |
| 228 | −0.043313 | 0.037479 | −0.011545 | −0.000221 | −0.030799 | 0.005134 | −0.005171 | 0.016086 | −0.006501 | 0.005336 | 0.045195 | 0.012957 | −0.031009 | 0.001327 |
| 229 | −0.012323 | −0.008173 | −0.003375 | 0.06909 | −0.003293 | −0.007768 | −0.012126 | 0.017786 | −0.028596 | 0.006929 | 0.005435 | 0.053711 | 0.00836 | 0.008067 |
| 230 | −0.055774 | −0.000433 | −0.026517 | 0.01833 | −0.019487 | −0.004765 | 0.008048 | −0.001081 | 0.015842 | 0.001374 | 0.015209 | −0.016795 | −0.009011 | 0.007196 |
| 231 | 0.01115 | 0.004013 | 0.016684 | 0.010482 | 0.004138 | −0.038871 | −0.002314 | 0.009285 | −0.018459 | 0.010154 | 0.013841 | 0.004086 | −0.024258 | 0.015761 |
| 232 | −0.007803 | −0.007857 | 0.032597 | −0.018829 | −0.020071 | 0.009383 | −0.002788 | 0.012576 | 0.05 | 0.012148 | 0.029568 | −0.019875 | −0.009248 | 0.029848 |
| 233 | −0.006386 | −0.015865 | −0.013161 | −0.019643 | 0.013578 | 0.026755 | 0.004154 | 0.004649 | 0.007616 | −0.003185 | −0.01774 | −0.068033 | 0.020291 | 0.015055 |
| 234 | −0.039129 | 0.022981 | 0.0147 | 0.004185 | −0.003659 | 0.005208 | −0.003937 | 0.014546 | −0.019933 | −0.003035 | 0.028499 | 0.03527 | −0.004814 | −0.008456 |
| 235 | −0.020087 | −0.005472 | −0.008275 | 0.001275 | 0.007251 | −0.018842 | 0.007451 | 0.007017 | −0.032481 | −0.024684 | −0.017299 | 0.010493 | 0.019252 | −0.018296 |
| 236 | 0.011465 | −0.020341 | −0.002886 | 0.019987 | −0.013496 | −0.003484 | 0.000492 | −0.015091 | 0.038741 | 0.005061 | 0.000945 | −0.019352 | −0.002281 | 0.022467 |
| 237 | 0.001786 | −0.03298 | −0.015967 | −0.007474 | −0.015677 | 0.007957 | −0.001411 | −0.012711 | −0.014045 | 0.005391 | −0.012499 | 0.005016 | −0.014788 | 0.012578 |
| 238 | −0.008042 | −0.016931 | −0.022322 | −0.028432 | −0.003055 | −0.001897 | −0.003945 | −0.00459 | −0.018927 | 0.002565 | −0.022764 | 0.002977 | −0.0128 | 0.000214 |
| 239 | −0.001752 | 0.010147 | −0.013919 | −0.014573 | 0.004955 | −0.00836 | −0.004888 | −0.008424 | −0.02079 | 0.003516 | −0.007899 | −0.021725 | −0.007611 | 0.000889 |
| 240 | 0.008267 | −0.014017 | 0.002409 | −0.037968 | 0.010696 | 0.009188 | −0.00191 | −0.000044 | 0.004673 | 0.007107 | −0.037693 | −0.042189 | −0.006466 | 0.022905 |
| 241 | −0.001303 | −0.020845 | 0.012205 | −0.020647 | 0.008163 | 0.034269 | −0.00082 | −0.016476 | 0.008663 | 0.005315 | −0.004579 | −0.049107 | 0.009906 | 0.017414 |
| 242 | −0.009988 | 0.002323 | −0.046721 | 0.01433 | 0.018221 | 0.006909 | 0.005547 | 0.00811 | 0.012838 | 0.005637 | −0.000392 | −0.025092 | 0.021994 | 0.006204 |
| 243 | −0.012851 | 0.003922 | −0.06214 | 0.008273 | 0.012081 | 0.00509 | −0.00461 | 0.030006 | 0.006359 | −0.019157 | −0.01421 | −0.028454 | 0.016873 | −0.040436 |
| 244 | 0.002618 | 0.01155 | 0.010347 | 0.005996 | 0.011395 | −0.016248 | 0.008069 | 0.033512 | 0.026636 | −0.009685 | −0.035211 | 0.013146 | 0.012414 | −0.01126 |
| 245 | 0.021823 | −0.012588 | 0.000431 | −0.001296 | −0.009236 | −0.011698 | −0.02455 | −0.024506 | −0.001634 | 0.006672 | −0.035702 | 0.025397 | 0.020362 | 0.01299 |
| 246 | −0.008531 | −0.004448 | −0.024854 | 0.00987 | 0.001709 | 0.007662 | 0.00478 | −0.020488 | −0.015342 | 0.014959 | 0.015061 | −0.002661 | 0.0091 | 0.017253 |
| 247 | −0.019323 | 0.003509 | −0.02689 | −0.007646 | 0.004054 | 0.011596 | 0.002998 | −0.00263 | −0.003635 | −0.004325 | 0.00467 | −0.013057 | −0.002128 | −0.004975 |
| 248 | −0.015178 | −0.004074 | 0.011116 | −0.029734 | −0.008399 | 0.006246 | −0.001884 | −0.013753 | 0.005233 | −0.021372 | 0.004687 | 0.011995 | 0.004596 | −0.014755 |
| 249 | −0.009605 | −0.064716 | 0.009673 | −0.043338 | −0.012603 | 0.028611 | 0.000011 | −0.018884 | 0.036763 | −0.001572 | −0.023873 | −0.041805 | 0.011658 | 0.010615 |
| 250 | 0.004491 | 0.003703 | 0.010166 | −0.008951 | −0.004797 | 0.011415 | 0.014221 | 0.014145 | 0.021948 | 0.009864 | −0.008739 | −0.004959 | −0.008102 | 0.027069 |
| 251 | −0.000209 | 0.010302 | −0.002324 | −0.006315 | 0.003229 | 0.009171 | 0.0199641 | 0.0191 | 0.0164891 | −0.000547 | −0.016307 | 0.0193211 | −0.001369 | 0.014118 |
| 252 | 0.006517 | 0.007983 | 0.01892 | −0.028331 | 0.01034 | 0.011069 | −0.012178 | 0.009198 | 0.008266 | 0.001271 | −0.013128 | 0.027271 | 0.016948 | −0.006796 |
| 253 | −0.005967 | −0.020957 | 0.011638 | 0.01514 | −0.018508 | 0.027404 | −0.010931 | 0.007221 | 0.033684 | 0.002783 | 0.03377 | 0.033924 | 0.003081 | −0.005394 |
| 254 | 0.004084 | 0.024248 | −0.005402 | 0.025724 | 0.009424 | −0.005512 | 0.014575 | 0.018135 | 0.027465 | 0.006176 | −0.014059 | −0.003027 | 0.003361 | 0.00647 |
| 255 | −0.000596 | 0.010691 | −0.002685 | 0.005332 | 0.016998 | −0.012691 | 0.016456 | 0.031943 | 0.018262 | −0.006713 | −0.046282 | 0.004441 | 0.0135 | −0.004403 |
| 256 | 0.011469 | −0.032784 | 0.036757 | −0.038286 | −0.005569 | 0.025571 | −0.006067 | 0.0048541 | 0.005255 | 0.004069 | −0.019219 | 0.026179 | 0.012826 | 0.027701 |
| 257 | 0.009897 | −0.005062 | 0.011186 | −0.04689 | 0.008754 | 0.018105 | −0.004959 | 0.009148 | 0.002176 | 0.0069261 | 0.010854 | 0.017991 | −0.000109 | −0.000697 |
| 258 | −0.004013 | 0.019257 | −0.013015 | −0.014657 | 0.004013 | 0.021874 | 0.00098 | −0.003327 | −0.000831 | −0.011257 | 0.009883 | −0.003117 | −0.019061 | −0.004425 |
| 259 | −0.011746 | −0.008251 | −0.029616 | 0.003026 | −0.013443 | 0.013192 | 0.022032 | 0.008354 | 0.022084 | −0.003432 | 0.001199 | −0.004941 | 0.001896 | 0.004101 |
| 260 | −0.018662 | 0.005758 | 0.014042 | −0.002988 | 0.000096 | 0.005924 | 0.024431 | 0.015535 | 0.015026 | 0.007906 | 0.019499 | 0.025045 | 0.012444 | −0.020679 |
| 261 | −0.016616 | 0.02107 | −0.011866 | −0.010408 | 0.017147 | 0.005543 | 0.005204 | 0.00526 | −0.023947 | 0.013387 | 0.0137 | 0.025024 | −0.014601 | −0.000715 |
| 262 | −0.011993 | 0.009565 | −0.021384 | 0.000517 | 0.003784 | 0.005033 | −0.005075 | −0.003696 | −0.00263 | 0.010483 | 0.007815 | −0.000467 | −0.003894 | 0.004484 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 263 | −0.003038 | 0.016341 | −0.023556 | −0.008022 | −0.00363 | 0.001001 | −0.003724 | −0.001774 | 0.006091 | −0.009979 | −0.000833 | 0.009801 | 0.005822 | −0.004543 |
| 264 | −0.012553 | −0.018473 | −0.001678 | 0.017116 | −0.013811 | −0.005737 | 0.010764 | −0.011184 | 0.000337 | −0.007318 | 0.006986 | −0.040923 | 0.00369 | −0.008764 |
| 265 | −0.006688 | 0.005569 | 0.006119 | 0.003851 | −0.000285 | −0.023374 | 0.003165 | −0.002163 | 0.006329 | 0.011498 | 0.007677 | −0.052316 | −0.012068 | −0.004706 |
| 266 | 0.002415 | 0.020027 | 0.007947 | −0.006715 | 0.012758 | −0.019359 | −0.004975 | 0.014307 | 0.001259 | 0.017172 | 0.008717 | 0.00533 | −0.01627 | −0.008493 |
| 267 | 0.006787 | 0.003746 | 0.017773 | 0.043222 | −0.016139 | −0.010882 | −0.005277 | 0.002392 | −0.008888 | 0.020205 | 0.026218 | 0.015822 | 0.002994 | 0.024592 |
| 268 | 0.013425 | 0.007728 | 0.033806 | 0.012487 | −0.007717 | −0.023136 | −0.017502 | −0.004828 | −0.000689 | 0.002508 | 0.02243 | −0.011506 | −0.00677 | −0.003148 |
| 269 | 0.014327 | 0.002477 | 0.044348 | 0.012006 | −0.000009 | −0.016967 | −0.010624 | 0.003048 | 0.01307 | 0.004798 | 0.017242 | 0.004278 | 0.005412 | −0.010438 |
| 270 | 0.001277 | 0.033186 | 0.034404 | 0.003177 | −0.005393 | −0.014061 | −0.003409 | −0.012679 | 0.007179 | −0.004576 | 0.016167 | −0.023424 | 0.003155 | −0.015827 |
| 271 | 0.020723 | −0.006201 | −0.004472 | 0.040038 | −0.048176 | −0.030607 | −0.05183 | −0.029194 | 0.002131 | −0.000698 | −0.012415 | 0.026277 | 0.004552 | 0.000971 |
| 272 | −0.002873 | −0.009914 | −0.017158 | 0.056139 | −0.011353 | −0.018357 | −0.015581 | 0.000079 | −0.031882 | −0.001285 | 0.002255 | 0.030198 | −0.00339 | 0.016887 |
| 273 | −0.021128 | −0.015369 | −0.009764 | 0.006369 | −0.000235 | −0.011155 | 0.00783 | 0.002608 | 0.019094 | −0.021424 | 0.005568 | −0.015891 | 0.001071 | −0.010997 |
| 274 | −0.019174 | −0.018025 | −0.011084 | 0.006074 | 0.005551 | −0.012803 | 0.012797 | 0.003556 | 0.020264 | −0.017941 | 0.003318 | −0.018402 | 0.007521 | −0.011727 |
| 275 | −0.053165 | 0.034557 | −0.055231 | 0.014438 | −0.01132 | −0.014903 | 0.031234 | −0.02027 | 0.027887 | −0.027051 | −0.005259 | −0.062611 | 0.019282 | −0.023593 |
| 276 | 0.011936 | −0.022292 | −0.006722 | 0.037837 | −0.009649 | −0.003185 | −0.008073 | −0.010161 | 0.013318 | 0.00857 | 0.007057 | −0.010501 | −0.011395 | 0.02979 |
| 277 | −0.007575 | −0.013943 | 0.001412 | 0.006852 | 0.004868 | −0.010378 | 0.009412 | −0.00961 | −0.004973 | 0.00689 | −0.000491 | −0.042361 | −0.009608 | 0.009532 |
| 278 | −0.009879 | 0.000705 | 0.014585 | 0.024608 | −0.010959 | −0.001758 | 0.026314 | −0.012263 | 0.009126 | 0.003741 | 0.001141 | −0.027896 | −0.005998 | 0.018944 |
| 279 | 0.000265 | 0.016544 | 0.00574 | −0.010785 | 0.002039 | −0.017856 | −0.001517 | −0.011555 | −0.012244 | −0.001518 | −0.015456 | −0.017498 | −0.003212 | −0.003874 |
| 280 | −0.010693 | −0.026333 | −0.03709 | 0.025823 | −0.003996 | 0.014063 | −0.002263 | 0.02788 | 0.019456 | −0.014735 | 0.016205 | −0.049671 | −0.000172 | −0.011498 |
| 281 | −0.004936 | 0.012372 | 0.002546 | 0.038368 | −0.016137 | 0.019716 | 0.006126 | −0.027012 | −0.009079 | 0.00568 | 0.042933 | −0.008422 | −0.012494 | 0.026274 |
| 282 | −0.007152 | 0.030105 | 0.00682 | 0.035981 | −0.024358 | 0.035933 | 0.019991 | −0.007457 | 0.016763 | −0.002595 | 0.035855 | −0.006584 | −0.007104 | 0.022178 |
| 283 | −0.013582 | 0.029582 | −0.006069 | −0.001652 | −0.0141 | 0.006946 | 0.002408 | −0.015927 | 0.008928 | −0.019293 | 0.013561 | −0.007192 | 0.004643 | −0.010417 |
| 284 | 0.007999 | 0.001105 | 0.016637 | −0.030553 | −0.001702 | 0.008605 | −0.00188 | −0.000652 | 0.000768 | −0.000753 | 0.014542 | 0.007331 | −0.004013 | 0.007691 |
| 285 | 0.004867 | 0.010073 | 0.019149 | −0.033508 | −0.005958 | 0.018172 | 0.002251 | 0.007394 | 0.018909 | 0.001651 | 0.015864 | 0.011166 | 0.00266 | 0.000133 |
| 286 | 0.01545 | 0.035181 | −0.003465 | −0.009121 | 0.015553 | 0.026017 | 0.005353 | 0.00419 | −0.010667 | −0.00459 | 0.002622 | −0.000618 | −0.010994 | 0.009154 |
| 287 | 0.00576 | 0.045735 | −0.002128 | −0.010249 | 0.000886 | 0.027441 | 0.001211 | 0.00373 | 0.004714 | −0.017258 | −0.010467 | −0.007038 | −0.007157 | −0.006059 |
| 288 | −0.014349 | 0.041992 | 0.005 | 0.00138 | −0.009781 | 0.015662 | 0.009029 | −0.015342 | 0.011126 | −0.018551 | 0.017325 | 0.010655 | −0.01833 | −0.00641 |
| 289 | −0.012982 | 0.019218 | 0.00017 | 0.006238 | 0.003037 | 0.000776 | 0.014366 | −0.0051 | 0.013683 | −0.006468 | 0.007955 | −0.020033 | 0.003508 | −0.007121 |
| 290 | −0.011596 | 0.00526 | −0.016771 | 0.023073 | −0.001963 | 0.016592 | 0.017788 | −0.012346 | 0.011087 | −0.007632 | 0.003577 | 0.032829 | 0.00033 | −0.013883 |
| 291 | −0.010292 | 0.003982 | −0.019464 | 0.016134 | −0.000565 | 0.017182 | 0.01529 | −0.00988 | 0.010293 | −0.006842 | 0.003266 | 0.028689 | −0.000438 | −0.015809 |
| 292 | −0.00768 | 0.008982 | −0.021382 | 0.013527 | 0.009021 | 0.016008 | 0.007206 | −0.002202 | 0.001212 | −0.001847 | −0.002328 | 0.032352 | −0.001032 | −0.01847 |
| 293 | 0.040036 | −0.012349 | −0.002771 | 0.021926 | −0.00239 | −0.003202 | −0.000251 | −0.002178 | 0.007978 | −0.014072 | −0.036172 | −0.019421 | −0.00954 | 0.011939 |
| 294 | −0.001078 | 0.002655 | −0.005546 | 0.012878 | −0.011419 | −0.008976 | 0.010156 | 0.002753 | 0.002126 | −0.016186 | −0.015286 | −0.01259 | 0.002739 | −0.015009 |
| 295 | 0.003386 | −0.040479 | −0.032267 | −0.015947 | −0.000049 | −0.004878 | 0.01422 | 0.010578 | 0.010398 | −0.011393 | −0.018223 | −0.023661 | −0.000899 | 0.002456 |
| 296 | −0.050668 | −0.011163 | −0.017765 | −0.015028 | 0.016889 | −0.000038 | 0.033285 | 0.028842 | 0.023079 | −0.010358 | −0.01185 | −0.01956 | 0.012317 | −0.017647 |
| 297 | 0.005363 | −0.041214 | −0.009718 | 0.007112 | 0.003085 | 0.012743 | 0.015226 | 0.008349 | 0.003771 | 0.000819 | 0.006147 | −0.005759 | −0.010692 | 0.008378 |
| 298 | −0.003734 | 0.008839 | 0.008556 | 0.022779 | −0.006308 | 0.025081 | 0.017658 | 0.036962 | 0.040372 | 0.003518 | 0.017921 | 0.083116 | 0.00251 | −0.005011 |
| 299 | 0.030304 | −0.013822 | 0.011175 | 0.045866 | −0.027269 | 0.007869 | −0.00855 | 0.007607 | 0.001653 | 0.011878 | 0.038637 | 0.002464 | −0.044536 | 0.00963 |
| 300 | −0.029531 | 0.011784 | −0.039684 | 0.021848 | 0.005769 | 0.038652 | 0.014955 | 0.008206 | −0.026316 | 0.008835 | 0.033197 | 0.035513 | −0.032075 | 0.021671 |
| 301 | 0.013154 | −0.020308 | 0.015535 | 0.018992 | −0.02963 | 0.003495 | 0.002206 | 0.006787 | 0.009895 | 0.005408 | 0.012908 | 0.021574 | −0.012241 | −0.001044 |
| 302 | −0.002267 | 0.000596 | −0.02631 | 0.022997 | −0.01169 | 0.004554 | 0.009005 | −0.007688 | −0.011904 | 0.009035 | 0.020949 | −0.005072 | 0.001806 | −0.015125 |
| 303 | 0.015031 | 0.024285 | −0.000743 | 0.059568 | −0.012064 | 0.025401 | −0.008278 | 0.033956 | −0.022903 | 0.019198 | 0.033704 | 0.026462 | −0.036458 | −0.010128 |
| 304 | 0.007803 | 0.027886 | −0.009611 | 0.049152 | −0.036455 | 0.026124 | −0.001677 | 0.007734 | −0.017734 | 0.005444 | 0.040693 | 0.029179 | −0.043598 | 0.00156 |
| 305 | 0.021739 | 0.058258 | −0.030556 | 0.054104 | −0.002816 | 0.003507 | 0.000054 | 0.002595 | −0.02115 | 0.000317 | 0.004771 | 0.024591 | −0.00847 | 0.015791 |
| 306 | −0.007864 | −0.03125 | −0.041337 | 0.017394 | 0.000332 | 0.021898 | 0.003913 | −0.021464 | −0.028124 | −0.014748 | −0.039577 | 0.001323 | −0.012814 | 0.015768 |
| 307 | 0.015493 | 0.020555 | −0.072597 | −0.02645 | −0.025471 | 0.034255 | 0.001028 | −0.033207 | 0.009733 | 0.001527 | 0.018425 | 0.033498 | −0.014266 | 0.031021 |
| 308 | 0.003039 | 0.057938 | 0.007876 | −0.059994 | 0.023419 | 0.010044 | 0.001533 | 0.022542 | 0.014052 | −0.022313 | −0.05883 | 0.024384 | 0.004351 | 0.019493 |
| 309 | 0.000852 | 0.003013 | −0.025581 | −0.001081 | −0.015944 | −0.012519 | 0.003921 | −0.010864 | 0.015365 | −0.003184 | −0.023033 | −0.021017 | 0.004063 | −0.004521 |
| 310 | −0.000364 | −0.007493 | −0.029055 | 0.022258 | −0.013865 | −0.014625 | 0.028619 | 0.005152 | 0.034808 | −0.009392 | −0.025354 | −0.055701 | 0.035438 | −0.020335 |
| 311 | 0.00443 | −0.008408 | −0.020681 | 0.018919 | 0.003396 | −0.011094 | 0.004292 | −0.015114 | 0.005269 | −0.011633 | −0.012327 | −0.002775 | 0.008386 | −0.011941 |
| 312 | −0.018518 | 0.032656 | −0.078331 | 0.03079 | 0.004983 | −0.012975 | −0.014653 | −0.018418 | 0.000219 | −0.023581 | −0.067258 | 0.003281 | 0.024223 | 0.008295 |

APPENDIX B3-continued

PCA Transformation
Matrix (340 × 340 Early/Late)

| | | | | | | | | | | | | | |
|---|---|---|---|---|---|---|---|---|---|---|---|---|---|
| 313 | −0.005276 | 0.006001 | 0.017038 | −0.012648 | 0.022306 | 0.018895 | 0.02052 | −0.004187 | −0.031617 | −0.015843 | 0.015113 | 0.000166 | 0.01341 | −0.006256 |
| 314 | 0.003755 | 0.024395 | 0.012424 | −0.052015 | −0.026135 | 0.065521 | 0.030882 | 0.016484 | 0.000808 | −0.036337 | 0.00875 | −0.014038 | 0.019001 | −0.017385 |
| 315 | 0.012299 | 0.009644 | −0.00712 | 0.001498 | 0.004806 | 0.000803 | −0.006186 | 0.006313 | −0.003673 | 0.011575 | 0.010079 | −0.011217 | −0.015458 | 0.006274 |
| 316 | −0.02853 | −0.057805 | 0.028827 | −0.04131 | 0.005687 | 0.015514 | 0.041255 | 0.051879 | 0.016292 | −0.012456 | −0.034305 | −0.042296 | 0.026888 | −0.071331 |
| 317 | 0.002799 | −0.009647 | 0.005178 | −0.029728 | −0.014156 | −0.012604 | 0.00718 | 0.006591 | 0.021261 | 0.005681 | −0.016223 | −0.006463 | 0.010821 | −0.000268 |
| 318 | 0.039089 | −0.050453 | −0.007227 | −0.027071 | −0.038894 | −0.006779 | 0.039483 | 0.014741 | 0.052412 | 0.009449 | −0.010217 | 0.055117 | 0.024269 | 0.013905 |
| 319 | 0.008766 | −0.019361 | 0.006875 | −0.004283 | −0.0068 | 0.001483 | −0.005339 | 0.01387 | 0.01654 | 0.010746 | 0.015607 | 0.008305 | −0.012708 | −0.007367 |
| 320 | −0.004795 | −0.034371 | −0.002329 | −0.03138 | 0.011753 | −0.000073 | 0.024535 | −0.000806 | −0.000434 | −0.021804 | −0.015208 | 0.010561 | 0.006464 | −0.011207 |
| 321 | −0.006219 | −0.001932 | 0.008889 | −0.009109 | −0.013874 | 0.022666 | 0.028892 | 0.002351 | −0.023867 | 0.00285 | 0.067788 | 0.006497 | −0.027995 | 0.012047 |
| 322 | 0.026797 | 0.005601 | 0.055541 | −0.0024 | −0.047154 | −0.051516 | 0.037173 | 0.003218 | −0.018173 | −0.015098 | −0.09843 | 0.020834 | 0.007452 | 0.027725 |
| 323 | 0.020233 | −0.012627 | −0.00089 | 0.006248 | 0.002296 | −0.030691 | 0.012679 | 0.006199 | −0.005447 | 0.010656 | 0.021539 | 0.021472 | −0.005114 | 0.027358 |
| 324 | −0.022021 | 0.034162 | −0.002999 | −0.009164 | −0.042793 | −0.002114 | −0.021156 | −0.0479 | 0.014124 | −0.032608 | 0.009548 | −0.035799 | −0.003589 | −0.063392 |
| 325 | −0.027175 | −0.0002 | 0.006722 | 0.013676 | 0.00614 | −0.010547 | 0.001533 | −0.001106 | −0.002951 | 0.003109 | −0.011862 | −0.017418 | 0.005663 | −0.023053 |
| 326 | 0.006303 | 0.015063 | −0.033478 | −4.004425 | 0.013323 | −0.023732 | −0.018099 | −0.058025 | −0.008784 | −0.010553 | −0.053354 | −0.058662 | 0.026302 | −0.0077 |
| 327 | −0.008078 | 0.005906 | −0.052572 | 0.010408 | 0.000965 | −0.027215 | −0.004538 | −0.00191 | −0.016664 | 0.006114 | 0.009789 | −0.001772 | −0.005543 | −0.003022 |
| 328 | −0.02555 | 0.027323 | 0.023417 | −0.030097 | 0.036509 | 0.01765 | 0.009713 | 0.013191 | −0.000165 | −0.022096 | −0.045436 | 0.065473 | 0.000015 | 0.0226 |
| 329 | 0.010083 | 0.001654 | −0.033291 | 0.012336 | 0.020465 | −0.03159 | −0.001701 | 0.004499 | −0.025992 | 0.01746 | 0.023114 | 0.000937 | −0.000471 | 0.004398 |
| 330 | −0.004616 | 0.003002 | 0.001385 | 0.061235 | −0.036076 | −0.004664 | 0.004142 | −0.010054 | −0.03419 | −0.011401 | −0.000221 | −0.009015 | 0.008098 | −0.017228 |
| 331 | 0.012216 | 0.016157 | −0.025544 | 0.01425 | 0.000225 | −0.025252 | −0.020936 | −0.01933 | −0.019403 | −0.00462 | −0.019785 | −0.016405 | −0.010411 | 0.002873 |
| 332 | 0.006185 | −0.055745 | 0.015763 | 0.023469 | −0.009632 | −0.007672 | 0.002433 | −0.053897 | −0.011724 | −0.014106 | −0.024348 | 0.028746 | 0.01288 | −0.024713 |
| 333 | −0.003274 | −0.021041 | 0.015011 | −0.011013 | −0.013645 | −0.012155 | −0.0035 | −0.017398 | 0.008554 | 0.00776 | −0.013208 | −0.004592 | −0.000323 | 0.004047 |
| 334 | −0.018981 | 0.014181 | −0.026324 | 0.021408 | 0.022366 | −0.003521 | −0.032199 | 0.003174 | −0.045723 | 0.012638 | −0.060103 | 0.056669 | 0.021074 | −0.001751 |
| 335 | 0.003346 | −0.01572 | −0.002312 | 0.019454 | −0.01272 | −0.02081 | −0.006768 | −0.031586 | 0.010116 | −0.011571 | −0.011649 | −0.003783 | 0.008524 | −0.016199 |
| 336 | −0.033476 | 0.008153 | −0.014382 | −0.030715 | −0.074923 | 0.026577 | −0.010928 | −0.014208 | 0.004602 | 0.003462 | −0.012276 | −0.037254 | −0.042904 | 0.039332 |
| 337 | 0.01435 | −0.04748 | 0.039678 | 0.03417 | −0.035119 | −0.000591 | −0.009307 | 0.009298 | 0.013793 | −0.000074 | −0.035693 | 0.042438 | −0.009613 | −0.013871 |
| 338 | −0.013181 | −0.011002 | 0.009702 | 0.003449 | 0.023791 | −0.009196 | −0.043792 | 0.029428 | 0.031783 | −0.001225 | −0.016543 | 0.012705 | 0.0124761 | −0.034279 |
| 339 | 0.026911 | 0.001185 | −0.018409 | 0.028525 | 0.003493 | −0.006453 | −0.004851 | −0.041283 | −0.036353 | 0.018339 | −0.011132 | 0.045139 | −0.002336 | 0.046564 |
| 340 | 0.017646 | −0.065355 | −0.026745 | −0.034512 | 0.015589 | 0.003151 | −0.017319 | 0.024945 | 0.017565 | 0.012328 | 0.000986 | −0.012643 | −0.008497 | −0.005495 |

| | EV | EW | EX | EY | EZ | FA | FB | FC | FD | FE | FF | FG | FH | FI |
|---|---|---|---|---|---|---|---|---|---|---|---|---|---|---|
| 1 | −0.020065 | 0.040003 | 0.073806 | 0.063836 | 0.015491 | 0.049019 | 0.057844 | 0.025207 | 0.018176 | 0.085182 | 0.035506 | 0.04207 | 0.060312 | 0.015229 |
| 2 | 0.128999 | −0.047034 | 0.019795 | −0.029936 | −0.03939 | 0.003283 | 0.041508 | −0.083846 | −0.06457 | 0.021746 | 0.040832 | −0.030786 | −0.073256 | −0.047711 |
| 3 | −0.054511 | −0.041559 | −0.080807 | −0.001687 | 0.015508 | 0.06687 | 0.009748 | 0.084197 | 0.029341 | 0.005342 | −0.04699 | −0.056634 | −0.029682 | −0.01207 |
| 4 | 0.077119 | 0.054656 | 0.03432 | −0.013034 | 0.048295 | −0.041897 | 0.016728 | 0.130351 | 0.035311 | −0.061985 | −0.081047 | 0.003014 | 0.01516 | 0.116831 |
| 5 | −0.066059 | −0.044792 | 0.046125 | 0.008005 | 0.008295 | −0.012069 | −0.01368 | −0.024758 | −0.097866 | 0.006458 | −0.033119 | 0.048379 | −0.017575 | −0.024669 |
| 6 | −0.127303 | −0.064132 | −0.054219 | −0.022598 | −0.006737 | 0.139813 | 0.012484 | 0.195703 | −0.06128 | −0.031545 | 0.020391 | −0.041652 | −0.06363 | −0.105549 |
| 7 | −0.054793 | −0.005484 | 0.0299 | −0.045227 | −0.098255 | 0.002622 | −0.02864 | −0.081503 | 0.047745 | 0.035292 | 0.01774 | −0.016529 | −0.02246 | −0.114078 |
| 8 | 0.012164 | 0.01663 | −0.074884 | −0.003438 | −0.033002 | −0.019712 | −0.044354 | −0.05105 | 0.112975 | −0.05643 | 0.000129 | −0.01676 | 0.026369 | −0.040054 |
| 9 | 0.020813 | 0.032943 | 0.004708 | −0.011129 | 0.08823 | 0.06821 | 0.040882 | −0.017489 | −0.133881 | −0.056642 | 0.008479 | −0.029627 | 0.046239 | −0.031462 |
| 10 | 0.048733 | 0.050684 | 0.041537 | 0.025089 | 0.037208 | 0.037957 | 0.019101 | 0.005725 | 0.038664 | 0.112472 | 0.011742 | 0.048816 | −0.002984 | 0.103182 |
| 11 | −0.022006 | 0.002403 | −0.002776 | 0.066941 | 0.046383 | −0.054325 | 0.029822 | 0.022685 | −0.003747 | −0.073098 | −0.04297 | −0.05442 | −0.018288 | 0.03902 |
| 12 | −0.059079 | 0.016139 | −0.084946 | −0.021555 | 0.015746 | 0.080715 | 0.020694 | 0.001409 | 0.034389 | −0.074134 | −0.071865 | 0.005941 | 0.007403 | 0.063064 |
| 13 | 0.028583 | 0.00428 | −0.066153 | −0.025115 | −0.079317 | 0.049284 | −0.048785 | 0.019934 | −0.12149 | −0.106708 | 0.081784 | −0.087931 | −0.001387 | −0.100806 |
| 14 | −0.163739 | 0.059502 | 0.006906 | 0.034943 | 0.098146 | 0.029582 | 0.007027 | 0.08417 | 0.13023 | 0.082312 | 0.147557 | 0.038845 | 0.043667 | −0.039666 |
| 15 | −0.131382 | 0.018249 | 0.068488 | 0.063215 | −0.012074 | 0.011431 | −0.000089 | −0.040472 | −0.222082 | 0.022705 | −0.064338 | −0.021663 | 0.044431 | 0.012379 |
| 16 | −0.069649 | −0.05394 | −0.002787 | −0.030392 | 0.054809 | 0.028553 | 0.001802 | −0.001329 | 0.108882 | 0.028108 | −0.059577 | −0.014316 | −0.118179 | −0.003133 |
| 17 | 0.106071 | −0.031068 | −0.077721 | 0.010883 | −0.082857 | 0.038018 | 0.00647 | −0.033537 | 0.043098 | −0.009377 | −0.115526 | −0.031572 | −0.005035 | 0.047221 |
| 18 | −0.088547 | 0.033245 | −0.010388 | 0.029336 | −0.000166 | −0.011497 | 0.008978 | −0.044703 | 0.118866 | 0.072587 | 0.055732 | 0.030276 | 0.06508 | −0.049491 |
| 19 | −0.002337 | 0.027233 | 0.039118 | 0.003342 | 0.017176 | −0.063086 | 0.014822 | 0.025083 | 0.072505 | 0.133083 | 0.038788 | 0.043448 | 0.014734 | −0.11945 |

APPENDIX B3-continued

PCA Transformation
Matrix (340 × 340 Early/Late)

| | | | | | | | | | | | | | |
|---|---|---|---|---|---|---|---|---|---|---|---|---|---|
| 20 | −0.041068 | 0.011328 | 0.011739 | −0.025939 | −0.037505 | −0.012218 | −0.080692 | 0.055118 | 0.035789 | 0.070944 | 0.051778 | −0.08868 | −0.018888 | −0.041971 |
| 21 | −0.080418 | 0.037316 | 0.088401 | −0.006988 | 0.007604 | −0.031621 | 0.005549 | −0.055956 | −0.053234 | −0.051194 | 0.013526 | −0.025082 | 0.011467 | −0.043632 |
| 22 | 0.048236 | 0.006283 | 0.004978 | −0.055164 | −0.025882 | −0.088789 | 0.036492 | −0.099888 | 0.053613 | 0.093388 | −0.048992 | −0.022593 | 0.027726 | −0.009422 |
| 23 | 0.160947 | 0.045773 | −0.000351 | −0.008214 | −0.042723 | −0.043167 | 0.003178 | −0.024551 | 0.082116 | 0.033207 | 0.047526 | 0.002356 | −0.029475 | −0.015644 |
| 24 | −0.055132 | 0.027579 | −0.024712 | −0.029515 | 0.01355 | 0.050512 | −0.007785 | 0.036669 | −0.043797 | 0.134429 | 0.007322 | −0.113751 | 0.025428 | 0.014613 |
| 25 | −0.003083 | −0.046822 | −0.042651 | 0.019687 | −0.039465 | −0.005343 | 0.012743 | 0.024436 | 0.009113 | −0.072843 | 0.054871 | 0.071658 | 0.01551 | 0.015432 |
| 26 | −0.04676 | −0.009402 | −0.05304 | −0.038746 | 0.064058 | −0.077124 | −0.001989 | 0.045678 | 0.00409 | −0.164974 | 0.100367 | −0.018103 | 0.006287 | −0.057585 |
| 27 | 0.060679 | 0.061359 | 0.092451 | 0.085948 | 0.037012 | 0.065475 | −0.048682 | 0.058196 | 0.066344 | −0.001001 | −0.062432 | 0.010946 | 0.026055 | 0.094249 |
| 28 | 0.003926 | −0.029792 | 0.003225 | 0.084946 | 0.128951 | −0.02101 | −0.045632 | −0.002471 | −0.047681 | −0.082803 | −0.043574 | 0.030142 | −0.09666 | −0.03162 |
| 29 | −0.066735 | 0.019392 | 0.015949 | 0.01215 | 0.025572 | 0.006704 | 0.00277 | 0.067803 | −0.026332 | −0.003192 | 0.040872 | −0.015851 | 0.025831 | −0.036719 |
| 30 | −0.005202 | 0.011767 | 0.010828 | 0.088285 | 0.02689 | −0.001009 | 0.033153 | −0.083296 | 0.024614 | 0.000742 | −0.043498 | −0.008343 | 0.048043 | 0.000487 |
| 31 | −0.10936 | 0.016697 | 0.026842 | −0.003586 | 0.065977 | 0.044192 | 0.011032 | −0.104254 | −0.061446 | −0.103949 | 0.016878 | 0.051882 | −0.051725 | −0.082714 |
| 32 | −0.034713 | 0.063814 | 0.053099 | −0.018555 | 0.062323 | 0.097473 | −0.033433 | 0.0848 | 0.006498 | 0.022021 | −0.010343 | 0.057649 | 0.00319 | −0.004242 |
| 33 | 0.003877 | 0.047294 | −0.011351 | −0.043587 | −0.055459 | 0.025351 | −0.060154 | −0.182804 | 0.021422 | 0.024274 | −0.067827 | −0.025208 | 0.052997 | 0.063568 |
| 34 | 0.023878 | 0.017294 | −0.11272 | −0.0111 | −0.070485 | −0.008614 | 0.023267 | −0.001357 | 0.005047 | 0.080979 | 0.012831 | 0.101713 | 0.053179 | 0.085385 |
| 35 | −0.01436 | 0.040548 | −0.021283 | −0.019418 | 0.076314 | −0.039328 | −0.045999 | −0.002361 | −0.001514 | −0.16955 | −0.012213 | −0.105102 | −0.012182 | −0.011055 |
| 36 | −0.008985 | 0.0453 | 0.100752 | 0.073678 | 0.033922 | 0.043766 | −0.003736 | −0.087166 | −0.065734 | −0.021008 | 0.077066 | 0.058117 | 0.032106 | −0.019353 |
| 37 | 0.07202 | −0.017208 | −0.014717 | −0.044634 | −0.016177 | −0.0478 | 0.056792 | −0.001585 | 0.07177 | −0.079975 | −0.044429 | −0.048273 | −0.058836 | 0.015164 |
| 38 | −0.05779 | −0.009244 | −0.020611 | −0.004809 | 0.001289 | 0.059942 | −0.032918 | −0.012301 | 0.019524 | 0.170489 | −0.036581 | −0.014932 | 0.002653 | −0.069128 |
| 39 | 0.03797 | −0.178437 | −0.06548 | −0.03591 | −0.033795 | 0.04622 | −0.01705 | 0.130119 | 0.054084 | −0.025328 | 0.098116 | 0.016974 | −0.073842 | 0.108151 |
| 40 | 0.007489 | 0.010058 | 0.012946 | −0.009084 | 0.028774 | −0.000822 | −0.021165 | 0.016742 | 0.01945 | 0.011903 | 0.031077 | 0.002906 | −0.005263 | −0.005238 |
| 41 | 0.072398 | 0.001069 | 0.148502 | −0.027062 | 0.105234 | −0.044417 | 0.010029 | 0.157704 | −0.10753 | −0.094677 | 0.18769 | −0.10889 | −0.057264 | 0.015485 |
| 42 | 0.005948 | −0.025975 | −0.063752 | 0.012054 | 0.023633 | −0.018426 | 0.0039 | −0.009295 | −4.013291 | −0.25887 | −0.063732 | −0.075082 | −0.017264 | −0.161953 |
| 43 | 0.021218 | −0.011619 | −0.048017 | 0.03091 | −0.066082 | −0.078457 | −0.168554 | −0.003893 | 0.022576 | 0.012898 | −0.034595 | −0.03506T | −0.104922 | 0.049302 |
| 44 | 0.112299 | 0.038933 | 0.099868 | 0.126478 | 0.01088 | 0.112569 | 0.011356 | 0.017014 | −0.022865 | 0.004097 | −0.001625 | 0.036086 | 0.02379 | 0.024874 |
| 45 | −0.010626 | −0.063066 | 0.063746 | 0.009006 | −0.091899 | −0.045528 | −0.007519 | −0.084001 | 0.088927 | −0.075079 | −0.062275 | 0.040406 | 0.015801 | 0.02341 |
| 46 | −0.039201 | 0.035852 | −0.01617 | −0.098218 | 0.067992 | −0.013243 | −0.035652 | −0.157166 | −0.003895 | 0.026214 | 0.019823 | 0.079257 | 0.012433 | 0.065294 |
| 47 | 0.071291 | −0.042952 | −0.005383 | −0.043866 | −0.069247 | −0.016845 | 0.007156 | −0.005643 | 0.029355 | 0.093396 | 0.05173 | −0.112518 | −0.039687 | −0.120044 |
| 48 | 0.041699 | −0.027314 | −0.06575 | −0.066218 | 0.033265 | −0.094665 | −0.004536 | 0.013436 | −0.119694 | −0.042702 | −0.137832 | 0.088404 | −0.014961 | −0.015558 |
| 49 | −0.009735 | 0.037516 | −0.021472 | −0.032385 | −0.017032 | −0.074256 | −0.009848 | 0.049071 | −0.004632 | 0.028064 | 0.009422 | −0.028492 | 0.035174 | −0.028348 |
| 50 | 0.010589 | −0.034808 | −0.046765 | 0.087248 | 0.088498 | −0.031684 | −0.00894 | −0.091665 | 0.122357 | −0.200072 | −0.051307 | −0.09896 | 0.006679 | 0.015932 |
| 51 | −0.104938 | 0.00878 | −0.034551 | 0.070299 | 0.004008 | −0.025608 | 0.020582 | −0.073765 | 0.028959 | −0.028873 | −0.036617 | −0.05912 | −0.024828 | 0.016883 |
| 52 | 0.113258 | −0.024164 | −0.007043 | −0.063011 | −0.131729 | 0.009504 | −0.067229 | 0.077391 | −0.054503 | 0.165268 | 0.014588 | 0.066551 | −0.049875 | −0.116408 |
| 53 | 0.131 | −0.044186 | 0.047405 | 0.074534 | 0.0382 | 0.137998 | −0.054756 | 0.151188 | 0.005357 | −0.037495 | −0.019261 | 0.006545 | −0.037046 | −0.005367 |
| 54 | −0.01247 | 0.00615 | 0.021447 | 0.025361 | −0.041623 | 0.036274 | −0.017497 | −0.103993 | −0.079753 | −0.024178 | −0.121612 | −0.012144 | −0.063229 | 0.096674 |
| 55 | −0.09208 | −0.003668 | −0.003289 | −0.070459 | 0.002358 | −0.036848 | 0.003474 | −0.057434 | 0.009466 | −0.051571 | −0.048216 | 0.020301 | −0.019052 | −0.071879 |
| 56 | −0.036727 | 0.013768 | −0.006866 | −0.003811 | −0.033591 | −0.081199 | −0.018463 | 0.097852 | 0.10769 | −0.148915 | 0.026197 | 0.050664 | 0.002071 | 0.00897 |
| 57 | −0.123463 | −0.077822 | −0.04341 | −0.047431 | −0.02538 | −0.092516 | 0.060978 | −0.015598 | −0.022345 | −0.094815 | −0.018677 | −0.069288 | −0.072237 | −0.051475 |
| 58 | −0.133961 | 0.031003 | 0.039027 | 0.13391 | 0.080692 | 0.020538 | 0.009519 | 0.100002 | 0.030148 | 0.090016 | −0.11278 | −0.046218 | 0.056325 | 0.012767 |
| 59 | 0.011391 | −0.110516 | −0.128258 | −0.055684 | −0.083584 | −0.031073 | 0.00301 | −0.081923 | −0.05505 | 0.012498 | −0.094403 | −0.006775 | −0.010849 | 0.040935 |
| 60 | −0.002313 | 0.009369 | −0.002778 | −0.004303 | −0.010786 | 0.0146 | 0.02156 | −0.030657 | −0.015522 | 0.002585 | −0.026897 | 0.042997 | 0.023449 | −0.011774 |
| 61 | −0.017635 | 0.028803 | −0.029521 | −0.020467 | −0.010162 | 0.015936 | −0.001748 | −0.031568 | 0.007148 | 0.042811 | −0.027142 | 0.012412 | 0.021484 | −0.00734 |
| 62 | 0.035401 | 0.043107 | −0.005052 | −0.004246 | −0.015443 | 0.014819 | 0.000408 | 0.004087 | 0.010992 | −0.008211 | 0.015594 | −0.007877 | 0.016347 | −0.009833 |
| 63 | −0.00224 | 0.026836 | −0.007282 | −0.016066 | 0.00795 | −0.006213 | 0.000727 | 0.0084 | 0.005771 | −0.007211 | 0.020683 | −0.00997 | 0.007745 | −0.009681 |
| 64 | 0.037079 | 0.00829 | −0.001825 | −0.009507 | −0.045314 | −0.006742 | −0.004552 | −0.020698 | −0.00257 | 0.007114 | 0.030731 | −0.002664 | 0.008263 | 0.022178 |
| 65 | 0.003796 | −0.012083 | −0.031818 | −0.018889 | −0.021882 | −0.004513 | 0.015942 | −0.017781 | −0.008744 | −0.014254 | −0.00056 | 0.021866 | 0.006353 | 0.003794 |
| 66 | −0.026322 | 0.026514 | 0.004662 | 0.005786 | 0.001432 | 0.037647 | 0.004921 | −0.019599 | 0.044354 | 0.028761 | −0.000359 | 0.009451 | 0.01901 | 0.027272 |
| 67 | −0.029042 | 0.007841 | 0.003209 | −0.001786 | 0.008538 | 0.018772 | 0.018124 | −0.009539 | −0.015918 | 0.057186 | 0.017718 | −0.014077 | 0.007218 | −0.056577 |
| 68 | 0.047809 | −0.015357 | −0.022608 | 0.023824 | 0.020356 | −0.028113 | 0.075463 | −0.002311 | −0.000592 | 0.000342 | −0.050823 | −0.03947 | 0.023086 | −0.008011 |
| 69 | 0.02771 | −0.02221 | 0.009027 | 0.02305 | −0.044768 | 0.011482 | 0.004138 | 0.014279 | 0.028179 | 0.000759 | −0.041767 | −0.020656 | −0.002396 | −0.012802 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 70 | 0.00428 | 0.008788 | 0.02352 | −0.011284 | −0.02212 | −0.007093 | 0.024736 | −0.005991 | 0.002652 | −0.007461 | −0.004112 | 0.0222 | 0.017339 | 0.005265 |
| 71 | 0.009424 | −0.016757 | −0.012543 | 0.009074 | −0.010301 | 0.002564 | 0.013369 | 0.003478 | 0.031559 | −0.006634 | −0.033897 | −0.004285 | −0.003625 | 0.027349 |
| 72 | −0.033525 | −0.026326 | −0.022388 | −0.010412 | −0.019002 | −0.008089 | −0.001777 | 0.041422 | 0.005489 | 0.000258 | −0.007885 | −0.010479 | 0.002464 | 0.004702 |
| 73 | −0.03474 | 0.008787 | 0.022142 | −0.040051 | 0.021807 | 0.016606 | 0.022093 | 0.070788 | 0.031016 | 0.084185 | 0.008655 | 0.026339 | 0.021738 | 0.012191 |
| 74 | 0.02641 | 0.033171 | 0.032873 | 0.021286 | 0.025256 | −0.038238 | −0.006206 | −0.037059 | −0.027649 | −0.026636 | −0.037998 | −0.005648 | 0.006678 | 0.06091 |
| 75 | 0.018945 | 0.006459 | 0.018449 | −0.015949 | −0.003862 | −0.00821 | 0.010754 | −0.018965 | −0.004901 | 0.000456 | −0.010561 | 0.022196 | 0.0074 | 0.014115 |
| 76 | −0.00409 | 0.014402 | 0.03135 | −0.020734 | −0.004326 | −0.016281 | −0.014946 | −0.036512 | 0.009079 | −0.026191 | −0.034697 | 0.006284 | −0.013448 | 0.012183 |
| 77 | 0.013687 | 0.001229 | 0.019873 | 0.0008 | −0.005152 | −0.007448 | 0.009779 | −0.012169 | 0.002779 | −0.019394 | −0.02271 | 0.019193 | 0.007895 | 0.018519 |
| 78 | 0.024864 | −0.001945 | 0.017767 | −0.01374 | −0.006419 | −0.010246 | 0.018138 | −0.025349 | −0.024185 | 0.006062 | −0.031307 | 0.038141 | 0.008225 | 0.026107 |
| 79 | 0.032431 | 0.002438 | 0.030917 | −0.011695 | −0.013008 | 0.00898 | 0.001001 | −0.029182 | 0.013544 | −0.000505 | −0.009997 | 0.006137 | 0.00234 | 0.018673 |
| 80 | −0.051384 | 0.014401 | −0.014675 | 8.002108 | −0.057562 | 0.010832 | 0.014712 | −0.044055 | −0.029003 | 0.010792 | 0.013499 | −0.005783 | 0.014374 | −0.015571 |
| 81 | −0.021705 | 0.043235 | 0.016798 | 0.015492 | −0.00233 | −0.054851 | −0.027077 | 0.021415 | 0.03687 | −0.012817 | −0.001562 | 0.017099 | 0.010824 | −0.029071 |
| 82 | −0.013165 | −0.008563 | 0.014611 | 0.006637 | −0.011704 | −0.011064 | 0.000919 | 0.003349 | 0.016733 | 0.01579 | 0.015107 | −0.009748 | 0.000284 | −0.009139 |
| 83 | 0.012463 | −0.01546 | 0.007897 | 0.006057 | −0.007807 | 0.004505 | 0.0114241 | −0.006561 | −0.013499 | 0.025585 | −0.006051 | 0.000683 | −0.013911 | 0.012408 |
| 84 | 0.003443 | −0.01292 | −0.005701 | 0.000221 | −0.014441 | 0.003127 | 0.0014531 | −0.022769 | 0.005877 | −0.003096 | −0.013395 | 0.001667 | −0.007177 | 0.007645 |
| 85 | −0.039697 | 0.010776 | −0.036864 | −0.031633 | −0.001939 | 0.009238 | −0.001667 | 0.032493 | 0.083606 | −0.019653 | 0.003353 | 0.004782 | 0.011505 | −0.006524 |
| 86 | −0.011477 | −0.024913 | −0.025689 | −0.019404 | −0.032361 | 0.009968 | −0.006187 | 0.04339 | 0.066011 | 0.045308 | −0.000504 | 0.018965 | −0.016587 | 0.021419 |
| 87 | 0.012833 | −0.004138 | −0.000798 | −0.027963 | −0.052092 | 0.007349 | 0.029112 | 0.002461 | 0.024018 | 0.066158 | 0.004324 | −0.005206 | −0.017474 | −0.034545 |
| 88 | −0.017088 | −0.019363 | 0.004294 | 0.011154 | −0.007695 | 0.009409 | 0.015458 | −0.004975 | −0.002911 | 0.032362 | −0.002035 | 0.001275 | −0.00901 | −0.016717 |
| 89 | 0.02627 | −0.020461 | 0.000222 | 0.009864 | −0.010077 | 0.002962 | 0.02181 | −0.022525 | −0.026451 | 0.019861 | −0.030002 | 0.001593 | −0.00813 | 0.013212 |
| 90 | 0.046117 | −0.004519 | 0.007126 | 0.004344 | −0.027689 | 0.009373 | 0.018137 | −0.011838 | −0.02193 | 0.033342 | −0.032963 | 0.000499 | −0.001663 | 0.011869 |
| 91 | 0.019444 | −0.021141 | 0.004112 | −0.004736 | −0.029803 | −0.010816 | −0.001503 | −0.019167 | −0.012209 | 0.00712 | 0.022761 | 0.011169 | 0.005263 | 0.01624 |
| 92 | −0.015183 | −0.036161 | −0.015893 | −0.034647 | −0.009272 | −0.02625 | −0.02081 | 0.038987 | −0.053526 | −0.005065 | 0.013759 | 0.03472 | −0.008701 | −0.014856 |
| 93 | −0.010991 | 0.011841 | 0.019708 | 0.001052 | −0.003703 | 0.009147 | 0.021123 | 0.024202 | −0.028579 | 0.023989 | −0.010544 | −0.005786 | 0.010168 | 0.001766 |
| 94 | 0.000278 | −0.012095 | 0.021843 | −0.00171 | 0.022063 | −0.002585 | 0.022738 | −0.024131 | 0.00554 | −0.02423 | 0.015265 | −0.018885 | −0.007369 | −0.009702 |
| 95 | −0.00815 | 0.029475 | 0.016806 | 0.032315 | 0.032521 | −0.033361 | 0.006833 | 0.015541 | 0.072856 | −0.014359 | 0.012263 | −0.026115 | 0.006452 | 0.02484 |
| 96 | −0.009923 | −0.000584 | 0.003528 | 0.009916 | 0.016041 | −0.013282 | 0.020392 | 0.01896 | 0.002684 | −0.018909 | −0.015376 | 0.019742 | 0.009889 | −0.009484 |
| 97 | 0.018088 | 0.031349 | 0.021414 | −0.01047 | 0.009908 | −0.009389 | −0.005698 | 0.013919 | −0.005937 | 0.000513 | 0.006474 | 0.001052 | −0.007448 | 0.001553 |
| 98 | 0.00163 | 0.018901 | 0.028371 | 0.005138 | 0.013009 | 0.009012 | −0.009726 | 0.000254 | −0.008059 | −0.001557 | 0.044881 | −0.009116 | −0.000712 | −0.013024 |
| 99 | −0.011769 | 0.003393 | 0.009561 | 0.018943 | 0.012471 | −0.002856 | −0.001676 | 0.001351 | 0.016148 | −0.000542 | 0.004608 | 0.016873 | 0.007149 | −0.007621 |
| 100 | −0.010635 | 0.015563 | 0.00197 | 0.001609 | 0.016451 | −0.021272 | −0.020054 | 0.005285 | −0.021459 | −0.002653 | 0.01735 | −0.003342 | −0.006096 | −0.024963 |
| 101 | −0.018736 | 0.035631 | 0.030963 | 0.006571 | 0.027981 | 0.001741 | 0.006731 | −0.013241 | −0.005214 | −0.011124 | 0.020728 | −0.016126 | 0.01041 | 0.000746 |
| 102 | −0.000641 | 0.030439 | −0.003172 | −0.019539 | −0.006439 | −0.033108 | 0.010187 | 0.025789 | 0.022959 | −0.000519 | 0.014961 | 0.010513 | −0.00079 | −0.02102 |
| 103 | 0.013254 | 0.011473 | −0.010024 | 0.019818 | 0.018188 | −0.007036 | 0.009154 | 0.058848 | −0.005734 | 0.000137 | 0.020886 | −0.010948 | −0.016625 | −0.013821 |
| 104 | −0.031667 | 0.039686 | 0.005407 | 0.006595 | −0.015353 | −0.023181 | −0.029236 | −0.029299 | −0.010544 | 0.029821 | −0.031946 | 0.019539 | −0.010335 | −0.011899 |
| 105 | 0.01745 | −0.00773 | −0.020202 | −0.029554 | 0.00471 | 0.019379 | 0.06235 | 0.010756 | −0.086966 | −0.000305 | −0.010294 | 0.037767 | 0.013562 | −0.059731 |
| 106 | −0.009255 | 0.004027 | 0.03917 | 0.020923 | 0.005248 | 0.018255 | −0.021221 | −0.020786 | 0.01947 | −0.025898 | 0.03661 | 0.000284 | −0.003003 | 0.008801 |
| 107 | −0.048058 | 0.007889 | 0.013946 | 0.031027 | 0.02105 | −0.003597 | 0.001317 | 0.006828 | 0.06602 | 0.016025 | −0.015548 | 0.024319 | 0.018054 | 0.012989 |
| 108 | −0.021135 | 0.014595 | 0.001837 | 0.009575 | 0.003063 | −0.013553 | 0.034637 | −0.081885 | 0.013836 | 0.038219 | −0.009507 | −0.030786 | 0.029591 | 0.002739 |
| 109 | 0.022624 | 0.016358 | −0.004849 | −0.017121 | −0.011441 | −0.016365 | 0.01447 | −0.023152 | −0.044292 | −0.033286 | −0.024095 | 0.010334 | 0.034892 | −0.016233 |
| 110 | −0.042452 | −0.023539 | −0.041356 | 0.007598 | 0.01512 | 0.025615 | −0.026217 | −0.045661 | 0.007135 | −0.094377 | −0.000651 | 0.024361 | 0.025243 | 0.021432 |
| 111 | 0.034563 | −0.014104 | 0.018685 | −0.04772 | −0.052848 | −0.011803 | 0.000918 | −0.061375 | 0.038533 | 0.070234 | 0.023116 | 0.019756 | 0.009345 | 0.057834 |
| 112 | 0.012363 | −0.026159 | 0.011547 | 0.02317 | 0.013797 | 0.035607 | 0.002087 | 0.015169 | −0.027182 | −0.014634 | −0.035043 | −0.041187 | −0.028993 | 0.005623 |
| 113 | 0.034956 | 0.011276 | 0.035903 | −0.01138 | 0.009786 | −0.023495 | 0.005421 | 0.017526 | 0.02464 | −0.060609 | 0.038591 | −0.013021 | 0.010563 | −0.022399 |
| 114 | −0.015152 | 0.038425 | 0.028988 | 0.07043 | 0.049513 | 0.047208 | 0.020611 | −0.023591 | −0.040613 | −0.011355 | −0.038335 | −0.000234 | 0.042023 | −0.026905 |
| 115 | −0.05975 | 0.022603 | 0.016565 | 0.000754 | 0.003542 | 0.026827 | −0.002695 | −0.054526 | 0.022271 | 0.033059 | 0.02988 | 0.052081 | 0.032809 | 0.033409 |
| 116 | 0.015474 | −0.00404 | −0.012371 | −0.040061 | 0.00823 | −0.012181 | 0.02976 | −0.030183 | −0.036344 | 0.039616 | −0.073588 | −0.057235 | 0.033202 | 0.051812 |
| 117 | 0.014199 | 0.021927 | 0.016259 | 0.000073 | 0.046586 | 0.02768 | −0.050302 | 0.098027 | 0.020074 | −0.021802 | 0.059727 | 0.014097 | −0.012024 | −0.015782 |
| 118 | 0.006681 | 0.016591 | −0.024546 | 0.006386 | −0.027892 | 0.006777 | −0.008919 | 0.040839 | 0.010589 | −0.051262 | 0.04228 | −0.040442 | 0.001324 | −0.052904 |
| 119 | −0.001558 | −0.044995 | −0.036896 | −0.014121 | −0.053822 | −0.021343 | −0.015833 | −0.01575 | −0.000829 | −0.026197 | −0.03386 | −0.045385 | −0.009845 | −0.023189 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 120 | 0.049111 | −0.001077 | −0.017569 | −0.010094 | −0.013697 | −0.004728 | −0.042163 | 0.01721 | −0.00246 | −0.004823 | −0.009705 | −0.020536 | −0.008859 | 0.039615 |
| 121 | 0.086526 | −0.028335 | −0.01325 | −8.004512 | −0.025293 | 0.009782 | −0.007329 | 0.027276 | −0.011357 | −0.047792 | 0.067542 | 0.001441 | −0.009972 | 0.036254 |
| 122 | −0.03031 | 0.014197 | 0.002026 | −0.000501 | 0.008242 | 0.005048 | −0.007946 | −0.005501 | 0.027744 | −0.035201 | 0.02787 | 0.000074 | 0.000509 | 0.015639 |
| 123 | −0.035817 | −0.012333 | −0.042493 | −0.012359 | −0.02994 | −0.02626 | −0.012655 | −0.032423 | 0.029574 | −0.032254 | 0.012453 | −0.01928 | 0.012916 | 0.006443 |
| 124 | 0.008725 | −0.020752 | −0.032075 | −0.025726 | −0.034781 | −0.010243 | −0.018698 | −0.020516 | −0.015337 | −0.014184 | −0.013095 | −0.036143 | −0.016835 | −0.016459 |
| 125 | 0.02622 | −0.003895 | −0.006957 | 0.009861 | −0.029102 | −0.016066 | −0.037546 | −0.01218 | 0.00741 | −0.056886 | 0.025101 | −0.021907 | −0.03414 | −0.012344 |
| 126 | 0.006796 | −0.007466 | −0.014823 | 0.006697 | −0.01518 | 0.000487 | −0.010574 | 0.02479 | 0.026752 | −0.049719 | 0.039513 | 0.007497 | 0.003005 | 0.000517 |
| 127 | 0.007494 | −0.043478 | −0.003398 | 0.022331 | −0.015216 | −0.008321 | −0.008666 | 0.002366 | 0.003961 | −0.025573 | 0.020302 | −0.007792 | −0.029365 | −0.016317 |
| 128 | −0.004222 | 0.006266 | −0.007524 | 0.016266 | −0.01389 | −0.032839 | −0.032073 | −0.016736 | −0.03053 | −0.032815 | −0.042545 | 0.007868 | −0.000573 | −0.001961 |
| 129 | 0.02144 | −0.042417 | −0.033106 | −0.022711 | −0.08094 | 0.041706 | 0.007632 | 0.029698 | −0.064713 | −0.02801 | −0.058378 | −0.039653 | −0.017631 | −0.014254 |
| 130 | 0.024843 | 0.008737 | −0.007156 | −0.037401 | −0.013068 | −0.031341 | 0.00317 | −0.004897 | −0.008728 | 0.01217 | −0.030216 | 0.022445 | 0.002116 | 0.044624 |
| 131 | 0.089789 | −0.031992 | 0.004813 | −0.054151 | −0.01978 | −0.019645 | 0.065107 | 0.080419 | 0.005245 | −0.032364 | −0.010255 | −0.010544 | 0.005283 | −0.016442 |
| 132 | 0.016796 | −0.008246 | −0.017686 | 0.002517 | −0.047881 | −0.000602 | −0.040542 | −0.000876 | 0.021686 | 0.081092 | −0.033194 | −0.013402 | −0.011032 | 0.012921 |
| 133 | 0.03517 | 0.002859 | 0.011991 | 0.015498 | −4.010933 | −0.027904 | −4.019512 | −4.037538 | 0.009193 | −4.048704 | 0.02228 | −4.027987 | −4.004938 | −0.047462 |
| 134 | −0.062976 | −0.008214 | −0.001944 | −0.0408 | 0.012455 | −0.039532 | 0.061359 | −0.000316 | −0.005616 | 0.008139 | −0.026401 | −0.025382 | −0.003772 | 0.069394 |
| 135 | 0.001392 | −0.019685 | −0.020393 | −0.023086 | −0.027695 | −0.031925 | −0.033376 | −0.027331 | −0.033321 | 0.001622 | −0.026249 | −0.028254 | −0.038056 | 0.006072 |
| 136 | 0.000619 | −0.048251 | −0.041519 | −0.090322 | −0.060509 | −0.035044 | −0.00666 | −0.02541 | −0.005322 | 0.016636 | 0.017607 | −0.032007 | −0.004148 | −0.043807 |
| 137 | 0.023499 | 0.009708 | 0.018635 | 0.020458 | 0.002624 | −0.001482 | −0.007306 | −0.003383 | −0.044733 | −0.070417 | −0.035661 | −0.045006 | −0.028892 | −0.014488 |
| 138 | 0.066791 | −0.007449 | 0.042234 | 0.003099 | −0.001511 | −0.043994 | 0.005706 | −0.016485 | −0.042018 | −0.034046 | −0.055081 | −0.03628 | −0.003672 | 0.030881 |
| 139 | −0.079578 | −0.01591 | −0.083076 | 0.009182 | −0.021546 | 0.034837 | −0.000253 | 0.001572 | 0.006497 | 0.009182 | −0.052348 | −0.026547 | 0.023798 | −0.019564 |
| 140 | 0.001249 | 0.014028 | 0.045866 | 0.000418 | 0.002367 | 0.025531 | −0.044609 | 0.033549 | 0.019854 | −0.018659 | −0.020978 | −0.018204 | 0.014155 | −0.017458 |
| 141 | −0.027199 | −0.022281 | −0.049048 | 0.015066 | 0.022557 | −0.035035 | −0.022011 | −0.029541 | 0.000614 | −0.012916 | −0.052484 | −0.020518 | −0.028233 | −0.016816 |
| 142 | 0.036348 | −0.02589 | −0.055589 | −0.094133 | −0.013315 | 0.001685 | −0.013009 | 0.02041 | −0.028119 | 0.011776 | 0.024591 | −0.005214 | −0.048712 | −0.029361 |
| 143 | −0.039545 | 0.007241 | −0.010199 | −0.026434 | −0.004814 | −0.06479 | −0.022181 | −0.04128 | −0.010607 | −0.008614 | −0.004091 | −0.019885 | −0.030315 | −0.011948 |
| 144 | −0.038372 | −0.038188 | −0.061171 | −0.064132 | −0.052913 | −0.040357 | −0.005038 | −0.028239 | −0.001614 | 0.019049 | −0.019547 | −0.047282 | −0.017725 | −0.032336 |
| 145 | −0.015993 | 0.013283 | 0.018012 | −0.032646 | −0.045658 | −0.022855 | −0.018094 | 0.021701 | −0.049734 | −0.002935 | 0.064451 | −0.035862 | −0.005995 | −0.042071 |
| 146 | 0.02022 | −0.002625 | −0.030319 | −0.020795 | −0.044228 | −0.025303 | −0.044314 | −0.005205 | 0.030186 | 0.027844 | −0.025841 | −0.042511 | −0.020953 | −0.000046 |
| 147 | −0.041867 | 0.016655 | −0.004607 | −0.054448 | 0.030927 | −0.033097 | −0.001104 | −0.018383 | 0.003472 | −0.016021 | −0.006225 | −0.000763 | −0.008221 | −0.033129 |
| 148 | −0.003387 | 0.037839 | 0.034349 | 0.010124 | 0.025554 | 0.026654 | −0.019755 | 0.017608 | 0.033863 | −0.041398 | −0.074243 | 0.002863 | 0.002086 | 0.023194 |
| 149 | −0.030762 | −0.00225 | 0.005042 | 0.024652 | 0.004614 | −0.022345 | −0.007835 | −0.009503 | 0.012683 | −0.038712 | −0.025207 | −0.014139 | −0.023592 | −0.008874 |
| 150 | 0.035838 | 0.009172 | 0.00275 | −0.022922 | −0.018492 | −0.015705 | −0.043601 | 0.029964 | −0.063369 | 0.01709 | 0.015927 | −0.039198 | −0.020028 | 0.018319 |
| 151 | 0.677025 | 0.01477 | −0.015337 | 0.008333 | 0.043542 | 0.004356 | −0.000582 | −0.025618 | 0.007238 | 0.00089 | 0.010262 | −0.022581 | 0.027656 | −0.077679 |
| 152 | 0.023938 | 0.878824 | −0.062158 | −0.025925 | −0.058088 | −0.008452 | 0.002611 | 0.011526 | −0.015825 | −0.031331 | −0.015253 | −0.025213 | −0.062418 | −0.015561 |
| 153 | −0.016204 | −0.067512 | 0.830021 | −0.054737 | −0.060043 | −0.016001 | −0.010468 | −0.019143 | 0.040983 | −0.039802 | −0.046809 | −0.024211 | −0.025201 | −0.016138 |
| 154 | 0.037159 | −0.041373 | −0.060177 | 0.8452 | −0.066701 | −0.052034 | 0.002502 | −0.016785 | −0.03082 | 0.022626 | 0.022677 | −0.005098 | −0.032256 | −0.027034 |
| 155 | 0.100422 | −0.063688 | −0.064594 | −0.063115 | 0.80276 | −0.025642 | −0.018294 | −0.062672 | 0.005297 | 0.064244 | −0.025163 | −0.008534 | −0.023692 | −0.009422 |
| 156 | 0.014105 | −0.021375 | −0.031353 | −0.060464 | −0.030824 | 0.828681 | 0.002524 | −0.062721 | 0.018943 | −0.043831 | −0.002058 | −0.009738 | −0.022102 | −0.015177 |
| 157 | 0.013245 | 0.005917 | 0.003998 | −0.005327 | −0.027593 | −0.004683 | 0.910382 | 0.002344 | 0.007976 | −0.00498 | 0.014488 | −0.01196 | −0.024042 | −0.012633 |
| 158 | −0.015244 | 0.01088 | −0.025869 | −0.017807 | −0.0421 | −0.06502 | 0.015541 | 0.660904 | −0.01554 | 0.001906 | −0.103821 | 0.017538 | 0.023788 | 0.012895 |
| 159 | 0.021264 | −0.014755 | 0.017641 | −0.022562 | −0.012435 | 0.018554 | −0.002384 | −0.00021 | 0.710787 | −0.039828 | −0.011017 | −0.012072 | −0.013159 | −0.023823 |
| 160 | −0.049827 | −0.029187 | −0.029705 | 0.022798 | 0.069277 | −0.044213 | −0.018986 | −0.004901 | −0.008733 | 0.57778 | −0.007728 | −0.067969 | −0.049958 | −0.051924 |
| 161 | −0.009195 | −0.021777 | −0.049153 | 0.031236 | −0.018859 | −0.008739 | 0.002792 | −0.089103 | −0.006642 | −0.024224 | 0.754581 | −0.011537 | −0.012423 | 0.075426 |
| 162 | −0.017258 | −0.017118 | −0.015439 | −8.007629 | 0.008635 | −0.021341 | −0.00174 | 0.01205 | −0.01004 | −0.056365 | 0.001945 | 0.842433 | −0.036124 | −0.056616 |
| 163 | 0.026941 | −0.055998 | −0.009214 | −0.032082 | −0.012078 | −0.019007 | −0.028494 | 0.018595 | −0.023646 | −0.045643 | 0.012583 | −0.029301 | 0.90118 | −0.028367 |
| 164 | −0.065887 | −0.023667 | −0.010687 | −0.039896 | −0.023584 | −0.017735 | 0.001197 | 0.01941 | −0.034665 | −0.012288 | 0.064918 | −0.03851 | −0.023433 | 0.762975 |
| 165 | −0.023696 | −0.05897 | −0.046477 | −0.007548 | −0.125433 | −0.001009 | −0.016877 | −0.003889 | 0.088022 | −0.055142 | −0.028725 | −0.014325 | −0.02886 | −0.039607 |
| 166 | 0.003057 | 0.01801 | 0.005402 | −0.025573 | 0.012967 | 0.015526 | −0.006316 | −0.018688 | −0.016185 | −0.059264 | 0.020244 | −0.0264191 | 0.018071 | −0.058823 |
| 167 | 0.025419 | 0.002 | −0.006123 | −0.016115 | −0.054726 | −0.046013 | −0.018279 | −0.043254 | 0.006079 | 0.056291 | 0.017259 | −0.017342 | 0.001851 | −0.050432 |
| 168 | −0.005291 | 0.004177 | −0.005911 | 0.026638 | 0.04566 | 0.009854 | 0.0093 | 0.033014 | 0.007849 | −0.040509 | 0.013964 | −0.00356 | −0.019376 | −0.030024 |
| 169 | 0.029334 | 0.014077 | −0.001624 | 0.009505 | −0.006771 | 0.003313 | −0.012426 | 0.006435 | 0.016735 | 0.005805 | −0.008801 | −0.010431 | 0.00675 | 0.024341 |

APPENDIX B3-continued

PCA Transformation Matrix (340 × 340 Early/Late)

| | | | | | | | | | | | | | | |
|---|---|---|---|---|---|---|---|---|---|---|---|---|---|---|
| 170 | 0.019431 | 0.015886 | −0.001998 | 0.011846 | 0.014916 | 0.005629 | 0.009889 | 0.011192 | 0.017877 | −0.007012 | −0.019062 | −0.01593 | 0.022148 | 0.026013 |
| 171 | 0.032106 | −0.017456 | −0.030718 | 0.022918 | −0.010163 | 0.001487 | 0.000205 | −0.001241 | 0.006615 | 0.009026 | −0.039849 | 0.00387 | 0.010867 | 0.039644 |
| 172 | −0.029335 | 0.015712 | −0.01216 | 0.015019 | −0.026653 | 0.000062 | −0.020864 | −0.037155 | −0.017664 | −0.002814 | −0.024966 | −0.004227 | 0.019452 | 0.015983 |
| 173 | −0.002536 | 0.01559 | −0.004311 | 0.02495 | −0.01611 | 0.031849 | 0.002274 | −0.027434 | −0.000134 | −0.043116 | −0.003022 | −0.004447 | 0.015406 | 0.0192 |
| 174 | −0.001464 | 0.018052 | 0.008091 | 0.011933 | −0.016339 | 0.023241 | 0.012415 | −0.055143 | 0.008365 | −0.013888 | −0.040361 | 0.0006 | 0.00437 | 0.02812 |
| 175 | −0.025067 | 0.002695 | 0.008627 | 0.026047 | −0.025704 | 0.024727 | −0.003986 | −0.014521 | 0.032607 | −0.029134 | −0.046547 | −0.020983 | −0.009263 | 0.004135 |
| 176 | 0.040621 | −0.004299 | 0.010328 | 0.017652 | 0.008588 | −0.051063 | −0.007966 | −0.017809 | 0.031364 | 0.03757 | −0.03119 | 0.003847 | −0.006332 | 0.019979 |
| 177 | −0.046906 | 0.033607 | −0.0025 | −0.002996 | 0.010378 | −0.029063 | 0.017723 | −0.04933 | −0.023205 | 0.009031 | −0.019667 | 0.026653 | 0.049443 | 0.000483 |
| 178 | −0.025597 | 0.017922 | 0.013002 | 0.039682 | 0.004675 | 0.038844 | −0.018088 | −0.010361 | −0.001804 | −0.013674 | −0.00021 | −0.008569 | 0.005053 | −0.008326 |
| 179 | 0.006607 | 0.007879 | 0.012394 | 0.006604 | −0.007288 | 0.01384 | −0.012011 | −0.003127 | 0.002382 | −0.003623 | 0.039102 | 0.009772 | 0.004028 | −0.015626 |
| 180 | 0.00622 | 0.011299 | 0.004763 | 0.017274 | 0.010524 | 0.027575 | −0.000078 | −0.005867 | 0.008377 | −0.023867 | 0.021852 | −0.003485 | 0.013803 | 0.004328 |
| 181 | −0.001107 | 0.014957 | 0.008142 | 0.014494 | 0.006368 | 0.021337 | −0.004725 | −0.013573 | 0.007278 | −0.014279 | 0.025795 | 0.002226 | 0.015046 | −0.000531 |
| 182 | −0.010391 | 0.008961 | 0.004272 | 0.00891 | 0.014203 | 0.010783 | −0.002051 | −0.023022 | −0.011857 | −0.012317 | 0.011815 | 0.010523 | 0.016118 | −0.01082 |
| 183 | 0.018958 | −0.014323 | −0.008542 | −0.007641 | −0.035829 | −0.021955 | −0.008934 | −0.02486 | −0.025742 | 0.008001 | 0.017959 | 0.03113 | 0.008487 | −0.008612 |
| 184 | 0.019189 | −0.021191 | 0.01511 | 0.006875 | −0.036657 | −0.018757 | −0.015038 | −0.004995 | −0.048124 | −0.02243 | −0.006188 | −0.001717 | −0.022814 | 0.046614 |
| 185 | 0.010829 | 0.024244 | 0.006957 | 0.017987 | 0.010847 | 0.014838 | −0.024369 | 0.032543 | −0.030387 | −0.013135 | 0.007045 | 0.051766 | 0.000432 | 0.057309 |
| 186 | −0.015648 | 0.013519 | −0.029539 | 0.010496 | −0.009122 | 0.053047 | 0.001189 | 0.026037 | 0.013106 | 0.007729 | −0.036436 | 0.018394 | 0.03772 | 0.03013 |
| 187 | −0.007399 | 0.017566 | −0.000477 | −0.006627 | −0.008505 | 0.023241 | 0.009698 | −0.01275 | −0.013855 | −0.003365 | 0.028133 | −0.010817 | 0.005884 | −0.009126 |
| 188 | −0.001041 | 0.011382 | −0.004504 | −0.022105 | −0.016428 | 0.005621 | 0.018518 | −0.03727 | −0.005471 | −0.004733 | −0.003988 | −0.011939 | 0.004112 | −0.00388 |
| 189 | 0.009374 | 0.016353 | 0.005603 | −0.038359 | −0.001406 | −0.0032 | 0.009312 | −0.033885 | −0.026609 | −0.011119 | 0.002137 | −0.024344 | −0.013706 | −0.006749 |
| 190 | −0.020882 | 0.009587 | 0.020198 | 0.020894 | 0.01481 | −0.02308 | −0.004465 | −0.020602 | 0.002886 | −0.020748 | −0.011961 | −0.012866 | −0.000663 | −0.013059 |
| 191 | −0.01097 | 0.010385 | 0.005974 | −0.000329 | −0.011392 | −0.022766 | −0.025636 | −0.013969 | 0.006877 | −0.00886 | −0.020407 | −0.001797 | −0.008532 | −0.003283 |
| 192 | −0.00651 | −0.023939 | 0.020915 | 0.001391 | −0.012702 | −0.022624 | −0.005581 | −0.025487 | −0.022649 | 0.026473 | 0.017257 | −0.010959 | −0.023347 | −0.041205 |
| 193 | −0.018104 | −0.024557 | −0.016602 | 0.008292 | 0.00486 | −0.008438 | 0.012868 | −0.015652 | 0.00806 | −0.014111 | −0.012153 | 0.007068 | −0.012811 | −0.019014 |
| 194 | −0.01934 | −0.003791 | −0.002194 | 0.000049 | −0.02943 | 0.000307 | −0.004276 | −0.027323 | 0.030836 | 0.017933 | 0.020664 | −0.003345 | 0.002666 | −0.018327 |
| 195 | −0.003328 | 0.017159 | 0.038925 | 0.007344 | −0.011775 | 0.018342 | −0.009155 | −0.034848 | −0.027304 | 0.005817 | 0.002394 | 0.007459 | 0.011069 | 0.005023 |
| 196 | −0.037788 | 0.024282 | 0.048081 | 0.019678 | 0.009438 | 0.027836 | −0.005582 | −0.03822 | −0.009827 | 0.014943 | −0.006515 | −0.01475 | 0.011958 | 0.005502 |
| 197 | −0.027356 | 0.009193 | 0.018297 | 0.016426 | 0.003025 | −0.035228 | −0.006235 | −0.044532 | −0.005045 | 0.001438 | −0.022339 | −0.006002 | −0.001425 | −0.02478 |
| 198 | 0.010093 | 0.024437 | 0.025365 | 0.024816 | −0.007291 | 0.009667 | −0.016732 | 0.009828 | −0.037893 | −0.002621 | 0.001756 | 0.014054 | 0.005667 | 0.015988 |
| 199 | −0.01497 | 0.005099 | 0.051066 | −0.003639 | 0.015367 | 0.022148 | −0.013389 | 0.026353 | −0.017784 | 0.030189 | −0.003122 | −0.00867 | −0.048389 | −0.043738 |
| 200 | −0.064643 | −0.011535 | −0.048303 | 0.018892 | −0.034983 | 0.01254 | −0.001558 | −0.038828 | −0.04583 | −0.012516 | −0.015911 | −0.004969 | 0.018761 | −0.077893 |
| 201 | 0.032317 | −0.01681 | −0.012307 | 0.014061 | 0.025833 | −0.010711 | 0.020845 | −0.00724 | 0.050951 | 0.011122 | −0.066867 | −0.021258 | −0.011211 | 0.021318 |
| 202 | −0.061251 | 0.003891 | 0.022332 | 0.019123 | 0.008321 | 0.019051 | 0.001903 | −0.004068 | −0.015857 | −0.012208 | 0.028428 | 0.006083 | 0.021851 | −0.021131 |
| 203 | 0.006075 | 0.002309 | 0.013621 | 0.009919 | −0.035222 | −0.007729 | −0.006793 | 0.013338 | −0.041612 | −0.017086 | 0.011935 | 0.011569 | −0.002873 | −0.014857 |
| 204 | 0.002381 | −0.033164 | 0.015484 | 0.009575 | −0.002068 | 0.010686 | −0.040286 | 0.059066 | −0.050213 | 0.027506 | −0.025618 | −0.016297 | −0.011862 | 0.043976 |
| 205 | −0.055093 | −0.035497 | 0.021757 | 0.015825 | 0.004533 | 0.004175 | −0.023122 | 0.01331 | −0.035545 | −0.031587 | 0.078451 | −0.020957 | −0.042384 | −0.069685 |
| 206 | 0.021783 | −0.006132 | −0.008017 | 0.006417 | 0.028561 | 0.011008 | 0.045235 | −0.055985 | 0.050784 | 0.032145 | −0.002623 | 0.028847 | −0.005061 | 0.04189 |
| 207 | −0.02352 | −0.025109 | −0.022689 | 0.010256 | −0.023776 | −0.000272 | −0.017233 | −0.043087 | 0.034381 | 0.00362 | −0.000836 | −0.023998 | −0.016212 | −0.064735 |
| 208 | 0.049122 | −0.054083 | −0.014524 | −0.00841 | −0.069103 | −0.039329 | 0.01103 | 0.024797 | −0.03531 | −0.006678 | 0.019988 | 0.016725 | −0.00748 | −0.004206 |
| 209 | −0.0403 | −0.013091 | 0.034875 | −0.00902 | −0.004059 | −0.020753 | −0.005606 | −0.113555 | −0.052165 | 0.046121 | −0.008212 | −0.021194 | −0.00253 | 0.014759 |
| 210 | 0.023909 | −0.012355 | 0.007205 | 0.009671 | −0.062944 | −0.04688 | −0.008746 | −0.02231 | −0.03169 | −0.007032 | −0.026072 | 0.017138 | 0.000038 | −0.011871 |
| 211 | −0.00294 | 0.008908 | −0.008945 | −0.035139 | −0.026866 | −0.050039 | −0.01448 | −0.001377 | −0.020482 | 0.01098 | 0.017142 | 0.020492 | 0.02106 | 0.002576 |
| 212 | 0.04155 | 0.002186 | −0.020563 | −0.075666 | −0.010948 | −0.032399 | −0.007297 | 0.077991 | −0.032021 | −0.018552 | 0.044711 | 0.033059 | −0.01763 | −0.082881 |
| 213 | 0.025229 | −0.004564 | 0.017814 | 0.050759 | −0.027912 | 0.006692 | 0.001785 | 0.015218 | 0.033665 | −0.082973 | −0.04269 | 0.020238 | 0.005638 | −0.004286 |
| 214 | 0.025903 | 0.004774 | 0.00762 | −0.008573 | −0.001954 | 0.010755 | −0.017777 | 0.001082 | −0.022228 | −0.008766 | 0.028895 | −0.006631 | 0.002821 | −0.001588 |
| 215 | −0.022572 | −0.015403 | −0.008855 | 0.003207 | −0.028813 | 0.027324 | −0.03557 | 0.014726 | −0.027015 | −0.024378 | 0.023908 | 0.049348 | −0.021807 | 0.001611 |
| 216 | −0.013784 | 0.001555 | −0.006662 | 0.025988 | 0.020084 | 0.027191 | 0.018465 | 0.007089 | 0.004213 | 0.008271 | 0.004445 | −0.016812 | 0.000039 | −0.010914 |
| 217 | −0.00728 | 0.0072 | 0.045047 | 0.018734 | −0.011281 | −0.006287 | −0.020191 | 0.074811 | 0.000981 | 0.039852 | 0.056123 | 0.008808 | 0.001798 | −0.009736 |
| 218 | 0.014963 | 0.005026 | 0.007047 | −0.003033 | −0.005282 | 0.005376 | −0.010679 | 0.012936 | −0.019833 | 0.009431 | −0.00764 | 0.004579 | 0.006633 | 0.044532 |
| 219 | 0.008767 | 0.016422 | 0.001247 | 0.00215 | −0.00594 | 0.010548 | −0.00448 | 0.008152 | 0.009189 | 0.033388 | 0.003913 | −0.02204 | 0.0113 | 0.01663 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 220 | 0.035164 | 0.022308 | 0.014142 | −0.002583 | −0.031801 | 0.000275 | −0.022243 | 0.014644 | −0.020749 | 0.016024 | 0.040714 | 0.005006 | 0.004218 | 0.024351 |
| 221 | 0.039092 | −0.010077 | −0.010898 | −0.005415 | −0.022077 | −0.01255 | −0.007599 | −0.007126 | −0.002721 | −0.038719 | 0.045067 | −0.004395 | −0.00491 | 0.020626 |
| 222 | 0.017592 | −0.033725 | 0.008559 | −0.000927 | −0.022771 | −0.026411 | −0.005711 | −0.034915 | −0.022173 | −0.016979 | 0.029354 | −0.015548 | −0.034671 | −0.021652 |
| 223 | 0.015078 | −0.023032 | −0.020438 | 0.012278 | −0.017254 | 0.001568 | 0.002765 | −0.02318 | 0.020025 | 0.00127 | 0.011875 | 0.006805 | −0.008115 | −0.005655 |
| 224 | 0.041517 | 0.005877 | 0.034161 | 0.018024 | 0.013906 | 0.006116 | 0.008689 | −0.035039 | −0.012094 | 0.027956 | 0.007221 | 0.03697 | 0.004125 | 0.010565 |
| 225 | 0.066953 | 0.004248 | 0.032146 | 0.008846 | −0.005502 | 0.000208 | 0.011161 | −0.035402 | −0.02129 | 0.019701 | 0.01184 | 0.036251 | 0.007465 | 0.007268 |
| 226 | 0.009962 | 0.004321 | −0.001868 | −0.011428 | 0.011573 | −0.0097 | 0.004406 | −0.003799 | −0.019831 | −0.008112 | −0.008028 | 0.003774 | 0.001461 | 0.029875 |
| 227 | 0.012278 | 0.020161 | 0.001742 | 0.018138 | 0.036103 | 0.031472 | 0.012662 | −0.031836 | −0.01963 | 0.020786 | −0.013099 | 0.03113 | 0.008615 | 0.037064 |
| 228 | 0.009848 | −0.025693 | 0.003178 | 0.020012 | 0.010713 | 0.006752 | 0.004748 | 0.003388 | −0.03256 | −0.038491 | 0.004332 | −0.030183 | −0.028816 | −0.008332 |
| 229 | 0.05148 | 0.025353 | 0.005431 | 0.014992 | 0.00608 | 0.011685 | 0.010888 | 0.05605 | −0.020969 | 0.003223 | 0.030723 | −0.022559 | −0.006104 | 0.041359 |
| 230 | −0.000176 | 0.016962 | −0.016874 | 0.016989 | 0.025628 | 0.025047 | 0.009625 | 0.000547 | −0.001821 | −0.02477 | −0.009069 | −0.00807 | −0.008471 | −0.011744 |
| 231 | −0.039795 | −0.004244 | −0.01252 | −0.003018 | 0.030875 | −0.002835 | 0.014871 | −0.024395 | −0.011811 | 0.002716 | −0.015312 | 0.032108 | 0.011788 | 0.022741 |
| 232 | 0.021974 | −0.006569 | 0.003666 | −0.007848 | −0.005926 | −0.020106 | −0.000429 | −0.049424 | −0.004137 | −0.045153 | −0.01013 | 0.004808 | −0.020945 | 0.00908 |
| 233 | 0.001107 | 0.013637 | −0.010348 | 0.014488 | −0.017788 | 0.024341 | −0.001532 | −0.004121 | 0.010291 | −0.028863 | −0.044316 | 0.021233 | 0.009623 | 0.039629 |
| 234 | 0.00435 | 0.013595 | −0.00259 | 0.038321 | 0.025334 | 0.031178 | 0.021871 | −0.008814 | −0.018282 | 0.002717 | −0.03324 | −0.014953 | 0.012376 | 0.003937 |
| 235 | −0.002186 | −0.001714 | −0.00777 | 0.012264 | 0.007446 | 0.003888 | −0.009318 | −0.001613 | −0.008142 | 0.003085 | −0.015737 | 0.003301 | −0.008476 | 0.011339 |
| 236 | 0.015288 | −0.001006 | −0.009079 | 0.009564 | 0.001954 | −0.035388 | 0.012504 | −0.021202 | 0.044721 | 0.015381 | −0.022901 | 0.014299 | 0.000863 | −0.009208 |
| 237 | −0.017483 | 0.000513 | 0.014215 | −0.007346 | 0.010283 | −0.020275 | 0.021046 | 0.019402 | −0.024985 | 0.005895 | −0.013921 | −0.033134 | 0.014454 | −0.04184 |
| 238 | −0.043201 | −0.004637 | 0.009162 | −0.006523 | 0.00456 | −0.000416 | 0.018333 | 0.024139 | 0.005979 | 0.014312 | −0.001794 | −0.023031 | 0.009515 | −0.03535 |
| 239 | −0.031866 | −0.017233 | 0.006749 | −0.001284 | −0.006377 | 0.015221 | −0.001847 | 0.014036 | 0.022878 | 0.025629 | −0.00716 | 0.008959 | −0.006908 | −0.007131 |
| 240 | −0.028128 | −0.002008 | 0.00439 | 0.01226 | 0.008595 | 0.013846 | 0.013419 | 0.038616 | 0.038707 | −0.024549 | 0.013037 | −0.01653 | 0.011212 | 0.004376 |
| 241 | 0.00535 | 0.003096 | 0.013518 | 0.011237 | −0.006513 | 0.01414 | 0.011539 | 0.021714 | 0.005494 | 0.007109 | −0.022641 | 0.004345 | 0.019089 | 0.024453 |
| 242 | 0.004516 | 0.002597 | −0.002417 | 0.007118 | 0.002497 | −0.015929 | 0.003991 | −0.027345 | 0.001581 | −0.004962 | −0.011012 | 0.028197 | −0.002712 | 0.023291 |
| 243 | −0.017567 | −0.007003 | −0.004495 | 0.01581 | 0.005838 | −0.007489 | −0.004046 | −0.008088 | −0.007219 | −0.009477 | −0.015839 | −0.008369 | −0.018215 | 0.016549 |
| 244 | 0.022619 | −0.018691 | −0.034093 | −0.009317 | −0.012362 | −0.00449 | 0.008014 | −0.01178 | 0.004403 | −0.011087 | 0.014952 | 0.014927 | −0.004073 | 0.018727 |
| 245 | 0.010147 | 0.001674 | −0.01386 | −0.006122 | −0.017329 | −0.018413 | −0.000503 | −0.028287 | 0.012591 | 0.019972 | 0.002422 | 0.025524 | −0.005201 | −0.00216 |
| 246 | −0.004492 | 0.021738 | −0.004966 | −0.013422 | −0.010572 | 0.006405 | −0.007729 | −0.021913 | −0.031265 | −0.006321 | −0.011485 | 0.008983 | 0.00255 | −0.023179 |
| 247 | 0.004827 | 0.02832 | 0.008288 | 0.011419 | −0.009738 | 0.000377 | −0.019813 | −0.010118 | 0.02022 | −0.008501 | −0.000234 | 0.004344 | 0.00167 | −0.011857 |
| 248 | 0.020279 | 0.012084 | −0.003715 | −0.002111 | −0.025503 | −0.017616 | −0.022135 | −0.018348 | 0.021773 | 0.000896 | 0.009155 | −0.01259 | −0.005134 | −0.000655 |
| 249 | −0.012975 | −0.039429 | 0.007568 | 0.006011 | −0.002647 | −0.034217 | 0.019137 | −0.00803 | 0.007408 | −0.003211 | −0.034691 | −0.02145 | −0.011966 | −0.009932 |
| 250 | −0.010418 | 0.001221 | −0.012471 | 0.017985 | 0.009327 | 0.023838 | 0.017909 | 0.007647 | 0.021544 | 0.02175 | −0.005662 | −0.001272 | 0.025471 | −0.000782 |
| 251 | 0.014385 | −0.000961 | −0.008515 | 0.007257 | 0.002702 | 0.004281 | 0.016414 | 0.017768 | 0.017108 | 0.003517 | 0.008651 | −0.007424 | 0.021399 | 0.002037 |
| 252 | 0.012476 | −0.001503 | 0.024226 | 0.017884 | 0.005057 | −0.010388 | 0.002834 | −0.017747 | −0.022312 | 0.03413 | −0.006511 | 0.03149 | 0.007319 | 0.019273 |
| 253 | 0.007838 | −0.022554 | 0.000541 | 0.009352 | −0.015446 | −0.022518 | 0.014884 | −0.014393 | −0.012295 | 0.015441 | −0.025801 | 0.004083 | −0.003325 | 0.025819 |
| 254 | 0.011862 | −0.014623 | −0.031286 | 0.009676 | −0.010137 | 0.022279 | 0.010053 | −0.001567 | 0.021963 | 0.023289 | −0.011404 | 0.013743 | −0.001503 | −0.000734 |
| 255 | 0.01102 | 0.010485 | −0.035191 | −0.011088 | −0.004865 | 0.008134 | 0.007693 | −0.007535 | −0.004134 | −0.019805 | 0.00134 | 0.007604 | 0.005108 | 0.001171 |
| 256 | 0.007848 | 0.003967 | 0.004771 | 0.003633 | −0.008865 | −0.004556 | 0.002525 | −0.006032 | −0.019689 | −0.049081 | −0.020896 | 0.012352 | −0.012119 | 0.006646 |
| 257 | −0.026892 | 0.001148 | 0.016062 | 0.02235 | 0.012574 | −0.002691 | −0.019189 | −0.017578 | 0.023981 | −0.029125 | 0.006726 | 0.009881 | −0.000209 | −0.018276 |
| 258 | −0.008896 | 0.00224 | 0.024313 | 0.010846 | 0.000301 | −0.023558 | −0.01819 | −0.017406 | 0.038807 | 0.008936 | 0.014277 | 0.008147 | −0.00427 | −0.022732 |
| 259 | 0.012613 | −0.034622 | −0.01212 | 0.018964 | −0.01293 | −0.005206 | 0.014713 | −0.020033 | −0.000699 | 0.021834 | −0.015808 | −0.015712 | −0.002734 | −0.017524 |
| 260 | 0.043789 | −0.018586 | 0.017884 | 0.032756 | −0.001956 | 0.022699 | 0.005439 | −0.005579 | −0.021936 | 0.043858 | 0.021183 | −0.007452 | 0.007663 | −0.002109 |
| 261 | 0.000033 | 0.001623 | 0.030134 | 0.01754 | 0.017112 | −0.00052 | 0.021106 | 0.008013 | −0.007406 | 0.015847 | 0.022843 | −0.014315 | 0.014901 | −0.012267 |
| 262 | −0.021822 | 0.005694 | 0.020549 | 0.012309 | 0.019641 | −0.016955 | −0.003469 | −0.027105 | 0.002906 | −0.017965 | 0.003426 | 0.011528 | −0.001667 | −0.00655 |
| 263 | −0.014306 | −0.00056 | −0.000411 | 0.012518 | 0.001904 | −0.023719 | −0.009472 | −0.031826 | 0.014868 | −0.000233 | −0.006015 | 0.009297 | −0.002557 | −0.010977 |
| 264 | 0.017904 | −0.037084 | −0.008113 | −0.003395 | −0.010558 | −0.004618 | 0.005714 | −0.012395 | −0.02504 | 0.020081 | −0.009687 | −0.022246 | −0.022492 | −0.031843 |
| 265 | 0.015016 | −0.018895 | 0.012131 | 0.006713 | 0.007927 | 0.028627 | 0.000801 | −0.008735 | −0.026039 | 0.040829 | −0.028519 | 0.003127 | −0.014504 | −0.035543 |
| 266 | 0.018868 | 0.014193 | 0.016594 | 0.006578 | 0.017235 | 0.015984 | 0.006265 | 0.01059 | −0.019285 | 0.026789 | 0.002443 | 0.001838 | 0.004031 | −0.015842 |
| 267 | 0.023302 | −0.010184 | −0.003544 | −0.001596 | 0.004332 | 0.016934 | 0.031589 | 0.020728 | −0.033469 | 0.005042 | −0.014328 | 0.01248 | −0.004463 | 0.067846 |
| 268 | 0.006398 | −0.000716 | 0.005549 | −0.007702 | −0.002412 | 0.009691 | −0.001216 | −0.008678 | −0.039114 | 0.017638 | −0.022125 | 0.018039 | −0.004244 | 0.033416 |
| 269 | 0.013852 | 0.004333 | 0.005931 | −0.011696 | 0.007758 | 0.000912 | 0.003982 | −0.00639 | −0.033243 | 0.000688 | −0.001121 | 0.013604 | 0.002427 | 0.038702 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 270 | −0.000381 | 0.009702 | −0.000515 | −0.001005 | 0.018871 | 0.015399 | 0.001172 | −0.018354 | −0.014524 | 0.00905 | −0.006816 | 0.005345 | 0.002326 | 0.036737 |
| 271 | 0.00693 | 0.020231 | −0.022008 | −0.001185 | 0.023537 | −0.050112 | 0.013137 | 0.021687 | 0.023869 | 0.062682 | 0.019533 | −0.017422 | 0.015394 | 0.024889 |
| 272 | 0.031256 | 0.019425 | −0.002216 | 0.001796 | 0.000696 | −0.011339 | 0.006884 | 0.041452 | 0.007385 | 0.006782 | 0.020473 | −0.027523 | 0.002157 | 0.028359 |
| 273 | 0.015685 | 0.009756 | −0.000554 | 0.000084 | −0.015683 | 0.015206 | −0.021823 | −0.000155 | −0.001427 | 0.021671 | −0.015949 | 0.001075 | −0.00326 | 0.027519 |
| 274 | 0.01695 | 0.013601 | 0.001285 | −0.000876 | −0.006575 | 0.018378 | −0.017311 | 0.005263 | 0.002643 | 0.018903 | −0.007646 | −0.00284 | 0.000935 | 0.024808 |
| 275 | −0.001258 | 0.018589 | −0.036489 | 0.015486 | 0.026239 | 0.030495 | −0.005555 | −0.001156 | 0.023652 | −0.010253 | −0.001712 | −0.023672 | −0.010922 | 0.005285 |
| 276 | 0.023949 | 0.01004 | 0.008659 | 0.014406 | 0.005523 | −0.034865 | 0.020212 | −0.004079 | 0.055166 | 0.038313 | −0.005691 | 0.002112 | 0.000314 | 0.006324 |
| 277 | 0.009874 | −0.017589 | 0.017783 | 0.001155 | 0.003332 | 0.009442 | 0.003782 | 0.00994 | 0.005503 | 0.002586 | −0.015786 | 0.000023 | −0.010653 | 0.002296 |
| 278 | 0.010197 | −0.027719 | −0.001997 | 0.000781 | 0.008903 | 0.008941 | 0.004145 | 0.003208 | 0.022008 | −0.012204 | −0.01156 | −0.005 | −0.011809 | 0.007083 |
| 279 | −0.021716 | −0.012309 | 0.002837 | −0.001522 | 0.005451 | 0.022412 | 0.001864 | 0.025296 | 0.04535 | 0.019707 | 0.017058 | −0.020216 | −0.008748 | −0.010812 |
| 280 | −0.0049 | −0.005485 | 0.006459 | 0.016085 | −0.006377 | −0.006082 | 0.014758 | −0.037988 | 0.00083 | 0.011321 | −0.038451 | −0.006007 | −0.017122 | 0.021639 |
| 281 | 0.004846 | 0.018882 | −0.015301 | −0.015438 | −0.007083 | −0.010845 | −0.01434 | −0.029908 | −0.003086 | −0.027266 | −0.016925 | 0.005544 | 0.002129 | −0.000035 |
| 282 | −0.005431 | 0.018019 | −0.016023 | 0.003571 | 0.016398 | −0.005122 | −0.016709 | −0.043176 | 0.024493 | −0.030142 | −0.009497 | 0.019099 | 0.000691 | 0.009589 |
| 283 | 0.020817 | 0.025685 | −0.014891 | 0.013056 | 0.005932 | 0.001031 | −0.021118 | 0.006736 | 0.056012 | −0.018416 | 0.009522 | −0.016595 | 0.002824 | 0.010849 |
| 284 | −0.017926 | −0.005816 | 0.003862 | 0.010898 | 0.009529 | 0.00005 | −0.012292 | −0.00358 | 0.022408 | −0.026393 | 0.009703 | −0.002214 | −0.001646 | −0.018698 |
| 285 | −0.0243 | −0.010413 | 0.000851 | 8.017549 | 0.022409 | 0.006232 | −0.012608 | −0.009027 | 0.024179 | −0.024421 | 0.001972 | 0.006585 | −0.002025 | −0.007885 |
| 286 | −0.022971 | 0.005136 | 0.015533 | 0.009447 | 0.017781 | −0.01246 | −0.003737 | 0.002995 | 0.046185 | −0.006115 | 0.029674 | 0.004846 | 0.007961 | −0.029204 |
| 287 | −0.025705 | 0.004438 | 0.005544 | 0.011592 | 0.026637 | −0.018671 | −0.009552 | −0.001819 | 0.056152 | −0.01683 | 0.02511 | −0.00498 | 0.00022 | −0.015343 |
| 288 | 0.01207 | 0.009223 | 0.02135 | −0.007009 | 0.015221 | −0.033029 | −0.015478 | 0.006172 | 0.041294 | 0.01157 | 0.031036 | −0.019751 | −0.010941 | −0.010601 |
| 289 | −0.001316 | 0.010172 | 0.019442 | 0.013117 | 0.021789 | −0.002844 | −0.016006 | −0.004811 | 0.01464 | −0.004484 | 0.005601 | −0.000976 | −0.01542 | −0.006045 |
| 290 | −0.038695 | −0.00122 | 0.000739 | −0.007861 | −0.005662 | −0.01358 | −0.004731 | 0.013929 | −0.040892 | 0.009171 | −0.023807 | −0.018275 | −0.000328 | 0.000463 |
| 291 | −0.043398 | 0.002473 | 0.003706 | −0.002987 | −0.000045 | −0.01175 | −0.00559 | 0.015374 | −0.036628 | 0.008472 | −0.02236 | −0.018773 | 0.001949 | −0.000356 |
| 292 | −0.052521 | 0.007455 | 0.006219 | −0.007977 | 0.005075 | −0.012599 | −0.004232 | 0.029493 | −0.035704 | 0.004257 | −0.009136 | −0.020607 | 0.001035 | −0.008146 |
| 293 | −0.027124 | −0.006856 | −0.035587 | 0.001151 | −0.018465 | −0.005679 | −0.003467 | −0.007581 | 0.0286 | −0.000052 | −0.037359 | 0.01582 | 0.013281 | 0.006592 |
| 294 | −0.005775 | −0.005247 | −0.00768 | −0.005589 | 0.008801 | 0.013008 | −0.008449 | 0.001544 | −0.031166 | 0.005384 | −0.014265 | 0.001555 | −0.010182 | 0.021237 |
| 295 | −0.0106 | 0.009002 | −0.00908 | 0.00496 | −0.011382 | 0.013855 | −0.02497 | 0.009081 | 0.019328 | −0.008571 | −0.024439 | 0.014185 | 0.004394 | 0.018525 |
| 296 | 0.047056 | 0.016895 | 0.013666 | −0.005665 | −0.014458 | 0.02223 | −0.013327 | 0.012407 | 0.002854 | −0.025526 | 0.002953 | 0.005932 | −0.016242 | 0.037085 |
| 297 | 0.004147 | −0.002079 | 0.005893 | −0.000757 | −0.011893 | 0.000787 | −0.019086 | 0.014608 | 0.014561 | −0.010375 | −0.01194 | 0.0111 | 0.001186 | 0.035622 |
| 298 | 0.014459 | 0.014999 | −0.001055 | 0.007991 | −0.025115 | 0.01094 | 0.009361 | −0.036038 | −0.006743 | 0.034878 | −0.001135 | −0.005871 | 0.014049 | −0.021684 |
| 299 | −0.008521 | −0.008912 | −0.005065 | −0.003641 | −0.013443 | −0.020938 | 0.000159 | −0.001161 | 0.003556 | 0.000952 | −0.021056 | 0.020029 | −0.000141 | 0.011943 |
| 300 | −0.103803 | 0.0305 | 0.017392 | 0.05295 | 0.035045 | 0.057579 | 0.026259 | 0.035561 | 0.031393 | −0.017931 | 0.017795 | −0.063539 | 0.012288 | −0.030297 |
| 301 | −0.009387 | −0.021233 | −0.012067 | 0.003272 | −0.006241 | −0.008471 | −0.010028 | −0.010164 | −0.012053 | −0.019059 | −0.020049 | 0.018244 | −0.011347 | −0.001793 |
| 302 | −0.031879 | −0.013232 | 0.002088 | 0.005216 | −0.002552 | 0.00614 | −0.010538 | −0.005218 | −0.024713 | −0.009913 | 0.000433 | 0.012367 | −0.019645 | −0.007963 |
| 303 | −0.020533 | −0.003263 | 0.017197 | 0.007234 | 0.003662 | −0.017916 | 0.00836 | −0.006626 | −0.003539 | −0.023595 | 0.037339 | 0.009679 | −0.009322 | −0.019543 |
| 304 | −0.021777 | −0.007417 | 0.007503 | −0.001857 | −0.016862 | −0.013927 | 0.014612 | −0.015423 | −0.001694 | 0.009181 | 0.004765 | −0.00437 | −0.007039 | −0.025242 |
| 305 | −0.040631 | 0.007187 | −0.029248 | 0.000582 | 0.015472 | −0.009819 | −0.005204 | −0.014112 | 0.000096 | −0.023215 | −0.01121 | 0.013718 | 0.009797 | −0.030747 |
| 306 | −0.030288 | −0.022722 | 0.004787 | 0.023708 | −0.010436 | 0.015605 | −0.014086 | 0.026712 | −0.009354 | 0.003245 | −0.024989 | −0.013841 | −0.000342 | −0.02552 |
| 307 | −0.089122 | −0.025937 | −0.046644 | 0.01377 | 0.014377 | 0.016767 | 0.033002 | −0.008209 | 0.02829 | 0.004917 | 0.019929 | −0.023535 | 0.036996 | −0.000607 |
| 308 | 0.017023 | 0.022875 | 0.016451 | −0.03226 | −0.033276 | 0.016401 | 0.004055 | −0.020804 | 0.025716 | 0.028722 | 0.008549 | −0.012132 | 0.002697 | −0.020217 |
| 309 | −0.024281 | −0.016806 | −0.03642 | −0.001463 | 0.007478 | −0.003662 | 0.007148 | −0.000743 | −0.003217 | −0.029652 | −0.025422 | 0.004705 | 0.002765 | 0.012701 |
| 310 | −0.011499 | −0.008378 | −0.056605 | 0.007367 | 0.001596 | 0.005817 | −0.00056 | −0.008465 | −0.001924 | −0.025409 | −0.020524 | 0.042514 | 0.017208 | −0.00758 |
| 311 | 0.018363 | −0.015938 | −0.019376 | −0.001043 | −0.035579 | 0.019856 | 0.007717 | −0.004138 | −0.025629 | 0.029735 | −0.031125 | −0.009012 | 0.006525 | 0.013423 |
| 312 | −0.018716 | 0.03516 | −0.001829 | −0.075776 | 0.026847 | −0.042566 | −0.030518 | −0.067547 | −0.033855 | −0.071422 | −0.017164 | −0.058746 | −0.02581 | 0.006975 |
| 313 | 0.041406 | 0.007559 | 0.010157 | −0.000661 | −0.028549 | 0.010764 | 0.002302 | 0.005999 | −0.012074 | 0.024495 | 0.005396 | −0.015 | 0.017362 | −0.016317 |
| 314 | −0.013281 | 0.022765 | 0.017584 | 0.04161 | 0.029881 | 0.045227 | −0.046566 | 0.063337 | −0.025606 | 0.03668 | 0.035898 | −0.033238 | 0.039651 | −0.03534 |
| 315 | −0.004981 | 0.007603 | 0.005196 | −0.000654 | 0.018045 | 0.002413 | 0.004224 | 0.016207 | 0.003403 | −0.005201 | 0.015116 | −0.003634 | 0.008939 | −0.003833 |
| 316 | 0.035075 | 0.005746 | 0.020738 | 0.013765 | 0.011415 | 0.030375 | −0.01928 | −0.048519 | −0.025305 | −0.042449 | 0.003936 | −0.016862 | 0.00086 | 0.024665 |
| 317 | −0.006078 | −0.002237 | −0.021134 | 0.023884 | 0.027174 | 0.023308 | −0.010638 | 0.006316 | 0.008812 | −0.033336 | −0.011182 | 0.004317 | 0.003274 | 0.00323 |
| 318 | 0.041704 | −0.018204 | −0.041859 | 0.010827 | −0.009467 | 0.010529 | 0.000935 | 0.003157 | −0.002241 | 0.029953 | 0.00367 | −0.002468 | 0.022224 | 0.000408 |
| 319 | 0.007517 | −0.008156 | −0.007824 | 0.014793 | 0.014309 | 0.000142 | −0.000233 | 0.011253 | 0.002583 | −0.0256 | 0.003214 | 0.0045 | 0.004997 | 0.012795 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 320 | 0.04388 | −0.011449 | −0.00476 | 0.000728 | −0.051237 | 0.024862 | −0.031444 | −0.015857 | −0.017455 | 0.014293 | −0.050677 | 0.003433 | −0.006362 | 0.01825 |
| 321 | 0.021731 | −0.027736 | 0.016966 | 0.006202 | −0.013889 | 0.024784 | −0.005914 | 0.034733 | −0.059733 | 0.01111 | 0.007798 | 0.004411 | −0.012222 | 0.000807 |
| 322 | −0.03038 | 0.000914 | −0.030582 | −0.041072 | 0.044253 | 0.00855 | 0.003002 | −0.008269 | 0.005294 | −0.002754 | 0.010718 | 0.006361 | −0.022958 | −0.037094 |
| 323 | 0.038646 | −0.013147 | −0.001606 | −0.02737 | −0.021415 | 0.020235 | −0.001633 | −0.011988 | −0.069511 | 0.042376 | −0.025953 | 0.014951 | −0.001027 | −0.051549 |
| 324 | −0.004188 | −0.026966 | −0.027583 | −0.031518 | −0.023967 | −0.024374 | −0.016877 | 0.002168 | 0.018343 | 0.05683 | 0.004776 | −0.033507 | −0.026413 | 0.005964 |
| 325 | 0.007813 | −0.002452 | 0.009299 | −0.008064 | 0.018555 | −0.000676 | 0.006662 | 0.012989 | −0.022718 | −0.022545 | 0.028753 | −0.013525 | −0.017311 | 0.023514 |
| 326 | −0.039195 | −0.0001 | −0.010724 | −0.016419 | −0.00331 | −0.038088 | 0.004526 | 0.007368 | −0.01394 | −0.033337 | 0.023748 | −0.023214 | −0.007598 | −0.021753 |
| 327 | 0.002726 | −0.001782 | −0.014646 | −0.014759 | −0.01895 | 0.003191 | 0.002262 | −0.004212 | −0.028256 | 0.004665 | 0.002375 | −0.000551 | −0.011546 | −0.025077 |
| 328 | 0.001457 | 0.000407 | 0.048579 | −0.035628 | 0.002694 | 0.003908 | 0.004302 | 0.013329 | −0.013452 | −0.024063 | −0.011172 | −0.021545 | −0.023431 | −0.021943 |
| 329 | 0.010877 | −0.007384 | 0.000947 | −0.014129 | −0.0135 | −0.00042 | −0.005118 | 0.006652 | −0.048689 | −0.022552 | 0.017286 | −0.002884 | −0.020844 | −0.0317 |
| 330 | 0.010487 | 0.000447 | −0.000585 | 0.003406 | 0.012236 | −0.023933 | −0.008319 | −0.001873 | −0.02879 | −0.008762 | −0.001911 | 0.027584 | −0.034334 | −0.014082 |
| 331 | −0.02239 | −0.003545 | −0.004333 | −0.016382 | −0.003823 | −0.004927 | −0.000332 | −0.001319 | −0.021074 | 0.004669 | 0.015569 | −0.022808 | −0.013514 | −0.020236 |
| 332 | −0.031145 | −0.01789 | −0.011107 | −0.009179 | −0.019954 | −0.013622 | 0.021084 | 0.01819 | −0.00879 | −0.019329 | 0.013027 | −0.008052 | −0.002527 | 0.004997 |
| 333 | −0.006234 | −0.016358 | −0.001811 | 0.002758 | 0.0082 | 0.002912 | 0.006383 | −0.004162 | −0.02197 | −0.005738 | 0.009121 | −0.014026 | −0.016091 | 0.011481 |
| 334 | −0.041831 | 0.025462 | 0.029655 | −0.041317 | 0.036703 | −0.043182 | −0.002884 | −0.001148 | −0.043617 | −0.002595 | 0.064536 | 0.006965 | −0.020103 | 0.001454 |
| 335 | −0.010057 | −0.022701 | −0.031385 | −0.013607 | −0.011637 | 0.00043 | 0.002911 | 0.001156 | −0.04107 | 0.002136 | −0.013884 | −0.022212 | −0.009525 | −0.003517 |
| 336 | −0.03861 | 0.0069 | −0.006406 | 0.044676 | 0.040702 | 0.012768 | 0.009762 | 0.010879 | −0.036367 | −0.060429 | −0.051257 | −0.009684 | 0.000754 | −0.027802 |
| 337 | 0.002085 | 0.012637 | 0.001658 | −0.006604 | 0.024037 | −0.024171 | −0.009669 | −0.011894 | −0.012069 | −0.016032 | −0.015723 | −0.017414 | −0.001341 | 0.015291 |
| 338 | 0.059951 | 0.02831 | 0.002391 | −0.01596 | −0.040328 | −0.030446 | 0.015943 | −0.031019 | 0.019128 | 0.036004 | 0.01059 | 0.054747 | 0.013004 | −0.00855 |
| 339 | −0.005682 | −0.028144 | 0.006122 | −0.015009 | −0.014591 | −0.011032 | 0.008066 | −0.017902 | −0.035544 | −0.021255 | 0.004896 | −0.016769 | 0.000089 | −0.032942 |
| 340 | −0.034997 | 0.032128 | 0.013069 | 0.030984 | 0.000781 | −0.024595 | −0.015037 | −0.002334 | 0.036846 | −0.034306 | 0.015974 | −0.009828 | 0.011963 | −4.035484 |

| | FJ | FK | FL | FM | FN | FO | FP | FQ | FR | FS | FT | FU | FV | FW |
|---|---|---|---|---|---|---|---|---|---|---|---|---|---|---|
| 1 | 0.053076 | 0.060451 | 0.030725 | 0.023739 | −0.013183 | −0.014935 | −0.020984 | −0.002681 | −0.001395 | −0.046236 | −0.04559 | −0.02801 | 0.024004 | 0.025258 |
| 2 | 0.134783 | −0.014054 | −0.049959 | −0.022452 | 0.021174 | 0.01526 | 0.036519 | 0.007466 | −0.038004 | −0.094084 | −0.064126 | 0.050776 | 0.005493 | 0.057607 |
| 3 | −0.073271 | −0.042099 | 0.017818 | −0.046408 | −0.021639 | −0.022043 | −0.015857 | −0.013795 | 0.018103 | 0.10337 | 0.055706 | 0.02404 | 0.024631 | 0.001592 |
| 4 | 0.018402 | 0.168506 | −0.036527 | −0.070321 | 0.018752 | 0.008292 | 0.028415 | 0.033964 | −0.022715 | 0.009847 | −0.003744 | −0.049246 | 0.044636 | −0.016183 |
| 5 | 0.004945 | −0.032619 | 0.027524 | 0.096847 | −0.019791 | −0.063514 | 0.017036 | −0.03429 | −0.040426 | 0.015135 | −0.001867 | −0.013138 | −0.061767 | −0.030506 |
| 6 | 0.000639 | −0.009428 | 0.05036 | −0.0393 | 0.011515 | 0.024986 | 0.005617 | 0.006014 | −0.081832 | −0.079532 | −0.089067 | 0.122352 | −0.003987 | −0.016636 |
| 7 | −0.023758 | −0.072407 | −0.092166 | −0.051679 | −0.058268 | −0.048995 | −0.015824 | −0.088689 | −0.015722 | −0.051596 | −0.047037 | −0.052586 | −0.040065 | −0.031607 |
| 8 | 0.075027 | −0.116716 | 0.059619 | −0.029885 | −0.037481 | −0.010603 | 0.013013 | −0.016962 | 0.00482 | 0.017334 | −0.045945 | 0.008215 | 0.022911 | 0.04798 |
| 9 | 0.064546 | −0.029723 | 0.013535 | −0.026685 | −0.06838 | −0.070164 | −0.062107 | −0.077746 | −0.051724 | −0.033657 | −0.05731 | 0.023952 | −0.056129 | 0.003683 |
| 10 | 0.050089 | −0.013072 | 0.108988 | 0.03447 | −0.02721 | −0.018239 | −0.02117 | 0.010034 | −0.036788 | 0.039794 | 0.041226 | 0.003294 | 0.046394 | 0.012839 |
| 11 | −0.017026 | 0.050704 | 0.014454 | −0.115399 | −0.019302 | −0.052029 | −0.093985 | −0.014682 | −0.080107 | −0.052087 | 0.041448 | −0.068193 | −0.014299 | −0.058446 |
| 12 | −0.018509 | 0.018847 | 0.02599 | 0.05021 | 0.015086 | −0.008149 | 0.006172 | −0.003911 | −0.017893 | −0.062749 | −0.001689 | 0.018549 | −0.095699 | 0.014176 |
| 13 | −0.051165 | −0.11298 | −0.06021 | 0.108089 | −0.041609 | −0.053242 | −0.012529 | 0.023025 | 0.029451 | 0.086645 | 0.035847 | 0.04532 | 0.064241 | −0.020787 |
| 14 | 0.07353 | −0.013999 | 0.008597 | −0.045313 | 0.046324 | 0.064032 | 0.05324 | −0.032766 | −0.005009 | −0.021722 | −0.012266 | 0.027588 | −0.028487 | 0.037802 |
| 15 | 0.046195 | −0.013549 | −0.007129 | −0.019865 | 0.03442 | 0.075452 | −0.034358 | −0.081681 | −0.090386 | −0.070175 | 0.000208 | 0.006871 | −0.058634 | −0.042526 |
| 16 | 0.024359 | −0.016802 | 0.098262 | −0.014015 | 0.029768 | 0.034536 | 0.007254 | 0.027845 | 0.065108 | 0.042675 | 0.042662 | 0.050731 | −0.032357 | 0.010591 |
| 17 | −0.033357 | 0.079858 | −0.047229 | −0.100139 | −0.037365 | −0.029754 | −0.046425 | −0.063598 | −0.086992 | −0.116783 | −0.088162 | −0.028617 | −0.046422 | 0.025531 |
| 18 | −0.124576 | −0.034648 | −0.047797 | −0.037813 | −0.058266 | −0.034291 | −0.077554 | −0.072637 | −0.053161 | −0.044344 | −0.03231 | −0.045673 | −0.074105 | −0.000385 |
| 19 | 0.005856 | −0.075595 | −0.055146 | −0.032747 | 0.018852 | −0.011322 | 0.003506 | 0.045067 | 0.040205 | 0.021027 | 0.084745 | −0.084077 | −0.062428 | 0.066305 |
| 20 | 0.117967 | 0.110007 | 0.060702 | −0.05104 | −0.075449 | −0.077624 | −0.025925 | 0.038652 | 0.078233 | −0.008618 | −0.079617 | −0.016443 | −0.059085 | −0.048479 |
| 21 | −0.005992 | −0.009339 | 0.065148 | −0.018479 | 0.000337 | −0.010619 | 0.001511 | −0.105162 | −0.032705 | −0.002026 | −0.183006 | −0.099497 | −0.052919 | 0.001311 |
| 22 | 0.062388 | 0.089574 | −0.084478 | 0.081339 | 0.019088 | 0.025817 | 0.041376 | −0.024075 | −0.059308 | −0.052032 | 0.023452 | −0.033644 | −0.114347 | −0.029901 |
| 23 | −0.020098 | −0.030071 | −0.049541 | 0.010661 | 0.01714 | 0.033465 | 0.018694 | 0.018619 | −0.013099 | −0.017573 | −0.018287 | −0.063552 | 0.042469 | −0.029351 |
| 24 | 0.090198 | 0.015054 | 0.013844 | −0.016357 | 0.093289 | 0.06319 | 0.056306 | 0.013517 | 0.009807 | −0.010654 | −0.02554 | 0.053702 | 0.012601 | −0.02465 |
| 25 | −0.036673 | 0.107384 | 0.024927 | −0.10815 | 0.033437 | 0.019922 | −0.001947 | −0.016726 | −0.047555 | 0.004317 | 0.029576 | 0.013846 | 0.092412 | 0.06772 |
| 26 | −0.124693 | −0.004171 | 0.059974 | 0.018797 | 0.05555 | 0.008401 | 0.036584 | 0.029644 | −0.021268 | 0.081893 | 0.018929 | −0.0698 | −0.030587 | 0.01192 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 27 | −0.037149 | −0.150181 | −0.002293 | 0.089536 | −0.014354 | 0.01566 | 0.054998 | −0.05273 | −0.031528 | −0.06008 | −0.063295 | −0.048659 | 0.001108 | 0.005172 |
| 28 | 0.058363 | 0.000289 | 0.040338 | −0.157509 | 0.025834 | 0.008016 | −0.048995 | −0.006925 | 0.037048 | 0.021976 | 0.038741 | −0.11759 | 0.014343 | 0.010834 |
| 29 | −0.034505 | −0.013766 | 0.045204 | 0.007314 | −0.014242 | −0.013167 | 0.003213 | −0.008329 | −0.011593 | 0.019506 | −0.008583 | −0.026923 | −0.001878 | −0.016959 |
| 30 | 0.069675 | −0.02281 | −0.051113 | −0.050371 | −0.089395 | −0.120292 | −0.064319 | 0.041487 | 0.040519 | 0.028676 | 0.080369 | −0.007491 | −0.043159 | −0.107028 |
| 31 | 0.103606 | 0.007024 | −0.086474 | 0.004452 | 0.103743 | 0.152402 | 0.134764 | 0.054029 | 0.004772 | −0.008033 | 0.022717 | 0.162387 | −0.082459 | −0.005972 |
| 32 | −0.08982 | −0.06706 | −0.016543 | −0.009051 | 0.000315 | 0.022208 | 0.014266 | 0.009451 | 0.010086 | −0.025863 | 0.018956 | 0.033357 | 0.105533 | −0.054657 |
| 33 | −0.033132 | −0.096134 | 0.0297 | 0.033997 | 0.057326 | 0.028974 | 0.0177 | −0.008485 | −0.038629 | −0.026013 | 0.128889 | 0.105348 | −0.014823 | 0.081968 |
| 34 | 0.142076 | −0.0746 | −0.011142 | 0.009425 | −0.004816 | −0.013668 | −0.053608 | −0.021221 | 0.045583 | −0.000809 | 0.051643 | 0.042224 | −0.19235 | 0.030224 |
| 35 | 0.081597 | −0.108861 | −0.068067 | 0.057831 | −0.043679 | −0.025113 | −0.045444 | −0.014302 | −0.048298 | −0.064126 | −0.04797 | 0.009616 | 0.061805 | 0.027924 |
| 36 | 0.001806 | 0.013768 | −0.000953 | −0.007396 | 0.096381 | 0.128565 | 0.053227 | 0.06053 | −0.005332 | 0.041929 | 0.097428 | 0.051086 | 0.064379 | −0.00013 |
| 37 | −0.049597 | −0.049379 | 0.0777 | −0.038799 | −0.043239 | −0.043079 | −0.090094 | 0.082234 | −0.009756 | −0.028506 | −0.085995 | −0.022242 | 0.203979 | 0.035677 |
| 38 | −0.055706 | 0.093981 | −0.018964 | −0.018101 | 0.036283 | 0.024952 | −0.006217 | 0.052434 | 0.002988 | 0.035316 | 0.012421 | −0.02574 | 0.087258 | −0.068837 |
| 39 | −0.061433 | 0.069368 | 0.013412 | 0.039899 | −0.01155 | 0.025958 | 0.002052 | 0.017908 | −0.044154 | 0.005178 | −0.002725 | 0.027671 | 0.088217 | 0.010028 |
| 40 | 0.006965 | −0.006211 | 0.010554 | 0.0119 | −0.00629 | −0.00404 | 0.007894 | 0.014072 | −0.000336 | 0.018752 | −0.002707 | 0.009538 | 0.007604 | −0.004108 |
| 41 | 0.15905 | −0.018962 | −0.037266 | −0.050336 | 0.023505 | 0.030398 | 0.032038 | 0.088687 | 0.101838 | 0.091619 | 0.189129 | 0.051214 | −0.10386 | −0.009341 |
| 42 | −0.064104 | −0.178036 | 0.04964 | −0.039733 | 0.057302 | 0.063701 | 0.060981 | 0.032703 | −0.011299 | 0.017458 | −0.016659 | 0.033129 | −0.037272 | −0.071247 |
| 43 | −0.028006 | 0.093115 | −0.095258 | 0.02336 | −0.082377 | −0.027618 | −0.049883 | −0.106626 | −0.035519 | −0.004402 | −0.056115 | −0.049409 | 0.080822 | −0.034634 |
| 44 | 0.008279 | 0.072445 | 0.064937 | −0.061012 | −0.001288 | −0.030698 | 0.013567 | −0.000993 | −0.107818 | −0.045952 | 0.001883 | 0.056429 | 0.103895 | −0.058295 |
| 45 | −0.1653 | 0.019868 | −0.035866 | 0.084924 | 0.016963 | 0.003006 | −0.043789 | 0.013401 | 0.015606 | −0.005686 | −0.069401 | −0.002223 | −0.006903 | 0.029151 |
| 46 | 0.102081 | −0.080452 | 0.006405 | −0.017876 | 0.002868 | 0.038333 | 0.022134 | 0.045374 | 0.006954 | −0.007565 | 0.021113 | −0.048613 | −0.047379 | 0.002824 |
| 47 | −0.153266 | −0.109721 | −0.074925 | −0.096509 | 0.014059 | 0.023085 | 0.021877 | 0.009877 | −0.025387 | −0.025268 | 0.103117 | −0.007247 | −0.030409 | 0.111046 |
| 48 | 0.109139 | 0.072148 | 0.01753 | −0.075305 | −0.00557 | −0.007565 | −0.039812 | −0.001046 | 0.037688 | −0.02455 | 0.01677 | 0.012211 | −0.028998 | 0.070871 |
| 49 | 0.146857 | 0.055805 | 0.024126 | 0.031679 | 0.006177 | 0.035291 | 0.047123 | −0.001886 | 0.029342 | 0.082669 | 0.150617 | 0.052018 | 0.050507 | 0.144278 |
| 50 | 0.134062 | 0.079444 | −0.010493 | −0.021999 | 0.021051 | 0.026077 | −0.00701 | 0.026043 | 0.017018 | 0.000031 | 0.014104 | 0.014053 | −0.02368 | 0.016142 |
| 51 | −0.016567 | 0.166155 | 0.016532 | −0.027752 | 0.023096 | 0.07589 | 0.043752 | −0.014309 | −0.019382 | 0.000598 | 0.012385 | 0.001187 | 0.010698 | −0.0246 |
| 52 | −0.047112 | 0.118884 | −0.120304 | 0.008029 | 0.056447 | 0.127855 | 0.047426 | 0.058653 | 0.051943 | 0.015255 | −0.006675 | −0.022635 | 0.010791 | −0.001388 |
| 53 | 0.060053 | −0.036908 | 0.099008 | −0.034011 | 0.012103 | 0.022671 | −0.003542 | 0.009143 | 0.026211 | 0.011424 | −0.035547 | −0.05895 | 0.02538 | 0.029243 |
| 54 | −0.093952 | 0.064452 | 0.102708 | 0.002645 | −0.016293 | 0.005111 | 0.05761 | −0.002886 | −0.001822 | −0.029297 | −0.030171 | −0.003017 | −0.057268 | −0.009768 |
| 55 | 0.081964 | 0.049129 | 0.005269 | 0.041954 | 0.008506 | 0.001021 | 0.031698 | −0.028725 | 0.026788 | 0.009716 | 0.059136 | 0.003986 | 0.020569 | 0.022724 |
| 56 | −0.199499 | −0.027273 | 0.002983 | −0.013627 | −0.014156 | −0.008428 | 0.007241 | −0.026739 | −0.040767 | −0.054253 | −0.018087 | 0.107985 | −0.159016 | 0.00083 |
| 57 | −0.093522 | −0.016989 | 0.024518 | −0.022823 | 0.051001 | 0.032664 | 0.120024 | −0.003604 | 0.007615 | −0.055414 | −0.055108 | −0.018579 | 0.101443 | 0.1019 |
| 58 | 0.011898 | −0.020395 | −0.092649 | 0.10272 | 0.002519 | 0.0111 | 0.001165 | 0.038415 | 0.102692 | 0.082351 | −0.040286 | −0.002245 | −0.03753 | 0.049512 |
| 59 | −0.049794 | −0.034645 | −0.01909 | 0.069752 | 0.062568 | 0.104371 | −0.042301 | −0.008561 | 0.036252 | 0.082973 | 0.070202 | −0.011954 | 0.041415 | −0.01649 |
| 60 | −0.061431 | −0.022139 | 0.000201 | 0.019329 | 0.030829 | 0.013631 | 0.023517 | 0.023443 | −0.002546 | −0.011012 | 0.007464 | −0.005448 | −0.01678 | 0.000137 |
| 61 | 0.01149 | −0.010388 | 0.009943 | 0.017005 | 0.007267 | −0.004674 | 0.026856 | 0.013005 | 0.007011 | −0.002285 | −0.002873 | 0.017536 | 0.012188 | −0.004762 |
| 62 | −0.004496 | −0.02415 | −0.02896 | −0.012348 | 0.020777 | 0.024774 | 0.002556 | 0.029432 | 0.010225 | −0.00514 | 0.029812 | 0.02101 | −0.021126 | 0.005861 |
| 63 | 0.017968 | 0.01167 | 0.027398 | −0.034407 | −0.008143 | −0.019925 | 0.01713 | −0.001269 | −0.012929 | −0.013651 | 0.008173 | 0.003408 | 0.007653 | −0.006113 |
| 64 | 0.034588 | −0.004067 | −0.010041 | 0.005288 | −0.039612 | −0.028061 | −0.002951 | −0.018305 | 0.001367 | −0.014348 | −0.002846 | 0.000277 | 0.015015 | 0.02666 |
| 65 | −0.029314 | 0.03051 | 0.011664 | 0.019831 | 0.016869 | 0.014615 | 0.013855 | 0.011636 | −0.005664 | 0.009645 | 0.012331 | 0.011113 | −0.017173 | 0.001082 |
| 66 | −0.046407 | −0.015448 | 0.012777 | 0.016453 | −0.008989 | −0.016763 | 0.009539 | 0.016099 | −0.008923 | −0.006583 | −0.009864 | −0.000233 | 0.034263 | −0.0345 |
| 67 | 0.020177 | 0.025467 | −0.006212 | −0.032214 | −0.007558 | −0.034454 | 0.00505 | 0.014188 | −0.003428 | −0.000266 | 0.002191 | 0.003642 | −0.013068 | −0.031343 |
| 68 | 0.010972 | 0.036917 | −0.035942 | −0.03617 | 0.018789 | 0.003811 | −0.006998 | 0.006415 | −0.020015 | −0.031121 | −0.007087 | −0.024528 | −0.036967 | 0.012544 |
| 69 | −0.02131 | 0.016742 | −0.008174 | 0.007101 | 0.019647 | 0.017295 | 0.003083 | 0.011125 | 0.015408 | 0.00388 | −0.002336 | 0.031983 | 0.000629 | 0.00469 |
| 70 | −0.021101 | 0.014506 | 0.019887 | −0.000525 | 0.020702 | 0.003374 | −0.00215 | 0.020261 | 0.008036 | −0.008892 | −0.039267 | 0.001933 | −0.008521 | 0.001121 |
| 71 | −0.010682 | 0.021224 | −0.000166 | 0.005122 | −0.02535 | −0.021987 | −0.022105 | −0.010854 | −0.016259 | −0.003938 | 0.017022 | −0.004669 | 0.013234 | −0.00894 |
| 72 | −0.011911 | 0.032701 | −0.015524 | −0.001356 | 0.004661 | 0.004336 | 0.002159 | −0.017334 | −0.008548 | 0.00894 | 0.046577 | −0.000932 | 0.007304 | 0.005218 |
| 73 | 0.01342 | 0.000813 | 0.00003 | −0.027544 | 0.001196 | 0.009348 | −0.012827 | 0.008679 | −0.007261 | −0.016224 | 0.00295 | 0.012627 | −0.042464 | −0.018344 |
| 74 | 0.021177 | −0.010987 | −0.017518 | 0.025091 | −0.000419 | 0.006725 | −0.00474 | −0.02341 | −0.024749 | 0.004615 | 0.037633 | −0.022802 | −0.005026 | 0.014266 |
| 75 | 0.002749 | 0.008898 | 0.013685 | −0.007211 | 0.009446 | 0.004649 | 0.001699 | 0.018336 | −0.003301 | −0.005816 | 0.008448 | 0.006148 | −0.006735 | 0.00133 |
| 76 | −0.008541 | 0.02439 | 0.020546 | 0.006956 | −0.001376 | −0.009941 | 0.002749 | 0.004022 | 0.005021 | 0.001178 | −0.020302 | −0.0151 | 0.014485 | 0.005683 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 77 | −0.005659 | 0.019126 | 0.018439 | −0.001834 | 0.008358 | 0.00136 | −0.003657 | 0.014102 | −0.005158 | −0.006281 | −0.003754 | 0.011809 | −0.002535 | −0.006987 |
| 78 | 0.023601 | 0.016419 | 0.016703 | 0.00067 | 0.009236 | 0.005894 | −0.011593 | 0.015339 | 0.0029 | −0.008359 | −0.00038 | 0.008617 | −0.009423 | −0.007626 |
| 79 | −0.002433 | −0.002698 | 0.016861 | 0.000544 | 0.019223 | 0.02409 | 0.015661 | 0.024053 | 0.001421 | −0.006251 | −0.010831 | −0.006878 | 0.014004 | 0.029377 |
| 80 | −0.038004 | −0.016679 | −0.004379 | 0.043179 | −0.037775 | −0.029299 | −0.011137 | −0.014535 | 0.021442 | −0.000133 | −0.013133 | 0.007569 | −0.020363 | −0.033518 |
| 81 | −0.043406 | 0.006425 | −0.003719 | 0.006796 | −0.002862 | −0.010301 | 0.004887 | −0.028249 | −0.016644 | 0.006293 | −0.018743 | −0.011107 | 0.038184 | −0.000229 |
| 82 | −0.003415 | 0.025243 | −0.016708 | 0.023352 | 0.000453 | −0.001492 | −0.009129 | 0.005462 | 0.011084 | −0.00394 | −0.018985 | −0.039198 | 0.023679 | 0.005394 |
| 83 | 0.017872 | 0.022758 | 0.004032 | 0.010818 | −0.008639 | −0.00922 | −0.010818 | −0.000968 | 0.008363 | −0.005432 | −0.009571 | −0.028328 | 0.022172 | 0.0086 |
| 84 | 0.009985 | 0.012597 | 0.003376 | 0.024182 | −0.010802 | −0.00374 | −0.007482 | −0.002314 | 0.007447 | −0.000676 | −0.009729 | −0.013085 | −0.004368 | −0.005773 |
| 85 | 0.002909 | −0.003702 | 0.030055 | −0.011153 | 0.015492 | 0.012821 | 0.027246 | 0.00164 | −0.009082 | 0.013808 | 0.012486 | 0.025161 | 0.099503 | 0.056088 |
| 86 | −0.033585 | 0.005806 | −0.020091 | 0.004627 | −0.007881 | −0.011088 | −0.002629 | −0.006603 | −0.005592 | 0.002037 | 0.027065 | 0.020816 | 0.008081 | −0.002665 |
| 87 | −0.01801 | 0.013031 | −0.011453 | 0.006013 | −0.00478 | 0.000828 | 0.022534 | 0.010438 | 0.010409 | 0.003874 | 0.009347 | 0.000961 | −0.002373 | −0.010962 |
| 88 | 0.009161 | −0.001807 | 0.006941 | 0.011856 | −0.01743 | −0.014847 | −0.024345 | 0.000895 | 0.014452 | −0.004511 | −0.017111 | −0.019412 | −0.000071 | −0.00800 |
| 89 | 0.036837 | 0.016612 | −0.005269 | 0.016389 | −0.007443 | −0.002842 | −0.021913 | −0.001464 | 0.014845 | −0.005787 | −0.005241 | −0.018039 | −0.004423 | 0.001559 |
| 90 | 0.021026 | 0.02349 | −0.015915 | 0.019929 | −0.0106f | −0.00943 | −0.007318 | −0.005987 | 0.007389 | −0.005868 | 0.002946 | −0.01338f | −0.00757 | 0.005885 |
| 91 | 0.021623 | 0.01654 | −0.030869 | 0.027045 | −0.006932 | −0.00388 | −0.004005 | −0.009007 | 0.001208 | −0.013584 | 0.000457 | −0.003047 | −0.008238 | 0.017536 |
| 92 | 0.025944 | 0.008944 | −0.026227 | 0.024531 | 0.008671 | 0.015871 | −0.000618 | 0.013468 | 0.019255 | 0.009045 | −0.026372 | 0.012576 | 0.002985 | −0.024855 |
| 93 | 0.02298 | 0.043577 | 0.004488 | 0.006692 | −0.006365 | −0.01915 | −0.000476 | −0.006369 | 0.001028 | −0.01632 | 0.000387 | 0.00193 | 0.014041 | 0.010344 |
| 94 | −0.003384 | −0.036455 | −0.003184 | −0.005082 | −0.006331 | −0.025126 | −0.019827 | 0.007053 | 0.001458 | −0.007079 | −0.006034 | −0.02384 | 0.020782 | −0.015641 |
| 95 | −0.008527 | −0.009598 | −0.041462 | −0.010418 | 0.01523 | 0.020456 | 0.009127 | −0.022968 | −0.024228 | −0.023924 | −0.016684 | −0.022996 | −0.035268 | 0.000852 |
| 96 | −0.069522 | −0.060991 | 0.036098 | −0.025354 | 0.005547 | −0.000098 | −0.000257 | 0.013196 | 0.007935 | 0.009635 | −0.01028 | −0.046013 | 0.015508 | 0.026314 |
| 97 | 0.017849 | −0.002659 | 0.019357 | −0.001838 | 0.000864 | −0.0023051 | 0.025001 | −0.004966 | 0.011851 | 0.002661 | 0.007978 | −0.009451 | 0.019473 | 0.011951 |
| 98 | 0.010513 | −0.008617 | −0.021886 | −0.000064 | −0.027457 | −0.024395 | −0.010504 | 0.002482 | 0.007369 | 0.018399 | 0.015398 | −0.013772 | 0.013307 | −0.041277 |
| 99 | −0.01665 | 0.006587 | 0.000532 | −0.006101 | 0.018074 | 0.019311 | 0.015151 | 0.004225 | 0.002804 | 0.015447 | 0.018945 | −0.002329 | 0.00395 | 0.012117 |
| 100 | 0.033301 | 0.014794 | −0.002817 | −0.02929 | 0.012718 | 0.014593 | −0.003963 | 0.011367 | 0.022201 | 0.033358 | 0.029399 | −0.031552 | 0.008678 | −0.020643 |
| 101 | 0.037865 | −0.013831 | −0.013712 | 0.015314 | −0.041619 | −0.048956 | −0.016649 | −0.000031 | 0.006818 | 0.010908 | 0.015986 | −0.008181 | 0.00813 | −0.032527 |
| 102 | −0.012276 | 0.039417 | 0.026233 | −0.026226 | 0.028693 | 0.033874 | 0.040056 | −0.028726 | −0.041274 | −0.035295 | −0.03537 | −0.011377 | 0.000181 | −0.000297 |
| 103 | 0.03874 | −0.009105 | −0.011135 | −0.003767 | −0.014886 | −0.007072 | 0.007524 | −0.033887 | −0.029882 | −0.012484 | −0.023874 | −0.000261 | −0.03897 | −0.027254 |
| 104 | −0.009225 | 0.024651 | −0.037302 | 0.033657 | 0.000881 | 0.027563 | 0.018139 | −0.015407 | −0.00357 | −0.000635 | 0.015105 | 0.020542 | −0.044628 | −0.004656 |
| 105 | −0.023304 | 0.004504 | 0.028413 | −0.013946 | −0.010403 | 0.006266 | −0.052487 | 0.02575 | 0.014183 | 0.039134 | 0.006063 | −0.006329 | 0.00658 | −0.02419 |
| 106 | 0.005312 | −0.020237 | −0.001324 | −0.007567 | −0.008562 | −0.005413 | 0.020084 | −0.009915 | −0.014828 | −0.033157 | −0.034129 | 0.003756 | −0.024209 | −0.031238 |
| 107 | −0.007956 | 0.01965 | 0.026439 | −0.021551 | −0.009345 | −0.017459 | −0.020669 | 0.005583 | 0.022065 | 0.009623 | 0.004639 | −0.027592 | 0.011641 | −0.026419 |
| 108 | 0.046987 | −0.038658 | −0.019304 | 0.028964 | −0.010095 | −0.00385 | −0.0128 | −0.015068 | 0.014526 | −0.006085 | 0.000226 | −0.02081 | −0.012517 | 0.02933 |
| 109 | −0.015283 | −0.069164 | −0.036982 | 0.02937 | 0.020785 | 0.034238 | 0.020023 | 0.003206 | −0.010645 | −0.012908 | 0.009579 | 0.003629 | −0.001346 | 0.028023 |
| 110 | 0.058907 | 0.009648 | 0.010129 | 0.027757 | 0.001746 | 0.003946 | 0.018112 | 0.01715 | 0.01021 | −0.010011 | 0.015852 | 0.032038 | 0.016456 | 0.00274 |
| 111 | −0.026326 | 0.002854 | −0.013398 | 0.053904 | 0.01485 | 0.037999 | 0.009663 | 0.015682 | 0.002496 | −0.001825 | 0.000506 | −0.044897 | 0.002483 | 0.008444 |
| 112 | 0.00575 | −0.019422 | 0.043345 | −0.009557 | −0.016914 | −0.019402 | −0.014974 | −0.014505 | 0.013704 | 0.010098 | −0.03786 | 0.015636 | 0.003033 | −0.004811 |
| 113 | −0.004473 | −0.050025 | −0.069611 | 0.0179 | 0.014281 | 0.033985 | 0.02594 | 0.005412 | −0.00302 | −0.024872 | −0.053499 | −0.011799 | 0.019593 | 0.00126 |
| 114 | 0.044425 | −0.03289 | −0.020033 | 0.005184 | −0.031687 | −0.045716 | −0.032545 | −0.044104 | −0.011534 | −0.006337 | −0.002937 | 0.044416 | 0.021056 | 0.050691 |
| 115 | −0.000233 | 0.041163 | −0.028773 | −0.016039 | 0.002685 | −0.001396 | −0.001579 | −0.014207 | −0.037468 | −0.025815 | −0.00434 | 0.007426 | −0.032674 | 0.004456 |
| 116 | 0.059848 | 0.022054 | 0.029128 | 0.027712 | −0.002094 | −0.013207 | −0.01222 | 0.0002 | 0.017656 | 0.008657 | 0.016918 | −0.029099 | 0.012297 | 0.021665 |
| 117 | −0.018931 | −0.028822 | 0.025514 | 0.02997 | −0.015504 | 0.002664 | 0.008549 | −0.017494 | 0.014728 | 0.059426 | −0.016986 | −0.02427 | −0.011647 | 0.025504 |
| 118 | −0.03928 | 0.019619 | −0.029683 | −0.039494 | 0.014641 | 0.029156 | −0.002073 | 0.015005 | 0.021132 | 0.037441 | 0.000674 | 0.002756 | 0.019386 | 0.008414 |
| 119 | −0.0151 | −0.034457 | −0.028811 | −0.015662 | −0.002162 | −0.006017 | −0.009599 | −0.021186 | 0.018894 | 0.010305 | 0.003254 | −0.006615 | −0.044535 | 0.002763 |
| 120 | 0.025723 | 0.000604 | −0.006509 | 0.017389 | −0.027468 | −0.005024 | −0.019237 | −0.040501 | −0.008701 | 0.001655 | −0.032428 | −0.030933 | −0.029623 | 0.007257 |
| 121 | −0.029663 | 0.03903 | −0.000444 | −0.015186 | 0.006992 | 0.019436 | −0.038198 | 0.000409 | −0.02833 | 0.008426 | 0.018056 | 0.005224 | 0.010869 | 0.009628 |
| 122 | −0.014889 | −0.004801 | 0.006948 | −0.010802 | 0.010043 | 0.01331 | 0.009112 | 0.011054 | 0.000411 | 0.005866 | −0.03675 | 0.012086 | 0.040123 | −0.000113 |
| 123 | 0.001958 | 0.012731 | −0.018268 | 0.005424 | 0.005729 | 0.009628 | −0.027967 | 0.000822 | 0.0043 | 0.020446 | −0.017669 | −0.000559 | 0.045248 | −0.001884 |
| 124 | 0.017094 | −0.054532 | −0.004331 | −0.011311 | −0.005798 | −0.011578 | −0.009808 | −0.012311 | 0.028787 | 0.016287 | −0.00784 | −0.011875 | −0.029641 | −0.00165 |
| 125 | −0.047404 | 0.019125 | −0.022394 | 0.013307 | −0.009134 | 0.021574 | 0.015414 | −0.020906 | −0.029131 | −0.012479 | −0.034956 | −0.002186 | 0.039722 | −0.004401 |
| 126 | −0.038082 | 0.013796 | −0.009068 | 0.007199 | 0.009965 | 0.022713 | −0.019697 | 0.011144 | −0.015018 | 0.022039 | −0.002611 | 0.027531 | −0.0005 | −0.029194 |

APPENDIX B3-continued

PCA Transformation
Matrix (340 × 340 Early/Late)

| | | | | | | | | | | | | | |
|---|---|---|---|---|---|---|---|---|---|---|---|---|---|
| 127 | −0.019811 | 0.037174 | −0.010954 | −0.023395 | −0.002283 | 0.00375 | −0.005307 | 0.004938 | −0.015743 | 0.004786 | −0.022061 | 0.009265 | −0.001694 | −0.025523 |
| 128 | −0.02833 | 0.013253 | −0.027085 | −0.007432 | 0.003612 | 0.006548 | −0.009688 | −0.013708 | −0.005904 | −0.001727 | 0.00742 | −0.007985 | 0.000163 | −0.015692 |
| 129 | −0.070261 | −0.042329 | 0.008101 | −0.004079 | −0.003745 | −0.003701 | 0.000554 | −0.008302 | −0.032039 | −0.004223 | −0.013772 | 0.067459 | 0.073982 | −0.021696 |
| 130 | 0.008405 | −0.020969 | −0.019391 | −0.04563 | −0.034143 | −0.055237 | −0.044999 | −0.01978 | −0.02551 | −0.047945 | −0.039605 | −0.028794 | −0.051543 | −0.011192 |
| 131 | 0.002265 | 0.009382 | 0.041264 | −0.021549 | −0.016065 | −0.032944 | −0.029627 | 0.029857 | 0.034538 | 0.029846 | 0.004289 | −0.051535 | 0.027203 | 0.014214 |
| 132 | 0.00598 | 0.021504 | −0.035667 | 0.022706 | −0.026746 | −0.011772 | −0.036983 | −0.020098 | 0.021066 | 0.006415 | −0.003373 | −0.037513 | 0.021465 | −0.000045 |
| 133 | −0.061949 | −0.024765 | −0.032574 | −0.018828 | −0.006131 | −0.004181 | 0.01278 | −0.005724 | −0.017113 | 0.011713 | 0.048013 | −0.0356 | 0.000091 | −0.021909 |
| 134 | 0.017753 | 0.047014 | 0.022493 | 0.019648 | 0.018946 | 0.002465 | 0.015913 | 0.013214 | 0.010901 | 0.014814 | 0.001051 | 0.050508 | −0.014475 | 0.015204 |
| 135 | −0.013896 | −0.006636 | −0.023872 | 0.011961 | −0.012235 | 0.002088 | −0.009334 | −0.019424 | 0.004169 | −0.001473 | −0.00516 | −0.011784 | −0.009461 | −0.003887 |
| 136 | −0.016345 | −0.010519 | −0.050197 | 0.000387 | 0.01663 | 0.009716 | 0.014391 | 0.018044 | 0.008736 | 0.011726 | 0.006978 | −0.028426 | 0.003117 | 0.019376 |
| 137 | 0.015996 | 0.020966 | −0.032844 | −0.029577 | 0.005736 | 0.014143 | 0.0099 | −0.006401 | −0.021596 | −0.011758 | −0.021332 | −0.003209 | 0.035885 | −0.055792 |
| 138 | 0.005598 | −0.077748 | 0.009877 | −0.012053 | −0.01557 | −0.030693 | −0.012989 | 0.011941 | 0.025794 | 0.006962 | 0.034779 | −0.019247 | −0.02475 | 0.011587 |
| 139 | 0.01394 | 0.027218 | −0.031816 | 0.033319 | −0.01788 | −0.015706 | −0.037668 | −0.028222 | −0.035919 | −0.025229 | −0.044514 | −0.018272 | 0.003718 | −0.049703 |
| 140 | 0.014866 | −0.014074 | −0.026037 | 0.02396 | 0.009539 | 0.004023 | 0.006197 | 0.020826 | 0.028578 | 0.023688 | 0.048162 | 0.05602 | 0.005824 | 0.007433 |
| 141 | −0.005775 | −0.003473 | −0.01269 | −0.026233 | −0.002766 | −0.005152 | −0.039852 | −0.002215 | 0.012097 | 0.007232 | 0.010359 | −0.012616 | 0.000876 | −0.015349 |
| 142 | 0.028699 | −0.067973 | 0.002863 | −0.015748 | −0.001863 | 0.002734 | 0.007881 | 0.015818 | 0.008789 | 0.017828 | 0.022509 | 0.033964 | 0.044907 | 0.036066 |
| 143 | −0.002045 | 0.007214 | −0.027949 | −0.006368 | −0.011773 | −0.00654 | 0.000306 | 0.003931 | 0.014246 | 0.005557 | 0.004043 | 0.00383 | 0.053239 | 0.015472 |
| 144 | −0.033641 | −0.044783 | −0.049136 | −0.006057 | 0.006554 | −0.005068 | 0.005065 | 0.000333 | 0.013145 | −0.006291 | 0.019896 | 0.019595 | −0.013174 | 0.009897 |
| 145 | −0.022674 | 0.013204 | −0.073217 | 0.012145 | −0.012413 | −0.013619 | 0.022448 | −0.010904 | −0.006096 | −0.011236 | −0.014851 | 0.028278 | 0.035134 | 0.010732 |
| 146 | −0.014002 | 0.011282 | −0.021582 | 0.012271 | −0.019785 | −0.006305 | −0.010589 | −0.021129 | 0.003343 | 0.000988 | −0.018505 | −0.018068 | 0.006964 | −0.007298 |
| 147 | 0.078254 | 0.011068 | −0.009334 | 0.003126 | −0.016567 | −0.007629 | −0.004338 | −0.011284 | 0.009636 | 0.013357 | 0.006254 | 0.018094 | −0.028574 | −0.009615 |
| 148 | −0.023523 | −0.057174 | 0.003968 | 0.007442 | 0.007545 | 0.001116 | 0.032899 | 0.004689 | −0.010571 | −0.000662 | −0.018643 | −0.015848 | −0.002389 | −0.027386 |
| 149 | −0.055808 | 0.018613 | −0.021748 | −0.010016 | −0.002368 | 0.003875 | −0.011045 | −0.006793 | −0.022381 | −0.010472 | −0.022478 | −0.006415 | 0.041405 | 0.009696 |
| 150 | 0.06685 | 0.025889 | −0.014599 | 0.016309 | −0.022662 | −0.002391 | 0.002316 | −0.02235 | 0.005363 | 0.004949 | −0.050554 | 0.002435 | 0.005967 | −0.019321 |
| 151 | −0.032554 | −0.013526 | 0.00984 | 0.015937 | 0.029066 | 0.029147 | 0.035149 | −0.03405 | −0.001655 | 0.003916 | −0.028339 | 0.043521 | −0.05193 | −0.011997 |
| 152 | −0.053604 | 0.02342 | 0.002411 | −0.013766 | 0.006469 | 0.004747 | −0.010593 | 0.010009 | −0.005281 | 0.009831 | −0.012556 | 0.007942 | 0.030676 | 0.007831 |
| 153 | −0.024596 | −0.00333 | 0.009723 | −0.007077 | 0.001023 | 0.003403 | −0.017713 | 0.000884 | −0.009525 | 0.00258 | 0.000286 | 0.023809 | 0.009714 | 0.011728 |
| 154 | 0.004861 | −0.00946 | −0.006231 | 0.009275 | 0.011574 | 0.011535 | 0.01767 | 0.020321 | 0.003402 | −0.005121 | 0.020579 | 0.008985 | 0.001857 | 0.030539 |
| 155 | −0.100594 | 0.022281 | −0.041675 | 0.03555 | −0.016674 | −0.005545 | −0.010804 | −0.014627 | −0.017731 | −0.028401 | −0.028507 | −0.003844 | 0.011466 | 0.008347 |
| 156 | −0.012234 | 0.024259 | −0.043629 | −0.01201 | −0.000464 | −0.005797 | −0.006007 | −0.004473 | 0.008635 | 0.00678 | 0.036797 | −0.051837 | −0.030988 | 0.025857 |
| 157 | −0.009219 | −0.013543 | −0.022735 | 0.022931 | −0.010594 | 0.009423 | 0.009904 | −0.016326 | 0.006224 | 0.014348 | −0.010261 | −0.010252 | 0.008009 | −0.009878 |
| 158 | 0.034197 | −0.00657 | −0.018641 | 0.016716 | 0.009204 | 0.011764 | −0.000263 | −0.030658 | −0.020139 | −0.037228 | 0.017664 | −0.025421 | −0.06187 | 0.000686 |
| 159 | 0.073279 | −0.003076 | −0.00049 | 0.014662 | 0.014334 | 0.019051 | 0.007846 | −0.001905 | 0.008847 | 0.020394 | 0.027052 | 0.033384 | −0.000956 | −0.026202 |
| 160 | −0.054815 | −0.055139 | 0.044776 | −0.022084 | 0.031067 | 0.026986 | 0.040153 | 0.012366 | −0.021089 | 0.008766 | −0.028148 | 0.040461 | 0.02071 | −0.004735 |
| 161 | −0.025818 | 0.025542 | 0.027431 | 0.015054 | −0.008042 | −0.011833 | −0.032383 | −0.02562 | −0.016573 | −0.030399 | −0.033342 | −0.018179 | 0.012211 | −0.013289 |
| 162 | 0.017663 | −0.013022 | −0.011552 | −0.022964 | −0.00672 | −0.016288 | 0.001025 | 0.002224 | 0.002209 | 0.005822 | −0.00671 | 0.002279 | 0.028336 | 0.001037 |
| 163 | −0.005877 | 0.018321 | 0.003232 | −0.037338 | 0.002456 | 0.011591 | 0.018476 | 0.005108 | 0.00162 | 0.001841 | −0.018671 | −0.000295 | 0.034003 | −0.002421 |
| 164 | −0.030123 | −0.061358 | −0.055076 | −0.038344 | 0.024084 | 0.021877 | 0.033164 | 0.014079 | 0.020402 | 0.016121 | −0.003017 | 0.007126 | −0.022756 | 0.005007 |
| 165 | 0.607301 | −0.030886 | −0.0076 | 0.020956 | 0.009521 | 0.007546 | 0.00926 | −0.013715 | −0.063621 | −0.012159 | −0.057839 | −0.031834 | 0.055129 | −0.020453 |
| 166 | −0.035427 | 0.712257 | 0.000819 | 0.052996 | −0.007415 | −0.015559 | 0.010838 | −0.00649 | 0.015353 | 0.012205 | 0.009667 | 0.0063 | −0.043694 | 0.025736 |
| 167 | −0.010744 | −0.006729 | 0.832004 | 0.023159 | −0.006505 | 0.011914 | −0.003115 | −0.005977 | 0.007056 | −0.010909 | 0.025946 | −0.008207 | −0.036625 | −0.01249 |
| 168 | 0.02399 | 0.047049 | 0.027634 | 0.833863 | 0.004068 | −0.00189 | −0.022328 | −0.003151 | −0.017549 | −0.035101 | −0.00476 | −0.01047 | 0.007345 | −0.005917 |
| 169 | 0.011023 | −0.007497 | −0.000386 | −0.002008 | 0.91021 | −0.092171 | −0.062838 | −0.040231 | −0.008292 | −0.021929 | −0.051312 | −0.042122 | 0.001508 | −0.016108 |
| 170 | 0.005172 | −0.013587 | 0.028814 | −0.014812 | −0.093673 | 0.868533 | −0.075401 | −0.036921 | −0.011513 | −0.023678 | −0.043651 | −0.045711 | −0.000727 | −0.011401 |
| 171 | −0.007119 | 0.007634 | 0.007573 | −0.024027 | −0.065148 | −0.073391 | 0.889806 | −0.02528 | −0.004462 | −0.007906 | −0.026654 | −0.040969 | 0.011304 | −0.020243 |
| 172 | −0.017978 | −0.005738 | −0.004445 | 0.010505 | −0.027674 | −0.018873 | −0.015684 | 0.90691 | −0.048831 | −0.044756 | −0.065037 | −0.02648 | −0.021349 | 0.001533 |
| 173 | −0.057443 | 0.01757 | 0.016276 | −0.017486 | −0.000759 | 0.004858 | −0.001566 | −0.050839 | 0.894947 | −0.073652 | −0.055596 | 0.005703 | 0.02731 | −0.009208 |
| 174 | −0.005314 | 0.016789 | −0.000903 | −0.02392 | −0.009141 | −0.005511 | −0.006242 | −0.049845 | −0.074831 | 0.873662 | −0.095852 | −0.002652 | −0.013161 | −0.000449 |
| 175 | −0.05615 | 0.021716 | 0.014584 | 0.015472 | −0.022748 | −0.017813 | −0.010097 | −0.052418 | −0.043557 | −0.082356 | 0.771428 | −0.053895 | 0.02791 | −0.025545 |
| 176 | −0.026368 | 0.022023 | −0.009116 | −0.019194 | −0.027513 | −0.037327 | −0.046024 | −0.02475 | 0.006437 | 0.000839 | −0.036572 | 0.848243 | 0.020594 | −0.009312 |

APPENDIX B3-continued

PCA Transformation
Matrix (340 × 340 Early/Late)

| | | | | | | | | | | | | | |
|---|---|---|---|---|---|---|---|---|---|---|---|---|---|
| 177 | 0.060207 | −0.012213 | −0.04309 | −0.003201 | −0.00471 | −0.000762 | −0.003946 | −0.034074 | 0.008236 | −0.032181 | 0.029671 | 0.018684 | 0.734474 | −0.025034 |
| 178 | −0.007527 | 0.015892 | −0.010807 | −0.007806 | −0.025034 | −0.018611 | −0.019835 | −0.006544 | −0.016126 | −0.003 | −0.026082 | −0.00088 | −0.028418 | 0.880842 |
| 179 | 0.008706 | −0.009018 | −0.015238 | −0.013036 | −0.029766 | −0.025486 | −0.022592 | 0.007049 | 0.014517 | 0.018321 | 0.018013 | −0.002665 | −0.012396 | −0.045589 |
| 180 | 0.010938 | −0.014467 | −0.004695 | −0.008353 | −0.028422 | −0.029665 | −0.022267 | 0.006503 | −0.001942 | 0.010155 | 0.017812 | −0.002243 | −0.002266 | −0.05078 |
| 181 | 0.011461 | −0.011842 | −0.007086 | 0.001138 | −0.029749 | −0.033591 | −0.020246 | 0.001175 | 0.001576 | 0.01198 | 0.019425 | −0.007558 | −0.008161 | −0.046437 |
| 182 | 0.017057 | −0.000018 | 0.011189 | −0.020252 | −0.005567 | −0.019647 | −0.014126 | −0.00052 | 0.005811 | 0.020509 | 0.02785 | −0.016387 | −0.021096 | −0.03548 |
| 183 | 0.000001 | 0.017601 | −0.007984 | −0.011931 | 0.00719 | 0.014837 | −0.037767 | 0.01194 | 0.02498 | 0.036047 | 0.035677 | −0.010746 | −0.008117 | −0.02893 |
| 184 | −0.004554 | −0.002661 | 0.002506 | 0.001038 | 0.010736 | 0.01958 | −0.035093 | −0.008013 | −0.00188 | −0.002936 | 0.024033 | −0.003819 | 0.053255 | −0.004164 |
| 185 | 0.002811 | −0.005418 | 0.029484 | −0.012788 | −0.000421 | 0.012537 | 0.019736 | −0.02555 | −0.006753 | −0.022649 | −0.029972 | −0.005213 | 0.000145 | 0.007369 |
| 186 | −0.008646 | −0.035436 | 0.021474 | −0.008102 | 0.030017 | 0.027244 | −0.002844 | −0.014604 | −0.016758 | −0.022106 | −0.004891 | 0.018959 | 0.004695 | 0.024216 |
| 187 | −0.006517 | 0.01263 | 0.016006 | −0.008348 | 0.019749 | 0.023117 | 0.033747 | −0.0198 | −0.045202 | −0.025478 | 0.002078 | 0.019752 | 0.001989 | −0.001072 |
| 188 | 0.008341 | 0.017582 | 0.01614 | −0.018793 | 0.014061 | 0.008713 | 0.024582 | −0.025715 | −0.039566 | −0.067043 | −0.024521 | 0.002469 | −0.011325 | 0.009589 |
| 189 | 0.073585 | 0.019075 | 0.021403 | −0.008515 | −0.000186 | −0.001819 | 0.008022 | −0.01531 | −0.001518 | −0.048695 | −0.068896 | −0.038673 | 0.015124 | 0.013712 |
| 190 | 0.003207 | −0.01256 | −0.028599 | 0.017089 | −0.007102 | −0.011545 | −0.013993 | 0.001747 | 0.017562 | 0.016233 | 0.000367 | −0.030217 | 0.016988 | −0.000848 |
| 191 | −0.002245 | −0.009731 | −0.016279 | 0.020263 | −0.018053 | −0.012203 | −0.014223 | −0.001959 | 0.021726 | 0.024175 | 0.026257 | −0.006348 | −0.010597 | 0.008976 |
| 192 | 0.020441 | 0.040024 | 0.001244 | −0.057939 | 0.017214 | 0.019519 | 0.006657 | 0.006735 | 0.010767 | 0.003691 | 0.025178 | 0.03642 | −0.020151 | −0.010971 |
| 193 | 0.002798 | 0.017878 | 0.026962 | −0.043866 | 0.022631 | 0.014685 | 0.006298 | −0.015434 | −0.022406 | −0.024087 | −0.016815 | −0.011167 | 0.012359 | 0.00317 |
| 194 | −0.019852 | 0.016984 | 0.017272 | −0.017044 | −0.009646 | 0.003353 | 0.002387 | −0.038869 | −0.025709 | −0.027937 | −0.075308 | −0.027333 | 0.026917 | −0.008211 |
| 195 | 0.001921 | −0.026384 | −0.006526 | 0.044033 | 0.014098 | 0.016328 | 0.030288 | −0.032914 | −0.009349 | 0.005121 | 0.006824 | −0.007446 | 0.022461 | 0.028106 |
| 196 | 0.023292 | −0.022252 | −0.012045 | 0.032194 | −0.001332 | −0.004661 | 0.014607 | −0.024066 | 0.003048 | −0.007548 | −0.029435 | −0.008967 | 0.005564 | 0.005802 |
| 197 | −0.008422 | 0.022168 | −0.026319 | 0.003396 | −0.00389 | −0.012506 | −0.008162 | −0.003917 | 0.020274 | 0.017126 | 0.013998 | −0.028939 | 0.005861 | 0.025554 |
| 198 | −0.028253 | −0.001769 | 0.017415 | 0.011601 | 0.005206 | −0.002485 | 0.004974 | −0.052311 | −0.004127 | 0.01028 | −0.02299 | −0.023093 | −0.04478 | −0.017897 |
| 199 | 0.010665 | −0.030482 | −0.045497 | −0.035476 | −0.028694 | −0.003214 | −0.008176 | −0.008296 | −0.005928 | −0.026395 | −0.044101 | −0.015403 | 0.030331 | −0.01792 |
| 200 | −0.036436 | −0.031388 | −0.027461 | 0.013169 | 0.020957 | 0.033863 | 0.003938 | −0.042091 | −0.003385 | 0.008342 | 0.001987 | 0.024398 | −0.06047 | −0.039599 |
| 201 | −0.044499 | 0.058435 | 0.013224 | −0.020918 | −0.012056 | −0.007349 | −0.026648 | 0.032243 | 0.011115 | 0.039488 | 0.052933 | −0.056491 | 0.031288 | −0.023521 |
| 202 | −0.089152 | −0.017965 | 0.007185 | −0.002434 | 0.013435 | 0.00522 | 0.007711 | −0.046038 | −0.033446 | −0.003115 | −0.028274 | 0.008396 | −0.015072 | −0.019616 |
| 203 | −0.014205 | 0.025884 | −0.014031 | −0.009371 | −0.022907 | −0.019321 | −0.00626 | −0.011496 | 0.005568 | 0.014168 | 0.000109 | 0.010243 | −0.031117 | −0.010061 |
| 204 | −0.056942 | 0.008009 | −0.018166 | 0.013103 | 0.004093 | 0.009059 | −0.004239 | −0.027841 | −0.010607 | 0.025254 | 0.031461 | −0.03043 | 0.028066 | 0.006097 |
| 205 | −0.026812 | −0.019933 | −0.023348 | 0.007692 | 0.038315 | 0.060821 | 0.051626 | 0.010447 | 0.002554 | 0.033015 | 0.014598 | −0.006288 | 0.055349 | −0.005018 |
| 206 | 0.057109 | 0.012589 | −0.040392 | 0.005705 | 0.003244 | 0.008991 | 0.012154 | 0.003126 | 0.010028 | 0.004904 | 0.028334 | 0.023602 | −0.001502 | 0.02276 |
| 207 | −0.021503 | 0.031372 | −0.06244 | −0.036807 | 0.015288 | 0.015926 | 0.011602 | −0.001721 | 0.004604 | −0.007195 | −0.026871 | −0.039465 | −0.046089 | −0.025062 |
| 208 | −0.063265 | 0.00233 | −0.024643 | 0.023268 | −0.028487 | −0.040072 | −0.010782 | −0.016028 | −0.000231 | 0.002929 | 0.004313 | −0.015377 | −0.023412 | 0.037484 |
| 209 | −0.021663 | −0.053487 | 0.039769 | −0.014462 | −0.002179 | −0.005448 | −0.003137 | −0.039104 | −0.029216 | −0.011946 | 0.00018 | −0.023648 | 0.003567 | 0.003957 |
| 210 | 0.020676 | 0.01219 | −0.009131 | 0.046735 | 0.004345 | 0.038473 | 0.00206 | 0.007345 | 0.017989 | 0.031364 | −0.02769 | −0.031868 | −0.047495 | −0.041512 |
| 211 | 0.007148 | −0.008316 | −0.013562 | 0.034348 | −0.003824 | 0.011097 | 0.002535 | −0.018717 | −0.040276 | 0.002828 | 0.037971 | 0.042805 | 0.000545 | −0.012819 |
| 212 | 0.025275 | −0.048245 | 0.002614 | 0.033364 | −0.008472 | −0.022858 | 0.009043 | −0.016463 | 0.013767 | 0.012512 | 0.016408 | −0.011645 | 0.015205 | 0.027221 |
| 213 | −0.000845 | −0.027496 | 0.009725 | 0.024506 | 0.020098 | 0.021822 | 0.022944 | 0.020736 | 0.026346 | 0.019825 | 0.002043 | 0.046886 | −0.04376 | −0.05194 |
| 214 | 0.040779 | −0.009329 | −0.002811 | −0.008962 | −0.015313 | −0.008669 | −0.02744 | 0.00857 | 0.013016 | 0.024846 | 0.027313 | 0.00006 | 0.012582 | −0.033865 |
| 215 | −0.010109 | −0.022051 | 0.003983 | 0.000283 | −0.023316 | 0.016085 | −0.008809 | 0.002822 | 0.022554 | 0.015688 | −0.004634 | 0.003204 | −0.000989 | −0.04518 |
| 216 | 0.024079 | 0.027397 | −0.002109 | −0.075172 | −0.015678 | −0.007555 | −0.040975 | 0.000951 | 0.001975 | −0.027517 | −0.025725 | −0.013992 | −0.004869 | −0.010483 |
| 217 | 0.036264 | 0.016166 | −0.003615 | −0.002681 | −0.006773 | 0.013257 | 0.004466 | −0.016104 | 0.023454 | 0.009382 | −0.032586 | −0.002466 | 0.002684 | 0.027028 |
| 218 | 0.019729 | 0.017772 | 0.015897 | 0.00383 | −0.017061 | −0.017527 | −0.021344 | −0.018224 | −0.023839 | −0.025573 | −0.025964 | −0.01647 | 0.034935 | 0.02404 |
| 219 | 0.03553 | 0.01252 | −0.00053 | −0.015057 | −0.027234 | −0.022682 | −0.040125 | −0.013262 | −0.009712 | −0.021021 | −0.028394 | −0.002548 | 0.016143 | 0.011514 |
| 220 | 0.035344 | −0.006096 | −0.002401 | 0.005979 | −0.00899 | 0.003589 | −0.006036 | −0.011826 | 0.017485 | −0.000353 | −0.005842 | −0.015948 | −0.01037 | 0.020504 |
| 221 | −0.021036 | 0.030091 | 0.007402 | −0.002429 | 0.011278 | 0.02612 | −0.005186 | −0.00102 | −0.037349 | −0.003734 | 0.011273 | 0.002232 | 0.020689 | 0.00866 |
| 222 | 0.016648 | 0.033428 | −0.000566 | −0.020692 | 0.002636 | 0.008257 | 0.005745 | 0.000491 | −0.024281 | −0.008568 | −0.004896 | 0.016855 | 0.003269 | −0.003324 |
| 223 | 0.001243 | 0.026928 | 0.011139 | −0.016369 | −0.000389 | 0.00364 | −0.011858 | −0.007263 | −0.039114 | −0.021014 | −0.033764 | −0.008571 | 0.022131 | −0.00412 |
| 224 | −0.006326 | −0.013262 | −0.048312 | −0.019543 | −0.00779 | 0.013391 | −0.016709 | −0.015728 | −0.009449 | −0.026361 | −0.009558 | −0.010552 | −0.031563 | −0.017714 |
| 225 | −0.01973 | −0.004153 | −0.056468 | −0.013605 | −0.011572 | 0.011515 | −0.017544 | −0.019543 | −0.015337 | −0.027095 | −0.00796 | 0.000554 | −0.030157 | −0.015598 |
| 226 | 0.015104 | −0.006657 | 0.021689 | 0.005871 | 0.005427 | 0.002202 | 0.001855 | 0.002175 | 0.01017 | 0.011119 | −0.00615 | −0.00159 | 0.008827 | 0.017303 |

APPENDIX B3-continued

PCA Transformation
Matrix (340 × 340 Early/Late)

| | | | | | | | | | | | | | |
|---|---|---|---|---|---|---|---|---|---|---|---|---|---|
| 227 | 0.06444 | 0.022751 | −0.023338 | −0.023085 | −0.019089 | 0.003024 | −0.010636 | −0.003281 | 0.006508 | −0.013207 | −0.029228 | 0.011874 | −0.043665 | −0.024665 |
| 228 | 0.030076 | 0.031699 | 0.012032 | −0.026226 | 0.008692 | −0.001363 | 0.001725 | 0.000808 | 0.013075 | 0.013581 | −0.023854 | 0.023201 | 0.054079 | 0.006296 |
| 229 | 0.031929 | 0.002248 | −0.004902 | −0.004223 | −0.020447 | −0.027689 | 0.009414 | −0.011714 | −0.001713 | −0.001906 | 0.042258 | 0.021047 | 0.020974 | 0.001903 |
| 230 | 0.021763 | 0.003208 | −0.015427 | −0.064926 | −0.008283 | 0.00436 | 0.004994 | −0.004025 | −0.007962 | −0.022212 | 0.002126 | 0.015948 | −0.020584 | −0.035832 |
| 231 | −0.011895 | −0.03849 | 0.015717 | 0.00942 | −0.004284 | −0.000444 | 0.008203 | −0.02553 | −0.007844 | 0.015218 | 0.000909 | −0.019636 | 0.022456 | 0.024216 |
| 232 | −0.015961 | −0.006907 | 0.010913 | 0.008592 | 0.018545 | 0.023999 | 0.020713 | −0.000443 | 0.016964 | −0.000363 | −0.016214 | −0.008485 | 0.017009 | 0.026553 |
| 233 | −0.033551 | 0.038151 | 0.017541 | 0.011633 | 0.008605 | 0.014764 | 0.013018 | 0.007533 | 0.004635 | −0.00268 | −0.010843 | 0.027262 | −0.028092 | −0.025515 |
| 234 | 0.015225 | 0.0327 | 0.007249 | −0.018959 | −0.01456 | −0.01882 | −0.011543 | 0.004597 | 0.017611 | 0.008835 | −0.026343 | 0.00677 | 0.008187 | −0.018346 |
| 235 | −0.011074 | 0.005343 | −0.007007 | 0.002356 | −0.014442 | −0.00745 | 0.00632 | −0.022605 | 0.007437 | 0.012238 | −0.021024 | 0.000837 | 0.006601 | −0.019143 |
| 236 | −0.023781 | −0.035652 | −0.016563 | 0.010676 | −0.000459 | −0.001109 | −0.006717 | −0.000595 | 0.019612 | 0.008902 | −0.021304 | −0.058101 | 0.005203 | 0.014865 |
| 237 | −0.013016 | −0.011777 | −0.015328 | 0.014455 | 0.003234 | −0.008906 | −0.000958 | 0.012066 | 0.010854 | 0.005875 | 0.0115 | −0.00416 | −0.021984 | 0.018406 |
| 238 | −0.008058 | 0.01438 | −0.010016 | −0.004732 | −0.004478 | −0.004923 | −0.007307 | 0.001861 | 0.004286 | 0.002806 | −0.000751 | 0.015238 | −0.000678 | 0.004437 |
| 239 | −0.018637 | 0.026024 | 0.002366 | −0.006434 | −0.000274 | 0.004358 | 0.001218 | −0.002441 | −0.004132 | −0.001007 | −0.019293 | 0.009761 | 0.021665 | −0.012561 |
| 240 | −0.055128 | −0.017248 | −0.013307 | 0.030556 | −0.002153 | −0.001177 | 0.00491 | 0.023713 | −0.001946 | 0.008226 | −0.014861 | 0.018272 | 0.021563 | −0.003725 |
| 241 | −0.026778 | 0.00951 | −0.008859 | 0.022749 | 0.00353 | 0.003729 | −0.003505 | 0.026631 | 0.027363 | 0.007935 | −0.00488 | 0.003824 | −0.016764 | −0.016114 |
| 242 | −0.002194 | 0.001767 | 0.008205 | 0.000667 | 0.002762 | 0.002818 | 0.004045 | −0.000501 | 0.010284 | 0.013536 | −0.003822 | −0.023417 | −0.019878 | −0.025533 |
| 243 | 0.035448 | 0.025756 | 0.02752 | −0.01565 | −0.002568 | 0.003274 | 0.005656 | −0.007222 | 0.016419 | 0.011713 | −0.018812 | 0.009641 | −0.012189 | −0.017406 |
| 244 | −0.003459 | 0.019679 | 0.012493 | 0.002455 | 0.013102 | 0.023645 | 0.002802 | 0.007705 | −0.006947 | 0.020684 | 0.04389 | 0.013005 | −0.001048 | −0.014994 |
| 245 | 0.016553 | 0.000698 | −0.023461 | −0.009164 | −0.007486 | −0.001045 | −0.000199 | −0.003131 | 0.003166 | −0.031389 | 0.032477 | 0.006312 | −0.024899 | −0.008855 |
| 246 | −0.010047 | −0.002384 | −0.006068 | −0.007306 | 0.001386 | −0.005694 | 0.004083 | 0.014603 | −0.00634 | −0.018304 | 0.006696 | −0.001979 | −0.012978 | −0.017125 |
| 247 | −0.009217 | −0.003675 | −0.021862 | −0.003183 | −0.000311 | 0.011645 | 0.003836 | 0.002046 | −0.00313 | −0.007585 | −0.014544 | −0.00808 | 0.006141 | −0.019548 |
| 248 | 0.005557 | −0.010401 | −0.031035 | 0.01166 | 0.004441 | 0.023488 | 0.006778 | −0.003016 | 0.012802 | 0.006377 | −0.001001 | −0.000291 | 0.008446 | 0.002683 |
| 249 | −0.022343 | 0.010028 | −0.001584 | −0.005273 | −0.00238 | −0.020354 | 0.000442 | 0.011071 | 0.017017 | 0.011557 | −0.002475 | −0.007709 | 0.009545 | 0.020877 |
| 250 | −0.027609 | −0.003291 | −0.010753 | 0.023171 | 0.000456 | −0.002614 | −0.012763 | 0.027932 | 0.003686 | 0.021278 | −0.010424 | −0.004833 | 0.011756 | −0.01148 |
| 251 | −0.03897 | −0.007323 | −0.028625 | 0.031256 | 0.002601 | 0.006123 | −0.004529 | 0.019478 | −0.001145 | 0.020169 | 0.000367 | 0.011351 | −0.011901 | −0.012573 |
| 252 | 0.026712 | 0.001236 | −0.022268 | 0.01992 | 0.005794 | 0.015797 | 0.014722 | −0.007285 | 0.035974 | 0.025152 | 0.019714 | −0.008582 | −0.030291 | −0.003922 |
| 253 | 0.000038 | 0.019033 | 0.021073 | 0.001419 | −0.008696 | −0.012896 | −0.018434 | −0.010208 | 0.033487 | 0.013683 | −0.011924 | −0.01989 | 0.009935 | 0.001652 |
| 254 | 0.002426 | 0.007853 | 0.019658 | −0.005624 | −0.003802 | −0.01234 | −0.005339 | −0.00403 | −0.027286 | −0.014522 | −0.013001 | 0.003933 | 0.015662 | −0.008457 |
| 255 | −0.000142 | 0.010528 | 0.016133 | −0.00596 | 0.001883 | −0.001762 | 0.003172 | 0.00422 | −0.017244 | −0.005481 | 0.019366 | 0.009413 | −0.008761 | −0.012171 |
| 256 | −0.010523 | 0.003293 | 0.001019 | −0.024928 | −0.000511 | −0.009657 | 0.003189 | −0.010505 | 0.006007 | −0.046728 | 0.035223 | −0.010913 | −0.025157 | 0.023157 |
| 257 | −0.010386 | 0.027964 | −0.019313 | −0.000919 | −0.004892 | −0.00506 | 0.007983 | −0.008438 | 0.011997 | 0.010507 | −0.009071 | −0.013878 | −0.015645 | −0.004226 |
| 258 | 0.006676 | 0.010696 | −0.036462 | 0.007291 | −0.011043 | 0.003735 | 0.001641 | −0.012745 | 0.00552 | −0.008684 | −0.024144 | −0.027719 | −0.011716 | −0.008278 |
| 259 | 0.007759 | 0.009179 | −0.016639 | 0.005855 | 0.00009 | −0.006996 | −0.007234 | 0.008416 | −0.000723 | 0.013438 | −0.005137 | 0.011509 | −0.004493 | −0.004911 |
| 260 | 0.018565 | −0.02419 | −0.040265 | 0.024582 | 0.008603 | 0.0107 | 0.011929 | −0.000324 | 0.012728 | 0.031023 | −0.002935 | −0.003511 | −0.004732 | −0.01432 |
| 261 | 0.013585 | −0.016628 | −0.048067 | 0.028299 | 0.01414 | 0.015316 | 0.024199 | 0.008225 | 0.013239 | 0.021687 | −0.00326 | −0.003607 | 0.01156 | 0.012605 |
| 262 | −0.010651 | −0.025505 | −0.023942 | 0.018342 | 0.011537 | 0.016522 | 0.021757 | −0.010511 | 0.008104 | 0.011303 | −0.016379 | −0.018237 | 0.01116 | −0.008265 |
| 263 | −0.003255 | −0.006924 | −0.019398 | 0.010524 | 0.004132 | 0.009239 | 0.00902 | −0.014574 | 0.01895 | 0.023665 | −0.006494 | −0.011046 | 0.00259 | −0.008065 |
| 264 | 0.03029 | 0.005897 | −0.005874 | −0.022883 | 0.001338 | −0.006277 | −0.002453 | 0.011886 | 0.003151 | 0.003095 | 0.006273 | 0.00389 | 0.020748 | 0.0102 |
| 265 | 0.042 | −0.022527 | 0.005814 | −0.008978 | 0.011167 | 0.00234 | 0.009631 | −0.000897 | 0.001201 | −0.000395 | −0.005169 | −0.00559 | 0.045796 | 0.030599 |
| 266 | 0.03848 | −0.014103 | 0.009327 | −0.00313 | 0.016274 | 0.01003 | 0.01691 | −0.001673 | −0.000648 | 0.002322 | 0.020301 | −0.005443 | 0.033293 | 0.033959 |
| 267 | 0.028482 | −0.004723 | 0.030601 | −0.003372 | −0.013448 | −0.026816 | −0.026708 | −0.005622 | 0.011027 | −0.008243 | 0.004132 | −0.010209 | 0.032095 | 0.013507 |
| 268 | −0.001359 | −0.00547 | 0.025575 | 0.010721 | 0.001174 | 0.001838 | −0.006685 | −0.002045 | 0.011496 | 0.01375 | −0.010363 | −0.003314 | 0.015378 | 0.008941 |
| 269 | 0.00446 | −0.012329 | 0.02605 | 0.015168 | 0.004202 | 0.004112 | −0.00052 | 0.000009 | 0.011759 | 0.017414 | 0.00224 | −0.001658 | −0.001724 | 0.014398 |
| 270 | 0.030173 | −0.000472 | 0.015024 | −0.000001 | 0.003123 | 0.003348 | 0.003128 | −0.000132 | 0.009913 | 0.01025 | −0.015136 | 0.003942 | −0.010016 | −0.001922 |
| 271 | −0.005083 | 0.006254 | −0.009436 | −0.021325 | 0.01225 | −0.010817 | −0.019424 | 0.018523 | 0.014564 | 0.04212 | 0.069681 | −0.015593 | 0.047408 | −0.000936 |
| 272 | 0.010545 | −0.026356 | −0.01526 | 0.016282 | −0.014082 | −0.027732 | 0.007219 | −0.010888 | −0.0004271 | 0.006402 | 0.032195 | 0.006604 | 0.036213 | 0.016063 |
| 273 | −0.004184 | −0.036679 | −0.013914 | 0.026579 | 0.004004 | 0.015687 | 0.019457 | −0.011216 | 0.002653 | 0.011182 | −0.00145 | 0.011249 | 0.006726 | −0.009191 |
| 274 | 0.003629 | −0.039815 | −0.011878 | 0.023095 | 0.006122 | 0.014932 | 0.022406 | −0.007041 | 0.005921 | 0.014626 | 0.004714 | 0.012475 | 0.000979 | −0.008663 |
| 275 | 0.059488 | −0.007557 | −0.029347 | −0.048614 | −0.00016 | 0.017671 | 0.015254 | −0.003855 | −0.00275 | −0.009301 | −0.0033 | 0.016274 | −0.035582 | −0.04119 |
| 276 | −0.01014 | −0.031528 | −0.026818 | 0.015261 | −0.012961 | −0.020585 | −0.006332 | −0.001036 | 0.021036 | 0.002978 | −0.020799 | −0.060794 | 0.014424 | 0.017188 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 277 | −0.011703 | −0.022094 | 0.014279 | 0.014272 | 0.006989 | −0.000765 | 0.008866 | −0.000508 | −0.015059 | −0.009938 | −0.013987 | 0.002563 | 0.017615 | 0.000009 |
| 278 | −0.017878 | −0.020987 | 0.015724 | 0.014873 | 0.017923 | 0.01102 | 0.011889 | −0.001328 | −0.019129 | −0.005127 | −0.007216 | 0.004812 | 0.012733 | −0.00616 |
| 279 | −0.001949 | 0.003943 | 0.009898 | −0.014398 | 0.001238 | −0.001626 | 0.000052 | 0.006633 | −0.003553 | −0.001585 | −0.020708 | 0.021226 | 0.030298 | −0.006103 |
| 280 | 0.01544 | 0.013636 | 0.045226 | −0.02295 | −0.005626 | −0.013633 | −0.004341 | −0.00346 | 0.025143 | −0.005629 | −0.035561 | −0.006443 | −0.005586 | 0.000845 |
| 281 | −0.000459 | −0.027735 | 0.009122 | −0.004862 | 0.00554 | −0.000756 | 0.006541− | 0.012208 | −0.008617 | −0.018413 | 0.013911 | 0.006888 | −0.005156 | −0.006304 |
| 282 | −0.002623 | −0.010899 | 0.011856 | −0.013947 | 0.011246 | 0.007122 | 0.005097 | 0.006369 | −0.01619 | −0.020811 | 0.011991 | 0.002237 | −0.019003 | −0.025624 |
| 283 | 0.015491 | −0.030165 | −0.011275 | −0.007902 | 0.01323 | 0.021655 | 0.002305 | 0.011779 | 0.004249 | 0.000684 | −0.008214 | 0.004427 | 0.019318 | −0.01233 |
| 284 | −0.01613 | 0.002695 | −0.018014 | −0.003914 | −0.000919 | −0.00433 | 0.001717 | −0.002377 | 0.011154 | 0.010377 | 0.00021 | −0.0076 | −0.003395 | 0.006404 |
| 285 | −0.013637 | 0.024889 | −0.006599 | −0.010045 | 0.002781 | −0.002559 | 0.000037 | −0.001266 | 0.008713 | 0.014527 | 0.00152 | −0.008353 | −0.006602 | −0.00813 |
| 286 | 0.020307 | 0.030115 | −0.018331 | −0.01632 | −0.01332 | −0.012238 | −0.001947 | −0.004959 | 0.004151 | −0.006343 | 0.00459 | −0.004145 | −0.037518 | −0.006948 |
| 287 | 0.025757 | 0.039064 | −0.009807 | −0.017168 | −0.007908 | −0.006018 | −0.000023 | −0.005075 | 0.003809 | −0.003215 | −0.001097 | −0.004784 | −0.034047 | −0.016436 |
| 288 | 0.030488 | −0.001379 | −0.031906 | −0.002678 | 0.008369 | 0.026361 | 0.004917 | 0.006968 | 0.010813 | −0.006499 | −0.012888 | −0.0216 | −0.010781 | −0.002939 |
| 289 | −0.012726 | −0.027369 | −0.00579 | 0.006207 | 0.01076 | 0.013025 | 0.018561 | −0.011566 | 0.012142 | 0.015162 | −0.017255 | −0.033285 | 0.006754 | −0.011221 |
| 290 | −0.00334 | 0.010245 | −0.000374 | 0.003235 | 0.02003 | 0.035488 | 0.006797 | −0.009721 | −0.007935 | −0.011037 | 0.002428 | 0.009276 | −0.031721 | −0.01504 |
| 291 | 0.001706 | 0.00782 | −0.001389 | 0.001597 | 0.018952 | 0.03342 | 0.00755 | −0.009982 | −0.009009 | −0.012548 | 0.0024 | 0.010886 | −0.031938 | −0.013774 |
| 292 | 0.008535 | 0.024642 | 0.003775 | −0.007068 | 0.015621 | 0.030425 | 0.01246 | −0.0042 | −0.009073 | −0.011383 | −0.00039 | 0.017435 | −0.028054 | −0.013179 |
| 293 | −0.072767 | 0.012217 | 0.005555 | 0.005621 | 0.004417 | 0.010857 | −0.009 | −0.002692 | −0.022521 | −0.012615 | −0.031814 | −0.016966 | 0.000614 | 0.010498 |
| 294 | 0.017879 | 0.002672 | 0.017587 | 0.009101 | 0.010357 | 0.018185 | 0.008953 | −0.001202 | −0.006221 | 0.002439 | −0.004926 | 0.003787 | 0.012818 | 0.005335 |
| 295 | −0.044644 | −0.026801 | −0.001748 | 0.020181 | 0.00439 | 0.005484 | 0.012308 | −0.005437 | −0.009782 | −0.000273 | −0.009847 | 0.007566 | 0.002412 | −0.005062 |
| 296 | 0.014181 | −0.000863 | 0.009721 | 0.000635 | 0.009406 | 0.02154 | 0.037555 | 0.002941 | −0.010473 | −0.003686 | −0.011846 | 0.027313 | 0.015442 | −0.012944 |
| 297 | −0.043988 | −0.020392 | −0.000777 | 0.031196 | 0.001146 | 0.002234 | 0.014027 | −0.000346 | −0.003301 | 0.000112 | −0.008247 | −0.010745 | −0.00053 | −0.001052 |
| 298 | 0.02194 | 0.010091 | 0.004136 | 0.010009 | −0.001169 | 0.005123 | −0.006391 | −0.000053 | −0.003385 | −0.010533 | −0.010614 | 0.006108 | −0.004086 | −0.002562 |
| 299 | −0.052141 | −0.018358 | 0.006301 | 0.03444 | 0.000765 | 0.002144 | −0.000299 | 0.002919 | 0.00242 | 0.00376 | −0.014791 | −0.004171 | −0.003332 | 0.025386 |
| 300 | −0.032138 | −0.007988 | 0.004621 | −0.004329 | −0.010644 | −0.032203 | −0.002496 | 0.000702 | −0.01347 | −0.022112 | −0.059906 | 0.016959 | 0.03468 | −0.046087 |
| 301 | −0.052292 | 0.009838 | 0.001172 | 0.014212 | 0.007915 | 0.007249 | −0.005693 | 0.000408 | 0.002843 | 0.011665 | −0.013433 | −0.006058 | 0.00489 | 0.008176 |
| 302 | −0.01609 | 0.0103 | 0.000149 | 0.002202 | 0.006203 | 0.004667 | 0.005899 | −0.002639 | 0.002554 | 0.004553 | −0.026064 | 0.006455 | −0.009537 | −0.01255 |
| 303 | 0.003443 | 0.007797 | 0.006238 | 0.027598 | 0.001389 | 0.006205 | 0.021223 | −0.001736 | −0.001381 | −0.008578 | −0.028265 | 0.015094 | −0.01445 | 0.013587 |
| 304 | −0.007054 | −0.003064 | −0.004626 | 0.033471 | 0.000385 | 0.00759 | 0.005794 | 0.000117 | 0.007493 | −0.014201 | −0.044309 | 0.022387 | −0.023943 | 0.011678 |
| 305 | −0.028079 | 0.061441 | 0.00056 | −0.026123 | 0.042847 | 0.035162 | 0.021589 | 0.005491 | 0.0058 | 0.019174 | 0.002513 | −0.01265 | 0.006484 | 0.013458 |
| 306 | −0.050492 | 0.018604 | −0.047785 | −0.006779 | −0.000327 | 0.022723 | −0.00738 | −0.003329 | −0.011202 | −0.002101 | −0.014271 | −0.030371 | 0.038796 | −0.000442 |
| 307 | 0.002245 | −0.001972 | 0.014904 | −0.021231 | −0.004491 | −0.014716 | −0.021092 | −0.032784 | −0.014781 | −0.018321 | 0.019132 | 0.036145 | −0.023252 | −0.013176 |
| 308 | −0.063263 | 0.083749 | 0.016979 | −0.029357 | −0.015839 | −0.022192 | −0.001512 | −0.004618 | −0.007315 | −0.003749 | 0.005442 | 0.033965 | −0.057578 | −0.031173 |
| 309 | −0.016437 | 0.007126 | 0.025673 | −0.001027 | 0.001583 | −0.010755 | −0.007744 | −0.004502 | −0.00939 | 0.0108 | −0.003207 | 0.000394 | 0.011885 | 0.007704 |
| 310 | 0.019685 | −0.021383 | 0.028597 | −0.017636 | −0.005606 | 0.000137 | −0.009624 | −0.010521 | 0.006436 | 0.026302 | 0.029267 | 0.002284 | −0.001231 | −0.003085 |
| 311 | −0.026665 | 0.01018 | 0.001888 | 0.027402 | 0.00456 | 0.004195 | −0.004581 | 0.001427 | 0.001361 | 0.009878 | −0.015513 | 0.009925 | 0.009971 | −0.011109 |
| 312 | 0.035998 | −0.034243 | 0.016965 | 0.044466 | −0.017913 | −0.007394 | 0.04172 | −0.022333 | −0.002584 | −0.022184 | −0.008614 | −0.018331 | −0.056468 | −0.034168 |
| 313 | −0.001655 | 0.016959 | −0.02029 | 0.021446 | −0.008242 | −0.012066 | 0.010126 | 0.000311 | −0.000522 | 0.006304 | 0.018906 | 0.007208 | −0.012892 | 0.004199 |
| 314 | 0.021756 | −0.055804 | 0.032931 | 0.034503 | −0.022494 | −0.036725 | 0.00659 | −0.021392 | 0.005494 | 0.029886 | 0.010292 | −0.026448 | 0.03069 | −0.01721 |
| 315 | −0.01557 | 0.01196 | 0.020989 | 0.001451 | 0.003333 | −0.004602 | 0.012361 | 0.012743 | −0.004132 | 0.012037 | 0.008669 | −0.007812 | 0.011462 | 0.01078 |
| 316 | 0.004479 | 0.042571 | 0.000176 | −0.001507 | −0.003519 | −0.01873 | −0.003434 | −0.013416 | −0.010621 | −0.010849 | −0.024605 | −0.007549 | −0.006682 | 0.002374 |
| 317 | −0.002652 | −0.007868 | 0.02409 | −0.002561 | 0.001657 | −0.012035 | 0.001285 | −0.006493 | −0.017131 | 0.009622 | 0.002804 | 0.000489 | 0.032865 | 0.005714 |
| 318 | 0.00878 | −0.007869 | 0.016144 | 0.016131 | 0.005339 | −0.003999 | −0.023566 | 0.014776 | 0.005267 | 0.03724 | 0.048356 | 0.009514 | −0.033365 | −0.001626 |
| 319 | −0.022278 | −0.000119 | 0.020723 | −0.000829 | −0.007015 | −0.012822 | −0.005413 | −0.006764 | −0.01772 | −0.0011 | −0.000783 | −0.009197 | 0.009692 | 0.01398 |
| 320 | −0.008844 | 0.024769 | −0.014166 | 0.022931 | −0.011232 | 0.003403 | −0.003999 | −0.016301 | −0.021895 | −0.032792 | −0.023812 | 0.015365 | −0.016526 | −0.003418 |
| 321 | 0.003415 | −0.016928 | −0.012039 | 0.020943 | 0.005769 | 0.009835 | 0.001576 | 0.018759 | 0.019933 | 0.013057 | 0.016171 | 0.01336 | −0.003461 | −0.001009 |
| 322 | 0.035644 | −0.004637 | 0.031536 | −0.029098 | −0.003756 | −0.018344 | −0.017823 | 0.007892 | 0.044791 | 0.028621 | −0.016863 | 0.004149 | −0.003523 | 0.016436 |
| 323 | 0.014324 | −0.034565 | −0.009709 | 0.021544 | −0.019934 | −0.018308 | −0.019877 | 0.010865 | 0.034632 | 0.025979 | 0.023816 | −0.008373 | −0.002914 | 0.010591 |
| 324 | −0.005611 | 0.040286 | −0.027265 | −0.018229 | 0.009898 | 0.008778 | −0.018229 | 0.018713 | 0.025613 | 0.026243 | −0.018518 | −0.021249 | 0.015716 | −0.020386 |
| 325 | 0.03968 | 0.014673 | 0.007786 | −0.008876 | 0.010953 | 0.00925 | 0.020285 | 0.00711 | 0.000305 | 0.008319 | 0.002422 | −0.008752 | 0.022499 | 0.019821 |
| 326 | 0.024806 | −0.011377 | −0.015643 | 0.002422 | 0.0136 | 0.003171 | 0.017911 | −0.002197 | 0.0094 | 0.019426 | 0.03663 | 0.020954 | −0.021657 | 0.012733 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 327 | 0.004096 | 0.00188 | −0.018212 | 0.007086 | 0.008206 | 0.010788 | 0.012079 | 0.007845 | 0.003177 | 0.009505 | 0.006977 | 0.022549 | 0.004942 | 0.002361 |
| 328 | −0.048957 | 0.071999 | 0.033803 | −0.037002 | 0.013616 | −0.000665 | 0.017405 | 0.006633 | −0.006884 | −0.01813 | −0.034283 | −0.017283 | 0.1054 | 0.026056 |
| 329 | −0.016623 | 0.001215 | −0.005219 | 0.0168 | 0.006891 | 0.004392 | 0.019931 | 0.007023 | 0.000717 | 0.027796 | 0.034344 | 0.018158 | 0.018476 | 0.006642 |
| 330 | 0.025511 | −0.014624 | −0.049644 | −0.00717 | −0.024477 | −0.024324 | −0.015785 | 0.000729 | 0.032349 | −0.010953 | −0.030315 | −0.047503 | −0.032317 | −0.016686 |
| 331 | 0.001943 | 0.007835 | 0.002315 | 0.007452 | 0.008121 | 0.010935 | 0.009131 | 0.014716 | 0.007562 | 0.012489 | 0.015062 | 0.008607 | 0.01455 | 0.00912 |
| 332 | −0.060374 | −0.037516 | −0.015472 | 0.001226 | 0.003841 | −0.014967 | −0.023397 | 0.006414 | 0.01488 | −0.02821 | −0.046801 | 0.01099 | −0.030849 | −0.012495 |
| 333 | −0.003977 | 0.016679 | 0.003765 | −0.009834 | 0.008106 | 0.002556 | 0.000753 | 0.010765 | 0.002556 | 0.012238 | 0.021386 | −0.005334 | 0.007251 | 0.013216 |
| 334 | 0.00534 | 0.063416 | −0.035207 | −0.024943 | 0.006738 | 0.015936 | 0.039468 | 0.003517 | −0.018138 | 0.015077 | 0.067384 | −0.019612 | −0.014676 | −0.002759 |
| 335 | 0.00754 | −0.007726 | 0.00436 | 0.013432 | 0.001191 | 0.002252 | −0.004247 | −0.009142 | 0.007038 | 0.006303 | 0.011986 | 0.004386 | −0.006311 | 0.020247 |
| 336 | −0.000353 | −0.011199 | −0.011407 | −0.016644 | 0.01767 | 0.015437 | −0.019354 | 0.015282 | 0.01312 | 0.002998 | 0.004831 | 0.013664 | −0.003051 | −0.006761 |
| 337 | −0.028587 | 0.006397 | 0.010517 | −0.018997 | −0.021585 | −0.034085 | −0.019752 | −0.014529 | −0.009912 | −0.001427 | 0.016504 | −0.014301 | −0.002234 | 0.018187 |
| 338 | −0.040418 | 0.006474 | −0.01118 | −0.01065 | 0.005477 | 0.03073 | 0.017096 | 0.011611 | 0.005884 | 0.016952 | −0.002106 | 0.010835 | 0.019651 | 0.009977 |
| 339 | −0.049084 | −0.023272 | −0.020249 | 0.005777 | −0.009147 | −0.019476 | −0.014562 | −0.005388 | −0.007155 | −0.00676 | −0.001386 | −0.001669 | 0.002014 | −0.005734 |
| 340 | −0.012568 | −0.016487 | −0.019106 | −0.05787 | 0.016853 | 0.026871 | 0.027705 | 0.007166 | 0.018196 | 0.033015 | 0.072845 | 0.016922 | −0.092783 | 0.015718 |

| | FX | FY | FZ | GA | GB | GC | GD | GE | GF | GG | GH | GI | GJ | GK |
|---|---|---|---|---|---|---|---|---|---|---|---|---|---|---|
| 1 | 0.027253 | 0.032531 | 0.021505 | 0.0347 | 0.033236 | 0.038951 | 0.03036 | 0.006051 | 0.029331 | −0.007202 | −0.024262 | 0.049023 | 0.041876 | −0.006579 |
| 2 | 0.065258 | 0.09261 | 0.079706 | 0.088439 | 0.064077 | 0.068095 | 0.012138 | 0.128754 | 0.018948 | 0.015506 | 0.056212 | 0.042871 | 0.090724 | −0.049806 |
| 3 | 0.020977 | 0.014858 | 0.022098 | 0.017769 | 0.038821 | 0.084327 | 0.000943 | 0.063487 | 0.04331 | 0.07521 | 0.09099 | 0.061525 | 0.024125 | 0.031528 |
| 4 | −0.025005 | −0.030097 | −0.019451 | −0.033346 | −0.018532 | −0.020642 | −0.004697 | 0.000381 | 0.006384 | 0.020041 | −0.004 | −0.000954 | 0.023636 | 0.042119 |
| 5 | 0.005053 | 0.000329 | −0.011277 | −0.018839 | 0.014694 | 0.002578 | 0.118388 | 0.048065 | −0.035687 | 0.008391 | 0.020329 | −0.011357 | −0.019139 | 0.005692 |
| 6 | 0.000921 | −0.004756 | 0.004594 | 0.0262 | 0.043686 | 0.028533 | 0.001747 | −0.10197 | −0.035489 | −0.008468 | −0.014522 | 0.053772 | −0.00228 | −0.068148 |
| 7 | −0.032319 | −0.035846 | −0.030825 | −0.048678 | 0.005264 | 0.023738 | 0.050588 | 0.025376 | −0.0147 | −0.044638 | −0.049359 | −0.023703 | −0.017161 | −0.016866 |
| 8 | −0.031833 | −0.020042 | −0.026259 | −0.030914 | −0.05274 | 0.006042 | −0.183633 | −0.118537 | −0.024838 | 0.00147 | −0.018594 | −0.026051 | −0.029783 | −0.027716 |
| 9 | −0.017501 | −0.023125 | −0.021015 | −0.013408 | 0.000495 | 0.033441 | 0.027668 | −0.007505 | −0.0373 | −0.014911 | −0.058796 | −0.013635 | −0.023977 | 0.004405 |
| 10 | −0.024 | −0.018766 | −0.004805 | −0.011992 | −0.016105 | −0.014031 | −0.039361 | 0.085091 | −0.043701 | 0.00365 | −0.013776 | 0.039467 | −0.003011 | −0.02285 |
| 11 | −0.020869 | −0.025799 | −0.025938 | −0.025405 | −0.002955 | −0.09207 | −0.034641 | 0.038258 | −0.001641 | −0.003786 | 0.041512 | −0.003351 | −0.00543 | 0.028941 |
| 12 | 0.03389 | −0.002692 | −0.009124 | −0.009557 | 0.041782 | 0.034384 | 0.016741 | −0.057346 | 0.001558 | −0.025748 | −0.030218 | 0.009115 | 0.013674 | 0.149538 |
| 13 | −0.06262 | −0.05605 | −0.071911 | −0.004393 | 0.011211 | 0.019262 | 0.033945 | 0.013018 | 0.047311 | 0.079579 | 0.029452 | −0.037617 | −0.010159 | 0.170971 |
| 14 | 0.023621 | 0.031422 | 0.026502 | 0.044473 | 0.044748 | 0.059822 | 0.074132 | −0.086484 | 0.017106 | 0.02501 | 0.030072 | 0.050091 | 0.057021 | 0.03132 |
| 15 | −0.010032 | 0.016599 | 0.004314 | −0.006163 | −0.103256 | −0.192361 | −0.079463 | −0.028097 | −0.001308 | 0.001412 | 0.012745 | −0.048925 | 0.020939 | −0.053726 |
| 16 | 0.00703 | 0.036534 | 0.009286 | −0.001018 | 0.001102 | −0.013843 | 0.000033 | 0.038121 | 0.051506 | 0.05369 | 0.030297 | 0.005716 | 0.011252 | −0.048883 |
| 17 | −0.002327 | −0.012709 | −0.012124 | −0.012091 | 0.03095 | −0.012111 | −0.029372 | −0.151823 | −0.05198 | −0.088493 | −0.096032 | 0.00397 | −0.011578 | 0.019536 |
| 18 | −0.037409 | −0.018098 | −0.001381 | 0.023121 | −0.030914 | 0.004893 | 0.0382 | −0.002815 | −0.020269 | −0.023508 | −0.039239 | 0.012112 | 0.005249 | 0.042806 |
| 19 | 0.030573 | 0.048924 | 0.023297 | −0.001835 | 0.012351 | −0.003958 | −0.010438 | 0.030329 | 0.048121 | 0.026914 | 0.026845 | 0.000088 | 0.008501 | 0.052303 |
| 20 | −0.046125 | −0.024025 | −0.028061 | −0.022598 | −0.005259 | 0.062135 | −0.005041 | 0.11627 | 0.04585 | −0.011318 | −0.069857 | −0.006453 | −0.056464 | −0.046856 |
| 21 | 0.03333 | 0.021652 | 0.031083 | −0.02497 | 0.001574 | 0.061039 | 0.003383 | −0.012535 | −0.012079 | −0.005885 | −0.063598 | 0.003346 | 0.03486 | 0.037539 |
| 22 | 0.037595 | 0.007535 | −0.005288 | 0.029234 | 0.04211 | 0.038613 | 0.06729 | −0.043073 | −0.017248 | −0.02372 | 0.017505 | −0.005557 | −0.009377 | 0.089358 |
| 23 | −0.031511 | −0.010667 | −0.022589 | 0.012962 | −0.024717 | −0.000214 | −0.035224 | 0.000578 | −0.019911 | −0.007335 | −0.02261 | −0.018522 | 0.003164 | −0.053633 |
| 24 | 0.052442 | 0.053361 | 0.046826 | 0.024308 | 0.002682 | −0.052023 | −0.002307 | 0.013574 | −0.035249 | −0.059805 | −0.050269 | 0.086802 | 0.12607 | −0.062274 |
| 25 | 0.022416 | 0.027262 | 0.012756 | 0.02227 | −0.009716 | 0.029027 | −0.028444 | 0.001524 | 0.044161 | 0.065317 | 0.105152 | 0.003702 | −0.009935 | −0.010577 |
| 26 | 0.022755 | 0.014632 | 0.006502 | −0.045535 | −0.022794 | 0.058364 | 0.011699 | 0.018466 | −0.052736 | −0.005494 | 0.003056 | −0.00398 | 0.044569 | 0.014151 |
| 27 | 0.046572 | 0.003078 | 0.011108 | 0.062909 | 0.122569 | 0.045623 | −0.045007 | −0.0024 | 0.011914 | −0.024843 | −0.002081 | −0.002906 | 0.02858 | 0.101491 |
| 28 | 0.003903 | 0.030508 | 0.013819 | −0.025774 | −0.026507 | −0.082606 | −0.081701 | −0.064005 | 0.036678 | 0.023122 | −0.02519 | 0.013937 | 0.012976 | −0.014048 |
| 29 | 0.007058 | −0.003614 | −0.00234 | −0.008709 | −0.001753 | −0.001692 | 0.007909 | 0.01275 | −0.017276 | −0.005042 | −0.014013 | 0.020717 | 0.015676 | 0.003597 |
| 30 | −0.085816 | −0.094505 | −0.077 | −0.047762 | −0.025535 | −0.000096 | 0.094748 | 0.017064 | 0.011232 | 0.000103 | 0.027624 | 0.010743 | 0.040371 | −0.053864 |
| 31 | −0.019831 | −0.023073 | −0.007005 | −0.019393 | −0.003834 | 0.027656 | −0.000161 | 0.048548 | −0.082322 | −0.054243 | −0.051418 | −0.024246 | −0.053374 | −0.045146 |
| 32 | −0.053137 | −0.032731 | −0.033586 | −0.021382 | −0.053904 | −0.075554 | −0.059996 | −0.017035 | −0.039397 | −0.038922 | −0.031117 | 0.014539 | 0.01215 | −0.024519 |
| 33 | 0.062177 | 0.054688 | 0.060241 | 0.028492 | 0.035334 | −0.00694 | 0.086262 | −0.181038 | −0.053381 | −0.037527 | 0.039078 | 0.047327 | −0.051657 | −0.032731 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 34 | −0.022567 | −0.010932 | −0.003934 | −0.017064 | −0.065799 | −0.084152 | −0.011925 | −0.104509 | 0.007985 | −0.004183 | −0.046841 | −0.01255 | −0.044667 | 0.026938 |
| 35 | 0.038275 | 0.01033 | 0.019972 | 0.053043 | 0.027868 | −0.059566 | 0.00623 | 0.070861 | 0.011112 | −0.029234 | −0.087909 | −0.024745 | −0.007997 | 0.031204 |
| 36 | −0.03795 | −0.033789 | −0.029793 | −0.038572 | −0.058395 | −0.0699 | −0.005561 | −0.014504 | 0.011389 | 0.036535 | 0.044287 | −0.011773 | −0.002015 | −0.001583 |
| 37 | 0.038213 | 0.025829 | 0.038072 | 0.080376 | 0.008048 | −0.097325 | 0.142509 | −0.020894 | 0.05544 | 0.051381 | −0.027516 | −0.065366 | −0.029905 | 0.070233 |
| 38 | −0.019799 | −0.031657 | −0.005054 | −0.009299 | −0.002515 | 0.058183 | 0.042611 | −0.037153 | −0.00217 | 0.017377 | 0.034652 | −0.063143 | −0.011369 | −0.057153 |
| 39 | −0.011245 | −0.024335 | −0.014345 | 0.036876 | 0.052102 | 0.001738 | −0.051096 | 0.005935 | −0.002922 | 0.031415 | 0.02705 | 0.079933 | 0.082268 | 0.072882 |
| 40 | −0.009276 | −0.010792 | −0.008531 | −0.011599 | 0.005444 | 0.027613 | −0.001445 | 0.010056 | −0.020385 | −0.02059 | −0.028028 | 0.012732 | 0.006179 | 0.016253 |
| 41 | −0.041842 | −0.04223 | −0.022035 | −0.008658 | −0.020075 | −0.060214 | 0.029089 | 0.001259 | 0.003713 | 0.027875 | −0.004447 | −0.013647 | −0.034261 | −0.083886 |
| 42 | 0.022133 | 0.020174 | 0.023617 | 0.016814 | 0.040941 | 0.082617 | 0.111554 | 0.008324 | 0.02584 | 0.040187 | 0.028766 | 0.043531 | 0.021649 | 0.00017 |
| 43 | −0.009091 | 0.018835 | 0.002561 | 0.019313 | 0.004989 | −0.035695 | 0.001615 | 0.059787 | 0.03118 | 0.067595 | 0.035865 | −0.021253 | −0.080812 | −0.052376 |
| 44 | 0.025245 | −0.023287 | −0.008743 | −0.016151 | 0.066807 | 0.025491 | −0.042783 | −0.021458 | −0.023767 | 0.005849 | 0.082407 | 0.002302 | 0.038143 | −0.00576 |
| 45 | −0.036556 | 0.005156 | −0.009521 | −0.003477 | −0.104252 | −0.107975 | 0.076386 | 0.053474 | 0.036804 | −0.004073 | −0.063496 | −0.010492 | −0.036223 | −0.077771 |
| 46 | 0.005198 | 0.002431 | −0.002424 | 0.011408 | 0.030518 | 0.057498 | −0.045406 | −0.025232 | 0.054608 | 0.066414 | 0.053073 | −0.031318 | −0.047895 | 0.016221 |
| 47 | 0.008987 | 0.007943 | 0.01586 | 0.012723 | 0.02728 | 0.039661 | 0.025058 | 0.046592 | −0.020378 | −0.029054 | 0.050213 | 0.022771 | −0.018388 | −0.078666 |
| 48 | 0.039168 | 0.031139 | 0.046381 | 0.024275 | 0.000492 | 0.073141 | −0.122238 | −0.030447 | 0.080394 | −0.004647 | −0.014217 | 0.04687 | 0.048861 | −0.036434 |
| 49 | 0.050623 | 0.051209 | 0.052426 | 0.056198 | 0.035458 | −0.026539 | 0.073874 | 0.003559 | −0.053363 | −0.033231 | −0.035713 | −0.015627 | −0.074612 | 0.023817 |
| 50 | 0.013132 | −0.003316 | 0.011791 | −0.010034 | 0.009893 | 0.047631 | 0.094717 | 0.101178 | 0.040801 | 0.016491 | 0.013449 | −0.009382 | 0.029824 | −0.046095 |
| 51 | 0.030136 | 0.031228 | 0.02029 | 0.041472 | −0.028472 | −0.054853 | −0.007553 | 0.043807 | −0.074103 | −0.047831 | −0.031022 | −0.004657 | −0.00443 | −0.052428 |
| 52 | 0.01669 | 0.065569 | 0.069257 | 0.039397 | −0.039044 | −0.029906 | 0.024397 | 0.01735 | −0.01003 | −0.022854 | −0.053881 | 0.050629 | 0.048614 | −0.002333 |
| 53 | 0.026666 | 0.028796 | 0.048853 | 0.030285 | −0.001846 | −0.056977 | 0.015124 | −0.095419 | −0.010406 | 0.000923 | −0.009372 | −0.034124 | −0.05128 | 0.02767 |
| 54 | 0.011654 | 0.017548 | 0.018108 | 0.039726 | 0.08414f | 0.059496 | −0.036195 | 0.06467 | −0.013039 | −0.011897 | −0.049437 | 0.095679 | 0.017808 | 0.035178 |
| 55 | 0.007153 | 0.042069 | 0.003665 | 0.025247 | 0.029156 | −0.000526 | 0.037828 | −0.016136 | 0.055716 | 0.053332 | 0.070642 | 0.011866 | −0.005445 | −0.022048 |
| 56 | 0.054024 | 0.06156 | 0.072763 | 0.099716 | 0.062059 | 0.006534 | −0.067708 | −0.011038 | 0.019688 | 0.009585 | 0.180179 | 0.030022 | −0.00158 | −0.015217 |
| 57 | 0.050029 | 0.041878 | 0.069938 | 0.040858 | 0.095722 | −0.035758 | −0.080523 | −0.008842 | −0.063601 | −0.124842 | −0.12122 | −0.04934 | 0.011031 | 0.001651 |
| 58 | 0.065366 | 0.059074 | 0.050996 | 0.083556 | 0.11102 | 0.099404 | 0.009441 | −0.063908 | 0.110831 | 0.167752 | 0.157947 | −0.087265 | −0.085206 | 0.076227 |
| 59 | 0.020422 | −0.015797 | 0.014382 | −0.005191 | −0.051788 | −0.074463 | 0.046742 | −0.038592 | 0.007209 | 0.043007 | 0.096484 | 0.029117 | 0.00115 | 0.011584 |
| 60 | 0.019414 | 0.010189 | 0.006447 | 0.003312 | 0.010628 | 0.028086 | −0.004237 | 0.006237 | 0.009909 | 0.000661 | 0.0281 | −0.018852 | 0.001398 | 0.027025 |
| 61 | −0.001572 | −0.002924 | −0.006911 | −0.014321 | 0.004669 | 0.02356 | −0.032976 | 0.010368 | −0.014993 | −0.026707 | −0.034599 | 0.015371 | 0.017978 | −0.003591 |
| 62 | 0.012489 | 0.009497 | 0.008393 | 0.012303 | −0.006173 | −0.00999 | 0.006188 | −0.034703 | 0.013215 | 0.008001 | 0.011483 | −0.014506 | −0.010592 | 0.03539 |
| 63 | 0.000169 | −0.005253 | −0.004789 | −0.009719 | 0.007935 | 0.00059 | −0.04478 | −0.004847 | −0.032031 | −0.044968 | −0.042302 | 0.019426 | 0.024236 | −0.002073 |
| 64 | −0.005735 | −0.008513 | −0.009944 | −0.001329 | −0.000318 | −0.014599 | −0.025102 | 0.018628 | −0.003281 | −0.017591 | −0.032866 | −0.007946 | −0.008241 | 0.014468 |
| 65 | 0.010141 | 0.005456 | 0.006042 | 0.005519 | 0.010379 | 0.042877 | −0.006306 | 0.005312 | 0.001833 | 0.012673 | 0.043781 | 0.007278 | 0.012989 | 0.002144 |
| 66 | −0.009303 | −0.019293 | −0.014737 | −0.006424 | 0.020132 | −0.003395 | −0.02454 | −0.031036 | −0.017901 | −0.00506 | 0.024 | −0.009899 | 0.003239 | 0.006806 |
| 67 | −0.017433 | −0.023634 | −0.019277 | −0.023844 | 0.010261 | 0.034444 | 0.021587 | −0.020262 | −0.014529 | −0.008358 | −0.003453 | 0.007563 | 0.005496 | −0.015852 |
| 68 | 0.032597 | 0.012939 | 0.025081 | 0.019369 | 0.038774 | 0.036756 | 0.013548 | −0.022269 | 0.007449 | −0.002029 | 0.021322 | −0.007191 | 0.032658 | 0.013578 |
| 69 | 0.002848 | 0.008849 | 0.009364 | 0.007902 | −0.017442 | −0.030573 | 0.020541 | −0.00693 | 0.00535 | −0.0048 | 0.004514 | 0.008327 | 0.002618 | −0.036128 |
| 70 | 0.007488 | 0.00409 | 0.009566 | −0.003093 | −0.016165 | −0.019407 | −0.004295 | −0.006963 | 0.00287 | −0.014659 | −0.022136 | −0.012316 | −0.000374 | −0.001412 |
| 71 | 0.006324 | −0.003948 | −0.001995 | 0.009838 | 0.00317 | 0.006505 | −0.010971 | 0.057586 | 0.016239 | 0.01034 | 0.036098 | 0.008535 | 0.014724 | 0.010962 |
| 72 | 0.004496 | −0.000942 | −0.006559 | −0.005735 | −0.011383 | −0.007435 | −0.009262 | 0.021166 | 0.009087 | 0.005024 | 0.038233 | 0.003765 | 0.004736 | −0.004478 |
| 73 | −0.000482 | −0.000829 | 0.008058 | −0.003869 | −0.012657 | 0.013193 | −0.022857 | −0.000854 | 0.024758 | 0.021196 | 0.051543 | 0.016186 | 0.021447 | −0.023582 |
| 74 | 0.016595 | 0.007202 | 0.009283 | 0.007091 | 0.001349 | −0.036693 | −0.004206 | 0.046662 | −0.016592 | 0.000933 | 0.015997 | −0.017391 | −0.018014 | 0.022499 |
| 75 | 0.006679 | −0.000782 | 0.003539 | 0.003462 | −0.000862 | −0.001336 | −0.011763 | 0.009661 | 0.011391 | 0.001097 | 0.008327 | 0.003607 | 0.007932 | 0.00012 |
| 76 | −0.003235 | 0.006434 | 0.001307 | 0.000893 | −0.010797 | −0.01844 | 0.009339 | 0.037341 | 0.008984 | −0.006982 | −0.038368 | 0.000841 | −0.00365 | 0.004773 |
| 77 | 0.005977 | −0.002326 | 0.002913 | 0.002285 | −0.005538 | −0.010965 | −0.012606 | 0.012462 | 0.010415 | −0.001345 | 0.007046 | −0.000284 | 0.006141 | −0.004051 |
| 78 | 0.010075 | −0.000204 | 0.007476 | 0.005032 | −0.008968 | −0.014539 | −0.010653 | 0.004409 | 0.017423 | 0.003725 | 0.01053 | 0.000888 | 0.007727 | 0.001118 |
| 79 | 0.015908 | 0.009037 | 0.014656 | 0.00568 | 0.001814 | −0.008095 | 0.004046 | 0.005195 | 0.00579 | −0.001935 | −0.011539 | −0.007248 | −0.002132 | 0.002737 |
| 80 | −0.038126 | −0.021703 | −0.032726 | −0.010538 | −0.013572 | −0.000364 | −0.028574 | 0.044696 | 0.015376 | 0.002669 | −0.019888 | 0.005489 | 0.005872 | 0.00013 |
| 81 | −0.007092 | 0.009175 | −0.009178 | −0.008891 | −0.008195 | −0.000806 | −0.016042 | 0.033461 | 0.00739 | 0.006864 | 0.00583 | 0.009265 | −0.007608 | 0.007198 |
| 82 | 0.005701 | 0.008831 | 0.005373 | 0.010468 | 0.001816 | −0.006269 | 0.040393 | 0.013614 | 0.012361 | 0.001027 | −0.015115 | −0.017367 | −0.00485 | 0.007325 |
| 83 | 0.006707 | 0.008723 | 0.006706 | 0.008197 | 0.008613 | 0.002862 | 0.008407 | 0.013199 | 0.005513 | −0.002313 | −0.016246 | 0.005355 | 0.010365 | 0.001393 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 84 | 0.001312 | −0.000495 | −0.003174 | 0.005676 | 0.009733 | 0.022126 | 0.006295 | 0.008683 | 0.007589 | 0.004659 | −0.001854 | 0.00722 | −0.005522 | 0.012371 |
| 85 | 0.006138 | 0.004553 | −0.002151 | −0.004061 | 0.009312 | 0.017476 | 0.01542 | −0.053122 | 0.013639 | 0.018202 | 0.007018 | 0.011329 | −0.003458 | 0.027793 |
| 86 | −0.011706 | −0.009459 | −0.009155 | −0.00846 | −0.00685 | −0.004201 | −0.0165 | 0.009129 | 0.000378 | −0.002662 | 0.021373 | 0.016945 | 0.003605 | −0.0036 |
| 87 | −0.014064 | −0.001125 | −0.004438 | −0.001281 | −0.00585 | 0.017048 | 0.017486 | 0.056992 | −0.017049 | −0.016911 | −0.011675 | 0.020552 | 0.004868 | −0.021822 |
| 88 | −0.000981 | 0.002744 | 0.001207 | 0.009063 | 0.003039 | 0.001811 | 0.025798 | 0.012256 | 0.012293 | 0.006814 | −0.002994 | −0.001683 | −0.001354 | −0.001013 |
| 89 | 0.007474 | 0.005081 | 0.00814 | 0.010755 | 0.001524 | −0.004434 | 0.018498 | 0.006168 | 0.009351 | 0.003213 | −0.000638 | 0.000937 | 0.002009 | 0.00581 |
| 90 | 0.008232 | 0.006693 | 0.00728 | 0.009152 | 0.009541 | 0.011403 | 0.012704 | 0.018763 | 0.001338 | −0.00392 | 0.002635 | 0.012943 | 0.011092 | 0.006767 |
| 91 | 0.005528 | 0.000658 | −0.000146 | 0.006762 | 0.012394 | 0.011114 | −0.001558 | −0.003431 | 0.009264 | 0.000033 | 0.011737 | −0.003553 | −0.005141 | 0.011893 |
| 92 | −0.010758 | −0.0048 | −0.006904 | −0.001258 | −0.014588 | 0.010674 | −0.007985 | −0.002307 | 0.030473 | 0.028256 | 0.01864 | 0.013631 | 0.016433 | 0.012455 |
| 93 | 0.012117 | 0.006832 | 0.005504 | 0.002983 | 0.014423 | 0.000946 | −0.018077 | −0.001042 | −0.002795 | −0.025731 | −0.02296 | 0.002489 | 0.018161 | 0.005541 |
| 94 | 0.008956 | −0.003268 | −0.002751 | −0.003236 | 0.016033 | 0.013615 | 0.052883 | 0.013285 | 0.020794 | 0.015718 | 0.017349 | −0.015903 | 0.011429 | 0.009733 |
| 95 | 0.004568 | 0.010919 | 0.007353 | 0.00337 | −0.011152 | −0.031695 | −0.004884 | −0.04076 | −0.030158 | −0.016236 | −0.016227 | 0.003132 | −0.003445 | −0.03601 |
| 96 | 0.007936 | −0.00463 | 0.010605 | −0.006608 | −0.005091 | −0.010337 | −0.041517 | −0.004411 | −0.007747 | −0.018269 | −0.020039 | −0.007758 | −0.010734 | 0.009543 |
| 97 | 0.00593 | 0.010367 | 0.011514 | 0.001414 | 0.01504 | 0.011842 | −0.004684 | 0.03081 | −0.011066 | −0.019758 | −0.029886 | 0.006384 | −0.001167 | −0.01349 |
| 98 | −0.050768 | −0.046431 | −0.049941 | −0.038643 | −0.031458 | −0.008027 | 0.011462 | 0.039152 | −0.002111 | 0.008123 | −0.017389 | −0.016587 | −0.013557 | −0.009366 |
| 99 | 0.000929 | 0.004313 | 0.007019 | −0.003357 | −0.004468 | 0.007613 | 0.005054 | 0.013835 | −0.004496 | −0.000017 | 0.007156 | 0.006958 | 0.002362 | −0.014555 |
| 100 | −0.025365 | −0.01145 | −0.016377 | −0.041748 | −0.066962 | −0.058134 | −0.007939 | 0.008782 | −0.018673 | −0.012193 | −0.041996 | −0.020554 | −0.015603 | −0.028385 |
| 101 | −0.040998 | −0.043933 | −0.048677 | −0.031104 | −0.007739 | −0.003358 | 0.011761 | 0.035204 | 0.005442 | 0.011961 | −0.016706 | −0.035484 | −0.031268 | 0.021283 |
| 102 | 0.00333 | 0.002334 | 0.004704 | −0.022916 | −0.021563 | −0.015367 | −0.04554 | 0.004931 | −0.074439 | −0.098201 | −0.106693 | 0.036446 | 0.017698 | −0.032814 |
| 103 | 0.003681 | −0.009173 | −0.010264 | −0.012254 | 0.019089 | 0.008419 | −0.025638 | −0.010722 | −0.031985 | −0.015888 | −0.019795 | −0.010298 | −0.010751 | 0.005932 |
| 104 | 0.00741 | 0.014721 | 0.011079 | 0.01202 | 0.004389 | 0.00721 | −0.022637 | 0.012563 | −0.015178 | −0.003624 | 0.010994 | −0.001452 | −0.036008 | −0.016952 |
| 105 | −0.026117 | −0.018256 | −0.014448 | −0.011553 | −0.065792 | −0.013206 | 0.01382 | 0.00413 | 0.011255 | 0.030702 | 0.005437 | −0.020768 | −0.008357 | 0.019051 |
| 106 | 0.008513 | −0.004524 | −0.002092 | 0.003364 | 0.036751 | 0.023499 | −0.004814 | 0.001474 | 0.008523 | −0.014082 | −0.004904 | 0.011737 | 0.030252 | 0.014462 |
| 107 | −0.001351 | 0.004624 | −0.000856 | 0.007294 | 0.002974 | 0.001276 | −0.00149 | 0.017614 | 0.052805 | 0.037243 | 0.049126 | 0.008123 | 0.027492 | 0.017406 |
| 108 | 0.006682 | 0.005956 | 0.001686 | 0.010867 | 0.010496 | −0.005242 | 0.008711 | 0.040551 | 0.021469 | −0.002949 | −0.039979 | 0.009988 | 0.02366 | 0.038078 |
| 109 | 0.018244 | 0.018715 | 0.014757 | 0.027345 | 0.004978 | −0.007936 | 0.015805 | −0.061384 | −0.001908 | −0.011721 | −0.024295 | 0.016923 | 0.011386 | 0.033055 |
| 110 | −0.00479 | −0.013035 | −0.020259 | −0.01326 | 0.002527 | 0.021785 | −0.042546 | −0.011548 | 0.020756 | 0.000496 | −0.011329 | 0.00682 | 0.007183 | 0.002392 |
| 111 | −0.00945 | −0.00295 | −0.008582 | 0.003724 | −0.022901 | −0.029043 | 0.003795 | 0.031929 | 0.003919 | −0.0028 | −0.032203 | 0.026065 | 0.009168 | 0.029907 |
| 112 | 0.010093 | 0.004957 | 0.00673 | −0.007099 | 0.000775 | −0.006999 | −0.035368 | 0.021422 | 0.003208 | −0.00512 | −0.024403 | 0.031827 | 0.027488 | −0.029264 |
| 113 | 0.006986 | 0.000753 | 0.007833 | 0.023874 | 0.017774 | 0.007639 | 0.01952 | 0.005326 | 0.022797 | 0.00295 | −0.011173 | 0.002513 | 0.045439 | 0.033638 |
| 114 | 0.007903 | 0.004031 | 0.011235 | −0.004154 | 0.01323 | 0.012673 | 0.014783 | −0.005356 | −0.012974 | −0.01142 | −0.004524 | 0.000046 | 0.028246 | −0.000073 |
| 115 | 0.001508 | −0.009858 | −0.012127 | −0.013003 | 0.005129 | 0.001782 | −0.019892 | −0.055512 | −0.018772 | −0.009736 | −0.008994 | −0.021507 | −0.026369 | 0.05127 |
| 116 | 0.013407 | 0.004247 | 0.00375 | −0.010251 | −0.020245 | −0.012496 | −0.006567 | 0.028056 | 0.000795 | −0.023191 | −0.040286 | 0.013393 | 0.031517 | −0.027458 |
| 117 | −0.001662 | 0.008615 | 0.003323 | −0.003833 | −0.005751 | 0.032423 | −0.057166 | 0.02614 | −0.027274 | 0.004774 | −0.012769 | 0.009956 | −0.022524 | 0.014773 |
| 118 | −0.02118 | −0.011742 | 0.000699 | −0.007159 | −0.040327 | −0.020601 | 0.001536 | −0.009726 | −0.023337 | −0.003866 | −0.017764 | −0.02214 | −0.028869 | 0.003452 |
| 119 | 0.009475 | 0.01361 | 0.013214 | 0.005641 | −0.003434 | −0.017248 | 0.006734 | −0.032803 | 0.007388 | 0.002468 | 0.021683 | −0.009744 | −0.013624 | −0.008708 |
| 120 | 0.000479 | −0.000631 | 0.002676 | −0.002597 | −0.001223 | −0.013433 | −0.02492 | −0.020856 | −0.020643 | −0.010728 | −0.019252 | −0.007024 | −0.022164 | 0.029337 |
| 121 | −0.018797 | −0.017692 | −0.0114 | −0.014056 | −0.05697 | −0.05509 | 0.00241 | −0.037387 | −0.034109 | −0.020493 | −0.026458 | 0.006994 | 0.019452 | −0.01966 |
| 122 | −0.014378 | −0.006657 | −0.012284 | −0.010254 | −0.016779 | −0.00197 | −0.045051 | −0.015412 | −0.003628 | 0.004982 | −0.024095 | 0.001169 | 0.004621 | −0.009219 |
| 123 | −0.008318 | 0.003502 | −0.006588 | −0.004277 | −0.045887 | −0.051219 | −0.010136 | −0.031695 | 0.015628 | 0.027274 | 0.007545 | −0.023749 | −0.00085 | 0.011862 |
| 124 | 0.008157 | 0.016415 | 0.009985 | −0.000375 | −0.009011 | −0.009523 | −0.011263 | −0.008067 | 0.013847 | 0.013206 | 0.006198 | −0.00638 | −0.005149 | −0.001976 |
| 125 | −0.007795 | −0.000898 | −0.002816 | 0.016894 | −0.0085161 | −0.015124 | −0.012174 | 0.036045 | −0.015937 | −0.005103 | −0.015075 | −0.019938 | −0.020876 | 0.000413 |
| 126 | −0.02321 | −0.01285 | −0.009524 | 0.008485 | −0.04341 | −0.018278 | 0.021285 | −0.007271 | −0.008978 | 0.021515 | 0.032323 | 0.007432 | 0.006109 | −0.027294 |
| 127 | −0.005307 | 0.000625 | 0.003486 | 0.014859 | −0.004524 | 0.025982 | 0.01252 | 0.03559 | 0.00342 | 0.02419 | 0.038954 | 0.004595 | 0.005934 | −0.048984 |
| 128 | 0.004662 | 0.00848 | 0.009494 | −0.000368 | −0.014172 | −0.020183 | −0.023298 | −0.005206 | 0.009666 | 0.00798 | 0.033201 | −0.017038 | −0.018243 | −0.02488 |
| 129 | 0.007649 | −0.004872 | 0.004351 | 0.005541 | 0.013246 | −0.022043 | 0.02026 | −0.042792 | −0.019655 | −0.007612 | 0.004509 | 0.052662 | 0.017884 | 0.001605 |
| 130 | 0.006243 | −0.008362 | 0.000739 | −0.007973 | 0.016034 | −0.002592 | −0.003997 | −0.080355 | 0.018599 | −0.001482 | −0.012318 | −0.008514 | −0.009667 | 0.027986 |
| 131 | 0.002608 | −0.003134 | −0.000692 | 0.002085 | −0.010245 | 0.002084 | 0.055247 | −0.021046 | 0.03326 | 0.026491 | −0.002685 | −0.02221 | −0.008818 | 0.007181 |
| 132 | 0.001449 | 0.013648 | 0.003803 | 0.006443 | −0.014463 | −0.02801 | −0.001236 | 0.005069 | 0.025303 | 0.018393 | 0.010354 | −0.0103 | −0.025241 | 0.002063 |
| 133 | 0.000077 | −0.009445 | −0.008539 | −0.01692 | 0.016895 | 0.042358 | 0.055707 | 0.027201 | −0.003295 | 0.010218 | 0.038548 | 0.001284 | −0.001301 | −0.010551 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 134 | 0.001088 | −0.010823 | −0.008232 | 0.01225 | 0.008215 | −0.001005 | 0.006349 | −0.019781 | −0.005093 | 0.015069 | 0.024635 | −0.041628 | −0.05006 | −0.021692 |
| 135 | 0.009433 | 0.009909 | 0.014302 | 0.011489 | −0.000023 | −0.019801 | −0.000389 | 0.023122 | −0.002483 | −0.0039 | 0.001199 | −0.007388 | −0.016376 | −0.008669 |
| 136 | −0.002678 | −0.004483 | −0.002444 | −0.015997 | −0.011686 | 0.019707 | 0.051299 | −0.000101 | 0.000952 | −0.001397 | −0.012355 | −0.015036 | −0.012887 | 0.018546 |
| 137 | −0.002702 | −0.013931 | −0.007603 | −0.001548 | 0.00767 | −0.012249 | 0.020492 | 0.004758 | 0.003955 | 0.013632 | 0.014772 | −0.031217 | −0.00707 | −0.003102 |
| 138 | −0.018702 | −0.019702 | −0.006149 | −0.000517 | 0.00633 | −0.016324 | −0.013443 | 0.006227 | 0.030347 | 0.006802 | 0.008448 | 0.003284 | 0.007174 | −0.016285 |
| 139 | 0.000439 | −0.017034 | −0.020282 | 0.004349 | 0.026954 | 0.01728 | 0.047103 | −0.047149 | 0.022291 | 0.006985 | −0.031053 | −0.010087 | 0.018947 | 0.070924 |
| 140 | −0.010508 | −0.011298 | −0.002959 | −0.002426 | 0.014781 | 0.016694 | 0.039551 | −0.030834 | 0.03467 | 0.025201 | 0.033034 | −0.011659 | −0.051109 | −0.036067 |
| 141 | −0.000798 | 0.005487 | 0.008684 | −0.002335 | −0.020248 | −0.025002 | −0.001217 | −0.002324 | 0.012346 | 0.007801 | 0.014606 | −0.017908 | −0.021267 | −0.03531 |
| 142 | −0.002062 | 0.00957 | 0.010218 | 0.003584 | 0.010736 | 0.004235 | −0.018635 | 0.001658 | −0.008133 | −0.002688 | −0.025304 | 0.041155 | 0.024031 | 0.000549 |
| 143 | −0.00537 | 0.007384 | −0.002155 | 0.000946 | 0.001257 | −0.013824 | −0.027081 | 0.030808 | 0.01272 | 0.002119 | −0.023909 | −0.010828 | −0.011167 | −0.016238 |
| 144 | 0.002839 | 0.006523 | 0.006507 | 0.000937 | 0.002711 | −0.023361 | −0.006523 | 0.000243 | −0.008817 | −0.028093 | −0.010861 | 0.00659 | 0.010028 | −0.015747 |
| 145 | −0.008283 | 0.004768 | −0.000377 | −0.000453 | 0.003607 | 0.000044 | −0.004885 | 0.05923 | −0.015769 | −0.018472 | −0.015306 | −0.014818 | −0.002832 | −0.020376 |
| 146 | 0.00374 | 0.010242 | 0.009523 | 0.013055 | 0.003906 | 0.00005 | 0.018879 | 0.013497 | 0.006504 | 0.002955 | 0.005585 | 0.00208 | −0.012668 | −0.014164 |
| 147 | −0.017157 | −0.006766 | −0.009593 | 0.006575 | 0.011401 | 0.028858 | 0.029154 | −0.003304 | 0.021347 | 0.016281 | 0.01108 | 0.030828 | 0.030201 | −0.001344 |
| 148 | −0.003525 | −0.017337 | 0.001834 | −0.008864 | 0.029076 | 0.000185 | 0.007964 | −0.054892 | −0.026307 | −0.018191 | −0.031084 | −0.007002 | −0.018113 | 0.010295 |
| 149 | 0.013355 | 0.008783 | 0.010299 | 0.008846 | 0.014396 | −0.007522 | 0.001108 | 0.008208 | 0.000597 | 0.013127 | 0.02059 | −0.045869 | −0.044309 | −0.001131 |
| 150 | −0.007653 | −0.003109 | 0.000954 | 0.000258 | −0.008876 | 0.003905 | −0.023041 | 0.026834 | −0.001034 | 0.001767 | −0.039122 | 0.004269 | 0.010213 | −0.007585 |
| 151 | 0.003111 | 0.008513 | 0.000995 | 0.001285 | 0.017529 | 0.021427 | 0.007904 | −0.026363 | 0.001052 | 0.008189 | 0.011347 | −0.020581 | −0.018494 | −0.009819 |
| 152 | 0.006499 | 0.008557 | 0.012203 | 0.014443 | 0.00817 | 0.003156 | 0.011823 | 0.01122 | 0.010098 | 0.019812 | 0.031062 | 0.020008 | 0.016619 | −0.021517 |
| 153 | 0.008101 | 0.009196 | 0.005628 | 0.011039 | 0.002527 | 0.012246 | −0.003308 | −0.038412 | 0.002033 | 0.004625 | 0.012116 | 0.025103 | 0.008533 | 0.021465 |
| 154 | 0.007813 | 0.013004 | 0.011666 | 0.005447 | −0.006012 | 0.006924 | 0.005398 | 0.005929 | −0.011615 | −0.025965 | −0.026728 | 0.0254 | 0.010956 | −0.006976 |
| 155 | −0.006458 | 0.004642 | 0.001555 | 0.01007 | −0.014782 | −0.013654 | 0.011064 | 0.007618 | −0.007688 | −0.024381 | −0.010554 | 0.017251 | −0.002422 | 0.001632 |
| 156 | 0.012017 | 0.022358 | 0.015459 | 0.007351 | −0.016177 | −0.019706 | 0.001589 | 0.052827 | 0.015723 | −0.008677 | 0.002822 | −0.013813 | −0.004947 | −0.019898 |
| 157 | −0.008183 | 0.00182 | −0.002885 | −0.003947 | −0.006814 | −0.000612 | −0.016401 | 0.009763 | 0.002303 | 0.005464 | −0.004801 | −0.000731 | −0.022 | −0.006124 |
| 158 | 0.002787 | 0.004874 | −0.002412 | −0.022748 | −0.020106 | 0.010169 | 0.034862 | 0.032896 | −0.010534 | −0.032317 | −0.023794 | −0.007539 | −0.006351 | −0.024741 |
| 159 | −0.009701 | −0.009556 | −0.001198 | −0.019907 | −0.032017 | −0.048229 | −0.03245 | 0.005818 | −0.019012 | −0.008161 | −0.018689 | −0.002972 | 0.00982 | −0.015576 |
| 160 | 0.011845 | 0.000069 | 0.004367 | 0.008152 | 0.021669 | 0.003872 | 0.02013 | −0.00291 | 0.005413 | 0.013481 | −0.001558 | −0.020693 | −0.012712 | 0.012505 |
| 161 | 0.032865 | 0.022077 | 0.023154 | 0.018136 | 0.026527 | −0.027323 | −0.004784 | −0.026641 | 0.023239 | 0.003786 | 0.015339 | 0.00793 | 0.00103 | 0.014637 |
| 162 | 0.012523 | 0.006518 | 0.009061 | 0.012374 | 0.028469 | 0.002735 | 0.050955 | 0.037944 | −0.011872 | −0.013456 | −0.025202 | −0.017288 | −0.004666 | −0.023458 |
| 163 | 0.003781 | 0.01697 | 0.014893 | 0.011782 | 0.014286 | −0.001184 | −0.014735 | 0.04798 | −0.002524 | 0.001766 | −0.014054 | 0.015924 | 0.007706 | −0.033994 |
| 164 | 0.000133 | 0.018221 | 0.014303 | −0.001701 | 0.005952 | 0.055039 | 0.054168 | 0.019515 | 0.003412 | −0.000337 | −0.000933 | −0.01669 | −0.005229 | −0.02428 |
| 165 | −0.000188 | −0.003565 | 0.002164 | 0.019693 | 0.0223 | 0.023092 | 0.004743 | −0.006333 | −0.024044 | −0.010927 | 0.043302 | 0.015518 | 0.006322 | 0.028069 |
| 166 | 0.009032 | −0.001972 | 0.002709 | 0.004888 | 0.028791 | 0.003625 | 0.008052 | −0.059811 | 0.005101 | 0.010648 | 0.006751 | −0.019551 | −0.022899 | 0.048251 |
| 167 | −0.021462 | −0.014115 | −0.016359 | −0.000534 | −0.008654 | −0.001252 | 0.033251 | 0.030036 | 0.010923 | 0.001578 | 0.011015 | −0.032023 | −0.015181 | 0.000979 |
| 168 | −0.005772 | −0.000793 | 0.008481 | −0.018025 | −0.018684 | −0.012771 | −0.037874 | −0.022151 | −0.006883 | −0.023894 | −0.020403 | 0.011166 | 0.015154 | −0.052916 |
| 169 | −0.020057 | −0.021778 | −0.024006 | −0.006791 | 0.007289 | 0.013243 | −0.00584 | 0.02347 | 0.017336 | 0.003588 | −0.025308 | −0.008724 | −0.012026 | 0.02833 |
| 170 | −0.013101 | −0.022404 | −0.024889 | −0.016925 | 0.018104 | 0.025381 | 0.009795 | 0.009753 | 0.018491 | −0.001201 | −0.021282 | −0.006437 | −0.000877 | 0.032696 |
| 171 | −0.022915 | −0.018333 | −0.018249 | −0.012696 | −0.040186 | −0.044673 | 0.008452 | −0.008273 | 0.034811 | 0.026969 | 0.005517 | −0.007742 | −0.005136 | 0.012187 |
| 172 | 0.010757 | 0.006834 | 0.003855 | 0.001079 | 0.00777 | −0.001013 | −0.024591 | −0.025001 | −0.018169 | −0.027041 | −0.024295 | 0.004406 | 0.004727 | 0.016115 |
| 173 | 0.012817 | −0.005217 | −0.000248 | 0.005586 | 0.016189 | −0.003159 | −0.011316 | −0.027761 | −0.044616 | −0.038535 | −0.013118 | 0.009827 | 0.016388 | 0.008671 |
| 174 | 0.023706 | 0.010927 | 0.015049 | 0.018495 | 0.02997 | −0.013919 | −0.018811 | −0.028651 | −0.025889 | −0.067274 | −0.060248 | 0.003942 | 0.0186 | 0.0053 |
| 175 | 0.018968 | 0.014675 | 0.013591 | 0.015642 | 0.024261 | 0.020601 | −0.015122 | −0.004232 | 0.00022 | −0.025513 | −0.0805181 | −0.024888 | 0.013182 | 0.032777 |
| 176 | −0.000699 | 0.001194 | −0.005204 | −0.019281 | −0.0181 | −0.01914 | −0.016044 | 0.02818 | 0.024543 | 0.003077 | −0.0316151 | −0.024436 | 0.010985 | 0.03714 |
| 177 | −0.003192 | −0.003916 | −0.001354 | −0.009781 | −0.003724 | 0.030068 | 0.005758 | −0.025168 | −0.008419 | −0.024622 | 0.008619 | 0.012476 | −0.017834 | 0.004854 |
| 178 | −0.053515 | −0.051546 | −0.052103 | −0.037562 | −0.031251 | −0.007784 | 0.014869 | 0.020536 | −0.004576 | 0.009953 | 0.00782 | −0.002818 | 0.010073 | −0.012938 |
| 179 | 0.932606 | −0.053838 | −0.05488 | −0.047732 | −0.054012 | −0.0235621 | −0.004113 | 0.017037 | −0.003712 | 0.002044 | −0.022795 | −0.011494 | −0.014222 | −0.018417 |
| 180 | −0.056738 | 0.936547 | −0.057666 | −0.047346 | −0.032727 | −0.011991 | 0.003671 | 0.002446 | −0.011321 | −0.003158 | −0.016957 | −0.01622 | −0.012209 | 0.002697 |
| 181 | −0.05551 | −0.055536 | 0.94035 | −0.048194 | −0.035178 | −0.009016 | −0.000324 | 0.010385 | −0.002857 | 0.003419 | −0.014094 | −0.013818 | −0.010644 | 0.004821 |
| 182 | −0.045179 | −0.044385 | −0.044563 | 0.933595 | −0.053015 | −0.017303 | −0.005629 | 0.003009 | −0.018824 | −0.01508 | −0.026867 | −0.008615 | −0.003538 | −0.016579 |
| 183 | −0.055093 | −0.029646 | −0.032212 | −0.051592 | 0.88114 | −0.090371 | −0.009061 | 0.00604 | −0.008986 | −0.004103 | −0.02356 | −0.012285 | −0.009016 | −0.050862 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 184 | −0.027052 | −0.009468 | −0.009794 | −0.019482 | −0.088927 | 0.818872 | −0.025769 | −0.028184 | −0.024764 | −0.0306 | −0.051681 | −0.025088 | −0.012913 | −0.030519 |
| 185 | −0.008823 | −0.006599 | −0.008774 | −0.021276 | −0.02007 | −0.026485 | 0.8150121 | −0.025981 | −0.0169381 | −0.031374 | −0.0264551 | 0.000356 | 0.010023 | −0.007906 |
| 186 | 0.015888 | −0.000041 | 0.004576 | 0.000212 | 0.004191 | −0.03727 | −0.021095 | 0.790611 | −0.01763 | −0.00987 | −0.001201 | −0.0078651 | −0.021551 | 0.038486 |
| 187 | −0.006481 | −0.013575 | −0.004838 | −0.019303 | −0.014618 | −0.023953 | −0.009076 | −0.025556 | 0.909198 | −0.079664 | −0.064146 | 0.006269 | −0.000331 | −0.025246 |
| 188 | 0.004149 | −0.005931 | 0.004526 | −0.01631 | −0.007209 | −0.032498 | −0.018334 | −0.015707 | −0.079918 | 0.885178 | −0.108298 | 0.010611 | 0.017617 | −0.022182 |
| 189 | −0.015273 | −0.013585 | −0.008352 | −0.035117 | −0.039287 | −0.06029 | −0.0128 | 0.003358 | −0.064476 | −0.111749 | 0.802384 | −0.010358 | 0.007122 | −0.000893 |
| 190 | −0.008623 | −0.011853 | −0.012994 | −0.013004 | −0.013154 | −0.029085 | 0.015733 | −0.00822 | 0.014548 | 0.017584 | 0.000485 | 0.916451 | −0.054722 | 0.014885 |
| 191 | −0.013286 | −0.009118 | −0.011379 | −0.008398 | −0.011182 | −0.019518 | 0.017659 | −0.016724 | 0.005433 | 0.016928 | 0.007501 | −0.052607 | 0.91487 | 0.004232 |
| 192 | −0.017368 | 0.005084 | 0.008506 | −0.017383 | −0.048512 | −0.014646 | −0.000666 | 0.033285 | −0.027911 | −0.026684 | 0.001044 | 0.012648 | −0.003571 | 0.843852 |
| 193 | 0.005174 | 0.009822 | 0.008904 | −0.012053 | −0.023256 | −0.036079 | −0.019881 | −0.037442 | −0.035808 | −0.036226 | −0.014562 | −0.009145 | −0.00207 | −0.05681 |
| 194 | −0.01817 | −0.016671 | −0.007915 | −0.014831 | −0.026017 | −0.013547 | −0.027771 | −0.01537 | −0.04623 | −0.057338 | −0.078705 | −0.019559 | −0.008139 | −0.02069 |
| 195 | 0.001476 | 0.002097 | −0.006861 | −0.007297 | 0.004285 | −0.007409 | −0.024098 | −0.056948 | −0.009911 | 0.005507 | −0.011681 | −0.021875 | −0.014344 | 0.015397 |
| 196 | −0.008847 | −0.01496 | −0.018772 | −0.022659 | 0.001239 | −0.013866 | −0.013187 | −0.039526 | −0.012548 | −0.01275 | −0.043662 | −0.04462 | −0.027788 | 0.002875 |
| 197 | 0.00585 | 0.002922 | 0.000915 | −0.016374 | −0.003595 | −0.003944 | 0.006905 | −0.00672 | 0.008126 | 0.012186 | 0.018307 | −0.073842 | −0.065152 | −0.01221 |
| 198 | 0.001663 | 0.015123 | 0.00892 | −0.006633 | −0.015451 | −0.012114 | −0.045127 | −0.043379 | −0.014082 | 0.000241 | 0.005601 | 0.015321 | 0.019185 | 0.002557 |
| 199 | −0.012233 | −0.005535 | 0.003197 | 0.021761 | 0.043832 | 0.001257 | 0.025047 | 0.006791 | 0.008827 | 0.008018 | −0.028191 | −0.012048 | −0.020664 | 0.033368 |
| 200 | −0.001781 | 0.011212 | 0.005099 | 0.010022 | −0.019873 | 0.010557 | 0.046918 | −0.040011 | 0.00469 | 0.019501 | 0.039522 | 0.026297 | 0.024902 | −0.007031 |
| 201 | −0.009827 | −0.014099 | −0.009007 | −0.006291 | −0.018208 | 0.020699 | −0.001345 | 0.044084 | 0.00183 | 0.016619 | 0.027502 | −0.00685 | −0.010415 | −0.016427 |
| 202 | 0.010848 | 0.007248 | 0.008797 | 0.004909 | 0.008144 | 0.025619 | 0.000671 | −0.066115 | −0.014265 | 0.010736 | 0.051033 | 0.010076 | 0.017987 | −0.008476 |
| 203 | −0.009333 | −0.001844 | 0.002023 | −0.007058 | −0.014872 | 0.003644 | 0.007372 | 0.038539 | −0.007248 | −0.005872 | −0.00813 | −0.021817 | −0.019401 | −0.021157 |
| 204 | 0.000332 | −0.006503 | −0.012764 | −0.011125 | −0.015328 | −0.040602 | −0.053692 | −0.032755 | −0.011497 | 0.005155 | 0.029591 | 0.008193 | −0.004589 | −0.012927 |
| 205 | −0.024007 | −0.024516 | −0.018761 | 0.004831 | 0.009625 | 0.0087 | −0.009161 | 0.023879 | 0.011706 | 0.021093 | −0.007253 | −0.035392 | −0.018491 | −0.005386 |

| | GL | GM | GN | GO | GP | GQ | GR | GS | GT | GU | GV | GW | GX | GY |
|---|---|---|---|---|---|---|---|---|---|---|---|---|---|---|
| 1 | 0.032567 | 0.01452 | 0.036924 | 0.017773 | 0.004642 | 0.03566 | 0.001731 | −0.04893 | 0.005495 | 0.00301 | −0.016061 | 0.125459 | −0.088361 | 0.008772 |
| 2 | −0.020862 | 0.037142 | 0.010635 | 0.065779 | 0.048583 | −0.043971 | 0.009048 | −0.005288 | 0.028159 | −0.009216 | −0.018871 | 0.161607 | 0.037066 | −0.045407 |
| 3 | 0.079736 | 0.047872 | 0.05217 | 0.049178 | 0.081161 | −0.024073 | −0.00541 | −0.046999 | −0.164226 | −0.019371 | −0.036122 | −0.077514 | 0.028532 | −0.033756 |
| 4 | 0.013731 | 0.062935 | 0.0077 | 0.025898 | −0.008278 | 0.023043 | −0.06644 | 0.098014 | 0.021941 | 0.095426 | −0.026944 | 0.051361 | 0.065143 | 0.104367 |
| 5 | −0.039106 | 0.031908 | −0.034291 | −0.01416 | −0.0338 | 0.013052 | −0.010286 | −0.060999 | 0.098081 | −0.046993 | −0.008548 | −0.028504 | 0.016968 | 0.023922 |
| 6 | −0.033899 | 0.014153 | 0.026754 | −0.009764 | 0.029001 | 0.024113 | −0.012467 | −0.029075 | 0.089897 | 0.003779 | 0.003073 | −0.021594 | −0.105505 | 0.055981 |
| 7 | 0.011627 | −0.087445 | −0.055967 | −0.089255 | −0.047309 | 0.041842 | −0.041843 | −0.025933 | 0.031555 | −0.027121 | −0.04941 | 0.033387 | −0.009943 | −0.126147 |
| 8 | −0.080374 | −0.094662 | −0.0935 | −0.075173 | −0.071308 | −0.017626 | 0.078816 | 0.001596 | −0.048966 | −0.022285 | 0.034647 | 0.069057 | 0.027068 | 0.115476 |
| 9 | −0.046106 | −0.011177 | −0.007432 | −0.023091 | −0.036345 | 0.030939 | −0.015501 | −0.020968 | −0.000683 | −0.033176 | −0.042193 | −0.012053 | 0.100915 | −0.016172 |
| 10 | −0.033759 | −0.069529 | −0.005266 | 0.019066 | 0.046139 | −0.024787 | 0.003341 | 0.0946 | −0.057096 | 0.040419 | −0.002922 | 0.030246 | −0.03469 | −0.040266 |
| 11 | −0.042442 | 0.060797 | 0.013405 | 0.042963 | 0.013138 | −0.026594 | −0.064329 | 0.072926 | −0.046623 | −0.014029 | −0.007652 | 0.032337 | 0.035058 | 0.141958 |
| 12 | 0.046073 | 0.050615 | −0.003385 | −0.005245 | −0.015896 | −0.011918 | −0.031121 | −0.082748 | −0.011562 | −0.006124 | −0.033531 | 0.005817 | 0.036075 | 0.032672 |
| 13 | 0.130649 | 0.053935 | −0.08842 | −0.02455 | 0.002878 | −0.053751 | −0.030456 | −0.048583 | 0.070659 | −0.009059 | −0.010477 | 0.013573 | −0.082034 | 0.036686 |
| 14 | −0.012989 | −0.019989 | −0.025338 | −0.005617 | 0.057901 | 0.023759 | −0.009836 | −0.11486 | 0.082849 | −0.113317 | 0.094141 | −0.053617 | −0.021967 | 0.036931 |
| 15 | −0.000373 | −0.010142 | −0.074009 | −0.05965 | 0.000553 | −0.052811 | 0.014459 | −0.103527 | 0.011369 | −0.035029 | −0.060344 | −0.148783 | −0.020558 | 0.068001 |
| 16 | −0.003042 | 0.057695 | −0.022981 | −0.020019 | 0.030983 | 0.017865 | −0.01848 | 0.043252 | 0.008498 | 0.068259 | 0.019601 | 0.024782 | −0.000258 | −0.162386 |
| 17 | −0.038284 | −0.024964 | −0.010239 | −0.058732 | −0.022239 | 0.058721 | −0.011851 | 0.036768 | −0.045488 | 0.051584 | 0.081406 | −0.065432 | 0.020185 | −0.131137 |
| 18 | 0.027334 | −0.11238 | −0.015616 | 0.034607 | 0.0622 | −0.007042 | −0.105056 | −0.096495 | 0.026519 | 0.005331 | 0.050483 | 0.136607 | −0.052372 | 0.059259 |
| 19 | 0.031095 | 0.137824 | 0.036304 | 0.014601 | −0.025256 | 0.040644 | −0.044245 | 0.052486 | −0.036476 | 0.065399 | 0.077299 | 0.035676 | 0.043816 | −0.065983 |
| 20 | 0.002277 | −0.081489 | 0.128558 | 0.043538 | −0.014755 | 0.091827 | −0.042434 | 0.134793 | −0.000408 | 0.144179 | −0.008382 | 0.03785 | 0.113717 | 0.219248 |
| 21 | 0.013045 | −0.058066 | −0.024734 | −0.014802 | −0.010914 | −0.158158 | −0.100157 | −0.01729 | 0.01725 | −0.085838 | −0.062319 | −0.014237 | 0.020535 | 0.064501 |
| 22 | −0.021982 | −0.053111 | −0.026115 | 0.009829 | 0.02325 | −0.023786 | 0.11603 | −0.04611 | −0.087508 | −0.05148 | 0.108386 | −0.076229 | −0.088543 | −0.104513 |
| 23 | −0.004198 | 0.003861 | −0.021722 | −0.002162 | 0.015363 | −0.032341 | −0.033694 | −0.017222 | −0.049165 | 0.058106 | 0.048874 | −0.007521 | 0.008186 | −0.042295 |
| 24 | −0.029634 | 0.016788 | 0.062079 | 0.0089 | 0.096823 | −0.010691 | 0.091076 | −0.043054 | 0.16993 | 0.009426 | 0.06377 | −0.008925 | 0.019471 | 0.009695 |
| 25 | −0.063631 | 0.017699 | 0.007613 | 0.069063 | 0.007468 | 0.051466 | 0.106917 | −0.007318 | 0.017346 | 0.037087 | 0.008536 | −0.04348 | −0.138151 | −0.016346 |

APPENDIX B3-continued

PCA Transformation Matrix (340 × 340 Early/Late)

| | | | | | | | | | | | | | | |
|---|---|---|---|---|---|---|---|---|---|---|---|---|---|---|
| 26 | −0.028059 | 0.019254 | −0.001859 | 0.022017 | −0.001313 | −0.046318 | 0.300831 | 0.019048 | −0.129262 | −0.049581 | 0.006793 | −0.058692 | 0.07905 | −0.013129 |
| 27 | 0.020833 | −0.010662 | −0.03934 | −0.030421 | 0.062299 | −0.018412 | −0.068442 | 0.044209 | 0.029977 | 0.031626 | −0.014694 | −0.01546 | −0.073941 | 0.031347 |
| 28 | −0.062213 | −0.039012 | −0.010645 | −0.001393 | −0.015556 | −0.119312 | −0.104967 | −0.050967 | 0.091123 | −0.037179 | −0.002214 | −0.133159 | −0.083986 | 0.040188 |
| 29 | 0.010257 | 0.024021 | 0.020929 | 0.012561 | 0.013009 | −0.024646 | 0.030627 | −0.013298 | −0.034154 | −0.027949 | −0.008419 | −0.018934 | −0.02084 | 0.040227 |
| 30 | −0.03069 | 0.016815 | 0.12717 | 0.044533 | 0.055522 | 0.08594 | −0.025925 | 0.004117 | −0.03522 | 0.062388 | −0.100294 | −0.025391 | 0.086125 | −0.063212 |
| 29 | −0.003928 | 0.021257 | 0.015731 | −0.048077 | −0.02281 | 0.077067 | −0.135619 | 0.008054 | 0.015918 | 0.046629 | −0.027237 | 0.030421 | −0.032787 | −0.049921 |
| 32 | −0.007955 | −0.047833 | −0.032829 | 0.002074 | 0.04445 | −0.03845 | 0.030003 | −0.026101 | −0.134761 | −0.059217 | 0.030401 | −0.135653 | 0.033824 | −0.127469 |
| 33 | 0.014722 | 0.061804 | −0.053135 | 0.011448 | 0.010555 | −0.020205 | −0.046487 | 0.008407 | −0.010003 | −0.059207 | 0.053839 | 0.031642 | 0.172863 | 0.09387 |
| 34 | −0.017223 | 0.025584 | −0.032646 | −0.00285 | −0.010687 | −0.082875 | 0.164099 | −0.028349 | 0.133123 | 0.054125 | −0.086455 | 0.117982 | 0.067132 | −0.120436 |
| 35 | 0.021689 | 0.023929 | 0.055061 | 0.006717 | 0.010669 | 0.107542 | −0.083361 | 0.069737 | 0.055871 | 0.131406 | 0.056592 | 0.043042 | −0.07023 | 0.066369 |
| 36 | 0.016183 | 0.026172 | 0.007247 | 0.008383 | −0.046615 | 0.075315 | 0.056072 | 0.020963 | 0.105269 | 0.022491 | 0.05696 | 0.122659 | −0.175719 | −0.010183 |
| 37 | 0.0147 | 0.011746 | 0.045858 | 0.008269 | −0.026063 | 0.108799 | −0.054197 | 0.066355 | −0.047924 | 0.014826 | 0.020789 | 0.059989 | 0.102832 | −0.092292 |
| 38 | −0.000026 | −0.080548 | −0.034776 | −0.041467 | −0.087904 | −0.032056 | −0.095184 | −0.019464 | −0.128733 | −0.070698 | −0.015416 | 0.103868 | −0.202455 | 0.073127 |
| 39 | 0.043583 | −0.027569 | −0.040437 | 0.007323 | 0.117012 | 0.051727 | −0.126306 | 0.109055 | 0.008103 | 0.003508 | 0.043731 | −0.116241 | 0.014935 | −0.055205 |
| 40 | −0.001598 | −0.002378 | 0.005272 | −0.001554 | −0.006585 | 0.031582 | 0.007073 | 0.041784 | 0.000271 | 0.01427 | 0.031718 | 0.000721 | 0.018176 | −0.009645 |
| 41 | 0.039903 | 0.064775 | −0.04081 | −0.037825 | −0.018553 | −0.01683 | −0.013711 | 0.016182 | −0.081989 | −0.039065 | −0.01225 | −0.00053 | −0.12066 | −0.046573 |
| 42 | −0.012167 | −0.01351 | 0.027375 | 0.080325 | 0.101072 | 0.040219 | −0.095332 | −0.136206 | −0.001021 | 0.001784 | −0.039639 | 0.146602 | −0.058203 | 0.053099 |
| 43 | 0.004993 | 0.016939 | 0.000003 | −0.005357 | −0.062319 | −0.029196 | 0.012447 | −0.031336 | 0.016515 | −0.011963 | −0.033772 | −0.054467 | −0.049775 | −0.002486 |
| 44 | −0.003316 | 0.030471 | −0.089298 | −0.062177 | −0.058562 | −0.023473 | 0.039709 | 0.047744 | 0.022941 | −0.02649 | −0.037811 | 0.025403 | 0.087181 | −0.0299 |
| 45 | −0.015757 | −0.041156 | −0.038311 | −0.054878 | −0.001056 | 0.007003 | 0.064938 | 0.015232 | −0.043059 | −0.015742 | −0.065265 | −0.062252 | −0.051273 | 0.023217 |
| 46 | −0.018485 | 0.035113 | 0.013542 | −0.006142 | −0.049969 | 0.09691 | −0.020746 | 0.110081 | −0.003953 | 0.053466 | −0.01051 | −0.008429 | −0.060135 | −0.054287 |
| 47 | −0.026781 | 0.024652 | 0.01329 | 0.032963 | −0.061118 | 0.04067 | −0.025785 | 0.015995 | −0.012899 | 0.021573 | 0.000747 | −0.135914 | −0.037035 | 0.090796 |
| 48 | 0.020253 | 0.021379 | 0.024053 | 0.047622 | 0.026442 | 0.069367 | 0.075801 | −0.002296 | −0.095692 | 0.004566 | 0.057751 | −0.039468 | 0.043514 | −0.00031 |
| 49 | 0.044832 | −0.043493 | 0.024503 | 0.02779 | −0.043504 | 0.10099 | −0.040333 | 0.055128 | 0.025548 | 0.126859 | −0.12554 | −0.041004 | −0.0501 | −0.062458 |
| 50 | 0.023689 | 0.054659 | 0.028362 | 0.015861 | −0.036769 | 0.027121 | 0.136436 | −0.0238 | −0.06883 | 0.021318 | 0.061695 | 0.041197 | 0.016763 | −0.153258 |
| 51 | −0.07942 | −0.04473 | −0.031968 | 0.02028 | −0.016298 | −0.022628 | 0.006895 | −0.057353 | −0.127557 | −0.00889 | −0.066508 | 0.046026 | 0.027186 | −0.085664 |
| 52 | −0.009977 | 0.012456 | 0.031565 | 0.067606 | 0.033672 | 0.002963 | −0.108997 | −0.007554 | 0.033211 | 0.062591 | −0.097036 | 0.025842 | 0.047045 | 0.019762 |
| 53 | −0.057625 | −0.012181 | −0.013657 | −0.00481 | 0.018584 | −0.054244 | −0.008199 | 0.005645 | −0.095942 | −0.005925 | 0.058132 | −0.059358 | −0.0381 | 0.071909 |
| 54 | 0.108965 | 0.043695 | −0.025611 | −0.016872 | 0.055724 | −0.021539 | 0.018008 | −0.008761 | −0.088996 | 0.037607 | 0.065777 | 0.027387 | −0.042992 | 0.038542 |
| 55 | −0.057385 | 0.094106 | −0.169964 | −0.069363 | −0.034409 | −0.097744 | −0.025385 | −0.061033 | 0.041366 | −0.029688 | 0.072119 | −0.020489 | 0.078613 | 0.073417 |
| 56 | −0.006966 | 0.02607 | 0.112125 | 0.078701 | −0.030107 | −0.060754 | 0.037551 | −0.024924 | 0.120136 | −0.117343 | −0.057436 | 0.033022 | 0.086436 | 0.011122 |
| 57 | −0.086549 | −0.107168 | −0.029009 | −0.028511 | −0.046368 | 0.015772 | −0.013293 | 0.081724 | 0.020195 | 0.013421 | −0.010806 | 0.052769 | −0.143867 | −0.067412 |
| 58 | 0.064982 | 0.076865 | −0.055508 | −0.0705 | −0.118909 | 0.021414 | −0.056184 | 0.037105 | −0.014721 | 0.011147 | 0.029769 | −0.091829 | 0.062428 | −0.053202 |
| 59 | −0.033346 | 0.032339 | 0.054229 | 0.051529 | −0.00938 | 0.047689 | 0.026674 | −0.084415 | −0.013253 | 0.030391 | 0.130434 | −0.010625 | −0.015949 | 0.040322 |
| 60 | 0.000887 | 0.015711 | 0.00022 | 0.008555 | −0.015073 | −0.006079 | 0.002577 | −0.01852 | −0.011958 | −0.002214 | −0.032227 | 0.017577 | −0.030415 | 0.021085 |
| 61 | −0.000971 | −0.006787 | −0.005379 | −0.01814 | 0.002299 | 0.017843 | 0.019855 | 0.003067 | 0.007086 | 0.02853 | 0.010829 | 0.039311 | 0.009566 | 0.002719 |
| 62 | 0.030164 | 0.023687 | 0.005917 | 0.00709 | −0.002186 | −0.015483 | −0.00048 | −0.014242 | 0.007874 | 0.013375 | −0.035889 | 0.040204 | 0.016908 | 0.018591 |
| 63 | −0.01471 | −0.022379 | −0.001317 | −0.007596 | 0.014725 | 0.005746 | 0.01824 | 0.020732 | −0.000559 | 0.008007 | 0.007375 | 0.02095 | 0.041426 | 0.009533 |
| 64 | 0.007044 | −0.004617 | −0.008951 | −0.018159 | −0.023822 | 0.030536 | 0.008646 | 0.024528 | 0.033302 | 0.041921 | −0.024745 | 0.008209 | 0.034118 | −0.016664 |
| 65 | 0.010331 | 0.011789 | 0.010499 | 0.020452 | −0.004954 | −0.008175 | 0.041414 | −0.005755 | −0.008439 | −0.000574 | −0.023196 | −0.006768 | 0.026348 | −0.013624 |
| 66 | −0.020147 | −0.000456 | −0.002784 | −0.02877 | −0.026961 | 0.003088 | 0.006298 | 0.039607 | 0.004862 | −0.006549 | 0.018351 | 0.005123 | 0.049942 | −0.026538 |
| 67 | −0.024135 | 0.004418 | 0.016034 | −0.010633 | −0.011183 | 0.00121 | 0.022835 | −0.002496 | 0.000622 | −0.012419 | 0.039127 | −0.006261 | 0.00559 | 0.017827 |
| 68 | −0.024118 | 0.007281 | 0.003418 | 0.017875 | −0.007071 | 0.008159 | −0.000739 | −0.010539 | −0.017239 | 0.014939 | 0.032606 | 0.042654 | 0.021744 | −0.034542 |
| 69 | −0.010314 | −0.013567 | −0.015422 | −0.015205 | −0.000643 | −0.000336 | 0.025482 | −0.024245 | 0.004285 | 0.005644 | −0.002563 | −0.023253 | 0.011794 | −0.00618 |
| 70 | 0.007004 | −0.002566 | 0.008564 | −0.013377 | −0.015604 | 0.000071 | 0.001916 | 0.034908 | 0.012644 | 0.009278 | −0.019775 | 0.034138 | 0.032024 | 0.021656 |
| 71 | 0.013868 | 0.004212 | 0.007082 | 0.022945 | 0.01129 | 0.011199 | 0.026466 | −0.015788 | −0.074954 | 0.006868 | −0.02766 | 0.003783 | −0.002169 | −0.021593 |
| 72 | 0.010326 | 0.024889 | 0.005538 | 0.013021 | −0.000144 | 0.026487 | 0.022229 | −0.040453 | −0.036733 | 0.007387 | −0.013322 | −0.037246 | −0.029916 | 0.046668 |
| 73 | 0.01034 | 0.022607 | 0.041103 | 0.020279 | 0.021243 | 0.030275 | 0.025257 | 0.020437 | −0.064236 | −0.018015 | 0.018803 | −0.007375 | 0.031303 | 0.004323 |
| 74 | 0.032929 | 0.048667 | −0.009598 | −0.000947 | −0.008301 | −0.01016 | −0.017593 | 0.024294 | −0.034935 | 0.023049 | 0.006218 | −0.025264 | 0.044952 | −0.002515 |
| 75 | 0.009327 | 0.004773 | −0.006858 | −0.003299 | −0.00265 | 0.014051 | 0.011504 | 0.029002 | −0.005042 | 0.012133 | −0.004517 | −0.007492 | 0.018718 | −0.005111 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 76 | 0.015004 | −0.008501 | −0.013421 | −0.013799 | 0.013893 | −0.003173 | −0.007718 | 0.041161 | −0.013574 | 0.024903 | −0.014256 | −0.025042 | 0.01163 | 0.010777 |
| 77 | 0.007127 | −0.003775 | −0.00649 | −0.007156 | −0.003286 | 0.006999 | 0.020877 | 0.023677 | −0.01116 | 0.005669 | −0.009174 | −0.006212 | 0.020423 | −0.007881 |
| 78 | 0.006525 | 0.003333 | −0.00043 | −0.0006 | −0.002218 | 0.013967 | 0.010635 | 0.017456 | −0.007116 | 0.009044 | −0.000158 | 0.008702 | 0.02609 | −0.008481 |
| 79 | 0.003661 | 0.005632 | −0.017039 | −0.018069 | −0.021832 | 0.026983 | 0.016717 | 0.058899 | −0.004832 | 0.030471 | −0.001119 | −0.015726 | 0.028228 | −0.015938 |
| 80 | 0.045791 | 0.028502 | −0.03673 | −0.027495 | −0.000935 | −0.019456 | 0.041681 | −0.042249 | 0.001154 | 0.016095 | −0.000051 | 0.085595 | −0.023183 | −0.02498 |
| 81 | 0.003945 | −0.010055 | −0.003138 | 0.014436 | 0.018687 | −0.011918 | −0.008476 | 0.012201 | 0.047174 | 0.019181 | 0.011574 | −0.051607 | 0.062546 | 0.083354 |
| 82 | 0.003121 | −0.010243 | −0.003957 | −0.003667 | −0.016909 | 0.008257 | −0.007591 | −0.006651 | −0.010375 | 0.003087 | −0.008441 | 0.019171 | −0.044327 | 0.005305 |
| 83 | 0.004216 | −0.00623 | −0.00894 | 0.000531 | −0.001668 | −0.008325 | −0.024009 | −0.009724 | −0.012762 | 0.003953 | −0.013335 | 0.026358 | −0.026053 | −0.000408 |
| 84 | 0.015418 | −0.010909 | −0.001288 | 0.004523 | 0.00095 | −0.007459 | −0.012559 | −0.016052 | −0.033838 | −0.001538 | −0.007869 | 0.027465 | −0.026892 | 0.001533 |
| 85 | 0.011103 | 0.017871 | −0.018972 | −0.006093 | 0.007036 | 0.056314 | 0.03163 | 0.004929 | 0.019222 | 0.014149 | 0.07592 | −0.010582 | −0.014422 | 0.000389 |
| 86 | 0.004168 | 0.001421 | 0.009581 | 0.014339 | 0.024437 | 0.010192 | 0.007052 | −0.002515 | −0.013298 | 0.002665 | −0.005403 | 0.01129 | −0.02152 | −0.012264 |
| 87 | −0.000892 | 0.008208 | 0.010119 | 0.020691 | 0.019084 | −0.004935 | −0.010805 | −0.019568 | −0.052702 | 0.02729 | −0.036104 | 0.064138 | −0.01428 | −0.005657 |
| 88 | 0.001589 | −0.012049 | 0.005102 | 0.000151 | −0.004487 | −0.000603 | −0.020707 | −0.027288 | −0.015719 | −0.007397 | −0.004437 | 0.020614 | −0.01662 | −0.008777 |
| 89 | −0.002363 | −0.002591 | 0.003603 | 0.009476 | −0.007064 | −0.009704 | −0.016373 | −0.02817 | −0.019566 | 0.002453 | 0.000514 | 0.034664 | −0.014185 | −0.007161 |
| 90 | 0.009511 | 0.010799 | −0.002025 | 0.008649 | −0.00333 | −0.016182 | 0.001273 | −0.023651 | −0.019138 | 0.011358 | −0.010706 | 0.033853 | 0.001545 | −0.007112 |
| 91 | 0.017247 | 0.00534 | −0.000249 | −0.002325 | −0.017917 | 0.013126 | 0.017718 | 0.000541 | 0.014762 | −0.001451 | 0.009531 | 0.009498 | −0.029035 | −0.005255 |
| 92 | 0.030593 | 0.008776 | 0.04786 | 0.036668 | 0.041147 | 0.037002 | −0.020922 | 0.001851 | 0.026379 | 0.012193 | 0.019718 | −0.038842 | 0.010258 | 0.049292 |
| 93 | 0.014483 | −0.006515 | −0.004384 | −0.005994 | −0.007898 | −0.014655 | 0.018079 | 0.001097 | 0.001985 | 0.000255 | −0.02328 | 0.011977 | −0.011648 | −0.0129 |
| 94 | 0.016671 | 0.016233 | 0.010196 | −0.003386 | −0.0023 | 0.031264 | −0.014403 | −0.011819 | −0.01615 | −0.019792 | 0.02736 | 0.04097 | −0.014409 | −0.029395 |
| 95 | −0.051277 | −0.010806 | −0.034121 | −0.014659 | −0.007963 | −0.045712 | 0.021919 | −0.023685 | 0.007951 | −0.026579 | 0.028712 | 0.007296 | 0.003242 | 0.002808 |
| 96 | −0.008116 | −0.012965 | 0.037466 | 0.007094 | −0.01919 | 0.038111 | 0.021719 | 0.027822 | −0.058815 | −0.003335 | 0.022631 | −0.000027 | −0.03926 | 0.015793 |
| 97 | 0.009589 | 0.005157 | −0.005565 | 0.005562 | 0.006035 | −0.001852 | −0.029365 | 0.019509 | −0.005627 | 0.030225 | 0.000769 | 0.026432 | 0.026052 | 0.013424 |
| 98 | 0.010544 | 0.003004 | −0.011498 | −0.018567 | −0.004581 | 0.017438 | −0.002315 | 0.000484 | −0.008272 | 0.01645 | 0.001071 | 0.000736 | −0.019453 | 0.008532 |
| 99 | 0.010244 | 0.001326 | 0.008479 | 0.008272 | 0.002467 | 0.012746 | 0.006733 | −0.002849 | −0.020673 | 0.006087 | 0.018999 | −0.01331 | −0.003835 | −0.014368 |
| 100 | −0.027963 | −0.005053 | 0.0001 | −0.005518 | −0.011382 | 0.007024 | 0.024277 | −0.005349 | −0.026898 | 0.019635 | −0.009728 | −0.011704 | 0.021351 | 0.017108 |
| 101 | 0.025552 | 0.011907 | −0.022407 | −0.032157 | −0.017224 | 0.015577 | −0.014475 | 0.024294 | −0.018051 | 0.026342 | 0.007426 | 0.015699 | 0.000844 | −0.002767 |
| 102 | −0.044181 | −0.066059 | 0.027354 | 0.018529 | 0.039771 | 0.00747 | 0.03036 | 0.006255 | −0.003269 | 0.018097 | 0.017294 | 0.03118 | −0.033617 | 0.021022 |
| 103 | −0.021874 | −0.013243 | −0.017924 | −0.012807 | −0.017696 | −0.022943 | −0.019791 | −0.007238 | 0.046756 | 0.015652 | −0.029228 | 0.006154 | 0.006363 | −0.052599 |
| 104 | 0.023303 | 0.014855 | 0.002405 | −0.004262 | −0.039308 | −0.011257 | −0.003518 | −0.016463 | −0.014342 | 0.011793 | −0.018571 | −0.00514 | 0.003349 | −0.022554 |
| 105 | 0.004505 | −0.018541 | 0.01644 | 0.027406 | −0.006841 | −0.00311 | −0.022027 | −0.063557 | −0.08688 | −0.023982 | −0.064303 | 0.004487 | 0.003789 | −0.019739 |
| 106 | 0.001588 | −0.004885 | 0.011277 | −0.005908 | 0.030943 | −0.0018 | −0.039763 | 0.026483 | 0.047842 | −0.01398 | −0.034361 | 0.019801 | 0.001745 | −0.005614 |
| 107 | 0.00946 | 0.007464 | 0.011333 | 0.016199 | 0.029099 | −0.002421 | 0.011279 | −0.00146 | −0.027759 | −0.005402 | 0.026006 | 0.033227 | 0.009366 | −0.004332 |
| 108 | 0.048534 | −0.000531 | −0.011063 | −0.011998 | 0.023883 | −0.008494 | 0.009615 | −0.000854 | 0.000364 | 0.022523 | 0.020378 | 0.020957 | −0.035136 | −0.088561 |
| 109 | 0.02507 | 0.000972 | −0.000127 | 0.007138 | 0.05469 | 0.052727 | 0.001449 | −0.040469 | −0.020798 | 0.015253 | 0.037717 | 0.002464 | −0.060973 | −0.003865 |
| 110 | 0.012222 | 0.017381 | −0.046983 | −0.024693 | −0.003385 | 0.043931 | 0.01855 | 0.008457 | 0.001905 | 0.017462 | 0.020303 | 0.028668 | 0.014716 | 0.000988 |
| 111 | 0.025697 | −0.011833 | −0.018301 | −0.008482 | 0.043022 | 0.003659 | −0.006148 | 0.049248 | −0.057399 | 0.00836 | 0.031551 | −0.031362 | −0.010942 | −0.002672 |
| 112 | 0.006661 | −0.015188 | 0.008727 | −0.019158 | 0.005939 | −0.045786 | 0.036199 | −0.01467 | 0.008095 | −0.028558 | −0.011027 | −0.04123 | 0.018211 | −0.048317 |
| 113 | 0.020315 | 0.004413 | 0.016671 | 0.00485 | 0.039296 | 0.031198 | −0.025807 | 0.013192 | 0.023015 | −0.001393 | 0.039718 | 0.016731 | −0.025238 | −0.037806 |
| 114 | 0.030903 | 0.045795 | −0.022333 | −0.029902 | −0.02922 | −0.008799 | −0.012058 | −0.023782 | 0.023663 | −0.025515 | −0.015141 | 0.029187 | 0.096292 | −0.05014 |
| 115 | 0.027545 | −0.026523 | −0.019633 | −0.039682 | −0.030493 | −0.004002 | −0.040314 | 0.039694 | 0.022066 | −0.025241 | −0.03129 | −0.030567 | 0.007058 | −0.047603 |
| 116 | −0.000487 | 0.008337 | −0.010469 | −0.009736 | 0.023843 | 0.000609 | 0.053829 | 0.020418 | −0.093066 | 0.046512 | 0.016571 | −0.077831 | 0.088455 | 0.039309 |
| 117 | 0.000935 | −0.02657 | 0.007429 | 0.006436 | 0.000981 | −0.041709 | −0.012505 | 0.042759 | −0.010038 | −0.009784 | −0.034027 | −0.075412 | 0.006197 | 0.02295 |
| 118 | 0.021067 | −0.006477 | 0.021594 | 0.014457 | −0.024889 | −0.021874 | 0.030917 | −0.004228 | −0.051875 | 0.021098 | −0.011855 | 0.044523 | −0.036028 | 0.013385 |
| 119 | −0.014299 | −0.009856 | −0.009338 | −0.008058 | −0.007554 | −0.022036 | 0.020997 | −0.027113 | −0.014494 | −0.021212 | −0.008445 | −0.021453 | 0.019705 | −0.016091 |
| 120 | −0.010678 | −0.016551 | 0.002466 | −0.000549 | −0.008812 | −0.024589 | −0.008576 | 0.039724 | 0.005093 | 0.011661 | −0.004729 | −0.058309 | 0.057539 | 0.017191 |
| 121 | 0.003433 | −0.005802 | −0.007712 | −0.003112 | 0.008483 | −0.005349 | −0.001718 | −0.00633 | 0.026901 | −0.012527 | −0.002669 | −0.013815 | 0.017418 | −0.00385 |
| 122 | −0.001212 | −0.026081 | −0.022865 | −0.022047 | 0.005233 | −0.017312 | −0.009986 | 0.026935 | −0.00557 | −0.012639 | −0.008438 | 0.003775 | −0.015606 | 0.003278 |
| 123 | −0.017059 | −0.024178 | −0.035061 | −0.016651 | −0.012629 | −0.023437 | 0.030532 | −0.001614 | 0.010674 | −0.017997 | −0.004167 | 0.014747 | 0.020955 | −0.00891 |
| 124 | −0.005863 | 0.001434 | −0.017887 | −0.010201 | 0.000569 | −0.043146 | 0.031276 | −0.015509 | −0.015584 | −0.013045 | −0.009871 | −0.003597 | 0.054864 | −0.02045 |
| 125 | −0.00253 | −0.035687 | −0.019242 | 0.000476 | −0.02382 | −0.013609 | 0.02326 | −0.025987 | −0.000383 | −0.004224 | −0.001301 | −0.00299 | −0.062033 | −0.018182 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 126 | 0.00047 | −0.008495 | 0.018196 | 0.02463 | 0.029321 | −0.024071 | 0.020838 | −0.027724 | −0.020114 | −0.021379 | −0.019683 | 0.003516 | −0.025364 | 0.006536 |
| 127 | −0.014853 | −0.012266 | 0.020435 | 0.022017 | 0.014168 | 0.003855 | −0.003781 | −0.013658 | −0.02444 | −0.008667 | −0.021843 | 0.008266 | −0.037526 | 0.010221 |
| 128 | −0.000828 | 0.018894 | 0.000239 | 0.008009 | −0.039398 | −0.018758 | 0.010752 | −0.026619 | 0.000882 | −0.012492 | −0.029196 | 0.004728 | −0.006755 | 0.030574 |
| 129 | 0.013732 | −0.016394 | −0.006589 | 0.006403 | 0.046343 | −0.01035 | −0.065706 | −0.03713 | 0.032395 | −0.043073 | −0.029341 | −0.081758 | 0.064459 | −0.004379 |
| 130 | 0.015709 | 0.002514 | 0.024139 | −0.004606 | −0.009875 | −0.004604 | −0.029306 | 0.029608 | 0.057607 | −0.001686 | −0.00927 | −0.007028 | 0.018244 | −0.02318 |
| 131 | −0.015401 | 0.011681 | −0.022912 | 0.00645 | −0.009697 | 0.004348 | 0.009884 | 0.014564 | −0.081634 | 0.020153 | −0.015647 | −0.012423 | 0.02821 | −0.072278 |
| 132 | 0.008044 | 0.003087 | 0.001315 | 0.000712 | −0.027563 | −0.001549 | −0.024629 | −0.01084 | 0.001274 | 0.02156 | −0.005153 | −0.015226 | −0.008926 | 0.00391 |
| 133 | 0.006625 | 0.018632 | −0.012995 | 0.02061 | −0.02614 | 0.02569 | 0.013217 | −0.038448 | −0.018797 | −0.004207 | −0.008302 | 0.048392 | −0.023452 | −0.013395 |
| 134 | 0.000545 | −0.023606 | −0.016006 | −0.040983 | −0.050379 | 0.001729 | 0.050727 | 0.022595 | −0.030899 | −0.034736 | 0.032164 | −0.032531 | −0.045688 | −0.062539 |
| 135 | −0.005021 | 0.000677 | 0.009946 | 0.005806 | −0.020164 | −0.005944 | 0.015634 | −0.011764 | −0.017942 | −0.003709 | 0.003064 | −0.014376 | −0.0108 | −0.001208 |
| 136 | −0.002138 | 0.001976 | −0.00222 | 0.009882 | −0.0017 | 0.053902 | −0.000457 | 0.0328 | −0.051418 | 0.017592 | 0.014174 | −0.005563 | 0.004486 | 0.015609 |
| 137 | 0.00044 | 0.021959 | −0.013679 | −0.010694 | −0.01522 | −0.012527 | −0.040359 | −0.030104 | −0.004531 | 0.007477 | −0.011603 | 0.030366 | −0.037231 | 0.003872 |
| 138 | 0.035026 | 0.007254 | 0.0311 | 0.024824 | 0.024438 | −0.000686 | −0.078046 | 0.039973 | 0.007543 | 0.042943 | 0.003754 | 0.007318 | −0.050905 | 0.057499 |
| 139 | 0.03993 | 0.006588 | −0.028047 | −0.044898 | 0.036811 | 0.02477 | 0.02686 | −0.050578 | −0.041739 | −0.003526 | 0.017865 | −0.002684 | −0.0871 | −0.044915 |
| 140 | 0.041856 | 0.017998 | −0.008572 | −0.020245 | −0.034835 | 0.011732 | −0.028497 | 0.009423 | 0.031166 | 0.003464 | 0.0005 | 0.010986 | −0.099388 | 0.015768 |
| 141 | −0.030496 | −0.005952 | 0.029362 | 0.022428 | −0.027116 | −0.009956 | −0.025548 | −0.031936 | −0.017402 | −0.006787 | 0.004112 | 0.010069 | −0.020409 | 0.032849 |
| 142 | 0.009493 | 0.016448 | 0.009676 | 0.018147 | 0.046788 | 0.01888 | −0.045032 | 0.052796 | 0.053366 | 0.032802 | 0.011961 | 0.002274 | 0.032554 | −0.028262 |
| 143 | 0.009439 | −0.008976 | −0.007598 | −0.009712 | −0.023415 | 0.02352 | −0.011732 | 0.037703 | 0.018863 | 0.018802 | −0.007276 | −0.004605 | −0.006438 | −0.03125 |
| 144 | −0.028205 | −0.012251 | −0.001712 | −0.002086 | 0.004223 | 0.002006 | 0.000482 | 0.011225 | 0.022487 | 0.002491 | 0.000422 | −0.00617 | 0.022993 | −0.010664 |
| 145 | 0.013308 | 0.005067 | −0.01095 | −0.010708 | −0.032769 | 0.021437 | 0.006197 | 0.02773 | 0.038151 | 0.002927 | −0.043373 | 0.040311 | −0.003033 | 0.009746 |
| 146 | −0.003205 | 0.000134 | 0.011895 | 0.008923 | −0.008605 | −0.006934 | 0.027341 | −0.006076 | −0.007109 | 0.011797 | 0.018565 | −0.022076 | 0.013971j | 0.002239 |
| 147 | −0.003956 | −0.007789 | 0.028832 | 0.023875 | 0.035493 | 0.007556 | −0.05248 | 0.015953 | 0.066146 | 0.005001 | 0.003329 | −0.024895 | 0.003137 | −0.046141 |
| 148 | −0.009183 | 0.012319 | −0.031146 | −0.030733 | 0.015887 | −0.046037 | −0.009197 | 0.053322 | −0.072892 | 0.01026 | −0.024713 | −0.003654 | −0.016563 | −0.024739 |
| 149 | 0.004214 | 0.012295 | −0.013165 | −0.020025 | −0.067593 | 0.013603 | −0.051754 | 0.022709 | −0.025668 | −0.002601 | −0.01574 | 0.001018 | 0.002788 | 0.003114 |
| 150 | 0.030961 | −0.019551 | 0.003885 | −0.001104 | 0.014502 | −0.021758 | 0.039819 | 0.008985 | 0.016409 | 0.014966 | 0.001289 | −0.027887 | 0.018862 | −0.011866 |
| 151 | 0.001407 | −0.038799 | −0.026719 | −0.05553 | −0.030416 | 0.001047 | −0.005164 | −0.058373 | 0.041461 | −0.061592 | 0.005751 | −0.028946 | −0.078599 | 0.02464 |
| 152 | −0.016292 | −0.006334 | 0.004115 | 0.013984 | 0.018247 | 0.00971 | 0.007509 | −0.004989 | −0.017818 | −0.015131 | 0.017111 | −0.042806 | −0.028307 | −0.024742 |
| 153 | −0.017656 | 0.002658 | 0.021173 | 0.033938 | 0.028492 | 0.017659 | 0.063251 | −0.028001 | −0.011579 | 0.02133 | 0.036706 | −0.006972 | 0.027891 | −0.029062 |
| 154 | −0.008444 | 0.002793 | 0.018305 | 0.028225 | 0.022887 | 0.031106 | 0.00943 | 0.039155 | −0.011644 | 0.019605 | 0.0151 | −0.009538 | 0.026757 | −0.000571 |
| 155 | 0.011687 | −0.018972 | −0.007096 | 0.011952 | 0.000622 | −0.00643 | 0.024507 | −0.008958 | 0.001985 | 0.021481 | −0.027273 | 0.021252 | 0.010859 | 0.003431 |
| 156 | −0.013358 | 0.00472 | 0.024709 | 0.036024 | −0.017482 | 0.018606 | 0.040595 | 0.019135 | −0.023906 | 0.017441 | 0.001777 | −0.000106 | 0.009275 | −0.0289 |
| 157 | 0.010759 | −0.010484 | −0.012 | −0.009412 | −0.011006 | −0.017254 | −0.014182 | 0.0096 | 0.020965 | 0.004299 | −0.005238 | −0.035501 | −0.006098 | 0.059743 |
| 158 | −0.008275 | −0.004655 | −0.021317 | −0.013021 | −0.02615 | 0.011102 | 0.013576 | −0.033964 | −0.035014 | 0.013062 | 0.013198 | 0.083707 | 0.012894 | −0.057594 |
| 159 | 0.01776 | 0.030941 | −0.011561 | −0.005077 | −0.013259 | −0.030619 | −0.010602 | −0.04646 | 0.032027 | −0.020924 | −0.061 | −0.026686 | −0.011525 | 0.08375 |
| 160 | −0.002673 | 0.028379 | −0.022688 | −0.004411 | 0.000073 | −0.007644 | 0.018131 | −0.028946 | −0.021661 | −0.032972 | −0.003815 | 0.02233 | −0.02538 | 0.016566 |
| 161 | −0.001613 | 0.024086 | 0.000116 | −0.008382 | 0.002798 | −0.004617 | −0.018055 | −0.010819 | −0.060879 | 0.026744 | 0.011492 | −0.04164 | 0.054442 | −0.014394 |
| 162 | −0.002534 | −0.002916 | 0.009815 | −0.002911 | −0.009446 | 0.005769 | −0.039976 | 0.007053 | −0.020922 | 0.012861 | 0.003111 | 0.006636 | −0.004845 | 0.028593 |
| 163 | −0.013261 | −0.001142 | −0.001206 | 0.003898 | 0.012603 | −0.014217 | −0.045484 | 0.01707 | 0.003644 | 0.000758 | −0.00592 | −0.011047 | −0.027756 | −0.0101 |
| 164 | −0.009017 | −0.007551 | 0.007204 | 0.007813 | −0.020741 | 0.011105 | −0.059294 | −0.057684 | 0.014043 | −0.015363 | −0.019127 | 0.040518 | −0.057867 | 0.02017 |
| 165 | 0.02079 | −0.045591 | −0.005481 | 0.014167 | 0.00754 | −0.037478 | −0.013431 | −0.03296 | −0.064898 | −0.066061 | −0.008908 | −0.038499 | −0.060879 | 0.035608 |
| 166 | 0.013035 | 0.009808 | −0.028832 | −0.022669 | 0.012606 | −0.025948 | −0.047821 | −0.012626 | 0.050053 | −0.02717 | 0.000655 | 0.011625 | −0.006704 | 0.016121 |
| 167 | 0.026235 | 0.021326 | −0.00214 | −0.009699 | −0.032924 | 0.026792 | −0.043725 | −0.02047 | 0.020991 | 0.023238 | −0.01624 | 0.016812 | −0.044001 | −0.049868 |
| 168 | −0.048876 | −0.020989 | 0.039993 | 0.025296 | 0.005384 | 0.013269 | −0.01036 | 0.001679 | −0.013565 | 0.003269 | −0.001171 | 0.012206 | 0.009865 | 0.004135 |
| 169 | 0.014605 | −0.012686 | 0.010085 | −0.005959 | −0.003959 | 0.002883 | −0.017606 | 0.018745 | −0.00951 | 0.018155 | −0.012369 | −0.008797 | 0.049837 | 0.001919 |
| 170 | 0.00822 | 0.00151 | 0.01322 | −0.00305 | −0.002205 | −0.005137 | −0.000465 | 0.023817 | −0.008715 | 0.00336 | −0.005446 | −0.004683 | 0.085318 | 0.015729 |
| 171 | 0.00212 | 0.000151 | 0.023024 | 0.010679 | −0.001973 | −0.007242 | 0.004576 | −0.012637 | −0.014635 | −0.000111 | 0.00332 | −0.020417 | 0.053601 | 0.002612 |
| 172 | −0.008283 | −0.035049 | −0.034105 | −0.02341 | −0.004711 | −0.048862 | 0.016192 | −0.051677 | 0.035566 | −0.036366 | −0.000522 | −0.036051 | 0.00621 | 0.025096 |
| 173 | −0.019605 | −0.028517 | −0.01636 | −0.006991 | 0.004664 | −0.006267 | 0.013244 | −0.016382 | 0.021969 | −0.024965 | 0.006508 | 0.001961 | −0.018326 | 0.027111 |
| 174 | −0.02777 | −0.031784 | −0.002414 | −0.018438 | 0.000737 | 0.003725 | −0.022864 | −0.005334 | 0.041639 | −0.006797 | 0.015517 | 0.036576 | −0.000893 | 0.00762 |
| 175 | −0.019472 | −0.06733 | −0.005171 | −0.042516 | −0.008131 | −0.033774 | −0.035798 | 0.007596 | 0.034915 | −0.014588 | 0.002389 | 0.012904 | 0.010247 | 0.025818 |

APPENDIX B3-continued

PCA Transformation
Matrix (340 × 340 Early/Late)

| | | | | | | | | | | | | | |
|---|---|---|---|---|---|---|---|---|---|---|---|---|---|
| 176 | −0.013333 | −0.022139 | −0.004959 | 0.001902 | −0.00728 | −0.029131 | −0.012528 | 0.01645 | −0.060947 | 0.015078 | 0.016399 | −0.035365 | −0.011786 | 0.012379 |
| 177 | 0.00582 | 0.019623 | 0.03479 | 0.014204 | 0.001853 | −0.026185 | 0.034651 | −0.0563 | 0.004667 | −0.013378 | −0.030635 | 0.014882 | 0.051847 | −0.017464 |
| 178 | −0.001276 | −0.015144 | 0.005891 | −0.010886 | 0.022676 | −0.02093 | −0.004662 | −0.043583 | −0.009862 | −0.017314 | −0.023935 | 0.022733 | 0.000548 | 0.006332 |
| 179 | 0.003098 | −0.016359 | −0.008393 | −0.014094 | 0.003448 | 0.001716 | 0.002503 | −0.000081 | −0.007068 | 0.013818 | −0.01437 | 0.012335 | −0.010725 | 0.003238 |
| 180 | 0.004065 | −0.014522 | −0.003927 | −0.016195 | 0.000391 | 0.014739 | 0.004839 | 0.005497 | −0.01998 | 0.014247 | −0.001178 | 0.01323 | −0.0151 | −0.003441 |
| 181 | 0.007788 | −0.004606 | −0.016337 | −0.021083 | 0.000092 | 0.00683 | 0.014209 | −0.002285 | −0.011304 | 0.011224 | −0.001289 | 0.00301 | −0.007513 | 0.001657 |
| 182 | −0.012268 | −0.00726 | −0.007446 | −0.012888 | −0.006058 | −0.006285 | 0.032588 | −0.003679 | −0.018567 | 0.00425 | −0.005334 | −0.00099 | 0.018813 | 0.013968 |
| 183 | −0.024982 | −0.020833 | −0.001269 | 0.004853 | −0.002519 | −0.020608 | 0.056662 | −0.032527 | −0.024509 | −0.00214 | −0.025483 | −0.008115 | 0.016622 | 0.015245 |
| 184 | −0.038946 | −0.026595 | −0.037795 | −0.03181 | −0.012432 | −0.037334 | 0.015799 | −0.006106 | 0.038747 | −0.013724 | −0.022944 | −0.032091 | −0.01006 | 0.008914 |
| 185 | −0.01853 | −0.031619 | −0.027665 | −0.02919 | −0.010636 | −0.050519 | 0.053729 | 0.034982 | 0.015721 | −0.002097 | 0.002439 | −0.042242 | 0.003004 | 0.034292 |
| 186 | −0.028741 | −0.021357 | −0.058138 | −0.04801 | −0.02079 | −0.035583 | 0.019068 | −0.032396 | 0.028234 | −0.061307 | 0.045295 | −0.06403 | 0.004664 | 0.004361 |
| 187 | −0.042705 | −0.051336 | −0.011799 | −0.008772 | 0.004043 | −0.013684 | 0.008896 | −0.003148 | −0.003178 | −0.011268 | −0.015937 | 0.009066 | 0.00221 | 0.009256 |
| 188 | −0.046962 | −0.061065 | 0.008501 | −0.005916 | 0.014053 | 0.004783 | 0.000986 | 0.010097 | 0.003842 | 0.010098 | −0.004835 | 0.030004 | 0.003416 | 0.008219 |
| 189 | −0.035259 | −0.07763 | −0.00749 | −0.031382 | 0.017336 | 0.007366 | −0.030888 | 0.039844 | 0.005732 | 0.050729 | −0.006936 | 0.041441 | −0.006318 | 0.011059 |
| 190 | −0.002974 | −0.009255 | −0.035539 | −0.044873 | −0.076864 | −0.003794 | −0.014985 | 0.01183 | −0.019757 | −0.001266 | −0.023563 | −0.001934 | −0.035107 | −0.025237 |
| 191 | 0.003306 | −0.002586 | −0.016667 | −0.022912 | −0.066282 | 0.00187 | −0.021001 | 0.015781 | −0.027243 | 0.010526 | −0.021136 | −0.01751 | −0.018062 | 0.00649 |
| 192 | −0.05739 | −0.019075 | 0.02535 | 0.008985 | −0.017371 | 0.002886 | 0.028932 | −0.019649 | −0.014259 | −0.013212 | −0.032713 | 0.002674 | 0.011737 | 0.012739 |
| 193 | 0.899514 | −0.040496 | −0.010043 | −0.004039 | −0.015739 | −0.018057 | 0.033662 | −0.00998 | 0.006844 | −0.023374 | 0.001832 | −0.02017 | 0.010579 | 0.010981 |
| 194 | −0.047903 | 0.859578 | −0.011624 | −0.019869 | −0.002528 | −0.016107 | −0.009604 | −0.001046 | −0.001577 | −0.016138 | −0.022181 | −0.000433 | −0.06391 | 0.001864 |
| 195 | 0.006103 | −0.011887 | 0.853002 | −0.085119 | −0.037407 | −0.076175 | 0.010793 | −0.02751 | 0.003626 | −0.056997 | 0.009758 | −0.028846 | −0.023287 | 0.000904 |
| 196 | 0.002091 | −0.022492 | −0.089633 | 0.901948 | −0.056151 | −0.030993 | −0.009207 | 0.003788 | 0.010964 | −0.028507 | 0.004964 | −0.026902 | −0.020999 | −0.011766 |
| 197 | −0.009352 | 0.008391 | −0.033034 | −0.045768 | 0.872234 | −0.006229 | −0.001159 | 0.008063 | −0.017118 | −0.013229 | −0.021587 | −0.003084 | −0.00985 | −0.008016 |
| 198 | −0.004149 | −0.014437 | −0.076506 | −0.02468 | 0.005233 | 0.827125 | 0.032634 | −0.074237 | 0.010841 | −0.100719 | −0.032394 | −0.032533 | 0.029645 | 0.035884 |
| 199 | 0.025218 | −0.019807 | 0.007523 | −0.008765 | 0.011847 | 0.031234 | 0.684725 | 0.040921 | 0.067991 | 0.035571 | −0.039825 | 0.031561 | −0.033642 | 0.058181 |
| 200 | 0.006835 | −0.003266 | −0.034893 | 0.002806 | 0.023278 | −0.070158 | 0.033057 | 0.80461 | 0.015053 | −0.092534 | −0.000589 | 0.010161 | −0.046532 | 0.011246 |
| 201 | 0.008784 | −0.003401 | 0.008468 | 0.023646 | 0.013661 | 0.007067 | 0.045506 | 0.010406 | 0.717704 | 0.000294 | 0.026177 | −0.049665 | 0.001592 | −0.061575 |
| 202 | −0.009584 | −0.034835 | −0.058212 | −0.029144 | −0.01114 | −0.096892 | 0.032481 | −0.096462 | −0.008601 | 0.838039 | 0.006618 | −0.052268 | −0.012834 | 0.011399 |
| 203 | 0.006467 | −0.018223 | 0.011277 | 0.007463 | −0.029829 | −0.015096 | −0.040719 | −0.000883 | 0.010148 | 0.006019 | 0.833063 | 0.026827 | 0.015057 | 0.003903 |
| 204 | −0.0092 | −0.009453 | −0.030495 | −0.031537 | 0.000127 | −0.034254 | 0.045497 | 0.001461 | −0.064317 | −0.049155 | 0.014972 | 0.701794 | 0.023444 | 0.019346 |
| 205 | 0.019531 | −0.065013 | −0.0358 | −0.03084 | −0.019845 | 0.013691 | −0.026906 | −0.041749 | 0.033461 | −0.007093 | 0.011551 | 0.056564 | 0.625123 | 0.003677 |
| 206 | 0.005655 | 0.006069 | −0.02292 | −0.034584 | −0.007297 | 0.031881 | 0.088375 | 0.007085 | −0.036206 | 0.005226 | −0.001268 | −0.008382 | −0.024237 | 0.687854 |
| 207 | −0.007433 | 0.030525 | 0.018511 | −0.020179 | −0.011917 | 0.019271 | −0.031933 | −0.007786 | 0.002124 | 0.032636 | 0.006383 | −0.058066 | 0.046494 | −0.012682 |
| 208 | 0.009031 | −0.015539 | −0.01227 | 0.001862 | −0.040807 | −0.032215 | 0.045018 | −0.028784 | −0.005376 | −0.04493 | −0.058319 | −0.029896 | −0.0433 | −0.046156 |
| 209 | −0.022716 | −0.049921 | 0.000323 | −0.011949 | −0.019785 | −0.004878 | −0.022824 | −0.021117 | 0.027229 | −0.055728 | −0.016578 | −0.030185 | −0.024482 | 0.038487 |
| 210 | 0.01108 | 0.032479 | −0.004535 | 0.010768 | −0.025171 | −0.023078 | 0.005038 | −0.028208 | −0.02548 | 0.008929 | −0.023015 | −0.01121 | 0.048683 | 0.047136 |
| 211 | 0.027164 | 0.026444 | 0.005714 | 0.010892 | 0.001413 | 0.026791 | 0.064455 | −0.014056 | −0.015152 | −0.013966 | 0.044477 | −0.049945 | 0.001252 | −0.009922 |
| 212 | 0.000637 | 0.052013 | −0.055812 | −0.007716 | 0.003125 | −0.067963 | 0.027244 | −0.036362 | 0.078079 | 0.004411 | 0.02044 | 0.041088 | −0.001859 | 0.05023 |
| 213 | −0.015093 | −0.036293 | 0.007821 | 0.003067 | 0.03285 | 0.006217 | 0.007966 | 0.018023 | 0.026042 | 0.02956 | −0.027717 | 0.013279 | 0.025665 | −0.034115 |
| 214 | −0.002149 | −0.010942 | −0.009959 | −0.013827 | 0.005855 | 0.007759 | 0.01605 | −0.004908 | −0.018804 | 0.00914 | 0.009789 | -4.0063 | 0.009012 | 0.010561 |
| 215 | −0.005468 | −0.016399 | −0.023056 | −0.018172 | 0.002191 | −0.004117 | 0.02526 | −0.032449 | 0.012888 | −0.002576 | 0.036479 | −0.042276 | −0.065259 | 0.009436 |
| 216 | 0.003753 | −0.009667 | 0.035539 | 0.012171 | 0.005268 | 0.013992 | −0.038579 | 0.005754 | −0.006627 | 0.009954 | 0.017581 | 0.035217 | −0.006937 | 0.012254 |
| 217 | 0.017349 | −0.048613 | −0.015109 | −0.005195 | 0.01696 | −0.029854 | −0.025548 | 0.002233 | 0.025637 | −0.026884 | −0.031821 | 0.002098 | −0.04887 | −0.009452 |
| 218 | 0.004075 | 0.023624 | −0.00887 | −0.001882 | −0.002379 | 0.009347 | 0.023628 | 0.015783 | 0.010929 | 0.000253 | 0.023653 | −0.019879 | −0.010474 | 0.018675 |
| 219 | 0.024056 | 0.016245 | 0.011809 | 0.007319 | 0.025346 | 0.001635 | −0.005365 | 0.010947 | 0.027385 | 0.006435 | 0.011327 | 0.034153 | 0.034359 | 0.018431 |
| 220 | 0.02355 | −0.011382 | −0.018389 | −0.008769 | −0.002261 | −0.031825 | 0.0136 | −0.012969 | 0.021938 | 0.005505 | −0.040972 | −0.006601 | −0.006945 | 0.008367 |
| 221 | 0.01533 | 0.0119 | 0.007438 | 0.022658 | 0.007019 | 0.006398 | 0.058753 | 0.00095 | 0.000233 | 0.001205 | 0.010755 | −0.002337 | −0.031083 | −0.003284 |
| 222 | −0.014045 | −0.000939 | 0.01078 | 0.010521 | 0.00699 | 0.021049 | 0.011688 | −0.006254 | 0.017403 | 0.007305 | −0.01651 | 0.026254 | −0.056526 | 0.019082 |
| 223 | −0.024018 | −0.014412 | 0.008879 | 0.011981 | 0.01049 | 0.024673 | 0.015389 | 0.004884 | 0.015597 | 0.019021 | 0.003155 | −0.000972 | −0.023935 | 0.012908 |
| 224 | 0.006111 | −0.01645 | −0.006215 | −0.007388 | −0.005459 | −0.030933 | −0.039437 | −0.023823 | −0.03715 | −0.053561 | 0.014136 | -4.030582 | −0.002901 | −0.029798 |
| 225 | 0.017182 | −0.012434 | −0.002368 | 0.007391 | −0.000778 | −0.027326 | −0.045619 | −0.028365 | −0.034186 | −0.049244 | 0.005539 | −0.010431 | 0.008334 | −0.012003 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 226 | −0.009061 | 0.009344 | −0.012053 | −0.001312 | −0.001713 | −0.022171 | 0.009786 | −0.0016 | 0.014305 | −0.008836 | −0.006734 | −0.007564 | 0.051068 | 0.025622 |
| 227 | −0.000109 | −0.011512 | 0.017268 | 0.000659 | 0.000625 | −0.016696 | 0.000358 | 0.005215 | −0.013273 | 0.003226 | −0.013095 | 0.008994 | 0.041893 | −0.064589 |
| 228 | −0.015924 | 0.009315 | 0.001511 | −0.015586 | −0.024582 | −0.003226 | −0.021289 | −0.019584 | 0.03577 | −0.025426 | −0.024239 | 0.000054 | −0.002911 | 0.002842 |
| 229 | 0.001051 | 0.019045 | −0.021868 | 0.008785 | 0.022263 | −0.010738 | −0.009695 | −0.015736 | 0.003519 | −0.00855 | −4.014987 | −0.000058 | 0.014901 | 0.027535 |
| 230 | 0.00161 | 0.00337 | 0.026309 | 0.013573 | 0.010634 | 0.016283 | −0.02666 | −0.012367 | −0.021705 | 0.015426 | 0.016883 | 0.038249 | −0.027479 | 0.010672 |
| 231 | −0.00279 | −0.001112 | −0.008519 | −0.005196 | −0.013377 | 0.016282 | 0.000326 | 0.032697 | 0.025499 | 0.013554 | 0.000793 | −0.014914 | −0.010151 | −0.013179 |
| 232 | −0.012873 | 0.003697 | −0.037297 | −0.025722 | −0.018539 | −0.046404 | −0.020148 | −0.025836 | 0.007074 | −0.027169 | 0.010131 | −0.020005 | −0.030204 | 0.029841 |
| 233 | 0.008469 | 0.020311 | −0.00297 | 0.004185 | 0.041667 | −0.017588 | 0.020018 | −0.029607 | −0.028848 | 0.004652 | 0.016159 | −0.008319 | −0.008014 | 0.024986 |
| 234 | 0.027705 | 0.03667 | 0.041724 | 0.011679 | −0.001265 | 0.030314 | 0.00764 | −0.021293 | 0.039874 | 0.032369 | −4.00057 | 0.059659 | 0.015027 | −0.018379 |
| 235 | 0.021874 | 0.010621 | 0.035374 | 0.011571 | 0.03022 | 0.019088 | 0.002161 | −0.025128 | 0.053961 | 0.015179 | 0.00492 | −0.004664 | −0.034859 | −0.018423 |
| 236 | 0.003217 | −0.00773 | −0.000257 | −0.009148 | −0.014988 | −0.000927 | −0.005842 | 0.005826 | 0.003341 | 0.016036 | 0.011372 | 0.00187 | −0.039753 | −0.037913 |
| 237 | 0.005949 | 0.003932 | 0.016861 | 0.003653 | −0.027315 | 0.022617 | −0.012273 | 0.014204 | −0.020774 | 0.006321 | 0.003439 | −0.002916 | −0.024482 | 0.015307 |
| 238 | 0.014856 | −0.008327 | 0.003671 | −0.004495 | −0.006932 | 0.017689 | −0.023409 | 0.005199 | −0.007712 | −0.005241 | 0.012707 | 0.028914 | −0.035245 | 0.017062 |
| 239 | 0.000632 | −0.009404 | −0.013608 | −0.01199 | 0.010284 | 0.000017 | −0.017071 | 0.009347 | 0.005088 | −0.018408 | 0.007775 | 0.016433 | −0.018598 | 0.011195 |
| 240 | −0.008361 | −0.013926 | 0.011046 | −0.007608 | 0.007336 | 0.011898 | −0.026078 | 0.027295 | −0.012499 | 0.005629 | −0.01792 | −0.023942 | −0.008299 | −0.011932 |
| 241 | 0.004637 | 0.016774 | 0.01701 | −0.004031 | 0.020028 | 0.013722 | 0.004664 | 0.003347 | −0.036522 | 0.017639 | 0.016473 | −0.034247 | 0.01399 | 0.010154 |
| 242 | 0.012683 | 0.008097 | 0.011288 | −0.000968 | 0.018759 | 0.001209 | 0.032082 | −0.008966 | 0.012739 | 0.008222 | −0.009489 | −0.003139 | −0.056552 | −0.03618 |
| 243 | 0.011138 | 0.000926 | 0.000971 | −0.008685 | 0.025764 | −0.013195 | 0.029394 | −0.015626 | −0.003558 | −0.013303 | −0.000472 | −0.027066 | −0.021937 | −0.017199 |
| 244 | −0.007155 | 0.003806 | 0.01241 | 0.029357 | 0.013145 | −0.006493 | 0.039138 | −0.006518 | −0.021275 | −0.000456 | 0.011193 | 0.000502 | 0.010833 | −0.039537 |
| 245 | −0.009582 | −0.010772 | 0.019532 | 0.017852 | 0.020043 | 0.019822 | −0.001903 | 0.003995 | 0.011411 | 0.026875 | 0.000677 | 0.023721 | −0.011383 | −0.04032 |
| 246 | 0.010992 | 0.007648 | 0.004648 | 0.002658 | 0.000966 | 0.014936 | −0.004901 | −0.005327 | 0.00461 | 0.025373 | −0.022774 | 0.027202 | −0.022426 | 0.02966 |
| 247 | 0.024833 | −0.010185 | −0.015777 | −0.015264 | −0.001014 | −0.004135 | −0.009954 | −0.004823 | 0.003034 | 0.011768 | −0.021692 | 0.021728 | −0.029784 | 0.004641 |
| 248 | 0.013991 | −0.013048 | −0.024067 | −0.021348 | −0.015086 | −0.017116 | 0.013502 | −0.015368 | 0.015861 | 0.003692 | −0.005025 | 0.006249 | −0.03974 | −0.00138 |
| 249 | −0.03265 | −0.007625 | 0.001548 | −0.003643 | 0.002435 | 0.004684 | −0.00485 | 0.007112 | −0.022564 | −0.00109 | −0.007076 | −0.049244 | −0.028454 | 0.003082 |
| 250 | −0.008724 | 0.001112 | 0.032752 | 0.011384 | −0.003096 | 0.025412 | −0.017304 | 0.019712 | −0.01357 | 0.029292 | −0.006346 | −0.003875 | 0.01643 | 0.007226 |
| 251 | 0.004438 | 0.009385 | 0.039155 | 0.014024 | 0.009231 | 0.020016 | 0.002562 | 0.001782 | −0.01829 | 0.00865 | −0.005525 | −0.019531 | 0.027367 | −0.013837 |
| 252 | −0.008017 | 0.003596 | −0.029445 | −0.025095 | −0.002161 | −0.016845 | 0.025437 | −0.009203 | −0.00421 | −0.011123 | −0.004682 | −0.04475 | 0.007185 | −0.035915 |
| 253 | −0.001827 | −0.010979 | 0.00392 | 0.001574 | −0.002943 | −0.008826 | 0.004329 | −0.025997 | −0.008191 | −0.007445 | −0.000223 | −0.027448 | −0.004546 | 0.01515 |
| 254 | −0.032139 | −0.011882 | 0.005086 | 0.00799 | 0.014804 | 0.005043 | 0.011936 | 0.014524 | 0.015262 | 0.013584 | 0.009127 | −0.023129 | 0.037958 | −0.009719 |
| 255 | −0.006331 | 0.001348 | 0.01781 | 0.020878 | 0.005392 | −0.004218 | 0.02935 | 0.0026 | 0.001137 | 0.015861 | −0.009804 | 0.004806 | 0.036493 | −0.013649 |
| 256 | −0.01721 | −0.003974 | −0.015401 | −0.006796 | −0.025018 | −0.0099 | 0.016994 | −0.01262 | 0.002358 | 0.003536 | −0.010488 | −0.016165 | −0.007462 | −0.000748 |
| 257 | 0.020255 | −0.001133 | −0.013944 | −0.013324 | −0.015575 | −0.009507 | −0.0143 | −0.018118 | 0.004138 | −0.001584 | −0.005509 | 0.006376 | −0.014943 | 0.001123 |
| 258 | 0.014355 | −0.018514 | −0.01663 | −0.023656 | −0.019988 | 0.010095 | −0.04845 | −0.00676 | −0.00553 | −0.001896 | 0.011919 | −0.005617 | −0.011 | −0.015515 |
| 259 | −0.023919 | 0.002342 | 0.024984 | 0.009045 | 0.009615 | 0.02766 | 0.007836 | −0.003548 | −0.00276 | 0.01614 | −0.014967 | −0.007594 | −0.001017 | −0.00155 |
| 260 | −0.016043 | −0.009324 | −0.022184 | −0.01516 | 0.016943 | −0.004607 | −0.01374 | −0.004824 | 0.017013 | 0.001527 | −0.02371 | −0.015488 | 0.01718 | −0.009422 |
| 261 | −0.001452 | −0.004595 | −0.040762 | −0.043655 | −0.022605 | 0.01574 | −0.008933 | 0.017329 | 0.007982 | 0.001466 | −0.020459 | −0.002618 | −0.00457 | −0.042722 |
| 262 | 0.005428 | −0.009347 | −0.037314 | −0.033936 | −0.011284 | −0.014113 | −0.006941 | −0.01777 | 0.013711 | −0.028699 | −0.0112 | 0.002071 | −0.047721 | −0.033874 |
| 263 | 0.006065 | −0.005807 | −0.011016 | −0.015146 | −0.006403 | −0.009605 | 0.014578 | −0.03156 | 0.011514 | −0.020126 | −0.011636 | −0.00052 | −0.028091 | −0.037158 |
| 264 | −0.041653 | −0.010172 | 0.0169 | 0.006216 | 0.001147 | 0.027491 | 0.005148 | 0.009112 | −0.010707 | 0.021996 | −0.010263 | −0.018884 | 0.002224 | 0.005923 |
| 265 | −0.041311 | −0.019176 | −0.054722 | −0.032424 | −0.010111 | −0.001504 | −0.037275 | 0.018771 | 0.002335 | 0.002685 | 0.002961 | −0.035916 | 0.033921 | 0.008454 |
| 266 | −0.007423 | −0.015271 | −0.070329 | −0.04057 | −0.023833 | −0.019825 | −0.006826 | 0.023056 | −0.000707 | −0.006326 | 0.001968 | −0.02231 | 0.031373 | −0.011835 |
| 267 | −0.011865 | 0.012985 | −0.019797 | 0.006929 | 0.013455 | −0.029687 | −0.032623 | −0.011348 | 0.015472 | −0.022918 | −0.010782 | −0.008966 | 0.04103 | 0.01231 |
| 268 | −0.00181 | 0.011239 | −0.013037 | −0.00477 | −0.002705 | −0.027517 | −0.012644 | −0.002202 | 0.014241 | −0.009977 | −0.0129091 | −0.016364 | 0.048802 | 0.029493 |
| 269 | 0.003259 | 0.007676 | −0.00787 | 0.000494 | 0.003076 | −0.025965 | 0.011893 | 0.000474 | 0.008222 | −0.008194 | 0.004566 | −0.019796 | 0.03905 | 0.020174 |
| 270 | −0.010715 | −0.001865 | −0.004465 | −0.007764 | −0.006702 | −0.032981 | 0.00989 | 0.00442 | 0.010122 | −0.009446 | −0.015883 | −0.002053 | 0.059596 | −0.016442 |
| 271 | 0.003589 | 0.011906 | 0.018542 | 0.040555 | 0.030606 | −0.004351 | −0.0066511 | −0.020201 | −0.018033 | −0.031853 | 0.005007 | −0.015374 | 0.039109 | 0.007244 |
| 272 | −0.004417 | 0.026097 | −0.025611 | 0.003827 | 0.010648 | −0.006624 | −0.014369 | −0.004504 | 0.01625 | −0.007726 | −0.022101 | 0.0089 | 0.032028 | 0.021891 |
| 273 | 0.003384 | 0.015697 | −0.019036 | −0.011806 | 0.004755 | −0.011034 | −0.01773 | −0.011327 | 0.007665 | −0.002756 | −0.005902 | −0.011833 | 0.010354 | 0.014948 |
| 274 | 0.005717 | 0.014902 | −0.015823 | −0.010755 | 0.009986 | −0.007696 | −0.010832 | −0.00783 | 0.001486 | 0.001073 | −0.00089f | −0.010906 | 0.010997 | 0.00685 |
| 275 | −0.011413 | −0.010431 | 0.016462 | 0.000303 | 0.016628 | −0.012671 | 0.001946 | −0.012826 | −0.01104 | 0.016098 | −0.007655 | 0.028271 | −0.006769 | −0.068155 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 276 | 0.008589 | 0.003408 | −0.002758 | −0.016191 | −0.017713 | 0.007621 | −0.026557 | 0.020059 | 0.009775 | 0.019257 | −0.000404 | 0.011942 | −0.028915 | −0.039157 |
| 277 | −0.01268 | 0.005028 | −0.01176 | −0.010039 | 0.001721 | 0.003044 | −0.014457 | 0.024333 | 0.011801 | −0.008528 | 0.018575 | 0.001325 | −0.016103 | −0.013378 |
| 278 | −0.028027 | −0.000589 | −0.005089 | −0.00179 | 0.004479 | −0.001833 | 0.010612 | 0.008659 | −0.003511 | −0.020987 | 0.035443 | −0.008799 | −0.016462 | −0.019889 |
| 279 | −0.009456 | −0.012058 | −0.01088 | −0.017727 | 0.008392 | −0.005348 | −0.005773 | 0.014646 | 0.016631 | −0.027691 | 0.015632 | 0.023314 | 0.002104 | −0.009465 |
| 280 | 0.006745 | 0.001837 | 0.018518 | −0.002262 | 0.00899 | −0.006165 | 0.00065 | −0.010741 | −0.01978 | −0.007913 | 0.009384 | −0.003978 | −0.008915 | −0.007714 |
| 281 | −0.006091 | 0.00662 | 0.00833 | 0.003538 | −0.004715 | 0.029847 | 0.006801 | −0.002989 | −0.021189 | 0.0166 | −0.021649 | −0.003962 | 0.028993 | 0.01603 |
| 282 | −0.008496 | 0.006271 | 0.013068 | 0.006746 | 0.00383 | 0.019013 | 0.024555 | −0.028598 | −0.038883 | −0.009251 | 0.013915 | −0.011176 | 0.021479 | −0.003167 |
| 283 | 0.00054 | −0.010063 | −0.011057 | −0.019609 | 0.001289 | −0.005255 | 0.045285 | −0.007019 | 0.003349 | −0.001434 | 0.000143 | 0.007137 | 0.002391 | −0.030698 |
| 284 | 0.005566 | 0.006829 | −0.00084 | −0.006684 | −0.01619 | 0.002535 | −0.00758 | −0.017579 | 0.001937 | −0.004172 | 0.002042 | −0.007035 | 0.000662 | −0.006273 |
| 285 | 0.005846 | 0.00635 | 0.002986 | −0.002514 | −0.008024 | −0.004591 | 0.007387 | −0.029261 | −0.015676 | −0.017517 | 0.015814 | −0.016173 | 0.001583 | −0.009891 |
| 286 | 0.004411 | −0.001709 | 0.01227 | −0.001455 | −0.005122 | 0.022086 | −0.019955 | −0.010775 | −0.033105 | −0.006456 | 0.022353 | −0.020668 | 0.044187 | −0.020809 |
| 287 | −0.003316 | −0.0083 | 0.014747 | 0.000257 | −0.001569 | 0.010095 | −0.001473 | −0.013767 | −0.038225 | −0.013964 | 0.032365 | −0.018874 | 0.042588 | −0.028004 |
| 288 | −0.005424 | −0.028059 | 0.010103 | −0.019218 | −0.026998 | 0.02332 | −0.030398 | 0.009765 | −0.001586 | 0.003367 | 0.009687 | −0.001312 | −0.003262 | −0.031276 |
| 289 | 0.00226 | −0.013377 | −0.043668 | −0.029219 | −0.00715 | −0.04972 | −0.021174 | −0.024935 | 0.004976 | −0.038898 | −0.010927 | −0.005027 | −0.013641 | −0.030217 |
| 290 | −0.010783 | −0.026453 | 0.015966 | −0.000978 | −0.001009 | 0.000782 | −0.019883 | −0.016074 | 0.007495 | −0.002069 | −0.021363 | −0.024559 | 0.00446 | 0.018265 |
| 291 | −0.008312 | −0.025052 | 0.013547 | −0.003799 | −0.001519 | 0.001101 | −0.01969 | −0.014312 | 0.009521 | −0.003077 | −0.020346 | −0.027047 | 0.004253 | 0.015456 |
| 292 | −0.00633 | −0.027851 | 0.020898 | −0.002745 | −0.000455 | 0.010036 | −0.016199 | −0.004163 | 0.008201 | 0.001942 | −0.025274 | −0.026688 | −0.001252 | 0.02065 |
| 293 | −0.011206 | −0.004511 | 0.033747 | 0.017736 | −0.015911 | 0.038998 | 0.041138 | 0.026335 | 0.017027 | 0.033726 | −0.014484 | −0.017493 | 0.001014 | −0.001634 |
| 294 | −0.008553 | 0.006337 | 0.001457 | −0.000483 | −0.005235 | 0.010198 | 0.014764 | 0.008301 | 0.006873 | 0.008112 | −0.001255 | −0.005053 | −0.02195 | −0.007934 |
| 295 | 0.011578 | 0.0096 | 0.005521 | −0.002705 | −0.005426 | 0.015158 | 0.010281 | 0.019956 | 0.017122 | 0.018907 | −0.025828 | 0.009488 | −0.031374 | 0.003273 |
| 296 | 0.000637 | −0.016428 | −0.007033 | −0.006339 | 0.009412 | −0.001814 | −0.01739 | 0.031028 | 0.011298 | 0.027294 | −0.058881 | 0.035209 | −0.030328 | −0.031193 |
| 297 | 0.014666 | 0.010009 | 0.013572 | −0.000151 | −0.00899 | 0.031217 | 0.006744 | 0.045324 | −0.000605 | 0.030169 | −0.029948 | −0.004288 | −0.023736 | 0.012917 |
| 298 | 0.004633 | 0.001581 | 0.015449 | 0.003174 | −0.003239 | 0.010513 | −0.016364 | −0.009817 | −0.000781 | 0.026091 | 0.008743 | 0.023005 | 0.028511 | −0.010994 |
| 299 | 0.011691 | 0.014376 | 0.013356 | 0.005196 | −0.02857 | 0.02123 | 0.002207 | 0.036106 | −0.020636 | 0.021998 | −0.040759 | −0.006372 | 0.025059 | 0.010303 |
| 300 | −0.003405 | −0.00487 | −0.00531 | −0.059531 | −0.035253 | 0.007113 | −0.027331 | 0.004503 | 0.009387 | −0.011104 | 0.047055 | 0.020392 | −0.008092 | 0.00389 |
| 301 | 0.007971 | 0.011896 | 0.01698 | 0.012318 | −0.018293 | 0.004263 | 0.017768 | −0.002432 | 0.007741 | 0.008733 | −0.022651 | 0.01463 | −0.024063 | 0.007866 |
| 302 | 0.011547 | −0.002235 | 0.00101 | −0.004216 | 0.000631 | −0.023854 | −0.004931 | −0.014404 | 0.010536 | −0.014174 | −0.033922 | 0.028419 | −0.031516 | −0.012396 |
| 303 | 0.009858 | 0.000356 | −0.01263 | −0.004577 | −0.014368 | −0.005428 | −0.003628 | 0.004958 | −0.021209 | −0.01319 | −0.021522 | 0.024928 | 0.007459 | −0.006317 |
| 304 | 0.000538 | −0.008654 | 0.007434 | −0.007783 | −0.035469 | −0.003018 | −0.00822 | −0.001637 | −0.022804 | −0.010733 | −0.036469 | 0.040653 | 0.015124 | −0.015387 |
| 305 | −0.008677 | 0.028141 | 0.011497 | 0.014812 | −0.022242 | −0.003574 | 0.07263 | −0.021024 | −0.022068 | −0.019569 | 0.005764 | −0.020408 | 0.05038 | −0.015625 |
| 306 | −0.012244 | −0.014581 | −0.013006 | −0.007871 | −0.031808 | 0.031368 | −0.029053 | 0.012816 | −0.01337 | 0.024808 | −0.048242 | −0.075415 | −0.068264 | −0.006985 |
| 307 | −0.034933 | −0.040921 | −0.010667 | −0.0237 | −0.021364 | 0.026408 | 0.038253 | −0.038969 | −0.017387 | −0.031809 | 0.010614 | −0.018513 | −0.062167 | −0.063838 |
| 308 | −0.001852 | −0.00425 | 0.019005 | 0.023502 | −0.000651 | −0.004116 | −0.042537 | −0.015185 | −0.015086 | −0.023842 | −0.071212 | 0.05262 | 0.070277 | 0.031824 |
| 309 | 0.001165 | −0.009749 | 0.019015 | 0.015748 | 0.006931 | 0.001351 | 0.020078 | 0.008238 | −0.005916 | −0.00127 | 0.012802 | 0.002173 | −0.011024 | −0.003605 |
| 310 | −0.001468 | −0.024202 | 0.017178 | 0.044368 | 0.049193 | −0.004106 | 0.012213 | −0.032762 | −0.034605 | 0.016924 | 0.005252 | 0.007224 | −0.001824 | −0.031841 |
| 311 | 0.001883 | 0.00108 | 0.004375 | −0.002579 | 0.006679 | −0.005102 | 0.028953 | −0.000041 | −0.013646 | 0.005891 | 0.00319 | −0.012511 | 0.021985 | 0.006213 |
| 312 | −0.005919 | 0.003873 | 0.014843 | 0.002811 | 0.027745 | −0.001469 | −0.014393 | 0.017805 | −0.033576 | 0.006587 | 0.005066 | −0.019102 | 0.018472 | 0.058307 |
| 313 | 0.008222 | 0.014823 | 0.001229 | 0.007589 | −0.01049 | 0.001811 | 0.054577 | −0.00288 | −0.026766 | 0.014272 | −0.001506 | 0.002622 | 0.019929 | 0.005066 |
| 314 | −0.019028 | −0.013591 | 0.004561 | −0.00082 | −0.021427 | −0.026089 | 0.092899 | −0.007472 | −0.043009 | −0.047374 | 0.027815 | −0.113748 | −0.023297 | 0.029378 |
| 315 | 0.009073 | −0.008662 | 0.011039 | 0.004305 | −0.007873 | 0.019567 | 0.003843 | 0.044186 | −0.040824 | 0.015276 | 0.008363 | −0.011384 | −0.002939 | 0.013025 |
| 316 | 0.043748 | 0.007744 | −0.010474 | 0.00388 | 0.003893 | −0.056774 | 0.026169 | 0.002617 | −0.004982 | −0.017476 | 0.018252 | 0.013535 | −0.008377 | −0.020523 |
| 317 | −0.006856 | −0.012695 | 0.003401 | 0.004891 | 0.008165 | 0.000649 | 0.01957 | 0.012003 | 0.01229 | 0.011285 | 0.022588 | −0.001356 | −0.032086 | 0.007694 |
| 318 | 0.00895 | −0.009323 | 0.033361 | 0.032299 | 0.01087 | −0.00077 | 0.037673 | −0.007837 | −0.015757 | 0.022167 | −0.004844 | 0.007353 | −0.039164 | 0.024865 |
| 319 | 0.011044 | −0.013932 | 0.008523 | 0.006745 | 0.004018 | 0.014421 | −0.00173 | 0.027265 | −0.017093 | 0.014499 | 0.035812 | −0.020551 | −0.018133 | 0.021551 |
| 320 | 0.017327 | 0.011201 | −0.000879 | −0.002201 | 0.01277 | 0.006642 | −0.035234 | 0.004459 | 0.028051 | 0.033951 | 0.015493 | −0.013494 | 0.017826 | 0.04009 |
| 321 | 0.0052 | 0.038282 | 0.005893 | −0.009661 | −0.034597 | 0.02084 | −0.014711 | 0.005454 | −0.017262 | 0.015119 | 0.006892 | 0.008076 | −0.041309 | −0.011535 |
| 322 | −0.01541 | −0.00308 | −0.020842 | −0.00305 | 0.057655 | 0.03558 | 0.005645 | −0.004612 | −0.060349 | −0.006238 | 0.013798 | 0.032745 | 0.020458 | −0.017917 |
| 323 | 0.023311 | 0.054747 | 0.014658 | 0.007401 | −0.013179 | 0.003677 | −0.035884 | −0.004839 | −0.037128 | 0.019039 | 0.002121 | −0.045584 | 0.046332 | 0.025025 |
| 324 | −0.001851 | −0.017742 | 0.010314 | 0.000593 | −0.010847 | −0.02416 | 0.010972 | −0.001948 | −0.024016 | −0.016161 | −0.039487 | −0.034604 | 0.032624 | −0.05769 |
| 325 | −0.000824 | −0.013083 | −0.01173 | −0.010606 | 0.001576 | 0.008661 | −0.012307 | 0.034338 | 0.010839 | 0.022702 | −0.000828 | 0.014834 | −0.04058 | −0.01245 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 326 | −0.021587 | 0.004819 | −0.028222 | −0.015682 | 0.014851 | −0.032185 | 0.038629 | −0.001877 | 0.019935 | −0.008642 | −0.002314 | −0.024043 | 0.01785 | 0.004804 |
| 327 | 0.021086 | 0.014713 | −0.000644 | −0.005004 | 0.002573 | 0.003558 | −0.020068 | −0.009569 | −0.001494 | 0.01145 | −0.010282 | 0.018643 | −0.020996 | −0.015838 |
| 328 | −0.027838 | 0.010315 | 0.001875 | −0.016999 | −0.035579 | 0.014091 | −0.004779 | 0.0385161 | −0.028851 | −0.039701 | 0.036165 | −0.070358 | 0.035695 | −0.002215 |
| 329 | 0.029969 | 0.035667 | −0.014879 | −0.00197 | 0.01568 | −0.017376 | −0.006999 | −0.008693 | −0.024978 | 0.001234 | −0.013885 | −0.012216 | −0.005387 | 0.018218 |
| 330 | −0.01615 | 0.03185 | −0.003296 | −0.007984 | 0.007031 | −0.028513 | −0.003894 | 0.002554 | −0.028755 | 0.007799 | 0.039233 | −0.005993 | 0.038132 | −0.009679 |
| 331 | 0.005104 | 0.0069 | −0.000785 | −0.00601 | −0.007008 | 0.008771 | −0.017587 | 0.018609 | −0.006756 | 0.009561 | 0.001181 | −0.00296 | −0.006075 | 0.008035 |
| 332 | 0.003585 | 0.024495 | 0.008591 | −0.009158 | 0.013339 | −0.015256 | 0.029077 | 0.002902 | 0.046053 | −0.020909 | 0.072198 | 0.033487 | 0.037816 | 0.031854 |
| 333 | 0.001826 | −0.007958 | −0.004025 | −0.007112 | −0.014439 | −0.004046 | −0.018614 | 0.020836 | 0.006563 | 0.010005 | 0.002163 | 0.009855 | −0.05259 | 0.001344 |
| 334 | 0.030678 | −0.001204 | −0.000875 | 0.01035 | 0.014459 | 0.023447 | −0.023762 | 0.00279 | −0.039577 | −0.017653 | −0.001195 | −0.029997 | −0.10852 | −0.009821 |
| 335 | 0.001723 | 0.005527 | −0.007371 | −0.003641 | 0.004225 | −0.005232 | 0.002518 | −0.015489 | 0.008719 | 0.014531 | 0.036884 | −0.029278 | −0.009057 | 0.02211 |
| 336 | −0.020471 | 0.018199 | 0.022096 | 0.005849 | −0.051977 | −0.008978 | −0.030796 | −0.022343 | −0.007133 | −0.012861 | −0.019404 | 0.018382 | −0.02946 | 0.009771 |
| 337 | 0.004727 | −0.013569 | 0.018853 | 0.020507 | −0.010116 | 0.000232 | −0.022352 | 0.021505 | −0.030998 | 0.002946 | −0.050001 | −0.039628 | 0.04794 | 0.01483 |
| 338 | 0.018563 | −0.017096 | −0.007089 | 0.016195 | 0.011696 | −0.018221 | 0.023369 | −0.01047 | −0.047692 | −0.015483 | 0.008659 | 0.020823 | −0.020885 | −0.091081 |
| 339 | −0.019627 | −0.005172 | 0.010007 | −0.01434 | −0.015206 | 0.013647 | −0.006219 | −0.00386 | 0.00428 | −0.035237 | −0.015666 | −0.034566 | 0.011716 | 0.001185 |
| 340 | 0.038497 | 0.029317 | −0.0042 | 0.010442 | 0.000622 | −0.0104 | 0.004686 | 0.023209 | −0.048928 | 0.032057 | −0.061409 | −0.029646 | 0.025967 | 0.015137 |

| | GZ | HA | HB | HC | HD | HE | HF | HG | HH | HI | HJ | HK | HL | HM |
|---|---|---|---|---|---|---|---|---|---|---|---|---|---|---|
| 1 | 0.089987 | −0.088414 | −0.066904 | −0.0522031 | 0.033294 | −0.007868 | 0.108139 | 0.044437 | 0.026049 | −0.033745 | −0.059343 | −0.035637 | −0.041927 | 0.015829 |
| 2 | 0.102424 | −0.005825 | −0.026729 | 0.032829 | 0.068685 | −0.001245 | 0.014513 | 0.102118 | 0.131006 | −0.015003 | −0.065927 | −0.041502 | −0.078178 | −0.049146 |
| 3 | −0.032145 | −0.00163 | 0.087679 | 0.102077 | 0.024168 | 0.003147 | 0.013027 | 0.016288 | 0.01488 | −0.027763 | −0.004755 | 0.022398 | −0.037541 | 0.002641 |
| 4 | −0.020727 | 0.076138 | 0.03539 | −0.091877 | 0.029721 | −0.008341 | 0.028802 | −0.020191 | 0.060156 | 0.040602 | 0.053793 | 0.006033 | −0.002699 | 0.073903 |
| 5 | −0.060625 | −0.086333 | −0.096305 | −0.041454 | −0.050048 | −0.027284 | −0.000707 | −0.009893 | −0.068057 | 0.13066 | 0.057224 | −0.030158 | 0.10675 | 0.077927 |
| 6 | −0.084469 | 0.002039 | 0.08638 | −0.046306 | 0.009272 | −0.018116 | 0.039929 | −0.008004 | −0.048529 | −0.03439 | 0.018519 | −0.048512 | −0.037658 | 0.012845 |
| 7 | 0.038625 | 0.005698 | −0.096625 | 0.027851 | 0.102288 | 0.061309 | −0.041386 | −0.036804 | 0.036177 | −0.03745 | −0.065052 | 0.045745 | −0.011231 | −0.099197 |
| 8 | −0.04932 | −0.038366 | −0.032058 | −0.058801 | 0.032213 | −0.037275 | 0.002062 | −0.040069 | −0.122864 | 0.029583 | −0.011854 | −0.034578 | 0.011605 | −0.000911 |
| 9 | 0.007743 | 0.069878 | 0.054132 | 0.053169 | 0.034654 | 0.001278 | 0.041565 | −0.032752 | 0.027319 | −0.027705 | 0.046257 | 0.007491 | 0.01291 | 0.066866 |
| 10 | 0.330592 | 0.060602 | −0.087938 | −0.10318 | 0.039525 | 0.055965 | −0.008117 | −0.003941 | 0.001191 | 0.056333 | −0.04086 | −0.026361 | −0.010429 | −0.034981 |
| 11 | 0.144913 | 0.126101 | 0.073767 | 0.032485 | −0.015569 | −0.003789 | −0.056089 | 0.017572 | 0.012069 | −0.139229 | −0.026587 | −0.03481 | −0.051817 | 0.024199 |
| 12 | 0.033059 | 0.037908 | −0.043386 | −0.091008 | 0.0880971 | −0.020458 | 0.030863 | 0.047503 | 0.037147 | 0.002424 | 0.082396 | −0.023824 | 0.005118 | −0.050766 |
| 13 | 0.011933 | −0.026859 | 0.053717 | −0.029551 | 0.023677 | −0.054798 | 0.025211 | −0.038321 | −0.03154 | 0.032246 | −0.002408 | 0.017741 | 0.002816 | −0.010848 |
| 14 | 0.009961 | 0.088772 | −0.051445 | 0.010224 | 0.00167 | 0.079894 | 0.04827 | 0.021282 | −0.046888 | −0.03716 | −0.047068 | −0.011902 | −0.019801 | 0.036056 |
| 15 | 0.059634 | −0.002222 | −0.175725 | −0.137091 | −0.085229 | 0.064967 | 0.05451 | −0.023426 | −0.044477 | 0.023267 | −0.102207 | −0.031943 | −0.034033 | −0.118758 |
| 16 | −0.112744 | 0.050383 | −0.079051 | 0.120219 | 0.056009 | −0.080681 | 0.004072 | −0.000185 | −0.046245 | 0.029563 | 0.013056 | 0.000614 | −0.018658 | 0.021594 |
| 17 | −0.089649 | 0.043372 | 0.026951 | 0.064698 | 0.043772 | 0.112228 | −0.099002 | 0.010763 | −0.008006 | −0.043058 | 0.04429 | −0.072373 | −0.0155 | 0.023142 |
| 18 | 0.012632 | 0.066368 | 0.048304 | 0.104974 | −0.047756 | −0.123003 | 0.085395 | −0.031913 | −0.047488 | −0.058032 | −0.044128 | 0.030532 | −0.045098 | −0.027534 |
| 19 | −0.147979 | −0.035384 | 0.075934 | −0.05456 | −0.064173 | −0.084439 | 0.046601 | 0.014261 | 0.061004 | −0.001664 | −0.0298 | −0.053153 | −0.044411 | −0.012012 |
| 20 | −0.030769 | 0.085403 | 0.047685 | −0.081812 | 0.063341 | 0.105278 | −0.177674 | −0.022203 | −0.039492 | −0.058171 | −0.025602 | 0.031747 | −0.003795 | −0.027399 |
| 21 | −0.166473 | 0.040576 | −0.11624 | −0.229553 | −0.064395 | −0.024889 | 0.008068 | 0.017181 | 0.04321 | −0.038351 | −0.0305 | −0.064464 | −0.006919 | 0.007269 |
| 22 | −0.009673 | −0.090299 | 0.068391 | 0.011848 | −0.068353 | −0.009967 | −0.095645 | 0.014034 | −0.017308 | 0.014995 | 0.001737 | −0.015871 | −0.020941 | 0.021783 |
| 23 | −0.101924 | 0.065183 | 0.056961 | −0.001929 | −0.029905 | −0.126059 | −0.032584 | −0.012402 | 0.023559 | 0.095437 | 0.003949 | 0.107989 | 0.119126 | −0.03149 |
| 24 | −0.010181 | 0.174312 | −0.05229 | 0.072509 | −0.029351 | −0.059187 | 0.026096 | 0.011696 | 0.117406 | −0.013675 | −0.014812 | 0.001656 | −0.030549 | −0.037813 |
| 25 | 0.015794 | −0.026039 | 0.118866 | 0.037883 | −0.042321 | 0.001476 | 0.03272 | 0.02271 | −0.110545 | −0.005693 | −0.020035 | −0.118816 | 0.054447 | −0.113885 |
| 26 | −0.04064 | −0.015308 | 0.016026 | 0.062473 | 0.036588 | −0.062851 | 0.069613 | 0.013839 | 0.101212 | 0.040276 | 0.050487 | 0.030072 | −0.000978 | −0.006399 |
| 27 | −0.084 | 0.088271 | 0.037136 | 0.041354 | 0.070671 | −0.008287 | −0.05046 | 0.049868 | 0.055814 | 0.020395 | 0.006452 | −0.036466 | 0.003153 | −0.017435 |
| 28 | −0.076925 | −0.059566 | −0.042169 | 0.127849 | 0.208025 | −0.001188 | −0.025669 | 0.007019 | −0.033206 | −0.051494 | −0.01506 | 0.042026 | 0.022343 | −0.034875 |
| 29 | 0.006497 | 0.025521 | 0.006958 | −0.013021 | 0.000975 | 0.002399 | 0.029756 | 0.000648 | 0.032452 | −0.027327 | −0.004329 | 0.001826 | −0.011388 | −0.004276 |
| 30 | −4.154896 | −4.03533 | −0.086543 | 0.00981 | 0.051517 | 0.094358 | −4.024679 | −0.036662 | −4.050883 | −0.039971 | 0.016293 | 0.012382 | −4.049135 | 0.03415 |
| 31 | −0.06815 | 0.13866 | 0.074007 | −0.06726 | −0.120689 | 0.043795 | −0.056077 | −0.00847 | 0.003132 | −0.009565 | 0.06273 | 0.102923 | 0.09581 | 0.048339 |
| 32 | 0.090504 | 0.027811 | −0.034708 | 0.088876 | −0.030442 | 0.006362 | −0.059299 | −0.039432 | −0.110017 | 0.034524 | 0.034382 | −0.001851 | 0.050311 | 0.065867 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 33 | 0.036022 | 0.04318 | −0.086195 | 0.086065 | −0.021427 | 0.157637 | 0.043262 | −0.00884 | 0.112151 | 0.051787 | −0.004992 | −0.021967 | −0.048346 | 0.027768 |
| 34 | 0.032479 | −0.100294 | 0.101754 | −0.03491 | 0.011714 | −0.109319 | −0.087675 | −0.014257 | −0.053029 | −0.042109 | −0.009778 | 0.011843 | −0.0345411 | −0.043944 |
| 35 | −0.030423 | −0.045882 | 0.000355 | 0.11444 | 0.013541 | −0.139609 | 0.118732 | −0.0189 | −0.03366 | −0.028484 | 0.058544 | −0.055455 | −0.0675 | 0.017064 |
| 36 | −0.021512 | 0.101991 | −0.066229 | −0.039644 | 0.027353 | 0.021798 | −0.184509 | −0.027025 | −0.127202 | −0.069992 | 0.002846 | −0.000719 | −0.047846 | 0.030618 |
| 37 | 0.0341 | 0.038386 | 0.013741 | −0.029793 | −0.036974 | 0.02743 | 0.065323 | −0.022767 | −0.021299 | −0.070327 | −0.006121 | −0.058717 | −0.094959 | −0.075925 |
| 38 | 0.000772 | 0.034521 | −0.086729 | 0.090868 | 0.03254 | −0.033252 | 0.120686 | 0.000974 | 0.064052 | −0.019697 | −0.003221 | 0.03074 | 0.01673 | 0.08723 |
| 39 | −0.047021 | −0.034766 | 0.010757 | −0.035829 | −0.03856 | 0.062325 | −0.024864 | −0.006522 | −0.051583 | −0.042294 | −0.071733 | 0.015492 | −0.013307 | 0.014604 |
| 40 | −0.003086 | 0.028043 | 0.019779 | −0.006808 | −0.030987 | −0.000556 | −0.021605 | −0.012739 | −0.012319 | −0.013555 | 0.001821 | 0.003113 | 0.005326 | 0.032375 |
| 41 | 0.059267 | −0.055076 | 0.038094 | 0.062057 | 0.024915 | 0.001498 | 0.025044 | −0.099578 | −0.03914 | −0.011073 | −0.044557 | −0.024593 | 0.016276 | −0.037 |
| 42 | 0.13127 | 0.028789 | 0.012567 | −0.155647 | 0.008444 | 0.034584 | −0.247009 | 0.025848 | 0.024027 | 0.016873 | −0.038352 | 0.054004 | 0.011644 | 0.008942 |
| 43 | 0.018147 | 0.02193 | −0.026592 | −0.102903 | −0.154082 | −0.054938 | 0.093321 | −0.018074 | −0.006713 | 0.042256 | −0.021411 | −0.064118 | −0.066367 | −0.013457 |
| 44 | −0.013158 | −0.027239 | 0.028507 | 0.045032 | −0.028624 | −0.08452 | −0.046379 | −0.000893 | 0.052266 | −0.025137 | 0.090785 | −0.009442 | −0.018541 | 0.036292 |
| 45 | 0.005979 | −0.027834 | 0.038197 | 0.043616 | 0.058975 | 0.066948 | −0.134361 | −0.02104 | 0.067833 | 0.057074 | −0.006114 | 0.018113 | 0.013372 | 0.059523 |
| 46 | 0.026247 | 0.032549 | −0.080566 | −0.04124 | 0.012886 | 0.095857 | 0.137491 | 0.017399 | −0.074685 | 0.010807 | 0.046451 | −0.052739 | 0.024506 | −0.024615 |
| 47 | −0.064372 | −0.027707 | −0.148129 | −0.031425 | −0.014557 | −0.013561 | 0.157028 | 0.042467 | 0.028689 | −0.102952 | 0.127177 | 0.035427 | 0.012983 | 0.040623 |
| 48 | 0.030932 | 0.040261 | 0.003994 | −0.013902 | −0.106868 | −0.069253 | 0.00973 | −0.009793 | 0.011982 | −0.034884 | −0.01639 | −0.024231 | −0.010888 | 0.057534 |
| 49 | 0.056245 | −0.071381 | 0.035347 | 0.063623 | −0.108586 | −0.045952 | −0.055468 | 0.025444 | 0.084242 | 0.02928 | −0.11227 | −0.001764 | 0.004274 | −0.070661 |
| 50 | −0.012231 | 0.063126 | 0.045774 | −0.038066 | −0.019813 | 0.09895 | 0.068414 | 0.000565 | 0.092139 | 0.012313 | 0.042046 | 0.003943 | 0.044616 | 0.088125 |
| 51 | −0.12871 | −0.033717 | 0.001639 | −0.104055 | 0.089139 | 0.164684 | 0.005904 | 0.007134 | −0.008474 | −0.038575 | −0.045024 | 0.026498 | −0.034616 | 0.004489 |
| 52 | −0.069146 | −0.028247 | 0.137741 | 0.015821 | 0.14337 | −0.043232 | 0.009572 | 0.020892 | −0.062898 | 0.001235 | −0.045765 | −0.029292 | 0.007182 | 0.013959 |
| 53 | 0.074054 | 0.008574 | 0.06147 | −0.047689 | 0.01532 | −0.025425 | −0.043649 | −0.019599 | −0.027339 | −0.032288 | −0.163223 | 0.009148 | −0.033129 | −0.073278 |
| 54 | 0.030572 | −0.008675 | 0.006423 | 0.03619 | 0.042287 | 0.06534 | 0.067702 | 0.014451 | −0.120852 | −0.066662 | −0.01718 | −0.012175 | −0.021167 | −0.038335 |
| 55 | 0.018189 | 0.079828 | 0.067197 | −0.103283 | −0.042138 | −0.339256 | 0.035935 | 0.037337 | −0.051735 | −0.000083 | 0.009475 | −0.020565 | −0.061461 | −0.007095 |
| 56 | 0.060277 | −0.148707 | −0.012808 | −0.004613 | −0.046049 | −0.05714 | −0.010452 | 0.0975 | −0.038769 | 0.017057 | −0.072904 | 0.023172 | 0.012671 | −0.02929 |
| 57 | 0.09222 | −0.069911 | −0.024509 | 0.122703 | 0.0685 | −0.021829 | −0.011321 | 0.091528 | 0.053634 | 0.055635 | −0.051942 | 0.055429 | 0.105982 | 0.065609 |
| 58 | 0.044733 | −0.010794 | 0.094605 | −0.052488 | 0.069208 | 0.121194 | −0.090804 | 0.088829 | −0.011497 | −0.020374 | −0.056681 | 0.002441 | 0.005689 | −0.035509 |
| 59 | −0.02988 | 0.069925 | −0.041758 | −0.11094 | −0.035901 | 0.005828 | −0.069923 | −0.045488 | −0.085554 | −0.013671 | 0.134925 | 0.024804 | 0.037752 | 0.07248 |
| 60 | 0.014403 | −0.027645 | −0.005043 | 0.008003 | 0.024176 | −0.024838 | 0.012926 | 0.041235 | 0.011746 | 0.015177 | 0.036605 | 0.001099 | 0.038644 | −0.020815 |
| 61 | 0.025443 | 0.017743 | −0.007158 | 0.021358 | 0.010903 | −0.029477 | 0.018175 | 0.003356 | 0.017969 | 0.034067 | 0.036126 | 0.008078 | 0.025171 | 0.015604 |
| 62 | 0.012538 | 0.009703 | 0.047207 | 0.015075 | 0.045167 | −0.020097 | −0.004455 | 0.007561 | 0.029917 | −0.038459 | −0.007 | 0.002749 | −0.05458 | −0.087221 |
| 63 | −0.010861 | 0.002215 | 0.015836 | 0.044856 | 0.012604 | −0.035727 | 0.012771 | −0.012662 | 0.011052 | −0.002795 | −0.004162 | 0.006767 | −0.006864 | −0.012674 |
| 64 | −0.017406 | −0.042795 | −0.002747 | −0.027586 | 0.004687 | −0.015216 | 0.034556 | −0.011196 | −0.031748 | −0.003828 | 0.00467 | −0.019357 | −0.006308 | −0.044733 |
| 65 | 0.005896 | −0.003613 | −0.003505 | −0.03241 | 0.00243 | −0.012881 | 0.000648 | 0.028929 | 0.024189 | 0.015799 | 0.006207 | 0.030858 | 0.021659 | −0.022861 |
| 66 | 0.000268 | 0.011217 | −0.02847 | 0.017639 | 0.045174 | 0.001202 | 0.014991 | 0.007773 | −0.02656 | 0.014157 | 0.026979 | 0.018131 | 0.012078 | 0.004836 |
| 77 | −0.055583 | 0.002587 | 0.021173 | 0.025759 | −0.003737 | −0.03424 | 0.021464 | −0.013829 | −0.025546 | −0.030219 | 0.036571 | 0.007544 | −0.006637 | 0.033809 |
| 68 | 0.027717 | 0.003983 | 0.038354 | 0.010443 | 0.049038 | −0.001107 | −0.014726 | 0.038556 | 0.069725 | −0.018949 | 0.023974 | 0.024737 | 0.004766 | 0.025583 |
| 69 | 0.006117 | −0.023979 | 0.000614 | 0.010339 | 0.040437 | 0.017435 | −0.091935 | −0.003824 | 0.014411 | 0.020056 | 0.003658 | 0.029455 | 0.013299 | 0.021069 |
| 70 | −0.023645 | −0.008918 | 0.018475 | 0.019409 | 0.016827 | −0.001584 | −0.040319 | −0.000794 | 0.036071 | 0.001444 | 0.014872 | 0.023966 | 0.019839 | 0.018997 |
| 71 | 0.028941 | −0.047436 | −0.004699 | 0.010944 | 0.00646 | −0.007318 | 0.036484 | 0.002362 | 0.00111 | 0.014379 | 0.011242 | −0.005191 | 0.002979 | 0.01071 |
| 72 | −0.021026 | −0.021769 | −0.0143 | −0.004094 | −0.04388 | −0.038849 | 0.042332 | −0.003444 | 0.002758 | 0.022445 | 0.008205 | −0.005164 | 0.01477 | −0.009348 |
| 73 | 0.061761 | 0.030912 | −0.028786 | −0.000492 | −0.036283 | 0.005446 | 0.024266 | −0.000187 | −0.023447 | −0.012264 | −0.00731 | −0.029251 | −0.024479 | 0.013754 |
| 74 | 0.024986 | 0.039559 | 0.002968 | −0.024358 | −0.08586 | −0.007726 | 0.04402 | −0.005925 | 0.048949 | 0.0144 | −0.007838 | 0.001941 | 0.001979 | −0.032154 |
| 75 | 0.002169 | −0.006431 | −0.005916 | 0.01023 | −0.002206 | −0.006351 | −0.007535 | −0.004388 | 0.005331 | 0.000229 | 0.027478 | 0.008118 | 0.012681 | 0.011328 |
| 76 | −0.004904 | 0.030905 | 0.005706 | 0.031437 | 0.012505 | −0.013056 | −0.019286 | −0.009655 | 0.02386 | 0.015328 | −0.010155 | 0.009617 | −0.002726 | −0.003349 |
| 77 | 0.005156 | −0.010494 | 0.00702 | 0.012611 | −0.003823 | −0.00019 | −0.035867 | −0.006465 | 0.013145 | 0.007014 | 0.021274 | 0.01299 | 0.015877 | 0.016978 |
| 78 | 0.013373 | −0.008073 | −0.000862 | 0.003191 | −0.012301 | −0.005806 | −0.031749 | −0.010002 | −0.000149 | 0.000503 | 0.028783 | 0.006019 | 0.012648 | 0.019492 |
| 79 | −0.014132 | 0.000066 | −0.021305 | −0.006998 | 0.035252 | 0.030864 | 0.005226 | 0.000148 | 0.003512 | −0.006055 | 0.026864 | 0.001096 | 0.009456 | 0.005312 |
| 80 | 0.002039 | −0.044447 | 0.014202 | −0.03045 | 0.004323 | −0.062439 | 0.060125 | −0.013783 | −0.076219 | −0.004696 | −0.002811 | −0.000689 | −0.00956 | −0.002378 |
| 81 | −0.006088 | 0.063335 | 0.050529 | −0.010097 | −0.064051 | −0.052316 | −0.111081 | 0.006966 | 0.029402 | 0.028691 | 0.013185 | 0.028867 | 0.009634 | 0.010632 |
| 82 | 0.025852 | −0.022573 | −0.017098 | −0.013901 | 0.021862 | 0.001282 | 0.028265 | 0.010657 | 0.021628 | −0.001068 | −0.025297 | −0.000634 | −0.000196 | −0.007487 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 83 | 0.029151 | −0.034454 | −0.035236 | −0.014479 | 0.033425 | −0.001181 | 0.044712 | 0.011481 | 0.014299 | −0.003686 | −0.015246 | −0.003451 | −0.005933 | −0.00346 |
| 84 | 0.010255 | −0.031264 | −0.000331 | −0.020809 | 0.020566 | 0.017192 | −0.002721 | 0.0061 | −0.003736 | −0.003532 | −0.008279 | 0.001132 | 0.00156 | 0.002206 |
| 85 | 0.011365 | 0.05098 | −0.001687 | −0.015249 | −0.052896 | −0.020523 | 0.027595 | −0.010569 | −0.027252 | 0.025725 | 0.005373 | −0.025785 | −0.008604 | 0.003036 |
| 86 | 0.020964 | −0.023079 | −0.001349 | 0.043528 | −0.010086 | −0.021644 | 0.010748 | −0.005789 | −0.006214 | 0.034798 | 0.000912 | 0.002614 | 0.008791 | 0.016663 |
| 87 | 0.016232 | −0.018731 | 0.015073 | −0.04029 | −0.015509 | −0.05665 | 0.027571 | 0.008249 | 0.002402 | 0.007576 | −0.001992 | 0.013618 | 0.003191 | 0.01373 |
| 88 | 0.021277 | −0.031357 | −0.023074 | −0.024347 | 0.014787 | 0.002752 | 0.018489 | 0.00646 | −0.015893 | −0.018261 | −0.014816 | 0.002057 | −0.004824 | −0.003408 |
| 89 | 0.037196 | −0.031901 | −0.020491 | −0.031512 | 0.030387 | 0.009687 | 0.009583 | 0.00757 | −0.002523 | −0.011796 | −0.002483 | 0.00058 | −0.002378 | 0.006813 |
| 90 | 0.035662 | −0.032633 | −0.013448 | −0.02041 | 0.037261 | −0.014374 | 0.021021 | 0.013701 | 0.015128 | −0.001484 | 0.000819 | −0.000056 | −0.006782 | −0.002858 |
| 91 | 0.006863 | −0.04445 | −0.006145 | 0.007362 | −0.007767 | 0.011556 | 0.014479 | 0.007397 | 0.002487 | −0.000086 | −0.005963 | −0.004536 | 0.00868 | −0.005891 |
| 92 | −0.051529 | 0.00032 | 0.008533 | −0.021891 | −0.07715 | 0.017646 | −0.076574 | −0.011619 | −0.028921 | 0.012252 | −0.003151 | 0.014389 | 0.019362 | 0.03482 |
| 93 | 0.007636 | −0.048561 | −0.003885 | 0.053019 | 0.038632 | −0.028817 | 0.032389 | 0.012773 | 0.024487 | 0.004835 | −0.009229 | −0.006793 | −0.000914 | −0.000719 |
| 94 | 0.018485 | −0.015596 | −0.052643 | 0.062079 | 0.030314 | 0.025888 | 0.033152 | −0.004109 | 0.016317 | −0.004605 | 0.011667 | −0.000242 | −0.001961 | −0.004631 |
| 95 | −0.00792 | −0.031143 | −0.002885 | 0.007748 | 0.049509 | 0.00033 | 0.001411 | 0.003834 | −0.012006 | 0.007952 | 0.01353 | −0.002433 | −0.007791 | 0.029863 |
| 96 | 0.017922 | −0.024471 | −0.024018 | −0.00597 | 0.004466 | 0.029524 | −0.00493 | −0.00042 | −0.02783 | −0.025585 | −0.007135 | 0.014097 | 0.029739 | 0.021147 |
| 97 | 0.039593 | 0.027118 | −0.001454 | 0.008393 | −0.00818 | −0.053375 | −0.01893 | 0.007631 | 0.014435 | 0.018424 | −0.012599 | 0.018644 | 0.021347 | −0.003439 |
| 98 | −0.020612 | 0.027617 | 0.007594 | 0.004604 | −0.005056 | −0.020472 | 0.014161 | −0.046213 | −0.042787 | 0.000978 | 0.027152 | 0.011213 | 0.011802 | 0.001725 |
| 99 | −0.0008 | 0.008606 | −0.009172 | −0.001104 | −0.018766 | 0.012283 | −0.028244 | 0.003481 | 0.002634 | 0.009237 | −0.010157 | 0.022449 | 0.019284 | 0.011666 |
| 100 | −0.011181 | 0.023697 | 0.004883 | −0.018936 | 0.00199 | −0.000797 | −0.007712 | −0.044556 | −0.016221 | 0.011742 | −0.009179 | 0.01286 | 0.00761 | −0.015519 |
| 101 | 0.00196 | 0.018849 | 0.036675 | 0.028969 | −0.007174 | −0.027903 | 0.00577 | −0.036636 | −0.031532 | 0.002722 | 0.025291 | 0.004201 | 0.00227 | −0.005268 |
| 102 | 0.002643 | 0.021624 | 0.017208 | −0.007877 | −0.036787 | −0.03358 | −0.07197 | −0.007496 | 0.018982 | 0.008548 | −0.004987 | 0.016309 | 0.018263 | 0.040403 |
| 103 | −0.033686 | −0.055172 | 0.005627 | −0.069542 | −0.044893 | −0.070651 | −0.047939 | 0.004108 | −0.006566 | 0.000962 | 0.032342 | 0.011324 | 0.009554 | 0.020874 |
| 104 | −0.007767 | −0.022623 | −0.002147 | −0.050019 | −0.045973 | −0.024412 | −0.007269 | 0.011663 | −0.018775 | 0.01204 | −0.003654 | 0.012367 | 0.000563 | −0.003787 |
| 105 | 0.045412 | 0.002389 | 0.026851 | −0.077417 | −0.017423 | −0.02964 | 0.010919 | −0.021782 | −0.03841 | −0.020372 | 0.008641 | 0.011708 | 0.010878 | −0.006879 |
| 106 | −0.087204 | −0.002365 | −0.014721 | −0.005741 | 0.024894 | 0.03208 | −0.016546 | 0.010755 | 0.003196 | −0.029303 | −0.010989 | −0.030538 | −0.040906 | −0.011445 |
| 107 | 0.004636 | 0.031276 | 0.012708 | 0.015347 | 0.016399 | −0.013053 | −0.045533 | 0.009724 | −0.029274 | −0.028764 | −0.043156 | −0.023901 | −0.047897 | −0.019065 |
| 108 | −0.002938 | −0.001139 | 0.011745 | 0.013763 | 0.000992 | −0.000286 | 0.011129 | 0.009119 | 0.026591 | −0.042426 | −0.025462 | −0.006683 | −0.041722 | −0.00945 |
| 109 | 0.037728 | −0.031704 | −0.007701 | 0.023998 | 0.001354 | 0.044386 | −0.04025 | −0.00021 | 0.005567 | 0.018772 | −0.032711 | −0.018779 | −0.043935 | −0.021191 |
| 110 | −0.04233 | −0.052423 | 0.009664 | −0.043625 | 0.003384 | 0.019292 | 0.009352 | −0.014921 | −0.04246 | 0.007674 | 0.008034 | −0.007384 | 0.004159 | 0.026981 |
| 111 | 0.027226 | 0.023347 | −0.000967 | −0.072047 | −0.003357 | 0.052395 | −0.02532 | −0.007149 | −0.01077 | −0.031777 | −0.036474 | −0.003686 | −0.032694 | −0.030305 |
| 112 | −0.051461 | −0.035258 | −0.0268 | 0.002293 | 0.03443 | 0.002197 | −0.023491 | −0.007532 | 0.006936 | −0.023722 | 0.020788 | −0.001409 | −0.022726 | 0.014804 |
| 113 | −0.034288 | 0.036059 | 0.011529 | −0.015345 | 0.012279 | 0.012849 | −0.048191 | 0.006314 | 0.00736 | −0.011964 | −0.019078 | −0.013621 | −0.02524 | 0.01074 |
| 114 | −0.03176 | 0.036771 | −0.037286 | 0.036435 | −0.017922 | −0.014146 | 0.088269 | 0.000114 | 0.100036 | −0.006501 | 0.010214 | −0.007865 | −0.046527 | 0.064483 |
| 115 | −0.081168 | −0.028318 | 0.028959 | 0.063671 | 0.002377 | 0.064597 | 0.003624 | −0.001418 | 0.003902 | −0.032151 | −0.008168 | −0.009651 | −0.009952 | −0.043139 |
| 116 | 0.00756 | 0.042263 | −0.050085 | −0.044728 | −0.029727 | −0.034518 | 0.064603 | −0.007401 | 0.078846 | 0.009287 | 0.043383 | 0.004786 | −0.026158 | 0.006403 |
| 117 | −0.009521 | −0.004829 | 0.021963 | −0.011362 | 0.024974 | −0.031796 | 0.003862 | 0.003109 | −0.007291 | 0.007444 | −0.047134 | 0.020882 | 0.024817 | −0.015399 |
| 118 | −0.025961 | 0.005513 | 0.083935 | 0.029619 | 0.005082 | −0.029787 | −0.005918 | −0.019658 | −0.024364 | −0.058373 | −0.032294 | 0.022363 | −0.011654 | −0.018904 |
| 119 | −0.025749 | −0.043714 | 0.004148 | 0.027262 | 0.03325 | 0.033457 | −0.064809 | 0.002724 | −0.000032 | −0.005238 | −0.038091 | 0.004336 | −0.005762 | −0.026298 |
| 120 | −0.011218 | 0.021467 | 0.004477 | −0.029732 | 0.005136 | 0.023422 | −0.021844 | −0.003374 | −0.011143 | −0.003847 | −0.013053 | −0.007037 | 0.001998 | −0.001383 |
| 121 | −0.054453 | −0.002269 | −0.040322 | −0.004899 | 0.009585 | 0.000272 | 0.071882 | −0.04284 | 0.00184 | −0.009257 | −0.004255 | 0.009233 | −0.008071 | −0.029483 |
| 122 | −0.022466 | 0.020429 | 0.009509 | 0.013387 | 0.023952 | 0.039178 | −0.017116 | −0.00466 | −0.017971 | −0.001476 | 0.007465 | −0.027379 | 0.003242 | 0.000114 |
| 123 | −0.008321 | 0.004573 | 0.0154 | −0.009686 | 0.024745 | 0.017071 | −0.023114 | −0.012308 | −0.0184 | −0.004165 | −0.018676 | −0.034013 | −0.038044 | −0.030934 |
| 124 | −0.010741 | −0.014607 | 0.01156 | 0.004402 | 0.038156 | 0.010248 | −0.04145 | −0.002516 | 0.008135 | −0.00412 | −0.02624 | −0.002616 | −0.017118 | −0.050352 |
| 125 | −0.016266 | −0.026015 | 0.014835 | −0.030734 | −0.027797 | −0.022049 | 0.011541 | −0.007873 | −0.047454 | 0.019416 | −0.004943 | 0.008389 | 0.026141 | −0.008955 |
| 126 | −0.027871 | −0.001341 | 0.014359 | −0.014283 | −0.028827 | −0.003123 | −0.001487 | −0.01808 | −0.024783 | −0.000835 | −0.026618 | −0.001025 | −0.009895 | −0.009078 |
| 127 | −0.046239 | −0.031998 | 0.009041 | −0.002814 | −0.016396 | 0.025073 | 0.011266 | −0.000394 | −0.017543 | −0.007884 | −0.024678 | −0.001437 | 0.004094 | −0.006466 |
| 128 | 0.00937 | −0.025651 | −0.017103 | −0.025292 | −0.040774 | −0.022134 | 0.014394 | 0.00394 | 0.008422 | 0.0182 | −0.001028 | 0.004217 | 0.012554 | 0.010902 |
| 129 | 0.036581 | −0.049829 | −0.026958 | −0.07318 | −0.024329 | 0.072995 | −0.088625 | −0.009769 | −0.02533 | −0.004622 | 0.012843 | 0.000185 | 0.000485 | 0.007709 |
| 130 | −0.015102 | −0.042378 | −0.033662 | 0.033175 | −0.006871 | 0.00914 | 0.011898 | −0.003267 | 0.006236 | −0.013522 | 0.025144 | −0.030744 | −0.021496 | −0.023385 |
| 131 | 0.019865 | −0.043495 | 0.052981 | −0.067259 | 0.004805 | −0.079794 | −0.032648 | −0.010042 | −0.01671 | 0.001487 | −0.004962 | −0.026401 | 0.019485 | −0.026179 |
| 132 | 0.013507 | −0.02954 | −0.023045 | −0.026321 | 0.018381 | 0.006571 | 0.015183 | −0.00149 | −0.015047 | 0.007586 | −0.028145 | −0.017511 | −0.015361 | −0.020728 |

APPENDIX B3-continued

PCA Transformation
Matrix (340 × 340 Early/Late)

| | | | | | | | | | | | | | |
|---|---|---|---|---|---|---|---|---|---|---|---|---|---|
| 133 | 0.001698 | −0.043803 | −0.054721 | −0.015305 | 0.022572 | −0.000858 | 0.015449 | −0.003112 | −0.009465 | −0.000676 | 0.03342 | −0.000472 | −0.001084 | 0.006114 |
| 134 | 0.0677 | −0.004112 | −0.045412 | −0.034855 | −0.085925 | 0.051902 | −0.025546 | 0.004189 | 0.009328 | 0.011737 | 0.006941 | 0.0292591 | 0.0366 | 0.000068 |
| 135 | 0.015632 | −0.012799 | −0.034687 | −0.009092 | −0.018717 | 0.00187 | 0.034714 | −0.003245 | −0.017984 | 0.001586 | 0.010704 | −0.0134341 | −0.00313 | 0.000897 |
| 136 | −0.003302 | 0.026191 | −0.00532 | −0.047682 | −0.035718 | 0.041594 | −0.006884 | −0.011443 | 0.032313 | −0.003807 | 0.00077 | −0.009482 | −0.002237 | 0.004163 |
| 137 | −0.025331 | 0.034602 | 0.026022 | −0.029609 | −0.030855 | −0.03688 | −0.004486 | −0.015398 | −0.006262 | −0.001537 | 0.018176 | −0.005808 | 0.001515 | −0.010932 |
| 138 | 0.006058 | −0.011294 | −0.106888 | −0.014899 | −0.006819 | 0.015783 | −0.055223 | −0.002663 | 0.011751 | 0.010614 | −0.022329 | 0.015623 | 0.01112 | 0.017314 |
| 139 | −0.022156 | 0.015855 | 0.094725 | 0.078437 | 0.01502 | −0.005577 | 0.036597 | −0.008041 | 0.005871 | −0.026901 | −0.02455 | −0.041043 | −0.051718 | −0.005699 |
| 140 | 0.075 | 0.03108 | 0.019178 | 0.034987 | −0.035647 | −0.039293 | −0.053842 | −0.012928 | 0.028925 | 0.030428 | −0.016355 | −0.00068 | 0.017906 | 0.011156 |
| 141 | −0.003277 | −0.011907 | −0.031899 | 0.017347 | −0.012905 | −0.003579 | 0.024901 | −0.000668 | 0.000587 | 0.000354 | 0.027463 | 0.013498 | 0.008145 | 0.055087 |
| 142 | 0.007062 | 0.033596 | 0.001279 | 0.061697 | 0.001508 | −0.0461 | 0.023861 | −0.006623 | 0.009863 | 0.001798 | 0.012282 | −0.002665 | −0.019723 | 0.013813 |
| 143 | −0.005392 | 0.01407 | −0.003632 | 0.045975 | −0.010382 | 0.005368 | −0.002763 | 0.000779 | −0.004695 | 0.007436 | 0.017383 | −0.021678 | −0.003428 | 0.005949 |
| 144 | −0.003745 | −0.00446 | −0.015679 | 0.051775 | 0.016826 | −0.011815 | −0.019734 | 0.013092 | 0.014302 | −0.00767 | 0.030553 | −0.004968 | −0.006195 | 0.01597 |
| 145 | 0.058708 | −0.020314 | −0.0109 | 0.031203 | 0.001932 | −0.0092 | 0.022025 | 0.010797 | 0.027652 | 0.008218 | −0.012527 | −0.018948 | −0.010589 | −0.005446 |
| 146 | 0.007568 | 0.019967 | −0.013104 | −0.030746 | −0.02736 | −0.016158 | 0.021363 | −0.000892 | −0.001318 | 0.009657 | −0.004435 | −0.005607 | −0.011502 | −0.001853 |
| 147 | −0.032707 | 0.050658 | −0.066493 | −0.037688 | 0.005096 | −0.024166 | −0.027707 | 0.005057 | −0.028269 | −0.000269 | −0.022186 | −0.006313 | −0.024522 | 0.040603 |
| 148 | −0.000036 | 0.036474 | 0.046072 | 0.013279 | −0.014852 | −0.051193 | −0.038485 | −0.000845 | 0.013643 | 0.006449 | 0.001572 | −0.01743 | −0.011643 | 0.038377 |
| 149 | −0.008939 | 0.00506 | 0.006262 | −0.015132 | −0.041351 | 0.00842 | 0.024747 | 0.014288 | 0.022124 | −0.008414 | 0.021234 | −0.000459 | 0.008706 | 0.011153 |
| 150 | −0.003031 | 0.018053 | 0.003572 | −0.041436 | −0.051196 | 0.00127 | 0.001228 | −0.028657 | −0.004598 | 0.017322 | −0.021472 | −0.010839 | −0.006259 | −0.019266 |
| 151 | −0.040803 | 0.019571 | −0.056803 | −0.0141 | −0.028782 | 0.034759 | 0.030153 | 0.020963 | −0.046388 | −0.015326 | −0.02811 | 0.004219 | −0.000042 | 0.008829 |
| 152 | −0.018991 | −0.044635 | 0.004982 | −0.000746 | −0.010079 | 0.027413 | −0.014894 | 0.006795 | −0.00815 | −0.007603 | −0.007386 | 0.004978 | 0.011969 | 0.011668 |
| 153 | −0.019177 | −0.004833 | 0.041114 | −0.00847 | −0.023644 | −0.009349 | −0.001813 | 0.011111 | −0.017961 | −0.003067 | 0.020199 | 0.001957 | −0.011842 | 0.010259 |
| 154 | 0.016791 | 0.0049 | −0.014137 | −0.008207 | −0.040017 | −0.044021 | 0.033921 | −0.00236 | 0.017449 | 0.02252 | 0.021138 | −0.011168 | 0.006373 | 0.000124 |
| 155 | −0.00585 | −0.050651 | 0.002743 | −0.056881 | −0.015418 | −0.003225 | −0.037571 | 0.008326 | 0.010367 | 0.011563 | −0.005367 | −0.001994 | −0.004975 | −0.0268 |
| 156 | −0.003692 | −0.044292 | −0.010297 | −0.010547 | −0.071584 | −0.041601 | 0.005808 | 0.011581 | 0.031165 | 0.026177 | −0.007996 | 0.003534 | 0.015304 | −0.000385 |
| 157 | −0.035732 | 0.010511 | −0.008283 | −0.023849 | −0.009257 | −0.007811 | −0.007387 | −0.016173 | −0.017378 | 0.016589 | −0.013749 | −0.004567 | −0.002196 | −0.013604 |
| 158 | −0.018447 | 0.026522 | −0.109758 | −0.033248 | −0.026778 | 0.06509 | 0.035728 | 0.008833 | 0.032595 | 0.005662 | 0.042325 | 0.008108 | −0.007446 | 0.023764 |
| 159 | 0.058554 | −0.024229 | −0.051564 | −0.068261 | −0.025414 | −0.006027 | 0.016571 | −0.025052 | −0.013581 | 0.00238 | −0.001025 | 0.000077 | 0.011865 | −0.007024 |
| 160 | −0.032812 | −0.007585 | 0.062302 | −0.036621 | 0.008946 | −0.005071 | −0.055442 | −0.0051 | −0.011133 | 0.013246 | −0.004757 | 0.020735 | 0.020282 | 0.00553 |
| 161 | 0.025485 | 0.029231 | −0.044411 | −0.035815 | −0.007909 | 0.040302 | −0.051307 | 0.032201 | 0.028629 | 0.010893 | 0.022921 | −0.009049 | −0.022381 | 0.036987 |
| 162 | −0.022214 | 0.029315 | −0.005077 | 0.025959 | 0.015937 | 0.010897 | 0.027678 | −0.00036 | 0.063076 | −0.022257 | −0.003977 | 0.007473 | −0.016949 | 0.003354 |
| 163 | −0.022553 | −0.007174 | 0.005374 | 0.013928 | 0.006835 | −0.024485 | 0.015415 | 0.000171 | −0.007745 | −0.003814 | −0.016817 | 0.003842 | 0.004063 | −0.009483 |
| 164 | −0.067375 | −0.014747 | 0.046563 | −0.001151 | −0.009418 | −0.081516 | −0.012884 | 0.012864 | 0.017912 | −0.021518 | −0.02283 | 0.024113 | 0.009394 | 0.0083 |
| 165 | −0.059547 | −0.046068 | −0.023139 | 0.011149 | 0.02273 | 0.016097 | −0.003448 | 0.036707 | 0.001521 | 0.01 | 0.020149 | 0.047216 | 0.033291 | 0.011126 |
| 166 | 0.022045 | −0.034117 | −0.060168 | −0.001843 | 0.026054 | −0.022947 | −0.029072 | 0.003496 | 0.005807 | 0.019982 | 0.008292 | 0.0134 | −0.004974 | −0.018084 |
| 167 | −0.045053 | −0.012589 | 0.026047 | 0.02947 | −0.013201 | −0.017722 | 0.014064 | −0.001277 | 0.022429 | 0.002173 | 0.019661 | 0.012414 | 0.00726 | 0.009404 |
| 168 | −0.017147 | 0.042341 | 0.02716 | 0.062968 | 0.031555 | 0.024719 | 0.008255 | −0.012106 | −0.019811 | −0.071587 | −0.009964 | −0.013506 | −0.01127 | −0.019425 |
| 169 | −0.00273 | −0.022327 | 0.010148 | 0.005112 | 0.013851 | −0.009939 | 0.040788 | −0.015541 | −0.02338 | −0.014087 | 0.003782 | −0.026048 | −0.023904 | −0.016699 |
| 170 | −0.002187 | −0.026439 | 0.000934 | 0.045805 | 0.024836 | −0.0247 | 0.054282 | −0.010056 | 0.011021 | −0.010602 | 0.021317 | −0.027567 | −0.025001 | −0.002143 |
| 171 | 0.020296 | −0.010196 | −0.006291 | 0.002667 | 0.003524 | 0.004043 | 0.031386 | −0.026634 | −0.02754 | −0.032916 | 0.007826 | −0.028379 | −0.03878 | −0.010679 |
| 172 | −0.013 | 0.003177 | −0.037862 | −0.031466 | −0.023934 | −0.017662 | 0.022725 | 0.008032 | 0.003644 | −0.000653 | −0.00822 | −0.015215 | −0.011447 | −0.012737 |
| 173 | −0.003775 | 0.02533 | −0.025834 | −0.018986 | −0.020607 | 0.007052 | 0.029775 | 0.009011 | 0.011835 | −0.016771 | 0.016131 | −0.020842 | −0.020156 | −0.010576 |
| 174 | 0.010881 | 0.028203 | −0.030092 | 0.006638 | 0.017867 | 0.015571 | 0.01753 | 0.026301 | 0.018618 | −0.030707 | 0.010209 | −0.028552 | −0.022058 | −0.007107 |
| 175 | −0.055597 | 0.046481 | 0.009609 | −0.067036 | 0.032184 | 0.02641 | −0.025266 | 0.03105 | 0.022603 | −0.012991 | −0.00372 | −0.01446 | −0.000802 | −0.000308 |
| 176 | −0.01853 | −0.001051 | −0.020752 | −0.010669 | 0.038221 | −0.026868 | 0.028966 | 0.002928 | 0.016871 | −0.011012 | −0.012838 | −0.008031 | −0.002348 | −0.019427 |
| 177 | −0.014681 | −0.030631 | 0.017359 | −0.037339 | −0.001498 | 0.037502 | −0.048892 | 0.010879 | −0.01463 | −0.02537 | −0.008368 | 0.013484 | 0.003117 | −0.009146 |
| 178 | −0.028108 | 0.031498 | 0.00608 | −0.02854 | 0.012876 | 0.017417 | −0.046609 | −0.037531 | −0.053304 | −0.00835 | 0.007101 | 0.015104 | −0.00662 | 0.004373 |
| 179 | −0.015767 | 0.011816 | 0.012124 | −0.000489 | 0.011765 | −0.002292 | −0.026409 | −0.051046 | −0.057964 | −0.001901 | 0.006483 | 0.017152 | 0.009648 | 0.004467 |
| 180 | −0.016693 | 0.02131 | 0.006359 | 0.004438 | 0.012679 | 0.011587 | −0.02612 | −0.048268 | −0.045265 | −0.008324 | 0.030276 | 0.016972 | 0.012258 | 0.014201 |
| 181 | −0.026733 | 0.014379 | 0.005027 | −0.001267 | 0.011835 | −0.002396 | −0.018743 | −0.044257 | −0.045395 | −0.001374 | 0.027813 | 0.010993 | 0.006766 | 0.004369 |
| 182 | −0.025953 | 0.023539 | −0.016697 | −0.006505 | 0.008847 | 0.003471 | −0.021819 | −0.042963 | −0.015295 | 0.004966 | 0.033582 | 0.017799 | 0.018006 | 0.020376 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 183 | −0.00394 | −0.004773 | −0.015802 | −0.046261 | −0.014586 | 0.00027 | −0.026463 | −0.058888 | −0.042527 | 0.013004 | −0.002345 | 0.017799 | 0.007891 | −0.00096 |
| 184 | 0.046897 | −0.023149 | −0.053048 | −0.006414 | 0.00797 | −0.011009 | −0.025901 | −0.046357 | −0.035243 | 0.008818 | −0.030843 | −0.002996 | −0.019935 | −0.028575 |
| 185 | 0.000161 | −0.020523 | −0.008421 | −0.000878 | 0.023504 | −0.024348 | −0.013098 | 0.001229 | −0.045611 | 0.018692 | −0.001377 | 0.00699 | 0.03162 | −0.023893 |
| 186 | −0.007105 | 0.000541 | −0.014259 | −0.006297 | 0.029516 | 0.042145 | −0.061703 | −0.004714 | −0.032974 | −0.015592 | −0.002085 | −0.021928 | −0.019885 | −0.010655 |
| 187 | −0.008114 | 0.014147 | −0.015214 | 0.01285 | 0.001836 | 0.012031 | −0.000931 | −0.012615 | 0.020778 | 0.010646 | 0.003232 | 0.023739 | 0.02075 | 0.013085 |
| 188 | −0.006514 | 0.019594 | −0.026087 | 0.043688 | 0.021645 | 0.002233 | −0.006898 | −0.001878 | 0.042571 | 0.001212 | 0.007429 | 0.017255 | 0.019069 | 0.02314 |
| 189 | −0.018804 | 0.045158 | 0.002777 | 0.02777 | 0.053287 | −0.008951 | −0.014411 | −0.034067 | 0.031704 | −0.003242 | −0.00429 | 0.007959 | 0.010857 | 0.015061 |
| 190 | −0.002771 | −0.019548 | −0.007252 | 0.003322 | 0.005627 | −0.008245 | 0.000872 | −0.006599 | 0.008421 | 0.018438 | 0.002052 | 0.011342 | 0.020789 | −0.012158 |
| 191 | 0.024404 | −0.023371 | 0.016163 | −0.020242 | −0.019754 | 0.009133 | −0.030552 | −0.012379 | −0.021813 | 0.014476 | −0.0033 | 0.007273 | 0.017709 | −0.013724 |
| 192 | −0.023178 | 0.00071 | −0.045407 | 0.003722 | −0.032115 | 0.020503 | 0.015256 | −0.017025 | 0.014425 | 0.012778 | 0.000051 | 0.019354 | 0.026957 | 0.02612 |
| 193 | −0.011556 | 0.004413 | −0.018972 | −0.009314 | 0.017167 | −0.003047 | −0.026526 | 0.008669 | −0.004581 | 0.005047 | 0.004454 | 0.00479 | 0.0172 | 0.015744 |
| 194 | 0.009387 | −0.005942 | −0.032842 | 0.011221 | 0.031854 | 0.039988 | −0.055564 | −0.00952 | −0.008809 | 0.006167 | −0.035013 | 0.025312 | 0.032125 | −0.005794 |
| 195 | 0.0175 | −0.014341 | −0.020061 | −0.019256 | 0.0171 | −0.049407 | 0.014211 | −0.00778 | 0.006264 | 0.024717 | −0.008565 | −0.000007 | −0.0022 | −0.015216 |
| 196 | −0.021993 | 0.011814 | −0.030374 | 0.007317 | 0.027008 | −0.003278 | 0.008506 | −0.015314 | 0.012477 | 0.0106 | 0.01123 | 0.00569 | 0.009135 | −0.007742 |
| 197 | −0.012059 | −0.036307 | −0.032413 | −0.019694 | −0.00239 | −0.012813 | 0.043853 | 0.009741 | 0.020677 | 0.01202 | 0.032617 | 0.008288 | 0.033859 | 0.007966 |
| 198 | 0.006779 | −0.036778 | −0.010171 | −0.03787 | 0.022457 | −0.061276 | 0.009029 | 0.008864 | 0.01853 | 0.016955 | −0.038362 | 0.010705 | −0.00992 | −0.017499 |
| 199 | −0.023649 | 0.058132 | −0.003252 | −0.010326 | 0.013829 | 0.015243 | −0.013017 | 0.003704 | −0.012259 | −0.034677 | −0.035998 | 0.002444 | 0.001067 | 0.003858 |
| 200 | −0.002127 | −0.029131 | −0.021651 | −0.063191 | −0.032397 | −0.031244 | 0.008836 | −0.000056 | −0.03275 | 0.001292 | −0.023759 | 0.015624 | −0.009645 | −0.000585 |
| 201 | 0.046749 | −0.005388 | 0.030819 | 0.015666 | −0.009106 | 0.06465 | 0.021967 | −0.015638 | 0.012942 | 0.00109 | −0.014047 | 0.009941 | 0.002302 | 0.019473 |
| 202 | 0.016404 | −0.031485 | −0.061141 | −0.012263 | −0.01096 | 0.030231 | 0.035995 | 0.009439 | 0.00424 | 0.000315 | −0.019984 | 0.001753 | 0.000143 | 0.009957 |
| 203 | −0.009013 | −0.07591 | −0.00255 | −9.01868 | 0.037008 | 0.015957 | 0.012282 | 0.009531 | 0.03819 | 0.016674 | −0.028275 | 0.009162 | 0.015148 | −0.024177 |
| 204 | −0.044386 | −0.016536 | −0.052619 | −0.014582 | −0.036911 | 0.055648 | −0.014014 | −0.011413 | −0.016664 | 0.009333 | 0.016747 | 0.007486 | 0.033006 | −0.023169 |
| 205 | 0.020557 | −0.043357 | −0.027415 | 0.055059 | 0.007689 | −0.05044 | 0.010451 | −0.009335 | −0.067694 | 0.000736 | −0.049983 | 0.003747 | 0.042236 | −0.015902 |
| 206 | −0.008714 | −0.058994 | 0.018315 | 0.100439 | 0.020539 | 0.045101 | 0.020034 | 0.003384 | 0.017107 | 0.019038 | 0.003482 | −0.012466 | 0.004604 | −0.017022 |
| 207 | 0.63314 | 0.018108 | 0.053912 | 0.002172 | 0.016974 | 0.009738 | 0.003938 | −0.020058 | −0.004796 | −0.039908 | 0.073662 | 0.009263 | 0.010097 | 0.030166 |
| 208 | −0.007581 | 0.755718 | −0.013503 | 0.016723 | 0.030814 | 0.000371 | 0.051261 | 0.023615 | −0.010114 | 0.028581 | −0.026827 | −0.017232 | 0.015796 | −0.027972 |
| 209 | 0.014432 | −0.020852 | 0.717321 | −0.068654 | −0.02194 | 0.073123 | 0.106303 | 0.001388 | 0.020954 | 0.010515 | 0.011886 | −0.002251 | 0.00008 | 0.012634 |
| 210 | 0.02419 | 0.01782 | −0.029172 | 0.624393 | −0.114418 | 0.028845 | −0.094026 | −0.004655 | −0.039239 | −0.000486 | −0.017957 | 0.000951 | −0.007049 | −0.016137 |
| 211 | 0.029919 | 0.028409 | −0.002731 | −0.093292 | 0.749375 | −0.065551 | −0.001934 | −0.026828 | −0.018534 | 0.022085 | 0.009326 | −0.012401 | 0.002749 | 0.00891 |
| 212 | −0.01933 | −0.020224 | 0.072395 | 0.019248 | −0.065651 | 0.641618 | 0.073797 | 0.003728 | −0.002467 | 0.026114 | 0.014876 | −0.004652 | −0.019484 | −0.006881 |
| 213 | 0.036669 | 0.022365 | 0.084916 | −0.035403 | 0.040603 | 0.074178 | 0.618042 | −0.006866 | −0.038858 | 0.013069 | −0.032595 | 0.056625 | 0.026201 | 0.012122 |
| 214 | −0.015731 | 0.022976 | 0.006935 | −0.009323 | −0.010605 | 0.004702 | −0.013487 | 0.928558 | −0.045124 | −0.000422 | 0.011292 | 0.003438 | −0.003153 | 0.00071 |
| 215 | −0.006967 | −0.043251 | 0.027616 | −0.064206 | 0.011204 | −0.003363 | −0.060151 | −0.044609 | 0.776974 | −0.028009 | −0.009766 | −0.02292 | 0.002839 | −0.039352 |
| 216 | 0.00409 | 0.040227 | 0.040449 | 0.021078 | 0.034731 | 0.022773 | −0.000479 | −0.001799 | −0.033873 | 0.883974 | −0.009393 | −0.016457 | −0.052264 | −0.017202 |
| 217 | 0.071781 | −0.044904 | 0.023592 | −0.002442 | 0.011272 | 0.021407 | −0.031519 | 0.011219 | −0.006948 | −0.007347 | 0.847888 | −0.018644 | −0.033323 | −0.076076 |
| 218 | 0.020399 | −0.004334 | −0.009645 | −0.02231 | −0.012177 | −0.000986 | 0.055371 | 0.004543 | −0.023532 | −0.01472 | 0.003265 | 0.91381 | −0.042648 | −0.027675 |
| 219 | 0.0158 | 0.019136 | 0.004631 | −0.006067 | 0.01487 | −0.004598 | 0.044143 | −0.000484 | 0.01243 | −0.063492 | −0.029382 | −0.055823 | 0.889642 | −0.035176 |
| 220 | 0.057562 | −0.030049 | 0.013625 | −0.024748 | 0.028384 | −0.011864 | 0.014669 | 0.004076 | −0.005488 | −0.010589 | −0.072759 | −0.021387 | −0.030485 | 0.863133 |
| 221 | −0.001446 | 0.007956 | −0.007983 | −0.036195 | −0.018214 | 0.002852 | 0.027722 | −0.00444 | −0.002244 | −0.011783 | −0.003251 | −0.016939 | −0.022876 | −0.034201 |
| 222 | −0.022274 | −0.012406 | −0.01999 | −0.017462 | −0.029563 | −0.009649 | 0.034021 | −0.003537 | 0.001578 | −0.009299 | −0.004436 | −0.014853 | −0.017747 | −0.00955 |
| 223 | −0.029942 | 0.00678 | 0.019617 | −0.028857 | −0.008692 | 0.005125 | −0.017001 | 0.008372 | −0.006891 | −0.022853 | 0.013165 | −0.019703 | −0.021577 | −0.025251 |
| 224 | 0.033767 | −0.011426 | 0.002023 | 0.021521 | −0.026788 | 0.01754 | 0.007672 | 0.002116 | −0.030083 | −0.049161 | −0.003989 | 0.01956 | 0.008806 | 0.004548 |
| 225 | 0.047129 | −0.01628 | 0.011307 | 0.01392 | −0.031337 | 0.010805 | 0.001255 | 0.004139 | −0.020104 | −0.043534 | 0.002845 | 0.022117 | 0.010083 | 0.009161 |
| 226 | 0.024585 | −0.007051 | −0.008944 | −0.009976 | 0.021935 | 0.004541 | 0.01064 | 0.00654 | 0.009537 | 0.022064 | 0.016845 | −0.000157 | 0.002689 | 0.007771 |
| 227 | 0.064488 | 0.01106 | 0.032602 | 0.015654 | 0.030569 | 0.04759 | 0.007374 | 0.009355 | −0.033924 | −0.025982 | 0.005388 | 0.018844 | 0.012769 | 0.005961 |
| 228 | −0.052571 | −0.025173 | −0.003065 | 0.045441 | 0.000301 | −0.000841 | 0.021614 | 0.000224 | 0.014624 | −0.004594 | 0.006803 | −0.001167 | 0.005114 | 0.017426 |
| 229 | −0.030333 | −0.011379 | 0.041773 | 0.071134 | 0.032787 | −0.006591 | −0.017905 | −0.008923 | −0.013942 | 0.004543 | 0.00474 | −0.002423 | 0.004024 | 0.008049 |
| 230 | −0.044203 | 0.058294 | 0.061079 | 0.022306 | −0.00658 | 0.002084 | −0.017724 | −0.009142 | −0.032336 | −0.061789 | 0.03151 | 0.02437 | 0.002969 | 0.020361 |
| 231 | 0.038539 | 0.000757 | −0.045325 | 0.002581 | −0.013419 | −0.005137 | 0.018845 | 0.026449 | 0.006963 | 0.007891 | 0.020351 | 0.020872 | 0.012873 | 0.018447 |
| 232 | −0.036616 | −0.014341 | 0.003307 | −0.012515 | −0.012355 | −0.051508 | 0.036452 | 0.009349 | −0.017189 | 0.006736 | 0.013449 | 0.010225 | 0.030014 | 0.008367 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 233 | −0.02047 | 0.024095 | 0.039063 | −0.02394 | −0.011721 | −0.000221 | −0.036662 | −0.002038 | −0.061462 | −0.001271 | 0.010084 | −0.016197 | 0.006337 | 0.01435 |
| 234 | −0.023547 | 0.01142 | −0.006133 | 0.039459 | 0.030006 | −0.016425 | 0.030233 | 0.014496 | −0.003669 | −0.025878 | 0.028605 | −0.002357 | −0.023109 | 0.006585 |
| 235 | 0.003093 | 0.005074 | −0.037077 | 0.050134 | −0.008823 | −0.028343 | 0.010695 | 0.018458 | −0.015514 | 0.004787 | 0.001435 | 0.006943 | −0.006971 | −0.001493 |
| 236 | −0.016716 | 0.0048 | −0.002586 | −0.031389 | −0.009186 | −0.037852 | −0.011301 | 0.013865 | 0.01501 | −0.00933 | 0.01551 | 0.015474 | 0.015841 | 0.01349 |
| 237 | 0.014778 | −0.024998 | 0.003746 | 0.019908 | −0.003435 | 0.02267 | 0.003034 | 0.00299 | 0.022782 | 0.010316 | 0.015237 | −0.001633 | 0.028469 | 0.046088 |
| 238 | 0.008847 | −0.001235 | 0.014093 | 0.013085 | −0.018229 | −0.006312 | 0.00095 | −0.004144 | 0.011896 | −0.032885 | −0.01774 | 0.003395 | −0.035175 | 0.026361 |
| 239 | −0.005533 | 0.004832 | −0.007152 | −0.011346 | −0.011897 | −0.00536 | −0.006735 | −0.000042 | −0.000122 | −0.029662 | −0.018768 | −0.00412 | −0.049075 | 0.023164 |
| 240 | −0.016288 | −0.019072 | 0.011584 | 0.019298 | 0.017577 | 0.004522 | 0.010353 | 0.011316 | 0.000201 | 0.019047 | −0.017793 | 0.018968 | 0.014521 | −0.002028 |
| 241 | −0.036619 | 0.016898 | 0.022167 | −0.010075 | 0.000408 | 0.001244 | −0.027513 | −0.007139 | −0.034117 | −0.005395 | 0.012367 | −0.003456 | 0.012925 | 0.004559 |
| 242 | −0.005314 | 0.009724 | −0.005903 | 0.012587 | −0.0161 | −0.01987 | −0.022852 | 0.004821 | −0.031646 | −0.003341 | 0.001562 | −0.007628 | 0.008989 | −0.017563 |
| 243 | 0.018123 | 0.0119 | 0.00441 | 0.023964 | −0.024366 | 0.005163 | −0.025441 | 0.007053 | −0.035102 | −0.017179 | −0.046124 | −0.006964 | −0.019936 | −0.025217 |
| 244 | −0.001173 | 0.002542 | 0.006875 | −0.024638 | −0.022529 | 0.006803 | −0.015357 | −0.009226 | −0.017189 | 0.008686 | 0.006984 | 0.022546 | 0.020394 | 0.009344 |
| 245 | −0.010896 | −0.003271 | −0.006449 | 0.019954 | 0.000368 | −0.018849 | −0.026745 | −0.000759 | −0.017023 | −0.007543 | 0.003582 | 0.005057 | 0.012705 | 0.007588 |
| 246 | 0.009065 | 0.000236 | −0.00683 | 0.001782 | 0.016381 | −0.023876 | 0.024095 | −0.00297 | −0.015435 | −0.008156 | 0.01739 | −0.014059 | −0.001703 | −0.029887 |
| 247 | 0.013209 | 0.02482 | 0.003251 | −0.027351 | −0.001964 | −0.027645 | −0.005169 | −0.003721 | −0.000168 | −0.020062 | −0.012162 | 0.003058 | −0.024525 | −0.039816 |
| 248 | 0.018487 | 0.008567 | −0.007514 | −0.035777 | −0.011233 | −0.039413 | 0.00658 | −0.005205 | −0.001548 | −0.009267 | −0.010674 | 0.010231 | −0.01747 | −0.040369 |
| 249 | −0.028154 | −0.042402 | −0.014492 | 0.021249 | −0.002846 | −0.020653 | 0.035575 | 0.01988 | 0.014687 | 0.014401 | −0.021948 | 0.008095 | 0.016646 | −0.001591 |
| 250 | −0.02675 | 0.005895 | 0.021145 | −0.005765 | 0.021949 | 0.01837 | 0.003825 | 0.006352 | 0.001215 | 0.007072 | 0.01069 | 0.021838 | 0.016844 | 0.000986 |
| 251 | −0.030381 | −0.010825 | 0.00808 | 0.00934 | 0.006799 | 0.013302 | 0.018618 | 0.006914 | 0.024607 | 0.02446 | 0.010641 | 0.028608 | 0.016934 | −0.002107 |
| 252 | 0.000347 | 0.010569 | −0.011116 | −0.0071 | 0.00749 | −0.006885 | −0.03448 | 0.003271 | −0.009737 | 0.029853 | −0.01783 | 0.025172 | 0.035896 | −0.007103 |
| 253 | −0.010082 | −0.011237 | 0.003639 | 0.021306 | −0.009041 | −0.011674 | −0.034215 | 0.001564 | −0.033299 | 0.001091 | 0.000423 | 0.007931 | 0.037031 | −0.000144 |
| 254 | −0.025976 | 0.003763 | 0.018417 | −0.002498 | −0.005354 | −0.014121 | −0.039772 | 0.010856 | −0.004441 | −0.012537 | 0.012303 | 0.009102 | −0.007857 | −0.008037 |
| 255 | 0.000736 | 0.008369 | 0.009205 | 0.000045 | 0.006194 | −0.025989 | −0.00243 | 0.006201 | 0.003244 | 0.000423 | 0.008735 | 0.02311 | 0.006505 | −0.025075 |
| 256 | 0.012968 | −0.020815 | −0.002892 | 0.052929 | 0.069476 | −0.04456 | −0.028961 | 0.013317 | −0.017904 | −0.015076 | −0.005904 | 0.012736 | 0.020053 | −0.045239 |
| 257 | −0.02738 | 0.008541 | 0.024382 | 0.005448 | 0.018957 | −0.010543 | −0.008356 | 0.004943 | 0.01033 | 0.01217 | −0.007883 | 0.022758 | 0.020828 | −0.003221 |
| 258 | 0.010038 | 0.015087 | 0.001746 | −0.027889 | −0.030095 | −0.019511 | −0.012277 | 0.003335 | −0.00558 | −0.005016 | −0.012212 | 0.010519 | 0.015481 | −0.007659 |
| 259 | −0.040268 | −0.010345 | −0.003543 | 0.003945 | −0.012418 | 0.008838 | 0.007776 | 0.004513 | 0.024773 | 0.005674 | 0.004151 | 0.014878 | 0.004136 | 0.012932 |
| 260 | −0.037385 | 0.010869 | −0.002032 | −0.010303 | 0.030525 | 0.0333 | −0.02958 | −0.011564 | 0.03347 | 0.030283 | −0.004051 | 0.039228 | 0.024965 | 0.004152 |
| 261 | −0.007271 | −0.009912 | −0.007108 | 0.021176 | 0.034903 | 0.001918 | 0.009216 | 0.004156 | 0.043723 | 0.029786 | −0.015866 | 0.030077 | 0.01672 | −0.009501 |
| 262 | −0.005167 | 0.005528 | −0.02148 | 0.00345 | −0.003746 | −0.019758 | 0.007892 | 0.005956 | 0.015094 | 0.021455 | −0.014019 | 0.0176 | 0.017625 | −0.00198 |
| 263 | −0.007249 | 0.012241 | −0.013806 | −0.001331 | −0.022152 | −0.016946 | −0.00278 | 0.003241 | 0.015361 | 0.018989 | −0.014225 | 0.02066 | 0.015813 | 0.001762 |
| 264 | −0.022277 | −0.006158 | −0.017042 | 0.020068 | −0.004158 | −0.005506 | 0.023249 | −0.005803 | 0.013905 | −0.011156 | 0.002273 | 0.007374 | −0.003528 | 0.003629 |
| 265 | 0.007087 | 0.015268 | −0.001744 | 0.019179 | 0.019456 | −0.025116 | −0.021997 | 0.001813 | 0.020769 | −0.012556 | −0.011783 | 0.01023 | −0.013501 | −0.008188 |
| 266 | 0.029947 | 0.004616 | −0.001748 | 0.022005 | 0.01819 | −0.046333 | −0.018348 | 0.003483 | 0.035649 | −0.009481 | −0.017782 | 0.019448 | −0.011878 | −0.028676 |
| 267 | 0.043595 | −0.04291 | 0.008815 | 0.024211 | 0.053887 | 0.016452 | −0.014778 | 0.001682 | −0.037748 | −0.007885 | −0.005105 | −0.021262 | −0.003699 | 0.000151 |
| 268 | 0.018193 | 0.00049 | −0.022903 | −0.022685 | 0.016991 | 0.007512 | 0.007212 | 0.0021 | −0.007648 | 0.012959 | 0.014889 | −0.002022 | 0.000336 | 0.010346 |
| 269 | 0.017734 | −0.001616 | −0.007165 | −0.006013 | 0.01434 | 0.008642 | −0.000618 | −0.002851 | −0.011359 | 0.016819 | 0.017979 | 0.004395 | 0.010481 | 0.00383 |
| 270 | 0.019762 | 0.005586 | −0.006625 | −0.005023 | 0.031271 | 0.027518 | 0.016887 | 0.003769 | 0.009258 | 0.01777 | 0.013977 | 0.010563 | 0.01196 | 0.00122 |
| 271 | 0.002565 | 0.015748 | −0.024817 | 0.042497 | −0.03178 | 0.026507 | 0.018458 | −0.013585 | 0.044161 | 0.00911 | 0.004225 | 0.005805 | −0.005367 | 0.035587 |
| 272 | −0.034266 | −0.021047 | 0.016403 | 0.06202 | 0.028859 | −0.017592 | 0.009579 | 0.002805 | 0.028399 | 0.030425 | 0.003189 | −0.005005 | −0.006951 | 0.016115 |
| 273 | −0.036786 | 0.034726 | 0.002432 | −0.023859 | −0.008428 | 0.019576 | −0.004857 | −0.003743 | 0.009372 | 0.036378 | 0.011968 | 0.011616 | 0.017397 | 0.004717 |
| 274 | −0.038791 | 0.038725 | 0.010138 | −0.008078 | −0.003447 | 0.020412 | −0.010721 | −0.006668 | 0.012878 | 0.03486 | 0.012774 | 0.01573 | 0.019906 | 0.00455 |
| 275 | −0.035401 | 0.038301 | 0.05966 | 0.021484 | 0.01849 | 0.024029 | 0.010977 | −0.01054 | −0.006626 | −0.025439 | 0.001675 | 0.029698 | 0.004178 | −0.007382 |
| 276 | −0.031094 | 0.002854 | −0.005792 | −0.004598 | 0.002796 | −0.035167 | −0.000272 | 0.017143 | 0.032458 | −0.006003 | 0.015854 | 0.007697 | 0.010956 | 0.017454 |
| 277 | 0.00301 | −0.005504 | −0.024925 | 0.000771 | −0.020538 | 0.008621 | −0.01099 | −0.000522 | 0.004283 | 0.019969 | 0.02099 | −0.020256 | 0.016328 | 0.054165 |
| 278 | −0.013246 | −0.009268 | −0.027153 | 0.000999 | −0.021852 | 0.018344 | −0.01571 | −0.002859 | 0.000208 | 0.023801 | 0.036342 | −0.01032 | 0.026482 | 0.064927 |
| 279 | −0.016809 | 0.006288 | −0.015317 | 0.012136 | −0.001923 | 0.003321 | 0.00762 | −0.006131 | 0.019718 | −0.025988 | −0.021113 | −0.001523 | −0.057683 | 0.021474 |
| 280 | 0.005799 | 0.010148 | −0.006418 | 0.041328 | −0.013484 | 0.02671 | −0.018998 | 0.01464 | −0.029209 | −0.025633 | −0.017799 | −0.010976 | 0.009011 | −0.003793 |
| 281 | 0.011337 | −0.002645 | −0.039486 | −0.023821 | −0.018069 | 0.007801 | 0.008519 | −0.001286 | 0.000403 | 0.011085 | 0.030339 | −0.016421 | 0.007937 | −0.03098 |
| 282 | 0.009769 | 0.023763 | −0.044495 | −0.026231 | −0.03965 | 0.015647 | 0.014022 | −0.002793 | −0.007165 | 0.007481 | 0.035022 | −0.006805 | 0.014682 | −0.021288 |

APPENDIX B3-continued

PCA Transformation Matrix (340 × 340 Early/Late)

| | | | | | | | | | | | | | | |
|---|---|---|---|---|---|---|---|---|---|---|---|---|---|---|
| 283 | 0.012191 | 0.031987 | −0.010273 | −0.011664 | 0.004864 | −0.007758 | −0.012265 | −0.009934 | 0.021338 | −0.008366 | −0.007729 | 0.00517 | −0.037801 | −0.04595 |
| 284 | −0.034925 | 0.002484 | 0.015013 | 0.019501 | 0.017604 | −0.000569 | 0.002623 | 0.001265 | 0.011323 | 0.012453 | 0.002837 | 0.014793 | 0.01517 | 0.000632 |
| 285 | −0.037801 | 0.01038 | 0.010412 | 0.014756 | 0.006714 | 0.008533 | 0.007719 | −0.002269 | 0.008132 | 0.013186 | 0.008181 | 0.017011 | 0.018532 | 0.007393 |
| 286 | −0.010566 | 0.015242 | 0.025036 | −0.002154 | −0.031681 | 0.00626 | −0.023208 | −0.001156 | −0.004251 | −0.009024 | −0.007449 | 0.007491 | 0.01295 | 0.002535 |
| 287 | −0.01147 | 0.026035 | 0.021161 | −0.001652 | −0.034565 | 0.010359 | −0.020087 | −0.003997 | −0.001609 | −0.003568 | −0.00487 | 0.011099 | 0.014048 | 0.008875 |
| 288 | 0.007599 | 0.020506 | −0.01192 | 0.001749 | −0.022409 | −0.0045041 | 0.003335 | −0.0097651 | 0.0111761 | −0.002826 | −0.013097 | 0.014923 | 0.015654 | −0.020296 |
| 289 | 0.010874 | 0.008648 | −0.016597 | −0.002137 | 0.016575 | −0.029347 | 0.013725 | 0.008106 | 0.024278 | 0.013526 | −0.028456 | 0.0234581 | 0.010231 | −0.026304 |
| 290 | 0.01606 | −0.000806 | −0.021762 | 0.00244 | −0.014487 | 0.017567 | −0.008701 | −0.003245 | −0.001293 | 0.014438 | −0.036098 | 0.019388 | 0.01679 | −0.024664 |
| 291 | 0.017395 | −0.000981 | −0.021596 | 0.004888 | −0.016474 | 0.019053 | −0.006805 | −0.002002 | −0.000098 | 0.013849 | −0.038858 | 0.01764 | 0.014672 | −0.025225 |
| 292 | 0.007003 | −0.000905 | −0.01139 | 0.010321 | −0.021577 | 0.014881 | −0.003493 | −0.002452 | −0.003243 | 0.00761 | −0.047058 | 0.016105 | 0.007531 | −0.028805 |
| 293 | −0.046399 | 0.006198 | −0.017624 | −0.031749 | 0.006306 | 0.005337 | −0.019508 | 0.021739 | −0.019791 | −0.020202 | 0.027707 | 0.003158 | −0.006629 | 0.027114 |
| 294 | 0.012655 | 0.003749 | −0.031135 | −0.029807 | −0.000089 | 0.009567 | 0.017024 | 0.003596 | −0.012314 | 0.006357 | 0.005097 | −0.015561 | −0.008664 | 0.009022 |
| 295 | −0.043015 | 0.014895 | 0.001438 | 0.016867 | 0.006906 | 0.001999 | −0.023212 | 0.010083 | 0.012909 | 0.025445 | 0.002922 | 0.008079 | 0.006957 | 0.004234 |
| 296 | −0.01049 | 0.000128 | 0.020525 | 0.015189 | 0.032421 | 0.015309 | −0.026273 | 0.00008 | 0.014594 | 0.047697 | −0.015815 | 0.008934 | 0.022827 | −0.030504 |
| 297 | −0.052121 | 0.003886 | −0.00965 | −0.001842 | 0.010044 | 0.012548 | −0.033764 | 0.012302 | 0.015753 | 0.018179 | 0.015751 | 0.004199 | 0.012833 | 0.001757 |
| 298 | −0.048531 | −0.007132 | 0.017893 | −0.060014 | −0.015229 | 0.022211 | −0.02296 | −0.011198 | 0.002194 | 0.0122551 | −0.008849 | −0.002668 | −0.015181 | −0.012909 |
| 299 | −0.030213 | −0.032062 | −0.016198 | −0.036086 | −0.01256 | 0.00575 | −0.00715 | 0.025722 | 0.031214 | 0.016581 | 0.026869 | 0.004553 | 0.005163 | 0.018441 |
| 300 | −0.042045 | 0.031348 | 0.02969 | 0.034312 | 0.021779 | 0.031683 | −0.019758 | −0.011011 | −0.012836 | −0.00933 | 0.010295 | 0.021641 | 0.0025374 | 0.008408 |
| 301 | −0.044686 | −0.024233 | −0.009988 | 0.001446 | 0.013069 | −0.018375 | 0.013242 | 0.012277 | 0.012027 | 0.012864 | 0.016257 | 0.008514 | 0.000222 | 0.017341 |
| 302 | −0.015178 | −0.04079 | −0.003254 | 0.007708 | 0.024907 | 0.002747 | 0.020219 | 0.009784 | 0.010085 | 0.008732 | −0.024054 | 0.000001 | −0.013553 | −0.01427 |
| 303 | −0.005801 | −0.046817 | 0.006179 | −0.031408 | −0.018916 | 0.005485 | −0.005905 | 0.023165 | 0.011762 | 0.01926 | −0.012708 | −0.004432 | 0.002807 | 0.013269 |
| 304 | −0.001073 | −0.064333 | −0.005824 | −0.02135 | 0.001253 | 0.012153 | 0.005556 | 0.028668 | 0.025454 | 0.018878 | −0.003579 | 0.000709 | 0.002519 | 0.013366 |
| 305 | −0.089792 | −0.00533 | 0.018746 | 0.007063 | 0.034781 | 0.02036 | 0.015713 | 0.016197 | 0.017722 | −0.011036 | 0.016701 | 0.006965 | −0.004356 | 0.019529 |
| 306 | −0.004006 | −0.009773 | −0.01548 | −0.005626 | 0.064694 | 0.03401 | 0.015027 | 0.026525 | −0.034449 | −0.006437 | −0.012357 | −0.013029 | 0.013665 | −0.015969 |
| 307 | 0.020911 | 0.017101 | −0.008496 | 0.086486 | −0.057136 | 0.017247 | −0.009449 | 0.00695 | −0.001776 | 0.005082 | 0.01582 | 0.00818 | 0.059596 | 0.028033 |
| 308 | −0.003163 | 0.076877 | 0.041438 | 0.023399 | 0.018975 | 0.018549 | −0.005797 | 0.003907 | 0.051732 | −0.002864 | 0.011927 | 0.018491 | 0.00887 | 0.012963 |
| 309 | 0.025555 | −0.012999 | 0.006582 | 0.017649 | −0.001146 | 0.005144 | −0.018294 | 0.009784 | 0.000568 | −0.000059 | 0.008376 | −0.002202 | −0.00444 | 0.018988 |
| 310 | 0.040212 | −0.028901 | 0.032188 | −0.010442 | −0.024222 | 0.000418 | −0.049116 | −0.009339 | −0.056562 | 0.008429 | −0.033908 | 0.004106 | 0.002805 | 0.000615 |
| 311 | −0.010409 | 0.03253 | 0.007727 | −0.018254 | 0.000491 | 0.010329 | −0.041605 | 0.000327 | 0.009935 | 0.005785 | 0.025307 | 0.013086 | 0.003258 | 0.027573 |
| 312 | −0.009037 | 0.038225 | 0.003938 | 0.026747 | 0.025649 | −0.026236 | −0.001249 | 0.017706 | −0.00632 | 0.010051 | 0.025828 | −0.012014 | −0.010013 | −0.017932 |
| 313 | 0.018994 | −0.003098 | 0.034292 | 0.003528 | 0.001503 | −0.031402 | −0.022825 | 0.006597 | 0.010316 | 0.005205 | 0.014872 | −0.000784 | −0.004789 | −0.003408 |
| 314 | −0.002719 | −0.052111 | −0.032121 | −0.038788 | −0.046185 | −0.007365 | −0.01413 | 0.004387 | −0.02177 | 0.008426 | −0.014869 | −0.027798 | 0.008145 | −0.002569 |
| 315 | 0.015893 | 0.011734 | 0.020656 | 0.028358 | −0.001405 | 0.007357 | −0.030803 | 0.010105 | 0.008499 | −0.001778 | 0.014396 | 0.001309 | 0.013742 | 0.012924 |
| 316 | −0.034912 | −0.013526 | 0.026353 | 0.076682 | 0.020371 | 0.001494 | 0.052823 | −0.009458 | 0.012526 | −0.007333 | −0.016088 | −0.001978 | −0.005136 | −0.000345 |
| 317 | 0.011363 | 0.01679 | 0.013305 | 0.037569 | 0.007161 | −0.017099 | −0.037719 | 0.002475 | 0.004636 | 0.012497 | 0.010425 | 0.00544 | 0.001099 | 0.015474 |
| 318 | 0.006586 | −0.024567 | −0.006297 | −0.0004 | −0.00955 | 0.006856 | −0.041783 | −0.006811 | 0.022339 | 0.014108 | 0.017032 | 0.026693 | 0.016428 | 0.027891 |
| 319 | 0.019132 | 0.006631 | 0.017531 | 0.027212 | −0.018663 | 0.003368 | −0.041617 | 0.005561 | −0.007847 | −0.001799 | 0.017245 | 0.000697 | 0.013201 | 0.012989 |
| 320 | 0.000902 | 0.010216 | 0.005169 | −0.031445 | −0.004524 | −0.002178 | −0.036372 | 0.008252 | −0.014636 | 0.000104 | 0.001876 | −0.011244 | −0.021729 | −0.00825 |
| 321 | 0.017322 | −0.018675 | −0.021067 | −0.041656 | −0.016311 | 0.014489 | 0.016678 | 0.00534 | 0.011632 | 0.028483 | 0.000181 | −0.005591 | 0.03339 | −0.006597 |
| 722 | 0.038438 | 0.010757 | 0.001387 | 0.012489 | 0.015604 | 0.012356 | 0.013612 | 0.009532 | 0.010958 | −0.014415 | −0.043713 | 0.018455 | −0.005902 | 0.010195 |
| 323 | −0.010611 | −0.008406 | 0.018903 | −0.029449 | −0.01921 | −0.040728 | 0.013328 | 0.00667 | −0.006366 | 0.003954 | 0.014679 | −0.002373 | 0.005933 | 0.003313 |
| 324 | −0.048183 | −0.029814 | −0.023077 | −0.028697 | −0.000169 | 0.039739 | 0.05509 | −0.013698 | 0.038163 | −0.003297 | −0.00055 | 0.004898 | −0.016336 | −0.019118 |
| 325 | 0.006459 | 0.005086 | 0.000593 | 0.018519 | 0.031989 | 0.006496 | 0.006167 | −0.00798 | −0.000573 | 0.001979 | −0.002827 | −0.010567 | −0.003417 | −0.012152 |
| 326 | 0.006361 | 0.022127 | 0.034547 | −0.005736 | −0.011864 | −0.053901 | −0.028191 | −0.01092 | 0.003092 | 0.00049 | −0.007225 | 0.008989 | −0.018353 | 0.002388 |
| 327 | −0.013174 | −0.008493 | 0.029853 | 0.018579 | −0.010376 | −0.013987 | −0.003176 | 0.001055 | 0.010543 | 0.011554 | −0.002016 | 0.002516 | −0.005451 | −0.000081 |
| 328 | −0.018823 | 0.021858 | −0.030954 | −0.010773 | 0.030721 | 0.018144 | 0.0723021 | 0.007742 | 0.015576 | 0.010912 | −0.002373 | −0.030715 | 0.007154 | −0.009614 |
| 329 | −0.002131 | −0.002345 | 0.021328 | −0.002847 | −0.022721 | −0.053262 | 0.020731 | 0.000964 | 0.028931 | 0.017373 | −0.000721 | 0.007009 | −0.007905 | −0.003606 |
| 330 | −0.015625 | −0.022847 | 0.03101 | −0.052424 | 0.033249 | −0.002808 | 0.019436 | −0.017399 | −0.051351 | 0.00877 | −0.013361 | −0.001156 | −0.006305 | 0.006594 |
| 331 | 0.0082 | 0.014524 | 0.001637 | 0.004827 | −0.003315 | −0.013673 | 0.000508 | 0.003302 | −0.008695 | −0.014621 | −0.000234 | −0.005269 | −0.015777 | 0.010012 |
| 332 | 0.005903 | 0.038074 | −0.001323 | −0.021298 | 0.012914 | 0.003069 | −0.019871 | −0.010007 | −0.026675 | −0.016684 | 0.01897 | 0.016218 | −0.006594 | 0.023753 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 333 | 0.006899 | −0.007893 | −0.009579 | 0.031792 | 0.03084 | −0.003128 | 0.011167 | 0.000256 | −0.006369 | −0.014009 | 0.006539 | 0.004265 | 0.000275 | 0.005604 |
| 334 | −0.000049 | −0.0317 | −0.03649 | 0.038489 | 0.020775 | 0.018741 | 0.085519 | −0.003512 | −0.033611 | 0.000098 | −0.020105 | −0.03302 | −0.013234 | −0.039407 |
| 335 | −0.000799 | 0.004055 | 0.004496 | 0.00537 | −0.00666 | −0.038107 | −0.001756 | 0.000452 | −0.027636 | −0.012438 | 0.023441 | −0.003929 | −0.005573 | 0.009497 |
| 336 | 0.030515 | 0.000917 | 0.037683 | −0.013518 | 0.020952 | 0.017211 | −0.045359 | 0.01455 | −0.012022 | −0.026636 | 0.010097 | −0.00246 | −0.002101 | 0.023749 |
| 337 | −0.022115 | −0.02642 | −0.049127 | 0.065897 | 0.029301 | 0.022169 | 0.05497 | 0.011271 | 0.049104 | 0.025396 | 0.002811 | 0.011183 | 0.008089 | −0.00824 |
| 338 | −0.01455 | −0.03201 | 0.044703 | −0.045892 | −0.042948 | 0.0365 | −0.014091 | −0.000885 | −0.023272 | 0.030142 | −0.029182 | −0.007286 | 0.003802 | −0.012966 |
| 339 | −0.026225 | −0.027872 | −0.044037 | 0.039137 | 0.023812 | 0.012308 | −0.004827 | 0.004493 | 0.016675 | 0.004062 | 0.009885 | 0.003553 | −0.002508 | 0.021625 |
| 340 | −0.077431 | −0.014127 | 0.02739 | −0.028584 | 0.038928 | 0.088819 | −0.046525 | 0.000709 | 0.007433 | −0.007737 | −0.010968 | 0.022163 | 0.009644 | −0.014176 |

| | HN | HO | HP | HQ | HR | HS | HT | HU | HV | HW | HX | HY | HZ | IA |
|---|---|---|---|---|---|---|---|---|---|---|---|---|---|---|
| 1 | 0.010172 | −0.01127 | −0.000065 | 0.001721 | −0.014064 | −0.015701 | 0.003229 | −0.072243 | 0.037112 | 0.063524 | −0.035913 | −0.079261 | −0.06979 | −0.123316 |
| 2 | −0.036528 | −0.085375 | −0.048164 | −0.040841 | −0.064017 | −0.043006 | −0.0986 | −0.016604 | −0.079106 | −0.012083 | −0.0018021 | 0.045574 | 0.06049 | −0.042182 |
| 3 | 0.010975 | 0.01555 | 0.004848 | −0.003836 | −0.014755 | −0.092115 | −0.115548 | −0.051285 | −0.069498 | −0.088607 | −0.061919 | 0.017101 | 0.010697 | −0.052821 |
| 4 | 0.003742 | 0.039229 | 0.05656 | 0.100983 | 0.085312 | −0.037288 | 0.014596 | 0.033935 | −0.019623 | −0.04381 | −0.042475 | 0.037601 | −0.012207 | −0.046566 |
| 5 | 0.068279 | −0.034253 | 0.016782 | 0.051477 | 0.080672 | −0.044358 | −0.001246 | 0.01731 | −0.06503 | 0.060225 | 0.030487 | 0.061792 | 0.026737 | 0.046869 |
| 6 | −0.105715 | −0.076196 | −0.08444 | 0.122995 | 0.139304 | 0.010827 | 0.05182 | 0.025478 | −0.002424 | −0.014098 | 0.083217 | 0.054596 | 0.009249 | 0.059571 |
| 7 | −0.009289 | 0.011213 | 0.012379 | −0.014594 | −0.0271 | 0.071035 | −0.009909 | 0.062854 | 0.079607 | −0.009052 | −0.0414 | 0.140216 | 0.146204 | 0.019991 |
| 8 | 0.03548 | 0.011628 | −0.017537 | 0.039248 | 0.043569 | −0.045703 | 0.025418 | −0.018882 | −0.007373 | 0.023948 | 0.004415 | −0.108734 | −0.021895 | −0.00346 |
| 9 | 0.006303 | 0.037682 | 0.009179 | −0.062638 | −0.084337 | −0.013759 | −0.054889 | −0.031998 | −0.067857 | −0.057467 | −0.052219 | −0.038253 | 0.052592 | −0.014775 |
| 10 | −0.050904 | −0.063331 | −0.044542 | 0.051365 | 0.045182 | −0.017942 | −0.073211 | 0.137212 | 0.069004 | 0.068954 | −0.011427 | 0.07709 | 0.00584 | 0.103653 |
| 11 | −0.027358 | 0.005762 | −0.020131 | −0.049385 | −0.04742 | 0.028131 | −0.02614 | 0.021082 | −0.05949 | −0.049294 | −0.053614 | 0.035052 | −0.018698 | 0.008449 |
| 12 | −0.009162 | 0.056176 | 0.024734 | 0.066174 | 0.0671231 | 0.038943 | 0.093053 | −0.044478 | −0.026496 | 0.052116 | 0.097957 | −0.027388 | −0.036991 | 0.003277 |
| 13 | 0.009396 | 0.052983 | 0.061502 | 0.065954 | 0.059533 | 0.049162 | 0.036588 | 0.038183 | −0.05016 | −0.029232 | 0.0185 | −0.017416 | −0.020906 | −0.018296 |
| 14 | 0.006823 | −0.010351 | −0.011702 | −0.070103 | −0.042387 | −0.01894 | −0.006306 | −0.008868 | −0.112553 | −0.059196 | 0.01714 | −0.009654 | 0.009744 | 0.063366 |
| 15 | −0.0628 | −0.045014 | −0.003629 | −0.030918 | −0.019889 | −0.018633 | −0.011993 | 0.022699 | 0.07177 | 0.067641 | 0.012932 | 0.029054 | 0.050587 | 0.039836 |
| 14 | 0.01781 | −0.048755 | −0.019231 | 0.061408 | 0.06821 | 0.046427 | 0.090113 | −0.043893 | 0.039756 | 0.039473 | −0.026017 | 0.001584 | −0.036018 | −0.086874 |
| 17 | 0.00926 | 0.029766 | −0.004669 | 0.031338 | 0.048435 | 0.000126 | −0.032321 | −0.007292 | −0.02693 | −0.016488 | 0.025716 | 0.009427 | −0.143533 | −0.08107 |
| 18 | −0.010177 | 0.025528 | −0.008969 | 0.0021 | −0.011984 | 0.01529 | −0.024026 | 0.126963 | 0.079637 | −0.017496 | −0.008778 | 0.030441 | 0.008474 | −0.03099 |
| 19 | 0.043491 | 0.048008 | 0.02611 | 0.04258 | 0.07488 | 0.066383 | 0.147825 | 0.113149 | 0.060262 | 0.030852 | 0.057937 | 0.04845 | 0.080368 | 0.070601 |
| 20 | 0.048663 | −4.000991 | −0.027938 | 0.060529 | 0.04798 | −4.007108 | −4.026495 | 0.041046 | 0.007939 | −4.047894 | 0.069307 | 0.072141 | 0.045586 | 0.02304 |
| 21 | −0.037645 | 0.016526 | 0.003563 | −0.001938 | −0.007043 | 0.033661 | 0.058296 | −0.019487 | 0.040182 | 0.026384 | 0.02603 | −0.039181 | −0.054062 | 0.025931 |
| 22 | −0.040866 | −0.030239 | −0.074286 | −0.062037 | −0.072537 | 0.059146 | 0.019413 | 0.036899 | −0.028381 | −0.017332 | 0.049301 | 0.004302 | 0.023775 | 0.028482 |
| 23 | −0.077698 | −0.007153 | −0.018513 | −0.034105 | −0.026242 | −0.027701 | −0.012476 | −0.018425 | −0.118563 | 0.017473 | 0.078482 | −0.08881 | −0.013807 | 0.036383 |
| 24 | 0.053526 | 0.023288 | 0.036423 | 0.086511 | 0.118319 | −0.009879 | 0.012741 | −0.026012 | 0.021933 | 0.023017 | 0.052813 | −0.025269 | −0.050109 | −0.113639 |
| 25 | −0.048319 | −0.056342 | −0.102553 | 0.028985 | 0.009078 | 0.061489 | 0.075641 | −0.019582 | −0.044952 | −0.035394 | 0.035142 | −0.050178 | −0.107115 | 0.04051 |
| 26 | −0.090835 | −0.00974 | −0.018855 | 0.060562 | 0.068103 | −0.004317 | 0.039058 | 0.055093 | 0.082611 | 0.095885 | −0.0178981 | 0.073999 | 0.030396 | 0.009615 |
| 27 | 0.017345 | 0.032706 | 0.004537 | 0.011888 | 0.018667 | 0.036307 | 0.068979 | 0.087647 | −0.121569 | −0.10665 | −0.013026 | −0.004861 | −0.002877 | 0.068141 |
| 28 | 0.034956 | 0.009838 | −0.018988 | −0.045966 | −0.014574 | −0.055458 | −0.034564 | −0.058376 | 0.035393 | 0.004411 | −0.016669 | −0.107338 | 0.04098 | 0.003722 |
| 29 | −0.025089 | 0.003766 | −0.003434 | 0.011799 | 0.03355 | 0.006606 | 0.021983 | 0.013273 | 0.03816 | 0.014322 | −0.001032 | −0.000871 | 0.001066 | 0.021422 |
| 30 | 0.027324 | −0.059303 | −0.009063 | 0.007613 | 0.035652 | 0.07662 | 0.012648 | −0.045186 | −0.04054 | −0.007019 | 0.071327 | 0.040435 | −0.036223 | −0.046514 |
| 31 | 0.075815 | −0.028887 | 0.010322 | −0.109136 | −0.097958 | 0.047448 | −0.097093 | −0.045216 | 0.06727 | −0.11266 | −0.032335 | −0.082379 | −0.053278 | 0.03449 |
| 32 | 0.069756 | 0.126402 | 0.1054 | −0.072463 | −0.057669 | 0.009761 | −0.0513 | 0.087723 | −0.004491 | 0.032016 | 0.015585 | 0.028695 | −0.040843 | 0.063238 |
| 33 | −0.035225 | 0.021892 | 0.035312 | 0.031268 | 0.003543 | −0.01398 | 0.092436 | −0.011099 | −0.026204 | 0.081162 | 0.055154 | −0.00615 | −0.029836 | 0.087912 |
| 34 | 0.022786 | 0.022967 | 0.016614 | −0.03595 | −0.018073 | −0.027419 | −0.080556 | 0.010321 | −0.03279 | −0.022629 | 0.016231 | −0.00396 | 0.004261 | 0.075824 |
| 35 | −0.013843 | −0.057809 | −0.043177 | −0.02772 | −0.037204 | −0.023658 | −0.013691 | −0.050335 | 0.02395 | 0.011369 | 0.017933 | −0.035285 | 0.004096 | 0.002177 |
| 36 | −0.102381 | −0.030211 | −0.010232 | 0.025318 | 0.018761 | −0.003814 | 0.009244 | −0.026933 | 0.000361 | −0.015514 | −0.044908 | 0.03046 | 0.02808 | −0.130985 |
| 37 | −0.01907 | −0.016026 | −0.03729 | −0.024371 | 0.004361 | −0.02541 | 0.023819 | −0.061151 | 0.022322 | 0.013864 | 0.081179 | −0.049804 | 0.080553 | 0.014663 |
| 38 | 0.036934 | −0.018031 | 0.028957 | −0.056675 | −0.035606 | 0.033369 | −0.015531 | 0.00928 | 0.026046 | −0.054214 | 0.083267 | 0.030989 | 0.025128 | 0.068681 |
| 39 | −0.062753 | −0.009512 | −0.046798 | −0.090455 | −0.101134 | 0.030979 | −0.033407 | 0.027423 | 0.003863 | 0.021544 | −0.024031 | 0.00904 | 0.042166 | 0.088311 |

APPENDIX B3-continued

PCA Transformation Matrix (340 × 340 Early/Late)

| | | | | | | | | | | | | | | |
|---|---|---|---|---|---|---|---|---|---|---|---|---|---|---|
| 40 | −0.00383 | 0.024239 | 0.004049 | 0.002478 | −0.00163 | 0.007558 | 0.003834 | 0.011379 | −0.001427 | −0.002732 | −0.013357 | 0.009377 | 0.014029 | −0.001501 |
| 41 | −0.014915 | −0.032865 | 0.089162 | −0.017819 | −0.027508 | −0.007413 | 0.037068 | −0.026001 | −0.127394 | −0.009528 | 0.15467 | −0.022949 | −0.010671 | 0.064949 |
| 42 | 0.025224 | −0.032187 | −0.055237 | 0.040208 | 0.008642 | −0.015691 | 0.038013 | 0.013868 | 0.067954 | 0.013392 | 0.008723 | 0.033488 | −0.018946 | −0.013234 |
| 43 | −0.05373 | −0.094592 | −0.046403 | 0.025061 | 0.019833 | 0.020971 | 0.061768 | −0.061822 | −0.008627 | 0.032501 | 0.016996 | −0.03527 | 0.013946 | 0.00096 |
| 44 | −0.033923 | −0.035154 | −0.069145 | −0.025625 | −0.051011 | 0.007436 | 0.00514 | −0.072959 | −0.004056 | −0.028505 | −0.002231 | 0.017437 | 0.048345 | −0.087835 |
| 45 | 0.005747 | −0.073929 | −0.024752 | 0.008585 | 0.003404 | −0.021747 | 0.070792 | −0.005322 | 0.038727 | 0.096958 | 0.064534 | −0.092351 | −0.058943 | 0.097343 |
| 46 | −0.031321 | −0.000413 | −0.046727 | 0.014645 | 0.05397 | −0.059347 | −0.108414 | 0.044979 | 0.115141 | 0.01039 | −0.145259 | −0.037589 | 0.017359 | −0.015231 |
| 47 | −0.00471 | −0.045028 | −0.017209 | −0.103316 | −0.109839 | 0.02238 | −0.004437 | 0.025623 | 0.000361 | −0.120359 | −0.054261 | −0.068761 | 0.037038 | 0.011165 |
| 48 | −0.00376 | −0.007176 | 0.018982 | −0.018817 | −0.029343 | 0.038858 | 0.004649 | 0.04789 | −0.010556 | −0.097811 | 0.021974 | 0.046144 | −0.031587 | 0.004681 |
| 49 | −0.015798 | 0.019255 | 0.022095 | 0.070728 | 0.07527 | 0.013447 | 0.070716 | −0.031934 | −0.054697 | 0.070518 | −0.041099 | 0.014512 | 0.063789 | 0.009573 |
| 50 | −0.039677 | −0.002094 | 0.045705 | −0.003774 | 0.017737 | −0.010503 | −0.112176 | 0.018811 | 0.126747 | 0.012987 | 0.060015 | −0.003664 | 0.036812 | 0.01726 |
| 51 | 0.019116 | −0.006788 | −0.016875 | 0.07768 | 0.091501 | 0.00332 | 0.016379 | 0.018595 | −0.119541 | −0.103952 | −0.008316 | 0.024598 | −0.017705 | 0.008843 |
| 52 | 0.020459 | 0.009836 | 0.019553 | −0.020448 | −0.033883 | −0.002609 | −0.051127 | 0.000285 | 0.044108 | 0.089414 | 0.102821 | −0.000465 | −0.04317 | 0.004534 |
| 53 | 0.041937 | 0.022339 | 0.023086 | −0.03414 | 0.003254 | 0.050481 | 0.024357 | −0.034991 | 0.04251 | −0.01504 | 0.007154 | −0.000302 | 0.013713 | 0.012957 |
| 54 | −0.001828 | −0.016628 | 0.05993 | −0.05039 | −0.040842 | 0.001729 | −0.067365 | 0.048469 | −0.027939 | −0.056662 | 0.048073 | −0.058891 | −0.126969 | −0.058493 |
| 55 | 0.015799 | −0.023895 | −0.004635 | −0.008391 | −0.010544 | −0.064871 | −0.020685 | 0.016123 | 0.029701 | 0.006647 | −0.045618 | −0.094192 | −0.046863 | 0.038513 |
| 56 | −0.017316 | 0.02292 | 0.070468 | −0.069893 | −0.075839 | 0.016438 | −0.043401 | 0.017613 | 0.054869 | −0.017085 | 0.035553 | −0.045696 | −0.019696 | 0.004743 |
| 57 | 0.02089 | 0.017769 | 0.057171 | 0.074988 | 0.09586 | 0.001417 | 0.019054 | −0.033488 | −0.002447 | 0.035944 | −0.080783 | −0.028773 | 0.099757 | 0.050168 |
| 58 | 0.068478 | 0.08712 | 0.025678 | −0.014635 | −0.011057 | −0.008619 | −0.064754 | 0.018334 | 0.004447 | 0.061591 | −0.023175 | 0.041861 | −0.025932 | −0.076844 |
| 59 | −0.051458 | 0.034425 | 0.006688 | 0.011358 | 0.001688 | 0.01228 | 0.044353 | 0.022536 | 0.038889 | −0.029676 | −0.07243 | 0.004811 | 0.031278 | −0.018593 |
| 60 | 0.027419 | 0.008262 | −0.003605 | −0.019582 | −0.018996 | 0.009956 | 0.006472 | 0.014544 | 0.015223 | −0.002452 | 0.006927 | −0.017946 | −0.0295 | 0.00706 |
| 61 | 0.047031 | 0.015421 | 0.014149 | 0.028497 | 0.032394 | −0.007025 | −0.005489 | 0.023042 | 0.029131 | 0.012296 | 0.007262 | −0.011893 | −0.025407 | −0.004849 |
| 62 | −0.019106 | 0.006916 | −0.012028 | −0.002013 | −0.013543 | 0.010425 | 0.025682 | −0.005733 | 0.003929 | −0.00667 | 0.039507 | −0.009036 | −0.000938 | −0.020544 |
| 63 | 0.014024 | 0.013877 | 0.00735 | 0.022565 | 0.022387 | 0.002219 | 0.012008 | 0.013026 | −0.004921 | −0.011126 | 0.015044 | 0.003793 | 0.011553 | 0.002449 |
| 64 | −0.00003 | −0.001843 | −0.003083 | 0.003257 | −0.003978 | −0.006646 | −0.002257 | −0.018898 | −0.015522 | −0.000862 | −0.002591 | −0.026553 | 0.020463 | −0.008141 |
| 65 | −0.052954 | −0.00336 | −0.010759 | 0.007515 | 0.001888 | 0.003935 | −0.017984 | 0.015762 | 0.018417 | 0.017614 | −0.009391 | 0.013187 | 0.007483 | −0.01112 |
| 66 | −0.001884 | 0.030299 | 0.015103 | 0.010571 | 0.023423 | −0.005052 | −0.027359 | 0.007666 | 0.033488 | 0.031797 | −0.01441 | −0.002228 | 0.009285 | −0.021079 |
| 67 | 0.013396 | −0.018752 | −0.014178 | −0.015047 | −0.005391 | 0.019988 | −0.007745 | −0.019439 | 0.004322 | −0.0266 | 0.03899 | −0.004414 | 0.00129 | −0.008765 |
| 68 | −0.014402 | 0.005423 | −0.015564 | −0.004966 | −0.019733 | −0.001561 | −0.030731 | 0.014413 | 0.008082 | −0.017163 | −0.007043 | 0.027574 | 0.023301 | −0.043073 |
| 69 | 0.02153 | −0.013226 | 0.002449 | 0.017719 | 0.010691 | −0.00693 | 0.013998 | −0.020239 | −0.006487 | 0.014122 | 0.031208 | −0.006938 | −0.020616 | −0.021226 |
| 70 | 0.012087 | 0.012372 | 0.009866 | 0.000863 | 0.00137 | −0.007464 | 0.006977 | −0.02152 | 0.015306 | 0.003396 | 0.001288 | −0.013499 | −0.007798 | −0.009177 |
| 71 | −0.007504 | −0.006438 | −0.00647 | 0.015425 | 0.003993 | −0.003916 | −0.011276 | 0.007707 | −0.021853 | −0.015477 | −0.021753 | 0.01543 | 0.01897 | −0.021293 |
| 72 | −0.008318 | −0.006244 | 0.000268 | 0.034868 | 0.027087 | 0.001937 | 0.051814 | −0.014123 | −0.040597 | −0.009597 | −0.015409 | 0.005216 | 0.010622 | −0.015369 |
| 73 | −0.025548 | 0.000634 | 0.003723 | −0.028458 | −0.031112 | −0.012569 | −0.039903 | 0.024044 | 0.035262 | 0.012691 | −0.00992 | 0.063399 | 0.017358 | −0.007962 |
| 74 | −0.019759 | 0.016992 | 0.02867 | −0.028082 | −0.025808 | 0.007516 | −0.006477 | 0.029926 | −0.00653 | −0.00841 | −0.028498 | 0.010221 | 0.025681 | 0.023845 |
| 75 | −0.002338 | −0.003032 | −0.004963 | −0.006214 | −0.006772 | −0.005901 | −0.014461 | 0.012873 | 0.017098 | −0.01332 | −0.008293 | −0.001163 | 0.001858 | −0.004695 |
| 76 | 0.003796 | −0.010013 | 0.003276 | 0.019703 | 0.02418 | −0.000337 | 0.010257 | 0.009679 | 0.012745 | 0.009027 | 0.003791 | −0.013017 | −0.011924 | 0.010818 |
| 77 | 0.000131 | −0.00276 | −0.003998 | −0.000513 | −0.00251 | −0.003102 | −0.006901 | 0.007507 | 0.016527 | −0.00842 | 0.001283 | 0.001403 | 0.001384 | −0.001377 |
| 78 | 0.004689 | 0.000396 | −0.003103 | −0.012159 | −0.014341 | −0.005858 | −0.014866 | 0.005324 | 0.015625 | −0.015609 | −0.009538 | 0.00456 | 0.004627 | −0.010011 |
| 79 | −0.006295 | −0.001284 | −0.003241 | −0.009813 | −0.006724 | −0.012607 | −0.023662 | 0.001299 | 0.040268 | 0.00671 | −0.016612 | −0.011472 | 0.01027 | −0.005575 |
| 80 | 0.006116 | 0.008009 | 0.035817 | 0.022515 | 0.018811 | −0.004714 | −0.026144 | 0.019569 | 0.006816 | −0.00227 | −0.012634 | −0.012491 | −0.049729 | −0.048207 |
| 81 | −0.004383 | 0.005636 | −0.031105 | 0.016761 | 0.000112 | −0.010848 | 0.041341 | 0.01717 | −0.018148 | 0.003498 | −0.030213 | 0.001591 | 0.004567 | 0.017871 |
| 82 | 0.003516 | −0.004001 | −0.000236 | 0.006598 | 0.007742 | 0.006919 | 0.015465 | −0.010661 | 0.016388 | 0.033742 | 0.000387 | −0.008769 | 0.003859 | −0.004133 |
| 83 | 0.007823 | −0.007218 | 0.000749 | 0.002873 | −0.001364 | −0.006634 | −0.004926 | −0.015824 | 0.002605 | 0.018684 | −0.015633 | −0.014751 | −0.005156 | −0.021277 |
| 84 | −0.000012 | 0.002751 | −0.003106 | −0.001644 | −0.00913 | −0.003139 | −0.008916 | −0.003237 | −0.001232 | 0.0041 | −0.010311 | −0.015429 | −0.012736 | −0.010549 |
| 85 | −0.017889 | 0.005187 | −0.009496 | 0.057413 | 0.057911 | −0.012982 | 0.044306 | −0.019021 | 0.009577 | 0.011573 | −0.024599 | −0.013047 | −0.008595 | −0.009961 |
| 86 | 0.005833 | −0.007623 | −0.000136 | 0.030635 | 0.021576 | 0.005333 | 0.019361 | −0.003518 | −0.018328 | 0.004642 | −0.009493 | 0.017868 | 0.00162 | 0.001022 |
| 87 | 0.022845 | −0.012698 | 0.006184 | 0.015707 | 0.008028 | 0.004087 | −0.000577 | −0.003334 | −0.015276 | −0.011237 | −0.014098 | −0.013526 | −0.023793 | −0.023584 |
| 88 | 0.017971 | −0.002416 | −0.001866 | −0.016858 | −0.013644 | −0.000574 | −0.017527 | −0.006708 | 0.019413 | 0.011252 | −0.005819 | −0.008544 | 0.00264 | −0.013073 |
| 89 | 0.012582 | 0.001677 | 0.006981 | −0.014605 | −0.020144 | −0.002504 | −0.020563 | −0.010565 | 0.001881 | 0.000758 | −0.012214 | −0.011851 | −0.003328 | −0.023711 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 90 | 0.008688 | 0.002939 | 0.016124 | −0.00229 | −0.013179 | −0.001269 | −0.019387 | 0.000543 | −0.007781 | 0.000297 | −0.008246 | −0.002154 | −0.012478 | −0.036224 |
| 91 | −0.014811 | −0.001105 | 0.000162 | −0.015404 | −0.023961 | 0.006721 | −0.004647 | −0.021674 | 0.000464 | 0.010884 | −0.020483 | −0.014787 | 0.004454 | −0.022596 |
| 92 | −0.004041 | 0.004953 | −0.010179 | −0.02292 | −0.027049 | 0.010019 | 0.012 | −0.023046 | −0.003974 | 0.009658 | −0.012407 | 0.016377 | 0.000015 | −0.007745 |
| 93 | 0.001956 | 0.011962 | 0.019336 | 0.019501 | 0.010871 | 0.000988 | 0.003147 | −0.019301 | −0.0114 | 0.016742 | 0.005303 | 0.001003 | 0.000127 | −0.027893 |
| 94 | 0.002333 | −0.006766 | −0.002222 | −0.021963 | −0.026862 | 0.000928 | 0.004256 | −0.036821 | 0.009311 | 0.014338 | −0.014131 | 0.020219 | 0.024239 | −0.040281 |
| 95 | −0.001777 | −0.010658 | −0.008075 | −0.010573 | −0.014982 | −0.048668 | −0.019163 | −0.01189 | −0.038701 | 0.021855 | 0.008294 | −0.025003 | −0.028868 | 0.01133 |
| 96 | 0.016273 | 0.029344 | 0.029464 | −0.022737 | −0.004466 | 0.003423 | −0.002996 | 0.014211 | 0.009429 | −0.026133 | −0.031694 | 0.002381 | 0.022243 | 0.010016 |
| 97 | 0.009261 | 0.010187 | 0.025134 | −0.006044 | −0.012441 | −0.022876 | −0.019247 | −0.005104 | −0.030951 | 0.00389 | −0.006436 | 0.009143 | −0.002458 | 0.007456 |
| 98 | −0.000753 | −0.008539 | 0.000085 | −0.002849 | −0.005096 | 0.004801 | −0.002033 | 0.001091 | −0.018021 | −0.016102 | −0.000137 | 0.004826 | 0.006708 | −0.005972 |
| 99 | −0.003849 | 0.003993 | 0.012903 | −0.012676 | −0.008991 | −0.010147 | −0.021305 | 0.00933 | 0.007039 | 0.003756 | −0.004808 | 0.018957 | 0.004816 | 0.005978 |
| 100 | 0.016609 | 0.004866 | 0.006944 | 0.028993 | 0.036811 | −0.003375 | 0.021913 | −0.003965 | 0.013598 | 0.022128 | 0.007249 | 0.018142 | 0.016975 | 0.00723 |
| 101 | 0.005968 | 0.0043 | 0.003616 | −0.002232 | −0.005159 | −0.000012 | −0.009442 | 0.005135 | −0.023699 | −0.014488 | −0.006385 | 0.013289 | 0.019126 | 0.003382 |
| 102 | −0.004343 | −0.007319 | −0.014682 | 0.028812 | 0.020771 | 0.000734 | 0.028141 | 0.004269 | −0.019851 | −0.015657 | −0.012127 | 0.01305 | −0.025223 | 0.013506 |
| 103 | 0.012222 | −0.004195 | −0.032585 | 0.001668 | −0.005988 | −0.003592 | −0.005388 | −0.023596 | −0.01736 | −0.014476 | −0.03597 | 0.015456 | 0.005584 | −0.025818 |
| 104 | −0.018207 | −0.002744 | 0.011685 | −0.005773 | −0.008241 | 0.0066191 | −0.0122491 | 0.0165691 | 0.002793 | 0.0085451 | 0.009051 | 0.0066721 | −0.0104271 | −0.00426 |
| 105 | −0.003535 | 0.025132 | −0.001162 | −0.015894 | −0.019418 | −0.007216 | −0.031372 | 0.012934 | 0.034616 | −0.006565 | −0.017825 | −0.010761 | 0.001192 | −0.029121 |
| 106 | −0.005413 | −0.026249 | −0.030924 | −0.000358 | −0.002783 | 0.02284 | 0.024577 | −0.022998 | 0.001445 | −0.018957 | 0.015373 | 0.001549 | −0.004117 | −0.002657 |
| 107 | 0.007048 | 0.01211 | 0.001193 | 0.013049 | 0.018985 | 0.009134 | 0.014224 | 0.034334 | 0.007967 | −0.005868 | 0.007888 | 0.042525 | 0.000016 | −0.011962 |
| 108 | −0.013839 | 0.015522 | 0.007129 | −0.024062 | −0.018301 | 0.000888 | −0.032375 | 0.022683 | 0.023124 | 0.003429 | −0.021884 | −0.014322 | 0.02728 | −0.008365 |
| 109 | −0.010234 | −0.008007 | −0.011057 | 0.032627 | 0.02571 | −0.01224 | 0.044235 | 0.009913 | −0.011991 | 0.026188 | −0.018518 | 0.020576 | −0.039939 | −0.039736 |
| 110 | 0.022095 | 0.01169 | −0.002569 | 0.016648 | 0.013907 | −0.025851 | −0.02404 | 0.002505 | 0.031874 | 0.007431 | −0.018556 | −0.004631 | −0.013308 | 0.011267 |
| 111 | −0.030372 | −0.002377 | −0.014446 | −0.06505 | −0.064361 | −0.006131 | −0.025889 | 0.050435 | 0.023495 | 0.016365 | −0.004676 | −0.023822 | 0.005399 | 0.070371 |
| 112 | 0.011997 | 0.000046 | 0.00574 | 0.004207 | 0.005013 | −0.029773 | −0.02449 | −0.034297 | 0.016647 | −0.005254 | 0.006523 | −0.024437 | 0.010949 | −0.04694 |
| 113 | −0.026798 | 0.001815 | 0.005387 | −0.033091 | −0.037466 | 0.009814 | −0.002283 | 0.006383 | −0.004742 | −0.00801 | 0.015041 | 0.01142 | 0.007035 | 0.003373 |
| 114 | 0.013953 | 0.028683 | 0.060748 | 0.005476 | 0.004294 | 0.022312 | 0.009331 | −0.013621 | −0.001476 | −0.00402 | −0.029319 | 0.026799 | 0.026663 | −0.051864 |
| 115 | −0.008005 | 0.029043 | −0.017464 | −0.038394 | −0.033258 | 0.007179 | −0.026708 | −0.006341 | 0.021889 | 0.001759 | −0.001804 | −0.006748 | 0.020437 | 0.02279 |
| 116 | 0.003389 | 0.001677 | 0.00481 | 0.019923 | 0.016131 | −0.032036 | −0.0003 | 0.01642 | 0.033217 | 0.020839 | −0.02499 | −0.010285 | −0.001522 | −0.008513 |
| 117 | 0.005827 | 0.037068 | 0.016301 | −0.016393 | −0.015927 | 0.001277 | −0.032249 | 0.01508 | 0.012284 | 0.013764 | −0.048965 | −0.014138 | −0.01786 | 0.008408 |
| 118 | −0.014433 | 0.033784 | 0.041127 | −0.020179 | −0.020392 | 0.027693 | −0.01264 | −0.025295 | −0.002099 | −0.02642 | 0.01768 | −0.012367 | −0.029213 | −0.029967 |
| 119 | 0.023149 | 0.01797 | 0.018982 | 0.005848 | 0.006999 | −0.005054 | −0.003844 | −0.013729 | −0.011996 | 0.000572 | 0.001988 | 0.018425 | 0.005654 | −0.007113 |
| 120 | −0.012867 | 0.03029 | 0.011144 | −0.014999 | −0.014737 | −0.002312 | −0.035175 | −0.002053 | −0.002679 | 0.009717 | −0.034622 | −0.001876 | −0.003873 | −0.002266 |
| 121 | −0.050146 | −0.019199 | 0.001853 | −0.014585 | −0.021525 | −0.000621 | 0.00013 | −0.028565 | 0.0123 | 0.014734 | 0.032161 | −0.022881 | −0.032934 | −0.013244 |
| 122 | 0.004973 | 0.004498 | −0.010534 | 0.010521 | 0.009337 | −0.022714 | −0.003897 | −0.009543 | −0.009606 | 0.0189781 | 0.01581 | −0.036781 | −0.059 | 0.01475 |
| 123 | −0.007766 | 0.009771 | −0.018771 | 0.036161 | 0.033242 | −0.022221 | 0.007168 | −0.006353 | 0.023969 | 0.04818 | 0.008079 | −0.007942 | −0.012301 | 0.001766 |
| 124 | 0.021919 | 0.022685 | 0.01244 | 0.008247 | 0.009624 | −0.018427 | −0.013286 | 0.002837 | −0.005276 | 0.003726 | 0.005523 | 0.015923 | 0.016127 | 0.006243 |
| 125 | −0.025507 | −0.014395 | −0.007289 | −0.00566 | −0.008635 | −0.006309 | −0.017287 | −0.0073 | −0.020678 | −0.019194 | 0.013538 | −0.037472 | 0.011069 | 0.004613 |
| 126 | −0.039481 | −0.027457 | −0.010268 | −0.016863 | −0.015992 | 0.018629 | 0.005175 | −0.002224 | −0.009834 | 0.006914 | 0.052842 | −0.011253 | −0.056407 | 0.024122 |
| 127 | −0.015872 | −0.058923 | −0.040118 | −0.021304 | −0.025518 | 0.016815 | −0.005194 | −0.024985 | −0.019864 | −0.022801 | 0.034505 | 0.00117 | −0.020645 | 0.005878 |
| 128 | −0.003875 | 0.005615 | 0.01807 | 0.012738 | 0.010653 | −0.001607 | 0.010647 | −0.013008 | 0.015896 | 0.008445 | −0.013028 | −0.00344 | −0.002219 | −0.021445 |
| 129 | 0.016545 | 0.009533 | −0.006528 | −0.016504 | −0.035781 | −0.02786 | −0.028556 | −0.039014 | −0.002418 | 0.011325 | 0.020559 | −0.007735 | −0.020754 | 0.013893 |
| 130 | −0.01652 | 0.001461 | −0.015107 | 0.002181 | 0.006964 | −0.009257 | −0.006097 | −0.018814 | 0.032239 | 0.017741 | 0.00912 | 0.012681 | −0.001158 | −0.019804 |
| 131 | 0.001495 | 0.022664 | 0.00395 | 0.012049 | 0.006921 | −0.009106 | 0.017291 | 0.005504 | −0.003701 | 0.025299 | 0.031342 | 0.004424 | −0.01988 | 0.01906 |
| 132 | 0.006549 | 0.014421 | 0.003769 | 0.027847 | 0.02579 | −0.000292 | 0.016045 | −0.008603 | 0.00217 | 0.037336 | −0.008755 | 0.007061 | 0.008489 | −0.028655 |
| 133 | −0.028231 | −0.018133 | −0.010181 | 0.019285 | −0.001255 | 0.002112 | 0.019067 | 0.007578 | 0.009222 | 0.012466 | −0.01895 | 0.05144 | 0.020942 | −0.053566 |
| 134 | 0.018003 | −0.000437 | 0.024522 | −0.027351 | −0.018314 | −0.00037 | −0.019655 | −0.006318 | −0.043663 | −0.057811 | −0.014113 | −0.017135 | −0.014681 | 0.028817 |
| 135 | 0.000263 | −0.008234 | 0.013682 | 0.000354 | 0.002977 | 0.004671 | −0.003303 | 0.001161 | 0.000144 | −0.006341 | −0.002891 | 0.003357 | 0.00969 | −0.00347 |
| 136 | 0.001925 | 0.007012 | −0.005724 | 0.022794 | 0.019896 | 0.021565 | 0.031176 | 0.030276 | 0.022484 | 0.007551 | −0.016589 | 0.051914 | 0.028276 | 0.032696 |
| 137 | −0.007741 | −0.017669 | −0.006521 | 0.010057 | 0.003961 | 0.009413 | 0.010334 | −0.043959 | −0.019841 | −0.039774 | 0.016939 | −0.006057 | −0.011077 | −0.038499 |
| 138 | −0.004699 | −0.010027 | 0.044236 | −0.002401 | −0.00299 | 0.016631 | 0.033935 | 0.014152 | −0.025576 | −0.009672 | 0.01703 | 0.000527 | −0.011001 | 0.005016 |
| 139 | −0.028561 | −0.019435 | −0.038056 | 0.013722 | 0.029482 | 0.026246 | 0.006047 | −0.003927 | −0.003615 | 0.001524 | 0.039792 | 0.037497 | −0.01692 | 0.014751 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 140 | −0.011111 | −0.003106 | 0.027974 | 0.034751 | 0.022639 | 0.012213 | 0.029235 | −0.013092 | 0.050241 | 0.041356 | 0.043016 | −0.011893 | −0.023884 | −0.00179 |
| 141 | 0.029124 | −0.006725 | 0.0009 | −0.000606 | 0.006135 | −0.008544 | 0.000696 | −0.025898 | 0.017291 | −0.010032 | −0.011013 | −0.018426 | 0.004832 | −0.005712 |
| 142 | −0.005436 | 0.002499 | 0.00151 | 0.0115 | 0.012563 | −0.029751 | −0.037096 | 0.00282 | 0.013685 | 0.004025 | −0.04661 | 0.011692 | 0.021516 | 0.004043 |
| 143 | −0.002382 | −0.005602 | −0.00482 | 0.032876 | 0.030503 | −0.020122 | 0.004931 | −0.001967 | −0.009738 | 0.021259 | −0.007184 | −0.004075 | 0.007195 | −0.000547 |
| 144 | 0.044119 | 0.010876 | 0.014528 | 0.01035 | 0.011663 | −0.003273 | −0.003869 | 0.02386 | 0.008102 | −0.002328 | 0.0007 | 0.011515 | 0.001412 | 0.030466 |
| 145 | 0.006636 | −0.0058 | 0.023637 | 0.016237 | −0.004409 | −0.001435 | −0.004503 | −0.01218 | −0.027417 | 0.01959 | −0.016417 | 0.04152 | 0.007654 | −0.021644 |
| 146 | −0.010748 | −0.005517 | 0.005562 | 0.016388 | 0.018645 | 0.004816 | −0.000922 | 0.004181 | 0.010949 | 0.004242 | 0.010299 | 0.000649 | −0.003254 | −0.0071 |
| 147 | −0.028942 | −0.014099 | 0.005445 | 0.017544 | 0.022883 | 0.018975 | −0.026457 | 0.020496 | 0.016302 | 0.000705 | −0.014333 | 0.018116 | −0.024781 | −0.007483 |
| 148 | 0.009903 | 0.007893 | 0.023043 | 0.001095 | 0.018269 | 0.021292 | 0.007893 | 0.009477 | 0.02048 | 0.017655 | 0.02329 | −0.005889 | −0.055663 | 0.049503 |
| 149 | −0.003306 | 0.000469 | −0.007638 | −0.01192 | −0.014639 | 0.00197 | 0.009904 | −0.022706 | 0.012032 | −0.004835 | −0.024167 | −0.008277 | 0.017494 | −0.000343 |
| 150 | −0.027311 | −0.004105 | 0.009504 | 0.010491 | 0.004876 | −0.006686 | −0.027471 | −0.002415 | −0.007384 | 0.006559 | 0.031475 | 0.021649 | 0.015615 | −0.005521 |
| 151 | 0.020202 | 0.001373 | 0.007479 | 0.028773 | 0.052702 | 0.007673 | 0.004623 | 0.028862 | 0.054197 | 0.001074 | −0.016682 | 0.019528 | 0.005751 | 0.041258 |
| 152 | −0.012494 | −0.035083 | −0.028369 | −0.010731 | −0.010014 | 0.005428 | −0.006975 | −0.018438 | 0.014809 | −0.001187 | 0.002508 | −0.001556 | 0.011625 | 0.012243 |
| 153 | −0.012577 | 0.005499 | −0.025452 | 0.038964 | 0.050261 | −0.003998 | −0.011389 | 0.013692 | 0.023751 | −0.003934 | −0.0097 | 0.001743 | −0.011799 | 0.005109 |
| 154 | −0.021665 | −0.00496 | −0.002113 | 0.01513 | 0.01192 | −0.010145 | 0.003483 | 0.029515 | 0.019661 | 0.015728 | −0.00676 | 0.007097 | 0.016566 | 0.045407 |
| 155 | −0.031914 | −0.020385 | −0.017248 | 0.018222 | 0.002189 | 0.02076 | 0.031666 | 0.01001 | −0.004499 | 0.021461 | 0.03324 | −0.007507 | −0.008719 | 0.006533 |
| 156 | −0.021829 | −0.022524 | −0.003482 | 0.002762 | 0.000373 | 0.00073 | 0.025124 | 0.016491 | 0.010034 | 0.016731 | −0.009205 | −0.000485 | 0.028659 | 0.032086 |
| 157 | −0.003156 | −0.005788 | −0.000317 | 0.006602 | 0.00433 | 0.003026 | 0.016374 | 0.003836 | 0.011313 | 0.010807 | 0.019103 | −0.009097 | 0.002302 | 0.024879 |
| 158 | −0.007956 | −0.031896 | −0.013359 | −0.017759 | −0.015226 | −0.003911 | −0.038662 | 0.008044 | 0.074845 | 0.004611 | −0.058216 | −0.028235 | −0.010002 | −0.035622 |
| 159 | −0.000223 | −0.004057 | 0.044082 | −0.007348 | −0.014137 | −0.020025 | −0.030213 | −0.038707 | −0.020375 | −0.00607 | −0.019024 | 0.008606 | 0.008345 | −0.032662 |
| 160 | −0.035432 | −0.021285 | 0.004787 | 0.023717 | 0.019213 | −0.010547 | 0.024641 | −0.042339 | 0.021744 | −0.010509 | 0.02298 | −0.052388 | −0.029087 | 0.030714 |
| 161 | 0.021924 | 0.009128 | 0.009165 | 0.025896 | 0.03643 | −0.003073 | 0.001813 | 0.001457 | 0.032785 | 0.014174 | −0.024126 | −0.004706 | −0.044061 | −0.04178 |
| 162 | 0.005786 | −0.012851 | 0.005888 | 0.029194 | 0.025416 | −0.000998 | 0.016732 | −0.034464 | −0.028989 | −0.015396 | 0.026345 | 0.002164 | 0.024617 | −0.01033 |
| 163 | −0.001359 | −0.040698 | −0.015012 | −0.010236 | −0.010605 | −0.005247 | −0.010298 | −0.031447 | −0.008305 | −0.018782 | 0.008453 | −0.020072 | 0.012294 | 0.013532 |
| 164 | 0.024142 | −0.011324 | −0.009724 | −0.000302 | −0.001271 | 0.03328 | 0.029359 | 0.004857 | 0.052311 | −0.011878 | 0.019733 | 0.029183 | 0.045273 | 0.016384 |
| 165 | −0.0474 | 0.009029 | −0.000913 | 0.003542 | −0.005576 | 0.041486 | 0.066797 | 0.056187 | 0.025608 | 0.002479 | 0.025836 | −0.016628 | −0.025564 | 0.03382 |
| 166 | 0.022401 | 0.028347 | 0.015208 | −0.01343 | −0.008566 | −0.0134 | 0.024108 | 0.02036 | 0.02503 | 0.022087 | −0.040547 | −0.009148 | 0.040866 | 0.037164 |
| 167 | 0.006096 | −0.0028 | 0.011635 | −0.034119 | −0.042647 | 0.026769 | −0.012369 | 0.007586 | −0.012797 | −0.013501 | 0.012229 | 0.012505 | 0.015726 | −0.004433 |
| 168 | 0.004345 | −0.001916 | −0.014171 | −0.013832 | −0.009572 | 0.005089 | −0.020016 | −0.023541 | 0.008301 | −0.05464 | 0.017256 | 0.007143 | −0.002486 | −0.014905 |
| 169 | 0.00662 | 0.009764 | −0.006453 | −0.003306 | −0.007559 | −0.001194 | −0.01855 | 0.003047 | −0.007764 | −0.003598 | −0.003894 | 0.004538 | 0.006734 | −0.013613 |
| 170 | 0.017577 | 0.016538 | −0.000561 | 0.011236 | 0.008232 | −0.000616 | 0.002366 | −0.002559 | −0.013712 | 0.00593 | 0.004305 | 0.014172 | 0.007073 | −0.016243 |
| 171 | −0.002519 | 0.009217 | −0.008643 | −0.014646 | −0.013313 | −0.002099 | −0.012906 | −0.004287 | 0.02975 | 0.018094 | 0.007133 | −0.000581 | −0.002732 | −0.021004 |
| 172 | −0.019778 | 0.006392 | −0.004693 | −0.004406 | −0.009049 | −0.002399 | 0.001307 | 0.000566 | −0.013026 | −0.008697 | −0.026513 | −0.011189 | −0.001301 | −0.001637 |
| 173 | −0.06503 | −0.026203 | −0.043264 | 0.001633 | −0.005062 | 0.005086 | 0.006198 | 0.00514 | −0.006734 | −0.017567 | −0.000837 | 0.003225 | 0.001319 | 0.003706 |
| 174 | −0.018461 | −0.012486 | −0.022064 | −0.019219 | −0.019517 | 0.00858 | −0.007552 | −0.002913 | 0.001854 | −0.015237 | 0.015748 | −0.01447 | −0.007864 | −0.001607 |
| 175 | 0.00918 | 0.004406 | −0.032816 | −0.000964 | 0.004444 | −0.001758 | −0.011277 | −0.025015 | 0.034527 | 0.005581 | 0.011912 | −0.037555 | −0.027235 | −0.015831 |
| 176 | 0.004334 | 0.018443 | −0.009191 | −0.006095 | 0.003561 | 0.00616 | 0.016482 | 0.024542 | 0.024173 | 0.022827 | −0.022455 | 0.004686 | 0.024221 | −0.001685 |
| 177 | 0.015294 | 0.021699 | 0.03506 | −0.043263 | −0.041199 | 0.027291 | −0.045473 | 0.060804 | 0.011314 | −0.029846 | 0.026476 | 0.030143 | −0.031434 | 0.012518 |
| 178 | 0.002934 | −0.009974 | −0.008339 | −0.00303 | −0.000942 | 0.015197 | −0.024021 | 0.007596 | 0.007868 | −0.015038 | 0.033838 | 0.029308 | −0.019188 | −0.019819 |
| 179 | 0.00436 | −0.002701 | 0.007672 | −0.00221 | −0.001485 | 0.008206 | −0.014435 | 0.014785 | 0.002309 | −0.006637 | 0.013112 | 0.010864 | −0.004725 | 0.008389 |
| 180 | −0.004445 | 0.004188 | 0.003056 | 0.00053 | 0.002346 | 0.015932 | −0.00924 | 0.013443 | −0.006622 | −0.02022 | 0.007165 | 0.01937 | 0.002454 | 0.002723 |
| 181 | −0.000731 | 0.001402 | −0.001807 | 0.005963 | 0.006258 | 0.011482 | 0.001107 | 0.014558 | −0.010136 | −0.011292 | 0.004839 | 0.012642 | −0.003453 | −0.00113 |
| 182 | 0.005484 | 0.007969 | 0.008638 | 0.015412 | 0.017587 | 0.00909 | 0.007248 | 0.012534 | 0.020968 | 0.005759 | −0.003956 | 0.026532 | 0.004418 | 0.002331 |
| 183 | 0.00007 | −0.005424 | 0.010779 | 0.002829 | 0.005376 | −0.003289 | 0.00727 | 0.006855 | 0.034729 | 0.029375 | 0.018751 | −0.000601 | −0.003054 | 0.019879 |
| 184 | −0.002573 | −0.009751 | 0.019761 | 0.005091 | 0.014238 | −0.015979 | 0.031312 | −0.032143 | 0.005265 | 0.052894 | 0.0137 | −0.031659 | 0.021073 | 0.030663 |
| 185 | −0.004044 | 0.028864 | 0.011695 | 0.000813 | 0.000356 | −0.019687 | −0.022672 | 0.010822 | −0.004508 | −0.010904 | −0.039709 | −0.027535 | −0.012637 | −0.004254 |
| 186 | −0.011842 | 0.044232 | 0.000754 | 0.012975 | 0.02425 | −0.000093 | 0.048445 | −0.020475 | −0.018939 | 0.026645 | 0.023622 | −0.026309 | −0.036404 | 0.010976 |
| 187 | −0.014683 | 0.002039 | 0.005056 | 0.015312 | 0.016317 | 0.006096 | 0.00449 | 0.00208 | −0.028121 | −0.00411 | −0.001651 | 0.011849 | 0.007907 | 0.027356 |
| 188 | 0.002075 | 0.006091 | 0.013091 | 0.015014 | 0.017909 | 0.014665 | 0.013269 | 0.002749 | −0.01496 | −0.004688 | 0.00753 | 0.006438 | 0.007048 | 0.025141 |
| 189 | 0.026507 | 0.009597 | 0.012952 | 0.027402 | 0.035351 | −0.001446 | 0.011672 | −0.012304 | −0.003173 | 0.017817 | 0.018842 | −0.01389 | 0.004964 | 0.03466 |

APPENDIX B3-continued

PCA Transformation Matrix (340 × 340 Early/Late)

| | | | | | | | | | | | | | | |
|---|---|---|---|---|---|---|---|---|---|---|---|---|---|---|
| 190 | 0.017011 | 0.007443 | 0.007853 | −0.003794 | 0.003051 | 0.009577 | 0.018801 | −0.021616 | 0.009382 | 0.011312 | −0.006983 | −0.003148 | 0.038493 | 0.014521 |
| 191 | 0.012072 | 0.008647 | 0.008686 | −0.000271 | 0.000262 | 0.005434 | 0.01651 | −0.007155 | −0.002197 | 0.006873 | −0.005552 | −0.009355 | 0.011481 | 0.030405 |
| 192 | 0.005812 | −0.05642 | −0.004501 | −0.00486 | −0.006446 | −0.012841 | −0.01133 | −0.03475 | 0.006639 | −0.002748 | 0.027945 | −0.00442 | −0.007589 | 0.01088 |
| 193 | 0.007578 | −0.019723 | −0.030523 | 0.012249 | 0.021448 | −0.007045 | 0.010791 | −0.021078 | 0.00058 | 0.001683 | −0.016976 | −0.010296 | 0.006661 | 0.023352 |
| 194 | −0.002638 | −0.005534 | −0.025392 | −0.000023 | −0.001275 | 0.006249 | −0.010322 | −0.000629 | 0.009432 | 0.00195+31 | −0.005047 | −0.000571 | 0.023623 | 0.034953 |
| 195 | −0.008067 | 0.003576 | 0.006568 | −0.009742 | −0.019037 | −0.024158 | 0.011687 | 0.004285 | −0.025667 | 0.016536 | −0.015547 | −0.028661 | 0.006512 | 0.031302 |
| 196 | 0.019283 | 0.006931 | 0.011861 | −0.009238 | −0.004416 | −0.00802 | 0.006571 | −0.020203 | −0.000658 | 0.012625 | −0.002675 | −0.0276 | 0.008692 | 0.011253 |
| 197 | 0.01897 | 0.014064 | 0.02226 | −0.003103 | 0.001204 | −0.000034 | 0.012586 | −0.024927 | 0.025993 | 0.011205 | −0.020283 | −0.018441 | 0.037701 | −0.004524 |
| 198 | −0.001856 | 0.021874 | 0.034141 | −0.022326 | −0.027515 | −0.0227 | −0.01056 | −0.000347 | −0.02131 | 0.012788 | 0.016505 | −0.040198 | −0.027751 | 0.020678 |
| 199 | 0.044204 | 0.008492 | −0.001115 | −0.037352 | −0.042023 | 0.009342 | −0.014791 | −0.016017 | −0.007529 | −0.030955 | −0.018404 | −0.010263 | 0.011194 | 0.018261 |
| 200 | 0.008658 | −0.003306 | 0.016424 | −0.014337 | −0.01341 | −0.002129 | 0.001168 | −0.000887 | −0.003456 | −0.012172 | 0.029795 | −0.02115 | −0.031922 | −0.020088 |
| 201 | −0.009652 | 0.009633 | 0.007936 | −0.02131 | −0.019611 | 0.017908 | −0.014886 | 0.049002 | −0.007591 | −0.010535 | 0.014353 | 0.042265 | −0.007783 | 0.027769 |
| 202 | −0.010969 | 0.010676 | 0.016276 | −0.047469 | −0.050486 | −0.007169 | −0.005876 | −0.004045 | −0.007866 | −0.00557 | 0.011114 | −0.018397 | −0.005811 | 0.022425 |
| 203 | 0.00674 | −0.019327 | 0.002568 | 0.011673 | −0.004267 | 0.006096 | 0.0065 | −0.036185 | −0.01947 | 0.011036 | 0.008837 | 0.004125 | 0.015281 | 0.011644 |
| 204 | −0.015777 | 0.012121 | −0.003953 | −0.053997 | −0.043038 | 0.00428 | 0.009663 | 0.00046 | −0.034906 | 0.010114 | 0.001595 | −0.027114 | −0.003684 | 0.054599 |
| 205 | −0.026989 | −0.068467 | −0.022282 | 0.01152 | 0.018765 | 0.032609 | 0.039545 | −0.020444 | −0.015054 | −0.041058 | 0.005348 | −0.032107 | 0.005918 | 0.006534 |
| 206 | 0.003721 | −0.000374 | −0.003336 | −0.022321 | −0.011071 | 0.015146 | −0.049854 | −0.015971 | 0.00366 | 0.011966 | −0.012611 | 0.018991 | 0.015148 | −0.025421 |
| 207 | 0.010159 | 0.007763 | −0.023832 | 0.009354 | 0.027524 | 0.041696 | 0.066417 | −0.0327 | −0.040763 | −0.060142 | 0.052394 | −0.027707 | −0.018472 | −0.011563 |
| 208 | −0.001906 | −0.015992 | −0.003525 | −0.013547 | −0.026053 | −0.006291 | 0.017043 | −0.036543 | −0.019085 | 0.037314 | 0.020675 | −0.019184 | 0.019819 | 0.009802 |
| 209 | −0.012461 | −0.045233 | 0.002763 | −0.007378 | −0.001839 | −0.008714 | 0.008111 | −0.008638 | 0.057058 | 0.025407 | −0.049058 | 0.001659 | 0.036406 | −0.020426 |
| 210 | −0.022368 | −0.011338 | −0.016273 | 0.003761 | 0.001468 | 0.014498 | 0.007523 | 0.056648 | 0.069314 | 0.006753 | −0.009377 | 0.011139 | −0.001716 | 0.022416 |
| 211 | −0.044262 | −0.014569 | −0.006298 | −0.029464 | −0.0262 | 0.027582 | 0.02268 | 0.025189 | 0.015934 | −0.01528 | −0.007048 | 0.010986 | 0.010197 | 0.032002 |
| 212 | −0.006273 | −0.004671 | 0.009414 | 0.006974 | 0.002575 | −0.018683 | 0.039136 | −0.007902 | 0.013097 | 0.016616 | −0.005373 | −0.050585 | 0.015649 | −0.002641 |
| 213 | 0.019633 | 0.021577 | −0.012389 | 0.019822 | 0.006765 | 0.020437 | 0.017948 | 0.002669 | −0.037121 | 0.014132 | 0.004971 | 0.048866 | −0.018632 | −0.001671 |
| 214 | −0.003272 | 0.0004 | 0.007256 | 0.006086 | 0.006813 | 0.001438 | 0.008235 | 0.001475 | −0.000716 | 0.000661 | 0.025777 | 0.009892 | 0.007079 | 0.016402 |
| 215 | 0.00253 | 0.001434 | −0.009315 | −0.028765 | −0.018355 | −0.008083 | −0.039917 | 0.011404 | 0.006947 | −0.017381 | 0.007654 | −0.034472 | −0.043779 | −0.000516 |
| 216 | 0.005856 | 0.015708 | −0.008999 | −0.050406 | −0.049509 | 0.018845 | −0.042162 | −0.00698 | 0.021865 | −0.055551 | −0.00306 | −0.002134 | −0.005877 | −0.038809 |
| 217 | −0.000006 | −0.003056 | 0.004762 | −0.012251 | −0.017706 | 0.007314 | −0.001477 | −0.009732 | −0.006317 | 0.027627 | 0.022763 | 0.011141 | 0.014175 | 0.019434 |
| 218 | −0.021023 | −0.013085 | −0.023066 | 0.020295 | 0.018715 | −0.002524 | 0.032883 | −0.001705 | −0.011144 | 0.017205 | 0.018118 | −0.00881 | −0.024966 | −0.003118 |
| 219 | −0.022427 | −0.015763 | −0.024914 | 0.008416 | −0.001324 | −0.00301 | 0.009456 | −0.007054 | 0.020325 | 0.004667 | 0.009814 | 0.012243 | 0.000341 | −0.038209 |
| 220 | −0.015662 | −0.002614 | −0.012232 | −0.00699 | −0.015355 | 0.000482 | 0.010248 | −0.006308 | −0.003452 | 0.023821 | 0.033881 | −0.01838 | 0.007994 | 0.007807 |
| 221 | 0.898064 | −0.039094 | −0.036886 | 0.010467 | 0.000357 | 0.001977 | 0.011786 | 0.007739 | 0.001565 | 0.011001 | 0.016847 | 0.006059 | 0.011918 | −0.000515 |
| 222 | −0.040075 | 0.904388 | −0.058492 | −0.003987 | −0.012906 | 0.000519 | 0.009517 | −0.037551 | −0.006097 | −0.016582 | 0.026704 | −0.013383 | −0.0005 | 0.001461 |
| 223 | −0.042513 | −0.056378 | 0.909156 | 0.004401 | −0.004617 | 0.002568 | 0.014928 | −0.019626 | 0.005424 | −0.00807 | −0.002888 | −0.00395 | 0.002551 | −0.006542 |
| 224 | 0.013776 | 0.012741 | 0.012433 | 0.845157 | −0.15536 | 0.001805 | −0.096738 | −0.01203 | 0.011931 | −0.046462 | −0.014642 | −0.039464 | −0.000509 | 0.012791 |
| 225 | 0.000292 | 0.008093 | 0.007936 | −0.152918 | 0.829681 | −0.000578 | −0.094394 | −0.013822 | 0.003305 | −0.048048 | −0.01782 | −0.03524 | −0.004577 | 0.001902 |
| 226 | 0.010268 | 0.002733 | 0.00441 | 0.008052 | 0.005914 | 0.924318 | −0.045345 | −0.021264 | −0.006616 | 0.02274 | −0.025749 | −0.024773 | −0.00638 | −0.007908 |
| 227 | 0.025073 | 0.01879 | 0.017737 | −0.081405 | −0.076199 | −0.054827 | 0.812888 | 0.001797 | 0.041207 | −0.030035 | −0.047522 | −0.002479 | −0.01343 | −0.030249 |
| 228 | 0.023606 | −0.028004 | −0.012352 | −0.013184 | −0.016974 | −0.024441 | 0.009538 | 0.861081 | −0.03853 | −0.001032 | −0.001057 | −0.068171 | −0.020726 | −0.060854 |
| 229 | 0.004781 | 0.007242 | 0.012596 | 0.009969 | −0.001139 | −0.016943 | 0.030554 | −0.04143 | 0.78244 | −0.069055 | 0.017443 | −0.011047 | −0.014742 | −0.001866 |
| 230 | 0.014782 | 0.013476 | 0.00462 | −0.039011 | −0.036997 | 0.017401 | −0.044148 | 0.007072 | −0.056424 | 0.855815 | −0.023384 | 0.00275 | −0.00228 | −0.015856 |
| 231 | 0.000782 | 0.019545 | −0.007586 | 0.003735 | 0.002578 | −0.030441 | −0.047745 | 0.003309 | 0.047481 | −0.009132 | 0.838293 | 0.015089 | 0.035506 | −0.054481 |
| 232 | 0.02336 | −0.003068 | 0.009434 | −0.041771 | −0.036858 | −0.027449 | 0.000902 | −0.062447 | −0.013012 | −0.006304 | −0.001991 | 0.859865 | −0.057115 | −0.002957 |
| 233 | 0.01499 | 0.000377 | 0.010375 | 0.008403 | 0.008373 | 0.008764 | 0.008913 | −0.003092 | −0.032835 | −0.008887 | 0.042282 | −0.05663 | 0.854633 | −0.029675 |
| 234 | 0.0238 | 0.010136 | 0.005821 | 0.029437 | 0.022342 | −0.011894 | −0.024371 | −0.058873 | 0.0269 | −0.003185 | −0.04934 | −0.008778 | −0.040515 | 0.825101 |
| 235 | 0.012359 | −0.013145 | −0.00295 | 0.00444 | 0.000578 | −0.004023 | −0.019911 | −0.053305 | 0.019554 | 0.000155 | −0.067113 | −0.016941 | −0.043055 | −0.126607 |
| 236 | 0.027343 | 0.019312 | 0.002824 | −0.020995 | −0.008196 | 0.018683 | 0.011462 | 0.013655 | 0.034246 | −0.014114 | −0.031447 | −0.034481 | 0.013054 | −0.001821 |
| 237 | 0.027874 | 0.02249 | 0.029518 | 0.006199 | 0.006125 | 0.022888 | 0.027612 | 0.014438 | 0.011222 | 0.012063 | 0.003543 | 0.0118 | 0.008818 | 0.009201 |
| 238 | 0.005529 | 0.003443 | 0.005883 | 0.005035 | −0.001797 | 0.026758 | 0.02691 | 0.005826 | 0.019723 | −0.024442 | −0.021887 | 0.021124 | 0.016651 | −0.018967 |
| 239 | 0.001985 | −0.013508 | −0.016353 | 0.003081 | −0.002231 | 0.015587 | 0.019968 | −0.004087 | 0.029072 | −0.015964 | −0.0348731 | 0.014013 | 0.002052 | −0.024182 |

APPENDIX B3-continued

PCA Transformation
Matrix (340 × 340 Early/Late)

| | | | | | | | | | | | | | |
|---|---|---|---|---|---|---|---|---|---|---|---|---|---|
| 240 | −0.004036 | −0.0008 | −0.000229 | 0.012394 | 0.017831 | 0.003204 | −0.003696 | −0.004716 | 0.00632 | 0.035329 | 0.014465 | −0.02029 | −0.031462 | 0.00554 |
| 241 | 0.020106 | 0.01388 | 0.016781 | 0.001346 | 0.005978 | 0.018561 | 0.018516 | 0.000631 | −0.010675 | 0.014964 | 0.044748 | −0.033727 | −0.090816 | −0.023562 |
| 242 | 0.005373 | −0.010772 | −0.010966 | −0.008278 | 0.000539 | 0.018953 | 0.006916 | −0.024896 | 0.008729 | −0.001088 | −0.021144 | −0.031396 | −0.045673 | −0.05405 |
| 243 | −0.006269 | −0.031333 | −0.017656 | −0.025893 | −0.021255 | 0.011361 | −0.005273 | −0.068712 | −0.007032 | 0.007823 | 0.001527 | −0.04031 | −0.044944 | −0.054043 |
| 244 | −0.050601 | 0.007022 | −0.000227 | 0.007581 | 0.00660f | 0.01417 | −0.010134 | 0.022263 | −0.000336 | −0.000261 | −0.014499 | 0.019424 | 0.011628 | 0.003463 |
| 245 | −0.000189 | 0.006124 | 0.007112 | 0.001778 | 0.001791 | 0.039677 | 0.014707 | 0.036199 | −0.014246 | −0.01457 | 0.011448 | 0.014737 | −0.004082 | 0.012632 |
| 246 | 0.017088 | −0.005821 | −0.003735 | 0.006702 | 0.005846 | 0.02492 | 0.020375 | 0.021415 | 0.020311 | −0.000375 | 0.033766 | 0.001622 | −0.024352 | −0.000885 |
| 247 | 0.001244 | −0.010303 | −0.012226 | −0.01686 | −0.020255 | 0.025199 | 0.009359 | 0.011543 | 0.029872 | −0.017018 | 0.016959 | −0.004193 | −0.00045 | −0.001508 |
| 248 | −0.006386 | −0.014613 | −0.007165 | −0.018971 | −0.023844 | 0.008312 | 0.004872 | −0.007855 | 0.024224 | −0.012809 | 0.007189 | −0.038332 | 0.003792 | −0.003982 |
| 249 | 0.018155 | −0.048088 | −0.021374 | −0.001695 | 0.00166 | 0.008095 | 0.017695 | −0.033463 | −0.00213 | 0.005216 | 0.023253 | −0.04844 | −0.035339 | 0.009778 |
| 250 | 0.002581 | 0.01166 | −0.013784 | 0.0163 | 0.020784 | 0.000871 | −0.015581 | 0.003855 | 0.023099 | 0.023748 | −0.008475 | 0.00008 | −0.013927 | −0.024884 |
| 251 | −0.017928 | 0.001693 | −0.006489 | 0.008969 | 0.005067 | 0.003148 | −0.00923 | −0.003005 | 0.018741 | 0.02728 | −0.000001 | −0.000206 | −0.018088 | −0.03753 |
| 252 | 0.009633 | 0.009995 | 0.012181 | −0.001481 | −0.004569 | −0.000247 | −0.013936 | −0.008285 | −0.009648 | 0.013082 | −0.039952 | −0.02035 | −0.023432 | −0.045482 |
| 253 | 0.022717 | 0.005237 | 0.003862 | −0.02793 | −0.029803 | −0.013541 | 0.002911 | −0.056393 | −0.048148 | −0.004031 | 0.00103 | −0.059371 | −0.023991 | −0.026089 |
| 254 | −0.017878 | −0.014326 | −0.053576 | −0.001318 | −0.001455 | 0.018612 | 0.007536 | −0.010906 | −0.000829 | 0.003655 | −0.009409 | 0.011635 | 0.006092 | −0.004813 |
| 255 | −0.039746 | 0.009656 | −0.007019 | 0.015655 | 0.015806 | 0.017861 | −0.006669 | 0.016152 | 0.008506 | 0.006929 | −0.000451 | 0.021493 | 0.011963 | −0.010306 |
| 256 | −0.017586 | 0.020272 | 0.027119 | 0.006217 | 0.007788 | 0.023188 | 0.031049 | 0.012994 | −0.050039 | −0.003104 | 0.03572 | −0.005557 | 0.014213 | 0.015149 |
| 257 | 0.007998 | 0.001977 | 0.01098 | −0.000825 | −0.002145 | −0.022516 | −0.034599 | 0.013013 | 0.015389 | −0.005045 | 0.001906 | −0.002315 | 0.00602 | 0.00154 |
| 258 | 0.014213 | −0.00616 | −0.002097 | −0.055772 | −0.054623 | −0.000738 | −0.036611 | 0.00592 | 0.040197 | 0.005408 | 0.011662 | −0.006616 | 0.014051 | 0.02361 |
| 259 | 0.000114 | −0.054228 | −0.042514 | −0.001866 | −0.005013 | 0.014522 | 0.005746 | −0.042676 | −0.001031 | −0.000132 | 0.006186 | −0.005294 | −0.012965 | −0.023138 |
| 260 | 0.008776 | −0.016179 | −0.026544 | 0.004911 | −0.010117 | 0.000819 | −0.002287 | −0.033297 | −0.020151 | 0.010076 | −0.027346 | 0.0055 | 0.009475 | −0.034498 |
| 261 | 0.008013 | −0.00346 | −0.004653 | 0.0079 | −0.001135 | −0.005443 | −0.004398 | −0.030134 | 0.003944 | 0.028808 | −0.036902 | 0.007983 | 0.02514 | −0.040363 |
| 262 | 0.018791 | 0.001131 | 0.007548 | −0.015786 | −0.011944 | 0.000224 | −0.000202 | −0.012756 | 0.008416 | −0.007278 | −0.03406 | −0.024277 | 0.014218 | −0.011658 |
| 263 | 0.019248 | −0.002627 | 0.007712 | −0.010285 | −0.007116 | 0.003591 | −0.001981 | −0.021804 | 0.010568 | −0.009454 | −0.027474 | −0.024285 | 0.005147 | −0.024377 |
| 264 | 0.003023 | −0.052739 | −0.030756 | −0.013602 | −0.009512 | 0.014419 | 0.004399 | −0.037591 | −0.000732 | −0.001501 | 0.019025 | 0.002719 | 0.013318 | 0.011056 |
| 265 | 0.017271 | −0.022529 | −0.038844 | −0.029324 | −0.032219 | 0.005099 | 0.007141 | −0.034259 | 0.005595 | 0.018721 | −0.010173 | 0.006975 | 0.033768 | 0.022101 |
| 266 | −0.006343 | 0.010779 | −0.014081 | −0.017081 | −0.025843 | 0.003798 | 0.011402 | −0.01391 | 0.002747 | 0.022791 | −0.020565 | 0.013848 | 0.045492 | 0.00201 |
| 267 | 0.020568 | 0.027762 | 0.013892 | −0.010967 | −0.011184 | −0.054275 | −0.020047 | −0.047539 | −0.098338 | 0.008846 | −0.011473 | −0.032162 | −0.00372 | 0.002088 |
| 268 | 0.011428 | 0.006728 | 0.011026 | 0.000307 | 0.000687 | −0.063085 | −0.042235 | −0.019706 | −0.003139 | 0.021739 | −0.027075 | −0.022774 | −0.011957 | −0.010368 |
| 269 | 0.000206 | 0.012364 | 0.01335 | −0.001805 | −0.002684 | −0.05871 | −0.042196 | −0.009606 | −0.010339 | 0.015452 | −0.022663 | −0.022825 | −0.007585 | −0.004938 |
| 270 | 0.016749 | 0.014277 | 0.015036 | −0.00429 | 0.000477 | −0.061833 | −0.082392 | −0.011494 | 0.019799 | 0.013769 | −0.02269 | −0.010474 | 0.00367 | −0.006011 |
| 271 | 0.010058 | 0.014685 | 0.012868 | 0.006357 | 0.007437 | −0.017727 | 0.037564 | −0.020893 | −0.092707 | 0.003691 | 0.023982 | 0.004562 | 0.005608 | 0.017812 |
| 272 | 0.004226 | 0.002883 | 0.00719 | 0.032549 | 0.023659 | −0.028379 | 0.04832 | −0.041053 | −0.168363 | −0.024813 | −0.000385 | −0.002421 | 0.010237 | 0.006985 |
| 273 | 0.004987 | 0.000732 | 0.007187 | 0.010186 | 0.011987 | −0.020326 | 0.000388 | 0.001009 | −0.066404 | −0.045505 | −0.007981 | −0.003784 | 0.001998 | 0.027265 |
| 274 | 0.005199 | 0.004993 | 0.009948 | 0.00946 | 0.011417 | −0.018663 | −0.002026 | 0.002837 | −0.068277 | −0.046503 | −0.00533 | 0.001796 | 0.002432 | 0.026221 |
| 275 | 0.020661 | 0.014022 | 0.012809 | −0.02615 | −0.009746 | 0.004707 | −0.0827 | 0.010576 | −0.017114 | −0.10182 | −0.001358 | 0.013211 | 0.019277 | 0.015775 |
| 276 | 0.03144 | 0.0171 | 0.006269 | −0.012177 | −0.000505 | 0.01308 | 0.026794 | −0.007699 | −0.024374 | −0.013534 | −0.025994 | −0.032252 | 0.012702 | −0.011382 |
| 277 | 0.019928 | 0.000802 | 0.0056 | 0.001645 | 0.00605 | 0.015994 | 0.026848 | −0.000636 | 0.013932 | 0.016599 | −0.010017 | 0.003512 | −0.004271 | 0.012319 |
| 278 | 0.017736 | 0.003455 | 0.000573 | −0.003152 | 0.002129 | 0.016923 | 0.027072 | −0.004404 | 0.008904 | 0.005678 | −0.013606 | −0.002265 | −0.004128 | 0.014031 |
| 279 | 0.003532 | −0.01069 | −0.011878 | 0.010549 | 0.011866 | 0.01143 | 0.027272 | −0.023959 | 0.023797 | −0.002993 | −0.016166 | 0.006485 | 0.014927 | −0.024456 |
| 280 | 0.019767 | −0.017139 | 0.001086 | −0.04502 | −0.033923 | 0.003616 | −0.00927 | −0.07792 | −0.033786 | −0.003103 | 0.022613 | −0.058296 | −0.060181 | −0.036018 |
| 281 | 0.018316 | −0.012125 | −0.014143 | −0.002128 | −0.001063 | 0.012222 | 0.032289 | 0.003019 | 0.004737 | 0.009837 | 0.039282 | −0.00085 | −0.019564 | 0.02692 |
| 282 | 0.009284 | −0.014321 | −0.016006 | −0.023593 | −0.016655 | 0.017556 | 0.013079 | 0.010057 | 0.017153 | −0.003609 | 0.042011 | −0.001837 | −0.026824 | 0.022775 |
| 283 | −0.008227 | −0.009073 | −0.018265 | 0.000948 | 0.005019 | 0.011897 | 0.023242 | −0.013063 | 0.024387 | 0.000815 | 0.023892 | −0.006371 | 0.011341 | −0.008616 |
| 284 | 0.005561 | 0.004489 | 0.011851 | 0.004914 | 0.008597 | −0.021693 | −0.015043 | −0.002329 | 0.001039 | 0.002735 | 0.008221 | −0.002161 | 0.011815 | 0.005542 |
| 285 | 0.004523 | 0.004185 | 0.009516 | 0.002504 | 0.00752 | −0.020634 | −0.022743 | 0.002386 | 0.011766 | −0.002643 | 0.009952 | −0.000569 | 0.003955 | −0.001754 |
| 286 | 0.007491 | 0.002367 | 0.005245 | −0.038083 | −0.034713 | −0.004676 | −0.037343 | 0.010129 | 0.012624 | 0.008908 | 0.032462 | 0.019152 | −0.003062 | 0.024438 |
| 287 | 0.003586 | 0.000743 | 0.005106 | −0.030436 | −0.024151 | −0.005628 | −0.038546 | 0.005061 | 0.015174 | 0.006757 | 0.03573 | 0.01376 | −0.00515 | 0.021947 |
| 288 | 0.016556 | 0.002213 | 0.009603 | −0.049242 | −0.039085 | −0.000377 | −0.023051 | −0.014331 | 0.038313 | 0.013441 | 0.027233 | −0.010444 | 0.036882 | 0.020927 |
| 289 | 0.023656 | 0.012696 | 0.014698 | −0.027271 | −0.021069 | −0.005263 | −0.012695 | −0.005143 | 0.014302 | 0.000685 | −0.008835 | −0.01926 | 0.022054 | 0.00766 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 290 | 0.010362 | 0.016627 | 0.025806 | −0.004669 | 0.002649 | 0.010626 | 0.00467 | 0.008697 | 0.020534 | 0.013037 | 0.011967 | 0.009244 | 0.030188 | 0.015454 |
| 291 | 0.00989 | 0.016112 | 0.025066 | −0.005774 | 0.002265 | 0.010412 | 0.002517 | 0.00844 | 0.022297 | 0.015396 | 0.012548 | 0.010295 | 0.03094 | 0.015635 |
| 292 | 0.006192 | 0.011032 | 0.020924 | 0.002111 | 0.010997 | 0.010875 | 0.004599 | 0.003527 | 0.016697 | 0.010206 | 0.01264 | 0.009533 | 0.025216 | 0.00693 |
| 293 | −0.02526 | −0.003745 | −0.019399 | 0.005672 | 0.014172 | −0.001055 | −0.009304 | 0.010944 | 0.029424 | 0.00139 | −0.025495 | 0.006776 | 0.005465 | −0.011981 |
| 294 | −0.008208 | −0.0162 | −0.006443 | 0.012308 | 0.017484 | −0.014547 | −0.01038 | −0.011383 | 0.002656 | −0.003919 | −0.015134 | 0.005762 | 0.008106 | −0.001101 |
| 295 | −0.011418 | −0.003092 | −0.001597 | 0.028293 | 0.031967 | 0.008547 | 0.027906 | 0.005979 | −0.032262 | −0.030682 | −0.010737 | 0.01843 | 0.012386 | 0.012244 |
| 296 | −0.009095 | −0.020794 | −0.011428 | 0.028649 | 0.020497 | −0.00661 | −0.000232 | −0.026682 | −0.047191 | −0.036921 | 0.008143 | 0.001267 | 0.006524 | 0.017158 |
| 297 | −0.016037 | −0.003692 | −0.008421 | 0.02321 | 0.021162 | 0.012416 | 0.040339 | 0.005563 | −0.040977 | −0.027375 | −0.018866 | 0.022545 | 0.020075 | 0.011916 |
| 298 | −0.000936 | 0.005707 | −0.016011 | 0.031651 | 0.027665 | 0.011767 | 0.041169 | −0.005659 | 0.009425 | 0.007577 | 0.022984 | −0.004035 | 0.016869 | −0.009491 |
| 299 | −0.011503 | −0.00922 | −0.017605 | 0.005292 | −0.002325 | −0.00438 | 0.031236 | −0.004729 | −0.000475 | 0.0088 | −0.02621 | 0.004167 | 0.023393 | 0.014704 |
| 300 | 0.035037 | 0.030511 | 0.01321 | 0.02049 | 0.033562 | 0.013235 | 0.022166 | −0.03078 | −0.014898 | −0.014878 | 0.014263 | 0.003981 | 0.005313 | −0.020574 |
| 301 | −0.010921 | −0.014022 | −0.006384 | 0.016462 | 0.013179 | −0.003863 | 0.020187 | −0.008937 | 0.011984 | −0.005891 | −0.015247 | −0.002894 | 0.020936 | −0.014889 |
| 302 | 0.005606 | −0.023371 | −0.005112 | 0.004157 | 0.003756 | −0.007141 | −0.007479 | −0.011636 | 0.015793 | −0.00477 | 0.011217 | 0.008376 | 0.012724 | 0.007509 |
| 303 | −0.01117 | −0.024583 | −0.020349 | −0.011245 | −0.022598 | −0.005829 | 0.011627 | −0.025397 | −0.01455 | 0.020782 | 0.001149 | −0.004943 | 0.007839 | 0.013072 |
| 304 | 0.006465 | −0.020755 | −0.013161 | −0.013658 | −0.024037 | −0.013613 | −0.002941 | −0.035302 | 0.008356 | 0.021785 | 0.006369 | −0.006995 | 0.015331 | 0.003686 |
| 305 | −0.011024 | 0.018565 | 0.004457 | 0.00514 | 0.006383 | −0.014224 | −0.003278 | −0.018624 | 0.005275 | −0.00327 | −0.003893 | 0.011297 | 0.001822 | −0.019709 |
| 306 | −0.014202 | −0.015412 | −0.020183 | −0.021325 | −0.018544 | 0.013954 | −0.023394 | 0.013945 | 0.019491 | −0.001225 | −0.011267 | 0.012626 | 0.026051 | 0.023827 |
| 307 | 0.016037 | 0.013405 | 0.000099 | −0.014835 | −0.005388 | 0.01733 | −0.005494 | −0.020877 | −0.025203 | −0.025019 | −0.024544 | −0.007447 | −0.016918 | 0.011637 |
| 308 | −0.002076 | −0.00223 | 0.003872 | 0.022495 | −0.00532 | 0.012308 | 0.016115 | −0.005224 | −0.034586 | −0.022934 | 0.032084 | −0.013992 | −0.050685 | −0.026503 |
| 309 | −0.00186 | 0.003392 | −0.005405 | 0.014598 | 0.015553 | −0.007722 | −0.013772 | −0.005094 | 0.024798 | −0.001775 | −0.021578 | 0.015678 | 0.00861 | −0.003107 |
| 310 | 0.011694 | 0.0176 | 0.00022 | −0.000082 | 0.003192 | 0.00603f | −0.029431 | 0.020835 | 0.025592 | −0.008299 | −0.016456 | 0.03039 | 0.000016 | 0.023711 |
| 311 | −0.000332 | 0.002123 | 0.004328 | 0.005529 | 0.004546 | −0.009435 | −0.015311 | −0.003653 | −0.015129 | −0.014217 | −0.001814 | 0.005921 | −0.009929 | −0.010518 |
| 312 | −0.005823 | −0.008499 | −0.012846 | 0.003526 | −0.004141 | −0.023873 | −0.006508 | −0.004411 | −0.04432 | −0.023307 | −0.024331 | −0.029202 | −0.019186 | 0.000078 |
| 313 | −0.004899 | −0.002211 | 0.004605 | 0.002785 | −0.008225 | −0.003992 | −0.015414 | 0.00863 | −0.019834 | −0.006066 | 0.010227 | 0.023315 | 0.006618 | −0.02001 |
| 314 | 0.013749 | 0.031032 | −0.007107 | 0.01322 | 0.023239 | 0.033782 | 0.042807 | −0.005853 | −0.012149 | 0.006513 | −0.010183 | 0.021816 | 0.016783 | −0.003783 |
| 315 | −0.005638 | 0.007918 | −0.006756 | −0.000621 | −0.003895 | −0.005103 | −0.008779 | 0.000279 | 0.0038 | 0.008081 | −0.010786 | 0.017508 | 0.002606 | 0.002096 |
| 316 | −0.018033 | 0.017419 | 0.032772 | −0.036987 | −0.040951 | 0.023263 | −0.024948 | −0.024687 | 0.015878 | 0.002466 | 0.041439 | −0.026185 | 0.002122 | −0.016471 |
| 317 | 0.000305 | 0.00099 | −0.014644 | 0.028966 | 0.031009 | −0.006515 | −0.000633 | −0.004885 | 0.009297 | −0.004879 | −0.025826 | 0.01388 | 0.013434 | −0.011566 |
| 318 | −0.005945 | −0.009711 | −0.01564 | 0.014029 | 0.009213 | −0.005976 | −0.005347 | 0.003049 | 0.005696 | −0.004095 | −0.008475 | 0.013903 | −0.004501 | −0.010078 |
| 319 | −0.014316 | 0.002964 | −0.015399 | −0.006269 | −0.011337 | −0.005225 | −0.007009 | 0.003257 | 0.006711 | 0.001633 | −0.016978 | 0.009424 | −0.000646 | −0.000205 |
| 320 | −0.003006 | −0.017739 | −0.012141 | −0.009128 | −0.018117 | −0.008052 | −0.020848 | 0.004232 | 0.022731 | 0.001878 | 0.016274 | −0.001194 | −0.031149 | −0.011908 |
| 321 | 0.015651 | −0.004592 | 0.018957 | 0.001937 | 0.006018 | 0.005314 | 0.011079 | −0.017179 | −0.006382 | 0.008736 | 0.003403 | 0.004196 | 0.009323 | 0.005369 |
| 322 | 0.057048 | 0.033286 | 0.018814 | −0.005712 | −0.001494 | 0.015819 | −0.01627 | −0.029878 | 0.045904 | −0.011487 | −0.049327 | −0.019133 | −0.014159 | −0.022886 |
| 323 | 0.025944 | 0.025581 | 0.018716 | −0.024209 | −0.022433 | −0.007658 | −0.01737 | 0.004777 | 0.022263 | 0.004613 | −0.02815 | −0.018833 | 0.000908 | −0.019905 |
| 324 | 0.00127 | −0.015778 | −0.017214 | −0.006013 | −0.003425 | −0.007167 | −0.007227 | −0.031897 | 0.044273 | 0.025927 | 0.048731 | −0.001 | 0.024671 | 0.027322 |
| 325 | −0.008247 | −0.015411 | −0.005813 | 0.023854 | 0.023933 | −0.011919 | −0.00119 | −0.023688 | −0.01965 | −0.003682 | −0.001484 | 0.005605 | 0.013735 | 0.00374 |
| 326 | 0.000177 | −0.024667 | 0.005407 | 0.008404 | 0.01336 | −0.010459 | −0.00195 | −0.000285 | −0.020002 | −0.006012 | 0.026065 | −0.007816 | 0.002268 | 0.059851 |
| 327 | 0.003635 | −0.012032 | −0.000605 | 0.004006 | 0.002693 | −0.007575 | −0.000913 | −0.023018 | −0.014893 | −0.007282 | 0.009614 | −0.003683 | −0.006598 | −0.002931 |
| 328 | −0.003045 | 0.005773 | 0.012904 | 0.010434 | 0.006858 | 0.002867 | 0.032785 | −0.031996 | 0.027433 | 0.00342 | 0.028169 | −0.033095 | 0.008091 | 0.011975 |
| 329 | −0.011445 | −0.020792 | 0.004404 | 0.006267 | −0.001365 | −0.006562 | 0.012158 | −0.002402 | −0.013453 | −0.000039 | 0.003862 | −0.009083 | −0.007154 | 0.008576 |
| 330 | 0.039326 | 0.012391 | 0.021247 | −0.005855 | 0.003557 | 0.004237 | −0.019537 | 0.023579 | 0.006016 | −0.006068 | 0.003032 | 0.000942 | −0.013581 | 0.015867 |
| 331 | −0.003572 | −0.011352 | 0.002702 | −0.004924 | −0.000666 | −0.009085 | −0.007839 | −0.018849 | 0.002624 | 0.014927 | 0.007254 | −0.007276 | −0.001206 | 0.005969 |
| 332 | 0.006789 | 0.011125 | 0.02945 | −0.015505 | −0.016666 | 0.005276 | −0.004274 | 0.020364 | 0.020063 | −0.019227 | 0.028869 | 0.005262 | −0.010706 | 0.018014 |
| 333 | −0.000646 | −0.008596 | 0.006342 | 0.00453 | 0.008349 | −0.009378 | −0.016222 | −0.01264 | 0.003147 | −0.007119 | −0.004688 | −0.007808 | 0.006767 | −0.00381 |
| 334 | −0.042273 | −0.0325 | −0.008108 | 0.025713 | 0.019255 | 0.005861 | 0.010671 | 0.030497 | −0.052361 | −0.027519 | 0.006344 | 0.030147 | −0.006324 | −0.001307 |
| 335 | 0.000877 | −0.00212 | 0.004416 | −0.002796 | −0.000117 | −0.013643 | −0.009226 | −0.006876 | −0.005689 | −0.00249 | 0.002005 | −0.016334 | −0.011811 | −0.001638 |
| 336 | 0.026565 | 0.020826 | 0.015802 | −0.008439 | 0.000113 | 0.007749 | −0.00107 | −0.027674 | 0.010878 | −0.020855 | 0.00525 | −0.009024 | 0.0072 | 0.001608 |
| 337 | −0.008283 | 0.001226 | 0.003546 | 0.006084 | −0.004289 | −0.004212 | 0.016677 | −0.008939 | −0.02382 | 0.00924 | 0.000717 | 0.004752 | 0.030025 | 0.008215 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 338 | −0.023333 | 0.005251 | −0.008543 | 0.000488 | −0.009637 | 0.001554 | −0.001726 | 0.026046 | −0.002191 | −0.028294 | 0.007674 | −0.020217 | −0.035808 | 0.008952 |
| 339 | 0.012567 | −0.003902 | 0.009152 | −0.013381 | −0.011538 | −0.008108 | 0.007497 | −0.025712 | 0.003414 | 0.017099 | −0.011779 | −0.008125 | 0.01644 | −0.011106 |
| 340 | −0.044445 | −0.012874 | −0.011554 | 0.013865 | −0.007508 | 0.00833 | 0.010498 | 0.025746 | −0.007105 | −0.013154 | 0.010674 | 0.025355 | −0.019636 | 0.035234 |

| | IB | IC | ID | IE | IF | IG | IH | II | IJ | IK | IL | IM | IN | IO |
|---|---|---|---|---|---|---|---|---|---|---|---|---|---|---|
| 1 | −0.08892 | −0.049684 | −0.038804 | −0.035143 | −0.035883 | −0.03506 | −0.064742 | −0.04032 | −0.016016 | 0.042984 | −0.01003 | 0.001857 | 0.029294 | 0.016587 |
| 2 | −0.004053 | 0.076832 | 0.059094 | 0.022383 | −0.004043 | 0.035509 | 0.085848 | 0.053253 | 0.013254 | 0.032563 | 0.022073 | 0.016415 | 0.020317 | 0.030891 |
| 3 | −0.056244 | 0.026785 | 0.059301 | 0.019637 | 0.020606 | −0.001982 | 0.025831 | 0.00381 | −0.027484 | 0.023976 | 0.101492 | 0.07529 | 0.030871 | 0.01682 |
| 4 | −0.010483 | −0.008633 | −0.017486 | −0.051843 | −0.058346 | −0.003634 | 0.020641 | 0.030662 | 0.067813 | 0.019494 | 0.083263 | −0.01073 | −0.031238 | −0.007962 |
| 5 | 0.057908 | 0.029255 | −0.017421 | 0.089464 | 0.086302 | 0.023306 | 0.021546 | 0.016603 | 0.103456 | 0.049446 | 0.058698 | −0.028032 | 0.086 | 0.129787 |
| 6 | 0.113982 | 0.085534 | 0.002827 | −0.028858 | −0.015383 | −0.041787 | 0.008264 | 0.084857 | 0.045033 | −0.030429 | 0.00665 | 0.011928 | 0.055381 | 0.054953 |
| 7 | −0.015757 | −0.000387 | 0.040477 | −0.011748 | −0.011994 | 0.064648 | 0.089623 | 0.035912 | 0.043682 | −0.012992 | −0.034054 | −0.008053 | −0.045694 | −0.038153 |
| 8 | 0.066853 | −0.022267 | −0.041563 | 0.01461 | 0.022639 | 0.002685 | 0.00208 | 0.00989 | −0.029538 | 0.028839 | 0.037454 | 0.007807 | 0.0055 | −0.047065 |
| 9 | 0.029505 | −0.001569 | −0.084107 | −0.038329 | 0.023679 | 0.018642 | 0.044417 | 0.058089 | 0.023163 | 0.007321 | 0.064828 | 0.027827 | 0.064448 | 0.053539 |
| 10 | 0.041141 | −0.014257 | 0.023556 | 0.06234 | 0.056268 | −0.041622 | 0.024578 | 0.031415 | 0.04645 | −0.041454 | −0.010401 | 0.002364 | −0.011232 | −0.02322 |
| 11 | 0.029085 | 0.012945 | −0.017134 | −0.017194 | −0.01788 | 0.005148 | 0.02238 | −0.061055 | −0.056273 | −0.016089 | −0.04883 | −0.028887 | −0.017078 | 0.039308 |
| 12 | 0.047674 | −0.024093 | 0.010837 | 0.035609 | 0.041715 | 0.006841 | −0.013501 | −0.002595 | −0.001553 | −0.000204 | −0.027134 | −0.088558 | −0.057613 | −0.041327 |
| 13 | 0.004544 | −0.035208 | −0.064931 | −0.030349 | 0.018286 | −0.016386 | 0.013493 | −0.010174 | 0.016105 | −0.000087 | 0.001565 | −0.062325 | −0.063042 | −0.04779 |
| 14 | −0.013583 | −0.031042 | 0.010798 | −0.009023 | −0.015993 | 0.061143 | 0.038626 | −0.004382 | −0.082191 | 0.03894 | 0.044864 | 0.064806 | −0.014523 | −0.017433 |
| 15 | 0.023981 | 0.050068 | 0.001378 | 0.026399 | 0.042028 | 0.016071 | 0.02501 | 0.008734 | −0.05406 | 0.047199 | 0.043877 | −0.036444 | −0.061861 | −0.054652 |
| 16 | −0.098015 | 0.020755 | −0.003844 | −0.040011 | −0.066904 | 0.044559 | 0.001362 | −0.0689 | −0.112842 | 0.002332 | −0.000283 | −0.014515 | −0.00055 | 0.001059 |
| 17 | −0.080362 | −0.003383 | 0.017213 | 0.046125 | 0.03639 | −0.002498 | −0.099022 | −0.041424 | 0.00259 | 0.060893 | −0.017508 | −0.008503 | 0.011697 | 0.024515 |
| 18 | 0.005702 | 0.000708 | 0.036646 | −0.056624 | −0.002894 | −0.067919 | −0.034354 | 0.054478 | 0.065823 | −0.016928 | −0.023906 | 0.025737 | −0.005532 | −0.012823 |
| 19 | 0.109938 | −0.089041 | −0.069272 | −0.024165 | 0.002692 | 0.049272 | 0.008568 | 0.039017 | 0.12159 | 0.044511 | −0.053114 | −0.035251 | 0.007889 | 0.034917 |
| 20 | 0.059107 | 0.050384 | −0.025421 | −0.008966 | 0.025474 | 0.054264 | 0.008314 | 0.075283 | 0.015359 | 0.040538 | −0.01704 | −0.00591 | 0.011237 | 0.023224 |
| 21 | 0.046342 | −0.044232 | −0.007139 | 0.012444 | 0.013093 | 0.015724 | −0.051205 | −0.044301 | −0.036958 | −0.044763 | 0.022292 | 0.047663 | 0.013074 | 0.032712 |
| 22 | 0.005921 | −0.015329 | −0.074873 | −0.073428 | −0.027088 | 0.047482 | 0.053259 | −0.034819 | −0.043545 | −0.022243 | −0.004021 | −0.009308 | −0.007851 | −0.031702 |
| 23 | 0.03159 | −0.011977 | 0.096274 | 0.141426 | 0.133852 | −0.072345 | −0.035353 | −0.004243 | −0.017317 | −0.069119 | −0.045666 | 0.033345 | 0.015032 | −0.000368 |
| 24 | −0.060362 | −0.01784 | 0.015623 | 0.030889 | 0.021214 | −0.054946 | −0.093937 | −0.048854 | −0.004518 | 0.036419 | −0.027048 | −0.050906 | −0.011911 | −0.038725 |
| 25 | 0.023685 | 0.019049 | 0.024178 | 0.065309 | 0.071421 | 0.007364 | −0.051816 | −0.03815 | −0.016712 | −0.01344 | −0.014147 | −0.081107 | −0.006118 | −0.006251 |
| 26 | 0.000556 | 0.021291 | 0.001152 | 0.017684 | 0.01208 | −0.049115 | −0.013737 | −0.013012 | −0.01351 | −0.041157 | 0.066943 | −0.015595 | 0.000182 | 0.028949 |
| 27 | 0.020272 | −0.081563 | 0.016521 | 0.030968 | 0.016889 | 0.002154 | −0.024892 | −0.0274861 | 0.066253 | 0.017677 | −0.071129 | 0.016654 | −0.028206 | −0.019269 |
| 28 | −0.033996 | −0.055011 | 0.037332 | 0.058729 | 0.026712 | 0.051993 | 0.062375 | −0.020933 | −0.000531 | 0.027047 | −0.014299 | −0.016118 | 0.007209 | −0.002411 |
| 29 | 0.02286 | −0.023782 | −0.011225 | 0.003855 | 0.007907 | −0.022319 | −0.02143 | −0.001374 | 0.007051 | −0.016644 | −0.013012 | 0.000247 | 0.00366 | 0.004617 |
| 30 | −0.055148 | 0.011339 | 0.040333 | 0.010742 | −0.010551 | −0.122049 | −0.100708 | −0.044742 | −0.105796 | −0.014251 | −0.070488 | −0.007878 | −0.003079 | 0.02064 |
| 31 | −0.001614 | −0.02098 | 0.000122 | −0.014227 | −0.010679 | −0.035049 | −0.030252 | −0.037206 | −0.028619 | 0.001766 | −0.017275 | −0.033217 | −0.043448 | −0.034052 |
| 32 | 0.036337 | 0.036614 | −0.008292 | 0.017429 | −0.014042 | −0.039725 | −0.037099 | 0.06266 | 0.088309 | 0.009894 | −0.072939 | −0.038885 | −0.001497 | 0.034299 |
| 33 | 0.093907 | 0.133439 | −0.011166 | −0.003644 | 0.003757 | −0.003175 | 0.00419 | 0.117173 | 0.027031 | −0.049049 | −0.002241 | 0.042997 | 0.078923 | 0.059935 |
| 34 | 0.090284 | −0.061607 | 0.038555 | 0.02261 | 0.006496 | 0.069333 | 0.043152 | −0.013302 | −0.002357 | −0.005331 | −0.022523 | −0.005582 | −0.014685 | −0.038659 |
| 35 | −0.007844 | 0.020368 | −0.014472 | −0.001187 | 0.034444 | −0.090228 | −0.03573 | 0.072958 | 0.083839 | 0.061129 | 0.00354 | −0.030039 | −0.009906 | −0.028401 |
| 36 | −0.050942 | −0.005335 | 0.037003 | −0.0165 | −0.026822 | 0.057564 | 0.015123 | −0.045805 | 0.008493 | −0.026221 | −0.015152 | 0.009213 | −0.01016 | −0.016718 |
| 37 | 0.077947 | −0.073838 | 0.034992 | 0.01826 | 0.024762 | −0.000738 | 0.022678 | −0.017905 | −0.022879 | 0.049948 | 0.064114 | −0.018586 | −0.054836 | −0.043021 |
| 38 | 0.08024 | 0.000149 | 0.000578 | −0.03493 | −0.050606 | 0.008547 | 0.04165 | 0.045126 | 0.044392 | 0.018703 | 0.027408 | −0.023127 | −0.038537 | −0.00594 |
| 39 | 0.05915 | 0.015648 | 0.070007 | 0.001524 | −0.060853 | −0.071382 | 0.002052 | 0.064884 | 0.028011 | −0.0681 | −0.034793 | 0.064714 | 0.020391 | 0.010122 |
| 40 | 0.023433 | −0.014208 | −0.008328 | −0.01301 | −0.000465 | −0.012568 | −0.005608 | 0.0131 | 0.030836 | −0.015767 | −0.002224 | 0.009207 | 0.016936 | 0.023281 |
| 41 | 0.08939 | 0.078405 | −0.048242 | −0.011153 | 0.049883 | −0.008804 | −0.071271 | 0.044597 | 0.016727 | −0.015535 | −0.008774 | 0.039122 | 0.05904 | 0.001593 |
| 42 | −0.017713 | −0.0176 | −0.018732 | −0.005545 | −0.0141491 | 0.01575 | 0.037695 | −0.007995 | −0.019165 | 0.034264 | 0.0317611 | −0.052771 | −0.048685 | −0.003486 |
| 43 | −0.081497 | −0.033194 | 0.051472 | 0.014185 | −0.043722 | 0.058427 | 0.061834 | −0.029884 | −0.087757 | 0.018306 | 0.0039541 | 0.0220681 | −0.040896 | −0.082878 |
| 44 | 0.003768 | 0.041412 | 0.051016 | −0.00076 | −0.040775 | 0.033594 | 0.03078 | 0.038154 | −0.000517 | −0.037187 | 0.019328 | 0.02533 | −0.025649 | −0.00461 |

APPENDIX B3-continued

PCA Transformation Matrix (340 × 340 Early/Late)

| | | | | | | | | | | | | | |
|---|---|---|---|---|---|---|---|---|---|---|---|---|---|
| 45 | 0.067776 | −0.038924 | −0.050218 | −0.047336 | −0.043313 | −0.066329 | −0.067192 | 0.007441 | 0.012974 | 0.075987 | 0.038503 | 0.030055 | 0.013107 | −0.004313 |
| 46 | −0.009878 | −0.002459 | 0.050031 | 0.054998 | 0.003517 | −0.038511 | 0.002905 | −0.061234 | 0.002619 | −0.008517 | 0.023886 | −0.017639 | 0.01182 | 0.011201 |
| 47 | 0.02196 | −0.08164 | −0.065837 | −0.040263 | 0.000966 | 0.031414 | 0.019368 | 0.034437 | 0.068626 | 0.028195 | −0.026158 | −0.038625 | −0.026113 | −0.059841 |
| 48 | 0.01583 | −0.03 | 0.009822 | −0.017491 | −0.017445 | 0.054458 | −0.062512 | 0.007298 | −0.010512 | −0.012464 | −0.131435 | −0.016612 | −0.025512 | −0.005866 |
| 49 | −0.027678 | 0.001108 | −0.031504 | −0.03124 | 0.025533 | −0.008379 | 0.054174 | −0.00596 | −0.033652 | −0.018734 | 0.000464 | 0.038033 | 0.016751 | 0.00339 |
| 50 | 0.080195 | −0.041036 | −0.068033 | 0.049779 | 0.09426 | 0.042829 | 0.057919 | 0.032675 | 0.039399 | −0.038128 | −0.004276 | 0.048038 | 0.025253 | 0.006008 |
| 51 | 0.086405 | 0.024585 | 0.057525 | −0.052401 | −0.079052 | −0.026381 | 0.007624 | 0.092999 | 0.110436 | −0.03904 | −0.07102 | 0.032077 | 0.001711 | −0.000066 |
| 52 | 0.009565 | 0.001791 | −0.058756 | 0.062592 | 0.03801 | 0.005726 | −0.042406 | −0.021601 | −0.008245 | −0.0042631 | −0.0397851 | −0.0515911 | −0.00836 | 0.016965 |
| 53 | −0.015759 | 0.01607 | 0.033397 | −0.069136 | −0.087466 | −0.022219 | −0.01262 | 0.029099 | −0.065957 | 0.0239151 | 0.0985051 | 0.0720341 | −0.00885 | −0.01915 |
| 54 | −0.035494 | 0.029834 | −0.000207 | −0.003911 | 0.00359 | 0.037695 | −0.04259 | −0.031326 | −0.102682 | 0.011976 | 0.02863 | −0.063206 | −0.011589 | 0.010604 |
| 55 | 0.001826 | 0.022961 | 0.111182 | −0.025156 | −0.0851 | −0.002162 | −0.020134 | 0.041724 | −0.001067 | 0.025806 | 0.013307 | 0.040937 | −0.002457 | −0.037244 |
| 56 | −0.042075 | 0.003346 | 0.017633 | 0.005669 | 0.013001 | −0.094394 | −0.019545 | 0.011939 | 0.014162 | −0.024293 | −0.028822 | 0.034359 | 0.00171 | −0.033039 |
| 57 | 0.013648 | −0.027534 | −0.039224 | −0.000605 | 0.018475 | −0.059797 | 0.057025 | 0.015488 | −0.056485 | −0.040287 | −0.048832 | 0.07253 | 0.067887 | 0.036895 |
| 58 | −0.009482 | −0.024123 | −0.057604 | −0.01172 | 0.027794 | −0.106635 | −0.101583 | 0.025419 | −0.019406 | 0.043302 | 0.044294 | 0.007476 | −0.00166 | −0.009357 |
| 59 | −0.050519 | −0.017997 | 0.021986 | −0.012041 | −0.013882 | 0.018862 | −0.018173 | 0.014289 | 0.028143 | −0.174463 | −0.011027 | 0.121436 | 0.093132 | 0.005881 |
| 60 | 0.0073 | −0.016995 | −0.004529 | 0.025467 | 0.019587 | −0.003829 | −0.015689 | −0.028488 | 0.013689 | 0.022115 | −0.005055 | −0.069007 | −0.033811 | −0.006349 |
| 61 | 0.001338 | −0.019358 | −0.01722 | 0.020698 | 0.017454 | −0.00517 | −0.013814 | −0.001741 | 0.021632 | 0.022826 | −0.015209 | −0.048881 | −0.015067 | −0.00847 |
| 62 | 0.000391 | 0.003236 | 0.020498 | −0.011919 | −0.005083 | 0.003166 | −0.002648 | −0.00902 | −0.017767 | 0.010295 | 0.000109 | −0.042769 | −0.063012 | −0.062817 |
| 63 | 0.016027 | 0.009947 | 0.005599 | 0.002383 | 0.004648 | −0.005493 | −0.001283 | 0.020873 | 0.018281 | −0.00041 | −0.023496 | −0.015145 | −0.004281 | −0.002575 |
| 64 | 0.005617 | −0.013575 | 0.008637 | 0.021606 | 0.027248 | 0.013742 | 0.004484 | 0.00839 | 0.008659 | 0.006604 | −0.010487 | −0.005575 | −0.007172 | −0.027671 |
| 65 | −0.006771 | 0.015608 | 0.035588 | 0.025327 | 0.0175 | −0.025988 | −0.000049 | −0.004558 | −0.018492 | −0.052462 | −0.008726 | 0.004607 | −0.002248 | −0.00111 |
| 66 | −0.008624 | 0.013506 | 0.032051 | 0.027328 | 0.006291 | −0.06654 | −0.023213 | 0.011769 | 0.004552 | −0.029222 | −0.003007 | 0.011744 | 0.01203 | 0.003276 |
| 67 | 0.011064 | 0.006267 | −0.015103 | −0.015765 | −0.004138 | −0.004095 | −0.011667 | 0.005699 | −0.027092 | 0.000611 | 0.010571 | −0.011777 | 0.011455 | 0.010573 |
| 68 | −0.005209 | −0.013925 | −0.024838 | −0.010723 | 0.018329 | −0.014016 | 0.000737 | 0.022936 | 0.009584 | −0.023345 | −0.003868 | 0.015321 | 0.010207 | 0.001773 |
| 69 | −0.014638 | 0.002958 | −0.014535 | −0.016496 | −0.010162 | −0.01223 | −0.024744 | 0.018275 | −0.002521 | 0.012277 | 0.00774 | 0.021234 | 0.002081 | −0.01522 |
| 70 | 0.008409 | −0.000857 | −0.010291 | −0.013831 | −0.010632 | −0.012861 | −0.022061 | −0.005512 | −0.001918 | −0.003499 | 0.014913 | 0.015147 | 0.006029 | 0.013793 |
| 71 | −0.003668 | 0.010572 | 0.00318 | −0.006826 | −0.002104 | −0.007627 | 0.017066 | 0.014292 | 0.016889 | −0.015288 | −0.00224 | 0.016788 | 0.007168 | 0.001726 |
| 72 | −0.016711 | 0.019639 | 0.009199 | −0.009174 | −0.00436 | 0.006812 | 0.004248 | 0.002555 | 0.001355 | 0.000622 | 0.007507 | 0.005312 | 0.005639 | −0.004033 |
| 73 | −0.009746 | 0.039708 | −0.005867 | −0.008392 | −0.010341 | 0.004675 | −0.003473 | −0.000434 | −0.026258 | 0.002836 | 0.028621 | 0.01762 | 0.006782 | 0.011253 |
| 74 | 0.011739 | −0.000799 | 0.011607 | 0.011442 | 0.025401 | −0.003126 | 0.014408 | 0.006291 | 0.019735 | −0.022146 | 0.005509 | 0.008579 | −0.007427 | −0.004031 |
| 75 | 0.010069 | 0.000498 | 0.004506 | −0.001664 | −0.003473 | −0.004841 | −0.012486 | 0.001824 | 0.013603 | −0.010113 | −0.006136 | 0.000551 | −0.00592 | −0.001847 |
| 76 | 0.001697 | 0.001688 | 0.008923 | −0.011521 | −0.013908 | −0.014704 | −0.012167 | −0.006012 | −0.013279 | 0.015016 | 0.011605 | −0.004027 | −0.015191 | −0.00351 |
| 77 | 0.013401 | 0.002612 | 0.00198 | −0.005906 | −0.006035 | −0.00871 | −0.012654 | 0.006442 | 0.012288 | −0.011576 | −0.00551 | 0.010162 | −0.003433 | −0.000149 |
| 78 | 0.003833 | 0.00329 | 0.006418 | −0.007526 | −0.011527 | 0.00519 | −0.013016 | 0.000009 | 0.008116 | −0.018937 | −0.007468 | 0.014435 | 0.003542 | 0.005201 |
| 79 | 0.017609 | −0.010517 | −0.007962 | 0.005966 | 0.003329 | −0.000589 | −0.009335 | 0.005502 | 0.015087 | −0.000344 | 0.017901 | 0.003315 | −0.004994 | −0.006803 |
| 80 | −0.016615 | 0.002302 | −0.006331 | −0.009883 | −0.004625 | −0.00582 | −0.029332 | −0.012086 | −0.005208 | −0.002226 | −0.027013 | −0.0191 | −0.001726 | −0.002835 |
| 81 | −0.022607 | −0.016425 | 0.005019 | −0.000354 | −0.000158 | 0.016472 | 0.017225 | −0.003821 | −0.006708 | 0.008527 | −0.009121 | 0.00332 | −0.019182 | −0.004631 |
| 82 | −0.00606 | −0.017115 | −0.008138 | −0.008655 | −0.00855 | −0.017068 | −0.010106 | −0.005586 | 0.00221 | 0.010452 | −0.000832 | −0.000287 | −0.000789 | −0.001427 |
| 83 | −0.018533 | −0.008729 | 0.003649 | −0.002488 | −0.011275 | −0.00525 | −0.004338 | −0.00304 | 0.001198 | 0.003251 | −0.005822 | 0.001728 | 0.008387 | 0.004967 |
| 84 | −0.006334 | −0.001418 | −0.003344 | −0.006665 | −0.008005 | 0.001279 | 0.001006 | −0.005264 | 0.001907 | −0.009939 | −0.007106 | 0.008091 | 0.014038 | 0.00989 |
| 85 | −0.019439 | −0.014591 | 0.005817 | −0.00063 | −0.000253 | 0.022557 | 0.015818 | −0.008964 | −0.018164 | 0.016805 | 0.034296 | 0.000137 | −0.011147 | −0.022646 |
| 86 | −0.017145 | 0.013152 | 0.008196 | −0.003655 | −0.011749 | −0.005395 | 0.012068 | 0.000135 | 0.001561 | −0.00285 | −0.007081 | 0.007743 | 0.009296 | −0.001231 |
| 87 | −0.014935 | −0.005991 | −0.008318 | −0.023269 | −0.025701 | −0.00648 | −0.002445 | −0.015779 | −0.013106 | 0.001509 | −0.001337 | −0.005426 | 0.003558 | 0.003315 |
| 88 | −0.009591 | −0.014376 | −0.002819 | −0.00568 | −0.006845 | −0.003349 | −0.005619 | −0.006255 | −0.003004 | 0.006175 | −0.005507 | 0.00371 | 0.009397 | 0.00779 |
| 89 | −0.018029 | −0.010262 | −0.007103 | −0.010196 | −0.008009 | 0.004527 | −0.002303 | 0.000399 | 0.002327 | −0.011011 | −0.005987 | 0.014286 | 0.017971 | 0.005743 |
| 90 | −0.027818 | −0.005082 | −0.005017 | −0.006074 | −0.003092 | 0.002331 | −0.006524 | 0.002096 | 0.009655 | −0.005387 | −0.004455 | 0.000661 | 0.008097 | −0.000605 |
| 91 | −0.025253 | 0.003261 | −0.005408 | −0.002974 | 0.001796 | 0.001034 | −0.003747 | −0.009042 | −0.005907 | −0.014185 | −0.010674 | 0.015623 | 0.020267 | 0.003679 |
| 92 | −0.033928 | 0.019366 | −0.003615 | −0.008965 | −0.02081 | 0.00042 | −0.012732 | −0.019411 | 0.042341 | 0.013174 | 0.004237 | 0.011693 | 0.015812 | 0.030884 |
| 93 | −0.011802 | 0.010953 | −0.021746 | −0.004268 | 0.009572 | −0.002103 | −0.004356 | 0.001789 | 0.003805 | −0.00032 | −0.021548 | −0.008449 | 0.011331 | 0.010473 |
| 94 | −0.04359 | 0.016583 | 0.001243 | 0.002263 | 0.004036 | 0.009455 | 0.007797 | −0.011398 | −0.011075 | 0.008584 | 0.023853 | −0.002843 | 0.008811 | 0.017349 |

APPENDIX B3-continued

PCA Transformation Matrix (340 × 340 Early/Late)

| | | | | | | | | | | | | | |
|---|---|---|---|---|---|---|---|---|---|---|---|---|---|
| 95 | 0.012119 | 0.007294 | −0.00298 | 0.006112 | 0.002481 | −0.026539 | −0.011457 | 0.030653 | 0.032495 | 0.018456 | 0.021192 | 0.023529 | 0.024136 | 0.000399 |
| 96 | 0.017601 | −0.047531 | −0.023982 | −0.000841 | 0.011166 | −0.007588 | −0.008097 | −0.009098 | 0.018779 | 0.003096 | 0.000597 | 0.003914 | 0.010967 | 0.016987 |
| 97 | −0.009207 | 0.015438 | 0.026791 | 0.031368 | 0.024829 | 0.008049 | 0.001109 | 0.015606 | 0.003386 | 0.00238 | −0.005456 | 0.007283 | 0.005683 | 0.014552 |
| 98 | −0.001903 | 0.005301 | −0.00069 | 0.001863 | 0.008669 | 0.007801 | 0.000968 | −0.005517 | 0.002856 | 0.003252 | 0.003954 | −0.016586 | −0.008906 | −0.004612 |
| 99 | −0.003655 | 0.001405 | 0.015787 | 0.016471 | 0.015038 | −0.002631 | −0.001763 | 0.013586 | 0.014173 | −0.001031 | 0.004208 | 0.016412 | 0.007291 | 0.012402 |
| 100 | 0.01105 | 0.004796 | −0.003644 | 0.006432 | 0.004392 | 0.014026 | 0.003828 | −0.001747 | −0.000431 | 0.007817 | 0.006787 | −0.01891 | −0.011058 | −0.004308 |
| 101 | 0.009768 | 0.015922 | −0.008736 | −0.006444 | 0.01394 | 0.00975 | 0.015921 | 0.004652 | 0.000005 | 0.008404 | 0.012161 | −0.013314 | −0.005686 | 0.002423 |
| 102 | −0.012203 | −0.013621 | −0.012379 | −0.008455 | −0.008796 | 0.018832 | 0.002791 | −0.014859 | 0.014917 | −0.005465 | −0.035255 | 0.000734 | 0.005591 | 0.014314 |
| 103 | −0.022578 | −0.020391 | 0.009787 | −0.002382 | −0.015462 | 0.011752 | 0.016479 | −0.004481 | 0.019795 | −0.004486 | −0.011424 | 0.003728 | −0.006825 | −0.004894 |
| 104 | −0.00611 | 0.007004 | 0.013377 | 0.003064 | 0.004216 | −0.007529 | −0.003055 | 0.00987 | 0.004708 | −0.017542 | −0.025993 | −0.002402 | −0.007875 | −0.01068 |
| 105 | 0.007039 | −0.026122 | −0.019516 | −0.016051 | 0.003185 | −0.00423 | −0.005621 | −0.032989 | −0.010047 | −0.019373 | 0.016676 | −0.015888 | −0.01562 | 0.000008 |
| 106 | −0.005563 | 0.003437 | 0.027349 | 0.002711 | −0.026778 | 0.002352 | −0.014759 | −0.023081 | −0.016963 | 0.006719 | −0.031072 | 0.003307 | −0.016819 | −0.006656 |
| 107 | −0.010981 | 0.006101 | 0.038607 | −0.012413 | −0.033056 | 0.009232 | −0.009836 | −0.005498 | −0.011992 | 0.009424 | −0.013771 | 0.011731 | −0.014049 | 0.000907 |
| 108 | 0.013457 | −0.04939 | −0.026886 | −0.018159 | 0.007734 | 0.016996 | 0.02171 | −0.01402 | −0.001007 | −0.001578 | −0.025742 | 0.01111 | −0.002418 | −0.014425 |
| 109 | −0.069607 | 0.015269 | −0.002109 | −0.033272 | −0.028006 | −0.031243 | −0.04259 | −0.01272 | −0.011678 | 0.037924 | 0.014656 | −0.008466 | −0.010445 | −0.00536 |
| 110 | 0.055983 | 0.028925 | 0.021937 | 0.003774 | −0.026962 | −0.007361 | −0.008475 | 0.058274 | 0.073955 | 0.014107 | −0.030789 | −0.010949 | 0.005978 | 0.012597 |
| 111 | 0.050194 | −0.030253 | 0.013242 | −0.003785 | −0.022551 | 0.003773 | 0.000226 | −0.005317 | 0.012189 | −0.00102 | −0.000761 | 0.004035 | −0.016037 | −0.024582 |
| 112 | −0.007429 | −0.019367 | −0.006928 | −0.001816 | −0.002624 | 0.01987 | 0.00091 | 0.005691 | 0.016325 | 0.010659 | 0.005092 | 0.022878 | 0.019939 | −0.003714 |
| 113 | −0.017107 | −0.026072 | 0.00129 | 0.001706 | 0.000235 | −0.019392 | −0.023653 | −0.006782 | 0.008164 | 0.008753 | −0.009968 | 0.022317 | −0.016146 | −0.017133 |
| 114 | −0.018956 | −0.013893 | −0.033751 | −0.043577 | −0.019481 | −0.001126 | 0.006151 | 0.042172 | 0.019876 | 0.002063 | −0.00447 | 0.042633 | 0.014787 | 0.019734 |
| 115 | 0.04258 | 0.017028 | 0.023245 | 0.00498 | 0.002149 | −0.003345 | 0.015884 | 0.002517 | 0.025339 | 0.005188 | 0.008218 | −0.016336 | −0.009798 | 0.003655 |
| 116 | 0.002072 | 0.003574 | −0.002607 | −0.019606 | −0.014998 | −0.021788 | −0.037812 | 0.027329 | −0.000548 | 0.005363 | 0.014594 | 0.015226 | 0.003077 | −0.017324 |
| 117 | −0.017155 | −0.019023 | −0.010741 | 0.008659 | 0.008192 | −0.046906 | −0.019542 | −0.006721 | 0.028734 | −0.005797 | 0.010864 | 0.007687 | 0.005401 | 0.004129 |
| 118 | −0.006734 | 0.008791 | −0.014824 | −0.036495 | −0.00757 | −0.022744 | −0.018405 | −0.002723 | −0.030709 | −0.022853 | 0.02539 | 0.007784 | −0.013275 | −0.017473 |
| 119 | −0.00959 | 0.023718 | 0.005356 | −0.003778 | −0.001949 | 0.001736 | −0.002013 | 0.007986 | −0.006348 | 0.009597 | 0.014141 | 0.022914 | 0.0184 | 0.004269 |
| 120 | −0.02433 | −0.002497 | −0.009325 | 0.014411 | 0.014538 | −0.002419 | 0.000897 | −0.014716 | −0.021085 | −0.022485 | 0.012181 | 0.032364 | 0.014608 | 0.001896 |
| 121 | −0.011765 | 0.007501 | 0.036684 | −0.028737 | 0.021726 | −0.028083 | −0.042947 | −0.001879 | 0.026974 | −0.0228 | −0.002502 | 0.002976 | −0.0102 | −0.023738 |
| 122 | 0.024027 | 0.004214 | 0.00307 | 0.025707 | 0.011433 | −0.022969 | −0.03588 | −0.014168 | 0.004976 | 0.01768 | −0.002979 | −0.016953 | −0.004855 | 0.001141 |
| 123 | 0.022275 | 0.010001 | 0.015734 | 0.006107 | −0.006829 | −0.017702 | −0.009629 | 0.000304 | 0.008926 | 0.006675 | 0.011075 | −0.000632 | −0.011295 | −0.022144 |
| 124 | 0.014004 | 0.01739 | 0.019433 | 0.015231 | 0.007716 | 0.020349 | 0.010427 | 0.012546 | 0.005248 | 0.011042 | 0.014066 | 0.004678 | 0.004553 | −0.002852 |
| 125 | 0.015164 | −0.014392 | 0.011726 | 0.018178 | 0.025184 | 0.002821 | 0.02709 | 0.011692 | 0.0242 | −0.004549 | 0.002813 | 0.001608 | −0.011462 | −0.026215 |
| 126 | 0.00928 | 0.022745 | 0.026038 | 0.002439 | −0.00475 | −0.057108 | −0.041769 | −0.007468 | −0.014044 | −0.023694 | 0.007311 | 0.007846 | −0.008318 | −0.00673 |
| 127 | 0.00618 | 0.029756 | 0.022965 | 0.002324 | −0.006437 | −0.025169 | −0.014675 | 0.004322 | −0.018225 | −0.004927 | 0.012831 | 0.004067 | 0.004111 | 0.009378 |
| 128 | −0.013181 | 0.006873 | 0.008235 | −0.000517 | −0.009649 | −0.007305 | 0.000541 | 0.000485 | 0.003366 | −0.009602 | −0.010236 | 0.00068 | −0.003884 | −0.002806 |
| 129 | 0.01513 | 0.01107 | 0.00144 | 0.029019 | 0.015481 | −0.008944 | −0.003366 | 0.022911 | 0.018024 | 0.00086 | −0.000929 | −0.012678 | −0.001459 | −0.002349 |
| 130 | −0.023292 | 0.003951 | 0.02606 | 0.021418 | 0.012358 | 0.000602 | −0.010684 | −0.027492 | −0.017134 | 0.008823 | 0.005668 | −0.01601 | −0.005591 | 0.000588 |
| 131 | 0.044342 | −0.012302 | 0.00083 | 0.014569 | 0.01983 | −0.007976 | −0.044102 | 0.002817 | 0.02578 | −0.005082 | 0.012073 | 0.002031 | 0.012506 | 0.016857 |
| 132 | −0.025013 | −0.002051 | 0.000635 | −0.001412 | −0.007923 | 0.007771 | 0.007633 | 0.005236 | 0.007913 | 0.004311 | −0.007818 | 0.005239 | 0.003598 | −0.010919 |
| 133 | −0.032642 | 0.019228 | 0.009296 | 0.0076 | 0.001458 | 0.024625 | 0.018895 | 0.0122281 | 0.035356 | −0.01544 | −0.00441 | −0.01619 | −0.003396 | 0.007928 |
| 134 | 0.010897 | −0.010966 | −0.000455 | −0.039091 | −0.017527 | −0.006481 | 0.001974 | −0.005479 | −0.007886 | 0.007079 | 0.03426 | 0.008001 | −0.001187 | −0.023082 |
| 135 | −0.016168 | 0.002771 | 0.00081 | 0.000205 | 0.00023 | 0.00944 | 0.00473 | −0.000906 | −0.005962 | −0.00963 | −0.003749 | 0.007569 | 0.006819 | −0.008017 |
| 136 | 0.035992 | 0.008029 | −0.016143 | −0.025552 | −0.02475 | 0.009856 | 0.00643 | 0.012187 | 0.019158 | 0.004494 | 0.016035 | −0.012192 | −0.002212 | 0.009982 |
| 137 | −0.023987 | 0.01616 | 0.025643 | 0.002771 | −0.001594 | 0.00684 | −0.000399 | −0.017792 | −0.025594 | −0.005429 | 0.017001 | −0.007683 | −0.025727 | −0.020416 |
| 138 | −0.013977 | −0.006268 | −0.014594 | −0.003175 | 0.015952 | −0.015573 | −0.02318 | −0.0011371 | −0.014379 | −0.002633 | −0.026503 | 0.009972 | 0.011499 | 0.008903 |
| 139 | −0.0037 | −0.002956 | −0.008497 | −0.00872 | −0.005099 | 0.008835 | 0.006939 | −0.046326 | −0.070564 | 0.021758 | 0.01703 | −0.021664 | −0.035374 | −0.007991 |
| 140 | −0.000216 | 0.016054 | −0.022899 | −0.010464 | 0.013012 | −0.021987 | −0.028853 | 0.008277 | 0.007904 | 0.004055 | −0.01123 | 0.005999 | 0.007141 | −0.015766 |
| 141 | −0.01278 | −0.0092 | −0.011392 | −0.013672 | −0.015357 | 0.002208 | 0.017312 | 0.006263 | −0.001647 | 0.002495 | −0.005701 | 0.011386 | 0.014616 | 0.007304 |
| 142 | −0.018311 | 0.009204 | 0.015388 | 0.017122 | −0.000246 | 0.00637 | 0.028815 | 0.001273 | 0.011225 | −0.004392 | −0.003161 | 0.000961 | 0.014467 | 0.013769 |
| 143 | 0.002542 | −0.00313 | −0.001705 | 0.022828 | 0.021535 | 0.00959 | 0.00645 | −0.010134 | 0.006461 | 0.01147 | −0.039778 | −0.018888 | −0.000157 | 0.001901 |
| 144 | 0.017231 | −0.001942 | −0.010998 | 0.002697 | −0.001236 | −0.008217 | −0.007707 | 0.013854 | 0.035601 | 0.018838 | −0.036855 | −0.021871 | 0.004572 | −0.004205 |

APPENDIX B3-continued

PCA Transformation
Matrix (340 × 340 Early/Late)

| | | | | | | | | | | | | | |
|---|---|---|---|---|---|---|---|---|---|---|---|---|---|
| 145 | −0.022561 | 0.036277 | −0.018067 | −0.009446 | −0.004705 | −0.006813 | 0.005385 | 0.021587 | 0.024878 | 0.031615 | −0.001782 | −0.026158 | −0.009783 | 0.000755 |
| 146 | −0.022597 | −0.008753 | 0.005803 | 0.004981 | 0.00307 | 0.00175 | 0.000274 | −0.002336 | −0.016658 | −0.007089 | 0.000037 | 0.012673 | −0.004751 | −0.022671 |
| 147 | −0.050059 | −0.006452 | 0.013529 | −0.003492 | −0.011476 | −0.032775 | −0.01833 | −0.027024 | −0.025192 | −0.02746 | −0.041122 | 0.02017 | 0.00586 | 0.00441 |
| 148 | 0.029538 | −0.002739 | 0.009104 | −0.003722 | −0.028838 | −0.060533 | −0.049905 | −0.018744 | −0.040615 | −0.001203 | 0.011544 | 0.008116 | −0.008631 | 0.00817 |
| 149 | 0.009799 | −0.005538 | 0.002047 | −0.007725 | −0.006409 | −0.00405 | 0.014642 | 0.010656 | 0.011261 | 0.00348 | 0.012163 | 0.006581 | −0.008502 | −0.000478 |
| 150 | 0.000021 | 0.012203 | −0.001117 | 0.020591 | 0.029454 | 0.02187 | 0.008009 | 0.004607 | −0.021429 | −0.012934 | 0.006832 | 0.0085161 | −0.004823 | −0.01503 |
| 151 | 0.026925 | 0.010426 | −0.01213 | −0.035249 | −0.019923 | −0.023393 | 0.000571 | 0.009846 | −0.012675 | 0.02576 | 0.011726 | −0.00235 | −0.002225 | 0.00318 |
| 152 | 0.005685 | 0.008368 | 0.012473 | −0.000098 | −0.014217 | −0.005172 | 0.009109 | 0.008472 | −0.010014 | −0.015324 | 0.012362 | 0.02124 | 0.025502 | 0.014206 |
| 153 | 0.001442 | −0.006091 | 0.020254 | 0.008411 | −0.00559 | −0.00287 | 0.0216471 | −0.003158 | −0.016363 | −0.021084 | −0.005851 | −0.003691 | 0.000921 | −0.006261 |
| 154 | 0.022401 | 0.017101 | 0.002598 | 0.010008 | 0.003894 | 0.007645 | 0.010964 | 0.00516 | 0.020612 | −0.018888 | −0.012841 | −0.010601 | 0.017385 | 0.011389 |
| 155 | 0.008852 | −0.008658 | 0.009295 | 0.00946 | −0.000125 | 0.019699 | 0.00795 | −0.008991 | −0.009971 | −0.022625 | −0.025644 | −0.008098 | −0.010026 | −0.021473 |
| 156 | 0.000155 | −0.025445 | −0.002337 | 0.011133 | 0.019303 | 0.009664 | 0.015199 | −0.021237 | −0.001604 | −0.014927 | −0.037588 | 0.00352 | 0.0046 | −0.00237 |
| 157 | 0.00548 | 0.003197 | 0.009531 | 0.014886 | 0.002269 | 0.011386 | 0.004801 | 0.010288 | 0.010237 | 0.007756 | −0.002801 | −0.002781 | −0.014037 | −0.020517 |
| 158 | −0.027386 | −0.009382 | 0.014253 | 0.002811 | −0.007347 | 0.040959 | 0.029426 | −0.038346 | −0.028975 | −0.018249 | −0.018583 | −0.009866 | −0.000343 | 0.002191 |
| 159 | −0.022947 | 0.044185 | −0.014208 | 0.003035 | 0.007172 | 0.022189 | 0.001322 | −0.00512 | −0.023938 | −0.009908 | 0.014688 | −0.018364 | 0.006853 | 0.014934 |
| 160 | 0.030484 | 0.022479 | 0.01791 | 0.00463 | 0.008198 | −0.044014 | −0.004572 | 0.020453 | −0.006971 | −0.004896 | 0.032668 | 0.011439 | −0.009541 | −0.002986 |
| 161 | −0.048811 | −0.016889 | 0.012178 | −0.008219 | −0.031177 | −0.010938 | −0.016643 | −0.023437 | −0.051481 | 0.007884 | 0.002172 | 0.003277 | −0.009782 | −0.001158 |
| 162 | 0.01499 | 0.018317 | −0.034394 | −0.018023 | 0.01858 | −0.009868 | 0.013721 | 0.029978 | 0.00194 | 0.01414 | 0.01552 | 0.007372 | 0.010299 | 0.000112 |
| 163 | −0.004389 | 0.01162 | 0.028187 | 0.013303 | −0.007878 | 0.015479 | 0.025154 | 0.001911 | −0.012011 | 0.004497 | 0.004992 | 0.001023 | 0.003013 | 0.000236 |
| 164 | 0.021967 | −0.00759 | −0.045819 | −0.032856 | −0.004155 | 0.020475 | 0.025187 | 0.014222 | 0.015793 | 0.022586 | −0.004578 | −0.022549 | −0.007932 | 0.013973 |
| 165 | 0.017836 | −0.024705 | 0.018976 | −0.000874 | −0.00961 | −0.07022 | −0.023029 | 0.011519 | 0.034195 | −0.034291 | −0.009977 | −0.011266 | −0.019801 | −0.007298 |
| 166 | 0.012592 | −0.027487 | −0.020612 | 0.00379 | 0.014729 | −0.019526 | 0.01203 | 0.006033 | 0.024764 | 0.019022 | 0.014953 | 0.002469 | 0.002228 | −0.007807 |
| 167 | −0.01425 | −0.020925 | −0.018224 | −0.001254 | 0.014045 | −0.002735 | 0.001026 | −0.005809 | 0.028611 | 0.010844 | −0.036282 | −0.020617 | −0.021012 | −0.025592 |
| 168 | 0.004093 | 0.018365 | 0.019626 | 0.010024 | 0.008205 | 0.030245 | 0.004944 | 0.00529 | −0.012952 | 0.008702 | −0.013454 | −0.014665 | −0.007563 | 0.006055 |
| 169 | −0.010571 | −0.005693 | 0.00041 | 0.005918 | 0.013818 | 0.000304 | 0.000389 | 0.00772 | 0.002194 | 0.015578 | 0.001899 | −0.000896 | −0.000534 | 0.001346 |
| 170 | −0.002744 | 0.004179 | −0.007928 | 0.002986 | 0.016222 | −0.003651 | −0.003761 | 0.015668 | 0.004239 | 0.021594 | 0.008663 | −0.007519 | 0.011542 | 0.023892 |
| 171 | −0.012995 | −0.012075 | 0.003373 | 0.000542 | 0.00276 | 0.000901 | −0.009152 | −0.002694 | −0.009322 | 0.006088 | 0.008286 | 0.001812 | −0.001121 | −0.003759 |
| 172 | −0.022051 | −0.009029 | 0.018574 | 0.004429 | 0.002422 | 0.018653 | 0.013518 | 0.000554 | −0.010157 | −0.003798 | 0.003272 | 0.022886 | −0.001796 | −0.012972 |
| 173 | 0.01369 | 0.014218 | 0.034194 | 0.011881 | 0.006031 | −0.006048 | 0.0177 | 0.015989 | 0.018761 | −0.014359 | 0.005542 | −0.001835 | −0.015108 | −0.008186 |
| 174 | 0.006383 | 0.000845 | 0.016632 | 0.008861 | 0.002938 | 0.009476 | 0.005413 | 0.007672 | 0.004271 | 0.016034 | −0.024915 | −0.013139 | −0.014152 | −0.007454 |
| 175 | −0.004049 | −0.044823 | 0.002294 | 0.012288 | −0.000077 | −0.014177 | −0.020099 | −0.024338 | −0.025013 | 0.035432 | 0.031214 | 0.001133 | −0.023908 | −0.009674 |
| 176 | −0.014375 | −0.051248 | 0.009698 | 0.016015 | 0.003456 | 0.011985 | 0.000951 | −0.027511 | −0.000171 | 0.00786 | −0.004143 | −0.005576 | −0.014753 | −0.002765 |
| 177 | 0.00724 | 0.010383 | −0.03677 | −0.017861 | 0.015043 | 0.015996 | −0.020515 | −0.013249 | −0.013965 | −0.008662 | −0.026509 | −0.011936 | 0.007978 | 0.010289 |
| 178 | −0.011074 | 0.024359 | 0.019775 | 0.004217 | −0.011666 | −0.007111 | −0.005728 | −0.016881 | −0.021315 | −0.003982 | 0.003164 | −0.019879 | −0.024874 | −0.003478 |
| 179 | 0.010772 | 0.008198 | −0.002614 | 0.000307 | 0.003081 | 0.004447 | −0.000698 | −0.003891 | −0.00029 | −0.000174 | −0.007458 | −0.01398 | −0.008788 | −0.002478 |
| 180 | 0.012394 | 0.00778 | −0.000226 | −0.00023 | 0.006017 | −0.001734 | 0.001166 | −0.001122 | 0.004974 | −0.015347 | −0.00745 | −0.008627 | −0.006609 | 0.000248 |
| 181 | 0.008186 | 0.005851 | 0.000117 | 0.000273 | 0.002929 | 0.007162 | 0.000858 | −0.006032 | 0.005053 | −0.00172 | −0.006923 | −0.02009 | −0.011894 | −0.002864 |
| 182 | 0.009911 | 0.009198 | −0.009907 | 0.001881 | 0.002305 | 0.022038 | 0.006593 | −0.004585 | 0.003746 | −0.011364 | −0.002198 | −0.014561 | −0.00032 | 0.012467 |
| 183 | 0.020492 | 0.000518 | −0.004017 | −0.001427 | −0.006405 | 0.012972 | −0.004379 | −0.006714 | 0.000834 | −0.010088 | −0.002525 | −0.006359 | −0.007245 | −0.012199 |
| 184 | 0.014353 | −0.000754 | 0.016752 | 0.000973 | −0.015124 | −0.002195 | 0.008827 | 0.002183 | −0.00235 | 0.007017 | −0.004123 | 0.008806 | −0.009096 | −0.034067 |
| 185 | −0.008776 | 0.000725 | 0.024385 | 0.032731 | 0.012023 | −0.002878 | −0.011834 | −0.002634 | 0.004509 | −0.011498 | −0.035217 | −0.00172 | −0.007795 | −0.02157 |
| 186 | 0.013437 | 0.000618 | 0.011377 | −0.004809 | −0.016439 | −0.007603 | −0.030181 | −0.001201 | −0.028077 | −0.008882 | 0.004135 | 0.017468 | 0.000564 | −0.01863 |
| 187 | 0.026558 | 0.029414 | 0.003161 | 0.000827 | 0.005498 | −0.014627 | 0.01559 | 0.024165 | 0.020617 | −0.030797 | −0.009853 | 0.011701 | 0.017522 | 0.018169 |
| 188 | 0.020162 | 0.01394 | −0.008268 | 0.000207 | 0.007768 | −0.002499 | 0.007741 | 0.016301 | 0.017562 | −0.01653 | −0.041084 | 0.00324 | 0.016467 | 0.020075 |
| 189 | 0.036206 | −0.014518 | −0.028477 | 0.002115 | 0.014059 | 0.016786 | 0.004216 | 0.000703 | 0.007662 | 0.016988 | −0.02283 | −0.013199 | 0.004093 | 0.013305 |
| 190 | 0.01227 | −0.019411 | −0.011099 | −0.006299 | 0.005375 | 0.005096 | 0.022095 | −0.004572 | −0.002173 | 0.016564 | 0.019319 | −0.003691 | −0.019786 | −0.01921 |
| 191 | 0.014731 | −0.001787 | −0.013351 | −0.012756 | 0.001988 | 0.010346 | 0.017917 | 0.004332 | −0.002861 | 0.005757 | 0.014259 | 0.002411 | −0.000925 | −0.008762 |
| 192 | 0.012371 | 0.041283 | 0.004026 | 0.009545 | 0.00429 | 0.002512 | −0.01093 | 0.021533 | −0.00182 | −0.003736 | −0.013139 | 0.018407 | 0.034535 | 0.021522 |
| 193 | 0.012829 | 0.007004 | 0.01813 | 0.006316 | −0.014589 | −0.004307 | 0.009285 | 0.007419 | −0.002512 | −0.005611 | −0.004241 | 0.017127 | 0.02028 | 0.012459 |
| 194 | 0.011846 | −0.00878 | 0.003194 | 0.003746 | 0.007948 | −0.003697 | 0.025542 | 0.004297 | −0.004682 | −0.011738 | −0.007851 | 0.021007 | −0.000534 | −0.008016 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 195 | 0.036183 | 0.000963 | 0.016232 | −0.006658 | −0.016961 | 0.023438 | 0.016675 | 0.028169 | 0.015921 | 0.007978 | 0.02007 | 0.01419 | −0.013212 | −0.028414 |
| 196 | 0.017828 | −0.010731 | −0.004602 | −0.003896 | −0.001099 | 0.009716 | −0.002155 | 0.005738 | −0.000482 | 0.026689 | 0.020837 | 0.003509 | −0.011998 | −0.023486 |
| 197 | 0.012736 | −0.023007 | −0.021915 | −0.005421 | 0.00929 | 0.022808 | 0.024102 | 0.009035 | 0.020331 | 0.007236 | 0.014976 | 0.001393 | 0.001015 | −0.008061 |
| 198 | 0.009055 | 0.001988 | 0.021083 | 0.002582 | −0.015749 | 0.010337 | 0.005557 | 0.004875 | −0.017769 | −0.011694 | 0.018407 | 0.02652 | −0.004494 | −0.016174 |
| 199 | −0.010363 | −0.006921 | 0.006752 | −0.003412 | −0.007024 | −0.014469 | 0.007572 | 0.003183 | 0.008809 | 0.02566 | −0.008487 | 0.001964 | −0.008819 | 0.015982 |
| 200 | −0.024355 | −0.007118 | 0.006291 | −0.018303 | −0.017679 | 0.02171 | 0.004749 | −0.010892 | −0.031773 | 0.002157 | 0.015829 | 0.003082 | −0.013794 | −0.02236 |
| 201 | 0.029851 | 0.023932 | −0.00658 | −0.020724 | −0.013179 | −0.024503 | −0.010886 | 0.026712 | −0.005714 | −0.025767 | 0.005283 | 0.018314 | 0.006755 | 0.020609 |
| 202 | 0.010695 | 0.0089 | 0.007518 | −0.011776 | −0.018821 | −0.000763 | 0.005897 | 0.01496 | −0.003316 | −0.008337 | 0.028327 | 0.030334 | 0.004611 | −0.00461 |
| 203 | 0.011599 | 0.007079 | −0.00943 | 0.006784 | 0.007239 | −0.001766 | 0.022097 | −0.005982 | −0.014091 | 0.003214 | 0.003821 | −0.012496 | −0.014496 | 0.001083 |
| 204 | 0.00338 | −0.002763 | 0.016336 | 0.032457 | 0.019822 | −0.031865 | −0.042609 | 0.004832 | −0.011061 | −0.0047 | −0.004133 | 0.009081 | −0.00146 | −0.020776 |
| 205 | −0.021981 | −0.031376 | −0.004597 | −0.018954 | −0.00206 | 0.011987 | 0.026134 | −0.045646 | −0.012323 | 0.013736 | 0.002504 | −0.020853 | −0.022774 | −0.038035 |
| 206 | −0.0238 | −0.02406 | 0.014425 | 0.021963 | 0.013731 | 0.004719 | 0.01316 | −0.023563 | 0.007168 | −0.003454 | −0.016896 | −0.004467 | −0.000501 | −0.010175 |
| 207 | 0.035825 | −0.019979 | 0.005579 | 0.00779 | 0.001613 | 0.015416 | −0.043724 | −0.016457 | 0.018222 | −0.006548 | 0.03368 | −0.008078 | 0.010563 | 0.025788 |
| 208 | 0.009283 | 0.002757 | −0.021286 | 0.000258 | 0.009435 | −0.008755 | 0.011653 | 0.024274 | 0.025967 | 0.005048 | 0.009692 | 0.003002 | 0.026814 | 0.00709 |
| 209 | −0.037312 | −0.005604 | 0.016172 | 0.010985 | −0.008121 | 0.005635 | 0.013974 | −0.00251 | 0.002225 | −0.004434 | 0.001969 | 0.009468 | 0.005882 | −0.00725 |
| 210 | 0.033601 | −0.06456 | 0.004042 | −0.009369 | −0.030884 | 0.031965 | 0.000444 | −0.026108 | −0.009429 | −0.02421 | −0.000429 | 0.004925 | −0.046962 | −0.0449 |
| 211 | 0.005697 | −0.006723 | 0.012758 | −0.012877 | −0.006726 | 0.011403 | 0.00469 | −0.018503 | −0.018108 | −0.030115 | −0.009687 | 0.014193 | −0.014059 | −0.019406 |
| 212 | −0.015239 | −0.021994 | 0.03473 | −0.00616 | −0.018861 | 0.012005 | 0.00324 | −0.003085 | 0.002347 | 0.00535 | −0.00054 | 0.00307 | −0.008564 | −0.025321 |
| 213 | −0.020962 | 0.006319 | −0.004102 | −0.009698 | −0.018051 | 0.008433 | 0.001361 | −0.030658 | −0.045957 | −0.013985 | −0.026779 | 0.017328 | −0.006205 | 0.009351 |
| 214 | 0.02555 | 0.016934 | −0.003633 | −0.003541 | 0.002678 | 0.013728 | −0.002335 | 0.012097 | 0.010606 | −0.010053 | 0.003516 | 0.000057 | 0.001666 | −0.003884 |
| 215 | −0.008791 | 0.003973 | 0.028576 | 0.015958 | −0.003786 | 0.008838 | −0.026827 | −0.024953 | −0.024335 | 0.003816 | −0.001335 | −0.021082 | −0.013259 | −0.028107 |
| 216 | −0.009712 | −0.012435 | −0.000792 | −0.030904 | −0.022252 | 0.018358 | −0.007869 | −0.009969 | −0.020232 | 0.003625 | −0.014364 | −0.007697 | −0.018361 | −0.014284 |
| 217 | −0.003907 | 0.003537 | 0.000761 | −0.01608 | −0.010085 | −0.005954 | 0.0033 | 0.002618 | −0.035482 | 0.024885 | 0.007839 | 0.023086 | −0.016578 | −0.026047 |
| 218 | 0.006292 | −0.001896 | −0.000873 | 0.011322 | 0.005839 | 0.019363 | −0.019037 | −0.009089 | 0.002847 | 0.023282 | 0.005527 | −0.021115 | −0.006332 | −0.007229 |
| 219 | −0.017986 | 0.00049 | 0.008987 | −0.035644 | −0.039007 | 0.016081 | −0.002743 | 0.004735 | −0.01464 | 0.025685 | 0.010889 | −0.000756 | −0.024799 | 0.030118 |
| 220 | 0.001181 | −0.000286 | 0.034545 | 0.025192 | 0.02585 | 0.012101 | −0.00157 | −0.010569 | −0.025678 | 0.018161 | 0.005249 | −0.030194 | −0.047821 | −0.06085 |
| 221 | 0.009986 | 0.014623 | 0.034166 | 0.020994 | 0.019399 | 0.002766 | 0.009967 | 0.001613 | −0.002994 | −0.04546 | 0.002937 | 0.012051 | −0.004542 | −0.016483 |
| 222 | −0.000939 | 0.014625 | 0.02172 | 0.003526 | −0.002802 | 0.015068 | 0.008966 | −0.007896 | −0.026987 | 0.006407 | 0.01099 | −0.002633 | −0.004157 | −0.010552 |
| 223 | −0.000539 | −0.00196 | 0.029381 | 0.00934 | −0.004699 | 0.013967 | 0.011818 | −0.014845 | −0.017613 | −0.000733 | 0.007443 | −0.011054 | −0.014845 | −0.012407 |
| 224 | −0.014584 | −0.016106 | 0.007944 | −0.000362 | −0.004322 | 0.006282 | 0.002327 | −0.008744 | −0.019393 | −0.002609 | 0.002191 | 0.015748 | −0.011356 | −0.017257 |
| 225 | −0.02285 | −0.00449 | 0.003579 | −0.003825 | −0.002261 | 0.011053 | 0.005134 | −0.000409 | −0.015151 | −0.013874 | 0.001239 | 0.019217 | −0.007229 | −0.014658 |
| 226 | −0.002728 | 0.009962 | 0.01359 | 0.027591 | 0.014836 | 0.003216 | 0.003877 | 0.010263 | 0.015757 | 0.021779 | 0.037643 | 0.017393 | 0.022541 | 0.013129 |
| 227 | −0.029307 | 0.00981 | 0.019882 | 0.034013 | 0.024259 | −0.01001 | 0.006005 | −0.002606 | 0.000891 | 0.008763 | 0.024015 | 0.010897 | 0.004901 | 0.00411 |
| 228 | −0.052558 | 0.009813 | 0.001715 | −0.000578 | −0.009749 | 0.00953 | −0.00505 | −0.030905 | −0.068551 | 0.023008 | 0.044869 | 0.02031 | 0.017406 | 0.004404 |
| 229 | 0.006241 | 0.034756 | 0.016508 | 0.006782 | 0.012217 | 0.019951 | 0.010495 | 0.012427 | −0.006348 | −0.001434 | −0.015116 | 0.018433 | 0.025705 | 0.024547 |
| 230 | −0.007081 | −0.005262 | 0.019862 | −0.024959 | −0.018719 | 0.032493 | 0.019054 | −0.002796 | 0.002507 | −0.012437 | −0.019998 | 0.00581 | −0.013988 | −0.007083 |
| 231 | −0.078545 | −0.015039 | 0.017305 | −0.015665 | −0.03404 | −0.003095 | 0.035103 | −0.022405 | 0.000574 | −0.010145 | 0.023055 | 0.027301 | 0.010999 | 0.007583 |
| 232 | −0.009691 | −0.039407 | 0.000554 | 0.00971 | 0.000662 | −0.007547 | −0.02868 | −0.037066 | −0.037778 | 0.016317 | 0.008859 | 0.004747 | 0.003793 | −0.022863 |
| 233 | −0.028485 | 0.006362 | 0.003371 | 0.004612 | −0.008322 | −0.03633 | −0.094713 | −0.047284 | −0.048789 | 0.00807 | −0.019487 | −0.030408 | −0.009295 | −0.002559 |
| 234 | −0.126455 | −0.002024 | −0.006517 | −0.017503 | −0.016637 | −0.004035 | −0.033072 | −0.054516 | −0.049569 | 0.019677 | 0.023945 | −0.01963 | −0.00688 | −0.003074 |
| 235 | 0.838855 | −0.008223 | 0.019289 | −0.004669 | −0.022186 | −0.013135 | −0.026257 | −0.076688 | −0.081963 | 0.016917 | 0.019314 | −0.003877 | −0.013097 | −0.01817 |
| 236 | −0.012906 | 0.899867 | −0.020249 | −0.004689 | −0.003963 | 0.015806 | 0.006195 | −0.049315 | −0.001955 | 0.012527 | −0.018207 | −0.012482 | −0.030284 | −0.031527 |
| 237 | 0.016989 | −0.015658 | 0.901488 | −0.033196 | 0.013835 | 0.005558 | 0.004048 | 0.002302 | 0.017271 | 0.012013 | 0.000971 | −0.018182 | 0.01816 | 0.026263 |
| 238 | −0.011744 | 0.001272 | −0.037147 | 0.916249 | −0.060649 | 0.001173 | 0.010943 | 0.014392 | −0.004543 | 0.003074 | 0.011454 | 0.017498 | −0.000173 | −0.003431 |
| 239 | −0.027297 | 0.002575 | 0.008266 | −0.06744 | 0.911346 | 0.002069 | 0.006963 | 0.002027 | −0.016851 | 0.005121 | 0.011317 | 0.019956 | −0.01151 | −0.011859 |
| 240 | 0.005627 | 0.011983 | 0.010007 | 0.008119 | 0.00991 | 0.882789 | −0.065187 | 0.011969 | 0.006026 | −0.006665 | −0.006739 | 0.010714 | 0.011123 | 0.002722 |
| 241 | −0.012431 | −0.002729 | −0.005018 | 0.008029 | 0.008179 | −0.06896 | 0.886722 | −0.026344 | −0.021309 | 0.00044 | −0.032238 | −0.015186 | 0.003163 | 0.000212 |
| 242 | −0.075964 | −0.040104 | 0.003845 | 0.012141 | −0.002435 | 0.013563 | −0.020738 | 0.894282 | −0.085595 | 0.010955 | −0.002134 | −0.036453 | −0.034402 | −0.023812 |
| 243 | −0.082045 | 0.001784 | 0.007251 | −0.007414 | −0.017494 | 0.008038 | −0.016042 | −0.082346 | 0.84109 | 0.009722 | 0.028711 | 0.002205 | −0.023165 | −0.027351 |
| 244 | 0.003662 | 0.020108 | 0.024526 | 0.011134 | 0.004575 | 0.013924 | 0.010528 | 0.004573 | −0.00304 | −0.917268 | −0.026265 | 0.035211 | 0.026379 | 0.014582 |

APPENDIX B3-continued

PCA Transformation
Matrix (340 × 340 Early/Late)

| | | | | | | | | | | | | | |
|---|---|---|---|---|---|---|---|---|---|---|---|---|---|
| 245 | 0.006201 | −0.0086 | 0.007175 | 0.013012 | 0.007406 | 0.000759 | −0.011132 | −0.004943 | 0.019511 | −0.031723 | 0.897619 | −0.016531 | −0.000422 | 0.002229 |
| 246 | 0.011486 | −0.007256 | −0.014824 | 0.009516 | 0.012504 | 0.012912 | −0.009602 | −0.019737 | 0.00717 | 0.030331 | −0.022115 | 0.911274 | −0.048597 | −0.019917 |
| 247 | −0.005869 | −0.033135 | 0.012471 | −0.007792 | −0.014112 | 0.015638 | 0.006412 | −0.024606 | −0.019687 | 0.021621 | −0.008035 | −0.042328 | 0.926588 | −0.061475 |
| 248 | −0.014595 | −0.039927 | 0.013689 | −0.007786 | −0.010005 | 0.012312 | 0.005618 | −0.019635 | −0.021971 | 0.009563 | −0.004402 | −0.012138 | −0.052801 | 0.924204 |
| 249 | −0.001201 | −0.006033 | 0.007387 | 0.000467 | 0.001666 | −0.072361 | −0.06334 | −0.001033 | −0.027722 | 0.01559 | −0.007994 | 0.004475 | 0.014164 | −0.00423 |
| 250 | −0.0007 | 0.002315 | −0.000671 | 0.008757 | 0.014827 | −0.078908 | −0.042924 | 0.003979 | 0.015529 | −0.012376 | 0.008517 | −0.003993 | 0.011891 | 0.012697 |
| 251 | −0.03189 | 0.011901 | 0.003512 | 0.011792 | 0.020301 | −0.08813 | −0.055928 | −0.000815 | 0.002715 | −0.02797 | 0.000325 | 0.013558 | 0.014619 | 0.002503 |
| 252 | −0.054116 | −0.010997 | 0.011956 | 0.018949 | 0.00634 | −0.022912 | −0.045333 | −0.042728 | −0.04388 | −0.019084 | −0.03581 | 0.017996 | 0.006373 | −0.012618 |
| 253 | −0.029742 | −0.015867 | −0.003407 | 0.018163 | 0.023092 | 0.016715 | −0.021075 | −0.042675 | −0.064102 | −0.000046 | 0.001004 | 0.015868 | 0.019066 | 0.004026 |
| 254 | −0.004433 | 0.00826 | 0.030324 | 0.006277 | −0.011324 | −0.015516 | 0.003341 | −0.002117 | −0.025727 | −0.024677 | −0.009651 | −0.001536 | −0.001858 | 0.003088 |
| 255 | −0.002834 | 0.021959 | 0.031536 | 0.019298 | 0.016422 | −0.024954 | 0.004922 | 0.002629 | −0.012903 | −0.052366 | −0.022876 | −0.005995 | −0.004379 | −0.000531 |
| 256 | 0.022744 | 0.016679 | 0.034606 | 0.026207 | 0.030568 | −0.002821 | −0.0124 | 0.020865 | 0.005174 | −0.025432 | −0.074684 | −0.010726 | 0.000749 | −0.006202 |
| 257 | 0.00596 | −0.00051 | 0.020919 | 0.017234 | 0.016599 | 0.00557 | 0.007751 | 0.019421 | 0.035122 | 0.018925 | 0.009938 | 0.006801 | 0.001212 | 0.004484 |
| 258 | −0.001215 | −0.026421 | 0.013373 | 0.020176 | 0.016916 | 0.011727 | 0.000772 | −0.00188 | −0.000401 | 0.019131 | −0.000552 | 0.006489 | −0.022351 | −0.021182 |
| 259 | −0.022712 | 0.002056 | 0.000143 | −0.002464 | −0.002018 | −0.036386 | −0.028037 | −0.014582 | −0.038499 | −0.001064 | 0.008255 | 0.004645 | 0.007629 | 0.001029 |
| 260 | −0.024772 | −0.00111 | −0.001887 | 0.009984 | 0.004631 | −0.025535 | −0.016894 | −0.009748 | −0.01822 | −0.011593 | 0.004611 | 0.014311 | 0.006409 | −0.004951 |
| 261 | −0.027917 | −0.004706 | −0.007245 | −0.002271 | 0.002401 | −0.042212 | −0.017282 | −0.004302 | −0.008655 | 0.00871 | 0.014861 | 0.008356 | −0.008037 | −0.018381 |
| 262 | −0.026222 | −0.038939 | 0.006385 | −0.00087 | −0.012258 | 0.001706 | 0.00996 | −0.033452 | −0.013709 | 0.017931 | 0.005602 | −0.002298 | −0.026633 | −0.027791 |
| 263 | −0.043905 | −0.042182 | 0.004273 | 0.000674 | −0.007172 | 0.013973 | 0.009864 | −0.044106 | −0.033853 | 0.01057 | 0.002676 | 0.005016 | −0.020512 | −0.027358 |
| 264 | 0.004629 | 0.013986 | 0.00818 | −0.001746 | −0.004277 | −0.01796 | −0.009386 | 0.011825 | −0.029577 | 0.001337 | 0.007409 | 0.001632 | 0.009009 | 0.00382 |
| 265 | 0.018092 | 0.010995 | 0.016086 | −0.008221 | −0.023675 | 0.003262 | 0.011764 | 0.028316 | −0.028327 | 0.011756 | 0.019489 | 0.00293 | −0.006164 | −0.003693 |
| 266 | 0.013352 | 0.004903 | 0.014369 | −0.006836 | −0.011984 | 0.011497 | 0.020735 | 0.022495 | −0.014677 | −0.007822 | −0.003487 | 0.000992 | −0.022321 | −0.023032 |
| 267 | 0.014061 | 0.021682 | 0.017012 | 0.018192 | 0.005461 | 0.010529 | 0.012512 | 0.010529 | −0.007124 | 0.006314 | 0.020561 | 0.025845 | 0.040295 | 0.033991 |
| 268 | −0.007168 | 0.009074 | 0.019141 | 0.024216 | 0.005045 | 0.003954 | −0.003078 | 0.004727 | 0.006604 | 0.013673 | 0.033947 | 0.018633 | 0.022333 | 0.01713 |
| 269 | −0.003548 | 0.010283 | 0.011812 | 0.026186 | 0.021258 | 0.003504 | −0.002709 | 0.004585 | 0.009215 | 0.001491 | 0.030701 | 0.021954 | 0.027984 | 0.016162 |
| 270 | 0.002837 | 0.012478 | 0.020179 | 0.03705 | 0.024156 | −0.005663 | 0.007989 | 0.012898 | 0.017902 | 0.006325 | 0.036119 | 0.019841 | 0.020273 | 0.011 |
| 271 | 0.016585 | −0.011661 | −0.003832 | 0.013649 | 0.012648 | 0.007029 | 0.008158 | −0.005271 | −0.002377 | −0.005578 | −0.01713 | 0.005129 | 0.010604 | 0.01698 |
| 272 | 0.007707 | 0.025302 | 0.013809 | 0.003537 | 0.001566 | 0.002519 | 0.018882 | 0.021604 | 0.007129 | 0.007625 | 0.004434 | 0.029542 | 0.028084 | 0.02455 |
| 273 | 0.009594 | 0.000507 | 0.029454 | 0.019681 | 0.00642 | 0.009727 | 0.009888 | 0.008637 | 0.01492 | −0.00173 | 0.014196 | 0.027089 | 0.006104 | −0.001734 |
| 274 | 0.009764 | 0.004056 | 0.025922 | 0.019603 | 0.011266 | 0.008748 | 0.00789 | 0.00935 | 0.014745 | −0.003335 | 0.014773 | 0.026815 | 0.008449 | 0.001798 |
| 275 | 0.012776 | −0.008664 | 0.029758 | 0.008008 | 0.006346 | 0.008797 | 0.03432 | 0.00612 | 0.008128 | −0.011321 | 0.001089 | 0.010981 | −0.019927 | −0.023622 |
| 276 | −0.017368 | −0.090106 | −0.016925 | −0.001467 | −0.001653 | 0.012261 | 0.002478 | −0.05035 | −0.006968 | 0.02245 | −0.018532 | −0.005435 | −0.020218 | −0.018214 |
| 277 | 0.004682 | −0.01382 | −0.045048 | −0.011421 | −0.014067 | 0.014996 | 0.009647 | −0.011368 | 0.007541 | 0.005844 | 0.002929 | −0.002681 | 0.014387 | 0.023838 |
| 278 | 0.003126 | −0.011941 | −0.040867 | −0.012293 | −0.016867 | 0.012614 | 0.012778 | −0.00727 | 0.013239 | −0.008961 | 0.005288 | 0.00891 | 0.023068 | 0.023597 |
| 279 | −0.017792 | 0.004537 | 0.002129 | −0.065682 | −0.080991 | −0.006041 | 0.013617 | 0.009822 | −0.01951 | 0.0096 | 0.023594 | 0.027653 | −0.005919 | −0.014035 |
| 280 | −0.052967 | −0.005743 | −0.004158 | 0.014298 | 0.013341 | 0.02033 | −0.028438 | −0.074557 | −0.135226 | 0.013919 | 0.021047 | 0.003198 | 0.004587 | 0.007474 |
| 281 | 0.020414 | −0.000769 | 0.008889 | 0.033366 | 0.022752 | 0.009469 | −0.01493 | −0.008515 | 0.003605 | 0.025895 | −0.018928 | −0.064523 | −0.04134 | −0.0196 |
| 282 | 0.0064 | −0.002491 | 0.029757 | 0.040021 | 0.021727 | 0.010317 | −0.018153 | −0.015471 | −0.007084 | 0.010909 | −0.019792 | −0.048471 | −0.039969 | −0.020937 |
| 283 | −0.013871 | −0.030663 | 0.028646 | −0.000647 | −0.016075 | 0.003665 | 0.003608 | −0.021327 | −0.03289 | 0.015596 | 0.00422 | −0.016597 | −0.066359 | −0.075014 |
| 284 | 0.007088 | 0.005493 | 0.018072 | 0.016672 | 0.018129 | −0.004829 | 0.001732 | 0.023957 | 0.031087 | 0.013699 | 0.016781 | 0.017294 | 0.015255 | 0.011832 |
| 285 | 0.002537 | 0.009329 | 0.025241 | 0.017511 | 0.013414 | −0.002979 | −0.001956 | 0.02114 | 0.028669 | 0.006137 | 0.01702 | 0.018228 | 0.01668 | 0.014454 |
| 286 | 0.009862 | 0.018797 | 0.017985 | 0.022839 | 0.026384 | −0.005316 | −0.018692 | 0.022833 | 0.008785 | 0.006116 | −0.003825 | 0.021221 | 0.013154 | 0.020032 |
| 287 | 0.00611 | 0.017239 | 0.023118 | 0.025084 | 0.025167 | −0.007611 | −0.017123 | 0.017367 | −0.00154 | −0.004478 | −0.003599 | 0.029721 | 0.014026 | 0.01465 |
| 288 | 0.002983 | −0.028454 | −0.001628 | 0.020679 | 0.028389 | 0.005272 | 0.004831 | −0.008687 | −0.001178 | 0.016461 | 0.007726 | 0.005061 | −0.02139 | −0.031618 |
| 289 | −0.008425 | −0.03286 | 0.022286 | 0.013146 | −0.003497 | 0.007726 | 0.018656 | −0.013837 | −0.006722 | 0.014558 | 0.015796 | −0.000773 | −0.030241 | −0.030699 |
| 290 | 0.002853 | 0.010428 | −0.019567 | −0.004495 | 0.012981 | −0.011041 | 0.009689 | 0.003413 | −0.01056 | −0.005457 | 0.003246 | −0.001822 | −0.004845 | −0.00965 |
| 291 | 0.003785 | 0.010834 | −0.020293 | −0.004035 | 0.013856 | −0.011946 | 0.010649 | 0.003856 | −0.012717 | −0.002139 | 0.003996 | −0.002724 | −0.006602 | −0.010131 |
| 292 | −0.000902 | 0.017398 | −0.018493 | −0.013117 | 0.005808 | −0.01878 | 0.006123 | 0.000838 | −0.01977 | 0.003594 | 0.006465 | −0.005703 | −0.008707 | −0.00923 |
| 293 | −0.000797 | −0.038181 | 0.001001 | 0.003132 | −0.005308 | −0.007452 | 0.002508 | −0.015373 | 0.00613 | 0.007355 | 0.005116 | −0.01346 | −0.012797 | −0.002434 |
| 294 | −0.006313 | −0.00462 | 0.009461 | 0.00618 | −0.005683 | 0.013063 | 0.012728 | −0.002954 | −0.003016 | 0.007761 | 0.020572 | 0.004534 | −0.000774 | −0.004043 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 295 | 0.001281 | −0.007983 | 0.018267 | 0.002729 | −0.006789 | 0.004383 | 0.017877 | −0.006313 | 0.007573 | 0.007876 | 0.006926 | −0.000798 | −0.013818 | −0.003675 |
| 296 | 0.000466 | 0.014901 | 0.032753 | 0.027942 | 0.016492 | 0.00712 | 0.024921 | −0.00748 | −0.007741 | −0.00141 | 0.014584 | 0.004081 | −0.0199 | −0.019982 |
| 297 | 0.002617 | −0.009452 | 0.016635 | 0.005004 | −0.005776 | 0.005372 | 0.006518 | −0.009132 | 0.012728 | −0.000274 | −0.005143 | 0.003134 | −0.007966 | 0.001176 |
| 298 | 0.016376 | −0.007138 | −0.021391 | −0.013776 | 0.003332 | 0.022959 | 0.015121 | 0.01264 | 0.007815 | 0.000155 | −0.003322 | −0.000032 | −0.001016 | −0.004777 |
| 299 | 0.012115 | −0.017287 | −0.004764 | −0.005257 | −0.010987 | 0.002835 | 0.008794 | 0.006584 | 0.006051 | 0.000909 | 0.004926 | 0.011237 | 0.001044 | 0.006376 |
| 300 | 0.001017 | 0.01407 | −0.024324 | −0.029416 | −0.004973 | −0.023802 | 0.00106 | 0.019406 | −0.002611 | 0.033828 | 0.03505 | −0.005594 | −0.001013 | 0.00732 |
| 301 | −0.007991 | −0.014015 | 0.003638 | −0.011807 | −0.016456 | 0.009541 | 0.017329 | 0.004361 | 0.014507 | 0.004482 | 0.01685 | 0.004768 | 0.00119 | 0.001127 |
| 302 | 0.001756 | 0.008426 | 0.018011 | −0.004635 | −0.016659 | 0.006642 | 0.019009 | 0.010528 | 0.004818 | 0.019005 | 0.024592 | −0.002397 | −0.008965 | −0.002913 |
| 303 | 0.008971 | 0.014379 | −0.010437 | −0.007662 | −0.00814 | 0.009406 | 0.014785 | 0.009061 | −0.02706 | 0.00344 | 0.011816 | 0.021815 | 0.008448 | 0.014469 |
| 304 | 0.006724 | 0.010767 | −0.020984 | −0.011524 | −0.004665 | 0.000214 | 0.01098 | 0.017363 | −0.011923 | 0.009735 | 0.019138 | 0.025342 | 0.014026 | 0.00846 |
| 305 | 0.003398 | 0.00544 | 0.003725 | 0.004373 | −0.007653 | 0.02637 | 0.010744 | 0.011518 | 0.014455 | −0.002394 | 0.01715 | −0.005302 | 0.004906 | 0.01854 |
| 306 | 0.003539 | −0.018255 | −0.012177 | 0.013822 | 0.01529 | −0.018126 | 0.010691 | 0.003162 | −0.000575 | 0.023265 | 0.017377 | −0.020724 | −0.032427 | −0.024138 |
| 307 | −0.013854 | 0.011684 | −0.00993 | 0.004892 | 0.021738 | −0.006967 | −0.007834 | −0.020808 | −0.030013 | −0.013317 | −0.02291 | 0.026852 | 0.032605 | 0.022282 |
| 308 | −0.006852 | 0.031549 | −0.017149 | −0.016697 | −0.002516 | 0.01289 | −0.011579 | −0.01404 | −0.022813 | −0.012331 | −0.002237 | −0.011856 | 0.010099 | 0.022747 |
| 309 | −0.015743 | −0.004285 | 0.00195 | −0.002916 | −0.001535 | 0.00176 | 0.015172 | −0.00395 | −0.00942 | −0.005713 | 0.019219 | 0.013603 | 0.006602 | 0.00663 |
| 310 | −0.008272 | 0.003709 | 0.017235 | 0.005057 | 0.001016 | 0.005054 | 0.018373 | 0.00477 | −0.022826 | −0.023901 | 0.000581 | 0.01815 | 0.000781 | 0.007456 |
| 311 | −0.008801 | −0.009769 | −0.001592 | 0.004637 | 0.003097 | 0.005072 | −0.008911 | −0.010151 | −0.012037 | −0.0034 | 0.010582 | 0.01415 | 0.002987 | 0.000231 |
| 312 | −0.042806 | 0.037739 | 0.009654 | 0.012572 | 0.00859 | 0.005313 | −0.000578 | −0.033401 | −0.042372 | 0.0043 | −0.003788 | −0.009577 | 0.008026 | 0.005298 |
| 313 | −0.006485 | 0.012959 | −0.009925 | −0.000792 | 0.014968 | 0.013677 | 0.002452 | 0.011439 | 0.007708 | 0.00779 | 0.015041 | −0.00128 | 0.000368 | −0.002533 |
| 314 | −0.004378 | −0.001719 | −0.024019 | −0.000942 | 0.000301 | −0.009816 | −0.01747 | 0.004497 | 0.003784 | −0.006764 | −0.02051 | 0.008395 | 0.011941 | 0.005455 |
| 315 | −0.002132 | 0.007835 | −0.012332 | 0.00943 | 0.018749 | 0.001036 | −0.001218 | −0.005023 | −0.00858 | 0.001059 | 0.01038 | 0.000104 | 0.004739 | 0.017007 |
| 316 | 0.013203 | 0.021421 | −0.025307 | −0.009476 | 0.01493 | 0.017957 | 0.023684 | 0.014336 | −0.023288 | −0.011001 | 0.035424 | −0.005261 | 0.00379 | 0.005938 |
| 317 | −0.018852 | −0.005068 | 0.009592 | 0.00374 | 0.002043 | 0.00585 | 0.024321 | −0.000578 | 0.005043 | 0.009335 | 0.015923 | 0.00213 | −0.002312 | 0.001283 |
| 318 | −0.008098 | −0.009714 | −0.02406 | −0.002246 | 0.012645 | 0.013462 | 0.014818 | −0.009908 | 0.013631 | −0.006311 | 0.002115 | −0.001173 | 0.00853 | 0.006067 |
| 319 | −0.016212 | 0.002831 | −0.001967 | 0.010602 | 0.020524 | 0.005156 | 0.000996 | −0.002529 | −0.008994 | −0.003668 | 0.006709 | 0.011206 | 0.009064 | 0.0126 |
| 320 | −0.024996 | 0.013049 | 0.014688 | 0.007648 | −0.001794 | 0.010533 | −0.012222 | 0.009693 | 0.001627 | 0.025428 | 0.007958 | −0.010377 | −0.015367 | −0.015114 |
| 321 | 0.004388 | 0.002454 | −0.006494 | 0.018637 | 0.014354 | −0.004351 | −0.013867 | −0.002348 | 0.005804 | 0.010306 | 0.005748 | 0.00015 | 0.006276 | 0.007324 |
| 322 | −0.047173 | −0.004919 | −0.013631 | −0.044601 | −0.045176 | −0.016462 | 0.005608 | −0.000102 | −0.011859 | 0.005476 | 0.014454 | 0.006986 | 0.018699 | 0.016912 |
| 323 | −0.021687 | −0.002937 | −0.020894 | −0.002301 | 0.002718 | 0.007462 | −0.010366 | −0.000867 | 0.001291 | 0.010289 | 0.009953 | 0.0005 | 0.018311 | 0.020485 |
| 324 | 0.036739 | −0.010654 | 0.016375 | 0.012236 | −0.005218 | −0.001189 | 0.004347 | 0.010981 | −0.001588 | −0.000458 | 0.017506 | −0.00424 | −0.0171 | −0.026582 |
| 325 | −0.002388 | 0.002922 | 0.01162 | 0.010477 | 0.012673 | 0.008991 | 0.00944 | −0.005459 | −0.011362 | 0.005389 | 0.021969 | 0.006914 | −0.002377 | −0.007132 |
| 326 | 0.032066 | −0.009138 | 0.009539 | 0.003076 | 0.007347 | −0.00428 | −0.002576 | 0.002568 | −0.020943 | 0.008767 | −0.004466 | 0.012598 | −0.008513 | −0.023269 |
| 327 | −0.01423 | 0.005683 | 0.00183 | −0.001514 | 0.000733 | 0.011075 | 0.00956 | −0.008651 | −0.017684 | 0.015522 | 0.018847 | −0.002893 | −0.006196 | −0.001389 |
| 328 | 0.015015 | −0.000784 | −0.009959 | 0.015303 | 0.014762 | 0.006067 | −0.014827 | 0.025042 | 0.028646 | 0.015799 | 0.002934 | −0.009412 | 0.002631 | −0.005181 |
| 329 | −0.007152 | 0.010025 | 0.011065 | 0.000605 | −0.002762 | −0.00028 | 0.000847 | 0.004208 | −0.004219 | 0.004717 | 0.007253 | −0.002079 | −0.006209 | −0.002024 |
| 330 | 0.004347 | −0.015766 | −0.005064 | 0.001445 | −0.010558 | −0.004742 | −0.018558 | 0.009797 | 0.008793 | 0.023738 | −0.02357 | −0.01619 | −0.004548 | 0.00039 |
| 331 | −0.002509 | 0.0032 | −0.005155 | −0.000406 | 0.001516 | −0.000183 | −0.001736 | −0.008221 | −0.029195 | 0.009522 | 0.011924 | 0.003721 | −0.000664 | −0.000203 |
| 332 | 0.017804 | −0.018838 | −0.014767 | −0.002943 | 0.006443 | 0.004474 | −0.027178 | 0.010298 | 0.003245 | 0.008818 | −0.019657 | −0.004998 | −0.004894 | −0.012659 |
| 333 | −0.002455 | −0.003745 | 0.003032 | 0.000619 | 0.00672 | −0.000674 | 0.005574 | −0.001642 | 0.0027 | 0.003789 | 0.010517 | 0.003618 | 0.004631 | −0.002759 |
| 334 | −0.023768 | 0.035391 | 0.028033 | 0.005556 | 0.009259 | −0.007123 | −0.007408 | −0.011579 | 0.012723 | −0.002057 | −0.016639 | −0.030107 | −0.014677 | −0.006735 |
| 335 | −0.014519 | −0.001535 | 0.00002 | 0.002508 | 0.012524 | 0.005809 | −0.013818 | 0.002054 | −0.018631 | −0.000106 | 0.008455 | 0.014186 | 0.01434 | −0.002619 |
| 336 | 0.010134 | −0.016627 | −0.028472 | −0.023812 | −0.00816 | 0.002377 | 0.012117 | 0.000208 | −0.007035 | 0.010534 | 0.012431 | 0.003086 | −0.005039 | −0.002439 |
| 337 | 0.002081 | 0.02285 | −0.003035 | 0.011427 | 0.025176 | −0.01273 | 0.016699 | 0.028851 | 0.006357 | 0.002109 | 0.002357 | −0.004259 | 0.005911 | 0.012401 |
| 338 | 0.001358 | −0.026261 | 0.002218 | 0.001769 | 0.001795 | 0.010709 | −0.006906 | −0.018718 | 0.002027 | −0.021724 | −0.021401 | 0.007654 | −0.010592 | −0.016535 |
| 339 | −0.024915 | 0.001842 | −0.01353 | −0.004991 | −0.006379 | −0.017564 | −0.00793 | −0.003286 | 0.007521 | 0.0252281 | 0.00584 | 0.007011 | 0.016506 | 0.014367 |
| 340 | 0.039099 | 0.022138 | −0.029805 | 0.011673 | 0.031705 | 0.028069 | 0.008161 | 0.005765 | −0.022645 | −0.020434 | −0.027967 | −0.0121621 | −0.011408 | 0.000643 |

APPENDIX B3-continued

PCA Transformation
Matrix (340 × 340 Early/Late)

| | IP | IQ | IR | IS | IT | IU | IV | IW | IX | IY | IZ | JA | JB | JC |
|---|---|---|---|---|---|---|---|---|---|---|---|---|---|---|
| 1 | −0.041388 | −0.027931 | −0.028489 | −0.029962 | −0.036733 | 0.03974 | 0.063666 | 0.065577 | 0.005403 | −0.011551 | −0.018524 | −0.003096 | −0.028831 | −0.007226 |
| 2 | 0.028419 | 0.021177 | 0.02151 | 0.032442 | 0.050263 | −0.000348 | 0.010936 | 0.014471 | −0.02288 | 0.042198 | −0.01894 | −0.0155 | −0.004416 | 0.00456 |
| 3 | 0.004524 | −0.026217 | −0.038209 | 0.00028 | −0.057596 | 0.039585 | 0.037244 | 0.085568 | −0.07125 | 0.016138 | −0.014125 | −0.036447 | −0.006666 | 0.001841 |
| 4 | 0.018843 | −0.01401 | 0.008219 | 0.063363 | 0.085106 | 0.052298 | 0.00789 | 0.064575 | −0.030436 | 0.040129 | 0.047704 | 0.022681 | −0.037267 | −0.006626 |
| 5 | −0.04662 | −0.022799 | 0.037353 | 0.038486 | −0.005937 | −0.010976 | 0.02908 | −0.003533 | −0.049015 | −0.016644 | −0.044154 | −0.010067 | 0.012317 | 0.000675 |
| 6 | 0.009889 | −0.027448 | −0.00647 | 0.080342 | 0.085276 | −0.047854 | −0.042342 | −0.061588 | 0.011267 | 0.1016 | −0.010875 | 0.059802 | 0.077557 | 0.100069 |
| 7 | 0.044829 | 0.031234 | 0.012779 | −0.022588 | 0.038746 | −0.00107 | −0.038893 | −0.092497 | −0.054985 | −0.067605 | 0.003147 | −0.029907 | −0.067836 | −0.039918 |
| 8 | −0.004672 | −0.013494 | −0.012283 | −0.075451 | −0.046609 | 0.009789 | 0.035105 | 0.04643 | 0.028061 | 0.02288 | −0.006876 | −0.050861 | −0.068028 | −0.023234 |
| 9 | 0.030231 | −0.039623 | −0.009352 | −0.002282 | −0.021 | 0.001388 | 0.001625 | 0.031158 | 0.011107 | 0.049529 | −0.004923 | −0.047935 | −0.032454 | −0.0165 |
| 10 | −0.047751 | −0.045792 | −0.038763 | −0.012947 | 0.087459 | −0.032238 | −0.031115 | 0.07137 | 0.024326 | −0.002465 | −0.047455 | −0.037987 | 0.003965 | 0.040267 |
| 11 | 0.037611 | 0.008123 | 0.048746 | −0.030575 | −0.012909 | −0.018211 | −0.018393 | −0.05607 | 0.040803 | 0.023724 | 0.017516 | 0.031016 | 0.014066 | −0.005607 |
| 12 | 0.065771 | −0.009277 | 0.008632 | 0.02256 | 0.001644 | −0.004335 | −0.066119 | −0.152757 | −0.011361 | −0.006406 | 0.049711 | 0.033294 | 0.018904 | −0.00385 |
| 13 | 0.025273 | −0.008342 | −0.002095 | −0.005214 | 0.070065 | 0.036043 | −0.024412 | 0.030416 | 0.015328 | 0.05063 | 0.039001 | −0.017312 | −0.02706 | −0.029049 |
| 14 | 0.056009 | 0.071166 | 0.064168 | 0.029772 | −0.018687 | 0.023619 | 0.071208 | 0.050842 | 0.027986 | −0.069963 | 0.027018 | 0.043079 | 0.02467 | −0.022194 |
| 15 | 0.008336 | 0.040983 | 0.01758 | −0.030266 | −0.005508 | 0.051473 | 0.024119 | −0.008537 | 0.014983 | −0.031666 | 0.006448 | −0.023291 | −0.058282 | −0.025154 |
| 16 | −0.029711 | 0.055366 | 0.02935 | −0.031401 | −0.030382 | −0.029335 | 0.02104 | 0.046792 | 0.06195 | 0.046434 | −0.030789 | −0.013205 | −0.016626 | −0.006887 |
| 17 | 0.038498 | 0.022409 | 0.00039 | −0.030548 | 0.042627 | 0.009946 | 0.030672 | −0.055147 | −0.023364 | −0.038177 | 0.027223 | 0.036119 | 0.00002 | 0.038893 |
| 18 | −0.033217 | −0.063987 | −0.046139 | −0.009077 | −0.000352 | 0.000458 | −0.02822 | −0.058341 | −0.054605 | −0.03904 | 0.016891 | −0.031961 | −0.014787 | 0.019866 |
| 19 | 0.034191 | 0.001285 | 0.019286 | 0.031514 | 0.082315 | 0.022048 | 0.050562 | 0.020292 | −0.008514 | −0.006159 | 0.050054 | 0.036982 | 0.016223 | −0.008075 |
| 20 | 0.031568 | 0.005878 | 0.057046 | 0.050769 | −0.049597 | −0.01113 | 0.004573 | −0.02864 | −0.052414 | −0.053762 | 0.033623 | 0.056541 | 0.098338 | 0.102771 |
| 21 | 0.019124 | 0.008678 | 0.030125 | 0.000529 | −0.060712 | 0.013374 | −0.001572 | 0.052783 | 0.029189 | −0.014677 | 0.035057 | 0.022806 | 0.049959 | −0.000012 |
| 22 | −0.022309 | 0.012529 | −0.005958 | 0.009015 | 0.000112 | −0.063988 | −0.028369 | −0.00005 | 0.044753 | 0.031411 | −0.026402 | −0.000558 | −0.001781 | −0.002203 |
| 23 | −0.028315 | −0.075667 | −0.085495 | −0.092093 | −0.075155 | −0.053988 | −0.089159 | −0.106932 | −0.048924 | −0.04234 | −0.030901 | −0.075101 | −0.05408 | −0.019414 |
| 24 | −0.065948 | −0.073332 | −0.053219 | −0.066761 | −0.021616 | −0.001043 | −0.009395 | 0.023281 | 0.021808 | 0.058455 | −0.046717 | −0.075959 | −0.049657 | −0.044054 |
| 25 | −0.118047 | −0.028371 | 0.041211 | 0.01071 | −0.089435 | −0.052258 | −0.015058 | −0.058174 | 0.010251 | 0.047876 | −0.046201 | 0.007428 | 0.056202 | 0.022396 |
| 26 | 0.004634 | −0.042549 | −0.091731 | 0.019009 | 0.108957 | −0.038403 | −0.085613 | 0.020625 | 0.015765 | 0.039594 | −0.02253 | −0.001737 | −0.055299 | 0.014624 |
| 27 | 0.009979 | 0.039287 | 0.017152 | −0.044828 | −0.000083 | 0.026694 | 0.038684 | −0.053278 | 0.00842 | 0.010644 | 0.030785 | −0.028844 | 0.010819 | −0.057719 |
| 28 | −0.029086 | 0.025727 | 0.04071 | −0.014509 | −0.021078 | −0.010905 | 0.007251 | −0.062581 | −0.082435 | −0.000882 | 0.038656 | 0.015343 | 0.05344 | −0.026711 |
| 29 | −0.006078 | −0.021083 | −0.022338 | −0.005413 | −0.008256 | −0.001844 | −0.01832 | −0.011069 | 0.002455 | −0.000237 | −0.002799 | 0.004905 | 0.010468 | 0.001363 |
| 30 | −0.164843 | −0.077188 | −0.072809 | −0.033436 | −0.006745 | −0.074007 | −0.048036 | −0.043283 | 0.045632 | 0.021276 | −0.144036 | −0.07198 | −0.030504 | 0.022442 |
| 31 | −0.007603 | −0.028466 | −0.033572 | −0.043933 | 0.043953 | −0.013473 | −0.004266 | 0.058008 | −0.005501 | −0.043484 | −0.059397 | −0.059898 | −0.057076 | −0.051976 |
| 32 | 0.077806 | 0.029479 | 0.060802 | 0.049079 | 0.050203 | 0.029304 | 0.018864 | −0.052188 | 0.016103 | 0.019626 | 0.133693 | 0.103533 | 0.079374 | 0.009781 |
| 33 | 0.00002 | 0.006315 | −0.006913 | 0.029544 | 0.051496 | −0.010792 | −0.018825 | −0.000409 | 0.069423 | 0.072131 | 0.00369 | −0.007959 | 0.042343 | 0.095675 |
| 34 | 0.048518 | 0.053039 | 0.109618 | 0.065358 | 0.000068 | −0.032629 | −0.012077 | −0.025991 | 0.049462 | 0.034297 | 0.020143 | 0.049739 | 0.063552 | 0.036094 |
| 35 | −0.045928 | −0.064994 | −0.068477 | 0.1314 | 0.030046 | 0.004809 | 0.025378 | 0.040655 | 0.029522 | −0.036517 | −0.050122 | 0.069786 | 0.007888 | 0.041232 |
| 36 | 0.105433 | 0.003721 | 0.0395 | −0.036747 | −0.01662 | 0.030787 | −0.001117 | −0.073175 | −0.044379 | 0.02263 | 0.036698 | −0.008468 | −0.018353 | −0.019169 |
| 37 | −0.008296 | 0.01116 | 0.035 | 0.099719 | −0.033273 | −0.003392 | 0.01622 | 0.018249 | 0.067448 | −0.016272 | 0.02417 | 0.090797 | 0.032281 | −0.014506 |
| 38 | 0.004765 | −0.002333 | 0.036911 | 0.097706 | 0.04288 | 0.021655 | 0.023733 | 0.095451 | −0.029228 | −0.054884 | 0.008572 | 0.095955 | 0.056254 | −0.004717 |
| 39 | −0.006826 | −0.034235 | −0.02797 | −0.018349 | 0.020502 | −0.075295 | −0.008224 | 0.053227 | −0.021311 | −0.059551 | −0.008872 | −0.09539 | −0.063413 | −0.009984 |
| 40 | 0.019524 | −0.020468 | −0.001509 | −0.008288 | 0.005556 | −0.010408 | 0.000635 | 0.021228 | −0.001061 | 0.008801 | 0.006248 | −0.014703 | −0.010453 | −0.001267 |
| 41 | −0.023512 | 0.058018 | −0.010444 | −0.053593 | −0.021398 | 0.127429 | 0.063328 | −0.057248 | 0.015347 | −0.004292 | 0.039239 | −0.019569 | −0.039648 | 0.010095 |
| 42 | 0.000262 | 0.00587 | 0.020051 | 0.053655 | 0.042645 | −0.018156 | 0.019443 | 0.0965 | −0.005345 | −0.036127 | −0.018537 | −0.043703 | −0.010914 | −0.026115 |
| 43 | 0.007291 | 0.065857 | 0.05022 | −0.012286 | 0.009795 | −0.003181 | 0.036754 | 0.063157 | −0.015614 | −0.045105 | −0.026117 | −0.029688 | 0.025348 | −0.040755 |
| 44 | 0.053142 | 0.008209 | −0.012894 | 0.002672 | 0.013288 | −0.079776 | −0.04716 | −0.012634 | 0.011199 | −0.026746 | −0.006277 | −0.0233 | −0.036392 | 0.011058 |
| 45 | −0.128466 | −0.029138 | −0.018194 | −0.020106 | −0.054923 | 0.057602 | 0.113973 | 0.011348 | −0.067624 | 0.003235 | −0.074303 | −0.02903 | −0.016801 | −0.039289 |
| 46 | −0.008653 | −0.066988 | −0.021486 | −0.066616 | 0.052442 | 0.017239 | −0.011488 | 0.011904 | −0.008776 | 0.015441 | 0.028421 | −0.001154 | −0.028558 | −0.038896 |
| 47 | −0.058246 | 0.023916 | 0.042895 | 0.057907 | 0.014025 | −0.007169 | 0.011387 | −0.064234 | 0.03847 | 0.0051 | −0.022246 | 0.024936 | 0.048353 | 0.049307 |
| 48 | −0.058173 | 0.057763 | 0.003301 | −0.124815 | −0.030386 | 0.011055 | −0.011557 | −0.118651 | 0.024325 | 0.002747 | −0.025529 | 0.009959 | −0.002463 | −0.021074 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 49 | 0.037847 | 0.019768 | 0.021763 | 0.052294 | −0.019547 | 0.003652 | −0.027026 | −0.024873 | 0.003341 | −0.013758 | 0.036934 | 0.125074 | 0.031319 | 0.031124 |
| 50 | 0.020802 | 0.041837 | 0.043728 | 0.036638 | 0.024633 | 0.08119 | 0.033687 | 0.041076 | −0.091885 | −0.069951 | 0.018469 | 0.051528 | 0.047672 | −0.002192 |
| 51 | −0.023296 | −0.016804 | 0.009517 | −0.013391 | 0.053093 | 0.006227 | 0.010159 | −0.024327 | −0.00501 | 0.062323 | 0.002281 | −0.010048 | −0.013653 | −0.011828 |
| 52 | 0.040397 | −0.010169 | −0.01737 | −0.0422 | −0.000953 | 0.017716 | 0.01415 | 0.010909 | 0.04214 | −0.03574 | −0.010336 | −0.046553 | −0.027927 | 0.019333 |
| 53 | −0.054671 | −0.01457 | 0.006744 | −0.008776 | 0.034699 | −0.025311 | 0.015595 | −0.026431 | 0.021542 | 0.006443 | −0.034273 | −0.049009 | −0.026701 | 0.005624 |
| 54 | 0.003083 | 0.032884 | 0.053671 | 0.053781 | −0.019797 | 0.035014 | −0.008069 | −0.024475 | −0.009736 | 0.011831 | 0.048235 | 0.119088 | 0.089811 | 0.035994 |
| 55 | −0.08683 | 0.056038 | 0.064773 | −0.050375 | 0.007601 | −0.011448 | 0.014021 | −0.058454 | −0.094109 | −0.090507 | 0.030534 | 0.075646 | 0.016275 | −0.010383 |
| 56 | −4.044615 | −4.00488 | −0.091079 | −4.000178 | 0.024072 | 0.037546 | −4.039891 | −4.062339 | −4.021915 | −0.027558 | 0.036175 | 0.126464 | 0.050859 | −4.009204 |
| 57 | −0.088315 | 0.024595 | 0.040498 | −0.062753 | −0.041259 | −0.00773 | −0.038529 | −0.147091 | 0.011398 | 0.009105 | 0.011053 | −0.024673 | −0.087874 | −0.045305 |
| 58 | −0.08918 | −0.125459 | −0.095404 | −0.092831 | −0.031604 | −0.031868 | 0.003751 | −0.003985 | −0.010562 | −0.031516 | −0.050685 | −0.082767 | −0.137407 | −0.008751 |
| 59 | 0.072421 | −0.04642 | −0.076678 | −0.024324 | −0.036916 | −0.017453 | −0.042246 | 0.039821 | 0.052949 | 0.032755 | 0.004407 | 0.009242 | 0.05098 | 0.02779 |
| 60 | −0.014754 | −0.014344 | 0.001232 | 0.020203 | −0.006035 | −0.007855 | −0.013592 | −0.025145 | 0.001487 | −0.005448 | −0.002765 | 0.021804 | 0.012025 | −0.011748 |
| 61 | −0.008882 | −0.0183 | −0.008943 | 0.000434 | 0.015085 | −0.003321 | −0.00235 | 0.029495 | 0.00046 | −0.004348 | −0.005831 | 0.001604 | −0.007671 | −0.008662 |
| 62 | 0.028595 | 0.00102 | −0.016322 | 0.016831 | 0.014871 | −0.000629 | −0.029389 | −0.039331 | 0.017584 | 0.011593 | 0.012065 | 0.005432 | −0.006286 | 0.004938 |
| 63 | −0.00226 | −0.002883 | −0.012216 | −0.006459 | 0.015132 | −0.009522 | −0.021458 | −0.01851 | 0.00321 | 0.003244 | 0.01045 | 0.001795 | −0.013579 | 0.000701 |
| 64 | 0.00225 | 0.008732 | 0.010722 | −0.006476 | −0.029065 | 0.00334 | −0.000584 | −0.02918 | −0.000197 | −0.020704 | 0.001737 | −0.013433 | −0.016377 | 0.000406 |
| 65 | −0.004121 | −0.030387 | −0.042225 | −0.025875 | 0.002661 | −0.030342 | −0.068642 | −0.046962 | −0.017156 | 0.00064 | −0.012387 | −0.00489 | −0.012797 | 0.006247 |
| 66 | −0.016793 | −0.057941 | −0.054008 | −0.027144 | 0.01872 | −0.030714 | −0.048643 | −0.027074 | −0.001542 | −0.003578 | −0.001449 | −0.011593 | −0.035231 | 0.000144 |
| 67 | −0.042253 | −0.02704 | −0.007671 | 0.015351 | −0.001829 | −0.045344 | −0.026563 | −0.002246 | 0.014437 | 0.011323 | −0.037595 | −0.006155 | 0.005845 | 0.025774 |
| 68 | −0.031943 | −0.031435 | −0.045602 | −0.023915 | 0.007613 | −0.027712 | −0.035222 | −0.025213 | 0.004603 | −0.002939 | −0.029332 | −0.047663 | −0.058792 | 0.006092 |
| 69 | −0.035957 | −0.005052 | −0.022987 | −0.018469 | −0.018199 | 0.002772 | 0.019324 | −0.010599 | −0.005589 | −0.001864 | −0.031486 | −0.019886 | −0.021645 | 0.006384 |
| 70 | 0.007273 | −0.016274 | −0.023122 | 0.003104 | −0.018179 | 0.008152 | −0.001494 | 0.002519 | 0.008864 | 0.00383 | 0.003726 | 0.022647 | −0.005171 | 0.000623 |
| 71 | −0.010219 | −0.012354 | −0.02197 | −0.013183 | −0.016101 | 0.013061 | 0.002093 | −0.007711 | −0.008123 | 0.015718 | −0.010717 | −0.011484 | −0.01561 | −0.007564 |
| 72 | −0.004005 | 0.002196 | −0.006279 | −0.014465 | −0.036701 | 0.017973 | 0.008059 | −0.028758 | −0.020232 | 0.003952 | −0.006884 | −0.010276 | −0.016805 | −0.010341 |
| 73 | 0.03802 | 0.002455 | −0.017591 | −0.002635 | −0.008982 | 0.022632 | 0.012339 | 0.019555 | 0.020085 | −0.011466 | 0.009201 | 0.016117 | −0.009505 | 0.014912 |
| 74 | 0.020042 | −0.00628 | −0.015251 | 0.001011 | 0.01685 | 0.014619 | −0.017139 | 0.002279 | −0.003605 | −0.00577 | 0.011694 | 0.008682 | −0.007105 | −0.014679 |
| 75 | −0.008958 | −0.008823 | −0.016753 | −0.012237 | −0.000894 | 0.000639 | −0.009555 | −0.016318 | 0.00463 | −0.000362 | 0.001508 | 0.012095 | −0.00494 | −0.000417 |
| 76 | −0.035988 | −0.008204 | −0.001386 | −0.007204 | −0.004679 | 0.007361 | 0.000041 | −0.015759 | −0.01693 | 0.00706 | −0.005993 | 0.012839 | −0.001316 | −0.011054 |
| 77 | −0.009744 | −0.008042 | −0.019953 | −0.012885 | −0.006152 | 0.00171 | −0.005511 | −0.013849 | −0.001462 | −0.001334 | −0.001163 | 0.010983 | −0.004864 | −0.003014 |
| 78 | 0.003668 | −0.003741 | −0.017927 | −0.01722 | −0.012248 | 0.001468 | −0.005242 | −0.009013 | 0.012555 | 0.000961 | 0.003073 | 0.014648 | 0.000363 | −0.002101 |
| 79 | −0.006773 | −0.011491 | −0.005825 | −0.000153 | 0.001459 | 0.004294 | 0.001854 | −0.006591 | 0.010398 | −0.005057 | −0.002079 | 0.002681 | −0.01659 | 0.005311 |
| 80 | 0.006184 | 0.009553 | 0.011876 | −0.001922 | −0.009115 | 0.035608 | 0.007626 | −0.002805 | −0.006342 | −0.00204 | 0.020095 | 0.020669 | −0.003722 | −0.000644 |
| 81 | 0.019616 | 0.012777 | 0.009366 | −0.000194 | −0.018526 | −0.030314 | −0.008647 | 0.004059 | −0.022566 | −0.01627 | 0.012985 | 0.008826 | 0.020862 | −0.00054 |
| 82 | −0.023338 | −0.010607 | −0.002138 | −0.003814 | −0.005712 | 0.007967 | 0.013529 | 0.000729 | −0.005523 | −0.017707 | −0.00861 | −0.004399 | −0.017246 | −0.008925 |
| 83 | −0.018951 | −0.001936 | −0.000812 | −0.011978 | −0.004341 | 0.004494 | 0.010385 | 0.009283 | −0.000724 | −0.003037 | −0.007757 | −0.01401 | −0.013325 | −0.003077 |
| 84 | 0.007304 | −0.001681 | −0.003203 | −0.006917 | −0.008034 | 0.007826 | 0.007111 | 0.013795 | −0.009982 | 0.002458 | 0.007368 | 0.004876 | 0.008955 | 0.001675 |
| 85 | −0.001208 | 0.01727 | 0.029534 | 0.014772 | −0.011423 | −0.000819 | 0.010495 | 0.017219 | −0.00165 | 0.000732 | 0.007359 | 0.011687 | −0.004614 | 0.000884 |
| 86 | −0.014395 | −0.001669 | −0.009339 | −0.016169 | −0.011732 | −0.002048 | 0.007164 | 0.001596 | −0.001864 | 0.018254 | −0.021102 | −0.037595 | −0.020489 | −0.003424 |
| 87 | −0.0153 | −0.004579 | 0.005882 | −0.004262 | −0.00718 | 0.003489 | 0.008491 | 0.024381 | 0.011724 | 0.018204 | −0.015385 | −0.01329 | −0.007855 | 0.001059 |
| 88 | −0.011974 | −0.00194 | 0.002141 | −0.003758 | −0.011947 | 0.000176 | 0.013262 | 0.01145 | 0.000557 | −0.014784 | −0.004139 | 0.003919 | 0.004738 | 0.001552 |
| 89 | −0.006041 | −0.001724 | −0.004838 | −0.009993 | −0.008522 | 0.005575 | 0.00765 | 0.009583 | 0.007709 | 0.003136 | −0.00485 | −0.00405 | 0.001029 | 0.003649 |
| 90 | −0.007783 | −0.004328 | −0.012975 | −0.009743 | 0.002556 | 0.00787 | −0.002385 | −0.001031 | 0.000169 | 0.008093 | −0.007618 | −0.004383 | −0.006664 | 0.006531 |
| 91 | 0.002134 | −0.000838 | −0.013901 | −0.0256 | −0.018272 | 0.004789 | −0.001064 | −0.014965 | −0.00682 | −0.004606 | −0.003934 | −0.013888 | −0.015805 | −0.001877 |
| 92 | 0.03044 | −4.004559 | −4.011766 | −4.003677 | −4.026639 | −4.020163 | −4.001813 | 0.032912 | 0.013063 | 0.001931 | −0.000758 | −4.007083 | 0.006721 | 0.001655 |
| 93 | −0.008095 | 0.00805 | −0.00524 | −0.010466 | −0.017195 | 0.010082 | −0.009436 | −0.031729 | 0.002871 | 0.015066 | 0.007023 | 0.012469 | −0.008799 | 0.008205 |
| 94 | 0.004671 | −0.000236 | −0.016344 | 0.016326 | −0.01232 | 0.005473 | 0.007179 | 0.019868 | 0.007204 | −0.016158 | −0.010145 | −0.006361 | −0.022418 | −0.008702 |
| 95 | −0.017562 | −0.010692 | −0.011717 | 0.016962 | 0.01552 | 0.00653 | 0.030676 | 0.020224 | 0.000617 | 0.001487 | −0.008409 | −0.014534 | −0.021741 | 0.011813 |
| 96 | −0.002571 | −0.023685 | −0.00672 | 0.001739 | −0.017966 | 0.016371 | 0.00657 | −0.023216 | 0.011077 | 0.007436 | 0.003729 | 0.020389 | −0.003308 | −0.01571 |
| 97 | 0.01341 | 0.014782 | 0.019443 | 0.00777 | −0.017605 | 0.00328 | −0.007744 | −0.024361 | −0.017825 | −0.037896 | 0.016636 | 0.018696 | 0.006926 | 0.010129 |
| 98 | 0.007954 | −0.002983 | 0.007143 | −0.002021 | −0.010565 | 0.005354 | 0.00112 | −0.001883 | −0.01168 | −0.007629 | −0.003756 | −0.0219 | −0.012122 | −0.006225 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 99 | 0.005685 | −0.005309 | −0.002318 | 0.006845 | 0.000694 | 0.005181 | 0.002211 | −0.004323 | −0.03209 | −0.028865 | 0.002237 | 0.009062 | 0.002557 | 0.005037 |
| 100 | 0.009877 | −0.003457 | 0.004529 | −0.014637 | 0.005527 | 0.005349 | 0.003519 | 0.0039 | 0.005054 | 0.001693 | −0.006569 | −0.030974 | −0.027824 | −0.009305 |
| 101 | 0.016181 | 0.00249 | 0.013579 | 0.016357 | −0.009398 | 0.002704 | −0.004636 | −0.004682 | −0.011654 | −0.010072 | 0.011176 | 0.006663 | −0.005395 | 0.00277 |
| 102 | 0.034515 | 0.019383 | 0.010753 | 0.007758 | 0.004923 | −0.007217 | 0.002026 | 0.008364 | 0.016272 | 0.006572 | 0.00412 | 0.013516 | 0.013416 | 0.00594 |
| 103 | 0.034965 | 0.011996 | 0.006477 | 0.014476 | 0.024435 | −0.042408 | −0.008756 | 0.030038 | 0.021091 | −0.018536 | 0.000597 | −0.0156881 | −0.016278 | 0.004776 |
| 104 | 0.023718 | −0.005307 | −0.017503 | −0.006808 | 0.019065 | −0.001078 | −0.023614 | −0.025567 | −0.012267 | −0.013461 | 0.007923 | 0.033551 | 0.012335 | 0.010128 |
| 105 | 0.028807 | −0.0221 | −0.022977 | −0.028663 | −0.018826 | 0.016764 | −0.015721 | 0.011123 | 0.016497 | 0.016546 | 0.018148 | 0.003445 | −0.005386 | −0.017536 |
| 106 | −0.00286 | 0.022633 | 0.007934 | −0.017331 | 0.00141 | −0.005545 | 0.014934 | −0.000782 | 0.009722 | −0.014056 | −0.00909 | −0.035507 | −0.007405 | −0.014515 |
| 107 | 0.004918 | 0.016524 | 0.02201 | −0.001608 | −0.012313 | 0.0104851 | 0.017235 | −0.0099 | −0.024987 | −0.019377 | 0.028018 | 0.037377 | 0.024083 | −0.007527 |
| 108 | 0.017064 | 0.008997 | 0.024875 | 0.005213 | −0.019533 | 0.021619 | 0.015962 | 0.012903 | −0.009342 | 0.000627 | 0.020302 | 0.014166 | 0.007119 | −0.015379 |
| 109 | −0.004648 | −0.010078 | −0.048135 | −0.007706 | 0.043837 | 0.021858 | 0.023812 | 0.0148 | 0.02036 | 0.019978 | −0.01133 | −0.015263 | −0.044647 | −0.005806 |
| 110 | −0.002897 | −0.00302 | 0.022555 | 0.00065 | 0.025471 | 0.008983 | 0.02761 | −0.001756 | −0.050213 | −0.030422 | 0.011656 | −0.009032 | −0.017445 | −0.002543 |
| 111 | 0.01696 | −0.007609 | 0.015372 | 0.00434 | −0.004256 | 0.009856 | 0.025767 | 0.03359 | −0.010128 | −0.023616 | 0.014404 | −0.005953 | 0.003307 | −0.014047 |
| 112 | 0.003871 | 0.012959 | 0.00114 | −0.005667 | −0.026339 | 0.017077 | 0.025411 | 0.016669 | −0.019927 | 0.021752 | 0.004213 | −0.009162 | 0.016098 | −0.003354 |
| 113 | 0.017909 | 0.004018 | −0.022092 | −0.004447 | 0.012082 | 0.028174 | 0.023853 | 0.012563 | 0.000626 | −0.03029 | 0.006606 | −0.013324 | −0.032778 | −0.030144 |
| 114 | 0.021781 | 0.011404 | −0.016681 | −0.012036 | 0.044215 | 0.02732 | 0.011274 | 0.021912 | 0.007974 | 0.019694 | −0.008255 | −0.01108 | −0.03 | −0.009837 |
| 115 | 0.036633 | −0.023582 | −0.001134 | 0.02104 | 0.006221 | −0.01377 | −0.016908 | −0.015326 | −0.034185 | −0.006651 | 0.030741 | 0.012891 | −0.001404 | −0.002634 |
| 116 | −0.048246 | −0.01326 | −0.0247 | −0.015307 | −0.010148 | 0.001847 | 0.000289 | 0.017369 | 0.010846 | 0.002407 | −0.021957 | −0.019615 | −0.022349 | 0.016711 |
| 117 | −0.003188 | −0.050725 | −0.050907 | −0.034907 | 0.018248 | −0.002593 | −0.010412 | 0.027672 | −0.014072 | 0.008607 | −0.007812 | −0.028668 | −0.022631 | −0.010287 |
| 118 | 0.040323 | −0.018396 | −0.007324 | 0.043034 | 0.001905 | 0.020029 | −0.02126 | 0.00054 | 0.01294 | 0.021809 | 0.025081 | 0.055576 | 0.018518 | 0.024892 |
| 119 | −0.012763 | 0.005906 | −0.002805 | −0.01817 | −0.012128 | 0.012129 | 0.012478 | −0.017921 | −0.012612 | 0.006867 | −0.002965 | −0.012447 | −0.016232 | −0.000915 |
| 120 | 0.033596 | −0.004259 | −0.013117 | −0.028966 | 0.000951 | −0.004827 | −0.012386 | 0.010926 | 0.018238 | −0.000485 | 0.007903 | −0.018042 | −0.008814 | 0.008485 |
| 121 | −0.003154 | −0.011085 | −0.054123 | −0.02249 | 0.019561 | 0.011999 | −0.012173 | 0.005397 | 0.001976 | −0.019473 | −0.021334 | −0.037532 | −0.033279 | 0.007069 |
| 122 | 0.008795 | −0.005617 | 0.004227 | −0.002641 | −0.008287 | 0.017188 | 0.027116 | 0.035767 | −0.001871 | 0.005932 | 0.019651 | 0.005956 | 0.005169 | −0.004551 |
| 123 | 0.007547 | −0.010083 | −0.003208 | −0.009979 | 0.002865 | 0.009701 | 0.016451 | 0.036045 | −0.002362 | 0.007484 | 0.013882 | −0.007456 | −0.019003 | −0.009029 |
| 124 | 0.01349 | 0.011713 | 0.01113 | −0.006757 | −0.000771 | 0.009072 | 0.00647 | −0.000409 | −0.007848 | 0.01182 | 0.015743 | −0.008675 | −0.002273 | −0.001827 |
| 125 | 0.006787 | 0.005113 | 0.01701 | 0.008581 | −0.008646 | 0.012216 | 0.000181 | −0.019508 | −0.030235 | −0.009681 | 0.014801 | 0.00161 | 0.00635 | −0.016363 |
| 126 | −0.016333 | −0.028541 | −0.039956 | 0.020509 | 0.017203 | −0.000758 | −0.007753 | 0.038205 | 0.010978 | 0.011831 | −0.020428 | 0.022684 | 0.022245 | 0.012722 |
| 127 | −0.050539 | −0.023963 | −0.021342 | 0.009885 | −0.008661 | −0.020143 | 0.003894 | 0.030209 | −0.00512 | 0.001741 | −0.052772 | −0.02245 | 0.000423 | 0.006507 |
| 128 | −0.001572 | −0.000761 | −0.005768 | −0.019403 | 0.003253 | 0.015088 | −0.006352 | −0.021805 | −0.012467 | 0.002333 | 0.005261 | 0.007281 | −0.00349 | −0.014007 |
| 129 | −0.00885 | 0.000118 | 0.003819 | 0.024727 | −0.013716 | −0.025865 | 0.000188 | 0.030286 | 0.022231 | 0.001354 | −0.008331 | −0.021348 | 0.012882 | 0.021927 |
| 130 | −0.002391 | 0.002266 | −0.007756 | 0.017723 | 0.001906 | −0.016327 | −0.026126 | −0.033233 | 0.014176 | 0.00113 | 0.008921 | 0.019436 | 0.011241 | 0.017869 |
| 131 | −0.038102 | 0.00387 | 0.017287 | 0.007654 | −0.036193 | −0.000102 | 0.000224 | −0.037428 | 0.00624 | −0.021773 | 0.018037 | 0.032858 | 0.004754 | 0.0188 |
| 132 | 0.007777 | −0.009154 | 0.001749 | −0.018078 | −0.015934 | 0.008253 | 0.013833 | −0.005649 | −0.009322 | −0.002191 | 0.000842 | −0.012449 | −0.004367 | 0.000669 |
| 133 | 0.021359 | 0.009676 | 0.001876 | 0.01697 | 0.029226 | 0.001854 | −0.013087 | −0.023692 | −0.015819 | −0.02497 | 0.002081 | −0.011522 | −0.016088 | 0.009851 |
| 134 | −0.037129 | 0.010395 | 0.017153 | 0.030291 | −0.012297 | 0.006048 | 0.002971 | 0.027014 | 0.006573 | 0.018598 | 0.00979 | 0.067489 | 0.019126 | −0.009396 |
| 135 | 0.002705 | 0.012506 | 0.002503 | −0.005445 | 0.002869 | 0.014096 | 0.002406 | −0.006221 | 0.016481 | 0.006584 | 0.001272 | 0.008959 | 0.011403 | −0.001338 |
| 136 | 0.002682 | −0.010213 | 0.016688 | 0.010126 | 0.026657 | −0.004228 | 0.004014 | 0.01184 | 0.013195 | 0.00638 | −0.007094 | −0.029647 | −0.028915 | 0.001798 |
| 137 | 0.001957 | 0.010278 | 0.005191 | −0.00132 | −0.006796 | 0.004055 | −0.009021 | −0.003009 | 0.000957 | −0.004938 | −0.002422 | −0.011811 | −0.01508 | −0.017968 |
| 138 | −0.049628 | 0.012799 | 0.006467 | 0.004306 | −0.022627 | 0.022387 | 0.000725 | −0.034058 | 0.004487 | 0.009231 | −0.00093 | 0.017956 | 0.024766 | 0.014665 |
| 139 | 0.023185 | 0.009904 | 0.003832 | 0.018832 | 0.008339 | −0.004331 | 0.010992 | 0.04096 | 0.01098 | −0.020207 | −0.023404 | 0.018054 | −0.012395 | −0.015495 |
| 140 | −0.041354 | −0.001932 | −0.005105 | −0.028534 | −0.021161 | 0.03119 | 0.009018 | −0.043693 | −0.047281 | −0.018805 | −0.004689 | 0.000303 | 0.005286 | 0.007824 |
| 141 | −0.013743 | 0.003471 | 0.006767 | 0.011993 | 0.001366 | 0.002911 | 0.018359 | 0.0307081 | 0.005681 | 0.006913 | −0.008162 | 0.013518 | 0.028163 | 0.001063 |
| 142 | 0.029141 | 0.010042 | 0.00407 | 0.009445 | 0.039261 | −0.008413 | −0.009207 | 0.038091 | 0.016324 | 0.024485 | 0.012732 | 0.001857 | 0.00553 | 0.010842 |
| 143 | 0.009503 | 0.02398 | 0.024718 | −0.017347 | −0.013632 | 0.014731 | 0.010344 | −0.017085 | −0.010871 | −0.001625 | 0.024872 | 0.017746 | 0.006296 | −0.009618 |
| 144 | −0.020484 | 0.011773 | 0.014836 | 0.006935 | 0.017217 | −0.00038 | 0.011426 | −0.003657 | 0.014081 | 0.007622 | 0.00382 | 0.009439 | 0.006767 | 0.004985 |
| 145 | 0.024977 | 0.011317 | 0.007873 | 0.014958 | 0.025702 | 0.029626 | 0.0138 | 0.000971 | −0.002071 | −0.007962 | 0.007899 | 0.00516 | −0.033162 | −0.002416 |
| 146 | −0.011638 | 0.005308 | 0.000611 | −0.006355 | 0.001711 | 0.000521 | −0.004293 | 0.004924 | 0.005087 | −0.007238 | −0.007663 | 0.005618 | 0.012912 | 0.006639 |
| 147 | −0.038752 | −0.003307 | −0.019334 | −0.036411 | 0.027436 | −0.008606 | −0.0254 | 0.005453 | 0.004633 | 0.002825 | −0.011138 | 0.027038 | 0.011558 | 0.001771 |
| 148 | −0.042947 | −0.01306 | 0.00585 | 0.009821 | 0.034731 | −0.017555 | −0.006732 | 0.003479 | 0.033508 | 0.015775 | −0.011935 | 0.008077 | −0.002134 | 0.003855 |

APPENDIX B3-continued

PCA Transformation
Matrix (340 × 340 Early/Late)

| | | | | | | | | | | | | | |
|---|---|---|---|---|---|---|---|---|---|---|---|---|---|
| 149 | 0.018104 | 0.001678 | 0.00421 | 0.014692 | 0.004179 | 0.001848 | 0.00544 | 0.003746 | −0.009158 | −0.024375 | 0.012386 | 0.021066 | −0.004354 | −0.00763 |
| 150 | 0.028652 | 0.017315 | 0.007398 | −0.006168 | −0.009449 | 0.008926 | −0.009894 | 0.021467 | 0.008081 | 0.000756 | 0.008821 | −0.018773 | −0.00074 | 0.006411 |
| 151 | −0.02112 | −0.001184 | 0.0237 | 0.018796 | 0.005672 | 0.01567 | 0.01759 | 0.015002 | −0.024407 | −0.021662 | 0.015572 | 0.05825 | 0.012398 | −0.008493 |
| 152 | −0.040031 | −0.004937 | −0.00244 | −0.001196 | −0.007797 | −0.025318 | 0.004485 | 0.016506 | −0.012158 | 0.005051 | −0.033213 | −0.026589 | −0.002012 | 0.002626 |
| 153 | 0.007691 | −0.005725 | 0.004572 | 0.023761 | 0.030812 | −0.037393 | −0.028288 | 0.019941 | 0.009307 | 0.025558 | −0.002867 | 0.026431 | 0.030828 | 0.018875 |
| 154 | 0.010852 | 0.010583 | 0.001476 | 0.008329 | 0.022216 | −0.001571 | −0.020909 | −0.003307 | 0.02083 | 0.014515 | 0.016826 | 0.029693 | 0.018811 | 0.01626 |
| 155 | 0.010572 | 0.012631 | 0.010544 | −0.006254 | −0.015629 | −0.016382 | −0.019606 | −0.030216 | 0.006412 | 0.005109 | −0.009293 | −0.008459 | 0.014531 | 0.014788 |
| 156 | −0.029605 | 0.025243 | 0.000795 | −0.019004 | −0.012037 | 0.01061 | −0.005488 | −0.020821 | −0.006393 | −0.022712 | −0.000365 | 0.025531 | −0.001541 | −0.019021 |
| 157 | 0.012221 | 0.010204 | 0.008403 | −0.005894 | 0.008504 | 0.007858 | 0.011077 | 0.007916 | −0.018128 | −0.019656 | 0.004982 | −0.011157 | 0.011541 | −0.00121 |
| 158 | −0.005158 | 0.010773 | 0.019615 | −0.023759 | 0.005602 | 0.005481 | −0.007285 | 0.019265 | −0.014646 | −0.007664 | −0.018683 | 0.000017 | 0.005692 | −0.021636 |
| 159 | 0.035639 | 0.018175 | 0.002051 | −0.029206 | 0.003973 | 0.032684 | −0.014393 | −0.009914 | 0.024709 | 0.026544 | 0.006929 | −0.016409 | −0.018724 | −0.006246 |
| 160 | −0.031474 | 0.013561 | −0.00728 | 0.026226 | 0.033019 | 0.02916 | −0.002958 | −0.018524 | −0.043595 | −0.013503 | 0.010675 | 0.030906 | −0.007791 | −0.024878 |
| 161 | −0.035674 | −0.001171 | −0.001851 | −0.015872 | −0.000832 | −0.014574 | −0.001601 | 0.003681 | 0.00556 | 0.013804 | −0.016597 | 0.025076 | 0.011933 | −0.008843 |
| 162 | −0.022022 | 0.001741 | 0.002255 | 0.027434 | −0.001817 | 0.012828 | 0.008194 | 0.01696 | 0.006531 | 0.005099 | −0.011627 | −0.003873 | −0.008558 | 0.014437 |
| 163 | −0.016736 | 0.023337 | 0.019798 | 0.001073 | 0.002017 | −0.004211 | 0.009528 | 0.010999 | −0.015401 | −0.004332 | −0.007916 | −0.011285 | 0.004393 | −0.011017 |
| 164 | 0.004863 | 0.011676 | 0.013717 | 0.021821 | 0.024372 | −0.000942 | 0.005047 | 0.002454 | −0.012234 | −0.026754 | −0.003638 | 0.011561 | −0.001148 | 0.001229 |
| 165 | −0.032614 | −0.04186 | −0.044514 | 0.028921 | 0.015933 | −0.019033 | −0.042127 | −0.045765 | −0.028138 | 0.005898 | 0.007869 | 0.019909 | 0.020719 | −0.003122 |
| 166 | 0.001821 | −0.004295 | −0.015182 | 0.010308 | 0.030557 | 0.001215 | 0.005009 | 0.008949 | 0.039402 | 0.016091 | 0.005114 | −0.03157 | −0.021605 | −0.010894 |
| 167 | 0.009006 | −0.004798 | −0.015752 | −0.015809 | 0.013225 | 0.018403 | 0.0099 | −0.010301 | −0.017308 | −0.029811 | −0.015065 | −0.030877 | −0.03797 | −0.023698 |
| 168 | 0.007875 | 0.023182 | 0.034321 | 0.014638 | −0.010871 | −0.000533 | −0.002017 | −0.041339 | −0.0032 | 0.000191 | 0.018727 | 0.025386 | 0.03081 | 0.017144 |
| 169 | −0.003 | −0.00272 | 0.001751 | 0.009682 | −0.014921 | −0.003242 | 0.000734 | −0.005609 | −0.006007 | −0.013444 | 0.002467 | 0.003385 | 0.011011 | 0.011616 |
| 170 | −0.024206 | −0.007694 | 0.00128 | 0.025252 | −0.015781 | −0.016122 | −0.010086 | −0.017395 | −0.000752 | 0.000837 | −0.004636 | 0.01119 | 0.016675 | 0.023203 |
| 171 | −0.002976 | −0.00738 | −0.002874 | 0.012849 | −0.01842 | −0.002874 | 0.006479 | 0.01183 | 0.005827 | −0.002337 | −0.001401 | 0.013111 | 0.026862 | 0.015 |
| 172 | 0.017078 | 0.019243 | 0.014003 | −0.010739 | −0.014791 | 0.000501 | −0.004082 | −0.017315 | −0.009455 | −0.011053 | 0.010523 | 0.000084 | 0.007668 | −0.009166 |
| 173 | 0.022074 | −0.007147 | −0.00334 | 0.029422 | 0.02435 | −0.022398 | −0.029847 | −0.026135 | −0.003386 | 0.002978 | 0.000597 | 0.011309 | 0.010918 | 0.009384 |
| 174 | 0.017348 | 0.018292 | 0.022502 | 0.018478 | 0.002468 | −0.007177 | −0.006386 | −0.057936 | 0.004099 | −0.013638 | 0.01167 | 0.025953 | 0.017779 | 0.001932 |
| 175 | −0.001178 | −0.017617 | 0.003707 | 0.005993 | −0.028065 | −0.01344 | 0.013879 | 0.027208 | −0.008286 | −0.02618 | −0.005746 | −0.013093 | −0.007846 | −0.025577 |
| 176 | −0.014885 | −0.009344 | 0.006042 | −0.021619 | −0.020862 | −0.005414 | 0.002752 | −0.015801 | −0.017045 | −0.02679 | 0.003454 | −0.02186 | −0.016829 | −0.026406 |
| 177 | 0.020212 | 0.010147 | −0.011274 | −0.013307 | 0.019105 | 0.018917 | −0.015812 | −0.039363 | 0.006436 | −0.001375 | 0.009464 | 0.028463 | 0.021715 | 0.019303 |
| 178 | 0.019529 | −0.010881 | −0.006398 | 0.001664 | 0.012108 | −0.006856 | −0.008442 | 0.026417 | −0.012153 | −0.010667 | −0.006247 | −0.016279 | 0.00067 | −0.007873 |
| 179 | 0.011021 | 0.003196 | 0.013215 | −0.004263 | 0.00013 | 0.007259 | 0.00186 | −0.003769 | −0.013837 | −0.004508 | 0.00268 | −0.013493 | −0.00005 | 0.003315 |
| 180 | 0.018233 | −0.00719 | 0.002539 | 0.005818 | 0.00496 | −0.004502 | −0.014322 | −0.010614 | −0.004827 | 0.000888 | 0.001646 | −0.009236 | −0.000226 | 0.006412 |
| 181 | 0.015143 | −0.001625 | 0.009088 | −0.000068 | 0.00156 | −0.002937 | −0.006676 | −0.009864 | −0.012025 | −0.000025 | 0.002071 | −0.012733 | −0.002929 | 0.00072 |
| 182 | 0.022912 | 0.003978 | 0.012359 | −0.001259 | 0.006931 | −0.003381 | −0.011066 | −0.003486 | −0.005507 | 0.00457 | 0.00072 | −0.014683 | −0.00069 | 0.00686 |
| 183 | 0.010819 | 0.007028 | 0.007647 | −0.014036 | −0.006249 | 0.018135 | 0.01173 | 0.013105 | 0.003241 | 0.009058 | −0.003494 | −0.015761 | 0.002201 | −0.001596 |
| 184 | −0.00176 | 0.028777 | 0.024487 | −0.013479 | −0.01094 | 0.021922 | 0.023111 | −0.025712 | 0.017505 | 0.009614 | 0.009221 | −0.010806 | −0.015323 | −0.01917 |
| 185 | 0.022707 | 0.006555 | −0.012888 | −0.067484 | −0.013735 | 0.003661 | −0.018554 | −0.057259 | −0.008849 | 0.013128 | 0.027717 | −0.025051 | −0.025543 | −0.017751 |
| 186 | 0.018113 | 0.007336 | 0.002053 | −0.020599 | 0.003499 | −0.025057 | −0.015095 | −0.05275 | 0.041745 | 0.026222 | 0.024541 | 0.004375 | −0.004066 | 0.015533 |
| 187 | 0.022653 | −0.007299 | −0.005691 | 0.009852 | 0.028381 | −0.016805 | −0.032744 | −0.024713 | 0.015786 | 0.023278 | −0.000475 | −0.006779 | −0.005291 | 0.017045 |
| 188 | 0.015835 | 0.011235 | 0.008782 | 0.00561 | 0.009577 | −0.007212 | −0.023547 | −0.057101 | 0.017267 | 0.011477 | 0.00403 | 0.0088 | 0.004369 | 0.012511 |
| 189 | 0.021397 | 0.018262 | 0.037478 | 0.009575 | −0.009714 | 0.008945 | 0.008271 | −0.022008 | 0.018738 | 0.001216 | 0.008179 | −0.007788 | −0.007686 | 0.000326 |
| 190 | −0.005851 | 0.007582 | 0.013749 | 0.001041 | −0.008913 | 0.007228 | 0.006618 | −0.012533 | −0.007563 | −0.023511 | 0.001659 | −0.00151 | −0.027803 | −0.024404 |
| 191 | 0.003319 | 0.01024 | 0.020433 | 0.009939 | −0.006674 | 0.004508 | 0.003901 | −0.016905 | −0.007039 | −0.009313 | 0.011871 | 0.024811 | 0.014909 | 0.007374 |
| 192 | −0.044024 | 0.012755 | 0.001368 | −0.019453 | −0.018669 | 0.008717 | 0.0192 | 0.004536 | −0.010151 | −0.002014 | −0.041585 | −0.015561 | 0.012393 | 0.018294 |
| 193 | −0.03631 | 0.000071 | 0.012319 | −0.018313 | −0.000837 | −0.03564 | −0.005635 | −0.025975 | 0.009139 | 0.015635 | −0.026397 | −0.021063 | −0.005894 | 0.000506 |
| 194 | −0.003188 | −0.001329 | 0.009866 | −0.004459 | −0.024925 | −0.017228 | −0.008876 | −0.010656 | −0.007179 | −0.013854 | −0.003681 | −0.016548 | −0.003079 | −0.004478 |
| 195 | 0.000661 | 0.031814 | 0.029353 | −0.033714 | 0.0025 | 0.008814 | 0.013276 | −0.022566 | −0.018713 | −0.015296 | 0.017261 | −0.033442 | −0.045556 | −0.024031 |
| 196 | −0.004216 | 0.01287 | 0.013754 | −0.02602 | −0.013991 | 0.01092 | 0.0186 | −0.013078 | −0.015102 | −0.025285 | 0.000653 | −0.028455 | −0.044635 | −0.025072 |
| 197 | 0.00279 | 0.01151 | 0.017248 | −0.001562 | −0.009512 | 0.016631 | 0.003282 | −0.027522 | −0.023754 | −0.029124 | 0.014343 | 0.02731 | −0.007608 | −0.011226 |
| 198 | 0.005511 | 0.03071 | 0.013064 | −0.025472 | 0.001832 | 0.01602 | −0.002241 | 0.001125 | −0.011992 | 0.010241 | 0.029328 | −0.009188 | 0.006974 | −0.014575 |

APPENDIX B3-continued

PCA Transformation
Matrix (340 × 340 Early/Late)

| | | | | | | | | | | | | | |
|---|---|---|---|---|---|---|---|---|---|---|---|---|---|
| 199 | 0.010893 | −0.004166 | 0.013751 | 0.004587 | −0.00488 | 0.004452 | 0.026376 | 0.029407 | −0.009261 | −0.055769 | 0.018136 | −0.014778 | −0.006306 | −0.012382 |
| 200 | 0.008698 | 0.024355 | 0.011812 | −0.00401 | −0.001298 | 0.024235 | 0.016294 | 0.024254 | −0.012043 | −0.007068 | 0.003931 | 0.004469 | 0.015137 | −0.023033 |
| 201 | −0.016672 | −0.020597 | −0.029587 | −0.00383 | 0.01756 | 0.007904 | 0.001008 | 0.020143 | −0.001347 | 0.008261 | −0.004206 | 0.009649 | −0.002206 | 0.011781 |
| 202 | −0.001394 | 0.016763 | −0.005507 | −0.012578 | 0.004023 | 0.017497 | 0.00956 | 0.015296 | −0.007924 | −0.003828 | 0.017723 | −0.001299 | 0.000084 | −0.023207 |
| 203 | −0.005534 | 0.007714 | 0.003433 | 8.002507 | −0.013598 | 0.013163 | −0.001612 | 0.001404 | 0.000327 | −0.002186 | −0.018279 | −0.018351 | −0.01565 | −0.008388 |
| 204 | −0.048722 | −0.017491 | −0.030807 | −0.052874 | −0.032042 | −0.027406 | −0.010394 | −0.055607 | −0.004572 | −0.00172 | −0.021329 | −0.041634 | −0.015586 | −0.00581 |
| 205 | −0.030596 | 0.015679 | 0.03609 | 0.007216 | −0.027545 | 0.036447 | 0.032623 | −0.003187 | −0.040663 | −0.012364 | −0.007593 | 0.00542 | −0.003549 | −0.048011 |
| 206 | −0.010428 | 0.002326 | −0.006446 | −0.013051 | 0.016955 | −0.008014 | 0.00548 | 0.015548 | −4.001437 | 0.00739 | −0.019472 | −0.02596 | −0.046728 | −0.03679 |
| 207 | 0.009925 | −0.015399 | −0.005147 | −0.005803 | −0.020796 | −0.026095 | −0.00187 | −0.026684 | −0.012102 | 0.012735 | −0.014262 | −0.024022 | 0.007936 | 0.002899 |
| 208 | −0.043325 | 0.001347 | −0.019861 | 0.022622 | −0.010545 | 0.002186 | 0.006424 | −0.019202 | −0.002299 | 0.006227 | −0.015303 | 0.00389 | −0.009246 | 0.009885 |
| 209 | −0.036479 | 0.008509 | −0.005641 | −0.013617 | 0.001799 | 0.013811 | 0.008032 | 0.028186 | 0.016259 | −0.013537 | −0.026604 | −0.021308 | −0.009997 | −0.013876 |
| 210 | 0.032698 | 0.012773 | 0.022245 | −0.034424 | 0.022678 | 0.003252 | 0.008995 | 0.052446 | 0.001718 | −0.038914 | 0.007382 | −0.018637 | 0.000887 | −0.019612 |
| 211 | 0.029881 | 0.025566 | 0.009173 | 0.004738 | 0.00494 | −0.009835 | −0.014039 | 0.022638 | 0.019192 | −0.02022 | 0.013063 | 0.041552 | 0.03154 | −0.00409 |
| 212 | −0.007409 | 0.033998 | 0.012546 | −0.007907 | −0.007885 | −0.009836 | −0.020019 | −0.039362 | −0.015014 | −0.025759 | 0.018803 | 0.032236 | 0.001269 | −0.014494 |
| 213 | 0.042632 | 0.009719 | 0.01323 | −0.032543 | −0.023926 | −0.040583 | −0.011528 | −0.036649 | −0.007963 | 0.006939 | 0.001532 | −0.029835 | −0.009847 | −0.00207 |
| 214 | 0.021289 | 0.004602 | 0.006135 | 0.001751 | 0.001227 | 0.010335 | 0.005664 | 0.009803 | 0.008202 | 0.007978 | 0.003787 | −0.015284 | 0.00165 | 0.009783 |
| 215 | 0.012274 | 0.007838 | 0.028754 | −0.015222 | −0.02685 | 0.002701 | 0.011948 | −0.030245 | −0.006615 | −0.007642 | 0.029327 | 0.02095 | 0.027462 | 0.003249 |
| 216 | 0.032394 | 0.004308 | 0.020634 | 0.020025 | −0.013956 | 0.001338 | 0.003532 | −0.008758 | 0.010983 | −0.006903 | 0.023535 | 0.035353 | 0.031056 | 0.013977 |
| 217 | −0.01904 | 0.016072 | 0.005244 | −0.03215 | −0.022021 | 0.023791 | 0.031374 | 0.0102 | −0.003771 | −0.022293 | 0.001299 | −0.024649 | −0.033853 | −0.020052 |
| 218 | 0.003338 | 0.015447 | 0.023062 | 0.012823 | −0.007887 | 0.010523 | 0.023202 | −0.001218 | 0.021653 | 0.008137 | 0.011253 | 0.022365 | 0.022292 | 0.008997 |
| 219 | 0.016738 | 0.014296 | 0.006323 | 0.023679 | 0.01595 | 0.008611 | 0.021347 | 0.036896 | 0.021822 | 0.006336 | 0.004105 | 0.011347 | 0.0089971 | 0.014947 |
| 220 | −0.002671 | 0.0083 | 0.001696 | −0.016826 | −0.027877 | 0.007304 | −0.010426 | −0.041505 | −0.002179 | −0.018255 | 0.005783 | −0.019256 | −0.017571 | −0.011691 |
| 221 | 0.023211 | −0.003106 | −0.017387 | 0.00282 | 0.00678 | −0.004355 | −0.033707 | −0.026085 | −0.008699 | 0.0054 | 0.000601 | 0.006008 | 0.010361 | 0.014872 |
| 222 | −0.044237 | 0.010627 | 0.00562 | 0.008651 | −0.014529 | −0.011334 | 0.011718 | 0.021449 | −0.005073 | −0.00865 | −0.055718 | −0.021475 | 0.003527 | 0.004616 |
| 223 | −0.012639 | −0.01386 | −0.0005 | 0.009572 | −0.014699 | −0.049874 | −0.010281 | 0.01116 | 0.000263 | −0.00032 | −0.040119 | −0.028312 | 0.003647 | 0.009264 |
| 224 | 0.018642 | 0.00931 | −0.00164 | −0.001081 | −0.018977 | 0.005999 | 0.012261 | 0.016187 | −0.000093 | −0.045956 | 0.011586 | 0.0113221 | 0.010245 | −0.017941 |
| 225 | 0.028049 | 0.009957 | −0.010506 | −0.00045 | −0.023666 | 0.006975 | 0.006141 | 0.019861 | −0.001023 | −0.045452 | 0.010333 | 0.005622 | 0.010092 | −0.009223 |
| 226 | 0.003755 | 0.002817 | 0.00349 | 0.000013 | −0.009387 | 0.021679 | 0.023798 | 0.025806 | −0.021376 | −0.004281 | 0.010528 | −0.003455 | −0.001809 | 0.003768 |
| 227 | 0.020284 | −0.017412 | −0.008716 | −0.004387 | 0.009711 | 0.018054 | 0.005094 | 0.036987 | −0.035967 | −0.031258 | 0.009316 | 0.005949 | 0.000188 | 0.000887 |
| 228 | −0.026235 | 0.011478 | 0.004628 | −0.008584 | −0.064428 | −0.002034 | 0.029664 | 0.041261 | 0.011272 | −0.000087 | −0.037109 | −0.033284 | −0.022646 | −0.016079 |
| 229 | 0.02338 | 0.027565 | 0.026857 | −0.00654 | −0.042678 | 0.003333 | 0.003458 | −0.055982 | 0.019105 | 0.048808 | 0.013611 | −0.00898 | 0.005252 | 0.004432 |
| 230 | 0.039123 | 0.020458 | 0.027267 | 0.015099 | 0.001055 | 0.00641 | −0.006541 | −0.017299 | −0.006209 | 0.013307 | 0.02778 | 0.035331 | 0.039885 | −0.003465 |
| 231 | 0.014138 | −0.013507 | −0.011827 | −0.026904 | 0.013239 | −0.008678 | −0.008474 | 0.030557 | −0.016177 | 0.006287 | 0.005306 | −0.019647 | −0.037146 | −0.025253 |
| 232 | −0.04356 | 0.010079 | 0.011017 | −0.037233 | −0.057671 | 0.017925 | 0.028246 | 0.002713 | −0.007919 | −0.008222 | 0.000538 | −0.00655 | −0.000278 | −0.034614 |
| 233 | −0.035881 | −0.011812 | −0.011178 | −0.033215 | −0.023028 | 0.004758 | 0.00893 | −0.003995 | 0.012845 | 0.019012 | −0.010547 | 0.009019 | 0.018726 | 0.006596 |
| 234 | 0.002446 | −0.026931 | −0.036759 | −0.027423 | −0.027531 | 0.007621 | −0.001722 | 0.030107 | −0.00375 | 0.01331 | −0.018652 | −0.024928 | −0.038112 | −0.013825 |
| 235 | −0.019914 | −0.009303 | −0.037196 | −0.041472 | −0.028002 | −0.001606 | 0.001498 | 0.038965 | −0.005331 | −0.008277 | −0.032129 | −0.031744 | −0.035855 | −0.031162 |
| 236 | −0.007511 | 0.004505 | 0.015346 | −0.015254 | −0.016231 | 0.00006 | 0.014865 | 0.015575 | 0.001545 | −0.018361 | 0.001787 | −0.006514 | −0.009365 | −0.046181 |
| 237 | 0.002754 | 0.000482 | 0.003127 | 0.022532 | 0.004012 | 0.020897 | 0.015954 | 0.0163 | 0.028397 | 0.01747 | 0.00675 | 0.022944 | 0.004572 | 0.009825 |
| 238 | 0.00359 | 0.007074 | 0.001537 | 0.021207 | 0.01817 | 0.009772 | 0.013797 | 0.029863 | 0.01373 | 0.016518 | 0.007978 | 0.025076 | 0.000153 | 0.00557 |
| 239 | −0.001077 | 0.010751 | 0.006274 | 0.00284 | 0.025106 | −0.007467 | 0.01956 | 0.046828 | 0.006588 | 0.009926 | −0.002634 | −0.001039 | −0.008727 | −0.008304 |
| 240 | −0.081304 | −0.075809 | −0.079504 | −0.030327 | 0.006614 | −0.019148 | −0.020645 | −0.01243 | −0.000768 | 0.005521 | −0.044232 | −0.037544 | −0.050883 | 0.00089 |
| 241 | −0.058142 | −0.046015 | −0.053637 | −0.056339 | −0.032256 | −0.003596 | −0.00214 | −0.031137 | 0.018675 | 0.005276 | −0.029951 | −0.026432 | −0.022896 | 0.003628 |
| 242 | −0.007833 | 0.009445 | 0.005631 | −0.040141 | −0.041524 | −0.003012 | 0.001073 | 0.011902 | 0.014064 | −0.000235 | −0.015068 | −0.015917 | −0.015455 | −0.04343 |
| 243 | −0.02793 | 0.022159 | 0.005748 | −0.044156 | −0.061206 | −0.016111 | 0.001626 | 0.023552 | 0.030779 | −0.004873 | −0.032782 | −0.023541 | −0.023338 | −0.022974 |
| 244 | 0.023569 | −0.016389 | −0.027751 | −0.021959 | 0.014544 | −0.02361 | −0.053036 | −0.019315 | 0.006834 | 0.023342 | 0.006373 | −0.0017761 | 0.007913 | 0.014063 |
| 245 | 0.005967 | 0.013261 | 0.004018 | −0.037279 | 0.000202 | −0.011164 | −0.023368 | −0.072155 | 0.007871 | 0.002373 | 0.007137 | 0.002537 | 0.012192 | −0.002508 |
| 246 | −0.001303 | 0.00124 | 0.016997 | 0.023847 | 0.012775 | −0.002124 | −0.011255 | −0.022216 | 0.012164 | 0.001293 | −0.000269 | 0.017477 | 0.010789 | −0.002061 |
| 247 | 0.009815 | 0.016224 | 0.013629 | 0.005165 | 0.007978 | 0.002479 | −0.00067 | 0.003352 | 0.001179 | −0.028501 | 0.00159 | −0.000836 | −0.011296 | −0.027061 |
| 248 | −0.007398 | 0.017104 | 0.003655 | −0.017802 | −0.01094 | 0.009857 | 0.005661 | 0.005088 | −0.00147 | −0.024811 | −0.005215 | −0.016132 | −0.018979 | −0.029838 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 249 | 0.835621 | −0.045343 | −0.0446 | −0.050762 | −0.043387 | −0.029389 | 0.002441 | −0.020642 | −0.001449 | 0.003483 | −0.089352 | −0.057055 | −0.042092 | −0.008479 |
| 250 | −0.046619 | 0.90805 | −0.074356 | −0.018539 | 0.003693 | −0.03217 | −0.030313 | 0.010048 | −0.001499 | 0.018088 | −0.045151 | −0.044846 | −0.039417 | 0.007946 |
| 251 | −0.046192 | −0.082754 | 0.88641 | −0.046555 | 0.007933 | −0.019526 | −0.036007 | 0.01031 | 0.003229 | 0.010189 | −0.053402 | −0.059543 | −0.060125 | 0.000422 |
| 252 | −0.042254 | −0.017845 | −0.04869 | 0.855472 | −0.046461 | −0.000619 | −0.007956 | −0.040044 | −0.009973 | −0.002711 | −0.035697 | −0.10403 | −0.089219 | −0.048687 |
| 253 | −0.024911 | 0.009286 | 0.013644 | −0.042849 | 0.88672 | 0.001731 | 0.014221 | −0.023724 | 0.000414 | −0.009721 | −0.009667 | −0.01557 | 0.002971 | −0.018054 |
| 254 | −0.019114 | −0.030186 | −0.016749 | −0.001094 | 0.000998 | 0.918876 | −0.048782 | −0.017525 | 0.020803 | 0.015249 | −0.038869 | −0.029741 | −0.006463 | 0.019485 |
| 255 | 0.008317 | −0.028373 | −0.032978 | −0.007749 | 0.019175 | −0.042969 | 0.921829 | −0.057209 | 0.00723 | 0.017233 | −0.003712 | 0.003227 | −0.002123 | 0.01844 |
| 256 | −0.012923 | 0.017365 | 0.012547 | −0.041825 | −0.032827 | −0.007631 | −0.054153 | 0.797103 | −0.020234 | −0.000544 | 0.023582 | 0.019953 | 0.003833 | 0.004752 |
| 257 | −0.004255 | −0.001579 | 0.007873 | −0.003456 | −0.006058 | 0.026378 | 0.015627 | −0.013225 | 0.914232 | −0.04423 | 0.012158 | 0.002741 | 0.001482 | −0.013471 |
| 258 | 0.003136 | 0.016005 | 0.011836 | −0.004844 | −0.017592 | 0.009244 | 0.021293 | 0.006703 | −0.038916 | 0.905665 | 0.003938 | 0.00299 | −0.007715 | −0.018579 |
| 259 | −0.084829 | −0.045875 | −0.049305 | −0.030239 | −0.023543 | −0.043535 | −0.007684 | 0.027951 | 0.017221 | 0.010617 | 0.902038 | −0.077475 | −0.045369 | −0.0003 |
| 260 | −0.049808 | −0.050243 | −0.05941 | −0.091634 | −0.025506 | −0.035157 | −0.006918 | 0.02555 | 0.00882 | 0.015483 | −0.084987 | 0.82788 | −0.113258 | −0.031151 |
| 261 | −0.045981 | −0.042991 | −0.063722 | −0.078629 | −0.009245 | −0.008651 | −0.003271 | 0.006612 | −0.00082 | −0.009828 | −0.058098 | −0.11986 | 0.867694 | −0.042943 |
| 262 | −0.014629 | 0.00594 | −0.002509 | −0.045441 | −0.01327 | 0.018203 | 0.020981 | 0.020746 | −0.017916 | −0.019672 | −0.00793 | −0.044236 | −0.055073 | 0.93249 |
| 263 | −0.014497 | 0.011008 | −0.000169 | −0.04688 | −0.027981 | 0.015056 | 0.019221 | 0.02909 | −0.017527 | −0.018373 | −0.016698 | −0.037764 | −0.034718 | −0.056644 |
| 264 | −0.072858 | −0.020317 | −0.01035 | 0.006761 | −0.0103 | −0.045094 | −0.012128 | −0.002905 | 0.024917 | 0.007234 | −0.074304 | −0.037462 | −0.014791 | 0.018704 |
| 265 | −0.049329 | −0.010909 | 0.010427 | −0.008768 | −0.008151 | −0.070341 | −0.014813 | −0.013623 | 0.025622 | −0.00705 | −0.057415 | −0.067291 | −0.045989 | 0.008043 |
| 266 | 0.002777 | 0.004837 | 0.000043 | −0.030188 | −0.000701 | −0.044462 | −0.033547 | −0.043292 | 0.017322 | −0.013508 | −0.010133 | −0.04865 | −0.060532 | −0.00459 |
| 267 | 0.014895 | 0.009711 | 0.037157 | 0.009742 | −0.052795 | 0.005999 | 0.018138 | −0.029417 | 0.011449 | 0.0268 | 0.028524 | 0.007336 | 0.014754 | 0.006649 |
| 268 | 0.009398 | 0.000809 | 0.00784 | −0.003462 | −0.013751 | 0.017157 | 0.020164 | 0.022408 | −0.014769 | −0.001163 | 0.012356 | −0.000628 | 0.007228 | 0.005661 |
| 269 | 0.013586 | −0.001581 | −0.001497 | −0.005312 | −0.016498 | 0.018079 | 0.009046 | 0.009498 | −0.014787 | 0.004374 | 0.01741 | −0.000934 | 0.007295 | 0.00912 |
| 270 | 0.006112 | −0.011957 | −0.0056 | −0.002655 | 0.004105 | 0.015128 | 0.006956 | 0.030517 | −0.024387 | −0.006474 | 0.007787 | −0.013317 | −0.005898 | 0.002849 |
| 271 | 0.00276 | 0.004826 | 0.009585 | 0.006527 | −0.024624 | −0.000637 | 0.010931 | 0.031683 | 0.032795 | 0.023115 | 0.000164 | −0.014035 | 0.006562 | −0.005733 |
| 272 | 0.005326 | 0.015537 | 0.012364 | 0.002162 | −0.021887 | 0.00324 | 0.012944 | −0.019576 | 0.017712 | 0.039984 | 0.000146 | −0.019759 | −0.01583 | −0.002833 |
| 273 | 0.00667 | 0.008036 | 0.004652 | −0.012814 | −0.001306 | 0.011815 | 0.013944 | 0.017015 | −0.007326 | 0.010149 | −0.000646 | −0.023222 | 0.000211 | −0.013955 |
| 274 | 0.009189 | 0.005987 | 0.001823 | −0.009962 | −0.000887 | 0.011049 | 0.010417 | 0.01504 | −0.006992 | 0.011423 | 0.000191 | −0.022881 | −0.000995 | −0.010207 |
| 275 | 0.017833 | 0.005079 | 0.012436 | 0.019866 | 0.036689 | 0.00404 | −0.010235 | 0.021926 | −0.005758 | 0.006206 | 0.008972 | 0.003306 | 0.010705 | −0.01118 |
| 276 | −0.003743 | 0.007349 | 0.0176 | −0.017636 | −0.029505 | 0.00329 | 0.02293 | 0.006198 | 0.006092 | −0.01527 | −0.000394 | −0.014017 | −0.021126 | −0.047011 |
| 277 | 0.010758 | 0.018066 | 0.02306 | 0.017695 | 0.013412 | −0.000429 | 0.026705 | 0.045571 | 0.03102 | 0.010707 | 0.002687 | 0.004021 | 0.007458 | −0.004114 |
| 278 | 0.013361 | 0.010761 | 0.011901 | 0.019852 | 0.016124 | −0.007398 | 0.022046 | 0.054539 | 0.03383 | 0.019352 | −0.000766 | −0.000233 | 0.010876 | −0.003978 |
| 279 | −0.001934 | 0.009317 | 0.00188 | 0.014957 | 0.034358 | −0.009991 | 0.019264 | 0.058274 | 0.020929 | 0.020711 | −0.004932 | −0.007573 | −0.015867 | −0.004157 |
| 280 | −0.02521 | 0.025579 | 0.03121 | −0.010534 | −0.094551 | −0.007699 | 0.012719 | 0.001633 | 0.033562 | −0.010635 | −0.019778 | 0.020541 | 0.026497 | −0.001242 |
| 281 | −0.002368 | 0.010454 | 0.012072 | 0.027131 | 0.006019 | −0.012036 | −0.005385 | −0.015274 | 0.026904 | −0.020073 | −0.007757 | 0.018058 | 0.014825 | 0.003262 |
| 282 | 0.001116 | 0.010038 | 0.003877 | 0.015594 | 0.009007 | −0.014858 | −0.009751 | −0.010122 | 0.01146 | −0.036615 | −0.007502 | 0.016634 | 0.021842 | −0.003801 |
| 283 | 0.006744 | 0.012945 | −0.007316 | −0.004871 | 0.016367 | −0.007057 | −0.002388 | 0.014627 | 0.021907 | −0.013172 | −0.010292 | −0.023946 | −0.031142 | −0.028658 |
| 284 | −0.006232 | −0.006368 | −0.000584 | 0.007384 | −0.002547 | 0.018896 | 0.012362 | −0.016053 | −0.057298 | −0.026396 | 0.006577 | 0.004832 | 0.003667 | −0.001779 |
| 285 | −0.008187 | −0.01014 | −0.006664 | 00001 28 | −0.001308 | 0.016505 | 0.009687 | −0.005991 | −0.064869 | −0.025192 | 0.00545 | 0.001443 | 0.007869 | −0.004266 |
| 286 | 0.006589 | 0.004682 | −0.002409 | 0.00771 | −0.004712 | 0.002861 | 0.006537 | −0.017395 | −0.043448 | −0.076094 | 0.007541 | 0.027157 | 0.015794 | 0.019305 |
| 287 | 0.00353 | 0.005259 | −0.006777 | 0.00021 | −0.003569 | 0.001323 | 0.002421 | −0.007907 | −0.03792 | −0.069282 | 0.005405 | 0.020879 | 0.014697 | 0.014567 |
| 288 | 0.013984 | 0.010717 | −0.004759 | 0.001441 | −0.013298 | 0.016364 | 0.016748 | 0.012928 | −0.00348 | −0.07267 | 0.003566 | −0.000591 | −0.02153 | −0.022298 |
| 289 | −0.008621 | 0.00993 | 0.006735 | −0.023132 | −0.001541 | 0.008082 | 0.0094 | 0.016661 | −0.018745 | −0.032321 | 0.004549 | −0.033332 | −0.036158 | −0.050792 |
| 290 | 0.007889 | −0.003468 | −0.01833 | −0.008456 | −0.004568 | 0.012855 | −0.009737 | −0.00677 | 0.01676 | −0.003884 | 0.008428 | 0.003565 | −0.017152 | −0.012453 |
| 291 | 0.006723 | −0.002846 | −0.016812 | −0.00766 | −0.002918 | 0.012389 | −0.008731 | −0.006583 | 0.015114 | −0.006139 | 0.008154 | 0.003622 | −0.018729 | −0.012453 |
| 292 | 0.003721 | −0.005129 | −0.018802 | −0.005798 | −0.000459 | 0.012553 | −0.010196 | −0.007366 | 0.011758 | −0.000944 | 0.00888 | 0.012939 | −0.018299 | −0.009991 |
| 293 | 0.001362 | −0.02109 | 0.010917 | 0.031571 | 0.001432 | −0.020096 | −0.011332 | −0.011786 | −0.003355 | 0.004905 | −0.007809 | 0.0283 | 0.016688 | 0.006543 |
| 294 | 0.003174 | 0.008143 | 0.015956 | 0.01023 | 0.010299 | 0.003992 | 0.011256 | 0.021068 | 0.009728 | 0.004227 | −0.004976 | −0.000862 | 0.00062 | −0.001738 |
| 295 | 0.006618 | 0.002089 | 0.010333 | 0.012582 | 0.006336 | 0.001896 | −0.000969 | −0.008616 | −0.01063 | 0.01876 | −0.001185 | 0.005144 | 0.004948 | −0.014544 |
| 296 | −0.002567 | 0.013604 | 0.002325 | −0.006721 | −0.004431 | 0.006282 | −0.004396 | 0.003386 | 0.000241 | 0.009639 | −0.009456 | −0.033017 | −0.021844 | −0.017573 |
| 297 | 0.011663 | 0.00118 | 0.003805 | 0.001344 | −0.009692 | −0.000453 | −0.001497 | −0.024313 | −0.005814 | 0.009659 | −0.001731 | −0.00614 | −0.003937 | −0.013434 |
| 298 | 0.026279 | −0.002147 | −0.001969 | 0.002247 | 0.000442 | −0.004122 | 0.003342 | 0.019912 | 0.009993 | 0.01067 | 0.005155 | −0.01872 | −0.000601 | 0.007183 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 299 | 0.011206 | 0.000807 | −0.003548 | 0.013699 | −0.006669 | −0.007753 | 0.005111 | 0.00926 | 0.009974 | −0.001251 | −0.005782 | 0.003881 | 0.00022 | 0.002117 |
| 300 | 0.016874 | −0.019794 | −0.001897 | 0.041641 | 0.0081 | −0.006387 | 0.00566 | 0.019644 | −0.005357 | 0.00071 | 0.014861 | 0.015795 | −0.013836 | 0.003074 |
| 301 | −0.000609 | −0.004653 | −0.001478 | 0.016109 | −0.001673 | 0.008347 | 0.007663 | 0.010588 | −0.020598 | 0.013468 | −0.005318 | 0.004105 | 0.006016 | −0.011292 |
| 302 | −0.007718 | 0.005677 | 0.004754 | 0.02587 | 0.016275 | 0.012715 | 0.016979 | 0.035812 | −0.020077 | −0.001652 | −0.005558 | 0.003278 | 0.003058 | −0.010691 |
| 303 | 0.020307 | 0.022514 | 0.006428 | 0.005595 | −0.007048 | 0.000079 | 0.016472 | 0.025181 | 0.006624 | −0.022902 | 0.000318 | −0.002601 | −0.010378 | 0.001843 |
| 304 | 0.0113 | 0.009351 | −0.012552 | 0.014322 | −0.010848 | 0.008633 | 0.022437 | 0.038433 | 0.014265 | −0.019761 | −0.00953 | 0.006877 | −0.007357 | 0.006851 |
| 305 | 0.028816 | −0.002707 | 0.004814 | 0.024905 | 0.012698 | 0.000824 | −0.006256 | 0.007999 | −0.01863 | 0.01215 | 0.011563 | 0.029132 | 0.011318 | 0.004404 |
| 306 | −0.035976 | −0.013636 | 0.009986 | 0.009251 | −0.004216 | 0.00169 | 0.010527 | −0.01473 | −0.013391 | −0.028412 | −0.01516 | −0.001156 | −0.020737 | −0.012916 |
| 307 | −0.00614 | 0.022445 | 0.022159 | −0.020201 | −0.049419 | −0.002229 | 0.008756 | −0.015458 | 0.000929 | −0.024104 | 0.009018 | 0.023906 | 0.015659 | −0.003689 |
| 308 | −0.000685 | 0.005995 | 0.000377 | −0.027684 | −0.024456 | 0.007823 | −0.015653 | −0.011773 | −0.012003 | 0.013924 | 0.001709 | −0.009309 | 0.019904 | 0.013065 |
| 309 | −0.000972 | −0.002429 | −0.000409 | 0.020311 | 0.005163 | −0.009483 | −0.007817 | 0.01883 | −0.000443 | 0.003094 | −0.001512 | 0.012711 | 0.011188 | 0.008846 |
| 310 | 0.002355 | 0.003959 | 0.015063 | 0.019801 | 0.009107 | −0.019484 | −0.013409 | 0.021626 | 0.010805 | −0.003468 | 0.005044 | 0.00973 | 0.025483 | 0.016829 |
| 311 | 0.00944 | −0.00151 | −0.003602 | −0.012295 | −0.01276 | −0.00208 | 0.001209 | 0.015877 | 0.004573 | 0.007439 | −0.011623 | −0.017567 | −0.00239 | 0.002511 |
| 312 | 0.012011 | 0.019799 | −0.009634 | −0.022253 | −0.012576 | 0.009297 | −0.013349 | −0.017542 | 0.007717 | −0.000521 | 0.016922 | 0.020596 | 0.013412 | −0.007575 |
| 313 | 0.009673 | 0.000859 | −0.000653 | 0.005684 | −0.003702 | 0.002397 | −0.006837 | −0.022098 | −0.014459 | −0.004805 | −0.005827 | −0.002393 | −0.002684 | 0.017255 |
| 314 | −0.01538 | −0.017221 | −0.009942 | −0.029144 | −0.00757 | −0.032533 | −0.010604 | −0.017935 | 0.02894 | 0.01601 | −0.009684 | −0.022923 | 0.003844 | 0.007362 |
| 315 | 0.020043 | −0.002709 | −0.001012 | 0.009719 | −0.007165 | −0.008371 | −0.00904 | −0.003606 | −0.003117 | −0.019114 | 0.008236 | 0.009726 | 0.001196 | 0.017462 |
| 316 | 0.004687 | −0.00159 | 0.020404 | 0.042857 | −0.01064 | 0.008728 | −0.018675 | −0.001037 | −0.014343 | 0.022449 | 0.015504 | 0.006484 | 0.019331 | 0.008563 |
| 317 | 0.00129 | −0.006523 | 0.006945 | 0.01135 | 0.009987 | −0.017408 | −0.006851 | 0.003347 | −0.022242 | 0.007291 | −0.006269j | −0.014192 | −0.000629 | −0.000543 |
| 318 | 0.012049 | −0.011741 | −0.011606 | 0.01281 | 0.001778 | −0.006465 | 0.000086 | 0.04017 | −0.005896 | 0.015559 | −0.020714 | −0.012319 | 0.019769 | 0.02217 |
| 319 | 0.017786 | 0.00278 | −0.000773 | 0.00903 | −0.01089 | −0.014199 | −0.008559 | −0.009041 | −0.011881 | −0.022927 | 0.008333 | 0.005725 | 0.011105 | 0.019793 |
| 320 | 0.003473 | 0.009572 | 0.00443 | 0.012684 | 0.01003 | −0.003557 | 0.009621 | 0.002285 | −0.021437 | −0.033126 | −0.006283 | 0.005778 | 0.01712 | 0.022669 |
| 321 | −0.000849 | 0.001128 | −0.005835 | −0.027233 | −0.006208 | 0.023491 | 0.020787 | −0.003141 | 0.001424 | −0.014367 | −0.010345 | −0.026979 | −0.024666 | −0.015176 |
| 322 | −0.028097 | −0.032448 | −0.012978 | 0.006791 | 0.020643 | −0.009834 | 0.002836 | 0.067761 | 0.015421 | 0.03191 | −0.006807 | 0.006688 | 0.014006 | −0.004363 |
| 323 | 0.014684 | −0.010938 | −0.014631 | −0.019757 | −0.005352 | 0.011666 | 0.00882 | 0.013339 | −0.011914 | −0.00415 | 0.011312 | 0.013863 | 0.014403 | 0.004532 |
| 324 | −0.032131 | −0.006511 | 0.000643 | 0.025641 | 0.000377 | −0.013553 | 0.004886 | 0.056065 | 0.015356 | −0.007308 | −0.023084 | −0.028764 | −0.004767 | 0.002865 |
| 325 | −0.00253 | 0.010487 | 0.01274 | 0.003836 | −0.001458 | 0.00428 | 0.001852 | −0.003838 | 0.006156 | −0.00312 | −0.004175 | −0.025411 | −0.026233 | −0.000126 |
| 326 | −0.040656 | 0.025656 | 0.019365 | −0.015417 | 0.003555 | −0.002926 | 0.002582 | −0.018706 | 0.005513 | −0.007063 | −0.021612 | −0.019124 | −0.015003 | −0.00057 |
| 327 | 0.016837 | 0.012934 | 0.003614 | 0.015625 | 0.007685 | 0.008998 | 0.010352 | 0.029479 | −0.002464 | −0.004659 | 0.000025 | 0.007709 | 0.000205 | −0.000306 |
| 328 | −0.050593 | 0.006761 | −0.003051 | −0.022416 | −0.020405 | 0.020842 | 0.009718 | −0.03084 | −0.011578 | −0.011039 | 0.004669 | 0.006914 | −0.00866 | −0.014126 |
| 329 | 0.002899 | 0.009755 | −0.010735 | −0.005586 | 0.017275 | 0.012185 | 0.002934 | 0.01794 | 0.019564 | −0.006103 | −0.00391 | −0.004176 | −0.006432 | −0.005201 |
| 330 | −0.023173 | −0.003718 | −0.005839 | −0.04357 | 0.035386 | 0.007538 | 0.018097 | −0.004705 | 0.002985 | 0.008704 | −0.011049 | −0.0518971 | −0.037959 | −0.018224 |
| 331 | 0.009112 | 0.012801 | 0.014113 | 0.011211 | −0.00146 | 0.003432 | 0.006707 | 0.009584 | 0.010573 | −0.01974 | 0.003851 | 0.017189 | 0.003028 | 0.011233 |
| 332 | −0.009889 | 0.015888 | 0.005081 | −0.010577 | −0.00593 | 0.01143 | 0.007901 | −0.015362 | 0.016263 | −0.002661 | 0.001425 | −0.017226 | −0.00691 | 0.001906 |
| 333 | −0.009701 | 0.001301 | 0.009152 | 0.007184 | 0.000045 | 0.007815 | 0.001497 | −0.009795 | −0.011662 | −0.004455 | 0.001675 | −0.000394 | −0.00324 | 0.005353 |
| 334 | −0.011931 | −0.000454 | −0.027606 | −0.025508 | 0.028753 | 0.032949 | −0.012031 | −0.038632 | −0.021017 | 0.001596 | 0.01137 | 0.004383 | −0.02634 | −0.014387 |
| 335 | −0.002736 | 0.011508 | 0.008733 | 0.006002 | −0.014337 | −0.004599 | −0.000848 | −0.012658 | 0.006665 | −0.011481 | 0.00247 | 0.013423 | 0.016165 | 0.023264 |
| 336 | 0.012715 | 0.005409 | 0.019794 | 0.024643 | 0.006156 | 0.012595 | 0.011157 | −0.01012 | 0.013148 | 0.009295 | 0.015565 | 0.035776 | 0.023877 | −0.001203 |
| 337 | −0.025129 | −0.007818 | −0.019308 | 0.008953 | −0.008196 | −0.002499 | −0.020064 | −0.023764 | −0.00184 | 0.011293 | −0.005409 | −0.005334 | −0.004537 | 0.008968 |
| 338 | 0.005374 | 0.018118 | −0.009234 | −0.02901 | 0.014177 | 0.016625 | 0.006827 | 0.043625 | 0.010205 | 0.021505 | 0.025504 | 0.004584 | 0.012086 | −0.010171 |
| 339 | −0.012776 | −0.00101 | −0.022379 | −0.016674 | −0.000179 | 0.016018 | 0.020598 | 0.000611 | −0.009964 | −0.008362 | −0.01008 | −0.009506 | −0.023887 | −0.018198 |
| 340 | 0.015428 | 0.026324 | 0.007821 | −0.016506 | 0.001034 | 0.010384 | −0.009389 | −0.01912 | −0.008245 | 0.00874 | 0.001008 | −0.01742 | 0.001272 | 0.036956 |

| | JD | JE | JF | JG | JH | JI | JJ | JK | JL | JM | JN | JO | JP | JQ |
|---|---|---|---|---|---|---|---|---|---|---|---|---|---|---|
| 1 | −0.021449 | 0.037127 | 0.078446 | 0.052769 | −0.013273 | −0.01391 | 0.004019 | 0.019846 | −0.006066 | 0.029375 | 0.066097 | 0.069208 | 0.10394 | −0.073445 |
| 2 | 0.027619 | −0.040331 | −0.029144 | 0.014757 | −0.053037 | −0.024813 | −0.012029 | −0.043638 | 0.039996 | −0.081786 | −0.010877 | −0.007755 | −0.004334 | 0.030622 |
| 3 | −0.038869 | 0.040514 | 0.061151 | 0.058673 | −0.088978 | −0.089601 | −0.093467 | −0.110949 | −0.075771 | −0.069963 | −0.085958 | −0.095351 | −0.121636 | 0.020241 |
| 4 | 0.021607 | 0.029559 | 0.052225 | 0.037317 | 0.004106 | −0.013327 | 0.002056 | −0.01682 | −0.042323 | −0.061109 | −0.045617 | −0.044094 | −0.06198 | −0.025486 |
| 5 | 0.011515 | −0.054772 | −0.058271 | 0.045239 | −0.084938 | −0.066004 | −0.051606 | −0.050323 | −0.01111 | −0.058332 | −0.051808 | −0.04167 | 0.037392 | 0.010171 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 6 | 0.104284 | −0.042585 | −0.002855 | 0.042094 | 0.001948 | −0.001193 | 0.01202 | 0.022202 | 0.108146 | 0.018429 | −0.010594 | −0.005334 | 0.004954 | 0.076692 |
| 7 | −0.051081 | −0.035625 | −0.077867 | −0.067458 | 0.056931 | 0.055778 | 0.071259 | 0.022466 | 0.109026 | 0.048267 | −0.013088 | −0.019392 | −0.049708 | 0.003936 |
| 8 | −0.016137 | 0.018787 | −0.020074 | −0.038974 | 0.02205 | 0.000205 | −0.015213 | −0.013695 | 0.058934 | −0.016539 | 0.001183 | 0.007324 | 0.03882 | −0.010918 |
| 9 | −0.011981 | −0.017472 | −0.058706 | −0.010765 | −0.035815 | −0.019497 | −0.020422 | −0.007452 | 0.029094 | −0.055659 | −0.033126 | −0.034519 | −0.013302 | 0.00632 |
| 10 | 0.020801 | −0.03599 | −0.023462 | 0.000284 | 0.057843 | −0.024216 | 0.032324 | 0.055965 | 0.070047 | −0.013818 | −0.011383 | −0.020518 | 0.019837 | – |
| 11 | 0.005874 | 0.055041 | 0.022673 | −0.033106 | −0.081361 | 0.020749 | 0.039269 | 0.044583 | −0.064292 | −0.028282 | 0.080473 | 0.088132 | 0.03346 | −0.006106 |
| 12 | 0.008878 | 0.053192 | 0.015877 | −0.026348 | −0.076902 | 0.032067 | 0.032034 | 0.032527 | −0.016938 | −0.000731 | 0.063905 | 0.067349 | 0.055074 | −0.038064 |
| 13 | −0.013701 | 0.078617 | 0.068723 | −0.012789 | 0.02835 | 0.042566 | 0.028072 | 0.032673 | 0.010562 | −0.024992 | −0.005753 | −0.005547 | −0.055821 | −0.023714 |
| 14 | −0.026016 | 0.007426 | −0.006131 | 0.01087 | −0.069712 | −0.005792 | −0.008173 | 0.012988 | −0.132859 | −0.097877 | −0.046246 | −0.048725 | −0.047782 | −0.068426 |
| 15 | −0.002142 | −0.001469 | −0.00406 | −0.045196 | 0.032131 | −0.02857 | −0.017101 | −0.015959 | 0.055049 | 0.058236 | −0.013576 | −0.004187 | 0.012543 | 0.080592 |
| 16 | −0.010509 | −0.024402 | −0.062998 | −0.045164 | 0.063914 | 0.017866 | 0.021893 | 0.042504 | 0.10486 | 0.036385 | 0.013465 | 0.007989 | 0.0395 | 0.035515 |
| 17 | 0.025758 | 0.032883 | 0.038466 | 0.016466 | 0.038513 | −0.002724 | 0.000674 | 0.0036 | 0.085536 | 0.024847 | 0.019099 | 0.011556 | 0.001805 | −0.029843 |
| 18 | 0.026137 | 0.017248 | −0.009746 | −0.009689 | 0.043014 | 0.009132 | −0.025033 | −0.011926 | 0.036769 | 0.074484 | 0.03743 | 0.033745 | −0.021316 | 0.043376 |
| 19 | 0.007737 | 0.051668 | 0.029599 | 0.002767 | 0.058909 | 0.057908 | 0.051724 | 0.067377 | −0.037158 | 0.018355 | 0.016622 | 0.014992 | 0.028581 | −0.0903 |
| 20 | 0.063884 | 0.000701 | 0.030347 | 0.043626 | 0.025706 | 0.00027 | −0.014666 | −0.023255 | 0.071538 | 0.050082 | 0.016352 | 0.009677 | −0.008915 | 0.051854 |
| 21 | 0.004814 | 0.043226 | 0.037931 | 0.020353 | −0.033813 | −0.011181 | −0.007431 | 0.002514 | −0.015923 | 0.038121 | 0.02453 | 0.024074 | 0.04615 | −0.051784 |
| 22 | 0.002371 | 0.004665 | −0.006797 | −0.023148 | 0.011699 | 0.092445 | 0.044923 | 0.066711 | −0.000101 | 0.005862 | 0.060759 | 0.054118 | −0.010898 | 0.007475 |
| 23 | −0.021143 | 0.001474 | −0.015291 | −0.061244 | −0.05906 | −0.024338 | −0.028942 | −0.017964 | −0.099356 | −0.106052 | −0.065056 | −0.071423 | −0.008312 | −0.061073 |
| 24 | −0.058547 | −0.017429 | 0.018963 | 0.005768 | 0.036265 | 0.003241 | 0.009831 | −0.046028 | −0.09396 | 0.016588 | 0.002314 | −0.002491 | −0.051217 | −0.017165 |
| 25 | 0.009653 | −0.063674 | −0.04551 | 0.031669 | −0.022728 | 0.056288 | 0.042074 | 0.06789 | 0.022932 | −0.003715 | −0.019444 | −0.017103 | 0.00897 | 0.054887 |
| 26 | 0.025245 | −0.048921 | −0.024461 | −0.060172 | 0.155194 | 0.028036 | −0.008346 | −0.00622 | 0.011283 | 0.042538 | 0.069427 | 0.047987 | 0.038143 | 0.040979 |
| 27 | −0.028144 | 0.048481 | 0.036257 | 0.033689 | 0.041992 | 0.033648 | 0.01766 | 0.036697 | 0.053717 | −0.104801 | −0.157376 | −0.155153 | −0.093451 | −0.104775 |
| 28 | −0.026862 | 0.003585 | −0.035593 | −0.024887 | −0.043831 | −0.045844 | −0.042278 | −0.043745 | −0.049588 | 0.05035 | 0.047203 | 0.04776 | −0.013235 | −0.014524 |
| 29 | −0.001818 | 0.006609 | 0.026744 | 0.004924 | 0.013824 | −0.000244 | 0.001965 | 0.00619 | −0.032649 | 0.031605 | 0.018555 | 0.019315 | 0.01618 | −0.018769 |
| 30 | −0.002492 | −0.16239 | −0.063256 | 0.045293 | −0.001584 | 0.060659 | 0.077597 | 0.046413 | −0.052304 | −0.051809 | 0.031298 | 0.02774 | −0.050942 | −0.027301 |
| 31 | −0.050513 | −0.045191 | −0.047861 | −0.003008 | 0.109429 | 0.033643 | 0.028077 | −0.0096 | 0.095953 | 0.101713 | −0.026446 | −0.027799 | −0.119939 | 0.003201 |
| 32 | 0.045429 | 0.031836 | −0.009435 | 0.004507 | −0.04091 | −0.01607 | 0.003589 | −0.004235 | −0.01205 | 0.004492 | 0.032981 | 0.028012 | 0.026671 | 0.042595 |
| 33 | 0.075417 | 0.005107 | −0.056021 | −0.044462 | −0.034335 | −0.03292 | −0.029615 | −0.006016 | −0.114755 | −0.061621 | −0.048166 | −0.044754 | 0.074767 | 0.128982 |
| 34 | 0.013979 | −0.022377 | −0.039883 | −0.034773 | −0.092818 | −0.033502 | −0.026405 | −0.05034 | −0.021134 | −0.034224 | −0.011326 | −0.01283 | −0.11173 | −0.052035 |
| 35 | 0.068863 | −0.051119 | −0.002077 | 0.033316 | −0.018858 | −0.004042 | −0.000884 | 0.010389 | 0.049516 | −0.021659 | 0.032894 | 0.034921 | 0.013619 | 0.021413 |
| 36 | −0.025843 | 0.039506 | 0.023677 | −0.015575 | 0.001723 | −0.032049 | −0.039233 | 0.00831 | 0.010548 | 0.031756 | 0.039634 | 0.039197 | 0.091795 | 0.000828 |
| 37 | −0.013139 | −0.023381 | −0.037343 | −0.015324 | −0.059771 | −0.026837 | −0.019092 | −0.016945 | −0.078059 | 0.006592 | 0.007459 | 0.015668 | −0.008228 | −0.076691 |
| 38 | 0.005857 | −0.023292 | −0.022658 | −0.011431 | 0.085268 | 0.010613 | 0.051374 | 0.007688 | −0.059116 | 0.013415 | −0.035997 | −0.032066 | −0.059476 | −0.001796 |
| 39 | 0.029433 | 0.003822 | −0.063962 | −9.077966 | −0.020484 | 0.024297 | 0.017629 | 0.012221 | 0.004279 | 0.026474 | 0.029206 | 0.029702 | 0.008912 | 0.017392 |
| 40 | 0.000362 | 0.008832 | −0.005612 | −0.009015 | 0.001149 | 0.003444 | −0.005182 | 0.006486 | 0.004039 | 0.00321 | 0.011045 | −0.000403 | 0.009463 | −0.007476 |
| 41 | 0.034247 | 0.011637 | 0.066864 | 0.020596 | −0.049784 | 0.015884 | −0.025816 | −0.001602 | −0.058317 | −0.071009 | −0.003435 | −0.018427 | −0.009591 | 0.037732 |
| 42 | −0.015628 | 0.004711 | −0.057169 | −0.027844 | 0.050148 | 0.017554 | 0.034966 | 0.02673 | −0.023741 | 0.032719 | 0.013832 | 0.011098 | 0.008106 | 0.026625 |
| 43 | −0.086776 | −0.029903 | −0.010624 | 0.025919 | 0.084455 | 0.009675 | 0.033697 | 0.027453 | −0.064733 | −0.029968 | −0.042708 | −0.018568 | 0.008246 | −0.048087 |
| 44 | 0.026356 | −0.003538 | −0.081928 | −0.13304 | 0.007034 | −0.001999 | 0.009829 | −0.013797 | 0.052367 | 0.004589 | 0.02929 | 0.029696 | 0.002673 | 0.034324 |
| 45 | −0.039094 | −0.034285 | 0.000548 | 0.080759 | −0.011271 | −0.027067 | −0.014259 | 0.029465 | 0.016748 | −0.003892 | 0.00677 | 0.014697 | 0.144934 | −0.04266 |
| 46 | 0.004184 | 0.042129 | 0.041054 | 0.033023 | −0.010507 | −0.052333 | −0.042132 | −0.084226 | 0.078683 | 0.072151 | −0.01642 | −0.009244 | −0.036875 | 0.01026 |
| 47 | 0.040344 | −0.083446 | −0.04714 | −0.026285 | 0.047627 | 0.020955 | 0.021495 | 0.04168 | 0.012729 | 0.032605 | 0.030086 | 0.031209 | −0.03232 | −0.065529 |
| 48 | −0.037293 | −0.02535 | −0.034465 | −0.062327 | 0.069133 | 0.031386 | 0.035922 | 0.066656 | −0.032415 | 0.03856 | 0.002043 | 0.006827 | 0.012027 | 0.004584 |
| 49 | −0.001891 | −0.011544 | −0.00202 | −0.045063 | −0.01517 | 0.02064 | 0.018747 | 0.050079 | −0.029419 | −0.060791 | 0.048439 | 0.041655 | 0.066749 | −0.03158 |
| 50 | −0.033288 | 0.026295 | 0.088646 | 0.078384 | 0.074348 | 0.031924 | 0.009465 | −0.060372 | 0.028072 | 0.107548 | 0.023316 | 0.014151 | −0.109275 | 0.004975 |
| 51 | −0.000083 | 0.023184 | 0.04193 | 0.01181 | −0.045029 | 0.004484 | 0.031797 | −0.001164 | −0.047723 | −0.09864 | −0.047816 | −0.032154 | −0.110904 | 0.010129 |
| 52 | 0.01039 | −0.017355 | −0.038271 | 0.002266 | −0.008569 | −0.028599 | 0.001878 | −0.015448 | 0.011153 | 0.03527 | 0.022724 | 0.033788 | 0.020795 | 0.016397 |
| 53 | 0.006993 | −0.074973 | −0.134325 | −0.066699 | −0.005097 | 0.027037 | 0.031795 | 0.022589 | 0.127208 | 0.043456 | −0.007108 | −0.009684 | −0.055388 | 0.037762 |
| 54 | 0.040917 | −0.008471 | 0.006063 | 0.016666 | −0.007183 | −0.025293 | −0.030337 | −0.00096 | 0.076664 | 0.047536 | 0.014349 | 0.010365 | −0.02219 | 0.037626 |
| 55 | −0.003188 | −0.00994 | −0.088261 | −0.06236 | −0.010327 | −0.060863 | −0.028145 | −0.020409 | 0.098365 | −0.000126 | −0.014127 | −0.003977 | 0.051164 | 0.028114 |

APPENDIX B3-continued

PCA Transformation
Matrix (340 × 340 Early/Late)

| | | | | | | | | | | | | | |
|---|---|---|---|---|---|---|---|---|---|---|---|---|---|
| 56 | −0.025864 | 0.083428 | 0.183647 | 0.120187 | 0.059459 | 0.032416 | 0.017419 | −0.013412 | 0.094236 | 0.04229 | −0.000536 | 0.009831 | −0.054504 | 0.028337 |
| 57 | −0.016324 | −0.033968 | −0.053997 | −0.071947 | −0.06211 | 0.009853 | −0.000916 | −0.022427 | 0.008828 | −0.034831 | 0.026068 | 0.025398 | −0.023205 | −0.041021 |
| 58 | 0.005989 | −0.004761 | −0.099986 | −0.101012 | −0.00154 | −0.015649 | −0.006197 | −0.018768 | −0.025566 | −0.004702 | 0.005949 | 0.008291 | 0.05874 | −0.042571 |
| 59 | −0.003191 | −0.001971 | 0.062129 | 0.085815 | −0.020118 | −0.018372 | −0.030848 | −0.002972 | 0.018098 | 0.015337 | −0.059124 | −0.053844 | −0.024638 | 0.009964 |
| 60 | 0.003498 | −0.000285 | −0.008393 | −0.004053 | 0.002457 | 0.006747 | 0.013799 | 0.010261 | 0.012994 | 0.015169 | 0.003139 | 0.005511 | 0.00937 | −0.008207 |
| 61 | −0.008322 | −0.000611 | −0.004938 | −0.005662 | 0.037353 | 0.000556 | 0.006473 | −0.012059 | 0.000155 | 0.018935 | −0.003646 | −0.003914 | −0.009491 | −0.009928 |
| 62 | 0.005452 | 0.012227 | −0.000583 | −0.032542 | 0.011309 | 0.019064 | 0.013943 | 0.013362 | −0.007099 | 0.002671 | 0.016242 | 0.01441 | −0.008117 | 0.006268 |
| 63 | 0.003768 | 0.004225 | −0.002639 | −0.026823 | 0.020052 | 0.015688 | 0.00866 | −0.002757 | −0.001043 | −0.002641 | 0.008288 | 0.004798 | −0.02264 | 0.013864 |
| 64 | −0.004647 | −0.006838 | −0.004095 | −0.009257 | −0.026237 | −0.001998 | −0.006521 | −0.008908 | 0.025717 | −0.012389 | −0.004449 | −0.002699 | −0.009426 | −0.018422 |
| 65 | 0.001 | −0.003718 | 0.00156 | −0.022337 | 0.014416 | 0.00264 | 0.000466 | −0.00748 | 0.016494 | 0.017842 | 0.009603 | 0.008423 | 0.006883 | 0.018406 |
| 66 | 0.007802 | 0.00076 | −0.006707 | −0.016582 | −0.001035 | −0.01051 | −0.005728 | −0.03527 | 0.024429 | 0.011718 | 0.001967 | 0.002451 | −0.010567 | 0.007123 |
| 67 | 0.016735 | −0.055677 | −0.049382 | −0.014701 | 0.0081 | 0.015229 | 0.0115 | 0.003393 | −0.01024 | 0.015774 | 0.02328 | 0.019337 | −0.023523 | 0.008879 |
| 68 | 0.013692 | −0.013853 | −0.027971 | −0.044953 | 0.012643 | 0.018369 | 0.007784 | −0.005946 | −0.010958 | 0.004286 | 0.018329 | 0.014589 | −0.028658 | −0.006067 |
| 69 | −0.005076 | −0.017618 | −0.010855 | −0.00306 | −0.004494 | −0.004368 | −0.000122 | 0.001647 | 0.015544 | −0.006723 | 0.003331 | 0.003587 | 0.015444 | 0.001574 |
| 70 | 0.006866 | 0.019283 | 0.027175 | 0.005049 | −0.021754 | −0.013469 | −0.009657 | −0.008464 | 0.010679 | 0.003456 | 0.007583 | 0.007117 | 0.015517 | −0.010178 |
| 71 | −0.008277 | 0.016845 | 0.038748 | 0.024719 | −0.03722 | 0.001606 | 0.000701 | −0.008187 | 0.013028 | −0.025545 | −0.005031 | −0.002262 | −0.021171 | 0.008008 |
| 72 | −0.014963 | 0.008278 | 0.029859 | 0.016427 | −0.028926 | 0.007284 | 0.007613 | 0.019846 | −0.01346 | −0.043116 | −0.015031 | −0.013383 | 0.0148 | 0.005643 |
| 73 | 0.017389 | 0.014901 | 0.028834 | 0.020813 | −0.012085 | −0.014139 | −0.012158 | −0.016011 | 0.012451 | 0.020555 | 0.006642 | 0.004482 | 0.018228 | 0.033724 |
| 74 | −0.009528 | 0.011831 | 0.012145 | −0.008457 | 0.006906 | 0.002836 | −0.003038 | −0.002197 | −0.013399 | −0.014577 | −0.028341 | −0.028058 | −0.02446 | −0.003445 |
| 75 | 0.008209 | 0.008209 | 0.00944 | −0.010104 | −0.004384 | −0.007035 | −0.007742 | −0.010619 | 0.019288 | 0.018129 | 0.006941 | 0.007336 | −0.005611 | 0.006252 |
| 76 | −0.007386 | −0.007194 | −0.010879 | −0.004034 | −0.002366 | −0.008165 | −0.004755 | −0.000423 | 0.017188 | 0.00604 | 0.003165 | 0.002907 | 0.011853 | 0.003157 |
| 77 | 0.002907 | 0.012036 | 0.015556 | −0.004647 | −0.00278 | −0.003519 | −0.004954 | −0.008539 | 0.021476 | 0.016124 | 0.006541 | 0.007015 | −0.002675 | 0.008629 |
| 78 | 0.004921 | 0.011703 | 0.014982 | −0.000787 | −0.016338 | −0.01127 | −0.011054 | −0.011312 | 0.022095 | 0.016643 | 0.002194 | 0.004084 | −0.002906 | 0.008508 |
| 79 | 0.013712 | −0.008649 | −0.018175 | −0.020937 | −0.003213 | −0.016751 | −0.015233 | −0.02195 | 0.042052 | 0.032305 | 0.006768 | 0.00664 | −0.001798 | −0.002329 |
| 80 | 0.000526 | 0.037962 | 0.056728 | 0.021054 | −0.006326 | −0.013673 | −0.006135 | −0.005056 | 0.052423 | 0.00981 | 0.005247 | 0.007152 | −0.002004 | 0.000498 |
| 81 | −0.012828 | 0.020519 | −0.00634 | −0.019156 | 0.022456 | −0.005479 | −0.010062 | 0.022309 | −0.041407 | −0.024323 | −0.005273 | −0.00599 | 0.051314 | −0.016354 |
| 82 | −0.007425 | −0.003774 | 0.001911 | 0.001469 | −0.003549 | 0.006353 | 0.012509 | 0.011265 | −0.006766 | 0.005198 | 0.021086 | 0.022278 | 0.028157 | −0.026237 |
| 83 | −0.002041 | −0.003703 | −0.000731 | −0.00065 | −0.014002 | −0.008804 | −0.001086 | −0.002868 | −0.001859 | 0.001651 | 0.012783 | 0.014929 | 0.017149 | −0.016562 |
| 84 | −0.001101 | 0.023171 | 0.029999 | 0.020889 | −0.010826 | −0.002016 | −0.002336 | 0.000421 | 0.014183 | 0.004974 | 0.007872 | 0.008639 | 0.012911 | −0.004785 |
| 85 | −0.01579 | 0.004654 | −0.015688 | −0.013516 | 0.000248 | −0.003736 | −0.007313 | 0.008904 | −0.029294 | −0.00314 | −0.01473 | −0.016577 | 0.019612 | −0.008948 |
| 86 | −0.013661 | 0.003933 | 0.014131 | 0.019109 | −0.018707 | 0.005355 | 0.00376 | 0.000205 | −0.013317 | −0.025871 | −0.016932 | −0.015851 | −0.007766 | 0.006964 |
| 87 | −0.00595 | −0.006698 | 0.012203 | 0.021641 | −0.018105 | −0.000088 | 0.010212 | 0.004644 | 0.009831 | −0.017493 | 0.001198 | 0.002337 | −0.010437 | −0.020166 |
| 88 | −0.002469 | −0.002752 | 0.002954 | 0.010564 | −0.007947 | −0.005907 | −0.000607 | −0.00312 | 0.014492 | 0.022827 | 0.017616 | 0.019383 | 0.010105 | −0.01522 |
| 89 | −0.000246 | −0.001884 | 0.010183 | 0.01703 | −0.019868 | −0.005959 | −0.003194 | −0.004548 | 0.014014 | 0.006939 | 0.008468 | 0.010935 | 0.000406 | −0.011277 |
| 90 | 0.000031 | −0.005225 | 0.010367 | 0.012697 | −0.006958 | −0.003299 | 0.000688 | −0.003104 | 0.021501 | −0.003326 | 0.002508 | 0.003634 | −0.00221 | −0.010435 |
| 91 | −0.004819 | 0.009894 | 0.023551 | 0.009849 | −0.006335 | 0.008876 | 0.0003 | 0.006826 | 0.021642 | 0.005641 | 0.013179 | 0.012988 | 0.023555 | −0.00451 |
| 92 | 0.006122 | 0.002308 | 0.009719 | 0.01566 | −0.009169 | 0.003299 | 0.001445 | 0.024323 | −0.023582 | −0.002383 | 0.012086 | 0.010844 | 0.045385 | 0.010102 |
| 93 | 0.00505 | 0.012117 | 0.021888 | −0.005449 | −0.011801 | 0.002447 | 0.001373 | 0.001408 | 0.005846 | −0.005149 | 0.020338 | 0.018832 | 0.017709 | 0.0044 |
| 94 | −0.00184 | −0.006359 | −0.004288 | 0.000699 | −0.013403 | 0.002734 | 0.00161 | 0.001787 | −0.0092 | −0.004202 | 0.008441 | 0.003903 | 0.017811 | 0.005653 |
| 95 | 0.022814 | −0.004007 | −0.002348 | 0.008234 | −0.037988 | −0.025964 | −0.025016 | −0.024025 | −0.044941 | −0.055353 | −0.001541 | −0.00172 | 0.007878 | −0.009676 |
| 96 | −0.012037 | 0.000135 | 0.009808 | 0.006262 | −0.022931 | −0.004283 | −0.003124 | 0.005662 | −0.017673 | 0.008048 | 0.003617 | 0.00363 | −0.001871 | −0.044142 |
| 97 | 0.006612 | −0.002744 | −0.022709 | −0.027216 | −0.030079 | −0.027816 | −0.019834 | −0.016685 | −0.023302 | −0.03113 | −0.015255 | −0.01863 | 0.00842 | 0.000225 |
| 98 | −0.004317 | −0.011722 | −0.008847 | 0.001355 | −0.000275 | 0.002981 | −0.000232 | 0.005109 | 0.002174 | −0.010499 | −0.006911 | −0.009788 | −0.005574 | 0.000537 |
| 99 | −0.001736 | −0.003593 | −0.003848 | −0.002866 | 0.003247 | −0.013724 | −0.013596 | −0.012229 | −0.016496 | 0.005723 | −0.003712 | −0.007287 | 0.001723 | 0.001021 |
| 100 | −0.013029 | −0.016719 | −0.025551 | −0.021358 | 0.007319 | −0.001182 | 0.002209 | −0.002447 | −0.026765 | 0.002797 | 0.007052 | 0.005916 | 0.000873 | 0.011358 |
| 101 | 0.009288 | 0.003058 | −0.007562 | −0.009165 | −0.016302 | 0.001308 | −0.006242 | −0.00001 | 0.010068 | −0.019468 | −0.004261 | −0.008331 | −0.005244 | 0.007124 |
| 102 | −0.004956 | 0.014774 | 0.02653 | 0.005703 | 0.01458 | 0.009496 | 0.006839 | 0.02355 | −0.021585 | −0.009286 | 0.012182 | 0.008455 | 0.01311 | −0.015617 |
| 103 | 0.011211 | 0.010416 | −0.012459 | −0.041143 | 0.000752 | 0.002316 | 0.007117 | −0.001123 | 0.008006 | −0.01126 | 0.01749 | 0.016408 | −0.019675 | −0.028247 |
| 104 | −0.000982 | 0.012113 | 0.01857 | −0.003388 | 0.020396 | −0.005725 | 0.001536 | 0.004304 | 0.010754 | 0.007423 | 0.0055861 | 0.009143 | 0.013079 | 0.002862 |
| 105 | −0.01723 | 0.029916 | 0.02713 | 0.006064 | −0.01179f | −0.018284 | −0.013748 | −0.005659 | 0.012592 | 0.048306 | 0.027413 | 0.031061 | 0.012839 | −0.002469 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 106 | −0.005665 | 0.010795 | 0.01084 | 0.010339 | 0.011414 | 0.020885 | 0.01911 | 0.008272 | 0.022197 | 0.001275 | −0.006784 | −0.005813 | −0.020352 | −0.003641 |
| 107 | −0.006817 | 0.02611 | 0.020702 | 0.015715 | −0.002963 | 0.00571 | 0.008661 | 0.007941 | −0.000222 | −0.001051 | 0.001708 | 0.000911 | 0.004825 | 0.004758 |
| 108 | −0.014991 | 0.031231 | 0.027134 | −0.000718 | −0.023414 | 0.003332 | −0.004743 | −0.00366 | −0.014333 | 0.017437 | 0.029621 | 0.025572 | −0.00747 | −0.044182 |
| 109 | 0.010252 | 0.001329 | 0.008887 | 0.004391 | 0.018192 | 0.001769 | −0.002015 | 0.035327 | −0.00754 | −0.027419 | 0.002929 | −0.000068 | 0.053561 | 0.003709 |
| 110 | 0.018708 | 0.027134 | −0.008885 | −0.021425 | −0.016443 | −0.010471 | 0.002403 | −0.015994 | 0.031578 | 0.01965 | 0.01221 | 0.016135 | 0.013934 | 0.041047 |
| 111 | −0.002615 | 0.020832 | 0.004956 | 0.001021 | −0.027202 | −0.009729 | −0.01018 | −0.000422 | −0.015796 | 0.020815 | 0.005731 | 0.006265 | 0.022691 | −0.029196 |
| 112 | −0.015596 | 0.012286 | 0.025376 | 0.020636 | −0.008733 | −0.028485 | −0.0305881 | −0.038491 | 0.015445 | 0.027916 | 0.010756 | 0.009457 | −0.006792 | −0.008086 |
| 113 | −0.012503 | 0.012253 | 0.025752 | 0.024286 | 0.011447 | 0.018975 | 0.011917 | 0.016884 | −0.004359 | −0.02069 | −0.014176 | −0.017858 | −0.006153 | −0.040017 |
| 114 | −0.019441 | −0.013439 | −0.016277 | −0.012823 | 0.04334 | 0.004982 | 0.015091 | 0.013409 | 0.001999 | −0.022089 | −0.009358 | −0.008541 | 0.003525 | −0.02611 |
| 115 | 0.009835 | 0.038755 | 0.00389 | −0.020464 | −0.023047 | 0.000861 | −0.006309 | −0.020698 | 0.000705 | 0.027857 | 0.021386 | 0.019498 | −0.005717 | 0.017304 |
| 116 | 0.017588 | −0.034202 | −0.023274 | −0.026728 | 0.017082 | −0.019665 | −0.019068 | −0.018768 | −0.005076 | 0.012212 | 0.006719 | 0.003105 | 0.015618 | 0.007411 |
| 117 | −0.015194 | 0.018134 | 0.006078 | −0.004779 | 0.031441 | −0.003286 | −0.006359 | −0.006678 | 0.03623 | 0.019536 | 0.004428 | 0.002079 | 0.00976 | −0.008196 |
| 118 | 0.013421 | −0.000441 | 0.025424 | 0.006925 | 0.003667 | 0.019788 | 0.015927 | 0.01607 | 0.014726 | 0.003617 | 0.033443 | 0.025688 | −0.026802 | 0.006678 |
| 119 | −0.007205 | −0.000044 | 0.000518 | 0.004189 | −0.018445 | −0.000231 | 0.000034 | −0.012191 | 0.017957 | −0.019781 | −0.011506 | −0.013415 | −0.019543 | 0.020781 |
| 120 | −0.000447 | 0.015842 | 0.010414 | −0.000969 | −0.001025 | −0.00626 | −0.012201 | −0.015258 | 0.034327 | 0.002989 | −0.003655 | −0.004035 | −0.012941 | −0.002035 |
| 121 | −0.001866 | −0.002378 | 0.023474 | −0.005962 | 0.04499 | −0.000929 | −0.008382 | −0.004476 | 0.004492 | 0.028814 | 0.001091 | −0.000208 | −0.003268 | 0.015346 |
| 122 | 0.007634 | 0.030493 | 0.027391 | 0.017638 | −0.007892 | −0.016581 | −0.015294 | −0.014141 | −0.022121 | −0.005883 | 0.004714 | 0.004523 | 0.029882 | −0.004788 |
| 123 | −0.00403 | 0.029242 | 0.019095 | 0.002407 | −0.003474 | −0.009797 | −0.009122 | −0.020198 | −0.012102 | 0.002071 | 0.015556 | 0.018535 | 0.024243 | 0.015375 |
| 124 | −0.003082 | 0.008246 | −0.006197 | −0.007613 | −0.017107 | −0.01311 | −0.012574 | −0.029984 | 0.009854 | −0.01471 | −0.018983 | −0.021456 | −0.027132 | 0.018325 |
| 125 | −0.016743 | 0.012579 | 0.020176 | 0.011565 | −0.001421 | −0.001297 | −0.009241 | −0.010901 | 0.018737 | −0.005275 | −0.012182 | −0.008997 | −0.030434 | −0.004135 |
| 126 | 0.009212 | −0.01191 | 0.035015 | 0.044082 | 0.024842 | 0.015137 | 0.015679 | 0.018594 | −0.002076 | −0.007476 | −0.001717 | −0.002098 | −0.003087 | 0.018701 |
| 127 | 0.005827 | −0.04598 | −0.015746 | 0.023253 | 0.014792 | 0.015757 | 0.018368 | 0.012612 | 0.009186 | −0.010349 | −0.011538 | −0.010036 | −0.017906 | 0.025881 |
| 128 | −0.015258 | 0.014696 | 0.023064 | 0.00464 | 0.005196 | −0.005012 | 0.008493 | 0.001567 | −0.009641 | −0.001286 | 0.000705 | 0.006974 | 0.010652 | 0.00886 |
| 129 | 0.008838 | −0.001558 | −0.023991 | −0.011534 | −0.0624 | −0.034566 | −0.015381 | −0.027968 | −0.055623 | 0.007177 | −0.00108 | 0.004252 | −0.000889 | 0.022537 |
| 130 | 0.022539 | 0.003578 | 0.009198 | −0.001069 | −0.025779 | −0.011136 | −0.011598 | −0.018219 | −0.016883 | 0.022423 | 0.021758 | 0.020447 | 0.001262 | −0.001807 |
| 131 | −0.025925 | −0.007093 | −0.026283 | −0.025555 | −0.053919 | −0.008763 | −0.000895 | 0.006569 | 0.008853 | −0.003654 | 0.014553 | 0.010064 | 0.03063 | −0.015523 |
| 132 | −0.01154 | 0.016813 | 0.012556 | 0.008425 | −0.032827 | −0.009574 | 0.006295 | 0.003584 | −0.007418 | −0.011393 | 0.003407 | 0.009873 | 0.029719 | −0.009925 |
| 133 | 0.011725 | −0.009096 | −0.015945 | −0.021573 | 0.01852 | 0.007631 | 0.011653 | 0.011832 | −0.001399 | −0.003075 | 0.022308 | 0.019978 | 0.023987 | 0.019075 |
| 134 | −0.008568 | −0.003087 | 0.028685 | 0.013626 | 0.004616 | 0.005911 | −0.002508 | −0.001678 | −0.023979 | −0.015548 | −0.02871 | −0.031734 | −0.037319 | −0.022356 |
| 135 | −0.006467 | −0.010269 | 0.014412 | 0.022193 | 0.003075 | −0.002216 | −0.00233 | −0.006319 | 0.012957 | 0.000142 | −0.008235 | −0.00465 | −0.019768 | 0.004847 |
| 136 | 0.012336 | −0.021794 | −0.038406 | −0.020755 | 0.003517 | 0.020714 | 0.02355 | 0.018573 | −0.013763 | 0.003425 | 0.008769 | 0.00658 | 0.011704 | 0.004631 |
| 137 | −0.012012 | −0.003551 | −0.001426 | −0.002654 | −0.001071 | 0.00824 | 0.014517 | 0.001538 | 0.006836 | −0.018465 | −0.025927 | −0.02466 | −0.046869 | 0.010573 |
| 138 | 0.020139 | −0.016451 | 0.019093 | 0.019294 | −0.004748 | 0.007584 | 0.003915 | 0.028658 | −0.019328 | −0.020268 | −0.006853 | −0.009551 | 0.019354 | −0.017953 |
| 139 | −0.016843 | 0.008342 | 0.002445 | −0.007494 | 0.012831 | 0.028294 | 0.037196 | 0.033061 | −0.004016 | −0.010827 | −0.005093 | −0.007485 | −0.030213 | −0.009856 |
| 140 | −0.012128 | 0.012284 | 0.009013 | 0.006532 | 0.034794 | 0.0072 | 0.006312 | 0.0105 | 0.015148 | 0.044096 | 0.006928 | 0.004979 | 0.053809 | 0.0263 |
| 141 | −0.00723 | −0.004551 | 0.013806 | 0.027547 | 0.00445 | −0.008416 | 0.000485 | −0.005443 | −0.032496 | 0.003307 | 0.005231 | 0.010373 | −0.013378 | 0.001432 |
| 142 | 0.010932 | −0.004443 | −0.016507 | −0.011083 | 0.002534 | −0.02983 | −0.024838 | −0.029884 | −0.001996 | 0.001833 | −0.009479 | −0.011477 | −0.014095 | 0.012066 |
| 143 | −0.009527 | 0.018011 | 0.015343 | −0.001686 | 0.003196 | −0.01569 | −0.01495 | −0.007745 | −0.039096 | −0.010185 | 0.011574 | 0.013733 | 0.03738 | −0.010047 |
| 144 | 0.008174 | −0.012657 | −0.005247 | 0.00619 | 0.012022 | 0.003418 | 0.00681 | −0.011021 | −0.007409 | −0.00358 | 0.00291 | 0.003606 | −0.019537 | 0.001909 |
| 145 | 0.006512 | −0.004772 | 0.006818 | −0.000705 | 0.004227 | 0.001141 | 0.013866 | 0.007258 | 0.004352 | −0.039613 | 0.011714 | 0.012817 | 0.036947 | 0.008866 |
| 146 | −0.013328 | −0.009741 | 0.010188 | 0.014861 | 0.023404 | 0.003395 | 0.006415 | −0.003141 | 0.002688 | 0.003109 | −0.013249 | −0.011592 | −0.023368 | −0.005615 |
| 147 | −0.011305 | −0.004076 | 0.028015 | 0.032132 | 0.034883 | 0.010808 | 0.015992 | 0.011657 | 0.019738 | 0.016875 | 0.009431 | 0.00917 | −0.008013 | −0.004292 |
| 148 | 0.018503 | −0.037295 | −0.058806 | −0.023584 | 0.007272 | 0.004097 | 0.017406 | 0.002432 | 0.010019 | −0.005947 | −0.004852 | −0.00886 | −0.022417 | −0.011842 |
| 149 | −0.00226 | 0.01427 | −0.001783 | −0.015357 | 0.008704 | −0.005393 | 0.003886 | 0.004158 | −0.00104 | 0.002631 | 0.001303 | 0.006278 | 0.016527 | −0.01246 |
| 150 | −0.002356 | −0.003781 | 0.009479 | −0.00242 | 0.016513 | −0.004645 | −0.015063 | −0.023287 | −0.00776 | 0.003856 | −0.014188 | −0.017767 | −0.029837 | 0.014485 |
| 151 | −0.004517 | 0.013416 | 0.016987 | 0.015232 | 0.035326 | 0.000025 | 0.004149 | −0.005168 | 0.018535 | 0.040792 | 0.002505 | 0.003701 | −0.007003 | 0.020939 |
| 152 | 0.000285 | −0.035484 | −0.027252 | 0.003473 | 0.000529 | 0.004175 | 0.004762 | −0.000627 | 0.019362 | 0.021723 | 0.005435 | 0.006907 | −0.005979 | 0.018298 |
| 153 | 0.003187 | −0.001102 | 0.006633 | 0.005392 | 0.014692 | 0.008454 | 0.009543 | −0.006049 | 0.003256 | 0.016757 | 0.010287 | 0.011061 | −0.040906 | 0.013442 |
| 154 | 0.019583 | −0.002228 | 0.012636 | 0.007944 | 0.001434 | −0.005002 | −0.00652 | −0.004587 | 0.007993 | 0.011042 | 0.002976 | 0.002489 | 0.01281 | 0.019254 |
| 155 | −0.002937 | −0.002195 | 0.010545 | 0.003546 | −0.005066 | 0.009917 | 0.016676 | 0.021384 | 0.023282 | −0.00031 | 0.003017 | 0.009114 | 0.024081 | −0.013971 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 156 | −0.023302 | 0.003836 | 0.038017 | 0.010882 | 0.020654 | 0.019869 | 0.008923 | 0.017789 | −0.042986 | −0.008024 | 0.019641 | 0.019642 | 0.015325 | −0.024013 |
| 157 | −0.0087 | 0.004461 | −0.001428 | 0.002889 | 0.033122 | −0.000256 | 0.000714 | 0.000122 | 0.014717 | 0.007787 | −0.018216 | −0.015872 | 0.001789 | 0.010268 |
| 158 | −0.028379 | −0.004063 | −0.00045 | 0.009248 | 0.02716 | −0.009503 | −0.003177 | −0.015738 | 0.028341 | 0.052637 | 0.01302 | 0.016943 | 0.000114 | 0.009869 |
| 159 | 0.003261 | −0.012841 | 0.001598 | −0.011649 | −0.025493 | −0.035815 | −0.02219 | −0.017411 | 0.010326 | −0.000964 | −0.002293 | 0.002931 | 0.009767 | 0.043101 |
| 160 | −0.007121 | 0.014495 | 0.018421 | 0.009088 | 0.026342 | 0.016563 | 0.005563 | 0.004943 | 0.048263 | 0.008826 | 0.005046 | 0.001675 | −0.018193 | 0.044434 |
| 161 | −0.016996 | −0.006721 | −0.014762 | 0.000549 | 0.003645 | −0.01691 | 0.008304 | 0.001916 | 0.011672 | 0.015182 | −0.00397 | 0.003958 | 0.00798 | −0.009902 |
| 162 | 0.010078 | −0.014292 | 0.001289 | −0.0047 | 0.005247 | 0.01377 | 0.010533 | −0.000887 | −0.02617 | −0.029363 | 0.003353 | −0.000839 | −0.026328 | 0.006958 |
| 163 | −0.009131 | −0.022551 | −0.02292 | −0.001601 | 0.001954 | −0.00627 | −0.001675 | −0.010161 | 0.015356 | 0.001638 | −0.011031 | −0.009801 | −0.025801 | 0.012954 |
| 164 | 0.000733 | −0.019073 | −0.03388 | −0.019659 | 0.059109 | 0.031674 | 0.036538 | 0.034355 | 0.036432 | 0.039606 | 0.027282 | 0.024083 | 0.004783 | 0.006456 |
| 165 | 0.002717 | 0.019764 | 0.030465 | 0.015133 | 0.046687 | 0.020968 | 0.021571 | 0.035562 | 0.005012 | 0.018676 | −0.004139 | −0.000922 | 0.018554 | −0.011797 |
| 166 | 0.011698 | 0.005812 | −0.029873 | −0.025372 | −0.005301 | −0.010434 | −0.017911 | −0.008374 | 0.016152 | −0.011068 | −0.022667 | −0.025064 | 0.003675 | −0.020899 |
| 167 | −0.021821 | −0.002297 | 0.013524 | 0.01159 | 0.023378 | 0.028183 | 0.030798 | 0.020944 | −0.015834 | −0.023069 | −0.007794 | −0.006952 | −0.021255 | −0.035653 |
| 168 | 0.009415 | −0.015889 | −0.01522 | −0.004561 | −0.002592 | 0.0087 | 0.010693 | −0.003977 | −0.002506 | 0.026281 | 0.019114 | 0.015262 | −0.044528 | 0.032473 |
| 169 | 0.006467 | 0.00072 | 0.004932 | 0.014534 | −0.019484 | −0.002123 | −0.002437 | −0.003831 | 0.022812 | −0.006874 | 0.002287 | 0.002946 | −0.005298 | −0.010196 |
| 170 | 0.019124 | −0.01096 | −0.011576 | 0.003296 | −0.030339 | −0.000328 | −0.00096 | −0.000943 | −0.000577 | −0.017777 | 0.014385 | 0.012561 | 0.010616 | −0.003857 |
| 171 | 0.002282 | −0.002028 | 0.009804 | 0.02279 | −0.017672 | −0.009487 | −0.004816 | −0.002924 | −0.00248 | 0.024406 | 0.023544 | 0.026581 | 0.013712 | −0.001123 |
| 172 | −0.015446 | 0.013016 | 0.006877 | −0.000897 | −0.008311 | −0.007562 | −0.006062 | −0.000858 | 0.016396 | −0.013774 | −0.018948 | −0.015976 | −0.005903 | −0.008725 |
| 173 | 0.014463 | 0.001983 | 0.000364 | −0.009312 | 0.007206 | 0.003821 | 0.00509 | 0.006448 | 0.022346 | −0.0003 | −0.004529 | −0.001485 | −0.004468 | 0.015969 |
| 174 | 0.011991 | 0.004156 | −0.002336 | −0.000445 | −0.01656 | 0.006262 | 0.013375 | 0.007921 | 0.041682 | 0.009497 | 0.009194 | 0.013918 | 0.000706 | −0.004573 |
| 175 | −0.015464 | 0.01321 | −0.003029 | 0.012428 | 0.002298 | −0.00805 | 0.001772 | −0.012254 | 0.045978 | 0.027119 | −0.006265 | −0.001907 | 0.000346 | −0.048286 |
| 176 | −0.017706 | 0.00236 | −0.015644 | −0.020538 | −0.010715 | 0.003909 | 0.006169 | 0.007734 | −0.02767 | 0.008146 | 0.020751 | 0.020287 | 0.014935 | −0.049787 |
| 177 | 0.012449 | 0.020284 | 0.05158 | 0.038792 | 0.019726 | 0.029844 | 0.013967 | 0.00651 | 0.054256 | 0.031842 | 0.017321 | 0.012692 | −0.044049 | 0.020741 |
| 178 | −0.007127 | 0.005254 | 0.016103 | 0.023604 | 0.018927 | 0.01116 | 0.018057 | −0.004796 | 0.022333 | 0.012688 | −0.003499 | −0.004262 | −0.039042 | 0.027016 |
| 179 | 0.001195 | −0.005807 | 0.000002 | 0.008836 | 0.007875 | 0.005105 | 0.002645 | 0.001972 | 0.020849 | 0.010896 | 0.005192 | 0.002412 | −0.00891 | 0.011917 |
| 180 | 0.00733 | −0.004585 | 0.001306 | 0.003301 | 0.002656 | 0.014056 | 0.008434 | 0.005055 | 0.01691 | 0.003925 | 0.00359 | −0.000505 | −0.021803 | 0.008572 |
| 181 | 0.002552 | 0.000792 | −0.000462 | −0.000823 | 0.003299 | 0.011188 | 0.007083 | 0.009326 | 0.015053 | −0.000147 | 0.005184 | 0.001984 | −0.004087 | 0.00574 |
| 182 | 0.003069 | −0.008576 | −0.011737 | −0.008652 | 0.014191 | 0.005843 | 0.003521 | 0.0013 | 0.007212 | 0.020884 | 0.015845 | 0.011368 | 0.003753 | 0.018019 |
| 183 | −0.011825 | −0.01085 | 0.008823 | 0.015996 | 0.009392 | −0.007283 | −0.00499 | −0.001826 | −0.004909 | 0.027539 | 0.014984 | 0.016612 | 0.016105 | 0.018201 |
| 184 | −0.0161 | −0.009369 | −0.008798 | −0.012267 | −0.039008 | −0.022107 | −0.013381 | −0.007234 | −0.014286 | −0.006847 | 0.01267 | 0.019981 | 0.028871 | 0.002364 |
| 185 | −0.004979 | 0.038333 | 0.025367 | −0.025055 | 0.004329 | −0.01353 | −0.022399 | −0.021917 | 0.047055 | 0.010715 | −0.00903 | −0.007338 | −0.001481 | 0.009571 |
| 186 | 0.017316 | 0.016662 | −0.032954 | −0.054195 | −0.032808 | −0.004831 | −0.00373 | 0.013135 | −0.02783 | −0.010456 | 0.008936 | 0.009796 | 0.035649 | −0.003515 |
| 187 | 0.017414 | −0.015036 | −0.014038 | −0.017454 | −0.004478 | 0.005158 | 0.003132 | −0.002309 | 0.004071 | −0.020065 | −0.001118 | −0.003205 | −0.016024 | 0.02198 |
| 188 | 0.013472 | −0.012541 | −0.005209 | −0.00939 | −0.010728 | 0.014685 | 0.013278 | 0.008481 | 0.015831 | −0.008327 | 0.014204 | 0.01198 | −0.007703 | 0.00684 |
| 189 | 0.006543 | −0.015119 | −0.028598 | −0.020472 | −0.028817 | −0.001966 | −0.001466 | −0.000669 | 0.004633 | 0.000732 | 0.023632 | 0.019984 | 0.006014 | −0.02032 |
| 190 | −0.016588 | −0.003175 | −0.023209 | −0.029678 | 0.005466 | 0.007691 | 0.008972 | 0.004793 | 0.004703 | −0.005255 | −0.00387 | −0.00301 | −0.000033 | −0.021822 |
| 191 | −0.001122 | 0.002733 | −0.009269 | −0.00601 | −0.005228 | −0.001461 | −0.001012 | 0.009172 | 0.011035 | −0.002621 | −0.004904 | −0.002905 | 0.015388 | −0.002223 |
| 192 | −0.002655 | −0.056034 | −0.012764 | 0.026925 | 0.031324 | −0.012678 | −0.002516 | −0.012334 | −0.000993 | 0.00793 | −0.013505 | −0.012029 | 0.003859 | 0.040412 |
| 193 | −0.000867 | −0.040906 | −0.049712 | −0.016454 | −0.006282 | −0.003181 | 0.004726 | −0.003309 | 0.01233 | −0.005603 | −0.000348 | 0.003228 | 0.000662 | 0.012107 |
| 194 | −0.008165 | −0.011001 | −0.016696 | −0.010047 | 0.003078 | 0.008494 | 0.002409 | −0.005411 | 0.021181 | 0.014763 | 0.004693 | 0.003269 | −0.011694 | −0.000151 |
| 195 | −0.004273 | 0.010708 | −0.061726 | −0.083715 | −0.015653 | −0.024567 | −0.021127 | −0.008791 | 0.002648 | −0.027036 | −0.021402 | −0.019546 | 0.029418 | −0.002308 |
| 196 | −0.01331 | −0.001716 | −0.043734 | −0.050747 | 0.001511 | −0.011434 | −0.009519 | −0.010116 | 0.018638 | −0.002654 | −0.013407 | −0.014079 | 0.014777 | −0.019609 |
| 197 | −0.014366 | 0.003002 | −0.007757 | −0.021266 | 0.012566 | −0.005021 | 0.001203 | −0.003529 | 0.011169 | 0.013656 | 0.007604 | 0.011224 | 0.021317 | −0.024518 |
| 198 | −0.011645 | 0.033274 | 0.01125 | −0.017284 | −0.020358 | −0.025101 | −0.022928 | −0.027012 | −0.020798 | −0.020569 | −0.013452 | −0.011947 | −0.011593 | 0.004987 |
| 199 | 0.005683 | 0.020713 | −0.021557 | 0.000133 | −0.035626 | −0.015678 | 0.005347 | 0.0027 | −0.002269 | −0.006168 | −0.02597 | −0.019047 | −0.01291 | −0.024653 |
| 200 | −0.033537 | 0.012577 | 0.021248 | 0.023384 | 0.003177 | −0.001595 | 0.006262 | 0.005676 | −0.020839 | −0.002357 | −0.01052 | −0.007176 | −0.025034 | 0.006224 |
| 201 | 0.012255 | −0.004327 | 0.005366 | −0.001722 | 0.013573 | 0.019574 | 0.016143 | 0.014139 | −0.025446 | −0.003011 | 0.009033 | 0.0029 | −0.015067 | 0.025057 |
| 202 | −0.017695 | 0.02541 | 0.014705 | 0.000155 | −0.000183 | −0.007739 | −0.008523 | −0.011254 | −0.036312 | −0.005277 | −0.013846 | −0.011932 | −0.001894 | 0.013609 |
| 203 | −0.014355 | −0.01141 | 0.003605 | 0.006817 | −0.012664 | −0.000341 | 0.015224 | −0.000036 | 0.002016 | −0.029545 | −0.00992 | −0.005295 | −0.009162 | −0.003917 |
| 204 | −0.007429 | −0.035107 | −0.041489 | −0.03748 | −0.01108 | −0.004169 | −0.008193 | 0.009373 | −0.039734 | −0.008472 | −0.005904 | −0.006956 | 0.024147 | −0.003432 |
| 205 | −0.03375 | −0.005118 | 0.021035 | 0.018437 | 0.031672 | 0.032049 | 0.021274 | 0.041312 | 0.026595 | 0.009539 | −0.009355 | −0.010944 | −0.012873 | −0.02444 |

APPENDIX B3-continued

PCA Transformation
Matrix (340 × 340 Early/Late)

| | | | | | | | | | | | | | |
|---|---|---|---|---|---|---|---|---|---|---|---|---|---|
| 206 | −0.035499 | −0.01959 | −0.025728 | −0.018501 | 0.006232 | 0.020595 | 0.015188 | −0.016611 | 0.004751 | 0.000414 | −0.000127 | −0.008284 | −0.055863 | −0.02404 |
| 207 | 0.002166 | −0.008209 | 0.00125 | 0.012706 | 0.011731 | 0.029463 | 0.027558 | 0.032899 | −0.006043 | −0.024673 | −0.018693 | −0.022154 | −0.035691 | −0.037718 |
| 208 | 0.01518 | −0.009804 | 0.014334 | 0.00746 | −0.043583 | 0.003499 | 0.000013 | 0.00516 | 0.001863 | −0.02322 | 0.023409 | 0.026623 | 0.026029 | −0.002216 |
| 209 | −0.013235 | −0.035598 | −0.001155 | 0.006965 | 0.031089 | −0.019497 | −0.007564 | −0.017129 | −0.010494 | 0.038373 | 0.00275 | 0.008623 | 0.022798 | −0.000529 |
| 210 | −0.026851 | 0.031151 | 0.034635 | 0.011491 | 0.039151 | 0.007217 | 0.019215 | 0.014018 | 0.026487 | 0.065622 | 0.004655 | 0.01499 | 0.00863 | −0.049337 |
| 211 | −0.014678 | 0.01074 | 0.03067 | 0.002701 | 0.048774 | 0.024337 | 0.01358 | 0.031892 | −0.011613 | 0.022364 | −0.00338 | −0.003275 | 0.006143 | −0.000139 |
| 212 | −0.006773 | −0.003141 | −0.032499 | −0.050527 | 0.008659 | −0.013464 | −0.011868 | 0.009653 | 0.040616 | −0.010027 | 0.009776 | 0.010015 | 0.033427 | −0.016761 |
| 213 | −0.012901 | 0.022501 | −0.020037 | −0.022634 | −0.022667 | 0.018265 | 0.012621 | 0.027798 | 0.026017 | −0.017323 | 0.020887 | 0.015417 | 0.041114 | 0.001473 |
| 214 | 0.005524 | −0.009942 | −0.005621 | 0.00282 | −0.001562 | −0.000317 | −0.005111 | −0.000522 | −0.002802 | 0.00404 | −0.002789 | −0.005278 | −0.006071 | 0.023169 |
| 215 | 0.007487 | 0.009565 | 0.006983 | 0.023745 | −0.03488 | −0.017381 | −0.021332 | −0.007193 | 0.073851 | 0.039979 | 0.008657 | 0.012601 | −0.004297 | 0.025357 |
| 216 | 0.010383 | 0.008858 | 0.007543 | 0.004146 | −0.012405 | 0.012842 | 0.01351 | 0.00776 | 0.018806 | 0.0439 | 0.043093 | 0.041482 | −0.02595 | −0.00307 |
| 217 | −0.021698 | 0.013396 | −0.003766 | −0.017666 | −0.005933 | 0.009445 | 0.007062 | 0.006874 | −0.003189 | −0.005152 | −0.000946 | −0.000299 | 0.008791 | 0.001284 |
| 218 | 0.013598 | 0.007169 | 0.009479 | 0.014042 | −0.020553 | −0.00488 | −0.003284 | 0.013224 | −0.000606 | −0.004908 | 0.004728 | 0.009488 | 0.039441 | −0.005549 |
| 219 | 0.00935 | 0.006385 | 0.007485 | 0.003063 | 0.007441 | −0.000863 | 0.002888 | 0.007106 | −0.003119 | 0.010687 | 0.021419 | 0.023323 | 0.015051 | 0.00054 |
| 220 | −0.013748 | 0.003714 | −0.012839 | −0.032603 | −0.014686 | 0.005804 | −0.000453 | −0.002184 | 0.00694 | 0.003149 | −0.000547 | −0.000033 | 0.001165 | 0.003826 |
| 221 | 0.008167 | 0.004171 | 0.027866 | 0.00149 | 0.015063 | 0.005124 | −0.00553 | 0.007821 | 0.001788 | 0.009203 | 0.007696 | 0.006793 | 0.018148 | 0.017304 |
| 222 | −0.004555 | −0.053122 | −0.021771 | 0.012095 | 0.025288 | 0.004071 | 0.004943 | 0.011202 | 0.008801 | 0.001984 | −0.007564 | −0.005097 | 0.002097 | 0.014522 |
| 223 | 0.004346 | −0.026995 | −0.034942 | −0.014314 | 0.009095 | 0.007013 | 0.006186 | 0.014809 | 0.01136 | 0.011722 | 0.007632 | 0.009596 | 0.017729 | 0.004547 |
| 224 | −0.010953 | 0.001503 | −0.008247 | −0.000944 | −0.015537 | −0.004682 | −0.005232 | −0.012942 | 0.005287 | 0.02778 | 0.005558 | 0.005379 | −0.036553 | −0.007986 |
| 225 | −0.005817 | 0.007747 | 0.000642 | 0.002777 | −0.015416 | −0.005597 | −0.007705 | −0.008266 | 0.006536 | 0.02018 | 0.003399 | 0.003443 | −0.022806 | 0.00305 |
| 226 | 0.003825 | 0.01385 | 0.010169 | 0.012156 | −0.042655 | −0.063854 | −0.057862 | −0.059147 | −0.029663 | −0.019327 | −0.018283 | −0.016264 | 0.013493 | 0.004677 |
| 227 | −0.001557 | 0.00692 | 0.015878 | 0.029929 | −0.01731 | −0.048997 | −0.044074 | −0.088835 | 0.043731 | 0.046672 | −0.005571 | −0.007213 | −0.079215 | 0.023312 |
| 228 | −0.027246 | −0.024907 | −0.02483 | −0.003852 | −0.043855 | −0.023361 | −0.01328 | −0.010431 | −0.042797 | −0.037285 | −0.003463 | −0.001992 | 0.015613 | −0.008322 |
| 229 | 0.007513 | 0.011477 | 0.00846 | −0.002717 | −0.115248 | −0.012463 | −0.013445 | 0.017623 | −0.09284 | −0.175115 | −0.057857 | −0.057788 | −0.01498 | −0.021864 |
| 230 | −0.004604 | 0.016938 | 0.033386 | 0.027837 | −0.002064 | 0.017287 | 0.013431 | 0.005482 | 0.020753 | −0.023012 | −0.043136 | −0.045476 | −0.110617 | −0.005483 |
| 231 | −0.01669 | 0.01757 | 0.001031 | −0.014089 | 0.0101011 | −0.028785 | −0.024839 | −0.028873 | 0.041781 | 0.020337 | −0.006225 | −0.005718 | −0.000417 | −0.006635 |
| 232 | −0.031403 | 0.014209 | 0.007336 | 0.004993 | −0.030865 | −0.023619 | −0.022607 | −0.007688 | −0.015377 | −0.003936 | −0.00357 | 0.001005 | 0.017488 | −0.038488 |
| 233 | 0.002053 | 0.012014 | 0.029589 | 0.033576 | −0.001079 | 0.00182 | 0.005579 | 0.023582 | 0.006088 | −0.000237 | 0.006721 | 0.00775 | 0.023837 | 0.001955 |
| 234 | −0.022672 | 0.010322 | 0.025325 | 0.014069 | 0.01518 | −0.009858 | −0.00493 | −0.011898 | 0.027471 | 0.025359 | 0.031727 | 0.029858 | 0.013164 | −0.003017 |
| 235 | −0.042963 | −0.005679 | 0.019022 | 0.021228 | 0.031968 | −0.002968 | −0.001132 | −0.000038 | 0.025576 | 0.014964 | 0.008701 | 0.006351 | 0.004983 | −0.010061 |
| 236 | −0.044341 | 0.013609 | 0.004636 | −0.006608 | 0.022582 | 0.018955 | 0.016893 | 0.017014 | −0.012402 | 0.025957 | 0.009886 | 0.010389 | −0.015793 | −0.088208 |
| 237 | 0.013997 | 0.008303 | 0.020005 | 0.0153 | 0.014356 | 0.023624 | 0.016521 | 0.029348 | 0.000261 | 0.011378 | 0.026809 | 0.025453 | 0.02698 | −0.011193 |
| 238 | 0.007965 | 0.007059 | 0.011649 | 0.003909 | 0.029417 | 0.025472 | 0.023606 | 0.034111 | 0.02361 | 0.013574 | 0.019465 | 0.018492 | 0.007692 | 0.004159 |
| 239 | −0.003043 | 0.000592 | −0.009859 | −0.006204 | 0.031375 | 0.011139 | 0.021001 | 0.022288 | 0.025469 | 0.01628 | 0.009875 | 0.012235 | 0.010562 | 0.004064 |
| 240 | 0.010457 | −0.020983 | −0.004201 | 0.001859 | 0.008723 | 0.005218 | 0.005959 | −0.003822 | 0.005645 | −0.006401 | 0.005479 | 0.005546 | 0.011593 | 0.00095 |
| 241 | 0.004635 | −0.010674 | 0.008501 | 0.013191 | 0.002831 | 0.009973 | 0.008965 | 0.020956 | 0.000049 | 0.006918 | 0.015843 | 0.014998 | 0.035557 | −0.012685 |
| 242 | −0.045929 | 0.008276 | 0.016127 | 0.005678 | 0.01394 | 0.016969 | 0.013002 | 0.019708 | 0.00345 | 0.020524 | 0.01923 | 0.017181 | 0.004672 | −0.036748 |
| 243 | −0.035365 | −0.020269 | −0.024765 | −0.022883 | 0.000516 | 0.010513 | 0.00685 | 0.01534 | −0.004378 | 0.007854 | 0.02343 | 0.020341 | 0.009053 | −0.000983 |
| 244 | 0.006754 | 0.008183 | 0.023611 | 0.002033 | 0.000779 | 0.01095 | 0.002365 | −0.002462 | 0.005483 | 0.004665 | 0.002148 | 0.000256 | −0.01965 | 0.024682 |
| 245 | −0.004293 | 0.008282 | 0.018991 | 0.000649 | 0.007841 | 0.035316 | 0.033386 | 0.032653 | 0.009576 | 0.002835 | 0.017991 | 0.018936 | −0.002339 | −0.009074 |
| 246 | 0.006301 | −0.008938 | −0.013915 | −0.012497 | 0.02558 | 0.022893 | 0.028469 | 0.026367 | 0.014628 | 0.029731 | 0.025713 | 0.027157 | 0.008878 | 0.006345 |
| 247 | −0.02344 | 0.003956 | −0.011099 | −0.027664 | 0.04484 | 0.02656 | 0.028937 | 0.0211 | 0.012816 | 0.028917 | 0.008037 | 0.008637 | −0.021055 | −0.01993 |
| 248 | −0.034652 | 0.001959 | −0.000076 | −0.019211 | 0.037259 | 0.016432 | 0.012539 | 0.007152 | 0.00772 | 0.021374 | −0.002582 | −0.001147 | −0.023207 | −0.026576 |
| 249 | −0.011459 | −0.075719 | −0.0574 | −0.010481 | 0.012624 | 0.010195 | 0.01339 | 0.012484 | −0.012447 | −0.005856 | −0.00657 | −0.004255 | 0.008076 | −0.005248 |
| 250 | 0.010048 | −0.018756 | −0.010808 | 0.003317 | 0.005523 | −0.001281 | 0.000746 | −0.011061 | 0.001974 | 0.010298 | 0.007432 | 0.007884 | 0.007262 | 0.001777 |
| 251 | −0.001443 | −0.011075 | 0.020129 | 0.012304 | 0.034196 | 0.009062 | 0.001664 | −0.007053 | 0.004313 | 0.005616 | −0.000133 | −0.001852 | 0.004294 | 0.007555 |
| 252 | −0.050284 | 0.007843 | −0.007687 | −0.031534 | 0.011949 | −0.000339 | −0.005402 | −0.004727 | 0.009453 | −0.000774 | −0.009917 | −0.009499 | 0.018988 | −0.013956 |
| 253 | −0.029644 | 0.001696 | 0.00008 | 0.005185 | −0.068004 | −0.019124 | −0.021991 | −0.000903 | −0.037527 | −0.02835 | −0.003334 | −0.002255 | 0.02891 | −0.024563 |
| 254 | 0.01488 | −0.041129 | −0.068728 | −0.049048 | −0.001053 | 0.014247 | 0.016385 | 0.013973 | 0.007027 | 0.003317 | 0.018254 | 0.017806 | 0.007069 | 0.010391 |
| 255 | 0.013886 | −0.010859 | −0.011491 | −0.030976 | 0.008439 | 0.016513 | 0.01215 | 0.000773 | 0.016878 | 0.011383 | 0.019442 | 0.016773 | −0.014199 | 0.026647 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 256 | 0.007689 | −0.009117 | −0.026027 | −0.04653 | −0.053605 | 0.015627 | 0.012507 | 0.023823 | 0.018858 | −0.023708 | 0.023644 | 0.023845 | 0.023922 | 0.007305 |
| 257 | −0.016835 | 0.016955 | 0.012875 | 0.016069 | 0.009946 | −0.01792 | −0.01751 | −0.027111 | 0.014637 | 0.012348 | −0.015388 | −0.017017 | −0.008501 | 0.002997 |
| 258 | −0.020178 | 0.002167 | −0.016048 | −0.013308 | 0.020207 | −0.000233 | 0.00023 | −0.009558 | 0.012303 | 0.037195 | 0.004364 | 0.00361 | −0.00537 | −0.021732 |
| 259 | −0.012712 | −0.072309 | −0.05387 | −0.008 | 0.024327 | 0.014119 | 0.017332 | 0.013011 | −0.007269 | −0.005676 | −0.005919 | −0.004983 | −0.001105 | 0.000093 |
| 260 | −0.030252 | −0.037826 | −0.0671 | −0.048376 | 0.009071 | 0.003142 | −0.000417 | −0.009014 | −0.02398 | −0.025463 | −0.027916 | −0.028677 | −0.004953 | −0.004465 |
| 261 | −0.028846 | −0.020601 | −0.0514 | −0.063779 | 0.020264 | 0.004556 | 0.002478 | −0.009265 | −0.003838 | −0.016273 | −0.007594 | −0.009375 | 0.010237 | −0.014014 |
| 262 | −0.05425 | 0.015357 | −0.002654 | −0.015958 | 0.019863 | 0.005333 | 0.00682 | −0.001782 | −0.00672 | −0.005168 | −0.020709 | −0.019304 | −0.016125 | −0.036819 |
| 263 | 0.935666 | 0.008913 | 0.007926 | 0.001847 | 0.026457 | 0.006752 | 0.007437 | −0.000588 | −0.014543 | 0.001149 | −0.019402 | −0.018683 | −0.020809 | −0.036754 |
| 264 | 0.009783 | 0.897011 | −0.092942 | −0.026913 | 0.009853 | 0.009406 | 0.017008 | 0.011659 | −0.003223 | −0.004349 | 0.003053 | 0.002791 | −0.006355 | 0.012492 |
| 265 | 0.01292 | −0.091413 | 0.828837 | −0.111869 | −0.009706 | −0.006119 | 0.007728 | 0.008227 | −0.00523 | −0.003619 | 0.006815 | 0.007309 | 0.026766 | 0.01481 |
| 266 | 0.005407 | −0.024912 | −0.108061 | 0.870266 | −0.000465 | 0.002963 | 0.004739 | 0.006739 | −0.010364 | 0.000396 | 0.024578 | 0.02196 | 0.030657 | 0.007526 |
| 267 | 0.016645 | 0.019059 | −0.006881 | 0.00235 | 0.832871 | −0.0587 | −0.046366 | −0.03331 | −0.072432 | −0.089923 | −0.008394 | −0.003393 | 0.023705 | −0.008737 |
| 268 | 0.004139 | 0.009879 | 0.002228 | 0.01175 | −0.048317 | 0.932163 | −0.055475 | −0.053513 | −0.021412 | −0.011418 | −0.01928 | −0.01533 | 0.019327 | 0.003186 |
| 269 | 0.007469 | 0.01671 | 0.015969 | 0.014393 | −0.044233 | −0.056971 | 0.940537 | −0.05225 | −0.01837 | −0.010417 | −0.016942 | −0.016858 | 0.010368 | 0.00831 |
| 270 | 0.000511 | 0.00855 | 0.007727 | 0.014718 | −0.027776 | −0.055745 | −0.052206 | 0.920012 | −0.00509 | 0.007195 | −0.023426 | −0.023331 | −0.036196 | 0.016149 |
| 271 | −0.014598 | 0.009061 | 0.010403 | −0.005088 | −0.060059 | −0.01134 | −0.007232 | 0.004323 | 0.801884 | −0.094508 | −0.01158 | −0.011822 | 0.007671 | −0.038398 |
| 272 | 0.003694 | 0.004756 | −0.001935 | −0.005605 | −0.094416 | −0.020149 | −0.014077 | 0.008066 | −0.099146 | 0.832345 | −0.060804 | −0.058955 | 0.001365 | −0.028995 |
| 273 | −0.015805 | 0.007098 | 0.01034 | 0.021255 | −0.013061 | −0.023379 | −0.018685 | −0.019928 | −0.023775 | −0.068406 | 0.904864 | −0.092083 | −0.055619 | −0.016077 |
| 274 | −0.012069 | 0.005776 | 0.008959 | 0.018331 | −0.011911 | −0.019802 | −0.018884 | −0.020012 | −0.024309 | −0.068312 | −0.091578 | 0.908706 | −0.058707 | −0.012679 |
| 275 | −0.01456 | −0.001271 | 0.018322 | 0.023395 | 0.01385 | 0.014211 | 0.009712 | −0.040925 | 0.018374 | −0.010347 | −0.059709 | −0.064073 | 0.823544 | 0.001326 |
| 276 | −0.041763 | 0.014448 | 0.006193 | −0.007441 | −0.013387 | 0.013404 | 0.01532 | 0.021716 | −0.046247 | −0.029588 | 0.000087 | 0.000515 | −0.001193 | 0.891686 |
| 277 | 0.006059 | 0.003807 | −0.00406 | 0.008056 | 0.006821 | 0.009993 | 0.013087 | 0.01708 | 0.012222 | 0.008195 | 0.006771 | 0.008286 | 0.019986 | −0.012805 |
| 278 | 0.004577 | 0.005346 | 0.005946 | 0.018 | 0.006921 | 0.015781 | 0.013457 | 0.014541 | 0.008965 | 0.003985 | 0.002589 | 0.003108 | 0.003266 | −0.006982 |
| 279 | 0.000083 | −0.005033 | −0.013889 | −0.01215 | 0.029983 | 0.014261 | 0.019642 | 0.013248 | 0.007188 | 0.005346 | 0.012882 | 0.012729 | −0.0006 | 0.001007 |
| 280 | −0.018083 | −0.024617 | −0.020806 | 0.002594 | −0.053034 | −0.010211 | −0.007391 | 0.008316 | −0.030074 | −0.009634 | 0.014538 | 0.012319 | 0.018531 | −0.02171 |
| 281 | 0.007168 | −0.020584 | −0.025555 | −0.01847 | 0.01369 | 0.014626 | 0.021738 | 0.018458 | −0.014196 | 0.005937 | 0.007661 | 0.009324 | 0.010582 | 0.002632 |
| 282 | −0.004566 | −0.014833 | −0.013616 | −0.007737 | 0.030402 | 0.020102 | 0.021036 | 0.011781 | −0.015374 | 0.024874 | 0.005239 | 0.004843 | −0.010781 | 0.006444 |
| 283 | −0.02985 | −0.006197 | −0.016697 | −0.036866 | 0.04824 | 0.026346 | 0.023228 | 0.007078 | −0.014853 | 0.010026 | −0.000194 | −0.002271 | −0.033777 | −0.022738 |
| 284 | −0.006299 | 0.00104 | 0.004857 | 0.018747 | −0.006261 | −0.018987 | −0.018566 | −0.023827 | −0.001991 | −0.007509 | −0.018486 | −0.020297 | −0.006532 | 0.001328 |
| 285 | −0.010625 | 0.005541 | 0.012788 | −0.02495 | 0.00458 | −0.017219 | −0.01905 | −0.028619 | −0.003923 | 0.00796 | −0.016927 | −0.019355 | −0.013873 | 0.011776 |
| 286 | 0.008926 | −0.004184 | −0.004416 | 0.00525 | 0.002278 | −0.002457 | −0.00537 | −0.011496 | 0.002335 | 0.018851 | 0.014447 | 0.009152 | 0.005547 | 0.011059 |
| 287 | 0.001713 | −0.001209 | 0.004927 | 0.009337 | 0.009876 | 0.000047 | −0.006833 | −0.019266 | −0.005556 | 0.020808 | 0.01075 | 0.004978 | −0.012352 | 0.013206 |
| 288 | −0.023395 | −0.002188 | −0.004601 | −0.012183 | 0.023242 | 0.008343 | 0.001407 | −0.015953 | −0.005364 | 0.030795 | 0.005426 | 0.002788 | −0.026113 | −0.024699 |
| 289 | −0.041339 | 0.009317 | −0.026228 | −0.035315 | 0.01182 | −0.002631 | 0.000814 | −0.019184 | −0.017214 | 0.001622 | −0.021051 | −0.021192 | −0.036485 | −0.026094 |
| 290 | −0.008999 | 0.00783 | 0.015984 | −0.001142 | 0.013671 | 0.010102 | 0.006156 | −0.00338 | 0.016426 | 0.01606 | −0.004032 | −0.002226 | −0.023269 | 0.022199 |
| 291 | −0.008498 | 0.007562 | 0.01303 | −0.004624 | 0.014799 | 0.010912 | 0.006981 | −0.003532 | 0.015158 | 0.017119 | −0.001495 | −0.000072 | −0.022083 | 0.022111 |
| 292 | −0.006028 | 0.007204 | 0.019163 | −0.002255 | 0.021142 | 0.014 | 0.009881 | 0.001826 | 0.019569 | 0.015636 | 0.005241 | 0.005819 | −0.016878 | 0.024317 |
| 293 | 0.000674 | −0.015394 | −0.007979 | 0.003993 | 0.012024 | −0.010314 | 0.000052 | 0.003919 | 0.011216 | 0.019966 | 0.014265 | 0.016881 | 0.011243 | −0.028911 |
| 294 | −0.002248 | −0.010513 | −0.007208 | 0.003472 | −0.002883 | −0.019229 | −0.01327 | −0.016658 | 0.003767 | −0.001237 | −0.019609 | −0.017272 | −0.017913 | −0.001163 |
| 295 | −0.013567 | 0.005766 | 0.009709 | 0.011666 | 0.013513 | 0.001276 | 0.006551 | 0.009107 | 0.005683 | −0.041593 | −0.05707 | −0.055676 | −0.029252 | −0.015457 |
| 296 | −0.015656 | 0.006241 | 0.008889 | 0.004003 | −0.004211 | −0.003184 | −0.005515 | −0.021726 | 0.017863 | −0.046974 | −0.076419 | −0.07642 | −0.075899 | 0.009449 |
| 297 | −0.007391 | 0.00781 | 0.013447 | 0.007345 | 0.001308 | 0.005247 | 0.006104 | 0.016827 | 0.007438 | −0.044671 | −0.045853 | −0.04512 | −0.0063 | −0.024932 |
| 298 | −0.000393 | 0.028234 | 0.021666 | 0.003746 | 0.003358 | 0.009651 | 0.003323 | 0.009834 | 0.005076 | 0.008515 | −0.001314 | 0.00038 | 0.002706 | 0.000287 |
| 299 | 0.0053 | 0.001433 | −0.000524 | −0.005538 | 0.003712 | −0.011814 | −0.006604 | 0.009393 | −0.001778 | −0.017158 | −0.012236 | −0.008915 | 0.033291 | −0.025438 |
| 300 | 0.011509 | 0.0204 | 0.011359 | 0.0003 | −0.000424 | 0.013481 | 0.01155 | 0.004295 | 0.009903 | −0.015771 | −0.003433 | −0.007796 | −0.016374 | −0.003114 |
| 301 | −0.011435 | −0.00018 | 0.013041 | 0.020353 | 0.014423 | −0.01029 | −0.006925 | 0.000353 | 0.012012 | −0.002362 | −0.01557 | −0.01247 | 0.004921 | −0.007093 |
| 302 | −0.006342 | −0.003219 | 0.006469 | 0.018553 | 0.010891 | −0.010301 | −0.004335 | −0.017513 | 0.013031 | 0.002772 | −0.021597 | −0.019955 | −0.029211 | 0.013486 |
| 303 | 0.010226 | 0.01209 | 0.00192 | −0.010593 | −0.0086 | −0.00345 | −0.006539 | 0.006614 | 0.006701 | −0.017309 | 0.010323 | 0.010824 | 0.038044 | −0.000063 |
| 304 | 0.008656 | 0.007594 | 0.015654 | 0.010644 | −0.004816 | −0.012612 | −0.009649 | −0.009565 | 0.0217 | −0.006892 | −0.000344 | 0.002581 | 0.021972 | 0.00023 |
| 305 | −0.003867 | 0.003643 | −0.00084 | −0.004877 | 0.005152 | −0.013046 | −0.003572 | −0.007685 | −0.034622 | −0.006432 | 0.001893 | 0.000004 | 0.001134 | 0.010604 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 306 | −0.001576 | −0.033696 | −0.035817 | −0.006334 | 0.016531 | 0.006509 | 0.019875 | 0.009287 | 0.046677 | 0.008262 | −0.015033 | −0.010771 | −0.019942 | −0.006926 |
| 307 | −0.011399 | 0.015116 | 0.026375 | 0.010311 | 0.004828 | 0.020834 | 0.013075 | 0.009945 | 0.011318 | −0.008491 | −0.009759 | −0.015209 | −0.019231 | 0.006435 |
| 308 | −0.013115 | 0.022364 | 0.022562 | 0.023783 | 0.024542 | 0.004128 | 0.006659 | 0.010973 | −0.003987 | −0.00957 | −0.016101 | −0.016257 | 0.013662 | 0.026646 |
| 309 | 0.001302 | 0.002845 | 0.007422 | 0.007573 | −0.001632 | −0.007295 | −0.014179 | −0.017966 | −0.001898 | 0.018688 | 0.00724 | 0.005564 | −0.018857 | 0.01019 |
| 310 | 0.006116 | −0.00682 | −0.015218 | 0.000959 | −0.015685 | 0.001516 | −0.004456 | −0.012876 | 0.004179 | 0.019282 | 0.000243 | −0.002703 | −0.054908 | 0.032584 |
| 311 | −0.008578 | −0.001823 | 0.006688 | 0.008288 | 0.004446 | −0.017078 | −0.016455 | −0.014397 | −0.002595 | −0.008151 | −0.024564 | −0.024576 | −0.01422 | −0.011374 |
| 312 | 0.000219 | 0.030201 | 0.039994 | 0.024613 | −0.008764 | −0.006312 | −0.017665 | −0.0066 | 0.034666 | −0.036208 | −0.020682 | −0.022831 | −0.003869 | 0.026586 |
| 313 | 0.006867 | −0.011445 | −0.005584 | −0.002133 | 0.00313 | −0.001044 | −0.00791 | −0.005367 | 0.022929 | −0.011226 | 0.000398 | −0.002891 | 0.001421 | 0.009625 |
| 314 | 0.000585 | 0.001901 | −0.006703 | −0.024598 | 0.00972 | 0.032347 | 0.026127 | 0.025345 | −0.003 | −0.002649 | 0.016963 | 0.015041 | 0.016639 | 0.001716 |
| 315 | 0.016243 | 0.008288 | −0.004009 | −0.018719 | 0.003963 | −0.004659 | −0.014463 | −0.005616 | −0.001516 | 0.012077 | 0.020119 | 0.014657 | 0.021752 | 0.007017 |
| 316 | 0.011548 | 0.000261 | −0.010304 | −0.005092 | −0.017011 | 0.013824 | −0.002817 | −0.011417 | 0.012212 | 0.024227 | 0.024853 | 0.018394 | −0.028375 | 0.040791 |
| 317 | −0.005731 | −0.000335 | −0.014892 | −0.010304 | 0.010182 | −0.003254 | −0.011019 | −0.011535 | 0.004436 | 0.007679 | 0.000608 | −0.002173 | −0.010884 | 0.008505 |
| 318 | 0.003443 | 0.011988 | 0.034663 | 0.017442 | 0.024036 | 0.000307 | −0.008951 | −0.001221 | −0.013205 | 0.015732 | 0.008715 | 0.005204 | 0.000439 | 0.003888 |
| 319 | 0.016652 | 0.00984 | −0.001147 | −0.012355 | 0.005834 | −0.004171 | −0.020379 | −0.002354 | 0.007984 | 0.020144 | 0.017605 | 0.012669 | 0.021227 | 0.009315 |
| 320 | 0.014236 | −0.002518 | −0.007739 | 0.005685 | 0.021835 | −0.014875 | −0.009052 | −0.004842 | 0.054874 | 0.030775 | −0.007969 | −0.00479 | 0.008027 | 0.022433 |
| 321 | −0.010643 | −0.002822 | 0.00876 | 0.010754 | 0.000311 | −0.005896 | 0.003334 | −0.002415 | 0.021723 | −0.007759 | −0.028697 | −0.024852 | 0.002546 | −0.009833 |
| 322 | −0.015333 | 0.005695 | 0.00205 | 0.025815 | −0.001876 | 0.005423 | 0.014679 | −0.001972 | 0.003165 | 0.031213 | 0.014994 | 0.015118 | −0.020107 | 0.012712 |
| 323 | 0.000573 | 0.013722 | 0.011529 | 0.016375 | −0.003926 | −0.020998 | −0.011907 | −0.001317 | 0.042073 | 0.019286 | −0.000243 | 0.00215 | 0.030759 | −0.001382 |
| 324 | −0.005779 | −0.032378 | −0.026989 | −0.011916 | 0.008674 | −0.006195 | 0.00248 | −0.032475 | −0.070979 | 0.020909 | −0.002489 | −0.002746 | −0.044251 | −0.001086 |
| 325 | 0.004942 | −0.013816 | −0.018797 | −0.01765 | −0.020947 | −0.009139 | −0.019823 | −0.020326 | −0.009746 | −0.014201 | −0.007666 | −0.011319 | −0.025703 | −0.001874 |
| 326 | −0.010716 | −0.032514 | −0.030373 | −0.020486 | 0.000763 | −0.003684 | −0.012465 | −0.01297 | −0.030054 | −0.019132 | −0.008578 | −0.010861 | −0.033407 | −0.006557 |
| 327 | −0.003692 | 0.004299 | 0.008167 | 0.005502 | 0.002752 | −0.009125 | −0.007481 | −0.003707 | −0.006884 | −0.015067 | −0.015559 | −0.016697 | −0.012547 | −0.001543 |
| 328 | −0.019987 | 0.002508 | 0.00027 | 0.002852 | 0.009939 | −0.001848 | 0.004463 | −0.00038 | 0.003246 | 0.024867 | −0.019203 | −0.01501 | 0.0152 | 0.01293 |
| 329 | −0.006905 | 0.002306 | 0.008187 | −0.002986 | 0.020144 | −0.007873 | −0.00705 | 0.003564 | −0.002974 | −0.012247 | −0.009826 | −0.010814 | 0.010278 | 0.004291 |
| 330 | −0.005908 | −0.003991 | −0.007893 | 0.007424 | −0.005319 | 0.003046 | 0.004633 | −0.002812 | 0.009953 | 0.002456 | −0.002518 | 0.000614 | −0.025592 | −0.012301 |
| 331 | 0.007758 | −0.006704 | −0.009472 | −0.011898 | −0.005637 | −0.014436 | −0.013036 | −0.007008 | −0.009276 | 0.004912 | 0.017978 | 0.016982 | 0.013827 | −0.0024 |
| 332 | 0.002763 | 0.007653 | 0.017248 | 0.011541 | 0.015574 | 0.001118 | −0.00981 | −0.004432 | −0.005093 | 0.023849 | −0.011425 | −0.011802 | −0.016315 | −0.006583 |
| 333 | 0.005779 | −0.004058 | 0.000135 | −0.003846 | −0.008472 | −0.012387 | −0.018825 | −0.01991 | 0.000364 | 0.012159 | 0.009299 | 0.007693 | −0.01609 | 0.000005 |
| 334 | 0.001386 | 0.020385 | 0.052447 | 0.01644 | 0.002252 | 0.014863 | 0.000179 | 0.011301 | −0.029124 | −0.02647 | 0.000211 | −0.002078 | −0.010558 | 0.022168 |
| 335 | 0.016015 | −0.014876 | −0.012627 | −0.006122 | −0.012493 | −0.018069 | −0.026051 | −0.010814 | 0.008295 | 0.00712 | 0.006856 | 0.004905 | −0.000142 | 0.002823 |
| 336 | −0.002731 | 0.010105 | 0.008226 | 0.016813 | −0.019378 | −0.000751 | 0.00616 | 0.001438 | −0.000059 | 0.007108 | 0.007457 | 0.012062 | −0.020161 | −0.006525 |
| 337 | 0.009363 | −0.011049 | −0.008239 | −0.012923 | 0.00054 | −0.002828 | −0.006605 | −0.003107 | −0.029747 | −0.030906 | −0.008384 | −0.009339 | 0.004675 | 0.02183 |
| 338 | −0.017037 | 0.047631 | 0.05987 | 0.02707 | 0.048057 | 0.006441 | −0.005316 | 0.00466 | −0.013676 | 0.006539 | −0.041514 | −0.041417 | −0.03146 | −0.012068 |
| 339 | −0.014502 | −0.001951 | 0.014699 | 0.018491 | 0.009672 | −0.006523 | −0.002225 | 0.001865 | 0.010701 | −0.007286 | 0.006213 | 0.007689 | 0.03225 | −0.00647 |
| 340 | 0.021312 | 0.01868 | 0.016804 | −0.018682 | 0.037441 | 0.014923 | 0.004435 | 0.017497 | −0.011324 | 0.002113 | −0.004142 | −0.011512 | −0.00068 | 0.028038 |

| | JR | JS | JT | JU | JV | JW | JX | JY | JZ | KA | KB | KC | KD | KE |
|---|---|---|---|---|---|---|---|---|---|---|---|---|---|---|
| 1 | −0.027815 | −0.014963 | −0.030467 | −0.04043 | 0.029659 | 0.022362 | 0.049835 | 0.017356 | 0.007426 | −0.000576 | 0.010204 | 0.009212 | 0.024097 | 0.046208 |
| 2 | 0.017546 | 0.024279 | −0.028458 | 0.003692 | 0.017485 | 0.018916 | 0.00668 | −0.019793 | −0.010321 | 0.015076 | 0.026784 | 0.066951 | 0.014435 | 0.07555 |
| 3 | 0.07775 | 0.061108 | 0.029658 | −0.025069 | 0.063885 | 0.056536 | 0.019465 | −0.073112 | −0.087487 | −0.02439 | −0.025838 | 0.041328 | −0.005344 | 0.020255 |
| 4 | −0.015324 | −0.000268 | −0.054466 | 0.127709 | 0.03584 | 0.070334 | −0.023793 | −0.017177 | −0.014101 | 0.060341 | 0.059514 | 0.019736 | 0.011353 | −0.022496 |
| 5 | −0.04958 | −0.037678 | 0.107849 | 0.023561 | −0.032533 | −0.024235 | 0.151601 | −0.053245 | −0.056983 | −0.047644 | −0.027192 | 0.001922 | −0.015222 | −0.01914 |
| 6 | 0.015226 | 0.040847 | −0.029958 | 0.045889 | 0.065078 | 0.083917 | 0.04456 | −0.013206 | −0.007444 | 0.040172 | 0.049378 | 0.102155 | 0.104482 | 0.036326 |
| 7 | 0.0387 | 0.052515 | 0.007535 | 0.023119 | −0.009756 | −0.002215 | −0.037728 | −0.040808 | −0.021132 | −0.048704 | −0.021596 | −0.04458 | −0.066053 | −0.006091 |
| 8 | −0.033127 | −0.052147 | −0.015801 | −0.006272 | −0.014606 | 0.018091 | −0.041609 | 0.030348 | 0.034589 | 0.046173 | 0.036563 | −0.013805 | 0.02512 | −0.006312 |
| 9 | 0.004275 | −0.001116 | 0.017194 | 0.03872 | 0.06411 | 0.094646 | 0.082157 | −0.010084 | 0.009449 | 0.042227 | 0.064191 | 0.035922 | 0.011407 | −0.047512 |
| 10 | −0.004628 | 0.007259 | 0.064721 | 0.058761 | −0.002077 | −0.015851 | −0.004414 | 0.041302 | 0.040764 | 0.014686 | 0.003596 | 0.030463 | 0.004826 | 0.043634 |
| 11 | −0.033978 | −0.010607 | 0.011754 | −0.035982 | 0.027941 | 0.028714 | 0.041273 | 0.068373 | 0.07454 | 0.026668 | 0.028527 | 0.040999 | 0.0069 | −0.012309 |
| 12 | 0.027226 | 0.003521 | 0.031223 | 0.023123 | −0.100019 | −0.119358 | −0.058146 | −0.005548 | −0.019041 | −0.005763 | −0.009729 | −0.005095 | −0.024034 | −0.019327 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 13 | −0.015265 | −0.001432 | −0.011109 | 0.072909 | 0.020555 | 0.049667 | −0.025643 | 0.032962 | 0.046186 | 0.095903 | 0.092278 | 0.082954 | −0.026217 | 0.047564 |
| 14 | −0.003531 | −0.023155 | −0.041184 | −0.102363 | −0.004427 | −0.057187 | −0.066873 | −0.005708 | 0.005958 | −0.079495 | −0.08226 | −0.071327 | −0.26774 | 0.027754 |
| 15 | 0.031107 | 0.058514 | 0.04565 | 0.016635 | −0.047569 | −0.026532 | −0.055052 | 0.020956 | 0.031542 | 0.02188 | 0.035068 | −0.053782 | −0.026774 | −0.176182 |
| 16 | −0.082703 | −0.090733 | −0.079637 | −0.073313 | −0.009187 | 0.000988 | −0.010284 | 0.055602 | 0.049626 | 0.072551 | 0.063301 | 0.009899 | −0.019539 | −0.057144 |
| 17 | −0.01296 | −0.012369 | 0.022446 | −0.025006 | −0.043003 | −0.06543 | −0.02002 | −0.039531 | −0.033074 | −0.10041 | −0.090027 | −0.029391 | 0.040688 | 0.054985 |
| 18 | 0.095053 | 0.106679 | 0.007683 | 0.096333 | 0.089867 | 0.060331 | 0.024892 | −0.044617 | −0.049978 | −0.030327 | −0.039517 | −0.023383 | 0.003215 | −0.046723 |
| 19 | −0.053247 | −0.03895 | −0.008542 | 0.113774 | −0.015111 | −0.007581 | 0.020302 | −0.018828 | −0.014193 | −0.021111 | 0.00874 | −0.010164 | −0.010377 | −0.035275 |
| 20 | 0.047408 | 0.047599 | 0.024055 | −0.01981 | −0.022546 | −0.016818 | 0.033449 | −0.025712 | −0.029602 | −0.091238 | −0.09581 | −0.0427 | 0.068507 | −0.031795 |
| 21 | −0.048929 | −0.047677 | 0.028873 | −0.10053 | 0.021881 | 0.014386 | 0.05766 | 0.032523 | 0.028849 | −0.018052 | −0.02699 | 0.023152 | −0.013226 | 0.031857 |
| 22 | −0.012991 | −0.054543 | −0.024787 | 0.034561 | 0.061568 | 0.048368 | 0.004243 | 0.057041 | 0.035696 | 0.047532 | 0.03098 | 0.0068 | 0.025256 | −0.03747 |
| 23 | 0.078004 | 0.076455 | 0.092058 | −0.068664 | −0.000784 | −0.034636 | −0.020045 | −0.051236 | −0.041827 | −0.062403 | −0.06175 | −0.059865 | −0.059219 | 0.009515 |
| 24 | 0.006144 | 0.000912 | −0.026914 | 0.019594 | −0.02244 | −0.011233 | −0.071718 | 0.020959 | 0.007862 | 0.068867 | 0.043081 | −0.042627 | −0.056287 | −0.09595 |
| 25 | 0.019625 | 0.003756 | 0.119413 | −0.061383 | −0.083776 | −0.074684 | 0.033644 | 0.007202 | 0.00591 | 0.048105 | 0.062151 | 0.109441 | 0.045943 | 0.042722 |
| 26 | 0.046978 | 0.01945 | −0.019584 | 0.065604 | −0.031702 | −0.057673 | −0.069943 | −0.005742 | −0.020079 | −0.019082 | −0.04125 | −0.009776 | −0.018573 | 0.010912 |
| 27 | −0.033462 | −0.032679 | 0.039323 | 0.056837 | 0.004792 | 0.009017 | −0.029903 | 0.01318 | 0.023959 | 0.077442 | 0.067831 | 0.004329 | −0.04867 | −0.008888 |
| 28 | 0.040045 | 0.031309 | 0.026743 | 0.019313 | 0.021856 | 0.00238 | 0.005678 | −0.053899 | −0.078674 | 0.011496 | 0.004784 | 0.012795 | −0.067585 | −0.009022 |
| 29 | 0.014326 | 0.012424 | 0.009392 | −0.01511 | 0.011025 | 0.004835 | 0.010427 | 0.005514 | 0.001098 | −0.003802 | −0.009903 | 0.004259 | −0.006732 | −0.005364 |
| 30 | 0.036215 | 0.049783 | −0.037392 | −0.082567 | −0.027732 | −0.018513 | −0.027263 | 0.005144 | 0.016975 | −0.038774 | −0.030503 | 0.040212 | 0.059265 | 0.044279 |
| 31 | −0.009337 | −0.018964 | 0.00299 | −0.011864 | −0.035957 | −0.067487 | −0.00784 | 0.009596 | −0.00192 | −0.031892 | −0.033198 | −0.051018 | −0.004493 | −0.026562 |
| 32 | −0.059034 | −0.06501 | −0.019161 | 0.073454 | −0.060074 | −0.052667 | −0.003225 | −0.001868 | −0.003725 | −0.006386 | 0.003251 | 0.033498 | −0.000322 | 0.015033 |
| 33 | −0.017622 | −0.019084 | −0.029938 | −0.020296 | −0.009832 | −0.008823 | 0.044432 | 0.023289 | 0.025773 | 0.012629 | 0.002 | 0.061003 | 0.059223 | 0.005943 |
| 34 | 0.012917 | 0.012478 | −0.011786 | −0.026182 | −0.014084 | 0.023875 | −0.053187 | 0.032732 | 0.06196 | 0.056573 | 0.055938 | 0.011334 | 0.000338 | 0.034714 |
| 35 | −0.001948 | −0.023737 | 0.033921 | 0.04084 | −0.072164 | −0.03294 | −0.009047 | 0.00245 | 0.037105 | −0.014373 | −0.008385 | −0.066881 | 0.060469 | −0.005746 |
| 36 | 0.032615 | 0.039465 | −0.013086 | 0.016862 | 0.072414 | 0.068134 | 0.00452 | −0.033162 | −0.028462 | 0.030966 | 0.040236 | 0.013943 | 0.029898 | 0.048011 |
| 37 | 0.023514 | 0.043923 | −0.033433 | −0.0717 | −0.066958 | −0.053624 | −0.109243 | 0.018797 | 0.028926 | 0.025029 | 0.011132 | −0.110553 | −0.049253 | −0.011144 |
| 38 | −0.018328 | −0.015566 | −0.054257 | 0.007933 | −0.011178 | −0.028309 | −0.014643 | −0.006538 | −0.024669 | −0.021078 | −0.02631 | −0.047767 | −0.035922 | 0.000886 |
| 39 | −0.020441 | −0.030727 | −0.059871 | 0.103235 | 0.064063 | 0.052569 | 0.037223 | 0.010817 | −0.00496 | −0.039205 | −0.02869 | −0.024778 | −0.014354 | −0.003373 |
| 40 | −0.00555 | −0.010933 | −0.003584 | 0.028619 | 0.026851 | 0.024676 | 0.020055 | 0.000359 | −0.000502 | −0.000986 | −0.00526 | −0.005016 | 0.01122 | 0.007919 |
| 41 | 0.005451 | −0.003813 | 0.02103 | 0.023792 | 0.016422 | 0.012614 | 0.01704 | −0.010948 | −0.010627 | −0.04557 | −0.05839 | −0.076541 | −0.005627 | −0.028241 |
| 42 | −0.022832 | −0.017299 | −0.003143 | 0.028892 | −0.086907 | −0.060925 | −0.046396 | 0.013536 | 0.02143 | −0.009321 | 0.001664 | −0.013832 | −0.055467 | −0.023947 |
| 43 | 0.000092 | 0.004696 | −0.047886 | −0.007619 | 0.003683 | −0.024534 | −0.069056 | −0.010298 | −0.015875 | 0.012504 | −0.019814 | −0.030934 | −0.045953 | 0.037279 |
| 44 | −0.025633 | −0.028144 | −0.043504 | 0.014939 | −0.013386 | −0.028347 | −0.044333 | 0.016596 | 0.003689 | −0.023088 | −0.026129 | 0.001694 | −0.00693 | 0.030814 |
| 45 | −0.020013 | −0.009231 | −0.021987 | −0.013776 | 0.048028 | 0.073667 | 0.037372 | −0.054742 | −0.04073 | 0.015405 | 0.034212 | 0.045199 | 0.033559 | 0.028236 |
| 46 | 0.03011 | 0.033436 | 0.016446 | 0.041816 | −0.03016 | −0.033576 | −0.008466 | −0.010217 | −0.017202 | 0.036422 | 0.029656 | −0.004045 | −0.013425 | 0.029279 |
| 47 | −0.00485 | −0.011313 | 0.001495 | 0.011328 | −0.030632 | −0.006274 | 0.010169 | 0.019007 | 0.044347 | 0.028394 | 0.054728 | −0.001409 | 0.028322 | 0.044428 |
| 48 | 0.035858 | 0.047929 | 0.038081 | 0.000681 | −0.041136 | −0.062582 | −0.02887 | 0.042212 | 0.011268 | 0.006613 | −0.007967 | 0.026412 | 0.034976 | 0.02113 |
| 49 | 0.026781 | 0.055464 | 0.020758 | −0.027988 | −0.007285 | 0.05837 | 0.022585 | −0.011317 | 0.028331 | −0.054054 | −0.02064 | −0.047649 | 0.042825 | −0.060325 |
| 50 | −0.066043 | −0.08029 | 0.060745 | 0.006515 | 0.042566 | −0.012177 | 0.008053 | −0.06358 | −0.086222 | −0.080201 | −0.109305 | −0.07546 | −0.018419 | 0.015401 |
| 51 | 0.063932 | 0.034877 | −0.059721 | 0.125851 | 0.01991 | 0.03179 | 0.001137 | 0.006998 | 0.00042 | 0.040208 | 0.023014 | 0.061313 | −0.008831 | −0.017921 |
| 52 | −0.058962 | −0.03591 | 0.071014 | −0.008323 | 0.004803 | 0.043955 | 0.048634 | 0.03553 | 0.057099 | 0.010251 | 0.017418 | −0.059258 | −0.000292 | −0.071024 |
| 53 | 0.000362 | −0.013762 | −0.114323 | −0.027689 | 0.068677 | 0.038423 | −0.063241 | −0.009261 | −0.013244 | 0.00285 | −0.008213 | −0.036604 | −0.055663 | −0.025966 |
| 54 | 0.022416 | 0.05869 | 0.037821 | −0.158275 | 0.002216 | 0.014836 | 0.068797 | 0.025162 | 0.020404 | 0.014672 | 0.022492 | 0.035203 | −0.004134 | −0.037764 |
| 55 | 0.061852 | 0.08954 | −0.039335 | 0.040744 | 0.046212 | 0.037847 | 0.034793 | −0.058864 | −0.055099 | −0.107888 | −0.082556 | 0.033849 | −0.026258 | 0.085231 |
| 56 | 0.026569 | 0.006363 | −0.00718 | 0.029219 | 0.008545 | −0.016027 | −0.018561 | −0.027616 | −0.02277 | −0.049507 | −0.05727 | −0.062643 | −0.01839 | −0.084989 |
| 57 | −0.030995 | −0.016745 | −0.003682 | −0.0619 | 0.088838 | 0.104181 | 0.055389 | −0.00374 | 0.019444 | 0.035886 | 0.011062 | 0.003327 | −0.027496 | −0.041909 |
| 58 | 0.040132 | 0.066568 | 0.046021 | −0.024127 | 0.014766 | 0.040025 | 0.003558 | 0.000043 | 0.013268 | −0.009651 | 0.000634 | −0.006388 | −0.021776 | 0.001538 |
| 59 | −0.019816 | −0.084699 | −0.007427 | 0.022202 | 0.079126 | 0.036217 | 0.020687 | −0.002791 | −0.014171 | 0.026579 | −0.001553 | 0.006579 | 0.035652 | −0.050752 |
| 60 | −0.001955 | −0.003613 | 0.039496 | −0.010102 | −0.072174 | −0.065261 | −0.005545 | 0.009462 | 0.008169 | 0.013521 | 0.023998 | 0.00775 | −0.015668 | −0.006127 |
| 61 | −0.018088 | −0.015553 | 0.016779 | 0.013501 | −0.048416 | −0.036829 | −0.009902 | 0.01162 | 0.009186 | 0.008915 | 0.010328 | −0.001933 | −0.006057 | −0.010946 |
| 62 | 0.050678 | 0.048421 | −0.015638 | 0.00832 | −0.0417 | −0.03245 | −0.084433 | 0.012493 | 0.018423 | 0.024759 | 0.022562 | −0.015797 | −0.00921 | −0.008148 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 63 | 0.013675 | 0.011945 | −0.003905 | 0.033126 | −0.016759 | −0.01008 | −0.013915 | 0.006493 | 0.003857 | −0.006448 | −0.009027 | −0.01175 | −0.004619 | −0.027294 |
| 64 | 0.013573 | 0.014231 | 0.026287 | −0.006045 | −0.021329 | −0.004219 | −0.005294 | −0.003362 | 0.008999 | −0.006931 | −0.000259 | −0.021797 | 0.004286 | 0.000521 |
| 65 | 0.043986 | 0.043866 | 0.01992 | −0.004039 | 0.002911 | −0.008646 | −0.005659 | −0.00978 | −0.014728 | −0.015129 | −0.01458 | 0.011418 | −0.002286 | 0.004543 |
| 66 | 0.01373 | 0.01148 | −0.013509 | 0.008734 | 0.008464 | 0.000473 | −0.010776 | −0.010806 | −0.010125 | −0.013553 | −0.018063 | −0.010053 | −0.014167 | −0.001698 |
| 67 | 0.008806 | 0.007667 | −0.015841 | −0.033895 | 0.018244 | 0.012251 | 0.016329 | 0.00548 | 0.000126 | −0.009039 | −0.010322 | 0.016631 | 0.021349 | 0.015565 |
| 68 | 0.014842 | 0.010003 | 0.01341 | 0.029294 | 0.031575 | 0.023121 | −0.003985 | 0.004136 | 0.002667 | 0.001648 | −0.004154 | −0.005753 | −0.001281 | −0.018775 |
| 69 | −0.009501 | −0.016048 | −0.015965 | −0.009976 | 0.008738 | 0.014453 | −0.014606 | −0.009169 | −0.005119 | −0.00593 | −0.005251 | −0.001474 | 0.009275 | −0.006805 |
| 70 | −0.011771 | −0.012981 | −0.013149 | −0.032076 | 0.001536 | 0.005817 | 0.000159 | 0.003086 | 0.006203 | −0.001046 | −0.000928 | −0.008419 | 0.007182 | −0.013959 |
| 71 | 0.001428 | −0.011807 | 0.007695 | 0.029657 | 0.015798 | 0.013824 | 0.009784 | −0.003771 | −0.012097 | 0.018925 | 0.014225 | 0.023292 | 0.010173 | −0.008339 |
| 72 | 0.01567 | 0.003792 | 0.007044 | 0.017002 | −0.005153 | −0.00632 | 0.005113 | −0.020842 | −0.026991 | −0.003402 | 0.001125 | 0.005329 | 0.012573 | −0.027619 |
| 73 | −0.012065 | −0.015082 | −0.007279 | −0.020381 | 0.002071 | −0.007941 | −0.008789 | 0.006845 | 0.003781 | −0.022621 | −0.020104 | −0.030057 | 0.027484 | −0.02723 |
| 74 | 0.010321 | 0.015526 | 0.031525 | 0.01929 | −0.001406 | −0.005576 | 0.000842 | −0.001349 | 0.001091 | −0.001382 | −0.00015 | −0.020089 | −0.020522 | −0.041012 |
| 75 | 0.001678 | 0.000143 | 0.004475 | 0.008126 | −0.009593 | −0.009148 | −0.00576 | 0.007021 | 0.003417 | 0.003057 | 0.001646 | −0.002629 | 0.004227 | −0.004975 |
| 76 | 0.01203 | 0.022313 | −0.004981 | −0.01271 | 0.006471 | 0.016152 | 0.000641 | −0.006588 | −0.005526 | 0.010065 | 0.010563 | 0.014533 | −0.005009 | −0.004213 |
| 77 | −0.002714 | −0.006571 | 0.000531 | 0.00842 | −0.002666 | −0.004829 | −0.006826 | 0.002832 | −0.002587 | −0.000182 | −0.004273 | −0.001575 | 0.004764 | −0.010338 |
| 78 | −0.005704 | −0.011371 | −0.001171 | 0.00133 | −0.002918 | −0.008339 | −0.003609 | 0.010745 | 0.003313 | 0.004537 | −0.000812 | −0.002977 | 0.008637 | −0.013716 |
| 79 | −0.012709 | −0.013323 | 0.005525 | −0.008618 | −0.008303 | 0.001226 | −0.006145 | 0.006252 | 0.011172 | 0.009609 | 0.010509 | −0.019729 | −0.00095 | 0.000155 |
| 80 | −0.002001 | 0.018171 | 0.010029 | −0.023376 | 0.016087 | 0.03123 | 0.033826 | 0.010141 | 0.01935 | 0.00809 | 0.015966 | 0.031949 | 0.004639 | 0.017033 |
| 81 | 0.012901 | 0.020541 | 0.014064 | 0.004177 | −0.004097 | −0.003071 | −0.004657 | −0.007674 | −0.002921 | −0.018332 | −0.013198 | 0.019597 | 0.008926 | 0.007722 |
| 82 | −0.002783 | −0.000506 | −0.008749 | −0.003439 | 0.0053 | 0.001088 | 0.003559 | −0.002494 | −0.002799 | −0.006127 | −0.007101 | −0.014527 | −0.011447 | 0.010712 |
| 83 | −0.003895 | −0.000189 | −0.007472 | −0.001861 | 0.009508 | 0.007034 | 0.016285 | 0.005701 | 0.000476 | 0.006398 | 0.005396 | 0.008305 | −0.005691 | 0.017115 |
| 84 | −0.003463 | −0.006909 | −0.001006 | 0.000138 | 0.01748 | 0.012512 | 0.025109 | 0.001339 | −0.007178 | 0.001718 | 0.000304 | 0.016505 | 0.006749 | 0.015661 |
| 85 | −0.005846 | −0.004106 | −0.00952 | −0.025063 | −0.007616 | −0.008276 | −0.025809 | −0.008742 | −0.008696 | 0.003452 | 0.003935 | 0.004385 | 0.011358 | 0.037883 |
| 86 | −0.013301 | −0.023526 | −0.012316 | 0.015341 | 0.015987 | 0.011378 | 0.004678 | −0.002936 | −0.00974 | 0.021785 | 0.015682 | 0.019888 | 0.011767 | 0.001135 |
| 87 | −0.015473 | −0.009269 | −0.0206 | −0.014617 | 0.019099 | 0.031335 | 0.026497 | 0.014412 | 0.017485 | 0.019321 | 0.025286 | 0.027373 | 0.008057 | 0.010229 |
| 88 | −0.004067 | −0.001168 | −0.0057 | −0.013583 | 0.008556 | 0.00125 | 0.017292 | 0.003157 | −0.001989 | −0.010463 | −0.009548 | −0.005986 | −0.004803 | 0.006785 |
| 89 | −0.00826 | −0.013295 | −0.005164 | −0.003018 | 0.021904 | 0.014055 | 0.019865 | 0.007704 | 0.001554 | 0.008943 | 0.005 | 0.009565 | 0.004015 | 0.006794 |
| 90 | −0.000916 | −0.00054 | 0.002799 | 0.004327 | 0.01646 | 0.017385 | 0.017193 | 0.003952 | 0.001844 | 0.01036 | 0.012332 | 0.018298 | 0.004819 | 0.011 |
| 91 | −0.001138 | −0.007112 | 0.002829 | −0.009364 | 0.021679 | 0.010584 | 0.020548 | −0.00453 | −0.009337 | −0.004978 | −0.00618 | 0.001227 | 0.014263 | 0.014854 |
| 92 | −0.014491 | −0.019489 | −0.019304 | −0.025324 | 0.00242 | −0.004114 | 0.012031 | 0.00893 | 0.00031 | −0.007173 | −0.007705 | 0.005688 | 0.033227 | −0.010615 |
| 93 | −0.004128 | 0.001209 | 0.012235 | −0.003854 | 0.01235 | 0.022193 | 0.024407 | 0.008941 | 0.005746 | 0.013817 | 0.0136 | 0.017009 | 0.014904 | −0.006873 |
| 94 | −0.009803 | −0.01905 | −0.004882 | −0.035032 | −0.022568 | −0.037253 | −0.004387 | −0.00503 | −0.009117 | −0.017873 | −0.017899 | −0.025853 | −0.016997 | 0.003387 |
| 95 | −0.003996 | −0.018277 | −0.007909 | 0.023095 | 0.013773 | 0.016025 | 0.000905 | −0.00988 | 0.000489 | −0.008075 | −0.011872 | −0.01077 | 0.004372 | 0.020909 |
| 96 | −0.00754 | −0.008759 | 0.018724 | −0.027822 | −0.000619 | 0.004442 | 0.012526 | 0.000548 | 0.005577 | 0.011076 | 0.017089 | −0.014475 | −0.008553 | −0.012473 |
| 97 | 0.011434 | 0.020685 | 0.033272 | −0.035075 | −0.022108 | −0.02062 | 0.015964 | −0.015046 | −0.00545 | −0.049091 | −0.041327 | −0.023912 | −0.01562 | 0.007732 |
| 98 | 0.007025 | 0.009912 | 0.012001 | 0.002393 | −0.001275 | 0.000897 | 0.005553 | −0.008118 | −0.005422 | −0.003294 | 0.001321 | −0.002994 | −0.002026 | 0.009876 |
| 99 | 0.013403 | 0.014048 | 0.018992 | −0.006973 | −0.000288 | −0.01242 | 0.009045 | −0.029722 | −0.030066 | −0.04683 | −0.040123 | −0.017374 | −0.003401 | 0.006557 |
| 100 | 0.006423 | 0.003988 | 0.001633 | 0.018831 | −0.022534 | −0.017536 | −0.023481 | 0.000037 | −0.000119 | 0.001303 | −0.002289 | −0.024083 | −0.014255 | −0.032146 |
| 101 | 0.009061 | 0.016628 | 0.017077 | −0.00539 | 0.000347 | 0.007791 | 0.014404 | −0.006381 | −0.000719 | −0.010347 | −0.003846 | 0.00264 | 0.005892 | 0.006857 |
| 102 | −0.023058 | −0.030598 | 0.004022 | 0.003484 | −0.0027 | −0.001572 | 0.01021 | 0.020488 | 0.022488 | −0.005834 | −0.007676 | −0.007483 | 0.019158 | −0.00782 |
| 103 | −0.02083 | −0.031262 | −0.015038 | 0.040022 | −0.020775 | −0.016209 | −0.01443 | 0.022147 | 0.026051 | −0.012813 | −0.013928 | −0.019767 | −0.00952 | 0.013688 |
| 104 | 0.026243 | 0.031783 | 0.017593 | 0.004582 | −0.004214 | −0.005823 | 0.005814 | −0.005182 | −0.002149 | −0.023272 | −0.020509 | −0.006954 | 0.009276 | −0.005251 |
| 105 | 0.021194 | 0.028233 | 0.015857 | 0.020192 | 0.007402 | 0.012322 | 0.002459 | 0.015291 | 0.007711 | 0.024599 | 0.030449 | 0.010142 | −0.003344 | −0.026457 |
| 106 | −0.0127 | −0.016025 | −0.022778 | −0.002519 | −0.010396 | −0.016995 | −0.018693 | 0.012269 | 0.009245 | −0.00363 | −0.011408 | −0.007455 | −0.006483 | 0.016291 |
| 107 | 0.014057 | 0.017453 | −0.022569 | −0.001935 | 0.006069 | −0.006163 | −0.018249 | −0.015564 | −0.022245 | −0.026849 | −0.026569 | 0.00559 | −0.008637 | 0.003181 |
| 108 | −0.006516 | 0.005442 | 0.008829 | −0.014023 | 0.047 | 0.062512 | 0.018942 | 0.007003 | 0.01516 | 0.021054 | 0.028351 | 0.011916 | −0.002371 | 0.007611 |
| 109 | 0.025456 | 0.030994 | −0.024855 | 0.020746 | −0.021897 | −0.009342 | −0.039012 | 0.000179 | 0.011073 | 0.006503 | 0.01728 | 0.013677 | 0.028426 | 0.008754 |
| 110 | −0.004575 | −0.007424 | −0.005342 | 0.075064 | −0.029982 | −0.022798 | 0.021513 | −0.021114 | −0.031944 | −0.034787 | −0.025317 | 0.013869 | 0.014549 | 0.041442 |
| 111 | 0.002995 | 0.004778 | −0.006426 | 0.00855 | 0.020237 | 0.027112 | 0.008496 | 0.009806 | 0.012785 | 0.001098 | 0.014488 | −0.014576 | −0.011205 | 0.007052 |
| 112 | −0.009844 | −0.015977 | −0.009581 | 0.007964 | 0.03258 | 0.039637 | 0.010264 | −0.011734 | −0.023396 | 0.019624 | 0.013226 | 0.012876 | −0.004597 | 0.004039 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 113 | −0.011506 | −0.015255 | −0.006961 | 0.007582 | 0.009743 | 0.005435 | −0.034895 | −0.009939 | 0.003849 | −0.017926 | −0.015437 | −0.037925 | −0.007613 | 0.019916 |
| 114 | −0.027089 | −0.008453 | −0.037165 | 0.015873 | 0.046109 | 0.045357 | 0.007094 | −0.009048 | 0.000031 | 0.002013 | 0.008898 | 0.035932 | 0.018252 | 0.025992 |
| 115 | 0.032342 | 0.030242 | 0.006839 | 0.025782 | −0.003694 | −0.003445 | 0.010416 | −0.020699 | −0.029398 | −0.015889 | −0.006616 | −0.002715 | 0.003999 | −0.006042 |
| 116 | 0.019515 | 0.018002 | −0.014966 | 0.022589 | −0.008176 | 0.002225 | −0.016586 | 0.00942 | 0.002879 | −0.002195 | −0.004882 | −0.000655 | 0.019007 | −0.019489 |
| 117 | 0.0033 | −0.003575 | 0.020129 | 0.040997 | 0.023717 | 0.032277 | 0.026249 | −0.000149 | 0.002232 | 0.004 | 0.010991 | −0.000142 | −0.020967 | 0.005508 |
| 118 | 0.016835 | 0.01238 | −0.024059 | −0.045503 | 0.028377 | 0.039147 | −0.01876 | −0.001426 | 0.013914 | 0.002671 | 0.003071 | −0.003452 | 0.016437 | 0.002939 |
| 119 | 0.010907 | 0.002347 | −0.008584 | −0.004831 | 0.01001 | 0.019635 | −0.00279 | −0.020391 | −0.015456 | −0.010464 | −0.009262 | −0.000462 | −0.007073 | −0.017782 |
| 120 | −0.014641 | −0.02372 | 0.00871 | −0.005079 | 0.029121 | 0.027904 | 0.005912 | 0.012591 | 0.01886 | 0.00112 | −0.007451 | −0.021163 | −0.000717 | −0.014786 |
| 121 | 0.021587 | 0.011253 | 0.004836 | 0.033893 | −0.012296 | −0.03197 | −0.031045 | −0.00474 | −0.009906 | −0.024741 | −0.029493 | −0.055255 | −0.011152 | −0.003895 |
| 122 | −0.014811 | −0.013937 | 0.010347 | −0.009748 | −0.02897 | −0.020239 | −0.003821 | 0.006036 | 0.005553 | 0.003816 | 0.002334 | 0.016622 | 0.011164 | 0.03672 |
| 123 | 0.006444 | 0.00012 | −0.017697 | 0.037271 | −0.006578 | 0.003819 | −0.033638 | 0.000216 | 0.000186 | 0.013455 | 0.005002 | 0.006274 | 0.003496 | 0.012014 |
| 124 | 0.015979 | 0.009652 | −0.002358 | 0.006317 | −0.012657 | −0.001914 | −0.020376 | −0.011366 | −0.009076 | 0.002589 | 0.000735 | 0.004117 | −0.02217 | −0.006793 |
| 125 | 0.016794 | 0.008337 | 0.021326 | 0.025364 | 0.014664 | 0.010851 | −0.00217 | −0.020321 | −0.019591 | 0.011212 | 0.002126 | −0.016868 | −0.019512 | 0.00047 |
| 126 | 0.010862 | 0.00343 | −0.017091 | −0.006417 | −0.002391 | −0.00977 | −0.021382 | 0.002196 | 0.003898 | −0.0093334 | −0.010746 | 0.004014 | 0.016855 | 0.012832 |
| 127 | 0.012504 | 0.007402 | −0.002734 | −0.021069 | −0.001885 | −0.008099 | 0.00959 | −0.003539 | −0.008148 | −0.008638 | −0.008726 | 0.010518 | 0.011167 | 0.008161 |
| 128 | 0.005481 | 0.008636 | −0.001474 | 0.014071 | −0.002606 | −0.00448 | −0.005888 | −0.008639 | −0.011601 | 0.007297 | 0.001157 | 0.004822 | −0.005619 | −0.009198 |
| 129 | −0.021233 | −0.013622 | 0.020698 | −0.00797 | −0.031652 | −0.00187 | 0.014331 | 0.021188 | 0.023474 | 0.004148 | 0.013933 | 0.025522 | 0.008542 | 0.012861 |
| 130 | 0.016292 | 0.021005 | 0.002772 | −0.027134 | −0.029291 | −0.032154 | −0.027429 | 0.000623 | −0.002467 | −0.002301 | −0.010237 | −0.012669 | 0.008434 | 0.01501 |
| 131 | −0.003425 | 0.004852 | 0.030503 | −0.009995 | −0.026514 | −0.005127 | 0.015493 | −0.004348 | 0.003823 | −0.036773 | −0.019085 | −0.011893 | −0.012035 | 0.024943 |
| 132 | −0.00272 | −0.002949 | −0.002867 | 0.007226 | 0.012466 | 0.019673 | 0.005427 | −0.006555 | −0.003585 | 0.010919 | 0.011537 | 0.001462 | −0.002955 | −0.002252 |
| 133 | 0.006849 | 0.003801 | 0.015243 | 0.031135 | −0.029042 | −0.031331 | 0.003045 | −0.016955 | −0.013759 | −0.031632 | −0.026022 | −0.011499 | −0.012455 | 0.031229 |
| 134 | 0.019221 | 0.011492 | −0.029289 | −0.026377 | −0.008563 | −0.010802 | −0.014802 | 0.009668 | 0.002559 | 0.011657 | 0.008356 | 0.000642 | −0.001511 | 0.000693 |
| 135 | −0.002064 | −0.010953 | −0.000585 | −0.00231 | 0.000663 | −0.005353 | −0.004736 | 0.005304 | 0.004492 | 0.01448 | −0.000056 | −0.010547 | −0.004391 | −0.014559 |
| 136 | −0.007989 | −0.009941 | −0.022101 | 0.029039 | −0.014582 | −0.002944 | −0.002091 | 0.004466 | 0.007761 | 0.003832 | 0.008827 | 0.004178 | 0.009392 | 0.013633 |
| 137 | 0.005567 | 0.005643 | −0.001242 | −0.012467 | −0.008946 | −0.013821 | −0.030678 | −0.000504 | −0.002728 | 0.010867 | −0.000803 | −0.011207 | −0.021305 | −0.008379 |
| 138 | −0.012691 | 0.003877 | 0.008556 | −0.041836 | 0.005939 | 0.022358 | 0.022883 | 0.003731 | 0.014177 | 0.009337 | 0.016983 | 0.016209 | 0.019549 | −0.006536 |
| 139 | −0.005167 | 0.005608 | 0.001449 | −0.047437 | 0.000887 | 0.000205 | −0.034319 | 0.016473 | 0.019693 | −0.001899 | −0.002306 | −0.009257 | −0.002296 | −0.004133 |
| 140 | −0.005241 | 0.010539 | 0.017946 | −0.003756 | 0.026327 | 0.025147 | 0.019664 | −0.032089 | −0.035872 | −0.017771 | −0.018353 | −0.002301 | 0.013015 | 0.024246 |
| 141 | −0.0147 | −0.027326 | −0.022966 | 0.006584 | 0.004017 | −0.0098 | 0.000146 | −0.001134 | −0.010148 | 0.01088 | −0.006195 | 0.001172 | 0.004276 | −0.008514 |
| 142 | −0.013564 | −0.002059 | −0.011433 | 0.019462 | 0.006285 | 0.025955 | 0.006129 | 0.007766 | 0.0166 | 0.020337 | 0.024782 | 0.015423 | 0.007917 | 0.023873 |
| 143 | 0.003696 | 0.018578 | 0.027364 | 0.00205 | −0.019415 | −0.005682 | 0.008313 | −0.002171 | 0.000825 | 0.004125 | −0.00021 | 0.00763 | 0.009977 | 0.01953 |
| 144 | −0.015721 | −0.019268 | −0.005211 | 0.035747 | −0.0278 | −0.007093 | −0.001055 | 0.008351 | 0.015873 | 0.009324 | 0.008441 | 0.007172 | 0.008222 | −0.004752 |
| 145 | −0.006516 | 0.00688 | 0.001547 | 0.015219 | −0.026913 | 0.000744 | 0.007633 | −0.002507 | 0.019572 | −0.010093 | 0.003489 | 0.005134 | 0.015511 | 0.024056 |
| 146 | 0.00227 | −0.00102 | −0.006139 | −0.01243 | 0.009234 | 0.003078 | −0.020341 | −0.000015 | 0.002393 | −0.000242 | −0.013221 | −0.01855 | −0.00896 | 0.000178 |
| 147 | 0.001139 | 0.010776 | −0.010574 | 0.004075 | 0.035963 | 0.035931 | 0.016481 | 0.0088 | 0.013313 | −0.014656 | −0.01268 | 0.023668 | 0.021455 | 0.032241 |
| 148 | −0.034355 | −0.019533 | −0.030471 | −0.037321 | 0.007932 | 0.021312 | −0.015153 | 0.020551 | 0.029964 | 0.016203 | 0.008553 | 0.018965 | −0.00499 | 0.032255 |
| 149 | −0.001961 | 0.001802 | −0.001048 | −0.000114 | −0.011364 | −0.017732 | −0.00099 | −0.00915 | −0.00763 | −0.016471 | −0.01746 | −0.018227 | −0.006975 | 0.00354 |
| 150 | 0.005484 | 0.008234 | 0.016458 | −0.008748 | 0.010035 | 0.012697 | −0.019164 | 0.010683 | 0.008503 | 0.012202 | −0.005134 | −0.022228 | −0.002101 | −0.015201 |
| 151 | 0.020373 | 0.02928 | −0.008018 | −0.010564 | 0.003739 | 0.003363 | 0.019951 | −0.01374 | −0.014113 | −0.027917 | −0.025066 | 0.004075 | 0.005943 | −0.029889 |
| 152 | −0.008274 | −0.014411 | −0.016284 | −0.001675 | 0.026888 | 0.020718 | 0.022591 | −0.009985 | −0.019751 | 0.000574 | −0.000532 | 0.017513 | 0.0019 | 0.007353 |
| 153 | 0.006934 | −0.005417 | −0.024053 | 0.014652 | −0.007079 | −0.009125 | −0.029657 | 0.004289 | −0.000492 | 0.01225 | 0.00206 | 0.023063 | 0.01435 | 0.012814 |
| 154 | −0.002819 | −0.004519 | 0.000976 | 0.024607 | −0.018442 | −0.007136 | 0.012357 | 0.010839 | 0.012435 | 0.001825 | 0.00455 | −0.001317 | 0.018879 | −0.001017 |
| 155 | −0.003569 | 0.002703 | −0.000425 | −0.022334 | 0.003954 | 0.018702 | 0.001477 | 0.010118 | 0.019347 | 0.018142 | 0.022994 | 0.01914 | 0.013923 | 0.013239 |
| 156 | 0.011686 | 0.009152 | 0.025068 | 0.007882 | −0.015301 | −0.018702 | 0.001327 | −0.003244 | −0.001844 | −0.024432 | −0.030003 | −0.030575 | −0.004546 | −0.016967 |
| 157 | 0.000058 | −0.003081 | 0.004782 | 0.018924 | −0.007355 | −0.008036 | −0.011375 | −0.009393 | −0.009594 | −0.006003 | −0.012454 | −0.019453 | −0.010648 | 0.00126 |
| 158 | 0.001932 | 0.005242 | 0.008479 | −0.040421 | −0.007314 | −0.020392 | 0.023593 | 0.002253 | −0.005196 | −0.000766 | −0.002241 | 0.02134 | 0.002581 | 0.011472 |
| 159 | 0.007279 | 0.024334 | 0.021333 | −0.003674 | −0.005803 | 0.014026 | 0.023503 | 0.021545 | 0.023369 | 0.029742 | 0.033502 | 0.023557 | 0.009147 | −0.034593 |
| 160 | 0.017497 | 0.006922 | 0.000807 | 0.015226 | −0.018606 | −0.026779 | −0.024014 | −0.038015 | −0.038204 | −0.033756 | −0.043606 | −0.004268 | −0.023837 | 0.018248 |
| 161 | −0.015289 | −0.004205 | −0.019062 | −0.034739 | −0.003085 | 0.000368 | −0.013469 | 0.012384 | 0.004575 | 0.025168 | 0.017979 | 0.033399 | 0.001127 | −0.023343 |
| 162 | −0.001932 | −0.002838 | −0.006745 | −0.004716 | 0.007144 | 0.021459 | 0.003883 | 0.000638 | 0.008877 | −0.002874 | −0.010124 | −0.019295 | −0.003055 | −0.018384 |

APPENDIX B3-continued

PCA Transformation
Matrix (340 × 340 Early/Late)

| | | | | | | | | | | | | | |
|---|---|---|---|---|---|---|---|---|---|---|---|---|---|
| 163 | −0.001612 | −0.001009 | −0.007653 | −0.0057 | 0.006267 | 0.004033 | 0.00922 | −0.007197 | −0.011942 | 0.002057 | −0.003038 | −0.004646 | −0.023793 | 0.002987 |
| 164 | −0.00653 | 0.005862 | 0.000524 | 0.010215 | −0.001274 | 0.010392 | 0.021847 | −0.013813 | −0.002406 | −0.035275 | −0.016637 | −0.009093 | −0.002449 | −0.002636 |
| 165 | 0.021189 | 0.018731 | −0.003734 | 0.01974 | 0.013233 | 0.007106 | 0.006934 | −0.022343 | −0.022469 | 0.014155 | 0.016994 | 0.032119 | −0.025342 | 0.000572 |
| 166 | −0.020032 | −0.020377 | −0.007065 | 0.01556 | −0.02219 | 0.001861 | −0.022886 | 0.012462 | 0.035001 | 0.035271 | 0.042354 | −0.0003651 | −0.025033 | 0.010992 |
| 167 | 0.001726 | 0.003626 | 0.018228 | 0.032345 | −0.001082 | 0.003384 | −0.006409 | −0.015469 | −0.002 | −0.009386 | −0.001197 | −0.025486 | −0.001976 | 0.006315 |
| 168 | 0.01839 | 0.016017 | 0.006737 | −0.024294 | −0.023977 | −0.034704 | −0.020128 | −0.009811 | −0.014901 | −0.020018 | −0.022959 | −0.008854 | 0.004548 | −0.009629 |
| 169 | 0.009277 | 0.014239 | 0.015604 | −0.007871 | −0.000065 | 0.004776 | 0.009478 | −0.005491 | −0.000971 | −0.011913 | −0.009395 | 0.003445 | 0.007308 | 0.017067 |
| 170 | 0.005629 | 0.011552 | 0.011183 | −0.017127 | −0.009062 | −0.004058 | 0.019077 | −0.005778 | −0.004239 | −0.015014 | −0.011381 | 0.022164 | 0.012024 | 0.024139 |
| 171 | 0.003876 | 0.003921 | −0.003004 | −0.00902 | 0.002474 | −0.003499 | −0.00975 | −0.001384 | −0.004701 | −0.000205 | −0.00281 | 0.003947 | 0.010269 | 0.003788 |
| 172 | 0.013419 | 0.010385 | 0.010812 | −0.010457 | 0.01614 | 0.009097 | −0.000378 | −0.006881 | −0.002874 | −0.003281 | −0.00557 | 0.008268 | −0.00791 | −0.000189 |
| 173 | 0.019933 | 0.017605 | 0.007059 | 0.017591 | −0.003483 | −0.012685 | −0.01331 | −0.003032 | −0.001134 | 0.001896 | 0.002225 | 0.009181 | 0.008953 | 0.009773 |
| 174 | −0.002442 | −0.001036 | 0.003519 | −0.019097 | −0.016938 | −0.025829 | −0.010873 | 0.004462 | 0.008841 | −0.002915 | −0.003975 | −0.011671 | 0.005342 | −0.002698 |
| 175 | −0.017555 | −0.015232 | −0.002714 | −0.051618 | 0.003963 | −0.002426 | −0.017631 | 0.002626 | 0.003813 | 0.008327 | −0.002348 | −0.018646 | −0.027407 | 0.006328 |
| 176 | 0.004953 | 0.003059 | 0.0161 | 0.004395 | 0.004128 | −0.007032 | −0.007464 | −0.006058 | −0.012093 | −0.001582 | −0.005793 | −0.018667 | −0.042271 | −0.004411 |
| 177 | 0.014566 | 0.006303 | 0.026002 | 0.000403 | −0.002712 | −0.009885 | 0.018949 | 0.007738 | 0.009095 | −0.030174 | −0.025132 | −0.01115 | 0.020906 | −0.053753 |
| 178 | 0.002404 | 0.001387 | −0.01241 | 0.007287 | −0.00355 | −0.012071 | −0.018692 | −0.000036 | −0.006836 | −0.009986 | −0.014223 | −0.004167 | −0.012811 | −0.015157 |
| 179 | 0.000473 | 0.006082 | 0.002511 | 0.005818 | 0.006131 | 0.010247 | 0.004711 | −0.006866 | −0.004069 | −0.006461 | −0.001092 | 0.0054 | 0.00832 | 0.010355 |
| 180 | −0.000516 | −0.00274 | 0.001553 | 0.008651 | 0.00281 | 0.000956 | −0.002784 | −0.002984 | −0.002983 | −0.004161 | −0.003034 | 0.004659 | 0.009804 | 0.011996 |
| 181 | 0.002506 | 0.00268 | 0.003623 | 0.012686 | −0.004623 | −0.002913 | −0.00048 | −0.004098 | −0.004469 | −0.002826 | 0.002368 | 0.012192 | 0.006593 | 0.015912 |
| 182 | −0.010824 | −0.013909 | 0.003472 | 0.008514 | −0.007167 | −0.010107 | 0.004918 | −0.002048 | −0.006908 | −0.007404 | −0.005987 | 0.010112 | 0.007321 | 0.001551 |
| 183 | −0.003091 | −0.007019 | −0.008983 | 0.017869 | −0.001218 | 0.001148 | −0.014485 | 0.000983 | −0.001447 | 0.009913 | 0.008449 | −0.002787 | 0.008735 | −0.01929 |
| 184 | −4.008778 | −4.007778 | −4.030357 | 0.018752 | 0.006414 | 0.020605 | −4.03261 | 0.006579 | 0.015412 | 0.034432 | 0.028019 | −4.02237 | −4.014626 | −4.038936 |
| 185 | 0.01189 | 0.0039 | 0.021182 | 0.023005 | −0.004181 | −0.006804 | −0.019428 | 0.00733 | 0.000755 | 0.027506 | 0.018773 | 0.012833 | −0.002282 | −0.011331 |
| 186 | 0.003582 | −0.004762 | −0.03882 | −0.01798 | −0.002332 | −0.007038 | −0.051613 | 0.016063 | 0.016624 | 0.015662 | 0.008217 | 0.009479 | 0.008092 | 0.019982 |
| 187 | 0.001035 | −0.004335 | −0.004717 | 0.017223 | 0.011304 | 0.01337 | 0.013267 | 0.005624 | 0.01116 | −0.000714 | −0.001556 | 0.004097 | 0.012279 | −0.013473 |
| 188 | −0.013739 | −0.018878 | 0.000743 | −0.001789 | 0.00019 | 0.001072 | 0.015039 | 0.009007 | 0.014592 | −0.005028 | −0.007527 | −0.008174 | 0.015642 | −0.024503 |
| 189 | −4.027647 | −0.023669 | 0.007686 | −4.018038 | −4.003538 | 0.0137 | 0.013344A | 0.017597 | 0.02724 | 0.01024 | 0.006092 | −4.024816 | 0.00325 | −4.020131 |
| 190 | 0.001081 | 0.000727 | 0.000787 | −0.002748 | −0.012884 | −0.011584 | −0.022526 | −0.00913 | −0.004087 | −0.000174 | −0.00288 | −0.029652 | −0.026801 | −0.006651 |
| 191 | 0.00775 | 0.009737 | 0.006417 | −0.010607 | −0.003927 | 0.00148 | 0.006936 | −0.009136 | −0.003081 | −0.007757 | −0.005628 | −0.005868 | 0.00235 | 0.003555 |
| 192 | 0.00041 | 0.00285 | 0.003305 | −0.026979 | −0.004086 | −0.009784 | 0.027327 | −0.015923 | −0.019373 | −0.033023 | −0.032638 | −0.00646 | 0.023199 | −0.006714 |
| 193 | −0.002697 | −0.01266 | −0.017478 | 0.003458 | 0.004187 | −0.00162 | 0.000329 | −0.001232 | −0.002157 | 0.002898 | −0.001622 | 0.014196 | 0.002051 | 0.00292 |
| 194 | 0.004749 | −0.003244 | 0.005773 | −0.012247 | 0.017707 | 0.016144 | −0.000758 | −0.000734 | 0.001314 | −0.002312 | −0.008881 | −0.013498 | −0.003217 | −0.009561 |
| 195 | 0.009323 | 0.018177 | −0.00528 | 0.022535 | 0.018054 | 0.025606 | −0.004516 | −0.002808 | 0.000844 | 0.009657 | 0.014767 | 0.016587 | −0.031557 | 0.035218 |
| 196 | −0.001844 | 0.003398 | −0.001881 | −0.013074 | 0.001246 | 0.004762 | −0.010203 | −0.007245 | −0.003637 | −0.004458 | −0.00249 | −0.018445 | −0.025448 | 0.010481 |
| 197 | 0.000791 | 0.001117 | 0.012379 | −0.004253 | −0.00903 | −0.013453 | 0.008334 | −0.022524 | −0.021726 | −0.021076 | −0.020255 | −0.024529 | −0.015866 | 0.006217 |
| 198 | 0.009532 | 0.008558 | −0.017536 | 0.004174 | 0.040603 | 0.03235 | −0.006249 | 0.00165 | −0.004528 | 0.01418 | 0.004225 | 0.030698 | −0.040695 | 0.00852 |
| 199 | −0.019253 | 0.008421 | 0.010696 | −0.007187 | 0.009095 | 0.020581 | 0.045492 | −0.00111 | 0.01241 | −0.025805 | −0.009848 | −0.02973 | −0.017682 | −0.019777 |
| 200 | 0.016529 | 0.012381 | −0.017968 | −0.007772 | 0.012809 | −0.001176 | −0.018505 | −0.010214 | −0.015475 | −0.005437 | −0.006678 | 0.011149 | −0.02607 | −0.011515 |
| 201 | 0.012057 | 0.000144 | −0.007023 | 0.012081 | 0.008717 | −0.011817 | −0.000564 | −0.000194 | −0.018727 | −0.021663 | −0.026942 | 0.016168 | 0.00642 | −0.002105 |
| 202 | 0.00899 | −0.001221 | −0.022649 | 0.002298 | 0.024544 | −0.001068 | −0.005927 | −0.007912 | −0.020189 | −0.010453 | −0.017433 | 0.012466 | −0.031358 | 0.013835 |
| 203 | 0.004119 | 0.01652 | 0.019729 | −0.01028 | −0.021461 | 0.008097 | 0.010134 | 0.003989 | 0.017225 | 0.009533 | 0.018512 | 0.004494 | −0.003224 | −0.019053 |
| 204 | 0.030683 | 0.016196 | 0.027828 | 0.006765 | −0.015663 | −0.022947 | −0.013804 | −0.008746 | −0.017907 | −0.012212 | −0.008604 | 0.00408 | −0.007022 | −0.009802 |
| 205 | 0.0025 | 0.003715 | 0.014383 | −0.014922 | 0.029632 | 0.029504 | 0.010608 | −0.015142 | −0.014945 | 0.039344 | 0.03895 | −0.002827 | −0.0244 | 0.015535 |
| 206 | −0.009123 | −0.02027 | 0.003431 | 0.007744 | −0.014649 | −0.015898 | −0.028175 | −0.007546 | 0.009243 | 0.009265 | 0.010784 | −0.007389 | −0.030451 | 0.025572 |
| 207 | 0.001539 | −0.013658 | −0.002673 | −0.002578 | −0.003368 | −0.006397 | 0.014431 | −0.021952 | −0.028195 | −0.014591 | −0.010479 | 0.00114 | 0.013274 | −0.002423 |
| 208 | 0.004915 | −0.00352 | 0.013738 | 0.01007 | −0.004017 | 0.014396 | 0.03172 | −0.00883 | −0.005881 | 0.002226 | 0.011529 | 0.016922 | 0.009696 | 0.011914 |
| 209 | −0.011096 | −0.012922 | −0.012516 | −0.012647 | −0.028092 | −0.036845 | −0.000535 | 0.011304 | 0.004851 | 0.001059 | −0.002487 | −0.020378 | −0.013487 | −0.012821 |
| 210 | −0.014118 | −0.005118 | −0.011779 | 0.029894 | −0.004414 | −0.012726 | −0.032714 | 0.026185 | 0.020955 | −0.009233 | −0.00858 | −0.010325 | −0.015194 | 0.014095 |
| 211 | −0.0037 | −0.002351 | −0.009072 | 0.003217 | −0.010939 | −0.030116 | −0.023153 | 0.014399 | 0.008223 | −0.026367 | −0.029063 | −0.027446 | 0.016363 | −0.008493 |
| 212 | 0.012395 | 0.023125 | −0.015061 | 0.028738 | 0.02055 | 0.027449 | −0.005653 | −0.012568 | −0.005401 | −0.011859 | −0.005441 | −0.011961 | −0.024895 | 0.016352 |

APPENDIX B3-continued

PCA Transformation
Matrix (340 × 340 Early/Late)

| | | | | | | | | | | | | | |
|---|---|---|---|---|---|---|---|---|---|---|---|---|---|
| 213 | −0.019712 | −0.022396 | −0.012913 | −0.021157 | 0.0131 | 0.027661 | −0.010433 | 0.004444 | 0.015046 | −0.00914 | −0.001058 | 0.02678 | 0.013469 | −0.000009 |
| 214 | −0.00226 | −0.006086 | −0.005978 | 0.017086 | 0.002204 | 0.004589 | −0.009083 | 0.000595 | −0.000562 | 0.002727 | −0.000118 | −0.008294 | 0.01065 | −0.005156 |
| 215 | 0.017144 | 0.013367 | 0.014348 | −0.015551 | −0.001279 | 0.001727 | −0.000331 | −0.001152 | −0.001555 | 0.005338 | 0.008921 | 0.009026 | 0.009201 | 0.012472 |
| 216 | 0.010645 | 0.010706 | −0.016192 | −0.028279 | 0.013378 | 0.008223 | −0.009724 | 0.013707 | 0.012632 | −0.002822 | −0.002685 | −0.006564 | 0.011474 | 0.003326 |
| 217 | 0.015528 | 0.028988 | −0.008123 | −0.017684 | 0.027794 | 0.03787 | −0.016543 | 0.006202 | 0.014629 | −0.00175 | −0.000049 | −0.024118 | −0.021457 | −0.021349 |
| 218 | −0.011797 | −0.009749 | 0.014721 | −0.006827 | −0.027551 | −0.022658 | −0.005196 | 0.015651 | 0.015607 | 0.018225 | 0.017143 | 0.012998 | 0.017416 | 0.022203 |
| 219 | 0.011411 | 0.019295 | −0.04248 | 0.005494 | 0.009289 | 0.017712 | −0.035831 | 0.018714 | 0.022323 | 0.016744 | 0.014477 | 0.003649 | 0.017602 | 0.017984 |
| 220 | 0.054164 | 0.055776 | 0.027307 | −0.013823 | −0.042066 | −0.033184 | −0.057172 | 0.004365 | 0.009978 | 0.008413 | 0.008619 | −0.030356 | −0.033677 | −0.019654 |
| 221 | 0.035053 | 0.031334 | 0.015978 | 0.007018 | 0.01184 | −0.001292 | −0.017377 | −0.008267 | −0.00974 | −0.002447 | −0.006068 | 0.00032 | 0.012767 | 0.020445 |
| 222 | 0.014751 | 0.018043 | 0.004314 | −0.03089 | −0.005163 | −0.008272 | 0.004392 | −0.00037 | −0.001475 | −0.004574 | −0.004652 | −0.000793 | 0.014617 | 0.019491 |
| 223 | 0.019948 | 0.014455 | 0.005481 | −0.00992 | −0.014063 | −0.018268 | −0.013413 | 0.006208 | 0.002478 | 0.006941 | 0.008126 | 0.014914 | 0.015689 | 0.028189 |
| 224 | 0.000645 | −0.008064 | 0.004249 | −0.036367 | 0.009548 | −0.013414 | −0.000714 | 0.00254 | −0.000184 | −0.0306251 | −0.026683 | −0.038911 | −0.02155 | −0.002037 |
| 225 | 0.002277 | −0.006521 | 0.012549 | −0.033178 | 0.013305 | −0.007449 | 0.010933 | 0.00363 | 0.00233 | −0.03202 | −0.025657 | −0.028595 | −0.009115 | 0.003103 |
| 226 | 0.012151 | 0.015198 | 0.01521 | 0.002071 | −0.000177 | 0.004513 | 0.012974 | −0.021501 | −0.02127 | −0.012459 | −0.012818 | −0.002723 | −0.003175 | 0.014953 |
| 227 | 0.019091 | 0.021827 | 0.033764 | −0.012039 | 0.016758 | 0.005534 | 0.014048 | −0.021805 | −0.024346 | −0.034385 | −0.03384 | −0.019619 | −0.007573 | 0.012663 |
| 228 | −0.013095 | −0.01909 | −0.022736 | −0.086351 | 0.000201 | 0.000015 | 0.002224 | −0.001532 | −0.003422 | 0.000059 | −0.006541 | −0.012526 | −0.007352 | 0.010774 |
| 229 | 0.019609 | 0.01535 | 0.005598 | −0.025084 | 0.00832f | 0.022979 | 0.01743 | 0.003064 | 0.015547 | 0.02384 | 0.027476 | 0.044654 | 0.013725 | 0.025383 |
| 230 | 0.020207 | 0.01152 | −0.010318 | −0.002745 | 0.016719 | 0.004228 | −0.01067 | −0.003099 | −0.00645 | 0.010054 | 0.006433 | 0.016227 | 0.004648 | 0.007019 |
| 231 | 0.003509 | 0.005929 | −0.014017 | 0.024626 | 0.031263 | 0.033076 | 0.014955 | −0.007343 | −0.006976 | 0.019312 | 0.024701 | 0.026851 | −0.005721 | 0.014713 |
| 232 | −0.006134 | −0.009706 | 0.000092 | −0.052758 | 0.008477 | 0.004517 | 0.012683 | 0.000006 | −0.00422 | 0.012958 | 0.008496 | −0.005492 | −0.024868 | 0.010739 |
| 233 | −0.007377 | −0.004354 | 0.005433 | −0.051647 | −0.018796 | −0.019653 | 0.007692 | 0.021596 | 0.015721 | 0.005924 | 0.005239 | 0.037913 | 0.022372 | 0.020257 |
| 234 | 0.002775 | 0.006371 | −0.015578 | −0.035891 | 0.004892 | 0.007758 | −0.006852 | 0.000757 | −0.005396 | 0.017457 | 0.015451 | 0.004426 | 0.00102 | −0.00721 |
| 235 | 0.00438 | 0.003767 | −0.016481 | −0.05247 | 0.003733 | −0.004002 | −0.018372 | −0.001108 | −0.004198 | 0.003604 | 0.00064 | −0.006459 | −0.013258 | −0.004339 |
| 236 | −0.025369 | −0.027174 | −0.001196 | −0.002468 | 0.000684 | −0.001289 | −0.023591 | 0.01217 | 0.012214 | 0.026655 | 0.024093 | −0.020711 | −0.038717 | 0.002818 |
| 237 | −0.052629 | −0.050085 | 0.01295 | 0.002277 | 0.005977 | 0.023339 | 0.043035 | 0.022243 | 0.028403 | 0.021454 | 0.026582 | 0.003524 | 0.023094 | −0.033999 |
| 238 | −0.011372 | −0.006827 | −0.058915 | 0.017679 | 0.04628 | 0.054662 | 0.007725 | 0.013174 | 0.014901 | 0.018671 | 0.021427 | 0.017586 | 0.024732 | −0.008833 |
| 239 | −0.011728 | −0.007654 | −0.08099 | 0.020633 | 0.038495 | 0.040159 | −0.0118 | 0.013618 | 0.008811 | 0.019672 | 0.019705 | 0.024969 | 0.009406 | 0.016196 |
| 240 | 0.021806 | 0.025587 | −0.002163 | 0.014394 | 0.010409 | 0.01729 | 0.003006 | −0.00781 | −0.0017 | −0.007944 | −0.006201 | 0.000435 | 0.008072 | 0.001546 |
| 241 | 0.00261 | 0.002781 | 0.011771 | −0.028878 | −0.016695 | −0.017684 | 0.001867 | 0.012934 | 0.009889 | −0.007968 | −0.008092 | 0.002306 | 0.017397 | −0.001564 |
| 242 | −0.013524 | −0.013362 | 0.005999 | −0.064588 | −0.021273 | −0.025037 | −0.02715 | 0.02521 | 0.019968 | 0.027956 | 0.02331 | −0.007245 | −0.025229 | −0.007564 |
| 243 | 0.000611 | 0.004285 | −0.024327 | −0.12595 | 0.004222 | −0.002858 | −0.035407 | 0.03252 | 0.02962 | 0.009969 | −0.001329 | −0.011919 | −0.013015 | −0.013923 |
| 244 | 0.008617 | −0.002121 | −0.002652 | 0.016549 | 0.036118 | 0.018862 | 0.008601 | 0.001858 | −0.00508 | −0.000118 | −0.008178 | 0.019062 | 0.009655 | −0.000085 |
| 245 | −0.009115 | −0.010371 | 0.016462 | 0.019816 | −0.011871 | −0.015978 | 0.008275 | 0.015092 | 0.0141 | −0.000087 | 0.000261 | 0.011406 | 0.012289 | −0.001251 |
| 246 | −0.001811 | 0.005701 | 0.025784 | 0.006327 | −0.070577 | −0.052874 | −0.017233 | 0.024547 | 0.025371 | 0.023524 | 0.030733 | 0.001207 | −0.002961 | −0.015935 |
| 247 | 0.010491 | 0.014346 | −0.007814 | 0.003204 | −0.037455 | −0.03454 | −0.06576 | 0.017761 | 0.019482 | 0.014186 | 0.012113 | −0.0286 | −0.028894 | −0.005294 |
| 248 | 0.016441 | 0.011661 | −0.012771 | 0.001687 | −0.011729 | −0.01285 | −0.063427 | 0.010102 | 0.011487 | 0.018722 | 0.010234 | −0.033934 | −0.029092 | −0.001897 |
| 249 | 0.02496 | 0.031028 | 0.007841 | −0.034403 | 0.004186 | 0.010292 | 0.019339 | −0.001188 | −0.003891 | 0.003694 | 0.003886 | 0.019358 | 0.00233 | 0.007879 |
| 250 | 0.020925 | 0.01993 | 0.009513 | 0.019551 | 0.009162 | 0.014663 | 0.011472 | −0.005849 | −0.005563 | 0.007732 | 0.011181 | 0.011556 | 0.011996 | −0.00584 |
| 251 | 0.026785 | 0.017979 | 0.008477 | 0.022943 | 0.010059 | 0.002336 | −0.006969 | −0.007188 | −0.009825 | −0.007789 | −0.01035 | −0.009006 | 0.009251 | −0.017591 |
| 252 | 0.013193 | 0.013542 | 0.019409 | −0.008967 | 0.025062 | 0.013717 | −0.000832 | 0.003784 | −0.004341 | 0.008821 | 0.003749 | 0.00567 | −0.022015 | −0.008998 |
| 253 | −0.000219 | −0.005499 | 0.030558 | −0.093871 | 0.006145 | 0.00298 | 0.025555 | 0.001205 | −0.002547 | 0.000202 | −0.002992 | −0.005524 | −0.00838 | −0.018388 |
| 254 | 0.013398 | 0.008997 | −0.014847 | −0.011519 | −0.00315 | −0.00475 | −0.010557 | 0.016746 | 0.015036 | 0.00563 | 0.006642 | 0.0243 | 0.011658 | 0.016868 |
| 255 | 0.035022 | 0.03197 | 0.007466 | 0.006805 | −0.003543 | −0.009405 | −0.016747 | 0.00384 | 0.002588 | −0.002358 | −0.005693 | 0.010082 | 0.003363 | −0.006617 |
| 256 | 0.051466 | 0.051889 | 0.038126 | −0.010422 | −0.013115 | −0.017283 | −0.000827 | −0.021979 | −0.01729 | −0.016796 | −0.01384 | 0.005977 | −0.005999 | −0.006591 |
| 257 | 0.031497 | 0.037663 | 0.031441 | 0.021696 | 0.014622 | 0.00306 | 0.024521 | −0.059608 | −0.065057 | −0.052423 | −0.044253 | −0.009623 | −0.019676 | 0.015084 |
| 258 | 0.003247 | 0.005327 | 0.028266 | −0.016952 | −0.017408 | −0.038587 | −0.007717 | −0.023786 | −0.024142 | −0.076506 | −0.072972 | −0.073864 | −0.033323 | −0.000232 |
| 259 | 0.006661 | 0.004889 | −0.002732 | −0.034707 | 0.004183 | 0.00553 | 0.003768 | 0.011058 | 0.010298 | 0.010141 | 0.00947 | 0.010637 | 0.014667 | 0.004451 |
| 260 | 0.002899 | −0.002507 | 0.004115 | 0.013398 | 0.026315 | 0.028969 | −0.002057 | 0.011962 | 0.009601 | 0.036949 | 0.032441 | 0.012775 | −0.016999 | −0.003272 |
| 261 | 0.011978 | 0.013914 | 0.000155 | 0.021505 | 0.011834 | 0.020905 | −0.01995 | 0.001754 | 0.006871 | 0.014567 | 0.015308 | −0.022263 | −0.025977 | −0.012691 |
| 262 | −0.004264 | −0.004472 | −0.006744 | 0.00897 | 0.002716 | −0.000604 | −0.025562 | −0.002977 | −0.005504 | 0.019303 | 0.015935 | −0.019672 | −0.050491 | −0.010228 |

APPENDIX B3-continued

PCA Transformation Matrix (340 × 340 Early/Late)

| | | | | | | | | | | | | | |
|---|---|---|---|---|---|---|---|---|---|---|---|---|---|
| 263 | −0.003498 | −0.005546 | −0.004193 | −0.016088 | 0.007714 | −0.00099 | −0.023284 | −0.004962 | −0.009565 | 0.01043 | 0.004572 | −0.017983 | −0.041224 | −0.008934 |
| 264 | 0.009627 | 0.011747 | −0.009686 | −0.040065 | −0.008091 | −0.000981 | 0.000344 | 0.007783 | 0.01279 | −0.000267 | 0.001416 | 0.001856 | 0.016165 | 0.007431 |
| 265 | 0.006868 | 0.015719 | −0.018811 | −0.027706 | −0.006547 | 0.007247 | −0.007935 | 0.017251 | 0.024094 | 0.005932 | 0.013204 | 0.006978 | −0.008299 | 0.017219 |
| 266 | 0.017414 | 0.022674 | −0.0117 | 0.004944 | −0.007624 | 0.000505 | −0.031976 | 0.020501 | 0.024038 | 0.003132 | 0.005624 | −0.012909 | −0.022641 | 0.00215 |
| 267 | 0.000137 | −0.000269 | 0.004614 | −0.038284 | 0.015533 | 0.030242 | 0.03735 | −0.003304 | 0.003813 | 0.015922 | 0.020432 | 0.03365 | 0.002036 | 0.016757 |
| 268 | 0.007056 | 0.014779 | 0.010445 | −0.012135 | 0.007144 | 0.011957 | 0.022187 | −0.016287 | −0.015928 | −0.006326 | −0.004497 | 0.007278 | −0.002387 | 0.013913 |
| 269 | 0.014078 | 0.014053 | 0.021657 | −0.006897 | 0.013386 | 0.012556 | 0.022361 | −0.017948 | −0.019429 | −0.006521 | −0.008313 | 0.003152 | 0.00074 | 0.007222 |
| 270 | 0.012794 | 0.011588 | 0.017989 | 0.006582 | 0.007533 | 0.003699 | 0.007672 | −0.023565 | −0.02723 | −0.013646 | −0.020266 | −0.011562 | −0.015397 | 0.003379 |
| 271 | −0.00348 | −0.007123 | −0.006352 | −0.010428 | −0.015495 | −0.015661 | −0.0122031 | 0.017326 | 0.01456 | 0.013098 | 0.00397 | 0.001998 | −0.008398 | 0.005503 |
| 272 | 0.009298 | 0.008191 | −0.011572 | −0.004743 | 0.007915 | 0.027948 | 0.007556 | −0.004346 | 0.012488 | 0.023137 | 0.026502 | 0.033347 | 0.005448 | 0.024682 |
| 273 | 0.010133 | 0.008311 | 0.004476 | 0.005201 | 0.006396 | 0.004398 | −0.010405 | −0.014688 | −0.011064 | 0.015812 | 0.011799 | 0.0082561 | −0.016102 | 0.007275 |
| 274 | 0.011175 | 0.007674 | 0.006703 | 0.003398 | 0.006011 | 0.003592 | −0.010378 | −0.01577 | −0.012058 | 0.011437 | 0.007828 | 0.005901 | −0.014584 | 0.006267 |
| 275 | 0.018613 | 0.005302 | −0.009821 | 0.021554 | 0.01275 | 0.001479 | −0.045415 | −0.008068 | −0.00933 | 0.013065 | −0.00242 | −0.018366 | −0.029213 | −0.013156 |
| 276 | −0.0264 | −0.024285 | −0.004796 | −0.020414 | −0.000861 | 0.002028 | −0.016727 | 0.009852 | 0.016298 | 0.020576 | 0.02154 | −0.020406 | −0.035772 | 0.015797 |
| 277 | 0.921244 | −0.079258 | −0.016739 | −0.002272 | 0.002245 | 0.007848 | 0.024971 | 0.026768 | 0.027338 | 0.02407 | 0.024113 | 0.007552 | 0.004148 | −0.003177 |
| 278 | −0.078829 | 0.903698 | −0.025975 | 0.00989 | 0.005815 | 0.000613 | 0.018408 | 0.024484 | 0.019257 | 0.025543 | 0.019038 | 0.007591 | 0.003699 | −0.005727 |
| 279 | −0.017796 | −0.018776 | 0.898348 | 0.018735 | 0.038635 | 0.039801 | −0.032117 | 0.01476 | 0.012196 | 0.02368 | 0.0173 | 0.008836 | 0.00329 | 0.014121 |
| 280 | −0.016721 | −0.011721 | 0.008937 | 0.817179 | −0.01373 | −0.021975 | 0.006628 | 0.024176 | 0.025318 | −0.010799 | −0.016541 | −0.012732 | −0.005365 | 0.000588 |
| 281 | −0.001989 | −0.007533 | 0.025433 | −0.010835 | 0.888052 | −0.106373 | −0.04527 | 0.02124 | 0.022162 | −0.012395 | −0.010443 | −0.029863 | −0.007047 | −0.009357 |
| 282 | 0.005471 | −0.010139 | 0.02063 | −0.015387 | −0.100808 | 0.87337 | −0.055411 | 0.008704 | −0.002945 | −0.03759 | −0.044521 | −0.042636 | −0.02035 | −0.002804 |
| 283 | 0.014833 | 0.002541 | −0.041191 | 0.007203 | −0.043069 | −0.050558 | 0.881161 | 0.017074 | 0.01665 | 0.019414 | 0.002358 | −0.049252 | −0.037458 | −0.002461 |
| 284 | 0.026554 | 0.026868 | 0.017778 | 0.012594 | 0.009712 | −0.000427 | 0.014855 | 0.945191 | −0.055409 | −0.045598 | −0.040126 | −0.012469 | −0.010905 | 0.013486 |
| 285 | 0.028831 | 0.024157 | 0.014623 | 0.018897 | 0.013121 | −0.009406 | 0.014199 | −0.056606 | 0.93148 | −0.048814 | −0.048436 | −0.008262 | −0.013517 | 0.01213 |
| 286 | 0.019099 | 0.018434 | 0.029781 | −0.019199 | −0.015836 | −0.043729 | 0.01634 | −0.0424 | −0.044548 | 0.883209 | −0.10791 | −0.053327 | 0.000323 | 0.012807 |
| 287 | 0.017479 | 0.009606 | 0.020442 | −0.018797 | −0.008771 | −0.045747 | 0.002933 | −0.037753 | −0.045769 | −0.107513 | 0.889244 | −0.057846 | −0.006993 | 0.008362 |
| 288 | −0.004291 | −0.014801 | 0.013039 | −0.009347 | −0.028811 | −0.045998 | −0.041852 | −0.008729 | −0.007181 | −0.050418 | −0.059072 | 0.883116 | −0.043023 | −0.045633 |
| 289 | 0.005359 | 0.003587 | −0.005972 | 0.008786 | −0.0049581 | −0.013615 | −0.036224 | −0.006179 | −0.009884 | 0.002427 | −0.004498 | −0.038401 | 0.925971 | −0.014855 |
| 290 | 0.000094 | −0.003817 | 0.005051 | 0.015478 | −0.002688 | 0.003929 | −0.011715 | 0.011245 | 0.013311 | 0.01124 | 0.00579 | −0.049026 | −0.016222 | 0.892413 |
| 291 | −0.000154 | −0.002266 | 0.005126 | 0.013762 | −0.003524 | 0.003168 | −0.013184 | 0.010625 | 0.013001 | 0.00864 | 0.003868 | −0.049441 | −0.016052 | −0.104327 |
| 292 | 0.009303 | 0.010899 | −0.003423 | 0.012559 | −0.001377 | 0.008924 | −0.013453 | 0.009207 | 0.011793 | 0.005872 | 0.003444 | −0.04519 | −0.007272 | −0.099781 |
| 293 | 0.007525 | 0.010929 | 0.002211 | −0.001027 | −0.002803 | 0.012245 | −0.002454 | −0.004137 | 0.005421 | 0.016508 | 0.023687 | 0.00017 | 0.012787 | 0.003806 |
| 294 | −0.003739 | −0.005945 | −0.004874 | 0.001802 | −0.003142 | −0.001954 | −0.009478 | 0.00358 | 0.004338 | 0.016564 | 0.011135 | −0.004784 | −0.003399 | 0.002131 |
| 295 | 0.008099 | 0.009388 | −0.005007 | 0.007553 | −0.003255 | 0.005952 | −0.018469 | −0.011982 | −0.005013 | 0.032018 | 0.03287 | 0.013878 | −0.007077 | −0.001135 |
| 296 | 0.009299 | 0.003895 | 0.013073 | −0.001503 | −0.015098 | −0.007502 | −0.033378 | −0.000646 | 0.004123 | 0.032232 | 0.022544 | −0.00726 | −0.021348 | −0.013321 |
| 297 | 0.005574 | 0.001075 | 0.003793 | 0.008482 | −0.011953 | −0.004354 | −0.010286 | −0.007261 | −0.001899 | 0.022106 | 0.023738 | 0.004765 | −0.001939 | −0.000393 |
| 298 | −0.00511 | −0.010233 | −0.008839 | 0.019487 | 0.005674 | 0.007312 | −0.003211 | 0.006257 | 0.004837 | 0.012509 | 0.011723 | 0.002439 | 0.012031 | −0.028795 |
| 299 | −0.003731 | −0.005351 | −0.00239 | −0.001212 | −0.017191 | −0.008742 | −0.000066 | 0.003359 | 0.009158 | 0.007716 | 0.011114 | 0.003684 | 0.01253 | 0.003566 |
| 300 | −0.006837 | −0.008919 | −0.035865 | −0.015593 | 0.006383 | 0.00345 | −0.009117 | −0.013092 | −0.00797 | −0.012408 | −0.010876 | −0.006978 | −0.003323 | −0.016496 |
| 301 | 0.008256 | 0.0038 | −0.010019 | 0.020665 | 0.013331 | 0.015977 | 0.004345 | −0.01882 | −0.02095 | 0.025379 | 0.024703 | 0.015408 | −0.000328 | −0.005971 |
| 302 | 0.011286 | 0.011428 | −0.012649 | 0.011014 | −0.000277 | 0.0006 | −0.006242 | −0.013839 | −0.017217 | 0.007892 | 0.005766 | 0.006283 | −0.014502 | −0.005407 |
| 303 | −0.013242 | −0.01579 | −0.007737 | −0.02668 | −0.004624 | −0.011695 | 0.011158 | 0.005756 | 0.008106 | −0.027752 | −0.02766 | −0.005209 | 0.011061 | 0.013964 |
| 304 | −0.015504 | −0.022243 | −0.008701 | −0.027369 | −0.007315 | −0.008234 | 0.00692 | 0.004769 | 0.009697 | −0.01905 | −0.021121 | −0.020165 | 0.0124 | −0.007205 |
| 305 | 0.017556 | 0.007979 | −0.000812 | 0.003965 | −0.008793 | −0.009512 | −0.000197 | −0.020227 | −0.02501 | −0.011146 | −0.00755 | 0.011395 | −0.000986 | 0.008043 |
| 306 | 0.005759 | 0.012947 | 0.03335 | 0.010195 | −0.01162 | 0.008988 | −0.007493 | −0.010274 | 0.006718 | 0.012199 | 0.026117 | −0.009018 | −0.008809 | −0.019061 |
| 307 | −0.017216 | −0.030834 | 0.011534 | −0.044449 | −0.010487 | −0.03378 | 0.014689 | −0.008098 | −0.010521 | −0.043714 | −0.046018 | −0.015734 | 0.005341 | −0.013071 |
| 308 | 0.015313 | 0.026299 | 0.006932 | −0.020334 | 0.015992 | 0.014913 | 0.044574 | −0.00118 | −0.00585 | −0.008044 | −0.005788 | 0.020975 | 0.003412 | −0.012249 |
| 309 | 0.000765 | −0.007458 | −0.001589 | −0.002229 | 0.0119871 | 0.00309 | 0.000146 | −0.003174 | −0.009522 | 0.000252 | −0.009547 | 0.009652 | 0.008037 | 0.004883 |
| 310 | 0.002812 | −0.005881 | 0.005192 | −0.005375 | 0.002852 | −0.004877 | −0.006009 | 0.003066 | 0.000498 | −0.010745 | −0.016414 | 0.018876 | 0.007989 | −0.003099 |
| 311 | −0.003049 | −0.004354 | 0.000256 | −0.014109 | 0.017153 | 0.015225 | −0.002343 | 0.001753 | 0.00171 | 0.010221 | 0.005774 | 0.008421 | 0.006532 | 0.00233 |
| 312 | 0.023626 | 0.011023 | 0.023072 | −0.017609 | −0.022023 | −0.020378 | 0.013147 | 0.01158 | 0.011795 | −0.009715 | −0.018433 | −0.011796 | −0.005041 | −0.02428 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 313 | 0.014553 | 0.013298 | 0.018198 | 0.003854 | 0.006981 | 0.010042 | 0.007731 | −0.014875 | −0.010247 | −0.017032 | −0.011292 | 0.002769 | 0.014024 | 0.009954 |
| 314 | −0.016473 | −0.037718 | −0.004573 | 0.0134 | −0.011747 | −0.020249 | −0.007415 | 0.019832 | 0.010009 | 0.002079 | −0.006192 | 0.020479 | 0.001422 | 0.023959 |
| 315 | −0.000191 | −0.002453 | 0.022957 | −0.017542 | −0.009946 | −0.015842 | 0.012775 | −0.002298 | −0.003404 | −0.031385 | −0.031041 | −0.013147 | 0.012178 | 0.006803 |
| 316 | −0.007619 | −0.014771 | −0.001205 | −0.030216 | 0.044733 | 0.03921 | 0.026614 | −0.006508 | −0.015023 | 0.029178 | 0.018872 | 0.019091 | −0.008268 | −0.012793 |
| 317 | 0.004732 | −0.002185 | −0.000726 | 0.020896 | 0.012375 | 0.004493 | −0.00578 | −0.016545 | −0.022589 | 0.007131 | 0.001262 | 0.018341 | 0.001142 | 0.016275 |
| 318 | −0.007792 | −0.02005 | 0.008387 | 0.018993 | 0.006555 | 0.002918 | 0.009675 | 0.002511 | −0.005295 | 0.008326 | 0.007313 | 0.013996 | 0.024644 | 0.005973 |
| 319 | 0.003022 | −0.002207 | 0.024365 | −0.013866 | 0.001674 | −0.014854 | 0.012919 | −0.009856 | −0.014239 | −0.033151 | −0.035388 | −0.006935 | 0.016569 | 0.011234 |
| 320 | 0.004633 | 0.011031 | 0.010782 | 0.000492 | −0.008885 | −0.009105 | 0.003419 | −0.010306 | −0.008249 | −0.026272 | −0.019363 | −0.011126 | 0.014394 | −0.001464 |
| 321 | −0.01699 | −0.0155 | 0.013822 | 0.000201 | −0.024596 | −0.027225 | 0.00071 | −0.007737 | −0.005761 | −0.007266 | −0.00364 | −0.020554 | −0.011969 | −0.01563 |
| 322 | −0.010038 | −0.022464 | −0.052353 | −0.005013 | 0.018942 | 0.014266 | 0.018902 | 0.009783 | 0.004046 | 0.018485 | 0.015519 | 0.032118 | −0.009607 | 0.004772 |
| 323 | −0.005914 | 0.002888 | 0.013075 | −0.003216 | 0.007253 | 0.01301 | 0.0394 | −0.013347 | −0.01193 | −0.017965 | 0.001639 | 0.021471 | 0.012261 | −0.001055 |
| 324 | 0.010707 | 0.001587 | −0.023427 | 0.004749 | −0.024365 | −0.024511 | −0.046639 | 0.007937 | −0.00239 | 0.011141 | −0.007655 | −0.034814 | −0.028886 | −0.003797 |
| 325 | 0.008414 | 0.004476 | 0.006944 | −0.006738 | 0.002356 | 0.000686 | −0.012533 | −0.000967 | 0.000791 | 0.005635 | −0.00488 | −0.015648 | −0.005501 | 0.007966 |
| 326 | 0.018852 | 0.022683 | 0.000524 | −0.002754 | 0.013918 | 0.015669 | −0.017725 | 0.000867 | 0.009069 | −0.010022 | −0.017728 | −0.002366 | −0.001168 | 0.014264 |
| 327 | 0.003522 | 0.007759 | −0.003033 | −0.016061 | −0.004553 | −0.002032 | −0.005768 | −0.005979 | −0.002088 | −0.007148 | −0.004356 | −0.001507 | 0.003396 | 0.003856 |
| 328 | −0.002128 | −0.004305 | 0.021233 | −0.001199 | −0.012762 | −0.018601 | 0.012548 | −0.013118 | −0.021857 | −0.007826 | −0.007917 | −0.0098291 | −0.020002 | −0.009122 |
| 329 | 0.012914 | 0.021054 | 0.003375 | 0.011057 | 0.001676 | 0.001636 | 0.006943 | −0.011537 | −0.01178 | −0.016388 | −0.008622 | 0.017723 | 0.000246 | 0.01385 |
| 330 | −0.004249 | −0.004977 | −0.008316 | 0.030632 | 0.008138 | −0.002045 | −0.004071 | 0.004406 | 0.001148 | 0.014436 | 0.008463 | 0.025071 | −0.008083 | 0.019194 |
| 331 | −0.001959 | 0.004051 | −0.003495 | −0.030155 | 0.000317 | 0.001952 | 0.00319 | 0.004251 | 0.011145 | −0.022449 | −0.022576 | −0.021235 | 0.0056781 | 0.003383 |
| 332 | −0.010345 | −0.01243 | −0.006859 | −0.013436 | 0.009612 | −0.006505 | −0.015571 | 0.011286 | 0.01109 | 0.013597 | 0.001254 | −0.003972 | −0.000505 | −0.000351 |
| 333 | 0.009238 | 0.008273 | 0.004358 | 0.00195 | 0.018049 | 0.014064 | 0.010627 | −0.009803 | −0.011445 | 0.000091 | −0.005355 | −0.005872 | −0.001354 | 0.004312 |
| 334 | 0.059118 | 0.05635 | 0.034248 | 0.048494 | −0.015301 | −0.024883 | 0.004553 | −0.010498 | −0.020443 | −0.013014 | −0.012982 | 0.007851 | 0.004288 | 0.005331 |
| 335 | 0.008472 | 0.00515 | 0.010044 | −0.022468 | 0.01076 | 0.005182 | 0.009951 | −0.00354 | −0.001227 | −0.017442 | −0.021203 | −0.005919 | 0.014127 | 0.001385 |
| 336 | −0.010298 | −0.015492 | −0.011243 | −0.004475 | 0.006663 | 0.003475 | −0.010782 | −0.000956 | 0.002291 | 0.016063 | 0.008148 | 0.004079 | 0.001941 | −0.009047 |
| 337 | 0.028438 | 0.024414 | 0.019406 | 0.013187 | −0.022024 | −0.014694 | 0.005289 | −0.008455 | −0.008137 | 0.004223 | 0.002809 | 0.003173 | 0.002037 | −0.031892 |
| 338 | 0.007273 | 0.012192 | 0.003323 | 0.0107 | 0.011761 | 0.006823 | −0.017769 | 0.013298 | 0.007388 | 0.027125 | 0.022224 | 0.031424 | 0.004337 | 0.028341 |
| 339 | −0.00436 | −0.005854 | −0.012483 | 0.014958 | 0.002091 | 0.005703 | 0.012608 | −0.018865 | −0.014386 | −0.019173 | −0.009537 | −0.011079 | 0.001199 | −0.011918 |
| 340 | 0.012495 | 0.023256 | 0.049594 | −0.025482 | −0.013741 | 0.002892 | 0.012929 | 0.007772 | 0.015738 | −0.009497 | 0.002141 | 0.038382 | 0.038836 | 0.014954 |

| | KF | KG | KH | KI | KJ | KK | KL | KM | KN | KO | KP | KQ | KR | KS |
|---|---|---|---|---|---|---|---|---|---|---|---|---|---|---|
| 1 | 0.042332 | 0.031247 | −0.026205 | −0.016239 | 0.048115 | 0.069299 | 0.031136 | −0.021677 | −0.010284 | −0.037828 | 0.002509 | 0.006442 | −0.040439 | −0.051796 |
| 2 | 0.073049 | 0.061952 | 0.057407 | 0.00201 | 0.002758 | −0.020385 | 0.012452 | 0.021179 | −0.015744 | 0.067627 | −0.03729 | −0.072283 | −0.110039 | −0.096903 |
| 3 | 0.019586 | 0.021022 | −0.019468 | −0.039761 | −0.062935 | −0.094219 | −0.048838 | −0.020131 | −0.03941 | −0.008678 | −0.054916 | −0.070565 | 0.011004 | −0.025434 |
| 4 | −0.023262 | −0.043812 | −0.082495 | −0.021366 | −0.069379 | −0.075869 | −0.047241 | 0.048052 | 0.014295 | −0.026029 | −0.029818 | 0.009394 | 0.097773 | 0.122367 |
| 5 | −0.017493 | −0.003771 | −0.066158 | −0.043469 | −0.030972 | 0.024039 | −0.022334 | 0.069617 | 0.03584 | 0.067525 | −0.009684 | −0.014425 | 0.064104 | 0.06808 |
| 6 | 0.029237 | 0.000029 | −0.021573 | −0.007331 | −0.016831 | 0.043449 | 0.008076 | 0.001182 | 0.000195 | −0.06669 | −0.004668 | −0.015926 | 0.011458 | −0.007499 |
| 7 | −0.004405 | 0.016382 | 0.045288 | 0.047877 | −0.012677 | −0.009326 | −0.003714 | 0.066099 | 0.059956 | −0.002648 | 0.038963 | −0.012575 | 0.092939 | 0.042117 |
| 8 | −0.008366 | −0.018659 | 0.051189 | 0.04699 | 0.053122 | 0.006194 | 0.06204 | −0.044479 | 0.019094 | 0.004532 | 0.049465 | 0.079821 | −0.034938 | −0.045917 |
| 9 | −0.041287 | −0.044771 | −0.113238 | −0.045988 | −0.04538 | 0.02658 | −0.018816 | −0.061794 | −0.046009 | −0.076452 | −0.066562 | 0.028649 | 0.002772 | −0.006279 |
| 10 | 0.044297 | 0.062415 | 0.028175 | −0.054278 | 0.031647 | −0.068831 | 0.056234 | −0.02661 | 0.014297 | 0.046592 | 0.032562 | −0.016065 | 0.007806 | 0.0031 |
| 11 | −0.019363 | −0.01606 | −0.007632 | 0.040513 | 0.021428 | 0.082569 | 0.02226 | 0.112792 | 0.055435 | −0.017946 | 0.063539 | 0.063884 | 0.045733 | 0.079204 |
| 12 | −0.019894 | −0.007169 | −0.016097 | −0.01606 | 0.023532 | 0.041689 | 0.002089 | −0.038117 | −0.029182 | 0.013003 | −0.033503 | 0.003136 | −0.046088 | −0.010919 |
| 13 | 0.043606 | 0.038736 | 0.055856 | 0.016494 | −0.008469 | −0.041411 | 0.035377 | −0.046146 | 0.067739 | −0.041817 | 0.021139 | 0.006414 | 0.023716 | 0.058759 |
| 14 | 0.019349 | 0.019852 | −0.025451 | −0.027752 | 0.014136 | 0.048828 | 0.029888 | 0.042886 | 0.012484 | −0.005276 | 0.0455 | 0.034593 | −0.057206 | −0.014822 |
| 15 | −0.180841 | −0.167658 | −0.038413 | −0.061591 | −0.022113 | −0.050402 | −0.010045 | −0.089219 | −0.034129 | −0.042844 | −0.017884 | −0.045635 | −0.038712 | −0.05307 |
| 16 | −0.051606 | −0.050022 | −0.02205 | −0.036648 | −0.037588 | −0.058896 | −0.033406 | −0.025371 | −0.051583 | 0.004147 | −0.064274 | −0.045493 | −0.036085 | −0.054958 |
| 17 | 0.056858 | 0.047838 | −0.030693 | −0.024845 | 0.008256 | 0.004763 | 0.007561 | −0.016936 | 0.043598 | −0.071269 | 0.045553 | 0.051048 | 0.030064 | 0.042411 |
| 18 | −0.044656 | −0.040457 | −0.016319 | 0.036369 | 0.034884 | 0.043258 | 0.061041 | −0.028921 | 0.040524 | 0.071884 | −0.018696 | 0.014267 | 0.039938 | 0.04361 |
| 19 | −0.037592 | −0.028047 | 0.029164 | 0.01325 | −0.014701 | 0.066978 | −0.014527 | −0.182245 | −0.043703 | −0.118537 | −0.04174 | −0.046304 | −0.017742 | −0.004588 |

APPENDIX B3-continued

PCA Transformation
Matrix (340 × 340 Early/Late)

| | | | | | | | | | | | | | |
|---|---|---|---|---|---|---|---|---|---|---|---|---|---|
| 20 | −0.02867 | −0.044263 | −0.015795 | 0.006615 | 0.004203 | −0.017067 | −0.038732 | −0.085724 | −0.040148 | −0.088643 | −0.008019 | −0.00418 | −0.06171 | −0.073519 |
| 21 | 0.032167 | 0.039885 | 0.002301 | −0.000514 | 0.037768 | 0.017136 | −0.006682 | −0.025528 | −0.039356 | 0.055647 | 0.006286 | 0.000552 | −0.080659 | −0.043234 |
| 22 | −0.036845 | −0.04559 | −0.012749 | 0.001378 | 0.028967 | −0.000996 | 0.035931 | −0.082917 | 0.072444 | 0.008065 | 0.012888 | 0.025819 | 0.022198 | 0.01675 |
| 23 | 0.00655 | 0.007409 | −0.017482 | 0.026853 | −0.042054 | −0.053442 | −0.012969 | −0.071133 | 0.000404 | −0.036507 | 0.01051j | 0.041346 | −0.022047 | −0.011302 |
| 24 | −0.095449 | −0.099705 | −0.010103 | 0.000824 | 0.003627 | 0.020877 | 0.029489 | 0.011316 | 0.109458 | −0.011196 | 0.034628 | 0.030902 | 0.157475 | 0.11213 |
| 25 | 0.046897 | 0.056099 | −0.006058 | −0.002142 | −0.039646 | −0.05463 | −0.024465 | 0.002963 | 0.015668 | 0.019146 | −0.020076 | −0.005004 | 0.029334 | 0.069314 |
| 26 | 0.010036 | −0.008623 | −0.069429 | −0.001196 | 0.008187 | 0.074926 | −0.016446 | 0.102217 | −0.052476 | 0.024958 | −0.036713 | −0.022237 | −0.047882 | −0.011158 |
| 27 | −0.004848 | 0.018859 | 0.009013 | −0.012671 | −0.129749 | −0.127923 | −0.166196 | 0.056096 | −0.049863 | 0.073131 | −0.017339 | 0.009265 | 0.035417 | 0.034698 |
| 28 | −0.012432 | −0.008617 | 0.048395 | 0.034157 | 0.060391 | 0.063558 | 0.09268 | 0.025445 | 0.074076 | 0.043441 | −0.017926 | −0.049006 | 0.077076 | 0.099757 |
| 29 | 0.005633 | −0.000254 | −0.013664 | 0.004874 | 0.014003 | 0.04081 | 0.009714 | 0.011983 | −0.00574 | −0.007565 | 0.012059 | 0.00519 | 0.007934 | 0.011135 |
| 30 | 0.0352 | 0.019636 | −0.030872 | 0.0109 | 0.011682 | 0.017314 | 0.007814 | −0.009058 | 0.023627 | −0.009312 | 0.033158 | 0.013685 | 0.013845 | 0.03665 |
| 31 | −0.027965 | −0.037482 | 0.062951 | 0.014475 | 0.016719 | −0.047206 | 0.030981 | 0.003782 | 0.01206 | −0.051223 | 0.037338 | −0.008447 | −0.028113 | −0.019979 |
| 32 | 0.010115 | 0.011975 | −0.025477 | 0.00009 | 0.009653 | 0.051445 | 0.021298 | 0.049826 | −0.002592 | −0.015044 | 0.008273 | 0.009597 | −0.008519 | 0.002592 |
| 33 | 0.002728 | 0.025444 | 0.050907 | −0.0084 | −0.004385 | −0.005093 | 0.027807 | −0.06791 | 0.004259 | 0.036985 | 0.047217 | 0.039408 | 0.000787 | −0.004649 |
| 34 | 0.036079 | 0.052731 | −0.133356 | −0.060911 | −0.066428 | −0.023862 | −0.041335 | 0.041704 | −0.062788 | 0.08299 | −0.036607 | −0.040901 | 0.01332 | −0.019731 |
| 35 | −0.003848 | 0.003917 | −0.036497 | −0.03092 | 0.009258 | 0.010836 | −0.0075 | −0.011172 | −0.045014 | −0.048943 | −0.031017 | −0.027394 | −0.029161 | −0.099721 |
| 36 | 0.05159 | 0.042231 | −0.141416 | −0.058798 | −0.052496 | 0.020714 | −0.070185 | −0.029273 | −0.018651 | 0.019819 | −0.097161 | 0.001309 | 0.017233 | 0.038477 |
| 37 | −0.008603 | −0.011558 | −0.024399 | −0.01623 | 0.028406 | −0.018717 | 0.030222 | −0.034661 | −0.009179 | −0.026997 | 0.013539 | 0.006665 | 0.025954 | −0.010906 |
| 38 | 0.003011 | −0.004519 | −0.011955 | −0.024572 | −0.064458 | −0.031765 | −0.016853 | 0.050941 | 0.00645 | −0.025186 | −0.027605 | −0.060042 | 0.020916 | −0.026983 |
| 39 | −0.006854 | −0.010332 | −0.02757 | 6.011529 | 0.034486 | 0.036504 | −0.011466 | 0.02189 | −0.000552 | 0.024335 | 0.020879 | 0.016171 | −0.023296 | 0.048609 |
| 40 | 0.008227 | 0.00706 | −0.031061 | −0.01537 | −0.007652 | 0.021408 | −0.009834 | −0.01749 | −0.003899 | −0.029604 | −0.00421 | 0.010602 | 0.003874 | 0.008609 |
| 41 | −0.022719 | −0.019457 | 0.181226 | 0.008692 | 0.087117 | −0.014237 | 0.04236 | 0.035411 | 0.063182 | 0.013079 | 0.057853 | 0.012539 | −0.014389 | −0.009627 |
| 42 | −0.025687 | −0.01649 | −0.036012 | −0.018109 | −0.011977 | −0.026376 | 0.006677 | −0.031918 | −0.018282 | 0.023901 | 0.004409 | −0.018012 | −0.027293 | −0.014293 |
| 43 | 0.034061 | 0.031227 | −0.050583 | −0.054389 | −0.0451 | 0.017983 | −0.027364 | −0.011031 | −0.047113 | 0.025425 | −0.060124 | −0.024156 | −0.033107 | 0.002151 |
| 44 | 0.026676 | 0.035155 | 0.038707 | 0.004736 | 0.031037 | −0.037253 | 0.015635 | −0.050512 | −0.04122 | −0.042757 | −0.009797 | −0.006504 | −0.069235 | −0.06595 |
| 45 | 0.03161 | 0.028846 | −0.067286 | 0.029993 | −0.046751 | 0.041675 | −0.045288 | 0.014836 | −0.081737 | 0.050436 | −0.098618 | −0.036536 | −0.025408 | −0.044823 |
| 46 | 0.024682 | 0.012686 | −0.071736 | −0.07414 | −0.051115 | −0.049897 | −0.066354 | 0.026632 | −0.039454 | 0.107701 | −0.020622 | −0.003566 | 0.016764 | 0.014665 |
| 47 | 0.044728 | 0.047862 | −0.089154 | 0.007232 | 0.030028 | 0.083116 | 0.003718 | 0.060313 | −0.035241 | 0.088791 | 0.003138 | 0.080565 | 0.057397 | 0.037442 |
| 48 | 0.021614 | 0.01573 | −0.007472 | −0.009898 | −0.019568 | 0.035726 | −0.024718 | 0.063077 | −0.039934 | 0.204057 | −0.029572 | 0.016233 | 0.011723 | 0.009238 |
| 49 | −0.065124 | −0.101595 | −0.013455 | 0.022685 | 0.011115 | 0.015416 | 0.003412 | 0.010965 | −0.019502 | 0.10831 | 0.032099 | 0.057204 | −0.009733 | 0.009988 |
| 50 | 0.002594 | 0.030728 | 0.001381 | 0.001139 | 0.040759 | 0.030757 | 0.072212 | 0.021962 | 0.078235 | 0.059831 | 0.028637 | 0.036894 | 0.03054 | 0.03478 |
| 51 | −0.008886 | −0.025055 | 0.000999 | −0.019551 | −0.008441 | −0.045735 | −0.015936 | −0.08872 | −0.020884 | −0.018496 | −0.027791 | −0.052103 | −0.024213 | −0.048046 |
| 52 | −0.06325 | −0.040053 | −0.041455 | −0.024568 | 0.038912 | −0.025519 | 0.043925 | 0.005001 | 0.015568 | 0.173442 | 0.008692 | 0.005935 | −0.002047 | −0.031423 |
| 53 | −0.02623 | −0.030945 | 0.041524 | −0.037533 | −0.019281 | −0.040706 | −0.004936 | −0.015981 | 0.048055 | −0.009524 | 0.001015 | −0.018158 | 0.026972 | 0.026887 |
| 54 | −0.038559 | −0.05554 | −0.003551 | 0.007981 | 0.028232 | 0.053927 | 0.041456 | 0.045629 | 0.051528 | −0.011688 | 0.026543 | −0.017746 | 0.034016 | 0.053272 |
| 55 | 0.083427 | 0.069716 | 0.029179 | 0.005675 | 0.047963 | 0.069646 | 0.051147 | 0.053505 | 0.032828 | 0.039311 | 0.033247 | 0.012861 | −0.003603 | 0.031131 |
| 56 | −0.082285 | −0.090123 | −0.043354 | 0.014972 | −0.043641 | −0.059197 | −0.01946 | −0.003429 | −0.006527 | −0.028155 | −0.029252 | −0.036607 | 0.002344 | −0.060372 |
| 57 | −0.046135 | −0.041277 | −0.030751 | −0.047846 | −0.022396 | −0.069037 | −0.025831 | 0.003742 | −0.033595 | −0.069235 | −0.019245 | −0.021716 | −0.080815 | −0.058161 |
| 58 | −0.007384 | −0.000021 | −0.026856 | 0.025373 | 0.021953 | 0.093779 | 0.01551 | 0.060008 | −0.04335 | −0.070664 | 0.020799 | 0.026751 | −0.004648 | −0.040949 |
| 59 | −0.032322 | 0.004318 | 0.047259 | 0.000948 | 0.038564 | 0.07959 | 0.022195 | −0.008956 | 0.01407 | −0.016786 | −0.015941 | 0.03218 | 0.053985 | 0.016154 |
| 60 | −0.003832 | 0.00305 | −0.011572 | −0.000096 | −0.022922 | −0.022902 | −0.026681 | 0.016251 | −0.026275 | 0.017042 | −0.017736 | −0.021135 | −0.006913 | −0.015497 |
| 61 | −0.010756 | −0.008775 | 0.005451 | 0.001699 | −0.000244 | −0.008274 | 0.015986 | −0.015458 | 0.007633 | −0.025591 | 0.012069 | −0.000031 | 0.015883 | 0.00143 |
| 62 | −0.006486 | −0.007324 | 0.027514 | 0.016038 | 0.004654 | −0.027105 | 0.002406 | −0.023709 | −0.0109 | 0.008676 | −0.004892 | −0.011789 | −0.006746 | −0.020707 |
| 63 | −0.027248 | −0.032466 | 0.024961 | 0.01304 | 0.014112 | −0.013755 | 0.015439 | −0.029554 | 0.02151 | −0.032093 | 0.019757 | 0.004745 | 0.012761 | 0.009621 |
| 64 | 0.002321 | 0.008071 | 0.002155 | −0.005747 | 0.013066 | −0.022737 | −0.00564 | −0.038517 | −0.011756 | −0.003401 | 0.005578 | 0.011912 | −0.012204 | −0.015483 |
| 65 | 0.003446 | −0.001787 | −0.0239 | 0.005367 | −0.007847 | −0.00229 | −0.00976 | 0.010674 | −0.015315 | 0.03297 | −0.010981 | 0.000203 | −0.01323 | −0.006077 |
| 66 | −0.003169 | −0.002564 | −0.014442 | −0.003791 | 0.001931 | −0.009015 | 0.006336 | −0.017272 | 0.011723 | −0.076241 | 0.013851 | 0.00689 | 0.012486 | −0.002756 |
| 67 | 0.014094 | 0.006032 | −0.007834 | 0.001621 | 0.023677 | 0.031716 | 0.039046 | −0.026879 | 0.034216 | −0.070424 | 0.014602 | 0.004373 | 0.018208 | 0.0164 |
| 68 | −0.018225 | −0.008553 | −0.011069 | −0.00118 | 0.021616 | 0.002273 | 0.028305 | −0.018364 | 0.008313 | −0.022207 | −0.000639 | 0.01452 | 0.005134 | −0.004314 |
| 69 | −0.005539 | −0.001875 | 0.013161 | 0.015544 | 0.014379 | −0.004401 | 0.020683 | −0.010419 | 0.004105 | 0.001447 | −0.003991 | 0.002857 | 0.002225 | −0.024894 |

APPENDIX B3-continued

PCA Transformation
Matrix (340 × 340 Early/Late)

| | | | | | | | | | | | | | |
|---|---|---|---|---|---|---|---|---|---|---|---|---|---|
| 70 | −0.0116 | −0.01344 | 0.005197 | 0.016463 | −0.006396 | −0.015639 | −0.012921 | −0.006161 | −0.027804 | −0.02457 | −0.013643 | −0.012269 | −0.021579 | −0.044453 |
| 71 | −0.008948 | −0.003229 | 0.010196 | −0.002726 | −0.007069 | −0.031713 | −0.011182 | −0.010871 | −0.012811 | 0.026407 | −0.024441 | −0.013991 | −0.009872 | −0.028265 |
| 70 | −0.027261 | −0.028326 | 0.004406 | 0.001727 | −0.021376 | −0.006712 | −0.033615 | 0.000257 | −0.012945 | 0.00262 | −0.021759 | 0.000813 | 0.000673 | 0.002135 |
| 73 | −0.026843 | −0.025198 | −0.030773 | −0.024636 | −0.013064 | −0.008136 | −0.02327 | 0.017515 | −0.029508 | 0.001216 | −0.008553 | −0.000683 | −0.022787 | −0.047716 |
| 74 | −0.042083 | −0.03513 | 0.026188 | 0.011726 | −0.011596 | −0.003587 | −0.009185 | 0.009226 | 0.005893 | 0.00374 | 0.012476 | 0.008252 | 0.026394 | 0.032624 |
| 75 | −0.004289 | −0.00389 | 0.003385 | 0.004705 | 0.003683 | −0.015983 | −0.003813 | 0.005411 | −0.011508 | 0.036344 | −0.005436 | −0.000428 | 0.002576 | −0.011461 |
| 76 | −0.004602 | −0.012928 | −0.007956 | 0.006539 | −0.017979 | −0.02086 | −0.012632 | 0.005421 | −0.004631 | 0.031931 | −0.018541 | −0.014459 | 0.011999 | 0.011788 |
| 77 | −0.009701 | −0.00828 | 0.010745 | 0.009997 | 0.001625 | −0.018756 | −0.003922 | −0.001894 | −0.013862 | 0.020943 | −0.010488 | −0.006799 | −0.005319 | −0.02168 |
| 78 | −0.010996 | −0.0074 | 0.020382 | 0.004819 | 0.007813 | −0.014445 | −0.001258 | 0.000603 | −0.014894 | 0.03307 | −0.010095 | −0.007567 | −0.007267 | −0.026833 |
| 79 | 0.000995 | 0.006746 | −0.025937 | −0.010068 | 0.003536 | −0.017131 | −0.010912 | 0.013271 | −0.018995 | 0.041667 | −0.00492 | 0.009026 | 0.007442 | −0.012616 |
| 80 | 0.016338 | 0.017191 | −0.000996 | −0.001385 | 0.004751 | 0.009332 | 0.008432 | −0.021683 | 0.002244 | −0.050123 | 0.006201 | −0.011811 | −0.017578 | −0.031082 |
| 81 | 0.005738 | 0.000065 | −0.017739 | 0.034901 | −0.013116 | 0.020414 | −0.009413 | −0.012315 | −0.032846 | −0.02055 | −0.007679 | 0.017216 | −0.02281 | 0.008518 |
| 82 | 0.009781 | 0.010323 | −0.001493 | 0.000006 | 0.012527 | 0.021444 | 0.004344 | 0.016879 | 0.002371 | −0.000378 | 0.00184 | −0.002052 | −0.008058 | −0.009384 |
| 83 | 0.016801 | 0.017364 | 0.018643 | −0.002177 | 0.0239 | 0.01286 | 0.016402 | 0.012299 | 0.005378 | 0.013754 | 0.005492 | −0.007035 | −0.009159 | −0.007641 |
| 84 | 0.015433 | 0.013605 | 0.02377 | 0.011104 | 0.016664 | 0.010939 | 0.00957 | 0.00229 | 0.00623 | 0.008869 | 0.006 | −0.002185 | −0.012323 | −0.012961 |
| 85 | 0.034508 | 0.03016 | −0.02741 | −0.01401 | −0.013729 | −0.012454 | 0.003671 | −0.004468 | 0.021538 | −0.017281 | 0.018771 | 0.036868 | 0.03488 | 0.051444 |
| 86 | 0.001618 | 0.006998 | 0.001453 | −0.007111 | −0.028301 | −0.041715 | −0.019352 | −0.000527 | −0.000465 | 0.000798 | −0.016151 | −0.012779 | 0.009938 | 0.000503 |
| 87 | 0.010668 | 0.004365 | 0.003254 | −0.000507 | 0.002357 | −0.017987 | 0.004466 | −0.015114 | −0.001724 | −0.00554 | 0.00362 | −0.003128 | −0.013034 | −0.019736 |
| 88 | 0.006616 | 0.007818 | 0.015737 | 0.004265 | 0.030829 | 0.029123 | 0.025195 | 0.005423 | 0.008169 | −0.004843 | 0.011871 | −0.00473 | −0.009207 | −0.017599 |
| 89 | 0.00869 | 0.013633 | 0.029133 | 0.000281 | 0.031679 | 0.017687 | 0.028003 | 0.003255 | 0.014034 | 0.007422 | 0.005917 | −0.003457 | −0.005079 | −0.013782 |
| 90 | 0.012863 | 0.015263 | 0.022069 | 0.004509 | 0.020809 | 0.006821 | 0.020942 | 0.012148 | 0.01806 | 0.016453 | 0.006631 | −0.000528 | 0.010542 | −0.000451 |
| 91 | 0.015123 | 0.015499 | 0.02075 | 0.011593 | 0.014901 | 0.016951 | 0.002189 | 0.012807 | 0.008978 | 0.006217 | 0.005581 | 0.009925 | −0.010905 | −0.006175 |
| 92 | −0.011162 | −0.02283 | −0.012915 | 0.014189 | −0.006644 | 0.033386 | −0.019531 | 0.012057 | −0.025796 | −0.003002 | −0.011231 | 0.000049 | −0.043197 | −0.015165 |
| 93 | −0.007263 | −0.008472 | 0.014734 | 0.004886 | 0.011393 | −0.010228 | 0.008219 | 0.001947 | 0.009149 | −0.005865 | 0.003162 | −0.003902 | −0.000972 | −0.014405 |
| 94 | 0.005289 | 0.014015 | 0.034009 | 0.005237 | 0.014079 | 0.004704 | 0.006799 | 0.020478 | 0.012631 | −0.039923 | 0.007647 | −0.012478 | −0.00579 | −0.017378 |
| 95 | 0.019577 | 0.024343 | −0.025896 | −0.004667 | 0.019836 | 0.02789 | 0.022923 | 0.024609 | 0.004496 | −0.024695 | 0.009732 | 0.009379 | −0.003597 | −0.016079 |
| 96 | −0.011509 | −0.009228 | −0.042512 | −0.005142 | −0.022312 | 0.023549 | −0.029426 | 0.0202 | −0.018598 | −0.021102 | −0.012986 | 0.004656 | 0.028993 | 0.007029 |
| 97 | 0.008119 | 0.011791 | −0.010168 | −0.013452 | −0.01174 | −0.018377 | −0.016809 | 0.014242 | −0.017118 | 0.004119 | 0.006229 | 0.000164 | −0.020152 | −0.014878 |
| 98 | 0.010458 | 0.010206 | 0.001552 | 0.005996 | −0.001159 | 0.001843 | −0.00274 | 0.005469 | 0.014481 | −0.025917 | 0.004669 | 0.011188 | 0.015026 | 0.02335 |
| 99 | 0.004992 | 0.005871 | −0.024047 | −0.005582 | −0.009668 | 0.00926 | −0.00757 | 0.004176 | −0.008576 | 0.000086 | −0.008121 | −0.005824 | −0.003671 | 0.001593 |
| 100 | −0.031413 | −0.0292 | 0.005918 | −0.004241 | 0.007872 | 0.003992 | 0.01035 | −0.016896 | 0.00963 | −0.013193 | 0.001907 | −0.001927 | 0.012613 | 0.012752 |
| 101 | 0.006173 | 0.005563 | 0.019373 | 0.009546 | 0.000078 | −0.008223 | 0.000137 | −0.009796 | 0.008088 | −0.061407 | 0.010553 | 0.003675 | −0.002575 | 0.003363 |
| 102 | −0.006183 | −0.012624 | −0.026396 | −0.004349 | −0.007436 | −0.007178 | −0.013167 | −0.013542 | −0.002906 | −0.017074 | 0.007438 | 0.013913 | −0.003912 | −0.005812 |
| 103 | 0.013182 | 0.013361 | −0.021506 | −0.019636 | 0.013206 | −0.006386 | −0.004722 | −0.017738 | −0.03452 | −0.029684 | 0.002954 | −0.003353 | −0.039852 | −0.040074 |
| 104 | −0.006801 | −0.012495 | −0.020483 | −0.004981 | −0.004524 | 0.018386 | 0.00002 | −0.021055 | −0.02736 | 0.003128 | −0.014055 | −0.012551 | −0.024096 | −0.038046 |
| 105 | −0.022292 | −0.02946 | −0.004157 | −0.001323 | 0.028306 | 0.005638 | 0.031517 | −0.034291 | −0.013805 | 0.039954 | −0.016933 | 0.004541 | −0.010123 | −0.019253 |
| 106 | 0.015868 | 0.02108 | 0.015605 | −0.011765 | −0.011318 | −0.048665 | −0.044021 | −0.023185 | −0.020082 | 0.015026 | −0.002599 | −0.02077 | −0.036958 | −0.026263 |
| 107 | 0.002437 | 0.002321 | 0.005617 | 0.004851 | −0.015353 | 0.001432 | −0.021035 | −0.004955 | −0.003857 | −0.011412 | −0.016148 | −0.026953 | −0.009682 | −0.00278 |
| 108 | 0.003701 | 0.008725 | −0.011251 | 0.009717 | 0.015701 | 0.034075 | 0.015784 | −0.03302 | 0.005407 | 0.008936 | 0.000686 | 0.003746 | 0.005866 | 0.00229 |
| 109 | 0.009044 | −0.004575 | 0.014599 | −0.004578 | −0.00189 | 0.00871 | −0.005631 | −0.019149 | −0.009708 | 0.001878 | 0.000222 | −0.005663 | −0.017427 | −0.010422 |
| 110 | 0.035224 | 0.037073 | −0.003577 | −0.004341 | 0.005469 | 0.017612 | −0.014277 | −0.007897 | −0.012656 | 0.017536 | 0.000779 | −0.007074 | −0.022812 | −0.013647 |
| 111 | 0.008217 | 0.010336 | −0.028265 | 0.002088 | 0.003153 | 0.023274 | −0.020541 | −0.009737 | −0.005704 | 0.02453 | 0.006661 | 0.006979 | 0.010672 | 0.017578 |
| 112 | 0.005275 | 0.00677 | 0.010255 | 0.004024 | 0.026004 | 0.01772 | 0.015664 | −0.021263 | −0.001833 | 0.005099 | −0.021755 | −0.017728 | 0.015185 | −0.01244 |
| 113 | 0.020665 | 0.024329 | −0.012979 | −0.002285 | −0.013561 | −0.013004 | −0.029245 | 0.008148 | −0.004618 | −0.005419 | −0.000872 | 0.005499 | −0.01698 | −0.011196 |
| 114 | 0.021468 | 0.022605 | 0.016587 | 0.009579 | 0.005529 | 0.049644 | 0.029081 | −0.007952 | −0.014915 | −0.012067 | −0.011037 | 0.010432 | −0.016956 | −0.009253 |
| 115 | −0.008956 | −0.015001 | −0.003624 | 0.018743 | −0.005762 | −0.010426 | −0.009797 | −0.025244 | 0.000612 | −0.02146 | −0.00553 | −0.020511 | 0.007874 | 0.011669 |
| 116 | −0.019125 | −0.021809 | 0.000067 | −0.007565 | 0.029088 | 0.023654 | 0.001441 | −0.012146 | −0.031188 | 0.024464 | 0.003068 | 0.022037 | −0.006675 | −0.012173 |
| 117 | 0.005756 | −0.003813 | −0.025908 | 0.01208 | −0.008791 | 0.010135 | −0.015093 | 0.044657 | −0.00054 | 0.048202 | 0.000203 | 0.017575 | 0.028873 | 0.02325 |
| 118 | 0.00306 | −0.01024 | −0.004858 | 0.026749 | 0.007396 | 0.019599 | 0.022405 | 0.020135 | 0.019359 | −0.044236 | 0.005356 | 0.007838 | 0.002953 | −0.006184 |
| 119 | −0.016225 | −0.012489 | 0.021375 | 0.012304 | −0.007653 | −0.010193 | −0.006259 | 0.01232 | 0.020551 | 0.000675 | 0.007259 | −0.008983 | 0.021665 | 0.000107 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 120 | −0.013421 | −0.010469 | −0.021676 | −0.01014 | 0.001733 | −0.00512 | −0.00693 | 0.0199 | 0.009162 | 0.029367 | 0.019223 | 0.036708 | 0.011499 | 0.014101 |
| 121 | 0.000879 | 0.002974 | 0.011631 | −0.00359 | 0.02731 | −0.011116 | 0.020613 | 0.013506 | 0.036993 | 0.039834 | 0.020316 | 0.022063 | 0.037927 | 0.035135 |
| 122 | 0.03513 | 0.030703 | 0.023038 | 0.019183 | 0.016814 | 0.000605 | 0.008886 | 0.016171 | −0.006369 | −0.007989 | 0.017078 | 0.003961 | −0.027795 | −0.01523 |
| 123 | 0.012085 | 0.012521 | 0.020689 | 0.014151 | 0.023916 | 0.00372 | 0.02342 | −0.008911 | 0.010588 | −0.001898 | 0.007198 | −0.003305 | −0.010259 | −0.0112 |
| 124 | −0.004999 | 0.001157 | 0.035245 | 0.008442 | −0.002865 | −0.014789 | −0.003135 | −0.001436 | 0.004935 | 0.00054 | 0.003596 | −0.022603 | 0.004659 | −0.011992 |
| 125 | 0.00068 | −0.000294 | −0.032911 | −0.015887 | −0.016095 | −0.029791 | −0.007395 | −0.025318 | 0.003826 | 0.008287 | −0.026049 | −0.005715 | −0.003248 | −0.002855 |
| 126 | 0.012521 | 0.000745 | −0.000751 | 0.017867 | −0.004251 | 0.002031 | 0.008093 | 0.023506 | 0.011369 | 0.012683 | 0.004943 | −0.003998 | −0.006505 | −0.004925 |
| 127 | 0.007812 | 0.000597 | 0.008852 | 0.010003 | −0.007194 | −0.011211 | −0.003984 | 0.011508 | −0.000254 | 0.005766 | −0.00926 | −0.02436 | −0.018481 | −0.01788 |
| 128 | −0.011025 | −0.010407 | −0.009887 | −0.002238 | −0.019478 | 0.004564 | −0.010822 | 0.009924 | −0.012959 | 0.019323 | −0.019964 | −0.009321 | 0.001116 | −0.005923 |
| 129 | 0.011318 | 0.023096 | 0.014756 | 0.009215 | 0.044978 | −0.008573 | 0.050277 | −0.012171 | 0.034378 | −0.000901 | 0.060075 | 0.021397 | 0.043037 | 0.024805 |
| 130 | 0.015635 | 0.015394 | −0.01164 | −0.008527 | −0.002092 | −0.015973 | −0.003617 | 0.016551 | 0.000392 | 0.015744 | 0.004942 | −0.010529 | 0.023373 | 0.015017 |
| 131 | 0.029334 | 0.032793 | −0.006238 | −0.004592 | 0.019599 | −0.01113 | −0.005176 | 0.015613 | −0.004128 | 0.035131 | 0.020311 | 0.024175 | 0.013589 | 0.005568 |
| 132 | −0.00201 | 0.004787 | −0.000439 | −0.005297 | −0.001643 | 0.013288 | 0.000871 | −0.025195 | 0.003362 | 0.005086 | −0.010198 | −0.000588 | 0.013668 | −0.005949 |
| 133 | 0.031606 | 0.041612 | −0.016053 | −0.006093 | 0.015276 | 0.023787 | −0.001524 | 0.029033 | 0.002287 | 0.045134 | −0.000696 | 0.009112 | 0.004397 | 0.010027 |
| 134 | 0.002003 | −0.019324 | 0.000597 | 0.001264 | −0.022074 | −0.015992 | −0.012874 | 0.037073 | 0.006305 | −0.088838 | 0.011231 | −0.005737 | 0.027477 | 0.009803 |
| 135 | −0.011727 | −0.00622 | 0.008352 | −0.017432 | 0.002408 | 0.003278 | −0.000694 | 0.012339 | −0.001115 | 0.019892 | −0.009724 | −0.01063 | 0.000581 | −0.01332 |
| 136 | 0.014404 | 0.013447 | −0.016776 | −0.006086 | −0.011117 | 0.012435 | −0.02711 | 0.019227 | −0.005705 | 0.024259 | 0.005017 | 0.013389 | 0.008986 | 0.022356 |
| 137 | −0.007691 | −0.004989 | 0.034705 | −0.007334 | −0.010133 | −0.054523 | −0.002758 | −0.00505 | 0.023676 | −0.033136 | 0.006981 | −0.009937 | 0.008574 | 0.006911 |
| 138 | −0.006364 | −0.008753 | −0.002871 | 0.004437 | −0.026602 | −0.017843 | −0.030171 | 0.004538 | −0.004075 | 0.019965 | −0.004187 | 0.0072 | 0.013865 | 0.026953 |
| 139 | −0.008748 | −0.007345 | −0.013043 | −0.015973 | −0.032183 | −0.004771 | −0.008121 | 0.011795 | 0.021554 | −0.043787 | 0.018397 | −0.015908 | 0.008724 | −0.001957 |
| 140 | 0.02264 | 0.0255 | 0.014917 | 0.006313 | −0.018355 | −0.011681 | −0.001789 | 0.022121 | 0.027843 | 0.039535 | 0.002564 | 0.021569 | 0.048231 | 0.032528 |
| 141 | −0.008905 | −0.005207 | −0.000005 | −0.012201 | 0.001067 | 0.01994 | 0.018351 | −0.011431 | −0.011854 | −0.011784 | −0.024836 | −0.020093 | −0.012213 | −0.024695 |
| 142 | 0.024346 | 0.01842 | −0.000804 | −0.006366 | −0.001317 | −0.010197 | 0.011072 | 0.031795 | 0.010417 | 0.04864 | 0.015274 | 0.005954 | 0.027629 | 0.030289 |
| 143 | 0.018089 | 0.014979 | 0.006196 | 0.008297 | 0.010826 | 0.015172 | 0.004816 | 0.010933 | −0.015124 | 0.018118 | −0.000715 | 0.002281 | −0.016348 | −0.006059 |
| 144 | −0.002258 | 0.004291 | 0.008384 | 0.007447 | 0.0083 | 0.008969 | 0.005867 | 0.029105 | 0.006722 | 0.003808 | 0.014759 | −0.00224 | 0.021109 | 0.003504 |
| 145 | 0.024307 | 0.019235 | −0.000467 | 0.001755 | −0.004295 | 0.004954 | −0.01331 | 0.041105 | −0.017302 | −0.026834 | −0.000156 | −0.008047 | −0.034447 | −0.035553 |
| 146 | 0.000545 | 0.002875 | −0.020093 | −0.015392 | −0.009346 | −0.004418 | 0.000809 | −0.000187 | 0.013197 | 0.013178 | 0.004999 | 0.01255 | 0.02303 | 0.008998 |
| 147 | 0.029947 | 0.013308 | −0.042535 | −0.0136 | −0.003242 | −0.003532 | 0.010246 | 0.023273 | 0.037598 | 0.059941 | 0.019043 | 0.021887 | 0.033261 | 0.042774 |
| 148 | 0.027738 | 0.026462 | −0.034254 | −0.024175 | −0.03767 | −0.029618 | −0.030868 | 0.057732 | −0.015904 | 0.017663 | 0.013945 | −0.002727 | 0.006938 | 0.012638 |
| 149 | 0.002237 | 0.003538 | 0.001169 | 0.003398 | −0.002431 | 0.009944 | −0.00749 | 0.001217 | −0.038456 | −0.041544 | −0.012587 | −0.007248 | −0.033978 | −0.035238 |
| 150 | −0.015424 | −0.016254 | −0.002697 | −0.016988 | −0.000249 | −0.024062 | 0.000124 | −0.009073 | 0.006663 | 0.020803 | 0.004553 | 0.001732 | −0.005388 | −0.003087 |
| 151 | −0.036527 | −0.045855 | −0.034297 | −0.009701 | −0.013621 | 0.037649 | −0.004394 | 0.01008 | −0.014285 | −0.082317 | −0.000789 | −0.033074 | −0.019389 | −0.030466 |
| 152 | 0.008135 | 0.006914 | 0.008444 | 0.007366 | 0.012172 | 0.017906 | 0.012918 | 0.018942 | 0.015587 | 0.011025 | −0.004799 | −0.013506 | 0.009112 | 0.015787 |
| 153 | 0.010196 | 0.003494 | −0.032792 | −0.00561 | −0.00436 | 0.017615 | 0.019982 | −0.0061 | 0.013481 | 0.005198 | 0.005569 | 0.005243 | 0.016328 | 0.019221 |
| 154 | 0.00326 | −0.0043 | −0.000761 | −0.006866 | 0.003047 | −0.007418 | −0.005834 | 0.011643 | 0.001779 | 0.05498 | 0.011852 | 0.012538 | 0.009537 | 0.007579 |
| 155 | 0.017192 | 0.020259 | −0.008991 | 0.013717 | −0.005856 | −0.011814 | −0.006823 | −0.032101 | −0.002985 | 0.038864 | −0.001767 | 0.009618 | −0.00261 | −0.007879 |
| 156 | −0.015891 | −0.01738 | −0.00789 | 0.009641 | 0.002213 | 0.010815 | −0.008064 | 0.005145 | −0.012912 | 0.04545 | −0.0066 | 0.000447 | −0.011968 | −0.002818 |
| 157 | 0.00144 | 0.004401 | 0.001851 | −0.001959 | −0.013721 | −0.009167 | −0.01619 | 0.000495 | −0.000798 | 0.03389 | −0.00391 | −0.000787 | 0.004535 | 0.005924 |
| 158 | 0.010454 | 0.016989 | −0.003166 | −0.007789 | 0.009101 | 0.011338 | 0.02093 | −0.044723 | 0.006453 | 0.054446 | −0.004981 | −0.005846 | −0.009564 | −0.006012 |
| 159 | −0.032014 | −0.035863 | 0.038144 | −0.02176 | 0.021096 | 0.006126 | 0.014202 | 0.020222 | 0.007814 | 0.023167 | 0.005886 | −0.013102 | −0.011365 | −0.00395 |
| 160 | 0.01371 | 0.007428 | 0.016313 | 0.007547 | −0.003418 | −0.021369 | −0.001923 | 0.024131 | 0.003218 | −0.028726 | −0.004673 | −0.022409 | −0.03521 | −0.007491 |
| 161 | −0.025869 | −0.024136 | −0.026828 | −0.014473 | −0.018666 | 0.009326 | 0.000426 | −0.002459 | −0.011494 | −0.000349 | −0.011447 | −0.008117 | 0.024166 | 0.01217 |
| 162 | −0.019592 | −0.020957 | 0.032097 | 0.007993 | 0.022069 | −0.002156 | 0.021804 | −0.011643 | 0.027127 | −0.054523 | 0.026995 | 0.014371 | 0.006426 | −0.007462 |
| 163 | 0.004083 | 0.00037 | 0.02962 | −0.002476 | 0.004424 | −0.02184 | 0.00693 | 0.014607 | 0.014163 | 0.009715 | −0.004293 | −0.030075 | −0.001673 | 0.004728 |
| 164 | −0.003093 | −0.007507 | 0.020483 | 0.022721 | 0.015034 | 0.026913 | 0.025378 | −0.022373 | 0.001972 | −0.017037 | 0.002562 | −0.01591 | −0.027256 | −0.034453 |
| 165 | 0.002789 | 0.003686 | −0.064739 | 0.026589 | −0.047544 | 0.001842 | −0.03987 | −0.001325 | −0.028477 | −0.037758 | −0.042668 | −0.020181 | 0.018379 | 0.014084 |
| 166 | 0.011586 | 0.027376 | 0.013248 | −0.003868 | −0.015371 | −0.013193 | −0.02156 | −0.000425 | −0.031125 | 0.007869 | 0.009917 | 0.001488 | −0.005667 | −0.022881 |
| 167 | 0.006883 | 0.01503 | −0.001487 | 0.013419 | −0.014293 | 0.003228 | −0.007072 | 0.00708 | 0.007189 | 0.003557 | −0.004171 | 0.003037 | 0.012344 | 0.000602 |
| 168 | −0.010213 | −0.010887 | 0.011286 | 0.003479 | 0.013693 | −0.007003 | 0.024133 | 0.000244 | 0.023764 | −0.02012 | 0.007509 | −0.004359 | 0.016774 | 0.019337 |
| 169 | 0.017263 | 0.019041 | −0.002288 | 0.001981 | 0.006358 | 0.00213 | 0.001793 | −0.01599 | −0.002883 | −0.017712 | 0.003271 | 0.005701 | −0.001578 | −0.003806 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 170 | 0.023414 | 0.025105 | −0.001502 | 0.007655 | 0.008014 | 0.016033 | 0.006437 | −0.00906 | −0.000781 | −0.034609 | 0.003738 | 0.005824 | 0.003834 | 0.005905 |
| 171 | 0.004838 | 0.011309 | −0.0062 | 0.004535 | 0.021852 | 0.039094 | 0.029997 | −0.012813 | 0.006338 | −0.010317 | −0.006563 | 0.002351 | 0.016862 | 0.009363 |
| 172 | −0.00045 | 0.004851 | −0.02234 | −0.010746 | −0.01324 | 0.006108 | −0.011382 | −0.00571 | −0.006649 | 0.004111 | −0.005946 | 0.00537 | −0.004723 | 0.000119 |
| 173 | 0.00839 | 0.007378 | −0.039661 | −0.013719 | −0.017568 | −0.010523 | −0.01342 | −0.013082 | −0.002732 | −0.016617 | −0.006797 | 0.006152 | 0.001534 | 0.007445 |
| 174 | −0.003059 | 0.002016 | −0.021254 | −0.013162 | −0.005129 | −0.005863 | −0.006419 | −0.015143 | −0.003044 | −0.023154 | −0.001778 | 0.001037 | −0.014932 | −0.021889 |
| 175 | 0.006526 | 0.008375 | −0.037651 | −0.006307 | −0.014832 | −0.016553 | −0.019615 | −0.02101 | −0.025419 | −0.065553 | −0.014602 | −0.013348 | −0.035466 | −0.043793 |
| 176 | −0.003581 | 0.006349 | −0.013387 | 0.00075 | 0.003076 | 0.023473 | −0.011315 | 0.003439 | −0.00188 | 0.015408 | −0.015839 | −0.005765 | 0.014153 | 0.02748 |
| 177 | −0.052697 | −0.05072 | −0.018097 | 0.001159 | −0.000496 | 0.019304 | −0.00081 | −0.002372 | 0.004595 | 0.023333 | 0.00635 | −0.001517 | 0.000387 | −0.014559 |
| 178 | −0.016184 | −0.016753 | −0.000086 | 0.002748 | −0.006985 | −0.018216 | 0.004756 | −0.012707 | 0.030796 | −0.05005 | 0.008902 | −0.01451 | 0.010713 | 0.007692 |
| 179 | 0.010274 | 0.008481 | 0.000885 | 0.01136 | 0.001323 | −0.002223 | 0.007697 | −0.000082 | 0.02091 | −0.013065 | 0.008131 | 0.007094 | 0.01281 | 0.021425 |
| 180 | 0.011631 | 0.012015 | 0.002034 | 0.009039 | −0.00023 | −0.004503 | 0.001795 | 0.002817 | 0.022714 | −0.029722 | 0.012899 | 0.015081 | 0.018889 | 0.025672 |
| 181 | 0.015276 | 0.014291 | 0.000309 | 0.011445 | −0.000872 | 0.003496 | −0.000801 | −0.002579 | 0.01759 | −0.025623 | 0.00782 | 0.011834 | 0.014233 | 0.025741 |
| 182 | 0.0016 | 0.004923 | 0.001086 | 0.007447 | 0.007106 | 0.014194 | 0.007282 | 0.002036 | 0.01363 | −0.01082 | 0.005087 | 0.008728 | 0.012565 | 0.024718 |
| 183 | −0.016398 | −0.013949 | 0.000685 | 0.007758 | 0.014611 | 0.014687 | 0.021027 | −0.014792 | 0.00798 | 0.024732 | −0.009331 | −0.001684 | 0.007858 | 0.006243 |
| 184 | −0.035981 | −0.028462 | 0.012258 | −0.008549 | 0.016855 | −0.001403 | 0.018469 | −0.008457 | 0.015387 | −0.002902 | −0.00414 | −0.008865 | 0.017473 | 0.009396 |
| 185 | −0.011126 | −0.010695 | 0.012966 | 0.002104 | −0.012245 | −0.032607 | −0.025936 | −0.007948 | −0.02566 | −0.010375 | −0.014268 | −0.006142 | −0.024699 | −0.02183 |
| 186 | 0.018225 | 0.018396 | 0.000481 | −0.002798 | 0.016944 | 0.026178 | 0.022039 | −0.001659 | 0.018196 | −0.017007 | 0.033682 | 0.039946 | 0.017475 | 0.021319 |
| 187 | −0.01357 | −0.018031 | 0.00069 | 0.000305 | 0.00516 | −0.011675 | 0.008928 | −0.004099 | 0.019678 | −0.013782 | 0.022407 | 0.018639 | 0.003977 | 0.006683 |
| 188 | −0.023338 | −0.022482 | 0.001229 | −0.000659 | 0.005018 | −0.012057 | 0.001197 | −0.009361 | 0.01498 | −0.008118 | 0.016298 | 0.016393 | −0.00169 | −0.005824 |
| 189 | −0.017724 | −0.01572 | 0.003426 | −0.007991 | 0.018509 | −0.011357 | 0.009165 | −0.016516 | 0.012807 | −0.005411 | 0.01568 | 0.011459 | −0.007104 | −0.006171 |
| 190 | −0.006381 | −0.000637 | 0.004795 | −0.007692 | −0.017223 | −0.024336 | −0.017663 | −0.006122 | −0.021707 | −0.036773 | −0.016654 | −0.016281 | −0.017818 | −0.026393 |
| 191 | 0.004255 | 0.003756 | 0.004264 | −0.001545 | −0.011159 | −0.004779 | −0.008796 | −0.006347 | −0.015854 | −0.018701 | −0.004271 | −0.000605 | −0.005666 | −0.011695 |
| 192 | −0.005722 | −0.009217 | 0.018611 | 0.006451 | 0.011188 | 0.006807 | 0.016267 | 0.008762 | −0.0004 | 0.020657 | 0.003371 | −0.002723 | −0.009699 | −0.026077 |
| 193 | 0.0033 | 0.002951 | −0.011413 | −0.008589 | 0.002649 | 0.003197 | 0.005651 | 0.003933 | 0.002552 | −0.007893 | −0.000074 | 0.002895 | −0.002304 | −0.001272 |
| 194 | −0.008562 | −0.008878 | −0.005475 | 0.003634 | 0.001129 | −0.034926 | 0.00238 | −0.016756 | 0.006963 | −0.002758 | 0.004037 | 0.001842 | −0.013657 | −0.019403 |
| 195 | 0.033749 | 0.040467 | 0.026282 | 0.000952 | 0.009391 | 0.000748 | 0.007035 | 0.018637 | −0.001936 | 0.032061 | 0.009853 | 0.006501 | −0.010738 | 0.002116 |
| 196 | 0.009867 | 0.015519 | 0.024329 | 0.003185 | 0.006641 | −0.001474 | 0.000474 | 0.006117 | −0.000641 | −0.033611 | 0.011882 | 0.004913 | −0.004205 | −0.010623 |
| 197 | 0.00681 | 0.011569 | 0.005851 | 0.000164 | 0.005325 | 0.019021 | 0.001714 | 0.001455 | −0.023144 | −0.027051 | −0.016014 | −0.003538 | −0.013998 | −0.026782 |
| 198 | 0.007404 | 0.010844 | 0.028611 | 0.006108 | 0.010518 | −0.004447 | 0.023614 | 0.005757 | 0.013023 | 0.02909 | 0.001157 | −0.020607 | −0.013767 | −0.001152 |
| 199 | −0.01958 | −0.015726 | 0.041365 | 0.00669 | 0.005353 | −0.039391 | 0.005725 | −0.016383 | 0.01075 | −0.026141 | 0.03066 | −0.001899 | −0.001709 | 0.007399 |
| 200 | −0.01315 | −0.011297 | 0.010835 | 0.002346 | 0.015664 | 0.038407 | 0.047502 | −0.010958 | 0.03624 | 0.018294 | 0.004665 | −0.012682 | 0.002865 | 0.002592 |
| 201 | −0.004282 | −0.008165 | 0.032345 | 0.005062 | 0.009644 | 0.005799 | 0.01064 | −0.021908 | −0.007887 | −0.022468 | −0.001754 | −0.011886 | −0.024283 | −0.024491 |
| 202 | 0.012113 | 0.014298 | 0.023665 | 0.009075 | 0.016369 | 0.024156 | 0.028028 | 0.019433 | 0.021568 | −0.005614 | 0.01159 | −0.006435 | −0.004763 | −0.002003 |
| 203 | −0.018386 | −0.017496 | −0.014483 | −0.009219 | −0.029255 | −0.062005 | −0.03599 | −0.002126 | −0.053868 | 0.043591 | −0.028113 | −0.033329 | −0.042808 | −0.051213 |
| 204 | −0.012246 | −0.012032 | −0.007046 | 0.014303 | 0.014751 | 0.050128 | −0.008897 | 0.036675 | −0.00178 | 0.018251 | 0.014963 | 0.032149 | 0.03434 | 0.050105 |
| 205 | 0.017151 | 0.009238 | 0.007293 | −0.017921 | −0.044655 | −0.042634 | −0.033506 | 0.030175 | 0.028655 | −0.001043 | −0.035305 | −0.04177 | 0.017909 | 0.022002 |
| 206 | 0.024605 | 0.031508 | −0.006454 | −0.022094 | −0.011656 | −0.034933 | −0.000052 | −0.007414 | 0.00384 | 0.001992 | −0.014151 | −0.031892 | 0.013543 | −0.004906 |
| 207 | −0.002027 | −0.005853 | −0.014151 | 0.03124 | −0.015957 | 0.023729 | −0.038724 | −0.048167 | −0.009732 | −0.036659 | −0.015027 | 0.007557 | 0.010696 | 0.019265 |
| 208 | 0.013031 | 0.014439 | 0.016171 | 0.00331 | 0.018041 | −0.00093 | 0.004868 | −0.01906 | −0.023561 | 0.014213 | −0.022852 | −0.040704 | −0.034309 | −0.052411 |
| 209 | −0.012511 | −0.006748 | −0.005949 | −0.023432 | 0.021965 | 0.016307 | 0.004863 | 0.010794 | −0.00661 | 0.051724 | 0.002813 | −0.00047 | 0.005019 | −0.003529 |
| 210 | 0.01161 | 0.013467 | −0.012191 | −0.006408 | 0.024728 | 0.030067 | −0.000251 | −0.044996 | −0.027331 | 0.023126 | 0.014412 | 0.015467 | −0.035107 | −0.010372 |
| 211 | −0.011049 | −0.020998 | −0.013365 | −0.001365 | −0.009915 | 0.023491 | −0.009107 | −0.010829 | −0.005858 | 0.005413 | 0.018528 | 0.034345 | −0.003758 | 0.016755 |
| 212 | 0.019472 | 0.013407 | −0.001142 | 0.000678 | 0.000399 | 0.018576 | 0.002651 | 0.021444 | −0.011121 | 0.054751 | −0.022754 | −0.003934 | −0.010739 | −0.001636 |
| 213 | 0.00051 | −0.000461 | −0.015799 | 0.027014 | −0.021213 | −0.022211 | −0.027781 | −0.015527 | −0.01092 | −0.033763 | −0.000484 | 0.008592 | −0.025877 | −0.009348 |
| 214 | −0.003308 | −0.001305 | 0.024399 | 0.006851 | 0.016515 | 0.004174 | 0.019134 | −0.011803 | 0.028915 | −0.00547 | 0.015899 | 0.015285 | 0.024383 | 0.023846 |
| 215 | 0.014276 | 0.011458 | −0.004724 | −0.004924 | 0.022393 | 0.014078 | 0.018245 | −0.00004 | 0.032237 | −0.012741 | 0.011084 | −0.001251 | 0.015575 | 0.018826 |
| 216 | 0.003698 | 0.002662 | 0.01224 | 0.017461 | 0.039597 | 0.043236 | 0.033985 | 0.00798 | 0.023861 | −0.028079 | 0.015875 | 0.00775 | 0.012756 | 0.005853 |
| 217 | −0.022863 | −0.026056 | 0.027304 | −0.001128 | −0.002809 | −0.037852 | −0.000336 | −0.017436 | 0.005096 | 0.016229 | 0.005675 | −0.023607 | −0.025239 | −0.029152 |
| 218 | 0.023329 | 0.026802 | 0.000101 | −0.020597 | 0.008339 | 0.01292 | −0.006718 | −0.002957 | −0.007492 | 0.016505 | −0.001958 | 0.004466 | −0.00518 | 0.002973 |
| 219 | 0.018079 | 0.014868 | 0.00488 | −0.005628 | 0.022591 | 0.021352 | 0.016147 | −0.022405 | −0.003187 | 0.003239 | −0.001476 | −0.00722 | −0.005179 | −0.011763 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 220 | −0.017515 | −0.01198 | 0.037346 | 0.001936 | 0.007392 | −0.038506 | −0.003371 | −0.022587 | −0.002734 | 0.029846 | 0.001966 | −0.019281 | −0.01102 | −0.017034 |
| 221 | 0.020353 | 0.017419 | −0.024293 | −0.006797 | −0.00263 | 0.006023 | −0.010582 | −0.004899 | −0.006629 | 0.036136 | −0.015346 | 0.006675 | −0.007159 | 0.006433 |
| 222 | 0.020513 | 0.015156 | −0.002941 | −0.011061 | −0.002409 | −0.013206 | −0.005861 | −0.000951 | −0.009207 | 0.032354 | −0.015025 | −0.018903 | −0.019459 | −0.016499 |
| 223 | 0.028482 | 0.026136 | −0.022696 | −0.003749 | −0.002524 | −0.000584 | −0.012 | −0.022624 | −0.023285 | 0.007715 | −0.017209 | −0.005491 | −0.020554 | −0.011947 |
| 224 | −0.001353 | 0.005818 | 0.017708 | 0.014932 | 0.028181 | 0.021467 | 0.031303 | 0.028263 | 0.01499 | 0.005739 | 0.019268 | 0.004035 | −0.005092 | −0.013157 |
| 225 | 0.00512 | 0.013539 | 0.021394 | 0.019822 | 0.029921 | 0.016523 | 0.030601 | 0.022429 | 0.006846 | 0.01481 | 0.015256 | 0.008557 | −0.017271 | −0.023991 |
| 226 | 0.015302 | 0.016158 | −0.010016 | −0.014319 | 0.008687 | −0.001174 | 0.005206 | 0.015557 | −0.014627 | 0.025146 | −0.00277 | −0.003728 | −0.006728 | −0.011166 |
| 227 | 0.010806 | 0.012832 | −0.014543 | −0.013273 | 0.016055 | −0.015656 | 0.032163 | 0.041185 | 0.022255 | 0.015885 | 0.016578 | −0.011557 | 0.012935 | −0.0089 |
| 228 | 0.011585 | 0.008097 | 0.021398 | −0.004521 | 0.015373 | −0.010623 | 0.014552 | −0.001199 | −0.001432 | −0.028407 | −0.000979 | −0.004241 | −0.026852 | −0.028421 |
| 229 | 0.025683 | 0.01904 | 0.015926 | 0.002772 | −0.03173 | −0.029751 | −0.036177 | 0.01304 | −0.001505 | −0.012657 | 0.004734 | 0.021015 | −0.011113 | 0.008392 |
| 230 | 0.007772 | 0.00188 | 0.010987 | 0.005948 | −0.034183 | −0.034347 | −0.023939 | 0.009396 | 0.01511 | −0.039475 | −0.000177 | −0.00179 | 0.025501 | 0.020414 |
| 231 | 0.013533 | 0.009482 | −0.036128 | −0.013353 | −0.024546 | −0.001113 | −0.032431 | 0.038032 | −0.032971 | 0.004158 | −0.020465 | −0.003326 | 0.004851 | 0.009971 |
| 232 | 0.01154 | 0.008409 | 0.017824 | 0.010461 | 0.021602 | 0.008346 | 0.02182 | −0.005702 | 0.007539 | 0.010842 | 0.00605 | 0.015418 | −0.00833 | 0.001399 |
| 233 | 0.019942 | 0.00931 | −0.000948 | 0.011764 | 0.008721 | 0.013146 | 0.012226 | 0.013515 | 0.02197 | 0.006088 | 0.02315 | 0.02394 | 0.006418 | 0.021837 |
| 234 | −0.006136 | −0.014221 | −0.009435 | 0.00306 | 0.01688 | 0.014226 | 0.017416 | −0.00397 | 0.01187 | −0.026272 | −0.014308 | 0.002859 | 0.013037 | 0.001769 |
| 235 | −0.003234 | −0.012533 | −0.013936 | −0.005474 | −0.006074 | −0.006449 | −0.003184 | 0.024811 | 0.012193 | −0.00319 | −0.008698 | −0.003184 | 0.011876 | 0.015252 |
| 236 | 0.003466 | 0.010422 | −0.025889 | 0.003424 | −0.009012 | 0.011591 | −0.010511 | −0.000564 | −0.011429 | 0.006477 | −0.01339 | 0.005353 | 0.018717 | 0.019703 |
| 237 | −0.033131 | −0.030781 | −0.000147 | 0.007821 | 0.010902 | 0.024715 | 0.013333 | −0.0082 | 0.002765 | −0.033776 | 0.005574 | 0.01836 | 0.003295 | −0.006309 |
| 238 | −0.008811 | −0.020618 | 0.00882 | 0.01285 | 0.003906 | 0.021204 | 0.007458 | −0.009343 | 0.000858 | −0.043365 | −0.005862 | −0.001674 | −0.000186 | −0.008092 |
| 239 | 0.01534 | 0.003174 | 0.001316 | 0.004939 | −0.002341 | 0.014594 | −0.004116 | 0.005161 | −0.007726 | −0.017672 | −0.010487 | −0.014089 | −0.005657 | −0.003525 |
| 240 | −0.001247 | −0.010276 | −0.010042 | 0.01259 | 0.000665 | −0.006977 | −0.000233 | 0.003235 | −0.00233 | −0.03192 | 0.010892 | 0.007668 | −0.000811 | −0.011966 |
| 241 | −0.00033 | −0.003853 | 0.010669 | 0.020863 | 0.023226 | 0.02919 | 0.00692 | 0.007732 | 0.00842 | −0.008657 | 0.021486 | 0.029782 | 0.007376 | 0.005128 |
| 242 | −0.006764 | −0.010042 | −0.017756 | −0.003202 | −0.013236 | −0.013938 | −0.016098 | 0.022162 | 0.00889 | 0.020529 | −0.003052 | 0.001995 | 0.011692 | 0.026916 |
| 243 | −0.016354 | −0.026407 | −0.000101 | −0.006587 | 0.009408 | −0.009742 | 0.014901 | 0.00752 | 0.009379 | −0.003353 | 0.014058 | 0.00357 | −0.030391 | −0.011127 |
| 244 | −0.000719 | −0.001568 | 0.007112 | −0.00832 | 0.0083 | 0.005554 | 0.012235 | −0.00284 | 0.018955 | 0.016477 | 0.010115 | 0.016398 | 0.006198 | 0.017848 |
| 245 | −0.001365 | 0.003662 | 0.016734 | 0.016609 | 0.005634 | 0.009088 | −0.001583 | −0.007562 | 0.01003 | 0.026314 | 0.009404 | 0.012405 | 0.001122 | 0.006059 |
| 246 | −0.014951 | −0.013964 | −0.006614 | 0.001616 | −0.002296 | −0.005291 | 0.000073 | −0.00048 | 0.004883 | 0.009691 | −0.000697 | −0.008865 | 0.014762 | 0.011643 |
| 247 | −0.005551 | −0.003434 | −0.003162 | 0.001191 | −0.010783 | −0.028307 | −0.009299 | −0.005168 | −0.008066 | 0.01125 | −0.005863 | −0.012633 | −0.001905 | −0.004388 |
| 248 | −0.000597 | 0.002781 | 0.010908 | 0.001997 | 0.002183 | −0.022891 | 0.003039 | −0.009768 | 0.000009 | 0.017379 | −0.003096 | −0.001821 | 0.00364 | −0.006271 |
| 249 | 0.006942 | 0.001477 | 0.001859 | 0.007499 | 0.000198 | −0.005864 | 0.001621 | 0.009535 | 0.000254 | 0.01431 | 0.00011 | −0.003825 | 0.014662 | 0.003814 |
| 250 | −0.006787 | −0.011535 | −0.023282 | 0.011547 | −0.001025 | 0.009527 | 0.003111 | −0.01478 | −0.001734 | −0.032267 | −0.003046 | 0.008887 | 0.017255 | 0.002449 |
| 251 | −0.017138 | −0.02132 | 0.006478 | 0.018869 | 0.008557 | −0.001032 | 0.007442 | −0.016161 | 0.000177 | −0.021987 | 0.003282 | 0.011243 | 0.004599 | −0.014131 |
| 252 | −0.008736 | −0.004939 | 0.025786 | 0.011444 | 0.004657 | −0.008796 | −0.006195 | 0.006124 | 0.00371 | 0.035576 | 0.004975 | 0.02072 | −0.001832 | 0.004911 |
| 253 | −0.015181 | −0.009617 | 0.004712 | 0.009474 | 0.007936 | 0.004971 | −0.001897 | −0.000761 | −0.006507 | 0.006781 | −0.005641 | 0.014651 | −0.014111 | −0.01191 |
| 254 | 0.015058 | 0.011081 | −0.021569 | 0.006654 | 0.004792 | 0.012789 | 0.005453 | −0.010668 | −0.00461 | −0.011558 | 0.006391 | 0.010877 | −0.003378 | 0.005998 |
| 255 | −0.008075 | −0.01281 | −0.011142 | 0.006919 | 0.001875 | −0.003653 | 0.007632 | −0.004336 | 0.0104 | 0.0052 | 0.007284 | 0.010199 | 0.006773 | 0.012154 |
| 256 | −0.005848 | −0.00005 | 0.006936 | 0.011399 | 0.00113 | 0.012347 | −0.012868 | 0.01807 | 0.003377 | 0.032981 | −0.009857 | 0.008191 | 0.00318 | 0.008324 |
| 257 | 0.013596 | 0.013588 | −0.006241 | 0.009141 | −0.014756 | 0.000975 | −0.009295 | 0.008159 | 0.003581 | 0.0082 | −0.02028 | −0.020713 | 0.006924 | 0.012547 |
| 258 | −0.000573 | 0.009694 | 0.007302 | 0.00229 | 0.020158 | 0.007203 | 0.011307 | 0.007595 | 0.000811 | 0.009529 | 0.01515 | 0.00107 | −0.019783 | −0.017652 |
| 259 | 0.004498 | 0.002656 | −0.009158 | 0.00285 | −0.003204 | −0.003009 | 0.000336 | −0.002318 | −0.006568 | 0.006355 | −0.003883 | 0.001433 | 0.000818 | −0.010094 |
| 260 | −0.0024 | 0.008446 | 0.010534 | 0.002653 | −0.006466 | −0.032508 | −0.011426 | −0.01788 | −0.005484 | 0.012516 | −0.003716 | 0.010338 | 0.000066 | 0.001413 |
| 261 | −0.013055 | −0.008505 | 0.007316 | 0.000895 | −0.0026 | −0.03 | −0.011469 | −0.000122 | −0.013973 | −0.011618 | −0.002942 | 0.003446 | −0.010034 | −0.021417 |
| 262 | −0.010527 | −0.007063 | 0.00206 | −0.002713 | −0.024734 | −0.028081 | −0.022301 | 0.009814 | −0.005783 | 0.003665 | −0.015795 | −0.015474 | 0.001522 | 0.002665 |
| 263 | −0.008888 | −0.00595 | −0.000996 | −0.000258 | −0.021203 | −0.01981 | −0.011865 | 0.002593 | 0.001368 | 0.011738 | −0.013363 | −0.008377 | 0.008594 | 0.007903 |
| 264 | 0.00762 | 0.004949 | −0.005904 | −0.003089 | 0.010143 | 0.012652 | 0.012559 | 0.020803 | 0.000302 | 0.018657 | 0.005423 | 0.001013 | 0.004676 | −0.001189 |
| 265 | 0.016119 | 0.021184 | −0.001959 | −0.003589 | 0.016929 | 0.017301 | 0.017286 | 0.019087 | −0.013932 | 0.027177 | 0.010219 | 0.006708 | −0.008126 | −0.003723 |
| 266 | 0.000374 | 0.005229 | 0.013089 | 0.005025 | 0.023006 | 0.006854 | 0.014033 | 0.003999 | −0.015117 | 0.019962 | 0.01252 | 0.01433 | −0.018696 | −0.012904 |
| 267 | 0.01704 | 0.022679 | 0.003105 | −0.011942 | 0.012897 | 0.006806 | 0.006959 | 0.010087 | −0.000184 | 0.001602 | 0.002718 | 0.001111 | −0.010029 | −0.00265 |
| 268 | 0.014945 | 0.016609 | −0.014235 | −0.016879 | 0.005523 | 0.005605 | 0.002575 | 0.015519 | −0.017458 | 0.025855 | −0.006677 | −0.006805 | −0.003685 | −0.007051 |
| 269 | 0.008938 | 0.010899 | −0.007521 | −0.012344 | 0.008092 | 0.000799 | 0.003247 | 0.009021 | −0.008837 | 0.021199 | −0.004701 | −0.000486 | −0.001172 | −0.001414 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 270 | 0.003258 | 0.008739 | −0.005206 | −0.019654 | 0.005225 | −0.024401 | 0.010884 | 0.009189 | 0.001155 | 0.01275 | 0.001598 | −0.014428 | 0.006001 | −0.008195 |
| 271 | 0.003106 | 0.005711 | −0.004183 | 0.00418 | 0.002584 | 0.022414 | −0.012004 | −0.004197 | 0.00623 | 0.013581 | 0.01577 | 0.022658 | 0.015463 | 0.031318 |
| 272 | 0.024194 | 0.021313 | −0.000823 | −0.006489 | −0.04265 | −0.0315 | −0.045291 | 0.00763 | −0.025101 | −0.010623 | −0.007942 | 0.008454 | −0.018685 | −0.008295 |
| 273 | 0.008749 | 0.013302 | 0.000044 | −0.018213 | −0.060291 | −0.061577 | −0.052382 | 0.001577 | −0.017942 | 0.000601 | −0.009421 | −0.007773 | 0.012573 | 0.00595 |
| 274 | 0.007687 | 0.01186 | 0.00174 | −0.015949 | −0.058698 | −0.061729 | −0.051174 | 0.003098 | −0.014095 | −0.003342 | −0.006281 | −0.005286 | 0.014227 | 0.008076 |
| 275 | −0.014633 | −0.011478 | 0.006511 | −0.019653 | −0.040611 | −0.083985 | −0.011414 | −0.002154 | 0.034062 | −0.03055 | 0.010498 | −0.024612 | 0.042469 | 0.01972 |
| 276 | 0.015767 | 0.019967 | −0.021305 | 0.004928 | −0.014802 | 0.009718 | −0.024639 | 0.007306 | −0.01976 | −0.007208 | −0.009329 | 0.012031 | 0.004214 | 0.010978 |
| 277 | −0.002997 | 0.003638 | 0.002291 | −0.005513 | 0.001791 | 0.004706 | 0.001972 | 0.007053 | 0.004511 | −0.014263 | 0.009323 | 0.009885 | 0.000087 | 0.005148 |
| 278 | −0.004645 | 0.003209 | 0.005861 | −0.005403 | 0.003433 | 0.005023 | 0.004036 | −0.000086 | 0.009366 | −0.024887 | 0.005833 | 0.009732 | 0.000466 | 0.002999 |
| 279 | 0.012297 | −0.000854 | 0.007922 | 0.003563 | 0.005626 | 0.008879 | 0.010441 | −0.010086 | 0.003747 | −0.041704 | −0.000566 | −0.008261 | −0.0053 | −0.007135 |
| 280 | 0.000393 | −0.001247 | 0.004568 | −0.000626 | 0.015061 | 0.007047 | 0.016891 | 0.018138 | 0.005716 | −0.007822 | 0.022647 | 0.011615 | −0.02883 | −0.020301 |
| 281 | −0.008557 | −0.001676 | 0.005012 | −0.00659 | 0.003004 | −0.012322 | −0.009284 | −0.002475 | −0.023628 | 0.017319 | 0.010499 | −0.002166 | −0.01884 | −0.022299 |
| 282 | −0.003026 | 0.00521 | 0.014177 | −0.006045 | 0.009728 | −0.001734 | 0.003583 | −0.000451 | −0.005171 | 0.010225 | 0.014132 | −0.003276 | −0.017286 | −0.012122 |
| 283 | −0.003078 | 0.00005 | 0.005998 | −0.006423 | −0.006755 | −0.034138 | −0.004615 | −0.011693 | −0.008583 | −0.002221 | −0.001232 | −0.007159 | −0.004799 | −0.014815 |
| 284 | 0.012914 | 0.013667 | −0.00725 | 0.001832 | −0.01223 | 0.00577 | −0.007919 | 0.004978 | −0.000149 | −0.00399 | −0.016519 | −0.013542 | 0.006436 | 0.007071 |
| 285 | 0.011092 | 0.01084 | 0.001349 | 0.004082 | −0.006541 | 0.010882 | 0.000476 | 0.002931 | 0.010753 | −0.00389 | −0.016468 | −0.017017 | 0.012316 | 0.01641 |
| 286 | 0.010591 | 0.012014 | 0.015702 | 0.013681 | 0.035027 | 0.036573 | 0.025634 | 0.007171 | 0.01274 | −0.007236 | 0.030331 | 0.012474 | −0.024196 | −0.013586 |
| 287 | 0.00609 | 0.008216 | 0.020461 | 0.008295 | 0.035291 | 0.026246 | 0.029711 | 0.003949 | 0.020513 | −0.009867 | 0.030663 | 0.010324 | −0.022403 | −0.012693 |
| 288 | −0.043338 | −0.032587 | 0.011689 | −0.005324 | 0.021604 | −0.013964 | 0.012338 | 0.000559 | 0.011349 | −0.001048 | 0.019723 | 0.008181 | −0.000759 | −0.020738 |
| 289 | −0.015043 | −0.006171 | 0.012102 | −0.005485 | −0.010617 | −0.029461 | −0.003622 | 0.011612 | 0.008092 | 0.011771 | −0.002082 | −0.020096 | 0.011378 | 0.008719 |
| 290 | −0.105139 | −0.101795 | 0.001788 | −0.006764 | −0.00632 | −0.029169 | 0.000168 | −0.02829 | 0.009112 | −0.024996 | 0.000202 | −0.007826 | 0.011961 | −0.0118 |
| 291 | 0.896919 | −0.10011 | 0.000898 | −0.006237 | −0.005634 | −0.02707 | 0.001816 | −0.02699 | 0.009583 | −0.025973 | 0.002479 | −0.006877 | 0.010596 | −0.011436 |
| 292 | −0.099404 | 0.893714 | −0.002932 | −0.002063 | −0.006653 | −0.024897 | −0.000304 | −0.025691 | 0.009563 | −0.032813 | 0.002811 | −0.005949 | 0.007799 | −0.010543 |
| 293 | 0.003639 | −0.001697 | 0.853817 | −0.035356 | −0.053181 | 0.017598 | −0.056591 | 0.015454 | −0.055111 | 0.017731 | −0.053106 | −0.00059 | 0.015504 | 0.005655 |
| 294 | 0.003224 | 0.005096 | −0.041903 | 0.950999 | −0.027712 | −0.027878 | −0.029284 | −0.004079 | −0.024367 | 0.008781 | −0.024995 | −0.01935 | −0.004515 | −0.010573 |
| 295 | −0.000283 | −0.002052 | −0.064724 | −0.030119 | 0.900964 | −0.064916 | −0.091419 | 0.001552 | −0.049461 | −0.005787 | −0.053266 | −0.028667 | 0.007911 | −0.001864 |
| 296 | −0.010065 | −0.005228 | −0.00083 | −0.040402 | −0.077603 | 0.843462 | −0.071762 | −0.033406 | −0.028378 | 0.001616 | −0.02815 | −0.039567 | −0.012797 | −0.028476 |
| 297 | 0.002083 | 0.003146 | −0.056195 | −0.025801 | −0.085385 | −0.054504 | 0.893233 | 0.006654 | −0.068435 | 0.002475 | −0.054102 | −0.021483 | −0.012906 | −0.016974 |
| 298 | −0.027426 | −0.024808 | 0.011643 | −0.012566 | −0.000225 | −0.029494 | 0.002974 | 0.858864 | −0.017768 | −0.07137 | −0.020465 | −0.014937 | −0.037106 | −0.041353 |
| 299 | 0.005109 | 0.006834 | −0.052227 | −0.022856 | −0.040746 | −0.010195 | −0.065071 | −0.019679 | 0.896176 | 0.000843 | −0.056876 | −0.025939 | −0.067541 | −0.071904 |
| 300 | −0.019083 | −0.025231 | 0.016271 | 0.008559 | −0.008424 | −0.005083 | 0.008083 | −0.068087 | 0.014379 | 0.76483 | 0.010424 | −0.01473 | −0.016043 | −0.026908 |
| 301 | −0.003175 | −0.004489 | −0.052744 | −0.023567 | −0.049995 | −0.014579 | −0.049781 | −0.019033 | −0.056296 | 0.002007 | 0.924803 | −0.044477 | −0.018083 | −0.026418 |
| 302 | −0.00445 | −0.004693 | −0.001979 | −0.021857 | −0.031579 | −0.0406 | −0.023636 | −0.019978 | −0.027504 | −0.017058 | −0.04245 | 0.931705 | −0.024953 | −0.037386 |
| 303 | 0.012529 | 0.010956 | 0.00735 | −0.013426 | 0.007299 | −0.007855 | −0.01302 | −0.041656 | −0.065796 | −0.023687 | −0.022056 | −0.026473 | 0.882236 | −0.099792 |
| 304 | −0.005603 | −0.002224 | 0.009759 | −0.016975 | 0.003193 | −0.022213 | −0.011633 | −0.051542 | −0.072195 | −0.037325 | −0.029881 | −0.038692 | −0.105453 | 0.871287 |
| 305 | 0.007125 | 0.003161 | −0.057857 | −0.009978 | −0.020854 | 0.028429 | −0.016661 | 0.003065 | −0.022952 | −0.007097 | −0.034014 | −0.019471 | 0.001497 | −0.003666 |
| 306 | −0.019498 | −0.012378 | −0.081194 | −0.035746 | −0.047202 | −0.037021 | −0.045482 | 0.02089 | −0.035591 | 0.008316 | −0.036642 | −0.016821 | 0.002295 | −0.008139 |
| 307 | −0.013733 | −0.010004 | −0.000153 | −0.007359 | −0.018331 | −0.009017 | −0.015334 | 0.011456 | −0.002121 | −0.061355 | 0.018302 | 0.024232 | −0.023788 | −0.021679 |
| 308 | −0.007386 | −0.016009 | −0.013502 | 0.010368 | −0.017241 | −0.029971 | −0.006791 | −0.012961 | 0.008342 | 0.024535 | 0.000072 | 0.028023 | 0.016326 | 0.018437 |
| 309 | 0.005336 | 0.007635 | −0.018882 | −0.023403 | −0.008693 | −0.017906 | −0.003873 | −0.008691 | −0.007587 | −0.011645 | −0.01716 | −0.021437 | −0.004404 | −0.003933 |
| 310 | −0.004491 | 0.002628 | −0.007549 | −0.028125 | −0.0065 | −0.038748 | 0.012243 | −0.040348 | 0.001187 | 0.017389 | −0.003605 | −0.025257 | −0.018324 | −0.005098 |
| 311 | 0.00511 | 0.007606 | −0.029782 | −0.018604 | −0.022995 | −0.018592 | −0.022475 | −0.009662 | −0.017572 | −0.013104 | −0.015579 | −0.00006 | −0.001734 | −0.007952 |
| 312 | −0.020401 | −0.027646 | 0.020666 | −0.015077 | −0.008587 | −0.038093 | −0.039331 | 0.000774 | −0.005249 | 0.004944 | 0.013933 | 0.00532 | −0.025636 | −0.026892 |
| 313 | 0.011926 | 0.012406 | −0.01638 | −0.007811 | −0.005548 | −0.006676 | −0.01064 | −0.006308 | −0.005322 | 0.005464 | −0.011809 | 0.005072 | −0.005802 | −0.009743 |
| 314 | 0.01981 | 0.021734 | 0.009912 | −0.012634 | 0.002971 | 0.022719 | −0.020924 | −0.032867 | −0.004895 | −0.029096 | 0.012796 | 0.021484 | −0.015516 | −0.015248 |
| 315 | 0.007122 | 0.006527 | −0.015264 | −0.011075 | 0.002194 | −0.005816 | −0.013777 | −0.0039 | −0.023897 | −0.015218 | −0.002334 | 0.004699 | −0.033083 | −0.021272 |
| 316 | −0.014015 | −0.010271 | −0.016611 | −0.00951 | −0.010188 | −0.020003 | 0.014501 | −0.034351 | 0.031171 | −0.009696 | −0.03181 | −0.024623 | 0.006279 | 0.019703 |
| 317 | 0.015459 | 0.015577 | −0.025572 | −0.020949 | −0.026659 | −0.02389 | −0.015757 | −0.01699 | −0.002403 | −0.017348 | −0.0276 | −0.016145 | 0.006103 | 0.018147 |
| 318 | 0.007164 | 0.006654 | −0.024076 | −0.009277 | −0.017713 | −0.009489 | −0.011968 | −0.028162 | −0.012505 | 0.015754 | −0.022648 | −0.002254 | 0.002116 | −0.004334 |
| 319 | 0.011495 | 0.0136 | −0.007696 | −0.007086 | 0.006457 | 0.003819 | −0.004719 | −0.010758 | −0.01565 | −0.018808 | −0.004988 | 0.005421 | −0.028995 | −0.007717 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 320 | 0.000785 | 0.003033 | −0.019524 | −0.017323 | −0.007957 | −0.016817 | −0.006961 | −0.024248 | −0.002444 | 0.006837 | −0.005769 | −0.006111 | 0.001511 | −0.002818 |
| 321 | −0.013498 | −0.005522 | 0.011717 | −0.026732 | −0.025797 | −0.031069 | −0.039823 | −0.008747 | −0.038813 | −0.012318 | −0.019987 | −0.018564 | −0.033118 | −0.039397 |
| 322 | 0.006483 | −0.003154 | 0.015999 | −0.008986 | −0.001278 | −0.003157 | 0.025616 | −0.047414 | 0.014568 | −0.061655 | −0.013 | −0.032019 | 0.005734 | −0.007291 |
| 323 | 0.000196 | −0.002974 | 0.025614 | 0.01043 | 0.012441 | 0.032564 | 0.011263 | −0.038171 | −0.014001 | −0.011996 | −0.00619 | 0.001307 | −0.015573 | −0.016915 |
| 324 | −0.003865 | 0.0038 | −0.012019 | −0.02009 | 0.007086 | −0.022475 | 0.007226 | −0.014213 | −0.0159 | 0.017159 | −0.008992 | −0.033805 | 0.004511 | −0.020284 |
| 325 | 0.009789 | 0.013151 | 0.003082 | −0.034469 | −0.002776 | −0.051702 | −0.013558 | −0.003234 | −0.001891 | 0.001843 | −0.006174 | −0.016086 | −0.01298 | −0.001174 |
| 326 | 0.013499 | 0.015667 | −0.00516 | −0.015649 | 0.004932 | −0.013967 | 0.009032 | 0.011429 | 0.008134 | 0.009988 | 0.013987 | −0.002305 | −0.000198 | 0.011342 |
| 327 | 0.004596 | 0.000371 | 0.009087 | −0.013113 | −0.014592 | −0.030374 | −0.004666 | −0.028509 | −0.012617 | −0.027303 | −0.010132 | −0.025453 | −0.025767 | −0.025081 |
| 328 | −0.005399 | 0.000514 | 0.016242 | −0.016839 | 0.001004 | −0.038709 | −0.001769 | −0.054401 | 0.018834 | −0.059833 | −0.002232 | −0.003521 | 0.02935 | 0.008759 |
| 329 | 0.013596 | 0.007258 | 0.030097 | 0.003502 | 0.000927 | −0.003727 | 0.001787 | −0.016652 | −0.012703 | −0.006875 | −0.008189 | −0.021278 | −0.028938 | −0.011051 |
| 330 | 0.017981 | 0.023142 | 0.030471 | −0.009249 | 0.010942 | 0.007352 | 0.018775 | −0.043201 | 0.006734 | −0.061147 | −0.006072 | −0.034035 | −0.02219 | −0.011867 |
| 331 | 0.003436 | 0.000909 | −0.014698 | −0.020899 | 0.014593 | 0.006739 | 0.007555 | −0.005561 | −0.010972 | −0.01217 | 0.004933 | −0.000428 | −0.029368 | −0.022116 |
| 332 | 0.003095 | 0.018078 | −0.013894 | −0.009453 | −0.009569 | 0.003237 | −0.004831 | −0.013387 | −0.003818 | −0.087556 | −0.00869 | −0.012683 | −0.001828 | −0.010904 |
| 333 | 0.005852 | 0.00703 | −0.006942 | −0.021288 | 0.002596 | −0.016286 | 0.000652 | 0.000221 | 0.005769 | −0.006152 | −0.012631 | −0.016229 | 0.005042 | 0.007791 |
| 334 | 0.005516 | −0.008301 | 0.035518 | −0.013623 | 0.004721 | −0.032155 | −0.010935 | 0.005292 | 0.026932 | 0.029838 | −0.001278 | −0.025947 | 0.006317 | 0.026488 |
| 335 | 0.003497 | 0.006391 | −0.004092 | −0.017687 | 0.023236 | 0.021487 | 0.017827 | −0.003484 | 0.000787 | −0.004622 | 0.003117 | 0.005695 | −0.010341 | −0.003533 |
| 336 | −0.008588 | −0.00243 | −0.008527 | −0.024844 | −0.010677 | −0.005312 | 0.002131 | −0.021827 | −0.018538 | −0.051176 | −0.026966 | −0.024939 | −0.018236 | −0.032215 |
| 337 | −0.031311 | −0.031628 | −0.025573 | −0.01408 | −0.028215 | −0.036242 | −0.029597 | −0.029025 | −0.046287 | 0.011071 | −0.039822 | −0.020168 | −0.02569 | −0.027256 |
| 338 | 0.029171 | 0.022238 | 0.024299 | −0.000058 | −0.019333 | −0.066721 | −0.000237 | −0.078984 | −0.009448 | −0.001603 | −0.001738 | −0.012277 | −0.017883 | −0.015541 |
| 339 | −0.009347 | −0.012791 | −0.008504 | −0.000061 | −0.001437 | 0.014871 | −0.010894 | −0.006379 | −0.009182 | −0.032102 | −0.013709 | −0.00589 | −0.007407 | −0.015188 |
| 340 | 0.008995 | 0.012675 | −0.009048 | 0.019023 | −0.017312 | −0.027308 | −0.024128 | −0.017104 | −0.046509 | 0.024997 | 0.006282 | 0.005898 | −0.038303 | −0.023769 |

| | KT | KU | KV | KW | KX | KY | KZ | LA | LB | LC | LD | LE | LF | LG |
|---|---|---|---|---|---|---|---|---|---|---|---|---|---|---|
| 1 | −0.007355 | 0.032789 | −0.074754 | −0.034326 | 0.01061 | 0.038956 | 0.018526 | 0.084486 | 0.020092 | −0.070569 | 0.008067 | 0.049366 | 0.03155 | −0.049021 |
| 2 | 0.014812 | 0.008158 | 0.084008 | 0.039198 | 0.032327 | 0.046461 | 0.005992 | 0.030047 | −0.065453 | 0.09981 | 0.027099 | −0.081288 | −0.004699 | 0.027303 |
| 3 | −0.063571 | −0.000836 | 0.006708 | −0.012395 | −0.116326 | −0.129417 | −0.093444 | −0.046742 | −0.08385 | −0.01875 | −0.074544 | −0.026095 | −0.10299 | −0.095009 |
| 4 | −0.067838 | −0.108554 | 0.16663 | −0.006964 | 0.006956 | 0.041977 | 0.014572 | 0.133037 | 0.009644 | 0.231827 | 0.042714 | −0.019515 | 0.000677 | 0.067153 |
| 5 | −0.015311 | 0.011647 | 0.112101 | 0.036586 | −0.027883 | −0.011165 | −0.011898 | 0.035864 | −0.057044 | −0.043024 | 0.016635 | 0.009416 | −0.032516 | 0.029149 |
| 6 | 0.023145 | 0.013527 | 0.049064 | 0.002061 | 0.057046 | 0.146641 | 0.021833 | 0.049955 | 0.043044 | 0.030479 | 0.063003 | 0.095615 | 0.041836 | 0.028691 |
| 7 | −0.034399 | −0.04935 | 0.021016 | −0.013465 | 0.053272 | 0.035261 | 0.058712 | 0.037122 | 0.00965 | 0.063099 | 0.079812 | 0.035447 | 0.069184 | 0.122135 |
| 8 | 0.038897 | 0.047153 | 0.052477 | 0.075378 | 0.021735 | 0.008584 | 0.025403 | −0.017165 | −0.01433 | −0.033609 | −0.00706 | 0.070472 | −0.011756 | −0.005276 |
| 9 | −0.100204 | −0.139411 | −0.099642 | −0.182696 | 0.028899 | 0.033408 | −0.049687 | −0.088915 | −0.021581 | 0.000252 | 0.007124 | −0.066521 | 0.006039 | 0.02196 |
| 10 | 0.122191 | −4.023095 | 0.085046 | 0.020113 | −0.05517 | −0.09732 | −0.035078 | 0.059667 | −4.020827 | 0.00985 | −0.030538 | 0.10264 | −0.065539 | −4.079151 |
| 11 | 0.041214 | −0.010677 | −0.07432 | −0.056008 | −0.004265 | 0.053567 | 0.031182 | −0.035251 | 0.032021 | 0.00585 | −0.021957 | 0.037417 | −0.009368 | 0.004943 |
| 12 | 0.015882 | 0.002567 | 0.078731 | −0.034642 | −0.016307 | −0.002099 | 0.030475 | −0.012546 | 0.003543 | 0.086006 | 0.003905 | −0.071558 | −0.029413 | 0.007083 |
| 13 | 0.064986 | −0.046689 | 0.039119 | −0.004534 | −0.009397 | −0.035951 | −0.018294 | 0.039808 | −0.014346 | −0.116723 | 0.019047 | −0.139684 | −0.032224 | −0.062762 |
| 14 | −0.038102 | −0.063155 | −0.050833 | 0.060705 | 0.017531 | −0.025411 | 0.019875 | 0.038553 | 0.032041 | −0.014697 | 0.006838 | 0.091216 | 0.041224 | 0.065367 |
| 15 | 0.018584 | −0.199832 | −0.062216 | 0.127685 | 0.018122 | −0.021999 | −0.050551 | 0.070586 | −0.015707 | 0.013185 | 0.010817 | −0.003382 | 0.021024 | −0.023182 |
| 16 | −0.015875 | −0.037517 | −0.036154 | −0.06726 | 0.033997 | 0.028358 | 0.017375 | −0.042619 | 0.054815 | 0.119675 | 0.036448 | −0.04121 | 0.036032 | 0.018208 |
| 17 | 0.018243 | 0.003815 | −0.136372 | −0.048637 | −0.023694 | 0.019563 | −0.067523 | 0.02881 | −0.062226 | 0.025051 | −0.072686 | 0.072825 | −0.07042 | −0.049402 |
| 18 | 0.134199 | 0.02519 | −0.045332 | −0.088538 | −0.032349 | −0.126969 | 0.020268 | 0.089565 | −0.011897 | 0.131348 | 0.006297 | −0.081551 | −0.041679 | 0.018711 |
| 19 | −0.031249 | 0.067244 | 0.073943 | 0.114672 | 0.007333 | −0.014349 | 0.032249 | 0.121 | 0.000759 | −0.05818 | −0.004929 | 0.002431 | −0.022659 | 0.003183 |
| 20 | 0.021387 | −0.030902 | −0.039661 | −0.107407 | −0.02009 | −0.018803 | −0.041728 | −0.115938 | −0.071381 | −0.093079 | −0.07798 | −0.022223 | −0.024356 | −0.060028 |
| 21 | −0.019391 | 0.025643 | 0.005151 | 0.015321 | −0.013528 | −0.053764 | 0.001768 | 0.021099 | 0.03923 | −0.09458 | −0.024822 | −0.116238 | 0.044279 | 0.052901 |
| 22 | −0.030057 | −0.030183 | 0.070447 | −0.000474 | −0.031776 | 0.006356 | 0.002841 | −0.167459 | −0.081778 | −0.100152 | −0.001506 | −0.131397 | −0.039655 | −0.054439 |
| 23 | −0.018652 | 0.051157 | −0.007806 | −0.008492 | 0.108875 | 0.054158 | 0.005119 | 0.019107 | 0.022692 | 0.036821 | 0.025691 | −0.002676 | 0.037267 | −0.044107 |
| 24 | 0.007382 | 0.08632 | −0.052316 | −0.069312 | 0.036811 | 0.099902 | −0.034275 | −0.011618 | −0.015604 | −0.114359 | 0.051653 | −0.004703 | −0.00929 | −0.014956 |
| 25 | −0.048389 | −0.148006 | −0.132436 | 0.027442 | −0.009956 | −0.117706 | 0.0208481 | 0.113441 | −0.018915 | −0.077877 | 0.011893 | −0.085386 | −0.030334 | 0.032557 |
| 26 | −0.160066 | −0.008443 | 0.037455 | 0.005091 | −0.035326 | 0.029569 | −0.014712 | −0.068534 | −0.050179 | −0.047987 | −0.07709 | −0.022227 | −0.016452 | −0.012454 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 27 | 0.094024 | −0.086834 | −0.050702 | −0.009384 | 0.027138 | 0.048867 | −0.044655 | −0.16257 | −0.00455 | −0.055816 | 0.017591 | 0.091121 | −0.006814 | 0.021044 |
| 28 | −0.070006 | −0.01214 | 0.078095 | 0.083497 | −0.017771 | −0.025197 | 0.078264 | 0.0345 | 0.108721 | 0.051183 | 0.039948 | −0.026704 | −0.057913 | −0.031598 |
| 29 | −0.016202 | 0.022549 | −0.019081 | −0.017992 | −0.005297 | 0.011628 | −0.007065 | −0.01438 | 0.01941 | −0.081646 | −0.021327 | 0.03921 | 0.009392 | −0.016875 |
| 30 | 0.03199 | −0.091061 | 0.020469 | 0.045158 | 0.003439 | −0.09666 | 0.012552 | 0.016361 | −0.005282 | −0.072307 | 0.028378 | −0.00001 | 0.014236 | 0.059588 |
| 31 | 0.043196 | 0.079501 | 0.001824 | −0.015624 | −0.003292 | −0.012556 | 0.0009 | 0.01004 | 0.019367 | 0.137727 | −0.005364 | 0.020773 | −0.009019 | 0.033505 |
| 32 | −0.015504 | −0.086752 | −0.02089 | 0.085376 | 0.051903 | −0.049623 | 0.032011 | 0.034945 | −0.00591 | −0.126675 | 0.01286 | −0.044945 | 0.010884 | 0.09366 |
| 33 | −0.031439 | 0.116546 | 0.011228 | −0.140005 | −0.009249 | −0.028699 | 0.010427 | −0.027792 | 0.037218 | −0.033187 | −0.001892 | −0.082453 | 0.015551 | −0.019499 |
| 34 | −0.054047 | 0.023295 | −0.039385 | 0.064197 | −0.039184 | −0.088171 | −0.039356 | 0.123958 | −0.005929 | 0.053892 | 0.036441 | −0.033776 | 0.006102 | −0.075094 |
| 35 | 0.005239 | −0.029046 | 0.074261 | 0.268031 | −0.028203 | −0.010639 | 0.033887 | −0.12424 | 0.024313 | −0.0153 | −0.003978 | 0.015136 | −0.013825 | −0.033039 |
| 36 | −0.110608 | 0.002647 | 0.125828 | 0.001444 | −0.035145 | 0.024301 | −0.055724 | 0.053048 | −0.07443 | 0.005129 | −0.053178 | −0.050827 | −0.086769 | −0.043625 |
| 37 | 0.025922 | 0.015945 | 0.097431 | −0.02947 | −0.014392 | 0.037319 | −0.007521 | −0.002954 | 0.032076 | 0.115251 | 0.011146 | 0.046911 | 0.032538 | 0.124652 |
| 38 | −0.022002 | −0.085294 | −0.099106 | −0.023455 | −0.017559 | 0.001953 | −0.045516 | 0.086623 | 0.008845 | −0.000986 | −0.039656 | 0.009235 | −0.021664 | −0.104121 |
| 39 | 0.030209 | −0.034406 | −0.015486 | 0.070314 | 0.010712 | 0.003295 | 0.008756 | 0.10311 | 0.056221 | 0.038829 | −0.008471 | −0.057928 | 0.003037 | 0.00984 |
| 40 | −0.025392 | 0.005981 | −0.001661 | −0.024732 | −0.000506 | 0.011146 | −0.012147 | 0.002688 | −0.006729 | −0.012064 | −0.017684 | −0.000057 | −0.009379 | −0.018522 |
| 41 | 0.095437 | 0.074473 | −0.069418 | −0.091017 | 0.051785 | 0.081929 | 0.042574 | −0.08777 | −0.011224 | 0.018462 | −0.001087 | 0.022632 | 0.083334 | 0.045765 |
| 42 | −0.009079 | −0.026838 | −0.010558 | −0.075575 | −0.006052 | −0.093825 | 0.025431 | −0.06694 | 0.025804 | −0.000855 | −0.011363 | 0.110131 | −0.017474 | −0.047571 |
| 43 | −4.003994 | 0.018433 | 0.045339 | −4.083497 | 0.0096 | 0.051112 | 0.000193 | −4.049749 | −4.003983 | −0.086143 | 0.027059 | −0.031198 | −4.029596 | 0.04057 |
| 44 | −0.006469 | 0.031235 | −0.006196 | −0.029925 | −0.01281 | 0.009871 | −0.002326 | 0.073315 | −0.052431 | −0.090828 | −0.048897 | −0.033017 | −0.025816 | 0.036782 |
| 45 | 0.02559 | −0.046386 | 0.01525 | −0.108028 | 0.021045 | 0.10025 | −0.037323 | 0.066747 | −0.001857 | 0.159018 | 0.026945 | −0.017915 | 0.01226 | −0.027084 |
| 46 | 0.013467 | −0.083368 | −0.050607 | −0.028413 | 0.013988 | 0.035859 | 0.058518 | −0.154302 | 0.055664 | −0.083125 | −0.016086 | 0.051441 | 0.008164 | 0.006189 |
| 47 | 0.03422 | −0.087597 | −0.004435 | −0.029552 | 0.043037 | 0.074849 | 0.009745 | 0.041156 | −0.048963 | −0.039317 | −0.004107 | 0.032527 | 0.032103 | −0.055784 |
| 48 | −0.032964 | 0.06755 | 0.029257 | 0.066253 | −0.023979 | −0.043089 | −0.021942 | 0.043019 | 0.03925 | −0.039917 | 0.017827 | 0.092789 | 0.005855 | 0.002643 |
| 49 | 0.017783 | −0.024273 | −0.062328 | 0.026092 | 0.009369 | −0.044911 | 0.064992 | 0.01653 | −0.014327 | −0.024847 | −0.037956 | 0.079463 | 0.009099 | −0.010771 |
| 50 | −0.039719 | −0.050878 | −0.069081 | 0.060413 | −0.00566 | −0.022364 | 0.017689 | 0.100291 | −0.013936 | −0.00953 | 0.016497 | −0.149479 | −0.017113 | −0.034295 |
| 51 | −0.083598 | 0.013418 | 0.026353 | −0.024095 | 0.033237 | −0.014703 | 0.01772 | −0.001281 | 0.045052 | −0.022629 | 0.07559 | 0.128755 | 0.05033 | 0.03406 |
| 52 | −0.059445 | −0.166218 | 0.14882 | −0.072875 | 0.012961 | −0.023607 | −0.039734 | 0.005063 | −0.039813 | 0.082897 | −0.017908 | 0.008147 | 0.054872 | 0.051204 |
| 53 | 0.047749 | 0.006544 | 0.100399 | 0.074768 | −0.016802 | −0.079579 | 0.015041 | 0.080239 | −0.02731 | −0.168824 | 0.014523 | −0.106669 | −0.056208 | 0.003766 |
| 54 | −0.029887 | 0.06793 | 0.187805 | 0.007517 | 0.036552 | 0.027728 | 0.024471 | −0.112712 | −0.001206 | 0.116221 | 0.009131 | −0.124993 | 0.073677 | 0.115506 |
| 55 | −0.013798 | −0.031333 | −0.023263 | −0.06009 | 0.022889 | 0.025079 | −0.011182 | −0.124995 | −0.05822 | 0.045995 | 0.008732 | 0.112679 | 0.01972 | 0.101465 |
| 56 | −0.018234 | −0.014007 | −0.021493 | −0.081569 | −0.019474 | 0.014437 | 0.023011 | −0.047338 | −0.00763 | −0.021098 | 0.032916 | 0.011156 | 0.03279 | 0.047109 |
| 57 | 0.019241 | −0.059404 | −0.104733 | 0.085036 | −0.081533 | −0.068749 | −0.015548 | −0.003904 | 0.016767 | −0.014967 | −0.060337 | −0.070307 | −0.059943 | 0.080531 |
| 58 | −0.01609 | −0.094317 | 0.043479 | 0.061902 | 0.021458 | 0.081313 | −0.00206 | 0.076953 | −0.009954 | −0.027714 | −0.015297 | 0.065673 | 0.039808 | 0.052026 |
| 59 | 0.021606 | 0.013282 | −0.069915 | 0.109058 | −0.022992 | −0.045284 | −0.045661 | −0.005622 | 0.02639 | 0.041487 | 0.051349 | 0.10467 | 0.028583 | 0.016099 |
| 60 | −0.005173 | −0.035855 | −0.011435 | 0.00855 | −0.009644 | −0.018565 | −0.002194 | −0.010397 | −0.008272 | 0.002864 | −0.015825 | 0.001126 | −0.007427 | −0.022398 |
| 61 | 0.001165 | 0.017916 | −0.003536 | 0.009765 | −0.003084 | −0.010252 | −0.009544 | −0.00328 | −0.003836 | −0.007036 | −0.006887 | 0.030368 | −0.013176 | −0.018462 |
| 62 | 0.001449 | 0.011732 | 0.047899 | −0.039952 | 0.002867 | 0.010595 | 0.010411 | −0.032377 | −0.007815 | 0.055206 | −0.000326 | −0.008343 | 0.006434 | −0.005855 |
| 63 | −0.013698 | 0.034595 | 0.003165 | −0.008662 | −0.002914 | −0.010549 | 0.008012 | −0.037827 | −0.003818 | −0.026357 | −0.006951 | 0.013901 | −0.006144 | 0.018601 |
| 64 | 0.008588 | −0.006524 | 0.009291 | 0.021811 | 0.000704 | −0.016456 | −0.001903 | −0.010676 | −0.023216 | −0.009272 | −0.001899 | −0.007582 | 0.006927 | 0.023149 |
| 65 | −0.030088 | −0.013563 | 0.00686 | −0.020567 | 0.006551 | 0.006108 | −0.001148 | 0.003204 | −0.004781 | 0.014963 | −0.003326 | −0.011003 | 0.011176 | −0.007934 |
| 66 | −0.011473 | −0.016499 | 0.005413 | −0.004382 | 0.00175 | 0.01565 | −0.003269 | −0.02299 | −0.005329 | −0.037789 | −0.008182 | 0.003229 | −0.00075 | 0.039357 |
| 67 | −0.02954 | 0.011782 | 0.030941 | −0.004979 | −0.017482 | −0.008107 | −0.013501 | −0.005331 | −0.030996 | −0.055207 | −0.014933 | −0.052192 | −0.01662 | 0.011591 |
| 68 | −0.007966 | −0.04715 | −0.033705 | −0.004507 | −0.017938 | −0.008377 | −0.019577 | 0.04006 | −0.016066 | 0.061412 | −0.00817 | −0.001548 | −0.012846 | −0.016054 |
| 69 | 0.01864 | −0.003418 | 0.015641 | −0.006395 | 0.006967 | 0.013215 | −0.012996 | 0.057452 | −0.020528 | 0.024913 | 0.018691 | 0.021706 | 0.006478 | −0.013807 |
| 70 | −0.003585 | 0.034113 | −0.01054 | −0.00386 | −0.002255 | 0.020836 | −0.002844 | 0.028268 | 0.019643 | 0.037073 | −0.004172 | −0.001028 | 0.02382 | 0.00245 |
| 71 | 0.020314 | −0.025298 | 0.005036 | 0.025311 | −0.015136 | −0.03001 | 0.008529 | 0.011566 | −0.016243 | −0.011773 | 0.017011 | −0.012906 | −0.009162 | −0.009773 |
| 72 | 0.002085 | −0.012196 | −0.031567 | 0.021915 | −0.000878 | −0.003506 | 0.006855 | 0.017032 | −0.018849 | −0.008014 | 0.009401 | 0.013034 | −0.008214 | −0.012981 |
| 73 | −0.001376 | −0.044255 | −0.01411 | 0.01735 | −0.009134 | 0.006499 | −0.015743 | −0.004284 | −0.02772 | 0.011383 | −0.027798 | 0.021211 | 0.01254 | 0.005275 |
| 74 | 0.013215 | 0.026484 | 0.033276 | 0.051253 | 0.014372 | 0.002921 | 0.017782 | 0.001222 | 0.00817 | 0.03135 | 0.016642 | −0.018636 | 0.012074 | 0.026871 |
| 75 | 0.013005 | 0.004585 | 0.008897 | 0.003776 | −0.001273 | 0.004552 | 0.006642 | 0.003839 | 0.004881 | 0.003599 | 0.000794 | 0.008279 | 0.013038 | 0.004353 |
| 76 | 0.000579 | −0.004193 | 0.060395 | −0.021162 | 0.002042 | 0.007146 | 0.007241 | −0.019123 | 0.00599 | 0.031508 | 0.008187 | −0.042942 | 0.000958 | 0.023573 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 77 | 0.01556 | 0.010627 | 0.000279 | 0.003917 | −0.005583 | 0.002145 | 0.002328 | 0.013924 | 0.004457 | 0.004295 | 0.002215 | 0.004105 | 0.007604 | 0.001889 |
| 78 | 0.023812 | 0.02049 | −0.002577 | 0.015792 | −0.008136 | −0.005497 | 0.000425 | 0.008605 | 0.010311 | 0.014806 | 0.007037 | 0.017671 | 0.015369 | 0.010046 |
| 79 | −0.01245 | −0.029894 | 0.043445 | 0.016863 | 0.002688 | 0.019179 | 0.000277 | 0.013747 | −0.005107 | 0.007754 | −0.005621 | −0.014224 | 0.01927 | 0.015341 |
| 80 | 0.005931 | 0.024531 | −0.028956 | 0.009023 | 0.021738 | 0.00096 | −0.009434 | −0.012431 | −0.003814 | −0.010255 | 0.016771 | −0.00086 | 0.044301 | 0.009547 |
| 81 | −0.014136 | 0.009836 | 0.010305 | −0.019538 | 0.002197 | −0.002198 | −0.005026 | −0.012778 | −0.004597 | 0.009021 | −0.018838 | 0.0316 | −0.021452 | −0.002511 |
| 82 | 0.007463 | −0.01686 | −0.022981 | −0.001371 | 0.0048711 | 0.017089 | 0.011116 | 0.028122 | 0.0076 | −0.0166981 | 0.0056331 | 0.0021921 | 0.011487 | −0.005047 |
| 83 | 0.016095 | 0.0087 | −0.003529 | 0.004774 | 0.000889 | 0.003466 | 0.009146 | 0.026121 | 0.014167 | 0.007595 | 0.010544 | 0.009673 | 0.009269 | −0.00691 |
| 84 | 0.011139 | 0.020948 | −0.009558 | −0.010258 | 0.00142 | 0.004709 | 0.011033 | −0.015804 | 0.009333 | −0.002028 | 0.006658 | 0.003066 | 0.007979 | −0.018373 |
| 85 | −0.035977 | 0.008091 | 0.03509 | 0.033754 | −0.020644 | −0.02351 | 0.000403 | 0.055065 | −0.006664 | −0.002207 | −0.006142 | 0.003022 | −0.033023 | 0.011311 |
| 86 | 0.021564 | 0.012753 | 0.001675 | −0.005513 | −0.025101 | −0.024975 | −0.004703 | 0.043191 | −0.010487 | 0.01983 | 0.010142 | −0.016549 | −0.030867 | −0.023691 |
| 87 | 0.027008 | 0.017844 | 0.009336 | −0.043253 | 0.011442 | −0.007617 | −0.000562 | 0.008753 | −0.024891 | 0.016497 | 0.010217 | 0.008738 | 0.015127 | −0.000662 |
| 88 | 0.026598 | 0.0067 | −0.025698 | 0.001569 | 0.000609 | −0.001476 | 0.004254 | 0.015358 | 0.007309 | −0.010277 | 0.008298 | 0.023845 | 0.013938 | −0.003605 |
| 89 | 0.024188 | 0.005422 | −0.006456 | 0.015253 | −0.004844 | −0.009655 | 0.000769 | 0.021178 | 0.005123 | 0.01558 | 0.01924 | 0.007408 | 0.009895 | −0.006523 |
| 90 | 0.010763 | 0.00033 | 0.02693 | 0.002612 | 0.002554 | 0.001338 | −0.002382 | 0.021133 | −0.017516 | 0.02334 | 0.020326 | 0.001361 | 0.011497 | −0.000974 |
| 91 | 0.011571 | 0.02007 | −0.030869 | 0.010451 | −0.001027 | 0.01786 | 0.00868 | 0.012208 | −0.004186 | −0.016832 | 0.002326 | −0.029115 | 0.003912 | −0.010362 |
| 92 | −0.008249 | 0.010172 | −0.007159 | 0.061085 | 0.003792 | −0.004024 | 0.003207 | 0.016977 | 0.026148 | −0.013451 | −0.004372 | −0.025661 | 0.008637 | −0.002009 |
| 93 | −0.014753 | −0.007302 | −0.013489 | 0.004093 | −0.010088 | 0.0067 | −0.002756 | 0.005808 | −0.007334 | −0.015816 | −0.00087 | −0.022057 | 0.002937 | −0.006774 |
| 94 | −0.008914 | 0.011905 | −0.029791 | 0.019776 | −0.003377 | 0.005956 | 0.018562 | −0.011196 | 0.015426 | 0.013982 | 0.001548 | −0.010967 | 0.01345 | 0.014976 |
| 95 | −0.034717 | 0.005858 | 0.02885 | 0.031631 | 0.016331 | 0.039431 | 0.016187 | 0.000694 | 0.002945 | 0.047581 | 0.015864 | 0.043336 | 0.016305 | 0.002856 |
| 96 | −0.030252 | 0.028231 | 0.043677 | 0.090435 | −0.018466 | −0.011296 | 0.002606 | 0.030081 | 0.01627 | −0.044843 | −0.011646 | 0.036553 | −0.005981 | 0.001521 |
| 97 | −0.021928 | 0.020048 | 0.001208 | 0.011145 | 0.000878 | −0.030003 | −0.004762 | −0.018258 | −0.01123 | 0.000018 | −0.025612 | 0.012952 | 0.001395 | 0.006749 |
| 98 | 0.004643 | −0.011405 | 0.006958 | −0.014186 | 0.02117 | 0.011553 | 0.004209 | −0.017829 | −0.010887 | 0.005645 | 0.005463 | −0.013366 | 0.007185 | 0.012901 |
| 99 | −0.030259 | 0.008248 | 0.011802 | 0.04155 | −0.010598 | −0.030901 | −0.007257 | 0.049528 | −0.013562 | −0.001481 | −0.01925 | −0.001069 | −0.017042 | −0.01527 |
| 100 | −0.028544 | 0.00688 | 0.030833 | 0.013414 | 0.003803 | −0.016692 | 0.006846 | 0.012331 | 0.00215 | −0.007511 | 0.002897 | 0.019277 | −0.003833 | 0.004225 |
| 101 | 0.011749 | −0.005223 | −0.000596 | 0.005632 | 0.004067 | −0.001143 | 0.005443 | −0.045139 | −0.013735 | 0.015807 | −0.009656 | −0.027027 | −0.00167 | 0.017105 |
| 102 | −0.03289 | 0.077498 | 0.000393 | 0.010172 | −0.010336 | −0.006038 | −0.007251 | −0.024514 | 0.003583 | −0.015955 | −0.018233 | 0.072478 | −0.01683 | −0.036468 |
| 103 | 0.002255 | 0.038793 | −0.034894 | 0.028803 | −0.004314 | −0.005108 | 0.008701 | 0.003694 | 0.004118 | −0.043952 | −0.010386 | 0.066259 | −0.005136 | −0.033153 |
| 104 | −0.026711 | 0.034972 | 0.063638 | 0.012137 | 0.013483 | 0.016741 | 0.010802 | −0.016018 | −0.005798 | 0.001277 | 0.003955 | 0.027576 | 0.017761 | 0.00302 |
| 105 | 0.025605 | −0.039956 | −0.021899 | −0.073932 | −0.005169 | −0.034656 | −0.020763 | 0.012637 | −0.000162 | 0.035187 | −0.006072 | 0.049356 | 0.010071 | −0.016034 |
| 106 | 0.015839 | 0.003639 | −0.019614 | −0.032691 | −0.013803 | −0.005291 | −0.004005 | −0.079096 | 0.004737 | −0.056618 | −0.016431 | −0.013769 | −0.003891 | 0.017548 |
| 107 | −0.005411 | −0.021814 | −0.018778 | 0.020409 | −0.014577 | −0.040769 | −0.002882 | −0.004708 | −0.010648 | −0.014255 | −0.007649 | 0.004678 | −0.012678 | 0.029205 |
| 108 | 0.002532 | 0.007615 | −0.005652 | 0.061953 | 0.001384 | −0.007541 | 0.002519 | −0.001965 | 0.00705 | −0.002695 | 0.00598 | −0.062587 | 0.003073 | −0.020966 |
| 109 | 0.017987 | 0.0289 | 0.038112 | 0.058856 | −0.003401 | −0.008746 | 0.004223 | −0.030671 | 0.001767 | 0.022381 | −0.007245 | 0.081675 | −0.007498 | −0.013572 |
| 110 | −0.03755 | 0.035381 | −0.004042 | 0.088263 | −0.002053 | −0.024209 | 0.027565 | 0.021899 | 0.022621 | −0.064332 | 0.002187 | 0.005321 | −0.008376 | −0.022672 |
| 111 | −0.005526 | −0.001863 | 0.054725 | 0.014215 | 0.017871 | 0.032264 | −0.012717 | −0.037934 | −0.003189 | 0.027867 | −0.007802 | −0.016485 | 0.020245 | −0.016944 |
| 112 | −0.010192 | 0.060204 | 0.040951 | 0.001132 | −0.010155 | 0.030652 | −0.019785 | −0.016603 | −0.009092 | −0.027468 | 0.008922 | −0.016715 | −0.011972 | −0.017605 |
| 113 | −0.012571 | −0.043481 | 0.027246 | 0.065971 | 0.011058 | 0.018079 | −0.01293 | −0.020683 | −0.006253 | 0.018197 | −0.001103 | 0.003374 | 0.012383 | 0.039402 |
| 114 | −0.007277 | 0.01509 | 0.015449 | 0.028952 | 0.004186 | −0.005003 | −0.011564 | 0.127605 | 0.00387 | 0.025575 | 0.024618 | −0.025964 | 0.001288 | 0.046129 |
| 115 | −0.038655 | 0.016615 | 0.001636 | −0.011571 | −0.022505 | −0.002317 | 0.021054 | 0.019136 | 0.010095 | 0.021387 | −0.022494 | −0.086441 | −0.023916 | 0.001298 |
| 116 | 0.024193 | −0.013023 | −0.030884 | 0.023049 | 0.000868 | 0.003156 | −0.035266 | −0.044948 | −0.025517 | −0.011394 | −0.016922 | 0.02132 | 0.007736 | −0.030289 |
| 117 | −0.033429 | 0.001853 | 0.060187 | −0.010808 | 0.015004 | 0.020337 | 0.017877 | −0.028283 | 0.007288 | −0.083017 | −0.004873 | 0.01377 | −0.003512 | −0.035884 |
| 118 | −0.042246 | −0.000041 | 0.01646 | 0.033497 | 0.007217 | −0.01908 | 0.011729 | 0.056544 | −0.015276 | 0.00965 | −0.006285 | −0.076812 | 0.016044 | 0.011977 |
| 119 | −0.009142 | −0.004816 | −0.031314 | 0.003433 | −0.009333 | −0.012495 | −0.007615 | −0.013827 | −0.023242 | −0.023579 | 0.00733 | −0.008241 | −0.002732 | −0.001934 |
| 120 | 0.000724 | −0.031049 | −0.00058 | −0.011604 | −0.002707 | 0.005535 | −0.013583 | −0.048671 | −0.010242 | −0.039299 | −0.012376 | −0.019811 | −0.002861 | −0.012256 |
| 121 | 0.000112 | 0.032906 | −0.010582 | −0.038042 | 0.011531 | 0.023548 | −0.014938 | 0.068236 | 0.016888 | 0.064557 | 0.012403 | 0.021626 | 0.016695 | −0.041352 |
| 122 | 0.008183 | 0.017013 | −0.025679 | 0.000036 | 0.009149 | 0.019453 | 0.004181 | −0.004219 | 0.021771 | 0.019403 | −0.019234 | 0.021931 | 0.003979 | 0.002094 |
| 123 | −0.001363 | −0.017342 | −0.028595 | 0.005176 | −0.01239 | −0.003863 | −0.008372 | 0.013086 | −0.000528 | 0.015503 | −0.003427 | 0.008011 | −0.010405 | −0.00078 |
| 124 | −0.013924 | 0.015194 | −0.007991 | 0.003786 | −0.000454 | −0.010552 | −0.007528 | −0.034534 | −0.015581 | −0.020646 | 0.007559 | −0.010013 | 0.003029 | 0.004336 |
| 125 | −0.013293 | −0.017253 | 0.034841 | −0.000539 | 0.005144 | −0.001391 | −0.002072 | −0.004156 | −0.023897 | −0.024456 | 0.010132 | −0.056363 | −0.01766 | −0.003422 |
| 126 | 0.005979 | −0.010572 | −0.012468 | 0.001883 | 0.026029 | 0.004645 | 0.006312 | 0.038459 | 0.01306 | 0.019841 | 0.022041 | 0.003967 | 0.029007 | −0.009954 |

APPENDIX B3-continued

PCA Transformation
Matrix (340 × 340 Early/Late)

| | | | | | | | | | | | | | |
|---|---|---|---|---|---|---|---|---|---|---|---|---|---|
| 127 | 0.002433 | −0.010908 | −0.00506 | 0.003444 | 0.015231 | −0.001107 | 0.009235 | 0.028419 | 0.00327 | 0.007378 | 0.015396 | −0.013757 | 0.015915 | 0.002371 |
| 128 | −0.012418 | 0.008449 | −0.002389 | 0.00374 | 0.00369 | 0.004888 | 0.015967 | 0.025585 | 0.013485 | −0.028406 | 0.015755 | 0.002122 | 0.00338 | 0.000611 |
| 129 | 0.007742 | 0.021165 | 0.047588 | 0.005218 | −0.020655 | −0.033272 | −0.020663 | 0.034006 | 0.002301 | −0.037556 | 0.006058 | 0.038866 | 0.003048 | 0.002804 |
| 130 | 0.015012 | 0.037069 | 0.007804 | 0.00331 | −0.029193 | 0.0005 | 0.017935 | 0.004945 | 0.029206 | 0.029557 | −0.004912 | −0.025973 | −0.006128 | 0.005717 |
| 131 | −0.002634 | −0.048459 | −0.057888 | −0.025255 | 0.015412 | −0.018475 | −0.004096 | 0.016055 | −0.019716 | −0.017146 | −0.008483 | 0.051468 | 0.039416 | 0.021384 |
| 132 | 0.006584 | −0.011052 | 0.019003 | 0.011615 | 0.013249 | 0.011102 | 0.013033 | 0.02399 | 0.00475 | −0.036557 | 0.025332 | 0.001538 | 0.003564 | −0.020061 |
| 133 | −0.039284 | −0.008254 | 0.028284 | −0.019513 | 0.007599 | −0.00893 | 0.033908 | −0.015858 | −0.023954 | −0.029468 | −0.006861 | 0.018178 | 0.010827 | 0.014606 |
| 134 | 0.00672 | 0.038793 | −0.072027 | −0.003273 | 0.004807 | 0.058266 | −0.014111 | 0.018474 | 0.009352 | 0.047045 | 0.017204 | 0.03198 | 0.02171 | −0.006466 |
| 135 | 0.017762 | 0.004235 | 0.010115 | 0.009626 | −0.008603 | 0.001307 | −0.004489 | −0.043245 | −0.008195 | −0.022338 | 0.009798 | −0.0053911 | 0.004719 | 0.017821 |
| 136 | −0.003226 | −0.018602 | −0.002438 | −0.006126 | −0.00872 | −0.005475 | −0.004093 | 0.016903 | −0.021095 | −0.019442 | −0.017346 | −0.023309 | −0.005636 | 0.002268 |
| 137 | 0.011275 | −0.012005 | −0.003714 | −0.010856 | 0.006029 | 0.000419 | 0.00132 | −0.023189 | −0.005803 | 0.011655 | 0.014219 | −0.01615 | 0.00245 | 0.039465 |
| 138 | 0.060985 | −0.007452 | 0.012742 | 0.062213 | 0.006987 | −0.022601 | 0.004263 | 0.029132 | 0.021283 | 0.018004 | 0.005708 | −0.041074 | 0.001428 | −0.030911 |
| 139 | −0.021144 | −0.06111 | −0.072194 | 0.03992 | −0.018995 | 0.004225 | −0.031852 | −0.046458 | 0.008669 | −0.008199 | −0.01332 | 0.018888 | −0.00578 | −0.033614 |
| 140 | 0.046104 | 0.01614 | −0.035506 | −0.094583 | −0.003672 | 0.028229 | 0.003481 | 0.02172 | −0.017684 | −0.036076 | −0.009062 | −0.037515 | −0.027814 | −0.044829 |
| 141 | 0.012358 | 0.008924 | −0.044594 | 0.014629 | −0.025081 | −0.029371 | 0.003265 | 0.011407 | 0.031595 | −0.010311 | 0.00579 | 0.011793 | −0.025308 | −0.042946 |
| 142 | 0.003583 | 0.026244 | 0.031396 | 0.007745 | −0.005373 | 0.001867 | −0.003901 | −0.021326 | 0.018185 | 0.042367 | −0.005247 | 0.025581 | −0.009815 | −0.002621 |
| 143 | 0.002508 | 0.014484 | −0.013057 | −0.013086 | −0.00171 | 0.025016 | 0.002941 | −0.043329 | 0.011787 | 0.022371 | −0.018482 | 0.031578 | −0.004723 | 0.022443 |
| 144 | 0.023855 | −0.013043 | −0.058802 | 0.000168 | −0.02037 | −0.004675 | −0.023101 | −0.035332 | −0.017102 | 0.003888 | −0.008802 | 0.036183 | −0.011258 | −0.000773 |
| 145 | −0.013549 | −0.023398 | −0.007794 | −0.004846 | 0.012392 | 0.039233 | −0.001369 | 0.004005 | −0.035238 | 0.001281 | −0.016013 | 0.009024 | 0.015647 | 0.034671 |
| 146 | 0.001635 | −0.014717 | 0.005414 | −0.024108 | 0.005494 | 0.009152 | −0.012397 | −0.029345 | −0.018968 | −0.047996 | 0.011309 | −0.007615 | 0.004438 | −0.00194 |
| 147 | −0.015417 | −0.070601 | 0.012591 | −0.013795 | 0.005171 | −0.007257 | 0.000462 | −0.040938 | 0.017841 | −0.017898 | 0.022898 | 0.027366 | 0.012991 | 0.012618 |
| 148 | 0.008676 | −0.017583 | 0.03531 | 0.012364 | −0.014097 | −0.020331 | −0.004484 | −0.031988 | −0.005028 | −0.038934 | −0.024022 | −0.034245 | −0.008498 | 0.043816 |
| 149 | 0.001127 | 0.006224 | −0.024236 | −0.00579 | −0.003151 | 0.02516 | 0.009328 | 0.024092 | 0.016615 | 0.032014 | −0.016183 | 0.022458 | 0.001314 | 0.020621 |
| 150 | −0.003297 | 0.003273 | 0.033202 | 0.014499 | 0.007397 | 0.004769 | −0.021799 | −0.016873 | −0.019364 | −0.038229 | 0.001403 | −0.064384 | 0.008344 | 0.005109 |
| 151 | −0.02931 | −0.043936 | −0.085421 | 0.037128 | −0.021298 | −0.005323 | −0.001599 | −0.015275 | 0.021717 | −0.035736 | −0.011392 | 0.039073 | 0.008354 | 0.025521 |
| 152 | 0.01124 | −0.000629 | −0.016455 | 0.013527 | −0.009817 | 0.003582 | −0.010601 | 0.049076 | 0.001301 | 0.016393 | 0.00825 | −0.022479 | −0.009734 | −0.007556 |
| 153 | −0.018253 | 0.009488 | −0.02698 | 0.031309 | −0.02452 | −0.036856 | −0.009875 | 0.00714 | 0.0071 | −0.010965 | 0.00552 | 0.008991 | −0.029502 | −0.041192 |
| 154 | 0.005266 | 0.014142 | −0.006784 | −0.027639 | 0.001625 | 0.017865 | −0.006265 | −0.066728 | −0.005467 | 0.014267 | −0.008611 | 0.024874 | 0.014832 | −0.003632 |
| 155 | 0.030855 | 0.015135 | 0.017913 | −0.055302 | 0.011685 | 0.016331 | −0.028589 | 0.027331 | −0.034753 | 0.023063 | 0.009935 | −0.029776 | 0.013111 | −0.022183 |
| 156 | −0.014401 | 0.016089 | −0.030675 | 0.015957 | −0.009784 | −0.008137 | 0.016581 | −0.037618 | 0.006953 | 0.019503 | −0.004887 | 0.025286 | 0.009522 | 0.000169 |
| 157 | −0.002455 | −0.000444 | 0.04358 | −0.01074 | 0.007277 | 0.010193 | 0.000935 | −0.038523 | −0.008859 | −0.053489 | −0.002167 | −0.017967 | −0.007949 | −0.012409 |
| 158 | −0.009998 | 0.039904 | −0.010949 | −0.014549 | −0.010332 | −0.041815 | 0.005861 | −0.053981 | 0.009888 | 0.049036 | 0.006099 | −0.051184 | −0.003582 | −0.015885 |
| 159 | 0.008395 | 0.003747 | 0.026027 | 0.031409 | −0.003578 | 0.001317 | −0.027881 | −0.019483 | −0.008053 | −0.029845 | −0.002335 | 0.008644 | 0.016336 | 0.004497 |
| 160 | −0.059515 | 0.012731 | 0.02387 | 0.028586 | −0.014768 | −0.016586 | 0.036923 | −0.067732 | 0.034731 | 0.017505 | 0.001969 | −0.026528 | −0.006211 | 0.049587 |
| 161 | 0.009514 | −0.018082 | 0.031488 | 0.033245 | −0.020065 | −0.011216 | −0.019884 | −0.006304 | 0.019276 | 0.04351 | 0.017937 | 0.023094 | −0.016423 | 0.011183 |
| 162 | 0.014579 | −0.005746 | −0.043534 | -4.031796 | 0.005622 | 0.031223 | −0.003536 | −0.057012 | −0.011041 | −0.027621 | −0.008192 | −0.012639 | 0.003263 | −0.012139 |
| 163 | −0.002587 | 0.0218 | 0.038268 | −0.011665 | 0.006985 | 0.019548 | 0.011021 | −0.026308 | 0.013945 | 0.036373 | 0.011688 | −0.014178 | 0.001532 | 0.026822 |
| 164 | −0.016385 | −0.02322 | −0.024722 | −0.014415 | 0.002536 | −0.017824 | 0.008179 | 0.008966 | −0.019827 | −0.03604 | −0.019521 | 0.02149 | 0.003369 | 0.000758 |
| 165 | −0.022452 | −0.030471 | 0.026969 | −0.069577 | −0.001577 | 0.018759 | −0.018423 | 0.026717 | 0.003583 | 0.02719 | −0.004803 | −0.037512 | −0.000662 | 0.004622 |
| 166 | 0.05406 | 0.025189 | 0.013255 | 0.051491 | −0.007818 | −0.017051 | 0.009065 | −0.071984 | 0.019542 | −0.057378 | −0.004259 | 0.031694 | −0.004522 | −0.022993 |
| 167 | 0.012558 | −0.041648 | −0.02093 | 0.000038 | 0.020351 | 0.027843 | −0.002439 | 0.021386 | −0.02162 | 0.045807 | 0.014423 | −0.009315 | 0.009062 | −0.009379 |
| 168 | −0.032757 | −0.017148 | −0.049616 | −0.012935 | −0.006686 | −0.042549 | 0.020484 | 0.038197 | 0.015035 | 0.012684 | −0.005767 | −0.005586 | −0.011871 | 0.03339 |
| 169 | 0.021186 | −0.018261 | −0.000037 | −0.003244 | −0.002294 | −0.016299 | 0.002928 | −0.030289 | −0.006473 | −0.026101 | 0.00153 | −0.023095 | −0.000456 | 0.013976 |
| 170 | 0.008873 | −0.002958 | −0.011063 | −0.011535 | −0.015713 | −0.023918 | 0.004527 | −0.019545 | −0.00518 | −0.037985 | −0.00514 | −0.045043 | −0.010667 | 0.01329 |
| 171 | 0.023889 | −0.020281 | −0.024762 | 0.00614 | −0.011812 | −0.025396 | −0.005897 | 0.043967 | 0.011888 | 0.009237 | 0.014072 | −0.020797 | −0.00595 | −0.009255 |
| 172 | −0.011093 | −0.01241 | −0.027544 | 0.010279 | −0.002155 | −0.01098 | −0.012614 | −0.018741 | −0.004677 | −0.035471 | 0.010259 | −0.016095 | −0.002851 | 0.007592 |
| 173 | −0.016804 | −0.012582 | 0.003921 | −0.00358 | −0.000447 | 0.015516 | −0.007105 | 0.003922 | −0.007229 | −0.002893 | −0.001286 | −0.008161 | −0.015412 | 0.001441 |
| 174 | 0.010481 | −0.004768 | −0.015314 | −0.000165 | 0.006778 | 0.028386 | 0.000934 | −0.021818 | 0.008258 | 0.029338 | 0.01016 | −0.01478 | 0.000806 | 0.028844 |
| 175 | −0.001735 | −0.021616 | 0.002511 | −0.008516 | 0.002578 | 0.041899 | −0.029556 | −0.014276 | 0.015096 | 0.010524 | −0.002561 | −0.034604 | 0.001482 | 0.030025 |
| 176 | −0.010087 | −0.03351 | 0.016843 | 0.049341 | −0.008555 | −0.021194 | 0.008957 | 0.004781 | 0.011426 | −0.021161 | −0.0068751 | −0.025377 | −0.017852 | −0.005956 |

APPENDIX B3-continued

PCA Transformation
Matrix (340 × 340 Early/Late)

| | | | | | | | | | | | | | |
|---|---|---|---|---|---|---|---|---|---|---|---|---|---|
| 177 | −0.00675 | −0.005909 | −0.035198 | −0.041539 | 0.002231 | −0.01718 | 0.008161 | −0.060379 | −0.018163 | 0.016738 | 0.01252 | −0.015071 | 0.033385 | −0.012729 |
| 178 | 0.00216 | −0.03078 | −0.007357 | −0.040033 | 0.016259 | −0.002751 | −0.005743 | −0.033251 | −0.008602 | −0.012138 | 0.014299 | −0.01195 | 0.007184 | 0.007893 |
| 179 | 0.015004 | −0.015364 | 0.001029 | −4.015528 | 0.014158 | −4.01207 | 0.00078 | 0.015859 | −4.008684 | 0.016546 | 0.005358 | −4.020755 | 0.000892 | −4.004242 |
| 180 | 0.015741 | −0.011683 | −0.009297 | 0.001969 | 0.005855 | −0.012658 | 0.00212 | 0.004553 | −0.005058 | −0.000062 | 0.001806 | −0.018825 | −0.006405 | −0.006317 |
| 181 | 0.006003 | −0.008606 | −0.000672 | −0.004755 | 0.012513 | −0.002349 | 0.004174 | −0.004733 | −0.008298 | −0.003334 | 0.004172 | −0.017749 | −0.004295 | −0.008644 |
| 182 | −0.015214 | 0.005179 | −0.001063 | 0.002825 | −0.003205 | −0.023133 | 0.000757 | 0.021571 | −0.005021 | −0.003604 | −0.005743 | −0.022527 | −0.011916 | −0.014337 |
| 183 | 0.001551 | −0.001988 | 0.006795 | 0.003479 | 0.007278 | −0.02508 | −0.010631 | 0.065175 | −0.001689 | 0.03142 | 0.01837 | −0.001079 | 0.006558 | −0.023334 |
| 184 | 0.030052 | 0.004461 | 0.019885 | 0.036812 | −0.000715 | 0.009924 | −0.008148 | 0.045501 | 0.015694 | 0.043379 | 0.029316 | 0.009154 | −0.002272 | 0.011463 |
| 185 | −0.003661 | 0.028625 | 0.015287 | 0.074476 | −0.000465 | 0.004788 | −0.004239 | −0.0125 | 0.010718 | −0.033516 | −0.0092371 | 0.0087561 | −0.0193181 | −0.012585 |
| 186 | −0.008882 | 0.021865 | −0.009695 | 0.008514 | −0.006022 | 0.01533 | −0.003814 | 0.028927 | 0.021534 | −0.037597 | −0.0008181 | 0.0360571 | −0.0068531 | 0.002149 |
| 187 | −0.008403 | 0.026873 | 0.000549 | −0.013817 | 0.006641 | −0.000379 | 0.001782 | −0.003398 | −0.004613 | −0.004336 | −0.001286 | 0.00858 | −0.001798 | 0.001892 |
| 188 | 0.004413 | 0.02945 | −0.023802 | −0.000066 | −0.002615 | −0.006078 | −0.000777 | −0.021265 | 0.002989 | 0.005533 | −0.002755 | −0.0017 | −0.006031 | 0.002328 |
| 189 | 0.007079 | 0.032535 | 0.013756 | 0.018925 | −0.004837 | −0.00725 | −0.006918 | −0.027729 | 0.019825 | 0.040241 | −0.008161 | −0.020911 | −0.007083 | 0.000575 |
| 190 | 0.002388 | −0.036855 | −0.028582 | 0.017769 | −0.011429 | −0.0016161 | −0.00081 | 0.011001 | 0.000618 | 0.001948 | −0.010556 | −0.013398 | −0.012099 | −0.004281 |
| 191 | 0.00995 | −0.000751 | −0.004719 | −0.022931 | −0.006663 | −0.001852 | 0.008359 | −0.0165 | −0.003453 | −0.005259 | −0.008916 | 0.004301 | −0.005749 | −0.010137 |
| 192 | 0.000483 | 0.025342 | −0.060023 | −0.059645 | 0.030355 | 0.022911 | −0.004387 | 0.025661 | −0.005268 | 0.009132 | 0.011774 | 0.050073 | 0.030018 | −0.003334 |
| 193 | −0.016756 | −0.013419 | −0.035896 | −0.001333 | −0.003297 | −0.004125 | −0.004343 | 0.006877 | 0.00199 | −0.021968 | 0.006397 | 0.045511 | −0.015198 | 0.008308 |
| 194 | 0.017915 | −0.028486 | −0.045738 | 0.00028 | −0.012262 | −0.036744 | −0.008135 | 0.005631 | 0.003603 | −0.017381 | −0.011684 | −0.008991 | −0.020696 | −0.020632 |
| 195 | −0.00705 | 0.009959 | 0.030555 | 0.003702 | 0.015724 | 0.028121 | −0.004406 | 0.009135 | −0.009208 | 0.011626 | 0.003007 | −0.002014 | 0.009253 | 0.014384 |
| 196 | 0.00604 | 0.009897 | −0.005557 | 0.001968 | 0.011248 | 0.046029 | −0.009725 | −0.008714 | −0.002854 | 0.010279 | −0.005354 | −0.003042 | 0.005635 | 0.013942 |
| 197 | −0.021238 | −0.007009 | −0.0231 | −0.005058 | −0.007245 | 0.023599 | 0.007646 | 0.028445 | −0.005858 | −0.002222 | −0.013383 | 0.004183 | −0.000615 | 0.004307 |
| 198 | −0.020963 | 0.024136 | 0.029858 | −0.029261 | 0.003726 | −0.008505 | −0.008198 | 0.001048 | −0.000972 | −0.021891 | 0.016919 | −0.054567 | 0.010746 | 0.000499 |
| 199 | 0.086634 | −0.036375 | −0.01033 | −0.03655 | 0.008503 | −0.016361 | 0.022038 | −0.001714 | 0.058622 | 0.092073 | −0.003519 | 0.041982 | 0.010068 | 0.044378 |
| 200 | −0.009557 | 0.004243 | −0.021595 | −0.011994 | 0.011354 | −0.034797 | −0.00421 | 0.023255 | −0.00595 | −0.016364 | 0.042179 | 0.009231 | 0.019747 | −0.003003 |
| 201 | −0.007984 | −0.021333 | −0.004426 | 0.025966 | −0.004016 | −0.045833 | 0.001103 | −0.003362 | −0.017018 | −0.030673 | −0.023804 | −0.005809 | −0.006671 | −0.0223 |
| 202 | −0.026876 | 0.00874 | −0.026652 | −0.041192 | −0.00002 | 0.011306 | −0.003836 | 0.007247 | 0.00432 | −0.053328 | 0.009252 | −0.010489 | 0.015938 | 0.022295 |
| 203 | −0.008888 | −0.064106 | −0.02047 | 0.071343 | −0.000508 | −0.021631 | 0.001129 | 0.014316 | 0.004306 | 0.031933 | −0.000454 | 0.001609 | 0.025304 | −0.00096 |
| 204 | −0.01292 | −0.049449 | 0.011311 | 0.057543 | 0.019553 | 0.038837 | −0.014038 | −0.011511 | −0.014919 | −0.113085 | −0.004986 | 0.008573 | −0.001629 | −0.0074 |
| 205 | 0.035934 | −0.0263 | −0.042915 | 0.060171 | −0.00939 | 0.002972 | 0.011814 | 0.017233 | 0.0097 | −0.021608 | −0.003655 | −0.023813 | −0.040145 | −0.062302 |
| 206 | −0.052787 | −0.011387 | −0.031285 | 0.041267 | 0.003949 | −0.011738 | 0.01014 | 0.040655 | −0.002281 | 0.01506 | 0.023999 | −0.035232 | −0.000751 | 0.020503 |
| 207 | −0.074125 | 0.017457 | 0.00363 | 0.000285 | 0.035641 | 0.045425 | −0.001791 | −0.013112 | 0.012658 | −0.004899 | 0.016134 | −0.032271 | 0.024208 | 0.019403 |
| 208 | −0.02119 | 0.011484 | 0.027224 | 0.062403 | −0.0213 | −0.017023 | 0.023553 | 0.040504 | −0.004852 | −0.044412 | 0.006813 | −0.028187 | 0.011686 | −0.020252 |
| 209 | 0.031557 | 0.005924 | −0.008417 | 0.033162 | 0.001201 | 0.001436 | 0.009355 | 0.018985 | 0.02875 | −0.041724 | 0.011506 | 0.034892 | 0.018068 | −0.008889 |
| 210 | 0.036742 | 0.006648 | 0.072741 | 0.021305 | 0.023067 | 0.007133 | −0.010737 | 0.05486 | −0.010932 | −0.035256 | 0.017532 | 0.074164 | 0.0349 | −0.004964 |
| 211 | 0.03935 | 0.058038 | −0.050456 | 0.020715 | 0.006531 | −0.001099 | −0.006773 | 0.006719 | −0.02377 | −0.080509 | −0.009651 | 0.017046 | 0.000621 | −0.00612 |
| 212 | 0.000835 | 0.044891 | 0.021149 | 0.018117 | −0.000738 | 0.002718 | −0.004701 | −0.042732 | −0.029658 | 0.001129 | −0.001427 | 0.007158 | −0.007296 | 0.014291 |
| 213 | 0.003118 | 0.004655 | 0.014229 | −0.029848 | −0.009916 | −0.025557 | −0.018 | −0.012537 | −0.02774 | 0.010975 | −0.018016 | 0.017048 | −0.034827 | −0.019106 |
| 214 | 0.011808 | 0.015921 | 0.01473 | 0.000943 | 0.012183 | −0.007658 | −0.000141 | 0.008335 | −0.001283 | −0.000011 | 0.013727 | −4.007607 | 0.006542 | 0.000361 |
| 215 | 0.008295 | −0.02163 | 0.060512 | 0.071105 | 0.004773 | −0.026668 | 0.006737 | −0.032577 | −0.012514 | −0.032867 | 0.012896 | 0.006941 | 0.004534 | 0.036588 |
| 216 | 0.006469 | −0.004023 | −0.022957 | 0.006291 | −0.007073 | −0.009377 | 0.009872 | 0.003555 | 0.010348 | 0.017053 | −0.005021 | −0.014158 | 0.005552 | 0.023243 |
| 217 | 0.015724 | −0.023585 | 0.003101 | 0.007502 | −0.000182 | −0.02173 | 0.005167 | 0.034507 | 0.001397 | −0.032819 | 0.00086 | −0.01361 | 0.008403 | 0.007961 |
| 218 | 0.008249 | −0.010744 | 0.014466 | 0.025412 | −0.008119 | 0.012778 | −0.004235 | −0.016416 | −0.00897 | −0.038837 | −0.007116 | 0.003044 | −0.004631 | 0.016713 |
| 219 | 0.004749 | 0.009855 | 0.039235 | −0.007833 | −0.009718 | 0.013064 | −0.00631 | −0.013848 | −0.00392 | 0.014382 | 0.001304 | −4.000495 | 0.004472 | 0.012343 |
| 220 | 0.014185 | −0.006545 | 0.025018 | −0.003613 | 0.008365 | −0.011961 | 0.010947 | −0.02301 | −0.009882 | −0.006176 | 0.006816 | −0.021979 | 0.012064 | 0.004511 |
| 221 | −0.027197 | −0.001819 | 0.023797 | −0.003639 | 0.012834 | 0.028766 | 0.000479 | 0.004566 | −0.006109 | 0.00949 | 0.000029 | −0.018157 | 0.00812 | −0.014688 |
| 222 | 0.00448 | 0.009961 | 0.007584 | −0.025046 | 0.004964 | 0.019324 | −0.00589 | −0.010201 | −0.009586 | 0.02682 | 0.002125 | 0.00637 | 0.006454 | −0.012307 |
| 223 | −0.008573 | −0.006278 | −0.001761 | −0.008488 | −0.003438 | 0.007269 | −0.004592 | −0.008847 | −0.003632 | −0.000083 | −0.009384 | 0.01407 | −0.016804 | −0.028002 |
| 224 | 0.010222 | −0.011737 | −0.024519 | 0.025679 | 0.007662 | −0.013871 | 0.005539 | −0.003512 | 0.003315 | 0.014801 | −0.002018 | −0.029774 | 0.019745 | 0.016775 |
| 225 | 0.009593 | −0.011091 | −0.025513 | 0.001067 | 0.008969 | −0.016257 | 0.001788 | −0.00609 | −0.003689 | 0.033477 | −0.004562 | −0.03223 | 0.025262 | 0.010966 |
| 226 | −0.016319 | 0.023246 | 0.016405 | −0.012777 | −0.01186 | 0.008547 | −0.01698 | −0.020976 | −0.005408 | 0.034382 | −0.014562 | 0.038917 | −0.004817 | −0.014334 |

APPENDIX B3-continued

PCA Transformation
Matrix (340 × 340 Early/Late)

| | | | | | | | | | | | | | |
|---|---|---|---|---|---|---|---|---|---|---|---|---|---|
| 227 | −0.009708 | −0.03034 | −0.005259 | 0.017385 | −0.013565 | −0.030551 | −0.014455 | −0.005584 | −0.019966 | 0.038113 | −0.011759 | −0.013483 | −0.005472 | −0.001856 |
| 228 | −0.025342 | 0.036243 | −0.0379 | −0.03377 | −0.008215 | 0.014482 | −0.00586 | −0.00263 | 0.014389 | 0.000858 | −0.007147 | −0.01705 | 0.001457 | 0.005442 |
| 229 | −0.011911 | 0.02327 | −0.003726 | −0.030493 | 0.02835 | 0.024285 | −0.001997 | −0.053328 | −0.007105 | −0.003078 | 0.017805 | 0.023425 | 0.014873 | 0.016025 |
| 230 | −0.001403 | −0.000157 | −0.04043 | −0.004172 | 0.004049 | −0.014978 | −0.003605 | −0.037635 | 0.001372 | 0.009008 | 0.014053 | 0.008929 | −0.002564 | 0.012996 |
| 231 | −0.009583 | −0.013264 | −0.031041 | 0.045267 | −0.022351 | −0.011084 | 0.003622 | −0.004328 | 0.015203 | −0.002064 | −0.014843 | 0.038164 | −0.025043 | −0.012237 |
| 232 | 0.00806 | 0.045939 | −0.012717 | −0.03092 | 0.014334 | 0.026368 | 0.004967 | −0.039646 | 0.024218 | 0.013774 | 0.006239 | −0.01536 | 0.011216 | 0.000585 |
| 233 | 0.015706 | 0.031386 | 0.001786 | −0.043158 | 0.020925 | 0.007968 | −0.005719 | −0.026127 | 0.000776 | 0.001995 | 0.006164 | 0.01124 | 0.01777 | 0.003936 |
| 234 | −0.014605 | 0.019125 | 0.003575 | −0.030273 | −0.003046 | 0.013037 | 0.001303 | −0.004039 | −0.008964 | 0.020805 | −0.000193 | −0.0171011 | −0.004757 | 0.008773 |
| 235 | 0.003449 | 0.000891 | −0.019353 | −0.009129 | −0.007036 | −0.003788 | −0.001462 | −0.039181 | −0.003389 | −0.001319 | −0.002593 | −0.000073 | −0.012919 | 0.001162 |
| 236 | 0.011377 | −0.004804 | −0.004745 | 0.037034 | −0.009153 | −0.005899 | −0.002924 | 0.026996 | 0.017067 | −0.000492 | 0.003656 | 0.004972 | −0.015422 | −0.018694 |
| 237 | 0.011344 | −0.029758 | −0.021089 | 0.006297 | −0.00658 | 0.010115 | 0.001964 | 0.008923 | −0.002129 | −0.017395 | −0.012076 | −0.015956 | 0.002553 | −0.018095 |
| 238 | 0.014203 | −0.00343 | −0.016016 | −0.013258 | −0.003776 | 0.015676 | 0.006448 | 0.014005 | 0.005738 | 0.016213 | 0.005184 | −0.001704 | 0.008267 | 0.008867 |
| 239 | 0.003883 | 0.008346 | 0.008758 | −0.015309 | 0.000855 | 0.023597 | 0.004835 | 0.014851 | 0.013792 | 0.014654 | 0.010375 | 0.016586 | 0.006478 | 0.02015 |
| 240 | 0.028421 | −0.019197 | −0.013136 | −0.001827 | 0.012978 | 0.022416 | 0.002779 | 0.008893 | 0.010463 | −0.009882 | 0.000624 | 0.026365 | 0.009118 | 0.003036 |
| 241 | 0.03628 | 0.018722 | −0.013525 | −0.013771 | 0.022112 | 0.023333 | −0.009824 | −0.009906 | −0.001991 | −0.018476 | 0.000352 | 0.029377 | 0.024237 | 0.012426 |
| 242 | 0.005907 | −0.002888 | −0.021463 | −0.011458 | −0.005133 | −0.003453 | −0.000016 | −0.039236 | 0.005115 | −0.004295 | −0.007337 | −0.018239 | −0.009019 | −0.008203 |
| 243 | 0.001172 | −0.007876 | −0.023431 | −0.022801 | −0.004595 | −0.009843 | −0.003683 | −0.052722 | 0.002416 | −0.01267 | −0.01637 | −0.047488 | 0.005589 | 0.016448 |
| 244 | −0.007607 | 0.013446 | −0.012709 | 0.004715 | 0.011774 | −0.013579 | 0.012479 | 0.015623 | 0.011371 | −0.011844 | 0.016451 | −0.00789 | 0.012569 | 0.00219 |
| 245 | 0.026067 | 0.020653 | −0.030433 | 0.019991 | 0.017296 | −0.011434 | 0.019676 | −0.005348 | 0.017653 | −0.021125 | 0.0207 | 0.022161 | 0.007881 | 0.004151 |
| 246 | −0.002015 | −0.017887 | 0.037631 | 0.00224 | 0.003501 | −0.005838 | 0.01186 | −0.017036 | −0.001351 | 0.008142 | 0.000752 | −0.01186 | −0.000892 | −0.004329 |
| 247 | 0.008666 | −0.025301 | 0.029681 | 0.003892 | 0.001548 | −0.007009 | 0.001677 | −0.001859 | −0.001315 | 0.019655 | 0.000663 | −0.008534 | −0.001925 | −0.000946 |
| 248 | 0.019969 | −0.003619 | 0.011958 | 0.000789 | 0.004281 | 0.007614 | −0.004438 | −0.008397 | −0.005257 | 0.013778 | 0.010195 | −0.001977 | 0.001071 | −0.012945 |
| 249 | 0.021798 | −0.015815 | −0.02266 | −0.009739 | 0.002213 | 0.002564 | −0.004676 | 0.007994 | 0.006063 | −0.02544 | 0.012746 | 0.011667 | 0.006907 | 0.002075 |
| 250 | 0.004552 | −0.018077 | 0.01138 | 0.002176 | 0.00571 | 0.007702 | −0.001936 | 0.028929 | 0.003094 | −0.007093 | 0.001259 | 0.009587 | −0.005048 | −0.020264 |
| 251 | 0.013391 | 0.003166 | −0.003902 | −0.013199 | 0.012695 | 0.024053 | −0.003552 | 0.001378 | 0.001307 | 0.001092 | 0.004289 | 0.030564 | 0.011348 | −0.018451 |
| 252 | 0.02123 | 0.008405 | −0.031576 | −0.028662 | 0.019088 | 0.01829 | −0.011627 | −0.014289 | −0.002612 | −0.022984 | 0.006589 | 0.030068 | 0.005754 | −0.000139 |
| 253 | 0.009333 | 0.005573 | −0.058282 | −0.016715 | −0.002039 | −0.015215 | −0.015007 | −0.022099 | 0.001641 | −0.004328 | −0.005587 | −0.022954 | 0.006806 | 0.000633 |
| 254 | −0.012284 | 0.004797 | 0.013383 | 0.010435 | −0.000897 | −0.008916 | 0.003364 | 0.007473 | 0.001213 | −0.028075 | −0.001093 | −0.003065 | −0.013581 | −0.003162 |
| 255 | −0.020153 | 0.000402 | 0.018166 | −0.000096 | 0.004571 | −0.01381 | 0.01424 | −0.009844 | 0.001175 | −0.011568 | 0.004705 | −0.020177 | 0.000763 | 0.006565 |
| 256 | −0.007698 | −0.000016 | 0.014145 | 0.00815 | 0.011696 | 0.002047 | 0.024976 | −0.02504 | −0.003274 | −0.00057 | 0.015382 | −0.01977 | 0.003639 | 0.045227 |
| 257 | −0.026508 | −0.003907 | 0.005703 | −0.019311 | −0.000466 | −0.003886 | −0.000523 | 0.017639 | −0.016838 | 0.032967 | −0.004931 | −0.023952 | −0.017147 | −0.006535 |
| 258 | 0.018809 | −0.014202 | −0.027553 | 0.01126 | −0.005184 | −0.019853 | −0.002251 | 0.001082 | −0.014161 | 0.010588 | −0.024712 | 0.010372 | −0.001244 | 0.007518 |
| 259 | 0.009822 | −0.003371 | −0.006841 | −0.010382 | 0.001214 | 0.003913 | −0.015404 | 0.021955 | −0.004624 | −0.003037 | 0.007854 | 0.010551 | 0.000549 | −0.024355 |
| 260 | 0.011855 | −0.00437 | 0.006795 | −0.032778 | 0.009558 | 0.004928 | −0.024817 | 0.030678 | −0.004874 | −0.002946 | 0.008471 | −0.008573 | −0.009826 | −0.032218 |
| 261 | −0.000803 | −0.020795 | −0.00018 | 0.001675 | 0.005829 | 0.028526 | −0.011119 | 0.024829 | −0.005527 | 0.022079 | −0.00534 | 0.018961 | 0.000431 | −0.00297 |
| 262 | −0.003237 | −0.013649 | −0.014723 | 0.004262 | 0.003677 | 0.011661 | −0.001482 | −0.007314 | 0.013376 | 0.007317 | 0.009495 | 0.002789 | −0.004599 | 0.008187 |
| 263 | −0.006774 | −0.002084 | −0.026557 | −0.017037 | −0.001127 | −0.004035 | −0.009173 | 0.000612 | 0.004141 | −0.003408 | 0.010641 | −0.001023 | −0.007706 | −0.004919 |
| 264 | 0.002209 | −0.015361 | 0.013996 | 0.020911 | 0.003566 | −0.007558 | −0.004127 | 0.023179 | −0.007418 | −0.001708 | 0.006902 | 0.001224 | 0.006399 | 0.012732 |
| 265 | −0.01219 | −0.016672 | 0.049651 | 0.024721 | −0.002198 | −0.015988 | −0.002432 | 0.029619 | −0.00197 | 0.002171 | −0.007814 | −0.002996 | −0.007579 | 0.027338 |
| 266 | −0.01755 | 0.010344 | 0.031052 | 0.022976 | −0.001345 | −0.00188 | 0.006486 | 0.019273 | −0.000398 | −0.008577 | −0.019609 | −0.001158 | −0.006428 | 0.007038 |
| 267 | −0.005724 | 0.013173 | 0.016105 | 0.020163 | −0.008566 | −0.016032 | 0.006228 | −0.002823 | 0.017627 | 0.020424 | 0.011323 | −0.008821 | 0.005532 | 0.027306 |
| 268 | −0.009773 | 0.01934 | 0.027178 | −0.013302 | −0.00947 | 0.004403 | −0.021764 | −0.004513 | −0.000649 | 0.033393 | −0.010258 | 0.028945 | 0.000586 | −0.002716 |
| 269 | −0.009822 | 0.027214 | 0.022106 | −0.00836 | −0.014115 | −0.002254 | −0.020283 | −0.021385 | −0.008036 | 0.026019 | −0.015114 | 0.006298 | −0.006226 | −0.011752 |
| 270 | −0.015624 | 0.007518 | 0.008762 | −0.012207 | −0.018581 | −0.013224 | −0.020488 | −0.007216 | −0.010349 | 0.020887 | −0.010728 | −0.002535 | −0.010888 | −0.008113 |
| 271 | −0.021751 | 0.03998 | −0.019049 | −0.017204 | −0.003521 | −0.015824 | 0.000338 | 0.033906 | 0.030124 | −0.015409 | 0.001421 | 0.030072 | 0.000381 | −0.023803 |
| 272 | −0.01874 | 0.007913 | −0.005917 | −0.019213 | 0.019225 | 0.026263 | −0.00384 | −0.0366 | 0.001775 | 0.004208 | 0.015085 | 0.038529 | 0.012746 | 0.011502 |
| 273 | 0.002415 | −0.007198 | −0.009636 | −0.024131 | 0.014661 | 0.014011 | −0.030504 | −0.025239 | −0.00122 | 0.006998 | 0.018485 | 0.04147 | 0.00722 | −0.0026 |
| 274 | −0.001798 | −0.005814 | −0.014424 | −0.022325 | 0.014039 | 0.009954 | −0.029503 | −0.028223 | −0.004506 | 0.004812 | 0.014055 | 0.033513 | 0.005571 | −0.005738 |
| 275 | −0.010944 | −0.033722 | −0.030474 | 0.017366 | −0.007775 | −0.043478 | −0.010922 | −0.016194 | −0.003172 | −0.003928 | 0.024723 | −0.021592 | −0.011056 | 0.002175 |
| 276 | 0.016816 | 0.007302 | −0.013194 | 0.02106 | 0.004424 | 0.022078 | 0.000651 | 0.016951 | 0.01725 | 0.008561 | 0.002507 | 0.018994 | −0.004057 | −0.00636 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 277 | 0.021402 | −0.002018 | −0.009643 | 0.02175 | −0.001832 | 0.011075 | 0.00254 | 0.022052 | 0.011313 | −0.018174 | −0.000629 | −0.008759 | −0.003566 | 0.003112 |
| 278 | 0.010679 | 0.004958 | −0.022793 | 0.031535 | −0.006027 | 0.003306 | 0.002871 | 0.01459 | 0.011454 | −0.035837 | 0.004226 | −0.012991 | −0.010318 | −0.009919 |
| 279 | 0.004219 | 0.023073 | 0.003561 | −0.023926 | 0.003168 | 0.033951 | 0.006932 | 0.020894 | 0.015671 | 0.004289 | 0.012464 | −0.000752 | 0.00384 | 0.016472 |
| 280 | 0.005624 | 0.024202 | −0.039187 | −0.015468 | −0.002977 | −0.016946 | −0.003168 | −0.038442 | 0.01106 | −0.005694 | −0.019546 | −0.047371 | 0.02024 | 0.025532 |
| 281 | 0.005544 | 0.003964 | 0.000829 | 0.018659 | 0.001112 | −0.020629 | 0.011946 | −0.031877 | 0.003392 | −0.022056 | −0.010605 | 0.040378 | 0.006013 | −0.002332 |
| 282 | 0.004768 | 0.022173 | −0.017359 | 0.01659 | −0.001551 | −0.03109 | 0.01336 | −0.024923 | 0.004071 | −0.032538 | −0.009092 | 0.026383 | −0.002889 | −0.003052 |
| 283 | 0.004728 | −0.000205 | 0.010992 | 0.010469 | 0.000516 | 0.005532 | −0.00235 | −0.004038 | 0.0026 | −0.002503 | 0.005832 | 0.014038 | −0.007363 | −0.008396 |
| 284 | −0.024071 | −0.002322 | −0.002472 | −0.011454 | −0.001833 | −0.002158 | −0.002542 | 0.016454 | −0.014161 | 0.020084 | −0.003041 | −0.010895 | −0.012771 | 0.002115 |
| 285 | −0.027987 | 0.0106 | −0.004085 | −0.014816 | −0.005082 | −0.007634 | −0.001767 | 0.020997 | −0.012025 | 0.010785 | −0.000741 | −0.020349 | −0.018702 | −0.002651 |
| 286 | −0.001561 | 0.014404 | −0.039706 | −0.00495 | −0.000593 | −0.025329 | 0.007087 | −0.000626 | −0.025979 | −0.009734 | −0.030833 | 0.018929 | 0.003167 | 0.016838 |
| 287 | −0.001894 | 0.024346 | −0.045043 | −0.009119 | −0.007018 | −0.02802 | 0.003806 | −0.011751 | −0.020895 | −0.019784 | −0.027917 | 0.009126 | −0.002805 | 0.012676 |
| 288 | 0.01991 | −0.005061 | −0.030235 | 0.005833 | −0.00292 | 0.003225 | −0.00033 | −0.019191 | −4.006615 | 0.013556 | −0.017721 | 0.018308 | 0.004808 | 0.004138 |
| 289 | −0.010313 | −0.007381 | 0.007127 | −0.010527 | 0.00293 | −0.004249 | 0.003235 | −0.009121 | 0.01081 | −0.002281 | 0.009267 | −0.012731 | −0.001173 | 0.013972 |
| 290 | 0.012241 | −0.042875 | −0.02387 | 0.004055 | −0.00048 | −0.005869 | −0.006545 | −0.020445 | 0.004817 | 0.012958 | 0.008998 | 0.002562 | 0.010703 | 0.009016 |
| 291 | 0.011754 | −0.043789 | −0.02255 | 0.008796 | −0.000003 | −0.005251 | −0.003584 | −0.016614 | 0.004974 | 0.009058 | 0.007611 | −0.000771 | 0.009529 | 0.009579 |
| 292 | 0.006373 | −0.038778 | −0.019085 | −0.001299 | 0.005213 | 0.007618 | 0.001275 | −0.024621 | 0.00361 | 0.007782 | 0.004237 | 0.005219 | 0.011917 | 0.013173 |
| 293 | −0.071127 | −0.072566 | 0.029158 | 0.012582 | −0.014407 | 0.01215 | −0.029806 | 0.01824 | −0.013166 | 0.002152 | −0.014616 | −0.00181 | −0.015559 | −0.023939 |
| 294 | −0.02136 | −0.027777 | 0.012341 | 0.017969 | −0.022783 | −0.011468 | −0.027614 | −0.009764 | −0.009141 | −0.019879 | −0.011234 | 0.00744 | −0.018447 | −0.017669 |
| 295 | −0.034438 | −0.044802 | −0.003766 | −0.011315 | −0.004323 | 0.009885 | −0.027243 | −0.011008 | −0.002581 | −0.001742 | 0.002564 | −0.004774 | −0.017498 | −0.023963 |
| 296 | −0.003844 | −0.042346 | −0.01058 | −0.038071 | −0.015038 | −0.029067 | −0.029961 | −0.038793 | −0.00891 | 0.016387 | −0.003593 | −0.014087 | −0.018288 | −0.020281 |
| 297 | −0.023594 | −0.036177 | −0.009958 | −0.002403 | −0.004705 | 0.020564 | −0.025139 | −0.036329 | −0.005527 | −0.011842 | −0.011321 | 0.008113 | −0.010447 | −0.021883 |
| 298 | −0.002865 | 0.017762 | 0.010013 | −0.010035 | −0.009393 | −0.030019 | −0.01868 | 0.00766 | −0.008346 | −0.027318 | −0.004492 | −0.031419 | −0.020205 | −0.03579 |
| 299 | −0.021444 | −0.016068 | −0.006129 | 0.008961 | −0.013864 | 0.007258 | −0.022083 | −0.005976 | 0.004878 | 0.011289 | −0.026742 | 0.026559 | 0.001324 | −0.024842 |
| 300 | −0.012733 | 0.006819 | −0.051687 | 0.013406 | 0.000589 | 0.030676 | −0.012359 | 0.0064 | 0.000855 | −0.016011 | −0.011676 | −0.023473 | −0.016889 | 0.010867 |
| 301 | −0.043738 | −0.025305 | 0.02181 | 0.00149 | −0.017698 | 0.000303 | −0.0212 | 0.016525 | −0.000713 | 0.028519 | 0.000886 | −0.029469 | −0.018331 | −0.02283 |
| 302 | −0.027221 | −0.009552 | 0.01944 | 0.012888 | −0.021431 | −0.019782 | −0.012518 | 0.010336 | 0.004543 | 0.023901 | 0.002864 | −0.02768 | −0.009559 | −0.007361 |
| 303 | −0.004946 | 0.011468 | −0.020053 | 0.010044 | −0.010334 | −0.011679 | −0.003967 | −0.017605 | −0.003015 | −0.004113 | −0.036713 | −0.00885 | 0.00526 | −0.00634 |
| 304 | 0.002741 | 0.004625 | −0.036269 | 0.002294 | −0.014478 | −0.001164 | −0.01744 | −0.021668 | −0.004385 | 0.008138 | −0.026979 | 0.017326 | 0.014964 | −0.018571 |
| 305 | 0.847033 | −0.017568 | 0.044071 | 0.018189 | −0.004636 | 0.005303 | −0.006641 | 0.013337 | −0.002574 | −0.012405 | −0.004669 | −0.015131 | 0.005905 | 0.006282 |
| 306 | −0.027927 | 0.768399 | −0.032886 | 0.037176 | 0.001186 | −0.012381 | −0.026937 | 0.024928 | −0.024309 | −0.003476 | −0.009819 | −0.006086 | −0.003191 | 0.003555 |
| 307 | 0.041299 | −0.0482 | 0.689096 | −0.054153 | −0.004517 | −0.02735 | −0.02354 | −0.010324 | −0.001571 | −0.079445 | −0.031123 | 0.031616 | −0.012183 | −0.048596 |
| 308 | −0.011175 | −0.014868 | −0.076236 | 0.678507 | 0.02894 | 0.044952 | −0.02102 | −0.086902 | −0.022801 | 0.058075 | −0.006589 | −0.006956 | 0.030856 | 0.008786 |
| 309 | −0.013548 | −0.001441 | −0.002525 | 0.033597 | 0.933879 | −0.065368 | −0.025947 | 0.006298 | −0.011908 | −0.018541 | −0.033182 | −0.030365 | −0.053476 | −0.031438 |
| 310 | −0.003402 | −0.030487 | −0.008714 | 0.088838 | −0.064256 | 0.82827 | −0.010079 | 0.042113 | −0.007844 | −0.057713 | −0.020137 | −0.045801 | −0.051842 | −0.023604 |
| 311 | −0.002917 | −0.01584 | −0.015625 | −0.023082 | −0.020861 | −0.00295 | 0.93543 | −0.000923 | −0.034234 | 0.001593 | −0.02169 | 0.000494 | −0.021437 | −0.036312 |
| 312 | −0.00782 | 0.002398 | −0.02079 | −0.081216 | 0.00015 | 0.036174 | −0.003843 | 0.670353 | −0.017275 | −0.055665 | −0.034067 | 0.038145 | 0.009645 | 0.009173 |
| 313 | −0.011068 | −0.021276 | 0.019884 | −0.024067 | −0.015299 | −0.009289 | −0.034419 | −0.0202281 | 0.922271 | −0.024937 | −0.029037 | −0.031005 | −0.024478 | −0.019127 |
| 314 | −0.006533 | 0.000996 | −0.044626 | 0.065392 | −0.017129 | −0.029544 | −0.002946 | −0.056307 | −0.041634 | 0.651553 | −0.034854 | −0.011817 | −0.041939 | −0.056544 |
| 315 | −0.009493 | −0.004346 | −0.021772 | −0.001708 | −0.038946 | −0.030102 | −0.022735 | −0.030878 | −0.030153 | −0.032111 | 0.93158 | −0.012843 | −0.039051 | −0.034807 |
| 316 | −0.060651 | −0.024635 | 0.062631 | 0.006048 | −0.023207 | −0.04721 | 0.002941 | 0.028189 | −0.017492 | −0.016242 | 0.000034 | 0.727245 | −0.029129 | 0.003041 |
| 317 | −0.013885 | 0.000087 | 0.013004 | 0.029154 | −0.05408 | −0.054159 | −0.023904 | 0.01463 | −0.023523 | −0.034243 | −0.032411 | −0.045254 | 0.917843 | −0.051629 |
| 318 | 0.009741 | 0.021061 | −0.03868 | −0.001374 | −0.033917 | −0.036093 | −0.031413 | 0.033595 | −0.018975 | −0.03986 | −0.029328 | −0.007219 | −0.053097 | 0.853822 |
| 319 | 0.012886 | 0.01206 | −0.026819 | 0.025077 | −0.046074 | −0.045943 | −0.02142 | −0.008009 | −0.021875 | −0.018361 | −0.05973 | −0.024778 | −0.054425 | −0.043302 |
| 320 | 0.014338 | −0.015196 | 0.033804 | −0.010648 | −0.01378 | −0.008029 | −0.034258 | −0.013777 | −0.035351 | 0.022519 | −0.017149 | −0.011123 | −0.023131 | −0.030962 |
| 321 | 0.03369 | −0.027702 | −0.059628 | −0.008852 | 0.004764 | 0.011292 | −0.023978 | 0.025709 | −0.013176 | −0.03138 | −0.011322 | 0.028363 | 0.002752 | −0.018173 |
| 322 | −0.030749 | 0.032867 | −0.012544 | −0.028747 | −0.02089 | −0.053137 | 0.024441 | −0.000764 | 0.048935 | −0.053063 | 0.017876 | −0.04137 | −0.016465 | −0.013644 |
| 323 | 0.014043 | −0.009699 | −0.000379 | 0.00434 | 0.010938 | −0.002817 | −0.012222 | −0.02325 | −0.021472 | −0.041129 | −0.012723 | 0.009911 | 0.001621 | −0.01478 |
| 324 | −0.035593 | −0.014728 | −0.004108 | −0.026813 | −0.008909 | −0.00526 | −0.010336 | 0.034355 | 0.01987 | −0.006137 | 0.010212 | −0.033374 | 0.020441 | −0.011048 |
| 325 | 0.002495 | −0.006032 | 0.019357 | 0.022833 | −0.044392 | −0.038832 | −0.020702 | −0.005177 | −0.014554 | 0.022117 | −0.031742 | −0.031442 | −0.037141 | −0.005591 |
| 326 | 0.000495 | 0.001391 | 0.010583 | −4.000513 | −0.039009 | −0.032543 | −0.041757 | −0.019641 | −0.034642 | 0.009113 | −0.020434 | 0.005547 | −0.026791 | −0.000659 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 327 | −0.005424 | 0.010227 | −0.003289 | −0.00229 | −0.01758 | −0.017442 | −0.022613 | −0.003675 | −0.011433 | 0.029519 | −0.020091 | −0.001562 | −0.015786 | −0.022262 |
| 328 | −0.075127 | −0.044278 | 0.026222 | −0.045233 | −0.004961 | 0.02839 | −0.023363 | −0.033275 | −0.008974 | −0.061714 | −0.003139 | −0.011689 | 0.002429 | 0.052873 |
| 329 | −0.000875 | 0.027691 | 0.024939 | −0.004303 | −0.005486 | −0.003556 | −0.016649 | −0.011595 | −0.018523 | 0.016483 | −0.019584 | 0.007043 | −0.011817 | −0.015487 |
| 330 | −0.006779 | 0.025746 | 0.094618 | 0.086628 | −0.005859 | −0.025155 | 0.001564 | 0.020957 | 0.013852 | −0.002323 | 0.024329 | −0.019695 | −0.01054 | 0.024213 |
| 331 | −0.000927 | −0.009368 | −0.007008 | −0.007156 | −0.024979 | −0.011153 | −0.026117 | −0.031448 | −0.020516 | −0.001013 | −0.043834 | 0.001361 | −0.013853 | −0.009337 |
| 332 | −0.000755 | 0.018819 | −0.008186 | 0.018967 | −0.0238 | 0.005539 | −0.054988 | 0.03633 | 0.003165 | 0.046708 | 0.002227 | −0.031614 | −0.003435 | 0.000017 |
| 333 | 0.007631 | −0.002228 | −0.00028 | 0.005428 | −0.042501 | −0.025787 | −0.02182 | 0.010585 | −0.014075 | 0.020997 | −0.029915 | −0.03377 | −0.040415 | −0.030484 |
| 334 | −0.016612 | −0.006475 | 0.057789 | 0.00708 | −0.017111 | −0.005788 | 0.026544 | −0.079881 | −0.00743 | 0.003106 | −0.016539 | 0.023048 | −0.009676 | 0.017105 |
| 335 | 0.017704 | 0.002139 | −0.015893 | 0.02925 | −0.03352 | −0.033344 | −0.034143 | −0.020925 | −0.026237 | −0.00051 | −0.029709 | −0.006593 | −0.024815 | −0.018042 |
| 336 | −0.004858 | −0.042257 | −0.021783 | 0.011897 | −0.043292 | −0.036757 | −0.016587 | 0.010665 | 0.000851 | −0.014987 | −0.013967 | −0.004858 | −0.034815 | −0.009378 |
| 337 | −0.03161 | −0.056898 | −0.015062 | −0.034812 | −0.012682 | −0.02789 | −0.00169 | −0.029451 | 0.006088 | 0.001412 | −0.014584 | −0.046132 | −0.010636 | −0.016966 |
| 338 | −0.009839 | 0.016269 | −0.009232 | −0.037937 | 0.007321 | −0.03126 | −0.017277 | 0.01704 | 0.008278 | −0.003723 | 0.003354 | 0.024156 | 0.010696 | −0.013426 |
| 339 | −0.00768 | −0.026289 | −0.044652 | −0.030657 | −0.007624 | 0.030419 | −0.026926 | −0.039827 | −0.017572 | −0.011052 | −0.017933 | 0.030941 | −0.009756 | −0.008691 |
| 340 | −0.0585 | −0.037623 | 0.008728 | −0.018166 | 0.015845 | −0.017747 | 0.015492 | 0.012247 | 0.010463 | 0.029022 | −0.023562 | −0.003157 | 0.028177 | −0.042078 |

| | LH | LI | LJ | LK | LL | LM | LN | LO | LP | LQ | LR | LS | LT | LU |
|---|---|---|---|---|---|---|---|---|---|---|---|---|---|---|
| 1 | 0.014383 | 0.014662 | −0.053105 | −0.054621 | −0.015636 | 0.012251 | 0.024432 | 0.091832 | 0.009744 | −0.038889 | 0.010281 | −0.007567 | 0.00727 | −0.013215 |
| 2 | 0.026883 | −0.013328 | −0.037785 | −0.028171 | −0.037482 | 0.066039 | −0.007791 | 0.044705 | −0.032866 | 0.117652 | −0.044004 | −0.039957 | 0.020014 | 0.027529 |
| 3 | −0.061619 | −0.014076 | −0.016038 | −0.020366 | −0.085703 | −0.05118 | −0.056197 | −0.082629 | −0.088336 | −0.008603 | −0.108224 | 0.023068 | −0.042153 | 0.021307 |
| 4 | 0.05476 | −0.016685 | 0.039692 | 0.071184 | 0.100434 | −0.035507 | −0.053752 | −0.000648 | 0.015924 | −0.055631 | 0.029837 | −0.022459 | 0.049342 | −0.024747 |
| 5 | 0.022088 | −0.019037 | −0.022182 | 0.106586 | 0.013954 | 0.05605 | −0.023423 | −0.04382 | 0.026311 | 0.0153091 | 0.033441 | −0.004133 | 0.020258 | 0.055536 |
| 6 | 0.053026 | 0.024801 | −0.01755 | 0.091925 | −0.002956 | −0.005413 | 0.040641 | 0.020121 | −0.002014 | 0.036126 | −0.004976 | 0.015995 | 0.020626 | 0.011226 |
| 7 | 0.100002 | 0.037085 | 0.020672 | −0.069678 | 0.005308 | −0.016699 | 0.046468 | 0.061672 | 0.038852 | −0.082296 | 0.037602 | 0.014606 | 0.085158 | 0.014708 |
| 8 | −0.00696 | 0.041184 | 0.053677 | 0.124349 | −0.01604 | 0.11929 | 0.013694 | 0.010391 | 0.02955 | 0.020315 | 0.038537 | −0.03803 | 0.036301 | 0.052974 |
| 9 | 0.021699 | 0.020409 | −0.033591 | −0.144044 | −0.127267 | 0.081983 | 0.052489 | 0.045652 | 0.003652 | −0.125532 | 0.010007 | −0.007547 | −0.005459 | −0.005966 |
| 10 | −0.044154 | −0.022369 | 0.008438 | −0.076951 | 0.016272 | 0.049334 | −0.067269 | −0.114056 | −0.003857 | −0.037403 | −0.063895 | −0.07569 | −0.026492 | −0.028324 |
| 11 | −0.014269 | 0.049583 | 0.026665 | 0.001921 | 0.040408 | 0.140223 | 0.050511 | −0.041107 | 0.061647 | 0.036753 | 0.012856 | −0.006844 | −0.019362 | −0.05125 |
| 12 | 0.008777 | 0.00769 | −0.028306 | −0.06288 | 0.005706 | 0.026217 | −0.035818 | −0.00029 | 0.011898 | 0.028257 | −0.028554 | −0.028647 | −0.019662 | 0.019687 |
| 13 | 0.022565 | −0.003344 | −0.011169 | −0.090324 | −0.083208 | 0.024512 | −0.020358 | −0.04144 | −0.038715 | −0.004806 | −0.063963 | −0.078115 | −0.016332 | −0.041033 |
| 14 | 0.012707 | 0.060898 | 0.045553 | −0.004074 | 0.060385 | 0.020861 | −0.021911 | −0.061444 | 0.004798 | 0.045052 | 0.046803 | −0.002374 | −0.044166 | −0.029947 |
| 15 | −0.005144 | −0.095715 | −0.109902 | 0.199074 | −0.020579 | −0.023876 | −0.020882 | −0.051877 | −0.031473 | −0.030976 | −0.034605 | 0.005309 | −0.043128 | −0.083597 |
| 16 | 0.037972 | −0.027936 | 0.004881 | −0.082915 | 0.003804 | −0.036915 | 0.00103 | 0.051059 | −0.003761 | −0.031836 | 0.012382 | 0.037945 | −0.001682 | −0.018136 |
| 17 | −0.105929 | −0.14238 | −0.052113 | 0.012685 | −0.014156 | 0.114885 | −0.06997 | −0.010898 | −0.054766 | −0.011558 | −0.025066 | −0.040238 | −0.05215 | −0.00043 |
| 18 | −0.062891 | −0.012061 | 0.102929 | 0.063194 | 0.087348 | −0.014573 | −0.043419 | −0.029586 | 0.03041 | 0.201845 | 0.070399 | 0.033009 | 0.017863 | −0.022619 |
| 19 | −0.012214 | 0.004143 | −0.071345 | −0.071255 | −0.131678 | 0.045203 | 0.024074 | −0.006982 | −0.045817 | −0.077475 | −0.083489 | −0.172991 | −0.000013 | −0.078147 |
| 20 | −0.066931 | −0.079162 | −0.019868 | −0.05676 | −0.051601 | −0.025275 | −0.013498 | 0.000055 | 0.015529 | −0.024066 | 0.039776 | −0.022352 | −0.035007 | −0.076732 |
| 21 | −0.005678 | 0.082048 | 0.001924 | −0.056792 | −0.012368 | −0.057703 | −0.039457 | 0.002638 | 0.022833 | −0.001166 | 0.006282 | 0.03352 | −0.018697 | 0.043462 |
| 22 | −0.000494 | −0.028113 | 0.148202 | 0.006461 | 0.021943 | 0.003986 | −0.000249 | −0.01658 | −0.000622 | −0.077844 | 0.037262 | 0.015604 | 0.020846 | 0.081972 |
| 23 | 0.030357 | 0.011658 | −0.025619 | 0.001753 | −0.053723 | −0.004396 | 0.060908 | 0.055924 | −0.022844 | 0.024177 | −0.012793 | −0.045973 | 0.012459 | 0.009529 |
| 24 | 0.094634 | 0.033736 | −0.00168 | −0.047371 | 0.038767 | −0.057863 | 0.039362 | −0.034014 | 0.049221 | −0.027903 | 0.038569 | 0.121731 | 0.017669 | −0.000806 |
| 25 | −0.012212 | 0.00989 | −0.041985 | −0.043305 | 0.000205 | 0.038542 | −0.004321 | 0.010087 | 0.012559 | −0.103775 | 0.007299 | 0.013532 | 0.053975 | −0.015531 |
| 26 | −0.036322 | 0.08686 | 0.031617 | 0.068602 | 0.057468 | −0.063725 | −0.034408 | −0.071314 | 0.009917 | 0.058133 | −0.05576 | 0.002139 | −0.039031 | −0.012588 |
| 27 | 0.000652 | −0.006355 | −0.046671 | 0.206819 | 0.029937 | 0.106981 | −0.012494 | 0.006378 | 0.033852 | 0.067535 | 0.013597 | 0.080773 | 0.053351 | 0.030462 |
| 28 | −0.013329 | 0.012871 | 0.082652 | −0.082385 | −0.027931 | −0.029763 | 0.002704 | 0.001617 | 0.002545 | 0.000745 | −0.026827 | −0.058014 | 0.036856 | 0.074671 |
| 29 | 0.012257 | 0.031108 | −0.006951 | −0.017672 | 0.00638 | −0.010943 | 0.01927 | −0.028879 | 0.013205 | −0.012632 | −0.022716 | 0.018792 | −0.016272 | −0.011315 |
| 30 | 0.044722 | 0.038202 | 0.00828 | 0.029864 | −0.003294 | −0.029102 | −0.013292 | −0.090228 | 0.011591 | 0.028294 | 0.009035 | −0.074846 | −0.030596 | 0.035694 |
| 31 | 0.007033 | 0.006976 | −0.043888 | −0.064165 | −0.016502 | 0.0422 | −0.032518 | −0.090704 | −0.067803 | 0.06079 | −0.07523 | −0.07201 | −0.020146 | 0.000075 |
| 32 | 0.038193 | 0.04004 | 0.003028 | 0.000661 | −0.02638 | −0.023794 | 0.069728 | 0.066902 | 0.035529 | −0.011322 | 0.015176 | −0.035102 | 0.014101 | 0.059746 |
| 33 | −0.003456 | −0.050918 | 0.027717 | −0.088369 | 0.009292 | −0.031092 | 0.015752 | 0.005651 | −0.003942 | −0.082112 | 0.016876 | 0.042571 | −0.022292 | −0.02859 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 34 | 0.043938 | 0.005449 | 0.004432 | −0.01899 | 0.073238 | −0.109642 | −0.0197 | −0.111514 | −0.010548 | 0.216265 | 0.064092 | −0.012172 | −0.0164 | −0.093786 |
| 35 | −0.023634 | −0.075098 | 0.029326 | −0.063247 | −0.017973 | 0.015336 | −0.0184 | −0.006531 | −0.027528 | 0.00723 | −0.01222 | −0.037734 | −0.043103 | −0.012588 |
| 36 | −0.039111 | −0.011152 | 0.01367 | 0.029655 | 0.021869 | 0.102063 | −0.059836 | −0.009726 | 0.000978 | −0.048154 | 0.009588 | 0.062698 | −0.065193 | −0.05532 |
| 37 | 0.035507 | 0.063647 | 0.02249 | 0.02178 | 0.028603 | −0.13076 | −0.041458 | −0.034484 | −0.009663 | −0.165003 | 0.030318 | 0.034399 | −0.042644 | −0.030582 |
| 38 | −0.002709 | −0.022808 | −0.022668 | 0.01535 | −0.011973 | −0.050405 | 0.018316 | 0.06046 | −0.049983 | 0.027074 | −0.013248 | 0.132385 | −0.043097 | 0.076938 |
| 39 | −0.042662 | −0.038691 | 0.01235 | 0.040032 | 0.045911 | −0.036671 | −0.005623 | 0.034257 | 0.043005 | 0.023028 | 0.00261 | 0.029727 | 0.004207 | −0.029019 |
| 40 | −0.007519 | 0.011072 | 0.005601 | −0.044921 | −0.006801 | 0.029333 | 0.005964 | 0.007697 | 0.012155 | −0.032866 | 0.004233 | −0.010449 | −0.003132 | −0.02525 |
| 41 | 0.016108 | 0.087721 | −0.088127 | 0.044619 | 0.0345681 | −0.026951 | −0.078631 | −0.069585 | 0.000815 | −0.013616 | −0.027191 | −0.026061 | −0.027402 | −0.026478 |
| 42 | −0.011466 | −0.034044 | 0.010877 | −0.045453 | 0.0312 | −0.009322 | 0.038422 | 0.034139 | −0.011367 | 0.07349 | 0.003697 | 0.072196 | 0.006271 | 0.045095 |
| 43 | 0.003175 | −0.027027 | −0.017794 | −0.023074 | 0.037217 | −0.103516 | 0.007067 | −0.038785 | −0.010107 | 0.003227 | −0.03769 | −0.080891 | −0.024437 | 0.014292 |
| 44 | −0.04247 | −0.011758 | −0.018435 | 0.131695 | −0.012632 | 0.017095 | −0.002611 | 0.04445 | −0.005315 | −0.011098 | −0.038837 | 0.130999 | −0.008172 | 0.116946 |
| 45 | 0.025383 | −0.004901 | −0.011352 | 0.004051 | −0.024042 | 0.025091 | 0.053196 | −0.05217 | −0.000457 | 0.013969 | −0.042268 | 0.015976 | 0.005271 | −0.014774 |
| 46 | 0.024156 | 0.033517 | −0.085169 | −0.074404 | −0.045253 | −0.058967 | −0.018351 | 0.095941 | 0.033671 | 0.0146 | 0.06954 | −0.000686 | 0.000913 | 0.141458 |
| 47 | −0.004524 | −0.008873 | −0.003143 | 0.036158 | −0.045277 | −0.012445 | 0.032522 | −0.009709 | 0.045865 | 0.018488 | 0.010726 | 0.059099 | −0.014627 | 0.006231 |
| 48 | −0.00517 | 0.022926 | −0.005302 | 0.000335 | −0.01999 | 0.031779 | 0.042124 | 0.002254 | 0.022277 | −0.036107 | 0.00229 | −0.098298 | 0.052828 | −0.087288 |
| 49 | −0.012479 | 0.032553 | 0.006408 | 0.033212 | −0.047783 | 0.084311 | −0.002472 | 0.025376 | −0.028798 | 0.110418 | −0.036282 | 0.264144 | −0.041699 | 0.361109 |
| 50 | 0.008017 | 0.009508 | 0.005291 | 0.096727 | 0.044516 | −0.029254 | 0.023611 | −0.010299 | 0.05114 | −0.040744 | 0.051366 | 0.053042 | 0.024369 | 0.025418 |
| 51 | 0.110184 | 0.054893 | 0.023417 | −0.085348 | 0.071362 | −0.063286 | 0.011643 | 0.003974 | 0.01642 | −0.027832 | 0.016087 | −0.073541 | 0.030592 | 0.09303 |
| 52 | 0.038333 | −0.067721 | −0.039331 | 0.090276 | −0.048524 | −0.035748 | −0.019752 | −0.026446 | −0.030584 | −0.068801 | −0.009058 | −0.044929 | −0.071626 | 0.043142 |
| 53 | 0.002556 | −0.047342 | −0.060816 | −0.175247 | −0.02736 | 0.011895 | −0.045304 | 0.013596 | 0.017965 | −0.032606 | 0.031428 | −0.086133 | 0.014563 | 0.045058 |
| 54 | 0.016222 | −0.046667 | 0.087345 | 0.050323 | −0.013153 | 0.080021 | 0.020947 | 0.059934 | −0.003301 | 0.026434 | −0.032085 | −0.015458 | −0.01612 | 0.02962 |
| 55 | 0.015457 | −0.090324 | 0.024423 | 0.038253 | −0.107466 | 0.061322 | 0.02171 | −0.150606 | −0.012855 | −0.102515 | −0.098179 | −0.005514 | −0.064917 | −0.003076 |
| 56 | 0.03206 | −0.037891 | −0.020092 | −0.080875 | −0.001256 | 0.047227 | 0.074287 | −0.007376 | 0.016194 | −0.166087 | 0.017169 | 0.017203 | 0.023154 | −0.078975 |
| 57 | −0.053658 | 0.074895 | −0.028424 | −0.008285 | 0.083844 | −0.008545 | −0.120882 | −0.108367 | −0.013719 | −0.089565 | 0.011895 | −0.065986 | −0.073016 | −0.099663 |
| 58 | −0.00062 | 0.01071 | −0.000733 | 0.014518 | −0.002515 | −0.039694 | 0.0346 | 0.023273 | 0.026015 | 0.075218 | 0.056793 | −0.026712 | −0.000903 | −0.031854 |
| 59 | 0.004826 | 0.033471 | −0.035424 | −0.017519 | −0.092605 | 0.043365 | 0.027089 | 0.039877 | 0.00484 | 0.099878 | −0.009365 | 0.028717 | 0.001701 | −0.007615 |
| 60 | −0.004284 | −0.014375 | −0.029863 | 0.009801 | −0.016964 | 0.013456 | 0.008181 | 0.022443 | −0.011505 | 0.014184 | −0.011759 | 0.024508 | 0.002101 | 0.015326 |
| 61 | 0.005306 | −0.013101 | 0.001103 | −0.005194 | −0.019617 | 0.019156 | 0.015055 | −0.001891 | −0.012857 | −0.011848 | −0.018944 | −0.0073 | 0.00186 | 0.000462 |
| 62 | 0.010014 | −0.004974 | 0.009634 | −0.008657 | 0.009966 | −0.035686 | −0.01373 | −0.010372 | −0.021124 | 0.019492 | −0.01719 | 0.020855 | −0.00995 | 0.001534 |
| 63 | 0.001566 | 0.008783 | 0.022513 | −0.000457 | 0.001577 | 0.012046 | −0.001866 | −0.016027 | 0.001218 | −0.056895 | −0.010897 | −0.009668 | 0.004176 | −0.000481 |
| 64 | −0.001445 | −0.012631 | −0.018472 | 0.018612 | −0.014163 | 0.000793 | −0.024614 | −0.013956 | 0.000253 | −0.045789 | 0.00006 | −0.019481 | −0.006116 | −0.010465 |
| 65 | 0.006198 | 0.006417 | −0.007247 | 0.004805 | −0.013077 | −0.008272 | 0.016775 | 0.019886 | 0.004086 | 0.009151 | −0.009755 | 0.03216 | 0.000843 | 0.022876 |
| 66 | 0.012716 | 0.004774 | −0.003932 | −0.017676 | −0.013132 | −0.009384 | 0.002629 | 0.001445 | 0.010655 | −0.075887 | 0.009214 | −0.01579 | −0.017854 | −0.013155 |
| 67 | −0.002172 | 0.006202 | 0.036945 | −0.025701 | −0.022254 | −0.016322 | −0.006939 | −0.048503 | −0.011617 | −0.056412 | −0.006138 | −0.041274 | −0.025064 | −0.035305 |
| 68 | −0.025579 | −0.013359 | 0.013707 | 0.023106 | 0.025017 | −0.005017 | −0.01879 | −0.008426 | −0.00148 | 0.002905 | 0.020249 | −0.009773 | 0.002298 | −0.053408 |
| 69 | 0.014561 | −0.021156 | 0.002515 | 0.007503 | −0.006642 | 0.007704 | 0.012835 | −0.009968 | −0.003029 | 0.006836 | −0.003481 | 0.019185 | 0.008637 | 0.013941 |
| 70 | 0.00852 | 0.018406 | −0.016139 | −0.026309 | −0.013357 | −0.004948 | 0.007421 | 0.024319 | −0.009763 | 0.011152 | 0.004024 | 0.022165 | 0.000632 | −0.00246 |
| 71 | 0.014254 | 0.018188 | −0.013357 | 0.020534 | −0.011444 | 0.006128 | 0.004631 | 0.025396 | 0.009532 | 0.004386 | −0.003471 | −0.00203 | 0.031055 | 0.045056 |
| 72 | 0.004556 | 0.005965 | −0.037809 | 0.049253 | −0.009219 | 0.017319 | 0.003397 | 0.014789 | 0.001993 | 0.012187 | −0.015084 | 0.023673 | 0.020124 | 0.024683 |
| 73 | −0.008802 | −0.005536 | −0.032975 | 0.039554 | −0.003579 | −0.005155 | −0.000138 | 0.016603 | 0.003743 | −0.020241 | 0.019729 | 0.01128 | −0.013719 | −0.045539 |
| 74 | 0.009279 | 0.006564 | −0.007906 | 0.022002 | −0.007764 | 0.031648 | 0.011762 | 0.002181 | 0.003901 | 0.022681 | −0.022771 | 0.001942 | 0.018027 | 0.025098 |
| 75 | 0.007366 | 0.0084 | −0.003194 | 0.009492 | −0.011102 | −0.005977 | 0.004139 | 0.014404 | 0.00791 | 0.003842 | 0.005321 | 0.025233 | 0.009731 | 0.030157 |
| 76 | 0.020478 | 0.001612 | 0.023134 | −0.037963 | −0.014404 | −0.002356 | −0.000871 | −0.012961 | 0.001341 | −0.02657 | −0.015292 | 0.004907 | 0.003301 | 0.037538 |
| 77 | 0.00469 | 0.009052 | −0.003345 | 0.012883 | −0.006886 | −0.001301 | 0.008907 | 0.011795 | 0.006045 | 0.00505 | 0.001288 | 0.027565 | 0.013774 | 0.027414 |
| 78 | 0.006243 | 0.011197 | −0.012336 | 0.007949 | −0.017367 | 0.00044 | 0.005341 | 0.023353 | 0.002719 | 0.023719 | 0.006677 | 0.019649 | 0.014312 | 0.025982 |
| 79 | 0.012382 | −0.000695 | −0.007242 | 0.013192 | −0.004384 | −0.023157 | −0.012015 | 0.015617 | 0.017473 | −0.029985 | 0.022626 | 0.028599 | −0.001871 | 0.024767 |
| 80 | 0.024326 | −0.01098 | −0.01549 | 0.013229 | −0.026452 | 0.010732 | 0.024278 | 0.009135 | −0.008871 | 0.000045 | −0.009498 | −0.056465 | −0.012302 | −0.071915 |
| 81 | −0.034778 | −0.011588 | 0.053114 | 0.026666 | −0.009618 | 0.03551 | 0.032851 | −0.031439 | −0.006244 | 0.026355 | −0.033701 | 0.013876 | 0.002242 | −0.014982 |
| 82 | 0.011128 | 0.013713 | −0.017727 | −0.01786 | 0.012586 | −0.0268 | −0.003325 | 0.013889 | 0.009969 | 0.003715 | 0.011604 | −0.004339 | −0.001311 | 0.002021 |
| 83 | 0.006066 | 0.005575 | −0.012542 | −0.012072 | 0.003445 | −0.015544 | −0.009533 | 0.020266 | 0.002959 | 0.013637 | −0.002568 | −0.019262 | 0.00623 | 0.006617 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 84 | 0.002602 | 0.006713 | 0.000732 | −0.007132 | −0.012655 | 0.0071 | 0.01086 | 0.037725 | 0.001493 | 0.026227 | −0.002168 | −0.000476 | 0.01554 | 0.032049 |
| 85 | −0.006234 | −0.003758 | 0.038704 | 0.003775 | 0.028845 | −0.002625 | −0.025709 | −0.029156 | −0.001653 | −0.10226 | 0.008948 | 0.010437 | 0.001472 | −0.039876 |
| 86 | 0.002519 | −0.002814 | −0.004281 | −0.003345 | 0.029431 | −0.010906 | −0.014926 | −0.016043 | −0.00406 | −0.00413 | −0.000644 | −0.024398 | 0.021597 | −0.036635 |
| 87 | 0.029426 | 0.013071 | −0.016414 | −0.011919 | −0.019343 | −0.000659 | 0.004071 | −0.00106 | −0.012751 | 0.014697 | −0.019461 | −0.024031 | 0.000182 | 0.019332 |
| 88 | 0.004039 | 0.007373 | −0.012466 | −0.0056 | −0.012934 | −0.012889 | 0.006318 | 0.015372 | 0.003405 | 0.020954 | 0.00518 | −0.012162 | 0.000841 | 0.001434 |
| 89 | 0.007525 | 0.002494 | −0.012097 | −0.019123 | −0.013748 | 0.00353 | −0.003571 | 0.020449 | 0.000468 | 0.025839 | 0.002895 | −0.027547 | 0.010207 | 0.002279 |
| 90 | 0.017766 | −0.008786 | −0.00657 | −0.002256 | −0.018286 | 0.017373 | 0.000622 | 0.016761 | −0.001481 | 0.010301 | −0.010576 | −0.019148 | 0.015399 | 0.012143 |
| 91 | −0.008323 | 0.000285 | −0.017844 | 0.003354 | −0.002558 | 0.013647 | −0.001668 | 0.030548 | 0.005818 | 0.01746 | 0.009321 | −0.003072 | 0.0146 | −0.006625 |
| 92 | −0.014974 | 0.002407 | −0.007923 | 0.013205 | −0.012599 | −0.012025 | 0.020879 | 0.046801 | −0.006313 | 0.085812 | 0.009995 | −0.009895 | 0.008586 | −0.017884 |
| 93 | 0.005827 | 0.00465 | 0.000669 | 0.023573 | 0.000061 | −0.001989 | −0.006156 | 0.008581 | −0.002873 | −0.048581 | −0.004424 | 0.012445 | 0.005566 | −0.003655 |
| 94 | 0.000064 | 0.012794 | −0.008819 | −0.032387 | 0.01048 | −0.017275 | −0.007092 | 0.047511 | −0.002283 | −0.016524 | 0.014517 | 0.004101 | 0.009636 | −0.027142 |
| 95 | 0.011033 | 0.003683 | 0.050627 | 0.026288 | 0.0737 | −0.02088 | −0.00565 | −0.030247 | 0.013264 | 0.033064 | 0.030942 | −0.041435 | 0.001777 | −0.031722 |
| 96 | −0.001532 | 0.051284 | −0.008629 | −0.034993 | −0.010776 | 0.036504 | 0.012947 | 0.023498 | 0.016065 | −0.031011 | 0.01883 | −0.036722 | 0.009206 | −0.026698 |
| 97 | −0.015393 | −0.019551 | −0.010161 | −0.021513 | −0.005167 | 0.011329 | −0.009115 | −0.004668 | −0.01048 | −0.008087 | −0.012773 | 0.002441 | −0.022932 | −0.007689 |
| 98 | 0.010297 | 0.011377 | 0.004987 | 0.019137 | −0.001364 | 0.00109 | 0.000045 | −0.004425 | 0.006847 | −0.002596 | 0.001679 | −0.02097 | 0.003285 | −0.015927 |
| 99 | −0.021312 | −0.012706 | −0.002291 | 0.001094 | −0.002217 | 0.008481 | −0.003413 | −0.005323 | −0.008891 | 0.011147 | −0.010884 | 0.00247 | −0.010191 | −0.001915 |
| 100 | 0.014815 | 0.020175 | −0.006735 | −0.015655 | 0.008389 | −0.027401 | −0.010487 | −0.027155 | 0.000874 | −0.015912 | −0.002212 | −0.052779 | −0.003841 | −0.008911 |
| 101 | −0.007155 | 0.002119 | 0.016263 | 0.015394 | −0.010902 | 0.014332 | −0.00985 | −0.014433 | −0.009072 | −0.009122 | −0.008294 | −0.021871 | −0.007072 | −0.02013 |
| 102 | −0.016179 | 0.008991 | 0.037363 | −0.018008 | 0.042328 | 0.044061 | 0.001615 | −0.011202 | −0.00534 | −0.013003 | −0.003795 | −0.008055 | 0.002595 | −0.006855 |
| 103 | −0.01872 | −0.007075 | −0.001236 | −0.002317 | 0.034457 | −0.0347 | −0.013434 | 0.001901 | −0.008171 | 0.078879 | 0.005828 | −0.002654 | −0.002647 | 0.027146 |
| 104 | 0.011923 | −0.013359 | 0.004375 | −0.013029 | −0.023751 | 0.007818 | 0.026945 | 0.009052 | −0.018215 | 0.020855 | −0.027302 | −0.024143 | −0.012538 | 0.038942 |
| 105 | 0.005544 | 0.041917 | −0.036177 | −0.007882 | −0.07696 | −0.0017 | 0.010472 | 0.021911 | −0.018472 | −0.000355 | −0.023905 | 0.00882 | −0.010752 | 0.056535 |
| 106 | −0.012539 | −0.0096 | −0.016133 | 0.023147 | 0.032518 | −0.026856 | −0.035035 | −0.019102 | 0.005116 | −0.025388 | 0.007171 | 0.007036 | −0.011703 | −0.014497 |
| 107 | −0.009818 | −0.00445 | 0.009624 | 0.015475 | 0.000344 | 0.013325 | 0.002848 | −0.003876 | 0.006408 | −0.005656 | 0.000893 | 0.007641 | −0.003264 | −0.019938 |
| 108 | 0.004675 | 0.018762 | 0.040909 | −0.004159 | −0.022547 | 0.001916 | 0.015237 | 0.001477 | 0.001326 | 0.022227 | 0.000519 | 0.025048 | −0.005781 | 0.011609 |
| 109 | −0.024677 | −0.030095 | 0.002315 | 0.005671 | −0.000391 | 0.044665 | −0.025565 | 0.013243 | −0.0425 | 0.063241 | −0.029972 | −0.031379 | −0.008015 | 0.017824 |
| 110 | −0.002749 | −0.032624 | −0.008741 | 0.017372 | 0.01146 | −0.014388 | 0.018796 | 0.039486 | 0.023502 | −0.0047 | 0.024191 | −0.025665 | 0.02369 | 0.000113 |
| 111 | 0.008061 | −0.014533 | 0.019012 | −0.014276 | −0.020235 | −0.004402 | 0.015882 | 0.002321 | 0.011307 | −0.023938 | −0.009958 | 0.000147 | −0.01342 | −0.012134 |
| 112 | 0.004366 | 0.011583 | 0.019171 | 0.01079 | −0.022574 | −0.026842 | 0.012388 | 0.004381 | 0.007355 | −0.027587 | −0.014635 | 0.026543 | 0.015308 | 0.021637 |
| 113 | 0.002241 | −0.000357 | −0.001374 | 0.022502 | 0.013941 | 0.014706 | −0.018196 | −0.010286 | −0.005269 | −0.029575 | 0.004775 | −0.02374 | −0.009375 | −0.057309 |
| 114 | 0.01139 | 0.0242 | −0.010608 | 0.004415 | −0.039378 | 0.064395 | 0.011474 | −0.013066 | −0.011664 | 0.006996 | −0.036443 | −0.027524 | 0.001805 | −0.013751 |
| 115 | −0.016559 | 0.002735 | 0.026613 | −0.012794 | 0.008915 | −0.03463 | −0.018219 | 0.018857 | −0.01302 | −0.007805 | 0.005074 | 0.043447 | 0.006127 | 0.054457 |
| 116 | −0.013885 | −0.020798 | −0.01207 | 0.058134 | −0.033602 | −0.042505 | −0.005717 | −0.026636 | 0.007689 | 0.012044 | −0.026082 | 0.02972 | −0.018633 | 0.010833 |
| 117 | 0.012683 | 0.020843 | 0.011665 | −0.101149 | −0.035517 | 0.033317 | 0.032986 | 0.029448 | 0.030027 | −0.019006 | −0.003556 | −0.00697 | 0.02542 | 0.069625 |
| 118 | 0.014226 | 0.035999 | 0.018349 | −0.051018 | −0.010007 | 0.001015 | 0.00374 | 0.011479 | −0.016569 | 0.044179 | −0.004329 | 0.007422 | −0.019909 | 0.023123 |
| 119 | 0.007673 | −0.013227 | −0.010988 | −0.013302 | −0.010834 | −0.006009 | 0.001735 | −0.005731 | −0.00286 | 0.011296 | 0.010547 | 0.007237 | 0.010647 | 0.009392 |
| 120 | −0.011433 | −0.020352 | −0.001929 | −0.021397 | −0.008673 | 0.018591 | −0.010063 | 0.000579 | 0.018876 | 0.003684 | 0.022862 | −0.006406 | −0.008275 | 0.021761 |
| 121 | −0.003837 | −0.029624 | −0.017506 | 0.013911 | 0.036227 | −0.023283 | −0.026805 | −0.009537 | 0.002391 | −0.030038 | −0.003782 | 0.011948 | −0.000814 | −0.040477 |
| 122 | −0.012677 | 0.024427 | 0.009629 | 0.025914 | 0.0194 | −0.001118 | −0.006238 | −0.001694 | −0.00429 | 0.026082 | −0.010279 | 0.005851 | −0.00606 | 0.006274 |
| 123 | −0.001254 | 0.009329 | 0.015569 | 0.02012 | 0.020415 | −0.033938 | −0.016 | −0.031855 | −0.001904 | 0.006277 | 0.000944 | 0.008178 | −0.010342 | −0.006955 |
| 124 | 0.014541 | 0.000875 | −0.013026 | −0.027169 | −0.023827 | −0.029945 | 0.003127 | −0.005678 | −0.00598 | 0.01626 | −0.004942 | −0.014039 | 0.01027 | −0.002317 |
| 125 | 0.006 | −0.005789 | 0.009856 | 0.012587 | 0.016383 | −0.015029 | −0.006998 | 0.003205 | 0.003306 | −0.026174 | 0.008942 | −0.011558 | 0.00663 | 0.019816 |
| 126 | 0.024144 | 0.013258 | 0.002928 | 0.005666 | 0.009176 | −0.00163 | 0.025138 | 0.003777 | −0.004697 | 0.057326 | −0.009185 | 0.026338 | 0.001725 | 0.029964 |
| 127 | 0.009201 | 0.002679 | −0.006491 | 0.010741 | 0.012959 | −0.014783 | 0.012758 | 0.020166 | −0.002633 | 0.042473 | 0.001594 | 0.001356 | 0.017738 | 0.021705 |
| 128 | 0.014879 | 0.004298 | −0.024283 | 0.003645 | 0.002444 | −0.014069 | 0.027014 | 0.026729 | 0.006728 | 0.017315 | 0.005433 | −0.005102 | 0.014594 | 0.020072 |
| 129 | 0.009255 | −0.025957 | 0.025877 | 0.016557 | −0.006515 | −0.054752 | 0.016912 | −0.025788 | −0.007323 | −0.084822 | −0.015772 | 0.036197 | 0.000548 | 0.002632 |
| 130 | −0.015758 | −0.011619 | 0.013381 | −0.010893 | 0.047745 | −0.078357 | −0.037248 | 0.005789 | −0.005002 | 0.020976 | 0.035177 | −0.000117 | 0.007083 | −0.020419 |
| 131 | 0.011544 | 0.010324 | −0.040046 | 0.006261 | −0.030348 | −0.04163 | −0.00248 | 0.015613 | 0.012944 | −0.075654 | 0.016184 | 0.041247 | 0.000029 | 0.028739 |
| 132 | 0.022363 | −0.021074 | −0.017211 | −0.05553 | −0.02637 | −0.017543 | 0.022842 | 0.047917 | 0.009645 | −0.009905 | 0.016774 | −0.024989 | 0.013431 | 0.027273 |
| 133 | −0.002557 | −0.001675 | 0.009566 | 0.034654 | 0.035648 | −0.01651 | −0.002872 | 0.042975 | 0.023216 | 0.015014 | 0.020218 | 0.026035 | 0.006643 | 0.04256 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 134 | 0.022288 | 0.032556 | 0.014868 | −0.053613 | 0.033724 | −0.027002 | 0.006504 | −0.005736 | −0.010225 | −0.016741 | 0.010467 | 0.04029 | 0.017652 | −0.03432 |
| 135 | 0.007887 | 0.004028 | −0.016896 | −0.01612 | −0.002817 | −0.016818 | −0.010388 | −0.008358 | 0.00149 | 0.013895 | −0.000642 | −0.032074 | −0.007572 | 0.001036 |
| 136 | 0.001403 | 0.011968 | −0.022935 | −0.032687 | 0.006098 | −0.041677 | −0.022771 | −0.003614 | 0.008048 | 0.011309 | 0.016936 | −0.01536 | −0.003996 | −0.013888 |
| 137 | 0.016462 | −0.002878 | −0.018212 | 0.033725 | 0.01913 | −0.027543 | −0.022456 | −0.002835 | −0.016613 | −0.012983 | −0.00635 | 0.004483 | 0.002714 | 0.013397 |
| 138 | −0.018775 | −0.028928 | −0.008315 | 0.007632 | −0.007676 | 0.03821 | −0.006766 | 0.01744 | 0.004425 | 0.036949 | 0.006223 | 0.008379 | 0.005269 | −0.034406 |
| 139 | −0.003825 | −0.023314 | 0.006867 | 0.063967 | 0.000666 | 0.004828 | 0.00262 | −0.021939 | −0.044532 | 0.020797 | −0.023601 | 0.028147 | −0.035607 | 0.006249 |
| 140 | −0.008631 | −0.031126 | −0.018498 | −0.010323 | −0.00171 | 0.003073 | 0.014926 | 0.000882 | 0.00884 | −0.045989 | 0.005793 | 0.089292 | 0.006581 | 0.016924 |
| 141 | −0.015231 | −0.00039 | −0.004484 | −0.046108 | −0.002704 | −0.028419 | 0.008828 | −0.000159 | −0.010815 | 0.048442 | 0.003248 | −0.036272 | −0.007158 | −0.006347 |
| 142 | −0.001194 | −0.007418 | 0.014649 | −0.031871 | −0.026894 | −0.004337 | −0.010239 | −0.016122 | −0.019533 | 0.005509 | −0.025303 | 0.00282 | −0.013845 | 0.003621 |
| 143 | −0.016654 | 0.020734 | 0.017762 | 0.039513 | 0.011232 | −0.012527 | −0.007402 | −0.023854 | −0.007679 | −0.002546 | −0.016936 | −0.003108 | −0.018912 | −0.002796 |
| 144 | −0.005016 | −0.010233 | 0.001319 | 0.013236 | 0.003133 | −0.016495 | −0.006917 | −0.062871 | −0.006478 | 0.016956 | −0.011131 | −0.000154 | −0.019335 | −0.040943 |
| 145 | 0.007013 | −0.001564 | −0.031049 | −0.011181 | 0.008863 | 0.017506 | −0.007515 | −0.005764 | −0.011995 | −0.009383 | −0.020277 | −0.018892 | −0.020564 | −0.033811 |
| 146 | 0.016773 | −0.019387 | 0.002169 | −0.022985 | −0.002667 | −0.031478 | 0.010148 | −0.01132 | 0.009298 | −0.028526 | 0.012221 | −0.007755 | −0.006648 | −0.001708 |
| 147 | 0.034883 | −0.006661 | 0.041163 | −0.070785 | −0.026388 | 0.019014 | 0.005048 | −0.036919 | 0.009856 | −0.077378 | 0.004974 | 0.000386 | −0.014081 | 0.018328 |
| 148 | 0.008325 | 0.016917 | 0.007509 | 0.032203 | 0.034673 | −0.028505 | −0.025841 | −0.036919 | −0.001881 | 0.030858 | −0.00847 | 0.005544 | −0.031844 | 0.040327 |
| 149 | −0.020879 | 0.006915 | −0.022386 | 0.006595 | 0.003766 | −0.011046 | 0.000432 | 0.014909 | −0.012818 | 0.007382 | −0.01466 | 0.001525 | −0.012626 | 0.004308 |
| 150 | 0.005845 | −0.003062 | 0.004297 | 0.033999 | 0.019439 | −0.060309 | −0.01687 | −0.006258 | 0.002496 | 0.006331 | 0.013415 | −0.00759 | 0.000688 | −0.015148 |
| 151 | 0.002448 | 0.028214 | 0.017138 | 0.016106 | 0.020083 | −0.028762 | 0.001979 | −0.057588 | −0.007633 | 0.002994 | 0.003323 | 0.030362 | −0.036139 | −0.036029 |
| 152 | −0.010224 | −0.010296 | −0.010224 | 0.005422 | −0.006169 | −0.020481 | 0.004121 | 0.004123 | −0.001383 | 0.011566 | −0.011067 | 0.003163 | 0.010281 | −0.006323 |
| 153 | −0.004753 | −0.015804 | 0.02483 | −0.022851 | −0.005687 | −0.021921 | 0.015796 | −0.01573 | −0.011886 | 0.043038 | −0.002777 | −0.00775 | −0.005853 | 0.006577 |
| 154 | 0.008855 | −0.004421 | −0.015912 | −0.029167 | −0.036637 | −0.01601 | −0.002025 | −0.003214 | −0.008848 | −0.03927 | −0.015524 | 0.006109 | −0.011846 | 0.004883 |
| 155 | 0.009437 | −0.041863 | −0.016548 | 0.020361 | −0.027428 | −0.000317 | 0.017728 | 0.015438 | −0.011624 | 0.009527 | −0.014407 | 0.011414 | −0.00116 | 0.001521 |
| 156 | −0.009566 | 0.018332 | 0.009407 | 0.005639 | 0.014802 | −0.015003 | 0.002656 | −0.032543 | −0.000947 | −0.009349 | −0.0079 | −0.024231 | −0.001658 | −0.0177 |
| 157 | −0.000671 | −0.029019 | −0.001055 | 0.002228 | −0.008015 | −0.01227 | 0.00564 | −0.002413 | 0.007053 | −0.004139 | −0.004909 | −0.005979 | 0.000307 | 0.018674 |
| 158 | 0.000742 | −0.025462 | 0.026548 | −0.035373 | −0.027781 | 0.023032 | 0.007967 | 0.02061 | −0.012237 | 0.026699 | −0.001424 | −0.00325 | −0.006969 | 0.050952 |
| 159 | 0.00711 | −0.002511 | −0.075514 | 0.025313 | −0.058101 | 0.023827 | −0.018607 | −0.008993 | −0.02723 | 0.020507 | −0.050178 | −0.027827 | −0.028392 | 0.001205 |
| 160 | −0.002619 | 0.020933 | 0.012998 | −0.016659 | 0.037749 | 0.006841 | −0.013484 | −0.044066 | −0.004005 | −0.064387 | −0.03244 | −0.024637 | −0.001965 | −0.019881 |
| 161 | 0.003318 | −0.049084 | 0.012874 | 0.014473 | −0.021643 | 0.021241 | 0.025253 | 0.008097 | −0.008632 | 0.006814 | −0.019293 | 0.001319 | −0.000014 | 0.037545 |
| 162 | 0.001226 | 0.006685 | 0.004479 | −0.014925 | 0.003718 | −0.026581 | −0.010648 | −0.023906 | −0.003196 | −0.034085 | −0.004555 | 0.029002 | −0.022497 | −0.001517 |
| 163 | 0.009028 | −0.003816 | −0.002508 | −0.031685 | −0.001818 | −0.024678 | −0.011032 | −0.00834 | −0.012453 | −0.030175 | −0.029206 | −0.033257 | 0.002753 | 0.001206 |
| 164 | −0.004674 | 0.008157 | −0.018514 | −0.021829 | −0.064994 | 0.002802 | 0.015237 | −0.015987 | −0.036521 | −0.005452 | −0.033749 | −0.005096 | −0.022734 | 0.008238 |
| 165 | −0.009443 | −0.00498 | 0.025605 | 0.020905 | 0.008944 | −0.019741 | 0.039374 | 0.030127 | 0.001108 | −0.039252 | −0.028089 | 0.034334 | 0.00297 | −0.029019 |
| 166 | −0.00943 | 0.009687 | −4.011826 | −0.027473 | −4.023315 | 0.002094 | −4.006991 | −4.013831 | −4.002975 | 0.056881 | 0.00553 | −4.0067191 | −0.003497 | −0.028366 |
| 167 | 0.014233 | −0.018582 | −0.019692 | 0.02104 | −0.008642 | −0.005467 | 0.007634 | −0.007741 | −0.022384 | 0.047204 | −0.007091 | −0.029386 | −0.001501 | −0.015747 |
| 168 | −0.012415 | 0.015984 | 0.002367 | −0.023633 | 0.021621 | −0.012806 | −0.011334 | 0.000073 | 0.004945 | −0.042641 | 0.017759 | −0.014874 | 0.006849 | −0.018807 |
| 169 | −0.008942 | −0.015677 | 0.007707 | −0.016088 | −0.019648 | −0.002303 | 0.001049 | 0.011998 | 0.009615 | −0.021119 | 0.011775 | −0.040086 | 0.008628 | −0.00952 |
| 170 | −0.015505 | −0.006407 | 0.018371 | −0.030642 | −0.014751 | −0.00362 | 0.00107 | 0.003477 | 0.014689 | −0.038416 | 0.013518 | −0.034133 | 0.009843 | −0.029507 |
| 171 | −0.011096 | −0.014784 | 0.00269 | −0.021884 | −0.020866 | −0.018752 | 0.014524 | 0.009379 | 0.009312 | 0.005602 | 0.011565 | −0.027695 | 0.004585 | −0.03063 |
| 172 | −0.005274 | −0.01526 | 0.010243 | 0.007787 | 0.001793 | 0.016132 | 0.004523 | −0.002438 | 0.007722 | 0.007539 | 0.005718 | 0.004346 | 0.005486 | −0.000258 |
| 173 | −0.01075 | −0.01797 | 0.014881 | 0.039235 | 0.030659 | 0.02656 | −0.002679 | 0.008961 | 0.006426 | −0.022601 | 0.001199 | 0.037495 | 0.000663 | 0.007974 |
| 174 | −0.001461 | −0.03113 | 0.001647 | 0.005018 | 0.029315 | 0.029406 | −0.002502 | 0.019211 | 0.008748 | −0.029529 | 0.025186 | −0.006327 | 0.001316 | −0.030269 |
| 175 | −0.002629 | −0.012146 | 0.004747 | −0.015327 | 0.022281 | −0.027924 | −0.004974 | 0.022386 | 0.004704 | −0.026525 | 0.029831 | −0.022936 | 0.002144 | −0.044111 |
| 176 | −0.016518 | 0.00856 | 0.008632 | −0.015462 | 0.000728 | −0.024732 | −0.011504 | 0.016232 | 0.0205 | 0.002261 | 0.010508 | −0.052573 | 0.010105 | −0.000956 |
| 177 | 0.013922 | −0.018752 | −0.005444 | −0.021744 | −0.007554 | 0.034463 | 0.01991 | −0.01464 | 0.005804 | 0.074548 | 0.027358 | −0.028453 | 0.007717 | −0.01352 |
| 178 | 0.024272 | −0.010688 | 0.007378 | 0.027933 | 0.010171 | −0.0136 | 0.018978 | 0.00402 | 0.00345 | 0.012077 | 0.007861 | −0.004993 | 0.003503 | 0.003592 |
| 179 | 0.005848 | −0.000851 | 0.007443 | 0.018459 | −0.001082 | 0.006409 | 0.001479 | −0.013692 | 0.004395 | 0.014542 | 0.004877 | −0.02905 | 0.002782 | −0.021125 |
| 180 | 0.001134 | 0.009318 | 0.011398 | 0.022652 | 0.008713 | 0.012212 | −0.00305 | −0.002607 | 0.009745 | 0.01739 | 0.012035 | −0.008898 | 0.005676 | −0.007316 |
| 181 | 0.00414 | 0.002341 | 0.013641 | 0.021986 | 0.000306 | 0.014449 | 0.004346 | −0.002467 | 0.009282 | 0.011266 | 0.004532 | −0.016623 | 0.008257 | −0.009896 |
| 182 | −0.003852 | 0.010075 | 0.008265 | 0.010928 | 0.003983 | 0.005809 | −0.002553 | −0.011594 | 0.010062 | 0.012015 | 0.002035 | −0.017479 | 0.004482 | −0.01297 |
| 183 | 0.016687 | 0.008635 | −0.009372 | 0.017044 | −0.004546 | −0.021354 | 0.008628 | −0.025159 | 0.002434 | 0.022788 | −0.002575 | −0.033394 | 0.00238 | −0.022435 |

APPENDIX B3-continued

PCA Transformation
Matrix (340 × 340 Early/Late)

| | | | | | | | | | | | | | |
|---|---|---|---|---|---|---|---|---|---|---|---|---|---|
| 184 | 0.019664 | −0.001618 | −0.011816 | 0.019097 | 0.029643 | −0.018844 | −0.022859 | −0.060143 | 0.002804 | −0.026815 | −0.008911 | −0.02508 | −0.017429 | −0.040688 |
| 185 | −0.023288 | −0.003662 | −0.013681 | 0.031503 | 0.004174 | 0.036459 | −0.003876 | 0.012111 | 0.010173 | −0.004362 | −0.005963 | −0.065314 | 0.024093 | −0.047646 |
| 186 | −0.007559 | 0.003987 | 0.023558 | 0.007774 | 0.030086 | −0.007435 | −0.014814 | −0.012535 | 0.005195 | −0.009103 | 0.029358 | 0.01635 | −0.011875 | −0.004294 |
| 187 | 0.00833 | 0.019108 | 0.015249 | 0.005947 | 0.027905 | 0.025175 | −0.011783 | −0.013744 | 0.003062 | −0.000145 | 0.002271 | 0.014639 | −0.004827 | 0.036298 |
| 188 | 0.000994 | 0.006499 | 0.008654 | −0.007413 | 0.027012 | 0.038214 | −0.014638 | −0.010612 | 0.006092 | −0.01876 | 0.011367 | 0.001172 | −0.005078 | 0.005876 |
| 189 | 0.000871 | 0.012406 | 0.017781 | −0.03295 | 0.028117 | 0.004708 | −0.044405 | −0.030749 | −0.001882 | −0.018127 | 0.012128 | −0.042356 | −0.018331 | −0.015538 |
| 190 | −0.007901 | 0.006933 | −0.022949 | −0.006262 | 0.005978 | −0.029356 | −0.024362 | −0.012255 | −0.014061 | −0.010789 | 0.002615 | −0.010432 | −0.011833 | −0.007107 |
| 191 | −0.009048 | −0.006813 | −0.009904 | −0.037389 | −0.016273 | −0.00408 | −0.002947 | −0.006535 | −0.011915 | −0.002683 | −0.0039 | −0.011636 | −0.009312 | 0.018321 |
| 192 | 0.01549 | 0.005914 | −0.033105 | 0.02935 | −0.001533 | −0.015374 | 0.029405 | −0.006406 | 0.002491 | −0.000982 | −0.000957 | 0.014964 | 0.004547 | 0.00485 |
| 193 | 0.002661 | 0.011366 | −0.000371 | −0.007329 | 0.019059 | 0.004828 | −0.002168 | −0.030959 | 0.013308 | −0.025492 | 0.014842 | −0.020559 | 0.002077 | −0.004231 |
| 194 | −0.018103 | 0.012434 | 0.030111 | −0.007184 | 0.03335 | −0.007777 | −0.019365 | 0.004041 | 0.006608 | 0.002265 | 0.031203 | 0.026977 | 0.006452 | 0.031347 |
| 195 | 0.003004 | −0.003999 | 0.021161 | 0.057301 | 0.011889 | −0.000998 | −0.014877 | −0.024819 | 0.001095 | −0.000931 | −0.016553 | 0.009083 | −0.00008 | 0.005636 |
| 196 | 0.000419 | 0.00031 | 0.001541 | 0.029039 | 0.007152 | −0.005305 | −0.01872 | −0.020242 | −0.003146 | −0.018405 | −0.003814 | 0.004264 | −0.007807 | −0.010657 |
| 197 | −0.008119 | 0.011634 | −0.029237 | −0.012163 | −0.020706 | −0.012352 | −0.004495 | 0.007271 | −0.006457 | −0.032686 | −0.004287 | −0.005048 | −0.010161 | 0.012373 |
| 198 | 0.016408 | 0.005938 | 0.024508 | 0.000984 | 0.004905 | −0.026973 | 0.005387 | −0.033209 | 0.000343 | 0.011752 | −0.022922 | −0.018679 | 0.00504 | −0.002652 |
| 199 | −0.017525 | −0.035314 | −0.022848 | −0.04411 | −0.027021 | 0.014117 | −0.028649 | 0.016945 | −0.028148 | 0.002153 | −0.008469 | −0.011613 | −0.019016 | 0.016821 |
| 200 | 0.033961 | 0.001995 | 0.011093 | 0.021215 | −0.014157 | −0.007049 | 0.035322 | −0.010468 | −0.015923 | 0.067645 | −0.011577 | 0.00975 | 0.002987 | 0.023826 |
| 201 | −0.01634 | 0.021983 | −0.005109 | −0.010878 | −0.037348 | −0.005755 | 0.016961 | 0.032945 | −0.012328 | −0.009141 | −0.038853 | −0.051049 | 0.002082 | 0.054225 |
| 202 | 0.010388 | 0.034606 | 0.022263 | 0.00399 | 0.015875 | −0.022684 | 0.01978 | −0.004389 | 0.009573 | −0.037422 | 0.00044 | 0.019984 | 0.009463 | −0.007354 |
| 203 | 0.020722 | 0.013706 | −0.052082 | −0.00809 | −0.002357 | −0.035494 | −0.008484 | 0.001229 | −0.016458 | 0.010321 | −0.015214 | 0.028264 | −0.004988 | 0.0533 |
| 204 | −0.008913 | 0.003263 | −0.008368 | 0.049848 | −0.038864 | −0.021188 | 0.026557 | −0.024277 | 0.025561 | −0.031717 | −0.032655 | 0.001547 | 0.005294 | 0.036519 |
| 205 | −0.016684 | 0.017074 | −0.009318 | 0.010503 | 0.034041 | 0.032724 | −0.039146 | 0.018813 | −0.024532 | 0.04789 | −0.010501 | 0.055712 | 0.000855 | 0.034008 |
| 206 | 0.035344 | 0.031552 | 0.002816 | −0.048514 | 0.021647 | −0.053101 | −0.010328 | 0.018265 | −0.01645 | −0.03452 | 0.005028 | −0.001271 | 0.024393 | 0.049831 |
| 207 | 0.021728 | 0.015667 | 0.000841 | 0.058638 | −0.03242 | −0.034039 | 0.014928 | 0.018342 | −0.006306 | 0.013375 | 0.002392 | −0.016495 | 0.011442 | 0.025052 |
| 208 | −0.004983 | −0.000895 | −0.014869 | −0.006563 | −0.007413 | −0.0417 | −0.006239 | 0.032691 | −0.01684 | −0.016763 | −0.00852 | −0.028535 | 0.021064 | 0.028582 |
| 209 | 0.0053 | 0.01021 | −0.016672 | 0.004232 | 0.016808 | −0.029031 | −0.009728 | 0.027157 | 0.031615 | −0.0119651 | 0.019668 | 0.03929 | 0.002333 | 0.018312 |
| 210 | 0.021614 | −0.0029 | −0.047403 | 0.029254 | −0.029322 | −0.018858 | 0.024038 | −0.016755 | 0.018697 | 0.030849 | −0.013095 | −0.067432 | 0.003285 | −0.022076 |
| 211 | −0.016038 | 0.001998 | −0.013846 | 0.065013 | −0.010141 | 0.015462 | 0.032088 | −0.014298 | −0.00146 | 0.031825 | −0.014988 | 0.049625 | −0.00472 | 0.013975 |
| 212 | −0.003996 | −0.020261 | 0.002276 | 0.042654 | −0.052521 | 0.02252 | 0.002499 | −0.055988 | −0.019937 | 0.008498 | −0.053996 | 0.007497 | −0.022216 | −0.014436 |
| 213 | −0.019078 | −0.017586 | 0.030152 | −0.013564 | 0.014396 | 0.078673 | 0.014799 | −0.020425 | −0.00189 | 0.060068 | 0.004565 | 0.020763 | 0.002847 | 0.005278 |
| 214 | 0.013204 | 0.010252 | 0.006479 | 0.014324 | −0.001214 | −0.012782 | −0.003251 | −0.012177 | 0.006215 | −0.001884 | 0.006755 | −0.019772 | 0.005514 | −0.008481 |
| 215 | 0.004318 | −0.020069 | 0.015913 | 0.024388 | −0.018857 | 0.016433 | −0.004237 | −0.009817 | 0.007395 | −0.007976 | 0.014108 | −0.073862 | −0.002534 | −0.023732 |
| 216 | −0.010215 | 0.011536 | 0.023232 | −0.034249 | −0.004614 | 0.007552 | 0.002655 | 0.014364 | 0.008701 | 0.014275 | 0.017711 | −0.001506 | −0.009142 | −0.01802 |
| 217 | 0.002195 | −0.003055 | −0.008393 | −0.037026 | 0.017824 | −0.016513 | −0.016749 | −0.007093 | −0.005887 | −0.03261 | 0.010105 | −0.008386 | 0.002429 | −0.012121 |
| 218 | −0.01223 | −0.01256 | −0.015348 | 0.019939 | 0.000939 | 0.011952 | −0.020176 | −0.000922 | 0.00716 | −0.040212 | −0.002082 | −0.011602 | −0.007607 | −0.013476 |
| 219 | −0.002723 | −0.019627 | 0.025688 | −0.011735 | 0.006643 | −0.022174 | −0.014177 | −0.014632 | −0.003627 | −0.017735 | −0.005575 | −0.001895 | −0.01717 | −0.031791 |
| 220 | 0.009772 | −0.010605 | −0.020059 | −0.025773 | 0.002394 | −0.037285 | −0.020443 | −0.004567 | −0.003975 | −0.014039 | −0.006496 | −0.003392 | 0.004693 | −0.000733 |
| 221 | −0.003956 | 0.004054 | 0.001808 | 0.034531 | 0.012875 | −0.003439 | −0.000024 | 0.0147 | 0.008506 | −0.008615 | −0.008392 | 0.034098 | −0.003799 | 0.002726 |
| 222 | −0.003518 | −0.013828 | −0.004979 | 0.030759 | 0.015693 | −0.010607 | −0.010496 | −0.019051 | −0.011398 | 0.004876 | −0.01692 | 0.017418 | −0.007312 | −0.001674 |
| 223 | −0.021591 | −0.014524 | 0.013223 | 0.014043 | 0.009783 | −0.009763 | −0.000766 | 0.008743 | −0.001716 | 0.019097 | −0.000469 | 0.021572 | 0.003363 | 0.010909 |
| 224 | −0.009453 | −0.006592 | 0.008907 | −0.014285 | −0.023613 | 0.007558 | 0.024257 | 0.024213 | −0.004425 | 0.026286 | 0.005875 | −0.007046 | 0.000022 | 0.006884 |
| 225 | −0.016212 | −0.016837 | 0.008453 | −0.011401 | −0.030057 | 0.017981 | 0.029574 | 0.038045 | −0.008202 | 0.027264 | 0.000045 | 0.001976 | 0.003486 | 0.001233 |
| 226 | −0.012422 | −0.012325 | −0.001858 | 0.022649 | 0.002391 | −0.022237 | −0.015704 | −0.021028 | −0.00757 | 0.007125 | −0.006015 | 0.001029 | −0.013558 | −0.004333 |
| 227 | −0.005394 | −0.026475 | 0.003187 | −0.010744 | −0.010401 | −0.012959 | −0.003545 | −0.001307 | −0.008112 | 0.032294 | 0.01513 | −0.022323 | −0.004672 | 0.013699 |
| 228 | −0.003364 | 0.010514 | −0.012766 | −0.028834 | 0.00597 | −0.034448 | −0.017636 | 0.002076 | −0.023135 | −0.030172 | −0.003326 | 0.024829 | −0.017825 | 0.011815 |
| 229 | 0.020854 | 0.034342 | 0.007861 | 0.023491 | 0.011741 | 0.053188 | −0.003392 | 0.001299 | −0.00424 | 0.025537 | 0.001624 | −0.011464 | 0.00789 | 0.010904 |
| 230 | 0.008367 | 0.013133 | 0.007528 | −0.005783 | −0.011196 | 0.034959 | 0.011664 | 0.016767 | −0.008279 | 0.030945 | 0.007686 | −0.007554 | 0.020414 | −0.003354 |
| 231 | −0.025048 | 0.003707 | −0.001226 | −0.016708 | −0.005642 | 0.018048 | −0.003816 | 0.032274 | 0.00706 | 0.040987 | 0.004955 | 0.018704 | 0.012995 | 0.017308 |
| 232 | 0.003511 | 0.00588 | 0.003034 | −0.018753 | −0.023613 | 0.005075 | 0.008368 | −0.008025 | −0.006428 | −0.027654 | −0.015359 | −0.01163 | −0.007109 | 0.00845 |
| 233 | 0.009135 | −0.018577 | 0.011776 | 0.009551 | 0.001247 | 0.045025 | 0.021 | −0.003525 | 0.001382 | 0.02009 | −0.009828 | −0.018799 | −0.002295 | 0.002528 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 234 | 0.000515 | −0.010749 | 0.005209 | −0.01668 | −0.00601 | 0.010651 | 0.000984 | 0.056351 | −0.001242 | 0.011975 | 0.013293 | 0.024054 | 0.006263 | 0.017479 |
| 235 | −0.010574 | −0.026722 | 0.006245 | −0.027644 | 0.000154 | 0.018808 | −0.003725 | 0.02721 | −0.010018 | 0.024218 | −0.005595 | 0.023207 | 0.000002 | 0.019662 |
| 236 | −0.001665 | 0.022606 | 0.008978 | −0.017532 | −0.003263 | −0.001564 | 0.005203 | −0.006429 | 0.00595 | 0.015325 | 0.004305 | −0.015188 | 0.009288 | −0.013216 |
| 237 | −0.008607 | 0.009691 | −0.006148 | −0.007561 | −0.018529 | 0.033186 | 0.008401 | 0.010917 | −0.000456 | −0.022766 | 0.00771 | −0.004575 | −0.003481 | −0.012081 |
| 238 | 0.001082 | 0.007949 | 0.02212 | −0.022424 | −0.003788 | 0.010024 | 0.008221 | 0.013641 | −0.005017 | −0.001293 | 0.002637 | 0.017889 | 0.001857 | −0.008164 |
| 239 | 0.00767 | −0.00125 | 0.02373 | −0.011067 | 0.011876 | −0.010691 | 0.00952 | 0.014786 | 0.001556 | 0.005597 | −0.001359 | 0.011998 | 0.006758 | −0.000228 |
| 240 | 0.008279 | 0.010764 | −0.009366 | −0.000003 | 0.008286 | −0.014582 | 0.004204 | −0.014062 | 0.00454 | −0.010127 | 0.000187 | −0.004071 | −0.006875 | 0.002184 |
| 241 | 0.005749 | 0.004001 | −0.018828 | 0.017672 | −0.012158 | 0.018123 | 0.014174 | −0.00596 | 0.012178 | 0.010238 | −0.000662 | −0.024748 | −0.00502 | −0.018698 |
| 242 | −0.001315 | 0.010217 | 0.003499 | 0.001457 | 0.013588 | 0.016418 | −0.005939 | 0.002681 | −0.000393 | 0.023501 | 0.001381 | 0.017939 | −0.001125 | 0.014916 |
| 243 | −0.009305 | 0.000101 | 0.018556 | −0.009676 | 0.014352 | −0.007585 | −0.012524 | −0.018225 | −0.012316 | 0.005674 | −0.000671 | 0.014419 | −0.02886 | 0.002865 |
| 244 | 0.01349 | 0.029606 | 0.005287 | 0.000669 | −0.003724 | 0.00669 | 0.01934 | 0.024205 | 0.014755 | 0.022487 | 0.005573 | 0.012679 | 0.013294 | 0.033283 |
| 245 | 0.011669 | 0.011738 | −0.002515 | 0.000151 | −0.000701 | 0.041504 | 0.02605 | 0.012188 | 0.017994 | 0.01352 | 0.006154 | −0.030874 | 0.01921 | −0.007089 |
| 246 | 0.011711 | −0.016541 | 0.001413 | 0.000257 | 0.000481 | 0.006376 | 0.004683 | 0.004603 | −0.001853 | −0.013729 | −0.007477 | −0.013308 | 0.001973 | −0.006005 |
| 247 | 0.006857 | −0.012223 | 0.011257 | 0.010566 | 0.018612 | −0.020472 | −0.005308 | −0.012677 | −0.006145 | 0.002432 | −0.009147 | 0.006009 | −0.002242 | −0.008131 |
| 248 | 0.009256 | −0.008469 | 0.008987 | 0.002616 | 0.012396 | −0.028837 | −0.005874 | −0.024226 | −0.004384 | −0.001904 | −0.008143 | 0.006787 | −0.001042 | −0.014452 |
| 249 | 0.008738 | 0.002451 | −0.00327 | −0.009292 | −0.00021 | −0.033106 | 0.005569 | −0.037982 | 0.006515 | −0.045348 | −0.002141 | −0.015908 | 0.008477 | −0.018238 |
| 250 | 0.00722 | 0.008195 | −0.00561 | −0.023671 | −0.01761 | −0.00905 | 0.015378 | 0.018516 | 0.00631 | 0.014144 | 0.011111 | −0.007045 | 0.006159 | 0.014562 |
| 251 | 0.005174 | 0.006179 | −0.016251 | −0.004635 | −0.016866 | −0.004679 | 0.01655 | 0.018031 | −0.002183 | 0.008606 | −0.006833 | −0.003993 | 0.00932 | 0.009742 |
| 252 | 0.004948 | 0.015102 | −0.029038 | 0.014443 | −0.01462 | 0.028626 | 0.009136 | −0.00384 | 0.015903 | −0.000564 | −0.001465 | −0.038233 | 0.019333 | −0.017026 |
| 253 | −0.011406 | 0.014398 | −0.006838 | 0.007201 | −0.018427 | 0.008903 | 0.008952 | 0.011542 | 0.004189 | 0.004504 | 0.014132 | 0.021028 | −0.001927 | −0.005389 |
| 254 | −0.005755 | −0.003583 | 0.031004 | −0.012372 | 0.004817 | −0.007338 | 0.012432 | 0.003104 | 0.008244 | 0.017408 | 0.009027 | 0.00843 | 0.004372 | 0.017855 |
| 255 | 0.011309 | 0.011438 | 0.014506 | −0.014516 | −0.001554 | −0.001478 | 0.009746 | 0.010219 | 0.008847 | 0.001769 | 0.002399 | 0.010305 | 0.0027 | 0.027148 |
| 256 | 0.011627 | 0.014594 | −0.008358 | −0.000667 | 0.002152 | 0.039346 | −0.000492 | −0.005748 | 0.025633 | −0.031134 | 0.006768 | −0.025981 | 0.005977 | −0.010073 |
| 257 | −0.009908 | −0.02262 | 0.00066 | 0.010951 | −0.010936 | 0.003786 | 0.004876 | −0.001062 | −0.004401 | 0.000846 | −0.014012 | 0.004776 | 0.009922 | 0.008122 |
| 258 | −0.029036 | −0.030936 | −0.0083 | 0.021217 | −0.000721 | −0.008707 | −0.009916 | −0.018784 | −0.006528 | 0.005481 | −0.004332 | 0.00506 | −0.019902 | −0.0032 |
| 259 | 0.005051 | −0.002376 | −0.004409 | −0.000428 | 0.002346 | −0.015289 | 0.00741 | −0.014857 | −0.003489 | 0.019901 | 0.001475 | −0.000449 | 0.005157 | −0.004027 |
| 260 | 0.003964 | 0.007188 | −0.014152 | 0.005667 | 0.019458 | −0.026901 | −0.012624 | −0.008799 | 0.008128 | 0.02564 | 0.01378 | −0.032743 | 0.023938 | −0.035535 |
| 261 | 0.003218 | 0.012594 | −0.01882 | 0.016573 | 0.02475 | −0.023039 | −0.025662 | −0.011759 | −0.002451 | −0.011793 | 0.005275 | −0.016742 | 0.005513 | −0.029443 |
| 262 | 0.013566 | 0.01937 | −0.007768 | 0.002904 | 0.012536 | −0.006137 | −0.00182 | −0.002313 | −0.001506 | −0.009305 | −0.003 | −0.002143 | 0.013642 | −0.005317 |
| 263 | 0.012824 | 0.015256 | −0.004518 | −0.012133 | 0.00006 | −0.005311 | 0.009015 | −0.007986 | −0.003976 | −0.007781 | −0.005291 | 0.004869 | 0.01192 | 0.000036 |
| 264 | 0.009343 | 0.004208 | 0.001336 | 0.003156 | 0.003938 | −0.028436 | −0.006191 | −0.028992 | −0.000284 | 0.013158 | 0.001981 | −0.003223 | −0.008748 | 0.008347 |
| 265 | −0.006468 | −0.008365 | 0.026053 | −0.005969 | 0.005646 | −0.03071 | −0.014219 | −0.028078 | 0.001625 | 0.005925 | 0.004567 | −0.001692 | −0.011534 | 0.008898 |
| 766 | −0.015123 | 0.004801 | 0.024497 | 0.007305 | 0.015234 | −0.020038 | −0.01559 | −0.010356 | 0.004287 | −0.003425 | −0.001209 | 0.015651 | −0.00923 | 0.006364 |
| 267 | 0.010834 | 0.02244 | 0.002765 | −0.029618 | 0.000248 | −0.002858 | −0.016117 | 0.002517 | 0.004125 | 0.002282 | 0.018688 | −0.023876 | −0.007221 | 0.00169 |
| 268 | −0.007619 | −0.013893 | −0.010507 | 0.013 | −0.014047 | −0.018197 | −0.011511 | −0.012436 | −0.008337 | 0.011529 | −0.010616 | −0.001806 | −0.018251 | −0.000671 |
| 269 | −0.01665 | −0.007397 | −0.000671 | 0.012508 | −0.008268 | −0.009751 | −0.019183 | −0.016707 | −0.006227 | 0.011269 | −0.006768 | −0.002659 | −0.013906 | −0.009044 |
| 270 | −0.002775 | −0.009338 | −0.007831 | −0.000461 | 0.004388 | −0.04488 | −0.023206 | −0.023982 | −0.006073 | 0.000007 | 0.004 | −0.004993 | −0.009737 | 0.000284 |
| 271 | 0.008531 | 0.059877 | 0.033336 | −0.002427 | 0.041763 | −0.049432 | 0.007093 | −0.024396 | 0.002621 | 0.019997 | 0.009615 | 0.010898 | −0.00815 | −0.00923 |
| 272 | 0.021242 | 0.029224 | −0.000878 | 0.022662 | 0.01663 | 0.015946 | −0.006973 | −0.007915 | −0.008731 | 0.018316 | 0.000912 | −0.002859 | 0.000367 | 0.003776 |
| 273 | 0.019729 | −0.006538 | −0.03069 | 0.030031 | −0.006874 | −0.00643 | −0.000379 | −0.006947 | −0.013658 | 0.01426 | −0.00442 | 0.000807 | 0.011378 | −0.007646 |
| 274 | 0.016984 | −0.003482 | −0.026592 | 0.027295 | −0.00532 | −0.005108 | −0.002799 | −0.006706 | −0.013737 | 0.016784 | −0.002688 | 0.005502 | 0.011123 | −0.006531 |
| 275 | 0.032262 | 0.007023 | 0.000969 | −0.017747 | 0.019574 | −0.044609 | −0.016892 | −0.027998 | −0.015227 | 0.014113 | 0.017449 | −0.019113 | 0.014681 | 0.006078 |
| 276 | 0.003555 | 0.03572 | 0.000318 | −0.008497 | 0.006101 | 0.006741 | −0.001475 | −0.001434 | 0.004509 | 0.0265 | 0.006492 | −0.014048 | 0.003838 | −0.008962 |
| 277 | −0.003395 | −0.0008 | −0.004918 | 0.010665 | 0.008838 | 0.027004 | 0.002423 | 0.013357 | 0.0084 | −0.011636 | 0.009789 | 0.004514 | 0.005135 | −0.003515 |
| 278 | −0.002243 | 0.006675 | 0.000132 | −0.006604 | 0.011061 | 0.022899 | 0.006254 | 0.018837 | 0.011149 | −0.006488 | 0.014331 | 0.001727 | 0.012734 | 0.002474 |
| 279 | 0.014063 | 0.01023 | 0.029214 | −0.027064 | 0.026897 | −0.034878 | −0.000784 | 0.003224 | 0.001155 | −0.010725 | 0.009375 | 0.014075 | 0.000673 | −0.008063 |
| 280 | −0.010815 | 0.010788 | 0.008418 | −0.027069 | −0.000936 | 0.005447 | −0.003579 | 0.004457 | −0.01064 | 0.01021 | 0.013777 | 0.019963 | −0.031115 | 0.004836 |
| 281 | −0.000645 | −0.011087 | −0.02192 | 0.006373 | 0.008759 | −0.015116 | −0.000269 | −0.002377 | −0.002932 | 0.001916 | −0.007048 | −0.001242 | −0.00727 | 0.010848 |
| 282 | −0.008086 | −0.008225 | −0.015222 | −0.002875 | 0.017376 | −0.015479 | 0.002801 | −0.001851 | 0.001161 | 0.011824 | −0.004966 | −0.010471 | −0.00259 | 0.004957 |
| 283 | 0.012133 | 0.006853 | 0.009384 | 0.002491 | 0.045666 | −0.058129 | −0.016077 | −0.027542 | −0.002981 | 0.007313 | 0.003806 | 0.008363 | −0.003316 | −0.016457 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 284 | −0.006325 | −0.010496 | −0.010005 | 0.001179 | −0.011356 | −0.007701 | −0.003348 | −0.007711 | −0.007378 | −0.002578 | −0.009042 | 0.001254 | −0.000573 | 0.005091 |
| 285 | −0.007608 | −0.008052 | −0.003893 | 0.000695 | −0.009619 | −0.013181 | 0.002383 | 0.000479 | −0.003292 | −0.003449 | −0.00976 | −0.00008 | 0.009385 | 0.010141 |
| 286 | −0.031856 | −0.021203 | −0.00628 | 0.00993 | −0.013279 | 0.010668 | −0.000217 | −0.019789 | −0.005273 | 0.00602 | −0.008957 | 0.000475 | −0.023073 | 0.014563 |
| 287 | −0.029523 | −0.012567 | 0.00129 | 0.003939 | 0.003992 | −0.006777 | −0.006837 | −0.028653 | −0.002315 | 0.002756 | −0.003156 | −0.003789 | −0.022226 | 0.009018 |
| 288 | −0.010496 | −0.006938 | −0.015442 | 0.009783 | 0.024086 | −0.036093 | −0.024118 | −0.020043 | −0.002367 | −0.01473 | 0.018232 | 0.021485 | −0.02146 | 0.001523 |
| 289 | 0.017146 | 0.010933 | 0.002252 | −0.021054 | 0.017339 | −0.042808 | −0.006286 | −0.009342 | 0.00195 | −0.016479 | 0.000173 | 0.001457 | 0.007878 | 0.00551 |
| 290 | 0.012935 | −0.010708 | −0.022236 | 0.01599 | −0.000769 | −0.002726 | −0.000096 | −0.003419 | −0.003937 | −0.025193 | 0.00814 | 0.022091 | −0.005973 | 0.004316 |
| 291 | 0.011534 | −0.01062 | −0.019588 | 0.019743 | 0.001862 | −0.003614 | 0.00014 | −0.004594 | −0.003137 | −0.024543 | 0.009289 | 0.022657 | −0.006219 | 0.004929 |
| 292 | 0.013165 | −0.00601 | −0.014321 | 0.019557 | 0.001099 | 0.000403 | 0.001645 | −0.001584 | −0.005132 | −0.029142 | 0.006051 | 0.02786 | −0.00752 | 0.01683 |
| 293 | −0.001428 | −0.016555 | 0.010462 | 0.015479 | 0.010096 | −0.015952 | 0.010526 | 0.001095 | 0.013249 | −0.007253 | 0.025907 | 0.033302 | −0.021226 | −0.011364 |
| 294 | −0.005529 | −0.017704 | −0.024063 | −0.009606 | 0.006446 | −0.022377 | −0.031242 | −0.018598 | −0.010582 | −0.022976 | −0.00132 | −0.007191 | −0.022989 | −0.015312 |
| 295 | 0.009696 | −0.01498 | −0.025341 | 0.007423 | 0.005882 | −0.001006 | 0.001471 | 0.011784 | −0.011074 | −0.001683 | 0.004368 | 0.026555 | 0.006101 | −0.013327 |
| 296 | 0.007347 | −0.024808 | −0.041162 | −0.002201 | 0.023909 | −0.031267 | −0.049214 | −0.010808 | −0.032077 | −0.051247 | −0.004231 | 0.014532 | 0.004131 | −0.001579 |
| 297 | −0.004417 | −0.005936 | −0.040005 | 0.021588 | 0.006599 | 0.002752 | −0.007482 | 0.022268 | −0.000253 | 0.008166 | 0.004825 | 0.026295 | 0.004375 | −0.013924 |
| 298 | −0.013197 | −0.031383 | −0.020852 | −0.051538 | −0.046579 | −0.005216 | −0.010064 | 0.006514 | −0.03273 | −0.064499 | −0.018558 | −0.051387 | −0.011066 | −0.02913 |
| 299 | −0.025645 | −0.003936 | −0.039724 | 0.011098 | −0.01581 | −0.019269 | −0.00189 | 0.014613 | −0.016537 | 0.030441 | −0.0177 | 0.002445 | −0.018927 | −0.018065 |
| 300 | −0.010295 | −0.00641 | −0.000441 | −0.050364 | −0.002008 | 0.004957 | −0.005303 | −0.006362 | −0.029858 | −0.071818 | −0.005547 | −0.047958 | −0.021489 | −0.095041 |
| 301 | −0.004326 | −0.010603 | −0.019705 | −0.014303 | −0.015595 | −0.01651 | −0.001138 | 0.016531 | −0.015391 | 0.001049 | −0.01462 | −0.001519 | −0.000469 | −0.0179 |
| 302 | 0.002897 | −0.015602 | −0.018104 | −0.028346 | −0.00005 | −0.043396 | −0.018401 | −0.006393 | −0.031919 | −0.004039 | −0.025104 | −0.021058 | −0.00406 | −0.019795 |
| 303 | −0.038021 | −0.004122 | −0.028046 | 0.00046 | −0.005712 | −0.001913 | −0.021793 | 0.000731 | −0.029648 | 0.024406 | −0.02572 | −0.032283 | −0.032605 | −0.018601 |
| 304 | −0.023918 | −0.012457 | −0.04488 | −0.015856 | −0.022653 | −0.022464 | −0.011152 | 0.011917 | −0.038553 | 0.011508 | −0.018819 | −0.018413 | −0.030924 | −0.017464 |
| 305 | 0.019394 | 0.012565 | 0.019393 | −0.026814 | −0.011918 | −0.035142 | 0.023599 | 0.019843 | −0.006416 | −0.061151 | −0.004246 | −0.003407 | −0.003544 | 0.002479 |
| 306 | 0.000918 | −0.038143 | −0.044996 | 0.051671 | −0.02385 | −0.015095 | −0.010633 | −0.005401 | −0.00234 | −0.049571 | 0.003918 | 0.022826 | −0.024431 | 0.005722 |
| 307 | −0.043461 | 0.005852 | −0.060616 | 0.018434 | 0.001469 | 0.027551 | 0.01394 | 0.012419 | −0.002279 | 0.041025 | 0.026513 | 0.095819 | −0.017513 | 0.001823 |
| 308 | 0.020636 | −0.00763 | −0.004155 | −0.041875 | −0.016659 | 0.010036 | 0.031765 | 0.018462 | 0.006489 | −0.082398 | 0.003306 | 0.077604 | −0.003449 | 0.026225 |
| 309 | −0.042578 | −0.014222 | 0.012015 | −0.026698 | 0.010416 | −0.011307 | −0.041428 | −0.039504 | −0.020114 | −0.009876 | −0.012639 | −0.005746 | −0.022542 | −0.025552 |
| 310 | −0.037041 | −0.020414 | 0.010445 | −0.043422 | −0.008093 | −0.013728 | −0.037701 | −0.038464 | −0.026081 | 0.028901 | −0.00611 | −0.039922 | −0.015708 | 0.005533 |
| 311 | −0.018481 | −0.024743 | −0.019345 | 0.026934 | −0.017894 | 0.005434 | −0.013613 | −0.033475 | −0.019251 | 0.001123 | −0.018644 | 0.004547 | −0.026865 | −0.042263 |
| 312 | −0.009526 | −0.022944 | 0.008768 | −0.025379 | −0.039061 | 0.040702 | −0.00636 | −0.008628 | −0.007699 | −0.058201 | −0.024333 | 0.006601 | −0.032759 | 0.043239 |
| 313 | −0.019374 | −0.031085 | −0.009576 | 0.030071 | −0.024978 | 0.02853 | −0.01482 | −0.026852 | −0.01101 | −0.010683 | −0.019434 | 0.009706 | −0.019405 | −0.000275 |
| 314 | −0.021983 | 0.021617 | −0.032352 | −0.043134 | −0.048499 | 0.001915 | 0.024425 | 0.023622 | 0.033493 | −0.053172 | 0.013811 | −0.006674 | 0.004034 | 0.046757 |
| 315 | −0.06276 | −0.015854 | −0.005273 | 0.007295 | −0.003989 | 0.017153 | −0.035873 | −0.019144 | −0.016732 | −0.004642 | −0.018448 | 0.015932 | −0.040071 | −0.004044 |
| 316 | 0.000447 | −0.018399 | 0.040773 | −0.071033 | 0.0024 | −0.03835 | −0.021942 | 0.02115 | −0.000342 | −0.062038 | 0.017953 | −0.009848 | 0.002995 | −0.016127 |
| 317 | −0.047347 | −0.026533 | 0.016596 | −0.022849 | 0.00994 | 0.017401 | −0.037599 | −0.034515 | −0.015048 | −0.005256 | −0.015366 | −0.006164 | −0.010681 | −0.016022 |
| 318 | −0.044875 | −0.034881 | −0.008261 | −0.016649 | −0.017206 | 0.016412 | 0.001709 | 0.007757 | −0.017174 | 0.067491 | −0.010207 | 0.032379 | −0.00302 | 0.00801 |
| 319 | 0.917386 | −0.033939 | 0.005132 | 0.014416 | 0.002528 | 0.032196 | −0.038585 | −0.01913 | −0.016948 | 0.024673 | −0.017922 | 0.002187 | −0.028988 | −0.025622 |
| 320 | −0.032843 | 0.89221 | −0.009777 | 0.016007 | −0.023655 | 0.024798 | −0.011818 | −0.011745 | −0.022608 | −0.013137 | −0.02196 | −0.001716 | −0.02184 | −0.020976 |
| 321 | −0.005797 | −0.012478 | 0.882484 | 0.005376 | −0.039369 | 0.00435 | −0.011564 | 0.01111 | −0.016753 | 0.001705 | −0.022723 | −0.019512 | −0.014291 | −0.018226 |
| 322 | 0.022355 | 0.011133 | 0.00182 | 0.699988 | −0.059744 | −0.022137 | 0.019263 | 0.034453 | −0.014451 | −0.088781 | 0.001801 | −0.086537 | 0.010329 | −0.018267 |
| 323 | −0.011647 | −0.03282 | −0.058788 | −0.040545 | 0.853473 | 0.056976 | 0.037367 | 0.033899 | −0.029195 | −0.016225 | −0.057832 | −0.035869 | −0.013925 | 0.033455 |
| 324 | 0.028745 | 0.020006 | −0.000048 | −0.024141 | 0.042502 | 0.806341 | −0.015853 | −0.018684 | −0.004142 | −0.02382 | 0.020421 | 0.0078 | −0.006337 | −0.011812 |
| 325 | −0.032383 | −0.003667 | −0.005013 | −0.002276 | 0.044189 | −0.02845 | 0.90826 | −0.060706 | −0.021264 | −0.014249 | −0.007904 | −0.023579 | −0.032618 | −0.033657 |
| 326 | −0.014103 | −0.000023 | 0.018989 | 8.027709 | 0.029061 | −0.019515 | −0.054804 | 0.836604 | −0.020805 | −0.022738 | −0.038758 | −0.044573 | −0.051172 | −0.084902 |
| 327 | −0.018699 | −0.025567 | −0.018657 | −0.009961 | −0.023557 | −0.000284 | −0.025238 | −0.022991 | 0.94784 | 0.007245 | −0.043705 | −0.012628 | −0.030177 | −0.006432 |
| 328 | 0.019582 | −0.014517 | −0.028146 | −0.082089 | −0.051652 | −0.022805 | −0.001979 | −0.008312 | 0.000515 | 0.667145 | −0.02328 | −0.048649 | −0.003595 | −0.077337 |
| 329 | −0.018652 | −0.017184 | −0.022392 | 0.006314 | −0.04986 | 0.029517 | −0.008027 | −0.035974 | −0.042178 | −0.002357 | 0.914581 | −0.023403 | −0.026033 | −0.00084 |
| 330 | 0.009905 | −0.008111 | −0.013352 | −0.087751 | −0.018893 | −0.009966 | −0.01974 | −0.049272 | −0.016349 | −0.043649 | −0.023088 | 0.749411 | 0.007802 | −0.143145 |
| 331 | −0.031954 | −0.01787 | −0.008965 | 0.001282 | −0.010608 | −0.00328 | −0.038116 | −0.055088 | −0.027033 | −0.013276 | −0.029526 | −0.000574 | 0.935082 | −0.017797 |
| 332 | −0.016242 | −0.023518 | −0.005485 | −0.020102 | 0.033228 | −0.025133 | −0.019117 | −0.073284 | −0.004255 | −0.059061 | 0.010521 | −0.119252 | −0.01688 | 0.735269 |
| 333 | −0.036193 | −0.016452 | −0.002497 | −0.010093 | 0.015494 | −0.009479 | −0.058449 | −0.046951 | −0.018866 | −0.00398 | −0.015572 | −0.007445 | −0.034142 | −0.027807 |

APPENDIX B3-continued

PCA Transformation
Matrix (340 × 340 Early/Late)

| | | | | | | | | | | | | | | |
|---|---|---|---|---|---|---|---|---|---|---|---|---|---|---|
| 334 | −0.008473 | 0.018234 | 0.011361 | −0.008091 | 0.017139 | 0.011596 | −0.061965 | −0.022586 | −0.020898 | −0.05703 | −0.043402 | −0.04532 | −0.009106 | 0.031903 |
| 335 | −0.044896 | −0.033547 | −0.000689 | 0.016944 | −0.017235 | 0.009365 | −0.041097 | −0.058371 | −0.022873 | 0.027878 | −0.025413 | −0.011531 | −0.047633 | −0.03324 |
| 336 | −0.016141 | 0.001588 | −0.030685 | −0.053616 | −0.016411 | 0.000396 | −0.021199 | −0.035574 | −0.026619 | −0.014849 | −0.008899 | −0.034163 | −0.034456 | −0.02581 |
| 337 | −0.016452 | −0.008876 | −0.008116 | −0.026449 | −0.010774 | −0.033841 | −0.01089 | 0.013611 | −0.007346 | −0.041353 | −0.007098 | 0.006658 | −0.004638 | 0.008407 |
| 338 | −0.003305 | 0.001508 | 0.002997 | −0.004105 | −0.022873 | −0.021959 | 0.005715 | 0.02012 | −0.04008 | −0.09553 | −0.021019 | −0.040099 | 0.018815 | −0.013092 |
| 339 | −0.014721 | −0.01712 | −0.033756 | −0.001016 | −0.0423181 | 0.030897 | 0.002364 | −0.014168 | −0.015866 | −0.056068 | −0.028974 | −0.001522 | −0.024776 | −0.018731 |
| 340 | −0.017414 | −0.002127 | 0.011116 | 0.060521 | 0.006772 | −0.01512 | 0.011557 | −0.01146 | −0.008833 | 0.014811 | −0.017812 | −0.010214 | 0.002905 | −0.02936 |

| | LV | LW | LX | LY | LZ | MA | MB | MC |
|---|---|---|---|---|---|---|---|---|
| 1 | 0.006018 | 0.0338 | 0.024659 | 0.037438 | 0.050891 | −0.029838 | −0.019169 | 0.020219 |
| 2 | 0.015466 | 0.000656 | 0.037542 | 0.003748 | −0.031836 | 0.000935 | −0.0166 | 0.083849 |
| 3 | −0.057554 | −0.072726 | −0.057803 | −0.026222 | −0.048667 | −0.01246 | −0.016246 | −0.132245 |
| 4 | −0.004373 | −0.052277 | 0.059571 | 0.030274 | −0.025765 | 0.005128 | 0.059742 | −0.083963 |
| 5 | −0.01632 | −0.05858 | −0.007954 | 0.026643 | 0.020784 | 0.144721 | −0.034261 | 0.19011 |
| 6 | 0.030548 | 0.021664 | 0.006316 | −0.04031 | 0.090578 | 0.036926 | 0.048821 | −0.067784 |
| 7 | 0.081422 | 0.009308 | 0.090516 | 0.108832 | 0.032248 | 0.0903 | 0.006397 | −0.051567 |
| 8 | −0.040303 | 0.052258 | 0.022583 | 0.041798 | 0.021114 | −0.088371 | 0.001465 | −0.129262 |
| 9 | 0.038529 | 0.113703 | −0.005355 | −0.080882 | −0.101831 | −0.007057 | −0.117737 | 0.066608 |
| 10 | −0.052556 | −0.073158 | −0.032079 | 0.014928 | 0.007966 | −0.096851 | 0.07307 | −0.031775 |
| 11 | −0.009435 | −0.002478 | 0.052467 | −0.066292 | 0.036799 | 0.170403 | −0.010446 | −0.058301 |
| 12 | −0.030408 | −0.099169 | −0.031872 | −0.057451 | −0.063556 | 0.21458 | 0.038473 | 0.05347 |
| 13 | −0.037023 | −0.056992 | −0.01279 | −0.006282 | −0.014156 | −0.063837 | 0.006931 | −0.015312 |
| 14 | 0.026089 | −0.071416 | −0.032402 | 0.015812 | 0.052656 | 0.035975 | 0.033756 | −0.003547 |
| 15 | −0.020797 | 0.005432 | −0.046568 | −0.022491 | −0.068975 | 0.005307 | −0.060688 | −0.118888 |
| 16 | 0.007276 | 0.026305 | −0.020704 | 0.086669 | −0.07574 | −0.000909 | 0.021608 | −0.098068 |
| 17 | −0.074331 | −0.059009 | −0.092045 | −0.007624 | 0.033341 | −0.006346 | −0.085893 | 0.056585 |
| 18 | −0.053788 | −0.021831 | −0.078099 | 0.01163 | −0.051513 | −0.056107 | 0.081627 | 0.088686 |
| 19 | −0.000515 | −0.027726 | 0.009087 | −0.025132 | 0.012874 | −0.076264 | −0.044064 | −0.008591 |
| 20 | −0.017607 | 0.07839 | −0.038781 | −0.010066 | −0.075635 | 0.0701 | 0.003414 | −0.058047 |
| 21 | 0.005254 | −0.017004 | −0.011404 | −0.009601 | 0.005924 | −0.029359 | 0.070036 | −0.065134 |
| 22 | 0.00072 | −0.160159 | 0.004301 | −0.018267 | −0.005639 | −0.075276 | −0.016525 | 0.049925 |
| 23 | 0.049677 | 0.070751 | 0.044566 | 0.082306 | −0.034084 | −0.060472 | 0.033978 | −0.045079 |
| 24 | 0.014263 | 0.086786 | 0.0223 | 0.046297 | 0.048208 | 0.127752 | −0.015432 | 0.212007 |
| 25 | 0.021564 | 0.013743 | −0.00676 | −0.028209 | −0.002917 | −0.079094 | 0.092559 | −0.024005 |
| 26 | −0.012113 | −0.064496 | −0.018247 | 0.065414 | −0.071696 | 0.042493 | −0.045436 | −0.064595 |
| 27 | 0.016836 | 0.039261 | 0.005572 | 0.00267 | −0.012578 | −0.02796 | −0.003214 | −0.00917 |
| 28 | −0.04633 | −0.053216 | −0.011638 | −0.038149 | −0.06709 | 0.018077 | −0.034322 | −0.072366 |
| 29 | 0.002022 | 0.019239 | 0.013183 | −0.007631 | 0.023399 | 0.045069 | −0.003386 | −0.01988 |
| 30 | 0.003419 | −0.034673 | 0.003255 | −0.015025 | −0.043577 | 0.033144 | −0.068598 | −0.069863 |
| 31 | −0.015667 | −0.010996 | 0.011577 | −0.056738 | 0.079418 | −0.008788 | 0.029316 | −0.055857 |
| 32 | 0.062377 | 0.041519 | 0.035936 | −0.01005 | −0.043343 | −0.027804 | −0.018648 | 0.058896 |
| 33 | 0.006491 | 0.023295 | −0.001109 | −0.003963 | −0.070655 | −0.081291 | 0.027595 | −0.148789 |
| 34 | −0.030975 | 0.2012 | −0.040407 | −0.056827 | 0.049678 | 0.025008 | 0.057617 | −0.03628 |
| 35 | −0.020236 | −0.002831 | −0.067203 | −0.059003 | −0.007202 | 0.145272 | −0.019772 | 0.100963 |
| 36 | −0.088778 | −0.066424 | −0.017077 | −0.08817 | 0.053731 | 0.001091 | −0.055337 | 0.005107 |
| 37 | −0.00724 | 0.039091 | 0.015676 | −0.060444 | −0.012963 | −0.102737 | −0.027864 | 0.1698 |
| 38 | −0.054138 | −0.012988 | 0.007411 | −0.034329 | −0.021478 | −0.037555 | −0.03205 | 0.084002 |
| 39 | −0.013652 | 0.017607 | 0.008787 | −0.151848 | 0.008833 | 0.04036 | −0.011296 | 0.023142 |
| 40 | −0.001877 | 0.0251 | 0.000392 | 0.006598 | 0.009293 | −0.002825 | −0.009644 | 0.015137 |

APPENDIX B3-continued

PCA Transformation
Matrix (340 × 340 Early/Late)

| | | | | | | | | |
|---|---|---|---|---|---|---|---|---|
| 41 | −0.05255 | −0.178566 | −0.033812 | −0.0182 | 0.000921 | 0.001975 | −0.02768 | −0.017376 |
| 42 | 0.053233 | 0.080356 | 0.03305 | −0.037539 | 0.013614 | −0.047507 | 0.002772 | −0.081076 |
| 43 | 0.015389 | −0.001318 | −0.001314 | 0.005722 | −0.029268 | −0.0061031 | 0.013016 | 0.038094 |
| 44 | −0.000144 | 0.062779 | 0.002312 | −0.015113 | 0.005118 | 0.033558 | 0.022686 | 0.028834 |
| 45 | 0.003746 | 0.081112 | 0.031233 | −0.006961 | −0.020683 | 0.0469 | −0.105601 | 0.007501 |
| 46 | −0.019216 | −0.12294 | 0.055978 | −0.017975 | −0.017405 | −0.007535 | 0.000904 | 0.001969 |
| 47 | −0.040228 | 0.038833 | −0.048045 | −0.016527 | −0.032638 | 0.064486 | 0.000925 | −0.133909 |
| 48 | 0.053563 | −0.049869 | 0.005057 | −0.003914 | −0.02223 | −0.08376 | 0.026062 | 0.009448 |
| 49 | 0.012931 | −0.029418 | −0.0065 | 0.035433 | −0.039546 | 0.039151 | 0.006045 | 0.001784 |
| 50 | 0.006483 | 0.138377 | 0.020982 | −0.040039 | 0.046823 | 0.02754 | 0.070992 | −0.084204 |
| 51 | 0.009473 | −0.110196 | 0.058131 | −0.037818 | −0.003019 | −0.094402 | 0.033784 | −0.00503 |
| 52 | −0.009829 | −0.023453 | −0.023788 | −0.033073 | 0.046508 | −0.017288 | −0.010921 | −0.022264 |
| 53 | −0.017497 | 0.079697 | 0.001066 | −0.084864 | 0.051652 | 0.078375 | 0.040205 | 0.154205 |
| 54 | 0.003008 | −0.060122 | −0.027853 | 0.109176 | 0.037946 | −0.008935 | 0.086082 | −0.020581 |
| 55 | −0.006052 | −0.006688 | −0.079632 | 0.028738 | 0.081785 | 0.01853 | −0.048032 | 0.043641 |
| 56 | 0.019507 | −0.011508 | 0.041515 | −0.049253 | −0.032508 | −0.088408 | −0.097486 | 0.034283 |
| 57 | −0.094823 | −0.023597 | −0.055604 | −0.052849 | −0.037317 | 0.012001 | −0.015333 | 0.014049 |
| 58 | 0.00839 | 0.03079 | −0.018543 | −0.077943 | −0.006333 | 0.016805 | 0.061964 | −0.068391 |
| 59 | 0.001749 | 0.081025 | −0.089046 | −0.028131 | 0.104576 | 0.032376 | −0.019196 | 0.145261 |
| 60 | −0.006102 | −0.006173 | 0.004381 | −0.028379 | −0.015175 | 0.016656 | −0.001621 | 0.020234 |
| 61 | 0.009626 | 0.023579 | 0.002132 | 0.029314 | 0.009307 | −0.007267 | 0.002147 | 0.017354 |
| 62 | −0.007404 | −0.023206 | 0.000757 | −0.041649 | −0.022821 | −0.005348 | 0.016332 | −0.041426 |
| 63 | 0.008058 | −0.019217 | 0.006301 | 0.030398 | −0.010965 | −0.015498 | −0.011406 | 0.006212 |
| 64 | −0.00391 | 0.01544 | −0.017105 | 0.015903 | 0.000769 | 0.007547 | 0.003076 | 0.000915 |
| 65 | 0.008978 | −0.007382 | 0.011834 | 0.019739 | −0.01868 | 0.004333 | 0.012648 | −0.029808 |
| 66 | −0.00809 | 0.002096 | 0.00751 | 0.005873 | 0.002009 | 0.007365 | −0.024452 | 0.026058 |
| 67 | −0.016165 | −0.012625 | −0.0235 | −0.022109 | 0.016599 | 0.003571 | −0.008005 | 0.011493 |
| 68 | −0.023019 | 0.007719 | −0.030324 | −0.040579 | −0.020718 | −0.023697 | 0.006153 | −0.005255 |
| 69 | 0.004239 | 0.035008 | −0.008107 | 0.000526 | 0.010154 | 0.023132 | −0.007758 | 0.001925 |
| 70 | 0.003727 | 0.031002 | 0.017299 | −0.005276 | 0.007859 | 0.018548 | −0.005607 | 0.020623 |
| 71 | 0.008129 | −0.030773 | 0.017596 | 0.006069 | −0.024323 | 0.024355 | 0.016382 | −0.005967 |
| 72 | 0.008012 | −0.031649 | 0.002397 | 0.023185 | −0.01447 | 0.076574 | 0.000419 | −0.011747 |
| 73 | 0.011115 | −0.022963 | 0.005062 | −0.002211 | 0.001861 | 0.037211 | −0.008305 | −0.03183 |
| 74 | 0.01601 | 0.001694 | 0.019782 | 0.01384 | −0.007715 | 0.016147 | 0.026675 | 0.001584 |
| 75 | 0.001063 | −0.0168 | 0.009763 | 0.006662 | −0.003984 | 0.006617 | 0.009582 | 0.012227 |
| 76 | 0.00337 | −0.026583 | 0.018287 | 0.022206 | −0.027676 | 0.021019 | 0.007 | 0.006285 |
| 77 | 0.004565 | −0.000646 | 0.01255 | 0.000178 | −0.003929 | 0.007226 | 0.00514 | 0.016685 |
| 78 | 0.005638 | −0.00366 | 0.005758 | −0.004785 | 0.005768 | 0.003184 | 0.004366 | 0.049623 |
| 79 | −0.007162 | 0.016184 | 0.006272 | 0.004514 | 0.005178 | 0.023885 | 0.017799 | −0.013381 |
| 80 | 0.00607 | 0.024091 | −0.012172 | 0.040053 | 0.053545 | −0.033789 | 0.015883 | −0.025742 |
| 81 | 0.034019 | 0.040443 | 0.000221 | 0.027924 | −0.029467 | −0.015951 | 0.006819 | −0.069165 |
| 82 | −0.007021 | 0.001385 | 0.008138 | 0.007652 | 0.006854 | 0.028217 | −0.000861 | 0.031777 |
| 83 | −0.009508 | −0.009035 | 0.000375 | 0.022347 | 0.0032 | 0.002136 | 0.006704 | 0.014713 |
| 84 | 0.005112 | −0.008416 | 0.012202 | 0.016912 | 0.009058 | −0.014669 | 0.004655 | −0.012108 |
| 85 | 0.008856 | −0.001888 | −0.001266 | 0.035988 | 0.033276 | −0.027002 | 0.049292 | −0.057796 |
| 86 | −0.006641 | −0.019358 | 0.00967 | 0.02699 | −0.008239 | 0.020204 | 0.017346 | −0.0305 |
| 87 | 0.00694 | 0.003719 | 0.01584 | 0.025247 | 0.026669 | −0.012346 | 0.020407 | −0.020541 |
| 88 | −0.003553 | 0.014888 | −0.005422 | 0.005493 | 0.016105 | −0.001935 | −0.007122 | 0.029301 |
| 89 | −0.00759 | 0.007028 | −0.009596 | −0.008239 | 0.014581 | −0.007568 | 0.000418 | 0.03606 |
| 90 | −0.000266 | −0.002069 | −0.002506 | 0.013619 | 0.011909 | −0.00176 | 0.005485 | 0.016141 |

APPENDIX B3-continued

PCA Transformation Matrix (340 × 340 Early/Late)

| | | | | | | | | |
|---|---|---|---|---|---|---|---|---|
| 91 | −0.003333 | −0.001083 | 0.00337 | 0.01903 | 0.011981 | 0.014654 | −0.005192 | 0.012606 |
| 92 | 0.031719 | 0.024064 | 0.013038 | 0.02921 | −0.006726 | 0.018155 | −0.01273 | 0.004446 |
| 93 | −0.005615 | −0.016598 | −0.000677 | 0.010229 | −0.016458 | −0.001175 | −0.003954 | −0.019827 |
| 94 | 0.005533 | −0.012976 | 0.009431 | 0.022063 | −0.008281 | 0.032374 | −0.01635 | 0.036265 |
| 95 | −0.003821 | −0.009278 | −0.007929 | −0.004101 | 0.018063 | 0.00792 | 0.006935 | −0.044031 |
| 96 | 0.001899 | 0.007631 | 0.023582 | −0.026076 | 0.030619 | 0.017537 | −0.010683 | 0.02161 |
| 97 | 0.002711 | 0.01762 | −0.012931 | 0.022235 | −0.005584 | 0.025136 | 0.020405 | 0.000231 |
| 98 | 0.006946 | −0.002528 | 0.006126 | 0.02046 | 0.003142 | 0.023822 | 0.004843 | −0.015254 |
| 99 | −0.007363 | 0.001443 | −0.008057 | 0.008103 | 0.004037 | 0.006122 | 0.004892 | −0.01157 |
| 100 | 0.004428 | −0.007457 | 0.009441 | −0.003989 | −0.000239 | 0.026276 | 0.00058 | −0.014918 |
| 101 | −0.000336 | −0.011483 | −0.004887 | 0.005306 | −0.009179 | 0.016825 | 0.007925 | −0.022316 |
| 102 | 0.016879 | −0.009341 | 0.012307 | 0.025175 | 0.045875 | −0.010226 | 0.008616 | −0.008312 |
| 103 | −0.0035 | 0.014172 | −0.017829 | −0.001961 | 0.020071 | 0.013813 | 0.020933 | −0.000276 |
| 104 | 0.010435 | −0.039413 | 0.001579 | −0.008209 | 0.004496 | −0.014632 | 0.015858 | −0.030448 |
| 105 | 0.000907 | −0.025013 | 0.001116 | −0.059292 | −0.015201 | −0.078969 | −0.030675 | 0.036934 |
| 106 | −0.013219 | −0.03321 | 0.001994 | −0.008411 | 0.00211 | −0.000296 | −0.016791 | −0.024754 |
| 107 | 0.00241 | −0.014248 | −0.001855 | 0.002247 | −0.000813 | −0.010344 | −0.009969 | 0.019942 |
| 108 | −0.003 | 0.029532 | −0.00254 | 0.004052 | 0.019517 | −0.017779 | 0.011751 | −0.025527 |
| 109 | 0.00153 | −0.097996 | −0.017676 | 0.010411 | 0.009867 | −0.052266 | −0.038561 | 0.023606 |
| 110 | 0.013264 | 0.024538 | 0.024072 | 0.023145 | 0.037791 | 0.031916 | 0.0176 | −0.020506 |
| 111 | 0.000386 | −0.004101 | 0.024661 | 0.048192 | 0.040326 | 0.000828 | −0.015662 | −0.00205 |
| 112 | −0.003479 | 0.035762 | −0.008139 | −0.005454 | 0.004735 | −0.000551 | −0.023974 | 0.005953 |
| 113 | 0.011786 | −0.015805 | 0.006689 | −0.005045 | 0.029443 | −0.022694 | −0.035081 | 0.0175 |
| 114 | 0.017282 | 0.058534 | −0.008494 | −0.020304 | −0.016693 | −0.020093 | −0.018351 | −0.008755 |
| 115 | −0.023579 | −0.062047 | 0.024005 | −0.007172 | −0.02817 | 0.001368 | −0.002589 | −0.025487 |
| 116 | −0.003605 | 0.036187 | −0.043387 | 0.035338 | −0.038067 | 0.037974 | −0.009168 | −0.005421 |
| 117 | 0.023548 | −0.005498 | 0.038748 | 0.025844 | −0.00437 | 0.01884 | 0.004433 | −0.030823 |
| 118 | −0.002003 | 0.036792 | 0.00218 | −0.033834 | 0.027777 | 0.001432 | 0.031763 | −0.034877 |
| 119 | −0.001447 | 0.009268 | −0.003385 | −0.004013 | −0.002153 | 0.021714 | −0.035433 | −0.005816 |
| 120 | −0.00309 | 0.019746 | −0.010117 | 0.001378 | −0.004775 | 0.032484 | −0.005057 | −0.015139 |
| 121 | −0.026946 | −0.015054 | −0.013869 | −0.048498 | 0.006813 | −0.018393 | −0.01999 | 0.013132 |
| 122 | 0.000093 | −0.014154 | 0.00952 | 0.013064 | 0.006468 | −0.038649 | 0.005541 | −0.05112 |
| 123 | −0.011762 | −0.005052 | −0.003721 | −0.006412 | 0.001344 | −0.032433 | −0.019002 | −0.00538 |
| 124 | 0.008929 | 0.026275 | 0.00104 | 0.003726 | −0.010447 | 0.00169 | −0.015533 | −0.008141 |
| 125 | −0.008366 | −0.003571 | 0.003629 | −0.011297 | −0.008227 | −0.034308 | 0.016435 | 0.028565 |
| 126 | 0.017904 | 0.003965 | 0.018489 | 0.013053 | 0.0129 | −0.036418 | −0.003741 | −0.003059 |
| 127 | 0.01296 | −0.001761 | 0.016954 | 0.013535 | −0.001859 | −0.018881 | 0.010799 | −0.002175 |
| 128 | 0.011001 | 0.008678 | 0.023444 | −0.024213 | −0.006973 | 0.010158 | 0.002949 | −0.001983 |
| 129 | 0.017745 | 0.034977 | 0.005038 | 0.002978 | 0.041524 | −0.029103 | −0.000098 | −0.043398 |
| 130 | −0.02238 | −0.044386 | −0.005736 | −0.00668 | −0.024011 | 0.013196 | 0.01106 | 0.005187 |
| 131 | 0.013372 | 0.030243 | −0.006316 | −0.000163 | 0.017013 | −0.028328 | 0.000264 | 0.041549 |
| 132 | 0.008265 | 0.007538 | 0.010888 | 0.001204 | 0.002202 | 0.037456 | 0.01066 | 0.021106 |
| 133 | 0.003932 | −0.045374 | 0.004603 | 0.020974 | −0.000343 | 0.030506 | 0.015348 | −0.027909 |
| 134 | −0.004255 | −0.019322 | 0.013913 | 0.016908 | −0.000421 | −0.059987 | −0.000721 | 0.049166 |
| 135 | −0.011 | −0.025292 | −0.019532 | −0.014637 | −0.00461 | 0.020176 | −0.004649 | 0.050967 |
| 136 | −0.004304 | −0.021822 | 0.013239 | 0.011814 | 0.004724 | 0.045105 | 0.001977 | 0.010504 |
| 137 | 0.000053 | −0.012522 | 0.00363 | −0.032342 | 0.014588 | −0.003884 | 0.024966 | 0.010465 |
| 138 | −0.018284 | 0.008791 | −0.009756 | 0.015446 | −0.049554 | −0.016036 | −0.011518 | −0.05411 |
| 139 | 0.002623 | −0.021611 | −0.017451 | 0.001557 | 0.052941 | 0.042017 | −0.012775 | −0.004679 |
| 140 | −0.012144 | 0.027822 | 0.008044 | −0.031885 | 0.008894 | 0.018876 | 0.015482 | −0.031274 |

APPENDIX B3-continued

PCA Transformation Matrix (340 × 340 Early/Late)

| | | | | | | | | |
|---|---|---|---|---|---|---|---|---|
| 141 | −0.02042 | 0.016093 | −0.020012 | −0.054241 | −0.028064 | −0.002977 | −0.015149 | 0.016595 |
| 142 | −0.002391 | 0.000318 | −0.005053 | 0.043691 | 0.005427 | −0.01688 | −0.010911 | −0.01545 |
| 143 | −0.008352 | −0.04163 | −0.007562 | 0.008554 | −0.02724 | −0.033086 | −0.011936 | −0.0304 |
| 144 | −0.023339 | 0.00531 | −0.031762 | −0.002207 | −0.005923 | 0.017697 | −0.047733 | 0.01435 |
| 145 | 0.003953 | −0.023064 | 0.008798 | 0.01348 | −0.001385 | 0.047144 | −0.024985 | 0.016546 |
| 146 | 0.006269 | 0.020945 | −0.007944 | 0.008775 | 0.004373 | 0.00321 | 0.011171 | 0.014819 |
| 147 | 0.007952 | −0.076028 | 0.003606 | 0.025873 | −0.004149 | −0.046931 | −0.032779 | −0.036621 |
| 148 | −0.009259 | 0.020557 | 0.004221 | −0.031544 | 0.02464 | 0.01551 | 0.027736 | −0.052057 |
| 149 | −0.009193 | 0.004436 | 0.000891 | −0.034046 | −0.012134 | 0.002752 | 0.005508 | −0.009302 |
| 150 | 0.012389 | 0.019895 | −0.006915 | 0.026573 | −0.011654 | −0.021375 | 0.036076 | −0.001953 |
| 151 | −0.01549 | −0.048648 | −0.029119 | −0.014118 | 0.013638 | 0.018568 | −0.005215 | −0.061395 |
| 152 | −0.010451 | 0.022024 | −0.007374 | 0.02445 | 0.015071 | 0.006137 | −0.017825 | 0.032645 |
| 153 | 0.001411 | 0.035967 | −0.016352 | 0.009984 | 0.016756 | −0.010632 | 0.005902 | −0.001615 |
| 154 | 0.004611 | −0.037991 | 0.001736 | 0.044128 | −0.001585 | −0.008323 | −0.028826 | 0.035632 |
| 155 | 0.003689 | 0.04251 | 0.003517 | 0.042813 | 0.01941 | −0.016314 | −0.006115 | 0.012767 |
| 156 | 0.001233 | −0.051255 | 0.004981 | 0.026944 | −0.028886 | −0.033425 | −0.028914 | −0.007073 |
| 157 | 0.004601 | 0.004759 | 0.002835 | 0.015105 | −0.005562 | 0.017134 | 0.004948 | −0.024526 |
| 158 | −0.008017 | −0.020841 | 0.004638 | 0.013612 | −0.004572 | −0.04586 | −0.006603 | −0.016949 |
| 159 | −0.014463 | −0.032283 | −0.021941 | −0.036391 | 0.011834 | 0.03931 | −0.041837 | 0.04527 |
| 160 | 0.008357 | −0.012834 | 0.015711 | −0.041202 | 0.004399 | −0.007641 | −0.009946 | −0.075982 |
| 161 | 0.005771 | 0.029136 | −0.009619 | −0.016052 | −0.012907 | 0.011138 | −0.010017 | 0.00545 |
| 162 | −0.014873 | 0.008635 | −0.016948 | −0.01596 | −0.024484 | 0.033035 | −0.009971 | −0.0214514 |
| 163 | −0.00495 | −0.023049 | 0.006038 | 0.02616 | 0.000006 | −0.002229 | −0.000365 | 0.0064021 |
| 164 | 0.006533 | −0.000511 | −0.00935 | −0.037848 | 0.020869 | −0.020355 | −0.028765 | −0.034692 |
| 165 | −0.009871 | −0.010127 | 0.011742 | 0.032191 | −0.03457 | −0.05519 | −0.023831 | −0.031367 |
| 166 | −0.001995 | 0.040547 | −0.012534 | −0.027152 | −0.00813 | −0.005696 | −0.029366 | −0.04128 |
| 167 | −0.006435 | −0.020982 | 0.002033 | −0.0111 | 0.002996 | 0.013449 | −0.024487 | −0.004558 |
| 168 | −0.001407 | 0.008668 | −0.000338 | −0.040471 | −0.012745 | −0.008162 | 0.0164 | −0.039353 |
| 169 | 0.009975 | 0.016744 | −0.008133 | 0.008857 | −0.025441 | 0.00859 | 0.000969 | 0.01325 |
| 170 | 0.007377 | 0.023906 | −0.011258 | 0.007138 | −0.047743 | 0.030385 | −0.005872 | 0.021989 |
| 171 | −0.001306 | 0.050806 | −0.018906 | −0.017865 | −0.020392 | 0.007426 | −0.016676 | 0.041116 |
| 172 | 0.01075 | 0.01817 | −0.019607 | 0.009654 | −0.002213 | 0.015553 | 0.004047 | 0.00784 |
| 173 | −0.000636 | −0.003302 | 0.001897 | −0.005328 | 0.005098 | 0.009362 | 0.008042 | 0.010299 |
| 174 | 0.001331 | 0.019287 | −0.001671 | −0.023845 | 0.006985 | 0.036191 | −0.001364 | 0.052717 |
| 175 | 0.011745 | 0.075373 | 0.006589 | −0.016323 | 0.015461 | 0.005929 | 0.011467 | 0.055514 |
| 176 | −0.011588 | −0.018326 | −0.000589 | 0.014511 | −0.027141 | 0.03425 | 0.001888 | 0.03039 |
| 177 | 0.006525 | −0.030921 | −0.010864 | −0.033838 | −0.004636 | 0.024445 | −0.014927 | −0.051167 |
| 178 | 0.016263 | 0.006135 | 0.021795 | 0.003692 | 0.01372 | 0.013448 | −0.011444 | −0.00836 |
| 179 | 0.001157 | 0.012962 | 0.007486 | 0.015614 | 0.0055 | 0.000826 | −0.002859 | −0.042505 |
| 180 | −0.000978 | 0.009134 | 0.006809 | 0.004834 | 0.007318 | 0.020242 | 0.003916 | −0.027807 |
| 181 | 0.004551 | 0.001832 | 0.008651 | 0.018136 | 0.002637 | 0.021162 | −0.00028 | −0.034651 |
| 182 | 0.000504 | 0.013224 | 0.003666 | 0.010675 | 0.000614 | 0.036401 | 0.002152 | −0.046386 |
| 183 | 0.002366 | 0.0333 | 0.006151 | 0.000764 | 0.007267 | −0.012319 | −0.01939 | −0.015609 |
| 184 | −0.028087 | 0.02282 | −0.010111 | −0.015791 | 0.008263 | 0.03299 | −0.04756 | 0.05028 |
| 185 | 0.001506 | 0.000942 | 0.003705 | 0.014068 | −0.008948 | −0.01386 | 0.011003 | −0.053489 |
| 186 | −0.010773 | −0.005674 | −0.022815 | −0.038525 | 0.026178 | −0.015867 | −0.002568 | −0.015281 |
| 187 | −0.00091 | −0.010131 | 0.008035 | 0.006774 | 0.010716 | 0.014707 | 0.004657 | −0.002813 |
| 188 | −0.004309 | 0.003862 | 0.000183 | 0.001826 | 0.00451 | 0.043858 | −0.009322 | 0.028015 |
| 189 | −0.014026 | 0.017888 | −0.008917 | 0.004187 | 0.009741 | 0.053748 | 0.004217 | 0.034641 |
| 190 | −0.022984 | −0.001565 | −0.005514 | −0.04285 | −0.029116 | 0.007358 | −0.010507 | 0.002 |

APPENDIX B3-continued

PCA Transformation Matrix (340 × 340 Early/Late)

| | | | | | | | | |
|---|---|---|---|---|---|---|---|---|
| 191 | −0.011077 | −0.004885 | −0.004693 | −0.03608 | −0.015118 | −0.003214 | 0.001942 | −0.025187 |
| 192 | 0.01692 | 0.044411 | 0.009338 | 0.009658 | 0.001824 | −0.020109 | −0.019062 | −0.03403 |
| 193 | −0.001018 | 0.026795 | −0.00186 | −0.026405 | 0.009028 | 0.007202 | −0.021646 | 0.015025 |
| 194 | −0.005594 | 0.011961 | 0.001502 | 0.006725 | −0.013812 | −0.027934 | 0.005595 | 0.003598 |
| 195 | −0.00687 | −0.017635 | −0.012216 | 0.028769 | 0.011524 | −0.017186 | 0.020559 | −0.037989 |
| 196 | −0.012863 | 0.003459 | −0.011795 | 0.007394 | 0.008614 | 0.026028 | −0.002555 | −0.013536 |
| 197 | −0.022321 | −0.002958 | −0.008416 | −0.043998 | −0.017883 | 0.013771 | −0.010268 | −0.000348 |
| 198 | 0.000507 | −0.001697 | −0.003761 | 0.006185 | −0.007955 | −0.042106 | 0.009292 | −0.036763 |
| 199 | −0.019741 | −0.036708 | −0.004293 | −0.017082 | −0.00532 | −0.007551 | 0.002283 | −0.005832 |
| 200 | 0.020944 | 0.000992 | −0.016071 | −0.008952 | 0.039981 | −0.034367 | −0.006954 | 0.021966 |
| 201 | 0.009365 | −0.062827 | 0.016201 | 0.003017 | −0.040146 | −0.059134 | 0.007284 | −0.043795 |
| 202 | 0.010803 | −0.040246 | 0.00902 | −0.003234 | 0.00209 | −0.056624 | −0.022874 | 0.005683 |
| 203 | 0.003111 | 0.001841 | 0.023133 | −0.017825 | −0.052919 | 0.003122 | −0.009397 | −0.075466 |
| 204 | 0.008501 | −0.030263 | −0.014021 | 0.025962 | −0.036623 | 0.065469 | −0.036294 | −0.034132 |
| 205 | −0.054362 | −0.086858 | −0.00984 | −0.004198 | 0.040569 | −0.012342 | 0.01436 | 0.036501 |
| 206 | 0.009309 | −0.023021 | 0.022941 | 0.021533 | 0.000756 | −0.058732 | 0.003196 | 0.035786 |
| 207 | 0.011321 | 0.004188 | 0.001683 | 0.010003 | 0.004423 | 0.020955 | −0.017782 | −0.066839 |
| 208 | −0.010981 | −0.053286 | −0.003182 | 0.003784 | −0.020401 | −0.03352 | −0.022903 | 0.015555 |
| 209 | −0.014171 | −0.039502 | −0.001998 | 0.052745 | −0.03093 | 0.016722 | −0.025705 | 0.010059 |
| 210 | 0.027672 | 0.034967 | 0.027711 | −0.00864 | 0.083021 | −0.039215 | 0.032937 | −0.05369 |
| 211 | 0.029343 | 0.021558 | 0.004909 | 0.023593 | 0.037268 | −0.035457 | 0.004988 | 0.044863 |
| 212 | 0.000387 | 0.037402 | −0.047168 | 0.027359 | 0.027395 | 0.027138 | −0.017902 | 0.087799 |
| 213 | 0.019805 | 0.062695 | 0.024374 | −0.029146 | 0.019769 | 0.019634 | −0.028373 | −0.064121 |
| 214 | 0.007356 | 0.014038 | 0.002861 | 0.008826 | 0.014276 | 0.001945 | −0.000095 | −0.004659 |
| 215 | −0.0043 | −0.02889 | −0.021506 | −0.007557 | 0.065764 | −0.021134 | 0.004966 | 0.006511 |
| 216 | −0.010221 | 0.018272 | −0.012919 | −0.045487 | 0.029663 | 0.019904 | 0.01121 | 0.013209 |
| 217 | 0.004509 | −0.020663 | 0.013958 | 0.003908 | −0.001616 | −0.057266 | 0.009632 | −0.00627 |
| 218 | −0.006508 | −0.031398 | −0.020217 | −0.011822 | 0.011894 | 0.008753 | 0.006394 | 0.045669 |
| 219 | −0.005414 | −0.008194 | −0.017699 | −0.006555 | 0.009356 | −0.011117 | 0.00002 | 0.009364 |
| 220 | 0.001331 | −0.015889 | −0.00139 | 0.002272 | −0.021009 | 0.000031 | 0.026893 | 0.00369 |
| 221 | −0.000246 | −0.021873 | 0.003112 | 0.018513 | 0.002948 | −0.011452 | 0.015203 | −0.029456 |
| 222 | −0.006424 | −0.013785 | −0.006337 | 0.016165 | 0.008826 | −0.009267 | 0.002324 | −0.010359 |
| 223 | 0.002976 | 0.011767 | −0.003267 | −0.000225 | 0.005269 | −0.001562 | 0.016197 | −0.013512 |
| 224 | 0.006102 | 0.018867 | 0.002363 | −0.023129 | 0.015962 | −0.023209 | −0.016078 | 0.033309 |
| 225 | 0.013657 | 0.023518 | 0.001351 | −0.015984 | 0.009274 | −0.036691 | −0.011351 | 0.017107 |
| 226 | −0.013246 | 0.003837 | −0.015084 | 0.001141 | −0.002654 | −0.001418 | −0.010867 | −0.004563 |
| 227 | −0.01013 | 0.022496 | −0.001959 | −0.024892 | 0.023153 | −0.012243 | 0.010617 | 0.003809 |
| 228 | −0.007237 | 0.026449 | −0.008947 | −0.017901 | 0.001101 | 0.013339 | −0.017627 | 0.020779 |
| 229 | 0.015112 | −0.04199 | 0.005901 | 0.007235 | −0.027098 | 0.010547 | −0.002122 | −0.005119 |
| 230 | 0.008598 | 0.005895 | 0.00828 | −0.034474 | 0.020303 | −0.024773 | 0.018709 | −0.01357 |
| 231 | −0.005244 | 0.005724 | 0.004194 | 0.023878 | 0.000043 | 0.0137 | 0.000383 | −0.021503 |
| 232 | −0.00794 | 0.016189 | −0.005849 | −0.001771 | 0.014513 | −0.035015 | −0.012075 | 0.009012 |
| 233 | 0.01284 | −0.014306 | −0.003479 | 0.017526 | 0.037215 | −0.02516 | 0.017558 | −0.017437 |
| 234 | 0.000614 | 0.009137 | −0.005579 | 0.006294 | 0.003425 | 0.024598 | 0.002807 | 0.036578 |
| 235 | 0.002709 | −0.017302 | −0.012295 | 0.045444 | 0.002445 | 0.023587 | −0.014053 | 0.035327 |
| 236 | −0.006444 | 0.034184 | 0.004973 | −0.006524 | 0.014624 | −0.011926 | −0.001011 | 0.019452 |
| 237 | −0.004909 | 0.000388 | −0.003508 | −0.032766 | −0.0115 | 0.004736 | −0.018217 | −0.010027 |
| 238 | 0.000347 | −0.007564 | 0.000775 | −0.010595 | 0.00794 | −0.021892 | −0.007976 | −0.000731 |
| 239 | 0.007367 | −0.004505 | 0.014091 | 0.019044 | 0.023668 | −0.019877 | −0.005681 | −0.000124 |
| 240 | −0.005655 | −0.00763 | 0.00833 | 0.001817 | −0.010398 | −0.010445 | −0.017127 | −0.005302 |

APPENDIX B3-continued

PCA Transformation
Matrix (340 × 340 Early/Late)

| | | | | | | | | |
|---|---|---|---|---|---|---|---|---|
| 241 | 0.004985 | −0.001344 | −0.010175 | 0.004699 | 0.019325 | 0.009125 | −0.010388 | 0.02051 |
| 242 | −0.001713 | −0.021477 | 0.008231 | 0.021419 | 0.011637 | 0.012833 | −0.003249 | 0.007066 |
| 243 | 0.003429 | −0.007279 | −0.012294 | 0.016837 | −0.002297 | −0.001455 | 0.006977 | −0.032935 |
| 244 | 0.014719 | 0.001159 | 0.015799 | 0.020415 | 0.014419 | −0.024706 | 0.019709 | −0.017729 |
| 245 | 0.016147 | −0.006073 | 0.014151 | 0.015352 | 0.007304 | 0.0017661 | −0.000899 | −0.001007 |
| 246 | 0.001876 | −0.022092 | 0.008951 | −0.004352 | −0.010617 | 0.024952 | 0.009274 | −0.001846 |
| 247 | 0.001574 | −0.002754 | 0.009582 | −0.002176 | −0.001526 | −0.004906 | 0.020605 | −0.02321 |
| 248 | −0.005103 | 0.010596 | −0.003968 | 0.001582 | 0.007752 | −0.019038 | 0.0139 | −0.012905 |
| 249 | −0.005465 | −0.001995 | −0.00735 | 0.008443 | −0.023244 | −0.029266 | −0.010644 | −0.004379 |
| 250 | −0.000209 | 0.017507 | 0.012838 | −0.012841 | −0.007448 | 0.005741 | −0.000555 | 0.007373 |
| 251 | 0.008771 | −0.012863 | 0.009317 | 0.011802 | −0.013708 | −0.014918 | −0.019243 | −0.00066 |
| 252 | 0.010712 | −0.016996 | 0.00972 | 0.029685 | −0.001884 | −0.012631 | −0.013216 | −0.030975 |
| 253 | 0.003748 | 0.038269 | −0.017308 | 0.00031 | −0.013833 | 0.014507 | −0.006642 | 0.026556 |
| 254 | 0.013215 | 0.035314 | 0.002002 | 0.007325 | 0.000017 | 0.015629 | 0.017187 | −0.004805 |
| 255 | 0.010399 | −0.003241 | 0.010216 | 0.006373 | −0.01526 | 0.013908 | 0.019784 | −0.015463 |
| 256 | −0.006798 | −0.031101 | −0.009399 | −0.026869 | −0.032058 | 0.079921 | −0.003135 | 0.014526 |
| 257 | −0.00628 | −0.002691 | 0.00265 | 0.012781 | −0.006681 | 0.011651 | 0.00078 | −0.013914 |
| 258 | −0.008762 | 0.006437 | −0.01997 | 0.00746 | 0.017368 | 0.019624 | 0.001571 | 0.024688 |
| 259 | 0.005595 | 0.029399 | −0.000276 | 0.005007 | −0.00145 | 0.005154 | −0.002026 | −0.009882 |
| 260 | 0.004385 | 0.028607 | 0.012527 | 0.018682 | −0.014957 | −0.00229 | 0.009087 | −0.050883 |
| 261 | 0.00673 | −0.015016 | 0.009337 | 0.015681 | −0.015618 | 0.006666 | −0.007983 | −0.029556 |
| 262 | 0.003585 | −0.012167 | 0.022529 | 0.01333 | −0.002412 | −0.014543 | −0.015727 | 0.011191 |
| 263 | 0.009824 | 0.010861 | 0.01676 | 0.015644 | 0.001726 | −0.019617 | −0.012012 | 0.004552 |
| 264 | 0.000742 | 0.034817 | −0.013161 | −0.002426 | −0.002838 | 0.029341 | 0.001523 | 0.012144 |
| 265 | 0.003064 | 0.049478 | −0.017316 | −0.008393 | −0.008239 | 0.032482 | 0.02187 | −0.007561 |
| 266 | −0.001839 | 0.011335 | −0.008652 | 0.00538 | −0.019076 | 0.020997 | 0.025675 | −0.032927 |
| 267 | −0.008758 | −0.006379 | −0.006642 | −0.02644 | −0.00266 | 0.04399 | −0.0032 | 0.050351 |
| 268 | −0.014496 | 0.010285 | −0.017596 | −0.000332 | 0.002867 | 0.003605 | −0.01005 | 0.006901 |
| 269 | −0.018533 | −0.002728 | −0.022794 | 0.00068 | −0.004172 | −0.004436 | −0.005869 | 0.002396 |
| 270 | −0.019288 | 0.014615 | −0.010195 | −0.009951 | −0.002988 | −0.004175 | 0.003157 | 0.000323 |
| 271 | 0.005252 | −0.027534 | 0.014062 | 0.010855 | −0.034849 | −0.025712 | −0.00085 | −0.009215 |
| 272 | 0.012549 | −0.023353 | 0.007459 | 0.010774 | −0.035631 | 0.007985 | −0.015397 | −0.01044 |
| 273 | 0.01065 | 0.016392 | 0.006395 | 0.007071 | −0.000735 | −0.036211 | 0.00336 | −0.019134 |
| 274 | 0.010565 | 0.01608 | 0.005163 | 0.009399 | −0.0032 | −0.032592 | 0.005152 | −0.023913 |
| 275 | −0.00429 | 0.018447 | 0.010403 | −0.032787 | 0.016097 | −0.036931 | 0.031215 | −0.018797 |
| 276 | −0.004979 | 0.017653 | 0.010237 | 0.005122 | 0.005674 | 0.013306 | −0.007492 | 0.026656 |
| 277 | 0.00314 | 0.026337 | 0.008296 | 0.00488 | 0.02348 | 0.008073 | −0.00601 | 0.017807 |
| 278 | 0.004585 | 0.026148 | 0.008315 | 0.00067 | 0.023905 | 0.007335 | −0.009398 | 0.02923 |
| 279 | 0.002207 | 0.01075 | 0.015164 | 0.013978 | 0.013541 | −0.025557 | −0.012849 | 0.005714 |
| 280 | 0.003086 | 0.028026 | −0.018141 | −0.001105 | 0.008658 | 0.014469 | 0.017914 | 0.005592 |
| 281 | 0.011949 | −0.008151 | 0.001197 | −0.003692 | −0.01937 | 0.030328 | 0.005117 | 0.004658 |
| 282 | 0.011434 | −0.017413 | −0.000793 | 0.001041 | −0.008601 | 0.023009 | 0.012923 | 0.025082 |
| 283 | 0.002795 | 0.016344 | 0.006956 | −0.006335 | −0.005939 | −0.008254 | 0.01053 | −0.009832 |
| 284 | −0.009127 | 0.001381 | −0.00751 | −0.003304 | −0.008927 | 0.017255 | −0.012563 | 0.007415 |
| 285 | −0.006177 | −0.008112 | −0.002751 | 0.004619 | −0.007966 | 0.008169 | −0.006831 | 0.013849 |
| 286 | 0.001507 | −0.01141 | −0.02167 | 0.007832 | 0.014544 | 0.031127 | −0.007133 | 0.015252 |
| 287 | −0.002435 | −0.01397 | −0.021968 | 0.006178 | 0.012631 | 0.020637 | −0.000598 | 0.019953 |
| 288 | −0.014646 | 0.006702 | −0.011639 | −0.009458 | 0.00583 | 0.028878 | −0.014361 | 0.059812 |
| 289 | −0.000003 | 0.000467 | 0.014448 | 0.011678 | −0.00862 | −0.008689 | 0.004398 | 0.020857 |
| 290 | −0.002537 | −0.001652 | −0.002917 | −0.014021 | −0.02542 | 0.014003 | −0.029434 | 0.028812 |

APPENDIX B3-continued

PCA Transformation
Matrix (340 × 340 Early/Late)

| | | | | | | | | |
|---|---|---|---|---|---|---|---|---|
| 291 | −0.001791 | −0.001659 | −0.001635 | −0.013678 | −0.025667 | 0.015143 | −0.0263 | 0.020452 |
| 292 | 0.001158 | −0.016796 | 0.00524 | −0.00668 | −0.026861 | 0.009438 | −0.029621 | 0.014508 |
| 293 | −0.012275 | 0.044926 | −0.004507 | −0.021507 | −0.011525 | 0.033565 | −0.019927 | −0.012488 |
| 294 | −0.024444 | −0.010633 | −0.02048 | −0.022059 | 0.000993 | 0.003698 | −0.005533 | 0.019147 |
| 295 | −0.000131 | 0.019871 | 0.016025 | −0.008614 | −0.030064 | −0.003837 | −0.010782 | −0.025979 |
| 296 | −0.01284 | −0.016555 | 0.012635 | −0.009676 | −0.034487 | −0.055748 | 0.016258 | −0.042593 |
| 297 | −0.0036 | 0.00489 | 0.011501 | −0.001083 | −0.033717 | 0.0289 | −0.015866 | −0.019589 |
| 298 | −0.006482 | 0.005917 | −0.011068 | −0.031935 | −0.015055 | −0.068532 | −0.010062 | −0.008656 |
| 299 | −0.005701 | 0.023921 | −0.011403 | −0.017266 | −0.042233 | −0.00086 | −0.016141 | −0.038053 |
| 300 | −0.012392 | 0.030236 | −0.008438 | −0.033482 | 0.006497 | 0.0074 | −0.02436 | 0.006282 |
| 301 | −0.014406 | 0.010888 | −0.006132 | −0.019166 | −0.03665 | −0.005773 | −0.023127 | 0.009873 |
| 302 | −0.015935 | −0.019563 | −0.003256 | −0.010286 | −0.017019 | −0.025847 | −0.008664 | 0.006187 |
| 303 | −0.00623 | −0.018084 | −0.018159 | −0.009892 | −0.020436 | −0.025408 | −0.003727 | −0.032961 |
| 304 | −0.007954 | 0.009584 | −0.021275 | −0.034647 | −0.019884 | −0.03063 | −0.020817 | −0.005804 |
| 305 | 0.018008 | −0.003478 | 0.015632 | −0.00916 | −0.00555 | −0.005164 | −0.01005 | −0.044601 |
| 306 | −0.020324 | 0.006074 | −0.019434 | −0.041358 | −0.043482 | 0.020047 | −0.029202 | −0.046659 |
| 307 | −0.010565 | 0.064836 | −0.036189 | −0.013003 | −0.015194 | 0.005768 | −0.03885 | 0.028439 |
| 308 | 0.01766 | −0.00303 | 0.023809 | 0.010522 | −0.054192 | −0.050095 | −0.020101 | −0.042334 |
| 309 | −0.038448 | −0.020144 | −0.034684 | −0.03026 | −0.007919 | −0.003768 | −0.002127 | 0.012368 |
| 310 | −0.016392 | 0.000373 | −0.036817 | −0.030068 | −0.003021 | −0.054715 | 0.032729 | −0.013983 |
| 311 | −0.021478 | 0.03412 | −0.029405 | −0.013871 | 0.002538 | −0.007034 | −0.025977 | 0.008515 |
| 312 | 0.007194 | −0.101947 | −0.014478 | 0.010038 | −0.033042 | 0.033153 | −0.055336 | 0.000061 |
| 313 | −0.015003 | 0.000503 | −0.026006 | −0.016104 | −0.005445 | 0.024482 | −0.012831 | 0.013704 |
| 314 | 0.015528 | 0.006586 | 0.001199 | −0.039265 | 0.002216 | 0.029567 | −0.011621 | 0.031723 |
| 315 | −0.033627 | −0.026846 | −0.032242 | −0.017506 | −0.019473 | 0.017129 | −0.006458 | −0.018316 |
| 316 | −0.02192 | 0.016652 | −0.000817 | −0.019353 | −0.05344 | −0.001395 | 0.035282 | 0.006488 |
| 317 | −0.036929 | −0.004387 | −0.025191 | −0.026786 | −0.017658 | 0.013403 | −0.00117 | 0.007341 |
| 318 | −0.029887 | 0.024879 | −0.017669 | −0.012369 | −0.01595 | −0.004265 | −0.010074 | −0.031413 |
| 319 | −0.038735 | −0.013842 | −0.049376 | −0.01357 | −0.016504 | 0.009163 | −0.000102 | −0.00606 |
| 320 | −0.021359 | 0.014614 | −0.038491 | 0.000125 | 0.008189 | 0.013086 | −0.01153 | 0.01196 |
| 321 | −0.015195 | 0.018338 | −0.007177 | −0.02944 | −0.005818 | 0.030348 | −0.0324 | 0.033384 |
| 322 | 0.009442 | 0.001741 | 0.025585 | −0.035159 | −0.015591 | −0.046366 | −0.007652 | 0.057468 |
| 323 | 0.011299 | 0.01946 | −0.01349 | −0.013949 | −0.001004 | −0.005033 | −0.051108 | 0.020128 |
| 324 | −0.009083 | 0.017642 | 0.004855 | −0.00071 | −0.030768 | −0.034313 | 0.022697 | −0.019958 |
| 325 | −0.056588 | −0.062816 | −0.040905 | −0.01708 | −0.009871 | 0.011465 | 0.016395 | 0.004358 |
| 326 | −0.042829 | −0.02361 | −0.050923 | −0.022375 | 0.012625 | 0.003854 | −0.015763 | −0.043692 |
| 327 | −0.020223 | −0.025144 | −0.022501 | −0.010401 | −0.000319 | −0.03074 | −0.01527 | −0.006328 |
| 328 | 0.005679 | −0.042175 | 0.014517 | −0.016692 | −0.014208 | −0.058983 | −0.043365 | 0.020468 |
| 329 | −0.010884 | −0.039137 | −0.017419 | 0.020538 | −0.002072 | −0.01421 | −0.022271 | −0.02631 |
| 330 | −0.004909 | −0.04231 | −0.001619 | −0.020267 | 0.015401 | −0.033004 | −0.001953 | −0.014494 |
| 331 | −0.041082 | −0.026511 | −0.044732 | −0.021391 | 0.003094 | 0.01632 | −0.024289 | 0.000952 |
| 332 | −0.027038 | 0.054886 | −0.037843 | −0.021021 | 0.015988 | −0.023123 | −0.016948 | −0.012044 |
| 333 | 0.934163 | −0.043952 | −0.043486 | −0.026927 | −0.009995 | 0.014065 | −0.008266 | 0.012836 |
| 334 | −0.036475 | 0.726255 | −0.005268 | 0.030214 | −0.029628 | −0.024904 | −0.004635 | −0.014259 |
| 335 | −0.04574 | −0.006876 | 0.919861 | −0.018946 | 0.006715 | 0.023378 | −0.01068 | 0.0284 |
| 336 | −0.038481 | 0.008207 | −0.027901 | 0.858255 | −0.003064 | 0.000793 | −0.025043 | 0.021223 |
| 337 | −0.009541 | −0.031433 | −0.008498 | −0.003364 | 0.873452 | −0.015811 | −0.02387 | −0.047374 |
| 338 | 0.019251 | −0.038953 | 0.021076 | 0.010616 | 0.000868 | 0.738277 | 0.013979 | −0.07591 |
| 339 | −0.016745 | −0.018486 | −0.011618 | −0.009654 | −0.022557 | 0.0157891 | 0.886852 | 0.042981 |

APPENDIX B4

PCA Transformation Matrix (82 × 82 Normal/Diseased)

| | A | B | C | D | E | F | G | H | I | J | K | L | M |
|---|---|---|---|---|---|---|---|---|---|---|---|---|---|
| 1 | 409.4/255.3>GPA:Lyso 16:0 | 0.114759 | −0.051905 | −0.013778 | −0.110977 | 0.221117 | −0.057009 | 0.087631 | −0.126223 | 0.080964 | 0.093727 | −0.025278 | 0.151599 |
| 2 | 437.4/283.3>GPAlyso 18:0 | 0.034866 | 0.088283 | −0.011396 | −0.136625 | 0.247874 | 0.151009 | 0.010982 | −0.126 | −0.038998 | −0.198221 | 0.037718 | 0.007115 |
| 3 | 647.8/255.3>GPA:16:0/16:0 | 0.115239 | −0.044186 | 0.14981 | −0.193332 | −0.039585 | 0.027614 | 0.053642 | 0.010153 | 0.090358 | 0.13925 | −0.025007 | 0.088774 |
| 4 | 673.8/281.3>GPA:18:1/16:0 | 0.055934 | 0.02702 | 0.213677 | −0.186921 | −0.196138 | 0.069761 | 0.024154 | 0.061457 | 0.031865 | 0.070003 | −0.000456 | −0.022459 |
| 5 | 699.8/281.3>GPA:36:2 | 0.055597 | 0.029329 | 0.210775 | −0.189003 | −0.212305 | 0.063259 | 0.042354 | 0.04886 | 0.014137 | 0.048541 | −0.017246 | −0.019335 |
| 6 | 701.8/283.3>GPA:36:1 | 0.044331 | 0.025896 | 0.219359 | −0.18489 | −0.204341 | 0.088021 | 0.030901 | 0.042881 | 0.007047 | 0.060986 | 0.010571 | −0.009524 |
| 7 | 703.8/283.3>GPA:36:0 | 0.088386 | 0.062411 | 0.188306 | −0.205886 | −0.057318 | 0.108775 | 0.068955 | −0.011409 | 0.02078 | −0.058672 | 0.046382 | −0.001894 |
| 8 | 721.8/281.3>GPA:16:0/22:5 | 0.143751 | 0.092109 | −0.051878 | −0.123848 | 0.143237 | −0.033527 | 0.080881 | 0.005872 | 0.02188 | −0.108493 | −0.018808 | −0.073239 |
| 9 | 723.8/283.3>GPA:18:0/20:4 | 0.047793 | 0.01543 | 0.194626 | −0.20441 | −0.191611 | 0.096465 | 0.057959 | 0.009987 | 0.009828 | 0.006154 | 0.018196 | −0.007425 |
| 10 | 731.8/283.3>GPA:38:0 | 0.112663 | 0.07029 | 0.149659 | −0.213156 | −0.015465 | 0.064339 | 0.06731 | 0.059256 | 0.027094 | 0.035105 | 0.005083 | −0.002569 |
| 11 | 757.8/281.3>GPA:40:1 | 0.102212 | 0.018106 | 0.173068 | −0.135695 | −0.211452 | −0.053478 | −0.030895 | −0.037733 | −0.019567 | −0.070057 | −0.073219 | 0.022795 |
| 12 | 759.8/283.3>GPA:40:0 | 0.082457 | 0.030179 | 0.200883 | −0.168812 | −0.163533 | 0.120186 | 0.015696 | 0.017822 | −0.036463 | 0.085138 | 0.091034 | 0.006522 |
| 13 | 483.4/255.3>GPGro:Lyso 16:0 | 0.116476 | 0.055434 | −0.07137 | −0.168625 | 0.219045 | −0.002162 | −0.01437 | 0.131646 | 0.022771 | 0.067748 | −0.000918 | −0.054605 |
| 14 | 507.4/279.3>GPGro:Lyso 18:2 | 0.084755 | 0.038955 | 0.004174 | −0.161687 | 0.279516 | 0.003025 | −0.068582 | 0.196936 | 0.083892 | 0.059977 | −0.022513 | −0.062261 |
| 15 | 509.4/281.3>GPGro:Lyso 18:1 | 0.036809 | 0.045452 | −0.09925 | −0.201575 | 0.187447 | 0.086097 | −0.149794 | 0.138368 | −0.146016 | 0.108618 | −0.08814 | −0.024014 |
| 16 | 511.4/283.3>GPGro:Lyso 18:0 | 0.099245 | 0.095536 | −0.06473 | −0.17404 | 0.218888 | −0.012759 | −0.03823 | 0.150967 | 0.054321 | 0.038387 | −0.009991 | −0.128261 |
| 17 | 743.8/279.3>GPGro:18:2/16:1 | 0.000306 | −0.031251 | 0.067245 | 0.226988 | −0.167013 | −0.109876 | −0.134992 | 0.148008 | 0.07772 | 0.063039 | −0.128438 | −0.074352 |
| 18 | 769.8/279.3>GPGro:18:2/18:2 | −0.047362 | −0.048801 | 0.149363 | 0.162023 | 0.066206 | 0.163835 | −0.207282 | 0.082342 | −0.152555 | 0.148842 | 0.082238 | 0.069439 |
| 19 | 771.8/279.3>GPGro:18:2/18:1 | −0.010114 | 0.039716 | 0.122877 | 0.148986 | −0.029076 | −0.274197 | 0.171412 | −0.003908 | 0.124022 | −0.137025 | −0.04511 | 0.046147 |
| 20 | 773.8/279.3>GPGro:18:2/18:0 | 0.022783 | 0.159315 | 0.05515 | −0.007967 | 0.171198 | −0.17077 | 0.087029 | 0.218397 | 0.162282 | −0.117904 | −0.003033 | −0.121665 |
| 21 | 775.8/281.3>GPGro:18:1/18:0 | 0.035719 | 0.152728 | −0.101139 | −0.159584 | 0.140089 | −0.019483 | 0.088398 | 0.198872 | −0.066928 | −0.032275 | −0.087114 | −0.150611 |
| 22 | 777.8/283.3>GPGro:18:0/18:0 | 0.132216 | 0.109429 | −0.032118 | −0.10222 | 0.179947 | −0.055154 | 0.070614 | 0.033115 | 0.042225 | −0.094011 | 0.043661 | −0.071902 |
| 23 | 476.6/196.1>Lyso GPEtn:Lyso18:2a | −0.057273 | −0.000286 | 0.234232 | 0.076985 | 0.169126 | 0.078949 | 0.071045 | −0.138562 | −0.002664 | −0.128005 | −0.071893 | −0.074736 |
| 24 | 478.4/196.1>Lyso GPEtn:Lyso 18:1 | −0.036966 | −0.008666 | 0.178244 | 0.059122 | 0.144355 | 0.2527 | −0.015708 | −0.195836 | −0.137145 | −0.098874 | −0.003303 | −0.162105 |
| 25 | 480.4/196.1>Lyso GPEtn:Lyso 18:0 | 0.083195 | −0.021459 | 0.023377 | 0.080471 | 0.078865 | 0.259405 | 0.02949 | −0.119379 | −0.093786 | 0.165049 | 0.140061 | 0.06671 |
| 26 | 500.4/196.1>Lyso GPEtn:Lyso 20:4 | −0.077714 | −0.101173 | 0.07984 | 0.022699 | 0.112746 | 0.261203 | −0.102647 | −0.142017 | −0.125497 | −0.147807 | 0.030004 | −0.251741 |
| 27 | 524.4/196.1>Lyso GPEtn:Lyso 22:6 | −0.085276 | −0.140801 | 0.059955 | 0.00748 | 0.091087 | 0.213403 | −0.098063 | −0.143522 | −0.187517 | −0.049772 | −0.030791 | −0.233785 |
| 28 | 520.4/184.1>GPCho:Lyso 18:2 | 0.043723 | −0.070168 | 0.224968 | 0.089802 | 0.176074 | −0.033108 | 0.052393 | −0.048958 | 0.07763 | 0.1074 | −0.092582 | 0.208565 |
| 29 | 544.4/184.1>GPCho:Lyso 20:4 | −0.019805 | −0.230432 | −0.006344 | −0.064596 | 0.08485 | 0.029276 | 0.154131 | −0.065453 | 0.03949 | −0.029109 | 0.192939 | 0.12334 |
| 30 | 568.4/184.1>GPCho:Lyso 22:6 | −0.027587 | −0.224793 | 0.012989 | −0.074323 | 0.08228 | −0.107818 | 0.093568 | −0.070711 | −0.118583 | 0.226332 | −0.076564 | 0.053397 |
| 31 | 570.4/184.1>GPCho:Lyso 22:5 | −0.042658 | −0.205554 | 0.037287 | −0.074979 | 0.104432 | −0.102977 | 0.18357 | −0.07623 | −0.11503 | 0.171328 | −0.097567 | 0.074327 |
| 32 | 678.5/184.1>GPCho:28:0a | 0.054681 | 0.115962 | 0.12006 | 0.058059 | 0.02265 | −0.045942 | 0.185717 | −0.095566 | −0.217952 | −0.039953 | 0.04958 | −0.150402 |
| 33 | 704.6/184.1>GPCho:30:1a | 0.164259 | −0.092 | −0.040425 | 0.009194 | −0.038398 | −0.032556 | −0.118678 | −0.136694 | 0.132106 | −0.000345 | −0.036496 | −0.16018 |
| 34 | 732.6/184.1>GPCho:32:1a | 0.100536 | 0.061317 | −0.160773 | −0.017742 | −0.07246 | 0.049648 | 0.181416 | −0.124905 | −0.105377 | −0.02658 | −0.286556 | 0.044199 |
| 35 | 734.6/184.1>GPCho:32:0a | 0.096861 | 0.063469 | −0.173175 | −0.051909 | −0.163999 | 0.012087 | −0.025338 | −0.126321 | −0.039239 | −0.220284 | −0.20561 | −0.019751 |
| 36 | 742.6/184.1>GPCho:34:2p, 34:3e | 0.051127 | 0.136408 | 0.151904 | −0.044687 | 0.017705 | −0.190119 | −0.022666 | −0.165526 | −0.101818 | 0.07455 | 0.082076 | −0.128359 |
| 37 | 744.6/184.1>GPCho:34:1p, 34:2e | −0.069467 | 0.043493 | 0.242191 | 0.0071 | 0.091061 | −0.156418 | −0.112471 | −0.079845 | 0.029719 | −0.108582 | −0.10264 | 0.041184 |
| 38 | 748.6/184.1>GPCho:34:0e | 0.081242 | 0.121693 | −0.033754 | −0.071782 | −0.079615 | −0.148515 | −0.185889 | −0.204608 | −0.13649 | −0.241832 | 0.03069 | 0.153106 |
| 39 | 756.6/184.1>GPCho:34:3a | −0.080158 | 0.234186 | 0.010982 | 0.037044 | 0.015483 | −0.020846 | −0.027672 | −0.024561 | −0.065869 | 0.046545 | 0.024379 | 0.072942 |
| 40 | 758.7/184.1>GPCho:34:2a | −0.042508 | 0.155796 | 0.022728 | 0.054399 | −0.05808 | 0.093417 | −0.228821 | 0.267954 | 0.007933 | 0.125095 | −0.283857 | −0.029941 |
| 41 | 762.6/184.1>GPCho:34:0a | 0.0287 | 0.133212 | −0.148055 | −0.037131 | −0.123136 | 0.028556 | 0.140236 | −0.0786071 | −0.20011 | −0.175819 | −0.365844 | −0.016345 |
| 42 | 768.6/184.1>GPCho:36:3p, 36:4e | −0.118886 | −0.125837 | 0.03275 | −0.161874 | 0.036888 | −0.094605 | −0.134723 | −0.0853491 | 0.0072881 | −0.115642 | 0.0598 | −0.078432 |
| 43 | 770.6/184.1>GPCho:36:2p, 36:3e | −0.090413 | 0.023063 | 0.17977 | −0.096231 | 0.097846 | −0.197034 | −0.144544 | −0.081979 | 0.037218 | −0.111824 | −0.070154 | 0.070605 |
| 44 | 772.6/184.1>GPCho:36:1p, 36:2e | 0.004049 | 0.194032 | 0.111378 | 0.015941 | 0.043028 | −0.135627 | −0.152931 | −0.111105 | −0.076651 | −0.107983 | 0.087574 | 0.237239 |
| 45 | 782.6/184.1>GPCho:36:4a | −0.129707 | −0.077698 | −0.117986 | −0.088742 | −0.091371 | 0.090636 | 0.095902 | 0.118986 | 0.069601 | −0.211633 | 0.216589 | −0.018946 |

APPENDIX B4-continued

PCA Transformation
Matrix (82 × 82
Normal/Diseased)

| | | | | | | | | | | | | | |
|---|---|---|---|---|---|---|---|---|---|---|---|---|---|
| 46 | 784.6/184.1>GPCho:36:3a | −0.141611 | 0.072148 | 0.053934 | −0.010025 | −0.012032 | 0.027254 | 0.203171 | 0.148698 | −0.04019 | −0.106507 | 0.063864 | 0.218314 |
| 47 | 786.6/184.1>GPCho:36:2a | −0.093682 | 0.137365 | 0.158851 | 0.121661 | 0.104201 | −0.008505 | 0.026608 | 0.087584 | −0.07947 | 0.00102 | −0.088998 | 0.153683 |
| 48 | 788.6/184.1>GPCho:36:1a | 0.040304 | 0.218352 | 0.02721 | 0.101228 | 0.020812 | −0.044236 | 0.139493 | −0.081815 | −0.19154 | 0.050707 | −0.047676 | 0.050019 |
| 49 | 792.6/184.1>GPCho:38:5p, 38:6e | −0.078427 | −0.09013 | 0.029384 | −0.156902 | 0.009149 | −0.238731 | −0.103282 | −0.113507 | −0.196886 | 0.148123 | −0.091174 | −0.122171 |
| 50 | 794.6/184.1>GPCho:38:4p, 38:5e | −0.105702 | −0.133246 | −0.015129 | −0.185129 | 0.023401 | −0.119935 | −0.179494 | −0.037017 | 0.007282 | −0.08196 | −0.030047 | 0.052927 |
| 51 | 796.6/184.1>GPCho:38:3p, 38:4e | −0.099955 | −0.093464 | −0.026052 | −0.198842 | −0.010895 | −0.141806 | −0.178284 | −0.033716 | 0.008619 | −0.197564 | 0.160245 | 0.103269 |
| 52 | 808.6/184.1>GPCho:38:5a | −0.15017 | −0.093883 | −0.062458 | −0.10286 | −0.023306 | −0.079624 | 0.148703 | 0.074362 | −0.158249 | −0.008849 | 0.069714 | −0.003672 |
| 53 | 810.6/184.1>GPCho:38:4a | −0.142177 | −0.064002 | −0.113963 | −0.09126 | −0.047104 | 0.017823 | 0.152833 | 0.097088 | 0.019118 | −0.165511 | 0.307726 | 0.04993 |
| 54 | 814.6/184.1>GPCho:38:2a | 0.173471 | −0.008572 | −0.104513 | −0.011661 | −0.059687 | −0.073428 | −0.042779 | −0.134583 | 0.098892 | 0.071601 | 0.058049 | −0.055484 |
| 55 | 816.6/184.1>GPCho:38:1a | 0.138507 | 0.100502 | 0.002794 | 0.093549 | 0.014677 | −0.131207 | −0.010504 | −0.100403 | 0.008388 | 0.194851 | 0.21742 | −0.186111 |
| 56 | 820.6/184.1>GPCho:40:5p, 40:6e | −0.111301 | −0.107239 | −0.009731 | −0.151242 | −0.002405 | −0.213591 | −0.118031 | −0.058003 | −0.163761 | 0.096687 | −0.032067 | 0.032142 |
| 57 | 826.6/184.1>GPCho:40:2p, 40:3e | 0.094571 | 0.215027 | −0.060295 | −0.003962 | −0.028229 | −0.038408 | −0.089231 | −0.039676 | −0.143054 | 0.006886 | 0.177908 | 0.010188 |
| 58 | 828.6/184.1>GPCho:40:1p, 40:2e | 0.123474 | 0.166354 | −0.047378 | 0.001635 | −0.034173 | −0.050881 | −0.116565 | 0.015472 | −0.222741 | −0.055241 | 0.190199 | 0.06339 |
| 59 | 834.6/184.1>GPCho:40:6a | −0.125619 | −0.104178 | −0.067288 | −0.102706 | −0.029394 | −0.143505 | 0.140659 | 0.023026 | −0.195974 | 0.16481 | −0.078675 | −0.0487 |
| 60 | 836.6/184.1>GPCho:40:5a | −0.086145 | 0.050116 | −0.114282 | −0.048375 | −0.089984 | −0.152406 | 0.203272 | 0.033177 | −0.298927 | 0.175369 | 0.117207 | −0.164399 |
| 61 | 703.8/184.4>SM:d18:1/16:0 | 0.163979 | −0.100076 | −0.048009 | −0.004666 | −0.034404 | −0.049889 | −0.13189 | −0.106711 | 0.148259 | 0.025651 | −0.005526 | −0.127198 |
| 62 | 731.8/184.4>SM:d18:1/18:0 | 0.154963 | −0.053326 | −0.13747 | 0.007934 | −0.077157 | 0.024042 | −0.01179 | −0.122108 | 0.135951 | 0.08482 | 0.033453 | 0.004356 |
| 63 | 787.9/184.4>SM:d18:1/22:0 | 0.014218 | 0.078623 | 0.173738 | 0.150818 | 0.129722 | −0.162663 | 0.123754 | −0.083932 | 0.117025 | 0.115723 | 0.109026 | −0.005758 |
| 64 | 813.9/184.4>SM:d18:1/24:1 | 0.165571 | −0.059888 | −0.096618 | −0.033682 | −0.059503 | −0.064771 | −0.044714 | −0.136737 | 0.153412 | 0.050337 | 0.056362 | −0.095133 |
| 65 | 841.9/184.4>SM:d18:1/26:1 | 0.108008 | 0.187231 | −0.074281 | 0.054199 | −0.061773 | 0.005022 | −0.045757 | −0.064551 | −0.079422 | 0.130164 | 0.288459 | −0.012642 |
| 66 | 843.9/184.4>SM:d18:1/26:0 | −0.077372 | 0.100996 | −0.083497 | −0.045188 | −0.003167 | 0.089345 | −0.246852 | 0.076341 | −0.115772 | 0.173105 | 0.09159 | 0.204435 |
| 67 | 538.7/264.4>Cer:d18:1/16:0 | 0.141523 | −0.092318 | −0.038171 | −0.076708 | 0.136315 | 0.054751 | −0.051883 | −0.039035 | −0.072634 | 0.02395 | −0.064597 | 0.268 |
| 68 | 566.7/264.4>Cer:d18:1/18:0 | 0.162111 | −0.047178 | −0.109401 | −0.007068 | 0.009547 | 0.097918 | 0.035782 | −0.093264 | 0.02229 | 0.067548 | −0.030602 | 0.210932 |
| 69 | 594.7/264.4>Cer:d18:1/20:0 | 0.174791 | −0.063685 | −0.053824 | 0.018389 | 0.013405 | 0.080164 | 0.046067 | −0.041733 | −0.064567 | −0.018417 | −0.032602 | 0.232816 |
| 70 | 622.8/264.4>Cer:d18:1/22:0 | 0.170333 | −0.07498 | 0.024385 | 0.035792 | 0.051476 | 0.018692 | 0.131279 | 0.020432 | −0.072242 | −0.08554 | 0.006966 | 0.118071 |
| 71 | 648.9/264.4>Cer:d18:1/24:1 | 0.183616 | −0.057341 | −0.052207 | −0.025506 | 0.01884 | 0.037202 | 0.053797 | −0.052111 | −0.021534 | −0.022467 | −0.047612 | 0.093569 |
| 72 | 650.9/264.4>Cer:d18:1/24:0 | 0.137283 | −0.08327 | 0.10557 | 0.078094 | 0.004296 | −0.046628 | 0.189092 | 0.021805 | −0.029262 | −0.087274 | 0.051087 | −0.150055 |
| 73 | 700.7/264.4>MonoHexCer:d18:1/16:0 | 0.148766 | −0.125579 | 0.039006 | 0.066748 | −0.024576 | −0.011 | −0.060293 | 0.167842 | −0.162174 | −0.119973 | 0.004391 | 0.065454 |
| 74 | 728.7/264.4>MonoHexCer:d18:1/18:0 | 0.175842 | −0.096098 | 0.032884 | 0.004635 | −0.011244 | −0.022753 | −0.003513 | −0.000892 | 0.007955 | −0.022096 | −0.061367 | −0.058954 |
| 75 | 784.8/264.4>MonoHexCer:d18:1/22:0 | 0.143405 | −0.132589 | 0.082307 | 0.082004 | 0.003743 | −0.052609 | −0.042946 | 0.17351 | −0.135752 | −0.091891 | 0.025424 | −0.038063 |
| 76 | 810.9/264.4>MonoHexCer:d18:1/24:1 | 0.164966 | −0.12527 | 0.017239 | 0.027677 | −0.033346 | −0.037078 | −0.046809 | 0.117975 | −0.105562 | −0.070293 | −0.02823 | 0.038479 |
| 77 | 812.9/264.4>MonoHexCer:d18:1/24:0 | 0.129991 | −0.134368 | 0.075979 | 0.086263 | −0.000067 | −0.052285 | −0.045865 | 0.203527 | −1.19604 | −0.101307 | 0.027478 | −0.033118 |
| 78 | 862.7/264.4>DiHexCer:d18:1/16:0 | 0.158259 | −0.131298 | 0.023141 | 0.079046 | −0.010829 | −0.044671 | −0.057141 | 0.080241 | −0.088688 | −0.061043 | 0.018828 | −0.092307 |
| 79 | 890.7/264.4>DiHexCer:d18:1/18:0 | 0.160167 | −0.118595 | 0.020827 | 0.067281 | 0.000415 | −0.034501 | −0.008959 | 0.139594 | −0.104587 | −0.094047 | 0.075572 | 0.09479 |
| 80 | 946.8/264.4>DiHexCer:d18:1/22:0 | −0.158405 | −0.127348 | 0.052891 | 0.062726 | 0.016964 | −0.069351 | −0.017328 | 0.120534 | −0.090938 | −0.040727 | 0.046343 | −0.046165 |
| 81 | 972.9/264.4>DiHexCer:d18:1/24:1 | 0.167871 | −0.118521 | 0.006863 | 0.034552 | −0.011151 | −0.0650121 | −0.046841 | 0.035922 | −0.046437 | −0.021776 | −0.030206 | −0.061891 |
| 82 | 974.9/264.4>DiHexCer:d18:1/24:0 | 0.150027 | −0.130848 | 0.056823 | 0.070369 | 0.014455 | −0.095055 | −0.02676 | 0.143224 | −0.107355 | −0.083686 | 0.052452 | −0.002574 |

| | N | O | P | Q | R | S | T | U | V | W | X | Y | Z | AA |
|---|---|---|---|---|---|---|---|---|---|---|---|---|---|---|
| 1 | −0.121301 | 0.241247 | −0.177961 | 0.058399 | −0.235537 | 0.103471 | −0.068486 | 0.072591 | −0.033091 | 0.188115 | −0.090353 | 0.036654 | −0.116176 | 0.016086 |
| 2 | 0.179797 | 0.012645 | −0.182498 | 0.084957 | −0.261371 | 0.063478 | 0.236355 | 0.120025 | 0.218312 | −0.01962 | −0.227994 | 0.065341 | −0.199534 | −0.113073 |
| 3 | −0.155376 | 0.119427 | −0.046512 | −0.09785 | −0.114476 | 0.011653 | −0.07771 | 0.039653 | −0.001837 | 0.142524 | −0.210222 | 0.04256 | 0.001071 | 0.189034 |
| 4 | −0.019364 | −0.035176 | −0.005559 | −0.019275 | 0.002901 | −0.00833 | 0.015337 | −0.022707 | 0.067102 | 0.010913 | −0.075808 | −0.046479 | −0.000765 | 0.069096 |
| 5 | −0.014578 | −0.014559 | 0.011186 | 0.012909 | 0.005381 | −0.00114 | 0.01313 | −0.025745 | 0.055927 | −0.005897 | −0.007938 | −0.041584 | 0.008837 | 0.046578 |
| 6 | 0.034102 | −0.042752 | −0.005289 | 0.006901 | −0.007924 | −0.005214 | 0.059055 | −0.071258 | 0.038453 | −0.011272 | 0.007958 | −0.02614 | 0.038414 | 0.004609 |
| 7 | 0.111572 | 0.054805 | −0.032196 | 0.084448 | −0.09849 | −0.021476 | 0.120124 | 0.055805 | 0.033681 | 0.013199 | −0.045447 | 0.017531 | −0.114628 | −0.112877 |
| 8 | 0.041645 | −0.061316 | −0.095786 | 0.029526 | 0.086688 | 0.172151 | 0.029233 | 0.177074 | −0.018493 | −0.004219 | 0.317067 | 0.15089 | 0.034536 | 0.162855 |
| 9 | 0.08431 | −0.039694 | 0.017122 | 0.085027 | −0.100808 | 0.002505 | 0.039709 | −0.049241 | 0.058669 | −0.040206 | −0.001867 | −0.146225 | −0.009398 | −0.0789 |

APPENDIX B4-continued

PCA Transformation Matrix (82 × 82 Normal/Diseased)

| | | | | | | | | | | | | | | |
|---|---|---|---|---|---|---|---|---|---|---|---|---|---|---|
| 10 | 0.044201 | −0.014544 | 0.057267 | 0.037329 | 0.154807 | 0.003226 | −0.039065 | 0.022117 | −0.129506 | −0.060003 | 0.069107 | 0.156985 | 0.064881 | −0.107184 |
| 11 | −0.039361 | −0.022893 | 0.05347 | 0.021884 | −0.122872 | 0.043793 | −0.077329 | −0.048209 | −0.074727 | −0.115059 | 0.289476 | 0.10184 | 0.097937 | 0.029775 |
| 12 | −0.019253 | −0.061921 | 0.031842 | −0.014351 | 0.065167 | −0.080226 | 0.075368 | 0.017374 | 0.017221 | −0.001187 | 0.087909 | 0.014524 | −0.127191 | 0.001399 |
| 13 | 0.023069 | 0.034907 | 0.05432 | −0.216558 | 0.065946 | −0.098481 | −0.114191 | −0.159221 | −0.091052 | −0.040843 | 0.03337 | −0.020909 | 0.072348 | −0.110752 |
| 14 | −0.012842 | 0.034556 | 0.064883 | −0.044304 | 0.104788 | −0.163694 | −0.078086 | −0.06016 | −0.132979 | −0.150807 | −0.032522 | −0.113756 | −0.069375 | −0.136392 |
| 15 | −0.117676 | 0.264949 | 0.143819 | 0.109357 | −0.083447 | −0.136829 | 0.001983 | −0.130752 | 0.023091 | −0.167532 | 0.133917 | −0.039706 | −0.164033 | 0.033454 |
| 16 | 0.046029 | −0.073318 | 0.004718 | −0.107673 | 0.138129 | −0.106949 | −0.026676 | −0.07344 | −0.095662 | −0.067566 | 0.038591 | −0.053344 | 0.103926 | −0.101806 |
| 17 | 0.108862 | 0.296529 | −0.077161 | 0.166715 | 0.01328 | −0.080701 | −0.22243 | 0.008243 | 0.204914 | −0.248615 | 0.094201 | 0.152293 | −0.28513 | −0.033023 |
| 18 | −0.121389 | −0.171458 | 0.061163 | −0.112932 | 0.111184 | −0.235933 | 0.065502 | 0.063814 | 0.033771 | −0.054836 | 0.092543 | 0.342653 | −0.185185 | 0.080097 |
| 19 | 0.148991 | 0.17041 | 0.252993 | 0.24976 | −0.180107 | 0.055998 | −0.090768 | −0.135061 | −0.04224 | 0.027322 | 0.224303 | 0.039339 | 0.043425 | −0.026476 |
| 20 | 0.058633 | −0.098137 | 0.085453 | 0.248069 | −0.12244 | −0.109319 | −0.053869 | −0.05396 | 0.135566 | −0.002635 | −0.063073 | −0.007221 | −0.038951 | 0.025455 |
| 21 | −0.151692 | −0.078336 | −0.017454 | 0.183183 | −0.085173 | −0.072695 | −0.037372 | 0.093056 | 0.256102 | 0.020437 | −0.103858 | 0.054197 | −0.071191 | 0.119127 |
| 22 | 0.04149 | −0.171928 | −0.01953 | 0.058979 | 0.073286 | 0.149239 | 0.093401 | 0.186525 | −0.04534 | 0.059972 | 0.325174 | 0.072706 | 0.108904 | 0.210377 |
| 23 | −0.068995 | 0.114242 | 0.029475 | 0.093507 | −0.101584 | −0.024334 | −0.137797 | 0.068323 | −0.192599 | −0.071683 | −0.075369 | −0.05764 | 0.22411 | −0.163225 |
| 24 | −0.100996 | 0.040378 | 0.053377 | 0.122978 | −0.14742 | 0.031502 | −0.061608 | −0.049796 | −0.154857 | −0.080264 | −0.052206 | −0.140107 | 0.077861 | 0.044439 |
| 25 | −0.250124 | −0.150279 | 0.015725 | 0.438143 | 0.112117 | 0.003273 | −0.267399 | 0.249031 | −0.183884 | −0.027689 | −0.026125 | 0.04567 | −0.084898 | 0.024229 |
| 26 | 0.141303 | −0.022184 | 0.095696 | −0.094363 | −0.047949 | 0.083892 | −0.0615 | −0.079781 | 0.143443 | 0.036701 | 0.136307 | −0.033637 | −0.010652 | −0.005021 |
| 27 | 0.183364 | −0.015917 | 0.057135 | −0.076746 | −0.035898 | 0.044333 | −0.062459 | −0.004705 | 0.16305 | −0.013199 | 0.183501 | −0.046934 | −0.048185 | −0.05298 |
| 28 | −0.087077 | 0.014576 | −0.230039 | 0.155856 | 0.182915 | 0.0129 | 0.034028 | −0.170414 | −0.080455 | −0.036226 | 0.109559 | −0.07948 | 0.013354 | −0.053974 |
| 29 | −0.083832 | 0.082803 | −0.126906 | 0.017713 | 0.046164 | −0.105925 | −0.066855 | −0.343746 | 0.123995 | 0.007538 | 0.083648 | −0.083648 | −0.004865 | 0.105523 |
| 30 | 0.095853 | −0.058001 | −0.189618 | 0.015708 | −0.059322 | −0.02649 | 0.00303 | −0.074663 | 0.097212 | −0.008381 | 0.10035 | −0.08709 | −0.008354 | −0.089124 |
| 31 | −0.025925 | −0.074828 | −0.171521 | −0.01868 | −0.048039 | −0.029653 | 0.015804 | −0.070898 | −0.0595 | −0.097516 | 0.124409 | −0.109409 | −0.049098 | 0.106623 |
| 32 | 0.05704 | 0.449466 | 0.051241 | −0.014166 | 0.2349 | −0.314779 | 0.183285 | −0.0021 | −0.144365 | 0.414442 | 0.013592 | 0.207204 | 0.053355 | −0.08244 |
| 33 | −0.037944 | −0.006134 | −0.127602 | 0.057907 | −0.021385 | −0.103159 | 0.06825 | 0.056199 | −0.03816 | −0.131508 | −0.086905 | 0.278096 | 0.027266 | 0.06754 |
| 34 | −0.236687 | 0.021984 | 0.081544 | −0.124096 | 0.028944 | −0.211008 | −0.073214 | 0.186411 | 0.269264 | 0.191266 | 0.128861 | −0.114895 | 0.039674 | −0.114363 |
| 35 | 0.00852 | −0.016212 | −0.094478 | 0.234334 | 0.030837 | −0.090712 | 0.08492 | −0.202737 | −0.121104 | −0.062565 | −0.07329 | 0.121211 | −0.136835 | 0.205991 |
| 36 | 0.075743 | 0.06694 | −0.142532 | −0.085232 | 0.089018 | −0.034566 | −0.328058 | 0.050794 | 0.296135 | −0.08195 | −0.086687 | 0.006215 | 0.273669 | 0.139022 |
| 37 | 0.018989 | 0.003196 | 0.004155 | −0.179299 | 0.028398 | −0.132816 | −0.098924 | 0.120619 | 0.037705 | −0.208208 | −0.211287 | 0.085145 | 0.125463 | 0.057114 |
| 38 | −0.034036 | −0.071625 | −0.118155 | −0.017885 | 0.0028 | −0.268714 | 0.148098 | 0.033789 | −0.1370634 | −0.052936 | 0.144588 | −0.135854 | −0.111282 | −0.043835 |
| 39 | −0.025782 | −0:051195 | −0.047398 | −0.043333 | −0.000408 | 0.158145 | −0.269675 | −0.192252 | 0.098754 | 0.179631 | 0.102236 | 0.031617 | −0.160572 | 0.050236 |
| 40 | 0.165387 | 0.057072 | −0.116815 | −0.00161 | 0.071964 | 0.197954 | 0.021546 | 0.080974 | −0.154915 | 0.232199 | −0.108837 | −0.226825 | −0.026732 | 0.056637 |
| 41 | −0.196668 | 0.031001 | −0.063929 | −0.075199 | 0.107738 | 0.060319 | −0.012501 | −0.09873 | 0.01542 | −0.282033 | −0.060459 | −0.085257 | −0.01978 | −0.032892 |
| 42 | −0.155324 | 0.04814 | 0.2001281 | 0.0752251 | 0.197761 | 0.1281461 | 0.031964 | −0.136721 | 0.1128661 | 0.030004 | −0.083352 | 0.065541 | −0.075295 | 0.061305 |
| 43 | −0.214778 | −0.010101 | 0.113867 | −0.119639 | 0.081642 | 0.184532 | −0.038906 | 0.143436 | 0.064755 | −0.0495941 | −0.061933 | 0.057377 | −0.053991 | −0.080043 |
| 44 | 0.188443 | −0.071053 | −0.106095 | −0.120835 | −0.137366 | −0.173444 | −0.151323 | 0.09657 | −0.132315 | −0.023368 | 0.053785 | −0.110381 | −0.122598 | 0.165629 |
| 45 | 0.034586 | 0.146341 | −0.075052 | −0.03734 | 0.040535 | −0.125476 | −0.182374 | −0.015333 | −0.008889 | −0.039583 | −0.043966 | −0.003101 | −0.018003 | 0.083976 |
| 46 | −0.21252 | 0.062038 | 0.00067 | −0.197113 | −0.078104 | 0.141046 | −0.097735 | 0.161635 | 0.054641 | −0.063295 | 0.084835 | 0.266506 | −0.150791 | −0.328872 |
| 47 | 0.077042 | −0.180564 | 0.205167 | 0.061126 | −0.086329 | −0.004711 | 0.130924 | −0.061174 | −0.041676 | 0.073074 | −0.05655 | 0.110343 | 0.068304 | 0.044116 |
| 48 | −0.191649 | −0.075873 | 0.189027 | −0.04672 | 0.021684 | 0.037312 | 0.129098 | −0.15011 | 0.082795 | −0.024469 | −0.053515 | −0.090642 | 0.058722 | 0.197642 |
| 49 | 0.076017 | −0.026593 | 0.08266 | 0.173762 | 0.162554 | 0.136245 | −0.079042 | −0.013823 | 0.110206 | 0.145552 | −0.00992 | 0.116384 | −0.012377 | −0.014632 |
| 50 | −0.110295 | −0.003499 | 0.212896 | 0.107064 | 0.055224 | 0.085294 | 0.019913 | −0.124081 | −0.051351 | 0.069919 | −0.035891 | 0.003253 | −0.096001 | 0.010075 |
| 51 | −0.130749 | 0.061611 | 0.059316 | 0.061164 | 0.142164 | 0.058691 | 0.050361 | 0.087137 | −0.020487 | 0.095048 | −0.064738 | −0.151985 | −0.033025 | −0.074355 |
| 52 | 0.08215 | −0.017467 | −0.03128 | −0.0858491 | −0.061924 | −0.0794281 | −0.096028 | 0.10115 | −0.0788331 | −0.089112 | 0.036416 | 0.036526 | −0.020059 | 0.09741 |
| 53 | 0.000488 | −0.040007 | 0.09289 | 0.009314 | −0.017054 | −0.085064 | −0.024646 | 0.004138 | 0.01102 | 0.011507 | 0.015976 | 0.00616 | 0.065743 | 0.195029 |
| 54 | −0.059461 | −0.008708 | 0.067484 | −0.061404 | −0.11345 | 0.140288 | 0.063785 | −0.001685 | −0.034771 | −0.056664 | 0.068097 | 0.057394 | 0.077948 | −0.187221 |
| 55 | −0.097877 | 0.034528 | −0.031415 | −0.13556 | −0.048879 | 0.160054 | 0.191408 | −0.091977 | 0.079667 | 0.062681 | 0.003533 | −0.013226 | −0.143786 | 0.004244 |
| 56 | 0.146147 | −0.035689 | −0.000561 | 0.035742 | −0.003323 | 0.042207 | −0.011853 | 0.16745 | −0.134843 | 0.067255 | −0.023039 | −0.078017 | −0.108032 | −0.046053 |
| 57 | 0.040197 | 0.003214 | −0.057231 | 0.044648 | −0.011108 | 0.101448 | −0.153136 | −0.141958 | −0.028866 | 0.030815 | −0.098994 | −0.02151 | −0.009255 | −0.073913 |
| 58 | 0.081828 | −0.023752 | −0.12433 | 0.074173 | 0.015868 | −0.017039 | −0.083572 | −0.04609 | 0.044994 | 0.038694 | 0.028016 | −0.057076 | −0.01673 | −0.188165 |

APPENDIX B4-continued

PCA Transformation Matrix (82 × 82 Normal/Diseased)

| | | | | | | | | | | | | | | |
|---|---|---|---|---|---|---|---|---|---|---|---|---|---|---|
| 59 | 0.134586 | −0.095233 | 0.023403 | 0.13413 | −0.074269 | −0.097164 | 0.042842 | 0.152871 | −0.003705 | 0.014248 | 0.027809 | 0.083786 | −0.052223 | −0.079178 |
| 60 | 0.027665 | −0.016187 | 0.087986 | 0.00801 | −0.130671 | 0.09135 | 0.030155 | 0.011688 | −0.230596 | −0.254386 | −0.249099 | 0.069983 | 0.098121 | −0.03537 |
| 61 | −0.058037 | −0.005617 | −0.085105 | 0.037616 | −0.002884 | −0.126931 | 0.088893 | 0.018989 | −0.045405 | −0.069238 | −0.071875 | 0.150344 | 0.142422 | 0.051294 |
| 62 | 0.076712 | −0.00876 | 0.163987 | 0.068618 | 0.081229 | −0.174785 | −0.093109 | 0.179107 | 0.142617 | 0.034416 | −0.069804 | −0.133421 | 0.056377 | −0.050588 |
| 63 | −0.002822 | −0.086388 | 0.179603 | 0.023588 | 0.034139 | −0.188432 | 0.286672 | 0.007976 | 0.170341 | −0.170328 | −0.030517 | −0.210098 | −0.156557 | −0.023585 |
| 64 | −0.027971 | −0.031616 | 0.052416 | −0.029579 | −0.09708 | 0.037468 | 0.034933 | 0.07127 | −0.004497 | −0.092652 | 0.12133 | −0.022535 | 0.016528 | −0.261133 |
| 65 | −0.057466 | 0.028906 | 0.041958 | 0.053832 | 0.012053 | 0.058509 | −0.094309 | −0.106694 | −0.054519 | −0.072511 | −0.052902 | 0.012403 | −0.064078 | −0.048241 |
| 66 | −0.054983 | 0.445987 | 0.089629 | 0.099661 | −0.144172 | 0.070102 | 0.243304 | 0.194039 | 0.109465 | −0.205333 | 0.200629 | −0.098638 | 0.288022 | 0.173635 |
| 67 | 0.195415 | 0.060103 | 0.0338041 | −0.1292661 | −0.0889861 | 0.0519021 | 0.056821 | −0.1886541 | 0.0402771 | −0.01248 | −0.113707 | 0.32245 | 0.159952 | 0.089277 |
| 68 | 0.198843 | −0.012978 | 0.271296 | −0.013851 | 0.040411 | −0.031252 | −0.083396 | 0.0484671 | 0.059485 | −0.008635 | −0.133144 | −0.011485 | −0.071944 | 0.053454 |
| 69 | 0.169525 | −0.025239 | 0.189869 | 0.024888 | 0.106289 | 0.047449 | −0.04404 | 0.032503 | 0.107593 | −0.063072 | −0.06813 | 0.009698 | −0.006843 | −0.001951 |
| 70 | 0.163078 | 0.064934 | 0.046326 | 0.010015 | 0.296007 | 0.178416 | 0.065803 | 0.069197 | 0.027217 | −0.173303 | −0.08655 | −0.042609 | −0.043314 | 0.055927 |
| 71 | 0.16354 | 0.038518 | 0.161637 | −0.055091 | 0.044686 | 0.094226 | −0.069736 | −0.046428 | −0.081959 | −0.07928 | −0.004208 | 0.049299 | −0.097509 | −0.033934 |
| 72 | 0.06525 | 0.216551 | −0.04018 | −0.120244 | 0.207139 | 0.203578 | 0.067359 | 0.153042 | −0.129437 | −0.147415 | −0.029906 | −0.128405 | −0.300443 | 0.128236 |
| 73 | −0.035141 | −0.058436 | −0.099435 | 0.144279 | 0.068322 | −0.014626 | 0.08614 | −0.061567 | 0.079804 | 0.0409 | −0.071881 | 0.033216 | 0.189016 | −0.136667 |
| 74 | −0.000242 | 0.045964 | 0.198136 | −0.070314 | −0.119933 | −0.098838 | −0.149641 | 0.13674 | −0.137483 | 0.147011 | −0.033016 | −0.090035 | −0.084411 | 0.121765 |
| 75 | −0.046449 | −0.0331 | −0.020187 | −0.032701 | −0.028597 | 0.030157 | 0.014305 | 0.023979 | −0.017519 | 0.017003 | −0.004871 | −0.005903 | 0.010347 | 0.031179 |
| 76 | −0.033017 | −0.055302 | 0.096182 | 0.000147 | −0.187915 | −0.022856 | −0.025609 | −0.087636 | −0.064328 | 0.039103 | 0.005467 | −0.021356 | 0.005851 | −0.176425 |
| 77 | −0.073097 | 0.006733 | −0.082256 | −0.011363 | −0.04185 | −0.008336 | 0.078293 | −0.039702 | 0.041543 | 0.024187 | −0.0367 | 0.041577 | −0.016588 | −0.100089 |
| 78 | −0.077124 | −0.036999 | 0.013942 | −0.079608 | −0.123622 | −0.011214 | 0.010931 | −0.020447 | −0.001824 | 0.054387 | −0.054434 | 0.027486 | −0.037646 | 0.102438 |
| 79 | 0.011926 | −0.017515 | −0.028222 | 0.141924 | 0.099731 | 0.012815 | −0.028115 | 0.098892 | 0.137976 | 0.019003 | −0.013027 | −0.123515 | 0.204926 | −0.109315 |
| 80 | −0.063693 | 0.021087 | 0.036921 | −0.068939 | −0.085947 | 0.022296 | −0.010076 | 0.096173 | 0.000222 | −0.010365 | 0.055808 | −0.129293 | −0.035606 | 0.178979 |
| 81 | −0.106462 | −0.029321 | 0.156765 | −0.11706 | −0.227923 | −0.014226 | −0.078616 | −0.024919 | −0.073675 | 0.072742 | 0.02998 | −0.036003 | −0.088216 | 0.10845 |
| 82 | −0.089351 | −0.014623 | −0.090741 | 0.0325351 | −0.020514 | 0.0426871 | 0.014863 | 0.0554091 | 0.083967 | −0.010453 | −0.0675341 | −0.07403 | 0.100169 | 0.023548 |

| | AB | AC | AD | AE | AF | AG | AH | AI | AJ | AK | AL | AM | AN | AO |
|---|---|---|---|---|---|---|---|---|---|---|---|---|---|---|
| 1 | −0.026542 | 0.005794 | −0.1006451 | 0.198849 | −0.05063 | 0.073017 | −0.140599 | 0.063973 | −0.156003 | 0.364772 | −0.027296 | 0.252101 | −0.088098 | 0.027736 |
| 2 | −0.233585 | −0.083084 | −0.1557731 | −0.125126 | 0.152749 | 0.105142 | 0.076228 | 0.093071 | −0.008073 | −0.121984 | 0.121888 | −0.256323 | 0.162878 | −0.084813 |
| 3 | 0.316006 | 0.010499 | 0.011313 | 0.093375 | −0.112201 | 0.262786 | 0.104369 | 0.189114 | 0.075006 | 0.086639 | −0.116061 | −0.081515 | 0.03983 | −0.121011 |
| 4 | 0.177786 | 0.038862 | 0.048155 | 0.028713 | −0.071113 | 0.114272 | 0.192325 | −0.0012 | 0.012219 | −0.088731 | −0.045744 | −0.176381 | −0.002093 | 0.099755 |
| 5 | 0.107314 | 0.019301 | 0.0278141 | −0.0212111 | −0.0165291 | 0.0402981 | 0.0929361 | −0.0264741 | 0.0144391 | −0.0245541 | −0.0053331 | −0.073142 | −0.000637 | 0.110117 |
| 6 | −0.029224 | −0.077657 | 0.038871 | −0.035094 | 0.039133 | −0.06441 | −0.007986 | −0.033476 | −0.040232 | 0.04791 | 0.075295 | 0.064652 | −0.109141 | 0.227459 |
| 7 | −0.162039 | −0.110913 | −0.012498 | −0.103866 | 0.030419 | 0.013164 | 0.035621 | 0.076905 | −0.025258 | −0.070344 | −0.039674 | 0.002305 | −0.133297 | −0.115714 |
| 8 | 0.132191 | −0.154686 | 0.107272 | 0.16553 | 0.038921 | −0.092616 | −0.067564 | 0.21664 | 0.06868 | 0.055207 | −0.009581 | −0.099375 | 0.064049 | −0.071129 |
| 9 | −0.165773 | −0.054812 | 0.022737 | 0.157966 | 0.034417 | −0.176705 | −0.188809 | −0.059516 | 0.024408 | 0.186034 | −0.041034 | 0.225474 | 0.217674 | −0.097972 |
| 10 | −0.101386 | −0.006232 | −0.069311 | −0.1128581 | −0.00958 | 0.049107 | −0.082968 | −0.029109 | 0.15316 | −0.042558 | 0.244203 | 0.095297 | −0.075949 | −0.242202 |
| 11 | −0.001657 | −0.00808 | −0.1474641 | −0.065995 | −0.024907 | 0.069391 | 0.011074 | 0.037309 | −0.2693441 | −0.0465821 | 0.112065 | −0.094511 | 0.067327 | 0.197283 |
| 12 | −0.007383 | 0.003001 | 0.0381821 | 0.031401 | 0.088564 | −0.088603 | −0.084611 | −0.057232 | −0.0163241 | 0.0464511 | −0.058685 | 0.110892 | −0.015543 | −0.169258 |
| 13 | −0.048485 | −0.020362 | 0.091607 | −0.077281 | 0.05096 | 0.035049 | 0.153378 | 0.022792 | 0.009495 | 0.187266 | −0.05646 | −0.066488 | 0.089337 | −0.140652 |
| 14 | −0.118397 | −0.036655 | 0.007864 | 0.061815 | −0.141457 | 0.15905 | −0.01789 | −0.036128 | −0.074105 | −0.13749 | −0.027069 | 0.113927 | −0.010398 | 0.140484 |
| 15 | −0.041919 | 0.091068 | −0.047217 | 0.214655 | −0.176824 | 0.076409 | −0.1538181 | 0.018935 | −0.088617 | −0.121154 | 0.04698 | −0.204783 | −0.15705 | 0.102917 |
| 16 | 0.008214 | −0.057064 | 0.020669 | −0.108664 | 0.028444 | 0.099123 | 0.096574 | −0.020996 | −0.00351 | 0.033276 | −0.017613 | 0.043649 | 0.078521 | −0.177164 |
| 17 | 0.151759 | −0.125709 | 0.163654 | 0.043434 | 0.207687 | 0.107611 | 0.012991 | 0.300494 | 0.073345 | −0.089298 | −0.004244 | 0.07913 | 0.062719 | −0.138496 |
| 18 | −0.034738 | −0.064055 | −0.068615 | −0.191881 | 0.17195 | −0.018367 | −0.18062 | 0.037243 | −0.218073 | 0.205261 | −0.050348 | 0.06916 | 0.062528 | 0.025403 |
| 19 | −0.073387 | 0.004089 | −0.169539 | 0.022729 | −0.057966 | 0.110151 | 0.010909 | −0.114035 | −0.025355 | 0.044007 | 0.072894 | 0.009027 | −0.044209 | −0.083175 |
| 20 | 0.178638 | −0.060422 | −0.074439 | −0.289496 | 0.160049 | 0.010999 | 0.14178 | −0.163777 | 0.029413 | 0.07485 | −0.157621 | 0.213014 | 0.003471 | 0.074596 |
| 21 | 0.23242 | 0.251194 | −0.003338 | −0.053503 | 0.036122 | −0.290282 | −0.113142 | −0.085001 | −0.05058 | −0.024536 | 0.053868 | 0.024434 | −0.117525 | 0.214497 |
| 22 | 0.021925 | −0.166929 | 0.05628 | 0.099398 | 0.010328 | −0.069107 | −0.049465 | 0.164534 | 0.070432 | −0.042431 | −0.138466 | 0.006047 | −0.058774 | 0.026847 |

APPENDIX B4-continued

PCA Transformation Matrix (82 × 82 Normal/Diseased)

| | | | | | | | | | | | | | | |
|---|---|---|---|---|---|---|---|---|---|---|---|---|---|---|
| 23 | 0.107382 | −0.143587 | 0.47259 | −0.027896 | 0.086013 | −0.080182 | −0.076321 | −0.098342 | −0.157667 | 0.131378 | 0.169043 | −0.041256 | −0.089381 | −0.01738 |
| 24 | 0.02443 | 0.068456 | 0.197156 | −0.099767 | 0.153823 | 0.026458 | −0.1533 | 0.099129 | 0.090681 | −0.080896 | −0.136012 | −0.126552 | −0.004706 | 0.090897 |
| 25 | −0.074442 | 0.137244 | −0.077136 | −0.018442 | −0.093373 | −0.035259 | 0.365441 | 0.042938 | 0.048693 | −0.022943 | 0.071512 | 0.117088 | 0.045853 | −0.12166 |
| 26 | 0.166273 | −0.015918 | −0.1538741 | 0.121487 | −0.0621991 | 0.18159 | 0.0599081 | −0.057575 | 0.1018461 | 0.0530271 | −0.0440131 | 0.184705 | 0.043027 | 0.022236 |
| 27 | 0.134377 | −0.00846 | −0.079093 | 0.0656771 | −0.1118651 | 0.0534421 | 0.119099 | −0.0599521 | −0.0516261 | 0.0117541 | −0.0798931 | 0.144661 | −0.075249 | 0.039114 |
| 28 | −0.126518 | −0.155918 | −0.151048 | −0.021826 | 0.091604 | −0.0751 | −0.071744 | 0.042206 | 0.235665 | −0.108788 | −0.052481 | −0.054011 | −0.02135 | 0.376485 |
| 29 | 0.027537 | −0.056944 | −0.016454 | −0.101959 | −0.117801 | −0.10846 | −0.00797 | 0.131896 | 0.042895 | −0.180242 | 0.039393 | 0.014983 | −0.04972 | −0.189006 |
| 30 | 0.100954 | −0.062783 | 0.02306 | −0.210105 | −0.1228221 | −0.077185 | −0.016605 | 0.006173 | −0.109272 | −0.084608 | −0.027913 | 0.02073 | 0.11012 | −0.122481 |
| 31 | 0.11676 | −0.018428 | −0.124275 | 0.045478 | 0.274073 | −0.007757 | 0.060644 | −0.217971 | −0.080097 | 0.001376 | −0.178928 | 0.057812 | −0.026605 | −0.109531 |
| 32 | 0.073857 | 0.067055 | −0.098107 | −0.009703 | 0.072089 | −0.06161 | 0.073479 | 0.065744 | −0.027962 | −0.01042 | −0.118397 | −0.005732 | 0.156528 | 0.063794 |
| 33 | 0.069892 | −0.06066 | −0.040643 | 0.012897 | −0.040024 | 0.091627 | −0.08732 | −0.201518 | −0.021217 | −0.114104 | 0.140896 | −0.064778 | −0.011058 | −0.091684 |
| 34 | −0.134606 | −0.191613 | 0.010816 | 0.001091 | 0.009996 | 0.061702 | 0.05779 | −0.065122 | −0.030227 | −0.104732 | 0.246218 | 0.196809 | −0.089341 | −0.002321 |
| 35 | −0.206257 | −0.043823 | 0.238952 | 0.014522 | −0.185503 | 0.026503 | 0.118139 | −0.151258 | −0.126723 | 0.015891 | −0.347583 | 0.171983 | 0.02384 | −0.060647 |
| 36 | −0.301541 | 0.350535 | −0.033914 | −0.027691 | 0.090593 | 0.007789 | −0.248221 | 0.042266 | 0.062126 | −0.065033 | −0.15113 | 0.033769 | −0.104806 | −0.121058 |
| 37 | −0.047245 | −0.173674 | −0.143653 | 0.077699 | −0.171791 | −0.194909 | 0.245316 | 0.20339 | −0.11242 | 0.058886 | −0.004072 | 0.086641 | −0.064715 | 0.120492 |
| 38 | 0.029791 | 0.167121 | 0.087058 | −0.01101 | 0.07243 | 0.247597 | 0.031753 | 0.083329 | 0.283864 | 0.04288 | −0.069691 | 0.099875 | −0.167497 | 0.113589 |
| 39 | −0.024228 | 0.004842 | 0.13248 | −0.015662 | 0.230757 | 0.174769 | 0.140214 | −0.129685 | 0.012517 | 0.037418 | 0.241059 | −0.063031 | −0.007608 | 0.021677 |
| 40 | −0.077438 | 0.06076 | −0.0030081 | 0.0143791 | 0.0834591 | −0.0485181 | −0.0087631 | 0.0761191 | 0.0392231 | 0.0093491 | 0.0140191 | 0.10479 | −0.00781 | −0.019935 |
| 41 | 0.098973 | −0.018377 | −0.1727981 | −0.0660571 | 0.0287591 | −0.1122481 | 0.018431 | 0.1181641 | 0.0660371 | 0.1791121 | 0.0494711 | −0.019392 | 0.190591 | −0.089514 |
| 42 | 0.005479 | −0.099455 | 0.024271 | 0.003462 | −0.006653 | −0.165104 | −0.033172 | 0.064622 | 0.1863981 | 0.0434841 | 0.0680191 | 0.113855 | 0.071183 | 0.017837 |
| 43 | −0.048849 | −0.059208 | −0.054988 | 0.14169 | 0.018514 | −0.001335 | 0.131968 | −0.080971 | −0.00554 | −0.160093 | −0.0533611 | 0.076325 | 0.079667 | −0.024189 |
| 44 | 0.122057 | 0.018518 | −0.002058 | −0.073169 | −0.108263 | −0.110052 | 0.030734 | −0.051456 | −0.061919 | −0.068312 | 0.101432 | 0.030362 | −0.016163 | −0.037339 |
| 45 | −0.071725 | −0.084424 | 0.124764 | −0.060406 | −0.065582 | −0.180361 | 0.08059 | 0.129905 | −0.08962 | 0.028099 | 0.017897 | −0.077166 | −0.007131 | 0.035697 |
| 46 | 0.021845 | 0.026963 | 0.156019 | −0.079531 | −0.161326 | 0.053437 | −0.129168 | −0.238857 | 0.178655 | −0.061276 | −0.31249 | −0.06717 | 0.030165 | 0.017941 |
| 47 | 0.024438 | 0.062611 | −0.098887 | −0.024024 | −0.184616 | 0.087458 | −0.105945 | 0.126164 | −0.120327 | −0.036371 | −0.045337 | 0.015248 | −0.061405 | −0.183445 |
| 48 | 0.065286 | −0.051285 | 0.069719 | −0.068996 | 0.054972 | 0.076703 | −0.046576 | 0.087683 | −0.184772 | −0.085408 | 0.026747 | −0.105781 | −0.025668 | −0.158419 |
| 49 | −0.165153 | 0.004576 | 0.114246 | −0.11154 | −0.175902 | 0.023876 | 0.113074 | −0.113352 | 0.106888 | 0.172826 | −0.074963 | −0.238818 | −0.053263 | 0.017796 |
| 50 | −0.091523 | −0.009624 | −0.026633 | 0.02104 | 0.213653 | −0.003582 | −0.036569 | 0.07016 | −0.213635 | 0.032241 | 0.018507 | −0.078102 | 0.070612 | −0.009743 |
| 51 | 0.224189 | 0.057365 | −0.019548 | −0.090997 | 0.197769 | 0.103292 | −0.139922 | 0.004713− | −0.04304 | −0.072559 | 0.044142 | 0.125471 | −0.042931 | −0.102486 |
| 52 | −0.143379 | 0.003969 | −0.0532351 | 0.1377151 | 0.2944261 | 0.0460211 | 0.228611 | −0.0916791 | −0.041282 | 0.224094 | −0.03999 | −0.247331 | −0.009778 | 0.110238 |
| 53 | −0.074993 | 0.062631 | −0.006829 | 0.054995 | 0.01623 | 0.096422 | 0.025055 | 0.054064 | −0.0140881 | −0.0104251 | 0.1215831 | 0.125924 | −0.012424 | 0.040367 |
| 54 | 0.025529 | 0.090881 | −0.009698 | −0.115435 | 0.006051 | −0.082326 | 0.063942 | 0.160786 | −0.178472 | −0.083756 | −0.120474 | 0.011576 | −0.030473 | 0.041806 |
| 55 | −0.076384 | −0.114748 | 0.218073 | −0.08543 | 0.009883 | −0.032654 | 0.187896 | 0.039067 | −0.139991 | −0.146092 | −0.050902 | 0.148039 | −0.133812 | 0.100709 |
| 76. | 0.125768 | −0.121913 | 0.109655 | −0.112568 | −0.051941 | −0.040544 | −0.053754 | −0.01438 | −0.057811 | −0.029848 | 0.063324 | −0.063429 | −0.034949 | −0.063831 |
| 57 | 0.134154 | −0.189987 | −0.086408 | 0.057839 | −0.106907 | −0.173355 | −0.056235 | −0.126768 | −0.009324 | 0.0101 | −0.030699 | −0.037454 | 0.096375 | −0.059157 |
| 58 | 0.122294 | −0.078699 | −0.0193 | 0.105299 | −0.16381 | −0.107376 | −0.116191 | −0.041399 | −0.065427 | 0.058605 | 0.01316 | −0.060252 | 0.109566 | 0.035565 |
| 59 | −0.000149 | 0.081473 | 0.191225 | 0.029242 | −0.113655 | 0.01241 | −0.03519 | 0.156592 | 0.069861 | −0.077528 | 0.195061 | 0.093927 | 0.122274 | 0.117591 |
| 60 | 0.033766 | −0.19933 | −0.121255 | 0.07319 | 0.103867 | 0.155795 | −0.072801 | 0.103098 | 0.133226 | −0.122465 | −0.032593 | 0.211792 | −0.075795 | 0.050364 |
| 61 | 0.112255 | 0.065739 | −0.050772 | 0.056763 | 0.026052 | 0.03418 | −0.103742 | −0.265707 | 0.042593 | 0.040539 | 0.045865 | −0.103432 | 0.053733 | −0.078771 |
| 62 | 0.020699 | −0.274065 | −0.021458 | 0.012692 | 0.100898 | 0.089492 | −0.134026 | −0.034221 | −0.036734 | 0.059946 | −0.08177 | −0.097682 | −0.118388 | 0.06428 |
| 63 | 0.02838 | 0.116161 | 0.138881 | 0.257863 | −0.086619 | −0.07075 | 0.087464 | −0.02556 | 0.187813 | 0.186205 | 0.104816 | −0.107549 | 0.152477 | −0.074637 |
| 64 | 0.008814 | 0.243606 | −0.013314 | −0.022293 | 0.03889 | −0.120541 | 0.098891 | 0.120164 | −0.068636 | 0.099517 | −0.006482 | 0.035977 | 0.028306 | 0.053365 |
| 65 | 0.004969 | −0.11487 | −0.102733 | 0.105106 | 0.052499 | 0.030639 | −0.020318 | −0.012709 | 0.013229 | 0.050681 | 0.065847 | −0.008349 | 0.098025 | 0.118375 |
| 66 | −0.021106 | −0.061005 | −0.013017 | −0.189436 | 0.005069 | −0.11391 | 0.184836 | −0.166295 | 0.115372 | 0.06859 | −0.04301 | 0.050753 | −0.001934 | −0.098991 |
| 67 | 0.068805 | 0.080028 | 0.226705 | 0.055719 | 0.111476 | −0.066094 | 0.094729 | −0.098345 | 0.127999 | −0.072865 | 0.2396321 | 0.228619 | 0.127667 | 0.168359 |
| 68 | −0.007385 | −0.072057 | 0.053469 | −0.015509 | 0.022982 | −0.032612 | −0.048406 | 0.044211 | 0.011687 | 0.011214 | −0.1885941 | 0.015083 | −0.127984 | 0.082266 |
| 69 | 0.058759 | −0.070407 | −0.000087 | 0.07964 | 0.076152 | −0.063047 | −0.057243 | −0.01315 | 0.00799 | 0.045997 | −0.144925 | −0.099506 | −0.044728 | 0.020458 |
| 70 | 0.008807 | 0.061711 | 0.106864 | −0.014362 | −0.002508 | 0.13378 | 0.01715 | −0.113936 | −0.105421 | −0.026011 | 0.039568 | 0.024619 | −0.037591 | 0.041389 |
| 71 | 0.074875 | 0.283472 | −0.053465 | −0.14669 | 0.002768 | −0.097874 | −0.020549 | 0.12353 | 0.038139 | −0.030019 | 0.025685 | 0.0191 | −0.031991 | 0.002634 |

APPENDIX B4-continued

PCA Transformation
Matrix (82 × 82
Normal/Diseased)

| | | | | | | | | | | | | | | |
|---|---|---|---|---|---|---|---|---|---|---|---|---|---|---|
| 72 | 0.050951 | 0.089083 | −0.109835 | −0.175691 | −0.093452 | −0.036783 | −0.03834 | −0.147706 | −0.106061 | 0.113426 | 0.162388 | 0.010324 | −0.128548 | 0.033829 |
| 73 | 0.064199 | −0.005104 | −0.0807 | 0.040803 | −0.030185 | 0.065835 | 0.056628 | 0.004985 | 0.00088 | 0.103825 | 0.094761 | −0.057181 | −0.021348 | 0.036356 |
| 74 | −0.004556 | −0.069531 | −0.128495 | 0.022758 | 0.083006 | −0.223196 | 0.017314 | −0.163009 | 0.126423 | −0.379597 | −0.082552 | −0.078943 | 0.253749 | −0.001528 |
| 75 | −0.074975 | −0.003405 | 0.049158 | 0.266566 | 0.052911 | −0.022411 | 0.086546 | −0.101722 | −0.035997 | −0.153748 | −0.00843 | −0.00071 | −0.153869 | −0.188468 |
| 76 | 0.023005 | 0.085463 | 0.002967 | 0.067457 | 0.154897 | −0.151744 | 0.081719 | 0.097155 | 0.092782 | 0.020691 | −0.06701 | −0.011852 | −0.112337 | −0.1082 |
| 77 | −0.070052 | 0.037976 | 0.023841 | 0.192736 | 0.068587 | −0.207446 | 0.095587 | 0.00272 | −0.048255 | −0.03844 | 0.002693 | −0.020514 | −0.270182 | −0.108043 |
| 78 | −0.033971 | −0.239468 | −0.073849 | −0.206816 | −0.143863 | 0.024476 | −0.089144 | 0.007769 | 0.302271 | 0.173673 | 0.109352 | −0.043259 | −0.25563 | −0.009678 |
| 79 | 0.037144 | −0.008375 | 0.016612 | −0.059451 | −0.046294 | 0.17536 | 0.067247 | 0.103081 | −0.150431 | 0.017552 | −0.078731 | −0.031136 | 0.092676 | 0.014486 |
| 80 | −0.178795 | 0.002347 | 0.129589 | 0.039569 | −0.069709 | 0.125585 | −0.170245 | −0.014995 | −0.07715 | −0.009661 | 0.045098 | 0.062541 | 0.390199 | 0.033621 |
| 81 | −0.146122 | 0.003431 | 0.0311451 | −0.2229071 | −0.0715091 | −0.0352461 | −0.0033351 | 0.1048161 | 0.1709391 | 0.1822971 | 0.011582 | −0.056954 | 0.06486 | 0.018665 |
| 82 | −0.038561 | 0.019721 | 0.0297351 | −0.1397671 | −0.038671 | 0.1403671 | −0.013914 | 0.0155161 | −0.024381 | −0.009 | −0.090145 | 0.112285 | 0.249826 | 0.15619 |

| | AP | AQ | AR | AS | AT | AU | AV | AW | AX | AY | AZ | BA | BB | BC |
|---|---|---|---|---|---|---|---|---|---|---|---|---|---|---|
| 1 | −0.169048 | 0.066719 | −0.135735 | 0.073373 | −0.030384 | 0.009981 | −0.049349 | 0.03642 | −0.165858 | 0.233922 | −0.052021 | 0.063255 | −0.015744 | 0.149039 |
| 2 | −0.029887 | 0.032622 | 0.114822 | 0.006783 | 0.08347 | 0.026512 | −0.086695 | 0.01616 | 0.032485 | 0.0012 | 0.072314 | −0.16467 | −0.038134 | 0.029708 |
| 3 | 0.044502 | −0.011002 | 0.08592 | 0.085072 | 0.124068 | −0.098801 | −0.0188 | 0.098603 | 0.085815 | −0.04031 | 0.025714 | −0.036675 | 0.070178 | −0.205188 |
| 4 | 0.113328 | 0.077992 | 0.088739 | 0.020335 | 0.146446 | −0.108857 | −0.134065 | −0.019279 | −0.042446 | −0.07362 | −0.156683 | −0.090621 | −0.004305 | 0.009758 |
| 5 | 0.064502 | 0.059357 | 0.03264 | 0.018377 | 0.042868 | 0.01448 | −0.070767 | −0.012399 | −0.051392 | 0.042069 | −0.05916 | −0.061245 | −0.043195 | 0.054155 |
| 6 | 0.028834 | −0.004838 | −0.045852 | 0.007553 | −0.026088 | 0.04431 | −0.021909 | 0.020464 | 0.169428 | 0.078482 | −0.035582 | 0.033161 | −0.078742 | 0.169897 |
| 7 | −0.026432 | −0.084764 | −0.259115 | 0.00419 | 0.01865 | 0.035264 | 0.141503 | −0.062277 | −0.012794 | −0.188463 | −0.036093 | 0.265334 | −0.084427 | −0.04849 |
| 8 | −0.082518 | 0.130371 | 0.005506 | −0.073552 | −0.008952 | −0.036876 | 0.00379 | −0.161427 | 0.185333 | −0.012251 | 0.035399 | 0.011523 | 0.124046 | −0.170123 |
| 9 | 0.236772 | −0.285295 | 0.052954 | −0.248225 | −0.132579 | −0.037908 | 0.086158 | 0.063194 | 0.233367 | 0.041587 | −0.019129 | −0.032393 | 0.105747 | 0.000295 |
| 10 | 0.094547 | 0.072092 | −0.051792 | 0.466592 | −0.076629 | 0.162371 | −0.13215 | 0.120564 | −0.086987 | −0.044886 | 0.001483 | 0.124132 | 0.251159 | −0.168013 |
| 11 | −0.370047 | 0.095259 | 0.246174 | −0.008109 | −0.103177 | 0.189439 | 0.154725 | 0.174952 | −0.016646 | 0.074532 | 0.127342 | 0.016201 | 0.089321 | 0.201599 |
| 12 | −0.207536 | 0.106707 | −0.126749 | −0.121392 | −0.038751 | −0.124529 | 0.040739 | −0.336436 | −0.341241 | 0.108131 | 0.135846 | −0.197564 | −0.247027 | −0.078077 |
| 13 | −0.142306 | −0.127751 | 0.177132 | −0.026849 | −0.090374 | 0.051529 | 0.045133 | −0.158803 | −0.003739 | 0.040655 | −0.035336 | 0.006036 | −0.155789 | −0.154474 |
| 14 | −0.038428 | 0.205457 | −0.252902 | 0.004664 | 0.025072 | −0.16133 | 0.067603 | 0.189154 | 0.144745 | −0.057238 | 0.145935 | 0.033659 | −0.020852 | −0.031227 |
| 15 | 0.173843 | −0.124495 | 0.058682 | −0.105316 | −0.082158 | 0.015447 | −0.079045 | −0.249489 | −0.068258 | −0.097365 | −0.046349 | −0.020321 | 0.127147 | 0.129937 |
| 16 | 0.114618 | −0.081022 | 0.137085 | −0.133891 | 0.02187 | 0.077875 | −0.12637 | 0.169508 | −0.105253 | 0.158433 | 0.032716 | −0.072617 | −0.168851 | 0.115751 |
| 17 | 0.104698 | −0.054649 | −0.054432 | 0.010314 | 0.007078 | 0.049959 | 0.186017 | 0.038822 | −0.073641 | 0.016214 | 0.122675 | −0.000903 | −0.077779 | 0.040283 |
| 18 | −0.024064 | 0.006323 | 0.087819 | 0.099428 | 0.202432 | 0.006593 | −0.208567 | 0.006649 | −0.026869 | −0.024782 | −0.083648 | 0.054369 | 0.079863 | −0.000288 |
| 19 | 0.088407 | −0.016626 | 0.175008 | 0.134925 | −0.025769 | −0.06035 | −0.260274 | −0.108791 | 0.017977 | −0.071469 | 0.037505 | −0.014563 | −0.263893 | −0.12539 |
| 20 | −0.125401 | −0.001939 | 0.052349 | 0.045721 | −0.023077 | −0.295419 | 0.088568 | −0.033974 | 0.001089 | 0.087098 | −0.118068 | −0.091441 | 0.256658 | 0.142434 |
| 21 | −0.035271 | −0.08444 | −0.016986 | 0.079511 | −0.056649 | 0.299344 | 0.069832 | 0.030666 | 0.056303 | −0.074906 | 0.064887 | 0.006988 | −0.117858 | −0.250788 |
| 22 | 0.16864 | −0.01355 | 0.004025 | −0.035522 | 0.121789 | 0.004569 | −0.004898 | 0.07425 | −0.055714 | −0.009235 | −0.01449 | 0.024016 | −0.122881 | 0.263668 |
| 23 | −0.047016 | −0.125461 | −0.070266 | 0.007686 | 0.220779 | 0.139506 | 0.022536 | −0.046266 | 0.001032 | −0.145255 | −0.097579 | −0.132526 | 0.062583 | −0.055145 |
| 24 | 0.069254 | 0.109432 | 0.133761 | 0.079689 | −0.078012 | −0.153642 | −0.084868 | 0.072802 | −0.172806 | 0.103956 | 0.169914 | 0.123083 | −0.056015 | 0.12258 |
| 25 | 0.040514 | −0.048719 | 0.161193 | −0.077884 | −0.180625 | −0.048736 | 0.083935 | −0.060526 | 0.111505 | −0.01784 | 0.016504 | −0.011411 | −0.050687 | 0.045141 |
| 26 | 0.007233 | −0.050715 | −0.046162 | −0.008606 | −0.076701 | 0.048098 | −0.054662 | 0.116587 | 0.061499 | 0.033949 | 0.035608 | 0.013504 | 0.038225 | −0.036912 |
| 27 | −0.039514 | 0.132964 | −0.049687 | 0.065025 | 0.005772 | 0.056947 | 0.123125 | −0.083712 | 0.021561 | 0.01597 | −0.129984 | −0.006714 | −0.025743 | −0.151768 |
| 28 | 0.057237 | 0.036649 | −0.063953 | 0.004379 | −0.012325 | −0.041208 | 0.069912 | 0.002388 | −0.01973 | 0.065656 | −0.139719 | −0.132181 | 0.002695 | −0.222635 |
| 29 | −0.091078 | −0.162397 | 0.134235 | −0.02691 | 0.102836 | 0.267576 | 0.032472 | −0.01859 | −0.015683 | 0.205946 | −0.039105 | 0.017137 | 0.150158 | 0.035913 |
| 30 | −0.184384 | 0.006008 | −0.018682 | −0.004235 | −0.030544 | −0.034767 | 0.003313 | 0.044295 | 0.130988 | −0.248431 | 0.038283 | −0.026411 | −0.023923 | 0.021034 |
| 31 | 0.186816 | 0.025038 | 0.000366 | 0.068732 | 0.096479 | −0.030042 | −0.089862 | 0.030793 | −0.000099 | −0.320613 | 0.152998 | 0.048479 | −0.111705 | 0.138057 |
| 32 | 0.055015 | 0.019551 | −0.020438 | −0.105722 | −0.135515 | 0.07012 | 0.056594 | 0.099072 | 0.052809 | −0.096401 | −0.032081 | −0.110945 | 0.067265 | 0.073787 |
| 33 | 0.097097 | −0.05592 | −0.057631 | 0.00882 | −0.027767 | −0.087026 | 0.110751 | 0.060873 | 0.160311 | 0.12065 | −0.128385 | 0.004752 | 0.025505 | 0.061841 |
| 34 | 0.134786 | 0.136723 | 0.174107 | 0.017724 | 0.286382 | −0.11825 | 0.138685 | −0.088502 | −0.025003 | 0.038458 | 0.101169 | −0.097732 | 0.057682 | 0.010697 |
| 35 | 0.028327 | 0.207366 | 0.028676 | −0.069735 | 0.085839 | 0.185288 | −0.097086 | 0.078333 | −0.075296 | −0.073529 | 0.01045 | 0.112128 | 0.042312 | −0.12542 |

APPENDIX B4-continued

| | PCA Transformation Matrix (82 × 82 Normal/Diseased) | | | | | | | | | | | | | |
|---|---|---|---|---|---|---|---|---|---|---|---|---|---|---|
| 36 | −0.017743 | 0.171644 | 0.102876 | −0.074214 | −0.004681 | −0.092867 | −0.001953 | 0.008456 | 0.051746 | −0.060212 | −0.056007 | 0.052521 | 0.031467 | −0.022778 |
| 37 | 0.027118 | −0.044927 | 0.002006 | −0.048365 | 0.028156 | 0.012731 | −0.089355 | −0.009178 | 0.119681 | −0.008847 | 0.106666 | 0.145561 | −0.144767 | 0.00093 |
| 38 | −0.228743 | −0.296052 | 0.084524 | 0.12103 | 0.10179 | −0.06144 | 0.045164 | −0.041181 | 0.151069 | 0.002454 | −0.036768 | 0.047031 | −0.101511 | −0.073095 |
| 39 | −0.004645 | 0.039217 | −0.216359 | −0.300626 | 0.020879 | 0.085879 | −0.269307 | 0.107808 | 0.07928 | 0.051652 | −0.124576 | 0.112255 | 0.029654 | −0.001804 |
| 40 | −0.107478 | −0.027329 | 0.199577 | 0.093861 | 0.044413 | 0.116355 | 0.002621 | −0.044723 | −0.00359 | −0.127074 | 0.120006 | 0.025868 | 0.074153 | 0.100003 |
| 41 | 0.025151 | 0.021002 | −0.136764 | 0.158415 | −0.209408 | −0.049829 | −0.132493 | −0.066064 | 0.005441 | 0.051272 | −0.190808 | −0.023674 | −0.015806 | 0.130566 |
| 42 | −0.050393 | −0.061134 | −0.0716191 | 0.04071 | 0.118533 | −0.1190421 | −0.234247 | −0.0659161 | 0.089611 | −0.034391 | 0.116853 | −0.009651 | 0 088761 | 0.018348 |
| 43 | −0.056058 | −0.198127 | 0.029151 | −0.092497 | −0.069938 | 0.115799 | 0.089489 | 0.133892 | −0.337451 | −0.187182 | −0.05671 | −0.078352 | 0.035025 | 0.056301 |
| 44 | 0.160651 | 0.03129 | −0.146386 | −0.099193 | −0.132805 | 0.035787 | −0.149402 | −0.116025 | −0.058048 | 0.016916 | 0.126309 | −0.286049 | 0.255799 | −0.038225 |
| 45 | −0.096545 | 0.155132 | −0.001235 | 0.081849 | −0.069379 | −0.192866 | −0.070742 | −0.009162 | −0.051385 | −0.00469 | −0.057717 | −0.073956 | −0.098675 | 0.052931 |
| 46 | 0.006593 | 0.047199 | 0.080121 | −0.062544 | −0.071317 | 0.006481 | −0.026353 | −0.016409 | 0.180888 | 0.036012 | 0.094565 | 0.083487 | 0.002199 | 0.065727 |
| 47 | 0.09754 | −0.026116 | −0.055074 | −0.018782 | 0.077247 | 0.004631 | 0.128926 | −0.1296 | 0.04307 | 0.094706 | −0.143161 | −0.013554 | −0.120968 | −0.029017 |
| 48 | −0.04419 | −0.15116 | −0.186548 | 0.002344 | −0.142111 | −0.146198 | 0.128046 | 0.174852 | 0.009333 | 0.102064 | 0.126051 | 0.122003 | −0.09631 | −0.068804 |
| 49 | −0.023174 | −0.146998 | −0.156297 | 0.158979 | 0.132027 | 0.008486 | 0.092227 | −0.08865 | −0.042695 | 0.184086 | 0.180078 | −0.135855 | −0.003239 | 0.13498 |
| 50 | 0.03713 | 0.169246 | 0.193188 | −0.163511 | 0.071134 | −0.147656 | 0.115452 | −0.001217 | 0.116105 | −0.027555 | −0.132855 | 0.042585 | 0.082392 | −0.239304 |
| 51 | 0.094713 | 0.173165 | 0.008159 | 0.050649 | −0.151647 | 0.129314 | 0.011901 | −0.04228 | 0.032553 | −0.080249 | −0.065699 | 0.009973 | −0.139007 | 0.12434 |
| 52 | 0.146972 | −0.101686 | −0.055057 | 0.131537 | −0.061533 | 0.032361 | 0.214499 | −0.045798 | −0.101896 | 0.039111 | −0.067338 | 0.136129 | 0.132903 | −0.093125 |
| 53 | 0.085992 | −0.081847 | −0.100502 | 0.032902 | 0.089113 | 0.033828 | 0.083771 | 0.128529 | −0.086209 | −0.105217 | 0.173155 | −0.02916 | −0.010866 | 0.045858 |
| 54 | 0.127532 | −0.037192 | −0.070178 | 0.020606 | −0.000271 | −0.068162 | −0.006529 | −0.047182 | −0.020193 | −0.032878 | 0.060462 | −0.069148 | 0.08837 | −0.108942 |
| 55 | 0.055731 | −0.081603 | 0.112491 | 0.161972 | −0.253012 | −0.007281 | −0.082058 | −0.106115 | −0.009966 | −0.04001 | 0.035945 | 0.033714 | 0.108678 | −0.021646 |
| 56 | 0.162186 | 0.197354 | 0.046539 | 0.02124 | −0.163299 | 0.03306 | 0.089418 | 0.053583 | 0.134638 | 0.291256 | 0.000207 | 0.105322 | −0.060422 | 0.002947 |
| 57 | −0.016525 | 0.030193 | 0.12991 | 0.088337 | 0.181186 | −0.035283 | 0.218072 | 0.072412 | −0.06519 | −0.140725 | −0.117 | 0.062404 | −0.081578 | −0.010393 |
| 58 | 0.118627 | −0.047497 | 0.113823 | 0.143891 | 0.103105 | −0.195823 | −0.007643 | 0.052728 | −0.195488 | −0.003182 | 0.005793 | 0.118361 | 0.067732 | −0.007699 |
| 59 | −0.165243 | −0.097369 | 0.024687 | −0.154925 | −0.032958 | −0.149655 | −0.256846 | 0.275367 | −0.153478 | −0.082069 | −0.196451 | 0.034208 | −0.104298 | −0.083224 |
| 60 | −0.100964 | 0.072954 | 0.059316 | −0.13272 | 0.12729 | 0.139069 | −0.088475 | −0.206369 | 0.006444 | 0.070596 | 0.013817 | −0.115951 | 0.173088 | −0.010192 |
| 61 | −0.071673 | −0.105401 | −0.011334 | −0.110928 | 0.022548 | 0.006475 | −0.034346 | −0.049555 | −0.030715 | −0.048798 | 0.095637 | −0.074042 | 0.014506 | 0.099156 |
| 62 | −0.046359 | −0.031524 | 0.063889 | −0.025558 | −0.142357 | 0.088757 | −0.166945 | −0.041921 | 0.077087 | 0.01842 | 0.025585 | 0.057788 | −0.110897 | −0.051513 |
| 63 | −0.063338 | 0.325914 | 0.10024 | 0.036914 | 0.033993 | 0.191036 | 0.05164 | 0.00697 | −0.029868 | 0.008518 | −0.001285 | 0.154998 | 0.10244 | 0.123762 |
| 64 | 0.132017 | 0.044137 | −0.078246 | 0.003505 | 0.050603 | −0.024199 | −0.058168 | 0.047079 | −0.135745 | 0.011932 | −0.11317 | −0.001095 | 0.006727 | −0.084641 |
| 65 | −0.058666 | 0.07115 | −0.096876 | 0.074581 | 0.141524 | 0.105225 | 0.065977 | 0.039941 | 0.17959 | −0.101481 | 0.047032 | −0.088512 | −0.239802 | 0.042164 |
| 66 | −0.064187 | 0.055509 | −0.081096 | −0.049846 | 0.09342 | −0.034493 | −0.043725 | 0.165002 | 0.035335 | 0.059993 | −0.071393 | 0.00202 | 0.002674 | −0.086279 |
| 67 | 0.082303 | 0.056162 | 0.157512 | 0.05235 | −0.121714 | −0.096209 | 0.1181 | −0.21935 | −0.006854 | −0.0165251 | 0.054622 | 0.180118 | −0.138144 | 0.060162 |
| 68 | 0.02595 | −0.118317 | 0.030804 | 0.125427 | −0.04937 | 0.005771 | −0.031343 | 0.130795 | 0.028336 | 0.023802 | −0.045878 | −0.045292 | 0.127787 | 0.137499 |
| 69 | −0.094446 | −0.034466 | 0.109541 | 0.005603 | −0.135468 | 0.094441 | −0.086894 | 0.160433 | −0.064762 | −0.088439 | 0.083234 | −0.211785 | −0.011694 | −0.173855 |
| 70 | −0.02417 | 0.076153 | −0.070599 | −0.063964 | 0.004882 | −0.024531 | 0.112943 | 0.022264 | −0.02887 | 0.010803 | −0.083575 | −0.143292 | 0.067231 | 0.068769 |
| 71 | 0.007481 | 0.001796 | −0.104238 | −0.050822 | 0.268385 | −0.012519 | 0.101657 | 0.016448 | −0.012983 | −0.028067 | −0.104774 | −0.039904 | −0.04019 | 0.159294 |
| 72 | −0.002358 | −0.13287 | 0.194267 | −0.150355 | 0.148609 | −0.104921 | −0.038475 | −0.0029 | 0.054365 | 0.071684 | 0.140309 | 0.158526 | −0.032526 | −0.141988 |
| 73 | −0.026895 | 0.076247 | −0.121968 | −0.084737 | −0.099758 | −0.112182 | −0.079309 | −0.019637 | −0.060724 | −0.051303 | 0.413632 | 0.046408 | 0.076327 | −0.080651 |
| 74 | −0.14218 | −0.046547 | −0.168838 | 0.018545 | 0.10919 | 0.022426 | −0.110582 | −0.10698 | −0.071239 | 0.15185 | −0.037507 | 0.293884 | −0.034078 | −0.029852 |
| 75 | −0.203813 | 0.078071 | −0.025937 | 0.145279 | −0.127075 | −0.055058 | −0.023683 | 0.036621 | 0.105251 | 0.015441 | −0.250038 | −0.202682 | −0.038292 | −0.028434 |
| 76 | −0.017034 | 0.072068 | −0.024506 | −0.127038 | 0.121101 | −0.00992 | 0.057394 | 0.162943 | 0.017552 | 0.127091 | 0.200205 | 0.058262 | 0.201702 | −0.060794 |
| 77 | 0.065016 | −0.042109 | 0.078876 | 0.075812 | 0.07505 | −0.017712 | −0.164759 | 0.123472 | 0.147148 | 0.136764 | −0.075077 | −0.08568 | −0.12868 | 0.157069 |
| 78 | 0.067668 | 0.073701 | 0.08128 | −0.231904 | −0.174008 | −0.037737 | 0.161776 | 0.100271 | −0.272355 | −0.216453 | −0.175072 | 0.099158 | −0.016004 | −0.008383 |
| 79 | −0.055312 | −0.065159 | −0.099679 | −0.085837 | 0.025712 | 0.08027 | −0.113063 | −0.299153 | 0.032395 | −0.136513 | −0.148284 | 0.317859 | 0.15454 | 0.163695 |
| 80 | −0.025749 | −0.134942 | −0.005212 | 0.225004 | −0.02893 | −0.128979 | 0.059659 | 0.01342 | 0.049312 | −0.042491 | −0.011668 | −0.110607 | 0.050283 | −0.024166 |
| 81 | 0.052313 | 0.141451 | −0.097195 | 0.01312 | −0.033592 | 0.147063 | 0.036739 | −0.061604 | 0.201843 | −0.25047 | 0.04058 | −0.194304 | −0.066686 | 0.120956 |
| 82 | 0.244044 | 0.036377 | −0.0009691 | 0.004961 | 0.0681381 | 0.2950841 | −0.014733 | −0.0133291 | −0.112202 | 0.2486331 | −0.039026 | −0.086736 | −0.170631 | −0.183877 |

APPENDIX B4-continued

PCA Transformation
Matrix (82 × 82
Normal/Diseased)

| | BD | BE | BF | BG | BH | BI | BJ | BK | BL | BM | BN | BO | BP | BQ |
|---|---|---|---|---|---|---|---|---|---|---|---|---|---|---|
| 1 | −0.0671 | 0.026472 | −0.060669 | 0.051168 | 0.027837 | −0.058365 | 0.046409 | −0.077825 | 0.085743 | −0.043331 | −0.11249 | −0.087966 | 0.060765 | −0.054089 |
| 2 | 0.016738 | 0.041159 | 0.068516 | 0.084415 | 0.089196 | 0.129925 | −0.074419 | 0.008767 | 0.090258 | 0.068138 | −0.105885 | 0.022281 | 0.020149 | −0.022218 |
| 3 | −0.121678 | −0.011211 | 0.050389 | −0.048928 | −0.096332 | 0.049403 | −0.07241 | 0.180888 | −0.082206 | 0.059938 | 0.092904 | 0.22283 | −0.035357 | 0.090797 |
| 4 | −0.021785 | 0.081765 | 0.004056 | 0.033783 | 0.217453 | −0.037514 | −0.035164 | 0.015436 | 0.070241 | −0.142971 | −0.032854 | −0.164064 | 0.049337 | −0.062085 |
| 5 | 0.038818 | −0.026972 | −0.007812 | 0.050887 | 0.172395 | −0.124674 | 0.034358 | −0.155206 | 0.100481 | −0.030357 | −0.057338 | −0.080443 | −0.042844 | −0.03147 |
| 6 | 0.138201 | −0.04906 | −0.13269 | 0.083316 | −0.072558 | 0.021904 | 0.160484 | −0.292868 | 0.095005 | 0.150258 | −0.0911 | 0.229442 | 0.021224 | −0.152221 |
| 7 | −0.02849 | −0.186312 | −0.310965 | −0.287462 | −0.004697 | −0.222234 | 0.120262 | 0.017273 | −0.089837 | −0.095299 | 0.123683 | 0.085192 | −0.116521 | 0.115675 |
| 8 | 0.189488 | 0.009274 | 0.035581 | −0.032001 | 0.081933 | −0.10194 | −0.010448 | −0.15889 | 0.122402 | −0.11564 | −0.039001 | −0.200478 | 0.078902 | 0.007903 |
| 9 | −0.26525 | 0.088934 | 0.142269 | 0.0062 | −0.072069 | −0.008288 | −0.226548 | 0.090875 | 0.088599 | −0.023696 | 0.011398 | −0.075199 | −0.029836 | −0.026375 |
| 10 | 0.087262 | −0.064493 | 0.121406 | 0.214024 | −0.20733 | 0.004162 | −0.031544 | −0.008872 | −0.043324 | 0.059765 | −0.039582 | −0.067025 | 0.071938 | −0.026023 |
| 11 | −0.092986 | 0.073967 | −0.115645 | −0.036493 | −0.007106 | 0.177187 | −0.013458 | 0.110116 | 0.025123 | −0.04317 | 0.047041 | −0.009016 | 0.030855 | 0.124866 |
| 12 | 0.225704 | 0.053259 | 0.205712 | −0.051826 | −0.028032 | 0.185273 | 0.038127 | 0.175124 | −0.179253 | 0.02573 | −0.012724 | −0.094551 | 0.028972 | −0.015016 |
| 13 | 0.022812 | 0.161867 | −0.004716 | −0.072184 | −0.004131 | −0.186481 | 0.119375 | −0.141562 | 0.230541 | −0.069325 | 0.064512 | 0.209948 | −0.06844 | −0.105361 |
| 14 | 0.013848 | −0.082319 | 0.00661 | −0.106389 | 0.149638 | 0.293438 | −0.132891 | 0.097841 | 0.07542 | −0.192971 | 0.123018 | −0.074224 | −0.178909 | −0.125687 |
| 15 | −0.054048 | −0.150949 | 0.173131 | 0.129 | −0.04522 | −0.032308 | 0.124017 | −0.059024 | −0.023502 | 0.093969 | −0.037598 | 0.022048 | 0.114239 | 0.069394 |
| 16 | −0.117344 | 0.173643 | −0.253394 | 0.02156 | −0.009936 | −0.049107 | −0.005854 | 0.036272 | −0.140893 | 0.087112 | −0.236597 | −0.0786 | 0.155271 | 0.15904 |
| 17 | −0.041016 | 0.054945 | −0.099426 | 0.061151 | −0.008425 | 0.042817 | −0.03415 | −0.091322 | 0.019925 | −0.023227 | −0.069005 | 0.031714 | 0.040254 | −0.083236 |
| 18 | −0.195133 | −0.053838 | 0.075931 | −0.101809 | 0.135087 | −0.130763 | −0.13532 | 0.036127 | 0.102546 | −0.063453 | 0.009915 | 0.071814 | −0.041938 | −0.015754 |
| 19 | −0.036159 | 0.008253 | 0.054043 | −0.194817 | 0.046256 | −0.09624 | −0.030956 | 0.179948 | 0.130585 | −0.036772 | −0.025004 | 0.006563 | −0.071356 | −0.035678 |
| 20 | 0.057579 | −0.163069 | 0.169249 | 0.067024 | 0.01581 | −0.02473 | 0.065417 | −0.126274 | −0.077994 | 0.017713 | 0.023089 | 0.012643 | −0.019543 | 0.056082 |
| 21 | −0.025216 | 0.195228 | −0.107131 | −0.111983 | −0.069511 | −0.055426 | −0.144776 | 0.116424 | −0.073899 | −0.000074 | −0.001762 | −0.047396 | −0.033279 | 0.009679 |
| 22 | −0.153639 | −0.111255 | 0.039459 | 0.088038 | −0.028374 | 0.042771 | 0.015538 | 0.155585 | −0.042292 | 0.103573 | 0.152068 | 0.208758 | −0.130482 | −0.09499 |
| 23 | −0.047143 | −0.040519 | 0.01451 | 0.106356 | 0.226501 | 0.131704 | 0.036167 | 0.054168 | 0.039674 | 0.124453 | −0.006782 | −0.03787 | −0.017339 | −0.01998 |
| 24 | −0.01049 | 0.144968 | 0.04733 | −0.151576 | −0.242803 | −0.177996 | −0.001686 | −0.105018 | −0.152493 | −0.235805 | 0.091274 | −0.070364 | 0.008858 | −0.019264 |
| 25 | 0.00652 | −0.084783 | −0.085398 | −0.019934 | 0.065386 | 0.078404 | 0.039706 | −0.017169 | 0.086234 | 0.052729 | 0.018274 | 0.013878 | 0.035776 | −0.03027 |
| 26 | 0.142583 | 0.016676 | 0.067455 | 0.030275 | 0.014956 | −0.01733 | −0.082762 | 0.006716 | 0.037309 | −0.075023 | 0.061923 | −0.073214 | −0.092935 | −0.091117 |
| 27 | −0.068846 | −0.057215 | −0.091388 | 0.023825 | 0.020372 | −0.030321 | 0.055738 | 0.094752 | 0.033273 | 0.196105 | −0.139665 | 0.1898 | 0.05317 | 0.076309 |
| 28 | 0.00808 | 0.169218 | 0.009568 | 0.004541 | 0.037715 | −0.074462 | −0.088856 | 0.090647 | −0.033106 | 0.002362 | −0.129173 | 0.191576 | 0.089851 | −0.022784 |
| 29 | 0.146208 | −0.054131 | 0.087821 | −0.183178 | 0.190572 | 0.036085 | −0.081156 | −0.101502 | −0.057752 | 0.034131 | 0.07565 | −0.0554 | −0.234637 | 0.067688 |
| 30 | −0.164522 | −0.018754 | 0.133951 | 0.150697 | −0.183797 | −0.138908 | 0.15202 | 0.000581 | −0.035379 | −0.147147 | 0.23486 | −0.064851 | 0.314147 | −0.152599 |
| 31 | 0.111801 | 0.001763 | −0.161406 | 0.007946 | −0.006792 | 0.121428 | −0.044997 | −0.071291 | 0.010592 | 0.178244 | −0.08377 | −0.170735 | −0.097903 | 0.172755 |
| 32 | 0.044039 | −0.030668 | −0.033324 | −0.003831 | −0.005968 | 0.044601 | −0.010746 | −0.03662 | −0.062982 | −0.002842 | 0.016581 | −0.06645 | 0.033502 | 0.022855 |
| 33 | 0.056799 | 0.208089 | 0.079392 | −0.13069 | −0.048947 | 0.025109 | 0.16009 | 0.045203 | −0.02906 | 0.039128 | 0.034173 | −0.088385 | 0.007328 | 0.084732 |
| 34 | −0.051815 | 0.104791 | 0.016184 | −0.046372 | −0.142863 | −0.063295 | 0.041342 | −0.050287 | 0.019303 | −0.106695 | −0.018949 | 0.025313 | −0.113288 | −0.040476 |
| 35 | 0.046082 | 0.132192 | 0.092432 | 0.086858 | 0.060761 | −0.013644 | −0.040142 | −0.08637 | 0.036837 | −0.012798 | 0.011342 | 0.120592 | 0.033621 | −0.006905 |
| 36 | −0.034697 | −0.024333 | −0.028949 | 0.076533 | 0.1907 | 0.02802 | 0.118333 | 0.032442 | 0.037619 | 0.029995 | −0.03011 | 0.063498 | −0.027233 | 0.00659 |
| 37 | 0.092923 | 0.044593 | 0.288333 | −0.146428 | −0.157876 | −0.0264 | −0.004423 | −0.133884 | −0.111323 | 0.194996 | −0.031683 | −0.158124 | 0.054262 | 0.01508 |
| 38 | −0.116402 | −0.081722 | −0.008138 | 0.060724 | −0.040569 | 0.054071 | 0.000265 | 0.022612 | −0.036728 | 0.048051 | −0.035372 | −0.12654 | 0.053199 | −0.017476 |
| 39 | −0.036267 | −0.003477 | 0.044381 | −0.135512 | −0.116811 | 0.089377 | 0.014006 | −0.03314 | −0.235908 | 0.089575 | 0.138006 | −0.005995 | 0.066679 | −0.106486 |
| 40 | 0.015321 | −0.081229 | 0.083425 | −0.121891 | 0.069573 | −0.001762 | 0.034432 | −0.01474 | 0.076543 | 0.015816 | 0.000676 | −0.126312 | −0.055481 | 0.103497 |
| 41 | −0.06695 | −0.089198 | −0.04703 | −0.00089 | 0.257508 | −0.035911 | 0.062989 | 0.138855 | −0.148164 | −0.028677 | 0.132017 | −0.005117 | −0.078607 | −0.059037 |
| 42 | −0.106588 | 0.102545 | −0.23708 | −0.075378 | −0.036182 | 0.242318 | 0.319512 | 0.033666 | 0.161071 | −0.180368 | −0.103317 | −0.043189 | 0.102795 | 0.205784 |
| 43 | 0.134394 | −0.033993 | −0.011471 | 0.107669 | 0.074787 | −0.18935 | −0.050593 | 0.095808 | −0.065603 | −0.077896 | 0.074244 | 0.069836 | 0.024114 | −0.094242 |
| 44 | 0.029013 | 0.020516 | −0.216362 | 0.063993 | −0.085823 | −0.090756 | −0.048597 | −0.017331 | 0.148328 | −0.195527 | 0.060338 | 0.064466 | −0.095024 | 0.120139 |
| 45 | −0.123493 | −0.063805 | −0.099099 | 0.185502 | −0.247102 | −0.019652 | −0.13381 | 0.177005 | 0.036646 | 0.178567 | 0.026119 | 0.003231 | −0.09367 | 0.012238 |
| 46 | 0.039502 | 0.002101 | −0.029887 | −0.00053 | 0.019611 | −0.005335 | 0.003709 | −0.048443 | 0.039793 | 0.055609 | −0.060064 | −0.068594 | 0.006694 | 0.060307 |
| 47 | −0.050137 | 0.246646 | −0.125977 | 0.185026 | 0.04415 | 0.169947 | 0.165724 | −0.090684 | −0.170886 | −0.026609 | 0.170246 | −0.015488 | 0.013721 | 0.033751 |

APPENDIX B4-continued

PCA Transformation
Matrix (82 × 82
Normal/Diseased)

| | | | | | | | | | | | | | | |
|---|---|---|---|---|---|---|---|---|---|---|---|---|---|---|
| 48 | 0.09968 | −0.189421 | 0.064104 | 0.059835 | −0.049209 | 0.015994 | −0.18284 | −0.015169 | 0.332872 | 0.024409 | −0.259082 | 0.052986 | 0.069366 | 0.06156 |
| 49 | −0.080583 | −0.028438 | 0.014125 | 0.036252 | −0.028261 | −0.042117 | −0.302027 | −0.092376 | −0.042686 | 0.020045 | 0.102636 | −0.030245 | −0.080202 | 0.051063 |
| 50 | 0.114007 | −0.137307 | −0.195996 | 0.071859 | −0.113119 | −0.133434 | −0.047121 | 0.036744 | −0.11964 | 0.113041 | 0.016166 | −0.171762 | −0.043317 | −0.108521 |
| 51 | −0.015125 | 0.198608 | 0.22184 | −0.045182 | −0.010546 | 0.070288 | −0.056351 | −0.160797 | 0.180258 | 0.115782 | 0.150321 | 0.23549 | −0.037683 | −0.02122 |
| 52 | 0.017449 | 0.156835 | 0.106721 | −0.042919 | −0.032555 | 0.191903 | 0.169211 | 0.03199 | 0.131967 | −0.131596 | 0.105671 | −0.006746 | 0.003824 | −0.026576 |
| 53 | −0.128769 | −0.019083 | 0.082107 | −0.039781 | 0.284 | −0.171299 | 0.066025 | −0.061691 | −0.189905 | −0.132624 | −0.14868 | −0.061637 | 0.276816 | −0.149966 |
| 54 | −0.151295 | −0.087951 | 0.011665 | −0.126392 | 0.061181 | 0.008892 | 0.047945 | −0.249684 | −0.013394 | 0.046245 | 0.073765 | −0.062932 | −0.08651 | −0.08429 |
| 55 | −0.082609 | 0.186926 | 0.039006 | 0.050823 | 0.081736 | 0.062822 | 0.099513 | 0.263865 | 0.017206 | 0.069921 | −0.009453 | −0.096006 | −0.045261 | −0.115906 |
| 56 | −0.049219 | −0.051356 | 0.073443 | −0.05699 | 0.230602 | −0.083857 | 0.071931 | 0.126747 | −0.173758 | −0.092221 | −0.25818 | −0.002844 | −0.1249 | −0.099027 |
| 57 | 0.036036 | −0.032042 | 0.037264 | −0.009096 | −0.062458 | 0.142803 | 0.003802 | −0.025466 | 0.013975 | −0.265774 | −0.129897 | 0.145563 | 0.179649 | −0.034329 |
| 58 | 0.094661 | −0.013471 | −0.072971 | −0.286911 | 0.066131 | 0.025787 | −0.009033 | 0.001082 | −0.008077 | 0.313304 | 0.05551 | −0.059284 | 0.113744 | −0.083041 |
| 59 | 0.168032 | 0.037536 | 0.098864 | −0.030392 | 0.02018 | −0.017389 | 0.10457 | −0.018321 | 0.10974 | 0.017512 | −0.028763 | 0.081154 | −0.151779 | 0.093899 |
| 60 | −0.021741 | −0.01554 | −0.111889 | −0.109022 | −0.075848 | 0.005964 | −0.180091 | −0.016306 | −0.022057 | 0.044433 | 0.0481 | 0.100098 | 0.050193 | −0.081697 |
| 61 | 0.063336 | −0.181009 | −0.049744 | −0.071615 | −0.116137 | −0.10425 | 0.072159 | 0.119297 | 0.041224 | −0.042302 | −0.122394 | 0.093475 | −0.151426 | −0.2566 |
| 62 | 0.132265 | −0.067731 | −0.074556 | 0.106721 | 0.202509 | 0.028894 | −0.162094 | 0.039233 | −0.004487 | −0.034638 | 0.31783 | −0.061813 | 0.31756 | 0.161772 |
| 63 | −0.071089 | −0.028204 | −0.091292 | −0.025021 | −0.057531 | −0.014216 | −0.001975 | −0.024563 | 0.007912 | 0.048231 | 0.080661 | 0.005594 | −0.003092 | −0.077293 |
| 64 | 0.007197 | −0.013761 | 0.029448 | 0.027898 | −0.00162 | 0.088251 | −0.227716 | −0.184954 | −0.098752 | −0.142084 | −0.09173 | 0.117959 | 0.047519 | 0.281554 |
| 65 | 0.007347 | 0.085743 | 0.153351 | 0.293 | 0.008942 | −0.317896 | 0.135405 | −0.013578 | −0.041519 | −0.031819 | 0.026173 | −0.140464 | −0.347612 | 0.259549 |
| 66 | 0.044611 | 0.095216 | −0.023458 | −0.032259 | 0.018449 | 0.017583 | −0.021104 | 0.017313 | −0.041035 | 0.008399 | 0.052547 | −0.02021 | −0.001933 | −0.05473 |
| 67 | −0.019688 | −0.156323 | −0.039178 | 0.096423 | 0.098285 | 0.026355 | −0.173983 | 0.013927 | −0.082599 | −0.077975 | 0.057855 | 0.028418 | 0.017623 | 0.10083 |
| 68 | 0.249507 | 0.136813 | −0.150422 | −0.013646 | −0.046031 | −0.129876 | 0.0817 | 0.116787 | 0.012699 | 0.031369 | −0.058138 | −0.009418 | −0.006957 | −0.135207 |
| 69 | −0.229304 | −0.117067 | 0.082922 | −0.02895 | −0.066059 | 0.270069 | 0.183977 | −0.200812 | −0.205477 | −0.051734 | −0.135984 | 0.00965 | −0.265037 | −0.100147 |
| 70 | −0.168527 | −0.013465 | 0.165885 | −0.299981 | −0.05855 | −0.182667 | 0.075326 | 0.081339 | 0.113333 | 0.073283 | 0.029057 | 0.015851 | 0.137206 | 0.346568 |
| 71 | 0.063921 | 0.194923 | −0.010024 | 0.017764 | −0.029248 | 0.010276 | −0.103483 | 0.101523 | 0.229148 | 0.085942 | 0.07994 | −0.208836 | 0.02047 | −0.282965 |
| 72 | 0.042317 | −0.016691 | −0.030051 | 0.204145 | 0.035551 | 0.018209 | −0.02676 | −0.077485 | −0.165755 | −0.081914 | 0.010425 | 0.129752 | 0.00521 | −0.074024 |
| 73 | −0.102221 | 0.1768 | −0.080562 | 0.088353 | 0.155661 | −0.108659 | 0.019257 | −0.075501 | 0.058902 | 0.154441 | 0.082477 | 0.099223 | −0.016044 | −0.142108 |
| 74 | −0.263565 | 0.025705 | 0.060644 | 0.081095 | 0.081824 | 0.005234 | 0.005443 | −0.084804 | 0.092473 | 0.11515 | −0.019344 | 0.027005 | 0.030102 | −0.007739 |
| 75 | −0.171374 | 0.038611 | −0.107007 | −0.05266 | −0.02887 | −0.108172 | −0.166283 | −0.189647 | −0.050071 | 0.004236 | −0.124158 | −0.170717 | 0.047313 | −0.085304 |
| 76 | 0.089042 | 0.00272 | 0.12258 | 0.150817 | 0.089834 | −0.133565 | 0.190016 | 0.248689 | −0.009126 | 0.114199 | 0.010405 | 0.059284 | 0.031954 | 0.190023 |
| 77 | 0.162203 | −0.09366 | 0.015469 | 0.005292 | −0.03166 | 0.062511 | −0.024691 | 0.04603 | 0.028816 | −0.277529 | 0.181945 | 0.150311 | 0.043179 | 0.026739 |
| 78 | −0.096768 | 0.042146 | −0.030163 | 0.050413 | 0.028363 | 0.070994 | −0.059816 | −0.100037 | 0.117718 | 0.013928 | 0.041076 | −0.209142 | −0.122361 | 0.091176 |
| 79 | 0.078163 | 0.139916 | 0.03489 | 0.079789 | −0.146926 | 0.054581 | −0.123587 | 0.146608 | −0.116673 | −0.201655 | −0.314098 | −0.016213 | −0.160699 | 0.000515 |
| 80 | 0.209654 | 0.150625 | −0.124917 | 0.00074 | 0.054426 | 0.016897 | 0.000355 | −0.140855 | −0.195277 | 0.132956 | 0.126181 | 0.114427 | −0.071246 | 0.084651 |
| 81 | 0.146986 | −0.052891 | 0.096811 | −0.171898 | 0.033008 | 0.039499 | −0.027258 | 0.064538 | −0.097775 | 0.043352 | −0.199656 | 0.143209 | 0.183301 | −0.048538 |
| 82 | 0.035128 | −0.342697 | −0.041386 | 0.040303 | −0.177007 | 0.049145 | 0.21351 | 0.069343 | 0.183195 | −0.028818 | 0.094236 | −0.238367 | 0.052613 | −0.046455 |

| | BR | BS | BT | BU | BV | BW | BX | BY | BZ | CA | CB | CC | CD | CE |
|---|---|---|---|---|---|---|---|---|---|---|---|---|---|---|
| 1 | 0.125526 | −0.05917 | 0.135668 | −0.106936 | 0.028181 | −0.030978 | −0.051264 | −0.076232 | 0.03616 | 0.004434 | −0.003782 | −0.064539 | 0.050026 | −0.013758 |
| 2 | −0.066932 | −0.05253 | −0.122626 | −0.054415 | 0.004196 | 0.02524 | −0.013494 | 0.072267 | −0.052483 | −0.012596 | 0.071361 | −0.044613 | −0.011781 | −0.01505 |
| 3 | −0.09196 | 0.058755 | −0.15249 | 0.223646 | −0.106657 | 0.128234 | 0.004635 | 0.110805 | −0.183505 | 0.008323 | −0.065246 | 0.042885 | −0.033708 | −0.001747 |
| 4 | 0.057715 | −0.035419 | 0.240167 | −0.279251 | 0.070014 | −0.190153 | 0.044871 | 0.005032 | 0.26325 | −0.021374 | 0.046028 | 0.055446 | 0.450908 | −0.004413 |
| 5 | 0.077867 | −0.08277 | −0.02153 | −0.104098 | −0.006676 | 0.054667 | −0.097029 | −0.230548 | −0.002263 | −0.055391 | 0.006375 | −0.195706 | −0.738209 | −0.003203 |
| 6 | 0.084514 | −0.072189 | −0.276851 | 0.205637 | 0.09439 | 0.094566 | −0.310936 | 0.097644 | −0.159114 | −0.138485 | 0.044087 | 0.077404 | 0.288263 | −0.009469 |
| 7 | −0.021997 | 0.123006 | 0.189667 | 0.162691 | −0.031913 | −0.158965 | 0.052586 | −0.002329 | 0.147603 | 0.014866 | −0.067908 | 0.089009 | −0.051621 | −0.000963 |
| 8 | −0.116928 | 0.144545 | −0.044889 | 0.130694 | 0.006311 | −0.015862 | −0.011103 | −0.297439 | −0.092314 | −0.103569 | 0.067337 | 0.19422 | 0.058546 | −0.004745 |
| 9 | −0.023597 | 0.073212 | −0.04709 | −0.090465 | 0.008605 | −0.019807 | 0.107008 | −0.118744 | −0.042004 | 0.077804 | −0.033992 | −0.008363 | 0.027795 | −0.001423 |
| 10 | 0.03873 | −0.086774 | 0.026709 | −0.106988 | −0.056465 | −0.014755 | 0.050466 | −0.037011 | −0.032974 | 0.118743 | 0.009007 | −0.09551 | 0.059681 | −0.000307 |
| 11 | −0.098694 | 0.036677 | 0.062108 | 0.026792 | −0.04614 | −0.059069 | 0.209522 | 0.062081 | −0.066062 | 0.062374 | 0.034065 | 0.037224 | −0.018112 | −0.00121 |

APPENDIX B4-continued

PCA Transformation Matrix (82 × 82 Normal/Diseased)

| | | | | | | | | | | | | | | |
|---|---|---|---|---|---|---|---|---|---|---|---|---|---|---|
| 12 | −0.068113 | −0.009262 | 0.012882 | 0.0111 | −0.000568 | 0.182047 | 0.007524 | 0.157149 | 0.005939 | −0.010247 | 0.013549 | −0.014986 | 0.017024 | −0.000607 |
| 13 | −0.02806 | −0.257858 | −0.021562 | −0.133587 | 0.20581 | −0.147561 | 0.18629 | 0.147603 | −0.141029 | 0.138175 | −0.022243 | 0.014863 | −0.029496 | −0.004108 |
| 14 | 0.044084 | 0.072601 | −0.143154 | −0.130529 | 0.049018 | 0.029627 | −0.094923 | −0.056793 | −0.083996 | −0.088752 | 0.081563 | 0.033147 | −0.019438 | −0.001343 |
| 15 | −0.09525 | 0.042094 | 0.002392 | 0.153557 | 0.016979 | −0.019032 | 0.054366 | 0.025308 | 0.09805 | 0.059797 | −0.02071 | 0.037316 | −0.029634 | −0.001162 |
| 16 | 0.031673 | 0.209596 | 0.182499 | 0.164105 | −0.185588 | 0.15612 | −0.169762 | −0.094534 | 0.063555 | −0.169811 | −0.014131 | −0.034858 | 0.04304 | −0.002987 |
| 17 | 0.099375 | −0.054139 | 0.010654 | −0.080723 | −0.044202 | −0.006153 | 0.012945 | 0.032794 | −0.050873 | 0.020703 | 0.100943 | −0.039267 | 0.026105 | −0.015076 |
| 18 | −0.01891 | 0.057764 | −0.052284 | 0.079283 | 0.093427 | 0.00921 | −0.069984 | −0.041469 | 0.06051 | −0.047186 | 0.012238 | 0.011502 | 0.004623 | −0.002991 |
| 19 | −0.057806 | 0.006638 | −0.089834 | 0.007988 | 0.071737 | 0.116703 | −0.20079 | −0.005101 | 0.069176 | −0.128306 | 0.001181 | 0.046152 | 0.025563 | −0.013621 |
| 20 | −0.028087 | 0.042079 | 0.010898 | 0.068173 | −0.097843 | −0.027965 | 0.109842 | −0.011415 | 0.004844 | 0.076388 | −0.13366 | 0.028878 | 0.022967 | −0.000485 |
| 21 | 0.019833 | −0.126833 | −0.026286 | −0.04891 | 0.031552 | 0.045834 | −0.056815 | 0.013287 | 0.031312 | −0.053805 | 0.069747 | −0.081098 | 0.03099 | −0.000462 |
| 22 | 0.153554 | −0.083459 | −0.011816 | −0.197084 | 0.02653 | 0.034151 | −0.036052 | 0.273487 | 0.157146 | 0.099068 | −0.043196 | −0.099099 | −0.067878 | −0.001546 |
| 23 | −0.025138 | −0.002184 | 0.062236 | 0.054233 | −0.032474 | 0.08617 | 0.05459 | 0.089445 | 0.026789 | −0.018725 | 0.043627 | 0.07099 | −0.043559 | −0.0065 |
| 24 | 0.057396 | 0.073077 | −0.147686 | −0.075197 | 0.01013 | −0.02128 | −0.061091 | −0.068887 | −0.093139 | 0.072255 | −0.080722 | −0.018194 | 0.057814 | −0.016295 |
| 25 | −0.030157 | −0.040113 | 0.024959 | −0.002491 | −0.005582 | −0.020532 | −0.053874 | 0.006677 | 0.033825 | −0.061962 | 0.044091 | 0.00629 | −0.009451 | −0.01785 |
| 26 | 0.156894 | −0.208265 | 0.203096 | 0.386515 | 0.035726 | 0.00945 | 0.107107 | 0.159104 | 0.130251 | −0.09204 | 0.207652 | −0.056051 | −0.041553 | −0.16188 |
| 27 | −0.164559 | 0.172103 | −0.032648 | −0.382162 | −0.067336 | 0.062151 | −0.10869 | −0.148481 | −0.148851 | 0.101037 | −0.238076 | 0.002887 | 0.058959 | −0.096947 |
| 28 | −0.098999 | 0.011746 | 0.156622 | 0.096139 | −0.03169 | −0.063014 | 0.085443 | 0.070148 | −0.044631 | −0.044692 | −0.02412 | −0.063137 | −0.04367 | −0.238116 |
| 29 | 0.160052 | 0.086458 | −0.131387 | −0.088421 | −0.042283 | 0.097965 | −0.092895 | −0.038324 | 0.112219 | 0.070014 | −0.032226 | −0.001085 | 0.08487 | −0.093334 |
| 30 | 0.014193 | −0.061957 | −0.010177 | −0.087757 | −0.079148 | 0.093355 | −0.106872 | 0.087198 | 0.118028 | −0.263096 | 0.004443 | 0.088722 | −0.069109 | −0.069114 |
| 31 | −0.064403 | −0.082911 | −0.063088 | 0.04864 | 0.175878 | −0.080173 | 0.154031 | −0.072542 | −0.119585 | 0.172917 | 0.056286 | 0.007989 | 0.010174 | −0.018293 |
| 32 | −0.0408 | −0.033008 | −0.064815 | −0.079075 | 0.043842 | 0.003763 | −0.034444 | 0.025074 | 0.02256 | −0.000099 | −0.00573 | −0.009464 | 0.006181 | −0.003418 |
| 33 | 0.104152 | 0.003718 | 0.142417 | −0.036899 | 0.453767 | 0.151707 | −0.026331 | 0.049627 | −0.033619 | −0.05519 | −0.299738 | 0.118201 | −0.075896 | −0.142899 |
| 34 | 0.036823 | 0.026239 | −0.004335 | 0.063292 | −0.022219 | −0.052357 | 0.032739 | −0.016447 | 0.018709 | −0.011689 | 0.000744 | 0.000164 | −0.000096 | −0.075151 |
| 35 | −0.043135 | −0.033296 | −0.015901 | 0.054309 | −0.103648 | −0.012665 | 0.039197 | 0.057851 | 0.00639 | −0.078863 | −0.069874 | −0.045791 | 0.013462 | −0.044533 |
| 36 | 0.023482 | −0.003016 | 0.029113 | 0.070421 | −0.006663 | 0.052839 | 0.044854 | 0.015879 | 0.023237 | −0.036186 | 0.0172 | 0.033356 | −0.00382 | −0.004966 |
| 37 | −0.085246 | 0.027803 | 0.061345 | −0.070935 | −0.091239 | −0.104377 | −0.076582 | 0.062774 | 0.081493 | 0.122555 | 0.071666 | −0.01059 | −0.052216 | −0.023393 |
| 38 | 0.036307 | −0.08027 | −0.029789 | −0.031768 | 0.059577 | 0.107334 | −0.0281 | −0.134336 | 0.055646 | 0.026935 | 0.054562 | −0.001876 | 0.02166 | −0.004436 |
| 39 | −0.186269 | −0:017583 | −0.072462 | −0.093673 | 0.049829 | −0.012683 | 0.050484 | −0.084352 | 0.077263 | 0.041403 | 0.004625 | −0.004604 | −0.027862 | −0.120052 |
| 40 | −0.01362 | 0.023817 | 0.010227 | −0.027835 | 0.064414 | 0.131588 | −0.053522 | 0.088315 | 0.030981 | −0.013223 | −0.12974 | 0.051718 | 0.007693 | −0.45549 |
| 41 | −0.007372 | 0.098246 | 0.000021 | 0.001761 | 0.036596 | 0.020963 | −0.107081 | 0.104607 | −0.118891 | 0.040458 | 0.094298 | 0.046495 | 0.012308 | −0.050277 |
| 42 | −0.056734 | −0.084229 | −0.138623 | −0.050529 | −0.070378 | −0.048282 | 0.095925 | 0.110415 | 0.091469 | −0.030539 | −0.105253 | −0.111142 | −0.038758 | −0.042722 |
| 43 | 0.055399 | −0.063347 | −0.246923 | 0.055631 | 0.129798 | 0.070569 | 0.043427 | −0.246803 | −0.000653 | −0.127547 | −0.194919 | 0.001226 | 0.111978 | −0.01711 |
| 44 | 0.087701 | 0.035264 | 0.082351 | −0.034628 | 0.015873 | 0.027585 | −0.114925 | 0.156678 | −0.11841 | 0.050322 | −0.052488 | −0.029515 | 0.003579 | −0.027339 |
| 45 | −0.027008 | −0.079216 | −0.009363 | 0.118701 | 0.22283 | −0.020523 | 0.098688 | −0.264223 | 0.098947 | −0.080693 | 0.004351 | −0.017228 | 0.013672 | −0.350777 |
| 46 | 0.019527 | 0.00842 | 0.073117 | −0.049244 | −0.069302 | 0.049099 | −0.092234 | 0.143885 | 0.00735 | 0.101369 | −0.032222 | 0.011393 | −0.009345 | −0.229059 |
| 47 | 0.13919 | −0.013402 | −0.143595 | −0.009695 | −0.018025 | −0.120577 | 0.129732 | −0.203208 | −0.08861 | 0.007291 | 0.177884 | −0.001748 | 0.008943 | −0.317526 |
| 48 | −0.007866 | −0.027981 | 0.095892 | −0.070234 | −0.027127 | 0.003909 | 0.01747 | 0.050986 | 0.102486 | −0.098462 | −0.148738 | 0.008736 | −0.002264 | −0.161296 |
| 49 | −0.039769 | 0.128494 | 0.095642 | 0.026387 | 0.131925 | −0.07197 | −0.06396 | 0.020127 | −0.147711 | −0.016594 | 0.103156 | 0.06248 | 0.004146 | −0.017065 |
| 50 | 0.240082 | −0.076673 | 0.186897 | −0.093858 | −0.072847 | 0.165854 | −0.150999 | 0.14948 | −0.121536 | 0.14319 | 0.073472 | 0.064192 | −0.029019 | −0.040174 |
| 51 | −0.090448 | 0.265182 | 0.173789 | −0.022745 | −0.012632 | −0.121187 | 0.010015 | −0.01642 | 0.023025 | −0.127558 | 0.104292 | 0.054252 | −0.040755 | −0.030335 |
| 52 | 0.138767 | 0.1416 | −0.054818 | 0.019799 | −0.218337 | 0.116255 | −0.081799 | 0.004648 | 0.15008 | −0.11822 | −0.063754 | −0.10219 | 0.018931 | −0.135289 |
| 53 | −0.170834 | −0.019807 | 0.076488 | −0.015711 | 0.081003 | −0.016378 | −0.025641 | 0.165744 | −0.324584 | 0.080485 | −0.006931 | 0.117647 | −0.034527 | −0.212516 |
| 54 | −0.187771 | 0.016413 | 0.087679 | 0.035123 | 0.06838 | 0.290653 | 0.120826 | −0.030466 | −0.060118 | −0.078491 | 0.046099 | −0.529164 | 0.174049 | −0.137287 |
| 55 | 0.120822 | 0.059737 | 0.035375 | 0.111413 | −0.056243 | −0.137177 | −0.135112 | −0.064436 | −0.126371 | 0.160792 | 0.091476 | 0.165551 | −0.07202 | −0.050195 |
| 56 | −0.170467 | −0.276068 | −0.175766 | 0.144314 | −0.064862 | −0.022306 | 0.120451 | −0.03191 | 0.168876 | 0.070785 | −0.094712 | −0.039846 | 0.054294 | −0.01535 |
| 57 | −0.031434 | 0.137178 | 0.022751 | 0.129294 | 0.204868 | 0.086524 | −0.194567 | −0.071712 | 0.134553 | 0.355873 | 0.189785 | −0.117935 | −0.030398 | −0.017746 |
| 58 | 0.167587 | −0.074457 | −0.063577 | −0.055611 | −0.125835 | −0.14336 | 0.198192 | 0.06444 | −0.182129 | −0.320729 | −0.078871 | 0.05606 | −0.028285 | −0.015183 |
| 59 | 0.116141 | 0.230324 | 0.061533 | 0.053211 | 0.013159 | 0.006112 | 0.055414 | 0.019031 | −0.130553 | 0.187427 | 0.02536 | −0.113914 | 0.031181 | −0.0896 |
| 60 | −0.011489 | −0.109549 | 0.047166 | −0.059884 | 0.054885 | −0.011027 | −0.02065 | −0.041718 | 0.097612 | −0.087996 | −0.041364 | 0.075717 | −0.039536 | −0.041414 |

APPENDIX B4-continued

PCA Transformation Matrix (82 × 82 Normal/Diseased)

| | | | | | | | | | | | | | |
|---|---|---|---|---|---|---|---|---|---|---|---|---|---|
| 61 | −0.052116 | 0.047095 | −0.081327 | −0.099419 | −0.333871 | −0.228727 | −0.062498 | −0.084087 | −0.020222 | 0.045055 | 0.227642 | −0.048424 | 0.032589 | −0.381216 |
| 62 | 0.072777 | −0.002409 | −0.083769 | 0.04302 | −0.026779 | −0.12188 | −0.07366 | 0.025521 | −0.062566 | 0.146889 | −0.153055 | −0.215208 | 0.043388 | −0.148395 |
| 63 | −0.077974 | 0.02099 | 0.100014 | 0.064656 | 0.094926 | 0.102762 | 0.020881 | 0.030717 | −0.019948 | −0.017212 | −0.049472 | −0.048081 | 0.009161 | −0.112315 |
| 64 | 0.050498 | −0.109176 | −0.204901 | −0.037245 | −0.034322 | −0.008545 | −0.012536 | 0.118963 | 0.183234 | 0.024841 | 0.032845 | 0.422582 | −0.111479 | −0.234427 |
| 65 | 0.029605 | 0.045102 | −0.057468 | −0.038006 | −0.189884 | 0.069491 | 0.107026 | 0.053182 | −0.035905 | −0.072646 | −0.108163 | 0.014277 | 0.079686 | −0.013387 |
| 66 | 0.044664 | −0.008635 | −0.010079 | −0.006453 | 0.009567 | −0.011316 | 0.009875 | −0.02106 | −0.031807 | 0.016965 | 0.008907 | −0.003336 | 0.009831 | −0.019794 |
| 67 | 0.026969 | 0.091331 | 0.020431 | −0.014774 | −0.00925 | −0.007171 | 0.028712 | 0.021397 | 0.029524 | −0.122323 | −0.024263 | −0.066359 | 0.002127 | −0.003979 |
| 68 | −0.209 | 0.193446 | −0.064333 | −0.173453 | 0.063514 | 0.285318 | 0.239063 | 0.068633 | 0.136395 | −0.054361 | 0.276272 | 0.185326 | −0.086047 | −0.00165 |
| 69 | 0.09505 | −0.045321 | 0.196558 | 0.02896 | 0.059763 | −0.17049 | −0.132892 | −0.110578 | −0.032422 | −0.081459 | −0.196043 | 0.141274 | −0.015809 | −0.000824 |
| 70 | 0.169722 | −0.257097 | −0.08196 | 0.030346 | −0.063937 | 0.067566 | −0.060049 | −0.095721 | −0.060783 | 0.108259 | 0.271827 | −0.061866 | 0.090811 | −0.002171 |
| 71 | −0.112713 | −0.039353 | −0.021811 | 0.240602 | −0.148657 | −0.15292 | −0.147484 | 0.007557 | 0.009787 | 0.175609 | −0.368899 | −0.009283 | −0.012467 | −0.004563 |
| 72 | 0.066808 | 0.190636 | −0.018991 | −0.059305 | 0.063738 | −0.04084 | 0.156148 | 0.048192 | 0.008319 | −0.093214 | −0.008361 | −0.069897 | −0.020034 | −0.013958 |
| 73 | 0.111208 | 0.049985 | −0.04536 | 0.036418 | −0.006184 | 0.26013 | 0.069123 | −0.106145 | 0.247881 | 0.325656 | −0.09813 | 0.145241 | 0.019057 | −0.001796 |
| 74 | 0.082356 | −0.060292 | 0.088599 | 0.029982 | −0.059373 | 0.137261 | 0.038407 | −0.05342 | −0.12879 | 0.006677 | 0.130034 | 0.140869 | 0.036779 | −0.00028 |
| 75 | 0.061867 | 0.253165 | −0.268767 | 0.069747 | 0.002486 | −0.126781 | 0.089347 | 0.320441 | 0.090769 | 0.016705 | −0.024965 | −0.143366 | −0.065233 | −0.001757 |
| 76 | −0.048256 | 0.069772 | −0.027849 | −0.03042 | 0.273037 | −0.316988 | −0.229057 | 0.028031 | 0.029478 | −0.182929 | 0.148504 | −0.149243 | −0.015014 | −0.002325 |
| 77 | −0.134867 | −0.185418 | 0.263734 | −0.018003 | −0.203161 | 0.182384 | 0.085211 | −0.159409 | −0.215507 | 0.019414 | −0.062501 | 0.082977 | 0.020496 | −0.002358 |
| 78 | −0.209893 | −0.121766 | −0.039869 | −0.069344 | −0.069226 | 0.083444 | −0.096567 | 0.062875 | −0.084482 | −0.084916 | 0.096746 | 0.042798 | 0.024793 | −0.004138 |
| 79 | −0.002832 | −0.052667 | 0.005512 | −0.018483 | 0.082916 | 0.041015 | −0.049356 | 0.069814 | −0.175091 | −0.09423 | −0.060324 | −0.117395 | −0.00784 | −0.000388 |
| 80 | −0.280088 | −0.175741 | 0.104502 | −0.039673 | −0.064053 | −0.086038 | −0.260438 | −0.056201 | 0.22068 | 0.032297 | −0.008747 | −0.064688 | 0.000661 | −0.000452 |
| 81 | 0.394281 | 0.079958 | 0.047898 | −0.011935 | −0.003594 | 0.022358 | 0.202416 | −0.151312 | 0.002585 | −0.008746 | −0.065706 | −0.070059 | 0.028916 | −0.00096 |
| 82 | −0.06756 | 0.154829 | −0.06704 | 0.053024 | 0.124989 | −0.039091 | 0.11554 | 0.042181 | 0.017323 | 0.065771 | −0.003922 | 0.118842 | −0.004081 | −0.000495 |

APPENDIX B5

PCA Transformation
Matrix (82 x 82; Benign/Malignant)

| | A | B | C | D | E | F | G | H | I | J | K | L | M |
|---|---|---|---|---|---|---|---|---|---|---|---|---|---|
| 1 | 409.4/255.3>GPA:Lyso 16:0 | −0.115804 | 0.036866 | 0.190288 | −0.077558 | −0.103124 | −0.020264 | 0.034268 | −0.202573 | 0.007009 | 0.034879 | −0.074285 | 0.087505 |
| 2 | 437.4/283.3>GPA:Lyso 18:0 | −0.073104 | −0.149793 | 0.164443 | −0.040301 | −0.138671 | 0.046442 | −0.005097 | −0.091212 | 0.044323 | −0.078475 | 0.16843 | 0.110508 |
| 3 | 647.8/255.3>GPA:16:0/16:0 | −0.120462 | 0.077948 | 0.181466 | −0.075297 | −0.001039 | 0.088859 | 0.004857 | −0.095556 | −0.060154 | 0.02959 | −0.105386 | 0.068568 |
| 4 | 673.8/281.3>GPA:18:1/16:0 | −0.084439 | −0.013882 | 0.145826 | −0.101584 | 0.267739 | 0.210619 | 0.004397 | 0.124187 | −0.086317 | 0.071983 | −0.059266 | 0.005609 |
| 5 | 699.8/281.3>GPA:36:2 | −0.080003 | −0.016736 | 0.146945 | −0.082111 | 0.313563 | 0.182352 | 0.010055 | 0.13018 | −0.050576 | 0.022415 | −0.089773 | 0.011456 |
| 6 | 701.8/283.3>GPA:36:1 | −0.068051 | −0.012919 | 0.142283 | −0.109399 | 0.301919 | 0.211851 | −0.000735 | 0.127635 | −0.060527 | 0.090897 | −0.027749 | 0.037914 |
| 7 | 703.8/283.3>GPA:36:0 | −0.131326 | −0.084891 | 0.169082 | −0.062883 | 0.05923 | 0.122987 | 0.002582 | 0.000213 | −0.022285 | −0.002231 | 0.120293 | 0.068805 |
| 8 | 721.8/281.3>GPA:16:0/22:5 | −0.143672 | −0.109338 | 0.119264 | −0.029032 | −0.059127 | −0.008042 | 0.060473 | −0.017439 | 0.01857 | −0.118687 | 0.086151 | −0.122186 |
| 9 | 723.8/283.3>GPA:18:0/20:4 | −0.063071 | −0.003776 | 0.169469 | −0.042068 | 0.282979 | 0.160269 | 0.018137 | 0.07177 | −0.054298 | 0.0545 | 0.030494 | 0.127332 |
| 10 | 731.8/283.3>GPA:38:0 | −0.133751 | −0.088425 | 0.160192 | −0.077478 | −0.021825 | 0.131253 | 0.039929 | 0.033861 | −0.032421 | −0.012855 | −0.004045 | 0.001071 |
| 11 | 757.8/281.3>GPA:40:1 | −0.121096 | 0.011659 | 0.045474 | −0.078979 | 0.240893 | −0.09927 | −0.122863 | 0.055759 | 0.052087 | −0.165888 | −0.075319 | −0.024441 |
| 12 | 759.8/283.3>GPA:40:0 | −0.111225 | −0.014334 | 0.070589 | −0.109236 | 0.169359 | 0.24622 | −0.06672 | 0.067571 | 0.079328 | 0.206746 | 0.061918 | 0.018431 |
| 13 | 483.4/255.3>GPGro:Lyso 16:0 | −0.118273 | −0.081409 | 0.17009 | −0.025946 | −0.230708 | 0.02773 | 0.014837 | 0.055211 | −0.090173 | 0.01586 | −0.033126 | −0.085504 |
| 14 | 507.4/279.3>GPGro:Lyso 18:2 | −0.090743 | −0.071027 | 0.160956 | −0.08103 | −0.271364 | 0.047329 | 0.018055 | 0.107301 | −0.156182 | 0.026178 | −0.062445 | −0.071729 |
| 15 | 509.4/281.3>GPGro:Lyso 18:1 | −0.037456 | −0.094046 | 0.187132 | 0.003671 | −0.232289 | 0.069563 | −0.113387 | 0.178623 | 0.031392 | 0.070213 | −0.240019 | −0.011291 |
| 16 | 511.4/283.3>GPGro:Lyso 18:0 | −0.100083 | −0.126027 | 0.161488 | −0.030663 | −0.216164 | 0.015789 | 0.026086 | 0.081924 | −0.116519 | 0.003588 | 0.002135 | −0.13223 |
| 17 | 743.8/279.3>GPGro:18:2/16:1 | 0.012676 | 0.092832 | −0.220208 | 0.009716 | 0.118367 | −0.05035 | −0.068267 | 0.197642 | −0.197009 | 0.082559 | −0.196055 | −0.003578 |
| 18 | 769.8/279.3>GPGro:18:2/18:2 | 0.049876 | 0.069104 | −0.207645 | −0.164377 | −0.122231 | 0.143708 | −0.109361 | 0.107564 | 0.083218 | 0.131945 | −0.015819 | 0.048297 |
| 19 | 771.8/279.3>GPGro:18:2/18:1 | −0.000085 | 0.020332 | −0.087904 | −0.135037 | 0.222181 | −0.215894 | 0.21778 | 0.00505 | −0.118614 | −0.145871 | 0.004558 | 0.049761 |
| 20 | 773.8/279.3>GPGro:18:2/18:0 | −0.044287 | −0.163224 | 0.044698 | −0.117062 | −0.065187 | −0.072302 | 0.204984 | 0.163271 | −0.244948 | −0.096974 | 0.048943 | −0.056384 |
| 21 | 775.8/281.3>GPGro:18:1/18:0 | −0.04127 | −0.181142 | 0.149227 | 0.005898 | −0.122326 | 0.014301 | 0.142247 | 0.172056 | −0.028331 | −0.104295 | −0.068267 | −0.094496 |
| 22 | 777.8/283.3>GPGro:18:0/18:0 | −0.133566 | −0.126683 | 0.092927 | −0.061615 | −0.096055 | −0.03602 | 0.087327 | −0.016353 | 0.003228 | −0.09464 | 0.138252 | −0.127168 |
| 23 | 476.6/196.1>Lyso GPEtn:Lyso18:2a | 0.047003 | 0.042893 | −0.054623 | −0.303944 | −0.011687 | 0.096923 | −0.013846 | −0.159327 | 0.000645 | −0.207931 | 0.002625 | −0.109046 |
| 24 | 478.4/196.1>Lyso GPEtn:Lyso 18:1 | 0.017312 | 0.026458 | −0.09234 | −0.226326 | −0.034146 | 0.242498 | −0.163798 | −0.130491 | 0.192281 | −0.100684 | −0.025479 | −0.187912 |
| 25 | 480.4/196.1>Lyso GPEtn:Lyso 18:0 | −0.096099 | 0.025982 | −0.094248 | −0.043294 | −0.015833 | 0.252967 | −0.023831 | −0.115626 | 0.175071 | 0.144584 | −0.044847 | 0.071875 |
| 26 | 500.4/196.1>Lyso GPEtn:Lyso 20:4 | 0.084543 | 0.104938 | −0.04126 | −0.095886 | −0.064818 | 0.229163 | −0.179038 | −0.026108 | 0.117492 | −0.101779 | 0.115538 | −0.31159 |
| 27 | 524.4/196.1>Lyso GPEtn:Lyso 22:6 | 0.09432 | 0.143258 | −0.000925 | −0.075798 | −0.061317 | 0.160141 | −0.142357 | −0.007305 | 0.176584 | −0.018137 | −0.015515 | −0.260344 |
| 28 | 520.4/184.1>GPCho:Lyso 18:2 | −0.05199 | 0.108223 | −0.060229 | −0.25573 | −0.084307 | 0.016521 | 0.090956 | −0.149771 | −0.023146 | 0.012253 | −0.143502 | 0.22652 |
| 29 | 544.4/184.1>GPCho:Lyso 20:4 | 0.015253 | 0.210931 | 0.135657 | 0.01189 | −0.05828 | 0.052892 | 0.093578 | −0.121718 | 0.070382 | 0.02207 | 0.129941 | 0.109287 |
| 30 | 568.4/184.1>GPCho:Lyso 22:6 | 0.033445 | 0.197687 | 0.147064 | −0.073423 | −0.053519 | −0.081787 | 0.120133 | −0.066067 | 0.124541 | 0.116244 | −0.17151 | 0.061328 |
| 31 | 570.4/184.1>GPCho:Lyso 22:5 | 0.047111 | 0.178615 | 0.148446 | −0.106737 | −0.03494 | −0.060219 | 0.188308 | −0.092241 | 0.1474 | 0.031387 | −0.149261 | 0.041756 |
| 32 | 678.5/184.1>GPCho:28:0a | −0.099252 | −0.113613 | −0.032926 | −0.104635 | 0.053261 | −0.023572 | 0.051613 | 0.023606 | 0.286954 | 0.050999 | 0.060494 | −0.219586 |
| 33 | 704.6/184.1>GPCho:30:1a | −0.154288 | 0.095283 | −0.001522 | 0.052447 | 0.040543 | −0.076895 | −0.13245 | −0.102575 | −0.110244 | 0.009176 | −0.025894 | −0.141899 |
| 34 | 732.6/184.1>GPCho:32:1a | −0.109662 | −0.072652 | 0.022786 | 0.135472 | 0.076607 | 0.054532 | 0.073299 | −0.123088 | 0.15842 | −0.233368 | −0.247001 | −0.027364 |
| 35 | 734.6/184.1>GPCho:32:0a | −0.090785 | −0.077283 | 0.022096 | 0.227134 | 0.130929 | −0.065625 | −0.130447 | −0.019362 | 0.103994 | −0.220221 | −0.115231 | 0.006518 |
| 36 | 742.6/184.1>GPCho:34:2p, 34:3e | −0.061789 | −0.11954 | 0.050356 | −0.199962 | 0.078043 | −0.186729 | −0.04261 | −0.062981 | 0.056927 | 0.111583 | 0.018021 | −0.136745 |
| 37 | 744.6/184.1>GPCho:34:1p, 34:2e | 0.077649 | −0.0196 | −0.006817 | −0.297543 | 0.010533 | −0.133855 | −0.109478 | −0.037072 | −0.077505 | −0.172323 | 0.018796 | 0.011716 |
| 38 | 748.6/184.1>GPCho:34:0e | −0.076943 | −0.125434 | 0.034475 | −0.023799 | 0.118755 | −0.207432 | −0.251905 | 0.002736 | 0.148697 | −0.110468 | 0.110824 | 0.173088 |
| 39 | 756.6/184.1>GPCho:34:3a | −0.088669 | −0.211479 | −0.06835 | −0.060211 | −0.012656 | −0.01722 | −0.013986 | −0.010455 | 0.054268 | 0.018331 | −0.021558 | 0.047894 |
| 40 | 758.7/184.1>GPCho:34:2a | 0.057768 | −0.146824 | −0.146288 | 0.011061 | −0.089254 | 0.066453 | −0.113249 | 0.206877 | −0.184414 | −0.013593 | −0.246409 | 0.053569 |
| 41 | 762.6/184.1>GPCho:34:0a | −0.034017 | −0.150023 | 0.024662 | 0.148357 | 0.122034 | 0.010308 | 0.03588 | 0.021249 | 0.21296 | −0.347652 | −0.250648 | −0.044416 |
| 42 | 768.6/184.1>GPCho:36:3p, 36:4e | 0.121453 | 0.084894 | 0.187545 | −0.05081 | 0.020841 | −0.076741 | −0.175693 | 0.012229 | −0.010081 | −0.030557 | 0.057818 | −0.060404 |
| 43 | 770.6/184.1>GPCho:36:2p, 36:3e | 0.093503 | −0.028893 | 0.107059 | −0.257621 | 0.034227 | −0.132539 | −0.154521 | −0.026585 | −0.058568 | −0.099709 | 0.017956 | 0.015691 |
| 44 | 772.6/184.1>GPCho:36:1p, 36:2e | −0.013664 | −0.177154 | −0.044607 | −0.176604 | 0.014884 | −0.134653 | −0.149144 | −0.029688 | 0.080572 | −0.030559 | 0.167525 | 0.233602 |
| 45 | 782.6/184.1>GPCho:36:4a | 0.12604 | 0.049013 | 0.090783 | 0.205531 | 0.018094 | 0.106091 | 0.012688 | 0.074917 | −0.009156 | −0.065152 | 0.264077 | −0.02946 |
| 46 | 784.6/184.1>GPCho:36:3a | 0.139635 | −0.061683 | 0.017312 | −0.032091 | 0.02414 | 0.119775 | 0.186636 | 0.081093 | 0.091228 | −0.089299 | 0.129055 | 0.132636 |

APPENDIX B5-continued

PCA Transformation
Matrix (82 x 82; Benign/Malignant)

| | | | | | | | | | | | | | |
|---|---|---|---|---|---|---|---|---|---|---|---|---|---|
| 47 | 786.6/184.1>GPCho:36:2a | 0.08489 | −0.114107 | −0.147069 | −0.204085 | −0.060547 | 0.028849 | 0.109329 | 0.061199 | 0.052947 | −0.069797 | −0.05175 | 0.144961 |
| 48 | 788.6/184.1>GPCho:36:1a | −0.059992 | −0.191384 | −0.111294 | −0.077718 | 0.033847 | −0.046591 | 0.111304 | −0.045181 | 0.219591 | −0.01716 | −0.09904 | 0.000087 |
| 49 | 792.6/184.1>GPCho:38:5p, 38:6e | 0.085459 | 0.057513 | 0.192085 | −0.101454 | 0.041294 | −0.208031 | −0.095492 | 0.042218 | 0.12581 | 0.117068 | −0.202028 | −0.074747 |
| 50 | 794.6/184.1>GPCho:38:4p, 38:5e | 0.115752 | 0.086103 | 0.198096 | −0.031671 | −0.009184 | −0.110401 | −0.192561 | 0.030088 | −0.024793 | −0.04978 | −0.014943 | 0.046872 |
| 51 | 796.6/184.1>GPCho:38:3p, 38:4e | 0.108576 | 0.051391 | 0.200978 | −0.016808 | 0.026677 | −0.114279 | −0.223742 | 0.056669 | −0.00904 | −0.024937 | 0.203481 | 0.102564 |
| 52 | 808.6/184.1>GPCho:38:5a | 0.15109 | 0.064136 | 0.138053 | 0.033516 | 0.008324 | −0.038225 | 0.140645 | 0.096881 | 0.133774 | 0.014498 | 0.060686 | −0.021493 |
| 53 | 810.6/184.1>GPCho:38:4a | 0.14192 | 0.035031 | 0.103862 | 0.135698 | 0.027069 | 0.044677 | 0.109981 | 0.057251 | 0.058768 | −0.015891 | 0.325457 | 0.019926 |
| 54 | 814.6/184.1>GPCho:38:2a | −0.168061 | 0.01458 | 0.023281 | 0.080778 | 0.047353 | −0.108656 | −0.066927 | −0.13411 | −0.044696 | 0.089191 | 0.021736 | −0.099766 |
| 55 | 816.6/184.1>GPCho:38:1a | −0.140782 | −0.068615 | −0.069336 | −0.045149 | 0.007233 | −0.142146 | 0.024884 | −0.081202 | 0.006676 | 0.285196 | 0.074289 | −0.20262 |
| 56 | 820.6/184.1>GPCho:40:5p, 40:6e | 0.120444 | 0.072677 | 0.17492 | −0.058638 | 0.003734 | −0.187906 | −0.090772 | 0.051621 | 0.113316 | 0.106219 | −0.073865 | 0.044146 |
| 57 | 826.6/184.1>GPCho:40:2p, 40:3e | −0.0999 | −0.2025 | −0.034145 | 0.026501 | −0.014882 | −0.068992 | −0.096396 | 0.046036 | 0.141188 | 0.101885 | 0.07093 | 0.016359 |
| 58 | 828.6/184.1>GPCho:40:1p, 40:2e | −0.122261 | −0.151749 | −0.042384 | −0.001044 | −0.015252 | −0.076554 | −0.108916 | 0.146884 | 0.187789 | 0.069626 | 0.126139 | 0.086348 |
| 59 | 834.6/184.1>GPCho:40:6a | 0.129983 | 0.074804 | 0.145563 | 0.008561 | 0.037131 | −0.103612 | 0.161081 | 0.072239! | 0.162893 | 0.094545 | −0.151411 | −0.023243 |
| 60 | 836.6/184.1>GPCho:40:5a | 0.086836 | −0.056007 | 0.08484 | 0.076852 | 0.062332 | −0.152752 | 0.227051 | 0.126787 | 0.271234 | 0.204549 | −0.064965 | −0.169095 |
| 61 | 703.8/184.4>SM:d18:1/16:0 | −0.153721 | 0.103874 | 0.013524 | 0.045085 | 0.031154 | −0.089226 | −0.136476 | −0.083329 | −0.1424 | 0.034185 | −0.015708 | −0.10718 |
| 62 | 731.8/184.4>SM:d18:1/18:0 | −0.150283 | 0.055277 | −0.010158 | 0.151122 | 0.045114 | −0.008587 | −0.050561 | −0.154254 | −0.078536 | 0.093953 | −0.018156 | −0.011159 |
| 63 | 787.9/184.4>SM:d18:1/22:0 | −0.037966 | −0.041943 | −0.118533 | −0.242869 | 0.064219 | −0.108742 | 0.233629 | −0.128168 | −0.101829 | 0.188674 | 0.059126 | 0.039742 |
| 64 | 813.9/184.4>SM:d18:1/24:1 | −0.160759 | 0.05732 | 0.050806 | 0.07813 | 0.072064 | −0.087265 | −0.059831 | −0.1318 | −0.112361 | 0.082633 | 0.042546 | −0.105824 |
| 65 | 841.9/184.4>SM:d18:1/26:1 | −0.112644 | −0.167579 | −0.09379 | 0.05597 | 0.018917 | −0.029987 | −0.048333 | −0.015819 | 0.111428 | 0.254811 | 0.083199 | −0.028398 |
| 66 | 843.9/184.4>SM:d18:1/26:0 | 0.077411 | −0.114434 | 0.005143 | 0.058093 | −0.10669 | 0.053972 | −0.217583 | 0.11692 | 0.056407 | 0.253071 | −0.091384 | 0.200538 |
| 67 | 538.7/264.4>Cer:d18:1/16:0 | −0.131827 | 0.08056 | 0.088649 | −0.000591 | −0.193491 | −0.002652 | −0.047736 | −0.06645 | 0.082827 | −0.048378 | −0.029741 | 0.217741 |
| 68 | 566.7/264.4>Cer:d18:1/18:0 | −0.155767 | 0.047838 | 0.001359 | 0.114119 | −0.060362 | 0.046698 | −0.004451 | −0.151826 | 0.044704 | 0.015998 | −0.039656 | 0.163253 |
| 69 | 594.7/264.4>Cer:d18:1/20:0 | −0.165386 | 0.071428 | −0.020739 | 0.058171 | −0.043637 | 0.038345 | 0.017595 | −0.051578 | 0.0987 | −0.04138 | −0.003061 | 0.203119 |
| 70 | 622.8/264.4>Cer:d18:1/22:0 | −0.161543 | 0.094158 | −0.01582 | 0.002204 | −0.033005 | 0.024961 | 0.098219 | 0.010481 | 0.086027 | −0.052809 | 0.091481 | 0.11237 |
| 71 | 648.9/264.4>Cer:d18:1/24:1 | −0.173225 | 0.060161 | 0.035752 | 0.056679 | −0.042026 | 0.012362 | 0.015606 | −0.064319 | 0.048258 | −0.062783 | −0.003543 | 0.072984 |
| 72 | 650.9/264.4>Cer:d18:1/24:0 | −0.137401 | 0.122163 | −0.029801 | −0.042195 | 0.051825 | −0.004891 | 0.152443 | 0.036543 | 0.014461 | −0.020823 | 0.151547 | −0.125706 |
| 73 | 700.7/264.4>MonoHexCer:d18:1/16:0 | −0.128333 | 0.144003 | −0.069931 | −0.021664 | −0.039722 | −0.021156 | −0.024894 | 0.230197 | 0.086046 | −0.076519 | 0.022099 | 0.098171 |
| 74 | 728.7/264.4>MonoHexCer:d18:1/18:0 | −0.163082 | 0.108849 | 0.001724 | −0.000675 | −0.000922 | −0.019017 | −0.022233 | 0.011177 | −0.034964 | −0.054021 | −0.040571 | −0.050981 |
| 75 | 784.8/264.4>MonoHexCer:d18:1/22:0 | −0.126082 | 0.154886 | −0.07689 | −0.067744 | −0.043425 | −0.043977 | 0.004459 | 0.220546 | 0.05529 | −0.045538 | 0.057348 | −0.027549 |
| 76 | 810.9/264.4>MonoHexCer:d18:1/24:1 | −0.146268 | 0.141974 | −0.025458 | −0.004951 | −0.035028 | −0.054458 | −0.015134 | 0.16461 | 0.03533 | −0.069606 | −0.025457 | 0.052833 |
| 77 | 812.9/264.4>MonoHexCer:d18:1/24:0 | −0.110929 | 0.156001 | −0.073779 | −0.059277 | −0.073033 | −0.054626 | 0.008158 | 0.26491 | 0.086597 | −0.047137 | 0.04659 | −0.003708 |
| 78 | 862.7/264.4>DiHexCer:d18:1/16:0 | −0.143347 | 0.14521 | −0.054401 | −0.006723 | −0.023289 | −0.055453 | −0.020089 | 0.146302 | 0.036288 | −0.022489 | 0.008858 | −0.077534 |
| 79 | 890.7/264.4>DiHexCer:d18:1/18:0 | −0.14289 | 0.138144 | −0.051237 | −0.016802 | −0.03494 | −0.019055 | 0.015658 | 0.165947 | 0.065188 | −0.032286 | 0.085591 | 0.105184 |
| 80 | 946.8/264.4>DiHexCer:d18:1/22:0 | −0.141482 | 0.148477 | −0.046266 | −0.056936 | −0.031934 | −0.053765 | 0.0155 | 0.150457 | 0.034381 | −0.005794 | 0.047752 | −0.053017 |
| 81 | 972.9/264.4>DiHexCer:d18:1/24:1 | −0.152406 | 0.130954 | −0.010727 | −0.010645 | −0.009513 | −0.073488 | −0.019662 | 0.082235 | 0.003582 | −0.042136 | −0.043889 | −0.071704 |
| 82 | 974.9/264.4>DiHexCer:d18:1/24:0 | −0.132608 | 0.15275 | −0.043904 | −0.0597 | −0.033342 | −0.073255 | 0.02452 | 0.184977 | 0.038167 | −0.032157 | 0.069307 | 0.02325 |

| | N | O | P | Q | R | S | T | U | V | W | X | Y | Z | AA |
|---|---|---|---|---|---|---|---|---|---|---|---|---|---|---|
| 1 | −0.15083 | 0.01665 | −0.236671 | 0.155521 | −0.092429 | 0.126787 | −0.016593 | 0.152693 | −0.008054 | 0.105365 | −0.1216 | 0.099226 | −0.050561 | 0.06236 |
| 2 | 0.058562 | −0.168492 | 0.00353 | 0.125461 | −0.134875 | 0.333729 | 0.192438 | 0.096096 | 0.050637 | −0.027895 | 0.037061 | −0.121827 | −0.174828 | 0.038498 |
| 3 | −0.225699 | 0.09703 | −0.210982 | −0.024603 | −0.086359 | 0.081575 | −0.119523 | 0.178049 | 0.02146 | −0.069487 | −0.12467 | −0.00505 | −0.045311 | 0.226546 |
| 4 | −0.066528 | −0.046699 | −0.022232 | −0.084444 | −0.005992 | 0.014118 | −0.034597 | 0.070442 | −0.04144 | −0.082442 | 0.056191 | −0.031268 | −0.017225 | 0.243763 |
| 5 | −0.032717 | −0.011198 | −0.030841 | −0.034263 | 0.051506 | −0.007422 | −0.006218 | 0.03369 | −0.043543 | −0.102171 | 0.045134 | −0.02497 | 0.049219 | 0.152114 |
| 6 | 0.050598 | −0.073566 | 0.035661 | −0.092268 | 0.033098 | 0.02724 | 0.010163 | −0.01192 | −0.022667 | −0.062401 | 0.005074 | −0.087084 | 0.052775 | 0.046636 |
| 7 | 0.121886 | −0.046303 | −0.010501 | 0.103883 | −0.125275 | 0.198016 | 0.127426 | −0.017878 | 0.02599 | 0.016863 | 0.068983 | 0.09219 | −0.134564 | 0.062921 |
| 8 | 0.092847 | −0.071617 | −0.031336 | 0.075694 | 0.119618 | 0.07379 | −0.003326 | −0.049146 | −0.05152 | −0.25409 | −0.019904 | 0.16059 | −0.039568 | −0.205548 |
| 9 | 0.147181 | 0.037334 | 0.062255 | 0.04697 | −0.058208 | 0.079903 | 0.02661 | 0.123971 | 0.147666 | 0.476889 | −0.042735 | 0.041516 | 0.17659 | −0.41921 |
| 10 | 0.141747 | 0.029537 | 0.028033 | 0.009689 | 0.135236 | −0.125049 | −0.093994 | −0.174816 | 0.054676 | −0.078133 | −0.178232 | −0.162748 | −0.031904 | 0.018864 |
| 11 | −0.012897 | 0.188152 | −0.085323 | 0.114355 | 0.037007 | −0.046736 | −0.21135 | −0.125279 | −0.250599 | −0.297204 | 0.012007 | −0.107321 | 0.038073 | −0.177783 |

APPENDIX B5-continued

PCA Transformation
Matrix (82 x 82; Benign/Malignant)

| | | | | | | | | | | | | | | |
|---|---|---|---|---|---|---|---|---|---|---|---|---|---|---|
| 12 | 0.002709 | −0.008403 | 0.141266 | −0.198867 | −0.046477 | −0.043944 | 0.027072 | −0.088124 | −0.116741 | −0.008694 | 0.059621 | 0.055681 | −0.139017 | −0.100941 |
| 13 | 0.019635 | 0.051467 | −0.051276 | −0.177546 | 0.009659 | −0.116263 | −0.131501 | −0.068273 | −0.052054 | 0.061608 | 0.015359 | −0.057696 | 0.034944 | 0.012217 |
| 14 | −0.020853 | 0.049506 | 0.010284 | −0.056739 | 0.015661 | −0.196251 | −0.067691 | −0.194104 | 0.03096 | 0.15342 | 0.038158 | 0.056054 | 0.000171 | 0.036916 |
| 15 | −0.096633 | 0.188339 | −0.086044 | 0.086642 | 0.046109 | −0.070399 | 0.191059 | −0.157273 | −0.176415 | 0.184595 | 0.116892 | 0.08754 | −0.066454 | −0.108448 |
| 16 | 0.062742 | −0.037051 | 0.06755 | −0.114086 | 0.026998 | −0.13513 | −0.110226 | −0.115277 | −0.001712 | 0.006826 | 0.026131 | −0.050721 | 0.130106 | 0.006173 |
| 17 | 0.086882 | −0.061038 | −0.279927 | 0.203076 | −0.002915 | −0.165451 | 0.103906 | −0.01854 | −0.039273 | −0.009369 | 0.174376 | 0.058281 | −0.379543 | −0.028297 |
| 18 | −0.080397 | 0.03491 | 0.16701 | −0.157557 | −0.106651 | −0.109413 | 0.056902 | −0.075352 | −0.023836 | −0.13711 | −0.005536 | −0.16536 | −0.285713 | −0.136834 |
| 19 | 0.177221 | 0.365179 | −0.072588 | 0.280901 | 0.058257 | −0.08709 | 0.10285 | −0.009627 | −0.214012 | 0.089104 | −0.064427 | 0.022375 | 0.026616 | 0.060769 |
| 20 | 0.026528 | 0.03786 | 0.19133 | 0.194507 | −0.155067 | −0.067416 | 0.078226 | 0.112568 | −0.039729 | −0.02742 | 0.14787 | −0.071999 | −0.030428 | 0.212311 |
| 21 | −0.127383 | −0.049722 | 0.10179 | 0.193002 | −0.120299 | −0.024925 | 0.164144 | 0.156426 | 0.003283 | −0.056402 | 0.065726 | −0.011945 | −0.122753 | −0.056105 |
| 22 | 0.095169 | −0.008313 | 0.115772 | 0.071904 | 0.080561 | 0.063834 | 0.029164 | −0.042523 | −0.015001 | −0.280783 | 0.018271 | 0.16526 | 0.09451 | −0.232353 |
| 23 | −0.039118 | 0.029972 | −0.123526 | 0.19639 | −0.044242 | 0.037444 | −0.030528 | −0.188878 | 0.110858 | 0.107561 | 0.016124 | −0.055316 | 0.050566 | 0.139049 |
| 24 | −0.102724 | 0.08437 | 0.126419 | 0.22691 | −0.009622 | 0.110198 | −0.111351 | −0.069228 | −0.00697 | 0.0843 | 0.180984 | 0.009205 | 0.041848 | 0.020789 |
| 25 | −0.124151 | −0.004228 | 0.242236 | 0.44948 | −0.049422 | −0.156626 | −0.112653 | −0.106252 | 0.194401 | −0.082928 | −0.096312 | 0.022329 | −0.065401 | −0.03152 |
| 26 | 0.223232 | 0.097723 | −0.058543 | −0.057579 | 0.037243 | −0.018564 | 0.042849 | 0.248578 | −0.07248 | 0.006888 | 0.014554 | 0.029454 | 0.038327 | 0.072743 |
| 27 | 0.297717 | 0.035608 | −0.067239 | −0.033857 | −0.048054 | 0.008232 | 0.106426 | 0.139388 | −0.088281 | −0.023714 | 0.110494 | 0.107583 | 0.024388 | 0.036533 |
| 28 | −0.068374 | −0.279009 | 0.025671 | 0.071234 | 0.172764 | −0.125483 | −0.035028 | −0.129655 | −0.050492 | 0.044898 | −0.013259 | 0.063764 | 0.087212 | −0.11265 |
| 29 | −0.14645 | −0.105477 | −0.083783 | 0.037108 | 0.03695 | −0.200141 | 0.028379 | 0.050496 | −0.298121 | 0.128442 | 0.147723 | 0.000909 | 0.078439 | 0.019911 |
| 30 | 0.105546 | −0.159459 | −0.025616 | −0.003091 | −0.068804 | 0.020816 | −0.056816 | 0.052072 | −0.091255 | −0.069309 | 0.098102 | 0.073319 | 0.080182 | −0.028171 |
| 31 | 0.017424 | −0.108306 | −0.001381 | −0.014514 | −0.02734 | 0.019224 | −0.131222 | −0.032413 | −0.087763 | 0.016762 | 0.214696 | 0.039681 | −0.007392 | 0.028363 |
| 32 | 0.0066 | −0.027916 | −0.244957 | −0.06713 | −0.063786 | −0.100503 | 0.288437 | −0.259951 | −0.108192 | 0.160927 | −0.481147 | 0.02898 | 0.063396 | 0.182025 |
| 33 | −0.019709 | −0.126099 | 0.065996 | 0.083347 | −0.062431 | 0.077614 | 0.067832 | −0.091915 | −0.036802 | −0.026687 | −0.071085 | −0.207833 | −0.1654 | 0.003018 |
| 34 | −0.167502 | 0.036723 | −0.066804 | −0.167529 | −0.26407 | −0.171458 | 0.278191 | −0.009227 | 0.156075 | −0.127855 | −0.002653 | 0.136358 | 0.115922 | −0.06987 |
| 35 | 0.025317 | −0.149032 | 0.183629 | 0.076449 | 0.018631 | 0.034949 | 0.064595 | −0.067563 | −0.211018 | 0.184537 | 0.010236 | −0.017856 | −0.20838 | 0.074722 |
| 36 | 0.078513 | −0.157858 | −0.223101 | 0.042238 | −0.066161 | −0.303664 | 0.044157 | 0.243794 | 0.109312 | −0.01609 | 0.130236 | −0.272038 | 0.109398 | −0.169386 |
| 37 | 0.002983 | −0.0152 | −0.094276 | −0.150195 | −0.073584 | −0.018252 | 0.050258 | −0.087188 | 0.256868 | 0.059109 | 0.092794 | −0.292517 | −0.050292 | −0.070885 |
| 38 | −0.030782 | −0.098462 | 0.056109 | −0.120275 | −0.139655 | −0.009999 | −0.014398 | −0.249204 | −0.101258 | −0.022658 | 0.066305 | 0.137481 | −0.041094 | 0.09212 |
| 39 | −0.026319 | 0.000103 | −0.067624 | −0.000497 | 0.041696 | −0.196963 | −0.199253 | 0.287583 | −0.118256 | −0.060464 | −0.028451 | 0.145854 | −0.16449 | 0.045467 |
| 40 | 0.172259 | −0.104308 | −0.073857 | −0.01754 | 0.057672 | 0.167541 | −0.137151 | 0.020418 | 0.140036 | 0.034952 | −0.087035 | 0.192619 | 0.091126 | 0.120627 |
| 41 | −0.098463 | −0.12004 | −0.039451 | −0.089179 | 0.207509 | 0.034751 | −0.0348 | −0.004339 | 0.118988 | 0.137649 | 0.220619 | −0.081803 | 0.008072 | −0.031463 |
| 42 | −0.125127 | 0.0642 | 0.143511 | 0.004203 | 0.244077 | −0.093925 | 0.177322 | 0.1076431 | 0.045847 | 0.089824 | −0.031862 | 0.021829 | −0.129599 | −0.044455 |
| 43 | −0.160601 | 0.07881 | 0.001664 | −0.080047 | 0.152577 | 0.014751 | 0.011531 | 0.0871141 | 0.215661 | −0.014822 | −0.019223 | 0.004955 | −0.115924 | −0.10775 |
| 44 | 0.154005 | 0.02029 | −0.093838 | −0.046865 | −0.246829 | −0.020503 | −0.207707 | −0.099193 | −0.047713 | 0.019153 | 0.173065 | 0.095797 | −0.02594 | 0.036592 |
| 45 | −0.047189 | −0.028044 | −0.145323 | 0.054517 | −0.088866 | −0.145953 | −0.017211 | −0.076238 | −0.023101 | 0.068401 | 0.125072 | −0.044962 | −0.058344 | −0.033414 |
| 46 | −0.19527 | 0.110699 | −0.221848 | −0.06211 | 0.055267 | 0.000534 | −0.050079 | 0.035975 | 0.131956 | −0.125685 | −0.256982 | 0.084459 | −0.253327 | −0.208105 |
| 47 | 0.09394 | 0.174381 | 0.22465 | −0.059404 | −0.010448 | 0.107322 | 0.059861 | 0.073795 | −0.100929 | −0.01631 | −0.124571 | −0.079295 | 0.093317 | 0.054951 |
| 48 | −0.166815 | 0.12238 | 0.132653 | −0.131381 | 0.124738 | 0.012163 | 0.069122 | 0.144571 | −0.077621 | −0.023061 | 0.190638 | −0.005161 | 0.064365 | 0.101972 |
| 49 | 0.143182 | −0.038885 | 0.124192 | 0.071068 | 0.088928 | −0.096095 | 0.113521 | 0.152758 | 0.064735 | −0.10943 | −0.158026 | 0.073875 | −0.062647 | −0.022346 |
| 50 | −0.095778 | 0.145297 | 0.182403 | 0.029839 | 0.116086 | −0.049058 | 0.036732 | 0.029247 | −0.03671 | 0.101247 | −0.035008 | 0.055757 | −0.040671 | 0.049007 |
| 51 | −0.137262 | 0.021682 | 0.067001 | 0.038107 | 0.133928 | −0.066958 | 0.049812 | −0.023322 | 0.099245 | −0.058151 | −0.025081 | 0.158813 | 0.077469 | 0.249712 |
| 52 | 0.040898 | 0.034573 | −0.060278 | −0.018538 | −0.136267 | −0.008267 | −0.105269 | −0.089567 | 0.065113 | −0.051034 | 0.106319 | −0.061156 | −0.083355 | −0.018231 |
| 53 | −0.076952 | 0.127479 | 0.042692 | 0.040608 | −0.066417 | −0.11389 | 0.005731 | −0.003136 | −0.074472 | −0.044556 | 0.080121 | −0.087387 | 0.055067 | 0.000282 |
| 54 | −0.042988 | 0.104815 | 0.012962 | 0.009657 | 0.083065 | 0.126466 | −0.060044 | 0.008865 | −0.025646 | −0.045249 | −0.011496 | −0.030128 | 0.088437 | −0.113797 |
| 55 | −0.137095 | −0.031258 | −0.012551 | −0.092227 | 0.090931 | 0.170724 | 0.023696 | 0.090031 | −0.079358 | −0.003019 | 0.081192 | 0.132874 | −0.114245 | −0.005683 |
| 56 | 0.155194 | 0.000558 | 0.05348 | 0.001941 | −0.105632 | 0.03053 | −0.065974 | −0.09139 | 0.127925 | −0.066576 | −0.02278 | 0.183986 | −0.005797 | 0.114823 |
| 57 | 0.027453 | −0.013939 | −0.025198 | 0.104514 | 0.031964 | −0.03737 | −0.130787 | 0.16628 | 0.05728 | 0.15056 | −0.001539 | −0.009116 | 0.018304 | 0.038085 |
| 58 | 0.073181 | −0.096261 | −0.046294 | 0.080744 | −0.055021 | −0.071317 | −0.029238 | 0.069072 | 0.038094 | 0.094238 | −0.011505 | 0.054451 | 0.047883 | −0.048076 |
| 59 | 0.147962 | −0.002168 | 0.083111 | 0.058902 | −0.15598 | 0.048341 | 0.030021 | −0.093156 | 0.036081 | −0.074079 | −0.090297 | 0.006738 | −0.111246 | −0.092868 |
| 60 | −0.008422 | 0.122701 | 0.043524 | 0.068815 | 0.072917 | 0.150074 | −0.183876 | −0.119054 | 0.18135 | 0.105695 | 0.047867 | −0.291617 | −0.04762 | 0.154264 |
| 61 | −0.038367 | −0.098488 | 0.058892 | 0.027037 | −0.044723 | 0.034236 | 0.043827 | −0.069627 | −0.055106 | 0.010807 | −0.072538 | −0.210733 | −0.014448 | 0.011638 |

APPENDIX B5-continued

PCA Transformation
Matrix (82 x 82; Benign/Malignant)

| | | | | | | | | | | | | | | |
|---|---|---|---|---|---|---|---|---|---|---|---|---|---|---|
| 62 | 0.072991 | 0.084481 | 0.050804 | 0.006184 | −0.133535 | −0.21579 | 0.154455 | −0.011951 | 0.259958 | −0.082711 | 0.093446 | 0.031669 | 0.055319 | 0.145635 |
| 63 | −0.055365 | 0.058537 | 0.137107 | −0.179189 | −0.008118 | 0.050497 | 0.277385 | −0.098293 | −0.047073 | 0.112692 | 0.124952 | 0.091638 | −0.013251 | 0.003234 |
| 64 | −0.000076 | 0.074563 | 0.022691 | 0.013023 | 0.001902 | 0.077243 | −0.030524 | −0.052076 | 0.006881 | −0.00626 | −0.020344 | 0.003998 | 0.099418 | −0.15271 |
| 65 | −0.096541 | 0.082 | −0.000774 | 0.102146 | 0.093172 | −0.106446 | −0.111423 | 0.046194 | 0.033676 | 0.100812 | −0.000727 | −0.040869 | −0.03475 | 0.050388 |
| 66 | −0.073595 | 0.203916 | −0.280368 | 0.147297 | 0.112554 | 0.248652 | 0.288181 | −0.151919 | −0.016308 | −0.19652 | 0.222061 | −0.131059 | 0.262146 | −0.068119 |
| 67 | 0.155245 | 0.085465 | −0.090322 | −0.113365 | 0.042303 | 0.107353 | 0.006528 | 0.112314 | −0.181491 | 0.016173 | −0.117653 | −0.339097 | −0.147839 | 0.022662 |
| 68 | 0.19004 | 0.22953 | 0.050321 | −0.062801 | −0.028796 | −0.100042 | 0.078477 | 0.048967 | 0.162831 | 0.021782 | 0.079411 | −0.010055 | −0.10651 | 0.068515 |
| 69 | 0.159777 | 0.134831 | 0.027478 | −0.045133 | 0.114778 | −0.112322 | 0.07972 | 0.071848 | 0.131683 | −0.035674 | 0.057988 | −0.049982 | −0.076684 | 0.000782 |
| 70 | 0.156655 | −0.027228 | −0.01454 | −0.023984 | 0.323272 | −0.028816 | 0.094369 | −0.053012 | 0.09569 | −0.032799 | 0.077347 | 0.004093 | −0.061615 | 0.105918 |
| 71 | 0.15943 | 0.151737 | −0.012974 | −0.030176 | 0.13064 | −0.014178 | −0.062456 | −0.030923 | −0.004007 | 0.03807 | 0.008361 | −0.011708 | −0.083814 | −0.008992 |
| 72 | 0.057362 | −0.047966 | −0.155787 | −0.015938 | 0.292854 | 0.099317 | −0.007094 | −0.165733 | 0.188448 | 0.039013 | 0.155548 | 0.163915 | −0.202912 | 0.080361 |
| 73 | −0.036031 | −0.162676 | 0.070369 | 0.059272 | 0.041158 | −0.018128 | 0.056531 | 0.061331 | −0.012243 | −0.038022 | −0.116731 | −0.120437 | 0.142468 | 0.042645 |
| 74 | −0.019146 | 0.218928 | 0.002214 | −0.012966 | −0.189301 | 0.008295 | −0.079202 | −0.039989 | 0.140773 | 0.064244 | 0.025365 | 0.132088 | −0.032947 | −0.008803 |
| 75 | −0.042653 | −0.012012 | −0.012553 | −0.011595 | −0.023076 | 0.060355 | −0.007837 | 0.04156 | −0.016145 | 0.075203 | −0.005477 | 0.044645 | −0.020507 | −0.013389 |
| 76 | −0.038938 | 0.106822 | 0.057299 | −0.005904 | −0.100118 | 0.054179 | −0.113019 | 0.038077 | −0.050873 | 0.10896 | −0.041314 | 0.03056 | 0.067621 | −0.066302 |
| 77 | −0.079153 | −0.088888 | −0.006827 | 0.001267 | −0.034434 | 0.072318 | 0.051539 | 0.041748 | −0.009541 | 0.13158 | −0.032962 | 0.010475 | −0.031289 | −0.098193 |
| 78 | −0.078631 | 0.02559 | 0.042668 | −0.083176 | −0.099 | 0.086189 | −0.023106 | 0.077031 | 0.056856 | −0.037401 | 0.027088 | −0.028347 | −0.014124 | 0.038768 |
| 79 | 0.002614 | −0.078931 | −0.002428 | 0.094891 | 0.040061 | −0.101265 | 0.112986 | 0.017055 | 0.107576 | −0.117146 | −0.004703 | 0.004861 | 0.225463 | 0.099981 |
| 80 | −0.08387 | 0.081281 | −0.050188 | −0.032781 | −0.060072 | 0.055053 | 0.011 | 0.000095 | 0.059007 | −0.007418 | 0.089772 | 0.078444 | −0.003146 | −0.069189 |
| 81 | −0.109396 | 0.201597 | 0.029953 | −0.081407 | −0.14846 | 0.056013 | −0.109976 | 0.039422 | 0.009556 | −0.020547 | 0.016569 | 0.04826 | −0.005774 | −0.020649 |
| 82 | −0.113745 | −0.084117 | −0.00782 | 0.044231 | 0.007885 | 0.024732 | 0.03849 | 0.061814 | 0.075446 | −0.063993 | 0.028943 | −0.048722 | 0.134936 | 0.043496 |

| | AB | AC | AD | AE | AF | AG | AH | AI | AJ | AK | AL | AM | AN | AO |
|---|---|---|---|---|---|---|---|---|---|---|---|---|---|---|
| 1 | −0.011919 | 0.021192 | −0.018657 | 0.152101 | −0.069473 | 0.124866 | −0.092824 | 0.012448 | −0.152932 | 0.119552 | −0.09735 | 0.190948 | −0.124084 | 0.047184 |
| 2 | 0.046472 | 0.20331 | 0.271214 | −0.069056 | −0.123345 | −0.231721 | 0.134919 | −0.182547 | 0.004753 | 0.161439 | 0.021362 | −0.007094 | −0.039809 | 0.112433 |
| 3 | −0.091742 | −0.157871 | 0.10412 | 0.208252 | 0.110735 | 0.151909 | −0.162965 | 0.074292 | −0.13101 | −0.010102 | −0.035842 | −0.112945 | 0.005248 | 0.003649 |
| 4 | 0.047017 | 0.006678 | −0.141899 | −0.001191 | −0.093031 | −0.007331 | −0.028019 | −0.029341 | 0.069936 | 0.035511 | 0.051726 | −0.052297 | 0.185944 | 0.050636 |
| 5 | −0.016295 | −0.00451 | −0.119281 | −0.038204 | 0 | −0.001244 | −0.028849 | −0.047011 | 0.184014 | 0.041137 | −0.059252 | −0.036895 | 0.116353 | 0.081818 |
| 6 | 0.03067 | 0.028084 | −0.044101 | −0.094726 | 0.01032 | −0.030129 | −0.003407 | −0.044239 | 0.137968 | 0.116134 | −0.0648 | 0.238201 | −0.06662 | 0.119218 |
| 7 | 0.094098 | 0.212293 | 0.225169 | −0.040963 | 0.178088 | −0.055459 | −0.04411 | 0.098366 | −0.060825 | −0.186567 | 0.122755 | 0.176958 | 0.146835 | −0.194634 |
| 8 | −0.09029 | −0.372872 | −0.011442 | 0.078973 | 0.064919 | 0.010169 | −0.044652 | −0.063689 | −0.022515 | 0.100002 | −0.01009 | 0.184614 | 0.049842 | −0.027964 |
| 9 | −0.0733 | −0.184701 | 0.148903 | −0.130741 | −0.022459 | 0.114637 | −0.12675 | 0.084861 | −0.137316 | 0.08056 | −0.099144 | −0.212977 | 0.044733 | −0.039087 |
| 10 | −0.056809 | 0.081582 | 0.16214 | 0.06253 | 0.071251 | −0.216156 | −0.024979 | −0.003924 | 0.232486 | 0.139999 | −0.038243 | −0.29896 | −0.161626 | −0.071144 |
| 11 | 0.062492 | 0.089817 | 0.175174 | 0.150115 | −0.227581 | 0.207312 | 0.135391 | −0.213471 | −0.202352 | 0.06022 | 0.130435 | −0.04254 | −0.119874 | 0.067425 |
| 12 | −0.007197 | −0.107187 | −0.050216 | 0.091905 | 0.008495 | −0.072312 | 0.230007 | 0.00729 | −0.225748 | −0.293591 | 0.162215 | 0.195734 | −0.228941 | −0.073074 |
| 13 | 0.07939 | −0.012605 | 0.032768 | −0.137224 | 0.062047 | 0.166756 | −0.032448 | −0.104626 | −0.066745 | −0.000549 | −0.085961 | 0.005038 | −0.088069 | 0.020267 |
| 14 | 0.095771 | 0.170839 | 0.009261 | −0.041141 | −0.095981 | 0.02096 | −0.004218 | 0.128896 | 0.005953 | −0.082835 | 0.117732 | 0.096339 | −0.023844 | −0.064562 |
| 15 | −0.037025 | 0.110539 | 0.015473 | 0.169187 | −0.174156 | 0.027433 | −0.053189 | 0.127119 | 0.201295 | 0.157023 | 0.113623 | 0.107529 | 0.216196 | 0.091861 |
| 16 | 0.035608 | −0.007683 | 0.103703 | −0.148918 | −0.019678 | 0.071044 | −0.09228 | 0.000277 | −0.047299 | −0.036665 | −0.057902 | −0.13981 | −0.077492 | −0.014372 |
| 17 | 0.179473 | −0.184565 | 0.11724 | 0.011141 | 0.231275 | −0.11511 | −0.173826 | 0.011344 | −0.049557 | 0.041632 | 0.112496 | −0.146488 | 0.02342 | −0.065324 |
| 18 | 0.067533 | −0.073767 | 0.236256 | −0.094985 | −0.035728 | 0.044561 | 0.039037 | −0.050899 | −0.166947 | 0.087864 | −0.354955 | −0.051671 | 0.160542 | 0.061936 |
| 19 | −0.048037 | 0.073563 | 0.134395 | −0.072452 | −0.082169 | −0.096842 | −0.021188 | −0.013549 | 0.12309 | −0.045292 | −0.115728 | 0.050744 | −0.123554 | 0.042044 |
| 20 | 0.144067 | −0.110918 | 0.003557 | −0.082886 | 0.096664 | 0.017635 | 0.029126 | 0.024781 | −0.144676 | −0.153204 | −0.178293 | −0.080227 | −0.164573 | 0.058304 |
| 21 | −0.003074 | −0.050449 | −0.293268 | 0.233588 | 0.050591 | 0.059182 | 0.118449 | −0.03978 | 0.048097 | −0.043308 | −0.047521 | −0.127877 | 0.041342 | 0.025218 |
| 22 | −0.136561 | −0.252642 | −0.011644 | 0.005445 | 0.082789 | −0.007618 | −0.149297 | 0.036779 | 0.016248 | −0.014529 | 0.008503 | 0.026352 | 0.095275 | 0.082719 |
| 23 | 0.255913 | −0.220452 | −0.182334 | −0.353996 | −0.076627 | 0.169735 | 0.181742 | 0.083809 | −0.079742 | 0.154375 | 0.073635 | 0.103095 | 0.101104 | −0.079042 |
| 24 | −0.009187 | −0.014262 | −0.084704 | −0.030142 | 0.154105 | −0.150765 | 0.1693 | 0.02803 | −0.003814 | 0.098073 | 0.043696 | −0.138153 | −0.021984 | 0.218706 |
| 25 | −0.128345 | 0.207383 | −0.107376 | 0.01346 | −0.001773 | 0.15346 | −0.288374 | −0.187344 | 0.017667 | −0.06577 | −0.071056 | −0.070388 | −0.092627 | −0.17151 |
| 26 | 0.023894 | −0.00098 | 0.082745 | 0.082577 | −0.018814 | 0.004803 | −0.226795 | 0.127288 | 0.082383 | 0.00612 | 0.030865 | −0.038172 | −0.106208 | −0.09899 |

APPENDIX B5-continued

PCA Transformation
Matrix (82 x 82; Benign/Malignant)

| | | | | | | | | | | | | | | |
|---|---|---|---|---|---|---|---|---|---|---|---|---|---|---|
| 27 | 0.152346 | 0.056094 | −0.019735 | 0.128601 | −0.070179 | 0.045009 | −0.123162 | 0.047341 | 0.041609 | −0.108866 | −0.069354 | 0.008829 | −0.187839 | 0.039729 |
| 28 | −0.006366 | −0.077098 | 0.100471 | 0.013918 | 0.111962 | −0.239391 | −0.02552 | 0.115372 | 0.112005 | 0.01068 | 0.070518 | 0.172207 | −0.13462 | 0.202109 |
| 29 | −0.08324 | −0.031316 | 0.155165 | 0.009743 | 0.224177 | 0.136907 | 0.093883 | −0.12041 | 0.075983 | −0.032246 | 0.068749 | −0.054701 | 0.055224 | 0.082983 |
| 30 | 0.136316 | 0.015498 | 0.127114 | −0.002366 | 0.025368 | 0.158881 | 0.177945 | −0.08282 | 0.064401 | −0.118258 | −0.028742 | −0.129481 | −0.006045 | −0.167846 |
| 31 | −0.023195 | −0.08551 | −0.006077 | −0.030472 | −0.197048 | −0.207151 | −0.105648 | 0.028187 | −0.034695 | −0.244337 | −0.22062 | −0.102667 | 0.063588 | −0.007152 |
| 32 | −0.081055 | −0.077508 | 0.003736 | 0.000531 | 0.137169 | −0.086155 | 0.014844 | −0.188698 | −0.082132 | −0.083195 | −0.10443 | −0.076131 | 0.161291 | 0.015348 |
| 33 | −0.076774 | −0.083507 | 0.075429 | 0.054371 | −0.172644 | −0.034636 | 0.027963 | 0.191403 | 0.11413 | −0.030105 | −0.039948 | −0.099814 | 0.050018 | −0.127414 |
| 34 | 0.060605 | 0.014828 | 0.125883 | −0.184937 | −0.164021 | −0.115015 | −0.057298 | −0.007793 | −0.046724 | −0.002062 | 0.034485 | −0.008698 | −0.23722 | −0.059879 |
| 35 | −0.155561 | 0.021108 | −0.070807 | −0.19986 | −0.033879 | 0.282863 | −0.093355 | 0.034465 | 0.023902 | −0.232593 | −0.051722 | 0.051916 | −0.10467 | 0.114196 |
| 36 | −0.224538 | 0.242723 | −0.154374 | 0.048189 | 0.062072 | −0.110399 | 0.156481 | 0.158812 | −0.256149 | 0.05473 | −0.042956 | −0.028882 | −0.00448 | 0.074797 |
| 37 | −0.026021 | 0.00758 | 0.044917 | 0.13601 | 0.11061 | 0.174366 | −0.215594 | −0.288283 | 0.143422 | −0.194285 | −0.018729 | 0.21445 | 0.057783 | −0.014784 |
| 38 | 0.062651 | 0.08915 | −0.074357 | 0.058155 | 0.207778 | 0.032593 | −0.216474 | 0.310828 | −0.164696 | 0.125903 | 0.017061 | −0.133129 | −0.116694 | 0.180264 |
| 39 | −0.058209 | −0.02771 | −0.020111 | −0.262296 | −0.070645 | −0.157477 | −0.085057 | −0.008939 | −0.084268 | 0.085485 | −0.020861 | 0.192953 | 0.038312 | −0.271118 |
| 40 | −0.180603 | 0.043131 | −0.042826 | −0.020905 | 0.044433 | 0.026319 | 0.05665 | −0.187696 | −0.177658 | 0.045606 | 0.057817 | −0.05507 | −0.071472 | 0.117495 |
| 41 | 0.123103 | 0.010417 | 0.033414 | 0.116967 | 0.133036 | −0.082548 | 0.022442 | −0.099619 | 0.085163 | 0.060765 | −0.165157 | −0.042211 | −0.06138 | −0.176166 |
| 42 | −0.064978 | −0.110602 | −0.009167 | −0.076922 | 0.187477 | −0.037919 | 0.05214 | −0.121849 | −0.023008 | 0.025546 | 0.012023 | 0.07459 | −0.09177 | −0.082873 |
| 43 | 0.018744 | 0.04097 | −0.002402 | −0.019944 | −0.098418 | 0.008088 | −0.142249 | −0.00045 | 0.050065 | −0.147977 | 0.234995 | −0.11972 | 0.000358 | −0.029078 |
| 44 | −0.134188 | −0.051887 | −0.058603 | −0.004803 | −0.019883 | 0.018849 | −0.027999 | −0.014937 | 0.219767 | −0.026682 | −0.054467 | 0.021559 | 0.077044 | −0.10134 |
| 45 | −0.003531 | 0.004535 | −0.012793 | −0.000914 | 0.068737 | 0.054523 | 0.102756 | −0.232973 | 0.019501 | 0.052844 | −0.02569 | 0.080521 | −0.036152 | 0.00613 |
| 46 | 0.208053 | 0.026048 | −0.050118 | −0.053186 | −0.009173 | 0.086447 | 0.143156 | 0.294818 | 0.15139 | −0.201903 | −0.095852 | −0.082991 | −0.080481 | 0.144823 |
| 47 | −0.03828 | 0.090491 | 0.118199 | 0.169075 | 0.051986 | 0.080988 | 0.023363 | 0.080868 | −0.04334 | −0.070812 | −0.002926 | 0.027594 | 0.101618 | 0.027761 |
| 48 | −0.051751 | −0.054905 | 0.11203 | −0.037194 | 0.000369 | 0.012758 | −0.037076 | 0.015516 | −0.039402 | 0.035585 | 0.099898 | −0.084245 | 0.313259 | −0.122449 |
| 49 | −0.047235 | 0.120602 | −0.084353 | −0.196897 | 0.07086 | 0.11465 | 0.097059 | 0.072284 | 0.138698 | −0.053963 | −0.054564 | 0.111656 | 0.035891 | 0.139009 |
| 50 | 0.023198 | −0.024315 | 0.120257 | −0.037524 | −0.127863 | −0.120055 | 0.023673 | −0.066489 | −0.220516 | 0.107394 | −0.078394 | 0.072107 | 0.074317 | −0.020045 |
| 51 | 0.077927 | −0.069697 | −0.001211 | 0.116917 | −0.014626 | −0.158925 | 0.05828 | −0.029083 | −0.069749 | −0.010179 | −0.089135 | −0.168251 | −0.085565 | −0.095932 |
| 52 | −0.043611 | −0.033294 | −0.155407 | −0.069156 | −0.199085 | −0.168185 | −0.225879 | −0.001026 | −0.059057 | 0.079718 | −0.109966 | 0.048676 | 0.123342 | 0.083476 |
| 53 | −0.113247 | 0.04914 | −0.039639 | −0.095596 | 0.014181 | 0.003681 | −0.148842 | 0.052278 | 0.029985 | 0.078975 | 0.105294 | −0.018637 | −0.003701 | −0.042122 |
| 54 | 0.289876 | 0.085726 | −0.005273 | −0.041937 | 0.080624 | −0.051105 | −0.059156 | −0.057538 | 0.049555 | −0.133487 | −0.079408 | 0.036945 | 0.148827 | 0.058547 |
| 55 | 0.075776 | 0.053043 | 0.039031 | −0.232485 | 0.013965 | 0.055904 | −0.148746 | −0.21987 | 0.066092 | −0.005025 | 0.041334 | −0.141961 | −0.084112 | 0.198532 |
| 56 | 0.013952 | −0.102184 | 0.032097 | −0.003643 | −0.032327 | 0.024963 | 0.091418 | −0.09059 | 0.126649 | 0.081705 | −0.134629 | −0.064869 | 0.005268 | −0.0283 |
| 57 | 0.090674 | −0.164317 | 0.071331 | 0.075802 | −0.114395 | 0.09008 | 0.172185 | −0.007182 | 0.101442 | −0.082032 | 0.002693 | −0.038603 | −0.07272 | −0.020835 |
| 58 | 0.241529 | −0.095934 | 0.027632 | 0.065403 | −0.124276 | 0.09151 | 0.117802 | 0.017584 | 0.170103 | 0.028924 | 0.04329 | −0.061696 | 0.052228 | 0.012273 |
| 59 | 0.077077 | 0.052928 | −0.074807 | −0.034254 | 0.151958 | 0.089467 | 0.000157 | −0.044984 | −0.074472 | 0.224163 | 0.269113 | −0.050166 | 0.002312 | −0.21151 |
| 60 | 0.020678 | −0.144972 | 0.148708 | 0.077918 | 0.070799 | −0.051969 | −0.087565 | 0.122975 | −0.112768 | −0.058664 | 0.193648 | 0.164645 | −0.128602 | 0.134236 |
| 61 | −0.104474 | −0.11841 | −0.050496 | 0.047714 | −0.153867 | 0.017388 | 0.08606 | 0.197688 | 0.008499 | −0.076013 | −0.02979 | −0.073235 | 0.09583 | −0.121112 |
| 62 | 0.022556 | −0.156814 | 0.11628 | 0.031187 | −0.087383 | 0.019231 | 0.033122 | 0.01691 | 0.041239 | 0.082655 | 0.042116 | 0.124586 | 0.006522 | 0.193953 |
| 63 | 0.05958 | −0.005754 | −0.233382 | 0.187977 | −0.090106 | 0.107363 | −0.01095 | −0.069668 | 0.072484 | 0.213176 | −0.000784 | −0.078748 | −0.264423 | −0.195238 |
| 64 | 0.312123 | 0.153649 | −0.155833 | 0.032262 | 0.075677 | −0.100908 | −0.079547 | −0.046796 | −0.033749 | 0.027377 | −0.08167 | 0.017445 | 0.082304 | −0.032282 |
| 65 | 0.065317 | −0.0493 | 0.044417 | 0.015858 | −0.022778 | −0.049233 | −0.021824 | −0.018755 | 0.104789 | 0.027689 | −0.032087 | 0.098066 | −0.09026 | −0.051748 |
| 66 | −0.11685 | −0.065389 | −0.07271 | −0.168436 | 0.054466 | −0.005453 | 0.005534 | 0.052318 | −0.029506 | −0.156448 | −0.196908 | 0.003503 | −0.152928 | −0.134885 |
| 67 | −0.013216 | −0.155625 | −0.251967 | −0.204903 | 0.016106 | −0.056122 | −0.064958 | −0.082821 | 0.043813 | 0.058603 | 0.197379 | −0.115051 | −0.151918 | −0.063399 |
| 68 | 0.008333 | −0.028389 | −0.058869 | 0.015615 | 0.094317 | 0.048919 | −0.001921 | −0.038654 | −0.018798 | 0.024223 | −0.009354 | −0.015783 | 0.082262 | 0.247594 |
| 69 | 0.04215 | −0.119287 | −0.057781 | 0.085588 | −0.048306 | 0.036811 | 0.024918 | −0.084278 | −0.006312 | 0.0159 | −0.010466 | 0.001107 | −0.010004 | 0.150697 |
| 70 | −0.014858 | 0.040685 | −0.09311 | −0.077855 | −0.119439 | 0.076661 | 0.032498 | 0.077298 | −0.131057 | 0.015492 | 0.037646 | −0.045542 | 0.037064 | −0.028406 |
| 71 | 0.073004 | 0.157572 | −0.142086 | 0.082705 | 0.206008 | −0.066434 | 0.11954 | 0.053154 | −0.108842 | −0.019347 | −0.125196 | −0.049398 | 0.134126 | −0.128407 |
| 72 | −0.200177 | 0.155508 | 0.062787 | 0.028051 | −0.110812 | 0.161861 | 0.082084 | 0.055151 | −0.091296 | 0.024902 | −0.192854 | 0.01982 | −0.01587 | −0.067026 |
| 73 | 0.109717 | −0.022523 | −0.022961 | 0.001582 | −0.066647 | −0.02498 | −0.052794 | 0.003292 | 0.051394 | 0.017381 | 0.01217 | 0.148554 | −0.052014 | −0.140566 |
| 74 | −0.213236 | −0.083446 | −0.046634 | −0.019172 | 0.016928 | −0.254201 | 0.158508 | −0.125163 | 0.114358 | −0.306708 | 0.168721 | −0.051227 | 0.038858 | −0.069712 |
| 75 | −0.086187 | 0.017189 | −0.080082 | 0.057028 | −0.164589 | −0.111747 | −0.028774 | −0.098276 | −0.070773 | −0.022543 | 0.053426 | −0.004792 | −0.112088 | 0.077356 |
| 76 | 0.146242 | −0.03065 | −0.113998 | 0.042098 | 0.083359 | −0.150836 | −0.070572 | −0.00046 | −0.093546 | −0.001571 | −0.091584 | 0.083658 | −0.047938 | −0.006084 |

APPENDIX B5-continued

PCA Transformation
Matrix (82 x 82; Benign/Malignant)

| | | | | | | | | | | | | | | |
|---|---|---|---|---|---|---|---|---|---|---|---|---|---|---|
| 77 | 0.031481 | 0.031519 | −0.113677 | 0.064802 | −0.097501 | −0.083503 | −0.098091 | −0.135049 | −0.017399 | 0.01577 | −0.092331 | 0.056134 | 0.058578 | 0.103152 |
| 78 | −0.13549 | −0.062589 | 0.148799 | 0.007973 | 0.130026 | 0.089181 | 0.067973 | 0.194107 | 0.158645 | 0.251979 | −0.111817 | 0.178486 | −0.145512 | −0.164889 |
| 79 | 0.104932 | 0.043732 | 0.048083 | −0.000552 | 0.024726 | 0.100148 | −0.073147 | −0.021329 | −0.123713 | −0.099518 | 0.142614 | 0.046584 | 0.167753 | −0.077571 |
| 80 | −0.132173 | 0.077246 | 0.075824 | −0.148346 | −0.019117 | 0.058158 | 0.099517 | 0.018657 | 0.010869 | 0.050911 | 0.224058 | −0.205418 | 0.023838 | 0.050368 |
| 81 | −0.112098 | 0.118858 | −0.008722 | −0.114916 | 0.254059 | 0.035484 | 0.151161 | 0.02835 | 0.136343 | 0.089812 | −0.16015 | 0.1023 | −0.026421 | −0.034158 |
| 82 | 0.010294 | 0.053907 | 0.054905 | −0.140191 | 0.073443 | 0.041562 | −0.094574 | 0.073873 | 0.107607 | −0.039879 | 0.040973 | −0.099302 | −0.054001 | 0.110523 |
| | AP | AQ | AR | AS | AT | AU | AV | AW | AX | AY | AZ | BA | BB | BC |
| 1 | −0.035528 | 0.213023 | −0.073775 | 0.048422 | −0.085349 | 0.241054 | −0.11462 | 0.321692 | −0.164962 | 0.166718 | −0.281427 | 0.002538 | −0.108055 | 0.000664 |
| 2 | 0.061286 | −0.050748 | 0.062951 | −0.021134 | 0.095243 | 0.087713 | 0.114056 | −0.094208 | 0.173421 | 0.06399 | 0.032141 | −0.048799 | −0.012229 | −0.270635 |
| 3 | 0.192493 | 0.051322 | 0.097874 | 0.029308 | 0.091295 | −0.136581 | 0.048669 | −0.121207 | 0.142955 | −0.007388 | 0.125736 | 0.024447 | 0.100519 | −0.01063 |
| 4 | −0.096172 | −0.140106 | 0.189981 | 0.018851 | 0.025127 | 0.021589 | −0.117442 | −0.014989 | 0.051328 | 0.308356 | 0.038269 | 0.036229 | −0.115014 | 0.141917 |
| 5 | −0.041835 | −0.015948 | 0.008473 | 0.035848 | 0.065143 | 0.176737 | 0.045838 | −0.058039 | −0.000643 | −0.034914 | −0.183166 | 0.095161 | −0.120191 | 0.066462 |
| 6 | −0.045953 | 0.013177 | −0.013378 | 0.034063 | −0.072832 | −0.027732 | −0.070814 | −0.051972 | −0.057103 | −0.202861 | 0.062292 | −0.010058 | −0.026225 | −0.208236 |
| 7 | 0.103205 | 0.093165 | 0.005444 | −0.155649 | 0.036998 | −0.077571 | 0.095726 | −0.015338 | −0.190821 | −0.255681 | −0.024161 | 0.041036 | −0.006576 | 0.368413 |
| 8 | −0.012021 | 0.082329 | 0.215148 | −0.003032 | −0.006746 | −0.116686 | −0.115611 | −0.025196 | 0.073235 | −0.056628 | 0.035437 | 0.144731 | 0.005189 | −0.028482 |
| 9 | −0.135204 | 0.017014 | −0.131019 | 0.046128 | −0.014106 | −0.054139 | 0.04124 | 0.037242 | 0.012738 | 0.017914 | 0.011307 | −0.011929 | 0.083351 | 0.002865 |
| 10 | 0.269916 | 0.068172 | 0.002731 | −0.104156 | −0.283556 | −0.041825 | −0.1216 | 0.093649 | −0.125155 | 0.093565 | 0.113148 | 0.10033 | 0.086379 | 0.013829 |
| 11 | −0.085005 | 0.024224 | −0.173224 | −0.056579 | 0.091515 | 0.044258 | 0.145808 | −0.034014 | −0.09774 | −0.081415 | −0.036227 | 0.118581 | 0.081528 | −0.052961 |
| 12 | 0.097084 | 0.001784 | −0.027566 | −0.008387 | −0.0631 | −0.062868 | 0.020602 | 0.198908 | 0.164015 | 0.033993 | −0.06437 | −0.262136 | 0.122799 | −0.156428 |
| 13 | 0.119148 | 0.049979 | 0.032757 | −0.020265 | 0.092894 | −0.020955 | 0.023251 | 0.006591 | 0.011022 | −0.089637 | 0.00106 | −0.144925 | −0.197952 | 0.035033 |
| 14 | −0.120016 | 0.038281 | 0.006886 | 0.017585 | 0.023312 | −0.159912 | −0.167399 | −0.057455 | 0.043474 | 0.031805 | −0.225431 | 0.138536 | 0.032536 | −0.113943 |
| 15 | −0.08793 | −0.046146 | −0.006745 | 0.030483 | −0.03103 | −0.005003 | 0.064457 | 0.040591 | −0.033634 | 0.07787 | 0.312079 | −0.156089 | 0.092861 | −0.073421 |
| 16 | 0.146201 | −0.063347 | −0.085658 | −0.094355 | 0.17908 | 0.216781 | 0.052992 | 0.022148 | 0.078432 | −0.066067 | −0.08093 | −0.07758 | −0.073354 | 0.125666 |
| 17 | 0.019206 | −0.063135 | 0.069164 | −0.198873 | 0.124342 | −0.051108 | 0.046413 | 0.138221 | −0.002376 | 0.033318 | −0.119506 | −0.011084 | −0.074635 | −0.089449 |
| 18 | −0.081897 | 0.12511 | 0.111996 | 0.079256 | −0.189257 | 0.251834 | −0.002427 | 0.06687 | −0.135232 | 0.017979 | 0.008848 | 0.015786 | −0.027805 | 0.154324 |
| 19 | 0.108396 | 0.002837 | 0.110117 | 0.105463 | −0.094127 | 0.004669 | −0.095249 | 0.002453 | 0.058759 | −0.047345 | −0.027652 | −0.308076 | 0.057503 | 0.073332 |
| 20 | −0.124306 | −0.007703 | −0.159663 | 0.248892 | 0.076775 | −0.079465 | 0.052524 | −0.022178 | 0.008483 | 0.220536 | 0.098885 | 0.135424 | −0.028834 | −0.141878 |
| 21 | −0.127563 | −0.015935 | −0.125129 | −0.024177 | −0.301974 | −0.002906 | 0.126501 | −0.047127 | −0.022271 | −0.286758 | −0.126316 | 0.006216 | 0.187634 | 0.176382 |
| 22 | −0.02194 | −0.087448 | 0.111114 | −0.061741 | 0.058654 | 0.097853 | −0.046714 | 0.041715 | −0.043076 | 0.164764 | −0.000688 | −0.168432 | −0.102141 | 0.014744 |
| 23 | 0.147705 | −0.071238 | 0.079004 | −0.07115 | −0.279303 | 0.003312 | 0.152761 | 0.052049 | 0.074724 | −0.088322 | 0.106898 | −0.012675 | −0.087921 | −0.033366 |
| 24 | 0.030252 | 0.012417 | −0.113687 | −0.044184 | 0.272896 | −0.028597 | −0.253089 | 0.019761 | −0.186211 | 0.099332 | −0.078314 | −0.054665 | 0.221656 | 0.124386 |
| 25 | −0.043217 | −0.105599 | 0.056453 | 0.013586 | 0.106151 | −0.132024 | 0.083758 | 0.004306 | 0.14325 | −0.048199 | 0.090878 | −0.097261 | −0.113769 | −0.062373 |
| 26 | 0.066105 | 0.065957 | −0.045086 | 0.060066 | −0.077509 | 0.082846 | −0.094944 | −0.069787 | 0.01473 | −0.01126 | −0.078626 | 0.091072 | 0.03056 | −0.024063 |
| 27 | −0.185916 | 0.031283 | 0.043547 | 0.017962 | −0.018958 | −0.000694 | 0.161595 | −0.046449 | 0.102834 | −0.073138 | 0.124442 | 0.030046 | −0.112385 | −0.025007 |
| 28 | −0.191723 | 0.037571 | −0.092513 | 0.086399 | −0.045251 | −0.017526 | 0.128118 | −0.133937 | 0.037419 | −0.015001 | −0.116957 | 0.1366 | −0.141593 | 0.05381 |
| 29 | 0.098322 | −0.250752 | −0.035905 | −0.05616 | −0.031563 | 0.171052 | 0.012697 | 0.128765 | 0.055455 | −0.183336 | 0.106582 | 0.116785 | −0.044221 | −0.053192 |
| 30 | −0.002294 | 0.003528 | 0.032371 | 0.09303 | −0.180285 | −0.071347 | −0.063686 | −0.159458 | 0.010266 | 0.199332 | 0.053244 | −0.017274 | 0.118612 | 0.045803 |
| 31 | 0.045384 | 0.026492 | 0.149994 | −0.134276 | −0.011682 | −0.049217 | −0.00058 | −0.165915 | −0.212995 | −0.026986 | −0.071313 | −0.177037 | 0.100534 | −0.106862 |
| 32 | −0.141711 | 0.036002 | −0.142301 | −0.070656 | 0.079777 | −0.034545 | 0.122753 | −0.161318 | 0.002309 | 0.044665 | −0.066041 | 0.005096 | 0.019194 | −0.069403 |
| 33 | −0.026265 | −0.00871 | −0.101445 | 0.061696 | 0.022538 | −0.081358 | −0.158771 | 0.138979 | 0.121589 | −0.084715 | −0.068001 | 0.10393 | −0.029381 | −0.080751 |
| 34 | −0.085024 | −0.279968 | 0.211691 | −0.043764 | −0.029026 | −0.026061 | 0.005174 | 0.162682 | −0.014765 | 0.113289 | −0.030395 | 0.134796 | 0.124637 | 0.106735 |
| 35 | 0.0146 | 0.096686 | 0.062556 | −0.299364 | −0.08657 | 0.073306 | −0.232601 | −0.115763 | −0.119889 | 0.039214 | 0.006522 | 0.099387 | −0.140415 | −0.07626 |
| 36 | −0.016946 | −0.030534 | 0.101203 | −0.137712 | −0.024471 | −0.103099 | −0.141051 | −0.012182 | −0.039356 | −0.063235 | 0.143984 | 0.019714 | −0.182844 | 0.020944 |
| 37 | −0.019076 | −0.104025 | 0.026319 | 0.110579 | −0.011387 | −0.047377 | −0.18565 | −0.004773 | −0.03683 | −0.045215 | −0.136192 | −0.042225 | 0.239602 | −0.019352 |
| 38 | 0.126822 | −0.062189 | 0.071021 | 0.358372 | −0.068733 | 0.008941 | 0.065969 | −0.089697 | −0.011078 | −0.077296 | 0.044823 | −0.102306 | 0.027828 | 0.035166 |
| 39 | −0.033891 | 0.020708 | −0.237658 | 0.019157 | 0.034045 | 0.211259 | −0.134214 | −0.07556 | 0.109125 | −0.086826 | 0.184582 | 0.002599 | 0.183899 | 0.027627 |
| 40 | 0.019954 | −0.059218 | 0.12641 | −0.061415 | −0.115809 | 0.021863 | 0.069419 | 0.00591 | −0.120531 | −0.052856 | 0.019484 | −0.055552 | 0.187071 | −0.022664 |
| 41 | −0.002746 | 0.276833 | −0.067181 | 0.128632 | 0.040937 | 0.019026 | 0.081348 | 0.143284 | 0.099937 | −0.042585 | 0.107385 | −0.087551 | −0.180945 | 0.006063 |

APPENDIX B5-continued

PCA Transformation
Matrix (82 x 82; Benign/Malignant)

| | | | | | | | | | | | | | | |
|---|---|---|---|---|---|---|---|---|---|---|---|---|---|---|
| 42 | 0.051341 | 0.077407 | 0.125226 | 0.090953 | −0.009948 | 0.050949 | 0.057609 | −0.031977 | −0.034599 | 0.092206 | 0.118189 | 0.140987 | 0.098381 | −0.137781 |
| 43 | 0.014654 | −0.090193 | −0.115052 | −0.15031 | −0.061333 | 0.121792 | 0.17723 | −0.146931 | −0.026491 | 0.101963 | −0.04646 | −0.039685 | −0.158129 | −0.109657 |
| 44 | −0.141454 | 0.109348 | −0.117842 | −0.142065 | −0.061532 | −0.029789 | 0.083438 | 0.086721 | 0.184965 | 0.293658 | 0.108568 | 0.132318 | 0.046257 | 0.099766 |
| 45 | 0.03393 | 0.073122 | −0.021137 | 0.049377 | 0.163544 | −0.118488 | −0.031432 | −0.040881 | 0.010513 | 0.207384 | −0.042373 | −0.124288 | −0.044107 | 0.177205 |
| 46 | 0.006007 | 0.029881 | −0.071757 | −0.042582 | 0.124246 | −0.070454 | −0.17677 | −0.053754 | −0.010544 | −0.059964 | 0.134076 | −0.029605 | −0.038123 | −0.012863 |
| 47 | −0.072512 | −0.067139 | 0.097811 | −0.036846 | 0.031377 | −0.049112 | −0.036021 | 0.159781 | 0.024383 | −0.031488 | −0.010933 | 0.077722 | −0.274607 | −0.07114 |
| 48 | 0.163631 | −0.030024 | −0.11913 | 0.067126 | 0.005862 | −0.182777 | −0.071073 | 0.048804 | 0.05791 | −0.052958 | −0.204664 | −0.085516 | −0.01441 | −0.110719 |
| 49 | 0.273236 | 0.029555 | −0.014415 | 0.113526 | 0.191774 | −0.007877 | 0.236405 | 0.247762 | −0.005872 | 0.148867 | −0.101257 | 0.001252 | 0.098898 | 0.112265 |
| 50 | −0.130401 | −0.032989 | 0.144588 | −0.058312 | 0.143531 | −0.15938 | −0.103108 | −0.210998 | 0.062074 | −0.075847 | 0.025131 | 0.097018 | −0.069662 | 0.248727 |
| 51 | −0.179169 | 0.005751 | −0.062661 | −0.175931 | −0.168332 | −0.002473 | −0.105497 | 0.106158 | −0.051814 | −0.014691 | −0.034398 | −0.191108 | −0.038592 | −0.03829 |
| 52 | 0.087651 | 0.127157 | −0.04726 | −0.00599 | 0.107278 | −0.053711 | 0.196632 | 0.013162 | −0.181794 | −0.093518 | −0.054309 | 0.023477 | 0.016947 | −0.213285 |
| 53 | −0.00015 | −0.074262 | 0.085769 | −0.014689 | −0.165432 | 0.009466 | 0.121586 | 0.139934 | −0.075723 | −0.007673 | −0.152959 | 0.13727 | 0.050597 | −0.042116 |
| 54 | −0.051831 | −0.079015 | 0.011923 | −0.022883 | −0.077255 | −0.071481 | 0.028633 | 0.038638 | 0.020245 | 0.018968 | 0.090603 | 0.040506 | 0.090734 | 0.165737 |
| 55 | −0.08022 | −0.04265 | −0.201078 | 0.012967 | −0.17886 | −0.19117 | −0.03051 | 0.077227 | −0.132109 | −0.000666 | 0.109635 | 0.028571 | −0.033402 | −0.024259 |
| 56 | −0.064584 | −0.078472 | −0.079509 | −0.036334 | 0.098912 | −0.104589 | −0.115959 | 0.287205 | 0.121148 | −0.307786 | 0.008684 | 0.101043 | −0.097153 | −0.021686 |
| 57 | 0.028909 | −0.119543 | 0.230322 | −0.000013 | 0.032982 | 0.035781 | 0.035309 | −0.102987 | −0.128899 | 0.002063 | −0.103541 | −0.062338 | −0.062139 | −0.111901 |
| 58 | 0.074859 | −0.071943 | 0.111705 | 0.042545 | 0.111941 | 0.067318 | −0.099785 | 0.002494 | −0.092288 | −0.042431 | −0.082091 | 0.074854 | 0.024271 | −0.022661 |
| 59 | 0.001196 | −0.014627 | −0.097298 | 0.125054 | −0.104845 | 0.178735 | −0.263207 | −0.311382 | 0.056627 | 0.060913 | −0.100802 | −0.055958 | −0.102493 | −0.017968 |
| 60 | −0.112784 | −0.031921 | 0.02374 | −0.13105 | −0.036184 | 0.135269 | 0.005381 | 0.100135 | 0.111181 | 0.080478 | 0.179082 | 0.092611 | 0.056432 | 0.136821 |
| 61 | 0.065564 | 0.03772 | 0.00092 | 0.037634 | 0.033885 | 0.098101 | 0.156855 | −0.047235 | 0.06397 | 0.03476 | 0.096376 | −0.049783 | 0.109312 | 0.039466 |
| 62 | 0.021488 | 0.087904 | −0.153025 | 0.049798 | −0.002251 | −0.00509 | −0.159394 | −0.086218 | 0.017674 | −0.106485 | 0.012931 | −0.11887 | −0.005258 | −0.035328 |
| 63 | 0.09906 | 0.150628 | 0.1203 | −0.20434 | 0.265274 | 0.137321 | 0.008906 | −0.024675 | −0.10518 | −0.055129 | 0.140215 | 0.107618 | 0.056713 | 0.076195 |
| 64 | −0.022799 | 0.021996 | 0.014255 | −0.021097 | −0.022021 | 0.062317 | −0.022136 | 0.0167 | 0.034752 | 0.051693 | −0.053169 | −0.097039 | −0.100912 | −0.073954 |
| 65 | −0.019825 | 0.084734 | 0.252128 | 0.155327 | −0.124082 | −0.002963 | 0.130101 | −0.112863 | −0.041039 | −0.064591 | −0.191348 | 0.044953 | 0.006546 | 0.03657 |
| 66 | 0.112199 | −0.018448 | −0.101046 | 0.032614 | −0.017162 | 0.054486 | −0.098388 | −0.116677 | 0.058959 | 0.006536 | −0.068161 | 0.123936 | −0.077556 | −0.000928 |
| 67 | −0.272242 | −0.08379 | 0.097193 | 0.165769 | 0.122376 | −0.161473 | −0.03335 | 0.134113 | −0.139422 | −0.126045 | 0.045679 | −0.169191 | −0.009589 | 0.110219 |
| 68 | 0.04589 | 0.015216 | −0.100817 | −0.113141 | −0.047165 | 0.010153 | −0.035486 | −0.051098 | −0.020016 | 0.028735 | 0.008247 | 0.127366 | 0.07139 | −0.083509 |
| 69 | 0.119959 | −0.002605 | −0.105217 | −0.098358 | −0.05249 | −0.045617 | 0.147544 | −0.226826 | 0.072986 | 0.049604 | 0.001175 | −0.023611 | −0.082345 | 0.158721 |
| 70 | −0.064778 | 0.075411 | −0.087894 | −0.068216 | −0.008282 | 0.003339 | 0.026036 | 0.083624 | 0.136176 | 0.026242 | −0.136263 | 0.003078 | 0.121568 | −0.003523 |
| 71 | −0.136168 | −0.168893 | 0.092323 | −0.021616 | 0.025401 | 0.137843 | 0.060362 | 0.053785 | 0.010652 | 0.105234 | −0.138755 | 0.064316 | 0.045196 | −0.134002 |
| 72 | −0.066292 | −0.277213 | 0.0134 | 0.256344 | 0.028416 | 0.008181 | −0.028826 | −0.018258 | −0.096033 | −0.025298 | 0.070694 | 0.101966 | 0.040397 | 0.033675 |
| 73 | 0.103966 | 0.03228 | −0.120146 | 0.014942 | 0.07299 | −0.154014 | 0.061686 | −0.007961 | −0.202682 | 0.117974 | 0.014722 | 0.147769 | 0.088803 | 0.0355 |
| 74 | 0.0131 | 0.016157 | −0.022783 | 0.253802 | 0.040863 | 0.296242 | 0.026425 | −0.002343 | −0.181934 | −0.100689 | 0.135437 | 0.081679 | −0.231711 | 0.022622 |
| 75 | 0.147197 | 0.024391 | −0.08131 | −0.012597 | −0.172756 | −0.123125 | −0.00961 | 0.043081 | 0.157232 | 0.054797 | −0.070201 | −0.020138 | −0.192142 | 0.280611 |
| 76 | 0.181987 | −0.176167 | −0.063684 | −0.070586 | 0.038072 | 0.006064 | −0.052868 | −0.039934 | −0.017494 | −0.061683 | 0.054238 | 0.282364 | 0.072497 | −0.154557 |
| 77 | 0.232476 | −0.151679 | 0.030695 | 0.002318 | −0.061125 | 0.079003 | −0.188727 | 0.044248 | 0.243027 | 0.018477 | 0.028865 | −0.046122 | −0.038351 | 0.006526 |
| 78 | −0.09259 | −0.293408 | −0.20485 | −0.17262 | 0.021081 | −0.053732 | 0.129888 | −0.118823 | −0.226158 | 0.082599 | −0.066261 | −0.25807 | −0.125097 | 0.002085 |
| 79 | −0.048084 | 0.218252 | 0.030694 | 0.019242 | −0.019464 | 0.024153 | −0.104646 | 0.117524 | −0.267811 | 0.045937 | 0.313096 | −0.120003 | −0.040368 | −0.121862 |
| 80 | −0.018521 | 0.323276 | 0.169828 | 0.09289 | 0.008805 | −0.152026 | 0.02309 | −0.01626 | 0.062339 | −0.009582 | −0.110313 | 0.132708 | −0.084905 | −0.060661 |
| 81 | −0.075693 | 0.180608 | 0.165088 | −0.179765 | −0.084475 | −0.129641 | 0.06177 | −0.060909 | 0.111409 | 0.003309 | −0.021249 | −0.046892 | 0.038956 | −0.148149 |
| 82 | −0.23749 | 0.131801 | 0.115232 | −0.109004 | 0.129751 | 0.306807 | −0.026505 | −0.020985 | 0.259453 | −0.150608 | −0.054441 | −0.126321 | 0.281271 | 0.020413 |

| | BD | BE | BF | BG | BH | BI | BJ | BK | BL | BM | BN | BO | BP | BQ |
|---|---|---|---|---|---|---|---|---|---|---|---|---|---|---|
| 1 | −0.001244 | 0.053817 | −0.074221 | 0.18658 | −0.097306 | 0.131889 | −0.084107 | 0.093251 | −0.013207 | 0.018218 | −0.015055 | 0.134484 | −0.014549 | 0.008797 |
| 2 | −0.003164 | 0.056341 | 0.080729 | −0.072774 | −0.000939 | 0.076721 | 0.009312 | −0.05224 | 0.120894 | 0.131214 | −0.043215 | −0.034155 | 0.093832 | 0.047183 |
| 3 | −0.189028 | −0.057907 | 0.2406 | −0.138098 | 0.102932 | −0.164626 | −0.051505 | −0.221259 | −0.022103 | −0.122669 | −0.014832 | −0.19171 | −0.037281 | 0.038609 |
| 4 | −0.04923 | −0.012928 | −0.065633 | −0.178057 | −0.395848 | 0.061083 | 0.211314 | 0.177015 | 0.010372 | 0.072426 | 0.047086 | 0.024126 | 0.115853 | −0.089276 |
| 5 | 0.062316 | −0.15214 | 0.036953 | 0.128558 | 0.226666 | 0.091014 | −0.173793 | −0.170004 | −0.061326 | 0.042194 | −0.100043 | 0.037459 | −0.051201 | 0.037288 |
| 6 | 0.06433 | 0.219319 | −0.164577 | 0.066254 | 0.185552 | −0.093438 | −0.100409 | −0.096457 | 0.048177 | −0.088452 | −0.048131 | −0.014359 | 0.004872 | 0.042349 |

APPENDIX B5-continued

PCA Transformation
Matrix (82 x 82; Benign/Malignant)

| | | | | | | | | | | | | | | |
|---|---|---|---|---|---|---|---|---|---|---|---|---|---|---|
| 7 | −0.05867 | −0.03354 | −0.145665 | 0.00523 | 0.03666 | −0.034035 | 0.118299 | 0.090945 | −0.171672 | −0.136525 | −0.031779 | 0.011367 | −0.099824 | −0.037469 |
| 8 | 0.21831 | −0.086789 | −0.050902 | 0.006299 | 0.121626 | 0.013341 | 0.128655 | 0.058792 | 0.099314 | −0.004564 | −0.147554 | 0.033041 | 0.174764 | −0.121351 |
| 9 | −0.02495 | 0.059053 | 0.005544 | −0.122595 | 0.028578 | 0.009392 | 0.058648 | 0.009821 | 0.095297 | 0.103595 | −0.012728 | −0.029808 | 0.020111 | 0.015435 |
| 10 | −0.027901 | 0.007467 | 0.191118 | 0.051106 | −0.039006 | 0.009162 | −0.014048 | 0.127652 | 0.104511 | 0.04147 | 0.136432 | 0.116493 | −0.093681 | 0.049243 |
| 11 | −0.069373 | 0.090026 | −0.099771 | −0.080188 | −0.008537 | 0.035654 | 0.204103 | 0.038374 | 0.02091 | −0.011612 | 0.064931 | −0.0064 | −0.116659 | 0.091647 |
| 12 | 0.058945 | −0.125272 | 0.178555 | 0.114903 | −0.150982 | −0.002856 | −0.101475 | 0.038731 | −0.093689 | 0 | 0.083206 | −0.009658 | −0.034559 | −0.046013 |
| 13 | 0.154948 | 0.005959 | 0.000234 | 0.047865 | −0.009747 | 0.069217 | −0.153329 | 0.065115 | −0.003611 | 0.100221 | −0.062445 | 0.079102 | 0.291143 | 0.125577 |
| 14 | −0.23965 | 0.015392 | 0.03728 | −0.021636 | 0.020659 | −0.129216 | 0.263662 | −0.301207 | −0.047842 | 0.31431 | −0.181959 | 0.066932 | −0.118758 | 0.019776 |
| 15 | −0.039127 | 0.012653 | −0.057083 | 0.049979 | 0.099582 | −0.001502 | −0.125207 | 0.147114 | 0.017728 | −0.217176 | 0.055332 | −0.072129 | 0.054263 | −0.077759 |
| 16 | 0.145067 | 0.07209 | −0.154998 | −0.039533 | −0.145937 | 0.143396 | −0.024766 | −0.022912 | 0.049584 | −0.223818 | −0.092831 | −0.256691 | −0.070925 | −0.12019 |
| 17 | 0.020276 | 0.166516 | −0.001937 | 0.078834 | −0.004024 | 0.003328 | −0.037372 | 0.047677 | 0.069565 | 0.096643 | −0.046158 | −0.057751 | 0.035408 | 0.112011 |
| 18 | −0.12095 | −0.100937 | 0.117586 | −0.041094 | 0.113368 | −0.049561 | 0.095088 | −0.08481 | −0.046004 | −0.050139 | −0.114286 | 0.054102 | 0.072102 | −0.091562 |
| 19 | 0.029941 | −0.144002 | 0.084238 | −0.05466 | −0.123692 | 0.043464 | −0.027436 | −0.183469 | −0.154135 | 0.003068 | −0.155246 | −0.008313 | 0.103222 | −0.094242 |
| 20 | −0.02518 | −0.150654 | −0.112931 | 0.079764 | 0.18951 | −0.082895 | −0.039434 | 0.195666 | −0.007015 | −0.142646 | 0.137981 | 0.079383 | −0.101395 | 0.039999 |
| 21 | 0.156405 | 0.072996 | 0.171713 | −0.04393 | −0.167455 | −0.006097 | 0.029912 | −0.14778 | 0.091341 | 0.08154 | 0.054206 | −0.003581 | 0.065316 | 0.061946 |
| 22 | −0.26588 | 0.126238 | 0.029703 | −0.08695 | −0.002857 | −0.010171 | −0.117424 | −0.047773 | −0.234175 | 0.144053 | 0.097999 | 0.007195 | −0.129092 | 0.006673 |
| 23 | −0.063074 | 0.084822 | 0.046434 | −0.015741 | −0.041731 | 0.063601 | 0.034182 | −0.013033 | 0.019817 | 0.003768 | 0.119599 | −0.043244 | −0.061353 | −0.044321 |
| 24 | 0.067549 | 0.004202 | −0.063337 | 0.005119 | 0.037791 | −0.205394 | −0.144885 | −0.01359 | −0.018715 | 0.07693 | −0.177197 | −0.061127 | 0.062916 | 0.048 |
| 25 | 0.011499 | −0.055877 | −0.073858 | 0.076527 | 0.006143 | 0.129201 | 0.085252 | −0.000637 | −0.043399 | −0.030577 | 0.022821 | 0.034482 | 0.091631 | −0.006286 |
| 26 | 0.137351 | 0.005664 | −0.005683 | 0.055626 | −0.041445 | −0.072995 | 0.153561 | 0.014742 | −0.043903 | −0.178955 | 0.247724 | −0.018765 | 0.006845 | 0.126865 |
| 27 | −0.147588 | −0.058396 | 0.073212 | −0.15128 | 0.030958 | 0.232629 | −0.097932 | 0.015746 | 0.09825 | 0.186423 | −0.198033 | 0.07404 | −0.059183 | −0.091335 |
| 28 | −0.012067 | −0.13351 | 0.143752 | −0.174093 | −0.115588 | 0.041009 | 0.032526 | 0.127755 | 0.039901 | −0.180055 | 0.005506 | −0.09201 | −0.077981 | 0.08881 |
| 29 | 0.060508 | −0.185107 | −0.092041 | −0.018141 | 0.098854 | −0.113874 | 0.06447 | −0.079735 | −0.025519 | 0.164064 | 0.07515 | 0.041694 | 0.015052 | −0.13167 |
| 30 | −0.001752 | 0.282991 | −0.07415 | −0.012169 | −0.007954 | −0.134718 | −0.068344 | 0.141806 | −0.167337 | 0.027354 | −0.048401 | −0.03722 | 0.225426 | −0.009544 |
| 31 | 0.071143 | 0.007145 | −0.160532 | 0.121751 | 0.074941 | 0.152803 | 0.086949 | −0.151365 | 0.170586 | 0.035613 | 0.148569 | 0.138337 | −0.044918 | 0.068101 |
| 32 | −0.00463 | 0.005133 | −0.054589 | 0.0579 | −0.018752 | −0.067403 | 0.033353 | 0.068166 | −0.008525 | 0.043291 | 0.011772 | 0.076453 | 0.050939 | −0.002625 |
| 33 | 0.001697 | −0.052174 | −0.293467 | −0.172799 | −0.126064 | −0.084593 | −0.129607 | −0.151568 | 0.024542 | −0.051232 | 0.018489 | 0.213584 | 0.040014 | −0.311548 |
| 34 | 0.093908 | −0.019055 | −0.038928 | 0.001136 | 0.059944 | −0.092536 | −0.108472 | −0.087682 | 0.010554 | −0.082996 | −0.013684 | −0.060913 | −0.078405 | 0.019656 |
| 35 | −0.095001 | 0.036903 | 0.210795 | −0.032034 | 0.051776 | −0.05467 | −0.016134 | 0.066559 | 0.077958 | −0.036203 | 0.059925 | −0.150345 | 0.036501 | 0.012012 |
| 36 | −0.118602 | 0.039272 | 0.015818 | 0.062921 | 0.02532 | 0.066371 | −0.021953 | −0.016797 | −0.092162 | −0.08608 | −0.017125 | −0.004189 | 0.024599 | −0.048427 |
| 37 | −0.050215 | −0.099498 | −0.061343 | −0.107876 | −0.030432 | 0.066642 | −0.127115 | 0.160348 | 0.133792 | 0.062525 | 0.097953 | −0.140278 | 0.033495 | −0.000398 |
| 38 | 0.000074 | 0.083326 | −0.094057 | −0.037709 | −0.070717 | 0.023443 | 0.000364 | −0.042949 | 0.086473 | 0.102849 | −0.000276 | 0.11176 | 0.111827 | 0.04819 |
| 39 | −0.03902 | −0.053118 | −0.031776 | −0.08995 | −0.023309 | −0.101858 | −0.118629 | 0.064981 | 0.152912 | 0.24759 | 0.045775 | −0.099474 | 0.056853 | 0.013972 |
| 40 | −0.057252 | −0.127611 | −0.121728 | 0.018316 | 0.036309 | 0.04022 | 0.042514 | −0.055798 | −0.068177 | −0.012489 | 0.039577 | 0.143883 | 0.039529 | −0.097517 |
| 41 | −0.024587 | −0.096256 | −0.030195 | 0.019557 | −0.071444 | −0.090893 | 0.105339 | 0.000525 | −0.26038 | 0.104597 | −0.006697 | 0.019887 | −0.007947 | −0.056081 |
| 42 | −0.126828 | 0.087898 | −0.237059 | 0.198514 | −0.228728 | 0.119506 | 0.090282 | −0.315919 | 0.047579 | −0.196307 | −0.104112 | −0.050502 | −0.004107 | 0.100832 |
| 43 | 0.201679 | 0.002928 | 0.124971 | −0.027279 | 0.158026 | −0.184531 | −0.09076 | 0.00312 | −0.207197 | 0.005498 | −0.0971 | 0.280595 | 0.120093 | −0.055645 |
| 44 | 0.176618 | 0.032176 | 0.02097 | 0.19593 | 0.032752 | 0.009015 | 0.122033 | −0.211868 | −0.029903 | −0.091048 | −0.040475 | 0.012433 | −0.046937 | −0.027163 |
| 45 | −0.03404 | 0.209508 | 0.181179 | −0.160348 | 0.056934 | 0.064208 | −0.087529 | −0.132469 | 0.066836 | −0.116371 | 0.102049 | 0.16751 | −0.100352 | −0.116036 |
| 46 | 0.045962 | 0.038898 | −0.150751 | −0.009999 | −0.011712 | 0.14269 | 0.060362 | 0.034358 | 0.040225 | 0.003633 | −0.007776 | −0.002957 | 0.023027 | 0.033656 |
| 47 | 0.062875 | 0.24534 | −0.035026 | 0.127599 | −0.061986 | −0.151147 | −0.074171 | −0.111296 | −0.013323 | 0.102074 | 0.100336 | −0.202422 | 0.036975 | −0.022247 |
| 48 | −0.094521 | 0.107711 | 0.121849 | 0.019886 | 0.078451 | 0.280297 | 0.093996 | 0.106164 | 0.191773 | −0.139236 | −0.135315 | 0.130475 | −0.102832 | −0.025586 |
| 49 | 0.054149 | −0.010349 | 0.060636 | −0.122775 | 0.132035 | −0.080826 | 0.202618 | 0.053095 | 0.127467 | 0.109861 | 0.096748 | 0.008297 | −0.045248 | −0.122545 |
| 50 | 0.1923 | −0.045953 | 0.128125 | 0.043046 | −0.141874 | 0.041401 | −0.106831 | 0.077797 | −0.074941 | 0.045424 | 0.187061 | 0.159691 | −0.023105 | 0.113014 |
| 51 | −0.083677 | −0.03445 | −0.09042 | −0.082723 | 0.247322 | 0.110302 | 0.069608 | 0.133904 | −0.006977 | 0.081143 | −0.021438 | −0.34365 | −0.04975 | −0.242176 |
| 52 | −0.031638 | −0.096714 | 0.044447 | −0.074439 | −0.210924 | −0.227696 | −0.011084 | 0.018429 | −0.174771 | −0.076281 | 0.037128 | −0.232952 | 0.02647 | −0.114265 |
| 53 | −0.116679 | −0.065179 | −0.049974 | 0.059656 | −0.037961 | −0.061485 | −0.018917 | 0.227887 | −0.008837 | 0.074587 | −0.207249 | 0.067956 | 0.132219 | 0.189581 |
| 54 | −0.16753 | −0.138732 | −0.056804 | 0.161515 | 0.018678 | −0.009815 | −0.076143 | −0.032671 | 0.04374 | 0.038725 | 0.031135 | −0.002581 | 0.126255 | 0.006439 |
| 55 | 0.025384 | 0.021229 | 0.036105 | −0.078062 | −0.173037 | 0.06753 | −0.003856 | −0.128043 | −0.206752 | −0.062224 | 0.001778 | −0.091675 | −0.053035 | 0.043546 |
| 56 | −0.090573 | 0.065264 | 0.11243 | −0.005868 | −0.121414 | −0.100826 | −0.172601 | 0.03059 | 0.038198 | −0.056791 | −0.054169 | 0.069723 | −0.049504 | 0.218108 |

APPENDIX B5-continued

PCA Transformation
Matrix (82 x 82; Benign/Malignant)

| | | | | | | | | | | | | | | |
|---|---|---|---|---|---|---|---|---|---|---|---|---|---|---|
| 57 | −0.001907 | −0.129882 | −0.015839 | −0.025762 | −0.154833 | −0.267157 | 0.115557 | 0.135339 | 0.097862 | −0.14806 | −0.286415 | 0.028593 | 0.00328 | −0.014859 |
| 58 | −0.109257 | −0.287606 | 0.076815 | 0.045276 | 0.051135 | 0.198681 | −0.112769 | −0.129286 | −0.125403 | −0.106386 | 0.182918 | −0.027945 | 0.015695 | 0.123442 |
| 59 | −0.00673 | −0.149021 | −0.028474 | 0.037084 | 0.037447 | 0.024363 | −0.081569 | −0.03966 | −0.058396 | −0.097413 | −0.087087 | −0.076519 | −0.140699 | −0.082484 |
| 60 | 0.044361 | −0.039644 | −0.002841 | −0.036509 | 0.089235 | 0.089713 | 0.048492 | −0.082037 | 0.080429 | 0.075094 | 0.01478 | 0.023049 | 0.083406 | 0.043709 |
| 61 | 0.128205 | −0.0075 | −0.000083 | 0.07147 | 0.039943 | 0.122974 | −0.092177 | 0.115818 | −0.161274 | 0.143278 | −0.185378 | −0.104958 | −0.178575 | 0.24134 |
| 62 | 0.063342 | 0.097796 | 0.074232 | 0.086342 | 0.096534 | −0.015359 | 0.348552 | 0.046221 | −0.172666 | 0.005105 | 0.052149 | −0.026227 | 0.288492 | 0.056115 |
| 63 | −0.049658 | −0.012151 | −0.024002 | −0.128214 | 0.052409 | −0.028884 | 0.074011 | 0.038207 | 0.047187 | 0.046494 | 0.029338 | 0.034788 | 0.044587 | −0.000427 |
| 64 | 0.030599 | −0.073931 | 0.194486 | 0.137337 | 0.063429 | −0.199423 | 0.085976 | −0.044925 | 0.323864 | −0.056667 | 0.052286 | −0.052578 | −0.018787 | −0.01316 |
| 65 | 0.121293 | 0.329697 | −0.117498 | −0.183379 | 0.143285 | −0.073085 | −0.171973 | 0.008079 | −0.084145 | 0.102951 | 0.18244 | −0.032439 | −0.183166 | −0.111608 |
| 66 | 0.030617 | −0.041858 | 0.032906 | −0.07048 | −0.078873 | −0.040416 | 0.057902 | −0.001755 | 0.018198 | 0.056725 | 0.039005 | 0.008853 | 0.007628 | 0.036446 |
| 67 | 0.014259 | 0.012198 | 0.055592 | 0.062166 | 0.136645 | −0.037531 | 0.178387 | 0.040525 | −0.062078 | −0.026767 | −0.010029 | 0.023809 | −0.101883 | −0.038362 |
| 68 | 0.21629 | −0.036791 | −0.070304 | −0.161919 | −0.084896 | 0.200289 | −0.050729 | 0.015078 | −0.085323 | 0.086889 | −0.135568 | 0.005041 | −0.221695 | −0.083858 |
| 69 | −0.230383 | −0.002367 | −0.190261 | 0.297881 | −0.161341 | −0.200615 | −0.154988 | 0.029384 | 0.148601 | 0.121494 | −0.007704 | −0.017164 | −0.136444 | −0.090277 |
| 70 | −0.210638 | −0.022476 | −0.093155 | −0.178687 | 0.112472 | −0.05218 | −0.171157 | −0.062179 | −0.051565 | −0.181169 | 0.163515 | 0.167756 | 0.247697 | 0.157113 |
| 71 | 0.17113 | 0.036085 | 0.010007 | −0.222738 | −0.003387 | 0.058082 | 0.043068 | −0.103869 | −0.056951 | −0.119561 | 0.063443 | −0.189716 | 0.168216 | 0.118621 |
| 72 | 0.105234 | 0.056464 | 0.207942 | 0.214334 | 0.018721 | −0.052102 | 0.006021 | 0.098051 | 0.037918 | 0.016601 | −0.117741 | −0.081971 | −0.141856 | −0.082121 |
| 73 | −0.035774 | 0.095963 | 0.120919 | 0.073419 | 0.003678 | 0.217469 | −0.080024 | −0.076853 | −0.098777 | 0.113909 | −0.181069 | −0.181453 | 0.224095 | −0.014971 |
| 74 | −0.20099 | 0.152179 | 0.033595 | −0.073011 | 0.011044 | 0.086057 | 0.011687 | 0.008506 | 0.105021 | −0.010868 | 0.056939 | 0.010469 | 0.110405 | 0.080693 |
| 75 | 0.055213 | 0.007456 | −0.126314 | −0.132738 | 0.134807 | −0.098728 | −0.010591 | −0.051604 | 0.218541 | −0.170896 | −0.178925 | −0.092494 | 0.112945 | 0.021524 |
| 76 | −0.007439 | 0.123329 | 0.140454 | 0.022643 | −0.000072 | 0.08143 | −0.01665 | 0.106865 | −0.131494 | −0.063768 | 0.005409 | 0.20878 | 0.052635 | −0.399699 |
| 77 | 0.022432 | 0.028365 | −0.158023 | −0.035764 | 0.099155 | −0.06729 | 0.223313 | 0.063836 | −0.196508 | 0.097279 | 0.071146 | −0.006065 | −0.247161 | 0.288981 |
| 78 | −0.012867 | −0.10858 | −0.0346 | −0.007844 | −0.08371 | 0.004449 | 0.067316 | −0.12798 | 0.082823 | 0.080477 | 0.192062 | 0.051583 | 0.035653 | 0.008591 |
| 79 | 0.268988 | −0.063879 | 0.032299 | −0.193585 | −0.134449 | −0.142634 | −0.090564 | −0.131082 | 0.171728 | 0.024683 | −0.070891 | 0.149998 | −0.190353 | 0.089079 |
| 80 | 0.118856 | −0.207855 | −0.036757 | 0.156219 | −0.002597 | 0.068894 | −0.074646 | 0.031058 | 0.062237 | 0.202027 | 0.263943 | −0.208958 | 0.08159 | −0.15481 |
| 81 | −0.047821 | −0.07027 | −0.079186 | −0.160749 | 0.025044 | 0.022103 | −0.035928 | 0.193768 | −0.047946 | −0.075655 | −0.125156 | 0.076672 | −0.095528 | 0.151496 |
| 82 | −0.064923 | 0.206765 | 0.135113 | 0.193146 | −0.14449 | −0.043166 | 0.039865 | 0.068477 | −0.001011 | −0.121292 | −0.001938 | 0.08584 | −0.048616 | −0.167981 |

| | BR | BS | BT | BU | BV | BW | BX | BY | BZ | CA | CB | CC | CD | CE |
|---|---|---|---|---|---|---|---|---|---|---|---|---|---|---|
| 1 | 0.024241 | −0.033777 | 0.017877 | −0.005716 | 0.086221 | −0.090588 | 0.030881 | −0.046743 | 0.03184 | −0.014991 | −0.022127 | 0.039833 | −0.124322 | −0.014119 |
| 2 | 0.00682 | 0.09934 | −0.043715 | −0.049648 | −0.053874 | 0.03354 | 0.030903 | 0.194401 | −0.021118 | 0.100404 | −0.069902 | −0.045182 | −0.048606 | −0.013674 |
| 3 | −0.041021 | 0.040161 | −0.088846 | −0.08222 | −0.119572 | 0.143903 | −0.044482 | −0.132716 | −0.004585 | −0.025715 | −0.006412 | −0.027557 | −0.035778 | −0.001383 |
| 4 | 0.051575 | 0.061021 | 0.160572 | −0.10396 | 0.022545 | −0.042854 | −0.086799 | −0.060489 | −0.208794 | 0.060646 | −0.03842 | −0.105501 | 0.061065 | −0.001695 |
| 5 | −0.03891 | −0.041426 | −0.16463 | 0.271177 | −0.175203 | −0.126986 | 0.033134 | 0.366046 | 0.273706 | 0.050037 | 0.123908 | −0.040885 | 0.076169 | −0.001278 |
| 6 | 0.049044 | −0.101595 | 0.015928 | −0.139565 | 0.209088 | 0.192442 | 0.050592 | −0.275018 | −0.039856 | −0.069459 | −0.271603 | 0.246644 | −0.170109 | −0.002765 |
| 7 | −0.011192 | −0.105146 | 0.066279 | 0.050746 | −0.050125 | −0.053675 | −0.053902 | −0.06431 | −0.03505 | −0.039675 | 0.031156 | 0.042994 | 0.156082 | −0.000613 |
| 8 | −0.120481 | −0.030416 | 0.010262 | −0.107084 | 0.081716 | −0.142235 | 0.125335 | −0.091635 | 0.158272 | −0.014208 | −0.03342 | −0.354094 | 0.056424 | −0.005077 |
| 9 | 0.020563 | 0.014019 | 0.009172 | −0.028633 | 0.017666 | −0.023623 | 0.007044 | 0.076384 | −0.014206 | −0.019854 | 0.079504 | −0.067071 | 0.014015 | −0.000658 |
| 10 | −0.037473 | −0.090846 | 0.083599 | 0.0724 | 0.031918 | −0.10359 | 0.056532 | −0.108578 | 0.072599 | 0.001143 | 0.207536 | 0.050945 | −0.078741 | −0.000239 |
| 11 | −0.022486 | 0.017038 | 0.010636 | 0.023614 | −0.035773 | 0.058595 | −0.024807 | 0.02717 | −0.048739 | 0.0007 | 0.05813 | −0.013548 | 0.059767 | −0.000815 |
| 12 | −0.078848 | 0.122882 | −0.08802 | 0.008867 | −0.024965 | −0.013533 | −0.001674 | 0.04211 | 0.023069 | −0.00882 | 0.049564 | −0.054316 | −0.047724 | −0.000345 |
| 13 | 0.02223 | −0.195822 | 0.020232 | −0.082317 | −0.059024 | 0.317178 | 0.160309 | 0.123524 | −0.301692 | −0.022895 | 0.211031 | 0.025376 | 0.310716 | −0.004472 |
| 14 | −0.075266 | 0.023916 | 0.059848 | −0.029679 | 0.09555 | −0.025589 | 0.094704 | 0.081025 | 0.086377 | 0.039598 | −0.127691 | −0.033059 | −0.020059 | −0.00136 |
| 15 | −0.080843 | 0.042283 | −0.050654 | −0.015495 | −0.032768 | −0.012018 | −0.105273 | 0.045387 | 0.070685 | 0.009163 | 0.015594 | −0.02217 | 0.089974 | −0.001225 |
| 16 | 0.158794 | 0.15524 | −0.158183 | 0.030992 | −0.089438 | −0.150841 | −0.113889 | −0.121528 | 0.080926 | 0.011881 | −0.175179 | −0.12312 | −0.311771 | −0.003223 |
| 17 | 0.082417 | 0.060622 | −0.020572 | 0.0075 | 0.045555 | 0.084174 | 0.065012 | 0.019431 | 0.033353 | 0.057461 | −0.008709 | 0.009624 | −0.100653 | −0.014881 |
| 18 | −0.011366 | −0.00267 | −0.028842 | −0.049696 | 0.025109 | −0.017566 | −0.057889 | −0.002872 | −0.027329 | 0.020879 | −0.126713 | 0.007526 | 0.034278 | −0.003072 |
| 19 | 0.013762 | −0.036238 | −0.040205 | −0.049825 | −0.004242 | −0.05372 | 0.010452 | −0.023707 | −0.084909 | 0.011178 | −0.160083 | −0.048659 | 0.050459 | −0.010474 |
| 20 | −0.136745 | 0.044853 | 0.023597 | −0.024276 | 0.03771 | −0.096333 | −0.003022 | −0.048194 | −0.036406 | −0.028575 | 0.043929 | 0.017688 | 0.029853 | −0.00046 |
| 21 | 0.18238 | −0.038932 | −0.042265 | 0.027768 | 0.020542 | 0.066122 | −0.029021 | −0.000642 | −0.099882 | 0.024238 | −0.040621 | 0.02318 | −0.057109 | −0.000492 |

APPENDIX B5-continued

PCA Transformation
Matrix (82 x 82; Benign/Malignant)

| | | | | | | | | | | | | | | |
|---|---|---|---|---|---|---|---|---|---|---|---|---|---|---|
| 22 | 0.033723 | 0.098982 | 0.023871 | 0.097514 | −0.005516 | 0.085802 | −0.113814 | 0.097425 | −0.06975 | 0.024139 | −0.035564 | 0.412385 | 0.004118 | −0.001642 |
| 23 | −0.083261 | 0.04406 | −0.035075 | 0.03902 | 0.013891 | 0.034555 | −0.02444 | 0.029846 | 0.118178 | −0.055322 | 0.062067 | 0.021609 | 0.000644 | −0.004418 |
| 24 | 0.041592 | −0.019705 | 0.022037 | −0.061826 | −0.103326 | −0.024999 | 0.031774 | −0.08531 | −0.077772 | 0.006016 | 0.020425 | −0.068021 | −0.010117 | −0.009723 |
| 25 | 0.007046 | −0.027215 | 0.018988 | 0.050625 | 0.077393 | 0.003076 | 0.052871 | 0.040458 | 0.044642 | 0.021134 | −0.106281 | 0.024962 | 0.009074 | −0.018439 |
| 26 | 0.005149 | 0.10185 | −0.113285 | −0.07299 | 0.218389 | 0.0936 | −0.013225 | 0.337164 | −0.046585 | 0.052307 | −0.20002 | −0.014965 | 0.106236 | −0.110786 |
| 27 | 0.043122 | −0.122679 | 0.0348 | 0.009978 | −0.156132 | −0.133245 | 0.048481 | −0.264556 | −0.022162 | −0.028986 | 0.187942 | 0.073413 | −0.135382 | −0.074197 |
| 28 | 0.031687 | −0.097009 | −0.071332 | 0.032124 | −0.070356 | 0.131304 | −0.032965 | 0.066915 | −0.118449 | −0.051859 | −0.032082 | −0.047716 | 0.012617 | −0.220082 |
| 29 | 0.070128 | 0.149363 | 0.084103 | −0.098872 | 0.177184 | −0.210639 | 0.054759 | −0.01879 | −0.075289 | 0.121721 | 0.088281 | 0.144377 | 0.003408 | −0.095221 |
| 30 | −0.010075 | 0.015892 | −0.094793 | 0.326159 | −0.088267 | −0.043403 | 0.234658 | 0.012754 | 0.080805 | −0.078951 | −0.219507 | 0.008681 | 0.008838 | −0.073784 |
| 31 | −0.028367 | 0.085772 | 0.093026 | −0.092486 | −0.00734 | 0.120123 | −0.31145 | −0.02301 | 0.074502 | −0.027302 | 0.10044 | −0.074623 | 0.03884 | −0.019594 |
| 32 | −0.013807 | 0.060441 | 0.010442 | 0.054833 | −0.025092 | 0.040666 | −0.045 | −0.03425 | −0.013977 | −0.016743 | −0.064915 | 0.013877 | −0.037279 | −0.00231 |
| 33 | 0.064544 | 0.048178 | −0.179913 | 0.029669 | −0.074559 | 0.138523 | 0.029215 | 0.037337 | −0.031315 | −0.275656 | 0.13667 | 0.075967 | 0.057102 | −0.145685 |
| 34 | 0.071673 | −0.099809 | 0.014966 | −0.035265 | 0.056257 | −0.004361 | 0.039464 | 0.002701 | −0.05266 | 0.027714 | 0.030318 | 0.008072 | 0.077975 | −0.07185 |
| 35 | −0.077184 | 0.010579 | −0.042154 | −0.006238 | −0.077273 | −0.060367 | 0.042417 | 0.029957 | −0.103606 | −0.005561 | −0.03932 | −0.04786 | −0.06138 | −0.046207 |
| 36 | −0.078558 | 0.045233 | −0.087622 | −0.02735 | −0.008331 | −0.02384 | 0.013796 | 0.037035 | 0.00727 | 0.037193 | −0.036953 | −0.07139 | 0.039244 | −0.004511 |
| 37 | 0.008751 | 0.012492 | 0.048724 | −0.027734 | −0.07762 | −0.04883 | −0.002485 | 0.028668 | 0.12966 | 0.097452 | 0.008093 | 0.086844 | 0.017483 | −0.019681 |
| 38 | 0.028604 | −0.004855 | −0.02746 | 0.078156 | 0.144785 | −0.084455 | −0.025936 | 0.044708 | 0.093153 | −0.014631 | −0.004743 | −0.028355 | 0.005834 | −0.004666 |
| 39 | 0.001353 | −0.054419 | 0.085729 | 0.173948 | 0.010562 | 0.019714 | −0.158503 | −0.019461 | 0.063646 | −0.109468 | 0.021235 | 0.00564 | 0.019373 | −0.12443 |
| 40 | −0.056984 | 0.122882 | −0.097881 | −0.058475 | −0.047884 | −0.082483 | 0.05655 | 0.017911 | −0.074512 | −0.046919 | −0.022344 | 0.075356 | 0.011229 | −0.477782 |
| 41 | −0.090897 | 0.151197 | 0.037908 | −0.06885 | −0.048453 | 0.131446 | −0.073 | −0.059353 | 0.102605 | 0.057548 | −0.073869 | 0.013681 | −0.033039 | −0.049965 |
| 42 | 0.012666 | −0.081653 | 0.130602 | 0.227782 | −0.161365 | −0.044002 | −0.016381 | −0.010853 | −0.163381 | 0.042679 | 0.082158 | 0.000895 | 0.048775 | −0.044016 |
| 43 | −0.013155 | 0.010417 | 0.070733 | 0.034844 | 0.105443 | −0.121988 | −0.144864 | −0.12202 | −0.139177 | −0.188712 | −0.04534 | −0.126276 | −0.063782 | −0.016816 |
| 44 | 0.098267 | −0.002904 | −0.121548 | −0.135247 | −0.11039 | 0.083985 | 0.10411 | −0.047576 | −0.103926 | 0.119318 | 0.074028 | 0.118721 | −0.050691 | −0.026861 |
| 45 | −0.023204 | −0.20978 | 0.001313 | 0.066798 | 0.198725 | 0.004639 | −0.192485 | 0.009221 | 0.096938 | −0.124591 | −0.027487 | −0.115637 | 0.001098 | −0.370556 |
| 46 | −0.041144 | 0.103724 | −0.07115 | −0.063862 | −0.100792 | −0.100253 | 0.07381 | 0.063229 | −0.007434 | 0.124447 | −0.00879 | 0.124728 | 0.001715 | −0.220569 |
| 47 | 0.102866 | −0.023811 | 0.142949 | 0.108536 | 0.063597 | 0.110179 | −0.085662 | −0.071713 | 0.173969 | 0.026519 | 0.208017 | −0.234275 | 0.000231 | −0.299545 |
| 48 | −0.022554 | −0.070688 | −0.060019 | −0.010836 | 0.027158 | −0.111338 | 0.207661 | 0.008809 | −0.1602 | −0.053627 | −0.044767 | 0.11169 | −0.047908 | −0.158292 |
| 49 | 0.036527 | 0.006178 | −0.004119 | −0.13034 | −0.016488 | 0.188091 | 0.046939 | 0.006434 | 0.100156 | −0.007851 | 0.011677 | −0.007224 | −0.030772 | −0.017837 |
| 50 | 0.029204 | 0.161985 | −0.141394 | −0.06413 | 0.020538 | 0.025978 | 0.21461 | −0.105545 | 0.226978 | 0.038939 | 0.041475 | 0.241194 | −0.13504 | −0.041873 |
| 51 | 0.087046 | −0.11504 | −0.046577 | −0.031827 | 0.063279 | 0.161175 | 0.091496 | 0.099494 | −0.01496 | −0.01448 | −0.028117 | −0.079181 | 0.085395 | −0.032399 |
| 52 | 0.008815 | −0.06123 | 0.044737 | 0.134525 | 0.145678 | −0.152315 | 0.339352 | 0.033516 | −0.099854 | 0.027697 | 0.136908 | 0.009134 | −0.066651 | −0.138934 |
| 53 | −0.121055 | 0.160995 | −0.117567 | −0.109379 | −0.339589 | 0.265339 | −0.088995 | −0.111422 | 0.124605 | −0.116716 | −0.105694 | −0.061116 | −0.056791 | −0.217176 |
| 54 | −0.211087 | −0.052416 | −0.137012 | 0.051954 | 0.220754 | 0.14247 | −0.034067 | 0.144646 | −0.212097 | 0.12677 | 0.095057 | −0.171798 | −0.477793 | −0.139254 |
| 55 | 0.035054 | −0.060507 | 0.043875 | −0.220459 | −0.023207 | −0.003908 | 0.002665 | 0.00145 | 0.357754 | −0.021398 | 0.047297 | −0.029776 | 0.136928 | −0.051627 |
| 56 | −0.233716 | 0.014795 | 0.015785 | −0.053426 | −0.003742 | −0.215222 | −0.276931 | 0.087493 | −0.179215 | 0.047494 | −0.163258 | −0.06402 | 0.104765 | −0.016499 |
| 57 | 0.018483 | −0.219996 | −0.171386 | 0.070187 | 0.168414 | 0.066299 | −0.182341 | −0.020324 | 0.193697 | 0.190246 | 0.131017 | 0.237262 | 0.008919 | −0.0186 |
| 58 | 0.125809 | 0.143268 | 0.327978 | 0.078977 | −0.009453 | 0.149722 | 0.16674 | −0.121674 | −0.022752 | −0.281632 | −0.107929 | −0.133799 | −0.039807 | −0.015866 |
| 59 | −0.004411 | 0.03082 | 0.014366 | −0.250535 | 0.024482 | 0.115511 | −0.064334 | −0.013659 | −0.052209 | 0.148553 | 0.229125 | −0.013501 | −0.060752 | −0.094367 |
| 60 | 0.139238 | −0.050301 | −0.043884 | 0.079001 | 0.059119 | −0.050447 | 0.008541 | 0.078051 | −0.002978 | −0.113992 | −0.135218 | 0.070369 | 0.090427 | −0.04155 |
| 61 | −0.013554 | −0.160186 | 0.282751 | −0.133474 | 0.082608 | −0.057319 | 0.040305 | 0.004308 | 0.050482 | 0.214313 | −0.172711 | 0.015177 | 0.053842 | −0.382917 |
| 62 | 0.077873 | 0.023783 | 0.103268 | 0.040287 | −0.202871 | −0.093407 | −0.162965 | 0.03527 | 0.011801 | −0.042904 | 0.216646 | 0.072677 | −0.190195 | −0.150457 |
| 63 | −0.073908 | 0.015119 | −0.084518 | 0.013424 | 0.038089 | 0.040172 | 0.013775 | 0.095197 | −0.007529 | −0.055185 | −0.023453 | 0.040649 | −0.066153 | −0.102347 |
| 64 | 0.153367 | 0.223678 | −0.0505 | 0.116926 | −0.124101 | −0.12671 | 0.017798 | −0.231869 | −0.030286 | 0.049754 | −0.099343 | 0.092758 | 0.371332 | −0.234269 |
| 65 | −0.108806 | 0.176359 | −0.003302 | −0.134456 | −0.197684 | −0.153327 | 0.027815 | 0.013189 | −0.231 | 0.158449 | 0.094663 | −0.10901 | 0.00788 | −0.013811 |
| 66 | 0.018664 | 0.001552 | 0.063115 | 0.014424 | 0.040451 | 0.013903 | −0.020057 | −0.028474 | 0.005778 | −0.033442 | 0.024143 | 0.002221 | −0.009836 | −0.02189 |
| 67 | 0.077366 | 0.052041 | 0.007806 | 0.119461 | −0.044232 | −0.038907 | −0.03072 | 0.038446 | −0.047248 | −0.018758 | −0.044479 | −0.01639 | −0.081558 | −0.004252 |
| 68 | −0.250072 | 0.179149 | −0.079183 | 0.307406 | 0.186381 | 0.24721 | −0.030906 | −0.171199 | −0.023039 | 0.091413 | −0.076627 | −0.048562 | 0.177969 | −0.001753 |
| 69 | 0.105149 | −0.064249 | 0.000082 | −0.295794 | −0.022409 | −0.12816 | 0.068003 | 0.161289 | 0.059243 | −0.256677 | −0.127882 | −0.049284 | 0.064274 | −0.000891 |
| 70 | 0.222706 | −0.065376 | −0.048567 | −0.018184 | 0.019598 | −0.018638 | 0.000306 | −0.170795 | 0.068179 | 0.426977 | 0.030261 | −0.105359 | 0.049235 | −0.002339 |
| 71 | −0.257249 | −0.180085 | 0.046189 | −0.220216 | −0.046244 | −0.146358 | −0.026848 | 0.067261 | 0.081047 | −0.321578 | 0.03745 | 0.223401 | −0.071831 | −0.004925 |

APPENDIX B5-continued

PCA Transformation
Matrix (82 x 82; Benign/Malignant)

| | | | | | | | | | | | | | | |
|---|---|---|---|---|---|---|---|---|---|---|---|---|---|---|
| 72 | 0.140389 | 0.118179 | 0.023371 | 0.067526 | −0.002955 | 0.144592 | −0.031793 | 0.03931 | −0.138654 | −0.073134 | 0.072737 | −0.026975 | −0.061325 | −0.014135 |
| 73 | 0.009862 | 0.249963 | −0.258953 | −0.132109 | 0.228379 | −0.156549 | −0.199806 | −0.056145 | −0.066463 | −0.060604 | 0.167127 | 0.084757 | 0.16775 | −0.001967 |
| 74 | 0.021396 | 0.061524 | −0.163494 | −0.107841 | 0.110279 | 0.061538 | 0.186982 | −0.082198 | 0.100576 | 0.03977 | −0.008229 | −0.099295 | 0.025747 | −0.000299 |
| 75 | −0.244646 | 0.22951 | 0.388333 | 0.128127 | 0.004176 | 0.058593 | 0.040936 | 0.105207 | 0.050296 | 0.057042 | 0.048426 | 0.207753 | −0.082066 | −0.001906 |
| 76 | 0.138332 | −0.177213 | 0.163851 | −0.041561 | −0.242457 | 0.101019 | −0.097829 | 0.16481 | 0.069263 | 0.219924 | −0.182734 | 0.012166 | −0.033146 | −0.002522 |
| 77 | 0.013275 | −0.23148 | −0.316912 | 0.070482 | −0.079059 | −0.04197 | 0.007923 | −0.16146 | −0.086847 | −0.113614 | 0.09547 | −0.117905 | 0.009716 | −0.002588 |
| 78 | −0.220472 | −0.058048 | −0.024166 | 0.068595 | −0.097795 | −0.035428 | 0.13787 | −0.120254 | 0.011722 | 0.139018 | −0.08095 | −0.115351 | −0.014934 | −0.004491 |
| 79 | 0.028004 | −0.022122 | −0.021732 | −0.059977 | −0.17287 | 0.006888 | 0.069562 | 0.183989 | −0.022981 | 0.010477 | −0.050189 | −0.04655 | −0.158369 | −0.000426 |
| 80 | −0.037838 | −0.244848 | −0.074174 | 0.084716 | −0.030533 | −0.054988 | −0.242166 | −0.098615 | −0.075346 | 0.020055 | −0.186007 | 0.16411 | −0.039334 | −0.000481 |
| 81 | 0.409089 | 0.212496 | 0.069737 | 0.033377 | 0.176029 | −0.076307 | −0.071942 | 0.170292 | 0.019875 | −0.136613 | 0.110045 | −0.078128 | −0.07548 | −0.001032 |
| 82 | −0.272339 | 0.01553 | 0.086301 | −0.053014 | 0.09285 | 0.061435 | 0.136134 | −0.067316 | 0.08006 | −0.071383 | 0.171578 | −0.016179 | 0.106177 | −0.000534 |

APPENDIX B6

PCA Transformation
Matrix (82 x 82; Early/Late)

| | A | B | C | D | E | F | G | H | I | J | K | L | M |
|---|---|---|---|---|---|---|---|---|---|---|---|---|---|
| 1 | 409.4/255.3>GPA:Lyso 16:0 | −0.136578 | 0.026918 | −0.179059 | −0.058653 | −0.086368 | −0.035633 | 0.050593 | 0.076582! | −0.029673 | 0.055756 | −0.098198 | −0.146524 |
| 2 | 437.4/283.3>GPA:Lyso 18:0 | −0.015366 | −0.135495 | −0.215613 | −0.077551 | −0.073632 | 0.002826 | 0.033492 | 0.087495 | 0.000544 | −0.073305 | −0.142556 | −0.067888 |
| 3 | 647.8/255.3>GPA:16:0/16:0 | −0.13907 | 0.070449 | −0.154405 | −0.030159 | 0.047484 | −0.092146 | −0.078325 | 0.065556 | −0.006695 | 0.100742 | 0.02398 | −0.038163 |
| 4 | 673.8/281.3>GPA:18:1/16:0 | −0.061678 | −0.005691 | −0.141111 | 0.045361 | 0.337125 | −0.095114 | −0.14442 | −0.071107 | −0.027071 | 0.024692 | 0.06676 | 0.042634 |
| 5 | 699.8/281.3>GPA:36:2 | −0.060796 | −0.004305 | −0.12786 | 0.035453 | 0.366895 | −0.066398 | −0.103301 | −0.052227 | 0.024814 | 0.022616 | 0.093339 | 0.015273 |
| 6 | 701.8/283.3>GPA:36:1 | −0.051018 | −0.002772 | −0.137887 | 0.054481 | 0.36088 | −0.07221 | −0.111322 | −0.085259 | −0.015496 | −0.051842 | 0.03455 | 0.077426 |
| 7 | 703.8/283.3>GPA:36:0 | −0.097364 | −0.074212 | −0.206745 | −0.015502 | 0.141843 | −0.04634 | −0.042623 | −0.013334 | −0.039838 | −0.132194 | −0.136083 | −0.089534 |
| 8 | 721.8/281.3>GPA:16:0/22:5 | −0.109125 | −0.104787 | −0.169056 | −0.044546 | −0.029471 | 0.027012 | 0.109969 | 0.062388 | 0.20541 | 0.059683 | −0.094813 | −0.05113 |
| 9 | 723.8/283.3>GPA:18:0/20:4 | −0.051718 | 0.016658 | −0.13275 | −0.004276 | 0.343435 | −0.019323 | −0.083136 | −0.047159 | −0.035261 | −0.144148 | −0.088091 | 0.013909 |
| 10 | 731.8/283.3>GPA:38:0 | −0.094978 | −0.066352 | −0.227167 | −0.04065 | 0.079164 | −0.07265 | −0.064126 | −0.007041 | 0.097928 | −0.143105 | −0.019096 | 0.045869 |
| 11 | 757.8/281.3>GPA:40:1 | −0.135536 | −0.01375 | −0.034636 | 0.07544 | 0.191388 | 0.160939 | 0.017959 | 0.067692 | 0.148989 | 0.016284 | 0.17465 | −0.111316 |
| 12 | 759.8/283.3>GPA:40:0 | −0.093994 | −0.032783 | −0.120054 | 0.058957 | 0.27879 | −0.099211 | −0.01188 | −0.168352 | −0.170967 | −0.036391 | 0.021923 | 0.15209 |
| 13 | 483.4/255.3>GPGro:Lyso 16:0 | −0.09227 | −0.058461 | −0.203505 | −0.104618 | −0.168808 | −0.087268 | −0.102923 | −0.022485 | −0.021792 | 0.001958 | 0.058842 | 0.170063 |
| 14 | 507.4/279.3>GPGro:Lyso 18:2 | −0.055789 | −0.048797 | −0.216786 | −0.043794 | −0.199415 | −0.12293 | −0.165808 | −0.01926 | −0.063594 | −0.028103 | 0.049554 | 0.072095 |
| 15 | 509.4/281.3>GPGro:Lyso 18:1 | −0.024097 | −0.08436 | −0.220862 | −0.133415 | −0.14023 | −0.093028 | −0.056738 | −0.03133 | −0.176016 | −0.016151 | 0.081471 | −0.088285 |
| 16 | 511.4/283.3>GPGro:Lyso 18:0 | −0.054802 | −0.096889 | −0.217789 | −0.089839 | −0.161526 | −0.058548 | −0.125228 | −0.045766 | 0.025905 | −0.014741 | 0.06452 | 0.125625 |
| 17 | 743.8/279.3>GPGro:18:2/16:1 | −0.002076 | 0.035006 | 0.211024 | 0.131241 | 0.075118 | 0.066019 | −0.197252 | −0.004421 | −0.072671 | −0.179592 | −0.088911 | −0.067915 |
| 18 | 769.8/279.3>GPGro:18:2/18:2 | 0.030048 | −0.009163 | 0.071401 | 0.234819 | −0.090737 | −0.120753 | −0.028416 | −0.128719 | −0.315541 | −0.03555 | 0.189375 | 0.254203 |
| 19 | 771.8/279.3>GPGro:18:2/18:1 | −0.003851 | 0.026715 | 0.085631 | 0.224263 | 0.05241 | 0.04589 | 0.013852 | −0.045266 | 0.373115 | −0.147984 | −0.111009 | −0.384538 |
| 20 | 773.8/279.3>GPGro:18:2/18:0 | 0.046154 | −0.140412 | −0.135872 | 0.075818 | −0.094208 | −0.070136 | −0.226267 | −0.076825 | 0.155637 | 0.009463 | 0.092463 | −0.256179 |
| 21 | 775.8/281.3>GPGroL18:1/18:0 | 0.04664 | −0.143574 | −0.185604 | −0.105163 | −0.060633 | −0.087316 | −0.070104 | −0.008481 | 0.059538 | 0.176164 | 0.127384 | −0.207047 |
| 22 | 777.8/283.3>GPGro:18:0/18:0 | −0.088128 | −0.126351 | −0.16496 | 0.000014 | −0.103398 | 0.01665 | 0.107601 | −0.025074 | 0.20373 | 0.065219 | −0.05773 | −0.098737 |
| 23 | 476.6/196.1>Lyso GPEtn:Lyso18:2a | 0.018471 | 0.018669 | −0.100978 | 0.282057 | −0.02 | −0.075543 | 0.066489 | 0.311767 | −0.034866 | 0.111099 | −0.044926 | −0.110701 |
| 24 | 478.4/196.1>Lyso GPEtn:Lyso 18:1 | 0.000865 | −0.030998 | −0.078351 | 0.236209 | 0.040053 | −0.083212 | 0.182205 | 0.25866 | −0.255625 | 0.119807 | 0.147797 | −0.218369 |
| 25 | 480.4/196.1>Lyso GPEtn:Lyso 18:0 | −0.10151 | −0.028701 | 0.011767 | 0.059814 | 0.122722 | −0.171887 | 0.209565 | 0.067183 | −0.305509 | 0.041674 | 0.032238 | −0.367704 |
| 26 | 500.4/196.1>Lyso GPEtn:Lyso 20:4 | 0.075828 | 0.130702 | −0.113021 | 0.153289 | 0.027997 | −0.006889 | 0.109728 | 0.205581 | −0.130963 | 0.023563 | −0.191492 | 0.052219 |
| 27 | 524.4/196.1>Lyso GPEtn:Lyso 22:6 | 0.051673 | 0.179821 | −0.100405 | 0.057279 | 0.021248 | −0.002517 | 0.231188 | 0.043179 | −0.164946 | −0.162377 | −0.040166 | 0.000696 |
| 28 | 520.4/184.1>GPCho:Lyso 18:2 | −0.085227 | 0.048257 | −0.067182 | 0.239202 | −0.092764 | −0.135681 | 0.073401 | 0.178525 | 0.012185 | −0.156124 | −0.01376 | 0.089545 |
| 29 | 544.4/184.1>GPCho:Lyso 20:4 | −0.035838 | 0.206625 | −0.087558 | −0.054615 | −0.036423 | −0.115853 | 0.104923 | 0.03615 | −0.038652 | 0.111368 | −0.100202 | 0.083504 |
| 30 | 568.4/184.1>GPCho:Lyso 22:6 | −0.03059 | 0.200741 | −0.116829 | −0.005233 | −0.052663 | −0.018792 | 0.175703 | −0.043222 | 0.016018 | −0.158981 | 0.060073 | 0.062921 |
| 31 | 570.4/184.1>GPCho:Lyso 22:5 | −0.000973 | 0.198068 | −0.125238 | 0.02829 | −0.041037 | −0.066966 | 0.196835 | −0.002073 | 0.081485 | −0.066984 | 0.103762 | 0.076341 |
| 32 | 678.5/184.1>GPCho:28:0a | −0.080828 | −0.145494 | −0.057774 | 0.051783 | 0.073488 | 0.034959 | 0.244513 | −0.102012 | 0.02759 | 0.184735 | −0.122239 | 0.091796 |
| 33 | 704.6/184.1>GPCho:30:1a | −0.172399 | 0.054349 | 0.049161 | −0.018986 | 0.01932 | 0.141604 | −0.074129 | 0.117328 | −0.03369 | 0.065718 | −0.07788 | −0.04596 |
| 34 | 732.6/184.1>GPCho:32:1a | −0.086286 | −0.073792 | 0.036344 | −0.161682 | 0.099474 | −0.12856 | 0.168175 | 0.204494 | 0.089634 | 0.117077 | 0.193753 | 0.108649 |
| 35 | 734.6/184.1>GPCho:32:0a | −0.049281 | −0.080865 | 0.106653 | −0.205866 | 0.1432 | 0.189461 | 0.078498 | 0.190146 | −0.000966 | −0.025434 | 0.166392 | −0.00217 |
| 36 | 742.6/184.1>GPCho:34:2p, 34:3e | −0.058543 | −0.157498 | −0.11838 | 0.113042 | 0.033712 | 0.18433 | 0.047299 | −0.026486 | 0.048774 | 0.052586 | −0.184217 | 0.078929 |
| 37 | 744.6/184.1>GPCho:34:1p, 34:2e | 0.049743 | −0.029049 | −0.116074 | 0.264279 | −0.066273 | 0.155395 | −0.05934 | 0.180679 | 0.035698 | 0.000784 | −0.039587 | 0.18942 |
| 38 | 748.6/184.1>GPCho:34:0e | −0.074607 | −0.149022 | −0.004825 | 0.032752 | 0.0525 | 0.312468 | 0.079252 | 0.048131 | −0.056003 | −0.032368 | 0.119332 | 0.168792 |
| 39 | 756.6/184.1>GPCho:34:3a | −0.032484 | −0.231159 | −0.010942 | 0.030458 | −0.016341 | 0.034167 | 0.026766 | −0.023723 | 0.0671 | −0.018678 | 0.05227 | 0.049687 |
| 40 | 758.7/184.1>GPCho:34:2a | 0.088236 | −0.152804 | 0.076161 | 0.021317 | −0.035725 | −0.004351 | −0.222656 | 0.045425 | −0.025224 | −0.284319 | 0.142812 | −0.03945 |
| 41 | 762.6/184.1>GPCho:34:0a | 0.032999 | −0.12087 | 0.037531 | −0.162348 | 0.149346 | −0.000864 | 0.164692 | 0.241797 | 0.166697 | 0.062464 | 0.248753 | 0.142503 |
| 42 | 768.6/184.1>GPCho:36:3p, 36:4e | 0.087556 | 0.142449 | −0.156341 | 0.001321 | 0.003095 | 0.201739 | −0.051989 | 0.013139 | −0.072273 | 0.140726 | −0.029445 | 0.01888 |
| 43 | 770.6/184.1>GPCho:36:2p, 36:3e | 0.065267 | −0.012065 | −0.18544 | 0.203044 | −0.039818 | 0.202712 | −0.090219 | 0.065347 | 0.034857 | 0.112631 | 0.019931 | 0.07588 |
| 44 | 772.6/184.1>GPCho:36:1p, 36:2e | −0.002048 | −0.193114 | −0.042603 | 0.12875 | −0.040689 | 0.193081 | 0.072647 | 0.011671 | −0.030407 | −0.168336 | 0.008273 | 0.074312 |
| 45 | 782.6/184.1>GPCho:36:4a | 0.131219 | 0.116998 | 0.011145 | −0.171091 | 0.063428 | −0.024302 | −0.049856 | −0.002447 | −0.036011 | 0.159616 | −0.142783 | 0.030883 |
| 46 | 784.6/184.1>GPCho:36:3a | 0.160295 | −0.008991 | −0.051484 | 0.029377 | 0.04418 | −0.17906 | 0.019599 | −0.05395 | 0.143158 | 0.166969 | −0.026258 | 0.055103 |

APPENDIX B6-continued

PCA Transformation
Matrix (82 x 82; Early/Late)

| | | | | | | | | | | | | | | |
|---|---|---|---|---|---|---|---|---|---|---|---|---|---|---|
| 47 | 786.6/184.1>GPCho:36:2a | 0.107223 | −0.127997 | 0.002874 | 0.174435 | −0.073519 | −0.119144 | 0.036611 | −0.05818 | 0.07568 | −0.177546 | 0.145929 | −0.079089 |
| 48 | 788.6/184.1>GPCho:36:1a | −0.003521 | −0.206881 | 0.035807 | 0.070171 | −0.005814 | −0.085162 | 0.215057 | −0.05101 | 0.059232 | 0.098332 | 0.161377 | 0.07651 |
| 49 | 792.6/184.1>GPCho:38:5p, 38:6e | 0.039284 | 0.09622 | −0.189558 | 0.016353 | 0.026192 | 0.270288 | 0.129735 | −0.124608 | 0.009704 | −0.144079 | 0.079857 | −0.081208 |
| 50 | 794.6/184.1>GPCho:38:4p, 38:5e | 0.076225 | 0.152756 | −0.152851 | −0.031439 | −0.048614 | 0.204486 | −0.098381 | 0.030348 | −0.08524 | 0.022136 | 0.088344 | −0.052556 |
| 51 | 796.6/184.1>GPCho:38:3p, 38:4e | 0.079899 | 0.113243 | −0.157448 | −0.035491 | −0.00047 | 0.271934 | −0.113869 | −0.044847 | −0.083447 | 0.13794 | −0.009948 | −0.073734 |
| 52 | 808.6/184.1>GPCho:38:5a | 0.136042 | 0.146951 | −0.079285 | −0.056477 | 0.013549 | −0.019432 | 0.103669 | −0.122742 | 0.085873 | 0.028651 | 0.056487 | 0.03517 |
| 53 | 810.6/184.1>GPCho:38:4a | 0.145887 | 0.114042 | −0.018668 | −0.106765 | 0.026868 | −0.047234 | 0.025763 | −0.126999 | 0.032735 | 0.190327 | −0.055152 | −0.039714 |
| 54 | 814.6/184.1>GPCho:38:2a | −0.181903 | −0.000093 | 0.045466 | −0.065367 | −0.014336 | 0.109727 | 0.031439 | −0.022282 | −0.037581 | 0.100987 | −0.067301 | −0.033942 |
| 55 | 816.6/184.1>GPCho:38:1a | −0.12717 | −0.110941 | 0.034373 | 0.098715 | −0.074959 | 0.065418 | 0.08994 | −0.250294 | −0.074878 | 0.188259 | −0.082514 | 0.097145 |
| 56 | 820.6/184.1>GPCho:40:5p, 40:6e | 0.072827 | 0.142171 | −0.146511 | −0.004546 | −0.030141 | 0.229839 | 0.119493 | −0.129626 | −0.033368 | −0.203851 | 0.11673 | −0.027198 |
| 57 | 826.6/184.1>GPCho:40:2p, 40:3e | −0.039473 | −0.2254 | 0.002973 | −0.0437 | −0.006089 | 0.134977 | 0.097917 | −0.059349 | −0.097292 | −0.017012 | −0.040057 | −0.057557 |
| 58 | 828.6/184.1>GPCho:40:1p, 40:2e | −0.07607 | −0.210299 | −0.005714 | −0.012184 | 0.004438 | 0.144476 | 0.111634 | −0.088936 | −0.110793 | −0.050951 | −0.033058 | 0.002655 |
| 59 | 834.6/184.1>GPCho:40:6a | 0.106038 | 0.155471 | −0.08874 | −0.043774 | 0.029866 | 0.027101 | 0.18814 | −0.160152 | 0.052622 | −0.135163 | 0.09839 | −0.059345 |
| 60 | 836.6/184.1>GPCho:40:5a | 0.122654 | 0.038813 | −0.020047 | −0.076037 | 0.028808 | 0.024709 | 0.258671 | −0.31547 | 0.020572 | 0.024525 | 0.142176 | −0.125638 |
| 61 | 703.8/184.4>SM:d18:1/16:0 | −0.175281 | 0.060803 | 0.041765 | −0.023639 | 0.007731 | 0.134615 | −0.11856 | 0.081743 | −0.046613 | 0.084762 | −0.070924 | −0.022294 |
| 62 | 731.8/184.4>SM:d18:1/18:0 | −0.15771 | 0.031602 | 0.095861 | −0.126012 | 0.032054 | −0.000935 | −0.018888 | 0.013428 | −0.100806 | −0.051254 | −0.140268 | −0.034413 |
| 63 | 787.9/184.4>SM:d18:1/22:0 | −0.034915 | −0.069845 | 0.02273 | 0.285376 | −0.039092 | −0.128526 | 0.050653 | −0.220932 | 0.040457 | 0.045595 | −0.145218 | 0.068507 |
| 64 | 813.9/184.4>SM:d18:1/24:1 | −0.17899 | 0.050782 | 0.031286 | −0.058552 | 0.021206 | 0.105166 | −0.033842 | −0.020241 | −0.040045 | 0.085583 | −0.115016 | −0.020037 |
| 65 | 841.9/184.4>SM:d18:1/26:1 | −0.063341 | −0.199542 | 0.073823 | −0.023832 | 0.008619 | 0.060549 | 0.10256 | −0.175559 | −0.171318 | 0.090918 | −0.089674 | −0.045221 |
| 66 | 843.9/184.4>SM:d18:1/26:0 | 0.07193 | −0.146667 | −0.048016 | −0.099216 | −0.067891 | −0.035135 | −0.006765 | −0.121014 | −0.29072 | −0.045902 | −0.048509 | −0.227717 |
| 67 | 538.7/264.4>Cer:d18:1/16:0 | −0.142242 | 0.033448 | −0.09435 | −0.10523 | −0.148229 | −0.007934 | 0.060552 | 0.091805 | −0.004677 | −0.152295 | −0.023397 | 0.073568 |
| 68 | 566.7/264.4>Cer:d18:1/18:0 | −0.160803 | 0.016079 | 0.047383 | −0.140396 | −0.054296 | −0.072674 | 0.067322 | 0.021635 | −0.069244 | −0.210085 | −0.076293 | 0.00435 |
| 69 | 594.7/264.4>Cer:d18:1/20:0 | −0.172989 | 0.020438 | 0.037903 | −0.096046 | −0.025323 | −0.058304 | 0.087537 | 0.020958 | 0.014798 | −0.180158 | −0.073386 | 0.033821 |
| 70 | 622.8/264.4>Cer:d18:1/22:0 | −0.174587 | 0.045926 | 0.002318 | −0.01203 | −0.026162 | −0.082588 | 0.086508 | −0.044505 | 0.116897 | −0.12969 | −0.126322 | 0.064931 |
| 71 | 648.9/264.4>Cer:d18:1/24:1 | −0.18003 | 0.03166 | −0.010177 | −0.096972 | −0.045584 | −0.016893 | 0.056997 | 0.027825 | 0.044892 | −0.151173 | −0.032884 | 0.00765 |
| 72 | 650.9/264.4>Cer:d18:1/24:0 | −0.139944 | 0.097577 | 0.008368 | 0.102159 | 0.020515 | −0.052467 | 0.037886 | −0.117716 | 0.180256 | 0.028409 | −0.190099 | 0.074538 |
| 73 | 700.7/264.4>MonoHexCer:d18:1/16:0 | −0.180889 | 0.075083 | 0.046535 | 0.041136 | −0.005365 | 0.033516 | −0.040045 | −0.015177 | 0.019077 | 0.001707 | 0.157858 | −0.058633 |
| 74 | 728.7/264.4>MonoHexCer:d18:1/18:0 | −0.182163 | 0.074672 | 0.013431 | 0.003025 | −0.02678 | 0.002908 | −0.031859 | 0.009586 | 0.003315 | −0.00366 | 0.096276 | −0.090522 |
| 75 | 784.8/264.4>MonoHexCer:d18:1/22:0 | −0.166011 | 0.085551 | 0.031445 | 0.112037 | −0.06181 | 0.020351 | −0.05178 | −0.099979 | 0.040825 | 0.052457 | 0.12096 | −0.036509 |
| 76 | 810.9/264.4>MonoHexCer:d18:1/24:1 | −0.174019 | 0.089408 | 0.027701 | 0.012556 | −0.054741 | 0.027562 | −0.038916 | −0.034517 | 0.001081 | −0.017102 | 0.215152 | −0.051864 |
| 77 | 812.9/264.4>MonoHexCer:d18:1/24:0 | −0.160006 | 0.096075 | 0.025037 | 0.105103 | −0.092382 | 0.026364 | −0.024355 | −0.101235 | 0.002992 | 0.088637 | 0.133098 | 0.023777 |
| 78 | 862.7/264.4>DiHexCer:d18:1/16:0 | −0.175317 | 0.085072 | 0.043653 | 0.037442 | −0.037644 | 0.031571 | −0.039425 | −0.054154 | 0.004806 | 0.073388 | 0.148249 | −0.006505 |
| 79 | 890.7/264.4>DiHexCer:d18:1/18:0 | −0.181824 | 0.070329 | 0.035695 | 0.036663 | −0.022086 | −0.027786 | −0.003397 | −0.070978 | 0.000885 | 0.000428 | −0.000133 | −0.091269 |
| 80 | 946.8/264.4>DiHexCer:d18:1/22:0 | −0.172009 | 0.081881 | 0.017889 | 0.094602 | −0.066074 | −0.022863 | −0.020225 | −0.088566 | −0.003312 | 0.090423 | 0.081756 | 0.012728 |
| 81 | 972.9/264.4>DiHexCer:d18:1/24:1 | −0.176857 | 0.08314 | 0.023134 | 0.027124 | −0.052376 | 0.01667 | −0.037757 | −0.028942 | −0.014648 | 0.083128 | 0.204802 | −0.021702 |
| 82 | 974.9/264.4>DiHexCer:d18:1/24:0 | −0.168763 | 0.089389 | 0.01261 | 0.09257 | −0.05651 | 0.010652 | −0.036838 | −0.079889 | 0.017903 | 0.122981 | 0.114884 | −0.037278 |

| | N | O | P | Q | R | S | T | U | V | W | X | Y | Z | AA |
|---|---|---|---|---|---|---|---|---|---|---|---|---|---|---|
| 1 | −0.092174 | 0.293313 | −0.043862 | 0.121739 | 0.017243 | 0.02755 | 0.039279 | 0.033333 | −0.026265 | 0.043844 | 0.146647 | 0.056482 | 0.041524 | 0.155149 |
| 2 | 0.210736 | 0.082006 | −0.181552 | 0.164293 | −0.178766 | −0.068917 | −0.089321 | 0.00705 | 0.002514 | −0.07526 | −0.10348 | 0.071779 | 0.168363 | −0.090637 |
| 3 | −0.078506 | 0.325413 | 0.036458 | 0.185286 | 0.033978 | −0.043814 | 0.062899 | −0.023873 | −0.026091 | 0.085843 | 0.091422 | −0.118898 | 0.064758 | −0.028475 |
| 4 | −0.054513 | 0.082122 | 0.03186 | 0.034643 | −0.022648 | −0.06334 | 0.04733 | −0.062312 | −0.155291 | 0.025052 | −0.070673 | −0.037784 | 0.06496 | −0.129695 |
| 5 | −0.050479 | 0.068378 | 0.068363 | −0.018644 | −0.041148 | −0.012195 | 0.021711 | −0.02819 | −0.08781 | 0.015581 | −0.005676 | −0.072428 | 0.013785 | −0.144526 |
| 6 | 0.006021 | −0.007361 | −0.012564 | −0.024518 | −0.086673 | −0.064811 | 0.013327 | 0.02561 | −0.016918 | −0.038075 | −0.057692 | −0.033455 | 0.037101 | 0.026394 |
| 7 | 0.10462 | 0.018598 | −0.213477 | 0.152511 | −0.07258 | −0.012153 | −0.100656 | −0.071286 | −0.084634 | −0.106099 | 0.096468 | 0.145985 | 0.105608 | −0.037516 |
| 8 | −0.029486 | −0.057572 | −0.084601 | 0.024415 | −0.154767 | 0.270576 | 0.202958 | −0.028276 | 0.1282 | −0.021415 | −0.262218 | −0.131745 | −0.029259 | 0.137546 |
| 9 | 0.152213 | −0.047245 | −0.087023 | 0.04314 | −0.031016 | −0.074187 | −0.148703 | −0.043633 | 0.279039 | 0.08456 | 0.187587 | −0.141985 | −0.107395 | 0.306707 |
| 10 | −0.043596 | −0.12483 | 0.096885 | −0.211406 | 0.08779 | −0.022871 | −0.040376 | 0.203926 | −0.012942 | −0.054414 | −0.051927 | −0.045073 | 0.114394 | −0.211074 |
| 11 | 0.008256 | 0.105474 | 0.025243 | −0.184904 | 0.14451 | 0.026175 | 0.289461 | 0.199871 | 0.108194 | −0.012347 | −0.201466 | 0.097525 | −0.325425 | −0.013657 |

APPENDIX B6-continued

PCA Transformation
Matrix (82 x 82; Early/Late)

| | | | | | | | | | | | | | | |
|---|---|---|---|---|---|---|---|---|---|---|---|---|---|---|
| 12 | 0.135623 | −0.005684 | −0.043117 | −0.058564 | 0.061455 | 0.108499 | 0.066037 | −0.002877 | 0.02338 | 0.054101 | −0.091557 | 0.056941 | −0.060913 | 0.171376 |
| 13 | −0.085185 | 0.007952 | 0.024806 | −0.118029 | 0.110302 | −0.082256 | 0.039862 | −0.026883 | −0.004221 | −0.066879 | −0.031008 | 0.066074 | −0.037343 | 0.067642 |
| 14 | −0.179903 | −0.159922 | 0.009354 | −0.143174 | 0.133548 | 0.013476 | −0.071541 | 0.015844 | −0.086443 | 0.064608 | 0.060377 | 0.10513 | −0.050517 | 0.091293 |
| 15 | −0.147598 | 0.060704 | 0.057078 | −0.146404 | −0.042608 | 0.080201 | −0.012064 | 0.195835 | −0.093701 | 0.161056 | 0.044149 | −0.051775 | −0.086465 | −0.001556 |
| 16 | −0.078895 | −0.194197 | −0.020864 | −0.107437 | 0.128941 | −0.071573 | 0.011252 | −0.045857 | −0.017822 | −0.014661 | 0.035701 | −0.021449 | −0.022158 | −0.034056 |
| 17 | −0.339492 | 0.158248 | 0.066597 | 0.168733 | 0.065194 | 0.229546 | 0.184835 | −0.001271 | −0.039983 | 0.131757 | −0.069381 | 0.106203 | 0.182775 | −0.08972 |
| 18 | 0.186653 | −0.048427 | 0.100107 | 0.062594 | 0.070617 | 0.189754 | 0.205979 | 0.135056 | 0.11202 | 0.025282 | −0.236863 | 0.066087 | 0.112343 | −0.038155 |
| 19 | 0.096958 | 0.138148 | 0.134941 | −0.118991 | 0.18931 | 0.005771 | −0.037006 | 0.153937 | −0.230464 | −0.003099 | −0.000271 | −0.011741 | −0.040274 | 0.025891 |
| 20 | 0.054363 | −0.112152 | −0.017074 | 0.164599 | 0.108739 | −0.091541 | 0.047385 | −0.206363 | −0.157061 | 0.15337 | −0.152072 | 0.175648 | 0.088123 | 0.023678 |
| 21 | −0.019364 | −0.058813 | 0.035115 | 0.154304 | −0.031724 | 0.043205 | 0.033911 | −0.032081 | 0.015633 | 0.064767 | −0.136315 | 0.153846 | −0.050972 | −0.098777 |
| 22 | 0.137393 | −0.227996 | −0.072065 | 0.040086 | −0.103906 | 0.207347 | 0.142189 | −0.028501 | 0.162542 | −0.025868 | −0.034498 | −0.198121 | −0.046515 | 0.020116 |
| 23 | −0.09277 | −0.01044 | 0.000469 | −0.046007 | 0.064483 | −0.085452 | −0.052954 | −0.144987 | 0.064602 | 0.080134 | −0.175692 | 0.089371 | 0.095333 | 0.188751 |
| 24 | 0.025698 | −0.053576 | −0.047997 | −0.2148 | −0.065393 | −0.060549 | 0.000252 | −0.114453 | 0.118307 | 0.035907 | −0.098746 | −0.028861 | 0.017072 | −0.102776 |
| 25 | −0.006366 | −0.225199 | 0.038362 | −0.067335 | 0.139532 | 0.109685 | 0.010071 | −0.022494 | 0.057852 | −0.068013 | 0.293508 | 0.159802 | 0.121317 | −0.031954 |
| 26 | −0.014235 | 0.031957 | 0.161921 | −0.045492 | −0.055816 | −0.176912 | −0.060348 | −0.111228 | −0.188465 | −0.241478 | −0.222854 | −0.125735 | 0.000795 | −0.022414 |
| 27 | −0.139513 | −0.038735 | 0.004046 | 0.092534 | −0.051039 | −0.039363 | 0.023472 | 0.008706 | −0.137543 | −0.116595 | −0.175938 | 0.236507 | −0.160448 | 0.096714 |
| 28 | −0.10939 | −0.065932 | −0.128684 | −0.043511 | 0.004935 | 0.220003 | 0.120926 | 0.086507 | −0.03857 | 0.142926 | 0.290219 | −0.185306 | 0.06416 | 0.067277 |
| 29 | 0.07286 | 0.177862 | −0.097822 | −0.059306 | 0.170392 | 0.090189 | 0.061495 | −0.104249 | −0.030708 | 0.018993 | 0.138134 | −0.181054 | −0.096952 | −0.22746 |
| 30 | −0.095308 | 0.044784 | −0.148354 | 0.181794 | 0.021543 | −0.040886 | 0.103409 | −0.083394 | −0.00431 | −0.034471 | −0.057438 | 0.005183 | −0.219063 | −0.15602 |
| 31 | −0.047912 | 0.106007 | −0.14529 | 0.048343 | 0.059584 | 0.058191 | 0.028591 | −0.070307 | −0.169467 | 0.198371 | 0.065994 | −0.029735 | −0.05174 | −0.089314 |
| 32 | −0.192989 | −0.032086 | 0.015637 | −0.038445 | 0.105988 | 0.121009 | −0.274626 | 0.350091 | −0.268832 | −0.17772 | −0.070232 | −0.147018 | 0.053167 | 0.208042 |
| 33 | −0.04363 | −0.102518 | −0.142603 | 0.045085 | −0.013712 | −0.028655 | 0.065495 | 0.17973 | 0.01815 | 0.248204 | −0.160749 | −0.052414 | 0.138162 | −0.059748 |
| 34 | −0.004037 | −0.110456 | 0.230573 | 0.428816 | 0.101425 | 0.0883 | −0.121118 | 0.146602 | −0.126526 | −0.003992 | −0.022477 | 0.035426 | −0.112418 | 0.075473 |
| 35 | 0.097013 | 0.004836 | −0.141961 | −0.129569 | −0.071209 | 0.173047 | −0.097561 | −0.005087 | −0.09707 | 0.102882 | −0.0117 | 0.060208 | 0.147674 | 0.086129 |
| 36 | −0.156112 | −0.035543 | 0.069545 | 0.095796 | 0.206655 | −0.041666 | −0.103611 | 0.033246 | 0.244372 | −0.058839 | −0.031881 | 0.018585 | 0.005366 | −0.32966 |
| 37 | 0.009728 | 0.002407 | 0.124766 | 0.105463 | 0.008355 | −0.189557 | −0.214178 | 0.147844 | 0.119737 | 0.170673 | 0.08202 | 0.104145 | −0.037459 | −0.014553 |
| 38 | 0.135462 | 0.006859 | −0.189235 | 0.018399 | 0.090863 | 0.197287 | −0.059729 | 0.014528 | −0.146927 | 0.075019 | 0.085 | 0.245181 | 0.101009 | −0.145985 |
| 39 | −0.061298 | 0.163718 | 0.082563 | 0.009222 | 0.162677 | 0.044916 | 0.145967 | −0.306207 | −0.052273 | −0.187459 | 0.018414 | −0.063363 | 0.247559 | 0.119233 |
| 40 | −0.2204 | 0.013143 | 0.01745 | −0.043847 | −0.194795 | 0.059533 | −0.155523 | −0.086045 | 0.019288 | −0.209253 | −0.018104 | −0.092477 | −0.010201 | 0.056747 |
| 41 | −0.149108 | 0.021957 | 0.105152 | −0.086356 | −0.22057 | −0.071789 | −0.056377 | −0.093641 | −0.008335 | 0.09339 | 0.050885 | 0.200648 | −0.029109 | −0.085929 |
| 42 | 0.093604 | −0.028101 | 0.261635 | −0.051344 | −0.162932 | 0.094044 | 0.041671 | −0.021047 | −0.00523 | −0.057218 | 0.012336 | −0.033301 | 0.140121 | 0.090197 |
| 43 | 0.068617 | 0.04356 | 0.219571 | 0.044963 | −0.085617 | −0.031602 | −0.008445 | 0.028916 | 0.106875 | 0.118524 | 0.208747 | 0.082206 | −0.006055 | 0.035401 |
| 44 | 0.112662 | 0.148792 | −0.143778 | −0.015832 | 0.233732 | 0.037632 | −0.158694 | −0.146898 | 0.04975 | 0.032445 | −0.028618 | 0.002411 | −0.095125 | −0.002987 |
| 45 | 0.025892 | 0.027752 | −0.045035 | −0.102139 | 0.187732 | 0.06673 | −0.113607 | −0.128074 | 0.070105 | −0.055218 | −0.164113 | 0.14283 | −0.068181 | −0.015196 |
| 46 | 0.006297 | 0.216169 | 0.123971 | 0.047331 | 0.090014 | 0.156237 | 0.126501 | 0.101287 | 0.286367 | −0.113531 | 0.140797 | 0.274132 | 0.011814 | 0.219095 |
| 47 | 0.230016 | 0.002159 | 0.013755 | −0.020727 | −0.056661 | −0.112519 | 0.014558 | 0.157745 | −0.031604 | −0.046748 | 0.078106 | −0.095292 | −0.104004 | −0.060969 |
| 48 | 0.120633 | 0.072962 | 0.141485 | 0.031908 | −0.124547 | −0.053116 | 0.042373 | −0.132996 | −0.147811 | 0.087873 | 0.043526 | −0.202142 | −0.01009 | −0.140868 |
| 49 | −0.110553 | −0.106342 | 0.215559 | 0.10936 | −0.069099 | 0.052613 | 0.115427 | 0.015273 | 0.102341 | −0.175949 | 0.168813 | −0.02581 | 0.154924 | −0.103832 |
| 50 | 0.136165 | 0.004731 | 0.110124 | −0.085083 | −0.026902 | 0.050156 | 0.091253 | −0.004125 | −0.181501 | 0.054463 | −0.02311 | −0.076548 | −0.050955 | 0.126773 |
| 51 | 0.101008 | −0.038094 | 0.140602 | −0.066102 | −0.018333 | 0.206194 | −0.022191 | −0.123465 | −0.236266 | 0.037431 | 0.069925 | −0.019252 | −0.058557 | −0.017891 |
| 52 | 0.017811 | 0.030893 | −0.037281 | −0.023997 | 0.110309 | 0.017117 | −0.098292 | −0.039751 | −0.011314 | 0.156054 | −0.047306 | 0.101599 | 0.157435 | 0.046251 |
| 53 | 0.242644 | −0.003483 | −0.004658 | −0.083656 | 0.163449 | 0.051863 | −0.097861 | −0.010643 | 0.01272 | −0.002416 | 0.007648 | −0.005433 | 0.085474 | −0.152703 |
| 54 | −0.004412 | −0.023767 | −0.035723 | −0.006734 | −0.101934 | −0.233484 | 0.231365 | 0.078894 | −0.028785 | −0.088645 | 0.132281 | 0.109747 | −0.070073 | 0.022794 |
| 55 | −0.064213 | 0.068525 | −0.070962 | 0.07611 | −0.209387 | −0.092184 | 0.134528 | −0.067082 | −0.104713 | −0.053535 | 0.004097 | 0.001846 | 0.062742 | 0.11707 |
| 56 | −0.068949 | −0.055431 | 0.000514 | 0.09619 | 0.02446 | 0.017366 | −0.026433 | −0.072746 | 0.01225 | 0.060337 | −0.026847 | −0.043844 | −0.129537 | 0.089409 |
| 57 | −0.036691 | 0.11093 | 0.062306 | −0.055383 | 0.093177 | −0.083892 | 0.008151 | −0.165681 | 0.053548 | 0.077477 | −0.008057 | −0.039897 | −0.128544 | 0.053378 |
| 58 | −0.028132 | 0.017632 | −0.005225 | −0.016833 | 0.135982 | −0.006316 | 0.009574 | −0.129948 | 0.064909 | 0.000775 | −0.007923 | 0.011199 | −0.125069 | 0.051982 |
| 59 | −0.045837 | −0.137111 | −0.083329 | 0.116392 | 0.017872 | −0.042515 | 0.001142 | 0.057564 | 0.069498 | −0.086229 | −0.147534 | 0.076972 | 0.15068 | 0.014735 |
| 60 | −0.197936 | 0.020704 | 0.005158 | −0.120921 | −0.02399 | −0.269675 | −0.06961 | 0.085147 | 0.165851 | 0.313323 | −0.025975 | −0.059931 | 0.243551 | 0.068649 |
| 61 | −0.018154 | −0.064107 | −0.102159 | −0.006729 | 0.012318 | −0.055217 | 0.015796 | 0.121081 | 0.047531 | 0.160215 | −0.100807 | −0.107113 | 0.035862 | −0.063546 |

APPENDIX B6-continued

PCA Transformation
Matrix (82 x 82; Early/Late)

| | | | | | | | | | | | | | | |
|---|---|---|---|---|---|---|---|---|---|---|---|---|---|---|
| 62 | −0.001422 | −0.203726 | 0.216002 | 0.224705 | 0.092619 | −0.010114 | −0.02689 | −0.078927 | −0.018013 | 0.212944 | −0.088941 | −0.123447 | −0.039826 | 0.070324 |
| 63 | 0.152484 | −0.122309 | −0.000924 | 0.070788 | −0.131587 | −0.073154 | 0.001396 | 0.04148 | −0.222581 | 0.183126 | −0.008326 | 0.173215 | −0.092175 | −0.018543 |
| 64 | 0.005317 | −0.110309 | −0.062477 | −0.008321 | −0.052489 | −0.199355 | 0.153477 | 0.091786 | −0.050951 | −0.080492 | 0.131158 | 0.230419 | −0.088195 | 0.01527 |
| 65 | −0.082207 | 0.049677 | 0.099165 | −0.097165 | 0.106384 | −0.088827 | 0.082609 | −0.050275 | −0.084043 | 0.060642 | −0.001206 | −0.05609 | 0.028882 | −0.009185 |
| 66 | 0.016339 | 0.296585 | 0.062236 | 0.062012 | −0.273172 | 0.19688 | −0.210599 | 0.212442 | 0.077158 | 0.06327 | −0.075618 | 0.038914 | −0.227402 | −0.145762 |
| 67 | 0.18134 | 0.286969 | 0.035607 | −0.073331 | 0.012152 | −0.129926 | 0.006516 | 0.185302 | 0.056727 | −0.027562 | −0.186708 | 0.025263 | 0.315026 | 0.078715 |
| 68 | 0.156481 | −0.006352 | 0.264698 | 0.045827 | 0.049844 | −0.055661 | −0.008611 | −0.051895 | 0.00732 | 0.068984 | −0.003249 | 0.002901 | 0.034025 | 0.021554 |
| 69 | 0.163568 | 0.031889 | 0.275274 | −0.018272 | −0.002773 | 0.019124 | 0.037144 | −0.084943 | 0.051077 | 0.133669 | −0.018542 | 0.064118 | −0.017689 | 0.051737 |
| 70 | 0.040439 | −0.049718 | 0.185666 | −0.200819 | −0.177008 | 0.161883 | −0.041433 | −0.109727 | 0.014339 | 0.107367 | −0.038444 | 0.131002 | 0.151961 | −0.042285 |
| 71 | 0.045694 | 0.033954 | 0.117551 | −0.184196 | −0.019657 | −0.054776 | 0.075194 | 0.002586 | −0.017953 | −0.087628 | 0.036354 | 0.184703 | −0.024885 | −0.170692 |
| 72 | −0.190211 | 0.020673 | 0.033957 | −0.182767 | −0.236254 | 0.144862 | −0.168038 | −0.218316 | 0.08868 | 0.127217 | −0.03523 | 0.151118 | −0.142118 | −0.051323 |
| 73 | 0.019663 | −0.051331 | −0.040108 | −0.02239 | −0.027438 | 0.01409 | −0.07871 | −0.020243 | −0.031129 | −0.130541 | −0.017219 | −0.003805 | 0.083448 | 0.069319 |
| 74 | 0.020466 | 0.016389 | 0.092278 | 0.064002 | 0.132336 | −0.033438 | −0.23406 | −0.04053 | 0.060734 | 0.030917 | −0.046606 | −0.089332 | −0.05959 | 0.07247 |
| 75 | 0.009248 | 0.063508 | −0.031068 | −0.062475 | −0.023706 | 0.070393 | −0.161259 | −0.026274 | −0.038486 | −0.00194 | −0.106402 | 0.062234 | −0.024594 | 0.120562 |
| 76 | 0.055113 | 0.071632 | −0.046124 | −0.022116 | 0.047066 | −0.11258 | −0.0093 | −0.023849 | −0.029038 | −0.041812 | 0.061125 | 0.062571 | −0.040307 | 0.143886 |
| 77 | 0.001186 | 0.057454 | −0.092337 | −0.028467 | −0.08571 | 0.058976 | −0.143657 | −0.012691 | −0.046258 | −0.058859 | 0.046369 | 0.10132 | 0.023624 | 0.095472 |
| 78 | 0.025694 | 0.031837 | 0.004025 | 0.06008 | −0.062546 | −0.07765 | −0.031567 | −0.123667 | 0.112284 | 0.026627 | −0.055486 | −0.143757 | −0.025376 | −0.002763 |
| 79 | 0.012247 | −0.104778 | 0.080411 | 0.076482 | 0.060424 | 0.114545 | −0.163038 | −0.082303 | 0.005913 | −0.150227 | 0.048448 | 0.044594 | −0.011479 | −0.067547 |
| 80 | −0.007676 | 0.047271 | 0.019832 | 0.013004 | −0.001123 | 0.099714 | −0.144144 | −0.008395 | 0.1295 | −0.071786 | −0.118933 | −0.039893 | −0.007349 | −0.104625 |
| 81 | 0.025542 | 0.076983 | 0.050075 | 0.016614 | 0.002408 | −0.06908 | −0.036971 | 0.018774 | 0.059834 | −0.192178 | −0.036836 | −0.029814 | −0.040715 | −0.047908 |
| 82 | −0.0137 | 0.001326 | −0.011881 | 0.088604 | −0.023311 | 0.030166 | −0.123481 | 0.013824 | 0.121542 | −0.073848 | 0.096317 | −0.01246 | 0.137479 | −0.178485 |

| | AB | AC | AD | AE | AF | AG | AH | AI | AJ | AK | AL | AM | AN | AO |
|---|---|---|---|---|---|---|---|---|---|---|---|---|---|---|
| 1 | −0.023684 | 0.038441 | −0.02201 | 0.043133 | −0.078982 | −0.196107 | −0.027417 | −0.025864 | −0.019444 | 0.121071 | 0.103326 | 0.132877 | 0.152964 | 0.064527 |
| 2 | −0.106938 | −0.122679 | 0.080722 | −0.110182 | 0.287171 | 0.017205 | −0.114088 | −0.15795 | 0.179021 | −0.112581 | 0.001854 | −0.081568 | 0.091046 | −0.159848 |
| 3 | −0.189675 | 0.164962 | 0.102371 | 0.015344 | −0.207537 | −0.03752 | 0.096363 | −0.112452 | −0.103973 | −0.213414 | 0.118834 | −0.038237 | 0.163872 | 0.079369 |
| 4 | −0.133374 | 0.052607 | −0.149373 | 0.132099 | 0.072195 | 0.023602 | 0.098973 | 0.109096 | 0.06429 | −0.166018 | −0.032795 | −0.124153 | −0.122861 | −0.01422 |
| 5 | −0.001016 | 0.047836 | −0.098913 | −0.017005 | 0.098846 | −0.015316 | 0.09419 | 0.122062 | 0.08826 | −0.011788 | −0.019863 | −0.033275 | −0.032439 | 0.084734 |
| 6 | 0.115899 | 0.014645 | −0.078426 | −0.029812 | 0.115507 | −0.075353 | 0.136485 | −0.043627 | 0.211596 | 0.078282 | −0.02651 | −0.026335 | 0.06836 | −0.041792 |
| 7 | −0.102093 | −0.174293 | 0.222101 | −0.136336 | −0.018118 | −0.092681 | −0.089596 | −0.143002 | 0.05703 | 0.172182 | 0.195523 | 0.198744 | −0.278217 | 0.117266 |
| 8 | 0.072048 | 0.176732 | 0.085971 | 0.020332 | 0.023561 | −0.017986 | 0.043474 | −0.144018 | 0.014011 | −0.001029 | 0.087218 | −0.066355 | 0.064314 | 0.045024 |
| 9 | 0.233244 | −0.079443 | 0.128543 | 0.088614 | −0.07609 | −0.106636 | −0.084157 | 0.205148 | −0.373437 | −0.113668 | −0.061613 | 0.071431 | 0.057309 | −0.1024 |
| 10 | 0.102046 | 0.128151 | 0.019268 | −0.277439 | −0.048379 | 0.070921 | 0.063387 | −0.141124 | −0.093823 | 0.003375 | 0.067936 | 0.16763 | −0.072296 | −0.302428 |
| 11 | −0.221537 | 0.101884 | 0.059424 | −0.005324 | 0.080247 | −0.092374 | −0.222557 | −0.014226 | −0.034339 | 0.024881 | 0.053997 | 0.172994 | 0.082275 | 0.029478 |
| 12 | −0.022898 | −0.085497 | 0.027773 | 0.057558 | −0.080527 | 0.239245 | −0.16016 | −0.193246 | 0.068858 | 0.18386 | −0.167549 | −0.143871 | 0.105442 | 0.176294 |
| 13 | −0.001336 | 0.005118 | −0.004596 | −0.063041 | −0.053769 | −0.049906 | 0.002497 | 0.012201 | −0.065383 | −0.121375 | 0.02763 | −0.083475 | −0.028173 | 0.068698 |
| 14 | −0.010588 | −0.078069 | −0.045963 | 0.013001 | −0.013931 | −0.084132 | −0.127057 | 0.044834 | 0.105098 | −0.025014 | 0.085489 | −0.033205 | −0.080467 | 0.074536 |
| 15 | 0.062834 | 0.039486 | −0.007748 | −0.061258 | 0.076642 | −0.153865 | −0.01808 | −0.024185 | −0.025237 | −0.013661 | −0.052711 | 0.04469 | −0.106167 | 0.079591 |
| 16 | −0.000534 | 0.003301 | −0.084681 | −0.00859 | −0.06015 | 0.063027 | −0.069193 | 0.161889 | −0.063903 | −0.059379 | −0.042076 | 0.159443 | −0.052264 | −0.008188 |
| 17 | 0.162008 | 0.101738 | 0.158758 | −0.000704 | −0.085486 | 0.117197 | −0.176014 | 0.003538 | −0.13899 | −0.08876 | 0.057595 | −0.09959 | −0.261915 | −0.074095 |
| 18 | −0.015934 | −0.239316 | 0.166711 | −0.021361 | 0.09255 | −0.2211 | 0.222805 | 0.025973 | −0.102222 | 0.018735 | 0.023744 | 0.181644 | 0.072444 | 0.051468 |
| 19 | 0.144078 | −0.16222 | −0.03166 | −0.135181 | 0.131519 | −0.104045 | 0.061807 | 0.032998 | −0.00914 | −0.075679 | −0.074239 | 0.016207 | 0.001768 | 0.085877 |
| 20 | 0.074189 | −0.141919 | 0.14551 | −0.018804 | −0.106687 | −0.014975 | 0.097296 | 0.196659 | −0.100366 | −0.166446 | −0.152676 | −0.104026 | 0.123912 | 0.043768 |
| 21 | 0.134683 | 0.070319 | −0.026234 | −0.032496 | −0.019733 | 0.072986 | 0.081084 | −0.103628 | −0.11439 | 0.278706 | −0.218574 | 0.029714 | 0.106442 | −0.116396 |
| 22 | 0.024042 | 0.178983 | −0.045555 | 0.082593 | 0.022604 | −0.016844 | 0.169955 | 0.117438 | −0.029381 | −0.102215 | 0.006946 | −0.138645 | −0.163262 | 0.174201 |
| 23 | 0.01415 | −0.188754 | −0.02 | 0.15195 | −0.162012 | −0.067477 | −0.060088 | −0.06562 | 0.17739 | −0.079527 | −0.115984 | 0.194574 | −0.140862 | 0.033812 |
| 24 | 0.084494 | −0.078168 | 0.011116 | −0.038022 | 0.06832 | 0.270105 | 0.110826 | 0.036824 | 0.006025 | −0.19118 | 0.268742 | −0.034937 | −0.082638 | −0.066431 |
| 25 | −0.259234 | 0.199866 | −0.131169 | 0.02782 | 0.029401 | −0.08347 | −0.035528 | −0.014596 | −0.20194 | 0.049719 | −0.071651 | −0.157049 | 0.016288 | −0.056827 |
| 26 | 0.137172 | 0.265337 | 0.007218 | −0.108632 | −0.111311 | −0.011005 | 0.020332 | 0.13799 | −0.112043 | 0.129461 | −0.063781 | 0.338155 | 0.070846 | 0.109057 |

APPENDIX B6-continued

PCA Transformation
Matrix (82 x 82; Early/Late)

| | | | | | | | | | | | | | | |
|---|---|---|---|---|---|---|---|---|---|---|---|---|---|---|
| 27 | 0.039337 | 0.076391 | −0.008216 | 0.038644 | 0.084234 | −0.195339 | 0.086631 | 0.031316 | −0.016506 | −0.028632 | −0.177768 | −0.238538 | −0.012051 | −0.095033 |
| 28 | 0.288294 | 0.010194 | 0.098982 | −0.071578 | 0.206422 | −0.032805 | −0.121075 | 0.078622 | 0.201854 | 0.018293 | −0.11263 | −0.070408 | 0.146047 | −0.079014 |
| 29 | 0.049163 | −0.07872 | 0.076757 | −0.042813 | −0.077005 | 0.04902 | −0.04713 | −0.117309 | −0.007593 | −0.095178 | −0.230033 | −0.010147 | 0.056668 | −0.06565 |
| 30 | −0.066049 | −0.134666 | −0.037303 | −0.129387 | −0.152543 | −0.008624 | −0.019475 | 0.049193 | −0.072478 | −0.015213 | −0.136396 | −0.051316 | 0.069375 | −0.017756 |
| 31 | 0.00172 | −0.171126 | −0.116601 | 0.072137 | 0.123861 | 0.136989 | 0.151977 | 0.003314 | −0.066818 | 0.0851 | 0.173912 | 0.061895 | −0.109823 | −0.048522 |
| 32 | −0.083961 | −0.12192 | 0.183709 | 0.06138 | −0.143269 | 0.128098 | 0.115444 | 0.029609 | −0.022555 | −0.090284 | 0.016134 | −0.116643 | −0.041109 | 0.042729 |
| 33 | −0.089208 | −0.123754 | −0.036203 | −0.077258 | −0.101557 | 0.060523 | 0.044579 | 0.032132 | −0.062523 | 0.243468 | −0.063084 | −0.040885 | 0.017643 | −0.140295 |
| 34 | 0.002281 | −0.061098 | −0.112357 | 0.160392 | 0.114313 | −0.112363 | −0.159616 | 0.013407 | 0.008063 | −0.020821 | −0.027895 | 0.127123 | −0.138713 | −0.153769 |
| 35 | 0.000241 | −0.176237 | −0.277723 | −0.132033 | −0.205966 | −0.146448 | 0.040825 | 0.016002 | −0.041757 | −0.214129 | −0.032052 | 0.068771 | 0.065055 | −0.035338 |
| 36 | 0.191398 | −0.176771 | −0.10241 | 0.38773 | 0.053848 | 0.029445 | −0.006594 | −0.197321 | −0.101964 | −0.10797 | 0.020677 | −0.015613 | 0.107788 | −0.128828 |
| 37 | −0.039281 | 0.092886 | 0.037001 | −0.112888 | 0.04537 | −0.130047 | 0.159953 | −0.082336 | −0.078198 | 0.133818 | −0.058485 | −0.263814 | −0.055011 | 0.128241 |
| 38 | 0.056902 | 0.294665 | 0.166264 | 0.017784 | −0.102009 | −0.077144 | 0.115105 | 0.119721 | 0.165075 | −0.168858 | −0.068799 | 0.084039 | 0.008996 | 0.038106 |
| 39 | 0.036222 | −0.012061 | −0.132059 | 0.117414 | 0.157973 | 0.002596 | −0.090795 | 0.045662 | −0.025421 | 0.23306 | −0.017723 | 0.044324 | 0.050747 | 0.047631 |
| 40 | −0.1804 | 0.069917 | −0.005441 | 0.121564 | 0.046734 | 0.013968 | 0.059002 | −0.127425 | −0.025035 | −0.086658 | −0.012544 | 0.070845 | 0.084885 | −0.097313 |
| 41 | 0.186165 | −0.054445 | 0.224965 | −0.155596 | 0.059112 | 0.028059 | −0.082116 | 0.039351 | −0.131745 | 0.064562 | 0.066545 | −0.077751 | 0.191694 | 0.077905 |
| 42 | 0.085528 | −0.093818 | 0.025912 | −0.03551 | −0.082455 | −0.031166 | −0.135658 | 0.024405 | 0.028311 | −0.048894 | −0.008768 | −0.064908 | 0.091224 | −0.044544 |
| 43 | −0.15261 | 0.107196 | 0.021496 | −0.022063 | 0.078684 | 0.11758 | −0.159571 | −0.01481 | 0.034617 | 0.008143 | −0.082611 | −0.016179 | −0.11003 | 0.029254 |
| 44 | −0.029081 | 0.147517 | −0.112827 | −0.068316 | 0.050782 | −0.002999 | −0.012886 | 0.002073 | −0.077947 | 0.03971 | −0.023334 | 0.041138 | −0.127671 | 0.147202 |
| 45 | 0.084322 | 0.022742 | 0.029746 | −0.165103 | 0.045589 | −0.079888 | −0.053711 | −0.068171 | −0.025352 | −0.142526 | 0.064874 | −0.272856 | −0.048904 | 0.165876 |
| 46 | −0.010379 | −0.037478 | −0.047848 | −0.201802 | −0.16918 | 0.161727 | 0.233465 | 0.122484 | 0.177271 | −0.025449 | 0.068003 | 0.088064 | −0.090932 | −0.173012 |
| 47 | −0.111734 | −0.029798 | 0.094738 | 0.093123 | −0.151493 | −0.076533 | 0.03695 | −0.028868 | 0.018984 | 0.018053 | −0.017445 | −0.057514 | 0.035127 | −0.072655 |
| 48 | −0.01957 | −0.049012 | 0.140329 | 0.010508 | −0.12985 | 0.057593 | −0.118921 | −0.00417 | −0.105581 | 0.057949 | −0.037986 | −0.061629 | −0.196287 | 0.11877 |
| 49 | 0.036319 | −0.231785 | −0.234865 | −0.192202 | −0.129177 | −0.029746 | −0.001632 | −0.098389 | −0.018877 | −0.017668 | 0.051853 | −0.046906 | −0.009246 | 0.241965 |
| 50 | −0.040975 | −0.095477 | 0.034214 | 0.218006 | 0.174852 | −0.078333 | −0.07768 | −0.03914 | −0.055252 | −0.111475 | 0.201086 | −0.036239 | −0.00841 | 0.012804 |
| 51 | −0.044217 | 0.011935 | 0.151593 | 0.073959 | −0.057758 | 0.116378 | 0.061517 | 0.010752 | 0.072738 | 0.090853 | −0.086514 | 0.049405 | 0.038909 | −0.290946 |
| 52 | 0.078284 | 0.085357 | −0.0251 | 0.100152 | 0.231022 | 0.017884 | 0.117117 | 0.025014 | −0.146303 | 0.119649 | 0.316616 | 0.047136 | 0.027399 | 0.063182 |
| 53 | 0.069856 | 0.063015 | −0.013524 | 0.058349 | 0.052551 | −0.180961 | −0.074161 | −0.002191 | −0.048016 | 0.061942 | −0.077777 | 0.03738 | −0.149919 | −0.066796 |
| 54 | 0.014823 | −0.105542 | 0.066763 | −0.012832 | 0.140082 | 0.019495 | 0.138208 | 0.037673 | −0.102252 | −0.043526 | −0.097958 | 0.094788 | −0.207412 | 0.03487 |
| 55 | −0.03444 | 0.003829 | −0.020177 | −0.161411 | 0.179515 | 0.010434 | 0.009803 | 0.11082 | −0.224813 | −0.143175 | −0.080033 | 0.007419 | −0.098759 | −0.134414 |
| 56 | −0.100399 | 0.026952 | −0.012153 | −0.056218 | −0.024302 | 0.058544 | 0.09346 | 0.05752 | −0.034947 | 0.061017 | 0.107431 | 0.015559 | 0.010885 | −0.178713 |
| 57 | −0.02493 | −0.123387 | 0.004172 | −0.029915 | −0.074884 | −0.0431 | 0.030224 | 0.029053 | 0.156168 | −0.013849 | −0.015078 | −0.022106 | 0.098715 | −0.220566 |
| 58 | 0.058251 | −0.028416 | 0.004301 | −0.076392 | −0.032884 | 0.069009 | 0.023127 | 0.085733 | 0.033981 | 0.035344 | 0.084576 | 0.067244 | −0.028745 | −0.060781 |
| 59 | 0.030041 | 0.139439 | 0.049546 | 0.044031 | −0.082973 | 0.106115 | −0.26636 | 0.115382 | 0.183335 | −0.068435 | −0.111291 | 0.049488 | −0.038862 | 0.075847 |
| 60 | −0.03905 | 0.088606 | 0.201292 | 0.065767 | 0.013448 | −0.058784 | −0.010139 | −0.13475 | 0.087563 | −0.082695 | −0.101139 | 0.1294 | 0.006659 | 0.021392 |
| 61 | −0.094215 | −0.058838 | −0.0999 | 0.031276 | −0.130351 | 0.036809 | 0.049551 | 0.053717 | −0.051695 | 0.144418 | −0.030479 | 0.029812 | −0.011154 | 0.148126 |
| 62 | 0.014805 | 0.039243 | 0.001735 | −0.127193 | 0.105518 | 0.035737 | 0.098262 | −0.047956 | 0.174275 | −0.097585 | 0.086308 | 0.132204 | 0.101912 | 0.177424 |
| 63 | 0.058757 | 0.158729 | −0.300143 | −0.020686 | −0.238459 | 0.025719 | −0.24246 | −0.049643 | 0.016828 | −0.074989 | 0.333884 | −0.009423 | 0.212043 | −0.108868 |
| 64 | 0.149014 | −0.000284 | 0.057224 | 0.113202 | 0.112985 | 0.108036 | −0.04573 | 0.059464 | 0.058006 | −0.052064 | 0.067305 | 0.083382 | −0.002801 | 0.025596 |
| 65 | 0.078594 | −0.000926 | 0.007576 | −0.133586 | 0.059762 | −0.218779 | −0.043437 | −0.025702 | 0.131748 | 0.136714 | 0.015181 | −0.127663 | 0.142049 | −0.044674 |
| 66 | 0.247537 | −0.033609 | −0.106889 | 0.088878 | −0.017437 | 0.097141 | −0.021922 | 0.17674 | 0.023772 | 0.047267 | −0.0113 | 0.056121 | −0.066691 | 0.154147 |
| 67 | −0.040553 | 0.070728 | −0.097383 | 0.141629 | 0.007947 | 0.030675 | −0.046519 | 0.249916 | −0.077367 | 0.050738 | −0.001729 | −0.185535 | 0.044157 | −0.170291 |
| 68 | 0.041778 | 0.082292 | 0.033303 | −0.013029 | −0.023704 | 0.074754 | 0.149933 | −0.116024 | −0.011919 | −0.156932 | −0.012775 | 0.015855 | 0.048268 | 0.055774 |
| 69 | 0.020175 | 0.072583 | −0.065416 | −0.071627 | 0.070131 | 0.063992 | 0.029921 | −0.154668 | −0.030322 | −0.114718 | −0.101254 | 0.030252 | −0.150766 | −0.114522 |
| 70 | −0.114527 | −0.11909 | −0.016815 | 0.085616 | −0.077874 | 0.006734 | −0.087077 | 0.026554 | −0.06009 | 0.093401 | −0.067596 | 0.040438 | −0.042238 | 0.091021 |
| 71 | 0.030886 | −0.054458 | 0.145745 | 0.253063 | −0.116928 | 0.060987 | 0.049652 | 0.124552 | 0.132545 | 0.026741 | −0.03122 | −0.083447 | −0.013101 | 0.089066 |
| 72 | −0.176312 | −0.055308 | −0.01778 | 0.080822 | 0.033109 | −0.218955 | 0.123949 | 0.111624 | 0.039602 | 0.048484 | 0.002203 | 0.025937 | 0.011839 | −0.083881 |
| 73 | 0.207728 | 0.014399 | −0.024726 | −0.044636 | −0.129136 | −0.087517 | 0.027218 | −0.029049 | −0.127533 | 0.241402 | 0.12073 | −0.192666 | −0.087802 | −0.07245 |
| 74 | −0.131378 | −0.043931 | 0.027904 | −0.173413 | 0.133962 | 0.28308 | −0.043651 | 0.277564 | 0.159157 | 0.137729 | 0.005968 | −0.144681 | 0.004549 | −0.003177 |
| 75 | 0.02827 | 0.014459 | −0.025905 | −0.086896 | 0.116047 | 0.085492 | −0.113926 | −0.20247 | −0.151611 | −0.087532 | −0.214888 | 0.068326 | −0.108676 | −0.05919 |
| 76 | 0.237681 | 0.072481 | 0.026187 | 0.154537 | −0.080177 | 0.148832 | 0.053874 | −0.15473 | 0.022145 | 0.038714 | 0.09024 | −0.012504 | 0.026331 | 0.035478 |

APPENDIX B6-continued

PCA Transformation
Matrix (82 x 82; Early/Late)

| | | | | | | | | | | | | | | |
|---|---|---|---|---|---|---|---|---|---|---|---|---|---|---|
| 77 | 0.065711 | 0.051126 | −0.144909 | 0.024441 | 0.054221 | 0.156268 | 0.172261 | −0.280076 | −0.008147 | −0.038697 | −0.203853 | 0.099572 | 0.099969 | 0.112074 |
| 78 | 0.155469 | 0.109114 | 0.005966 | 0.027629 | −0.157213 | −0.291509 | −0.004575 | −0.033633 | 0.268977 | 0.062185 | 0.040767 | −0.048945 | −0.352016 | −0.171236 |
| 79 | −0.071571 | 0.01777 | 0.362337 | 0.059692 | −0.023039 | −0.033704 | 0.103634 | 0.007056 | −0.032593 | 0.088785 | 0.143224 | 0.027228 | 0.118054 | −0.041457 |
| 80 | −0.080701 | −0.037885 | 0.094162 | −0.166191 | 0.076656 | −0.018933 | −0.309541 | 0.08251 | −0.097654 | −0.145194 | 0.107707 | 0.023071 | 0.068116 | −0.022553 |
| 81 | 0.102168 | −0.083456 | −0.029785 | −0.063653 | −0.057115 | −0.142055 | −0.008744 | −0.088248 | 0.096534 | −0.077848 | 0.088983 | −0.125744 | 0.028541 | −0.012069 |
| 82 | 0.025289 | 0.049215 | −0.089023 | −0.006854 | 0.101676 | −0.059382 | −0.004722 | 0.263118 | 0.096773 | −0.066083 | −0.093957 | 0.162932 | 0.210203 | 0.090395 |

| | AP | AQ | AR | AS | AT | AU | AV | AW | AX | AY | AZ | BA | BB | BC |
|---|---|---|---|---|---|---|---|---|---|---|---|---|---|---|
| 1 | −0.128015 | 0.013874 | 0.220834 | 0.004928 | 0.138755 | 0.02684 | 0.084136 | −0.174416 | −0.126365 | −0.08755 | 0.064346 | 0.061445 | −0.155246 | −0.223855 |
| 2 | −0.106745 | 0.030619 | −0.135033 | 0.113712 | −0.095393 | −0.019505 | −0.197775 | −0.025406 | −0.155542 | 0.125995 | −0.047975 | −0.029508 | −0.109773 | −0.190905 |
| 3 | −0.068058 | 0.008295 | −0.180286 | −0.070604 | −0.022385 | −0.104421 | −0.133635 | 0.125429 | 0.188275 | 0.057397 | −0.256828 | 0.171982 | −0.080683 | 0.168095 |
| 4 | −0.023405 | 0.03907 | −0.022463 | 0.130917 | 0.082709 | 0.154304 | −0.021821 | 0.187015 | 0.043054 | −0.256382 | 0.282708 | 0.039018 | 0.095346 | 0.045264 |
| 5 | −0.105848 | 0.003157 | 0.090928 | −0.002606 | 0.096293 | −0.141298 | 0.147912 | −0.230377 | 0.010747 | 0.281361 | −0.094721 | −0.028954 | −0.103936 | 0.058738 |
| 6 | 0.061511 | −0.070402 | 0.097216 | −0.130744 | −0.047972 | 0.063066 | −0.081243 | −0.020461 | −0.144721 | 0.178604 | −0.172093 | −0.202196 | 0.01625 | 0.011955 |
| 7 | 0.118383 | 0.018967 | −0.013434 | −0.162543 | 0.125794 | −0.189977 | 0.066764 | 0.036944 | 0.062808 | −0.191704 | 0.083397 | −0.080635 | 0.0724 | 0.091977 |
| 8 | 0.135332 | 0.149532 | 0.004186 | −0.040353 | −0.030862 | 0.092617 | 0.082477 | −0.165221 | 0.142663 | 0.170141 | −0.137526 | −0.045461 | 0.19545 | 0.046516 |
| 9 | −0.065024 | −0.059963 | −0.118762 | 0.062794 | −0.109143 | −0.100493 | −0.068738 | −0.0164 | −0.13052 | −0.060197 | −0.008087 | 0.083653 | 0.112521 | −0.012069 |
| 10 | 0.045003 | 0.003342 | 0.060765 | 0.098123 | 0.042374 | 0.112372 | −0.137677 | −0.005025 | 0.256947 | 0.037573 | 0.025426 | 0.162603 | −0.025441 | −0.197522 |
| 11 | −0.149634 | −0.051692 | 0.086157 | 0.10079 | 0.001657 | 0.031349 | −0.104976 | 0.141226 | −0.193542 | −0.11241 | −0.079008 | −0.105155 | −0.021823 | −0.111108 |
| 12 | 0.171543 | 0.109879 | −0.021548 | −0.007223 | −0.189999 | 0.163476 | 0.125316 | −0.036952 | 0.133055 | −0.122671 | 0.023213 | 0.086865 | −0.159049 | −0.047339 |
| 13 | 0.10652 | −0.011221 | 0.131015 | −0.121236 | −0.012754 | −0.130791 | 0.184711 | 0.022799 | −0.018883 | 0.081413 | 0.05736 | −0.083163 | −0.10454 | −0.13375 |
| 14 | 0.042374 | 0.036838 | −0.122125 | −0.025092 | −0.108406 | 0.069002 | −0.118697 | −0.095219 | −0.074656 | −0.072945 | 0.032344 | 0.228599 | −0.060869 | 0.005036 |
| 15 | 0.099121 | 0.003074 | 0.061929 | 0.074784 | −0.078171 | 0.074274 | −0.175738 | 0.125635 | −0.21978 | 0.080642 | 0.084648 | −0.152857 | 0.087383 | 0.28614 |
| 16 | −0.066433 | −0.022641 | −0.073403 | −0.103309 | −0.006925 | −0.092485 | 0.104318 | −0.08195 | −0.11341 | −0.018325 | −0.138647 | −0.16139 | −0.028937 | 0.001086 |
| 17 | 0.122043 | 0.07939 | −0.036689 | 0.008352 | −0.165033 | −0.131547 | −0.097904 | −0.036134 | −0.093198 | 0.065534 | 0.064199 | −0.176994 | −0.139109 | −0.123235 |
| 18 | −0.096864 | −0.02369 | 0.065803 | 0.013693 | 0.008979 | −0.240508 | −0.043833 | −0.00846 | 0.084437 | 0.087461 | 0.087967 | 0.143195 | −0.03338 | −0.048909 |
| 19 | 0.092223 | −0.009422 | −0.035879 | −0.132682 | −0.146495 | −0.071525 | 0.09264 | −0.109114 | −0.001357 | −0.060925 | 0.016278 | 0.248523 | −0.132673 | 0.098055 |
| 20 | −0.028136 | 0.03311 | 0.110338 | 0.09634 | 0.181424 | 0.148192 | −0.03482 | −0.027343 | 0.023667 | 0.138946 | 0.008389 | −0.036182 | 0.157303 | −0.132743 |
| 21 | −0.099657 | 0.007375 | −0.234267 | 0.03916 | −0.06957 | −0.193364 | 0.242795 | 0.11388 | 0.013718 | −0.141865 | −0.011717 | 0.046864 | −0.060638 | 0.209599 |
| 22 | 0.078105 | −0.100364 | 0.076764 | −0.080078 | −0.133018 | −0.16508 | −0.183022 | 0.152066 | 0.038659 | −0.125122 | −0.039419 | 0.047778 | −0.126962 | −0.085737 |
| 23 | −0.175166 | −0.162598 | 0.119016 | −0.060263 | −0.178099 | 0.179638 | −0.107443 | 0.048892 | 0.24063 | 0.044118 | −0.073287 | −0.205092 | −0.000123 | 0.056293 |
| 24 | −0.011814 | 0.142501 | −0.035474 | 0.089923 | −0.007821 | −0.080861 | 0.104938 | −0.138703 | −0.263361 | −0.134159 | −0.011477 | 0.13647 | −0.138233 | 0.096434 |
| 25 | 0.075697 | −0.116543 | 0.048484 | −0.136915 | 0.013158 | 0.029137 | 0.01797 | −0.093829 | 0.063669 | 0.115282 | 0.063401 | −0.001178 | 0.084278 | −0.160587 |
| 26 | 0.178154 | 0.109101 | −0.104399 | −0.012024 | 0.034276 | −0.041344 | −0.013815 | 0.146193 | −0.052582 | 0.014339 | 0.023917 | −0.010557 | 0.051256 | −0.101288 |
| 27 | 0.005558 | 0.000809 | −0.161693 | 0.013386 | 0.085341 | −0.136853 | −0.076981 | 0.050165 | 0.065835 | −0.084522 | −0.074682 | −0.057458 | 0.048198 | 0.049282 |
| 28 | −0.073358 | 0.033929 | −0.065052 | 0.143312 | 0.252782 | 0.048659 | 0.085511 | 0.176892 | 0.144688 | −0.103386 | −0.050808 | −0.038285 | −0.035304 | −0.015627 |
| 29 | −0.060761 | 0.049522 | 0.240372 | 0.045309 | −0.060185 | −0.193435 | −0.031607 | −0.08118 | −0.03262 | 0.137033 | 0.075333 | −0.046545 | 0.140864 | 0.133378 |
| 30 | 0.056374 | −0.13905 | 0.005017 | −0.081277 | −0.048812 | 0.157879 | −0.003541 | 0.007628 | −0.035124 | −0.053527 | 0.134929 | 0.074559 | −0.308344 | −0.056674 |
| 31 | 0.143801 | −0.094786 | −0.038465 | −0.097558 | −0.268351 | 0.111333 | 0.131507 | 0.08921 | −0.039557 | 0.119898 | −0.140138 | 0.10298 | 0.209167 | −0.11058 |
| 32 | −0.18732 | −0.146607 | −0.083124 | 0.065124 | 0.048026 | −0.108657 | 0.023446 | −0.075271 | −0.069462 | 0.034287 | 0.166111 | −0.055028 | −0.025941 | −0.020201 |
| 33 | 0.021623 | −0.014363 | −0.049244 | −0.06614 | 0.127653 | 0.044144 | −0.119241 | −0.048555 | −0.264887 | 0.011911 | 0.032992 | 0.178425 | 0.223276 | 0.005228 |
| 34 | 0.059532 | 0.266807 | −0.042599 | 0.078915 | −0.103256 | 0.022798 | −0.036718 | −0.038326 | −0.031592 | 0.078624 | −0.075844 | 0.084758 | −0.013181 | −0.065566 |
| 35 | 0.350406 | 0.049903 | 0.062389 | 0.076356 | 0.097145 | −0.164567 | 0.056885 | 0.203771 | 0.104271 | 0.051255 | −0.063722 | −0.089636 | −0.158788 | −0.027441 |
| 36 | 0.121884 | −0.079979 | 0.073816 | −0.196633 | 0.204293 | 0.004627 | 0.035233 | 0.07793 | −0.038005 | −0.067037 | −0.085746 | −0.077865 | −0.052512 | 0.024652 |
| 37 | 0.203688 | 0.109941 | 0.237265 | 0.037435 | −0.054515 | 0.019696 | −0.024236 | −0.05689 | 0.002212 | −0.131461 | −0.006566 | 0.050928 | 0.035358 | 0.055404 |
| 38 | −0.181322 | 0.015473 | 0.004504 | −0.231597 | −0.077952 | 0.12478 | 0.037334 | 0.044545 | −0.09504 | −0.132275 | −0.048061 | 0.08213 | 0.08219 | 0.117892 |
| 39 | 0.154188 | −0.146906 | 0.085392 | 0.141987 | 0.077346 | −0.074858 | −0.118337 | −0.003456 | −0.132 | −0.076018 | 0.050792 | 0.07783 | −0.006655 | 0.130092 |
| 40 | −0.127749 | −0.000468 | 0.10431 | −0.107918 | −0.15115 | 0.004673 | 0.040257 | 0.004739 | 0.055575 | −0.057393 | −0.012752 | 0.212983 | 0.047031 | 0.02998 |
| 41 | −0.045921 | −0.256407 | 0.085492 | −0.061886 | −0.003827 | −0.018844 | 0.021877 | −0.095163 | 0.034619 | −0.029678 | 0.165149 | −0.01802 | 0.008062 | −0.043472 |

APPENDIX B6-continued

PCA Transformation
Matrix (82 x 82; Early/Late)

| | | | | | | | | | | | | | | |
|---|---|---|---|---|---|---|---|---|---|---|---|---|---|---|
| 42 | 0.004544 | 0.004999 | −0.022077 | −0.322849 | −0.122808 | 0.207783 | −0.048716 | 0.107884 | −0.164499 | 0.173731 | 0.04822 | 0.190951 | −0.083398 | −0.014935 |
| 43 | 0.025236 | −0.040132 | −0.135319 | 0.096387 | 0.08967 | −0.176376 | 0.088541 | 0.041553 | 0.065961 | 0.248125 | 0.027815 | 0.053596 | −0.155766 | −0.040524 |
| 44 | −0.021586 | −0.102915 | −0.226671 | 0.211466 | −0.006205 | 0.193064 | 0.056268 | −0.128819 | 0.004236 | 0.222537 | 0.0732 | −0.004313 | 0.050073 | −0.019489 |
| 45 | 0.033986 | 0.029625 | 0.003309 | 0.122612 | −0.043566 | −0.087086 | −0.076208 | 0.012334 | −0.09399 | −0.027785 | −0.1017 | −0.017372 | 0.060439 | −0.063044 |
| 46 | 0.122492 | −0.006158 | −0.108266 | −0.026542 | 0.123867 | 0.113505 | 0.013747 | −0.04054 | −0.088207 | −0.072214 | −0.081622 | −0.061071 | 0.131641 | 0.054666 |
| 47 | 0.122917 | 0.028456 | −0.085342 | −0.140394 | −0.025433 | −0.027837 | 0.054543 | 0.019051 | −0.120714 | 0.067298 | 0.014691 | −0.344258 | −0.079264 | −0.078625 |
| 48 | −0.019927 | 0.112442 | 0.036449 | −0.054333 | 0.054493 | 0.03914 | −0.166857 | −0.125426 | −0.000282 | −0.057169 | −0.085645 | −0.016677 | 0.110198 | −0.0471 |
| 49 | −0.305369 | 0.156028 | 0.021913 | 0.185499 | −0.14925 | −0.017987 | 0.11503 | 0.14012 | −0.031767 | −0.071716 | 0.035581 | −0.100561 | 0.242468 | −0.089266 |
| 50 | 0.123693 | 0.038988 | −0.061411 | −0.015924 | 0.278321 | 0.024822 | 0.130391 | −0.036486 | 0.038523 | 0.01096 | 0.00332 | −0.004096 | 0.113028 | 0.068485 |
| 51 | 0.067339 | −0.14813 | 0.065954 | 0.112331 | −0.14132 | −0.061815 | −0.02529 | −0.182254 | 0.11556 | −0.221531 | −0.012606 | −0.147495 | −0.044767 | −0.168237 |
| 52 | −0.139065 | −0.103403 | −0.138843 | −0.090037 | −0.075532 | −0.019893 | −0.072956 | 0.127964 | 0.121992 | 0.071014 | 0.102483 | −0.120114 | −0.1215 | −0.083155 |
| 53 | −0.153794 | 0.150861 | 0.097426 | 0.015666 | 0.084709 | 0.130644 | −0.057599 | 0.052764 | 0.038511 | −0.084384 | 0.068631 | 0.042046 | −0.174145 | 0.0221 |
| 54 | 0.062977 | 0.07145 | 0.102149 | −0.036296 | −0.040784 | 0.070131 | −0.079136 | −0.015357 | 0.160875 | 0.052923 | 0.084099 | 0.032217 | −0.067602 | 0.162749 |
| 55 | 0.0249 | −0.076475 | 0.016001 | 0.018594 | 0.041683 | 0.20356 | 0.111781 | 0.107239 | −0.072304 | −0.081936 | −0.130653 | −0.028299 | −0.137062 | −0.115887 |
| 56 | 0.024493 | 0.021035 | 0.063273 | 0.003197 | 0.129304 | −0.032875 | −0.216649 | −0.273387 | 0.04074 | −0.039479 | −0.118307 | −0.096055 | −0.045972 | 0.205448 |
| 57 | 0.002122 | 0.14074 | −0.098113 | 0.055001 | −0.094489 | −0.053471 | −0.012557 | 0.137123 | 0.055193 | 0.132034 | 0.353179 | 0.015652 | −0.063866 | 0.11723 |
| 58 | −0.043843 | 0.224317 | 0.120339 | 0.006197 | 0.014444 | −0.068024 | −0.081376 | −0.002637 | 0.166306 | 0.073603 | −0.175445 | 0.109631 | −0.008258 | −0.04055 |
| 59 | 0.063363 | −0.065662 | 0.13201 | −0.066978 | 0.199638 | −0.080047 | 0.06203 | −0.066858 | −0.05805 | 0.175063 | 0.041327 | 0.245315 | −0.007425 | 0.117921 |
| 60 | 0.146333 | 0.07378 | −0.01139 | 0.129757 | −0.047356 | 0.001438 | 0.034556 | 0.048177 | 0.037838 | −0.065635 | −0.042114 | −0.022833 | −0.024525 | −0.031394 |
| 61 | −0.030049 | −0.076923 | −0.208903 | 0.027857 | 0.080239 | 0.017035 | 0.097884 | −0.005711 | 0.084985 | 0.094446 | 0.03862 | −0.042986 | −0.0336 | −0.045484 |
| 62 | 0.003676 | −0.067089 | 0.076243 | −0.014777 | −0.042723 | −0.005499 | 0.099153 | −0.125482 | −0.048218 | −0.204437 | 0.001638 | −0.140665 | −0.088746 | −0.016772 |
| 63 | −0.021986 | −0.067076 | 0.12696 | 0.118819 | −0.055924 | −0.126691 | −0.037566 | 0.059305 | 0.001787 | 0.002325 | 0.062432 | 0.018474 | 0.075584 | 0.10323 |
| 64 | −0.034229 | −0.036561 | 0.064286 | 0.107861 | −0.165577 | −0.065148 | 0.013435 | −0.054606 | 0.140432 | 0.130889 | −0.021289 | 0.03035 | 0.037378 | 0.094077 |
| 65 | 0.003361 | −0.010243 | −0.152012 | −0.231177 | −0.050686 | −0.059933 | 0.000751 | 0.00099 | 0.003202 | 0.007388 | −0.22731 | 0.031762 | 0.147187 | −0.047824 |
| 66 | 0.009079 | −0.122828 | 0.112213 | −0.000555 | 0.089121 | 0.107048 | −0.012176 | 0.024303 | 0.12247 | 0.038349 | −0.051656 | 0.034412 | 0.014007 | −0.081811 |
| 67 | −0.022175 | 0.041844 | 0.195936 | 0.045324 | −0.216935 | −0.066902 | 0.178331 | −0.094099 | 0.073583 | −0.131278 | 0.009318 | −0.07266 | 0.102201 | 0.069218 |
| 68 | −0.063831 | 0.04504 | −0.018373 | 0.073941 | 0.125371 | 0.208288 | 0.132151 | −0.065484 | −0.086061 | −0.010573 | −0.10145 | 0.002008 | −0.086589 | −0.057855 |
| 69 | −0.10819 | −0.207448 | −0.090377 | −0.191964 | 0.075813 | −0.028837 | −0.027335 | 0.042266 | −0.043972 | 0.050872 | 0.287357 | −0.087773 | 0.07543 | 0.146604 |
| 70 | −0.000169 | −0.093665 | −0.061291 | 0.107242 | 0.051932 | −0.019238 | −0.240898 | −0.027106 | −0.038525 | −0.050355 | −0.221533 | 0.038005 | −0.068784 | 0.135583 |
| 71 | 0.036796 | 0.077088 | −0.220677 | 0.091439 | 0.01607 | −0.065872 | 0.049287 | 0.039852 | −0.022623 | 0.003 | −0.131512 | 0.010581 | 0.027884 | −0.110368 |
| 72 | −0.076654 | 0.273624 | 0.013894 | −0.040404 | 0.080109 | −0.042424 | 0.069475 | −0.053296 | −0.016034 | 0.060231 | 0.118521 | 0.040025 | −0.000597 | −0.128018 |
| 73 | −0.210291 | 0.171026 | −0.005526 | 0.008001 | 0.010897 | 0.167848 | −0.003161 | −0.037907 | 0.026027 | 0.11337 | −0.095381 | −0.174053 | −0.28543 | 0.234732 |
| 74 | −0.059964 | −0.000625 | 0.173353 | −0.159023 | 0.060519 | −0.142304 | −0.125561 | 0.342176 | 0.070719 | 0.027121 | −0.023333 | −0.025183 | 0.002496 | −0.055203 |
| 75 | −0.071682 | 0.031979 | 0.028432 | −0.062502 | −0.000145 | −0.111619 | 0.145357 | 0.009025 | 0.051253 | −0.009011 | −0.178214 | −0.008804 | 0.258054 | −0.106301 |
| 76 | 0.013629 | 0.237666 | −0.022255 | −0.160194 | 0.130388 | −0.040938 | −0.214921 | 0.080235 | −0.039424 | −0.03543 | 0.204618 | −0.011832 | 0.082134 | −0.240008 |
| 77 | 0.029919 | 0.000202 | 0.041481 | 0.06056 | 0.053984 | −0.091452 | −0.134656 | −0.015073 | −0.21299 | 0.019906 | 0.018471 | 0.002652 | −0.098179 | 0.030343 |
| 78 | −0.003434 | −0.231191 | 0.019418 | 0.083028 | −0.046505 | −0.111437 | 0.210675 | 0.007156 | −0.1248 | −0.013052 | 0.023814 | 0.130352 | −0.015963 | −0.134758 |
| 79 | 0.203994 | −0.101798 | 0.152554 | 0.28744 | −0.102137 | 0.16816 | 0.140726 | 0.28594 | −0.147265 | 0.194074 | −0.042438 | 0.018558 | 0.042935 | 0.141251 |
| 80 | 0.082771 | 0.077834 | −0.096743 | −0.146041 | 0.045337 | 0.135623 | 0.149448 | −0.03692 | 0.102833 | −0.12317 | 0.025437 | −0.126547 | 0.025811 | 0.194848 |
| 81 | 0.106256 | −0.29873 | −0.156236 | 0.12629 | 0.075971 | 0.051849 | −0.17533 | −0.151394 | 0.207333 | −0.075334 | 0.00441 | 0.080972 | 0.103095 | −0.037568 |
| 82 | 0.169488 | 0.112393 | −0.186632 | −0.004639 | −0.209503 | −0.019129 | −0.161715 | −0.230317 | 0.033193 | −0.043074 | 0.155315 | −0.162007 | 0.042875 | −0.028912 |

| | BD | BE | BF | BG | BH | BI | BJ | BK | BL | BM | BN | BO | BP | BQ |
|---|---|---|---|---|---|---|---|---|---|---|---|---|---|---|
| 1 | 0.1423 | −0.105041 | 0.120322 | −0.185157 | −0.084361 | −0.027808 | −0.066903 | −0.083795 | 0.143778 | 0.045327 | 0.024448 | −0.081701 | −0.0301 | −0.064087 |
| 2 | −0.037435 | 0.053287 | −0.20129 | −0.055687 | 0.151536 | −0.069299 | 0.06972 | 0.026781 | 0.012864 | −0.007614 | 0.129805 | −0.115336 | −0.126943 | −0.048296 |
| 3 | 0.012647 | −0.006154 | 0.142037 | 0.040427 | −0.041959 | −0.054623 | −0.031197 | −0.027581 | −0.103591 | −0.039235 | −0.035324 | 0.027352 | −0.051832 | −0.111605 |
| 4 | 0.106994 | 0.016588 | −0.04861 | 0.094046 | 0.096802 | −0.17119 | −0.103739 | −0.045125 | 0.060608 | 0.113718 | 0.35329 | 0.063838 | 0.026013 | −0.033601 |
| 5 | −0.130912 | 0.012919 | 0.220274 | −0.141416 | 0.061063 | 0.170465 | 0.071748 | 0.064983 | −0.006357 | 0.018223 | 0.047326 | −0.136872 | 0.188819 | 0.111531 |
| 6 | 0.026557 | −0.220408 | −0.14267 | 0.045794 | −0.177837 | −0.095817 | 0.111242 | −0.052553 | 0.095748 | −0.008714 | −0.385501 | 0.01757 | −0.188646 | −0.086152 |

APPENDIX B6-continued

PCA Transformation
Matrix (82 x 82; Early/Late)

| | | | | | | | | | | | | | |
|---|---|---|---|---|---|---|---|---|---|---|---|---|---|
| 7 | −0.056568 | 0.085365 | 0.079194 | 0.205321 | −0.061913 | 0.125944 | −0.021328 | −0.037222 | 0.058355 | −0.037633 | −0.066661 | 0.054192 | 0.185013 | 0.112013 |
| 8 | 0.086305 | −0.074215 | 0.079106 | 0.088807 | 0.075401 | 0.034273 | −0.012681 | 0.039672 | −0.043769 | −0.032448 | 0.134687 | −0.10773 | −0.084397 | −0.047382 |
| 9 | 0.047142 | −0.006587 | −0.067491 | −0.052067 | 0.038329 | 0.059776 | 0.034936 | 0.041402 | −0.064595 | −0.025712 | 0.099646 | −0.05539 | −0.039148 | 0.056267 |
| 10 | 0.114593 | 0.07792 | −0.021209 | −0.165996 | −0.117121 | 0.039351 | −0.028331 | −0.006569 | −0.103946 | −0.002572 | −0.064944 | 0.193833 | 0.059503 | 0.025439 |
| 11 | −0.126984 | 0.015017 | −0.164473 | 0.178786 | 0.037827 | 0.114374 | −0.065872 | 0.042728 | −0.04883 | −0.083631 | 0.019233 | −0.055447 | 0.1261 | 0.046692 |
| 12 | −0.027805 | 0.051221 | 0.044462 | −0.117101 | 0.066741 | −0.101793 | −0.073442 | −0.06524 | 0.00691 | −0.046309 | −0.028337 | 0.041406 | −0.03921 | −0.071223 |
| 13 | 0.255126 | 0.07056 | −0.172633 | 0.023108 | 0.031911 | 0.190865 | −0.013515 | −0.128669 | 0.012361 | 0.057032 | 0.193755 | −0.093688 | −0.065794 | −0.104682 |
| 14 | −0.009973 | −0.246314 | −0.023792 | 0.217815 | 0.119064 | −0.107115 | 0.198787 | 0.166484 | −0.118695 | 0.0905 | −0.081979 | −0.039796 | 0.106984 | −0.014008 |
| 15 | −0.126093 | 0.242851 | 0.223143 | −0.093212 | −0.049112 | −0.139466 | 0.066702 | 0.094266 | −0.048497 | 0.039857 | 0.008232 | −0.183458 | −0.119175 | 0.13951 |
| 16 | 0.021598 | −0.021746 | −0.061386 | −0.093148 | 0.015303 | −0.103677 | −0.240552 | −0.185517 | 0.156276 | −0.22477 | −0.022176 | 0.082202 | 0.100876 | −0.048448 |
| 17 | 0.024704 | −0.103136 | −0.096711 | −0.054562 | −0.090348 | −0.019106 | −0.009304 | −0.02548 | 0.090816 | 0.00032 | 0.019885 | −0.039981 | −0.028101 | 0.039355 |
| 18 | −0.022769 | 0.007682 | 0.068774 | 0.098384 | 0.042042 | −0.042213 | −0.000469 | −0.047264 | 0.113206 | 0.047796 | 0.014053 | −0.051844 | −0.036837 | −0.034229 |
| 19 | 0.103436 | 0.065389 | −0.035098 | 0.067111 | 0.073962 | −0.167854 | 0.013912 | −0.121898 | 0.014921 | −0.012753 | −0.039287 | −0.029544 | −0.006694 | −0.09158 |
| 20 | −0.111244 | 0.014498 | 0.002512 | 0.007082 | 0.106745 | 0.189168 | 0.024245 | 0.121968 | −0.017287 | −0.033609 | −0.068863 | 0.044689 | −0.002629 | −0.063643 |
| 21 | −0.099853 | −0.14552 | −0.185562 | 0.064521 | −0.247154 | −0.088507 | −0.063217 | −0.015819 | −0.001869 | 0.080647 | 0.011291 | −0.099946 | −0.059896 | −0.002532 |
| 22 | −0.023491 | −0.000956 | 0.055465 | −0.062571 | 0.034137 | −0.006265 | 0.052073 | −0.04263 | 0.237553 | 0.100653 | −0.112525 | 0.16477 | 0.098711 | 0.154629 |
| 23 | −0.001136 | −0.010137 | −0.031018 | −0.065472 | −0.047903 | −0.127887 | −0.032874 | −0.120021 | 0.00139 | 0.038119 | 0.077981 | 0.099303 | 0.011294 | 0.076263 |
| 24 | 0.014356 | −0.057624 | 0.075848 | −0.051036 | −0.15174 | 0.139089 | 0.047947 | 0.0198 | −0.066595 | −0.051041 | 0.037814 | 0.098292 | −0.021957 | −0.007218 |
| 25 | −0.060565 | 0.028576 | −0.082531 | 0.071668 | 0.117369 | −0.057022 | 0.009106 | −0.003525 | −0.014934 | 0.005032 | −0.102028 | −0.086874 | −0.057688 | −0.095848 |
| 26 | −0.120962 | −0.03465 | 0.025063 | 0.044543 | 0.256108 | −0.008739 | 0.053602 | 0.002144 | 0.040123 | 0.093373 | −0.028906 | −0.081064 | −0.084392 | −0.115681 |
| 27 | 0.382526 | 0.113094 | −0.062106 | −0.074908 | −0.073022 | 0.010217 | 0.018384 | 0.167394 | 0.082143 | −0.068537 | −0.069235 | −0.040921 | 0.216592 | 0.128057 |
| 28 | −0.130047 | −0.012484 | 0.004974 | 0.022463 | −0.012221 | 0.036648 | 0.072999 | −0.126915 | 0.00558 | 0.010055 | 0.040028 | −0.08386 | 0.13167 | −0.131755 |
| 29 | 0.065125 | −0.188341 | −0.15502 | 0.266049 | 0.044065 | −0.113299 | 0.065847 | 0.161332 | 0.031687 | −0.025925 | −0.037209 | 0.225541 | 0.076035 | 0.075957 |
| 30 | −0.220726 | 0.103023 | 0.032755 | −0.199989 | −0.074557 | 0.123258 | 0.147178 | 0.059759 | −0.026158 | 0.175345 | −0.060678 | 0.115844 | −0.167188 | 0.122778 |
| 31 | −0.016731 | 0.154653 | −0.099605 | 0.123353 | 0.101359 | 0.132808 | −0.08613 | 0.055784 | 0.099201 | −0.021731 | 0.073689 | −0.119291 | −0.032551 | −0.024758 |
| 32 | −0.166513 | −0.018329 | −0.131504 | 0.020581 | −0.057203 | 0.028631 | −0.04648 | 0.067523 | 0.047449 | 0.041537 | 0.008036 | 0.014481 | −0.141007 | 0.019566 |
| 33 | 0.139202 | −0.08633 | 0.142552 | −0.06333 | 0.165643 | −0.162405 | −0.111649 | −0.027429 | 0.101292 | 0.158884 | −0.062889 | 0.094866 | 0.077386 | 0.04176 |
| 34 | 0.031755 | −0.077686 | 0.148995 | 0.037312 | 0.010313 | 0.125354 | 0.122443 | −0.144049 | −0.012803 | −0.051343 | −0.012572 | 0.176117 | 0.03448 | −0.050451 |
| 35 | −0.14266 | −0.15639 | −0.112601 | −0.000968 | −0.022375 | −0.067299 | −0.067005 | 0.115993 | 0.018363 | 0.100187 | 0.083181 | −0.079915 | 0.049769 | 0.016062 |
| 36 | −0.052412 | 0.103968 | 0.133123 | 0.066644 | 0.072317 | −0.055808 | 0.038578 | 0.04108 | 0.027544 | 0.00672 | −0.014542 | −0.16901 | 0.035828 | −0.040919 |
| 37 | −0.142566 | −0.168587 | −0.090431 | 0.019498 | −0.040011 | 0.120985 | −0.080314 | −0.02396 | −0.13415 | −0.03825 | 0.068417 | −0.069643 | −0.076047 | 0.062099 |
| 38 | 0.087802 | 0.034894 | −0.036369 | −0.074985 | 0.079236 | 0.076662 | 0.087926 | −0.026356 | −0.114874 | 0.000813 | −0.10993 | 0.079793 | −0.101711 | −0.042525 |
| 39 | 0.098693 | −0.033343 | −0.083548 | −0.023393 | −0.006588 | 0.124688 | 0.168155 | 0.069641 | −0.14934 | 0.086572 | −0.027962 | 0.228333 | −0.084358 | 0.104511 |
| 40 | −0.118355 | −0.007148 | −0.047297 | 0.051038 | 0.032799 | −0.011676 | 0.231525 | 0.021434 | 0.227948 | 0.089575 | 0.014141 | −0.083361 | 0.086918 | −0.043719 |
| 41 | 0.122138 | 0.107201 | 0.119064 | 0.091315 | 0.042021 | −0.248251 | 0.10939 | −0.030135 | 0.181353 | −0.015861 | 0.048109 | 0.081331 | −0.04126 | −0.022738 |
| 42 | 0.050469 | −0.011731 | −0.013787 | 0.106679 | −0.252917 | 0.108584 | −0.060593 | 0.087354 | 0.078132 | −0.012584 | 0.087728 | −0.038545 | 0.272634 | −0.007821 |
| 43 | −0.042016 | 0.177503 | −0.088361 | 0.003446 | 0.176913 | −0.126621 | −0.015316 | 0.173753 | 0.103942 | 0.050929 | −0.054045 | 0.234388 | 0.022187 | 0.011886 |
| 44 | 0.055404 | −0.166402 | 0.186279 | 0.068241 | −0.25615 | −0.023344 | −0.0295 | 0.089056 | 0.278825 | 0.021001 | 0.054053 | −0.046629 | 0.092552 | −0.03225 |
| 45 | −0.123083 | 0.109514 | 0.140313 | 0.054095 | 0.019456 | −0.061838 | 0.156423 | −0.331103 | −0.024312 | 0.064918 | −0.042805 | 0.072217 | 0.101843 | −0.179721 |
| 46 | −0.019201 | 0.092289 | −0.046609 | −0.04843 | 0.073461 | −0.036189 | 0.186163 | 0.082531 | 0.101708 | 0.083384 | 0.020748 | −0.08376 | 0.051021 | 0.028215 |
| 47 | 0.199997 | −0.118749 | 0.244049 | 0.025679 | −0.040528 | −0.149794 | 0.115859 | 0.032149 | −0.222669 | 0.193224 | 0.199052 | 0.151136 | 0.064898 | −0.065959 |
| 48 | −0.003883 | 0.063639 | −0.282437 | −0.178316 | −0.067096 | −0.065816 | 0.01126 | −0.078958 | −0.050665 | 0.130677 | −0.138726 | −0.330402 | 0.262866 | −0.050997 |
| 49 | 0.053207 | −0.099621 | 0.05889 | −0.05449 | 0.033333 | −0.032461 | 0.060445 | −0.038621 | −0.072419 | −0.003732 | −0.031776 | 0.017582 | −0.054382 | −0.05698 |
| 50 | 0.046295 | 0.10143 | −0.12627 | −0.130671 | −0.123612 | −0.069535 | 0.004038 | −0.118169 | 0.046755 | 0.024922 | −0.173707 | 0.11831 | −0.247128 | 0.057796 |
| 51 | 0.024229 | −0.068104 | 0.212836 | 0.099443 | 0.072551 | 0.093819 | 0.131475 | −0.05615 | −0.084798 | −0.087105 | 0.067832 | −0.159745 | −0.008961 | 0.129965 |
| 52 | −0.055482 | −0.230789 | −0.023936 | −0.153603 | 0.132532 | −0.162261 | 0.025152 | 0.034155 | −0.269369 | −0.03879 | −0.023145 | −0.039605 | 0.152053 | 0.129259 |
| 53 | 0.036707 | −0.009229 | −0.005387 | −0.075706 | −0.112618 | −0.001243 | 0.091728 | 0.136883 | 0.254457 | 0.105168 | 0.103345 | −0.110371 | −0.068589 | −0.134807 |
| 54 | −0.071869 | −0.210267 | −0.024994 | −0.16548 | 0.060506 | −0.083682 | 0.222436 | 0.026808 | 0.127963 | −0.381186 | 0.158082 | −0.024325 | −0.038361 | −0.01437 |
| 55 | −0.047623 | −0.052844 | 0.170803 | 0.291599 | −0.100008 | −0.150652 | −0.029978 | −0.044255 | −0.140362 | −0.028549 | −0.122297 | 0.026753 | 0.052083 | −0.119955 |
| 56 | −0.168714 | −0.065293 | −0.100375 | 0.023567 | 0.055764 | −0.126856 | 0.013665 | −0.205745 | 0.133197 | 0.127714 | 0.146803 | 0.098186 | 0.059451 | −0.300179 |

APPENDIX B6-continued

PCA Transformation
Matrix (82 x 82; Early/Late)

| | | | | | | | | | | | | | | |
|---|---|---|---|---|---|---|---|---|---|---|---|---|---|---|
| 57 | −0.023959 | 0.068424 | 0.107191 | −0.092993 | 0.186715 | 0.033214 | −0.069676 | −0.176155 | 0.01348 | −0.077806 | −0.310735 | −0.107257 | 0.179429 | −0.000685 |
| 58 | 0.206503 | 0.179815 | −0.061254 | 0.088719 | −0.107073 | −0.228236 | 0.022065 | 0.125402 | −0.194089 | 0.021566 | 0.085321 | −0.100181 | −0.193329 | 0.028678 |
| 59 | −0.090177 | −0.021906 | 0.043376 | 0.068681 | −0.063679 | −0.157598 | −0.014938 | −0.066068 | −0.207323 | −0.125735 | 0.145368 | −0.106137 | 0.051463 | 0.085054 |
| 60 | 0.124464 | −0.028059 | 0.005655 | 0.152447 | 0.035402 | 0.248543 | 0.079252 | 0.008187 | 0.194429 | 0.059778 | −0.094051 | 0.067946 | −0.030393 | −0.032308 |
| 61 | 0.118095 | 0.157277 | −0.171278 | 0.088897 | −0.130243 | 0.051745 | 0.610454 | −0.151967 | −0.084941 | −0.040711 | 0.04621 | −0.049796 | 0.100244 | −0.062345 |
| 62 | 0.003898 | 0.131033 | −0.049523 | −0.045347 | −0.02459 | −0.095146 | −0.02547 | 0.460692 | −0.02292 | −0.006493 | −0.019323 | 0.043741 | 0.154609 | −0.214925 |
| 63 | 0.01676 | −0.007347 | 0.007455 | 0.017061 | −0.037332 | 0.025975 | 0.164146 | −0.016137 | 0.200955 | −0.124538 | 0.010095 | −0.031219 | −0.060453 | 0.060452 |
| 64 | 0.004394 | −0.042975 | 0.008748 | −0.002586 | −0.031066 | 0.094127 | −0.094537 | −0.054728 | −0.042307 | 0.660632 | −0.009544 | −0.06678 | 0.070957 | −0.030791 |
| 65 | −0.191636 | −0.038191 | −0.048716 | −0.152806 | 0.027468 | 0.102429 | 0.031005 | −0.038616 | 0.076667 | 0.011893 | 0.412094 | 0.244036 | 0.063283 | 0.139044 |
| 66 | 0.03562 | −0.069115 | −0.133379 | 0.065528 | 0.1304 | 0.078089 | −0.039338 | −0.047241 | −0.068678 | −0.036844 | −0.009854 | 0.23045 | 0.0594 | −0.075202 |
| 67 | −0.144253 | 0.115125 | 0.009296 | −0.012683 | −0.062523 | −0.052214 | 0.068139 | 0.060174 | −0.015991 | −0.033683 | −0.107877 | 0.040733 | 0.210365 | −0.064524 |
| 68 | −0.042294 | −0.058812 | −0.088987 | 0.197567 | 0.069265 | −0.137719 | 0.042317 | −0.238205 | 0.101396 | 0.091948 | 0.006247 | −0.068674 | 0.01065 | 0.581519 |
| 69 | −0.079032 | −0.056042 | −0.010593 | 0.040248 | −0.074474 | 0.23542 | −0.024671 | −0.109347 | −0.125856 | 0.028727 | 0.04474 | 0.032308 | −0.100848 | −0.226817 |
| 70 | 0.017064 | 0.049349 | 0.11376 | 0.011421 | 0.022535 | 0.058632 | −0.026574 | 0.020027 | −0.022631 | −0.018111 | 0.076315 | −0.060882 | −0.128872 | −0.103914 |
| 71 | −0.054527 | −0.188301 | 0.093742 | −0.042871 | 0.020852 | −0.008606 | −0.011939 | 0.128712 | 0.137547 | −0.080019 | −0.036678 | −0.020297 | −0.115984 | −0.118651 |
| 72 | −0.073973 | −0.021348 | −0.085416 | 0.017513 | −0.148311 | −0.040134 | −0.017517 | −0.004327 | −0.136203 | 0.042631 | −0.037251 | 0.119218 | 0.035646 | 0.054523 |
| 73 | 0.016767 | 0.202788 | −0.009053 | 0.248758 | 0.244845 | 0.11574 | −0.080446 | 0.091785 | 0.063769 | −0.002155 | 0.008149 | 0.093028 | −0.041269 | 0.038379 |
| 74 | 0.1556 | −0.117982 | 0.127237 | 0.050261 | −0.087619 | 0.069505 | 0.014001 | −0.050436 | 0.112091 | 0.018628 | 0.011249 | −0.156623 | −0.150989 | 0.05409 |
| 75 | −0.092869 | 0.077281 | 0.191561 | −0.165992 | −0.040806 | −0.076386 | 0.098655 | 0.099507 | 0.005405 | 0.077476 | 0.006032 | 0.070925 | −0.030315 | 0.071678 |
| 76 | −0.239836 | 0.058914 | −0.002357 | 0.058069 | −0.101727 | −0.099682 | 0.080436 | 0.091039 | 0.058753 | −0.014711 | 0.016799 | 0.088679 | 0.040157 | −0.03849 |
| 77 | 0.215876 | 0.003294 | −0.051291 | −0.132654 | 0.159422 | 0.090905 | −0.025659 | −0.112768 | −0.05809 | −0.046573 | 0.058947 | −0.054118 | 0.207852 | −0.040169 |
| 78 | −0.028244 | 0.030816 | −0.051512 | −0.039968 | 0.162611 | −0.153239 | 0.004834 | −0.013684 | −0.057212 | −0.017421 | 0.004599 | −0.08378 | −0.130445 | −0.065345 |
| 79 | 0.003096 | 0.034854 | −0.107489 | −0.173742 | −0.116433 | −0.114157 | 0.027603 | −0.069585 | 0.012373 | −0.052725 | 0.094796 | 0.09483 | 0.183144 | −0.084778 |
| 80 | 0.108105 | −0.257622 | −0.082101 | −0.179517 | 0.245212 | 0.026556 | 0.096966 | 0.073779 | 0.044403 | 0.10979 | −0.071339 | −0.047116 | −0.038296 | 0.064012 |
| 81 | −0.007884 | −0.104507 | 0.003121 | 0.0411 | −0.092834 | 0.057781 | −0.121906 | 0.072028 | −0.021297 | −0.058822 | −0.061481 | −0.087487 | 0.076677 | 0.020444 |
| 82 | −0.039352 | 0.236924 | −0.045621 | 0.097178 | −0.170057 | −0.043449 | −0.109872 | −0.125528 | 0.027699 | −0.034969 | 0.0503031 | 0.015527 | −0.093559 | 0.097953 |

| | BR | BS | BT | BU | BV | BW | BX | BY | BZ | CA | CB | CC | CD | CE |
|---|---|---|---|---|---|---|---|---|---|---|---|---|---|---|
| 1 | 0.046513 | 0.042885 | 0.002603 | −0.064058 | 0.213955 | 0.050605 | 0.151954 | −0.086492 | −0.100442 | 0.095072 | 0.12313 | 0.302718 | 0.083708 | 0.142626 |
| 2 | 0.093313 | −0.019678 | 0.014889 | 0.086548 | 0.037405 | 0.079315 | 0.090615 | 0.140551 | −0.056754 | −0.001965 | 0.043317 | −0.064155 | −0.017583 | −0.207122 |
| 3 | −0.009719 | −0.125017 | −0.116678 | −0.063668 | 0.006286 | 0.039191 | −0.114594 | 0.00492 | −0.055809 | −0.147494 | −0.157786 | −0.14231 | −0.181503 | −0.12673 |
| 4 | −0.081497 | −0.051515 | 0.023845 | −0.096217 | 0.108516 | −0.204954 | 0.184808 | 0.036628 | 0.011365 | 0.081398 | 0.066334 | 0.047727 | 0.040818 | −0.026786 |
| 5 | 0.247332 | 0.171567 | 0.085668 | 0.156461 | −0.129019 | 0.129167 | 0.071451 | 0.274562 | 0.154187 | −0.087833 | 0.074183 | −0.015528 | −0.00347 | 0.069232 |
| 6 | −0.15372 | −0.004045 | −0.098893 | −0.189187 | 0.05722 | −0.231873 | −0.035467 | −0.12576 | −0.036892 | −0.134382 | 0.026084 | 0.063163 | −0.011058 | 0.029101 |
| 7 | −0.014793 | −0.047133 | 0.022995 | −0.053698 | −0.128117 | −0.075347 | −0.031055 | −0.088223 | 0.092974 | 0.035191 | −0.060958 | −0.058623 | 0.016912 | 0.04377 |
| 8 | −0.151947 | −0.122062 | −0.019132 | −0.170444 | −0.028469 | 0.040957 | −0.063883 | 0.150214 | 0.056694 | 0.074658 | 0.087567 | −0.206117 | 0.146608 | 0.245499 |
| 9 | −0.113643 | 0.005662 | 0.117842 | 0.034451 | 0.070919 | 0.050652 | −0.053633 | 0.025927 | 0.056988 | −0.02884 | 0.039378 | −0.035931 | 0.060962 | 0.031396 |
| 10 | −0.121314 | 0.031684 | 0.126574 | 0.037005 | 0.101602 | 0.152002 | −0.047724 | 0.025697 | 0.010938 | 0.118601 | −0.094463 | 0.09536 | −0.115468 | 0.069346 |
| 11 | 0.046833 | 0.02414 | −0.028553 | −0.039213 | −0.003358 | 0.032736 | −0.004242 | −0.068919 | 0.024362 | −0.017709 | −0.107643 | −0.054612 | −0.05755 | 0.029302 |
| 12 | 0.191598 | −0.022952 | −0.090724 | 0.121757 | −0.100147 | 0.234134 | −0.077388 | −0.16539 | −0.143993 | 0.098419 | −0.022902 | 0.022536 | 0.021956 | −0.080301 |
| 13 | −0.051995 | 0.267166 | 0.178757 | 0.173624 | −0.139674 | −0.238264 | −0.098989 | −0.13998 | −0.235389 | −0.214748 | −0.004608 | −0.219025 | −0.039144 | −0.034224 |
| 14 | 0.016184 | −0.020267 | −0.127563 | 0.017606 | 0.091477 | 0.150387 | 0.169784 | −0.03365 | 0.194288 | −0.153631 | 0.230005 | −0.101196 | −0.202003 | 0.177526 |
| 15 | −0.052898 | −0.141009 | 0.105886 | 0.085005 | −0.113626 | 0.004096 | −0.143707 | −0.060779 | −0.121196 | 0.098808 | 0.011011 | 0.12163 | 0.120692 | −0.127241 |
| 16 | 0.133131 | −0.209949 | −0.217287 | −0.246073 | 0.057581 | 0.048362 | −0.010829 | 0.299574 | −0.032354 | 0.111566 | −0.032101 | −0.104592 | 0.250325 | −0.16018 |
| 17 | −0.027312 | 0.044921 | −0.042008 | −0.000239 | −0.008206 | 0.102459 | 0.068418 | −0.058286 | 0.133505 | −0.015759 | −0.002808 | −0.049287 | 0.102901 | −0.0903 |
| 18 | −0.081877 | −0.112114 | 0.022582 | −0.019788 | 0.105058 | −0.012616 | 0.008608 | 0.113502 | −0.010589 | 0.016902 | 0.041791 | 0.025952 | −0.026659 | −0.030096 |
| 19 | −0.003784 | −0.061385 | 0.034279 | 0.00622 | −0.057719 | −0.080059 | −0.083995 | 0.107749 | −0.094626 | 0.046975 | 0.130012 | −0.057976 | 0.037144 | −0.056543 |
| 20 | 0.0362 | −0.026426 | −0.138608 | −0.045184 | −0.109488 | 0.025052 | −0.072963 | −0.226623 | −0.01022 | 0.134586 | −0.109798 | 0.121426 | −0.03335 | 0.005241 |
| 21 | −0.057365 | 0.158139 | 0.059746 | 0.187513 | 0.064186 | −0.026403 | 0.044078 | 0.070801 | 0.104786 | −0.000072 | −0.059275 | 0.07383 | 0.0334 | 0.053125 |

APPENDIX B6-continued

PCA Transformation
Matrix (82 x 82; Early/Late)

| | | | | | | | | | | | | | | |
|---|---|---|---|---|---|---|---|---|---|---|---|---|---|---|
| 22 | 0.118671 | 0.089342 | 0.035509 | 0.02351 | 0.016721 | 0.002949 | 0.112914 | −0.12241 | 0.039139 | −0.087084 | 0.044463 | 0.168391 | −0.074241 | −0.21733 |
| 23 | −0.003517 | 0.047709 | 0.216639 | 0.061659 | −0.007212 | 0.052171 | −0.092632 | 0.115421 | 0.09799 | −0.101997 | 0.028419 | −0.010172 | −0.000602 | 0.029246 |
| 24 | −0.036252 | −0.011598 | −0.088994 | −0.095879 | −0.036732 | −0.013241 | −0.061112 | −0.133792 | −0.137744 | 0.01238 | 0.037706 | −0.025308 | 0.038931 | 0.030886 |
| 25 | −0.066178 | −0.03335 | 0.036452 | 0.026968 | −0.029916 | −0.064002 | 0.039842 | 0.105803 | 0.071505 | 0.054493 | −0.091626 | −0.077463 | 0.01843 | −0.091278 |
| 26 | 0.065735 | 0.034174 | −0.104675 | 0.097199 | 0.013319 | 0.039273 | 0.081927 | −0.110986 | 0.060808 | 0.012628 | 0.037034 | −0.036966 | 0.074776 | −0.107229 |
| 27 | 0.102344 | 0.001268 | −0.106829 | −0.088487 | −0.02503 | 0.137586 | −0.103951 | 0.07551 | −0.16514 | 0.01559 | 0.005743 | 0.048071 | −0.093745 | 0.128248 |
| 28 | 0.07997 | 0.007947 | −0.041668 | 0.026972 | 0.002601 | −0.142938 | −0.005061 | −0.0336 | 0.02506 | −0.056007 | −0.175582 | −0.07342 | 0.019897 | −0.008567 |
| 29 | 0.085363 | 0.161154 | 0.082215 | −0.024185 | −0.019201 | 0.052854 | 0.020664 | −0.05589 | −0.064491 | 0.276106 | 0.05499 | −0.016577 | 0.03768 | −0.058666 |
| 30 | −0.020549 | −0.076987 | 0.003002 | −0.107876 | 0.054804 | −0.238844 | −0.031478 | 0.111618 | 0.165983 | 0.081233 | 0.05051 | −0.229513 | 0.075116 | 0.087032 |
| 31 | −0.07736 | 0.067496 | −0.033177 | −0.038912 | 0.12093 | 0.181959 | −0.003769 | 0.011127 | 0.053368 | −0.192348 | −0.174566 | 0.244301 | 0.094039 | 0.026997 |
| 32 | 0.027089 | 0.017732 | −0.068448 | −0.032012 | −0.025329 | 0.005897 | −0.004587 | −0.004192 | 0.034472 | −0.02759 | −0.180253 | 0.043203 | −0.009419 | 0.059058 |
| 33 | 0.250224 | 0.086357 | 0.071489 | 0.062448 | 0.013646 | −0.123556 | −0.188203 | −0.01641 | −0.044291 | −0.195774 | −0.100724 | −0.181008 | 0.059145 | 0.050795 |
| 34 | −0.007458 | 0.034621 | 0.034395 | −0.000158 | −0.075432 | −0.121808 | −0.068738 | −0.068473 | −0.010359 | 0.100092 | 0.015039 | −0.014902 | 0.063071 | −0.102237 |
| 35 | 0.058327 | −0.075645 | −0.038154 | −0.044571 | 0.080329 | 0.078147 | −0.051464 | 0.009677 | −0.071035 | 0.01665 | 0.041686 | 0.000958 | −0.022051 | 0.076868 |
| 36 | −0.019077 | −0.057531 | −0.082287 | 0.111703 | 0.052132 | 0.031547 | −0.000775 | −0.077198 | −0.042274 | 0.078489 | 0.071207 | −0.031073 | −0.065976 | 0.046693 |
| 37 | 0.107995 | 0.066627 | 0.100853 | −0.279959 | 0.019078 | 0.0706 | 0.080761 | 0.128047 | −0.011439 | 0.032331 | −0.1006 | −0.015625 | 0.016167 | −0.134222 |
| 38 | −0.083122 | 0.079766 | 0.002419 | 0.174512 | 0.003391 | 0.082895 | 0.054241 | 0.043479 | −0.048669 | 0.04401 | 0.060167 | −0.0352 | 0.19158 | 0.054695 |
| 39 | 0.004374 | −0.169477 | 0.061397 | 0.034514 | 0.007862 | 0.122688 | 0.009337 | 0.181661 | −0.160617 | −0.118562 | −0.247838 | −0.032534 | 0.053927 | 0.018346 |
| 40 | 0.207611 | 0.145268 | 0.080846 | −0.139283 | 0.108146 | 0.024901 | −0.236996 | −0.113321 | −0.054387 | 0.151473 | −0.131906 | −0.040243 | 0.179728 | 0.060554 |
| 41 | −0.004338 | −0.038149 | −0.050207 | −0.067809 | −0.069803 | 0.097732 | 0.037478 | −0.044436 | 0.116936 | −0.055549 | −0.028937 | −0.031255 | −0.102917 | −0.150043 |
| 42 | 0.037238 | −0.126004 | 0.033286 | 0.064288 | −0.118337 | −0.13381 | 0.21386 | 0.072589 | −0.006967 | 0.149185 | −0.25041 | 0.050706 | −0.007969 | 0.01273 |
| 43 | −0.1337 | −0.035038 | −0.045367 | −0.034527 | 0.030632 | −0.083527 | −0.180087 | −0.0841 | −0.036456 | −0.082577 | 0.119928 | 0.119408 | 0.227346 | 0.275514 |
| 44 | −0.039327 | 0.036061 | −0.047311 | 0.102306 | 0.098501 | −0.14313 | −0.108382 | −0.005624 | −0.005141 | 0.092644 | −0.037178 | −0.062135 | −0.214546 | −0.158495 |
| 45 | 0.030892 | −0.006797 | 0.04043 | 0.079319 | 0.270458 | −0.070909 | −0.072382 | 0.120896 | 0.060416 | 0.009115 | −0.235541 | 0.120797 | 0.140768 | 0.237806 |
| 46 | 0.083936 | 0.060256 | 0.023288 | −0.034762 | 0.087607 | 0.034032 | 0.002245 | −0.007138 | −0.007647 | 0.115842 | 0.010027 | −0.140968 | −0.034772 | −0.147473 |
| 47 | −0.001818 | 0.099934 | −0.10352 | 0.036286 | 0.12458 | 0.124148 | 0.063696 | −0.009786 | 0.082912 | −0.035125 | −0.238412 | 0.018988 | 0.137599 | 0.046968 |
| 48 | −0.014826 | −0.094391 | 0.056779 | 0.032379 | 0.213628 | −0.052737 | −0.06914 | −0.029008 | −0.081692 | 0.025746 | 0.094094 | −0.104209 | −0.046488 | 0.107663 |
| 49 | 0.000824 | 0.031877 | −0.067801 | 0.022261 | −0.027627 | 0.064019 | −0.108888 | −0.014573 | 0.003182 | −0.064669 | 0.041785 | −0.057237 | −0.031923 | −0.035388 |
| 50 | 0.093915 | 0.212306 | 0.075625 | 0.0363 | 0.175094 | 0.128747 | 0.016309 | −0.024158 | 0.281527 | 0.153216 | −0.029464 | −0.198302 | −0.081367 | −0.125855 |
| 51 | 0.016238 | −0.073832 | −0.033568 | −0.057293 | 0.150746 | −0.166342 | −0.178174 | 0.053826 | −0.075863 | −0.130827 | 0.057025 | 0.002536 | −0.08093 | −0.111105 |
| 52 | 0.148794 | 0.051065 | 0.077288 | −0.084289 | −0.08123 | −0.150969 | −0.020993 | −0.157566 | −0.139542 | 0.216023 | −0.041167 | −0.137582 | 0.093482 | 0.059614 |
| 73 | −0.02093 | 0.01438 | −0.066455 | −0.273612 | −0.188772 | 0.238082 | −0.145235 | −0.083688 | 0.084438 | −0.308905 | −0.097999 | −0.17523 | 0.135184 | −0.000518 |
| 54 | −0.004507 | 0.027218 | −0.171777 | 0.22024 | 0.194192 | −0.047309 | 0.020433 | −0.042695 | −0.024485 | −0.02642 | −0.241204 | −0.047342 | 0.00593 | 0.126498 |
| 55 | 0.018511 | 0.149484 | 0.239148 | −0.08164 | −0.090687 | 0.190998 | −0.146047 | 0.055618 | 0.021067 | 0.042254 | 0.121591 | −0.012866 | 0.03439 | 0.02193 |
| 56 | −0.116001 | −0.087019 | 0.118136 | 0.133307 | −0.300683 | 0.098241 | 0.156471 | −0.065128 | −0.080932 | −0.008601 | −0.020936 | 0.053186 | −0.032196 | 0.072652 |
| 57 | −0.158709 | 0.236679 | 0.061006 | −0.241417 | 0.024633 | 0.067793 | 0.214776 | −0.009206 | −0.010361 | −0.112605 | −0.120034 | −0.030272 | 0.022049 | −0.053093 |
| 58 | 0.354205 | −0.023854 | −0.044179 | −0.08332 | −0.107253 | −0.291834 | 0.067104 | −0.037246 | 0.294263 | −0.04935 | −0.067699 | 0.166898 | 0.125283 | −0.006482 |
| 59 | −0.087562 | 0.091606 | 0.092781 | −0.14151 | 0.276448 | 0.03946 | −0.08689 | −0.112585 | −0.06885 | −0.136494 | −0.031205 | 0.070668 | −0.015566 | −0.209064 |
| 60 | 0.151837 | −0.063443 | −0.033657 | 0.125764 | 0.068179 | −0.092687 | 0.068568 | 0.134481 | 0.036637 | 0.063998 | 0.044657 | −0.05803 | 0.068107 | −0.014737 |
| 61 | −0.028791 | −0.040165 | 0.046012 | −0.173668 | −0.067785 | 0.10715 | 0.092964 | −0.000061 | −0.087792 | 0.08929 | 0.061603 | 0.117815 | 0.082768 | −0.136091 |
| 62 | −0.11515 | 0.076247 | 0.122641 | 0.00691 | 0.163211 | 0.006344 | −0.019984 | 0.032234 | −0.004125 | −0.019227 | −0.165194 | −0.096234 | 0.042419 | −0.083476 |
| 63 | 0.069072 | −0.054479 | 0.10039 | 0.053696 | 0.012488 | −0.008654 | −0.004637 | 0.03544 | −0.000252 | −0.001099 | −0.063769 | −0.084829 | 0.035902 | 0.047562 |
| 64 | −0.030786 | −0.042646 | −0.124351 | −0.116431 | 0.030898 | 0.052129 | −0.058514 | 0.022506 | −0.087372 | 0.13005 | −0.080213 | −0.026 | −0.001707 | −0.125139 |
| 65 | −0.121503 | 0.057082 | −0.016425 | −0.13683 | 0.063223 | 0.02743 | −0.148748 | −0.155804 | 0.106777 | 0.072958 | 0.166293 | 0.008861 | −0.041479 | −0.049891 |
| 66 | 0.024946 | 0.004075 | −0.033021 | −0.055576 | 0.019144 | −0.009176 | 0.004428 | 0.099877 | −0.046439 | −0.082802 | −0.079232 | −0.149321 | −0.040397 | 0.017155 |
| 67 | −0.09353 | −0.045602 | −0.138989 | 0.077181 | −0.04288 | −0.101451 | −0.059722 | −0.065768 | 0.227012 | −0.021329 | 0.048532 | −0.010094 | −0.007249 | −0.018609 |
| 68 | −0.087234 | −0.032115 | −0.075717 | 0.023392 | −0.117614 | 0.050463 | 0.010397 | −0.006231 | −0.022121 | −0.089728 | −0.120985 | −0.013831 | 0.071688 | 0.110809 |
| 69 | 0.391052 | −0.119038 | −0.052758 | −0.056304 | 0.110402 | 0.064148 | −0.052674 | −0.099796 | 0.021694 | −0.114101 | 0.152908 | 0.127035 | −0.045982 | 0.053202 |
| 70 | −0.139751 | 0.487103 | −0.221865 | −0.119513 | −0.048836 | −0.124914 | 0.052888 | 0.093226 | −0.03648 | 0.198208 | −0.032455 | 0.004259 | 0.02362 | 0.045644 |
| 71 | 0.029103 | −0.21276 | 0.577646 | −0.124811 | −0.032353 | −0.012565 | 0.009209 | −0.040587 | 0.037104 | 0.01627 | −0.069143 | 0.030827 | 0.00379 | 0.046129 |

APPENDIX B6-continued

PCA Transformation
Matrix (82 x 82; Early/Late)

| | | | | | | | | | | | | | | |
|---|---|---|---|---|---|---|---|---|---|---|---|---|---|---|
| 72 | −0.074107 | −0.172054 | −0.085782 | 0.259565 | 0.082362 | 0.065582 | −0.115804 | −0.052818 | −0.044646 | −0.074218 | −0.072435 | −0.036123 | 0.090078 | −0.266733 |
| 73 | 0.061813 | −0.047126 | 0.097938 | −0.000222 | 0.359902 | −0.009211 | 0.049247 | −0.067397 | −0.074343 | 0.027611 | 0.042415 | −0.043162 | −0.017662 | −0.096802 |
| 74 | −0.137147 | −0.075293 | −0.021169 | 0.122103 | 0.089002 | 0.212777 | −0.052542 | 0.018554 | 0.038674 | 0.20569 | 0.063721 | −0.139997 | 0.063889 | 0.09312 |
| 75 | −0.032058 | −0.073393 | 0.020188 | −0.133959 | 0.023928 | −0.067894 | 0.50093 | −0.089794 | −0.198531 | −0.137232 | −0.040265 | −0.172869 | −0.032041 | 0.025343 |
| 76 | −0.030869 | 0.201259 | −0.063237 | −0.008846 | −0.092137 | −0.053235 | −0.173384 | 0.424661 | −0.105433 | −0.07488 | 0.110297 | 0.107919 | −0.052414 | −0.063418 |
| 77 | −0.145131 | −0.114307 | 0.063794 | −0.064625 | −0.052645 | −0.024656 | −0.117893 | −0.128702 | 0.489869 | 0.063701 | −0.069619 | −0.003169 | −0.043104 | −0.074299 |
| 78 | 0.032334 | −0.038636 | −0.122864 | 0.006253 | −0.161876 | 0.052503 | −0.064015 | 0.014302 | −0.013181 | 0.259328 | −0.213693 | −0.015003 | −0.210189 | 0.077342 |
| 79 | 0.149956 | 0.025583 | −0.067208 | −0.031563 | −0.012151 | −0.018074 | 0.044371 | 0.060334 | −0.005074 | −0.121575 | 0.255617 | −0.06494 | −0.02633 | 0.053853 |
| 80 | −0.001709 | 0.029778 | 0.031256 | −0.035538 | −0.059877 | −0.100494 | −0.131081 | 0.162458 | 0.018041 | −0.058369 | −0.098003 | 0.403413 | −0.102218 | −0.086403 |
| 81 | 0.018038 | 0.065224 | −0.041881 | 0.149125 | −0.039554 | 0.026782 | 0.074042 | −0.134099 | 0.018119 | −0.088589 | 0.085485 | −0.017017 | 0.566182 | −0.148837 |
| 82 | 0.181337 | 0.087438 | 0.040959 | −0.070259 | 0.040636 | 0.087236 | −0.010531 | −0.145378 | −0.057879 | −0.005043 | −0.098016 | −0.075981 | −0.167363 | 0.285627 |

APPENDIX B7

PCA Transformation
Matrix (77 × 77; Normal/Diseased)

| | A | B | C | D | E | F | G | H | I | J | K | L |
|---|---|---|---|---|---|---|---|---|---|---|---|---|
| 1 | 494.4/184.1>GPCho:Lyso 16:1 | 0.002997 | 0.062696 | 0.031314 | −0.081471 | −0.324152 | 0.13776 | −0.158994 | 0.138371 | −0.070351 | −0.061116 | −0.085673 |
| 2 | 496.4/184.1>GPCho:Lyso 16:0 | −0.095838 | 0.031641 | 0.04649 | −0.020923 | −0.193528 | −0.041146 | −0.34561 | −0.03968 | −0.066205 | 0.173704 | 0.297156 |
| 3 | 520.4/184.1>GPCho:Lyso 18:2 | −0.00842 | −0.057422 | 0.27412 | −0.069902 | −0.044983 | 0.099001 | −0.163597 | 0.046346 | −0.029071 | 0.012535 | 0.106476 |
| 4 | 522.4/184.1>GPCho:Lyso 18:1 | −0.083418 | −0.021083 | 0.111513 | −0.072058 | −0.258684 | 0.206289 | −0.247697 | 0.04681 | −0.011944 | −0.004995 | 0.066908 |
| 5 | 524.4/184.1>GPCho:Lyso 18:0 | −0.063104 | 0.051141 | 0.163883 | −0.029857 | −0.230045 | −0.097753 | −0.234266 | 0.042785 | 0.042606 | −0.012397 | 0.18003 |
| 6 | 544.4/184.1>GPCho:Lyso 20:4 | 0.040093 | −0.201638 | 0.040811 | 0.027115 | −0.133974 | −0.063623 | −0.044753 | 0.126926 | −0.041815 | −0.083017 | 0.172645 |
| 7 | 568.4/184.1>GPCho:Lyso 22:6 | 0.041973 | −0.188431 | 0.064084 | 0.087102 | −0.161888 | −0.00798 | −0.081168 | −0.061841 | −0.122746 | 0.206642 | −0.066783 |
| 8 | 570.4/184.1>GPCho:Lyso 22:5 | 0.062674 | −0.171277 | 0.08064 | 0.056566 | −0.220534 | 0.005224 | −0.078285 | −0.01968 | −0.07499 | 0.13535 | −0.041574 |
| 9 | 678.5/184.1>GPCho:28:0 | −0.037045 | 0.143161 | 0.109468 | −0.018445 | −0.136571 | 0.008469 | 0.198421 | −0.114042 | −0.312015 | −0.097274 | 0.185557 |
| 10 | 678.5/184.1>GPCho:28:0a | −0.036756 | 0.136073 | 0.118652 | −0.022191 | −0.137837 | 0.015113 | 0.199294 | −0.106887 | −0.319057 | −0.097882 | 0.197061 |
| 11 | 704.6/184.1>GPCho:30:1a | −0.180737 | −0.111254 | 0.012585 | 0.066393 | 0.060165 | 0.074609 | 0.011603 | −0.074838 | 0.013997 | −0.041546 | 0.042369 |
| 12 | 706.6/184.1>GPCho:30:0a | −0.120117 | −0.035636 | 0.069689 | 0.053756 | −0.102523 | 0.110527 | 0.270962 | −0.1708 | −0.206421 | −0.226944 | 0.097284 |
| 13 | 718.6/184.1>GPCho:32:0p, 32:1e | −0.120864 | 0.059793 | 0.07405 | 0.213661 | −0.035254 | 0.091308 | 0.116132 | 0.013673 | −0.110223 | 0.095648 | −0.046495 |
| 14 | 730.8/184.1>GPCho:32:2 | −0.129443 | −0.034558 | 0.026916 | 0.035016 | −0.040837 | −0.059641 | 0.113726 | 0.360132 | −0.182605 | 0.18178 | −0.176013 |
| 15 | 732.6/184.1>GPCho:32:1a | −0.100711 | 0.044821 | −0.178274 | −0.079355 | −0.184906 | 0.087854 | 0.082083 | 0.119517 | −0.11743 | −0.048817 | −0.228422 |
| 16 | 734.6/184.1>GPCho:32:0a | −0.094581 | 0.032495 | −0.210572 | 0.033347 | −0.005098 | 0.185628 | 0.114539 | −0.094485 | 0.065304 | −0.037364 | 0.122631 |
| 17 | 742.6/184.1>GPCho:34:2p, 34:3e | −0.036163 | 0.139545 | 0.153488 | 0.147029 | −0.062841 | 0.037043 | 0.020427 | −0.008005 | 0.003619 | 0.133382 | −0.023145 |
| 18 | 744.6/184.1>GPCho:34:1p, 34:2e | 0.101182 | 0.038707 | 0.226609 | 0.092617 | 0.035284 | 0.153939 | 0.0613 | 0.04082 | 0.056147 | −0.042104 | −0.091173 |
| 19 | 746.6/184.1>GPCho:34:0p, 34:1e | −0.016847 | 0.087263 | −0.024537 | 0.20312 | 0.017291 | 0.355235 | −0.048829 | 0.068653 | 0.107279 | −0.157211 | −0.082645 |
| 20 | 748.6/184.1>GPCho:34:0e | −0.059931 | 0.119976 | −0.038283 | 0.235587 | 0.012251 | 0.199006 | 0.063089 | 0.081478 | 0.039969 | −0.129581 | 0.005402 |
| 21 | 756.6/184.1>GPCho:34:3a | −0.068489 | 0.221988 | 0.015664 | −0.02934 | 0.031683 | −0.003837 | −0.083045 | 0.050725 | 0.109629 | 0.08651 | 0.002884 |
| 22 | 758.7/184.1>GPCho:34:2a | 0.116699 | 0.083218 | −0.001491 | −0.094664 | 0.257285 | 0.060971 | −0.049256 | −0.0873 | −0.090882 | 0.13558 | −0.026772 |
| 23 | 760.6/184.1>GPCho:34:1a | 0.028388 | 0.117941 | −0.235796 | −0.062285 | −0.069932 | 0.188476 | −0.022394 | −0.053221 | −0.01763 | 0.036263 | −0.08533 |
| 24 | 762.6/184.1>GPCho:34:0a | 0.006341 | 0.114376 | −0.217941 | −0.063236 | −0.147441 | 0.195307 | 0.072824 | −0.032149 | 0.042156 | 0.033431 | −0.03956 |
| 25 | 768.6/184.1>GPCho:36:3p, 36:4e | 0.136762 | −0.122702 | 0.020886 | 0.170364 | −0.029824 | 0.051482 | −0.05778 | −0.01762 | 0.073588 | −0.120012 | −0.023903 |
| 26 | 770.6/184.1>GPCho:36:2p, 36:3e | 0.129471 | 0.005206 | 0.157352 | 0.156723 | −0.009043 | 0.121822 | −0.072327 | 0.045398 | 0.161527 | −0.13246 | −0.136683 |
| 27 | 772.6/184.1>GPCho:36:1p, 36:2e | 0.036059 | 0.178125 | 0.130644 | 0.136215 | 0.088557 | 0.085218 | 0.048693 | 0.150019 | 0.035189 | 0.014343 | 0.001549 |
| 28 | 774.6/184.1>GPCho:36:0p, 36:1e | 0.013038 | 0.166671 | 0.034679 | 0.21509 | −0.047889 | 0.013726 | 0.117112 | 0.129756 | −0.140718 | −0.028867 | 0.021913 |
| 29 | 782.6/184.1>GPCho:36:4a | 0.145866 | −0.098689 | −0.126996 | 0.012873 | 0.018777 | −0.107648 | 0.159536 | 0.133601 | −0.021278 | −0.095796 | 0.174661 |
| 30 | 784.6/184.1>GPCho:36:3a | 0.181463 | 0.040174 | 0.010018 | −0.06241 | −0.058203 | −0.085305 | 0.05297 | 0.161267 | 0.067344 | −0.149849 | 0.049181 |
| 31 | 786.6/184.1>GPCho:36:2a | 0.14646 | 0.094954 | 0.157272 | −0.08636 | 0.041082 | 0.003064 | 0.019568 | 0.022484 | 0.052795 | −0.033827 | −0.059492 |
| 32 | 788.6/184.1>GPCho:36:1a | −0.00306 | 0.222951 | 0.048493 | −0.081148 | −0.120141 | −0.036049 | −0.02153 | −0.037465 | 0.078785 | −0.055093 | −0.124722 |
| 33 | 790.8/184.1>GPCho:36:0 | −0.035983 | 0.219095 | 0.009951 | 0.003007 | −0.174331 | −0.040205 | −0.00261 | −0.054988 | 0.084109 | −0.008284 | −0.139538 |
| 34 | 792.6/184.1>GPCho:38:5p, 38:6e | 0.103886 | −0.079288 | 0.037331 | 0.226368 | −0.10732 | 0.050236 | −0.066169 | −0.169695 | −0.027935 | 0.186632 | −0.122383 |
| 35 | 794.6/184.1>GPCho:38:4p, 38:5e | 0.129732 | −0.132652 | −0.019043 | 0.187348 | −0.009605 | 0.082581 | −0.089705 | −0.010281 | 0.083319 | −0.061022 | −0.066134 |
| 36 | 796.6/184.1>GPCho:38:3p, 38:4e | 0.128105 | −0.096772 | −0.03583 | 0.234021 | 0.000518 | 0.038086 | −0.049207 | 0.063263 | 0.069396 | −0.144802 | 0.034974 |
| 37 | 798.6/184.1>GPCho:38:2p, 38:3e | 0.065089 | 0.139786 | −0.067589 | 0.240476 | 0.012003 | −0.055045 | 0.003077 | 0.07618 | 0.081406 | −0.056928 | 0.162999 |
| 38 | 800.6/184.1>GPCho:38:1p, 38:2e | −0.089612 | 0.120096 | 0.103254 | 0.222456 | 0.023295 | −0.032343 | 0.014921 | 0.103969 | −0.074711 | 0.045177 | 0.043331 |
| 39 | 808.6/184.1>GPCho:38:5a | 0.169407 | −0.087533 | −0.058968 | 0.080232 | −0.118999 | −0.094255 | 0.102398 | 0.03249 | −0.051098 | 0.089004 | −0.010935 |
| 40 | 810.6/184.1>GPCho:38:4a | 0.15594 | −0.080509 | −0.102777 | 0.041248 | −0.053805 | −0.179858 | 0.120119 | 0.155229 | 0.049343 | −0.128654 | 0.095423 |
| 41 | 812.6/184.1>GPCho:38:3a | 0.076589 | 0.020029 | −0.106138 | 0.021824 | −0.163116 | −0.299636 | 0.033391 | 0.192301 | 0.152653 | −0.216611 | 0.03454 |
| 42 | 814.6/184.1>GPCho:38:2a | −0.195508 | −0.028575 | −0.060501 | 0.0804 | 0.011238 | −0.058589 | −0.044768 | −0.076488 | 0.10981 | −0.057027 | −0.05092 |
| 43 | 816.6/184.1>GPCho:38:1a | −0.152128 | 0.105354 | 0.08871 | 0.047315 | 0.000257 | −0.189652 | −0.040461 | −0.197838 | 0.056765 | −0.047486 | −0.075354 |
| 44 | 820.6/184.1>GPCho:40:5p, 40:6e | 0.13197 | −0.092727 | 0.003204 | 0.236475 | −0.055956 | 0.027837 | −0.006316 | −0.073869 | −0.072385 | 0.170263 | −0.116531 |
| 45 | 822.6/184.1>GPCho:40:4p, 40:5e | 0.0806 | 0.061819 | −0.094531 | 0.270683 | 0.010598 | −0.020105 | 0.009047 | −0.113742 | 0.041213 | 0.183053 | 0.073677 |
| 46 | 824.6/184.1>GPCho:40:3p, 40:4e | 0.054317 | 0.114739 | −0.118297 | 0.256367 | 0.022371 | −0.033583 | −0.035119 | −0.111437 | 0.105331 | 0.041674 | 0.13078 |

APPENDIX B7-continued

PCA Transformation
Matrix (77 × 77; Normal/Diseased)

| | | | | | | | | | | | | |
|---|---|---|---|---|---|---|---|---|---|---|---|---|
| 47 | 826.6/184.1>GPCho:40:2p, 40:3e | −0.087932 | 0.208618 | −0.063167 | 0.072144 | 0.055837 | −0.048698 | −0.04528 | −0.018677 | 0.059374 | 0.09701 | 0.153208 |
| 48 | 828.6/184.1>GPCho:40:1p, 40:2e | −0.109685 | 0.176255 | −0.048338 | 0.088194 | 0.054381 | −0.014243 | −0.034659 | −0.001223 | −0.014597 | 0.090536 | 0.200634 |
| 49 | 834.6/184.1>GPCho:40:6a | 0.139604 | −0.096133 | −0.050788 | 0.097906 | −0.158047 | −0.074232 | 0.076052 | −0.093021 | −0.098364 | 0.205297 | −0.153554 |
| 50 | 836.6/184.1>GPCho:40:5a | 0.108569 | 0.049588 | −0.113144 | 0.090113 | −0.177125 | −0.214905 | 0.096644 | −0.158985 | −0.012372 | 0.211503 | −0.02576 |
| 51 | 838.6/184.1>GPCho:40:4a | 0.056794 | 0.157178 | −0.124397 | 0.041729 | −0.136225 | −0.229792 | 0.052727 | −0.072712 | 0.089691 | 0.027653 | 0.092443 |
| 52 | 701.5/184.1>SM:18/16:1 | −0.159042 | −0.098924 | 0.057102 | 0.038081 | 0.027287 | 0.024855 | −0.021582 | 0.13889 | −0.018034 | 0.055746 | 0.111753 |
| 53 | 703.5/184.1>SM:18/16:0 | −0.179131 | −0.116573 | 0.022002 | 0.041161 | 0.065669 | 0.066468 | −0.008124 | −0.056291 | −0.019199 | −0.03834 | 0.10527 |
| 54 | 703.8/184.4>SM:d18:1/16:0 | −0.178436 | −0.119843 | 0.009231 | 0.078323 | 0.064877 | 0.050941 | −0.020509 | −0.061581 | 0.012717 | −0.042136 | 0.038167 |
| 55 | 705.8/184.4>SM:d18:0/16:0 | −0.178883 | −0.119779 | 0.013625 | 0.059454 | 0.03845 | 0.036218 | 0.068078 | −0.107497 | −0.002223 | −0.099796 | 0.050084 |
| 56 | 727.6/184.1>SM:18/18:2 | −0.127641 | 0.022582 | 0.050795 | 0.080883 | 0.104272 | −0.112322 | 0.007457 | 0.344597 | −0.004749 | 0.110959 | −0.071665 |
| 57 | 729.6/184.1>SM:18/18:1 | −0.166843 | −0.074505 | −0.065282 | 0.037941 | 0.037293 | −0.054213 | −0.011948 | 0.261584 | −0.048819 | 0.181952 | −0.099831 |
| 58 | 731.6/184.1>SM:18/18:0 | −0.183093 | −0.070894 | −0.091922 | 0.003494 | 0.036236 | −0.057144 | 0.055127 | 0.082401 | −0.057928 | 0.05902 | −0.081888 |
| 59 | 731.8/184.4>SM:d18:1/18:0 | −0.181692 | −0.073515 | −0.09641 | 0.011889 | 0.035258 | −0.057485 | 0.053259 | 0.078658 | −0.046295 | 0.050674 | −0.095324 |
| 60 | 733.8/184.4>SM:d18:0/18:0 | −0.131457 | 0.00301 | −0.176557 | −0.066721 | −0.120917 | −0.010075 | 0.111736 | 0.022012 | −0.109375 | −0.072075 | −0.182617 |
| 61 | 757.6/184.1>SM:18/20:1 | −0.114012 | 0.177925 | 0.038616 | 0.002896 | 0.045976 | −0.011007 | −0.090465 | 0.172941 | 0.093143 | 0.135251 | −0.060543 |
| 62 | 759.6/184.1>SM:18/20:0 | 0.131855 | 0.074311 | 0.072475 | −0.110163 | 0.219508 | 0.049925 | 0.092262 | −0.072463 | −0.050569 | 0.183103 | −0.006097 |
| 63 | 759.8/184.4>SM:d18:1/20:0 | 0.126957 | 0.064807 | 0.094733 | −0.118335 | 0.206278 | 0.066875 | 0.130346 | −0.062415 | −0.051074 | 0.167868 | −0.012978 |
| 64 | 761.8/184.4>SM:d18:0/20:0 | 0.012964 | 0.109404 | −0.209288 | −0.061762 | −0.147822 | 0.199136 | 0.050981 | −0.036994 | 0.021937 | 0.054647 | −0.069933 |
| 65 | 773.6/184.1>SM:18/21:0 | −0.007573 | 0.07187 | 0.206657 | 0.159249 | −0.003647 | −0.0549 | 0.172997 | 0.126855 | −0.1832 | −0.013971 | 0.022026 |
| 66 | 787.6/184.1>SM:18/22:0 | 0.076677 | 0.07288 | 0.24742 | −0.054344 | 0.000912 | −0.073709 | 0.100305 | −0.03611 | 0.042878 | −0.064231 | −0.141159 |
| 67 | 787.9/184.4>SM:d18:1/22:0 | 0.038658 | 0.048502 | 0.269046 | −0.030946 | −0.022224 | −0.114141 | 0.083074 | −0.030195 | 0.074653 | −0.1188 | −0.186335 |
| 68 | 789.9/184.4>SM:d18:0/22:0 | −0.019792 | 0.204975 | 0.0222 | −0.054958 | −0.175401 | −0.032203 | −0.010972 | −0.024829 | 0.083502 | −0.088789 | −0.184714 |
| 69 | 813.6/184.1>SM:18/24:1 | −0.187263 | −0.082368 | −0.061001 | 0.084163 | 0.014931 | −0.049727 | −0.011681 | −0.044078 | 0.084227 | −0.055149 | −0.081259 |
| 70 | 813.9/184.4>SM:d18:1/24:1 | −0.186049 | −0.084646 | −0.050473 | 0.087349 | 0.018781 | −0.03418 | −0.000585 | −0.048248 | 0.090024 | −0.061588 | −0.0788 |
| 71 | 815.6/184.1>SM:18/24:0 | −0.148513 | −0.074385 | 0.083848 | 0.099668 | −0.0159 | −0.161482 | 0.013419 | −0.173782 | 0.062269 | −0.101708 | −0.149634 |
| 72 | 815.9/184.4>SM:d18:0/24:1 | −0.143422 | −0.093755 | 0.098358 | 0.06572 | 0.021117 | −0.156856 | −0.007498 | −0.180279 | −0.019396 | −0.122409 | −0.125164 |
| 73 | 817.9/184.4>SM:d18:0/24:0 | −0.082118 | 0.141564 | 0.037997 | 0.066682 | 0.065503 | −0.206238 | −0.170604 | −0.172242 | −0.102278 | −0.069728 | −0.220059 |
| 74 | 841.9/184.4>SM:d18:1/26:1 | −0.117381 | 0.182032 | −0.063404 | 0.01743 | 0.05043 | −0.159344 | −0.062602 | −0.018665 | 0.032946 | 0.024895 | 0.093868 |
| 75 | 843.9/184.4>SM:d18:0/26:1 | 0.100143 | 0.074655 | −0.113444 | 0.05621 | 0.157212 | −0.064088 | −0.267292 | 0.010415 | −0.333708 | −0.171263 | −0.071445 |
| 76 | 843.9/184.4>SM:d18:1/26:0 | 0.100192 | 0.076221 | −0.112709 | 0.056806 | 0.153285 | −0.067211 | −0.26613 | 0.009123 | −0.332215 | −0.171594 | −0.082982 |
| 77 | 845.9/184.4>SM:d18:0/26:0 | 0.097588 | 0.063344 | −0.155572 | 0.077479 | 0.098929 | −0.013059 | −0.26236 | 0.0293 | −0.322393 | −0.177397 | −0.092343 |

| | M | N | O | P | Q | R | S | T | U | V | W | X | Y | Z |
|---|---|---|---|---|---|---|---|---|---|---|---|---|---|---|
| 1 | 0.174133 | −0.075013 | 0.217843 | −0.042338 | 0.080777 | 0.219996 | −0.038581 | 0.092594 | −0.123408 | −0.198549 | 0.092144 | −0.005901 | 0.167299 | −0.249779 |
| 2 | −0.020788 | −0.082094 | 0.136447 | 0.01101 | 0.091444 | −0.036678 | 0.295102 | 0.050845 | −0.264725 | 0.071983 | 0.088998 | −0.059145 | −0.050408 | −0.026345 |
| 3 | −0.011583 | 0.06096 | −0.029837 | 0.130563 | 0.099969 | −0.001006 | −0.159723 | −0.018445 | −0.072965 | 0.068491 | 0.092387 | −0.022843 | 0.087385 | 0.196291 |
| 4 | 0.065095 | 0.007877 | −0.077537 | 0.124323 | 0.042108 | 0.066838 | 0.024277 | −0.115988 | 0.034031 | 0.142762 | −0.076206 | 0.050152 | 0.054149 | 0.079036 |
| 5 | −0.164281 | 0.166079 | 0.009355 | −0.14383 | −0.008987 | −0.059902 | 0.299494 | 0.031316 | −0.081512 | 0.046215 | 0.086605 | 0.011025 | −0.076734 | −0.036793 |
| 6 | −0.024817 | 0.106167 | 0.009327 | 0.322834 | −0.160977 | −0.034529 | −0.216401 | 0.049248 | 0.091654 | −0.123252 | −0.026137 | −0.173304 | 0.141687 | 0.090835 |
| 7 | 0.08137 | 0.151378 | 0.021451 | 0.072885 | 0.022034 | −0.016696 | −0.27712 | 0.020466 | 0.096323 | −0.032506 | −0.083713 | 0.021939 | −0.038553 | 0.152146 |
| 8 | 0.101787 | 0.130983 | −0.037273 | 0.060838 | 0.011574 | 0.053099 | −0.208569 | 0.036493 | 0.010063 | 0.068651 | −0.195173 | −0.108199 | −0.080396 | −0.028962 |
| 9 | −0.177227 | −0.172573 | 0.014992 | −0.013622 | −0.048468 | −0.073643 | −0.140852 | −0.289267 | −0.051915 | −0.041806 | −0.078192 | 0.033468 | −0.057865 | −0.00868 |
| 10 | −0.172522 | −0.170091 | 0.018617 | −0.065638 | −0.029286 | −0.040011 | −0.11993 | −0.298872 | 0.026482 | −0.022748 | −0.058495 | −0.048932 | 0.015522 | 0.024839 |
| 11 | −0.016351 | −0.020108 | −0.136532 | −0.048631 | −0.020566 | 0.103114 | −0.007881 | 0.194317 | 0.083262 | 0.035654 | −0.092481 | 0.060898 | −0.060864 | 0.002627 |
| 12 | −0.080524 | −0.085927 | 0.184093 | −0.132064 | 0.033606 | 0.24987 | −0.005427 | 0.263479 | −0.037189 | 0.134354 | −0.084318 | −0.038117 | −0.082652 | 0.019447 |
| 13 | 0.059541 | 0.02586 | −0.131091 | −0.018364 | −0.168292 | −0.127153 | −0.115406 | 0.043202 | 0.020085 | 0.242724 | 0.526628 | −0.151456 | 0.31509 | −0.006751 |
| 14 | −0.173427 | −0.295131 | −0.022118 | 0.029059 | 0.124945 | 0.046697 | 0.065864 | 0.067036 | −0.036502 | 0.061134 | −0.026199 | −0.245701 | −0.265346 | 0.032585 |
| 15 | −0.002323 | −0.023239 | 0.190993 | 0.013103 | 0.124842 | 0.069091 | −0.059422 | 0.09286 | 0.132281 | −0.116603 | 0.187636 | −0.022406 | 0.00325 | −0.031773 |
| 16 | −0.077125 | 0.181384 | 0.048389 | −0.118035 | −0.151619 | 0.045311 | 0.120445 | 0.23868 | −0.241238 | −0.215182 | −0.061071 | −0.107839 | 0.093121 | 0.418257 |

APPENDIX B7-continued

PCA Transformation
Matrix (77 × 77; Normal/Diseased)

| | | | | | | | | | | | | | | |
|---|---|---|---|---|---|---|---|---|---|---|---|---|---|---|
| 17 | 0.002092 | −0.235852 | 0.056585 | −0.039313 | −0.172803 | −0.432891 | 0.035913 | 0.32502 | 0.081282 | 0.180794 | −0.160947 | 0.178752 | 0.219774 | 0.009851 |
| 18 | −0.020935 | −0.156314 | −0.094679 | 0.021472 | 0.148272 | −0.06583 | 0.082266 | 0.208993 | 0.008018 | 0.059948 | −0.037979 | −0.071781 | 0.06016 | −0.192456 |
| 19 | 0.021406 | 0.062826 | −0.106655 | −0.113268 | −0.028901 | 0.048661 | −0.143223 | −0.070868 | −0.192059 | 0.083757 | 0.131046 | −0.216598 | −0.15587 | −0.067112 |
| 20 | 0.028836 | 0.245438 | 0.004752 | −0.030522 | −0.14338 | 0.008698 | −0.021702 | −0.14556 | −0.220039 | 0.200963 | 0.061035 | 0.022615 | −0.182331 | 0.144687 |
| 21 | −0.02414 | −0.032348 | 0.260718 | −0.028699 | −0.170169 | −0.03712 | −0.179563 | 0.080439 | 0.008497 | −0.09531 | −0.112335 | −0.095553 | −0.101156 | −0.01985 |
| 22 | 0.053676 | −0.069975 | 0.187576 | −0.190756 | −0.04158 | 0.15125 | 0.184631 | −0.095745 | 0.261753 | 0.129944 | 0.042111 | −0.107087 | 0.045301 | 0.100933 |
| 23 | 0.123736 | −0.083785 | −0.081586 | −0.018316 | −0.021627 | −0.00857 | 0.153685 | −0.144157 | 0.144169 | −0.019121 | −0.031621 | −0.02183 | 0.028109 | 0.033117 |
| 24 | 0.117032 | −0.062993 | −0.157224 | 0.076871 | −0.029454 | −0.035511 | 0.025158 | −0.0225 | −0.028642 | −0.049295 | −0.036607 | −0.005568 | 0.108637 | 0.019316 |
| 25 | −0.192124 | −0.17461 | 0.002298 | 0.10746 | −0.210316 | −0.033453 | 0.078705 | −0.059366 | 0.047956 | −0.1708 | 0.138838 | −0.008923 | 0.088513 | −0.015073 |
| 26 | −0.059041 | −0.255251 | 0.052864 | −0.035443 | 0.079354 | 0.000138 | 0.026263 | 0.000716 | −0.011969 | 0.018597 | 0.034406 | 0.064053 | −0.002292 | −0.026089 |
| 27 | 0.04473 | 0.205232 | 0.098861 | −0.010369 | 0.079614 | −0.024596 | −0.046396 | 0.125567 | −0.014233 | 0.025228 | −0.182806 | −0.091411 | −0.0106 | −0.118703 |
| 28 | 0.20351 | 0.217387 | −0.005584 | 0.117037 | 0.09324 | −0.006146 | 0.215805 | −0.088435 | 0.160011 | 0.014311 | −0.103975 | −0.006744 | −0.010851 | −0.000317 |
| 29 | 0.023224 | −0.028269 | 0.078246 | 0.165042 | −0.209176 | −0.05052 | 0.066526 | 0.107595 | −0.00851 | −0.050379 | −0.030386 | −0.085025 | 0.128499 | −0.082261 |
| 30 | 0.123409 | −0.123488 | 0.095147 | −0.06902 | 0.097396 | 0.046716 | −0.202182 | 0.062203 | −0.022602 | 0.179959 | 0.127477 | 0.202514 | −0.029834 | 0.17729 |
| 31 | −0.147679 | 0.156049 | −0.058659 | −0.19889 | 0.062002 | 0.106888 | −0.066489 | 0.037313 | 0.196232 | −0.005154 | 0.103143 | −0.088811 | −0.000205 | −0.046335 |
| 32 | −0.140805 | 0.089036 | −0.145355 | −0.025933 | −0.000337 | 0.074356 | −0.048651 | −0.026231 | 0.156181 | −0.092322 | −0.058724 | −0.098204 | 0.043587 | 0.066513 |
| 33 | −0.118412 | 0.023703 | −0.03951 | 0.01198 | −0.075221 | −0.035322 | 0.046466 | 0.00351 | 0.062705 | −0.036557 | −0.16423 | −0.019808 | 0.035418 | 0.130499 |
| 34 | −0.149915 | −0.070238 | 0.107481 | −0.1743 | −0.146693 | −0.123102 | 0.029242 | 0.007742 | 0.078057 | −0.140078 | 0.066408 | 0.174541 | 0.006927 | 0.158241 |
| 35 | −0.196972 | −0.06033 | 0.083133 | −0.000012 | −0.086635 | 0.044661 | 0.006461 | −0.117263 | −0.05439 | −0.117029 | −0.020163 | −0.089861 | 0.006838 | −0.130732 |
| 36 | −0.107299 | −0.059362 | 0.115875 | 0.133669 | −0.034311 | −0.001822 | 0.127867 | −0.190045 | −0.031376 | 0.062677 | −0.016073 | 0.071388 | −0.150286 | −0.027674 |
| 37 | 0.026263 | −0.084658 | 0.079076 | 0.176481 | 0.266282 | 0.093928 | −0.046046 | 0.073347 | 0.136859 | 0.021242 | −0.059503 | 0.226296 | −0.035547 | 0.177676 |
| 38 | 0.245989 | −0.035228 | −0.039903 | −0.093381 | 0.006059 | −0.017163 | 0.052846 | 0.067044 | 0.092472 | −0.26401 | −0.094676 | 0.0096 | 0.017799 | 0.034575 |
| 39 | 0.067199 | 0.043782 | −0.005722 | −0.058891 | −0.153989 | 0.034138 | −0.063758 | 0.040913 | −0.03948 | 0.070379 | −0.109745 | −0.058186 | −0.054213 | −0.247578 |
| 40 | −0.035374 | 0.084085 | 0.033502 | 0.02186 | −0.206038 | −0.021557 | 0.085289 | 0.043366 | −0.022439 | −0.034057 | −0.013691 | −0.070526 | −0.020679 | −0.124619 |
| 41 | 0.142593 | −0.145596 | −0.047 | −0.230938 | 0.098591 | −0.14823 | −0.147095 | 0.01691 | −0.062923 | 0.072417 | 0.12884 | 0.063967 | −0.13216 | 0.300786 |
| 42 | 0.041286 | 0.000276 | 0.049105 | −0.102488 | 0.174008 | −0.146241 | −0.136264 | −0.11001 | −0.032479 | −0.026934 | −0.121617 | −0.143656 | 0.106568 | −0.022063 |
| 43 | 0.086192 | −0.054561 | 0.044839 | 0.048533 | −0.051549 | 0.081206 | −0.039474 | −0.052879 | 0.028489 | −0.12628 | 0.050933 | −0.217041 | 0.055587 | 0.164645 |
| 44 | −0.039774 | 0.080126 | 0.086965 | −0.048505 | 0.060575 | 0.057576 | 0.018984 | −0.05427 | −0.006417 | 0.012686 | −0.015237 | 0.028459 | −0.116251 | 0.020975 |
| 45 | −0.137841 | −0.052546 | −0.007263 | 0.168571 | 0.265696 | 0.218448 | −0.110427 | 0.03205 | 0.026653 | 0.009053 | 0.013848 | −0.065746 | 0.189508 | 0.054055 |
| 46 | −0.1262 | −0.074104 | −0.02835 | 0.154299 | 0.175616 | 0.127239 | 0.024076 | 0.002713 | 0.031764 | −0.122332 | 0.087399 | −0.100875 | −0.00046 | 0.018916 |
| 47 | −0.053295 | 0.0251 | 0.056475 | 0.036914 | 0.010082 | −0.017797 | −0.134489 | 0.04197 | 0.05399 | −0.122503 | 0.089726 | 0.072811 | 0.007459 | −0.113361 |
| 48 | 0.020502 | 0.162452 | 0.083831 | −0.010734 | −0.025789 | −0.042551 | −0.117644 | −0.101842 | 0.152777 | −0.071032 | 0.203331 | 0.328142 | −0.187831 | −0.24323 |
| 49 | 0.01351 | 0.12504 | 0.037796 | −0.185667 | −0.060286 | 0.027415 | −0.033484 | 0.005621 | −0.129235 | −0.05126 | 0.041111 | 0.221278 | −0.107201 | 0.037075 |
| 50 | 0.032916 | 0.018296 | −0.213214 | −0.169615 | 0.050301 | 0.069191 | −0.002915 | 0.046896 | −0.155904 | 0.085797 | 0.024617 | −0.085385 | 0.014319 | −0.121867 |
| 51 | −0.006656 | −0.077406 | −0.220728 | −0.024447 | 0.06758 | 0.096593 | 0.031283 | 0.022353 | −0.078169 | 0.099167 | −0.074576 | −0.149267 | 0.022981 | −0.155003 |
| 52 | 0.068652 | −0.197149 | −0.350777 | −0.101504 | −0.067291 | 0.137977 | −0.040357 | 0.119335 | −0.032293 | −0.367465 | 0.127329 | 0.124443 | −0.075985 | 0.042753 |
| 53 | −0.026193 | 0.016699 | −0.189985 | −0.037534 | −0.032576 | 0.075819 | −0.107469 | 0.067905 | 0.10532 | −0.040971 | 0.01814 | 0.127918 | −0.082942 | −0.140597 |
| 54 | −0.021939 | −0.025306 | −0.10537 | −0.033758 | −0.000552 | 0.04717 | 0.018328 | 0.07202 | 0.014413 | 0.040348 | −0.167384 | 0.115291 | −0.131796 | −0.035544 |
| 55 | −0.0565 | 0.016042 | −0.020461 | 0.005806 | 0.044987 | 0.08401 | 0.009174 | 0.17133 | −0.082006 | 0.020244 | −0.082251 | 0.102679 | 0.029413 | −0.112974 |
| 56 | −0.082309 | 0.000881 | 0.025713 | −0.141986 | −0.153152 | 0.415383 | 0.007892 | −0.255002 | −0.179263 | 0.09782 | −0.216999 | 0.273079 | 0.478486 | 0.033743 |
| 57 | −0.127971 | −0.083887 | −0.1938 | 0.061345 | −0.042511 | 0.00401 | 0.064786 | −0.079783 | 0.017082 | 0.014523 | 0.098276 | −0.025826 | −0.118053 | 0.092214 |
| 58 | −0.209339 | 0.113717 | 0.028784 | 0.104499 | 0.130008 | −0.144484 | 0.048598 | −0.008123 | 0.042025 | 0.054665 | 0.039375 | −0.020093 | 0.010216 | 0.050692 |
| 59 | −0.205673 | 0.09835 | 0.056092 | 0.101592 | 0.134952 | −0.154737 | 0.090682 | −0.009721 | 0.022171 | 0.076387 | −0.020368 | −0.022433 | −0.017045 | 0.072373 |
| 60 | −0.114052 | 0.102081 | 0.252615 | 0.125241 | 0.092872 | 0.023655 | 0.039503 | 0.140736 | −0.047302 | −0.081934 | 0.197455 | 0.187165 | 0.066186 | −0.100076 |
| 61 | −0.009877 | −0.100497 | 0.158202 | −0.008788 | −0.220213 | −0.029852 | −0.182312 | −0.017393 | −0.051376 | −0.167827 | −0.116785 | −0.129189 | −0.221359 | −0.054393 |
| 62 | 0.063087 | −0.038386 | 0.021165 | 0.143152 | 0.090751 | −0.024478 | −0.072755 | −0.002105 | −0.316813 | −0.118062 | 0.057599 | 0.026144 | −0.07517 | 0.030823 |
| 63 | 0.055242 | −0.091244 | 0.035215 | 0.221712 | 0.011247 | −0.014828 | −0.068999 | 0.037849 | −0.297821 | 0.02784 | 0.017261 | 0.037002 | −0.042071 | 0.021177 |
| 64 | 0.096887 | −0.11684 | −0.172073 | 0.244083 | −0.052383 | −0.099657 | 0.035473 | −0.103466 | −0.121187 | −0.003411 | −0.081515 | 0.212037 | −0.019478 | −0.045403 |
| 65 | 0.273158 | 0.153062 | −0.029853 | 0.071558 | 0.020293 | −0.066924 | 0.258262 | −0.033904 | −0.005777 | −0.158058 | 0.036333 | −0.063879 | −0.025625 | 0.043102 |
| 66 | −0.18432 | 0.155421 | −0.120486 | −0.030131 | 0.111104 | −0.065288 | 0.031092 | −0.036886 | −0.074753 | −0.23421 | 0.078638 | 0.097933 | 0.019792 | −0.039267 |

APPENDIX B7-continued

PCA Transformation
Matrix (77 × 77; Normal/Diseased)

| | | | | | | | | | | | | | | |
|---|---|---|---|---|---|---|---|---|---|---|---|---|---|---|
| 67 | −0.113174 | 0.126154 | −0.100502 | 0.138725 | 0.042238 | −0.024686 | 0.027231 | 0.023341 | −0.192177 | −0.084337 | 0.006091 | 0.128408 | 0.040565 | 0.003328 |
| 68 | −0.126873 | 0.048049 | −0.154286 | 0.192503 | −0.122446 | 0.076784 | 0.014099 | 0.088525 | 0.08655 | 0.090057 | −0.105916 | 0.120668 | −0.121246 | −0.003157 |
| 69 | 0.033337 | 0.014367 | 0.055603 | −0.073612 | 0.118718 | −0.176639 | −0.115008 | −0.138135 | −0.062398 | −0.002255 | −0.054331 | −0.023756 | 0.078093 | −0.085548 |
| 70 | 0.057286 | 0.002008 | 0.078529 | −0.037809 | 0.090115 | −0.18102 | −0.111758 | −0.102599 | −0.106582 | 0.052401 | −0.11647 | −0.002736 | 0.102427 | −0.129769 |
| 71 | 0.236493 | −0.111997 | 0.107914 | 0.005373 | 0.087411 | −0.026068 | 0.136591 | −0.144813 | −0.152999 | −0.153073 | −0.02211 | −0.038685 | 0.023073 | 0.029848 |
| 72 | 0.225762 | −0.098141 | 0.002871 | 0.153552 | −0.147087 | 0.121803 | 0.072165 | −0.083959 | 0.121533 | 0.073303 | 0.150988 | 0.00794 | −0.069081 | −0.096292 |
| 73 | 0.064076 | −0.034929 | 0.071416 | 0.225448 | −0.264489 | 0.221452 | −0.006729 | 0.130804 | −0.062592 | 0.184213 | 0.048506 | 0.026271 | −0.150634 | 0.110158 |
| 74 | −0.097361 | 0.029236 | −0.01782 | 0.046932 | −0.09166 | 0.003812 | −0.080761 | 0.0483 | −0.116503 | 0.110968 | 0.107627 | −0.01602 | 0.066779 | −0.145076 |
| 75 | −0.033403 | 0.021856 | −0.102839 | −0.030404 | 0.0308 | −0.072585 | −0.057875 | 0.093734 | −0.056207 | −0.027766 | −0.034532 | −0.008987 | 0.063856 | −0.002067 |
| 76 | −0.040198 | 0.018092 | −0.099844 | −0.030976 | 0.043564 | −0.066293 | −0.060006 | 0.090076 | −0.088403 | −0.041656 | −0.036597 | −0.011691 | 0.084331 | 0.017618 |
| 77 | −0.0085 | 0.009011 | −0.111568 | −0.0706 | 0.029866 | −0.094929 | −0.01786 | 0.034842 | −0.046358 | −0.05135 | −0.094028 | 0.045292 | −0.004638 | −0.041367 |

| | AA | AB | AC | AD | AE | AF | AG | AH | AI | AJ | AK | AL | AM | AN |
|---|---|---|---|---|---|---|---|---|---|---|---|---|---|---|
| 1 | 0.158251 | −0.024808 | 0.042347 | −0.05445 | 0.212502 | −0.052203 | 0.266143 | −0.20243 | 0.048528 | −0.023156 | 0.027164 | −0.181094 | 0.086172 | −0.131646 |
| 2 | −0.227582 | −0.106472 | −0.028423 | −0.020064 | 0.20343 | 0.098679 | −0.017334 | 0.275255 | 0.124568 | 0.008588 | 0.048002 | −0.014178 | 0.006064 | −0.034354 |
| 3 | 0.026131 | 0.244812 | −0.016353 | 0.098062 | −0.252802 | −0.105646 | −0.088189 | −0.129043 | −0.318819 | 0.101222 | 0.058943 | −0.000969 | −0.087122 | −0.159612 |
| 4 | 0.089788 | 0.078004 | 0.078466 | −0.153632 | −0.11855 | 0.010103 | −0.086705 | −0.156069 | −0.100258 | 0.136227 | −0.052122 | −0.136186 | −0.079123 | −0.009075 |
| 5 | 0.109474 | −0.177206 | 0.04603 | 0.043437 | −0.21545 | −0.07407 | −0.022957 | −0.013948 | 0.077829 | −0.110009 | 0.020502 | 0.193141 | 0.080435 | 0.105535 |
| 6 | 0.032958 | −0.01104 | −0.181423 | −0.037001 | 0.193987 | 0.083981 | −0.111639 | −0.088181 | 0.034953 | 0.136043 | 0.044294 | −0.011058 | −0.022375 | 0.145105 |
| 7 | −0.103336 | −0.029406 | −0.195166 | 0.045119 | 0.188178 | 0.047126 | −0.074759 | 0.053635 | 0.013121 | −0.102627 | −0.015639 | 0.190935 | −0.122922 | 0.034863 |
| 8 | 0.000585 | 0.076957 | −0.075776 | 0.283442 | −0.175633 | 0.011693 | 0.118261 | 0.102659 | 0.059012 | −0.319268 | −0.006481 | −0.063076 | 0.144255 | 0.153493 |
| 9 | 0.034748 | −0.015005 | 0.015699 | 0.003713 | 0.038237 | −0.097074 | 0.063169 | −0.032793 | 0.053491 | −0.11861 | 0.007778 | 0.043109 | −0.126877 | 0.026936 |
| 10 | −0.0394 | −0.056459 | 0.022402 | −0.035086 | −0.014002 | −0.027869 | 0.110393 | −0.03339 | 0.008658 | −0.105237 | −0.02369 | −0.033842 | −0.105552 | −0.089297 |
| 11 | −0.015869 | 0.038394 | 0.138712 | −0.017075 | 0.087962 | 0.179206 | 0.111037 | −0.118171 | 0.082439 | 0.011135 | 0.012954 | −0.01016 | −0.253491 | −0.151421 |
| 12 | −0.027234 | −0.031095 | 0.034887 | 0.061631 | −0.114724 | 0.130493 | −0.260695 | 0.029499 | −0.147542 | 0.152963 | 0.003042 | −0.002636 | 0.267104 | 0.23252 |
| 13 | 0.121907 | −0.083107 | 0.16134 | 0.050219 | −0.035008 | 0.282528 | 0.174339 | 0.149306 | 0.041018 | −0.009753 | 0.194385 | −0.015541 | 0.000565 | 0.137639 |
| 14 | 0.001894 | −0.201884 | −0.216139 | 0.0541 | 0.09006 | 0.005677 | −0.015238 | −0.092697 | −0.069122 | 0.195082 | 0.018883 | −0.009559 | −0.013715 | −0.066098 |
| 15 | −0.01411 | 0.101138 | −0.095963 | 0.075117 | 0.035457 | −0.094982 | 0.098646 | 0.017276 | 0.143927 | 0.017727 | −0.125575 | 0.116739 | −0.002779 | −0.019271 |
| 16 | −0.115335 | −0.092767 | −0.13147 | 0.140532 | −0.083756 | −0.002002 | 0.09173 | −0.292829 | 0.048733 | −0.184561 | −0.02204 | −0.227947 | 0.005781 | −0.045967 |
| 17 | 0.128941 | 0.098681 | −0.277514 | −0.166418 | −0.020416 | 0.008224 | 0.088676 | −0.120447 | −0.008992 | −0.11358 | −0.284636 | 0.085524 | 0.18168 | −0.089528 |
| 18 | −0.31805 | 0.008821 | −0.129675 | −0.082461 | 0.043436 | −0.160437 | −0.179094 | −0.097746 | −0.058962 | 0.029441 | 0.220302 | 0.006503 | −0.082804 | 0.117188 |
| 19 | 0.064885 | 0.038215 | −0.1348 | −0.122678 | −0.049187 | −0.175571 | −0.20435 | −0.031207 | 0.267441 | −0.228884 | 0.023475 | 0.206921 | −0.180887 | −0.156585 |
| 20 | −0.024835 | 0.07683 | −0.195085 | −0.058002 | 0.101928 | −0.070541 | 0.149591 | 0.128558 | −0.108174 | 0.321134 | −0.038547 | 0.020713 | 0.185742 | −0.121959 |
| 21 | 0.005512 | 0.106396 | 0.223335 | 0.053771 | −0.081727 | 0.080663 | 0.027376 | −0.03427 | −0.022688 | 0.13923 | 0.039225 | 0.091431 | −0.101508 | 0.036908 |
| 22 | 0.243583 | 0.092755 | −0.120176 | 0.079125 | −0.032559 | −0.071352 | 0.089854 | −0.077018 | −0.030759 | −0.060559 | 0.036599 | −0.039626 | −0.056806 | 0.084102 |
| 23 | −0.091034 | −0.036573 | −0.046762 | 0.066172 | −0.044622 | 0.013472 | −0.064307 | 0.007433 | −0.053453 | 0.10891 | −0.121981 | 0.155765 | 0.001717 | 0.240115 |
| 24 | −0.260407 | −0.157999 | 0.092693 | 0.153982 | −0.015267 | 0.086935 | 0.009827 | 0.028667 | −0.087744 | 0.001532 | 0.001559 | 0.056768 | 0.055424 | 0.023694 |
| 25 | −0.060957 | 0.031893 | 0.172314 | 0.197898 | 0.204254 | −0.014636 | −0.086375 | −0.003742 | −0.126308 | −0.005956 | 0.03169 | 0.005141 | 0.213529 | −0.034883 |
| 26 | −0.143902 | 0.099781 | 0.009642 | 0.148684 | −0.067553 | −0.001009 | 0.042669 | −0.026239 | −0.053932 | −0.197363 | 0.22962 | −0.027402 | −0.098083 | 0.158371 |
| 27 | −0.187758 | −0.133091 | 0.09097 | −0.02457 | 0.093831 | 0.00199 | 0.237872 | 0.079623 | −0.201705 | −0.08836 | −0.150555 | −0.085184 | −0.21053 | 0.147438 |
| 28 | 0.015949 | 0.034542 | 0.104032 | 0.048711 | 0.018527 | −0.065429 | 0.003342 | 0.04647 | −0.176756 | 0.043283 | 0.106604 | −0.15826 | 0.034337 | −0.038973 |
| 29 | −0.10041 | −0.08509 | −0.002668 | −0.213176 | −0.093184 | −0.043037 | −0.06222 | 0.038243 | 0.030424 | −0.031346 | 0.070867 | 0.11194 | −0.063542 | −0.157056 |
| 30 | −0.270658 | −0.007157 | 0.157672 | −0.084984 | −0.120005 | 0.222975 | −0.137944 | 0.082278 | 0.165296 | −0.053455 | −0.3028 | −0.025107 | 0.011113 | −0.134215 |
| 31 | 0.021978 | −0.170565 | −0.046565 | 0.062708 | 0.153832 | 0.069193 | −0.080495 | 0.014362 | −0.098878 | −0.048719 | −0.137764 | −0.039323 | 0.014378 | −0.186408 |
| 32 | −0.108965 | 0.024555 | −0.006216 | −0.15046 | 0.074134 | −0.077526 | −0.009492 | 0.199413 | 0.04445 | −0.122707 | 0.030392 | 0.024032 | 0.191076 | 0.040244 |
| 33 | 0.081388 | 0.100771 | −0.091678 | −0.16569 | 0.061686 | −0.012873 | 0.027904 | 0.31545 | −0.032405 | 0.001413 | 0.148259 | −0.031664 | 0.050424 | −0.032959 |
| 34 | −0.124102 | 0.084243 | 0.082821 | 0.093013 | 0.051891 | −0.199003 | −0.058936 | 0.066831 | 0.159867 | 0.32274 | 0.047524 | −0.240914 | −0.218149 | −0.107192 |
| 35 | 0.086534 | 0.091938 | 0.018049 | 0.03925 | −0.002341 | −0.018171 | −0.130182 | −0.002334 | −0.032261 | −0.121934 | −0.224915 | −0.15181 | 0.25147 | 0.073325 |
| 36 | 0.111779 | 0.059676 | −0.005624 | −0.018499 | 0.015409 | 0.203268 | 0.085099 | 0.065997 | −0.14186 | −0.187489 | −0.148668 | −0.007273 | −0.058319 | −0.045736 |

APPENDIX B7-continued

PCA Transformation
Matrix (77 × 77; Normal/Diseased)

| | | | | | | | | | | | | | | |
|---|---|---|---|---|---|---|---|---|---|---|---|---|---|---|
| 37 | −0.00252 | −0.06396 | 0.100735 | 0.053843 | 0.046973 | −0.109981 | 0.21966 | −0.056213 | −0.021208 | −0.107805 | 0.203389 | 0.10076 | 0.139659 | −0.207465 |
| 38 | 0.247293 | −0.179616 | 0.03936 | 0.217029 | −0.089352 | 0.066234 | −0.374177 | 0.166085 | 0.001386 | −0.072384 | 0.053529 | −0.051044 | −0.063579 | −0.278916 |
| 39 | −0.106399 | 0.037707 | −0.046241 | −0.013804 | −0.375883 | −0.099566 | 0.143359 | 0.118954 | 0.11835 | 0.134753 | 0.065397 | −0.264003 | −0.023577 | −0.054813 |
| 40 | 0.098685 | −0.066526 | −0.042956 | −0.059878 | −0.010994 | −0.096176 | 0.102942 | −0.000079 | −0.115056 | −0.010177 | 0.115658 | 0.067861 | −0.119822 | 0.034131 |
| 41 | 0.136733 | 0.051406 | −0.022653 | 0.098816 | 0.115522 | −0.122377 | 0.015946 | −0.015441 | 0.023055 | 0.030228 | 0.121701 | −0.126579 | −0.024154 | 0.29074 |
| 42 | −0.030584 | −0.091861 | 0.009461 | −0.067604 | 0.125523 | −0.024881 | −0.076831 | 0.073017 | −0.098633 | −0.014294 | −0.091503 | −0.106977 | 0.023805 | −0.011205 |
| 43 | −0.184267 | 0.094547 | −0.020646 | −0.095443 | −0.02566 | −0.009412 | 0.043543 | 0.102393 | −0.120788 | −0.07957 | 0.061806 | 0.028715 | 0.035596 | −0.159529 |
| 44 | −0.07995 | −0.054391 | 0.122235 | −0.089402 | −0.007781 | 0.064471 | 0.0834 | 0.059618 | −0.00125 | 0.030337 | −0.204375 | −0.065435 | −0.111236 | 0.095391 |
| 45 | 0.124213 | −0.185619 | 0.11698 | −0.201709 | −0.216315 | −0.208908 | 0.053462 | −0.048023 | 0.132661 | 0.138646 | −0.081167 | 0.103959 | 0.141539 | 0.083401 |
| 46 | 0.112933 | 0.051589 | −0.192631 | −0.027 | −0.047104 | 0.270439 | −0.039494 | −0.026447 | 0.114425 | 0.110922 | −0.044556 | 0.052411 | −0.169577 | 0.064518 |
| 47 | −0.046073 | −0.024838 | −0.131833 | 0.165548 | −0.023014 | −0.043274 | −0.027705 | −0.057852 | −0.045522 | −0.080039 | 0.026416 | 0.017362 | −0.11166 | 0.238148 |
| 48 | −0.141478 | −0.02282 | −0.318358 | 0.018142 | −0.050424 | 0.06811 | −0.127934 | −0.123163 | −0.025122 | 0.002832 | 0.060781 | −0.163854 | 0.178783 | 0.023285 |
| 49 | 0.047052 | −0.137769 | 0.083896 | −0.182828 | 0.063368 | −0.007613 | −0.097479 | −0.202045 | −0.133963 | −0.09975 | 0.188828 | 0.261274 | −0.01416 | −0.001923 |
| 50 | 0.000883 | 0.19153 | 0.086967 | 0.037854 | 0.083107 | −0.016371 | −0.080511 | −0.136633 | −0.232132 | −0.053492 | 0.015946 | 0.11318 | 0.109783 | −0.166885 |
| 51 | 0.034454 | 0.320406 | −0.125866 | 0.18098 | 0.074458 | 0.166533 | −0.019137 | −0.067495 | 0.061118 | 0.053056 | −0.116162 | −0.12421 | −0.078417 | −0.114455 |
| 52 | 0.049112 | 0.011694 | −0.014345 | −0.183696 | −0.13875 | −0.209812 | 0.085448 | 0.268081 | −0.185977 | −0.043748 | −0.251873 | −0.047876 | −0.042387 | 0.152377 |
| 53 | −0.102779 | 0.090001 | 0.070747 | 0.01169 | 0.12205 | −0.029437 | 0.124714 | −0.064665 | 0.05967 | 0.007722 | 0.089758 | 0.008727 | 0.17331 | −0.032128 |
| 54 | 0.131433 | 0.117962 | 0.000884 | 0.035893 | 0.183316 | 0.005867 | 0.189886 | 0.082695 | 0.157309 | 0.05699 | 0.050982 | 0.113345 | 0.00754 | 0.076397 |
| 55 | 0.102513 | 0.101942 | 0.097794 | 0.019923 | 0.03422 | 0.0651 | −0.030726 | 0.121555 | −0.044747 | −0.03786 | 0.078217 | 0.032416 | −0.111704 | −0.008704 |
| 56 | −0.122673 | 0.053697 | −0.119853 | 0.046959 | 0.051258 | 0.048547 | −0.103589 | 0.025461 | 0.108504 | −0.022288 | 0.069504 | 0.063961 | −0.017312 | 0.080995 |
| 57 | −0.04219 | −0.053588 | 0.030232 | −0.051622 | −0.091482 | 0.114148 | 0.056268 | −0.135078 | −0.11406 | −0.169702 | −0.014643 | −0.175749 | 0.074036 | −0.060359 |
| 58 | −0.13406 | 0.140655 | 0.109858 | 0.043715 | −0.061476 | −0.085297 | −0.029549 | −0.031727 | 0.072551 | −0.124873 | 0.025968 | −0.01346 | 0.0963 | −0.040627 |
| 59 | −0.055812 | 0.115336 | 0.097652 | 0.05553 | −0.050938 | −0.070952 | −0.024471 | −0.002015 | 0.093315 | −0.110368 | 0.018096 | −0.018977 | −0.04132 | −0.011921 |
| 60 | 0.100884 | 0.227137 | −0.081211 | −0.037041 | −0.094773 | 0.013021 | −0.119374 | 0.233289 | −0.174593 | −0.076796 | −0.017261 | 0.015824 | −0.161767 | −0.051055 |
| 61 | −0.016465 | 0.113384 | 0.226878 | 0.037321 | −0.147491 | 0.179548 | 0.014687 | −0.065147 | 0.048466 | 0.107536 | 0.066194 | 0.217217 | 0.153526 | −0.022244 |
| 62 | 0.045383 | 0.161418 | −0.022723 | −0.214941 | 0.068222 | −0.003841 | −0.04717 | 0.017229 | 0.01709 | −0.008408 | 0.173505 | −0.130897 | 0.180447 | 0.074206 |
| 63 | 0.1284 | −0.086372 | −0.014716 | 0.191777 | 0.091436 | −0.057242 | −0.030137 | 0.199094 | 0.110596 | −0.135449 | −0.017356 | −0.151373 | 0.040978 | −0.039544 |
| 64 | 0.046837 | −0.071805 | 0.060138 | 0.093164 | 0.007154 | 0.044975 | −0.029528 | −0.056403 | −0.078389 | 0.007083 | −0.022118 | 0.057147 | −0.098127 | 0.019789 |
| 65 | −0.022001 | 0.286753 | 0.203023 | −0.051969 | 0.147911 | −0.045453 | −0.147412 | −0.179689 | 0.276011 | −0.019599 | −0.207158 | 0.060811 | 0.044329 | 0.201222 |
| 66 | −0.038828 | −0.058469 | −0.037748 | −0.121255 | −0.056252 | 0.308669 | 0.111499 | −0.150689 | 0.028498 | 0.056013 | −0.003052 | −0.100603 | −0.058639 | 0.012641 |
| 67 | 0.073264 | −0.132104 | −0.072672 | 0.362718 | −0.07441 | −0.068611 | 0.143137 | 0.010597 | 0.029284 | 0.231102 | −0.181641 | 0.240003 | 0.028244 | −0.03568 |
| 68 | 0.123305 | −0.086551 | 0.062989 | −0.102174 | −0.072598 | 0.00421 | −0.145922 | −0.042145 | 0.244261 | −0.036338 | 0.147735 | −0.262099 | −0.029528 | 0.081836 |
| 69 | 0.063607 | −0.100586 | 0.060889 | −0.123239 | 0.022326 | 0.048813 | −0.065191 | −0.121391 | −0.038073 | 0.022089 | −0.037568 | −0.127119 | 0.073292 | 0.056739 |
| 70 | 0.135085 | −0.235426 | 0.041148 | 0.05869 | 0.000024 | −0.083428 | −0.117528 | −0.004774 | 0.03297 | 0.07336 | 0.010364 | −0.107461 | 0.011828 | −0.021014 |
| 71 | −0.078809 | 0.033705 | −0.173138 | −0.073258 | −0.215549 | 0.108241 | 0.148329 | −0.054924 | −0.031377 | −0.011578 | 0.086992 | 0.067976 | −0.068429 | 0.083133 |
| 72 | −0.183383 | −0.108575 | −0.118528 | 0.087701 | −0.088995 | −0.142856 | 0.049155 | −0.078791 | 0.138069 | −0.008401 | −0.053055 | 0.010829 | 0.069929 | −0.164137 |
| 73 | 0.03586 | −0.149172 | 0.037645 | −0.088702 | 0.139059 | −0.022771 | −0.071862 | −0.105641 | −0.141261 | −0.110187 | −0.104875 | −0.086556 | −0.095879 | 0.11016 |
| 74 | −0.090606 | 0.053783 | 0.14355 | 0.088772 | 0.074325 | −0.318433 | −0.050384 | −0.098566 | −0.11722 | −0.002799 | −0.197964 | −0.020994 | −0.185428 | 0.071125 |
| 75 | −0.02203 | −0.011946 | 0.015864 | 0.027932 | −0.056157 | −0.00811 | 0.005715 | 0.004102 | 0.068737 | 0.044586 | 0.027081 | −0.018499 | 0.042692 | −0.032509 |
| 76 | −0.028572 | 0.010397 | 0.02789 | 0.021883 | −0.046339 | 0.001873 | 0.051698 | −0.018011 | 0.035572 | 0.053015 | −0.016769 | 0.011578 | 0.05898 | 0.000493 |
| 77 | −0.039592 | 0.033442 | −0.069711 | −0.007111 | −0.067637 | 0.130339 | 0.002367 | 0.010467 | −0.068093 | 0.0035 | 0.080885 | 0.051913 | −0.005091 | 0.019617 |

| | AO | AP | AQ | AR | AS | AT | AU | AV | AW | AX | AY | AZ | BA | BB |
|---|---|---|---|---|---|---|---|---|---|---|---|---|---|---|
| 1 | 0.073131 | −0.117913 | 0.079159 | −0.091431 | 0.071289 | −0.00383 | 0.021385 | −0.094095 | 0.047038 | −0.104145 | 0.071019 | −0.057715 | 0.091422 | −0.066155 |
| 2 | 0.013344 | 0.249178 | −0.092901 | 0.08007 | −0.090696 | 0.014017 | 0.278521 | 0.030462 | −0.036266 | 0.031132 | −0.191087 | 0.013613 | 0.050726 | 0.004718 |
| 3 | −0.287953 | 0.088019 | 0.104102 | 0.030613 | −0.040985 | −0.152494 | −0.095341 | 0.065143 | −0.192 | 0.136232 | −0.164422 | −0.089914 | 0.193989 | −0.066988 |
| 4 | 0.212152 | −0.310922 | 0.003666 | 0.018491 | −0.032214 | −0.135719 | 0.168905 | 0.046472 | 0.021553 | 0.006117 | 0.144134 | 0.126867 | −0.142214 | −0.000987 |
| 5 | −0.132691 | −0.110576 | 0.025312 | 0.004059 | 0.065871 | 0.113014 | −0.421658 | −0.006256 | 0.074847 | 0.020462 | 0.178749 | −0.128844 | −0.110616 | 0.086795 |
| 6 | 0.155447 | 0.147276 | −0.124855 | 0.05628 | 0.120059 | 0.073608 | −0.141179 | −0.040678 | 0.355846 | −0.066929 | −0.206442 | 0.007827 | −0.015821 | −0.025209 |

APPENDIX B7-continued

PCA Transformation
Matrix (77 × 77; Normal/Diseased)

| | | | | | | | | | | | | | | |
|---|---|---|---|---|---|---|---|---|---|---|---|---|---|---|
| 7 | 0.008031 | −0.013647 | 0.089122 | −0.078355 | −0.150843 | 0.016897 | −0.001536 | −0.109659 | −0.081205 | −0.176345 | 0.092016 | −0.147601 | −0.107033 | 0.162729 |
| 8 | 0.019816 | 0.008069 | 0.022417 | −0.024424 | 0.092058 | 0.315441 | 0.047618 | −0.046002 | −0.157943 | 0.026259 | 0.13849 | 0.170593 | 0.052292 | −0.08713 |
| 9 | 0.029728 | 0.005492 | −0.107879 | 0.03455 | 0.016295 | −0.089709 | 0.1256 | 0.034888 | −0.091913 | 0.015962 | 0.027643 | 0.085719 | 0.143552 | −0.089672 |
| 10 | 0.026889 | 0.069302 | −0.034416 | 0.052465 | 0.092096 | 0.049944 | −0.104349 | −0.023708 | 0.014975 | −0.01249 | 0.009398 | −0.08949 | −0.084977 | 0.164106 |
| 11 | −0.204217 | 0.127343 | 0.055866 | −0.020551 | −0.026056 | 0.074049 | 0.089621 | −0.186623 | 0.070724 | 0.155729 | 0.031438 | −0.111269 | 0.035522 | −0.067611 |
| 12 | 0.011351 | −0.085641 | 0.208173 | 0.017585 | −0.135168 | 0.115644 | 0.035089 | 0.066567 | 0.132145 | 0.021355 | −0.107241 | −0.014384 | −0.067622 | −0.002959 |
| 13 | −0.02628 | 0.008906 | −0.014468 | −0.048601 | −0.073936 | −0.117917 | −0.063759 | 0.012178 | −0.065374 | −0.079316 | 0.030809 | 0.147602 | −0.028206 | −0.009115 |
| 14 | −0.049849 | −0.061963 | −0.012181 | −0.233861 | −0.065506 | −0.065034 | −0.127609 | −0.030512 | −0.046087 | −0.104395 | 0.008392 | 0.054154 | 0.00017 | −0.198134 |
| 15 | −0.339494 | 0.113119 | 0.11944 | 0.13517 | 0.090019 | −0.064314 | −0.013947 | 0.110318 | 0.044237 | 0.240453 | 0.105972 | 0.088857 | −0.098209 | 0.126108 |
| 16 | 0.085743 | 0.048236 | −0.09112 | 0.002294 | −0.018425 | −0.17711 | −0.076974 | −0.043236 | −0.167818 | −0.104325 | 0.075524 | 0.088279 | 0.033331 | 0.060378 |
| 17 | −0.012686 | −0.050835 | −0.000034 | 0.013876 | −0.097083 | 0.019493 | 0.120518 | 0.038265 | 0.048936 | 0.011261 | −0.061521 | −0.073262 | 0.011574 | 0.049796 |
| 18 | 0.07587 | 0.078423 | −0.091096 | 0.188409 | 0.108496 | 0.002093 | 0.018271 | −0.290974 | −0.213713 | 0.067518 | 0.237639 | 0.114721 | −0.055245 | 0.12652 |
| 19 | 0.09493 | −0.026266 | −0.079885 | −0.126817 | −0.187526 | 0.1655 | 0.034977 | 0.095971 | 0.060556 | 0.142634 | −0.180442 | 0.016902 | −0.084352 | −0.122708 |
| 20 | −0.023655 | 0.091133 | 0.102518 | 0.124872 | 0.297595 | 0.141684 | 0.117195 | −0.111617 | 0.058734 | −0.103081 | 0.131547 | −0.101355 | 0.108322 | 0.045048 |
| 21 | 0.033108 | 0.181877 | −0.101813 | 0.089202 | −0.158241 | −0.079702 | −0.060477 | −0.145713 | 0.012154 | 0.089806 | 0.089602 | 0.174244 | −0.124753 | −0.023413 |
| 22 | 0.150388 | 0.213592 | 0.070263 | −0.011007 | 0.084833 | 0.109101 | 0.083011 | −0.145768 | 0.027338 | −0.0718 | −0.071229 | −0.1345 | −0.063203 | −0.197158 |
| 23 | 0.002124 | −0.088735 | −0.084021 | −0.046181 | 0.00227 | 0.118459 | −0.044367 | 0.096894 | −0.142348 | −0.152829 | 0.000286 | 0.163099 | −0.046651 | −0.053523 |
| 24 | −0.154008 | −0.108356 | 0.024027 | 0.042887 | −0.120754 | 0.035036 | 0.017121 | −0.176428 | 0.19284 | 0.023757 | −0.138936 | −0.213208 | 0.10894 | −0.049878 |
| 25 | 0.15309 | −0.024485 | 0.065584 | 0.025576 | 0.150456 | 0.120278 | 0.037676 | 0.039027 | −0.219953 | 0.258187 | 0.040131 | −0.008761 | 0.052688 | −0.133521 |
| 26 | −0.059416 | 0.076228 | −0.052973 | 0.006108 | 0.173232 | −0.137943 | −0.05968 | 0.098411 | 0.279618 | −0.297142 | 0.013745 | −0.232392 | −0.001278 | 0.012384 |
| 27 | 0.141179 | −0.009183 | 0.056657 | 0.051479 | 0.128047 | −0.091733 | −0.176419 | 0.326079 | −0.054211 | 0.070127 | −0.262011 | 0.01443 | −0.064048 | −0.016172 |
| 28 | 0.100241 | 0.177462 | −0.174868 | −0.294777 | −0.292165 | 0.020646 | 0.077485 | 0.11389 | 0.085169 | 0.103542 | 0.289315 | −0.181837 | −0.005684 | 0.210432 |
| 29 | −0.098214 | 0.085975 | 0.233732 | −0.228852 | 0.019575 | 0.029089 | −0.064713 | 0.128662 | −0.033693 | −0.007333 | 0.149486 | −0.026659 | −0.014649 | −0.044924 |
| 30 | 0.175554 | 0.028193 | −0.079816 | −0.203807 | 0.197833 | −0.031013 | −0.032522 | −0.011514 | 0.005892 | 0.034132 | 0.171189 | 0.045498 | 0.063461 | −0.071086 |
| 31 | 0.042845 | −0.186934 | −0.125839 | 0.183434 | −0.17478 | 0.027999 | −0.068095 | −0.085824 | 0.207734 | 0.077592 | −0.055532 | 0.080437 | 0.286873 | 0.270133 |
| 32 | −0.00877 | −0.042627 | 0.193133 | 0.054957 | 0.001166 | −0.187732 | 0.155395 | 0.049951 | −0.1189 | −0.117521 | −0.12087 | 0.042146 | −0.105814 | 0.044247 |
| 33 | 0.037297 | −0.120948 | −0.042494 | −0.179684 | 0.09148 | −0.008512 | −0.2626 | −0.135049 | −0.05777 | 0.157155 | −0.029077 | −0.116163 | 0.214934 | −0.261161 |
| 34 | 0.012876 | −0.119324 | 0.059895 | −0.028146 | −0.094027 | 0.195178 | −0.147418 | 0.124795 | 0.088371 | 0.028375 | −0.007937 | 0.142336 | −0.053063 | 0.068019 |
| 35 | −0.165095 | 0.127557 | −0.216951 | −0.250447 | −0.14126 | −0.162206 | 0.08048 | 0.05693 | 0.029814 | 0.006827 | −0.050981 | −0.044241 | −0.048491 | 0.072307 |
| 36 | −0.114632 | −0.022734 | 0.231488 | 0.147183 | −0.132913 | −0.061397 | −0.067715 | −0.257253 | 0.071115 | −0.133604 | 0.029143 | 0.234511 | −0.049821 | 0.071359 |
| 37 | −0.019985 | −0.025152 | −0.001246 | 0.125166 | −0.212185 | 0.238623 | −0.085785 | 0.098899 | −0.030555 | −0.100667 | −0.129831 | 0.183381 | −0.064613 | −0.175701 |
| 38 | −0.116858 | −0.05975 | 0.014516 | 0.00611 | 0.391755 | −0.05186 | 0.153943 | −0.030252 | −0.024904 | −0.128223 | −0.151596 | 0.071924 | −0.058351 | 0.094576 |
| 39 | −0.11171 | −0.149402 | −0.165153 | 0.228068 | 0.016717 | 0.012035 | 0.122968 | 0.035597 | 0.11074 | −0.024293 | −0.057131 | −0.068866 | −0.029565 | −0.098517 |
| 40 | −0.042467 | −0.219881 | −0.039395 | 0.083308 | −0.071935 | −0.099396 | 0.166033 | −0.123629 | −0.123298 | 0.08501 | −0.036603 | 0.057538 | −0.023851 | 0.023187 |
| 41 | −0.021952 | −0.063457 | −0.064369 | −0.00713 | −0.111143 | −0.035402 | 0.105905 | −0.103961 | −0.099849 | 0.063194 | −0.118273 | −0.118243 | −0.026681 | 0.12427 |
| 42 | −0.106742 | −0.008399 | 0.034415 | 0.112134 | −0.045693 | 0.000197 | −0.052683 | −0.085259 | −0.045601 | 0.032632 | 0.164637 | −0.078758 | −0.067082 | −0.129844 |
| 43 | −0.084075 | −0.095636 | −0.012939 | −0.06304 | −0.033262 | −0.030645 | 0.074258 | −0.062891 | 0.17408 | 0.001942 | 0.14176 | 0.015959 | −0.30683 | −0.028383 |
| 44 | −0.02903 | −0.016185 | 0.163894 | −0.129295 | 0.01348 | −0.221119 | −0.028543 | −0.168495 | −0.125028 | 0.053143 | −0.159953 | −0.099855 | 0.047659 | −0.061499 |
| 45 | −0.041435 | 0.093879 | −0.184491 | −0.051635 | 0.133889 | 0.010408 | 0.011588 | −0.238347 | −0.044768 | 0.080482 | −0.092423 | −0.030125 | 0.050919 | 0.201651 |
| 46 | 0.108536 | −0.203807 | 0.082792 | 0.226408 | −0.02244 | −0.089989 | 0.071372 | 0.223732 | −0.051621 | −0.071439 | 0.247324 | −0.187822 | 0.041563 | −0.07834 |
| 47 | 0.002049 | −0.088715 | 0.197989 | −0.154245 | 0.031227 | 0.064882 | 0.213878 | 0.081845 | 0.156291 | 0.259561 | 0.128878 | −0.006904 | 0.32802 | −0.019543 |
| 48 | −0.00645 | −0.008136 | −0.085259 | −0.081503 | 0.015236 | −0.197856 | −0.144049 | −0.187413 | −0.015469 | 0.060942 | −0.057149 | 0.079367 | −0.17325 | −0.193708 |
| 49 | 0.076215 | 0.057603 | 0.046747 | 0.082494 | 0.052903 | −0.127976 | 0.092962 | 0.132591 | 0.017701 | 0.018234 | 0.057053 | −0.189409 | −0.023349 | −0.045352 |
| 50 | 0.144767 | 0.15377 | −0.002477 | 0.055539 | 0.020514 | −0.079146 | −0.079682 | −0.015604 | 0.209335 | −0.010244 | 0.038041 | 0.259543 | 0.070809 | −0.131127 |
| 51 | −0.03716 | 0.077544 | 0.010942 | −0.018139 | 0.027426 | 0.029513 | −0.161454 | 0.127469 | −0.136997 | −0.001242 | −0.051907 | −0.129541 | −0.088127 | 0.107087 |
| 52 | 0.085367 | 0.189656 | −0.015353 | 0.126013 | −0.139141 | 0.023732 | −0.06533 | 0.017562 | 0.106854 | −0.109449 | 0.131566 | 0.007739 | 0.087772 | −0.128513 |
| 53 | −0.093336 | −0.040438 | −0.049179 | −0.01976 | 0.004827 | −0.071107 | 0.058554 | 0.098891 | −0.087684 | −0.037483 | −0.074564 | −0.141858 | −0.19268 | 0.012797 |
| 54 | 0.042344 | −0.046095 | −0.08949 | −0.118109 | 0.174497 | −0.14654 | −0.10154 | 0.07322 | 0.044069 | 0.078962 | 0.085904 | 0.1786 | 0.048956 | 0.218106 |
| 55 | 0.125054 | −0.189099 | −0.080992 | −0.155339 | −0.014419 | 0.009789 | −0.044744 | −0.191065 | −0.086764 | −0.026408 | −0.062155 | −0.081119 | 0.030331 | −0.06054 |
| 56 | −0.070419 | −0.022192 | −0.007169 | 0.071763 | −0.109696 | 0.01226 | −0.038548 | 0.009984 | −0.010375 | 0.048533 | 0.004028 | 0.028668 | −0.001847 | 0.014113 |

APPENDIX B7-continued

PCA Transformation
Matrix (77 × 77; Normal/Diseased)

| | | | | | | | | | | | | | | |
|---|---|---|---|---|---|---|---|---|---|---|---|---|---|---|
| 57 | 0.184001 | −0.029118 | 0.145024 | 0.064304 | 0.097729 | 0.171552 | 0.080679 | 0.02532 | −0.017049 | 0.260262 | −0.09443 | −0.048996 | −0.151566 | 0.215347 |
| 58 | 0.01844 | −0.115868 | −0.065736 | 0.017548 | 0.057892 | −0.055633 | 0.08561 | 0.008021 | 0.116815 | −0.079771 | −0.001256 | −0.051512 | 0.095407 | −0.096042 |
| 59 | 0.048782 | −0.069412 | −0.089576 | 0.048665 | 0.062742 | −0.092765 | 0.097349 | −0.019952 | 0.216782 | −0.111993 | 0.035148 | 0.047926 | 0.132052 | −0.072257 |
| 60 | 0.197157 | 0.089567 | −0.156893 | 0.111406 | −0.032936 | 0.130167 | −0.037561 | −0.026978 | −0.180623 | −0.079444 | −0.109294 | −0.07422 | −0.043284 | 0.116304 |
| 61 | 0.136112 | −0.035044 | −0.039693 | 0.061378 | −0.072564 | 0.047523 | 0.008362 | −0.03679 | −0.110005 | −0.132579 | −0.004975 | −0.172551 | 0.137867 | 0.157902 |
| 62 | −0.102595 | −0.148551 | 0.099084 | −0.108899 | 0.011772 | 0.050235 | −0.087096 | 0.133949 | 0.01901 | −0.113321 | −0.063886 | 0.156838 | 0.059129 | 0.206757 |
| 63 | 0.048763 | −0.081872 | 0.062203 | 0.145339 | −0.114232 | −0.053039 | −0.09485 | −0.112922 | 0.080539 | 0.178492 | 0.19183 | −0.182533 | −0.136128 | −0.030186 |
| 64 | −0.053323 | 0.00017 | −0.108547 | 0.003073 | 0.04994 | 0.014511 | −0.107249 | −0.07616 | 0.059195 | 0.039804 | −0.118424 | −0.03125 | −0.076019 | 0.064362 |
| 65 | −0.089847 | −0.063434 | 0.034599 | 0.181633 | −0.04343 | 0.007125 | −0.06822 | −0.118998 | −0.029003 | 0.014517 | −0.061907 | −0.011274 | 0.069986 | −0.16225 |
| 66 | −0.158136 | 0.024246 | −0.104939 | −0.118052 | −0.054437 | 0.374018 | 0.151608 | −0.05281 | −0.091871 | −0.146687 | −0.002082 | −0.009491 | −0.011225 | −0.103419 |
| 67 | 0.142992 | 0.110321 | −0.01164 | −0.068231 | −0.0149 | −0.126539 | 0.163005 | 0.045822 | 0.040808 | 0.008266 | −0.000472 | 0.055025 | −0.182857 | −0.107692 |
| 68 | 0.056631 | 0.328268 | 0.307152 | 0.042878 | −0.071222 | −0.08097 | 0.016638 | −0.024043 | 0.043028 | −0.01972 | −0.031974 | 0.056822 | 0.047062 | 0.006901 |
| 69 | 0.054742 | 0.138689 | 0.000272 | 0.157611 | 0.073431 | 0.160654 | −0.159667 | 0.096393 | −0.036873 | 0.052121 | 0.033605 | −0.095783 | −0.052638 | −0.027475 |
| 70 | −0.014503 | 0.072712 | 0.106285 | 0.044834 | −0.126847 | −0.034343 | 0.018851 | 0.09345 | −0.070316 | −0.123203 | 0.062321 | 0.083082 | 0.139519 | −0.078779 |
| 71 | 0.115923 | −0.02662 | 0.090968 | −0.122757 | 0.031556 | 0.006837 | 0.005259 | −0.081244 | 0.168044 | 0.246748 | −0.183687 | 0.159006 | 0.026827 | 0.113823 |
| 72 | 0.188287 | −0.008921 | 0.049145 | 0.068139 | −0.142728 | −0.085239 | −0.174703 | 0.012314 | −0.162544 | −0.130019 | −0.081896 | −0.11855 | 0.28348 | 0.133237 |
| 73 | −0.25533 | −0.083613 | −0.33791 | 0.078944 | 0.115756 | 0.082879 | 0.026766 | 0.154215 | −0.028351 | 0.037997 | 0.066657 | 0.037724 | 0.034158 | −0.080469 |
| 74 | 0.002363 | −0.089241 | 0.235638 | −0.22296 | 0.055407 | 0.177252 | 0.06752 | −0.170514 | 0.022028 | −0.278688 | −0.040934 | 0.007213 | −0.07972 | 0.121451 |
| 75 | 0.105316 | −0.049843 | 0.064158 | 0.037868 | −0.044301 | −0.04248 | −0.035614 | −0.102206 | 0.02147 | 0.028696 | 0.005966 | −0.003955 | −0.096869 | −0.016282 |
| 76 | 0.116272 | −0.060947 | 0.047632 | 0.015709 | −0.012038 | −0.037063 | −0.051478 | −0.026922 | 0.043453 | 0.084351 | −0.066164 | −0.132513 | −0.124506 | −0.073167 |
| 77 | −0.119713 | 0.098084 | 0.00395 | −0.026155 | −0.03526 | 0.00178 | −0.011766 | 0.012114 | −0.023336 | −0.065294 | 0.080823 | 0.126306 | 0.237768 | 0.10799 |

| | BC | BD | BE | BF | BG | BH | BI | BJ | BK | BL | BM | BN | BO | BP |
|---|---|---|---|---|---|---|---|---|---|---|---|---|---|---|
| 1 | 0.105186 | −0.079865 | 0.012822 | −0.086787 | 0.022693 | −0.065532 | −0.065244 | −0.082491 | −0.023503 | 0.078267 | −0.077171 | 0.059356 | −0.031011 | −0.235191 |
| 2 | −0.012633 | 0.040313 | 0.060419 | 0.001501 | 0.062866 | 0.021456 | 0.01275 | −0.009914 | −0.065745 | −0.101266 | −0.048711 | 0.019088 | 0.053812 | 0.068966 |
| 3 | 0.041943 | 0.041659 | 0.049094 | −0.064031 | −0.071075 | 0.082422 | −0.059811 | −0.147327 | −0.075611 | 0.027577 | −0.12954 | 0.099339 | −0.078496 | −0.104381 |
| 4 | −0.138835 | −0.02483 | 0.035348 | 0.097917 | 0.110583 | 0.081288 | 0.211735 | 0.187514 | 0.201093 | −0.003581 | 0.159516 | −0.157049 | 0.124147 | 0.21456 |
| 5 | 0.003345 | −0.069593 | −0.10729 | 0.07368 | −0.1162 | −0.136019 | −0.05182 | −0.036557 | 0.043436 | 0.077608 | 0.105432 | −0.094113 | −0.105254 | −0.034359 |
| 6 | 0.16184 | −0.068638 | −0.180011 | −0.013706 | −0.121607 | 0.080744 | 0.098795 | −0.029099 | −0.039062 | −0.095353 | −0.023336 | −0.071346 | −0.099684 | 0.063206 |
| 7 | −0.117615 | −0.121728 | 0.338091 | 0.065729 | 0.023332 | −0.274951 | −0.004036 | −0.015178 | −0.078557 | 0.232822 | 0.065387 | 0.028263 | 0.13309 | −0.128579 |
| 8 | −0.064031 | 0.147994 | −0.230185 | −0.010255 | 0.091711 | 0.103186 | −0.125298 | 0.111148 | 0.122393 | −0.192752 | −0.053936 | 0.072237 | −0.090263 | 0.056267 |
| 9 | 0.070496 | −0.136584 | −0.058878 | 0.252402 | −0.301208 | −0.106114 | −0.166585 | 0.036121 | 0.134797 | 0.148209 | −0.025005 | −0.023005 | −0.024091 | 0.104536 |
| 10 | −0.003367 | 0.130679 | 0.029085 | −0.245528 | 0.362007 | 0.051608 | 0.113287 | −0.055672 | −0.078455 | −0.05981 | 0.005715 | −0.027316 | −0.066552 | −0.095452 |
| 11 | 0.07829 | 0.077227 | −0.226546 | 0.099315 | 0.040678 | −0.411054 | 0.288641 | −0.122104 | 0.265212 | −0.039434 | 0.077067 | 0.042758 | −0.150876 | −0.004429 |
| 12 | 0.040726 | −0.131629 | 0.033336 | 0.026374 | 0.040214 | −0.044789 | 0.031902 | 0.030727 | −0.029078 | −0.081817 | −0.043314 | 0.08476 | 0.158942 | −0.08812 |
| 13 | 0.070034 | −0.003073 | 0.103877 | −0.033318 | −0.062773 | −0.045085 | 0.010269 | 0.073278 | 0.061651 | −0.02695 | 0.034249 | 0.007724 | 0.012353 | 0.016038 |
| 14 | −0.19009 | 0.247748 | −0.041788 | −0.01362 | −0.146865 | 0.028193 | −0.006228 | 0.017011 | −0.014971 | 0.0209 | 0.136393 | −0.015423 | −0.052038 | 0.021591 |
| 15 | −0.055007 | −0.152577 | 0.069905 | 0.040906 | 0.023878 | 0.077145 | 0.079672 | −0.016019 | −0.040833 | −0.222992 | −0.051093 | −0.090825 | 0.000368 | 0.254675 |
| 16 | 0.012645 | 0.032155 | 0.027951 | −0.022215 | −0.038537 | 0.002882 | 0.037783 | −0.001249 | −0.097454 | 0.006117 | 0.067765 | 0.00972 | 0.078931 | 0.096303 |
| 17 | −0.05707 | 0.006705 | −0.115912 | 0.014044 | −0.015674 | 0.034468 | −0.00435 | −0.071508 | −0.040329 | −0.005865 | 0.001815 | 0.016273 | −0.037052 | 0.001668 |
| 18 | 0.207769 | −0.14093 | 0.026238 | −0.162463 | −0.046288 | −0.034138 | −0.116322 | 0.019285 | 0.076974 | −0.028658 | −0.068398 | −0.102431 | −0.04126 | 0.040778 |
| 19 | −0.005538 | −0.061843 | −0.082917 | −0.080693 | 0.059217 | 0.026612 | 0.044597 | −0.025144 | −0.084713 | 0.026985 | 0.030811 | −0.005722 | 0.058823 | −0.024268 |
| 20 | −0.074727 | 0.008335 | 0.049496 | 0.152518 | −0.065494 | 0.014827 | −0.047584 | 0.065439 | 0.103531 | 0.023842 | −0.027658 | −0.024733 | −0.085732 | −0.044661 |
| 21 | −0.113029 | 0.202028 | −0.12595 | 0.03554 | −0.02974 | −0.012985 | 0.015858 | 0.18489 | 0.001302 | 0.007474 | −0.190338 | −0.061359 | 0.21596 | −0.156274 |
| 22 | −0.022228 | −0.067943 | 0.077687 | −0.048735 | 0.04027 | −0.037529 | −0.140389 | 0.110136 | 0.010809 | −0.042761 | 0.140837 | −0.103185 | −0.060737 | 0.045635 |
| 23 | 0.124076 | −0.041815 | −0.017033 | 0.059928 | −0.05814 | −0.074653 | 0.250215 | −0.282462 | −0.040774 | 0.088303 | −0.273415 | 0.041431 | −0.108478 | −0.09886 |
| 24 | −0.057237 | 0.0928 | −0.114234 | −0.128249 | 0.084732 | 0.132805 | −0.148027 | 0.162312 | 0.150116 | 0.277947 | −0.048471 | −0.16813 | −0.191231 | 0.036889 |
| 25 | −0.317751 | −0.028301 | −0.035815 | −0.086077 | −0.010415 | −0.162645 | 0.101875 | −0.128356 | −0.016056 | 0.090024 | 0.184867 | 0.166811 | 0.066773 | 0.103364 |
| 26 | −0.018702 | 0.101948 | −0.043692 | 0.30296 | 0.116134 | 0.070022 | 0.156406 | 0.118066 | −0.152912 | 0.064698 | 0.003413 | 0.144673 | 0.085161 | 0.084303 |

APPENDIX B7-continued

PCA Transformation
Matrix (77 × 77; Normal/Diseased)

| | | | | | | | | | | | | | | |
|---|---|---|---|---|---|---|---|---|---|---|---|---|---|---|
| 27 | −0.260361 | −0.08404 | 0.075664 | 0.041408 | 0.08138 | −0.101344 | −0.031519 | −0.103462 | 0.175077 | −0.065819 | −0.03965 | −0.097631 | −0.095354 | −0.077299 |
| 28 | 0.014526 | −0.028389 | −0.16794 | −0.112565 | −0.097373 | −0.007966 | 0.034545 | −0.056313 | −0.133237 | −0.028291 | −0.013889 | 0.045188 | −0.025628 | 0.022242 |
| 29 | 0.020135 | −0.021287 | 0.082528 | 0.01069 | 0.238093 | 0.171848 | −0.102964 | 0.060719 | 0.27329 | 0.146492 | 0.019153 | −0.001375 | 0.133018 | 0.081798 |
| 30 | 0.017652 | 0.050153 | 0.000344 | −0.009677 | −0.138279 | −0.079843 | −0.04559 | 0.065085 | −0.164224 | −0.056014 | 0.019066 | 0.004606 | −0.13893 | −0.106577 |
| 31 | −0.011368 | 0.070817 | 0.033339 | 0.002678 | 0.001528 | 0.000597 | −0.137849 | 0.059454 | 0.068439 | −0.026533 | 0.050188 | 0.20731 | 0.073899 | 0.170051 |
| 32 | 0.07078 | 0.167107 | −0.092751 | −0.080563 | −0.163913 | 0.107178 | 0.213185 | 0.031114 | 0.003542 | 0.028831 | 0.199041 | 0.038011 | −0.195817 | −0.114255 |
| 33 | 0.134149 | −0.011613 | 0.059279 | −0.055675 | 0.114026 | −0.117455 | 0.093573 | 0.093293 | −0.041366 | −0.137917 | −0.194996 | 0.031119 | 0.291785 | 0.009022 |
| 34 | 0.026711 | −0.015317 | 0.001437 | 0.012396 | 0.037824 | 0.105232 | −0.064531 | 0.119785 | 0.004563 | −0.041353 | 0.015658 | −0.076341 | −0.206781 | −0.163872 |
| 35 | 0.142721 | 0.105888 | 0.236904 | 0.110507 | −0.069944 | −0.076064 | −0.081594 | 0.005662 | 0.324576 | −0.096546 | −0.107158 | −0.127574 | −0.100754 | −0.07741 |
| 36 | −0.085542 | −0.002194 | −0.02286 | −0.319578 | −0.045917 | −0.050726 | 0.062689 | −0.008641 | −0.171262 | 0.06752 | −0.158809 | −0.193373 | 0.035129 | 0.039656 |
| 37 | 0.234573 | −0.01396 | 0.158305 | 0.058414 | −0.116066 | 0.024636 | 0.034426 | 0.055626 | 0.099359 | −0.002524 | 0.076078 | 0.011521 | 0.01014 | 0.094502 |
| 38 | −0.000861 | −0.04997 | −0.046097 | −0.018568 | −0.060817 | −0.006636 | 0.02501 | −0.002817 | 0.063983 | −0.006196 | −0.067553 | −0.136731 | 0.099799 | −0.038267 |
| 39 | 0.061126 | 0.157112 | 0.176534 | −0.136941 | −0.108754 | −0.174258 | 0.065964 | −0.216194 | −0.095601 | 0.123335 | 0.099101 | 0.035757 | 0.143146 | 0.128889 |
| 40 | −0.013474 | −0.094862 | −0.05774 | 0.274983 | −0.000455 | −0.024023 | 0.066568 | 0.179969 | −0.237734 | −0.183732 | 0.02549 | 0.028637 | −0.180925 | −0.22333 |
| 41 | −0.089749 | −0.04035 | −0.070449 | −0.078967 | 0.177299 | 0.003637 | −0.037124 | −0.198454 | 0.205591 | −0.00113 | −0.018263 | −0.116991 | 0.064337 | 0.023488 |
| 42 | 0.171583 | 0.089038 | 0.085739 | 0.143916 | 0.047346 | −0.036653 | −0.011961 | 0.180629 | 0.025579 | −0.007675 | 0.068572 | −0.073689 | 0.044316 | −0.071765 |
| 43 | −0.125601 | −0.015406 | −0.044005 | 0.142302 | 0.0115 | −0.025405 | −0.198373 | −0.250401 | −0.106687 | −0.10291 | 0.014556 | 0.044096 | −0.125503 | 0.207124 |
| 44 | 0.283644 | −0.252344 | −0.322301 | 0.072923 | −0.016455 | 0.191861 | −0.063168 | −0.079595 | −0.071337 | 0.033611 | 0.171813 | −0.007281 | 0.146602 | 0.200428 |
| 45 | −0.246928 | 0.008499 | 0.005322 | 0.057434 | 0.095524 | −0.003989 | 0.114688 | 0.050862 | −0.061262 | 0.063736 | −0.010284 | 0.032824 | −0.019407 | −0.055425 |
| 46 | 0.055939 | 0.123108 | −0.123734 | −0.066379 | 0.076124 | −0.003841 | −0.264696 | −0.142281 | 0.111019 | −0.15 | −0.053254 | 0.087223 | −0.005432 | −0.157281 |
| 47 | 0.020573 | 0.100632 | 0.107262 | 0.04119 | −0.102081 | −0.011757 | 0.092494 | 0.042831 | −0.212518 | 0.114263 | 0.045188 | −0.296565 | 0.042701 | 0.052077 |
| 48 | −0.030752 | −0.041463 | 0.004451 | −0.016469 | 0.198225 | 0.007798 | 0.075982 | −0.024202 | 0.106676 | 0.010462 | 0.022641 | 0.181445 | −0.109943 | 0.047415 |
| 49 | −0.021049 | 0.165714 | 0.043603 | −0.202314 | −0.147562 | 0.034184 | 0.125587 | 0.142454 | 0.102677 | −0.197933 | −0.224139 | 0.07634 | −0.09476 | 0.146668 |
| 50 | −0.032877 | −0.06908 | −0.048583 | 0.184244 | 0.144498 | 0.076312 | −0.004151 | −0.230749 | −0.014239 | 0.088935 | 0.036177 | −0.196819 | 0.05 | −0.132566 |
| 51 | −0.040808 | −0.239174 | 0.075856 | −0.077288 | −0.112349 | −0.028363 | 0.156655 | 0.369975 | −0.018249 | 0.07898 | −0.021495 | 0.064768 | −0.097963 | 0.126784 |
| 52 | −0.049804 | −0.161685 | 0.034975 | −0.08758 | −0.005301 | −0.036355 | 0.009617 | 0.103216 | 0.010638 | −0.039951 | 0.001146 | 0.05005 | −0.021034 | 0.042997 |
| 53 | −0.113075 | −0.045575 | −0.190782 | −0.085834 | −0.086815 | 0.093366 | −0.198589 | 0.167051 | −0.158227 | 0.024429 | 0.031951 | −0.091571 | 0.184062 | −0.241442 |
| 54 | 0.059006 | 0.148682 | 0.054364 | −0.036263 | −0.001505 | 0.201264 | −0.065251 | −0.13213 | 0.025757 | 0.200302 | −0.105177 | 0.108838 | 0.085151 | 0.109003 |
| 55 | −0.049905 | 0.076757 | 0.29472 | 0.025216 | 0.040032 | 0.175819 | −0.028561 | −0.106939 | −0.153973 | −0.132391 | −0.006902 | −0.20369 | −0.378378 | 0.152161 |
| 56 | −0.043382 | −0.031612 | −0.086936 | 0.001061 | 0.001074 | −0.012307 | −0.039816 | −0.070962 | 0.023143 | −0.044496 | 0.010944 | −0.032286 | 0.032338 | 0.005698 |
| 57 | 0.306823 | 0.063209 | 0.096306 | 0.216305 | 0.171919 | −0.01335 | −0.029423 | 0.036723 | −0.122863 | 0.080069 | −0.201114 | 0.05498 | −0.002366 | −0.07398 |
| 58 | −0.029467 | −0.216961 | −0.028946 | −0.196571 | 0.009464 | −0.099969 | −0.058511 | 0.018261 | 0.015052 | −0.098247 | 0.023571 | −0.178817 | 0.051811 | −0.135905 |
| 59 | −0.093253 | −0.203391 | 0.053264 | −0.070942 | 0.02151 | −0.031515 | 0.086992 | 0.015452 | 0.161343 | −0.014114 | −0.099908 | 0.16749 | −0.019821 | −0.096312 |
| 60 | −0.002966 | 0.193266 | −0.198171 | 0.109828 | −0.003411 | −0.014654 | −0.035948 | 0.017892 | 0.090722 | 0.264494 | 0.119337 | −0.003211 | 0.003324 | 0.012325 |
| 61 | 0.113682 | −0.26287 | 0.095724 | −0.051231 | 0.065304 | 0.072366 | 0.015893 | −0.084502 | 0.040056 | −0.008547 | 0.135661 | 0.02384 | −0.144155 | 0.140498 |
| 62 | 0.016022 | 0.048234 | −0.201837 | −0.001781 | 0.106404 | −0.377532 | −0.007968 | 0.077604 | −0.024591 | −0.029525 | 0.032511 | −0.160476 | −0.063783 | 0.145562 |
| 63 | −0.021268 | −0.105839 | 0.006179 | 0.073193 | −0.12982 | 0.27852 | 0.302302 | −0.118347 | 0.11675 | −0.013355 | 0.019208 | 0.053161 | −0.000935 | −0.182896 |
| 64 | −0.062492 | −0.018739 | 0.090615 | 0.083287 | −0.057446 | −0.114336 | −0.290259 | −0.003731 | −0.079327 | −0.385446 | 0.18247 | 0.116926 | 0.159506 | −0.003824 |
| 65 | −0.01067 | 0.247477 | 0.14244 | 0.09766 | 0.103095 | 0.029326 | −0.032213 | 0.074563 | −0.082054 | 0.054683 | 0.057168 | 0.11604 | −0.00228 | 0.014619 |
| 66 | −0.193307 | −0.129021 | 0.031915 | 0.105665 | −0.037628 | 0.222954 | 0.091712 | −0.066023 | 0.013958 | −0.034117 | −0.17692 | −0.085562 | 0.154398 | 0.026025 |
| 67 | 0.2551 | 0.047683 | 0.016213 | −0.115462 | 0.250848 | −0.154894 | 0.001916 | 0.068587 | −0.038094 | 0.030794 | 0.103683 | −0.095502 | 0.009593 | 0.027451 |
| 68 | −0.124775 | −0.001017 | 0.125564 | 0.043433 | −0.039952 | −0.024389 | −0.186628 | −0.125213 | −0.022269 | 0.053837 | 0.013148 | −0.008813 | −0.097976 | −0.036377 |
| 69 | 0.047539 | 0.115649 | 0.039605 | −0.082884 | −0.193133 | 0.064568 | 0.051417 | −0.128485 | −0.064031 | −0.016023 | 0.206714 | −0.159307 | 0.104311 | 0.050609 |
| 70 | −0.069126 | −0.116714 | −0.137788 | 0.030023 | 0.192507 | −0.06263 | −0.025056 | 0.092561 | −0.203549 | 0.069047 | −0.133868 | 0.265998 | −0.201025 | 0.157743 |
| 71 | −0.054027 | −0.056473 | 0.07431 | −0.139594 | −0.208715 | 0.02181 | −0.016337 | 0.128823 | 0.172229 | 0.074009 | 0.106305 | 0.218943 | −0.044432 | −0.170917 |
| 72 | −0.067255 | 0.061267 | −0.075926 | 0.150316 | −0.003329 | −0.030282 | 0.13601 | −0.004409 | 0.088866 | −0.202455 | −0.152373 | −0.273978 | 0.117907 | −0.009068 |
| 73 | 0.076156 | −0.107364 | 0.006126 | −0.151204 | 0.104431 | 0.063692 | −0.024286 | 0.090259 | −0.032389 | 0.174874 | 0.040329 | −0.00718 | −0.051311 | −0.046083 |
| 74 | 0.091683 | 0.135928 | −0.010624 | −0.103249 | −0.130714 | 0.045237 | 0.035339 | −0.063441 | 0.100362 | −0.179232 | −0.028126 | 0.231682 | 0.155135 | 0.055666 |

APPENDIX B7-continued

PCA Transformation
Matrix (77 × 77; Normal/Diseased)

| | | | | | | | | | | | | | | |
|---|---|---|---|---|---|---|---|---|---|---|---|---|---|---|
| 75 | −0.076898 | −0.068741 | −0.013227 | 0.127289 | −0.075923 | 0.015353 | −0.097689 | −0.029926 | 0.021033 | 0.120721 | −0.19233 | 0.047051 | 0.032823 | 0.056963 |
| 76 | −0.030794 | 0.083216 | −0.01341 | −0.040495 | −0.070886 | −0.116151 | −0.007759 | 0.080775 | −0.027157 | −0.016917 | −0.170495 | −0.066859 | −0.040399 | 0.168221 |
| 77 | 0.041099 | 0.019883 | 0.046183 | 0.008093 | 0.141548 | 0.110493 | 0.140855 | −0.011129 | 0.019482 | −0.189113 | 0.385951 | 0.024705 | 0.012695 | −0.204303 |

| | BQ | BR | BS | BT | BU | BV | BW | BX | BY | BZ |
|---|---|---|---|---|---|---|---|---|---|---|
| 1 | 0.054005 | −0.109496 | 0.071113 | 0.148232 | −0.083013 | 0.059838 | −0.016244 | −0.016375 | −0.001747 | −0.008639 |
| 2 | 0.030212 | 0.082034 | −0.035334 | 0.05197 | 0.020757 | −0.013332 | 0.02586 | −0.00343 | 0.016795 | −0.155219 |
| 3 | 0.049127 | 0.047565 | 0.064921 | 0.020317 | −0.04339 | 0.008027 | 0.05112 | −0.010633 | −0.008942 | −0.193607 |
| 4 | −0.031444 | −0.011652 | −0.04047 | −0.073607 | 0.096399 | −0.08394 | 0.019983 | 0.018894 | 0.008426 | −0.096794 |
| 5 | −0.088072 | −0.077959 | 0.0197 | −0.140859 | −0.044855 | 0.040466 | −0.053756 | −0.008034 | −0.0357 | −0.074566 |
| 6 | −0.134105 | −0.01574 | 0.090969 | −0.099156 | −0.001287 | −0.000086 | −0.090555 | −0.019168 | 0.021864 | −0.078226 |
| 7 | −0.025487 | −0.021942 | −0.146686 | −0.073646 | −0.066703 | 0.0321 | 0.131349 | 0.038264 | −0.028404 | −0.056266 |
| 8 | 0.110237 | 0.079124 | −0.028217 | 0.125806 | 0.033396 | 0.006946 | −0.010361 | −0.005941 | 0.006908 | −0.015076 |
| 9 | −0.281881 | 0.087195 | −0.013899 | 0.228483 | −0.049188 | 0.085583 | 0.035539 | 0.050004 | −0.005809 | −0.002536 |
| 10 | 0.282524 | −0.066491 | −0.087402 | −0.264952 | 0.030364 | −0.134488 | −0.074849 | −0.037605 | 0.017537 | −0.002625 |
| 11 | 0.051357 | 0.032664 | −0.014084 | 0.026585 | 0.164809 | 0.067037 | 0.043837 | −0.017454 | 0.053291 | −0.101975 |
| 12 | 0.02328 | −0.031894 | 0.120817 | 0.064938 | −0.045129 | 0.055281 | 0.115188 | −0.01755 | −0.010356 | −0.011123 |
| 13 | 0.052614 | 0.007938 | 0.030066 | −0.005425 | 0.02799 | −0.026134 | −0.001098 | 0.005851 | −0.002546 | −0.004688 |
| 14 | 0.050151 | 0.012808 | 0.015106 | −0.017935 | 0.071077 | −0.029385 | −0.021587 | −0.00998 | 0.009393 | −0.011907 |
| 15 | −0.169351 | 0.195605 | −0.16418 | −0.149771 | −0.023117 | 0.0047 | 0.037189 | −0.00668 | −0.028571 | −0.051876 |
| 16 | −0.031207 | 0.069269 | 0.002806 | −0.018084 | 0.060984 | 0.003089 | −0.00901 | 0.01416 | −0.009002 | −0.03086 |
| 17 | 0.00368 | 0.021524 | −0.016604 | −0.000486 | −0.094094 | −0.027221 | −0.05434 | −0.01752 | 0.009062 | −0.003793 |
| 18 | 0.007149 | −0.115243 | 0.022029 | −0.067017 | 0.080635 | 0.004953 | 0.030542 | 0.021724 | −0.067229 | −0.019454 |
| 19 | −0.009198 | 0.008576 | 0.071309 | 0.011214 | −0.107514 | −0.00889 | 0.030233 | −0.026446 | −0.007948 | −0.013859 |
| 20 | 0.085293 | −0.107264 | −0.117074 | −0.028605 | −0.003385 | 0.034105 | −0.102225 | 0.025313 | 0.034172 | −0.003147 |
| 21 | −0.038933 | −0.250202 | −0.188864 | −0.033141 | −0.296098 | 0.124257 | −0.091352 | −0.036631 | 0.052652 | −0.089189 |
| 22 | −0.123282 | 0.001342 | 0.098893 | −0.111175 | −0.019562 | 0.03134 | 0.107146 | −0.041464 | −0.034575 | −0.382501 |
| 23 | 0.089852 | 0.003864 | −0.092799 | 0.147043 | 0.018708 | −0.141848 | −0.261602 | 0.05728 | 0.076926 | −0.326042 |
| 24 | −0.158509 | −0.001739 | −0.026815 | −0.060054 | −0.15077 | −0.169199 | 0.267017 | −0.064364 | −0.075968 | −0.034674 |
| 25 | −0.047785 | 0.019112 | 0.007749 | −0.123623 | −0.218987 | −0.04508 | −0.057654 | −0.027809 | 0.015297 | −0.037416 |
| 26 | 0.030681 | 0.130182 | −0.119124 | 0.105016 | 0.002236 | 0.042169 | 0.001573 | 0.025551 | 0.089901 | −0.014708 |
| 27 | −0.118407 | −0.010234 | 0.112127 | 0.017595 | 0.070136 | −0.040737 | 0.022728 | −0.01813 | 0.007137 | −0.021268 |
| 28 | −0.048945 | 0.182107 | −0.017535 | −0.016427 | −0.084368 | 0.097946 | 0.023954 | −0.018154 | −0.001898 | −0.011764 |
| 29 | 0.078805 | 0.002661 | −0.04595 | 0.190796 | 0.037559 | 0.207483 | −0.112473 | 0.038856 | 0.022737 | −0.306433 |
| 30 | −0.076921 | 0.030629 | 0.045912 | −0.114338 | 0.024288 | −0.055749 | 0.082594 | −0.022378 | −0.044616 | −0.200111 |
| 31 | 0.0688 | 0.013082 | −0.143265 | 0.144325 | 0.03278 | −0.023091 | −0.164981 | 0.051955 | 0.061869 | −0.283056 |
| 33 | 0.03141 | −0.03549 | 0.043587 | −0.071274 | 0.000417 | 0.471515 | 0.093044 | −0.064741 | 0.002562 | −0.114885 |
| 33 | −0.166033 | 0.035357 | −0.087455 | 0.001975 | 0.223878 | −0.093287 | 0.102734 | −0.028302 | −0.069935 | −0.009558 |
| 34 | 0.002648 | 0.071071 | 0.089795 | 0.143852 | 0.083507 | 0.085079 | 0.07111 | 0.013168 | −0.011357 | −0.014388 |
| 35 | 0.041444 | −0.143052 | −0.073225 | −0.179659 | 0.14715 | −0.083631 | 0.054995 | −0.00863 | −0.028899 | −0.034778 |
| 36 | −0.106306 | 0.108088 | 0.160129 | 0.169641 | 0.158902 | 0.086615 | 0.002897 | −0.003618 | −0.030178 | −0.026395 |
| 37 | 0.066502 | −0.112037 | −0.06431 | −0.167667 | −0.017482 | −0.104688 | −0.016342 | 0.004729 | −0.002505 | −0.009653 |
| 38 | 0.022264 | 0.001613 | −0.038221 | −0.016757 | −0.048831 | −0.044794 | 0.019887 | 0.027483 | −0.016916 | −0.012492 |
| 39 | −0.14533 | −0.015642 | 0.055256 | −0.116364 | −0.050846 | 0.03889 | −0.0766 | −0.022439 | 0.005417 | −0.116976 |
| 40 | 0.199083 | 0.099778 | −0.062628 | −0.024414 | −0.065733 | −0.237773 | 0.298184 | 0.013335 | −0.022326 | −0.186335 |
| 41 | −0.034841 | −0.053073 | 0.028585 | 0.054517 | 0.020076 | 0.09819 | −0.092677 | −0.002375 | −0.006094 | −0.082214 |
| 42 | 0.042609 | 0.384684 | 0.406611 | −0.081422 | −0.251059 | −0.077581 | −0.28254 | 0.01733 | 0.093751 | −0.093744 |
| 43 | −0.001515 | −0.318983 | 0.177313 | 0.204108 | 0.060626 | −0.204936 | 0.008583 | −0.008292 | −0.04073 | −0.035473 |
| 44 | 0.16376 | −0.172122 | −0.096344 | −0.0933 | −0.156374 | −0.06118 | −0.131887 | −0.010451 | −0.021496 | −0.013018 |

APPENDIX B7-continued

PCA Transformation
Matrix (77 × 77; Normal/Diseased)

| | | | | | | | | | | |
|---|---|---|---|---|---|---|---|---|---|---|
| 45 | −0.083079 | 0.052482 | 0.102249 | 0.193592 | 0.047039 | 0.023849 | −0.011047 | 0.015255 | 0.020241 | −0.010224 |
| 46 | −0.085721 | 0.069745 | −0.123376 | −0.094347 | −0.057958 | 0.035834 | 0.067038 | −0.002346 | −0.017155 | −0.00729 |
| 47 | 0.205404 | −0.170941 | 0.136576 | −0.043211 | 0.198393 | 0.022061 | −0.106109 | −0.049629 | −0.04507 | −0.013177 |
| 48 | −0.000256 | 0.084878 | 0.005281 | 0.10903 | −0.078914 | 0.050864 | 0.097506 | 0.015212 | 0.024394 | −0.011127 |
| 49 | −0.057167 | −0.071867 | 0.151592 | 0.05523 | 0.003758 | −0.127297 | −0.093132 | −0.089421 | 0.076126 | −0.074356 |
| 50 | −0.01437 | 0.159509 | −0.066781 | −0.16277 | 0.099278 | 0.108547 | 0.052137 | 0.093169 | −0.050781 | −0.03321 |
| 51 | 0.061175 | −0.190796 | 0.064124 | 0.129973 | −0.090485 | −0.052642 | −0.040493 | −0.071556 | 0.054196 | −0.014973 |
| 52 | 0.080229 | −0.023494 | −0.036367 | −0.005096 | −0.082295 | −0.002587 | 0.047946 | −0.019408 | 0.034351 | −0.035965 |
| 53 | −0.152669 | 0.069401 | −0.087387 | −0.014239 | 0.297909 | −0.15442 | −0.288369 | 0.027113 | −0.186815 | −0.259397 |
| 54 | 0.064553 | −0.039293 | 0.291005 | −0.106222 | −0.166889 | −0.081866 | 0.322859 | 0.057381 | 0.092029 | −0.271839 |
| 55 | −0.134618 | 0.026367 | −0.266206 | 0.029165 | −0.195211 | 0.175812 | −0.24685 | −0.076312 | 0.022168 | −0.046341 |
| 56 | 0.037024 | 0.019445 | −0.003132 | −0.008231 | −0.031725 | −0.003965 | −0.018628 | −0.003993 | −0.012182 | −0.002538 |
| 57 | −0.243523 | −0.094966 | −0.003462 | 0.041226 | −0.06914 | 0.105804 | −0.008698 | −0.013621 | −0.017269 | −0.035028 |
| 58 | 0.047371 | −0.107049 | −0.049744 | 0.078273 | −0.051012 | −0.011773 | 0.08034 | 0.147222 | 0.637828 | −0.107665 |
| 59 | 0.158128 | −0.044489 | 0.063453 | 0.023696 | −0.166102 | 0.030382 | −0.100211 | −0.18023 | −0.595497 | −0.106324 |
| 60 | 0.043809 | −0.051732 | 0.139396 | −0.049744 | 0.160031 | −0.100202 | −0.021183 | 0.049787 | 0.000804 | −0.026185 |
| 61 | 0.053665 | 0.2429 | 0.125182 | 0.001081 | 0.212154 | −0.027839 | 0.035683 | 0.049515 | −0.027819 | −0.020047 |
| 62 | 0.001913 | 0.082985 | −0.078068 | −0.056148 | −0.178063 | −0.060039 | −0.024084 | −0.106948 | −0.052715 | −0.179936 |
| 63 | −0.07655 | −0.068189 | 0.007575 | 0.007822 | 0.107744 | −0.053765 | −0.02254 | 0.096788 | 0.039632 | −0.150063 |
| 64 | 0.178349 | −0.076601 | 0.185107 | −0.041857 | 0.066758 | 0.330709 | −0.01613 | −0.037596 | 0.011321 | −0.117329 |
| 65 | −0.026691 | −0.069981 | 0.021382 | 0.031228 | 0.128087 | −0.019277 | −0.003045 | 0.000783 | 0.012991 | −0.015869 |
| 66 | −0.009701 | −0.000922 | 0.130013 | −0.170243 | −0.069817 | 0.077547 | 0.09794 | 0.048649 | 0.006445 | −0.124489 |
| 67 | −0.041345 | 0.044093 | −0.009046 | 0.175105 | −0.011819 | −0.050148 | −0.01627 | −0.105692 | −0.028968 | −0.092366 |
| 68 | 0.08295 | 0.095568 | −0.037906 | 0.019222 | −0.097163 | −0.318713 | −0.120456 | 0.098857 | 0.035725 | −0.02185 |
| 69 | 0.137724 | −0.010727 | −0.315461 | 0.340005 | 0.014064 | −0.044166 | 0.349428 | −0.140274 | −0.139131 | −0.188386 |
| 70 | −0.192591 | −0.262182 | −0.045425 | −0.269288 | 0.233344 | 0.119095 | 0.048291 | 0.088837 | 0.033075 | −0.165046 |
| 71 | −0.009582 | 0.129316 | −0.190715 | −0.14395 | 0.062199 | −0.003544 | −0.122476 | 0.073517 | 0.083341 | −0.057359 |
| 72 | −0.002115 | −0.046441 | 0.106904 | −0.032163 | −0.107842 | 0.068182 | 0.043118 | −0.049895 | −0.0445 | −0.049807 |
| 73 | 0.040398 | 0.072139 | −0.070798 | −0.032169 | −0.005265 | 0.125214 | 0.007758 | −0.007879 | 0.008778 | −0.005966 |
| 74 | −0.183495 | 0.135248 | −0.078137 | −0.083744 | −0.019236 | −0.127566 | 0.101115 | 0.028536 | 0.005656 | −0.009918 |
| 75 | 0.129365 | 0.134619 | −0.029039 | −0.095417 | 0.165639 | 0.023283 | 0.01025 | −0.632872 | 0.211195 | −0.016086 |
| 76 | 0.200021 | 0.046075 | −0.032296 | 0.005735 | −0.036018 | 0.112881 | 0.044988 | 0.623822 | −0.183228 | −0.015955 |
| 77 | −0.349585 | −0.236882 | 0.090309 | 0.110365 | −0.098976 | −0.158597 | −0.044264 | 0.004491 | −0.033625 | −0.013298 |

APPENDIX B8

PCA Transformation
Matrix (77 × 77; Benign/Malignant)

| | A | B | C | D | E | F | G | H | I | J | K | L |
|---|---|---|---|---|---|---|---|---|---|---|---|---|
| 1 | 494.4/184.1>GPCho:Lyso 16:1 | −0.000129 | −0.058696 | −0.079206 | −0.080314 | −0.325215 | 0.146202 | −0.056446 | −0.116835 | −0.037161 | −0.178955 | 0.004163 |
| 2 | 496.4/184.1>GPCho:Lyso 16:0 | −0.08701 | −0.021779 | −0.077139 | −0.025044 | −0.203501 | −0.031882 | −0.377693 | −0.072644 | 0.176958 | 0.077568 | −0.164888 |
| 3 | 520.4/184.1>GPCho:Lyso 18:2 | −0.035401 | 0.08965 | −0.230702 | −0.14749 | −0.046006 | 0.127806 | −0.18934 | −0.081235 | 0.035557 | 0.014593 | −0.061367 |
| 4 | 522.4/184.1>GPCho:Lyso 18:1 | −0.087612 | 0.030144 | −0.112095 | −0.077541 | −0.263245 | 0.200313 | −0.207387 | −0.07802 | −0.031191 | 0.004276 | −0.044094 |
| 5 | 524.4/184.1>GPCho:Lyso 18:0 | −0.072172 | −0.03937 | −0.186022 | −0.070211 | −0.23005 | −0.080222 | −0.189218 | −0.055995 | −0.026943 | 0.045723 | −0.149723 |
| 6 | 544.4/184.1>GPCho:Lyso 20:4 | 0.035229 | 0.203031 | −0.049255 | 0.041409 | −0.132745 | −0.05661 | −0.07228 | −0.170217 | 0.002495 | −0.048128 | −0.17568 |
| 7 | 568.4/184.1>GPCho:Lyso 22:6 | 0.048943 | 0.180531 | −0.118728 | 0.06724 | −0.141831 | −0.001784 | −0.106963 | 0.009501 | 0.210763 | 0.021123 | 0.12723 |
| 8 | 570.4/184.1>GPCho:Lyso 22:5 | 0.067048 | 0.163024 | −0.133092 | 0.037614 | −0.196412 | 0.004471 | −0.064222 | −0.001448 | 0.137812 | 0.040987 | 0.083806 |
| 9 | 678.5/184.1>GPCho:28:0 | −0.089287 | −0.155607 | −0.07389 | 0.001781 | −0.1141 | −0.039424 | 0.070948 | 0.066237 | 0.239035 | −0.237517 | −0.137768 |
| 10 | 678.5/184.1>GPCho:28:0a | −0.09203 | −0.14219 | −0.084238 | 0.000529 | −0.114475 | −0.037837 | 0.069611 | 0.049091 | 0.241624 | −0.262628 | −0.154822 |
| 11 | 704.6/184.1>GPCho:30:1a | −0.173154 | 0.113144 | 0.006904 | 0.074182 | 0.058846 | 0.061226 | −0.026883 | 0.08348 | −0.024967 | −0.01765 | −0.035612 |
| 12 | 706.6/184.1>GPCho:30:0a | −0.130607 | 0.072184 | −0.011571 | 0.084718 | −0.07708 | 0.079515 | 0.173973 | 0.221115 | 0.054793 | −0.305713 | −0.054185 |
| 13 | 718.6/184.1>GPCho:32:0p, 32:1e | −0.125226 | −0.053057 | −0.125252 | 0.174243 | 0.017076 | 0.085306 | 0.101808 | −0.010435 | 0.175384 | −0.020604 | 0.093028 |
| 14 | 730.8/184.1>GPCho:32:2 | −0.122379 | 0.062338 | −0.048065 | 0.020404 | 0.005501 | −0.01112 | 0.132466 | −0.409059 | 0.061956 | 0.043249 | 0.263449 |
| 15 | 732.6/184.1>GPCho:32:1a | −0.101643 | −0.055051 | 0.161767 | −0.017506 | −0.201895 | 0.086842 | 0.141137 | −0.118708 | −0.023614 | −0.205649 | 0.226382 |
| 16 | 734.6/184.1>GPCho:32:0a | −0.08228 | −0.054176 | 0.217947 | 0.119447 | −0.047052 | 0.146689 | 0.067518 | 0.126018 | 0.005632 | 0.026237 | −0.07342 |
| 17 | 742.6/184.1>GPCho:34:2p, 34:3e | −0.059436 | −0.122226 | −0.194401 | 0.098149 | −0.038734 | 0.042863 | 0.003771 | −0.031874 | 0.079658 | 0.102363 | 0.11582 |
| 18 | 744.6/184.1>GPCho:34:1p, 34:2e | 0.096939 | −0.020307 | −0.237722 | 0.011803 | 0.056252 | 0.190591 | 0.095324 | 0.003932 | −0.109709 | −0.027108 | 0.056572 |
| 19 | 746.6/184.1>GPCho:34:0p, 34:1e | −0.010414 | −0.119808 | −0.040273 | 0.194405 | 0.007658 | 0.320273 | 0.01255 | 0.039981 | −0.218304 | −0.02771 | −0.023964 |
| 20 | 748.6/184.1>GPCho:34:0e | −0.053032 | −0.139507 | −0.043757 | 0.218033 | 0.026442 | 0.188505 | 0.103237 | 0.010322 | −0.083471 | −0.067311 | −0.088427 |
| 21 | 756.6/184.1>GPCho:34:3a | −0.080715 | −0.21412 | −0.019707 | −0.052984 | 0.018316 | 0.014831 | −0.049873 | −0.052183 | −0.035974 | 0.123684 | −0.012466 |
| 22 | 758.7/184.1>GPCho:34:2a | 0.119265 | −0.092914 | 0.042623 | −0.121501 | 0.241493 | 0.068912 | −0.050121 | 0.067994 | 0.105146 | −0.007263 | 0.079215 |
| 23 | 760.6/184.1>GPCho:34:1a | 0.043351 | −0.14998 | 0.215389 | 0.011899 | −0.103379 | 0.158997 | −0.003614 | 0.045489 | 0.001878 | 0.014067 | 0.105249 |
| 24 | 762.6/184.1>GPCho:34:0a | 0.011395 | −0.136456 | 0.205927 | 0.012127 | −0.183264 | 0.159586 | 0.081196 | 0.04515 | 0.021204 | 0.073132 | 0.039532 |
| 25 | 768.6/184.1>GPCho:36:3p, 36:4e | 0.141629 | 0.100214 | −0.061222 | 0.168467 | −0.030558 | 0.05319 | −0.054851 | −0.000674 | −0.169195 | 0.017493 | 0.018149 |
| 26 | 770.6/184.1>GPCho:36:2p, 36:3e | 0.124804 | −0.011571 | −0.199363 | 0.10122 | 0.003295 | 0.133313 | −0.004053 | 0.005457 | −0.253354 | 0.024187 | 0.060149 |
| 27 | 772.6/184.1>GPCho:36:1p, 36:2e | 0.019666 | −0.179363 | −0.165563 | 0.06285 | 0.110278 | 0.110169 | 0.096413 | −0.093904 | −0.008013 | −0.01806 | −0.080323 |
| 28 | 774.6/184.1>GPCho:36:0p, 36:1e | 0.012362 | −0.165851 | −0.118264 | 0.183619 | 0.007313 | 0.018125 | 0.15991 | −0.094157 | 0.10703 | −0.125142 | −0.067048 |
| 29 | 782.6/184.1>GPCho:36:4a | 0.146913 | 0.08385 | 0.133873 | 0.064858 | 0.014465 | −0.10662 | 0.148504 | −0.12701 | 0.008656 | −0.062246 | −0.170789 |
| 30 | 784.6/184.1>GPCho:36:3a | 0.176958 | −0.032158 | −0.008367 | −0.062149 | −0.066186 | −0.101613 | 0.11944 | −0.118029 | −0.081843 | −0.082011 | −0.143873 |
| 31 | 786.6/184.1>GPCho:36:2a | 0.130521 | −0.091539 | −0.137165 | −0.16184 | 0.04013 | 0.01383 | 0.046922 | 0.02845 | −0.069077 | −0.023385 | 0.007018 |
| 32 | 788.6/184.1>GPCho:36:1a | −0.031539 | −0.215708 | −0.053761 | −0.098307 | −0.118108 | −0.047112 | −0.000654 | 0.044079 | −0.136322 | 0.032165 | 0.103154 |
| 33 | 790.8/184.1>GPCho:36:0 | −0.054828 | −0.208969 | −0.053669 | −0.002343 | −0.167993 | −0.047046 | 0.023401 | 0.049809 | −0.11688 | 0.064511 | 0.151711 |
| 34 | 792.6/184.1>GPCho:38:5p, 38:6e | 0.110978 | 0.063429 | −0.121441 | 0.195431 | −0.086622 | 0.054479 | −0.092615 | 0.110212 | 0.099608 | 0.060785 | 0.208935 |
| 35 | 794.6/184.1>GPCho:38:4p, 38:5e | 0.141025 | 0.100214 | −0.048384 | 0.187585 | −0.012683 | 0.086878 | −0.065988 | 0.00734 | −0.158429 | 0.026718 | 0.058755 |
| 36 | 796.6/184.1>GPCho:38:3p, 38:4e | 0.138463 | 0.066052 | −0.044464 | 0.226955 | 0.0138 | 0.046501 | −0.028539 | −0.044829 | −0.163074 | −0.010679 | −0.075537 |
| 37 | 798.6/184.1>GPCho:38:2p, 38:3e | 0.06589 | −0.145504 | −0.009417 | 0.24681 | 0.034346 | −0.045268 | −0.022546 | −0.086919 | −0.035113 | 0.053535 | −0.15551 |
| 38 | 800.6/184.1>GPCho:38:1p, 38:2e | −0.086354 | −0.114182 | −0.167387 | 0.177683 | 0.078777 | −0.015738 | 0.064998 | −0.089831 | 0.092909 | −0.011173 | −0.043688 |
| 39 | 808.6/184.1>GPCho:38:5a | 0.17555 | 0.074953 | −0.010645 | 0.085577 | −0.093165 | −0.097506 | 0.116856 | −0.024784 | 0.110003 | −0.00423 | 0.02651 |
| 40 | 810.6/184.1>GPCho:38:4a | 0.161877 | 0.063152 | 0.063907 | 0.071418 | −0.051121 | −0.172385 | 0.163399 | −0.117482 | −0.08565 | −0.025937 | −0.143522 |
| 41 | 812.6/184.1>GPCho:38:3a | 0.085504 | −0.01814 | 0.035041 | 0.064433 | −0.153962 | −0.320601 | 0.132135 | −0.147255 | −0.225884 | 0.016592 | −0.143745 |
| 42 | 814.6/184.1>GPCho:38:2a | −0.185246 | 0.031044 | 0.031157 | 0.10859 | 0.010055 | −0.069282 | −0.043843 | 0.082383 | −0.124369 | 0.033207 | 0.011071 |
| 43 | 816.6/184.1>GPCho:38:1a | −0.15907 | −0.079398 | −0.096091 | 0.019827 | 0.027155 | −0.190093 | −0.054395 | 0.178491 | −0.056975 | 0.022312 | 0.050143 |
| 44 | 820.6/184.1>GPCho:40:5p, 40:6e | 0.143104 | 0.072117 | −0.099549 | 0.20043 | −0.028926 | 0.030025 | −0.014316 | 0.050581 | 0.134961 | 0.018067 | 0.162267 |
| 45 | 822.6/184.1>GPCho:40:4p, 40:5e | 0.087309 | −0.070596 | 0.013578 | 0.27446 | 0.030927 | −0.023208 | −0.086056 | 0.041981 | 0.115267 | 0.175462 | 0.089027 |
| 46 | 824.6/184.1>GPCho:40:3p, 40:4e | 0.057167 | −0.131622 | 0.039078 | 0.268798 | 0.033 | −0.04 | −0.109298 | 0.066486 | −0.003981 | 0.139845 | −0.027858 |

APPENDIX B8-continued

PCA Transformation
Matrix (77 × 77; Benign/Malignant)

| | | P | Q | R | S | T | U | V | W | X | Y | Z |
|---|---|---|---|---|---|---|---|---|---|---|---|---|
| 47 | 826.6/184.1>GPCho:40:2p, 40:3e | −0.091879 | −0.209665 | 0.038864 | 0.069827 | 0.049432 | −0.043501 | −0.076178 | −0.011951 | 0.077892 | 0.119714 | −0.089207 |
| 48 | 828.6/184.1>GPCho:40:1p, 40:2e | −0.107427 | −0.17873 | 0.010651 | 0.076305 | 0.057404 | −0.00499 | −0.054898 | −0.011913 | 0.163634 | 0.026699 | −0.196016 |
| 49 | 834.6/184.1>GPCho:40:6a | 0.15106 | 0.082718 | −0.036399 | 0.095362 | −0.133312 | −0.068765 | 0.068664 | 0.087648 | 0.204945 | 0.010444 | 0.198165 |
| 50 | 836.6/184.1>GPCho:40:5a | 0.11837 | −0.046889 | 0.022464 | 0.112527 | −0.158368 | −0.236736 | 0.059581 | 0.132954 | 0.20526 | 0.143012 | 0.119619 |
| 51 | 838.6/184.1>GPCho:40:4a | 0.05514 | −0.160041 | 0.068672 | 0.076616 | −0.13061 | −0.264448 | 0.029229 | 0.051083 | −0.000758 | 0.152681 | −0.044257 |
| 52 | 701.5/184.1>SM:18/16:1 | −0.154006 | 0.104622 | −0.042907 | 0.040827 | 0.046078 | 0.048991 | −0.000407 | −0.153422 | 0.054024 | 0.059253 | −0.074896 |
| 53 | 703.5/184.1>SM:18/16:0 | −0.172215 | 0.116356 | 0.00619 | 0.048473 | 0.061736 | 0.060119 | −0.051175 | 0.053735 | 0.019552 | −0.023826 | −0.113853 |
| 54 | 703.8/184.4>SM:d18:1/16:0 | −0.168 | 0.121974 | −0.004951 | 0.084245 | 0.068076 | 0.053896 | −0.051021 | 0.071455 | −0.043468 | −0.002447 | −0.041554 |
| 55 | 705.8/184.4>SM:d18:0/16:0 | −0.168532 | 0.126145 | 0.014835 | 0.072292 | 0.033491 | 0.023535 | 0.019634 | 0.124984 | −0.033711 | −0.07375 | −0.03628 |
| 56 | 727.6/184.1>SM:18/18:2 | −0.121927 | −0.021783 | −0.088814 | 0.019708 | 0.143516 | −0.058827 | 0.10061 | −0.313354 | −0.017845 | 0.070376 | 0.09422 |
| 57 | 729.6/184.1>SM:18/18:1 | −0.156668 | 0.073842 | 0.027047 | 0.046577 | 0.058077 | −0.020699 | 0.019972 | −0.318957 | 0.061048 | 0.134957 | 0.167071 |
| 58 | 731.6/184.1>SM:18/18:0 | −0.175259 | 0.072191 | 0.094288 | 0.035757 | 0.037186 | −0.051833 | 0.027486 | −0.115914 | 0.025051 | 0.001145 | 0.152315 |
| 59 | 731.8/184.4>SM:d18:1/18:0 | −0.173623 | 0.074809 | 0.094321 | 0.045825 | 0.038996 | −0.051111 | 0.031591 | −0.108665 | 0.003134 | 0.006108 | 0.167776 |
| 60 | 733.8/184.4>SM:d18:0/18:0 | −0.131513 | −0.00651 | 0.166545 | −0.002229 | −0.13341 | −0.028746 | 0.12208 | −0.018912 | 0.001337 | −0.222642 | 0.208608 |
| 61 | 757.6/184.1>SM:18/20:1 | −0.117641 | −0.16962 | −0.059824 | −0.030624 | 0.041644 | 0.022326 | −0.022087 | −0.170098 | −0.039092 | 0.163666 | 0.040942 |
| 62 | 759.6/184.1>SM:18/20:0 | 0.124897 | −0.061331 | 0.010236 | −0.157089 | 0.219889 | 0.087661 | 0.02051 | 0.070827 | 0.192414 | 0.072206 | 0.041926 |
| 63 | 759.8/184.4>SM:d18:1/20:0 | 0.118216 | −0.047893 | −0.005912 | −0.17547 | 0.212083 | 0.094627 | 0.061741 | 0.065769 | 0.182854 | 0.093674 | 0.03995 |
| 64 | 761.8/184.4>SM:d18:0/20:0 | 0.021081 | −0.131135 | 0.196769 | 0.007055 | −0.182376 | 0.17157 | 0.047821 | 0.02208 | 0.017652 | 0.097475 | 0.068935 |
| 65 | 773.6/184.1>SM:18/21:0 | −0.014448 | −0.048459 | −0.246804 | 0.089268 | 0.081395 | −0.018361 | 0.223284 | −0.081174 | 0.161013 | −0.140947 | −0.090414 |
| 66 | 787.6/184.1>SM:18/22:0 | 0.052529 | −0.053699 | −0.2447 | −0.162527 | 0.021716 | −0.071111 | 0.13016 | 0.077782 | −0.089869 | −0.052939 | 0.112422 |
| 67 | 787.9/184.4>SM:d18:1/22:0 | 0.004026 | −0.025215 | −0.269455 | −0.13925 | 0.006788 | −0.122713 | 0.132454 | 0.089559 | −0.139725 | −0.011954 | 0.125227 |
| 68 | 789.9/184.4>SM:d18:0/22:0 | −0.039355 | −0.198995 | −0.051735 | −0.077678 | −0.172573 | −0.049793 | 0.026017 | 0.024945 | −0.164419 | 0.02623 | 0.133348 |
| 69 | 813.6/184.1>SM:18/24:1 | −0.177907 | 0.082439 | 0.028597 | 0.110397 | 0.016702 | −0.060322 | −0.005585 | 0.057098 | −0.111421 | 0.006995 | 0.0256 |
| 70 | 813.9/184.4>SM:d18:1/24:1 | −0.175834 | 0.082881 | 0.024977 | 0.108615 | 0.020803 | −0.046938 | 0.011989 | 0.072709 | −0.108588 | 0.022504 | 0.024313 |
| 71 | 815.6/184.1>SM:18/24:0 | −0.137852 | 0.086642 | −0.109185 | 0.077986 | 0.019379 | −0.160603 | 0.043108 | 0.200582 | −0.084091 | −0.024127 | 0.063998 |
| 72 | 815.9/184.4>SM:d18:0/24:1 | −0.135148 | 0.100213 | −0.115323 | 0.027508 | 0.059423 | −0.168358 | 0.001333 | 0.188827 | −0.04168 | −0.069347 | 0.012353 |
| 73 | 817.9/184.4>SM:d18:0/24:0 | −0.072215 | −0.141226 | −0.097039 | 0.001602 | 0.092634 | −0.210193 | −0.180503 | 0.118511 | −0.068445 | −0.121668 | 0.192711 |
| 74 | 841.9/184.4>SM:d18:1/26:1 | −0.11995 | −0.177811 | 0.045612 | 0.015226 | 0.048058 | −0.163273 | −0.091346 | −0.017292 | 0.003289 | 0.071912 | −0.050026 |
| 75 | 843.9/184.4>SM:d18:0/26:1 | 0.109162 | −0.097996 | 0.068406 | 0.06598 | 0.14086 | −0.086265 | −0.284224 | −0.106825 | −0.010453 | −0.327268 | 0.112458 |
| 76 | 843.9/184.4>SM:d18:1/26:0 | 0.108215 | −0.099384 | 0.066338 | 0.067251 | 0.138374 | −0.089251 | −0.283874 | −0.105755 | −0.017357 | −0.324097 | 0.126997 |
| 77 | 845.9/184.4>SM:d18:0/26:0 | 0.113277 | −0.095496 | 0.088438 | 0.103261 | 0.088014 | −0.042373 | −0.262985 | −0.115074 | −0.038981 | −0.326076 | 0.120408 |

| | M | N | O | P | Q | R | S | T | U | V | W | X | Y | Z |
|---|---|---|---|---|---|---|---|---|---|---|---|---|---|---|
| 1 | 0.192651 | −0.026922 | 0.132186 | −0.009052 | 0.194108 | −0.156947 | 0.240041 | −0.097007 | 0.073704 | −0.022749 | 0.049972 | −0.107673 | 0.109679 | −0.215322 |
| 2 | 0.049926 | 0.08794 | 0.096685 | 0.104465 | −0.083037 | 0.186499 | 0.217644 | −0.240594 | 0.229551 | 0.01399 | 0.075826 | −0.066948 | −0.185305 | 0.131194 |
| 3 | −0.063905 | −0.142398 | 0.038138 | 0.100669 | 0.128091 | −0.020883 | −0.042525 | −0.085697 | −0.194833 | −0.138825 | 0.040948 | 0.070403 | −0.056694 | −0.019504 |
| 4 | 0.026327 | −0.125785 | −0.023457 | 0.148391 | 0.054863 | −0.033966 | −0.085704 | −0.025521 | 0.036646 | −0.037348 | −0.036789 | 0.131123 | 0.017906 | −0.069155 |
| 5 | −0.219674 | 0.06325 | −0.075577 | −0.009665 | −0.152689 | 0.161044 | 0.11093 | −0.071016 | 0.142134 | −0.080367 | 0.054874 | 0.068592 | 0.105519 | −0.064475 |
| 6 | −0.059425 | −0.11106 | 0.158307 | 0.082805 | −0.149108 | −0.07047 | −0.092184 | 0.146147 | −0.157097 | 0.153829 | 0.075888 | −0.213111 | 0.214187 | 0.077905 |
| 7 | −0.055741 | −0.189753 | 0.064887 | −0.108367 | 0.0641 | −0.105135 | −0.097784 | 0.135294 | −0.124541 | 0.030069 | −0.036287 | −0.076599 | 0.031516 | 0.214304 |
| 8 | −0.042489 | −0.178987 | 0.027505 | −0.024094 | 0.094151 | −0.129969 | −0.004214 | 0.104208 | −0.148643 | 0.218488 | −0.0403 | 0.00637 | 0.001136 | 0.010549 |
| 9 | 0.050609 | 0.303066 | 0.001432 | −0.035187 | 0.018171 | 0.011685 | −0.242157 | −0.090874 | −0.041933 | 0.092776 | −0.118123 | −0.098437 | −0.00507 | 0.071154 |
| 10 | 0.044671 | 0.310788 | −0.030368 | −0.006794 | 0.021769 | 0.004776 | −0.288927 | −0.081291 | 0.036817 | 0.121497 | −0.037778 | −0.088162 | 0.040816 | 0.077351 |
| 11 | −0.017129 | 0.063594 | −0.123675 | 0.051059 | 0.000761 | −0.065808 | 0.127129 | 0.118318 | −0.071203 | 0.009405 | −0.040267 | 0.145855 | −0.04833 | 0.010382 |
| 12 | −0.054311 | 0.248116 | 0.134392 | 0.071084 | 0.119114 | −0.093296 | 0.232345 | 0.047646 | −0.042915 | 0.100898 | 0.037178 | 0.113728 | −0.027216 | 0.054156 |
| 13 | −0.003729 | −0.015758 | −0.149677 | −0.02969 | −0.134771 | −0.026235 | −0.166298 | −0.212331 | −0.064565 | −0.150466 | 0.488435 | 0.119708 | 0.235576 | −0.215191 |
| 14 | 0.091951 | 0.215292 | −0.029704 | 0.129959 | 0.104073 | 0.083005 | 0.043417 | 0.04074 | −0.001538 | 0.122203 | 0.181332 | −0.176421 | −0.031146 | 0.185436 |
| 15 | 0.022701 | −0.011727 | 0.149517 | −0.061501 | 0.172095 | 0.024038 | 0.034705 | 0.132325 | −0.021071 | −0.12019 | 0.095666 | −0.098604 | −0.056392 | −0.049836 |
| 16 | −0.175389 | −0.009537 | −0.015331 | 0.001388 | −0.232096 | −0.156082 | 0.366881 | −0.071484 | 0.070781 | −0.09013 | −0.013327 | −0.23163 | 0.068678 | 0.343029 |

APPENDIX B8-continued

PCA Transformation
Matrix (77 × 77; Benign/Malignant)

| | | | | | | | | | | | | | | |
|---|---|---|---|---|---|---|---|---|---|---|---|---|---|---|
| 17 | 0.24733 | 0.114793 | 0.004623 | −0.276936 | −0.308704 | 0.220921 | 0.159489 | 0.059113 | −0.260384 | 0.056513 | −0.050714 | 0.276032 | 0.201678 | −0.031059 |
| 18 | 0.141499 | 0.11746 | −0.107699 | 0.101271 | 0.082727 | 0.196968 | 0.07248 | 0.038062 | −0.066226 | 0.204807 | 0.068251 | 0.058906 | −0.176333 | 0.133352 |
| 19 | −0.066011 | −0.048073 | −0.131996 | 0.004588 | 0.044209 | −0.166618 | −0.045141 | −0.124509 | −0.14015 | 0.016061 | 0.229262 | −0.117802 | −0.08544 | −0.055664 |
| 20 | −0.166062 | −0.1634 | −0.000545 | 0.029932 | −0.135515 | −0.120442 | −0.083579 | −0.231333 | −0.055692 | −0.070735 | 0.094063 | −0.001623 | −0.204936 | 0.145649 |
| 21 | 0.026476 | 0.041237 | 0.238247 | −0.259437 | −0.045461 | −0.140641 | 0.064726 | 0.06581 | −0.020541 | 0.102495 | −0.001577 | −0.011884 | −0.1511 | −0.131127 |
| 22 | 0.035298 | 0.081105 | 0.031042 | −0.049098 | 0.077336 | −0.061659 | 0.026967 | 0.118998 | 0.288292 | −0.096763 | 0.168225 | 0.111503 | 0.128778 | −0.089467 |
| 23 | 0.152515 | −0.084668 | −0.119064 | 0.024548 | −0.015288 | 0.010503 | −0.130465 | 0.088193 | 0.241298 | −0.014641 | −0.047226 | 0.01527 | 0.025159 | 0.016588 |
| 24 | 0.145472 | −0.086305 | −0.107445 | 0.079385 | −0.051157 | 0.035945 | −0.069597 | −0.039653 | 0.038799 | 0.091083 | −0.091544 | −0.03104 | 0.013475 | 0.178057 |
| 25 | 0.06093 | 0.232523 | 0.049805 | 0.05332 | −0.205272 | 0.013269 | −0.090118 | −0.025952 | 0.093688 | −0.072197 | −0.049426 | −0.156147 | −0.036088 | −0.053356 |
| 26 | 0.172621 | 0.158457 | 0.034381 | −0.002452 | 0.089752 | 0.053873 | −0.00095 | −0.015348 | −0.008937 | −0.048921 | −0.043198 | 0.07679 | −0.087921 | 0.00439 |
| 27 | −0.15155 | −0.134555 | 0.091703 | −0.108892 | 0.022828 | 0.017507 | 0.127608 | −0.014817 | −0.017506 | 0.279951 | 0.011986 | 0.025019 | −0.096004 | 0.100485 |
| 28 | −0.049263 | −0.27166 | −0.007439 | 0.138993 | 0.003938 | 0.111739 | −0.019664 | 0.11241 | 0.155525 | 0.018277 | −0.049018 | 0.110278 | 0.064788 | −0.021359 |
| 29 | 0.047668 | 0.029955 | 0.128309 | 0.078314 | −0.259993 | −0.01002 | −0.0066 | 0.030611 | −0.03197 | 0.144662 | 0.051541 | 0.012482 | 0.078377 | −0.013868 |
| 30 | 0.108672 | 0.035591 | 0.103144 | −0.067493 | 0.164334 | −0.063356 | −0.061983 | −0.07488 | −0.090316 | −0.204603 | −0.023898 | 0.165648 | −0.172674 | 0.20615 |
| 31 | −0.249386 | 0.126587 | −0.122847 | −0.101163 | 0.14587 | −0.038842 | −0.024743 | 0.119068 | 0.066536 | −0.006714 | 0.118752 | −0.040763 | 0.122946 | 0.0475 |
| 32 | −0.160228 | 0.019973 | −0.097147 | 0.04063 | 0.004039 | −0.093093 | −0.054204 | 0.178813 | 0.035601 | 0.108276 | 0.017471 | −0.041789 | −0.031191 | 0.102599 |
| 33 | −0.060069 | 0.004492 | −0.000751 | 0.014881 | −0.131143 | −0.005975 | 0.045587 | 0.125696 | −0.002678 | 0.073425 | −0.025992 | 0.085435 | 0.095863 | 0.09082 |
| 34 | −0.020003 | 0.146957 | 0.004378 | −0.254523 | −0.132036 | −0.003043 | 0.021621 | 0.025649 | 0.15855 | −0.248669 | −0.129284 | 0.031315 | −0.132038 | 0.126817 |
| 35 | −0.05448 | 0.15954 | 0.076639 | 0.009468 | −0.011932 | −0.07424 | −0.042311 | −0.039977 | 0.032304 | 0.067566 | −0.095539 | −0.175819 | −0.00619 | −0.205657 |
| 36 | −0.017517 | 0.075696 | 0.161801 | 0.123338 | −0.086216 | 0.093311 | −0.15063 | −0.039911 | 0.012517 | −0.029131 | −0.09507 | −0.001274 | −0.055026 | −0.132629 |
| 37 | 0.027996 | −0.004115 | 0.17628 | 0.086968 | 0.229247 | 0.118742 | 0.050003 | 0.106562 | −0.078571 | −0.172047 | −0.069453 | 0.198914 | 0.069064 | 0.224723 |
| 38 | 0.139491 | −0.124864 | −0.071122 | −0.105399 | 0.037257 | 0.00428 | 0.151994 | 0.161068 | 0.103899 | −0.058541 | −0.125844 | −0.154043 | 0.25515 | −0.023336 |
| 39 | 0.004907 | −0.028807 | −0.00628 | −0.043964 | −0.053284 | −0.12901 | −0.002929 | 0.045983 | −0.044559 | 0.157826 | −0.035676 | 0.094484 | −0.148926 | −0.114292 |
| 40 | −0.073474 | 0.01956 | 0.046447 | −0.009484 | −0.21417 | −0.047609 | 0.046818 | 0.027826 | −0.000862 | 0.066979 | 0.096364 | −0.013173 | 0.057304 | −0.12494 |
| 41 | 0.141781 | −0.032428 | −0.161143 | −0.226888 | 0.140466 | 0.018991 | 0.074725 | −0.10093 | −0.140582 | −0.269021 | 0.147749 | −0.015071 | −0.008781 | 0.175098 |
| 42 | 0.024028 | −0.094544 | −0.01286 | −0.184068 | 0.171434 | 0.065061 | −0.042984 | −0.114215 | 0.045357 | 0.199171 | 0.01331 | −0.1005 | 0.046136 | 0.077587 |
| 43 | 0.110545 | −0.059182 | 0.0768 | 0.067567 | −0.03132 | −0.132009 | −0.027671 | 0.101415 | 0.092331 | 0.022984 | 0.135699 | −0.108336 | −0.065103 | 0.084824 |
| 44 | −0.101147 | −0.009286 | 0.069039 | −0.028075 | 0.041503 | −0.017115 | −0.045292 | 0.008162 | 0.079407 | −0.002493 | −0.003776 | −0.007169 | −0.128544 | 0.03676 |
| 45 | −0.109184 | 0.085775 | 0.143221 | 0.174784 | 0.288715 | 0.027366 | −0.004564 | −0.015941 | −0.028405 | 0.015659 | 0.09621 | 0.027855 | 0.251134 | 0.021496 |
| 46 | −0.048776 | 0.087257 | 0.079516 | 0.206367 | 0.139692 | 0.068975 | 0.041928 | 0.12186 | −0.006041 | −0.054072 | 0.014407 | −0.208934 | 0.098757 | −0.092041 |
| 47 | −0.052934 | 0.037153 | 0.063916 | −0.07963 | 0.067185 | 0.0169 | −0.012406 | 0.076891 | −0.117509 | −0.04715 | −0.065269 | −0.100567 | 0.050059 | −0.023258 |
| 48 | −0.111688 | −0.04849 | 0.028553 | −0.105248 | 0.042224 | 0.015002 | −0.225485 | 0.149374 | −0.133445 | −0.238146 | −0.180116 | −0.105663 | −0.130561 | −0.108391 |
| 49 | −0.077876 | −0.017239 | −0.024957 | −0.150467 | −0.041301 | −0.147726 | 0.020295 | −0.114841 | −0.054757 | −0.13766 | −0.045235 | −0.010181 | −0.038089 | 0.044723 |
| 50 | −0.021764 | 0.010055 | −0.238792 | 0.064738 | 0.09262 | −0.09118 | 0.123055 | −0.14895 | −0.054248 | 0.099011 | 0.02965 | 0.056312 | −0.162529 | −0.143278 |
| 51 | 0.037799 | 0.028428 | −0.179663 | 0.220055 | 0.135454 | −0.00965 | 0.131914 | −0.029812 | −0.052233 | 0.148361 | −0.027049 | 0.009591 | −0.126247 | −0.215135 |
| 52 | 0.159524 | 0.145885 | −0.302713 | 0.072198 | −0.016577 | −0.184847 | 0.146579 | 0.14467 | −0.162412 | −0.203542 | −0.093983 | −0.209195 | 0.01937 | −0.019366 |
| 53 | −0.047792 | 0.060609 | −0.170501 | 0.022624 | 0.03399 | −0.086723 | −0.019509 | 0.133321 | −0.143301 | −0.029106 | −0.084192 | 0.060147 | −0.126953 | −0.045309 |
| 54 | −0.004732 | 0.049561 | −0.097036 | 0.025462 | −0.00089 | −0.01711 | 0.09755 | 0.082994 | −0.093178 | 0.042036 | −0.116766 | 0.120363 | 0.001888 | −0.010472 |
| 55 | −0.0541 | 0.066722 | 0.013905 | 0.069672 | 0.01738 | 0.010088 | 0.18107 | −0.02195 | −0.113904 | 0.01881 | −0.102585 | 0.122074 | 0.04553 | −0.116818 |
| 56 | −0.049291 | 0.057531 | 0.045973 | 0.112738 | 0.060215 | −0.463055 | −0.023971 | −0.327382 | 0.234503 | 0.022716 | −0.3918 | 0.243498 | 0.181662 | 0.046888 |
| 57 | −0.008641 | 0.083293 | −0.139795 | 0.139227 | −0.071812 | 0.002124 | −0.117636 | 0.021607 | 0.000098 | −0.067803 | 0.072945 | −0.080946 | −0.088229 | 0.037464 |
| 58 | −0.197411 | −0.000497 | 0.056922 | 0.025754 | −0.008052 | 0.219053 | −0.049428 | 0.003779 | 0.007288 | −0.004213 | −0.008551 | 0.059659 | −0.168435 | 0.046522 |
| 59 | −0.182199 | 0.001182 | 0.082905 | 0.015456 | −0.012903 | 0.245142 | −0.019706 | −0.013161 | 0.029732 | 0.018765 | −0.011385 | 0.072485 | −0.129528 | 0.053125 |
| 60 | −0.111598 | −0.002527 | 0.283513 | 0.039928 | −0.001608 | 0.092894 | 0.128095 | −0.013956 | −0.103993 | −0.238478 | −0.06387 | −0.004651 | −0.012327 | −0.257974 |
| 61 | 0.103229 | 0.042656 | 0.183085 | −0.199976 | −0.071829 | −0.17418 | −0.009963 | 0.088722 | −0.010552 | 0.114735 | −0.023286 | −0.140807 | −0.225674 | −0.161604 |
| 62 | 0.083305 | −0.056214 | 0.082963 | 0.086269 | 0.013114 | 0.016188 | 0.104796 | −0.149208 | −0.207407 | −0.016817 | −0.014406 | −0.161651 | −0.103874 | −0.031594 |
| 63 | 0.114581 | 0.015464 | 0.171137 | 0.114236 | −0.025647 | 0.065766 | 0.060151 | −0.18947 | −0.212777 | 0.013467 | −0.015809 | −0.105904 | 0.088065 | 0.072327 |
| 64 | 0.199539 | −0.113173 | −0.040419 | 0.153133 | −0.108982 | 0.09458 | −0.131671 | −0.111872 | −0.149007 | −0.037293 | −0.208311 | 0.011985 | 0.054878 | −0.016771 |
| 65 | 0.063619 | −0.28838 | −0.050395 | 0.108711 | −0.090753 | 0.101774 | 0.150023 | 0.062487 | 0.200278 | −0.055214 | −0.029138 | −0.056732 | −0.218558 | −0.131822 |
| 66 | −0.209854 | 0.01617 | −0.133867 | 0.012551 | 0.001113 | 0.115222 | −0.016166 | −0.026349 | 0.002636 | −0.10932 | −0.154246 | −0.238713 | 0.035221 | −0.100483 |

APPENDIX B8-continued

PCA Transformation
Matrix (77 × 77; Benign/Malignant)

| | | | | | | | | | | | | | | |
|---|---|---|---|---|---|---|---|---|---|---|---|---|---|---|
| 67 | −0.112906 | −0.046791 | 0.021115 | 0.113532 | −0.044199 | 0.11563 | 0.049222 | −0.188119 | −0.123992 | −0.08213 | −0.199434 | −0.188312 | 0.129152 | 0.06667 |
| 68 | −0.108075 | 0.024081 | −0.015048 | 0.178652 | −0.129206 | −0.020191 | −0.093387 | 0.144628 | −0.16052 | 0.024603 | −0.088099 | 0.103255 | 0.041315 | 0.00318 |
| 69 | 0.027887 | −0.091244 | −0.012828 | −0.181103 | 0.106002 | 0.085007 | −0.111639 | −0.167578 | −0.001051 | 0.098512 | −0.014791 | −0.084333 | 0.048213 | −0.062062 |
| 70 | 0.042938 | −0.088864 | 0.035163 | −0.199447 | 0.095723 | 0.104497 | −0.093932 | −0.227098 | −0.009249 | 0.155392 | −0.052056 | −0.02946 | 0.161875 | −0.011635 |
| 71 | 0.276513 | −0.13996 | 0.062924 | 0.042624 | 0.027733 | 0.049063 | 0.023858 | −0.059968 | 0.130679 | −0.007603 | −0.055478 | −0.15839 | −0.039431 | −0.004887 |
| 72 | 0.240848 | −0.065821 | 0.056464 | 0.173077 | −0.072614 | −0.072824 | −0.182876 | 0.126416 | 0.091904 | −0.09445 | 0.066008 | 0.047699 | −0.083952 | 0.042228 |
| 73 | 0.111075 | −0.037296 | 0.206531 | 0.18641 | −0.173092 | −0.246733 | −0.017157 | 0.015178 | −0.131311 | −0.08561 | 0.184778 | 0.066915 | 0.006425 | 0.150382 |
| 74 | −0.076418 | 0.052927 | 0.034127 | 0.018834 | −0.036375 | −0.03845 | 0.011209 | −0.170795 | −0.081635 | 0.011103 | 0.085087 | 0.065537 | −0.13961 | −0.081212 |
| 75 | −0.002361 | −0.035321 | −0.133695 | −0.023949 | −0.027928 | 0.019512 | 0.048693 | −0.031202 | −0.055388 | 0.06207 | −0.043501 | −0.012806 | 0.0228 | 0.017444 |
| 76 | 0.001949 | −0.038813 | −0.125528 | −0.011701 | −0.02505 | 0.017387 | 0.077189 | −0.063414 | −0.070332 | 0.060503 | −0.05031 | −0.038784 | 0.014709 | 0.016422 |
| 77 | 0.035516 | −0.071477 | −0.171028 | −0.04208 | −0.03031 | 0.013297 | 0.022656 | −0.013598 | −0.078902 | 0.063237 | −0.113335 | −0.014441 | −0.032665 | −0.016851 |

| | AA | AB | AC | AD | AE | AF | AG | AH | AI | AJ | AK | AL | AM | AN |
|---|---|---|---|---|---|---|---|---|---|---|---|---|---|---|
| 1 | 0.141044 | −0.064019 | 0.032028 | −0.01237 | 0.187379 | −0.160749 | 0.177897 | −0.130456 | 0.126093 | −0.166465 | 0.17313 | −0.205866 | 0.025392 | −0.021211 |
| 2 | 0.086978 | −0.129158 | −0.232279 | 0.151278 | −0.091795 | −0.054948 | −0.090216 | 0.211898 | 0.144305 | 0.083667 | −0.012064 | −0.093537 | −0.060907 | 0.140419 |
| 3 | −0.049344 | 0.227232 | 0.140707 | −0.205486 | −0.061684 | 0.270634 | −0.09812 | −0.165858 | −0.171491 | −0.02704 | −0.073175 | −0.153412 | −0.107291 | −0.165436 |
| 4 | −0.132722 | −0.011736 | 0.059005 | −0.163277 | −0.12167 | 0.049177 | 0.145483 | −0.182638 | −0.075964 | −0.00964 | 0.050119 | 0.092605 | 0.08517 | −0.092753 |
| 5 | −0.038591 | −0.234493 | 0.141676 | −0.022189 | 0.107883 | 0.015277 | −0.143622 | 0.105843 | −0.100429 | −0.030856 | −0.062908 | 0.200383 | 0.049855 | 0.015364 |
| 6 | 0.018686 | 0.248588 | −0.150681 | −0.053977 | −0.138406 | −0.088273 | 0.181357 | −0.022339 | −0.003568 | −0.01901 | −0.146029 | 0.057432 | 0.122903 | −0.062268 |
| 7 | 0.042387 | 0.091344 | −0.198509 | 0.103048 | −0.034195 | −0.056417 | −0.010837 | −0.029114 | 0.014637 | 0.026637 | 0.086112 | 0.178625 | −0.270194 | 0.133806 |
| 8 | 0.026004 | 0.017647 | 0.089583 | 0.274982 | 0.191857 | 0.289127 | −0.067262 | 0.248018 | −0.066502 | −0.023073 | 0.035695 | 0.019306 | 0.185678 | −0.014359 |
| 9 | −0.160835 | 0.091716 | 0.030977 | −0.008104 | 0.02178 | −0.015128 | 0.040397 | −0.008516 | −0.052053 | −0.101875 | 0.02209 | 0.065787 | 0.030287 | 0.124865 |
| 10 | −0.118758 | 0.124435 | 0.126632 | −0.022013 | 0.098429 | 0.046408 | 0.041989 | 0.031029 | −0.050738 | −0.067474 | 0.089611 | 0.015529 | −0.091226 | −0.009182 |
| 11 | −0.043656 | −0.038283 | 0.073728 | 0.209476 | −0.107053 | −0.168751 | 0.137792 | −0.055549 | −0.044004 | 0.077516 | 0.160511 | −0.137712 | −0.1662 | −0.064767 |
| 12 | −0.026474 | −0.083331 | −0.007262 | −0.043195 | −0.240282 | 0.118639 | −0.133969 | −0.085416 | 0.059946 | 0.149336 | −0.125499 | −0.016715 | 0.11777 | −0.117844 |
| 13 | 0.218443 | 0.115579 | 0.080101 | 0.297847 | −0.180154 | 0.070718 | 0.101851 | 0.139664 | 0.19752 | 0.022519 | −0.091898 | 0.039941 | −0.050399 | 0.014526 |
| 14 | −0.164423 | −0.229672 | −0.152413 | 0.020292 | 0.019586 | 0.009346 | −0.004861 | −0.145897 | 0.051335 | 0.029233 | −0.086049 | −0.092127 | −0.012811 | −0.196701 |
| 15 | 0.067515 | 0.069773 | −0.07944 | 0.095603 | 0.292903 | −0.081109 | 0.0246 | 0.047271 | −0.101437 | 0.053747 | −0.004915 | −0.036716 | −0.104407 | 0.084852 |
| 16 | 0.042964 | 0.072743 | 0.150403 | 0.058773 | 0.051048 | 0.196082 | 0.238722 | −0.022385 | −0.208867 | −0.212081 | 0.006213 | −0.029176 | 0.126438 | −0.038543 |
| 17 | −0.029926 | 0.008691 | −0.175739 | −0.139681 | 0.153095 | 0.082153 | 0.195415 | −0.109808 | −0.224883 | 0.222262 | 0.035784 | −0.118189 | 0.08308 | 0.167602 |
| 18 | 0.32076 | 0.001125 | −0.166168 | −0.194274 | −0.081209 | 0.031584 | 0.063063 | 0.037608 | −0.028648 | −0.204244 | −0.175217 | 0.212806 | 0.025042 | −0.08775 |
| 19 | −0.110529 | −0.13362 | −0.118762 | −0.035639 | 0.066116 | −0.110102 | −0.036723 | 0.240975 | −0.347821 | −0.007172 | 0.057762 | 0.075283 | −0.257802 | 0.039856 |
| 20 | −0.230613 | −0.066753 | −0.208352 | −0.091925 | 0.159111 | 0.116864 | −0.037682 | −0.018759 | 0.124669 | 0.088088 | −0.123135 | −0.125324 | 0.108012 | −0.017917 |
| 21 | −0.104365 | 0.059844 | 0.165871 | 0.054207 | −0.134197 | −0.013883 | 0.063138 | 0.018059 | 0.039625 | 0.032497 | −0.169584 | 0.076061 | −0.107314 | −0.072413 |
| 22 | −0.195645 | 0.07301 | −0.046508 | 0.012259 | 0.095522 | 0.147554 | 0.049266 | 0.010656 | 0.007852 | −0.14832 | 0.037556 | 0.051592 | 0.052423 | −0.011516 |
| 23 | −0.004092 | −0.000428 | −0.047662 | 0.00118 | 0.03869 | 0.062496 | −0.024497 | −0.088252 | 0.021656 | 0.116096 | −0.120027 | 0.173768 | 0.116454 | 0.051725 |
| 24 | 0.242556 | 0.004944 | 0.157218 | 0.059631 | −0.088479 | 0.008771 | −0.050229 | −0.102152 | 0.022859 | 0.160595 | −0.013974 | −0.06746 | −0.058847 | −0.035598 |
| 25 | 0.175752 | 0.208972 | 0.072845 | 0.064452 | −0.036852 | −0.053038 | −0.134039 | −0.08218 | 0.058278 | −0.030754 | −0.111084 | −0.09212 | 0.13324 | −0.047971 |
| 26 | 0.141022 | 0.098498 | 0.065894 | 0.100235 | −0.047854 | 0.083995 | −0.003088 | 0.053255 | 0.028471 | −0.30751 | 0.07096 | 0.060822 | 0.065684 | 0.133738 |
| 27 | 0.129618 | −0.061473 | 0.137934 | 0.097598 | 0.036208 | 0.084937 | −0.021351 | −0.195146 | 0.184532 | 0.01512 | 0.240526 | 0.245563 | 0.064245 | 0.099531 |
| 28 | −0.034702 | 0.077321 | 0.056292 | −0.053893 | −0.034564 | 0.02106 | −0.095828 | −0.019616 | 0.19838 | 0.000936 | −0.043439 | −0.32799 | −0.037695 | −0.052666 |
| 29 | 0.158879 | −0.080319 | 0.029583 | −0.141189 | −0.034761 | −0.069834 | −0.003651 | 0.126917 | −0.142024 | 0.039492 | 0.078245 | −0.058016 | −0.263049 | −0.079439 |
| 30 | 0.041053 | −0.069954 | 0.101016 | 0.159488 | −0.228024 | −0.055419 | 0.054294 | 0.172716 | −0.229104 | 0.309852 | −0.004389 | 0.037675 | 0.141982 | 0.012912 |
| 31 | 0.091363 | −0.031601 | −0.129461 | 0.035783 | −0.007977 | 0.007808 | −0.169154 | −0.223879 | −0.120546 | 0.11721 | 0.037114 | −0.014288 | −0.020281 | 0.009763 |
| 32 | 0.103894 | 0.129962 | −0.016852 | −0.111 | 0.003512 | −0.054888 | −0.091383 | 0.1311 | 0.138193 | 0.006074 | 0.046338 | −0.038528 | −0.036639 | 0.165663 |
| 33 | −0.127912 | 0.108544 | −0.114744 | −0.145575 | −0.090697 | 0.066317 | −0.061654 | 0.174082 | 0.198427 | 0.025795 | 0.038132 | −0.052206 | −0.034463 | −0.045758 |
| 34 | 0.004094 | 0.152648 | −0.041415 | −0.063148 | 0.052067 | −0.037201 | 0.026494 | 0.057793 | 0.007858 | 0.052569 | 0.097201 | −0.043278 | −0.114263 | −0.42041 |
| 35 | 0.001387 | 0.10483 | −0.009651 | −0.012236 | 0.079759 | −0.06196 | −0.125796 | 0.041003 | −0.058581 | 0.101739 | −0.038719 | −0.232958 | 0.188039 | 0.152356 |
| 36 | −0.187211 | −0.006812 | −0.036548 | 0.104351 | 0.004476 | 0.152414 | −0.079645 | −0.139737 | 0.023109 | 0.013911 | 0.256628 | 0.041509 | −0.13092 | 0.174038 |

APPENDIX B8-continued

PCA Transformation
Matrix (77 × 77; Benign/Malignant)

| | | | | | | | | | | | | | | |
|---|---|---|---|---|---|---|---|---|---|---|---|---|---|---|
| 37 | 0.01254 | −0.0383 | 0.165616 | 0.029198 | 0.086444 | 0.035626 | −0.011644 | −0.026149 | 0.03063 | −0.100991 | −0.053765 | −0.162949 | −0.257259 | 0.118289 |
| 38 | −0.020098 | −0.059444 | 0.013534 | 0.115786 | −0.190517 | −0.038328 | −0.379718 | 0.067223 | −0.27673 | −0.14138 | −0.03919 | −0.102542 | 0.062588 | −0.03179 |
| 39 | 0.029552 | −0.243447 | 0.108639 | −0.006561 | 0.157073 | 0.208391 | 0.009255 | 0.149157 | 0.035691 | 0.000969 | −0.025495 | −0.026465 | 0.174735 | −0.122486 |
| 40 | 0.039857 | −0.109933 | −0.019581 | −0.101373 | 0.069951 | 0.072618 | 0.014562 | −0.143108 | 0.095245 | −0.095644 | 0.040057 | 0.038732 | −0.125205 | 0.031168 |
| 41 | −0.158507 | 0.185026 | −0.051591 | 0.006934 | 0.000418 | 0.011646 | 0.041489 | 0.016443 | 0.217169 | −0.095991 | 0.022675 | 0.055941 | 0.135141 | −0.061038 |
| 42 | 0.051622 | 0.064698 | −0.046003 | −0.081218 | −0.055303 | −0.023902 | −0.113831 | −0.032747 | 0.006743 | 0.084457 | 0.134956 | −0.04352 | 0.017797 | −0.065718 |
| 43 | 0.078453 | 0.140246 | 0.056437 | −0.094261 | −0.027853 | 0.14229 | −0.002318 | 0.028155 | −0.053796 | 0.086309 | −0.001144 | −0.120595 | −0.113063 | 0.137471 |
| 44 | −0.047085 | −0.041889 | 0.077586 | 0.040013 | 0.006276 | −0.074236 | 0.040387 | −0.069588 | 0.150407 | 0.194189 | 0.188798 | 0.051277 | 0.034667 | −0.12614 |
| 45 | 0.006389 | −0.087599 | 0.252453 | −0.289381 | 0.112731 | −0.191804 | 0.151142 | 0.195351 | 0.022944 | 0.1383 | −0.122685 | 0.062995 | 0.131197 | 0.040711 |
| 46 | −0.077969 | −0.013565 | −0.133519 | 0.079969 | −0.152819 | 0.059994 | 0.180414 | −0.087044 | −0.051241 | 0.059182 | −0.021211 | 0.225234 | −0.00715 | −0.123026 |
| 47 | 0.220014 | 0.015197 | −0.061311 | 0.061777 | 0.04659 | 0.087823 | 0.008234 | −0.114349 | 0.024986 | −0.056197 | 0.07632 | 0.076853 | −0.008991 | −0.068076 |
| 48 | 0.213703 | −0.250976 | −0.281809 | −0.043655 | 0.019662 | 0.066172 | 0.055294 | −0.000796 | 0.044082 | −0.134688 | −0.074647 | −0.064605 | 0.172959 | −0.052313 |
| 49 | −0.016473 | −0.217461 | 0.024885 | −0.137965 | −0.179952 | −0.206846 | −0.047331 | −0.185844 | 0.005849 | −0.298384 | −0.076688 | 0.061498 | −0.113279 | 0.167007 |
| 50 | 0.00292 | 0.07702 | 0.00904 | −0.090339 | −0.049928 | 0.013454 | −0.114391 | −0.150227 | −0.11388 | −0.121616 | −0.13001 | −0.081289 | −0.044826 | 0.12987 |
| 51 | −0.078049 | 0.164153 | −0.197456 | 0.206228 | 0.026663 | 0.08413 | 0.081499 | −0.023403 | −0.162153 | 0.037894 | 0.04658 | −0.049993 | 0.01515 | −0.09088 |
| 52 | 0.020838 | 0.008132 | 0.169248 | −0.257016 | 0.087759 | 0.065387 | −0.216809 | 0.147761 | 0.179074 | 0.205821 | 0.200366 | 0.20534 | 0.029286 | 0.110575 |
| 53 | 0.155154 | 0.017778 | 0.025325 | 0.054399 | 0.081379 | −0.150814 | 0.122158 | −0.022225 | 0.114942 | −0.012974 | −0.099109 | −0.166248 | 0.049613 | 0.09149 |
| 54 | −0.201614 | 0.054869 | −0.097311 | 0.163215 | 0.165393 | −0.140534 | 0.039696 | −0.009832 | 0.191862 | −0.06633 | −0.147338 | 0.085848 | −0.016633 | 0.061239 |
| 55 | 0.00067 | 0.009924 | 0.006611 | 0.06661 | −0.110426 | −0.004726 | −0.063008 | −0.041857 | 0.083844 | −0.026677 | 0.013687 | 0.077168 | −0.080098 | −0.064071 |
| 56 | 0.14259 | 0.083679 | −0.23385 | −0.021841 | −0.019157 | 0.039151 | 0.104368 | 0.095603 | −0.040847 | 0.003777 | −0.018925 | 0.084986 | −0.032289 | 0.030176 |
| 57 | −0.033186 | −0.080959 | 0.148498 | 0.061945 | −0.061237 | 0.158384 | −0.007525 | −0.140128 | −0.054332 | −0.065857 | 0.141075 | −0.070136 | 0.012884 | 0.017198 |
| 58 | 0.079644 | 0.132042 | 0.105549 | −0.032385 | 0.013957 | −0.01626 | 0.045912 | 0.06546 | −0.122868 | −0.090958 | −0.023308 | −0.051798 | 0.098444 | 0.136845 |
| 59 | −0.034509 | 0.111619 | 0.062323 | 0.004292 | 0.004655 | −0.02651 | 0.03778 | 0.072328 | −0.118796 | −0.15315 | 0.059812 | 0.033823 | 0.078459 | 0.122298 |
| 60 | 0.094474 | 0.065998 | −0.127203 | −0.094659 | −0.112652 | 0.194577 | −0.1787 | 0.092375 | 0.009112 | 0.056112 | 0.006457 | 0.182722 | −0.026329 | 0.004307 |
| 61 | −0.126767 | −0.040467 | 0.213662 | 0.065169 | −0.12023 | −0.042776 | 0.031762 | 0.004592 | 0.031247 | −0.006253 | −0.275398 | 0.004518 | −0.095362 | −0.026314 |
| 62 | −0.048811 | 0.047876 | −0.060971 | −0.210907 | −0.100267 | −0.013476 | 0.064253 | 0.164461 | 0.126318 | −0.040078 | 0.089556 | −0.159683 | 0.006673 | 0.074974 |
| 63 | −0.053063 | 0.079349 | −0.030259 | 0.179152 | 0.086678 | −0.03051 | −0.1967 | 0.089221 | 0.029395 | −0.089431 | 0.14505 | −0.015829 | 0.058001 | −0.163095 |
| 64 | −0.025341 | −0.057779 | 0.070874 | 0.067615 | −0.04345 | −0.076092 | −0.055607 | −0.108256 | 0.025154 | 0.035382 | −0.031295 | 0.122965 | 0.018806 | 0.003155 |
| 65 | −0.072745 | 0.211407 | 0.014615 | −0.038079 | 0.023742 | −0.343592 | 0.055348 | 0.002711 | −0.132553 | 0.058516 | 0.073562 | 0.201912 | 0.127526 | −0.014834 |
| 66 | 0.084697 | −0.162904 | 0.045781 | 0.059972 | −0.173625 | 0.073367 | 0.362337 | 0.032616 | −0.004624 | 0.1691 | 0.153773 | −0.187755 | 0.01322 | 0.036224 |
| 67 | −0.021932 | −0.004218 | 0.117245 | 0.165892 | 0.277488 | −0.046651 | −0.043173 | −0.100662 | 0.046827 | 0.123775 | −0.378267 | 0.086325 | −0.153855 | −0.026267 |
| 68 | −0.119424 | −0.09504 | 0.037771 | 0.034776 | −0.115379 | −0.180413 | −0.002508 | 0.231191 | 0.053631 | −0.268624 | 0.207724 | −0.020958 | 0.030138 | −0.24045 |
| 69 | −0.020552 | −0.031507 | 0.045873 | −0.090489 | −0.103531 | −0.050951 | −0.007815 | −0.012194 | −0.022392 | −0.017385 | 0.025692 | 0.017668 | 0.187266 | −0.048793 |
| 70 | 0.000547 | −0.117778 | −0.013282 | −0.031846 | 0.011122 | −0.066472 | −0.081941 | 0.022753 | −0.003813 | −0.065224 | 0.100995 | −0.091203 | 0.029166 | −0.145513 |
| 71 | −0.060895 | −0.123873 | 0.046421 | −0.09539 | −0.031088 | 0.269176 | 0.213445 | 0.05586 | 0.063968 | −0.031554 | 0.047991 | 0.109414 | −0.165827 | 0.102756 |
| 72 | 0.156188 | −0.165995 | −0.028399 | 0.011226 | 0.231985 | 0.015699 | −0.016844 | 0.035718 | −0.087364 | −0.074382 | −0.078806 | 0.020239 | −0.042519 | −0.211298 |
| 73 | −0.01202 | −0.119727 | −0.017433 | 0.063798 | −0.040793 | −0.149602 | −0.097273 | −0.22518 | −0.066052 | 0.013067 | 0.123918 | −0.010746 | 0.315133 | 0.173635 |
| 74 | 0.232561 | 0.129249 | 0.060546 | −0.101474 | 0.211215 | −0.095512 | −0.086264 | −0.168087 | −0.040626 | 0.086744 | 0.163262 | 0.095094 | −0.067936 | −0.240516 |
| 75 | 0.008808 | 0.002301 | 0.061469 | −0.001764 | 0.008625 | 0.01506 | 0.050595 | 0.039314 | −0.011398 | −0.019901 | −0.033929 | 0.042647 | −0.031625 | −0.091556 |
| 76 | 0.012576 | 0.018868 | 0.101277 | −0.01037 | 0.009188 | −0.008017 | 0.059272 | 0.001251 | 0.016298 | 0.004997 | −0.072681 | 0.055448 | −0.012976 | −0.09692 |
| 77 | 0.007693 | −0.043406 | −0.023107 | 0.03429 | −0.079073 | 0.116975 | −0.014567 | 0.046338 | 0.02771 | 0.025439 | −0.060167 | −0.050015 | −0.076927 | 0.0467 |

| | AO | AP | AQ | AR | AS | AT | AU | AV | AW | AX | AY | AZ | BA | BB |
|---|---|---|---|---|---|---|---|---|---|---|---|---|---|---|
| 1 | 0.103284 | −0.041092 | 0.107724 | −0.078158 | 0.095253 | −0.118842 | 0.019569 | −0.066204 | 0.070478 | −0.15015 | 0.009723 | −0.151516 | 0.151325 | −0.066446 |
| 2 | −0.144306 | 0.0019 | −0.05032 | −0.017118 | −0.167097 | 0.004298 | 0.053053 | 0.130677 | 0.062867 | 0.133537 | 0.194189 | 0.057168 | 0.00954 | 0.01908 |
| 3 | −0.038227 | −0.100956 | −0.101177 | 0.173247 | 0.009597 | 0.323539 | −0.130475 | 0.096193 | −0.068349 | 0.14404 | 0.138966 | 0.081529 | 0.144204 | 0.142456 |
| 4 | 0.188417 | −0.007999 | −0.138863 | −0.158783 | 0.002796 | −0.159459 | 0.201337 | 0.034063 | −0.031711 | −0.008151 | −0.017595 | −0.087501 | −0.301914 | −0.059994 |
| 5 | 0.075055 | 0.01309 | 0.119847 | 0.074465 | 0.128948 | 0.142156 | −0.094259 | −0.125361 | −0.147051 | −0.189721 | −0.377314 | 0.105241 | 0.051399 | −0.06074 |
| 6 | −0.225537 | 0.074893 | 0.0037 | 0.116875 | −0.044479 | −0.076756 | 0.043229 | −0.162658 | 0.269721 | −0.152045 | −0.036358 | 0.134601 | −0.159131 | −0.027832 |

APPENDIX B8-continued

PCA Transformation
Matrix (77 × 77; Benign/Malignant)

| | | | | | | | | | | | | | | |
|---|---|---|---|---|---|---|---|---|---|---|---|---|---|---|
| 7 | 0.00904 | 0.108576 | 0.058284 | −0.14032 | 0.075662 | −0.094063 | −0.027865 | −0.079901 | −0.332459 | 0.019452 | −0.078129 | −0.033776 | 0.107795 | 0.019716 |
| 8 | 0.043097 | 0.161831 | 0.144468 | −0.104092 | −0.07409 | −0.0654 | −0.110911 | 0.068066 | 0.071362 | 0.063891 | −0.035194 | −0.105317 | 0.068265 | 0.069052 |
| 9 | −0.035517 | −0.015565 | −0.175239 | −0.054932 | 0.022075 | 0.079285 | 0.019339 | 0.177501 | −0.039836 | −0.132285 | −0.112551 | −0.026587 | −0.168529 | 0.057246 |
| 10 | 0.016751 | −0.091059 | 0.087447 | 0.064145 | −0.051213 | −0.132494 | −0.05263 | −0.125674 | 0.055834 | 0.222737 | 0.040188 | −0.008064 | 0.277139 | −0.065799 |
| 11 | 0.079269 | −0.051499 | 0.00463 | 0.011557 | −0.232478 | 0.010558 | −0.248331 | 0.079068 | 0.079535 | −0.095521 | −0.086863 | 0.099248 | 0.021849 | −0.095937 |
| 12 | 0.022731 | 0.320192 | 0.073527 | −0.055118 | 0.047492 | 0.228279 | 0.092124 | 0.009141 | 0.01574 | −0.034192 | −0.009602 | 0.03695 | −0.067062 | −0.068215 |
| 13 | 0.025577 | −0.082201 | −0.061976 | −0.050454 | 0.100438 | 0.128877 | −0.055959 | −0.091616 | 0.01926 | −0.058076 | 0.03836 | −0.065329 | −0.103113 | 0.001824 |
| 14 | −0.030866 | 0.071253 | −0.113708 | −0.024137 | 0.168568 | −0.042186 | −0.056558 | −0.17225 | −0.061017 | 0.044623 | 0.061762 | 0.056041 | −0.056956 | 0.236457 |
| 15 | 0.068525 | −0.119432 | 0.016763 | 0.276351 | −0.183078 | 0.268819 | −0.09925 | 0.02865 | −0.10122 | −0.037995 | −0.007148 | 0.079652 | −0.132114 | 0.051748 |
| 16 | −0.090768 | −0.139253 | −0.029353 | −0.14434 | 0.111357 | 0.002288 | −0.169994 | −0.015666 | −0.135213 | 0.047575 | 0.117237 | −0.070396 | −0.105113 | −0.023465 |
| 17 | −0.000255 | 0.033712 | 0.107234 | −0.097695 | −0.01051 | 0.015373 | 0.110386 | 0.083612 | −0.063297 | 0.067133 | 0.084464 | 0.052577 | −0.045104 | −0.035558 |
| 18 | −0.023995 | −0.096407 | 0.071403 | −0.108303 | −0.177466 | −0.038324 | −0.343035 | 0.076794 | 0.01762 | −0.029175 | −0.171111 | −0.123754 | 0.056332 | −0.133516 |
| 19 | −0.148288 | 0.175778 | −0.109568 | −0.042663 | 0.114061 | −0.083776 | 0.157171 | 0.230197 | 0.206813 | 0.036049 | −0.069831 | 0.0012 | 0.104503 | 0.051084 |
| 20 | 0.190054 | −0.01403 | 0.202776 | 0.101386 | −0.264473 | −0.133931 | 0.068706 | −0.200423 | −0.123828 | −0.124236 | 0.00216 | 0.077403 | −0.032194 | 0.026869 |
| 21 | −0.161335 | −0.116773 | −0.002964 | −0.059265 | −0.171145 | −0.11244 | −0.164492 | −0.028579 | 0.072379 | 0.034131 | 0.022438 | 0.10414 | −0.099209 | 0.016085 |
| 22 | −0.112171 | 0.229664 | 0.157669 | −0.031704 | −0.037172 | −0.094841 | −0.068141 | −0.028199 | 0.00608 | 0.007292 | 0.157042 | 0.161795 | 0.060187 | −0.058095 |
| 23 | −0.086596 | 0.205211 | −0.002959 | 0.014276 | 0.105934 | 0.104096 | −0.100703 | −0.011172 | 0.077913 | 0.083061 | −0.111799 | −0.199648 | −0.03494 | 0.08589 |
| 24 | 0.008399 | 0.007966 | −0.029572 | −0.158624 | −0.100622 | 0.047129 | 0.077591 | −0.095017 | 0.03957 | 0.027897 | −0.075114 | 0.222281 | 0.150519 | 0.03059 |
| 25 | 0.135335 | −0.008996 | 0.192979 | 0.106112 | 0.005813 | −0.098251 | 0.071875 | 0.26864 | −0.082257 | 0.026213 | 0.011189 | −0.210095 | −0.01298 | 0.290191 |
| 26 | −0.010551 | 0.083963 | −0.09811 | 0.151589 | −0.010999 | −0.045566 | 0.166077 | −0.338096 | −0.064443 | −0.010246 | 0.112482 | 0.301347 | −0.028168 | −0.114238 |
| 27 | −0.14924 | −0.100329 | −0.054978 | 0.337645 | 0.204272 | −0.012789 | 0.169774 | 0.097437 | −0.109825 | 0.165358 | 0.040272 | −0.036549 | −0.027178 | 0.015408 |
| 28 | −0.268133 | 0.094631 | −0.074582 | −0.015567 | −0.098466 | −0.177728 | −0.010542 | 0.179082 | −0.238739 | −0.136973 | −0.139617 | −0.076296 | 0.05788 | −0.204242 |
| 29 | 0.068942 | 0.081014 | 0.034474 | 0.184014 | 0.140261 | 0.029654 | 0.000945 | −0.051948 | −0.113391 | −0.012062 | 0.058559 | −0.058614 | 0.062061 | −0.10901 |
| 30 | 0.134697 | −0.042678 | 0.04167 | 0.066753 | 0.107784 | −0.203924 | −0.065219 | 0.002241 | −0.065997 | −0.129742 | 0.172985 | −0.126302 | −0.064116 | −0.077705 |
| 31 | −0.068182 | −0.309389 | −0.122127 | −0.165277 | −0.060961 | −0.102009 | 0.118722 | 0.00389 | 0.014033 | −0.213032 | 0.0018 | −0.033542 | 0.046903 | 0.003545 |
| 32 | 0.223144 | 0.031494 | 0.05126 | −0.116919 | 0.0138 | 0.13193 | 0.083149 | 0.037238 | 0.058578 | 0.217155 | 0.009317 | 0.049279 | −0.334702 | 0.021151 |
| 33 | 0.192532 | −0.130863 | 0.048567 | 0.103767 | 0.316122 | −0.044983 | −0.160269 | 0.047131 | 0.118753 | −0.185063 | 0.130029 | −0.020193 | 0.230569 | 0.111221 |
| 34 | −0.114889 | −0.047738 | −0.119934 | 0.160318 | −0.005778 | −0.020284 | 0.117198 | −0.071572 | 0.155748 | 0.011872 | −0.20875 | −0.091243 | −0.004908 | −0.00687 |
| 35 | −0.09639 | 0.111433 | −0.220368 | −0.109248 | 0.210696 | 0.070085 | −0.161063 | 0.080596 | −0.1363 | −0.066451 | 0.034812 | 0.206801 | 0.064323 | −0.167106 |
| 36 | 0.029495 | −0.05729 | 0.109396 | −0.230474 | −0.092393 | 0.066786 | −0.263369 | −0.170105 | 0.018852 | 0.04668 | 0.027868 | −0.140052 | −0.125597 | 0.075195 |
| 37 | −0.164258 | 0.015133 | 0.199501 | −0.113557 | 0.178746 | 0.106452 | 0.071492 | −0.06956 | 0.296593 | −0.065707 | −0.118667 | −0.040845 | −0.107577 | 0.175348 |
| 38 | 0.267141 | 0.004027 | −0.169544 | 0.110886 | −0.119057 | −0.085957 | −0.039624 | −0.147896 | 0.057971 | 0.187332 | −0.089532 | −0.038411 | −0.132066 | 0.022383 |
| 39 | 0.059189 | −0.078657 | −0.169713 | −0.047629 | −0.136095 | 0.079018 | 0.157337 | −0.081921 | 0.17883 | −0.017647 | −0.004722 | 0.04862 | 0.150687 | 0.098531 |
| 40 | 0.12686 | −0.130455 | −0.15765 | −0.116747 | −0.160981 | 0.045068 | −0.012681 | 0.122024 | 0.086281 | 0.090813 | −0.070245 | 0.081183 | −0.032599 | 0.059482 |
| 41 | 0.001006 | 0.113951 | −0.136708 | −0.185684 | −0.045389 | 0.065004 | 0.002825 | 0.160894 | −0.099906 | 0.168169 | −0.122935 | 0.058191 | 0.150588 | −0.01809 |
| 42 | 0.052508 | −0.14267 | 0.154427 | −0.080287 | 0.045476 | 0.015965 | −0.12404 | −0.026802 | 0.060552 | −0.069885 | 0.021892 | 0.137212 | 0.040065 | −0.037111 |
| 43 | 0.129938 | −0.013974 | −0.042127 | −0.049512 | −0.007281 | −0.119003 | 0.130003 | −0.085402 | −0.04769 | −0.020765 | −0.005378 | 0.137067 | 0.079365 | −0.084946 |
| 44 | 0.080059 | −0.075503 | −0.092034 | −0.076554 | 0.12077 | 0.128358 | −0.084194 | 0.060352 | 0.123097 | −0.027461 | 0.04374 | 0.108933 | −0.153383 | −0.240219 |
| 45 | 0.03685 | −0.099964 | −0.094297 | 0.038121 | −0.135032 | −0.173554 | −0.123816 | 0.08775 | −0.151618 | 0.149176 | 0.024083 | 0.07073 | −0.043872 | 0.112846 |
| 46 | 0.142133 | −0.085044 | 0.137614 | −0.009998 | −0.110381 | 0.21604 | 0.277786 | −0.068169 | −0.085232 | 0.019253 | 0.026216 | −0.099638 | 0.289396 | −0.116983 |
| 47 | 0.156184 | 0.306701 | −0.125765 | 0.101707 | −0.212796 | 0.061127 | 0.021696 | 0.25786 | 0.030165 | −0.308442 | 0.19668 | −0.075998 | 0.029491 | 0.027617 |
| 48 | 0.015707 | −0.076831 | −0.036429 | −0.075575 | 0.26479 | −0.030974 | −0.179597 | −0.029022 | 0.101693 | 0.03397 | 0.08226 | 0.133939 | 0.005451 | −0.054695 |
| 49 | 0.020596 | 0.097925 | 0.151142 | 0.068511 | −0.042999 | 0.037555 | −0.030186 | 0.072241 | −0.120682 | −0.014979 | 0.044481 | 0.143119 | −0.02378 | −0.039138 |
| 50 | −0.112119 | −0.071324 | 0.073215 | 0.024889 | 0.004994 | −0.11008 | 0.050923 | −0.082529 | 0.13631 | −0.149516 | 0.192305 | −0.133135 | −0.071942 | 0.104631 |
| 51 | −0.121534 | −0.092697 | 0.040187 | 0.153348 | 0.134611 | 0.020559 | −0.021971 | −0.014342 | −0.148919 | 0.037852 | −0.185575 | 0.056746 | −0.162893 | −0.135302 |
| 52 | −0.24712 | −0.061957 | 0.068704 | −0.028337 | −0.095691 | 0.040817 | 0.030139 | −0.113262 | −0.032218 | −0.197101 | 0.10146 | −0.077722 | −0.035732 | −0.052357 |
| 53 | 0.008097 | −0.045847 | 0.123806 | 0.019458 | 0.013396 | 0.012671 | 0.145605 | −0.024244 | −0.014856 | 0.197786 | −0.176395 | 0.074551 | 0.015559 | 0.01642 |
| 54 | 0.103503 | −0.082913 | −0.165094 | 0.187132 | 0.057813 | −0.147391 | −0.027085 | −0.00575 | 0.002961 | −0.009349 | 0.020139 | −0.15707 | 0.011207 | 0.0139 |
| 55 | 0.080278 | 0.032941 | −0.124947 | −0.149904 | 0.150044 | −0.178652 | −0.017115 | 0.009579 | −0.079464 | 0.060211 | 0.060717 | 0.111642 | 0.145165 | 0.255566 |
| 56 | −0.00732 | −0.029755 | 0.010026 | −0.029257 | −0.044435 | 0.144656 | 0.018383 | 0.047593 | 0.011508 | −0.007528 | −0.076895 | 0.039208 | 0.044644 | 0.027979 |

APPENDIX B8-continued

PCA Transformation
Matrix (77 × 77; Benign/Malignant)

| | | | | | | | | | | | | | | |
|---|---|---|---|---|---|---|---|---|---|---|---|---|---|---|
| 57 | 0.107046 | 0.044511 | 0.210391 | 0.071847 | 0.051914 | −0.169505 | −0.000124 | 0.281698 | 0.147278 | 0.10915 | −0.021789 | 0.063863 | 0.01844 | −0.295533 |
| 58 | 0.051626 | 0.037354 | −0.065976 | −0.107898 | 0.000743 | 0.061435 | 0.103062 | −0.053845 | 0.026412 | −0.148648 | −0.060823 | −0.063651 | 0.160762 | −0.018425 |
| 59 | 0.002422 | 0.001702 | −0.184786 | −0.088163 | −0.04011 | −0.02686 | 0.124729 | −0.086386 | 0.004388 | −0.182 | 0.019773 | −0.092548 | 0.037658 | −0.001424 |
| 60 | −0.148172 | −0.129522 | 0.073245 | −0.045461 | −0.020149 | −0.264935 | 0.066 | 0.060203 | 0.04408 | 0.202279 | −0.099169 | 0.017498 | −0.02412 | −0.079332 |
| 61 | −0.020625 | −0.011563 | 0.060988 | −0.175839 | 0.060544 | 0.085011 | 0.08195 | −0.003104 | −0.185657 | −0.074239 | −0.126323 | −0.118002 | 0.080134 | −0.00823 |
| 62 | 0.174172 | 0.029684 | −0.07616 | 0.005422 | 0.092585 | 0.120288 | −0.005282 | −0.138841 | 0.021172 | 0.092042 | −0.166917 | −0.252478 | −0.036148 | −0.142693 |
| 63 | 0.055597 | −0.121772 | 0.116238 | −0.124717 | 0.00369 | −0.028051 | 0.117963 | 0.144772 | −0.04948 | −0.221547 | −0.199036 | 0.215228 | −0.129059 | 0.132645 |
| 64 | −0.053969 | −0.058781 | −0.131058 | 0.055939 | 0.00481 | −0.041919 | −0.035854 | −0.045065 | −0.011271 | −0.037816 | 0.005463 | 0.176615 | 0.129858 | 0.026152 |
| 65 | 0.050414 | −0.000684 | 0.09944 | −0.161354 | 0.04613 | 0.145313 | −0.021844 | 0.016404 | 0.098795 | 0.03335 | 0.184069 | 0.111468 | 0.090535 | 0.163134 |
| 66 | −0.143024 | 0.153095 | 0.03608 | 0.026388 | −0.085566 | −0.068893 | −0.00811 | −0.087367 | −0.067399 | 0.055073 | −0.098024 | 0.003144 | 0.016863 | 0.315819 |
| 67 | 0.017122 | 0.101134 | 0.006393 | −0.03664 | 0.004522 | −0.011746 | −0.015609 | −0.006767 | 0.18887 | 0.059785 | 0.170341 | −0.058919 | 0.000693 | −0.298199 |
| 68 | −0.139734 | 0.062074 | 0.068701 | −0.022797 | −0.114862 | 0.105296 | 0.006963 | 0.026175 | −0.085165 | 0.015395 | 0.214608 | −0.018965 | −0.057626 | −0.029014 |
| 69 | −0.108334 | −0.013848 | 0.308549 | 0.136352 | 0.010558 | 0.029678 | −0.016819 | 0.061369 | 0.040037 | −0.07286 | −0.043983 | 0.046552 | −0.046521 | 0.105125 |
| 70 | −0.128637 | −0.04323 | −0.030389 | −0.096938 | −0.058042 | 0.138083 | 0.092791 | −0.088303 | −0.035644 | 0.133286 | 0.135136 | −0.246541 | −0.046437 | −0.143189 |
| 71 | 0.07014 | 0.048553 | −0.157133 | 0.142768 | 0.025712 | −0.039022 | −0.073635 | 0.140567 | 0.082369 | −0.186522 | −0.102642 | 0.076024 | −0.097439 | 0.074317 |
| 72 | −0.110067 | −0.1466 | 0.036343 | −0.132649 | 0.097385 | 0.018984 | 0.11564 | 0.063601 | −0.245398 | −0.011655 | 0.130224 | −0.004291 | −0.134022 | 0.027946 |
| 73 | −0.155388 | −0.044276 | −0.113924 | 0.075184 | −0.062124 | 0.068993 | −0.105572 | −0.023571 | 0.135092 | 0.057124 | −0.190852 | −0.127937 | 0.191698 | 0.018758 |
| 74 | 0.056564 | 0.377351 | −0.061688 | −0.039502 | −0.014433 | −0.167217 | −0.178576 | −0.223728 | −0.051528 | 0.030726 | −0.058599 | −0.030885 | −0.095678 | 0.079951 |
| 75 | 0.057141 | −0.052041 | 0.048492 | −0.10078 | 0.045047 | −0.050725 | 0.074789 | 0.026058 | −0.017488 | 0.003345 | −0.027406 | 0.082184 | −0.021731 | 0.052129 |
| 76 | 0.074015 | 0.00146 | 0.065257 | −0.027963 | 0.074783 | −0.008081 | 0.071357 | 0.044371 | 0.064226 | −0.005023 | −0.011129 | 0.128053 | −0.042346 | −0.066136 |
| 77 | −0.040235 | −0.027878 | −0.068759 | 0.012641 | −0.075742 | 0.083697 | −0.099167 | −0.063134 | −0.131953 | −0.103176 | 0.123148 | −0.088542 | −0.042236 | 0.035549 |

| | BC | BD | BE | BF | BG | BH | BI | BJ | BK | BL | BM | BN | BO | BP |
|---|---|---|---|---|---|---|---|---|---|---|---|---|---|---|
| 1 | 0.001483 | −0.05932 | 0.049437 | −0.07031 | 0.019196 | −0.117165 | 0.015532 | −0.044515 | 0.02835 | −0.01511 | −0.089719 | 0.099969 | −0.062342 | 0.175449 |
| 2 | −0.032471 | −0.024155 | 0.103326 | 0.027379 | −0.037085 | −0.048762 | 0.014334 | 0.057379 | 0.043828 | 0.029878 | −0.007623 | −0.018833 | 0.015131 | −0.085693 |
| 3 | −0.018427 | 0.004492 | 0.025905 | −0.161075 | 0.044152 | −0.047524 | 0.024296 | −0.07176 | 0.012424 | −0.004083 | −0.05419 | 0.060387 | −0.118991 | 0.028329 |
| 4 | −0.02473 | 0.138716 | 0.009079 | 0.259489 | 0.12399 | 0.141664 | 0.001235 | −0.062713 | −0.059737 | 0.017441 | 0.063179 | −0.184683 | 0.216653 | −0.161398 |
| 5 | −0.005369 | −0.003719 | −0.205402 | −0.01416 | −0.059648 | 0.089281 | −0.013848 | 0.013631 | −0.046874 | −0.005845 | 0.112585 | 0.014035 | −0.101882 | 0.141849 |
| 6 | −0.160264 | −0.11636 | −0.023043 | −0.106483 | −0.068135 | −0.08922 | −0.079387 | 0.107508 | 0.131016 | −0.047541 | 0.142042 | −0.110841 | −0.035228 | 0.08408 |
| 7 | 0.016707 | 0.101996 | 0.012373 | 0.162127 | −0.22142 | 0.020191 | 0.102994 | −0.177138 | −0.045868 | 0.235402 | −0.052205 | −0.035777 | −0.066867 | −0.089195 |
| 8 | 0.08739 | −0.151024 | −0.068883 | −0.036109 | 0.122032 | 0.03367 | −0.097229 | 0.126194 | −0.111688 | −0.263248 | −0.124197 | 0.170184 | 0.140673 | −0.043709 |
| 9 | 0.059231 | −0.149812 | 0.082375 | −0.226557 | −0.018162 | −0.143153 | 0.129181 | −0.073617 | −0.368166 | 0.053857 | 0.160994 | 0.091791 | 0.106849 | 0.085297 |
| 10 | −0.09356 | 0.095983 | −0.024879 | 0.105787 | 0.010032 | 0.147041 | −0.071085 | −0.001614 | 0.3297 | −0.071813 | −0.14544 | −0.118563 | −0.110164 | −0.094214 |
| 11 | −0.230123 | −0.173997 | −0.372159 | −0.075447 | −0.065252 | −0.048528 | 0.210423 | −0.23993 | 0.099026 | −0.113849 | −0.010815 | −0.059432 | 0.149602 | −0.030608 |
| 12 | −0.010704 | 0.004405 | −0.058684 | 0.24292 | −0.108782 | 0.042402 | −0.089407 | 0.126488 | −0.011309 | 0.044182 | −0.165838 | −0.0418 | 0.049445 | 0.037347 |
| 13 | 0.118208 | 0.000371 | 0.047759 | 0.052178 | 0.018302 | −0.004985 | 0.012038 | −0.071561 | 0.033253 | −0.027933 | −0.009554 | −0.031561 | 0.023517 | −0.027791 |
| 14 | 0.169666 | 0.103818 | −0.22982 | −0.09517 | 0.052525 | 0.024171 | −0.01283 | −0.116057 | −0.008663 | −0.054176 | −0.023764 | 0.099214 | −0.009972 | 0.074731 |
| 15 | −0.083776 | 0.070999 | 0.038983 | 0.211561 | −0.006895 | −0.006001 | 0.055566 | 0.233388 | −0.008862 | 0.008104 | 0.246395 | −0.075875 | 0.057041 | −0.172755 |
| 16 | 0.052818 | 0.093116 | 0.019914 | −0.058627 | −0.066376 | 0.079155 | 0.027199 | 0.031031 | 0.047084 | 0.119006 | 0.01227 | 0.022477 | −0.009521 | −0.00556 |
| 17 | −0.022331 | −0.01208 | −0.029927 | −0.042134 | 0.010884 | −0.030418 | 0.022982 | 0.012829 | 0.123624 | 0.022515 | −0.00825 | 0.025419 | −0.059502 | 0.032161 |
| 18 | 0.00871 | 0.011682 | 0.185306 | 0.039341 | 0.083497 | −0.096867 | 0.045602 | −0.000161 | −0.062992 | −0.008344 | 0.061129 | −0.024638 | −0.018231 | −0.027696 |
| 19 | −0.079696 | 0.148291 | −0.104155 | −0.040088 | 0.002599 | −0.030457 | −0.064263 | 0.068347 | 0.019771 | 0.050118 | −0.001814 | −0.040884 | −0.020239 | 0.111059 |
| 20 | −0.039905 | −0.189998 | 0.142262 | 0.01224 | 0.008789 | −0.060775 | −0.006349 | −0.157528 | −0.075988 | −0.080349 | −0.059743 | 0.064216 | −0.062336 | −0.071559 |
| 21 | 0.207719 | 0.079436 | −0.157378 | 0.121982 | 0.115244 | 0.063378 | 0.089274 | 0.18997 | −0.173161 | 0.052428 | −0.115229 | −0.06163 | −0.103762 | 0.016148 |
| 22 | −0.044689 | 0.024911 | 0.057309 | 0.055784 | 0.075437 | −0.210074 | −0.16011 | −0.159759 | −0.072303 | 0.041478 | 0.136857 | −0.07038 | 0.155451 | 0.097092 |
| 23 | −0.187109 | −0.021566 | −0.045904 | −0.097176 | −0.13194 | 0.036113 | 0.282536 | −0.014176 | 0.054193 | −0.152904 | −0.110978 | 0.016795 | −0.205846 | −0.066599 |
| 24 | −0.027826 | −0.134602 | −0.120242 | −0.059996 | 0.192609 | 0.039638 | −0.324438 | −0.14175 | −0.061227 | 0.024338 | 0.272497 | −0.029067 | −0.091556 | −0.129212 |
| 25 | −0.049311 | 0.10774 | −0.247549 | 0.035131 | −0.038984 | −0.171216 | 0.019245 | −0.147872 | −0.012093 | 0.13813 | −0.03513 | −0.063707 | 0.097208 | −0.019352 |
| 26 | −0.147038 | 0.090615 | −0.095672 | −0.145089 | −0.192094 | 0.272738 | 0.026486 | 0.044744 | −0.10116 | 0.024283 | −0.058492 | 0.116102 | −0.000097 | −0.093441 |

APPENDIX B8-continued

PCA Transformation
Matrix (77 × 77; Benign/Malignant)

| | | | | | | | | | | | | | | |
|---|---|---|---|---|---|---|---|---|---|---|---|---|---|---|
| 27 | −0.050427 | −0.165472 | −0.118065 | 0.144056 | 0.075311 | −0.16787 | 0.021909 | −0.054495 | 0.059877 | −0.101628 | 0.073592 | −0.130598 | 0.069543 | 0.092816 |
| 28 | 0.063577 | 0.273132 | −0.093481 | −0.111031 | 0.030154 | 0.087862 | 0.077701 | 0.169946 | 0.118727 | −0.006672 | 0.086179 | 0.057991 | −0.020758 | 0.013351 |
| 29 | −0.042373 | −0.064477 | 0.092155 | 0.125391 | 0.289047 | 0.165799 | 0.033359 | −0.07973 | −0.15974 | 0.101752 | 0.012521 | 0.249069 | 0.125587 | −0.012072 |
| 30 | 0.109738 | 0.122853 | 0.010906 | −0.137543 | −0.022561 | −0.058709 | −0.014753 | 0.011529 | 0.089455 | −0.157943 | 0.048973 | −0.034113 | −0.086129 | 0.034639 |
| 31 | 0.134671 | −0.263994 | −0.03749 | −0.009886 | −0.154715 | 0.017424 | −0.117453 | 0.124806 | 0.137577 | 0.130983 | −0.063036 | 0.156119 | 0.073594 | −0.178357 |
| 32 | 0.066583 | 0.06957 | 0.066115 | −0.164257 | 0.133417 | 0.131283 | 0.038551 | −0.032017 | 0.272572 | −0.120499 | 0.044388 | 0.144993 | 0.090987 | 0.165023 |
| 33 | −0.125533 | 0.022854 | −0.035244 | −0.103119 | −0.045812 | −0.035355 | −0.145671 | 0.206824 | −0.163975 | 0.075185 | −0.046322 | −0.251495 | 0.089798 | −0.194139 |
| 34 | 0.122481 | −0.024482 | 0.079992 | 0.132524 | −0.04547 | 0.075324 | −0.084376 | −0.00516 | 0.019139 | −0.237858 | 0.084621 | 0.127567 | 0.144259 | 0.112061 |
| 35 | 0.207338 | −0.231592 | 0.095562 | 0.117906 | 0.107778 | 0.083399 | 0.128214 | −0.093481 | 0.0712 | −0.122898 | −0.011764 | −0.206693 | −0.065525 | −0.152859 |
| 36 | 0.058661 | 0.059383 | −0.138714 | 0.062788 | 0.031591 | −0.064839 | −0.21067 | 0.180344 | 0.068259 | 0.061217 | 0.241252 | 0.053946 | −0.066904 | 0.13328 |
| 37 | 0.08571 | −0.108905 | 0.160693 | 0.021422 | −0.064285 | 0.002996 | 0.094692 | −0.121013 | −0.052654 | −0.013211 | −0.05599 | −0.131011 | 0.030471 | −0.123114 |
| 38 | −0.076897 | −0.074974 | 0.132653 | 0.067341 | 0.072954 | −0.189397 | −0.03156 | 0.008966 | 0.013398 | 0.108252 | −0.064346 | −0.093478 | −0.107585 | 0.036694 |
| 39 | 0.101006 | 0.158436 | 0.044151 | −0.105176 | −0.147117 | −0.043821 | 0.224999 | −0.116532 | 0.140766 | 0.325611 | 0.25627 | −0.230967 | 0.050851 | 0.001336 |
| 40 | −0.039812 | 0.164587 | 0.079036 | 0.053421 | −0.232038 | −0.006486 | −0.020713 | −0.03717 | −0.103913 | −0.322647 | −0.286742 | −0.018747 | −0.064083 | −0.051794 |
| 41 | −0.139004 | −0.16082 | −0.097624 | 0.144009 | 0.120374 | 0.016495 | 0.009926 | 0.073655 | 0.017755 | 0.105832 | 0.043681 | −0.00494 | 0.027177 | 0.079802 |
| 42 | 0.089001 | 0.138323 | 0.132014 | 0.077389 | −0.019429 | 0.171064 | 0.044436 | −0.22202 | −0.056302 | −0.075798 | 0.045139 | −0.250451 | 0.007333 | 0.362886 |
| 43 | 0.052844 | 0.061437 | 4.148781 | 0.033525 | −0.105986 | −0.259067 | 0.253843 | 0.06785 | −0.208513 | −0.114622 | 0.06641 | 0.147153 | 0.01561 | 0.092676 |
| 44 | −0.320446 | 0.064292 | 0.124461 | −0.139156 | 0.12691 | −0.141681 | −0.030791 | 0.069588 | −0.080185 | 0.245549 | −0.1597 | 0.148767 | −0.283472 | 0.062966 |
| 45 | −0.120062 | −0.068129 | −0.053174 | 0.039681 | −0.155373 | 0.056581 | −0.135365 | −0.028148 | −0.022887 | 0.009635 | 0.001777 | 0.07198 | 0.079532 | 0.04617 |
| 46 | 0.109435 | −0.034924 | 0.015357 | −0.143768 | 0.223201 | 0.015672 | 0.240021 | 0.146914 | 0.052271 | −0.055643 | −0.016215 | −0.048405 | 0.069613 | 0.016861 |
| 47 | 0.074968 | 0.0915 | −0.016878 | 0.003381 | −0.132439 | 0.187515 | −0.238263 | −0.121111 | −0.063364 | −0.048635 | 0.061347 | 0.01296 | −0.25558 | 0.084867 |
| 48 | −0.137948 | 0.0845 | −0.18337 | 0.146637 | 0.094385 | −0.017726 | 0.062746 | −0.040616 | 0.029959 | −0.051853 | 0.02635 | 0.135157 | 0.17637 | −0.072523 |
| 49 | 0.12105 | 0.048113 | −0.013446 | −0.247833 | 0.123238 | −0.113748 | −0.092428 | 0.083619 | 0.099118 | −0.197613 | 0.015591 | −0.213643 | 0.082373 | −0.075506 |
| 50 | −0.197512 | −0.097656 | −0.137624 | 0.224628 | 0.129793 | 0.158172 | 0.117854 | 0.05427 | −0.048947 | 0.022645 | 0.096114 | 0.080901 | −0.133193 | 0.103719 |
| 51 | 0.003055 | 0.179348 | 0.101992 | −0.031498 | −0.128694 | −0.155586 | −0.261486 | −0.183192 | −0.010374 | −0.056512 | −0.058987 | −0.027211 | 0.050985 | −0.111936 |
| 52 | −0.031025 | 0.13839 | 0.046403 | 0.029846 | 0.080605 | −0.116834 | −0.009049 | −0.043855 | −0.01853 | −0.095429 | −0.034539 | −0.027336 | 0.020107 | −0.101799 |
| 53 | 0.149953 | 0.080683 | −0.007716 | −0.061836 | 0.045935 | −0.038374 | −0.213815 | 0.127741 | −0.094161 | 0.216352 | −0.1484 | 0.006413 | −0.019076 | 0.076918 |
| 54 | 0.120986 | −0.052215 | 0.06288 | −0.102117 | 0.14782 | 0.213731 | 0.013838 | 0.013223 | −0.064965 | 0.019658 | 0.081235 | −0.065422 | −0.183189 | 0.031515 |
| 55 | −0.13544 | 0.050234 | 0.277577 | 0.012771 | −0.100665 | −0.099355 | 0.052329 | 0.120525 | 0.129017 | −0.211344 | 0.369796 | 0.221158 | −0.013577 | −0.037869 |
| 56 | −0.022413 | −0.019038 | −0.077333 | 0.056102 | 0.011915 | −0.014947 | 0.01383 | 0.063478 | 0.017 | 0.028599 | −0.00431 | 0.016867 | −0.036255 | 0.042362 |
| 57 | 0.007049 | −0.188272 | 0.178425 | 0.02043 | −0.236664 | 0.170121 | 0.062064 | 0.19458 | −0.090664 | 0.052605 | 0.118667 | −0.048513 | 0.032875 | −0.007389 |
| 58 | −0.055332 | 0.080185 | −0.016873 | 0.083298 | 0.087787 | −0.203867 | −0.139204 | 0.038901 | 0.040096 | −0.004838 | −0.076273 | −0.031446 | 0.036907 | 0.115437 |
| 59 | −0.072423 | 0.000083 | 0.010978 | 0.055197 | 0.09397 | −0.092196 | 0.019116 | −0.071056 | 0.093646 | −0.099555 | −0.186828 | −0.046592 | −0.049098 | −0.029437 |
| 60 | 0.007696 | −0.147722 | −0.090008 | −0.234157 | 0.014493 | 0.108384 | −0.018245 | −0.244029 | −0.058223 | 0.076377 | −0.017748 | −0.033708 | −0.071081 | 0.057435 |
| 61 | −0.284292 | −0.080304 | 0.196802 | −0.04929 | −0.088963 | 0.047342 | −0.167142 | −0.105309 | 0.133052 | −0.036204 | 0.057183 | 0.071547 | 0.058757 | −0.055521 |
| 62 | 0.089383 | −0.152553 | −0.194259 | 0.094028 | −0.275316 | 0.00169 | −0.070347 | 0.04639 | 0.056478 | −0.035419 | 0.131563 | −0.075435 | −0.109178 | 0.027123 |
| 63 | −0.167622 | 0.136141 | −0.018205 | −0.017159 | 0.145802 | 0.155108 | 0.129384 | 0.094671 | 0.076273 | −0.030179 | −0.088837 | −0.056392 | 0.056316 | −0.009724 |
| 64 | 0.169423 | −0.049808 | 0.076526 | 0.157189 | −0.14369 | −0.1714 | 0.0006 | 0.178071 | −0.023375 | −0.018937 | −0.22355 | 0.064305 | 0.142374 | 0.262416 |
| 65 | 0.127256 | −0.0672 | −0.05657 | −0.049292 | −0.151981 | 0.200335 | −0.067298 | −0.03862 | −0.100973 | −0.007856 | −0.010715 | 0.040298 | 0.113372 | −0.0701 |
| 66 | −0.137273 | 0.005605 | 0.157573 | 0.045431 | 0.077651 | 0.073669 | 0.052447 | 0.075176 | −0.196898 | −0.056579 | −0.011943 | −0.172397 | −0.095861 | 0.038654 |
| 67 | −0.057426 | 0.11398 | −0.00887 | 0.082319 | −0.027901 | −0.057607 | 0.012912 | −0.115541 | 0.017425 | 0.048705 | 0.041852 | 0.027061 | 0.1382 | 0.020259 |
| 68 | 0.140684 | −0.137685 | 0.01114 | 0.151154 | −0.064273 | −0.130457 | 0.079126 | −0.162935 | 0.07611 | 0.093954 | −0.014856 | 0.090976 | −0.156051 | −0.018827 |
| 69 | 0.076137 | 0.045707 | 0.07159 | 0.055314 | −0.121779 | −0.00557 | 0.087428 | 0.038326 | 0.187601 | 0.147078 | 0.023154 | 0.287529 | −0.033251 | −0.115629 |
| 70 | −0.071103 | 0.049057 | −0.134081 | −0.191443 | −0.065487 | −0.022429 | −0.06843 | 0.085765 | −0.259019 | −0.115546 | 0.049331 | −0.034849 | 0.113489 | −0.257623 |
| 71 | 0.146263 | −0.117332 | −0.055073 | −0.010432 | 0.13624 | −0.001543 | −0.136408 | −0.051479 | 0.263216 | 0.138043 | −0.124446 | 0.096731 | 0.063112 | −0.165437 |
| 72 | −0.101824 | −0.222125 | −0.028359 | 0.015238 | −0.047584 | 0.020999 | −0.104358 | 0.156889 | 0.04681 | −0.100582 | −0.001455 | −0.255902 | −0.185337 | 0.18301 |
| 73 | −0.019434 | 0.157243 | 0.09752 | 0.03729 | 0.087553 | 0.155256 | −0.075888 | −0.086483 | −0.052339 | −0.002832 | 0.055117 | 0.071169 | 0.056803 | −0.058579 |
| 74 | 0.051339 | −0.107353 | 0.061625 | −0.185848 | 0.020715 | −0.078437 | 0.116169 | 0.184825 | 0.102812 | 0.152214 | −0.080813 | −0.151415 | 0.12682 | −0.12263 |

APPENDIX B8-continued

PCA Transformation
Matrix (77 × 77; Benign/Malignant)

| | | | | | | | | | | | | | | |
|---|---|---|---|---|---|---|---|---|---|---|---|---|---|---|
| 75 | 0.01041 | −0.025746 | −0.042612 | 0.086906 | 0.074118 | −0.013034 | −0.010563 | −0.014974 | −0.092134 | −0.004249 | −0.061868 | 0.042527 | −0.200621 | −0.169561 |
| 76 | 0.125448 | 0.063124 | −0.09505 | 0.06402 | −0.033188 | −0.14049 | −0.000422 | 0.042452 | 0.008934 | −0.128249 | 0.144398 | 0.013577 | −0.155829 | −0.130613 |
| 77 | −0.140495 | −0.083702 | 0.058909 | −0.104885 | −0.112196 | 0.169656 | −0.046194 | 0.038189 | 0.07138 | 0.093486 | −0.127898 | −0.050442 | 0.376724 | 0.294908 |

| | BQ | BR | BS | BT | BU | BV | BW | BX | BY | BZ |
|---|---|---|---|---|---|---|---|---|---|---|
| 1 | −0.009525 | −0.0083 | 0.022276 | 0.127853 | 0.112219 | −0.078151 | −0.167769 | −0.049994 | −0.090032 | 0.008946 |
| 2 | 0.013735 | 0.014117 | −0.090287 | −0.095177 | −0.037977 | −0.02397 | −0.044725 | 0.013089 | 0.010565 | 0.15806 |
| 3 | 0.05736 | 0.052558 | 0.033172 | 0.027519 | 0.008083 | −0.054379 | −0.118044 | −0.039211 | −0.035033 | 0.174097 |
| 4 | −0.111355 | −0.105191 | −0.114174 | −0.085582 | −0.02202 | −0.001815 | 0.154358 | 0.054663 | 0.087282 | 0.099849 |
| 5 | 0.002506 | 0.000723 | 0.175538 | 0.105557 | −0.003394 | 0.089694 | 0.12848 | 0.012966 | 0.021042 | 0.074925 |
| 6 | 0.036237 | 0.047851 | 0.0993 | −0.007096 | 0.02353 | 0.008643 | 0.048628 | 0.033505 | −0.060023 | 0.077891 |
| 7 | −0.070658 | 0.081795 | 0.070667 | 0.180005 | −0.041727 | 0.061021 | −0.156141 | −0.112267 | −0.063303 | 0.059689 |
| 8 | 0.11765 | −0.087119 | −0.119632 | −0.108485 | −0.071161 | 0.089094 | 0.067699 | 0.043332 | 0.115019 | 0.016055 |
| 9 | 0.031704 | 0.070827 | −0.202844 | 0.067465 | −0.038584 | 0.085497 | −0.11834 | 0.02303 | −0.005427 | 0.001629 |
| 10 | −0.083042 | −0.106404 | 0.108586 | −0.050157 | 0.016414 | 0.019957 | 0.164026 | −0.01232 | 0.044822 | 0.001691 |
| 11 | −0.179056 | 0.024772 | −0.051381 | −0.10919 | −0.035518 | 0.100471 | −0.124323 | 0.054691 | 0.033178 | 0.10338 |
| 12 | 0.125263 | 0.017961 | 0.105943 | 0.014374 | −0.015619 | −0.139214 | −0.181426 | −0.041986 | −0.05323 | 0.010434 |
| 13 | −0.004077 | 0.00748 | −0.017965 | −0.03109 | 0.018886 | −0.044145 | −0.015215 | 0.005507 | −0.008989 | 0.004714 |
| 14 | −0.108456 | −0.012808 | −0.040521 | −0.024325 | −0.032142 | 0.045121 | 0.10912 | 0.050332 | 0.054021 | 0.012031 |
| 15 | 0.109733 | 0.044049 | 0.024981 | −0.027345 | −0.079292 | 0.063962 | 0.128326 | 0.063601 | 0.035964 | 0.04877 |
| 16 | −0.030379 | 0.028292 | −0.004644 | −0.078365 | −0.062809 | 0.006539 | 0.018515 | 0.012653 | 0.034472 | 0.032163 |
| 17 | 0.101205 | −0.019179 | −0.004396 | 0.01115 | −0.017504 | 0.018429 | 0.023498 | −0.012162 | −0.018232 | 0.003371 |
| 18 | −0.10745 | 0.017917 | 0.121017 | −0.006463 | 0.000452 | −0.059315 | 0.053189 | 0.003037 | 0.048701 | 0.016283 |
| 19 | 0.060976 | −0.04104 | −0.00695 | 0.043214 | −0.042706 | −0.003338 | −0.017553 | 0.014437 | 0.023361 | 0.014326 |
| 20 | −0.050716 | −0.005627 | 0.022422 | 0.016531 | 0.120746 | 0.12465 | −0.007247 | −0.071218 | −0.059709 | 0.003351 |
| 21 | −0.007743 | −0.226644 | −0.01194 | 0.222181 | 0.263505 | 0.199656 | −0.082927 | −0.056046 | −0.108889 | 0.09151 |
| 22 | −0.025927 | 0.063772 | 0.10441 | 0.099336 | −0.165345 | 0.108045 | 0.009958 | 0.042213 | 0.063848 | 0.401635 |
| 23 | 0.034833 | 0.03997 | −0.183174 | −0.068298 | 0.28549 | −0.099688 | 0.067616 | −0.057688 | −0.15569 | 0.323364 |
| 24 | 0.133819 | −0.117966 | −0.039026 | 0.332646 | −0.110934 | −0.113834 | −0.032444 | 0.004804 | 0.02224 | 0.034305 |
| 25 | 0.221605 | −0.129638 | 0.157347 | 0.008681 | −0.012988 | 0.18454 | 0.053567 | −0.022685 | 0.02559 | 0.037866 |
| 26 | 0.074317 | −0.000535 | −0.173124 | −0.084614 | −0.050333 | 0.102043 | −0.089016 | −0.002127 | −0.026499 | 0.014299 |
| 27 | −0.081732 | 0.05585 | −0.037236 | 0.037062 | 0.0052 | −0.070215 | 0.034713 | 0.040531 | −0.03575 | 0.020611 |
| 28 | 0.095371 | 0.052516 | −0.055125 | −0.026299 | −0.094152 | 0.102448 | −0.037927 | 0.060176 | 0.025821 | 0.011977 |
| 29 | −0.020421 | −0.094506 | −0.073881 | −0.172259 | 0.182969 | 0.03748 | −0.07598 | −0.042136 | 0.044841 | 0.320322 |
| 30 | −0.009013 | 0.170431 | 0.043601 | 0.148091 | −0.112326 | −0.00775 | 0.058618 | 0.02964 | −0.054288 | 0.194799 |
| 31 | 0.137451 | −0.097241 | −0.032482 | −0.171519 | 0.078661 | 0.037407 | 0.032196 | −0.052394 | −0.01012 | 0.263472 |
| 32 | −0.149264 | 0.007373 | 0.243021 | 0.031883 | −0.020379 | 0.157453 | −0.24342 | −0.005584 | −0.026388 | 0.110474 |
| 33 | −0.161897 | 0.104823 | −0.159786 | 0.017804 | 0.014567 | −0.018014 | −0.098436 | 0.05327 | 0.076548 | 0.009443 |
| 34 | −0.061358 | 0.100141 | −0.033053 | 0.068728 | 0.012374 | −0.110295 | −0.050155 | 0.026109 | −0.053045 | 0.015029 |
| 35 | −0.227745 | 0.052471 | 0.037793 | 0.083831 | −0.012784 | −0.018795 | 0.101133 | 0.021618 | −0.004406 | 0.03601 |
| 36 | −0.048049 | 0.126358 | −0.069525 | −0.10401 | 0.096643 | −0.249438 | −0.136717 | 0.021153 | −0.019367 | 0.028146 |
| 37 | −0.03871 | −0.152216 | 0.108521 | −0.041883 | −0.024611 | 0.062966 | 0.12399 | 0.000999 | 0.063265 | 0.009699 |
| 38 | −0.061457 | 0.030748 | −0.080735 | 0.02921 | −0.005152 | −0.012104 | −0.042721 | −0.025752 | 0.000175 | 0.012379 |
| 39 | −0.056114 | −0.012894 | 0.073902 | −0.083929 | 0.108233 | −0.032405 | −0.108022 | 0.029646 | −0.018396 | 0.120074 |
| 40 | 0.0439 | 0.075397 | −0.127064 | 0.251096 | −0.322918 | −0.024194 | 0.044368 | 0.001232 | 0.004202 | 0.190411 |
| 41 | −0.03914 | −0.062255 | 0.005907 | −0.079599 | 0.092651 | −0.019648 | −0.008685 | −0.010929 | 0.045582 | 0.079854 |
| 42 | 0.384912 | 0.097071 | −0.183472 | −0.212543 | 0.019541 | 0.113079 | 0.069625 | 0.018852 | −0.029668 | 0.095618 |
| 43 | −0.035346 | −0.138299 | 0.150143 | −0.094349 | 0.02199 | −0.415286 | 0.24395 | 0.064913 | 0.070426 | 0.036348 |
| 44 | 0.032233 | −0.182057 | 0.087608 | −0.041369 | −0.070059 | 0.134368 | 0.218524 | 0.010295 | 0.123318 | 0.014028 |

APPENDIX B8-continued

PCA Transformation
Matrix (77 × 77; Benign/Malignant)

| | | | | | | | | | | |
|---|---|---|---|---|---|---|---|---|---|---|
| 45 | 0.053573 | 0.052003 | −0.034752 | −0.006517 | 0.093005 | −0.135613 | −0.103826 | −0.060945 | −0.073749 | 0.010556 |
| 46 | 0.01854 | 0.059954 | −0.090679 | 0.125994 | −0.09587 | 0.114471 | −0.003482 | 0.034283 | 0.003318 | 0.00762 |
| 47 | −0.260186 | −0.035406 | 0.060973 | −0.116051 | 0.133336 | −0.004734 | 0.082505 | 0.064762 | 0.071065 | 0.013759 |
| 48 | 0.179663 | −0.012351 | 0.054403 | 0.05063 | −0.046341 | −0.078499 | −0.08934 | −0.041936 | −0.036884 | 0.011633 |
| 49 | 0.072889 | −0.174318 | −0.058992 | −0.156392 | 0.150399 | −0.118395 | 0.035461 | 0.08461 | −0.009117 | 0.078616 |
| 50 | −0.066791 | 0.248489 | 0.044453 | 0.064815 | −0.144066 | 0.08419 | 0.070014 | −0.043857 | −0.002012 | 0.033667 |
| 51 | 0.027986 | −0.192114 | 0.039422 | −0.008388 | 0.173251 | −0.033959 | −0.102861 | −0.005313 | −0.055605 | 0.014656 |
| 52 | 0.038751 | −0.054543 | −0.023007 | 0.006464 | 0.004171 | 0.033154 | −0.059509 | 0.001666 | −0.023533 | 0.036537 |
| 53 | −0.123568 | 0.385887 | −0.156793 | 0.051325 | 0.176623 | −0.006705 | 0.275317 | 0.057329 | 0.099286 | 0.264333 |
| 54 | 0.191827 | −0.238148 | 0.178309 | −0.046257 | −0.281171 | −0.28144 | −0.090729 | −0.09728 | −0.04098 | 0.272338 |
| 55 | 0.020393 | −0.084729 | −0.005738 | 0.114753 | 0.215894 | 0.266426 | 0.183773 | 0.04607 | −0.061152 | 0.048003 |
| 56 | 0.044975 | −0.029903 | 0.015165 | −0.016035 | −0.028216 | 0.006118 | 0.038145 | 0.01001 | 0.040481 | 0.002595 |
| 57 | 0.093698 | 0.030933 | 0.116606 | 0.142155 | 0.100861 | −0.027244 | −0.093239 | −0.044231 | −0.129794 | 0.034606 |
| 58 | −0.183907 | −0.205609 | −0.180716 | −0.089551 | −0.159884 | 0.071616 | −0.002927 | −0.199747 | −0.531802 | 0.109979 |
| 59 | 0.232272 | 0.090729 | 0.11061 | 0.201347 | 0.298644 | −0.062101 | −0.208163 | 0.132992 | 0.459185 | 0.107605 |
| 60 | −0.122817 | 0.008123 | −0.003377 | −0.109146 | −0.064589 | −0.017082 | 0.077256 | −0.008086 | 0.066731 | 0.025623 |
| 61 | 0.053794 | 0.178568 | 0.029492 | −0.239132 | −0.168588 | −0.100165 | 0.008883 | −0.003629 | 0.083379 | 0.021085 |
| 62 | 0.104276 | −0.166327 | −0.087432 | 0.034636 | −0.059485 | 0.209348 | 0.063685 | 0.141088 | 0.088558 | 0.175634 |
| 63 | −0.079432 | 0.085459 | 0.035659 | 0.057114 | 0.081159 | −0.232937 | 0.057427 | −0.10546 | −0.103812 | 0.147204 |
| 64 | −0.09166 | 0.048849 | 0.284529 | −0.254363 | −0.130301 | 0.167661 | −0.108986 | 0.044126 | 0.110282 | 0.114398 |
| 65 | −0.003946 | −0.021219 | 0.087734 | −0.01124 | 0.038457 | −0.048556 | 0.046808 | −0.024985 | −0.016869 | 0.014901 |
| 66 | 0.001037 | −0.059358 | 0.084969 | −0.094549 | −0.047498 | −0.026601 | −0.089815 | −0.068896 | 0.051113 | 0.099814 |
| 67 | −0.008027 | 0.021973 | −0.183598 | 0.07282 | 0.071812 | −0.015558 | −0.037711 | 0.121502 | −0.008812 | 0.080254 |
| 68 | 0.193435 | 0.068655 | −0.076538 | 0.052996 | −0.035527 | −0.127269 | 0.260784 | −0.071952 | −0.117152 | 0.021348 |
| 69 | −0.265902 | −0.244701 | −0.20319 | 0.157763 | −0.222505 | −0.134272 | −0.135734 | 0.174881 | 0.202882 | 0.188317 |
| 70 | −0.106762 | 0.118996 | 0.388082 | 0.027531 | 0.038237 | 0.077249 | 0.06066 | −0.109524 | −0.118546 | 0.164756 |
| 71 | 0.130613 | 0.200081 | 0.084998 | 0.05447 | 0.021512 | 0.115104 | 0.103707 | −0.110122 | −0.164066 | 0.059413 |
| 72 | −0.107161 | −0.12433 | −0.119296 | 0.034302 | 0.002376 | 0.127706 | −0.181438 | 0.029125 | 0.069542 | 0.051226 |
| 73 | −0.004867 | 0.001427 | 0.003167 | 0.022395 | 0.006844 | 0.109933 | −0.023245 | −0.00213 | 0.017387 | 0.005943 |
| 74 | 0.118202 | 0.059283 | −0.052079 | −0.003226 | −0.176968 | −0.024105 | 0.00071 | 0.010968 | 0.014563 | 0.010196 |
| 75 | 0.060021 | 0.103411 | 0.119229 | −0.138718 | −0.018969 | 0.000571 | −0.1403 | 0.609342 | −0.309661 | 0.017809 |
| 76 | −0.018738 | 0.08418 | −0.09186 | −0.13889 | −0.019768 | 0.047554 | −0.112289 | −0.590215 | 0.267155 | 0.017679 |
| 77 | −0.032094 | −0.190049 | 0.020411 | 0.292645 | 0.059659 | −0.117654 | 0.248735 | −0.031045 | 0.021424 | 0.014642 |

APPENDIX B9

PCA Transformation
Matrix (77 × 77; Early/Late)

| | A | B | C | D | E | F | G | H |
|---|---|---|---|---|---|---|---|---|
| 1 | 494.4/184.1>GPCho:Lyso 16:1 | −0.010683 | −0.062621 | 0.027248 | −0.026219 | −0.335284 | 0.19554 | 0.025475 |
| 2 | 496.4/184.1>GPCho:Lyso 16:0 | 0.069254 | −0.068194 | 0.020311 | −0.137287 | −0.212396 | −0.037232 | 0.081205 |
| 3 | 520.4/184.1>GPCho:Lyso 18:2 | 0.068864 | 0.040834 | 0.196951 | 0.178798 | −0.101984 | 0.142708 | 0.095704 |
| 4 | 522.4/184.1>GPCho:Lyso 18:1 | 0.088072 | −0.00825 | 0.043798 | 0.009224 | −0.296581 | 0.225544 | −0.013445 |
| 5 | 524.4/184.1>GPCho:Lyso 18:0 | 0.050109 | −0.082548 | 0.130096 | −0.005983 | −0.280482 | −0.09001 | −0.036971 |
| 6 | 544.4/184.1>GPCho:Lyso 20:4 | 0.013953 | 0.187946 | 0.063318 | −0.051514 | −0.144667 | −0.051741 | 0.074773 |
| 7 | 568.4/184.1>GPCho:Lyso 22:6 | 0.010899 | 0.170255 | 0.119905 | −0.077648 | −0.117704 | 0.020852 | 0.125072 |
| 8 | 570.4/184.1>GPCho:Lyso 22:5 | −0.024189 | 0.164479 | 0.131283 | −0.047226 | −0.174672 | 0.047435 | 0.086045 |
| 9 | 678.5/184.1>GPCho:28:0 | 0.076097 | −0.165159 | 0.049633 | −0.070143 | −0.140589 | −0.037294 | 0.034 |
| 10 | 678.5/184.1>GPCho:28:0a | 0.081693 | −0.151866 | 0.064318 | −0.075024 | −0.156379 | −0.032279 | 0.041031 |
| 11 | 704.6/184.1>GPCho:30:1a | 0.193398 | 0.073618 | 0.004978 | −0.046974 | 0.07565 | 0.040122 | −0.078774 |
| 12 | 706.6/184.1>GPCho:30:0a | 0.161585 | 0.05853 | 0.005547 | −0.094095 | −0.04542 | 0.036823 | −0.173403 |
| 13 | 718.6/184.1>GPCho:32:0p, 32:1e | 0.135957 | −0.06569 | 0.152926 | −0.111818 | 0.039484 | 0.082917 | 0.142184 |
| 14 | 730.8/184.1>GPCho:32:2 | 0.150594 | 0.034485 | −0.013378 | −0.011068 | −0.008404 | 0.024928 | 0.407199 |
| 15 | 732.6/184.1>GPCho:32:1a | 0.073625 | −0.040878 | −0.197402 | −0.051424 | −0.204303 | 0.101188 | 0.123603 |
| 16 | 734.6/184.1>GPCho:32:0a | 0.03987 | −0.046254 | −0.209133 | −0.185613 | 0.055487 | 0.129972 | −0.151517 |
| 17 | 742.6/184.1>GPCho:34:2p, 34:3e | 0.058367 | −0.15652 | 0.150393 | −0.072266 | 0.010433 | 0.079936 | 0.075349 |
| 18 | 744.6/184.1>GPCho:34:1p, 34:2e | −0.059501 | −0.029706 | 0.243472 | 0.06943 | 0.057321 | 0.197658 | −0.026028 |
| 19 | 746.6/184.1>GPCho:34:0p, 34:1e | 0.019457 | −0.115878 | 0.081861 | −0.149376 | 0.078956 | 0.280225 | −0.172601 |
| 20 | 748.6/184.1>GPCho:34:0e | 0.070091 | −0.145173 | 0.071781 | −0.142427 | 0.086864 | 0.159702 | −0.142589 |
| 21 | 756.6/184.1>GPCho:34:3a | 0.019203 | −0.216671 | −0.009206 | 0.0168 | 0.010688 | 0.035228 | −0.008751 |
| 22 | 758.7/184.1>GPCho:34:2a | −0.130503 | −0.093417 | −0.039428 | 0.123202 | 0.215203 | 0.057036 | 0.029898 |
| 23 | 760.6/184.1>GPCho:34:1a | −0.092885 | −0.102309 | −0.206564 | −0.06713 | −0.06941 | 0.171964 | −0.039599 |
| 24 | 762.6/184.1>GPCho:34:0a | −0.076499 | −0.084442 | −0.203645 | −0.091377 | −0.118414 | 0.191942 | −0.043234 |
| 25 | 768.6/184.1>GPCho:36:3p, 36:4e | −0.103814 | 0.129608 | 0.135707 | −0.149685 | 0.024041 | 0.025594 | −0.059261 |
| 26 | 770.6/184.1>GPCho:36:2p, 36:3e | −0.090417 | −0.008183 | 0.249015 | −0.030991 | 0.036311 | 0.127553 | −0.093214 |
| 27 | 772.6/184.1>GPCho:36:1p, 36:2e | −0.015283 | −0.186242 | 0.139416 | −0.018712 | 0.097921 | 0.107317 | 0.012548 |
| 28 | 774.6/184.1>GPCho:36:0p, 36:1e | −0.003105 | −0.166344 | 0.156411 | −0.120071 | −0.025109 | 0.047658 | 0.121477 |
| 29 | 782.6/184.1>GPCho:36:4a | −0.139261 | 0.130293 | −0.075834 | −0.07355 | 0.027422 | −0.081789 | 0.046593 |
| 30 | 784.6/184.1>GPCho:36:3a | −0.184625 | 0.012288 | 0.030689 | 0.069828 | −0.101481 | −0.060512 | 0.047553 |
| 31 | 786.6/184.1>GPCho:36:2a | −0.14279 | −0.093214 | 0.103044 | 0.168902 | −0.001439 | −0.009359 | −0.033657 |
| 32 | 788.6/184.1>GPCho:36:1a | −0.030288 | −0.200938 | 0.001685 | 0.071822 | −0.13992 | −0.045029 | −0.078364 |
| 33 | 790.8/184.1>GPCho:36:0 | −0.005709 | −0.204905 | 0.007121 | −0.008344 | −0.163734 | −0.033029 | −0.077559 |
| 34 | 792.6/184.1>GPCho:38:5p, 38:6e | −0.067505 | 0.080164 | 0.182611 | −0.214073 | −0.028097 | 0.054567 | 0.042334 |
| 35 | 794.6/184.1>GPCho:38:4p, 38:5e | −0.096712 | 0.142271 | 0.123049 | −0.155769 | 0.067413 | 0.051087 | −0.056042 |
| 36 | 796.6/184.1>GPCho:38:3p, 38:4e | −0.099757 | 0.109103 | 0.127804 | −0.196274 | 0.078237 | 0.01035 | −0.093561 |
| 37 | 798.6/184.1>GPCho:38:2p, 38:3e | −0.07341 | −0.119951 | 0.081436 | −0.254204 | 0.075651 | −0.053248 | −0.013279 |
| 38 | 800.6/184.1>GPCho:38:1p, 38:2e | 0.087317 | −0.134019 | 0.188052 | −0.098348 | 0.057735 | 0.026785 | 0.130747 |
| 39 | 808.6/184.1>GPCho:38:5a | −0.154189 | 0.131286 | 0.057141 | −0.075564 | −0.077768 | −0.040391 | 0.068377 |
| 40 | 810.6/184.1>GPCho:38:4a | −0.1581 | 0.114595 | −0.007262 | −0.058953 | −0.047117 | −0.131176 | −0.015771 |
| 41 | 812.6/184.1>GPCho:38:3a | −0.096723 | 0.038049 | 0.018902 | −0.023586 | −0.186887 | −0.246734 | 0.003879 |
| 42 | 814.6/184.1>GPCho:38:2a | 0.195472 | 0.019704 | −0.019287 | −0.08312 | 0.015901 | −0.084748 | −0.1482 |
| 43 | 816.6/184.1>GPCho:38:1a | 0.133234 | −0.117755 | 0.099804 | 0.021032 | −0.007373 | −0.200839 | −0.143211 |
| 44 | 820.6/184.1>GPCho:40:5p, 40:6e | −0.093315 | 0.116033 | 0.161906 | −0.18699 | 0.015765 | 0.038187 | 0.079876 |
| 45 | 822.6/184.1>GPCho:40:4p, 40:5e | −0.084916 | −0.013598 | 0.062147 | −0.300057 | 0.126044 | −0.052689 | 0.049406 |
| 46 | 824.6/184.1>GPCho:40:3p, 40:4e | −0.080705 | −0.091459 | 0.027734 | −0.283436 | 0.116446 | −0.080604 | −0.060893 |

APPENDIX B9-continued

PCA Transformation
Matrix (77 × 77; Early/Late)

| | | | | | | | | | | |
|---|---|---|---|---|---|---|---|---|---|---|
| 47 | 826.6/184.1>GPCho:40:2p, 40:3e | | | 0.034385 | −0.212008 | −0.032769 | −0.109713 | 0.067979 | −0.045811 | 0.02792 |
| 48 | 828.6/184.1>GPCho:40:1p, 40:2e | | | 0.075771 | −0.203734 | 0.005579 | −0.104127 | 0.054004 | −0.033018 | 0.039052 |
| 49 | 834.6/184.1>GPCho:40:6a | | | −0.123826 | 0.133728 | 0.076228 | −0.107221 | −0.087112 | −0.029187 | 0.093786 |
| 50 | 836.6/184.1>GPCho:40:5a | | | −0.147413 | 0.031042 | 0.02156 | −0.134205 | −0.090746 | −0.167277 | 0.056509 |
| 51 | 838.6/184.1>GPCho:40:4a | | | −0.130804 | −0.092637 | −0.041765 | −0.112063 | −0.093568 | −0.21821 | −0.021772 |
| 52 | 701.5/184.1>SM:18/16:1 | | | 0.174863 | 0.054533 | 0.041256 | −0.006086 | 0.04713 | 0.065263 | 0.181832 |
| 53 | 703.5/184.1>SM:18/16:0 | | | 0.197672 | 0.073169 | 0.007975 | −0.035504 | 0.068736 | 0.021334 | −0.051376 |
| 54 | 703.8/184.4>SM:d18:1/16:0 | | | 0.190912 | 0.079085 | 0.009778 | −0.046261 | 0.090404 | 0.016235 | −0.094065 |
| 55 | 705.8/184.4>SM:d18:0/16:0 | | | 0.185708 | 0.091908 | −0.00808 | −0.048309 | 0.065687 | −0.019604 | −0.11922 |
| 56 | 727.6/184.1>SM:18/18:2 | | | 0.138094 | −0.052216 | 0.067345 | 0.064218 | 0.125262 | −0.031739 | 0.269082 |
| 57 | 729.6/184.1>SM:18/18:1 | | | 0.166297 | 0.044619 | −0.040686 | −0.027865 | 0.052039 | 0.00332 | 0.346542 |
| 58 | 731.6/184.1>SM:18/18:0 | | | 0.177202 | 0.050606 | −0.115017 | −0.034289 | 0.037592 | −0.079784 | 0.146137 |
| 59 | 731.8/184.4>SM:d18:1/18:0 | | | 0.177617 | 0.052992 | −0.115591 | −0.041088 | 0.044994 | −0.077715 | 0.124917 |
| 60 | 733.8/184.4>SM:d18:0/18:0 | | | 0.108678 | −0.005076 | −0.203139 | −0.049095 | −0.121503 | −0.056448 | 0.082278 |
| 61 | 757.6/184.1>SM:18/20:1 | | | 0.072954 | −0.191597 | 0.025487 | 0.026063 | 0.027517 | 0.057079 | 0.098408 |
| 62 | 759.6/184.1>SM:18/20:0 | | | −0.138628 | −0.047605 | −0.023747 | 0.162555 | 0.221363 | 0.078181 | 0.078125 |
| 63 | 759.8/184.4>SM:d18:1/20:0 | | | −0.133676 | −0.041488 | −0.02293 | 0.163623 | 0.222516 | 0.083383 | 0.080458 |
| 64 | 761.8/184.4>SM:d18:0/20:0 | | | −0.087383 | −0.076648 | −0.202983 | −0.079866 | −0.103958 | 0.195487 | −0.017219 |
| 65 | 773.6/184.1>SM:18/21:0 | | | 0.062995 | −0.075392 | 0.248463 | 0.028988 | 0.010502 | 0.046947 | 0.138379 |
| 66 | 787.6/184.1>SM:18/22:0 | | | −0.047036 | −0.07085 | 0.189389 | 0.237948 | −0.047586 | −0.099195 | −0.014702 |
| 67 | 787.9/184.4>SM:d18:1/22:0 | | | −0.002832 | −0.052333 | 0.210723 | 0.234121 | −0.04487 | −0.143759 | −0.070552 |
| 68 | 789.9/184.4>SM:d18:0/22:0 | | | −0.024043 | −0.184906 | −0.003083 | 0.044162 | −0.182462 | −0.05006 | −0.072662 |
| 69 | 813.6/184.1>SM:18/24:1 | | | 0.194602 | 0.070344 | −0.008136 | −0.062272 | 0.018756 | −0.077431 | −0.099914 |
| 70 | 813.9/184.4>SM:d18:1/24:1 | | | 0.19116 | 0.069747 | −0.005777 | −0.070742 | 0.034726 | −0.06122 | −0.124911 |
| 71 | 815.6/184.1>SM:18/24:0 | | | 0.159363 | 0.061639 | 0.126831 | 0.014389 | −0.011496 | −0.150537 | −0.166856 |
| 72 | 815.9/184.4>SM:d18:0/24:1 | | | 0.155088 | 0.052273 | 0.125887 | 0.035572 | 0.003477 | −0.175547 | −0.149638 |
| 73 | 817.9/184.4>SM:d18:0/24:0 | | | 0.051608 | −0.167417 | 0.083564 | 0.021214 | 0.033368 | −0.236814 | −0.059018 |
| 74 | 841.9/184.4>SM:d18:1/26:1 | | | 0.069608 | −0.191903 | −0.051959 | −0.047083 | 0.040654 | −0.174985 | −0.001794 |
| 75 | 843.9/184.4>SM:d18:0/26:1 | | | −0.099793 | −0.121445 | −0.046608 | −0.085257 | 0.082891 | −0.182677 | 0.130758 |
| 76 | 843.9/184.4>SM:d18:1/26:0 | | | −0.100002 | −0.120435 | −0.045562 | −0.085924 | 0.081284 | −0.184259 | 0.132051 |
| 77 | 845.9/184.4>SM:d18:0/26:0 | | | −0.110449 | −0.108505 | −0.061291 | −0.120914 | 0.046226 | −0.123136 | 0.13281 |
| | I | J | K | L | M | N | O | P | Q | R |
| 1 | −0.17576 | −0.088068 | −0.01078 | −0.105942 | 0.015303 | −0.018944 | −0.131115 | −0.024904 | 0.200233 | 0.151066 |
| 2 | −0.272092 | 0.073641 | −0.361804 | 0.057305 | 0.123679 | 0.218042 | −0.0173 | 0.09317 | −0.200065 | −0.029733 |
| 3 | −0.193758 | 0.143015 | −0.029671 | 0.069318 | 0.09964 | 0.020918 | −0.049638 | 0.094867 | 0.039896 | −0.039632 |
| 4 | −0.1965 | 0.0443 | −0.043598 | 0.145636 | 0.030338 | 0.046773 | −0.14231 | −0.000966 | −0.060523 | 0.039228 |
| 5 | −0.08763 | 0.071248 | 0.049475 | 0.120998 | 0.239979 | 0.184009 | 0.181092 | 0.065072 | −0.294644 | 0.024779 |
| 6 | −0.095893 | −0.008414 | 0.028909 | 0.060456 | 0.109542 | −0.26485 | −0.064384 | 0.263909 | 0.048481 | −0.219226 |
| 7 | −0.014925 | 0.267879 | −0.024147 | 0.013017 | −0.105456 | −0.219919 | −0.005277 | 0.01803 | 0.167316 | −0.108755 |
| 8 | −0.019339 | 0.192187 | −0.003123 | 0.032478 | 0.000675 | −0.167004 | −0.110314 | 0.09505 | 0.166455 | −0.108756 |
| 9 | 0.039954 | −0.077872 | −0.121467 | −0.343995 | −0.045764 | 0.152489 | 0.074984 | 0.116459 | 0.072797 | 0.033279 |
| 10 | 0.062086 | −0.061181 | −0.120618 | −0.332756 | −0.025676 | 0.183852 | 0.050833 | 0.099438 | 0.038744 | 0.043468 |
| 11 | −0.013125 | −0.022358 | 0.016942 | −0.002348 | 0.114395 | 0.072246 | −0.045094 | −0.078133 | 0.054438 | −0.034327 |
| 12 | −0.028447 | −0.014088 | 0.13105 | −0.373853 | 0.067988 | 0.212805 | −0.088383 | 0.106668 | 0.243306 | 0.027498 |
| 13 | 0.151788 | 0.099166 | 0.003314 | −0.109964 | −0.045966 | −0.042824 | 0.015693 | −0.162404 | −0.136537 | 0.120004 |
| 14 | 0.060454 | −0.216702 | 0.096219 | 0.116223 | −0.062829 | 0.062256 | −0.106818 | −0.10947 | 0.106976 | −0.006014 |
| 15 | 0.020162 | −0.057835 | 0.239394 | −0.119002 | −0.192807 | −0.067396 | 0.039554 | −0.088035 | 0.235275 | −0.006613 |
| 16 | 0.11576 | 0.101409 | 0.099928 | −0.087474 | 0.251411 | −0.01449 | −0.023652 | 0.058471 | −0.134714 | 0.047557 |

APPENDIX B9-continued

PCA Transformation Matrix (77 × 77; Early/Late)

| | | | | | | | | | | |
|---|---|---|---|---|---|---|---|---|---|---|
| 17 | 0.044491 | −0.183329 | −0.117049 | −0.087962 | −0.104558 | −0.058088 | 0.299174 | −0.057585 | −0.035404 | −0.099534 |
| 18 | −0.040972 | −0.18584 | 0.042353 | −0.029738 | −0.065394 | 0.126432 | −0.041973 | −0.174205 | 0.086233 | −0.27591 |
| 19 | −0.010243 | −0.050863 | 0.185995 | 0.0536 | 0.118155 | −0.158564 | −0.139331 | −0.069501 | 0.029896 | 0.222678 |
| 20 | 0.110897 | 0.05082 | 0.164925 | −0.065909 | 0.091471 | −0.158114 | −0.116693 | 0.06433 | −0.199131 | 0.147236 |
| 21 | −0.002306 | −0.026163 | −0.07004 | 0.114075 | −0.12416 | −0.104268 | 0.155872 | 0.295312 | 0.141985 | 0.140137 |
| 22 | −0.072547 | 0.108249 | −0.054653 | −0.028453 | −0.059579 | 0.122216 | 0.043416 | −0.022577 | 0.070402 | 0.148961 |
| 23 | 0.00728 | 0.00944 | −0.081233 | 0.057414 | −0.139904 | −0.019318 | −0.060321 | −0.185734 | −0.088667 | 0.031971 |
| 24 | 0.109988 | −0.010236 | −0.119297 | 0.009034 | −0.072646 | −0.03116 | −0.099982 | −0.158255 | −0.094499 | −0.104935 |
| 25 | −0.091573 | −0.184804 | 0.058742 | 0.007842 | −0.176434 | 0.103911 | 0.003142 | 0.042098 | −0.193824 | 0.019713 |
| 26 | −0.106796 | −0.25011 | 0.04403 | 0.068353 | −0.158395 | 0.097612 | 0.02591 | −0.09539 | 0.030312 | −0.091591 |
| 27 | 0.050674 | 0.069914 | 0.104662 | −0.017301 | 0.135396 | −0.140604 | 0.052155 | 0.153272 | 0.059826 | −0.077485 |
| 28 | 0.106879 | 0.099303 | 0.058688 | −0.120504 | 0.09983 | −0.142494 | −0.102858 | −0.065656 | −0.125227 | −0.234819 |
| 29 | 0.103805 | −0.179457 | 0.011339 | −0.148961 | 0.077205 | −0.103961 | −0.061164 | 0.238046 | −0.154212 | −0.113741 |
| 30 | 0.019591 | −0.232153 | −0.05402 | −0.061935 | 0.025144 | −0.05303 | 0.060765 | 0.097951 | 0.076525 | 0.113473 |
| 31 | 0.00042 | 0.110716 | 0.219782 | 0.052114 | 0.090421 | 0.08191 | 0.113426 | −0.106364 | 0.166313 | 0.156383 |
| 32 | 0.057518 | 0.066715 | 0.159865 | 0.120967 | −0.037447 | 0.030709 | −0.079649 | −0.024036 | 0.071004 | −0.078791 |
| 33 | 0.069729 | 0.008803 | 0.119516 | 0.124429 | −0.087764 | −0.004032 | −0.01199 | 0.046978 | −0.012807 | −0.090691 |
| 34 | 0.010082 | 0.116272 | −0.041405 | 0.02563 | −0.222591 | 0.109351 | 0.282124 | −0.060816 | −0.118156 | 0.145288 |
| 35 | −0.128396 | −0.072565 | 0.134707 | 0.062828 | −0.104612 | 0.041979 | −0.038654 | 0.115393 | 0.005299 | 0.106946 |
| 36 | −0.093461 | −0.162403 | 0.106942 | 0.015577 | −0.129601 | 0.084442 | 0.007072 | 0.167728 | −0.149885 | −0.009048 |
| 37 | −0.007171 | −0.133768 | −0.037718 | 0.045161 | 0.103419 | 0.059252 | 0.030771 | 0.052922 | 0.157253 | −0.253287 |
| 38 | 0.044881 | −0.02591 | −0.051722 | −0.009447 | 0.095991 | −0.154528 | 0.098753 | −0.122951 | 0.028895 | 0.023722 |
| 39 | 0.138621 | 0.005631 | 0.019776 | −0.054161 | −0.007498 | −0.073796 | −0.103689 | 0.079469 | −0.006842 | 0.063704 |
| 40 | 0.125075 | −0.148926 | 0.155386 | −0.062484 | 0.11656 | −0.094251 | −0.00439 | 0.12394 | −0.108604 | 0.051144 |
| 41 | 0.149067 | −0.327506 | −0.019096 | 0.075044 | 0.203038 | −0.188192 | 0.186343 | −0.179141 | 0.126232 | 0.110013 |
| 42 | −0.019381 | 0.052695 | −0.065339 | 0.106417 | −0.040346 | −0.128917 | 0.111582 | −0.093955 | 0.114822 | 0.051395 |
| 43 | 0.023662 | 0.057978 | −0.110553 | 0.018381 | −0.163066 | −0.08575 | −0.169728 | −0.011343 | 0.076795 | 0.002673 |
| 44 | 0.057009 | 0.204266 | 0.030956 | 0.006059 | −0.136417 | 0.038453 | 0.004546 | 0.014216 | 0.03414 | 0.049815 |
| 45 | 0.044701 | 0.128235 | 0.008964 | 0.131352 | 0.017988 | 0.184294 | −0.099622 | 0.017575 | 0.214338 | −0.053481 |
| 46 | −0.016597 | 0.007785 | 0.031335 | 0.190557 | −0.016029 | 0.148621 | −0.08332 | −0.030782 | 0.167449 | −0.070112 |
| 47 | 0.010495 | 0.027024 | −0.018659 | 0.080552 | 0.022187 | −0.006329 | 0.103886 | 0.078027 | 0.098207 | −0.065897 |
| 48 | 0.0278 | 0.076327 | 0.002623 | 0.034471 | −0.005279 | −0.054179 | 0.105721 | 0.098773 | 0.004565 | −0.001645 |
| 49 | 0.15946 | 0.199431 | 0.028025 | −0.117846 | −0.098766 | −0.020539 | 0.044926 | −0.056198 | −0.031859 | 0.197151 |
| 50 | 0.243957 | 0.181378 | −0.129031 | 0.005225 | 0.034317 | 0.155342 | −0.134496 | −0.15319 | 0.093243 | 0.126204 |
| 51 | 0.145751 | −0.050907 | −0.086774 | 0.132506 | 0.101765 | 0.136623 | −0.223217 | −0.081645 | 0.123989 | −0.015752 |
| 52 | 0.056058 | −0.216239 | −0.064859 | −0.004381 | 0.229665 | 0.053254 | −0.04812 | −0.106734 | 0.085619 | 0.09676 |
| 53 | −0.018027 | −0.010534 | 0.011 | −0.008116 | 0.127392 | 0.043062 | −0.051486 | −0.06755 | 0.071939 | −0.060899 |
| 54 | −0.037039 | −0.049616 | 0.013372 | 0.017931 | 0.093974 | 0.02546 | −0.011038 | −0.035686 | 0.068222 | −0.077765 |
| 55 | −0.041507 | 0.00266 | 0.065424 | −0.098675 | 0.076181 | 0.116451 | −0.024691 | 0.01222 | 0.048174 | −0.040869 |
| 56 | −0.005084 | −0.098356 | 0.083921 | 0.094701 | −0.012181 | 0.111346 | −0.340956 | 0.16154 | −0.122188 | 0.337212 |
| 57 | 0.082569 | −0.109391 | 0.066303 | 0.166276 | −0.036523 | 0.070065 | −0.087347 | −0.062217 | −0.112638 | 0.038728 |
| 58 | 0.034741 | 0.075882 | 0.148007 | 0.058901 | −0.087892 | 0.08597 | 0.101246 | 0.028747 | −0.0874 | −0.204875 |
| 59 | 0.033824 | 0.057871 | 0.146928 | 0.065155 | −0.099171 | 0.08495 | 0.116136 | 0.027457 | −0.081594 | −0.196721 |
| 60 | −0.034285 | 0.036265 | 0.301706 | −0.220314 | −0.226164 | 0.090575 | 0.059259 | 0.094172 | 0.049392 | 0.003484 |
| 61 | 0.021759 | −0.105481 | −0.07307 | 0.17682 | −0.159534 | −0.148066 | 0.063129 | 0.289337 | 0.098997 | 0.146631 |
| 62 | 0.016918 | 0.077963 | −0.156144 | −0.109716 | −0.023307 | 0.020938 | −0.077556 | 0.071719 | 0.068583 | −0.082793 |
| 63 | 0.039369 | 0.038955 | −0.157625 | −0.154805 | −0.070059 | 0.025773 | −0.067919 | 0.08764 | 0.025752 | −0.138597 |
| 64 | 0.086153 | −0.085119 | −0.110815 | 0.006763 | −0.148114 | −0.051017 | −0.090858 | −0.1138 | −0.176825 | −0.108861 |
| 65 | 0.192271 | 0.041345 | −0.050555 | −0.167015 | 0.10488 | −0.103805 | −0.050219 | −0.042359 | −0.124883 | −0.108547 |
| 66 | 0.048846 | 0.081951 | 0.223679 | 0.006853 | 0.022492 | 0.14258 | 0.084646 | −0.129836 | −0.059659 | 0.023747 |

APPENDIX B9-continued

PCA Transformation
Matrix (77 × 77; Early/Late)

| | | | | | | | | | | |
|---|---|---|---|---|---|---|---|---|---|---|
| 67 | 0.091347 | 0.022369 | 0.175667 | −0.053374 | −0.046272 | 0.056461 | −0.013477 | −0.075158 | −0.089361 | −0.085832 |
| 68 | 0.081304 | −0.0527 | 0.216834 | 0.12444 | −0.094724 | 0.022307 | −0.129356 | 0.050212 | −0.092568 | −0.180793 |
| 69 | −0.008474 | 0.0166 | −0.034233 | 0.068008 | −0.057769 | −0.119699 | 0.131533 | −0.065708 | −0.006057 | 0.086515 |
| 70 | −0.001205 | 0.003224 | −0.041479 | 0.028735 | −0.068754 | −0.135988 | 0.12639 | −0.081067 | −0.020814 | 0.051961 |
| 71 | −0.002653 | −0.064114 | −0.163532 | −0.052161 | −0.15924 | −0.080072 | −0.099775 | −0.106554 | −0.013387 | 0.019609 |
| 72 | 0.021578 | −0.061853 | −0.107419 | −0.091924 | −0.205847 | −0.100942 | −0.246595 | −0.072571 | −0.094108 | −0.027676 |
| 73 | −0.102495 | 0.002984 | 0.008567 | −0.053839 | −0.205251 | −0.134709 | −0.273059 | 0.050213 | −0.032184 | 0.066195 |
| 74 | 0.054144 | 0.025394 | −0.048335 | 0.039256 | 0.024135 | 0.099391 | −0.020814 | 0.132242 | −0.060577 | 0.024476 |
| 75 | −0.347484 | 0.033302 | 0.08331 | −0.130289 | 0.058178 | −0.108725 | −0.016653 | −0.147566 | −0.042142 | 0.009907 |
| 76 | −0.348655 | 0.030656 | 0.079928 | −0.129524 | 0.056667 | −0.106353 | −0.030162 | −0.154625 | −0.044188 | 0.004257 |
| 77 | −0.364235 | 0.001482 | 0.094389 | −0.130356 | 0.024901 | −0.164778 | −0.006777 | −0.188091 | −0.055915 | 0.007124 |

| | S | T | U | V | W | X | Y | Z | AA | AB |
|---|---|---|---|---|---|---|---|---|---|---|
| 1 | 0.077442 | −0.032993 | −0.120186 | 0.003021 | −0.071116 | 0.011397 | 0.244329 | −0.037457 | 0.117569 | 0.216293 |
| 2 | 0.272797 | −0.197866 | −0.053456 | 0.199295 | 0.000092 | −0.064846 | −0.174826 | 0.211802 | 0.197726 | −0.112249 |
| 3 | −0.072296 | −0.153845 | −0.057089 | −0.014051 | 0.083504 | −0.091726 | 0.119784 | −0.285285 | −0.293919 | 0.178463 |
| 4 | −0.067435 | 0.04586 | −0.049613 | −0.110154 | 0.02006 | 0.083687 | 0.095371 | −0.128589 | −0.258216 | −0.028999 |
| 5 | 0.060207 | −0.01741 | −0.11963 | −0.123756 | 0.090643 | −0.035275 | 0.058441 | 0.036899 | 0.19109 | −0.122299 |
| 6 | −0.179277 | −0.019881 | 0.039738 | −0.063103 | −0.151789 | −0.034452 | −0.203739 | −0.059928 | 0.005274 | 0.183658 |
| 7 | −0.052026 | 0.013984 | 0.087959 | 0.118376 | −0.021421 | 0.126834 | −0.224706 | −0.037581 | 0.114665 | −0.000579 |
| 8 | −0.096796 | 0.040784 | 0.03295 | 0.021395 | 0.188903 | 0.020716 | −0.003845 | 0.185834 | 0.128871 | 0.082839 |
| 9 | −0.208561 | 0.004969 | 0.190664 | −0.155246 | 0.050607 | −0.019769 | −0.024326 | 0.124601 | −0.11711 | 0.017664 |
| 10 | −0.256149 | −0.049884 | 0.223437 | +310.260997 | 0.02103 | −0.033581 | −0.154088 | 0.036682 | −0.093512 | 0.025027 |
| 11 | −0.044952 | 0.194505 | −0.078281 | 0.191283 | 0.113254 | 0.118784 | −0.153853 | 0.078881 | −0.018794 | −0.032988 |
| 12 | 0.082817 | 0.067517 | 0.027702 | 0.106321 | 0.036028 | 0.010006 | −0.100545 | −0.074881 | −0.038787 | −0.208519 |
| 13 | −0.199222 | −0.179457 | −0.273797 | −0.013558 | −0.04153 | 0.008288 | −0.187697 | −0.214879 | 0.212341 | 0.089533 |
| 14 | 0.063502 | −0.096902 | 0.060424 | −0.100277 | 0.14918 | −0.047252 | −0.204179 | 0.159082 | 0.036465 | −0.092907 |
| 15 | 0.211434 | −0.081771 | −0.021214 | −0.010549 | −0.035315 | −0.024683 | 0.04306 | 0.109448 | 0.152721 | 0.232476 |
| 16 | 0.136436 | 0.017958 | 0.277815 | 0.173842 | 0.228693 | 0.093356 | 0.017947 | −0.038534 | 0.066915 | 0.425108 |
| 17 | −0.219976 | 0.161188 | −0.275913 | 0.085678 | −0.080457 | 0.030132 | −0.125635 | 0.059231 | 0.034319 | 0.23586 |
| 18 | 0.032494 | −0.189236 | 0.085976 | 0.217735 | −0.228031 | −0.227729 | −0.064998 | 0.142885 | −0.073486 | −0.034952 |
| 19 | −0.040089 | −0.22489 | −0.211271 | −0.048339 | 0.090167 | −0.138208 | −0.075353 | 0.13428 | −0.024588 | −0.008667 |
| 20 | 0.111143 | −0.218787 | 0.007076 | 0.000074 | 0.056863 | −0.004042 | −0.247882 | 0.051156 | −0.212751 | −0.042447 |
| 21 | 0.036292 | 0.168199 | −0.042361 | 0.104619 | 0.114805 | −0.065774 | 0.048849 | 0.109074 | −0.087649 | −0.023741 |
| 22 | 0.173174 | 0.167153 | −0.051862 | −0.335739 | −0.065735 | 0.029833 | −0.174527 | −0.049946 | −0.012389 | 0.091233 |
| 23 | 0.047791 | 0.098647 | 0.148184 | −0.15135 | −0.090191 | −0.016545 | −0.042752 | −0.049677 | 0.067196 | 0.058096 |
| 24 | −0.130636 | −0.080057 | 0.203074 | 0.159309 | 0.033904 | 0.006353 | 0.072774 | −0.011852 | 0.005888 | −0.107065 |
| 25 | −0.026367 | 0.049821 | 0.15598 | 0.156008 | −0.015817 | −0.134622 | −0.027724 | −0.217579 | 0.024124 | 0.093983 |
| 26 | 0.057513 | −0.03199 | −0.002158 | 0.068777 | −0.016013 | −0.006783 | 0.090746 | 0.039528 | −0.121426 | −0.029762 |
| 27 | 0.045877 | −0.044973 | 0.123435 | 0.073434 | −0.047073 | −0.068734 | 0.059056 | 0.152989 | −0.005061 | −0.154038 |
| 28 | 0.125564 | 0.16546 | 0.038043 | −0.195601 | −0.113765 | 0.014241 | 0.108168 | −0.076807 | −0.142505 | −0.074579 |
| 29 | −0.057244 | −0.072767 | 0.0029 | 0.024104 | −0.134428 | −0.032241 | 0.053144 | −0.055555 | 0.135935 | −0.05726 |
| 30 | 0.148558 | −0.227868 | 0.0336 | 0.165059 | 0.058904 | 0.368521 | −0.078177 | −0.026056 | −0.029446 | −0.123401 |
| 31 | −0.058708 | −0.070735 | 0.102922 | −0.028201 | −0.121305 | −0.040726 | −0.055802 | 0.041079 | 0.073719 | −0.062108 |
| 32 | −0.032522 | 0.075635 | 0.183151 | 0.073273 | −0.121454 | −0.141896 | −0.064798 | −0.104091 | 0.086172 | −0.111298 |
| 33 | −0.028517 | 0.172406 | −0.019776 | 0.042556 | −0.129467 | 0.062738 | −0.137082 | −0.117614 | 0.089372 | −0.140461 |
| 34 | 0.122952 | 0.131685 | 0.112545 | 0.217809 | −0.062825 | 0.107872 | −0.015095 | −0.076219 | −0.067287 | 0.134424 |
| 35 | −0.0739 | 0.08771 | 0.047453 | −0.02796 | −0.004297 | −0.185507 | 0.169707 | 0.080189 | 0.152209 | 0.06142 |
| 36 | −0.034603 | 0.057321 | −0.054331 | −0.19122 | 0.147299 | −0.03735 | −0.078508 | 0.033815 | 0.019874 | 0.020654 |

APPENDIX B9-continued

PCA Transformation
Matrix (77 × 77; Early/Late)

| | | | | | | | | | | |
|---|---|---|---|---|---|---|---|---|---|---|
| 37 | 0.14393 | −0.119279 | 0.012635 | −0.056108 | 0.033806 | 0.310709 | 0.120513 | −0.098312 | −0.129272 | 0.056285 |
| 38 | 0.065011 | 0.149759 | 0.047241 | −0.03597 | 0.029931 | 0.077683 | 0.164039 | 0.056927 | 0.167145 | −0.154804 |
| 39 | −0.05446 | 0.037335 | −0.003876 | 0.0109 | 0.139 | −0.100652 | 0.152433 | 0.212548 | −0.018954 | −0.093608 |
| 40 | −0.018314 | 0.042725 | −0.02745 | −0.057366 | −0.074842 | −0.195417 | 0.046454 | −0.008399 | 0.027407 | −0.022626 |
| 41 | 0.122196 | −0.092279 | −0.045727 | 0.039545 | 0.010267 | 0.039698 | −0.090606 | −0.190279 | −0.174145 | 0.05274 |
| 42 | −0.061869 | −0.118867 | 0.09798 | 0.02973 | −0.13731 | −0.096411 | 0.053093 | 0.07689 | 0.087435 | −0.091041 |
| 43 | 0.104634 | 0.019406 | 0.17133 | 0.013561 | 0.019503 | −0.130338 | −0.039478 | −0.136859 | 0.029331 | 0.012283 |
| 44 | 0.066501 | −0.000576 | 0.050459 | 0.023437 | 0.041969 | 0.036707 | −0.01073 | 0.005164 | 0.059697 | −0.099216 |
| 45 | −0.06934 | −0.191493 | −0.048923 | −0.204938 | −0.054775 | 0.137032 | 0.178237 | −0.089862 | 0.068855 | −0.092583 |
| 46 | 0.016814 | −0.010182 | −0.037531 | −0.111456 | 0.146174 | 0.034685 | −0.086457 | −0.134159 | 0.137869 | 0.096603 |
| 47 | −0.128367 | −0.086221 | 0.084802 | 0.118956 | 0.006099 | −0.043451 | 0.070601 | −0.078506 | 0.071277 | 0.071428 |
| 48 | −0.052338 | −0.113142 | 0.031086 | 0.039252 | −0.056563 | 0.092632 | 0.097123 | −0.082578 | 0.031734 | −0.072855 |
| 49 | −0.01468 | 0.025599 | −0.063605 | 0.145662 | 0.044877 | 0.047942 | 0.006569 | −0.074409 | −0.178639 | −0.190068 |
| 50 | −0.073446 | 0.031995 | −0.124847 | 0.137009 | −0.017289 | −0.190695 | 0.109721 | 0.106489 | −0.289338 | 0.035354 |
| 51 | −0.000833 | 0.133514 | −0.179929 | 0.03985 | −0.004409 | −0.094521 | −0.084986 | 0.213386 | −0.028935 | 0.242291 |
| 52 | −0.082412 | 0.145032 | 0.084828 | 0.065776 | 0.154355 | −0.164912 | 0.15586 | −0.31995 | 0.251271 | −0.128588 |
| 53 | −0.09594 | 0.116022 | 0.037357 | 0.179638 | −0.023189 | −0.01003 | −0.013228 | −0.05181 | −0.119262 | 0.034911 |
| 54 | −0.024911 | 0.230877 | −0.08164 | 0.007816 | −0.026774 | 0.123586 | −0.077329 | 0.165991 | −0.043363 | −0.003781 |
| 55 | −0.056034 | 0.133135 | −0.176891 | 0.136887 | 0.007934 | 0.074784 | 0.114152 | −0.034605 | 0.013369 | −0.074482 |
| 56 | −0.096642 | 0.043626 | 0.127064 | 0.120831 | −0.408903 | 0.351749 | 0.130582 | 0.153121 | 0.005424 | 0.08819 |
| 57 | −0.020304 | −0.055282 | 0.108493 | −0.02745 | 0.208507 | −0.080779 | −0.125237 | −0.089569 | −0.079227 | −0.035521 |
| 58 | 0.084039 | −0.091519 | 0.036272 | 0.016713 | 0.003452 | −0.072905 | 0.058873 | 0.029401 | −0.187494 | 0.072733 |
| 59 | 0.104098 | −0.060581 | −0.017676 | −0.038419 | 0.02391 | −0.047033 | 0.058203 | 0.127401 | −0.166107 | 0.037772 |
| 60 | 0.150668 | −0.072346 | −0.26299 | 0.062552 | −0.038861 | −0.058018 | 0.122212 | −0.146001 | 0.05645 | −0.083899 |
| 61 | 0.07021 | 0.132727 | 0.015854 | 0.06873 r | 0.252939 | −0.107138 | 0.093539 | −0.004594 | −0.116979 | −0.007513 |
| 62 | 0.008736 | −0.091897 | −0.07832 | 0.108267 | 0.093782 | −0.08549 | 0.029395 | −0.136815 | −0.003262 | −0.012891 |
| 63 | −0.064799 | −0.115851 | −0.19104 | 0.080664 | 0.176265 | 0.035208 | 0.043578 | 0.030678 | 0.137542 | 0.000693 |
| 64 | −0.188222 | 0.016431 | −0.073911 | 0.033451 | 0.097158 | 0.123189 | 0.139018 | 0.041373 | 0.007165 | −0.096043 |
| 65 | 0.348666 | 0.181832 | −0.095217 | −0.030879 | −0.102891 | −0.119419 | 0.123322 | 0.025753 | 0.040966 | 0.100724 |
| 66 | −0.11127 | −0.033862 | 0.098887 | 0.095639 | 0.250107 | 0.047864 | 0.028785 | 0.01447 | 0.101537 | 0.100469 |
| 67 | −0.083371 | −0.117068 | 0.072339 | 0.004585 | 0.190285 | 0.198515 | 0.141375 | 0.139773 | 0.093602 | 0.219183 |
| 68 | −0.124104 | 0.138069 | −0.165877 | 0.048571 | 0.124069 | 0.141061 | −0.014726 | −0.029567 | −0.029517 | −0.15115 |
| 69 | −0.08975 | −0.107919 | −0.037964 | −0.05919 | −0.026021 | −0.040891 | 0.08197 | 0.011952 | −0.048091 | −0.018874 |
| 70 | −0.146973 | −0.157657 | −0.061874 | −0.072212 | −0.062312 | 0.075268 | 0.18004 | 0.143563 | −0.028675 | −0.017722 |
| 71 | 0.124834 | −0.042546 | 0.117459 | −0.120632 | 0.17042 | −0.039582 | 0.118462 | 0.056493 | 0.064033 | −0.043221 |
| 72 | 0.132271 | −0.074929 | 0.009717 | −0.069237 | 0.007607 | 0.073811 | 0.094647 | −0.080592 | 0.019272 | 0.057443 |
| 73 | 0.036743 | −0.002497 | −0.139788 | 0.108739 | 0.050305 | 0.005577 | −0.199228 | −0.092853 | 0.005312 | 0.015035 |
| 74 | −0.08778 | −0.143431 | −0.062466 | 0.162133 | −0.133222 | −0.222016 | 0.094027 | −0.057091 | 0.016509 | 0.144692 |
| 75 | −0.066412 | 0.036875 | 0.01731 | 0.041346 | 0.045282 | −0.017031 | 0.036519 | 0.015405 | −0.073839 | −0.022227 |
| 76 | −0.065394 | 0.042551 | 0.033774 | 0.049876 | 0.052348 | −0.019444 | 0.05038 | −0.003861 | −0.067715 | −0.003716 |
| 77 | −0.06893 | 0.069616 | 0.049507 | 0.071251 | 0.084448 | −0.023554 | 0.004735 | 0.092517 | −0.045433 | −0.034509 |

| | AC | AD | AE | AF | AG | AH | AI | AJ | AK | AL |
|---|---|---|---|---|---|---|---|---|---|---|
| 1 | 0.04201 | −0.100807 | −0.035313 | −0.177364 | −0.076136 | 0.177 | 0.07421 | −0.316918 | −0.085818 | −0.054812 |
| 2 | 0.095255 | −0.140506 | −0.102445 | 0.115844 | 0.129019 | 0.024115 | −0.161823 | 0.030813 | 0.088596 | 0.06049 |
| 3 | −0.221742 | 0.029511 | 0.042088 | −0.059749 | 0.285133 | −0.196169 | −0.035516 | 0.107485 | 0.114295 | −0.09031 |
| 4 | 0.025835 | 0.045532 | 0.050084 | 0.008047 | −0.290654 | −0.02702 | 0.186474 | 0.147957 | −0.101429 | −0.146925 |
| 5 | −0.137246 | 0.165422 | 0.04177 | −0.15349 | −0.054347 | 0.083014 | 0.100204 | −0.055606 | 0.037344 | 0.013674 |
| 6 | 0.159765 | −0.11932 | −0.041464 | 0.02599 | 0.111944 | 0.032006 | 0.170996 | 0.102168 | 0.010801 | 0.136513 |

APPENDIX B9-continued

PCA Transformation
Matrix (77 × 77; Early/Late)

| | | | | | | | | | | |
|---|---|---|---|---|---|---|---|---|---|---|
| 7 | 0.104894 | −0.086761 | 0.221215 | −0.016252 | −0.194706 | 0.101665 | −0.076023 | 0.052235 | −0.030785 | 0.01254 |
| 8 | −0.075616 | 0.307686 | −0.011755 | 0.169561 | 0.090887 | −0.050099 | −0.058667 | −0.132708 | −0.024713 | 0.047054 |
| 9 | 0.1705 | −0.005752 | −0.055884 | −0.028748 | 0.003541 | 0.000293 | 0.063915 | 0.086397 | 0.052716 | −0.121744 |
| 10 | 0.118714 | 0.047725 | −0.004662 | 0.02545 | −0.026989 | −0.038494 | −0.017824 | −0.088012 | −0.054568 | 0.144802 |
| 11 | −0.05098 | −0.046887 | 0.058869 | −0.053099 | −0.103077 | −0.012238 | 0.065998 | −0.216431 | 0.150175 | −0.061151 |
| 12 | −0.099489 | −0.002082 | 0.060099 | −0.070036 | 0.186303 | −0.037043 | −0.132044 | 0.185134 | 0.091708 | 0.007788 |
| 13 | −0.154951 | −0.128502 | −0.392512 | 0.229761 | 0.023544 | −0.080133 | −0.17526 | −0.031391 | −0.175386 | −0.123806 |
| 14 | −0.173917 | −0.019453 | 0.16954 | −0.143297 | 0.131919 | 0.20679 | −0.010584 | 0.039446 | −0.137834 | −0.014445 |
| 15 | 0.051593 | −0.027763 | 0.002604 | −0.01749 | 0.026906 | −0.033626 | −0.046398 | −0.151271 | 0.0083 | −0.109702 |
| 16 | −0.114733 | 0.072261 | −0.204419 | −0.140536 | 0.065228 | 0.043606 | 0.215333 | 0.014794 | 0.098494 | 0.089101 |
| 17 | −0.257907 | 0.164445 | 0.019381 | −0.1449 | −0.187903 | −0.070775 | 0.063407 | 0.02612 | 0.212485 | 0.050141 |
| 18 | −0.185067 | 0.042899 | −0.05171 | 0.099222 | −0.015452 | 0.080946 | 0.205744 | −0.005383 | 0.247883 | 0.157945 |
| 19 | 0.181207 | −0.040871 | 0.251854 | −0.059332 | −0.118712 | −0.251488 | −0.161539 | 0.103008 | 0.0447 | 0.293043 |
| 20 | 0.07129 | 0.20338 | 0.090589 | 0.165727 | 0.036885 | 0.099088 | 0.099965 | −0.166972 | −0.05115 | −0.092277 |
| 21 | −0.088521 | −0.081891 | −0.072447 | 0.184214 | −0.025032 | 0.048186 | −0.004608 | −0.024494 | 0.033089 | 0.176445 |
| 22 | −0.063198 | 0.010454 | 0.027606 | 0.068044 | 0.111401 | 0.064356 | −0.061281 | −0.128261 | 0.066237 | 0.098552 |
| 23 | −0.067056 | 0.057458 | 0.06409 | 0.031363 | 0.046439 | 0.091409 | −0.012687 | 0.194383 | 0.00587 | 0.070911 |
| 24 | −0.083182 | 0.019427 | −0.007005 | 0.036176 | −0.033711 | −0.037127 | −0.197265 | 0.033421 | 0.105619 | −0.109649 |
| 25 | 0.119627 | 0.032032 | −0.164716 | −0.043488 | 0.097677 | 0.062936 | 0.032102 | 0.018148 | −0.245271 | 0.0338 |
| 26 | 0.105708 | −0.058521 | −0.116892 | −0.014323 | 0.065032 | 0.015827 | 0.02105 | −0.005117 | −0.221257 | 0.03232 |
| 27 | −0.089081 | −0.12617 | −0.102065 | 0.036625 | 0.008661 | 0.184151 | 0.246292 | 0.074471 | −0.149524 | −0.210568 |
| 28 | −0.067794 | −0.122328 | 0.075052 | 0.134301 | 0.110007 | 0.019939 | −0.045928 | −0.008255 | −0.022791 | 0.095482 |
| 29 | −0.126397 | −0.146176 | 0.151844 | −0.15276 | −0.058461 | −0.129106 | 0.009375 | −0.071269 | −0.006167 | 0.227594 |
| 30 | 0.027921 | 0.128867 | −0.089451 | −0.008111 | −0.222072 | −0.295009 | 0.032067 | 0.133419 | −0.123992 | 0.024169 |
| 31 | −0.063016 | 0.020728 | −0.019171 | −0.109776 | −0.077841 | 0.01128 | 0.000937 | 0.13087 | −0.038311 | −0.202096 |
| 32 | 0.12141 | 0.068217 | −0.085872 | 0.03952 | −0.008268 | −0.078761 | −0.101825 | −0.118547 | 0.002485 | −0.07665 |
| 33 | −0.042301 | 0.165192 | 0.002179 | −0.103374 | 0.071168 | −0.139197 | 0.102267 | −0.094965 | 0.126376 | −0.03722 |
| 34 | 0.050457 | 0.101857 | 0.347356 | 0.192616 | 0.121589 | −0.075037 | 0.098889 | −0.026517 | −0.109389 | 0.062243 |
| 35 | 0.062793 | 0.095982 | −0.084377 | −0.172283 | 0.109191 | 0.000706 | −0.236757 | 0.058204 | 0.080035 | 0.026633 |
| 36 | 0.067108 | −0.042874 | 0.116214 | 0.017654 | −0.072284 | −0.022295 | −0.070161 | −0.171152 | 0.12312 | −0.382338 |
| 37 | −0.16395 | −0.054366 | 0.119812 | −0.0651 | 0.083864 | −0.041148 | −0.255105 | −0.202605 | 0.002366 | −0.086149 |
| 38 | 0.065913 | 0.146832 | −0.020277 | −0.26083 | 0.21587 | −0.206817 | 0.062336 | 0.021612 | −0.307842 | 0.093451 |
| 39 | −0.202222 | 0.221512 | −0.103806 | 0.201096 | 0.024034 | −0.080797 | −0.03112 | −0.023193 | −0.094634 | −0.096803 |
| 40 | −0.167098 | −0.097916 | 0.024132 | 0.044445 | −0.106437 | 0.000486 | −0.0041 | 0.012731 | 0.017681 | −0.121024 |
| 41 | 0.172234 | 0.134271 | −0.062308 | 0.141526 | 0.098703 | 0.226298 | −0.044443 | 0.002587 | 0.177799 | −0.081427 |
| 42 | 0.037457 | 0.033589 | 0.020889 | −0.071168 | 0.088613 | −0.12043 | 0.051968 | −0.106186 | 0.137069 | −0.054712 |
| 43 | −0.055809 | 0.113366 | 0.027378 | −0.02758 | −0.135747 | −0.190436 | −0.043583 | −0.058414 | −0.053775 | 0.043065 |
| 44 | −0.007786 | 0.010178 | 0.020601 | 0.000124 | −0.131791 | 0.070186 | 0.036497 | 0.050495 | 0.229014 | −0.21041 |
| 45 | 0.024369 | 0.188492 | −0.209403 | 0.064228 | −0.230127 | 0.201405 | 0.085008 | −0.060448 | 0.088246 | 0.310801 |
| 46 | 0.075305 | −0.172694 | −0.049615 | 0.034084 | 0.014108 | −0.099727 | 0.184943 | 0.268352 | 0.07761 | −0.070935 |
| 47 | 0.059655 | −0.151885 | 0.13199 | −0.028755 | −0.003037 | −0.035038 | 0.036548 | 0.103138 | −0.025636 | −0.144811 |
| 48 | −0.131221 | −0.112691 | 0.059758 | −0.043067 | 0.050051 | 0.03622 | −0.054645 | 0.017884 | −0.042733 | −0.086507 |
| 49 | 0.021621 | −0.246728 | −0.037443 | −0.282414 | 0.048607 | 0.150998 | 0.051396 | −0.053439 | 0.112963 | 0.075921 |
| 50 | −0.009191 | 0.00725 | −0.021852 | −0.132802 | 0.066118 | −0.013659 | 0.029054 | −0.016702 | 0.000179 | 0.08098 |
| 51 | −0.030292 | −0.097715 | 0.073333 | 0.104256 | 0.085178 | −0.226135 | 0.113908 | 0.105642 | −0.13922 | −0.125877 |
| 52 | 0.104965 | 0.14949 | 0.124614 | 0.211383 | −0.000428 | 0.031294 | 0.033171 | 0.059307 | 0.147117 | −0.007998 |
| 53 | 0.026315 | −0.074577 | −0.100444 | 0.057997 | −0.130745 | 0.081556 | −0.215521 | −0.13753 | −0.1323 | −0.017506 |
| 54 | 0.042167 | 0.045125 | −0.0401 | 0.028013 | −0.046902 | 0.166635 | 0.062645 | 0.094321 | −0.223633 | −0.004983 |
| 55 | −0.018155 | −0.004341 | 0.030211 | 0.063596 | −0.052134 | 0.027384 | −0.049806 | 0.072217 | −0.079969 | −0.007804 |
| 56 | 0.044255 | −0.014368 | −0.021315 | 0.094348 | 0.056435 | −0.103047 | 0.040867 | −0.031957 | 0.195917 | −0.061894 |

APPENDIX B9-continued

PCA Transformation
Matrix (77 × 77; Early/Late)

| | | | | | | | | | | |
|---|---|---|---|---|---|---|---|---|---|---|
| 57 | −0.015365 | −0.049041 | 0.050774 | −0.147703 | −0.022499 | −0.056398 | 0.139355 | −0.08311 | 0.034703 | 0.052526 |
| 58 | 0.068511 | 0.135466 | −0.131856 | −0.069913 | −0.147932 | −0.131776 | −0.162463 | −0.0243 | 0.030224 | −0.043839 |
| 59 | 0.126701 | 0.097835 | −0.11903 | −0.058658 | −0.094737 | −0.110541 | 0.004495 | 0.060285 | −0.054397 | −0.012132 |
| 60 | −0.045387 | 0.01213 | 0.064599 | 0.247818 | 0.037843 | −0.066422 | 0.219408 | 0.155771 | −0.016249 | 0.093116 |
| 61 | −0.046429 | −0.10542 | −0.121214 | 0.069526 | −0.078122 | 0.107894 | −0.146041 | 0.09387 | 0.101588 | 0.088606 |
| 62 | 0.191104 | 0.054915 | 0.019652 | −0.059704 | −0.011309 | −0.091894 | 0.065514 | −0.184208 | −0.002172 | −0.087642 |
| 63 | 0.184223 | 0.148165 | 0.070166 | −0.022415 | 0.166378 | 0.053197 | 0.204098 | −0.049657 | 0.011664 | −0.149445 |
| 64 | 0.057006 | −0.043836 | 0.01598 | −0.022171 | −0.025866 | 0.089027 | −0.008524 | 0.126371 | −0.008053 | −0.0198 |
| 65 | 0.333283 | −0.03793 | −0.055254 | −0.069742 | −0.168863 | −0.040577 | −0.083503 | 0.147168 | 0.179232 | −0.084552 |
| 66 | 0.019033 | −0.281617 | 0.004761 | 0.070405 | −0.07177 | −0.06953 | 0.000142 | −0.133779 | −0.058142 | 0.169042 |
| 67 | 0.054636 | 0.024836 | 0.133045 | 0.063658 | 0.013976 | 0.18968 | −0.162631 | 0.246766 | 0.101111 | 0.081218 |
| 68 | 0.204099 | −0.053664 | −0.028273 | 0.052974 | 0.236755 | 0.021163 | 0.0204 | −0.199195 | 0.105842 | 0.09898 |
| 69 | 0.120463 | −0.072885 | −0.09013 | 0.002144 | 0.121036 | −0.023647 | 0.1689 | −0.130348 | 0.066604 | 0.041952 |
| 70 | 0.073776 | 0.026004 | 0.039891 | −0.006302 | 0.246175 | 0.043793 | −0.01128 | 0.112559 | 0.096525 | −0.091305 |
| 71 | −0.117863 | −0.2229 | 0.02508 | 0.079593 | −0.138365 | −0.116103 | 0.262849 | −0.118193 | 0.055401 | −0.034176 |
| 72 | −0.168917 | 0.019961 | 0.051942 | 0.042349 | 0.009703 | 0.109476 | 0.000286 | 0.015384 | −0.021834 | 0.018269 |
| 73 | −0.047851 | 0.178201 | −0.12222 | −0.319531 | 0.020045 | 0.184157 | −0.024413 | 0.159878 | −0.008992 | −0.026296 |
| 74 | 0.015299 | 0.109971 | 0.36119 | 0.004136 | −0.120634 | 0.266661 | −0.063492 | −0.07218 | −0.208278 | −0.015986 |
| 75 | 0.012085 | 0.068153 | 0.011572 | 0.058781 | −0.080331 | 0.01658 | 0.033031 | −0.041596 | −0.005928 | 0.026568 |
| 76 | 0.047053 | 0.067381 | 0.015582 | 0.079031 | −0.064113 | −0.032014 | 0.032621 | −0.023697 | 0.067504 | 0.045015 |
| 77 | −0.059024 | −0.086958 | −0.033269 | 0.023134 | 0.02978 | −0.031449 | −0.024763 | 0.012861 | 0.074537 | −0.055198 |

| | AM | AN | AO | AP | AQ | AR | AS | AT | AU | AV |
|---|---|---|---|---|---|---|---|---|---|---|
| 1 | 0.138737 | −0.018449 | −0.14062 | 0.122001 | −0.051816 | 0.14887 | −0.018784 | −0.101135 | −0.123599 | −0.120974 |
| 2 | 0.090789 | 0.180351 | 0.032298 | −0.074861 | −0.187413 | −0.088661 | 0.100325 | 0.080277 | −0.042351 | 0.045274 |
| 3 | −0.136626 | 0.156858 | 0.189497 | −0.024523 | 0.021242 | 0.158241 | 0.155396 | 0.169994 | 0.087733 | −0.01561 |
| 4 | 0.208207 | −0.050952 | 0.036944 | −0.010098 | −0.015294 | −0.331314 | −0.022569 | −0.095782 | −0.030741 | −0.006409 |
| 5 | −0.267285 | −0.097947 | −0.075484 | 0.101866 | 0.217867 | 0.116675 | −0.188768 | −0.049115 | 0.031258 | −0.004865 |
| 6 | −0.052885 | −0.006025 | 0.060635 | 0.03364 | −0.025166 | −0.090035 | −0.18162 | −0.188868 | −0.144581 | 0.043759 |
| 7 | −0.11004 | 0.07777 | −0.123905 | 0.018549 | 0.12468 | 0.099321 | 0.081482 | −0.009858 | 0.092749 | −0.036561 |
| 8 | 0.06649 | −0.316638 | −0.033662 | −0.140377 | −0.024081 | 0.213068 | −0.091464 | 0.192942 | 0.049406 | 0.039606 |
| 9 | −0.157408 | −0.023128 | −0.018464 | 0.034646 | 0.146698 | −0.040628 | 0.158032 | 0.153437 | −0.153151 | 0.08112 |
| 10 | 0.002543 | 0.003926 | 0.085566 | 0.118005 | −0.136002 | 0.070094 | −0.016046 | −0.138823 | 0.219002 | 0.040258 |
| 11 | 0.021721 | −0.118048 | 0.185679 | 0.060531 | −0.245613 | 0.050948 | −0.145862 | 0.075716 | −0.221516 | −0.085432 |
| 12 | 0.126008 | −0.150821 | 0.009008 | −0.021394 | 0.059183 | 0.012624 | −0.109708 | −0.136712 | −0.124738 | −0.139788 |
| 13 | −0.048196 | −0.12504 | 0.00742 | 0.086401 | 0.116801 | −0.080442 | −0.059972 | −0.066783 | −0.119921 | −0.023248 |
| 14 | 0.077026 | 0.160192 | 0.00651 | 0.031084 | 0.235433 | −0.006202 | 0.027281 | −0.048448 | −0.058469 | −0.098129 |
| 15 | −0.153289 | 0.156844 | 0.179298 | −0.159031 | −0.10491 | −0.088227 | −0.012277 | 0.021454 | 0.071141 | 0.001823 |
| 16 | 0.031968 | 0.015656 | 0.000594 | 0.07423 | 0.109094 | −0.167128 | −0.013535 | 0.006423 | 0.022766 | 0.062963 |
| 17 | 0.085736 | 0.14059 | −0.116095 | −0.149491 | −0.047896 | −0.0865 | −0.006817 | 0.164951 | −0.049249 | 0.027241 |
| 18 | 0.079499 | −0.125949 | 0.068823 | 0.033505 | 0.001891 | 0.078805 | −0.033724 | −0.184591 | 0.170588 | 0.042238 |
| 19 | −0.096785 | −0.061089 | 0.136567 | 0.081534 | 0.060931 | −0.098077 | 0.107066 | 0.056573 | −0.08655 | −0.051878 |
| 20 | 0.018406 | 0.267417 | −0.164376 | −0.211369 | 0.009674 | 0.180844 | −0.080273 | −0.080061 | 0.0213 | 0.070894 |
| 21 | 0.03175 | 0.046693 | 0.048271 | −0.010727 | −0.056792 | −0.104099 | −0.029124 | −0.015296 | 0.018855 | −0.019397 |
| 22 | 0.047896 | −0.192643 | −0.00051 | −0.021969 | 0.091287 | 0.037214 | 0.015081 | 0.077433 | −0.207997 | −0.069525 |
| 23 | −0.07147 | −0.186045 | 0.07645 | −0.17288 | 0.101817 | 0.096393 | −0.022981 | −0.066188 | 0.154062 | −0.029284 |
| 24 | −0.107191 | −0.037733 | −0.018452 | 0.202066 | −0.049951 | 0.093801 | −0.067333 | 0.194597 | 0.003819 | −0.089951 |
| 25 | 0.228165 | 0.074031 | 0.056598 | −0.067191 | 0.07121 | 0.115455 | −0.014798 | 0.122604 | −0.011642 | −0.322729 |
| 26 | −0.275829 | −0.060687 | −0.047374 | −0.025212 | 0.14518 | −0.055911 | −0.221444 | 0.05819 | −0.172388 | 0.185064 |

APPENDIX B9-continued

PCA Transformation
Matrix (77 × 77; Early/Late)

| | | | | | | | | | | |
|---|---|---|---|---|---|---|---|---|---|---|
| 27 | −0.216527 | −0.195448 | −0.069942 | 0.047152 | −0.080725 | −0.043355 | 0.227626 | 0.225087 | −0.014587 | −0.195856 |
| 28 | 0.186673 | 0.117206 | −0.270855 | 0.071105 | −0.162975 | −0.104105 | −0.035761 | 0.108702 | −0.103176 | −0.2565 |
| 29 | −0.121443 | −0.04655 | −0.075263 | 0.049217 | 0.016448 | −0.054224 | −0.026484 | 0.062686 | 0.02577 | −0.080149 |
| 30 | 0.168841 | −0.099852 | −0.154188 | −0.131618 | 0.097515 | 0.032276 | −0.053497 | 0.072129 | 0.02976 | −0.066938 |
| 31 | 0.042036 | 0.098702 | −0.149433 | 0.092419 | −0.319444 | 0.067613 | −0.092166 | −0.022288 | −0.073444 | 0.154513 |
| 32 | 0.05081 | 0.086905 | 0.098481 | 0.028508 | 0.137015 | −0.254842 | −0.128231 | 0.228427 | 0.089212 | 0.158842 |
| 33 | −0.003815 | 0.250296 | −0.027747 | 0.047511 | 0.247056 | 0.126817 | 0.187673 | −0.163068 | −0.068039 | −0.085961 |
| 34 | −0.140713 | −0.022738 | 0.063714 | 0.199405 | −0.137845 | −0.051771 | 0.110429 | −0.139782 | −0.094655 | 0.040791 |
| 35 | 0.054546 | 0.010465 | −0.281754 | −0.03672 | 0.013773 | −0.123458 | 0.300694 | −0.030371 | −0.086588 | 0.157161 |
| 36 | 0.051281 | −0.017342 | 0.05383 | −0.07857 | −0.070428 | 0.021434 | −0.137924 | 0.12144 | 0.313921 | −0.146768 |
| 37 | −0.124389 | −0.034818 | −0.147438 | 0.026825 | −0.00447 | −0.095453 | 0.064856 | −0.09026 | 0.069474 | 0.147612 |
| 38 | 0.059444 | 0.021971 | 0.333967 | 0.042761 | −0.159995 | 0.001487 | −0.118054 | 0.019779 | 0.155609 | 0.000475 |
| 39 | 0.04809 | 0.013286 | 0.050819 | 0.072611 | −0.013657 | 0.04621 | 0.109571 | −0.220556 | −0.19727 | 0.173071 |
| 40 | 0.077575 | 0.150382 | 0.287847 | 0.012605 | −0.134884 | 0.026558 | 0.043922 | −0.069225 | −0.058166 | 0.087147 |
| 41 | −0.004622 | −0.083145 | 0.142342 | 0.13465 | −0.013084 | 0.019134 | 0.185029 | 0.068397 | −0.050928 | −0.089717 |
| 42 | 0.174381 | −0.041949 | −0.091563 | 0.193984 | 0.12733 | −0.046972 | −0.018311 | −0.083221 | −0.032917 | −0.089299 |
| 43 | −0.016348 | 0.147677 | −0.081875 | 0.051366 | −0.097261 | 0.046256 | −0.007916 | 0.089323 | −0.14921 | −0.014092 |
| 44 | 0.035009 | −0.113199 | 0.128898 | 0.072471 | 0.121811 | −0.303733 | 0.051435 | −0.047975 | 0.04227 | −0.119229 |
| 45 | −0.016332 | 0.184966 | 0.211801 | −0.010197 | −0.004255 | 0.008502 | 0.057838 | 0.130138 | 0.013965 | −0.105319 |
| 46 | 0.023305 | 0.023611 | −0.106062 | 0.114657 | −0.179083 | 0.289125 | −0.138114 | −0.081602 | −0.03813 | 0.15393 |
| 47 | 0.133189 | −0.07857 | 0.116985 | −0.332583 | 0.108359 | 0.183842 | 0.030334 | 0.131079 | −0.242623 | 0.046175 |
| 48 | 0.202246 | −0.127667 | 0.121337 | −0.249109 | 0.0510811 | −0.088805 | 0.052985 | −0.331659 | 0.125447 | 0.097604 |
| 49 | −0.093354 | 0.118716 | 0.036244 | −0.049364 | 0.078732 | 0.056699 | −0.211779 | 0.110962 | −0.049553 | 0.197169 |
| 50 | 0.038822 | −0.004578 | −0.124482 | −0.281866 | −0.015495 | −0.041972 | −0.066438 | −0.01835 | 0.063241 | −0.121391 |
| 51 | −0.06858 | 0.001896 | −0.063059 | 0.125207 | 0.162813 | −0.099897 | −0.034098 | −0.015041 | 0.164518 | −0.124956 |
| 52 | −0.247522 | 0.049288 | −0.192399 | −0.281473 | −0.100366 | −0.138952 | −0.099216 | −0.12257 | −0.018319 | −0.071012 |
| 53 | −0.043807 | 0.053859 | −0.07575 | 0.051506 | 0.036453 | −0.017552 | −0.005408 | −0.038436 | 0.196634 | 0.13994 |
| 54 | −0.051775 | 0.13568 | 0.004099 | −0.082758 | 0.0625 | −0.045512 | 0.123816 | 0.069462 | 0.076255 | 0.114855 |
| 55 | 0.084322 | 0.078507 | 0.118761 | 0.171022 | 0.157769 | 0.222163 | 0.203851 | 0.056316 | 0.062225 | −0.036861 |
| 56 | −0.11921 | 0.000121 | 0.02922 | 0.000982 | 0.002932 | 0.10026 | −0.035438 | 0.0216 | 0.003899 | −0.036845 |
| 57 | 0.221369 | −0.184918 | −0.096691 | 0.175311 | −0.093433 | −0.039462 | 0.137562 | 0.192092 | 0.042098 | 0.258733 |
| 58 | −0.080234 | −0.033258 | 0.006552 | −0.0004471 | −0.045322 | 0.036925 | −0.015073 | −0.124345 | −0.147034 | −0.119917 |
| 59 | −0.092424 | −0.047685 | −0.008351 | −0.051245 | −0.048498 | 0.041241 | −0.062433 | −0.128275 | −0.169074 | −0.177707 |
| 60 | −0.007371 | −0.020446 | −0.13074 | 0.064603 | −0.04846 | −0.021792 | −0.009923 | 0.196218 | 0.177852 | 0.12051 |
| 61 | −0.000383 | 0.06216 | −0.043211 | 0.222005 | 0.111449 | 0.124937 | −0.227021 | −0.098096 | 0.102629 | −0.070196 |
| 62 | −0.09447 | 0.036838 | 0.062247 | 0.0576 | 0.027268 | −0.082268 | −0.055586 | −0.151624 | 0.049662 | −0.040463 |
| 63 | 0.115132 | 0.15207 | −0.036284 | 0.158336 | 0.075394 | −0.095573 | 0.001351 | −0.021466 | −0.054222 | 0.001922 |
| 64 | −0.044985 | 0.04321 | 0.002423 | 0.029341 | −0.142567 | 0.184867 | 0.156123 | −0.139488 | −0.056653 | 0.020255 |
| 65 | 0.106864 | −0.126447 | 0.030484 | 0.008419 | 0.129837 | 0.211327 | 0.048725 | −0.031438 | 0.105454 | 0.158948 |
| 66 | 0.031611 | −0.00536 | −0.049766 | −0.039543 | −0.041181 | 0.037555 | 0.19078 | −0.12817 | 0.158395 | −0.196941 |
| 67 | 0.092924 | 0.113048 | 0.029194 | −0.004017 | 0.001897 | −0.109624 | −0.119254 | 0.025222 | −0.08291 | −0.040737 |
| 68 | 0.034691 | −0.189286 | 0.060744 | −0.100273 | −0.033295 | −0.058383 | 0.052314 | −0.004673 | −0.103124 | 0.086948 |
| 69 | 0.041158 | −0.09507 | −0.181487 | −0.076173 | 0.00453 | 0.062538 | 0.166667 | −0.013371 | 0.155895 | 0.039229 |
| 70 | 0.059964 | 0.047887 | −0.08306 | 0.103428 | −0.027484 | −0.054314 | −0.235939 | 0.053287 | 0.100349 | −0.145003 |
| 71 | −0.140923 | 0.040609 | 0.085485 | −0.148598 | 0.080072 | 0.012411 | 0.093951 | −0.009347 | −0.141404 | −0.046407 |
| 72 | 0.072268 | −0.02092 | 0.070459 | 0.032904 | 0.052351 | −0.052616 | −0.074864 | 0.039868 | −0.020263 | 0.221976 |
| 73 | −0.228261 | −0.166445 | −0.004816 | −0.015473 | −0.286208 | −0.082133 | 0.149061 | −0.096419 | 0.132974 | −0.123204 |

APPENDIX B9-continued

PCA Transformation
Matrix (77 × 77; Early/Late)

| | | | | | | | | | | |
|---|---|---|---|---|---|---|---|---|---|---|
| 74 | 0.051971 | −0.176928 | 0.061542 | 0.053701 | 0.023045 | 0.043274 | −0.08087 | 0.071879 | −0.091997 | 0.038907 |
| 75 | 0.017004 | −0.022807 | −0.021882 | 0.044412 | 0.045502 | 0.035818 | −0.016569 | −0.037495 | 0.048206 | 0.028426 |
| 76 | 0.037876 | −0.018589 | −0.014355 | 0.062932 | 0.121153 | −0.021336 | −0.004771 | −0.012181 | −0.044273 | 0.036666 |
| 77 | −0.037662 | 0.071723 | 0.07088 | −0.04482 | 0.090561 | 0.020942 | −0.079926 | −0.017819 | −0.025055 | −0.016083 |
| | AW | AX | AY | AZ | BA | BB | BC | BD | BE | BF |
| 1 | −0.040053 | 0.186977 | −0.059307 | −0.047655 | 0.114081 | −0.15051 | −0.01323 | 0.017241 | 0.150517 | 0.063524 |
| 2 | 0.014037 | 0.022271 | 0.006165 | 0.070663 | 0.044654 | 0.040175 | 0.050956 | −0.028761 | 0.077899 | 0.091306 |
| 3 | −0.092893 | −0.107557 | −0.006158 | −0.044285 | 0.037915 | −0.115912 | −0.042861 | 0.023625 | −0.087589 | 0.104614 |
| 4 | 0.12938 | 0.031875 | 0.063396 | −0.073656 | −0.068808 | 0.08281 | 0.117023 | −0.097505 | −0.145067 | −0.047099 |
| 5 | −0.028013 | −0.03643 | 0.149506 | 0.02421 | −0.048354 | 0.002474 | −0.076302 | 0.122703 | −0.015315 | −0.197729 |
| 6 | 0.183101 | −0.081281 | −0.259062 | 0.086558 | −0.076509 | −0.043964 | −0.040066 | −0.038858 | 0.056291 | −0.06183 |
| 7 | −0.13939 | −0.026381 | 0.230663 | 0.181287 | 0.133323 | −0.008667 | −0.176358 | −0.148931 | 0.06841 | 0.131893 |
| 8 | 0.127287 | 0.142308 | −0.07574 | 0.01096 | −0.070537 | 0.099917 | 0.119554 | 0.032446 | −0.001239 | −0.006799 |
| 9 | −0.22114 | −0.042388 | −0.188974 | −0.149368 | 0.028529 | 0.09652 | −0.009898 | −0.162619 | 0.084995 | 0.031028 |
| 10 | 0.104925 | 0.026765 | 0.298001 | 0.157101 | −0.023429 | −0.028656 | 0.094417 | 0.04309 | −0.055289 | −0.023222 |
| 11 | −0.144722 | −0.122467 | 0.102874 | 0.050742 | −0.032499 | 0.088313 | 0.148509 | −0.170895 | −0.07148 | 0.059075 |
| 12 | 0.14041 | −0.032965 | −0.085504 | 0.000263 | 0.042733 | 0.007693 | −0.121888 | 0.215501 | −0.067648 | 0.063878 |
| 13 | −0.0328 | 0.045463 | 0.022536 | −0.116232 | 0.069045 | 0.027189 | −0.130397 | −0.039917 | −0.127649 | −0.041073 |
| 14 | 0.026983 | 0.09905 | −0.101131 | −0.211113 | −0.05691 | −0.178016 | 0.084304 | −0.002785 | −0.036898 | 0.057388 |
| 15 | −0.00329 | −0.224489 | 0.210421 | −0.000145 | −0.150503 | 0.164991 | −0.027793 | 0.149383 | −0.220135 | −0.085763 |
| 16 | −0.033873 | −0.032445 | 0.014926 | 0.011903 | 0.02256 | −0.087855 | −0.055775 | −0.068259 | 0.092341 | 0.056066 |
| 17 | 0.143662 | 0.083476 | −0.017626 | 0.1074 | 0.047318 | −0.051015 | 0.024833 | 0.05941 | 0.064731 | 0.076775 |
| 18 | −0.125002 | 0.035055 | −0.022102 | −0.060662 | 0.056059 | 0.02642 | −0.082665 | −0.06317 | −0.060458 | −0.197817 |
| 19 | −0.099093 | 0.117744 | 0.026899 | 0.046552 | −0.143601 | 0.115411 | 0.023071 | 0.01391 | 0.153545 | −0.057041 |
| 20 | 0.12633 | −0.013182 | −0.091703 | 0.043168 | 0.138109 | −0.090227 | 0.048526 | −0.021321 | −0.106677 | 0.021243 |
| 21 | −0.152485 | −0.025232 | −0.037453 | −0.082146 | −0.135856 | −0.151095 | −0.087666 | 0.084289 | −0.143782 | 0.019655 |
| 22 | 0.123465 | 0.005454 | −0.098589 | 0.113354 | −0.039547 | −0.065597 | 0.059691 | −0.062337 | 0.041582 | 0.10878 |
| 23 | −0.043598 | 0.000942 | 0.070688 | 0.04403 | 0.208998 | 0.153366 | −0.010323 | −0.052287 | 0.034895 | −0.033456 |
| 24 | 0.156021 | −0.10421 | −0.042059 | 0.101804 | −0.263204 | −0.316415 | −0.050242 | −0.135636 | −0.12555 | 0.055962 |
| 25 | −0.221799 | 0.072617 | 0.026904 | 0.093203 | −0.116028 | 0.167507 | 0.053424 | 0.014378 | 0.001802 | −0.064468 |
| 26 | 0.145596 | −0.241861 | 0.142338 | 0.23619 | −0.002335 | −0.174474 | 0.095253 | 0.094549 | 0.202625 | 0.250882 |
| 27 | 0.096154 | 0.207741 | 0.105073 | −0.00771 | 0.097859 | 0.153807 | 0.170957 | −0.002086 | −0.074453 | 0.145918 |
| 28 | −0.06544 | −0.225477 | 0.141818 | 0.063233 | −0.100548 | 0.009302 | −0.182214 | 0.066527 | 0.05569 | −0.122267 |
| 29 | −0.071081 | 0.132246 | 0.065751 | −0.196931 | −0.099678 | −0.12359 | 0.141613 | 0.032773 | −0.114343 | 0.022197 |
| 30 | 0.005813 | −0.160906 | −0.027905 | −0.077921 | 0.034762 | 0.044767 | −0.13082 | −0.005442 | −0.102526 | 0.076475 |
| 31 | −0.12397 | −0.034189 | −0.111257 | 0.08513 | −0.048383 | 0.02364 | −0.06756 | −0.106499 | −0.020087 | −0.080996 |
| 32 | 0.242323 | 0.286006 | −0.033309 | −0.133266 | −0.105898 | −0.00497 | −0.138569 | 0.10398 | 0.094559 | 0.006501 |
| 33 | −0.100939 | −0.041571 | −0.053224 | 0.078947 | −0.19805 | 0.260488 | 0.089679 | −0.080742 | 0.040323 | 0.25506 |
| 34 | 0.145977 | 0.091992 | −0.031315 | −0.2967 | −0.004218 | 0.005686 | −0.031977 | 0.003571 | −0.079173 | 0.004331 |
| 35 | 0.096254 | −0.028745 | 0.056184 | 0.130378 | 0.070117 | −0.033999 | −0.007559 | −0.213307 | −0.346135 | −0.056446 |
| 36 | −0.033304 | −0.031643 | −0.078243 | −0.117419 | −0.00182 | −0.150517 | −0.105542 | −0.128149 | 0.10552 | −0.031303 |
| 37 | 0.049872 | 0.096073 | −0.093262 | −0.00727 | 0.050653 | 0.23403 | −0.037071 | −0.031779 | 0.076058 | −0.141654 |
| 38 | −0.041352 | 0.013365 | −0.189805 | 0.130701 | 0.112685 | −0.023069 | −0.107407 | −0.081021 | −0.011662 | 0.013679 |
| 39 | −0.191141 | −0.140647 | 0.100698 | −0.049695 | −0.153062 | −0.053836 | 0.00165 | −0.011499 | 0.248091 | −0.02733 |
| 40 | 0.207429 | −0.010539 | 0.075644 | 0.032226 | 0.279127 | 0.13225 | −0.048353 | 0.079678 | 0.046372 | 0.219558 |
| 41 | 0.012916 | 0.114469 | 0.075895 | 0.150895 | −0.084869 | −0.112583 | 0.041626 | −0.065022 | 0.012084 | −0.112939 |
| 42 | 0.146774 | −0.230325 | 0.122966 | −0.229815 | 0.208631 | −0.089355 | −0.032754 | −0.121465 | 0.022267 | 0.068881 |
| 43 | −0.087695 | 0.097887 | −0.039158 | 0.037101 | 0.226505 | −0.220985 | 0.25874 | 0.140741 | 0.051292 | −0.263867 |

APPENDIX B9-continued

PCA Transformation
Matrix (77 × 77; Early/Late)

| | | | | | | | | | | |
|---|---|---|---|---|---|---|---|---|---|---|
| 44 | −0.120035 | −0.082955 | −0.123747 | 0.200164 | 0.059887 | −0.093381 | 0.079913 | 0.362525 | 0.106017 | −0.036416 |
| 45 | 0.068425 | −0.184147 | −0.100567 | −0.105626 | 0.074484 | −0.015395 | 0.038133 | −0.082746 | −0.064256 | 0.062103 |
| 46 | −0.040543 | 0.177941 | 0.131219 | −0.114567 | −0.210126 | −0.019175 | −0.029826 | 0.095285 | −0.037652 | 0.147739 |
| 47 | 0.050558 | −0.140061 | 0.152498 | −0.124776 | 0.078948 | −0.013689 | 0.088223 | 0.105007 | 0.06743 | −0.267688 |
| 48 | −0.075042 | 0.134115 | 0.054582 | 0.253192 | −0.19939 | −0.262444 | 0.170484 | −0.174058 | 0.030234 | 0.040726 |
| 49 | 0.009253 | 0.025431 | −0.066855 | 0.031357 | 0.010887 | 0.02318 | 0.151419 | −0.046754 | −0.163049 | −0.203437 |
| 50 | 0.094269 | 0.154064 | 0.142012 | −0.061192 | −0.097439 | 0.067175 | −0.159354 | −0.065448 | 0.142291 | 0.125921 |
| 51 | −0.042351 | −0.12244 | −0.109379 | 0.17814 | 0.206219 | −0.04832 | 0.15826 | −0.005073 | −0.190353 | −0.066937 |
| 52 | 0.007349 | −0.028913 | −0.0158 | −0.000791 | 0.031045 | 0.033824 | 0.072587 | −0.033662 | 0.015965 | 0.038195 |
| 53 | −0.14114 | 0.006532 | −0.239357 | 0.027646 | −0.029871 | 0.162735 | 0.084658 | 0.050316 | −0.033594 | 0.032977 |
| 54 | −0.0726 | −0.022106 | 0.153111 | −0.192014 | −0.093185 | −0.22253 | −0.113589 | 0.041907 | 0.073302 | −0.083983 |
| 55 | 0.264884 | 0.103709 | 0.127454 | 0.152816 | 0.024871 | −0.057684 | −0.099379 | −0.026157 | 0.026267 | −0.129114 |
| 56 | 0.038453 | 0.055904 | 0.059986 | 0.091083 | −0.031317 | −0.014855 | −0.050067 | 0.057023 | 0.069918 | −0.079228 |
| 57 | 0.029715 | −0.071073 | 0.06429 | 0.127543 | 0.078217 | 0.10183 | −0.12424 | 0.057135 | 0.074501 | 0.064196 |
| 58 | −0.034093 | 0.117478 | −0.037361 | 0.009529 | −0.016512 | 0.018869 | 0.116922 | 0.129609 | 0.071405 | 0.12872 |
| 59 | 0.091437 | 0.110447 | 0.010399 | 0.108594 | 0.066683 | −0.034957 | −0.090922 | −0.200331 | −0.08954 | −0.1446 |
| 60 | −0.048815 | 0.02884 | −0.116958 | 0.114383 | 0.046094 | −0.087278 | 0.088101 | −0.219934 | 0.204859 | 0.011687 |
| 61 | 0.101317 | −0.014843 | 0.060537 | 0.021145 | 0.106609 | 0.202659 | −0.038041 | −0.058487 | 0.022052 | −0.061553 |
| 62 | −0.080677 | 0.07841 | 0.177268 | −0.02152 | 0.157164 | −0.083625 | −0.108283 | −0.068695 | 0.093521 | 0.135827 |
| 63 | 0.159009 | −0.000914 | 0.03826 | 0.112271 | −0.180384 | 0.160613 | 0.036017 | 0.05588 | −0.076844 | −0.219242 |
| 64 | 0.060958 | 0.010793 | −0.245684 | −0.004835 | 0.141599 | 0.006233 | 0.006194 | 0.218803 | 0.054923 | −0.020272 |
| 65 | 0.041297 | −0.088614 | −0.09626 | −0.174786 | −0.110587 | −0.071783 | 0.106831 | −0.046534 | −0.080781 | 0.096192 |
| 66 | 0.253628 | −0.227094 | −0.1021 | −0.066187 | −0.088793 | −0.01603 | 0.242469 | −0.062191 | 0.117455 | −0.001331 |
| 67 | −0.099432 | 0.173666 | 0.01522 | 0.032081 | 0.130827 | −0.02139 | −0.143072 | 0.057053 | −0.023127 | 0.118822 |
| 68 | −0.165203 | 0.004701 | 0.070117 | −0.084127 | 0.245907 | −0.099113 | −0.070972 | −0.069355 | −0.151427 | 0.041301 |
| 69 | −0.027907 | −0.070893 | −0.077052+31 | 0.049994 | −0.080577 | 0.029206 | −0.146504 | 0.355282 | 0.042292 | 0.005524 |
| 70 | −0.070545 | 0.044487 | 0.007271 | −0.059456 | −0.022833 | 0.102858 | 0.216127 | −0.047979 | 0.018469 | 0.160808 |
| 71 | 0.052369 | 0.167448 | −0.167803 | 0.188124 | −0.141538 | 0.019024 | −0.339415 | −0.118557 | −0.156075 | 0.022484 |
| 72 | 0.012832 | −0.052284 | 0.161436 | −0.061937 | −0.057687 | 0.180935 | 0.21333 | −0.07494 | −0.007221 | 0.076222 |
| 73 | 0.12142 | −0.133057 | −0.007254 | −0.12532 | −0.091301 | −0.028791 | −0.061598 | −0.007139 | 0.097389 | −0.050002 |
| 74 | −0.046819 | −0.219877 | −0.195987 | 0.076786 | −0.10325 | 0.080945 | −0.202742 | −0.029262 | −0.076397 | 0.116607 |
| 75 | −0.036544 | 0.048931 | 0.042506 | 0.046272 | −0.005706 | −0.074379 | 0.044222 | 0.248186 | −0.373287 | 0.279444 |
| 76 | −0.101731 | 0.0602 | 0.025456 | −0.021452 | 0.032097 | −0.020231 | 0.010888 | −0.040302 | 0.02743 | −0.147501 |
| 77 | 0.137169 | −0.06102 | −0.05651 | −0.085258 | −0.02131 | 0.109903 | −0.048037 | −0.139332 | 0.202819 | −0.047151 |

| | BG | BH | BI | BJ | BK | BL | BM | BN | BO | BP |
|---|---|---|---|---|---|---|---|---|---|---|
| 1 | −0.14359 | 0.146639 | −0.016028 | −0.050847 | −0.166618 | −0.045569 | −0.118859 | 0.063015 | −0.019458 | −0.054995 |
| 2 | 0.027549 | 0.042748 | 0.030546 | 0.151035 | 0.027508 | −0.004461 | −0.00349 | −0.00821 | 0.081559 | 0.044513 |
| 3 | −0.00937 | 0.046057 | 0.012202 | 0.062316 | −0.018604 | −0.015316 | 0.051673 | −0.113941 | 0.101405 | −0.087971 |
| 4 | 0.055683 | −0.157991 | −0.064034 | 0.116909 | 0.105033 | −0.007018 | 0.043585 | 0.018722 | −0.023019 | 0.285311 |
| 5 | −0.05002 | −0.011299 | −0.087442 | −0.092814 | 0.083457 | 0.172148 | 0.222561 | 0.098381 | −0.001968 | −0.02657 |
| 6 | −0.036209 | 0.138805 | 0.134219 | −0.011922 | −0.057822 | 0.103974 | 0.123144 | 0.040539 | 0.131762 | 0.058865 |
| 7 | 0.011144 | −0.326627 | −0.068883 | 0.029644 | −0.062836 | 0.057039 | 0.149853 | 0.011789 | −0.056837 | 0.009991 |
| 8 | 0.098769 | 0.060212 | −0.009229 | −0.069131 | 0.197414 | 0.021422 | −0.109032 | 0.07077 | 0.077821 | −0.054947 |
| 9 | 0.200082 | −0.076257 | −0.098295 | −0.104171 | −0.075481 | 0.116136 | −0.058348 | 0.084512 | 0.131318 | −0.043061 |
| 10 | −0.148808 | 0.12328 | 0.049567 | −0.021262 | 0.048377 | −0.14961 | 0.059971 | −0.10952 | −0.057727 | −0.014249 |
| 11 | −0.007034 | 0.095553 | 0.265312 | −0.043783 | 0.055857 | 0.020609 | 0.058417 | −0.089327 | 0.098124 | −0.040047 |
| 12 | −0.074622 | −0.16437 | 0.005354 | 0.157449 | 0.138881 | 0.08978 | −0.072085 | 0.076642 | −0.062276 | 0.002475 |
| 13 | −0.027637 | −0.012765 | 0.114705 | −0.017644 | −0.033882 | 0.075686 | −0.039063 | −0.055694 | 0.055291 | 0.098185 |

APPENDIX B9-continued

PCA Transformation Matrix (77 × 77; Early/Late)

| | | | | | | | | | | |
|---|---|---|---|---|---|---|---|---|---|---|
| 14 | −0.066356 | −0.037247 | 0.053862 | −0.021406 | 0.17908 | 0.010479 | 0.026136 | −0.11297 | 0.036193 | −0.106423 |
| 15 | 0.205494 | 0.002723 | −0.070505 | 0.059497 | −0.026156 | 0.072017 | 0.135455 | 0.017356 | 0.03151 | 0.102698 |
| 16 | −0.008307 | −0.120174 | 0.067202 | 0.061776 | 0.034007 | 0.044606 | 0.07898 | −0.098184 | −0.020983 | −0.069664 |
| 17 | 0.005045 | −0.101551 | −0.115335 | 0.13272 | 0.13343 | −0.094662 | −0.026952 | 0.025184 | −0.004718 | −0.092645 |
| 18 | 0.054348 | −0.024497 | −0.023896 | −0.089919 | −0.084201 | 0.089285 | 0.09618 | 0.009637 | −0.087697 | 0.121022 |
| 19 | −0.00985 | 0.026541 | 0.043444 | −0.006378 | 0.031193 | 0.055336 | 0.004699 | 0.026917 | −0.022042 | −0.086377 |
| 20 | 0.055799 | 0.030528 | −0.174331 | −0.030903 | −0.078993 | −0.129207 | −0.014094 | 0.086969 | 0.125248 | 0.065067 |
| 21 | −0.25568 | −0.123089 | 0.073626 | −0.330252 | −0.08042 | −0.115291 | 0.165909 | 0.073156 | 0.278926 | 0.091643 |
| 22 | 0.148823 | 0.081468 | −0.133756 | 0.114289 | −0.039168 | 0.092094 | 0.401329 | 0.075175 | 0.001486 | 0.255773 |
| 23 | −0.306211 | 0.038627 | 0.192521 | 0.163571 | −0.032052 | 0.041519 | −0.085344 | −0.018493 | 0.34301 | −0.022921 |
| 24 | −0.020095 | 0.118658 | −0.136475 | −0.057737 | −0.00056 | 0.1322 | −0.145743 | 0.180576 | −0.023706 | 0.205065 |
| 25 | 0.169054 | −0.112252 | −0.027091 | −0.008897 | 0.109491 | −0.078997 | 0.07772 | 0.244223 | 0.081851 | 0.01412 |
| 26 | 0.004331 | −0.036302 | 0.082981 | 0.06321 | −0.054719 | 0.000465 | −0.051605 | −0.087471 | 0.05425 | −0.046628 |
| 27 | −0.022751 | 0.055524 | 0.067151 | 0.042599 | −0.006403 | 0.001515 | 0.094525 | −0.113394 | −0.091246 | 0.063402 |
| 28 | −0.0202 | 0.097353 | 0.022622 | −0.065249 | 0.110394 | 0.035662 | 0.042627 | −0.03027 | −0.039042 | −0.214454 |
| 29 | 0.030175 | 0.060743 | −0.154242 | 0.348125 | −0.08254 | −0.094679 | 0.021633 | 0.008208 | 0.250093 | 0.126152 |
| 30 | −0.079702 | 0.180249 | 0.039922 | −0.099446 | −0.041373 | 0.122269 | 0.17423 | −0.086644 | 0.012929 | −0.089315 |
| 31 | −0.018462 | 0.021455 | 0.017794 | 0.278171 | 0.051024 | 0.030104 | 0.024208 | 0.185648 | 0.360806 | −0.170617 |
| 32 | 0.021113 | −0.040425 | 0.142064 | 0.021699 | 0.025981 | −0.126663 | 0.158372 | 0.00204 | 0.017904 | −0.190586 |
| 33 | −0.086643 | 0.230967 | 0.149989 | −0.014286 | −0.013855 | −0.002613 | −0.123851 | −0.075137 | −0.026762 | 0.208004 |
| 34 | −0.058209 | 0.137814 | 0.00583 | 0.080419 | −0.040682 | 0.105247 | −0.029072 | 0.09768 | −0.095551 | −0.150103 |
| 35 | −0.148075 | 0.077965 | −0.004275 | −0.141818 | 0.141857 | 0.088453 | 0.090121 | −0.103087 | −0.019399 | 0.0151 |
| 36 | −0.038389 | 0.026941 | 0.212487 | 0.121621 | −0.102431 | 0.109197 | 0.088368 | −0.177086 | −0.065967 | 0.009599 |
| 37 | 0.056279 | −0.143431 | 0.165009 | −0.06551 | 0.038043 | −0.085884 | −0.039708 | 0.126493 | 0.159525 | 0.20754 |
| 38 | 0.03202 | −0.017848 | −0.168467 | −0.001504 | −0.050243 | 0.01658 | 0.028974 | −0.123461 | 0.010402 | 0.193582 |
| 39 | −0.038256 | −0.104588 | 0.089412 | 0.287518 | −0.03981 | −0.21365 | 0.142898 | 0.037553 | −0.117976 | 0.099366 |
| 40 | 0.004125 | 0.005456 | −0.069772 | −0.189469 | 0.076967 | 0.302401 | −0.083337 | 0.09339 | 0.035466 | 0.042402 |
| 41 | −0.093379 | −0.067893 | −0.050445 | 0.0964 | 0.142201 | 0.038552 | 0.057035 | −0.092423 | 0.046483 | 0.02533 |
| 42 | 0.225027 | 0.055192 | −0.011537 | 0.046166 | 0.019119 | −0.126828 | 0.16269 | −0.091209 | 0.116624 | 0.019169 |
| 43 | −0.078754 | −0.182501 | 0.125708 | 0.023087 | −0.03184 | 0.308858 | 0.007899 | −0.107755 | −0.021195 | 0.199177 |
| 44 | −0.044473 | 0.159404 | −0.244233 | −0.078065 | −0.016409 | −0.128686 | −0.114508 | −0.114636 | 0.259595 | 0.024274 |
| 45 | −0.064969 | −0.016323 | 0.051382 | 0.135177 | 0.001426 | 0.047334 | −0.02452 | 0.137956 | −0.086763 | −0.114068 |
| 46 | 0.043445 | −0.053768 | −0.232073 | −0.119252 | 0.058374 | −0.058878 | 0.000502 | −0.177147 | 0.004255 | 0.069008 |
| 47 | −0.203733 | 0.202147 | −0.042822 | 0.087844 | 0.002029 | −0.058545 | 0.099294 | 0.104971 | −0.104636 | 0.051198 |
| 48 | 0.177251 | 0.057183 | 0.055497 | 0.005476 | −0.041559 | 0.189457 | 0.008559 | 0.102906 | −0.096541 | −0.215636 |
| 49 | 0.054525 | 0.05742 | 0.178816 | −0.055184 | 0.069423 | −0.103984 | 0.033106 | 0.0274 | −0.098049 | 0.086456 |
| 50 | 0.01504 | 0.034136 | −0.017452 | 0.011868 | −0.145405 | 0.221239 | 0.091977 | −0.170218 | 0.17623 | 0.095808 |
| 51 | 0.049115 | 0.071256 | 0.027501 | −0.001376 | −0.000708 | −0.101464 | 0.034447 | 0.245174 | −0.115142 | −0.103676 |
| 52 | 0.095722 | 0.030888 | 0.043323 | −0.058224 | −0.148913 | −0.08161 | 0.037542 | 0.048864 | 0.012228 | 0.013802 |
| 53 | −0.247333 | 0.238645 | −0.319766 | 0.20802 | 0.045172 | 0.077657 | 0.267489 | −0.135647 | −0.088966 | −0.044931 |
| 54 | 0.031549 | 0.189766 | 0.040109 | 0.031156 | 0.144769 | 0.286741 | −0.13055 | 0.142135 | 0.155411 | 0.172608 |
| 55 | 0.077398 | 0.026138 | 0.035938 | −0.055362 | −0.274557 | −0.171489 | 0.138996 | 0.088921 | 0.251458 | −0.019729 |
| 56 | −0.013 | −0.131977 | −0.02689 | 0.007904 | 0.131629 | 0.045307 | 0.019593 | −0.04558 | 0.009155 | 0.015476 |
| 57 | −0.07015 | 0.063107 | 0.05494 | 0.003519 | −0.179957 | 0.016078 | 0.025796 | 0.26725 | 0.019071 | 0.087963 |
| 58 | −0.018199 | 0.023892 | −0.042375 | −0.100001 | −0.159506 | 0.1726331 | 0.1364781 | 0.152766 | 0.008201 | −0.097552 |
| 59 | −0.094618 | 0.012411 | −0.018297 | 0.083239 | 0.089174 | −0.207681 | −0.129795 | −0.150319 | 0.124919 | 0.019698 |
| 60 | −0.047316 | 0.056037 | 0.049608 | 0.002108 | 0.139423 | 0.037392 | 0.069854 | −0.053079 | −0.021805 | 0.088203 |
| 61 | 0.223085 | 0.119602 | −0.049013 | 0.292196 | 0.029941 | 0.146872 | −0.149929 | 0.000348 | −0.025029 | −0.050082 |
| 62 | −0.083738 | 0.122869 | 0.005348 | −0.044892 | 0.532804 | −0.020131 | 0.097622 | 0.246109 | 0.088321 | 0.070274 |
| 63 | −0.158277 | −0.099223 | −0.006428 | 0.104614 | −0.21076 | 0.262844 | −0.034333 | −0.096012 | 0.063831 | −0.064396 |

APPENDIX B9-continued

PCA Transformation
Matrix (77 × 77; Early/Late)

| | | | | | | | | | | |
|---|---|---|---|---|---|---|---|---|---|---|
| 64 | 0.191526 | −0.027976 | 0.130334 | −0.029066 | 0.183358 | 0.032565 | 0.410589 | −0.136348 | 0.080702 | −0.096316 |
| 65 | −0.054459 | −0.094717 | 0.121615 | 0.04979 | 0.020722 | −0.033198 | −0.003172 | 0.088482 | 0.037 | 0.010742 |
| 66 | −0.012632 | −0.158525 | −0.031578 | −0.013948 | 0.114988 | 0.065838r | −0.052734 | −0.029282 | 0.187658 | 0.063334 |
| 67 | 0.037072 | 0.271098 | 0.121298 | 0.054489 | −0.069559 | −0.098839 | 0.04529 | 0.032421 | −0.119714 | 0.300889 |
| 68 | −0.039918 | −0.13337 | −0.26229 | 0.147486 | −0.07497 | 0.073638 | −0.051707 | 0.021017 | 0.030776 | −0.113118 |
| 69 | 0.018687 | 0.033208 | 0.107082 | 0.139838 | 0.153687 | 0.036088 | −0.116922 | 0.022316 | −0.045546 | 0.149621 |
| 70 | −0.19513 | −0.12903 | 0.019195 | −0.029922 | −0.022093 | 0.089855 | 0.124139 | 0.236534 | 0.038855 | −0.006815 |
| 71 | −0.066669 | 0.033453 | −0.012244 | 0.128505 | 0.063908 | −0.000192 | 0.057912 | 0.101074 | −0.000292 | −0.137846 |
| 72 | −0.031245 | 0.088656 | −0.157089 | −0.095939 | 0.060438 | −0.015355 | 0.066197 | −0.052986 | 0.192781 | −0.151098 |
| 73 | 0.040109 | 0.083391 | −0.003381 | −0.010969 | −0.074547 | −0.115506 | 0.040794 | 0.139537 | −0.082169 | −0.044158 |
| 74 | 0.018702 | −0.12914 | 0.01839 | −0.030307 | 0.110253 | −0.037331 | −0.066084 | −0.203809 | 0.016945 | 0.077661 |
| 75 | 0.008022 | −0.110715 | 0.235771 | 0.157064 | −0.060728 | 0.036718 | 0.010082 | 0.051744 | 0.05458 | −0.000966 |
| 76 | 0.272618 | 0.197245 | 0.010521 | −0.064601 | 0.03084 | 0.078336 | −0.081841 | −0.144096 | 0.13141 | −0.059304 |
| 77 | −0.300253 | −0.105131 | −0.191662 | −0.047581 | 0.009093 | −0.065722 | 0.029259 | 0.075077 | −0.106777 | 0.097244 |

| | BQ | BR | BS | BT | BU | BV | BW | BX | BY | BZ |
|---|---|---|---|---|---|---|---|---|---|---|
| 1 | −0.110462 | 0.007975 | −0.034485 | 0.014599 | 0.067012 | 0.072946 | 0.083736 | 0.071371 | 0.089467 | 0.027627 |
| 2 | 0.061677 | −0.025638 | −0.014133 | −0.009119 | 0.067959 | 0.072585 | 0.065106 | −0.037454 | 0.012589 | −0.039873 |
| 3 | −0.064722 | 0.05379 | −0.005882 | 0.055382 | −0.055956 | 0.077 | 0.05723 | 0.046643 | 0.102349 | 0.152695 |
| 4 | 0.07801 | 0.060183 | −0.005711 | 0.056191 | 0.013511 | 0.070968 | −0.047392 | −0.169839 | −0.054272 | −0.107068 |
| 5 | −0.10886 | 0.029065 | −0.013783 | −0.110886 | −0.083757 | −0.059319 | −0.065482 | 0.063867 | −0.006148 | −0.011199 |
| 6 | 0.040442 | −0.010957 | −0.013163 | −0.144975 | −0.042094 | −0.244816 | 0.154852 | 0.103388 | −0.021978 | −0.048736 |
| 7 | −0.096737 | 0.139407 | 0.032051 | 0.066185 | 0.144885 | 0.092971 | −0.079581 | 0.000769 | 0.150272 | −0.051637 |
| 8 | 0.099242 | −0.144274 | −0.036389 | 0.037871 | 0.009512 | 0.200107 | −0.120117 | −0.177159 | −0.12765 | 0.044932 |
| 9 | −0.193538 | 0.015476 | −0.037874 | −0.153569 | 0.009779 | 0.117365 | 0.065193 | −0.072203 | −0.225527 | −0.109555 |
| 10 | 0.210702 | 0.064977 | 0.073492 | 0.204768 | −0.021894 | 0.005659 | −0.056747 | 0.095594 | 0.082283 | 0.149199 |
| 11 | −0.266601 | 0.332955 | 0.094944 | 0.101302 | −0.182223 | −0.039603 | 0.00836 | 0.000832 | −0.09479 | 0.017683 |
| 12 | −0.124971 | −0.098215 | −0.108498 | −0.048786 | 0.077822 | −0.132993 | −0.006494 | −0.066918 | −0.096109 | 0.235785 |
| 13 | −0.00963 | −0.03153 | 0.040426 | 0.0868 | 0.048726 | −0.012943 | −0.066452 | −0.065791 | −0.017817 | 0.017729 |
| 14 | 0.201513 | 0.196654 | 0.108368 | −0.061426 | −0.05647 | 0.010521 | −0.042691 | 0.004807 | −0.091479 | −0.108483 |
| 15 | 0.012924 | −0.1019 | 0.049354 | −0.148777 | −0.085618 | −0.11097 | 0.071321 | −0.100124 | −0.006665 | 0.066711 |
| 16 | 0.190947 | −0.009644 | 0.115951 | 0.048487 | 0.153217 | 0.107994 | −0.037053 | −0.032919 | −0.051909 | −0.003695 |
| 17 | 0.048241 | −0.012877 | −0.098573 | −0.112405 | −0.054034 | −0.084387 | 0.125357 | 0.066739 | 0.100245 | −0.055464 |
| 18 | −0.024643 | −0.026782 | 0.088343 | 0.068602 | 0.15108 | 0.120708 | 0.091631 | −0.02488 | −0.06414 | −0.023267 |
| 19 | 0.086379 | −0.027258 | −0.081092 | −0.075139 | 0.063989 | 0.081164 | −0.003695 | 0.149147 | −0.015939 | 0.027741 |
| 20 | −0.196692 | 0.048931 | 0.000663 | 0.078544 | −0.091482 | −0.092289 | 0.014093 | −0.052461 | 0.007582 | −0.057191 |
| 21 | 0.007842 | 0.00893 | −0.118327 | −0.082457 | 0.053235 | 0.078145 | −0.232221 | −0.114447 | 0.143037 | −0.029735 |
| 22 | 0.029281 | 0.08859 | 0.098933 | 0.002683 | 0.098584 | 0.186617 | 0.09084 | 0.070746 | 0.073971 | 0.074823 |
| 23 | −0.038201 | 0.061198 | −0.217031 | −0.059655 | −0.218371 | 0.074753 | 0.215895 | −0.08848 | 0.043872 | −0.133859 |
| 24 | 0.066299 | 0.143273 | −0.013551 | −0.131841 | 0.028616 | −0.040078 | −0.021523 | 0.175172 | 0.089232 | −0.085344 |
| 25 | 0.048746 | 0.082827 | −0.063449 | −0.035088 | −0.152628 | −0.008264 | −0.106703 | 0.196241 | 0.054107 | 0.10758 |
| 26 | 0.02919 | −0.037969 | 0.05291 | 0.023595 | −0.047139 | 0.098899 | −0.158742 | −0.209106 | −0.027786 | −0.024578 |
| 27 | 0.095781 | 0.012489 | −0.10657 | −0.124352 | −0.014036 | −0.176379 | 0.081477 | 0.037042 | 0.150547 | 0.099468 |
| 28 | −0.006102 | −0.063303 | −0.03697 | −0.009179 | 0.00597 | 0.147152 | 0.094162 | −0.107291 | −0.150124 | −0.077697 |
| 29 | −0.149652 | 0.043263 | 0.033774 | 0.149437 | 0.024455 | 0.087121 | −0.043434 | −0.266867 | −0.04143 | 0.079451 |
| 30 | 0.070861 | 0.082009 | 0.071116 | −0.049391 | −0.026728 | 0.070424 | 0.238173 | 0.042113 | 0.010901 | 0.128576 |
| 31 | 0.224254 | 0.059999 | 0.012431 | 0.033375 | 0.16238 | −0.032609 | −0.155648 | −0.04467 | −0.039429 | 0.086275 |
| 32 | −0.275946 | 0.149035 | 0.081538 | 0.079049 | 0.012185 | 0.097338 | 0.174184 | 0.035661 | 0.08355 | 0.023544 |
| 33 | 0.061737 | −0.172349 | 0.059048 | 0.022851 | 0.156321 | 0.028771 | −0.088307 | −0.100013 | −0.003609 | 0.026393 |

APPENDIX B9-continued

PCA Transformation
Matrix (77 × 77; Early/Late)

| | | | | | | | | | | |
|---|---|---|---|---|---|---|---|---|---|---|
| 34 | −0.006497 | 0.034467 | 0.050455 | −0.082694 | 0.012606 | −0.015442 | −0.027478 | −0.043201 | −0.027807 | 0.042735 |
| 35 | −0.135222 | 0.067327 | 0.045272 | 0.135794 | −0.009931 | −0.10012 | 0.109268 | −0.059118 | −0.052184 | −0.044415 |
| 36 | 0.081944 | −0.109384 | −0.114093 | −0.097739 | 0.232122 | −0.031367 | −0.018301 | −0.072892 | 0.024209 | −0.063647 |
| 37 | 0.077787 | 0.072711 | 0.029237 | 0.061544 | −0.09816 | 0.014573 | −0.068478 | 0.214005 | 0.032916 | −0.020489 |
| 38 | −0.089851 | 0.047412 | −0.060684 | 0.093233 | 0.130379 | −0.049646 | 0.034494 | −0.003019 | −0.000306 | −0.186994 |
| 39 | −0.038853 | 0.037813 | −0.009065 | −0.073012 | −0.075162 | −0.01254 | 0.244094 | 0.108503 | 0.131795 | −0.100751 |
| 40 | 0.058795 | 0.124771 | 0.073238 | −0.07058 | −0.059691 | 0.380701 | −0.075266 | 0.042409 | 0.065699 | −0.037078 |
| 41 | −0.115449 | −0.109849 | −0.112993 | 0.084615 | 0.057331 | −0.001611 | −0.031978 | −0.121671 | −0.044539 | −0.050505 |
| 42 | 0.094555 | −0.098961 | −0.356501 | 0.01471 | −0.215319 | 0.14526 | −0.146956 | 0.123434 | −0.018139 | 0.058121 |
| 43 | 0.073645 | −0.048795 | 0.073907 | −0.164277 | −0.095932 | −0.041613 | 0.058056 | −0.065828 | −0.093841 | 0.159556 |
| 44 | 0.002113 | −0.025723 | 0.148238 | 0.116081 | −0.049476 | −0.033359 | 0.071559 | 0.13834 | −0.095358 | 0.102246 |
| 45 | −0.061646 | 0.033368 | −0.020639 | −0.069506 | −0.013388 | −0.072489 | −0.069205 | −0.087335 | 0.059843 | 0.0486 |
| 46 | −0.043231 | −0.018173 | −0.087986 | −0.046159 | −0.117791 | 0.079104 | 0.191637 | −0.057305 | 0.002746r | −0.027534 |
| 47 | −0.033166 | −0.029597 | 0.151361 | 0.139794 | 0.15841 | 0.028093 | −0.156523 | 0.098264 | −0.045297 | −0.272691 |
| 48 | −0.132144 | 0.001275 | −0.073164 | −0.156945 | −0.101522 | 0.064766 | 0.013512 | −0.102479 | −0.054837 | 0.197749 |
| 49 | 0.162093 | −0.083358 | −0.210956 | −0.006638 | 0.061772 | 0.21972 | 0.234144 | −0.026892 | 0.075095 | −0.009029 |
| 50 | −0.012531 | −0.001143 | 0.096704 | −0.030219 | −0.024531 | −0.199189 | −0.164537 | 0.100263 | −0.082786 | −0.00345 |
| 51 | −0.060074 | 0.10165 | −0.083941 | 0.040467 | 0.118569 | 0.035893 | −0.007669 | −0.075496 | 0.085482 | 0.068294 |
| 52 | 0.110083 | 0.037797 | −0.021742 | −0.015212 | 0.130761 | 0.118792 | 0.063102 | 0.065256 | 0.04614 | 0.111157 |
| 53 | 0.020466 | −0.071457 | −0.042175 | −0.219456 | −0.187175 | 0.182937 | −0.098719 | 0.002296 | 0.018882 | −0.110193 |
| 54 | −0.045122 | −0.144684 | −0.098315 | 0.258478 | 0.05805 | 0.099188 | 0.157304 | 0.167412 | 0.122138 | 0.249025 |
| 55 | 0.226184 | 0.019477 | 0.115965 | −0.179069 | 0.031431 | −0.046697 | 0.192141 | −0.199456 | −0.235974 | −0.063067 |
| 56 | 0.006292 | −0.039645 | −0.089232 | −0.002002 | −0.012007 | 0.027002 | −0.036477 | 0.025119 | 0.002441 | −0.062808 |
| 57 | −0.163917 | −0.260222 | −0.011874 | −0.087914 | −0.031105 | −0.082647 | −0.045303 | −0.094728 | 0.119869 | 0.119959 |
| 58 | 0.161032 | 0.130415 | −0.352045 | 0.367495 | 0.10439 | −0.060102 | 0.155482 | −0.127378 | 0.032449 | −0.153439 |
| 59 | −0.186789 | −0.056428 | 0.122269 | −0.292189 | 0.199011 | 0.315738 | −0.028169 | 0.138082 | 0.11552 | 0.183632 |
| 60 | −0.021141 | 0.072576 | −0.022826 | 0.149024 | −0.110737 | −0.006446 | −0.130293 | 0.172228 | −0.091076 | −0.092728 |
| 61 | −0.071198 | 0.040311 | 0.096916 | 0.13916 | 0.041439 | −0.080373 | 0.086963 | 0.060442 | −0.113315 | 0.023579 |
| 62 | 0.029672 | −0.073617 | −0.001696 | −0.148053 | 0.030375 | −0.120632 | 0.11686 | −0.130616 | −0.121464 | −0.090163 |
| 63 | −0.040569 | 0.105925 | −0.176664 | 0.04613 | −0.082374 | 0.204471 | −0.0925 | 0.03965 | 0.084367 | 0.01792 |
| 64 | −0.123829 | −0.10103 | 0.05643 | 0.101847 | 0.104386 | −0.034082 | −0.136277 | −0.033947 | 0.034884 | 0.195243 |
| 65 | 0.081568 | 0.077788 | 0.095341 | −0.001957 | −0.14267 | −0.057136 | −0.135498 | 0.032779 | 0.075719 | 0.107656 |
| 66 | −0.13237 | −0.08828 | −0.03628 | 0.018053 | 0.025912 | 0.013074 | 0.185511 | 0.041352 | 0.087347 | −0.133937 |
| 67 | −0.050266 | 0.082738 | −0.133031 | −0.06578 | −0.117713 | 0.010313 | −0.102115 | −0.090912 | −0.041931 | 0.043374 |
| 68 | 0.307282 | 0.057503 | 0.058547 | −0.02055 | −0.027669 | −0.041845 | 0.084229 | 0.117557 | 0.014219 | 0.082303 |
| 69 | 0.031325 | 0.547836 | 0.011973 | −0.149812 | 0.169337 | 0.064856 | 0.043152 | −0.136818 | −0.028923 | 0.015618 |
| 70 | 0.012693 | −0.174014 | 0.444639 | 0.063294 | −0.042856 | 0.084516 | 0.207504 | −0.056347 | 0.151647 | −0.011638 |
| 71 | 0.098921 | −0.12176 | 0.040674 | 0.225884 | −0.161843 | 0.011763 | −0.019021 | 0.014742 | 0.052467 | −0.05864 |
| 72 | −0.060611 | 0.097929 | −0.154763 | −0.146364 | 0.473746 | −0.167878 | −0.012783 | 0.146025 | 0.061327 | 0.030424 |
| 73 | 0.013585 | 0.018615 | 0.082364 | 0.027742 | −0.092529 | 0.218784 | −0.039912 | −0.017534 | −0.021651 | −0.134684 |
| 74 | 0.116202 | −0.05912 | 0.004541 | 0.10902 | −0.00379 | 0.009649 | 0.248129 | −0.078698 | 0.041385 | 0.141842 |
| 75 | −0.082109 | −0.159699 | −0.02445 | −0.027649 | 0.118993 | 0.080087 | 0.011793 | 0.340224 | −0.293116 | −0.149282 |
| 76 | 0.100327 | 0.047373 | 0.160863 | −0.041238 | −0.069207 | −0.089834 | −0.067897 | −0.205908 | 0.553528 | −0.173695 |
| 77 | 0.005705 | 0.124274 | −0.102894 | 0.061632 | −0.002104 | −0.083355 | 0.000043 | −0.147607 | −0.184522 | 0.481797 |

APPENDIX C1

SVM Model Weights
(340; Normal/Diseased)

SVM−light Version V6.01
0 # kernel type
3 # kernel parameter -d
1 # kernel parameter -g
1 # kernel parameter -s
1 # kernel parameter -r
empty# kernel parameter -u
340 # highest feature index
138 # number of training documents
78 # number of support vectors plus 1
0.67854397 # threshold b, each following line is a SV (starting with alpha*y)
−0.0011415251604807632 1:−6.2484217 2:2.8692274 3:3.9726458 4:4.5728879 5:3.1217315
6:1.431265 7:0.44778323 8:1.02934 9:1.1082938 10:1.1373868 11:1.9316131 12:0.28561696
13:−3.060276 14:0.38243186 15:0.76406515 16:1.25282 17:0.95133108 18:1.8977604 19:0.33501664
20:0.67167497 21:−0.11577946 22:1.6258748 23:−0.61664796 24:−1.2282914 25:−1.6443142
26:−0.90777022 27:1.2275497 28:1.0568956 29:2.1236527 30:−0.26141879 31:0.03845077
32:−0.58085138 33:−0.78061342 34:1.2447574 35:0.24944715 36:−0.3606073 37:−0.23068826
38:0.78405386 39:−0.43722236 40:0.28527892 41:−1.2349344 42:−1.6965803 43:0.25968778
44:0.74408704 45:−0.11024579 46:−0.70728445 47:1.5416214 48:0.5093556 49:0.50813681
50:−0.10848369 51:−0.72595042 52:−1.0701329 53:1.2242886 54:−0.44644347 55:0.22465287
56:1.0197572 57:−1.3624406 58:0.96072525 59:−1.3194218 60:−0.52487147 61:−0.1581929
62:0.0047937976 63:0.096934691 64:1.8773297 65:1.0675534 66:−0.37953418 67:−0.30575103
68:−0.14885564 69:−0.7085318 70:−0.082562283 71:0.71772766 72:−0.6834473 73:0.37860462
74:−0.3881411 75:−0.17689922 76:0.89653313 77:0.48991525 78:−0.13384825 79:−0.7523219
80:−0.15887904 81:−0.72565669 82:−0.071575895 83:0.26591104 84:−0.036035866 85:0.11221373
86:0.30020183 87:0.48851889 88:−0.056364294 89:0.66078192 90:−1.0552732 91:−0.49472538
92:0.19626696 93:0.3516041 94:−0.90524662 95:0.48864928 96:1.0635862 97:−0.67823666
98:0.97963518 99:−1.2187407 100:0.25271565 101:−0.10477167 102:−0.094989687
103:−0.14250714 104:0.77763522 105:−0.67844582 106:0.10758131 107:−0.59481978 108:0.12150268
109:−0.25061738 110:−0.31553453 111:−0.2249333 112:−0.14794669 113:−0.29111996
114:0.42366493 115:0.32037699 116:−0.38479248 117:−0.35609257 118:0.21150146
119:0.29969886 120:−0.056325451 121:0.18981926 122:0.36390802 123:−0.22452836
124:−0.014986999 125:−0.07822156 126:0.078114182 127:−0.31460276 128:0.33136594
129:0.14089347 130:−0.11384387 131:0.2209356 132:−0.30368382 133:−0.021809017
134:0.13270371 135:0.02210488 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133 174:0.00017559867 175:0.001684437
176:−0.0034504069 177:0.0018235954 178:−0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938
190:−0.0034640408 191:−0.00026976471 192:0.00097010034 193:−0.0011612385 194:−0.0015113452
195:0.00062438019 196:−0.00013164691 197:0.0020616048 198:0.0010445472
199:−0.0049765292 200:9.8877339e−005 201:0.0028779099 202:−0.0036701721 203:0.00099803088
204:0.00068234798 205:0.002192216 206:0.0033146022 207:0.00050616561 208:−0.0031757453
209:0.0028448526 210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097
228:−0.0016731552 229:0.00047607321 230:−0.011432272.231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387

APPENDIX C1-continued

| SVM Model Weights (340; Normal/Diseased) |
|---|
| 338:−0.0027431778 339:−0.0055160136 340:0.0031345901 # −0.0019987040978036159 1:−5.5317745 2:−3.2781949 3:1.4514818 4:4.4336934 5:0.22635397 6:2.3636923 7:2.9700732 8:−0.24828267 9:−2.3608406 10:−1.9967079 11:−0.73264194 12:1.0981561 13:−1.8951033 14:0.55268621 15:1.5258482 16:0.17173247 17:0.14921966 18:0.91354114 19:1.1576183 20:0.82168186 21:−0.59960753 22:−0.3806065 23:0.036252648 24:0.40446517 25:−0.041981112 26:0.5394733 27:0.10547557 28:−0.18626553 29:0.43777582 30:−1.2531258 31:−0.57186949 32:0.10621319 33:0.55403918 34:−0.30708826 35:0.042276658 36:−0.97170401 37:1.5680649 38:−0.35357198 39:−0.31896117 40:0.1885691 41:0.14435399 42:−0.80022198 43:0.050054323 44:0.21044557 45:0.9939636 46:0.016742287 47:−0.0084441807 48:0.42134136 49:−1.3300655 50:0.14887142 51:−1.5286498 52:1.0831087 53:0.01669452 54:−1.0117697 55:−1.5333623 56:−0.23926201 57:1.1092873 58:−0.30872497 59:−0.0068817809 60:−0.08816056 61:−0.23867473 62:0.14579196 63:0.93483233 64:−1.314449 65:0.67001724 66:−0.43909997 67:−0.21468382 68:−0.029038141 69:0.6566391 70:0.66849053 71:−0.68139273 72:−0.19444059 73:1.0253628 74:−0.39257091 75:0.16086669 76:0.59910434 77:−0.099923208 78:−1.3054628 79:−1.3442253 80:1.4393352 81:0.25903618 82:−0.08239346 83:−0.32068664 84:0.9061048 85:−0.81428427 86:0.10483883 87:0.78024024 88:−0.28707725 89:0.37337458 90:0.26700154 91:−0.1439804 92:−0.77208322 93:−0.18243469 94:−0.67778766 95:0.43233031 96:0.08580488 97:0.50075346 98:−0.25803816 99:−0.60087615 100:0.17977718 101:0.009441345 102:0.20656237 103:−0.17051774 104:−0.11870009 105:0.17388996 106:−0.179243 107:−0.78554499 108:−0.83105779 109:−0.13264436 110:0.96408862 111:−0.10831727 112:0.10464411 113:−0.69846845 114:−0.63966185 115:0.1620747 116:0.22842549 117:−0.068682909 118:0.10341078 119:−0.37485048 120:0.18794569 121:−0.16108523 122:0.2544432 123:−0.087778352 124:−0.24145311 125:0.19625695 126:−0.41050631 127:0.46743992 128:−0.078798428 129:0.050098442 130:−0.11853292 131:−0.53845382 132:−0.191057 133:0.17174664 134:0.16784234 135:−0.28137264 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0011487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # −0.0034319981554139273 1:11.063172 2:−4.1735458 3:−2.1705191 4:3.1756155 5:−2.6342511 6:0.35717416 7:−2.6251674 8:−2.3413982 9:1.3099627 10:2.2732904 11:1.9024211 12:−2.9932053 13:2.0243397 14:−0.28601316 15:0.81185395 16:−2.5839396 17:2.4302902 18:3.7185061 19:−0.9046219 20:0.72545081 21:−1.4551767 22:1.4636325 23:−0.15903565 24:−1.6384495 25:0.075246438 26:−0.20895387 27:0.26143897 28:1.2070005 29:2.0606019 30:2.1030214 31:−0.69226116 32:2.1005497 33:0.75281036 34:2.7544527 35:0.082330272 36:0.38176236 37:−1.5440055 38:0.26154569 39:−1.1583414 40:0.12141833 41:−0.16811602 42:1.2153684 43:1.6256666 44:0.55115259 45:0.25212508 46:−0.090178415 47:0.071696945 48:−0.092321232 49:−1.1144848 50:−0.012306355 51:0.28413066 52:−0.67935228 53:1.2980931 54:−0.13099827 |

APPENDIX C1-continued

| SVM Model Weights (340; Normal/Diseased) |
|---|
| 55:0.12346329 56:0.11142293 57:0.27578577 58:−0.050162587 59:−1.1625016 60:−0.77165097 61:−0.012743402 62:−0.40751636 63:1.8688 64:0.48271897 65:−0.584391 66:−0.41269445 67:−0.61985165 68:0.26657802 69:0.40913209 70:0.17663826 71:−1.1105018 72:0.71721327 73:0.40302157 74:−0.82035613 75:−0.8042627 76:−0.47997978 77:−0.1955671 78:−0.19370109 79:−0.35962215 80:−0.2477721 81:1.1621563 82:−0.70190388 83:−0.085306503 84:−0.30679044 85:0.45231619 86:0.019608933 87:−0.010397393 88:−1.239265 89:−0.47596693 90:0.51871115 91:0.428707 92:−0.27526024 93:−0.25018066 94:0.50646722 95:−0.39119193 96:−0.24217156 97:0.42900217 98:−0.2648038 99:0.13672093 100:0.50403929 101:0.15778866 102:0.67659736 103:−0.048415028 104:0.11952205 105:0.71793604 106:−0.65702438 107:−0.12218437 108:0.23302214 109:−0.24624877 110:0.79546916 111:−0.14148891 112:−0.10892753 113:0.060863588 114:0.85004985 115:0.20567821 116:0.02877306 117:−0.42616463 118:0.17896028 119:0.34737083 120:−0.17568201 121:−0.21698052 122:−0.20276235 123:0.31455246 124:0.075520784 125:−0.33748752 126:−0.11602205 127:−0.1612832 128:0.54019374 129:0.20805612 130:−0.15536913 131:−0.044152133 132:0.14521536 133:0.0065865624 134:0.028667204 135:0.15785635 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.0034319981554139273 1:−5.7919517 2:−2.1810565 3:0.89991498 4:4.4267159 5:0.42934251 6:0.0051537198 7:2.4697821 8:−0.77805513 9:0.41163149 10:−2.9729836 11:−0.4103817 12:0.5306235 13:0.1541082 14:0.88863766 15:1.8568023 16:−1.138868 17:−2.3147066 18:−1.5117507 19:0.69398737 20:0.65491122 21:2.016608 22:−1.9388435 23:−0.48158178 24:0.49413031 25:1.759385 26:0.56169939 27:1.358276 28:−0.67969912 29:−0.17309627 30:−0.31775782 31:0.089694984 32:0.026966177 33:0.12238708 34:−0.54287702 35:0.92235756 36:−1.1001273 37:−0.63166147 38:−0.11067349 39:1.2273777 40:−1.2410905 41:−1.389986 42:−1.4577581 43:0.55986434 44:−0.86515212 45:1.1510192 46:−1.5532745 47:−0.23236232 48:1.539893 49:−0.75711602 50:−0.37118486 51:−0.023546115 52:−1.4525793 53:0.74840224 54:−1.3073236 55:−0.42132354 56:−0.044209357 57:0.59822321 58:−1.0615158 59:−0.21888712 60:0.48570648 61:0.086135194 62:−0.55055785 63:0.19289941 64:1.4558742 65:0.47681028 66:−1.5687805 67:0.88204062 68:−0.90476662 69:0.31320921 70:−1.8967479 71:1.0429516 72:0.22732769 73:0.76303196 74:0.99647546 75:−0.16086195 76:−0.079184987 77:−0.31307292 78:−0.28297859 79:0.53510016 80:−0.61627305 81:1.2682763 82:−0.86660659 83:0.79760998 84:0.88989186 85:0.31910986 86:0.30828616 87:0.10880225 88:−0.32300088 89:0.2482516 90:0.73883563 91:−0.29639083 92:−0.071727216 93:0.29177046 94:−0.11549116 95:0.1442111 96:0.15351339 97:−0.34574953 98:−1.0521226 99:−0.00024694949 100:0.62961411 101:−0.27220163 102:−0.23599112 103:−0.77224076 104:−0.58291781 105:0.37459138 106:−0.21903124 |

APPENDIX C1-continued

| SVM Model Weights (340; Normal/Diseased) |
|---|
| 107:−0.20094772 108:0.11205977 109:0.032487899 110:−0.70163465 111:0.36078116 112:0.52375674 113:0.23465632 114:−0.14732425 115:0.25871086 116:0.30047008 117:0.20038417 118:0.50773978 119:−0.090070978 120:−0.31659314 121:0.2785669 122:0.017405029 123:−0.19067985 124:0.33105844 125:0.13414019 126:−0.2206354 127:−0.041879795 128:0.11636984 129:−0.027531331 130:0.013377704 131:0.0040420946 132:0.095371231 133:−0.1024501 134:−0.34976953 135:0.19571705 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:−1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.0034319981554139273 1:−4.8213444 2:1.5760788 3:−0.57018983 4:4.005219 5:−2.8392484 6:1.7106702 7:9.8552361 8:2.2270277 9:−1.4904127 10:−7.1802697 11:−3.0619631 12:−0.14209715 13:−1.4537175 14:−2.877516 15:−1.1271073 16:0.53900164 17:−1.8657733 18:−0.53384638 19:1.5783185 20:−0.68478709 21:0.032381013 22:−1.4166883 23:−0.0025301133 24:−1.1854193 25:−0.62957221 26:−3.2034943 27:0.077824026 28:1.7398168 29:−0.01426788 30:−0.64900607 31:−0.21030807 32:0.88778365 33:0.076254755 34:2.1417699 35:−0.27708969 36:0.31239855 37:0.70956808 38:−0.64874792 39:0.1058379 40:−0.42606917 41:0.72831851 42:−0.25673389 43:0.2500523 44:−1.6403226 45:2.1886477 46:−2.2809436 47:−0.1286744 48:−0.12771322 49:0.68130213 50:1.0067925 51:−0.92800182 52:0.26234749 53:−0.089902036 54:−0.42107287 55:−1.3764564 56:−1.510673 57:−0.43247876 58:−0.68712801 59:0.7631014 60:−0.82621932 61:1.5242251 62:−0.56152421 63:−0.57718027 64:−0.29271552 65:−0.19943641 66:−0.54750919 67:0.22625037 68:0.1774147 69:−1.4245882 70:−0.1029859 71:0.00042244355 72:1.3596847 73:1.0236553 74:−0.48945808 75:−0.15918885 76:−0.12789704 77:−0.1897447 78:0.099541761 79:−0.28899437 80:0.19369102 81:0.60415381 82:−0.13581827 83:−0.12477767 84:−0.75226313 85:−1.4051485 86:−1.3270912 87:−0.27294436 88:−0.17954999 89:−0.4420633 90:0.22422667 91:−0.9636271 92:1.0058788 93:−0.051285181 94:0.28411558 95:−0.20359176 96:0.16821519 97:−0.0063997959 98:0.59462065 99:0.23772943 100:0.020809731 101:0.17293215 102:−0.041189268 103:0.27283588 104:0.068614408 105:−0.48364761 106:−0.60488576 107:0.19049406 108:0.33091903 109:0.118357 110:0.020485993 111:−0.36667657 112:−0.26907983 113:−0.069352731 114:0.26436314 115:−0.41242686 116:0.14569035 117:−0.0087670833 118:−0.047765266 119:0.057778087 120:0.62842041 121:0.25619072 122:−0.20833282 123:0.15089604 124:0.21913984 125:0.011435734 126:−0.010265729 127:−0.21045032 128:−0.092223473 129:0.1509573 130:0.04844344 131:0.10513306 132:−0.014935663 133:−0.1716301 134:0.10946822 135:0.027854124 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 |

APPENDIX C1-continued

| SVM Model Weights (340; Normal/Diseased) |
|---|
| 153:−0.0020869875 154:−0.0023751855 155:1.1204498e−006 156:0.0039485889<br>157:−0.00011155871 158:0.00070337567 159:0.0012323871 160:0.0021008069 161:0.0028489598<br>162:0.00029079549 163:0.0020081406 164:0.0044465163 165:0.007065278 166:0.0012901861<br>167:0.0037493915 168:−0.0023597497 169:−0.00012567961 170:0.00047573209 171:7.8875659e−005<br>172:−0.0056320974 173:−0.0067036133 174:0.00017559867 175:0.001684437<br>176:−0.0034504069 177:0.0018235954 178:−0.001383971 179:0.0004998623 180:−0.00066253374<br>181:0.0015807585 182:0.00412085 183:0.0021063511 184:0.00072732504 185:−0.0012095358<br>186:−0.0030121093 187:−0.0020631803 188:−0.00068084424 189:0.0002527938<br>190:−0.0034640408 191:−0.00026976471 192:0.00097010034 193:−0.0011612385 194:−0.0015113452<br>195:0.00062438019 196:−0.00013164691 197:0.0020616048 198:0.0010445472<br>199:−0.0049765292 200:9.8877339e−005 201:0.0028779099 202:−0.0036701721 203:0.00099803088<br>204:0.00068234798 205:0.002192216 206:0.0033146022 207:0.00050616561 208:−0.0031757453<br>209:0.0028448526 210:0.00092352234 211:−0.0022140611 212:−0.0013608048 213:0.0051376815<br>214:−0.0017870248 215:−0.0027518668 216:0.00043837572 217:−0.027317183 218:−0.024619192<br>219:−0.01382506 220:−0.015382294 221:−0.016386922 222:−0.0094594397 223:−0.0056853383<br>224:−0.00050634646 225:−0.00087913428 226:−0.023968795 227:−0.0034698097<br>228:−0.0016731552 229:0.00047607321 230:−0.011432272 231:−0.00036644109 232:−0.0025967851<br>233:0.0015593689 234:−0.0042631673 235:−0.0053286692 236:−0.0059999214 237:−0.087129325<br>238:−0.063751429 239:−0.0045496477 240:−0.0073839114 241:0.0014150206 242:−0.0042075687<br>243:−0.0022374168 244:−0.041910719 245:−0.030919394 246:−0.049301699 247:−0.019442754<br>248:−0.0019611341 249:−0.0072449106 250:−0.0051453672 251:−0.0072873179 252:−0.005927789<br>253:−0.0018599511 254:−0.017141052 255:−0.023494685 256:−0.01788312 257:−0.01943502<br>258:−0.0060224077 259:−0.0073500308 260:−0.0064477329 261:−0.0002986097 262:−0.0014349599<br>263:−0.0020359957 264:−0.0082596857 265:−0.006963369 266:−0.0016096481 267:−0.0083991755<br>268:−0.046351645 269:−0.046128571 270:−0.011141608 271:0.0020650877 272:−0.0010642689<br>273:−0.018076098 274:−0.016929928 275:−0.0052876701 276:−0.0025432054 277:−0.04111632<br>278:−0.031511344 279:−0.019488858 280:−0.0036160324 281:−0.032332413 282:−0.023754911<br>283:−0.0030713808 284:−0.033357695 285:−0.027144579 286:−0.0093234172 287:−0.0091438433<br>288:0.00080924761 289:−0.0040808818 290:−0.00058058492 291:0.00025530611<br>292:0.00042821659 293:−0.0017559038 294:−0.00030293313 295:−0.0004816725<br>296:−0.00057298481 297:−0.00086739491 298:0.0020803961 299:0.00010370808 300:0.00075778627<br>301:0.00074104586 302:−0.00021793939 303:0.0013351805 304:−0.0006143825<br>305:0.0025815656 306:7.1731614e−005 307:−0.0052312948 308:−0.00063595735<br>309:0.0015091125 310:−0.00024647679 311:−0.0050271503 312:−0.00065122027<br>313:−0.00070704299 314:−0.0038100008 315:0.0022923627 316:0.0019759815 317:0.00079242635<br>318:0.0045642676 319:0.001573379 320:0.0015903091 321:0.00074843148 322:−0.00091753813<br>323:0.0021253934 324:0.0013280844 325:−0.0030691659 326:−0.0033078301 327:0.0012743858<br>328:0.0024482214 329:0.0018192574 330:0.0026370357 331:0.0017312634 332:0.00066732749<br>333:0.00034391912 334:0.0037949879 335:0.0018411272 336:0.0051615993 337:0.0017553387<br>338:−0.0027431778 339:−0.0055160136 340:0.0031345901 #<br>−0.0034319981554139273 1:8.4564133 2:−3.6954048 3:−0.36950901 4:2.0615106 5:0.32085344<br>6:−2.5327203 7:−0.28457209 8:−1.186967 9:−1.2540523 10:2.2149053 11:−2.8718159 12:0.93030947<br>13:−2.0749297 14:−0.2423725 15:−1.8521192 16:−1.5626588 17:3.2296343 18:0.065072417<br>19:0.17800856 20:0.73286116 21:1.1539247 22:1.1033744 23:0.1072376 24:−0.81941801<br>25:−1.7166369 26:−0.49180382 27:−0.88959998 28:−0.783346 29:0.55402172 30:−0.21719469<br>31:−0.38976419 32:−1.8080884 33:0.093785204 34:−0.34544724 35:2.3562729 36:−0.55151314<br>37:1.1748444 38:0.35242981 39:−0.68477893 40:−0.089026608 41:0.21341442 42:0.93687207<br>43:0.044087749 44:−0.26936442 45:1.4698968 46:−0.94894558 47:−0.20715962 48:0.17709284<br>49:−0.092726924 50:−0.03063637 51:−0.053195205 52:−1.4915875 53:−0.091144487 54:1.1582738<br>55:−2.4273913 56:0.10436805 57:−0.16633649 58:−0.67621684 59:−0.74687052 60:0.37081623<br>61:−1.4236872 62:0.54976654 63:−0.023168497 64:−0.61734682 65:0.34305745 66:0.54878235<br>67:1.023862 68:0.95399183 69:0.61367548 70:0.2599085 71:0.75868374 72:0.27436996<br>73:0.23401526 74:−0.75373387 75:−1.3631232 76:0.77333856 77:−0.3686007 78:−0.066425569<br>79:0.82971358 80:−0.27613378 81:0.3844921 82:0.093253352 83:−0.62704402 84:−0.84857655<br>85:0.058126319 86:−0.34825379 87:−0.44060946 88:0.3343448 89:−0.61846036 90:−0.40606138<br>91:1.278663 92:−0.065161608 93:0.0057740607 94:0.72780412 95:0.53399944 96:−0.12172013<br>97:−0.89835423 98:0.41797453 99:0.13312228 100:0.14268644 101:−0.61742043 102:−0.13092716<br>103:−0.34983107 104:−0.041657399 105:−0.49653813 106:−0.076033384 107:−0.30043787<br>108:−0.16424669 109:−0.24185894 110:0.10712297 111:0.15874013 112:−0.23471656<br>113:−0.033890154 114:0.030354928 115:0.39794296 116:0.40289733 117:0.22425254 118:−0.73588479<br>119:−0.16229978 120:−0.70940739 121:0.29919609 122:−0.0080191102 123:−0.22732708<br>124:0.79446983 125:0.13968551 126:0.12227754 127:0.033713445 128:−0.17334862<br>129:0.1498903 130:−0.061867706 131:−0.19532421 132:0.058789115 133:0.054021295<br>134:0.0071761222 135:−0.29731074 136:−0.0036672305 137:9.853208e−005 138:−0.017125415<br>139:0.0062208101 140:0.00056613336 141:0.0012280536 142:−0.00039310646<br>143:−0.0063707544 144:0.0015248039 145:−0.0029345977 146:−0.00076821423 147:0.00013666278<br>148:−0.0051379474 149:0.0066761598 150:−0.0024066679 151:0.0038081626 152:−0.0013487631<br>153:−0.0020869875 154:−0.0023751855 155:1.1204498e−006 156:0.0039485889<br>157:−0.00011155871 158:0.00070337567 159:0.0012323871 160:0.0021008069 161:0.0028489598<br>162:0.00029079549 163:0.0020081406 164:0.0044465163 165:0.007065278 166:0.0012901861<br>167:0.0037493915 168:−0.0023597497 169:−0.00012567961 170:0.00047573209 171:7.8875659e−005<br>172:−0.0056320974 173:−0.0067036133 174:0.00017559867 175:0.001684437<br>176:−0.0034504069 177:0.0018235954 178:−0.001383971 179:0.0004998623 180:−0.00066253374<br>181:0.0015807585 182:0.00412085 183:0.0021063511 184:0.00072732504 185:−0.0012095358<br>186:−0.0030121093 187:−0.0020631803 188:−0.00068084424 189:0.0002527938<br>190:−0.0034640408 191:−0.00026976471 192:0.00097010034 193:−0.0011612385 194:−0.0015113452<br>195:0.00062438019 196:−0.00013164691 197:0.0020616048 198:0.0010445472 |

APPENDIX C1-continued

SVM Model Weights
(340; Normal/Diseased)

199:−0.0049765292 200:9.8877339e-005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e-005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 #
0.0027017411680786115 1:−8.7888012 2:−5.0174055 3:15.464613 4:12.69648 5:0.48444548 6:4.1684113 7:−0.74741292 8:−3.0366001 9:3.0165656 10:0.36663359 11:0.090890579 12:1.0652288 13:−1.5409054 14:0.2649897 15:−0.43269604 16:−0.038893078 17:−0.77519739 18:0.81574935 19:−1.0314269 20:−3.2741005 21:−1.5639375 22:−0.5126884 23:0.82985568 24:−1.0077952 25:1.0022768 26:0.1195637 27:1.2333072 28:−1.1778735 29:0.83554494 30:−0.10847708 31:1.3086255 32:−1.6946321 33:1.2967862 34:−0.79051191 35:0.56799436 36:−1.7944912 37:0.58153147 38:−3.3880858 39:2.1127441 40:−0.35073772 41:0.3430565 42:−0.19415511 43:0.87412983 44:−1.4260486 45:−0.2287287 46:0.86864233 47:−0.34647352 48:−1.0671141 49:0.81541055 50:−1.2651246 51:1.6905305 52:−0.76940089 53:1.2428665 54:−0.253553 55:0.75670892 56:0.037519887 57:1.3644034 58:−1.3079399 59:0.41920772 60:−1.4656103 61:−0.38064155 62:−1.4655507 63:0.85689932 64:−0.25574639 65:−0.94760424 66:0.048869174 67:0.52866745 68:0.64850807 69:0.541134 70:−1.4543862 71:0.067330085 72:0.054305743 73:−0.48869985 74:−1.1989335 75:0.44269657 76:0.71393716 77:−0.32942852 78:0.4908244 79:0.13667721 80:0.75521457 81:−0.23717679 82:0.74724638 83:−0.19844957 84:−0.66304415 85:0.4589403 86:−0.41549325 87:0.84629393 88:0.30515087 89:0.21237767 90:−0.89250696 91:0.038783573 92:−0.18975438 93:0.20923898 94:−0.19858038 95:−0.4777692 96:−0.87259448 97:−0.12023643 98:0.41243643 99:0.24959414 100:−0.010782805 101:0.031865936 102:0.28773546 103:0.11154114 104:0.055913877 105:−0.048088338 106:0.37550211 107:−0.29136792 108:0.39171529 109:−0.0071665524 110:0.084823608 111:−0.23609819 112:−0.22450648 113:0.15887335 114:−0.13393964 115:−0.046204716 116:−0.096150249 117:−0.38202289 118:0.21397366 119:0.04011764 120:−0.033773161 121:0.14804859 122:0.013776889 123:0.062574401 124:−0.03248312 125:0.18471891 126:−0.065728314 127:0.21946739 128:−0.099114761 129:0.21744357 130:0.27350184 131:−0.062139168 132:0.025091942 133:−0.074193038 134:0.080150649 135:0.21900623 136:−0.0036672305 137:9.853208e-005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e-006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e-005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e-005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168

APPENDIX C1-continued

SVM Model Weights
(340; Normal/Diseased)

244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−00.0027431778 339:−00.0055160136
340:0.0031345901 #
0.0034319981554139273 1:−2.6544154 2:−1.6780306 3:0.060192857 4:4.1504841 5:0.24912068
6:−6.624095 7:0.57551324 8:−0.40938711 9:0.95585006 10:−1.6248276 11:2.5019817
12:0.56307358 13:0.95418429 14:0.88776869 15:3.2650585 16:−0.68683743 17:−2.1359942
18:1.4519684 19:2.2777252 20:−0.086952887 21:0.98849201 22:−0.43877348 23:2.5149901
24:−0.61557049 25:−1.8795074 26:−2.9768124 27:0.79192317 28:−0.13132951 29:−0.029296318
30:0.93309855 31:−0.7005055 32:0.71704352 33:−0.25660962 34:−2.2047393 35:−0.25032863
36:0.71683908 37:−0.74325979 38:−0.43488362 39:0.098624043 40:0.35353583 41:0.48026922
42:0.35613587 43:0.23364027 44:−0.19640292 45:−0.059701335 46:−0.36572802 47:−0.56502438
48:0.17310216 49:1.1000975 50:0.49338856 51:−0.50896662 52:0.042086825 53:0.79794669
54:−2.1193681 55:0.25861913 56:−0.33582497 57:−0.012439645 58:0.20513313 59:−0.60620952
60:0.54638368 61:−0.81247282 62:0.62839669 63:0.48116341 64:0.38637295 65:−0.24869362
66:0.84799761 67:0.30435371 68:−0.0083769634 69:−0.36916006 70:1.1698636 71:−0.28332841
72:−0.16254009 73:0.60171705 74:−0.3651886 75:0.13924569 76:0.14928086 77:−0.22138734
78:−0.23113471 79:0.71544218 80:−0.68907952 81:0.25123066 82:0.35675538 83:0.7597639
84:−1.4002386 85:1.2163451 86:−0.39963025 87:0.50460058 88:0.9311859 89:−0.035857338
90:0.20145109 91:0.56187814 92:−0.00098289666 93:0.18569236 94:−0.90521616 95:0.58429497
96:0.89183861 97:0.020912996 98:−0.005451675 99:0.033450056 100:0.61778504
101:0.05631901 102:0.80241334 103:0.80124873 104:−0.19415718 105:−0.12153812
106:0.33368483 107:0.1332514 108:0.11274892 109:0.43854931 110:−0.46008971
111:−0.030246915 112:0.88152426 113:0.097098045 114:0.046684071 115:0.20595978
116:0.16985013 117:0.15701078 118:−0.25029105 119:−0.34454104 120:0.30681372
121:−0.39321345 122:−0.35919693 123:0.15618342 124:−0.25364962 125:−0.084704638
126:−0.50931698 127:0.18625343 128:−0.14921896 129:0.13651654 130:−0.18056574 131:0.071665302
132:0.4186812 133:−0.19416773 134:0.37088791 135:−0.2010105 136:−0.0036672305
137:9.853208e−005 138:−0.017125415 139:0.0062208101 140:0.00056613336 141:0.0012280536
142:−0.00039310646 143:−0.0063707544 144:0.0015248039 145:−0.0029345977
146:−0.00076821423 147:0.00013666278 148:−0.0051379474 149:0.0066761598 150:−0.0024066679
151:0.0038081626 152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761

APPENDIX C1-continued

SVM Model Weights
(340; Normal/Diseased)

289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
0.0034319981554139273 1:−4.2092881 2:−2.4297073 3:2.3812873 4:3.7497678 5:−3.525115
6:−4.9855132 7:6.1610827 8:2.7601898 9:−2.8208137 10:−3.3654191 11:−0.56684256 12:0.35663861
13:−2.660598 14:−1.8712988 15:−1.387481 16:−2.1275451 17:−0.54285592 18:−1.2628362
19:2.989496 20:−1.130962 21:0.9517414 22:−1.2566395 23:−0.34647283 24:0.77426749
25:−1.3361136 26:−1.7966329 27:0.40518939 28:−1.1118909 29:−1.0633837 30:−0.41736361
31:−0.84764743 32:1.1794119 33:1.6799232 34:−0.63335872 35:1.6104892 36:−1.1103476
37:0.63073111 38:0.48384947 39:0.89936668 40:−0.082325786 41:0.76218665 42:0.97860414
43:−0.37083343 44:0.59187639 45:1.1464876 46:1.1205767 47:−0.8635487 48:1.3752649
49:0.51784384 50:−0.69380736 51:0.72513711 52:0.21139859 53:−0.93220896 54:0.48446506
55:1.2326409 56:0.69779438 57:−0.010709514 58:−1.1019911 59:−1.4584427 60:0.24385148
61:0.9553318 62:0.52746499 63:0.75839889 64:−1.0763538 65:−1.1380903 66:−0.043663036
67:0.55343688 68:−1.0342745 69:−1.0344036 70:0.79018819 71:−1.7690177 72:−0.66686332
73:−0.34390387 74:1.0351527 75:−0.86768883 76:−0.31033605 77:0.18996391 78:−0.22393461
79:0.12826207 80:−0.28926349 81:−0.012549644 82:−1.2416493 83:−1.5032756 84:0.082687184
85:1.2248921 86:0.18344188 87:0.40543467 88:−0.036672145 89:0.049684782 90:−0.37984914
91:−0.22777097 92:−0.14267235 93:0.41303235 94:−0.140533 95:0.028687863 96:0.66761196
97:−0.65218747 98:0.52985412 99:0.0063670813 100:−0.14858533 101:0.4830938 102:−0.53542697
103:−0.27086106 104:−0.21960017 105:−0.22140765 106:0.3210586 107:0.6337716
108:−0.17943282 109:−0.31492969 110:0.34741938 111:−0.2334467 112:−0.19010915 113:0.35179803
114:−0.13610896 115:−0.11633465 116:−0.50814229 117:−0.14944653 118:0.31658381
119:0.17294919 120:−0.18883821 121:−0.070355289 122:0.14691432 123:−0.067781903
124:0.16578886 125:−0.40197206 126:−0.038871594 127:0.10111403 128:0.18132031
129:−0.14124268 130:−0.011328657 131:−0.32373616 132:−0.0019076664 133:0.095955566
134:−0.043801256 135:0.20514773 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133 174:0.00017559867 175:0.001684437
176:−0.0034504069 177:0.0018235954 178:−0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938
190:−0.0034640408 191:−0.00026976471 192:0.00097010034 193:−0.0011612385 194:−0.0015113452
195:0.00062438019 196:−0.00013164691 197:0.0020616048 198:0.0010445472
199:−0.0049765292 200:9.8877339e−005 201:0.0028779099 202:−0.0036701721 203:0.00099803088
204:0.00068234798 205:0.002192216 206:0.0033146022 207:0.00050616561 208:−0.0031757453
209:0.0028448526 210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097
228:−0.0016731552 229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749

APPENDIX C1-continued

SVM Model Weights
(340; Normal/Diseased)

333:0.00034391912 334:0.0037949879 335:0.0018411272 336:0.0051615993 337:0.0017553387
338:−0.0027431778 339:−0.0055160136 340:0.0031345901 #
0.0034319981554139273 1:−7.509798 2:−4.5393901 3:−2.8062258 4:3.4199057 5:3.2766123
6:−6.2061114 7:−3.7431328 8:0.69338125 9:1.6215347 10:1.2656826 11:2.7182131 12:−0.35331067
13:−0.94589573 14:0.90906739 15:0.93549758 16:0.38136375 17:0.90199894 18:−0.53325403
19:−1.0350369 20:0.1937726 21:0.45757112 22:0.39697847 23:−0.39251831 24:1.403145
25:−2.4881928 26:1.5786802 27:1.5884699 28:0.32738572 29:0.77424771 30:−0.48961881
31:−0.69184321 32:−0.11602285 33:0.25669566 34:0.45848355 35:−2.2879128 36:−0.97574413
37:0.34878814 38:−0.32084075 39:−0.51838773 40:−0.48434633 41:0.40164044 42:−1.2636504
43:1.3239561 44:−0.48785928 45:0.056154378 46:1.0239472 47:0.50110769 48:0.0026843392
49:1.1051512 50:−0.25809002 51:0.46542385 52:0.097595304 53:−0.8211751 54:1.3499396
55:−0.55995923 56:−1.3507671 57:0.88989532 58:−0.62262529 59:1.4444965 60:−0.48785457
61:−0.5163992 62:−0.56071895 63:−0.19808592 64:1.1346015 65:−1.5523173 66:1.5615344
67:−0.05772467 68:−0.64757806 69:−1.8814909 70:0.69906181 71:0.21192646 72:−1.3310343
73:0.59936488 74:0.050508223 75:−0.035055101 76:−0.060202323 77:1.5310905 78:0.32611093
79:−1.7685404 80:−0.47976485 81:−0.17680326 82:0.0080885431 83:−0.59574872 84:−0.47070134
85:−0.022143023 86:0.295084 87:−0.37883916 88:−0.034981117 89:1.137392 90:0.77776331
91:0.27295676 92:0.22188742 93:0.4453505 94:−0.40577534 95:−0.6665104 96:−0.59053838
97:−0.68325025 98:−0.057355829 99:0.26135218 100:0.076433465 101:0.64764386 102:−0.14395231
103:−0.27579483 104:−0.45135194 105:0.079337493 106:−0.81073594 107:−0.36825472
108:−0.24335791 109:0.3524237 110:−0.13799277 111:−0.21156082 112:0.17572561 113:0.075513721
114:0.1794613 115:0.23240829 116:0.66189498 117:0.35326475 118:−0.26618981
119:−0.11951475 120:−0.15367769 121:−0.13597105 122:−0.11813584 123:−0.13011122 124:0.13159281
125:−0.061072338 126:0.11232304 127:0.015226905 128:0.10234105 129:0.15158094
130:−0.12353852 131:−0.052670654 132:−0.050947152 133:0.087743796 134:−0.15804203
135:0.0023846379 136:−0.0036672305 137:9.853208e−005 138:−0.017125415 139:0.0062208101
140:0.00056613336 141:0.0012280536 142:−0.00039310646 143:−0.0063707544
144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889 157:−0.00011155871
158:0.00070337567 159:0.0012323871 160:0.0021008069 161:0.0028489598 162:0.00029079549
163:0.0020081406 164:0.0044465163 165:0.007065278 166:0.0012901861 167:0.0037493915
168:−0.0023597497 169:−0.00012567961 170:0.00047573209 171:7.8875659e−005
172:−0.0056320974 173:−0.0067036133 174:0.00017559867 175:0.001684437 176:−0.0034504069
177:0.0018235954 178:−0.001383971 179:0.0004998623 180:−0.00066253374 181:0.0015807585
182:0.00412085 183:0.0021063511 184:0.00072732504 185:−0.0012095358 186:−0.0030121093
187:−0.0020631803 188:−0.00068084424 189:0.0002527938 190:−0.0034640408
191:−0.00026976471 192:0.00097010034 193:−0.0011612385 194:−0.0015113452 195:0.00062438019
196:−0.00013164691 197:0.0020616048 198:0.0010445472 199:−0.0049765292 200:9.8877339e−005
201:0.0028779099 202:−0.0036701721 203:0.00099803088 204:0.00068234798
205:0.002192216 206:0.0033146022 207:0.00050616561 208:−0.0031757453 209:0.0028448526
210:0.00092352234 211:−0.0022140611 212:−0.0013608048 213:−0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097 228:−0.0016731552
229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
−0.0034319981554139273 1:10.097442 2:−1.8614138 3:1.4156544 4:1.4052474 5:0.31974572
6:−5.6366968 7:−2.7028873 8:−2.4760547 9:2.5067186 10:2.0757139 11:−2.1181877 12:−0.90601051
13:1.0449494 14:−0.63680339 15:−1.3693681 16:−1.4672149 17:2.2615716 18:1.0364233
19:−0.88492882 20:0.77747375 21:−0.23462507 22:−0.168164 23:0.030179759 24:−1.0176415
25:0.83552551 26:−0.99221385 27:0.31474352 28:−1.0523298 29:0.55194938 30:0.16242579
31:0.45075864 32:0.82697576 33:−0.70048535 34:0.77331382 35:1.29409 36:−0.094384804
37:0.64095533 38:−0.2618013 39:−1.0752306 40:−0.16970454 41:0.6047948 42:0.27205655
43:0.83269829 44:0.11379907 45:0.66776836 46:−0.56533515 47:−0.43901965 48:0.8195048

APPENDIX C1-continued

| SVM Model Weights (340; Normal/Diseased) |
|---|
| 49:0.98343772 50:−0.65349871 51:−0.019731186 52:−0.95981377 53:0.32438889 54:0.69812906 55:0.20094955 56:1.2491561 57:0.031027239 58:0.082117409 59:0.30294687 60:0.62821972 61:2.1786509 62:0.24057224 63:−0.22619005 64:−0.35955474 65:−0.33847553 66:0.33624274 67:0.44285411 68:−1.5966766 69:0.037208516 70:−1.1043345 71:0.57435846 72:−0.01608846 73:0.53170288 74:0.37930936 75:0.31339011 76:0.80519551 77:−0.92552328 78:0.28643498 79:0.40159059 80:−0.38341659 81:0.36391017 82:−0.51450759 83:−0.63291878 84:−0.46120426 85:−0.27918485 86:0.34871864 87:0.17048147 88:0.7253527 89:0.67305189 90:0.37838539 91:−0.090282358 92:0.17472583 93:−0.43493021 94:−0.022548378 95:−0.8307212 96:−0.57434338 97:−0.0081778113 98:0.14487791 99:−0.44569278 100:−0.51137346 101:−0.40962029 102:−0.19341755 103:0.098778024 104:−0.20596282 105:0.089972042 106:0.34845185 107:−0.15214404 108:0.26501644 109:0.35877842 110:−0.041504294 111:0.17308976 112:0.60561126 113:−0.12003516 114:0.39659998 115:−0.31480551 116:0.17561488 117:−0.20844509 118:−0.18373808 119:0.22723368 120:0.58503014 121:−0.13597277 122:0.32092217 123:−0.17124058 124:−0.74381268 125:0.36247513 126:0.29147545 127:−0.13300234 128:0.5308761 129:−0.37754473 130:0.12713683 131:−0.46769437 132:0.01638568 133:0.078148909 134:0.13933928 135:−0.65848154 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.0034319981554139273 1:7.2203302 2:−4.6925292 3:−0.71862835 4:2.4329977 5:0.17405996 6:−2.3858955 7:−3.6205564 8:−1.2306844 9:0.62873197 10:2.9880207 11:−0.4485932 12:−0.12904745 13:−0.65154469 14:0.80697656 15:−1.029856 16:1.529476 17:2.8022256 18:−1.0489378 19:−0.44924599 20:−0.80383497 21:−0.25904307 22:0.53846246 23:0.71031916 24:−2.3672302 25:−0.91945183 26:−0.78370333 27:0.12203253 28:0.72611457 29:−0.22881122 30:−0.79196155 31:−0.02377972 32:0.20235474 33:0.21350279 34:1.3739451 35:0.098526865 36:2.815995 37:−0.91403037 38:−0.5698511 39:−1.2917552 40:−1.4901602 41:−1.3911369 42:1.7263176 43:−1.0613565 44:−0.66679603 45:−0.70240986 46:−0.8640815 47:−0.099078871 48:−1.2030772 49:0.17561798 50:−1.004133 51:−0.090904243 52:0.0029521906 53:−0.59214115 54:0.60327482 55:0.8842234 56:−0.22315407 57:0.62547201 58:0.95840544 59:−0.34876853 60:0.53333133 61:−0.96676898 62:−1.5946102 63:0.70361596 64:−1.0295923 65:−0.18397623 66:0.10510585 67:0.11890922 68:−1.470775 69:1.7038034 70:−1.1788989 71:0.71039879 72:−0.02496448 73:1.0265777 74:0.72668654 75:−0.24382575 76:0.31476215 77:0.64805585 78:0.056707695 79:−0.032253273 80:−0.35613647 81:−0.29307088 82:−0.47884226 83:−0.031227961 84:−0.68177027 85:0.40402326 86:−1.0378106 87:−0.48057619 88:0.26687387 89:0.44517103 90:−0.13185617 91:−0.79598153 92:0.39016315 93:−0.038426097 94:−0.35109511 95:0.6302461 96:0.8314721 97:0.7800287 98:−0.36230257 99:0.42321414 100:−0.27125373 101:0.88582152 102:−0.041244105 103:0.39312255 104:−0.75197482 105:−0.20754905 106:0.1807169 107:−0.55275667 |

APPENDIX C1-continued

SVM Model Weights
(340; Normal/Diseased)

108:−0.46475485 109:0.0042910981 110:0.24430723 111:−0.63012105 112:−0.38737828
113:0.41612518 114:−0.12385218 115:−0.14095131 116:−0.072537988 117:0.41645119
118:0.25029391 119:0.12736414 120:−0.016967688 121:0.25864527 122:0.25795731
123:0.027023425 124:0.20076473 125:0.13234307 126:−0.20298678 127:−0.035363138
128:−0.23712821 129:−0.19125806 130:−0.38495818 131:−0.0039612763 132:−0.33421212
133:−0.089831248 134:−0.043627694 135:0.0078531522 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:−0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
−0.0027359298660988348 1:3.5329537 2:−10.95813 3:3.4194798 4:−7.8480668 5:3.7418206
6:−3.0329297 7:−2.0779335 8:−0.86376679 9:−0.23510407 10:2.2805333 11:−1.7733712
12:−0.88370395 13:0.80895215 14:4.2387309 15:−2.0776055 16:3.0777144 17:−0.79243094
18:0.84162772 19:−0.077937923 20:0.28963533 21:−1.3790681 22:1.4894168 23:0.018758779
24:−2.0270684 25:−0.68106169 26:−7.2576551 27:−1.8796045 28:2.9182773 29:−2.6407745
30:−2.0767155 31:0.86707813 32:−1.6518435 33:1.633288 34:−2.9613552 35:−4.4285808
36:−1.0467037 37:0.41871238 38:1.6681521 39:1.0266926 40:0.95897007 41:−3.4459255
42:−0.19771677 43:1.4036087 44:1.6188563 45:2.5977178 46:0.98996758 47:−0.82927483
48:0.61392421 49:−1.1662588 50:−0.98937833 51:−0.28667507 52:−0.93937808 53:0.97598058
54:0.52989149 55:−0.094056919 56:−0.48669103 57:0.83300668 58:−0.096311115 59:0.76985174
60:−0.19955865 61:0.70920098 62:−0.098080747 63:−0.58614087 64:−0.30448323 65:0.43787375
66:0.42960981 67:−0.62090302 68:0.67657304 69:−0.28415462 70:−0.60854691 71:−0.17868806
72:0.30537838 73:−0.17963754 74:0.36392453 75:0.4541378 76:0.098703489 77:−0.14385869
78:0.14480381 79:0.54459673 80:−0.32749698 81:0.5294469 82:−0.03399723 83:−0.085196897
84:0.036676209 85:−0.032222539 86:0.26534978 87:−0.024877865 88:0.26086593 89:−0.35706815
90:−0.38940847 91:−0.095371976 92:0.10332019 93:−0.0060825497 94:−0.34425345
95:−0.061376423 96:−0.250002 97:0.2352906 98:0.014484519 99:0.019998256 100:−0.32741973
101:0.19991307 102:−0.059084386 103:−0.069849722 104:0.014789577 105:0.29857653
106:−0.061006036 107:0.14511563 108:−0.16235837 109:−0.0017506834 110:0.25018567
111:−0.16615517 112:0.045857236 113:−0.083681598 114:−0.11050341 115:0.26918638
116:−0.031854916 117:0.097531058 118:0.087358326 119:0.047551025 120:−0.12220226
121:−0.073003165 122:0.075672865 123:−0.045106046 124:0.10887643 125:−0.22239558
126:−0.022245571 127:−0.15675882 128:0.1121482 129:0.040888242 130:0.0091433143
131:0.10210536 132:−0.077158056 133:0.037190031 134:0.049587522 135:−0.012612961
136:−0.0036672305 137:9.853208e−005 138:−0.017125415 139:0.0062208101 140:0.00056613336
141:0.0012280536 142:−0.00039310646 143:−0.0063707544 144:0.0015248039
145:−0.0029345977 146:−0.00076821423 147:0.00013666278 148:−0.0051379474 149:0.0066761598

APPENDIX C1-continued

| SVM Model Weights (340; Normal/Diseased) |
|---|
| 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246−:0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281−:0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # −0.0031316547997133743 1:10.264601 2:−0.059173197 3:1.2563672 4:0.93355006 5:0.10213261 6:−3.12937 7:0.1210808 8:−1.4454924 9:2.8236961 10:1.1237521 11:−3.9188919 12:−2.4904826 13:2.0705259 14:−0.87547851 15:−1.8442463 16:0.21780729 17:2.4239211 18:1.4910609 19:−1.729903 20:2.1160944 21:−1.7531475 22:−0.63739741 23:0.51525068 24:−2.1273396 25:0.43934068 26:−1.0054997 27:−1.7345521 28:−0.25552028 29:0.75789368 30:−1.0863563 31:1.4560143 32:1.7285388 33:0.094971634 34:0.95385522 35:−0.35644263 36:0.83385187 37:−0.56441391 38:0.26436624 39:−1.6112218 40:−0.29825702 41:0.97394598 42:−0.066852339 43:0.05723669 44:−0.2698839 45:0.12173406 46:−0.052312899 47:−1.6940966 48:1.4239658 49:1.2168394 50:1.3187749 51:−0.8759495 52:−0.22878745 53:0.0077490155 54:0.91228098 55:0.33469588 56:0.29470313 57:0.13694796 58:−0.91457546 59:−0.60467321 60:0.67347729 61:−0.37298837 62:0.57097292 63:−0.22237512 64:−0.33819744 65:−0.72712189 66:−0.15334231 67:0.11498885 68:−0.916785 69:−0.51799488 70:−0.48970297 71:−0.80190605 72:−0.031837724 73:0.73535842 74:−0.54567927 75:0.80711287 76:−0.38004223 77:−0.30100656 78:−0.51487565 79:−0.23349914 80:0.84564257 81:−0.43879128 82:−0.30966088 83:0.36664808 84:0.50657499 85:−0.53866541 86:0.13018405 87:0.1478551 88:1.2998698 89:−0.13508122 90:−0.0042357319 91:0.71661621 92:−0.21197355 93:0.87527633 94:−0.43137002 95:1.2418118 96:−0.41445854 97:0.21784753 98:0.40599355 99:0.03621532 100:−0.23641126 101:−0.31113592 102:−0.27580515 103:−0.448697 104:−0.55185413 105:−0.060220264 106:−0.084133178 107:−0.79462415 108:0.20238611 109:−0.069631435 110:−0.50526172 111:0.18115249 112:−0.31725854 113:−0.17745025 114:−0.27442679 115:−0.00098058628 116:−0.1830962 117:−0.13506769 118:0.08511965 119:−0.40842044 120:−0.030195696 121:−0.03650872 122:−0.45793927 123:0.18231007 124:−0.35971758 125:−0.13607821 126:0.3413052 127:0.022233941 128:−0.11121289 129:0.17808008 130:0.04543281 131:0.42961389 132:0.26634941 133:0.35952568 134:−0.14164415 135:0.59662807 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 |

APPENDIX C1-continued

| SVM Model Weights (340; Normal/Diseased) |
|---|
| 195:0.00062438019 196:−0.00013164691 197:0.0020616048 198:0.0010445472 199:−0.0049765292 200:9.8877339e-005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e-005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.0017047695258676798 1:8.3293247 2:−3.9943771 3:−1.2766048 4:1.7569972 5:2.6435943 6:−2.9492621 7:−2.3212342 8:−2.6703773 9:1.6562256 10:0.99037993 11:−1.6012954 12:−0.34458488 13:0.13430169 14:0.21423897 15:−1.2481678 16:−0.74102271 17:2.3277071 18:−0.68662477 19:−2.159126 20:0.51672584 21:0.24277323 22:0.73280674 23:1.1756219 24:0.25978401 25:0.63631743 26:1.7079741 27:2.0787354 28:−1.5707715 29:0.65416503 30:0.26913345 31:2.2607591 32:0.35912016 33:0.65344459 34:0.75340146 35:−0.57042199 36:−0.74616569 37:0.49215052 38:−0.49467999 39:0.41213545 40:0.45474479 41:−0.1624404 42:−0.15442291 43:−0.006333814 44:−0.83312565 45:−0.39217919 46:−1.3772601 47:0.84278703 48:−0.30854723 49:0.16744663 50:0.63391715 51:0.039532144 52:0.74026698 53:−0.42207003 54:−0.590087 55:−0.36480734 56:−0.69397259 57:0.26235241 58:−0.33095819 59:0.10752961 60:−0.31946054 61:0.14592922 62:0.65290701 63:0.52099472 64:−1.0849066 65:0.14312524 66:0.047710914 67:0.52469856 68:−0.45751137 69:0.21821585 70:−0.11044776 71:0.40490064 72:0.34637508 73:−0.50340813 74:−0.07373298 75:−0.21722183 76:0.55678886 77:0.44857395 78:−0.3983981 79:−0.21097562 80:−0.21726133 81:0.77907968 82:0.12184522 83:−0.35409185 84:0.42927939 85:−0.37174541 86:1.1881471 87:−0.17306812 88:−0.083240569 89:−0.54907328 90:0.32718092 91:−0.73995781 92:0.40705347 93:0.28813541 94:−0.26045853 95:−0.40955299 96:−0.12572637 97:−0.36811334 98:0.27649081 99:−0.29904482 100:−0.54955459 101:−0.37619653 102:−0.60832101 103:0.51092577 104:0.78697848 105:0.25848758 106:0.088439323 107:0.070940167 108:−0.46263182 109:−0.078742944 110:−0.24494691 111:−0.63427389 112:0.31611168 113:0.160592 114:−0.047104497 115:0.76102859 116:−0.82229227 117:0.80871314 118:0.3091296 119:−0.34607694 120:−0.28656325 121:0.27505815 122:−0.11336336 123:0.98069334 124:−0.16031924 125:−0.79357618 126:−0.13158225 127:−0.15878426 128:−0.27900419 129:−0.036468007 130:0.20241836 131:0.071653768 132:0.25721821 133:−0.25297976 134:0.16544876 135:−0.18717253 136:−0.0036672305 137:9.853208e-005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e-006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e-005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e-005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:0.0027518668 216:0.00043837572 217:0.027317183 218:0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 |

APPENDIX C1-continued

SVM Model Weights
(340; Normal/Diseased)

243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
0.0034319981554139273 1:4.0929852 2:1.4835061 3:6.1188703 4:−10.270689 5:2.5785246
6:−3.0121825 7:5.101213 8:1.347518 9:−3.5204203 10:2.21015 11:−5.8079023 12:−2.5663617
13:−0.33926055 14:2.6436672 15:−1.0706563 16:−0.81574434 17:−3.7340477 18:7.6981411
19:−2.4521976 20:−1.4685667 21:0.33123419 22:−9.4077196 23:−0.35484156 24:−0.17792068
25:−3.6837096 26:4.7119341 27:−5.0051475 28:1.248998 29:0.87546146 30:−1.9852268 31:−1.1443926
32:−1.4047424 33:0.22170831 34:−0.6524421 35:0.39878628 36:1.2928823 37:0.18981601
38:1.3192978 39:−1.4391513 40:−1.0323067 41:0.3658849 42:0.1672495 43:1.9239275
44:−1.1866595 45:−0.21402705 46:0.64624435 47:0.65488696 48:−1.2625316 49:−0.69013387
50:−0.32074571 51:0.27624661 52:−0.064966165 53:1.1192961 54:−0.32037497 55:0.49531639
56:−0.92731094 57:−0.63326555 58:−0.23282745 59:0.37688258 60:−0.067128718 61:0.65384096
62:0.18629821 63:−0.20528869 64:0.18397641 65:0.31394571 66:−0.36168703 67:0.23028509
68:−0.41653144 69:0.46200734 70:−0.18024899 71:−0.099146627 72:−0.84744304 73:−0.043899365
74:−0.052784499 75:−0.28761339 76:−0.30889967 77:0.18458949 78:0.024246849 79:−0.21060209
80:0.19436322 81:0.11929421 82:−0.11581916 83:−0.056519356 84:0.04534936 85:0.41549221
86:0.085935034 87:0.13137645 88:−0.017532332 89:0.067202449 90:−0.10915218
91:−0.085174158 92:0.29068413 93:0.2926307 94:0.060283277 95:0.018072564 96:−0.098022886
97:−0.15867223 98:0.010256243 99:0.089763269 100:−0.020495217 101:−0.039462265
102:0.047161911 103:0.096931636 104:0.12819229 105:0.07517647 106:0.17980841
107:0.035823017 108:−0.017471896 109:0.17312534 110:0.032054223 111:0.027204277
112:−0.037720092 113:0.14985901 114:0.094467551 115:0.1592768 116:−0.041001573
117:0.014223807 118:0.030344447 119:−0.022475053 120:−0.034849949 121:0.030777428
122:0.039635137 123:0.096572749 124:0.050145131 125:−0.070469633 126:−0.083560094
127:−0.029772749 128:−0.083051004 129:−0.060377385 130:0.025555383 131:−0.012382057
132:−0.0055278521 133:−0.11941805 134:0.13074152 135:−0.095291696 136:−0.0036672305
137:9.853208e−005 138:−0.017125415 139:0.0062208101 140:0.00056613336 141:0.0012280536
142:−0.00039310646 143:−0.0063707544 144:0.0015248039 145:−0.0029345977
146:−0.00076821423 147:0.00013666278 148:−0.0051379474 149:0.0066761598 150:−0.0024066679
151:0.0038081626 152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761

APPENDIX C1-continued

| SVM Model Weights<br>(340; Normal/Diseased) |
|---|
| 289:−0.0040808818 290:−0.00058058492 291:0.00025530611 292:0.00042821659<br>293:−0.0017559038 294:0.00030293313 295:−0.0004816725 296:−0.00057298481 297:−0.00086739491<br>298:0.0020803961 299:0.00010370808 300:0.00075778627 301:0.00074104586<br>302:−0.00021793939 303:0.0013351805 304:−0.0006143825 305:0.0025815656 306:7.1731614e−005<br>307:−0.0052312948 308:−0.00063595735 309:0.0015091125 310:−0.00024647679<br>311:−0.0050271503 312:−0.00065122027 313:−0.00070704299 314:−0.0038100008 315:0.0022923627<br>316:0.0019759815 317:0.00079242635 318:0.0045642676 319:0.001573379 320:0.0015903091<br>321:0.00074843148 322:−0.00091753813 323:0.0021253934 324:0.0013280844<br>325:−0.0030691659 326:−0.0033078301 327:0.0012743858 328:0.0024482214 329:0.0018192574<br>330:0.0026370357 331:0.0017312634 332:0.00066732749 333:0.00034391912 334:0.0037949879<br>335:0.0018411272 336:0.0051615993 337:0.0017553387 338:−0.0027431778 339:−0.0055160136<br>340:0.0031345901 #<br>0.0034319981554139273 1:−0.17285712 2:5.3579178 3:−0.74000329 4:0.99322218 5:−6.1377206<br>6:0.59887767 7:0.042126093 8:−0.2397196 9:1.3158681 10:1.9585021 11:−2.8881965<br>12:−2.0061564 13:0.65251106 14:−1.2070966 15:−0.58103746 16:0.42443126 17:−0.66891319<br>18:1.3253081 19:0.98001778 20:−0.39893013 21:−0.8579973 22:1.2817551 23:−0.42398727<br>24:1.3232685 25:0.21813056 26:−0.35450104 27:−0.12951463 28:−0.43908429 29:−1.0419377<br>30:−1.6454725 31:−0.12625751 32:−0.41548735 33:0.67890793 34:−0.418008 35:0.2621589<br>36:0.049831923 37:−1.4470059 38:1.1266959 39:0.58603501 40:1.4245315 41:−0.17537774<br>42:−1.3361218 43:0.083461992 44:−1.5330092 45:−0.35139784 46:−0.055380493 47:0.5069105<br>48:−0.65670156 49:0.082980849 50:1.0968806 51:−0.67249388 52:−0.45360234 53:−1.2057146<br>54:1.5455887 55:0.079480849 56:1.4911444 57:0.76370496 58:−0.55405068 59:−0.61118889<br>60:0.36784449 61:0.66775882 62:0.91460311 63:0.0053329607 64:0.34343752 65:1.1612324<br>66:0.16291295 67:−0.19362122 68:−0.19218297 69:−1.3981386 70:−0.28877142 71:−0.51815724<br>72:0.15315264 73:0.49423894 74:−0.12288372 75:0.37653589 76:0.041707151 77:0.88474351<br>78:−0.13657476 79:0.23490222 80:0.00163262 81:−0.75146848 82:0.91966087 83:−0.22570723<br>84:0.34171563 85:−0.21373966 86:0.31872326 87:−0.78817838 88:0.28528082 89:0.14605407<br>90:−0.57167596 91:0.002654057 92:−0.91813678 93:−0.76230198 94:0.2691302 95:−0.10982502<br>96:−0.072105132 97:−0.20987023 98:−0.25559843 99:0.3780562 100:0.99376112 101:−0.05746891<br>102:0.64589149 103:0.26559427 104:−0.43345085 105:−0.1614309 106:0.18858121<br>107:−0.96498543 108:0.5708046 109:0.49519452 110:0.68853563 111:0.64929813 112:−0.21356772<br>113:0.99805456 114:−0.03316183 115:−0.14789551 116:−0.294723 117:0.62947917<br>118:0.15023042 119:0.0025454098 120:0.19112815 121:0.26406813 122:0.12071398<br>123:0.24705248 124:0.095722117 125:−0.18742472 126:−0.57242161 127:−0.28109661<br>128:0.19482248 129:0.088822171 130:0.25467208 131:−0.29063213 132:−0.040046476<br>133:−0.3349281 134:0.037675228 135:−0.015702298 136:−0.0036672305 137:9.853208e−005<br>138:−0.017125415 139:0.0062208101 140:0.00056613336 141:0.0012280536 142:−0.00039310646<br>143:−0.0063707544 144:0.0015248039 145:−0.0029345977 146:−0.00076821423<br>147:0.00013666278 148:−0.0051379474 149:0.0066761598 150:−0.0024066679 151:0.0038081626<br>152:−0.0013487631 153:−0.0020869875 154:−0.0023751855 155:1.1204498e−006<br>156:0.0039485889 157:−0.00011155871 158:0.00070337567 159:0.0012323871<br>160:0.0021008069 161:0.0028489598 162:0.00029079549 163:0.0020081406 164:0.0044465163<br>165:0.007065278 166:0.0012901861 167:0.0037493915 168:−0.0023597497 169:−0.00012567961<br>170:0.00047573209 171:7.8875659e−005 172:−0.0056320974 173:−0.0067036133<br>174:0.00017559867 175:0.001684437 176:−0.0034504069 177:0.0018235954 178:−0.001383971<br>179:0.0004998623 180:−0.00066253374 181:0.0015807585 182:0.00412085 183:0.0021063511<br>184:0.00072732504 185:−0.0012095358 186:−0.0030121093 187:−0.0020631803<br>188:−0.00068084424 189:0.0002527938 190:−0.0034640408 191:−0.00026976471 192:0.00097010034<br>193:−0.0011612385 194:−0.0015113452 195:0.00062438019 196:−0.00013164691<br>197:0.0020616048 198:0.0010445472 199:−0.0049765292 200:9.8877339e−005 201:0.0028779099<br>202:−0.0036701721 203:0.00099803088 204:0.00068234798 205:0.002192216 206:0.0033146022<br>207:0.00050616561 208:−0.0031757453 209:0.0028448526 210:0.00092352234<br>211:−0.0022140611 212:−0.0013608048 213:0.0051376815 214:−0.0017870248 215:−0.0027518668<br>216:0.00043837572 217:−0.027317183 218:−0.024619192 219:−0.01382506 220:−0.015382294<br>221:−0.016386922 222:−0.0094594397 223:−0.0056853383 224:−0.00050634646<br>225:−0.00087913428 226:−0.023968795 227:−0.0034698097 228:−0.0016731552 229:0.00047607321<br>230:−0.011432272 231:−0.00036644109 232:−0.0025967851 233:0.0015593689<br>234:−0.0042631673 235:−0.0053286692 236:−0.0059999214 237:−0.087129325 238:−0.063751429<br>239:−0.0045496477 240:−0.0073839114 241:0.0014150206 242:−0.0042075687 243:−0.0022374168<br>244:−0.041910719 245:−0.030919394 246:−0.049301699 247:−0.019442754 248:−0.0019611341<br>249:−0.0072449106 250:−0.0051453672 251:−0.0072873179 252:−0.005927789 253:−0.0018599511<br>254:−0.017141052 255:−0.023494685 256:−0.01788312 257:−0.01943502 258:−0.0060224077<br>259:−0.0073500308 260:−0.0064477329 261:−0.0002986097 262:−0.0014349599 263:−0.0020359957<br>264:−0.0082596857 265:−0.006963369 266:−0.0016096481 267:−0.0083991755 268:−0.046351645<br>269:−0.046128571 270:−0.011141608 271:0.0020650877 272:−0.0010642689 273:−0.018076098<br>274:−0.016929928 275:−0.0052876701 276:−0.0025432054 277:−0.04111632 278:−0.031511344<br>279:−0.019488858 280:−0.0036160324 281:−0.032332413 282:−0.023754911 283:−0.0030713808<br>284:−0.033357695 285:−0.027144579 286:−0.0093234172 287:−0.0091438433 288:0.00080924761<br>289:−0.0040808818 290:−0.00058058492 291:0.00025530611 292:0.00042821659<br>293:−0.0017559038 294:0.00030293313 295:−0.0004816725 296:−0.00057298481 297:−0.00086739491<br>298:0.0020803961 299:0.00010370808 300:0.00075778627 301:0.00074104586<br>302:−0.00021793939 303:0.0013351805 304:−0.0006143825 305:0.0025815656 306:7.1731614e−005<br>307:−0.0052312948 308:−0.00063595735 309:0.0015091125 310:−0.00024647679<br>311:−0.0050271503 312:−0.00065122027 313:−0.00070704299 314:−0.0038100008 315:0.0022923627<br>316:0.0019759815 317:0.00079242635 318:0.0045642676 319:0.001573379 320:0.0015903091<br>321:0.00074843148 322:−0.00091753813 323:0.0021253934 324:0.0013280844<br>325:−0.0030691659 326:−0.0033078301 327:0.0012743858 328:0.0024482214 329:0.0018192574 |

APPENDIX C1-continued

SVM Model Weights
(340; Normal/Diseased)

330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 #
0.0034319981554139273 1:7.5575404 2:1.2708558 3:−2.5564513 4:2.3454616 5:−4.0419817 6:3.6907179 7:3.6983776 8:0.66216749 9:1.8481812 10:−4.4674816 11:0.81366938 12:2.0454063 13:1.2286377 14:−0.79411447 15:2.6960921 16:2.3801267 17:−3.9791861 18:−1.2930653 19:−0.071555428 20:−1.6138343 21:0.35226038 22:−0.16730696 23:1.6548449 24:0.18559873 25:2.1241612 26:0.31977135 27:−0.93729568 28:1.5951219 29:0.61639202 30:−0.88338506 31:−0.30948994 32:−1.1341227 33:0.053725217 34:0.55166566 35:−0.088504292 36:1.1535082 37:−1.6387075 38:0.47641572 39:0.78401601 40:−0.17910491 41:0.44150418 42:1.0853348 43:−0.90102106 44:−0.23553529 45:−1.2330498 46:−1.1346302 47:−1.2718041 48:−0.23164549 49:1.5911038 50:−1.3972417 51:0.51193959 52:0.10215104 53:1.3947874 54:0.50654709 55:−0.28716737 56:0.52380943 57:−0.6641522 58:−0.4423224 59:0.043580774 60:−0.17660081 61:−0.65470898 62:0.54345536 63:−0.89972711 64:1.3129793 65:−1.4059575 66:1.1218358 67:0.13474494 68:−0.11640819 69:−1.0111084 70:0.22180116 71:−0.57438076 72:0.35917073 73:−0.29428148 74:0.77561665 75:0.76326346 76:−0.02471507 77:−0.45806614 78:−0.38149336 79:0.58453786 80:0.11966577 81:0.73335242 82:0.11628031 83:0.52007282 84:0.35929218 85:−0.34161055 86:1.1650881 87:−0.77597189 88:−0.093616754 89:0.44901651 90:−0.75724018 91:−0.28887293 92:−0.015948901 93:0.28654936 94:−0.24469861 95:0.16087621 96:0.38882983 97:−0.2379609 98:0.18166639 99:0.99717265 100:−0.36347431 101:−0.20353559 102:−0.09105657 103:−0.36705038 104:0.22776908 105:1.018031 106:0.1724837 107:−0.66061884 108:0.096505478 109:−0.49662256 110:0.69764537 111:−0.11248508 112:−0.41569951 113:−0.46046427 114:0.46255407 115:0.36619538 116:0.2065323 117:0.005401467 118:0.13303521 119:−0.17530727 120:−0.24173807 121:−0.042658359 122:0.44329885 123:0.16453099 124:0.0010040628 125:0.18674748 126:0.31579533 127:0.036493905 128:−0.24614115 129:−0.10206834 130:−0.44825599 131:−0.2268146 132:0.0013816013 133:−0.13990803 134:0.23651586 135:−0.20495464 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 #
0.0034319981554139273 1:4.8310957 2:−0.51966381 3:3.2191603 4:−5.9580889 5:−3.9725423 6:0.56513089 7:5.1268225 8:−0.1668672 9:0.36320001 10:−3.7878082 11:−0.10110246 12:−0.6566487 13:5.6380572 14:2.660486 15:−3.7514431 16:3.8383276 17:−2.368597 18:−2.6838796 19:−0.51957881 20:−1.0350298 21:−2.689707 22:−0.040914409 23:−2.89046 24:−0.017867085 25:2.3588343 26:0.7256881 27:0.82110369 28:−0.69781995 29:−2.8904381 30:−0.0058995388 31:0.3508876 32:0.23750982 33:−1.1175548 34:0.65478104 35:2.9058352 36:−1.0202932 37:1.486963 38:1.0728838 39:−3.0690415 40:−0.14180592 41:−2.1934268 42:−0.5380643

APPENDIX C1-continued

SVM Model Weights
(340; Normal/Diseased)

43:0.7140224 44:−2.0659578 45:−0.12305688 46:2.9920449 47:−2.1582038 48:1.3255918
49:1.483328 50:0.30026016 51:0.87408745 52:−0.61406249 53:1.0657183 54:−1.4992493
55:−0.23971069 56:0.43577427 57:1.691076 58:0.65021253 59:−0.31427428 60:0.72341466
61:−1.265844 62:−0.10906541 63:−0.088984825 64:0.091691613 65:−0.14957437 66:0.71384794
67:−0.30230176 68:−0.050637566 69:−0.12429062 70:1.6292779 71:0.75504225 72:−0.40864852
73:−0.22019285 74:−0.15642677 75:0.23244423 76:0.27070737 77:−0.15731111 78:0.30020115
79:−0.24489987 80:0.34977928 81:0.35565168 82:0.19694737 83:0.14676331 84:0.16930567
85:−0.051620871 86:−0.70444131 87:0.051552422 88:−0.45496103 89:0.040747102 90:0.32198319
91:−0.049458537 92:0.2997323 93:−0.39576438 94:0.26309776 95:0.20585851 96:−0.16946292
97:0.16999578 98:0.15485273 99:−0.24851924 100:0.1823023 101:−0.22852308 102:0.33441302
103:−0.016284542 104:0.26192731 105:−0.39392173 106:−0.10512904 107:−0.045703731
108:−0.28352123 109:−0.19358872 110:−0.0348906 111:−0.49047658 112:0.19167899 113:0.31319672
114:0.46503049 115:−0.086396135 116:−0.042555541 117:0.37822258 118:0.022551414
119:0.13535589 120:−0.17788902 121:0.21112897 122:0.03455741 123:−0.064876564
124:−0.25643948 125:−0.15818171 126:0.095095024 127:−0.060543213 128:0.056997914
129:−0.12580784 130:−0.01077826 131:−0.11873192 132:−0.044320796 133:−0.1622535
134:−0.0076787225 135:0.10457502 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133 174:0.00017559867 175:0.001684437
176:−0.0034504069 177:0.0018235954 178:0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938
190:−0.0034640408 191:−0.00026976471 192:0.00097010034 193:−0.0011612385 194:−0.0015113452
195:0.00062438019 196:−0.00013164691 197:0.0020616048 198:0.0010445472
199:−0.0049765292 200:9.8877339e−005 201:0.0028779099 202:−0.0036701721 203:0.00099803088
204:0.00068234798 205:0.002192216 206:0.0033146022 207:0.00050616561 208:−0.0031757453
209:0.0028448526 210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097
228:−0.0016731552 229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
0.0034319981554139273 1:4.4914255 2:−0.24480897 3:−2.2583835 4:0.88322991 5:−2.5046406
6:1.9969134 7:−0.0044047181 8:−0.26928857 9:−1.4914516 10:−1.5938169 11:0.76435322
12:3.0260527 13:−1.8695457 14:1.0035132 15:0.51201451 16:−1.4259228 17:−1.8684331
18:0.50730628 19:0.90998501 20:0.74316335 21:1.3944154 22:0.29851213 23:0.39861822
24:0.86132103 25:0.21757281 26:0.94610828 27:1.2375537 28:−0.34744972 29:−1.3769326
30:−1.0923102 31:−0.24452628 32:−0.025521526 33:0.082867205 34:0.21253513 35:−0.5278852
36:0.95895612 37:0.25863516 38:1.6546474 39:−1.2401502 40:0.82902467 41:0.31838235
42:−1.2486559 43:−0.6841439 44:0.22977807 45:−0.83940697 46:−0.79875743 47:0.11707787
48:−0.17272606 49:0.15384579 50:0.087365143 51:0.25894096 52:−0.15067339 53:−0.52227491
54:−1.1062934 55:1.2150086 56:−0.64603966 57:0.18616955 58:−0.6439392 59:0.42169374
60:−0.56355494 61:0.50825572 62:0.05969793 63:0.50939173 64:−0.44535851 65:−0.46299797
66:0.16085759 67:−0.30113783 68:0.13701017 69:1.0244386 70:−0.45194241 71:−0.27729821
72:−0.52808696 73:0.40316921 74:−0.45404562 75:0.6495536 76:0.74272209 77:−0.57873446
78:−0.49307254 79:−0.58688003 80:−0.94545007 81:0.055477004 82:−0.50724208 83:1.0299
84:−0.17139539 85:0.41131699 86:−0.50083166 87:0.057573095 88:0.44515693 89:0.10329576
90:0.030825738 91:1.016457 92:−0.35091561 93:−0.99571693 94:−0.2610175 95:−0.54971737
96:−0.31146067 97:0.033759736 98:−0.52411568 99:0.59184355 100:−0.51342702 101:0.12122373

APPENDIX C1-continued

| SVM Model Weights (340; Normal/Diseased) |
| --- |
| 102:−0.86879963 103:−0.38051108 104:0.45723778 105:−0.16968335 106:0.2920008 107:0.14555357 108:−0.45782804 109:−0.60129797 110:0.1201843 111:0.25632823 112:0.07917951 113:−0.075758159 114:−0.10241938 115:−0.40189445 116:−0.040193915 117:0.3045702 118:−0.50425249 119:−0.3751021 120:0.25430804 121:0.40555459 122:0.36890763 123:−0.30513316 124:0.14127444 125:−0.26494399 126:0.28463182 127:−0.59107149 128:0.361027 129:0.66624409 130:0.052389495 131:−0.061801124 132:−0.07516773 133:−0.089944959 134:0.61868852 135:0.37964967 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.0034319981554139273 1:−0.40237048 2:3.0508842 3:−0.87237811 4:−0.24187045 5:−8.52349 6:4.217833 7:1.0044558 8:−0.71493214 9:0.38238505 10:−0.80563587 11:0.89346939 12:2.4719095 13:1.3058728 14:−0.975398 15:1.7273053 16:−2.1807504 17:−4.3538771 18:−2.3977282 19:−1.7475402 20:1.4739785 21:0.91152471 22:1.1646342 23:0.61799443 24:1.2027286 25:−0.072075672 26:−0.23120642 27:−1.5628221 28:0.30661285 29:0.27028155 30:−0.59216547 31:−0.37261039 32:−1.004298 33:0.18646973 34:−0.77777117 35:−0.070579112 36:−0.52634406 37:0.11652174 38:0.38695204 39:−2.1880736 40:−0.5080148 41:0.067998908 42:0.26474997 43:0.73836499 44:−0.67228192 45:0.33195686 46:−0.7153669 47:0.93102401 48:−0.88505077 49:0.74354327 50:−1.1693422 51:−1.4053208 52:0.26272804 53:−0.73029745 54:0.45781791 55:0.60853875 56:−0.29050004 57:0.63503903 58:−0.88025033 59:−0.39223021 60:0.16995771 61:−0.68475896 62:1.9526094 63:0.32150131 64:−0.7642808 65:0.71404803 66:−0.55241185 67:−0.70457369 68:0.39290434 69:−0.42997518 70:−0.34252283 71:0.57953405 72:−0.17546353 73:−0.32685208 74:−0.63259292 75:0.83298308 76:1.148315 77:−0.34813735 78:0.91191739 79:−0.4794181 80:−0.29130724 81:0.4239091 82:−0.27805558 83:−0.43199664 84:−0.022172065 85:−0.487692 86:−0.59831047 87:0.16403101 88:−0.37728003 89:−0.18734641 90:0.18628497 91:0.7397089 92:−0.031634498 93:−0.017114725 94:−0.049366385 95:−0.28790811 96:0.46115655 97:0.03124826 98:0.45391756 99:0.51527613 100:−0.41876033 101:0.98967677 102:−0.32042894 103:0.88592428 104:0.40551567 105:0.34332806 106:−0.19711217 107:−0.56756896 108:−0.47781155 109:−0.26562905 110:−0.27830315 111:0.34320518 112:0.43936971 113:0.88862503 114:−0.29489154 115:0.37292674 116:−0.17644976 117:−0.8563928 118:0.42583412 119:0.28563336 120:−0.20364963 121:−0.27988282 122:0.039580666 123:−0.099811919 124:−0.0023117636 125:0.29368147 126:0.047110412 127:−0.060042862 128:0.0918753 129:−0.23014206 130:0.019294089 131:0.3222453 132:0.22207454 133:0.17423692 134:−0.30387014 135:−0.11105014 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 |

APPENDIX C1-continued

| SVM Model Weights (340; Normal/Diseased) |
|---|
| 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.0034319981554139273 1:−12.11614 2:7.1385088 3:3.1919744 4:−0.5384708 5:−2.1869912 6:−3.1748075 7:−0.84486699 8:−0.32319507 9:2.3280804 10:0.71962136 11:−0.085431561 12:−1.8759428 13:0.50136417 14:−1.3576798 15:1.9139546 16:−1.2165844 17:−1.3537034 18:−1.0146867 19:1.2403105 20:0.67722082 21:2.3335445 22:−1.3236587 23:−1.2116036 24:−2.895117 25:0.93300378 26:−0.81829029 27:−0.27387846 28:−2.5765381 29:0.15226839 30:−0.44577959 31:1.6107903 32:1.9374447 33:−0.68141097 34:0.75793529 35:−2.0861123 36:−0.031873871 37:−0.72435808 38:0.17355822 39:0.32460123 40:−0.60567987 41:−0.12146416 42:0.77332103 43:0.67675757 44:−2.4846942 45:−1.8086733 46:1.400087 47:0.81786352 48:0.79804885 49:−0.52081394 50:−0.68013966 51:−0.8645705 52:−0.36793041 53:−0.15984587 54:−0.82175982 55:1.6989828 56:0.76421434 57:0.86074358 58:−0.97666752 59:2.2772253 60:0.41359618 61:0.42457017 62:0.046061017 63:0.60289222 64:−1.0145038 65:0.27962157 66:−0.71596462 67:−1.4960284 68:0.1988855 69:0.31735668 70:1.605931 71:0.44322997 72:0.86184591 73:0.51222146 74:−0.038134608 75:−0.28676793 76:−0.42548701 77:−0.43623599 78:−0.066509075 79:0.5596121 80:−1.1059752 81:−0.38695255 82:0.15660313 83:−0.16217946 84:−0.055483129 85:−0.24807593 86:0.87708724 87:−0.90965044 88:−0.52320778 89:−0.68246764 90:−0.32283726 91:0.38744152 92:−0.16893156 93:0.60248536 94:0.84136903 95:0.24490239 96:−0.070712507 97:−0.55634844 98:0.022900539 99:−0.21133968 100:−0.033571839 101:0.12963003 102:−0.13300546 103:−0.10209697 104:−0.27399036 105:−0.072617367 106:0.19057739 107:−0.46740237 108:0.0048037795 109:0.2758362 110:−0.4383539 111:−0.73740518 112:−0.36572513 113:−0.51437032 114:−0.043739472 115:0.33208808 116:−0.32564586 117:−0.12614974 118:0.023812069 119:−0.06978412 120:0.15351143 121:−0.093798496 122:0.023225717 123:−0.36531058 124:0.22265516 125:0.32511252 126:−0.010753365 127:0.094489023 128:0.18636356 129:0.28320748 130:−0.14530391 131:−0.035404619 132:−0.23507687 133:−0.023081305 134:0.17631181 135:−0.14442371 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 |

APPENDIX C1-continued

| SVM Model Weights (340; Normal/Diseased) |
|---|
| 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # −0.0034319981554139273 1:−3.074358 2:1.3200911 3:−0.80671835 4:2.0445714 5:−2.9063234 6:−4.6124997 7:2.0404482 8:0.62350243 9:0.60801113 10:−3.675019 11:0.71826524 12:3.6740007 13:0.53053898 14:−0.1440471 15:1.2151409 16:−1.9254417 17:−2.8270991 18:−1.5436376 19:1.5189598 20:−0.13233209 21:2.8288872 22:1.7279948 23:0.49313927 24:−3.4384861 25:−4.041759 26:0.0057617472 27:−0.86247671 28:1.3864318 29:−0.5651021 30:1.4912993 31:0.70514905 32:1.1217334 33:−0.45903251 34:−2.1538389 35:−0.71733856 36:−0.31227741 37:−0.12458951 38:0.4296701 39:−0.8281135 40:−0.099171795 41:0.91281277 42:−0.073144831 43:−0.50181496 44:−1.4281214 45:0.94214213 46:−0.68833256 47:0.73023897 48:0.99343449 49:−0.64603591 50:0.37665179 51:0.75236219 52:0.20090242 53:1.6063961 54:0.31331399 55:−0.53897274 56:0.33906302 57:−0.20035845 58:0.22891816 59:−0.98087275 60:−0.19053073 61:−0.26519907 62:−2.0439668 63:−0.81633365 64:0.26945484 65:−1.1713725 66:0.32175192 67:−0.39676601 68:−1.2761947 69:0.95289999 70:−0.19126898 71:−0.52938193 72:0.29760873 73:−1.2102565 74:−0.0075565306 75:0.19323081 76:−0.63605744 77:1.0378774 78:−0.06476748 79:−0.48405239 80:−0.37442154 81:−0.89993054 82:0.4111765 83:−1.0060922 84:0.53183049 85:−0.45563287 86:0.16968358 87:−0.45802447 88:0.40387097 89:0.2125842 90:0.41796631 91:−0.047091555 92:−0.2539691 93:−1.1628112 94:0.29029825 95:0.18090288 96:−0.25169617 97:0.54040033 98:−0.65820724 99:−0.3025254 100:0.050546654 101:−1.129313 102:0.32123724 103:0.33231941 104:0.22819054 105:−0.0042978795 106:−0.24708681 107:−0.050751317 108:−0.23648635 109:0.062578768 110:−0.1175883 111:−0.072291121 112:−0.11866668 113:0.5486567 114:−0.038887206 115:0.75130099 116:−0.29792345 117:−0.55575573 118:−0.058953892 119:0.016973015 120:0.056484003 121:0.15374902 122:0.27129269 123:−0.14119118 124:0.046411678 125:0.13361439 126:0.26004538 127:0.0050802319 128:−0.17759718 129:−0.043236971 130:0.29534963 131:0.10151437 132:0.032549489 133:0.13454169 134:0.20521727 135:0.043016076 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 |

APPENDIX C1-continued

| SVM Model Weights (340; Normal/Diseased) |
|---|
| 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # −0.0034319981554139273 1:2.682493 2:11.122195 3:4.206923 4:−1.4622859 5:2.6953654 6:−2.2655728 7:4.8538051 8:5.8362741 9:−1.2447271 10:−0.63010204 11:1.3284103 12:0.62615931 13:−0.30675834 14:−0.4801302 15:2.4601552 16:1.1991416 17:−1.1574873 18:0.61701268 19:2.2572458 20:1.4125764 21:−0.94063079 22:0.98931623 23:−1.2553878 24:−0.67660838 25:−0.31599128 26:0.47997627 27:−1.587342 28:−1.7354906 29:1.3572588 30:−0.30153325 31:0.60223311 32:2.4844804 33:−2.4688098 34:0.45046955 35:1.0528731 36:−2.1922636 37:−1.2375084 38:−1.4075315 39:0.66435403 40:−2.1051486 41:−1.0544809 42:0.77028394 43:−0.89421213 44:−0.01773737 45:−0.47295702 46:0.58288544 47:0.2111946 48:1.3527038 49:−0.080127321 50:0.48317146 51:−1.2236339 52:0.5580551 53:0.85040069 54:1.4942495 55:−1.0360185 56:−1.3499321 57:−0.0054569864 58:0.81168169 59:1.7660463 60:0.27508137 61:−0.51414585 62:0.27423105 63:0.44076794 64:0.010816055 65:−0.47298872 66:0.81987906 67:−0.098804124 68:−0.46406594 69:0.6341064 70:0.31627035 71:−0.062214967 72:−1.4903973 73:−0.42703351 74:−0.57125616 75:−0.035451923 76:1.1853507 77:0.60526383 78:−0.48796123 79:0.97815019 80:−0.68207729 81:0.25026202 82:0.24979776 83:0.016412685 84:0.11594161 85:0.0089153852 86:−0.40602753 87:0.11064657 88:0.49761772 89:−0.63030243 90:−0.45299536 91:−0.51591766 92:−0.10573899 93:−0.25862992 94:−0.66403419 95:0.28555954 96:−0.12843256 97:0.08971867 98:−0.22286613 99:−0.1449877 100:−0.74900949 101:0.20830265 102:−0.31508273 103:−0.11288205 104:0.097524643 105:0.81944829 106:0.071675174 107:0.25241631 108:0.77607149 109:0.016043954 110:0.73551005 111:0.27446678 112:0.23592021 113:0.097468197 114:−0.17914838 115:−0.1479997 116:0.22372115 117:−0.19786657 118:−0.015229989 119:0.22953537 120:−0.21642524 121:0.33818474 122:−0.29020324 123:0.28381917 124:0.096970655 125:−0.031694237 126:−0.36813354 127:−0.39928171 128:0.20994283 129:0.22024599 130:0.25496694 131:0.16285868 132:−0.2601772 133:0.10431271 134:−0.18185806 135:−0.069102958 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 |

APPENDIX C1-continued

| SVM Model Weights (340; Normal/Diseased) |
|---|
| 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # 0.0034319981554139273 1:0.59667957 2:−11.827269 3:0.20600793 4:−4.1515388 5:5.5969896 6:−3.8011801 7:−0.29551542 8:−4.6395001 9:−3.4394548 10:1.4789293 11:0.37074792 12:−2.7612343 13:−0.040486466 14:−0.73112339 15:−1.3585581 16:1.5774809 17:−3.180407 18:−0.29355109 19:1.3384612 20:−5.0804014 21:1.5053214 22:0.73490274 23:−4.830143 24:4.8124661 25:0.44843206 26:−0.19545943 27:0.24023308 28:4.4027333 29:5.2329941 30:1.176523 31:2.8222477 32:4.0621142 33:2.3800118 34:−3.0317044 35:0.87739044 36:0.41121566 37:1.6855221 38:0.55244011 39:−0.71052158 40:2.5928686 41:−0.14377376 42:−0.34617746 43:−2.0218463 44:−0.3130531 45:−0.98937351 46:−0.64656675 47:0.95119798 48:0.55703652 49:0.57706296 50:−0.45926842 51:−0.98095632 52:−0.11625404 53:0.18176861 54:0.13455464 55:−0.21698648 56:0.51767534 57:−0.47635695 58:−0.39904693 59:0.61882967 60:0.057070259 61:−0.24861169 62:0.056957696 63:0.81587791 64:−0.013675157 65:−1.0445228 66:−0.27801517 67:0.12983292 68:0.27910516 69:0.29829064 70:0.28584638 71:0.63583302 72:−0.17568482 73:0.13753381 74:−0.23729491 75:−0.43226141 76:−0.11776592 77:−0.90897405 78:0.11062974 79:−0.21575411 80:−0.048541885 81:−0.3580533 82:−0.2560235 83:0.26640245 84:0.28587043 85:−0.39213607 86:−0.22304581 87:−0.42175221 88:0.12778507 89:0.12025977 90:−0.63611841 91:0.042656537 92:0.44216374 93:−0.1015946 94:0.19681969 95:0.032479074 96:−0.28008166 97:0.30654496 98:−0.12331007 99:−0.083260104 100:−0.032194793 101:0.11773236 102:−0.064598955 103:0.25232285 104:−0.41223374 105:−0.14131932 106:0.094873436 107:0.087123774 108:0.21026024 109:0.07980486 110:−0.01481969 111:0.066620782 112:−0.016888469 113:0.026096277 114:−0.024452215 115:−0.047453228 116:0.10341555 117:−0.069423661 118:0.13545996 119:−0.24342193 120:−0.21726654 121:−0.043684866 122:0.058270585 123:0.18585016 124:0.019479567 125:0.061534069 126:−0.15206677 127:−0.058601908 128:0.13626719 129:−0.040486496 130:−0.040063731 131:0.045826234 132:0.045917019 133:0.054584589 134:−0.069070183 135:−0.0189026 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.0194302 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 |

APPENDIX C1-continued

SVM Model Weights
(340; Normal/Diseased)

330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
0.0032083303651680244 1:9.6229353 2:−11.464231 3:4.1598067 4:−3.3941331 5:4.1509666
6:1.546693 7:4.3594489 8:2.2675736 9:−7.5672388 10:3.2643189 11:7.6341481 12:−1.8415549
13:2.2022524 14:−6.6046128 15:−1.4669977 16:−0.62688833 17:0.30700147 18:2.1391397
19:−0.59542352 20:−0.46061856 21:−1.7516705 22:−1.7772889 23:−1.2461953 24:−3.7455966
25:0.93802625 26:1.9527825 27:1.9288 28:−0.054740768 29:−0.64815861 30:−3.302285
31:0.8848452 32:0.34685737 33:−4.2761202 34:−1.4045439 35:−2.5042417 36:2.0580082
37:1.2458475 38:−2.4746141 39:1.3653669 40:0.27495795 41:−0.53184092 42:0.294159
43:−3.4988699 44:−0.36391535 45:0.013886777 46:0.11503884 47:−0.066243589 48:0.51242113
49:−1.2058492 50:−0.65748274 51:0.010243749 52:−1.0761719 53:−0.025190989 54:−0.5794028
55:−0.11958646 56:−0.076222733 57:−0.96427655 58:−0.40716705 59:−1.8620995 60:0.48778456
61:−0.11708479 62:0.12640536 63:0.16012475 64:−0.44476369 65:−0.38889754 66:−0.53000444
67:0.27671438 68:0.23756695 69:−1.3401867 70:0.16650194 71:0.61802739 72:−0.093269974
73:−0.28750378 74:0.44459164 75:0.44572949 76:0.39498365 77:0.36121634 78:−0.29221752
79:0.11955436 80:−0.26415828 81:−0.062166933 82:0.01595111 83:−0.31023872 84:−0.49856728
85:−0.073556148 86:0.2346469 87:−0.14745834 88:−0.58042079 89:−0.27640826 90:0.54834336
91:0.30368304 92:−0.18068478 93:−0.52147001 94:0.22172539 95:−0.17695418 96:−0.16760626
97:0.047468878 98:0.43309161 99:0.37203526 100:0.10840502 101:0.39886776 102:0.32449752
103:−0.27920568 104:0.015125466 105:0.016040847 106:−0.21282452 107:−0.26584285
108:−0.26779282 109:0.14082214 110:−0.14503345 111:0.23157236 112:0.26014876 113:0.014481938
114:−0.02916058 115:−0.070024066 116:−0.0025725258 117:−0.037619319 118:−0.0077701132
119:0.042662077 120:−0.0773191 121:−0.0757486 122:0.13973655 123:0.058686435
124:−0.15730287 125:0.024562623 126:0.071768649 127:−0.01692272 128:−0.089761756
129:0.12698679 130:0.21955249 131:−0.036448218 132:−0.030725809 133:0.028406963
134:−0.0041619628 135:0.01391092 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133 174:0.00017559867 175:0.001684437
176:−0.0034504069 177:0.0018235954 178:−0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938
190:−0.0034640408 191:−0.00026976471 192:0.00097010034 193:−0.0011612385 194:−0.0015113452
195:0.00062438019 196:−0.00013164691 197:0.0020616048 198:0.0010445472
199:−0.0049765292 200:9.8877339e−005 201:0.0028779099 202:−0.0036701721 203:0.00099803088
204:0.00068234798 205:0.002192216 206:0.0033146022 207:0.00050616561 208:−0.0031757453
209:0.0028448526 210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.6034698097
228:−0.0016731552 229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
−0.0015939870926883625 1:−7.4997253 2:4.4368262 3:−2.9816823 4:−3.2905457 5:−7.8223085
6:5.5449471 7:0.26657972 8:−1.4545244 9:−0.12112358 10:0.36736658 11:1.3500887
12:2.6143444 13:0.8353107 14:0.6069836 15:−0.57392049 16:−1.7705781 17:0.074982144
18:−1.3446496 19:−3.4150405 20:0.11493096 21:−0.62300509 22:−0.056075014 23:−0.84774786
24:0.94183409 25:−0.027781744 26:−0.79541111 27:−2.3700309 28:0.34954032 29:−0.31329978
30:0.97368103 31:0.77245986 32:−0.67884284 33:−1.7504072 34:−2.391221 35:0.083415404
36:−1.9214619 37:−0.7868306 38:−0.92057556 39:−2.0276494 40:0.288537 41:−1.5791048

APPENDIX C1-continued

| SVM Model Weights (340; Normal/Diseased) |
|---|
| 42:0.91143805 43:−0.80769163 44:0.47642806 45:−1.7863086 46:−1.493109 47:0.302784 48:−0.055297635 49:−0.016376823 50:−0.17008308 51:−0.24937692 52:−0.64883745 53:0.00060224853 54:0.25627023 55:0.80983388 56:−0.61239278 57:−0.71748292 58:−0.80918968 59:−0.5118615 60:0.31323686 61:0.83679247 62:−0.89665455 63:−0.34058276 64:−1.2529209 65:−0.7296108 66:−0.63929236 67:−0.24356525 68:0.72444028 69:−0.10387129 70:0.24494018 71:0.70650542 72:−0.3703928 73:0.3357864 74:−0.20377003 75:−0.90150124 76:0.79134268 77:−0.12168025 78:0.17380694 79:−0.086510047 80:0.067077324 81:0.13328306 82:0.67633224 83:−0.9618206 84:0.20394857 85:0.1517325 86:1.0346502 87:0.53699476 88:1.4037936 89:0.082299776 90:0.51651537 91:−0.1331668 92:0.49096477 93:0.55968136 94:−0.45929629 95:0.13745704 96:−0.057781253 97:0.07302165 98:−0.46587041 99:−0.12942116 100:1.2046416 101:−0.010231865 102:−0.14934839 103:−0.28579372 104:0.2305035 105:0.48780185 106:−0.51815635 107:0.15188494 108:0.25398615 109:−0.69408584 110:−0.14664534 111:0.030618666 112:−0.57057595 113:0.10640582 114:0.58058107 115:−0.58403891 116:0.069108859 117:0.62333924 118:0.13177703 119:0.3496547 120:0.47469035 121:−0.21698946 122:0.0096817799 123:−0.025226032 124:0.1320491 125:−0.18954135 126:−0.15524918 127:0.31710109 128:−0.11795855 129:0.15935433 130:−0.045581292 131:−0.011549506 132:−0.078083694 133:0.26787254 134:0.16358735 135:−0.049957488 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:11204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # 0.0034319981554139273 1:3.5839531 2:−5.883049 3:−4.1707263 4:2.668844 5:−0.41040224 6:−0.95485866 7:−0.55179292 8:−1.9773617 9:−0.17881806 10:−1.001881 11:2.653228 12:1.7653873 13:−0.3574464 14:0.60210371 15:0.91023183 16:1.1576729 17:−0.5881654 18:0.7762832 19:1.5496694 20:−0.84777153 21:0.53634214 22:−0.85376447 23:0.56399333 24:0.27470717 25:0.43654314 26:−0.068430081 27:−0.01878595 28:−0.35401875 29:0.97802097 30:1.0260972 31:0.090353049 32:−1.5823214 33:−0.66183901 34:−0.35473683 35:0.31219536 36:1.321782 37:−0.10658298 38:0.37130693 39:0.95498109 40:−0.42194906 41:−0.38221079 42:0.77177846 43:−0.016424144 44:−1.3272197 45:0.0035217868 46:−0.090253808 47:0.04113742 48:0.11804217 49:−1.9058766 50:0.72675604 51:−1.0927874 52:−0.49189433 53:−0.69180405 54:−0.091230541 55:−0.85680449 56:−0.49585167 57:0.26901877 58:0.75938016 59:0.84990495 60:−0.24252474 61:0.37672266 62:0.53485793 63:0.43563795 64:0.43031749 65:0.64165699 66:0.38401568 67:0.11291075 68:0.63343042 69:0.41156557 70:0.75446075 71:−0.38473544 72:0.56635094 73:−0.46696714 74:−0.70581251 75:0.023400884 76:−0.41346964 77:−1.430331 78:−0.42817894 79:0.2327694 80:0.26672408 81:0.20924288 82:0.30024919 83:−0.29518965 84:0.10202514 85:0.72934097 86:0.095154114 87:−0.43278944 88:0.58955455 89:0.70504868 90:−0.32077006 91:−0.45377767 92:−0.5903635 93:−0.41557035 94:−0.35873139 95:−0.69236827 96:−0.2166281 97:−0.91312081 98:0.33627343 99:−0.65022963 100:−0.22873628 101:0.073755279 |

APPENDIX C1-continued

SVM Model Weights
(340; Normal/Diseased)

102:−0.28477678 103:−0.28926757 104:−1.1250086 105:0.45337877 106:−0.45823035 107:−0.43574345
108:−0.63711619 109:−0.56669188 110:−0.40914211 111:0.0082243131 112:0.087610126
113:0.66194248 114:0.58199036 115:−0.24508597 116:−0.19771665 117:−0.42856571
118:−0.73119789 119:0.19806954 120:0.37247425 121:0.12117126 122:0.0036323396 123:0.19421768
124:−0.27722415 125:−0.35143659 126:0.034127496 127:0.20987651 128:−0.25472102
129:−0.55852264 130:0.006120278 131:0.33967084 132:−0.52636373 133:−0.10150271
134:−0.072770365 135:0.31490892 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133 174:0.00017559867 175:0.001684437
176:−0.0034504069 177:0.0018235954 178:−0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938
190:−0.0034640408 191:−0.00026976471 192:0.00097010034 193:−0.0011612385 194:−0.0015113452
195:0.00062438019 196:−0.00013164691 197:0.0020616048 198:0.0010445472
199:−0.0049765292 200:9.8877339e−005 201:0.0028779099 202:−0.0036701721 203:0.00099803088
204:0.00068234798 205:0.002192216 206:0.0033146022 207:0.00050616561 208:−0.0031757453
209:0.0028448526 210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097
228:−0.0016731552 229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
0.0034319981554139273 1:3.9010017 2:−5.5965748 3:−3.4673359 4:3.8046615 5:−0.80037314
6:−2.4926233 7:−0.65297276 8:−1.2992364 9:0.5986374 10:−0.76736987 11:1.0571005 12:0.28337967
13:−1.2857354 14:−0.26973414 15:−1.2984749 16:2.5997679 17:−0.13204159 18:0.39124656
19:−0.49126437 20:−1.188978 21:−0.021166831 22:0.5348773 23:−0.33920935 24:0.28458688
25:0.99250501 26:0.56726456 27:−0.045532424 28:0.12138137 29:1.0281024 30:−0.11518206
31:−0.46092334 32:−0.71239334 33:−0.41137099 34:−0.0074320761 35:0.15266328 36:1.4160883
37:−0.65966898 38:0.60130179 39:0.13380145 40:−0.32677779 41:−1.4254662 42:−0.070341729
43:0.86671621 44:−0.063052483 45:−1.248728 46:0.96862358 47:0.67674959 48:−0.089700386
49:0.34273475 50:−0.34479642 51:−0.032356691 52:0.50782025 53:−0.45508158 54:0.41873366
55:−1.5648514 56:−1.130119 57:0.62267995 58:−1.7532282 59:0.35311949 60:0.10332357
61:−0.52477038 62:−0.49120677 63:−0.78596723 64:−0.048472244 65:0.14055537 66:−0.39380437
67:−0.063648462 68:0.15314686 69:0.33958638 70:0.32310656 71:−0.77177393 72:0.29027194
73:−0.35018161 74:−0.043229166 75:−0.34670517 76:0.21358065 77:0.00060069456 78:−0.3655521
79:0.79942805 80:−0.76392227 81:0.084121495 82:0.54889029 83:0.81910717 84:0.56165129
85:1.4063003 86:−0.57837188 87:0.45148107 88:−0.3174257 89:0.87369037 90:0.61911416
91:−0.25930297 92:0.51029682 93:−0.67216766 94:0.60300803 95:−0.14273056 96:0.5953576
97:−0.48643908 98:0.41215062 99:−0.035658658 100:0.25204182 101:−0.38218647 102:−0.26450488
103:−0.17855796 104:−0.12992834 105:−0.54721981 106:0.056506511 107:−0.29469997
108:0.084127516 109:0.16221343 110:0.54439348 111:0.12306155 112:0.085833848
113:−0.54037279 114:−0.33571401 115:0.27703506 116:−0.52600837 117:0.27983457 118:0.31606394
119:0.49031234 120:0.80367947 121:−0.64342391 122:0.0066169007 123:0.33146441
124:0.1393441 125:0.30393684 126:0.25799295 127:−0.41761872 128:−0.20890269
129:0.022179041 130:0.31772971 131:0.020162186 132:0.32351559 133:0.74810362
134:−0.083276793 135:−0.0014183105 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631

APPENDIX C1-continued

| SVM Model Weights (340; Normal/Diseased) |
|---|
| 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.0015421317677794251 1:8.6169634 2:−14.909825 3:4.5661917 4:−14.234359 5:−3.8803411 6:8.3793383 7:1.91558 8:2.890739 9:3.0715823 10:−3.6336942 11:5.559761 12:−6.221118 13:7.0444469 14:11.942661 15:−3.5210028 16:3.0451481 17:0.8645637 18:0.90090793 19:3.8014674 20:3.3772614 21:4.4967599 22:1.2317743 23:−4.7559361 24:−1.5627382 25:−1.5317196 26:−1.1812898 27:0.70844483 28:−3.8020139 29:1.3617872 30:−1.9134895 31:−1.6170208 32:−0.33920389 33:2.4329834 34:0.17155254 35:0.18837711 36:−0.27561921 37:−0.36969551 38:−1.4717805 39:0.4519023 40:−0.55164379 41:2.1655481 42:0.56525373 43:−0.60632938 44:0.23338282 45:−0.43923751 46:−1.0631796 47:0.89960551 48:−0.81924933 49:0.16573533 50:−0.36088058 51:−0.17395359 52:0.81688082 53:−0.45888543 54:0.19650544 55:−0.069430716 56:−0.062226437 57:−0.5745849 58:−0.068097599 59:−0.12771016 60:−0.053144429 61:−0.34997377 62:−0.18044128 63:0.26831853 64:0.17465159 65:0.0027803043 66:−0.33679929 67:0.26543939 68:−0.37960342 69:−0.26108712 70:−0.32440886 71:−0.050954357 72:0.1843335 73:0.054415613 74:−0.39490819 75:0.12460218 76:−0.060419071 77:0.20380537 78:0.16639464 79:0.25643727 80:0.089747302 81:−0.075347483 82:0.46585262 83:−0.1707512 84:0.21907172 85:0.048297625 86:0.068604268 87:0.14866361 88:−0.098568939 89:0.27236167 90:0.058945496 91:−0.065741405 92:−0.14342982 93:0.16299166 94:−0.062212203 95:−0.15697548 96:0.096842386 97:−0.0053891013 98:−0.030053159 99:0.10920835 100:0.059288606 101:−0.042502955 102:−0.17796583 103:0.076037645 104:0.15239628 105:0.01761502 106:0.046148468 107:−0.039352447 108:0.038781438 109:−0.076163754 110:−0.11290068 111:0.098261282 112:−0.046796966 113:−0.10989556 114:0.19607675 115:−0.070407122 116:−0.064193472 117:−0.020375742 118:−0.044051461 119:−0.061806012 120:0.17198198 121:−0.0049647731 122:−0.15808681 123:−0.13291511 124:0.070180118 125:0.029588487 126:0.049912274 127:0.077471457 128:−0.012670009 129:−0.016919944 130:0.062297463 131:−0.085567452 132:0.047927633 133:0.012903525 134:0.022868866 135:0.0048360182 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 |

APPENDIX C1-continued

| SVM Model Weights (340; Normal/Diseased) |
|---|
| 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:−0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.00036533755356574541 1:12.672485 2:−7.516613 3:−4.2664714 4:2.3894684 5:−1.9428385 6:4.471509 7:1.2204065 8:−1.250452 9:−0.63588476 10:−2.9151223 11:1.88151 12:0.55072552 13:−0.24201356 14:1.4921519 15:4.6928411 16:−1.2068832 17:−1.4440265 18:2.1307447 19:−0.056857955 20:0.72109979 21:0.98974639 22:0.18897299 23:0.70602745 24:−1.4431446 25:1.2278879 26:−0.92486399 27:−0.64960492 28:0.42849684 29:0.57922465 30:0.13556732 31:0.04900476 32:0.78963053 33:−0.3302474 34:1.5677528 35:−0.25550574 36:−0.019869922 37:−0.33791691 38:−0.53458244 39:−0.43368188 40:1.0035195 41:−0.61409533 42:−1.4128333 43:1.3993968 44:−0.30553368 45:0.3655259 46:1.4206858 47:−0.82553267 48:0.17962474 49:−0.0064832438 50:−0.17397274 51:0.60829043 52:0.30540645 53:−0.36179671 54:0.2895571 55:1.2090135 56:−0.69002241 57:−0.37445688 58:−0.81388384 59:−0.9509446 60:−1.4237492 61:0.69672018 62:−0.40041146 63:0.13335143 64:−0.22215128 65:−0.31002694 66:0.86585885 67:0.90976191 68:0.70821398 69:0.20594257 70:0.28823617 71:0.41324094 72:0.44531196 73:−0.38454822 74:0.423778 75:−0.34325457 76:−0.054807279 77:0.64922255 78:−1.0403811 79:−0.23182102 80:0.87733185 81:−1.3414996 82:0.059485011 83:0.28990865 84:0.58551192 85:−0.070296429 86:−0.24462253 87:−0.529284 88:0.52060139 89:0.25932848 90:0.058699455 91:0.2333052 92:−0.42803776 93:−0.044403497 94:0.17142425 95:0.79691029 96:−0.3843385 97:−0.35634202 98:−0.53144592 99:0.25573096 100:−0.26852316 101:0.43637502 102:−0.10010843 103:−0.028138697 104:−0.1453246 105:−0.44031784 106:−0.27631199 107:0.34643885 108:0.23516673 109:−0.99918944 110:−0.90041947 111:−0.039793108 112:−0.041254759 113:−0.48520124 114:−0.31510493 115:−0.22084631 116:−0.15508503 117:−0.014936347 118:−0.14568318 119:0.52625322 120:−0.35733846 121:−0.29942891 122:−0.05238089 123:0.29766941 124:−0.0088121239 125:0.30891523 126:−0.64157474 127:−0.51629728 128:0.082558386 129:−0.33449855 130:0.10181956 131:−0.0003489982 132:0.031934083 133:−0.25455543 134:−0.12486257 135:−0.48811859 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 |

APPENDIX C1-continued

| SVM Model Weights (340; Normal/Diseased) |
|---|
| 243:−0.0022374168 244:−0.041910719 245:−0.030919394 246:−0.049301699 247:−0.019442754 |
| 248:−0.0019611341 249:−0.0072449106 250:−0.0051453672 251:−0.0072873179 252:−0.005927789 |
| 253:−0.0018599511 254:−0.017141052 255:−0.023494685 256:−0.01788312 257:−0.01943502 |
| 258:−0.0060224077 259:−0.0073500308 260:−0.0064477329 261:−0.0002986097 262:−0.0014349599 |
| 263:−0.0020359957 264:−0.0082596857 265:−0.006963369 266:−0.0016096481 267:−0.0083991755 |
| 268:−0.046351645 269:−0.046128571 270:−0.011141608 271:0.0020650877 272:−0.0010642689 |
| 273:−0.018076098 274:−0.016929928 275:−0.0052876701 276:−0.0025432054 277:−0.04111632 |
| 278:−0.031511344 279:−0.019488858 280:−0.0036160324 281:−0.032332413 282:−0.023754911 |
| 283:−0.0030713808 284:−0.033357695 285:−0.027144579 286:−0.0093234172 287:−0.0091438433 |
| 288:0.00080924761 289:−0.0040808818 290:−0.00058058492 291:0.00025530611 |
| 292:0.00042821659 293:−0.0017559038 294:0.00030293313 295:−0.0004816725 |
| 296:−0.00057298481 297:−0.00086739491 298:0.0020803961 299:0.00010370808 300:0.00075778627 |
| 301:0.00074104586 302:−0.00021793939 303:0.0013351805 304:−0.0006143825 |
| 305:0.0025815656 306:7.1731614e−005 307:−0.0052312948 308:−0.00063595735 |
| 309:0.0015091125 310:−0.00024647679 311:−0.0050271503 312:−0.00065122027 |
| 313:−0.00070704299 314:−0.0038100008 315:0.0022923627 316:0.0019759815 317:0.00079242635 |
| 318:0.0045642676 319:0.001573379 320:0.0015903091 321:0.00074843148 322:−0.00091753813 |
| 323:0.0021253934 324:0.0013280844 325:−0.0030691659 326:−0.0033078301 327:0.0012743858 |
| 328:0.0024482214 329:0.0018192574 330:0.0026370357 331:0.0017312634 332:0.00066732749 |
| 333:0.00034391912 334:0.0037949879 335:0.0018411272 336:0.0051615993 337:0.0017553387 |
| 338:−0.0027431778 339:−0.0055160136 340:0.0031345901 # |
| −0.0034319981554139273 1:2.8188708 2:−6.6911874 3:−1.9094163 4:3.7313151 5:2.2988858 |
| 6:−4.5035233 7:3.6753259 8:1.7877527 9:−0.5697372 10:−3.8303387 11:0.54380357 12:0.98700315 |
| 13:−2.3476851 14:0.22088082 15:−0.25059032 16:1.7471974 17:1.6776427 18:−0.41471028 |
| 19:−0.1232703 20:−0.28474811 21:0.86388719 22:−1.7560869 23:−0.21651681 24:1.5879062 |
| 25:2.5298426 26:0.18274429 27:0.93223476 28:−0.68994981 29:0.58218873 30:−0.33872893 |
| 31:0.060827699 32:−0.68644226 33:0.32874823 34:0.45281684 35:−0.79672253 36:−0.75384116 |
| 37:−1.4258924 38:0.48256019 39:0.79279554 40:0.2963959 41:−0.28191131 42:−1.4866642 |
| 43:0.39201823 44:−0.014203273 45:0.7232601 46:−0.28205287 47:−0.18092456 48:−0.13885227 |
| 49:−1.136531 50:0.62042958 51:−1.1368109 52:−1.3643904 53:−3.218905 54:0.85185713 |
| 55:1.6619301 56:−1.2445153 57:−0.015923033 58:0.56667179 59:0.14499521 60:1.221099 |
| 61:0.59760261 62:−1.1682231 63:−1.0689197 64:−0.12711421 65:−0.28777412 66:0.16776499 |
| 67:−0.4115392 68:−0.82982016 69:0.2006533 70:−0.17664079 71:0.083957829 72:−1.1858773 |
| 73:0.47938693 74:−1.1153183 75:0.059068814 76:−0.14203176 77:0.28411403 78:0.081551403 |
| 79:0.12319593 80:0.40994462 81:0.43776467 82:0.45384017 83:0.15771131 84:−0.59814417 |
| 85:−0.031907167 86:−0.054946788 87:−0.56812823 88:−0.40123889 89:−0.39883354 90:0.026511235 |
| 91:0.45387119 92:0.6748569 93:−0.70448226 94:0.34613639 95:0.41215506 96:0.011098406 |
| 97:−0.05687581 98:0.2185836 99:0.035946041 100:0.30100411 101:−0.93043023 102:−0.08193785 |
| 103:1.0971287 104:0.11226976 105:0.39689255 106:0.75860739 107:0.1140068 108:−0.19236445 |
| 109:−0.39832118 110:0.027373783 111:0.23604588 112:−0.1271385 113:−0.42327589 |
| 114:0.62857467 115:0.075037517 116:0.10440345 117:−0.30189478 118:0.33006802 |
| 119:0.42267591 120:−0.75703239 121:−0.39182872 122:0.11163515 123:−0.18934086 |
| 124:−0.45198298 125:0.093402192 126:−0.22966436 127:0.23876883 128:−0.20838569 129:0.15961587 |
| 130:−0.028421296 131:−0.1161066 132:−0.073261589 133:0.036725137 134:0.042099621 |
| 135:0.19322306 136:−0.0036672305 137:9.853208e−005 138:−0.017125415 139:0.0062208101 |
| 140:0.00056613336 141:0.0012280536 142:−0.00039310646 143:−0.0063707544 |
| 144:0.0015248039 145:−0.0029345977 146:−0.00076821423 147:0.00013666278 |
| 148:−0.0051379474 149:0.0066761598 150:−0.0024066679 151:0.0038081626 152:−0.0013487631 |
| 153:−0.0020869875 154:−0.0023751855 155:1.1204498e−006 156:0.0039485889 157:−0.00011155871 |
| 158:0.00070337567 159:0.0012323871 160:0.0021008069 161:0.0028489598 162:0.00029079549 |
| 163:0.0020081406 164:0.0044465163 165:0.007065278 166:0.0012901861 167:0.0037493915 |
| 168:−0.0023597497 169:−0.00012567961 170:0.00047573209 171:7.8875659e−005 |
| 172:−0.0056320974 173:−0.0067036133 174:0.00017559867 175:0.001684437 176:−0.0034504069 |
| 177:0.0018235954 178:−0.001383971 179:0.0004998623 180:−0.00066253374 181:0.0015807585 |
| 182:0.00412085 183:0.0021063511 184:0.00072732504 185:−0.0012095358 186:−0.0030121093 |
| 187:−0.0020631803 188:−0.00068084424 189:0.0002527938 190:−0.0034640408 |
| 191:−0.00026976471 192:0.00097010034 193:−0.0011612385 194:−0.0015113452 195:0.00062438019 |
| 196:−0.00013164691 197:0.0020616048 198:0.0010445472 199:−0.0049765292 200:9.8877339e−005 |
| 201:0.0028779099 202:−0.0036701721 203:0.00099803088 204:0.00068234798 |
| 205:0.002192216 206:0.0033146022 207:0.00050616561 208:−0.0031757453 209:0.0028448526 |
| 210:0.00092352234 211:−0.0022140611 212:−0.0013608048 213:0.0051376815 |
| 214:−0.0017870248 215:−0.0027518668 216:0.00043837572 217:−0.027317183 218:−0.024619192 |
| 219:−0.01382506 220:−0.015382294 221:−0.016386922 222:−0.0094594397 223:−0.0056853383 |
| 224:−0.00050634646 225:−0.00087913428 226:−0.023968795 227:−0.0034698097 228:−0.0016731552 |
| 229:0.00047607321 230:−0.011432272 231:−0.00036644109 232:−0.0025967851 |
| 233:0.0015593689 234:−0.0042631673 235:−0.0053286692 236:−0.0059999214 237:−0.087129325 |
| 238:−0.063751429 239:−0.0045496477 240:−0.0073839114 241:0.0014150206 242:−0.0042075687 |
| 243:−0.0022374168 244:−0.041910719 245:−0.030919394 246:−0.049301699 247:−0.019442754 |
| 248:−0.0019611341 249:−0.0072449106 250:−0.0051453672 251:−0.0072873179 252:−0.005927789 |
| 253:−0.0018599511 254:−0.017141052 255:−0.023494685 256:−0.01788312 257:−0.01943502 |
| 258:−0.0060224077 259:−0.0073500308 260:−0.0064477329 261:−0.0002986097 262:−0.0014349599 |
| 263:−0.0020359957 264:−0.0082596857 265:−0.006963369 266:−0.0016096481 267:−0.0083991755 |
| 268:−0.046351645 269:−0.046128571 270:−0.011141608 271:0.0020650877 272:−0.0010642689 |
| 273:−0.018076098 274:−0.016929928 275:−0.0052876701 276:−0.0025432054 277:−0.04111632 |
| 278:−0.031511344 279:−0.019488858 280:−0.0036160324 281:−0.032332413 282:−0.023754911 |
| 283:−0.0030713808 284:−0.033357695 285:−0.027144579 286:−0.0093234172 287:−0.0091438433 |
| 288:0.00080924761 289:−0.0040808818 290:−0.00058058492 291:0.00025530611 |

APPENDIX C1-continued

| SVM Model Weights (340; Normal/Diseased) |
|---|
| 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e-005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # 0.0034319981554139273 1:3.9855435 2:−2.1551187 3:0.63115042 4:1.5583338 5:−3.9991305 6:−3.0780492 7:2.0848374 8:2.7543757 9:−2.3052657 10:1.416037 11:0.10207489 12:3.0797191 13:−1.0896925 14:1.9548575 15:−0.089594446 16:−1.3948822 17:2.7305973 18:−0.86904126 19:2.5512304 20:−2.1800091 21:0.86764246 22:0.11505432 23:0.20976232 24:−1.2548302 25:−2.8737543 26:3.077101 27:1.5563121 28:0.16239864 29:0.67452103 30:1.2004149 31:−0.94163388 32:−3.336623 33:−0.12538108 34:−1.4093879 35:−1.4058474 36:0.069847085 37:−0.71715277 38:1.0935538 39:−0.28317529 40:−0.34645393 41:−0.031229772 42:0.76986682 43:−1.5068744 44:−0.61947757 45:2.0491185 46:0.34174487 47:−0.169028 48:0.72976196 49:−0.36800814 50:0.64198077 51:1.0225791 52:0.052821398 53:−0.84884322 54:−0.13224651 55:−0.94264621 56:−0.095210724 57:−0.26225153 58:1.0290097 59:0.7017597 60:0.74610132 61:−0.24856976 62:0.14428349 63:1.0233965 64:1.1792885 65:−0.50222903 66:0.061810724 67:−0.88351119 68:0.39995912 69:0.14672771 70:0.60004687 71:0.84775209 72:0.52471834 73:0.32894376 74:−0.12081071 75:−0.36660975 76:0.52416295 77:0.1678348 78:−0.082099371 79:0.458909 80:0.13918488 81:0.21450907 82:−0.61503118 83:0.89800525 84:0.90652812 85:−1.189242 86:−0.028606925 87:0.53557283 88:0.4146761 89:−0.098317742 90:0.33122516 91:0.59063131 92:−0.21258628 93:0.62106973 94:−0.24541797 95:−0.49155685 96:−0.66964304 97:−0.29655823 98:−0.21810697 99:0.11341745 100:0.18099786 101:0.23542088 102:0.0083696228 103:0.40902957 104:−0.21222977 105:−0.05211205 106:0.4418321 107:−0.29293782 108:0.86808956 109:−0.014603523 110:0.35152662 111:−0.62879217 112:−0.29049611 113:−0.13363758 114:−0.44623661 115:−0.77619213 116:−0.60026032 117:0.032173056 118:0.39933661 119:0.49773356 120:−0.070244059 121:−0.25866073 122:0.21846148 123:−0.22583768 124:−0.15568508 125:−0.17772239 126:0.21922976 127:0.0029597152 128:0.08440768 129:−0.19301203 130:−0.17102554 131:0.19247067 132:0.45737845 133:−0.16157816 134:0.04961931 135:−0.031475145 136:−0.0036672305 137:9.853208e-005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e-006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e-005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e-005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e-005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 |

APPENDIX C1-continued

| SVM Model Weights (340; Normal/Diseased) |
|---|
| 335:0.0018411272 336:0.0051615993 337:0.0017553387 338:−0.0027431778 339:−0.0055160136 340:0.0031345901 # 0.0019987335665197547 1:−1.3733028 2:0.68064439 3:7.460279 4:5.9247279 5:−1.6578373 6:0.2775822 7:−24.075966 8:11.05617 9:−14.703788 10:−13.254814 11:−6.6166501 12:−4.9200807 13:6.9956851 14:−2.1158919 15:0.052510254 16:1.4040208 17:0.6028744 18:−0.2575106 19:−1.8322359 20:0.60171747 21:0.94980544 22:−1.0066327 23:0.71674079 24:0.54565024 25:0.33633724 26:−0.38488925 27:0.34494358 28:0.48877886 29:1.5505414 30:0.72180462 31:−0.16976073 32:−0.75829542 33:−0.55314094 34:−0.41896018 35:−0.27545577 36:0.19334559 37:−0.76371801 38:0.35365519 39:0.11516842 40:−0.19414537 41:−0.19628513 42:0.1318195 43:−0.31227034 44:−0.14665678 45:0.197209 46:0.035161458 47:−0.55002463 48:−0.14159618 49:0.21202643 50:−0.17859973 51:−0.023498023 52:−0.042595364 53:−0.074978627 54:−0.036567062 55:0.026178882 56:0.2204465 57:0.13098165 58:−0.08143688 59:−0.0015269634 60:0.0031346004 61:0.1256801 62:0.042953506 63:0.23303264 64:0.017880833 65:0.12163436 66:−0.4547798 67:0.087979041 68:0.21580996 69:−0.067932546 70:0.31557688 71:−0.20528316 72:−0.084230073 73:−0.16125476 74:0.060367841 75:−0.1926917 76:0.43555477 77:0.083085731 78:−0.28572324 79:0.17345585 80:−0.11412895 81:−0.14141244 82:0.31385398 83:−0.21436949 84:0.056894932 85:0.086059354 86:−0.29815629 87:−0.02677156 88:0.12819742 89:0.13987367 90:0.03727863 91:−0.054893039 92:−0.0076572034 93:0.058677074 94:−0.043105233 95:−0.023878284 96:−0.0070990552 97:−0.016499043 98:−0.25243765 99:−0.029225711 100:−0.0023560792 101:−0.026776342 102:−0.081129409 103:0.069048062 104:0.12788278 105:0.013897446 106:−0.18104143 107:0.02573462 108:−0.053703941 109:0.1500701 110:−0.0044054887 111:0.03336614 112:−0.10695036 113:−0.034270018 114:0.02224292 115:−0.12014373 116:−0.0037340699 117:−0.1605304 118:0.034352936 119:−0.061260741 120:−0.12747684 121:0.088393144 122:−0.032941289 123:−0.033298016 124:−0.043190151 125:−0.048079088 126:0.10846137 127:−0.034567349 128:−0.030937709 129:0.027721135 130:0.035717871 131:−0.041788366 132:−0.0063367924 133:−0.038440183 134:0.019154413 135:−0.028233228 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # 0.0034319981554139273 1:0.59482116 2:0.49655741 3:−0.84351039 4:0.95068574 5:−4.0811591 6:−1.6533675 7:−4.1306829 8:−0.31580341 9:1.3122809 10:2.5053549 11:1.1380405 12:1.6289359 13:−0.9442184 14:0.22938868 15:−1.1697842 16:−0.82826602 17:0.10561418 18:0.46374807 19:0.66422725 20:0.77281559 21:1.1046627 22:−0.6667912 23:−1.117923 24:−0.25013828 25:0.26400575 26:1.502566 27:−0.40917194 28:1.3861501 29:−0.38779527 30:1.9878159 31:−0.58013052 32:1.4944628 33:−1.0788684 34:−0.68354863 35:−1.2108407 36:0.73782116 37:−0.37877095 38:0.56748658 39:−0.71442455 40:0.35037532 41:0.92144632 42:−0.76375842 |

APPENDIX C1-continued

| SVM Model Weights (340; Normal/Diseased) |
|---|
| 43:0.26950735 44:−0.46418089 45:1.2684388 46:−1.2894572 47:0.38453567 48:0.77755392 |
| 49:−0.10420168 50:−1.4918073 51:−0.25433838 52:1.6992041 53:0.88712889 54:−0.22789903 |
| 55:0.050006922 56:0.15781982 57:1.0430646 58:1.4553399 59:0.30592921 60:−0.82809275 |
| 61:−0.5042758 62:0.82383734 63:−0.17589451 64:0.057196233 65:−0.19309768 66:−0.15504383 |
| 67:0.9045462 68:0.84916884 69:−0.75964236 70:−1.1753159 71:−0.14933059 72:−1.0553643 |
| 73:−0.49198627 74:−0.11928473 75:−0.14321804 76:0.39056829 77:0.14312863 78:−0.16039832 |
| 79:0.37343377 80:−0.10230464 81:1.5838434 82:0.73417324 83:−0.8083868 84:−0.4950597 |
| 85:−0.06964846 86:0.62892491 87:−0.29976925 88:0.25842452 89:0.028638957 90:−0.33459154 |
| 91:−0.24210803 92:−0.82720351 93:−0.22896078 94:0.78647345 95:0.46265402 96:0.078497663 |
| 97:−0.18079901 98:0.21655272 99:0.31645006 100:0.50116485 101:0.26560119 102:−0.33812389 |
| 103:−0.096657857 104:0.28111076 105:−0.56710929 106:−0.0047988808 107:0.42831671 |
| 108:−0.20065956 109:0.092494853 110:0.3442561 111:−0.41454321 112:−0.053289983 |
| 113:−0.48771751 114:−0.032995634 115:−0.11933296 116:−0.34164333 117:0.52497447 |
| 118:−0.013933582 119:0.14257583 120:0.053262141 121:0.30114564 122:−0.62769198 |
| 123:−0.33805439 124:−0.68059772 125:0.8316856 126:−0.35851765 127:−0.089781739 |
| 128:0.044436738 129:−0.37309718 130:−0.10005014 131:0.027314916 132:−0.038178127 |
| 133:0.017973892 134:0.052275162 135:0.4627085 136:−0.0036672305 137:9.853208e−005 |
| 138:−0.017125415 139:0.0062208101 140:0.00056613336 141:0.0012280536 142:−0.00039310646 |
| 143:−0.0063707544 144:0.0015248039 145:−0.0029345977 146:−0.00076821423 |
| 147:0.00013666278 148−:0.0051379474 149:0.0066761598 150:−0.0024066679 151:0.0038081626 |
| 152:−0.0013487631 153:−0.0020869875 154:−0.0023751855 155:1.1204498e−006 |
| 156:0.0039485889 157:−0.00011155871 158:0.00070337567 159:0.0012323871 |
| 160:0.0021008069 161:0.0028489598 162:0.00029079549 163:0.0020081406 164:0.0044465163 |
| 165:0.007065278 166:0.0012901861 167:0.0037493915 168:−0.0023597497 169:−0.00012567961 |
| 170:0.00047573209 171:7.8875659e−005 172:−0.0056320974 173:−0.0067036133 |
| 174:0.00017559867 175:0.001684437 176:−0.0034504069 177:0.0018235954 178:−0.001383971 |
| 179:0.0004998623 180:−0.00066253374 181:0.0015807585 182:0.00412085 183:0.0021063511 |
| 184:0.00072732504 185:−0.0012095358 186:−0.0030121093 187:−0.0020631803 |
| 188:−0.00068084424 189:0.0002527938 190:−0.0034640408 191:−0.00026976471 192:0.00097010034 |
| 193:−0.0011612385 194:−0.0015113452 195:0.00062438019 196:−0.00013164691 |
| 197:0.0020616048 198:0.0010445472 199:−0.0049765292 200:9.8877339e−005 201:0.0028779099 |
| 202:−0.0036701721 203:0.00099803088 204:0.00068234798 205:0.002192216 206:0.0033146022 |
| 207:0.00050616561 208:−0.0031757453 209:0.0028448526 210:0.00092352234 |
| 211:−0.0022140611 212:−0.0013608048 213:0.0051376815 214:−0.0017870248 215:−0.0027518668 |
| 216:0.00043837572 217:−0.027317183 218:−0.024619192 219:−0.01382506 220:−0.015382294 |
| 221:−0.016386922 222:−0.0094594397 223:−0.0056853383 224:−0.00050634646 |
| 225:−0.00087913428 226:−0.023968795 227:−0.0034698097 228:−0.0016731552 229:0.00047607321 |
| 230:−0.011432272 231:−0.00036644109 232:−0.0025967851 233:0.0015593689 |
| 234:−0.0042631673 235:−0.0053286692 236:−0.0059999214 237:−0.087129325 238:−0.063751429 |
| 239:−0.0045496477 240:−0.0073839114 241:0.0014150206 242:−0.0042075687 243:−0.0022374168 |
| 244:−0.041910719 245:−0.030919394 246:−0.049301699 247:−0.019442754 248:−0.0019611341 |
| 249:−0.0072449106 250:−0.0051453672 251:−0.0072873179 252:−0.005927789 253:−0.0018599511 |
| 254:−0.017141052 255:−0.023494685 256:−0.01788312 257:−0.01943502 258:−0.0060224077 |
| 259:−0.0073500308 260:−0.0064477329 261:−0.0002986097 262:−0.0014349599 263:−0.0020359957 |
| 264:−0.0082596857 265:−0.006963369 266:−0.0016096481 267:−0.0083991755 268:−0.046351645 |
| 269:−0.046128571 270:−0.011141608 271:0.0020650877 272:−0.0010642689 273:−0.018076098 |
| 274:−0.016929928 275:−0.0052876701 276:−0.0025432054 277:−0.04111632 278:−0.031511344 |
| 279:−0.019488858 280:−0.0036160324 281:−0.032332413 282:−0.023754911 283:−0.0030713808 |
| 284:−0.033357695 285:−0.027144579 286:−0.0093234172 287:−0.0091438433 288:0.00080924761 |
| 289:−0.0040808818 290:−0.00058058492 291:0.00025530611 292:0.00042821659 |
| 293:−0.0017559038 294:0.00030293313 295:−0.0004816725 296:−0.00057298481 297:−0.00086739491 |
| 298:0.0020803961 299:0.00010370808 300:0.00075778627 301:0.00074104586 |
| 302:−0.00021793939 303:0.0013351805 304:−0.0006143825 305:0.0025815656 306:7.1731614e−005 |
| 307:−0.0052312948 308:−0.00063595735 309:0.0015091125 310:−0.00024647679 |
| 311:−0.0050271503 312:−0.00065122027 313:−0.00070704299 314:−0.0038100008 315:0.0022923627 |
| 316:0.0019759815 317:0.00079242635 318:0.0045642676 319:0.001573379 320:0.0015903091 |
| 321:0.00074843148 322:−0.00091753813 323:0.0021253934 324:0.0013280844 |
| 325:−0.0030691659 326:−0.0033078301 327:0.0012743858 328:0.0024482214 329:0.0018192574 |
| 330:0.0026370357 331:0.0017312634 332:0.00066732749 333:0.00034391912 334:0.0037949879 |
| 335:0.0018411272 336:0.0051615993 337:0.0017553387 338:−0.0027431778 339:−0.0055160136 |
| 340:0.0031345901 # |
| 0.0031325744665863229 1:3.5110908 2:5.6174746 3:2.5606756 4:2.5834703 5:−7.6688213 |
| 6:−1.8434024 7:0.36071539 8:−0.45174024 9:2.6003997 10:0.5911482 11:−0.69220406 12:−2.2800779 |
| 13:1.8533925 14:−2.5804775 15:−1.1866112 16:−0.066687576 17:−1.5089196 18:−0.10368342 |
| 19:−0.087623782 20:−1.4943944 21:−0.86205274 22:0.7565676 23:−0.6693539 24:−0.71513188 |
| 25:1.2250738 26:0.0098061906 27:−0.40017042 28:−1.8319592 29:−0.0011238796 30:−1.8154995 |
| 31:0.2129721 32:−0.13248554 33:1.5796499 34:0.19158417 35:0.85793179 36:−0.3565852 |
| 37:−1.0822763 38:0.4891347 39:−0.13301478 40:0.34163928 41:0.06102673 42:−0.069330193 |
| 43:−0.16624564 44:−0.48438731 45:1.4786725 46:−1.8397158 47:0.69001108 48:0.91062814 |
| 49:0.020527706 50:0.13495424 51:−0.19287805 52:−0.74348158 53:−0.49106395 54:0.66449344 |
| 55:0.35523808 56:0.55576336 57:−0.49555805 58:1.5226892 59:−0.17116992 60:0.67154306 |
| 61:0.10370273 62:0.33758521 63:−0.30460584 64:−0.49617913 65:−0.24739511 66:0.73925906 |
| 67:−0.47236478 68:1.2099721 69:−0.032575484 70:−0.45242611 71:0.057035528 72:−0.46597356 |
| 73:−1.9234182 74:0.66382247 75:−0.52942693 76:−0.1035816 77:0.54878628 78:−1.7526437 |
| 79:−0.62102193 80:0.47183159 81:0.064084068 82:−0.35465324 83:−0.56368434 84:0.20363657 |
| 85:0.86101019 86:−0.76883537 87:0.17909677 88:−0.13035373 89:−0.30408055 90:0.073972978 |
| 91:0.60987514 92:0.78021365 93:0.53768206 94:−0.31102461 95:−0.51355314 96:−0.8174147 |

APPENDIX C1-continued

SVM Model Weights
(340; Normal/Diseased)

97:0.049540658 98:−0.56837559 99:0.010215698 100:0.56681705 101:0.21574417
102:0.18563138 103:0.0094845127 104:0.01989164 105:−0.13237675 106:0.83710998
107:−0.036966644 108:−0.77437228 109:0.20050789 110:0.044023968 111:−0.22260447
112:0.30727577 113:−0.59516901 114:0.1541591 115:0.019847022 116:0.19107249
117:0.0017406802 118:0.22522518 119:−0.37917262 120:0.59146839 121:−0.30348045
122:−0.054416969 123:0.51411492 124:0.382925 125:0.42478335 126:0.2201353 127:0.052761309
128:0.059751611 129:0.12411474 130:0.006737045 131:0.50253427 132:−0.38896278
133:−0.20190725 134:−0.11862744 135:−0.07166449 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:−0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
0.0034319981554139273 1:−1.2529821 2:1.393857 3:−0.40100932 4:0.80536771 5:−1.3698692
6:−4.2985444 7:−1.2300457 8:−1.6063071 9:1.3245063 10:2.534188 11:0.30171067 12:−0.74766284
13:3.4337008 14:0.50606573 15:4.3205433 16:0.94489902 17:−1.1800903 18:0.30085227
19:2.3550503 20:0.028076174 21:0.092185527 22:−0.054449778 23:1.274248 24:0.50065464
25:−1.1810657 26:1.0509241 27:−0.37393656 28:1.4507658 29:−1.8970845 30:1.2786201
31:0.26944366 32:−0.44957161 33:0.55799627 34:0.42565152 35:−0.50317258 36:1.2242279
37:−0.90718025 38:−0.22057383 39:0.89371914 40:−0.96436113 41:0.072177835 42:0.12445948
43:−1.6282943 44:0.078577504 45:−0.27634692 46:−0.035018735 47:−0.74332857 48:0.69187576
49:−0.74214166 50:0.72583973 51:−0.18807527 52:0.55824578 53:−0.5105381 54:0.34671339
55:0.23379517 56:−0.01904987 57:0.84335953 58:0.42913693 59:−1.2054484 60:−0.043084856
61:0.37992552 62:0.095283762 63:0.82956094 64:0.10494255 65:−0.31794438 66:−0.87085748
67:−2.1185856 68:0.28819486 69:−0.10490542 70:0.77444106 71:0.21397087 72:0.04484868
73:−0.1544427 74:−0.72419685 75:0.13790646 76:0.015397458 77:−0.66600096 78:1.1760044
79:0.48632273 80:1.5986381 81:1.1003675 82:0.19111913 83:−0.58480859 84:−0.2775254
85:0.275657 86:0.48834723 87:0.082033329 88:−0.28643975 89:0.72222316 90:0.24960896
91:−0.3258312 92:0.75809407 93:1.3115189 94:−0.84288025 95:0.28469461 96:−0.28144529
97:0.23324743 98:−0.42922881 99:0.40623993 100:−0.49336997 101:−0.1402445 102:−0.35526395
103:0.29490137 104:0.028230479 105:−1.209311 106:−0.014610616 107:0.1493403
108:0.10583811 109:0.08707945 110:−0.0893327 111:0.63148069 112:0.076761745
113:−0.2844643 114:0.31688702 115:0.45908958 116:0.040474951 117:0.093938112 118:−0.45347995
119:0.1510208 120:−0.026302498 121:0.38324666 122:0.58747828 123:0.22637787
124:0.20643677 125:0.27133456 126:−0.14284681 127:−0.29063538 128:0.070089884
129:0.1710581 130:0.40775952 131:−0.31571603 132:0.0012719868 133:0.052294984
134:−0.2020907 135:0.041005831 136:−0.0036672305 137:9.853208e−005 138:−0.017125415
139:0.0062208101 140:0.00056613336 141:0.0012280536 142:−0.00039310646

APPENDIX C1-continued

SVM Model Weights
(340; Normal/Diseased)

143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133174:0.00017559867 175:0.001684437
176:−0.0034504069 177:0.0018235954 178:−0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938
190:−0.0034640408 191:−0.00026976471 192:0.00097010034 193:−0.0011612385 194:−0.0015113452
195:0.00062438019 196:−0.00013164691 197:0.0020616048 198:0.0010445472
199:−0.0049765292 200:9.8877339e−005 201:0.0028779099 202:−0.0036701721 203:0.00099803088
204:0.00068234798 205:0.002192216 206:0.0033146022 207:0.00050616561 208:−0.0031757453
209:0.0028448526 210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097
228:−0.0016731552 229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
−0.0034319981554139273 1:−6.5375977 2:2.1123948 3:1.1355326 4:−2.3440728 5:−0.40250897
6:−5.1222434 7:2.0590734 8:0.87406713 9:−0.42407495 10:1.3824636 11:−0.80428976 12:−1.7772833
13:6.3438635 14:2.1855338 15:2.9639337 16:0.69173807 17:−0.41536355 18:−1.5802912
19:1.2215521 20:2.8985655 21:−0.068783447 22:3.3010855 23:0.2179627 24:4.0880098
25:0.94239813 26:4.1142564 27:2.5587342 28:3.4989934 29:−1.4943497 30:−1.0253848
31:1.2891228 32:0.19311364 33:−1.4917337 34:−0.40490827 35:1.2551166 36:1.0866218
37:2.749121 38:−0.95984066 39:−1.5400003 40:−1.4382766 41:1.1438725 42:1.8228887
43:0.45887417 44:1.3158252 45:1.8924459 46:1.5149728 47:0.47897026 48:−1.0465672
49:0.049777627 50:1.819648 51:0.14531961 52:−0.031018037 53:0.33217061 54:1.054731
55:0.38953736 56:−0.84029639 57:0.49298248 58:−0.39699548 59:−0.70166439 60:−0.95547146
61:0.74615616 62:−1.2175609 63:−0.09551914 64:−0.040590521 65:1.4343472 66:0.17118558
67:0.16519417 68:0.11700103 69:0.058235288 70:−0.86078101 71:−0.27289188 72:0.58181089
73:−0.85354793 74:0.15490662 75:−0.460251 76:−0.82907426 77:0.016911654 78:−0.27042994
79:0.7150737 80:−0.3998346 81:0.17056635 82:−0.16897039 83:−0.21618274 84:0.026753411
85:0.079761699 86:0.53720021 87:0.29263553 88:0.46407098 89:−0.28705877 90:−0.53804845
91:−0.083854906 92:0.46788815 93:−0.29520747 94:0.068325058 95:0.44259748 96:0.040507834
97:−0.79649287 98:0.36965564 99:0.15610714 100:0.24624342 101:0.33344293 102:−0.049116693
103:0.21491592 104:−0.19786303 105:0.55915242 106:0.086026192 107:−0.42804053
108:−0.15867032 109:0.27248678 110:−0.30683452 111:−0.29971489 112:−0.19257328 113:−0.38490406
114:−0.11202357 115:−0.1701887 116:0.21125674 117:−0.16649055 118:0.14343941
119:−0.093759537 120:0.10848325 121:−0.11846392 122:0.35855272 123:−0.071847282
124:−0.13645978 125:0.072031558 126:−0.28300413 127:−0.059585273 128:0.12359983
129:0.32319039 130:−0.051716141 131:0.16017263 132:0.015883218 133:−0.033865739
134:0.19289009 135:0.048813734 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133 174:0.00017559867 175:0.001684437
176:−0.0034504069 177:0.0018235954 178:−0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938

APPENDIX C1-continued

SVM Model Weights
(340; Normal/Diseased)

190:−0.0034640408 191:−0.00026976471 192:0.00097010034 193:−0.0011612385 194:−0.0015113452
195:0.00062438019 196:−0.00013164691 197:0.0020616048 198:0.0010445472
199:−0.0049765292 200:9.8877339e−005 201:0.0028779099 202:−0.0036701721 203:0.00099803088
204:0.00068234798 205:0.002192216 206:0.0033146022 207:0.00050616561 208:−0.0031757453
209:0.0028448526 210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097
228:−0.0016731552 229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257−:0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
−0.0034319981554139273 1:−0.60706848 2:−0.56179869 3:−2.8295784 4:2.1079314 5:−2.16576
6:−1.5902358 7:−3.8995321 8:−1.391099 9:1.3323318 10:2.3022547 11:−0.15200429 12:−1.7236745
13:−0.28189707 14:0.092928797 15:0.5678165 16:0.16910324 17:−1.7369378 18:1.1536523
19:0.4399763 20:0.94320494 21:−1.0564628 22:−0.40919417 23:−2.1857901 24:0.065937854
25:0.19628744 26:1.2588513 27:1.2625566 28:0.59739804 29:−1.7135398 30:0.37543643
31:−1.0696378 32:1.652465 33:−0.32052153 34:0.4178119 35:0.82741022 36:0.23162919
37:1.2215804 38:0.47287229 39:0.669622 40:−0.10720342 41:−0.34346694 42:−0.44582871
43:−0.1102373 44:0.1677283 45:−1.2041866 46:−0.97990817 47:−2.2895584 48:−0.11250075
49:−0.8322044 50:−0.024652796 51:−1.3362759 52:−0.14697382 53:−0.081530415 54:0.65578473
55:0.84578443 56:0.124378 57:−0.048972573 58:0.0070974482 59:0.73587078 60:−0.97483116
61:0.19108705 62:−0.75764817 63:0.017253783 64:0.37827864 65:−0.21863103 66:−0.42593646
67:−0.52796865 68:0.62855148 69:0.14516357 70:0.16399099 71:−0.28082269 72:−0.035006855
73:0.21659459 74:1.3164793 75:−0.17866343 76:0.24791805 77:0.62605935 78:0.45940989
79:0.69573057 80:0.71832937 81:−0.42727691 82:−0.32615939 83:−0.28442365 84:−1.3224995
85:−0.47572079 86:0.11412273 87:0.35794756 88:0.30290192 89:0.42681575 90:0.75971884
91:−0.45050859 92:0.32633391 93:−0.10428542 94:0.15158299 95:−0.29513499 96:−0.26781413
97:0.11819297 98:0.34320262 99:−0.37755403 100:0.1883643 101:−0.42627811 102:−0.18861955
103:−0.25941187 104:0.81041211 105:0.28098387 106:0.55561215 107:−0.66978216
108:0.26184267 109:−0.5240131 110:0.51668859 111:−0.17422822 112:0.46413377
113:0.15254496 114:−0.19430003 115:−0.09640865 116:−0.37656128 117:−0.40266412
118:−0.32158232 119:−0.77949405 120:−0.037294488 121:−0.61971009 122:−0.36642665
123:−0.79455006 124:0.5838899 125:−0.29188615 126:−0.30021444 127:−0.32980245 128:−0.44631222
129:−0.33568916 130:0.0072017759 131:0.18447824 132:0.17114799 133:−0.15524147
134:−0.19535366 135:0.010804381 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133 174:0.00017559867 175:0.001684437
176:−0.0034504069 177:0.0018235954 178:−0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938
190:−0.0034640408 191:−0.00026976471 192:0.00097010034 193:−0.0011612385 194:−0.0015113452
195:0.00062438019 196:−0.00013164691 197:0.0020616048 198:0.0010445472
199:−0.0049765292 200:9.8877339e−005 201:0.0028779099 202:−0.0036701721 203:0.00099803088
204:0.00068234798 205:0.002192216 206:0.0033146022 207:0.00050616561 208:−0.0031757453
209:0.0028448526 210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097
228:−0.0016731552 229:0.00047607321 230:−0.011432272 231:−0.00036644109 232:−0.0025967851
233:0.0015593689 234:−0.0042631673 235:−0.0053286692 236:−0.0059999214 237:−0.087129325

APPENDIX C1-continued

| SVM Model Weights (340; Normal/Diseased) |
|---|
| 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # −0.0034319981554139273 1:−1.3632743 2:−1.9445323 3:0.65233999 4:−0.58333957 5:−2.1690819 6:−1.557755 7:−3.9043965 8:−0.30472508 9:0.2361026 10:0.85410559 11:3.0135179 12:0.60649604 13:−1.2247649 14:0.6844058 15:0.44654614 16:−1.1434579 17:0.58581215 18:−0.4943729 19:2.888381 20:−1.4632667 21:0.035331994 22:0.34741896 23:−1.0578666 24:−1.6146865 25:1.7983127 26:0.18128556 27:−1.9081653 28:2.5913491 29:−2.3153069 30:0.58279341 31:−1.00468 32:1.4105986 33:0.32527116 34:1.7262596 35:−0.7636652 36:−0.6239388 37:−1.2229923 38:0.92973059 39:1.2896794 40:−0.54387486 41:1.815182 42:1.2686126 43:0.026493588 44:0.13799661 45:0.038556926 46:1.6906935 47:1.5857954 48:−0.63974899 49:−0.19294812 50:0.36613348 51:2.5498624 52:−0.62005687 53:0.41496003 54:0.48494276 55:0.018885197 56:−0.24577679 57:−0.0083116852 58:−0.62871617 59:0.81586206 60:0.94185793 61:−1.1134834 62:1.7222621 63:0.96535265 64:−1.1845593 65:1.0662568 66:0.74076414 67:1.2916409 68:−0.3489947 69:−1.1012481 70:−0.31059921 71:0.12768701 72:−0.8858223 73:0.7715655 74:0.89574414 75:−0.61715019 76:0.54230756 77:−1.045996 78:0.67768413 79:−0.73282576 80:0.23836881 81:0.13851836 82:−0.30754682 83:0.015328793 84:−0.28529775 85:−0.51043022 86:−0.59714639 87:−0.11183778 88:0.11600714 89:0.33050406 90:−0.40183187 91:−0.55495155 92:0.69483292 93:−0.030177858 94:0.051240943 95:−0.067810789 96:0.12009942 97:0.060447887 98:−0.78094363 99:0.10887952 100:0.72515273 101:−0.85825855 102:0.47904605 103:0.10572934 104:0.22952671 105:0.24822652 106:−0.39131927 107:−0.17019869 108:−0.0048041134 109:−0.29701149 110:−0.28170228 111:0.32302824 112:0.35721096 113:−0.51821142 114:−0.149049 115:−0.30888659 116:−0.55437291 117:−0.21446767 118:0.077094577 119:−0.16246751 120:−0.15014498 121:0.033474043 122:0.29328528 123:0.035680152 124:−0.06882707 125:−0.11773612 126:0.072734416 127:0.006365994 128:−0.27049014 129:0.15621305 130:0.28391689 131:0.344648 132:−0.30017859 133:0.098633222 134:0.097014897 135:−0.047203265 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 |

APPENDIX C1-continued

| SVM Model Weights (340; Normal/Diseased) |
|---|
| 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| 0.0034319981554139273 1:3.6875272 2:3.0250661 3:0.29052538 4:1.6621389 5:−1.077208 6:−1.4265242 7:5.6980257 8:2.4122481 9:−0.23186241 10:−3.5392511 11:−0.22240373 12:0.3499389 13:−0.74368799 14:−0.38710013 15:−2.0126009 16:−1.6567438 17:0.18400183 18:2.4745722 19:0.029114984 20:−0.20238526 21:0.36805978 22:1.5960912 23:0.6498906 24:−1.1362889 25:−0.62198257 26:0.18703945 27:1.2769275 28:−0.82102513 29:1.5383286 30:1.641359 31:−0.11083211 32:−0.73535907 33:0.12018158 34:−1.9625522 35:−0.033817839 36:−0.69495207 37:0.84588385 38:−0.34971488 39:0.27114922 40:1.1997342 41:−1.5652107 42:−0.71289748 43:−0.47851917 44:0.85789436 45:−0.94423765 46:0.032212444 47:0.23876941 48:−2.2591531 49:0.65750432 50:1.5780753 51:1.9137375 52:0.07368347 53:0.069766484 54:−0.38831636 55:1.0103614 56:0.64284617 57:0.26976886 58:−0.3094748 59:1.0858464 60:−0.38908195 61:−1.7455355 62:0.42903882 63:−0.42164421 64:−1.0976751 65:0.47146344 66:−1.7880417 67:−1.6078222 68:−0.31294608 69:−0.4832885 70:−0.69922173 71:−1.3377334 72:−0.26947746 73:0.7479955 74:0.045744106 75:0.10229278 76:0.30118969 77:0.6811837 78:−0.45769265 79:0.27169511 80:0.44472837 81:−0.29408213 82:−1.1094222 83:0.3666563 84:−0.045561716 85:0.18670417 86:0.56415009 87:−0.11433779 88:0.20290005 89:−1.0556993 90:−0.5976212 91:−0.089318469 92:−0.0057319254 93:−0.073113471 94:−0.17188995 95:0.39476091 96:−0.17765622 97:−0.39548203 98:−0.31302878 99:0.42452362 100:−0.056253672 101:−0.47864839 102:−0.025919076 103:0.096916229 104:0.027402377 105:0.015727635 106:−0.52887905 107:−0.0062635564 108:−0.49763083 109:0.6224966 110:0.032929033 111:−0.55686539 112:0.42677939 113:−0.14102013 114:0.73409796 115:−0.45192954 116:0.51410705 117:0.034478687 118:−0.35689452 119:−0.011386579 120:−0.0029351646 121:−0.021493971 122:0.22056937 123:−0.0045534759 124:0.039128121 125:0.21568246 126:0.065558903 127:−0.33998546 128:−0.076104723 129:−0.58559448 130:0.12305989 131:0.092112459 132:−0.023360334 133:0.14563508 134:−0.28518763 135:−0.026241686 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 |

APPENDIX C1-continued

SVM Model Weights
(340; Normal/Diseased)

330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
0.0034319981554139273 1:10.933654 2:6.4248862 3:3.2384374 4:0.14409828 5:2.0443769
6:−0.96650457 7:−2.7591114 8:3.8425102 9:1.286938 10:−2.7674775 11:4.7782588 12:2.5789647
13:0.5836091 14:0.25201192 15:2.1731467 16:−1.2429184 17:−2.0514996 18:−0.21137145
19:3.2398725 20:−0.54532427 21:−0.87394041 22:−1.0946345 23:0.33414531 24:−0.46712443
25:0.761127 26:0.69790411 27:−0.95681322 28:−1.1794156 29:−0.8807224 30:−1.3876348
31:0.28623164 32:0.90492404 33:0.48581135 34:0.92738605 35:0.39698663 36:0.48640934
37:0.40271929 38:0.89204979 39:−1.2035446 40:1.3811755 41:−1.0077406 42:0.095975496
43:0.081236303 44:−0.27388161 45:0.43766725 46:−1.2321532 47:0.5831117 48:0.12279975
49:−0.31562462 50:1.7708108 51:−0.088413909 52:−1.2922177 53:−0.42708319 54:1.741316
55:−0.46906748 56:−0.091270804 57:−0.66427916 58:0.14182013 59:−0.056508265 60:−1.7402322
61:0.27224803 62:1.1451247 63:−0.65408528 64:−1.0457289 65:−0.051288955 66:−0.80570686
67:1.0002974 68:0.42793864 69:0.51741147 70:0.47157639 71:0.59070158 72:−0.16071473
73:−0.089933135 74:−0.33037904 75:1.2456383 76:−0.6323474 77:0.48095614 78:1.2343533
79:0.13654871 80:−0.73044246 81:−0.41132534 82:−0.18622157 83:0.49650639 84:−0.74608111
85:0.91862726 86:0.30114627 87:0.25944051 88:−0.75798339 89:−0.0956062 90:0.056009207
91:−0.93178469 92:−0.34544295 93:−0.35667893 94:−1.1800114 95:−0.65725023 96:−0.4534899
97:0.53535557 98:0.14212164 99:0.049174767 100:0.56335914 101:−0.34140998
102:−0.070805512 103:−0.27334151 104:−0.0039870292 105:−0.45039079 106:−0.049886834
107:−0.004565747 108:0.34987667 109:0.1166205 110:−0.20696275 111:−0.35821131 112:−0.75638342
113:−0.30853245 114:−0.32193542 115:−0.032231439 116:0.16625163 117:0.080795206
118:0.023019888 119:−0.21747378 120:−0.43029138 121:−0.076045305 122:0.15438259
123:0.20693475 124:0.076103754 125:0.050283808 126:−0.012497452 127:0.5167554
128:0.37512276 129:−0.38496837 130:−0.23641486 131:0.16555128 132:0.23625681
133:0.27457133 134:0.099129945 135:−0.057866845 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:−0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286−:0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
0.0034319981554139273 1:−0.40706003 2:−7.1397123 3:2.6859665 4:−7.0096903 5:3.0317152
6:−4.3316078 7:1.4683849 8:−2.7222147 9:−2.3974659 10:1.5284376 11:−2.2683592 12:−1.688279
13:−0.69580024 14:−0.165719 15:−0.095550545 16:−0.76551509 17:−3.3442504 18:0.72300565
19:3.3406658 20:0.19809642 21:−1.6887234 22:−2.3278005 23:−1.3378291 24:3.505214
25:−1.6693422 26:−3.1288674 27:2.3521557 28:0.59533548 29:−1.276844 30:−0.11495301
31:4.1659765 32:−1.3004161 33:−5.8988891 34:2.8472443 35:−0.29545334 36:−4.1669316

APPENDIX C1-continued

| SVM Model Weights (340; Normal/Diseased) |
|---|
| 37:−2.3669634 38:2.4650891 39:0.46121722 40:1.6261921 41:2.2180104 42:1.5175546 43:−0.25555608 44:0.84000587 45:−0.069663025 46:−1.3411472 47:−0.33703804 48:−1.6543316 49:0.025696442 50:−0.70928001 51:1.2521927 52:0.80985659 53:−0.25006622 54:0.75404704 55:−0.097098581 56:1.020278 57:0.80506575 58:0.20001346 59:0.030074423 60:−0.25281274 61:−0.50338525 62:−0.038949292 63:−0.12667872 64:−0.23509546 65:−0.10394531 66:−0.68150729 67:0.32079381 68:−0.017649971 69:1.0972716 70:−0.062842958 71:0.067879252 72:0.62627828 73:−0.29855132 74:−0.07247974 75:0.33787322 76:0.40759748 77:0.69339627 78:−0.27269831 79:−0.29921198 80:0.3968524 81:−0.082895368 82:−0.020286532 83:0.31697649 84:0.13875051 85:0.32336545 86:−0.28411227 87:−0.11308259 88:−0.1360822 89:0.34385523 90:0.3937214 91:0.040391378 92:−0.36977676 93:0.28433147 94:0.040394466 95:0.11587242 96:0.15589859 97:−0.19559988 98:−0.024758732 99:−0.062763132 100:0.011111774 101:0.069484137 102:−0.036218368 103:0.19050491 104:−0.018268865 105:0.027673149 106:−0.048857551 107:−0.18509105 108:0.083567955 109:0.027324546 110:−0.13914543 111:−0.048291504 112:0.10988387 113:−0.066464081 114:0.041141599 115:0.085553147 116:0.094267316 117:−0.056311987 118:−0.091130406 119:0.21467622 120:0.13654287 121:−0.095273346 122:−0.19139628 123:0.081190117 124:0.028709168 125:0.04738662 126:0.24163833 127:0.062439539 128:−0.069767214 129:0.062194467 130:−0.16131501 131:−0.11901218 132:−0.00034159876 133:−0.04819677 134:−0.07644289 135:0.078903913 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # −0.0034319981554139273 1:5.5017767 2:0.76866108 3:3.5021136 4:−3.4441924 5:−1.7227199 6:−2.3480663 7:5.2186608 8:2.0708718 9:1.1557996 10:−2.8974543 11:−1.7903497 12:−1.0666572 13:1.2271978 14:1.5467659 15:−3.7293766 16:2.8392794 17:1.2993569 18:2.5210259 19:−1.9889575 20:1.5789289 21:−2.0791085 22:−0.16521527 23:1.1609622 24:−2.1516325 25:0.2511712 26:0.19739714 27:4.1415296 28:0.97708219 29:−3.1115251 30:6.4011049 31:−3.1671309 32:−1.5625285 33:−1.1289238 34:−0.8072629 35:−0.060927153 36:−0.66443217 37:2.3702629 38:−0.16842309 39:−0.4935627 40:2.0837352 41:0.80638069 42:1.5681704 43:1.1968515 44:−0.87553591 45:−2.2585204 46:−0.74682492 47:1.2382894 48:1.0413882 49:−1.0842441 50:−0.2513561 51:−0.91843736 52:−1.3671836 53:−1.1596954 54:0.26116666 55:−0.84180433 56:0.26325849 57:0.46045518 58:−0.35954237 59:0.095890306 60:−0.93630034 61:0.89843744 62:0.52230662 63:0.49175408 64:0.74472219 65:−1.0776283 66:−0.29318652 67:0.27382204 68:0.06797459 69:0.38458759 70:−0.14918885 71:−0.084517807 72:−0.55330855 73:−0.27780494 74:1.0952821 75:−0.2640903 76:−0.080420539 77:−0.56950516 78:−0.014582542 79:−0.98771346 80:−0.4344278 81:−0.19744191 82:0.34438324 83:0.67537814 84:0.053237647 85:0.015955647 86:0.35000312 87:−0.80852437 88:0.15167473 89:−0.49606982 90:−0.61942643 |

APPENDIX C1-continued

| SVM Model Weights (340; Normal/Diseased) |
|---|
| 91:−0.21039526 92:0.27886364 93:0.26335257 94:−0.40555432 95:0.21670502 96:0.27674332 97:0.094229855 98:−0.14936881 99:0.27394944 100:−0.28099453 101:0.22439933 102:0.035959233 103:0.32972571 104:−0.14133739 105:−0.14090203 106:0.039193571 107:0.011332417 108:0.096545659 109:−0.0046955626 110:0.090976082 111:0.39119565 112:−0.005056249 113:0.0022151032 114:−0.52396691 115:0.045902133 116:0.092070244 117:−0.1861043 118:0.21312852 119:0.0096034352 120:−0.030817525 121:−0.091185309 122:−0.19852459 123:0.093788259 124:0.11718982 125:0.21673851 126:0.056335893 127:0.16344781 128:−0.0058643324 129:0.17316958 130:0.12993692 131:−0.030138636 132:−0.17875375 133:0.021982102 134:−0.065788575 135:−0.023161959 136:−0.0036672305 137:9.853208e−005 138:−0.017125415 139:0.0062208101 140:0.00056613336 141:0.0012280536 142:−0.00039310646 143:−0.0063707544 144:0.0015248039 145−:0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.0017478150550285895 1:−7.5607929 2:4.9967093 3:−1.264623 4:1.5839788 5:−3.1135581 6:−1.7120829 7:4.2883148 8:0.10269687 9:−1.0577402 10:−0.98678935 11:−3.2682719 12:−2.218318 13:0.040950354 14:−1.4008325 15:−0.96606475 16:−0.28105533 17:−0.47668806 18:1.2778534 19:1.9604092 20:1.4759794 21:2.3012459 22:1.6083701 23:−1.4667403 24:0.63299334 25:0.97550392 26:−0.54523748 27:0.59301919 28:3.1892025 29:0.069494046 30:−0.062061142 31:−0.66459078 32:−0.29568297 33:0.53681523 34:2.0728886 35:0.60553735 36:0.82829171 37:0.86545765 38:0.52002668 39:0.55903029 40:−0.33308479 41:−0.73884112 42:0.15741917 43:−0.38348535 44:−0.33616903 45:−0.20357849 46:2.0278337 47:1.0588315 48:0.61091554 49:−0.81337583 50:−1.5761976 51:0.23632507 52:0.94802552 53:−0.5830254 54:−1.6032152 55:1.3840418 56:−0.51162708 57:−0.20480803 58:0.83730423 59:0.51563877 60:0.61808813 61:0.56924182 62:−0.77530587 63:−0.0090414956 64:−0.033454075 65:−0.19037022 66:0.034517366 67:0.45609969 68:0.10079073 69:0.51457125 70:−1.0463495 71:−1.2487614 72:0.78104967 73:−0.20238008 74:−0.31103361 75:−0.12727672 76:2.1968956 77:0.97095293 78:1.0261937 79:−0.40294078 80:−0.44990107 81:0.3605907 82:0.83272147 83:−0.57420367 84:0.34378755 85:0.20394959 86:0.54164338 87:−0.35926723 88:−0.39825404 89:−0.64205307 90:0.59346592 91:1.1435597 92:−0.057810221 93:−0.019218 94:−1.0919204 95:−0.45123491 96:0.12415867 97:0.31998202 98:0.65927428 99:0.017214894 100:−0.10224611 101:−0.53348273 102:0.69101948 103:−0.698798 104:−0.28382832 105:−0.30568269 106:0.14065288 107:−0.12050519 108:0.39194202 109:−0.079414107 110:−0.29646572 111:0.47219637 112:−0.26385772 113:−0.065177754 114:−0.10920458 115:−0.25679943 116:0.15648159 117:0.18953295 118:−0.20878601 119:−0.29837388 120:−0.090249047 121:0.074154943 122:0.0039142771 123:0.41833293 124:−0.082887545 125:−0.038029969 126:0.13444678 127:0.052840874 128:−0.21969235 129:−0.2998597 130:−0.36949524 131:0.22898072 132:0.05183354 133:0.062183738 134:−0.14366834 135:−0.12232868 136−0.0036672305 |

APPENDIX C1-continued

SVM Model Weights
(340; Normal/Diseased)

137:9.853208e-005 138:-0.017125415 139:0.0062208101 140:0.00056613336 141:0.0012280536
142:-0.00039310646 143:-0.0063707544 144:0.0015248039 145:-0.0029345977
146:-0.00076821423 147:0.00013666278 148:-0.0051379474 149:0.0066761598 150:-0.0024066679
151:0.0038081626 152:-0.0013487631 153:-0.0020869875 154:-0.0023751855 155:1.1204498e-006
156:0.0039485889 157:-0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:-0.0023597497 169:-0.00012567961
170:0.00047573209 171:7.8875659e-005 172:-0.0056320974 173:-0.0067036133
174:0.00017559867 175:0.001684437 176:-0.0034504069 177:0.0018235954 178:-0.001383971
179:0.0004998623 180:-0.00066253374 181:0.0015807585 182:0.00412085 183:0.0021063511
184:0.00072732504 185:-0.0012095358 186:-0.0030121093 187:-0.0020631803
188:-0.00068084424 189:0.0002527938 190:-0.0034640408 191:-0.00026976471 192:0.00097010034
193:-0.0011612385 194:-0.0015113452 195:0.00062438019 196:-0.00013164691
197:0.0020616048 198:0.0010445472 199:-0.0049765292 200:9.8877339e-005 201:0.0028779099
202:-0.0036701721 203:0.00099803088 204:0.00068234798 205:0.002192216 206:0.0033146022
207:0.00050616561 208:-0.0031757453 209:0.0028448526210:0.000923
211:-0.0022140611 212:-0.0013608048 213:0.0051376815 214:-0.0017870248 215:-0.0027518668
216:0.00043837572 217:-0.027317183 218:-0.024619192 219:-0.01382506 220:-0.015382294
221:-0.016386922 222:-0.0094594397 223:-0.0056853383 224:-0.00050634646
225:-0.00087913428 226:-0.023968795 227:-0.0034698097 228:-0.0016731552 229:0.00047607321
230:-0.011432272 231:-0.00036644109 232:-0.0025967851 233:0.0015593689
234:-0.0042631673 235:-0.0053286692 236:-0.0059999214 237:-0.087129325 238:-0.063751429
239:-0.0045496477 240:-0.0073839114 241:0.0014150206 242:-0.0042075687 243:-0.0022374168
244:-0.041910719 245:-0.030919394 246:-0.049301699 247:-0.019442754 248:-0.0019611341
249:-0.0072449106 250:-0.0051453672 251:-0.0072873179 252:-0.005927789 253:-0.0018599511
254:-0.017141052 255:-0.023494685 256:-0.01788312 257:-0.01943502 258:-0.0060224077
259:-0.0073500308 260:-0.0064477329 261:-0.0002986097 262:-0.0014349599 263:-0.0020359957
264:-0.0082596857 265:-0.006963369 266:-0.0016096481 267:-0.0083991755 268:-0.046351645
269:-0.046128571 270:-0.011141608 271:0.0020650877 272:-0.0010642689 273:-0.018076098
274:-0.016929928 275:-0.0052876701 276:-0.0025432054 277:-0.04111632 278:-0.031511344
279:-0.019488858 280:-0.0036160324 281:-0.032332413 282:-0.023754911 283:-0.0030713808
284:-0.033357695 285:-0.027144579 286:-0.0093234172 287:-0.0091438433 288:0.00080924761
289:-0.0040808818 290:-0.00058058492 291:0.00025530611 292:0.00042821659
293:-0.0017559038 294:0.00030293313 295:-0.0004816725 296:-0.00057298481 297:-0.00086739491
298:0.0020803961 299:0.00010370808 300:0.00075778627 301:0.00074104586
302:-0.00021793939 303:0.0013351805 304:-0.0006143825 305:0.0025815656 306:7.1731614e-005
307:-0.0052312948 308:-0.00063595735 309:0.0015091125 310:-0.00024647679
311:-0.0050271503 312:-0.00065122027 313:-0.00070704299 314:-0.0038100008 315:0.0022923627
316:0.0019759815 317:0.00079242635 318:0.0045642676 319:0.001573379 320:0.0015903091
321:0.00074843148 322:-0.00091753813 323:0.0021253934 324:0.0013280844
325:-0.0030691659 326:-0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:-0.0027431778 339:-0.0055160136
340:0.0031345901 #
-0.0025489065960105145 1:16.392971 2:-4.7027459 3:-2.2550261 4:-0.21748754 5:-4.5716577
6:5.9160895 7:5.429513 8:2.0746083 9:-4.2725348 10:-4.7335415 11:1.0379436 12:5.0396523
13:-2.4807262 14:2.5711129 15:2.5762944 16:-6.0362124 17:1.442536 18:2.5452075 19:-0.87619179
20:1.0887364 21:1.1883737 22:0.69489425 23:0.91156578 24:0.8202377 25:1.1617807
26:1.6182382 27:0.34300202 28:0.76539904 29:0.33116844 30:0.065732196 31:1.1510335
32:0.55732244 33:0.99700636 34:0.67217964 35:-0.66296524 36:-0.86372066 37:0.43462038
38:0.064805917 39:-0.10519884 40:0.84757334 41:0.067920893 42:-0.18248896 43:0.15334356
44:1.7386529 45:0.34560779 46:0.12476955 47:-2.1366498 48:0.058745317 49:-0.30172783
50:-0.74402666 51:0.53211993 52:-0.92503977 53:0.84559625 54:1.4197814 55:1.0785793
56:0.53916639 57:-0.68887943 58:-0.093460314 59:0.80369282 60:-0.7160964 61:-0.90808797
62:0.46412528 63:0.87957537 64:0.59649271 65:1.0608096 66:0.46454391 67:-0.64940065
68:0.99365824 69:-0.32061386 70:0.6111899 71:0.16018821 72:0.077451304 73:0.23101214
74:-0.24294817 75:-1.5528877 76:-0.097729526 77:0.55013484 78:0.22187085 79:0.2558637
80:-0.37704936 81:0.046806384 82:1.2514741 83:0.042035438 84:-0.016180828 85:0.28515542
86:-0.30722845 87:-0.86694443 88:0.11009838 89:-0.066572987 90:0.70142096 91:-0.93494213
92:0.40131098 93:0.41900817 94:0.25365081 95:0.14092642 96:-0.3349984 97:0.65535557
98:0.39964882 99:-0.29724681 100:-0.43414906 101:-0.076998442 102:-0.0021279654
103:-0.120182 104:-0.46770826 105:-0.2342044 106:0.63475507 107:-0.11029183 108:-0.067821957
109:0.55323797 110:-0.25449121 111:0.17435461 112:0.30987397 113:0.46150491
114:-0.21759985 115:0.183112 116:0.17959078 117:0.077756479 118:0.58794653 119:-0.25394571
120:0.47770235 121:0.40079489 122:0.077578716 123:-0.19039564 124:-0.31271484
125:-0.062937662 126:0.2125199 127:0.14255671 128:-0.13672383 129:0.16542396 130:-0.15656392
131:-0.14200482 132:-0.1648611 133:0.19795504 134:-0.001785985 135:0.078113474
136:-0.0036672305 137:9.853208e-005 138:-0.017125415 139:0.0062208101 140:0.00056613336
141:0.0012280536 142:-0.00039310646 143:-0.0063707544 144:0.0015248039
145:-0.0029345977 146:-0.00076821423 147:0.00013666278 148:-0.0051379474 149:0.0066761598
150:-0.0024066679 151:0.0038081626 152:-0.0013487631 153:-0.0020869875
154:-0.0023751855 155:1.1204498e-006 156:0.0039485889 157:-0.00011155871 158:0.00070337567
159:0.0012323871 160:0.0021008069 161:0.0028489598 162:0.00029079549 163:0.0020081406
164:0.0044465163 165:0.007065278 166:0.0012901861 167:0.0037493915 168:-0.0023597497
169:-0.00012567961 170:0.00047573209 171:7.8875659e-005 172:-0.0056320974
173:-0.0067036133 174:0.00017559867 175:0.001684437 176:-0.0034504069 177:0.0018235954
178:-0.001383971 179:0.0004998623 180:-0.00066253374 181:0.0015807585 182:0.00412085

APPENDIX C1-continued

| SVM Model Weights (340; Normal/Diseased) |
|---|
| 183:0.0021063511 184:0.00072732504 185:–0.0012095358 186:–0.0030121093 187:–0.0020631803 188:–0.00068084424 189:0.0002527938 190:–0.0034640408 191:–0.00026976471 192:0.00097010034 193:–0.0011612385 194:–0.0015113452 195:0.00062438019 196:–0.00013164691 197:0.0020616048 198:0.0010445472 199:–0.0049765292 200:9.8877339e–005 201:0.0028779099 202:–0.0036701721 203:0.00099803088 204:0.00068234798 205:0.002192216 206:0.0033146022 207:0.00050616561 208:–0.0031757453 209:0.0028448526 210:0.00092352234 211:–0.0022140611 212:–0.0013608048 213:0.0051376815 214:–0.0017870248 215:–0.0027518668 216:0.00043837572 217:–0.027317183 218:–0.024619192 219:–0.01382506 220:–0.015382294 221:–0.016386922 222:–0.0094594397 223:–0.0056853383 224:–0.00050634646 225:–0.00087913428 226:–0.023968795 227:–0.0034698097 228:–0.0016731552 229:0.00047607321 230:–0.011432272 231:–0.00036644109 232:–0.0025967851 233:0.0015593689 234:–0.0042631673 235:–0.0053286692 236:–0.0059999214 237:–0.087129325 238:–0.063751429 239:–0.0045496477 240:–0.0073839114 241:0.0014150206 242:–0.0042075687 243:–0.0022374168 244:–0.041910719 245:–0.030919394 246:–0.049301699 247:–0.019442754 248:–0.0019611341 249:–0.0072449106 250:–0.0051453672 251:–0.0072873179 252:–0.005927789 253:–0.0018599511 254:–0.017141052 255:–0.023494685 256:–0.01788312 257:–0.01943502 258:–0.0060224077 259:–0.0073500308 260:–0.0064477329 261:–0.0002986097 262:–0.0014349599 263:–0.0020359957 264:–0.0082596857 265:–0.006963369 266:–0.0016096481 267:–0.0083991755 268:–0.046351645 269:–0.046128571 270:–0.011141608 271:0.0020650877 272:–0.0010642689 273:–0.018076098 274:–0.016929928 275:–0.0052876701 276:–0.0025432054 277:–0.04111632 278:–0.031511344 279:–0.019488858 280:–0.0036160324 281:–0.032332413 282:–0.023754911 283:–0.0030713808 284:–0.033357695 285:–0.027144579 286:–0.0093234172 287:–0.0091438433 288:0.00080924761 289:–0.0040808818 290:–0.00058058492 291:0.00025530611 292:0.00042821659 293:–0.0017559038 294:0.00030293313 295:–0.0004816725 296:–0.00057298481 297:–0.00086739491 298:0.0020803961 299:0.00010370808 300:0.00075778627 301:0.00074104586 302:–0.00021793939 303:0.0013351805 304:–0.0006143825 305:0.0025815656 306:7.1731614e–005 307:–0.0052312948 308:–0.00063595735 309:0.0015091125 310:–0.00024647679 311–:0.0050271503 312:–0.00065122027 313:–0.00070704299 314:–0.0038100008 315:0.0022923627 316:0.0019759815 317:0.00079242635 318:0.0045642676 319:0.001573379 320:0.0015903091 321:0.00074843148 322:–0.00091753813 323:0.0021253934 324:0.0013280844 325:–0.0030691659 326:–0.0033078301 327:–0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:–0.0027431778 339:–0.0055160136 340:0.0031345901 # |
| –0.00021694412544797254 1:5.7605891 2:9.8290195 3:1.8789825 4:–1.1318272 5:7.9504757 6:0.34706745 7:–3.3513935 8:1.2476839 9:3.0434899 10:–0.36745211 11:3.7199888 12:1.8109978 13:–2.7700968 14:0.89088112 15:–6.2266636 16:–0.63499314 17:–0.95308942 18:–3.2592905 19:–0.27639693 20:1.4911562 21:–0.95498282 22:–2.6575968 23:–0.99992591 24:–0.11102299 25:–1.6752316 26:–0.4156343 27:0.33910745 28:1.8173996 29:0.76929176 30:1.4767234 31:0.56392443 32:–1.1427271 33:0.47812706 34:2.2496631 35:2.182483 36:1.8318955 37:–2.9768569 38:–3.1288815 39:0.5895263 40:4.7589025 41:–0.59536803 42:–0.80722958 43:–0.34699696 44:–0.9802708 45:1.6393638 46:1.0442442 47:0.32212991 48:0.25918323 49:–1.7139337 50:–0.17995603 51:0.19763853 52:1.0865116 53:0.86287361 54:0.60442656 55:0.86261737 56:–1.1502584 57:0.92417842 58:–0.64244395 59:0.17892943 60:–0.91824561 61:–0.24928856 62:–0.034462687 63:0.70051718 64:1.00837 65:1.2452569 66:0.16973068 67:0.041958362 68:–0.59003532 69:–0.53037918 70:0.89056855 71:0.3251256 72:0.051477909 73:–0.44470191 74:0.57884252 75:0.85947841 76:–0.1458649 77:–0.23340164 78:–0.17262885 79:0.57736421 80:0.061778106 81:–0.018538158 82:–0.14533332 83:–0.82432085 84:0.49507469 85:–0.14818789 86:0.12730397 87:0.20189728 88:0.70823449 89:–0.50241673 90:0.42246193 91:0.63044739 92:0.50862873 93:0.20819801 94:0.26308593 95:–0.043910567 96:0.76509541 97:0.15793175 98:–0.26816332 99:0.084403165 100:–0.20572771 101:–0.1376276 102:–0.30192712 103:0.026766492 104:0.13220508 105:0.12338309 106:0.29491246 107:–0.27875268 108:–0.29653773 109:0.066153549 110:0.074190728 111:0.062084291 112:–0.059445068 113:0.14017068 114:0.089980848 115:–0.37553215 116:0.29876247 117:–0.045087591 118:–0.019912641 119:–0.11419063 120:0.075319394 121:0.041240875 122:0.040776737 123:–0.024914727 124:0.10218149 125:0.015685819 126:0.044775065 127:0.072801702 128:0.038063526 129:0.12310021 130:–0.053280022 131:–0.024600053 132:0.0933327 133:0.12956059 134:0.052018698 135:–0.063025571 136:–0.0036672305 137:9.853208e–005 138:–0.017125415 139:0.0062208101 140:0.00056613336 141:0.0012280536 142:–0.00039310646 143:–0.0063707544 144:0.0015248039 145:–0.0029345977 146:–0.00076821423 147:0.00013666278 148:–0.0051379474 149:0.0066761598 150:–0.0024066679 151:0.0038081626 152:–0.0013487631 153:–0.0020869875 154:–0.0023751855 155:1.1204498e–006 156:0.0039485889 157:–0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:–0.0023597497 169:–0.00012567961 170:0.00047573209 171:7.8875659e–005 172:–0.0056320974 173:–0.0067036133 174:0.00017559867 175:0.001684437 176:–0.0034504069 177:0.0018235954 178:–0.001383971 179:0.0004998623 180:–0.00066253374 181:0.0015807585 182:0.00412085 183:0.0021063511 184:0.00072732504 185:–0.0012095358 186:–0.0030121093 187:–0.0020631803 188:–0.00068084424 189:0.0002527938 190:–0.0034640408 191:–0.00026976471 192:0.00097010034 193:–0.0011612385 194:–0.0015113452 195:0.00062438019 196:–0.00013164691 197:0.0020616048 198:0.0010445472 199:–0.0049765292 200:9.8877339e–005 201:0.0028779099 202:–0.0036701721 203:0.00099803088 204:0.00068234798 205:0.002192216 206:0.0033146022 207:0.00050616561 208:–0.0031757453 209:0.0028448526 210:0.00092352234 211:–0.0022140611 212:–0.0013608048 213:0.0051376815 214:–0.0017870248 215:–0.0027518668 216:0.00043837572 217:–0.027317183 218:–0.024619192 219:–0.01382506 220:–0.015382294 221:–0.016386922 222:–0.0094594397 223:–0.0056853383 224:–0.00050634646 |

APPENDIX C1-continued

| SVM Model Weights (340; Normal/Diseased) |
|---|
| 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # 0.0034319981554139273 1:−1.513376 2:−1.8505038 3:−3.1226563 4:3.4844956 5:−1.8776969 6:−1.47199 7:0.80681765 8:−0.75451481 9:−0.47854143 10:0.9895125 11:−0.8022784 12:−1.1363293 13:−0.39838672 14:−0.53547555 15:−1.0331632 16:−0.12748334 17:1.5773466 18:−0.048117671 19:0.64761943 20:−1.1173811 21:0.22006649 22:0.42375195 23:0.70772225 24:0.90536618 25:0.068708986 26:1.2127565 27:0.79518342 28:1.7149159 29:−1.3412409 30:0.84027767 31:−1.9769535 32:−1.1390235 33:−0.19975612 34:−0.14863788 35:−0.99266446 36:0.42730525 37:−1.4593364 38:−0.050251674 39:−0.92185473 40:−0.37061065 41:0.61643738 42:0.16165736 43:−0.59203166 44:1.5533814 45:0.28165334 46:1.1489488 47:0.023842113 48:0.53270268 49:0.22172646 50:0.37802032 51:−0.37980214 52:0.74919069 53:0.75821257 54:1.0981214 55:−0.73057991 56:−1.1890702 57:1.5371476 58:0.77694148 59:0.55919814 60:1.1852288 61:−0.25287256 62:−0.53572887 63:0.99268645 64:−0.54913682 65:−0.5330345 66:−1.5217758 67:0.36674589 68:−0.14583459 69:−0.96768582 70:−0.087492332 71:0.77057946 72:0.61932683 73:0.68469149 74:−1.3130057 75:1.0343505 76:0.12145463 77:0.82462418 78:−0.74196804 79:0.12187001 80:−0.20082386 81:−0.52221185 82:−0.088906214 83:0.80470431 84:0.32073456 85:0.30284989 86:−0.34572381 87:−0.16798222 88:0.26834223 89:−0.085149854 90:−0.46381941 91:−0.28497866 92:−0.083240099 93:0.23497051 94:0.71247041 95:0.10818352 96:−0.067431778 97:0.14230578 98:0.34811494 99:−0.17548287 100:−0.28705376 101:0.26572925 102:0.11269118 103:−0.90378141 104:0.5389303 105:0.18243779 106:0.48281679 107:0.63226885 108:−0.047447182 109:−0.34102982 110:−0.57374471 111:0.4625105 112:−0.16108145 113:0.42875457 114:0.74632806 115:0.24888358 116:−0.17780352 117:−0.075309783 118:0.44869909 119:−0.80715179 120:0.074523486 121:−0.43639556 122:−0.15139017 123:0.099250935 124:0.43534672 125:0.27857891 126:0.039848961 127:0.32865775 128:0.27167287 129:−0.4430134 130:0.37659815 131:−0.19536941 132:−0.25548661 133:−0.11555226 134:0.29351884 135:−0.14999919 136:−0.0036672305 137:9.853208e−005 138:−0.017125415 139:0.0062208101 140:0.00056613336.141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 |

APPENDIX C1-continued

SVM Model Weights
(340; Normal/Diseased)

273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
0.0034319981554139273 1:−2.9766047 2:2.3910513 3:−0.0033213915 4:−0.17175539 5:−6.0470386
6:−1.3497559 7:−0.36723912 8:0.20253371 9:−0.012134829 10:1.6765274 11:1.0212137
12:1.540747 13:−0.44459653 14:2.285203 15:−2.1024718 16:−2.3299692 17:−0.22237271
18:−1.540495 19:−1.7433741 20:−0.86427718 21:3.2597923 22:−0.9036212 23:−0.33261031
24:0.08034569 25:0.31062645 26:0.62380868 27:0.30884013 28:0.93615496 29:−0.55678594
30:0.83648986 31:2.2175543 32:−3.9626403 33:0.67159081 34:−0.12033869 35:0.051533122
36:1.9251186 37:−0.50044167 38:0.91387403 39:1.315704 40:0.64285749 41:−0.69283903
42:1.6269565 43:0.97460204 44:0.094993889 45:−1.448289 46:0.48921242 47:−0.24176522
48:1.2643825 49:1.7443092 50:−0.70274568 51:0.24876195 52:0.43642703 53:−0.60853028
54:0.059798267 55:0.13331567 56:0.8999694 57:−0.95040554 58:1.6903936 59:−0.78197664
60:−0.024035554 61:0.50674534 62:−0.80088967 63:0.19888808 64:−0.327461 65:−0.15733092
66:−0.25754383 67:0.87108743 68:0.32690728 69:−1.6650847 70:0.39882895 71:−0.14998643
72:0.15765926 73:0.068408899 74:−0.43477553 75:0.37428498 76:0.203853 77:−0.098876506
78:0.77563006 79:−0.14145415 80:0.13966918 81:−0.21151921 82:−1.1710844 83:0.31694144
84:0.29759014 85:0.23627378 86:−0.092135094 87:1.2209444 88:−0.5446806 89:−0.43929076
90:0.73736781 91:−0.55304527 92:−0.66342461 93:−0.83785564 94:0.33425888 95:0.63092983
96:−0.55766058 97:0.35235989 98:0.22620907 99:−0.3337062 100:0.023882609 101:−0.17901589
102:−0.7864933 103:0.6957624 104:−0.49392122 105:0.41317111 106:−0.13489716
107:−0.3420338 108:0.25884572 109:0.18038958 110:−0.0060654548 111:−0.089531191
112:0.06296584 113:−0.38787681 114:−0.22121978 115:0.19375634 116:0.50431353
117:−0.15176535 118:−0.11273892 119:−0.15365359 120:−0.091838799 121:0.32395056
122:−0.62842178 123:0.1432551 124:0.22065035 125:−0.048689816 126:−0.30507016 127:−0.22730111
128:−0.081573524 129:0.22219233 130:0.16054086 131:0.049703121 132:−0.45559883
133:0.11796858 134:0.10735185 135:−0.13397379 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627

APPENDIX C1-continued

SVM Model Weights
(340; Normal/Diseased)

316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
0.0034319981554139273 1:1.4998577 2:−0.833125 3:0.15874894 4:−0.16305982 5:−6.3999782
6:−3.0114808 7:−2.3441393 8:−0.62991965 9:0.48263061 10:1.2088264 11:2.9173965 12:0.93438792
13:−1.1417776 14:0.47276586 15:1.2369784 16:−0.55091071 17:−0.66656023 18:−2.6298883
19:−2.2242267 20:−0.40263057 21:0.19578533 22:−0.36221969 23:−1.7459612 24:−1.1249856
25:−0.96496415 26:0.97178137 27:−0.89674354 28:0.18115836 29:−0.2664201 30:−0.84420794
31:0.99844122 32:0.3935703 33:−0.92425972 34:0.84827334 35:0.18696381 36:−0.61741596
37:−0.27812341 38:0.82220787 39:1.5204298 40:−0.024465038 41:−1.4631784 42:1.8447262
43:−0.38213187 44:0.12529095 45:−1.3761704 46:−0.041299947 47:−0.019116471 48:−1.0498253
49:0.63776499 50:0.88740844 51:1.2011482 52:0.41635996 53:0.10563747 54:−0.58376336
55:0.27111086 56:−0.8262558 57:1.1927794 58:−0.5591445 59:−0.032716781 60:0.93659627
61:1.1629854 62:−0.14906347 63:0.06745334 64:2.1141806 65:0.062371463 66:0.2405418
67:0.31143147 68:0.5432331 69:−0.45986184 70:−1.0745176 71:0.55840057 72:−0.72463292
73:0.062870719 74:−0.83106136 75:−1.02478 76:−1.2473516 77:0.050191764 78:−0.74776781
79:0.46886358 80:−0.20920451 81:−0.3985875 82:0.2346088 83:−0.31092039 84:−0.41067883
85:−0.38236198 86:−0.32828122 87:−0.13168074 88:−0.65530121 89:−1.1595361 90:−0.96060157
91:0.26395658 92:−0.28265053 93:−0.013547269 94:−1.13686 95:0.027409265 96:0.20472966
97:0.55087811 98:0.21734166 99:−0.64037561 100:−0.34522218 101:−0.36959693
102:−0.45125923 103:0.23045701 104:−0.51938421 105:−0.48705339 106:−0.82742482 107:0.1872315
108:−0.76833683 109:−0.39742014 110:0.37114617 111:0.5425716 112:−0.29124007
113:−0.10644489 114:−0.16034076 115:−0.055143073 116:−0.021569245 117:−0.0066969153
118:0.25269786 119:−0.42335254 120:0.31398213 121:−0.26026762 122:−0.20239964
123:−0.35671863 124:−0.19627297 125:−0.029190052 126:0.18270841 127:−0.038641684
128:0.080900714 129:−0.13840856 130:0.08480376 131:−0.27147114 132:0.44246787
133:−0.25776327 134:−0.13087656 135:−0.12904176 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
−0.0034319981554139273 1:1.8426523 2:−1.0022681 3:−1.8142201 4:4.7052956 5:−3.3947911
6:−3.9205186 7:2.2534845 8:−0.65490913 9:0.93505371 10:−1.3716303 11:−2.4469345 12:−1.6224073
13:−0.52282864 14:−2.9351051 15:−0.0068617496 16:0.46865952 17:−1.560643 18:−0.21292216

APPENDIX C1-continued

SVM Model Weights
(340; Normal/Diseased)

19:2.1473019 20:−0.67687339 21:−0.28722957 22:0.56001335 23:−0.094829082 24:−1.3970063
25:0.98717302 26:−0.4236204 27:−0.92757404 28:0.3730565 29:1.0406255 30:−0.88888693
31:−1.4504825 32:−0.6683532 33:−0.33247265 34:−0.033092454 35:0.26896572 36:1.5959476
37:0.010037191 38:−0.81271714 39:0.0030672953 40:0.50752759 41:−0.4395774 42:0.31354156
43:1.1316957 44:1.0628705 45:0.81664729 46:−0.44994509 47:1.8356267 48:−0.94820237
49:1.1194025 50:−0.49359241 51:−0.27994666 52:1.309444 53:0.021853868 54:0.30842969
55:−0.78456146 56:0.28993934 57:0.94030941 58:−0.034615789 59:−0.35700414 60:0.35395202
61:0.061831497 62:−0.74912906 63:0.12902097 64:−0.34087849 65:0.35399655 66:−0.27148318
67:−0.64102411 68:−0.23167168 69:−0.33912688 70:0.031118577 71:0.612023 72:−0.31107095
73:−0.78582859 74:1.0256356 75:−0.19048233 76:−0.4532049 77:0.2822164 78:−0.194115
79:−0.24197151 80:0.38782927 81:−0.33452025 82:0.41326469 83:1.3208663 84:0.19393028
85:0.45549294 86:0.07890036 87:−0.599401 88:−0.35813239 89:−0.758766 90:−0.21080847
91:−0.07081385 92:0.31630668 93:0.72324228 94:−0.14209431 95:−0.5681029 96:−0.53165948
97:0.49915966 98:0.0021087122 99:−0.72314292 100:0.98972875 101:0.73643148
102:−0.019651005 103:0.075585939 104:0.038109794 105:0.70555723 106:0.51785624
107:0.12796681 108:0.14555179 109:−0.62779212 110:−0.3596524 111:−0.12123301
112:0.046545986 113:0.17191418 114:0.020494144 115:0.0086749699 116:−0.31709561
117:−0.075676717 118:−0.90533519 119:−0.027939418 120:−0.19563891 121:−0.84516889
122:−0.23876828 123:−0.47341564 124:−0.50515723 125:−0.21032868 126:0.12874357 127:−0.12194417
128:−0.1925377 129:0.24482122 130:0.019612819 131:−0.48789504 132:0.21904406
133:0.46626651 134:−0.20635547 135:−0.08080674 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
−0.0034319981554139273 1:−9.4932261 2:−2.4200175 3:−0.99547184 4:3.386457 5:−0.25609118
6:−2.623518 7:−2.4135804 8:−0.39986932 9:2.1378477 10:1.8484613 11:0.7939347 12:−1.8100283
13:0.086847119 14:−1.0847259 15:0.014694811 16:−0.061961468 17:1.11698 18:0.37644273
19:0.43925872 20:1.019256 21:−0.034235802 22:−1.0565522 23:0.18581668 24:−1.7383976
25:2.1731598 26:0.71717995 27:1.3705052 28:0.42550248 29:−0.29724944 30:−1.2346706
31:−0.56772882 32:0.35246193 33:−0.03986638 34:−0.38854089 35:−0.65117943 36:−1.2889299
37:−0.93312246 38:0.5973838 39:0.4066982 40:−1.2644749 41:0.99629927 42:−0.57985032
43:−0.63576305 44:−1.8356446 45:−1.0743715 46:−0.14329678 47:−0.8826586 48:−0.37040722
49:−0.6788758 50:−0.45492631 51:−0.89243484 52:−0.057133693 53:0.31184465 54:0.084423982
55:−0.56936181 56:−0.10785694 57:−1.0227678 58:−1.2069671 59:−0.4624708 60:−0.46327126
61:−0.94274431 62:0.62106037 63:−0.7299782 64:0.32808968 65:0.70177394 66:0.07611876
67:0.44077566 68:1.2233313 69:−0.31044862 70:−0.9895606 71:0.20284437 72:0.54383928

APPENDIX C1-continued

| SVM Model Weights (340; Normal/Diseased) |
|---|
| 73:−1.5249349 74:−0.45136279 75:0.15737078 76:−1.0366597 77:0.69401526 78:1.8774619 79:−1.3141834 80:−0.35478765 81:0.68788713 82:0.34662926 83:0.46135426 84:0.89465719 85:−0.21682085 86:−0.56248474 87:0.36605811 88:0.62789202 89:−0.60549015 90:0.042345077 91:0.37237728 92:0.30609837 93:0.25562957 94:−0.032219864 95:0.97003841 96:0.46520367 97:0.08052551 98:−0.54221892 99:−0.49070641 100:−0.15332189 101:−0.038513858 102:−0.41552392 103:0.09081585 104:−0.57363886 105:−0.15578696 106:0.40950146 107:0.57133073 108:0.095161363 109:0.092112131 110:0.47553059 111:−0.66320163 112:0.15343548 113:0.39384419 114:0.35065937 115:−0.54612589 116:0.085567772 117:−0.2152615 118:−0.26243281 119:−0.32773164 120:−0.18304932 121:−0.4524942 122:0.28405121 123:0.17056018 124:−0.078690931 125:−0.32918683 126:−0.00560176 127:−0.24626188 128:0.24803571 129:−0.21311688 130:−0.1183672 131:−0.42568853 132:−0.23056392 133:0.30853862 134:0.1633389 135:−0.10645273 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:−0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.0034319981554139273 1:−5.7653995 2:−7.7065129 3:−1.7101065 4:2.9592018 5:0.76229161 6:−3.6607392 7:−1.3269446 8:0.56657773 9:1.139729 10:0.17632462 11:2.1677668 12:1.3118943 13:−0.52651542 14:−0.3446798 15:−1.5242846 16:0.45261335 17:1.8554153 18:−2.0332828 19:1.0373086 20:−0.59927064 21:1.2456559 22:−0.52233613 23:0.24843232 24:−0.57826668 25:0.20601466 26:1.0337256 27:1.3346144 28:1.0033516 29:−0.14132218 30:−0.44747621 31:−2.1312487 32:1.0729326 33:0.63819945 34:−1.0156969 35:−0.12516639 36:−1.7160656 37:−0.74329221 38:−0.031156909 39:−0.38357505 40:0.23199198 41:−0.6455729 42:−0.53660375 43:1.8243196 44:−0.228793 45:−1.1999203 46:0.15424994 47:−2.392344 48:−0.84571058 49:0.38441601 50:−1.4214644 51:−0.23135762 52:0.99908489 53:0.30190232 54:1.2513613 55:0.15170304 56:1.1843537 57:−1.0560424 58:−0.0013475108 59:−0.63009286 60:0.33963561 61:0.38146102 62:0.10609791 63:−1.1965718 64:1.3627383 65:1.5931025 66:−2.627198 67:0.10647382 68:−1.9954445 69:0.65885431 70:1.384408 71:0.94649565 72:0.17098832 73:−0.62934065 74:−1.0389315 75:−0.28657356 76:−0.1330131 77:0.39319348 78:−0.030887162 79:0.11736631 80:−0.45598289 81:0.36185947 82:−0.79248106 83:−0.34403181 84:−0.20294397 85:−0.21804844 86:−0.17831732 87:−0.024510611 88:0.16076228 89:−0.32158056 90:−0.6044206 91:−0.074197479 92:0.074977025 93:0.18668127 94:−0.062036157 95:−0.25265589 96:−0.79632926 97:0.045378052 98:0.36430773 99:0.84773159 100:−0.16500252 101:0.084113456 102:0.69042814 103:−0.31792277 104:0.20665745 105:0.095547594 106:−0.34500083 107:0.25514463 108:−0.22103278 109:−0.4399268 110:0.23940758 111:0.27695754 112:0.10488176 113:−0.13489641 114:−0.66484725 115:−0.19028845 116:−0.10949807 117:0.11622622 118:−0.49623901 119:0.035860494 120:0.28680035 121:0.02956542 122:0.084283307 123:0.42693636 124:−0.25623819 125:0.076775856 126:−0.1623843 |

APPENDIX C1-continued

| SVM Model Weights (340; Normal/Diseased) |
|---|
| 127:0.14631408 128:−0.15941425 129:0.29983637 130:−0.14497517 131:0.30814034 132:−0.15905522 133:−0.026160153 134:0.033009481 135:−0.030927602 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:−0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| 0.0034319981554139273 1:5.4943523 2:3.8203344 3:3.2906234 4:0.16825591 5:−4.9035769 6:−0.52033991 7:3.1050794 8:2.5860252 9:2.6400912 10:−3.4708204 11:2.3735955 12:1.9459182 13:3.1852815 14:1.206341 15:−3.3552761 16:−2.1890383 17:1.5772523 18:−0.99846894 19:−1.9426285 20:1.7405504 21:−2.5103328 22:−0.1712421 23:0.62044519 24:1.7075816 25:0.18535832 26:−0.3251397 27:0.50698811 28:2.1281648 29:−1.4055895 30:0.44488609 31:0.082362577 32:0.50587648 33:1.4535089 34:−0.1660212 35:−1.0464996 36:−0.32472673 37:−3.2258751 38:−1.0420521 39:0.26829112 40:−0.26259658 41:0.66264814 42:−1.5650598 43:−2.8255298 44:−0.47267067 45:−0.26437676 46:1.4970443 47:1.6494414 48:−1.150957 49:0.48409933 50:−0.97914815 51:−1.1762872 52:−0.67540783 53:0.9785468 54:−0.10272652 55:−0.44946235 56:−0.6475299 57:−0.19610074 58:0.57770157 59:0.62224936 60:1.2325798 61:2.0817311 62:1.3649201 63:−1.5788438 64:0.3441278 65:−0.82410073 66:0.38950849 67:0.63741684 68:0.81976885 69:1.8669279 70:−0.093081616 71:−0.50634414 72:0.70292288 73:−0.21797721 74:−0.81374848 75:−0.97752309 76:−0.00052603154 77:−0.047995523 78:0.56340075 79:−0.13965929 80:0.74398124 81:−1.0789561 82:−1.6268255 83:0.34880072 84:−0.23649105 85:0.58947003 86:−0.1383841 87:−0.2034663 88:0.13705519 89:0.15726337 90:0.14639254 91:−0.39643821 92:−0.24904472 93:0.1635053 94:0.39251247 95:0.093715906 96:−0.054773234 97:−0.16500287 98:0.33907735 99:−0.26833045 100:0.22000352 101:0.31445241 102:0.05850713 103:−0.43375942 104:0.11185712 105:0.065139204 106:−0.3343353 107:−0.2239103 108:−0.14626871 109:0.46071982 110:0.11659521 111:−0.24896008 112:0.4000096 113:−0.071827605 114:−0.050723191 115:0.29207581 116:−0.1172537 117:0.11612654 118:−0.12722747 119:−0.0064618452 120:−0.26983282 121:0.1812467 122:0.1834754 123:−0.28311354 124:−0.14607435 125:0.03647206 126:−0.17979737 127:−0.010307481 128:−0.13341153 129:0.12626275 130:0.0066001578 131:−0.13002723 132:0.20033009 133:−0.051966283 134:−0.099335626 135:0.0067797294 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 |

APPENDIX C1-continued

SVM Model Weights
(340; Normal/Diseased)

172:−0.0056320974 173:−0.0067036133 174:0.00017559867 175:0.001684437 176:−0.0034504069
177:0.0018235954 178:−0.001383971 179:0.0004998623 180:−0.00066253374 181:0.0015807585
182:0.00412085 183:0.0021063511 184:0.00072732504 185:−0.0012095358 186:−0.0030121093
187:−0.0020631803 188:−0.00068084424 189:0.0002527938 190:−0.0034640408
191:−0.00026976471 192:0.00097010034 193:−0.0011612385 194:−0.0015113452 195:0.00062438019
196:−0.00013164691 197:0.0020616048 198:0.0010445472 199:−0.0049765292 200:9.8877339e−005
201:0.0028779099 202:−0.0036701721 203:0.00099803088 204:0.00068234798
205:0.002192216 206:0.0033146022 207:0.00050616561 208:−0.0031757453 209:0.0028448526
210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097 228:−0.0016731552
229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
−0.0034319981554139273 1:2.0158556 2:5.64184 3:1.2100551 4:0.38732079 5:−0.91638023
6:0.86250663 7:−5.9655256 8:1.9825593 9:−3.4821234 10:0.86993414 11:−1.6572517
12:−0.76582778 13:0.11991637 14:0.039823018 15:−1.6965232 16:−0.86651272 17:0.55945367
18:0.67926311 19:1.2445376 20:−0.74454379 21:−0.71011066 22:2.5852528 23:−1.3076165
24:−0.46179819 25:−2.4348414 26:1.8081855 27:1.3103861 28:−1.3082397 29:−0.89139622
30:−2.1623175 31:1.5018917 32:−0.46999404 33:−0.27754453 34:1.9421457 35:0.8924948
36:−0.59410006 37:1.1388235 38:−0.40503344 39:1.266946 40:1.3438236 41:−0.20875518
42:−1.152586 43:0.35084587 44:−0.66025627 45:0.27601939 46:0.50508291 47:1.0504811
48:−0.0061990432 49:0.89158946 50:−0.740192 51:0.37023339 52:0.18432029 53:0.49898073
54:−1.0100789 55:−0.98633426 56:0.052206729 57:−1.1405525 58:0.059401955 59:0.6115393
60:−0.038578793 61:1.044669 62:0.41048342 63:0.4342218 64:−0.19823729 65:0.45956901
66:1.2680084 67:−1.5415982 68:0.26044369 69:0.67990941 70:−0.20977019 71:0.17940669
72:−0.6234647 73:−0.15683755 74:−0.12970166 75:0.23375361 76:−1.0716821 77:−0.34470367
78:−0.15326777 79:−0.88641953 80:−0.051476792 81:0.60701138 82:−1.132746 83:0.27538162
84:−0.67856759 85:−0.77390039 86:0.37120631 87:0.24407847 88:0.31105894 89:−0.44230959
90:−0.01191919 91:−0.52496779 92:−0.31745291 93:−0.20105523 94:−0.049534883 95:0.65129679
96:0.073534958 97:0.14456718 98:0.49296263 99:0.99296147 100:−0.022943899 101:−0.10830843
102:0.51143181 103:0.11781275 104:−0.63564694 105:0.30319691 106:0.44465125
107:0.55975741 108:0.53839016 109:−0.92177403 110:−0.4046326 111:0.41702613
112:0.090463668 113:0.28243372 114:0.24284993 115:0.69989187 116:0.017668614
117:0.49144834 118:0.079083249 119:0.21885723 120:0.4498165 121:−0.35448828
122:0.17714088 123:−0.16964117 124:0.28235051 125:0.17662004 126:−0.20059519
127:0.12534058 128:−0.20563948 129:−0.30541384 130:−0.071801089 131:−0.028010791
132:−0.052578609 133:0.41542912 134:0.0065091765 135:0.18064836 136:−0.0036672305
137:9.853208e−005 138:−0.017125415 139:0.0062208101 140:0.00056613336 141:0.0012280536
142:−0.00039310646 143:−0.0063707544 144:0.0015248039 145:−0.0029345977
146:−0.00076821423 147:0.00013666278 148:−0.0051379474 149:0.0066761598 150:−0.0024066679
151:0.0038081626 152:−0.0013487631 153:−0.0020869875 154:−0.0023751855 155:1.1204498e−006
156:0.0039485889 157:−0.00011155871 158:0.00070337567 159:0.0012323871
166:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209.171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668

APPENDIX C1-continued

SVM Model Weights
(340; Normal/Diseased)

216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
−0.0034319981554139273 1:12.198691 2:−4.6254134 3:0.4309229 4:−0.0045036334 5:1.6533217
6:−1.6674639 7:−0.58168441 8:−2.0143023 9:−0.36359423 10:−1.1387699 11:0.4026781
12:3.4342923 13:0.077531099 14:0.59686226 15:1.4676325 16:−1.0380758 17:2.0957778
18:−0.18262574 19:1.3347188 20:0.81862861 21:1.8272871 22:−1.1508977 23:0.6757282 24:1.425102
25:4.0549784 26:0.38353825 27:−1.8369131 28:−0.13398515 29:−0.57104951 30:0.22000989
31:0.12870221 32:0.7133007 33:−0.35001582 34:0.0011888057 35:−0.90330213 36:1.5864959
37:−0.25036854 38:−0.020135572 39:−0.67250866 40:−0.66962731 41:−0.76892602 42:0.42453542
43:−1.3383957 44:0.089187309 45:1.4743941 46:−0.58752674 47:−0.13003859 48:−0.085984677
49:1.88237 50:−0.092915475 51:−0.16898575 52:−1.2927262 53:1.1112242 54:−0.56929666
55:0.51432651 56:1.5974669 57:0.29192296 58:1.3793269 59:1.3311955 60:−1.1512399
61:1.1414181 62:−0.42488316 63:1.02485 64:0.80391228 65:−0.12326206 66:−0.0096905828
67:−0.25598711 68:−0.56333989 69:0.47411421 70:−0.52220768 71:0.62780327 72:−0.63821578
73:0.044849351 74:0.30436012 75:0.85827565 76:−0.35568988 77:0.48760805 78:0.55250949
79:−0.48662898 80:1.1320682 81:−0.4279331 82:0.55387139 83:−0.18235028 84:0.64431673
85:−0.12753169 86:−0.067573681 87:−0.052215297 88:−0.55798137 89:−0.36272204 90:−0.40898284
91:1.0214362 92:0.35930005 93:−0.34361362 94:−0.14425266 95:0.30535591 96:0.60389847
97:−1.3605524 98:0.064752296 99:0.25823164 100:−0.26117915 101:−0.099516183 102:0.38991141
103:0.25776377 104:0.46403474 105:0.11795826 106:−0.52819687 107:0.32982376
108:−0.015468006 109:0.35649645 110:0.21989878 111:0.10516962 112:0.24890202 113:0.025377037
114:−0.28131869 115:−0.21714623 116:−0.34393078 117:0.10866149 118:−0.22075211
119:0.17918086 120:0.44859427 121:−0.10357872 122:−0.44898194 123:0.083177678
124:0.6973539 125:−0.40110606 126:−0.10662927 127:0.46295655 128:−0.045621336
129:0.020998118 130:0.04747786 131:−0.25109187 132:−0.08680921 133:0.3704755
134:−0.089532435 135:−0.0020852075 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133 174:0.00017559867 175:0.001684437
176:−0.0034504069 177:0.0018235954 178:−0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938
190:−0.0034640408 191:−0.00026976471 192:0.00097010034 193:−0.0011612385 194:−0.0015113452
195:0.00062438019 196:−0.00013164691 197:0.0020616048 198:0.0010445472
199:−0.0049765292 200:9.8877339e−005 201:0.0028779099 202:−0.0036701721 203:0.00099803088
204:0.00068234798 205:0.002192216 206:0.0033146022 207:0.00050616561 208:−0.0031757453
209:0.0028448526 210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097
228:−0.0016731552 229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599

APPENDIX C1-continued

| SVM Model Weights (340; Normal/Diseased) |
| --- |

263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
−0.0028276038133164647 1:−0.92056668 2:7.982316 3:2.7672982 4:−5.6989779 5:−2.0040121
6:1.3560103 7:0.47844598 8:−0.88915581 9:0.29286313 10:1.9550498 11:0.73400009
12:0.67523128 13:4.2900996 14:1.759645 15:3.1263313 16:3.4484181 17:1.1700882
18:−2.5563493 19:0.37533271 20:−0.79565668 21:−1.3620112 22:−0.24505715 23:2.6705673
24:0.91925913 25:−1.7523115 26:2.7090824 27:−2.4245808 28:−0.3016541 29:1.0368193
30:1.349012 31:1.3343428 32:1.1360695 33:−1.0604455 34:−0.55855429 35:−1.4334891
36:0.31644401 37:4.0981212 38:−0.76405543 39:2.4361506 40:−0.072746783 41:1.3639972
42:−2.7133963 43:0.58745974 44:1.215488 45:0.71256995 46:−0.63146925 47:1.1245365
48:0.68571043 49:0.12023477 50:−2.9852123 51:0.48245761 52:−0.60535866 53:−0.42614096
54:0.895666 55:1.536912 56:0.41395107 57:1.3474098 58:−0.11917051 59:−0.72688085
60:0.94913411 61:0.62710458 62:0.84917873 63:0.10144996 64:0.94962496 65:0.48940825
66:0.1560725 67:0.10165013 68:−0.73191041 69:0.0017839102 70:0.48697016 71:−0.49387777
72:0.68558019 73:0.53076398 74:−0.7026388 75:0.14259262 76:0.0749093 77:0.1046522
78:−0.71482873 79:−0.096147284 80:0.26972616 81:0.37506589 82:0.2323183 83:0.59012479
84:−0.22533044 85:0.45790485 86:−0.93499082 87:−0.033955473 88:0.5987255 89:−0.8467778
90:0.45219356 91:−0.44050017 92:−0.20194368 93:−0.31016046 94:0.13768268 95:−0.016728459
96:0.40278655 97:0.42470405 98:−0.23021986 99:−0.11911887 100:0.17097282 101:−0.45682582
102:−0.34545216 103:−0.059974384 104:0.094054952 105:−0.16447034 106:−0.25329623
107:−0.16933984 108:0.20767117 109:−0.16069634 110:0.043291464 111:−0.53366786
112:−0.065921195 113:0.18177918 114:0.18708153 115:−0.36620402 116:−0.27697492
117:0.057236377 118:−0.27236256 119:0.054895297 120:−0.16744445 121:−0.25060037
122:−0.14989623 123:0.26708692 124:0.381244 125:−0.012803463 126:0.38954791 127:0.073961154
128:0.010790307 129:0.080572113 130:−0.19666478 131:−0.07909739 132:−0.14938612
133:0.023856048 134:−0.15885867 135:−0.11238814 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005

APPENDIX C1-continued

| SVM Model Weights (340; Normal/Diseased) |
|---|
| 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| 0.0034319981554139273 1:−12.323371 2:−2.5419991 3:−1.609848 4:4.4974389 5:−3.7014587 6:−4.0358763 7:2.6280291 8:4.9896169 9:2.5341156 10:−1.446465 11:0.80235535 12:−2.3242402 13:−1.1710668 14:−0.41775832 15:−4.1889386 16:−1.1208876 17:0.92109925 18:−1.9065992 19:−1.8256842 20:−2.3905437 21:1.7596356 22:−1.4175112 23:0.18312508 24:3.5366721 25:−0.89412063 26:−3.6899207 27:1.4042687 28:−0.66406071 29:−0.58963937 30:−2.340239 31:−2.9288216 32:−0.79229331 33:−0.91411191 34:2.9614749 35:−0.89132273 36:1.7922473 37:2354436 38:0.53673452 39:−0.18893766 40:−1.2241523 41:0.79943401 42:−1.4271966 43:−0.86519498 44:1.1074665 45:−2.1866074 46:−0.57520199 47:0.82644343 48:−0.090864554 49:−1.2602122 50:0.36414298 51:−0.040461358 52:−1.4667616 53:2.691318 54:0.92768717 55:−0.39435172 56:0.9569068 57:1.4663866 58:−0.10978934 59:−0.15809369 60:−1.1098099 61:−0.49797028 62:0.18566647 63:−0.83051121 64:0.23004419 65:0.095365636 66:0.65703654 67:−0.83133465 68:0.38520044 69:0.29496205 70:0.26739585 71:0.77351087 72:−1.0678705 73:0.89645118 74:−0.21810022 75:−0.8048836 76:−0.17026433 77:−0.14614077 78:−0.25395 79:0.718638 80:0.84217626 81:0.2479565 82:0.064400159 83:−0.662857 84:0.38506141 85:0.030625224 86:0.65420347 87:0.49891934 88:0.028129011 89:−0.057228126 90:0.26811397 91:0.36951756 92:−0.45381945 93:−0.66364729 94:0.34991813 95:0.091937244 96:0.059569277 97:0.47495991 98:−0.42050424 99:0.053332731 100:−0.37811899 101:0.36115694 102:0.078206286 103:0.30216146 104:−0.36571035 105:0.22643599 106:0.17953895 107:0.4388347 108:0.20245242 109:0.09512078 110:−0.39573279 111:−0.023548797 112:−0.14197768 113:−0.090567835 114:−0.080832958 115:−0.24264121 116:−0.32855439 117:−0.17986266 118:0.025512995 119:−0.096746631 120:−0.11808167 121:0.081009306 122:−0.024545608 123:0.4439528 124:−0.06531889 125:−0.031536646 126:0.10069836 127:−0.056873329 128:−0.080573268 129:0.019438546 130:−0.003010618 131:0.22513352 132:0.14307666 133:0.02698415 134:−0.02975351 135:−0.10584338 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.000.65122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| 0.0034319981554139273 1:3.4503579 2:−4.2435541 3:−3.5084748 4:4.1104755 5:−2.2494571 |

APPENDIX C1-continued

| SVM Model Weights (340; Normal/Diseased) |
| --- |
| 6:−1.1301751 7:1.2851278 8:−1.3474931 9:0.074681044 10:−1.1245632 11:0.0059922114 12:−0.65546483 13:−1.0927281 14:−1.6123801 15:−2.0109613 16:0.8245908 17:−0.20697463 18:1.6903372 19:0.20574044 20:−0.52657861 21:−0.15481399 22:−0.95674044 23:−0.12188616 24:0.3153148 25:1.220279 26:−0.46595594 27:1.2647409 28:−1.0921087 29:0.63332158 30:0.31533015 31:0.49947315 32:0.52631956 33:0.52140331 34:−1.471079 35:−0.3043865 36:0.6245653 37:−0.54806453 38:−0.14093906 39:0.97424895 40:−0.78888589 41:−0.30943748 42:0.2295381 43:−0.26546445 44:−0.69476426 45:−0.13171944 46:0.094888531 47:0.10638277 48:−0.43834734 49:0.36926419 50:0.16866605 51:−0.16950628 52:1.0210851 53:−0.12908459 54:0.2574836 55:0.16228732 56:−0.32980037 57:1.2871718 58:−0.695324 59:−0.44037962 60:0.13058139 61:−0.81643009 62:0.085330784 63:0.63842231 64:−0.39016843 65:0.074462868 66:0.62911004 67:−0.055147562 68:0.13169409 69:0.51636732 70:−0.58961576 71:−0.18650682 72:0.22953425 73:−0.46220464 74:−0.064442351 75:0.15822068 76:−0.82707661 77:−0.18713538 78:−0.54458982 79:−0.12780048 80:1.0517936 81:0.39728534 82:−0.30585971 83:−0.20047277 84:0.61465275 85:0.41496634 86:0.36339089 87:0.4240995 88:−0.048659079 89:−0.43183196 90:0.90765584 91:−1.2010933 92:0.21343851 93:−0.19759792 94:−0.19610697 95:0.32138336 96:−0.042523447 97:−0.61365408 98:0.13067096 99:0.080782674 100:−0.26087698 101:−0.098387398 102:0.39236504 103:0.26647487 104:0.59064674 105:−0.37054184 106:−0.28795782 107:0.24207512 108:0.42263624 109:0.34861243 110:0.060841627 111:0.94690883 112:−0.53198099 113:0.55987149 114:−0.1490411 115:0.061857134 116:−0.018884091 117:0.46472266 118:−0.25346598 119:0.019241994 120:−0.28012112 121:−0.29143104 122:−0.19309302 123:−0.94427973 124:−0.30762994 125:−0.022436086 126:0.45589927 127:−0.031995092 128:0.42745173 129:0.32627714 130:−0.56456834 131:0.71519703 132:−0.39422357 133:−0.057930395 134:0.13270946 135:−0.44415176 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.0013490120335021018 1:−1.2745243 2:1.3725504 3:−0.40984562 4:−2.6292028 5:−5.3895054 6:5.9739404 7:−4.5711613 8:2.2052009 9:−5.2465138 10:−0.67647785 11:1.0394732 12:2.7295601 13:−2.7722533 14:1.1244704 15:−0.89633745 16:−0.9274469 17:1.6699194 18:−1.6771654 19:−0.72681016 20:−0.44002792 21:−0.26600459 22:−0.98991096 23:−0.93116117 24:0.69509518 25:0.92285657 26:−0.063109092 27:−1.1735464 28:−0.5015974 29:−0.96754038 30:−0.37860304 31:0.082809262 32:1.2631295 33:−0.43986905 34:−0.93515766 35:−0.39846018 36:−1.7811431 37:0.96436918 38:−0.86943996 39:−0.1857571 40:−0.052335016 41:0.77989316 42:1.9585305 43:0.5136919 44:0.70290852 45:−0.65992278 46:−0.62819904 47:0.042234074 48:−0.27403095 49:−1.5831054 50:0.57542837 51:1.2535095 52:−0.27763495 53:0.30042842 54:−0.026697634 55:0.83986866 56:−1.7717499 57:0.56075555 58:−0.32618308 59:−1.2565497 60:0.24616675 |

APPENDIX C1-continued

| SVM Model Weights (340; Normal/Diseased) |
|---|
| 61:−0.31638002 62:0.1136407 63:−0.524584 64:0.49817708 65:−0.77622032 66:0.67375588 67:−0.68531972 68:−0.88069934 69:−0.59614903 70:−0.48646048 71:−0.26088428 72:0.92441028 73:0.9558959 74:−0.80790859 75:0.9994542 76:−1.1186945 77:−0.54430348 78:0.31087041 79:−0.12128209 80:0.049723487 81:−0.068356842 82:−1.0160431 83:0.24992315 84:0.64890897 85:0.035451155 86:0.47344312 87:−0.63606417 88:−0.25533685 89:0.12384438 90:−0.38119489 91:0.93362528 92:0.90957248 93:−0.53976035 94:0.037433326 95:−0.29013798 96:0.13491242 97:−0.3933484 98:−0.040989075 99:−1.1761559 100:−0.015528644 101:0.59950584 102:0.36507317 103:−0.14597462 104:0.29010144 105:−0.61899203 106:0.88645005 107:−0.22018719 108:0.73146123 109:−0.21052855 110:0.50387311 111:−0.23996586 112:0.47525749 113:−0.027271563 114:−0.30505991 115:0.44151479 116:0.28475326 117:0.32241207 118:−0.40282109 119:0.05447254 120:0.16844749 121:0.4222981 122:−0.21605109 123:0.2627207 124:−0.059958767 125:0.23325685 126:−0.25208417 127:−0.0084206685 128:−0.14462355 129:−0.25611815 130:−0.11666627 131:0.26215807 132:−0.15383783 133:0.038570508 134:−0.10287643 135:−0.016915072 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| 2.9087399042421842e−005 1:6.3584962 2:−6.3778191 3:3.2515109 4:5.1755161 5:4.2499866 6:−11.99882 7:−1.5156378 8:4.1527638 9:−0.18030602 10:−1.1761832 11:5.4542184 12:2.0691378 13:−1.6560538 14:0.79019296 15:1.8808135 16:1.9049292 17:1.8592358 18:−2.1669643 19:−0.048648611 20:−2.5740819 21:−0.70472515 22:0.8201015 23:0.71556932 24:−1.80097 25:−2.5610666 26:0.59389859 27:−0.78396356 28:0.11526062 29:−0.09563344 30:−2.0597372 31:0.75164664 32:1.7167188 33:−0.8780849 34:−0.94556618 35:3.2067571 36:−0.55151516 37:−1.2391465 38:−1.4040649 39:−2.0579765 40:−0.10920454 41:1.5984117 42:1.5354701 43:2.2374403 44:1.6578482 45:−0.069791123 46:0.43039051 47:0.53295434 48:0.75136089 49:−0.90726262 50:−0.59872472 51:−0.23022404 52:−0.99246538 53:−1.8657418 54:−1.3137063 55:0.69614094 56:0.54208493 57:−0.83017355 58:−0.029540086 59:1.9364667 60:−0.29958665 61:0.17397369 62:0.79381496 63:−1.6109239 64:0.96843368 65:0.052511267 66:0.11731391 67:−0.83705848 68:0.82254171 69:−0.26468176 70:−0.76873767 71:−0.29751939 72:1.3841127 73:0.52975595 74:0.60065693 75:0.36754712 76:1.0355914 77:−0.21337773 78:−0.11204219 79:−0.12291181 80:0.96028787 81:−0.050827105 82:0.62444359 83:0.15589094 84:0.66139913 85:0.18312415 86:0.71563566 87:0.82202756 88:−0.67771763 89:0.029627522 90:−0.11528786 91:−0.32177019 92:0.036026612 93:−0.29614452 94:0.58259195 95:0.59359843 96:−0.1144006 97:0.46879435 98:−0.030567918 99:0.29963395 100:0.19607882 101:0.52465147 102:−0.12843208 103:−0.026177958 104:0.097037271 105:−0.29722077 106:−0.28496021 107:0.26209804 108:−0.11052902 109:0.018481122 110:−0.031377397 111:0.27456823 112:−0.069907784 113:0.43416947 114:0.14551146 115:−0.049010582 116:−0.099174909 117:0.066310599 |

APPENDIX C1-continued

SVM Model Weights
(340; Normal/Diseased)

118:0.0079132402 119:−0.29500219 120:−0.10235194 121:0.12036052 122:−0.050956193
123:0.042007901 124:0.093738332 125:−0.07834883 126:0.070866764 127:−0.054744665
128:−0.088775136 129:0.065360546 130:−0.014001296 131:−0.030975103 132:0.0053515499
133:−0.085055254 134:0.082705922 135:−0.012115293 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.0087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
−0.0034319981554139273 1:4.132174 2:−6.2578673 3:−4.4534831 4:3.3225648 5:0.92792118
6:0.13495214 7:2.4636238 8:0.043804433 9:−0.12212539 10:−3.6037035 11:−0.16387007
12:2.1024275 13:−0.8426888 14:−0.28110489 15:−1.0565786 16:1.7971499 17:0.89108872
18:−0.19204256 19:−0.37601933 20:0.29086679 21:−0.93570775 22:0.9933148 23:0.49556109
24:0.30878216 25:−0.06323579 26:1.3881254 27:1.156985 28:−0.836025 29:1.0145077
30:−0.14229111 31:−0.17155382 32:−0.026234334 33:−1.2460279 34:−1.0607399 35:−2.3045077
36:0.15773092 37:−1.859993 38:1.3026433 39:−1.4954717 40:0.91123676 41:1.6476334
42:−0.016044997 43:1.1311302 44:0.65482485 45:−0.50996262 46:0.20572463 47:0.20633431
48:0.9185195 49:−0.0069128866 50:−0.8106612 51:0.44928578 52:1.769662 53:0.28103986
54:−0.39396164 55:0.82345629 56:−0.58649194 57:0.011862372 58:−0.77182484 59:−1.0363826
60:0.64749193 61:0.57068056 62:−0.73007858 63:−0.097035326 64:−0.10577562 65:−0.12638293
66:0.89023834 67:−0.20933913 68:0.59134924 69:1.16711 70:0.092131026 71:0.64477086
72:−0.56461102 73:0.98778188 74:0.59265774 75:−0.39949697 76:−0.89452052 77:−1.2504236
78:0.47944611 79:0.56021106 80:0.039773744 81:−0.26168171 82:0.69073153 83:−0.76336658
84:−0.085453652 85:−1.1681105 86:−0.9619711 87:1.0533458 88:−0.65426141 89:−0.50253868
90:−0.50269806 91:−0.13963236 92:−0.50752902 93:0.15625508 94:−0.62914884 95:−0.3012099
96:0.4230749 97:−0.089510016 98:0.26636773 99:0.8350811 100:0.84154308 101:−0.38260472
102:−0.34248057 103:−0.85043406 104:0.36148816 105:0.27237701 106:0.72118211
107:−0.17630355 108:−0.042348653 109:0.92093176 110:−0.2516692 111:−0.23777437 112:−0.24916553
113:0.11487173 114:−0.052202534 115:0.24373937 116:0.32101712 117:−0.082912222
118:−0.35500783 119:−0.032889597 120:0.017829873 121:0.0062567834 122:0.0066715754
123:0.30178577 124:0.030751809 125:−0.31628978 126:−0.10335981 127:−0.17665714
128:0.21421066 129:−0.29181227 130:0.23632011 131:0.063385211 132:−0.3044723
133:−0.010433782 134:−0.34844893 135:−0.051801763 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:1.1204498e−006
156:0.0039485889 157:−0.00011155871 158:0.00070337567 159:0.0012323871

APPENDIX C1-continued

SVM Model Weights
(340; Normal/Diseased)

160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
−0.00093395672008240397 1:−9.2383366 2:2.0031359 3:−2.7472436 4:−0.29943109 5:−5.6568513
6:3.7322798 7:5.1578135 8:2.1428649 9:−2.7855699 10:−0.25731304 11:−2.9800839
12:−0.47946775 13:−2.2630336 14:−0.45474353 15:−5.7471838 16:2.3978477 17:4.3268204
18:−3.0305762 19:1.3055806 20:−2.1667976 21:−0.78709322 22:−1.6385171 23:−1.2645901
24:−0.72841704 25:−1.361117 26:2.6740563 27:0.99330205 28:0.56622869 29:0.021516191
30:−1.0199603 31:2.8918629 32:0.17529561 33:1.3039639 34:0.66107935 35:−0.73529148
36:1.6549188 37:−2.4072337 38:1.3072208 39:−0.56783468 40:−1.3100624 41:0.3624413
42:−0.26424339 43:0.42006019 44:1.9382477 45:−0.51278996 46:0.47823575 47:0.0037102359
48:0.95446652 49:1.0228879 50:−1.393595 51:−1.2037687 52:−0.73327082 53:−1.1920532
54:0.10549983 55:−0.13279434 56:0.3578119 57:0.38885364 58:−0.95124429 59:−1.0567375
60:−1.8370425 61:−0.6606943 62:0.70864707 63:0.67599821 64:−0.37370375 65:0.20003127
66:0.63242871 67:0.15085423 68:0.057238787 69:0.17639741 70:−0.23044479 71:−0.20157395
72:0.62036103 73:−0.25716212 74:0.71563143 75:0.7609778 76:−0.050195843 77:−0.25451463
78:−0.1692701 79:−0.078648195 80:−0.74276435 81:−0.010895328 82:0.77240366 83:0.27615985
84:−0.90610391 85:−0.029832665 86:0.16903952 87:−0.25067636 88:0.086275116 89:−0.15264727
90:−0.1570916 91:−0.070674807 92:−0.24385354 93:0.25232759 94:−0.41044292 95:0.16169809
96:−0.6508168 97:−0.20916058 98:−0.76756066 99:−1.0653344 100:−0.73948568 101:−0.34985223
102:0.4395743 103:−0.088321015 104:0.52526557 105:0.38539556 106:−0.39978862
107:0.42003214 108:−0.27074355 109:0.24175136 110:0.0015339421 111:0.10471925
112:0.12488673 113:0.0014199329 114:0.15878834 115:−0.11603529 116:0.25505471
117:−0.1048518 118:−0.15892263 119:0.41111663 120:0.29234418 121:−0.036175299 122:0.29229996
123:−0.10580225 124:0.1544362 125:0.2344081 126:−0.47872171 127:0.17721082
128:−0.16191941 129:−0.0076283012 130:0.00037610251 131:0.13791676 132:0.39722022
133:−0.11411838 134:−0.11229561 135:0.055424809 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:11 204498e−006
156:0.0039485889157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099

APPENDIX C1-continued

SVM Model Weights
(340; Normal/Diseased)

202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
−0.0034319981554139273 1:1.5939288 2:−0.68451202 3:−1.9828767 4:2.687711 5:−2.3559065
6:−0.40762001 7:−0.38349798 8:1.4480487 9:0.19084418 10:0.57923073 11:0.15427236
12:0.30517232 13:−2.8470616 14:−0.89354444 15:−1.8082743 16:0.90372598 17:−0.8944034
18:−0.19528657 19:0.37987849 20:−0.72632611 21:0.74004036 22:0.51418865 23:−1.1826543
24:−0.68684179 25:1.3350503 26:1.3483067 27:−1.1749243 28:0.0035296429 29:0.40864256
30:−1.0857723 31:−2.2653854 32:1.132339 33:0.75138783 34:1.6571852 35:−0.66929579
36:0.01038154 37:0.11476938 38:−0.28282329 39:−0.0039718393 40:−0.42626029 41:−0.1703448
42:−1.2294829 43:0.49754259 44:0.78424221 45:0.40770197 46:0.2548393 47:0.34366134
48:0.42368001 49:−0.0031600283 50:−0.55383235 51:1.7163563 52:0.033633709 53:−0.73686308
54:0.89823377 55:−0.037769046 56:−0.27557534 57:−1.1176921 58:1.4940319 59:0.26057047
60:−0.62359345 61:0.52774233 62:−0.72299153 63:0.15405934 64:−1.3268715 65:−0.1421221
66:−1.6126971 67:−0.030900931 68:0.54111493 69:0.80216682 70:1.0123219 71:0.067640841
72:0.20240721 73:−0.87775278 74:0.26203439 75:0.33620653 76:0.026765861 77:−0.89195812
78:0.46182638 79:0.41690511 80:0.53303576 81:0.3838982 82:0.19043288 83:−0.31487751
84:−0.2211739 85:−0.094877258 86:0.17287305 87:−0.30642956 88:0.66487998 89:−0.089803152
90:−0.62361205 91:−0.014874261 92:−0.42866713 93:−0.33329934 94:−0.30627686 95:0.52704877
96:0.84512198 97:−0.40205273 98:−0.44091523 99:−0.80510819 100:0.30291346 101:0.60111904
102:0.20042421 103:0.40679386 104:−0.017157659 105:0.14144382 106:−0.41348898
107:−0.36466545 108:0.51369566 109:−0.0098067196 110:−0.10126246 111:−0.16242722
112:0.32992208 113:0.36952221 114:−0.41399992 115:0.42152765 116:0.94466555
117:0.49779215 118:0.2205174 119:−0.16299078 120:−0.066795915 121:−0.5987168
122:−0.088584416 123:0.052586496 124:−0.22363149 125:−0.054559864 126:0.98960513
127:−0.16185355 128:−0.000530185 129:0.1322419 130:0.32524756 131:−0.22171825 132:0.12896192
133:−0.41668513 134:−0.0040682456 135:0.17874803 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:11204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168

APPENDIX C1-continued

SVM Model Weights
(340; Normal/Diseased)

244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844
325:−0.0030691659 326:−0.0033078301 327:0.0012743858 328:0.0024482214 329:0.0018192574
330:0.0026370357 331:0.0017312634 332:0.00066732749 333:0.00034391912 334:0.0037949879
335:0.0018411272 336:0.0051615993 337:0.0017553387 338:−0.0027431778 339:−0.0055160136
340:0.0031345901 #
0.0034319981554139273 1:3.194849 2:0.43900785 3:−1.9627602 4:1.2485242 5:−5.9852576
6:0.33253258 7:−1.8617131 8:−0.86069912 9:0.550134 10:1.0473752 11:1.0903063
12:0.014737786 13:−0.93575341 14:−0.49048775 15:−0.22670957 16:0.033254467 17:−1.1327134
18:0.51697665 19:−0.088372737 20:−0.88697433 21:−1.1650202 22:0.80797178 23:−0.92340988
24:−1.0851067 25:−0.81728846 26:0.33128548 27:−0.55782062 28:−1.3039638 29:0.34368724
30:0.6521095 31:−0.99489051 32:0.014531549 33:−0.2099172 34:−0.99392444 35:1.1560659
36:−0.05918486 37:0.16560514 38:1.1157157 39:−0.6798988 40:0.2000774 41:−2.4399419
42:0.062852286 43:−0.59827936 44:−0.64824188 45:−0.74368501 46:−0.35463345 47:0.14426918
48:−0.25484803 49:−0.85277611 50:−0.49318787 51:−0.58561718 52:0.6080265 53:−0.54487962
54:0.38094941 55:0.58301115 56:−0.83181024 57:1.4327674 58:−0.32032874 59:−0.7785061
60:0.2222829 61:0.2062933 62:−0.33664161 63:0.40453207 64:−0.063989356 65:1.0704974
66:0.85856509 67:−0.34260032 68:−0.81909335 69:0.24490944 70:−0.8815605 71:−0.40375853
72:0.30855694 73:−0.22328483 74:0.11981357 75:0.20845959 76:−0.27041709 77:0.18642138
78:−0.021063909 79:0.14842433 80:0.18297967 81:−0.94384241 82:0.65075558 83:−0.23166057
84:−0.19040057 85:−0.88623601 86:−0.18320793 87:−0.026504304 88:−0.025206773 89:0.53336507
90:0.25503281 91:−0.42970529 92:−0.798118 93:0.62125385 94:0.75689876 95:0.27264342
96:−0.077018738 97:−0.32638183 98:0.87572664 99:−0.010225996 100:0.48457241 101:0.31294566
102:−0.42489517 103:0.23156941 104:−0.12934007 105:0.20684706 106:−0.44312671
107:0.96399832 108:0.75644094 109:0.37421459 110:−0.031186122 111:0.30256855
112:1.3347543 113:−0.93485653 114:−0.0039332365 115:−0.17325649 116:0.24396519
117:−0.35073361 118:0.11285204 119:−0.2026833 120:−0.23775786 121:0.36879483 122:0.45299327
123:0.45982772 124:0.34988415 125:−0.15529042 126:0.50012702 127:0.31022221
128:−0.056554925 129:0.022206482 130:−0.40370545 131:−0.030165229 132:0.048384361
133:−0.100467 134:0.29780763 135:0.18085416 136:−0.0036672305 137:9.853208e−005
138:−0.017125415 139:0.0062208101 140:0.00056613336 141:0.0012280536 142:−0.00039310646
143:−0.0063707544 144:0.0015248039 145:−0.0029345977 146:−0.00076821423
147:0.00013666278 148:−0.0051379474 149:0.0066761598 150:−0.0024066679 151:0.0038081626
152:−0.0013487631 153:−0.0020869875 154:−0.0023751855 155:1.1204498e−006
156:0.0039485889 157:−0.00011155871 158:0.00070337567 159:0.001323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761

APPENDIX C1-continued

| SVM Model Weights (340; Normal/Diseased) |
|---|
| 289:−0.0040808818 290:−0.00058058492 291:0.00025530611 292:0.00042821659<br>293:−0.0017559038 294:0.00030293313 295:−0.0004816725 296:−0.00057298481 297:−0.00086739491<br>298:0.0020803961 299:0.00010370808 300:0.00075778627 301:0.00074104586<br>302:−0.00021793939 303:0.0013351805 304:−0.0006143825 305:0.0025815656 306:7.1731614e−005<br>307:−0.0052312948 308:−0.00063595735 309:0.0015091125 310:−0.00024647679<br>311:−0.0050271503 312:−0.00065122027 313:−0.00070704299 314:−0.0038100008 315:0.0022923627<br>316:0.0019759815 317:0.00079242635 318:0.0045642676 319:0.001573379 320:0.0015903091<br>321:0.00074843148 322:0.00091753813 323:0.0021253934 324:0.0013280844<br>325:−0.0030691659 326:−0.0033078301 327:0.0012743858 328:0.0024482214 329:0.0018192574<br>330:0.0026370357 331:0.0017312634 332:0.00066732749 333:0.00034391912 334:0.0037949879<br>335:0.0018411272 336:0.0051615993 337:0.0017553387 338:−0.0027431778 339:−0.0055160136<br>340:0.0031345901 #<br>0.0034319981554139273 1:5.3318014 2:2.8600442 3:−0.63892436 4:2.671339 5:−5.2220407<br>6:0.021795753 7:−0.1497921 8:−0.35194841 9:2.4227602 10:0.78205884 11:−0.273817<br>12:−1.8752793 13:0.1105957 14:−1.5807208 15:0.86257154 16:1.7695898 17:−2.1386125<br>18:13988218 19:0.15350451 20:−1.6646396 21:−1.2468495 22:1.1442618 23:0.22816287<br>24:−0.59291494 25:−1.2557151 26:−0.16814576 27:−0.27625111 28:−0.94614822 29:−0.90841764<br>30:−0.55482227 31:−0.69049489 32:−0.52906591 33:0.1456854 34:−0.15881176 35:0.79538953<br>36:0.14933707 37:0.35109264 38:1.6287683 39:0.30482042 40:−0.16101275 41:−1.1122111<br>42:0.92197961 43:−0.65001202 44:−0.29940131 45:0.82114142 46:−2.3014662 47:0.019852048<br>48:−1.4395304 49:−0.61461782 50:−0.66179311 51:0.33406314 52:0.71744514 53:−0.31344864<br>54:−0.36929134 55:1.0807132 56:0.64560848 57:0.36599183 58:0.63315117 59:−0.59978986<br>60:0.47401521 61:−0.04233579 62:0.43825498 63:−0.18208194 64:0.93805003 65:0.6489799<br>66:1.0274676 67:0.30374503 68:0.093746543 69:0.65355974 70:0.93731129 71:0.31009677<br>72:1.0268996 73:1.0494651 74:0.12953329 75:−0.13468555 76:0.082101204 77:0.082376562<br>78:0.093450055 79:−1.2197555 80:−0.51803309 81:−0.14628641 82:0.43446764 83:−0.35269833<br>84:0.45715046 85:0.71453136 86:0.29029518 87:0.45547223 88:0.34717581 89:−0.18215664<br>90:0.19789974 91:−0.088763468 92:0.68219513 93:0.042047709 94:0.77511251 95:−0.37109309<br>96:0.42795303 97:−0.27017939 98:0.14396903 99:0.22546157 100:−1.2837176 101:−0.029369317<br>102:0.56320822 103:−0.35629776 104:−0.0023324771 105:0.2750378 106:−0.3135393<br>107:0.12949888 108:0.47269785 109:0.023282005 110:−0.17463878 111:−0.34355715<br>112:−0.28921083 113:−0.48279077 114:−0.22426187 115:−0.15045841 116:0.59637153 117:0.16885878<br>118:0.19599013 119:−0.36954916 120:−0.3749094 121:−0.13710088 122:0.039765418<br>123:−0.48465356 124:−0.45843944 125:−0.12944523 126:−0.44463918 127:0.15867536<br>128:0.064863451 129:0.026821014 130:1.0378103 131:0.02990902 132:−0.038629875<br>133:0.18360603 134:−0.055364098 135:0.1851873 136:−0.0036672305 137:9.853208e−005<br>138:−0.017125415 139:0.0062208101 140:0.00056613336 141:0.0012280536 142:−0.00039310646<br>143:−0.0063707544 144:0.0015248039 145:−0.0029345977 146:−0.00076821423<br>147:0.00013666278 148:−0.0051379474 149:0.0066761598 150:−0.0024066679 151:0.0038081626<br>152:−0.0013487631 153:−0.0020869875 154:−0.0023751855 155:1.1204498e−006<br>156:0.0039485889 157:−0.00011155871 158:0.00070337567 159:0.0012323871<br>160:0.0021008069 161:0.0028489598 162:0.00029079549 163:0.0020081406 164:0.0044465163<br>165:0.007065278 166:0.0012901861 167:0.0037493915 168:−0.0023597497 169:−0.00012567961<br>170:0.00047573209 171:7.8875659e−005 172:−0.0056320974 173:−0.0067036133<br>174:0.00017559867 175:0.001684437 176:−0.0034504069 177:0.0018235954 178:−0.001383971<br>179:0.0004998623 180:−0.00066253374 181:0.0015807585 182:0.00412085 183:0.0021063511<br>184:0.00072732504 185:−0.0012095358 186:−0.0030121093 187:−0.0020631803<br>188:−0.00068084424 189:0.0002527938 190:−0.0034640408 191:−0.00026976471 192:0.00097010034<br>193:−0.0011612385 194:−0.0015113452 195:0.00062438019 196:−0.00013164691<br>197:0.0020616048 198:0.0010445472 199:−0.0049765292 200:9.8877339e−005 201:0.0028779099<br>202:−0.0036701721 203:0.00099803088 204:0.00068234798 205:0.002192216 206:0.0033146022<br>207:0.00050616561 208:−0.0031757453 209:0.0028448526 210:0.00092352234<br>211:−0.0022140611 212:−0.0013608048 213:0.0051376815 214:−0.0017870248 215:−0.0027518668<br>216:0.00043837572 217:−0.027317183 218:−0.024619192 219:−0.01382506 220:−0.015382294<br>221:−0.016386922 222:−0.0094594397 223:−0.0056853383 224:−0.00050634646<br>225:−0.00087913428 226:−0.023968795 227:−0.0034698097 228:−0.0016731552 229:0.00047607321<br>230:−0.011432272 231:−0.00036644109 232:−0.0025967851 233:0.0015593689<br>234:−0.0042631673 235:−0.0053286692 236:−0.0059999214 237:−0.087129325 238:−0.063751429<br>239:−0.0045496477 240:−0.0073839114 241:0.0014150206 242:−0.0042075687 243:−0.0022374168<br>244:−0.041910719 245:−0.030919394 246:−0.049301699 247:−0.019442754 248:−0.0019611341<br>249:−0.0072449106 250:−0.0051453672 251:−0.0072873179 252:−0.005927789 253:−0.0018599511<br>254:−0.017141052 255:−0.023494685 256:−0.01788312 257:−0.01943502 258:−0.0060224077<br>259:−0.0073500308 260:−0.0064477329 261:−0.0002986097 262:−0.0014349599 263:−0.0020359957<br>264:−0.0082596857 265:−0.006963369 266:−0.0016096481 267:−0.0083991755 268:−0.046351645<br>269:−0.046128571 270:−0.011141608 271:0.0020650877 272:−0.0010642689 273:−0.018076098<br>274:−0.016929928 275:−0.0052876701 276:−0.0025432054 277:−0.04111632 278:−0.031511344<br>279:−0.019488858 280:−0.0036160324 281:−0.032332413 282:−0.023754911 283:−0.0030713808<br>284:−0.033357695 285:−0.027144579 286:−0.0093234172 287:−0.0091438433 288:0.00080924761<br>289:−0.0040808818 290:−0.00058058492 291:0.00025530611 292:0.00042821659<br>293:−0.0017559038 294:0.00030293313 295:−0.0004816725 296:−0.00057298481 297:−0.00086739491<br>298:0.0020803961 299:0.00010370808 300:0.00075778627 301:0.00074104586<br>302:−0.00021793939 303:0.0013351805 304:−0.0006143825 305:0.0025815656 306:7.1731614e−005<br>307:−0.0052312948 308:−0.00063595735 309:0.0015091125 310:−0.00024647679<br>311:−0.0050271503 312:−0.00065122027 313:−0.00070704299 314:−0.0038100008 315:0.0022923627<br>316:0.0019759815 317:0.00079242635 318:0.0045642676 319:0.001573379 320:0.0015903091<br>321:0.00074843148 322:−0.00091753813 323:0.0021253934 324:0.0013280844<br>325:−0.0030691659 326:−0.0033078301 327:0.0012743858 328:0.0024482214 329:0.0018192574 |

APPENDIX C1-continued

SVM Model Weights
(340; Normal/Diseased)

330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 #
0.0034319981554139273 1:2.7049806 2:1.0712382 3:−0.60530049 4:3.1470454 5:−6.2567849 6:−1.7234993 7:−2.0789998 8:−0.55858582 9:1.1510547 10:3.0091002 11:0.27469772 12:−1.7099465 13:0.52950001 14:−1.3216618 15:−1.2992212 16:0.25060481 17:0.48826501 18:0.98599839 19:0.92709947 20:−1.5546227 21:−1.628973 22:2.1816301 23:−0.39126211 24:−0.38967183 25:−0.50289649 26:0.25889975 27:−0.35903266 28:1.0430959 29:1.2041683 30:−1.9328635 31:0.015573424 32:−0.5285145 33:0.25673017 34:−0.50455731 35:0.87040234 36:0.59407818 37:1.0408165 38:0.83375084 39:0.59187216 40:0.58443272 41:1.0092293 42:0.22197787 43:−0.44589493 44:−1.1379919 45:0.3581925 46:0.70814025 47:−0.42151362 48:−0.052317169 49:−0.11082876 50:0.2889609 51:1.2139032 52:−1.1592975 53:−0.059054762 54:−0.18548462 55:−0.77073801 56:0.26250359 57:−0.36623242 58:−0.031984866 59:0.26953441 60:−0.85498047 61:0.36182615 62:−0.74242324 63:−0.29094225 64:−0.91586173 65:0.30981737 66:−0.32983193 67:−1.3585093 68:−0.12513724 69:−0.010376908 70:0.38823065 71:−0.0060941791 72:0.27587929 73:0.25745854 74:−1.291971 75:0.42582241 76:−0.36651218 77:0.31846911 78:0.88084328 79:−0.77209193 80:−0.33607072 81:−0.31164974 82:0.25311977 83:0.36149731 84:−0.057023317 85:0.27844882 86:0.32876754 87:−0.43379608 88:0.4907667 89:0.29749528 90:0.39854935 91:−0.26912612 92:0.23791645 93:−0.003690999 94:−0.22356121 95:0.31378654 96:1.1218181 97:−0.1037571 98:−0.51191521 99:0.60179859 100:0.19405703 101:−0.32132247 102:−1.0804 103:−1.244925 104:0.16302757 105:0.28936464 106:0.444536 107:0.44657806 108:−0.61659807 109:0.051829234 110:0.35321143 111:0.29924968 112:0.36832678 113:−0.23925641 114:−0.1771376 115:−0.093931518 116:−0.051425207 117:−0.40548342 118:0.29844424 119:0.64568764 120:0.021042168 121:0.43931574 122:−0.90042299 123:−0.13475586 124:−0.31575981 125:−0.024523925 126:−0.02215652 127:0.33809316 128:−0.025578916 129:0.21336968 130:0.038657527 131:0.1715418 132:0.14620356 133:−0.50939941 134:−0.25099418 135:−0.32685781 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 #
0.0029048610626985971 1:2.6485436 2:−0.39832091 3:3.7447002 4:−2.1478522 5:−5.6797609 6:−5.3180451 7:0.0458709 8:−0.33030915 9:1.79348 10:−1.4856584 11:1.9551603 12:0.15802991 13:2.1567461 14:1.0581138 15:0.24001168 16:0.21704598 17:0.36217123 18:−1.7393889 19:−0.86479646 20:0.28050035 21:−0.62279636 22:0.46538505 23:−1.2491378 24:0.49455559 25:3.2503259 26:2.6528273 27:−0.90466022 28:2.0810993 29:−1.800808 30:−0.65186924 31:1.1478062 32:−1.1883457 33:−1.9486394 34:−0.40922812 35:1.3789246 36:0.44635722 37:−0.52121764 38:0.59901804 39:3.750737 40:0.50481492 41:−1.0930679 42:−1.0418009

APPENDIX C1-continued

| SVM Model Weights (340; Normal/Diseased) |
|---|
| 43:2.3580823 44:0.41928837 45:0.43175229 46:−1.7687958 47:1.5241576 48:0.047912914 49:−0.011029373 50:1.999184 51:−1.5378287 52:0.81118917 53:−0.59545577 54:−1.478533 55:0.2204963 56:0.21527496 57:−1.5467908 58:0.040827062 59:0.088919461 60:−1.1570362 61:−1.1377196 62:−0.35034156 63:−0.27653784 64:−0.89409906 65:−0.82165486 66:−0.084878348 67:0.71434367 68:−0.84567839 69:−0.036878616 70:0.38060263 71:−0.40381098 72:−0.46761507 73:1.3047739 74:−0.26679948 75:−0.76907367 76:−0.60177022 77:0.047061063 78:0.65042329 79:0.55717415 80:0.1702593 81:−0.30285549 82:0.35264146 83:−0.40650514 84:0.22974481 85:−0.19868746 86:−0.47476405 87:0.36343929 88:1.0777737 89:−0.012342887 90:−0.29064631 91:0.45745492 92:−0.48784018 93:0.59721577 94:0.38002604 95:−0.57114393 96:−0.16883458 97:0.48802984 98:−0.27438253 99:0.086777598 100:−0.76459801 101:0.74515593 102:0.87388647 103:−0.58475381 104:−6.8664529e−005 105:−0.30276695 106:0.078480236 107:0.10368462 108:−0.17813639 109:0.26296818 110:0.11882183 111:−0.027596835 112:0.21213761 113:−0.054298706 114:0.17405806 115:0.41722238 116:−0.27272609 117:−0.075912334 118:0.1319824 119:0.3687596 120:−0.16810474 121:−0.014954013 122:0.016595332 123:−0.095552042 124:0.11352359 125:−0.10565997 126:0.35341632 127:−0.039049342 128:0.12530626 129:−0.03634569 130:−0.21122634 131:−0.0049572014 132:−0.045888804 133:0.045374833 134:0.087704875 135:−0.090682462 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| 0.0016463608108803368 1:−5.0323195 2:−2.8937032 3:0.9245494 4:4.0953684 5:−0.48259613 6:−10.957071 7:−1.3562635 8:1.5278653 9:1.908803 10:1.5891732 11:1.9105272 12:−1.7403718 13:0.79528445 14:1.4411625 15:2.055773 16:−0.47434691 17:0.84861767 18:0.96878743 19:1.2661024 20:0.39621857 21:0.02885787 22:−2.1331224 23:1.1653996 24:1.7666892 25:−0.5342958 26:−0.058051892 27:0.22720467 28:−1.8131837 29:−0.33533868 30:0.51968986 31:−2.8554194 32:−0.39893693 33:−1.3069463 34:−1.2616062 35:−0.50449288 36:−0.30745259 37:0.78427112 38:−1.7781194 39:−3.1630948 40:1.5530428 41:−0.52526122 42:−1.3863609 43:−0.75657463 44:1.3458173 45:−0.41903311 46:−0.60242832 47:−0.73190629 48:−1.1985373 49:0.9617061 50:−1.0572286 51:−1.0892643 52:2.7433617 53:−0.29182494 54:−1.1755396 55:0.30320728 56:0.59947592 57:−0.57867312 58:−0.31572407 59:0.67291749 60:−0.25184411 61:−0.12825929 62:0.14712813 63:0.072493941 64:−0.93540007 65:0.23385698 66:1.2352091 67:0.40883824 68:0.90679425 69:−0.78691781 70:−0.43946591 71:0.061390832 72:0.43101066 73:−0.65560371 74:−0.11186254 75:0.84073192 76:−0.76387501 77:−0.085754573 78:0.28736416 79:0.57194638 80:0.18722515 81:0.20813055 82:−0.77415365 83:−0.11878719 84:−0.66424346 85:0.10148657 86:−0.44752237 87:−0.71743089 88:−0.16741936 89:−0.26290193 90:0.12664582 91:0.34051278 92:0.21044105 93:−0.14037225 94:−0.030440379 95:−0.080103606 96:0.001516659 97:0.12230273 98:−0.34304601 99:−0.84433419 100:−0.27329749 101:−0.85424352 |

APPENDIX C1-continued

SVM Model Weights
(340; Normal/Diseased)

102:0.43549636 103:−0.53498381 104:−0.51170874 105:0.036937252 106:−0.16164991
107:−0.34457445 108:0.21543145 109:−0.31550542 110:0.14729781 111:0.17318971 112:−0.24259767
113:−0.31764826 114:−0.028606372 115:0.097100101 116:−0.072211348 117:−0.030194836
118:0.92152005 119:0.56367224 120:0.022018356 121:0.55472898 122:0.15909594
123:−0.016504714 124:0.27040243 125:−0.24056274 126:0.21324211 127:0.013955995
128:−0.027860435 129:0.099007659 130:0.142767 131:0.13695309 132:−0.19236313 133:−0.15692993
134:−0.14951144 135:−0.042818893 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133 174:0.00017559867 175:0.001684437
176:−0.0034504069 177:0.0018235954 178:−0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938
190:−0.0034640408 191:−0.00026976471 192:0.00097010034 193:−0.0011612385 194:−0.0015113452
195:0.00062438019 196:−0.00013164691 197:0.0020616048 198:0.0010445472
199:−0.0049765292 200:9.8877339e−005 201:0.0028779099 202:−0.0036701721 203:0.00099803088
204:0.00068234798 205:0.002192216 206:0.0033146022 207:0.00050616561 208:−0.0031757453
209:0.0028448526 210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097
228:−0.0016731552 229:−0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
−0.0033250251752435121 1:−2.2816663 2:−0.1950358 3:−5.0425577 4:1.724364 5:−0.82801467
6:2.5474527 7:−4.9610643 8:−0.55181468 9:−0.79765153 10:2.3832989 11:0.10773348
12:1.0693098 13:−1.2152728 14:0.79049957 15:0.0099222139 16:−1.4971162 17:−2.0980864
18:1.5831172 19:0.44416675 20:0.65041918 21:0.34350562 22:0.71617293 23:−1.3270057
24:1.3510978 25:−1.3417459 26:0.16030331 27:1.2561779 28:0.30793247 29:−1.5139967
30:−1.4691375 31:−0.77589041 32:−0.13834539 33:0.60559732 34:−0.23270255 35:−0.91066253
36:1.1967326 37:−0.38090953 38:0.92491049 39:0.22646277 40:0.0545705 41:−0.51402158
42:0.036931422 43:−0.34624645 44:−0.26213413 45:−0.54855555 46:0.65808016 47:0.60549748
48:−1.3048626 49:−0.02858902 50:1.158542 51:−0.51622027 52:−0.48286453 53:−0.42171869
54:0.15448236 55:0.22208098 56:−0.96829629 57:−0.81633997 58:0.69672573 59:0.43771729
60:−0.33384237 61:−0.30339918 62:−0.23418264 63:−1.0594679 64:−0.28116763 65:−1.0582877
66:0.24212617 67:−0.021668741 68:−0.38854149 69:−0.025471134 70:−0.057951681
71:−0.28464383 72:0.55788136 73:−0.14839807 74:1.2589951 75:−0.17693742 76:−0.42702228
77:−0.80403411 78:−1.2830989 79:0.43489653 80:−0.29964188 81:0.53392845 82:0.30745533
83:0.32345781 84:−0.031299688 85:−0.084129535 86:−0.091957755 87:0.82083333
88:−0.16892581 89:0.14701359 90:−0.092742957 91:0.30413979 92:−0.3388353 93:0.53230518
94:0.032915041 95:0.35364595 96:−0.080694951 97:0.12824225 98:0.64884341 99:0.15401942
100:−0.38473433 101:−1.091372 102:0.17073807 103:−0.021730918 104:0.51771468
105:−0.5221678 106:−0.44072565 107:−0.13892123 108:0.32019505 109:−0.5990485 110:−0.065223642
111:−0.8375352 112:0.60072982 113:0.99915087 114:−0.0082924906 115:−0.51159799
116:−0.08830981 117:−0.14848702 118:0.25263357 119:−0.071752489 120:−0.11685174
121:0.34134734 122:−0.19654071 123:0.38066959 124:−0.20949158 125:0.4713724
126:−0.011627856 127:0.52436131 128:0.40084165 129:0.56871146 130:−0.025380548
131:−0.30069289 132:−0.24094978 133:0.11057184 134:−0.4643788 135:−0.16252849
136:−0.0036672305 137:9.853208e−005 138:−0.017125415 139:0.0062208101 140:0.00056613336
141:0.0012280536 142:−0.00039310646 143:−0.0063707544 144:0.0015248039
145:−0.0029345977 146:−0.00076821423 147:0.00013666278 148:−0.0051379474 149:0.0066761598

APPENDIX C1-continued

SVM Model Weights
(340; Normal/Diseased)

150:−0.0024066679 151:0.0038081626 152:−0.0013487631 153:−0.0020869875
154:−0.0023751855 155:1.1204498e−006 156:0.0039485889 157:−0.00011155871 158:0.00070337567
159:0.0012323871 160:0.0021008069 161:0.0028489598 162:0.00029079549 163:0.0020081406
164:0.0044465163 165:0.007065278 166:0.0012901861 167:0.0037493915 168:−0.0023597497
169:−0.00012567961 170:0.00047573209 171:7.8875659e−005 172:−0.0056320974
173:−0.0067036133 174:0.00017559867 175:0.001684437 176:−0.0034504069 177:0.0018235954
178:−0.001383971 179:0.0004998623 180:−0.00066253374 181:0.0015807585 182:0.00412085
183:0.0021063511 184:0.00072732504 185:−0.0012095358 186:−0.0030121093
187:−0.0020631803 188:−0.00068084424 189:0.0002527938 190:−0.0034640408 191:−0.00026976471
192:0.00097010034 193:−0.0011612385 194:−0.0015113452 195:0.00062438019
196:−0.00013164691 197:0.0020616048 198:0.0010445472 199:−0.0049765292 200:9.8877339e−005
201:0.0028779099 202:−0.0036701721 203:0.00099803088 204:0.00068234798 205:0.002192216
206:0.0033146022 207:0.00050616561 208:−0.0031757453 209:0.0028448526
210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097 228:−0.0016731552
229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
−0.00033015749009876694 1:−8.2891655 2:−0.42698517 3:7.9929414 4:−21.96343 5:−2.5162337
6:−2.332407 7:−3.5282142 8:−10.863458 9:2.4572353 10:−9.3228836 11:1.7616936 12:−1.5003358
13:−5.9558101 14:−5.6671357 15:1.9989141 16:0.0007951344 17:2.2202916 18:1.6051667
19:−0.46657437 20:−0.14883198 21:0.32293826 22:1.809746 23:0.50881672 24:0.20460126
25:−0.99105644 26:0.68109101 27:0.21133116 28:−0.1266762 29:−0.35163447 30:−0.48319864
31:−0.44588166 32:−0.81961346 33:0.4458102 34:0.25585374 35:0.22169833 36:0.50088394
37:−0.18526353 38:−0.57342333 39:−0.4100264 40:−0.49656498 41:−0.048766967 42:−0.27916297
43:−0.21427028 44:0.23489569 45:−0.055255346 46:0.14571071 47:−0.38773367 48:0.24204808
49:−0.025501506 50:0.22812733 51:0.016479289 52:0.0047244946 53:−0.10513508 54:0.0340891
55:−0.11792875 56:0.014585208 57:0.10346211 58:0.086079985 59:0.13638112 60:−0.029077984
61:−0.066002205 62:−0.0022148392 63:−0.051324606 64:−0.23397739 65:0.030481266 66:0.039421767
67:0.14640144 68:0.054071993 69:−0.018368751 70:−0.0066018607 71:0.13411276
72:0.026797809 73:−0.10997321 74:0.010199982 75:0.1154227 76:−0.065298446
77:−0.0083012516 78:−0.037069004 79:0.10039674 80:0.071657665 81:0.12727965 82:−0.11805948
83:0.00066952186 84:−0.054706763 85:0.091746822 86:0.029696872 87:0.061503891
88:0.03245607 89:−0.052378852 90:0.077654056 91:−0.050794069 92:−0.060988717
93:−0.055440236 94:0.0037542861 95:0.073643796 96:0.039003935 97:0.06855385 98:0.015820434
99:0.021465937 100:0.0077944845 101:−0.0019617444 102:−0.044610556 103:−0.02758692
104:0.028581213 105:0.083054505 106:0.033804782 107:−0.032350469 108:0.096636586
109:0.031704508 110:0.04338941 111:−0.059521303 112:−0.018208284 113:−0.0042061959
114:−0.041491624 115:−0.024438348 116:−0.016554918 117:−0.012899144 118:0.0028049359
119:0.06729117 120:−0.047828618 121:0.0087301023 122:0.017425304 123:0.01092264
124:−0.034315046 125:0.012841884 126:−0.046630777 127:0.00085983245 128:0.022828637
129:0.017506592 130:0.0044898908 131:0.0091082333 132:−0.0030817804 133:−0.044458587
134:−0.033935066 135:0.019090308 136:−0.0036672305 137:9.853208e−005 138:−0.017125415
139:0.0062208101 140:0.00056613336 141:0.0012280536 142:−0.00039310646
143:−0.0063707544 144:0.0015248039 145:−0.0029345977 146:−0.00076821423 147:0.00013666278
148:−0.0051379474 149:0.0066761598 150:−0.0024066679 151:0.0038081626 152:−0.0013487631
153:−0.0020869875 154:−0.0023751855 155:1.1204498e−006 156:0.0039485889
157:−0.00011155871 158:0.00070337567 159:0.0012323871 160:0.0021008069 161:0.0028489598
162:0.00029079549 163:0.0020081406 164:0.0044465163 165:0.007065278 166:0.0012901861
167:0.0037493915 168:−0.0023597497 169:−0.00012567961 170:0.00047573209 171:7.8875659e−005
172:−0.0056320974 173:−0.0067036133 174:0.00017559867 175:0.001684437
176:−0.0034504069 177:0.0018235954 178:−0.001383971 179:0.0004998623 180:−0.00066253374
181:0.0015807585 182:0.00412085 183:0.0021063511 184:0.00072732504 185:−0.0012095358
186:−0.0030121093 187:−0.0020631803 188:−0.00068084424 189:0.0002527938

APPENDIX C1-continued

| SVM Model Weights (340; Normal/Diseased) |
| --- |
| 190:−0.0034640408 191:−0.00026976471 192:0.00097010034 193:−0.0011612385 194:−0.0015113452 |
| 195:0.00062438019 196:−0.00013164691 197:0.0020616048 198:0.0010445472 |
| 199:−0.0049765292 200:9.8877339e−005 201:0.0028779099 202:−0.0036701721 203:0.00099803088 |
| 204:0.00068234798 205:0.002192216 206:0.0033146022 207:0.00050616561 208:−0.0031757453 |
| 209:0.0028448526 210:0.00092352234 211:−0.0022140611 212:−0.0013608048 213:0.0051376815 |
| 214:−0.0017870248 215:−0.0027518668 216:0.00043837572 217:−0.027317183 218:−0.024619192 |
| 219:−0.01382506 220:−0.015382294 221:−0.016386922 222:−0.0094594397 223:−0.0056853383 |
| 224:−0.00050634646 225:−0.00087913428 226:−0.023968795 227:−0.0034698097 |
| 228:−0.0016731552 229:0.00047607321 230:−0.011432272 231:−0.00036644109 232:−0.0025967851 |
| 233:0.0015593689 234:−0.0042631673 235:−0.0053286692 236:−0.0059999214 237:−0.087129325 |
| 238:−0.063751429 239:−0.0045496477 240:−0.0073839114 241:0.0014150206 242:−0.0042075687 |
| 243:−0.0022374168 244:−0.041910719 245:−0.030919394 246:−0.049301699 247:−0.019442754 |
| 248:−0.0019611341 249:−0.0072449106 250:−0.0051453672 251:−0.0072873179 252:−0.005927789 |
| 253:−0.0018599511 254:−0.017141052 255:−0.023494685 256:−0.01788312 257:−0.01943502 |
| 258:−0.0060224077 259:−0.0073500308 260:−0.0064477329 261:−0.0002986097 262:−0.0014349599 |
| 263:−0.0020359957 264:−0.0082596857 265:−0.006963369 266:−0.0016096481 267:−0.0083991755 |
| 268:−0.046351645 269:−0.046128571 270:−0.011141608 271:0.0020650877 272:−0.0010642689 |
| 273:−0.018076098 274:−0.016929928 275:−0.0052876701 276:−0.0025432054 277:−0.04111632 |
| 278:−0.031511344 279:−0.019488858 280:−0.0036160324 281:−0.032332413 282:−0.023754911 |
| 283:−0.0030713808 284:−0.033357695 285:−0.027144579 286:−0.0093234172 287:−0.0091438433 |
| 288:0.00080924761 289:−0.0040808818 290:−0.00058058492 291:0.00025530611 |
| 292:0.00042821659 293:−0.0017559038 294:0.00030293313 295:−0.0004816725 |
| 296:−0.00057298481 297:−0.00086739491 298:0.0020803961 299:0.00010370808 300:0.00075778627 |
| 301:0.00074104586 302:−0.00021793939 303:0.0013351805 304:−0.0006143825 |
| 305:0.0025815656 306:7.1731614e−005 307:0.0052312948 308:−0.00063595735 |
| 309:0.0015091125 310:−0.00024647679 311:−0.0050271503 312:−0.00065122027 |
| 313:−0.00070704299 314:−0.0038100008 315:0.0022923627 316:0.0019759815 317:0.00079242635 |
| 318:0.0045642676 319:0.001573379 320:0.0015903091 321:0.00074843148 322:−0.00091753813 |
| 323:0.0021253934 324:0.0013280844 325:−0.0030691659 326:−0.0033078301 327:0.0012743858 |
| 328:0.0024482214 329:0.0018192574 330:0.0026370357 331:0.0017312634 332:0.00066732749 |
| 333:0.00034391912 334:0.0037949879 335:0.0018411272 336:0.0051615993 337:0.0017553387 |
| 338:−0.0027431778 339:−0.0055160136 340:0.0031345901 # |
| −0.0013710258026271968 1:−2.1708891 2:2.2614357 3:−3.51179 4:−0.65605903 5:−2.0876923 |
| 6:0.98526502 7:−3.7276006 8:−2.333333 9:−0.7626673 10:1.9041126 11:0.56286615 12:1.27456 |
| 13:−1.2070498 14:0.76551163 15:−1.425539 16:−1.9847383 17:−2.0789609 18:1.3220781 |
| 19:−0.015966244 20:1.4032682 21:−0.23330304 22:−0.94637066 23:−0.78442478 24:−0.38136712 |
| 25:−0.44472805 26:−0.95212942 27:0.25056025 28:−1.7206384 29:−1.8087838 30:0.83157372 |
| 31:0.91639489 32:1.6293341 33:0.61387813 34:−0.16359013 35:0.75835514 36:−0.092014663 |
| 37:0.92941236 38:0.35514775 39:0.31088394 40:−0.25040948 41:−0.1788341 42:−1.0098658 |
| 43:−1.4341083 44:−0.36132643 45:−0.64555091 46:0.057727657 47:−0.47578892 48:−0.47918755 |
| 49:−1.2079383 50:−0.050135203 51:−0.40510011 52:0.27559119 53:−1.9835401 54:−0.44731498 |
| 55:0.19911686 56:0.20567349 57:0.97765356 58:1.0810498 59:0.21141325 60:0.25757796 |
| 61:1.0486588 62:0.15312012 63:0.87443727 64:0.49931028 65:0.0023828757 66:0.50078958 |
| 67:−0.12524912 68:0.034663875 69:−1.2526684 70:−0.3739877 71:0.25519511 72:0.2986595 |
| 73:−0.08473713 74:−0.54999202 75:−0.89657128 76:−0.16769353 77:0.38914543 78:−0.33761916 |
| 79:0.11389606 80:0.027786236 81:0.6460126 82:−0.13587488 83:0.40820572 84:0.15633218 |
| 85:−0.14094087 86:−0.20809449 87:0.74054438 88:−0.25139296 89:1.1260117 90:−1.3143275 |
| 91:−0.46715069 92:0.57460195 93:−0.063116185 94:0.1029439 95:0.64652425 96:−0.20054601 |
| 97:0.12008557 98:−0.17232335 99:0.10496075 100:−0.054766476 101:−0.088421926 102:0.852938 |
| 103:−0.72469574 104:0.49914837 105:0.77904516 106:0.25209782 107:−0.011075819 |
| 108:−0.60671139 109:0.53202111 110:−0.53377032 111:−0.24046279 112:−0.63954484 113:0.39428145 |
| 114:−0.54313946 115:−0.10488129 116:0.57026488 117:−0.3239105 118:−0.19530284 |
| 119:0.68384516 120:−0.23742828 121:0.10258719 122:−0.3336356 123:0.33422935 124:0.1184826 |
| 125:0.039112374 126:0.44578251 127:−0.36247495 128:−0.24737006 129:−0.082863517 |
| 130:−0.071303368 131:−0.10474084 132:0.37541941 133:0.30259365 134:0.36427543 135:−0.12953481 |
| 136:−0.0036672305 137:9.853208e−005 138:−0.017125415 139:0.0062208101 140:0.00056613336 |
| 141:0.0012280536 142:−0.00039310646 143:−0.0063707544 144:0.0015248039 |
| 145:−0.0029345977 146:−0.00076821423 147:0.00013666278 148:−0.0051379474 149:0.0066761598 |
| 150:−0.0024066679 151:0.0038081626 152:−0.0013487631 153:−0.0020869875 |
| 154:−0.0023751855 155:1.1204498e−006 156:0.0039485889 157:−0.00011155871 158:0.00070337567 |
| 159:0.0012323871 160:0.0021008069 161:0.0028489598 162:0.00029079549 163:0.0020081406 |
| 164:0.0044465163 165:0.007065278 166:0.0012901861 167:0.0037493915 168:−0.0023597497 |
| 169:−0.00012567961 170:0.00047573209 171:7.8875659e−005 172:−0.0056320974 |
| 173:−0.0067036133 174:0.00017559867 175:0.001684437 176:−0.0034504069 177:0.0018235954 |
| 178:−0.001383971 179:0.0004998623 180:−0.00066253374 181:0.0015807585 182:0.00412085 |
| 183:0.0021063511 184:0.00072732504 185:−0.0012095358 186:−0.0030121093 |
| 187:−0.0020631803 188:−0.00068084424 189:0.0002527938 190:−0.0034640408 191:−0.00026976471 |
| 192:0.00097010034 193:−0.0011612385 194:−0.0015113452 195:0.00062438019 |
| 196:−0.00013164691 197:0.0020616048 198:0.0010445472 199:−0.0049765292 200:9.8877339e−005 |
| 201:0.0028779099 202:−0.0036701721 203:0.00099803088 204:0.00068234798 205:0.002192216 |
| 206:0.0033146022 207:0.00050616561 208:−0.0031757453 209:0.0028448526 |
| 210:0.00092352234 211:−0.0022140611 212:−0.0013608048 213:−0.0051376815 |
| 214:−0.0017870248 215:−0.0027518668 216:0.00043837572 217:−0.027317183 218:−0.024619192 |
| 219:−0.01382506 220:−0.015382294 221:−0.016386922 222:−0.0094594397 223:−0.0056853383 |
| 224:−0.00050634646 225:−0.00087913428 226:−0.023968795 227:−0.0034698097 228:−0.0016731552 |
| 229:0.00047607321 230:−0.011432272 231:−0.00036644109 232:−0.0025967851 |
| 233:0.0015593689 234:−0.0042631673 235:−0.0053286692 236:−0.0059999214 237:−0.087129325 |

APPENDIX C1-continued

SVM Model Weights
(340; Normal/Diseased)

238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911
283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
−0.00012900446570094666 1:−4.1156435 2:−0.34006771 3:8.4351921 4:−14.735023 5:2.3358378
6:−6.4112816 7:1.5974257 8:−3.843544 9:−9.0954008 10:4.760253 11:−3.9502704 12:2.7603168
13:0.43952861 14:5.5260024 15:3.1865094 16:−6.4434667 17:−1.9002872 18:−6.7885156
19:0.16282603 20:0.52738881 21:−6.3669405 22:−1.5121588 23:0.72735524 24:−3.7408514
25:3.781415 26:−1.5523477 27:3.5449743 28:−0.18590957 29:5.2692285 30:0.36765394
31:−3.1490333 32:−0.66037738 33:1.007771 34:−0.61638629 35:0.74850076 36:1.2301011
37:−0.73134118 38:0.83485031 39:0.8798697 40:−1.2472433 41:0.93989688 42:−0.71822441
43:0.32871962 44:0.47559053 45:−0.90758634 46:−0.18236195 47:0.26476479 48:0.3338339
49:0.17463125 50:0.71907938 51:−0.2087025 52:0.58152407 53:0.30969498 54:0.79729444
55:0.21376763 56:−0.21582489 57:0.062268022 58:0.20543171 59:−0.055415176 60:−0.12182273
61:0.306467 62:−0.15245672 63:−0.50928122 64:−0.34476313 65:0.10096245 66:0.39556009
67:−0.60022378 68:0.34298474 69:−0.10788257 70:0.062733725 71:−0.12500487 72:0.19981076
73:0.028175019 74:0.12437224 75:0.062091012 76:0.27516529 77:0.22774903 78:−0.073975861
79:−0.27044097 80:0.066835359 81:−0.083587073 82:0.14524968 83:−0.28966823
84:−0.085532948 85:−0.090635799 86:0.020650297 87:−0.026096297 88:−0.21583928 89:0.2540783
90:−0.01140138 91:−0.11683923 92:−0.26697689 93:−0.2789408 94:−0.016539348 95:−0.072444096
96:0.23261037 97:−0.24536203 98:−0.022389531 99:0.22053359 100:−0.0055219964
101:−0.26679716 102:0.22971785 103:−0.026652239 104:−0.016328905 105:−0.12228309
106:−0.017999101 107:0.17828508 108:−0.056941263 109:−0.29281148 110:−0.10635471
111:0.041504174 112:−0.090567395 113:0.084453858 114:0.04857713 115:0.0080720913
116:0.14025536 117:0.17133811 118:0.074459136 119:−0.093730755 120:0.082958043
121:0.11174686 122:−0.071193583 123:−0.0058376351 124:0.040897187 125:0.089402698
126:0.0074354531 127:−0.022732906 128:−0.011971565 129:0.019385995 130:0.02091643
131:0.062720709 132:0.06656754 133:0.035928123 134:0.0026474444 135:0.032510031
136:−0.0036672305 137:9.853208e−005 138:−0.017125415 139:0.0062208101 140:0.00056613336
141:0.0012280536 142:−0.00039310646 143:−0.0063707544 144:0.0015248039
145:−0.0029345977 146:−0.00076821423 147:0.00013666278 148:−0.0051379474 149:0.0066761598
150:−0.0024066679 151:0.0038081626 152:−0.0013487631 153:−0.0020869875
154:−0.0023751855 155:1.1204498e−006 156:0.0039485889 157:−0.00011155871 158:0.00070337567
159:0.0012323871 160:0.0021008069 161:0.0028489598 162:0.00029079549 163:0.0020081406
164:0.0044465163 165:0.007065278 166:0.0012901861 167:0.0037493915 168:−0.0023597497
169:−0.00012567961 170:0.00047573209 171:7.8875659e−005 172:−0.0056320974
173:−0.0067036133 174:0.00017559867 175:0.001684437 176:−0.0034504069 177:0.0018235954
178:−0.001383971 179:0.0004998623 180:−0.00066253374 181:0.0015807585 182:0.00412085
183:0.0021063511 184:0.00072732504 185:−0.0012095358 186:−0.0030121093
187:−0.0020631803 188:−0.00068084424 189:0.0002527938 190:−0.0034640408 191:−0.00026976471
192:0.00097010034 193:−0.0011612385 194:−0.0015113452 195:0.00062438019
196:−0.00013164691 197:0.0020616048 198:0.0010445472 199:−0.0049765292 200:9.8877339e−005
201:0.0028779099 202:−0.0036701721 203:−0.00099803088 204:0.00068234798 205:0.002192216
206:0.0033146022 207:0.00050616561 208:−0.0031757453 209:0.0028448526
210:0.00092352234 211:−0.0022140611 212:−0.0013608048 213:0.0051376815
214:−0.0017870248 215:−0.0027518668 216:0.00043837572 217:−0.027317183 218:−0.024619192
219:−0.01382506 220:−0.015382294 221:−0.016386922 222:−0.0094594397 223:−0.0056853383
224:−0.00050634646 225:−0.00087913428 226:−0.023968795 227:−0.0034698097 228:−0.0016731552
229:0.00047607321 230:−0.011432272 231:−0.00036644109 232:−0.0025967851
233:0.0015593689 234:−0.0042631673 235:−0.0053286692 236:−0.0059999214 237:−0.087129325
238:−0.063751429 239:−0.0045496477 240:−0.0073839114 241:0.0014150206 242:−0.0042075687
243:−0.0022374168 244:−0.041910719 245:−0.030919394 246:−0.049301699 247:−0.019442754
248:−0.0019611341 249:−0.0072449106 250:−0.0051453672 251:−0.0072873179 252:−0.005927789
253:−0.0018599511 254:−0.017141052 255:−0.023494685 256:−0.01788312 257:−0.01943502
258:−0.0060224077 259:−0.0073500308 260:−0.0064477329 261:−0.0002986097 262:−0.0014349599
263:−0.0020359957 264:−0.0082596857 265:−0.006963369 266:−0.0016096481 267:−0.0083991755
268:−0.046351645 269:−0.046128571 270:−0.011141608 271:0.0020650877 272:−0.0010642689
273:−0.018076098 274:−0.016929928 275:−0.0052876701 276:−0.0025432054 277:−0.04111632
278:−0.031511344 279:−0.019488858 280:−0.0036160324 281:−0.032332413 282:−0.023754911

APPENDIX C1-continued

SVM Model Weights
(340; Normal/Diseased)

283:−0.0030713808 284:−0.033357695 285:−0.027144579 286:−0.0093234172 287:−0.0091438433
288:0.00080924761 289:−0.0040808818 290:−0.00058058492 291:0.00025530611
292:0.00042821659 293:−0.0017559038 294:0.00030293313 295:−0.0004816725
296:−0.00057298481 297:−0.00086739491 298:0.0020803961 299:0.00010370808 300:0.00075778627
301:0.00074104586 302:−0.00021793939 303:0.0013351805 304:−0.0006143825
305:0.0025815656 306:7.1731614e−005 307:−0.0052312948 308:−0.00063595735
309:0.0015091125 310:−0.00024647679 311:−0.0050271503 312:−0.00065122027
313:−0.00070704299 314:−0.0038100008 315:0.0022923627 316:0.0019759815 317:0.00079242635
318:0.0045642676 319:0.001573379 320:0.0015903091 321:0.00074843148 322:−0.00091753813
323:0.0021253934 324:0.0013280844 325:−0.0030691659 326:−0.0033078301 327:0.0012743858
328:0.0024482214 329:0.0018192574 330:0.0026370357 331:0.0017312634 332:0.00066732749
333:0.00034391912 334:0.0037949879 335:0.0018411272 336:0.0051615993 337:0.0017553387
338:−0.0027431778 339:−0.0055160136 340:0.0031345901 #
−0.00012932098769911893 1:−0.65065694 2:−11.223598 3:1.5055434 4:−4.3927703 5:−0.60701919
6:8.6285686 7:−1.9276042 8:10.040118 9:7.8989391 10:1.4171855 11:1.1073941 12:−14.540407
13:−10.239526 14:3.6424522 15:−3.7669489 16:−3.0639727 17:−2.6669984 18:−3.3562353
19:1.1029365 20:3.2188668 21:−1.3355631 22:0.76778799 23:7.7980146 24:1.9258534
25:0.155596 26:1.4333936 27:−0.77129906 28:1.0654082 29:1.3451784 30:0.48762089
31:1.1563978 32:1.6590519 33:−1.8909501 34:−1.4574517 35:0.56878603 36:1.0720688
37:−0.074896112 38:0.67724591 39:0.11796083 40:−0.80937344 41:−0.72812855 42:0.62427038
43:−0.14251851 44:−1.2614839 45:0.80392224 46:0.055927221 47:−0.51965183 48:0.68937206
49:−0.029368833 50:0.29346243 51:0.54400104 52:0.026291719 53:−0.36792743 54:−0.33510557
55:0.01633551 56:0.62049705 57:−0.23660533 58:−0.29055452 59:0.21570383 60:0.47372437
61:0.33341625 62:−0.42971212 63:−0.16324264 64:−0.11314408 65:−0.25130454 66:−0.077694908
67:−0.30443865 68:0.48772439 69:−0.18433747 70:0.12364767 71:−0.03648885 72:−0.4479292
73:−0.10614621 74:−0.071375042 75:−0.12610583 76:0.27633363 77:−0.26804826 78:−0.071432278
79:−0.14241533 80:0.01881632 81:−0.16835345 82:−0.039293341 83:0.22493207 84:−0.046756189
85:−0.11474198 86:−0.13416764 87:−0.11974655 88:−0.18672298 89:0.068480782 90:−0.11168448
91:−0.13745856 92:−0.053178217 93:−0.1196205 94:−0.059177827 95:−0.23895411 96:−0.16846043
97:0.074212946 98:−0.0081631783 99:−0.080792852 100:0.010322931 101:−0.090231359
102:0.24106196 103:0.023264579 104:0.10420329 105:−0.13601382 106:−0.0042355363
107:0.11146924 108:0.03451322 109:−0.11563939 110:0.0099846423 111:0.032353658
112:0.08137513 113:0.036952905 114:0.0075508715 115:0.051353753 116:0.028533757
117:0.080033883 118:0.017001057 119:0.030621406 120:−0.020350801 121:−0.016398866
122:0.064432539 123:0.020675234 124:0.054768387 125:0.042931769 126:0.015917649
127:0.058229867 128:−0.051847477 129:−0.018157952 130:−0.059494838 131:−0.049216989
132:−0.051627278 133:0.045514364 134:−0.022174053 135:0.0055948645 136:−0.0036672305
137:9.853208e−005 138:−0.017125415 139:0.0062208101 140:0.00056613336 141:0.0012280536
142:−0.00039310646 143:−0.0063707544 144:0.0015248039 145:−0.0029345977
146:−0.00076821423 147:0.00013666278 148:−0.0051379474 149:0.0066761598 150:−0.0024066679
151:0.0038081626 152:−0.0013487631 153:−0.0020869875 154:−0.0023751855 155:1.1204498e−006
156:0.0039485889 157:−0.00011155871 158:0.00070337567 159:0.0012323871
160:0.0021008069 161:0.0028489598 162:0.00029079549 163:0.0020081406 164:0.0044465163
165:0.007065278 166:0.0012901861 167:0.0037493915 168:−0.0023597497 169:−0.00012567961
170:0.00047573209 171:7.8875659e−005 172:−0.0056320974 173:−0.0067036133
174:0.00017559867 175:0.001684437 176:−0.0034504069 177:0.0018235954 178:−0.001383971
179:0.0004998623 180:−0.00066253374 181:0.0015807585 182:0.00412085 183:0.0021063511
184:0.00072732504 185:−0.0012095358 186:−0.0030121093 187:−0.0020631803
188:−0.00068084424 189:0.0002527938 190:−0.0034640408 191:−0.00026976471 192:0.00097010034
193:−0.0011612385 194:−0.0015113452 195:0.00062438019 196:−0.00013164691
197:0.0020616048 198:0.0010445472 199:−0.0049765292 200:9.8877339e−005 201:0.0028779099
202:−0.0036701721 203:0.00099803088 204:0.00068234798 205:0.002192216 206:0.0033146022
207:0.00050616561 208:−0.0031757453 209:0.0028448526 210:0.00092352234
211:−0.0022140611 212:−0.0013608048 213:0.0051376815 214:−0.0017870248 215:−0.0027518668
216:0.00043837572 217:−0.027317183 218:−0.024619192 219:−0.01382506 220:−0.015382294
221:−0.016386922 222:−0.0094594397 223:−0.0056853383 224:−0.00050634646
225:−0.00087913428 226:−0.023968795 227:−0.0034698097 228:−0.0016731552 229:0.00047607321
230:−0.011432272 231:−0.00036644109 232:−0.0025967851 233:0.0015593689
234:−0.0042631673 235:−0.0053286692 236:−0.0059999214 237:−0.087129325 238:−0.063751429
239:−0.0045496477 240:−0.0073839114 241:0.0014150206 242:−0.0042075687 243:−0.0022374168
244:−0.041910719 245:−0.030919394 246:−0.049301699 247:−0.019442754 248:−0.0019611341
249:−0.0072449106 250:−0.0051453672 251:−0.0072873179 252:−0.005927789 253:−0.0018599511
254:−0.017141052 255:−0.023494685 256:−0.01788312 257:−0.01943502 258:−0.0060224077
259:−0.0073500308 260:−0.0064477329 261:−0.0002986097 262:−0.0014349599 263:−0.0020359957
264:−0.0082596857 265:−0.006963369 266:−0.0016096481 267:−0.0083991755 268:−0.046351645
269:−0.046128571 270:−0.011141608 271:0.0020650877 272:−0.0010642689 273:−0.018076098
274:−0.016929928 275:−0.0052876701 276:−0.0025432054 277:−0.04111632 278:−0.031511344
279:−0.019488858 280:−0.0036160324 281:−0.032332413 282:−0.023754911 283:−0.0030713808
284:−0.033357695 285:−0.027144579 286:−0.0093234172 287:−0.0091438433 288:0.00080924761
289:−0.0040808818 290:−0.00058058492 291:0.00025530611 292:0.00042821659
293:−0.0017559038 294:0.00030293313 295:−0.0004816725 296:−0.00057298481 297:−0.00086739491
298:0.0020803961 299:0.00010370808 300:0.00075778627 301:0.00074104586
302:−0.00021793939 303:0.0013351805 304:−0.0006143825 305:0.0025815656 306:7.1731614e−005
307:−0.0052312948 308:−0.00063595735 309:0.0015091125 310:−0.00024647679
311:−0.0050271503 312:−0.00065122027 313:−0.00070704299 314:−0.0038100008 315:0.0022923627
316:0.0019759815 317:0.00079242635 318:0.0045642676 319:0.001573379 320:0.0015903091
321:0.00074843148 322:−0.00091753813 323:0.0021253934 324:0.0013280844

APPENDIX C1-continued

| SVM Model Weights (340; Normal/Diseased) |
|---|
| 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −0.00025618839285440316 1:1.2380526 2:6.2734895 3:0.58176476 4:−0.18845265 5:0.95705378 6:0.28784919 7:−0.46276212 8:−0.51710206 9:0.76353443 10:2.6615283 11:1.4559362 12:−0.38926667 13:1.7957709 14:0.44136238 15:3.6968684 16:2.0517492 17:1.2257472 18:−0.0037159321 19:0.047719728 20:0.43442419 21:−0.65809464 22:1.4208165 23:1.4070851 24:0.67525446 25:−0.24455935 26:0.16233224 27:−0.13480142 28:−0.26588619 29:1.8219868 30:−0.42708546 31:0.1047719 32:−0.78840756 33:0.90967578 34:0.5203284 35:0.35464984 36:−0.13433941 37:0.43185562 38:1.0523111 39:−0.26393235 40:1.1023602 41:−0.4250038 42:−0.44484338 43:−0.48972157 44:−0.027601799 45:0.56181395 46:−1.2650515 47:0.14227198 48:−0.57984716 49:−0.35134196 50:−1.0418026 51:−0.19757465 52:−0.57490361 53:0.17539091 54:0.15281017 55:0.58470583 56:−1.1123278 57:1.2199504 58:−0.43157127 59:1.0315589 60:0.37258533 61:−0.79094052 62:−0.74351996 63:−0.97267073 64:−0.34391591 65:0.31752416 66:−0.64545923 67:1.4758652 68:0.35093981 69:−0.87086546 70:0.11758564 71:−0.1760256 72:−0.97367996 73:−0.29235399 74:0.51659071 75:−0.89112943 76:0.23322439 77:−1.2678198 78:0.40858251 79:0.23541886 80:−1.1555972 81:−1.0754782 82:−0.99601054 83:−0.092877455 84:0.52989942 85:−0.537687 86:0.31971961 87:0.15677428 88:−0.92677659 89:−0.15221228 90:1.4032124 91:−0.24829739 92:−0.080516569 93:−0.064661287 94:−0.71952105 95:1.6714014 96:−0.56214857 97:−0.53043419 98:−0.30962712 99:0.1063592 100:−0.44118908 101:0.48422915 102:0.99163204 103:−0.029411443 104:0.39145091 105:−0.29760256 106:0.53245884 107:0.17660668 108:0.13701656 109:0.041900426 110:0.28206196 111:0.15984876 112:−0.28847924 113:0.14860727 114:0.23763703 115:0.056475263 116:−0.24749815 117:−0.40372667 118:−0.47092992 119:0.24538058 120:0.43835026 121:0.071213655 122:−0.1649581 123:0.13573727 124:−0.15372387 125:−0.051922388 126:0.26439261 127:0.22841637 128:−0.19923955 129:−0.045456704 130:0.223327 131:−0.28625253 132:0.012182434 133:−0.33590463 134:0.045404188 135:0.17477839 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |
| −1.822469996101117e−006 1:−8.2891655 2:−0.42698517 3:7.9929414 4:−21.96343 5:−2.5162337 6:−2.332407 7:−3.5282142 8:−10.863458 9:2.4572353 10:−9.3228836 11:1.7616936 12:−1.5003358 13:−5.9558101 14:−5.6671357 15:1.9989141 16:0.0007951344 17:2.2202916 18:1.6051667 19:−0.46657437 20:−0.14883198 21:0.32293826 22:1.809746 23:0.50881672 24:0.20460126 25:−0.99105644 26:0.68109101 27:0.21133116 28:−0.1266762 29:−0.35163447 30:−0.48319864 31:−0.44588166 32:−0.81961346 33:0.4458102 34:0.25585374 35:0.22169833 36:0.50088394 |

APPENDIX C1-continued

| SVM Model Weights (340; Normal/Diseased) |
|---|
| 37:−0.18526353 38:−0.57342333 39:−0.4100264 40:−0.49656498 41:−0.048766967 42:−0.27916297 43:−0.21427028 44:0.23489569 45:−0.055255346 46:0.14571071 47:−0.38773367 48:0.24204808 49:−0.025501506 50:0.22812733 51:0.016479289 52:0.0047244946 53:−0.10513508 54:0.0340891 55:−0.11792875 56:0.014585208 57:0.10346211 58:0.086079985 59:0.13638112 60:−0.029077984 61:−0.066002205 62:−0.0022148392 63:−0.051324606 64:0.23397739 65:0.030481266 66:0.039421767 67:0.14640144 68:0.054071993 69:−0.018368751 70:−0.0066018607 71:0.13411276 72:0.026797809 73:−0.10997321 74:0.010199982 75:0.1154227 76:−0.065298446 77:−0.0083012516 78:−0.037069004 79:0.10039674 80:0.071657665 81:0.12727965 82:−0.11805948 83:0.00066952186 84:−0.054706763 85:0.091746822 86:0.029696872 87:0.061503891 88:0.03245607 89:−0.052378852 90:0.077654056 91:−0.050794069 92:−0.060988717 93:−0.055440236 94:0.0037542861 95:0.073643796 96:0.039003935 97:0.06855385 98:0.015820434 99:0.021465937 100:0.0077944845 101:−0.0019617444 102:−0.044610556 103:−0.02758692 104:0.028581213 105:0.083054505 106:0.033804782 107:−0.032350469 108:0.096636586 109:0.031704508 110:0.04338941 111:−0.059521303 112:−0.018208284 113:−0.0042061959 114:−0.041491624 115:−0.024438348 116:−0.016554918 117:−0.012899144 118:0.0028049359 119:0.06729117 120:−0.047828618 121:0.0087301023 122:0.017425304 123:0.01092264 124:−0.034315046 125:0.012841884 126:−0.046630777 127:0.00085983245 128:0.022828637 129:0.017506592 130:0.0044898908 131:0.0091082333 132:−0.0030817804 133:−0.044458587 134:−0.033935066 135:0.019090308 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:−0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # 3.1141530976140584e−005 1:0.23982425 2:−2.2714684 3:2.7530899 4:−0.43534729 5:−2.13143725 6:−6.5755577 7:−0.23095936 8:2.4990304 9:0.5341723 10:0.474659 11:4.083261 12:0.4186067 13:1.0172553 14:3.2780108 15:0.36603203 16:2.1767581 17:2.6592224 18:0.28363878 19:1.2787055 20:−2.7076814 21:−2.8657753 22:0.7609598 23:0.75307113 24:2.2299948 25:−0.22061571 26:1.3376261 27:−2.2725747 28:−0.38882238 29:0.67952865 30:1.555928 31:0.10306518 32:1.0196824 33:0.34012586 34:1.5915979 35:−0.66413891 36:−1.6473995 37:−0.57017684 38:1.3736212 39:0.27528748 40:−0.72598064 41:−0.99590254 42:−2.4370754 43:−1.106745 44:0.0070058061 45:−1.6885 46:0.73374856 47:−2.1671956 48:0.18995385 49:−0.40758225 50:1.3748928 51:0.42502078 52:−0.47098222 53:0.77174622 54:−1.4447688 55:−0.9513852 56:−0.74914551 57:−1.4335645 58:0.15501319 59:−0.70597559 60:−0.71346951 61:0.17186414 62:−0.49394378 63:−0.36525911 64:−0.88786191 65:0.57959801 66:0.01567691 67:−0.086151116 68:−0.40630969 69:−1.0540781 70:−1.372297 71:−0.0055705337 72:0.64706087 73:−0.29820356 74:0.34114784 75:−0.11990818 76:0.62212431 77:−0.79698873 78:−1.0118636 79:−0.50075036 80:−0.33878428 81:−0.25166044 82:0.020956567 83:−0.3969045 84:0.24251559 85:0.55688226 86:−0.060546517 87:−0.67644072 88:−0.083061516 89:−0.40007842 90:0.60753351 |

APPENDIX C1-continued

| SVM Model Weights (340; Normal/Diseased) |
|---|
| 91:0.37825751 92:−0.12762758 93:1.0505396 94:0.346627 95:−0.80647266 96:0.66907626 97:0.28694856 98:0.46163556 99:0.22819805 100:0.0759262 101:0.028915809 102:−0.20079345 103:0.98194212 104:0.15251906 105:0.6114341 106:0.20421335 107:−0.19041851 108:0.002931691 109:0.25667602 110:−0.19782954 111:0.035900418 112:−0.64252096 113:0.16462967 114:−0.68771815 115:0.081782721 116:0.091236867 117:−0.095214687 118:−0.52825224 119:0.060998734 120:0.059148341 121:0.16658965 122:−0.17567663 123:−0.23029633 124:0.2215855 125:0.3467598 126:−0.00039247944 127:0.12656112 128:0.21096483 129:−0.22154965 130:0.095295489 131:−0.10339074 132:−0.096810713 133:0.02793801 134:0.13953027 135:0.032407463 136:−0.0036672305 137:9.853208e−005 138:−0.017125415 139:0.0062208101 140:0.00056613336 141:0.0012280536 142:−0.00039310646 143:−0.0063707544 144:0.0015248039 145:−0.0029345977 146:−0.00076821423 147:0.00013666278 148:−0.0051379474 149:0.0066761598 150:−0.0024066679 151:0.0038081626 152:−0.0013487631 153:−0.0020869875 154:−0.0023751855 155:1.1204498e−006 156:0.0039485889 157:−0.00011155871 158:0.00070337567 159:0.0012323871 160:0.0021008069 161:0.0028489598 162:0.00029079549 163:0.0020081406 164:0.0044465163 165:0.007065278 166:0.0012901861 167:0.0037493915 168:−0.0023597497 169:−0.00012567961 170:0.00047573209 171:7.8875659e−005 172:−0.0056320974 173:−0.0067036133 174:0.00017559867 175:0.001684437 176:−0.0034504069 177:0.0018235954 178:−0.001383971 179:0.0004998623 180:−0.00066253374 181:0.0015807585 182:0.00412085 183:0.0021063511 184:0.00072732504 185:−0.0012095358 186:−0.0030121093 187:−0.0020631803 188:−0.00068084424 189:0.0002527938 190:−0.0034640408 191:−0.00026976471 192:0.00097010034 193:−0.0011612385 194:−0.0015113452 195:0.00062438019 196:−0.00013164691 197:0.0020616048 198:0.0010445472 199:−0.0049765292 200:9.8877339e−005 201:0.0028779099 202:−0.0036701721 203:0.00099803088 204:0.00068234798 205:0.002192216 206:0.0033146022 207:0.00050616561 208:−0.0031757453 209:0.0028448526 210:0.00092352234 211:−0.0022140611 212:−0.0013608048 213:0.0051376815 214:0.0017870248 215:−0.0027518668 216:0.00043837572 217:−0.027317183 218:−0.024619192 219:−0.01382506 220:−0.015382294 221:−0.016386922 222:−0.0094594397 223:−0.0056853383 224:−0.00050634646 225:−0.00087913428 226:−0.023968795 227:−0.0034698097 228:−0.0016731552 229:0.00047607321 230:−0.011432272 231:−0.00036644109 232:−0.0025967851 233:0.0015593689 234:−0.0042631673 235:−0.0053286692 236:−0.0059999214 237:−0.087129325 238:−0.063751429 239:−0.0045496477 240:−0.0073839114 241:0.0014150206 242:−0.0042075687 243:−0.0022374168 244:−0.041910719 245:−0.030919394 246:−0.049301699 247:−0.019442754 248:−0.0019611341 249:−0.0072449106 250:−0.0051453672 251:−0.0072873179 252:−0.005927789 253:−0.0018599511 254:−0.017141052 255:−0.023494685 256:−0.01788312 257:−0.01943502 258:−0.0060224077 259:−0.0073500308 260:−0.0064477329 261:−0.0002986097 262:−0.0014349599 263:−0.0020359957 264:−0.0082596857 265:−0.006963369 266:−0.0016096481 267:−0.0083991755 268:−0.046351645 269:−0.046128571 270:−0.011141608 271:0.0020650877 272:−0.0010642689 273:−0.018076098 274:−0.016929928 275:−0.0052876701 276:−0.0025432054 277:−0.04111632 278:−0.031511344 279:−0.019488858 280:−0.0036160324 281:−0.032332413 282:−0.023754911 283:−0.0030713808 284:−0.033357695 285:−0.027144579 286:−0.0093234172 287:−0.0091438433 288:0.00080924761 289:−0.0040808818 290:−0.00058058492 291:0.00025530611 292:0.00042821659 293:−0.0017559038 294:0.00030293313 295:−0.0004816725 296:−0.00057298481 297:−0.00086739491 298:0.0020803961 299:0.00010370808 300:0.00075778627 301:0.00074104586 302:−0.00021793939 303:0.0013351805 304:−0.0006143825 305:0.0025815656 306:7.1731614e−005 307:−0.0052312948 308:−0.00063595735 309:0.0015091125 310:−0.00024647679 311:−0.0050271503 312:−0.00065122027 313:−0.00070704299 314:−0.0038100008 315:0.0022923627 316:0.0019759815 317:0.00079242635 318:0.0045642676 319:0.001573379 320:0.0015903091 321:0.00074843148 322:−0.00091753813 323:0.0021253934 324:0.0013280844 325:−0.0030691659 326:−0.0033078301 327:0.0012743858 328:0.0024482214 329:0.0018192574 330:0.0026370357 331:0.0017312634 332:0.00066732749 333:0.00034391912 334:0.0037949879 335:0.0018411272 336:0.0051615993 337:0.0017553387 338:−0.0027431778 339:−0.0055160136 340:0.0031345901 # |

APPENDIX C2

| SVM ModelWeights (340; Benign/Malignant) |
|---|
| SVM-light Version V6.01<br>0 # kernel type<br>3 # kernel parameter -d<br>1 # kernel parameter -g<br>1 # kernel parameter -s<br>1 # kernel parameter -r<br>empty# kernel parameter -u<br>340 # highest feature index<br>99 # number of training documents<br>65 # number of support vectors plus 1<br>−0.37652729 # threshold b, each following line is a SV (starting with alpha*y)<br>−0.0033153142499855108 1:−0.23311329 2:−1.5340611 3:−0.56233943 4:−7.4785199 5:−3.6518826 6:−4.7517338 7:−0.41352883 8:−1.1385972 9:−2.3377373 10:0.89005411 11:−3.0769937 12:0.91200078 13:−1.0174296 14:−0.29183522 15:5.4507852 16:1.9547648 17:2.4246554 18: −2.5977473 19:0.059181549 20:0.9693011 21:−1.3478724 22:1.2955381 23:0.29502755 24: −0.31393111 25:−0.025742445 26:−1.3289164 27:−1.1254236 28:0.11153328 29:1.9973383 |

APPENDIX C2-continued

| SVM ModelWeights (340; Benign/Malignant) |
|---|
| 30:1.257899 31:0.91507447 32:0.72226965 33:0.39845112 34:−1.3278019 35:−0.95194173 36: −2.0961843 37:−1.1352364 38:−0.64997375 39:0.065316387 40:−0.38678196 41:0.77325523 42:1.3836633 43:1.3171499 44:0.053990051 45:0.77371556 46:2.1609168 47:−1.3172421 48:0.39412561 49:0.23929304 50:1.105505 51:0.84551901 52:−0.40700731 53:−0.40167317 54: −0.76905733 55:−0.42601669 56:1.0445652 57:1.9075065 58:1.0322175 59:−0.4670966 60:0.30819783 61:0.74754339 62:−0.26703897 63:0.57786393 64:−0.32511202 65:0.16155197 66: −0.72578001 67:−0.066891424 68:0.11020496 69:−0.62233603 70:−0.98494661 71:−0.0048836544 72:0.43202633 73:0.55178761 74:−0.32371372 75:−0.18778911 76:−0.38373259 77:−0.52735662 78:0.35236505 79:0.060871631 80:−1.1960546 81:−0.47478089 82:0.44778258 83:−0.11591902 84:−0.41117722 85:0.94405186 86:−0.52732617 87:0.035399996 88:0.058130287 89:0.0309637 90:0.083736248 91:−0.81783479 92:0.40891954 93:−0.56611413 94:0.29939261 95:0.1568504 96: −0.14485334 97:0.0039280006 98:0.010595871 99:−0.0072948104 100:0.0007581744 101:0.0015444086 102:0.00086657552 103:0.0014506713 104:0.00027309253 105: −0.0003779236 106:−0.0033040401 107:−0.002894687 108:0.0012058502 109:0.0026374348 110: −0.0018928888 111:−0.0024273857 112:−0.0003231481 113:0.00057429477 114:−0.00070962519 115:0.0011349921 116:−0.0046544136 117:6.0590241e−007 118:0.00074805523 119: −0.0025794252 120:0.00037352511 121:−0.0022889439 122:0.0011132049 123:−0.0024242986 124:−0.0045571304 125:−0.0020117455 126:−0.0092068724 127:−0.0077256206 128: −0.00070437411 129:0.0012516935 130:0.00055489031 131:0.0013429716 132:0.00036176579 133:−0.0026087298 134:5.3104148e−005 135:−0.001098063 136:0.0010348612 137: −0.00068726367 138:−0.00074436213 139:0.0027458151 140:0.0010222673 141:−0.0018521026 142:−0.00061301264 143:−0.001804522 144:−0.00021584153 145:0.0015449577 146: −0.0015697054 147:−0.00097707158 148:−0.0011295594 149:−0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242:−0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:−0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # −0.003315314249985510 8 1:5.7773232 2:−0.2485496 3:−4.9756732 4:2.3672733 5:−1.7608249 6: −4.6183424 7:−6.1881247 8:−1.4636059 9:0.42568609 10:0.91490215 11:2.9737656 12:1.4572622 13:2.3844304 14:3.479558 15:−2.172904 16:1.3687432 17:−2.2401547 18:2.038378 19:−1.0956939 20:2.6179361 21:4.8499289 22:−1.0542914 23:−1.1590868 24:2.5353518 25:0.69207913 26: −5.589396 27:1.1018655 28:4.4162931 29:2.5424984 30:−0.49032038 31:1.8779082 32:−2.026341 33:−3.0662463 34:−1.2714849 35:−1.7003183 36:0.089564629 37:−0.045071993 38:1.3744485 39: −1.2290742 40:1.29223 41:0.27818131 42:−0.72624052 43:0.26687896 44:−0.15784797 45:0.26189137 46:−0.28338087 47:0.54031122 48:−0.3526116 49:0.74344003 50:−1.500893 51:0.69248003 52:−0.87673593 53:0.35906056 54:−0.0430285 55:−0.05152908 56:−0.055442557 57:−0.063158438 58:0.29045451 59:−0.47792071 60:−0.71567893 61:0.2203918 62:0.75583583 63:−0.33738095 64:0.40889195 65:0.36191818 66:−0.52839923 67:0.72879851 68:0.44805676 69:0.1652946 70:−0.25166011 71:0.23027706 72:0.59822512 73:−0.41949832 74:−0.62871504 75: |

APPENDIX C2-continued

| SVM ModelWeights (340; Benign/Malignant) |
|---|
| −0.47131854 76:−0.10790173 77:0.11770677 78:0.30318615 79:−0.15497944 80:−0.43600088 81: −0.14937481 82:0.14475852 83:−0.094878353 84:0.014042439 85:0.16163081 86:0.25650221 87:0.1918962 88:0.034946408 89:−0.046857253 90:−0.028248392 91:−0.015145044 92: −0.062450223 93:0.23711321 94:−0.12942047 95:−0.10125817 96:0.095526397 97:0.0039280006 98:0.010595871 99:−0.0072948104 100:0.0007581744 101:0.0015444086 102:0.00086657552 103:0.0014506713 104:0.00027309253 105:−0.0003779236 106:−0.0033040401 107:−0.002894687 108:0.0012058502 109:0.0026374348 110:−0.0018928888 111:−0.0024273857 112:−0.0003231481 113:0.00057429477 114:−0.00070962519 115:0.0011349921 116:−0.0046544136 117:6.0590241e −007 118:0.00074805523 119:−0.0025794252 120:0.00037352511 121:−0.0022889439 122:0.0011132049 123:−0.0024242986 124:−0.0045571304 125:−0.0020117455 126: −0.0092068724 127:−0.0077256206 128:−0.00070437411 129:0.0012516935 130:0.00055489031 131:0.0013429716 132:0.00036176579 133:−0.0026087298 134:5.3104148e−005 135: −0.001098063 136:0.0010348612 137:−0.00068726367 138:−0.00074436213 139:0.0027458151 140:0.0010222673 141:−0.0018521026 142:−0.00061301264 143:−0.001804522 144: −0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155:−0.0035724007 156:0.0011358063 157:−0.0012884629 158: −0.0031973415 159:0.00045693576 160:−0.0012730506 161:0.0014123393 162:0.003461167 163: −0.0029414443 164:−0.00037983558 165:−0.0023911442 166:0.0021477563 167:9.2110975e−005 168:−0.0026100944 169:−0.0034047128 170:−0.0029387963 171:−0.0023030045 172: −0.0054465104 173:−0.0021478815 174:−0.0022738085 175:0.00050098688 176:−0.0021780876 177:2.5619611e−005 178:−0.0010297548 179:0.000299401 180:0.0002858036 181:0.0015720503 182:0.0012860922 183:0.0015920103 184:0.0034542123 185:−0.0054590856 186:−0.0013231005 187:−0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212: −0.00063428417 213:0.0051512984 214:0.00089924945 215:−0.00035291715 216:−0.0026578247 217:−0.031516869 218:−0.018453332 219:−0.012905908 220:−0.015366459 221:−0.013814257 222:−0.007569442 223:−0.0047048843 224:0.00062012818 225:0.0014852113 226:−0.019181944 227:−0.005778844 228:−0.0022216991 229:−0.0013164993 230:−0.011913291 231:−0.0048886021 232:−0.0050922348 233:−0.00091115123 234:−0.0028072072 235:−0.0020788321 236: −0.0069042598 237:−0.092131011 238:−0.068610474 239:−0.0047269738 240:−0.0084348312 241: −0.0050073303 242:−0.003040591 243:−0.0038143608 244:−0.040638726 245:−0.02857391 246: −0.0472783 247:−0.020520929 248:−0.0018310277 249:−0.0055512898 250:−0.0060781906 251: −0.0072731995 252:−0.006453387 253:−0.0049183252 254:−0.014674404 255:−0.026012832 256: −0.021858063 257:−0.021156041 258:−0.0072407476 259:−0.0034868279 260:−0.0014243352 261: −0.0010014101 262:−0.0013208789 263:−0.0028763453 264:−0.0076750983 265:−0.0046692337 266:−0.0012726086 267:−0.0068167564 268:−0.04353733 269:−0.046706751 270:−0.010794718 271:−0.0024784503 272:−0.0059213047 273:−0.016445309 274:−0.016014025 275:−0.0077815265 276:−0.0023459131 277:−0.040564284 278:−0.032950211 279:−0.017959842 280:−0.0040876623 281:−0.026083954 282:−0.022933906 283:−0.0027156388 284:−0.035015725 285:−0.029552883 286:−0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # −0.0033153142499855108 1:2.3662179 2:1.6748204 3:3.8486438 4:1.4897406 5:−0.9291935 6: −7.1160836 7:−1.9521724 8:1.1360776 9:−1.8011853 10:2.2141206 11:1.7985709 12:−2.1508341 13:1.6635997 14:0.10243254 15:−0.36165324 16:1.0803972 17:0.49766871 18:0.0012823264 19: −0.98907411 20:−2.9658399 21:0.10815067 22:1.4386787 23:−1.396909 24:−0.14514606 25: −0.095915295 26:−0.20809935 27:−1.45952 28:−0.80965692 29:−0.10805699 30:0.23815021 31: −0.7416473 32:0.14330949 33:0.084148057 34:0.099837765 35:−2.0965025 36:−0.92405814 37: −0.084430851 38:−0.96411276 39:−1.1714625 40:0.35370091 41:0.54465806 42:0.024007868 43: −1.4951186 44:−1.5395824 45:1.2847537 46:0.72993517 47:−0.69907892 48:−0.5942564 49: −0.5684616 50:1.1084251 51:−0.76730984 52:0.28232136 53:0.12850039 54:−0.92810959 55: −1.2326117 56:−1.144209 57:0.19738084 58:0.55337465 59:−0.89919609 60:−0.69901681 61:0.4998959 62:−0.0089700799 63:−0.96022487 64:0.5021655 65:−1.2189608 66:0.82021332 67: −0.11272306 68:−0.123798 69:0.019708304 70:−0.24779686 71:−0.85190767 72:0.48128524 73: −1.2304204 74:0.93169534 75:−1.5035605 76:−1.2377514 77:0.28679666 78:0.21370013 79:0.081786178 80:1.162581 81:0.40195379 82:−0.67829359 83:0.50082994 84:0.24331501 85: −0.63211483 86:0.25782165 87:−0.40200973 88:0.94659495 89:−0.26826444 90:0.068528414 91: −0.52930117 92:0.30778074 93:−0.046182852 94:−0.041630726 95:0.040594142 96:0.31364647 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 |

APPENDIX C2-continued

SVM ModelWeights
(340; Benign/Malignant)

116:−0.0046544136 117:6.0590241e−007 118:0.00074805523 119:−0.0025794252
120:0.00037352511 121:−0.0022889439 122:0.0011132049 123:−0.0024242986 124:
−0.0045571304 125:−0.0020117455 126:−0.0092068724 127:−0.0077256206 128:−0.00070437411
129:0.0012516935 130:0.00055489031 131:0.0013429716 132:0.00036176579 133:
−0.0026087298 134:5.3104148e−005 135:−0.001098063 136:0.0010348612 137:−0.00068726367
138:−0.00074436213 139:0.0027458151 140:0.0010222673 141:−0.0018521026 142:
−0.00061301264 143:−0.001804522 144:−0.00021584153 145:0.0015449577 146:−0.0015697054
147:−0.00097707158 148:−0.0011295594 149:0.0028935266 150:−0.00053708232
151:0.0018405041 152:−0.002562111 153:−0.0013092471 154:−0.00046263589 155:
−0.0035724007 156:0.0011358063 157:−0.0012884629 158:−0.0031973415 159:0.00045693576
160:−0.0012730506 161:0.0014123393 162:0.003461167 163:−0.0029414443 164:−0.00037983558
165:−0.0023911442 166:0.0021477563 167:9.2110975e−005 168:−0.0026100944 169:
−0.0034047128 170:−0.0029387963 171:−0.0023030045 172:−0.0054465104 173:−0.0021478815
174:−0.0022738085 175:0.00050098688 176:−0.0021780876 177:2.5619611e−005 178:
−0.0010297548 179:0.000299401 180:0.0002858036 181:0.0015720503 182:0.0012860922
183:0.0015920103 184:0.0034542123 185:−0.0054590856 186:−0.0013231005 187:
−0.00026378682 188:−5.6713336e−005 189:0.0016455925 190:0.00055903167 191:0.00040327062
192:−0.00066433422 193:−0.0014816546 194:0.0016943325 195:0.00012320606
196:0.0006577372 197:0.00056744454 198:−0.0023361598 199:0.0042997436 200:−0.0016990597
201:0.0030764227 202:−0.0027063258 203:0.00046884044 204:−0.00031649071
205:0.00065622263 206:−0.0026635081 207:−0.0039158296 208:0.0020220254 209:0.0012250372
210:−0.0028663045 211:−0.0012186989 212:−0.00063428417 213:0.0051512984
214:0.00089924945 215:−0.00035291715 216:−0.0026578247 217:−0.031516869 218:
−0.018453332 219:−0.012905908 220:−0.015366459 221:−0.013814257 222:−0.007569442 223:
−0.0047048843 224:0.00062012818 225:0.0014852113 226:−0.019181944 227:−0.005778844 228:
−0.0022216991 229:−0.0013164993 230:−0.011913291 231:−0.0048886021 232:−0.0050922348
233:−0.00091115123 234:−0.0028072072 235:−0.0020788321 236:−0.0069042598 237:
−0.092131011 238:−0.068610474 239:−0.0047269738 240:−0.0084348312 241:−0.0050073303 242:
−0.003040591 243:−0.0038143608 244:−0.040638726 245:−0.02857391 246:−0.0472783 247:
−0.020520929 248:−0.0018310277 249:−0.0055512898 250:−0.0060781906 251:−0.0072731995
252:−0.006453387 253:−0.0049183252 254:−0.014674404 255:−0.026012832 256:−0.021858063
257:−0.021156041 258:−0.0072407476 259:−0.0034868279 260:−0.0014243352 261:−0.0010014101
262:−0.0013208789 263:−0.0028763453 264:−0.0076750983 265:−0.0046692337 266:
−0.0012726086 267:−0.0068167564 268:−0.04353733 269:−0.046706751 270:−0.010794718 271:
−0.0024784503 272:−0.0059213047 273:−0.016445309 274:−0.016014025 275:−0.0077815265 276:
−0.0023459131 277:−0.040564284 278:−0.032950211 279:−0.017959842 280:−0.0040876623 281:
−0.026083954 282:−0.022933906 283:−0.0027156388 284:−0.035015725 285:−0.029552883 286:
−0.010026687 287:−0.011907991 288:0.0022531124 289:−0.002897898 290:−0.00044569091
291:0.00010489624 292:−0.00053147622 293:−0.00073173334 294:−0.000621646 295:
−0.00016437711 296:−0.00049518317 297:0.00021529767 298:0.00052096118 299:−4.636059e−005
300:−0.0021831172 301:−0.0014980205 302:−0.00038898826 303:0.00068646355
304:0.0026823219 305:−0.0040565808 306:−0.0020829935 307:−0.0013752591 308:
−0.00034383399 309:2.7236187e−005 310:−0.00070534449 311:−0.0012802118 312:−0.0030920727
313:−0.00088650011 314:−0.00014303472 315:0.00071791362 316:0.00019783134
317:2.9171604e−006 318:0.00037660156 319:0.0011750009 320:−0.0016896301 321:
−0.0015126425 322:−0.00083564757 323:0.0010692998 324:−0.0016934061 325:−0.00029338882
326:−0.0034646564 327:−7.9289544e−005 328:0.0023930578 329:0.00048041579
330:0.00021849622 331:4.0310828e−005 332:−0.0032790094 333:−0.00015884312 334:
−0.00031949134 335:3.3427419e−005 336:0.00084852462 337:0.00044620238 338:−0.0032407208
339:0.00048842531 340:0.00094149791 #
−0.0033153142499855108 1:−5.2307115 2:5.5413795 3:4.0636749 4:−6.2058477 5:4.1717806
6:1.6895379 7:0.53004158 8:−4.6441884 9:3.1082587 10:0.048623063 11:−1.3503591
12:0.17829828 13:−0.59768867 14:0.87042594 15:−0.4560613 16:−0.69823253 17:−0.94882631 18:
−1.0522534 19:−2.2051711 20:−2.6186538 21:1.3570184 22:−3.7802284 23:1.1904382 24:2.3432648
25:−1.1689653 26:2.4562342 27:0.067852028 28:−2.5447171 29:2.2677996 30:0.92332506 31:
−2.3834748 32:−0.49822828 33:−0.17621896 34:0.51221931 35:−3.6821847 36:−0.38832191
37:1.3851066 38:1.8787074 39:−0.19868882 40:0.63223851 41:0.81729114 42:0.5081135 43:
−0.64843142 44:−1.4564943 45:1.2146252 46:0.12510775 47:1.2823189 48:0.75310415 49:
−0.65507919 50:−1.0283387 51:−0.81086957 52:−0.84513521 53:−0.20092514 54:0.041422322 55:
−0.96993876 56:0.5406127 57:0.16784817 58:0.052268587 59:−1.0685024 60:−1.1371231 61:
−0.29202485 62:−1.5704151 63:−0.014245392 64:−0.24259058 65:1.4461937 66:0.37964907 67:
−0.13091937 68:0.052078299 69:−0.20226718 70:−0.91403842 71:0.89176095 72:−0.60484374
73:0.27189174 74:0.012570418 75:0.70590878 76:−0.089948945 77:0.62381929 78:−0.47178656
79:−0.026025595 80:0.56783694 81:−0.21542034 82:0.19036613 83:−0.091159619 84:−0.25391325
85:0.54905295 86:0.19299547 87:0.25178668 88:−0.043965578 89:−0.1485941 90:0.36930624 91:
−2.8203658e−005 92:−0.25145429 93:0.083629481 94:0.069254786 95:0.061303578 96:
−0.30719167 97:0.0039280006 98:0.010595871 99:−0.0072948104 100:0.0007581744
101:0.0015444086 102:0.00086657552 103:0.0014506713 104:0.00027309253 105:
−0.0003779236 106:−0.0033040401 107:−0.002894687 108:0.0012058502 109:0.0026374348 110:
−0.0018928888 111:0.0024273857 112:0.0003231481 113:0.00057429477 114:0.00070962519
115:0.0011349921 116:−0.0046544136 117:6.0590241e−007 118:0.00074805523 119:
−0.0025794252 120:0.00037352511 121:−0.0022889439 122:0.0011132049 123:−0.0024242986
124:−0.0045571304 125:−0.0020117455 126:−0.0092068724 127:−0.0077256206 128:
−0.00070437411 129:0.0012516935 130:0.00055489031 131:0.0013429716 132:0.00036176579
133:−0.0026087298 134:5.3104148e−005 135:−0.001098063 136:0.0010348612 137:
−0.00068726367 138:−0.00074436213 139:0.0027458151 140:0.0010222673 141:−0.0018521026
142:−0.00061301264 143:−0.001804522 144:−0.00021584153 145:0.0015449577 146:

APPENDIX C2-continued

| SVM ModelWeights (340; Benign/Malignant) |
| --- |

–0.0015697054 147:–0.00097707158 148:–0.0011295594 149:0.0028935266 150:–0.00053708232 151:0.0018405041 152:–0.002562111 153:–0.0013092471 154:–0.00046263589 155: –0.0035724007 156:0.0011358063 157:–0.0012884629 158:–0.0031973415 159:0.00045693576 160:–0.0012730506 161:0.0014123393 162:0.003461167 163:–0.0029414443 164:–0.00037983558 165:–0.0023911442 166:0.0021477563 167:9.2110975e–005 168:–0.0026100944 169:– –0.0034047128 170:–0.0029387963 171:–0.0023030045 172:–0.0054465104 173:–0.0021478815 174:–0.0022738085 175:0.00050098688 176:–0.0021780876 177:2.5619611e–005 178: –0.0010297548 179:0.000299401 180:0.0002858036 181:0.0015720503 182:0.0012860922 183:0.0015920103 184:0.0034542123 185:–0.0054590856 186:–0.0013231005 187: –0.00026378682 188:–5.6713336e–005 189:0.0016455925 190:0.00055903167 191:0.00040327062 192:–0.00066433422 193:–0.0014816546 194:0.0016943325 195:0.00012320606 196:0.0006577372 197:0.00056744454 198:–0.0023361598 199:0.0042997436 200:–0.0016990597 201:0.0030764227 202:–0.0027063258 203:0.00046884044 204:–0.00031649071 205:0.00065622263 206:–0.0026635081 207:–0.0039158296 208:0.0020220254 209:0.0012250372 210:–0.0028663045 211:–0.0012186989 212:–0.00063428417 213:0.0051512984 214:0.00089924945 215:–0.00035291715 216:–0.0026578247 217:–0.031516869 218: –0.018453332 219:–0.012905908 220:–0.015366459 221:–0.013814257 222:–0.007569442 223: –0.0047048843 224:0.00062012818 225:0.0014852113 226:–0.019181944 227:–0.005778844 228: –0.0022216991 229:–0.0013164993 230:–0.011913291 231:–0.0048886021 232:–0.0050922348 233:–0.00091115123 234:–0.0028072072 235:–0.0020788321 236:–0.0069042598 237: –0.092131011 238:–0.068610474 239:–0.0047269738 240:–0.0084348312 241:–0.0050073303 242: –0.003040591 243:–0.0038143608 244:–0.040638726 245:–0.02857391 246:–0.0472783 247: –0.020520929 248:–0.0018310277 249:–0.0055512898 250:–0.0060781906 251:–0.0072731995 252:–0.006453387 253:–0.0049183252 254:–0.014674404 255:–0.026012832 256:–0.021858063 257:–0.021156041 258:–0.0072407476 259:–0.0034868279 260:–0.0014243352 261:–0.0010014101 262:–0.0013208789 263:–0.0028763453 264:–0.0076750983 265:–0.0046692337 266: –0.0012726086 267:–0.0068167564 268:–0.04353733 269:–0.046706751 270:–0.010794718 271: –0.0024784503 272:–0.0059213047 273:–0.016445309 274:–0.016014025 275:–0.0077815265 276: –0.0023459131 277:–0.040564284 278:–0.032950211 279:–0.017959842 280:–0.0040876623 281: –0.026083954 282:–0.022933906 283:–0.0027156388 284:–0.035015725 285:–0.029552883 286: –0.010026687 287:–0.011907991 288:0.0022531124 289:–0.002897898 290:–0.00044569091 291:0.00010489624 292:–0.00053147622 293:–0.00073173334 294:–0.000621646 295: –0.00016437711 296:–0.00049518317 297:0.00021529767 298:0.00052096118 299:–4.636059e–005 300:–0.0021831172 301:–0.0014980205 302:–0.00038898826 303:0.00068646355 304:0.0026823219 305:–0.0040565808 306:–0.0020829935 307:–0.0013752591 308: –0.00034383399 309:2.7236187e–005 310:–0.00070534449 311:–0.0012802118 312:–0.0030920727 313:–0.00088650011 314:–0.00014303472 315:0.00071791362 316:0.00019783134 317:2.9171604e–006 318:0.00037660156 319:0.0011750009 320:–0.0016896301 321: –0.0015126425 322:–0.00083564757 323:0.0010692998 324:–0.0016934061 325:–0.00029338882 326:–0.0034646564 327:–7.9289544e–005 328:0.0023930578 329:0.00048041579 330:0.00021849622 331:4.0310828e–005 332:–0.0032790094 333:–0.00015884312 334: –0.00031949134 335:3.3427419e–005 336:0.00084852462 337:0.00044620238 338:–0.0032407208 339:0.00048842531 340:0.00094149791 #
–0.0024925461124968747 1:3.8347991 2:0.4250325 3:–15.678971 4:7.1875505 5:0.54047203 6: –4.0046563 7:1.9759779 8:1.9077226 9:10.761656 10:–8.7568007 11:–1.4441179 12:–0.30809698 13:–1.9578561 14:–4.2252517 15:8.2054901 16:–1.636007 17:2.6754603 18:7.3106451 19: –4.4067588 20:–2.1794596 21:3.0483193 22:–0.39562172 23:–1.4235375 24:1.0369247 25: –0.085445531 26:0.30943248 27:–3.5057745 28:1.2857898 29:0.37323707 30:–1.1636015 31: –0.86200023 32:–0.39294812 33:0.30153993 34:–0.14372639 35:0.73093683 36:0.12857766 37:0.41396561 38:–0.94348228 39:0.1596809 40:–0.35982186 41:–0.081217997 42:–0.14757583 43:0.31640163 44:–0.98368734 45:–0.13041568 46:0.27535918 47:–0.72610444 48:–0.27246878 49:0.10889015 50:0.083886296 51:–0.64067858 52:0.56922275 53:–0.44650257 54:0.023570085 55:–0.27306849 56:–0.18727268 57:–0.20339593 58:–0.0058271685 59:–0.099581204 60:0.39475891 61:0.19308588 62:–0.0053478032 63:0.096731231 64:0.26979297 65:0.15184869 66:–0.18696959 67:–0.15064354 68:–0.30398273 69:0.083900169 70:0.10426281 71:0.35618588 72:–0.34764102 73:0.30011776 74:–0.033746786 75:0.050758284 76:0.22227693 77:0.062899485 78:0.11515583 79:–0.32982102 80:0.17524947 81:–0.12747638 82:0.20460217 83:–0.097438082 84:0.16689576 85:–0.036133129 86:0.12806532 87:0.034909908 88:0.00037136837 89:–0.1285702 90:–0.16128434 91:–0.091103457 92:0.1129477 93:–0.10997864 94:–0.019782269 95:–0.05915641 96:–0.11404625 97:0.0039280006 98:0.010595871 99:–0.0072948104 100:0.0007581744 101:0.0015444086 102:0.00086657552 103:0.0014506713 104:0.00027309253 105: –0.0003779236 106:0.0033040401 107:0.002894687 108:0.0012058502 109:0.0026374348 110: –0.0018928888 111:–0.0024273857 112:–0.0003231481 113:0.00057429477 114:–0.00070962519 115:0.0011349921 116:–0.0046544136 117:6.0590241e–007 118:0.00074805523 119: –0.0025794252 120:0.00037352511 121:–0.0022889439 122:0.0011132049 123:–0.0024242986 124:–0.0045571304 125:–0.0020117455 126:–0.0092068724 127:–0.0077256206 128: –0.00070437411 129:0.0012516935 130:0.00055489031 131:0.0013429716 132:0.00036176579 133:0.0026087298 134:5.3104148e–005 135:–0.001098063 136:0.0010348612 137: –0.00068726367 138:–0.00074436213 139:0.0027458151 140:0.0010222673 141:–0.0018521026 142:–0.00061301264 143:–0.001804522 144:–0.00021584153 145:0.0015449577 146: –0.0015697054 147:–0.00097707158 148:–0.0011295594 149:0.0028935266 150:–0.00053708232 151:0.0018405041 152:–0.002562111 153:–0.0013092471 154:–0.00046263589 155: –0.0035724007 156:0.0011358063 157:–0.0012884629 158:–0.0031973415 159:0.00045693576 160:–0.0012730506 161:0.0014123393 162:0.003461167 163:–0.0029414443 164:–0.00037983558 165:–0.0023911442 166:0.0021477563 167:9.2110975e–005 168:–0.0026100944 169: –0.0034047128 170:–0.0029387963 171:–0.0023030045 172:–0.0054465104 173:–0.0021478815 174:–0.0022738085 175:0.00050098688 176:–0.0021780876 177:2.5619611e–005 178:

APPENDIX C2-continued

| SVM ModelWeights (340; Benign/Malignant) |
| --- |

−0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:−0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:0.0027156388 284:0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
−0.0033153142499855108 1:0.2945444 2:1.5663686 3:2.0269644 4:−1.3007404 5:2.2870119 6: −3.3503802 7:1.4742044 8:3.5182641 9:−3.8660257 10:−0.30044997 11:2.4009323 12:0.023592524 13:−0.092459396 14:−1.9675099 15:−0.52797329 16:1.6415339 17:−1.3027037 18:1.1715622 19: −1.3815528 20:0.1912863 21:0.80708176 22:−1.3128206 23:−1.3250409 24:−1.3467921 25:0.47949335 26:−0.77753985 27:1.4726981 28:−0.20863654 29:−0.41831556 30:−1.5252051 31: −0.68172175 32:−0.19234197 33:−0.57685065 34:0.22692519 35:−0.10171806 36:−1.639927 37:1.1498389 38:0.52990198 39:2.0820906 40:0.74807709 41:0.10239747 42:−1.1050204 43: −0.53352898 44:0.79966813 45:−1.5530518 46:−1.0456312 47:0.0035056134 48:−0.96574444 49:1.1126325 50:−0.064588472 51:−0.55075049 52:0.9495334 53:−0.32114556 54:0.42454228 55:0.18516833 56:−0.18974295 57:−0.049605269 58:0.17790461 59:−0.38122171 60:0.46975023 61:0.2750861 62:−0.81585729 63:0.034077615 64:0.58590645 65:−0.85271186 66:−0.40590015 67:0.8237015 68:−1.0428532 69:−1.5778298 70:0.83420289 71:0.1530309 72:−0.019400565 73: −0.35515225 74:0.97543013 75:0.45758843 76:−0.66852099 77:0.23889022 78:−0.48623368 79:0.5784654 80:−0.0082634836 81:0.18652764 82:−0.058095567 83:−0.15391538 84:−0.6177271 85:0.99040502 86:0.12622501 87:0.067504495 88:−0.35967568 89:0.29403573 90:0.78033966 91:0.076892845 92:0.82474387 93:−0.27701139 94:0.83341122 95:−0.98628277 96:−0.25490871 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124: −0.0045571304 125:−0.0020117455 126:−0.0092068724 127:−0.0077256206 128:−0.00070437411 129:0.0012516935 130:0.00055489031 131:0.0013429716 132:0.00036176579 133: −0.0026087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372

APPENDIX C2-continued

| SVM ModelWeights (340; Benign/Malignant) |
|---|
| 210:–0.0028663045 211:–0.0012186989 212:–0.00063428417 213:0.0051512984 214:0.00089924945 215:–0.00035291715 216:–0.0026578247 217:–0.031516869 218: –0.018453332 219:–0.012905908 220:–0.015366459 221:–0.013814257 222:–0.007569442 223: –0.0047048843 224:0.00062012818 225:0.0014852113 226:–0.019181944 227:–0.005778844 228: –0.0022216991 229:–0.0013164993 230:–0.011913291 231:–0.0048886021 232:–0.0050922348 233:–0.00091115123 234:–0.0028072072 235:–0.0020788321 236:–0.0069042598 237: –0.092131011 238:–0.068610474 239:–0.0047269738 240:–0.0084348312 241:–0.0050073303 242: –0.003040591 243:–0.0038143608 244:–0.040638726 245:–0.02857391 246:–0.0472783 247: –0.020520929 248:–0.0018310277 249:–0.0055512898 250:–0.0060781906 251:–0.0072731995 252:–0.006453387 253:–0.0049183252 254:–0.014674404 255:–0.026012832 256:–0.021858063 257:–0.021156041 258:–0.0072407476 259:–0.0034868279 260:–0.0014243352 261:–0.0010014101 262:–0.0013208789 263:–0.0028763453 264:–0.0076750983 265:–0.0046692337 266: –0.0012726086 267:–0.0068167564 268:–0.04353733 269:–0.046706751 270:–0.010794718 271: –0.0024784503 272:–0.0059213047 273–:0.016445309 274:–0.016014025 275:–0.0077815265 276: –0.0023459131 277:–0.040564284 278:–0.032950211 279:–0.017959842 280:–0.0040876623 281: –0.026083954 282:–0.022933906 283:–0.0027156388 284:–0.035015725 285:–0.029552883 286: –0.010026687 287:–0.011907991 288:0.0022531124 289:–0.002897898 290:–0.00044569091 291:0.00010489624 292:–0.00053147622 293:–0.00073173334 294:–0.000621646 295: –0.00016437711 296:–0.00049518317 297:0.00021529767 298:0.00052096118 299:–4.636059e–005 300:–0.0021831172 301:–0.0014980205 302:–0.00038898826 303:0.00068646355 304:0.0026823219 305:–0.0040565808 306:–0.0020829935 307:0.0013752591 308: –0.00034383399 309:2.7236187e–005 310:–0.00070534449 311:–0.0012802118 312:–0.0030920727 313:–0.00088650011 314:–0.00014303472 315:0.00071791362 316:0.00019783134 317:2.9171604e–006 318:0.00037660156 319:0.0011750009 320:–0.0016896301 321: –0.0015126425 322:–0.00083564757 323:0.0010692998 324:–0.0016934061 325:–0.00029338882 326:–0.0034646564 327:–7.9289544e–005 328:0.0023930578 329:0.00048041579 330:0.00021849622 331:4.0310828e–005 332:–0.0032790094 333:–0.00015884312 334: –0.00031949134 335:3.3427419e–005 336:0.00084852462 337:0.00044620238 338:–0.0032407208 339:0.00048842531 340:0.00094149791 # |
| 0.001162764277538797 1:–6.6617446 2:2.1398783 3:4.6612291 4:4.1200266 5:–9.3816519 6: –0.51241511 7:1.9775529 8:–2.3050761 9:0.16089861 10:2.2131913 11:–1.6792704 12:3.1526086 13:0.84659821 14:–2.3553936 15:2.7890522 16:1.8426282 17:0.29614833 18:0.99678963 19:1.0124475 20:–0.8951236 21:–0.28949109 22:–2.5569632 23:1.5312668 24:–1.8644742 25:0.57216853 26:0.16517471 27:0.74864984 28:0.27347502 29:–0.47111201 30:–0.25048435 31: –1.4497271 32:–1.4426607 33:–0.011552157 34:–1.0720286 35:–1.815498 36:1.3534091 37: –0.46674749 38:–0.952268 39:1.464447 40:–0.074659206 41:0.48858941 42:0.57241172 43: –0.52673846 44:0.54606819 45:–0.59332341 46:0.2707729 47:0.54184961 48:–1.816597 49: –0.69199657 50:0.63413811 51:1.6984042 52:–1.0161058 53:–0.38531092 54:1.0689594 55:1.4721197 56:–0.043617524 57:–1.307793 58:0.55282313 59:0.2953912 60:–0.90128732 61: –1.319623 62:0.10041022 63:–1.1754335 64:–0.082541145 65:–0.88779491 66:1.0713943 67: –0.0046418332 68:1.8259735 69:–0.039097067 70:–0.065624237 71:0.047109779 72:–0.49761131 73:0.37601602 74:–0.94081354 75:0.215638 76:–0.17871481 77:–0.26326942 78:0.53398281 79: –0.62913889 80:0.27845526 81:1.0219557 82:0.40206265 83:–0.15983522 84:0.28322443 85:0.080510534 86:–0.60540879 87:–0.090221278 88:0.21645001 89:–0.066882223 90: –0.0013322314 91:–0.50253069 92:0.27706829 93:–0.04270146 94:0.27069563 95:–0.21266104 96: –0.44723687 97:0.0039280006 98:0.010595871 99:–0.0072948104 100:0.0007581744 101:0.0015444086 102:0.00086657552 103:0.0014506713 104:0.00027309253 105: –0.0003779236 106:–0.0033040401 107:–0.002894687 108:0.0012058502 109:0.0026374348 110: –0.0018928888 111:–0.0024273857 112:–0.0003231481 113:0.00057429477 114:–0.00070962519 115:0.0011349921 116:–0.0046544136 117:6.0590241e–007 118:0.00074805523 119: –0.0025794252 120:0.00037352511 121:–0.0022889439 122:0.0011132049 123:–0.0024242986 124:–0.0045571304 125:–0.0020117455 126:–0.0092068724 127:–0.0077256206 128: –0.00070437411 129:0.0012516935 130:0.00055489031 131:0.0013429716 132:0.00036176579 133:–0.0026087298 134:5.3104148e–005 135:–0.001098063 136:0.0010348612 137: –0.00068726367 138:–0.00074436213 139:0.0027458151 140:0.0010222673 141:–0.0018521026 142:–0.00061301264 143:–0.001804522 144:–0.00021584153 145:0.0015449577 146: –0.0015697054 147:–0.00097707158 148:–0.0011295594 149:0.0028935266 150:–0.00053708232 151:0.0018405041 152:–0.002562111 153:–0.0013092471 154:–0.00046263589 155: –0.0035724007 156:–0.0011358063 157:–0.0012884629 158:–0.0031973415 159:0.00045693576 160:–0.0012730506 161:0.0014123393 162:0.003461167 163:–0.0029414443 164:–0.00037983558 165:–0.0023911442 166:0.0021477563 167:9.2110975e–005 168:–0.0026100944 169: –0.0034047128 170:–0.0029387963 171:–0.0023030045 172:–0.0054465104 173:–0.0021478815 174:–0.0022738085 175:0.00050098688 176:–0.0021780876 177:2.5619611e–005 178: –0.0010297548 179:0.000299401 180:0.0002858036 181:0.0015720503 182:0.0012860922 , 183:0.0015920103 184:0.0034542123 185:–0.0054590856 186:–0.0013231005 187: –0.00026378682 188:–5.6713336e–005 189:0.0016455925 190:0.00055903167 191:0.00040327062 192:–0.00066433422 193:–0.0014816546 194:0.0016943325 195:0.00012320606 196:0.0006577372 197:0.00056744454 198:–0.0023361598 199:0.0042997436 200:–0.0016990597 201:0.0030764227 202:–0.0027063258 203:0.00046884044 204:–0.00031649071 205:0.00065622263 206:–0.0026635081 207:–0.0039158296 208:0.0020220254 209:0.0012250372 210:–0.0028663045 211:–0.0012186989 212:–0.00063428417 213:0.0051512984 214:0.00089924945 215:–0.00035291715 216:–0.0026578247 217:–0.031516869 218: –0.018453332 219:–0.012905908 220:–0.015366459 221:–0.013814257 222:–0.007569442 223: –0.0047048843 224:0.00062012818 225:0.0014852113 226:–0.019181944 227:–0.005778844 228: –0.0022216991 229:–0.0013164993 230:–0.011913291 231:–0.0048886021 232:–0.0050922348 233:–0.00091115123 234:–0.0028072072 235:–0.0020788321 236:–0.0069042598 237: –0.092131011 238:–0.068610474 239:–0.0047269738 240:–0.0084348312 241:–0.0050073303 242: |

APPENDIX C2-continued

SVM ModelWeights
(340; Benign/Malignant)

−0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:0.0022531124 289:0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302−:0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
0.0016230441128773699 1:−1.4225143 2:−3.3811448 3:−1.3460624 4:−2.4572864 5:−1.2485046 6:1.5272132 7:3.8467693 8:3.6000576 9:−2.5641577 10:−0.67970216 11:−1.2237694 12: −0.66455346 13:−1.7749182 14:1.801129 15:−0.073441938 16:−1.0443138 17:2.9320962 18: −0.62133968 19:0.24629931 20:−2.5408921 21:−1.9696916 22:−0.15611142 23:−0.55407423 24:017331484 25:−2.6666267 26:0.11005254 27:−0.76523972 28:0.82345724 29:2.1196442 30: −0.10236285 31:1.7822025 32:−0.34777778 33:−2.6759152 34:0.95936936 35:−0.20149407 36: −0.27700329 37:1.0371037 38:−0.35205483 39:−1.3395022 40:−1.517821 41:−1.6165372 42:1.5603799 43:−0.14268057 44:1.0620614 45:−0.2145381 46:0.025638459 47:−0.10914129 48: −0.17478488 49:0.4742581 50:−0.48568475 51:−0.023864167 52:0.11586545 53:−0.062558644 54:0.021825971 55:0.30173782 56:−0.29385743 57:−0.56683713 58:0.94771284 59:0.29573876 60:0.014790609 61:−0.34971812 62:−0.33196506 63:−0.87879521 64:0.40384069 65:0.058484275 66:−0.13888034 67:0.19267932 68:0.83802092 69:−0.60410917 70:0.38784978 71:−0.045576707 72:−0.18632713 73:−0.15257339 74:0.1837924 75:0.1415422 76:0.25753227 77:0.00010349972 78:−0.44107446 79:0.05193444 80:0.12665264 81:−0.25195363 82:−0.21478599 83:−0.11333102 84:0.080544256 85:−0.26152048 86:−0.025861861 87:0.1800579 88:0.13319503 89:−0.0088331206 90:−0.020957014 91:0.16615254 92:−0.032219119 93:−0.030672744 94:0.15073164 95:0.074428804 96:−0.020996239 97:0.0039280006 98:0.010595871 99:−0.0072948104 100:0.0007581744 101:0.0015444086 102:0.00086657552 103:0.0014506713 104:0.00027309253 105:−0.0003779236 106:−0.0033040401 107:−0.002894687 108:0.0012058502 109:0.0026374348 110:−0.0018928888 111:−0.0024273857 112:−0.0003231481 113:0.00057429477 114: −0.00070962519 115:0.0011349921 116:−0.0046544136 117:6.0590241e−007 118:0.00074805523 119:−0.0025794252 120:0.00037352511 121:−0.0022889439 122:0.0011132049 123: −0.0024242986 124:−0.0045571304 125:−0.0020117455 126:−0.0092068724 127:−0.0077256206 128:−0.00070437411 129:0.0012516935 130:0.00055489031 131:0.0013429716 132:0.00036176579 133:−0.0026087298 134:5.3104148e−005 135:−0.001098063 136:0.0010348612 137:−0.00068726367 138:−0.00074436213 139:0.0027458151 140:0.0010222673 141:−0.0018521026 142:−0.00061301264 143:−0.001804522 144: −0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155:−0.0035724007 156:0.0011358063 157:−0.0012884629 158: −0.0031973415 159:0.00045693576 160:−0.0012730506 161:0.0014123393 162:0.003461167 163: −0.0029414443 164:−0.00037983558 165:−0.0023911442 166:0.0021477563 167:9.2110975e−005 168:−0.0026100944 169:−0.0034047128 170:−0.0029387963 171:−0.0023030045 172: −0.0054465104 173:−0.0021478815 174:−0.0022738085 175:0.00050098688 176:−0.0021780876 177:2.5619611e−005 178:−0.0010297548 179:0.000299401 180:0.0002858036 181:0.0015720503 182:0.0012860922 183:0.0015920103 184:0.0034542123 185:−0.0054590856 186:−0.0013231005 187:−0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212: −0.00063428417 213:0.0051512984 214:0.00089924945 215:−0.00035291715 216:−0.0026578247 217:−0.031516869 218:−0.018453332 219:−0.012905908 220:−0.015366459 221:−0.013814257 222:−0.007569442 223:−0.0047048843 224:0.00062012818 225:0.0014852113 226:−0.019181944 227:−0.005778844 228:−0.0022216991 229:−0.0013164993 230:−0.011913291 231:−0.0048886021 232:−0.0050922348 233:−0.00091115123 234:−0.0028072072 235:−0.0020788321 236: −0.0069042598 237:−0.092131011 238:−0.068610474 239:−0.0047269738 240:−0.0084348312 241: −0.0050073303 242:−0.003040591 243:−0.0038143608 244:−0.040638726 245:−0.02857391 246: −0.0472783 247:−0.020520929 248:−0.0018310277 249:−0.0055512898 250:−0.0060781906 251: −0.0072731995 252:−0.006453387 253:−0.0049183252 254:−0.014674404 255:−0.026012832 256: −0.021858063 257:−0.021156041 258:−0.0072407476 259:−0.0034868279 260:−0.0014243352 261: −0.0010014101 262:−0.0013208789 263:−0.0028763453 264:−0.0076750983 265:−0.0046692337 266:−0.0012726086 267:−0.0068167564 268:−0.04353733 269:−0.046706751 270:−0.010794718 271:−0.0024784503 272:−0.0059213047 273:−0.016445309 274:−0.016014025 275:−0.0077815265

APPENDIX C2-continued

SVM ModelWeights
(340; Benign/Malignant)

276:−0.0023459131 277:−0.040564284 278:−0.032950211 279:−0.017959842 280:−0.0040876623
281:−0.026083954 282:−0.022933906 283:−0.0027156388 284:−0.035015725 285:−0.029552883
286:−0.010026687 287:−0.011907991 288:0.0022531124 289:−0.002897898 290:−0.00044569091
291:0.00010489624 292:−0.00053147622 293:−0.00073173334 294:−0.000621646 295:
−0.00016437711 296:−0.00049518317 297:0.00021529767 298:0.00052096118 299:−4.636059e−005
300:−0.0021831172 301:−0.0014980205 302:−0.00038898826 303:0.00068646355
304:0.0026823219 305:−0.0040565808 306:−0.0020829935 307:−0.0013752591 308:
−0.00034383399 309:2.7236187e−005 310:−0.00070534449 311:−0.0012802118 312:−0.0030920727
313:−0.00088650011 314:−0.00014303472 315:0.00071791362 316:0.00019783134
317:2.9171604e−006 318:0.00037660156 319:0.0011750009 320:−0.0016896301 321:
−0.0015126425 322:−0.00083564757 323:0.0010692998 324:−0.0016934061 325:−0.00029338882
326:−0.0034646564 327:−7.9289544e−005 328:0.0023930578 329:0.00048041579
330:0.00021849622 331:4.0310828e−005 332:−0.0032790094 333:−0.00015884312 334:
−0.00031949134 335:3.3427419e−005 336:0.00084852462 337:0.00044620238 338:−0.0032407208
339:0.00048842531 340:0.00094149791 #
−0.0019305885786775911 1:−0.27885634 2:9.8825912 3:5.0959301 4:11.570415 5:−1.236788
6:1.985296 7:5.2343593 8:0.62978274 9:2.3628919 10:−4.0060329 11:−1.5498919 12:−5.6165047
13:1.9572977 14:1.525573 15:−1.4694535 16:−0.72089523 17:6.3752151 18:−3.8398392 19:
−0.22521774 20:2.0210238 21:−2.0194118 22:−0.11568941 23:−2.104739 24:1.9838831
25:3.0514641 26:0.59763795 27:1.0259111 28:0.36511812 29:−1.4264234 30:0.1027429
31:2.357899 32:−1.9932759 33:0.25746295 34:−1.3807032 35:−0.80859441 36:−1.3570629 37:
−0.43601882 38:1.2783484 39:0.33894697 40:−0.14031106 41:0.36673552 42:0.78659517
43:2.2073028 44:−1.7938133 45:−3.3127129 46:0.55814505 47:0.23499101 48:−0.31328574 49:
−0.3678259 50:−1.0919495 51:−0.54220551 52:−0.10577908 53:0.056796744 54:−1.0248491
55:0.364755 56:−0.1218835 57:−0.37480712 58:0.69237989 59:−0.72456926 60:0.11871188 61:
−0.29808462 62:−0.33266142 63:0.51533318 64:−0.40029058 65:−0.54870594 66:0.74644834 67:
−0.043202028 68:−0.4499062 69:0.57941437 70:−0.13789555 71:0.21616811 72:0.22102049 73:
−0.23642012 74:−0.23389414 75:−0.18306223 76:−0.10923698 77:0.082572661 78:−0.31490263 79:
−0.28321487 80:0.21753868 81:0.26736733 82:−0.25724804 83:0.3210631 84:0.074870519
85:0.12955892 86:0.14472702 87:0.19907668 88:−0.26064119 89:0.10771916 90:0.18520375
91:0.070189074 92:0.11561537 93:−0.081808254 94:−0.060622647 95:0.29384622 96:−0.32301018
97:0.0039280006 98:0.010595871 99:−0.0072948104 100:0.0007581744 101:0.0015444086
102:0.00086657552 103:0.0014506713 104:0.00027309253 105:−0.0003779236 106:
−0.0033040401 107:−0.002894687 108:0.0012058502 109:0.0026374348 110:−0.0018928888 111:
−0.0024273857 112:−0.0003231481 113:0.00057429477 114:−0.00070962519 115:0.0011349921
116:−0.0046544136 117:6.0590241e−007 118:0.00074805523 119:−0.0025794252
120:0.00037352511 121:−0.0022889439 122:0.0011132049 123:−0.0024242986 124:
−0.0045571304 125:−0.0020117455 126:−0.0092068724 127:−0.0077256206 128:−0.00070437411
129:0.0012516935 130:0.00055489031 131:0.0013429716 132:0.00036176579 133:
−0.0026087298 134:5.3104148e−005 135:−0.001098063 136:0.0010348612 137:−0.00068726367
138:−0.00074436213 139:0.0027458151 140:0.0010222673 141:−0.0018521026 142:
−0.00061301264 143:−0.001804522 144:−0.00021584153 145:0.0015449577 146:−0.0015697054
147:−0.00097707158 148:−0.0011295594 149:0.0028935266 150:−0.00053708232
151:0.0018405041 152:−0.002562111 153:−0.0013092471 154:−0.00046263589 155:
−0.0035724007 156:−0.0011358063 157:−0.0012884629 158:−0.0031973415 159:0.00045693576
160:−0.0012730506 161:0.0014123393 162:0.003461167 163:−0.0029414443 164:−0.00037983558
165:−0.0023911442 166:0.0021477563 167:9.2110975e−005 168:−0.0026100944 169:
−0.0034047128 170:−0.0029387963 171:−0.0023030045 172:−0.0054465104 173:−0.0021478815
174:−0.0022738085 175:0.00050098688 176:−0.0021780876 177:2.5619611e−005 178:
−0.0010297548 179:0.000299401 180:0.0002858036 181:0.0015720503 182:0.0012860922
183:0.0015920103 184:0.0034542123 185:−0.0054590856 186:−0.0013231005 187:
−0.00026378682 188:−5.6713336e−005 189:0.0016455925 190:0.00055903167 191:0.00040327062
192:−0.00066433422 193:−0.0014816546 194:0.0016943325 195:0.00012320606
196:0.0006577372 197:0.00056744454 198:−0.0023361598 199:0.0042997436 200:−0.0016990597
201:0.0030764227 202:−0.0027063258 203:0.00046884044 204:−0.00031649071
205:0.00065622263 206:−0.0026635081 207:−0.0039158296 208:0.0020220254 209:0.0012250372
210:−0.0028663045 211:−0.0012186989 212:−0.00063428417 213:0.0051512984
214:0.00089924945 215:−0.00035291715 216:−0.0026578247 217:−0.031516869 218:
−0.018453332 219:−0.012905908 220:−0.015366459 221:−0.013814257 222:−0.007569442 223:
−0.0047048843 224:0.00062012818 225:0.0014852113 226:−0.019181944 227:−0.005778844 228:
−0.0022216991 229:−0.0013164993 230:−0.011913291 231:−0.0048886021 232:−0.0050922348
233:−0.00091115123 234:−0.0028072072 235:−0.0020788321 236:−0.0069042598 237:
−0.092131011 238:−0.068610474 239:−0.0047269738 240:−0.0084348312 241:−0.0050073303 242:
−0.003040591 243:−0.0038143608 244:−0.040638726 245:−0.02857391 246:−0.0472783 247:
−0.020520929 248:−0.0018310277 249:−0.0055512898 250:−0.0060781906 251:−0.0072731995
252:−0.006453387 253:−0.0049183252 254:−0.014674404 255:−0.026012832 256:−0.021858063
257:−0.021156041 258:−0.0072407476 259:−0.0034868279 260:−0.0014243352 261:−0.0010014101
262:−0.0013208789 263:−0.0028763453 264:−0.0076750983 265:−0.0046692337 266:
−0.0012726086 267:−0.0068167564 268:−0.04353733 269:−0.046706751 270:−0.010794718 271:
−0.0024784503 272:−0.0059213047 273:−0.016445309 274:−0.016014025 275:−0.0077815265 276:
−0.0023459131 277:−0.040564284 278:−0.032950211 279:−0.017959842 280:−0.0040876623 281:
−0.026083954 282:−0.022933906 283:−0.0027156388 284:−0.035015725 285:−0.029552883 286:
−0.010026687 287:−0.011907991 288:0.0022531124 289:−0.002897898 290:−0.00044569091
291:0.00010489624 292:−0.00053147622 293:−0.00073173334 294:−0.000621646 295:
−0.00016437711 296:−0.00049518317 297:0.00021529767 298:0.00052096118 299:−4.636059e−005
300:−0.0021831172 301:−0.0014980205 302:−0.00038898826 303:0.00068646355
304:0.0026823219 305:−0.0040565808 306:−0.0020829935 307:−0.0013752591 308:

APPENDIX C2-continued

SVM ModelWeights
(340; Benign/Malignant)

−0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
−0.0019243722565294337 1:0.43924162 2:11.232109 3:−3.9407368 4:−2.2011461 5:−11.28683 6:11.626836 7:−2.2610507 8:1.9518424 9:−9.4666557 10:−3.7131739 11:10.517995 12:−6.7265964 13:−4.0587149 14:6.8698277 15:6.0822682 16:−1.0870117 17:1.8049608 18:−3.1073513 19: −2.3271327 20:1.4725494 21:3.9342456 22:1.8926948 23:3.0023232 24:0.81837815 25: −0.33446386 26:0.58317035 27:−0.11714862 28:−0.81818438 29:−0.47216067 30:−0.54521555 31: −2.5090654 32:−0.71020037 33:−0.075489208 34:−0.15132225 35:0.75384641 36:0.67422163 37: −0.83866471 38:0.21326746 39:0.2087258 40:−0.65981603 41:0.031596351 42:−0.67660743 43: −0.17599575 44:0.40585941 45:0.66532815 46:−0.32825023 47:0.21217279 48:−0.21592824 49:0.049525786 50:0.23724128 51:0.015045444 52:0.42865586 53:0.066027313 54:−0.063017264 55:0.014561494 56:0.30450827 57:−0.55682224 58:0.034693249 59:−0.099208049 60: −0.030663054 61:0.25848621 62:−0.17410555 63:0.31677112 64:0.37713161 65:0.081454352 66: −0.13391829 67:0.060628474 68:0.0038285842 69:0.083007328 70:0.072671026 71:0.18354052 72:−0.029333215 73:0.14277005 74:−0.0031624066 75:−0.28545249 76:−0.04553153 77:0.2340052 78:0.10836186 79:−0.26486248 80:0.1415502 81:0.034146793 82:0.019663593 83:−0.11012109 84:0.042360976 85:0.053964235 86:0.012122418 87:0.02180534 88:0.041960888 89:−0.02017046 90:0.010602157 91:−0.048801117 92:0.039203722 93:0.055861782 94:−0.069935106 95: −0.067185134 96:0.059299849 97:0.0039280006 98:0.010595871 99:−0.0072948104 100:0.0007581744 101:0.0015444086 102:0.00086657552 103:0.0014506713 104:0.00027309253 105:−0.0003779236 106:−0.0033040401 107:−0.002894687 108:0.0012058502 109:0.0026374348 110:−0.0018928888 111:−0.0024273857 112:−0.0003231481 113:0.00057429477 114: −0.00070962519 115:0.0011349921 116:−0.0046544136 117:6.0590236e−007 118:0.00074805523 119:−0.0025794252 120:0.00037352511 121:−0.0022889439 122:0.0011132049 123: −0.0024242986 124:−0.0045571304 125:−0.0020117455 126:−0.0092068724 127:−0.0077256206 128:−0.00070437411 129:0.0012516935 130:0.00055489031 131:0.0013429716 132:0.00036176579 133:−0.0026087298 134:5.3104148e−005 135:−0.001098063 136:0.0010348612 137:−0.00068726367 138:−0.00074436213 139:0.0027458151 140:0.0010222673 141:−0.0018521026 142:−0.00061301264 143:−0.001804522 144: −0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155:−0.0035724007 156:0.0011358063 157:−0.0012884629 158: −0.0031973415 159:0.00045693576 160:−0.0012730506 161:0.0014123393 162:0.003461167 163: −0.0029414443 164:−0.00037983558 165:−0.0023911442 166:0.0021477563 167:9.2110975e−005 168:−0.0026100944 169:−0.0034047128 170:−0.0029387963 171:−0.0023030045 172: −0.0054465104 173:−0.0021478815 174:−0.0022738085 175:0.00050098688 176:−0.0021780876 177:2.5619611e−005 178:−0.0010297548 179:0.000299401 180:0.0002858036 181:0.0015720503 182:0.0012860922 183:0.0015920103 184:0.0034542123 185:−0.0054590856 186:−0.0013231005 187:−0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212: −0.00063428417 213:0.0051512984 214:0.00089924945 215:−0.00035291715 216:−0.0026578247 217:−0.031516869 218:−0.018453332 219:−0.012905908 220:−0.015366459 221:−0.013814257 222:−0.007569442 223:−0.0047048843 224:0.00062012818 225:0.0014852113 226:−0.019181944 227:−0.005778844 228:−0.0022216991 229:−0.0013164993 230:−0.011913291 231:−0.0048886021 232:−0.0050922348 233:−0.00091115123 234:−0.0028072072 235:−0.0020788321 236: −0.0069042598 237:−0.092131011 238:−0.068610474 239:−0.0047269738 240:−0.0084348312 241: −0.0050073303 242:−0.003040591 243:−0.0038143608 244:−0.040638726 245:−0.02857391 246: −0.0472783 247−:0.020520929 248:−0.0018310277 249:−0.0055512898 250:−0.0060781906 251: −0.0072731995 252:−0.006453387 253:−0.0049183252 254:−0.014674404 255:−0.026012832 256: −0.021858063 257:0.021156041 258:−0.0072407476 259:−0.0034868279 260:−0.0014243352 261: −0.0010014101 262:−0.0013208789 263:−0.0028763453 264:−0.0076750983 265:−0.0046692337 266:−0.0012726086 267:−0.0068167564 268:−0.04353733 269:−0.046706751 270:−0.010794718 271:−0.0024784503 272:−0.0059213047 273:−0.016445309 274:−0.016014025 275:−0.0077815265 276:−0.0023459131 277:−0.040564284 278:−0.032950211 279:−0.017959842 280:−0.0040876623 281:−0.026083954 282:−0.022933906 283:−0.0027156388 284:−0.035015725 285:−0.029552883 286:−0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208

APPENDIX C2-continued

SVM ModelWeights
(340; Benign/Malignant)

339:0.00048842531 340:0.00094149791 #
−0.0033153142499855108 1:4.2058864 2:−10.273238 3:0.86963367 4:0.76485717 5:0.58796382
6:6.4885211 7:−0.5382148 8:1.6879342 9:0.99313658 10:1.3948026 11:−0.040827319 12:−1.919044
13:−2.0231805 14:1.3912067 15:−0.651649 16:3.206111 17:1.5296158 18:1.1393459 19:
−0.41099066 20:−0.96875608 21:0.36818328 22:−0.98741603 23:1.1284338 24:−3.8232245
25:0.81427598 26:−0.40313891 27:−1.2148914 28:0.74097633 29:0.53082883 30:−1.3979726
31:2.3583498 32:1.422774 33:1.4029665 34:−1.1116167 35:−0.12920739 36:−1.2420616 37:
−0.28832686 38:−0.50600088 39:1.1798551 40:0.19203396 41:−0.64383477 42:−1.9600604 43:
−3.0673683 44:−1.7651753 45:−0.47080824 46:0.2957764 47:0.74461073 48:−1.0844226 49:
−1.805436 50:−0.79785281 51:0.92456198 52:1.1694111 53:1.044863 54:0.16566463 55:
−0.46273881 56:0.75328708 57:0.41227534 58:1.1220003 59:0.14123106 60:0.16303807
61:0.97278911 62:−1.6178106 63:−0.48137847 64:0.71833807 65:0.20115498 66:−0.058812018
67:0.086899623 68:−0.080147691 69:1.0477471 70:0.42553627 71:−0.27966115 72:0.43006679
73:−0.63558483 74:−0.64211845 75:0.61957252 76:−0.24969929 77:0.14041242 78:0.56654406
79:0.4596808 80:−0.087941766 81:−0.55924523 82:0.10006484 83:−0.11043978 84:−0.50888997
85:−0.21049897 86:−0.23463774 87:0.40061915 88:−0.45953149 89:0.015510526 90:−0.080896795
91:0.061849281 92:−0.70906591 93:0.057222754 94:0.23230948 95:0.49240923 96:−0.057280418
97:0.0039280006 98:0.010595871 99:−0.0072948104 100:0.0007581744 101:0.0015444086
102:0.00086657552 103:0.0014506713 104:0.00027309253 105:−0.0003779236 106:
−0.0033040401 107:−0.002894687 108:0.0012058502 109:0.0026374348 110:−0.0018928888 111:
−0.0024273857 112:−0.0003231481 113:0.00057429477 114:−0.00070962519 115:0.0011349921
116:−0.0046544136 117:6.0590241e−007 118:0.00074805523 119:−0.0025794252
120:0.00037352511 121:−0.0022889439 122:0.0011132049 123:−0.0024242986 124:
−0.0045571304 125:−0.0020117455 126:−0.0092068724 127:−0.0077256206 128:−0.00070437411
129:0.0012516935 130:0.00055489031 131:0.0013429716 132:0.00036176579 133:
−0.0026087298 134:5.3104148e−005 135:−0.001098063 136:0.0010348612 137:−0.00068726367
138:−0.00074436213 139:0.0027458151 140:0.0010222673 141:−0.0018521026 142:
−0.00061301264 143:−0.001804522 144:−0.00021584153 145:0.0015449577 146:−0.0015697054
147:−0.00097707158 148:−0.0011295594 149:0.0028935266 150:−0.00053708232
151:0.0018405041 152:−0.002562111 153:−0.0013092471 154:−0.00046263589 155:
−0.0035724007 156:0.0011358063 157:−0.0012884629 158:−0.0031973415 159:0.00045693576
160:−0.0012730506 161:0.0014123393 162:0.003461167 163:−0.0029414443 164:−0.00037983558
165:−0.0023911442 166:0.0021477563 167:9.2110975e−005 168:−0.0026100944 169:
−0.0034047128 170:−0.0029387963 171:−0.0023030045 172:−0.0054465104 173:−0.0021478815
174:−0.0022738085 175:0.00050098688 176:−0.0021780876 177:2.5619611e−005 178:
−0.0010297548 179:0.000299401 180:0.0002858036 181:0.0015720503 182:0.0012860922
183:0.0015920103 184:0.0034542123 185:−0.0054590856 186:−0.0013231005 187:
−0.00026378682 188:−5.6713336e−005 189:0.0016455925 190:0.00055903167 191:0.00040327062
192:−0.00066433422 193:−0.0014816546 194:0.0016943325 195:0.00012320606
196:0.0006577372 197:0.00056744454 198:−0.0023361598 199:0.0042997436 200:−0.0016990597
201:0.0030764227 202:−0.0027063258 203:0.00046884044 204:−0.00031649071
.205:0.00065622263 206:−0.0026635081 207:−0.0039158296 208:0.0020220254 209:0.0012250372
210:−0.0028663045 211:−0.0012186989 212:−0.00063428417 213:0.0051512984
214:0.00089924945 215:−0.00035291715 216:−0.0026578247 217:−0.031516869 218:
−0.018453332 219:−0.012905908 220:−0.015366459 221:−0.013814257 222:−0.007569442 223:
−0.0047048843 224:0.00062012818 225:0.0014852113 226:−0.019181944 227:−0.005778844 228:
−0.0022216991 229:−0.0013164993 230:−0.011913291 231:−0.0048886021 232:−0.0050922348
233:−0.00091115123 234:−0.0028072072 235:−0.0020788321 236:−0.0069042598 237:
−0.092131011 238:−0.068610474 239:−0.0047269738 240:−0.0084348312 241:−0.0050073303 242:
−0.003040591 243:−0.0038143608 244:−0.040638726 245:−0.02857391 246:−0.0472783 247:
−0.020520929 248:−0.0018310277 249:−0.0055512898 250:−0.0060781906 251:−0.0072731995
252:−0.006453387 253:−0.0049183252 254:−0.014674404 255:−0.026012832 256:−0.021858063
257:−0.021156041 258:−0.0072407476 259:−0.0034868279 260:−0.0014243352 261:−0.0010014101
262:−0.0013208789 263:−0.0028763453 264:−0.0076750983 265:−0.0046692337 266:
−0.0012726086 267:−0.0068167564 268:−0.04353733 269:−0.046706751 270:−0.010794718 271:
−0.0024784503 272:−0.0059213047 273:−0.016445309 274:−0.016014025 275:−0.0077815266 276:
−0.0023459131 277:−0.040564284 278:−0.032950211 279:−0.017959842 280:−0.0040876623 281:
−0.026083954 282:−0.022933906 283:−0.0027156388 284:−0.035015725 285:−0.029552883 286:
−0.010026687 287:−0.011907991 288:0.0022531124 289:−0.002897898 290:−0.00044569091
291:0.00010489624 292:−0.00053147622 293:−0.00073173334 294:−0.000621646 295:
−0.00016437711 296:−0.00049518317 297:0.00021529767 298:0.00052096118 299:−4.636059e−005
300:−0.0021831172 301:−0.0014980205 302:−0.00038898826 303:0.00068646355
304:0.0026823219 305:−0.0040565808 306:−0.0020829935 307:−0.0013752591 308:
−0.00034383399 309:2.7236187e−005 310:−0.00070534449 311:−0.0012802118 312:−0.0030920727
313:−0.00088650011 314:−0.00014303472 315:0.00071791362 316:0.00019783134
317:2.9171604e−006 318:0.00037660156 319:0.0011750009 320:−0.0016896301 321:
−0.0015126425 322:−0.00083564757 323:−0.0010692998 324:−0.0016934061 325:−0.00029338882
326:−0.0034646564 327:−7.9289544e−005 328:0.0023930578 329:0.00048041579
330:0.00021849622 331:4.0310828e−005 332:−0.0032790094 333:−0.00015884312 334:
−0.00031949134 335:3.3427419e−005 336:0.00084852462 337:0.00044620238 338:−0.0032407208
339:0.00048842531 340:0.00094149791 #
−0.0033153142499855108 1:−4.0771055 2:−1.1504505 3:2.7464559 4:−3.183337 5:2.1268644 6:
−3.9230978 7:0.34163719 8:2.0293679 9:−4.1811166 10:1.3721042 11:0.75773573 12:−2.5267835
13:0.18023184 14:1.253926 15:1.903635 16:4.277389 17:−1.0687795 18:2.2155018 19:−1.165033
20:0.49952036 21:−0.53572905 22:−2.7601488 23:0.46436167 24:−1.0921776 25:0.40821484 26:
−1.8236394 27:−0.6932615 28:−0.47530422 29:−1.0037123 30:−1.4111601 31:−0.97893435
32:0.59495652 33:−0.61701107 34:0.9906022 35:0.68052351 36:−0.63597757 37:−0.46423337 38:

APPENDIX C2-continued

| SVM ModelWeights (340; Benign/Malignant) |
|---|
| −0.89762545 39:0.13971765 40:−0.3625131 41:1.1963357 42:2.2367857 43:0.054969501 44: −0.94110113 45:−1.5583142 46:−0.44915068 47:−0.34900296 48:2.1110771 49:−0.28557867 50: −0.040807333 51:−0.40374312 52:−1.1042058 53:0.65662706 54:0.30161396 55:0.22354984 56: −0.87246823 57:−1.0906 58:−1.0315273 59:−0.56604338 60:0.19954501 61:−0.13208917 62: −0.10269781 63:−0.60582912 64:−0.43352944 65:−0.17152943 66:−0.55465734 67:1.6623362 68: −0.50636709 69:−0.233804 70:−0.50829476 71:0.15316477 72:0.020214388 73:0.51832306 74: −0.44554862 75:−0.4672696 76:1.2049603 77:−0.17821534 78:0.35580134 79:−0.073194116 80:0.50485861 81:−0.38585055 82:−0.44239968 83:0.056880467 84:−0.12791957 85:−0.73388392 86:−0.76353788 87:−0.59957105 88:−0.60963315 89:0.50289297 90:0.97014892 91:−0.60125482 92:−0.63076407 93:−0.05503669 94:−0.25775599 95:0.29309192 96:0.035216358 97:0.0039280006 98:0.010595871 99:−0.0072948104 100:0.0007581744 101:0.0015444086 102:0.00086657552 103:0.0014506713 104:0.00027309253 105:−0.0003779236 106:−0.0033040401 107:−0.002894687 108:0.0012058502 109:0.0026374348 110:−0.0018928888 111:−0.0024273857 112−:0.0003231481 113:0.00057429477 114:−0.00070962519 115:0.0011349921 116:−0.0046544136 117:6.0590241e-007 118:0.00074805523 119:−0.0025794252 120:0.00037352511 121:−0.0022889439 122:0.0011132049 123:−0.0024242986 124:−0.0045571304 125:−0.0020117455 126: −0.0092068724 127:−0.0077256206 128:−0.00070437411 129:0.0012516935 130:0.00055489031 131:0.0013429716 132:0.00036176579 133:−0.0026087298 134:5.3104148e−005 135: −0.001098063 136:0.0010348612 137:−0.00068726367 138:−0.00074436213 139:0.0027458151 140:0.0010222673 141:−0.0018521026 142:−0.00061301264 143:−0.001804522 144: −0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155:−0.0035724007 156:0.0011358063 157:−0.0012884629 158: −0.0031973415 159:0.00045693576 160:−0.0012730506 161:0.0014123393 162:0.003461167 163: 0.0029414443 164:−0.00037983558 165:−0.0023911442 166:0.0021477563 167:9.2110975e−005 168:−0.0026100944 169:−0.0034047128 170:−0.0029387963 171:−0.0023030045 172: −0.0054465104 173:−0.0021478815 174:−0.0022738085 175:0.00050098688 176:−0.0021780876 177:2.5619611e−005 178:−0.0010297548 179:0.000299401 180:0.0002858036 181:0.0015720503 182:0.0012860922 183:0.0015920103 184:0.0034542123 185:−0.0054590856 186:−0.0013231005 187:−0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212: −0.00063428417 213:0.0051512984 214:0.00089924945 215:−0.00035291715 216:−0.0026578247 217:−0.031516869 218:−0.018453332 219:−0.012905908 220:−0.015366459 221:−0.013814257 222:−0.007569442 223:−0.0047048843 224:0.00062012818 225:0.0014852113 226:−0.019181944 227:−0.005778844 228:−0.0022216991 229:−0.0013164993 230:−0.011913291 231:−0.0048886021 232:−0.0050922348 233:−0.00091115123 234:−0.0028072072 235:−0.0020788321 236: −0.0069042598 237:−0.092131011 238:−0.068610474 239:−0.0047269738 240:−0.0084348312 241: −0.0050073303 242:−0.003040591 243:−0.0038143608 244:−0.040638726 245:−0.02857391 246: −0.0472783 247:−0.020520929 248:−0.0018310277 249:−0.0055512898 250:−0.0060781906 251: −0.0072731995 252:−0.006453387 253:−0.0049183252 254:−0.014674404 255:−0.026012832 256: −0.021858063 257:−0.021156041 258:−0.0072407476 259:−0.0034868279 260:−0.0014243352 261: −0.0010014101 262:−0.0013208789 263:−0.0028763453 264:−0.0076750983 265:−0.0046692337 266:−0.0012726086 267:−0.0068167564 268:−0.04353733 269:−0.046706751 270:−0.010794718 271:−0.0024784503 272:−0.0059213047 273:−0.016445309 274:−0.016014025 275:−0.0077815265 276:−0.0023459131 277:−0.040564284 278:−0.032950211 279:−0.017959842 280:−0.0040876623 281:−0.026083954 282:−0.022933906 283:−0.0027156388 284:−0.035015725 285:−0.029552883 286:−0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:0.00083564757 323:0.0010692998 324:0.0016934061 325:0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # |
| −0.00096575758764302693 1:−2.6901774 2:0.12484454 3:−5.7668495 4:3.0192795 5:3.5229359 6:1.7700055 7:2.5609665 8:0.29128727 9:7.6276684 10:−8.8952122 11:−0.96227884 12:−1.0497365 13:−1.2142708 14:4.7062192 15:3.6511281 16:8.7197504 17:−5.4372635 18:−4.8534231 19:8.6003857 20:−2.3985815 21:3.356118 22:−0.72012883 23:−2.1830902 24:−0.51483166 25:0.088666141 26:−0.73958147 27:−0.082041442 28:−1.527185 29:−1.286461 30:−0.21008573 31: −0.20750855 32:0.99752599 33:−0.46010032 34:−0.93256456 35:−0.4783504 36:−0.16327481 37:1.1467155 38:0.089615069 39:−0.46824008 40:−0.29320472 41:0.11233055 42:0.067520261 43:−0.10295373 44:1.1885079 45:−0.0014238653 46:0.18009517 47:0.61626351 48:0.19040526 49:0.29867285 50:0.19637226 51:0.32745302 52:−0.459636 53:−0.26479769 54:0.14241518 55:0.33911103 56:−0.24151367 57:0.49422511 58:0.28986484 59:0.25873479 60:0.34820062 61: −0.20878318 62:0.033185318 63:0.22426644 64:−0.28322926 65:0.068976313 66:0.056422386 67:0.21299103 68:−0.028575726 69:0.1761578 70:0.16310479 71:−0.011603817 72:0.20116013 73:−0.18685398 74:0.38147083 75:−0.13860913 76:0.021649625 77:−0.061052207 78:−0.29507366 79:0.30973631 80:0.18700933 81:0.21704787 82:−0.081009842 83:−0.058521919 84:−0.11607506 |

APPENDIX C2-continued

| SVM ModelWeights (340; Benign/Malignant) |
|---|
| 85:−0.18982829 86:−0.028044887 87:0.10236598 88:0.3133322 89:0.18735105 90:−0.088616364 91:−0.00029514689 92:0.023634661 93:−0.056740329 94:−0.032674894 95:0.063991047 96:0.046832096 97:0.0039280006 98:0.010595871 99:−0.0072948104 100:0.0007581744 101:0.0015444086 102:0.00086657552 103:0.0014506713 104:0.00027309253 105: −0.0003779236 106:−0.0033040401 107:−0.002894687 108:0.0012058502 109:0.0026374348 110: −0.0018928888 111:−0.0024273857 112:−0.0003231481 113:0.00057429477 114:−0.00070962519 115:0.0011349921 116:−0.0046544136 117:6.0590241e−007 118:0.00074805523 119: −0.0025794252 120:0.00037352511 121:−0.0022889439 122:0.0011132049 123:−0.0024242986 124:−0.0045571304 125:−0.0020117455 126:−0.0092068724 127:−0.0077256206 128: −0.00070437411 129:0.0012516935 130:0.00055489031 131:0.0013429716 132:0.00036176579 133:−0.0026087298 134:5.3104148e−005 135:−0.001098063 136:0.0010348612 137: −0.00068726367 138:−0.00074436213 139:0.0027458151 140:0.0010222673 141:−0.0018521026 142:−0.00061301264 143:−0.001804522 144:−0.00021584153 145:0.0015449577 146: −0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922, 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # |
| 0.0033153142499855108 1:7.9274554 2:4.6073709 3:1.4603447 4:2.0189972 5:0.78566617 6: −1.9227256 7:2.3366702 8:3.8609731 9:−1.7538786 10:−1.9488626 11:1.0148774 12:1.0113562 13:0.048932023 14:0.18989503 15:−2.6325822 16:−1.2078793 17:−0.14492357 18:2.2336729 19:1.5534426 20:0.35241047 21:0.80466956 22:1.8033856 23:−1.1963571 24:0.040374711 25:0.84861618 26:1.267494 27:−0.13946263 28:−1.7854359 29:−0.44070604 30:1.0542413 31: −1.2373537 32:1.3077921 33:0.041555852 34:−2.5827558 35:−0.43862686 36:−1.175679 37: −0.36042389 38:−0.17961439 39:−1.2788309 40:1.3294245 41:1.2669107 42:−2.5629046 43: −0.61600578 44:1.0869129 45:0.16643843 46:0.41818899 47:−0.63434148 48:1.260896 49: −1.4160058 50:−0.47209889 51:−0.61638838 52:0.43397504 53:−1.1642369 54:−1.3824058 55:0.054856647 56:−0.68154693 57:−1.2291157 58:1.1269206 59:0.42816728 60:−0.81057531 61: −0.35877511 62:−0.75165677 63:−0.63177156 64:0.20773476 65:0.13551633 66:−0.5237487 67: −0.51673758 68:0.30764231 69:−0.88030827 70:−0.46954823 71:−1.061381 72:−0.25684392 73: −0.044407751 74:−0.88750231 75:−0.013286038 76:1.4483461 77:−1.314014 78:−0.73927134 79: −0.64270085 80:−0.63794053 81:−0.60478133 82:−0.30900621 83:−0.12258168 84:−0.42564362 85: −0.26520431 86:−0.11208617 87:0.43734992 88:−0.28163466 89:−0.39385688 90:0.17103058 91:0.0020245016 92:0.35858369 93:0.29947466 94:−0.3636224 95:−0.3772828 96:0.036321074 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590241e−007 118:0.00074805523 119:−0.0025794252 |

APPENDIX C2-continued

SVM ModelWeights
(340; Benign/Malignant)

120:0.00037352511 121:−0.0022889439 122:0.0011132049 123:−0.0024242986 124: −0.0045571304 125:−0.0020117455 126:−0.0092068724 127:−0.0077256206 128:−0.00070437411 129:0.0012516935 130:0.00055489031 131:0.0013429716 132:0.00036176579 133: −0.0026087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
0.0033153142499855108 1:8.918601 2:−2.3055892 3:3.1710715 4:−0.15590623 5:4.4929414 6:8.9671669 7:3.5218017 8:−0.39461762 9:2.7775333 10:1.1787916 11:0.15996362 12:2.4074681 13:−3.6746743 14:0.4590081 15:−1.2401536 16:−0.21795638 17:−2.150651 18:1.5083847 19: −2.3201568 20:−1.4036152 21:1.2891895 22:1.8004652 23:−2.8867595 24:−0.48214114 25: −0.6927855 26:1.416193 27:0.6444248 28:−1.7029501 29:0.43822736 30:−0.49788377 31: −0.52655113 32:−1.7165399 33:−1.1928347 34:−0.22806802 35:0.57792765 36:−1.309574 37: −2.4833274 38:0.51614594 39:−1.1733458 40:0.19606277 41:−0.48785424 42:0.74374002 43:1.6714115 44:−1.012743 45:0.2366548 46:0.19854921 47:0.11224885 48:−0.12991515 49:0.75364155 50:1.8194386 51:0.83108264 52:−0.0015029972 53:1.4728006 54:0.20966282 55:0.92609775 56:−0.79182535 57:−0.32760841 58:−0.0991785 59:−1.0574496 60:0.37978888 61: −0.10320935 62:0.60087049 63:−0.052789245 64:0.46512586 65:0.98970068 66:1.4638492 67: −0.57553667 68:−0.0046812133 69:−0.0082963342 70:−0.15113865 71:−1.3569248 72:0.56353962 73:−0.0099311648 74:−0.091379911 75:0.49824885 76:0.06418056 77:0.8926155 78:0.67386544 79:0.96177387 80:−0.68476832 81:0.09199404 82:0.31347424 83:−0.13139787 84:−0.28070489 85:−0.36300245 86:−0.56763732 87:0.36510098 88:−0.10910114 89:0.47624874 90:0.35608,894 91:−0.29683739 92:0.36191809 93:0.56255788 94:−0.27379358 95:−0.32124305 96:−0.1674033 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124: −0.0045571304 125:−0.0020117455 126:−0.0092068724 127:−0.0077256206 128:−0.00070437411 129:0.0012516935 130:0.00055489031 131:0.0013429716 132:0.00036176579 133: −0.0026087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232

APPENDIX C2-continued

SVM ModelWeights
(340; Benign/Malignant)

151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
0.0033153142499855108 1:3.1450987 2:3.0755467 3:3.8123691 4:−5.2419996 5:3.5220785 6:2.7474384 7:3.2287869 8:−0.89663881 9:1.4479074 10:0.22962917 11:−0.68433446 12:0.67356664 13:−2.3352745 14:0.13635983 15:−1.3551366 16:−0.17511296 17:−0.53919446 18:0.34350392 19:−1.4785919 20:0.38314915 21:1.0084164 22:−0.74683142 23:−1.01981 24:0.92450368 25:0.048945725 26:2.4303942 27:1.9733022 28:−1.084133 29:2.4037261 30: −0.20327578 31:−0.21382751 32:0.38244691 33:−1.5787801 34:0.58106166 35:0.56194413 36: −1.0568376 37:−0.39388707 38:0.77245092 39:0.22725876 40:0.56400257 41:−0.71169043 42: −1.4364457 43:0.15108694 44:0.1501902 45:−1.2559881 46:−0.47359699 47:0.88458729 48: −1.0644742 49:−0.26796979 50:0.45492792 51:−0.35489604 52:−0.0036850711 53:0.67428136 54:0.18258713 55:0.66911966 56:0.85411978 57:1.4131602 58:−0.17310233 59:0.26988244 60:0.63591391 61:−1.492577 62:1.1587889 63:0.24478087 64:−0.0090595074 65:0.09246061 66: −0.010267213 67:0.0090993661 68:−0.34929219 69:0.63706648 70:0.64416522 71:0.43840125 72: −0.15390216 73:−0.22265123 74:0.4152877 75:−0.98270524 76:−0.076135524 77:−1.5789219 78:0.80812001 79:−1.4226592 80:0.69282353 81:−1.2014222 82:−0.40982008 83:−0.36414981 84: −0.32098812 85:−0.34560445 86:0.05994729 87:−0.19077258 88:0.18567137 89:−0.060702454 90: −0.55258489 91:−0.90128028 92:−0.32713971 93:−0.72972381 94:0.11568306 95:−0.33518696 96:0.11770641 97:0.0039280006 98:0.010595871 99:−0.0072948104 100:0.0007581744 101:0.0015444086 102:0.00086657552 103:0.0014506713 104:0.00027309253 105: −0.0003779236 106:−0.0033040401 107:−0.002894687 108:0.0012058502 109:0.0026374348 110: −0.0018928888 111:−0.0024273857 112:−0.0003231481 113:0.00057429477 114:−0.00070962519 115:0.0011349921 116:−0.0046544136 117:6.0590241e−007 118:0.00074805523 119: −0.0025794252 120:0.00037352511 121:−0.0022889439 122:0.0011132049 123:−0.0024242986 124:−0.0045571304 125:−0.0020117455 126:−0.0092068724 127:−0.0077256206 128: −0.00070437411 129:0.0012516935 130:0.00055489031 131:0.0013429716 132:0.00036176579 133:−0.0026087298 134:5.3104148e−005 135:−0.001098063 136:0.0010348612 137: −0.00068726367 138:−0.00074436213 139:0.0027458151 140:0.0010222673 141:−0.0018521026 142:−0.00061301264 143:−0.001804522 144:−0.00021584153 145:0.0015449577 146: −0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922

APPENDIX C2-continued

SVM ModelWeights
(340; Benign/Malignant)

183:0.0015920103 184:0.0034542123 185:−0.0054590856 186:−0.0013231005 187:
−0.00026378682 188:−5.6713336e−005 189:0.0016455925 190:0.00055903167 191:0.00040327062
192:−0.00066433422 193:−0.0014816546 194:0.0016943325 195:0.00012320606
196:0.0006577372 197:0.00056744454 198:−0.0023361598 199:0.0042997436 200:0.0016990597
201:0.0030764227 202:−0.0027063258 203:0.00046884044 204:−0.00031649071
205:0.00065622263 206:−0.0026635081 207:−0.0039158296 208:0.0020220254 209:0.0012250372
210:−0.0028663045 211:−0.0012186989 212:−0.00063428417 213:0.0051512984
214:0.00089924945 215:−0.00035291715 216:−0.0026578247 217:−0.031516869 218:
−0.018453332 219:−0.012905908 220:−0.015366459 221:−0.013814257 222:−0.007569442 223:
−0.0047048843 224:0.00062012818 225:0.0014852113 226:−0.019181944 227:−0.005778844 228:
−0.0022216991 229:−0.0013164993 230:−0.011913291 231:−0.0048886021 232:−0.0050922348
233:−0.00091115123 234:−0.0028072072 235:−0.0020788321 236:−0.0069042598 237:
−0.092131011 238:−0.068610474 239:−0.0047269738 240:−0.0084348312 241:−0.0050073303 242:
−0.003040591 243:−0.0038143608 244:−0.040638726 245:−0.02857391 246:−0.0472783 247:
−0.020520929 248:−0.0018310277 249:−0.0055512898 250:−0.0060781906 251:−0.0072731995
252:−0.006453387 253:−0.0049183252 254:−0.014674404 255:−0.026012832 256:−0.021858063
257:−0.021156041 258:−0.0072407476 259:−0.0034868279 260:−0.0014243352 261:−0.0010014101
262:−0.0013208789 263:−0.0028763453 264:−0.0076750983 265:−0.0046692337 266:
−0.0012726086 267:−0.0068167564 268:−0.04353733 269:−0.046706751 270:−0.010794718 271:
−0.0024784503 272:−0.0059213047 273:−0.016445309 274:−0.016014025 275:−0.0077815265 276:
−0.0023459131 277:−0.040564284 278:−0.032950211 279:−0.017959842 280:−0.0040876623 281:
−0.026083954 282:−0.022933906 283:−0.0027156388 284:−0.035015725 285:−0.029552883 286:
−0.010026687 287:−0.011907991 288:0.0022531124 289:−0.002897898 290:−0.00044569091
291:0.00010489624 292:−0.00053147622 293:−0.00073173334 294:−0.000621646 295:
−0.00016437711 296:−0.00049518317 297:0.00021529767 298:0.00052096118 299:−4.636059e−005
300:−0.0021831172 301:−0.0014980205 302:−0.00038898826 303:0.00068646355
304:0.0026823219 305:−0.0040565808 306:−0.0020829935 307:−0.0013752591 308:
−0.00034383399 309:2.7236187e−005 310:−0.00070534449 311:−0.0012802118 312:−0.0030920727
313:−0.00088650011 314:−0.00014303472 315:0.00071791362 316:0.00019783134
317:2.9171604e−006 318:0.00037660156 319:0.0011750009 320:−0.0016896301 321:
−0.0015126425 322:−0.00083564757 323:0.0010692998 324:−0.0016934061 325:−0.00029338882
326:−0.0034646564 327:−7.9289544e−005 328:0.0023930578 329:0.00048041579
330:0.00021849622 331:4.0310828e−005 332:−0.0032790094 333:−0.00015884312 334:
−0.00031949134 335:3.3427419e−005 336:0.00084852462 337:0.00044620238 338:−0.0032407208
339:0.00048842531 340:0.00094149791 #
0.0033153142499855108 1:1.6040151 2:0.24394807 3:−0.09684144 4:−2.4873862 5:1.2782253 6:
−3.957773 7:1.591818 8:5.2486348 9:−3.780654 10:0.71394485 11:0.55227733 12:2.4138548 13:
−0.35664403 14:0.24096936 15:0.61735266 16:−1.0579739 17:−0.3856262 18:0.43396828
19:0.52961248 20:−0.58919561 21:0.35186648 22:−0.27301615 23:−0.5683229 24:−0.66487145 25:
−0.83458596 26:−1.3270503 27:1.6758934 28:−0.087032422 29:0.037628613 30:0.15866874 31:
−1.4669696 32:0.069000371 33:−0.95354003 34:−0.042669386 35:−0.15571766 36:2.2095904
37:0.081673302 38:−0.59341264 39:0.79293787 40:−0.73346049 41:−0.10772487 42:0.011551697
43:−1.4501675 44:0.17495763 45:−0.097596668 46:1.0937287 47:−1.4059062 48:0.44559744
49:1.4810617 50:−0.18444139 51:−1.2559286 52:−1.2589086 53:−1.1882739 54:−0.43347055
55:0.94245815 56:0.26500198 57:1.3265449 58:0.17797512 59:−0.11993234 60:0.26297709
61:0.67024577 62:0.11923546 63:0.35726729 64:−0.64151269 65:−0.47890148 66:1.0967112 67:
−0.12874754 68:−0.9067179 69:0.91967088 70:0.95822871 71:−0.20772138 72:1.1771448
73:0.3509993 74:−0.51153505 75:1.0094274 76:−0.8650856 77:0.41146982 78:0.15137386 79:
−0.95347089 80:0.16219261 81:−0.45549694 82:−0.73642898 83:−0.00017498361 84:−0.47792503
85:−0.35363454 86:−0.0076037394 87:0.39873832 88:−0.13728669 89:−0.64319247
90:0.036472682 91:0.28540239 92:−0.0080603445 93:0.24347825 94:−0.71214676 95:0.24580777
96:−1.1087687 97:0.0039280006 98:0.010595871 99:−0.0072948104 100:0.0007581744
101:0.0015444086 102:0.00086657552 103:0.0014506713 104:0.00027309253 105:
−0.0003779236 106:−0.0033040401 107:−0.002894687 108:0.0012058502 109:0.0026374348 110:
−0.0018928888 111:−0.0024273857 112:−0.0003231481 113:0.00057429477 114:−0.00070962519
115:0.0011349921 116:−0.0046544136 117:6.0590241e−007 118:0.00074805523 119:
−0.0025794252 120:0.00037352511 121:−0.0022889439 122:0.0011132049 123:−0.0024242986
124:−0.0045571304 125:−0.0020117455 126:−0.0092068724 127:−0.0077256206 128:
−0.00070437411 129:0.0012516935 130:0.00055489031 131:0.0013429716 132:0.00036176579
133:−0.0026087298 134:5.3104148e−005 135:−0.001098063 136:0.0010348612 137:
−0.00068726367 138:−0.00074436213 139:0.0027458151 140:0.0010222673 141:−0.0018521026
142:−0.00061301264 143:−0.001804522 144:−0.00021584153 145:0.0015449577 146:
−0.0015697054 147:−0.00097707158 148:−0.0011295594 149:0.0028935266 150:−0.00053708232
151:0.0018405041 152:−0.002562111 153:−0.0013092471 154:−0.00046263589 155:
−0.0035724007 156:0.0011358063 157:−0.0012884629 158:−0.0031973415 159:0.00045693576
160:−0.0012730506 161:0.0014123393 162:0.003461167 163:−0.0029414443 164:−0.00037983558
165:−0.0023911442 166:0.0021477563 167:9.2110975e−005 168:−0.0026100944 169:
−0.0034047128 170:−0.0029387963 171:−0.0023030045 172:−0.0054465104 173:−0.0021478815
174:−0.0022738085 175:0.00050098688 176:−0.0021780876 177:2.5619611e−005 178:
−0.0010297548 179:0.000299401 180:0.0002858036 181:0.0015720503 182:0.0012860922
183:0.0015920103 184:0.0034542123 185:−0.0054590856 186:−0.0013231005 187:
−0.00026378682 188:−5.6713336e−005 189:0.0016455925 190:0.00055903167 191:0.00040327062
192:−0.00066433422 193:−0.0014816546 194:0.0016943325 195:0.00012320606
196:0.0006577372 197:0.00056744454 198:−0.0023361598 199:0.0042997436 200:−0.0016990597
201:0.0030764227 202:−0.0027063258 203:0.00046884044 204:−0.00031649071
205:0.00065622263 206:−0.0026635081 207:−0.0039158296 208:0.0020220254 209:0.0012250372
210:−0.0028663045 211:−0.0012186989 212:−0.00063428417 213:0.0051512984

APPENDIX C2-continued

SVM ModelWeights
(340; Benign/Malignant)

214:0.00089924945 215:−0.00035291715 216:−0.0026578247 217:−0.031516869 218:
−0.018453332 219:−0.012905908 220:−0.015366459 221:−0.013814257 222:−0.007569442 223:
−0.0047048843 224:0.00062012818 225:0.0014852113 226:−0.019181944 227:−0.005778844 228:
−0.0022216991 229:−0.0013164993 230:−0.011913291 231:−0.0048886021 232:−0.0050922348
233:−0.00091115123 234:−0.0028072072 235:−0.0020788321 236:−0.0069042598 237:
−0.092131011 238:−0.068610474 239:−0.0047269738 240:−0.0084348312 241:−0.0050073303 242:
−0.003040591 243:−0.0038143608 244:−0.040638726 245:−0.02857391 246:−0.0472783 247:
−0.020520929 248:−0.0018310277 249:−0.0055512898 250:−0.0060781906 251:−0.0072731995
252:−0.006453387 253:−0.0049183252 254:−0.014674404 255:−0.026012832 256:−0.021858063
257:−0.021156041 258:−0.0072407476 259:−0.0034868279 260:−0.0014243352 261:−0.0010014101
262:−0.0013208789 263:−0.0028763453 264:−0.0076750983 265:−0.0046692337 266:
−0.0012726086 267:−0.0068167564 268:−0.04353733 269:−0.046706751 270:−0.010794718 271:
−0.0024784503 272:−0.0059213047 273:−0.016445309 274:−0.016014025 275:−0.0077815265 276:
−0.0023459131 277:−0.040564284 278:−0.032950211 279:−0.017959842 280:−0.0040876623,281:
−0.026083954 282:−0.022933906 283:−0.0027156388 284:−0.035015725 285:−0.029552883 286:
−0.010026687 287:−0.011907991 288:0.0022531124 289:−0.002897898 290:−0.00044569091
291:0.00010489624 292:−0.00053147622 293:−0.00073173334 294:−0.000621646 295:
−0.00016437711 296:−0.00049518317 297:0.00021529767 298:0.00052096118 299:−4.636059e−005
300:−0.0021831172 301:−0.0014980205 302:−0.00038898826 303:0.00068646355
304:0.0026823219 305:−0.0040565808 306:−0.0020829935 307:−0.0013752591 308:
−0.00034383399 309:2.7236187e−005 310:−0.00070534449 311:−0.0012802118 312:−0.0030920727
313:−0.00088650011 314:−0.00014303472 315:0.00071791362 316:0.00019783134
317:2.9171604e−006 318:0.00037660156 319:0.0011750009 320:−0.0016896301 321:
−0.0015126425 322:−0.00083564757 323:0.0010692998 324:−0.0016934061 325:−0.00029338882
326:−0.0034646564 327:−7.9289544e−005 328:0.0023930578 329:0.00048041579
330:0.00021849622 331:4.0310828e−005 332:−0.0032790094 333:−0.00015884312 334:
−0.00031949134 335:3.3427419e−005 336:0.00084852462 337:0.00044620238 338:−0.0032407208
339:0.00048842531 340:0.00094149791 #
−0.00081645242570519945 1:11.480239 2:4.4015856 3:2.7414548 4:−1.7944015 5:0.020670321
6:−3.172972 7:1.7720693 8:0.33977011 9:−4.4583831 10:−1.7358112 11:2.1295266 12:1.8335074
13:0.42079771 14:−3.1428821 15:−0.35652745 16:−2.6052432 17:−4.2545991 18:0.119913 19:
−1.3009126 20:1.0571593 21:1.7554218 22:0.98222196 23:−2.4740789 24:2.3750913 25:−1.2592227
26:−1.2876878 27:−1.3512036 28:−0.99439675 29:−0.6929304 30:2.0188313 31:0.39963567
32:1.9517349 33:1.1965405 34:−0.96466547 35:1.5519712 36:0.37793252 37:−0.006880715 38:
−0.34347305 39:0.069352545 40:0.40852034 41:−0.1222181 42:0.5076071 43:−0.59228605 44:
−0.22037746 45:−1.0914367 46:0.544662 47:1.3248136 48:−0.10031602 49:0.41528448 50:
−0.84254622 51:0.090518124 52:−0.36615625 53:0.93545157 54:0.65838861 55:0.038296822 56:
−1.7492578 57:0.14129707 58:0.39605069 59:−0.57719308 60:0.39486134 61:−0.01404435 62:
−0.79504615 63:0.92434222 64:1.1236246 65:−0.91369331 66:0.25839856 67:−1.2276139
68:1.7978841 69:0.44832402 70:0.10241497 71:0.012899262 72:0.17863631 73:0.71144456
74:0.29484099 75:0.059212424 76:0.26446101 77:−0.15068734 78:−0.12540962 79:−0.035991069
80:0.058723163 81:0.23377629 82:0.064840928 83:−0.88246381 84:−0.19494149 85:0.40759304
86:0.39069259 87:−0.31211245 88:0.56729746 89:0.66767365 90:0.39072677 91:0.22175135 92:
−0.54132664 93:−0.64071018 94:0.2146394 95:0.71209687 96:−0.26509205 97:0.0039280006
98:0.010595871 99:−0.0072948104 100:0.0007581744 101:0.0015444086 102:0.00086657552
103:0.0014506713 104:0.00027309253 105:−0.0003779236 106:−0.0033040401 107:−0.002894687
108:0.0012058502 109:0.0026374348 110:−0.0018928888 111:−0.0024273857 112:−0.0003231481
113:0.00057429477 114:−0.00070962519 115:0.0011349921 116:−0.0046544136 117:6.0590241e−
007 118:0.00074805523 119:−0.0025794252 120:0.00037352511 121:−0.0022889439
122:0.0011132049 123:−0.0024242986 124:−0.0045571304 125:−0.0020117455 126:
−0.0092068724 127:−0.0077256206 128:−0.00070437411 129:0.0012516935 130:0.00055489031
131:0.0013429716 132:0.00036176579 133:−0.0026087298 134:5.3104148e−005 135:
−0.001098063 136:0.0010348612 137:−0.00068726367 138:−0.00074436213 139:0.0027458151
140:0.0010222673 141:−0.0018521026 142:−0.00061301264 143:−0.001804522 144:
−0.00021584153 145:0.0015449577 146:−0.0015697054 147:−0.00097707158 148:−0.0011295594
149:0.0028935266 150:−0.00053708232 151:0.0018405041 152:−0.002562111 153:−0.0013092471
154:−0.00046263589 155:−0.0035724007 156:0.0011358063 157:−0.0012884629 158:
−0.0031973415 159:0.00045693576 160:−0.0012730506 161:0.0014123393 162:0.003461167 163:
−0.0029414443 164:−0.00037983558 165:−0.0023911442 166:0.0021477563 167:9.2110975e−005
168:−0.0026100944 169:−0.0034047128 170:−0.0029387963 171:−0.0023030045 172:
−0.0054465104 173:−0.0021478815 174:−0.0022738085 175:0.00050098688 176:−0.0021780876
177:2.5619611e−005 178:−0.0010297548 179:0.000299401 180:0.0002858036 181:0.0015720503
182:0.0012860922 183:0.0015920103 184:0.0034542123 185:−0.0054590856 186:−0.0013231005
187:−0.00026378682 188:−5.6713336e−005 189:0.0016455925 190:0.00055903167
191:0.00040327062 192:−0.00066433422 193:−0.0014816546 194:0.0016943325
195:0.00012320606 196:0.0006577372 197:0.00056744454 198:−0.0023361598
199:0.0042997436 200:−0.0016990597 201:0.0030764227 202:−0.0027063258 203:0.00046884044
204:−0.00031649071 205:0.00065622263 206:−0.0026635081 207:−0.0039158296
208:0.0020220254 209:0.0012250372 210:−0.0028663045 211:−0.0012186989 212:
−0.00063428417 213:0.0051512984 214:0.00089924945 215:−0.00035291715 216:−0.0026578247
217:−0.031516869 218:−0.018453332 219:−0.012905908 220:−0.015366459 221:−0.013814257
222:−0.007569442 223:−0.0047048843 224:−0.00062012818 225:−0.0014852113 226:−0.019181944
227:−0.005778844 228:−0.0022216991 229:−0.0013164993 230:−0.011913291 231:−0.0048886021
232:−0.0050922348 233:−0.00091115123 234:−0.0028072072 235:−0.0020788321 236:
−0.0069042598 237:−0.092131011 238:−0.068610474 239:−0.0047269738 240:−0.0084348312 241:
−0.0050073303 242:−0.003040591 243:−0.0038143608 244:−0.040638726 245:−0.02857391 246:
−0.0472783 247:−0.020520929 248:−0.0018310277 249:−0.0055512898 250:−0.0060781906 251:

APPENDIX C2-continued

| SVM ModelWeights (340; Benign/Malignant) |
|---|
| −0.0072731995 252:−0.006453387 253:−0.0049183252 254:−0.014674404 255:−0.026012832 256: −0.021858063 257:−0.021156041 258:−0.0072407476 259:−0.0034868279 260:−0.0014243352 261: −0.0010014101 262:−0.0013208789 263:−0.0028763453 264:−0.0076750983 265:−0.0046692337 266:−0.0012726086 267:−0.0068167564 268:−0.04353733 269:−0.046706751 270:−0.010794718 271:−0.0024784503 272:−0.0059213047 273:−0.016445309 274:−0.016014025 275:−0.0077815265 276:−0.0023459131 277:−0.040564284 278:−0.032950211 279:−0.017959842 280:−0.0040876623 281:−0.026083954 282:−0.022933906 283:−0.0027156388 284:−0.035015725 285:−0.029552883 286:−0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: **996** −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # −0.0030258876238576835 1:12.400963 2:4.2546644 3:−0.41324967 4:3.0709786 5:−0.27842081 6: −1.2178549 7:2.344552 8:−0.065143779 9:1.4606165 10:1.0544931 11:−2.142359 12:2.1907766 13: −1.5534158 14:−0.69449091 15:0.29213595 16:−3.1575935 17:1.0698617 18:−2.5730839 19:0.0092338799 20:−2.99612 21:−0.1943074 22:−0.86630803 23:1.6802975 24:−1.0868572 25: −1.5044321 26:−1.582459 27:1.117466 28:−0.57524675 29:0.018987674 30:1.4091095 31: −1.0078969 32:15285796 33:0.31792575 34:−0.12233579 35:−0.34751469 36:0.051566206 37: −0.022006385 38:0.26128823 39:−1.0277607 40:−1.3792479 41:0.59065032 42:−2.1147952 43: −0.15735847 44:1.2849991 45:−0.53021276 46:0.85332453 47:−2.4224534 48:−1.7809808 49: −0.53126109 50:−1.4790729 51−:0.88244933 52:−0.72955728 53:1.2992866 54:0.40387648 55:0.015153798 56:0.11678315 57:−0.38129348 58:0.88556302 59:−0.087197445 60:038062981 61:0.42040733 62:0.92759228 63:−0.3889952 64:−0.19115527 65:0.35612798 66:−0.088825949 67:−0.0031237327 68:−1.119221 69:0.26062384 70:−0.45653608 71:1.213123 72:0.24663816 73:0.32365286 74:0.69991243 75:0.0058952384 76:−0.10694939 77:−0.14535566 78:0.55809158 79:0.056639977 80:−0.66649711 81:0.91455543 82:0.41167188 83:−0.37185481 84:0.77568609 85:−0.37804151 86:0.45219046 87:0.28834942 88:−0.34672615 89:0.56919694 90:0.98183829 91: −0.143377943 92:−0.44850191 93:0.056993715 94:−0.30620858 95:−0.21971673 96:0.54302704 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124: −0.0045571304 125:−0.0020117455 126:−0.0092068724 127:−0.0077256206 128:−0.00070437411 129:0.0012516935 130:0.00055489031 131:−0.0013429716 132:0.00036176579 133: −0.0026087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922, 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:0.0027063258 203:0.00046884044 204:−0.00031649071 205:0.00065622263 206:−0.0026635081 207:−0.0039158296 208:0.0020220254 209:0.0012250372 210:0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: |

APPENDIX C2-continued

SVM ModelWeights
(340; Benign/Malignant)

−0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
−0.0020758489311177072 1:11.932061 2:−0.54239619 3:4.2213945 4:−5.9421682 5:−2.619386 6:2.3564994 7:−2.7465849 8:−3.8928757 9:−4.162075 10:−1.7486995 11:0.47773656 12:−4.1929479 13:−2.0677514 14:−6.5466743 15:0.092173383 16:0.91300637 17:−1.0412949 18:3.4058571 19:3.6996002 20:3.7471523 21:−0.1068441 22:1.0975643 23:−1.3388216 24:1.3413877 25:3.6972344 26:1.4300827 27:−0.18405136 28:0.59656787 29:0.032527361 30:−3.2063987 31:1.3294622 32:1.2466725 33:−0.6915769 34:2.29409 35:−1.6047076 36:−0.53606254 37:2.0452888 38:−0.7539885 39:0.77716249 40:−3.2375765 41:0.10940029 42:−1.2017024 43:0.92225856 44:−0.76386726 45:−0.2991994 46:0.59694391 47:−0.55408794 48:−0.46362504 49:0.58976698 50:0.62997901 51:−0.031874478 52:−1.2171367 53:−0.050087653 54:−0.59428918 55:−0.059566271 56:−0.22709765 57:0.178231 58:0.34874552 59:0.91884744 60:−1.374855 61:0.59586394 62:0.01659002 63:0.39488176 64:0.23214574 65:1.2436252 66:0.88398963 67: −0.21129984 68:0.16651997 69:−0.46138206 70:−0.45318407 71:0.22434828 72:0.11926489 73:0.49209055 74:0.43054074 75:0.14348413 76:−0.013169435 77:−0.051100992 78:0.080900505 79:−0.18882868 80:0.1539721 81:0.23456702 82:0.33220461 83:−0.068677895 84:−0.2610451 85: −0.46393099 86:0.03763498 87:0.102527 88:0.24075451 89:−0.042621341 90:0.11195915 91:0.33464432 92:−0.2762607 93:0.13110967 94:−0.057256978 95:−0.13463478 96:0.22564662 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:−0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124: −0.0045571304 125:−0.0020117455 126:−0.0092068724 127:−0.0077256206 128:−0.00070437411 129:0.0012516935 130:0.00055489031 131:0.0013429716 132:0.00036176579 133: −0.0026087298 134:5.3104148e−005 135:−0.001098063 136:0.0010348612 137:−0.00068724367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134

APPENDIX C2-continued

SVM ModelWeights
(340; Benign/Malignant)

317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
0.0018811642850218558 1:−7.7966084 2:1.8707227 3:−23.323887 4:1.0747559 5:1.0184501 6: −3.600925 7:9.3491745 8:−7.7337961 9:−1.2228185 10:7.7243834 11:2.0076487 12:−4.368228 13: −1.5946441 14:−0.2912291 15:−2.0482881 16:−0.38283157 17:−1.6580502 18:−1.0132759 19: −0.17344542 20:0.65646726 21:−0.49175465 22:0.29616475 23:−0.65766221 24:−0.40362445 25:0.31434533 26:0.98643875 27:0.016180724 28:0.12472247 29:−0.22155482 30:−0.0517218 31: −0.0058854236 32:0.09278781 33:0.34776777 34:−0.21737053 35:−0.091020077 36:0.035350032 37:0.2550841 38:−0.072128683 39:0.0050051538 40:−0.072953671 41:0.1237232 42:−0.10784111 43:−0.24674198 44:0.10156032 45:−0.11400478 46:−0.0051734848 47:0.070060618 48: −0.062755756 49:−0.1003389 50:−0.024766795 51:0.042309508 52:−0.045899741 53:−0.018923813 54:0.026509475 55:−0.013425832 56:−0.057100177 57:0.062299002 58:−0.0071787904 59: −0.017751466 60:−0.080059178 61:0.10251214 62:0.19948693 63:−0.017395765 64:−0.065834261 65:0.05320783 66:0.13003403 67:0.045583595 68:0.015333543 69:−0.10374861 70:0.017438892 71:−0.12824923 72:0.1228321 73:0.006350534 74:−0.13356683 75:0.01609605 76:0.019531524 77:−0.02920058 78:−0.017909111 79:−0.032119624 80:−0.081862949 81:0.026391055 82: −0.053974025 83:−0.042487528 84:−0.040375195 85:0.027134888 86:−0.085319266 87:0.014382792 88:0.036518779 89:0.0069534658 90:−0.0058595454 91:0.039325532 92: 0.022480814 93:0.026283203 94:0.041790705 95:0.047353256 96:−0.023455868 97:0.0039280006 98:0.010595871 99:−0.0072948104 100:0.0007581744 101:0.0015444086 102:0.00086657552 103:0.0014506713 104:0.00027309253 105:−0.0003779236 106:−0.0033040401 107:−0.002894687 108:0.0012058502 109:0.0026374348 110:−0.0018928888 111:−0.0024273857 112:−0.0003231481 113:0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124:−0.0045571304 125:−0.0020117455 126: −0.0092068724 127:−0.0077256206 128:−0.00070437411 129:0.0012516935 130:0.00055489031 131:0.0013429716 132:0.00036176579 133:−0.0026087298 134:5.3104148e−005 135: −0.001098063 136:0.0010348612 137:−0.00068726367 138:−0.00074436213 139:0.0027458151 140:0.0010222673 141:−0.0018521026 142:−0.00061301264 143:−0.001804522 144: −0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155:−0.0035724007 156:0.0011358063 157:−0.0012884629 158: −0.0031973415 159:0.00045693576 160:−0.0012730506 161:0.0014123393 162:0.003461167 163: −0.0029414443 164:−0.00037983558 165:−0.0023911442 166:0.0021477563 167:9.2110975e−005 168:−0.0026100944 169:−0.0034047128 170:−0.0029387963 171:−0.0023030045 172: −0.0054465104 173:−0.0021478815 174:−0.0022738085 175:0.00050098688 176:−0.0021780876 177:2.5619611e−005 178:−0.0010297548 179:0.000299401 180:0.0002858036 181:0.0015720503 182:0.0012860922 183:0.0015920103 184:0.0034542123 185:−0.0054590856 186:−0.0013231005 187:−0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212: −0.00063428417 213:0.0051512984 214:0.00089924945 215:−0.00035291715 216:−0.0026578247 217:−0.031516869 218:−0.018453332 219:−0.012905908 220:−0.015366459 221:−0.013814257 222:−0.007569442 223:−0.0047048843 224:0.00062012818 225:0.0014852113 226:−0.019181944 227:−0.005778844 228:−0.0022216991 229:−0.0013164993 230:−0.011913291 231:−0.0048886021 232:−0.0050922348 233:−0.00091115123 234:−0.0028072072 235:−0.0020788321 236: −0.0069042598 237:−0.092131011 238:−0.068610474 239:−0.0047269738 240:−0.0084348312 241: −0.0050073303 242:−0.003040591 243:−0.0038143608 244:−0.040638726 245:−0.02857391 246: −0.0472783 247:−0.020520929 248:−0.0018310277 249:−0.0055512898 250:−0.0060781906 251: −0.0072731995 252:−0.006453387 253:−0.0049183252 254:−0.014674404 255:−0.026012832 256: −0.021858063 257:−0.021156041 258:−0.0072407476 259:−0.0034868279 260:−0.0014243352 261: −0.0010014101 262:−0.0013208789 263:−0.0028763453 264:−0.0076750983 265:−0.0046692337 266:−0.0012726086 267:−0.0068167564 268:−0.04353733 269:−0.046706751 270:−0.010794718 271:−0.0024784503 272:−0.0059213047 273:−0.016445309 274:−0.016014025 275:−0.0077815265 276:−0.0023459131 277:−0.040564284 278:−0.032950211 279:−0.017959842 280:−0.0040876623 281:−0.026083954 282:−0.022933906 283:−0.0027156388 284:−0.035015725 285:−0.029552883 286:−0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
0.0015027662542705742 1:−3.8587921 2:−16.208611 3:−2.6007581 4:2.9952328 5:−2.9244998 6:

APPENDIX C2-continued

| SVM ModelWeights (340; Benign/Malignant) |
| --- |
| −2.1342196 7:−8.6919346 8:2.102823 9:−0.65605307 10:−3.5787513 11:0.57963091 12:−3.8771913 13:1.4609568 14:1.0911566 15:−2.6927843 16:−0.73983127 17:−2.9269328 18:−3.2514834 19: −1.6491545 20:−2.8616376 21:−2.9949863 22:0.38679239 23:−0.50630879 24:0.66747051 25: −0.56378025 26:2.5836411 27:−0.59832889 28:0.37365031 29:2.3311179 30:1.4624356 31:0.31802523 32:−0.90313685 33:−1.2535348 34:−0.47041008 35:1.9334433 36:1.0617839 37:4.1906142 38:0.26222989 39:0.44094789 40:−0.27469787 41:2.5724795 42:−0.9394781 43: −0.5121271 44:−1.7902449 45:−0.76117063 46:−1.2025639 47:−0.75431925 48:−0.27811137 49: −0.86414403 50:−0.0057006418 51:1.9052811 52:0.40665537 53:−1.2708704 54:−0.33689812 55:0.49392983 56:−0.045317728 57:−0.43321306 58:−0.7863214 59:−0.14774203 60:0.080907896 61:0.56522685 62:0.60004711 63:0.2153769 64:0.029641049 65:0.096503533 66:0.31114331 67: −0.58736598 68:−0.25519821 69:−0.1153139 70:−0.040961515 71:−0.26411968 72:0.11253919 73:0.82753402 74:−0.017763685 75:−0.18250082 76:0.085465781 77:0.029048748 78:0.57212704 79:0.087843932 80:−0.32256076 81:0.06564676 82:−0.047518075 83:−0.3899799 84:−0.23717856 85:0.054492351 86:−0.093572512 87:0.0057938704 88:−0.028118499 89:0.37925208 90:0.081810564 91:−0.40198913 92:0.1882457 93:−0.17574753 94:−0.31153521 95:−0.084950246 96:−0.15318221 97:0.0039280006 98:0.010595871 99:−0.0072948104 100:0.0007581744 101:0.0015444086 102:0.00086657552 103:0.0014506713 104:0.00027309253 105: −0.0003779236 106:−0.0033040401 107:−0.002894687 108:0.0012058502 109:0.0026374348 110: −0.0018928888 111:−0.0024273857 112:−0.0003231481 113:0.00057429477 114:−0.00070962519 115:0.0011349921 116:−0.0046544136 117:6.0590241e−007 118:0.00074805523 119: −0.0025794252 120:0.00037352511 121:−0.0022889439 122:0.0011132049 123:−0.0024242986 124:−0.0045571304 125:−0.0020117455 126:−0.0092068724 127:−0.0077256206 128: −0.00070437411 129:0.0012516935 130:0.00055489031 131:0.0013429716 132:0.00036176579 133:−0.0026087298 134:5.3104148e−005 135:−0.001098063 136:0.0010348612 137: −0.00068726367 138:−0.00074436213 139:0.0027458151 140:0.0010222673 141:−0.0018521026 142:−0.00061301264 143:−0.001804522 144:−0.00021584153 145:0.0015449577 146: −0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # 0.0033153142499855108 1:−0.42324471 2:2.5828345 3:−1.8410451 4:−0.4363316 5:0.067014627 6:−1.8869078 7:2.7124326 8:3.5093668 9:−2.1161191 10:0.31742153 11:2.0527875 12:2.6345732 13:−0.53119665 14:−1.2637744 15:0.19591911 16:−2.386672 17:0.98163056 18:0.015205857 19:1.3719232 20:−3.8242466 21:0.63041341 22:2.2860601 23:−2.2027335 24:−1.1924071 25:0.088403225 26:−2.2897179 27:1.8068643 28:−0.78437859 29:−0.35509837 30:−0.57099378 31:0.79047942 32:2.1919038 33:0.32323298 34:−0.1085334 35:0.71788019 36:0.46938607 37: −1.4283434 38:−1.6121867 39:−0.56469077 40:−0.47763538 41:−0.81906885 42:0.6883561 43:2.4099319 44:−2.0321629 45:0.78628761 46:−1.5318716 47:1.581475 48:0.28450912 49: |

APPENDIX C2-continued

SVM ModelWeights
(340; Benign/Malignant)

−1.8042477 50:−1.1501552 51:0.96483588 52:−1.007615 53:−1.9168314 54:0.10064875 55:1.0965402 56:2.0633764 57:−0.23728377 58:−0.65973568 59:−0.16923778 60:−1.4804031 61:0.57514387 62:0.26726937 63:0.31430072 64:−0.079305612 65:0.16362113 66:−0.24121113 67:−0.32369888 68:−0.16671567 69:0.011938976 70:0.57545716 71:0.10028149 72:−0.55875379 73:0.090979785 74:−0.28152052 75:−0.74530959 76:−0.68932241 77:−0.21559061 78:−0.13300842 79:1.0360554 80:0.84739202 81:−0.079618588 82:0.39879352 83:−0.38048029 84:−0.13616773 85:0.24391849 86:0.28922558 87:0.093983881 88:−0.27600482 89:−0.41217899 90:0.41511154 91:−0.052721132 92:−0.23836724 93:−0.11657015 94:−0.11322521 95:−0.30037713 96:0.08614935 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124: −0.0045571304 125:−0.0020117455 126:−0.0092068724 127:−0.0077256206 128:−0.00070437411 129:0.0012516935 130:0.00055489031 131:0.0013429716 132:0.00036176579 133: −0.0026087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 181:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815245 276: −0.0023459131 277:−0.040564284 278:−0.032950211 279:−0.017959842 280:−0.0040876623,281: −0.026083954 282:−0.022933906 283:−0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
−0.0033153142499855108 1:1.9507116 2:−11.019697 3:−2.6828804 4:5.4480629 5:5.7107086 6:6.9693308 7:2.66974 8:3.2545464 9:−1.9070691 10:0.99127346 11:−2.2294374 12:2.7105196 13: −3.1338248 14:1.5385495 15:−0.67776555 16:1.5831238 17:−0.5545975 18:0.12189388 19: −3.4824948 20:0.54062164 21:−1.5836126 22:−2.3674173 23:−1.9569142 24:0.007869835 25:0.49454546 26:−2.1373594 27:1.9552969 28:1.1393875 29:−1.3862598 30:1.9857892 31:0.16729748 32:0.81011742 33:−1.4185259 34:0.24046826 35:0.82870692 36:0.15950572 37: −0.79740018 38:−0.16591235 39:0.96315569 40:−2.1959643 41:2.8853498 42:−0.43963414 43:0.85861981 44:0.64902544 45:2.0380046 46:1.5051774 47:1.3050799 48:1.0160776 49:0.51463306 50:0.30809772 51:0.47857744 52:2.0385702 53:0.6751821 54:−0.74133307 55: −0.57322341 56:0.13433874 57:−0.27051914 58:−0.51146394 59:1.6747578 60:0.12013735 61:0.54918289 62:−1.1039402 63:0.057252187 64:−0.21718289 65:0.30045113 66:0.86003029 67:0.25052261 68:0.12187614 69:−0.087335959 70:−0.15423696 71:0.54607618 72:−0.4881106 73:−0.41245741 74:0.19769716 75:−0.89351356 76:−0.13735279 77:−0.2327853 78:−0.23674634 79:−0.98305404 80:0.52078742 81:0.63322812 82:0.58455044 83:−0.090681896 84:0.022197129 85:0.30395666 86:0.30433914 87:−0.217499 88:0.05495261 89:−0.13069777 90:0.089781485

APPENDIX C2-continued

| SVM ModelWeights (340; Benign/Malignant) |
| --- |
| 91:0.030463779 92:0.15014772 93:0.060836539 94:0.16221549 95:0.082676701 96:−0.1661652 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590236e−007 118:0.00074805523 119:−0.0025794252 120:0.00037352511 121:−0.0022889439 122:0.0011132049 123:−0.0024242986 124: −0.0045571304 125:−0.0020117455 126:−0.0092068724 127:−0.0077256206 128:−0.00070437411 129:0.0012516935 130:0.00055489031 131:0.0013429716 132:0.00036176579 133: −0.01126087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:0.0049183252 254:0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:−0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:−0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # |
| −0.0033153142499855108 1:−1.3436253 2:−0.93941635 3:0.34727129 4:−4.000988 5:3.6346951 6: −2.0202615 7:2.8455384 8:2.3817055 9:−1.1053888 10:−0.021449149 11:0.5917924 12:1.05388 13: −0.72289419 14:0.42895883 15:2.1116214 16:0.92751497 17:1.8995572 18:1.0356827 19: −0.83366108 20:−0.16999248 21:−0.48544282 22:−1.7330638 23:1.7139575 24:1.0412071 25: −0.094441161 26:0.47909549 27:2.0350492 28:−0.79608703 29:−0.017424189 30:−1.4338908 31: −0.18901214 32:−0.35805777 33:−0.99202484 34:0.13780618 35:−0.15510346 36:−1.3227181 37: −0.10028049 38:0.26590782 39:0.93775231 40:1.2771348 41:−0.42096636 42:0.78392965 43: −0.35746196 44:0.32524577 45:−0.44138062 46:−1.7038687 47:−0.31887752 48:−0.026019525 49:0.00052639912 50:−1.0878571 51:−0.18844727 52:−0.059497412 53:0.59026122 54:−1.0394223 55:1.0100427 56:1.132426 57:1.2046562 58:0.21211471 59:0.59887296 60:−0.21160595 61:1.0129697 62:−1.1150941 63:0.070315979 64:1.0367281 65:−0.34955642 66:0.32304484 67: −1.1201361 68:−0.48632643 69:−0.64808732 70:−1.1307749 71:−0.79533523 72:0.47282416 73:0.96091819 74:−0.89764357 75:−0.57210386 76:0.10012428 77:−0.027124282 78:−0.25215131 79:0.33998123 80:−0.23809782 81:1.1138523 82:0.016608508 83:0.14363414 84:1.3560621 85: −0.93441159 86:0.64719403 87:−0.48639837 88:−0.51724219 89:0.36221823 90:−1.1195625 91:0.13481082 92:0.30573699 93:−0.35263085 94:−0.050153632 95:0.15032227 96:0.0079603 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124: |

APPENDIX C2-continued

SVM ModelWeights
(340; Benign/Malignant)

−0.0045571304 125:−0.0020117455 126:−0.0092068724 127:−0.0077256206 128:−0.00070437411 129:0.0012516935 130:0.00055489031 131:0.0013429716 132:0.00036176579 133: −0.0026087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
−0.003315314249985510 8 1:3.9146221 2:9.5838127 3:−2.1989262 4:2.483418 5:2.2109056 6:2.3148644 7:−1.6744893 8:2.0438197 9:−0.22050218 10:0.95947695 11:1.7617443 12:1.0714002 13:−2.0813811 14:0.52549028 15:0.8533324 16:2.6622386 17:−2.1034327 18:−0.13717787 19: −2.1242678 20:1.0191004 21:−1.0218762 22:−1.8217447 23:1.2176883 24:0.32349762 25: −1.7366513 26:0.13325104 27:1.2317364 28:−1.6418275 29:−1.1362265 30:1.0577126 31:0.8307243 32:−0.038968693 33:1.0813892 34:−0.26267028 35:−0.40768319 36:−1.5068281 37:0.24804747 38: −2.8056893 39:−1.4992043 40:−0.87992305 41:0.15084013 42:−0.46094763 43:0.088341065 44: −0.45993951 45:−1.8586137 46:−0.12604149 47:−0.77085721 48:−0.3926746 49:1.5514119 50:0.3039287 51:−0.020093013 52:−1.7802604 53:0.85846531 54:−0.49611357 55:−1.8293589 56:0.416605 57:−1.5735593 58:−0.32552642 59:−0.281872 60:−0.74955857 61:0.14202702 62:0.61847329 63:0.38252032 64:−0.94535166 65:−0.10739016 66:−0.40688729 67:−0.64594442 68:0.9584676 69:1.6266457 70:0.14564814 71:0.057670958 72:−0.51033443 73:0.092842311 74: −0.80618852 75:0.62784499 76:−0.57284373 77:0.41931754 78:−0.82127243 79:0.076667011 80: −0.051802412 81:−0.8036865 82:−0.40587062 83:0.18605494 84:0.039897773 85:0.10903195 86:0.40717348 87:−0.3650966 88:−0.25333995 89:−0.30965137 90:−0.34480369 91:0.17502359 92:0.55318487 93:−0.45254979 94:0.12390731 95:−0.58431411 96:0.44539803 97:0.0039280006 98:0.010595871 99:−0.0072948104 100:0.0007581744 101:0.0015444086 102:0.00086657552 103:0.0014506713 104:0.00027309253 105:−0.0003779236 106:−0.0033040401 107:−0.002894687 108:0.0012058502 109:0.0026374348 110:−0.0018928888 111:−0.0024273857 112:−0.0003231481 113:0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124:−0.0045571304 125:−0.0020117455 126: −0.0092068724 127:−0.0077256206 128:−0.00070437411 129:0.0012516935 130:0.00055489031 131:0.0013429716 132:0.00036176579 133:−0.0026087298 134:5.3104148e−005 135: −0.001098063 136:0.0010348612 137:−0.00068726367 138:−0.00074436213 139:0.0027458151 140:0.0010222673 141:−0.0018521026 142:−0.00061301264 143:−0.001804522 144: −0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155:−0.0035724007 156:0.0011358063 157:−0.0012884629 158:

APPENDIX C2-continued

| SVM ModelWeights (340; Benign/Malignant) |
| --- |
| −0.0031973415 159:0.00045693576 160:−0.0012730506 161:0.0014123393 162:0.003461167 163: −0.0029414443 164:−0.00037983558 165:−0.0023911442 166:0.0021477563 167:9.2110975e−005 168:−0.0026100944 169:−0.0034047128 170:−0.0029387963 171:−0.0023030045 172: −0.0054465104 173:−0.0021478815 174:−0.0022738085 175:0.00050098688 176:−0.0021780876 177:2.5619611e−005 178:−0.0010297548 179:0.000299401 180:0.0002858036 181:0.0015720503 182:0.0012860922 183:0.0015920103 184:0.0034542123 185:−0.0054590856 186:−0.0013231005 187:−0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212: −0.00063428417 213:0.0051512984 214:0.00089924945 215:−0.00035291715 216:−0.0026578247 217:−0.031516869 218:−0.018453332 219:−0.012905908 220:−0.015366459 221:−0.013814257 222:−0.007569442 223:−0.0047048843 224:0.00062012818 225:0.0014852113 226:0.019181944 227:−0.005778844 228:−0.0022216991 229:−0.0013164993 230:−0.011913291 231:−0.0048886021 232:−0.0050922348 233:−0.00091115123 234:−0.0028072072 235:−0.0020788321 236: −0.0069042598 237:−0.092131011 238:−0.068610474 239:−0.0047269738 240:−0.0084348312 241: −0.0050073303 242:−0.003040591 243:−0.0038143608 244:−0.040638726 245:−0.02857391 246: −0.0472783 247:−0.020520929 248:−0.0018310277 249:−0.0055512898 250:−0.0060781906 251: −0.0072731995 252:−0.006453387 253:−0.0049183252 254:−0.014674404 255:−0.026012832 256: −0.021858063 257:−0.021156041 258:−0.0072407476 259:−0.0034868279 260:−0.0014243352 261: −0.0010014101 262:−0.0013208789 263:0.0028763453 264:0.0076750983 265:−0.0046692337 266:−0.0012726086 267:−0.0068167564 268:−0.04353733 269:−0.046706751 270:−0.010794718 271:−0.0024784503 272:−0.0059213047 273:−0.016445309 274:−0.016014025 275:−0.0077815265 276:−0.0023459131 277:−0.040564284 278:−0.032950211 279:0.017959842 280:−0.0040876623 281:−0.026083954 282:−0.022933906 283:−0.0027156388 284:−0.035015725 285:−0.029552883 286:−0.010026687 287:−0.011907991 288:0.0022531124 289:−0.002897898 290:−0.00044569091 291:−0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # |
| 0.0033153142499855108 1:9.2099752 2:0.10233181 3:1.9269702 4:−2.1939819 5:−1.9438351 6:3.0239697 7:−5.1489539 8:−5.0794964 9:−1.1390828 10:0.33780786 11:1.8522336 12:−7.0093985 13:−2.1220815 14:−7.3823423 15:1.5933274 16:3.5308435 17:2.6375818 18:2.7540584 19: −0.99151331 20:0.0083616357 21:0.54905522 22:0.68470973 23:−1.4407222 24:−1.9258854 25: −0.28219196 26:−0.25906509 27:−0.60497737 28:−1.8318855 29:−2.0681658 30:2.9541204 31:2.6221907 32:−0.93029034 33:−1.8050101 34:0.52987593 35:0.48732564 36:0.91307831 37:0.12632039 38:0.6361919 39:−2.6943514 40:3.1532407 41:−0.1327378 42:0.31272578 43: −0.35162035 44:1.9987303 45:0.43408412 46:0.083819687 47:0.53805685 48:0.55005115 49: −0.69969761 50:−1.0889786 51:0.44436994 52:−0.47532484 53:0.11296681 54:−0.26162675 55:0.083675936 56:0.43792534 57:0.46311471 58:−0.87382078 59:1.1646171 60:0.038086068 61: −0.10682595 62:−0.32176739 63:−0.87397802 64:−1.7255341 65:−0.12923253 66:−0.0063713025 67:−0.32136509 68:−0.46372363 69:0.2720727 70:−0.040819522 71:0.093332551 72:−0.10163796 73:0.054285415 74:0.51410824 75:0.42510664 76:−0.44858062 77:0.094385475 78:−0.039332729 79:0.11206785 80:0.043272279 81:0.3098256 82:−0.31685907 83:−0.15600948 84:0.26660839 85:0.095404632 86:0.07407812 87:0.23526323 88:−0.087359466 89:0.40686274 90:−0.051494688 91:−0.23362625 92:0.050865389 93:−0.11867395 94:−0.046460025 95:−0.08569926 96:−0.38963827 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124: −0.0045571304 125:−0.0020117455 126:−0.0092068724 127:−0.0077256206 128:−0.00070437411 129:0.0012516935 130:0.00055489031 131:0.0013429716 132:0.00036176579 133: −0.0026087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 |

APPENDIX C2-continued

SVM ModelWeights
(340; Benign/Malignant)

192:−0.00066433422 193:−0.0014816546 194:0.0016943325 195:0.00012320606
196:0.0006577372 197:0.00056744454 198:−0.0023361598 199:0.0042997436 200:−0.0016990597
201:0.0030764227 202:−0.0027063258 203:0.00046884044 204:−0.00031649071
205:0.00065622263 206:−0.0026635081 207:−0.0039158296 208:0.0020220254 209:0.0012250372
210:−0.0028663045 211:−0.0012186989 212:−0.00063428417 213:0.0051512984
214:0.00089924945 215:−0.00035291715 216:−0.0026578247 217:−0.031516869 218:
−0.018453332 219:−0.012905908 220:−0.015366459 221:−0.013814257 222:−0.007569442 223:
−0.0047048843 224:0.00062012818 225:0.0014852113 226:−0.019181944 227:−0.005778844 228:
−0.0022216991 229:−0.0013164993 230:−0.011913291 231:−0.0048886021 232:−0.0050922348
233:−0.00091115123 234:−0.0028072072 235:−0.0020788321 236:−0.0069042598 237:
−0.092131011 238:−0.068610474 239:−0.0047269738 240:−0.0084348312 241:−0.0050073303 242:
−0.003040591 243:−0.0038143608 244:−0.040638726 245:−0.02857391 246:−0.0472783 247:
−0.020520929 248:−0.0018310277 249:−0.0055512898 250:−0.0060781906 251:−0.0072731995
252:−0.006453387 253:−0.0049183252 254:−0.014674404 255:−0.026012832 256:−0.021858063
257:−0.021156041 258:−0.0072407476 259:−0.0034868279 260:−0.0014243352 261:−0.0010014101
262:−0.0013208789 263:−0.0028763453 264:−0.0076750983 265:−0.0046692337 266:
−0.0012726086 267:−0.0068167564 268:−0.04353733 269:−0.046706751 270:−0.010794718 271:
−0.0024784503 272:−0.0059213047 273:−0.016445309 274:−0.016014025 275:−0.0077815265 276:
−0.0023459131 277:−0.040564284 278:−0.032950211 279:−0.017959842 280:−0.0040876623 281:
−0.026083954 282:−0.022933906 283:−0.0027156388 284:−0.035015725 285:−0.029552883 286:
−0.010026687 287:−0.011907991 288:0.0022531124 289:−0.002897898 290:−0.00044569091
291:0.00010489624 292:−0.00053147622 293:−0.00073173334 294:−0.000621646 295:
−0.00016437711 296:−0.00049518317 297:0.00021529767 298:0.00052096118 299:−4.636059e−005
300:−0.0021831172 301:−0.0014980205 302:−0.00038898826 303:0.00068646355
304:0.0026823219 305:−0.0040565808 306:−0.0020829935 307:−0.0013752591 308:
−0.00034383399 309:2.7236187e−005 310:−0.00070534449 311:−0.0012802118 312:−0.0030920727
313:−0.00088650011 314:−0.00014303472 315:0.00071791362 316:0.00019783134
317:2.9171604e−006 318:0.00037660156 319:0.0011750009 320:−0.0016896301 321:
−0.0015126425 322:−0.00083564757 323:0.0010692998 324:−0.0016934061 325:−0.00029338882
326:−0.0034646564 327:−7.9289544e−005 328:0.0023930578 329:0.00048041579
330:0.00021849622 331:4.0310828e−005 332:−0.0032790094 333:−0.00015884312 334:
−0.00031949134 335:3.3427419e−005 336:0.00084852462 337:0.00044620238 338:−0.0032407208
339:0.00048842531 340:0.00094149791 #
0.0033153142499855108 1:4.8919382 2:6.5307918 3:4.6522961 4:0.50912267 5:1.0186707 6:
−1.6481709 7:−1.5135888 8:−1.650799 9:2.0391626 10:3.3697751 11:0.28303525 12:0.80901867
13:−0.7322185 14:2.4035478 15:−0.92959404 16:−0.11080018 17:1.1656927 18:−0.061241843
19:0.093886204 20:0.41603193 21:1.5590807 22:−0.079786256 23:−1.3937597 24:−0.93761557
25:−1.2395495 26:0.47965881 27:−1.8439426 28:−1.0782979 29:2.3248599 30:−0.25143835,31:
−0.11789405 32:0.25579667 33:−0.023998141 34:−0.48568967 35:−0.30022782 36:2.9556475
37:0.45612425 38:−0.54248434 39:−0.51530242 40:−0.71495318 41:−0.029934257 42:0.019748591
43:0.59214228 44:0.064154685 45:−0.10139915 46:−0.24000387 47:0.70566356 48:0.43672034
49:1.5145738 50:0.32631695 51:0.011702045 52:1.2934036 53:0.23414563 54:−2.2872193 55:
−0.83546925 56:−0.38473645 57:0.040741041 58:0.21569888 59:−0.32376489 60:−1.4367403 61:
−0.24261849 62:−0.6142832 63:1.1440008 64:−1.2322909 65:−0.65854615 66:0.067190781
67:0.18490925 68:−0.73051834 69:−0.037479538 70:1.7830526 71:0.53027761 72:−0.33125749
73:0.54123253 74:−0.90944654 75:0.51352841 76:0.45196581 77:−1.105139 78:1.0859764
79:0.75343102 80:−0.30513814 81:0.98500597 82:0.011409609 83:0.49440524 84:−0.14414717
85:−0.52839154 86:0.30832028 87:−0.39584917 88:−0.15387513 89:0.25125772 90:−0.10931044
91:−0.18379685 92:0.016592529 93:0.2826708 94:0.77563244 95:0.12899201 96:0.15736498
97:0.0039280006 98:0.010595871 99:−0.0072948104 100:0.0007581744 101:0.0015444086
102:0.00086657552 103:0.0014506713 104:0.00027309253 105:−0.0003779236 106:
−0.0033040401 107:−0.002894687 108:0.0012058502 109:0.0026374348 110:−0.0018928888 111:
−0.0024273857 112:−0.0003231481 113:0.00057429477 114:−0.00070962519 115:0.0011349921
116:−0.0046544136 117:6.0590241e−007 118:0.00074805523 119:−0.0025794252
120:0.00037352511 121:−0.0022889439 122:0.0011132049 123:−0.0024242986 124:
−0.0045571304 125:−0.0020117455 126:−0.0092068724 127:−0.0077256206 128:−0.00070437411
129:0.0012516935 130:0.00055489031 131:0.0013429716 132:0.00036176579 133:
−0.0026087298 134:5.3104148e−005 135:−0.001098063 136:0.0010348612 137:−0.00068726367
138:−0.00074436213 139:0.0027458151 140:0.0010222673 141:−0.0018521026 142:
−0.00061301264 143:−0.001804522 144:−0.00021584153 145:0.0015449577 146:−0.0015697054
147:−0.00097707158 148:−00011295594 149:0.0028935266 150:−0.00053708232
151:0.0018405041 152:0.002562111 153:−0.0013092471 154:−0.00046263589 155:
−0.0035724007 156:0.0011358063 157:−0.0012884S29 158:−0.0031973415 159:0.00045693576
160:−0.001 2730506 161:0.0014123393 162:0.003461167 163:−0.0029414443 164:−0.00037983558
165:−0.0023911442 166:0.0021477563 167:9.2110975e−005 168:−0.0026100944 169:
−0.0034047128 170:−0.0029387963 171:−0.023030045 172:−0.0054465104 173:−0.0021478815
174:−0.0022738085 175:0.00050098688 176:−0.0021780876 177:2.5619611e−005 178:
−0.0010297548 1790.000299401 180:0.0002858036 181:0.0015720503 182:0.0012860922
183:0.0015920103 184:0.0034542123 185:−0.0054590856 186:−0.0013231005 187:
−0.00026378682 188:−5.6713336e−005 189:0.0016455925 190:0.00055903167 191:0.00040327062
192:−0.00066433422 193:−0.0014816546 194:0.0016943325 195:0.00012320606
196:0.0006577372 197:0.00056744454 198:−00023361598 199:0.0042997436 200:−00016990597
201:0.0030764227 202:−0.0027063258 203:0.00046884044 204:−0.00031649071
205:0.00065622263 206:−0.0026635081 207:−0.0039158296 208:0.0020220254 209:00012250372
210:−0.0028663045 211:−00012186989 212:−0.00063428417 213:0.0051512984
214:0.00089924945 215:−0.00035291715 216:−0.0026578247 217:−0031516869 218:
−0.018453332 219:−0.012905908 220:−0.015366459 221:−0.013814257 222:−0007569442 223:

APPENDIX C2-continued

SVM ModelWeights
(340; Benign/Malignant)

−0.0047048843 224:0.00062012818 225:0.0014852113 226:−0019181944 227:−0005778844 228:
−0.0022216991 229:−0.0013164993 230:−0.011913291 231:−0.0048886021 232:−0.0050922348
233:−0.00091115123 234:−0.0028072072 235:−0.0020788321 236:−0.0069042598 237:
−0.092131011 238:−0.068610474 239:−0.0047269738 240:−0.0084348312 241:−0.0050073303 242:
−0.003040591 243:−0.0038143608 244:−0.040638726 245:−0.02857391 246:−0.0472783 247:
−0.020520929 248:−0.0018310277 249:−0.0055512898 250:−0.0060781906 251:−00072731995
252:−0006453387 253:−0.0049183252 254:−0014674404 255:−0.026012832 256:−0.021858063
257:−0021156041 258:−0.0072407476 259:−0.0034868279 260:−0.0014243352 261:−0.0010014101
262:−00013208789 263:−0.0028763453 264:−0.0076750983 265:−0.0046692337 266:
−0.0012726086 267:−0.0068167564 268:−0.04353733 269:−0.046706751 270:−0010794718 271:
−0.0024784503 272:−0005921 3047 273:−0016445309 274:−0016014025 275:−0.0077815265 276:
−0.0023459131 277:−0040564284 278:−0.032950211 279:−0017959842 280:−00040876623 281:
−0.026083954 282:−0022933906 283:−00027156388 284:−0035015725 285:−0.029552883 286:
−0.010026687 287:−0.011907991 288:0.0022531124 289:−0.002897898 290:−0.00044569091
291:0.00010489624 292:−000053147622 293:−0.00073173334 294:−0000621646 295:
−0.00016437711 296:−0.00049518317 297:0.00021529767 298:0.00052096118 299:−4.636059e−005
300:−00021831172 301:−0.0014980205 302:−000038898826 303:0.00068646355
304:0.0026823219 305:−0.0040565808 306:−00020829935 307:−0.0013752591 308:
−0.00034383399 309:2.7236187e−005 310:−0.00070534449 311:−0.0012802118 312:−00030920727
313:−0.00088650011 314:−000014303472 315:0.00071791362 316:0.00019783134
317:2.9171604e−006 318:0.00037660156 319:0.0011750009 320:−00016896301 321:
−0.0015126425 322:−0.00083564757 323:0.0010692998 324:−00016934061 325:−0.00029338882
326:−0.0034646564 327:−7.9289544e−005 328:0.0023930578 329:0.00048041579
330:000021849622 331:40310828e−005 332:−00032790094 333:−0.00015884312 334:
−0.00031949134 335:3.3427419e−005 336:0.00084852462 337:0.00044620238 338:−00032407208
339:0.00048842531 340:0.00094149791 #
0.0033153142499855108 1:3.3829088 2:2.943239 3:3.1921368 4:−7.1808729 5:−0.58675814
6:0.78415442 7:2.0849354 8:−2.3231814 9:−1.2042598 10:−0.67835438 11:−3.815778 12:
−0.030315256 13:−1.90111 53 14:0.15897124 15:−0.94414741 16:1.256176 17:1.2059518 18:
−2.8228135 19:−0.78729898 20:−0.21089606 21:1.2398977 22:0.40475592 23:−2.1799212 24:
−1.4266895 25:0.61812282 26:0.20725577 27:−2.2211232 28:10998532 29:1.8443335
30:0.45508903 31:0.81324655 32:0.1167727 33:024159066 34:−0.94804347 35:0.43025914 36:
−1.5013132 37:−0.41262493 38:−0.27913424 39:1.452195 40:0.89614612 41:0.45674798 42:
−0.69670659 43:0.20472988 44:−0.68425399 45:1.8435879 46:0.36953163 47:−0.14509733 48:
−0.059769865 49:−0.8294245 50:0.11404043 51:−0.55319852 52:−0.68372446 53:−0.91018629
54:0.94105601 55:−10993478 56:0.56316334 57:−1.2337679 58:−0.96762305 59:0.86326998 60:
−0.35409802 61:−1.7822696 62:0.67693377 63:0.59586 64:0.77106255 65:−0.08978609 66:
−0.55685008 67:1.2705643 68:−0.11793981 69:0.20805952 70:0.71785802 71:−0.9783408
72:0.13318537 73:0.63180852 74:0.044601873 75:0.2948941 76:−0.057511415 77:0.80193365
78:0.1222982 79:−0.57889193 80:−0.61818993 81:−0.11715686 82:0.32118329 83:0.84990716
84:0.5679155 85:−0.84811169 86:0.93442708 87:−0.53476751 88:0.030788347 89:0.33149239
90:0.31148005 91:0.75499552 92:0.19272661 93:−0.61854583 94:−0.16499107 95:−0.07209684
96:−0.46436217 97:0.0039280006 98:0.010595871 99:−0.0072948104 100:0.0007581744
101:0.0015444086 102:0.00086657552 103:0.0014506713 104:0.00027309253 105:
−0.0003779236 106:−0.0033040401 107:−0.002894687 108:0.0012058502 109:0.0026374348 110:
−0.0018928888 111:−0.0024273857 112:−0.0003231481 113:0.00057429477 114:−0.00070962519
115:0.0011349921 116:−0.0046544136 117:6.0590241e−007 118:0.00074805523 119:
−0.0025794252 120:0.00037352511 121:−0.0022889439 122:0.0011132049 123:−0.0024242986
124:−0.0045571304 125:−0.0020117455 126:−0.0092068724 127:−0.0077256206 128:
−0.00070437411 129:0.0012516935 130:0.00055489031 131:0.0013429716 132:0.00036176579
133:−0.0026087298 134:5.3104148e−005 135:−0.001098063 136:0.0010348612 137:
−0.00068726367 138:−0.00074436213 139:0.0027458151 140:0.0010222673 141:−0.0018521026
142:−0.00061301264 143:−0.001804522 144:−0.00021584153 145:0.0015449577 146:
−0.0015697054 147:−0.00097707158 148:−0.0011295594 149:0.0028935266 150:−0.00053708232
151:0.0018405041 152:−0.002562111 153:−0.0013092471 154:−0.00046263589 155:
−0.0035724007 156:0.0011358063 157:−0.0012884629 158:−0.0031973415 159:0.00045693576
160:−0.0012730506 161:0.0014123393 162:0.003461167 163:−0.0029414443 164:−0.00037983558
165:−0.0023911442 166:0.0021477563 167:9.2110975e−005 168:−0.0026100944 169:
−0.0034047128 170:−0.0029387963 171:−0.0023030045 172:−0.0054465104 173:−0.0021478815
174:−0.0022738085 175:0.00050098688 176:−0.0021780876 177:2.5619611e−005 178:
−0.0010297548 179:0.000299401 180:0.0002858036 181:0.0015720503 182:0.0012860922
183:0.0015920103 184:0.0034542123 185:−0.0054590856 186:−0.0013231005 187:
−0.00026378682 188:−5.6713336e−005 189:0.0016455925 190:0.00055903167 191:0.00040327062
192:−0.00066433422 193:−0.0014816546 194:0.0016943325 195:0.00012320606
196:0.0006577372 197:0.00056744454 198:−0.0023361598 199:0.0042997436 200:−0.0016990597
201:0.0030764227 202:−0.0027063258 203:0.00046884044 204:−0.00031649071
205:0.00065622263 206:−0.0026635081 207:−0.0039158296 208:0.0020220254 209:0.0012250372
210:−0.0028663045 211:−0.0012186989 212:−0.00063428417 213:0.0051512984
214:0.00089924945 215:−0.00035291715 216:−0.0026578247 217:−0.031516869 218:
−0.018453332 219:−0.012905908 220:−0.015366459 221:−0.013814257 222:−0.007569442 223:
−0.0047048843 224:0.00062012818 225:0.0014852113 226:−0.019181944 227:−0.005778844 228:
−0.0022216991 229:−0.0013164993 230:−0.011913291 231:−0.0048886021 232:−0.0050922348
233:−0.00091115123 234:−0.0028072072 235:−0.0020788321 236:−0.0069042598 237:
−0.092131011 238:−0.068610474 239:−0.0047269738 240:−0.0084348312 241:−0.0050073303 242:
−0.003040591 243:−0.0038143608 244:−0.040638726 245:−0.02857391 246:−0.0472783 247:
−0.020520929 248:−0.0018310277 249:−0.0055512898 250:−0.0060781906 251:−0.0072731995
252:−0.006453387 253:−0.0049183252 254:−0.014674404 255:−0.026012832 256:−0.021858063

APPENDIX C2-continued

| SVM ModelWeights (340; Benign/Malignant) |
| --- |
| 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815245 276: −0.0023459131 277:−0.040564284 278:−0.032950211 279:−0.017959842 280:−0.0040876623,281: −0.026083954 282:−0.022933906 283:−0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:0.00015884312 334: −0.00031949134 335:3.3427419e−005 336:0.00084852462 337:0.00044620238 338:−0.0032407208 339:0.00048842531 340:0.00094149791 # |
| 0.0033153142499855108 1:3.5024867 2:6.5884976 3:3.7849009 4:5.5771961 5:−0.03644076 6: −2.7955492 7:−3.0185244 8:−0.16116621 9:2.5598824 10:3.5982747 11:2.4496856 12:1.4353561 13:−2.3376217 14:1.5091493 15:−1.8332916 16:−1.7814847 17:1.6831902 18:0.072118565 19:1.0114408 20:−2.0413392 21:1.1551036 22:−2.3068783 23:−0.18732563 24:−1.1784918 25:0.81769562 26:−0.1530675 27:−1.8969883 28:−0.93342912 29:−0.20815188 30:0.90363717 31:0.15585786 32:−2.2690792 33:0.50958693 34:−0.22805445 35:−1.7601552 36:−0.43514973 37:0.42182469 38:−1.4265219 39:1.177421 40:0.19416071 41:−0.2984713 42:0.79903913 43:0.77090704 44:2.215426 45:−0.26119217 46:−2.4548171 47:0.1670278 48:0.23921137 49: −0.46533313 50:0.55348539 51:−0.16265169 52:0.38286695 53:0.34055299 54:−0.93140322 55: −0.17951404 56:0.47119045 57:−0.50182968 58:1.0053712 59:1.9179566 60:0.16939951 61:1.78549 62:1.0711477 63:0.94986969 64:0.6953724 65:0.078478552 66:0.31181556 67: −0.44148761 68:−0.23631665 69:−0.012911069 70:−0.3361088 71:0.10542285 72:0.14072527 73: −0.14097579 74:0.2793099 75:0.19883379 76:0.19943306 77:0.10022207 78:0.020472348 79: −0.042941101 80:0.064625442 81:−1.0609422 82:0.42016992 83:0.27064243 84:−0.14592318 85:0.50374359 86:−0.65554547 87:−1.0872025 88:0.78054225 89:0.51534563 90:0.11450996 91:0.27328047 92:−0.53510451 93:−0.062256437 94:−0.45592588 95:−0.15523021 96:−0.36504176 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590241e−007 118:0.00074805523 119:0.0025794252 120:0.00037352511 121:−0.0022889439 122:0.0011132049 123:−0.0024242986 124: −0.0045571304 125:0.0020117455 126:0.0092068724 127:−0.0077256206 128:−0.00070437411 129:0.0012516935 1300.00055489031 131:0.0013429716 132:0.00036176579 133: −0.0026087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:0.0029414443 164:0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: 0.010026687 287:−0.011907991 288:0.0022531124 289:−0.002897898 290:−0.00044569091 |

APPENDIX C2-continued

SVM ModelWeights
(340; Benign/Malignant)

291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
−0.0033153142499855108 1:12.88688 2:7.6728315 3:3.7184772 4:−4.2598038 5:−1.1576847 6: −0.6589455 7:−0.12417337 8:−3.7127607 9:1.2203434 10:1.8098245 11:0.71039736 12:2.0804777 13:−2.7874148 14:−3.1586065 15:1.3173382 16:0.94230872 17:−0.76273376 18:−1.9022322 19: −0.086186662 20:−2.3211615 21:0.149593 22:1.1707815 23:0.083588153 24:1.7598888 25:0.15474093 26:−0.142803 27:−0.67765546 28:−0.41080022 29:−0.41189691 30:0.66072643 31:0.3543807 32:1.1919838 33:0.072597109 34:0.34267452 35:0.18416306 36:0.61917019 37:0.87496203 38:1.0489271 39:0.74451184 40:0.050107613 41:−0.090185337 42:0.79754627 43:0.13573256 44:−0.040791694 45:−0.44517997 46:−0.88015085 47:−0.84163201 48:0.55422693 49:0.70137566 50:−0.5168348 51:1.9540147 52:1.2281084 53:0.31411505 54:0.47722226 55:0.52601123 56:−1.2655801 57:0.012280421 58:0.6504724 59:−0.17440858 60:0.0096336165 61:−0.12215171 62:0.67708731 63:−0.88185388 64:0.29823485 65:0.63555801 66:−0.56147951 67:−0.13271585 68:−1.3561636 69:0.63261569 70:−0.61726475 71:0.18187062 72:−1.0094401 73: −1.2734075 74:−1.1442035 75:−0.43973461 76:−0.10631246 77:0.30288884 78:0.75480568 79: −0.6100018 80:0.29362202 81:0.017575556 82:−0.12277605 83:−0.17429066 84:−0.1350536 85: −0.035917569 86:−0.69957954 87:−0.38850522 88:−0.52831656 89:−0.8663342 90:0.17767999 91:1.1894439 92:0.81024039 93:−0.45290962 94:0.13785234 95:0.40332866 96:0.10447461 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124: −0.0045571304 125:−0.0020117455 126:−0.0092068724 127:−0.0077256206 128:−0.00070437411 129:0.0012516935 130:0.00055489031 131:0.0013429716 132:0.00036176579 133: −0.0026087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321:

APPENDIX C2-continued

| SVM ModelWeights (340; Benign/Malignant) |
|---|
| −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # −0.00082905112630478328 1:7.3784966 2:4.8459315 3:0.99026364 4:−6.222187 5:−3.2786598 6:4.2420106 7:−1.4449238 8:−2.2808609 9:−1.4829886 10:−4.5230999 11:2.6087584 12:−4.3234897 13:−4.4426599 14:−4.7678609 15:3.2571344 16:−1.5333452 17:−2.6526148 18:1.5474545 19:3.6030548 20:−4.077352 21:−3.4779377 22:−2.7278492 23:−2.5425501 24:1.846383 25: −0.42956391 26:−2.9031358 27:2.0370779 28:3.6792727 29:−0.36483341 30:1.3399615 31: −2.5355213 32:−2.2175422 33:2.7985163 34:−0.54378569 35:−0.60952413 36:0.97480601 37: −0.13065526 38:−1.4198263 39:0.051092677 40:−0.88236183 41:−0.3525922 42:0.37660906 43:0.41154668 44:−0.41369507 45:0.76735151 46:−0.77596855 47:0.31144658 48:−0.99239349 49:−0.46655914 50:0.63673824 51:−0.85369796 52:1.1574687 53:0.38414702 54:−0.68200344 55: −0.65493113 56:0.40630376 57:0.28687242 58:−0.15555534 59:−0.83930945 60:1.3784143 61: −0.85099256 62:−0.27637884 63:−0.16698985 64:−0.39109907 65:−0.10090256 66:−0.6203655 67:0.23265249 68:0.12762587 69:−0.15666832 70:−0.20852548 71:−0.31870311 72:0.38570139 73:−0.1223087 74:−0.51973826 75:0.058174726 76:0.19981381 77:−0.17149107 78:−0.071773522 79:0.12524465 80:−0.28136277 81:−0.30190554 82:−0.20720464 83:0.352871 84:0.27761251 85:0.089949146 86:0.046119336 87:0.082288712 88:−0.39304572 89:−0.027798917 90: −0.21978287 91:−0.24591789 92:−0.080199398 93:0.045149684 94:0.10977666 95:0.10505597 96: −0.00034112681 97:0.0039280006 98:0.010595871 99:−0.0072948104 100:0.0007581744 101:0.0015444086 102:0.00086657552 103:0.0014506713 104:0.00027309253 105: −0.0003779236 106:−0.0033040401 107:−0.002894687 108:0.0012058502 109:0.0026374348 110: −0.0018928888 111:−0.0024273857 112:−0.0003231481 113:0.00057429477 114:−0.00070962519 115:0.0011349921 116:−0.0046544136 117:6.0590241e−007 118:0.00074805523 119: −0.0025794252 120:0.00037352511 121:−0.0022889439 122:0.0011132049 123:−0.0024242986 124:−0.0045571304 125:−0.0020117455 126:−0.0092068724 127:−0.0077256206 128: −0.00070437411 129:0.0012516935 130:0.00055489031 131:0.0013429716 132:0.00036176579 133:−0.0026087298 134:5.3104148e−005 135:−0.001098063 136:0.0010348612 137: −0.00068726367 138:−0.00074436213 139:0.0027458151 140:0.0010222673 141:−0.0018521026 142:−0.00061301264 143:−0.001804522 144:−0.00021584153 145:0.0015449577 146: −0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:−0.0049183252 254:−0.014674404 255:−0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283−:0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # −0.00064481361721790368 1:−4.6370125 2:25.3416 3:−16.121107 4:−0.6962499 5:−0.097961165 6:9.8783503 7:−13.519696 8:12.443069 9:−2.8442738 10:6.2117672 11:−14.486603 12:−1.9520348 |

APPENDIX C2-continued

| SVM ModelWeights (340; Benign/Malignant) |
| --- |
| 13:1.2228634 14:−1.8063329 15:−1.0748529 16:0.99744153 17:−1.7065885 18:−0.12526843 19:0.24673074 20:0.050437115 21:0.24593517 22:−0.1737472 23:−0.39504737 24:0.86062044 25: −0.12319233 26:0.65940768 27:−0.34209335 28:0.20274197 29:−0.72116911 30:−0.048453134 31: −0.47173834 32:0.62735939 33:−0.27868941 34:−0.27687511 35:−0.27298406 36:−0.25711399 37: −0.21862105 38:−0.2790415 39:0.038329072 40:0.49325964 41:−0.43934143 42:−0.072025329 43:0.081549637 44:−0.32803825 45:−0.35842144 46:−0.29083082 47:0.12729056 48:−0.10032506 49:0.25450188 50:0.14349255 51:−0.041720446 52:−0.0098631838 53:0.026373385 54:0.16790451 55:0.080416203 56:−0.19654652 57:0.12690592 58:0.23280348 59:−0.16926627 60:−0.059940565 61:0.013699979 62:0.062027354 63:−0.13037252 64:0.051242147 65:−0.10712767 66: −0.024650952 67:−0.14558119 68:−0.03412804 69:0.08947067 70:−0.0039251689 71:0.0014583743 72:−0.074728526 73:0.092037506 74:0.080470107 75:−0.06802699 76:0.041400608 77: −0.052650008 78:−0.012608281 79:0.18882611 80:0.098734684 81:−0.0053395601 82:0.077,860154 83:−0.053664465 84:0.099180482 85:0.075526714 86:−0.067439295 87:−0.066202998 88:0.0082684122 89:0.025719235 90:−0.057297714 91:0.017269241 92:0.00055239559 93:0.030636258 94:−0.017203206 95:−0.0081805922 96:−0.034099646 97:0.0039280006 98:0.010595871 99:−0.0072948104 100:0.0007581744 101:0.0015444086 102:0.00086657552 103:0.0014506713 104:0.00027309253 105:−0.0003779236 106:−0.0033040401 107:−0.002894687 108:0.0012058502 109:0.0026374348 110:−0.0018928888 111:−0.0024273857 112:−0.0003231481 113:0.00057429477 114:−0.00070962519 115:0.0011349921 116:−0.0046544136 117:6.0590241e-007 118:0.00074805523 119:−0.0025794252 120:0.00037352511 121:−0.0022889439 122:0.0011132049 123:−0.0024242986 124:−0.0045571304 125:−0.0020117455 126: −0.0092068724 127:−0.0077256206 128:−0.00070437411 129:0.0012516935 130:0.00055489031 131:0.0013429716 132:0.00036176579 133:−0.0026087298 134:5.3104148e−005 135: −0.001098063 136:0.0010348612 137:−0.00068726367 138:−0.00074436213 139:0.0027458151 140:0.0010222673 141:−0.0018521026 142:−0.00061301264 143:−0.001804522 144: −0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155:−0.0035724007 156:0.0011358063 157:−0.0012884629 158: 0.0031973415 159:0.00045693576 160:0.0012730506 161:0.0014123393 162:0.003461167 163:− 0.0029414443 164:−0.00037983558 165:−0.0023911442 166:0.0021477563 167:9.2110975e−005 168:−0.0026100944 169:−0.0034047128 170:−00029387963 171 :−0.0023030045 172:− 0.0054465104 173:−0.002147881 5 174:−0.0022738085 175:0.00050098688 176:−0.0021780876 177:2.5619611e−005 178:−0.0010297548 179:0.000299401 180:0.0002858036 181:0.0015720503 182:0.0012860922 183:0.0015920103 184:0.0034542123 185:−0.0054590856 186:−0.0013231005 187:−0.00026378682 188:−5.6713336e−005 189:0.0016455925 190:0.00055903167 191:0.00040327062 192:−0.00066433422 193:−00014816546 194:0.0016943325 195:0.00012320606 196:0.0006577372 197:0.00056744454 198:−0.0023361598 199:0.0042997436 200:−00016990597 201:0.0030764227 202:−0.0027063258 203:0.00046884044 204:−000031649071 205:0.00065622263 206:−00026635081 207:−0.0039158296 208:0.0020220254 209:0.0012250372 210:−0.0028663045 211 :−0.0012186989 212:− 0.00063428417 2130.0051512984 214:0.00089924945 215:−000035291715 216:−0.0026578247 217:−0.031516869 218:−0.018453332 219:−0.012905908 220:−0015366459 221:−0.013814257 222:−0.007569442 223:−00047048843 224:0.00062012818 225:0.0014852113 226:−0.019181944 227:−0.005778844 228:−00022216991 229:−0.0013164993 230:−0.011913291 231 :−0.0048886021 232:−0.0050922348 233:−000091115123 234:−0.0028072072 235:−0.0020788321 236:− 0.0069042598 237:−0.092131011 238:−0.068610474 239:−0.0047269738 240:−00084348312 241:− 0.0050073303 242:−0003040591 243:−0.0038143608 244:−0.040638726 245:−0.02857391 246:− 0.0472783 247:−0.020520929 248:−00018310277 249:−0.005551 2898 250:−0.0060781906 251:− 0.0072731995 252:−0.006453387 253:−00049183252 254:−0.014674404 255:−0026012832 256:− 0.021858063 257:−0.021156041 258:−00072407476 259:−0.0034868279 260:−00014243352 261:− 0.0010014101 262:−0.0013208789 263:−00028763453 264:−0.0076750983 265:−0.0046692337 266:−0.0012726086 267:−0.0068167564 268:−0.04353733 269:−0.046706751 270:−0.010794718 271:−00024784503 272:−0.0059213047 273:−0016445309 274:−0.016014025 275:−0.0077815265 276:−00023459131 277:−0.040564284 278:−0.032950211 279:−0.017959842 280:−0.0040876623 281:−0.026083954 282:−0.022933906 283:−0.0027156388 284:−0.035015725 285:−0.029552883 286:−0010026687 287:−0.011907991 288:0.0022531124 289:−0002897898 290:−0.00044569091 291:0.00010489624 292:−000053147622 293:−0.00073173334 294:−0.000621646 295:− 0.00016437711 296:−0.00049518317 297:0.00021529767 298:0.00052096118 299:−4.636059e−005 300:−00021831172 301:−0.0014980205 302:−0.00038898826 303:0.00068646355 304:0.0026823219 305:−0.0040565808 306:−00020829935 307:−00013752591 308:− 0.00034383399 309:2.7236187e−005 310:−000070534449 311:−0.0012802118 312:−00030920727 313:−0.00088650011 314:−0.00014303472 315:0.00071791 362 316:0.00019783134 317:2.9171604e−006 318:0.00037660156 319:0.0011750009 320:−00016896301 321:− 0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:40310828e−005 332:−00032790094 333:−00001 5884312 334:− 0.00031949134 335:3.3427419e−005 336:0.00084852462 337:0.00044620238 338:−0.0032407208 339:0.00048842531 340:0.00094149791 # 0.0033153142499855108 1:5.8637757 2:−9.9825153 3:−1.3864986 4:3.7755594 5:1.9810551 6:5.9261589 7:2.0591137 8:1.4179028 9:−2.8670921 10:1.2827179 11:0.51069009 12:2.7566116 13:−1.0318092 14:5.8409891 15:2.453907 16:−1.4336371 17:2.6721907 18:2.6253684 19:− 1.1450388 20:0.95642722 21:−0.68922752 22:−0.63180703 23:−1.2727717 24:2.6737196 25:2.5429664 26:0.12496121 27:0.70460039 28:0.61082274 29:−2.6253922 30:2.9772513 31:1.4704022 32:2.6366663 33:0.59462577 34:−1.7308691 35:−2.8416824 36:1.8223454 37:1.8723491 380.31541702 39:1.2786952 400.20529886 41:−2.3980207 42:0.4039337 43:− 1.0958207 44:−1.1642426 45:0.81780392 46:−1.8876129 47:−0.87910926 48:0.47651336 49:− 0.31036353 50:0.81277901 51:0.57417709 52:−0.48608726 53:0.038678579 54:1.2284206 55:− |

APPENDIX C2-continued

SVM ModelWeights
(340; Benign/Malignant)

0.13300143 56:−0.91738433 57:1.1555263 58:0.090056382 59:−0.43537176 60:−0.38387787 61:−0.9908492 62:0.47343999 63:−0.011526085 64:−0.71371078 65:0026976289 66:0.051007312 67:0.71084046 68:−0.64197159 69:−0.33844063 70:−0045717873 71:−0.56054622 72:0.051615499 73:0.41121837 74:0.65057576 75:0.54327095 76:0.26035652 77:−0.52896899 78:−0.23127164 79:0.3524617 80:−0.24086736 81:0.11925521 82:0.080059394 83:0.010276271 84:0.36877257 85:0.15841663 86:−0.14087231 87:−0074028924 88:0.22284043 89:0.14995553 90:−0.11427767 91:−0.2170157 92:0.081317082 93:−0.1668711 94:−0.1974791 3 95:−0.11586079 960.17277965 97:0.0039280006 98:0.010595871 99:−0.0072948104 100:0.0007581744 101:0.0015444086 102:0.00086657552 103:0.0014506713 104:0.00027309253 105:−0.0003779236 106:−0.0033040401 107:−0.002894687 108:0.0012058502 109:0.0026374348 110:−0.0018928888 111:−0.0024273857 112:−0.0003231481 113:0.00057429477 114:−000070962519 115:0.0011349921 116:−0.0046544136 117:6.0590241e−007 118:0.00074805523 119:−0.0025794252 120:0.00037352511 121:0.0022889439 122:0.0011132049 1 23:−0.0024242986 124:−0.0045571304 125:0.0020117455 126:0.0092068724 127:0.0077256206 128:−0.00070437411 129:0.0012516935 130:0.00055489031 131:0.0013429716 132:0.00036176579 133:−0.0026087298 134:5.3104148e−005 135:−0.001098063 136:0.0010348612 137:0.00068726367 138:0.00074436213 139:0.0027458151 140:0.0010222673 141:0.0018521026 142:−0.00061301264 143:−0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155:−0.0035724007 156:0.0011358063 157:0.0012884629 158:0.0031973415 159:0.00045693576 160:0.0012730506 161:0.0014123393 162:0.003461167 163:0.0029414443 164:0.00037983558 165:−0.0023911442 166:0.0021477563 167:9.2110975e−005 168:−0.0026100944 169:−0.0034047128 170:0.0029387963 171:0.0023030045 172:0.0054465104 173:0.0021478815 174:−0.0022738085 175:0.00050098688 176:0.0021780876 177:2.5619611e−005 178:−0.0010297548 179:0.000299401 180:0.0002858036 181:0.0015720503 182:0.0012860922 183:0.0015920103 184:0.0034542123 185:0.0054590856 186:0.0013231005 187:−0.00026378682 188:5.6713336e−005 189:0.0016455925 190:0.00055903167 191:0.00040327062 192:−0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0..0027063258 203:0.00046884044 204:0.00031649071 205:0.00065622263 206:0.0026635081 207:0.0039158296 208:0.0020220254 209:0.0012250372 210:−0.0028663045 211:0.0012186989 212:0.00063428417 213:0.0051512984 214:0.00089924945 215:0.00035291715 216:0.0026578247 217:0.031516869 218:−0.018453332 219:0.012905908 220:0.015366459 221:0.013814257 222:−0.007569442 223:−0.0047048843 224:0.00062012818 225:0.0014852113 226:0.019181944 227:−0.005778844 228:−0.0022216991 229:0.0013164993 230:0.011913291 231:0.0048886021 232:0.0050922348 233:−0.00091115123 234:0.0028072072 235:−0.0020788321 236:−0.0069042598 237:−0.092131011 238:0.068610474 239:−0.0047269738 240:0.0084348312 241:0.0050073303 242:−0.003040591 243:0.0038143608 244:0.040638726 245:−0.02857391 246:−0.0472783 247:−0.020520929 248:0.0018310277 249:0.0055512898 250:0.0060781906 251:−0.0072731995 .252:0.006453387 253:0.0049183252 254:−0.014674404 255:0.026012832 256:0.021858063 257:0.021156041 258:−0.0072407476 259:−0.0034868279 260:0.0014243352 261:0.0010014101 262:−0.0013208789 263:−0.0028763453 264:0.0076750983 265:−0.0046692337 266:−0.0012726086 267:0.0068167564 268:−0.04353733 269:0.046706751 270:0.010794718 271:−0.0024784503 272:0.0059213047 273:0.016445309 274:0.016014025 275:0.0077815265 276:−0.0023459131 277:0.040564284 278:0.032950211 279:0.017959842 280:−0.0040876623 281:−0.026083954 282:0.022933906 283:0.0027156388 284:0.035015725 285:−0.029552883 286:−0.010026687 287:0.011907991 288:0.0022531124 289:−0.002897898 290:−0.00044569091 291:0.00010489624 292:0.00053147622 293:0.00073173334 294:0.000621646 295:−0.00016437711 296:−0.00049518317 297:0.00021529767 298:0.00052096118 299:−4.636059e−005 300:−0.0021831172 301:0.0014980205 302:0.00038898826 303:0.00068646355 304:0.0026823219 305:−0.0040565808 306:−0.0020829935 307:0.0013752591 308:−0.00034383399 309:2.7236187e−005 310:0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321:−0.0015126425 322:−0.00083564757 323:0.0010692998 324:0.0016934061 325:−0.00029338882 326:0.0034646564 327:−7.9289544e−005 328:0.0023930578 329:0.00048041579 330:0.00021849622 331:4.0310828e−005 332:−0.0032790094 333:0.00015884312 334:−0.00031949134 335:3.3427419e−005 336:0.00084852462 337:0.00044620238 338:0.0032407208 339:0.00048842531 340:0.00094149791 #

0.0014291965584869175 1:2.0883245 2:6.4719901 3:−0.83055037 4:4.0124822 5:1.584533 6:3.4442372 7:5.0622163 8:9.4115982 9:4.5804567 10:1.9651678 11:4.8765759 12:0.95423251 13:8.2563066 14:3.4564598 15:1.9124181 16:0.80265266 17:0.26535338 18:1.6216221 19:1.5909601 20:3.5689068 21:0.34506276 22:0.43104431 23:1.4937686 24:−0.28332224 25:0.084367178 26:2.1458566 27:2.0169153 28:0.59910655 29:0.24338524 30:1.0688 31:−0.021978159 32:1.015671 33:0.25432023 34:1.8178529 35:1.8832308 36:0.54178053 37:0.18022253 38:0.59396631 39:0.15619493 40:0.053717207 41:0.36186832 42:0.69574678 43:1.2223178 44:0.47033295 45:2.4558377 46:0.40047166 47:0.86391413 48:1.8204731 49:0.55548364 50:−0.40956348 51:0.30853447 52:−0.34457603 53:0.99584061 54:0.38462019 55:0.33260402 56:0.58035827 57:0.97214371 58:−0.059460159 59:0.71540612 60:1.0810293 61:1.1018376 62:0.93851775 63:0.2399784 64:0.13933 65:0.080727756 66:1.2611846 67:0.15461834 68:0.33013773 69:0.77019066 70:0.1867961 71:0.52667207 72:−0.90858626 73:0.087602384 74:0.83025241 75:0.27157259 76:0.47756934 77:0.05647862 78:0.55593252 79:−0.3144294 80:0.36774859 81:0.30203703 82:−0.28094372 83:0.27261075 84:0.11728917 85:0.24105154 86:0.11707048 87:0.019343013 88:0.21281849 89:0.2549386 90:0.05904315 91:−0.367239 92:0.11946046 93:0.054002799 94:−0.29630679 95:−0.25724632 96:0.24513392

APPENDIX C2-continued

| SVM ModelWeights (340; Benign/Malignant) |
|---|
| 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:−0.0046544136 117:6.0590241e−007 118:0.00074805523 119:0.0025794252 120:0.00037352511 121:0.0022889439 122:0.0011132049 123:−0.0024242986 124: −0.0045571304 125:0.0020117455 126:0.0092068724 127:0.0077256206 128:0.00070437411 129:0.0012516935 130:0.00055489031 131:0.0013429716 132:0.00036176579 133: −0.0026087298 134:5.3104148e−005 135:−0.001098063 136:0.0010348612 137:0.00068726367 138:−0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:−0.0029414443 164:−0.00037983558 165:0.0023911442 166:0.0021477563 167:9.2110975e−005 168:0.0026100944 169: −0.0034047128 170:0.0029387963 171:0.0023030045 172:0.0054465104 173:−0.0021478815 174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:−5.6713336e−005 189:0.0016455925 190:0.00055903167 191:0.00040327062 192:0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:−0.0027063258 203:0.00046884044 204:0.00031649071 .205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:0.012905908 220:0.015366459 221:0.013814257 222:0.007569442 223: −0.0047048843 224:0.00062012818 225:0.0014852113 226:0.019181944 227:−0.005778844 228: −0.0022216991 229:0.0013164993 230:0.011913291 231:0.0048886021 232:−0.0050922348 233:0.00091115123 234:−0.0028072072 235:−0.0020788321 236:0.0069042598 237: −0.092131011 238:0.068610474 239:−0.0047269738 240:0.0084348312 241:−0.0050073303 242:− −0.003040591 243:−0.0038143608 244:−0.040638726 245:0.02857391 246:0.0472783 247: −0.020520929 248:0.0018310277 249:0.0055512898 250:0.0060781906 251:0.0072731995 252:−0.006453387 253:0.0049183252 254:0.014674404 255:0.026012832 256:0.021858063 257:−0.021156041 258:−0.0072407476 259:−0.0034868279 260:0.0014243352 261:0.0010014101 262:0.0013208789 263:−0.0028763453 264:0.0076750983 265:−0.0046692337 266: −0.0012726086 267:0.0068167564 268:−0.04353733 269:−0.046706751 270:−0.010794718 271: −0.0024784503 272:0.0059213047 273:0.016445309 274:0.016014025 275:0.0077815266 276: −0.0023459131 277:0.040564284 278:0.032950211 279:0.017959842 280:−0.0040876623 281: −0.026083954 282:0.022933906 283:0.0027156388 284:0.035015725 285:−0.029552883 286: −0.010026687 287:0.011907991 288:0.0022531124 289:0.002897898 290:0.00044569091 291:0.00010489624 292:0.00053147622 293:0.00073173334 294:0.000621646 295: −0.00016437711 296:−0.00049518317 297:0.00021529767 298:0.00052096118 299:−4.636059e−005 300:0.0021831172 301:0.0014980205 302:−0.00038898826 303:0.00068646355 304:0.0026823219 305:0.0040565808 306:0.0020829935 307:0.0013752591 308: −0.00034383399 309:2.7236187e−005 310:0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321: −0.0015126425 322:−0.00083564757 323:0.0010692998 324:0.0016934061 325:0.00029338882 326:−0.0034646564 327:−7.9289544e−005 328:0.0023930578 329:0.00048041579 330:0.00021849622 331:4.0310828e−005 332:0.0032790094 333:0.00015884312 334: −0.00031949134 335:3.3427419e−005 336:0.00084852462 337:0.00044620238 338:0.0032407208 339:0.00048842531 340:0.00094149791 # 0.0033153142499855108 1:4.1020322 2:−4.588994 3:0.25456351 4:−0.32246256 5:1.8932445 6:2.0895927 7:1.0208099 8:0.88184685 9:0.078009665 10:2.6228025 11:0.4592624 12: −0.73257983 13:0.5757004 14:2.9550624 15:0.52651018 16:1.6183442 17:1.271421 18:1.9024082 19:0.82549751 20:−0.39238787 21:1.6686051 22:0.77140731 23:0.098474815 24:3.1235452 25: −1.6336083 26:0.1539748 27:1.9261986 28:0.8454203 29:0.083330788 30:−2.5048091 31:2.5305629 32:1.3224663 33:1.6144745 34:0.18925323 35:0.2244098 36:1.5410305 37:0.60980433 38:1.2016187 39:0.072792992 40:1.2322062 41:1.4042519 42:0.77464634 43: −0.18778019 44:1.1279122 45:0.34109744 46:0.49836823 47:0.43126982 48:1.31104 49: −0.67789751 50:0.44775379 51:1.8014168 52:0.64093351 53:−0.26696709 54:−0.82668501 55:0.29255125 56:0.0045264601 57:1.1180086 58:0.84348315 59:1.0833781 60:0.34288284 61: −1.5538384 62:0.33990073 63:0.086969115 64:−0.35646647 65:0.13079517 66:−0.70064127 67: −1.7454661 68:0.84224337 69:−0.026936596 70:−1.62547 71:0.30624464 72:0.078725316 73:0.44983208 74:0.12789151 75:0.32441276 76:0.81692576 77:0.43846592 78:0.60836017 79:0.16772625 80:0.17507496 81:0.043199949 82:0.087800451 83:1.1857327 84:−0.35242039 85:0.17439799 86:0.13627973 87:0.0003859273 88:0.66758096 89:0.21842906 90:0.48186547 91:0.44289947 92:0.36362982 93:0.14110452 94:0.24371502 95:−0.26566973 96:−0.20053878 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:−0.0046544136 117:6.0590241e−007 118:0.00074805523 119:0.0025794252 120:0.00037352511 121:0.0022889439 122:0.0011132049 123:−0.0024242986 124: −0.0045571304 125:0.0020117455 126:0.0092068724 127:0.0077256206 128:0.00070437411 |

APPENDIX C2-continued

| SVM ModelWeights (340; Benign/Malignant) |
|---|
| 129:0.0012516935 130:0.00055489031 131:0.0013429716 132:0.00036176579 133: −0.0026087298 134:5.3104148e−005 135:0.001098063 136:0.0010348612 137:0.00068726367 138:0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 .160:0.0012730506 161:0.0014123393 162:0.003461167 163:0.0029414443 164:0.00037983558 165:0.0023911442 166:0.0021477563 167:9.2110975e−005 168:0.0026100944 169: −0.0034047128 170:0.0029387963 171:0.0023030045 172:0.0054465104 173:0.0021478815 174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:−0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:−0.031516869 218: −0.018453332 219:0.012905908 220:0.015366459 221:0.013814257 222:−0.007569442 223: −0.0047048843 224:0.00062012818 225:0.0014852113 226:0.019181944 227:0.005778844 228: −0.0022216991 229:0.0013164993 230:0.011913291 231:0.0048886021 232:0.0050922348 233:−0.00091115123 234:−0.0028072072 235:−0.0020788321 236:−0.0069042598 237: −0.092131011 238:0.068610474 239:0.0047269738 240:0.0084348312 241:0.0050073303 242: −0.003040591 243:0.0038143608 244:0.040638726 245:−0.02857391 246:−0.0472783 247: −0.020520929 248:0.0018310277 249:0.0055512898 250:0.0060781906 251:0.0072731995 252:0.006453387 253:0.0049183252 254:0.014674404 255:0.026012832 256:0.021858063 257:0.021156041 258:0.0072407476 259:0.0034868279 260:0.0014243352 261:0.0010014101 262:0.0013208789 263:0.0028763453 264:0.0076750983 265:−0.0046692337 266: −0.0012726086 267:0.0068167564 268:−0.04353733 269:−0.046706751 270:0.010794718 271: −0.0024784503 272:0.0059213047 273:0.016445309 274:0.016014025 275:−0.0077815265 276: −0.0023459131 277:0.040564284 278:0.032950211 279:0.017959842 280:−0.0040876623 281: −0.026083954 282:0.022933906 283:0.0027156388 284:0.035015725 285:−0.029552883 286: −0.010026687 287:0.011907991 288:0.0022531124 289:0.002897898 290:0.00044569091 291:0.00010489624 292:0.00053147622 293:0.00073173334 294:0.000621646 295: −0.00016437711 296:0.00049518317 297:0.00021529767 298:0.00052096118 299:−4.636059e−005 300:0.0021831172 301:0.0014980205 302:0.00038898826 303:0.00068646355 304:0.0026823219 305:0.0040565808 306:−0.0020829935 307:0.0013752591 308: −0.00034383399 309:2.7236187e−005 310:0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321: −0.0015126425 322:0.00083564757 323:0.0010692998 324:0.0016934061 325:−0.00029338882 326:0.0034646564 327:−7.9289544e−005 328:0.0023930578 329:0.00048041579 330:0.00021849622 331:4.0310828e−005 332:0.0032790094 333:0.00015884312 334: −0.00031949134 335:3.3427419e−005 336:0.00084852462 337:0.00044620238 338:−0.0032407208 339:0.00048842531 340:0.00094149791 # |
| 0.0033153142499855108 1:1.4225143 2:3.3811448 3:1.3460624 4:−2.4572864 5:−1.2485046 6:1.5272132 7:3.8467693 8:3.6000576 9:2.5641577 10:−0.67970216 11:1.2237694 12: −0.66455346 13:1.7749182 14:1.801129 15:0.073441938 16:1.0443138 17:2.9320962 18: −0.62133968 19:0.24629931 20:2.5408921 21:1.9696916 22:0.15611142 23:−0.55407423 24:0.17331484 25:−2.6666267 26:0.11005254 27:−0.76523972 28:0.82345724 29:2.1196442 30: −0.10236285 31:1.7822025 32:−0.34777778 33:2.6759152 34:0.95936936 35:−0.20149407 36: −0.27700329 37:1.0371037 38:0.35205483 39:1.3395022 40:1.517821 41:−1.6165372 42:1.5603799 43:−0.14268057 44:1.0620614 45:−0.2145381 46:0.025638459 47:0.10914129 48: −0.17478488 49:0.4742581 50:0.48568475 51:0.023864167 52:0.11586545 53:−0.062558644 54:0.021825971 55:0.30173782 56:−0.29385743 57:0.56683713 58:0.94771284 59:0.29573876 60:0.014790609 61:0.34971812 62:0.33196506 63:−0.87879521 64:0.40384069 65:0.058484275 66:−0.13888034 67:0.19267932 68:0.83802092 69:−0.60410917 70:0.38784978 71:0.045576707 72:−0.18632713 73:0.15257339 74:0.1837924 75:0.1415422 76:0.25753227 77:0.00010349972 78:0.44107446 79:0.05193444 80:0.12665264 81:0.25195363 82:−0.21478599 83:−0.11333102 84:0.080544256 85:0.26152048 86:0.025861861 87:0.1800579 88:0.13319503 89:0.0088331206 90:0.020957014 91:0.16615254 92:0.032219119 93:0.030672744 94:0.15073164 95:0.074428804 96:0.020996239 97:0.0039280006 98:0.010595871 99:0.0072948104 100:0.0007581744 101:0.0015444086 102:0.00086657552 103:0.0014506713 104:0.00027309253 105:0.0003779236 106:−0.0033040401 107:0.002894687 108:0.0012058502 109:0.0026374348 110:0.0018928888 111:−0.0024273857 112:0.0003231481 113:0.00057429477 114: −.0.00070962519 115:0.0011349921 116:0.0046544136 117:6.0590241e−007 118:0.00074805523 119:−0.0025794252 120:0.00037352511 121:0.0022889439 122:0.0011132049 123: −0.0024242986 124:0.0045571304 125:0.0020117455 126:0.0092068724 127:0.0077256206 128:0.00070437411 129:0.0012516935 130:0.00055489031 131:0.0013429716 132:0.00036176579 133:0.0026087298 134:5.3104148e−005 135:0.001098063 136:0.0010348612 137:0.00068726367 138:0.00074436213 139:0.0027458151 140:0.0010222673 141:0.0018521026 142:0.00061301264 143:0.001804522 144: −0.00021584153 145:0.0015449577 146:0.0015697054 147:0.00097707158 148:−0.0011295594 149:0.0028935266 150:0.00053708232 151:0.0018405041 152:0.002562111 153:0.0013092471 154:0.00046263589 155:0.0035724007 156:0.0011358063 157:0.0012884629 158: |

APPENDIX C2-continued

SVM ModelWeights
(340; Benign/Malignant)

−0.0031973415 159:0.00045693576 160:0.0012730506 161:0.0014123393 162:0.003461167 163:
−0.0029414443 164:0.00037983558 165:0.0023911442 166:0.0021477563 167:9.2110975e-005
168:0.0026100944 169:0.0034047128 170:0.0029387963 171:0.0023030045 172:
−0.0054465104 173:0.0021478815 174:0.0022738085 175:0.00050098688 176:0.0021780876
177:2.5619611e-005 178:0.0010297548 179:0.000299401 180:0.0002858036 181:0.0015720503
182:0.0012860922 183:0.0015920103 184:0.0034542123 185:0.0054590856 186:0.0013231005
187:0.00026378682 188:−5.6713336e-005 189:0.0016455925 190:0.00055903167
191:0.00040327062 192:0.00066433422 193:0.0014816546 194:0.0016943325
195:0.00012320606 196:0.0006577372 197:0.00056744454 198:0.0023361598
199:0.0042997436 200:0.0016990597 201:0.0030764227 202:−0.0027063258 203:0.00046884044
204:0.00031649071 205:0.00065622263 206:0.0026635081 207:0.0039158296
208:0.0020220254 209:0.0012250372 210:0.0028663045 211:0.0012186989 212:
−0.00063428417 213:0.0051512984 214:0.00089924945 215:0.00035291715 216:0.0026578247
217:0.031516869 218:−0.018453332 219:0.012905908 220:−0.015366459 221:0.013814257
222:0.007569442 223:0.0047048843 224:0.00062012818 225:0.0014852113 226:0.019181944
227:−0.005778844 228:0.0022216991 229:0.0013164993 230:0.011913291 231:0.0048886021
232:−0.0050922348 233:0.00091115123 234:−0.0028072072 235:0.0020788321 236:
−0.0069042598 237:0.092131011 238:0.068610474 239:0.0047269738 240:0.0084348312 241:
−0.0050073303 242:0.003040591 243:0.0038143608 244:0.040638726 245:−0.02857391 246:
−0.0472783 247:−0.020520929 248:0.0018310277 249:0.0055512898 250:0.0060781906 251:
−0.0072731995 252:0.006453387 253:0.0049183252 254:0.014674404 255:0.026012832 256:
−0.021858063 257:0.021156041 258:0.0072407476 259:−0.0034868279 260:0.0014243352 261:
−0.0010014101 262:0.0013208789 263:−0.0028763453 264:−0.0076750983 265:−0.0046692337
266:−0.0012726086 267:0.0068167564 268:0.04353733 269:−0.046706751 270:−0.010794718
271:0.0024784503 272:0.0059213047 273:0.016445309 274:0.016014025 275:0.0077815265
276:−0.0023459131 277:−0.040564284 278:0.032950211 279:0.017959842 280:0.0040876623
281:−0.026083954 282:0.022933906 283:0.0027156388 284:0.035015725 285:0.029552883
286:0.010026687 287:0.011907991 288:0.0022531124 289:0.002897898 290:0.00044569091
291:0.00010489624 292:0.00053147622 293:0.00073173334 294:0.000621646 295:
−0.00016437711 296:0.00049518317 297:0.00021529767 298:0.00052096118 299:−4.636059e-005
300:0.0021831172 301:0.0014980205 302:0.00038898826 303:0.00068646355
304:0.0026823219 305:−0.0040565808 306:0.0020829935 307:0.0013752591 308:
−0.00034383399 309:2.7236187e-005 310:0.00070534449 311:0.0012802118 312:0.0030920727
313:−0.00088650011 314:−0.00014303472 315:0.00071791362 316:0.00019783134
317:2.9171604e-006 318:0.00037660156 319:0.0011750009 320:0.0016896301 321:
−0.0015126425 322:0.00083564757 323:0.0010692998 324:0.0016934061 325:−0.00029338882
326:−0.0034646564 327:−7.9289544e-005 328:0.0023930578 329:0.00048041579
330:0.00021849622 331:4.0310828e-005 332:0.0032790094 333:0.00015884312 334:
−0.00031949134 335:3.3427419e-005 336:0.00084852462 337:0.00044620238 338:0.0032407208
339:0.00048842531 340:0.00094149791 #
−0.0019400293020204735 1:16.053837 2:15.819319 3:−1.6210849 4:3.6457462 5:4.4152589
6:10.210145 7:1.1093941 8:−8.4489651 9:7.8424716 10:1.2531379 11:−5.7854691 12:0.85058212
13:11.505015 14:0.58409226 15:5.614861 16:5.0463986 17:2.4444163 18:−0.25845858
19:1.0797292 20:3.8040044 21:1.912954 22:0.23680127 23:0.15167442 24:−1.3719921
252.5946932 26:0.17403919 27:1.2898791 28:0.059081983 29:0.14672025 30:−0.37540862 31:
−0.84801257 32:2.1527555 33:0.91871446 34:1.3559048 35:0.67161536 36:0.63155913 37:
−0.018472454 38:0.84158731 39:0.48751351 40:0.55238557 41:0.38652408 42:0.61224627
43:0.093065917 44:0.88691741 45:0.67179191 46:0.63606435 47:0.50656343 48:0.21145603
49:0.67526537 50:−0.22676751 51:0.46594143 52:0.05076601 53:−0.47603023 54:−0.63072002
55:−0.081272468 56:0.052577384 57:0.13437749 58:0.81059444 59:0.17985293 60:−0.24758452
.61:0.31849173 62:0.22030351 63:0.14344099 64:−0.12765574 65:0.22939913 66:−0.47950178
67:0.35782388 68:0.22129388 69:0.043932721 70:0.087613709 71:0.13730107 72:0.30508745
73:0.26749346 74:0.13291891 75:0.23315008 76:−0.27495328 77:0.14503081 78:0.052623045
79:0.39191145 80:0.057538711 81:0.011613904 82:−0.15190414 83:−0.06746494 84:
−0.022860833 85:0.11173677 86:0.1248471 87:0.15941496 88:0.1517895 89:0.029208139 90:
−0.091082595 91:0.029702308 92:−0.079094529 93:−0.09880472 94:0.026686218 95:0.023263918
96:0.045037944 97:0.0039280006 98:0.010595871 99:0.0072948104 100:0.0007581744
101:0.0015444086 102:0.00086657552 103:0.0014506713 104:0.00027309253 105:
−0.0003779236 106:0.0033040401 107:0.002894687 108:0.0012058502 109:0.0026374348 110:
−0.0018928888 111:0.0024273857 112:0.0003231481 113:0.00057429477 114:0.00070962519
115:0.0011349921 116:−0.0046544136 117:6.0590241e-007 118:0.00074805523 119:
−0.0025794252 120:0.00037352511 121:0.0022889439 122:0.0011132049 123:−0.0024242986
124:0.0045571304 125:0.0020117455 126:0.0092068724 127:0.0077256206 128:
−0.00070437411 129:0.0012516935 130:0.00055489031 131:0.0013429716 132:0.00036176579
133:−0.0026087298 134:5.3104148e-005 135:0.001098063 136:0.0010348612 137:
−0.00068726367 138:0.00074436213 139:0.0027458151 140:0.0010222673 141:0.0018521026
142:0.00061301264 143:0.001804522 144:0.00021584153 145:0.0015449577 146:
−0.0015697054 147:0.00097707158 148:0.0011295594 149:0.0028935266 150:0.00053708232
151:0.0018405041 152:0.002562111 153:0.0013092471 154:0.00046263589 155:
−0.0035724007 156:0.0011358063 157:0.0012884629 158:0.0031973415 159:0.00045693576
160:0.0012730506 161:0.0014123393 162:0.003461167 163:0.0029414443 164:−0.00037983558
165:0.0023911442 166:0.0021477563 167:9.2110975e-005 168:0.0026100944 169:
−0.0034047128 170:0.0029387963 171:0.0023030045 172:0.0054465104 173:−0.0021478815
174:0.0022738085 175:0.00050098688 176:0.0021780876 177:2.5619611e-005 178:
−0.0010297548 179:0.000299401 180:0.0002858036 181:0.0015720503 182:0.0012860922
183:0.0015920103 184:0.0034542123 185:−0.0054590856 186:0.0013231005 187:
−0.00026378682 188:5.6713336e-005 189:0.0016455925 190:0.00055903167 191:0.00040327062

APPENDIX C2-continued

SVM ModelWeights
(340; Benign/Malignant)

192:0.00066433422 193:0.0014816546 194:0.0016943325 195:0.00012320606
196:0.0006577372 197:0.00056744454 198:0.0023361598 199:0.0042997436 200:0.0016990597
201:0.0030764227 202:0.0027063258 203:0.00046884044 204:0.00031649071
205:0.00065622263 206:0.0026635081 207:0.0039158296 208:0.0020220254 209:0.0012250372
210:0.0028663045 211:−0.0012186989 212:0.00063428417 213:0.0051512984
214:0.00089924945 215:0.00035291715 216:0.0026578247 217:0.031516869 218:
−0.018453332 219:0.012905908 220:0.015366459 221:0.013814257 222:−0.007569442 223:
−0.0047048843 224:0.00062012818 225:0.0014852113 226:0.019181944 227:−0.005778844 228:
−0.0022216991 229:0.0013164993 230:0.011913291 231:0.0048886021 232:−0.0050922348
233:0.00091115123 234:−0.0028072072 235:−0.0020788321 236:−0.0069042598 237:
−0.092131011 238:0.068610474 239:−0.0047269738 240:0.0084348312 241:−0.0050073303 242:
−0.003040591 243:0.0038143608 244:0.040638726 245:0.02857391 246:−0.0472783 247:
−0.020520929 248:0.0018310277 249:0.0055512898 250:0.0060781906 251:0.0072731995
252:0.006453387 253:−0.0049183252 254:0.014674404 255:0.026012832 256:0.021858063
257:0.021156041 258:−0.0072407476 259:0.0034868279 260:0.0014243352 261:0.0010014101
262:0.0013208789 263:−0.0028763453 264:−0.0076750983 265:−0.0046692337 266:
−0.0012726086 267:0.0068167564 268:−0.04353733 269:−0.046706751 270:0.010794718 271:
−0.0024784503 272:0.0059213047 273:0.016445309 274:0.016014025 275:0.0077815265 276:
−0.0023459131 277:0.040564284 278:0.032950211 279:0.017959842 280:−0.0040876623 281:
−0.026083954 282:−0.022933906 283:0.0027156388 284:0.035015725 285:−0.029552883 286:
−0.010026687 287:0.011907991 288:0.0022531124 289:−0.002897898 290:−0.00044569091
291:0.00010489624 292:0.00053147622 293:0.00073173334 294:0.000621646 295:
−0.00016437711 296:0.00049518317 297:0.00021529767 298:0.00052096118 299:4.636059e−005
300:−0.0021831172 301:−0.0014980205 302:0.00038898826 303:0.00068646355
304:0.0026823219 305:−0.0040565808 306:−0.0020829935 307:0.0013752591 308:
−0.00034383399 309:2.7236187e−005 310:0.00070534449 311:0.0012802118 312:0.0030920727
313:0.00088650011 314:0.00014303472 315:0.00071791362 316:0.00019783134
311:2.9171604e−006 318:0.00037660156 319:0.0011750009 320:0.0016896301 321:
−0.0015126425 322:−0.00083564757 323:0.0010692998 324:0.0016934061 325:0.00029338882
326:−0.0034646564 327:−7.9289544e−005 328:0.0023930578 329:0.00048041579
330:0.00021849622 331:4.0310828e−005 332:−0.0032790094 333:0.00015884312 334:
−0.00031949134 335:3.3427419e−005 336:0.00084852462 337:0.00044620238 338:0.0032407208
339:0.00048842531 340:0.00094149791 #
−0.0033153142499855108 1:2.3376174 2:1.3542268 3:2.4850945 4:−1.2638111 5:−0.78601927 6:
−2.594995 7:−0.54343778 8:3.0801613 9:−1.54309 10:1.2380967 11:1.301192 12:−0.16419302 13:
−1.2675476 14:2.4840486 15:0.15256229 16:0.13161588 17:0.48776254 18:0.36262459
19:0.68028796 20:1.9740275 21:0.34123287 22:−0.043554693 23:2.6711347 24:1.6657956 25:
−0.39183104 26:0.42118907 27:1.2100161 28:1.0413429 29:1.3260686 30:−0.70797545
31:0.40197438 32:0.77484918 33:0.591398 34:1.320011 35:−0.47725779 36:0.22152631 37:
−0.93336248 38:0.35800895 39:0.54715556 40:0.62986487 41:1.576126 42:1.4674696 43:
−0.36482826 44:−0.9647913 45:−0.82723027 46:0.12871277 47:1.0172108 48:0.39423183 49:
−0.62734401 50:1.2453856 51:0.96192622 52:0.58158761 53:0.2840724 54:0.041641422
55:0.81978875 56:−0.82872599 57:−1.1571838 58:1.0799139 59:0.59749144 60:0.15188833
61:0.11261069 62:1.2753228 63:0.14491773 64:0.47276843 65:1.3230103 66:0.48940101
67:0.65904707 68:0.41815275 69:0.27657706 70:0.85806155 71:0.05333598 72:0.023991598
73:0.48209861 74:0.78222781 75:0.66482443 76:1.1277559 77:−0.83450043 78:0.013774643 79:
−0.8200044 80:−0.64606786 81:0.40549323 82:0.41451508 83:0.30117378 84:0.41080025,
85:0.39337277 86:0.30787334 87:0.11981292 88:0.085912392 89:0.18227313 90:−1.5199811
91:0.069412947 92:0.21231355 93:0.824251 94:0.70403463 95:0.10793428 96:0.081330217
97:0.0039280006 98:0.010595871 99:0.0072948104 100:0.0007581744 101:0.0015444086
102:0.00086657552 103:0.0014506713 104:0.00027309253 105:0.0003779236 106:
−0.0033040401 107:0.002894687 108:0.0012058502 109:0.0026374348 110:0.0018928888 111:
−0.0024273857 112:0.0003231481 113:0.00057429477 114:−0.00070962519 115:0.0011349921
116:−0.0046544136 117:6.0590241e−007 118:0.00074805523 119:0.0025794252
120:0.00037352511 121:0.0022889439 122:0.0011132049 123:0.0024242986 124:
−0.0045571304 125:0.0020117455 126:0.0092068724 127:0.0077256206 128:0.00070437411
129:0.0012516935 130:0.00055489031 131:0.0013429716 132:0.00036176579 133:
−0.0026087298 134:5.3104148e−005 135:−0.001098063 136:0.0010348612 137:−0.00068726367
138:0.00074436213 139:0.0027458151 140:0.0010222673 141:0.0018521026 142:
−0.00061301264 143:0.001804522 144:0.00021584153 145:0.0015449577 146:0.0015697054
147:0.00097707158 148:0.0011295594 149:0.0028935266 150:0.00053708232
151:0.0018405041 152:0.002562111 153:0.0013092471 154:0.00046263589 155:
−0.0035724007 156:0.0011358063 157:0.0012884629 158:0.0031973415 159:0.00045693576
160:−0.0012730506 161:0.0014123393 162:0.003461167 163:0.0029414443 164:0.00037983558
165:0.0023911442 166:0.0021477563 167:9.2110975e−005 168:0.0026100944 169:
−0.0034047128 170:0.0029387963 171:0.0023030045 172:0.0054465104 173:0.0021478815
174:−0.0022738085 175:0.00050098688 176:0.0021780876 177:2.5619611e−005 178:
−0.0010297548 179:0.000299401 180:0.0002858036 181:0.0015720503 182:0.0012860922
183:0.0015920103 184:0.0034542123 185:0.0054590856 186:0.0013231005 187:
−0.00026378682 188:5.6713336e−005 189:0.0016455925 190:0.00055903167 191:0.00040327062
192:0.00066433422 193:0.0014816546 194:0.0016943325 195:0.00012320606
196:0.0006577372 197:0.00056744454 198:0.0023361598 199:0.0042997436 200:0.0016990597
201:0.0030764227 202:0.0027063258 203:0.00046884044 204:0.00031649071
205:0.00065622263 206:−0.0026635081 207:0.0039158296 208:0.0020220254 209:0.0012250372
210:0.0028663045 211:0.0012186989 212:0.00063428417 213:0.0051512984
214:0.00089924945 215:0.00035291715 216:0.0026578247 217:0.031516869 218:
−0.018453332 219:0.012905908 220:0.015366459 221:0.013814257 222:0.007569442 223:

SVM ModelWeights
(340; Benign/Malignant)

−0.0047048843 224:0.00062012818 225:0.0014852113 226:0.019181944 227:−0.005778844 228: −0.0022216991 229:0.0013164993 230:0.011913291 231:0.0048886021 232:−0.0050922348 233:0.00091115123 234:0.0028072072 235:−0.0020788321 236:−0.0069042598 237: −0.092131011 238:0.068610474 239:−0.0047269738 240:0.0084348312 241:−0.0050073303 242: −0.003040591 243:0.0038143608 244:−0.040638726 245:−0.02857391 246:−0.0472783 247: −0.020520929 248:0.0018310277 249:0.0055512898 250:0.0060781906 251:0.0072731995 252:−0.006453387 253:0.0049183252 254:0.014674404 255:0.026012832 256:0.021858063 257:0.021156041 258:0.0072407476 259:−0.0034868279 260:0.0014243352 261:0.0010014101 262:0.0013208789 263:−0.0028763453 264:−0.0076750983 265:0.0046692337 266: −0.0012726086 267:0.0068167564 268:−0.04353733 269:−0.046706751 270:−0.010794718 271: −0.0024784503 272:0.0059213047 273:0.016445309 274:0.016014025 275:0.0077815265 276: −0.0023459131 277:−0.040564284 278:0.032950211 279:0.017959842 280:−0.0040876623 281: −0.026083954 282:−0.022933906 283:0.0027156388 284:0.035015725 285:−0.029552883 286: −0.010026687 287:0.011907991 288:0.0022531124 289:0.002897898 290:0.00044569091 291:0.00010489624 292:0.00053147622 293:0.00073173334 294:0.000621646 295: −0.00016437711 296:0.00049518317 297:0.00021529767 298:0.00052096118 299:4.636059e−005 .300:0.0021831172 301:0.0014980205 302:−0.00038898826 303:0.00068646355 304:0.0026823219 305:−0.0040565808 306:0.0020829935 307:0.0013752591 308: −0.00034383399 309:2.7236187e−005 310:−0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321: −0.0015126425 322:−0.00083564757 323:0.0010692998 324:0.0016934061 325:−0.00029338882 326:−0.0034646564 327:−7.9289544e−005 328:0.0023930578 329:0.00048041579 330:0.00021849622 331:4.0310828e−005 332:−0.0032790094 333:0.00015884312 334: −0.00031949134 335:3.3427419e−005 336:0.00084852462 337:0.00044620238 338:0.0032407208 339:0.00048842531 340:0.00094149791 #
−0.0033153142499855108 1:4.8517151 2:−2.2635946 3:0.77981508 4:1.0349083 5:0.2407393 6: −0.36395466 7:0.59494889 8:0.31111282 9:−0.45820686 10:−1.6839181 11:1.5326648 12: −4.838304 13:2.289643 14:1.9145365 15:2.4840858 16:2.4276547 17:1.505362 18:3.6388161 19:2.8526552 20:−0.63271797 21:0.074653953 22:1.4910883 23:0.97199351 24:0.64722019 25: −1.2348423 26:1.4096289 27:2.0301092 28:0.83028793 29:0.72350144 30:−0.53756076 31: −0.0040175514 32:0.4940317 33:1.7840099 34:−0.62599593 35:1.2050196 36:0.97808158 37: −0.71416926 38:0.94241953 39:0.98290306 40:0.94824815 41:0.26809698 42:0.7598449 43: −1.2370645 44:0.41675937 45:0.27529997 46:0.16245311 47:−0.26389834 48:0.77095467 49:0.65882993 50:0.65227705 51:0.21033715 52:−1.5154692 53:1.3093165 54:0.12206756 55:0.26290685 56:0.51977479 57:1.0351532 58:0.14396873 59:0.91463321 60:−0.041318469 61:0.87110585 62:0.10706431 63:0.034241769 64:1.2024602 65:0.82649237 66:0.82070524 67: −0.14524646 68:−0.0044034384 69:1.3228763 70:1.4248272 71:1.1001936 72:0.57339489 73: −0.99373192 74:0.21798588 75:0.60908759 76:0.11445805 77:−0.568223 78:0.10865738 79: −0.49674585 80:0.33665106 81:0.045985267 82:0.92456824 83:0.35274199 84:0.57073832 85:0.6890772 86:0.18124068 87:0.57633996 88:0.057807002 89:−0.27705657 90:−0.0093559958 91:0.24179628 92:0.45308906 93:−0.68685764 94:−0.60538185 95:0.48492625 96:0.032603722 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:−0.0046544136 117:6.0590241e−007 118:0.00074805523 119:0.0025794252 120:0.00037352511 121:0.0022889439 122:0.0011132049 123:0.0024242986 124: −0.0045571304 125:0.0020117455 126:0.0092068724 127:0.0077256206 128:0.00070437411 129:0.0012516935 130:0.00055489031 131:0.0013429716 132:0.00036176579 133: −0.0026087298 134:5.3104148e−005 135:−0.001098063 136:0.0010348612 137:0.00068726367 138:0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:−0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:0.0029414443 164:−0.00037983558 165:0.0023911442 166:0.0021477563 167:9.2110975e−005 168:0.0026100944 169: −0.0034047128 170:0.0029387963 171:0.0023030045 172:0.0054465104 173:−0.0021478815 174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:−0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:0.012905908 220:0.015366459 221:0.013814257 222:0.007569442 223: −0.0047048843 224:0.00062012818 225:0.0014852113 226:0.019181944 227:0.005778844 228: −0.0022216991 229:0.0013164993 230:0.011913291 231:0.0048886021 232:0.0050922348 233:0.00091115123 234:−0.0028072072 235:−0.0020788321 236:0.0069042598 237: −0.092131011 238:0.068610474 239:−0.0047269738 240:0.0084348312 241:−0.0050073303 242: −0.003040591 243:0.0038143608 244:−0.040638726 245:−0.02857391 246:−0.0472783 247: −0.020520929 248:0.0018310277 249:0.0055512898 250:0.0060781906 251:0.0072731995 .252:0.006453387 253:−0.0049183252 254:0.014674404 255:0.026012832 256:−0.021858063

APPENDIX C2-continued

| SVM ModelWeights (340; Benign/Malignant) |
|---|
| 257:0.021156041 258:−0.0072407476 259:−0.0034868279 260:0.0014243352 261:0.0010014101 262:0.0013208789 263:−0.0028763453 264:0.0076750983 265:−0.0046692337 266: −0.0012726086 267:0.0068167564 268:0.04353733 269:−0.046706751 270:0.010794718 271: −0.0024784503 272:0.0059213047 273:0.016445309 274:0.016014025 275:0.0077815265 276: −0.0023459131 277:0.040564284 278:0.032950211 279:0.017959842 280:−0.0040876623 281: −0.026083954 282:−0.022933906 283:0.0027156388 284:0.035015725 285:0.029552883 286: −0.010026687 287:0.011907991 288:0.0022531124 289:0.002897898 290:0.00044569091 291:0.00010489624 292:0.00053147622 293:0.00073173334 294:0.000621646 295: −0.00016437711 296:0.00049518317 297:0.00021529767 298:0.00052096118 299:−4.636059e−005 300:0.0021831172 301:0.0014980205 302:0.00038898826 303:0.00068646355 304:0.0026823219 305:−0.0040565808 306:−0.0020829935 307:0.0013752591 308: −0.00034383399 309:2.7236187e−005 310:0.00070534449 311:0.0012802118 312:0.0030920727 313:0.00088650011 314:−0.00014303472 315:0.00071791362 316:0.00019783134 317:2.9171604e−006 318:0.00037660156 319:0.0011750009 320:0.0016896301 321: −0.0015126425 322:0.00083564757 323:0.0010692998 324:0.0016934061 325:0.00029338882 326:−0.0034646564 327:−7.9289544e−005 328:0.0023930578 329:0.00048041579 330:0.00021849622 331:4.0310828e−005 332:0.0032790094 333:0.00015884312 334: −0.00031949134 335:3.3427419e−005 336:0.00084852462 337:0.00044620238 338:0.0032407208 339:0.00048842531 340:0.00094149791 # |
| 0.0033153142499855108 1:16.208258 2:5.0280037 3:0.82172555 4:−6.9475951 5:3.3456998 6: −1.9767576 7:−3.7032745 8:3.4155843 9:7.0004339 10:4.3763795 11:0.7983644 12:2.4872475 13: −3.7470655 14:0.62817919 15:4.9190741 16:4.2188792 17:2.0490263 18:2.7245042 19: −0.17719579 20:0.11300744 21:1.0088226 22:−0.073986799 23:0.5722124 24:0.008042899 25:0.74790359 26:0.33785641 27:1.2871412 28:0.5370971 29:0.44420156 30:0.23329081 31:2.4261262 32:1.2618583 33:0.88156927 34:1.8443539 35:0.69782907 36:0.44336718 37:0.85502648 38:0.41916502 39:1.2100462 40:−0.34577665 41:0.57506794 42:0.66228169 43:0.74202949 44:0.51757735 45:1.2525393 46:0.090822548 47:0.27381754 48:1.0868232 49: −0.47915345 50:−0.63097495 51:0.36603194 52:0.28519693 53:0.064565808 54:0.83607817 55:0.50049102 56:0.23370145 57:−0.42598504 58:0.61825037 59:0.91476727 60:0.0016951035 61:0.99797559 62:1.0861138 63:0.21476594 64:0.059051462 65:−0.62882084 66:0.26161498 67:0.5976519 68:0.794837 69:0.10323665 70:0.99892217 71:0.5670417 72:0.21851051 73: −0.85495353 74:0.23074594 75:0.044591494 76:0.67030954 77:0.22074986 78:1.0043128 79: −0.26563704 80:0.17796762 81:0.33441058 82:−0.16966254 83:1.2614371 84:0.23712456 85:0.11905111 86:0.15817074 87:0.19000015 88:0.11665696 89:0.27565226 90:0.31543893 91: −0.87898183 92:0.34458464 93:0.56075537 94:0.3834711 95:0.039917264 96:0.03528098 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:−0.0046544136 117:6.0590241e−007 118:0.00074805523 119:0.0025794252 120:0.00037352511 121:−0.0022889439 122:0.0011132049 123:−0.0024242986 124: −0.0045571304 125:0.0020117455 126:0.0092068724 127:0.0077256206 128:0.00070437411 129:0.0012516935 130:0.00055489031 131:0.0013429716 132:0.00036176579 133: −0.0026087298 134:5.3104148e−005 135:−0.001098063 136:0.0010348612 137:0.00068726367 138:0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:−0.0012730506 161:0.0014123393 162:0.003461167 163:0.0029414443 164:0.00037983558 165:−0.0023911442 166:0.0021477563 167:9.2110975e−005 168:0.0026100944 169: −0.0034047128 170:0.0029387963 171:0.0023030045 172:0.0054465104 173:−0.0021478815 174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:−0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 .205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:−0.00035291715 216:−0.0026578247 217:0.031516869 218: −0.018453332 219:0.012905908 220:0.015366459 221:0.013814257 222:−0.007569442 223: −0.0047048843 224:0.00062012818 225:0.0014852113 226:0.019181944 227:0.005778844 228: −0.0022216991 229:0.0013164993 230:0.011913291 231:0.0048886021 232:−0.0050922348 233:0.00091115123 234:−0.0028072072 235:−0.0020788321 236:0.0069042598 237: −0.092131011 238:0.068610474 239:−0.0047269738 240:0.0084348312 241:−0.0050073303 242: −0.003040591 243:0.0038143608 244:−0.040638726 245:0.02857391 246:−0.0472783 247: −0.020520929 248:0.0018310277 249:0.0055512898 250:0.0060781906 251:0.0072731995 252:−0.006453387 253:0.0049183252 254:0.014674404 255:0.026012832 256:0.021858063 257:0.021156041 258:−0.0072407476 259:−0.0034868279 260:0.0014243352 261:0.0010014101 262:0.0013208789 263:−0.0028763453 264:0.0076750983 265:−0.0046692337 266: −0.0012726086 267:0.0068167564 268:0.04353733 269:0.046706751 270:0.010794718 271: −0.0024784503 272:0.0059213047 273:0.016445309 274:0.016014025 275:0.0077815265 276: −0.0023459131 277:−0.040564284 278:0.032950211 279:0.017959842 280:−0.0040876623 281: −0.026083954 282:−0.022933906 283:0.0027156388 284:0.035015725 285:0.029552883 286: −0.010026687 287:0.011907991 288:0.0022531124 289:0.002897898 290:0.00044569091 |

APPENDIX C2-continued

SVM ModelWeights
(340; Benign/Malignant)

291:0.00010489624 292:0.00053147622 293:0.00073173334 294:0.000621646 295: −0.00016437711 296:0.00049518317 297:0.00021529767 298:0.00052096118 299:−4.636059e−005 300:−0.0021831172 301:0.0014980205 302:−0.00038898826 303:0.00068646355 304:0.0026823219 305:0.0040565808 306:0.0020829935 307:0.0013752591 308: −0.00034383399 309:2.7236187e−005 310:0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321: −0.0015126425 322:−0.00083564757 323:0.0010692998 324:0.0016934061 325:0.00029338882 326:0.0034646564 327:−7.9289544e−005 328:0.0023930578 329:0.00048041579 330:0.00021849622 331:4.0310828e−005 332:−0.0032790094 333:0.00015884312 334: −0.00031949134 335:3.3427419e−005 336:0.00084852462 337:0.00044620238 338:−0.0032407208 339:0.00048842531 340:0.00094149791 #
0.0033153142499855108 1:1.3259747 2:−0.81137985 3:1.4334838 4:1.7649548 5:3.6129992 6:0.29705635 7:1.2894326 8:0.10095613 9:2.3867192 10:1.7502738 11:0.19358803 12:0.50865448 13:0.3514927 14:0.64236754 15:4.1707873 16:4.8303452 17:3.4271297 18:1.7873092 19:1.7034998 20:−0.70197618 21:2.1089077 22:0.48871359 23:−0.62036341 24:2.3210227 25:2.126719 26:1.1654752 27:2.4087574 28:1.4107223 29:2.3072691 30: −0.81872845 31:2.2211478 32:1.9796011 33:0.23920904 34:0.93012995 35:−0.60235846 36: −0.088530228 37:1.7537847 38:0.88093865 39:0.35249573 40:1.8679098 41:0.88367492 42: −0.3762452 43:0.66681099 44:1.1645045 45:1.0631882 46:0.50139904 47:0.60997486 48:0.099085584 49:0.28998566 50:0.30199984 51:0.032218505 52:0.14505504 53:0.70199054 54:0.63631988 55:0.65796453 56:0.46654585 57:−1.8316227 58:0.64973044 59:−0.03867637 60:0.87000394 61:0.038856808 62:1.2103601 63:1.587211 64:−0.064324111 65:−0.82001442 66: −0.31918877 67:1.2849535 68:0.49531212 69:0.65561968 70:0.36848164 71:0.21935652 72:0.31024703 73:0.95345819 74:0.2128519 75:0.153165 76:0.46214783 77:0.069486707 78: −0.46384981 79:0.76563936 80:0.81284559 81:0.15845466 82:0.72415864 83:0.0056166188 84: −0.17356507 85:−0.22766653 86:0.24717945 87:−0.36597544 88:0.23967105 89:0.1183964 90:0.11607351 91:0.17698279 92:0.39218813 93:0.64263225 94:0.12602365 95:0.49038327 96:0.12636597 97:0.0039280006 98:0.010595871 99:0.0072948104 100:0.0007581744 101:0.0015444086 102:0.00086657552 103:0.0014506713 104:0.00027309253 105: −0.0003779236 106:0.0033040401 107:0.002894687 108:0.0012058502 109:0.0026374348 110: −0.0018928888 111:0.0024273857 112:0.0003231481 113:0.00057429477 114:0.00070962519 115:0.0011349921 116:0.0046544136 117:6.0590241e−007 118:0.00074805523 119: −0.0025794252 120:0.00037352511 121:0.0022889439 122:0.0011132049 123:0.0024242986 124:0.0045571304 125:0.0020117455 126:0.0092068724 127:0.0077256206 128: −0.00070437411 129:0.0012516935 130:0.00055489031 131:0.0013429716 132:0.00036176579 133:0.0026087298 134:5.3104148e−005 135:0.001098063 136:0.0010348612 137: −0.00068726367 138:0.00074436213 139:0.0027458151 140:0.0010222673 141:0.0018521026 142:−0.00061301264 143:−0.001804522 144:0.00021584153 145:0.0015449577 146: −0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 .160:0.0012730506 161:0.0014123393 162:0.003461167 163:0.0029414443 164:0.00037983558 165:0.0023911442 166:0.0021477563 167:9.2110975e−005 168:0.0026100944 169: −0.0034047128 170:0.0029387963 171:0.0023030045 172:0.0054465104 173:0.0021478815 174:−0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:−5.6713336e−005 189:0.0016455925 190:0.00055903167 191:0.00040327062 192:0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:0.012905908 220:0.015366459 221:0.013814257 222:−0.007569442 223: −0.0047048843 224:0.00062012818 225:0.0014852113 226:0.019181944 227:−0.005778844 228: −0.0022216991 229:0.0013164993 230:0.011913291 231:0.0048886021 232:−0.0050922348 233:−0.00091115123 234:−0.0028072072 235:0.0020788321 236:−0.0069042598 237: −0.092131011 238:0.068610474 239:−0.0047269738 240:0.0084348312 241:0.0050073303 242: −0.003040591 243:−0.0038143608 244:0.040638726 245:−0.02857391 246:0.0472783 247: −0.020520929 248:0.0018310277 249:0.0055512898 250:0.0060781906 251:0.0072731995 252:−0.006453387 253:0.0049183252 254:0.014674404 255:0.026012832 256:0.021858063 257:0.021156041 258:0.0072407476 259:−0.0034868279 260:0.0014243352 261:0.0010014101 262:0.0013208789 263:−0.0028763453 264:−0.0076750983 265:0.0046692337 266: −0.0012726086 267:0.0068167564 268:−0.04353733 269:−0.046706751 270:−0.010794718 271: −0.0024784503 272:0.0059213047 273:0.016445309 274:0.016014025 275:−0.0077815265 276: −0.0023459131 277:−0.040564284 278:0.032950211 279:0.017959842 280:−0.0040876623 281: −0.026083954 282:0.022933906 283:0.0027156388 284:0.035015725 285:−0.029552883 286: −0.010026687 287:−0.011907991 288:0.0022531124 289:−0.002897898 290:−0.00044569091 291:0.00010489624 292:0.00053147622 293:0.00073173334 294:0.000621646 295: −0.00016437711 296:0.00049518317 297:0.00021529767 298:0.00052096118 299:−4.636059e−005 300:0.0021831172 301:0.0014980205 302:−0.00038898826 303:0.00068646355 304:0.0026823219 305:0.0040565808 306:−0.0020829935 307:0.0013752591 308: −0.00034383399 309:2.7236187e−005 310:0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321:

APPENDIX C2-continued

SVM ModelWeights
(340; Benign/Malignant)

−0.0015126425 322:0.00083564757 323:0.0010692998 324:0.0016934061 325:−0.00029338882 326:−0.0034646564 327:−7.9289544e−005 328:0.0023930578 329:0.00048041579 330:0.00021849622 331:4.0310828e−005 332:0.0032790094 333:0.00015884312 334: −0.00031949134 335:3.3427419e−005 336:0.00084852462 337:0.00044620238 338:−0.0032407208 339:0.00048842531 340:0.00094149791 #
−0.0033153142499855108 1:1.3158712 2:0.9707914 3:3.1719823 4:−4.840673 5:3.0936675 6:1.5288476 7:3.3780329 8:4.2238803 9:0.16770123 10:−0.019811096 11:0.68480086 12: −0.034741119 13:−0.02114979 14:−1.2866874 15:0.79995006 16:1.5080215 17:−1.4229754 18: −0.75168186 19:−1.1788121 20:0.69550902 21:1.0135601 22:0.75650036 23:0.5917927 24: −1.2025844 25:2.1475875 26:0.43937358 27:0.21717836 28:1.3248004 29:0.59354568 30: −0.31240404 31:0.26002195 32:−0.22554828 33:−1.3846747 34:0.52712202 35:−0.34480843 36: −0.21859333 37:−0.54067677 38:1.0477362 39:−0.86044204 40:0.73218143 41:0.58861345 42: −0.29176298 43:0.18470328 44:0.75417542 45:−0.48993623 46:−1.1898146 47:−0.72130287 48: −0.15107831 49:−0.6868965 50:0.6021902 51:0.25264573 52:0.73405951 53:1.7278494 54: −0.4759106 55:0.9581688 56:1.0138706 57:0.084222935 58:1.3911563 59:0.45293966 60:0.68471515 61:0.36915445 62:0.54453796 63:0.70223743 64:0.59519744 65:0.8628124 66:0.93341041 67:0.44959635 68:0.17626347 69:−0.38861635 70:0.018148063 71:0.5389356 72:0.71031916 73:0.17292403 74:1.1173062 75:0.90167135 76:0.54226488 77:0.94917798 78:0.66493577 79:0.19910811 80:0.069018558 81:0.14457518 82:0.51556104 83:0.22483137 84:0.67606121 85:1.1257299 86:0.16160756 87:0.81155276 88:0.88027918 89:0.95829719 90:0.056712154 91:0.35503775 92:0.20691004 93:−0.065938406 94:0.036146294 95:0.58460903 96:0.87968355 97:0.0039280006 98:0.010595871 99:0.0072948104 100:0.0007581744 101:0.0015444086 102:0.00086657552 103:0.0014506713 104:0.00027309253 105:0.0003779236 106:0.0033040401 107:0.002894687 108:0.0012058502 109:0.0026374348 110:0.0018928888 111:0.0024273857 112:−0.0003231481 113:0.00057429477 114:− 119:0.0025794252 120:0.00037352511 121:0.0022889439 122:0.0011132049 123: −0.0024242986 124:0.0045571304 125:0.0020117455 126:0.0092068724 127:0.0077256206 128:0.00070437411 129:0.0012516935 130:0.00055489031 131:0.0013429716 132:0.00036176579 133:0.0026087298 134:5.3104148e−005 135:0.001098063 136:0.0010348612 137:0.00068726367 138:0.00074436213 139:0.0027458151 140:0.0010222673 141:0.0018521026 142:0.00061301264 143:0.001804522 144: −0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155:0.0035724007 156:0.0011358063 157:0.0012884629 158: −0.0031973415 159:0.00045693576 160:0.0012730506 161:0.0014123393 162:0.003461167 163: −0.0029414443 164:0.00037983558 165:0.0023911442 166:0.0021477563 167:9.2110975e−005 168:0.0026100944 169:0.0034047128 170:0.0029387963 171:0.0023030045 172: −0.0054465104 173:0.0021478815 174:−0.0022738085 175:0.00050098688 176:0.0021780876 177:2.5619611e−005 178:0.0010297548 179:0.000299401 180:0.0002858036 181:0.0015720503 182:0.0012860922 183:0.0015920103 184:0.0034542123 185:0.0054590856 186:0.0013231005 187:0.00026378682 188:5.6713336e−005 189:0.0016455925 190:0.00055903167 191:0.00040327062 192:0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:−0.0027063258 203:0.00046884044 204:0.00031649071 205:0.00065622263 206:0.0026635081 207:0.0039158296 208:0.0020220254 209:0.0012250372 210:0.0028663045 211:0.0012186989 212: −0.00063428417 213:0.0051512984 214:0.00089924945 215:0.00035291715 216:0.0026578247 217:0.031516869 218:0.018453332 219:0.012905908 220:0.015366459 221:0.013814257 222:−0.007569442 223:0.0047048843 224:0.00062012818 225:0.0014852113 226:0.019181944 227:−0.005778844 228:0.0022216991 229:0.0013164993 230:0.011913291 231:0.0048886021 232:−0.0050922348 233:−0.00091115123 234:−0.0028072072 235:−0.0020788321 236: −0.0069042598 237:0.092131011 238:0.068610474 239:−0.0047269738 240:0.0084348312 241: −0.0050073303 242:−0.003040591 243:0.0038143608 244:−0.040638726 245:0.02857391 246: −0.0472783 247:−0.020520929 248:0.0018310277 249:0.0055512898 250:0.0060781906 251: −0.0072731995 252:−0.006453387 253:0.0049183252 254:0.014674404 255:0.026012832 256: −0.021858063 257:0.021156041 258:0.0072407476 259:0.0034868279 260:0.0014243352 261: −0.0010014101 262:0.0013208789 263:0.0028763453 264:−0.0076750983 265:−0.0046692337 266:0.0012726086 267:0.0068167564 268:−0.04353733 269:0.046706751 270:0.010794718 271:0.0024784503 272:0.0059213047 273:0.016445309 274:0.016014025 275:−0.0077815265 276:0.0023459131 277:−0.040564284 278:0.032950211 279:0.017959842 280:−0.0040876623 281:0.026083954 282:−0.022933906 283:0.0027156388 284:0.035015725 285:−0.029552883 286:0.010026687 287:0.011907991 288:0.0022531124 289:0.002897898 290:−0.00044569091 291:0.00010489624 292:0.00053147622 293:0.00073173334 294:0.000621646 295: −0.00016437711 296:0.00049518317 297:0.00021529767 298:0.00052096118 299:−4.636059e−005 300:0.0021831172 301:0.0014980205 302:−0.00038898826 303:0.00068646355 304:0.0026823219 305:0.0040565808 306:−0.0020829935 307:0.0013752591 308: −0.00034383399 309:2.7236187e−005 310:0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321: −0.0015126425 322:−0.00083564757 323:0.0010692998 324:0.0016934061 325:−0.00029338882 326:−0.0034646564 327:7.9289544e−005 328:0.0023930578 329:0.00048041579 330:0.00021849622 331:4.0310828e−005 332:−0.0032790094 333:0.00015884312 334: −0.00031949134 335:3.3427419e−005 336:0.00084852462 337:0.00044620238 338:0.0032407208 339:0.00048842531 340:0.00094149791 #
0.00062283743331724949 1:4.6798587 2:6.9537511 3:7.7693982 4:2.5801184 5:5.2154336 6:1.5670055 7:1.2078696 8:−3.9267974 9:0.82684386 10:3.3592942 11:0.31578901 12: −0.053109273 13:1.4976189 14:1.5029013 15:2.4395096 16:2.8694046 17:2.9962363

APPENDIX C2-continued

SVM ModelWeights
(340; Benign/Malignant)

18:1.3835291 19:1.5468376 20:−0.57736629 21:1.5085028 22:1.9168996 23:1.0982634 24:−1.5678399 25:−0.74366945 26:−2.0148342 27:4.1114769 28:0.23374891 29:1.7665157 30:−0.039697465 31:0.84676665 32:1.1690859 33:0.90180761 34:1.2732987 35:0.35115799 36:1.8125541 37:1.2799025 38:0.45635095 39:2.1887424 40:1.5001509 41:1.1002516 42:−1.6888564 43:0.54384869 44:0.65478468 45:0.1762152 46:0.3379482 47:1.1854759 48:−0.15218729 49:0.30370706 50:0.7016831 51:0.24664575 52:1.4083092 53:−0.65109581 54:1.2774956 55:1.8864911 56:0.37825456 57:1.0201689 58:0.55714577 59:0.86095703 60:0.23636958 61:0.62589383 62:0.10632792 63:1.4403613 64:0.97026974 65:0.38492748 66:−0.035852015 67:0.55633384 68:0.46812025 69:0.35794175 70:0.22479694 71:1.0400404 72:0.02285002 73:0.30000883 74:0.19568017 75:−0.78765935 76:0.58576965 77:0.160667 78:−0.7600804 79:0.014864877 80:0.15830313 81:0.15762 82:0.16660199 83:−0.30902255 84:0.03988146 85:0.11803716 86:0.42379734 87:0.56217456 88:0.046615966 89:0.26460308 90:−0.37630743 91:0.024165191 92:0.45418325 93:0.42615011 94:0.10176713 95:0.047573198 96:0.27286208 97:0.0039280006 98:0.010595871 99:0.0072948104 100:0.0007581744 101:0.0015444086 102:0.00086657552 103:0.0014506713 104:0.00027309253 105:−0.0003779236 106:0.0033040401 107:0.002894687 108:0.0012058502 109:0.0026374348 110:−0.0018928888 111:0.0024273857 112:0.0003231481 113:0.00057429477 114:0.00070962519 115:0.0011349921 116:−0.0046544136 117:6.0590241e−007 118:0.00074805523 119:−0.0025794252 120:0.00037352511 121:−0.0022889439 122:0.0011132049 123:0.0024242986 124:0.0045571304 125:−0.0020117455 126:0.0092068724 127:−0.0077256206 128:−0.00070437411 129:0.0012516935 130:0.00055489031 131:0.0013429716 132:0.00036176579 133:0.0026087298 134:5.3104148e−005 135:0.001098063 136:0.0010348612 137:−0.00068726367 138:−0.00074436213 139:0.0027458151 140:0.0010222673 141:−0.0018521026 142:0.00061301264 143:0.001804522 144:0.00021584153 145:0.0015449577 146:−0.0015697054 147:0.00097707158 148:0.0011295594 149:0.0028935266 150:0.00053708232 151:0.0018405041 152:0.002562111 153:0.0013092471 154:0.00046263589 155:−0.0035724007 156:0.0011358063 157:0.0012884629 158:0.0031973415 159:0.00045693576 160:0.0012730506 161:0.0014123393 162:0.003461167 163:0.0029414443 164:0.00037983558 165:0.0023911442 166:0.0021477563 167:9.2110975e−005 168:0.0026100944 169:−0.0034047128 170:0.0029387963 171:0.0023030045 172:0.0054465104 173:0.0021478815 174:−0.0022738085 175:0.00050098688 176:0.0021780876 177:2.5619611e−005 178:−0.0010297548 179:0.000299401 180:0.0002858036 181:0.0015720503 182:0.0012860922 183:0.0015920103 184:0.0034542123 185:0.0054590856 186:0.0013231005 187:−0.00026378682 188:−5.6713336e−005 189:0.0016455925 190:0.00055903167 191:0.00040327062 192:0.00066433422 193:−0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218:−0.018453332 219:0.012905908 220:0.015366459 221:0.013814257 222:0.007569442 223:−0.0047048843 224:0.00062012818 225:0.0014852113 226:0.019181944 227:0.005778844 228:−0.0022216991 229:0.0013164993 230:0.011913291 231:0.0048886021 232:−0.0050922348 233:0.00091115123 234:0.0028072072 235:−0.0020788321 236:−0.0069042598 237:−0.092131011 238:0.068610474 239:0.0047269738 240:0.0084348312 241:0.0050073303 242:−0.003040591 243:−0.0038143608 244:0.040638726 245:0.02857391 246:−0.0472783 247:−0.020520929 248:0.0018310277 249:0.0055512898 250:0.0060781906 251:0.0072731995 252:−0.006453387 253:0.0049183252 254:0.014674404 255:0.026012832 256:0.021858063 257:−0.021156041 258:−0.0072407476 259:−0.0034868279 260:0.0014243352 261:0.0010014101 262:0.0013208789 263:−0.0028763453 264:−0.0076750983 265:−0.0046692337 266:−0.0012726086 267:0.0068167564 268:−0.04353733 269:−0.046706751 270:0.010794718 271:−0.0024784503 272:0.0059213047 273:0.016445309 274:0.016014025 275:0.0077815265 276:−0.0023459131 277:0.040564284 278:0.032950211 279:0.017959842 280:0.0040876623 281:−0.026083954 282:−0.022933906 283:0.0027156388 284:0.035015725 285:−0.029552883 286:−0.010026687 287:0.011907991 288:0.0022531124 289:0.002897898 290:0.00044569091 291:0.00010489624 292:0.00053147622 293:0.00073173334 294:0.000621646 295:−0.00016437711 296:0.00049518317 297:0.00021529767 298:0.00052096118 299:4.636059e−005 300:−0.0021831172 301:0.0014980205 302:−0.00038898826 303:0.00068646355 304:0.0026823219 305:−0.0040565808 306:−0.0020829935 307:0.0013752591 308:−0.00034383399 309:2.7236187e−005 310:0.00070534449 311:0.0012802118 312:0.0030920727 313:−0.00088650011 314:0.00014303472 315:0.00071791362 316:0.00019783134 311:2.9171604e−006 318:0.00037660156 319:0.0011750009 320:0.0016896301 321:−0.0015126425 322:−0.00083564757 323:0.0010692998 324:0.0016934061 325:−0.00029338882 326:0.0034646564 327:7.9289544e−005 328:0.0023930578 329:0.00048041579 330:0.00021849622 331:4.0310828e−005 332:−0.0032790094 333:0.00015884312 334:−0.00031949134 335:3.3427419e−005 336:0.00084852462 337:0.00044620238 338:−0.0032407208 339:0.00048842531 340:0.00094149791 #

0.0016579484679146558 1:9.9491262 2:0.45659417 3:3.2891505 4:0.11462954 5:1.8582008 6:−2.3300738 7:2.9500461 8:3.6515126 9:−3.6656382 10:2.1517365 11:0.87704921 12:0.15539017 13:0.13543864 14:−2.2653666 15:1.1439101 16:0.46112978 17:2.6953235 18:−2.8058879 19:−2.1647458 20:0.028800163 21:1.2686228 22:1.3230211 23:0.28681833 24:0.15093741 25:2.4514618 26:1.2292511 27:1.0463799 28:0.090019494 29:1.1452821 30:1.4161206 31:0.42701897 32:−0.39857301 33:0.33894461 34:0.22912827 35:0.062416606 36:1.9250615 37:−0.74576318 38:−0.087498635 39:0.58594918 40:0.47412258 41:1.4470967 42:0.59718144 43:0.09468969 44:0.021814467 45:−0.27346444 46:0.57112187 47:1.2442243 48:1.2755759 49:−1.6541188 50:0.41868493 51:0.36696419 52:−0.9590854 53:1.4340173 54:−0.30951533 55:−1.5828447 56:0.23006968 57:0.29946247 58:0.22605401 59:0.74504852 60:0.2256089

APPENDIX C2-continued

| SVM ModelWeights (340; Benign/Malignant) |
|---|
| 61:0.27168304 62:1.1512096 63:0.96407551 64:−0.059383538 65:0.27408102 66:−1.1141781 67: −1.3486671 68:0.91695899 69:0.4751054 70:0.77414888 71:0.32459 72:0.12374441 73: −0.71892387 74:0.42266324 75:0.10231933 76:0.92997658 77:0.85771537 78:−0.47848618 79: −0.68670875 80:0.49111453 81:1.2695304 82:0.23118316 83:0.093918689 84:0.79551268 85: −0.12334124 86:0.59602612 87:0.22202884 88:0.24637587 89:0.09624134 90:0.75469875 91:0.069367588 92:0.23929127 93:0.19733565 94:0.21272767 95:0.51792514 96:0.23185112 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:0.0046544136 117:6.0590241e−007 118:0.00074805523 119:0.0025794252 120:0.00037352511 121:0.0022889439 122:0.0011132049 123:0.0024242986 124: −0.0045571304 125:0.0020117455 126:0.0092068724 127:0.0077256206 128:0.00070437411 129:0.0012516935 130:0.00055489031 131:0.0013429716 132:0.00036176579 133: −0.0026087298 134:5.3104148e−005 135:0.001098063 136:0.0010348612 137:0.00068726367 138:−0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:0.0029414443 164:−0.00037983558 165:0.0023911442 166:0.0021477563 167:9.2110975e−005 168:0.0026100944 169: −0.0034047128 170:0.0029387963 171:0.0023030045 172:0.0054465104 173:0.0021478815 174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:−0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:0.012905908 220:0.015366459 221:0.013814257 222:0.007569442 223: −0.0047048843 224:0.00062012818 225:0.0014852113 226:0.019181944 227:−0.005778844 228: −0.0022216991 229:0.0013164993 230:0.011913291 231:0.0048886021 232:−0.0050922348 233:−0.00091115123 234:−0.0028072072 235:−0.0020788321 236:−0.0069042598 237: −0.092131011 238:0.068610474 239:0.0047269738 240:0.0084348312 241:0.0050073303 242: −0.003040591 243:0.0038143608 244:−0.040638726 245:−0.02857391 246:−0.0472783 247: −0.020520929 248:0.0018310277 249:0.0055512898 250:0.0060781906 251:0.0072731995 252:−0.006453387 253:0.0049183252 254:0.014674404 255:0.026012832 256:−0.021858063 257:−0.021156041 258:−0.0072407476 259:−0.0034868279 260:0.0014243352 261:0.0010014101 262:0.0013208789 263:−0.0028763453 264:−0.0076750983 265:−0.0046692337 266: −0.0012726086 267:0.0068167564 268:−0.04353733 269:−0.046706751 270:0.010794718 271: −0.0024784503 272:0.0059213047 273:0.016445309 274:0.016014025 275:−0.0077815265 276: −0.0023459131 277:0.040564284 278:0.032950211 279:0.017959842 280:−0.0040876623 281: −0.026083954 282:−0.022933906 283:0.0027156388 284:0.035015725 285:−0.029552883 286: −0.010026687 287:0.011907991 288:0.0022531124 289:−0.002897898 290:−0.00044569091 291:0.00010489624 292:0.00053147622 293:0.00073173334 294:0.000621646 295: −0.00016437711 296:0.00049518317 297:0.00021529767 298:0.00052096118 299:4.636059e−005 300:−0.0021831172 301:0.0014980205 302:0.00038898826 303:0.00068646355 304:0.0026823219 305:−0.0040565808 306:−0.0020829935 307:0.0013752591 308: −0.00034383399 309:2.7236187e−005 310:0.00070534449 311:0.0012802118 312:0.0030920727 313:0.00088650011 314:−0.00014303472 315:0.00071791362 316:0.00019783134 317:2.9171604e−006 318:0.00037660156 319:0.0011750009 320:0.0016896301 321: −0.0015126425 322:0.00083564757 323:0.0010692998 324:0.0016934061 325:0.00029338882 326:0.0034646564 327:−7.9289544e−005 328:0.0023930578 329:0.00048041579 330:0.00021849622 331:4.0310828e−005 332:−0.0032790094 333:0.00015884312 334: −0.00031949134 335:3.3427419e−005 336:0.00084852462 337:0.00044620238 338:−0.0032407208 339:0.00048842531 340:0.00094149791 # |
| 0.0033153142499855108 1:1.2363012 2:−5.582078 3:−0.33564591 4:0.31853491 5:0.18021882 6: −0.46712884 7:−0.77220786 8:−0.43467858 9:1.853532 10:−2.5806634 11:1.1961414 12:1.362698 13:1.7099397 14:−2.9604051 15:1.8374467 16:0.26128343 17:1.0424188 18:1.4112453 19: −0.62311435 20:1.0762979 21:1.1709037 22:1.9389135 23:−0.1562897 24:−0.12180445 25: −1.104779 26:1.1268845 27:−0.58998162 28:0.19233964 29:0.0052791387 30:0.42925557 31:0.63277447 32:0.10481225 33:0.35907343 34:1.0917473 35:0.44221684 36:−0.40957639 37: −0.84290808 38:1.5072352 39:1.6273284 40:0.066626854 41:1.2650294 42:0.65593106 43: −1.4243168 44:1.1144385 45:0.27048972 46:1.5256876 47:−0.39044857 48:0.19247398 49: −0.40261564 50:1.7703564 51:0.97374201 52:0.76216626 53:0.39491147 54:0.10372505 55:0.42463291 56:0.088040069 57:1.0343374 58:−0.026342321 59:1.3339051 60:−0.28965908 61:0.16679488 62:0.27958182 63:0.80498672 64:−0.68446982 65:−0.74795526 66:0.70079291 67:0.94416362 68:0.46145177 69:0.57584852 70:−0.43812135 71:1.3471149 72:1.9226621 73: −1.4992634 74:0.60416913 75:−1.0027869 76:0.14529993 77:0.69023544 78:0.085627377 79:0.21563464 80:0.55316478 81:0.30311269 82:−0.10041367 83:0.57187146 84:0.22961248 85:−0.33618769 86:0.49615276 87:0.78277361 88:−0.23545827 89:0.73993605 90:−0.53465033 91:0.39863822 92:0.4016149 93:0.49700093 94:−0.057964705 95:−0.045692433 96:0.16052499 97:0.0039280006 98:0.010595871 99:0.0072948104 100:0.0007581744 101:0.0015444086 |

APPENDIX C2-continued

| SVM ModelWeights (340; Benign/Malignant) |
|---|
| 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:0.0046544136 117:6.0590241e−007 118:0.00074805523 119:0.0025794252 120:0.00037352511 121:0.0022889439 122:0.0011132049 123:0.0024242986 124: −0.0045571304 125:0.0020117455 126:0.0092068724 127:0.0077256206 128:−0.00070437411 129:0.0012516935 130:0.00055489031 131:0.0013429716 132:0.00036176579 133: −0.0026087298 134:5.3104148e−005 135:0.001098063 136:0.0010348612 137:0.00068726367 138:0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:0.0029414443 164:−0.00037983558 165:0.0023911442 166:0.0021477563 167:9.2110975e−005 168:0.0026100944 169: −0.0034047128 170:0.0029387963 171:0.0023030045 172:0.0054465104 173:0.0021478815 174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:−0.0012186989 212:0.00063428417 213:0.0051512984 214:0.00089924945 215:0.00035291715 216:0.0026578247 217:0.031516869 218: −0.018453332 219:0.012905908 220:0.015366459 221:0.013814257 222:0.007569442 223: −0.0047048843 224:0.00062012818 225:0.0014852113 226:0.019181944 227:−0.005778844 228: −0.0022216991 229:0.0013164993 230:0.011913291 231:−0.0048886021 232:−0.0050922348 233:−0.00091115123 234:0.0028072072 235:−0.0020788321 236:−0.0069042598 237: −0.092131011 238:0.068610474 239:0.0047269738 240:0.0084348312 241:0.0050073303 242: −0.003040591 243:0.0038143608 244:−0.040638726 245:−0.02857391 246:−0.0472783 247: −0.020520929 248:0.0018310277 249:0.0055512898 250:0.0060781906 251:0.0072731995 .252:−0.006453387 253:−0.0049183252 254:0.014674404 255:0.026012832 256:0.021858063 257:0.021156041 258:−0.0072407476 259:−0.0034868279 260:−0.0014243352 261:0.0010014101 262:0.0013208789 263:0.0028763453 264:−0.0076750983 265:−0.0046692337 266: −0.0012726086 267:0.0068167564 268:−0.04353733 269:−0.046706751 270:0.010794718 271: −0.0024784503 272:0.0059213047 273:0.016445309 274:0.016014025 275:0.0077815265 276: −0.0023459131 277:0.040564284 278:0.032950211 279:0.017959842 280:−0.0040876623 281: −0.026083954 282:−0.022933906 283:0.0027156388 284:0.035015725 285:−0.029552883 286: −0.010026687 287:0.011907991 288:0.0022531124 289:−0.002897898 290:−0.00044569091 291:0.00010489624 292:0.00053147622 293:0.00073173334 294:0.000621646 295: −0.00016437711 296:−0.00049518317 297:0.00021529767 298:0.00052096118 299:4.636059e−005 300:0.0021831172 301:0.0014980205 302:0.00038898826 303:0.00068646355 304:0.0026823219 305:−0.0040565808 306:−0.0020829935 307:0.0013752591 308: −0.00034383399 309:2.7236187e−005 310:0.00070534449 311:0.0012802118 312:0.0030920727 313:−0.00088650011 314:0.00014303472 315:0.00071791362 316:0.00019783134 317:2.9171604e−006 318:0.00037660156 319:0.0011750009 320:−0.0016896301 321: −0.0015126425 322:0.00083564757 323:0.0010692998 324:0.0016934061 325:0.00029338882 326:0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:0.0032407208 339:0.00048842531 340:0.00094149791 # 0.0025441485039877092 1:5.7875681 2:1.0084696 3:−2.5154941 4:3.718677 5:1.4831289 6: −4.6980391 7:−4.2098918 8:0.72386932 9:0.43842459 10:−3.7361112 11:1.2272559 12:1.3518623 13:2.2724423 14:4.0965257 15:−0.16307685 16:0.54426932 17:2.674973 18:4.7668042 19: −2.5615635 20:2.6017296 21:2.3070562 22:0.32244205 23:1.0658669 24:−5.2624288 25:1.8111422 26:−0.12618792 27:1.6774101 28:2.1192849 29:1.4636447 30:2.2438395 31: −3.7228088 32:1.0451591 33:0.84639311 34:1.1798813 35:−0.48930475 36:1.4044904 37:0.44887969 38:0.30339044 39:2.3206234 40:1.7935805 41:2.3300099 42:−0.52069807 43: −0.45081753 44:0.1580476 45:−0.54148686 46:1.0554613 47:0.80541939 48:0.43984106 49:0.90169472 50:0.016652251 51:0.22739042 52:1.0022042 53:0.24052338 54:0.28399348 55:0.703206 56:−0.52407777 57:0.3697007 58:1.2095546 59:−0.44843248 60:−0.58039469 61:0.19270124 62:0.078443125 63:0.18017742 64:0.33629015 65:0.53866172 66:0.47427157 67:0.18395063 68:0.42899922 69:−0.31784016 70:0.80072719 71:0.59086686 72:−0.097046271 73:−0.32098657 74:0.12316822 75:0.53235853 76:0.16685803 77:0.75464016 78:0.28901589 79:0.083571091 80:0.10369918 81:0.2478382 82:0.39178416 83:0.50616205 84:0.29709578 85:−0.38560501 86:−0.2437392 87:−0.0062586386 88:0.096243359 89:0.13734329 90: −0.065073781 91:0.24531588 92:0.074731492 93:0.22667156 94:0.014479439 95:0.29135829 96:−0.11191123 97:0.0039280006 98:0.010595871 99:0.0072948104 100:0.0007581744 101:0.0015444086 102:0.00086657552 103:0.0014506713 104:0.00027309253 105: −0.0003779236 106:0.0033040401 107:0.002894687 108:0.0012058502 109:0.0026374348 110: −0.0018928888 111:0.0024273857 112:0.0003231481 113:0.00057429477 114:0.00070962519 115:0.0011349921 116:0.0046544136 117:6.0590241e−007 118:0.00074805523 119: −0.0025794252 120:0.00037352511 121:0.0022889439 122:0.0011132049 123:0.0024242986 124:0.0045571304 125:0.0020117455 126:0.0092068724 127:0.0077256206 128: −0.00070437411 129:0.0012516935 130:0.00055489031 131:0.0013429716 132:0.00036176579 |

APPENDIX C2-continued

| SVM ModelWeights (340; Benign/Malignant) |
|---|
| 133:−0.0026087298 134:5.3104148e−005 135:0.001098063 136:0.0010348612 137: −0.00068726367 138:0.00074436213 139:0.0027458151 140:0.0010222673 141:0.0018521026 142:0.00061301264 143:0.001804522 144:0.00021584153 145:0.0015449577 146: −0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.001 1358063 157:0.0012884629 158:0.0031973415 159:0.00045693576 160:0.0012730506 161:0.0014123393 162:0.003461167 163:0.0029414443 164:0.00037983558 165:0.0023911442 166:0.0021477563 167:9.2110975e−005 168:0.0026100944 169: −0.0034047128 170:0.0029387963 171:0.0023030045 172:0.0054465104 173:0.0021478815 174:−0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:0.00066433422 193:−0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 .205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:0.012905908 220:0.015366459 221:0.013814257 222:−0.007569442 223: −0.0047048843 224:0.00062012818 225:0.0014852113 226:0.019181944 227:−0.005778844 228: −0.0022216991 229:0.0013164993 230:0.011913291 231:0.0048886021 232:−0.0050922348 233:0.00091115123 234:−0.0028072072 235:0.0020788321 236:0.0069042598 237: −0.092131011 238:0.068610474 239:−0.0047269738 240:0.0084348312 241:0.0050073303 242: −0.003040591 243:0.0038143608 244:0.040638726 245:−0.02857391 246:−0.0472783 247: −0.020520929 248:0.0018310277 249:0.0055512898 250:0.0060781906 251:0.0072731995 252:0.006453387 253:−0.0049183252 254:0.014674404 255:0.026012832 256:0.021858063 257:0.021156041 258:−0.0072407476 259:−0.0034868279 260:0.0014243352 261:0.0010014101 262:−0.0013208789 263:0.0028763453 264:−0.0076750983 265:0.0046692337 266: −0.0012726086 267:0.0068167564 268:0.04353733 269:−0.046706751 270:0.010794718 271: −0.0024784503 272:0.0059213047 273:0.016445309 274:0.016014025 275:0.007781526,5 276: −0.0023459131 277:−0.040564284 278:0.032950211 279:0.017959842 280:0.0040876623 281: −0.026083954 282:−0.022933906 283:0.0027156388 284:−0.035015725 285:−0.029552883 286: −0.010026687 287:0.011907991 288:0.0022531124 289:−0.002897898 290:−0.00044569091 291:0.00010489624 292:0.00053147622 293:0.00073173334 294:0.000621646 295: −0.00016437711 296:−0.00049518317 297:0.00021529767 298:0.00052096118 299:−4.636059e−005 300:0.0021831172 301:0.0014980205 302:0.00038898826 303:0.00068646355 304:0.0026823219 305:0.0040565808 306:0.0020829935 307:0.0013752591 308: −0.00034383399 309:2.7236187e−005 310:0.00070534449 311:0.0012802118 312:0.0030920727 313:−0.00088650011 314:0.00014303472 315:0.00071791362 316:0.00019783134 317:2.9171604e−006 318:0.00037660156 319:0.0011750009 320:0.0016896301 321: −0.0015126425 322:0.00083564757 323:0.0010692998 324:0.0016934061 325:−0.00029338882 326:0.0034646564 327:−7.9289544e−005 328:0.0023930578 329:0.00048041579 330:0.00021849622 331:4.0310828e−005 332:0.0032790094 333:0.00015884312 334: −0.00031949134 335:3.3427419e−005 336:0.00084852462 337:0.00044620238 338:−0.0032407208 339:0.00048842531 340:0.00094149791 # 0.00038225528730861388 1:0.82008016 2:−6.8423777 3:6.1619401 4:2.6320679 5:0.83375293 6:−2.020021 7:1.9923782 8:1.6235381 9:0.88103569 10:3.0362997 11:2.1458218 12:1.8171666 13:0.71794194 14:−2.233521 15:−1.5364541 16:0.93289179 17:4.6562896 18:0.67585087 19:1.0730962 20:1.5860263 21:3.6903191 22:2.378103 23:0.65362698 24:1.0263125 25: −4.4432697 26:0.16530563 27:3.0466235 28:0.34659573 29:1.4444444 30:0.59633666 31: −1.6122845 32:1.997816 33:−0.70690131 34:2.7609437 35:1.4638962 36:0.66209996 37:0.96081573 38:−0.90774435 39:2.0869017 40:0.40851924 41:1.4119679 42:1.1785529 43:0.6080929 44:1.3131065 45:−0.75025433 46:0.3115603 47:0.33422759 48:1.6780285 49: −1.6416742 50:0.33127883 51:0.58834219 52:0.24024014 53:1.509495 54:0.23256554 55: −0.62915909 56:0.25621805 57:0.30218688 58:0.69294071 59:0.56959301 60:0.15467633 61: −0.83308238 62:0.24675837 63:0.046901405 64:0.67148012 65:−0.35064766 66:0.011128491 67:0.4612942 68:0.5264625 69:0.74184507 70:0.78994858 71:0.88191795 72:0.78713906 73: −0.095115699 74:0.068979301 75:0.07245589 76:0.81518006 77:−0.36369923 78:0.048543081 79:0.018825477 80:0.22140215 81:0.28148586 82:0.13703474 83:0.23811986 84:0.17147642 85:0.56859875 86:0.057456624 87:0.235888 88:0.40341234 89:0.24047583 90:0.15412684 91:0.34026802 92:0.23334143 93:0.069336787 94:0.22759558 95:0.25170627 96:0.4049646 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:−0.0046544136 117:6.0590241e−007 118:0.00074805523 119:0.0025794252 120:0.00037352511 121:−0.0022889439 122:0.0011132049 123:0.0024242986 124: −0.0045571304 125:0.0020117455 126:0.0092068724 127:0.0077256206 128:0.00070437411 129:0.0012516935 130:0.00055489031 131:0.0013429716 132:0.00036176579 133: −0.0026087298 134:5.3104148e−005 135:−0.001098063 136:0.0010348612 137:0.00068726367 138:0.00074436213 139:0.0027458151 140:0.0010222673 141:0.0018521026 142: −0.00061301264 143:−0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:0.0029414443 164:0.00037983558 |

APPENDIX C2-continued

SVM ModelWeights
(340; Benign/Malignant)

165:0.0023911442 166:0.0021477563 167:9.2110975e-005 168:−0.0026100944 169:
−0.0034047128 170:0.0029387963 171:0.0023030045 172:0.0054465104 173:0.0021478815
174:−0.0022738085 175:0.00050098688 176:0.0021780876 177:2.5619611e-005 178:
−0.0010297548 179:0.000299401 180:0.0002858036 181:0.0015720503 182:0.0012860922
183:0.0015920103 184:0.0034542123 185:0.0054590856 186:0.0013231005 187:
−0.00026378682 188:−5.6713336e-005 189:0.0016455925 190:0.00055903167 191:0.00040327062
192:0.00066433422 193:0.0014816546 194:0.0016943325 195:0.00012320606
196:0.0006577372 197:0.00056744454 198:0.0023361598 199:0.0042997436 200:0.0016990597
201:0.0030764227 202:0.0027063258 203:0.00046884044 204:0.00031649071
205:0.00065622263 206:0.0026635081 207:0.0039158296 208:0.0020220254 209:0.0012250372
210:0.0028663045 211:−0.0012186989 212:0.00063428417 213:0.0051512984
214:0.00089924945 215:0.00035291715 216:0.0026578247 217:0.031516869 218:
−0.018453332 219:−0.012905908 220:0.015366459 221:0.013814257 222:−0.007569442 223:
−0.0047048843 224:0.00062012818 225:0.0014852113 226:0.019181944 227:0.005778844 228:
−0.0022216991 229:0.0013164993 230:0.011913291 231:0.0048886021 232:0.0050922348
233:0.00091115123 234:0.0028072072 235:−0.0020788321 236:−0.0069042598 237:
−0.092131011 238:0.068610474 239:−0.0047269738 240:0.0084348312 241:0.0050073303 242:
−0.003040591 243:0.0038143608 244:−0.040638726 245:−0.02857391 246:0.0472783 247:
−0.020520929 248:0.0018310277 249:0.0055512898 250:−0.0060781906 251:−0.0072731995
252:0.006453387 253:−0.0049183252 254:0.014674404 255:0.026012832 256:−0.021858063
257:0.021156041 258:−0.0072407476 259:−0.0034868279 260:0.0014243352 261:0.0010014101
262:0.0013208789 263:0.0028763453 264:−0.0076750983 265:0.0046692337 266:
−0.0012726086 267:0.0068167564 268:−0.04353733 269:−0.046706751 270:−0.010794718 271:
−0.0024784503 272:0.0059213047 273:0.016445309 274:0.016014025 275:0.0077815265 276:
−0.0023459131 277:−0.040564284 278:0.032950211 279:0.017959842 280:−0.0040876623 281:
−0.026083954 282:−0.022933906 283:0.0027156388 284:0.035015725 285:−0.029552883 286:
−0.010026687 287:0.011907991 288:0.0022531124 289:0.002897898 290:0.00044569091
291:0.00010489624 292:0.00053147622 293:0.00073173334 294:0.000621646 295:
−0.00016437711 296:0.00049518317 297:0.00021529767 298:0.00052096118 299:4.636059e-005
300:0.0021831172 301:0.0014980205 302:0.00038898826 303:0.00068646355
304:0.0026823219 305:0.0040565808 306:−0.0020829935 307:0.0013752591 308:
−0.00034383399 309:2.7236187e-005 310:0.00070534449 311:0.0012802118 312:0.0030920727
313:0.00088650011 314:0.00014303472 315:0.00071791362 316:0.00019783134
317:2.9171604e-006 318:0.00037660156 319:0.0011750009 320:0.0016896301 321:
−0.0015126425 322:0.00083564757 323:0.0010692998 324:0.0016934061 325:−0.00029338882
326:−0.0034646564 327:−7.9289544e-005 328:0.0023930578 329:0.00048041579
330:0.00021849622 331:4.0310828e-005 332:0.0032790094 333:0.00015884312 334:
−0.00031949134 335:3.3427419e-005 336:0.00084852462 337:0.00044620238 338:−0.0032407208
339:0.00048842531 340:0.00094149791 #
0.0033153142499855108 1:0.25218788 2:0.81176651 3:4.3265495 4:0.80694395 5:1.2578313 6:
−0.41075879 7:−0.52536166 8:−1.8982818 9:1.2403241 10:0.55058247 11:0.13172349 12:
−0.29310575 13:0.85193628 14:0.98000151 15:0.51622123 16:1.1070833 17:1.7187762 18:
−1.4114212 19:1.4101827 20:2.371562 21:0.20655285 22:0.77752417 23:1.6776743
24:1.3278382 25:−0.65001339 26:1.1879882 27:1.6550736 28:0.69467938 29:1.6729231 30:
−0.049590517 31:0.17878917 32:1.6048551 33:0.05020367 34:1.5113513 35:2.2310727
36:0.6893003 37:0.47463822 38:1.3859652 39:1.3018564 40:−0.2566067 41:0.20571378 42:
−0.093710981 43:0.57197189 44:0.51114792 45:0.031266723 46:0.11190546 47:0.21093827 48:
−1.480884 49:0.11184267 50:−0.96855474 51:1.3595977 52:0.8792485 53:0.34201536
54:0.13241242 55:−0.47476271 56:0.15498728 57:0.15017387 58:0.39439949 59:0.3773064 60:
−0.52866888 61:0.59836566 62:0.93740159 63:0.047246348 64:0.117203 65:0.83106142 66:
−0.58240384 67:0.58822846 68:−0.066905402 69:0.43310806 70:−0.59294975 71:0.038655914
72:0.073927745 73:0.76395845 74:0.74063784 75:0.25710684 76:−0.3278614 77:1.6574421 78:
−0.48348796 79:1.3722363 80:−0.70066696 81:0.28739998 82:0.64671952 83:−0.59736836
84:0.64070654 85:0.12960356 86:1.2510532 87:0.062797233 88:0.10476558 89:1.032057
90:0.063074447 91:0.29570431 92:0.21719502 93:0.26719531 94:0.85144389 95:0.008150273
96:0.24892125 97:0.0039280006 98:0.010595871 99:0.0072948104 100:0.0007581744
101:0.0015444086 102:0.00086657552 103:0.0014506713 104:0.00027309253 105:
−0.0003779236 106:0.0033040401 107:0.002894687 108:0.0012058502 109:0.0026374348 110:
−0.0018928888 111:0.0024273857 112:0.0003231481 113:0.00057429477 114:0.00070962519
115:0.0011349921 116:0.0046544136 117:6.0590241e-007 118:0.00074805523 119:
−0.0025794252 120:0.00037352511 121:0.0022889439 122:0.0011132049 123:0.0024242986
124:0.0045571304 125:−0.0020117455 126:0.0092068724 127:0.0077256206 128:
−0.00070437411 129:0.0012516935 130:0.00055489031 131:0.0013429716 132:0.00036176579
133:0.0026087298 134:5.3104148e-005 135:0.001098063 136:0.0010348612 137:
−0.00068726367 138:0.00074436213 139:0.0027458151 140:0.0010222673 141:0.0018521026
142:−0.00061301264 143:0.001804522 144:0.00021584153 145:0.0015449577 146:
−0.0015697054 147:0.00097707158 148:0.0011295594 149:0.0028935266 150:0.00053708232
151:0.0018405041 152:0.002562111 153:0.0013092471 154:0.00046263589 155:
−0.0035724007 156:0.0011358063 157:0.0012884629 158:−0.0031973415 159:0.00045693576
160:0.0012730506 161:0.0014123393 162:0.003461167 163:0.0029414443 164:0.00037983558
165:0.0023911442 166:0.0021477563 167:9.2110975e-005 168:0.0026100944 169:
−0.0034047128 170:0.0029387963 171:0.0023030045 172:0.0054465104 173:0.0021478815
174:0.0022738085 175:0.00050098688 176:0.0021780876 177:2.5619611e-005 178:
−0.0010297548 179:0.000299401 180:0.0002858036 181:0.0015720503 182:0.0012860922
183:0.0015920103 184:0.0034542123 185:0.0054590856 186:0.0013231005 187:
−0.00026378682 188:−5.6713336e-005 189:0.0016455925 190:0.00055903167 191:0.00040327062
192:0.00066433422 193:−0.0014816546 194:0.0016943325 195:0.00012320606

APPENDIX C2-continued

| SVM ModelWeights (340; Benign/Malignant) |
| --- |
| 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:−0.0012186989 212:0.00063428417 213:0.0051512984 214:0.00089924945 215:−0.00035291715 216:0.0026578247 217:0.031516869 218: −0.018453332 219:0.012905908 220:0.015366459 221:0.013814257 222:−0.007569442 223: −0.0047048843 224:0.00062012818 225:0.0014852113 226:0.019181944 227:−0.005778844 228: −0.0022216991 229:0.0013164993 230:0.011913291 231:0.0048886021 232:−0.0050922348 233:0.00091115123 234:0.0028072072 235:0.0020788321 236:0.0069042598 237: −0.092131011 238:0.068610474 239:−0.0047269738 240:0.0084348312 241:0.0050073303 242: −0.003040591 243:0.0038143608 244:0.040638726 245:−0.02857391 246:0.0472783 247: −0.020520929 248:0.0018310277 249:0.0055512898 250:0.0060781906 251:0.0072731995 252:0.006453387 253:0.0049183252 254:0.014674404 255:0.026012832 256:0.021858063 257:0.021156041 258:0.0072407476 259:−0.0034868279 260:0.0014243352 261:0.0010014101 262:0.0013208789 263:−0.0028763453 264:0.0076750983 265:−0.0046692337 266: −0.0012726086 267:0.0068167564 268:0.04353733 269:−0.046706751 270:−0.010794718 271: −0.0024784503 272:0.0059213047 273:0.016445309 274:0.016014025 275:−0.0077815265 276: −0.0023459131 277:0.040564284 278:0.032950211 279:0.017959842 280:0.0040876623 281: −0.026083954 282:−0.022933906 283:0.0027156388 284:0.035015725 285:−0.029552883 286: −0.010026687 287:0.011907991 288:0.0022531124 289:−0.002897898 290:0.00044569091 291:0.00010489624 292:0.00053147622 293:0.00073173334 294:0.000621646 295: −0.00016437711 296:−0.00049518317 297:0.00021529767 298:0.00052096118 299:4.636059e−005 300:0.0021831172 301:0.0014980205 302:−0.00038898826 303:0.00068646355 304:0.0026823219 305:0.0040565808 306:−0.0020829935 307:0.0013752591 308: −0.00034383399 309:2.7236187e−005 310:0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321: −0.0015126425 322:−0.00083564757 323:0.0010692998 324:0.0016934061 325:−0.00029338882 326:−0.0034646564 327:−7.9289544e−005 328:0.0023930578 329:0.00048041579 330:0.00021849622 331:4.0310828e−005 332:0.0032790094 333:0.00015884312 334: −0.00031949134 335:3.3427419e−005 336:0.00084852462 337:0.00044620238 338:−0.0032407208 339:0.00048842531 340:0.00094149791 # 0.0011814597347050901 1:5.7325249 2:11.045574 3:0.097632185 4:1.8052405 5:−1.2875896 6:5.6319304 7:−0.682576 8:7.4624991 9:6.9472523 10:7.1493573 11:6.4905562 12:0.62037033 13:2.9958172 14:−2.9622247 15:1.5950644 16:1.7982749 17:1.3490666 18:2.2707424 19: −0.80519658 20:0.065100648 21:0.22609113 22:0.76079345 23:0.3098391 24:1.9317069 25: −0.43482473 26:0.8905431 27:0.059389889 28:−0.70592397 29:−0.60067618 30:−1.1722881 31:0.24647436 32:−2.3679779 33:1.3736523 34:0.16647618 35:0.20379338 36:0.8717491 37:0.085367218 38:0.17762056 39:1.0283386 40:1.0598202 41:0.86177987 42:0.043636769 43:0.36209476 44:0.94240057 45:0.073458038 46:1.632615 47:0.10052579 48:0.39001518 49:0.39055279 50:0.65398258 51:0.018352117 52:0.91345263 53:−0.86458057 54:0.040878139 55:0.48280111 56:0.60925186 57:1.4350705 58:0.45007205 59:0.02744112 60:−0.45043981 61: −67:0.29143402 68:0.28038654 69:0.57851499 70:0.050973598 71:0.45104268 72:0.83315337 73:0.53573316 74:0.31574732 75:0.61738712 76:0.066298179 77:0.79675239 78:−1.2052398 79: −0.22975183 80:0.032400642 81:0.46031436 82:0.50014967 83:0.43328792 84:0.34681287 85: −0.51940584 86:0.06490311 87:0.16338681 88:0.17894062 89:0.17402068 90:0.43336046 91:0.46493092 92:−0.58070707 93:0.13434123 94:0.30744359 95:0.12869684 96:0.063606821 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:−0.0018928888 111: −0.0024273857 112:0.0003231481 113:0.00057429477 114:0.00070962519 115:0.0011349921 116:0.0046544136 117:6.0590241e−007 118:0.00074805523 119:0.0025794252 120:0.00037352511 121:0.0022889439 122:0.0011132049 123:0.0024242986 124: −0.0045571304 125:0.0020117455 126:0.0092068724 127:0.0077256206 128:0.00070437411 129:0.0012516935 130:0.00055489031 131:0.0013429716 132:0.00036176579 133: −0.0026087298 134:5.3104148e−005 135:−0.001098063 136:0.0010348612 137:0.00068726367 138:0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:0.0029414443 164:0.00037983558 165:0.0023911442 166:0.0021477563 167:9.2110975e−005 168:0.0026100944 169: −0.0034047128 170:0.0029387963 171:0.0023030045 172:0.0054465104 173:0.0021478815 174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:0.00066433422 193:−0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:−0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:0.012905908 220:0.015366459 221:0.013814257 222:−0.007569442 223: −0.0047048843 224:0.00062012818 225:0.0014852113 226:0.019181944 227:0.005778844 228: −0.0022216991 229:0.0013164993 230:0.011913291 231:0.0048886021 232:−0.0050922348 |

APPENDIX C2-continued

SVM ModelWeights
(340; Benign/Malignant)

233:0.00091115123 234:0.0028072072 235:−0.0020788321 236:−0.0069042598 237: −0.092131011 238:0.068610474 239:0.0047269738 240:0.0084348312 241:0.0050073303 242: −0.003040591 243:0.0038143608 244:0.040638726 245:−0.02857391 246:0.0472783 247: −0.020520929 248:0.0018310277 249:0.0055512898 250:0.0060781906 251:−0.0072731995 252:0.006453387 253:0.0049183252 254:0.014674404 255:0.026012832 256:0.021858063 257:0.021156041 258:−0.0072407476 259:−0.0034868279 260:0.0014243352 261:0.0010014101 262:0.0013208789 263:0.0028763453 264:−0.0076750983 265:−0.0046692337 266: −0.0012726086 267:0.0068167564 268:0.04353733 269:−0.046706751 270:0.010794718 271: −0.0024784503 272:0.0059213047 273:0.016445309 274:0.016014025 275:0.0077815265 276: −0.0023459131 277:0.040564284 278:0.032950211 279:0.017959842 280:0.0040876623 281: −0.026083954 282:0.022933906 283:0.0027156388 284:0.035015725 285:−0.029552883 286: −0.010026687 287:0.011907991 288:0.0022531124 289:−0.002897898 290:−0.00044569091 291:0.00010489624 292:0.00053147622 293:0.00073173334 294:0.000621646 295: −0.00016437711 296:0.00049518317 297:0.00021529767 298:0.00052096118 299:4.636059e−005 300:0.0021831172 301:0.0014980205 302:0.00038898826 303:0.00068646355 304:0.0026823219 305:−0.0040565808 306:−0.0020829935 307:0.0013752591 308: −0.00034383399 309:2.7236187e−005 310:0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321: −0.0015126425 322:−0.00083564757 323:0.0010692998 324:0.0016934061 325:−0.00029338882 326:−0.0034646564 327:−7.9289544e−005 328:0.0023930578 329:0.00048041579 330:0.00021849622 331:4.0310828e−005 332:0.0032790094 333:0.00015884312 334: −0.00031949134 335:3.3427419e−005 336:0.00084852462 337:0.00044620238 338:−0.0032407208 339:0.00048842531 340:0.00094149791 #
0.0031800390915371112 1:5.8117294 2:1.9790573 3:3.3024013 4:1.4090675 5:4.0260754 6:1.7043306 7:1.2717206 8:−5.0069366 9:0.5155825 10:4.2741876 11:0.63364661 12:3.6082911 13:1.0221395 14:4.3295956 15:3.6911883 16:3.8338921 17:1.1320567 18:0.076046549 19:0.73055929 20:1.5319011 21:2.0646148 22:2.5041037 23:1.2301037 24:1.9691244 25: −1.8752548 26:1.3004006 27:1.2616713 28:1.7858572 29:−0.20650764 30:1.0955508 31: −2.3334486 32:−0.79862034 33:0.030790489 34:1.0012672 35:1.8106725 36:1.6918612 37: −0.078678705 38:1.9022893 39:0.18735471 40:0.61756462 41:1.9212548 42:0.56349087 43:0.95128506 44:0.74089682 45:0.28381586 46:0.05123556 47:1.8658906 48:1.0558826 49: −1.4784955 50:0.056897756 51:1.3088051 52:0.60886765 53:−1.3749502 54:0.55317581 55: −0.20789304 56:−0.57680702 57:0.19929507 58:0.070962057 59:0.18337604 60:0.60094124 61:0.4337717 62:1.0110999 63:0.20664433 64:−0.84325552 65:0.20657222 66:0.31070495 67: −0.8924616 68:0.24730444 69:−0.72580957 70:−0.3408629 71:1.2265911 72:−0.74530989 73:0.55862898 74:0.2842778 75:0.71336466 76:0.10710888 77:0.22261065 78:0.51533312 79: −0.75857943 80:0.56938082 81:0.73724353 82:−0.78785485 83:0.52528638 84:0.078715399 85:0.10680436 86:−0.23703557 87:0.046045572 88:−0.002719589 89:0.10899653 90:0.31914085 91:−0.28593984 92:−0.23503149 93:0.10061869 94:−0.23567325 95:0.067099698 96:−0.21490467 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:0.0046544136 117:6.0590241e−007 118:0.00074805523 119:0.0025794252 120:0.00037352511 121:0.0022889439 122:0.0011132049 123:0.0024242986 124: −0.0045571304 125:0.0020117455 126:0.0092068724 127:0.0077256206 128:−0.00070437411 129:0.0012516935 130:0.00055489031 131:0.0013429716 132:0.00036176579 133: −0.0026087298 134:5.3104148e−005 135:0.001098063 136:0.0010348612 137:0.00068726367 138:0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:0.0029414443 164:−0.00037983558 165:0.0023911442 166:0.0021477563 167:9.2110975e−005 168:0.0026100944 169: −0.0034047128 170:0.0029387963 171:0.0023030045 172:0.0054465104 173:−0.0021478815 174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:−5.6713336e−005 189:0.0016455925 190:0.00055903167 191:0.00040327062 192:0.00066433422 193:−0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:−0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:0.012905908 220:0.015366459 221:−0.013814257 222:−0.007569442 223: −0.0047048843 224:0.00062012818 225:0.0014852113 226:0.019181944 227:0.005778844 228: −0.0022216991 229:0.0013164993 230:0.011913291 231:0.0048886021 232:−0.0050922348 233:0.00091115123 234:−0.0028072072 235:0.0020788321 236:−0.0069042598 237: −0.092131011 238:0.068610474 239:0.0047269738 240:0.0084348312 241:0.0050073303 242: −0.003040591 243:0.0038143608 244:−0.040638726 245:−0.02857391 246:−0.0472783 247: −0.020520929 248:0.0018310277 249:0.0055512898 250:0.0060781906 251:0.0072731995 252:−0.006453387 253:0.0049183252 254:0.014674404 255:0.026012832 256:0.021858063 257:0.021156041 258:−0.0072407476 259:−0.0034868279 260:0.0014243352 261:0.0010014101 262:0.0013208789 263:0.0028763453 264:−0.0076750983 265:−0.0046692337 266:

APPENDIX C2-continued

SVM ModelWeights
(340; Benign/Malignant)

−0.0012726086 267:0.0068167564 268:−0.04353733 269:0.046706751 270:−0.010794718 271: −0.0024784503 272:0.0059213047 273:0.016445309 274:0.016014025 275:0.0077815265 276: −0.0023459131 277:0.040564284 278:0.032950211 279:0.017959842 280:−0.0040876623 281: −0.026083954 282:−0.022933906 283:0.0027156388 284:0.035015725 285:−0.029552883 286: −0.010026687 287:0.011907991 288:0.0022531124 289:−0.002897898 290:−0.00044569091 291:0.00010489624 292:0.00053147622 293:0.00073173334 294:0.000621646 295: −0.00016437711 296:0.00049518317 297:0.00021529767 298:0.00052096118 299:−4.636059e−005 300:0.0021831172 301:0.0014980205 302:−0.00038898826 303:0.00068646355 304:0.0026823219 305:−0.0040565808 306:−0.0020829935 307:0.0013752591 308: −0.00034383399 309:2.7236187e−005 310:0.00070534449 311:0.0012802118 312:0.0030920727 313:0.00088650011 314:−0.00014303472 315:0.00071791362 316:0.00019783134 317:2.9171604e−006 318:0.00037660156 319:0.0011750009 320:0.0016896301 321: −0.0015126425 322:−0.00083564757 323:0.0010692998 324:0.0016934061 325:−0.00029338882 326:0.0034646564 327:7.9289544e−005 328:0.0023930578 329:0.00048041579 330:0.00021849622 331:4.0310828e−005 332:0.0032790094 333:−0.00015884312 334: −0.00031949134 335:3.3427419e−005 336:0.00084852462 337:0.00044620238 338:−0.0032407208 339:0.00048842531 340:0.00094149791 #
−0.0024183988673148219 1:5.9847097 2:0.83190614 3:3.2076981 4:3.8079975 5:1.3198755 6: −4.9284029 7:−0.4078356 8:0.23064108 9:−0.31782413 10:0.086775824 11:0.070308164 12: −2.4426701 13:1.4531602 14:0.78984618 15:0.82668793 16:2.0980465 17:0.18104351 18: −0.76579428 19:0.26044092 20:1.7634895 21:−1.7859451 22:−0.54260099 23:1.1592693 24:0.60947007 25:3.0047128 26:0.48909226 27:−0.18609163 28:1.3466139 29:1.112694 30: −0.26890093 31:0.45765018 32:0.42124534 33:0.386136 34:0.84868169 35:1.6364788 36: −0.028519887 37:1.2765138 38:1.6163156 39:2.7834327 40:1.8628697 41:2.5658431 42:0.72739297 43:0.64852452 44:1.1074948 45:0.97743762 46:1.3194482 47:1.5037328 48: −0.39539778 49:0.032376789 50:0.45744652 51:−1.2490126 52:1.6085756 53:0.3176223 54:0.092892468 55:0.17702933 56:0.027009025 57:−0.34548298 58:0.6999858 59:0.5645808 60:2.1313853 61:−0.12644149 62:−1.4977815 63:0.35250148 64:−0.5773651 65:0.59365129 66:0.57536352 67:−0.19167207 68:−0.25678271 69:0.29192075 70:−0.69047707 71:0.38122773 72:0.73858052 73:−0.34531942 74:0.093373567 75:0.23268723 76:0.5194428 77:0.40209553 78:0.17498569 79:−0.27617094 80:0.44819397 81:−0.40320599 82:1.053353 83:0.61412567 84: −0.54235631 85:−0.046558283 86:0.69069844 87:0.29973266 88:−0.48473459 89:0.46672389 90:0.041762356 91:−0.5280605 92:0.45706305 93:0.044412743 94:0.22903217 95:0.16006809 96:0.17317018 97:0.0039280006 98:0.010595871 99:0.0072948104 100:00007581744 101:0.0015444086 102:0.00086657552 103:0.0014506713 104:0.00027309253 105: −0.0003779236 106:−0.0033040401 107:0.002894687 108:0.0012058502 109:0.0026374348 110: −0.0018928888 111:−0.0024273857 112:0.0003231481 113:0.00057429477 114:0.00070962519 115:0.0011349921 116:0.0046544136 117:6.0590241e−007 118:0.00074805523 119: −0.0025794252 120:0.00037352511 121:0.0022889439 122:0.0011132049 123:0.0024242986 124:0.0045571304 125:0.0020117455 126:0.0092068724 127:0.0077256206 128: −0.00070437411 129:0.0012516935 130:0.00055489031 131:0.0013429716 132:0.00036176579 133:0.0026087298 134:5.3104148e−005 135:0.001098063 136:0.0010348612 137: −0.00068726367 138:−0.00074436213 139:0.0027458151 140:0.0010222673 141:0.0018521026 142:0.00061301264 143:−0.001804522 144:0.00021584153 145:0.0015449577 146: −0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:0.0029414443 164:0.00037983558 165:0.0023911442 166:0.0021477563 167:9.2110975e−005 168:0.0026100944 169: −0.0034047128 170:0.0029387963 171:0.0023030045 172:0.0054465104 173:0.0021478815 174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:−5.6713336e−005 189:0.0016455925 190:0.00055903167 191:0.00040327062 192:0.00066433422 193:0.0014816546 194:0.0016943325 195:0.00012320606 196:0.0006577372 197:0.00056744454 198:0.0023361598 199:0.0042997436 200:−0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:0.012905908 220:0.015366459 221:0.013814257 222:−0.007569442 223: −0.0047048843 224:0.00062012818 225:0.0014852113 226:0.019181944 227:0.005778844 228: −0.0022216991 229:0.0013164993 230:0.011913291 231:0.0048886021 232:0.0050922348 233:0.00091115123 234:−0.0028072072 235:−0.0020788321 236:−0.0069042598 237: −0.092131011 238:0.068610474 239:−0.0047269738 240:0.0084348312 241:−0.0050073303 242: −0.003040591 243:0.0038143608 244:−0.040638726 245:0.02857391 246:−0.0472783 247: −0.020520929 248:0.0018310277 249:0.0055512898 250:0.0060781906 251:0.0072731995 252:−0.006453387 253:0.0049183252 254:0.014674404 255:0.026012832 256:0.021858063 257:0.021156041 258:−0.0072407476 259:−0.0034868279 260:0.0014243352 261:0.0010014101 262:0.0013208789 263:−0.0028763453 264:0.0076750983 265:−0.0046692337 266: −0.0012726086 267:0.0068167564 268:−0.04353733 269:−0.046706751 270:0.010794718 271: −0.0024784503 272:0.0059213047 273:0.016445309 274:0.016014025 275:0.0077815265 276: −0.0023459131 277:0.040564284 278:0.032950211 279:0.017959842 280:0.0040876623 281: −0.026083954 282:−0.022933906 283:0.0027156388 284:0.035015725 285:0.029552883 286: −0.010026687 287:0.011907991 288:0.0022531124 289:0.002897898 290:−0.00044569091 291:0.00010489624 292:0.00053147622 293:0.00073173334 294:0.000621646 295: −0.00016437711 296:0.00049518317 297:0.00021529767 298:0.00052096118 299:−4.636059e−005

APPENDIX C2-continued

SVM ModelWeights
(340; Benign/Malignant)

300:0.0021831172 301:−0.0014980205 302:−0.00038898826 303:0.00068646355
304:0.0026823219 305:−0.0040565808 306:0.0020829935 307:0.0013752591 308:
−0.00034383399 309:2.7236187e−005 310:0.00070534449 311:0.0012802118 312:0.0030920727
313:−0.00088650011 314:0.00014303472 315:0.00071791362 316:0.00019783134
317:2.9171604e−006 318:0.00037660156 319:0.0011750009 320:0.0016896301 321:
−0.0015126425 322:0.00083564757 323:0.0010692998 324:0.0016934061 325:0.00029338882
326:0.0034646564 327:−7.9289544e−005 328:0.0023930578 329:0.00048041579
330:0.00021849622 331:4.0310828e−005 332:0.0032790094 333:0.00015884312 334:
−0.00031949134 335:3.3427419e−005 336:0.00084852462 337:0.00044620238 338:0.0032407208
339:0.00048842531 340:0.00094149791 #
−0.0033153142499855108 1:5.7209835 2:0.23666459 3:1.730386 4:0.35195339 5:0.080441706
6:0.4397411 7:0.79212171 8:−3.2328453 9:0.53677988 10:1.278559 11:1.9872284 12:−3.541455
13:1.268319 14:0.80598712 15:1.9951948 16:1.6678131 17:0.39204028 18:0.14329085
19:0.0522938 20:3.9440317 21:0.70164174 22:0.37428939 23:1.37909 24:−0.080555849 25:
−0.21866828 26:0.26640299 27:0.11733657 28:0.54316443 29:0.98517901 30:0.26204801 31:
−0.19700877 32:0.53598785 33:−0.78479302 34:1.9096892 35:0.21801066 36:0.68265325
37:0.061487831 38:1.0199002 39:0.14417441 40:0.060175069 41:2.7730792 42:0.2983031 43:
−0.44488677 44:0.98700613 45:0.61365366 46:1.1833302 47:0.68848914 48:1.2433225
49:1.9442695 50:0.60836315 51:0.33906472 52:0.95265335 53:0.22811827 54:1.6679398
55:0.2450835 56:1.3480361 57:0.38068792 58:1.285329 59:0.64653748 60:1.0222931
61:0.41674906 62:1.0298935 63:1.5975699 64:0.53876853 65:1.5039648 66:0.16029453 67:
−0.27558342 68:0.2916702 69:0.0036349858 70:−0.85938823 71:0.5335471 72:−1.0547386 73:
−0.0090008266 74:0.11001433 75:0.20822597 76:−0.074708924 77:0.24800478 78:0.29446042
79:0.97626752 80:−0.87793279 81:0.14734183 82:0.15992483 83:−0.14554277 84:0.44493255
85:0.05211214 86:0.14523202 87:0.47606155 88:0.45266959 89:0.34108949 90:0.32113761
91:−0.23841642 92:0.39311221 93:0.56485057 94:0.15750122 95:0.66756612 96:0.47440732
97:0.0039280006 98:0.010595871 99:0.0072948104 100:0.0007581744 101:0.0015444086
102:0.00086657552 103:0.0014506713 104:0.00027309253 105:0.0003779236 106:
−0.0033040401 107:0.002894687 108:0.0012058502 109:0.0026374348 110:0.0018928888 111:
−0.0024273857 112:0.0003231481 113:0.00057429477 114:0.00070962519 115:0.0011349921
116:0.0046544136 117:6.0590241e−007 118:0.00074805523 119:0.0025794252
120:0.00037352511 121:0.0022889439 122:0.0011132049 123:0.0024242986 124:
−0.0045571304 125:0.0020117455 126:0.0092068724 127:0.0077256206 128:0.00070437411
129:0.0012516935 130:0.00055489031 131:0.0013429716 132:0.00036176579 133:
−0.0026087298 134:5.3104148e−005 135:−0.001098063 136:0.0010348612 137:0.00068726367
138:0.00074436213 139:0.0027458151 140:0.0010222673 141:0.0018521026 142:
−0.00061301264 143:0.001804522 144:0.00021584153 145:0.0015449577 146:0.0015697054
147:0.00097707158 148:0.0011295594 149:0.0028935266 150:0.00053708232
151:0.0018405041 152:0.002562111 153:0.0013092471 154:0.00046263589 155:
−0.0035724007 156:0.0011358063 157:0.0012884629 158:0.0031973415 159:0.00045693576
160:0.0012730506 161:0.0014123393 162:0.003461167 163:0.0029414443 164:0.00037983558
165:−0.0023911442 166:0.0021477563 167:9.2110975e−005 168:0.0026100944 169:
−0.0034047128 170:0.0029387963 171:0.0023030045 172:0.0054465104 173:0.0021478815
174:−0.0022738085 175:0.00050098688 176:0.0021780876 177:2.5619611e−005 178:
−0.0010297548 179:0.000299401 180:0.0002858036 181:0.0015720503 182:0.0012860922
183:0.0015920103 184:0.0034542123 185:0.0054590856 186:0.0013231005 187:
−0.00026378682 188:−5.6713336e−005 189:0.0016455925 190:0.00055903167 191:0.00040327062
192:−0.00066433422 193:0.0014816546 194:0.0016943325 195:0.00012320606
196:0.0006577372 197:0.00056744454 198:0.0023361598 199:0.0042997436 200:0.0016990597
201:0.0030764227 202:0.0027063258 203:0.00046884044 204:0.00031649071
205:0.00065622263 206:0.0026635081 207:0.0039158296 208:0.0020220254 209:0.0012250372
210:−0.0028663045 211:0.0012186989 212:0.00063428417 213:0.0051512984
214:0.00089924945 215:0.00035291715 216:0.0026578247 217:0.031516869 218:
−0.018453332 219:−0.012905908 220:0.015366459 221:−0.013814257 222:0.007569442 223:
−0.0047048843 224:0.00062012818 225:0.0014852113 226:0.019181944 227:−0.005778844 228:
−0.0022216991 229:0.0013164993 230:0.011913291 231:0.0048886021 232:−0.0050922348
233:0.00091115123 234:0.0028072072 235:0.0020788321 236:−0.0069042598 237:
−0.092131011 238:0.068610474 239:0.0047269738 240:0.0084348312 241:−0.0050073303 242:
−0.003040591 243:0.0038143608 244:0.040638726 245:−0.02857391 246:−0.0472783 247:
−0.020520929 248:0.0018310277 249:0.0055512898 250:0.0060781906 251:0.0072731995
252:−0.006453387 253:0.0049183252 254:0.014674404 255:0.026012832 256:0.021858063
257:0.021156041 258:−0.0072407476 259:−0.0034868279 260:0.0014243352 261:0.0010014101
262:0.0013208789 263:0.0028763453 264:0.0076750983 265:−0.0046692337 266:
−0.0012726086 267:0.0068167564 268:0.04353733 269:0.046706751 270:0.010794718 271:
−0.0024784503 272:0.0059213047 273:0.016445309 274:0.016014025 275:0.0077815265 276:
−0.0023459131 277:0.040564284 278:0.032950211 279:0.017959842 280:−0.0040876623 281:
−0.026083954 282:0.022933906 283:0.0027156388 284:0.035015725 285:−0.029552883 286:
−0.010026687 287:0.011907991 288:0.0022531124 289:−0.002897898 290:−0.00044569091
291:0.00010489624 292:0.00053147622 293:0.00073173334 294:0.000621646 295:
−0.00016437711 296:−0.00049518317 297:0.00021529767 298:0.00052096118 299:−4.636059e−005
300:−0.0021831172 301:−0.0014980205 302:0.00038898826 303:0.00068646355
304:0.0026823219 305:0.0040565808 306:−0.0020829935 307:0.0013752591 308:
−0.00034383399 309:2.7236187e−005 310:0.00070534449 311:0.0012802118 312:0.0030920727
313:0.00088650011 314:0.00014303472 315:0.00071791362 316:0.00019783134
317:2.9171604e−006 318:0.00037660156 319:0.0011750009 320:0.0016896301 321:
−0.0015126425 322:0.00083564757 323:0.0010692998 324:0.0016934061 325:0.00029338882
326:−0.0034646564 327:−7.9289544e−005 328:0.0023930578 329:0.00048041579

APPENDIX C2-continued

| SVM ModelWeights (340; Benign/Malignant) |
|---|

330:0.00021849622 331:4.0310828e−005 332:−0.0032790094 333:0.00015884312 334: −0.00031949134 335:3.3427419e−005 336:0.00084852462 337:0.00044620238 338:−0.0032407208 339:0.00048842531 340:0.00094149791 #
−0.0022051346595895732 1:3.3504007 2:6.2324839 3:2.6426129 4:1.492183 5:3.0097013 6: −1.152725 7:3.869487 8:0.46534666 9:1.5877725 10:2.5205293 11:0.012004626 12:1.0621814 13:0.17664123 14:−2.0569618 15:−1.6601045 16:1.1510824 17:0.25813934 18:0.13201335 19: −1.131669 20:1.1496286 21:1.575572 22:0.2038112 23:0.46738106 24:−0.70897067 25: −0.56662709 26:−0.48662603 27:0.020907728 28:−0.37763599 29:1.4949493 30:−0.64525312 31: −0.63886672 32:−0.58693498 33:1.0291035 34:0.49202242 35:0.2502974 36:0.76210868 37: −0.27610156 38:2.3534727 39:1.025668 40:0.061278824 41:1.5647804 42:0.74536902 43: −0.10340484 44:0.52367389 45:0.24083184 46:1.1846058 47:−0.3576465 48:0.83624595 49:1.9942691 50:0.12304199 51:0.87746346 52:1.2957979 53:1.8208426 54:1.5262439 55: −1.1147339 56:−0.90715885 57:0.27381408 58:1.2977566 59:−0.025077818 60:−0.53921193 61: −0.32603326 62:−0.31038827 63:1.2054646 64:0.10846778 65:0.61878496 66:1.1695999 67: −0.69651842 68:0.47412398 69:0.48150793 70:1.3362669 71:0.62126261 72:0.075418077 73:0.87004262 74:−0.46395355 75:0.59036511 76:1.090446 77:0.03209864 78:0.10529161 79:0.70742953 80:0.31867182 81:0.35844326 82:0.79198897 83:0.59871656 84:0.163928 85: −0.49811831 86:0.10127752 87:0.49906915 88:0.57758665 89:0.082276538 90:0.37697205 91: −0.45461333 92:−0.55460352 93:0.0619094 94:−0.73073453 95:−0.26036748 96:0.10186397 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:0.0046544136 117:6.0590241e−007 118:0.00074805523 119:0.0025794252 120:0.00037352511 121:0.0022889439 122:0.0011132049 123:0.0024242986 124: −0.0045571304 125:0.0020117455 126:0.0092068724 127:0.0077256206 128:0.00070437411 129:0.0012516935 130:0.00055489031 131:0.0013429716 132:0.00036176579 133: −0.0026087298 134:5.3104148e−005 135:0.001098063 136:0.0010348612 137:0.00068726367 138:0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 .160:0.0012730506 161:0.0014123393 162:0.003461167 163:0.0029414443 164:0.00037983558 165:0.0023911442 166:0.0021477563 167:9.2110975e−005 168:−0.0026100944 169: −0.0034047128 170:0.0029387963 171:0.0023030045 172:0.0054465104 173:0.0021478815 174:−0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:0.00066433422 193:−0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:0.012905908 220:0.015366459 221:0.013814257 222:−0.007569442 223: −0.0047048843 224:0.00062012818 225:0.0014852113 226:0.019181944 227:−0.005778844 228: −0.0022216991 229:0.0013164993 230:0.011913291 231:0.0048886021 232:−0.0050922348 233:−0.00091115123 234:−0.0028072072 235:−0.0020788321 236:0.0069042598 237: −0.092131011 238:0.068610474 239:−0.0047269738 240:0.0084348312 241:0.0050073303 242: −0.003040591 243:0.0038143608 244:−0.040638726 245:0.02857391 246:−0.0472783 247: −0.020520929 248:0.0018310277 249:0.0055512898 250:0.0060781906 251:−0.0072731995 252:−0.006453387 253:−0.0049183252 254:0.014674404 255:0.026012832 256:0.021858063 257:0.021156041 258:−0.0072407476 259:−0.0034868279 260:0.0014243352 261:0.0010014101 262:0.0013208789 263:−0.0028763453 264:−0.0076750983 265:0.0046692337 266: −0.0012726086 267:0.0068167564 268:0.04353733 269:−0.046706751 270:0.010794718 271: −0.0024784503 272:0.0059213047 273:0.016445309 274:0.016014025 275:0.0077815265 276: −0.0023459131 277:−0.040564284 278:0.032950211 279:0.017959842 280:0.0040876623 281: −0.026083954 282:0.022933906 283:0.0027156388 284:0.035015725 285:−0.029552883 286: −0.010026687 287:0.011907991 288:0.0022531124 289:−0.002897898 290:−0.00044569091 291:0.00010489624 292:0.00053147622 293:0.00073173334 294:0.000621646 295: −0.00016437711 296:0.00049518317 297:0.00021529767 298:0.00052096118 299:−4.636059e−005 300:0.0021831172 301:0.0014980205 302:0.00038898826 303:0.00068646355 304:0.0026823219 305:0.0040565808 306:0.0020829935 307:0.0013752591 308: −0.00034383399 309:2.7236187e−005 310:0.00070534449 311:0.0012802118 312:0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:0.0016934061 325:0.00029338882 326:−0.0034646564 327:7.9289544e−005 328:0.0023930578 329:0.00048041579 330:0.00021849622 331:4.0310828e−005 332:−0.0032790094 333:0.00015884312 334: −0.00031949134 335:3.3427419e−005 336:0.00084852462 337:0.00044620238 338:0.0032407208 339:0.00048842531 340:0.00094149791 #
−0.0019388357372294319 1:7.2026958 2:2.506717 3:1.6384877 4:2.1010149 5:2.6597629 6: −2.2723093 7:2.6085973 8:2.0390947 9:0.71968418 10:−1.0824095 11:1.1634985 12:0.56328827 13:0.013427491 14:0.22713479 15:1.2914221 16:0.4034566 17:0.095398933 18:0.86121124 19:0.20695956 20:0.28110185 21:1.1006707 22:1.2550631 23:1.8677807 24:0.83824652 25:

APPENDIX C2-continued

| SVM ModelWeights (340; Benign/Malignant) |
|---|
| −0.20042829 26:0.23248933 27:1.6082169 28:0.2339604 29:0.94725752 30:1.2839389 31: −0.95752859 32:0.26085943 33:0.96349519 34:−0.53986728 35:0.96847063 36:−0.5258432 37:0.44683513 38:0.016518893 39:0.53123569 40:0.73466289 41:0.14847454 42:0.39979953 43:−1.189554 44:−0.085250653 45:0.78965682 46:0.61769366 47:−0.27439302 48:−0.7249788 49:0.75479484 50:1.3104892 51:1.6286936 52:−0.97226423 53:−0.25266522 54:1.4067597 55: −0.92626107 56:0.99213964 57:0.16685288 58:−0.51933849 59:0.14818022 60:−0.14942604 61:0.25867373 62:0.020739969 63:1.0102789 64:0.43018341 65:0.57322633 66:0.20108385 67:0.59315741 68:0.19920386 69:0.8077935 70:0.36393169 71:0.35045397 72:0.13032785 73:0.19120462 74:0.92244279 75:0.71011055 76:0.78690231 77:0.34503469 78:0.20833312 79: −0.82746303 80:0.17615448 81:0.47272056 82:0.7111606 83:0.0077136639 84:0.91128999 85: −0.508798 86:1.3149154 87:0.82740068 88:0.99760932 89:0.46667439 90:0.18975885 91:0.053894941 92:0.43155012 93:0.49435949 94:1.0697258 95:0.26373157 96:0.36716774 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:0.0046544136 117:6.0590241e−007 118:0.00074805523 119:0.0025794252 120:0.00037352511 121:−0.0022889439 122:0.0011132049 123:−0.0024242986 124: −0.0045571304 125:0.0020117455 126:0.0092068724 127:0.0077256206 128:−0.00070437411 129:0.0012516935 130:0.00055489031 131:0.0013429716 132:0.00036176579 133: −0.0026087298 134:5.3104148e−005 135:−0.001098063 136:0.0010348612 137:0.00068726367 138:0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:0.0029414443 164:0.00037983558 165:0.0023911442 166:0.0021477563 167:9.2110975e−005 168:0.0026100944 169: −0.0034047128 170:−0.0029387963 171:0.0023030045 172:0.0054465104 173:−0.0021478815 174:−0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:−5.6713336e−005 189:0.0016455925 190:0.00055903167 191:0.00040327062 192:0.00066433422 193:−0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:0.012905908 220:0.015366459 221:0.013814257 222:−0.007569442 223: −0.0047048843 224:0.00062012818 225:0.0014852113 226:0.019181944 227:0.005778844 228: −0.0022216991 229:0.0013164993 230:0.011913291 231:0.0048886021 232:0.0050922348 233:0.00091115123 234:−0.0028072072 235:−0.0020788321 236:−0.0069042598 237: −0.092131011 238:0.068610474 239:−0.0047269738 240:0.0084348312 241:0.0050073303 242: −0.003040591 243:0.0038143608 244:−0.040638726 245:−0.02857391 246:0.0472783 247: −0.020520929 248:0.0018310277 249:0.0055512898 250:0.0060781906 251:0.0072731995 252:0.006453387 253:−0.0049183252 254:0.014674404 255:0.026012832 256:−0.021858063 257:0.021156041 258:−0.0072407476 259:0.0034868279 260:0.0014243352 261:0.0010014101 262:0.0013208789 263:−0.0028763453 264:0.0076750983 265:0.0046692337 266: −0.0012726086 267:0.0068167564 268:0.04353733 269:−0.046706751 270:0.010794718 271: −0.0024784503 272:0.0059213047 273:0.016445309 274:0.016014025 275:−0.0077815265 276: −0.0023459131 277:−0.040564284 278:0.032950211 279:0.017959842 280:−0.0040876623 281: −0.026083954 282:0.022933906 283:0.0027156388 284:0.035015725 285:−0.029552883 286: −0.010026687 287:0.011907991 288:0.0022531124 289:−0.002897898 290:−0.00044569091 291:0.00010489624 292:0.00053147622 293:0.00073173334 294:0.000621646 295: −0.00016437711 296:−0.00049518317 297:0.00021529767 298:0.00052096118 299:−4.636059e−005 300:0.0021831172 301:−0.0014980205 302:−0.00038898826 303:0.00068646355 304:0.0026823219 305:0.0040565808 306:−0.0020829935 307:0.0013752591 308: −0.00034383399 309:2.7236187e−005 310:0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321: −0.0015126425 322:−0.00083564757 323:0.0010692998 324:0.0016934061 325:0.00029338882 326:−0.0034646564 327:−7.9289544e−005 328:0.0023930578 329:0.00048041579 330:0.00021849622 331:4.0310828e−005 332:−0.0032790094 333:0.00015884312 334: −0.00031949134 335:3.3427419e−005 336:0.00084852462 337:0.00044620238 338:0.0032407208 339:0.00048842531 340:0.00094149791 # |
| 0.00094804616560001289 1:−0.26397073 2:−4.3800235 3:0.96010846 4:−6.5841908 5:1.6685443 6:−0.56736088 7:−0.083688535 8:2.66816 9:1.6018287 10:2.2983365 11:3.507324 12:0.0095484713 13:1.2482775 14:0.31201324 15:0.47953141 16:0.59642285 17:0.47637615 18:−1.1856458 19:−1.6341721 20:3.4143758 21:−0.020608557 22:0.73003125 23:0.81526971 24: −1.5109706 25:−0.14740245 26:0.54324085 27:−0.27993053 28:−1.0582408 29:0.91323972 30:1.3065295 31:0.65528071 32:1.5894922 33:0.89412045 34:3.1973541 35:−0.72293127 36:2.4681482 37:0.33120728 38:0.91447645 39:0.69795197 40:−0.21701232 41:1.0900477 42:0.67749697 43:−0.33487478 44:0.69148785 45:0.26212937 46:0.54704535 47:0.89142299 48:0.87253165 49:0.30725515 50:0.01050829 51:0.067594275 52:−0.76299405 53:−0.5275268 54:0.60136604 55:0.93226683 56:0.88733613 57:0.38411763 58:0.32900149 59:0.90254068 .60:1.6998997 61:0.58596885 62:0.34130809 63:0.56362987 64:0.38372657 65:0.83891815 66: |

APPENDIX C2-continued

| SVM ModelWeights (340; Benign/Malignant) |
|---|
| −0.5779351 67:1.0001854 68:0.8855077 69:0.49604541 70:0.061250381 71:1.2289635 72:0.77946144 73:0.10443769 74:0.53655225 75:−0.47988957 76:0.35080016 77:0.081329726 78:0.8766126 79:0.17184246 80:0.59839505 81:0.80135769 82:0.43899104 83:0.051791977 84:0.13997768 85:0.69018161 86:0.35188946 87:0.63329929 88:0.1815916 89:0.069914095 90:0.31960812 91:0.083477527 92:0.50268704 93:1.083508 94:0.35221416 95:−0.089989774 96:0.43912902 97:0.0039280006 98:0.010595871 99:0.0072948104 100:0.0007581744 101:0.0015444086 102:0.00086657552 103:0.0014506713 104:0.00027309253 105:−0.0003779236 106:0.0033040401 107:0.002894687 108:0.0012058502 109:0.0026374348 110:−0.0018928888 111:0.0024273857 112:0.0003231481 113:0.00057429477 114:0.00070962519 115:0.0011349921 116:0.0046544136 117:6.0590241e−007 118:0.00074805523 119:−0.0025794252 120:0.00037352511 121:0.0022889439 122:0.0011132049 123:0.0024242986 124:0.0045571304 125:0.0020117455 126:0.0092068724 127:0.0077256206 128:−0.00070437411 129:0.0012516935 130:0.00055489031 131:0.0013429716 132:0.00036176579 133:0.0026087298 134:5.3104148e−005 135:0.001098063 136:0.0010348612 137:−0.00068726367 138:−0.00074436213 139:0.0027458151 140:0.0010222673 141:0.0018521026 142:0.00061301264 143:0.001804522 144:0.00021584153 145:0.0015449577 146:−0.0015697054 147:0.00097707158 148:0.0011295594 149:0.0028935266 150:0.00053708232 151:0.0018405041 152:0.002562111 153:0.0013092471 154:0.00046263589 155:−0.0035724007 156:0.0011358063 157:0.0012884629 158:0.0031973415 159:0.00045693576 160:0.0012730506 161:0.0014123393 162:0.003461167 163:0.0029414443 164:−0.00037983558 165:0.0023911442 166:0.0021477563 167:9.2110975e−005 168:0.0026100944 169:−0.0034047128 170:0.0029387963 171:0.0023030045 172:0.0054465104 173:0.0021478815 174:0.0022738085 175:0.00050098688 176:0.0021780876 177:2.5619611e−005 178:−0.0010297548 179:0.000299401 180:0.0002858036 181:0.0015720503 182:0.0012860922 183:0.0015920103 184:0.0034542123 185:0.0054590856 186:0.0013231005 187:−0.00026378682 188:5.6713336e−005 189:0.0016455925 190:0.00055903167 191:0.00040327062 192:0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:−0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218:−0.018453332 219:0.012905908 220:0.015366459 221:0.013814257 222:0.007569442 223:−0.0047048843 224:0.00062012818 225:0.0014852113 226:0.019181944 227:−0.005778844 228:−0.0022216991 229:0.0013164993 230:0.011913291 231:0.0048886021 232:−0.0050922348 233:0.00091115123 234:−0.0028072072 235:0.0020788321 236:−0.0069042598 237:−0.092131011 238:0.068610474 239:−0.0047269738 240:0.0084348312 241:0.0050073303 242:−0.003040591 243:0.0038143608 244:−0.040638726 245:−0.02857391 246:−0.0472783 247:−0.020520929 248:0.0018310277 249:0.0055512898 250:0.0060781906 251:0.0072731995 252:0.006453387 253:0.0049183252 254:0.014674404 255:0.026012832 256:0.021858063 257:0.021156041 258:−0.0072407476 259:−0.0034868279 260:0.0014243352 261:0.0010014101 262:0.0013208789 263:−0.0028763453 264:−0.0076750983 265:−0.0046692337 266:−0.0012726086 267:0.0068167564 268:−0.04353733 269:0.046706751 270:0.010794718 271:−0.0024784503 272:0.0059213047 273:0.016445309 274:0.016014025 275:0.0077815265 276:−0.0023459131 277:0.040564284 278:0.032950211 279:0.017959842 280:−0.0040876623 281:−0.026083954 282:0.022933906 283:0.0027156388 284:0.035015725 285:0.029552883 286:−0.010026687 287:0.011907991 288:0.0022531124 289:0.002897898 290:−0.00044569091 291:0.00010489624 292:0.00053147622 293:0.00073173334 294:0.000621646 295:−0.00016437711 296:0.00049518317 297:0.00021529767 298:0.00052096118 299:−4.636059e−005 300:−0.0021831172 301:0.0014980205 302:0.00038898826 303:0.00068646355 304:0.0026823219 305:−0.0040565808 306:−0.0020829935 307:0.0013752591 308:−0.00034383399 309:2.7236187e−005 310:0.00070534449 311:0.0012802118 312:0.0030920727 313:−0.00088650011 314:0.00014303472 315:0.00071791362 316:0.00019783134 317:2.9171604e−006 318:0.00037660156 319:0.0011750009 320:0.0016896301 321:−0.0015126425 322:0.00083564757 323:0.0010692998 324:0.0016934061 325:−0.00029338882 326:−0.0034646564 327:7.9289544e−005 328:0.0023930578 329:0.00048041579 330:0.00021849622 331:4.0310828e−005 332:−0.0032790094 333:0.00015884312 334:−0.00031949134 335:3.3427419e−005 336:0.00084852462 337:0.00044620238 338:−0.0032407208 339:0.00048842531 340:0.00094149791 # −0.00071798523183447878 1:7.9486814 2:6.313159 3:3.4036202 4:3.6738026 5:0.8484242 6:−1.12104 7:1.1878948 8:2.2317212 9:2.0272512 10:0.52818286 11:1.7246594 12:1.3033267 13:−0.41194135 14:1.4738997 15:0.94791991 16:0.43159148 17:0.86042041 18:0.72649908 19:0.24455844 20:1.5337915 21:−0.070671529 22:−3.2864313 23:1.042661 24:0.57346916 25:−0.17784877 26:0.62522596 27:1.3299311 28:1.430204 29:1.229068 30:1.6345702 31:0.82010353 32:2.4077256 33:0.46431184 34:0.70158809 35:2.1816514 36:2.2421138 37:1.5970308 38:0.18138181 39:1.1032536 40:1.472198 41:0.50239062 42:0.62110627 43:−0.23183186 44:−2.0542288 45:0.34160188 46:0.02542842 47:0.14262132 48:0.046494257 49:1.6358472 50:0.54953927 51:0.5901584 52:0.77110654 53:−0.17316507 54:1.5964856 55:1.0319989 56:0.74831015 57:0.90131527 58:0.02119487 59:0.85915452 60:0.83274412 61:0.26454583 62:0.052552998 63:0.96018612 64:−0.27045661 65:0.034029823 66:0.25971562 67:0.087616593 68:0.21399029 69:1.1747633 70:0.74932021 71:−0.52223557 72:0.5713945 73:0.40078789 74:−0.2828753 75:0.14939854 76:0.32377112 77:0.066406585 78:−0.022806602 79:0.20015027 80:0.26603687 81:0.21412492 82:0.73513877 83:0.27894762 84:0.16934811 85:0.11708372 86:0.11781476 87:1.1381788 88:0.63588184 89:0.32901144 90:0.022063501 91:0.64123589 92:−0.63978565 93:0.52019113 94:0.17302194 95:0.70685029 96:0.46147156 97:0.0039280006 98:0.010595871 99:0.0072948104 100:0.0007581744 101:0.0015444086 102:0.00086657552 103:0.0014506713 104:0.00027309253 105:0.0003779236 106:0.0033040401 107:0.002894687 |

APPENDIX C2-continued

SVM ModelWeights
(340; Benign/Malignant)

108:0.0012058502 109:0.0026374348 110:0.0018928888 111:0.0024273857 112:0.0003231481 113:0.00057429477 114:0.00070962519 115:0.0011349921 116:0.0046544136 117:6.0590241e–007 118:0.00074805523 119:0.0025794252 120:0.00037352511 121:0.0022889439 122:0.0011132049 123:0.0024242986 124:0.0045571304 125:0.0020117455 126:–0.0092068724 127:0.0077256206 128:0.00070437411 129:0.0012516935 130:0.00055489031 131:0.0013429716 132:0.00036176579 133:0.0026087298 134:5.3104148e–005 135:–0.001098063 136:0.0010348612 137:0.00068726367 138:0.00074436213 139:0.0027458151 140:0.0010222673 141:0.0018521026 142:0.00061301264 143:0.001804522 144:–0.00021584153 145:0.0015449577 146:0.0015697054 147:0.00097707158 148:0.0011295594 149:0.0028935266 150:0.00053708232 151:0.0018405041 152:0.002562111 153:–0.0013092471 154:0.00046263589 155:0.0035724007 156:0.0011358063 157:0.0012884629 158:–0.0031973415 159:0.00045693576 160:–0.0012730506 161:0.0014123393 162:0.003461167 163:–0.0029414443 164:0.00037983558 165:0.0023911442 166:0.0021477563 167:9.2110975e–005 168:0.0026100944 169:0.0034047128 170:0.0029387963 171:0.0023030045 172:–0.0054465104 173:0.0021478815 174:–0.0022738085 175:0.00050098688 176:0.0021780876 177:2.5619611e–005 178:–0.0010297548 179:0.000299401 180:0.0002858036 181:0.0015720503 182:0.0012860922 183:0.0015920103 184:0.0034542123 185:0.0054590856 186:0.0013231005 187:0.00026378682 188:–5.6713336e–005 189:0.0016455925 190:0.00055903167 191:0.00040327062 192:0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:–0.00063428417 213:0.0051512984 214:0.00089924945 215:0.00035291715 216:0.0026578247 217:0.031516869 218:0.018453332 219:0.012905908 220:0.015366459 221:0.013814257 222:–0.007569442 223:0.0047048843 224:0.00062012818 225:0.0014852113 226:0.019181944 227:0.005778844 228:0.0022216991 229:0.0013164993 230:0.011913291 231:0.0048886021 232:–0.0050922348 233:0.00091115123 234:0.0028072072 235:0.0020788321 236:–0.0069042598 237:0.092131011 238:0.068610474 239:–0.0047269738 240:–0.0084348312 241:–0.0050073303 242:–0.003040591 243:0.0038143608 244:–0.040638726 245:–0.02857391 246:–0.0472783 247:0.020520929 248:0.0018310277 249:0.0055512898 250:0.0060781906 251:–0.0072731995 252:0.006453387 253:0.0049183252 254:–0.014674404 255:0.026012832 256:–0.021858063 257:0.021156041 258:–0.0072407476 259:–0.0034868279 260:0.0014243352 261:–0.0010014101 262:0.0013208789 263:–0.0028763453 264:0.0076750983 265:0.0046692337 266:0.0012726086 267:0.0068167564 268:0.04353733 269:–0.046706751 270:–0.010794718 271:0.0024784503 272:0.0059213047 273:0.016445309 274:0.016014025 275:0.0077815265 276:0.0023459131 277:–0.040564284 278:0.032950211 279:0.017959842 280:–0.0040876623 281:0.026083954 282:–0.022933906 283:0.0027156388 284:0.035015725 285:–0.029552883 286:–0.010026687 287:0.011907991 288:0.0022531124 289:–0.002897898 290:0.00044569091 291:0.00010489624 292:0.00053147622 293:0.00073173334 294:0.000621646 295:–0.00016437711 296:–0.00049518317 297:0.00021529767 298:0.00052096118 299:4.636059e–005 300:–0.0021831172 301:–0.0014980205 302:–0.00038898826 303:0.00068646355 304:0.0026823219 305:–0.0040565808 306:0.0020829935 307:0.0013752591 308:–0.00034383399 309:2.7236187e–005 310:0.00070534449 311:0.0012802118 312:0.0030920727 313:0.00088650011 314:0.00014303472 315:0.00071791362 316:0.00019783134 317:2.9171604e–006 318:0.00037660156 319:0.0011750009 320:0.0016896301 321:–0.0015126425 322:–0.00083564757 323:0.0010692998 324:0.0016934061 325:–0.00029338882 326:–0.0034646564 327:7.9289544e–005 328:0.0023930578 329:0.00048041579 330:0.00021849622 331:4.0310828e–005 332:–0.0032790094 333:0.00015884312 334:–0.00031949134 335:3.3427419e–005 336:0.00084852462 337:0.00044620238 338:0.0032407208 339:0.00048842531 340:0.00094149791 #
–0.00094629083477538339 1:9.1230593 2:3.9607098 3:1.5756338 4:4.1874185 5:2.1461926 6:–1.7388706 7:2.1186652 8:1.0513726 9:1.2865088 10:–0.81872839 11:0.040312272 12:–0.15184851 13:0.31572929 14:0.15833652 15:0.26118129 16:1.0505745 17:1.0178174 18:0.16850244 19:1.525844 20:2.4251978 21:2.1380534 22:1.7921528 23:0.70529109 24:–0.86903912 25:0.90763175 26:2.0566919 27:0.52910912 28:0.33037242 29:0.33875701 30:1.0200107 31:0.34964737 32:–0.46560356 33:0.52523929 34:0.24413136 35:0.48999044 36:0.046803989 37:0.035574108 38:0.76940674 39:0.22491753 40:0.11223246 41:0.28678265 42:0.95212728 43:0.11985786 44:0.6971736 45:1.0102677 46:1.1753534 47:–0.68612713 48:–1.0194079 49:0.0044652228 50:0.47938496 51:0.16353835 52:–0.54597574 53:0.90813696 54:–0.37022072 55:0.17169508 56:–0.53953499 57:0.77884901 58:0.27515292 59:0.63446444 60:0.59566504 61:0.56384295 62:0.18165052 63:–0.71566111 64:0.78215849 65:0.62599987 66:0.41566026 67:0.41583338 68:0.75958508 69:0.45774817 70:0.33390945 71:–0.6251325 72:–0.33184326 73:0.10600477 74:1.3817265 75:0.72555315 76:0.64912313 77:1.1465611 78:–0.30240169 79:0.36051276 80:0.71007937 81:0.11025462 82:0.7955364 83:0.56237835 84:–0.34528831 85:0.098673992 86:0.1231902 87:0.55380547 88:1.6304933 89:1.33736 90:0.16333365 91:0.38016465 92:0.68087202 93:0.030846301 94:0.59149367 95:0.0958841 96:0.12936662 97:0.0039280006 98:0.010595871 99:0.0072948104 100:0.0007581744 101:0.0015444086 102:0.00086657552 103:0.0014506713 104:0.00027309253 105:–0.0003779236 106:0.0033040401 107:0.002894687 108:0.0012058502 109:0.0026374348 110:–0.0018928888 111:0.0024273857 112:0.0003231481 113:0.00057429477 114:0.00070962519 115:0.0011349921 116:–0.0046544136 117:6.0590241e–007 118:0.00074805523 119:–0.0025794252 120:0.00037352511 121:–0.0022889439 122:0.0011132049 123:–0.0024242986 124:0.0045571304 125:0.0020117455 126:0.0092068724 127:0.0077256206 128:–0.00070437411 129:0.0012516935 130:0.00055489031 131:0.0013429716 132:0.00036176579 133:0.0026087298 134:5.3104148e–005 135:0.001098063 136:0.0010348612 137:–0.00068726367 138:–0.00074436213 139:0.0027458151 140:0.0010222673 141:0.0018521026

APPENDIX C2-continued

| SVM ModelWeights (340; Benign/Malignant) |
| --- |
| 142:0.00061301264 143:−0.001804522 144:0.00021584153 145:0.0015449577 146: −0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:0.0029414443 164:0.00037983558 165:0.0023911442 166:0.0021477563 167:9.2110975e−005 168:0.0026100944 169: −0.0034047128 170:0.0029387963 171:0.0023030045 172:0.0054465104 173:0.0021478815 174:−0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:−0.00031649071 205:0.00065622263 206:0.0026635081 207:0.0039158296 208:0.0020220254 209:0.0012250372 210:0.0028663045 211:−0.0012186989 212:0.00063428417 213:0.0051512984 214:0.00089924945 215:−0.00035291715 216:0.0026578247 217:0.031516869 218: −0.018453332 219:0.012905908 220:0.015366459 221:0.013814257 222:−0.007569442 223: −0.0047048843 224:0.00062012818 225:0.0014852113 226:0.019181944 227:−0.005778844 228: −0.0022216991 229:0.0013164993 230:0.011913291 231:0.0048886021 232:−0.0050922348 233:0.00091115123 234:−0.0028072072 235:0.0020788321 236:−0.0069042598 237: −0.092131011 238:0.068610474 239:−0.0047269738 240:0.0084348312 241:−0.0050073303 242: −0.003040591 243:0.0038143608 244:−0.040638726 245:−0.02857391 246:−0.0472783 247: −0.020520929 248:0.0018310277 249:0.0055512898 250:0.0060781906 251:0.0072731995 252:−0.006453387 253:0.0049183252 254:0.014674404 255:0.026012832 256:0.021858063 .257:−0.021156041 258:−0.0072407476 259:−0.0034868279 260:0.0014243352 261:0.0010014101 262:−0.0013208789 263:0.0028763453 264:−0.0076750983 265:−0.0046692337 266: −0.0012726086 267:0.0068167564 268:−0.04353733 269:0.046706751 270:0.010794718 271: −0.0024784503 272:0.0059213047 273:0.016445309 274:0.016014025 275:−0.0077815265 276: −0.0023459131 277:0.040564284 278:0.032950211 279:0.017959842 280:0.0040876623 281: −0.026083954 282:−0.022933906 283:0.0027156388 284:0.035015725 285:0.029552883 286: −0.010026687 287:0.011907991 288:0.0022531124 289:0.002897898 290:−0.00044569091 291:0.00010489624 292:0.00053147622 293:0.00073173334 294:0.000621646 295: −0.00016437711 296:0.00049518317 297:0.00021529767 298:0.00052096118 299:4.636059e−005 300:−0.0021831172 301:0.0014980205 302:−0.00038898826 303:0.00068646355 304:0.0026823219 305:−0.0040565808 306:0.0020829935 307:0.0013752591 308: −0.00034383399 309:2.7236187e−005 310:0.00070534449 311:0.0012802118 312:0.0030920727 313:0.00088650011 314:0.00014303472 315:0.00071791362 316:0.00019783134 317:2.9171604e−006 318:0.00037660156 319:0.0011750009 320:0.0016896301 321: −0.0015126425 322:−0.00083564757 323:0.0010692998 324:0.0016934061 325:−0.00029338882 326:−0.0034646564 327:7.9289544e−005 328:0.0023930578 329:0.00048041579 330:0.00021849622 331:4.0310828e−005 332:−0.0032790094 333:0.00015884312 334: −0.00031949134 335:3.3427419e−005 336:0.00084852462 337:0.00044620238 338:0.0032407208 339:0.00048842531 340:0.00094149791 # |
| 0.0011294587668324177 1:4.4828572 2:8.2223415 3:2.9781563 4:4.4289684 5:0.42227414 6: −1.5717493 7:1.3719559 8:2.9812431 9:1.8863599 10:0.47722155 11:0.19453254 12:2.5298641 13:0.71065784 14:1.6114749 15:0.81230092 16:3.0162938 17:2.6504457 18:0.69255483 19:1.447444 20:0.55961889 21:1.1205018 22:0.18635012 23:3.4599066 24:0.89394116 25:2.299516 26:0.76571792 27:−0.62200737 28:1.4238536 29:0.92606449 30:1.6690691 31:0.42135558 32:1.2490917 33:1.0898836 34:0.0085214814 35:0.80851263 36:0.29543334 37:2.4276736 38:0.76313913 39:0.54523146 40:1.8881035 41:1.1382017 42:0.65388203 43: −1.0992905 44:0.8885656 45:0.2763125 46:1.4083475 47:0.99239188 48:0.79970312 49:0.63563782 50:1.8465155 51:0.75423354 52:0.62939847 53:2.2419858 54:1.0266342 55: −0.89636725 56:1.2229573 57:0.85758764 58:1.6142527 59:0.36832121 60:0.45254123 61:0.36916149 62:0.42660204 63:0.17117092 64:0.85252941 65:0.81801111 66:−0.86623806 67: −0.38438568 68:1.0171686 69:0.93268329 70:0.056972943 71:0.26466134 72:0.27018225 73:0.17719872 74:0.70610046 75:0.04636937 76:0.086477168 77:0.29317954 78:−0.56059808 79:0.090993397 80:0.9166767 81:0.061696541 82:0.32518891 83:−0.77507943 84:0.61390239 85:0.17143469 86:0.12792408 87:0.25940463 88:0.44887921 89:−0.48372209 90:0.28919423 91:0.06262473 92:0.13472146 93:0.045202162 94:−0.073239826 95:0.18658872 96:0.20809834 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:0.0046544136 117:6.0590241e−007 118:0.00074805523 119:0.0025794252 120:0.00037352511 121:−0.0022889439 122:0.0011132049 123:0.0024242986 124: −0.0045571304 125:0.0020117455 126:0.0092068724 127:0.0077256206 128:0.00070437411 129:0.0012516935 130:0.00055489031 131:0.0013429716 132:0.00036176579 133: −0.0026087298 134:5.3104148e−005 135:0.001098063 136:0.0010348612 137:0.00068726367 138:0.00074436213 139:0.0027458151 140:0.0010222673 141:0.0018521026 142: −0.00061301264 143:0.001804522 144:0.00021584153 145:0.0015449577 146:0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:−0.0012730506 161:0.0014123393 162:0.003461167 163:0.0029414443 164:0.00037983558 165:0.0023911442 166:0.0021477563 167:9.2110975e−005 168:−0.0026100944 169: −0.0034047128 170:0.0029387963 171:0.0023030045 172:0.0054465104 173:−0.0021478815 |

APPENDIX C2-continued

SVM ModelWeights
(340; Benign/Malignant)

174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071 205:0.00065622263 206:0.0026635081 207:0.0039158296 208:0.0020220254 209:0.0012250372 210:0.0028663045 211:0.0012186989 212:0.00063428417 213:0.0051512984 214:0.00089924945 215:0.00035291715 216:0.0026578247 217:0.031516869 218: −0.018453332 219:−0.012905908 220:−0.015366459 221:−0.013814257 222:0.007569442 223: −0.0047048843 224:0.00062012818 225:0.0014852113 226:0.019181944 227:−0.005778844 228: −0.0022216991 229:0.0013164993 230:0.011913291 231:0.0048886021 232:−0.0050922348 233:0.00091115123 234:−0.0028072072 235:−0.0020788321 236:−0.0069042598 237: −0.092131011 238:0.068610474 239:0.0047269738 240:0.0084348312 241:0.0050073303 242: −0.003040591 243:0.0038143608 244:−0.040638726 245:−0.02857391 246:−0.0472783 247: −0.020520929 248:0.0018310277 249:0.0055512898 250:0.0060781906 251:0.0072731995 252:0.006453387 253:−0.0049183252 254:0.014674404 255:0.026012832 256:0.021858063 257:0.021156041 258:−0.0072407476 259:−0.0034868279 260:0.0014243352 261:0.0010014101 262:0.0013208789 263:−0.0028763453 264:0.0076750983 265:0.0046692337 266: −0.0012726086 267:0.0068167564 268:−0.04353733 269:−0.046706751 270:0.010794718 271: −0.0024784503 272:0.0059213047 273:0.016445309 274:0.016014025 275:0.0077815265 276: −0.0023459131 277:0.040564284 278:−0.03 2950211 279:0.017959842 280:0.0040876623 281 −0.026083954 282:0.022933906 283:0.0027156388 284:0.035015725 285:0.029552883 286: −0.010026687 287:0.011907991 288:0.0022531124 289:−0.002897898 290:−0.00044569091 291:0.00010489624 292:0.00053147622 293:0.00073173334 294:0.000621646 295: −0.00016437711 296:−0.00049518317 297:0.00021529767 298:0.00052096118 299:−4.636059e−005 300:0.0021831172 301:0.0014980205 302:0.00038898826 303:0.00068646355 304:0.0026823219 305:0.0040565808 306:−0.0020829935 307:0.0013752591 308: −0.00034383399 309:2.7236187e−005 310:0.00070534449 311:0.0012802118 312:0.0030920727 313:0.00088650011 314:−0.00014303472 315:0.00071791362 316:0.00019783134 317:2.9171604e−006 318:0.00037660156 319:0.0011750009 320:0.0016896301 321: −0.0015126425 322:0.00083564757 323:0.0010692998 324:0.0016934061 325:−0.00029338882 326:−0.0034646564 327:7.9289544e−005 328:0.0023930578 329:0.00048041579 330:0.00021849622 331:4.0310828e−005 332:−0.0032790094 333:0.00015884312 334: −0.00031949134 335:3.3427419e−005 336:0.00084852462 337:0.00044620238 338:−0.0032407208 339:0.00048842531 340:0.00094149791 #
0.0017236454057197211 1:−7.236392 2:−3.5836346 3:1.7660971 4:−0.32848185 5:−1.2832146 6: −6.0978584 7:−3.6553211 8:−0.17175604 9:0.25727716 10:0.22893712 11:2.0433552 12: −2.5095832 13:2.2301786 14:0.89164317 15:0.035530206 16:0.43601635 17:1.5672219 18: −2.1941028 19:−1.6846048 20:−1.9031192 21:1.5150453 22:−0.067690462 23:−0.7034052 24: −0.92714 25:2.8568938 26:0.54916203 27:−0.33980703 28:1.3728271 29:1.5007032 30:1.5150614 31:0.58766556 32:0.91855782 33:1.5538375 34:0.69479793 35:0.36874688 36:0.54761487 37: −1.9475741 38:1.2176952 39:1.0730724 40:1.9726436 41:0.30647516 42:1.2092241 43:0.63217318 44:0.77174801 45:−0.40446022 46:0.10491796 47:1.0020102 48:0.61819273 49:0.47567961 50:0.013156149 51:1.4068747 52:0.2815071 53:0.55821782 54:0.062364895 55:0.7315644 56:0.60225677 57:1.223998 58:1.6821091 59:0.7918604 60:0.1890564 61: −0.84034485 62:−0.26253659 63:0.36804584 64:0.50272626 65:2.2546327 66:0.16593432 67: −0.23399231 68:1.3119842 69:0.49496078 70:0.88905048 71:0.9499805 72:0.87751204 73:0.32013476 74:0.63699913 75:0.19273549 76:1.1294738 77:0.65565783 78:0.36823535 79:0.82951087 80:0.12251247 81:0.012268872 82:−0.73517323 83:0.17581578 84:0.48176602 85:−0.18737254 86:−0.1223734 87:0.17085168 88:0.12654561 89:0.51247317 90:0.11162367 91: −0.092082798 92:0.43368423 93:0.19904512 94:0.18185323 95:0.040728513 96:0.024205608 97:0.0039280006 98:0.010595871 99:0.0072948104 100:0.0007581744 101:0.0015444086 102:0.00086657552 103:0.0014506713 104:0.00027309253 105:0.0003779236 106: −0.0033040401 107:0.002894687 108:0.0012058502 109:0.0026374348 110:0.0018928888 111: −0.0024273857 112:0.0003231481 113:0.00057429477 114:0.00070962519 115:0.0011349921 116:0.0046544136 117:6.0590241e−007 118:0.00074805523 119:0.0025794252 120:0.00037352511 121:0.0022889439 122:0.0011132049 123:0.0024242986 124: −0.0045571304 125:0.0020117455 126:0.0092068724 127:0.0077256206 128:−0.00070437411 129:0.0012516935 130:0.00055489031 131:0.0013429716 132:0.00036176579 133: −0.0026087298 134:5.3104148e−005 135:0.001098063 136:0.0010348612 137:0.00068726367 138:0.00074436213 139:0.0027458151 140:0.0010222673 141:0.0018521026 142: −0.00061301264 143:0.001804522 144:0.00021584153 145:0.0015449577 146:−0.0015697054 147:0.00097707158 148:0.0011295594 149:0.0028935266 150:0.00053708232 151:0.0018405041 152:0.002562111 153:0.0013092471 154:0.00046263589 155: −0.0035724007 156:0.0011358063 157:0.0012884629 158:0.0031973415 159:0.00045693576 160:0.0012730506 161:0.0014123393 162:0.003461167 163:0.0029414443 164:0.00037983558 165:0.0023911442 166:0.0021477563 167:9.2110975e−005 168:0.0026100944 169: −0.0034047128 170:0.0029387963 171:0.0023030045 172:0.0054465104 173:−0.0021478815 174:0.0022738085 175:0.00050098688 176:0.0021780876 177:2.5619611e−005 178: −0.0010297548 179:0.000299401 180:0.0002858036 181:0.0015720503 182:0.0012860922 183:0.0015920103 184:0.0034542123 185:0.0054590856 186:0.0013231005 187: −0.00026378682 188:5.6713336e−005 189:0.0016455925 190:0.00055903167 191:0.00040327062 192:−0.00066433422 193:0.0014816546 194:0.0016943325 195:0.00012320606 196:0.0006577372 197:0.00056744454 198:0.0023361598 199:0.0042997436 200:0.0016990597 201:0.0030764227 202:0.0027063258 203:0.00046884044 204:0.00031649071

APPENDIX C2-continued

SVM ModelWeights
(340; Benign/Malignant)

205:0.00065622263 206:0.0026635081 207:0.0039158296 208:0.0020220254 209:0.0012250372
210:0.0028663045 211:0.0012186989 212:0.00063428417 213:0.0051512984
214:0.00089924945 215:0.00035291715 216:0.0026578247 217:0.031516869 218:
−0.018453332 219:0.012905908 220:0.015366459 221:−0.013814257 222:0.007569442 223:
−0.0047048843 224:0.00062012818 225:0.0014852113 226:0.019181944 227:−0.005778844 228:
−0.0022216991 229:0.0013164993 230:0.011913291 231:0.0048886021 232:−0.0050922348
233:0.00091115123 234:−0.0028072072 235:0.0020788321 236:0.0069042598 237:
−0.092131011 238:0.068610474 239:−0.0047269738 240:0.0084348312 241:−0.0050073303 242:
−0.003040591 243:0.0038143608 244:−0.040638726 245:−0.02857391 246:−0.0472783 247:
−0.020520929 248:0.0018310277 249:0.0055512898 250:0.0060781906 251:0.0072731995
252:−0.006453387 253:0.0049183252 254:0.014674404 255:0.026012832 256:−0.021858063
257:0.021156041 258:0.0072407476 259:−0.0034868279 260:0.0014243352 261:0.0010014101
262:0.0013208789 263:0.0028763453 264:−0.0076750983 265:−0.0046692337 266:
−0.0012726086 267:0.0068167564 268:−0.04353733 269:−0.046706751 270:0.010794718 271:
−0.0024784503 272:0.0059213047 273:0.016445309 274:0.016014025 275:0.0077815265 276:
−0.0023459131 277:0.040564284 278:0.032950211 279:0.017959842 280:0.0040876623 281:
−0.026083954 282:0.022933906 283:0.0027156388 284:0.035015725 285:−0.029552883 286:
−0.010026687 287:0.011907991 288:0.0022531124 289:−0.002897898 290:−0.00044569091
291:0.00010489624 292:0.00053147622 293:0.00073173334 294:0.000621646 295:
−0.00016437711 296:0.00049518317 297:0.00021529767 298:0.00052096118 299:−4.636059e−005
300:−0.0021831172 301:−0.0014980205 302:−0.00038898826 303:0.00068646355
304:0.0026823219 305:−0.0040565808 306:−0.0020829935 307:−0.0013752591 308:
−0.00034383399 309:2.7236187e−005 310:−0.00070534449 311:−0.0012802118 312:−0.0030920727
313:−0.00088650011 314:−0.00014303472 315:0.00071791362 316:0.00019783134
317:2.9171604e−006 318:0.00037660156 319:0.0011750009 320:−0.0016896301 321:
−0.0015126425 322:−0.00083564757 323:0.0010692998 324:−0.0016934061 325:−0.00029338882
326:−0.0034646564 327:−7.9289544e−005 328:0.0023930578 329:0.00048041579
330:0.00021849622 331:4.0310828e−005 332:−0.0032790094 333:−0.00015884312 334:
−0.00031949134 335:3.3427419e−005 336:0.00084852462 337:0.00044620238 338:−0.0032407208
339:0.00048842531 340:0.00094149791 #
0.00078124598767986505 1:−2.1706476 2:−1.9825846 3:1.6808629 4:−9.7863483 5:2.5575449
6:0.7057032 7:−0.42950332 8:−4.667141 9:1.9971507 10:−3.3588634 11:−3.4667838 12:
−0.52633959 13:0.2974067 14:−0.51303798 15:−2.2043688 16:−0.18758157 17:−1.5001959 18:
−0.4526135 19:−2.3206253 20:0.72880054 21:0.85751021 22:1.4700875 23:1.5989654 24:
−1.6109285 25:0.75946838 26:−1.3694041 27:0.069941387 28:−1.2863573 29:−0.71581751 30:
−0.4410125 31:0.85237789 32:0.15556917 33:0.31887108 34:−2.2846727 35:−0.30999845
36:0.024915421 37:1.3966018 38:0.65068775 39:0.19363178 40:−0.14380559 41:−1.6299479
42:0.70048577 43:0.078471817 44:0.073357344 45:1.3000478 46:0.16561341 47:−0.030399367
48:0.12559915 49:0.21890526 50:0.94152272 51:−0.81626856 52:1.3058451 53:0.72284049 54:
−0.17456944 55:0.13139088 56:0.092829317 57:−2.0562599 58:0.53846145 59:−0.1364658 60:
−0.29483664 61:1.29243 62:1.3714556 63:−0.13506477 64:0.47543222 65:−0.59440666
66:0.78138715 67:0.66857392 68:0.38525146 69:0.58482617 70:−0.029068982 71:0.72725481
72:0.37568855 73:1.510435 74:0.38365117 75:−0.96987337 76:0.28935903 77:−0.69556022 78:
−0.091853529 79:0.37636095 80:0.43708503 81:0.26550123 82:−1.0570695 83:0.35788676
84:6.43593568 85:0.79885823 86:−0.45753843 87:0.94902861 88:−0.64771193 89:−0.46155131
90:−0.28816476 91:0.17756711 92:−0.12709361 93:−0.22965741 94:−0.047014233 95:−0.12411006
96:−0.29446343 97:0.0039280006 98:0.010595871 99:−0.0072948104 100:0.0007581744
101:0.0015444086 102:0.00086657552 103:0.0014506713 104:0.00027309253 105:
−0.0003779236 106:−0.0033040401 107:−0.002894687 108:0.0012058502 109:0.0026374348 110:
−0.0018928888 111:−0.0024273857 112:−0.0003231481 113:0.00057429477 114:−0.00070962519
115:0.0011349921 116:−0.0046544136 117:6.0590241e−007 118:0.00074805523 119:
−0.0025794252 120:0.00037352511 121:−0.0022889439 122:0.0011132049 123:−0.0024242986
124:−0.0045571304 125:−0.0020117455 126:−0.0092068724 127:−0.0077256206 128:
−0.00070437411 129:0.0012516935 130:0.00055489031 131:0.0013429716 132:0.00036176579
133:−0.0026087298 134:5.3104148e−005 135:−0.001098063 136:0.0010348612 137:
−0.00068726367 138:−0.00074436213 139:0.0027458151 140:0.0010222673 141:−0.0018521026
142:−0.00061301264 143:−0.001804522 144:−0.00021584153 145:0.0015449577 146:
−0.0015697054 147:−0.00097707158 148:−0.0011295594 149:0.0028935266 150:−0.00053708232
151:0.0018405041 152:−0.002562111 153:−0.0013092471 154:−0.00046263589 155:
−0.0035724007 156:0.0011358063 157:−0.0012884629 158:−0.0031973415 159:0.00045693576
160:−0.0012730506 161:0.0014123393 162:0.003461167 163:−0.0029414443 164:−0.00037983558
165:−0.0023911442 166:0.0021477563 167:9.2110975e−005 168:−0.0026100944 169:
−0.0034047128 170:−0.0029387963 171:−0.0023030045 172:−0.0054465104 173:−0.0021478815
174:−0.0022738085 175:0.00050098688 176:−0.0021780876 177:2.5619611e−005 178:
−0.0010297548 179:0.000299401 180:0.0002858036 181:0.0015720503 182:0.0012860922
183:0.0015920103 184:0.0034542123 185:−0.0054590856 186:−0.0013231005 187:
−0.00026378682 188:−5.6713336e−005 189:0.0016455925 190:0.00055903167 191:0.00040327062
192:−0.00066433422 193:−0.0014816546 194:0.0016943325 195:0.00012320606
196:0.0006577372 197:0.00056744454 198:−0.0023361598 199:0.0042997436 200:−0.0016990597
201:0.0030764227 202:−0.0027063258 203:0.00046884044 204:−0.00031649071
205:0.00065622263 206:−0.0026635081 207:−0.0039158296 208:0.0020220254 209:0.0012250372
210:−0.0028663045 211:−0.0012186989 212:−0.00063428417 213:0.0051512984
214:0.00089924945 215:−0.00035291715 216:−0.0026578247 217:−0.031516869 218:
−0.018453332 219:−0.012905908 220:−0.015366459 221:−0.013814257 222:−0.007569442 223:
−0.0047048843 224:0.00062012818 225:0.0014852113 226:−0.019181944 227:−0.005778844 228:
−0.0022216991 229:−0.0013164993 230:−0.011913291 231:−0.0048886021 232:−0.0050922348
233:−0.00091115123 234:−0.0028072072 235:−0.0020788321 236:−0.0069042598 237:

APPENDIX C2-continued

SVM ModelWeights
(340; Benign/Malignant)

−0.092131011 238:−0.068610474 239:−0.0047269738 240:−0.0084348312 241:−0.0050073303 242:
−0.003040591 243:−0.0038143608 244:−0.040638726 245:−0.02857391 246:−0.0472783 247:
−0.020520929 248:−0.0018310277 249:−0.0055512898 250:−0.0060781906 251:−0.0072731995
252:−0.006453387 253:−0.0049183252 254:−0.014674404 255:−0.026012832 256:−0.021858063
257:−0.021156041 258:−0.0072407476 259:−0.0034868279 260:−0.0014243352 261:−0.0010014101
262:−0.0013208789 263:−0.0028763453 264:−0.0076750983 265:−0.0046692337 266:
−0.0012726086 267:−0.0068167564 268:−0.04353733 269:−0.046706751 270:−0.010794718 271:
−0.0024784503 272:−0.0059213047 273:−0.016445309 274:−0.016014025 275:−0.0077815265 276:
−0.0023459131 277:−0.040564284 278:−0.032950211 279:−0.017959842 280:−0.0040876623 281:
−0.026083954 282:−0.022933906 283:−0.0027156388 284:−0.035015725 285:0.029552883 286:
−0.010026687 287:−0.011907991 288:−0.0022531124 289:−0.002897898 290:−0.00044569091
291:0.00010489624 292:−0.00053147622 293:−0.00073173334 294:−0.000621646 295:
−0.00016437711 296:−0.00049518317 297:0.00021529767 298:0.00052096118 299:−4.636059e−005
300:−0.0021831172 301:−0.0014980205 302:−0.00038898826 303:0.00068646355
304:0.0026823219 305:−0.0040565808 306:−0.0020829935 307:−0.0013752591 308:
−0.00034383399 309:2.7236187e−005 310:−0.00070534449 311:−0.0012802118 312:−0.0030920727
313:−0.00088650011 314:−0.00014303472 315:0.00071791362 316:0.00019783134
317:2.9171604e−006 318:0.00037660156 319:0.0011750009 320:−0.0016896301 321:
−0.0015126425 322:−0.00083564757 323:0.0010692998 324:−0.0016934061 325:−0.00029338882
326:−0.0034646564 327:−7.9289544e−005 328:0.0023930578 329:0.00048041579
330:0.00021849622 331:4.0310828e−005 332:−0.0032790094 333:−0.00015884312 334:
−0.00031949134 335:3.3427419e−005 336:0.00084852462 337:0.00044620238 338:−0.0032407208
339:0.00048842531 340:0.00094149791 #
0.0033153142499855108 1:5.8637757 2:−9.9825153 3:−1.3864986 4:3.7755594 5:1.9810551
6:5.9261589 7:2.0591137 8:1.4179028 9:−2.8670921 10:1.2827179 11:0.51069009 12:2.7566116
13:−1.0318092 14:5.8409891 15:2.453907 16:−1.4336371 17:2.6721907 18:2.6253684 19:
−1.1450388 20:0.95642722 21:−0.68922752 22:−0.63180703 23:−1.2727717 24:2.6737196
25:2.5429664 26:0.12496121 27:0.70460039 28:0.61082274 29:−2.6253922 30:2.9772513
31:1.4704022 32:2.6366663 33:0.59462577 34:−1.7308691 35:−2.8416824 36:1.8223454
37:1.8723491 38:0.31541702 39:1.2786952 40:0.20529886 41: −2.3980207 42:0.4039337 43:
−1.0958207 44:−1.1642426 45:0.81780392 46:−1.8876129 47:−0.87910926 48:0.47651336 49:
−0.31036353 50:0.81277901 51:0.57417709 52:−0.48608726 53:0.038678579 54:1.2284206 55:
−0.13300143 56:−0.91738433 57:1.1555263 58:0.090056382 59:−0.43537176 60:−0.38387787 61:
−0.9908492 62:0.47343999 63:−0.011526085 64:−0.71371078 65:0.026976289 66:0.051007312
67:0.71084046 68:−0.64197159 69:−0.33844063 70:−0.045717873 71:−0.56054622 72:0.051615499
73:0.41121837 74:0.65057576 75:0.54327095 76:0.26035652 77:−0.52896899 78:−0.23127164
79:0.3524617 80:−0.24086736 81:0.11925521 82:0.080059394 83:0.010276271 84:0.36877257
85:0.15841663 86:−0.14087231 87:−0.074028924 88:0.22284043 89:0.14995553 90:−0.11427767
91:−0.2170157 92:0.081317082 93:−0.1668711 94:−0.19747913 95:−0.11586079 96:0.17277965
97:0.0039280006 98:0.010595871 99:−00072948104 100:0.0007581744 101:0.0015444086
102:0.00086657552 103:0.0014506713 104:0.00027309253 105:−0.0003779236 106:
−0.0033040401 107:−0.002894687 108:0.0012058502 109:0.0026374348 110:−0.0018928888 111:
−0.0024273857 112:−0.0003231481 113:0.00057429477 114:−0.00070962519 115:0.0011349921
116:−0.0046544136 117:6.0590241e−007 118:0.00074805523 119:−0.0025794252
120:0.00037352511 121:−0.0022889439 122:0.0011132049 123:−0.0024242986 124:
−0.0045571304 125:−0.0020117455 126:−0.0092068724 127:−0.0077256206 128:−0.00070437411
129:0.0012516935 130:0.00055489031 131:0.0013429716 132:0.00036176579 133:
−0.0026087298 134:5.3104148e−005 135:−0.001098063 136:0.0010348612 137:−0.00068726367
138:−0.00074436213 139:0.0027458151 140:0.0010222673 141:−0.0018521026 142:
−0.00061301264 143:−0.001804522 144:−0.00021584153 145:0.0015449577 146:−0.0015697054
147:−0.00097707158 148:−0.0011295594 149:0.0028935266 150:−0.00053708232
151:0.0018405041 152:−0.002562111 153:−0.0013092471 154:−0.00046263589 155:
−0.0035724007 156:0.0011358063 157:−0.0012884629 158:−0.0031973415 159:0.00045693576
160:−0.0012730506 161:0.0014123393 162:0.003461167 163:−0.0029414443 164:−0.00037983558
165:−0.0023911442 166:0.0021477563 167:9.2110975e−005 168:−0.0026100944 169:
−0.0034047128 170:−0.0029387963 171:−0.0023030045 172:−0.0054465104 173:−0.0021478815
174:−0.0022738085 175:0.00050098688 176:−0.0021780876 177:2.5619611e−005 178:
−0.0010297548 179:0.000299401 180:0.0002858036 181:0.0015720503 182:0.0012860922
183:0.0015920103 184:0.0034542123 185:−0.0054590856 186:0.0013231005 187:
−0.00026378682 188:−5.6713336e−005 189:0.0016455925 190:0.00055903167 191:0.00040327062
192:−0.00066433422 193:−0.0014816546 194:0.0016943325 195:0.00012320606
196:0.0006577372 197:0.00056744454 198:−0.0023361598 199:0.0042997436 200:−0.0016990597
201:0.0030764227 202:−0.0027063258 203:0.00046884044 204:−0.00031649071
205:0.00065622263 206:−0.0026635081 207:−0.0039158296 208:0.0020220254 209:0.0012250372
210:−0.0028663045 211:−0.0012186989 212:−0.00063428417 213:0.0051512984
214:0.00089924945 215:−0.00035291715 216:−0.0026578247 217:−0.031516869 218:
−0.018453332 219:−0.012905908 220:−0.015366459 221:−0.013814257 222:−0.007569442 223:
−0.0047048843 224:0.00062012818 225:0.0014852113 226:−0.019181944 227:−0.005778844 228:
−0.0022216991 229:−0.0013164993 230:−0.011913291 231:−0.0048886021 232:−0.0050922348
233:−0.00091115123 234:−0.0028072072 235:−0.0020788321 236:−0.0069042598 237:
−0.092131011 238:−0.068610474 239:−0.0047269738 240:−0.0084348312 241:−0.0050073303 242:
−0.003040591 243:−0.0038143608 244:−0.040638726 245:−0.02857391 246:−0.0472783 247:
−0.020520929 248:−0.0018310277 249:−0.0055512898 250:−0.0060781906 251:−0.0072731995
252:0.006453387 253:0.0049183252 254:0.014674404 255:−0.026012832 256:−0.021858063
257:0.021156041 258:−0.0072407476 259:0.0034868279 260:−0.0014243352 261:−0.0010014101
262:−0.0013208789 263:−0.0028763453 264:−0.0076750983 265:−0.0046692337 266:
−0.0012726086 267:−0.0068167564 268:−0.04353733 269:−0.046706751 270:−0.010794718 271:

APPENDIX C2-continued

SVM ModelWeights
(340; Benign/Malignant)

−0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 #
0.00099702391646504587 1:−8.6541967 2:3.1313093 3:3.124423 4:3.0343151 5:−1.5841113 6: −2.2087634 7:1.7894588 8:2.8694017 9:−4.4243951 10:−0.45494816 11:1.0369818 12:1.0938125 13:0.27073804 14:−1.4201082 15:−1.1111952 16:1−.1544274 17:−0.61541378 18:0.89156842 19:0.24313243 20:−0.96249247 21:1.2922262 22:−0.69232893 23:0.14764817 24:−1.3923763 25:0.6387915 26:0.084550619 27:−1.4210426 28:−0.043041125 29:0.70565158 30:−2.2790606 31:0.31711981 32:−0.29398012 33:−0.1432732 34:−1.0997872 35:0.89468467 36:0.17898633 37:0.22860222 38:0.046035666 39:1.3129162 40:0.072972745 41:−0.31119242 42:0.24485055 43:1.016295 44:1.1550423 45:0.57052416 46:0.30313149 47:0.47155845 48:−0.252554 49:0.75614375 50:−0.27084967 51:1.2873342 52:−0.50668657 53:−1.0563754 54:0.68687969 55: −1.4469496 56:1.1780907 57:0.29481086 58:−0.39441538 59:−1.1455108 60:1.0291282 61: −0.2951265 62:−0.63262415 63:−1.7717614 64:−0.38663942 65:0.96479446 66:2.2799258 67:0.080531135 68:−0.7447601 69:1.3578986 70:−0.52199012 71:−0.15072392 72:−0.57423425 73:0.075259708 74:0.38988864 75:−0.050941281 76:0.39107621 77:−0.97717643 78:−0.43727434 79:0.064068362 80:−0.97314757 81:−0.12114869 82:−1.2026515 83:0.25698236 84:−0.0038959796 85:0.6433928 86:0.47606063 87:−0.52713388 88:0.33512068 89:0.42516679 90:0.011945772 91:0.27900955 92:0.12157471 93:0.17567495 94:−0.1259127 95:0.29254019 96:0.55650336 97:0.0039280006 98:0.010595871 99:−0.0072948104 100:0.0007581744 101:0.0015444086 102:0.00086657552 103:0.0014506713 104:0.00027309253 105:−0.0003779236 106: −0.0033040401 107:−0.002894687 108:0.0012058502 109:0.0026374348 110:−0.0018928888 111: −0.0024273857 112:−0.0003231481 113:0.00057429477 114:−0.00070962519 115:0.0011349921 116:−0.0046544136 117:6.0590241e−007 118:0.00074805523 119:−0.0025794252 120:0.00037352511 121:−0.0022889439 122:0.0011132049 123:−0.0024242986 124: −0.0045571304 125:−0.0020117455 126:−0.0092068724 127:−0.0077256206 128:−0.00070437411 129:0.0012516935 130:0.00055489031 131:0.0013429716 132:0.00036176579 133: −0.0026087298 134:5.3104148e−005 135:−0.001098063 136:0.0010348612 137:−0.00068726367 138:−0.00074436213 139:0.0027458151 140:0.0010222673 141:−0.0018521026 142: −0.00061301264 143:−0.001804522 144:−0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155: −0.0035724007 156:0.0011358063 157:−0.0012884629 158:−0.0031973415 159:0.00045693576 160:−0.0012730506 161:0.0014123393 162:0.003461167 163:−0.0029414443 164:−0.00037983558 165:−0.0023911442 166:0.0021477563 167:9.2110975e−005 168:−0.0026100944 169: −0.0034047128 170:−0.0029387963 171:−0.0023030045 172:−0.0054465104 173:−0.0021478815 174:−0.0022738085 175:0.00050098688 176:−0.0021780876 177:2.5619611e−005 178: −0.0010297548 179:0.000299401 180:0.0002858036 181:0.0015720503 182:0.0012860922 183:0.0015920103 184:0.0034542123 185:−0.0054590856 186:−0.0013231005 187: −0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212:−0.00063428417 213:0.0051512984 214:0.00089924945 215:−0.00035291715 216:−0.0026578247 217:−0.031516869 218: −0.018453332 219:−0.012905908 220:−0.015366459 221:−0.013814257 222:−0.007569442 223: −0.0047048843 224:0.00062012818 225:0.0014852113 226:−0.019181944 227:−0.005778844 228: −0.0022216991 229:−0.0013164993 230:−0.011913291 231:−0.0048886021 232:−0.0050922348 233:−0.00091115123 234:−0.0028072072 235:−0.0020788321 236:−0.0069042598 237: −0.092131011 238:−0.068610474 239:−0.0047269738 240:−0.0084348312 241:−0.0050073303 242: −0.003040591 243:−0.0038143608 244:−0.040638726 245:−0.02857391 246:−0.0472783 247: −0.020520929 248:−0.0018310277 249:−0.0055512898 250:−0.0060781906 251:−0.0072731995 252:−0.006453387 253:0.0049183252 254:0.014674404 255:0.026012832 256:−0.021858063 257:−0.021156041 258:−0.0072407476 259:−0.0034868279 260:−0.0014243352 261:−0.0010014101 262:−0.0013208789 263:−0.0028763453 264:−0.0076750983 265:−0.0046692337 266: −0.0012726086 267:−0.0068167564 268:−0.04353733 269:−0.046706751 270:−0.010794718 271: −0.0024784503 272:−0.0059213047 273:−0.016445309 274:−0.016014025 275:−0.0077815265 276: −0.0023459131 277:−0.040564284 278:−0.032950211 279:−0.017959842 280:−0.0040876623 281: −0.026083954 282:−0.022933906 283:−0.0027156388 284:−0.035015725 285:−0.029552883 286: −0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355

APPENDIX C2-continued

| SVM ModelWeights (340; Benign/Malignant) |
|---|
| 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:−0.00015884312 334: −0.00031949134 335:3.3427419e−005 336:0.00084852462 337:0.00044620238 338:−0.0032407208 339:0.00048842531 340:0.00094149791 # −3.5502731913815261e−006 1:9.8041286 2:15.643085 3:−14.213445 4:−5.6504297 5:−2.8406351 6:4.8410215 7:−6.6080933 8:−7.4779692 9:−0.5772323 10:−6.2781529 11:8.2602367 12:11.970333 13:6.336812 14:1.1768038 15:−1.7457997 16:1.5841151 17:1.5440294 18:−0.17547397 19: −0.62377983 20:0.05088732 21:−5.221839 22:−2.9309611 23:−0.88320798 24:−1.282207 25: −0.28119931 26:2.1707978 27:−0.44439083 28:0.69384325 29:−0.84158903 30:−2.1587796 31:0.8452878 32:0.89773905 33:−1.0026301 34:−1.1124955 35:0.88503838 36:0.4235985 37: −0.14904873 38:−0.026293054 39:−0.73154718 40:0.40854758 41:0.2893393 42:0.90045565 43: −0.402109 44:−0.20215705 45:−0.19731572 46:0.68088818 47:−0.2196051 48:0.31383833 49: −0.55526811 50:0.1787241 51:−0.36807919 52:−0.2236544 53:0.31867594 54:−0.11530373 55: −0.38835302 56:0.088300563 57:0.29786986 58:0.16426006 59:0.2670193 60:0.2008242 61:0.04549478 62:0.010833706 63:−0.10576705 64:−0.018023184 65:−0.31581616 66:0.4111937 67:0.0011363255 68:−0.32500958 69:0.052457977 70:0.18141507 71:0.010820718 72:−0.1970809 73:0.031182472 74:0.20898099 75:0.092877805 76:−0.0068197995 77:−0.047145113 78: −0.0074180369 79:0.075367324 80:0.21236798 81:0.063954644 82:0.33653501 83:0.087007843 84:−0.14029463 85:−0.086541794 86:0.02149646 87:0.066968374 88:0.10309727 89:0.022807948 90:0.04239285 91:0.013292185 92:0.012786527 93:0.0087664425 94:−0.081786327 95: −0.063556984 96:−0.022940626 97:0.0039280006 98:0.010595871 99:−0.0072948104 100:0.0007581744 101:0.0015444086 102:0.00086657552 103:0.0014506713 104:0.00027309253 105:−0.0003779236 106:−0.0033040401 107:−0.002894687 108:0.0012058502 109:0.0026374348 110:−.0018928888 111:−0.0024273857 112:−0.0003231481 113:0.00057429477 114: −0.00070962519 115:0.0011349921 116:−0.0046544136 117:6.0590241e−007 118:0.00074805523 119:−0.0025794252 120:0.00037352511 121:−0.0022889439 122:0.0011132049 123: −0.0024242986 124:−0.0045571304 125:−0.0020117455 126:−0.0092068724 127:−0.0077256206 128:−0.00070437411 129:0.0012516935 130:0.00055489031 131:0.0013429716 132:0.00036176579 133:−0.0026087298 134:5.3104148e−005 135:−0.001098063 136:0.0010348612 137:−0.00068726367 138:−0.00074436213 139:0.0027458151 140:0.0010222673 141:−0.0018521026 142:−0.00061301264 143:−0.001804522 144: −0.00021584153 145:0.0015449577 146:−0.0015697054 147:−0.00097707158 148:−0.0011295594 149:0.0028935266 150:−0.00053708232 151:0.0018405041 152:−0.002562111 153:−0.0013092471 154:−0.00046263589 155:−0.0035724007 156:0.0011358063 157:−0.0012884629 158: −0.0031973415 159:0.00045693576 160:−0.0012730506 161:0.0014123393 162:0.003461167 163: −0.0029414443 164:−0.00037983558 165:−0.0023911442 166:0.0021477563 167:9.2110975e−005 168:−0.0026100944 169:−0.0034047128 170:−0.0029387963 171:−0.0023030045 172: −0.0054465104 173:−0.0021478815 174:−0.0022738085 175:0.00050098688 176:−0.0021780876 177:2.5619611e−005 178:−0.0010297548 179:0.000299401 180:0.0002858036 181:0.0015720503 182:0.0012860922 183:0.0015920103 184:0.0034542123 185:−0.0054590856 186:−0.0013231005 187:−0.00026378682 188:−5.6713336e−005 189:0.0016455925 190:0.00055903167 191:0.00040327062 192:−0.00066433422 193:−0.0014816546 194:0.0016943325 195:0.00012320606 196:0.0006577372 197:0.00056744454 198:−0.0023361598 199:0.0042997436 200:−0.0016990597 201:0.0030764227 202:−0.0027063258 203:0.00046884044 204:−0.00031649071 205:0.00065622263 206:−0.0026635081 207:−0.0039158296 208:0.0020220254 209:0.0012250372 210:−0.0028663045 211:−0.0012186989 212: −0.00063428417 213:0.0051512984 214:0.00089924945 215:−0.00035291715 216:−0.0026578247 217:−0.031516869 218:−0.018453332 219:−0.012905908 220:−0.015366459 221:−0.013814257 222:−0.007569442 223:−0.0047048843 224:0.00062012818 225:0.0014852113 226:−0.019181944 227:−0.005778844 228:−0.0022216991 229:−0.0013164993 230:−0.011913291 231:−0.0048886021 232:−0.0050922348 233:−0.00091115123 234:−0.0028072072 235:−0.0020788321 236: −0.0069042598 237:−0.092131011 238:−0.068610474 239:−0.0047269738 240:−0.0084348312 241: −0.0050073303 242:−0.003040591 243:0.0038143608 244:−0.040638726 245:−0.02857391 246: −0.0472783 247:−0.020520929 248:−0.0018310277 249:−0.0055512898 250:−0.0060781906 251: −0.0072731995 252:−0.006453387 253:−0.0049183252 254:−0.014674404 255:−0.026012832 256: −0.021858063 257:−0.021156041 258:−0.0072407476 259:−0.0034868279 260:−0.0014243352 261: −0.0010014101 262:−0.0013208789 263:−0.0028763453 264:−0.0076750983 265:−0.0046692337 266:−0.0012726086 267:−0.0068167564 268:−0.04353733 269:−0.046706751 270:−0.010794718 271:−0.0024784503 272:−0.0059213047 273:−0.016445309 274:−0.016014025 275:−0.0077815265 276:−0.0023459131 277:−0.040564284 278:−0.032950211 279:−0.017959842 280:−0.0040876623 281:−0.026083954 282:−0.022933906 283:−0.0027156388 284:−0.035015725 285:−0.029552883 286:−0.010026687 287:−0.011907991 288:0.0022531124 289:−0.002897898 290:−0.00044569091 291:0.00010489624 292:−0.00053147622 293:−0.00073173334 294:−0.000621646 295: −0.00016437711 296:−0.00049518317 297:0.00021529767 298:0.00052096118 299:−4.636059e−005 300:−0.0021831172 301:−0.0014980205 302:−0.00038898826 303:0.00068646355 304:0.0026823219 305:−0.0040565808 306:−0.0020829935 307:−0.0013752591 308: −0.00034383399 309:2.7236187e−005 310:−0.00070534449 311:−0.0012802118 312:−0.0030920727 313:−0.00088650011 314:−0.00014303472 315:0.00071791362 316:0.00019783134 317:2.9171604e−006 318:0.00037660156 319:0.0011750009 320:−0.0016896301 321: −0.0015126425 322:−0.00083564757 323:0.0010692998 324:−0.0016934061 325:−0.00029338882 326:−0.0034646564 327:−7.9289544e−005 328:0.0023930578 329:0.00048041579 330:0.00021849622 331:4.0310828e−005 332:−0.0032790094 333:0.00015884312 334: |

APPENDIX C2-continued

| SVM ModelWeights (340; Benign/Malignant) |
|---|
| −0.00031949134 335:3.3427419e−005 336:0.00084852462 337:0.00044620238 338:−0.0032407208 339:0.00048842531 340:0.00094149791 # |

APPENDIX C3

| SVM Model Weights (340; Early/Late) |
|---|
| SVM-light Version V6.01<br>0 # kernel type<br>3 # kernel parameter -d<br>1 # kernel parameter -g<br>1 # kernel parameter -s<br>1 # kernel parameter -r<br>empty# kernel parameter -u<br>340 # highest feature index<br>59 # number of training documents<br>47 # number of support vectors plus 1<br>−0.46078775 # threshold b, each following line is a SV (starting with alpha*y)<br>0.003263013586870337 1:2.9703248 2:−1.9154285 3:−1.4705251 4:−3.6158135 5:−0.88654208 6:−5.2746539 7:3.5916541 8:−1.5249115 9:0.42257392 10:0.1542328 11:−0.79797947 12:1.5178829 13:−4.328999 14:−1.9303721 15:−3.6791089 16:2.030098 17:3.196708 18:0.70455837 19:−0.99888653 20:−0.90641922 21:−1.3292599 22:−1.3334385 23:−0.034880091 24:−0.21998923 25:−1.0224223 26:−0.27785692 27:0.887824 28:−0.88122153 29:2.4520988 30:−1.8591628 31:−0.2047378 32:−0.43277052 33:1.3049064 34:0.28490406 35:0.58858889 36:0.31118494 37:−0.75974351 38:0.30014536 39:0.16725326 40:0.28239837 41:0.85730082 42:0.18312453 43:0.73757261 44:0.23835303 45:0.42016032 46:−0.027372906 47:0.12297571 48:0.091952026 49:0.19956252 50:0.14478266 51:−0.31726134 52:0.075183503 53:0.078598507 54:−0.32566643 55:0.26622328 56:−0.10797127 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 |

APPENDIX C3-continued

| SVM Model Weights (340; Early/Late) |
| --- |
| 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # −0.0028429600743467816 1:−13.079961 2:1.0930103 3:2.5594432 4:0.53382522 5:−14.319618 6:−7.9226675 7:−5.8632889 8:−4.1756377 9:−1.4476115 10:−1.2879921 11:−0.88051426 12:0.80407524 13:0.68481839 14:−1.0680926 15:−0.58902317 16:1.5674455 17:−1.3136758 18:1.8976649 19:0.99831778 20:0.30186781 21:−1.2339196 22:1.8443847 23:1.7902417 24:2.6849024 25:−1.6639206 26:−0.94131452 27:−1.724227 28:0.95484877 29:1.2411916 30:0.94278502 31:−0.31173104 32:1.1069901 33:−1.0650786 34:1.0388733 35:−1.1440469 36:1.801355 37:0.34765008 38:2.0440075 39:1.0830725 40:−0.11946082 41:0.065369211 42:0.60018569 43:−1.6837276 44:0.66784209 45:−0.69387454 46:0.7953223 47:−0.41097218 48:0.2578046 49:−0.30210593 50:0.66700733 51:0.79959631 52:−0.11242599 53:−0.74902785 54:−0.82433671 55:−0.45018244 56:0.55889755 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 |

APPENDIX C3-continued

SVM Model Weights
(340; Early/Late)

304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
−0.00099756979063644934 1:−4.7208257 2:4.0732508 3:1.5652837 4:4.0598516 5:−9.3037663
6:−0.83973908 7:−0.71216238 8:−0.83917409 9:−0.058870234 10:3.7083743 11:2.5553396
12:0.70841408 13:1.3753837 14:0.24954933 15:−0.0149606 16:−0.040375799 17:−0.17532998
18:1.7250814 19:0.88794386 20:1.113205 21:0.10319968 22:−1.2477883 23:−2.4926963
24:−0.94231015 25:1.4475657 26:2.4376483 27:1.81165 28:0.68418247 29:−1.7247032 30:0.68413621
31:1.0965656 32:0.72656965 33:0.26861012 34:2.0053701 35:2.0690022 36:−1.2135777
37:−1.5699004 38:−0.53900796 39:−1.3077862 40:−1.0385492 41:0.74263275 42:1.2781017
43:0.7582199 44:1.0456978 45:0.21704477 46:2.6449811 47:1.8006939 48:0.66939378
49:0.00098386058 50:0.46474424 51:0.14940944 52:−0.75969249 53:−0.2440035 54:−0.17267539
55:0.22942427 56:−1.0117854 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786
104:−0.001393425 105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086 118:−0.0008155898
119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:0.00021409123 131:8.4772248e−005
132:0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005
214:−0.00089089427 215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248
327:−0.00017874227 328:0.0024365219 329:−0.00083040918 330:0.00055475923 331:2.3758541e−005
332:0.0013844321 333:0.00018908412 334:−4.6850397e−005 335:0.00017908432

APPENDIX C3-continued

SVM Model Weights
(340; Early/Late)

336:0.0027642041 337:−0.00026057736 338:−0.0019368717 339:0.0012275067 340:−0.0021567047 #
−0.003263013586870337 1:−1.9800807 2:2.2620521 3:2.8543808 4:1.8967757 5:−8.6841125
6:7.2651377 7:−6.1430531 8:2.780396 9:5.0979185 10:3.9032483 11:−2.852982 12:1.1858057
13:−0.31181017 14:2.4165611 15:0.65978038 16:−0.98159003 17:−0.47111213 18:0.2488336
19:−2.4543958 20:1.345574 21:1.3306577 22:1.0412785 23:−1.6139855 24:−0.58955914 25:−1.5438869
26:1.2458951 27:−1.0349149 28:−3.0767884 29:1.2092717 30:−0.32970193 31:−1.1355613
32:0.41798267 33:1.5676863 34:1.6036789 35:0.75510448 36:−1.0092349 37:−0.069946937
38:−1.9267184 39:1.4684548 40:1.5948615 41:0.18582146 42:1.4165688 43:−0.64861572
44:0.14727257 45:−0.036436558 46:−1.9363652 47:−0.38919815 48:1.392267 49:−0.37833858
50:−0.38228285 51:0.44738469 52:0.23698284 53:0.49579591 54:0.21296412 55:0.62224996
56:−0.1965612 57:0.0009495847 58:−0.00063543959 59:0.00017326932 60:0.0011059562
61:0.0022817524 62:−0.0032958018 63:0.00029474383 64:0.0021514872 65:−0.0054451232
66:−0.0024786978 67:3.7493555e−005 68:0.00035079228 69:0.0023467517 70:0.001588242
71:0.001914337 72:0.0012793314 73:0.0016132059 74:0.00040791018 75:0.0013395234
76:0.00060126832 77:0.0017832168 78:0.0019726807 79:0.0013805456 80:−0.00077531522
81:3.2110733e−005 82:0.0011871321 83:0.00056208909 84:0.0005204202 85:0.0010900472
86:0.0016796719 87:0.0010130677 88:0.00086538575 89:0.0014052332 90:0.0012018452
91:0.00018189113 92:0.00057689246 93:0.0018313623 94:0.0026408355 95:0.00079052034
96:0.0019842789 97:−0.0015824389 98:−0.00092224235 99:−0.0010365265 100:−8.9265384e−005
101:−0.00011542163 102:0.0024433194 103:0.0015950786 104:−0.001393425 105:−0.00076850987
106:−0.0017206173 107:−0.0011140696 108:−0.0020789856 109:0.0013786858
110:−0.00081737712 111:−0.0025310477 112:−0.0010236512 113:−0.00049510651
114:0.0013168686 115:−0.0017368494 116:−0.00051662087 117:−0.0011937086 118:−0.0008155898
119:−0.0014308705 120:−0.00060646527 121:−0.0023188046 122:−0.00047986541
123:−0.0017967777 124:−0.0028703539 125:−0.0008995044 126:−0.0044899271 127:−0.0037051167
128:0.00010453928 129:0.0017558743 130:−0.00021409123 131:8.4772248e−005
132:−0.00059640477 133:0.00091315049 134:0.0029517044 135:0.0012407211 136:0.001771849
137:0.00061086519 138:0.0016401729 139:11190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173−:0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027942227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.00060386706196996942 1:1.2953433 2:−10.811604 3:10.668916 4:7.6443572 5:4.8650537
6:−2.3720403 7:−0.53300303 8:1.4913656 9:2.2692528 10:−4.1517024 11:5.0973153 12:−3.961812
13:−4.989172 14:5.9122295 15:2.8848045 16:−2.1117735 17:1.1214025 18:4.17628 19:−0.35360423
20:−0.57471097 21:−4.3517232 22:0.99931109 23:−0.83541495 24:−0.81100011 25:1.5716805
26:−0.70921725 27:−1.5307126 28:−0.17174035 29:−0.33846083 30:−1.4841211 31:−0.62835532
32:1.5003964 33:−0.36885175 34:−0.91448486 35:−0.17173344 36:0.59208959 37:−0.70629734

APPENDIX C3-continued

| SVM Model Weights (340; Early/Late) |
| --- |
| 38:0.2362466 39:0.29450372 40:0.050759379 41:−0.65440804 42:0.98319513 43:−0.49021548 44:0.74737632 45:−0.06180748 46:−0.011289967 47:0.84981161 48:0.22749481 49:−0.25232136 50:−0.37800777 51:−0.26025736 52:−0.098334007 53:0.44000566 54:−0.074621581 55:0.14722836 56:0.13270916 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513676 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # 0.0018154440402891883 1:−7.4905663 2:−4.2124224 3:2.557915 4:−5.2878695 5:0.80657786 6:−0.37115183 7:1.6812637 8:−3.7509978 9:0.51045167 10:4.1135268 11:0.76780587 12:1.3013476 13:−0.53182048 14:1.9176185 15:1.1816503 16:−0.35555935 17:−1.2507631 18:−1.747479 19:−1.9851712 20:−5.4316225 21:−0.64183134 22:−0.1643706 23:0.49522722 24:−0.50650555 25:1.0811261 26:0.4170202 27:0.59523118 28:−0.86196548 29:0.98918843 30:2.7127433 31:0.09164647 32:1.818579 33:−0.2627672 34:−1.4432161 35:−2.6616316 36:−1.7954003 37:1.4497789 38:−0.026815932 39:0.10891506 40:0.39038053 41:1.1279498 42:−0.46706548 43:−0.043462954 44:0.95625806 45:1.2252256 46:1.529254 47:−0.070296757 48:−1.0965108 49:−1.1075377 50:0.40098587 51:−0.39495179 52:1.1051384 53:0.0084416987 54:−0.055172343 55:1.228945 56:−0.13040337 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 |

APPENDIX C3-continued

SVM Model Weights
(340; Early/Late)

75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005
214:−0.00089089427 215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:−0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.00097418464150607364 1:6.7611756 2:−14.71443 3:8.2472305 4:7.897903 5:2.2104344
6:1.6990815 7:−5.5606017 8:−3.6665649 9:0.020383494 10:−2.7719841 11:4.6774445 12:7.1823139
13:0.92396528 14:−5.7546 15:−2.7706814 16:−6.6301026 17:−2.2711689 18:−1.306276
19:−1.7461162 20:1.3542767 21:−1.3777606 22:0.60129839 23:0.24038176 24:−1.4764284
25:−1.0552083 26:−1.0486079 27:1.2815171 28:−0.14424071 29:−0.014129613 30:0.8364315
31:−0.93981826 32:−0.82154411 33:−0.51832187 34:1.1584929 35:0.8353551 36:0.14221531
37:0.50732559 38:−0.15574506 39:−0.080617838 40:0.63888073 41:0.45644015 42:−0.64732808
43:0.5694508 44:−0.11251554 45:−0.1094914 46:0.092000626 47:−0.11982939 48:−0.33667779
49:0.061028276 50:0.10834024 51:0.053820822 52:0.26874837 53:−0.29877242 54:0.13643929
55:0.10052268 56:0.17111219 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856

APPENDIX C3-continued

| SVM Model Weights (340; Early/Late) |
|---|
| 109:0.0013786858 110:−0.00081737712 111:−0.0025310477 112:−0.0010236512 113:−0.00049510651 |
| 114:0.0013168686 115:−0.0017368494 116:−0.00051662087 117:−0.0011937086 |
| 118:−0.0008155898 119:−0.0014308705 120:−0.00060646527 121:−0.0023188046 122:−0.00047986541 |
| 123:−0.0017967777 124:−0.0028703539 125:−0.0008995044 126:−0.0044899271 |
| 127:−0.0037051167 128:0.00010453928 129:0.0017558743 130:−0.00021409123 131:8.4772248e−005 |
| 132:−0.00059640477 133:0.00091315049 134:0.0029517044 135:0.0012407211 |
| 136:0.001771849 137:0.00061086519 138:0.0016401729 139:1.1190635e−005 140:0.00066645071 |
| 141:0.0020694127 142:−0.0019681684 143:−0.0010553099 144:0.0023889465 145:0.0018726855 |
| 146:−0.00070473028 147:−0.0012693994 148:0.0013133255 149:0.0017171054 150:−0.0023144449 |
| 151:0.0023775783 152:−0.00045603843 153:−0.0020286744 154:−3.1378081e−006 |
| 155:−0.0017911249 156:0.00026146293 157:−0.00066072296 158:−0.0012093179 |
| 159:0.00038491705 160:0.00085559086 161:0.0025676095 162:0.0016044743 163:−0.00089113193 |
| 164:0.0024120815 165:0.0010050905 166:0.0013388922 167:−1.9663272e−005 |
| 168:−0.00063788053 169:−0.001915552 170:−0.0015327755 171:−0.00080461183 172:−0.0022213417 |
| 173:−0.0012071569 174:0.00085961225 175:1.1924029e−005 176:−0.00010044254 |
| 177:0.0011742229 178:−0.00082149269 179:−0.0016058821 180:−0.0010348763 181:−0.00091460953 |
| 182:−0.0004915254 183:−0.00073268131 184:0.00074214442 185:−0.0018549222 |
| 186:−0.00029827142 187:−0.0012626129 188:0.0011506754 189:0.0014984758 190:0.001521907 |
| 191:0.0011545231 192:−0.0017103127 193:−0.0005076346 194:−0.00046162415 195:−0.00039687741 |
| 196:0.0006169476 197:0.0019146017 198:−0.001938576 199:0.00174745 200:−0.00036255008 |
| 201:0.001886385 202:0.00071268051 203:−0.0015044769 204:−0.00094833004 |
| 205:−0.0020877882 206:−0.0016524799 207:−0.002788797 208:0.001349878 209:0.001943506 |
| 210:−0.00086329813 211:0.00089030684 212:−0.0019820002 213:6.8280075e−005 |
| 214:−0.00089089427 215:−0.0011382027 216:−0.0011946515 217:−0.031154955 218:−0.018805003 |
| 219:−0.01448297 220:−0.014768096 221:−0.01189405 222:−0.0050329659 223:−0.0038689009 |
| 224:2.2608641e−005 225:−0.00011902419 226:−0.018885663 227:−0.0053921309 228:−0.0018284534 |
| 229:−0.0052720057 230:−0.009582757 231:−0.0060223294 232:−0.0011540388 |
| 233:−0.0011784985 234:−0.0036054854 235:−0.0014334067 236:−0.0057753613 237:−0.092932746 |
| 238:−0.071324907 239:−0.0057371478 240:−0.006171681 241:−0.0023048196 242:−0.0031618457 |
| 243:−0.0039265179 244:−0.036298919 245:−0.026567493 246:−0.048627507 247:−0.022513576 |
| 248:−0.0027006424 249:−0.0030078713 250:−0.0061391126 251:−0.0061381557 252:−0.0049137147 |
| 253:−0.0035512438 254:−0.012955156 255:−0.022692045 256:−0.019110594 257:−0.019834602 |
| 258:−0.0055528483 259:−0.0031212247 260:−0.0048848111 261:−0.0025836895 |
| 262:−0.0010775019 263:−0.0019687952 264:−0.0064801569 265:−0.0049881209 266:−0.0030259397 |
| 267:−0.0079323547 268:−0.043975201 269:−0.047393609 270:−0.0097410055 271:−0.0014055291 |
| 272:−0.0071474779 273:−0.015365882 274:−0.01525611 275:−0.0060280701 276:−0.0022994229 |
| 277:−0.044466536 278:−0.037435107 279:−0.021463662 280:−0.0029869985 281:−0.030177595 |
| 282:−0.023953391 283:−0.005625559 284:−0.035487764 285:−0.029201077 286:−0.011287678 |
| 287:−0.0095548136 288:−5.3504686e−005 289:−0.0016710128 290:0.0016311913 |
| 291:0.0015074767 292:0.0012213683 293:−0.0015347537 294:−7.1857015e−005 295:−0.0013649603 |
| 296:−0.0018400808 297:−0.0011357415 298:0.00029335488 299:−0.00027912227 |
| 300:0.003004099 301:−0.00078015722 302:−0.00046966597 303:−0.00038853599 |
| 304:0.0011859888 305:−0.0017202824 306:0.0010953069 307:0.0015855392 308:−0.0017361958 |
| 309:0.0011252258 310:0.00020620346 311:−0.0008949365 312:−0.00079829368 313:−0.00031991332 |
| 314:0.0018246222 315:0.00081679551 316:0.00071390043 317:0.00014404937 |
| 318:0.00030348785 319:0.0007406784 320:0.00051131583 321:0.0007617402 322:0.0015480069 |
| 323:0.00016401848 324:−0.0024698905 325:−0.00046456934 326:−0.0014662248 327:−0.00017874227 |
| 328:0.0024365219 329:−0.00083040918 330:0.00055475923 331:−2.3758541e−005 |
| 332:0.0013844321 333:0.00018908412 334:−4.6850397e−005 335:0.00017908432 |
| 336:0.0027642041 337:−0.00026057736 338:−0.0019368717 339:0.0012275067 340:−0.0021567047 # |
| 0.003263013586870337 1:−4.7538085 2:−0.59608591 3:1.9817924 4:0.188968 5:1.4622716 |
| 6:2.7846963 7:−0.015608484 8:−0.34373811 9:−0.33039114 10:1.4307724 11:0.19272146 |
| 12:−0.23617357 13:−0.0479552 14:2.1887279 15:−0.70616794 16:1.0666244 17:−2.6240268 |
| 18:−0.24965028 19:0.62618273 20:0.39855644 21:−0.77940083 22:−1.0156705 23:0.63041109 |
| 24:−0.12485303 25:−0.042265873 26:0.166668 27:0.74196172 28:3.572463 29:1.9412031 |
| 30:2.2433181 31:0.82924473 32:−0.9799 33:0.84773189 34:0.17739867 35:0.80027115 |
| 36:0.98595488 37:−0.35706881 38:0.18436019 39:0.54515535 40:0.16205844 41:1.3908807 |
| 42:−0.064833641 43:0.29049823 44:−0.8086499 45:2.148047 46:−0.92554474 47:0.78878492 |
| 48:1.6272061 49:−2.0635402 50:−0.98432845 51:−1.0829464 52:−1.1132796 53:0.54404491 |
| 54:0.82486242 55:−0.77055466 56:1.5471666 57:0.0009495847 58:−0.00063543959 |
| 59:0.00017326932 60:0.0011059562 61:0.0022817524 62:−0.0032958018 63:0.00029474383 |
| 64:−0.0021514872 65:−0.0054451232 66:−0.0024786978 67:3.7493555e−005 68:0.00035079228 |
| 69:0.0023467517 70:0.001588242 71:0.001914337 72:0.0012793314 73:0.0016132059 |
| 74:0.00040791018 75:0.0013395234 76:0.00060126832 77:0.0017832168 78:0.0019726807 |
| 79:0.0013805456 80:−0.00077531522 81:3.2110733e−005 82:0.0011871321 83:0.00056208909 |
| 84:0.0005204202 85:0.0010900472 86:0.0016796719 87:0.0010130677 88:0.00086538575 |
| 89:0.0014052332 90:0.0012018452 91:0.00018189113 92:0.00057689246 93:0.0018313623 |
| 94:0.0026408355 95:0.00079052034 96:0.0019842789 97:−0.0015824389 98:−0.00092224235 |
| 99:−0.0010365265 100:−8.9265384e−005 101:−0.00011542163 102:0.0024433194 103:0.0015950786 |
| 104:−0.001393425 105:−0.00076850987 106:−0.0017206173 107:−0.0011140696 108:−0.0020789856 |
| 109:0.0013786858 110:−0.00081737712 111:−0.0025310477 112:−0.0010236512 |
| 113:−0.00049510651 114:0.0013168686 115:−0.0017368494 116:−0.00051662087 |
| 117:−0.0011937086 118:−0.0008155898 119:−0.0014308705 120:−0.00060646527 121:−0.0023188046 |
| 122:−0.00047986541 123:−0.0017967777 124:−0.0028703539 125:−0.0008995044 126:−0.0044899271 |
| 127:−0.0037051167 128:0.00010453928 129:0.0017558743 130:−0.00021409123 |
| 131:8.4772248e−005 132:−0.00059640477 133:0.00091315049 134:0.0029517044 |
| 135:0.0012407211 136:0.001771849 137:0.00061086519 138:0.0016401729 139:1.1190635e−005 |

APPENDIX C3-continued

| SVM Model Weights (340; Early/Late) |
|---|
| 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # 0.003263013586870337 1:−8.3236828 2:−2.2087071 3:−0.27089623 4:2.6121626 5:2.6397204 6:3.6725602 7:2.614264 8:2.3370502 9:−2.1257644 10:−0.6181981 11:0.25396436 12:1.6628995 13:−0.4154028 14:3.5387452 15:2.3750374 16:3.0965297 17:−4.5929313 18:−0.2210283 19:3.013021 20:−0.56659156 21:−1.3427184 22:1.5178272 23:1.9356618 24:−0.78502053 25:−4.484839 26:−0.76929528 27:2.2739475 28:−4.4582672 29:−0.69363391 30:−0.32333046 31:1.2145813 32:1.0306679 33:0.56277591 34:0.6252628 35:1.3868178 36:0.95188469 37:0.76303911 38:0.64999557 39:−1.9922973 40:−0.72694093 41:0.86111587 42:−0.41919318 43:0.025058085 44:−0.73094058 45:0.0028740941 46:−0.55918264 47:0.36742008 48:−0.26092228 49:0.45736969 50:0.37089363 51:−0.49157661 52:−0.10223648 53:−0.12217113 54:−0.58239323 55:0.10917395 56:−0.078273892 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 |

APPENDIX C3-continued

| SVM Model Weights (340; Early/Late) |
|---|
| 173:−0.0012071569 174:0.00085961225 175:1.1924029e−005 176:−0.00010044254 |
| 177:0.0011742229 178:−0.00082149269 179:−0.0016058821 180:−0.0010348763 181:−0.00091460953 |
| 182:−0.0004915254 183:−0.00073268131 184:0.00074214442 185:−0.0018549222 |
| 186:−0.00029827142 187:−0.0012626129 188:0.0011506754 189:0.0014984758 190:0.001521907 |
| 191:0.0011545231 192:−0.0017103127 193:−0.0005076346 194:−0.00046162415 195:−0.00039687741 |
| 196:0.0006169476 197:0.0019146017 198:−0.001938576 199:0.00174745 200:−0.00036255008 |
| 201:0.001886385 202:0.00071268051 203:−0.0015044769 204:−0.00094833004 |
| 205:0.0020877882 206:−0.0016524799 207:−0.002788797 208:0.001349878 209:0.001943506 |
| 210:−0.00086329813 211:0.00089030684 212:−0.0019820002 213:6.8280075e−005 214:−0.00089089427 |
| 215:−0.0011382027 216:−0.0011946515 217:−0.031154955 218:−0.018805003 |
| 219:−0.01448297 220:−0.014768096 221:−0.01189405 222:−0.0050329659 223:−0.0038689009 |
| 224:2.2608641e−005 225:−0.00011902419 226:−0.018885663 227:−0.0053921309 228:−0.0018284534 |
| 229:−0.0052720057 230:−0.009582757 231:−0.0060223294 232:−0.0011540388 |
| 233:−0.0011784985 234:−0.0036054854 235:−0.0014334067 236:−0.0057753613 237:−0.092932746 |
| 238:−0.071324907 239:−0.0057371478 240:−0.006171681 241:−0.0023048196 242:−0.0031618457 |
| 243:−0.0039265179 244:−0.036298919 245:−0.026567493 246:−0.048627507 247:−0.022513576 |
| 248:−0.0027006424 249:−0.0030078713 250:−0.0061391126 251:−0.0061381557 252:−0.0049137147 |
| 253:−0.0035512438 254:−0.012955156 255:−0.022692045 256:−0.019110594 257:−0.019834602 |
| 258:−0.0055528483 259:−0.0031212247 260:−0.0048848111 261:−0.0025836895 |
| 262:−0.0010775019 263:−0.0019687952 264:−0.0064801569 265:−0.0049881209 266:−0.0030259397 |
| 267:−0.0079323547 268:−0.043975201 269:−0.047393609 270:−0.0097410055 271:−0.0014055291 |
| 272:−0.0071474779 273:−0.015365882 274:−0.01525611 275:−0.0060280701 276:−0.0022994229 |
| 277:−0.044466536 278:−0.037435107 279:−0.021463662 280:−0.0029869985 281:−0.030177595 |
| 282:−0.023953391 283:−0.005625559 284:−0.035487764 285:−0.029201077 286:−0.011287678 |
| 287:−0.0095548136 288:−5.3504686e−005 289:−0.0016710128 290:0.0016311913 |
| 291:0.0015074767 292:0.0012213683 293:−0.0015347537 294:−7.1857015e−005 295:−0.0013649603 |
| 296:−0.0018400808 297:−0.0011357415 298:0.00029335488 299:−0.00027912227 |
| 300:0.003004099 301:−0.00078015722 302:−0.00046966597 303:−0.00038853599 |
| 304:0.0011859888 305:−0.0017202824 306:0.0010953069 307:0.0015855392 308:−0.0017361958 |
| 309:0.0011252258 310:0.00020620346 311:−0.0008949365 312:−0.00079829368 313:−0.00031991332 |
| 314:0.0018246222 315:0.00081679551 316:0.00071390043 317:0.00014404937 |
| 318:0.00030348785 319:0.0007406784 320:0.00051131583 321:0.0007617402 322:0.0015480069 |
| 323:0.00016401848 324:−0.0024698905 325:−0.00046456934 326:−0.0014662248 327:−0.00017874227 |
| 328:0.0024365219 329:−0.00083040918 330:0.00055475923 331:−2.3758541e−005 |
| 332:0.0013844321 333:0.00018908412 334:−4.6850397e−005 335:0.00017908432 |
| 336:0.0027642041 337:−0.00026057736 338:−0.0019368717 339:0.0012275067 340:−0.0021567047 # |
| −0.003263013586870337 1:−0.24590166 2:−8.1644478 3:3.5928798 4:−1.0753064 5:−2.0135837 |
| 6:−0.10096657 7:−1.1228001 8:−3.6788621 9:−1.2726107 10:−2.0068936 11:−2.3925679 12:1.0569448 |
| 13:−0.40451995 14:0.88951957 15:−4.2740674 16:2.5109732 17:−1.3839777 18:−1.826614 |
| 19:0.79616469 20:−3.4918079 21:2.5179839 22:2.6169379 23:1.2478143 24:−2.9698548 |
| 25:4.3714228 26:−0.19307458 27:−1.039034 28:−1.4048718 29:−1.5676883 30:−1.3980765 |
| 31:1.1577379 32:−1.6144001 33:−1.1187478 34:−0.030886892 35:0.68731695 36:−1.4642311 |
| 37:−0.28218594 38:0.97064406 39:−0.63970482 40:0.7588104 41:−0.14460278 42:0.4816044 |
| 43:−1.057313 44:−0.95472586 45:−1.2895756 46:0.30930915 47:−0.14780316 48:1.2880782 |
| 49:−0.33680031 50:−0.59040457 51:−0.13015135 52:−0.36234295 53:1.2290097 54:−0.58924288 |
| 55:−0.38097394 56:0.21798027 57:0.0009495847 58:−0.00063543959 59:0.00017326932 |
| 60:0.0011059562 61:0.0022817524 62:−0.0032958018 63:0.00029474383 64:−0.0021514872 |
| 65:−0.0054451232 66:−0.0024786978 67:3.7493555e−005 68:0.00035079228 69:0.0023467517 |
| 70:0.001588242 71:0.001914337 72:0.0012793314 73:0.0016132059 74:0.00040791018 |
| 75:0.0013395234 76:0.00060126832 77:0.0017832168 78:0.0019726807 79:0.0013805456 |
| 80:−0.00077531522 81:3.2110733e−005 82:0.0011871321 83:0.00056208909 84:0.0005204202 |
| 85:0.0010900472 86:0.0016796719 87:0.0010130677 88:0.00086538575 89:0.0014052332 |
| 90:0.0012018452 91:0.00018189113 92:0.00057689246 93:0.0018313623 94:0.0026408355 |
| 95:0.00079052034 96:0.0019842789 97:−0.0015824389 98:−0.00092224235 99:−0.0010365265 |
| 100:−8.9265384e−005 101:−0.00011542163 102:0.0024433194 103:0.0015950786 |
| 104:−0.001393425 105:−0.00076850987 106:−0.0017206173 107:−0.0011140696 108:−0.0020789856 |
| 109:0.0013786858 110:−0.00081737712 111:−0.0025310477 112:−0.0010236512 113:−0.00049510651 |
| 114:0.0013168686 115:−0.0017368494 116:−0.00051662087 117:−0.0011937086 |
| 118:−0.0008155898 119:−0.0014308705 120:−0.00060646527 121:−0.0023188046 122:−0.00047986541 |
| 123:−0.0017967777 124:−0.0028703539 125:−0.0008995044 126:−0.0044899271 |
| 127:−0.0037051167 128:0.00010453928 129:0.0017558743 130:−0.00021409123 131:8.4772248e−005 |
| 132:−0.00059640477 133:0.00091315049 134:0.0029517044 135:0.0012407211 |
| 136:0.001771849 137:0.00061086519 138:0.0016401729 139:1.1190635e−005 140:0.00066645071 |
| 141:0.0020694127 142:−0.0019681684 143:−0.0010553099 144:0.0023889465 145:0.0018726855 |
| 146:−0.00070473028 147:−0.0012693994 148:0.0013133255 149:0.0017171054 150:−0.0023144449 |
| 151:0.0023775783 152:−0.00045603843 153:−0.0020286744 154−:3.1378081e−006 |
| 155:−0.0017911249 156:0.00026146293 157:−0.00066072296 158:−0.0012093179 |
| 159:0.00038491705 160:0.00085559086 161:0.0025676095 162:0.0016044743 163:−0.00089113193 |
| 164:0.0024120815 165:0.0010050905 166:0.0013388922 167:−1.9663272e−005 |
| 168:−0.00063788053 169:−0.001915552 170:−0.0015327755 171:−0.00080461183 172:−0.0022213417 |
| 173:−0.0012071569 174:0.00085961225 175:1.1924029e−005 176:−0.00010044254 |
| 177:0.0011742229 178:−0.00082149269 179:−0.0016058821 180:−0.0010348763 181:−0.00091460953 |
| 182:−0.0004915254 183:−0.00073268131 184:0.00074214442 185:−0.0018549222 |
| 186:−0.00029827142 187:−0.0012626129 188:0.0011506754 189:0.0014984758 190:0.001521907 |
| 191:0.0011545231 192:−0.0017103127 193:−0.0005076346 194:−0.00046162415 195:−0.00039687741 |
| 196:0.0006169476 197:0.0019146017 198:−0.001938576 199:0.00174745 200:−0.00036255008 |
| 201:0.001886385 202:0.00071268051 203:−0.0015044769 204:−0.00094833004 |

APPENDIX C3-continued

SVM Model Weights
(340; Early/Late)

205:0.0020877882 206:−0.0016524799 207:−0.002788797 208:0.001349878 209:0.001943506
210:−0.00086329813 211:0.00089030684 212:−0.0019820002 213:6.8280075e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
−0.003263013586870337 1:−7.5296364 2:−0.089652337 3:1.6496497 4:−2.9499371 5:−0.089410551
6:−1.4661449 7:5.7495131 8:−0.59138709 9:−2.9437177 10:0.49092665 11:0.25325522
12:−5.5844264 13:−0.58515418 14:−1.6031579 15:−3.2792425 16:−2.5045371 17:−1.9578328
18:0.72970074 19:0.5297811 20:1.2443616 21:0.022985032 22:0.98236364 23:0.047812771
24:−1.324574 25:−0.34963769 26:0.14184867 27:0.71378028 28:0.39638865 29:−0.35865536
30:−0.62940234 31:0.51807815 32:1.1381087 33:−0.87863255 34:−1.210515 35:−1.7179273
36:−1.1261417 37:−0.48560384 38:−0.4191128 39:−1.5731698 40:1.8958013 41:0.46835396
42:−0.10821192 43:0.69468832 44:0.40906781 45:−0.25131008 46:−1.9610106 47:0.11883042
48:1.243423 49:−0.93002588 50:1.0313464 51:0.48004711 52:0.35595828 53:−2.107121
54:0.36519721 55:−1.2451171 56:−1.0899005 57:0.0009495847 58:−0.00063543959
59:0.00017326932 60:0.0011059562 61:0.0022817524 62:−0.0032958018 63:0.00029474383
64:−0.0021514872 65:−0.0054451232 66:−0.0024786978 67:3.7493555e−005 68:0.00035079228
69:0.0023467517 70:0.001588242 71:0.001914337 72:0.0012793314 73:0.0016132059
74:0.00040791018 75:0.0013395234 76:0.00060126832 77:0.0017832168 78:0.0019726807
79:0.0013805456 80:−0.00077531522 81:3.2110733e−005 82:0.0011871321 83:0.00056208909
84:0.0005204202 85:0.0010900472 86:0.0016796719 87:0.0010130677 88:0.00086538575
89:0.0014052332 90:0.0012018452 91:0.00018189113 92:0.00057689246 93:0.0018313623
94:0.0026408355 95:0.00079052034 96:0.0019842789 97:−0.0015824389 98:−0.00092224235
99:−0.0010365265 100:−8.9265384e−005 101:−0.00011542163 102:0.0024433194 103:0.0015950786
104:−0.001393425 105:−0.00076850987 106:−0.0017206173 107:−0.0011140696 108:−0.0020789856
109:0.0013786858 110:−0.00081737712 111:−0.0025310477 112:−0.0010236512
113:−0.00049510651 114:0.0013168686 115:−0.0017368494 116:−0.00051662087 117:−0.0611937086
118:−0.0008155898 119:−0.0014308705 120:−0.00060646527 121:−0.0023188046
122:−0.00047986541 123:−0.0017967777 124:−0.0028703539 125:−0.0008995044 126:−0.0044899271
127:−0.0037051167 128:0.00010453928 129:0.0017558743 130:−0.00021409123
131:8.4772248e−005 132:−0.00059640477 133:0.00091315049 134:0.0029517044
135:0.0012407211 136:0.001771849 137:0.00061086519 138:0.0016401729 139:1.1190635e−005
140:0.00066645071 141:0.0020694127 142:−0.0019681684 143:−0.0010553099 144:0.0023889465
145:0.0018726855 146:−0.00070473028 147:−0.0012693994 148:0.0013133255 149:0.0017171054
150:−0.0023144449 151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746

APPENDIX C3-continued

SVM Model Weights
(340; Early/Late)

238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
−0.003263013586870337 1:1.7432362 2:2.2080975 3:−0.45811424 4:−0.25904602 5:3.5310566
6:−1.0701555 7:2.6190839 8:−1.5763268 9:−0.24684133 10:7.6938968 11:−1.0055476 12:0.37766281
13:0.39471114 14:0.32477632 15:0.26778743 16:0.88798404 17:−1.6143467 18:5.739316
19:−3.8111773 20:−0.13830076 21:−1.5627664 22:0.48013633 23:1.9933881 24:1.3006287
25:2.1235414 26:−0.84740353 27:1.1789974 28:1.5507125 29:−2.3316514 30:−0.99013168
31:−2.1526787 32:0.15070185 33:0.69957173 34:1.2233592 35:1.0863832 36:−0.076190881
37:1.7095969 38:−1.058123 39:−0.42751789 40:0.24727733 41:−0.34472501 42:−0.35372955
43:−0.22552487 44:−1.7159878 45:−0.55329216 46:0.2536802 47:−1.7885152 48:0.4957023
49:0.49600843 50:0.71038604 51:−0.90450937 52:−0.050310001 53:−0.56466287 54:−0.2654599
55:0.043809652 56:0.48585305 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786
104:−0.001393425 105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291

APPENDIX C3-continued

| SVM Model Weights (340; Early/Late) |
|---|
| 272:−0.0071474779 273:−0.015365882 274:−0.01525611 275:−0.0060280701 276:−0.0022994229 |
| 277:−0.044466536 278:−0.037435107 279:−0.021463662 280:−0.0029869985 281:−0.030177595 |
| 282:−0.023953391 283:−0.005625559 284:−0.035487764 285:−0.029201077 286:−0.011287678 |
| 287:−0.0095548136 288:−5.3504686e−005 289:−0.0016710128 290:0.0016311913 |
| 291:0.0015074767 292:0.0012213683 293:−0.0015347537 294:−7.1857015e−005 295:−0.0013649603 |
| 296:−0.0018400808 297:−0.0011357415 298:0.00029335488 299:−0.00027912227 |
| 300:0.003004099 301:−0.00078015722 302:−0.00046966597 303:−0.00038853599 |
| 304:0.0011859888 305:−0.0017202824 306:0.0010953069 307:0.0015855392 308:−0.0017361958 |
| 309:0.0011252258 310:0.00020620346 311:−0.0008949365 312:−0.00079829368 313:−0.00031991332 |
| 314:0.0018246222 315:0.00081679551 316:0.00071390043 317:0.00014404937 |
| 318:0.00030348785 319:0.0007406784 320:0.00051131583 321:0.0007617402 322:0.0015480069 |
| 323:0.00016401848 324:−0.0024698905 325:−0.00046456934 326:−0.0014662248 327:−0.00017874227 |
| 328:0.0024365219 329:−0.00083040918 330:0.00055475923 331:−2.3758541e−005 |
| 332:0.0013844321 333:0.00018908412 334:−4.6850397e−005 335:0.00017908432 |
| 336:0.0027642041 337:−0.00026057736 338:−0.0019368717 339:0.0012275067 340:−0.0021567047 # |
| −0.003263013586870337 1:8.6113596 2:0.035663262 3:0.78688341 4:1.3550853 5:3.178411 |
| 6:−1.0208944 7:−0.012796087 8:0.31668177 9:1.7832772 10:2.1886377 11:−2.8534501 12:1.0220896 |
| 13:0.030270895 14:−0.66597974 15:0.43166605 16:3.9161992 17:0.4159708 18:1.3348063 |
| 19:4.40974 20:1.7781575 21:−3.0399804 22:−0.25343016 23:−1.007033 24:−0.641725 25:1.4820757 |
| 26:−1.3819367 27:−0.68774104 28:−2.3879135 29:0.10838588 30:3.4089692 31:−2.6494894 |
| 32:−1.3129921 33:−0.84585792 34:0.80604839 35:−1.7579656 36:−0.32661092 37:−1.5601457 |
| 38:0.44571051 39:−0.8390938 40:0.54495227 41:−0.36589965 42:−1.3181593 43:1.8035884 |
| 44:0.50529796 45:−1.1740551 46:0.36618665 47:−0.66754192 48:0.46522495 49:−0.18312241 |
| 50:−0.61056685 51:0.83316934 52:−0.40324357 53:−0.22963038 54:1.1396058 55:0.39036396 |
| 56:0.24890029 57:0.0009495847 58:−0.00063543959 59:0.00017326932 60:0.0011059562 |
| 61:0.0022817524 62:−0.0032958018 63:0.00029474383 64:−0.0021514872 65:−0.0054451232 |
| 66:−0.0024786978 67:3.7493555e−005 68:0.00035079228 69:0.0023467517 70:0.001588242 |
| 71:0.001914337 72:0.0012793314 73:0.0016132059 74:0.00040791018 75:0.0013395234 |
| 76:0.00060126832 77:0.0017832168 78:0.0019726807 79:0.0013805456 80:−0.00077531522 |
| 81:3.2110733e−005 82:0.0011871321 83:0.00056208909 84:0.0005204202 85:0.0010900472 |
| 86:0.0016796719 87:0.0010130677 88:0.00086538575 89:0.0014052332 90:0.0012018452 |
| 91:0.00018189113 92:0.00057689246 93:0.0018313623 94:0.0026408355 95:0.00079052034 |
| 96:0.0019842789 97:−0.0015824389 98:−0.00092224235 99:−0.0010365265 100:−8.9265384e−005 |
| 101:−0.00011542163 102:0.0024433194 103:0.0015950786 104:−0.001393425 105:−0.00076850987 |
| 106:−0.0017206173 107:−0.0011140696 108:−0.0020789856 109:0.0013786858 |
| 110:−0.00081737712 111:−0.0025310477 112:−0.0010236512 113:−0.00049510651 |
| 114:0.0013168686 115:−0.0017368494 116:−0.00051662087 117:−0.0011937086 118:−0.0008155898 |
| 119:−0.0014308705 120:−0.00060646527 121:−0.0023188046 122:−0.00047986541 |
| 123:−0.0017967777 124:−0.0028703539 125:−0.0008995044 126:−0.0044899271 127:−0.0037051167 |
| 128:0.00010453928 129:0.0017558743 130:−0.00021409123 131:8.4772248e−005 |
| 132:−0.00059640477 133:0.00091315049 134:0.0029517044 135:0.0012407211 136:0.001771849 |
| 137:0.00061086519 138:0.0016401729 139:1.1190635e−005 140:0.00066645071 |
| 141:0.0020694127 142:−0.0019681684 143:−0.0010553099 144:0.0023889465 145:0.0018726855 |
| 146:−0.00070473028 147:−0.0012693994 148:0.0013133255 149:0.0017171054 150:−0.0023144449 |
| 151:0.0023775783 152:0.00045603843 153:−0.0020286744 154:−3.1378081e−006 |
| 155:−0.0017911249 156:0.00026146293 157:−0.00066072296 158:−0.0012093179 |
| 159:0.00038491705 160:0.00085559086 161:0.0025676095 162:0.0016044743 163:−0.00089113193 |
| 164:0.0024120815 165:0.0010050905 166:0.0013388922 167:−1.9663272e−005 |
| 168:−0.00063788053 169:−0.001915552 170:−0.0015327755 171:−0.00080461183 172:−0.0022213417 |
| 173:−0.0012071569 174:0.00085961225 175:1.1924029e−005 176:−0.00010044254 |
| 177:0.0011742229 178:−0.00082149269 179:−0.0016058821 180:−0.0010348763 181:−0.00091460953 |
| 182:−0.0004915254 183:−0.00073268131 184:0.00074214442 185:−0.0018549222 |
| 186:−0.00029827142 187:−0.0012626129 188:0.0011506754 189:0.0014984758 190:0.001521907 |
| 191:0.0011545231 192:−0.0017103127 193:−0.0005076346 194:−0.00046162415 195:−0.00039687741 |
| 196:0.0006169476 197:0.0019146017 198:−0.001938576 199:0.00174745 200:−0.00036255008 |
| 201:0.001886385 202:0.00071268051 203:−0.0015044769 204:−0.00094833004 |
| 205:0.0020877882 206:−0.0016524799 207:−0.002788797 208:0.001349878 209:0.001943506 |
| 210:−0.00086329813 211:0.00089030684 212:−0.0019820002 213:6.8280075e−005 |
| 214:−0.00089089427 215:−0.0011382027 216:−0.0011946515 217:−0.031154955 218:−0.018805003 |
| 219:−0.01448297 220:−0.014768096 221:−0.01189405 222:−0.0050329659 223:−0.0038689009 |
| 224:2.2608641e−005 225:−0.00011902419 226:−0.018885663 227:−0.0053921309 228:−0.0018284534 |
| 229:−0.0052720057 230:−0.009582757 231:−0.0060223294 232:−0.0011540388 |
| 233:−0.0011784985 234:−0.0036054854 235:−0.0014334067 236:−0.0057753613 237:−0.092932746 |
| 238:−0.071324907 239:−0.0057371478 240:−0.006171681 241:−0.0023048196 242:−0.0031618457 |
| 243:−0.0039265179 244:−0.036298919 245:−0.026567493 246:−0.048627507 247:−0.022513576 |
| 248:−0.0027006424 249:−0.0030078713 250:−0.0061391126 251:−0.0061381557 252:−0.0049137147 |
| 253:−0.0035512438 254:−0.012955156 255:−0.022692045 256:−0.019110594 257:−0.019834602 |
| 258:−0.0055528483 259:−0.0031212247 260:−0.0048848111 261:−0.0025836895 |
| 262:−0.0010775019 263:−0.0019687952 264:−0.0064801569 265:−0.0049881209 266:−0.0030259397 |
| 267:−0.0079323547 268:−0.043975201 269:−0.047393609 270:−0.0097410055 271:−0.0014055291 |
| 272:−0.0071474779 273:−0.015365882 274:−0.01525611 275:−0.0060280701 276:−0.0022994229 |
| 277:−0.044466536 278:−0.037435107 279:−0.021463662 280:−0.0029869985 281:−0.030177595 |
| 282:−0.023953391 283:−0.005625559 284:−0.035487764 285:−0.029201077 |
| 286:−0.011287678 287:−0.0095548136 288:−5.3504686e−005 289:−0.0016710128 290:0.0016311913 |
| 291:0.0015074767 292:0.0012213683 293:−0.0015347537 294:−7.1857015e−005 295:−0.0013649603 |
| 296:−0.0018400808 297:−0.0011357415 298:0.00029335488 299:−0.00027912227 |
| 300:0.003004099 301:−0.00078015722 302:−0.00046966597 303:−0.00038853599 |

APPENDIX C3-continued

SVM Model Weights
(340; Early/Late)

304:0.0011859888 305:−0.0017202824 306:0.0010953069 307:0.0015855392 308:−0.0017361958
309:0.0011252258 310:0.00020620346 311:−0.0008949365 312:−0.00079829368
313:−0.00031991332 314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.003263013586870337 1:17.764666 2:13.276847 3:−6.217092 4:0.85309285 5:−3.2269576
6:7.2593732 7:−5.8735247 8:3.7184291 9:0.69418424 10:−1.9208281 11:7.0488067 12:−3.0298989
13:−0.76913738 14:−3.5875182 15:−0.66790712 16:3.6537671 17:−2.8991296 18:0.19188908
19:0.011105056 20:−3.2731891 21:0.068219468 22:1.9221981 23:−1.1808108 24:0.87695962
25:0.19940683 26:−1.0992702 27:2.4589097 28:0.62231517 29:−0.79621994 30:−1.1352015
31:−1.88065 32:−0.0081547666 33:−0.70600635 34:−0.4687255 35:−0.14779152 36:−1.3467897
37:−1.0534955 38:1.2117174 39:1.5018312 40:−0.66517234 41:0.91468376 42:0.016846249
43:0.0320279 44:1.0009896 45:0.22842567 46:−0.68814802 47:−0.24605151 48:−0.37284866
49:−0.091795325 50:0.14488226 51:−0.43977004 52:0.20938379 53:−0.24951455 54:−0.092171393
55:−0.062024627 56:0.24971899 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280082e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432

APPENDIX C3-continued

SVM Model Weights
(340; Early/Late)

336:0.0027642041 337:−0.00026057736 338:−0.0019368717 339:0.0012275067 340:−0.0021567047 #
0.003263013586870337 1:2.5751998 2:10.221202 3:−0.95512414 4:9.3179073 5:−1.7831018
6:4.4525976 7:2.2225649 8:1.906949 9:2.5413458 10:−3.9868 11:−0.63038528 12:2.1551003
13:−1.2248868 14:1.4060228 15:−1.4359819 16:−1.2918285 17:1.0110083 18:−0.061929401
19:1.4711499 20:−1.4881929 21:0.80258656 22:−1.1465348 23:−1.5264565 24:0.27148193
25:1.1045482 26:2.2288132 27:0.50440538 28:0.18125741 29:0.3346369 30:−1.7561769
31:1.2301488 32:2.4653473 33:2.2793252 34:0.34436762 35:−1.717563 36:0.78135854
37:1.5482913 38:−0.3626014 39:−0.56852841 40:0.39892247 41:0.89233398 42:−1.4358878
43:0.64159596 44:−0.55421036 45:−1.5430975 46:1.3811736 47:−0.78434789 48:−0.21523786
49:−0.32041973 50:0.67920256 51:0.90812522 52:0.10603599 53:0.11899571 54:0.81252283
55:−1.1085294 56:1.4521186 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280082e−005
214:−0.00089089427 215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309
228:−0.0018284534 229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.003263013586870337 1:−5.463172 2:7.882761 3:−2.6611001 4:4.7720952 5:−2.6212659
6:−0.66245055 7:6.5618205 8:0.32615471 9:1.1786789 10:−4.1691036 11:−0.4203403 12:1.7752379
13:−0.11802472 14:−2.7309148 15:−1.7289203 16:−0.47674027 17:−0.095811032 18:0.75439733
19:0.075886451 20:0.13598223 21:−0.72880638 22:−1.1294914 23:1.3876489 24:1.3553932
25:−1.501804 26:−1.3678044 27:−3.9636581 28:−0.33515278 29:−4.5743499 30:1.060473 31:1.2314618
32:0.14404362 33:1.9053147 34:0.21452859 35:−0.28400692 36:−1.4552145 37:0.40343893

APPENDIX C3-continued

SVM Model Weights
(340; Early/Late)

38:0.31537935 39:1.3406228 40:−0.58248907 41:−1.2276702 42:−0.44912559 43:1.5652546
44:0.86094886 45:0.59833056 46:−0.37570837 47:−0.0020856087 48:0.72526038 49:−0.88049543
50:−0.21417078 51:−1.5004665 52:0.59476405 53:0.69179738 54:−0.28262526 55:0.29808122
56:−0.39380914 57:0.0009495847 58:−0.00063543959 59:0.00017326932 60:0.0011059562
61:0.0022817524 62:−0.0032958018 63:0.00029474383 64:−0.0021514872 65:−0.0054451232
66:−0.0024786978 67:3.7493555e−005 68:0.00035079228 69:0.0023467517 70:0.001588242
71:0.001914337 72:0.0012793314 73:0.0016132059 74:0.00040791018 75:0.0013395234
76:0.00060126832 77:0.0017832168 78:0.0019726807 79:0.0013805456 80:−0.00077531522
81:3.2110733e−005 82:0.0011871321 83:0.00056208909 84:0.0005204202 85:0.0010900472
86:0.0016796719 87:0.0010130677 88:0.00086538575 89:0.0014052332 90:0.0012018452
91:0.00018189113 92:0.00057689246 93:0.0018313623 94:0.0026408355 95:0.00079052034
96:0.0019842789 97:−0.0015824389 98:−0.00092224235 99:−0.0010365265 100:−8.9265384e−005
101:−0.00011542163 102:0.0024433194 103:0.0015950786 104:−0.001393425 105:−0.00076850987
106:−0.0017206173 107:−0.0011140696 108:−0.0020789856 109:0.0013786858
110:−0.00081737712 111:−0.0025310477 112:−0.0010236512 113:−0.00049510651
114:0.0013168686 115:−0.0017368494 116:−0.00051662087 117:−0.0011937086 118:−0.0008155898
119:−0.0014308705 120:−0.00060646527 121:−0.0023188046 122:−0.00047986541
123:−0.0017967777 124:−0.0028703539 125:−0.0008995044 126:−0.0044899271 127:−0.0037051167
128:0.00010453928 129:0.0017558743 130:−0.00021409123 131:8.4772248e−005
132:−0.00059640477 133:0.00091315049 134:0.0029517044 135:0.0012407211 136:0.001771849
137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.09232746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.0023963480454683721 1:5.4242792 2:8.5105228 3:−3.6257584 4:−4.6308413 5:−0.75645578
6:−0.45588413 7:−0.88993597 8:−5.7085314 9:−1.9537624 10:−0.09565293 11:0.38187858
12:−1.137969 13:−0.76989567 14:0.38682535 15:−1.6267631 16:−0.19945671 17:1.2119049
18:0.22235118 19:−0.8249591 20:−2.607296 21:−0.31416124 22:2.4226515 23:−0.036228649
24:0.044377733 25:−0.85722339 26:1.6688207 27:−3.1746669 28:−0.53754961 29:−1.5170302
30:1.2003756 31:−1.0720835 32:0.67520529 33:−0.65237749 34:0.67227352 35:2.4610274
36:0.93812031 37:1.1232651 38:−0.14917752 39:−1.1775687 40:0.92472392 41:−0.046555012
42:1.5438993 43:0.75920689 44:−0.40638646 45:0.84706259 46:−1.2272241 47:1.2393662
48:−1.6440406 49:0.48244566 50:0.60142046 51:1.1816202 52:−0.1325352 53:0.40169922
54:2.0415785 55:0.1321009 56:0.54975611 57:0.0009495847 58:−0.00063543959
59:0.00017326932 60:0.0011059562 61:0.0022817524 62:−0.0032958018 63:0.00029474383
64:−0.0021514872 65:−0.0054451232 66:−0.0024786978 67:3.7493555e−005 68:0.00035079228
69:0.0023467517 70:0.001588242 71:0.001914337 72:0.0012793314 73:0.0016132059

APPENDIX C3-continued

| SVM Model Weights (340; Early/Late) |
|---|
| 74:0.00040791018 75:0.0013395234 76:0.00060126832 77:0.0017832168 78:0.0019726807 |
| 79:0.0013805456 80:−0.00077531522 81:3.2110733e−005 82:0.0011871321 83:0.00056208909 |
| 84:0.0005204202 85:0.0010900472 86:0.0016796719 87:0.0010130677 88:0.00086538575 |
| 89:0.0014052332 90:0.0012018452 91:0.00018189113 92:0.00057689246 93:0.0018313623 |
| 94:0.0026408355 95:0.00079052034 96:0.0019842789 97:−0.0015824389 98:−0.00092224235 |
| 99:−0.0010365265 100:−8.9265384e−005 101:−0.00011542163 102:0.0024433194 103:0.0015950786 |
| 104:−0.001393425 105:−0.00076850987 106:−0.0017206173 107:−0.0011140696 108:−0.0020789856 |
| 109:0.0013786858 110:−0.00081737712 111:−0.0025310477 112:−0.0010236512 |
| 113:−0.00049510651 114:0.0013168686 115:−0.0017368494 116:−0.00051662087 117:−0.0011937086 |
| 118:−0.0008155898 119:−0.0014308705 120:−0.00060646527 121:−0.0023188046 |
| 122:−0.00047986541 123:−0.0017967777 124:−0.0028703539 125:−0.0008995044 126:−0.0044899271 |
| 127:−0.0037051167 128:0.00010453928 129:0.0017558743 130:−0.00021409123 |
| 131:8.4772248e−005 132:−0.00059640477 133:0.00091315049 134:0.0029517044 |
| 135:0.0012407211 136:0.001771849 137:0.00061086519 138:0.0016401729 139:1.1190635e−005 |
| 140:0.00066645071 141:0.0020694127 142:−0.0019681684 143:−0.0010553099 144:0.0023889465 |
| 145:0.0018726855 146:−0.00070473028 147:−0.0012693994 148:0.0013133255 149:0.0017171054 |
| 150:−0.0023144449 151:0.0023775783 152:−0.00045603843 153:−0.0020286744 154:−3.1378081e−006 |
| 155:−0.0017911249 156:0.00026146293 157:−0.00066072296 158:−0.0012093179 |
| 159:0.00038491705 160:0.00085559086 161:0.0025676095 162:0.0016044743 163:−0.00089113193 |
| 164:0.0024120815 165:0.0010050905 166:0.0013388922 167:−1.9663272e−005 |
| 168:−0.00063788053 169:−0.001915552 170:−0.0015327755 171:−0.00080461183 172:−0.0022213417 |
| 173:−0.0012071569 174:0.00085961225 175:1.1924029e−005 176:−0.00010044254 |
| 177:0.0011742229 178:−0.00082149269 179:−0.0016058821 180:−0.0010348763 181:−0.00091460953 |
| 182:−0.0004915254 183:−0.00073268131 184:0.00074214442 185:−0.0018549222 |
| 186:−0.00029827142 187:−0.0012626129 188:0.0011506754 189:0.0014984758 190:0.001521907 |
| 191:0.0011545231 192:−0.0017103127 193:−0.0005076346 194:−0.00046162415 195:−0.00039687741 |
| 196:0.0006169476 197:0.0019146017 198:−0.001938576 199:0.00174745 200:−0.00036255008 |
| 201:0.001886385 202:0.00071268051 203:−0.0015044769 204:−0.00094833004 |
| 205:0.0020877882 206:−0.0016524799 207:−0.002788797 208:0.001349878 209:0.001943506 |
| 210:−0.00086329813 211:0.00089030684 212:−0.0019820002 213:6.8280075e−005 214:−0.00089089427 |
| 215:−0.0011382027 216:−0.0011946515 217:−0.031154955 218:−0.018805003 |
| 219:−0.01448297 220:−0.014768096 221:−0.01189405 222:−0.0050329659 223:−0.0038689009 |
| 224:2.2608641e−005 225:−0.00011902419 226:−0.018885663 227:−0.0053921309 228:−0.0018284534 |
| 229:−0.0052720057 230:−0.009582757 231:−0.0060223294 232:−0.0011540388 |
| 233:−0.0011784985 234:−0.0036054854 235:−0.0014334067 236:−0.0057753613 237:−0.092932746 |
| 238:−0.071324907 239:−0.0057371478 240:−0.006171681 241:−0.0023048196 242:−0.0031618457 |
| 243:−0.0039265179 244:−0.036298919 245:−0.026567493 246:−0.048627507 247:−0.022513576 |
| 248:−0.0027006424 249:−0.0030078713 250:−0.0061391126 251:−0.0061381557 252:−0.0049137147 |
| 253:−0.0035512438 254:−0.012955156 255:−0.022692045 256:−0.019110594 257:−0.019834602 |
| 258:−0.0055528483 259:−0.0031212247 260:−0.0048848111 261:−0.0025836895 |
| 262:−0.0010775019 263:−0.0019687952 264:−0.0064801569 265:−0.0049881209 266:−0.0030259397 |
| 267:−0.0079323547 268:−0.043975201 269:−0.047393609 270:−0.0097410055 271:−0.0014055291 |
| 272:−0.0071474779 273:−0.015365882 274:−0.01525611 275:−0.0060280701 276:−0.0022994229 |
| 277:−0.044466536 278:−0.037435107 279:−0.021463662 280:−0.0029869985 281:−0.030177595 |
| 282:−0.023953391 283:−0.005625559 284:−0.035487764 285:−0.029201077 286:−0.011287678 |
| 287:−0.0095548136 288:−5.3504686e−005 289:−0.0016710128 290:0.0016311913 |
| 291:0.0015074767 292:0.0012213683 293:−0.0015347537 294:−7.1857015e−005 295:−0.0013649603 |
| 296:−0.0018400808 297:−0.0011357415 298:0.00029335488 299:−0.00027912227 |
| 300:0.003004099 301:−0.00078015722 302:−0.00046966597 303:−0.00038853599 |
| 304:0.0011859888 305:−0.0017202824 306:0.0010953069 307:0.0015855392 308:−0.0017361958 |
| 309:0.0011252258 310:0.00020620346 311:−0.0008949365 312:−0.00079829368 313:−0.00031991332 |
| 314:0.0018246222 315:0.00081679551 316:0.00071390043 317:0.00014404937 |
| 318:0.00030348785 319:0.0007406784 320:0.00051131583 321:0.0007617402 322:0.0015480069 |
| 323:0.00016401848 324:−0.0024698905 325:−0.00046456934 326:−0.0014662248 327:−0.00017874227 |
| 328:0.0024365219 329:0.00083040918 330:−0.00055475923 331:−2.3758541e−005 |
| 332:0.0013844321 333:0.00018908412 334:−4.6850397e−005 335:0.00017908432 |
| 336:0.0027642041 337:−0.00026057736 338:−0.0019368717 339:0.0012275067 340:−0.0021567047 # |
| 0.0026927785065002439 1:−5.8183594 2:11.128675 3:0.79399675 4:5.2573433 5:4.4285293 |
| 6:0.95433325 7:−0.69111842 8:−4.1106591 9:2.5315742 10:2.0295665 11:−2.6745369 |
| 12:0.84233916 13:−1.7253991 14:2.8288822 15:−2.9223824 16:−2.9646323 17:3.0143211 |
| 18:2.6608479 19:3.9952185 20:1.4995718 21:2.1989398 22:−0.47424674 23:1.3009776 |
| 24:−0.16630308 25:1.0945835 26:0.041169818 27:2.9997933 28:−0.13137996 29:−0.63695759 |
| 30:1.4042147 31:−0.41155079 32:−1.1410439 33:−0.95365351 34:−1.3116107 35:1.0361317 |
| 36:0.094957031 37:1.8969471 38:0.70636696 39:0.98500276 40:−0.70368975 41:1.107469 |
| 42:0.28593799 43:−1.0727774 44:2.3539567 45:−0.2301666 46:−1.369817 47:0.032493874 |
| 48:−0.78619826 49:0.50169325 50:−0.67888361 51:−0.14426404 52:0.59420002 53:0.2140806 |
| 54:−0.46581495 55:−0.23613326 56:−0.14059499 57:0.0009495847 58:−0.00063543959 |
| 59:0.00017326932 60:0.0011059562 61:0.0022817524 62:−0.0032958018 63:0.00029474383 |
| 64:−0.0021514872 65:−0.0054451232 66:−0.0024786978 67:3.7493555e−005 68:0.00035079228 |
| 69:0.0023467517 70:0.001588242 71:0.001914337 72:0.0012793314 73:0.0016132059 |
| 74:0.00040791018 75:0.0013395234 76:0.00060126832 77:0.0017832168 78:0.0019726807 |
| 79:0.0013805456 80:−0.00077531522 81:3.2110733e−005 82:0.0011871321 83:0.00056208909 |
| 84:0.0005204202 85:0.0010900472 86:0.0016796719 87:0.0010130677 88:0.00086538575 |
| 89:0.0014052332 90:0.0012018452 91:0.00018189113 92:0.00057689246 93:0.0018313623 |
| 94:0.0026408355 95:0.00079052034 96:0.0019842789 97:−0.0015824389 98:−0.00092224235 |
| 99:−0.0010365265 100:−8.9265384e−005 101:−0.00011542163 102:0.0024433194 103:0.0015950786 |
| 104:−0.001393425 105:−0.00076850987 106:−0.0017206173 107:−0.0011140696 108:−0.0020789856 |

APPENDIX C3-continued

| SVM Model Weights (340; Early/Late) |
|---|
| 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # −0.003263013586870337 1:4.3136711 2:11.85136 3:−2.4349139 4:4.3976011 5:−0.064428166 6:3.3004136 7:0.26722765 8:0.083926447 9:2.1508505 10:−1.2738918 11:−1.768934 12:0.17292808 13:0.44556588 14:−0.59223634 15:−0.96534908 16:−1.6171639 17:1.2820607 18:−0.84876287 19:1.4367297 20:−0.6155647 21:−2.36043 22:−0.019897325 23:−1.2100018 24:−0.45661017 25:0.22039026 26:−0.91286564 27:0.937419 28:−0.13718922 29:0.74340838 30:0.70248711 31:0.43081525 32:−1.2747772 33:0.4775075 34:−2.2567503 35:−0.24196947 36:−0.66949981 37:1.1833178 38:1.0137376 39:−0.2061992 40:0.95708007 41:−2.7814839 42:0.68686748 43:−1.0831043 44:−2.3519526 45:1.717508 46:0.6327315 47:1.1638249 48:1.0267545 49:0.69539011 50:0.68839854 51:0.70271391 52:−0.74343067 53:−1.4116489 54:−1.0324525 55:1.1390431 56:0.35386369 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 |

APPENDIX C3-continued

| SVM Model Weights (340; Early/Late) |
|---|

141:0.0020694127 142:-0.0019681684 143:-0.0010553099 144:0.0023889465 145:0.0018726855
146:-0.00070473028 147:-0.0012693994 148:0.0013133255 149:0.0017171054 150:-0.0023144449
151:0.0023775783 152:-0.00045603843 153:-0.0020286744 154:-3.1378081e-006
155:-0.0017911249 156:0.00026146293 157:-0.00066072296 158:-0.0012093179
159:0.00038491705 160:0.00085559086 161:0.0025676095 162:0.0016044743 163:-0.00089113193
164:0.0024120815 165:0.0010050905 166:0.0013388922 167:-1.9663272e-005
168:-0.00063788053 169:-0.001915552 170:-0.0015327755 171:-0.00080461183 172:-0.0022213417
173:-0.0012071569 174:0.00085961225 175:1.1924029e-005 176:-0.00010044254
177:0.0011742229 178:-0.00082149269 179:-0.0016058821 180:-0.0010348763 181:-0.00091460953
182:-0.0004915254 183:-0.00073268131 184:0.00074214442 185:-0.0018549222
186:-0.00029827142 187:-0.0012626129 188:0.0011506754 189:0.0014984758 190:0.001521907
191:0.0011545231 192:-0.0017103127 193:-0.0005076346 194:-0.00046162415 195:-0.00039687741
196:0.0006169476 197:0.0019146017 198:-0.001938576 199:0.00174745 200:-0.00036255008
201:0.001886385 202:0.00071268051 203:-0.0015044769 204:-0.00094833004
205:0.0020877882 206:-0.0016524799 207:-0.002788797 208:0.001349878 209:0.001943506
210:-0.00086329813 211:0.00089030684 212:-0.0019820002 213:6.8280075e-005
214:-0.00089089427 215:-0.0011382027 216:-0.0011946515 217:-0.031154955 218:-0.018805003
219:-0.01448297 220:-0.014768096 221:-0.01189405 222:-0.0050329659 223:-0.0038689009
224:2.2608641e-005 225:-0.00011902419 226:-0.018885663 227:-0.0053921309 228:-0.0018284534
229:-0.0052720057 230:-0.009582757 231:-0.0060223294 232:-0.0011540388
233:-0.0011784985 234:-0.0036054854 235:-0.0014334067 236:-0.0057753613 237:-0.092932746
238:-0.071324907 239:-0.0057371478 240:-0.006171681 241:-0.0023048196 242:-0.0031618457
243:-0.0039265179 244:-0.036298919 245:-0.026567493 246:-0.048627507 247:-0.022513576
248:-0.0027006424 249:-0.0030078713 250:-0.0061391126 251:-0.0061381557 252:-0.0049137147
253:-0.0035512438 254:-0.012955156 255:-0.022692045 256:-0.019110594 257:-0.019834602
258:-0.0055528483 259:-0.0031212247 260:-0.0048848111 261:-0.0025836895
262:-0.0010775019 263:-0.0019687952 264:-0.0064801569 265:-0.0049881209 266:-0.0030259397
267:-0.0079323547 268:-0.043975201 269:-0.047393609 270:-0.0097410055 271:-0.0014055291
272:-0.0071474779 273:-0.015365882 274:-0.01525611 275:-0.0060280701 276:-0.0022994229
277:-0.044466536 278:-0.037435107 279:-0.021463662 280:-0.0029869985 281:-0.030177595
282:-0.023953391 283:-0.005625559 284:-0.035487764 285:-0.029201077 286:-0.011287678
287:-0.0095548136 288:-5.3504686e-005 289:-0.0016710128 290:0.0016311913
291:0.0015074767 292:0.0012213683 293:-0.0015347537 294:-7.1857015e-005 295:-0.0013649603
296:-0.0018400808 297:-0.0011357415 298:0.00029335488 299:-0.00027912227
300:0.003004099 301:-0.00078015722 302:-0.00046966597 303:-0.00038853599
304:0.0011859888 305:-0.0017202824 306:0.0010953069 307:0.0015855392 308:-0.0017361958
309:0.0011252258 310:0.00020620346 311:-0.0008949365 312:-0.00079829368 313:-0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:-0.0024698905 325:-0.00046456934 326:-0.0014662248 327:-0.00017874227
328:0.0024365219 329:-0.00083040918 330:0.00055475923 331:-2.3758541e-005
332:0.0013844321 333:0.00018908412 334:-4.6850397e-005 335:0.00017908432
336:0.0027642041 337:-0.00026057736 338:-0.0019368717 339:0.0012275067 340:-0.0021567047 #
-0.003263013586870337 1:7.9950004 2:7.8763146 3:-2.6768916 4:4.3499146 5:-0.26874429
6:-1.2617569 7:7.5231724 8:-1.001968 9:-3.2742054 10:-4.0525489 11:-3.2061014 12:1.1717849
13:-0.077940315 14:-0.21310687 15:5.9929557 16:-3.0397136 17:-2.1435318 18:-1.0098519
19:-2.4063938 20:-0.1814501 21:1.1750045 22:0.60953563 23:0.6414243 24:4.1224709 25:3.3680656
26:0.56308722 27:0.8397575 28:-1.1192403 29:1.2833984 30:-0.095799439 31:0.44614187
32:-1.7961432 33:-0.16294682 34:1.2279147 35:0.12392759 36:1.0085716 37:-1.2530149
38:1.3775395 39:-1.2154675 40:1.3844229 41:0.84347206 42:1.3588188 43:0.49808076
44:0.89308292 45:0.24031922 46:-0.34828675 47:-0.21975373 48:0.27022728 49:0.023851894
50:-0.59532106 51:-0.16824791 52:0.54748046 53:-0.34892443 54:-0.19209315 55:0.43247184
56:-0.036076903 57:0.0009495847 58:-0.00063543959 59:0.00017326932 60:0.0011059562
61:0.0022817524 62:-0.0032958018 63:0.00029474383 64:-0.0021514872 65:-0.0054451232
66:-0.0024786978 67:3.7493555e-005 68:0.00035079228 69:0.0023467517 70:0.001588242
71:0.001914337 72:0.0012793314 73:0.0016132059 74:0.00040791018 75:0.0013395234
76:0.00060126832 77:0.0017832168 78:0.0019726807 79:0.0013805456 80:-0.00077531522
81:3.2110733e-005 82:0.0011871321 83:0.00056208909 84:0.0005204202 85:0.0010900472
86:0.0016796719 87:0.0010130677 88:0.00086538575 89:0.0014052332 90:0.0012018452
91:0.00018189113 92:0.00057689246 93:0.0018313623 94:0.0026408355 95:0.00079052034
96:0.0019842789 97:-0.0015824389 98:-0.00092224235 99:-0.0010365265 100:-8.9265384e-005
101:-0.00011542163 102:0.0024433194 103:0.0015950786 104:-0.001393425 105:-0.00076850987
106:-0.0017206173 107:-0.0011140696 108:-0.0020789856 109:0.0013786858
110:-0.00081737712 111:-0.0025310477 112:-0.0010236512 113:-0.00049510651
114:0.0013168686 115:-0.0017368494 116:-0.00051662087 117:-0.0011937086 118:-0.0008155898
119:-0.0014308705 120:-0.00060646527 121:-0.0023188046 122:-0.00047986541
123:-0.0017967777 124:-0.0028703539 125:-0.0008995044 126:-0.0044899271 127:-0.0037051167
128:0.00010453928 129:0.0017558743 130:-0.00021409123 131:8.4772248e-005
132:-0.00059640477 133:0.00091315049 134:0.0029517044 135:0.0012407211 136:0.001771849
137:0.00061086519 138:0.0016401729 139:1.1190635e-005 140:0.00066645071
141:0.0020694127 142:-0.0019681684 143:-0.0010553099 144:0.0023889465 145:0.0018726855
146:-0.00070473028 147:-0.0012693994 148:0.0013133255 149:0.0017171054 150:-0.0023144449
151:0.0023775783 152:-0.00045603843 153:-0.0020286744 154:-3.1378081e-006
155:-0.0017911249 156:0.00026146293 157:-0.00066072296 158:-0.0012093179
159:0.00038491705 160:0.00085559086 161:0.0025676095 162:0.0016044743 163:-0.00089113193
164:0.0024120815 165:0.0010050905 166:0.0013388922 167:-1.9663272e-005
168:-0.00063788053 169:-0.001915552 170:-0.0015327755 171:-0.00080461183 172:-0.0022213417

APPENDIX C3-continued

SVM Model Weights
(340; Early/Late)

173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280082e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
−0.003263013586870337 1:11.704061 2:6.5949616 3:0.45483977 4:4.3702846 5:0.58678722
6:4.2801876 7:−6.5564938 8:−2.7858698 9:−10.711282 10:5.1795998 11:0.23074189 12:2.5389693
13:−7.9909263 14:−0.42881522 15:3.1987579 16:−0.885517 17:0.47581372 18:0.5075509
19:0.6129297 20:0.87700886 21:2.9646459 22:−2.4006853 23:1.8537773 24:−0.3296504
25:−0.99861437 26:−2.0937648 27:−1.8252416 28:0.2058742 29:0.44918847 30:−0.57538432
31:0.84618878 32:0.69699323 33:−0.34345084 34:−1.1655228 35:−0.53105354 36:−0.52976108
37:−0.90983158 38:−0.22549088 39:0.11226936 40:−0.062483769 41:−0.61575305 42:−0.41575837
43:−0.12159781 44:−0.66372013 45:−0.29864317 46:0.53406799 47:0.37851506 48:−0.065740414
49:−0.52697623 50:0.19244891 51:0.10414321 52:−0.32026809 53:0.1686599 54:0.19469196
55:−0.24605314 56:−0.45055935 57:0.0009495847 58:−0.00063543959 59:0.00017326932
60:0.0011059562 61:0.0022817524 62:−0.0032958018 63:0.00029474383 64:−0.0021514872
65:−0.0054451232 66:0.0024786978 67:3.7493555e−005 68:−0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758.190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004

APPENDIX C3-continued

| SVM Model Weights (340; Early/Late) |
|---|
| 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110591 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # −0.003263013586870337 1:2.1832664 2:5.4387846 3:1.7195971 4:2.0288308 5:0.93580216 6:1.0958407 7:−1.1356411 8:−1.3170016 9:0.4036161 10:0.66208827 11:−1.1981317 12:−3.9873779 13:1.083784 14:−1.2963853 15:−2.180872 16:−1.6959615 17:−0.21459815 18:−2.1435783 19:−0.18801655 20:−2.7198138 21:−0.46923888 22:−1.1304476 23:0.37281671 24:−0.29892316 25:−1.6967143 26:−1.0425665 27:0.52042228 28:0.18850514 29:−0.075532474 30:1.3673506 31:−0.20927349 32:1.8332825 33:−0.18675824 34:−0.77807641 35:−0.29415804 36:2.7382598 37:−1.1937499 38:−0.80527872 39:−0.51797247 40:−0.67693812 41:0.0044574765 42:1.3281074 43:−0.66870785 44:−0.55758661 45:−0.25713173 46:1.3463974 47:−1.2159724 48:1.9850761 49:1.9673864 50:−1.6905873 51:−0.81580597 52:1.1663288 53:0.48344821 54:1.0232606 55:−0.16654444 56:−0.84504533 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 |

APPENDIX C3-continued

SVM Model Weights
(340; Early/Late)

238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
−0.003263013586870337 1:12.366791 2:6.0081248 3:1.7113053 4:2.7979217 5:6.9255257
6:−8.9968224 7:−2.4731126 8:−1.0733718 9:1.2842386 10:−2.012439 11:−0.15039405 12:−2.9278686
13:−0.12789282 14:0.48431939 15:1.1856391 16:1.6238549 17:−0.51580727 18:−2.8973534
19:−1.2217386 20:2.441119 21:−0.56590825 22:−0.95627594 23:2.3723722 24:−2.3519976
25:−1.8573409 26:2.5932043 27:0.28923574 28:0.91411924 29:0.16916099 30:0.7578814
31:0.86746114 32:0.06571959 33:1.2952554 34:1.8225979 35:−1.0471101 36:−2.594789
37:0.91302282 38:1.0032086 39:0.58218884 40:0.82992595 41:0.2371375 42:1.4115078
43:−1.3569217 44:0.005501179 45:−1.3219823 46:0.22467521 47:−0.31165296 48:−0.91066778
49:0.5282858 50:−0.29014909 51:−1.201354 52:−1.1576918 53:−0.61281228 54:0.62632042
55:0.06742622 56:−0.1271946 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291

APPENDIX C3-continued

SVM Model Weights
(340; Early/Late)

272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.0032183444859477115 1:5.0472207 2:−15.336944 3:10.763581 4:0.12245622 5:−1.045119
6:5.0700855 7:0.022931358 8:1.0390165 9:−1.5287296 10:−1.8780161 11:−5.8217788 12:−3.495168
13:−2.9807045 14:−0.93120396 15:−0.96876276 16:1.1067419 17:2.2245276 18:−0.5159561
19:−0.56864065 20:−1.6035483 21:−0.071308769 22:0.71298867 23:−2.427552 24:6.1049132
25:−2.299476426:0.17956683 27:2.0975831 28:0.88850158 29:−1.187152 30:1.2519076
31:0.40507555 32:−0.65364575 33:−0.062440809 34:0.60360342 35:0.65818083 36:−1.6613714
37:0.84727097 38:−0.78944671 39:−0.60838294 40:−0.033466902 41:−0.67201972 42:−0.76183414
43:−0.99352539 44:−0.0064195753 45:−0.52377898 46:0.28889599 47:0.2890828 48:−0.56622463
49:−0.41732529 50:−0.63713801 51:0.12666783 52:−0.54518992 53:−0.025319166 54:0.21451463
55:−0.32560554 56:−0.35243595 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491708 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599

APPENDIX C3-continued

| SVM Model Weights (340; Early/Late) |
| --- |
| 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # 0.003263013586870337 1:12.019065 2:−4.8004398 3:4.4707756 4:4.196064 5:4.823154 6:−7.7504168 7:3.056613 8:−2.0674977 9:5.8091102 10:1.8406044 11:−2.3205659 12:1.760255 13:0.70300639 14:−4.6173835 15:1.6834904 16:2.0209546 17:−5.0978332 18:3.7654126 19:1.4629006 20:−0.6220144 21:3.7241907 22:−0.58752209 23:−3.6073112 24:−0.23158151 25:−1.1288562 26:1.0939022 27:−1.4788034 28:0.19784832 29:0.93105268 30:−1.0950043 31:0.56641442 32:−0.034652114 33:−0.94231671 34:−0.8641625 35:−1.1210113 36:0.079980716 37:0.87809104 38:−0.33434898 39:−0.33466536 40:−1.4810408 41:−0.49689689 42:0.90456569 43:−0.28511754 44:−0.53556454 45:1.160269 46:−0.3488988 47:0.64909834 48:−0.40839958 49:0.15539719 50:−0.44201076 51:0.21913791 52:0.60194045 53:0.22291826 54:−0.071047604 55:−0.63064337 56:−0.066468649 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 |

APPENDIX C3-continued

| SVM Model Weights (340; Early/Late) |
|---|
| 336:0.0027642041 337:−0.00026057736 338:−0.0019368717 339:0.0012275067 340:−0.0021567047 # 0.003263013586870337 1:−3.3880587 2:−2.6414342 3:2.8064957 4:−1.3999835 5:−2.6332676 6:6.3005533 7:1.1491936 8:2.35604 9:0.27799395 10:1.1523478 11:−3.8036392 12:−3.2891657 13:−0.86931056 14:0.55123371 15:−0.44594151 16:−0.88298255 17:0.41254392 18:0.54672933 19:−2.0287313 20:0.3622455 21:2.7641249 22:1.2421728 23:−2.0061574 24:−3.2011676 25:−0.53145313 26:−0.64420927 27:−0.75167179 28:1.4715383 29:−0.25729042 30:−0.43156871 31:0.4395895 32:0.71389002 33:−1.5089703 34:1.3503698 35:−0.56789869 36:2.040731 37:1.0265932 38:2.6680079 39:0.87354589 40:0.1352763 41:0.076715931 42:−0.56060839 43:2.752434 44:−0.307383 45:−0.30603793 46:0.37662676 47:−0.044100873 48:−1.2202348 49:0.38019869 50:−1.2669642 51:−0.7716381 52:−0.98420757 53:−0.99687314 54:−0.68999916 55:0.97318304 56:−0.070498936 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:−0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # −0.003263013586870337 1:9.7260504 2:−7.8163357 3:6.8109908 4:4.9323745 5:−1.6638223 6:3.745981 7:−0.47318304 8:2.3136632 9:0.40887526 10:0.53233683 11:0.34330738 12:0.35754034 13:1.4566673 14:−0.30523223 15:−1.4400436 16:3.4091852 17:0.3001543 18:−1.9154788 19:1.5003307 20:1.25828 21:0.19474351 22:1.4655597 23:4.9832253 24:1.5780417 25:1.8085375 26:3.7642848 27:−1.0302637 28:−0.35661903 29:0.23552622 30:−0.92275572 31:−0.18625316 32:−0.60383582 33:0.16416991 34:−2.4490721 35:0.100034 36:2.124181 |

APPENDIX C3-continued

| SVM Model Weights (340; Early/Late) |
|---|
| 37:0.56455523 38:−2.1926215 39:1.3556439 40:−0.77462763 41:−0.13219014 42:0.85297424 43:1.3223977 44:0.24121812 45:0.21751313 46:0.46913549 47:0.1792874 48:−0.3500976 49:−0.47990501 50:0.17952639 51:−0.27410603 52:−0.095224842 53:−1.4586954 54:0.095760696 55:0.51284748 56:−0.62424648 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # −0.003263013586870337 1:−7.6496434 2:2.703886 3:0.28662038 4:1.7879531 5:−3.0434427 6:−1.193588 7:6.320919 8:0.0046777669 9:−1.8738962 10:−0.86983484 11:−0.90390557 12:−0.33946124 13:−2.0940609 14:0.3616263 15:−0.41190428 16:−1.1988773 17:−0.26797518 18:−1.5384048 19:1.2224176 20:1.0135792 21:−0.91025347 22:0.67726129 23:−0.097032793 24:−1.0411915 25:0.20235281 26:0.80218315 27:−1.1149094 28:−0.075297311 29:−1.420293 30:0.039273173 31:−1.0670592 32:0.24752171 33:−0.81297511 34:0.55062044 35:−0.051494792 36:−1.2710344 37:−2.9904377 38:−2.3883932 39:1.0788088 40:−0.61928475 41:1.4220651 42:−0.63513494 43:−1.2401781 44:−1.5525755 45:1.7100438 46:0.21073915 47:−0.97540486 48:−2.0641823 49:0.83937091 50:−1.4945658 51:0.61103535 52:0.08287628 53:−0.89165288 54:−0.99374753 55:−0.38182953 56:0.98232764 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 |

APPENDIX C3-continued

SVM Model Weights
(340; Early/Late)

74:0.00040791018 75:0.0013395234 76:0.00060126832 77:0.0017832168 78:0.0019726807
79:0.0013805456 80:−0.00077531522 81:3.2110733e−005 82:0.0011871321 83:0.00056208909
84:110005204202 85:0.0010900472 86:0.0016796719 87:0.0010130677 88:0.00086538575
89:0.0014052332 90:0.0012018452 91:0.00018189113 92:0.00057689246 93:0.0018313623
94:0.0026408355 95:0.00079052034 96:0.0019842789 97:−0.0015824389 98:−0.00092224235
99:−0.0010365265 100:−8.9265384e−005 101:−0.00011542163 102:0.0024433194 103:0.0015950786
104:−0.001393425 105:−0.00076850987 106:−0.0017206173 107:−0.0011140696 108:−0.0020789856
109:0.0013786858 110:−0.00081737712 111:−0.0025310477 112:−0.0010236512
113:−0.00049510651 114:0.0013168686 115:−0.0017368494 116:−0.00051662087 117:−0.0011937086
118:−0.0008155898 119:−0.0014308705 120:−0.00060646527 121:−0.0023188046
122:−0.00047986541 123:−0.0017967777 124:−0.0028703539 125:−0.0008995044 126:−0.0044899271
127:−0.0037051167 128:0.00010453928 129:0.0017558743 130:−0.00021409123
131:8.4772248e−005 132:−0.00059640477 133:0.00091315049 134:0.0029517044
135:0.0012407211 136:0.001771849 137:0.00061086519 138:0.0016401729 139:1.1190635e−005
140:0.00066645071 141:0.0020694127 142:−0.0019681684 143:−0.0010553099 144:0.0023889465
145:0.0018726855 146:−0.00070473028 147:−0.0012693994 148:0.0013133255 149:0.0017171054
150:−0.0023144449 151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005
214:−0.00089089427 215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309
228:−0.0018284534 229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
−0.003263013586870337 1:3.8433597 2:2.4452479 3:−2.7605469 4:−2.1829417 5:−0.22223227
6:0.20662466 7:8.3353586 8:1.2071977 9:0.19084433 10:0.58242756 11:0.57760549
12:−0.43349019 13:−0.25145283 14:−1.5430319 15:0.15049267 16:0.13998732 17:0.16344859
18:−0.80469674 19:0.63106662 20:2.2429247 21:−0.69218796 22:0.5077576 23:−1.6572852
24:−1.3704666 25:0.15443374 26:−1.487389 27:1.7199481 28:−1.1768694 29:−0.65691537
30:−0.91387093 31:1.9700028 32:−0.17521015 33:−2.4380445 34:1.2323334 35:0.6152029
36:2.0528264 37:0.37548435 38:−0.73991114 39:2.3915479 40:0.54931939 41:−0.84648585
42:0.14254348 43:−2.3261664 44:−0.0031731338 45:0.20233566 46:0.8536253 47:−1.0667627
48:−0.49675515 49:−2.1055298 50:1.0263213 51:0.065273702 52:−0.17051326 53:0.70307672
54:1.4163642 55:0.7076391 56:−0.55523521 57:0.0009495847 58:−0.00063543959
59:0.00017326932 60:0.0011059562 61:0.0022817524 62:−0.0032958018 63:0.00029474383
64:−0.0021514872 65:−0.0054451232 66:−0.0024786978 67:3.7493555e−005 68:0.00035079228
69:0.0023467517 70:0.001588242 71:0.001914337 72:0.0012793314 73:0.0016132059
74:0.00040791018 75:0.0013395234 76:0.00060126832 77:0.0017832168 78:0.0019726807
79:0.0013805456 80:−0.00077531522 81:3.2110733e−005 82:0.0011871321 83:0.00056208909
84:0.0005204202 85:0.0010900472 86:0.0016796719 87:0.0010130677 88:0.00086538575
89:0.0014052332 90:0.0012018452 91:0.00018189113 92:0.00057689246 93:0.0018313623
94:0.0026408355 95:0.00079052034 96:0.0019842789 97:−0.0015824389 98:−0.00092224235
99:−0.0010365265 100:−8.9265384e−005 101:−0.00011542163 102:0.0024433194 103:0.0015950786
104:−0.001393425 105:−0.00076850987 106:−0.0017206173 107:−0.0011140696 108:−0.0020789856

APPENDIX C3-continued

| SVM Model Weights (340; Early/Late) |
|---|
| 109:0.0013786858 110:−0.00081737712 111:−0.0025310477 112:−0.0010236512 |
| 113:−0.00049510651 114:0.0013168686 115:−0.0017368494 116:−0.00051662087 117:−0.0011937086 |
| 118:−0.0008155898 119:−0.0014308705 120:−0.00060646527 121:−0.0023188046 |
| 122:−0.00047986541 123:−0.0017967777 124:−0.0028703539 125:−0.0008995044 126:−0.0044899271 |
| 127:−0.0037051167 128:0.00010453928 129:0.0017558743 130:−0.00021409123 |
| 131:8.4772248e−005 132:−0.00059640477 133:0.00091315049 134:0.0029517044 |
| 135:0.0012407211 136:0.001771849 137:0.00061086519 138:0.0016401729 139:1.1190635e−005 |
| 140:0.00066645071 141:0.0020694127 142:−0.0019681684 143:−0.0010553099 144:0.0023889465 |
| 145:0.0018726855 146:−0.00070473028 147:−0.0012693994 148:0.0013133255 149:0.0017171054 |
| 150:−0.0023144449 151:0.0023775783 152:−0.00045603843 153:−0.0020286744 154:−3.1378081e−006 |
| 155:−0.0017911249 156:0.00026146293 157:−0.00066072296 158:−0.0012093179 |
| 159:0.00038491705 160:0.00085559086 161:0.0025676095 162:0.0016044743 163:−0.00089113193 |
| 164:0.0024120815 165:0.0010050905 166:0.0013388922 167:−1.9663272e−005 |
| 168:−0.00063788053 169:−0.001915552 170:−0.0015327755 171:−0.00080461183 172:−0.0022213417 |
| 173:−0.0012071569 174:0.00085961225 175:1.1924029e−005 176:−0.00010044254 |
| 177:0.0011742229 178:−0.00082149269 179:−0.0016058821 180:−0.0010348763 181:−0.00091460953 |
| 182:−0.0004915254 183:−0.00073268131 184:−0.00074214442 185:−0.0018549222 |
| 186:−0.00029827142 187:−0.0012626129 188:0.0011506754 189:0.0014984758 190:0.001521907 |
| 191:0.0011545231 192:−0.0017103127 193:−0.0005076346 194:−0.00046162415 195:−0.00039687741 |
| 196:0.0006169476 197:0.0019146017 198:−0.001938576 199:0.00174745 200:−0.00036255008 |
| 201:0.001886385 202:0.00071268051 203:−0.0015044769 204:−0.00094833004 |
| 205:0.0020877882 206:−0.0016524799 207:−0.002788797 208:0.001349878 209:0.001943506 |
| 210:−0.00086329813 211:0.00089030684 212:−0.0019820002 213:6.8280075e−005 |
| 214:−0.00089089427 215:−0.0011382027 216:−0.0011946515 217:−0.031154955 218:−0.018805003 |
| 219:−0.01448297 220:−0.014768096 221:−0.01189405 222:−0.0050329659 223:−0.0038689009 |
| 224:2.2608641e−005 225:−0.00011902419 226:−0.018885663 227:−0.0053921309 |
| 228:−0.0018284534 229:−0.0052720057 230:−0.009582757 231:−0.0060223294 232:−0.0011540388 |
| 233:−0.0011784985 234:−0.0036054854 235:−0.0014334067 236:−0.0057753613 237:−0.092932746 |
| 238:−0.071324907 239:−0.0057371478 240:−0.006171681 241:−0.0023048196 242:−0.0031618457 |
| 243:−0.0039265179 244:−0.036298919 245:−0.026567493 246:−0.048627507 247:−0.022513576 |
| 248:−0.0027006424 249:−0.0030078713 250:−0.0061391126 251:−0.0061381557 252:−0.0049137147 |
| 253:−0.0035512438 254:−0.012955156 255:−0.022692045 256:−0.019110594 257:−0.019834602 |
| 258:−0.0055528483 259:−0.0031212247 260:−0.0048848111 261:−0.0025836895 |
| 262:−0.0010775019 263:−0.0019687952 264:−0.0064801569 265:−0.0049881209 266:−0.0030259397 |
| 267:−0.0079323547 268:−0.043975201 269:−0.047393609 270:−0.0097410055 271:−0.0014055291 |
| 272:−0.0071474779 273:−0.015365882 274:−0.01525611 275:−0.0060280701 276:−0.0022994229 |
| 277:−0.044466536 278:−0.037435107 279:−0.021463662 280:−0.0029869985 281:−0.030177595 |
| 282:−0.023953391 283:−0.005625559 284:−0.035487764 285:−0.029201077 286:−0.011287678 |
| 287:−0.0095548136 288:−5.3504686e−005 289:−0.0016710128 290:0.0016311913 |
| 291:0.0015074767 292:0.0012213683 293:−0.0015347537 294:−7.1857015e−005 295:−0.0013649603 |
| 296:−0.0018400808 297:−0.0011357415 298:0.00029335488 299:−0.00027912227 |
| 300:0.003004099 301:−0.00078015722 302:−0.00046966597 303:−0.00038853599 |
| 304:0.0011859888 305:−0.0017202824 306:0.0010953069 307:0.0015855392 308:−0.0017361958 |
| 309:0.0011252258 310:0.00020620346 311:−0.0008949365 312:−0.00079829368 313:−0.00031991332 |
| 314:0.0018246222 315:0.00081679551 316:0.00071390043 317:0.00014404937 |
| 318:0.00030348785 319:0.0007406784 320:0.00051131583 321:0.0007617402 322:0.0015480069 |
| 323:0.00016401848 324:−0.0024698905 325:−0.00046456934 326:−0.0014662248 327:−0.00017874227 |
| 328:0.0024365219 329:−0.00083040918 330:0.00055475923 331:−2.3758541e−005 |
| 332:0.0013844321 333:0.00018908412 334:−4.6850397e−005 335:0.00017908432 |
| 336:0.0027642041 337:−0.00026057736 338:−0.0019368717 339:0.0012275067 340:−0.0021567047 # |
| 0.003263013586870337 1:4.9163074 2:8.6507969 3:−2.8113577 4:−2.7883282 5:3.6005468 |
| 6:−3.0850611 7:−1.1117666 8:−1.8606527 9:−0.43682045 10:−0.8709569 11:−0.20078206 12:−1.726822 |
| 13:−0.41964892 14:1.0194467 15:−0.13852639 16:0.38812613 17:−1.9748995 18:−0.94841814 |
| 19:−2.4416196 20:−0.80338186 21:−2.112071 22:−0.32373482 23:1.1838528 24:−1.0883764 |
| 25:−0.86285484 26:0.36459005 27:2.0366642 28:1.6910253 29:−1.0555723 30:0.68032825 |
| 31:0.30717254 32:−1.4960066 33:0.21581893 34:0.84493101 35:−1.536992 36:1.8034772 |
| 37:0.22908193 38:−2.0604062 39:0.25210926 40:−0.48998925 41:−0.80221105 42:−0.23084036 |
| 43:1.2399592 44:−0.15893972 45:−1.2630113 46:−0.363563 47:1.1858115 48:−0.35309884 |
| 49:−0.97076398 50:−0.6110034 51:2.2889514 52:0.20005424 53:1.4213701 54:−1.9199978 |
| 55:−0.13937609 56:−0.56550848 57:0.0009495847 58:−0.00063543959 59:0.00017326932 |
| 60:0.0011059562 61:0.0022817524 62:−0.0032958018 63:0.00029474383 64:−0.0021514872 |
| 65:−0.0054451232 66:−0.0024786978 67:3.7493555e−005 68:0.00035079228 69:0.0023467517 |
| 70:0.001588242 71:0.001914337 72:0.0012793314 73:0.0016132059 74:0.00040791018 |
| 75:0.0013395234 76:0.00060126832 77:0.0017832168 78:0.0019726807 79:0.0013805456 |
| 80:−0.00077531522 81:3.2110733e−005 82:0.0011871321 83:0.00056208909 84:0.0005204202 |
| 85:0.0010900472 86:0.0016796719 87:0.0010130677 88:0.00086538575 89:0.0014052332 |
| 90:0.0012018452 91:0.00018189113 92:0.00057689246 93:0.0018313623 94:0.0026408355 |
| 95:0.00079052034 96:0.0019842789 97:−0.0015824389 98:−0.00092224235 99:−0.0010365265 |
| 100:−8.9265384e−005 101:−0.00011542163 102:0.0024433194 103:0.0015950786 104:−0.001393425 |
| 105:−0.00076850987 106:−0.0017206173 107:−0.0011140696 108:−0.0020789856 |
| 109:0.0013786858 110:−0.00081737712 111:−0.0025310477 112:−0.0010236512 113:−0.00049510651 |
| 114:0.0013168686 115:−0.0017368494 116:−0.00051662087 117:−0.0011937086 |
| 118:−0.0008155898 119:−0.0014308705 120:−0.00060646527 121:−0.0023188046 122:−0.00047986541 |
| 123:−0.0017967777 124:−0.0028703539 125:−0.0008995044 126:−0.0044899271 |
| 127:−0.0037051167 128:0.00010453928 129:0.0017558743 130:−0.00021409123 131:8.4772248e−005 |
| 132:−0.00059640477 133:0.00091315049 134:0.0029517044 135:0.0012407211 |
| 136:0.001771849 137:0.00061086519 138:0.0016401729 139:1.1190635e−005 140:0.00066645071 |

APPENDIX C3-continued

SVM Model Weights
(340; Early/Late)

141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763
181:−0.00091460953 182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005
214:−0.00089089427 215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005
295:−0.0013649603 296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.00088570097973736991 1:0.6300419 2:4.7734146 3:−1.2489752 4:−8.6097279 5:2.008311
6:−6.2184939 7:−6.5808897 8:2.7158918 9:−2.4301894 10:−1.2175536 11:−2.2188854 12:4.2264996
13:0.93197346 14:6.044878 15:−1.9431387 16:−0.16680923 17:−1.8877845 18:0.58306974
19:−3.674577 20:1.0183392 21:−0.6716578 22:0.09610986 23:−2.1211574 24:0.99420094
25:−0.4703958 26:0.74925768 27:1.062624 28:−1.8707883 29:−0.82231814 30:−0.45962375
31:2.0175238 32:−0.81920165 33:−1.7209393 34:−1.5601432 35:0.26762301 36:−0.3487784
37:−0.77708137 38:−0.33194357 39:1.8212304 40:−0.35933191 41:−1.2618924 42:−0.8380754
43:1.0074747 44:0.51855934 45:−0.12327518 46:0.61761105 47:0.52314264 48:0.37312344
49:0.71764398 50:−0.29008627 51:−0.55794001 52:0.71641487 53:1.080235 54:0.89552879
55:−0.76276541 56:0.75647557 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417

APPENDIX C3-continued

| SVM Model Weights (340; Early/Late) |
| --- |

173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280082e−005
214:−0.00089089427 215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:0−.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.003263013586870337 1:4.2723708 2:1.0816427 3:−5.1717262 4:−9.1334429 5:−1.5630178
6:−4.2477694 7:−1.4042612 8:8.0716524 9:−0.61411405 10:−1.2446501 11:3.4675648 12:4.4002695
13:0.21902591 14:0.50494504 15:−0.82781434 16:−3.6835434 17:2.1844773 18:1.9099612
19:2.0609009 20:1.1665273 21:−0.24986534 22:−0.78420079 23:0.5788486 24:1.6854416
25:0.16731662 26:1.1378598 27:0.14232612 28:0.27002251 29:0.88255745 30:0.67109448
31:1.0879683 32:1.10175 33:−1.8246135 34:−0.0084914742 35:−1.0067412 36:−0.92044687
37:0.70606804 38:−0.23283091 39:−1.322379 40:−1.7937051 41:0.27961293 42:1.3750051
43:0.65474033 44:−1.502453 45:−0.20695175 46:−1.0827332 47:−1.7445792 48:0.16901226
49:−0.55134284 50:−0.87512439 51:−0.054948792 52:−1.6097244 53:0.47666496 54:−0.15991913
55:0.46501839 56:−0.6946938 57:0.0009495847 58:−0.00063543959 59:0.00017326932
60:0.0011059562 61:0.0022817524 62:−0.0032958018 63:0.00029474383 64:0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004

APPENDIX C3-continued

| SVM Model Weights (340; Early/Late) |
|---|
| 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # 0.0026579988350554653 1:8.4171867 2:5.161294 3:1.8632329 4:5.0714602 5:5.020833 6:−0.54171818 7:−0.74185503 8:−5.2189178 9:6.4979911 10:1.7390909 11:−2.4017231 12:0.7056089 13:4.4163647 14:4.5082531 15:0.24772555 16:−1.049571 17:3.4169843 18:−2.5641735 19:−0.78975821 20:−0.5222187 21:0.89725953 22:3.7222507 23:1.0190701 24:0.7194767 25:−1.119658 26:−2.1368935 27:−0.54928917 28:1.0772496 29:1.3982881 30:−1.1084408 31:−0.12536865 32:1.1006286 33:−0.43901601 34:1.1063771 35:0.71711397 36:−0.84509456 37:−2.4609451 38:0.68434292 39:−0.64825416 40:−2.0648291 41:−0.44888297 42:−1.0822344 43:0.51638848 44:−0.57787544 45:0.29730579 46:−0.18524137 47:−0.18624319 48:−0.13633247 49:−1.2936491 50:1.1114132 51:−0.12494335 52:0.32624847 53:−0.27875072 54:−0.098541729 55:−0.45952901 56:−0.61816746 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 |

APPENDIX C3-continued

| SVM Model Weights (340; Early/Late) |
|---|
| 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # −0.0013793984127039756 1:13.466636 2:3.3573108 3:5.5644298 4:0.57824087 5:1.6920621 6:−4.2968526 7:−2.6953287 8:12.022702 9:−0.46672329 10:3.9010904 11:0.45902482 12:−2.2463238 13:0.8365761 14:1.4948182 15:−2.4529717 16:−0.018621992 17:−0.018616691 18:−1.1184366 19:2.0151198 20:1.3533055 21:0.72912431 22:0.03273252 23:0.87820792 24:0.90275949 25:0.52287197 26:−1.414227 27:−1.1956365 28:1.5341172 29:−0.20564413 30:0.82979262 31:2.2867506 32:0.16699626 33:−0.2037773 34:1.3190736 35:0.43436375 36:0.012350954 37:−0.05768029 38:0.40372571 39:−0.64488149 40:2.1604466 41:0.53956074 42:−0.20766212 43:0.26843727 44:0.45486873 45:1.3371893 46:0.18679692 47:−0.2628372 48:−0.3535971 49:1.1567792 50:1.3093958 51:0.5129692 52:1.626673 53:1.0476021 54:−0.84348559 55:0.21671142 56:0.50009787 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 |

APPENDIX C3-continued

SVM Model Weights
(340; Early/Late)

272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
−0.003263013586870337 1:8.0561037 2:−1.9924136 3:0.82999653 4:−3.7921369 5:−0.51860911
6:−6.4783216 7:1.8349005 8:9.0483742 9:−5.104785 10:0.79596269 11:−3.5503304 12:0.75062472
13:4.4150515 14:0.4702543 15:0.7237826 16:−3.622617 17:−0.06912373 18:−0.52799076
19:1.5017456 20:−3.5132833 21:−0.99361396 22:−0.92652875 23:−0.38866544 24:−1.7653948
25:−0.16442132 26:−0.61083925 27:−0.67040193 28:−0.2000851 29:−0.59121299 30:−0.51341027
31:−3.8886027 32:−0.1798937 33:2.6713161 34:−0.14334825 35:0.89026397 36:0.85009325
37:0.19307545 38:0.44975233 39:0.91792029 40:−0.53343427 41:0.32704374 42:−0.82176453
43:−1.5447295 44:0.5786891 45:−0.61071676 46:0.086533055 47:1.4453341 48:0.0016415269
49:−0.93683887 50:−0.099545226 51:−0.047955405 52:−0.3801434 53:−0.59374726 54:0.13185878
55:−0.20707117 56:−0.28867543 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005
214:−0.00089089427 215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.0411287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599

APPENDIX C3-continued

| SVM Model Weights (340; Early/Late) |
|---|
| 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # 0.0030172463327856796 1:−3.0042043 2:−3.113188 3:0.97381061 4:3.8624547 5:0.49664947 6:6.8813305 7:3.981081 8:0.12391745 9:−7.6547618 10:−2.7285914 11:−0.53179222 12:−0.30781594 13:7.1988821 14:−0.44064531 15:1.0810283 16:0.82087684 17:2.8132896 18:6.1163325 19:−0.52160966 20:−1.1575588 21:−0.34605175 22:1.7179306 23:1.239956 24:−2.2303703 25:−2.0092707 26:1.3119591 27:0.4040986 28:0.94076431 29:2.2957568 30:0.35625714 31:1.05492 32:−1.8137116 33:0.085117221 34:−0.17722237 35:−0.93875301 36:−1.492783 37:−0.82638711 38:−0.040122535 39:1.2046241 40:0.11793934 41:−0.12299792 42:0.31207559 43:0.16833082 44:−0.06479533 45:−0.038384501 46:0.38733277 47:−0.22372454 48:−0.20940353 49:0.85714841 50:0.39960006 51:0.34220061 52:0.65982866 53:0.95779282 54:0.46020558 55:−0.084201649 56:−0.048425782 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 |

APPENDIX C3-continued

| SVM Model Weights (340; Early/Late) |
|---|
| 336:0.0027642041 337:−0.00026057736 338:−0.0019368717 339:0.0012275067 340:−0.0021567047 # 0.003263013586870337 1:5.9731479 2:−2.2345276 3:2.4485157 4:0.69162613 5:0.90995193 6:0.060546741 7:1.8535619 8:−4.2391319 9:−3.620893 10:−0.84653771 11:1.5584985 12:−0.72690475 13:1.0212981 14:0.82094777 15:0.12706149 16:0.44026414 17:0.51657689 18:−1.7734509 19:−0.82144797 20:−0.95747542 21:0.71957904 22:−0.80198896 23:−2.2893806 24:−0.034846626 25:1.8044568 26:0.59219909 27:−0.66372091 28:−1.2759969 29:0.34522814 30:1.7603507 31:0.1729089 32:0.50999016 33:−0.050911739 34:0.95418978 35:−1.2323328 36:1.371628 37:0.25137526 38:−1.2536705 39:0.76166493 40:−1.084955 41:−0.45288616 42:−1.5072262 43:−0.27096277 44:1.378207 45:0.97615772 46:−1.5166835 47:−0.55975312 48:0.69940495 49:1.9877241 50:2.0888352 51:−0.83042544 52:−2.227911 53:0.45020425 54:−0.86201608 55:−0.60144496 56:−0.13532874 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # 0.003263013586870337 1:2.9703248 2:−1.9154285 3:−1.4705251 4:−3.6158135 5:−0.88654208 6:−5.2746539 7:3.5916541 8:−1.5249115 9:0.42257392 10:0.1542328 11:−0.79797947 12:1.5178829 13:−4.328999 14:−1.9303721 15:−3.6791089 16:2.030098 17:3.196708 18:0.70455837 19:−0.99888653 20:−0.90641922 21:−1.3292599 22:−1.3334385 23:−0.034880091 24:−0.21998923 25:−1.0224223 26:−0.27785692 27:0.887824 28:−0.88122153 29:2.4520988 30:−1.8591628 31:−0.2047378 32:−0.43277052 33:1.3049064 34:0.28490406 35:0.58858889 36:0.31118494 37:−0.75974351 |

APPENDIX C3-continued

SVM Model Weights
(340; Early/Late)

38:0.30014536 39:0.16725326 40:0.28239837 41:0.85730082 42:0.18312453
43:0.73757261 44:0.23835303 45:0.42016032 46:−0.027372906 47:0.12297571 48:0.091952026
49:0.19956252 50:0.14478266 51:−0.31726134 52:0.075183503 53:0.078598507 54:−0.32566643
55:0.26622328 56:−0.10797127 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786
104:−0.001393425 105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:11190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005
214:−0.00089089427 215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
−0.003263013586870337 1:−6.6983242 2:−9.0942469 3:1.7515687 4:−0.034388322 5:−4.4506936
6:0.60848588 7:4.9920249 8:0.42073253 9:−1.6036102 10:4.4492455 11:0.61170918 12:1.7242055
13:−2.4792538 14:1.1316463 15:0.55399567 16:−0.67547733 17:−0.71950591 18:−3.7744215
19:0.12060646 20:1.7497555 21:−0.85744029 22:−0.2730225 23:−0.18385465 24:0.064841606
25:−0.29801944 26:3.2788053 27:1.8581574 28:1.7073642 29:−1.5964348 30:−1.0948637
31:−1.7955403 32:−0.33725154 33:0.59672004 34:−0.64073378 35:−1.2621409 36:−0.2854811
37:−0.77229369 38:3.2878306 39:0.32339731 40:−1.8727088 41:−1.8741317 42:0.62994355
43:0.24595919 44:−0.30926743 45:0.034467354 46:−1.114936 47:−0.47947472 48:0.27271232
49:0.7489326 50:0.69949538 51:0.75706381 52:0.79426801 53:1.113898 54:0.79861182
55:0.13863973 56:0.32391682 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018

APPENDIX C3-continued

| SVM Model Weights (340; Early/Late) |
|---|
| 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # −0.003263013586870337 1:1.5687745 2:2.8747225 3:−4.5921497 4:0.64045548 5:−1.2402862 6:−1.6395731 7:6.439642 8:2.6914668 9:−1.4795072 10:−1.9112765 11:1.2422292 12:1.8375124 13:−0.94092149 14:−1.5335485 15:0.75675613 16:2.4802206 17:0.34209159 18:−1.2560471 19:−2.1931856 20:3.7075293 21:1.1574953 22:3.5674658 23:0.15892406 24:−0.82145321 25:0.33991763 26:0.49271733 27:0.052549031 28:1.1602603 29:2.4897397 30:1.3658088 31:−1.7658501 32:3.6958034 33:−1.048786 34:−1.3994727 35:2.1602569 36:−1.0454955 37:1.4556481 38:−0.61492872 39:−0.61211729 40:0.33369657 41:−1.1614405 42:−1.7464546 43:−0.42068875 44:0.88658863 45:−0.50272441 46:0.30446854 47:0.77701253 48:1.0611333 49:0.34844396 50:−1.1361352 51:0.098503217 52:0.3325029 53:0.73619086 54:−0.41577715 55:0.065231077 56:0.1329993 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 |

APPENDIX C3-continued

| SVM Model Weights (340; Early/Late) |
|---|
| 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # −0.003263013586870337 1:0.12176631 2:1.5119995 3:−0.2009106 4:2.364769 5:−2.1576962 6:5.2755914 7:5.1912417 8:3.4393139 9:2.883764 10:5.7631373 11:2.7202239 12:−0.32031089 13:2.678786 14:−0.60210669 15:−1.4041533 16:−0.1163752 17:−0.39201191 18:−1.0063212 19:−4.5707445 20:1.3226789 21:−2.5034225 22:−1.5694625 23:−0.089195952 24:0.82619452 25:0.2266219 26:−1.857953 27:−2.5074837 28:−1.8170778 29:0.85228193 30:0.48416921 31:1.206537 32:−1.4583262 33:0.2215921 34:−2.5907068 35:0.39124185 36:−0.14954042 37:0.2999247 38:1.4811584 39:−0.8232218 40:−0.53053021 41:1.00964 42:0.62065589 43:−0.81233174 44:0.47553596 45:−0.9810462 46:0.35647628 47:0.067086481 48:−1.3161986 49:0.13868965 50:−0.60173982 51:0.69744349 52:−1.1355891 53:0.34819937 54:−0.12546013 55:−1.6039717 56:−0.23121783 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 |

APPENDIX C3-continued

| SVM Model Weights (340; Early/Late) |
|---|

141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.0014965176130378463 1:4.3982258 2:−0.16226812 3:0.28672937 4:−6.4362116 5:2.2866001
6:1.5062218 7:−1.2038572 8:−4.7404804 9:−2.3843164 10:2.2418141 11:−0.27465099
12:−2.8525231 13:2.1683853 14:−2.2989886 15:1.1782279 16:−1.7451806 17:−0.13980241
18:−0.97569644 19:2.1530244 20:0.67875266 21:−1.6640399 22:−0.19732694 23:−3.0789464
24:−0.19650537 25:−1.093295 26:1.5532137 27:−1.5915536 28:0.39503294 29:0.4357492
30:−0.26054665 31:1.5233505 32:0.020384328 33:0.68401867 34:−1.9224312 35:1.9247659
36:0.039446298 37:−0.81243855 38:−0.69054139 39:−0.79842049 40:−0.71187359 41:0.059527773
42:0.51264888 43:0.056126643 44:0.94826233 45:−2.3683159 46:−0.48733464 47:−1.115755
48:0.089708 49:−0.8857457 50:0.39930597 51:−0.80264562 52:0.59585118 53:−0.15955684
54:−1.1931409 55:1.2970268 56:1.7515355 57:0.0009495847 58:−0.00063543959 59:0.00017326932
60:0.0011059562 61:0.0022817524 62:−0.0032958018 63:0.00029474383 64:−0.0021514872
65:−0.0054451232 66:−0.0024786978 67:3.7493555e−005 68:0.00035079228 69:0.0023467517
70:0.001588242 71:0.001914337 72:0.0012793314 73:0.0016132059 74:0.00040791018
75:0.0013395234 76:0.00060126832 77:0.0017832168 78:0.0019726807 79:0.0013805456
80:−0.00077531522 81:3.2110733e−005 82:0.0011871321 83:0.00056208909 84:0.0005204202
85:0.0010900472 86:0.0016796719 87:0.0010130677 88:0.00086538575 89:0.0014052332
90:0.0012018452 91:0.00018189113 92:0.00057689246 93:0.0018313623 94:0.0026408355
95:0.00079052034 96:0.0019842789 97:−0.0015824389 98:−0.00092224235 99:−0.0010365265
100:−8.9265384e−005 101:−0.00011542163 102:0.0024433194 103:0.0015950786 104:−0.001393425
105:−0.00076850987 106:−0.0017206173 107:−0.0011140696 108:−0.0020789856
109:0.0013786858 110:−0.00081737712 111:−0.0025310477 112:−0.0010236512 113:−0.00049510651
114:0.0013168686 115:−0.0017368494 116:−0.00051662087 117:−0.0011937086
118:−0.0008155898 119:−0.0014308705 120:−0.00060646527 121:−0.0023188046 122:−0.00047986541
123:−0.0017967777 124:−0.0028703539 125:−0.0008995044 126:−0.0044899271
127:−0.0037051167 128:0.00010453928 129:0.0017558743 130:−0.00021409123 131:8.4772248e−005
132:−0.00059640477 133:0.00091315049 134:0.0029517044 135:0.0012407211
136:0.001771849 137:0.00061086519 138:0.0016401729 139:1.1190635e−005 140:0.00066645071
141:0.0020694127 142:−0.0019681684 143:−0.0010553099 144:0.0023889465 145:0.0018726855
146:−0.00070473028 147:−0.0012693994 148:0.0013133255 149:0.0017171054 150:−0.0023144449
151:0.0023775783 152:−0.00045603843 153:−0.0020286744 154:−3.1378081e−006
155:−0.0017911249 156:0.00026146293 157:−0.00066072296 158:−0.0012093179
159:0.00038491705 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417

APPENDIX C3-continued

SVM Model Weights
(340; Early/Late)

173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004
205:0.0020877882 206:−0.0016524799 207:−0.002788797 208:0.001349878 209:0.001943506
210:−0.00086329813 211:0.00089030684 212:−0.0019820002 213:6.8280075e−005 214:−0.00089089427
215:−0.0011382027 216:−0.0011946515 217:−0.031154955 218:−0.018805003
219:−0.01448297 220:−0.014768096 221:−0.01189405 222:−0.0050329659 223:−0.0038689009
224:2.2608641e−005 225:−0.00011902419 226:−0.018885663 227:−0.0053921309 228:−0.0018284534
229:−0.0052720057 230:−0.009582757 231:−0.0060223294 232:−0.0011540388
233:−0.0011784985 234:−0.0036054854 235:−0.0014334067 236:−0.0057753613 237:−0.092932746
238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.00072055836256387535 1:−8.2843933 2:3.6966038 3:−0.46435714 4:1.5304902 5:1.1075522
6:1.9134642 7:−0.79442489 8:0.52520049 9:0.83645153 10:−2.6971796 11:−0.88591361
12:1.3652115 13:0.92740053 14:1.9873277 15:−3.1379786 16:1.0197264 17:−2.7746265
18:0.68137848 19:−1.3835444 20:1.2694755 21:0.34423488 22:−1.891607 23:0.15474756
24:1.2157984 25:−0.04881968 26:−0.55643517 27:−1.6764784 28:2.4692996 29:0.067258775
30:−1.8768005 31:−0.14590223 32:−0.94142735 33:−0.80213898 34:−0.50326455 35:−1.2780002
36:0.13170069 37:−0.80249226 38:−0.58796179 39:−1.7767088 40:−0.65758491 41:1.6625999
42:−1.8933594 43:−1.8352563 44:0.28400037 45:−0.64471543 46:−0.70836622 47:1.023016
48:−0.0095212217 49:0.77695823 50:0.31655601 51:0.17602722 52:−0.44220364 53:0.20299678
54:0.98908013 55:2.5351987 56:−0.41776881 57:0.0009495847 58:−0.00063543959
59:0.00017326932 60:0.0011059562 61:0.0022817524 62:−0.0032958018 63:0.00029474383
64:−0.0021514872 65:−0.0054451232 66:−0.0024786978 67:3.7493555e−005 68:0.00035079228
69:0.0023467517 70:0.001588242 71:0.001914337 72:0.0012793314 73:0.0016132059
74:0.00040791018 75:0.0013395234 76:0.00060126832 77:0.0017832168 78:0.0019726807
79:0.0013805456 80:−0.00077531522 81:3.2110733e−005 82:0.0011871321 83:0.00056208909
84:0.0005204202 85:0.0010900472 86:0.0016796719 87:0.0010130677 88:0.00086538575
89:0.0014052332 90:0.0012018452 91:0.00018189113 92:0.00057689246 93:0.0018313623
94:0.0026408355 95:0.00079052034 96:0.0019842789 97:−0.0015824389 98:−0.00092224235
99:−0.0010365265 100:−8.9265384e−005 101:−0.00011542163 102:0.0024433194 103:0.0015950786
104:−0.001393425 105:−0.00076850987 106:−0.0017206173 107:−0.0011140696 108:−0.0020789856
109:0.0013786858 110:−0.00081737712 111:−0.0025310477 112:−0.0010236512
113:−0.00049510651 114:0.0013168686 115:−0.0017368494 116:−0.00051662087
117:−0.0011937086 118:−0.0008155898 119:−0.0014308705 120:−0.00060646527 121:−0.0023188046
122:−0.00047986541 123:−0.0017967777 124:−0.0028703539 125:−0.0008995044 126:−0.0044899271
127:−0.0037051167 128:0.00010453928 129:0.0017558743 130:−0.00021409123
131:8.4772248e−005 132:−0.00059640477 133:0.00091315049 134:0.0029517044
135:0.0012407211 136:0.001771849 137:0.00061086519 138:0.0016401729 139:1.1190635e−005
140:0.00066645071 141:0.0020694127 142:−0.0019681684 143:−0.0010553099 144:0.0023889465
145:0.0018726855 146:−0.00070473028 147:−0.0012693994 148:0.0013133255 149:0.0017171054
150:−0.0023144449 151:0.0023775783 152:−0.00045603843 153:−0.0020286744 154:−3.1378081e−006
155:−0.0017911249 156:0.00026146293 157:−0.00066072296 158:−0.0012093179
159:0.00038491708 160:0.00085559086 161:0.0025676095 162:0.0016044743 163:−0.00089113193
164:0.0024120815 165:0.0010050905 166:0.0013388922 167:−1.9663272e−005
168:−0.00063788053 169:−0.001915552 170:−0.0015327755 171:−0.00080461183 172:−0.0022213417
173:−0.0012071569 174:0.00085961225 175:1.1924029e−005 176:−0.00010044254
177:0.0011742229 178:−0.00082149269 179:−0.0016058821 180:−0.0010348763 181:−0.00091460953
182:−0.0004915254 183:−0.00073268131 184:0.00074214442 185:−0.0018549222
186:−0.00029827142 187:−0.0012626129 188:0.0011506754 189:0.0014984758 190:0.001521907
191:0.0011545231 192:−0.0017103127 193:−0.0005076346 194:−0.00046162415 195:−0.00039687741
196:0.0006169476 197:0.0019146017 198:−0.001938576 199:0.00174745 200:−0.00036255008
201:0.001886385 202:0.00071268051 203:−0.0015044769 204:−0.00094833004

APPENDIX C3-continued

| SVM Model Weights (340; Early/Late) |
| --- |
| 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # 0.00090918234784548757 1:−6.122613 2:−0.55014724 3:0.29037741 4:−7.820363 5:−0.075020343 6:3.8448997 7:0.31839412 8:2.5894465 9:0.42450967 10:−2.6556973 11:−1.0042195 12:−3.5184166 13:−1.6911469 14:−1.1769295 15:0.024770757 16:−1.4050843 17:0.087066472 18:−0.95585454 19:−0.48107174 20:1.9910818 21:1.4393178 22:−0.28986773 23:2.0448291 24:−0.93548518 25:0.62121999 26:−3.1084788 27:−0.12058441 28:−1.0080323 29:1.2899083 30:−0.75200337 31:−1.2419468 32:−1.4561284 33:−0.41465601 34:1.9404265 35:−1.2137595 36:−1.0310935 37:1.5804566 38:−1.6227396 39:−1.3698378 40:−3.1060567 41:−0.70550668 42:1.8586001 43:0.36955735 44:1.0749351 45:0.40818423 46:1.1543205 47:0.68963659 48:0.30432531 49:0.10152308 50:0.73522979 51:−0.12000543 52:0.40799132 53:−0.19432676 54:0.41782823 55:−0.2914685 56:1.4504484 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 |

APPENDIX C3-continued

SVM Model Weights
(340; Early/Late)

238:−0.071324907 239:−0.0057371478 240:−0.006171681 241:−0.0023048196 242:−0.0031618457
243:−0.0039265179 244:−0.036298919 245:−0.026567493 246:−0.048627507 247:−0.022513576
248:−0.0027006424 249:−0.0030078713 250:−0.0061391126 251:−0.0061381557 252:−0.0049137147
253:−0.0035512438 254:−0.012955156 255:−0.022692045 256:−0.019110594 257:−0.019834602
258:−0.0055528483 259:−0.0031212247 260:−0.0048848111 261:−0.0025836895
262:−0.0010775019 263:−0.0019687952 264:−0.0064801569 265:−0.0049881209 266:−0.0030259397
267:−0.0079323547 268:−0.043975201 269:−0.047393609 270:−0.0097410055 271:−0.0014055291
272:−0.0071474779 273:−0.015365882 274:−0.01525611 275:−0.0060280701 276:−0.0022994229
277:−0.044466536 278:−0.037435107 279:−0.021463662 280:−0.0029869985 281:−0.030177595
282:−0.023953391 283:−0.005625559 284:−0.035487764 285:−0.029201077 286:−0.011287678
287:−0.0095548136 288:−5.3504686e−005 289:−0.0016710128 290:0.0016311913
291:0.0015074767 292:0.0012213683 293:−0.0015347537 294:−7.1857015e−005 295:−0.0013649603
296:−0.0018400808 297:−0.0011357415 298:0.00029335488 299:−0.00027912227
300:0.003004099 301:−0.00078015722 302:−0.00046966597 303:−0.00038853599
304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #
0.00012532704104316504 1:−2.988956 2:−14.541928 3:−24.152397 4:7.8578658 5:0.62039638
6:−1.4124461 7:−3.5245433 8:0.23765643 9:0.59025252 10:0.51212358 11:−1.3314158 12:−2.0315864
13:−0.2914176 14:0.37882963 15:0.082344197 16:−0.57432884 17:−0.080625705 18:−0.14113382
19:−0.13893105 20:−0.28207991 21:0.12245945 22:−0.23306957 23:−0.074358061 24:0.075329393
25:0.095754124 26:0.17469533 27:−0.15946545 28:0.030569298 29:−0.041504841 30:0.1790569
31:0.18031198 32:−0.18188456 33:−0.14256233 34:−0.087481722 35:0.093072012
36:−0.0096975714 37:0.055885319 38:−0.26989311 39:0.060945775 40:0.025113981 41:−0.020692149
42:−0.027143152 43:0.010555366 44:0.17869918 45:0.10947593 46:0.10241339 47:−0.066085763
48:−0.047175925 49:−0.069109127 50:0.098929293 51:0.0071666436 52:0.011446619
53:−0.12375915 54:0.034906533 55:−0.055961743 56:−0.0013580584 57:0.0009495847
58:−0.00063543959 59:0.00017326932 60:0.0011059562 61:0.0022817524 62:−0.0032958018
63:0.00029474383 64:−0.0021514872 65:−0.0054451232 66:−0.0024786978 67:3.7493555e−005
68:0.00035079228 69:0.0023467517 70:0.001588242 71:0.001914337 72:0.0012793314
73:0.0016132059 74:0.00040791018 75:0.0013395234 76:0.00060126832 77:0.0017832168
78:0.0019726807 79:0.0013805456 80:−0.00077531522 81:3.2110733e−005 82:0.0011871321
83:0.00056208909 84:0.0005204202 85:0.0010900472 86:0.0016796719 87:0.0010130677
88:0.00086538575 89:0.0014052332 90:0.0012018452 91:0.00018189113 92:0.00057689246
93:0.0018313623 94:0.0026408355 95:0.00079052034 96:0.0019842789 97:−0.0015824389
98:−0.00092224235 99:−0.0010365265 100:−8.9265384e−005 101:−0.00011542163 102:0.0024433194
103:0.0015950786 104:−0.001393425 105:−0.00076850987 106:−0.0017206173 107:−0.0011140696
108:−0.0020789856 109:0.0013786858 110:−0.00081737712 111:−0.0025310477
112:−0.0010236512 113:−0.00049510651 114:0.0013168686 115:−0.0017368494 116:−0.00051662087
117:−0.0011937086 118:−0.0008155898 119:−0.0014308705 120:−0.00060646527
121:−0.0023188046 122:−0.00047986541 123:−0.0017967777 124:−0.0028703539 125:−0.0008995044
126:−0.0044899271 127:−0.0037051167 128:0.00010453928 129:0.0017558743
130:−0.00021409123 131:8.4772248e−005 132:−0.00059640477 133:0.00091315049
134:0.0029517044 135:0.0012407211 136:0.001771849 137:0.00061086519 138:0.0016401729
139:1.1190635e−005 140:0.00066645071 141:0.0020694127 142:−0.0019681684 143:−0.0010553099
144:0.0023889465 145:0.0018726855 146:−0.00070473028 147:−0.0012693994
148:0.0013133255 149:0.0017171054 150:−0.0023144449 151:0.0023775783 152:−0.00045603843
153:−0.0020286744 154:−3.1378081e−006 155:−0.0017911249 156:0.00026146293
157:−0.00066072296 158:−0.0012093179 159:0.00038491705 160:0.00085559086 161:0.0025676095
162:0.0016044743 163:−0.00089113193 164:0.0024120815 165:0.0010050905 166:0.0013388922
167:−1.9663272e−005 168:−0.00063788053 169:−0.001915552 170:−0.0015327755
171:−0.00080461183 172:−0.0022213417 173:−0.0012071569 174:0.00085961225 175:1.1924029e−005
176:−0.00010044254 177:0.0011742229 178:−0.00082149269 179:−0.0016058821 180:−0.0010348763
181:−0.00091460953 182:−0.0004915254 183:−0.00073268131 184:0.00074214442
185:−0.0018549222 186:−0.00029827142 187:−0.0012626129 188:0.0011506754
189:0.0014984758 190:0.001521907 191:0.0011545231 192:−0.0017103127 193:−0.0005076346
194:−0.00046162415 195:−0.00039687741 196:0.0006169476 197:0.0019146017 198:−0.001938576
199:0.00174745 200:−0.00036255008 201:0.001886385 202:0.00071268051 203:−0.0015044769
204:−0.00094833004 205:0.0020877882 206:−0.0016524799 207:−0.002788797 208:0.001349878
209:0.001943506 210:−0.00086329813 211:0.00089030684 212:−0.0019820002 213:6.8280075e−005
214:−0.00089089427 215:−0.0011382027 216:−0.0011946515 217:−0.031154955
218:−0.018805003 219:−0.01448297 220:−0.014768096 221:−0.01189405 222:−0.0050329659
223:−0.0038689009 224:2.2608641e−005 225:−0.00011902419 226:−0.018885663
227:−0.0053921309 228:−0.0.0018284534 229:−0.0052720057 230:−0.009582757 231:−0.0060223294
232:−0.0011540388 233:−0.0011784985 234:−0.0036054854 235:−0.0014334067 236:−0.0057753613
237:−0.092932746 238:−0.071324907 239:−0.0057371478 240:−0.006171681 241:−0.0023048196
242:−0.0031618457 243:−0.0039265179 244:−0.036298919 245:−0.026567493 246:−0.048627507
247:−0.022513576 248:−0.0027006424 249:−0.0030078713 250:−0.0061391126 251:−0.0061381557
252:−0.0049137147 253:−0.0035512438 254:−0.012955156 255:−0.022692045 256:−0.019110594
257:−0.019834602 258:−0.0055528483 259:−0.0031212247 260:−0.0048848111 261:−0.0025836895
262:−0.0010775019 263:−0.0019687952 264:−0.0064801569 265:−0.0049881209
266:−0.0030259397 267:−0.0079323547 268:−0.043975201 269:−0.047393609 270:−0.0097410055

APPENDIX C3-continued

| SVM Model Weights (340; Early/Late) |
|---|
| 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 304:0.0011859888 305:−0.0017202824 306:0.0010953069 307:0.0015855392 308:−0.0017361958 309:0.0011252258 310:0.00020620346 311:−0.0008949365 312:−0.00079829368 313:−0.00031991332 314:0.0018246222 315:0.00081679551 316:0.00071390043 317:0.00014404937 318:0.00030348785 319:0.0007406784 320:0.00051131583 321:0.0007617402 322:0.0015480069 323:0.00016401848 324:−0.0024698905 325:−0.00046456934 326:−0.0014662248 327:−0.00017874227 328:0.0024365219 329:−0.00083040918 330:0.00055475923 331:−2.3758541e−005 332:0.0013844321 333:0.00018908412 334:−4.6850397e−005 335:0.00017908432 336:0.0027642041 337:−0.00026057736 338:−0.0019368717 339:0.0012275067 340:−0.0021567047 # 2.1497918288429496e−005 1:−34.113136 2:9.1733046 3:5.3838677 4:7.6956291 5:13.459892 6:−3.5612979 7:−7.1091042 8:5.5747619 9:−2.8808331 10:1.8228761 11:−0.80162328 12:0.45366946 13:0.35113454 14:−5.9756327 15:1.5504394 16:1.9655282 17:2.4146829 18:−2.2898633 19:−0.88621074 20:−1.1601353 21:−0.79647011 22:1.5297979 23:−1.7144865 24:0.64629495 25:1.1985551 26:0.55810708 27:−0.25598845 28:−0.38665497 29:−0.00039836648 30:−1.1873535 31:−0.085017577 32:−0.069415957 33:−0.41498676 34:0.24881725 35:0.18458879 36:0.20159762 37:0.18202665 38:−0.081453502 39:0.168487 40:−0.027624954 41:0.18284768 42:0.38703957 43:0.40067115 44:0.0030078939 45:0.25092465 46:−0.28690481 47:−0.096155189 48:0.052919824 49:−0.31122819 50:0.11490654 51:0.10996526 52:−0.24321437 53:0.19623207 54:0.099348456 55:−0.077123351 56:−0.11627381 57:0.0009495847 58:−0.00063543959 59:0.00017326932 60:0.0011059562 61:0.0022817524 62:−0.0032958018 63:0.00029474383 64:−0.0021514872 65:−0.0054451232 66:−0.0024786978 67:3.7493555e−005 68:0.00035079228 69:0.0023467517 70:0.001588242 71:0.001914337 72:0.0012793314 73:0.0016132059 74:0.00040791018 75:0.0013395234 76:0.00060126832 77:0.0017832168 78:0.0019726807 79:0.0013805456 80:−0.00077531522 81:3.2110733e−005 82:0.0011871321 83:0.00056208909 84:0.0005204202 85:0.0010900472 86:0.0016796719 87:0.0010130677 88:0.00086538575 89:0.0014052332 90:0.0012018452 91:0.00018189113 92:0.00057689246 93:0.0018313623 94:0.0026408355 95:0.00079052034 96:0.0019842789 97:−0.0015824389 98:−0.00092224235 99:−0.0010365265 100:−8.9265384e−005 101:−0.00011542163 102:0.0024433194 103:0.0015950786 104:−0.001393425 105:−0.00076850987 106:−0.0017206173 107:−0.0011140696 108:−0.0020789856 109:0.0013786858 110:−0.00081737712 111:−0.0025310477 112:−0.0010236512 113:−0.00049510651 114:0.0013168686 115:−0.0017368494 116:−0.00051662087 117:−0.0011937086 118:−0.0008155898 119:−0.0014308705 120:−0.00060646527 121:−0.0023188046 122:−0.00047986541 123:−0.0017967777 124:−0.0028703539 125:−0.0008995044 126:−0.0044899271 127:−0.0037051167 128:0.00010453928 129:0.0017558743 130:−0.00021409123 131:8.4772248e−005 132:−0.00059640477 133:0.00091315049 134:0.0029517044 135:0.0012407211 136:0.001771849 137:0.00061086519 138:0.0016401729 139:1.1190635e−005 140:0.00066645071 141:0.0020694127 142:−0.0019681684 143:−0.0010553099 144:0.0023889465 145:0.0018726855 146:−0.00070473028 147:−0.0012693994 148:0.0013133255 149:0.0017171054 150:−0.0023144449 151:0.0023775783 152:−0.00045603843 153:−0.0020286744 154:−3.1378081e−006 155:−0.0017911249 156:0.00026146293 157:−0.00066072296 158:−0.0012093179 159:0.00038491705 160:0.00085559086 161:0.0025676095 162:0.0016044743 163:−0.00089113193 164:0.0024120815 165:0.0010050905 166:0.0013388922 167:−1.9663272e−005 168:−0.00063788053 169:−0.001915552 170:−0.0015327755 171:−0.00080461183 172:−0.0022213417 173:−0.0012071569 174:0.00085961225 175:1.1924029e−005 176:−0.00010044254 177:0.0011742229 178:−0.00082149269 179:−0.0016058821 180:−0.0010348763 181:−0.00091460953 182:−0.0004915254 183:−0.00073268131 184:0.00074214442 185:−0.0018549222 186:−0.00029827142 187:−0.0012626129 188:0.0011506754 189:0.0014984758 190:0.001521907 191:0.0011545231 192:−0.0017103127 193:−0.0005076346 194:−0.00046162415 195:−0.00039687741 196:0.0006169476 197:0.0019146017 198:−0.001938576 199:0.00174745 200:−0.00036255008 201:0.001886385 202:0.00071268051 203:−0.0015044769 204:−0.00094833004 205:0.0020877882 206:−0.0016524799 207:−0.002788797 208:0.001349878 209:0.001943506 210:−0.00086329813 211:0.00089030684 212:−0.0019820002 213:6.8280075e−005 214:−0.00089089427 215:−0.0011382027 216:−0.0011946515 217:−0.031154955 218:−0.018805003 219:−0.01448297 220:−0.014768096 221:−0.01189405 222:−0.0050329659 223:−0.0038689009 224:2.2608641e−005 225:−0.00011902419 226:−0.018885663 227:−0.0053921309 228:−0.0018284534 229:−0.0052720057 230:−0.009582757 231:−0.0060223294 232:−0.0011540388 233:−0.0011784985 234:−0.0036054854 235:−0.0014334067 236:−0.0057753613 237:−0.092932746 238:−0.071324907 239:−0.0057371478 240:−0.006171681 241:−0.0023048196 242:−0.0031618457 243:−0.0039265179 244:−0.036298919 245:−0.026567493 246:−0.048627507 247:−0.022513576 248:−0.0027006424 249:−0.0030078713 250:−0.0061391126 251:−0.0061381557 252:−0.0049137147 253:−0.0035512438 254:−0.012955156 255:−0.022692045 256:−0.019110594 257:−0.019834602 258:−0.0055528483 259:−0.0031212247 260:−0.0048848111 261:−0.0025836895 262:−0.0010775019 263:−0.0019687952 264:−0.0064801569 265:−0.0049881209 266:−0.0030259397 267:−0.0079323547 268:−0.043975201 269:−0.047393609 270:−0.0097410055 271:−0.0014055291 272:−0.0071474779 273:−0.015365882 274:−0.01525611 275:−0.0060280701 276:−0.0022994229 277:−0.044466536 278:−0.037435107 279:−0.021463662 280:−0.0029869985 281:−0.030177595 282:−0.023953391 283:−0.005625559 284:−0.035487764 285:−0.029201077 286:−0.011287678 287:−0.0095548136 288:−5.3504686e−005 289:−0.0016710128 290:0.0016311913 291:0.0015074767 292:0.0012213683 293:−0.0015347537 294:−7.1857015e−005 295:−0.0013649603 296:−0.0018400808 297:−0.0011357415 298:0.00029335488 299:−0.00027912227 300:0.003004099 301:−0.00078015722 302:−0.00046966597 303:−0.00038853599 |

APPENDIX C3-continued

SVM Model Weights
(340; Early/Late)

304:0.0011859888 305:−0.0017202824 306:0.0010953069 307:0.0015855392 308:−0.0017361958
309:0.0011252258 310:0.00020620346 311:−0.0008949365 312:−0.00079829368 313:−0.00031991332
314:0.0018246222 315:0.00081679551 316:0.00071390043 317:0.00014404937
318:0.00030348785 319:0.0007406784 320:0.00051131583 321:0.0007617402 322:0.0015480069
323:0.00016401848 324:−0.0024698905 325:−0.00046456934 326:−0.0014662248 327:−0.00017874227
328:0.0024365219 329:−0.00083040918 330:0.00055475923 331:−2.3758541e−005
332:0.0013844321 333:0.00018908412 334:−4.6850397e−005 335:0.00017908432
336:0.0027642041 337:−0.00026057736 338:−0.0019368717 339:0.0012275067 340:−0.0021567047 #

APPENDIX C4

SVM Model Weights
(85; Normal/Diseased)

SVM-light Version V6.01
0 # kernel type
3 # kernel parameter - d
1 # kernel parameter - g
1 # kernel parameter - s
1 # kernel parameter - r
empty # kernel parameter - u
85 # highest feature index
138 # number of training documents
75 # number of support vectors plus 1
0.68943175 # threshold b, each following line is a SV (starting with alpha*y)
−0.0011669793294833025 1: −6.2484217 2: 2.8692274 3: 3.9726458 4: 4.5728879 5: 3.1217315
6: 1.431265 7: 0.44778323 8: 1.02934 9: −1.1082938 10: 1.1373868 11: 1.9316131 12: −0.28561696 13:
−3.060276 14: 0.38243186 15: −0.76406515 16: 1.25282 17: 0.95133108 18: 1.8977604 19: −0.33501664
20: 0.67167497 21: −0.11577946 22: 1.6258748 23: −0.61664796 24: −1.2282914 25: −1.6443142 26:
−0.90777022 27: 1.2275497 28: 1.0568956 29: 2.1236527 30: −0.26141879 31: 0.03845077 32:
−0.58085138 33: −0.78061342 34: 1.2447574 35: 0.24944715 36: −0.3606073 37: −0.23068826
38: 0.78405386 39: −0.43722236 40: 0.28527892 41: −1.2349344 42: −1.6965803 43: 0.25968778
44: 0.74408704 45: −0.11024579 46: −0.70728445 47: 1.5416214 48: 0.5093556 49: 0.50813681 50:
−0.10848369 51: −0.72595042 52: −1.0701329 53: 1.2242886 54: −0.44644347 55: 0.22465287
56: 1.0197572 57: −1.3624406 58: 0.96072525 59: −1.3194218 60: −0.52487147 61: −0.1581929
62: 0.0047937976 63: 0.096934691 64: 1.8773297 65: 1.0675534 66: −0.37953418 67: −0.30575103
68: −0.14885564 69: −0.7085318 70: −0.082562283 71: 0.71772766 72: −0.6834473 73: 0.37860462 74:
−0.3881411 75: −0.17689922 76: 0.89653313 77: 0.48991525 78: −0.13384825 79: −0.7523219 80:
−0.15887904 81: −0.72565669 82: −0.071575895 83: 0.26591104 84: −0.036035866 85: 0.11221373 #
−0.0015650989582460004 1: −5.5317745 2: −3.2781949 3: 1.4514818 4: 4.4336934 5: 0.22635397
6: 2.3636923 7: 2.9700732 8: −0.24828267 9: −2.3608406 10: −1.9967079 11: −0.73264194
12: 1.0981561 13: −1.8951033 14: 0.55268621 15: 1.5258482 16: 0.17173247 17: 0.14921966
18: 0.91354114 19: 1.1576183 20: 0.82168186 21: −0.59960753 22: −0.3806065 23: 0.036252648
24: 0.40446517 25: −0.041981112 26: 0.5394733 27: 0.10547557 28: −0.18626553 29: 0.43777582 30:
−1.2531258 31: −0.57186949 32: 0.10621319 33: 0.55403918 34: −0.30708826 35: 0.042276658 36:
−0.97170401 37: 1.5680649 38: −0.35357198 39: −0.31896117 40: 0.1885691 41: 0.14435399 42:
−0.80022198 43: 0.050054323 44: 0.21044557 45: 0.9939636 46: 0.016742287 47: −0.0084441807
48: 0.42134136 49: −1.3300655 50: 0.14887142 51: −1.5286498 52: 1.0831087 53: 0.01669452 54:
−1.0117697 55: −1.5333623 56: −0.23926201 57: 1.1092873 58: −0.30872497 59: −0.0068817809 60:
−0.08816056 61: −0.23867473 62: 0.14579196 63: 0.93483233 64: −1.314449 65: 0.67001724 66:
−0.43909997 67: −0.21468382 68: −0.029038141 69: 0.6566391 70: 0.66849053 71: −0.68139273 72:
−0.19444059 73: 1.0253628 74: −0.39257091 75: 0.16086669 76: 0.59910434 77: −0.099923208 78:
−1.3054628 79: −1.3442253 80: 1.4393352 81: 0.25903618 82: −0.08239346 83: −0.32068664
84: 0.9061048 85: −0.81428427 #
−0.0035207597532646157 1: 8.4564133 2: −3.6954048 3: −0.36950901 4: 2.0615106 5: 0.32085344 6:
−2.5327203 7: −0.28457209 8: −1.186967 9: −1.2540523 10: 2.2149053 11: −2.8718159 12: 0.93030947
13: −2.0749297 14: −0.2423725 15: −1.8521192 16: −1.5626588 17: 3.2296343 18: 0.065072417
19: 0.17800856 20: 0.73286116 21: 1.1539247 22: 1.1033744 23: 0.1072376 24: −0.81941801 25:
−1.7166369 26: −0.49180382 27: −0.88959998 28: −0.783346 29: 0.55402172 30: −0.21719469 31:
−0.38976419 32: −1.8080884 33: 0.093785204 34: −0.34544724 35: 2.3562729 36: −0.55151314
37: 1.1748444 38: 0.35242981 39: −0.68477893 40: −0.089026608 41: 0.21341442 42: 0.93687207
43: 0.044087749 44: −0.26936442 45: 1.4698968 46: −0.94894558 47: −0.20715962 48: 0.17709284
49: −0.092726924 50: −0.03063637 51: −0.053195205 52: −1.4915875 53: −0.091144487 54: 1.1582738
55: −2.4273913 56: 0.10436805 57: −0.16633649 58: −0.67621684 59: −0.74687052 60: 0.37081623 61:
−1.4236872 62: 0.54976654 63: −0.023168497 64: −0.61734682 65: 0.34305745 66: 0.54878235
67: 1.023862 68: 0.95399183 69: 0.61367548 70: 0.2599085 71: 0.75868374 72: 0.27436996
73: 0.23401526 74: −0.75373387 75: −1.3631232 76: 0.77333856 77: −0.3686007 78: −0.066425569
79: 0.82971358 80: −0.27613378 81: 0.3844921 82: 0.093253352 83: −0.62704402 84: −0.84857655
85: 0.058126319 #
−0.0035207597532646157 1: −5.7919517 2: −2.1810565 3: 0.89991498 4: 4.4267159 5: 0.42934251
6: 0.0051537198 7: 2.4697821 8: −0.77805513 9: 0.41163149 10: −2.9729836 11: −0.4103817
12: 0.5306235 13: 0.1541082 14: 0.88863766 15: 1.8568023 16: −1.138868 17: −2.3147066 18:
−1.5117507 19: 0.69398737 20: 0.65491122 21: 2.016608 22: −1.9388435 23: −0.48158178
24: 0.49413031 25: 1.759385 26: 0.56169939 27: 1.358276 28: −0.67969912 29: −0.17309627 30:

APPENDIX C4-continued

SVM Model Weights
(85; Normal/Diseased)

−0.31775782 31: 0.089694984 32: 0.026966177 33: 0.12238708 34: −0.54287702 35: 0.92235756 36: −1.1001273 37: −0.63166147 38: −0.11067349 39: 1.2273777 40: −1.2410905 41: −1.389986 42: −1.4577581 43: 0.55986434 44: −0.86515212 45: 1.1510192 46: −1.5532745 47: −0.23236232 48: 1.539893 49: −0.75711602 50: −0.37118486 51: −0.023546115 52: −1.4525793 53: 0.74840224 54: −1.3073236 55: −0.42132354 56: −0.044209357 57: 0.59822321 58: −1.0615158 59: −0.21888712 60: 0.48570648 61: 0.086135194 62: −0.55055785 63: 0.19289941 64: 1.4558742 65: 0.47681028 66: −1.5687805 67: 0.88204062 68: −0.90476662 69: 0.31320921 70: −1.8967479 71: 1.0429516 72: 0.22732769 73: 0.76303196 74: 0.99647546 75: −0.16086195 76: −0.079184987 77: −0.31307292 78: −0.28297859 79: 0.53510016 80: −0.61627305 81: 1.2682763 82: −0.86660659 83: 0.79760998 84: 0.88989186 85: 0.31910986 #

−0.0035207597532646157 1: −4.8213444 2: 1.5760788 3: −0.57018983 4: 4.005219 5: −2.8392484 6: 1.7106702 7: 9.8552361 8: 2.2270277 9: −1.4904127 10: −7.1802697 11: −3.0619631 12: −0.14209715 13: −1.4537175 14: −2.877516 15: −1.1271073 16: 0.53900164 17: −1.8657733 18: −0.53384638 19: 1.5783185 20: −0.68478709 21: 0.032381013 22: −1.4166883 23: −0.0025301133 24: −1.1854193 25: 0.62957221 26: −3.2034943 27: 0.077824026 28: 1.7398168 29: −0.01426788 30: −0.64900607 31: −0.21030807 32: 0.88778365 33: 0.076254755 34: 2.1417699 35: −0.27708969 36: 0.31239855 37: 0.70956808 38: −0.64874792 39: 0.1058379 40: −0.42606917 41: 0.72831851 42: −0.25673389 43: 0.2500523 44: −1.6403226 45: 2.1886477 46: −2.2809436 47: −0.1286744 48: −0.12771322 49: 0.68130213 50: 1.0067925 51: −0.92800182 52: 0.26234749 53: −0.089902036 54: −0.42107287 55: −1.3764564 56: −1.510673 57: −0.43247876 58: −0.68712801 59: 0.7631014 60: −0.82621932 61: 1.5242251 62: −0.56152421 63: −0.57718027 64: −0.29271552 65: −0.19943641 66: −0.54750919 67: 0.22625037 68: 0.1774147 69: −1.4245882 70: −0.1029859 71: 0.00042244355 72: 1.3596847 73: 1.0236553 74: −0.48945808 75: −0.15918885 76: −0.12789704 77: −0.1897447 78: 0.099541761 79: −0.28899437 80: 0.19369102 81: 0.60415381 82: −0.13581827 83: −0.12477767 84: −0.75226313 85: −1.41051485 #

−3.4280994110505209e−005 1: −4.1156435 2: −0.34006771 3: 8.4351921 4: −14.735023 5: 2.3358378 6: −6.4112816 7: 1.5974257 8: −3.843544 9: −9.0954008 10: 4.760253 11: −3.9502704 12: 2.7603168 13: 0.43952861 14: 5.5260024 15: 3.1865094 16: −6.4434667 17: −1.9002872 18: −6.7885156 19: 0.16282603 20: 0.52738881 21: −6.3669405 22: −1.5121588 23: 0.72735524 24: −3.7408514 25: 3.781415 26: −1.5523477 27: 3.5449743 28: −0.18590957 29: 5.2692285 30: 0.36765394 31: −3.1490333 32: −0.66037738 33: 1.007771 34: −0.61638629 35: 0.74850076 36: 1.2301011 37: −0.73134118 38: 0.83485031 39: 0.8798697 40: −1.2472433 41: 0.93989688 42: −0.71822441 43: 0.32871962 44: 0.47559053 45: −0.90758634 46: −0.18236195 47: 0.26476479 48: 0.3338339 49: 0.17463125 50: 0.71907938 51: −0.2087025 52: 0.58152407 53: 0.30969498 54: 0.79729444 55: 0.21376763 56: −0.21582489 57: 0.062268022 58: 0.20543171 59: −0.055415176 60: −0.12182273 61: 0.306467 62: −0.15245672 63: −0.50928122 64: −0.34476313 65: 0.10096245 66: 0.39556009 67: −0.60022378 68: 0.34298474 69: −0.10788257 70: 0.062733725 71: −0.12500487 72: 0.19981076 73: 0.028175019 74: 0.12437224 75: 0.062091012 76: 0.27516529 77: 0.22774903 78: −0.073975861 79: −0.27044097 80: 0.066835359 81: −0.083587073 82: 0.14524968 83: −0.28966823 84: −0.085532948 85: −0.090635799 #

0.0026466146997776037 1: −8.7888012 2: −5.0174055 3: 15.464613 4: 12.69648 5: 0.48444548 6: 4.1684113 7: −0.74741292 8: −3.0366001 9: 3.0165656 10: 0.36663359 11: 0.090890579 12: 1.0652288 13: −1.5409054 14: 0.2649897 15: −0.43269604 16: −0.038893078 17: −0.77519739 18: 0.81574935 19: −1.0314269 20: −3.2741005 21: −1.5639375 22: −0.5126884 23: 0.82985568 24: −1.0077952 25: 1.0022768 26: 0.1195637 27: 1.2333072 28: −1.1778735 29: 0.83554494 30: −0.10847708 31: 1.3086255 32: −1.6946321 33: 1.2967862 34: −0.79051191 35: 0.56799436 36: −1.7944912 37: 0.58153147 38: −3.3880858 39: 2.1127441 40: −0.35073772 41: 0.3430565 42: −0.19415511 43: 0.87412983 44: −1.4260486 45: −0.2287287 46: 0.86864233 47: −0.34647352 48: −1.0671141 49: 0.81541055 50: −1.2651246 51: 1.6905305 52: −0.76940089 53: 1.2428665 54: −0.253553 55: 0.75670892 56: 0.037519887 57: 1.3644034 58: −1.3079399 59: 0.41920772 60: −1.4656103 61: −0.38064155 62: −1.4655507 63: 0.85689932 64: −0.25574639 65: −0.94760424 66: 0.048869174 67: 0.52866745 68: 0.64850807 69: 0.541134 70: −1.4543862 71: 0.067330085 72: 0.054305743 73: −0.48869985 74: −1.1989335 75: 0.44269657 76: 0.71393716 77: −0.32942852 78: 0.4908244 79: 0.13667721 80: 0.75521457 81: −0.23717679 82: 0.74724638 83: −0.19844957 84: −0.66304415 85: 0.4589403 #

0.0035207597532646157 1: −2.6544154 2: −1.6780306 3: 0.060192857 4: 4.1504841 5: 0.24912068 6: −6.624095 7: 0.57551324 8: −0.40938711 9: 0.95585006 10: −1.6248276 11: 2.5019817 12: 0.56307358 13: 0.95418429 14: 0.88776869 15: 3.2650585 16: −0.68683743 17: −2.1359942 18: 1.4519684 19: 2.2777252 20: −0.086952887 21: 0.98849201 22: −0.43877348 23: 2.5149901 24: −0.61557049 25: −1.8795074 26: −2.9768124 27: 0.79192317 28: −0.13132951 29: −0.029296318 30: 0.93309855 31: −0.7005055 32: 0.71704352 33: −0.25660962 34: −2.2047393 35: −0.25032863 36: 0.71683908 37: −0.74325979 38: −0.43488362 39: 0.098624043 40: 0.35353583 41: 0.48026922 42: 0.35613587 43: 0.23364027 44: −0.19640292 45: −0.059701335 46: −0.36572802 47: −0.56502438 48: 0.17310216 49: 1.1000975 50: 0.49338856 51: −0.50896662 52: 0.042086825 53: 0.79794669 54: −2.1193681 55: 0.25861913 56: −0.33582497 57: −0.012439645 58: 0.20513313 59: −0.60620952 60: 0.54638368 61: −0.81247282 62: 0.62839669 63: 0.48116341 64: 0.38637295 65: −0.24869362 66: 0.84799761 67: 0.30435371 68: −0.0083769634 69: −0.36916006 70: 1.1698636 71: −0.28332841 72: −0.16254009 73: 0.60171705 74: −0.3651886 75: 0.13924569 76: 0.14928086 77: −0.22138734 78: −0.23113471 79: 0.71544218 80: −0.68907952 81: 0.25123066 82: 0.35675538 83: 0.7597639 84: −1.4002386 85: 1.2163451 #

0.0035207597532646157 1: −4.2092881 2: −2.4297073 3: 2.3812873 4: 3.7497678 5: −3.525115 6: −4.9855132 7: 6.1610827 8: 2.7601898 9: −2.8208137 10: −3.3654191 11: −0.56684256 12: 0.35663861 13: −2.660598 14: −1.8712988 15: −1.387481 16: −2.1275451 17: −0.54285592 18: −1.2628362 19: 2.989496 20: −1.130962 21: 0.9517414 22: −1.2566395 23: −0.34647283 24: 0.77426749 25: −1.3361136 26: −1.7966329 27: 0.40518939 28: −1.1118909 29: −1.0633837 30: −0.41736361 31: −0.84764743 32: 1.1794119 33: 1.6799232 34: −0.63335872 35: 1.6104892 36: −1.1103476 37: 0.63073111 38: 0.48384947 39: 0.89936668 40: −0.082325786 41: 0.76218665 42: 0.97860414 43:

APPENDIX C4-continued

| SVM Model Weights (85; Normal/Diseased) |
|---|
| −0.37083343 44: 0.59187639 45: 1.1464876 46: 1.1205767 47: −0.8635487 48: 1.3752649 49: 0.51784384 50: −0.69380736 51: 0.72513711 52: 0.21139859 53: −0.93220896 54: 0.48446506 55: 1.2326409 56: 0.69779438 57: −0.010709514 58: −1.1019911 59: −1.4584427 60: 0.24385148 61: 0.9553318 62: 0.52746499 63: 0.75839889 64: −1.0763538 65: −1.1380903 66: −0.043663036 67: 0.55343688 68: −1.0342745 69: −1.0344036 70: 0.79018819 71: −1.7690177 72: −0.66686332 73: −0.34390387 74: 1.0351527 75: −0.86768883 76: −0.31033605 77: 0.18996391 78: −0.22393461 79: 0.12826207 80: −0.28926349 81: −0.012549644 82: −1.2416493 83: −1.5032756 84: 0.082687184 85: 1.2248921 # |
| 0.0035207597532646157 1: −7.509798 2: −4.5393901 3: −2.8062258 4: 3.4199057 5: 3.2766123 6: −6.2061114 7: −3.7431328 8: 0.69338125 9: 1.6215347 10: 1.2656826 11: 2.7182131 12: −0.35331067 13: −0.94589573 14: 0.90906739 15: 0.93549758 16: 0.38136375 17: 0.90199894 18: −0.53325403 19: −1.0350369 20: 0.1937726 21: 0.45757112 22: 0.39697847 23: −0.39251831 24: 1.403145 25: −2.4881928 26: 1.5786802 27: 1.5884699 28: 0.32738572 29: 0.77424771 30: −0.48961881 31: −0.69184321 32: −0.11602285 33: 0.25669566 34: 0.45848355 35: −2.2879128 36: −0.97574413 37: 0.34878814 38: −0.32084075 39: −0.51838773 40: −0.48434633 41: 0.40164044 42: −1.2636504 43: 1.3239561 44: −0.48785928 45: 0.056154378 46: 1.0239472 47: 0.50110769 48: 0.0026843392 49: 1.1051512 50: −0.25809002 51: 0.46542385 52: 0.097595304 53: −0.8211751 54: 1.3499396 55: −0.55995923 56: −1.3507671 57: 0.88989532 58: −0.62262529 59: 1.4444965 60: −0.48785457 61: −0.5163992 62: −0.56071895 63: −0.19808592 64: 1.1346015 65: −1.5523173 66: 1.5615344 67: −0.05772467 68: −0.64757806 69: −1.8814909 70: 0.69906181 71: 0.21192646 72: −1.3310343 73: 0.59936488 74: 0.050508223 75: −0.035055101 76: −0.060202323 77: 1.5310905 78: 0.32611093 79: −1.7685404 80: −0.47976485 81: −0.17680326 82: 0.0080885431 83: −0.59574872 84: −0.47070134 85: −0.022143023 # |
| −0.0035207597532646157 1: 10.097442 2: −1.8614138 3: 1.4156544 4: 1.4052474 5: 0.31974572 6: −5.6366968 7: −2.7028873 8: −2.4760547 9: 2.5067186 10: 2.0757139 11: −2.1181877 12: −0.90601051 13: 1.0449494 14: −0.63680339 15: −1.3693681 16: −1.4672149 17: 2.2615716 18: 1.0364233 19: −0.88492882 20: 0.77747375 21: −0.23462507 22: −0.168164 23: 0.030179759 24: −1.0176415 25: 0.83552551 26: −0.99221385 27: 0.31474352 28: −1.0523298 29: 0.55194938 30: 0.16242579 31: 0.45075864 32: 0.82697576 33: −0.70048535 34: 0.77331382 35: 1.29409 36: −0.094384804 37: 0.64095533 38: −0.2618013 39: −1.0752306 40: −0.16970454 41: 0.6047948 42: 0.27205655 43: 0.83269829 44: 0.11379907 45: 0.66776836 46: −0.56533515 47: −0.43901965 48: 0.8195048 49: 0.98343772 50: −0.65349871 51: −0.019731186 52: −0.95981377 53: 0.32438889 54: 0.69812906 55: 0.20094955 56: 1.2491561 57: 0.031027239 58: 0.082117409 59: 0.30294687 60: 0.62821972 61: 2.1786509 62: 0.24057224 63: −0.22619005 64: −0.35955474 65: −0.33847553 66: 0.33624274 67: 0.44285411 68: −1.5966766 69: 0.037208516 70: −1.1043345 71: 0.57435846 72: −0.01608846 73: 0.53170288 74: 0.37930936 75: 0.31339011 76: 0.80519551 77: −0.92552328 78: 0.28643498 79: 0.40159059 80: −0.38341659 81: 0.36391017 82: −0.51450759 83: −0.63291878 84: −0.46120426 85: −0.27918485 # |
| −0.0035207597532646157 1: 7.2203302 2: −4.6925292 3: −0.71862835 4: 2.4329977 5: 0.17405996 6: −2.3858955 7: −3.6205564 8: −1.2306844 9: 0.62873197 10: 2.9880207 11: −0.4485932 12: −0.12904745 13: −0.65154469 14: 0.80697656 15: −1.029856 16: 1.529476 17: 2.8022256 18: −1.0489378 19: −0.44924599 20: −0.80383497 21: −0.25904307 22: 0.53846246 23: 0.71031916 24: −2.3672302 25: −0.91945183 26: −0.78370333 27: 0.12203253 28: 0.72611457 29: −0.22881122 30: −0.79196155 31: −0.02377972 32: 0.20235474 33: 0.21350279 34: 1.3739451 35: 0.098526865 36: 2.815995 37: −0.91403037 38: −0.5698511 39: −1.2917552 40: −1.4901602 41: −1.3911369 42: 1.7263176 43: −1.0613565 44: −0.66679603 45: −0.70240986 46: −0.8640815 47: −0.099078871 48: −1.2030772 49: 0.17561798 50: −1.004133 51: −0.090904243 52: 0.0029521906 53: −0.59214115 54: 0.60327482 55: 0.8842234 56: −0.22315407 57: 0.62547201 58: 0.95840544 59: −0.34876853 60: 0.53333133 61: −0.96676898 62: −1.5946102 63: 0.70361596 64: −1.0295923 65: −0.18397623 66: 0.10510585 67: 0.11890922 68: −1.470775 69: 1.7038034 70: −1.1788989 71: 0.71039879 72: −0.02496448 73: 1.0265777 74: 0.72668654 75: −0.24382575 76: 0.31476215 77: 0.64805585 78: 0.056707695 79: −0.032253273 80: −0.35613647 81: −0.29307088 82: −0.47884226 83: −0.031227961 84: −0.68177027 85: 0.40402326 # |
| −0.0028758957132167203 1: 3.5329537 2: −10.95813 3: 3.4194798 4: −7.8480668 5: 3.7418206 6: −3.0329297 7: −2.0779335 8: −0.86376679 9: −0.23510407 10: 2.2805333 11: −1.7733712 12: −0.88370395 13: 0.80895215 14: 4.2387309 15: −2.0776055 16: 3.0777144 17: −0.79243094 18: 0.84162772 19: −0.077937923 20: 0.28963533 21: −1.3790681 22: 1.4894168 23: 0.018758779 24: −2.0270684 25: −0.68106169 26: −7.2576551 27: −1.8796045 28: 2.9182773 29: −2.6407745 30: −2.0767155 31: 0.86707813 32: −1.6518435 33: 1.633288 34: −2.9613552 35: −4.4285808 36: −1.0467037 37: 0.41871238 38: 1.6681521 39: 1.0266926 40: 0.95897007 41: −3.4459255 42: −0.19771677 43: 1.4036087 44: 1.6188563 45: 2.5977178 46: 0.98996758 47: −0.82927483 48: 0.61392421 49: −1.1662588 50: −0.98937833 51: −0.28667507 52: −0.93937808 53: 0.97598058 54: 0.52989149 55: −0.094056919 56: −0.48669103 57: 0.83300668 58: −0.096311115 59: 0.76985174 60: −0.19955865 61: 0.70920098 62: −0.098080747 63: −0.58614087 64: −0.30448323 65: 0.43787375 66: 0.42960981 67: −0.62090302 68: 0.67657304 69: −0.28415462 70: −0.60854691 71: −0.17868806 72: 0.30537838 73: −0.17963754 74: 0.36392453 75: 0.4541378 76: 0.098703489 77: −0.14385869 78: 0.14480381 79: 0.54459673 80: −0.32749698 81: 0.5294469 82: −0.03399723 83: −0.085196897 84: 0.036676209 85: −0.032222539 # |
| −0.0032274031575531114 1: 10.264601 2: −0.059173197 3: 1.2563672 4: 0.93355006 5: 0.10213261 6: −3.12937 7: 0.1210808 8: −1.4454924 9: 2.8236961 10: 1.1237521 11: −3.9188919 12: −2.4904826 13: 2.0705259 14: −0.87547851 15: −1.8442463 16: 0.21780729 17: 2.4239211 18: 1.4910609 19: −1.729903 20: 2.1160944 21: −1.7531475 22: −0.63739741 23: 0.51525068 24: −2.1273396 25: 0.43934068 26: −1.0054997 27: −1.7345521 28: −0.25552028 29: 0.75789368 30: −1.0863563 31: 1.4560143 32: 1.7285388 33: 0.094971634 34: 0.95385522 35: −0.35644263 36: 0.83385187 37: −0.56441391 38: 0.26436624 39: −1.6112218 40: −0.29825702 41: 0.97394598 42: −0.066852339 43: 0.05723669 44: −0.2698839 45: 0.12173406 46: −0.052312899 47: −1.6940966 48: 1.4239658 49: 1.2168394 50: 1.3187749 51: −0.8759495 52: −0.22878745 53: 0.0077490155 54: 0.91228098 |

APPENDIX C4-continued

SVM Model Weights
(85; Normal/Diseased)

55: 0.33469588 56: 0.29470313 57: 0.13694796 58: −0.91457546 59: −0.60467321 60: 0.67347729 61: −0.37298837 62: 0.57097292 63: −0.22237512 64: −0.33819744 65: −0.72712189 66: −0.15334231 67: 0.11498885 68: −0.916785 69: −0.51799488 70: −0.48970297 71: −0.80190605 72: −0.031837724 73: 0.73535842 74: −0.54567927 75: 0.80711287 76: −0.38004223 77: −0.30100656 78: −0.51487565 79: −0.23349914 80: 0.84564257 81: −0.43879128 82: −0.30966088 83: 0.36664808 84: 0.50657499 85: −0.53866541 #
−0.0016056377696593623 1: 8.3293247 2: −3.9943771 3: −1.2766048 4: 1.7569972 5: 2.6435943 6: −2.9492621 7: −2.3212342 8: −2.6703773 9: 1.6562256 10: 0.99037993 11: −1.6012954 12: 0.34458488 13: 0.13430169 14: 0.21423897 15: −1.2481678 16: −0.74102271 17: 2.3277071 18: −0.68662477 19: −2.159126 20: 0.51672584 21: 0.24277323 22: 0.73280674 23: 1.1756219 24: 0.25978401 25: 0.63631743 26: 1.7079741 27: 2.0787354 28: −1.5707715 29: 0.65416503 30: 0.26913345 31: 2.2607591 32: 0.35912016 33: 0.65344459 34: 0.75340146 35: −0.57042199 36: −0.74616569 37: 0.49215052 38: −0.49467999 39: 0.41213545 40: 0.45474479 41: −0.1624404 42: −0.15442291 43: −0.006333814 44: −0.83312565 45: −0.39217919 46: −1.3772601 47: 0.84278703 48: −0.30854723 49: 0.16744663 50: 0.63391715 51: 0.039532144 52: 0.74026698 53: −0.42207003 54: −0.590087 55: −0.36480734 56: −0.69397259 57: 0.26235241 58: −0.33095819 59: 0.10752961 60: −0.31946054 61: 0.14592922 62: 0.65290701 63: 0.52099472 64: −1.0849066 65: 0.14312524 66: 0.047710914 67: 0.52469856 68: −0.45751137 69: 0.21821585 70: −0.11044776 71: 0.40490064 72: 0.34637508 73: −0.50340813 74: −0.07373298 75: −0.21722183 76: 0.55678886 77: 0.44857395 78: −0.3983981 79: −0.21097562 80: −0.21726133 81: 0.77907968 82: 0.12184522 83: −0.35409185 84: 0.42927939 85: −0.37174541 #
0.0035207597532646157 1: 4.0929852 2: 1.4835061 3: 6.1188703 4: −10.270689 5: 2.5785246 6: −3.0121825 7: 5.101213 8: 1.347518 9: −3.5204203 10: 2.21015 11: −5.8079023 12: −2.5663617 13: −0.33926055 14: 2.6436672 15: −1.0706563 16: −0.81574434 17: −3.7340477 18: 7.6981411 19: −2.4521976 20: −1.4685667 21: 0.33123419 22: −9.4077196 23: −0.35484156 24: −0.17792068 25: −3.6837096 26: 4.7119341 27: −5.0051475 28: 1.248998 29: 0.87546146 30: −1.9852268 31: −1.1443926 32: −1.4047424 33: 0.22170831 34: −0.6524421 35: 0.39878628 36: 1.2928823 37: 0.18981601 38: 1.3192978 39: −1.4391513 40: −1.0323067 41: 0.3658849 42: 0.1672495 43: 1.9239275 44: −1.1866595 45: −0.21402705 46: 0.64624435 47: 0.65488696 48: −1.2625316 49: −0.69013387 50: −0.32074571 51: 0.27624661 52: −0.064966165 53: 1.1192961 54: −0.32037497 55: 0.49531639 56: −0.92731094 57: −0.63326555 58: −0.23282745 59: 0.37688258 60: −0.067128718 61: 0.65384096 62: 0.18629821 63: −0.20528869 64: 0.18397641 65: 0.31394571 66: −0.36168703 67: 0.23028509 68: −0.41653144 69: 0.46200734 70: −0.18024899 71: −0.099146627 72: −0.84744304 73: −0.043899365 74: −0.052784499 75: −0.28761339 76: −0.30889967 77: 0.18458949 78: 0.024246849 79: −0.21060209 80: 0.19436322 81: 0.11929421 82: −0.11581916 83: −0.056519356 84: 0.04534936 85: 0.41549221 #
0.0035207597532646157 1: −0.17285712 2: 5.3579178 3: −0.74000329 4: 0.99322218 5: −6.1377206 6: 0.59887767 7: 0.042126093 8: −0.2397196 9: 1.3158681 10: 1.9585021 11: −2.8881965 12: −2.0061564 13: 0.65251106 14: −1.2070966 15: −0.58103746 16: 0.42443126 17: −0.66891319 18: 1.3253081 19: 0.98001778 20: −0.39893013 21: −0.8579973 22: 1.2817551 23: −0.42398727 24: 1.3232685 25: 0.21813056 26: −0.35450104 27: −0.12951463 28: −0.43908429 29: −1.0419377 30: −1.6454725 31: −0.12625751 32: −0.41548735 33: 0.67890793 34: −0.418008 35: 0.2621589 36: 0.049831923 37: −1.4470059 38: 1.1266959 39: 0.58603501 40: 1.4245315 41: −0.17537774 42: −1.3361218 43: 0.083461992 44: −1.5330092 45: −0.35139784 46: −0.055380493 47: 0.5069105 48: −0.65670156 49: 0.082980849 50: 1.0968806 51: −0.67249388 52: −0.45360234 53: −1.2057146 54: 1.5455887 55: 0.079480849 56: 1.4911444 57: 0.76370496 58: −0.55405068 59: −0.61118889 60: 0.36784449 61: 0.66775882 62: 0.91460311 63: 0.0053329607 64: 0.34343752 65: 1.1612324 66: 0.16291295 67: −0.19362122 68: −0.19218297 69: −1.3981386 70: −0.28877142 71: −0.51815724 72: 0.15315264 73: 0.49423894 74: −0.12288372 75: 0.37653589 76: 0.041707151 77: 0.88474351 78: −0.13657476 79: 0.23490222 80: 0.00163262 81: −0.75146848 82: 0.91966087 83: −0.22570723 84: 0.34171563 85: −0.21373966 #
0.0035207597532646157 1: 7.5575404 2: 1.2708558 3: −2.5564513 4: 2.3454616 5: −4.0419817 6: 3.6907179 7: 3.6983776 8: 0.66216749 9: 1.8481812 10: −4.4674816 11: 0.81366938 12: 2.0454063 13: 1.2286377 14: 0.79411447 15: 2.6960921 16: 2.3801267 17: −3.9791861 18: −1.2930653 19: −0.071555428 20: −1.6138343 21: 0.35226038 22: −0.16730696 23: 1.6548449 24: 0.18559873 25: 2.1241612 26: 0.31977135 27: −0.93729568 28: 1.5951219 29: 0.61639202 30: −0.88338506 31: −0.30948994 32: −1.1341227 33: 0.053725217 34: 0.55166566 35: −0.088504292 36: 1.1535082 37: −1.0387075 38: 0.47641572 39: 0.78401601 40: −0.17910491 41: 0.44150418 42: 1.0853348 43: −0.90102106 44: −0.23553529 45: −1.2330498 46: −1.1346302 47: −1.2718041 48: −0.23164549 49: 1.5911038 50: −1.3972417 51: 0.51193959 52: 0.10215104 53: 1.3947874 54: 0.50654709 55: −0.28716737 56: 0.52380943 57: −0.6641522 58: −0.4423224 59: 0.043580774 60: −0.17660081 61: −0.65470898 62: 0.54345536 63: −0.89972711 64: 1.3129793 65: −1.4059575 66: 1.1218358 67: 0.13474494 68: −0.11640819 69: −1.0111084 70: 0.22180116 71: −0.57438076 72: 0.35917073 73: −0.29428148 74: 0.77561665 75: 0.76326346 76: −0.02471507 77: −0.45806614 78: −0.38149336 79: 0.58453786 80: 0.11966577 81: 0.73335242 82: 0.11628031 83: 0.52007282 84: 0.35929218 85: −0.34161055 #
0.0035207597532646157 1: 4.4914255 2: −0.24480897 3: −2.2583835 4: 0.88322991 5: −2.5046406 6: 1.9969134 7: −0.0044047181 8: −0.26928857 9: −1.4914516 10: −1.5938169 11: 0.76435322 12: 3.0260527.13: −1.8695457 14: 1.0035132 15: 0.51201451 16: −1.4259228 17: −1.8684331 18: 0.50730628 19: 0.90998501 20: 0.74316335 21: 1.3944154 22: 0.29851213 23: 0.39861822 24: 0.86132103 25: 0.21757281 26: 0.94610828 27: 1.2375537 28: −0.34744972 29: −1.3769326 30: −1.0923102 31: −0.24452628 32: −0.025521526 33: 0.082867205 34: 0.21253513 35: −0.5278852 36: 0.95895612 37: 0.25863516 38: 1.6546474 39: −1.2401502 40: 0.82902467 41: 0.31838235 42: −1.2486559 43: −0.6841439 44: 0.22977807 45: −0.83940697 46: −0.79875743 47: 0.11707787 48: −0.17272606 49: 0.15384579 50: 0.087365143 51: 0.25894096 52: −0.15067339 53: −0.52227491 54: −1.1062934 55: 1.2150086 56: −0.64603966 57: 0.18616955 58: −0.6439392 59: 0.42169374 60: −0.56355494 61: 0.50825572 62: 0.05969793 63: 0.50939173 64: −0.44535851 65: −0.46299797 66: 0.16085759 67: −0.30113783 68: 0.13701017 69: 1.0244386 70: −0.45194241 71: −0.27729821 72:

APPENDIX C4-continued

| SVM Model Weights (85; Normal/Diseased) |
| --- |

−0.52808696 73: 0.40316921 74: −0.45404562 75: 0.6495536 76: 0.74272209 77: −0.57873446 78: −0.49307254 79: −0.58688003 80: −0.94545007 81: 0.055477004 82: −0.50724208 83: 1.0299 84: −0.17139539 85: 0.41131699 #
0.0035207597532646157 1: 4.8310957 2: −0.51966381 3: 3.2191603 4: −5.9580889 5: −3.9725423 6: 0.56513089 7: 5.1268225 8: −0.1668672 9: 0.36320001 10: −3.7878082 11: −0.10110246 12: −0.6566487 13: 5.6380572 14: 2.660486 15: −3.7514431 16: 3.8383276 17: −2.368597 18: −2.6838796 19: −0.51957881 20: −1.0350298 21: −2.689707 22: −0.040914409 23: −2.89046 24: −0.017867085 25: 2.3588343 26: 0.7256881 27: 0.82110369 28: −0.69781995 29: −2.8904381 30: −0.0058995388 31: 0.3508876 32: 0.23750982 33: −1.1175548 34: 0.65478104 35: 2.9058352 36: −1.0202932 37: 1.486963 38: 1.0728838 39: −3.0690415 40: −0.14180592 41: −2.1934268 42: −0.5380643 43: 0.7140224 44: −2.0659578 45: −0.12305688 46: 2.9920449 47: −2.1582038 48: 1.3255918 49: 1.483328 50: 0.30026016 51: 0.87408745 52: −0.61406249 53: 1.0657183 54: −1.4992493 55: −0.23971069 56: 0.43577427 57: 1.691076 58: 0.65021253 59: −0.31427428 60: 0.72341466 61: −1.265844 62: −0.10906541 63: −0.088984825 64: 0.091691613 65: −0.14957437 66: 0.71384794 67: −0.30230176 68: −0.050637566 69: −0.12429062 70: 1.6292779 71: 0.75504225 72: −0.40864852 73: −0.22019285 74: −0.15642677 75: 0.23244423 76: 0.27070737 77: −0.15731111 78: 0.30020115 79: −0.24489987 80: 0.34977928 81: 0.35565168 82: 0.19694737 83: 0.14676331 84: 0.16930567 85: −0.051620871 #
−0.0035207597532646157 1: −0.40237048 2: 3.0508842 3: −0.87237811 4: −0.24187045 5: −8.52349 6: 4.217833 7: 1.0044558 8: −0.71493214 9: 0.38238505 10: −0.80563587 11: 0.89346939 12: 2.4719095 13: 1.3058728 14: −0.975398 15: 1.7273053 16: −2.1807504 17: −4.3538771 18: −2.3977282 19: −1.7475402 20: 1.4739785 21: 0.91152471 22: 1.1646342 23: 0.61799443 24: 1.2027286 25: −0.072075672 26: −0.23120642 27: −1.5628221 28: 0.30661285 29: 0.27028155 30: −0.59216547 31: −0.37261039 32: −1.004298 33: 0.18646973 34: −0.77777117 35: −0.070579112 36: −0.52634406 37: 0.11652174 38: 0.38695204 39: −2.1880736 40: −0.5080148 41: 0.067998908 42: 0.26474997 43: 0.73836499 44: −0.67228192 45: 0.33195686 46: −0.7153669 47: 0.93102401 48: −0.88505077 49: 0.74354327 50: −1.1693422 51: −1.4053208 52: 0.26272804 53: −0.73029745 54: 0.45781791 55: 0.60853875 56: −0.29050004 57: 0.63503903 58: −0.88025033 59: −0.39223021 60: 0.16995771 61: −0.68475896 62: 1.9526094 63: 0.32150131 64: −0.7642808 65: 0.71404803 66: −0.55241185 67: −0.70457369 68: 0.39290434 69: −0.42997518 70: −0.34252283 71: 0.57953405 72: −0.17546353 73: −0.32685208 74: −0.63259292 75: 0.83298308 76: 1.148315 77: −0.34813735 78: 0.91191739 79: −0.4794181 80: −0.29130724 81: 0.4239091 82: −0.27805558 83: −0.43199664 84: −0.022172065 85: −0.487692 #
−0.0035207597532646157 1: −12.11614 2: 7.1385088 3: 3.1919744 4: −0.5384708 5: −2.1869912 6: −3.1748075 7: −0.84486699 8: −0.32319507 9: 2.3280804 10: 0.71962136 11: −0.085431561 12: −1.8759428 13: 0.50136417 14: −1.3576798 15: 1.9139546 16: −1.2165844 17: −1.3537034 18: −1.0146867 19: 1.2403105 20: 0.67722082 21: 2.3335445 22: −1.3236587 23: −1.2116036 24: −2.895117 25: 0.93300378 26: −0.81829029 27: −0.27387846 28: −2.5765381 29: 0.15226839 30: −0.44577959 31: 1.6107903 32: 1.9374447 33: −0.68141097 34: 0.75793529 35: −2.0861123 36: −0.031873871 37: −0.72435808 38: 0.17355822 39: 0.32460123 40: −0.60567987 41: −0.12146416 42: 0.77332103 43: 0.67675757 44: −2.4846942 45: −1.8086733 46: 1.400087 47: 0.81786352 48: 0.79804885 49: −0.52081394 50: −0.68013966 51: −0.8645705 52: −0.36793041 53: −0.15984587 54: −0.82175982 55: 1.6989828 56: 0.76421434 57: 0.86074358 58: −0.97666752 59: 2.2772253 60: 0.41359618 61: 0.42457017 62: 0.046061017 63: 0.60289222 64: −1.0145038 65: 0.27962157 66: −0.71596462 67: −1.4960284 68: 0.1988855 69: 0.31735668 70: 1.605931 71: 0.44322997 72: 0.86184591 73: 0.51222146 74: −0.038134608 75: −0.28676793 76: −0.42548701 77: −0.43623599 78: −0.066509075 79: 0.5596121 80: −1.1059752 81: −0.38695255 82: 0.15660313 83: −0.16217946 84: −0.055483129 85: −0.24807593 #
−0.0035207597532646157 1: −3.074358 2: 1.3200911 3: −0.80671835 4: 2.0445714 5: −2.9063234 6: −4.6124997 7: 2.0404482 8: 0.62350243 9: 0.60801113 10: −3.675019 11: 0.71826524 12: 3.6740007 13: 0.53053898 14: −0.1440471 15: 1.2151409 16: −1.9254417 17: −2.8270991 18: −1.5436376 19: 1.5189598 20: −0.13233209 21: 2.8288872 22: 1.7279948 23: 0.49313927 24: −3.4384861 25: −4.041759 26: 0.0057617472 27: −0.86247671 28: 1.3864318 29: −0.5651021 30: 1.4912993 31: 0.70514905 32: 1.1217334 33: −0.45903251 34: −2.1538389 35: −0.71733856 36: −0.31227741 37: −0.12458951 38: 0.4296701 39: −0.8281135 40: −0.099171795 41: 0.91281277 42: −0.073144831 43: −0.50181496 44: −1.4281214 45: 0.94214213 46: −0.68833256 47: 0.73023897 48: 0.99343449 49: −0.64603591 50: 0.37665179 51: 0.75236219 52: 0.20090242 53: 1.6063961 54: 0.31331399 55: −0.53897274 56: 0.33906302 57: −0.20035845 58: 0.22891816 59: −0.98087275 60: −0.19053073 61: −0.26519907 62: −2.0439668 63: −0.81633365 64: 0.26945484 65: −1.1713725 66: 0.32175192 67: −0.39676601 68: −1.2761947 69: 0.95289999 70: −0.19126898 71: −0.52938193 72: 0.29760873 73: −1.2102565 74: −0.0075565306 75: 0.19323081 76: −0.63605744 77: 1.0378774 78: −0.06476748 79: −0.48405239 80: −0.37442154 81: −0.89993054 82: 0.4111765 83: −1.0060922 84: 0.53183049 85: −0.45563287 #
−0.0035207597532646157 1: 2.682493 2: 11.122195 3: 4.206923 4: −1.4622859 5: 2.6953654 6: −2.2655728 7: 4.8538051 8: 5.8362741 9: −1.2447271 10: −0.63010204 11: 1.3284103 12: 0.62615931 13: −0.30675834 14: −0.4801302 15: 2.4601552 16: 1.1991416 17: −1.1574873 18: 0.61701268 19: 2.2572458 20: 1.4125764 21: −0.94063079 22: 0.98931623 23: −1.2553878 24: −0.67660838 25: −0.31599128 26: 0.47997627 27: −1.587342 28: −1.7354906 29: 1.3572588 30: −0.30153325 31: 0.60223311 32: 2.4844804 33: −2.4688098 34: 0.45046955 35: 1.0528731 36: −2.1922636 37: −1.2375084 38: −1.4075315 39: 0.66435403 40: −2.1051486 41: −1.0544809 42: 0.77028394 43: −0.89421213 44: −0.01773737 45: −0.47295702 46: 0.58288544 47: 0.2111946 48: 1.3527038 49: −0.080127321 50: 0.48317146 51: −1.2236339 52: 0.5580551 53: 0.85040069 54: 1.4942495 55: −1.0360185 56: −1.3499321 57: −0.0054569864 58: 0.81168169 59: 1.7660463 60: 0.27508137 61: −0.51414585 62: 0.27423105 63: 0.44076794 64: 0.010816055 65: −0.47298872 66: 0.81987906 67: −0.098804124 68: −0.46406594 69: 0.6341064 70: 0.31627035 71: −0.062214967 72: −1.4903973 73: −0.42703351 74: −0.57125616 75: −0.035451923 76: 1.1853507 77: 0.60526383 78: −0.48796123 79: 0.97815019 80: −0.68207729 81: 0.25026202 82: 0.24979776 83: 0.016412685 84: 0.11594161

APPENDIX C4-continued

SVM Model Weights
(85; Normal/Diseased)

85: 0.0089153852 #
0.0035207597532646157 1: 0.59667957 2: −11.827269 3: 0.20600793 4: −4.1515388 5: 5.5969896 6: −3.8011801 7: −0.29551542 8: −4.6395001 9: −3.4394548 10: 1.4789293 11: 0.37074792 12: −2.7612343 13: −0.040486466 14: −0.73112339 15: −1.3585581 16: 1.5774809 17: −3.180407 18: −0.29355109 19: 1.3384612 20: −5.0804014 21: 1.5053214 22: 0.73490274 23: −4.830143 24: 4.8124661 25: 0.44843206 26: −0.19545943 27: 0.24023308 28: 4.4027333 29: 5.2329941 30: 1.176523 31: 2.8222477 32: 4.0621142 33: 2.3800118 34: −3.0317044 35: 0.87739044 36: 0.41121566 37: 1.6855221 38: 0.55244011 39: −0.71052158 40: 2.5928686 41: −0.14377376 42: −0.34617746 43: −2.0218463 44: −0.3130531 45: −0.98937351 46: −0.64656675 47: 0.95119798 48: 0.55703652 49: 0.57706296 50: −0.45926842 51: −0.98095632 52: −0.11625404 53: 0.18176861 54: 0.13455464 55: −0.21698648 56: 0.51767534 57: −0.47635695 58: −0.39904693 59: 0.61882967 60: 0.057070259 61: −0.24861169 62: 0.056957696 63: 0.81587791 64: −0.013675157 65: −1.0445228 66: −0.27801517 67: 0.12983292 68: 0.27910516 69: 0.29829064 70: 0.28584638 71: 0.63583302 72: −0.17568482 73: 0.13753381 74: −0.23729491 75: −0.43226141 76: −0.11776592 77: −0.90897405 78: 0.11062974 79: −0.21575411 80: −0.048541885 81: −0.3580533 82: −0.2560235 83: 0.26640245 84: 0.28587043 85: −0.39213607 #
0.0031812890906329555 1: 9.6229353 2: −11.464231 3: 4.1598067 4: −3.3941331 5: 4.1509666 6: 1.546693 7: 4.3594489 8: 2.2675736 9: −7.5672388 10: 3.2643189 11: 7.6341481 12: −1.8415549 13: 2.2022524 14: −6.6046128 15: −1.4669977 16: −0.62688833 17: 0.30700147 18: 2.1391397 19: −0.59542352 20: −0.46061856 21: −1.7516705 22: −1.7772889 23: −1.2461953 24: −3.7455966 25: 0.93802625 26: 1.9527825 27: 1.9288 28: −0.054740768 29: −0.64815861 30: −3.302285 31: 0.8848452 32: 0.34685737 33: −4.2761202 34: −1.4045439 35: −2.5042417 36: 2.0580082 37: 1.2458475 38: −2.4746141 39: 1.3653669 40: 0.27495795 41: −0.53184092 42: 0.294159 43: −3.4988699 44: −0.36391535 45: 0.013886777 46: 0.11503884 47: −0.066243589 48: 0.51242113 49: −1.2058492 50: −0.65748274 51: 0.010243749 52: −1.0761719 53: −0.025190989 54: −0.5794028 55: −0.11958646 56: −0.076222733 57: −0.96427655 58: −0.40716705 59: −1.8620995 60: 0.48778456 61: −0.11708479 62: 0.12640536 63: 0.16012475 64: −0.44476369 65: −0.38889754 66: −0.53000444 67: 0.27671438 68: 0.23756695 69: −1.3401867 70: 0.16650194 71: 0.61802739 72: −0.093269974 73: −0.28750378 74: 0.44459164 75: 0.44572949 76: 0.39498365 77: 0.36121634 78: −0.29221752 79: 0.11955436 80: −0.26415828 81: −0.062166933 82: 0.01595111 83: −0.31023872 84: −0.49856728 85: −0.073556148 #
−0.00036511409167891862 1: −8.2891655 2: −0.42698517 3: 7.9929414 4: −21.96343 5: −2.5162337 6: −2.332407 7: −3.5282142 8: −10.863458 9: 2.4572353 10: −9.3228836 11: 1.7616936 12: −1.5003358 13: −5.9558101 14: −5.6671357 15: 1.9989141 16: 0.0007951344 17: 2.2202916 18: 1.6051667 19: −0.46657437 20: −0.14883198 21: 0.32293826 22: 1.809746 23: 0.50881672 24: 0.20460126 25: −0.99105644 26: 0.68109101 27: 0.21133116 28: −0.1266762 29: −0.35163447 30: −0.48319864 31: −0.44588166 32: −0.81961346 33: 0.4458102 34: 0.25585374 35: 0.22169833 36: 0.50088394 37: −0.18526353 38: −0.57342333 39: −0.4100264 40: −0.49656498 41: −0.048766967 42: −0.27916297 43: −0.21427028 44: 0.23489569 45: −0.055255346 46: 0.14571071 47: −0.38773367 48: 0.24204808 49: −0.025501506 50: 0.22812733 51: 0.016479289 52: 0.0047244946 53: −0.10513508 54: 0.0340891 55: −0.11792875 56: 0.014585208 57: 0.10346211 58: 0.086079985 59: 0.13638112 60: −0.029077984 61: −0.066002205 62: −0.0022148392 63: −0.051324606 64: 0.23397739 65: 0.030481266 66: 0.039421767 67: 0.14640144 68: 0.054071993 69: −0.018368751 70: −0.0066018607 71: 0.13411276 72: 0.026797809 73: −0.10997321 74: 0.010199982 75: 0.1154227 76: −0.065298446 77: −0.0083012516 78: −0.037069004 79: 0.10039674 80: 0.071657665 81: 0.12727965 82: −0.11805948 83: 0.00066952186 84: −0.054706763 85: 0.091746822 #
0.0035207597532646157 1: 3.5839531 2: −5.883049 3: −4.1707263 4: 2.668844 5: −0.41040224 6: −0.95485866 7: −0.55179292 8: −1.9773617 9: −0.17881806 10: −1.001881 11: 2.653228 12: 1.7653873 13: −0.3574464 14: 0.60210371 15: 0.91023183 16: 1.1576729 17: −0.5881654 18: 0.7762832 19: 1.5496694 20: −0.84777153 21: 0.53634214 22: −0.85376447 23: 0.56399333 24: 0.27470717 25: 0.43654314 26: −0.068430081 27: −0.01878595 28: −0.35401875 29: 0.97802097 30: 1.0260972 31: 0.090353049 32: −1.5823214 33: −0.66183901 34: −0.35473683 35: 0.31219536 36: 1.321782 37: −0.10658298 38: 0.37130693 39: 0.95498109 40: −0.42194906 41: −0.38221079 42: 0.77177846 43: −0.016424144 44: −1.3272197 45: 0.0035217868 46: −0.090253808 47: 0.04113742 48: 0.11804217 49: −1.9058766 50: 0.72675604 51: −1.0927874 52: −0.49189433 53: −0.69180405 54: −0.091230541 55: −0.85680449 56: −0.49585167 57: 0.26901877 58: 0.75938016 59: 0.84990495 60: −0.24252474 61: 0.37672266 62: 0.53485793 63: 0.43563795 64: 0.43031749 65: 0.64165699 66: 0.38401568 67: 0.11291075 68: 0.63343042 69: 0.41156557 70: 0.75446075 71: −0.38473544 72: 0.56635094 73: −0.46696714 74: −0.70581251 75: 0.023400884 76: −0.41346964 77: −1.430331 78: −0.42817894 79: 0.2327694 80: 0.26672408 81: 0.20924288 82: 0.30024919 83: −0.29518965 84: 0.10202514 85: 0.72934097 #
0.0035207597532646157 1: 3.9010017 2: −5.5965748 3: −3.4673359 4: 3.8046615 5: −0.80037314 6: −2.4926233 7: −0.65297276 8: −1.2992364 9: 0.5986374 10: −0.76736987 11: 1.0571005 12: 0.28337967 13: −1.2857354 14: −0.26973414 15: −1.2984749 16: 2.5997679 17: −0.13204159 18: 0.39124656 19: −0.49126437 20: −1.188978 21: −0.021166831 22: 0.5348773 23: −0.33920935 24: 0.28458688 25: 0.99250501 26: 0.56726456 27: −0.045532424 28: 0.12138137 29: 1.0281024 30: −0.11518206 31: −0.46092334 32: −0.71239334 33: −0.41137099 34: −0.0074320761 35: 0.15266328 36: 1.4160883 37: −0.65966898 38: 0.60130179 39: 0.13380145 40: −0.32677779 41: −1.4254662 42: −0.070341729 43: 0.86671621 44: −0.063052483 45: −1.248728 46: 0.96862358 47: 0.67674959 48: −0.089700386 49: 0.34273475 50: −0.34479642 51: −0.032356691 52: 0.50782025 53: −0.45508158 54: 0.41873366 55: −1.5648514 56: −1.130119 57: 0.62267995 58: −1.7532282 59: 0.35311949 60: 0.10332357 61: −0.52477038 62: −0.49120677 63: −0.78596723 64: −0.048472244 65: 0.14055537 66: −0.39380437 67: −0.063648462 68: 0.15314686 69: 0.33958638 70: 0.32310656 71: −0.77177393 72: 0.29027194 73: −0.35018161 74: −0.043229166 75: −0.34670517 76: 0.21358065 77: 0.00060069456 78: −0.3655521 79: 0.79942805 80: −0.76392227 81: 0.084121495 82: 0.54889029 83: 0.81910717 84: 0.56165129 85: 1.4063003 #
−0.0015279378434102139 1: 8.6169634 2: −14.909825 3: 4.5661917 4: −14.234359 5: −3.8803411

APPENDIX C4-continued

SVM Model Weights
(85; Normal/Diseased)

6: 8.3793383 7: 1.91558 8: 2.890739 9: 3.0715823 10: −3.6336942 11: 5.559761 12: −6.221118 13: 7.0444469 14: 11.942661 15: −3.5210028 16: 3.0451481 17: 0.8645637 18: 0.90090793 19: 3.8014674 20: 3.3772614 21: 4.4967599 22: 1.2317743 23: −4.7559361 24: −1.5627382 25: −1.5317196 26: −1.1812898 27: 0.70844483 28: −3.8020139 29: 1.3617872 30: −1.9134895 31: −1.6170208 32: −0.33920389 33: 2.4329834 34: 0.17155254 35: 0.18837711 36: −0.27561921 37: −0.36969551 38: −1.4717805 39: 0.4519023 40: −0.55164379 41: 2.1655481 42: 0.56525373 43: −0.60632938 44: 0.23338282 45: −0.43923751 46: −1.0631796 47: 0.89960551 48: −0.81924933 49: 0.16573533 50: −0.36088058 51: −0.17395359 52: 0.81688082 53: −0.45888543 54: 0.19650544 55: −0.069430716 56: −0.062226437 57: −0.5745849 58: −0.068097599 59: −0.12771016 60: −0.053144429 61: −0.34997377 62: −0.18044128 63: 0.26831853 64: 0.17465159 65: 0.0027803043 66: −0.33679929 67: 0.26543939 68: −0.37960342 69: −0.26108712 70: −0.32440886 71: −0.050954357 72: 0.1843335 73: 0.054415613 74: −0.39490819 75: 0.12460218 76: −0.060419071 77: 0.20380537 78: 0.16639464 79: 0.25643727 80: 0.089747302 81: −0.075347483 82: 0.46585262 83: −0.1707512 84: 0.21907172 85: 0.048297625 #
−0.00025525531194609907 1: 12.672485 2: −7.516613 3: −4.2664714 4: 2.3894684 5: −1.9428385 6: 4.471509 7: 1.2204065 8: −1.250452 9: −0.63588476 10: −2.9151223 11: 1.88151 12: 0.55072552 13: −0.24201356 14: 1.4921519 15: 4.6928411 16: −1.2068832 17: −1.4440265 18: 2.1307447 19: −0.056857955 20: 0.72109979 21: 0.98974639 22: 0.18897299 23: 0.70602745 24: −1.4431446 25: 1.2278879 26: −0.92486399 27: −0.64960492 28: 0.42849684 29: 0.57922465 30: 0.13556732 31: 0.04900476 32: 0.78963053 33: −0.3302474 34: 1.5677528 35: −0.25550574 36: −0.019869922 37: −0.33791691 38: −0.53458244 39: −0.43368188 40: 1.0035195 41: −0.61409533 42: −1.4128333 43: 1.3993968 44: −0.30553368 45: 0.3655259 46: 1.4206858 47: −0.82553267 48: 0.17962474 49: −0.0064832438 50: −0.17397274 51: 0.60829043 52: 0.30540645 53: −0.36179671 54: 0.2895571 55: 1.2090135 56: −0.69002241 57: −0.37445688 58: −0.81388384 59: −0.9509446 60: −1.4237492 61: 0.69672018 62: −0.40041146 63: 0.13335143 64: −0.22215128 65: −0.31002694 66: 0.86585885 67: 0.90976191 68: 0.70821398 69: 0.20594257 70: 0.28823617 71: 0.41324094 72: 0.44531196 73: −0.38454822 74: 0.423778 75: −0.34325457 76: −0.054807279 77: 0.64922255 78: −1.0403811 79: −0.23182102 80: 0.87733185 81: −1.3414996 82: 0.059485011 83: 0.28990865 84: 0.58551192 85: −0.070296429 #
−0.0035207597532646157 1: 2.8188708 2: −6.6911874 3: −1.9094163 4: 3.7313151 5: 2.2988858 6: −4.5035233 7: 3.6753259 8: 1.7877527 9: −0.5697372 10: −3.8303387 11: 0.54380357 12: 0.98700315 13: −2.3476851 14: 0.22088082 15: −0.25059032 16: 1.7471974 17: 1.6776427 18: −0.41471028 19: −0.1232703 20: −0.28474811 21: 0.86388719 22: −1.7560869 23: −0.21651681 24: 1.5879062 25: 2.5298426 26: 0.18274429 27: 0.93223476 28: −0.68994981 29: 0.58218873 30: −0.33872893 31: 0.060827699 32: −0.68644226 33: 0.32874823 34: 0.45281684 35: −0.79672253 36: −0.75384116 37: −1.4258924 38: 0.48256019 39: 0.79279554 40: 0.2963959 41: −0.28191131 42: −1.4866642 43: 0.39201823 44: −0.014203273 45: 0.7232601 46: −0.28205287 47: −0.18092456 48: −0.13885227 49: −1.136531 50: 0.62042958 51: −1.1368109 52: −1.3643904 53: −3.218905 54: 0.85185713 55: 1.6619301 56: −1.2445153 57: −0.015923033 58: 0.56667179 59: 0.14499521 60: 1.221099 61: 0.59760261 62: −1.1682231 63: −1.0689197 64: −0.12711421 65: −0.28777412 66: 0.16776499 67: −0.4115392 68: −0.82982016 69: 0.2006533 70: −0.17664079 71: 0.083957829 72: −1.1858773 73: 0.47938693 74: −1.1153183 75: 0.059068814 76: −0.14203176 77: 0.28411403 78: 0.081551403 79: 0.12319593 80: 0.40994462 81: 0.43776467 82: 0.45384017 83: 0.15771131 84: −0.59814417 85: −0.031907167 #
0.0032004405585445671 1: 2.6485436 2: −0.39832091 3: 3.7447002 4: −2.1478522 5: −5.6797609 6: −5.3180451 7: 0.0458709 8: −0.33030915 9: 1.79348 10: −1.4856584 11: 1.9551603 12: 0.15802991 13: 2.1567461 14: 1.0581138 15: 0.24001168 16: 0.21704598 17: 0.36217123 18: −1.7393889 19: −0.86479646 20: 0.28050035 21: −0.62279636 22: 0.46538505 23: −1.2491378 24: 0.49455559 25: 3.2503259 26: 2.6528273 27: −0.90466022 28: 2.0810993 29: −1.800808 30: −0.65186924 31: 1.1478062 32: −1.1883457 33: −1.9486394 34: −0.40922812 35: 1.3789246 36: 0.44635722 37: −0.52121764 38: 0.59901804 39: 3.750737 40: 0.50481492 41: −1.0930679 42: −1.0418009 43: 2.3580823 44: 0.41928837 45: 0.43175229 46: −1.7687958 47: 1.5241576 48: 0.047912914 49: −0.011029373 50: 1.999184 51: −1.5378287 52: 0.81118917 53: −0.59545577 54: −1.478533 55: 0.2204963 56: 0.21527496 57: −1.5467908 58: 0.040827062 59: 0.088919461 60: −1.1570362 61: −1.1377196 62: −0.35034156 63: −0.27653784 64: −0.89409906 65: −0.82165486 66: −0.084878348 67: 0.71434367 68: −0.84567839 69: −0.036878616 70: 0.38060263 71: −0.40381098 72: −0.46761507 73: 1.3047739 74: −0.26679948 75: −0.76907367 76: −0.60177022 77: 0.047061063 78: 0.65042329 79: 0.55717415 80: 0.1702593 81: −0.30285549 82: 0.35264146 83: −0.40650514 84: 0.22974481 85: −0.19868746 #
0.0020736580573559255 1: −1.3733028 2: 0.68064439 3: 7.460279 4: 5.9247279 5: −1.6578373 6: 0.2775822 7: −24.075966 8: 11.05617 9: −14.703788 10: −13.254814 11: −6.6166501 12: −4.9200807 13: 6.9956851 14: −2.1158919 15: 0.052510254 16: 1.4040208 17: 0.6028744 18: −0.2575106 19: −1.8322359 20: 0.60171747 21: 0.94980544 22: −1.0066327 23: 0.71674079 24: 0.54565024 25: 0.33633724 26: −0.38488925 27: 0.34494358 28: 0.48877886 29: 1.5505414 30: 0.72180462 31: −0.16976073 32: −0.75829542 33: −0.55314094 34: −0.41896018 35: −0.27545577 36: 0.19334559 37: −0.76371801 38: 0.35365519 39: 0.11516842 40: −0.19414537 41: −0.19628513 42: 0.1318195 43: −0.31227034 44: −0.14665678 45: 0.197209 46: 0.035161458 47: −0.55002463 48: −0.14159618 49: 0.21202643 50: −0.17859973 51: −0.023498023 52: −0.042595364 53: −0.074978627 54: −0.056567062 55: 0.026178882 56: 0.2204465 57: 0.13098165 58: −0.08143688 59: −0.0015269634 60: 0.0031346004 61: 0.1256801 62: 0.042953506 63: 0.23303264 64: 0.017880833 65: 0.12163436 66: −0.4547798 67: 0.087979041 68: 0.21580996 69: −0.067932546 70: 0.31557688 71: −0.20528316 72: −0.084230073 73: −0.16125476 74: 0.060367841 75: −0.1926917 76: 0.43555477 77: 0.083085731 78: −0.28572324 79: 0.17345585 80: −0.11412895 81: −0.14141244 82: 0.31385398 83: −0.21436949 84: 0.056894932 85: 0.086059354 #
0.0035207597532646157 1: 0.59482116 2: 0.49655741 3: −0.84351039 4: 0.95068574 5: −4.0811591 6: −1.6533675 7: −4.1306829 8: −0.31580341 9: 1.3122809 10: 2.5053549 11: 1.1380405 12: 1.6289359 13: −0.9442184 14: 0.22938868 15: −1.1697842 16: −0.82826602 17: 0.10561418 18: 0.46374807

APPENDIX C4-continued

| SVM Model Weights (85; Normal/Diseased) |
|---|
| 19: 0.66422725 20: 0.77281559 21: 1.1046627 22: −0.6667912 23: −1.117923 24: −0.25013828 25: 0.26400575 26: 1.502566 27: −0.40917194 28: 1.3861501 29: −0.38779527 30: 1.9878159 31: −0.58013052 32: 1.4944628 33: −1.0788684 34: −0.68354863 35: −1.2108407 36: 0.73782116 37: −0.37877095 38: 0.56748658 39: −0.71442455 40: 0.35037532 41: 0.92144632 42: −0.76375842 43: 0.26950735 44: −0.46418089 45: 1.2684388 46: −1.2894572 47: 0.38453567 48: 0.77755392 49: −0.10420168 50: −1.4918073 51: −0.25433838 52: 1.6992041 53: 0.88712889 54: −0.22789903 55: 0.050006922 56: 0.15781982 57: 1.0430646 58: 1.4553399 59: 0.30592921 60: −0.82809275 61: −0.5042758 62: 0.82383734 63: −0.17589451 64: 0.057196233 65: −0.19309768 66: −0.15504383 67: 0.9045462 68: 0.84916884 69: −0.75964236 70: −1.1753159 71: −0.14933059 72: −1.0553643 73: −0.49198627 74: −0.11928473 75: −0.14321804 76: 0.39056829 77: 0.14312863 78: −0.16039832 79: 0.37343377 80: −0.10230464 81: 1.5838434 82: 0.73417324 83: −0.8083868 84: −0.4950597 85: −0.06964846 # |
| 0.0030221398364785441 1: 3.5110908 2: 5.6174746 3: 2.5606756 4: 2.5834703 5: −7.6688213 6: −1.8434024 7: 0.36071539 8: −0.45174024 9: 2.6003997 10: 0.5911482 11: −0.69220406 12: −2.2800779 13: 1.8533925 14: −2.5804775 15: −1.1866112 16: −0.066687576 17: −1.5089196 18: −0.10368342 19: −0.087623782 20: −1.4943944 21: −0.86205274 22: 0.7565676 23: −0.6693539 24: −0.71513188 25: 1.2250738 26: 0.0098061906 27: −0.40017042 28: −1.8319592 29: −0.0011238796 30: −1.8154995 31: 0.2129721 32: −0.13248554 33: 1.5796499 34: 0.19158417 35: 0.85793179 36: −0.3565852 37: −1.0822763 38: 0.4891347 39: −0.13301478 40: 0.34163928 41: 0.06102673 42: −0.069330193 43: −0.16624564 44: −0.48438731 45: 1.4786725 46: −1.8397158 47: 0.69001108 48: 0.91062814 49: 0.020527706 50: 0.13495424 51: −0.19287805 52: −0.74348158 53: −0.49106395 54: 0.66449344 55: 0.35523808 56: 0.55576336 57: −0.49555805 58: 1.5226892 59: −0.17116992 60: 0.67154306 61: 0.10370273 62: 0.33758521 63: −0.30460584 64: 0.49617913 65: −0.24739511 66: 0.73925906 67: −0.47236478 68: 1.2099721 69: −0.032575484 70: −0.45242611 71: 0.057035528 72: −0.46597356 73: −1.9234182 74: 0.66382247 75: −0.52942693 76: −0.1035816 77: 0.54878628 78: −1.7526437 79: −0.62102193 80: 0.47183159 81: 0.064084068 82: −0.35465324 83: −0.56368434 84: 0.20363657 85: 0.86101019 # |
| 0.0035207597532646157 1: −1.2529821 2: 1.393857 3: −0.40100932 4: 0.80536771 5: −1.3698692 6: −4.2985444 7: −1.2300457 8: −1.6063071 9: 1.3245063 10: 2.534188 11: 0.30171067 12: −0.74766284 13: 3.4337008 14: 0.50606573 15: 4.3205433 16: 0.94489902 17: −1.1800903 18: 0.30085227 19: 2.3550503 20: 0.028076174 21: 0.092185527 22: −0.054449778 23: 1.274248 24: 0.50065464 25: −1.1810657 26: 1.0509241 27: −0.37393656 28: 1.4507658 29: −1.8970845 30: 1.2786201 31: 0.26944366 32: −0.44957161 33: 0.55799627 34: 0.42565152 35: −0.50317258 36: 1.2242279 37: −0.90718025 38: −0.22057383 39: 0.89371914 40: −0.96436113 41: 0.072177835 42: 0.12445948 43: −1.6282943 44: 0.078577504 45: −0.27634692 46: −0.035018735 47: −0.74332857 48: 0.69187576 49: −0.74214166 50: 0.72583973 51: −0.18807527 52: 0.55824578 53: −0.5105381 54: 0.34671339 55: 0.23379517 56: −0.01904987 57: 0.84335953 58: 0.42913693 59: −1.2054484 60: −0.043084856 61: 0.37992552 62: 0.095283762 63: 0.82956094 64: 0.10494255 65: −0.31794438 66: −0.87085748 67: −2.1185856 68: 0.28819486 69: −0.10490542 70: 0.77444106 71: 0.21397087 72: 0.04484868 73: −0.1544427 74: −0.72419685 75: 0.13790646 76: 0.015397458 77: −0.66600096 78: 1.1760044 79: 0.48632273 80: 1.5986381 81: 1.1003675 82: 0.19111913 83: −0.58480859 84: −0.2775254 85: 0.275657 # |
| −0.0035207597532646157 1: −0.60706848 2: −0.56179869 3: −2.8295784 4: 2.1079314 5: −2.16576 6: −1.5902358 7: −3.8995321 8: −1.391099 9: 1.3323318 10: 2.3022547 11: −0.15200429 12: −1.7236745 13: −0.28189707 14: 0.092928797 15: 0.5678165 16: 0.16910324 17: −1.7369378 18: 1.1536523 19: 0.4399763 20: 0.94320494 21: −1.0564628 22: −0.40919417 23: −2.1857901 24: 0.065937854 25: 0.19628744 26: 1.2588513 27: 1.2625566 28: 0.59739804 29: −1.7135398 30: 0.37543643 31: −1.0696378 32: 1.652465 33: −0.32052153 34: 0.4178119 35: 0.82741022 36: 0.23162919 37: 1.2215804 38: 0.47287229 39: 0.669622 40: −0.10720342 41: −0.34346694 42: −0.44582871 43: −0.1102373 44: 0.1677283 45: −1.2041866 46: −0.97990817 47: −2.2895584 48: −0.11250075 49: −0.8322044 50: −0.024652796 51: −1.3362759 52: −0.14697382 53: −0.081530415 54: 0.65578473 55: 0.84578443 56: 0.124378 57: −0.048972573 58: 0.0070974482 59: 0.73587078 60: −0.97483116 61: 0.19108705 62: −0.75764817 63: 0.017253783 64: 0.37827864 65: −0.21863103 66: −0.42593646 67: −0.52796865 68: 0.62855148 69: 0.14516357 70: 0.16399099 71: −0.28082269 72: −0.035006855 73: 0.21659459 74: 1.3164793 75: −0.17866343 76: 0.24791805 77: 0.62605935 78: 0.45940989 79: 0.69573057 80: 0.71832937 81: −0.42727691 82: −0.32615939 83: −0.28442365 84: −1.3224995 85: −0.47572079 # |
| −0.0035207597532646157 1: −6.5375977 2: 2.1123948 3: 1.1355326 4: −2.3440728 5: −0.40250897 6: −5.1222434 7: 2.0590734 8: 0.87406713 9: −0.42407495 10: 1.3824636 11: −0.80428976 12: −1.7772833 13: 6.3438635 14: 2.1855338 15: 2.9639337 16: 0.69173807 17: −0.41536355 18: −1.5802912 19: 1.2215521 20: 2.8985655 21: −0.068783447 22: 3.3010855 23: 0.2179627 24: 4.0880098 25: 0.94239813 26: 4.1142564 27: 2.5587342 28: 3.4989934 29: −1.4943497 30: −1.0253848 31: 1.2891228 32: 0.19311364 33: −1.4917337 34: −0.40490827 35: 1.2551166 36: 1.0866218 37: 2.749121 38: −0.95984066 39: −1.5400003 40: −1.4382766 41: 1.1438725 42: 1.8228887 43: 0.45887417 44: 1.3158252 45: 1.8924459 46: 1.5149728 47: 0.47897026 48: −1.0465672 49: 0.049777627 50: 1.819648 51: 0.14531961 52: −0.031018037 53: 0.33217061 54: 1.054731 55: 0.38953736 56: −0.84029639 57: 0.49298248 58: −0.39699548 59: −0.70166439 60: −0.95547146 61: 0.74615616 62: −1.2175609 63: −0.09551914 64: −0.040590521 65: 1.4343472 66: 0.17118558 67: 0.16519417 68: 0.11700103 69: 0.058235288 70: −0.86078101 71: −0.27289188 72: 0.58181089 73: −0.85354793 74: 0.15490662 75: −0.460251 76: −0.82907426 77: 0.016911654 78: −0.27042994 79: 0.7150737 80: −0.3998346 81: 0.17056635 82: −0.16897039 83: −0.21618274 84: 0.026753411 85: 0.079761699 # |
| −0.0035207597532646157 1: −1.3632743 2: −1.9445323 3: 0.65233999 4: −0.58333957 5: −2.1690819 6: −1.557755 7: −3.9043965 8: −0.30472508 9: 0.2361026 10: 0.85410559 11: 3.0135179 12: 0.60649604 13: −1.2247649 14: 0.6844058 15: 0.44654614 16: −1.1434579 17: 0.58581215 18: −0.4943729 19: 2.888381 20: −1.4632667 21: 0.035331994 22: 0.34741896 23: −1.0578666 24: −1.6146865 25: 1.7983127 26: 0.18128556 27: −1.9081653 28: 2.5913491 29: −2.3153069 30: 0.58279341 31: |

APPENDIX C4-continued

SVM Model Weights
(85; Normal/Diseased)

−1.00468 32: 1.4105986 33: 0.32527116 34: 1.7262596 35: −0.7636652 36: −0.6239388 37: −1.2229923 38: 0.92973059 39: 1.2896794 40: −0.54387486 41: 1.815182 42: 1.2686126 43: 0.026493588 44: 0.13799661 45: 0.038556926 46: 1.6906935 47: 1.5857954 48: −0.63974899 49: −0.19294812 50: 0.36613348 51: 2.5498624 52: −0.62005687 53: 0.41496003 54: 0.48494276 55: 0.018885197 56: −0.24577679 57: −0.0083116852 58: −0.62871617 59: 0.81586206 60: 0.94185793 61: −1.1134834 62: 1.7222621 63: 0.96535265 64: −1.1845593 65: 1.0662568 66: 0.74076414 67: 1.2916409 68: −0.3489947 69: −1.1012481 70: −0.31059921 71: 0.12768701 72: −0.8858223 73: 0.7715655 74: 0.89574414 75: −0.61715019 76: 0.54230756 77: −1.045996 78: 0.67768413 79: −0.73282576 80: 0.23836881 81: 0.13851836 82: −0.30754682 83: 0.015328793 84: −0.28529775 85: −0.51043022 #
0.0035207597532646157 1: 3.6875272 2: 3.0250661 3: 0.29052538 4: 1.6621389 5: −1.077208 6: −1.4265242 7: 5.6980257 8: 2.4122481 9: −0.23186241 10: −3.5392511 11: −0.22240373 12: 0.3499389 13: −0.74368799 14: −0.38710013 15: −2.0126009 16: −1.6567438 17: 0.18400183 18: 2.4745722 19: 0.029114984 20: −0.20238526 21: 0.36805978 22: 1.5960912 23: 0.6498906 24: −1.1362889 25: −0.62198257 26: 0.18703945 27: 1.2769275 28: −0.82102513 29: 1.5383286 30: 1.641359 31: −0.11083211 32: −0.73535907 33: 0.12018158 34: −1.9625522 35: −0.033817839 36: −0.69495207 37: 0.84588385 38: −0.34971488 39: 0.27114922 40: 1.1997342 41: −1.5652107 42: −0.71289748 43: −0.47851917 44: 0.85789436 45: −0.94423765 46: 0.032212444 47: 0.23876941 48: −2.2591531 49: 0.65750432 50: 1.5780753 51: 1.9137375 52: 0.07368347 53: 0.069766484 54: −0.38831636 55: 1.0103614 56: 0.64284617 57: 0.26976886 58: −0.3094748 59: 1.0858464 60: −0.38908195 61: −1.7455355 62: 0.42903882 63: −0.42164421 64: −1.0976751 65: 0.47146344 66: −1.7880417 67: −1.6078222 68: −0.31294608 69: −0.4832885 70: −0.69922173 71: −1.3377334 72: −0.26947746 73: 0.7479955 74: 0.045744106 75: 0.10229278 76: 0.30118969 77: 0.6811837 78: −0.45769265 79: 0.27169511 80: 0.44472837 81: −0.29408213 82: −1.1094222 83: 0.3666563 84: −0.045561716 85: 0.18670417 #
0.0035207597532646157 1: 10.933654 2: 6.4248862 3: 3.2384374 4: 0.14409828 5: 2.0443769 6: −0.96650457 7: −2.7591114 8: 3.8425102 9: 1.286938 10: −2.7674775 11: 4.7782588 12: 2.5789647 13: 0.5836091 14: 0.25201192 15: 2.1731467 16: −1.2429184 17: −2.0514996 18: −0.21137145 19: 3.2398725 20: −0.54532427 21: −0.87394041 22: −1.0946345 23: 0.33414531 24: −0.46712443 25: 0.761127 26: 0.69790411 27: −0.95681322 28: −1.1794156 29: −0.8807224 30: −1.3876348 31: 0.28623164 32: 0.90492404 33: 0.48581135 34: 0.92738605 35: 0.39698663 36: 0.48640934 37: 0.40271929 38: 0.89204979 39: −1.2035446 40: 1.3811755 41: −1.0077406 42: 0.095975496 43: 0.081236303 44: −0.27388161 45: 0.43766725 46: −1.2321532 47: 0.5831117 48: 0.12279975 49: −0.31562462 50: 1.7708108 51: −0.088413909 52: −1.2922177 53: −0.42708319 54: 1.741316 55: −0.46906748 56: −0.091270804 57: 0.66427916 58: 0.14182013 59: −0.056508265 60: −1.7402322 61: 0.27224803 62: 1.1451247 63: −0.65408528 64: −1.0457289 65: −0.051288955 66: −0.80570686 67: 1.0002974 68: 0.42793864 69: 0.51741147 70: 0.47157639 71: 0.59070158 72: −0.16071473 73: −0.089933135 74: −0.33037904 75: 1.2456383 76: −0.6323474 77: 0.48095614 78: 1.2343533 79: 0.13654871 80: −0.73044246 81: −0.41132534 82: −0.18622157 83: 0.49650639 84: −0.74608111 85: 0.91862726 #
0.0035207597532646157 1: −0.40706003 2: −7.1397123 3: 2.6859665 4: −7.0096903 5: 3.0317152 6: −4.3316078 7: 1.4683849 8: −2.7222147 9: −2.3974659 10: 1.5284376 11: −2.2683592 12: −1.688279 13: −0.69580024 14: −0.165719 15: −0.095550545 16: −0.76551509 17: −3.3442504 18: 0.72300565 19: 3.3406658 20: 0.19809642 21: −1.6887234 22: −2.3278005 23: −1.3378291 24: 3.505214 25: −1.6693422 26: −3.1288674 27: 2.3521557 28: 0.59533548 29: −1.276844 30: −0.11495301 31: 4.1659765 32: −1.3004161 33: −5.8988891 34: 2.8472443 35: −0.29545334 36: −4.1669316 37: −2.3669634 38: 2.4650891 39: 0.46121722 40: 1.6261921 41: 2.2180104 42: 1.5175546 43: −0.25555608 44: 0.84000587 45: −0.069663025 46: −1.3411472 47: −0.33703804 48: −1.6543316 49: 0.025696442 50: −0.70928001 51: 1.2521927 52: 0.80985659 53: −0.25006622 54: 0.75404704 55: −0.097098581 56: 1.020278 57: 0.80506575 58: 0.20001346 59: 0.030074423 60: −0.25281274 61: −0.50338525 62: −0.038949292 63: −0.12667872 64: −0.23509546 65: −0.10394531 66: −0.68150729 67: 0.32079381 68: −0.017649971 69: 1.0972716 70: −0.062842958 71: 0.067879252 72: 0.62627828 73: −0.29855132 74: −0.07247974 75: 0.33787322 76: 0.40759748 77: 0.69339627 78: −0.27269831 79: −0.29921198 80: 0.3968524 81: −0.082895368 82: −0.020286532 83: 0.31697649 84: 0.13875051 85: 0.32336545 #
−0.0035207597532646157 1: 5.5017767 2: 0.76866108 3: 3.5021136 4: −3.4441924 5: −1.7227199 6: −2.3480663 7: 5.2186608 8: 2.0708718 9: 1.1557996 10: −2.8974543 11: −1.7903497 12: −1.0666572 13: 1.2271978 14: 1.5467659 15: −3.7293766 16: 2.8392794 17: 1.2993569 18: 2.5210259 19: −1.9889575 20: 1.5789289 21: −2.0791085 22: −0.16521527 23: 1.1609622 24: −2.1516325 25: 0.2511712 26: 0.19739714 27: 4.1415296 28: 0.97708219 29: −3.1115251 30: 6.4011049 31: −3.1671309 32: −1.5625285 33: −1.1289238 34: −0.8072629 35: −0.06092153 36: −0.66443217 37: 2.3702629 38: −0.16842309 39: −0.4935627 40: 2.0837352 41: 0.80638069 42: 1.5681704 43: 1.1968515 44: −0.87553591 45: −2.2585204 46: −0.74682492 47: 1.2382894 48: 1.0413882 49: −1.0842441 50: −0.2513561 51: −0.91843736 52: −1.3671836 53: −1.1596954 54: 0.26116666 55: −0.84180433 56: 0.26325849 57: 0.46045518 58: −0.35954237 59: 0.095890306 60: −0.93630034 61: 0.89843744 62: 0.52230662 63: 0.49175408 64: 0.74472219 65: −1.0776283 66: −0.29318652 67: 0.27382204 68: 0.06797459 69: 0.38458759 70: −0.14918885 71: −0.084517807 72: −0.55330855 73: −0.27780494 74: 1.0952821 75: −0.2640903 76: −0.080420539 77: −0.56950516 78: −0.014582542 79: −0.98771346 80: −0.4344278 81: −0.19744191 82: 0.34438324 83: 0.67537814 84: 0.053237647 85: 0.015955647 #
−0.0017544086143438482 1: −7.5607929 2: 4.9967093 3: −1.264623 4: 1.5839788 5: −3.1135581 6: −1.7120829 7: 4.2883148 8: 0.10269687 9: −1.0577402 10: −0.98678935 11: −3.2682719 12: −2.218318 13: 0.040950354 14: −1.4008325 15: −0.96606475 16: −0.28105533 17: −0.47668806 18: 1.2778534 19: 1.9604092 20: 1.4759794 21: 2.3012459 22: 1.6083701 23: −1.4667403 24: 0.63299334 25: 0.97550392 26: −0.54523748 27: 0.59301919 28: 3.1892025 29: 0.069494046 30: −0.062061142 31: −0.66459078 32: −0.29568297 33: 0.53681523 34: 2.0728886 35: 0.60553735 36: 0.82829171 37: 0.86545765 38: 0.52002668 39: 0.55903029 40: −0.33308479 41: −0.73884112 42: 0.15741917 43: −0.38348535 44: −0.33616903 45: −0.20357849 46: 2.0278337 47: 1.0588315 48: 0.61091554 49:

APPENDIX C4-continued

| SVM Model Weights (85; Normal/Diseased) |
|---|
| −0.81337583 50: −1.5761976 51: 0.23632507 52: 0.94802552 53: −0.5830254 54: −1.6032152 55: 1.3840418 56: −0.51162708 57: −0.20480803 58: 0.83730423 59: 0.51563877 60: 0.61808813 61: 0.56924182 62: −0.77530587 63: −0.0090414956 64: −0.033454075 65: −0.19037022 66: 0.034517366 67: 0.45609969 68: 0.10079073 69: 0.51457125 70: −1.0463495 71: −1.2487614 72: 0.78104967 73: −0.20238008 74: −0.31103361 75: −0.12727672 76: 2.1968956 77: 0.97095293 78: 1.0261937 79: −0.40294078 80: −0.44990107 81: 0.3605907 82: 0.83272147 83: −0.57420367 84: 0.34378755 85: 0.20394959 # |
| −0.00029241901246946484 1: 5.7605891 2: 9.8290195 3: 1.8789825 4: −1.1318272 5: 7.9504757 6: 0.34706745 7: −3.3513935 8: 1.2476839 9: 3.0434899 10: −0.36745211 11: 3.7199888 12: 1.8109978 13: −2.7700968 14: 0.89088112 15: −6.2266636 16: −0.63499314 17: −0.95308942 18: −3.2592905 19: −0.27639693 20: 1.4911562 21: −0.95498282 22: −2.6575968 23: −0.99992591 24: −0.11102299 25: −1.6752316 26: −0.4156343 27: 0.33910745 28: 1.8173996 29: 0.76929176 30: 1.4767234 31: 0.56392443 32: −1.1427271 33: 0.47812706 34: 2.2496631 35: 2.182483 36: 1.8318955 37: −2.9768569 38: −3.1288815 39: 0.5895263 40: 4.7589025 41: −0.59536803 42: −0.80722958 43: −0.34699696 44: −0.9802708 45: 1.6393638 46: 1.0442442 47: 0.32212991 48: 0.25918323 49: −1.7139337 50: −0.17995603 51: 0.19763853 52: 1.0865116 53: 0.86287361 54: 0.60442656 55: 0.86261737 56: −1.1502584 57: 0.92417842 58: −0.64244395 59: 0.17892943 60: −0.91824561 61: −0.24928856 62: −0.034462687 63: 0.70051718 64: 1.00837 65: 1.2452569 66: 0.16973068 67: 0.041958362 68: −0.59003532 69: −0.53037918 70: 0.89056855 71: 0.3251256 72: 0.051477909 73: −0.44470191 74: 0.57884252 75: 0.85947841 76: −0.1458649 77: −0.23340164 78: −0.17262885 79: 0.57736421 80: 0.061778106 81: −0.018538158 82: −0.14533332 83: −0.82432085 84: 0.49507469 85: −0.14818789 # |
| −0.002838187186173749 1: 16.392971 2: −4.7027459 3: −2.2550261 4: −0.21748754 5: −4.5716577 6: 5.9160895 7: 5.429513 8: 2.0746083 9: −4.2725348 10: −4.7335415 11: 1.0379436 12: 5.0396523 13: −2.4807262 14: 2.5711129 15: 2.5762944 16: −6.0362124 17: 1.442536 18: 2.5452075 19: −0.87619179 20: 1.0887364 21: 1.1883737 22: 0.69489425 23: 0.91156578 24: 0.8202377 25: 1.1617807 26: 1.6182382 27: 0.34300202 28: 0.76539904 29: 0.33116844 30: 0.065732196 31: 1.1510335 32: 0.55732244 33: 0.99700636 34: 0.67217964 35: −0.66296524 36: −0.86372066 37: 0.43462038 38: 0.064805917 39: −0.10519884 40: 0.84757334 41: 0.067920893 42: −0.18248896 43: 0.15334356 44: 1.7386529 45: 0.34560779 46: 0.12476955 47: −2.1366498 48: 0.058745317 49: −0.30172783 50: −0.74402666 51: 053211993 52: −0.92503977 53: 0.84559625 54: 1.4197814 55: 1.0785793 56: 0.53916639 57: −0.68887943 58: −0.093460314 59: 0.80369282 60: −0.7160964 61: −0.90808797 62: 0.46412528 63: 0.87957537 64: 0.59649271 65: 1.0608096 66: 0.46454391 67: −0.64940065 68: 0.99365824 69: −0.32061386 70: 0.6111899 71: 0.16018821 72: 0.077451304 73: 0.23101214 74: −0.24294817 75: −1.5528877 76: −0.097729526 77: 0.55013484 78: 0.22187085 79: 0.2558637 80: −0.37704936 81: 0.046806384 82: 1.2514741 83: 0.042035438 84: −0.016180828 85: 0.28515542 # |
| 0.0035207597532646157 1: −1.513376 2: −1.8505038 3: −3.1226563 4: 3.4844956 5: −1.8776969 6: −1.47199 7: 0.80681765 8: −0.75451481 9: −0.47854143 10: 0.9895125 11: −0.8022784 12: −1.1363293 13: −0.39838672 14: −0.53547555 15: −1.0331632 16: −0.12748334 17: 1.5773466 18: −0.048117671 19: 0.64761943 20: −1.1173811 21: 0.22006649 22: 0.42375195 23: 0.70772225 24: 0.90536618 25: 0.068708986 26: 1.2127565 27: 0.79518342 28: 1.7149159 29: −1.3412409 30: 0.84027767 31: −1.9769535 32: −1.1390235 33: −0.19975612 34: −0.14863788 35: −0.99266446 36: 0.42730525 37: −1.4593364 38: −0.050251674 39: −0.92185473 40: −0.37061065 41: 0.61643738 42: 0.16165736 43: −0.59203166 44: 1.5533814 45: 0.28165334 46: 1.1489488 47: 0.023842113 48: 0.53270268 49: 0.22172646 50: 0.37802032 51: −0.37980214 52: 0.74919069 53: 0.75821257 54: 1.0981214 55: −0.73057991 56: −1.1890702 57: 1.5371476 58: 0.77694148 59: 0.55919814 60: 1.1852288 61: −0.25287256 62: −0.53572887 63: 0.99268645 64: −0.54913682 65: −0.5330345 66: −1.5217758 67: 0.36674589 68: −0.14583459 69: −0.96768582 70: −0.087492332 71: 0.77057946 72: 0.61932683 73: 0.68469149 74: −1.3130057 75: 1.0343505 76: 0.12145463 77: 0.82462418 78: −0.74196804 79: 0.12187001 80: −0.20082386 81: −0.52221185 82: −0.088906214 83: 0.80470431 84: 0.32073456 85: 0.30284989 # |
| 0.0035207597532646157 1: −2.9766047 2: 2.3910513 3: −0.0033213915 4: −0.17175539 5: −6.0470386 6: −1.3497559 7: −0.36723912 8: 0.20253371 9: −0.012134829 10: 1.6765274 11: 1.0212137 12: 1.540747 13: −0.44459653 14: 2.285203 15: −2.1024718 16: −2.3299692 17: −0.22237271 18: −1.540495 19: −1.7433741 20: −0.86427718 21: 3.2597923 22: −0.9036212 23: −0.33261031 24: 0.08034569 25: 0.31062645 26: 0.62380868 27: 0.30884013 28: 0.93615496 29: −0.55678594 30: 0.83648986 31: 2.2175543 32: −3.9626403 33: 0.67159081 34: −0.12033869 35: 0.051533122 36: 1.9251186 37: −0.50044167 38: 0.91387403 39: 1.315704 40: 0.64285749 41: −0.69283903 42: 1.6269565 43: 0.97460204 44: 0.094993889 45: −1.448289 46: 0.48921242 47: −0.24176522 48: 1.2643825 49: 1.7443092 50: −0.70274568 51: 0.24876195 52: 0.43642703 53: −0.60853028 54: 0.059798267 55: 0.13331567 56: 0.8999694 57: −0.95040554 58: 1.6903936 59: −0.78197664 60: −0.024035554 61: 0.50674534 62: −0.80088967 63: 0.19888808 64: −0.327461 65: −0.15733092 66: −0.25754383 67: 0.87108743 68: 0.32690728 69: −1.6650847 70: 0.39882895 71: −0.14998643 72: 0.15765926 73: 0.068408899 74: −0.43477553 75: 0.37428498 76: 0.203853 77: −0.098876506 78: 0.77563006 79: −0.14145415 80: 0.13966918 81: −0.21151921 82: −1.1710844 83: 0.31694144 84: 0.29759014 85: 0.23627378 # |
| 0.0035207597532646157 1: 1.4998577 2: −0.833125 3: 0.15874894 4: −0.16305982 5: −6.3999782 6: −3.0114808 7: −2.3441393 8: −0.62991965 9: 0.48263061 10: 1.2088264 11: 2.9173965 12: 0.93438792 13: −1.1417776 14: 0.47276586 15: 1.2369784 16: −0.55091071 17: −0.66656023 18: −2.6298883 19: −2.2242267 20: −0.40263057 21: 0.19578533 22: −0.36221969 23: −1.7459612 24: −1.1249856 25: −0.96496415 26: 0.97178137 27: −0.89674354 28: 0.18115836 29: −0.2664201 30: −0.84420794 31: 0.99844122 32: 0.3935703 33: −0.92425972 34: 0.84827334 35: 0.18696381 36: −0.61741596 37: −0.27812341 38: 0.82220787 39: 1.5204298 40: −0.024465038 41: −1.4631784 42: 1.8447262 43: −0.38213187 44: 0.12529095 45: −1.3761704 46: −0.041299947 47: −0.019116471 48: −1.0498253 49: 0.63776499 50: 0.88740844 51: 1.2011482 52: 0.41635996 53: 0.10563747 54: −0.58376336 55: 0.27111086 56: −0.8262558 57: 1.1927794 58: −0.5591445 59: −0.032716781 60: 0.93659627 61: 1.1629854 62: −0.14906347 63: 0.06745334 64: 2.1141806 65: 0.062371463 66: 0.2405418 |

APPENDIX C4-continued

| SVM Model Weights (85; Normal/Diseased) |
|---|
| 67: 0.31143147 68: 0.5432331 69: −0.45986184 70: −1.0745176 71: 0.55840057 72: −0.72463292 73: 0.062870719 74: −0.83106136 75: −1.02478 76: −1.2473516 77: 0.050191764 78: −0.74776781 79: 0.46886358 80: −0.20920451 81: −0.3985875 82: 0.2346088 83: −0.31092039 84: −0.41067883 85: −0.38236198 # |
| −0.0035207597532646157 1: 1.8426523 2: −1.0022681 3: −1.8142201 4: 4.7052956 5: −3.3947911 6: −3.9205186 7: 2.2534845 8: −0.65490913 9: 0.93505371 10: −1.3716303 11: −2.4469345 12: −1.6224073 13: −0.52282864 14: −2.9351051 15: −0.0068617496 16: 0.46865952 17: −1.560643 18: −0.21292216 19: 2.1473019 20: −0.67687339 21: −0.28722957 22: 0.56001335 23: −0.094829082 24: −1.3970063 25: 0.98717302 26: −0.4236204 27: −0.92757404 28: 0.3730565 29: 1.0406255 30: −0.88888693 31: −1.4504825 32: −0.6683532 33: −0.33247265 34: −0.033092454 35: 0.26896572 36: 1.5959476 37: 0.010037191 38: −0.81271714 39: 0.0030672953 40: 0.50752759 41: −0.4395774 42: 0.31354156 43: 1.1316957 44: 1.0628705 45: 0.81664729 46: −0.44994509 47: 1.8356267 48: −0.94820237 49: 1.1194025 50: −0.49359241 51: −0.27994666 52: 1.309444 53: 0.021853868 54: 0.30842969 55: −0.78456146 56: 0.28993934 57: 0.94030941 58: −0.034615789 59: −0.35700414 60: 0.35395202 61: 0.061831497 62: −0.74912906 63: 0.12902097 64: −0.34087849 65: 0.35399655 66: −0.27148318 67: −0.64102411 68: −0.23167168 69: −0.33912688 70: 0.031118577 71: 0.612023 72: −0.31107095 73: −0.78582859 74: 1.0256356 75: −0.19048233 76: −0.4532049 77: 0.2822164 78: −0.194115 79: −0.24197151 80: 0.38782927 81: −0.33452025 82: 0.41326469 83: 1.3208663 84: 0.19393028 85: 0.45549294 # |
| −0.0035207597532646157 1: −9.4932261 2: −2.4200175 3: −0.99547184 4: 3.386457 5: −0.25609118 6: −2.623518 7: −2.4135804 8: −0.39986932 9: 2.1378477 10: 1.8484613 11: 0.7939347 12: −1.8100283 13: 0.086847119 14: −1.0847259 15: 0.014694811 16: −0.061961468 17: 1.11698 18: 0.37644273 19: 0.43925872 20: 1.019256 21: −0.034235802 22: −1.0565522 23: 0.18581668 24: −1.7383976 25: 2.1731598 26: 0.71717995 27: 1.3705052 28: 0.42550248 29: −0.29724944 30: −1.2346706 31: −0.56772882 32: 0.35246193 33: −0.03986638 34: −0.38854089 35: −0.65117943 36: −1.2889299 37: −0.93312246 38: 0.5973838 39: 0.4066982 40: −1.2644749 41: 0.99629927 42: −0.57985032 43: −0.63576305 44: −1.8356446 45: −1.0743715 46: −0.14329678 47: −0.8826586 48: −0.37040722 49: −0.6788758 50: −0.45492631 51: −0.89243484 52: −0.057133693 53: 0.31184465 54: 0.084423982 55: −0.56936181 56: −0.10785694 57: −1.0227678 58: −1.2069671 59: −0.4624708 60: −0.46327126 61: −0.94274431 62: 0.62106037 63: −0.7299782 64: 0.32808968 65: 0.70177394 66: 0.07611876 67: 0.44077566 68: 1.2233313 69: −0.31044862 70: −0.9895606 71: 0.20284437 72: 0.54383928 73: −1.5249349 74: −0.45136279 75: 0.15737078 76: −1.0366597 77: 0.69401526 78: 1.8774619 79: −1.3141834 80: −0.35478765 81: 0.68788713 82: 0.34662926 83: 0.46135426 84: 0.89465719 85: −0.21682085 # |
| −0.0035207597532646157 1: −5.7653995 2: −7.7065129 3: −1.7101065 4: 2.9592018 5: 0.76229161 6: −3.6607392 7: −1.3269446 8: 0.56657773 9: 1.139729 10: 0.17632462 11: 2.1677668 12: 1.3118943 13: −0.52651542 14: −0.3446798 15: −1.5242846 16: 0.45261335 17: 1.8554153 18: −2.0332828 19: 1.0373086 20: −0.59927064 21: 1.2456559 22: −0.52233613 23: 0.24843232 24: −0.57826668 25: 0.20601466 26: 1.0337256 27: 1.3346144 28: 1.0033516 29: −0.14132218 30: −0.44747621 31: −2.1312487 32: 1.0729326 33: 0.63819945 34: −1.0156969 35: −0.12516639 36: −1.7160656 37: −0.74329221 38: −0.031156909 39: −0.38357505 40: 0.23199198 41: −0.6455729 42: −0.53660375 43: 1.8243196 44: −0.228793 45: −1.1999203 46: 0.15424994 47: −2.392344 48: −0.84571058 49: 0.38441601 50: −1.4214644 51: −0.23135762 52: 0.99908489 53: 0.30190232 54: 1.2513613 55: 0.15170304 56: 1.1843537 57: −1.0560424 58: −0.0013475108 59: −0.63009286 60: 0.33963561 61: 0.38146102 62: 0.10609791 63: −1.1965718 64: 1.3627383 65: 1.5931025 66: −2.627198 67: 0.10647382 68: −1.9954445 69: 0.65885431 70: 1.384408 71: 0.94649565 72: 0.17098832 73: −0.62934065 74: −1.0389315 75: −0.28657356 76: −0.1330131 77: 0.39319348 78: −0.030887162 79: 0.11736631 80: −0.45598289 81: 0.36185947 82: −0.79248106 83: −0.34403181 84: −0.20294397 85: −0.21804844 # |
| 0.0035207597532646157 1: 5.4943523 2: 3.8203344 3: 3.2906234 4: 0.16825591 5: −4.9035769 6: −0.52033991 7: 3.1050794 8: 2.5860252 9: 2.6400912 10: −3.4708204 11: 2.3735955 12: 1.9459182 13: 3.1852815 14: 1.206341 15: −3.3552761 16: −2.1890383 17: 1.5772523 18: −0.99846894 19: −1.9426285 20: 1.7405504 21: −2.5103328 22: −0.1712421 23: 0.62044519 24: 1.7075816 25: 0.18535832 26: −0.3251397 27: 0.50698811 28: 2.1281648 29: −1.4055895 30: 0.44488609 31: 0.082362577 32: 0.50587648 33: 1.4535089 34: −0.1660212 35: −1.0464996 36: −0.32472673 37: −3.2258751 38: −1.0420521 39: 0.26829112 40: −0.26259658 41: 0.66264814 42: −1.5650598 43: −2.8255298 44: −0.47267067 45: −0.26437676 46: 1.4970443 47: 1.6494414 48: −1.150957 49: 0.48409933 50: −0.97914815 51: −1.1762872 52: −0.67540783 53: 0.9785468 54: −0.10272652 55: −0.44946235 56: −0.6475299 57: −0.19610074 58: 0.57770157 59: 0.62224936 60: 1.2325798 61: 2.0817311 62: 1.3649201 63: −1.5788438 64: 0.3441278 65: −0.82410073 66: 0.38950849 67: 0.63741684 68: 0.81976885 69: 1.8669279 70: −0.093081616 71: −0.50634414 72: 0.70292288 73: −0.21797721 74: −0.81374848 75: −0.97752309 76: −0.00052603154 77: −0.047995523 78: 0.56340075 79: −0.13965929 80: 0.74398124 81: −1.0789561 82: −1.6268255 83: 0.34880072 84: −0.23649105 85: 0.58947003 # |
| −0.0035207597532646157 1: 12.198691 2: −4.6254134 3: 0.4309229 4: −0.0045036334 5: 1.6533217 6: −1.6674639 7: −0.58168441 8: −2.0143023 9: −0.36359423 10: −1.1387699 11: 0.4026781 12: 3.4342923 13: 0.077531099 14: 0.59686226 15: 1.4676325 16: −1.0380758 17: 2.0957778 18: −0.18262574 19: 1.3347188 20: 0.81862861 21: 1.8272871 22: −1.1508977 23: 0.6757282 24: 1.425102 25: 4.0549784 26: 0.38353825 27: −1.8369131 28: −0.13398515 29: −0.57104951 30: 0.22000989 31: 0.12870221 32: 0.7133007 33: −0.35001582 34: 0.0011888057 35: −0.90330213 36: 1.5864959 37: −0.25036854 38: −0.020135572 39: −0.67250866 40: −0.66962731 41: −0.76892602 42: 0.42453542 43: −1.3383957 44: 0.089187309 45: 1.4743941 46: −0.58752674 47: −0.13003859 48: −0.085984677 49: 1.88237 50: −0.092915475 51: −0.16898575 52: −1.2927262 53: 1.1112242 54: −0.56929666 55: 0.51432651 56: 1.5974669 57: 0.29192296 58: 1.3793269 59: 1.3311955 60: −1.1512399 61: 1.1414181 62: −0.42488316 63: 1.02485 64: 0.80391228 65: −0.12326206 66: −0.0096905828 67: −0.25598711 68: −0.56333989 69: 0.47411421 70: −0.52220768 71: 0.62780327 72: −0.63821578 73: 0.044849351 74: 0.30436012 75: 0.85827565 76: −0.35568988 77: 0.48760805 78: 0.55250949 79: |

APPENDIX C4-continued

SVM Model Weights
(85; Normal/Diseased)

−0.48662898 80: 1.1320682 81: −0.4279331 82: 0.55387139 83: −0.18235028 84: 0.64431673 85: −0.12753169 #
−0.0031231746471605997 1: −0.92056668 2: 7.982316 3: 2.7672982 4: −5.6989779 5: −2.0040121 6: 1.3560103 7: 0.47844598 8: −0.88915581 9: 0.29286313 10: 1.9550498 11: 0.73400009 12: 0.67523128 13: 4.2900996 14: 1.759645 15: 3.1263313 16: 3.4484181 17: 1.1700882 18: −2.5563493 19: 0.37533271 20: −0.79565668 21: −1.3620112 22: −0.24505715 23: 2.6705673 24: 0.91925913 25: −1.7523115 26: 2.7090824 27: −2.4245808 28: −0.3016541 29: 1.0368193 30: 1.349012 31: 1.3343428 32: 1.1360695 33: −1.0604455 34: −0.55855429 35: −1.4334891 36: 0.31644401 37: 4.0981212 38: −0.76405543 39: 2.4361506 40: −0.072746783 41: 1.3639972 42: −2.7133963 43: 0.58745974 44: 1.215488 45: 0.71256995 46: −0.63146925 47: 1.1245365 48: 0.68571043 49: 0.12023477 50: −2.9852123 51: 0.48245761 52: −0.60535866 53: −0.42614096 54: 0.895666 55: 1.536912 56: 0.41395107 57: 1.3474098 58: −0.11917051 59: −0.72688085 60: 0.94913411 61: 0.62710458 62: 0.84917873 63: 0.10144996 64: 0.94962496 65: 0.48940825 66: 0.1560725 67: 0.10165013 68: −0.73191041 69: 0.0017839102 70: 0.48697016 71: −0.49387777 72: 0.68558019 73: 0.53076398 74: −0.7026388 75: 0.14259262 76: 0.0749093 77: 0.1046522 78: −0.71482873 79: −0.096147284 80: 0.26972616 81: 0.37506589 82: 0.2323183 83: 0.59012479 84: −0.22533044 85: 0.45790485 #
−0.0035207597532646157 1: 2.0158556 2: 5.64184 3: 1.2100551 4: 0.38732079 5: −0.91638023 6: 0.86250663 7: −5.9655256 8: 1.9825593 9: −3.4821234 10: 0.86993414 11: −1.6572517 12: −0.76582778 13: 0.11991637 14: 0.039823018 15: −1.6965232 16: −0.86651272 17: 0.55945367 18: 0.67926311 19: 1.2445376 20: −0.74454379 21: −0.71011066 22: 2.5852528 23: −1.3076165 24: −0.46179819 25: −2.4348414 26: 1.8081855 27: 1.3103861 28: −1.3082397 29: −0.89139622 30: −2.1623175 31: 1.5018917 32: −0.46999404 33: −0.27754453 34: 1.9421457 35: 0.8924948 36: −0.59410006 37: 1.1388235 38: −0.40503344 39: 1.266946 40: 1.3438236 41: −0.20875518 42: −1.152586 43: 0.35084587 44: −0.66025627 45: 0.27601939 46: 0.50508291 47: 1.0504811 48: −0.0061990432 49: 0.89158946 50: −0.740192 51: 0.37023339 52: 0.18432029 53: 0.49898073 54: −1.0100789 55: −0.98633426 56: 0.052206729 57: −1.1405525 58: 0.059401955 59: 0.6115393 60: −0.038578793 61: 1.044669 62: 0.41048342 63: 0.4342218 64: −0.19823729 65: 0.45956901 66: 1.2680084 67: −1.5415982 68: 0.26044369 69: 0.67990941 70: −0.20977019 71: 0.17940669 72: −0.6234647 73: −0.15683755 74: −0.12970166 75: 0.23375361 76: −1.0716821 77: −0.34470367 78: −0.15326777 79: −0.88641953 80: −0.051476792 81: 0.60701138 82: −1.132746 83: 0.27538162 84: −0.67856759 85: −0.77390039 #
0.0035207597532646157 1: −12.323371 2: −2.5419991 3: −1.609848 4: 4.4974389 5: −3.7014587 6: −4.0358763 7: 2.6280291 8: 4.9896169 9: 2.5341156 10: −1.446465 11: 0.80235535 12: −2.3242402 13: −1.1710668 14: −0.41775832 15: −4.1889386 16: −1.1208876 17: 0.92109925 18: −1.9065992 19: −1.8256842 20: −2.3905437 21: 1.7596356 22: −1.4175112 23: 0.18312508 24: 3.5366721 25: −0.89412063 26: −3.6899207 27: 1.4042687 28: −0.66406071 29: −0.58963937 30: −2.340239 31: −2.9288216 32: −0.79229331 33: −0.91411191 34: 2.9614749 35: −0.89132273 36: 1.7922473 37: 2.2354436 38: 0.53673452 39: −0.18893766 40: −1.2241523 41: 0.79943401 42: −1.4271966 43: −0.86519498 44: 1.1074665 45: −2.1866074 46: −0.57520199 47: 0.82644343 48: −0.090864554 49: −1.2602122 50: 0.36414298 51: −0.040461358 52: −1.4667616 53: 2.691318 54: 0.92768717 55: −0.39435172 56: 0.9569068 57: 1.4663866 58: −0.10978934 59: −0.15809369 60: −1.1098099 61: −0.49797028 62: 0.18566647 63: −0.83051121 64: 0.23004419 65: 0.095365636 66: 0.65703654 67: −0.83133465 68: 0.38520044 69: 0.29496205 70: 0.26739585 71: 0.77351087 72: −1.0678705 73: 0.89645118 74: −0.21810022 75: −0.8048836 76: −0.17026433 77: −0.14614077 78: −0.25395 79: 0.718638 80: 0.84217626 81: 0.2479565 82: 0.064400159 83: −0.662857 84: 0.38506141 85: 0.030625224 #
0.0035207597532646157 1: 3.4503579 2: −4.2435541 3: −3.5084748 4: 4.1104755 5: −2.2494571 6: −1.1301751 7: 1.2851278 8: −1.3474931 9: 0.074681044 10: −1.1245632 11: 0.0059922114 12: −0.65546483 13: −1.0927281 14: −1.6123801 15: −2.0109613 16: 0.8245908 17: −0.20697463 18: 1.6903372 19: 0.20574044 20: −0.52657861 21: −0.15481399 22: −0.95674044 23: −0.12188616 24: 0.3153148 25: 1.220279 26: −0.46595594 27: 1.2647409 28: −1.0921087 29: 0.63332158 30: 0.31533015 31: 0.49947315 32: 0.52631956 33: 0.52140331 34: −1.471079 35: −0.3043865 36: 0.6245653 37: −0.54806453 38: −0.14093906 39: 0.97424895 40: −0.78888589 41: −0.30943748 42: 0.2295381 43: −0.26546445 44: −0.69476426 45: −0.13171944 46: 0.094888531 47: 0.10638277 48: −0.43834734 49: 0.36926419 50: 0.16866605 51: −0.16950628 52: 1.0210851 53: −0.12908459 54: 0.2574836 55: 0.16228732 56: −0.32980037 57: 1.2871718 58: −0.695324 59: −0.44037962 60: 0.13058139 61: −0.81643009 62: 0.085330784 63: 0.63842231 64: −0.39016843 65: 0.074462868 66: 0.62911004 67: −0.055147562 68: 0.13169409 69: 0.51636732 70: −0.58961576 71: −0.18650682 72: 0.22953425 73: −0.46220464 74: −0.064442351 75: 0.15822068 76: −0.82707661 77: −0.18713538 78: −0.54458982 79: −0.12780048 80: 1.0517936 81: 0.39728534 82: −0.30585971 83: −0.20047277 84: 0.61465275 85: 0.41496634 #
0.0010824465213198314 1: −5.0323195 2: −2.8937032 3: 0.9245494 4: 4.0953684 5: −0.48259613 6: −10.957071 7: −1.3562635 8: 1.5278653 9: 1.908803 10: 1.5891732 11: 1.9105272 12: −1.7403718 13: 0.79528445 14: 1.4411625 15: 2.055773 16: −0.47434691 17: 0.84861767 18: 0.96878743 19: 1.2661024 20: 0.39621857 21: 0.02885787 22: −2.1331224 23: 1.1653996 24: 1.7666892 25: −0.5342958 26: −0.058051892 27: 0.22720467 28: −1.8131837 29: −0.33533868 30: 0.51968986 31: −2.8554194 32: −0.39893693 33: −1.3069463 34: −1.2616062 35: −0.50449288 36: −0.30745259 37: 0.78427112 38: −1.7781194 39: −3.1630948 40: 1.5530428 41: −0.52526122 42: −1.3863609 43: −0.75657463 44: 1.3458173 45: −0.41903311 46: −0.60242832 47: −0.73190629 48: −1.1985373 49: 0.9617061 50: −1.0572286 51: −1.0892643 52: 2.7433617 53: −0.29182494 54: −1.1755396 55: 0.30320728 56: 0.59947592 57: −0.57867312 58: −0.31572407 59: 0.67291749 60: −0.25184411 61: −0.12825929 62: 0.14712813 63: 0.072493941 64: −0.93540007 65: 0.23385698 66: 1.2352091 67: 0.40883824 68: 0.90679425 69: −0.78691781 70: −0.43946591 71: 0.061390832 72: 0.43101066 73: −0.65560371 74: −0.11186254 75: 0.84073192 76: −0.76387501 77: −0.085754573 78: 0.28736416 79: 0.57194638 80: 0.18722515 81: 0.20813055 82: −0.77415365 83: −0.11878719 84: −0.66424346 85: 0.10148657 #

APPENDIX C4-continued

SVM Model Weights
(85; Normal/Diseased)

0.00026606620812858508 1: 6.3584962 2: −6.3778191 3: 3.2515109 4: 5.1755161 5: 4.2499866 6: −11.99882 7: −1.5156378 8: 4.1527638 9: −0.18030602 10: −1.1761832 11: 5.4542184 12: 2.0691378 13: −1.6560538 14: 0.79019296 15: 1.8808135 16: 1.9049292 17: 1.8592358 18: −2.1669643 19: −0.048648611 20: −2.5740819 21: −0.70472515 22: 0.8201015 23: 0.71556932 24: −1.80097 25: −2.5610666 26: 0.59389859 27: −0.78396356 28: 0.11526062 29: −0.09563344 30: −2.0597372 31: 0.75164664 32: 1.7167188 33: −0.8780849 34: −0.94556618 35: 3.2067571 36: −0.55151516 37: −1.2391465 38: −1.4040649 39: −2.0579765 40: −0.10920454 41: 1.5984117 42: 1.5354701 43: 2.2374403 44: 1.6578482 45: −0.069791123 46: 0.43039051 47: 0.53295434 48: 0.75136089 49: −0.90726262 50: −0.59872472 51: −0.23022404 52: −0.99246538 53: −1.8657418 54: −1.3137063 55: 0.69614094 56: 0.54208493 57: −0.83017355 58: −0.029540086 59: 1.9364667 60: −0.29958665 61: 0.17397369 62: 0.79381496 63: −1.6109239 64: 0.96843368 65: 0.052511267 66: 0.11731391 67: −0.83705848 68: 0.82254171 69: −0.26468176 70: −0.76873767 71: −0.29751939 72: 1.3841127 73: 0.52975595 74: 0.60065693 75: 0.36754712 76: 1.0355914 77: −0.21337773 78: −0.11204219 79: −0.12291181 80: 0.96028787 81: −0.050827105 82: 0.62444359 83: 0.15589094 84: 0.66139913 85: 0.18312415 #
−0.0035207597532646157 1: 4.132174 2: −6.2578673 3: −4.4534831 4: 3.3225648 5: 0.92792118 6: 0.13495214 7: 2.4636238 8: 0.043804433 9: −0.12212539 10: −3.6037035 11: −0.16387007 12:2.1024275 13: −0.8426888 14: −0.28110489 15: −1.0565786 16: 1.7971499 17: 0.89108872 18: −0.19204256 19: −0.37601933 20: 0.29086679 21: −0.93570775 22: 0.9933148 23: 0.49556109 24: 0.30878216 25: −0.06323579 26: 1.3881254 27: 1.156985 28: −0.836025 29: 1.0145077 30: −0.14229111 31: −0.17155382 32: −0.026234334 33: −1.2460279 34: −1.0607399 35: −2.3045077 36: 0.15773092 37: −1.859993 38: 1.3026433 39: −1.4954717 40: 0.91123676 41: 1.6476334 42: −0.016044997 43: 1.1311302 44: 0.65482485 45: −0.50996262 46: 0.20572463 47: 0.20633431 48: 0.9185195 49: −0.0069128866 50: −0.8106612 51: 0.44928578 52: 1.769662 53: 0.28103986 54: −0.39396164 55: 0.82345629 56: −0.58649194 57: 0.011862372 58: −0.77182484 59: −1.0363826 60: 0.64749193 61: 0.57068056 62: −0.73007858 63: −0.097035326 64: −0.10577562 65: −0.12638293 66: 0.89023834 67: −0.20933913 68: 0.59134924 69: 1.16711 70: 0.092131026 71: 0.64477086 72: −0.56461102 73: 0.98778188 74: 0.59265774 75: −0.39949697 76: −0.89452052 77: −1.2504236 78: 0.47944611 79: 0.56021106 80: 0.039773744 81: −0.26168171 82: 0.69073153 83: −0.76336658 84: −0.085453652 85: −1.1681105 #
−0.00098181610508975021 1: −9.2383366 2: 2.0031359 3: −2.7472436 4: −0.29943109 5: −5.6568513 6: 3.7322798 7: 5.1578135 8: 2.1428649 9: −2.7855699 10: −0.25731304 11: −2.9800839 12: −0.47946775 13: −2.2630336 14: −0.45474353 15: −5.7471838 16: 2.3978477 17: 4.3268204 18: −3.0305762 19: 1.3055806 20: −2.1667976 21: −0.78709322 22: −1.6385171 23: −1.2645901 24: −0.72841704 25: −1.361117 26: 2.6740563 27: 0.99330205 28: 0.56622869 29: 0.021516191 30: −1.0199603 31: 2.8918629 32: 0.17529561 33: 1.3039639 34: 0.66107935 35: −0.73529148 36: 1.6549188 37: −2.4072337 38: 1.3072208 39: −0.56783468 40: −1.3100624 41: 0.3624413 42: −0.26424339 43: 0.42006019 44: 1.9382477 45: −0.51278996 46: 0.47823575 47: 0.0037102359 48: 0.95446652 49: 1.0228879 50: −1.393595 51: −1.2037687 52: −0.73327082 53: −1.1920532 54: 0.10549983 55: −0.13279434 56: 0.3578119 57: 0.38885364 58: −0.95124429 59: −1.0567375 60: −1.8370425 61: −0.6606943 62: 0.70864707 63: 0.67599821 64: −0.37370375 65: 0.20003127 66: 0.63242871 67: 0.15085423 68: 0.057238787 69: 0.17639741 70: −0.23044479 71: −0.20157395 72: 0.62036103 73: −0.25716212 74: 0.71563143 75: 0.7609778 76: −0.050195843 77: −0.25451463 78: −0.1692701 79: −0.078648195 80: −0.74276435 81: −0.010895328 82: 0.77240366 83: 0.27615985 84: −0.90610391 85: −0.029832665 #
−0.0035207597532646157 1: 1.5939288 2: −0.68451202 3: −1.9828767 4: 2.687711 5: −2.3559065 6: −0.40762001 7: −0.38349798 8: 1.4480487 9: 0.19084418 10: 0.57923073 11: 0.15427236 12: 0.30517232 13: −2.8470616 14: −0.89354444 15: −1.8082743 16: 0.90372598 17: −0.8944034 18: −0.19528657 19: 0.37987849 20: −0.72632611 21: 0.74004036 22: 0.51418865 23: −1.1826543 24: −0.68684179 25: 1.3350503 26: 1.3483067 27: −1.1749243 28: 0.0035296429 29: 0.40864256 30: −1.0857723 31: −2.2653854 32: 1.132339 33: −0.75138783 34: 1.6571852 35: −0.66929579 36: 0.01038154 37: 0.11476938 38: −0.28282329 39: −0.0039718393 40: −0.42626029 41: −0.1703448 42: −1.2294829 43: 0.49754259 44: 0.78424221 45: 0.40770197 46: 0.2548393 47: 0.34366134 48: 0.42368001 49: −0.0031600283 50: −0.55383235 51: 1.7163563 52: 0.033633709 53: −0.73686308 54: 0.89823377 55: −0.037769046 56: −0.27557534 57: −1.1176921 58: 1.4940319 59: 0.26057047 60: −0.62359345 61: 0.52774233 62: −0.72299153 63: 0.15405934 64: −1.3268715 65: −0.1421221 66: −1.6126971 67: −0.030900931 68: 0.54111493 69: 0.80216682 70: 1.0123219 71: 0.067640841 72: 0.20240721 73: −0.87775278 74: 0.26203439 75: 0.33620653 76: 0.026765861 77: −0.89195812 78: 0.46182638 79: 0.41690511 80: 0.53303576 81: 0.3838982 82: 0.19043288 83: −0.31487751 84: −0.2211739 85: −0.094877258 #
0.0035207597532646157 1: 3.194849 2: 0.43900785 3: −1.9627602 4: 1.2485242 5: −5.9852576 6: 0.33253258 7: −1.8617131 8: −0.86069912 9: 0.550134 10: 1.0473752 11: 1.0903063 12: 0.014737786 13: −0.93575341 14: −0.49048775 15: −0.22670957 16: 0.033254467 17: −1.1327134 18: 0.51697665 19: −0.088372737 20: −0.88697433 21: −1.1650202 22: 0.80797178 23: −0.92340988 24: −1.0851067 25: −0.81728846 26: 0.33128548 27: −0.55782062 28: −1.3039638 29: 034368724 30: 0.6521095 31: −0.99489051 32: 0.014531549 33: −0.2099172 34: −0.99392444 35: 1.1560659 36: −0.05918486 37: 0.16560514 38: 1.1157157 39: −0.6798988 40: 0.2000774 41: −2.4399419 42: 0.062852286 43: −0.59827936 44: −0.64824188 45: −0.74368501 46: −0.35463345 47: 0.14426918 48: −0.25484803 49: −0.85277611 50: −0.49318787 51: −0.58561718 52: 0.6080265 53: −0.54487962 54: 0.38094941 55: 0.58301115 56: −0.83181024 57: 1.4327674 58: −0.32032874 59: −0.7785061 60: 0.2222829 61: 0.2062933 62: −0.33664161 63: 0.40453207 64: −0.063989356 65: 1.0704974 66: 0.85856509 67: −0.34260032 68: −0.81909335 69: 0.24490944 70: −0.8815605 71: −0.40375853 72: 0.30855694 73: −0.22328483 74: 0.11981357 75: 0.20845959 76: −0.27041709 77: 0.18642138 78: −0.021063909 79: 0.14842433 80: 0.18297967 81: −0.94384241 82: 0.65075558 83: −0.23166057 84: −0.19040057 85: −0.88623601 #
0.0035207597532646157 1: 5.3318014 2: 2.8600442 3: −0.63892436 4: 2.671339 5: −5.2220407 6: 0.021795753 7: −0.1497921 8: −0.35194841 9: 2.4227602 10: 0.78205884 11: −0.273817 12:

APPENDIX C4-continued

SVM Model Weights
(85; Normal/Diseased)

−1.8752793 13: 0.1105957 14: −1.5807208 15: 0.86257154 16: 1.7695898 17: −2.1386125
18: 0.13988218 19: 0.15350451 20: −1.6646396 21: −1.2468495 22: 1.1442618 23: 0.22816287 24:
−0.59291494 25: −1.2557151 26: −0.16814576 27: −0.27625111 28: −0.94614822 29: 0.90841764 30:
−0.55482227 31: −0.69049489 32: −0.52906591 33: 0.1456854 34: −0.15881176 35: 0.79538953
36: 0.14933707 37: 0.35109264 38: 1.6287683 39: 0.30482042 40: −0.16101275 41: −1.1122111
42: 0.92197961 43: −0.65001202 44: −0.29940131 45: 0.82114142 46: −2.3014662 47: 0.019852048
48: −1.4395304 49: −0.61461782 50: −0.66179311 51: 0.33406314 52: 0.71744514 53: −0.31344864 54:
−0.36929134 55: 1.0807132 56: 0.64560848 57: 0.36599183 58: 0.63315117 59: −0.59978986
60: 0.47401521 61: −0.04233579 62: 0.43825498 63: −0.18208194 64: 0.93805003 65: 0.6489799
66: 1.0274676 67: 0.30374503 68: 0.093746543 69: 0.65355974 70: 0.93731129 71: 0.31009677
72: 1.0268996 73: 1.0494651 74: 0.12953329 75: −0.13468555 76: 0.082101204 77: 0.082376562
78: 0.093450055 79: −1.2197555 80: −0.51803309 81: −0.14628641 82: 0.43446764 83: −0.35269833
84: 0.45715046 85: 0.71453136 #
0.0035207597532646157 1: 3.9855435 2: −2.1551187 3: 0.63115042 4: 1.5583338 5: −3.9991305 6:
−3.0780492 7: 2.0848374 8: 2.7543757 9: −2.3052657 10: 1.416037 11: 0.10207489 12: 3.0797191 13:
−1.0896925 14: 1.9548575 15: −0.089594446 16: −1.3948822 17: 2.7305973 18: −0.86904126
19: 2.5512304 20: −2.1800091 21: 0.86764246 22: 0.11505432 23: 0.20976232 24: −1.2548302 25:
−2.8737543 26: 3.077101 27: 1.5563121 28: 0.16239864 29: 0.67452103 30: 1.2004149 31:
−0.94163388 32: −3.336623 33: −0.12538108 34: −1.4093879 35: −1.4058474 36: 0.069847085 37:
−0.71715277 38: 1.0935538 39: −0.28317529 40: −0.34645393 41: −0.031229772 42: 0.76986682 43:
−1.5068744 44: −0.61947757 45: 2.0491185 46: 0.34174487 47: −0.169028 48: 0.72976196 49:
−0.36800814 50: 0.64198077 51: 1.0225791 52: 0.052821398 53: −0.84884322 54: −0.13224651 55:
−0.94264621 56: −0.095210724 57: −0.26225153 58: 1.0290097 59: 0.7017597 60: 0.74610132 61:
−0.24856976 62: 0.14428349 63: 1.0233965 64: 1.1792885 65: −0.50222903 66: 0.061810724 67:
−0.88351119 68: 0.39995912 69: 0.14672771 70: 0.60004687 71: 0.84775209 72: 0.52471834
73: 0.32894376 74: −0.12081071 75: −0.36660975 76: 0.52416295 77: 0.1678348 78: −0.082099371
79: 0.458909 80: 0.13918488 81: 0.21450907 82: −0.61503118 83: 0.89800525 84: 0.90652812 85:
−1.189242 #
−0.0035207597532646157 1: 11.063172 2: −4.1735458 3: −2.1705191 4: 3.1756155 5: −2.6342511
6: 0.35717416 7: −2.6251674 8: −2.3413982 9: 1.3099627 10: 2.2732904 11: 1.9024211 12: −2.9932053
13: 2.0243397 14: −0.28601316 15: 0.81185395 16: −2.5839396 17: 2.4302902 18: 3.7185061 19:
−0.9046219 20: 0.72545081 21: −1.4551767 22: 1.4636325 23: −0.15903565 24: −1.6384495
25: 0.075246438 26: −0.20895387 27: 0.26143897 28: 1.2070005 29: 2.0606019 30: 2.1030214 31:
−0.69226116 32: 2.1005497 33: 0.75281036 34: 2.7544527 35: 0.082330272 36: 0.38176236 37:
−1.5440055 38: 0.26154569 39: −1.1583414 40: 0.12141833 41: −0.16811602 42: 1.2153684
43: 1.6256666 44: 0.55115259 45: 0.25212508 46: −0.090178415 47: 0.071696945 48: 0.092321232
49: −1.1144848 50: −0.012306355 51: 0.28413066 52: −0.67935228 53: 1.2980931 54: −0.13099827
55: 0.12346329 56: 0.11142293 57: 0.27578577 58: −0.050162587 59: −1.1625016 60: −0.77165097
61: −0.012743402 62: −0.40751636 63: 1.8688 64: 0.48271897 65: −0.584391 66: −0.41269445 67:
−0.61985165 68: 0.26657802 69: 0.40913209 70: 0.17663826 71: −1.1105018 72: 0.71721327
73: 0.40302157 74: −0.82035613 75: −0.8042627 76: −0.47997978 77: −0.1955671 78: −0.19370109 79:
−0.35962215 80: −0.2477721 81: 1.1621563 82: −0.70190388 83: −0.085306503 84: −0.30679044
85: 0.45231619 #
−0.0014555372962281161 1: −7.4997253 2: 4.4368262 3: −2.9816823 4: −3.2905457 5: −7.8223085
6: 5.5449471 7: 0.26657972 8: −1.4545244 9: −0.12112358 10: 0.36736658 11: 1.3500887
12: 2.6143444 13: 0.8353107 14: 0.606983 6 15: −0.57392049 16: −1.7705781 17: 0.074982144 18:
−1.3446496 19: −3.4150405 20: 0.11493096 21: −0.62300509 22: −0.056075014 23: −0.84774786
24: 0.94183409 25: −0.027781744 26: −0.79541111 27: −2.3700309 28: 0.34954032 29: −0.31329978
30: 0.97368103 31: 0.77245986 32: −0.67884284 33: −1.7504072 34: −2.391221 35: 0.083415404 36:
−1.9214619 37: −0.7868306 38: −0.92057556 39: −2.0276494 40: 0.288537 41: −1.5791048
42: 0.91143805 43: −0.80769163 44: 0.47642806 45: −1.7863086 46: −1.493109 47: 0.302784 48:
−0.055297635 49: −0.016376823 50: −0.17008308 51: −0.24937692 52: −0.64883745 53: 0.00060224853
54: 0.25627023 55: 0.80983388 56: −0.61239278 57: −0.71748292 58: −0.80918968 59: −0.5118615
60: 0.31323686 61: 0.83679247 62: −0.89665455 63: −0.34058276 64: −1.2529209 65: −0.7296108 66:
−0.63929236 67: −0.24356525 68: 0.72444028 69: −0.10387129 70: 0.24494018 71: 0.70650542 72:
−0.3703928 73: 0.3357864 74: −0.20377003 75: −0.90150124 76: 0.79134268 77: −0.12168025
78: 0.17380694 79: −0.086510047 80: 0.067077324 81: 0.13328306 82: 0.67633224 83: −0.9618206
84: 0.20394857 85: 0.1517325 #
0.0035207597532646157 1: 2.7049806 2: 1.0712382 3: −0.60530049 4: 3.1470454 5: −6.2567849 6:
−1.7234993 7: −2.0789998 8: −0.55858582 9: 1.1510547 10: 3.0091002 11: 0.27469772 12: −1.7099465
13:0.52950001 14: −1.3216618 15: −1.2992212 16: 0.25060481 17: 0.48826501 18: 0.98599839
19: 0.92709947 20: −1.5546227 21: −1.628973 22: 2.1816301 23: −0.39126211 24: −0.38967183 25:
−0.50289649 26: 0.25889975 27: −0.35903266 28: 1.0430959 29: 1.2041683 30: −1.9328635
31: 0.015573424 32: −0.5285145 33: 0.25673017 34: −0.50455731 35: 0.87040234 36: 0.59407818
37: 1.0408165 38: 0.83375084 39: 0.59187216 40: 0.58443272 41: 1.0092293 42: 0.22197787 43:
−0.44589493 44: −1.1379919 45: 0.3581925 46: 0.70814025 47: −0.42151362 48: −0.052317169 49:
−0.11082876 50: 0.2889609 51: 1.2139032 52: −1.1592975 53: −0.059054762 54: −0.18548462 55:
−0.77073801 56: 0.26250359 57: −0.36623242 58: −0.031984866 59: 0.26953441 60: −0.85498047
61: 0.36182615 62: −0.74242324 63: −0.29094225 64: −0.91586173 65: 0.30981737 66: −0.32983193
67: −1.3585093 68: −0.12513724 69: −0.010376908 70: 0.38823065 71: −0.0060941791 72: 0.27587929
73: 0.25745854 74: −1.291971 75: 0.42582241 76: −0.36651218 77: 0.31846911 78: 0.88084328 79:
−0.77209193 80: −0.33607072 81: −0.31164974 82: 0.25311977 83: 0.36149731 84: −0.057023317
85: 0.27844882 #
−0.0016257259442838685 1: −1.2745243 2: 1.3725504 3: −0.40984562 4: −2.6292028 5: −5.3895054
6: 5.9739404 7: −4.5711613 8: 2.2052009 9: −5.2465138 10: −0.67647785 11: 1.0394732 12: 2.7295601
13: −2.7722533 14: 1.1244704 15: −0.89633745 16: −0.9274469 17: 1.6699194 18: −1.6771654 19:
−0.72681016 20: −0.44002792 21: −0.26600459 22: −0.98991096 23: −0.93116117 24: 0.69509518

APPENDIX C4-continued

SVM Model Weights
(85; Normal/Diseased)

25: 0.92285657 26: −0.063109092 27: −1.1735464 28: −0.5015974 29: −0.96754038 30: −0.37860304 31: 0.082809262 32: 1.2631295 33: −0.43986905 34: −0.93515766 35: −0.39846018 36: −1.7811431 37: 0.96436918 38: −0.86943996 39: −0.1857571 40: −0.052335016 41: 0.77989316 42: 1.9585305 43: 0.5136919 44: 0.70290852 45: −0.65992278 46: −0.62819904 47: 0.042234074 48: −0.27403095 49: −1.5831054 50: 0.57542837 51: 1.2535095 52: −0.27763495 53: 0.30042842 54: −0.026697634 55: 0.83986866 56: −1.7717499 57: 0.56075555 58: −0.32618308 59: −1.2565497 60: 0.24616675 61: −0.31638002 62: 0.1136407 63: −0.524584 64: 0.49817708 65: −0.77622032 66: 0.67375588 67: −0.68531972 68: −0.88069934 69: −0.59614903 70: −0.48646048 71: −0.26088428 72: 0.92441028 73: 0.9558959 74: −0.80790859 75: 0.9994542 76: −1.1186945 77: −0.54430348 78: 0.31087041 79: −0.12128209 80: 0.049723487 81: −0.068356842 82: −1.0160431 83: 0.24992315 84: 0.64890897 85: 0.035451155 #
−0.0035207597532646157 1: −2.2816663 2: −0.1950358 3: −5.0425577 4: 1.724364 5: −0.82801467 6: 2.5474527 7: −4.9610643 8: −0.55181468 9: −0.79765153 10: 2.3832989 11: 0.10773348 12: 1.0693098 13: −1.2152728 14: 0.79049957 15: 0.0099222139 16: −1.4971162 17: −2.0980864 18: 1.5831172 19: 0.44416675 20: 0.65041918 21: 0.34350562 22: 0.71617293 23: −1.3270057 24: 1.3510978 25: −1.3417459 26: 0.16030331 27: 1.2561779 28: 0.30793247 29: −1.5139967 30: −1.4691375 31: −0.77589041 32: −0.13834539 33: 0.60559732 34: −0.23270255 35: −0.91066253 36: 1.1967326 37: −0.38090953 38: 0.92491049 39: 0.22646277 40: 0.0545705 41: −0.51402158 42: 0.036931422 43: −0.34624645 44: −0.26213413 45: −0.54855555 46: 0.65808016 47: 0.60549748 48: −1.3048626 49: −0.02858902 50: 1.158542 51: −0.51622027 52: −0.48286453 53: −0.42171869 54: 0.15448236 55: 0.22208098 56: −0.96829629 57: −0.81633997 58: 0.69672573 59: 0.43771729 60: −0.33384237 61: −0.30339918 62: −0.23418264 63: −1.0594679 64: −0.28116763 65: −1.0582877 66: 0.24212617 67: −0.021668741 68: −0.38854149 69: −0.025471134 70: −0.057951681 71: −0.28464383 72: 0.55788136 73: −0.14839807 74: 1.2589951 75: −0.17693742 76: −0.42702228 77: −0.80403411 78: −1.2830989 79: 0.43489653 80: −0.29964188 81: 0.53392845 82: 0.30745533 83: 0.32345781 84: −0.031299688 85: −0.084129535 #
−0.0012501409361290879 1: 2.1708891 2: 2.2614357 3: −3.51179 4: −0.65605903 5: −2.0876923 6: 0.98526502 7: −3.7276006 8: −2.333333 9: −0.7626673 10: 1.9041126 11: 0.56286615 12: 1.27456 13: −1.2070498 14: 0.76551163 15: −1.425539 16: −1.9847383 17: −2.0789609 18: 1.3220781 19: −0.015966244 20: 1.4032682 21: −0.23330304 22: −0.94637066 23: −0.78442478 24: −0.38136712 25: −0.44472805 26: −0.95212942 27: 0.25056025 28: −1.7206384 29: −1.8087838 30: 0.83157372 31: 0.91639489 32: 1.6293341 33: 0.61387813 34: −0.16359013 35: 0.75835514 36: −0.092014663 37: 0.92941236 38: 0.35514775 39: 0.31088394 40: −0.25040948 41: −0.1788341 42: −1.0098658 43: −1.4341083 44: −0.36132643 45: −0.64555091 46: 0.057727657 47: −0.47578892 48: −0.47918755 49: −1.2079383 50: −0.050135203 51: −0.40510011 52: 0.27559119 53: −1.9835401 54: −0.44731498 55: 0.19911686 56: 0.20567349 57: 0.97765356 58: 1.0810498 59: 0.21141325 60: 0.25757796 61: 1.0486588 62: 0.15312012 63: 0.87443727 64: 0.49931028 65: 0.0023828757 66: 0.50078958 67: −0.12524912 68: 0.034663875 69: −1.2526684 70: −0.3739877 71: 0.25519511 72: 0.2986595 73: −0.08473713 74: −0.54999202 75: −0.89657128 76: −0.16769353 77: 0.38914543 78: −0.33761916 79: 0.11389606 80: 0.027786236 81: 0.6460126 82: −0.13587488 83: 0.40820572 84: 0.15633218 85: −0.14094087 #
−8.9921320849170767e−005 1: −0.65065694 2: −11.223598 3: 1.5055434 4: −4.3927703 5: −0.60701919 6: 8.6285686 7: −1.9276042 8: 10.040118 9: 7.8989391 10: 1.4171855 11: 1.1073941 12: −14.540407 13: −10.239526 14: 3.6424522 15: −3.7669489 16: −3.0639727 17: −2.6669984 18: −3.3562353 19: 1.1029365 20: 3.2188668 21: −1.3355631 22: 0.76778799 23: 7.7980146 24: 1.9258534 25: 0.155596 26: 1.4333936 27: −0.77129906 28: 1.0654082 29: 1.3451784 30: 0.48762089 31: 1.1563978 32: 1.6590519 33: −1.8909501 34: −1.4574517 35: 0.56878603 36: 1.0720688 37: −0.074896112 38: 0.67724591 39: 0.11796083 40: −0.80937344 41: −0.72812855 42: 0.62427038 43: −0.14251851 44: −1.2614839 45: 0.80392224 46: 0.055927221 47: −0.51965183 48: 0.68937206 49: −0.029368833 50: 0.29346243 51: 0.54400104 52: 0.026291719 53: −0.36792743 54: −0.33510557 55: 0.01633551 56: 0.62049705 57: −0.23660533 58: −0.29055452 59: 0.21570383 60: 0.47372437 61: 0.33341625 62: −0.42971212 63: −0.16324264 64: −0.11314408 65: −0.25130454 66: −0.077694908 67: −0.30443865 68: 0.48772439 69: −0.18433747 70: 0.12364767 71: −0.03648885 72: −0.4479292 73: −0.10614621 74: −0.071375042 75: −0.12610583 76: 0.27633363 77: −0.26804826 78: −0.071432278 79: −0.14241533 80: 0.01881632 81: −0.16835345 82: −0.039293341 83: 0.22493207 84: −0.046756189 85: −0.11474198 #

APPENDIX C5

SVM Model Weights
(87; Benign/Malignant)

SVM-light Version V6.01
0 # kernel type
3 # kernel parameter - d
1 # kernel parameter - g
1 # kernel parameter - s
1 # kernel parameter - r
empty # kernel parameter - u
87 # highest feature index
99 # number of training documents
66 # number of support vectors plus 1
0.37432449 # threshold b, each following line is a SV (starting with alpha*y)
0.0019345539215048922 1: 16.053837 2: −15.819319 3: −1.6210849 4: 3.6457462 5: 4.4152589

APPENDIX C5-continued

| SVM Model Weights (87; Benign/Malignant) |
| --- |

6: 10.210145 7: 1.1093941 8: −8.4489651 9: −7.8424716 10: 1.2531379 11: −5.7854691 12: 0.85058212 13: 11.505015 14: 0.58409226 15: 5.614861 16: −5.0463986 17: −2.4444163 18: −0.25845858 19: 1.0797292 20: −3.8040044 21: 1.912954 22: 0.23680127 23: −0.15167442 24: −1.3719921 25: 2.5946932 26: 0.17403919 27: −1.2898791 28: 0.059081983 29: 0.14672025 30: −0.37540862 31: −0.84801257 32: −2.1527555 33: 0.91871446 34: 1.3559048 35: 0.67161536 36: −0.63155913 37: −0.018472454 38: −0.84158731 39: −0.48751351 40: 0.55238557 41: 0.38652408 42: 0.61224627 43: 0.093065917 44: 0.88691741 45: −0.67179191 46: −0.63606435 47: 0.50656343 48: 0.21145603 49: 0.67526537 50: −0.22676751 51: −0.46594143 52: 0.05076601 53: −0.47603023 54: −0.63072002 55: −0.081272468 56: 0.052577384 57: −0.13437749 58: 0.81059444 59: −0.17985293 60: −0.24758452 61: −0.31849173 62: −0.22030351 63: 0.14344099 64: −0.12765574 65: 0.22939913 66: −0.47950178 67: 0.35782388 68: −0.22129388 69: 0.043932721 70: 0.087613709 71: −0.13730107 72: 0.30508745 73: −0.26749346 74: −0.13291891 75: −0.23315008 76: −0.27495328 77: −0.14503081 78: 0.052623045 79: −0.39191145 80: 0.057538711 81: −0.011613904 82: −0.15190414 83: −0.06746494 84: −0.022860833 85: 0.11173677 86: 0.1248471 87: 0.15941496 #
−0.0011947279454286176 1: −6.6617446 2: 2.1398783 3: 4.6612291 4: 4.1200266 5: −9.3816519 6: −0.51241511 7: 1.9775529 8: −2.3050761 9: 0.16089861 10: 2.2131913 11: −1.6792704 12: 3.1526086 13: 0.84659821 14: −2.3553936 15: 2.7890522 16: 1.8426282 17: 0.29614833 18: 0.99678963 19: 1.0124475 20: −0.8951236 21: −0.28949109 22: −2.5569632 23: 1.5312668 24: −1.8644742 25: 0.57216853 26: 0.16517471 27: 0.74864984 28: 0.27347502 29: −0.47111201 30: −0.25048435 31: −1.4497271 32: −1.4426607 33: −0.011552157 34: −1.0720286 35: −1.815498 36: 1.3534091 37: −0.46674749 38: −0.952268 39: 1.464447 40: −0.074659206 41: 0.48858941 42: −0.57241172 43: −0.52673846 44: 0.54606819 45: −0.59332341 46: 0.2707729 47: 0.54184961 48: −1.816597 49: −0.69199657 50: 0.63413811 51: 1.6984042 52: −1.0161058 53: −0.38531092 54: 1.0689594 55: 1.4721197 56: −0.043617524 57: −1.307793 58: 0.55282313 59: 0.2953912 60: −0.90128732 61: −1.319623 62: 0.10041022 63: −1.1754335 64: −0.082541145 65: −0.88779491 66: 1.0713943 67: −0.0046418332 68: 1.8259735 69: −0.039097067 70: −0.065624237 71: 0.047109779 72: −0.49761131 73: 0.37601602 74: −0.94081354 75: 0.215638 76: −0.17871481 77: −0.26326942 78: 0.53398281 79: −0.62913889 80: 0.27845526 81: 1.0219557 82: 0.40206265 83: −0.15983522 84: 0.28322443 85: 0.080510534 86: −0.60540879 87: −0.090221278 #
−0.003330576550580226 1: 5.8117294 2: −1.9790573 3: 3.3024013 4: 1.4090675 5: 4.0260754 6: 1.7043306 7: −1.2717206 8: −5.0069366 9: −0.5155825 10: 4.2741876 11: −0.63364661 12: 3.6082911 13: −1.0221395 14: 4.3295956 15: −3.6911883 16: 3.8338921 17: 1.1320567 18: 0.076046549 19: 0.73055929 20: 1.5319011 21: 2.0646148 22: 2.5041037 23: −1.2301037 24: 1.9691244 25: −1.8752548 26: −1.3004006 27: −1.2616713 28: 1.7858572 29: −0.20650764 30: −1.0955508 31: −2.3334486 32: −0.79862034 33: 0.030790489 34: 1.0012672 35: 1.8106725 36: −1.6918612 37: −0.078678705 38: −1.9022893 39: −0.18735471 40: 0.61756462 41: −1.9212548 42: −0.56349087 43: 0.95128506 44: −0.74089682 45: −0.28381586 46: 0.05123556 47: −1.8658906 48: −1.0558826 49: −1.4784955 50: 0.056897756 51: 1.3088051 52: 0.60886765 53: −1.3749502 54: 0.55317581 55: −0.20789304 56: −0.57680702 57: −0.19929507 58: 0.070962057 59: −0.18337604 60: 0.60094124 61: 0.4337717 62: −1.0110999 63: 0.20664433 64: −0.84325552 65: 0.20657222 66: −0.31070495 67: −0.8924616 68: −0.24730444 69: −0.72580957 70: −0.3408629 71: 1.2265911 72: −0.74530989 73: 0.55862898 74: 0.2842778 75: 0.71336466 76: −0.10710888 77: 0.22261065 78: −0.51533312 79: −0.75857943 80: 0.56938082 81: 0.73724353 82: −0.78785485 83: 0.52528638 84: 0.078715399 85: 0.10680436 86: −0.23703557 87: 0.046045572 #
0.003330576550580226 1: −0.23311329 2: −1.5340611 3: −0.56233943 4: −7.4785199 5: −3.6518826 6: −4.7517338 7: −0.41352883 8: −1.1385972 9: −2.3377373 10: 0.89005411 11: −3.0769937 12: 0.91200078 13: −1.0174296 14: −0.29183522 15: 5.4507852 16: 1.9547648 17: 2.4246554 18: −2.5977473 19: 0.059181549 20: 0.9693011 21: −1.3478724 22: 1.2955381 23: 0.29502755 24: −0.31393111 25: −0.025742445 26: −1.3289164 27: −1.1254236 28: 0.11153328 29: 1.9973383 30: 1.257899 31: 0.91507447 32: 0.72226965 33: 0.39845112 34: −1.3278019 35: −0.95194173 36: −2.0961843 37: −1.1352364 38: −0.64997375 39: 0.065316387 40: −0.38678196 41: 0.77325523 42: 1.3836633 43: 1.3171499 44: 0.053990051 45: 0.77371556 46: 2.1609168 47: −1.3172421 48: 0.39412561 49: 0.23929304 50: 1.105505 51: 0.84551901 52: −0.40700731 53: −0.40167317 54: −0.76905733 55: −0.42601669 56: 1.0445652 57: 1.9075065 58: 1.0322175 59: −0.4670966 60: 0.30819783 61: 0.74754339 62: −0.26703897 63: 0.57786393 64: −0.32511202 65: 0.16155197 66: −0.72578001 67: −0.066891424 68: 0.11020496 69: −0.62233603 70: −0.98494661 71: −0.0048836544 72: 0.43202633 73: 0.55178761 74: −0.32371372 75: −0.18778911 76: −0.38373259 77: −0.52735662 78: 0.35236505 79: 0.060871631 80: −1.1960546 81: −0.47478089 82: 0.44778258 83: −0.11591902 84: −0.41117722 85: 0.94405186 86: −0.52732617 87: 0.035399996 #
0.003330576550580226 1: 5.7773232 2: −0.2485496 3: −4.9756732 4: 2.3672733 5: −1.7608249 6: −4.6183424 7: −6.1881247 8: −1.4636059 9: 0.42568609 10: 0.91490215 11: 2.9737656 12: 1.4572622 13: 2.3844304 14: 3.479558 15: −2.172904 16: 1.3687432 17: −2.2401547 18: 2.038378 19: −1.0956939 20: 2.6179361 21: 4.8499289 22: −1.0542914 23: −1.1590868 24: 2.5353518 25: 0.69207913 26: −5.589396 27: 1.1018655 28: 4.4162931 29: 2.5424984 30: −0.49032038 31: 1.8779082 32: −2.026341 33: −3.0662463 34: −1.2714849 35: −1.7003183 36: 0.089564629 37: −0.045071993 38: 1.3744485 39: −1.2290742 40: 1.29223 41: 0.27818131 42: −0.72624052 43: 0.26687896 44: −0.15784797 45: 0.26189137 46: −0.28338087 47: 0.54031122 48: −0.3526116 49: 0.74344003 50: −1.500893 51: 0.69248003 52: −0.87673593 53: 0.35906056 54: −0.0430285 55: −0.05152908 56: −0.055442557 57: −0.063158438 58: 0.29045451 59: −0.47792071 60: −0.71567893 61: 0.2203918 62: 0.75583583 63: −0.33738095 64: 0.40889195 65: 0.36191818 66: −0.52839923 67: 0.72879851 68: 0.44805676 69: 0.1652946 70: −0.25166011 71: 0.23027706 72: 0.59822512 73: −0.41949832 74: −0.62871504 75: −0.47131854 76: −0.10790173 77: 0.11770677 78: 0.30318615 79: −0.15497944 80: −0.43600088 81: −0.14937481 82: 0.14475852 83: −0.094878353 84: 0.014042439 85: 0.16163081 86: 0.25650221 87: 0.1918962 #
0.003330576550580226 1: 2.3662179 2: 1.6748204 3: 3.8486438 4: 1.4897406 5: −0.9291935 6: −7.1160836 7: −1.9521724 8: 1.1360776 9: −1.8011853 10: 2.2141206 11: 1.7985709 12: −2.1508341 13: 1.6635997 14: 0.10243254 15: −0.36165324 16: 1.0803972 17: 0.49766871 18: 0.0012823264 19:

APPENDIX C5-continued

SVM Model Weights
(87; Benign/Malignant)

−0.98907411 20: −2.9658399 21: 0.10815067 22: 1.4386787 23: −1.396909 24: −0.14514606 25: −0.095915295 26: −0.20809935 27: −1.45952 28: −0.80965692 29: −0.10805699 30: 0.23815021 31: −0.7416473 32: 0.14330949 33: 0.084148057 34: 0.099837765 35: −2.0965025 36: −0.92405814 37: −0.084430851 38: −0.96411276 39: −1.1714625 40: 0.35370091 41: 0.54465806 42: 0.024007868 43: −1.4951186 44: −1.5395824 45: 1.2847537 46: 0.72993517 47: −0.69907892 48: −0.5942564 49: −0.5684616 50: 1.1084251 51: −0.76730984 52: 0.28232136 53: 0.12850039 54: −0.92810959 55: −1.2326117 56: −1.144209 57: 0.19738084 58: 0.55337465 59: −0.89919609 60: −0.69901681 61: 0.4998959 62: −0.0089700799 63: −0.96022487 64: 0.5021655 65: −1.2189608 66: 0.82021332 67: −0.11272306 68: −0.123798 69: 0.019708304 70: −0.24779686 71: −0.85190767 72: 0.48128524 73: −1.2304204 74: 0.93169534 75: −1.5035605 76: −1.2377514 77: 0.28679666 78: 0.21370013 79: 0.081786178 80: 1.162581 81: 0.40195379 82: −0.67829359 83: 0.50082994 84: 0.24331501 85: −0.63211483 86: 0.25782165 87: −0.40200973 #
0.003330576550580226 1: −5.2307115 2: 5.5413795 3: 4.0636749 4: −6.2058477 5: 4.1717806 6: 1.6895379 7: 0.53004158 8: −4.6441884 9: 3.1082587 10: 0.048623063 11: −1.3503591 12: 0.17829828 13: −0.59768867 14: 0.87042594 15: −0.4560613 16: −0.69823253 17: −0.94882631 18: −1.0522534 19: −2.2051711 20: −2.6186538 21: 1.3570184 22:−3.7802284 23: 1.1904382 24: 2.3432648 25: −1.1689653 26: 2.4562342 27: 0.067852028 28: −2.5447171 29: 2.2677996 30: 0.92332506 31: −2.3834748 32: −0.49822828 33: −0.17621896 34: 0.51221931 35: −3.6821847 36: −0.38832191 37: 1.3851066 38: 1.8787074 39: −0.19868882 40: 0.63223851 41: 0.81729114 42: 0.5081135 43: −0.64843142 44: −1.4564943 45: 1.2146252 46: 0.12510775 47: 1.2823189 48: 0.75310415 49: −0.65507919 50: −1.0283387 51: −0.81086957 52: −0.84513521 53: −0.20092514 54: 0.041422322 55: −0.96993876 56: 0.5406127 57: 0.16784817 58: 0.052268587 59: −1.0685024 60: −1.1371231 61: −0.29202485 62: −1.5704151 63: −0.014245392 64: −0.24259058 65: 1.4461937 66: 0.37964907 67: −0.13091937 68: 0.052078299 69: −0.20226718 70: −0.91403842 71: 0.89176095 72: 0.60484374 73: 0.27189174 74: 0.012570418 75: 0.70590878 76: −0.089948945 77: 0.62381929 78: −0.47178656 79: −0.026025595 80: 0.56783694 81: −0.21542034 82: 0.19036613 83: −0.091159619 84: −0.25391325 85: 0.54905295 86: 0.19299547 87: 0.25178668 #
0.0024897955642017252 1: −3.8347991 2: 0.4250325 3: −15.678971 4: 7.1875505 5: 0.54047203 6: −4.0046563 7: 1.9759779 8: 1.9077226 9: 10.761656 10: −8.7568007 11: −1.4441179 12: −0.30809698 13: −1.9578561 14: −4.2252517 15: 8.2054901 16: −1.636007 17: 2.6754603 18: 7.3106451 19: −4.4067588 20: −2.1794596 21: 3.0483193 22: −0.39562172 23: −1.4235375 24: 1.0369247 25: −0.085445531 26: 0.30943248 27: −3.5057745 28: 1.2857898 29: 0.37323707 30: −1.1636015 31: −0.86200023 32: −0.39294812 33: 0.30153993 34: −0.14372639 35: 0.73093683 36: 0.12857766 37: 0.41396561 38: −0.94348228 39: 0.1596809 40: −0.35982186 41: −0.081217997 42: −0.14757583 43: 0.31640163 44: −0.98368734 45: −0.13041568 46: 0.27535918 47: −0.72610444 48: −0.27246878 49: 0.10889015 50: 0.083886296 51: −0.64067858 52: 0.56922275 53: −0.44650257 54: 0.023570085 55: −0.27306849 56: −0.18727268 57: −0.20339593 58: −0.0058271685 59: −0.099581204 60: 0.39475891 61: 0.19308588 62: −0.0053478032 63: 0.096731231 64: 0.26979297 65: 0.15184869 66: −0.18696959 67: −0.15064354 68: −0.30398273 69: 0.083900169 70: 0.10426281 71: 0.35618588 72: −0.34764102 73: 0.30011776 74: −0.033746786 75: 0.050758284 76: 0.22227693 77: 0.062899485 78: 0.11515583 79: −0.32982102 80: 0.17524947 81: −0.12747638 82: 0.20460217 83: −0.097438082 84: 0.16689576 85: −0.036133129 86: 0.12806532 87: 0.034909908 #
−0.003330576550580226 1: 7.9274554 2: 4.6073709 3: 1.4603447 4: 2.0189972 5: 0.78566617 6: −1.9227256 7: 2.3366702 8: 3.8609731 9: −1.7538786 10: −1.9488626 11: 1.0148774 12: 1.0113562 13: 0.048932023 14: 0.18989503 15: −2.6325822 16: −1.2078793 17: −0.14492357 18: 2.2336729 19: 1.5534426 20: 0.35241047 21: 0.80466956 22: 1.8033856 23: −1.1963571 24: 0.040374711 25: 0.84861618 26: 1.267494 27: −0.13946263 28: −1.7854359 29: −0.44070604 30: 1.0542413 31: −1.2373537 32: 1.3077921 33: 0.041555852 34: −2.5827558 35: −0.43862686 36: −1.175679 37: −0.36042389 38: −0.17961439 39: −1.2788309 40: 1.3294245 41: 1.2669107 42: −2.5629046 43: −0.61600578 44: 1.0869129 45: 0.16643843 46: 0.41818899 47: −0.63434148 48: 1.260896 49: −1.4160058 50: −0.47209889 51: −0.61638838 52: 0.43397504 53: −1.1642369 54: −1.3824058 55: 0.054856647 56: −0.68154693 57: −1.2291157 58: 1.1269206 59: 0.42816728 60: −0.81057531 61: −0.35877511 62: −0.75165677 63: −0.63177156 64: 0.20773476 65: 0.13551633 66: −0.5237487 67: −0.51673758 68: 0.30764231 69: −0.88030827 70: −0.46954823 71: −1.061381 72: −0.25684392 73: −0.044407751 74: −0.88750231 75: −0.013286038 76: 1.4483461 77: −1.314014 78: −0.73927134 79: −0.64270085 80: −0.63794053 81: −0.60478133 82: −0.30900621 83: −0.12258168 84: −0.42564362 85: −0.26520431 86: −0.11208617 87: 0.43734992 #
−0.003330576550580226 1: 8.918601 2: −2.3055892 3: 3.1710715 4: −0.15590623 5: 4.4929414 6: 8.9671669 7: 3.5218017 8: −0.39461762 9: 2.7775333 10: 1.1787916 11: 0.15996362 12: 2.4074681 13: −3.6746743 14: 0.4590081 15: −1.2401536 16: −0.21795638 17: −2.150651 18: 1.5083847 19: −2.3201568 20: −1.4036152 21: 1.2891895 22: 1.8004652 23: −2.8867595 24: −0.48214114 25: −0.6927855 26: 1.416193 27: 0.6444248 28: −1.7029501 29: 0.43822736 30: −0.49788377 31: −0.52655113 32: −1.7165399 33: −1.1928347 34: −0.22806802 35: 0.57792765 36: −1.309574 37: −2.4833274 38: 0.51614594 39: −1.1733458 40: 0.19606277 41: −0.48785424 42: 0.74374002 43: 1.6714115 44: −1.012743 45: 0.2366548 46: 0.19854921 47: 0.11224885 48: −0.12991515 49: 0.75364155 50: 1.8194386 51: 0.83108264 52: −0.0015029972 53: 1.4728006 54: 0.20966282 55: 0.92609775 56: −0.79182535 57: −0.32760841 58: −0.0991785 59: −1.0574496 60: 0.37978888 61: −0.10320935 62: 0.60087049 63: −0.052789245 64: 0.46512586 65: 0.98970068 66: 1.4638492 67: −0.57553667 68: −0.0046812133 69: −0.0082963342 70: −0.15113865 71: −1.3569248 72: 0.56353962 73: −0.0099311648 74: −0.091379911 75: 0.49824885 76: 0.06418056 77: 0.8926155 78: 0.67386544 79: 0.96177387 80: −0.68476832 81: 0.09199404 82: 0.31347424 83: −0.13139787 84: −0.28070489 85: −0.36300245 86: −0.56763732 87: 0.36510098 #
−0.003330576550580226 1: 1.6040151 2: 0.24394807 3: −0.09684144 4: −2.4873862 5: 1.2782253 6: −3.957773 7: 1.591818 8: 5.2486348 9: −3.780654 10: 0.71394485 11: 0.55227733 12: 2.4138548 13: −0.35664403 14: 0.24096936 15: 0.61735266 16: −1.0579739 17: −0.3856262 18: 0.43396828 19: 0.52961248 20: −0.58919561 21: 0.35186648 22: −0.27301615 23: −0.5683229 24: −0.66487145 25: −0.83458596 26: −1.3270503 27: 1.6758934 28: −0.087032422 29: 0.037628613 30: 0.15866874 31:

APPENDIX C5-continued

| SVM Model Weights (87; Benign/Malignant) |
|---|
| −1.4669696 32: 0.069000371 33: −0.95354003 34: −0.042669386 35: −0.15571766 36: 2.2095904 37: 0.081673302 38: −0.59341264 39: 0.79293787 40: −0.73346049 41: −0.10772487 42: 0.011551697 43: −1.4501675 44: 0.17495763 45: −0.097596668 46: 1.0937287 47: −1.4059062 48: 0.44559744 49: 1.4810617 50: −0.18444139 51: −1.2559286 52: −1.2589086 53: −1.1882739 54: −0.43347055 55: 0.94245815 56: 0.26500198 57: 1.3265449 58: 0.17797512 59: −0.11993234 60: 0.26297709 61: 0.67024577 62: 0.11923546 63: 0.35726729 64: −0.64151269 65: −0.47890148 66: 1.0967112 67: −0.12874754 68: −0.9067179 69: 0.91967088 70: 0.95822871 71: −0.20772138 72: 1.1771448 73: 0.3509993 74: −0.51153505 75: 1.0094274 76: −0.8650856 77: 0.41146982 78: 0.15137386 79: −0.95347089 80: 0.16219261 81: −0.45549694 82: −0.73642898 83: −0.00017498361 84: −0.47792503 85: −0.35363454 86: −0.0076037394 87: 0.39873832 # |
| −0.003330576550580226 1: 3.1450987 2: 3.0755467 3: 3.8123691 4: −5.2419996 5: 3.5220785 6: 2.7474384 7: 3.2287869 8: −0.89663881 9: 1.4479074 10: 0.22962917 11: −0.68433446 12: 0.67356664 13: −2.3352745 14: 0.13635983 15: −1.3551366 16: −0.17511296 17: −0.53919446 18: 0.34350392 19: −1.4785919 20: 0.38314915 21: 1.0084164 22: −0.74683142 23: −1.01981 24: 0.92450368 25: 0.048945725 26: 2.4303942 27: 1.9733022 28: −1.084133 29: 2.4037261 30: −0.20327578 31: −0.21382751 32: 0.38244691 33: −1.5787801 34: 0.58106166 35: 0.56194413 36: −1.0568376 37: −0.39388707 38: 0.77245092 39: 0.22725876 40: 0.56400257 41: −0.71169043 42: −1.4364457 43: 0.15108694 44: 0.1501902 45: −1.2559881 46: −0.47359699 47: 0.88458729 48: −1.0644742 49: −0.26796979 50: 0.45492792 51: −0.35489604 52: −0.0036850711 53: 0.67428136 54: 0.18258713 55: 0.66911966 56: 0.85411978 57: 1.4131602 58: −0.17310233 59: 0.26988244 60: 0.63591391 61: −1.492577 62: 1.1587889 63: 0.24478087 64: −0.0090595074 65: 0.09246061 66: −0.010267213 67: 0.0090993661 68: −0.34929219 69: 0.63706648 70: 0.64416522 71: 0.43840125 72: −0.15390216 73: −0.22265123 74: 0.4152877 75: −0.98270524 76: −0.076135524 77: −1.5789219 78: 0.80812001 79: −1.4226592 80: 0.69282353 81: −1.2014222 82: −0.40982008 83: −0.36414981 84: −0.32098812 85: −0.34560445 86: 0.05994729 87: −0.19077258 # |
| 0.0019500884505873116 1: −0.27885634 2: 9.8825912 3: 5.0959301 4: 11.570415 5: −1.236788 6: 1.985296 7: 5.2343593 8: 0.62978274 9: 2.3628919 10: −4.0060329 11: −1.5498919 12: −5.6165047 13: 1.9572977 14: 1.525573 15: −1.4694535 16: −0.72089523 17: 6.3752151 18: −3.8398392 19: −0.22521774 20: 2.0210238 21: −2.0194118 22: −0.11568941 23: −2.104739 24: 1.9838831 25: 3.0514641 26: 0.59763795 27: 1.0259111 28: 0.36511812 29: −1.4264234 30: 0.1027429 31: 2.357899 32: −1.9932759 33: 0.25746295 34: −1.3807032 35: −0.80859441 36: −1.3570629 37: −0.43601882 38: 1.2783484 39: 0.33894697 40: −0.14031106 41: 0.36673552 42: 0.78659517 43: 2.2073028 44: −1.7938133 45: −3.3127129 46: 0.55814505 47: 0.23499101 48: −0.31328574 49: −0.3678259 50: −1.0919495 51: −0.54220551 52: −0.10577908 53: 0.056796744 54: −1.0248491 55: 0.364755 56: −0.1218835 57: −0.37480712 58: 0.69237989 59: −0.72456926 60: 0.11871188 61: −0.29808462 62: −0.33266142 63: 0.51533318 64: −0.40029058 65: −0.54870594 66: 0.74644834 67: −0.043202028 68: −0.4499062 69: 0.57941437 70: −0.13789555 71: 0.21616811 72: 0.22102049 73: −0.23642012 74: −0.23389414 75: −0.18306223 76: −0.10923698 77: 0.082572661 78: −0.31490263 79: −0.28321487 80: 0.21753868 81: 0.26736733 82: −0.25724804 83: 0.3210631 84: 0.074870519 85: 0.12955892 86: 0.14472702 87: 0.19907668 # |
| 0.0018972403340262014 1: 0.43924162 2: 11.232109 3: −3.9407368 4: −2.2011461 5: −11.28683 6: 11.626836 7: −2.2610507 8: 1.9518424 9: −9.4666557 10: −3.7131739 11: 10.517995 12: −6.7265964 13: −4.0587149 14: 6.8698277 15: 6.0822682 16: −1.0870117 17: 1.8049608 18: −3.1073513 19: −2.3271327 20: 1.4725494 21: 3.9342456 22: 1.8926948 23: 3.0023232 24: 0.81837815 25: −0.33446386 26: 0.58317035 27: −0.11714862 28: −0.81818438 29: −0.47216067 30: −0.54521555 31: −2.5090654 32: −0.71020037 33: −0.075489208 34: −0.15132225 35: 0.75384641 36: 0.67422163 37: −0.83866471 38: 0.21326746 39: 0.2087258 40: −0.65981603 41: 0.031596351 42: −0.67660743 43: −0.17599575 44: 0.40585941 45: 0.66532815 46: −0.32825023 47: 0.21217279 48: −0.21592824 49: 0.049525786 50: 0.23724128 51: 0.015045444 52: 0.42865586 53: 0.066027313 54: −0.063017264 55: 0.014561494 56: 0.30450827 57: −0.55682224 58: 0.034693249 59: −0.099208049 60: −0.030663054 61: 0.25848621 62: −0.17410555 63: 0.31677112 64: 0.37713161 65: 0.081454352 66: −0.13391829 67: 0.060628474 68: 0.0038285842 69: 0.083007328 70: 0.072671026 71: 0.18354052 72: −0.029333215 73: 0.14277005 74: −0.0031624066 75: −0.28545249 76: −0.04553153 77: 0.2340052 78: 0.10836186 79: −0.26486248 80: 0.1415502 81: 0.034146793 82: 0.019663593 83: −0.11012109 84: 0.042360976 85: 0.053964235 86: 0.012122418 87: 0.02180534 # |
| 0.003330576550580226 1: 4.2058864 2: −10.273238 3: 0.86963367 4: 0.76485717 5: 0.58796382 6: 6.4885211 7: −0.5382148 8: 1.6879342 9: 0.99313658 10: 1.3948026 11: −0.040827319 12: −1.919044 13: −2.0231805 14: 1.3912067 15: −0.651649 16: 3.206111 17: 1.5296158 18: 1.1393459 19: −0.41099066 20: −0.96875608 21: 0.36818328 22: −0.98741603 23: 1.1284338 24: −3.8232245 25: 0.81427598 26: −0.40313891 27: −1.2148914 28: 0.74097633 29: 0.53082883 30: −1.3979726 31: 2.3583498 32: 1.422774 33: 1.4029665 34: −1.1116167 35: −0.12920739 36: −1.2420616 37: −0.28832686 38: −0.50600088 39: 1.1798551 40: 0.19203396 41: −0.64383477 42: −1.9600604 43: −3.0673683 44: −1.7651753 45: −0.47080824 46: 0.2957764 47: 0.74461073 48: −1.0844226 49: −1.805436 50: −0.79785281 51: 0.92456198 52: 1.1694111 53: 1.044863 54: 0.16566463 55: −0.46273881 56: 0.75328708 57: 0.41227534 58: 1.1220003 59: 0.14123106 60: 0.16303807 61: 0.97278911 62: −1.6178106 63: −0.48137847 64: 0.71833807 65: 0.20115498 66: −0.058812018 67: 0.086899623 68: −0.080147691 69: 1.0477471 70: 0.42553627 71: −0.27966115 72: 0.43006679 73: −0.63558483 74: −0.64211845 75: 0.61957252 76: −0.24969929 77: 0.14041242 78: 0.56654406 79: 0.4596808 80: −0.087941766 81: −0.55924523 82: 0.10006484 83: −0.11043978 84: −0.50888997 85: −0.21049897 86: −0.23463774 87: 0.40061915 # |
| 0.003330576550580226 1: −4.0771055 2: −1.1504505 3: 2.7464559 4: −3.183337 5: 2.1268644 6: −3.9230978 7: 0.34163719 8: 2.0293679 9: −4.1811166 10: 1.3721042 11: 0.75773573 12: −2.5267835 13: 0.18023184 14: 1.253926 15: 1.903635 16: 4.277389 17: −1.0687795 18: 2.2155018 19: −1.165033 20: 0.49952036 21: −0.53572905 22: −2.7601488 23: 0.46436167 24: −1.0921776 25: 0.40821484 26: −1.8236394 27: −0.6932615 28: −0.47530422 29: −1.0037123 30: −1.4111601 31: −0.97893435 32: 0.59495652 33: −0.61701107 34: 0.9906022 35: 0.68052351 36: −0.63597757 37: −0.46423337 38: −0.89762545 39: 0.13971765 40: −0.3625131 41: 1.1963357 42: 2.2367857 43: 0.054969501 44: |

APPENDIX C5-continued

| SVM Model Weights (87; Benign/Malignant) |
|---|
| −0.94110113 45: −1.5583142 46: −0.44915068 47: −0.34900296 48: 2.1110771 49: −0.28557867 50: −0.040807333 51: −0.40374312 52: −1.1042058 53: 0.65662706 54: 0.30161396 55: 0.22354984 56: −0.87246823 57: −1.0906 58: −1.0315273 59: −0.56604338 60: 0.19954501 61: −0.13208917 62: −0.10269781 63: −0.60582912 64: −0.43352944 65: −0.17152943 66: −0.55465734 67: 1.6623362 68: −0.50636709 69: −0.233804 70: −0.50829476 71: 0.15316477 72: 0.020214388 73: 0.51832306 74: −0.44554862 75: −0.4672696 76: 1.2049603 77: −0.17821534 78: 0.35580134 79: −0.073194116 80: 0.50485861 81: −0.38585055 82: −0.44239968 83: 0.056880467 84: −0.12791957 85: −0.73388392 86: −0.76353788 87: −0.59957105 # |
| 0.00093557632919481044 1: −2.6901774 2: 0.12484454 3: −5.7668495 4: 3.0192795 5: 3.5229359 6: 1.7700055 7: 2.5609665 8: 0.29128727 9: 7.6276684 10: −8.8952122 11: −0.96227884 12: −1.0497365 13: −1.2142708 14: 4.7062192 15: 3.6511281 16: 8.7197504 17: −5.4372635 18: −4.8534231 19: 8.6003857 20: −2.3985815 21: 3.356118 22: −0.72012883 23: −2.1830902 24: −0.51483166 25: 0.088666141 26: −0.73958147 27: −0.082041442 28: −1.527185 29: −1.286461 30: −0.21008573 31: −0.20750855 32: 0.99752599 33: −0.46010032 34: −0.93256456 35: −0.4783504 36: −0.16327481 37: 1.1467155 38: 0.089615069 39: −0.46824008 40: −0.29320472 41: 0.11233055 42: 0.067520261 43: −0.10295373 44: 1.1885079 45: −0.0014238653 46: 0.18009517 47: 0.61626351 48: 0.19040526 49: 0.29867285 50: 0.19637226 51: 0.32745302 52: −0.459636 53: −0.26479769 54: 0.14241518 55: 0.33911103 56: −0.24151367 57: 0.49422511 58: 0.28986484 59: 0.25873479 60: 0.34820062 61: −0.20878318 62: 0.033185318 63: 0.22426644 64: −0.28322926 65: 0.068976313 66: 0.056422386 67: 0.21299103 68: −0.028575726 69: 0.1761578 70: 0.16310479 71: −0.011603817 72: 0.20116013 73: −0.18685398 74: 0.38147083 75: −0.13860913 76: 0.021649625 77: −0.061052207 78: −0.29507366 79: 0.30973631 80: 0.18700933 81: 0.21704787 82: −0.081009842 83: −0.058521919 84: −0.11607506 85: −0.18982829 86: −0.028044887 87: 0.10236598 # |
| −0.0013476262818821014 1: −7.7966084 2: 1.8707227 3: −23.323887 4: 1.0747559 5: 1.0184501 6: −3.600925 7: 9.3491745 8: −7.7337961 9: −1.2228185 10: 7.7243834 11: 2.0076487 12: −4.368228 13: −1.5946441 14: −0.2912291 15: −2.0482881 16: −0.38283157 17: −1.6580502 18: −1.0132759 19: −0.17344542 20: 0.65646726 21: −0.49175465 22: 0.29616475 23: −0.65766221 24: −0.40362445 25: 0.31434533 26: 0.98643875 27: 0.016180724 28: 0.12472247 29: −0.22155482 30: −0.0517218 31: −0.0058854236 32: 0.09278781 33: 0.34776777 34: −0.21737053 35: −0.091020077 36: 0.035350032 37: 0.2550841 38: −0.072128683 39: 0.0050051538 40: −0.072953671 41: 0.1237232 42: −0.10784111 43: −0.24674198 44: 0.10156032 45: −0.11400478 46: −0.0051734848 47: 0.070060618 48: −0.062755756 49: −0.1003389 50: −0.024766795 51: 0.042309508 52: −0.045899741 53: −0.018923813 54: 0.026509475 55: −0.013425832 56: −0.057100177 57: 0.062299002 58: −0.0071787904 59: −0.017751466 60: −0.080059178 61: 0.10251214 62: 0.19948693 63: −0.017395765 64: −0.065834261 65: 0.05320783 66: 0.13003403 67: 0.045583595 68: 0.015333543 69: −0.10374861 70: 0.017438892 71: −0.12824923 72: 0.1228321 73: 0.006350534 74: −0.13356683 75: 0.01609605 76: 0.019531524 77: −0.02920058 78: −0.017909111 79: −0.032119624 80: −0.081862949 81: 0.026391055 82: −0.053974025 83: −0.042487528 84: −0.040375195 85: 0.027134888 86: −0.085319266 87: 0.014382792 # |
| −0.0016357233873406716 1: −3.8587921 2: −16.208611 3: −2.6007581 4: 2.9952328 5: −2.9244998 6: −2.1342196 7: −8.6919346 8: 2.102823 9: −0.65605307 10: −3.5787513 11: 0.57963091 12: −3.8771913 13: 1.4609568 14: 1.0911566 15: −2.6927843 16: −0.73983127 17: −2.9269328 18: −3.2514834 19: −1.6491545 20: −2.8616376 21: −2.9949863 22: 0.38679239 23: −0.50630879 24: 0.66747051 25: −0.56378025 26: 2.5836411 27: −0.59832889 28: 0.37365031 29: 2.3311179 30: 1.4624356 31: 0.31802523 32: −0.90313685 33: −1.2535348 34: −0.47041008 35: 1.9334433 36: 1.0617839 37: 4.1906142 38: 0.26222989 39: 0.44094789 40: −0.27469787 41: 2.5724795 42: −0.9394781 43: −0.5121271 44: −1.7902449 45: −0.76117063 46: −1.2025639 47: −0.75431925 48: −0.27811137 49: −0.86414403 50: −0.0057006418 51: 1.9052811 52: 0.40665537 53: −1.2708704 54: −0.33689812 55: 0.49392983 56: −0.045317728 57: −0.43321306 58: −0.7863214 59: −0.14774203 60: 0.080907896 61: 0.56522685 62: 0.60004711 63: 0.2153769 64: 0.029641049 65: 0.096503533 66: 0.31114331 67: −0.58736598 68: −0.25519821 69: −0.1153139 70: −0.040961515 71: −0.26411968 72: 0.11253919 73: 0.82753402 74: −0.017763685 75: −0.18250082 76: 0.085465781 77: 0.029048748 78: 0.57212704 79: 0.087843932 80: −0.32256076 81: 0.06564676 82: −0.047518075 83: −0.3899799 84: −0.23717856 85: 0.054492351 86: −0.093572512 87: 0.0057938704 # |
| 0.003330576550580226 1: 5.7209835 2: 0.23666459 3: 1.730386 4: 0.35195339 5: 0.080441706 6: 0.4397411 7: 0.79212171 8: −3.2328453 9: 0.53677988 10: −1.278559 11: −1.9872284 12: −3.541455 13: 1.268319 14: −0.80598712 15: −1.9951948 16: 1.6678131 17: 0.39204028 18: −0.14329085 19: 0.0522938 20: −3.9440317 21: −0.70164174 22: 0.37428939 23: 1.37909 24: −0.080555849 25: −0.21866828 26: −0.26640299 27: −0.11733657 28: 0.54316443 29: −0.98517901 30: −0.26204801 31: −0.19700877 32: −0.53598785 33: −0.78479302 34: −1.9096892 35: 0.21801066 36: 0.68265325 37: 0.061487831 38: 1.0199002 39: 0.14417441 40: −0.060175069 41: −2.7730792 42: 0.2983031 43: −0.44488677 44: −0.98700613 45: −0.61365366 46: 1.1833302 47: −0.68848914 48: 1.2433225 49: 1.9442695 50: −0.60836315 51: −0.33906472 52: 0.95265335 53: 0.22811827 54: 1.6679398 55: 0.2450835 56: 1.3480361 57: 0.38068792 58: −1.285329 59: 0.64653748 60: −1.0222931 61: 0.41674906 62: −1.0298935 63: 1.5975699 64: 0.53876853 65: −1.5039648 66: −0.16029453 67: −0.27558342 68: 0.2916702 69: 0.0036349858 70: −0.85938823 71: −0.5335471 72: −1.0547386 73: −0.0090008266 74: −0.11001433 75: −0.20822597 76: −0.074708924 77: 0.24800478 78: 0.29446042 79: −0.97626752 80: −0.87793279 81: 0.14734183 82: −0.15992483 83: −0.14554277 84: −0.44493255 85: −0.05211214 86: −0.14523202 87: −0.47606155 # |
| 0.00072702940903027961 1: 11.480239 2: 4.4015856 3: 2.7414548 4: −1.7944015 5: 0.020670321 6: −3.172972 7: 1.7720693 8: 0.33977011 9: −4.4583831 10: −1.7358112 11: 2.1295266 12: 1.8335074 13: 0.42079771 14: −3.1428821 15: −0.35652745 16: −2.6052432 17: −4.2545991 18: 0.119913 19: −1.3009126 20: 1.0571593 21: 1.7554218 22: 0.98222196 23: −2.4740789 24: 2.3750913 25: −1.2592227 26: −1.2876878 27: −1.3512036 28: −0.99439675 29: −0.6929304 30: 2.0188313 31: 0.39963567 32: 1.9517349 33: 1.1965405 34: −0.96466547 35: 1.5519712 36: 0.37793252 37: −0.006880715 38: −0.34347305 39: 0.069352545 40: 0.40852034 41: −0.1222181 42: 0.5076071 43: −0.59228605 44: −0.22037746 45: −1.0914367 46: 0.544662 47: 1.3248136 48: −0.10031602 49: 0.41528448 50: |

APPENDIX C5-continued

| SVM Model Weights (87; Benign/Malignant) |
|---|
| −0.84254622 51: 0.090518124 52: −0.36615625 53: 0.93545157 54: 0.65838861 55: 0.038296822 56: −1.7492578 57: 0.14129707 58: 0.39605069 59: −0.57719308 60: 0.39486134 61: −0.01404435 62: −0.79504615 63: 0.92434222 64: 1.1236246 65: −0.91369331 66: 0.25839856 67: −1.2276139 68: 1.7978841 69: 0.44832402 70: 0.10241497 71: 0.012899262 72: 0.17863631 73: 0.71144456 74: 0.29484099 75: 0.059212424 76: 0.26446101 77: −0.15068734 78: −0.12540962 79: −0.035991069 80: 0.058723163 81: 0.23377629 82: 0.064840928 83: −0.88246381 84: −0.19494149 85: 0.40759304 86: 0.39069259 87: −0.31211245 # |
| 0.0029534900415909534 1: 12.400963 2: 4.2546644 3: −0.41324967 4: 3.0709786 5: −0.27842081 6: −1.2178549 7: 2.344552 8: −0.065143779 9: 1.4606165 10: 1.0544931 11: −2.142359 12: 2.1907766 13: −1.5534158 14: −0.69449091 15: 0.29213595 16: −3.1575935 17: 1.0698617 18: −2.5730839 19: 0.0092338799 20: −2.99612 21: −0.1943074 22: −0.86630803 23: 1.6802975 24: −1.0868572 25: −1.5044321 26: −1.582459 27: 1.117466 28: −0.57524675 29: 0.018987674 30: 1.4091095 31: −1.0078969 32: 1.5285796 33: 0.31792575 34: −0.12233579 35: −0.34751469 36: 0.051566206 37: −0.022006385 38: 0.26128823 39: −1.0277607 40: −1.3792479 41: 0.59065032 42: −2.1147952 43: −0.15735847 44: 1.2849991 45: −0.53021276 46: 0.85332453 47: −2.4224534 48: −1.7809808 49: −0.53126109 50: −1.4790729 51: −0.88244933 52: −0.72955728 53: 1.2992866 54: 0.40387648 55: 0.015153798 56: 0.11678315 57: −0.38129348 58: 0.88556302 59: −0.087197445 60: 0.38062981 61: 0.42040733 62: 0.92759228 63: −0.3889952 64: −0.19115527 65: 0.35612798 66: −0.088825949 67: −0.0031237327 68: −1.119221 69: 0.26062384 70: −0.45653608 71: 1.213123 72: 0.24663816 73: 0.32365286 74: 0.69991243 75: 0.0058952384 76: −0.10694939 77: −0.14535566 78: 0.55809158 79: 0.056639977 80: −0.66649711 81: 0.91455543 82: 0.41167188 83: −0.37185481 84: 0.77568609 85: −0.37804151 86: 0.45219046 87: 0.28834942 # |
| 0.0020268778993984839 1: 11.932061 2: −0.54239619 3: 4.2213945 4: −5.9421682 5: −2.619386 6: 2.3564994 7: −2.7465849 8: −3.8928757 9: −4.162075 10: −1.7486995 11: 0.47773656 12: −4.1929479 13: −2.0677514 14: −6.5466743 15: 0.092173383 16: 0.91300637 17: −1.0412949 18: 3.4058571 19: 3.6996002 20: 3.7471523 21: −0.1068441 22: 1.0975643 23: −1.3388216 24: 1.3413877 25: 3.6972344 26: 1.4300827 27: −0.18405136 28: 0.59656787 29: 0.032527361 30: −3.2063987 31: 1.3294622 32: 1.2466725 33: −0.6915769 34: 2.29409 35: −1.6047076 36: −0.53606254 37: 2.0452888 38: −0.7539885 39: 0.77716249 40: −3.2375765 41: 0.10940029 42: −1.2017024 43: 0.92225856 44: −0.76386726 45: −0.2991994 46: 0.59694391 47: −0.55408794 48: −0.46362504 49: 0.58976698 50: 0.62997901 51: −0.031874478 52: −1.2171367 53: −0.050087653 54: −0.59428918 55: −0.059566271 56: −0.22709765 57: 0.178231 58: 0.34874552 59: 0.91884744 60: −1.374855 61: 0.59586394 62: 0.01659002 63: 0.39488176 64: 0.23214574 65: 1.2436252 66: 0.88398963 67: −0.21129984 68: 0.16651997 69: −0.46138206 70: −0.45318407 71: 0.22434828 72: 0.11926489 73: 0.49209055 74: 0.43054074 75: 0.14348413 76: −0.013169435 77: −0.051100992 78: 0.080900505 79: −0.18882868 80: 0.1539721 81: 0.23456702 82: 0.33220461 83: −0.068677895 84: −0.2610451 85: −0.46393099 86: 0.03763498 87: 0.102527 # |
| −0.003330576550580226 1: 9.2099752 2: 0.10233181 3: 1.9269702 4: −2.1939819 5: −1.9438351 6: 3.0239697 7: −5.1489539 8: −5.0794964 9: −1.1390828 10: 0.33780786 11: 1.8522336 12: −7.0093985 13: −2.1220815 14: −7.3823423 15: 1.5933274 16: 3.5308435 17: 2.6375818 18: 2.7540584 19: −0.99151331 20: 0.0083616357 21: 0.54905522 22: 0.68470973 23: −1.4407222 24: −1.9258854 25: −0.28219196 26: −0.25906509 27: −0.60497737 28: −1.8318855 29: −2.0681658 30: 2.9541204 31: 2.6221907 32: −0.93029034 33: −1.8050101 34: 0.52987593 35: 0.48732564 36: 0.91307831 37: 0.12632039 38: 0.6361919 39: −2.6943514 40: 3.1532407 41: −0.1327378 42: 0.31272578 43: −0.35162035 44: 1.9987303 45: 0.43408412 46: 0.083819687 47: 0.53805685 48: 0.55005115 49: −0.69969761 50: −1.0889786 51: 0.44436994 52: −0.47532484 53: 0.11296681 54: −0.26162675 55: 0.083675936 56: 0.43792534 57: 0.46311471 58: −0.87382078 59: 1.1646171 60: 0.038086068 61: −0.10682595 62: −0.32176739 63: −0.87397802 64: −1.7255341 65: −0.12923253 66: −0.0063713025 67: −0.32136509 68: −0.46372363 69: 0.2720727 70: −0.040819522 71: 0.093332551 72: −0.10163796 73: 0.054285415 74: 0.51410824 75: 0.42510664 76: −0.44858062 77: 0.094385475 78: −0.039332729 79: 0.11206785 80: 0.043272279 81: 0.3098256 82: −0.31685907 83: −0.15600948 84: 0.26660839 85: 0.095404632 86: 0.07407812 87: 0.23526323 # |
| −0.003330576550580226 1: 4.8919382 2: 6.5307918 3: 4.6522961 4: 0.50912267 5: 1.0186707 6: −1.6481709 7: −1.5135888 8: −1.650799 9: 2.0391626 10: 3.3697751 11: 0.28303525 12: 0.80901867 13: −0.7322185 14: 2.4035478 15: −0.92959404 16: −0.11080018 17: 1.1656927 18: −0.061241843 19: 0.093886204 20: 0.41603193 21: 1.5590807 22: −0.079786256 23: −1.3937597 24: −0.93761557 25: −1.2395495 26: 0.47965881 27: −1.8439426 28: −1.0782979 29: 2.3248599 30: −0.25143835 31: −0.11789405 32: 0.25579667 33: −0.023998141 34: −0.48568967 35: −0.30022782 36: 2.9556475 37: 0.45612425 38: −0.54248434 39: −0.51530242 40: −0.71495318 41: −0.029934257 42: 0.019748591 43: 0.59214228 44: 0.064154685 45: −0.10139915 46: −0.24000387 47: 0.70566356 48: 0.43672034 49: 1.5145738 50: 0.32631695 51: 0.011702045 52: 1.2934036 53: 0.23414563 54: −2.2872193 55: −0.83546925 56: −0.38473645 57: 0.040741041 58: 0.21569888 59: −0.32376489 60: −1.4367403 61: −0.24261849 62: −0.6142832 63: 1.1440008 64: −1.2322909 65: −0.65854615 66: 0.067190781 67: 0.18490925 68: −0.73051834 69: −0.037479538 70: 1.7830526 71: 0.53027761 72: −0.33125749 73: 0.54123253 74: −0.90944654 75: 0.51352841 76: 0.45196581 77: −1.105139 78: 1.0859764 79: 0.75343102 80: −0.30513814 81: 0.98500597 82: 0.011409609 83: 0.49440524 84: −0.14414717 85: −0.52839154 86: 0.30832028 87: −0.39584917 # |
| −0.003330576550580226 1: 3.3829088 2: 2.943239 3: 3.1921368 4: −7.1808729 5: −0.58675814 6: 0.78415442 7: 2.0849354 8: −2.3231814 9: −1.2042598 10: −0.67835438 11: −3.815778 12: −0.030315256 13: −1.9011153 14: 0.15897124 15: −0.94414741 16: 1.256176 17: 1.2059518 18: −2.8228135 19: −0.78729898 20: −0.21089606 21: 1.2398977 22: 0.40475592 23: −2.1799212 24: −1.4266895 25: 0.61812282 26: 0.20725577 27: −2.2211232 28: 1.0998532 29: 1.8443335 30: 0.45508903 31: 0.81324655 32: 0.1167727 33: 0.24159066 34: −0.94804347 35: 0.43025914 36: −1.5013132 37: −0.41262493 38: −0.27913424 39: 1.452195 40: 0.89614612 41: 0.45674798 42: −0.69670659 43: 0.20472988 44: −0.68425399 45: 1.8435879 46: 0.36953163 47: −0.14509733 48: −0.059769865 49: −0.8294245 50: 0.11404043 51: −0.55319852 52: −0.68372446 53: −0.91018629 54: 0.94105601 55: −1.0993478 56: 0.56316334 57: −1.2337679 58: −0.96762305 59: 0.86326998 60: |

APPENDIX C5-continued

SVM Model Weights
(87; Benign/Malignant)

−0.35409802 61: −1.7822696 62: 0.67693377 63: 0.59586 64: 0.77106255 65: −0.08978609 66: −0.55685008 67: 1.2705643 68: −0.11793981 69: 0.20805952 70: 0.71785802 71: −0.9783408 72: 0.13318537 73: 0.63180852 74: 0.044601873 75: 0.2948941 76: −0.057511415 77: 0.80193365 78: 0.1222982 79: −0.57889193 80: −0.61818993 81: 0.11715686 82: 0.32118329 83: 0.84990716 84: 0.5679155 85: −0.84811169 86: 0.93442708 87: −0.53476751 #
−0.003330576550580226 1: 3.5024867 2: 6.5884976 3: 3.7849009 4: 5.5771961 5: −0.03644076 6: −2.7955492 7: −3.0185244 8: −0.16116621 9: 2.5598824 10: 3.5982747 11: 2.4496856 12: 1.4353561 13: −2.3376217 14: 1.5091493 15: −1.8332916 16: −1.7814847 17: 1.6831902 18: 0.072118565 19: 1.0114408 20: −2.0413392 21: 1.1551036 22: −2.3068783 23: −0.18732563 24: −1.1784918 25: 0.81769562 26: −0.1530675 27: −1.8969883 28: −0.93342912 29: −0.20815188 30: 0.90363717 31: 0.15585786 32: −2.2690792 33: 0.50958693 34: −0.22805445 35: −1.7601552 36: −0.43514973 37: 0.42182469 38: −1.4265219 39: 1.177421 40: 0.19416071 41: −0.2984713 42: 0.79903913 43: 0.77090704 44: 2.215426 45: −0.26119217 46: −2.4548171 47: 0.1670278 48: 0.23921137 49: −0.46533313 50: 0.55348539 51: −0.16265169 52: 0.38286695 53: 0.34055299 54: −0.93140322 55: −0.17951404 56: 0.47119045 57: −0.50182968 58: 1.0053712 59: 1.9179566 60: 0.16939951 61: 1.78549 62: 1.0711477 63: 0.94986969 64: 0.6953724 65: 0.078478552 66: 0.31181556 67: −0.44148761 68: −0.23631665 69: −0.012911069 70: −0.3361088 71: 0.10542285 72: 0.14072527 73: −0.14097579 74: 0.2793099 75: 0.19883379 76: 0.19943306 77: 0.10022207 78: 0.020472348 79: −0.042941101 80: 0.064625442 81: −1.0609422 82: 0.42016992 83: 0.27064243 84: −0.14592318 85: 0.50374359 86: −0.65554547 87: −1.0872025 #
0.003330576550580226 1: 1.9507116 2: −11.019697 3: −2.6828804 4: 5.4480629 5: 5.7107086 6: 6.9693308 7: 2.66974 8: 3.2545464 9: −1.9070691 10: 0.99127346 11: −2.2294374 12: 2.7105196 13: −3.1338248 14: 1.5385495 15: −0.67776555 16: 1.5831238 17: −0.5545975 18: 0.12189388 19: −3.4824948 20: 0.54062164 21: −1.5836126 22: −2.3674173 23: −1.9569142 24: 0.007869835 25: 0.49454546 26: −2.1373594 27: 1.9552969 28: 1.1393875 29: −1.3862598 30: 1.9857892 31: 0.16729748 32: 0.81011742 33: −1.4185259 34: 0.24046826 35: 0.82870692 36: 0.15950572 37: −0.79740018 38: −0.16591235 39: 0.96315569 40: −2.1959643 41: 2.8853498 42: −0.43963414 43: 0.85861981 44: 0.64902544 45: 2.0380046 46: 1.5051774 47: 1.3050799 48: 1.0160776 49: 0.51463306 50: 0.30809772 51: 0.47857744 52: 2.0385702 53: 0.6751821 54: −0.74133307 55: −0.57322341 56: 0.13433874 57: −0.27051914 58: −0.51146394 59: 1.6747578 60: 0.12013735 61: 0.54918289 62: −1.1039402 63: 0.057252187 64: −0.21718289 65: 0.30045113 66: 0.86003029 67: 0.25052261 68: 0.12187614 69: −0.087335959 70: −0.15423696 71: 0.54607618 72: −0.4881106 73: −0.41245741 74: 0.19769716 75: −0.89351356 76: −0.13735279 77: −0.2327853 78: −0.23674634 79: −0.98305404 80: 0.52078742 81: 0.63322812 82: 0.58455044 83: −0.090681896 84: 0.022197129 85: 0.30395666 86: 0.30433914 87: −0.217499 #
0.003330576550580226 1: −1.3436253 2: −0.93941635 3: 0.34727129 4: −4.000988 5: 3.6346951 6: −2.0202615 7: 2.8455384 8: 2.3817055 9: −1.1053888 10: −0.021449149 11: 0.5917924 12: 1.05388 13: −0.72289419 14: 0.42895883 15: 2.1116214 16: 0.92751497 17: −1.8995572 18: 1.0356827 19: −0.83366108 20: −0.16999248 21: −0.48544282 22: −1.7330638 23: 1.7139575 24: 1.0412071 25: −0.094441161 26: 0.47909549 27: 2.0350492 28: −0.79608703 29: −0.017424189 30: −1.4338908 31: −0.18901214 32: −0.35805777 33: −0.99202484 34: 0.13780618 35: −0.15510346 36: −1.3227181 37: −0.10028049 38: 0.26590782 39: 0.93775231 40: 1.2771348 41: −0.42096636 42: 0.78392965 43: −0.35746196 44: 0.32524577 45: −0.44138062 46: −1.7038687 47: −0.31887752 48: −0.026019525 49: 0.00052639912 50: −1.0878571 51: −0.18844727 52: −0.059497412 53: 0.59026122 54: −1.0394223 55: 1.0100427 56: 1.132426 57: 1.2046562 58: 0.21211471 59: 0.59887296 60: −0.21160595 61: 1.0129697 62: −1.1150941 63: 0.070315979 64: 1.0367281 65: −0.34955642 66: 0.32304484 67: −1.1201361 68: −0.48632643 69: −0.64808732 70: −1.1307749 71: −0.79533523 72: 0.47282416 73: 0.96091819 74: −0.89764357 75: −0.57210386 76: 0.10012428 77: −0.027124282 78: −0.25215131 79: 0.33998123 80: −0.23809782 81: 1.1138523 82: 0.016608508 83: 0.14363414 84: 1.3560621 85: −0.93441159 86: 0.64719403 87: −0.48639837 #
0.003330576550580226 1: −1.3158712 2: 0.9707914 3: 3.1719823 4: −4.840673 5: 3.0936675 6: 1.5288476 7: 3.3780329 8: 4.2238803 9: −0.16770123 10: −0.019811096 11: 0.68480086 12: −0.034741119 13: −0.02114979 14: −1.2866874 15: 0.79995006 16: 1.5080215 17: −1.4229754 18: −0.75168186 19: −1.1788121 20: 0.69550902 21: −1.0135601 22: −0.75650036 23: −0.5917927 24: −1.2025844 25: 2.1475875 26: 0.43937358 27: 0.21717836 28: −1.3248004 29: 0.59354568 30: −0.31240404 31: 0.26002195 32: −0.22554828 33: −1.3846747 34: 0.52712202 35: −0.34480843 36: −0.21859333 37: −0.54067677 38: −1.0477362 39: −0.86044204 40: 0.73218143 41: −0.58861345 42: −0.29176298 43: 0.18470328 44: 0.75417542 45: −0.48993623 46: −1.1898146 47: −0.72130287 48: −0.15107831 49: −0.6868965 50: −0.6021902 51: −0.25264573 52: 0.73405951 53: −1.7278494 54: −0.4759106 55: −0.9581688 56: −1.0138706 57: −0.084222935 58: −1.3911563 59: 0.45293966 60: 0.68471515 61: −0.36915445 62: 0.54453796 63: 0.70223743 64: 0.59519744 65: −0.8628124 66: 0.93341041 67: 0.44959635 68: −0.17626347 69: −0.38861635 70: −0.018148063 71: 0.5389356 72: 0.71031916 73: −0.17292403 74: −1.1173062 75: 0.90167135 76: 0.54226488 77: 0.94917798 78: 0.66493577 79: −0.19910811 80: −0.069018558 81: 0.14457518 82: 0.51556104 83: −0.22483137 84: 0.67606121 85: 1.1257299 86: 0.16160756 87: 0.81155276 #
−0.0018087115978009983 1: −9.9491262 2: −0.45659417 3: 3.2891505 4: −0.11462954 5: 1.8582008 6: −2.3300738 7: 2.9500461 8: 3.6515126 9: −3.6656382 10: −2.1517365 11: −0.87704921 12: 0.15539017 13: −0.13543864 14: −2.2653666 15: 1.1439101 16: −0.46112978 17: −2.6953235 18: −2.8058879 19: −2.1647458 20: −0.028800163 21: −1.2686228 22: −1.3230211 23: 0.28681833 24: 0.15093741 25: 2.4514618 26: −1.2292511 27: −1.0463799 28: −0.090019494 29: 1.1452821 30: −1.4161206 31: 0.42701897 32: −0.39857301 33: 0.33894461 34: −0.22912827 35: 0.062416606 36: 1.9250615 37: −0.74576318 38: −0.087498635 39: −0.58594918 40: −0.47412258 41: −1.4470967 42: −0.59718144 43: 0.09468969 44: −0.021814467 45: −0.27346444 46: 0.57112187 47: 1.2442243 48: 1.2755759 49: −1.6541188 50: 0.41868493 51: 0.36696419 52: −0.9590854 53: 1.4340173 54: −0.30951533 55: −1.5828447 56: 0.23006968 57: 0.29946247 58: 0.22605401 59: −0.74504852 60: −0.2256089 61: 0.27168304 62: 1.1512096 63: −0.96407551 64: −0.059383538 65: −0.27408102 66: −1.1141781 67: −1.3486671 68: −0.91695899 69: −0.4751054 70: 0.77414888 71: 0.32459 72:

APPENDIX C5-continued

| SVM Model Weights (87; Benign/Malignant) |
|---|
| −0.12374441 73: −0.71892387 74: 0.42266324 75: 0.10231933 76: 0.92997658 77: 0.85771537 78: −0.47848618 79: −0.68670875 80: −0.49111453 81: 1.2695304 82: 0.23118316 83: 0.093918689 84: −0.79551268 85: −0.12334124 86: −0.59602612 87: 0.22202884 # |
| −0.003330576550580226 1: 5.8637757 2: −9.9825153 3: −1.3864986 4: 3.7755594 5: 1.9810551 6: 5.9261589 7: 2.0591137 8: 1.4179028 9: −2.8670921 10: 1.2827179 11: 0.51069009 12: 2.7566116 13: −1.0318092 14: 5.8409891 15: 2.453907 16: −1.4336371 17: 2.6721907 18: 2.6253684 19: −1.1450388 20: 0.95642722 21: −0.68922752 22: −0.63180703 23: −1.2727717 24: 2.6737196 25: 2.5429664 26: 0.12496121 27: 0.70460039 28: 0.61082274 29: −2.6253922 30: 2.9772513 31: 1.4704022 32: 2.6366663 33: 0.59462577 34: −1.7308691 35: −2.8416824 36: 1.8223454 37: 1.8723491 38: 0.31541702 39: 1.2786952 40: 0.20529886 41: −2.3980207 42: 0.4039337 43: −1.0958207 44: −1.1642426 45: 0.81780392 46: −1.8876129 47: −0.87910926 48: 0.47651336 49: −0.31036353 50: 0.81277901 51: 0.57417709 52: −0.48608726 53: 0.038678579 54: 1.2284206 55: −0.13300143 56: −0.91738433 57: 1.1555263 58: 0.090056382 59: −0.43537176 60: −0.38387787 61: −0.9908492 62: 0.47343999 63: −0.011526085 64: −0.71371078 65: 0.026976289 66: 0.051007312 67: 0.71084046 68: −0.64197159 69: −0.33844063 70: −0.045717873 71: −0.56054622 72: 0.051615499 73: 0.41121837 74: 0.65057576 75: 0.54327095 76: 0.26035652 77: −0.52896899 78: −0.23127164 79: 0.3524617 80: −0.24086736 81: 0.11925521 82: 0.080059394 83: 0.010276271 84: 0.36877257 85: 0.15841663 86: −0.14087231 87: −0.074028924 # |
| −0.0015858157829818217 1: 2.0883245 2: −6.4719901 3: −0.83055037 4: −4.0124822 5: −1.584533 6: 3.4442372 7: 5.0622163 8: 9.4115982 9: 4.5804567 10: 1.9651678 11: 4.8765759 12: −0.95423251 13: 8.2563066 14: −3.4564598 15: −1.9124181 16: 0.80265266 17: 0.26535338 18: −1.6216221 19: 1.5909601 20: 3.5689068 21: 0.34506276 22: −0.43104431 23: −1.4937686 24: −0.28332224 25: 0.084367178 26: 2.1458566 27: −2.0169153 28: 0.59910655 29: −0.24338524 30: 1.0688 31: −0.021978159 32: 1.015671 33: 0.25432023 34: 1.8178529 35: −1.8832308 36: 0.54178053 37: 0.18022253 38: 0.59396631 39: 0.15619493 40: −0.053717207 41: −0.36186832 42: 0.69574678 43: 1.2223178 44: 0.47033295 45: 2.4558377 46: −0.40047166 47: −0.86391413 48: −1.8204731 49: 0.55548364 50: −0.40956348 51: −0.30853447 52: −0.34457603 53: 0.99584061 54: 0.38462019 55: 0.33260402 56: 0.58035827 57: −0.97214371 58: −0.059460159 59: −0.71540612 60: 1.0810293 61: 1.1018376 62: −0.93851775 63: 0.2399784 64: 0.13933 65: 0.080727756 66: −1.2611846 67: 0.15461834 68: −0.33013773 69: 0.77019066 70: 0.1867961 71: −0.52667207 72: −0.90858626 73: 0.087602384 74: −0.83025241 75: −0.27157259 76: 0.47756934 77: 0.05647862 78: 0.55593252 79: −0.3144294 80: 0.36774859 81: 0.30203703 82: −0.28094372 83: −0.27261075 84: −0.11728917 85: 0.24105154 86: 0.11707048 87: 0.019343013 # |
| −0.003330576550580226 1: −1.3259747 2: −0.81137985 3: 1.4334838 4: −1.7649548 5: 3.6129992 6: 0.29705635 7: 1.2894326 8: −0.10095613 9: −2.3867192 10: 1.7502738 11: −0.19358803 12: 0.50865448 13: 0.3514927 14: −0.64236754 15: 4.1707873 16: 4.8303452 17: 3.4271297 18: 1.7873092 19: −1.7034998 20: −0.70197618 21: −2.1089077 22: −0.48871359 23: −0.62036341 24: 2.3210227 25: 2.126719 26: 1.1654752 27: 2.4087574 28: 1.4107223 29: 2.3072691 30: −0.81872845 31: −2.2211478 32: 1.9796011 33: 0.23920904 34: 0.93012995 35: −0.60235846 36: −0.088530228 37: 1.7537847 38: 0.88093865 39: −0.35249573 40: 1.8679098 41: 0.88367492 42: −0.3762452 43: 0.66681099 44: 1.1645045 45: 1.0631882 46: 0.50139904 47: 0.60997486 48: 0.099085584 49: −0.28998566 50: 0.30199984 51: 0.032218505 52: 0.14505504 53: −0.70199054 54: 0.63631988 55: 0.65796453 56: 0.46654585 57: −1.8316227 58: 0.64973044 59: −0.03867637 60: 0.87000394 61: −0.038856808 62: 1.2103601 63: 1.587211 64: −0.064324111 65: −0.82001442 66: −0.31918877 67: −1.2849535 68: 0.49531212 69: 0.65561968 70: 0.36848164 71: 0.21935652 72: 0.31024703 73: −0.95345819 74: 0.2128519 75: −0.153165 76: −0.46214783 77: −0.069486707 78: −0.46384981 79: 0.76563936 80: −0.81284559 81: 0.15845466 82: −0.72415864 83: −0.0056166188 84: −0.17356507 85: −0.22766653 86: −0.24717945 87: −0.36597544 # |
| −0.003330576550580226 1: −1.4225143 2: −3.3811448 3: −1.3460624 4: −2.4572864 5: −1.2485046 6: 1.5272132 7: 3.8467693 8: 3.6000576 9: −2.5641577 10: −0.67970216 11: −1.2237694 12: −0.66455346 13: −1.7749182 14: 1.801129 15: −0.073441938 16: −1.0443138 17: 2.9320962 18: −0.62133968 19: 0.24629931 20: −2.5408921 21: −1.9696916 22: −0.15611142 23: −0.55407423 24: 0.17331484 25: −2.6666267 26: 0.11005254 27: −0.76523972 28: 0.82345724 29: 2.1196442 30: −0.10236285 31: 1.7822025 32: −0.34777778 33: −2.6759152 34: 0.95936936 35: −0.20149407 36: −0.27700329 37: 1.0371037 38: −0.35205483 39: −1.3395022 40: −1.517821 41: −1.6165372 42: 1.5603799 43: −0.14268057 44: 1.0620614 45: −0.2145381 46: 0.025638459 47: −0.10914129 48: −0.17478488 49: 0.4742581 50: −0.48568475 51: −0.023864167 52: 0.11586545 53: −0.062558644 54: 0.021825971 55: 0.30173782 56: −0.29385743 57: −0.56683713 58: 0.94771284 59: 0.29573876 60: 0.014790609 61: −0.34971812 62: −0.33196506 63: −0.87879521 64: 0.40384069 65: 0.058484275 66: −0.13888034 67: 0.19267932 68: 0.83802092 69: 0.60410917 70: 0.38784978 71: −0.045576707 72: −0.18632713 73: −0.15257339 74: 0.1837924 75: 0.1415422 76: 0.25753227 77: 0.00010349972 78: −0.44107446 79: 0.05193444 80: 0.12665264 81: −0.25195363 82: −0.21478599 83: −0.11333102 84: 0.080544256 85: −0.26152048 86: −0.025861861 87: 0.1800579 # |
| 0.003330576550580226 1: 12.88688 2: 7.6728315 3: 3.7184772 4: −4.2598038 5: −1.1576847 6: −0.6589455 7: −0.12417337 8: −3.7127607 9: 1.2203434 10: 1.8098245 11: 0.71039736 12: 2.0804777 13: −2.7874148 14: −3.1586065 15: 1.3173382 16: 0.94230872 17: −0.76273376 18: −1.9022322 19: −0.086186662 20: −2.3211615 21: 0.149593 22: 1.1707815 23: 0.083588153 24: 1.7598888 25: 0.15474093 26: −0.142803 27: −0.67765546 28: −0.41080022 29: −0.41189691 30: 0.66072643 31: 0.3543807 32: 1.1919838 33: 0.072597109 34: 0.34267452 35: 0.18416306 36: 0.61917019 37: 0.87496203 38: 1.0489271 39: 0.74451184 40: 0.050107613 41: −0.090185337 42: 0.79754627 43: 0.13573256 44: −0.040791694 45: −0.44517997 46: −0.88015085 47: −0.84163201 48: 0.55422693 49: 0.70137566 50: −0.5168348 51: 1.9540147 52: 1.2281084 53: 0.31411505 54: 0.47722226 55: 0.52601123 56: −1.2655801 57: 0.012280421 58: 0.6504724 59: −0.17440858 60: 0.0096336165 61: −0.12215171 62: 0.67708731 63: −0.88185388 64: 0.29823485 65: 0.63555801 66: −0.56147951 67: −0.13271585 68: −1.3561636 69: 0.63261569 70: −0.61726475 71: 0.18187062 72: −1.0094401 73: −1.2734075 74: −1.1442035 75: −0.43973461 76: −0.10631246 77: 0.30288884 78: 0.75480568 79: −0.6100018 80: 0.29362202 81: 0.017575556 82: −0.12277605 83: −0.17429066 84: −0.1350536 85: |

APPENDIX C5-continued

| SVM Model Weights (87; Benign/Malignant) |
|---|
| −0.035917569 86: −0.69957954 87: −0.38850522 # 0.00091470626985905084 1: 7.3784966 2: 4.8459315 3: 0.99026364 4: −6.222187 5: −3.2786598 6: 4.2420106 7: −1.4449238 8: −2.2808609 9: −1.4829886 10: −4.5230999 11: 2.6087584 12: −4.3234897 13: −4.4426599 14: −4.7678609 15: −3.2571344 16: −1.5333452 17: −2.6526148 18: 1.5474545 19: 3.6030548 20: −4.077352 21: −3.4779377 22: −2.7278492 23: −2.5425501 24: 1.846383 25: −0.42956391 26: −2.9031358 27: 2.0370779 28: 3.6792727 29: −0.36483341 30: 1.3399615 31: −2.5355213 32: −2.2175422 33: 2.7985163 34: −0.54378569 35: −0.60952413 36: 0.97480601 37: −0.13065526 38: −1.4198263 39: 0.051092677 40: −0.88236183 41: −0.3525922 42: 0.37660906 43: 0.41154668 44: −0.41369507 45: 0.76735151 46: −0.77596855 47: 0.31144658 48: −0.99239349 49: −0.46655914 50: 0.63673824 51: −0.85369796 52: 1.1574687 53: 0.38414702 54: −0.68200344 55: −0.65493113 56: 0.40630376 57: 0.28687242 58: −0.15555534 59: −0.83930945 60: 1.3784143 61: −0.85099256 62: −0.27637884 63: −0.16698985 64: −0.39109907 65: −0.10090256 66: −0.6203655 67: 0.23265249 68: 0.12762587 69: −0.15666832 70: −0.20852548 71: −0.31870311 72: 0.38570139 73: −0.1223087 74: −0.51973826 75: 0.058174726 76: 0.19981381 77: −0.17149107 78: −0.071773522 79: 0.12524465 80: −0.28136277 81: −0.30190554 82: −0.20720464 83: 0.352871 84: 0.27761251 85: 0.089949146 86: 0.046119336 87: 0.082288712 # −0.003330576550580226 1: 16.208258 2: 5.0280037 3: 0.82172555 4: −6.9475951 5: −3.3456998 6: −1.9767576 7: −3.7032745 8: −3.4155843 9: 7.0004339 10: 4.3763795 11: −0.7983644 12: 2.4872475 13: −3.7470655 14: −0.62817919 15: 4.9190741 16: −4.2188792 17: −2.0490263 18: −2.7245042 19: −0.17719579 20: −0.11300744 21: 1.0088226 22: −0.073986799 23: 0.5722124 24: 0.008042899 25: 0.74790359 26: 0.33785641 27: 1.2871412 28: 0.5370971 29: 0.44420156 30: 0.23329081 31: 2.4261262 32: 1.2618583 33: 0.88156927 34: 1.8443539 35: 0.69782907 36: 0.44336718 37: 0.85502648 38: 0.41916502 39: 1.2100462 40: −0.34577665 41: 0.57506794 42: −0.66228169 43: 0.74202949 44: 0.51757735 45: −1.2525393 46: 0.090822548 47: −0.27381754 48: 1.0868232 49: −0.47915345 50: −0.63097495 51: 0.36603194 52: 0.28519693 53: 0.064565808 54: 0.83607817 55: 0.50049102 56: 0.23370145 57: −0.42598504 58: −0.61825037 59: −0.91476727 60: −0.0016951035 61: 0.99797559 62: −1.0861138 63: −0.21476594 64: 0.059051462 65: −0.62882084 66: 0.26161498 67: 0.5976519 68: 0.794837 69: −0.10323665 70: 0.99892217 71: −0.5670417 72: 0.21851051 73: −0.85495353 74: 0.23074594 75: 0.044591494 76: 0.67030954 77: 0.22074986 78: −1.0043128 79: −0.26563704 80: 0.17796762 81: −0.33441058 82: −0.16966254 83: 1.2614371 84: 0.23712456 85: 0.11905111 86: 0.15817074 87: 0.19000015 # 0.003330576550580226 1: 3.9146221 2: −9.5838127 3: −2.1989262 4: 2.483418 5: 2.2109056 6: 2.3148644 7: −1.6744893 8: 2.0438197 9: −0.22050218 10: 0.95947695 11: 1.7617443 12: 1.0714002 13: −2.0813811 14: 0.52549028 15: 0.8533324 16: 2.6622386 17: −2.1034327 18: −0.13717787 19: −2.1242678 20: 1.0191004 21: −1.0218762 22: −1.8217447 23: 1.2176883 24: 0.32349762 25: −1.7366513 26: 0.13325104 27: 1.2317364 28: −1.6418275 29: −1.1362265 30: 1.0577126 31: 0.8307243 32: −0.038968693 33: 1.0813892 34: −0.26267028 35: −0.40768319 36: −1.5068281 37: 0.24804747 38: −2.8056893 39: −1.4992043 40: −0.87992305 41: 0.15084013 42: −0.46094763 43: 0.088341065 44: −0.45993951 45: −1.8586137 46: −0.12604149 47: −0.77085721 48: −0.3926746 49: 1.5514119 50: 0.3039287 51: −0.020093013 52: −1.7802604 53: 0.85846531 54: −0.49611357 55: −1.8293589 56: 0.416605 57: −1.5735593 58: −0.32552642 59: −0.281872 60: −0.74955857 61: 0.14202702 62: 0.61847329 63: 0.38252032 64: −0.94535166 65: −0.10739016 66: −0.40688729 67: −0.64594442 68: 0.9584676 69: 1.6266457 70: 0.14564814 71: 0.057670958 72: −0.51033443 73: 0.092842311 74: −0.80618852 75: 0.62784499 76: −0.57284373 77: 0.41931754 78: −0.82127243 79: 0.076667011 80: −0.051802412 81: −0.8036865 82: −0.40587062 83: 0.18605494 84: 0.039897773 85: 0.10903195 86: 0.40717348 87: −0.3650966 # 0.003330576550580226 1: 4.8517151 2: −2.2635946 3: 0.77981508 4: 1.0349083 5: 0.2407393 6: −0.36395466 7: 0.59494889 8: −0.31111282 9: −0.45820686 10: −1.6839181 11: −1.5326648 12: −4.838304 13: 2.289643 14: 1.9145365 15: −2.4840858 16: 2.4276547 17: 1.505362 18: 3.6388161 19: 2.8526552 20: −0.63271797 21: −0.074653953 22: 1.4910883 23: 0.97199351 24: −0.64722019 25: −1.2348423 26: 1.4096289 27: 2.0301092 28: 0.83028793 29: 0.72350144 30: −0.53756076 31: −0.0040175514 32: 0.4940317 33: 1.7840099 34: −0.62599593 35: 1.2050196 36: 0.97808158 37: −0.71416926 38: 0.94241953 39: −0.98290306 40: 0.94824815 41: 0.26809698 42: 0.7598449 43: −1.2370645 44: −0.41675937 45: 0.27529997 46: −0.16245311 47: −0.26389834 48: 0.77095467 49: 0.65882993 50: 0.65227705 51: −0.21033715 52: −1.5154692 53: 1.3093165 54: −0.12206756 55: 0.26290685 56: 0.51977479 57: −1.0351532 58: −0.14396873 59: −0.91463321 60: −0.041318469 61: 0.87110585 62: 0.10706431 63: −0.034241769 64: 1.2024602 65: 0.82649237 66: 0.82070524 67: −0.14524646 68: −0.0044034384 69: −1.3228763 70: 1.4248272 71: 1.1001936 72: −0.57339489 73: −0.99373192 74: 0.21798588 75: 0.60908759 76: −0.11445805 77: −0.568223 78: 0.10865738 79: −0.49674585 80: −0.33665106 81: 0.045985267 82: 0.92456824 83: 0.35274199 84: 0.57073832 85: 0.6890772 86: 0.18124068 87: −0.57633996 # −0.003330576550580226 1: 1.2363012 2: −5.582078 3: −0.33564591 4: 0.31853491 5: 0.18021882 6: −0.46712884 7: −0.77220786 8: −0.43467858 9: −1.853532 10: −2.5806634 11: −1.1961414 12: 1.362698 13: −1.7099397 14: −2.9604051 15: −1.8374467 16: 0.26128343 17: 1.0424188 18: −1.4112453 19: −0.62311435 20: 1.0762979 21: 1.1709037 22: 1.9389135 23: −0.1562897 24: −0.12180445 25: −1.104779 26: 1.1268845 27: −0.58998162 28: 0.19233964 29: −0.0052791387 30: 0.42925557 31: 0.63277447 32: 0.10481225 33: −0.35907343 34: −1.0917473 35: −0.44221684 36: −0.40957639 37: −0.84290808 38: −1.5072352 39: 1.6273284 40: 0.066626854 41: 1.2650294 42: 0.65593106 43: −1.4243168 44: 1.1144385 45: −0.27048972 46: −1.5256876 47: −0.39044857 48: 0.19247398 49: −0.40261564 50: 1.7703564 51: −0.97374201 52: −0.76216626 53: −0.39491147 54: 0.10372505 55: 0.42463291 56: −0.088040069 57: 1.0343374 58: −0.026342321 59: −1.3339051 60: −0.28965908 61: 0.16679488 62: 0.27958182 63: 0.80498672 64: −0.68446982 65: −0.74795526 66: 0.70079291 67: 0.94416362 68: 0.46145177 69: −0.57584852 70: −0.43812135 71: 1.3471149 72: −1.9226621 73: −1.44992634 74: −0.60416913 75: −1.0027869 76: 0.14529993 77: 0.69023544 78: 0.085627377 79: 0.21563464 80: −0.55316478 81: −0.30311269 82: −0.10041367 83: −0.57187146 84: 0.22961248 85: −0.33618769 86: 0.49615276 87: 0.78277361 # −0.0025541627312868354 1: −5.7875681 2: −1.0084696 3: −2.5154941 4: 3.718677 5: 1.4831289 6: |

APPENDIX C5-continued

| SVM Model Weights (87; Benign/Malignant) |
|---|
| −4.6980391 7: −4.2098918 8: 0.72386932 9: −0.43842459 10: −3.7361112 11: 1.2272559 12: 1.3518623 13: 2.2724423 14: −4.0965257 15: −0.16307685 16: 0.54426932 17: 2.674973 18: −4.7668042 19: −2.5615635 20: 2.6017296 21: 2.3070562 22: −0.32244205 23: −1.0658669 24: −5.2624288 25: 1.8111422 26: −0.12618792 27: 1.6774101 28: 2.1192849 29: 1.4636447 30: 2.2438395 31: −3.7228088 32: 1.0451591 33: 0.84639311 34: 1.1798813 35: −0.48930475 36: −1.4044904 37: 0.44887969 38: 0.30339044 39: −2.3206234 40: −1.7935805 41: −2.3300099 42: −0.52069807 43: −0.45081753 44: −0.1580476 45: −0.54148686 46: −1.0554613 47: 0.80541939 48: 0.43984106 49: 0.90169472 50: −0.016652251 51: 0.22739042 52: 1.0022042 53: 0.24052338 54: 0.28399348 55: 0.703206 56: −0.52407777 57: 0.3697007 58: −1.2095546 59: −0.44843248 60: −0.58039469 61: 0.19270124 62: 0.078443125 63: −0.18017742 64: −0.33629015 65: 0.53866172 66: 0.47427157 67: −0.18395063 68: 0.42899922 69: −0.31784016 70: −0.80072719 71: −0.59086686 72: −0.097046271 73: −0.32098657 74: 0.12316822 75: 0.53235853 76: −0.16685803 77: −0.75464016 78: −0.28901589 79: −0.083571091 80: −0.10369918 81: −0.2478382 82: 0.39178416 83: 0.50616205 84: 0.29709578 85: −0.38560501 86: −0.2437392 87: −0.0062586386 # |
| −0.003330576550580226 1: 4.1020322 2: −4.588994 3: −0.25456351 4: −0.32246256 5: 1.8932445 6: 2.0895927 7: −1.0208099 8: 0.88184685 9: 0.078009665 10: 2.6228025 11: −0.4592624 12: −0.73257983 13: 0.5757004 14: 2.9550624 15: 0.52651018 16: 1.6183442 17: 1.271421 18: 1.9024082 19: −0.82549751 20: −0.39238787 21: 1.6686051 22: 0.77140731 23: 0.098474815 24: −3.1235452 25: −1.6336083 26: −0.1539748 27: 1.9261986 28: 0.8454203 29: 0.083330788 30: −2.5048091 31: 2.5305629 32: 1.3224663 33: 1.6144745 34: −0.18925323 35: 0.2244098 36: 1.5410305 37: 0.60980433 38: 1.2016187 39: 0.072792992 40: −1.2322062 41: 1.4042519 42: 0.77464634 43: −0.18778019 44: 1.1279122 45: −0.34109744 46: −0.49836823 47: 0.43126982 48: −1.31104 49: −0.67789751 50: −0.44775379 51: −1.8014168 52: 0.64093351 53: −0.26696709 54: −0.82668501 55: 0.29255125 56: 0.0045264601 57: 1.1180086 58: −0.84348315 59: −1.0833781 60: 0.34288284 61: −1.5538384 62: 0.33990073 63: 0.086969115 64: −0.35646647 65: −0.13079517 66: −0.70064127 67: −1.7454661 68: 0.84224337 69: −0.026936596 70: −1.62547 71: 0.30624464 72: −0.078725316 73: 0.44983208 74: 0.12789151 75: −0.32441276 76: 0.81692576 77: 0.43846592 78: 0.60836017 79: 0.16772625 80: 0.17507496 81: −0.043199949 82: −0.087800451 83: 1.1857327 84: −0.35242039 85: 0.17439799 86: −0.13627973 87: −0.0003859273 # |
| 0.003330576550580226 1: 2.3376174 2: 1.3542268 3: 2.4850945 4: −1.2638111 5: −0.78601927 6: −2.594995 7: −0.54343778 8: 3.0801613 9: −1.54309 10: 1.2380967 11: 1.301192 12: −0.16419302 13: −1.2675476 14: 2.4840486 15: −0.15256229 16: 0.13161588 17: 0.48776254 18: −0.36262459 19: 0.68028796 20: −1.9740275 21: −0.34123287 22: −0.043554693 23: −2.6711347 24: −1.6657956 25: −0.39183104 26: −0.42118907 27: −1.2100161 28: −1.0413429 29: −1.3260686 30: −0.70797545 31: 0.40197438 32: 0.77484918 33: 0.591398 34: 1.320011 35: −0.47725779 36: 0.22152631 37: −0.93336248 38: 0.35800895 39: 0.54715556 40: 0.62986487 41: 1.576126 42: 1.4674696 43: −0.36482826 44: −0.9647913 45: −0.82723027 46: 0.12871277 47: −1.0172108 48: 0.39423183 49: −0.62734401 50: −1.2453856 51: −0.96192622 52: 0.58158761 53: 0.2840724 54: −0.041641422 55: 0.81978875 56: −0.82872599 57: −1.1571838 58: −1.0799139 59: −0.59749144 60: 0.15188833 61: 0.11261069 62: 1.2753228 63: −0.14491773 64: 0.47276843 65: 1.3230103 66: −0.48940101 67: 0.65904707 68: 0.41815275 69: 0.27657706 70: −0.85806155 71: −0.05333598 72: −0.023991598 73: 0.48209861 74: 0.78222781 75: 0.66482443 76: −1.1277559 77: −0.83450043 78: 0.013774643 79: −0.8200044 80: −0.64606786 81: 0.40549323 82: 0.41451508 83: −0.30117378 84: −0.41080025 85: 0.39337277 86: 0.30787334 87: −0.11981292 # |
| 0.00050287777532010162 1: 7.9486814 2: 6.313159 3: 3.4036202 4: 3.6738026 5: 0.8484242 6: −1.12104 7: 1.1878948 8: −2.2317212 9: 2.0272512 10: 0.52818286 11: −1.7246594 12: −1.3033267 13: −0.41194135 14: 1.4738997 15: 0.94791991 16: 0.43159148 17: 0.86042041 18: −0.72649908 19: 0.24455844 20: 1.5337915 21: −0.070671529 22: −3.2864313 23: 1.042661 24: 0.57346916 25: −0.17784877 26: 0.62522596 27: −1.3299311 28: 1.430204 29: 1.229068 30: 1.6345702 31: −0.82010353 32: 2.4077256 33: 0.46431184 34: 0.70158809 35: 2.1816514 36: 2.2421138 37: −1.5970308 38: 0.18138181 39: 1.1032536 40: 1.472198 41: 0.50239062 42: 0.62110627 43: −0.23183186 44: −2.0542288 45: 0.34160188 46: 0.02542842 47: −0.14262132 48: −0.046494257 49: 1.6358472 50: 0.54953927 51: 0.5901584 52: −0.77110654 53: −0.17316507 54: −1.5964856 55: 1.0319989 56: 0.74831015 57: −0.90131527 58: 0.02119487 59: 0.85915452 60: 0.83274412 61: 0.26454583 62: 0.052552998 63: −0.96018612 64: −0.27045661 65: 0.034029823 66: 0.25971562 67: −0.087616593 68: 0.21399029 69: −1.1747633 70: −0.74932021 71: −0.52223557 72: 0.5713945 73: −0.40078789 74: −0.2828753 75: 0.14939854 76: −0.32377112 77: 0.066406585 78: −0.022806602 79: 0.20015027 80: 0.26603687 81: −0.21412492 82: −0.73513877 83: 0.27894762 84: −0.16934811 85: 0.11708372 86: 0.11781476 87: 1.1381788 # |
| 0.00063239879863878959 1: −4.6370125 2: 25.3416 3: −16.121107 4: −0.6962499 5: −0.097961165 6: 9.8783503 7: −13.519696 8: 12.443069 9: −2.8442738 10: 6.2117672 11: −14.486603 12: −1.9520348 13: 1.2228634 14: −1.8063329 15: −1.0748529 16: 0.99744153 17: −1.7065885 18: −0.12526843 19: 0.24673074 20: 0.050437115 21: 0.24593517 22: −0.1737472 23: −0.39504737 24: 0.86062044 25: −0.12319233 26: 0.65940768 27: −0.34209335 28: 0.20274197 29: −0.72116911 30: −0.048453134 31: −0.47173834 32: 0.62735939 33: −0.27868941 34: −0.27687511 35: −0.27298406 36: −0.25711399 37: −0.21862105 38: −0.2790415 39: 0.038329072 40: 0.49325964 41: −0.43934143 42: −0.072025329 43: 0.081549637 44: −0.32803825 45: −0.35842144 46: −0.29083082 47: 0.12729056 48: −0.10032506 49: 0.25450188 50: 0.14349255 51: −0.041720446 52: −0.0098631838 53: 0.026373385 54: 0.16790451 55: 0.080416203 56: −0.19654652 57: 0.12690592 58: 0.23280348 59: −0.16926627 60: −0.059940565 61: 0.013699979 62: 0.062027354 63: −0.13037252 64: 0.051242147 65: −0.10712767 66: −0.024650952 67: −0.14558119 68: −0.03412804 69: 0.08947067 70: −0.0039251689 71: 0.0014583743 72: −0.074728526 73: 0.092037506 74: 0.080470107 75: −0.06802699 76: 0.041400608 77: −0.052650008 78: −0.012608281 79: 0.18882611 80: 0.098734684 81: −0.0053395601 82: 0.077860154 83: −0.053664465 84: 0.099180482 85: 0.075526714 86: −0.067439295 87: −0.066202998 # |
| −0.003330576550580226 1: −0.42324471 2: 2.5828345 3: −1.8410451 4: −0.4363316 5: 0.067014627 6: −1.8869078 7: 2.7124326 8: 3.5093668 9: −2.1161191 10: 0.31742153 11: 2.0527875 12: 2.6345732 13: −0.53119665 14: −1.2637744 15: 0.19591911 16: −2.386672 17: 0.98163056 18: 0.015205857 |

APPENDIX C5-continued

SVM Model Weights
(87; Benign/Malignant)

19: 1.3719232 20: −3.8242466 21: 0.63041341 22: 2.2860601 23: −2.2027335 24: −1.1924071
25: 0.088403225 26: −2.2897179 27: 1.8068643 28: −0.78437859 29: −0.35509837 30: −0.57099378
31: 0.79047942 32: 2.1919038 33: 0.32323298 34: −0.1085334 35: 0.71788019 36: 0.46938607 37:
−1.4283434 38: −1.6121867 39: −0.56469077 40: −0.47763538 41: −0.81906885 42: 0.6883561
43: 2.4099319 44: −2.0321629 45: 0.78628761 46: −1.5318716 47: 1.581475 48: 0.28450912 49:
−1.8042477 50: −1.1501552 51: 0.96483588 52: −1.007615 53: −1.9168314 54: 0.10064875
55: 1.0965402 56: 2.0633764 57: −0.23728377 58: −0.65973568 59: −0.16923778 60: −1.4804031
61: 0.57514387 62: 0.26726937 63: 0.31430072 64: −0.079305612 65: 0.16362113 66: −0.24121113
67: −0.32369888 68: −0.16671567 69: 0.011938976 70: 0.57545716 71: 0.10028149 72: −0.55875379
73: 0.090979785 74: −0.28152052 75: −0.74530959 76: −0.68932241 77: −0.21559061 78: −0.13300842
79: 1.0360554 80: 0.84739202 81: −0.079618588 82: 0.39879352 83: −0.38048029 84: −0.13616773
85: 0.24391849 86: 0.28922558 87: 0.093983881 #
−0.0033305765505802261: 0.25218788 2: 0.81176651 3: 4.3265495 4: 0.80694395 5: 1.2578313 6:
−0.41075879 7: −0.52536166 8: −1.8982818 9: 1.2403241 10: 0.55058247 11: −0.13172349 12:
−0.29310575 13: −0.85193628 14: 0.98000151 15: 0.51622123 16: 1.1070833 17: −1.7187762 18:
−1.4114212 19: −1.4101827 20: 2.371562 21: −0.20655285 22: −0.77752417 23: −1.6776743
24: 1.3278382 25: −0.65001339 26: 1.1879882 27: −1.6550736 28: −0.69467938 29: 1.6729231 30:
−0.049590517 31: 0.17878917 32: −1.6048551 33: 0.05020367 34: 1.5113513 35: 2.2310727
36: 0.6893003 37: −0.47463822 38: −1.3859652 39: 1.3018564 40: −0.2566067 41: −0.20571378 42:
−0.093710981 43: −0.57197189 44: −0.51114792 45: 0.031266723 46: −0.11190546 47: 0.21093827 48:
−1.480884 49: 0.11184267 50: −0.96855474 51: −1.3595977 52: −0.8792485 53: 0.34201536
54: 0.13241242 55: −0.47476271 56: 0.15498728 57: 0.15017387 58: −0.39439949 59: 0.3773064 60:
−0.52866888 61: −0.59836566 62: −0.93740159 63: −0.047246348 64: −0.117203 65: −0.83106142 66:
−0.58240384 67: 0.58822846 68: −0.066905402 69: 0.43310806 70: −0.59294975 71: −0.038655914
72: 0.073927745 73: −0.76395845 74: 0.74063784 75: −0.25710684 76: −0.3278614 77: −1.6574421 78:
−0.48348796 79: 1.3722363 80: −0.70066696 81: 0.28739998 82: 0.64671952 83: −0.59736836
84: 0.64070654 85: 0.12960356 86: −1.2510532 87: 0.062797233 #
−0.00088639363690490129 1: −0.26397073 2: −4.3800235 3: 0.96010846 4: −6.5841908 5: 1.6685443
6: −0.56736088 7: −0.083688535 8: −2.66816 9: −1.6018287 10: −2.2983365 11: −3.507324
12: 0.0095484713 13: 1.2482775 14: −0.31201324 15: 0.47953141 16: 0.59642285 17: −0.47637615
18: −1.1856458 19: −1.6341721 20: 3.4143758 21: −0.020608557 22: 0.73003125 23: −0.81526971 24:
−1.5109706 25: −0.14740245 26: 0.54324085 27: −0.27993053 28: −1.0582408 29: 0.91323972
30: 1.3065295 31: 0.65528071 32: −1.5894922 33: 0.89412045 34: −3.1973541 35: −0.72293127
36: 2.4681482 37: −0.33120728 38: −0.91447645 39: 0.69795197 40: −0.21701232 41: −1.0900477
42: 0.67749697 43: −0.33487478 44: −0.69148785 45: −0.26212937 46: 0.54704535 47: 0.89142299
48: −0.87253165 49: −0.30725515 50: 0.01050829 51: −0.067594275 52: −0.76299405 53: −0.5275268
54: 0.60136604 55: 0.93226683 56: −0.88733613 57: −0.38411763 58: −0.32900149 59: 0.90254068
60: 1.6998997 61: 0.58596885 62: −0.34130809 63: −0.56362987 64: 0.38372657 65: 0.83891815 66:
−0.5779351 67: −1.0001854 68: −0.8855077 69: −0.49604541 70: 0.061250381 71: 1.2289635
72: 0.77946144 73: 0.10443769 74: −0.53655225 75: −0.47988957 76: −0.35080016 77: −0.081329726
78: −0.8766126 79: −0.17184246 80: 0.59839505 81: −0.80135769 82: 0.43899104 83: 0.051791977
84: 0.13997768 85: −0.69018161 86: 0.35188946 87: −0.63329929 #
0.0033305765505802261: 0.2945444 2: 1.5663686 3: 2.0269644 4: −1.3007404 5: 2.2870119 6:
−3.3503802 7: 1.4742044 8: 3.5182641 9: −3.8660257 10: −0.30044997 11: 2.4009323 12: 0.023592524
13: −0.092459396 14: −1.9675099 15: −0.52797329 16: 1.6415339 17: −1.3027037 18: 1.1715622 19:
−1.3815528 20: 0.1912863 21: 0.80708176 22: −1.3128206 23: −1.3250409 24: −1.3467921
25: 0.47949335 26: −0.77753985 27: 1.4726981 28: −0.20863654 29: −0.41831556 30: −1.5252051 31:
−0.68172175 32: −0.19234197 33: −0.57685065 34: 0.22692519 35: −0.10171806 36: −1.639927
37: 1.1498389 38: 0.52990198 39: 2.0820906 40: 0.74807709 41: 0.10239747 42: −1.1050204 43:
−0.53352898 44: 0.79966813 45: −1.5530518 46: −1.0456312 47: 0.0035056134 48: −0.96574444
49: 1.1126325 50: −0.064588472 51: −0.55075049 52: 0.9495334 53: −0.32114556 54: 0.42454228
55: 0.18516833 56: −0.18974295 57: −0.049605269 58: 0.17790461 59: −0.38122171 60: 0.46975023
61: 0.2750861 62: −0.81585729 63: 0.034077615 64: 0.58590645 65: −0.85271186 66: −0.40590015
67: 0.8237015 68: −1.0428532 69: −1.5778298 70: 0.83420289 71: 0.1530309 72: −0.019400565 73:
−0.35515225 74: 0.97543013 75: 0.45758843 76: −0.66852099 77: 0.23889022 78: −0.48623368
79: 0.5784654 80: −0.0082634836 81: 0.18652764 82: −0.058095567 83: −0.15391538 84: −0.6177271
85: 0.99040502 86: 0.12622501 87: 0.067504495 #
0.0018465421767685771 1: 7.2026958 2: 2.506717 3: 1.6384877 4: 2.1010149 5: 2.6597629 6:
−2.2723093 7: 2.6085973 8: 2.0390947 9: −0.71968418 10: −1.0824095 11: −1.1634985 12: 0.56328827
13: 0.013427491 14: −0.22713479 15: −1.2914221 16: −0.4034566 17: −0.095398933 18: 0.86121124
19: −0.20695956 20: −0.28110185 21: −1.1006707 22: 1.2550631 23: 1.8677807 24: 0.83824652 25:
−0.20042829 26: −0.23248933 27: 1.6082169 28: 0.2339604 29: −0.94725752 30: −1.2839389 31:
−0.95752859 32: 0.26085943 33: 0.96349519 34: −0.53986728 35: 0.96847063 36: −0.5258432
37: 0.44683513 38: −0.016518893 39: −0.53123569 40: 0.73466289 41: −0.14847454 42: 0.39979953
43: −1.189554 44: −0.085250653 45: 0.78965682 46: −0.61769366 47: −0.27439302 48: −0.7249788
49: 0.75479484 50: −1.3104892 51: 1.6286936 52: −0.97226423 53: −0.25266522 54: −1.4067597 55:
−0.92626107 56: 0.99213964 57: −0.16685288 58: −0.51933849 59: −0.14818022 60: −0.14942604
61: 0.25867373 62: 0.020739969 63: 1.0102789 64: −0.43018341 65: 0.57322633 66: −0.20108385
67: 0.59315741 68: −0.19920386 69: 0.8077935 70: 0.36393169 71: −0.35045397 72: −0.13032785
73: 0.19120462 74: 0.92244279 75: −0.71011055 76: 0.78690231 77: 0.34503469 78: −0.20833312 79:
−0.82746303 80: 0.17615448 81: −0.47272056 82: 0.7111606 83: −0.0077136639 84: 0.91128999 85:
−0.508798 86: −1.3149154 87: 0.82740068 #
0.0023954962635083453 1: 5.9847097 2: 0.83190614 3: 3.2076981 4: 3.8079975 5: 1.3198755 6:
−4.9284029 7: −0.4078356 8: 0.23064108 9: −0.31782413 10: 0.086775824 11: −0.070308164 12:
−2.4426701 13: 1.4531602 14: 0.78984618 15: 0.82668793 16: 2.0980465 17: −0.18104351 18:
−0.76579428 19: 0.26044092 20: 1.7634895 21: −1.7859451 22: −0.54260099 23: 1.1592693
24: 0.60947007 25: −3.0047128 26: 0.48909226 27: −0.18609163 28: 1.3466139 29: −1.112694 30:

APPENDIX C5-continued

SVM Model Weights
(87; Benign/Malignant)

−0.26890093 31: −0.45765018 32: 0.42124534 33: 0.386136 34: 0.84868169 35: 1.6364788 36: −0.028519887 37: 1.2765138 38: −1.6163156 39: 2.7834327 40: 1.8628697 41: −2.5658431 42: 0.72739297 43: 0.64852452 44: 1.1074948 45: 0.97743762 46: 1.3194482 47: 1.5037328 48: −0.39539778 49: −0.032376789 50: −0.45744652 51: −1.2490126 52: 1.6085756 53: −0.3176223 54: 0.092892468 55: −0.17702933 56: 0.027009025 57: −0.34548298 58: 0.6999858 59: −0.5645808 60: −2.1313853 61: −0.12644149 62: 1.4977815 63: −0.35250148 64: −0.5773651 65: 0.59365129 66: 0.57536352 67: −0.19167207 68: −0.25678271 69: 0.29192075 70: −0.69047707 71: −0.38122773 72: 0.73858052 73: −0.34531942 74: −0.093373567 75: 0.23268723 76: 0.5194428 77: 0.40209553 78: 0.17498569 79: −0.27617094 80: 0.44819397 81: −0.40320599 82: 1.053353 83: −0.61412567 84: −0.54235631 85: −0.046558283 86: 0.69069844 87: 0.29973266 #
−0.0010327106926006091 1: −4.4828572 2: 8.2223415 3: 2.9781563 4: 4.4289684 5: −0.42227414 6: −1.5717493 7: 1.3719559 8: 2.9812431 9: −1.8863599 10: 0.47722155 11: 0.19453254 12: 2.5298641 13: −0.71065784 14: 1.6114749 15: −0.81230092 16: −3.0162938 17: 2.6504457 18: −0.69255483 19: 1.447444 20: −0.55961889 21: 1.1205018 22: 0.18635012 23: −3.4599066 24: −0.89394116 25: 2.299516 26: −0.76571792 27: −0.62200737 28: −1.4238536 29: 0.92606449 30: −1.6690691 31: 0.42135558 32: −1.2490917 33: 1.0898836 34: −0.0085214814 35: 0.80851263 36: 0.29543334 37: 2.4276736 38: 0.76313913 39: 0.54523146 40: 1.8881035 41: 1.1382017 42: 0.65388203 43: −1.0992905 44: 0.8885656 45: −0.2763125 46: 1.4083475 47: −0.99239188 48: −0.79970312 49: 0.63563782 50: 1.8465155 51: 0.75423354 52: 0.62939847 53: 2.2419858 54: 1.0266342 55: −0.89636725 56: 1.2229573 57: 0.85758764 58: −1.6142527 59: 0.36832121 60: −0.45254123 61: 0.36916149 62: 0.42660204 63: 0.17117092 64: −0.85252941 65: 0.81801111 66: −0.86623806 67: −0.38438568 68: 1.0171686 69: −0.93268329 70: 0.056972943 71: −0.26466134 72: 0.27018225 73: 0.17719872 74: −0.70610046 75: 0.04636937 76: 0.086477168 77: 0.29317954 78: −0.56059808 79: 0.090993397 80: 0.9166767 81: −0.061696541 82: −0.32518891 83: −0.77507943 84: 0.61390239 85: 0.17143469 86: 0.12792408 87: 0.25940463 #
−0.00053937311723063384 1: −7.7966084 2: 1.8707227 3: −23.323887 4: 1.0747559 5: 1.0184501 6: −3.600925 7: 9.3491745 8: −7.7337961 9: −1.2228185 10: 7.7243834 11: 2.0076487 12: −4.368228 13: −1.5946441 14: −0.2912291 15: −2.0482881 16: −0.38283157 17: −1.6580502 18: −1.0132759 19: −0.17344542 20: 0.65646726 21: −0.49175465 22: 0.29616475 23: −0.65766221 24: −0.40362445 25: 0.31434533 26: 0.98643875 27: 0.016180724 28: 0.12472247 29: −0.22155482 30: −0.0517218 31: −0.0058854236 32: 0.09278781 33: 0.34776777 34: −0.21737053 35: −0.091020077 36: 0.035350032 37: 0.2550841 38: −0.072128683 39: 0.0050051538 40: −0.072953671 41: 0.1237232 42: −0.10784111 43: −0.24674198 44: 0.10156032 45: −0.11400478 46: −0.0051734848 47: 0.070060618 48: −0.062755756 49: −0.1003389 50: −0.024766795 51: 0.042309508 52: −0.045899741 53: −0.018923813 54: 0.026509475 55: −0.013425832 56: −0.057100177 57: 0.062299002 58: −0.0071787904 59: −0.017751466 60: −0.080059178 61: 0.10251214 62: 0.19948693 63: −0.017395765 64: −0.065834261 65: 0.05320783 66: 0.13003403 67: 0.045583595 68: 0.015333543 69: −0.10374861 70: 0.017438892 71: −0.12824923 72: 0.1228321 73: 0.006350534 74: −0.13356683 75: 0.01609605 76: 0.019531524 77: −0.02920058 78: −0.017909111 79: −0.032119624 80: −0.081862949 81: 0.026391055 82: −0.053974025 83: −0.042487528 84: −0.040375195 85: 0.027134888 86: −0.085319266 87: 0.014382792 #
−0.00051766030504957889 1: −4.6798587 2: 6.9537511 3: 7.7693982 4: 2.5801184 5: 5.2154336 6: 1.5670055 7: −1.2078696 8: −3.9267974 9: −0.82684386 10: 3.3592942 11: −0.31578901 12: −0.053109273 13: −1.4976189 14: 1.5029013 15: −2.4395096 16: 2.8694046 17: 2.9962363 18: 1.3835291 19: −1.5468376 20: −0.57736629 21: −1.5085028 22: −1.9168996 23: 1.0982634 24: −1.5078399 25: −0.74366945 26: −2.0148342 27: −4.1114769 28: 0.23374891 29: −1.7665157 30: −0.039697465 31: −0.84676665 32: −1.1690859 33: 0.90180761 34: 1.2732987 35: 0.35115799 36: 1.8125541 37: 1.2799025 38: 0.45635095 39: −2.1887424 40: −1.5001509 41: 1.1002516 42: −1.6888564 43: 0.54384869 44: 0.65478468 45: −0.1762152 46: 0.3379482 47: 1.1854759 48: −0.15218729 49: −0.30370706 50: 0.7016831 51: −0.24664575 52: −1.4083092 53: −0.65109581 54: 1.2774956 55: 1.8864911 56: −0.37825456 57: 1.0201689 58: 0.55714577 59: −0.86095703 60: 0.23636958 61: 0.62589383 62: −0.10632792 63: 1.4403613 64: 0.97026974 65: 0.38492748 66: −0.035852015 67: 0.55633384 68: −0.46812025 69: 0.35794175 70: 0.22479694 71: −1.0400404 72: 0.02285002 73: 0.30000883 74: −0.19568017 75: −0.78765935 76: 0.58576965 77: 0.160667 78: −0.7600804 79: 0.014864877 80: −0.15830313 81: −0.15762 82: 0.16660199 83: −0.30902255 84: 0.03988146 85: 0.11803716 86: 0.42379734 87: 0.56217456 #
0.0012106666522769668 1: 8.938942 2: 3.6820235 3: 1.8444127 4: 3.1469421 5: −0.85917765 6: −3.1263924 7: 1.5923287 8: 2.7571449 9: 1.3356986 10: −1.0054343 11: −0.72609353 12: 0−.88047606 13: −0.052594084 14: 1.6568137 15: −0.2300657 16: −3.0733943 17: −1.024448 18: −0.33218354 19: 0.51852953 20: 1.423895 21: −1.7680084 22: 1.262127 23: −0.50992119 24: 1.1018715 25: 0.25038528 26: 1.5296953 27: 0.27678546 28: 1.4986688 29: 0.17097917 30: −1.2639122 31: 0.24007957 32: −1.168492 33: 0.14996158 34: −0.20664392 35: −0.67253661 36: −1.5472181 37: −0.55073613 38: −1.0028018 39: −0.75595587 40: −0.56938845 41: 1.4879873 42: 1.0382421 43: −1.6404175 44: 0.53891242 45: 1.5716094 46: 0.9801414 47: 2.6480227 48: 1.2949426 49: −0.72611874 50: 0.32097936 51: 0.25212988 52: 0.30690432 53: −0.90482062 54: 1.2643476 55: 1.5482213 56: −0.61030972 57: 0.5315522 58: −0.28144377 59: −0.26615247 60: −0.11889279 61: 1.3707041 62: −0.46235996 63: 0.11489861 64: −0.59105039 65: −0.26497191 66: −0.5130477 67: 0.097227156 68: 0.029428869 69: 1.0888489 70: −0.23034456 71: 0.84919131 72: 0.72287005 73: −0.20516318 74: 0.51046306 75: 1.5295547 76: 0.43179569 77: −0.047804844 78: 1.0349206 79: −0.070755199 80: 0.00070227258 81: 0.0333343 82: −0.65981573 83: −0.06182842 84: 1.0218269 85: −0.16569792 86: −0.28810197 87: −0.26579428 #
0.0016428417121487752 1: 9.1230593 2: 3.9607098 3: 1.5756338 4: 4.1874185 5: 2.1461926 6: −1.7388706 7: 2.1186652 8: 1.0513726 9: −1.2865088 10: −0.81872839 11: 0.040312272 12: −0.15184851 13: 0.31572929 14: 0.15833652 15: −0.26118129 16: −1.0505745 17: −1.0178174 18: 0.16850244 19: 1.525844 20: 2.4251978 21: 2.1380534 22: −1.7921528 23: 0.70529109 24: −0.86903912 25: −0.90763175 26: 2.0566919 27: −0.52910912 28: 0.33037242 29: 0.33875701 30: 1.0200107 31: 0.34964737 32: −0.46560356 33: −0.52523929 34: −0.24413136 35: 0.48999044

APPENDIX C5-continued

| SVM Model Weights (87; Benign/Malignant) |
|---|
| 36: 0.046803989 37: 0.035574108 38: 0.76940674 39: −0.22491753 40: 0.11223246 41: 0.28678265 42: 0.95212728 43: 0.11985786 44: −0.6971736 45: 1.0102677 46: −1.1753534 47: −0.68612713 48: −1.0194079 49: 0.0044652228 50: 0.47938496 51: 0.16353835 52: −0.54597574 53: −0.90813696 54: −0.37022072 55: 0.17169508 56: −0.53953499 57: 0.77884901 58: 0.27515292 59: 0.63446444 60: 0.59566504 61: 0.56384295 62: 0.18165052 63: −0.71566111 64: −0.78215849 65: −0.62599987 66: 0.41566026 67: −0.41583338 68: 0.75958508 69: 0.45774817 70: 0.33390945 71: −0.6251325 72: −0.33184326 73: 0.10600477 74: 1.3817265 75: −0.72555315 76: 0.64912313 77: 1.1465611 78: −0.30240169 79: −0.36051276 80: −0.71007937 81: 0.11025462 82: 0.7955364 83: 0.56237835 84: −0.34528831 85: 0.098673992 86: 0.1231902 87: −0.55380547 # |
| −0.0015755487835087932 1: −7.236392 2: −3.5836346 3: 1.7660971 4: −0.32848185 5: −1.2832146 6: −6.0978584 7: −3.6553211 8: −0.17175604 9: −0.25727716 10: 0.22893712 11: 2.0433552 12: −2.5095832 13: 2.2301786 14: 0.89164317 15: 0.035530206 16: 0.43601635 17: −1.5672219 18: −2.1941028 19: −1.6846048 20: −1.9031192 21: −1.5150453 22: −0.067690462 23: −0.7034052 24: −0.92714 25: 2.8568938 26: −0.54916203 27: −0.33980703 28: 1.3728271 29: −1.5007032 30: 1.5150614 31: −0.58766556 32: 0.91855782 33: −1.5538375 34: 0.69479793 35: 0.36874688 36: 0.54761487 37: −1.9475741 38: −1.2176952 39: 1.0730724 40: 1.9726436 41: −0.30647516 42: −1.2092241 43: 0.63217318 44: −0.77174801 45: −0.40446022 46: 0.10491796 47: −1.0020102 48: 0.61819273 49: 0.47567961 50: 0.013156149 51: −1.4068747 52: 0.2815071 53: 0.55821782 54: −0.062364895 55: 0.7315644 56: 0.60225677 57: 1.223998 58: 1.6821091 59: 0.7918604 60: 0.1890564 61: −0.84034485 62: −0.26253659 63: 0.36804584 64: 0.50272626 65: 2.2546327 66: 0.16593432 67: −0.23399231 68: 1.3119842 69: 0.49496078 70: 0.88905048 71: 0.9499805 72: −0.87751204 73: 0.32013476 74: 0.63699913 75: 0.19273549 76: 1.1294738 77: 0.65565783 78: 0.36823535 79: 0.82951087 80: 0.12251247 81: −0.012268872 82: −0.73517323 83: 0.17581578 84: 0.48176602 85: −0.18737254 86: −0.1223734 87: −0.17085168 # |
| −0.0010432053323105542 1: 5.7325249 2: −11.045574 3: −0.097632185 4: −1.8052405 5: −1.2875896 6: 5.6319304 7: −0.682576 8: 7.4624991 9: 6.9472523 10: 7.1493573 11: 6.4905562 12: −0.62037033 13: 2.9958172 14: −2.9622247 15: 1.5950644 16: 1.7982749 17: −1.3490666 18: −2.2707424 19: −0.80519658 20: −0.065100648 21: −0.22609113 22: 0.76079345 23: 0.3098391 24: 1.9317069 25: −0.43482473 26: −0.8905431 27: 0.059389889 28: −0.70592397 29: −0.60067618 30: −1.1722881 31: 0.24647436 32: −2.3679779 33: 1.3736523 34: −0.16647618 35: −0.20379338 36: 0.8717491 37: 0.085367218 38: −0.17762056 39: −1.0283386 40: 1.0598202 41: 0.86177987 42: −0.043636769 43: 0.36209476 44: −0.94240057 45: 0.073458038 46: 1.632615 47: −0.10052579 48: 0.39001518 49: 0.39055279 50: 0.65398258 51: −0.018352117 52: 0.91345263 53: −0.86458057 54: −0.040878139 55: 0.48280111 56: 0.60925186 57: 1.4350705 58: 0.45007205 59: −0.02744112 60: −0.45043981 61: −0.5089047 62: 1.3592848 63: −0.85350883 64: 1.1968377 65: −0.85319293 66: 0.63211513 67: 0.29143402 68: −0.28038654 69: −0.57851499 70: −0.050973598 71: 0.45104268 72: −0.83315337 73: 0.53573316 74: 0.31574732 75: 0.61738712 76: 0.066298179 77: −0.79675239 78: −1.2052398 79: −0.22975183 80: −0.032400642 81: −0.46031436 82: 0.50014967 83: 0.43328792 84: 0.34681287 85: −0.51940584 86: −0.06490311 87: 0.16338681 # |
| −0.00070130340853126461 1: −2.1706476 2: −1.9825846 3: 1.6808629 4: −9.7863483 5: 2.5575449 6: 0.7057032 7: −0.42950332 8: −4.667141 9: 1.9971507 10: −3.3588634 11: −3.4667838 12: −0.52633959 13: 0.2974067 14: −0.51303798 15: −2.2043688 16: −0.18758157 17: −1.5001959 18: −0.4526135 19: −2.3206253 20: 0.72880054 21: 0.85751021 22: 1.4700875 23: 1.5989654 24: −1.6109285 25: 0.75946838 26: −1.3694041 27: 0.069941387 28: −1.2863573 29: −0.71581751 30: −0.4410125 31: 0.85237789 32: 0.15556917 33: 0.31887108 34: −2.2846727 35: −0.30999845 36: 0.024915421 37: 1.3966018 38: 0.65068775 39: 0.19363178 40: −0.14380559 41: −1.6299479 42: 0.70048577 43: 0.078471817 44: 0.073357344 45: 1.3000478 46: 0.16561341 47: −0.030399367 48: 0.12559915 49: 0.21890526 50: 0.94152272 51: −0.81626856 52: 1.3058451 53: 0.72284049 54: −0.17456944 55: 0.13139088 56: 0.092829317 57: −2.0562599 58: 0.53846145 59: −0.1364658 60: −0.29483664 61: 1.29243 62: 1.3714556 63: −0.13506477 64: 0.47543222 65: −0.59440666 66: 0.78138715 67: 0.66857392 68: 0.38525146 69: 0.58482617 70: −0.029068982 71: 0.72725481 72: 0.37568855 73: 1.510435 74: 0.38365117 75: −0.96987337 76: 0.28935903 77: −0.69556022 78: −0.091853529 79: 0.37636095 80: 0.43708503 81: 0.26550123 82: −1.0570695 83: 0.35788676 84: 0.43593568 85: 0.79885823 86: −0.45753843 87: 0.94902861 # |
| 0.0018901694147291296 1: 3.3504007 2: 6.2324839 3: 2.6426129 4: 1.492183 5: 3.0097013 6: −1.152725 7: 3.869487 8: 0.46534666 9: −1.5877725 10: −2.5205293 11: 0.012004626 12: −1.0621814 13: −0.17664123 14: −2.0569618 15: −1.6601045 16: 1.1510824 17: 0.25813934 18: 0.13201335 19: −1.131669 20: 1.1496286 21: −1.575572 22: 0.2038112 23: 0.46738106 24: −0.70897067 25: −0.56662709 26: −0.48662603 27: 0.020907728 28: −0.37763599 29: −1.4949493 30: −0.64525312 31: −0.63886672 32: −0.58693498 33: 1.0291035 34: 0.49202242 35: −0.2502974 36: −0.76210868 37: −0.27610156 38: 2.3534727 39: 1.025668 40: 0.061278824 41: 1.5647804 42: 0.74536902 43: −0.10340484 44: 0.52367389 45: −0.24083184 46: −1.1846058 47: −0.3576465 48: 0.83624595 49: 1.9942691 50: −0.12304199 51: 0.87746346 52: 1.2957979 53: −1.8208426 54: 1.5262439 55: −1.1147339 56: −0.90715885 57: 0.27381408 58: 1.2977566 59: −0.025077818 60: −0.53921193 61: −0.32603326 62: −0.31038827 63: −1.2054646 64: −0.10846778 65: 0.61878496 66: −1.1695999 67: −0.69651842 68: 0.47412398 69: 0.48150793 70: 1.3362669 71: 0.62126261 72: 0.075418077 73: 0.87004262 74: −0.46395355 75: −0.59036511 76: −1.090446 77: 0.03209864 78: 0.10529161 79: 0.70742953 80: −0.31867182 81: −0.35844326 82: 0.79198897 83: 0.59871656 84: 0.163928 85: −0.49811831 86: −0.10127752 87: 0.49906915 # |
| −0.0015344058313885955 1: −1.4225143 2: −3.3811448 3: −1.3460624 4: −2.4572864 5: −1.2485046 6: 1.5272132 7: 3.8467693 8: 3.6000576 9: −2.5641577 10: −0.67970216 11: −1.2237694 12: −0.66455346 13: −1.7749182 14: 1.801129 15: −0.073441938 16: −1.0443138 17: 2.9320962 18: −0.62133968 19: 0.24629931 20: −2.5408921 21: −1.9696916 22: −0.15611142 23: −0.55407423 24: 0.17331484 25: −2.6666267 26: 0.11005254 27: −0.76523972 28: 0.82345724 29: 2.1196442 30: −0.10236285 31: 1.7822025 32: −0.34777778 33: −2.6759152 34: 0.95936936 35: −0.20149407 36: −0.27700329 37: 1.0371037 38: −0.35205483 39: −1.3395022 40: −1.517821 41: −1.6165372 42: 1.5603799 43: −0.14268057 44: 1.0620614 45: −0.2145381 46: 0.025638459 47: −0.10914129 48: |

APPENDIX C5-continued

SVM Model Weights
(87; Benign/Malignant)

−0.17478488 49: 0.4742581 50: −0.48568475 51: −0.023864167 52: 0.11586545 53: −0.062558644 54: 0.021825971 55: 0.30173782 56: −0.29385743 57: −0.56683713 58: 0.94771284 59: 0.29573876 60: 0.014790609 61: −0.34971812 62: −0.33196506 63: −0.87879521 64: 0.40384069 65: 0.058484275 66: −0.13888034 67: 0.19267932 68: 0.83802092 69: −0.60410917 70: 0.38784978 71: −0.045576707 72: −0.18632713 73: −0.15257339 74: 0.1837924 75: 0.1415422 76: 0.25753227 77: 0.00010349972 78: −0.44107446 79: 0.05193444 80: 0.12665264 81: −0.25195363 82: −0.21478599 83: −0.11333102 84: 0.080544256 85: −0.26152048 86: −0.025861861 87: 0.1800579 #
2.9940250202306032e−006 1: 9.8041286 2: 15.643085 3: −14.213445 4: −5.6504297 5: −2.8406351 6: 4.8410215 7: −6.6080933 8: −7.4779692 9: −0.5772323 10: −6.2781529 11: 8.2602367 12: 11.970333 13: 6.336812 14: 1.1768038 15: −1.7457997 16: 1.5841151 17: 1.5440294 18: −0.17547397 19: −0.62377983 20: 0.05088732 21: −5.221839 22: −2.9309611 23: −0.88320798 24: −1.282207 25: −0.28119931 26: 2.1707978 27: −0.44439083 28: 0.69384325 29: −0.84158903 30: −2.1587796 31: 0.8452878 32: 0.89773905 33: −1.0026301 34: −1.1124955 35: 0.88503838 36: −0.4235985 37: −0.14904873 38: −0.026293054 39: −0.73154718 40: 0.40854758 41: 0.2893393 42: 0.90045565 43: −0.402109 44: −0.20215705 45: −0.19731572 46: 0.68088818 47: −0.2196051 48: 0.31383833 49: −0.55526811 50: 0.1787241 51: −0.36807919 52: −0.2236544 53: 0.31867594 54: −0.11530373 55: −0.38835302 56: 0.088300563 57: 0.29786986 58: 0.16426006 59: 0.2670193 60: 0.2008242 61: 0.04549478 62: 0.010833706 63: −0.10576705 64: −0.018023184 65: −0.31581616 66: 0.4111937 67: 0.0011363255 68: −0.32500958 69: 0.052457977 70: 0.18141507 71: 0.010820718 72: −0.1970809 73: 0.031182472 74: 0.20898099 75: 0.092877805 76: −0.0068197995 77: −0.047145113 78: −0.0074180369 79: 0.075367324 80: 0.21236798 81: 0.063954644 82: 0.33653501 83: 0.087007843 84: −0.14029463 85: −0.086541794 86: 0.02149646 87: 0.066968374 #
−0.0010055342539319553 1: −8.6541967 2: 3.1313093 3: 3.124423 4: 3.0343151 5: −1.5841113 6: −2.2087634 7: 1.7894588 8: 2.8694017 9: −4.4243951 10: −0.45494816 11: 1.0369818 12: 1.0938125 13: 0.27073804 14: −1.4201082 15: −1.1111952 16: −1.1544274 17: −0.61541378 18: 0.89156842 19: 0.24313243 20: −0.96249247 21: 1.2922262 22: −0.69232893 23: 0.14764817 24: −1.3923763 25: 0.6387915 26: 0.084550619 27: −1.4210426 28: −0.043041125 29: 0.70565158 30: −2.2790606 31: 0.31711981 32: −0.29398012 33: −0.1432732 34: −1.0997872 35: 0.89468467 36: 0.17898633 37: 0.22860222 38: 0.046035666 39: 1.3129162 40: 0.072972745 41: −0.31119242 42: 0.24485055 43: 1.016295 44: 1.1550423 45: 0.57052416 46: 0.30313149 47: 0.47155845 48: −0.252554 49: 0.75614375 50: −0.27084967 51: 1.2873342 52: −0.50668657 53: −1.0563754 54: 0.68687969 55: −1.4469496 56: 1.1780907 57: 0.29481086 58: −0.39441538 59: −1.1455108 60: 1.0291282 61: −0.2951265 62: −0.63262415 63: −1.7717614 64: −0.38663942 65: 0.96479446 66: 2.2799258 67: 0.080531135 68: −0.7447601 69: 1.3578986 70: −0.52199012 71: −0.15072392 72: −0.57423425 73: 0.075259708 74: 0.38988864 75: −0.050941281 76: 0.39107621 77: −0.97717643 78: −0.43727434 79: 0.064068362 80: −0.97314757 81: −0.12114869 82: −1.2026515 83: 0.25698236 84: −0.0038959796 85: 0.6433928 86: 0.47606063 87: −0.52713388 #
−0.00032928884846625999 1: −0.82008016 2: −6.8423777 3: −6.1619401 4: −2.6320679 5: 0.83375293 6: −2.020021 7: −1.9923782 8: −1.6235381 9: −0.88103569 10: −3.0362997 11: −2.1458218 12: 1.8171666 13: 0.71794194 14: −2.233521 15: −1.5364541 16: 0.93289179 17: 4.6562896 18: −0.67585087 19: 1.0730962 20: 1.5860263 21: 3.6903191 22: 2.378103 23: 0.65362698 24: −1.0263125 25: −4.4432697 26: 0.16530563 27: 3.0466235 28: 0.34659573 29: −1.4444444 30: 0.59633666 31: −1.6122845 32: −1.997816 33: −0.70690131 34: 2.7609437 35: −1.4638962 36: 0.66209996 37: 0.96081573 38: −0.90774435 39: 2.0869017 40: 0.40851924 41: 1.4119679 42: 1.1785529 43: 0.6080929 44: −1.3131065 45: −0.75025433 46: 0.3115603 47: −0.33422759 48: 1.6780285 49: −1.6416742 50: 0.33127883 51: 0.58834219 52: −0.24024014 53: 1.509495 54: 0.23256554 55: −0.62915909 56: 0.25621805 57: 0.30218688 58: 0.69294071 59: 0.56959301 60: 0.15467633 61: −0.83308238 62: −0.24675837 63: −0.046901405 64: 0.67148012 65: −0.35064766 66: −0.011128491 67: −0.4612942 68: −0.5264625 69: 0.74184507 70: 0.78994858 71: −0.88191795 72: 0.78713906 73: −0.095115699 74: −0.068979301 75: −0.07245589 76: 0.81518006 77: −0.36369923 78: −0.048543081 79: −0.018825477 80: −0.22140215 81: 0.28148586 82: −0.13703474 83: −0.23811986 84: 0.17147642 85: 0.56859875 86: 0.057456624 87: 0.235888 #

APPENDIX C6

SVM Model Weights
(44; Early/Late)

SVM-light Version V6.01
0 # kernel type
3 # kernel parameter -d
1 # kernel parameter -g
1 # kernel parameter -s
1 # kernel parameter -r
empty# kernel parameter -u
44 # highest feature index
59 # number of training documents
48 # number of support vectors plus 1
0.47058211 # threshold b, each following line is a SV (starting with alpha*y)
−0.00056677276769644645 1:1.2953433 2:−10.811604 3:10.668916 4:7.6443572 5:4.8650537 6:−2.3720403 7:−0.53300303 8:1.4913656 9:2.2692528 10:−4.1517024 11:5.0973153 12:3.961812 13:−4.989172 14:5.9122295 15:2.8848045 16:−2.1117735 17:1.1214025 18:4.17628 19:−0.35360423 20:−0.57471097 21:−4.3517232 22:0.99931109 23:−0.83541495 24:−0.81100011 25:1.5716805 26:−0.70921725 27:−1.5307126 28:−0.17174035 29:−0.33846083 30:−1.4841211 31:−0.62835532

APPENDIX C6-continued

| SVM Model Weights (44; Early/Late) |
|---|
| 32:1.5003964 33:−0.36885175 34:−0.91448486 35:−0.17173344 36:0.59208959 37:−0.70629734 38:0.2362466 39:0.29450372 40:0.050759379 41:−0.65440804 42:0.98319513 43:−0.49021548 44:0.74737632 # |
| −0.0022301785905226978 1:−7.4905663 2:−4.2124224 3:2.557915 4:−5.2878695 5:0.80657786 6:−0.37115183 7:1.6812637 8:−3.7509978 9:0.51045167 10:4.1135268 11:0.76780587 12:1.3013476 13:−0.53182048 14:1.9176185 15:1.1816503 16:−0.35555935 17:−1.2507631 18:−1.747479 19:−1.9851712 20:−5.4316225 21:−0.64183134 22:−0.1643706 23:0.49522722 24:−0.50650555 25:1.0811261 26:0.4170202 27:0.59523118 28:−0.86196548 29:0.98918843 30:2.7127433 31:0.09164647 32:1.818579 33:−0.2627672 34:−1.4432161 35:−2.6616316 36:−1.7954003 37:1.4497789 38:−0.026815932 39:0.10891506 40:0.39038053 41:1.1279498 42:−0.46706548 43:−0.043462954 44:0.95625806 # |
| −0.0010049106558795064 1:6.7611756 2:−14.71443 3:8.2472305 4:7.897903 5:2.2104344 6:1.6990815 7:−5.5606017 8:−3.6665649 9:0.020383494 10:−2.7719841 11:4.6774445 12:7.1823139 13:0.92396528 14:−5.7546 15:−2.7706814 16:−6.6301026 17:−2.2711689 18:−1.306276 19:−1.7461162 20:1.3542767 21:−1.3777606 22:0.60129839 23:0.24038176 24:−1.4764284 25:−1.0552083 26:−1.0486079 27:1.2815171 28:−0.14424071 29:−0.014129613 30:0.8364315 31:−0.93981826 32:−0.82154411 33:−0.51832187 34:1.1584929 35:0.8353551 36:0.14221531 37:0.50732559 38:−0.15574506 39:−0.080617838 40:0.63888073 41:0.45644015 42:−0.64732808 43:0.5694508 44:−0.11251554 # |
| −0.0033549197977613297 1:−4.7538085 2:−0.59608591 3:1.9817924 4:0.188968 5:1.4622716 6:2.7846963 7:−0.015608484 8:−0.34373811 9:−0.33039114 10:1.4307724 11:0.19272146 12:−0.23617357 13:−0.0479552 14:2.1887279 15:−0.70616794 16:1.0666244 17:−2.6240268 18:−0.24965028 19:0.62618273 20:0.39855644 21:−0.77940083 22:−1.0156705 23:0.63041109 24:−0.12485303 25:−0.042265873 26:0.166668 27:0.74196172 28:3.572463 29:1.9412031 30:2.2433181 31:0.82924473 32:−0.9799 33:0.84773189 34:0.17739867 35:0.80027115 36:0.98595488 37:−0.35706881 38:0.18436019 39:0.54515535 40:0.16205844 41:1.3908807 42:−0.064833641 43:0.29049823 44:−0.8086499 # |
| −0.0033549197977613297 1:−8.3236828 2:−2.2087071 3:−0.27089623 4:2.6121626 5:2.6397204 6:3.6725602 7:2.614264 8:2.3370502 9:−2.1257644 10:−0.6181981 11:0.25396436 12:1.6628995 13:−0.4154028 14:3.5387452 15:2.3750374 16:3.0965297 17:−4.5929313 18:−0.2210283 19:3.013021 20:−0.56659156 21:−1.3427184 22:1.5178272 23:1.9356618 24:−0.78502053 25:−4.484839 26:−0.76929528 27:2.2739475 28:−4.4582672 29:−0.69363391 30:−0.32333046 31:1.2145813 32:1.0306679 33:0.56277591 34:0.6252628 35:1.3868178 36:0.95188469 37:0.76303911 38:0.64999557 39:−1.9922973 40:−0.72694093 41:0.86111587 42:−0.41919318 43:0.025058085 44:−0.73094058 # |
| −0.0011736639682222783 1:4.3982258 2:−0.16226812 3:0.28672937 4:−6.4362116 5:2.2866001 6:1.5062218 7:−1.2038572 8:−4.7404804 9:−2.3843164 10:2.2418141 11:−0.27465099 12:−2.8525231 13:2.1683853 14:−2.2989886 15:1.1782279 16:−1.7451806 17:−0.13980241 18:−0.97569644 19:2.1530244 20:0.67875266 21:−1.6640399 22:−0.19732694 23:−3.0789464 24:−0.19650537 25:−1.093295 26:1.5532137 27:−1.5915536 28:0.39503294 29:0.4357492 30:−0.26054665 31:1.5233505 32:0.020384328 33:0.68401867 34:−1.9224312 35:1.9247659 36:0.039446298 37:−0.81243855 38:−0.69054139 39:−0.79842049 40:−0.71187359 41:0.059527773 42:0.51264888 43:0.056126643 44:0.94826233 # |
| 0.0027994252146913896 1:−13.079961 2:1.0930103 3:2.5594432 4:0.53382522 5:−14.319618 6:−7.9226675 7:−5.8632889 8:−4.1756377 9:−1.4476115 10:−1.2879921 11:−0.88051426 12:0.80407524 13:0.68481839 14:−1.0680926 15:−0.58902317 16:1.5674455 17:−1.3136758 18:1.8976649 19:0.99831778 20:0.30186781 21:−1.2339196 22:1.8443847 23:1.7902417 24:2.6849024 25:−1.6639206 26:−0.94131452 27:−1.724227 28:0.95484877 29:1.2411916 30:0.94278502 31:−0.31173104 32:1.1069901 33:−1.0650786 34:1.0388733 35:−1.1440469 36:1.801355 37:0.34765008 38:2.0440075 39:1.0830725 40:−0.11946082 41:0.065369211 42:0.60018569 43:−1.6837276 44:0.66784209 # |
| 0.0014965832552085222 1:−4.7208257 2:4.0732508 3:1.5652837 4:4.0598516 5:−9.3037663 6:−0.83973908 7:−0.71216238 8:−0.83917409 9:−0.058870234 10:3.7083743 11:2.5553396 12:0.70841408 13:1.3753837 14:0.24954933 15:−0.0149606 16:−0.040375799 17:−0.17532998 18:1.7250814 19:0.88794386 20:1.113205 21:0.10319968 22:−1.2477883 23:−2.4926963 24:−0.94231015 25:1.4475657 26:2.4376483 27:1.81165 28:0.68418247 29:−1.7247032 30:0.68413621 31:1.0965656 32:0.72656965 33:0.26861012 34:2.0053701 35:2.0690022 36:−1.2135777 37:−1.5699004 38:−0.53900796 39:−1.3077862 40:−1.0385492 41:0.74263275 42:1.2781017 43:0.7582199 44:1.0456978 # |
| 0.0033549197977613297 1:−1.9800807 2:2.2620521 3:2.8543808 4:1.8967757 5:−8.6841125 6:7.2651377 7:−6.1430531 8:2.780396 9:5.0979185 10:3.9032483 11:−2.852982 12:1.1858057 13:−0.31181017 14:2.4165611 15:0.65978038 16:−0.98159003 17:−0.47111213 18:0.2488336 19:−2.4543958 20:1.345574 21:1.3306577 22:1.0412785 23:−1.6139855 24:−0.58955914 25:−1.5438869 26:1.2458951 27:−1.0349149 28:−3.0767884 29:1.2092717 30:−0.32970193 31:−1.1355613 32:0.41798267 33:1.5676863 34:1.6036789 35:−0.75510448 36:−1.0092349 37:−0.069946937 38:−1.9267184 39:1.4684548 40:1.5948615 41:0.18582146 42:1.4165688 43:−0.64861572 44:0.14727257 # |
| −0.6033549197977613297 1:17.764666 2:13.276847 3:−6.217092 4:0.85309285 5:−3.2269576 6:7.2593732 7:−5.8735247 8:3.7184291 9:0.69418424 10:−1.9208281 11:7.0488067 12:−3.0298989 13:−0.76913738 14:−3.5875182 15:−0.66790712 16:3.6537671 17:−2.8991296 18:0.19188908 19:0.011105056 20:−3.2731891 21:0.068219468 22:1.9221981 23:−1.1808108 24:0.87695962 25:0.19940683 26:−1.0992702 27:2.4589097 28:0.62231517 29:−0.79621994 30:−1.1352015 31:−1.88065 32:−0.0081547666 33:−0.70600635 34:−0.4687255 35:−0.14779152 36:−1.3467897 37:−1.0534955 38:1.2117174 39:1.5018312 40:−0.66517234 41:0.91468376 42:0.016846249 43:0.0320279 44:1.0009896 # |
| −0.0033549197977613297 1:2.5751998 2:10.221202 3:−0.95512414 4:9.3179073 5:−1.7831018 6:4.4525976 7:2.2225649 8:1.906949 9:2.5413458 10:−3.9868 11:−0.63038528 12:2.1551003 |

APPENDIX C6-continued

| SVM Model Weights (44; Early/Late) |
|---|
| 13:−1.2248868 14:1.4060228 15:−1.4359819 16:−1.2918285 17:1.0110083 18:−0.061929401 19:1.4711499 20:−1.4881929 21:0.80258656 22:−1.1465348 23:−1.5264565 24:0.27148193 25:1.1045482 26:2.2288132 27:0.50440538 28:0.18125741 29:0.3346369 30:−1.7561769 31:1.2301488 32:2.4653473 33:2.2793252 34:0.34436762 35:−1.717563 36:0.78135854 37:1.5482913 38:−0.3626014 39:−0.56852841 40:0.39892247 41:0.89233398 42:−1.4358878 43:0.64159596 44:−0.55421036 # |
| −0.0033549197977613297 1:−5.463172 2:7.882761 3:−2.6611001 4:4.7720952 5:−2.6212659 6:−0.66245055 7:6.5618205 8:0.32615471 9:1.1786789 10:−4.1691036 11:−0.4203403 12:1.7752379 13:−0.11802472 14:−2.7309148 15:−1.7289203 16:−0.47674027 17:−0.095811032 18:0.75439733 19:0.075886451 20:0.13598223 21:−0.72880638 22:−1.1294914 23:1.3876489 24:1.3553932 25:−1.501804 26:−1.3678044 27:−3.9636581 28:−0.33515278 29:−4.5743499 30:1.060473 31:1.2314618 32:0.14404362 33:1.9053147 34:0.21452859 35:−0.28400692 36:−1.4552145 37:0.40343893 38:0.31537935 39:1.3406228 40:−0.58248907 41:−1.2276702 42:−0.44912559 43:1.5652546 44:0.86094886 # |
| −0.0032144096193390736 1:5.4242792 2:8.5105228 3:−3.6257584 4:−4.6308413 5:−0.75645578 6:−0.45588413 7:−0.88993597 8:−5.7085314 9:−1.9537624 10:−0.09565293 11:0.38187858 12:−1.137969 13:−0.76989567 14:0.38682535 15:−1.6267631 16:−0.19945671 17:1.2119049 18:0.22235118 19:−0.8249591 20:−2.607296 21:−0.31416124 22:2.4226515 23:−0.036228649 24:0.044377733 25:−0.85722339 26:1.6688207 27:−3.1746669 28:−0.53754961 29:−1.5170302 30:1.2003756 31:−1.0720835 32:0.67520529 33:−0.65237749 34:0.67227352 35:2.4610274 36:0.93812031 37:1.1232651 38:−0.14917752 39:−1.1775687 40:0.92472392 41:−0.046555012 42:1.5438993 43:0.75920689 44:−0.40638646 # |
| −0.0029377774178558748 1:−5.8183594 2:11.128675 3:0.79399675 4:5.2573433 5:4.4285293 6:0.95433325 7:−0.69111842 8:−4.1106591 9:2.5315742 10:2.0295665 11:−2.6745369 12:0.84233916 13:−1.7253991 14:2.8288822 15:−2.9223824 16:2.9646323 17:3.0143211 18:2.6608479 19:3.9952185 20:1.4995718 21:2.1989398 22:−0.47424674 23:1.3009776 24:−0.16630308 25:1.0945835 26:0.041169818 27:2.9997933 28:−0.13137996 29:−0.63695759 30:1.4042147 31:−0.41155079 32:−1.1410439 33:−0.95365351 34:−1.3116107 35:1.0361317 36:0.094957031 37:1.8969471 38:0.70636696 39:0.98500276 40:−0.70368975 41:1.107469 42:0.28593799 43:−1.0727774 44:2.3539567 # |
| 0.0033549197977613297 1:−0.24590166 2:−8.1644478 3:3.5928798 4:−1.0753064 5:−2.0135837 6:−0.10096657 7:−1.1228001 8:−3.6788621 9:−1.2726107 10:−2.0068936 11:−2.3925679 12:1.0569448 13:−0.40451995 14:0.88951957 15:−4.2740674 16:2.5109732 17:−1.3839777 18:−1.826614 19:0.79616469 20:−3.4918079 21:2.5179839 22:2.6169379 23:1.2478143 24:−2.9698548 25:4.3714228 26:−0.19307458 27:−1.039034 28:−1.4048718 29:−1.5676883 30:−1.3980765 31:1.1577379 32:−1.6144001 33:−1.1187478 34:−0.030886892 35:0.68731695 36:−1.4642311 37:−0.28218594 38:0.97064406 39:−0.63970482 40:0.7588104 41:−0.14460278 42:0.4816044 43:−1.057313 44:−0.95472586 # |
| 0.0033549197977613297 1:−7.5296364 2:−0.089652337 3:1.6496497 4:−2.9499371 5:−0.089410551 6:−1.4661449 7:5.7495131 8:−0.59138709 9:−2.9437177 10:0.49092665 11:0.25325522 12:−5.5844264 13:−0.58515418 14:−1.6031579 15:−3.2792425 16:−2.5045371 17:−1.9578328 18:0.72970074 19:0.5297811 20:1.2443616 21:0.022985032 22:0.98236364 23:0.047812771 24:−1.324574 25:−0.34963769 26:0.14184867 27:0.71378028 28:0.39638865 29:−0.35865536 30:−0.62940234 31:0.51807815 32:1.1381087 33:−0.87863255 34:−1.210515 35:−1.7179273 36:−1.1261417 37:−0.48560384 38:−0.4191128 39:−1.5731698 40:1.8958013 41:0.46835396 42:−0.10821192 43:0.69468832 44:0.40906781 # |
| 0.0033549197977613297 1:1.7432362 2:2.2080975 3:−0.45811424 4:−0.25904602 5:3.5310566 6:−1.0701555 7:2.6190839 8:−1.5763268 9:−0.24684133 10:7.6938968 11:−1.0055476 12:0.37766281 13:0.39471114 14:0.32477632 15:0.26778743 16:0.88798404 17:−1.6143467 18:5.739316 19:−3.8111773 20:−0.13830076 21:−1.5627664 22:0.48013633 23:1.9933881 24:1.3006287 25:2.1235414 26:−0.84740353 27:1.1789974 28:1.5507125 29:−2.3316514 30:−0.99013168 31:−2.1526787 32:0.15070185 33:0.69957173 34:1.2233592 35:1.0863832 36:−0.076190881 37:1.7095969 38:−1.058123 39:−0.42751789 40:0.24727733 41:−0.34472501 42:−0.35372955 43:−0.22552487 44:−1.7159878 # |
| 0.0033549197977613297 1:8.6113596 2:0.035663262 3:0.78688341 4:1.3550853 5:3.178411 6:−1.0208944 7:−0.012796087 8:0.31668177 9:1.7832772 10:2.1886377 11:−2.8534501 12:1.0220896 13:0.030270895 14:−0.66597974 15:0.43166605 16:3.9161992 17:0.4159708 18:1.3348063 19:4.40974 20:1.7781575 21:−3.0399804 22:−0.25343016 23:−1.007033 24:−0.641725 25:1.4820757 26:−1.3819367 27:−0.68774104 28:−2.3879135 29:0.10838588 30:3.4089692 31:−2.6494894 32:−1.3129921 33:−0.84585792 34:0.80604839 35:−1.7579656 36:−0.32661092 37:−1.5601457 38:0.44571051 39:−0.8390938 40:0.54495227 41:−0.36589965 42:−1.3181593 43:1.8035884 44:0.50529796 # |
| −0.0031919358747512184 1:5.0472207 2:−15.336944 3:10.763581 4:0.12245622 5:−1.045119 6:5.0700855 7:0.022931358 8:1.0390165 9:−1.5287296 10:−1.8780161 11:−5.8217788 12:−3.495168 13:−2.9807045 14:−0.93120396 15:−0.96876276 16:1.1067419 17:2.2245276 18:−0.5159561 19:−0.56864065 20:−1.6035483 21:−0.071308769 22:0.71298867 23:−2.427552 24:6.1049132 25:−2.2994764 26:0.17956683 27:2.0975831 28:0.88850158 29:−1.187152 30:1.2519076 31:0.40507555 32:−0.65364575 33:−0.062440809 34:0.60360342 35:0.65818083 36:−1.6613714 37:0.84727097 38:−0.78944671 39:−0.60838294 40:−0.033466902 41:−0.67201972 42:−0.76183414 43:−0.99352539 44:−0.0064195753 # |
| −0.0033549197977613297 1:12.019065 2:−4.8004398 3:4.4707756 4:4.196064 5:4.823154 6:−7.7504168 7:3.056613 8:−2.0674977 9:5.8091102 10:1.8406044 11:−2.3205659 12:1.760255 13:0.70300639 14:−4.6173835 15:1.6834904 16:2.0209546 17:−5.0978332 18:3.7654126 19:1.4629006 20:−0.6220144 21:3.7241907 22:−0.58752209 23:−3.6073112 24:−0.23158151 25:−1.1288562 26:1.0939022 27:−1.4788034 28:0.19784832 29:0.93105268 30:−1.0950043 31:0.56641442 32:−0.034652114 33:−0.94231671 34:−0.8641625 35:−1.1210113 36:0.079980716 37:0.87809104 38:−0.33434898 39:−0.33466536 40:−1.4810408 41:−0.49689689 42:0.90456569 |

APPENDIX C6-continued

SVM Model Weights
(44; Early/Late)

43:−0.28511754 44:−0.53556454 #
−0.0033549197977613297 1:−3.3880587 2:−2.6414342 3:2.8064957 4:−1.3999835 5:−2.6332676 6:6.3005533 7:1.1491936 8:2.35604 9:0.27799395 10:1.1523478 11:−3.8036392 12:−3.2891657 13:−0.86931056 14:0.55123371 15:−0.44594151 16:−0.88298255 17:0.41254392 18:0.54672933 19:−2.0287313 20:0.3622455 21:2.7641249 22:1.2421728 23:−2.0061574 24:−3.2011676 25:−0.53145313 26:−0.64420927 27:−0.75167179 28:1.4715383 29:−0.25729042 30:−0.43156871 31:0.4395895 32:0.71389002 33:−1.5089703 34:1.3503698 35:−0.56789869 36:2.040731 37:1.0265932 38:2.6680079 39:0.87354589 40:0.1352763 41:0.076715931 42:−0.56060839 43:2.752434 44:−0.307383 #
0.0033549197977613297 1:4.3136711 2:11.85136 3:−2.4349139 4:4.3976011 5:−0.064428166 6:3.3004136 7:0.26722765 8:0.083926447 9:2.1508505 10:−1.2738918 11:−1.768934 12:0.17292808 13:0.44556588 14:−0.59223634 15:−0.96534908 16:−1.6171639 17:1.2820607 18:−0.84876287 19:1.4367297 20:−0.6155647 21:−2.36043 22:−0.019897325 23:−1.2100018 24:−0.45661017 25:0.22039026 26:−0.91286564 27:0.937419 28:−0.13718922 29:0.74340838 30:0.70248711 31:0.43081525 32:−1.2747772 33:0.4775075 34:−2.2567503 35:−0.24196947 36:−0.66949981 37:1.1833178 38:1.0137376 39:−0.2061992 40:0.95708007 41:2.7814839 42:0.68686748 43:−1.0831043 44:−2.3519526 #
0.0033549197977613297 1:7.9950004 2:7.8763146 3:−2.6768916 4:4.3499146 5:−0.26874429 6:−1.2617569 7:7.5231724 8:−1.001968 9:−3.2742054 10:−4.0525489 11:−3.2061014 12:1.1717849 13:−0.077940315 14:−0.21310687 15:5.9929557 16:−3.0397136 17:−2.1435318 18:−1.0098519 19:−2.4063938 20:−0.1814501 21:1.1750045 22:0.60953563 23:0.6414243 24:4.1224709 25:3.3680656 26:0.56308722 27:0.8397575 28:−1.1192403 29:1.2833984 30:−0.095799439 31:0.44614187 32:−1.7961432 33:−0.16294682 34:1.2279147 35:0.12392759 36:1.0085716 37:−1.2530149 38:1.3775395 39:−1.2154675 40:1.3844229 41:0.84347206 42:1.3588188 43:0.49808076 44:0.89308292 #
0.0033549197977613297 1:11.704061 2:6.5949616 3:0.45483977 4:4.3702846 5:0.58678722 6:4.2801876 7:−6.5564938 8:−2.7858698 9:−10.711282 10:5.1795998 11:−0.23074189 12:2.5389693 13:−7.9909263 14:−0.42881522 15:3.1987579 16:−0.885517 17:0.47581372 18:0.5075509 19:0.6129297 20:0.87700886 21:2.9646459 22:−2.4006853 23:1.8537773 24:−0.3296504 25:−0.99861437 26:−2.0937648 27:−1.8252416 28:0.2058742 29:0.44918847 30:−0.57538432 31:0.84618878 32:0.69699323 33:−0.34345084 34:−1.1655228 35:−0.53105354 36:−0.52976108 37:−0.90983158 38:−0.22549088 39:0.11226936 40:−0.062483769 41:−0.61575305 42:−0.41575837 43:−0.12159781 44:−0.66372013 #
0.0033549197977613297 1:2.1832664 2:5.4387846 3:1.7195971 4:2.0288308 5:0.93580216 6:1.0958407 7:−1.1356411 8:−1.3170016 9:0.4036161 10:0.66208827 11:−1.1981317 12:−3.9873779 13:1.083784 14:−1.2963853 15:−2.180872 16:−1.6959615 17:−0.21459815 18:−2.1435783 19:−0.18801655 20:−2.7198138 21:−0.46923888 22:−1.1304476 23:0.37281671 24:−0.29892316 25:−1.6967143 26:−1.0425665 27:0.52042228 28:0.18850514 29:−0.075532474 30:1.3673506 31:−0.20927349 32:1.8332825 33:−0.18675824 34:−0.77807641 35:−0.29415804 36:2.7382598 37:−1.1937499 38:−0.80527872 39:−0.51797247 40:−0.67693812 41:0.0044574765 42:1.3281074 43:−0.66870785 44:−0.55758661 #
0.0033549197977613297 1:12.366791 2:6.0081248 3:1.7113053 4:2.7979217 5:6.9255257 6:−8.9968224 7:−2.4731126 8:−1.0733718 9:1.2842386 10:−2.012439 11:−0.15039405 12:−2.9278686 13:−0.12789282 14:0.48431939 15:1.1856391 16:1.6238549 17:−0.51580727 18:−2.8973534 19:−1.2217386 20:2.441119 21:−0.56590825 22:−0.95627594 23:2.3723722 24:−2.3519976 25:−1.8573409 26:2.5932043 27:0.28923574 28:0.91411924 29:0.16916099 30:0.7578814 31:0.86746114 32:0.06571959 33:1.2952554 34:1.8225979 35:−1.0471101 36:−2.594789 37:0.91302282 38:1.0032086 39:0.58218884 40:0.82992595 41:0.2371375 42:1.4115078 43:−1.3569217 44:0.005501179 #
−0.0033549197977613297 1:4.9163074 2:8.6507969 3:−2.8113577 4:−2.7883282 5:3.6005468 6:−3.0850611 7:−1.1117666 8:−1.8606527 9:−0.43682045 10:−0.8709569 11:−0.20078206 12:−1.726822 13:−0.41964892 14:1.0194467 15:−0.13852639 16:0.38812613 17:−1.9748995 18:−0.94841814 19:−2.4416196 20:−0.80338186 21:−2.112071 22:−0.32373482 23:1.1838528 24:−1.0883764 25:−0.86285484 26:0.36459005 27:2.0366642 28:1.6910253 29:−1.0555723 30:0.68032825 31:0.30717254 32:−1.4960066 33:0.21581893 34:0.84493101 35:−1.536992 36:1.8034772 37:0.22908193 38:−2.0604062 39:0.25210926 40:−0.48998925 41:−0.80221105 42:−0.23084036 43:1.2399592 44:−0.15893972 #
−0.00010287624276736327 1:−2.988956 2:−14.541928 3:−24.152397 4:7.8578658 5:0.62039638 6:−1.4124461 7:−3.5245433 8:0.23765643 9:0.59025252 10:0.51212358 11:−1.3314158 12:−2.0315864 13:−0.2914176 14:0.37882963 15:0.082344197 16:−0.57432884 17:0.080625705 18:−0.14113382 19:−0.13893105 20:−0.28207991 21:0.12245945 22:−0.23306957 23:−0.074358061 24:0.075329393 25:0.095754124 26:0.17469533 27:−0.15946545 28:0.030569298 29:−0.041504841 30:0.1790569 31:0.18031198 32:−0.18188456 33:−0.14256233 34:−0.087481722 35:0.093072012 36:−0.0096975714 37:0.055885319 38:−0.26989311 39:0.060945775 40:0.025113981 41:−0.020692149 42:−0.027143152 43:0.010555366 44:0.17869918 #
−0.0023923167636648989 1:8.4171867 2:5.161294 3:1.8632329 4:5.0714602 5:5.020833 6:−0.54171818 7:−0.74185503 8:−5.2189178 9:6.4979911 10:1.7390909 11:−2.4017231 12:0.7056089 13:4.4163647 14:4.5082531 15:0.24772555 16:−1.049571 17:3.4169843 18:−2.5641735 19:−0.78975821 20:−0.5222187 21:0.89725953 22:3.7222507 23:1.0190701 24:0.7194767 25:−1.119658 26:−2.1368935 27:−0.54928917 28:1.0772496 29:1.3982881 30:−1.1084408 31:−0.12536865 32:1.1006286 33:−0.43901601 34:1.1063771 35:0.71711397 36:−0.84509456 37:−2.4609451 38:0.68434292 39:−0.64825416 40:−2.0648291 41:−0.44888297 42:−1.0822344 43:0.51638848 44:−0.57787544 #
−0.0033549197977613297 1:4.2723708 2:1.0816427 3:−5.1717262 4:−9.1334429 5:−1.5630178 6:−4.2477694 7:−1.4042612 8:8.0716524 9:−0.61411405 10:−1.2446501 11:3.4675648 12:4.4002695 13:0.21902591 14:0.50494504 15:−0.82781434 16:−3.6835434 17:2.1844773 18:1.9099612 19:2.0609009 20:−1.1665273 21:−0.24986534 22:0.78420079 23:0.5788486 24:1.6854416

APPENDIX C6-continued

| SVM Model Weights (44; Early/Late) |
|---|
| 25:0.16731662 26:1.1378598 27:0.14232612 28:0.27002251 29:0.88255745 30:0.67109448 31:1.0879683 32:1.10175 33:−1.8246135 34:−0.0084914742 35:−1.0067412 36:−0.92044687 37:0.70606804 38:−0.23283091 39:−1.322379 40:−1.7937051 41:0.27961293 42:1.3750051 43:0.65474033 44:−1.502453 # |
| 0.0033549197977613297 1:9.7260504 2:−7.8163357 3:6.8109908 4:4.9323745 5:−1.6638223 6:3.745981 7:−0.47318304 8:2.3136632 9:0.40887526 10:0.53233683 11:0.34330738 12:0.35754034 13:1.4566673 14:−0.30523223 15:−1.4400436 16:3.4091852 17:0.3001543 18:−1.9154788 19:1.5003307 20:1.25828 21:0.19474351 22:1.4655597 23:4.9832253 24:1.5780417 25:1.8085375 26:3.7642848 27:−1.0302637 28:−0.35661903 29:0.23552622 30:−0.92275572 31:−0.18625316 32:−0.60383582 33:0.16416991 34:−2.4490721 35:0.100034 36:2.124181 37:0.56455523 38:−2.1926215 39:1.3556439 40:−0.77462763 41:0.13219014 42:0.85297424 43:1.3223977 44:0.24121812 # |
| 0.0033549197977613297 1:1.5687745 2:2.8747225 3:−4.5921497 4:0.64045548 5:1.2402862 6:−1.6395731 7:6.439642 8:2.6914668 9:−1.4795072 10:−1.9112765 11:1.2422292 12:1.8375124 13:−0.94092149 14:−1.5335485 15:0.75675613 16:2.4802206 17:0.34209159 18:−1.2560471 19:−2.1931856 20:3.7075293 21:1.1574953 22:3.5674658 23:0.15892406 24:−0.82145321 25:0.33991763 26:0.49271733 27:0.052549031 28:1.1602603 29:2.4897397 30:1.3658088 31:−1.7658501 32:3.6958034 33:−1.048786 34:−1.3994727 35:2.1602569 36:−1.0454955 37:1.4556481 38:−0.61492872 39:−0.61211729 40:0.33369657 41:−1.1614405 42:−1.7464546 43:−0.42068875 44:0.88658863 # |
| 0.0033549197977613297 1:−7.6496434 2:2.703886 3:0.28662038 4:1.7879531 5:−3.0434427 6:−1.193588 7:6.320919 8:0.0046777669 9:−1.8738962 10:−0.86983484 11:−0.90390557 12:−0.33946124 13:−2.0940609 14:0.3616263 15:−0.41190428 16:−1.1988773 17:−0.26797518 18:−1.5384048 19:1.2224176 20:1.0135792 21:−0.91025347 22:0.67726129 23:−0.097032793 24:−1.0411915 25:0.20235281 26:0.80218315 27:−1.1149094 28:−0.075297311 29:−1.420293 30:0.039273173 31:−1.0670592 32:0.24752171 33:−0.81297511 34:0.55062044 35:−0.051494792 36:−1.2710344 37:−2.9904377 38:−2.3883932 39:1.0788088 40:−0.61928475 41:1.4220651 42:−0.63513494 43:−1.2401781 44:−1.5525755 # |
| −0.0030898033669306242 1:−3.0042043 2:−3.113188 3:0.97381061 4:3.8624547 5:0.49664947 6:6.8813305 7:3.981081 8:0.12391745 9:−7.6547618 10:−2.7285914 11:−0.53179222 12:−0.30781594 13:7.1988821 14:−0.44064531 15:1.0810283 16:0.82087684 17:2.8132896 18:6.1163325 19:−0.52160966 20:−1.1575588 21:−0.34605175 22:1.7179306 23:1.239956 24:−2.2303703 25:−2.0092707 26:1.3119591 27:0.4040986 28:0.94076431 29:2.2957568 30:0.35625714 31:1.05492 32:−1.8137116 33:0.085117221 34:−0.17722237 35:−0.93875301 36:−1.492783 37:−0.82638711 38:−0.040122535 39:1.2046241 40:0.11793934 41:−0.12299792 42:0.31207559 43:0.16833082 44:−0.06479533 # |
| −0.0033549197977613297 1:5.9731479 2:−2.2345276 3:2.4485157 4:0.69162613 5:0.90995193 6:0.060546741 7:1.8535619 8:−4.2391319 9:−3.620893 10:−0.84653771 11:1.5584985 12:−0.72690475 13:1.0212981 14:0.82094777 15:0.12706149 16:0.44026414 17:0.51657689 18:−1.7734509 19:−0.82144797 20:−0.95747542 21:0.71957904 22:−0.80198896 23:−2.2893806 24:−0.034846626 25:1.8044568 26:0.59219909 27:−0.66372091 28:−1.2759969 29:0.34522814 30:1.7603507 31:0.1729089 32:0.50999016 33:−0.050911739 34:0.95418978 35:−1.2323328 36:1.371628 37:0.25137526 38:−1.2536705 39:0.76166493 40:−1.084955 41:−0.45288616 42:−1.5072262 43:−0.27096277 44:1.378207 # |
| 0.00082887483474428547 1:13.466636 2:−3.3573108 3:5.5644298 4:0.57824087 5:1.6920621 6:−4.2968526 7:−2.6953287 8:12.022702 9:−0.46672329 10:3.9010904 11:0.45902482 12:−2.2463238 13:0.8365761 14:1.4948182 15:−2.4529717 16:−0.018621992 17:−0.018616691 18:−1.1184366 19:2.0151198 20:1.3533055 21:0.72912431 22:0.03273252 23:0.87820792 24:0.90275949 25:0.52287197 26:−1.414227 27:−1.1956365 28:1.5341172 29:−0.20564413 30:0.82979262 31:2.2867506 32:0.16699626 33:−0.2037773 34:1.3190736 35:0.43436375 36:0.012350954 37:−0.05768029 38:0.40372571 39:−0.64488149 40:2.1604466 41:0.53956074 42:−0.20766212 43:0.26843727 44:0.45486873 # |
| 0.0033549197977613297 1:3.8433597 2:2.4452479 3:−2.7605469 4:−2.1829417 5:−0.22223227 6:0.20662466 7:8.3353586 8:1.2071977 9:0.19084433 10:0.58242756 11:0.57760549 12:−0.43349019 13:−0.25145283 14:−1.5430319 15:0.15049267 16:0.13998732 17:0.16344859 18:−0.80469674 19:0.63106662 20:2.2429247 21:−0.69218796 22:0.5077576 23:−1.6572852 24:−1.3704666 25:0.15443374 26:−1.487389 27:1.7199481 28:−1.1768694 29:−0.65691537 30:−0.91387093 31:1.9700028 32:−0.17521015 33:−2.4380445 34:1.2323334 35:0.6152029 36:2.0528264 37:0.37548435 38:−0.73991114 39:2.3915479 40:0.54931939 41:−0.84648585 42:0.14254348 43:−2.3261664 44:−0.0031731338 # |
| −0.0033549197977613297 1:2.9703248 2:−1.9154285 3:−1.4705251 4:−3.6158135 5:−0.88654208 6:−5.2746539 7:3.5916541 8:−1.5249115 9:0.42257392 10:0.1542328 11:−0.79797947 12:1.5178829 13:−4.328999 14:−1.9303721 15:−3.6791089 16:2.030098 17:3.196708 18:0.70455837 19:−0.99888653 20:−0.90641922 21:−1.3292599 22:−1.3334385 23:−0.034880091 24:−0.21998923 25:−1.0224223 26:−0.27785692 27:0.887824 28:−0.88122153 29:2.4520988 30:−1.8591628 31:−0.2047378 32:−0.43277052 33:1.3049064 34:0.28490406 35:0.58858889 36:0.31118494 37:−0.75974351 38:0.30014536 39:0.16725326 40:0.28239837 41:0.85730082 42:0.18312453 43:0.73757261 44:0.23835303 # |
| 0.0033549197977613297 1:−6.6983242 2:−9.0942469 3:1.7515687 4:−0.034388322 5:−4.4506936 6:0.60848588 7:4.9920249 8:0.42073253 9:−1.6036102 10:4.4492455 11:0.61170918 12:1.7242055 13:−2.4792538 14:1.1316463 15:0.55399567 16:−0.67547733 17:−0.71950591 18:−3.7744215 19:0.12060646 20:1.7497555 21:−0.85744029 22:−0.2730225 23:−0.18385465 24:0.064841606 25:−0.29801944 26:3.2788053 27:1.8581574 28:1.7073642 29:−1.5964348 30:−1.0948637 31:−1.7955403 32:−0.33725154 33:0.59672004 34:−0.64073378 35:−1.2621409 36:−0.2854811 37:−0.77229369 38:3.2878306 39:0.32339731 40:−1.8727088 41:−1.8741317 42:0.62994355 43:0.24595919 44:−0.30926743 # |
| 0.0033549197977613297 1:8.0561037 2:−1.9924136 3:0.82999653 4:−3.7921369 5:−0.51860911 |

APPENDIX C6-continued

SVM Model Weights
(44; Early/Late)

6:−6.4783216 7:1.8349005 8:9.0483742 9:−5.104785 10:0.79596269 11:−3.5503304 12:0.75062472
13:4.4150515 14:0.4702543 15:0.7237826 16:−3.622617 17:−0.06912373 18:−0.52799076
19:1.5017456 20:−3.5132833 21:0.99361396 22:−0.92652875 23:−0.38866544 24:−1.7653948
25:−0.16442132 26:−0.61083925 27:−0.67040193 28:−0.2000851 29:−0.59121299 30:−0.51341027
31:−3.8886027 32:−0.1798937 33:2.6713161 34:−0.14334825 35:0.89026397 36:0.85009325
37:0.19307545 38:0.44975233 39:0.91792029 40:−0.53343427 41:0.32704374 42:−0.82176453
43:−1.5447295 44:0.5786891 #
0.0033549197977613297 1:0.12176631 2:1.5119995 3:−0.2009106 4:2.364769 5:−2.1576962
6:5.2755914 7:5.1912417 8:3.4393139 9:2.883764 10:5.7631373 11:2.7202239 12:−0.32031089
13:2.678786 14:−0.60210669 15:−1.4041533 16:−0.1163752 17:−0.39201191 18:−1.0063212
19:−4.5707445 20:1.3226789 21:−2.5034225 22:−1.5694625 23:−0.089195952 24:0.82619452
25:0.2266219 26:−1.857953 27:−2.5074837 28:−1.8170778 29:0.85228193 30:0.48416921
31:1.206537 32:−1.4583262 33:0.2215921 34:−2.5907068 35:0.39124185 36:−0.14954042
37:0.2999247 38:1.4811584 39:−0.8232218 40:−0.53053021 41:1.00964 42:0.62065589
43:−0.81233174 44:0.47553596 #
−0.0033549197977613297 1:2.9703248 2:−1.9154285 3:−1.4705251 4:−3.6158135 5:−0.88654208
6:−5.2746539 7:3.5916541 8:−1.5249115 9:0.42257392 10:0.1542328 11:−0.79797947 12:1.5178829
13:−4.328999 14:−1.9303721 15:−3.6791089 16:2.030098 17:3.196708 18:0.70455837
19:−0.99888653 20:−0.90641922 21:−1.3292599 22:−1.3334385 23:−0.034880091 24:−0.21998923
25:−1.0224223 26:−0.27785692 27:0.887824 28:−0.88122153 29:2.4520988 30:−1.8591628
31:−0.2047378 32:−0.43277052 33:1.3049064 34:0.28490406 35:0.58858889 36:0.31118494
37:−0.75974351 38:0.30014536 39:0.16725326 40:0.28239837 41:0.85730082 42:0.18312453
43:0.73757261 44:0.23835303 #
−0.00094526216742025517 1:−8.2843933 2:3.6966038 3:−0.46435714 4:1.5304902 5:1.1075522
6:1.9134642 7:−0.79442489 8:0.52520049 9:0.83645153 10:−2.6971796 11:−0.88591361
12:1.3652115 13:0.92740053 14:1.9873277 15:−3.1379786 16:1.0197264 17:−2.7746265
18:0.68137848 19:−1.3835444 20:1.2694755 21:0.34423488 22:−1.891607 23:0.15474756
24:1.2157984 25:−0.04881968 26:−0.55643517 27:−1.6764784 28:2.4692996 29:0.067258775
30:−1.8768005 31:−0.14590223 32:−0.94142735 33:−0.80213898 34:−0.50326455 35:−1.2780002
36:0.13170069 37:−0.80249226 38:−0.58796179 39:−1.7767088 40:−0.65758491 41:1.6625999
42:−1.8933594 43:−1.8352563 44:0.28400037 #
−0.00070168824838637636 1:−6.122613 2:−0.55014724 3:0.29037741 4:−7.820363 5:−0.075020343
6:3.8448997 7:0.31839412 8:2.5894465 9:0.42450967 10:−2.6556973 11:−1.0042195 12:−3.5184166
13:−1.6911469 14:−1.1769295 15:0.024770757 16:−1.4050843 17:0.087066472 18:−0.95585454
19:−0.48107174 20:1.9910818 21:1.4393178 22:−0.28986773 23:2.0448291 24:−0.93548518
25:0.62121999 26:−3.1084788 27:−0.12058441 28:1.0080323 29:1.2899083 30:−0.75200337
31:−1.2419468 32:−1.4561284 33:−0.41465601 34:1.9404265 35:−1.2137595 36:−1.0310935
37:1.5804566 38:−1.6227396 39:−1.3698378 40:−3.1060567 41:−0.70550668 42:1.8586001
43:0.36955735 44:1.0749351 #
−0.00028453538790302203 1:0.6300419 2:4.7734146 3:−1.2489752 4:−8.6097279 5:2.008311
6:−6.2184939 7:−6.5808897 8:2.7158918 9:−2.4301894 10:−1.2175536 11:−2.2188854 12:4.2264996
13:0.93197346 14:6.044878 15:−1.9431387 16:−0.16680923 17:−1.8877845 18:0.58306974
19:−3.674577 20:1.0183392 21:−0.6716578 22:0.09610986 23:−2.1211574 24:0.99420094
25:−0.4703958 26:0.74925768 27:1.062624 28:−1.8707883 29:−0.82231814 30:−0.45962375
31:2.0175238 32:−0.81920165 33:−1.7209393 34:−1.5601432 35:0.26762301 36:−0.3487784
37:−0.77708137 38:−0.33194357 39:1.8212304 40:−0.35933191 41:−1.2618924 42:−0.8380754
43:1.0074747 44:0.51855934 #
−5.9459020420257161e−005 1:−34.113136 2:9.1733046 3:5.3838677 4:7.6956291 5:13.459892
6:−3.5612979 7:−7.1091042 8:5.5747619 9:−2.8808331 10:1.8228761 11:−0.80162328 12:0.45366946
13:0.35113454 14:−5.9756327 15:1.5504394 16:1.9655282 17:2.4146829 18:−2.2898633
19:−0.88621074 20:−1.1601353 21:−0.79647011 22:1.5297979 23:−1.7144865 24:0.64629495
25:1.1985551 26:0.55810708 27:−0.25598845 28:−0.38665497 29:−0.00039836648 30:−1.1873535
31:−0.085017577 32:−0.069415957 33:−0.41498676 34:0.24881725 35:0.18458879 36:0.20159762
37:0.18202665 38:−0.081453502 39:0.168487 40:−0.027624954 41:0.18284768 42:0.38703957
43:0.40067115 44:0.0030078939 #
−3.8922016909529161e−006 1:−2.988956 2:−14.541928 3:−24.152397 4:7.8578658 5:0.62039638
6:−1.4124461 7:−3.5245433 8:0.23765643 9:0.59025252 10:0.51212358 11:−1.3314158 12:−2.0315864
13:−0.2914176 14:0.37882963 15:0.082344197 16:−0.57432884 17:0.080625705 18:−0.14113382
19:−0.13893105 20:−0.28207991 21:0.12245945 22:−0.23306957 23:−0.074358061 24:0.075329393
25:0.095754124 26:0.17469533 27:−0.15946545 28:0.030569298 29:−0.041504841 30:0.1790569
31:0.18031198 32:−0.18188456 33:−0.14256233 34:−0.087481722 35:0.093072012
36:−0.0096975714 37:0.055885319 38:−0.26989311 39:0.060945775 40:0.025113981 41:−0.020692149
42:−0.027143152 43:0.010555366 44:0.17869918 #

APPENDIX C7

SVM Model Weights
(10; Normal/Diseased)

SVM-light Version V6.01
0 # kernel type
3 # kernel parameter -d
1 # kernel parameter -g
1 # kernel parameter -s APPENDIX C7-continued SVM Model Weights
(10; Normal/Diseased)

1 # kernel parameter -r
empty# kernel parameter -u
10 # highest feature index
138 # number of training documents
71 # number of support vectors plus 1
1.0883106 # threshold b, each following line is a SV (starting with alpha*y)
−0.0058224718477910675 1:−4.8213444 2:1.5760788 3:−0.57018983 4:4.005219 5:−2.8392484
6:1.7106702 7:9.8552361 8:2.2270277 9:−1.4904127 10:−7.1802697 #
−0.0058224718477910675 1:9.4857044 2:0.34912884 3:0.49210653 4:0.40934604 5:0.36403582
6:−2.1638162 7:4.2396574 8:0.71271384 9:−2.6265984 10:−0.67596924 #
−0.0030633937881404216 1:−3.3906956 2:16.927059 3:4.5530434 4:−1.3870215 5:1.6440891
6:−2.1803629 7:5.6633768 8:5.4171095 9:−0.78184611 10:4.4131618 #
−0.0058224718477910675 1:−5.5317745 2:−3.2781949 3:1.4514818 4:4.4336934 5:0.22635397
6:2.3636923 7:2.9700732 8:−0.24828267 9:−2.3608406 10:−1.9967079 #
−0.0058224718477910675 1:−12.11614 2:7.1385088 3:3.1919744 4:−0.5384708 5:−2.1869912
6:−3.1748075 7:−0.84486699 8:−0.32319507 9:2.3280804 10:0.71962136 #
−0.0043431632527545375 1:−7.7268705 2:−24.503897 3:3.4747212 4:−17.230532 5:−1.5916975
6:4.966423 7:−3.4034503 8:18.305843 9:12.179471 10:5.2980161 #
0.0058224718477910675 1:3.6875272 2:3.0250661 3:0.29052538 4:1.6621389 5:−1.077208
6:−1.4265242 7:5.6980257 8:2.4122481 9:−0.23186241 10:−3.5392511 #
0.0058224718477910675 1:4.4914255 2:−0.24480897 3:−2.2583835 4:0.88322991 5:−2.5046406
6:1.9969134 7:−0.0044047181 8:−0.26928857 9:−1.4914516 10:−1.5938169 #
0.0058224718477910675 1:3.5839531 2:−5.883049 3:−4.1707263 4:2.668844 5:−0.41040224
6:−0.95485866 7:−0.55179292 8:−1.9773617 9:−0.17881806 10:−1.001881 #
−0.0058224718477910675 1:16.392971 2:−4.7027459 3:−2.2550261 4:−0.21748754 5:−4.5716577
6:5.9160895 7:5.429513 8:2.0746083 9:−4.2725348 10:−4.7335415 #
0.0058224718477910675 1:−2.9766047 2:2.3910513 3:−0.0033213915 4:−0.17175539 5:−6.0470386
6:−1.3497559 7:−0.36723912 8:0.20253371 9:−0.012134829 10:1.6765274 #
0.0058224718477910675 1:−12.323371 2:−2.5419991 3:−1.609848 4:4.4974389 5:−3.7014587
6:−4.0358763 7:2.6280291 8:4.9896169 9:2.5341156 10:−1.446465 #
0.0058224718477910675 1:4.0929852 2:1.4835061 3:6.1188703 4:−10.270689 5:2.5785246
6:−3.0121825 7:5.101213 8:1.347518 9:−3.5204203 10:2.21015 #
−0.0058224718477910675 1:10.097442 2:−1.8614138 3:1.4156544 4:1.4052474 5:0.31974572
6:−5.6366968 7:−2.7028873 8:−2.4760547 9:2.5067186 10:2.0757139 #
0.0017544354748585118 1:−1.3733028 2:0.68064439 3:7.460279 4:5.9247279 5:−1.6578373
6:0.2775822 7:−24.075966 8:11.05617 9:−14.703788 10:−13.254814 #
−0.0058224718477910675 1:−5.7653995 2:−7.7065129 3:−1.7101065 4:2.9592018 5:0.76229161
6:−3.6607392 7:−1.3269446 8:0.56657773 9:1.139729 10:0.17632462 #
−0.0058224718477910675 1:−4.1156435 2:−0.34006771 3:8.4351921 4:−14.735023 5:2.3358378
6:−6.4112816 7:1.5974257 8:−3.843544 9:−9.0954008 10:4.760253 #
0.0058224718477910675 1:−7.509798 2:−4.5393901 3:−2.8062258 4:3.4199057 5:3.2766123
6:−6.2061114 7:−3.7431328 8:0.69338125 9:1.6215347 10:1.2656826 #
−0.0058224718477910675 1:2.8188708 2:−6.6911874 3:−1.9094163 4:3.7313151 5:2.2988858
6:−4.5035233 7:3.6753259 8:1.7877527 9:−0.5697372 10:−3.8303387 #
0.0058224718477910675 1:8.9275894 2:−15.020937 3:10.042231 4:−1.3609071 5:6.4316907
6:4.8265376 7:5.9696269 8:2.2046807 9:−11.892014 10:6.7493229 #
0.0058224718477910675 1:7.5575404 2:1.2708558 3:−2.5564513 4:2.3454616 5:−4.0419817
6:3.6907179 7:3.6983776 8:0.66216749 9:1.8481812 10:−4.4674816 #
0.0058224718477910675 1:4.8310957 2:−0.51966381 3:3.2191603 4:−5.9580889 5:−3.9725423
6:0.56513089 7:5.1268225 8:−0.1668672 9:0.36320001 10:−3.7878082 #
−0.0058224718477910675 1:−5.7919517 2:−2.1810565 3:0.89991498 4:4.4267159 5:0.42934251
6:0.0051537198 7:2.4697821 8:−0.77805513 9:0.41163149 10:−2.9729836 #
−0.0058224718477910675 1:1.8426523 2:−1.0022681 3:−1.8142201 4:4.7052956 5:−3.3947911
6:−3.9205186 7:2.2534845 8:−0.65490913 9:0.93505371 10:−1.3716303 #
0.0058224718477910675 1:−0.40706003 2:−7.1397123 3:2.6859665 4:−7.0096903 5:3.0317152
6:−4.3316078 7:1.4683849 8:−2.7222147 9:−2.3974659 10:1.5284376 #
0.0058224718477910675 1:1.4998577 2:−0.833125 3:0.15874894 4:−0.16305982 5:−6.3999782
6:−3.0114808 7:−2.3441393 8:−0.62991965 9:0.48263061 10:1.2088264 #
0.0058224718477910675 1:−1.2529821 2:1.393857 3:−0.40100932 4:0.80536771 5:−1.3698692
6:−4.2985444 7:−1.2300457 8:−1.6063071 9:1.3245063 10:2.534188 #
0.0058224718477910675 1:9.6229353 2:−11.464231 3:4.1598067 4:−3.3941331 5:4.1509666
6:1.546693 7:4.3594489 8:2.2675736 9:−7.5672388 10:3.2643189 #
−0.0058224718477910675 1:−3.074358 2:1.3200911 3:−0.80671835 4:2.0445714 5:−2.9063234
6:−4.6124997 7:2.0404482 8:0.62350243 9:0.60801113 10:−3.675019 #
−0.0058224718477910675 1:7.2203302 2:−4.6925292 3:−0.71862835 4:2.4329977 5:0.17405996
6:−2.3858955 7:−3.6205564 8:−1.2306844 9:0.62873197 10:2.9880207 #
−0.0058224718477910675 1:−1.3632743 2:−1.9445323 3:0.65233999 4:−0.58333957 5:−2.1690819
6:−1.557755 7:−3.9043965 8:−0.30472508 9:0.2361026 10:0.85410559 #
0.0058224718477910675 1:10.933654 2:6.4248862 3:3.2384374 4:0.14409828 5:2.0443769
6:−0.96650457 7:−2.7591114 8:3.8425102 9:1.286938 10:−2.7674775 #
0.0058224718477910675 1:5.4943523 2:3.8203344 3:3.2906234 4:0.16825591 5:−4.9035769
6:−0.52033991 7:3.1050794 8:2.5860252 9:2.6400912 10:−3.4708204 #
0.0058224718477910675 1:−4.2092881 2:−2.4297073 3:2.3812873 4:3.7497678 5:−3.525115
6:−4.9855132 7:6.1610827 81.7601898 9:−2.8208137 10:−3.3654191 #
−0.0058224718477910675 1:5.5017767 2:0.76866108 3:3.5021136 4:−3.4441924 5:−1.7227199
6:−2.3480663 7:5.2186608 8:2.0708718 9:1.1557996 10:−2.8974543 #
0.0023869171181780369 1:−8.7888012 2:−5.0174055 3:15.464613 4:12.69648 5:0.48444548

APPENDIX C7-continued

| SVM Model Weights (10; Normal/Diseased) |
| --- |
| 6:4.1684113 7:−0.74741292 8:−3.0366001 9:3.0165656 10:0.36663359 # |
| 0.0058224718477910675 1:−5.0323195 2:−2.8937032 3:0.9245494 4:4.0953684 5:−0.48259613 |
| 6:−10.957071 7:−1.3562635 8:1.5278653 9:1.908803 10:1.5891732 # |
| 0.0058224718477910675 1:0.59667957 2:−11.827269 3:0.20600793 4:−4.1515388 5:5.5969896 |
| 6:−3.8011801 7:−0.29551542 8:−4.6395001 9:−3.4394548 10:1.4789293 # |
| −0.0058224718477910675 1:9.0571957 2:−1.9548935 3:−0.75283456 4:1.8611076 5:2.1321533 |
| 6:−1.0634044 7:1.7300889 8:−1.4033413 9:−1.565226 10:0.95930284 # |
| 0.0058224718477910675 1:−0.17285712 2:5.3579178 3:−0.74000329 4:0.99322218 5:−6.1377206 |
| 6:0.59887767 7:0.042126093 8:−0.2397196 9:1.3158681 10:1.9585021 # |
| −0.0058224718477910675 1:2.0158556 2:5.64184 3:1.2100551 4:0.38732079 5:−0.91638023 |
| 6:0.86250663 7:−5.9655256 8:1.9825593 9:−3.4821234 10:0.86993414 # |
| −0.0058224718477910675 1:8.4564133 2:−3.6954048 3:−0.36950901 4:2.0615106 5:0.32085344 |
| 6:−2.5327203 7:−0.28457209 8:−1.186967 9:−1.2540523 10:2.2149053 # |
| −0.0058224718477910675 1:−0.60706848 2:−0.56179869 3:−2.8295784 4:2.1079314 5:−2.16576 |
| 6:−1.5902358 7:−3.8995321 8:−1.391099 9:1.3323318 10:2.3022547 # |
| 0.0058224718477910675 1:3.9010017 2:−5.5965748 3:−3.4673359 4:3.8046615 5:−0.80037314 |
| 6:−2.4926233 7:−0.65297276 8:−1.2992364 9:0.5986374 10:−0.76736987 # |
| −0.0058224718477910675 1:11.063172 2:−4.1735458 3:−2.1705191 4:3.1756155 5:−2.6342511 |
| 6:0.35717416 7:−2.6251674 8:−2.3413982 9:1.3099627 10:2.2732904 # |
| 0.0058224718477910675 1:−1.513376 2:−1.8505038 3:−3.1226563 4:3.4844956 5:−1.8776969 |
| 6:−1.47199 7:0.80681765 8:−0.75451481 9:−0.47854143 10:0.9895125 # |
| 0.0058224718477910675 1:5.3318014 2:2.8600442 3:−0.63892436 4:2.671339 5:5.2220407 |
| 6:0.021795753 7:−0.1497921 8:−0.35194841 9:2.4227602 10:0.78205884 # |
| −0.0036313248346271365 1:−9.2383366 2:2.0031359 3:−2.7472436 4:−0.29943109 5:−5.6568513 |
| 6:3.7322798 7:5.1578135 8:2.1428649 9:−2.7855699 10:−0.25731304 # |
| 0.0058224718477910675 1:3.194849 2:0.43900785 3:−1.9627602 4:1.2485242 5:−5.9852576 |
| 6:0.33253258 7:−1.8617131 8:−0.86069912 9:0.550134 10:1.0473752 # |
| −0.0058224718477910675 1:5.654953 2:−0.53522277 3:−1.9235955 4:2.7848213 5:1.0320071 |
| 6:−3.5737214 7:1.3059427 8:−2.7621024 9:0.64108217 10:−0.40291178 # |
| 0.0058224718477910675 1:−2.6544154 2:−1.6780306 3:0.060192857 4:4.1504841 5:0.24912068 |
| 6:−6.624095 7:0.57551324 8:−0.40938711 9:0.95585006 10:−1.6248276 # |
| 0.0058224718477910675 1:0.23982425 2:−2.2714684 3:2.7530899 4:−0.43534729 5:−2.1343725 |
| 6:−6.5755577 7:−0.23095936 8:2.4990304 9:0.5341723 10:0.474659 # |
| 0.0058224718477910675 1:2.5546148 2:4.1075654 3:2.0542722 4:1.7574935 5:−6.4822512 |
| 6:−3.3165057 7:−1.2411754 8:−1.2139313 9:3.3224194 10:2.2444251 # |
| 0.0058224718477910675 1:0.59482116 2:0.49655741 3:−0.84351039 4:0.95068574 5:−4.0811591 |
| 6:−1.6533675 7:−4.1306829 8:−0.31580341 9:1.3122809 10:2.5053549 # |
| −0.0058224718477910675 1:−9.4932261 2:−2.4200175 3:−0.99547184 4:3.386457 5:−0.25609118 |
| 6:−2.623518 7:−2.4135804 8:−0.39986932 9:2.1378477 10:1.8484613 # |
| −0.0058224718477910675 1:10.264601 2:−0.059173197 3:1.2563672 4:0.93355006 5:0.10213261 |
| 6:−3.12937 7:0.1210808 8:−1.4454924 9:2.8236961 10:1.1237521 # |
| −0.0058224718477910675 1:−0.40237048 2:3.0508842 3:−0.87237811 4:−0.24187045 5:−8.52349 |
| 6:4.217833 7:1.0044558 8:−0.71493214 9:0.38238505 10:−0.80563587 # |
| 0.0058224718477910675 1:3.4503579 2:−4.2435541 3:−3.5084748 4:4.1104755 5:−2.2494571 |
| 6:−1.1301751 7:1.2851278 8:−1.3474931 9:0.074681044 10:−1.1245632 # |
| −0.0057869865337552553 1:8.3293247 2:−3.9943771 3:−1.2766048 4:1.7569972 5:2.6435943 |
| 6:−2.9492621 7:−2.3212342 8:−2.6703773 9:1.6562256 10:0.99037993 # |
| −0.0058224718477910675 1:1.5939288 2:−0.68451202 3:−1.9828767 4:2.687711 5:−2.3559065 |
| 6:−0.40762001 7:−0.38349798 8:1.4480487 9:0.19084418 10:0.57923073 # |
| −0.0058224718477910675 1:−6.5375977 2:2.1123948 3:1.1355326 4:−2.3440728 5:−0.40250897 |
| 6:−5.1222434 7:2.0590734 8:0.87406713 9:−0.42407495 10:1.3824636 # |
| 0.0058224718477910675 1:3.5110908 2:5.6174746 3:2.5606756 4:2.5834703 5:−7.6688213 |
| 6:−1.8434024 7:0.36071539 8:−0.45174024 9:2.6003997 10:0.5911482 # |
| −0.00064705185971957596 1:3.5329537 2:−10.95813 3:3.4194798 4:−7.8480668 5:3.7418206 |
| 6:−3.0329297 7:−2.0779335 8:−0.86376679 9:−0.23510407 10:2.2805333 # |
| −0.0058224718477910675 1:−7.5607929 2:4.9967093 3:−1.264623 4:1.5839788 5:−3.1135581 |
| 6:−1.7120829 7:4.2883148 81110269687 9:−1.0577402 10:−0.98678935 # |
| −0.0058224718477910675 1:−1.2745243 2:1.3725504 3:−0.40984562 4:−2.6292028 5:−5.3895054 |
| 6:5.9739404 7:−4.5711613 8:2.2052009 9:−5.2465138 10:−0.67647785 # |
| 0.0058224718477910675 1:3.9855435 2:−2.1551187 3:0.63115042 4:1.5583338 5:−3.9991305 |
| 6:−3.0780492 7:2.0848374 8:2.7543757 9:−2.3052657 10:1.416037 # |
| −0.0058224718477910675 1:12.198691 2:−4.6254134 3:0.4309229 4:−0.0045036334 5:1.6533217 |
| 6:−1.6674639 7:−0.58168441 8:−2.0143023 9:−0.36359423 10:−1.1387699 # |
| 0.0058224718477910675 1:2.7049806 2:1.0712382 3:−0.60530049 4:3.1470454 5:−6.2567849 |
| 6:−1.7234993 7:−2.0789998 8:−0.55858582 9:1.1510547 10:3.0091002 # |
| 0.0016856239803782424 1:2.6485436 2:−0.39832091 3:3.7447002 4:−2.1478522 5:−5.6797609 |
| 6:−5.3180451 7:0.0458709 8:−0.33030915 9:1.79348 10:−1.4856584 # |
| −0.0058224718477910675 1:8.7892799 2:−0.5433358 3:0.67584097 4:1.3441595 5:2.1046317 |
| 6:−2.3882663 7:0.25097188 8:−1.9213748 9:1.8338643 10:−0.65807337 # |

APPENDIX C8

| SVM Model Weights (29; Benign/Malignant) |
| --- |

SVM-light Version V6.01
0 # kernel type
3 # kernel parameter -d
1 # kernel parameter -g
1 # kernel parameter -s
1 # kernel parameter -r
empty# kernel parameter -u
29 # highest feature index
99 # number of training documents
56 # number of support vectors plus 1
0.41759311 # threshold b, each following line is a SV (starting with alpha*y)
−0.0038912456187004405 1:−0.42324471 2:2.5828345 3:−1.8410451 4:−0.4363316 5:0.067014627 6:−1.8869078 7:2.7124326 8:3.5093668 9:−2.1161191 10:0.31742153 11:2.0527875 12:2.6345732 13:−0.53119665 14:−1.2637744 15:0.19591911 16:−2.386672 17:0.98163056 18:0.015205857 19:1.3719232 20:−3.8242466 21:0.63041341 22:2.2860601 23:−2.2027335 24:−1.1924071 25:0.088403225 26:−2.2897179 27:1.8068643 28:−0.78437859 29:−0.35509837 #
0.0020402683483578803 1:16.053837 2:−15.819319 3:−1.6210849 4:3.6457462 5:4.4152589 6:10.210145 7:1.1093941 8:−8.4489651 9:−7.8424716 10:1.2531379 11:−5.7854691 12:0.85058212 13:11.505015 14:0.58409226 15:5.614861 16:−5.0463986 17:−2.4444163 18:−0.25845858 19:1.0797292 20:−3.8040044 21:1.912954 22:0.23680127 23:−0.15167442 24:−1.3719921 25:2.5946932 26:0.17403919 27:−1.2898791 28:0.059081983 29:0.14672025 #
−0.0020713424289802566 1:5.8117294 2:−1.9790573 3:3.3024013 4:1.4090675 5:4.0260754 6:1.7043306 7:−1.2717206 8:−5.0069366 9:−0.5155825 10:4.2741876 11:−0.63364661 12:3.6082911 13:−1.0221395 14:4.3295956 15:−3.6911883 16:3.8338921 17:1.1320567 18:0.076046549 19:0.73055929 20:1.5319011 21:2.0646148 22:2.5041037 23:−1.2301037 24:1.9691244 25:−1.8752548 26:−1.3004006 27:−1.2616713 28:1.7858572 29:−0.20650764 #
0.0038912456187004405 1:−0.23311329 2:−1.5340611 3:−0.56233943 4:−7.4785199 5:−3.6518826 6:−4.7517338 7:−0.41352883 8:−1.1385972 9:−2.3377373 10:0.89005411 11:−3.0769937 12:0.91200078 13:−1.0174296 14:−0.29183522 15:5.4507852 16:1.9547648 17:2.4246554 18:−2.5977473 19:0.059181549 20:0.9693011 21:−1.3478724 22:1.2955381 23:0.29502755 24:−0.31393111 25:−0.025742445 26:−1.3289164 27:−1.1254236 28:0.11153328 29:1.9973383 #
0.0038912456187004405 1:5.7773232 2:−0.2485496 3:−4.9756732 4:2.3672733 5:−1.7608249 6:−4.6183424 7:−6.1881247 8:−1.4636059 9:0.42568609 10:0.91490215 11:2.9737656 12:1.4572622 13:2.3844304 14:3.479558 15:−2.172904 16:1.3687432 17:−2.2401547 18:2.038378 19:−1.0956939 20:2.6179361 21:4.8499289 22:−1.0542914 23:−1.1590868 24:2.5353518 25:0.69207913 26:−5.589396 27:1.1018655 28:4.4162931 29:2.5424984 #
0.0038912456187004405 1:2.3662179 2:1.6748204 3:3.8486438 4:1.4897406 5:−0.9291935 6:−7.1160836 7:−1.9521724 8:1.1360776 9:−1.8011853 10:2.2141206 11:1.7985709 12:−2.1508341 13:1.6635997 14:0.10243254 15:−0.36165324 16:1.0803972 17:0.49766871 18:0.0012823264 19:−0.98907411 20:−2.9658399 21:0.10815067 22:1.4386787 23:−1.396909 24:−0.14514606 25:−0.095915295 26:−0.20809935 27:−1.45952 28:−0.80965692 29:−0.10805699 #
0.0038912456187004405 1:−5.2307115 2:5.5413795 3:4.0636749 4:−6.2058477 5:4.1717806 6:1.6895379 7:0.53004158 8:−4.6441884 9:3.1082587 10:0.048623063 11:−1.3503591 12:0.17829828 13:−0.59768867 14:0.87042594 15:−0.4560613 16:−0.69823253 17:−0.94882631 18:−1.0522534 19:−2.2051711 20:−2.6186538 21:1.3570184 22:−3.7802284 23:1.1904382 24:2.3432648 25:−1.1689653 26:2.4562342 27:0.067852028 28:−2.5447171 29:2.2677996 #
0.0025697199378155304 1:−3.8347991 2:0.4250325 3:−15.678971 4:7.1875505 5:0.54047203 6:−4.0046563 7:1.9759779 8:1.9077226 9:10.761656 10:−8.7568007 11:−1.4441179 12:−0.30809698 13:−1.9578561 14:−4.2252517 15:8.2054901 16:−1.636007 17:2.6754603 18:7.3106451 19:−4.4067588 20:−2.1794596 21:3.0483193 22:−0.39562172 23:−1.4235375 24:1.0369247 25:−0.085445531 26:0.30943248 27:−3.5057745 28:1.2857898 29:0.37323707 #
−0.0038912456187004405 1:7.9274554 2:4.6073709 3:1.4603447 4:2.0189972 5:0.78566617 6:−1.9227256 7:2.3366702 8:3.8609731 9:−1.7538786 10:−1.9488626 11:1.0148774 12:1.0113562 13:0.048932023 14:0.18989503 15:−2.6325822 16:−1.2078793 17:−0.14492357 18:2.2336729 19:1.5534426 20:0.35241047 21:0.80466956 22:1.8033856 23:−1.1963571 24:0.040374711 25:0.84861618 26:1.267494 27:−0.13946263 28:−1.7854359 29:−0.44070604 #
−0.0038912456187004405 1:3.1450987 2:3.0755467 3:3.8123691 4:−5.2419996 5:3.5220785 6:2.7474384 7:3.2287869 8:−0.89663881 9:1.4479074 10:0.22962917 11:−0.68433446 12:0.67356664 13:−2.3352745 14:0.13635983 15:−1.3551366 16:−0.17511296 17:−0.53919446 18:0.34350392 19:−1.4785919 20:0.38314915 21:1.0084164 22:−0.74683142 23:−1.01981 24:0.92450368 25:0.048945725 26:2.4303942 27:1.9733022 28:−1.084133 29:2.4037261 #
−0.0038912456187004405 1:8.918601 2:−2.3055892 3:3.1710715 4:−0.15590623 5:4.4929414 6:8.9671669 7:3.5218017 8:−0.39461762 9:2.7775333 10:1.1787916 11:0.15996362 12:2.4074681 13:−3.6746743 14:0.4590081 15:−1.2401536 16:−0.21795638 17:−2.150651 18:1.5083847 19:−2.3201568 20:−1.4036152 21:1.2891895 22:1.8004652 23:−2.8867595 24:−0.48214114 25:−0.6927855 26:1.416193 27:0.6444248 28:−1.7029501 29:0.43822736 #
−0.0038912456187004405 1:1.6040151 2:0.24394807 3:−0.09684144 4:−2.4873862 5:1.2782253 6:−3.957773 7:1.591818 8:5.2486348 9:−3.780654 10:0.71394485 11:0.55227733 12:2.4138548 13:−0.35664403 14:0.24096936 15:0.61735266 16:−1.0579739 17:−0.3856262 18:0.43396828 19:0.52961248 20:−0.58919561 21:0.35186648 22:−0.27301615 23:−0.5683229 24:−0.66487145 25:−0.83458596 26:−1.3270503 27:1.6758934 28:−0.087032422 29:0.037628613 #
0.0029153664726271483 1:−0.27885634 2:9.8825912 3:5.0959301 4:11.570415 5:−1.236788 6:1.985296 7:5.2343593 8:0.62978274 9:2.3628919 10:−4.0060329 11:−1.5498919 12:−5.6165047 13:1.9572977 14:1.525573 15:−1.4694535 16:−0.72089523 17:6.3752151 18:−3.8398392 19:−0.22521774 20:2.0210238 21:−2.0194118 22:−0.11568941 23:−2.104739 24:1.9838831 25:3.0514641 26:0.59763795 27:1.0259111 28:0.36511812 29:−1.4264234 #
0.0017872161318243855 1:0.43924162 2:11.232109 3:−3.9407368 4:2.2011461 5:−11.28683

APPENDIX C8-continued

| SVM Model Weights (29; Benign/Malignant) |
|---|
| 6:11.626836 7:−2.2610507 8:1.9518424 9:−9.4666557 10:−3.7131739 11:10.517995 12:−6.7265964 13:−4.0587149 14:6.8698277 15:6.0822682 16:−1.0870117 17:1.8049608 18:−3.1073513 19:−2.3271327 20:1.4725494 21:3.9342456 22:1.8926948 23:3.0023232 24:0.81837815 25:−0.33446386 26:0.58317035 27:−0.11714862 28:−0.81818438 29:−0.47216067 # |
| 0.0038912456187004405 1:4.2058864 2:−10.273238 3:0.86963367 4:0.76485717 5:0.58796382 6:6.4885211 7:−0.5382148 8:1.6879342 9:0.99313658 10:1.3948026 11:−0.040827319 12:−1.919044 13:−2.0231805 14:1.3912067 15:−0.651649 16:3.206111 17:1.5296158 18:1.1393459 19:−0.41099066 20:−0.96875608 21:0.36818328 22:−0.98741603 23:1.1284338 24:−3.8232245 25:0.81427598 26:−0.40313891 27:−1.2148914 28:0.74097633 29:0.53082883 # |
| 0.0038912456187004405 1:−4.0771055 2:−1.1504505 3:2.7464559 4:−3.183337 5:2.1268644 6:−3.9230978 7:0.34163719 8:2.0293679 9:−4.1811166 10:1.3721042 11:0.75773573 12:−2.5267835 13:0.18023184 14:1.253926 15:1.903635 16:4.277389 17:−1.0687795 18:2.2155018 19:−1.165033 20:0.49952036 21:−0.53572905 22:−2.7601488 23:0.46436167 24:−1.0921776 25:0.40821484 26:−1.8236394 27:−0.6932615 28:−0.47530422 29:−1.0037123 # |
| 0.00061202670939240875 1:−2.6901774 2:0.12484454 3:−5.7668495 4:3.0192795 5:3.5229359 6:1.7700055 7:2.5609665 8:0.29128727 9:7.6276684 10:−8.8952122 11:−0.96227884 12:−1.0497365 13:−1.2142708 14:4.7062192 15:3.6511281 16:8.7197504 17:−5.4372635 18:−4.8534231 19:8.6003857 20:−2.3985815 21:3.356118 22:−0.72012883 23:−2.1830902 24:−0.51483166 25:0.088666141 26:−0.73958147 27:−0.082041442 28:−1.527185 29:−1.286461 # |
| −0.0017436815099869493 1:−3.8587921 2:−16.208611 3:−2.6007581 4:2.99523 28 5:−2.9244998 6:−2.1342196 7:−8.6919346 8:2.102823 9:−0.65605307 10:−3.5787513 11:0.57963091 12:−3.8771913 13:1.4609568 14:1.0911566 15:−2.6927843 16:−0.73983127 17:−2.9269328 18:−3.2514834 19:−1.6491545 20:−2.8616376 21:−2.9949863 22:0.38679239 23:−0.50630879 24:0.66747051 25:−0.56378025 26:2.5836411 27:−0.59832889 28:0.37365031 29:2.3311179 # |
| −0.0021063297906959884 1:−5.7875681 2:−1.0084696 3:−2.5154941 4:3.718677 5:1.4831289 6:−4.6980391 7:−4.2098918 8:0.72386932 9:−0.43842459 10:−3.7361112 11:1.2272559 12:1.3518623 13:2.2724423 14:−4.0965257 15:−0.16307685 16:0.54426932 17:2.674973 18:−4.7668042 19:−2.5615635 20:2.6017296 21:2.3070562 22:−0.32244205 23:−1.0658669 24:−5.2624288 25:1.8111422 26:−0.12618792 27:1.6774101 28:2.1192849 29:1.4636447 # |
| −0.0005094806136037083 1:−7.7966084 2:1.8707227 3:−23.323887 4:1.0747559 5:1.0184501 6:−3.600925 7:9.3491745 8:−7.7337961 9:−1.2228185 10:7.7243834 11:2.0076487 12:−4.368228 13:−1.5946441 14:−0.2912291 15:−2.0482881 16:−0.38283157 17:−1.6580502 18:−1.0132759 19:−0.17344542 20:0.65646726 21:−0.49175465 22:0.29616475 23:−0.65766221 24:−0.40362445 25:0.31434533 26:0.98643875 27:0.016180724 28:0.12472247 29:−0.22155482 # |
| 0.0038912456187004405 1:8.938942 2:3.6820235 3:1.8444127 4:3.1469421 5:−0.85917765 6:−3.1263924 7:1.5923287 8:2.7571449 9:1.3356986 10:−1.0054343 11:−0.72609353 12:−0.88047606 13:−0.052594084 14:1.6568137 15:−0.2300657 16:−3.0733943 17:−1.024448 18:−0.33218354 19:0.51852953 20:1.423895 21:−1.7680084 22:1.262127 23:−0.50992119 24:1.1018715 25:0.25038528 26:1.5296953 27:0.27678546 28:1.4986688 29:0.17097917 # |
| 0.0030592818752240335 1:12.400963 2:4.2546644 3:−0.41324967 4:3.0709786 5:−0.27842081 6:−1.2178549 7:2.344552 8:−0.065143779 9:1.4606165 10:1.0544931 11:−2.142359 12:2.1907766 13:−1.5534158 14:−0.69449091 15:0.29213595 16:−3.1575935 17:1.0698617 18:−2.5730839 19:0.0092338799 20:−2.99612 21:−0.1943074 22:−0.86630803 23:1.6802975 24:−1.0868572 25:−1.5044321 26:−1.582459 27:1.117466 28:−0.57524675 29:0.018987674 # |
| 0.00026578971968965401 1:9.8041286 2:15.643085 3:−14.213445 4:−5.6504297 5:−2.8406351 6:4.8410215 7:−6.6080933 8:−7.4779692 9:−0.5772323 10:−6.2781529 11:8.2602367 12:11.970333 13:6.336812 14:1.1768038 15:−1.7457997 16:1.5841151 17:1.5440294 18:−0.17547397 19:−0.62377983 20:0.05088732 21:−5.221839 22:−2.9309611 23:−0.88320798 24:−1.282207 25:−0.28119931 26:2.1707978 27:−0.44439083 28:0.69384325 29:−0.84158903 # |
| 0.0038912456187004405 1:11.932061 2:−0.54239619 3:4.2213945 4:−5.9421682 5:−2.619386 6:2.3564994 7:−2.7465849 8:−3.8928757 9:−4.162075 10:−1.7486995 11:0.47773656 12:−4.1929479 13:−2.0677514 14:−6.5466743 15:0.092173383 16:0.91300637 17:−1.0412949 18:3.4058571 19:3.6996002 20:3.7471523 21:−0.1068441 22:1.0975643 23:−1.3388216 24:1.3413877 25:3.6972344 26:1.4300827 27:−0.18405136 28:0.59656787 29:0.032527361 # |
| −0.0038912456187004405 1:9.2099752 2:0.10233181 3:1.9269702 4:−2.1939819 5:−1.9438351 6:3.0239697 7:−5.1489539 8:−5.0794964 9:−1.1390828 10:0.33780786 11:1.8522336 12:−7.0093985 13:−2.1220815 14:−7.3823423 15:1.5933274 16:3.5308435 17:2.6375818 18:2.7540584 19:−0.99151331 20:0.0083616357 21:0.54905522 22:0.68470973 23:−1.4407222 24:−1.9258854 25:−0.28219196 26:−0.25906509 27:−0.60497737 28:−1.8318855 29:−2.0681658 # |
| −0.0038912456187004405 1:3.3829088 2:2.943239 3:3.1921368 4:−7.1808729 5:−0.58675814 6:0.78415442 7:2.0849354 8:−2.3231814 9:−1.2042598 10:−0.67835438 11:−3.815778 12:−0.030315256 13:−1.9011153 14:0.15897124 15:−0.94414741 16:1.256176 17:1.2059518 18:−2.8228135 19:−0.78729898 20:−0.21089606 21:1.2398977 22:0.40475592 23:−2.1799212 24:−1.4266895 25:0.61812282 26:0.20725577 27:−2.2211232 28:1.0998532 29:1.8443335 # |
| −0.0038912456187004405 1:4.8919382 2:6.5307918 3:4.6522961 4:0.50912267 5:1.0186707 6:−1.6481709 7:−1.5135888 8:−1.650799 9:2.0391626 10:3.3697751 11:0.28303525 12:0.80901867 13:−0.7322185 14:2.403 5478 15:−0.92959404 16:−0.11080018 17:1.1656927 18:−0.061241843 19:0.093886204 20:0.41603193 21:1.5590807 22:−0.079786256 23:−1.3937597 24:−0.93761557 25:−1.2395495 26:0.47965881 27:−1.8439426 28:−1.0782979 29:2.3248599 # |
| 0.0038912456187004405 1:1.9507116 2:−11.019697 3:−2.6828804 4:5.4480629 5:5.7107086 6:6.9693308 7:2.66974 8:3.2545464 9:−1.9070691 10:0.99127346 11:−2.2294374 12:2.7105196 13:−3.1338248 14:1.5385495 15:−0.67776555 16:1.5831238 17:−0.5545975 18:0.12189388 19:−3.4824948 20:0.54062164 21:−1.5836126 22:−2.3674173 23:−1.9569142 24:0.007869835 25:0.49454546 26:−2.1373594 27:1.9552969 28:1.1393875 29:−1.3862598 # |
| 0.0038912456187004405 1:−1.3436253 2:−0.93941635 3:0.34727129 4:−4.000988 5:3.6346951 6:−2.0202615 7:2.8455384 8:2.3817055 9:−1.1053888 10:−0.021449149 11:0.5917924 12:1.05388 13:−0.72289419 14:0.42895883 15:2.1116214 16:0.92751497 17:−1.8995572 18:1.0356827 |

APPENDIX C8-continued

| SVM Model Weights (29; Benign/Malignant) |
|---|
| 19:−0.83366108 20:−0.16999248 21:−0.48544282 22:−1.7330638 23:1.7139575 24:1.0412071 25:−0.094441161 26:0.47909549 27:2.0350492 28:−0.79608703 29:−0.017424189 # 0.0038912456187004405 1:3.9146221 2:−9.5838127 3:−2.1989262 4:2.483418 5:2.2109056 6:2.3148644 7:−1.6744893 8:2.0438197 9:−0.22050218 10:0.95947695 11:1.7617443 12:1.0714002 13:−2.0813811 14:0.52549028 15:0.8533324 16:2.6622386 17:−2.1034327 18:−0.13717787 19:−2.1242678 20:1.0191004 21:−1.0218762 22:−1.8217447 23:1.2176883 24:0.32349762 25:−1.7366513 26:0.13325104 27:1.2317364 28:−1.6418275 29:−1.1362265 # −0.0038912456187004405 1:5.8637757 2:−9.9825153 3:−1.3864986 4:3.7755594 5:1.9810551 6:5.9261589 7:2.0591137 8:1.4179028 9:−2.8670921 10:1.2827179 11:0.51069009 12:2.7566116 13:−1.0318092 14:5.8409891 15:2.453907 16:−1.4336371 17:2.6721907 18:2.6253684 19:−1.1450388 20:0.95642722 21:−0.68922752 22:−0.63180703 23:−1.2727717 24:2.6737196 25:2.5429664 26:0.12496121 27:0.70460039 28:0.61082274 29:−2.6253922 # −0.0019445007847796406 1:−1.4225143 2:−3.3811448 3:−1.3460624 4:−2.4572864 5:−1.2485046 6:1.5272132 7:3.8467693 8:3.6000576 9:−2.5641577 10:−0.67970216 11:−1.2237694 12:−0.66455346 13:−1.7749182 14:1.801129 15:−0.073441938 16:−1.0443138 17:2.9320962 18:−0.62133968 19:0.24629931 20:−2.5408921 21:−1.9696916 22:−0.15611142 23:−0.55407423 24:0.17331484 25:−2.6666267 26:0.11005254 27:−0.76523972 28:0.82345724 29:2.1196442 # 0.0038912456187004405 1:5.7209835 2:0.23666459 3:1.730386 4:0.35195339 5:0.080441706 6:0.4397411 7:0.79212171 8:−3.2328453 9:0.53677988 10:−1.278559 11:−1.9872284 12:−3.541455 13:1.268319 14:−0.80598712 15:−1.9951948 16:1.6678131 17:0.39204028 18:−0.14329085 19:0.0522938 20:−3.9440317 21:−0.70164174 22:0.37428939 23:1.37909 24:−0.080555849 25:−0.21866828 26:−0.26640299 27:−0.11733657 28:0.54316443 29:−0.98517901 # 0.0038912456187004405 1:12.88688 2:7.6728315 3:3.7184772 4:−4.2598038 5:−1.1576847 6:−0.6589455 7:−0.12417337 8:−3.7127607 9:1.2203434 10:1.8098245 11:0.71039736 12:2.0804777 13:−2.7874148 14:−3.1586065 15:1.3173382 16:0.94230872 17:−0.76273376 18:−1.9022322 19:−0.086186662 20:−2.3211615 21:0.149593 22:1.1707815 23:0.083588153 24:1.7598888 25:0.15474093 26:−0.142803 27:−0.67765546 28:−0.41080022 29:−0.41189691 # −0.0030400640321260092 1:−7.236392 2:−3.5836346 3:1.7660971 4:−0.32848185 5:−1.2832146 6:−6.0978584 7:−3.6553211 8:−0.17175604 9:−0.25727716 10:0.22893712 11:2.0433552 12:−2.5095832 13:2.2301786 14:0.89164317 15:0.035530206 16:0.43601635 17:−1.5672219 18:−2.1941028 19:−1.6846048 20:−1.9031192 21:−1.5150453 22:−0.067690462 23:−0.7034052 24:−0.92714 25:2.8568938 26:−0.54916203 27:−0.33980703 28:1.3728271 29:−1.5007032 # −0.0038912456187004405 1:16.208258 2:5.0280037 3:0.82172555 4:−6.9475951 5:−3.3456998 6:−1.9767576 7:−3.7032745 8:−3.4155843 9:7.0004339 10:4.3763795 11:−0.7983644 12:2.4872475 13:−3.7470655 14:−0.62817919 15:4.9190741 16:−4.2188792 17:−2.0490263 18:−2.7245042 19:−0.17719579 20:−0.11300744 21:1.0088226 22:−0.073986799 23:0.5722124 24:0.008042899 25:0.74790359 26:0.33785641 27:1.2871412 28:0.5370971 29:0.44420156 # −0.0038912456187004405 1:−1.3259747 2:−0.81137985 3:1.4334838 4:−1.7649548 5:3.6129992 6:0.29705635 7:1.2894326 8:−0.10095613 9:−2.3867192 10:1.7502738 11:−0.19358803 12:0.50865448 13:0.3514927 14:−0.64236754 15:4.1707873 16:4.8303452 17:3.4271297 18:1.7873092 19:−1.7034998 20:−0.70197618 21:−2.1089077 22:−0.48871359 23:−0.62036341 24:2.3210227 25:2.126719 26:1.1654752 27:2.4087574 28:1.4107223 29:2.3072691 # −0.0038912456187004405 1:0.25218788 2:0.81176651 3:4.3265495 4:0.80694395 5:1.2578313 6:−0.41075879 7:−0.52536166 8:−1.8982818 9:1.2403241 10:0.55058247 11:−0.13172349 12:−0.29310575 13:−0.85193628 14:0.98000151 15:0.51622123 16:1.1070833 17:−1.7187762 18:−1.4114212 19:−1.4101827 20:2.371562 21:−0.20655285 22:−0.77752417 23:−1.6776743 24:1.3278382 25:−0.65001339 26:1.1879882 27:−1.6550736 28:−0.69467938 29:1.6729231 # 0.0038912456187004405 1:2.3376174 2:1.3542268 3:2.4850945 4:−1.2638111 5:−0.78601927 6:−2.594995 7:−0.54343778 8:3.0801613 9:−1.54309 10:1.2380967 11:1.301192 12:−0.16419302 13:−1.2675476 14:2.4840486 15:−0.15256229 16:0.13161588 17:0.48776254 18:−0.36262459 19:0.68028796 20:−1.9740275 21:−0.34123287 22:−0.043554693 23:−2.6711347 24:−1.6657956 25:−0.39183104 26:−0.42118907 27:−1.2100161 28:−1.0413429 29:−1.3260686 # 0.0038912456187004405 1:−1.3158712 2:0.9707914 3:3.1719823 4:−4.840673 5:3.0936675 6:1.5288476 7:3.3780329 8:4.2238803 9:−0.16770123 10:−0.019811096 11:0.68480086 12:−0.034741119 13:−0.02114979 14:−1.2866874 15:0.79995006 16:1.5080215 17:−1.4229754 18:−0.75168186 19:−1.1788121 20:0.69550902 21:−1.0135601 22:−0.75650036 23:−0.5917927 24:−1.2025844 25:2.1475875 26:0.43937358 27:0.21717836 28:−1.3248004 29:0.59354568 # 0.0038912456187004405 1:4.8517151 2:−2.2635946 3:0.77981508 4:1.0349083 5:0.2407393 6:−0.36395466 7:0.59494889 8:−0.31111282 9:−0.45820686 10:−1.6839181 11:−1.5326648 12:−4.838304 13:2.289643 14:1.9145365 15:−2.4840858 16:2.4276547 17:1.505362 18:3.6388161 19:2.8526552 20:−0.63271797 21:−0.074653953 22:1.4910883 23:0.97199351 24:−0.64722019 25:−1.2348423 26:1.4096289 27:2.0301092 28:0.83028793 29:0.72350144 # −0.0027545455202329936 1:2.0883245 2:−6.4719901 3:−0.83055037 4:−4.0124822 5:−1.584533 6:3.4442372 7:5.0622163 8:9.4115982 9:4.5804567 10:1.9651678 11:4.8765759 12:−0.95423251 13:8.2563066 14:−3.4564598 15:−1.9124181 16:0.80265266 17:0.26535338 18:−1.6216221 19:1.5909601 20:3.5689068 21:0.34506276 22:−0.43104431 23:−1.4937686 24:−0.28332224 25:0.084367178 26:2.1458566 27:−2.0169153 28:0.59910655 29:−0.24338524 # −0.0020303933504211245 1:−9.9491262 2:−0.45659417 3:3.2891505 4:−0.11462954 5:1.8582008 6:−2.3300738 7:2.9500461 8:3.6515126 9:−3.6656382 10:−2.1517365 11:−0.87704921 1 12:0.15539017 13:−0.13543864 14:−2.2653666 15:1.1439101 16:−0.46112978 17:−2.6953235 18:−2.8058879 19:−2.1647458 20:−0.028800163 21:−1.2686228 22:−1.3230211 23:0.28681833 24:0.15093741 25:2.4514618 26:−1.2292511 27:−1.0463799 28:−0.090019494 29:1.1452821 # −0.0038553465630628793 1:−1.4225143 2:−3.3811448 3:−1.3460624 4:−2.4572864 5:−1.2485046 6:1.5272132 7:3.8467693 8:3.6000576 9:−2.5641577 10:−0.67970216 11:−1.2237694 12:−0.66455346 13:−1.7749182 14:1.801129 15:−0.073441938 16:−1.0443138 17:2.9320962 18:−0.62133968 19:0.24629931 20:−2.5408921 21:−1.9696916 22:−0.15611142 23:−0.55407423 24:0.17331484 25:−2.6666267 26:0.11005254 27:−0.76523972 28:0.82345724 29:2.1196442 # |

APPENDIX C8-continued

| SVM Model Weights (29; Benign/Malignant) |
|---|
| 0.0038912456187004405 1:3.3504007 2:6.2324839 3:2.6426129 4:1.492183 5:3.0097013 6:−1.152725 7:3.869487 8:0.46534666 9:−1.5877725 10:−2.5205293 11:0.012004626 12:−1.0621814 13:−0.17664123 14:−2.0569618 15:−1.6601045 16:1.1510824 17:0.25813934 18:0.13201335 19:−1.131669 20:1.1496286 21:−1.575572 22:0.2038112 23:0.46738106 24:−0.70897067 25:−0.56662709 26:−0.48662603 27:0.020907728 28:−0.37763599 29:−1.4949493 # |
| 0.0020860413043267655 1:7.2026958 2:2.506717 3:1.6384877 4:2.1010149 5:2.6597629 6:−2.2723093 7:2.6085973 8:2.0390947 9:−0.71968418 10:−1.0824095 11:−1.1634985 12:0.56328827 13:0.013427491 14:−0.22713479 15:−1.2914221 16:−0.4034566 17:−0.095398933 18:0.86121124 19:−0.20695956 20:−0.28110185 21:−1.1006707 22:1.2550631 23:1.8677807 24:0.83824652 25:−0.20042829 26:−0.23248933 27:1.6082169 28:0.2339604 29:−0.94725752 # |
| −0.0038912456187004405 1:3.5024867 2:6.5884976 3:3.7849009 4:5.5771961 5:−0.03644076 6:−2.7955492 7:−3.0185244 8:−0.16116621 9:2.5598824 10:3.5982747 11:2.4496856 12:1.4353561 13:−2.3376217 14:1.5091493 15:−1.8332916 16:−1.7814847 17:1.6831902 18:0.072118565 19:1.0114408 20:−2.0413392 21:1.1551036 22:−2.3068783 23:−0.18732563 24:−1.1784918 25:0.81769562 26:−0.1530675 27:−1.8969883 28:−0.93342912 29:−0.20815188 # |
| −0.0024522298820238162 1:−0.26397073 2:−4.3800235 3:0.96010846 4:−6.5841908 5:1.6685443 6:−0.56736088 7:−0.083688535 8:−2.66816 9:−1.6018287 10:−2.2983365 11:−3.507324 12:0.0095484713 13:1.2482775 14:−0.31201324 15:0.47953141 16:0.59642285 17:−0.47637615 18:−1.1856458 19:−1.6341721 20:3.4143758 21:−0.020608557 22:0.73003125 23:−0.81526971 24:−1.5109706 25:−0.14740245 26:0.54324085 27:−0.27993053 28:−1.0582408 29:0.91323972 # |
| −0.0038912456187004405 1:4.1020322 2:−4.588994 3:−0.25456351 4:−0.32246256 5:1.8932445 6:2.0895927 7:−1.0208099 8:0.88184685 9:0.078009665 10:2.6228025 11:−0.4592624 12:−0.73257983 13:0.5757004 14:2.9550624 15:0.52651018 16:1.6183442 17:1.271421 18:1.9024082 19:−0.82549751 20:−0.39238787 21:1.6686051 22:0.77140731 23:0.098474815 24:−3.1235452 25:−1.6336083 26:−0.1539748 27:1.9261986 28:0.8454203 29:0.083330788 # |
| −0.0038912456187004405 1:1.2363012 2:−5.582078 3:−0.33564591 4:0.31853491 5:0.18021882 6:−0.46712884 7:−0.77220786 8:−0.43467858 9:−1.853532 10:−2.5806634 11:−1.1961414 12:1.362698 13:−1.7099397 14:−2.9604051 15:−1.8374467 16:0.26128343 17:1.0424188 18:−1.4112453 19:−0.62311435 20:1.0762979 21:1.1709037 22:1.9389135 23:−0.1562897 24:−0.12180445 25:−1.104779 26:1.1268845 27:−0.58998162 28:0.19233964 29:−0.0052791387 # |
| −0.0013349286371904696 1:−7.7966084 2:1.8707227 3:−23.323887 4:1.0747559 5:1.0184501 6:−3.600925 7:9.3491745 8:−7.7337961 9:−1.2228185 10:7.7243834 11:2.0076487 12:−4.368228 13:−1.5946441 14:−0.2912291 15:−2.0482881 16:−0.38283157 17:−1.6580502 18:−1.0132759 19:−0.17344542 20:0.65646726 21:−0.49175465 22:0.29616475 23:−0.65766221 24:−0.40362445 25:0.31434533 26:0.98643875 27:0.016180724 28:0.12472247 29:−0.22155482 # |
| 0.00049845306018736827 1:−4.6370125 2:25.3416 3:−16.121107 4:−0.6962499 5:−0.097961165 6:9.8783503 7:−13.519696 8:12.443069 9:−2.8442738 10:6.2117672 11:−14.486603 12:−1.9520348 13:1.2228634 14:−1.8063329 15:−1.0748529 16:0.99744153 17:−1.7065885 18:−0.12526843 19:0.24673074 20:0.050437115 21:0.24593517 22:−0.1737472 23:−0.39504737 24:0.86062044 25:−0.12319233 26:0.65940768 27:−0.34209335 28:0.20274197 29:−0.72116911 # |
| 0.0038912456187004405 1:0.2945444 2:1.5663686 3:2.0269644 4:−1.3007404 5:2.2870119 6:−3.3503802 7:1.4742044 8:3.5182641 9:−3.8660257 10:−0.30044997 11:2.4009323 12:0.023592524 13:−0.092459396 14:−1.9675099 15:−0.52797329 16:1.6415339 17:−1.3027037 18:1.1715622 19:−1.3815528 20:0.1912863 21:0.80708176 22:−1.3128206 23:−1.3250409 24:−1.3467921 25:0.47949335 26:−0.77753985 27:1.4726981 28:−0.20863654 29:−0.41831556 # |
| −0.0020646145995383684 1:−4.6798587 2:6.9537511 3:7.7693982 4:2.5801184 5:5.2154336 6:1.5670055 7:−1.2078696 8:−3.9267974 9:−0.82684386 10:3.3592942 11:−0.31578901 12:−0.053109273 13:−1.4976189 14:1.5029013 15:−2.4395096 16:2.8694046 17:2.9962363 18:1.3835291 19:−1.5468376 20:−0.57736629 21:−1.5085028 22:−1.9168996 23:1.0982634 24:−1.5078399 25:−0.74366945 26:−2.0148342 27:−4.1114769 28:0.23374891 29:−1.7665157 # |
| −0.0016004427029042917 1:−6.6617446 2:2.1398783 3:4.6612291 4:4.1200266 5:−9.3816519 6:−0.51241511 7:1.9775529 8:−2.3050761 9:0.16089861 10:2.2131913 11:−1.6792704 12:3.156086 13:0.84659821 14:−2.3553936 15:2.7890522 16:1.8426282 17:0.29614833 18:0.99678963 19:1.0124475 20:−0.8951236 21:−0.28949109 22:−2.5569632 23:1.5312668 24:−1.8644742 25:0.57216853 26:0.16517471 27:0.74864984 28:0.27347502 29:−0.47111201 # |

APPENDIX C9

| SVM Model Weights (9; Early/Late) |
|---|
| SVM-light Version V6.01 |
| 0 # kernel type |
| 3 # kernel parameter -d |
| 1 # kernel parameter -g |
| 1 # kernel parameter -s |
| 1 # kernel parameter -r |
| empty# kernel parameter -u |
| 9 # highest feature index |
| 59 # number of training documents |
| 41 # number of support vectors plus 1 |
| 0.51655237 # threshold b, each following line is a SV (starting with alpha*y) |
| −0.0050915505695401271 1:−8.3236828 2:−2.2087071 3:−0.27089623 4:2.6121626 5:2.6397204 6:3.6725602 7:2.614264 8:2.3370502 9:−2.1257644 # |

APPENDIX C9-continued

| SVM Model Weights (9; Early/Late) |
|---|
| −0.001830136480510669 1:8.4171867 2:5.161294 3:1.8632329 4:5.0714602 5:5.020833 6:−0.54171818 7:−0.74185503 8:−5.2189178 9:6.4979911 # |
| −0.0050915505695401271 1:12.019065 2:−4.8004398 3:4.4707756 4:4.196064 5:4.823154 6:−7.7504168 7:3.056613 8:−2.0674977 9:5.8091102 # |
| 0.0050915505695401271 1:0.12176631 2:1.5119995 3:−0.2009106 4:2.364769 5:−2.1576962 6:5.2755914 7:5.1912417 8:3.4393139 9:2.883764 # |
| 0.0041073606848502859 1:−13.079961 2:1.0930103 3:2.5594432 4:0.53382522 5:−14.319618 6:−7.9226675 7:−5.8632889 8:−4.1756377 9:−1.4476115 # |
| −0.0050915505695401271 1:−3.3880587 2:−2.6414342 3:2.8064957 4:−1.3999835 5:−2.6332676 6:6.3005533 7:1.1491936 8:2.35604 9:0.27799395 # |
| −0.0050915505695401271 1:2.5751998 2:10.221202 3:−0.95512414 4:9.3179073 5:−1.7831018 6:4.4525976 7:2.2225649 8:1.906949 9:2.5413458 # |
| 0.0050915505695401271 1:12.366791 2:6.0081248 3:1.7113053 4:2.7979217 5:6.9255257 6:−8.9968224 7:−2.4731126 8:−1.0733718 9:1.2842386 # |
| 0.0050915505695401271 1:8.6113596 2:0.035663262 3:0.78688341 4:1.3550853 5:3.178411 6:−1.0208944 7:−0.012796087 8:0.31668177 9:1.7832772 # |
| 0.0050915505695401271 1:9.7260504 2:−7.8163357 3:6.8109908 4:4.9323745 5:−1.6638223 6:3.745981 7:−0.47318304 8:2.3136632 9:0.40887526 # |
| −0.0016763983261444369 1:6.7611756 2:−14.71443 3:8.2472305 4:7.897903 5:2.2104344 6:1.6990815 7:−5.5606017 8:−3.6665649 9:0.020383494 # |
| 0.0050915505695401271 1:−7.6496434 2:2.703886 3:0.28662038 4:1.7879531 5:−3.0434427 6:−1.193588 7:6.320919 8:0.0046777669 9:−1.8738962 # |
| −0.0050915505695401271 1:4.2723708 2:1.0816427 3:−5.1717262 4:−9.1334429 5:−1.5630178 6:−4.2477694 7:−1.4042612 8:8.0716524 9:−0.61411405 # |
| −0.0050915505695401271 1:5.4242792 2:8.5105228 3:−3.6257584 4:−4.6308413 5:−0.75645578 6:−0.45588413 7:−0.88993597 8:−5.7085314 9:−1.9537624 # |
| −0.0050915505695401271 1:0.6300419 2:4.7734146 3:−1.2489752 4:−8.6097279 5:2.008311 6:−6.2184939 7:−6.5808897 8:2.7158918 9:−2.4301894 # |
| −0.0050915505695401271 1:−5.463172 2:7.882761 3:−2.6611001 4:4.7720952 5:−2.6212659 6:−0.66245055 7:6.5618205 8:0.32615471 9:1.1786789 # |
| 0.0050915505695401271 1:−0.24590166 2:−8.1644478 3:3.5928798 4:−1.0753064 5:−2.0135837 6:−0.10096657 7:−1.1228001 8:−3.6788621 9:−1.2726107 # |
| 0.0050915505695401271 1:−6.6983242 2:−9.0942469 3:1.7515687 4:−0.034388322 5:−4.4506936 6:0.60848588 7:4.9920249 8:0.42073253 9:−1.6036102 # |
| 0.0050915505695401271 1:−1.9800807 2:2.2620521 3:2.8543808 4:1.8967757 5:−8.6841125 6:7.2651377 7:−6.1430531 8:2.780396 9:5.0979185 # |
| −0.0050915505695401271 1:5.0472207 2:−15.336944 3:10.763581 4:0.12245622 5:−1.045119 6:5.0700855 7:0.022931358 8:1.0390165 9:−1.5287296 # |
| −0.0050915505695401271 1:1.2953433 2:−10.811604 3:10.668916 4:7.6443572 5:4.8650537 6:−2.3720403 7:−0.53300303 8:1.4913656 9:2.2692528 # |
| 0.0028402704586087501 1:7.9950004 2:7.8763146 3:−2.6768916 4:4.3499146 5:−0.26874429 6:−1.2617569 7:7.5231724 8:−1.001968 9:−3.2742054 # |
| 0.0050915505695401271 1:4.3136711 2:11.85136 3:−2.4349139 4:4.3976011 5:−0.064428166 6:3.3004136 7:0.26722765 8:0.083926447 9:2.1508505 # |
| 0.0050915505695401271 1:1.7432362 2:2.2080975 3:−0.45811424 4:−0.25904602 5:3.5310566 6:−1.0701555 7:2.6190839 8:−1.5763268 9:−0.24684133 # |
| −0.0050915505695401271 1:17.764666 2:13.276847 3:−6.217092 4:0.85309285 5:−3.2269576 6:7.2593732 7:−5.8735247 8:3.7184291 9:0.69418424 # |
| −0.0050915505695401271 1:2.9703248 2:−1.9154285 3:−1.4705251 4:−3.6158135 5:−0.88654208 6:−5.2746539 7:3.5916541 8:−1.5249115 9:0.42257392 # |
| −0.0050915505695401271 1:5.9731479 2:−2.2345276 3:2.4485157 4:0.69162613 5:0.90995193 6:0.060546741 7:1.8535619 8:−4.2391319 9:−3.620893 # |
| 0.0050915505695401271 1:11.704061 2:6.5949616 3:0.45483977 4:4.3702846 5:0.58678722 6:4.2801876 7:−6.5564938 8:−2.7858698 9:−10.711282 # |
| 0.0050915505695401271 1:8.0561037 2:−1.9924136 3:0.82999653 4:−3.7921369 5:−0.51860911 6:−6.4783216 7:1.8349005 8:9.0483742 9:−5.104785 # |
| 0.0050915505695401271 1:3.8433597 2:2.4452479 3:−2.7605469 4:−2.1829417 5:−0.22223227 6:0.20662466 7:8.3353586 8:1.2071977 9:0.19084433 # |
| 0.0050915505695401271 1:−7.5296364 2:−0.089652337 3:1.6496497 4:−2.9499371 5:−0.089410551 6:−1.4661449 7:5.7495131 8:−0.59138709 9:−2.9437177 # |
| −0.0050915505695401271 1:4.9163074 2:8.6507969 3:−2.8113577 4:−2.7883282 5:3.6005468 6:−3.0850611 7:−1.1117666 8:−1.8606527 9:−0.43682045 # |
| −0.0050915505695401271 1:2.9703248 2:−1.9154285 3:−1.4705251 4:−3.6158135 5:−0.88654208 6:−5.2746539 7:3.5916541 8:−1.5249115 9:0.42257392 # |
| 0.0050915505695401271 1:2.1832664 2:5.4387846 3:1.7195971 4:2.0288308 5:0.93580216 6:1.0958407 7:−1.1356411 8:−1.3170016 9:0.4036161 # |
| −0.0050915505695401271 1:−3.0042043 2:−3.113188 3:0.97381061 4:3.8624547 5:0.49664947 6:6.8813305 7:3.981081 8:0.12391745 9:−7.6547618 # |
| −0.001825325896597868 1:−4.7538085 2:−0.59608591 3:1.9817924 4:0.188968 5:1.4622716 6:2.7846963 7:−0.015608484 8:−0.34373811 9:−0.33039114 # |
| 0.0050915505695401271 1:1.5687745 2:2.8747225 3:−4.5921497 4:0.64045548 5:−1.2402862 6:−1.6395731 7:6.439642 8:2.6914668 9:−1.4795072 # |

APPENDIX C9-continued

| SVM Model Weights (9; Early/Late) |
|---|
| 0.0050915505695401271 1:13.466636 2:−3.3573108 3:5.5644298 4:0.57824087 5:1.6920621 6:−4.2968526 7:−2.6953287 8:12.022702 9:−0.46672329 # |
| −0.0050915505695401271 1:−8.2843933 2:3.6966038 3:−0.46435714 4:1.5304902 5:1.1075522 6:1.9134642 7:−0.79442489 8:0.52520049 9:0.83645153 # |
| −0.0016146717504300374 1:−5.3749466 2:−0.57213622 3:1.9126483 4:−0.20721766 5:2.5620048 6:0.42490456 7:2.1423569 8:2.1214426 9:2.944675 # |

APPENDIX C10

SVM Model Weights
(82; Normal/Diseased)

SVM-light Version V6.01
0 # kernel type
3 # kernel parameter -d
1 # kernel parameter -g
1 # kernel parameter -s
1 # kernel parameter -r
empty# kernel parameter -u
82 # highest feature index
138 # number of training documents
66 # number of support vectors plus 1
0.91588255 # threshold b, each following line is a SV (starting with alpha*y)
−0.0076483405254407864 1:4.5847425 2:2.2634013 3:2.0592687 4:−5.0744176 5:0.49108469 6:0.22187696 7:−0.36198542 8:0.55549079 9:1.16945 10:−0.87860185 11:−1.1730505 12:−0.3179169 13:0.23897839 14:0.0276103 15:−0.61931932 16:−0.36701918 17:0.615264 18:0.36962268 19:0.44902951 20:−0.33884093 21:1.0904425 22:−0.38783035 23:−0.37142119 24:0.39539182 25:−0.4826895 26:−0.21500368 27:−0.67627174 28:0.3106209 29:−0.19005503 30:−0.4044213 31:0.18639822 32:0.53177643 33:−0.0049400758 34:0.10411026 35:0.68578869 36:0.6420173 37:0.20198441 38:−0.2101412 39:0.064416796 40:−0.47914064 41:0.10461269 42:−0.16773476 43:−0.24920754 44:0.18940452 45:−0.1689584 46:0.062387589 47:−0.45937023 48:−0.33496517 49:−0.14661789 50:−0.22380395 51:−0.074915603 52:−0.1020799 53:−0.0018175301 54:−0.30253807 55:0.095320068 56:−0.015116707 57:0.21616898 58:0.050350856 59:0.12480601 60:−0.16774625 61:−0.0094391638 62:−0.15444873 63:−0.085922405 64:0.12145302 65:−0.061998256 66:−5.1350667e−005 67:0.060637005 68:0.098352186 69:0.0060797031 70:−0.10896418 71:−0.12341803 72:0.051324908 73:−0.029632403 74:0.058390208 75:0.11286738 76:−0.061157502 77:−0.065740541 78:0.058845371 79:0.0075725247 80:0.030219166 81:−0.056935508 82:0.25329241 #
−0.00044922431503931562 1:2.7292669 2:−0.87484086 3:1.3847753 4:−2.5739579 5:−1.6700684 6:1.5497742 7:2.4080608 8:−0.16631955 9:0.71711522 10:0.83663976 11:−0.34217042 12:−0.62897521 13:−0.24687213 14:0.016595371 15:−0.068257757 16:0.74069893 17:0.046216469 18:−0.15484238 19:−0.22101912 20:0.51348305 21:−0.085669801 22:−0.29448444 23:0.5208143 24:−0.14858969 25:−0.43966821 26:−0.56693649 27:0.55913043 28:0.22785313 29:−0.56943578 30:−0.35407853 31:−0.24522364 32:0.55069065 33:0.20480718 34:0.30379486 35:0.16293195 36:0.15258834 37:0.060010027 38:0.003893218 39:0.10791249 40:0.025357278 41:0.01221049 42:−0.13418299 43:0.22918029 44:−0.24793933 45:−0.043030676 46:−0.15973574 47:0.022680411 48:−0.22957636 49:−0.30749011 50:−0.011659611 51:−0.29319248 52:0.068978317 53:−0.015883964 54:−0.084682703 55:−0.090296596 56:−0.17299882 57:0.17286356 58:0.11593377 59:0.079820968 60:0.10089025 61:0.0374109 62:−0.057096943 63:0.029226493 64:−0.13218029 65:−0.01847516 66:−0.11948834 67:0.050875507 68:−0.20623796 69:0.062507994 70:−0.001748995 71:0.10765689 72:−0.15362611 73:0.010407766 74:−0.01776205 75:−0.045297291 76:−0.096473232 77:−0.038755342 78:0.04264988 79:−0.0060658264 80:−0.048446387 81:−0.0060270764 82:0.25329241 #
−0.014371081791088378 1:−5.1113815 2:0.57726955 3:−0.16488729 4:0.74226958 5:−0.30446488 6:0.886015 7:1.8407021 8:0.18502738 9:−0.11585715 10:1.9997953 11:−1.855323 12:1.511979 13:−1.6631278 14:0.7318204 15:−0.44916517 16:−1.2758362 17:−0.5231505 18:0.33729729 19:0.2270249 20:0.12768893 21:0.70871359 22:0.14002234 23:−0.16169912 24:−0.23062897 25:0.23679484 26:−0.28617558 27:−0.16430555 28:−0.16047885 29:−0.26272172 30:1.0595289 31:0.080195658 32:0.23094855 33:−0.0027916753 34:0.027821295 35:−0.087868601 36:0.0089416346 37:0.086345434 38:0.089552544 39:0.13538322 40:−0.083581984 41:−0.036680561 42:0.29984289 43:−0.19133432 44:−0.18991344 45:−0.038103603 46:0.060575396 47:−0.21550873 48:0.19764003 49:−0.31966409 50:−0.11456911 51:−0.12018149 52:0.06280674 53:0.056707256 54:0.1730841 55:−0.12535621 56:0.13015634 57:0.024985867 58:0.0010376547 59:−0.32023323 60:0.025551204 61:0.0029451507 62:−0.01172725 63:0.085252084 64:0.039614592 65:0.034663673 66:0.021892343 67:0.06643419 68:−0.12030014 69:0.066777527 70:0.085736215 71:0.014435894 72:0.11806186 73:0.085510179 74:−0.025865363 75:0.032559432 76:−0.031891055 77:0.068707459 78:−0.041551165 79:−0.068723224 80:0.0071537192 81:−0.049376685 82:0.25329241 #
−0.014371081791088378 1:2.2287729 2:−1.5711297 3:1.9142879 4:−2.4105821 5:−0.82760811 6:−0.051177371 7:2.3851252 8:0.23879933 9:−0.22404511 10:0.9515605 11:1.3752612 12:−0.47283813 13:−0.62004745 14:−0.15891433 15:−0.23082669 16:0.22891361 17:0.2984466 18:0.40207329 19:−0.25207257 20:1.114337 21:−0.085014805 22:−0.23101467 23:1.0295955 24:−0.13797589 25:−0.86484188 26:−0.36626312 27:0.47487071 28:0.29537171 29:0.37726468 30:0.34178337 31:−0.33228907 32:0.20104116 33:0.33601233 34:−0.41333455 35:−0.12814856

APPENDIX C10-continued

SVM Model Weights
(82; Normal/Diseased)

36:−0.11505847 37:−0.34001675 38:0.017345911 39:0.69055814 40:−0.20999053 41:−0.28078789 42:0.031112036 43:0.49086183 44:0.078199729 45:−0.11319491 46:0.024288604 47:−0.32287583 48:−0.39810702 49:−0.13391301 50:0.36462301 51:0.32107246 52:−0.14707287 53:0.016873788 54:−0.1542756 55:0.17066027 56:−0.040824272 57:−0.11435414 58:0.048499148 59:−0.11851748 60:0.25437239 61:0.12829477 62:0.001029599 63:−0.073667184 64:−0.094490662 65:0.069974028 66:−0.020970093 67:0.17274797 68:−0.0263604 69:−0.0022221897 70:−0.010828389 71:−0.059272483 72:0.084768288 73:−0.11710385 74:0.038728788 75:0.10109479 76:−0.0091925208 77:−0.03793776 78:−0.0065581268 79:0.081904575 80:0.014569444 81:−0.013232046 82:0.25329241 #
−0.012790167282685186 1:1.4574884 2:0.015848074 3:−0.33706057 4:−2.7190514 5:−0.23856521 6:1.1282589 7:4.770062 8:−1.29501 9:−1.9618376 10:−1.1694449 11:0.52534366 12:0.20604922 13:−2.2680326 14:0.31232414 15:−0.22935958 16:−0.12984578 17:1.4539638 18:−0.66572165 19:−0.61231405 20:0.11244271 21:0.14783788 22:0.11083714 23:0.29934567 24:−0.87440795 25:0.15323026 26:1.0258993 27:0.27414846 28:−0.04812938 29:−0.12562743 30:0.19762035 31:−0.17843114 32:0.40907478 33:0.25319341 34:0.048380677 35:−0.19457053 36:−0.23681453 37:0.13493825 38:0.17903772 39:0.35236469 40:−0.53913647 41:0.080974691 42:−0.26547015 43:−0.30515867 44:0.010836482 45:0.12052717 46:0.074725874 47:−0.17282738 48:−0.11382633 49:−0.11617535 50:0.19010371 51:−0.0024177416 52:0.19004396 53:−0.16984753 54:0.094210982 55:0.2869454 56:−0.038896669 57:0.092624567 58:−0.12117749 59:0.095160618 60:0.022614149 61:−0.22998363 62:−0.035386126 63:0.088216156 64:0.0059904926 65:−0.12207601 66:−0.044122107 67:−0.16771907 68:0.089419238 69:−0.0554187 70:−0.04553055 71:0.022514403 72:0.074693039 73:−0.091671467 74:0.018955754 75:−0.11902653 76:−0.038560998 77:0.034875493 78:−0.11377853 79:−0.00077183789 80:−0.061335351 81:−0.088626988 82:0.25329241 #
0.014371081791088378 1:0.06615974 2:0.82899189 3:3.7103472 4:0.46607265 5:−0.7831766 6:−1.6723894 7:−1.4600012 8:1.1860324 9:1.239713 10:0.81957269 11:−0.32550952 12:−0.55861676 13:−0.18325511 14:−0.22688431 15:−0.21395828 16:−0.93185627 17:0.20886678 18:0.13881239 19:−0.33757123 20:0.44255421 21:0.31845215 22:0.056041222 23:−1.5434151 24:−0.14916039 25:0.18890569 26:0.67844182 27:1.3269674 28:0.55836189 29:0.19340102 30:0.43353793 31:−0.99362516 32:0.91038316 33:1.1408969 34:0.31660739 35:0.34252787 36:−0.72257799 37:−0.46841586 38:−1.0209457 39:0.24468613 40:−0.075987726 41:0.45763588 42:0.089487724 43:0.36740333 44:−0.040773667 45:0.42630103 46:−0.39231455 47:−0.34097144 48:0.10832095 49:−0.035751157 50:−0.17712952 51:−0.22984697 52:−0.15966576 53:0.054046173 54:−0.1670076 55:−0.24421507 56:0.26292667 57:0.058809381 58:−0.085042097 59:0.1784807 60:−0.090719037 61:−0.076136403 62:0.18277626 63:−0.014541054 64:−0.12680072 65:0.0041166362 66:−0.05693952 67:−0.009223762 68:0.077097706 69:−0.072531514 70:0.030093649 71:0.077202767 72:−0.067946836 73:0.015153731 74:−0.094144031 75:0.067356981 76:0.0079724956 77:0.030221352 78:0.002898871 79:0.012197466 80:−0.0044414075 81:0.030008562 82:0.25329241 #
0.014371081791088378 1:3.9638965 2:−0.36049458 3:10.393447 4:−6.0010238 5:−4.7190962 6:0.41640604 7:−0.26739401 8:1.0713867 9:−0.31974295 10:−0.88768101 11:−0.13179372 12:−0.08601705 13:−0.12007866 14:0.88547117 15:0.6711638 16:−0.63679755 17:1.0436785 18:−0.20595425 19:0.19097529 20:0.62846404 21:−0.16020004 22:0.46306559 23:0.048650976 24:0.28169036 25:−0.60569304 26:−0.37091634 27:−0.12243859 28:0.21760912 29:−0.23224078 30:−0.52316302 31:0.51549333 32:−0.64715832 33:−0.15821511 34:−0.095805489 35:−0.023212345 36:−0.35592464 37:−0.24998397 38:−0.13912265 39:0.067599528 40:−0.074657343 41:−0.15317573 42:0.423792 43:0.18411036 44:−0.042168655 45:0.26337865 46:0.57878953 47:0.39212322 48:0.058100116 49:−0.21698788 50:−0.064674288 51:0.063105181 52:0.031948261 53:0.10002521 54:0.02464137 55:0.051568132 56:−0.25280839 57:0.080034398 58:0.26760021 59:0.20775615 60:−0.048556402 61:−0.08541014 62:0.24948281 63:−0.082818843 64:−0.14832869 65:0.12030313 66:−0.054670993 67:−0.05423595 68:0.10971306 69:−0.014325269 70:−0.044792432 71:0.20490377 72:−0.0062538898 73:0.026925711 74:0.043139815 75:0.029467251 76:−0.0021748471 77:0.0485989 78:0.064881511 79:−0.024845082 80:−0.043836217 81:−0.0997077 82:0.25329241 #
0.014371081791088378 1:−0.012769639 2:0.16790693 3:2.2407362 4:−0.65757632 5:2.1763229 6:−0.27352577 7:1.5930518 8:0.38376945 9:1.6629692 10:−1.3885146 11:2.3340931 12:−0.054302484 13:−0.17919821 14:0.42166984 15:0.2118218716:0.5195474 17:0.067542337 18:−0.86686736 19:0.86120147 20:−0.14290035 21:−0.2029241 22:0.4419525 23:0.82795292 24:0.23999192 25:0.51351893 26:−0.19925565 27:−0.5412268 28:−0.13415499 29:−0.068471946 30:0.4770731 31:0.029407311 32:0.5765447 33:−0.56791747 34:−0.13480355 35:0.44296059 36:−0.064839892 37:−0.15890415 38:0.21500614 39:−0.18021694 40:−0.60670781 41:−0.047837473 42:0.022065988 43:−0.25367579 44:0.62644428 45:0.27425531 46:0.13100083 47:−0.50767177 48:0.2815612 49:−0.091984488 50:−0.28374043 51:0.033678703 52:0.14927301 53:0.14131416 54:−0.036364838 55:0.031883806 56:0.065345913 57:−0.037159827 58:−0.071655668 59:0.15219162 60:0.026322618 61:−0.065573119 62:0.048991051 63:−0.084432766 64:−0.057116892 65:0.24003533 66:0.0039681606 67:−0.0093432497 68:−0.017792653 69:−0.05870457 70:0.023568843 71:−0.065016292 72:−0.0044201193 73:0.015904099 74:−0.075103998 75:0.064098649 76:0.0098518692 77:0.062355176 78:0.05770335 79:−0.10099295 80:0.034868445 81:0.015963936 82:0.25329241 #
0.010140794447390309 1:−4.1371694 2:3.247313 3:1.5488372 4:2.1306124 5:0.076607205 6:0.77619171 7:2.1699479 8:1.0553551 9:−1.6450247 10:−0.256722 11:−1.023086 12:0.0088802725 13:0.69740379 14:0.35752964 15:0.78221714 16:0.015664212 17:−0.66256732 18:0.013428795 19:0.38016322 20:0.42372048 21:−0.76154864 22:1.5354502 23:−0.81900328 24:0.40335721 25:0.43321145 26:−0.49061343 27:0.21595629 28:0.061132494 29:0.24946894 30:−0.61602104 31:−0.29535908 32:−0.086960718 33:−0.82157582 34:−0.17725144 35:−0.62329596 36:−0.58398896 37:−0.26470143 38:−0.23674664 39:−0.16934665 40:−0.13747382 41:−0.08068835 42:−0.50744444 43:−0.21849048 44:−0.15728588 45:−0.40683433 46:0.089571439 47:−0.22218646 48:−0.26643953

APPENDIX C10-continued

SVM Model Weights
(82; Normal/Diseased)

49:−0.21469624 50:0.048496488 51:−0.035119418 52:−0.090131447 53:0.037757535
54:−0.35595295 55:−0.13658559 56:−0.054087948 57:−0.083727963 58:0.052598465 59:0.085117072
60:0.11267716 61:0.13963972 62:0.0078268088 63:0.25140557 64:0.024301574
65:−0.0076780352 66:−0.1301339 67:−0.14596663 68:−0.11988603 69:0.067040093 70:0.12744001
71:0.032765571 72:0.1281205 73:0.061594952 74:−0.031729899 75:0.081476592 76:−0.08268398
77:−0.067217961 78:0.0087663494 79:0.0098926937 80:−0.0090905735 81:0.039001472
82:0.25329241 #
0.014371081791088378 1:3.6803861 2:−3.383316 3:2.6263463 4:−0.11964729 5:2.393744
6:−2.8033917 7:−1.4413491 8:1.5224484 9:1.8574331 10:−0.045176703 11:−0.26056677
12:−0.91296232 13:0.53769797 14:0.12464325 15:−1.5257736 16:0.0065172375 17:0.16323173
18:0.57849044 19:0.3868342 20:0.7542969 21:−0.26354387 22:−0.46942788 23:0.14543609
24:0.075713098 25:−0.29288822 26:0.56308526 27:−0.40826803 28:0.073977292 29:−0.20787065
30:0.13102642 31:0.00035501234 32:0.25087476 33:−0.24365909 34:−0.42595544 35:0.060347307
36:−0.12909004 37:−0.14663725 38:0.34130844 39:0.34116295 40:−0.12632339 41:−0.48732257
42:0.18367004 43:−0.42145506 44:0.2766315 45:−0.13402918 46:−0.27153131 47:0.24115941
48:0.030122265 49:0.034082003 50:0.20779416 51:−0.21837978 52:−0.065812759
53:−0.077067494 54:−0.038395625 55:−0.13360102 56:−0.32544705 57:0.19000578 58:−0.011514278
59:−0.055158172 60:−0.012644858 61:−0.0072809733 62:0.11915585 63:0.17997804
64:−0.057244699 65:−0.19111633 66:0.019482378 67:−0.10509145 68:−0.15546803 69:−0.14434534
70:0.012139316 71:0.027630648 72:0.061719794 73:0.0098098945 74:0.011975448
75:−0.031700905 76:−0.017836515 77:−0.0094708651 78:−0.077912182 79:−0.019385353
80:−0.012621189 81:−0.013810867 82:0.25329241 #
−0.014371081791088378 1:−6.2911754 2:−0.33154821 3:2.414753 4:1.0904108 5:0.57706022
6:−1.4319143 7:−1.7905619 8:−1.1273483 9:0.62155408 10:0.79449165 11:−0.44127455 12:1.936054
13:0.58078474 14:0.033164572 15:−0.044798613 16:−0.62758458 17:0.32621294 18:−0.95531911
19:0.75106478 20:0.65697551 21:−0.5813753 22:−0.034206238 23:0.26181296 24:0.061108191
25:−0.29467076 26:−0.18484378 27:0.88564676 28:−0.10793303 29:0.6550312 30:−0.088795416
31:0.0096849464 32:−0.081404671 33:−0.16644143 34:−0.19583501 35:−0.25153825
36:0.098348863 37:0.26091307 38:0.10535178 39:0.017809503 40:0.089981742 41:0.40348145
42:0.1128048 43:0.18216892 44:0.29997975 45:−0.27850741 46:0.4457044 47:−0.11780976
48:−0.26756835 49:−0.033972185 50:0.045925472 51:−0.00088148023 52:−0.070664935
53:0.20158044 54:0.08260829 55:−0.093603566 56:0.10176333 57:0.051761001 58:−0.11161759
59:0.078998119 60:−0.095937975 61:−0.10439479 62:0.069873109 63:0.30256033 64:0.093203656
65:−0.080625921 66:0.041989177 67:−0.076998971 68:−0.049412522 69:−0.0010920394
70:0.011841179 71:−0.00012070101 72:0.060432691 73:0.02278533 74:−0.09382841
75:−0.020158742 76:0.02458903 77:0.032093987 78:−0.036760859 79:−0.059564136 80:0.0073090857
81:−0.012033216 82:0.25329241 #
−0.0055663887400561624 1:7.5600095 2:−11.206866 3:3.0734401 4:6.6675763 5:0.56220853
6:1.7533294 7:−2.4755189 8:7.1283174 9:−6.3222933 10:−1.9066242 11:1.686049 12:3.1836298
13:−0.11008647 14:−0.47785965 15:−2.9055338 16:1.9649364 17:2.0460181 18:0.21192932
19:0.52190208 20:−0.57973236 21:1.4056532 22:−0.43432754 23:−0.63994479 24:0.37334344
25:1.6209371 26:−0.80080259 27:0.56663495 28:−0.2411693 29:−0.18885052 30:−0.26599684
31:0.018342448 32:0.25679478 33:0.26941288 34:−0.030926351 35:−0.30656919 36:0.13426434
37:0.21872109 38:−0.010530269 39:0.06377358 40:−0.019184245 41:−0.00068895466
42:0.1695777 43:0.076885462 44:−0.1422419 45:−0.092319533 46:0.082383759 47:−0.07128039
48:−0.0017274675 49:−0.052341443 50:0.040855333 51:0.067533478 52:−0.018576792
53:−0.030705014 54:−0.12237284 55:−0.027723813 56:−0.029973468 57:−0.011589891 58:0.060792223
59:−0.039217584 60:0.017904056 61:−0.035995733 62:−0.013372438 63:−0.026217587
64:−0.0077372417 65:0.025181262 66:0.04035626 67:−0.00054352538 68:−0.005767677
69:0.043089751 70:−0.024131538 71:−0.011423401 72:0.023911273 73:−0.014854904
74:−0.019994328 75:−0.0087489393 76:0.013398531 77:−0.0083918357 78:0.0037705479
79:0.0036385492 80:−0.0084521333 81:0.00060540921 82:0.25329241 #
−0.014371081791088378 1:−6.0427446 2:−2.2942531 3:1.7665267 4:0.24104188 5:0.05302066
6:−0.65499085 7:−2.2508273 8:−0.58677131 9:1.8983141 10:−0.60792536 11:−0.61068189
12:0.90856034 13:−0.051281676 14:−0.47347507 15:0.59544098 16:−0.20183299 17:0.66765237
18:−0.22371037 19:0.011542096 20:−0.62673527 21:−0.4327623 22:−0.16975054 23:0.16413261
24:0.23278002 25:0.0046928497 26:−0.210575 27:0.57754338 28:0.021914244 29:−0.32897565
30:0.50235379 31:0.49477726 32:−0.19662215 33:−0.17688251 34:0.43916401 35:−0.34179768
36:−0.28719062 37:0.27171001 38:0.0099805389 39:−0.065548085 40:−0.17761378 41:0.44311571
42:−0.16055381 43:0.2588228 44:0.356906 45:−0.25702626 46:0.34241146 47:0.035489589
48:−0.087052964 49:0.005755974 50:−0.30426183 51:0.13479213 52:0.057545237 53:−0.064516015
54:−0.041568179 55:0.31732023 56:0.088190354 57:0.061988279 58:0.062836811 59:−0.30461231
60:−0.10091273 61:−0.065438919 62:−0.056244068 63:−0.00015518715 64:0.076446712
65:−0.076848172 66:−0.078847811 67:0.0087593179 68:−0.013409368 69:0.10315542 70:−0.13130958
71:0.082615353 72:0.023463249 73:−0.12341658 74:−0.11428598 75:0.10732516 76:0.058815319
77:0.048135847 78:−0.076815382 79:0.097012222 80:−0.052658875 81:−0.0095535312
82:0.25329241 #
−0.014371081791088378 1:0.032119375 2:−0.11809584 3:2.1360173 4:2.0512309 5:0.89222878
6:−0.39003006 7:−1.9414886 8:1.8421218 9:1.2863975 10:−0.8708607 11:−0.091651775
12:0.090948768 13:−0.73991352 14:−0.99880159 15:0.43535626 16:0.21856615 17:−0.23930903
18:−0.22786051 19:−0.44525531 20:0.31482485 21:−0.20232427 22:−0.19022959 23:0.078739755
24:0.58435839 25:−0.27984121 26:0.26633874 27:0.11877418 28:−0.23983058 29:0.4422152
30:−0.65171093 31:0.74981868 32:0.30158442 33:−0.88743174 34:−0.51526433 35:−0.27156922
36:0.18388171 37:−0.056392461 38:−0.1363073 39:0.47089884 40:0.26797923 41:−0.22702375
42:−0.40387371 43:0.10113742 44:0.15141408 45:0.38246739 46:0.0042423746 47:0.0072439043
48:−0.19346309 49:0.0077932407 50:−0.061037708 51:0.1065983 52:0.046168827 53:0.096873768
54:0.1893784 55:−0.18854593 56:−0.0020919098 57:−0.0061527779 58:−0.41573647

APPENDIX C10-continued

| SVM Model Weights (82; Normal/Diseased) |
|---|
| 59:0.095826067 60:0.10766485 61:−0.16556598 62:−0.01122171 63:0.032306243 64:−0.14764972 65:0.049841542 66:−0.03756002 67:0.12502031 68:0.12935309 69:0.10088674 70:0.089521088 71:−0.11152785 72:0.036221862 73:0.073285319 74:0.035094831 75:−0.087618344 76:0.023657883 77:0.071551301 78:0.042617798 79:0.063766234 80:−0.024794083 81:0.0062677944 82:0.25329241 # |
| −0.014371081791088378 1:−6.8444982 2:−0.67081594 3:0.78908235 4:0.90495342 5:−1.5253073 6:−0.85245174 7:−2.0621061 8:−0.38565096 9:1.7308034 10:−1.0100794 11:−0.29632479 12:0.4710829 13:0.70629627 14:−0.24393921 15:0.85331804 16:−0.11409777 17:−0.056702696 18:−1.0600469 19:−0.14985374 20:0.531663 21:0.0037747934 22:−0.1185537 23:0.62785983 24:0.34188637 25:0.41162553 26:0.078405388 27:0.14154691 28:0.047454808 29:−0.16734748 30:0.38317207 31:−0.041209783 32:−0.088877186 33:0.3768093 34:0.2984463 35:−0.54275906 36:0.49366173 37:0.35959271 38:0.34264225 39:−0.015594763 40:−0.24267282 41:−0.03299509 42:−0.0080984058 43:0.19575833 44:−0.20981693 45:0.2940782 46:0.1673755 47:−0.32508108 48:0.11447848 49:0.12654655 50:0.1308234 51:−0.028056517 52:0.18311964 53:−0.16149956 54:−0.10682806 55:−0.044393551 56:−0.048205018 57:0.19252259 58:−0.23667762 59:0.047196396 60:−0.15432329 61:−0.047469445 62:0.011105429 63:0.082035676 64:0.03135239 65:0.10900541 66:−0.063973896 67:−0.05986141 68:−0.17266303 69:−0.084595196 70:−0.05756199 71:−0.11037008 72:−0.026960775 73:0.004685991 74:0.042266723 75:0.022531377 76:−0.020153707 77:−0.090982839 78:0.016833995 79:0.087431401 80:0.0059268074 81:0.040343598 82:0.25329241 # |
| 0.014371081791088378 1:−5.8997812 2:−0.43082115 3:−1.8980318 4:−1.1697601 5:−1.3073525 6:−0.21801195 7:3.576349 8:1.1246392 9:−2.1337941 10:−0.43831295 11:2.0966227 12:−0.19355604 13:0.31669274 14:0.26986292 15:0.17263962 16:−0.42185301 17:0.87249577 18:0.059252266 19:−1.6848979 20:−0.7696352 21:−0.42338499 22:0.20169574 23:0.085185103 24:−0.22855495 25:0.41996938 26:0.29405114 27:−0.86857146 28:0.1784066 29:−0.052480277 30:0.22091232 31:0.56136143 32:0.1475556 33:0.52395034 34:−0.15741901 35:0.29494062 36:0.24160613 37:−0.17903697 38:−0.78855848 39:0.071278051 40:0.1162355 41:−0.27214628 42:−0.50193983 43:0.070323519 44:0.30191693 45:−0.051018227 46:0.010760454 47:0.63021773 48:−0.33557719 49:0.050247598 50:0.070755698 51:−0.25414976 52:0.022398766 53:−0.011261068 54:−0.27318543 55:0.028218282 56:0.14511426 57:0.19780368 58:−0.1547322 59:−0.16323167 60:−0.14006078 61:0.11106031 62:−0.04976707 63:0.33804101 64:−0.069027431 65:0.25202602 66:0.17354612 67:−0.041310545 68:−0.13214482 69:−0.029418631 70:−0.097097382 71:0.03947828 72:0.013589907 73:0.11003853 74:−0.032907866 75:0.085027345 76:0.09880086 77:0.030141551 78:0.057553545 79:0.024348887 80:0.034383919 81:−0.037184104 82:0.25329241 # |
| 0.014371081791088378 1:−2.5109749 2:0.47807598 3:−1.6844766 4:1.4923682 5:−1.2148795 6:0.838889 7:1.9064817 8:2.2714243 9:0.88263375 10:0.42249376 11:0.71731615 12:0.021338582 13:−0.02829697 14:−0.34000656 15:−1.2128325 16:−0.45739123 17:−0.64468175 18:−0.18318769 19:−0.023497388 20:−0.32469469 21:−0.2152589 22:0.018175134 23:0.58018172 24:0.53330719 25:−0.033656619 26:−0.45612741 27:0.1873823 28:0.002734659 29:−0.12017396 30:0.084703878 31:0.03466408 32:0.3672398 33:−0.32899913 34:0.22373621 35:0.21340086 36:−0.51913774 37:−0.7799384 38:0.41012725 39:0.020277422 40:−0.1783268 41:−0.13257091 42:−0.069151655 43:0.26569706 44:−0.13337305 45:0.15128145 46:−0.11448255 47:−0.06978748 48:0.038996942 49:0.22553994 50:0.076887831 51:0.088754304 52:−0.081065692 53:0.01638128 54:0.20377974 55:−0.063422523 56:−0.016669946 57:−0.0055070403 58:0.20942272 59:0.089951754 60:0.0073118992 61:−0.023328373 62:−0.29891464 63:0.15648349 64:0.050855875 65:0.012495726 66:0.0063293944 67:0.032252699 68:−0.04352675 69:−0.056493919 70:−0.055005439 71:0.018937372 72:−0.0019040022 73:0.0027660404 74:0.070419207 75:−0.077461638 76:0.085045666 77:0.072235517 78:−0.0062333569 79:−0.03773066 80:−0.01532511 81:−0.063425124 82:0.25329241 # |
| 0.014371081791088378 1:−1.26361 2:3.3836086 3:0.81772143 4:1.4750563 5:1.5914512 6:4.4661193 7:1.3093367 8:−1.8483263 9:−2.2057548 10:1.7677203 11:−0.24599285 12:−0.66646421 13:−1.0781813 14:0.55211741 15:−0.6860401 16:−1.0814471 17:0.018195715 18:−0.15328483 19:0.39476219 20:1.3755138 21:−0.025881356 22:−0.74440396 23:−1.1534657 24:0.91008627 25:0.00068105949 26:−0.3520554 27:−0.45552614 28:0.32108212 29:0.1472235 30:−0.24090932 31:0.31023282 32:−0.10801363 33:−0.16989356 34:0.48647556 35:−0.37672669 36:0.054345746 37:0.19963665 38:−0.48056811 39:−0.41126305 40:−0.45404658 41:−0.1887565 42:0.12553735 43:−0.34539199 44:0.04151167 45:0.15788841 46:0.11210428 47:0.030770093 48:0.079333708 49:0.022298075 50:0.025678286 51:0.41651532 52:0.14260364 53:−0.052502602 54:−0.17797372 55:−0.14035514 56:−0.21930592 57:−0.0056129838 58:−0.060061038 59:−0.12160099 60:−0.17971112 61:0.037148319 62:0.096509479 63:0.055976581 64:−0.072011344 65:−0.13649841 66:0.08958105 67:0.035684876 68:0.1460212 69:1.7755583e−005 70:0.12277698 71:−0.042404465 72:−0.20186207 73:−0.053846516 74:−0.073742546 75:−0.10836264 76:0.1219011 77:−0.082848266 78:0.04130993 79:−0.031955443 80:−0.021111501 81:0.0025025744 82:0.25329241 # |
| 0.014371081791088378 1:0.40318605 2:2.8663054 3:−0.10761927 4:2.7486448 5:−2.1411502 6:−1.0664608 7:0.085744604 8:−1.2780683 9:−1.2669294 10:−0.17690255 11:−0.12264714 12:−0.53043371 13:−0.28566968 14:0.74049652 15:−0.95664024 16:−0.80509835 17:−0.73836279 18:−0.021718033 19:−0.56745547 20:−0.90991509 21:−0.15685536 22:−0.31473094 23:0.23180459 24:−0.05583882 25:−0.25527993 26:−0.47645861 27:0.41751254 28:−0.5695594 29:−0.23506841 30:−0.35427865 31:−0.21719298 32:−0.0018052902 33:−0.074756473 34:−0.42836496 35:0.029852936 36:−0.58429658 37:0.58278036 38:0.22274098 39:−0.054105129 40:0.1814536 41:0.075631209 42:0.0072739045 43:−0.075652882 44:−0.033003766 45:0.15518606 46:−0.099876814 47:0.2315187 48:0.048440639 49:−0.049111921 50:0.17749941 51:−0.090137519 52:−0.065180384 53:0.12669912 54:−0.020098273 55:−0.041329514 56:0.15423527 57:0.031366881 58:−0.28443292 59:−0.27453333 60:0.034703646 61:0.10519245 62:−0.014362165 63:−0.086428434 64:−0.18141192 65:0.063100941 66:−0.01853578 67:0.0029890554 68:0.035743434 69:0.00096162932 |

APPENDIX C10-continued

| SVM Model Weights (82; Normal/Diseased) |
|---|
| 70:−0.02557517 71:−0.072258428 72:−0.070781901 73:−0.091054782 74:−0.0049574855 75:0.056021247 76:0.049303189 77:0.026807508 78:0.037548583 79:0.010849881 80:0.00506728 81:−0.075166389 82:0.25329241 # |
| 0.014371081791088378 1:−1.6712141 2:2.3919587 3:0.49178827 4:−0.95237738 5:1.7086816 6:−0.086744487 7:3.0472524 8:0.48604348 9:−0.90352476 10:1.8597959 11:−1.1408889 12:1.0090487 13:−0.89271063 14:0.91446865 15:0.48014361 16:−0.86044335 17:1.002522 18:0.71325761 19:0.48577225 20:1.1102482 21:0.68385476 22:0.32870358 23:−0.070378996 24:0.47764394 25:0.066088229 26:−0.56832731 27:−0.53314847 28:−0.49583834 29:0.34372634 30:−0.044137914 31:0.30458117 32:0.29500982 33:0.51554859 34:−0.3652086 35:0.095339701 36:−0.61318243 37:−0.10103861 38:0.2599676 39:−0.17364021 40:−0.1766223 41:−0.23599496 42:−0.046590667 43:−0.064370431 44:−0.26495481 45:−0.34535214 46:−0.2179686 47:0.26411498 48:0.068896614 49:0.2932317 50:−0.20728762 51:−0.28921679 52:−0.15075696 53:0.27824175 54:0.34107968 55:0.04799192 56:−0.060297459 57:−0.086595491 58:0.063428275 59:0.051238902 60:−0.30705446 61:0.13086054 62:−0.02681252 63:−0.039995302 64:0.027519802 65:0.011346187 66:−0.022367191 67:0.088818073 68:0.16908786 69:−0.047578987 70:−0.055261441 71:−0.10137115 72:−0.073881082 73:0.016444644 74:0.0034697505 75:0.022061273 76:−0.09315376 77:0.028341139 78:−0.023250699 79:0.094959848 80:−0.025907686 81:0.034736209 82:0.25329241 # |
| 0.014371081791088378 1:−2.7895725 2:1.4355584 3:2.1953652 4:2.4886854 5:0.62598842 6:0.83918959 7:0.51678389 8:1.1869923 9:2.5024664 10:−1.6917404 11:−0.95654958 12:2.1381874 13:−1.7291743 14:0.35777313 15:−0.53910244 16:−0.13950135 17:−0.96974945 18:1.0978501 19:0.50021154 20:−0.22891597 21:−0.4039512 22:−0.91947883 23:0.7026884 24:0.40972477 25:−0.21648316 26:−0.63700694 27:−0.25882831 28:0.043598037 29:−0.42077249 30:−0.15058325 31:0.37921295 32:−0.020307709 33:0.28444818 34:−0.34290516 35:0.086913921 36:0.25775102 37:−0.7976433 38:−0.38572249 39:−0.2849552 40:0.069534048 41:0.087549545 42:−0.011445804 43:0.12894829 44:−0.15607941 45:−0.29646993 46:−0.0058567235 47:−0.04477372 48:−0.028155912 49:−0.30048275 50:−0.014888221 51:−0.17145225 52:0.10608047 53:−0.30674717 54:−0.09836974 55:0.16539836 56:0.083136439 57:−0.24667794 58:−0.050652042 59:0.032507453 60:−0.025482209 61:−0.024832299 62:−0.0030350632 63:−0.074655138 64:−0.17327681 65:−0.14795719 66:0.076594219 67:0.12902378 68:−0.043942571 69:−0.092854701 70:−0.011057142 71:−0.018071271 72:0.044070967 73:−0.08393991 74:0.0067454386 75:0.061829854 76:0.013420491 77:0.043701302 78:−0.027847053 79:−0.05306711 80:−0.018448954 81:0.049803432 82:0.25329241 # |
| −0.014371081791088378 1:0.33095098 2:7.6342816 3:−0.52201921 4:−3.321856 5:4.7346787 6:0.87662041 7:1.1792169 8:0.18118884 9:−0.6140644 10:−0.3773514 11:0.31409085 12:−0.31206053 13:−0.61933213 14:−1.2531929 15:0.32133192 16:0.76557356 17:0.022583621 18:−0.11288887 19:−0.87596291 20:0.16352759 21:0.91092724 22:−0.84108925 23:0.22505504 24:0.14446537 25:0.49118423 26:0.15799452 27:0.75147492 28:−0.45861977 29:0.19834095 30:−0.21124585 31:0.061338119 32:−0.63503015 33:0.2163108 34:0.22774342 35:−0.080905147 36:0.23970407 37:−0.011915832 38:−0.073457547 39:−0.069530487 40:0.10668084 41:−0.22877498 42:0.00027975201 43:0.15557131 44:0.14697385 45:−0.31441194 46:−0.29905641 47:−0.06365215 48:0.046732217 49:−0.051229097 50:0.19549561 51:−0.25697255 52:−0.037893165 53:0.090026349 54:−0.060175765 55:0.18640916 56:−0.080258079 57:0.15948784 58:0.06866762 59:0.14220145 60:−0.16259545 61:0.038652621 62:0.04635654 63:−0.11137922 64:0.15704307 65:0.20364094 66:0.090868734 67:0.11366525 68:−0.16438502 69:−0.010643563 70:0.02873197 71:0.047899194 72:−0.091893487 73:0.096058115 74:−0.0026567413 75:0.066286206 76:0.023174321 77:0.078776374 78:−0.068127558 79:−0.015330745 80:0.0041523818 81:0.033513471 82:0.25329241 # |
| −0.014371081791088378 1:0.39179108 2:1.7604795 3:−1.0547895 4:3.2785881 5:−3.0231071 6:−0.45013994 7:2.61131 8:1.252444 9:−1.8012906 10:0.49729681 11:1.8875666 12:−0.11081514 13:0.60079718 14:0.17753549 15:1.1019816 16:−0.19631812 17:−0.59657872 18:0.85135156 19:0.096810386 20:−0.762613 21:−0.3628495 22:−0.22317162 23:−0.38828939 24:−0.396528.36 25:−0.2012544 26:−0.85573673 27:−0.050470203 28:−0.086968079 29:−0.28143242 30:0.58006781 31:−0.015192202 32:−0.036746971 33:−0.25384519 34:−0.31505802 35:0.34487239 36:0.16051285 37:0.08287777 38:0.55975235 39:0.56815648 40:−0.26505998 41:0.1789909 42:0.20638096 43:0.38074276 44:0.031830557 45:0.22150782 46:−0.12355172 47:0.17361011 48:0.27912021 49:0.40480542 50:−0.097099192 51:−0.09492033 52:−0.32739455 53:−0.1349532 54:−0.12438698 55:−0.058416624 56:−0.22307913 57:0.078992359 58:−0.083497547 59:0.014389225 60:−0.17107596 61:−0.027994405 62:0.051253933 63:−0.0096493522 64:0.038747251 65:0.043816548 66:−0.15261744 67:0.0061370675 68:0.010998365 69:−0.073338471 70:0.070489883 71:0.00048124173 72:0.0033559983 73:−0.1173143 74:−0.0093150102 75:−0.019778799 76:0.061944958 77:−0.17449103 78:0.063401021 79:0.0027022141 80:0.005131497 81:0.02158306 82:0.25329241 # |
| 0.014371081791088378 1:−1.6879857 2:−6.3618093 3:1.6913548 4:0.65733463 5:2.3925114 6:2.6060944 7:−2.0069878 8:−1.8359069 9:−0.58866799 10:0.59539658 11:0.17804295 12:−1.9013586 13:−0.81792754 14:−0.59221917 15:−0.049872674 16:−0.63125944 17:1.003877 18:−0.35896239 19:−0.0006466324 20:−0.27938423 21:0.43797824 22:0.16159621 23:0.86024743 24:0.11528484 25:−0.29002795 26:0.18493521 27:0.28892779 28:0.19938286 29:−0.5241949 30:−0.61230177 31:−0.28926277 32:−0.65261674 33:0.27812475 34:−0.42605954 35:0.13420232 36:−0.24654177 37:−0.162928 38:0.13758932 39:0.11383753 40:0.47700512 41:−0.056262396 42:−0.049793806 43:−0.12529169 44:0.26192901 45:0.18028818 46:0.20800892 47:0.049365703 48:0.17542955 49:0.24260254 50:−0.13670516 51:−0.38179177 52:0.26778433 53:0.32891425 54:−0.33751085 55:−0.33781996 56:−0.052736275 57:−0.20112416 58:0.012140824 59:−0.10520463 60:0.067837618 61:−0.14393544 62:−0.16461192 63:0.077245958 64:0.028511703 65:−0.12176114 66:−0.015509538 67:0.28928107 68:0.011405483 69:0.085909136 70:−0.029192718 71:−0.021930479 72:−0.042123832 73:0.034344546 74:0.0029628596 75:0.039048839 76:−0.052951615 77:−0.035603598 78:0.0064464104 79:0.020607302 80:0.037455752 |

APPENDIX C10-continued

| SVM Model Weights (82; Normal/Diseased) |
|---|
| 81:−0.0092717353 82:0.25329241 # |
| 0.014371081791088378 1:−4.4199657 2:−4.3907685 3:1.2562128 4:−0.37993807 5:0.63287181 |
| 6:−2.1203623 7:1.1456695 8:−0.56502068 9:−0.084575847 10:−0.44528866 11:−0.63158774 |
| 12:−0.75912005 13:0.50797874 14:−0.33129719 15:−0.20643009 16:0.311584 17:0.11107267 |
| 18:0.067017421 19:−0.460798 20:−0.25446153 21:0.28213504 22:−0.069342628 23:0.18576097 |
| 24:0.064234734 25:0.060541634 26:0.30079058 27:−0.60330588 28:−0.69447643 29:−0.18994376 |
| 30:0.078992747 31:0.043445524 32:−0.29727209 33:0.63747901 34:0.032936722 35:−0.15514255 |
| 36:0.38121408 37:−0.099617302 38:−0.42663234 39:0.054005116 40:−0.043151319 |
| 41:−0.044334553 42:−0.22261797 43:−0.01120665 44:0.25292879 45:0.2124763 46:0.076861568 |
| 47:0.2133105 48:0.069120817 49:−0.32321119 50:0.12202964 51:−0.34076053 52:−0.062985525 |
| 53:0.11422034 54:−0.00019600346 55:0.20905067 56:0.11345094 57:0.18042772 58:0.18654525 |
| 59:−0.13657875 60:0.16028108 61:0.042597752 62:−0.16648717 63:0.020041479 64:0.098276176 |
| 65:0.042147629 66:−0.11807261 67:−0.021237738 68:0.10123348 69:0.068163715 70:0.24706022 |
| 71:−0.0055927006 72:−0.091392614 73:−0.085621513 74:0.026716059 75:−0.0524523 |
| 76:−0.0082009388 77:−0.080118604 78:0.024665469 79:−0.018244687 80:−0.10774477 81:0.06556277 |
| 82:0.25329241 # |
| 0.014371081791088378 1:−3.8009903 2:−3.712745 3:0.035972014 4:−0.29274768 5:0.30894205 |
| 6:−0.051934857 7:1.3533156 8:−0.30238849 9:2.1054666 10:−1.0627549 11:1.07925 12:0.033111423 |
| 13:−0.025141882 14:−0.15083164 15:−0.13110662 16:0.46184546 17:−0.26736799 18:−0.098167084 |
| 19:0.012707644 20:−0.74169838 21:0.24415287 22:0.29223081 23:0.44178495 24:−0.15242128 |
| 25:−0.53285432 26:−0.27422145 27:0.0088788997 28:−0.25391474 29:−0.53365928 30:−0.46449012 |
| 31:−0.54598719 32:−0.42985302 33:0.076727137 34:0.25129828 35:0.14773342 36:−0.25915271 |
| 37:0.49318647 38:−0.23454799 39:−0.22261906 40:−0.18280679 41:−0.16568577 42:−0.019092988 |
| 43:0.28418142 44:−0.19112669 45:−0.073105901 46:−0.20049676 47:−0.033859272 |
| 48:−0.095328569 49:−0.17620195 50:0.06332536 51:−0.12334346 52:0.10732521 53:0.012209306 |
| 54:−0.093764633 55:−0.024187654 56:−0.11709578 57:−0.13697803 58:−0.092686981 59:0.11749276 |
| 60:−0.21411923 61:0.026352197 62:−0.054685757 63:0.082908273 64:0.016426267 |
| 65:−0.0075805415 66:0.13098004 67:0.035055134 68:0.10365851 69:0.078652427 70:−0.0025166064 |
| 71:−0.0088681933 72:0.026783306 73:−0.053607099 74:0.037180062 75:−0.060114242 |
| 76:0.041664574 77:0.051833551 78:0.05481777 79:−0.027881617 80:−0.0030249455 |
| 81:0.034290392 82:0.25329241 # |
| −0.014371081791088378 1:−5.6870971 2:−3.8633118 3:0.5502708 4:3.2217255 5:−0.78175759 |
| 6:7.6200829 7:−1.6317638 8:1.3913993 9:−1.5253075 10:−1.6085379 11:−0.29080987 |
| 12:−2.3878469 13:1.3862033 14:−0.67028159 15:1.1507096 16:−2.1945915 17:0.3283675 |
| 18:0.93808556 19:−1.4475281 20:0.71833432 21:−0.58230352 22:1.1630721 23:0.96855032 |
| 24:0.84522974 25:0.2488184 26:0.33633187 27:0.36562845 28:0.062045995 29:0.070227616 |
| 30:0.34514588 31:−0.8193208 32:0.596057 33:0.096730314 34:0.0036321157 35:−0.87291569 |
| 36:0.36554244 37:−0.35814509 38:0.60456467 39:−0.30750424 40:−0.2449463 41:0.21808925 |
| 42:−0.012626919 43:−0.25464663 44:0.26890334 45:−0.39484441 46:−0.32938027 47:0.16226266 |
| 48:0.11844889 49:−0.17337257 50:−0.031896431 51:−0.26933131 52:0.018946234 53:−0.27470267 |
| 54:0.022666637 55:0.2171565 56:0.07139264 57:−0.00057589676 58:0.094515152 |
| 59:0.099881791 60:−0.054072827 61:−0.090190567 62:0.075763471 63:−0.064131543 |
| 64:−0.050282713 65:0.075506695 66:0.001712936 67:0.13952082 68:0.073892675 69:0.061752494 |
| 70:0.034252256 71:−0.0087319519 72:−0.013301839 73:0.027320119 74:−0.031841647 |
| 75:−0.068410456 76:0.044859413 77:0.00037850515 78:−0.0183778 79:0.0047583864 80:0.037245952 |
| 81:−0.034871854 82:0.25329241 # |
| −0.014371081791088378 1:−3.5434668 2:−3.1934402 3:1.063877 4:−1.6397682 5:2.7323604 |
| 6:−0.35087371 7:2.5169282 8:−0.14428514 9:−0.072467037 10:0.76018471 11:−1.2748876 |
| 12:0.18729535 13:0.009676869 14:−0.62244159 15:−1.1017917 16:0.90493476 17:−0.43650272 |
| 18:−0.28636745 19:−1.1385707 20:0.035441749 21:−0.63875026 22:−0.35696188 23:0.76036102 |
| 24:−0.18247259 25:−0.32365471 26:−0.76277816 27:−0.019070659 28:−0.39289239 29:0.033597656 |
| 30:−0.0502593 31:−0.18443197 32:0.077162221 33:0.39236328 34:0.54777235 35:0.089053363 |
| 36:−0.16615406 37:−0.27837387 38:−0.095668189 39:−0.38135219 40:0.014063733 41:0.38594639 |
| 42:−0.012612532 43:−0.21282899 44:0.059666738 45:0.460518 46:−0.23913723 47:0.021162152 |
| 48:−0.053106524 49:0.013263262 50:−0.26919654 51:0.35722664 52:−0.33070409 |
| 53:−0.049044874 54:−0.11497188 55:0.2477473 56:−0.14363593 57:−0.31514663 58:−0.012106147 |
| 59:−0.15271853 60:−0.015632421 61:−0.2432075 62:0.0059246742 63:0.092618003 64:0.022069488 |
| 65:0.062213317 66:−0.049550116 67:−0.15363108 68:0.0012269747 69:−0.0176946 |
| 70:−0.00041702227 71:−0.1008773 72:0.041230172 73:0.09954042 74:−0.034144524 75:−0.011634476 |
| 76:0.037617467 77:−0.10289951 78:0.0057351305 79:0.03597641 80:−0.0019008811 |
| 81:0.0065082707 82:0.25329241 # |
| 0.014371081791088378 1:−2.8528001 2:1.0200286 3:3.4109762 4:3.3333311 5:1.0811552 |
| 6:−0.90926313 7:−0.066572592 8:−0.078273267 9:−0.69617331 10:0.90766191 11:0.22328934 |
| 12:0.020680832 13:0.69335735 14:−0.23330054 15:0.16490267 16:−0.51006645 17:−0.036910553 |
| 18:0.86227834 19:−1.6823598 20:0.57845354 21:−0.042305458 22:0.13733156 23:−0.30985823 |
| 24:−0.3465707 25:−0.07561028 26:0.21634971 27:0.55721086 28:0.36036351 29:0.2500689 |
| 30:−0.51939505 31:−0.034316037 32:−0.31952652 33:−0.21510515 34:−0.098683521 35:0.03388213 |
| 36:0.070551232 37:0.42654166 38:0.032890543 39:0.040162489 40:0.07311783 |
| 41:−0.0093292985 42:0.17319316 43:0.01131756 44:−0.18613157 45:0.36358306 46:0.02252809 |
| 47:−0.18621118 48:−0.087856874 49:−0.19327007 50:−0.019877661 51:−0.14151971 52:0.14031564 |
| 53:0.079054043 54:−0.066365227 55:−0.068676084 56:0.1675217 57:−0.068346232 |
| 58:0.037199736 59:−0.088745952 60:−0.19727731 61:−0.1115559 62:−0.1711906 63:−0.045923334 |
| 64:0.06122876 65:−0.05049203 66:0.11534942 67:0.063185915 68:0.092893109 69:−0.2434848 |
| 70:−0.15058945 71:−0.013301116 72:0.018010281 73:0.013190226 74:−0.018021589 |
| 75:−0.09148033 76:−0.0049685887 77:−0.0024031231 78:−0.058593303 79:−0.050791197 |
| 80:−0.034712054 81:0.015786134 82:0.25329241 # |
| −0.014371081791088378 1:−3.2634594 2:−5.0213122 3:1.9020625 4:1.7079902 5:0.97207415 |

APPENDIX C10-continued

| SVM Model Weights (82; Normal/Diseased) |
|---|
| 6:3.8924689 7:−2.5940638 8:−0.70774519 9:−0.25629976 10:0.81892556 11:0.38619879 12:−0.15325919 13:−0.074360669 14:−0.39633775 15:0.78593242 16:−1.3330709 17:1.2396652 18:−0.21575621 19:0.2125102 20:−0.51848459 21:0.59641975 22:0.42528111 23:0.31153455 24:0.58852816 25:−0.27147868 26:0.70595235 27:0.56736892 28:−0.11742917 29:−0.37774593 30:0.35657141 31:0.15097851 32:−0.52336407 33:−0.5170837 34:−0.2214773 35:0.70922124 36:−0.24117717 37:−0.32067811 38:0.2037853 39:0.048133839 40:−0.28065404 41:0.014471174 42:0.32584718 43:−0.18879434 44:−0.12287803 45:0.042606592 46:−0.050198268 47:0.15698735 48:−0.24888973 49:−0.28695926 50:−0.093139835 51:−0.031743858 52:−0.038437013 53:−0.030304886 54:−0.1663989 55:−0.070192777 56:−0.036103643 57:−0.2458805 58:−0.20082615 59:−0.12449863 60:0.082503043 61:0.23670565 62:0.070099197 63:−0.14095411 64:0.28306434 65:0.10236634 66:0.058942951 67:−0.12078229 68:−0.10195816 69:−0.25820881 70:0.16092059 71:−0.0017915048 72:−0.017487062 73:−0.026134707 74:0.06684906 75:0.032874446 76:−0.068502083 77:−0.0026230318 78:0.058820307 79:0.019293908 80:−0.071163058 81:−0.0049694078 82:0.25329241 # |
| 0.014371081791088378 1:−5.2983923 2:4.6186671 3:0.32040823 4:−0.85480094 5:2.3312964 6:0.21440503 7:0.32360309 8:2.3184035 9:1.2571456 10:−1.218997 11:1.934774 12:0.19233947 13:0.41002691 14:−1.169475 15:−0.21663104 16:−0.35222641 17:−0.88321835 18:−0.4160383 19:−0.72724265 20:0.12944403 21:0.5905863 22:−0.18882026 23:−0.9451372 24:−0.25931895 25:−0.48865369 26:0.35786819 27:0.81933069 28:−0.13143569 29:−0.017690632 30:−0.36567909 31:−0.3938787 32:−0.48210523 33:0.21408096 34:0.05016081 35:−0.31452391 36:0.18297358 37:0.0036423032 38:0.24831475 39:−0.10269532 40:0.17264152 41:−0.15684274 42:−0.13049379 43:−0.39119583 44:−0.28301951 45:0.16169156 46:−0.10612797 47:0.0010680594 48:−0.02018475 49:0.072016209 50:0.028930346 51:0.37138739 52:−0.28711724 53:0.19583331 54:0.078421444 55:0.098418333 56:0.068729691 57:0.21777299 58:0.22816817 59:−0.07177116 60:0.10912821 61:−0.069120266 62:0.043012902 63:0.058935553 64:−0.029425716 65:−0.13223951 66:0.029221667 67:0.0042196959 68:0.011744753 69:−0.0075895409 70:−0.024904374 71:0.046353363 72:0.14024784 73:0.01882888 74:0.0018848602 75:0.042022321 76:0.015587076 77:−0.046860471 78:0.089595802 79:0.020865589 80:−0.030778017 81:−0.030822437 82:0.25329241 # |
| 0.014371081791088378 1:−0.24722062 2:1.021608 3:1.5501559 4:3.2902031 5:−0.49222863 6:−1.9560024 7:−0.92939031 8:1.4876535 9:1.0370933 10:−0.36374095 11:−0.4861829 12:0.1032975 13:0.528579 14:−0.96912348 15:−0.23487149 16:−0.83355951 17:−0.387339 18:−0.58359802 19:0.21712805 20:0.38237441 21:0.09947791 22:−0.16424721 23:0.35367629 24:0.084093593 25:0.12899007 26:0.45458376 27:−0.34916359 28:0.35748491 29:−0.43494329 30:−0.10152685 31:−0.34019619 32:0.34502137 33:0.10305439 34:−0.016456453 35:−0.18658113 36:−0.23528469 37:0.10276341 38:0.33133993 39:−0.011614426 40:0.20836087 41:−0.012584786 42:−0.42018011 43:0.095638655 44:−0.0085080154 45:0.33823514 46:0.13128404 47:−0.018268339 48:−0.33195341 49:0.26194677 50:−0.026845433 51:0.069850951 52:−0.26760072 53:−0.19235161 54:−0.095196679 55:0.050548993 56:−0.29852253 57:0.11790613 58:0.14210743 59:−0.18985862 60:−0.23244654 61:−0.048005931 62:−0.019129382 63:−0.14945954 64:−0.077993378 65:0.048314512 66:0.021168858 67:0.042940009 68:−0.2197926 69:−0.0098903598 70:−0.010487368 71:−0.085927643 72:−0.087017842 73:0.017524334 74:0.050407231 75:0.043739706 76:−0.062575437 77:0.039350938 78:0.044338919 79:0.008738325 80:−0.043556225 81:−0.018409744 82:0.25329241 # |
| 0.014371081791088378 1:−0.24006036 2:1.2987419 3:1.3847564 4:0.97640204 5:0.46242422 6:−1.5046915 7:−1.0122844 8:−1.102639 9:1.3300987 10:−0.34568265 11:2.1003592 12:−0.11675802 13:−0.46899459 14:0.19244784 15:0.07685405 16:0.71301258 17:−0.63476497 18:0.38921136 19:−0.023635989 20:−0.64281601 21:−0.016276253 22:0.12397807 23:0.3101885 24:0.3401413 25:0.54301238 26:−0.32616353 27:−0.083738521 28:−0.0084973574 29:−0.73669964 30:−0.33580789 31:−0.53309637 32:0.012451741 33:−0.081417225 34:−0.52033496 35:0.027060391 36:0.31348398 37:0.048283663 38:0.20261776 39:−0.13500793 40:0.38858005 41:−0.0040374761 42:−0.093377456 43:0.099225268 44:0.27533141 45:−0.012928622 46:−0.12362498 47:−0.010367705 48:0.065071747 49:−0.24295954 50:−0.061973441 51:0.09964066 52:0.24756482 53:0.19689161 54:−0.14599808 55:0.16532803 56:0.0015929472 57:0.20683303 58:0.033291202 59:−0.036692645 60:−0.091093637 61:0.21312402 62:0.20616214 63:0.084026352 64:−0.045431811 65:−0.035906781 66:−0.046873961 67:−0.14025684 68:0.17433511 69:−0.22525661 70:−0.086938269 71:0.080348141 72:0.0062055024 73:−0.078187622 74:−0.1589289 75:0.0075107603 76:−0.041517355 77:−0.00070993445 78:−0.02639441 79:0.062034179 80:0.083361171 81:0.014046115 82:0.25329241 # |
| −0.014371081791088378 1:0.93071336 2:0.25796089 3:1.5878607 4:1.6732655 5:1.4052185 6:−0.65342021 7:2.1494508 8:1.0677431 9:1.4429301 10:−1.3129328 11:2.4255221 12:0.97526366 13:−1.2684118 14:−1.0568238 15:1.1750267 16:−0.47596914 17:−0.075968221 18:0.85617268 19:0.82672971 20:−0.42792845 21:−0.00025690225 22:−0.71902186 23:0.65715361 24:−0.1163074 25:0.083939068 26:1.0107378 27:−0.18176933 28:0.67247927 29:−0.40131259 30:0.49951798 31:0.36349186 32:−0.038894281 33:−0.049246512 34:−0.41141742 35:0.015810994 36:−0.26397026 37:0.19000803 38:−0.35271525 39:−0.26594201 40:−0.098627262 41:0.66702807 42:−0.048650097 43:−0.11134079 44:−0.3120937 45:0.065067329 46:0.28272298 47:0.091944821 48:0.19418879 49:−0.2628434 50:−0.041713528 51:−0.027868813 52:−0.16760296 53:−0.20598158 54:0.031317752 55:−0.0017733488 56:−0.16556241 57:0.21156561 58:−0.10237342 59:0.029394116 60:0.30294427 61:−0.0052800835 62:−0.073022515 63:−0.0037743894 64:0.10853308 65:−0.19614968 66:0.028645262 67:−0.079191186 68:−0.00097313762 69:0.13494968 70:−0.049570885 71:−0.048664529 72:−0.12627561 73:0.027650231 74:0.035301235 75:−0.077467248 76:−0.038830537 77:−0.054935161 78:−0.012568251 79:0.062212598 80:0.056865722 81:0.00056475936 82:0.25329241 # |
| −0.014371081791088378 1:3.7863922 2:0.66319549 3:1.3860481 4:1.8325212 5:1.5193493 6:−0.68611771 7:−0.72895217 8:−1.3048335 9:−0.11339167 10:0.077651016 11:1.2147416 12:−1.2399189 13:−0.78615898 14:0.34963882 15:−1.164503 16:0.0087263603 17:−0.38142896 |

APPENDIX C10-continued

| SVM Model Weights (82; Normal/Diseased) |
|---|
| 18:1.3150532 19:−0.82910264 20:0.010550016 21:−0.87727344 22:0.047165852 23:−0.2765846 24:−0.87827247 25:0.51746887 26:0.078066781 27:−0.020991212 28:0.12256682 29:0.060843956 30:0.47947761 31:−0.32846221 32:−0.32975331 33:0.071028918 34:0.27401778 35:−0.032070786 36:0.36200655 37:0.72460943 38:0.0027375529 39:−0.12004218 40:0.56851399 41:0.062307909 42:−0.13800503 43:−0.17798422 44:−0.64196491 45:−0.028743492 46:0.15735579 47:0.032729186 48:0.021045268 49:−0.017215909 50:−0.23906985 51:−0.054384645 52:−0.11240782 53:0.053792801 54:−0.12050851 55:0.042202506 56:−0.23140216 57:−0.21024653 58:0.13245463 59:0.35426146 60:−0.036642741 61:0.071249686 62:−0.041649621 63:−0.0075351642 64:−0.039503351 65:0.07450977 66:0.020409836 67:0.0056895884 68:−0.087321058 69:−0.012613475 70:0.13160089 71:0.024951065 72:−0.040102389 73:−0.18910305 74:0.095829375 75:0.0063762935 76:0.047007602 77:0.11354433 78:−0.068469882 79:0.091735877 80:0.0014397945 81:−0.033435855 82:0.25329241 # |
| −0.0085281134994479035 1:3.9302077 2:2.9690502 3:−0.3668285 4:0.083044372 5:0.061366528 6:−1.456148 7:1.4005681 8:−2.0769053 9:−0.83422083 10:0.12414838 11:−0.28980708 12:−0.3149552 13:−1.335645 14:0.32743561 15:−0.7778517 16:−0.87359035 17:0.5611335 18:0.49952477 19:−0.2653015 20:0.57363564 21:0.63289952 22:0.29973975 23:1.4165958 24:0.47083759 25:0.50855809 26:0.045122672 27:−0.016947806 28:−0.46374902 29:−0.1263701 30:0.58436489 31:−0.28844664 32:0.28629345 33:−0.36837327 34:0.67685032 35:−0.091536388 36:0.28573895 37:−0.52166951 38:−0.25795138 39:0.19390035 40:0.26024377 41:0.31076005 42:−0.04231156 43:0.15080294 44:−0.10906595 45:0.019748179 46:−0.22087131 47:0.17843133 48:−0.11574392 49:0.47414023 50:0.039467689 51:0.16545571 52:0.13681169 53:0.34379753 54:0.13126323 55:−0.039907183 56:−0.11707788 57:−0.10863321 58:0.10702937 59:0.080011643 60:0.081400953 61:−0.0096556209 62:0.12347572 63:−0.11967333 64:0.095572226 65:−0.11134003 66:−0.0051062908 67:−0.050637148 68:−0.00075069617 69:0.039818965 70:−0.092754774 71:0.023076879 72:−0.05059433 73:−0.02042052 74:−0.094831832 75:0.033265751 76:0.037393827 77:−0.043768842 78:0.077458456 79:−0.01043008 80:0.0085707894 81:−0.021156481 82:0.25329241 # |
| 0.013771216502228904 1:−5.6553664 2:−3.7415822 3:1.886261 4:−0.75849944 5:4.9463425 6:8.1314068 7:−2.1414881 8:−3.1854358 9:−1.700667 10:−2.459758 11:−0.057135232 12:−1.4052527 13:2.0007102 14:−0.13673449 15:0.31861341 16:0.0071324613 17:−1.185956 18:0.28442001 19:0.29326087 20:−0.256681 21:0.93093979 22:−0.30115369 23:−0.16750212 24:−0.13148315 25:−0.67614365 26:−0.13445561 27:0.22285883 28:0.21142063 29:−0.47532123 30:−0.1245566 31:0.25720379 32:0.81621158 33:0.13022262 34:0.0064217304 35:0.41881406 36:−0.50353456 37:−0.26708892 38:−0.23285171 39:−0.025173008 40:0.62062681 41:−0.22625732 42:0.50239623 43:0.18009084 44:−0.0061095674 45:−0.0025227969 46:−0.025823858 47:−0.2923795 48:0.09713126 49:−0.18363987 50:0.27773163 51:0.15734918 52:−0.058510266 53:−0.014603482 54:0.086676836 55:0.22794923 56:−0.057332981 57:0.15132058 58:−0.0031526228 59:−0.022694873 60:−0.19629519 61:0.10944411 62:−0.10287096 63:0.092859678 64:−0.16171014 65:−0.070101596 66:0.077352896 67:−0.16233787 68:−0.064663351 69:0.065016247 70:−0.097760133 71:−0.049562223 72:0.04393721 73:−0.029695369 74:0.041346569 75:−0.063791782 76:−0.01250024 77:0.011236841 78:−0.017093761 79:0.059222452 80:−0.02638761 81:0.0037533157 82:0.25329241 # |
| 0.01437108179l088378 1:−0.33105719 2:−2.6650863 3:0.99426222 4:1.1767578 5:2.0480959 6:3.2963808 7:−0.87305534 8:−1.5969872 9:−0.34631911 10:1.2152302 11:1.0833389 12:−1.2164828 13:−1.8733256 14:−0.10324189 15:−0.78252494 16:−0.045712411 17:0.35618326 18:−0.67688125 19:0.14490172 20:−0.30649906 21:−0.64697838 22:0.056471251 23:−0.22695646 24:0.42867228 25:−0.051198941 26:0.22824669 27:0.69632101 28:0.093061544 29:−0.084686242 30:−0.48359695 31:0.041666448 32:−0.23258643 33:0.034102205 34:−0.28167668 35:0.84035516 36:0.33780119 37:0.065529823 38:0.11440316 39:−0.51977485 40:−0.054946475 41:0.25532919 42:−0.31202087 43:0.13850679 44:0.20354114 45:−0.19949935 46:−0.2295607 47:−0.067834862 48:−0.10886261 49:0.091546446 50:−0.24904199 51:−0.1166163 52:−0.11864711 53:0.21401004 54:0.39432833 55:0.018828705 56:−0.29762065 57:−0.1065848 58:−0.15671715 59:−0.061372112 60:0.083340473 61:−0.081413165 62:0.064286545 63:−0.11562716 64:−0.0036586761 65:0.067578174 66:5.0753319e−005 67:−0.071959965 68:−0.0091415988 69:0.021394027 70:−0.022879208 71:0.023791276 72:0.16370761 73:0.011479094 74:−0.043475218 75:0.052193675 76:0.036188111 77:−0.01212345 78:−0.0060516056 79:0.10634781 80:−0.019956317 81:−0.015404238 82:0.25329241 # |
| −0.014371081791088378 1:−7.589458 2:−1.3411139 3:0.086163498 4:0.39717948 5:0.26949018 6:0.64076924 7:0.87279654 8:1.5715289 9:1.6310817 10:0.76806736 11:0.96146107 12:2.1062965 13:0.69298291 14:−0.43221003 15:−0.52149051 16:−0.2687197 17:−0.12473437 18:−0.73030311 19:−0.57674229 20:0.0040965239 21:0.20310938 22:0.63035458 23:0.56569672 24:−0.451307 25:0.019065307 26:0.50202614 27:−0.091599323 28:0.39082119 29:−0.36614007 30:−0.057842504 31:−0.41896448 32:−0.44279677 33:0.29672346 34:0.019739551 35:0.23004217 36:−0.032822952 37:−0.013011935 38:0.065466024 39:−0.053251248 40:0.055746015 41:0.088243581 42:0.23047946 43:−0.095380485 44:−0.35992533 45:−0.17402458 46:0.11911383 47:−0.04672429 48:−0.17038393 49:0.19919606 50:−0.050675761 51:0.015174688 52:−0.16853875 53:0.27063078 54:0.086994357 55:0.11011154 56:0.1119871 57:0.026199693 58:−0.070133924 59:−0.019465908 60:−0.046306171 61:−0.021892572 62:−0.26800495 63:−0.021744302 64:0.018939083 65:0.15363991 66:−0.0082030799 67:0.16367571 68:0.13993712 69:−0.047283798 70:0.048063178 71:−0.081182145 72:−0.035025347 73:−0.017831862 74:−0.07894478 75:−0.037059117 76:−0.070370384 77:−0.0055711675 78:−0.051374152 79:−0.090574555 80:0.014027417 81:−0.0048481328 82:0.25329241 # |
| −0.014371081791088378 1:−6.0060444 2:−0.19980124 3:1.1959471 4:0.26226512 5:−0.0030859362 6:−1.3043574 7:−1.1903094 8:−1.8057019 9:−1.2297759 10:0.72306752 11:−0.56693953 12:1.1138197 13:0.59304643 14:−0.089964397 15:0.23340377 16:−0.18416882 17:0.14068964 18:−0.90192533 19:0.206176 20:0.11493195 21:−0.57975084 22:0.68767858 23:0.22503585 24:−0.02321627 25:0.53108859 26:0.071912132 27:0.47262487 28:0.42929879 29:0.31673509 |

APPENDIX C10-continued

| SVM Model Weights (82; Normal/Diseased) |
|---|
| 30:−0.071964651 31:0.41331834 32:0.18550907 33:−0.025432391 34:−0.054851852 35:0.045877971 36:0.11350977 37:−0.11488757 38:−0.24813743 39:−0.32373527 40:0.19036114 41:−0.15808345 42:0.044606976 43:−0.044148028 44:0.00024701361 45:−0.25318947 46:0.073976532 47:0.29763213 48:0.10764767 49:0.27654451 50:0.3704831 51:−0.13158143 52:−0.15525711 53:−0.23933831 54:0.097839303 55:0.086061373 56:−0.072859228 57:−0.082069971 58:0.027189957 59:−0.003003682 60:0.0177978 61:−0.18255159 62:0.042090308 63:−0.061958861 64:0.013443044 65:−0.044643857 66:−0.071160354 67:0.02483674 68:0.065339498 69:−0.025357882 70:0.019737197 71:−0.091961451 72:−0.039262749 73:−0.030747605 74:−0.039356671 75:0.040748172 76:−0.082341552 77:0.10567741 78:0.074384764 79:0.052057836 80:−0.016411221 81:0.012312029 82:0.25329241 # |
| 0.014371081791088378 1:5.4940791 2:−0.85364658 3:2.336175 4:1.5782386 5:1.9727908 6:−1.4011421 7:1.7937381 8:0.9656086 9:−0.9443633 10:−0.55620784 11:−1.4247454 12:−0.28747544 13:0.76858479 14:2.5772064 15:−0.90391368 16:−0.27281693 17:1.0934781 18:0.74998313 19:0.75000507 20:0.18189369 21:−0.6769172 22:0.89265847 23:−0.57212096 24:0.07335937 25:−1.1337161 26:1.1457827 27:0.084534772 28:0.31174129 29:−0.97406167 30:−0.29106101 31:−0.16810438 32:0.29329383 33:−0.55956566 34:0.35723925 35:−0.36258745 36:0.48933762 37:0.1681111 38:0.42217499 39:0.16908439 40:0.39814988 41:0.48942387 42:−0.21556474 43:−0.19726108 44:0.26855129 45:0.15114452 46:−0.27603841 47:0.12405454 48:0.22485404 49:−0.24237101 50:0.23580043 51:0.29816079 52:−0.17535585 53:0.0056593996 54:−0.079239421 55:0.058914881 56:0.29799297 57:−0.14404254 58:0.018898854 59:−0.0083813528 60:0.046925627 61:−0.008466756 62:−0.0097630052 63:−0.05389474 64:0.055569451 65:0.12939659 66:0.1504513 67:0.056953579 68:0.068155617 69:−0.0066341194 70:−0.032909311 71:0.031892523 72:0.0060809553 73:0.018820964 74:0.12340568 75:0.093844615 76:0.026946627 77:−0.018794058 78:−0.031279027 79:0.012281653 80:−0.00088746304 81:0.051837441 82:0.25329241 # |
| 0.014371081791088378 1:1.185019 2:2.1902387 3:1.0453033 4:3.9202256 5:−0.6040588 6:−0.18307683 7:0.10143254 8:1.1900427 9:0.33155039 10:0.27479821 11:−0.25718796 12:−0.084739693 13:−0.2313996 14:0.79425991 15:−0.59067237 16:−0.58661538 17:−0.36386985 18:1.5204959 19:−0.0069870381 20:−0.76155502 21:−0.17894091 22:1.1256846 23:0.75592905 24:−0.5453431 25:0.058894824 26:0.0031735643 27:−0.80928463 28:−0.096643738 29:0.28834152 30:−0.55305308 31:−0.22774118 32:−0.25720027 33:0.26552722 34:−0.034625527 35:0.15176201 36:0.14492092 37:−0.042334002 38:−0.052873202 39:−0.19578862 40:0.038178496 41:0.15686074 42:0.30073029 43:0.28040284 44:0.094269447 45:−0.049678084 46:−0.32769161 47:−0.13634787 48:−0.059951399 49:0.017142247 50:−0.065991551 51:0.12180275 52:−0.021997515 53:0.075566128 54:−0.10983963 55:0.16031726 56:−0.19199076 57:0.28763849 58:−0.053302854 59:−0.09107317 60:0.1452786 61:−0.1154953 62:0.097272262 63:−0.059752725 64:−0.0015569539 65:−0.15728714 66:0.14467762 67:−0.016847927 68:−0.11047788 69:0.11981525 70:0.063133284 71:0.11987154 72:−0.052880362 73:0.045872442 74:−0.016259374 75:−0.056762427 76:−0.082631156 77:0.10219926 78:−0.032336883 79:0.018344725 80:0.021021402 81:0.0035529283 82:0.25329241 # |
| 0.014371081791088378 1:−0.38630006 2:−1.8006481 3:0.60955268 4:0.91089231 5:−0.43602678 6:−0.99246675 7:0.28624627 8:−0.40677938 9:0.2095155 10:−0.58778411 11:−0.9828608 12:0.44003859 13:−0.50291401 14:0.090660505 15:−0.71692938 16:−0.18350209 17:−1.4307336 18:−0.54722542 19:0.30411422 20:0.069043539 21:−0.52616191 22:0.11608297 23:0.71036768 24:−0.23542279 25:0.30398631 26:−0.31489393 27:0.00040904712 28:−0.66504103 29:−0.74788278 30:−0.35057646 31:0.018990032 32:0.055832047 33:0.1243569 34:−0.51174098 35:0.030637762 36:0.3785294 37:−0.11768714 38:−0.20610489 39:−0.15566348 40:0.28454918 41:−0.320824 42:−0.30273417 43:−0.085154422 44:0.046957672 45:−0.19310521 46:−0.05736329 47:−0.30603343 48:−0.14447299 49:0.1030443 50:0.071294263 51:0.11479841 52:−0.026447037 53:−0.18013929 54:0.052149501 55:−0.20705734 56:0.13545978 57:−0.12867589 58:−0.037053749 59:0.037554447 60:0.04825639 61:−0.15420838 62:0.15911366 63:0.069692515 64:−0.18353136 65:0.059781238 66:−0.053167932 67:0.00030385124 68:0.060133442 69:0.013954473 70:−0.096828125 71:0.018247738 72:−0.18578175 73:−0.10711753 74:−0.023155756 75:0.017616699 76:0.00059520453 77:0.046367254 78:−0.0091739288 79:−0.015368443 80:−0.034211561 81:−0.020202376 82:0.25329241 # |
| −0.0024023167320973114 1:3.5514643 2:−0.80591679 3:−0.76087856 4:1.3388174 5:−1.0576854 6:−4.231174 7:0.5487839 8:−0.19942884 9:−2.3506091 10:1.4028975 11:0.020640725 12:−2.3183215 13:0.18694052 14:−0.51539564 15:−0.053429484 16:−0.66072494 17:−0.78368461 18:−0.71222562 19:0.68741179 20:0.53828311 21:0.307322 22:−0.47074169 23:−0.66754222 24:0.17080431 25:0.30543944 26:0.81343883 27:−0.3450183 28:−0.58456844 29:−0.43099189 30:−0.53545105 31:−0.14462677 32:0.75727379 33:−0.41741154 34:−0.28289309 35:0.5305137 36:0.26783296 37:0.34580052 38:−0.041660309 39:−0.40001264 40:−0.14083479 41:0.12103543 42:0.30152544 43:−0.019901171 44:−0.13543169 45:−0.47610357 46:−0.043992501 47:0.14654323 48:−0.0430401 49:−0.1256963 50:−0.16491956 51:−0.2499916 52:−0.15961339 53:−0.20364854 54:0.014457815 55:0.10814077 56:0.062771849 57:−0.13241605 58:−0.018527394 59:0.070952684 60:0.12224351 61:−0.1695568 62:−0.040436968 63:−0.021974457 64:−0.047000673 65:−0.010486727 66:−0.017547689 67:0.033521861 68:−0.14163546 69:−0.032448363 70:−0.1676403 71:0.014629217 72:0.015661072 73:0.050350249 74:0.01500129 75:−0.033859197 76:0.13050522 77:0.0065503558 78:0.093899302 79:−0.032602075 80:−0.055071797 81:0.029641287 82:0.25329241 # |
| −0.014371081791088378 1:5.1095123 2:−2.4761388 3:2.5752778 4:0.059661031 5:0.32248768 6:−2.5309174 7:−1.6645325 8:−0.20479648 9:0.081693351 10:−0.55409986 11:−0.10096719 12:−0.91516399 13:0.27209026 14:0.34063512 15:−0.0031274084 16:0.15395834 17:0.17143552 18:0.22386897 19:−0.902363 20:0.69932628 21:−0.084947661 22:−0.40941343 23:0.12778102 24:0.044231519 25:−0.044283669 26:0.31326804 27:−0.11952202 28:0.70139021 29:−0.0073033138 30:0.027237574 31:0.47829232 32:0.024897277 33:−0.30396476 34:−0.57689291 35:−0.084239855 36:−0.18268502 37:0.38174069 38:−0.14088745 39:0.13941221 40:−0.089080662 |

APPENDIX C10-continued

| SVM Model Weights (82; Normal/Diseased) |
|---|
| 41:−0.25207111 42:0.33853728 43:0.024353011 44:−0.36173511 45:0.54177362 46:−0.21571654 47:0.0016917221 48:0.156738 49:0.19071811 50:0.11758964 51:0.14542854 52:−0.18343793 53:−0.074023858 54:0.045562297 55:0.34281719 56:0.0049857614 57:0.0016132119 58:−0.033560809 59:−0.062579066 60:−0.096484207 61:0.20621368 62:0.16876608 63:0.052898828 64:0.0073956922 65:0.051171381 66:−0.087403953 67:0.14755337 68:−0.034084827 69:0.17398864 70:0.066102423 71:−0.02473628 72:0.042083733 73:0.12303758 74:−0.14842665 75:0.022765962 76:−0.068391897 77:0.017301979 78:−0.026088566 79:−0.012687141 80:−0.0060474086 81:0.016045243 82:0.25329241 # |
| 0.014371081791088378 1:−3.5681252 2:−0.54916602 3:0.81628841 4:1.6673336 5:0.42477477 6:2.1605878 7:1.1556263 8:−2.0018859 9:−2.386224 10:−0.39669135 11:0.023593171 12:−1.8799342 13:−0.6878348 14:0.089146674 15:1.0023392 16:0.23772731 17:0.64889944 18:1.023319 19:−0.49552768 20:−0.13850328 21:−0.64445734 22:0.28276247 23:−0.80878228 24:−1.085646 25:0.69625771 26:−0.35825157 27:0.35963959 28:0.090102591 29:0.47164929 30:0.3734611 31:0.033266015 32:−0.3273668 33:0.3595801 34:−0.5553171 35:0.24587965 36:0.063094027 37:0.15982012 38:0.13838081 39:−0.30710071 40:0.0066439286 41:−0.39193189 42:−0.027455941 43:0.10716059 44:0.087011389 45:0.36844838 46:0.05791508 47:−0.15002903 48:−0.075342238 49:−0.09559802 50:0.19686718 51:0.17379324 52:0.048583902 53:0.036112964 54:−0.022304952 55:0.05002661 56:−0.086880647 57:−0.19211872 58:−0.013721011 59:−0.09687528 60:0.026527267 61:−0.0217 62:0.017723922 63:−0.019391436 64:0.10564248 65:−0.042861681 66:−0.05136342 67:0.029839005 68:−0.098450981 69:0.14347453 70:−0.032051183 71:−0.028175529 72:−0.0023921896 73:−0.014324715 74:−0.060193665 75:−0.0046057799 76:0.012137768 77:0.050583966 78:0.05254348 79:−0.090507828 80:0.057100765 81:−0.0060325088 82:0.25329241 # |
| 0.014371081791088378 1:−3.3881943 2:−3.1668506 3:0.527794 4:0.24149242 5:0.004750743 6:−1.386202 7:1.7419318 8:−0.96224862 9:−0.63633907 10:−0.56107396 11:−0.94390172 12:−0.67597753 13:0.13280298 14:0.54191756 15:−0.030646026 16:0.0018167257 17:0.23198757 18:−0.89275271 19:0.40625209 20:0.27266949 21:0.14335875 22:0.57184035 23:0.68303841 24:−0.23034833 25:−0.14104229 26:−0.43394035 27:0.49066976 28:−0.25545734 29:0.24596576 30:−0.27954617 31:−0.2971085 32:−0.32535896 33:0.42527416 34:−0.47965842 35:0.25562277 36:−0.085593872 37:0.25096431 38:0.16239063 39:0.11214952 40:−0.0084497184 41:0.13490598 42:−0.070323765 43:−0.22421789 44:−0.29533544 45:0.044393152 46:0.10288908 47:−0.075510904 48:0.54546088 49:0.098748706 50:0.17811441 51:−0.25560257 52:−0.26793972 53:−0.14791542 54:−0.16524024 55:0.1203716 56:0.0018212297 57:−0.097199574 58:0.17228779 59:−0.078913286 60:0.16133347 61:−0.031943351 62:−0.005081661 63:0.085454315 64:−0.092681684 65:−0.079952441 66:0.23691352 67:−0.21717541 68:0.075750217 69:−0.094490416 70:−0.059633728 71:−0.00022882567 72:−0.024391744 73:0.074532986 74:−0.050372101 75:0.063384697 76:0.068015404 77:0.073155299 78:−0.004430973 79:0.03836536 80:−0.028315587 81:0.025396785 82:0.25329241 # |
| −0.014371081791088378 1:−8.5246038 2:0.9074679 3:−2.7555718 4:1.5403835 5:−1.8067617 6:3.6070597 7:4.4293327 8:4.4307685 9:1.414203 10:0.5209555 11:−0.78362066 12:0.72324747 13:−0.47343642 14:0.07153856 15:−0.22767411 16:−0.12647142 17:−0.85402316 18:−0.18525343 19:−0.430599 20:0.3738074 21:0.94976586 22:−0.044942535 23:0.57803977 24:0.3697392 25:0.27196908 26:0.23466733 27:−0.0434452 28:0.51486307 29:0.15924601 30:−0.22660583 31:−0.40173823 32:−0.1412705 33:−0.1955653 34:−0.16838753 35:0.72638953 36:0.15417624 37:0.066709116 38:0.40393749 39:0.083203629 40:0.10362241 41:−0.25454813 42:0.20961504 43:−0.14409098 44:−0.023328224 45:0.1657213 46:0.16589102 47:−0.045453433 48:−0.024731101 49:0.17240331 50:0.084457435 51:0.063094415 52:0.23195204 53:−0.17078973 54:−0.10905758 55:−0.10243058 56:0.15977946 57:−0.16790831 58:−0.014362374 59:−0.037493046 60:0.04397824 61:0.069658026 62:0.12357085 63:−0.089721031 64:0.05253401 65:−0.17180762 66:−0.084314272 67:−0.045402661 68:−0.023338184 69:0.054151248 70:−0.066715375 71:0.085866369 72:−0.066137403 73:0.035247758 74:0.0068677729 75:−0.0039487248 76:0.072591804 77:−0.0095591703 78:−0.028299512 79:0.082492538 80:0.014172931 81:0.025822531 82:0.25329241 # |
| −0.014371081791088378 1:−4.2371645 2:1.7374002 3:1.3482993 4:0.71180379 5:0.81615049 6:0.4527123 7:0.45152387 8:−0.80970752 9:−0.60006851 10:−0.55377895 11:−1.6456956 12:0.67270631 13:−0.95607603 14:−0.15722676 15:0.67821246 16:−0.60216576 17:0.046959009 18:−0.32484612 19:0.57572937 20:0.77646405 21:−0.73917431 22:0.51766837 23:−0.14535685 24:−0.13138698 25:0.45721135 26:−0.28648517 27:−0.078699902 28:−0.32577753 29:−0.22121628 30:−0.036188532 31:0.0030110157 32:0.50473005 33:−0.13786721 34:0.086804859 35:−0.23375264 36:0.32682058 37:0.034542538 38:0.20881547 39:0.13696684 40:0.12690262 41:−0.4814513 42:−0.19663344 43:0.32300219 44:−0.19266158 45:0.39886814 46:0.23783877 47:−0.07292036 48:−0.20219803 49:−0.27486116 50:−0.05452951 51:0.061756376 52:0.0085545117 53:0.23623489 54:−0.05499094 55:−0.016136192 56:0.043816701 57:−0.045276355 58:0.24717139 59:0.08585567 60:0.037351333 61:0.027095819 62:−0.13086917 63:−0.0029066552 64:0.19525298 65:0.010392052 66:0.083238035 67:−0.069147311 68:−0.045814961 69:−0.034713838 70:−0.11154228 71:0.030639699 72:−0.0059695845 73:−0.083074063 74:−0.017830916 75:−0.0625245296 76:−0.027969079 77:0.036442418 78:0.05210958 79:0.068601303 80:0.030501585 81:0.036888901 82:0.25329241 # |
| −0.0080037918871916115 1:1.6766474 2:0.45756668 3:−1.4985887 4:2.3855984 5:−1.1036179 6:−0.49273595 7:−0.29302374 8:0.66346633 9:1.9152356 10:0.94522071 11:0.32922864 12:−1.5404371 13:−0.37242171 14:−0.40718827 15:0.21434268 16:0.048315845 17:−0.34184596 18:−0.46805233 19:0.83121926 20:−0.3536022 21:0.79378718 22:0.46028283 23:0.34886634 24:0.40246615 25:0.021495026 26:−0.6959542 27:−0.024956781 28:−0.40436602 29:0.18743458 30:−0.53660572 31:0.15057945 32:0.4539153 33:−0.10880911 34:−0.35643631 35:0.079679951 36:−0.11606438 37:0.31468132 38:−0.10555407 39:−0.17685692 40:0.12124016 41:0.29649201 42:0.14660747 43:0.17971228 44:−0.035159893 45:0.017502384 46:−0.28023472 47:0.16772541 48:−0.02012063 49:−0.20065339 50:0.15412942 51:0.27870384 52:0.1567253 53:0.20654441 |

APPENDIX C10-continued

| SVM Model Weights (82; Normal/Diseased) |
|---|
| 54:0.048161495 55:0.034127269 56:−0.064071693 57:0.14445961 58:0.12986979 59:0.17733227 60:0.028391318 61:−0.12800728 62:−0.016384872 63:0.069354199 64:0.09102124 65:0.23635034 66:0.043592431 67:−0.056930635 68:−0.02151628 69:−0.0016589399 70:−0.040629428 71:−0.058815006 72:0.041844949 73:0.023114428 74:−0.021511167 75:−0.096810117 76:−0.057457149 77:−0.0394537 78:−0.019802228 79:−0.029444 80:0.0034204565 81:0.023696892 82:0.25329241 # |
| 0.014371081791088378 1:−2.2322705 2:0.74181461 3:0.84532404 4:2.5803435 5:−1.1262349 6:−1.2088184 7:0.42223772 8:−0.51363695 9:0.57426703 10:−0.57797384 11:0.064572133 12:−0.42861834 13:0.060570169 14:0.22628218 15:1.2368364 16:−0.11278967 17:−0.40467715 18:0.41756651 19:0.29528514 20:−0.49806568 21:0.59824657 22:−0.18003148 23:0.16111095 24:−0.060067926 25:−0.12523375 26:−0.73377478 27:0.24235617 28:−0.17062862 29:0.30923927 30:−0.13154019 31:−0.07156083 32:−0.058435567 33:0.36122811 34:0.1384677 35:−0.019374989 36:−0.11455721 37:0.87378287 38:0.094738692 39:−0.52949804 40:−0.26436421 41:0.29127905 42:−0.11046177 43:−0.045419961 44:0.24893293 45:0.19640008 46:0.15901937 47:0.067328811 48:−0.2304941 49:0.1957881 50:−0.070094936 51:0.11336564 52:−0.039514013 53:−0.23859742 54:−0.19623412 55:−0.045213986 56:0.20354366 57:−0.16165321 58:0.034334715 59:−0.060162049 60:0.050428573 61:−0.12376691 62:0.075092681 63:0.051058736 64:−0.12927751 65:0.065846413 66:0.18370058 67:0.086476915 68:0.047534175 69:−0.016441995 70:0.023222169 71:0.075991832 72:0.021495489 73:−0.034811907 74:0.10039274 75:0.028248103 76:−0.16436528 77:−0.026183313 78:0.042440012 79:−0.011350903 80:−0.074554428 81:−0.018083826 82:0.25329241 # |
| −0.014371081791088378 1:8.3683205 2:4.6259403 3:1.9140006 4:0.015392498 5:0.57495821 6:−1.7813979 7:−1.5663985 8:−0.77268773 9:−1.4010577 10:−0.1764127 11:2.3337519 12:−0.45155379 13:−0.60601854 14:−0.77628994 15:0.56542647 16:0.58742404 17:−0.73926377 18:−0.091698505 19:−0.31322187 20:0.0056855557 21:−0.23417522 22:0.2823104 23:1.3271514 24:0.5236308 25:−0.53858918 26:0.39212427 27:0.15511134 28:0.16291967 29:0.61137956 30:0.55026132 31:−0.24400783 32:−0.030835217 33:0.14078557 34:−0.66542441 35:−0.1112772 36:0.029874096 37:−0.02279472 38:−0.50287396 39:0.093248621 40:−0.16505408 41:−0.51377225 42:0.47509375 43:0.18164295 44:−0.03962082 45:−0.55845159 46:0.29759082 47:−0.15764906 48:0.2441625 49:−0.19601965 50:−0.07994096 51:0.15711743 52:−0.3463569 53:−0.12437369 54:−0.0089948094 55:−0.10712227 56:0.18035796 57:−0.18139641 58:−0.12614664 59:−0.10864617 60:−0.17479292 61:−0.062321994 62:−0.1139451 63:−0.11535085 64:0.12119568 65:0.10166536 66:0.05661869 67:−0.11948786 68:0.037208691 69:0.14854226 70:−0.086262174 71:0.11862405 72:−0.057957403 73:−0.042318795 74:0.037054107 75:−0.020538874 76:−0.041133996 77:−0.051306974 78:−0.022764111 79:−0.016869515 80:−0.039997876 81:0.028001718 82:0.25329241 # |
| −0.014371081791088378 1:−0.23430242 2:−0.45101142 3:1.0539198 4:1.5549108 5:−0.46208069 6:−2.631983 7:−1.5220255 8:−0.19955496 9:0.77234399 10:0.3942154 11:−0.0072434871 12:−1.538555 13:−0.21327397 14:−0.077078827 15:−0.29067889 16:−0.42706844 17:−0.31102949 18:−0.10136428 19:−0.14569463 20:−0.019246804 21:0.573057 22:−0.26190004 23:0.073557243 24:0.10338195 25:0.47985965 26:−0.081041366 27:−0.31906974 28:−0.40826657 29:−0.1673921 30:0.20444912 31:−0.019879183 32:−0.28789434 33:0.35378161 34:0.48095334 35:−0.49697256 36:−0.31633696 37:−0.068199493 38:0.10295124 39:0.0857476 40:0.10428765 41:−0.28587079 42:−0.077615365 43:0.14860032 44:0.3026914 45:−0.19341877 46:0.11911124 47:0.036496475 48:−0.027814202 49:−0.20068879 50:−0.004379794 51:0.27715033 52:−0.15180981 53:0.1156102 54:0.11292004 55:0.04918376 56:0.22714649 57:0.013093065 58:−0.027531156 59:0.13995156 60:0.19309238 61:0.077233687 62:0.0065496322 63:−0.089581281 64:−0.042374786 65:0.13915572 66:0.16194297 67:−0.09371186 68:−0.064767003 69:−0.022218553 70:0.15238297 71:0.069438443 72:0.011508629 73:−0.075146727 74:−0.0026895758 75:−0.066132218 76:0.02267134 77:0.01532228 78:0.04212895 79:−0.021143641 80:0.012464686 81:−0.012811703 82:0.25329241 # |
| 0.014371081791088378 1:−4.0325742 2:1.8504711 3:0.48906687 4:0.89870805 5:−1.3134961 6:−2.293004 7:0.57011026 8:−1.198624 9:−0.68395478 10:−0.51761723 11:0.68021297 12:−0.17806946 13:−0.23316154 14:0.19015592 15:0.80817044 16:−0.23277596 17:0.092033677 18:0.015895482 19:−0.005160233 20:−0.56173581 21:0.40119252 22:−0.6079855 23:−0.40683448 24:0.50341117 25:−0.33685583 26:−0.54430878 27:0.2435935 28:−0.54935205 29:−0.30005914 30:0.12744683 31:−0.23013848 32:0.06308569 33:0.32889959 34:0.25243089 35:0.47687492 36:−0.089121684 37:0.42693794 38:0.11594587 39:0.0047115204 40:−0.48584211 41:0.12488224 42:−0.20760028 43:−0.25606221 44:0.19113761 45:−0.046437375 46:0.061192121 47:0.16105816 48:−0.079605639 49:0.028356401 50:0.083020404 51:0.021485722 52:0.07922326 53:−0.0025215533 54:0.13496411 55:0.0053077522 56:−0.055819567 57:−0.042264584 58:−0.083478808 59:−0.013632423 60:0.10095557 61:0.06671226 62:0.061676014 63:0.07211969 64:−0.091592051 65:−0.038746938 66:0.10339088 67:0.063236684 68:−0.13129975 69:0.031576373 70:0.044604562 71:−0.032479197 72:0.0042029591 73:0.065466404 74:−0.077217028 75:−0.019089345 76:−0.075796142 77:0.039981309 78:−0.077513561 79:0.058981717 80:0.018206874 81:−0.029647503 82:0.25329241 # |
| −0.014371081791088378 1:−2.8981442 2:−0.6212002 3:1.7078279 4:−0.33196875 5:0.5989573 6:−2.8596346 7:1.5315436 8:−2.0105133 9:−1.4254268 10:−0.63541001 11:0.3005468 12:0.48102951 13:−0.61673254 14:−0.24671869 15:−0.41754958 16:−0.43830523 17:0.073965512 18:−0.19417059 19:−1.1972581 20:−0.33855054 21:0.56400204 22:−0.40437153 23:−0.026458969 24:−0.15247945 25:−0.066467531 26:0.24253429 27:−0.49859995 28:0.39888442 29:−0.48676011 30:0.13936524 31:0.1989423 32:0.12716278 33:−0.08278773 34:0.30841479 35:−0.066056773 36:0.15126064 37:−0.13456585 38:0.098305985 39:−0.6951772 40:−0.050344191 41:−0.26637584 42:−0.044020362 43:0.16816528 44:−0.031940237 45:0.23994687 46:0.0065711122 47:−0.29748967 48:0.1485505 49:0.070860408 50:0.24053638 51:−0.07989303 52:−0.05722056 53:−0.021423893 54:−0.027593307 55:−0.12468952 56:0.09480501 57:−0.18684584 58:0.035493899 59:0.2241869 60:0.034441318 61:−0.0067434851 62:0.22559185 63:0.038438529 64:0.1684932 65:−0.094352365 66:−0.0090871044 67:0.047666479 68:0.010674056 69:0.15723762 70:−0.063844085 |

APPENDIX C10-continued

| SVM Model Weights (82; Normal/Diseased) |
|---|
| 71:0.029393764 72:0.10231032 73:0.03880693 74:0.036908031 75:0.067678422 76:0.020666204 77:0.037337776 78:−0.038556647 79:0.015375296 80:−0.070716277 81:0.01984572 82:0.25329241 # |
| 0.014371081791088378 1:−1.4334817 2:0.90635735 3:2.1941264 4:3.1292043 5:0.26899421 6:−1.5484147 7:−0.93183094 8:0.65979451 9:0.86501998 10:0.69524258 11:−0.0033796795 12:−0.55779296 13:0.083482578 14:0.082041077 15:1.3403329 16:0.90228742 17:−0.058276027 18:2.0597355 19:−0.42797115 20:−0.86450082 21:0.90464163 22:0.73496294 23:0.28015259 24:0.35474181 25:−0.23638216 26:−0.15789628 27:−0.52309102 28:−0.37985617 29:0.287357 30:−0.56460238 31:0.37594208 32:−0.12875263 33:0.30352685 34:0.22884804 35:0.11167674 36:−0.20184764 37:−0.12710242 38:0.071013451 39:−0.045144837 40:−0.070461117 41:−0.019546293 42:0.065657027 43:0.14732917 44:0.018210998 45:−0.08014039 46:−0.11323337 47:−0.10019921 48:−0.10349691 49:0.020390021 50:0.090517618 51:−0.069692895 52:−0.021243189 53:0.14680925 54:0.0094662113 55:0.20897961 56:−0.0039457348 57:−0.091748476 58:0.13405176 59:−0.13937454 60:0.086304344 61:−0.12049349 62:0.21512045 63:0.058249764 64:0.073772818 65:0.0051474692 66:−0.16456354 67:0.083159164 68:−0.09391316 69:0.049482822 70:−0.098997042 71:0.083106592 72:0.017373484 73:−0.047681063 74:−0.028320642 75:4.0248819e−005 76:0.099030524 77:−0.10897497 78:−0.10352039 79:−0.060780682 80:−0.048596408 81:0.011235066 82:0.25329241 # |
| −0.014371081791088378 1:0.87059343 2:3.5878329 3:0.091554113 4:0.65345514 5:−0.47271317 6:−0.41384 7:−2.6189659 8:−0.12342864 9:1.5793581 10:−0.57370228 11:−1.3925625 12:−1.3556814 13:−1.2156334 14:0.49033341 15:−0.75910914 16:−0.66140902 17:0.21495797 18:1.322399 19:−0.42816734 20:−0.20139475 21:0.41710365 22:−0.66904598 23:−1.2503546 24:0.005865877 25:−0.075833492 26:−0.21863435 27:1.012139 28:0.38559043 29:0.22252241 30:−0.16451129 31:0.27448875 32:−0.19241415 33:0.19588548 34:0.010073803 35:−0.0058676698 36:0.00043716095 37:−0.017203512 38:−0.054450903 39:0.10513259 40:−0.29013771 41:−0.021617958 42:−0.60723102 43:−0.37005702 44:−0.054461829 45:−0.12877238 46:−0.23909518 47:0.13163029 48:0.18145508 49:−0.14183284 50:−0.31191406 51:0.15128855 52:0.11796327 53:0.19483642 54:0.072434336 55:0.098596357 56:−0.12887383 57:−0.0083674965 58:−0.24935839 59:−0.052760802 60:−0.010853617 61:0.085026577 62:−0.14680558 63:0.030738041 64:0.10266052 65:0.056526169 66:−0.063461311 67:−0.035973392 68:−0.10422022 69:0.098920599 70:−0.1844677 71:−0.014507533 72:−0.0056383871 73:−0.046550557 74:0.029349633 75:−0.05021812 76:0.0094082886 77:0.011692385 78:0.028477151 79:−0.029827924 80:−0.023342822 81:0.03091486 82:0.25329241 # |
| −0.014371081791088378 1:2.0827031 2:−4.5386529 3:2.791043 4:0.44649953 5:1.8717917 6:−1.5514507 7:−0.19173834 8:0.45179471 9:1.252743 10:−1.1577836 11:−0.99996018 12:0.51202804 13:0.21233207 14:−0.57810223 15:0.56387746 16:0.41448116 17:0.40147379 18:0.64566773 19:0.19013332 20:0.93090487 21:−0.53239536 22:−0.59026563 23:0.088252522 24:−1.0106578 25:−0.70878637 26:0.25647855 27:−0.024093486 28:−0.66579211 29:−0.15322554 30:0.24319333 31:−0.23693293 32:−0.49839178 33:0.007481074 34:−0.26763889 35:−0.15550058 36:−0.22630225 37:0.022563102 38:0.20322861 39:0.19503964 40:0.03580828 41:−0.19238393 42:−0.54305172 43:0.37427443 44:0.0062787877 45:−0.31011084 46:−0.33694553 47:−0.065238088 48:−0.022011872 49:0.025083838 50:0.028750926 51:−0.015624864 52:0.11465702 53:−0.069135807 54:−0.1922397 55:−0.34337896 56:0.094019294 57:0.053727783 58:0.0031050623 59:−0.016574457 60:−0.17301671 61:−0.058214545 62:−0.031321365 63:−0.1675214 64:−0.026916441 65:0.0039826082 66:0.12901579 67:−0.014975218 68:−0.039207086 69:0.062321864 70:0.029636266 71:−0.11686625 72:0.0075011854 73:0.018350322 74:−0.059716556 75:−0.0026313206 76:0.12975903 77:−0.033259977 78:−0.021897722 79:−0.03100355 80:−0.019817473 81:−0.089121908 82:0.25329241 # |
| −0.014371081791088378 1:−5.3239007 2:−1.271459 3:1.1219707 4:0.8795929 5:−0.11123593 6:0.049162205 7:−0.89622259 8:−0.61372954 9:1.5200393 10:0.58412057 11:−1.8329904 12:1.5775675 13:−0.34692562 14:−0.012877946 15:0.36438867 16:−0.4585036 17:0.063771129 18:0.31401601 19:0.86736262 20:0.13597916 21:0.55855584 22:−0.35006842 23:−0.014235095 24:−0.22553623 25:0.27074212 26:−0.47627738 27:0.4447929 28:0.13853005 29:−0.11119195 30:0.36050612 31:−0.07328327 32:−0.060440011 33:−0.37381712 34:0.22676152 35:0.25114605 36:0.51616573 37:0.23550244 38:0.06805402 39:0.32421982 40:−0.23539694 41:0.053735215 42:−0.038038298 43:−0.034686971 44:0.094751537 45:−0.012227111 46:−0.13375652 47:−0.1259481 48:−0.11651698 49:−0.071619377 50:0.10677592 51:−0.34058329 52:0.015812801 53:−0.067406513 54:0.21103315 55:0.041218095 56:0.020049199 57:−0.13044091 58:0.13511893 59:0.038044367 60:−0.17959379 61:−0.0071755145 62:0.0087408954 63:0.11011105 64:−0.062928498 65:0.035096791 66:0.16027978 67:−0.046912234 68:−0.015259732 69:0.12188949 70:0.084019214 71:0.1574484 72:−0.066938996 73:0.074207745 74:−0.026839223 75:−0.01708868 76:0.0057022288 77:−0.11029728 78:−0.0079312706 79:0.021477114 80:−0.02083559 81:−0.015407534 82:0.25329241 # |
| 0.014371081791088378 1:−1.7712733 2:0.85992974 3:2.3454196 4:3.1139693 5:−1.0714633 6:−1.7581615 7:−0.51479608 8:−0.98839289 9:0.39092192 10:−1.292107 11:−0.14927527 12:0.10043197 13:−0.043331504 14:0.39880082 15:0.010120268 16:−0.82551122 17:0.083098657 18:−0.12866859 19:−0.70402157 20:−0.65012646 21:−0.02339028 22:−1.4680903 23:0.046125181 24:0.84387946 25:−0.2265238 26:−0.14147067 27:0.52711749 28:−0.21664049 29:−0.2467404 30:−0.30438596 31:−0.050076567 32:−0.14185542 33:−0.089490563 34:−0.5232743 35:−0.055797219 36:−0.085122578 37:0.034332749 38:−0.2829197 39:0.0018594543 40:−0.1876 41:−0.094008774 42:−0.32108229 43:−0.19397746 44:−0.23942305 45:−0.048982996 46:0.12056146 47:0.14099196 48:0.18051358 49:0.2295133 50:0.19360952 51:−0.1103296 52:0.014821607 53:−0.16108313 54:0.16580546 55:0.16796973 56:0.11402052 57:0.24539067 58:0.16182666 59:0.085798874 60:−0.085405707 61:0.017833026 62:0.0018330675 63:−0.15083119 64:0.081316978 65:−0.098727234 66:0.018731356 67:−0.0060362304 68:0.03532853 69:0.088845044 70:0.10642132 71:0.075240389 72:−0.0017270686 73:0.051559579 74:−0.014961725 75:0.090149663 76:0.063269325 77:−0.0039378311 78:0.059029229 79:−0.018420469 80:0.013638197 |

APPENDIX C10-continued

| SVM Model Weights (82; Normal/Diseased) |
|---|
| 81:0.0058866376 82:0.25329241 # −0.013935452226682356 1:−5.8643632 2:−0.93534768 3:0.49938962 4:−0.93064308 5:−0.185434 6:−1.534196 7:−0.38749206 8:−0.89597219 9:−0.34875399 10:0.63001502 11:1.5652692 12:1.2590816 13:−0.51468796 14:−0.22045068 15:0.3293018 16:−0.27674249 17:0.086240664 18:0.19819136 19:−0.39232901 20:−0.37032464 21:0.38547245 22:0.73479778 23:−0.1816659 24:−0.021749923 25:−0.0039368388 26:0.13101645 27:−0.22941405 28:0.41755274 29:−0.1255347 30:−0.098276161 31:−0.0093230065 32:0.14494233 33:−0.29186839 34:0.33509961 35:−0.22010842 36:0.16008277 37:0.21455543 38:−0.10557131 39:0.13239385 40:0.089197315 41:0.10390823 42:0.11813315 43:0.039862566 44:−0.25545901 45:−0.36260548 46:−0.011953123 47:−0.020825984 48:0.092442289 49:0.24586442 50:0.32035184 51:−0.19072071 52:0.1109019 53:0.2683475 54:−0.055612121 55:−0.16262183 56:−0.007963703 57:−0.06148446 58:−0.02106435 59:−0.10918737 60:0.022327263 61:−0.080045484 62:0.10327489 63:−0.072775885 64:−0.075304672 65:0.052243993 66:−0.17375943 67:−0.085869133 68:−0.025927415 69:−0.033862192 70:0.003378497 71:0.036485743 72:0.02648801 73:0.038889419 74:0.0030899784 75:−0.071033508 76:−0.0090249451 77:0.0040854583 78:0.0087336292 79:0.014930444 80:−0.02574002 81:−0.017401123 82:0.25329241 # |
| −0.014371081791088378 1:−1.1154265 2:−0.65115529 3:0.78471106 4:0.66504043 5:0.77643335 6:−2.0906224 7:0.34513348 8:0.96412081 9:−0.59056032 10:−0.078536183 11:−1.2666911 12:−0.12625353 13:0.15398303 14:−1.1170033 15:0.081318125 16:−0.038733624 17:−0.31742609 18:−0.42565271 19:−0.6428268 20:0.44600609 21:0.39984989 22:−0.83137399 23:−0.37285015 24:−0.54521942 25:0.057914514 26:1.1564509 27:−0.029537503 28:−0.072775751 29:−0.63849616 30:−0.60283434 31:0.38105869 32:−0.27240914 33:−0.20034775 34:0.4241789 35:−0.010323828 36:0.51174611 37:−0.25457942 38:0.2709513 39:0.059532259 40:0.17014623 41:−0.075634539 42:0.12154446 43:0.090053745 44:−0.10367984 45:−0.034247566 46:0.18424711 47:−0.29232064 48:−0.14740901 49:0.1492925 50:0.00058022176 51:−0.087720893 52:−0.033356212 53:−0.20035958 54:0.2253872 55:0.12879528 56:−0.23089486 57:−0.1055094 58:−0.13547257 59:−0.10747704 60:−0.0092957551 61:0.10458979 62:−0.077063024 63:−0.02096506 64:0.0042612529 65:−0.0011343539 66:−0.0065472969 67:−0.10382 68:0.05947791 69:−0.026584987 70:0.1416434 71:0.14961426 72:−0.031604376 73:−0.070630185 74:−0.12112147 75:0.13053244 76:−0.038431559 77:0.020394776 78:0.033698909 79:−0.058031898 80:0.075310543 81:0.015562753 82:0.25329241 # |
| −0.0087763075857475708 1:1.5905032 2:5.3645372 3:−1.4477293 4:1.8198627 5:−1.1767664 6:0.81288171 7:−0.67526293 8:−1.1132079 9:0.28507367 10:−0.012736053 11:1.0111644 12:0.75601494 13:0.98898768 14:−0.69530016 15:−0.097560644 16:1.3494476 17:−1.0568211 18:0.18170927 19:0.12219389 20:−0.41637009 21:−0.35449636 22:0.077368096 23:−0.47044316 24:0.21345852 25:−0.34096071 26:−0.15059784 27:0.35658416 28:0.3400493 29:−0.34867704 30:0.56223273 31:−0.43449125 32:0.27360469 33:0.43707809 34:0.21761405 35:−0.43889114 36:−0.038312916 37:0.255097 38:0.087097213 39:−0.14609973 40:−0.25476536 41:−0.43897498 42:−0.13708156 43:−0.096403405 44:0.10123724 45:−0.048603624 46:0.0046454594 47:0.28983507 48:−0.26345158 49:0.050361965 50:−0.12226773 51:0.15456964 52:0.17078514 53:−0.17840773 54:0.25593066 55:−0.093079463 56:−0.17126484 57:−0.14548442 58:0.10084035 59:−0.16368657 60:0.093007393 61:0.26340434 62:−0.014753903 63:−0.035710178 64:−0.061668005 65:0.06639538 66:−0.060775947 67:−0.036008667 68:0.17328157 69:−0.14019264 70:−0.11088976 71:0.065311126 72:−0.091783993 73:0.1820229 74:0.11078074 75:0.01981158 76:0.017440848 77:0.056806833 78:−0.060073696 79:0.0051125907 80:0.030296072 81:0.036278382 82:0.25329241 # |
| 0.0083237638245155857 1:−2.2393372 2:4.199626 3:2.5598192 4:2.467262 5:−0.83616585 6:−2.2503364 7:0.39702567 8:−2.0303228 9:−1.6285394 10:−0.62717658 11:0.40632513 12:−0.2438425 13:−0.21972954 14:0.39473441 15:−0.22718349 16:−0.51952434 17:−0.25986105 18:−0.4086445 19:−1.2832011 20:−0.42313382 21:0.57975292 22:−1.1609888 23:−0.48961833 24:−0.49401966 25:0.72498322 26:0.2920382 27:−0.3599973 28:0.65332633 29:0.26832682 30:−0.50291193 31:0.049351253 32:−0.12447462 33:−0.94793898 34:0.28927991 35:0.33756259 36:−0.5084886 37:−0.44958425 38:0.32846445 39:−0.22288465 40:−0.151096 41:0.28991494 42:0.2534031 43:0.36223406 44:−0.075824156 45:−0.46438354 46:−0.37752223 47:−0.12931581 48:−0.17827615 49:0.033764981 50:0.084633477 51:0.12486546 52:0.11227116 53:−0.11604822 54:−0.088474527 55:−0.14175765 56:0.22630401 57:0.011179022 58:−0.055442378 59:−0.030087344 60:−0.0095982794 61:0.12357093 62:−0.047852658 63:0.19976191 64:−0.11461759 65:0.032792922 66:0.04960895 67:0.040194597 68:0.10348131 69:0.004130546 70:0.046396118 71:0.016336117 72:0.038217518 73:−0.052427962 74:0.054562915 75:0.015991095 76:−0.074550532 77:−0.057401836 78:−0.036572538 79:0.048689198 80:0.0020374097 81:−0.028651439 82:0.25329241 # |
| 0.0071221644380766985 1:−5.4423494 2:−0.58802104 3:5.524426 4:−1.624148 5:6.7409973 6:−1.3937613 7:−0.35392043 8:1.0985852 9:2.5859268 10:−1.0802349 11:0.24384615 12:0.91363966 13:−0.50276214 14:−0.89652449 15:1.2317376 16:0.67724931 17:0.73762757 18:−0.30085871 19:−0.1159915 20:−0.48025069 21:−0.50364071 22:−1.5698023 23:−0.44514489 24:−0.11812235 25:0.076312713 26:0.11099086 27:−0.58268464 28:−0.77682894 29:0.54886699 30:0.10645868 31:−1.1519066 32:0.1148726 33:0.014013563 34:0.1877993 35:0.077201612 36:−0.0033134457 37:−0.17110914 38:−0.18452464 39:0.20830691 40:0.057996828 41:−0.19142845 42:0.57352281 43:−0.29680991 44:0.29264197 45:−0.18688387 46:−0.17933765 47:0.29997057 48:0.3198947 49:0.13645113 50:0.18196066 51:0.13275661 52:0.19360863 53:0.1438975 54:−0.042380612 55:−0.050588559 56:−0.11479136 57:−0.2503086 58:−0.0037292538 59:0.0022796106 60:0.063194968 61:−0.10953682 62:−0.00513366 63:0.14069435 64:−0.027389221 65:−0.0051202965 66:−0.057197187 67:−0.05615497 68:−0.061383404 69:−0.026006866 70:0.07195735 71:−0.045136459 72:−0.051242962 73:−0.063313864 74:0.067755125 75:0.035193127 76:0.029761201 77:0.0056933551 78:0.017063322 79:0.056272577 80:−0.039614562 81:−0.004273002 82:0.25329241 # |

APPENDIX C11

SVM Model Weights
(82; Benign/Malignant)

SVM-light Version V6.01
0 # kernel type
3 # kernel parameter -d
1 # kernel parameter -g
1 # kernel parameter -s
1 # kernel parameter -r
empty# kernel parameter -u
82 # highest feature index
99 # number of training documents
56 # number of support vectors plus 1
0.45569806 # threshold b, each following line is a SV (starting with alpha*y)
0.013907467001722892 1:3.1567101 2:0.16618904 3:1.8542163 4:0.014481023 5:1.3972945 6:−3.1025994 7:−3.4176571 8:−0.45484769 9:1.1210192 10:−0.38685206 11:−1.5205327 12:0.68543404 13:−1.75438 14:0.53878391 15:2.7158511 16:−0.56557649 17:1.2554321 18:−0.47308835 19:0.68576759 20:0.97994357 21:−0.292142 22:0.39044076 23:−0.15855564 24:0.038191736 25:−0.31132123 26:0.53109151 27:−0.5032022 28:0.5605045 29:0.20520987 30:0.293466 31:−0.26168749 32:0.37033597 33:−0.29431155 34:0.10337116 35:−0.11785443 36:−0.28718862 37:0.32803136 38:0.29440144 39:−0.082999088 40:−0.014069064 41:0.085100941 42:0.062163971 43:−0.10818884 44:0.26157206 45:0.30576223 46:−0.39297685 47:−0.35423461 48:−0.087857343 49:0.10254776 50:−0.1561446 51:−0.016422139 52:0.07234285 53:0.013479226 54:−0.046674255 55:0.046594094 56:0.093331829 57:0.035379875 58:0.11953397 59:0.036969446 60:0.063316084 61:0.082851306 62:−0.1032842 63:0.13859528 64:0.041353751 65:−0.024971092 66:−0.026600137 67:0.029097036 68:0.018415105 69:−0.0062900544 70:0.035226297 71:0.010622519 72:−0.039238021 73:0.015994981 74:−0.0045444495 75:−0.03215915 76:0.024089301 77:0.012362846 78:−0.049592819 79:−0.0032664295 80:0.019039923 81:−0.011157157 82:0.25567371 #
−0.013907467001722892 1:0.002651917 2:0.98606867 3:2.3826811 4:1.1390226 5:0.12783521 6:−0.54945189 7:1.730462 8:−1.0582304 9:0.29667062 10:0.025138268 11:−0.34364295 12:−0.24810615 13:0.63317603 14:−0.5921548 15:−0.46557185 16:0.085824318 17:0.78309184 18:0.65660352 19:0.48798752 20:−0.67073804 21:−0.32879993 22:0.086128756 23:−0.02290489 24:−0.71815228 25:−1.0004225 26:−0.2888827 27:0.44291174 28:−0.17778675 29:−0.16520225 30:0.19636671 31:−0.3525435 32:0.01298329 33:−0.32772034 34:0.076057971 35:−0.35886341 36:−0.040958837 37:0.082929745 38:−0.21441554 39:−0.35400665 40:−0.27622771 41:−0.22728202 42:0.21941765 43:−0.27094331 44:−0.041872539 45:−0.15448959 46:−0.021528801 47:0.20137747 48:0.25446901 49:0.290241 50:0.055019837 51:−0.017734742 52:−0.044442583 53:−0.12903592 54:−0.044102933 55:−0.029337408 56:−0.0025109963 57:−0.20523353 58:0.069687195 59:0.088491611 60:−0.14346558 61:0.13515595 62:0.054679595 63:0.026407499 64:−0.04021319 65:0.1348345 66:0.014721237 67:−0.021316452 68:0.017826751 69:0.054467481 70:0.088076189 71:−0.0059712916 72:0.077442929 73:−0.0027787003 74:−0.01858215 75:0.029905282 76:0.043979332 77:0.097268574 78:0.013925444 79:−0.0067048757 80:−0.024549417 81:−0.018623218 82:0.25567371 #
0.013907467001722892 1:0.080933683 2:−1.1914428 3:−3.4632533 4:1.155984 5:2.4505055 6:−0.48683998 7:3.2953207 8:1.5352644 9:1.8355713 10:1.3896872 11:1.0753843 12:−0.034180783 13:0.35684481 14:1.5341158 15:−0.64546579 16:0.12234416 17:0.57575071 18:0.15887658 19:−0.29182664 20:0.46651709 21:0.29582661 22:2.101083 23:−0.71179837 24:−0.021273606 25:0.48117211 26:−0.11492103 27:0.34172928 28:−0.29126027 29:0.4420194 30:−0.41723165 31:0.025297057 32:−0.15456693 33:0.10863433 34:0.15622525 35:−0.15762766 36:0.078451499 37:−0.22811173 38:−0.48609617 39:−0.55162007 40:−0.13283053 41:−0.050343122 42:−0.15764947 43:0.25334856 44:0.061278328 45:0.027302107 46:−0.16040276 47:0.062136248 48:−0.23032755 49:0.27913967 50:−0.16669102 51:−0.077022836 52:−0.033983383 53:0.20982005 54:0.053779136 55:0.01178002 56:0.0066895927 57:−0.1356044 58:−0.10798105 59:0.15816236 60:−0.02375962 61:0.035936434 62:0.10734662 63:−0.06747932 64:0.056676835 65:−0.00065177749 66:−0.015038575 67:0.036054466 68:0.09175051 69:−0.047434662 70:−0.0073538097 71:−0.0088641308 72:−0.07059288 73:−0.097584553 74:0.047180023 75:0.057489462 76:0.0051211752 77:0.012965675 78:−0.025874568 79:0.012731925 80:0.0013606574 81:0.0022765554 82:0.25567371 #
0.013907467001722892 1:3.2137563 2:0.47746769 3:0.48038164 4:−3.7653837 5:1.2339842 6:−2.0872419 7:1.1595073 8:−1.3046167 9:1.9119325 10:−1.0545735 11:0.61526155 12:−0.24651189 13:−0.4924134 14:−0.078388341 15:−0.95829707 16:0.27138114 17:−0.10419766 18:−1.2434648 19:−0.07081046 20:0.36508694 21:0.060325716 22:0.48514739 23:0.68073261 24:−0.45294562 25:−0.23691821 26:−0.041596867 27:−0.21548308 28:0.70605165 29:0.09917222 30:0.21392259 31:0.22936337 32:−0.11731907 33:−0.041600302 34:0.095469855 35:−0.41523668 36:0.10409098 37:−0.30141127 38:0.35239288 39:−0.19246656 40:0.34217504 41:0.34814653 42:−0.26780447 43:−0.1243982 44:−0.01815049 45:−0.057028007 46:0.11627141 47:−0.086791828 48:0.092508137 49:0.0018598757 50:−0.040142961 51:0.069872767 52:0.074374996 53:−0.19912603 54:0.076588184 55:−0.093404651 56:0.10183166 57:0.060058489 58:−0.13849878 59:−0.15906949 60:0.1800503 61:0.035952922 62:−0.12798084 63:−0.083410777 64:−0.20457396 65:0.035567068 66:0.019876361 67:0.087410249 68:0.02310947 69:0.09201736 70:0.027875891 71:−0.026512658 72:0.01697951 73:0.0045687994 74:−0.02609979 75:−0.014867129 76:0.066753574 77:−0.010795198 78:0.032971065 79:0.039688867 80:−0.048311502 81:−0.00027685586 82:0.25567371 #
0.013907467001722892 1:−2.7918429 2:3.7392309 3:0.96980011 4:5.581255 5:0.33731475 6:1.179503 7:0.89744556 8:−2.5802081 9:0.25951603 10:−0.84403944 11:1.2862083 12:−0.16128187 13:−0.11803147 14:−1.9132354 15:−0.11223348 16:1.0232759 17:−0.62201375 18:0.94165522 19:1.5683089 20:−0.45407972 21:−0.26419452 22:0.51423109 23:0.35349846 24:−0.092069693 25:−1.1951565 26:0.53779632 27:−0.15563972 28:1.0795906 29:0.57995433 30:−0.41967639 31:−0.25984129 32:0.52238524 33:0.088213466 34:−0.33170569 35:0.091871276

SVM Model Weights
(82; Benign/Malignant)

36:0.32154143 37:−0.24431969 38:−0.28046533 39:−0.11163279 40:0.14938606 41:−0.1531287
42:−0.20925696 43:−0.45577037 44:−0.3075608 45:0.24592124 46:0.30894414 47:−0.00029260028
48:−0.089255512 49:0.14482489 50:−0.18223053 51:−0.046016071 52:0.18327117 53:0.086313628
54:−0.1815256 55:0.14078927 56:−0.095226422 57:−0.037365079 58:−0.1549547 59:−0.075251564
60:0.13708013 61:−0.14474814 62:−0.026806368 63:0.015333725 64:0.081638411
65:−0.0070111523 66:−0.02307344 67:−0.023115141 68:−0.036209293 69:0.014039898
70:0.018128078 71:0.082819954 72:0.045986831 73:−0.016791828 74:0.036390752
75:−0.019287534 76:0.016352588 77:0.0063856659 78:0.0082372231 79:−0.0043017734
80:0.028264908 81:0.0051311255 82:0.25567371 #
0.013907467001722892 1:−3.619926 2:−2.6293223 3:−5.8518434 4:−1.5757899 5:−2.9437122
6:5.5407448 7:−0.82116526 8:−3.466711 9:0.0021926758 10:3.0869479 11:−1.0016136
12:1.2197683 13:−1.436379 14:0.31899369 15:0.93561667 16:1.6176525 17:−0.39378786
18:−0.18749779 19:−1.8418909 20:−0.43583691 21:1.432151 22:−0.823071 23:−0.8023172
24:−0.52592236 25:−1.0698589 26:−0.44165942 27:−0.78191882 28:0.22653167 29:0.41191986
30:−0.060874555 31:−0.26568279 32:−0.38131109 33:−0.31830141 34:−0.45852211 35:−0.058234289
36:0.29590148 37:−0.68837774 38:−0.20077451 39:−0.062276743 40:−0.35707316 41:0.19054121
42:−0.15077025 43:−0.078146808 44:0.12414627 45:−0.023111818 46:−0.15437129
47:−0.033677876 48:−0.13043354 49:0.092869744 50:−0.012675262 51:−0.10580228 52:−0.027187418
53:−0.17423774 54:−0.10509105 55:−0.030380335 56:0.068291731 57:0.097614437
58:0.070459813 59:0.054557417 60:−0.02352139 61:0.088585123 62:0.037247963
63:0.0078980811 64:−0.052348923 65:0.0084877722 66:−0.015368021 67:−0.037530847
68:0.007361141 69:−0.032553211 70:−0.015326261 71:−0.026421729 72:−0.0069468748
73:0.013459054 74:0.041822456 75:−0.053651877 76:−0.0050171232 77:0.0043700207
78:0.0053782254 79:6.9578549e−005 80:0.00097944599 81:−5.70134e−005 82:0.25567371 #
−0.013907467001722892 1:6.5781665 2:2.1187475 3:−0.7835753 4:−2.8270266 5:0.1337319
6:−0.18630271 7:−1.7452089 8:−0.98421592 9:−1.8634179 10:−1.1380285 11:0.34646344
12:0.54238832 13:0.26588807 14:0.45058212 15:0.45961592 16:−0.28031725 17:0.66470343
18:−0.51538295 19:−0.1657657 20:−0.45943725 21:−0.49348325 22:0.37306851 23:−0.1414268
24:−0.29623803 25:−0.16292128 26:0.16967954 27:0.32698357 28:−0.37567034 29:0.37099364
30:0.59596163 31:−0.0015005484 32:−0.41130692 33:−0.34374326 34:−0.49081743 35:0.45261174
36:0.056836125 37:0.094040535 38:−0.30606082 39:0.2526404 40:0.028356994 41:0.098269232
42:−0.12199362 43:0.14226985 44:−0.31726238 45:−0.24740721 46:−0.19374534 47:−0.056049012
48:−0.052241877 49:−0.20541354 50:−0.14743847 51:−0.085847393 52:−0.11035357 53:0.15058087
54:0.0083219986 55:0.30017507 56:0.084475629 57:−0.02588613 58:0.0027963538
59:−0.024245178 60:0.045104075 61:0.012391422 62:0.15603219 63:−0.010205535 64:−0.10566497
65:0.20527013 66:−0.056743622 67:−0.1028032 68:0.14594384 69:0.12454806 70:−0.031454634
71:0.087476976 72:0.08834368 73:0.063018188 74:0.02898792 75:0.043453537 76:0.062644392
77:−0.013960996 78:−0.014934716 79:−0.011682215 80:0.014400378 81:0.0073678829
82:0.25567371 #
−0.013907467001722892 1:8.6937275 2:−1.1400434 3:−2.1519079 4:3.580739 5:−0.322896
6:3.9132211 7:5.2217107 8:1.1789006 9:−1.0246336 10:−0.96747965 11:−0.29383633
12:0.76610166 13:−0.79461324 14:0.4043839 15:−1.0012354 16:0.29168835 17:−0.56701225
18:−0.069885537 19:0.14974712 20:0.35432532 21:−0.31716883 22:−0.59514731 23:−0.22238307
24:−0.12135573 25:0.047585681 26:−0.70089114 27:−0.078941204 28:0.098712035 29:−0.41009673
30:−0.13532054 31:0.51622146 32:0.16921167 33:0.32283872 34:0.52671987 35:−0.048735265
36:−0.15821755 37:−0.039334863 38:0.0048291734 39:−0.54441392 40:−0.19081639
41:0.086660512 42:0.073062316 43:0.030611349 44:0.06409578 45:−0.19361813 46:0.020256663
47:−0.21615875 48:0.12167526 49:−0.080530636 50:−0.21931982 51:0.13648947 52:−0.067624554
53:−0.04258389 54:0.088686369 55:0.097700112 56:0.18430485 57:−0.037396338 58:0.044195484
59:−0.20795707 60:0.19515324 61:−0.035412516 62:−0.091619283 63:0.14196961 64:0.036034033
65:−0.023479406 66:0.019341901 67:−0.067119963 68:0.038271904 69:0.036672547
70:−0.028922372 71:−0.0060990094 72:0.0088292509 73:0.0023125587 74:0.015565125
75:0.022060553 76:−0.016011426 77:−0.0079317112 78:0.011026716 79:−0.038202453
80:0.048583072 81:−0.0042654183 82:0.25567371 #
−0.013907467001722892 1:1.0243195 2:−0.38197148 3:−3.7814343 4:−2.2250402 5:0.47157016
6:−2.1615746 7:0.96844673 8:1.0164919 9:−2.0591228 10:−0.6572175 11:0.37804231 12:0.44079155
13:0.3109242 14:0.035389163 15:−0.33573273 16:−0.74668443 17:−0.57036757 18:−0.076940089
19:−0.08777532 20:−0.24845943 21:−0.27566159 22:−0.45323232 23:0.036193147 24:−0.39798844
25:−0.064215995 26:−0.12832147 27:−0.51961374 28:0.56388164 29:0.33960932 30:0.11790788
31:0.010629584 32:0.31375942 33:−0.3635692 34:0.11770105 35:0.1948024 36:−0.53220505
37:−0.015388041 38:0.055305894 39:0.11751298 40:0.15316819 41:−0.3353864 42:−0.15304482
43:0.41588679 44:0.43531179 45:−0.31292126 46:0.064552836 47:0.083345257 48:0.063418671
49:0.36416233 50:0.1777045 51:0.021986378 52:−0.051301539 53:0.091295533 54:0.094320573
55:0.13744071 56:0.047318276 57:0.15952836 58:0.033521026 59:0.076471284 60:−0.035316687
61:−0.15475383 62:0.078926347 63:−0.046019707 64:−0.069484062 65:−0.068120748
66:0.062563717 67:0.0014837421 68:0.030301386 69:−0.037804812 70:−0.013911921
71:−0.048225295 72:0.083848305 73:0.076321773 74:−0.018071061 75:−0.055793755 76:0.012113683
77:0.042205438 78:0.012898841 79:0.035085335 80:0.048108593 81:−0.0096882842
82:0.25567371 #
−0.013907467001722892 1:2.2212989 2:2.2423356 3:0.54245722 4:4.6349773 5:−0.11698673
6:0.1273587 7:−0.32963273 8:−0.40856531 9:−2.4360094 10:−0.10716601 11:1.0242654
12:−0.7633462 13:−0.62989014 14:−0.65141433 15:0.20816107 16:0.2149162 17:−0.10790395
18:0.062655389 19:0.10254406 20:−0.094486028 21:−0.70745504 22:0.059736516 23:−0.30498576
24:0.054204363 25:0.21246172 26:−0.52425498 27:0.81914634 28:0.048554443 29:−0.17359619
30:−0.23885868 31:0.25071031 32:−0.22767279 33:0.22731103 34:−0.30027446 35:0.1434586
36:0.20617312 37:0.066609994 38:0.031440154 39:0.11149884 40:0.049886927 41−:0.068462618
42:−0.3243098 43:−0.0012718373 44:−0.083923958 45:0.18864746 46:−0.10086386 47:−0.3053132

APPENDIX C11-continued

| SVM Model Weights (82; Benign/Malignant) |
|---|
| 48:−0.14435789 49:0.026048217 50:0.12950943 51:−0.045977823 52:−0.0020502491 53:−0.18364553 54:0.028195389 55:−0.19675305 56:0.10230119 57:−0.049513366 58:0.18105845 59:0.19450617 60:0.12170141 61:−0.055088673 62:0.065109655 63:0.20906085 64:−0.063107416 65:−0.017050805 66:0.00010687527 67:0.015721906 68:0.0062088915 69:−0.05739858 70:0.14055385 71:−0.066592857 72:0.013350928 73:0.058735143 74:0.016233783 75:−0.048403196 76:0.042300489 77:−0.0023901218 78:0.031673688 79:−0.0068418281 80:0.0092385178 81:−0.014091139 82:0.25567371 # |
| −0.0085858012089370835 1:−1.3254935 2:−4.82131 3:−3.0696814 4:0.47993213 5:0.82052201 6:−0.34809491 7:−0.31098643 8:−0.91316992 9:0.27424634 10:0.51772237 11:0.85809773 12:0.90295136 13:0.74651027 14:0.45621145 15:0.44970477 16:1.3667926 17:−0.50160086 18:0.70031488 19:−0.33182815 20:0.39681572 21:−0.8752895 22:0.44086796 23:−0.13647421 24:−0.22896612 25:−0.3569037 26:0.68794847 27:0.43931317 28:0.49743056 29:0.17149527 30:0.67385966 31:−0.19279872 32:0.42393622 33:−0.25739413 34:−0.21672966 35:−0.053589214 36:−0.18433735 37:0.45720103 38:0.3844561 39:−0.048400849 40:−0.32128289 41:0.27001503 42:−0.017244074 43:0.20652708 44:0.10910439 45:0.13481122 46:−0.18037997 47:0.18652654 48:0.23005758 49:−0.088411964 50:−0.049571555 51:0.10868713 52:−0.21518077 53:0.14662643 54:−0.080307372 55:−0.055205084 56:0.29687792 57:−0.34123605 58:0.056296293 59:−0.096458957 60:0.014342502 61:−0.03401291 62:−0.055514019 63:−0.038223349 64:0.070947193 65:0.018410154 66:0.1130692 67:−0.0073749996 68:−0.099752046 69:−0.040401001 70:−0.081922077 71:−0.072609454 72:0.088830002 73:−0.044365808 74:0.038890094 75:−0.027900867 76:−0.012964657 77:−0.011553071 78:0.013520855 79:−0.018533291 80:−0.014131732 81:0.038447794 82:0.25567371 # |
| 0.013907467001722892 1:1.4806626 2:−4.8635139 3:3.2236488 4:1.7933227 5:−1.316788 6:−1.0017112 7:0.47548813 8:1.6735988 9:0.66981721 10:0.24094659 11:−1.0107924 12:−1.1080424 13:−0.00806004 14:−1.0655001 15:0.69547391 16:−0.23062928 17:0.38047528 18:−0.50040817 19:−0.71245897 20:0.27748254 21:0.92888379 22:−0.047542933 23:−0.55884403 24:0.52523893 25:−0.34099689 26:−0.11326764 27:0.24935542 28:−0.27659222 29:0.3617793 30:0.13711159 31:0.03563977 32:0.43898481 33:−0.030524582 34:−0.18930535 35:0.26575625 36:−0.051591638 37:0.093289182 38:−0.12283277 39:−0.0087459367 40:−0.15349482 41:0.076120593 42:−0.090644263 43:0.26222029 44:−0.42837751 45:−0.037280269 46:0.032799728 47:−0.028520888 48:−0.16733062 49:−0.0046878331 50:−0.57103378 51:0.1325575 52:−0.18325704 53:−0.10590571 54:0.069956727 55:0.16672798 56:−0.13117546 57:0.1553829 58:−0.15503366 59:−0.17099887 60:0.093083881 61:0.026113816 62:0.14021461 63:−0.031965856 64:−0.095597953 65:−0.11084546 66:−0.012837233 67:0.082926385 68:−0.011535439 69:0.011916623 70:0.03308095 71:−0.031754006 72:0.0014486267 73:0.0124491 74:−0.035814222 75:0.015123948 76:−0.047888789 77:0.048203971 78:0.016241761 79:0.011316194 80:0.034494244 81:0.015111173 82:0.25567371 # |
| 0.013907467001722892 1:0.5282346 2:−5.484405 3:1.4931254 4:−0.14043914 5:−2.2096224 6:−0.59316844 7:1.6756516 8:0.90240264 9:0.39984435 10:1.2447444 11:−0.28950989 12:−1.6651386 13:0.28873664 14:−0.58520627 15:0.30581889 16:0.26979491 17:−0.75517011 18:0.47092143 19:0.40895745 20:−0.23498023 21:−0.7098344 22:−0.29512653 23:−1.2106169 24:−0.27367452 25:0.044541284 26:0.49630541 27:0.068383642 28:−0.36716366 29:0.18695824 30:0.63265276 31:0.45222038 32:−0.056348816 33:0.20280178 34:−0.1906321 35:−0.353551 36:0.16343439 37:−0.28218001 38:0.16846286 39:0.078423202 40:0.083406515 41:0.39002004 42:0.29232916 43:0.11815859 44:0.08957018 45:0.038236845 46:0.28640682 47:−0.02373923 48:−0.078649454 49:0.14222306 50:0.066447333 51:−0.083863318 52:0.12524372 53:−0.035551179 54:0.023687186 55:−0.21581374 56:−0.029654844 57:0.095358692 58:0.17166713 59:−0.1162771 60:−0.12052445 61:−0.17919333 62:−0.10123057 63:0.11041252 64:0.0026177783 65:−0.022417426 66:−0.036060501 67:−0.035753701 68:0.06705036 69:0.093109563 70:0.013771997 71:0.089644045 72:0.031394012 73:−0.012064199 74:0.033468664 75:0.050581343 76:0.0081060557 77:0.0074956147 78:−0.010660128 79:0.00035801323 80:0.0026250796 81:0.026720919 82:0.25567371 # |
| 0.013907467001722892 1:2.3386104 2:6.3404236 3:3.2294741 4:−1.9317672 5:0.071201861 6:−0.044307262 7:−2.0207732 8:−2.488713 9:−0.6283133 10:0.4825606 11:−0.28122392 12:0.21676083 13:−1.6348528 14:−0.82939267 15:0.034967743 16:0.7632736 17:0.20813568 18:0.63286573 19:−0.47898716 20:1.2485386 21:0.10064972 22:0.98327351 23:−0.26787534 24:0.64377373 25:0.99090523 26:−0.55202091 27:0.10633966 28:0.03703085 29:0.57455915 30:0.22084522 31:−0.36619347 32:−0.22556315 33:0.34115922 34:−0.042702142 35:−0.091154702 36:0.12385885 37:−0.31401032 38:−0.4164632 39:−0.12481187 40:0.1729352 41:0.025761804 42:0.19804724 43:−0.0485407 44:0.19925766 45:−0.28257406 46:0.28749916 47:−0.076349206 48:−0.029022479 49:0.045146827 50:0.23469912 51:−0.22822835 52:−0.16896489 53:0.16428801 54:−0.10073017 55:−0.04911986 56:0.014340572 57:0.055428687 58:0.017072277 59:−0.23835564 60:0.11120624 61:−0.040464722 62:0.015790841 63:0.05838633 64:0.030759592 65:0.090752535 66:0.097924195 67:0.059431423 68:0.018375611 69:−0.025880037 70:−0.085142791 71:0.037109379 72:0.017843693 73:0.033101507 74:−0.086792372 75:−0.019385036 76:−0.03993091 77:−0.022123052 78:0.025371514 79:0.0099139242 80:0.021407833 81:0.0026641551 82:0.25567371 # |
| 0.013907467001722892 1:0.92531532 2:3.2725589 3:−0.54186034 4:−0.046084434 5:−0.71063632 6:−1.065266 7:−0.23375395 8:7.6197457 9:1.6625646 10:−1.5000564 11:−2.0660326 12:−0.19870608 13:−0.39216396 14:1.1567287 15:−0.35612366 16:0.3130272 17:−2.0931723 18:0.11011051 19:0.84284449 20:0.013501336 21:0.046461876 22:1.5516397 23:−0.27960607 24:0.69059569 25:−1.2106048 26:−1.2763588 27:−0.12032586 28:0.093579069 29:−0.32920837 30:0.48157367 31:−0.42374054 32:−0.14591351 33:0.1176537 34:−0.18161951 35:0.25301832 36:0.66938704 37:−0.057802666 38:−0.13343674 39:0.62735879 40:−0.044096556 41:0.18705167 42:−0.17194651 43:0.074589595 44:0.21269155 45:0.089623697 46:0.059762586 47:−0.029209353 48:0.03704172 49:−0.030952863 50:0.015506134 51:0.025615251 52:0.0052244631 53:−0.086779736 54:−0.093574241 55:−0.046916589 56:−0.08362405 57:−0.074757271 58:0.01333593 |

APPENDIX C11-continued

| SVM Model Weights (82; Benign/Malignant) |
|---|
| 59:0.024787342 60:0.035859052 61:0.042486023 62:0.0084086601 63:0.010098801 64:0.02284532 65:0.052486856 66:−0.04926512 67:−0.03656625 68:0.010819905 69:−0.045482125 70:−0.058025505 71:−0.016828215 72:0.031890634 73:0.030433306 74:−0.011717948 75:−0.044479515 76:−0.015215926 77:−0.0023755697 78:0.0034599551 79:0.00051749329 80:−0.010226478 81:3.801932e−005 82:0.25567371 # |
| 0.013907467001722892 1:−0.31337216 2:−4.4379792 3:2.3582401 4:0.41416493 5:−3.3641348 6:−1.0418055 7:−0.19555733 8:0.45191205 9:−2.1584406 10:1.1324015 11:0.68982244 12:−1.1676755 13:1.3409806 14:−1.6426444 15:0.69537538 16:−0.98763561 17:−0.32675835 18:0.67812878 19:−0.66984165 20:0.031228915 21:0.27176726 22:0.26936069 23:−0.16906807 24:−0.32627869 25:1.1193974 26:0.10977805 27:−0.43033385 28:−0.95668203 29:−0.25422433 30:−0.34753612 31:−0.38752791 32:0.58244002 33:−0.48634967 34:−0.2025563 35:−0.24161176 36:0.17671585 37:−0.24065688 38:−0.050498847 39:−0.28307024 40:0.26477423 41:0.47382107 42:−0.025447302 43:0.20467587 44:0.2217512 45:0.37574086 46:0.061973073 47:0.10667551 48:0.16203311 49:−0.073726997 50:0.021588469 51:−0.20430367 52:−0.040195208 53:−0.025409846 54:−0.030112945 55:0.16444026 56:−0.23417957 57:−0.27572164 58:−0.11283974 59:−0.05794502 60:0.010915354 61:−0.064104564 62:−0.03133551 63:0.080254652 64:−0.09139505 65:0.026808115 66:0.029095002 67:0.009047363 68:−0.00056003552 69:0.025533518 70:−0.079846606 71:−0.023178091 72:−0.02144677 73:0.050213989 74:−0.012168776 75:−0.067602694 76:0.028939376 77:0.021039849 78:0.00042727476 79:−0.021793403 80:−0.0057580168 81:−0.01654646 82:0.25567371 # |
| −0.013907467001722892 1:0.45722565 2:−3.4882009 3:0.22903383 4:0.17644122 5:0.85509831 6:−0.75209802 7:−0.76988745 8:−0.25909516 9:0.070875362 10:0.33397809 11:0.9078024 12:0.60130185 13:1.4851665 14:−0.2751933 15:−0.68341434 16:0.62224263 17:0.3703852 18:−0.66993684 19:−0.38562521 20:0.44285867 21:−0.29626027 22:0.8824321 23:−0.33962312 24:−0.29496264 25:−0.39299873 26:−0.21916553 27:−0.19340031 28:−0.84466314 29:0.30001366 30:0.15318669 31:0.43855944 32:0.081678972 33:0.32938871 34:0.35739893 35:−0.19378594 36:0.084175169 37:0.14802684 38:−0.006124665 39:−0.18371508 40:−0.16712031 41:−0.21613251 42:0.1259155 43:0.19873482 44:−0.18885405 45:0.11871104 46:−0.070632331 47:−0.36830303 48:−0.056283124 49:−0.039440956 50:0.23799692 51:0.12331919 52:−0.0024904897 53:0.14506921 54:−0.41753608 55:0.045860883 56:0.032534719 57:0.32123819 58:−0.26298875 59:−0.059578236 60:−0.10466552 61:−0.069041453 62:0.0084336242 63:0.05241622 64:−0.021091243 65:0.011123164 66:−0.11084538 67:−0.061537236 68:0.0087701716 69:0.035102431 70:−0.045404438 71:−0.088742957 72:0.080612667 73:0.0088466061 74:−0.020630445 75:−0.057637192 76:0.056012552 77:−0.050903127 78:0.018998409 79:−0.031038254 80:−0.021991439 81:−0.0093716355 82:0.25567371 # |
| −0.013907467001722892 1:−0.50929236 2:6.8492913 3:5.502048 4:1.1457709 5:−0.9338426 6:−2.1301727 7:1.7956586 8:−0.66483825 9:2.2789998 10:0.75155294 11:−0.25644207 12:−0.3254098 13:2.1627822 14:−0.85244954 15:0.88481462 16:0.50038588 17:0.029978361 18:−0.24679281 19:−0.30118141 20:−0.16269626 21:0.21018057 22:−1.3089206 23:0.81075418 24:1.5648531 25:0.047895078 26:0.21980281 27:−0.0047928062 28:−0.26051944 29:0.74385637 30:0.10023853 31:0.2821621 32:0.030019484 33:0.46246049 34:−0.083249241 35:0.35066962 36:−0.15394858 37:−0.56206924 38:−0.23051488 39:0.30362546 40:−0.46205294 41:0.16208228 42:−0.12200882 43:0.042528152 44:0.11466414 45:−0.38148123 46:−0.064043842 47:−0.16025119 48:−0.054537609 49:−0.040860493 50:0.032025494 51:−0.035186172 52:0.039553311 53:0.11930292 54:0.098108754 55:−0.095932513 56:0.22016686 57:−0.22589338 58:−0.03821544 59:−0.011686561 60:0.0094576897 61:−0.038782436 62:0.004929869 63:−0.035483625 64:0.094123557 65:0.033616606 66:−0.033419874 67:−0.0117603 68:−0.015409783 69:0.05488776 70:0.03093696 71:−0.087859683 72:0.018139809 73:0.017661583 74:−0.024666099 75:−0.029220678 76:−0.0032365189 77:0.043464635 78:−0.04635058 79:−0.006553371 80:−0.028600674 81:−0.021738222 82:0.25567371 # |
| 0.013907467001722892 1:4.9114671 2:1.881025 3:−0.4312326 4:−1.0641655 5:0.12501696 6:−0.95208728 7:−0.58141273 8:−1.4765189 9:−1.3497494 10:0.35631537 11:−0.21563196 12:0.44910482 13:0.26629686 14:0.64632457 15:0.58735436 16:−0.09227664 17:0.005969726 18:−0.32810408 19:0.67150372 20:0.50061023 21:−0.34934878 22:−0.17875439 23:−0.80896491 24:−0.39762643 25:−0.00054659497 26:0.093216814 27:0.29907921 28:0.17596127 29:0.21848349 30:−0.27703223 31:−0.021470813 32:0.4143658 33:0.48387161 34:0.37036732 35:0.40087342 36:0.1912006 37:0.045577448 38:0.50788224 39:0.25323871 40:−0.11682525 41:0.052113917 42:−0.014039285 43:0.099360727 44:0.32851189 45:−0.02387289 46:0.020685224 47:−0.21830137 48:−0.0026333325 49:0.36951706 50:−0.07711494 51:−0.1117034 52:0.1104875 53:−0.13321654 54:0.16284394 55:−0.076749213 56:−0.25630099 57:0.091850482 58:0.031225596 59:−0.096682802 60:−0.04278731 61:0.0061245607 62:−0.0032536373 63:0.024920253 64:−0.037868697 65:−0.024464281 66:−0.029764362 67:−0.086410515 68:0.042764217 69:0.08203695 70:−0.0575905 71:−0.045105629 72:0.012023785 73:−0.0032137455 74:0.0097442456 75:0.0048417118 76:0.02938132 77:0.038581576 78:−0.054621015 79:−0.052942444 80:−0.0097415131 81:0.021002205 82:0.25567371 # |
| −0.013907467001722892 1:6.7265453 2:−1.2866944 3:3.306459 4:3.0915554 5:0.055125013 6:−0.78283739 7:−1.8778273 8:2.7428708 9:1.8306189 10:2.2603297 11:−0.64129949 12:−0.50751668 13:−1.5948424 14:1.0712078 15:0.093467981 16:1.9911685 17:1.0591158 18:−0.47631627 19:−0.3054975 20:0.19572568 21:0.40692455 22:0.16577286 23:−0.19739529 24:0.37667075 25:−1.2619156 26:0.98176974 27:0.14582489 28:−0.45676509 29:−0.14546716 30:0.17664181 31:0.22698779 32:−0.015698573 33:−0.41211262 34:−0.1934886 35:0.0096197678 36:−0.031518675 37:−0.16534263 38:0.38527951 39:−0.33609757 40:0.48295787 41:−0.43648294 42:−0.0045264582 43:0.16016203 44:−0.10982558 45:−0.34294978 46:0.17653741 47:0.12474554 48:0.32409367 49:−0.039160468 50:0.26603052 51:−0.15840669 52:0.034365859 53:0.014296507 54:0.058963902 55:−0.053289052 56:−0.15648252 57:0.075846903 58:0.062794432 59:0.17199801 60:0.16369674 61:−0.10577346 62:0.072707146 63:0.084549032 64:0.012649695 65:−0.097975172 66:0.083616994 67:0.033059128 68:0.025682602 69:0.078859486 70:−0.052846812 |

APPENDIX C11-continued

SVM Model Weights
(82; Benign/Malignant)

71:−0.0023348203 72:0.020238888 73:−0.024740614 74:0.012658974 75:0.017390255
76:0.0021343629 77:0.013402897 78:0.0044597201 79:−0.002695275 80:−0.004668586
81:−0.013233411 82:0.25567371 #
−1.7072495123712783e−005 1:1.5452918 2:−7.1051722 3:1.5400574 4:0.31541255 5:−2.5128579
6:1.5362226 7:3.1012273 8:1.4823833 9:−1.2105137 10:−0.65580684 11:0.28774333
12:−0.90604997 13:−2.7234855 14:0.22590409 15:−0.28487211 16:−0.76438886 17:−0.612086
18:−0.20570815 19:0.93921202 20:0.73710173 21:−0.30659217 22:−0.69799072 23:0.9010272
24:0.055343203 25:−0.14589931 26:0.64925295 27:0.54710197 28:−0.23555608 29:0.085658111
30:0.5640856 31:−0.76448351 32:−0.050297733 33:−0.27225679 34:−0.098018602 35:0.08810433
36:−0.080082409 37:−0.29018632 38:−0.25814721 39:−0.040683508 40:−0.071939394
41:−0.1246088 42:0.0092769023 43:−0.12875327 44:0.22308037 45:−0.19514188 46:−0.28013644
47:0.37833536 48:−0.069209494 49:0.01326542 50:0.060387515 51:−0.043147374 52:0.29177517
53:0.17386179 54:0.025403481 55:−0.028271306 56:0.17681091 57:0.25203118 58:−0.29405716
59:−0.07518737 60:−0.15565519 61:−0.033752076 62:0.036341839 63:0.080811851
64:0.0017416074 65:−0.016262833 66:0.006181607 67:−0.054864045 68:0.032488722
69:0.031279992 70:−0.0037821492 71:−0.049426507 72:−0.026016336 73:−0.0074690362
74:0.035574779 75:−0.05231994 76:−0.0018968838 77:−0.022011682 78:0.016774161
79:−0.025810841 80:−0.018425204 81:−0.010104886 82:0.25567371 #
0.013907467001722892 1:5.7750597 2:1.2413872 3:−1.1963661 4:−2.0657933 5:0.40659559
6:0.49501371 7:−0.25784954 8:−1.4359365 9:−1.4816524 10:−0.79915047 11:−1.1229846
12:1.3343574 13:−0.068226963 14:0.24130811 15:−0.18656228 16:−0.77089977 17:0.62134808
18:0.71038228 19:0.68043411 20:0.18307337 21:0.25654551 22:0.22210953 23:0.015973803
24:−0.10899169 25:0.34026659 26:−0.21481249 27:0.57612687 28:−0.25969267 29:−0.00093713409
30:0.33880439 31:0.062518843 32:0.026924446 33:−0.044380542 34:0.22179085 35:0.12358794
36:0.38530976 37:−0.11988334 38:−0.18692164 39:−0.097517706 40:−0.34240344 41:0.053591926
42:0.28156355 43:0.13503785 44:0.12422437 45:0.14186762 46:0.23501907 47:−0.11156823
48:0.14907226 49:0.083217897 50:0.1704023 51:0.058815289 52:−0.12508999 53:−0.35887522
54:0.083101414 55:0.20775758 56:−0.021943498 57:−0.086027376 58:−0.020585524
59:0.041906465 60:0.14034607 61:0.083318733 62:0.004301751 63:−0.120638 64:0.05463789
65:−0.11770767 66:0.021522788 67:−0.071698181 68:−0.064277127 69:0.09282548 70:0.0073431199
71:−0.0041235308 72:−0.0018476698 73:−0.049712203 74:0.082828738 75:−0.039430786
76:0.032420084 77:−0.035563286 78:0.034488231 79:0.041123342 80:−0.016431013
81:−0.035637904 82:0.25567371 #
0.0059321838758126001 1:7.8969736 2:0.92601794 3:−0.67777443 4:−0.55101442 5:−0.8483538
6:1.133891 7:1.9279255 8:−0.36689714 9:−1.3092664 10:0.50407153 11:1.1446353 12:2.0337307
13:0.19430958 14:−0.031579688 15:−0.47634846 16:−0.19303134 17:−0.83120674 18:−0.81479317
19:−0.31509691 20:0.083579786 21:−0.58641762 22:−0.11711371 23:−0.083241984 24:0.31352392
25:0.54030591 26:−0.21814451 27:−0.68464237 28:0.17611556 29:−0.21217175 30:0.22453187
31:0.28514081 32:0.21957262 33:−0.10568819 34:−0.33947974 35:0.41626236 36:−0.31217927
37:−0.31725654 38:0.39849886 39:−0.033833142 40:−0.023524726 41:−0.39644381 42:−0.04659792
43:−0.1045945 44:−0.030585894 45:0.076296397 46:−0.07705164 47:0.023822628 48:−0.17652473
49:0.058780029 50:0.25980118 51:0.11905475 52:0.21615972 53:−0.064653613 54:−0.13955368
55:0.08933007 56:−0.18854204 57:−0.18888269 58:−0.020038534 59:0.19834851 60:−0.021020414
61:0.087139934 62:0.015825838 63:0.087334767 64:−0.087769322 65:0.066207908
66:−0.042856663 67:0.23534076 68:−0.060736533 69:0.075532936 70:−0.033088207 71:0.040556259
72:0.097355284 73:−0.047938652 74:−0.03784965 75:0.015495322 76:−0.095825158
77:−0.018465571 78:0.0066424366 79:−0.02361773 80:−0.0025011539 81:0.0033580973
82:0.25567371 #
−0.013907467001722892 1:0.73667067 2:0.57689101 3:−2.6979506 4:−3.327141 5:−0.67344189
6:0.039681029 7:−0.52642554 8:0.97267109 9:−2.2449265 10:−1.1802616 11:0.63944525
12:0.25607955 13:−0.76529783 14:0.58871859 15:0.77088851 16:0.77833068 17:−0.24253497
18:−0.19133268 19:−0.50323439 20:−0.26331607 21:0.063135564 22:−0.36104283 23:0.23057953
24:−0.24973908 25:−0.84037572 26:−0.15458417 27:0.20157091 28:−0.58805823 29:0.3385275
30:−0.83091402 31:−0.11370262 32:0.18096507 33:0.99642253 34:0.58041859 35:−0.43670434
36:0.037521597 37:−0.020368401 38:−0.25062132 39:0.24034923 40:0.32140419 41:−0.027384052
42:0.39551824 43:−0.011310609 44:0.14956598 45:−0.041891981 46:0.16419475 47:0.092045188
48:0.23672377 49:−0.31105936 50:−0.11614683 51:−0.031762369 52:−0.13805984 53:0.24754202
54:0.011226078 55:−0.1048087 56:−0.067295991 57:−0.12066343 58:−0.0052694501
59:0.041601948 60:−0.16585311 61:0.16877776 62:−0.10345203 63:0.050677657 64:−0.012582332
65:−0.10267125 66:−0.027802406 67:0.068567954 68:0.012743017 69:0.037426125
70:0.037635617 71:−0.0021199489 72:0.082846627 73:−0.011924988 74:−0.0071722507
75:−0.016278813 76:0.0030037272 77:0.041900769 78:0.015947433 79:0.023219859 80:0.027716408
81:−0.0054158745 82:0.25567371 #
−0.013907467001722892 1:3.9510243 2:2.5357125 3:2.0708675 4:−3.1424963 5:−1.4777241
6:1.0290573 7:2.4022179 8:−1.5407528 9:0.50040889 10:−1.3063754 11:−0.85427392
12:−0.27371067 13:0.42133543 14:−0.65560776 15:−0.1473923 16:1.6519809 17:−0.64535689
18:−0.19239971 19:−0.67702591 20:−0.8053599 21:−0.028416276 22:0.29436937 23:0.32449856
24:0.62685961 25:−0.1725231 26:−0.050195839 27:0.82813507 28:0.2202708 29:0.37998229
30:−0.31223077 31:0.47942221 32:−0.16758649 33:−0.27837166 34:0.37075794 35:0.37963516
36:−0.2199927 37:0.054357257 38:0.54777002 39:−0.013775124 40:0.18810743 41:0.46099341
42:−0.21565595 43:0.33451882 44:−0.31924656 45:0.22467512 46:−0.31382826 47:0.048348255
48:−0.16443725 49:0.13124336 50:0.33873451 51:−0.11771236 52:−0.063911349 53:0.14679374
54:0.12716164 55:0.098429099 56:0.019175077 57:0.11585929 58:−0.078180403 59:0.07249321
60:−0.013315481 61:0.13098404 62:−0.25718629 63:0.099447787 64:0.036771197
65:−0.028462475 66:0.038101979 67:−0.069853261 68:0.060544711 69:−0.040522601
70:−0.061978254 71:0.082902133 72:−0.036021128 73:−0.0065449202 74:0.039985109
75:−0.0058732582 76:−0.014843535 77:0.018123534 78:0.020565489 79:0.032844674

APPENDIX C11-continued

SVM Model Weights
(82; Benign/Malignant)

80:0.0027310967 81:−0.011110446 82:0.25567371 #
−0.013907467001722892 1:−2.9036043 2:−0.015519645 3:−2.12027 4:−3.3686247 5:−0.64384031
6:−0.77465332 7:−0.62911189 8:−1.4085542 9:0.29523042 10:0.068283439 11:0.95215201
12:−1.7381456 13:−0.76153582 14:−0.59636599 15:−1.1151897 16:1.6271036 17:0.51722294
18:0.54393601 19:−1.0967673 20:0.1607904 21:0.54946733 22:1.0153968 23:0.24043703
24:0.22614165 25:0.76501763 26:0.21507396 27:−0.17508405 28:0.091650218 29:−0.5685249
30:−0.43302134 31:0.086169973 32:0.44863382 33:0.0026869907 34:0.097948067 35:0.20386726
36:0.80023646 37:0.26964593 38:0.75347573 39:0.099260323 40:−0.33721927 41:−0.27831656
42:−0.26210928 43:0.0015067747 44:0.074263498 45:−0.13575707 46:0.056361642 47:0.34145796
48:−0.20454875 49:0.004581504 50:−0.070252538 51:0.060309697 52:0.059917849
53:0.060752217 54:0.12090433 55:−0.017430415 56:0.012467152 57:0.10000558 58:0.10616747
59:−0.054620955 60:0.062504694 61:0.024738129 62:0.033996195 63:−0.064383343
64:0.02988499 65:−0.038954813 66:−0.17739484 67:−0.09570951 68:0.030525655 69:0.045430642
70:0.04964295 71:−0.036810983 72:0.093061611 73:0.013555715 74:0.009561535
75:−0.031814493 76:−0.021449508 77:0.025517909 78:0.00029861977 79:−0.053519465
80:0.0029554837 81:−0.013174587 82:0.25567371 #
−0.013907467001722892 1:−4.6945429 2:−0.12180254 3:−5.4195595 4:−0.39896238 5:−1.1973656
6:1.1230381 7:−0.18971685 8:−0.79674339 9:1.556335 10:3.1867778 11:0.41255832
12:0.49717498 13:−0.39642346 14:−0.21752775 15:1.1833861 16:−1.8946335 17:−0.45730442
18:−0.3270669 19:0.59144479 20:−1.0068889 21:0.12804824 22:0.54577202 23:1.0277002
24:0.33942112 25:−0.22028325 26:−0.38777325 27:0.67974013 28:0.16676253 29:−0.069625311
30:−0.33583745 31:0.38871211 32:0.18896358 33:−0.1129126 34:0.064698204 35:−0.19369583
36:0.074449643 37:0.25621057 38:0.033426873 39:0.22339192 40:0.13368924 41:−0.11091734
42:0.13790497 43:0.21622027 44:0.0095193852 45:−0.06749931 46:−0.088926688
47:−0.049865335 48:−0.01809849 49:−0.0093459161 50:−0.0081770439 51:−0.12157734
52:0.043861423 53:−0.037204597 54:−0.07146202 55:0.016820243 56:0.0014766408
57:0.020146597 58:−0.043318357 59:−0.066056281 60:0.036098436 61:−0.08672668
62:−0.0023345535 63:−0.004739529 64:0.0090177674 65:0.0012144109 66:0.046158109
67:0.024586432 68:0.023633081 69:0.058330487 70:−0.01281919 71:−0.00010383644
72:0.012760108 73:0.010051476 74:−0.0022090706 75:0.011002054 76:−0.012289023
77:−0.0057613701 78:−0.0061325124 79:−0.0057473416 80:−0.0070351125 81:−0.0044562882
82:0.25567371 #
0.01134196256418994 1:7.4913383 2:−3.9047859 3:3.4765828 4:3.2329626 5:0.53025079
6:−0.78293818 7:−3.3953798 8:0.84023571 9:2.4344132 10:−0.43644863 11:4.1481657 12:2.5037875
13:−1.0712774 14:0.33500415 15:−1.2716551 16:−1.3413087 17:−1.0281113 18:1.4125737
19:−0.87757838 20:−1.0456495 21:1.7271733 22:−1.3155528 23:0.073792525 24:0.31123686
25:0.24695192 26:0.21360777 27:0.49629357 28:0.42675802 29:0.059230618 30:0.33964923
31:−0.33399045 32:−0.58854604 33:0.36823723 34:0.44327813 35:0.12133251 36:0.13571331
37:−0.011232215 38:0.22995608 39:−0.13251711 40:0.071975075 41:0.16731115 42:−0.069807798
43:0.10954643 44:0.18464498 45:0.17958513 46:−0.21301012 47:−0.0039448678 48:0.071943671
49:0.13296703 50:−0.0094828401 51:−0.049736559 52:0.032725573 53:0.091237344
54:−0.011919759 55:−0.091542624 56:−0.17174599 57:−0.061598003 58:−0.076554053 59:0.031846739
60:0.095506616 61:−0.049488027 62:0.031939235 63:−0.021930469 64:0.019977897
65:0.01592839 66:−0.13698398 67:−0.012340744 68:0.018055525 69:0.0011063165
70:−0.023735138 71:0.016703816 72:0.012794195 73:0.016682323 74:0.0050433376 75:0.014445791
76:0.045591265 77:0.0078134555 78:0.009789031 79:0.006489147 80:0.00072819984
81:0.011334216 82:0.25567371 #
0.013907467001722892 1:4.5205097 2:0.41893819 3:1.9438838 4:2.3802967 5:1.1299727
6:−0.60927874 7:−1.6264855 8:−1.0794646 9:1.5356162 10:0.22162989 11:0.63960916 12:0.85726005
13:−1.3424219 14:−0.65330589 15:−0.06476891 16:0.15953566 17:−0.14324568 18:−1.1498603
19:−0.32901207 20:0.079452172 21:−0.68063188 22:0.069432564 23:−0.3368676 24:0.27922544
25:−0.10262812 26:0.49262851 27:−0.24836577 28:0.191719 29:0.24267754 30:0.036177903
31:0.33137774 32:0.47188544 33:−0.086073026 34:0.40695095 35:−0.029295916 36:0.35678744
37:0.38728294 38:−0.34142995 39:−0.39300621 40:0.059112456 41:0.091618136 42:−0.12471116
43:−0.027963066 44:0.30494934 45:−0.32965988 46:0.015835421 47:−0.20211118 48:0.081562079
49:−0.27155653 50:−0.00037299481 51:0.13697444 52:−0.10090417 53:−0.086653844
54:−0.076424427 55:−0.05438754 56:−0.045778614 57:−0.10751832 58:−0.032505516 59:0.062980413
60:−0.24401571 61:−0.0015253403 62:0.045377731 63:−0.17513771 64:0.029685367
65:−0.1139576 66:−0.034587804 67:−0.1086087 68:0.0040583196 69:0.023088133 70:0.012975481
71:0.17019075 72:−0.035210948 73:0.06559618 74:0.035694119 75:−0.057021894
76:−0.091509789 77:−0.0012289417 78:0.032053754 79:−0.015924675 80:−0.030761207
81:−0.00081250304 82:0.25567371 #
−0.013907467001722892 1:4.9674916 2:−0.14554876 3:3.9842103 4:3.9956763 5:−2.2815819
6:1.1563058 7:−1.0191106 8:0.89716405 9:−2.8952029 10:−1.0914352 11:1.1478691
12:−0.45935875 13:−0.84680182 14:−0.48790786 15:0.91546565 16:0.19231048 17:−0.2439796
18:0.15177831 19:0.33076715 20:−0.52583331 21:−0.070626922 22:0.26622617 23:0.48583946
24:−0.047150921 25:−0.11219881 26:0.17808281 27:−0.047525957 28:−0.2929171 29:−0.15415367
30:0.058237724 31:−0.066451058 32:−0.50528657 33:−0.12466695 34:−0.28051186 35:−0.60495669
36:0.39991304 37:−0.20782937 38:0.27797747 39:0.089417182 40:0.042685047 41:−0.20166583
42:0.57370871 43:0.13477498 44:0.081074737 45:−0.20080233 46:−0.26178983 47:−0.061383769
48:−0.56866574 49:0.098209366 50:−0.00030178568 51:−0.069005974 52:−0.12234493
53:−0.066305265 54:0.015552847 55:0.10759126 56:0.07063552 57:0.056278311 58:0.18731274
59:−0.05263561 60:−0.035553332 61:0.025258247 62:−0.20842436 63:−0.28205624 64:0.014638638
65:9.7043448e−005 66:−0.0013818711 67:−0.010797383 68:−0.025900869 69:−0.066828564
70:−0.031161498 71:0.028685115 72:0.016492067 73:−0.039411314 74:−0.014713936 75:0.039363552
76:0.0018916043 77:0.0077915136 78:0.010886333 79:−0.038772773 80:0.010228094
81:−0.012744837 82:0.25567371 #

APPENDIX C11-continued

SVM Model Weights
(82; Benign/Malignant)

−0.013907467001722892 1:2.6516142 2:−3.8636723 3:1.7285326 4:−0.84835768 5:−1.9525275 6:−0.92642868 7:−0.060927413 8:1.025564 9:−1.4356234 10:−0.97310477 11:0.47097158 12:0.12962496 13:−0.25148878 14:−0.16546416 15:1.2693143 16:−1.1558002 17:0.1032875 18:0.56368762 19:0.0051629222 20:0.37761489 21:0.66011411 22:0.037132129 23:−0.85185379 24:0.3529858 25:0.25559223 26:−0.31852514 27:−0.16459604 28:0.08962936 29:0.14884865 30:0.078124739 31:−0.19779387 32:0.27305156 33:0.24598782 34:0.068362668 35:−0.052747477 36:−0.52633303 37:−0.32990932 38:−0.0136431 39:0.037923459 40:−0.02533986 41:−0.19024712 42:−0.45001119 43:−0.055180714 44:−0.15930174 45:0.22999269 46:−0.0079800794 47:−0.016092271 48:0.015435272 49:−0.16377443 50:−0.12950993 51:−0.095816039 52:0.14398758 53:−0.1553358 54:−0.24008743 55:−0.01991231 56:0.26443577 57:−0.0038756519 58:0.063613832 59:0.11179768 60:0.028500328 61:−0.048583873 62:−0.014190953 63:−0.082301058 64:0.066078283 65:−0.16223717 66:−0.052412942 67:−0.058284212 68:0.064628504 69:0.11475239 70:−0.0058859428 71:−0.018668987 72:0.044482555 73:−0.035470415 74:0.024470866 75:0.05869643 76:−0.035615463 77:−0.039454173 78:0.0076882099 79:0.0068195364 80:−0.0047788676 81:−0.026510926 82:0.25567371 #
−0.013907467001722892 1:5.5802693 2:1.231027 3:5.2537742 4:1.1331453 5:−0.69274801 6:−0.75143504 7:1.6902506 8:−0.60275358 9:1.5832503 10:−1.310573 11:1.6000917 12:0.21132684 13:1.6547322 14:0.78536803 15:1.5024594 16:−1.2832142 17:0.78004318 18:0.048497245 19:0.70713526 20:0.19592576 21:0.82509714 22:−0.66395086 23:−0.9106859 24:−0.52759343 25:−0.68078071 26:−0.42227072 27:−0.046701767 28:−0.11758283 29:−0.13602474 30:−0.55472362 31:0.32127804 32:−0.29026672 33:0.026724029 34:−0.67982489 35:0.11683097 36:0.38105908 37:0.81339836 38:0.064792126 39:−0.1046989 40:−0.37246537 41:0.079448678 42:0.080249004 43:−0.079302184 44:0.15513282 45:0.13945366 46:0.07593812 47:0.23029169 48:−0.011501194 49:0.18339215 50:0.31819478 51:−0.10053135 52:−0.040146928 53:0.13056313 54:0.0334806 55:−0.073444404 56:0.026649972 57:0.13169459 58:−0.08387766 59:−0.054674823 60:0.087010965 61:0.16560693 62:0.10817504 63:−0.0034023994 64:−0.047860574 65:−0.022291096 66:0.15961564 67:−0.07335978 68:0.0081768567 69:0.031859081 70:−0.024155067 71:0.0053942795 72:0.0085884286 73:−0.013401117 74:−0.04092462 75:−0.034990955 76:−0.068524428 77:−0.024430975 78:0.024381608 79:−0.0061947964 80:0.011881717 81:0.0049195392 82:0.25567371 #
−0.013907467001722892 1:2.8263021 2:2.0819416 3:0.27921975 4:3.5768628 5:2.1439619 6:−0.928078 7:0.57754159 8:0.18754894 9:0.85823959 10:−0.20131943 11:0.9482286 12:−0.3214485 13:0.82514054 14:−0.37589139 15:−0.46151185 16:−0.14956723 17:1.0633585 18:−0.23653288 19:−0.69588399 20:−0.36893174 21:0.80763328 22:0.93069547 23:0.5691483 24:0.051402833 25:−0.49605268 26:−0.35761532 27:0.29959068 28:0.071002714 29:−0.32978484 30:0.074714996 31:0.29977348 32:0.051678911 33:−0.065063447 34:−0.19315234 35:0.12445268 36:−0.083052307 37:−0.27206311 38:−0.14154203 39:−0.0099441661 40:−0.13220401 41:−0.084780566 42:0.29198474 43:−0.17320052 44:0.14757854 45:0.36334974 46:−0.00088060874 47:0.25512359 48:−0.15208158 49:0.081146725 50:0.13082041 51:0.18624927 52:−0.12077775 53:−0.27191135 54:−0.10174364 55:−0.089331053 56:0.24547873 57:0.12048637 58:0.012943591 59:−0.064267114 60:−0.22911343 61:−0.06396129 62:−0.10194229 63:0.1018229 64:0.05100688 65:−0.035625666 66:−0.097171009 67:0.052742429 68:−0.012774102 69:0.12951221 70:−0.11032252 71:−0.014010696 72:−0.087575667 73:0.086608738 74:−0.031695276 75:−0.039034512 76:−0.0098189032 77:0.036850549 78:−0.0081621092 79:−0.0044356552 80:0.017246954 81:0.014129912 82:0.25567371 #
−0.006008193170703828 1:−0.95156485 2:−1.4612938 3:−1.9358456 4:4.142127 5:2.3198798 6:−0.8098883 7:−0.062391788 8:−0.2045166 9:0.59073448 10:−0.35547227 11:1.1693912 12:0.04870981 13:0.38277781 14:−0.84573781 15:−0.69391251 16:−0.30454978 17:−0.048881855 18:0.79620856 19:−0.67925942 20:−0.58325279 21:−0.14840429 22:1.0766706 23:−0.12342793 24:−0.30171189 25:−0.35856178 26:−0.050720979 27:0.17337419 28:0.35579562 29:0.0016297076 30:0.14343478 31:0.012612592 32:0.29579583 33:0.001519282 34:0.24851383 35:0.29560471 36:−0.71149588 37:−0.54203129 38:0.14251469 39:0.042433999 40:−0.083985254 41:0.21143067 42:0.29311562 43:−0.015808009 44:0.010919767 45:−0.12606128 46:−0.18861698 47:−0.092081122 48:−0.050991539 49:−0.12376861 50:−0.12954277 51:0.067679785 52:−0.021818671 53:−0.028279521 54:0.20420086 55:−0.18519723 56:0.021138323 57:0.15057296 58:0.17164539 59:0.072332397 60:−0.079251938 61:0.027409907 62:0.21861017 63:−0.032445319 64:−0.12992743 65:−0.025126725 66:0.099937499 67:−0.039133847 68:−0.070081063 69:−0.039291058 70:−0.061459426 71:0.075261489 72:0.00022250738 73:0.0096261436 74:−0.091079406 75:−0.031815041 76:0.061698385 77:−0.021042818 78:0.017599938 79:−0.020616282 80:0.024593076 81:−0.020546319 82:0.25567371 #
0.013907467001722892 1:−0.90334266 2:−0.17248048 3:−2.7752664 4:1.1900781 5:0.094684064 6:−1.1127622 7:0.95915526 8:−0.11894368 9:−1.9841946 10:0.98468214 11:−0.063944846 12:−1.2487289 13:−0.61380386 14:−0.081862666 15:0.45095441 16:−0.14827082 17:−0.34864795 18:−0.10256285 19:0.78000957 20:0.132852 21:−0.70506185 22:−0.5006085 23:−0.51431841 24:0.064407617 25:−0.012871034 26:0.20345646 27:0.69678706 28:−0.055522114 29:0.49264035 30:−0.57151598 31:−0.14761893 32:−0.36137059 33:0.24056736 34:0.31852552 35:0.38182795 36:0.15162958 37:−0.16074447 38:−0.10231055 39:−0.29446667 40:−0.034709014 41:0.013383803 42:−0.45942831 43:−0.26025862 44:0.11545254 45:0.19368258 46:−0.11176641 47:−0.073980585 48:0.1160283 49:−0.22157539 50:0.11302762 51:0.15371066 52:0.011127962 53:0.082207575 54:−0.14845748 55:0.038335916 56:−0.11641344 57:0.17554255 58:0.16148333 59:0.18758091 60:−0.0087398672 61:0.11934838 62:−0.06777487 63:−0.16490252 64:0.025555857 65:0.082081333 66:0.068066739 67:0.012967656 68:−0.030097725 69:0.036972791 70:−0.071138203 71:−0.035688844 72:−0.03923003 73:0.019451048 74:−0.086258583 75:0.015425643 76:0.0086982613 77:−0.014518014 78:−0.028397392 79:−0.03541936 80:−0.0071728951 81:0.013880501 82:0.25567371 #
0.013907467001722892 1:1.8544763 2:0.59755039 3:−0.79748476 4:−2.3416038 5:−0.31617919 6:−1.7428496 7:1.4032595 8:0.70431572 9:−0.32135081 10:−1.2155011 11:−0.66844577

APPENDIX C11-continued

| SVM Model Weights (82; Benign/Malignant) |
|---|
| 12:−0.022841355 13:0.20576999 14:0.034293417 15:0.37033224 16:0.11670563 17:−0.54367113 18:−0.28741112 19:−0.19359446 20:0.18392375 21:0.75075698 22:−0.18692803 23:1.5600741 24:−0.59214377 25:−0.071142018 26:−0.032774579 27:−0.6389212 28:0.060992721 29:0.13494793 30:0.37196639 31:0.57425427 32:0.23330681 33:0.080437966 34:−0.25248474 35:−0.28238821 36:−0.095884562 37:−0.53492713 38:0.26298654 39:−0.051503278 40:0.072312817 41:−0.43661448 42:0.38524631 43:0.0637393 44:0.012160919 45:0.16305904 46:0.17714104 47:−0.07988701 48:−0.011625712 49:0.034479149 50:−0.024200199 51:−0.023429319 52:−0.17002793 53:0.16121902 54:0.032292444 55:−0.0012829674 56:−0.01598312 57:−0.18066128 58:0.14492384 59:0.086638808 60:0.10272907 61:0.015681462 62:0.15333435 63:0.018104296 64:−0.038739048 65:0.035916463 66:−0.069279827 67:−0.19349106 68:−0.0097160777 69:0.012230255 70:0.045809574 71:0.0089093447 72:−0.11629963 73:0.0044422564 74:−0.031537056 75:0.025053348 76:−0.031081989 77:−0.057609919 78:−0.015531697 79:−0.012613344 80:−0.017734094 81:0.025515305 82:0.25567371 # |
| 0.013907467001722892 1:−2.6282666 2:0.83478689 3:−1.0721512 4:−0.50045788 5:0.90949649 6:−4.4946704 7:1.6457027 8:1.1746408 9:1.4231101 10:1.4456066 11:−0.88033259 12:−2.1333191 13:−0.021883188 14:−0.25062913 15:−0.083297908 16:−0.85392404 17:−0.90693456 18:0.2970351 19:0.45055535 20:−0.09995576 21:0.51076323 22:−0.43670028 23:0.36476621 24:−0.95451641 25:−0.20031053 26:0.67508286 27:−0.93244702 28:0.13081406 29:0.49241167 30:0.19104499 31:0.10779955 32:−0.14122751 33:0.20688738 34:0.58228528 35:0.24433109 36:0.23911078 37:−0.24889952 38:0.098726369 39:−0.30660385 40:−0.31343117 41:−0.16456582 42:−0.01780645 43:−0.25943229 44:−0.18028945 45:−0.013832724 46:−0.30424732 47:0.011103727 48:0.19893953 49:0.15702514 50:0.157456 51:−0.10128386 52:−0.37126845 53:−0.15268441 54:−0.026283927 55:0.057599667 56:−0.1776019 57:0.030656785 58:0.080303207 59:−0.19281329 60:−0.05002901 61:0.070550852 62:−0.049463794 63:−0.0031679443 64:−0.0080655394 65:0.03979427 66:−0.021794694 67:0.10237613 68:0.10694979 69:−0.042682458 70:−0.0027413336 71:−0.012581909 72:0.031564515 73:0.02635918 74:0.060980991 75:−0.025426019 76:−0.009149556 77:−0.055161502 78:−0.0061266674 79:−0.00096103584 80:0.026131971 81:−0.0097358981 82:0.25567371 # |
| 0.013907467001722892 1:1.−1127092 2:1.023582 3:−1.5002574 4:1.8848284 5:−2.006686 6:2.490242 7:−0.87186319 8:−1.4726433 9:0.6027776 10:1.1853744 11:−0.53339785 12:−1.2645619 13:−1.2797507 14:−1.4723375 15:0.71425682 16:−0.95632237 17:0.41502073 18:0.36608824 19:0.20266438 20:−0.64730287 21:−0.50698137 22:0.33851576 23:−0.19023597 24:−0.2465242 25:−0.4008525 26:−0.33370984 27:−0.55771083 28:−0.068153739 29:−0.41869354 30:0.28123131 31:0.014431863 32:−0.38049388 33:0.35358033 34:−0.090570942 35:−0.077888496 36:−0.19125997 37:0.069411792 38:0.44386697 39:0.093403146 40:−0.26473638 41:0.31485 42:−0.33032715 43:0.010382273 44:0.42881086 45:−0.21265373 46:0.18693933 47:−0.10689343 48:0.30427253 49:−0.02460172 50:0.23295447 51:0.27729601 52:0.059468519 53:0.060993299 54:0.161459 55:0.19150555 56:0.095879868 57:−0.022795422 58:−0.22619762 59:−0.052827813 60:−0.05607108 61:0.078360587 62:0.090560146 63:0.048996687 64:0.029384816 65:−0.044721246 66:−0.16036934 67:0.00092239247 68:0.075319141 69:−0.023949515 70:0.032674041 71:0.05127484 72:−0.029712975 73:−0.10757741 74:−0.11360387 75:0.039749134 76:0.024440231 77:0.00040882183 78:0.021113714 79:0.014207585 80:0.0073096775 81:0.01038999 82:0.25567371 # |
| −0.013907467001722892 1:−4.6945429 2:−0.12180254 3:−5.4195595 4:−0.39896238 5:−1.1973656 6:1.1230381 7:−0.18971685 8:−0.79674339 9:1.556335 10:3.1867778 11:0.41255832 12:0.49717498 13:−0.39642346 14:−0.21752775 15:1.1833861 16:−1.8946335 17:−0.45730442 18:−0.3270669 19:0.59144479 20:−1.0068889 21:0.12804824 22:0.54577202 23:1.0277002 24:0.33942112 25:−0.22028325 26:−0.38777325 27:0.67974013 28:0.16676253 29:−0.069625311 30:−0.33583745 31:0.38871211 32:0.18896358 33:−0.1129126 34:0.064698204 35:−0.19369583 36:0.074449643 37:0.25621057 38:0.033426873 39:0.22339192 40:0.13368924 41:−0.11091734 42:0.13790497 43:0.21622027 44:0.0095193852 45:−0.06749931 46:−0.088926688 47:−0.049865335 48:−0.01809849 49:−0.0093459161 50:−0.0081770439 51:−0.12157734 52:0.043861423 53:−0.037204597 54:−0.07146202 55:0.016820243 56:0.0014766408 57:0.020146597 58:−0.043318357 59:−0.066056281 60:0.036098436 61:−0.08672668 62:−0.0023345535 63:−0.004739529 64:0.0090177674 65:0.0012144109 66:0.046158109 67:0.024586432 68:0.023633081 69:0.058330487 70:−0.01281919 71:−0.00010383644 72:0.012760108 73:0.010051476 74:−0.0022090706 75:0.011002054 76:−0.012289023 77:−0.0057613701 78:−0.0061325124 79:−0.0057473416 80:−0.0070351125 81:−0.0044562882 82:0.25567371 # |
| 0.012954086512475399 1:8.9885941 2:1.8290443 3:0.6682806 4:1.8977114 5:0.2111315 6:1.4486016 7:1.5891277 8:0.51667082 9:−0.45382538 10:0.37770146 11:1.4604316 12:−0.53692782 13:0.33008865 14:0.12025584 15:−0.47337285 16:0.81005949 17:−0.90420789 18:−1.1529511 19:0.14843556 20:0.52506375 21:−0.14618051 22:−0.38169765 23:0.28298774 24:−0.17610143 25:−0.16045612 26:−0.38617054 27:−0.23377834 28:−0.17096598 29:−0.31132868 30:−0.28275463 31:0.567393 32:−0.003180447 33:−0.30157489 34:−0.10600054 35:−0.067518502 36:0.12645781 37:0.32555887 38:0.024926931 39:0.027674131 40:−0.089047395 41:0.2231729 42:−0.057629377 43:−0.2478247 44:0.051743515 45:−0.056137752 46:−0.037311137 47:0.091319703 48:−0.052318834 49:−0.12788996 50:−0.063007563 51:−0.27891973 52:0.17528422 53:0.10212162 54:−0.20058389 55:0.11364536 56:0.042440534 57:−0.13886581 58:0.16312324 59:0.029018704 60:−0.081211433 61:0.022779236 62:0.12002778 63:−0.057416808 64:−0.032383278 65:−0.10886707 66:−0.047755949 67:0.07679946 68:0.20172027 69:0.016547197 70:−0.036911912 71:0.045635313 72:−0.055165216 73:−0.0016069475 74:0.0022157095 75:−0.080787316 76:0.094537109 77:−0.0010178279 78:−0.040378872 79:0.016298061 80:0.0086559476 81:0.0042480147 82:0.25567371 # |
| 0.013222397728898374 1:6.1311321 2:−1.449001 3:−0.57033795 4:2.829073 5:−0.54553241 6:0.52253419 7:−0.31110352 8:1.1493531 9:−1.8091886 10:1.7111456 11:−1.4512421 12:1.3597342 13:0.48646131 14:−0.33656454 15:−1.0743009 16:0.014130141 17:0.2635656 18:0.82064271 |

APPENDIX C11-continued

SVM Model Weights
(82; Benign/Malignant)

19:0.022797845 20:−0.011084788 21:−0.23568472 22:−0.49814716 23:0.084631167 24:0.37609193
25:0.4684315 26:−0.15267721 27:−0.55006868 28:0.21759127 29:−0.93633556 30:0.21583951
31:0.4219662 32:0.59709024 33:0.15824614 34:−0.20452014 35:0.09279108 36:0.051853437
37:0.43101412 38:−0.19706321 39:−0.097142942 40:−0.043110125 41:−0.14639351 42:−0.22077551
43:−0.23835321 44:0.134718 45:−0.32846063 46:−0.22746591 47:−0.029558768 48:−0.22208628
49:−0.084680356 50:−0.26163554 51:−0.1501175 52:−0.13144459 53:0.12858143 54:−0.038044959
55:−0.25411266 56:−0.13101526 57:0.19287843 58:0.0013226281 59:−0.11266329 60:0.046038356
61:0.011316258 62:−0.098507404 63:−0.042892944 64:−0.052089367 65:0.12561588
66:0.083012052 67:−0.022982076 68:−0.021355366 69:0.0024144817 70:0.001330824
71:−0.0090090735 72:−0.019158173 73:−0.070744455 74:0.0018014011 75:−0.043636497
76:0.025647169 77:0.014638677 78:−0.015977712 79:0.07013841 80:−0.029147873
81:−0.0038464246 82:0.25567371 #
−0.013907467001722892 1:2.0031488 2:−0.67842001 3:0.44213089 4:0.6811651 5:−0.78669143
6:−1.0678015 7:1.4386762 8:1.3017488 9:0.75788456 10:−0.45266727 11:−1.0440437 12:−0.6593917
13:−0.39494324 14:0.021119917 15:2.0002339 16:−0.21656482 17:−0.88875836 18:0.69003016
19:−1.772155 20:−0.25708261 21:0.38368368 22:−0.077066489 23:0.5909707 24:−0.17227726
25:0.46461707 26:0.16448818 27:0.078015275 28:−0.66810292 29:0.38202372 30:0.17369455
31:−0.18925241 32:−0.16194759 33:−0.037100539 34:0.21753789 35:−0.0020654835 36:0.027552705
37:0.55491364 38:0.28649354 39:0.096833304 40:0.076695696 41:−0.46253744 42:−0.4057757
43:−0.23572676 44:−0.097260721 45:−0.055168856 46:0.31552151 47:−0.14050844 48:−0.2015069
49:0.098560065 50:−0.19676666 51:0.37422544 52:−0.022199269 53:−0.11253084
54:−0.075697213 55:0.14363527 56:−0.0037540165 57:−0.027954381 58:−0.030636728 59:0.13821042
60:−0.16577704 61:−0.037911136 62:−0.085799456 63:0.1292695 64:−0.047572818
65:0.095524371 66:0.089045763 67:−0.076423198 68:−0.04064459 69:0.0051778844
70:−0.063186496 71:0.064982608 72:−0.028092701 73:−0.064993031 74:−0.00011155089
75:−0.056291964 76:0.045785759 77:0.02574181 78:0.028734505 79:0.014406766 80:−0.0033712317
81:0.0051492788 82:0.25567371 #
−0.013907467001722892 1:3.9212999 2:3.566597 3:1.8374902 4:0.43481648 5:−0.32375222
6:−0.22354333 7:2.7280138 8:−0.64180356 9:1.3553795 10:−1.284534 11:−0.44129243 12:0.76390254
13:1.0450907 14:0.55469579 15:1.2354478 16:0.30634344 17:0.0069720512 18:0.55400532
19:−0.86681271 20:−0.72659063 21:−1.04723 22:0.62293088 23:0.44831875 24:−0.54442555
25:−0.40406826 26:0.61084908 27:0.20908979 28:−0.32455501 29:−0.52932245 30:−0.51294595
31:−0.47475162 32:−1.0189837 33:−0.60586298 34:0.018532177 35:0.027400291 36:−0.2816073
37:−0.21930307 38:0.077345341 39:−0.14125608 40:0.12979583 41:−0.12148686 42:−0.16431832
43:0.12497108 44:0.30679032 45:0.27466041 46:−0.047262106 47:−0.32783848 48:0.11711142
49:−0.43185791 50:−0.13590674 51:−0.044483338 52:0.096823931 53:0.01660171 54:0.13181353
55:−0.13089696 56:−0.11710397 57:0.11604164 58:0.034584589 59:−0.27541587 60:0.009696289
61:−0.05325662 62:0.085433245 63:−0.090851635 64:−0.041413523 65:0.03277754
66:−0.098245278 67:0.081262179 68:−0.014922589 69:0.01877556 70:0.036610972 71:−0.041879177
72:0.019671474 73:−0.029775064 74:0.047633257 75:−0.045100961 76:−0.065669894
77:−1.5598301e−006 78:−0.0089921178 79:−0.009113933 80:0.0062781661 81:−0.0070028822
82:0.25567371 #
0.0086083549442791084 1:−4.8538885 2:11.710081 3:−6.1273899 4:−2.1153672 5:−4.4813523
6:1.4796681 7:−0.44303796 8:7.079536 9:3.3811548 10:−0.5132193 11:1.3672465 12:3.1838846
13:−0.29501393 14:−3.5256567 15:−0.061914153 16:1.1134801 17:1.275921 18:−0.70325166
19:0.61716264 20:0.51627302 21:−0.0069604195 22:−0.70252401 23:−0.39224711 24:−1.1683948
25:0.82210463 26:0.46094421 27:0.64264548 28:−0.25475097 29:0.19444466 30:−0.0011032472
31:−0.27570698 32:0.14102077 33:−0.10242313 34:−0.11378312 35:0.0038855532
36:−0.086297758 37:0.016517581 38:0.093544208 39:−0.078683227 40:−0.065110862
41:0.0084226159 42:−0.0030192798 43:−0.091996312 44:−0.016666805 45:0.059278809
46:−0.021474335 47:−0.0078619346 48:−0.068695121 49:0.045661371 50:0.036525968
51:0.0021103951 52:−0.034267608 53:−0.030208096 54:0.04568686 55:0.0035646434
56:0.044756554 57:0.068234123 58:0.033329569 59:−0.022423359 60:−0.027939791
61:−0.0045029349 62:0.0027859767 63:−0.0059253825 64:−0.017926294 65:0.0038082977
66:−0.0024527879 67:0.003707815 68:0.022540096 69:0.012512609 70:0.0024222319
71:0.014129626 72:−0.010344648 73:−0.0067008771 74:0.0057701045 75:−0.011191138
76:0.002803969 77:−0.0004737273 78:0.0051786685 79:−0.0074322252 80:0.0015181281
81:−0.00055338157 82:0.25567371 #
0.013907467001722892 1:−0.93003571 2:1.9523538 3:−1.3415461 4:2.4822686 5:0.19890998
6:−1.3313334 7:0.068564743 8:1.1664286 9:−1.6925697 10:0.64675099 11:0.43679509 12:−1.2038205
13:−1.0886772 14:−1.1802665 15:−1.2105626 16:−0.52334678 17:−0.015777761 18:0.52192599
19:−0.69480109 20:0.51186997 21:−0.17781456 22:−0.16893376 23:0.2202893 24:0.04695994
25:−0.23932269 26:−0.26738259 27:−0.37583995 28:−0.097258806 29:0.31264219 30:−0.33379513
31:−0.057046022 32:−0.26168492 33:0.14598083 34:−0.25049546 35:−0.0063634012 36:−0.15654676
37:0.27867839 38:0.3609097 39:0.031608328 40:0.20994972 41:−0.14257182 42:−0.01695567
43:0.031696908 44:−0.13628739 45:0.14854252 46:0.11900226 47:0.052805219 48:0.20748328
49:−0.11481464 50:−0.16765293 51:−0.28109935 52:−0.034576949 53:−0.13761055 54:0.13690926
55:−0.016474174 56:0.26700494 57:0.019943472 58:−0.22473879 59:0.052825619 60:0.048054855
61:0.19356035 62:−0.0046279067 63:−0.028773671 64:−0.074693203 65:−0.086811244
66:0.11018614 67:−0.0007967506 68:0.032238793 69:−0.10468556 70:0.00088952942
71:−0.004508703 72:0.0078438055 73:0.10606468 74:0.012737298 75:0.040625557 76:−0.0024400048
77:−0.0085069044 78:−0.015561501 79:−0.047353297 80:−0.056701999 81:0.016181318
82:0.25567371 #
−0.013868326505241599 1:−1.6070163 2:−1.4052042 3:−4.0777016 4:2.3651009 5:1.1612253
6:0.75643831 7:1.1978906 8:0.95098656 9:−2.0611238 10:−0.27574006 11:−1.9000568
12:0.34110045 13:−0.076513924 14:0.25994152 15:0.15452176 16:−0.1924206 17:−0.10815294
18:0.022219649 19:−0.18281053 20:0.96562475 21:0.038445167 22:−0.53843951 23:0.30832392

APPENDIX C11-continued

SVM Model Weights
(82; Benign/Malignant)

24:0.42351493 25:−0.12960196 26:1.5336051 27:−0.20165344 28:−0.01682375 29:0.073752783
30:−0.3915596 31:0.1210214 32:−0.08615502 33:−0.096842602 34:−0.0070559354 35:−0.11877518
36:0.27118748 37:0.35530332 38:−0.43410465 39:−0.015395478 40:−0.063821651
41:−0.076799929 42:−0.00010866803 43:0.57033777 44:−0.02278202 45:0.31349382 46:0.066868268
47:0.017357457 48:−0.14546211 49:0.27975646 50:0.079885893 51:−0.058864441
52:−0.087735489 53:−0.046799622 54:0.11227116 55:−0.29120412 56:0.099196032 57:0.049391106
58:−0.18051778 59:0.057342004 60:0.049808994 61:0.10630471 62:0.030029463 63:0.010906108
64:0.042480599 65:0.12332004 66:−0.18001336 67:0.072331712 68:−0.067071445 69:0.035150338
70:0.049997542 71:0.13350214 72:0.046294019 73:0.019821577 74:−0.072682619
75:−0.0099783475 76:0.031325772 77:−0.024302775 78:0.0030211271 79:0.0055105453
80:0.00023924046 81:−0.0033595334 82:0.25567371 #
−0.010287182018494238 1:−3.6045039 2:−2.6820505 3:−0.37993345 4:−1.3927106 5:1.2953225
6:−1.4589797 7:0.82863575 8:−1.49134 9:1.7670006 10:−0.52219647 11:−0.30546001 12:−1.1860214
13:−1.0020293 14:−0.41430363 15:−1.7545762 16:−0.2967518 17:0.40785378 18:−0.59492874
19:0.41539657 20:0.058743171 21:0.14152229 22:−0.67042965 23:−0.7818079 24:0.44719395
25:0.39812925 26:−1.0744703 27:−0.10559598 28:−0.53489947 29:0.55216408 30:0.19978507
31:0.073598556 32:0.21343429 33:−0.47784299 34:0.17236954 35:−0.21911983 36:0.01257569
37:−0.26263791 38:−0.0061564129 39:0.42373967 40:0.33201087 41:−0.2279844 42:0.19577718
43:0.20928508 44:0.045495301 45:0.36827281 46:−0.4428651 47:−0.01399814 48:0.031118467
49:−0.1407575 50:0.098976381 51:0.17404512 52:0.17451191 53:−0.073980682 54:−0.071008936
55:−0.14925669 56:−0.039997995 57:−0.030250147 58:−0.02634345 59:−0.073953852
60:0.10451249 61:0.043762267 62:0.066126816 63:−0.060991239 64:0.037385963
65:0.082934633 66:0.10119417 67:−0.052110482 68:0.062524348 69:0.0040958631
70:0.12281678 71:0.094138131 72:0.0069719465 73:−0.096599311 74:0.0076357406
75:−0.090300873 76:−0.0086369254 77:0.051993534 78:0.013033064 79:−0.039026793
80:0.019860353 81:0.01500743 82:0.25567371 #
−0.013907467001722892 1:−0.029553974 2:1.1957196 3:0.61999649 4:0.71083826 5:0.17549181
6:−2.3301337 7:0.97077262 8:0.58165997 9:0.030121624 10:1.3949789 11:2.0851276
12:−1.8459338 13:−1.4897755 14:0.78728217 15:1.3469397 16:−0.19942141 17:0.50883973
18:0.22627038 19:−0.036830902 20:0.83976758 21:0.38402358 22:−0.40425029 23:−0.080880001
24:−0.74652475 25:0.36664006 26:−0.97949159 27:0.023829354 28:0.59824419 29:0.26942089
30:−0.3533175 31:0.38241255 32:−0.0019619528 33:−0.20920593 34:−0.018472206 35:0.67914933
36:−0.0010762719 37:0.16722722 38:−0.36606553 39:0.24336375 40:0.23017181 41:−0.053131726
42:0.15948923 43:0.029117379 44:0.061404489 45:−0.048055328 46:0.26286668 47:0.058831047
48:0.1334981 49:−0.036070727 50:0.0013411797 51:−0.0019771275 52:0.015354604 53:0.1222948
54:0.24071427 55:0.035047222 56:0.20032105 57:0.044402551 58:0.14550228 59:−0.06231229
60:−0.016845841 61:−0.076930247 62:0.040880624 63:0.064999685 64:−0.04636566
65:0.08030995 66:−0.16689803 67:0.064327404 68:−0.11008617 69:−0.02087692 70:−0.083477795
71:0.080636069 72:0.011140353 73:−0.065788276 74:0.10886487 75:−0.057353571
76:0.015810991 77:−0.0068874885 78:0.019137098 79:−0.015532231 80:−0.02345923
81:−0.010197603 82:0.25567371 #
0.013907467001722892 1:4.4362383 2:−1.6793963 3:−1.566292 4:−3.2077858 5:−0.11678144
6:0.7605294 7:0.29261148 8:−1.278756 9:1.1692907 10:−2.11836 11:0.52350706 12:−0.30659074
13:−0.63028836 14:0.67320037 15:−0.27765042 16:−0.42263666 17:−0.20966066 18:0.55657989
19:0.48068836 20:−1.1350296 21:0.61448622 22:0.11811619 23:−0.79956645 24:−0.092827193
25:0.35141432 26:0.72457081 27:0.15202697 28:−0.044791702 29:0.42401895 30:−0.31778312
31:−0.022386912 32:0.28809917 33:0.28285724 34:0.01201927 35:−0.645464 36:0.014711171
37:0.20914036 38:0.20477214 39:−0.093773507 40:0.16199635 41:0.15505062 42:−0.034417354
43:−0.12293445 44:−0.075000361 45:−0.10459624 46:0.2939519 47:0.38339579 48:−0.14820908
49:−0.28643247 50:0.075699151 51:0.16899164 52:0.034425896 53:−0.03567699 54:−0.06551481
55:0.06629619 56:0.13784975 57:0.15962863 58:0.25510088 59:0.025308501 60:0.12040595
61:−0.07515613 62:0.15167382 63:0.039869078 64:0.13904765 65:0.15746514 66:−0.011108508
67:0.088991702 68:0.0076717408 69:−0.010888851 70:0.0083461413 71:−0.064647026
72:−0.061004426 73:0.015027825 74:−0.036001131 75:−0.031109048 76:0.0010749488
77:−0.00092590484 78:−0.027721051 79:0.010505742 80:−0.024915585 81:−0.0061497437
82:0.25567371 #
−0.013907467001722892 1:−0.37857983 2:−3.1108689 3:−1.5834622 4:−1.3426373 5:0.54694682
6:−0.38148504 7:−2.0734801 8:0.0047648158 9:−2.357964 10:−1.0196906 11:−0.72981006
12:−1.1445125 13:−1.1846863 14:−0.92250514 15:−0.8718431 16:0.061195843 17:1.1091851
18:0.74069268 19:−0.60632581 20:1.0782501 21:0.86193287 22:0.31244257 23:0.57742274
24:−0.47402048 25:−0.70036286 26:0.66894895 27:0.60239846 28:−0.10635167 29:−0.5586589
30:0.071726315 31:0.41283643 32:0.14371471 33:0.10558783 34:0.19127405 35:0.097074881
36:−0.29764381 37:0.041922342 38:−0.49174398 39:0.69082326 40:−0.52308041 41:0.29848841
42:−0.28855282 43:−0.19248204 44:0.029485142 45:0.14557739 46:−0.23288836 47:0.03455437
48:−0.017498391 49:0.042841069 50:0.19948523 51:0.097905472 52:0.055405904 53:0.15912542
54:0.019523405 55:−0.00086101226 56:−0.13273484 57:−0.13073885 58:0.12126263
59:−0.042046476 60:0.025787855 61:−0.13941061 62:−0.053604525 63:−0.0052043996
64:−0.065407723 65:−0.0039703646 66:0.052017268 67:0.12066881 68:0.10263842 69:0.046252824
70:0.011715115 71:0.026410792 72:−0.04527035 73:0.0065903608 74:0.020485729
75:0.032959186 76:−0.050943431 77:−0.0060377745 78:0.036216259 79:−0.0092947185
80:−0.0099762734 81:0.00053479668 82:0.25567371 #
0.013907467001722892 1:0.96451378 2:0.74506444 3:−1.8287807 4:−2.2337189 5:0.70528638
6:−2.6976771 7:−0.50955325 8:0.082813539 9:−1.3721836 10:0.25417566 11:−0.091573454
12:−1.4882948 13:−0.27992651 14:−0.22746059 15:−0.6088056 16:0.024793975 17:−0.22156215
18:−0.18072195 19:0.10881592 20:0.082345754 21:−0.13435215 22:−0.19221406 23:0.34319305
24:−0.55437326 25:0.031420056 26:−0.31870744 27:0.2597647 28:0.15074149 29:0.35541058
30:0.10976756 31:0.035092495 32:0.17241041 33:−0.049967669 34:−0.8761546 35:0.091068119

APPENDIX C11-continued

| SVM Model Weights (82; Benign/Malignant) |
| --- |
| 36:−0.41322049 37:0.42111424 38:0.16279258 39:−0.19285816 40:0.26147491 41:0.10701151 42:−0.062286235 43:−0.091022246 44:−0.13316067 45:−0.046054926 46:−0.18365099 47:0.16694836 48:0.099099152 49:−0.099710472 50:0.13639663 51:−0.05594169 52:0.18959399 53:−0.085140981 54:−0.15233687 55:−0.12635775 56:−0.10323367 57:−0.032698553 58:−0.051967654 59:−0.092892386 60:−0.048081353 61:0.1134521 62:−0.0097223511 63:−0.19677512 64:0.038886372 65:−0.008903442 66:−0.19350731 67:−0.10775119 68:−0.087278858 69:−0.0070919083 70:−0.063219547 71:−0.039190117 72:−0.032200355 73:0.00085241214 74:−0.011032113 75:0.02572496 76:−0.021514339 77:0.030158129 78:−0.0019987961 79:0.061064892 80:0.053908188 81:−0.010019804 82:0.25567371 # |
| −0.0073890429098904071 1:−4.41471 2:2.683203 3:0.37872982 4:−4.0112801 5:1.669834 6:−1.2786617 7:−1.2676958 8:0.9784404 9:−1.1621584 10:−0.19251882 11:0.17948005 12:−0.74097878 13:0.44499308 14:−0.0070625329 15:−0.6527788 16:0.57128209 17:0.1815735 18:−0.460302 19:−0.24062113 20:−0.29436147 21:0.2046137 22:−0.23127641 23:0.26728085 24:−0.29189453 25:−0.42844203 26:0.11890949 27:−0.5828563 28:0.27136496 29:−0.52650899 30:−0.12449619 31:−0.41865614 32:−0.38618717 33:0.75262243 34:0.16398448 35:−0.42862841 36:−0.079917386 37:−0.034457237 38:0.049663253 39:−0.026839441 40:−0.20840488 41:−0.11020567 42:−0.20190364 43:0.29403234 44:0.038728327 45:0.16312243 46:0.17596419 47:−0.29706264 48:−0.12227666 49:0.28870571 50:0.044383127 51:−0.1945674 52:0.35483041 53:0.18753126 54:−0.10233945 55:0.11218945 56:0.17729792 57:0.012970475 58:−0.052975312 59:−0.0026825017 60:0.0075710067 61:−0.10903102 62:0.09177313 63:−0.122404 64:−0.14133085 65:−0.039609388 66:0.14082959 67:−0.0014556659 68:−0.11085978 69:0.080959745 70:−0.042901337 71:0.050149068 72:−0.054357212 73:−0.040712882 74:0.04342806 75:−0.048064422 76:0.001157394 77:0.038050488 78:−0.012103624 79:−0.0075672837 80:0.016288035 81:0.00388755 82:0.25567371 # |
| −0.0039069580022910669 1:−1.0928398 2:4.5564847 3:0.13658141 4:−4.018383 5:−0.24057193 6:−0.45240521 7:0.43761325 8:−0.23020941 9:−1.8528987 10:−1.8275429 11:0.49437732 12:0.72341979 13:0.62888783 14:0.43660501 15:0.70101285 16:0.65181589 17:0.699884 18:0.60464865 19:0.14881693 20:−0.66960847 21:1.0808402 22:0.73256737 23:0.81082785 24:1.0199807 25:−0.17035381 26:−0.53764629 27:−0.42332968 28:−0.2965571 29:0.56804597 30:−0.069201685 31:−0.28442693 32:0.50515532 33:−0.1098742 34:−0.23597126 35:0.12981954 36:−0.2726315 37:0.23585126 38:−0.19442731 39:−0.4222765 40:0.0092189899 41:−0.016361179 42:−0.0073068822 43:−0.36419266 44:0.52316409 45:0.00054344506 46:−0.17763405 47:0.097439691 48:−0.13253364 49:−0.10772908 50:0.062215112 51:−0.14229205 52:−0.0018253193 53:−0.20546296 54:0.19488296 55:−0.10865132 56:−0.089947186 57:0.13023221 58:−0.089442343 59:0.048431564 60:−0.078044161 61:−0.1097814 62:−0.035178315 63:0.062205702 64:−0.048839353 65:−0.10717151 66:−0.0057327133 67:0.0297626 68:0.083072841 69:−0.024313437 70:0.041320756 71:0.03339909 72:0.070824169 73:−0.07068871 74:0.019567905 75:0.012559616 76:0.049304418 77:−0.045164108 78:−0.0079365019 79:−0.013983565 80:−0.0076463781 81:0.036134619 82:0.25567371 # |
| 0.0098444903871761705 1:3.4000976 2:4.353354 3:0.20291679 4:−0.56321834 5:0.3359561 6:−1.3302954 7:−1.2524338 8:−1.9435711 9:−0.7544232 10:1.8748814 11:−0.66350937 12:−0.95615405 13:1.1766428 14:−0.67985052 15:−0.69076073 16:0.65135092 17:−0.25158882 18:−0.33583677 19:0.22454788 20:0.97624737 21:−0.061259232 22:−0.24438164 23:1.3978306 24:−0.045107901 25:0.90150547 26:0.18234044 27:0.40132105 28:0.0025857005 29:−0.3534779 30:−0.00051128899 31:−0.5115388 32:−0.68650419 33:0.01065794 34:−0.31668335 35:−0.12371469 36:0.18158373 37:0.099708207 38:−0.27020627 39:−0.14006697 40:0.067367613 41:0.049405299 42:0.087938987 43:0.1306714 44:−0.039579701 45:−0.0073669022 46:−0.083823189 47:−0.12140501 48:0.38544589 49:0.12294596 50:−0.22681904 51:0.174869 52:0.029952586 53:−0.21804394 54:−0.13114847 55:−0.19033335 56:0.060533609 57:0.10420916 58:0.083379082 59:0.15737703 60:0.077796958 61:−0.032270338 62:0.060652126 63:0.10343604 64:0.121602 65:−0.082902558 66:−0.031383011 67:−0.057323907 68:0.13476953 69:−0.023190375 70:−0.11172605 71:−0.0031230941 72:0.029506981 73:−0.080234401 74:−0.012763577 75:−0.014051927 76:−0.01854565 77:0.012363502 78:0.01565909 79:−0.0066379169 80:0.021184601 81:0.012500747 82:0.25567371 # |
| 0.0020665672995731979 1:5.2955265 2:−0.65797424 3:−1.0571982 4:−0.72376168 5:0.087484695 6:1.3326952 7:2.0818608 8:−1.217063 9:0.57185346 10:−0.14195058 11:−2.1278417 12:0.85920882 13:−1.7434322 14:0.044522069 15:−1.6611717 16:−1.070134 17:0.065382555 18:0.55782706 19:0.18667004 20:0.45247704 21:0.42276645 22:0.23630776 23:−0.35079005 24:0.0028711383 25:0.27257296 26:−0.34024805 27:0.083222635 28:−0.052973963 29:0.061597131 30:0.19715723 31:−0.49887934 32:−0.29694211 33:−0.32361487 34:−0.058306769 35:−0.23700592 36:−0.051193722 37:0.32658741 38:0.1350269 39:−0.028302681 40:−0.21207443 41:0.0975096 42:0.14156008 43:−0.1836036 44:−0.36535913 45:0.022620961 46:0.18160005 47:−0.21237148 48:−0.048351623 49:−0.1228329 50:0.28498444 51:−0.083813787 52:−0.15850542 53:0.039593969 54:0.099234149 55:−0.045176018 56:0.082574204 57:−0.075926609 58:−0.1059874 59:0.0605998 60:−0.05003868 61:−0.17068541 62:−0.033420015 63:−0.0086220056 64:−0.0997288 65:−0.12466743 66:−0.075003199 67:0.029930672 68:−0.069341287 69:−0.0075586229 70:−0.046565507 71:0.055340845 72:0.053100009 73:0.03331941 74:8.5853564e−005 75:−0.032220732 76:−0.011131383 77:0.046809517 78:−0.12941684 79:−0.0058566034 80:0.007817734 81:−0.0038185893 82:0.25567371 # |

APPENDIX C12

SVM Model Weights
(82; Early/Late)

SVM-light Version V6.01
0 # kernel type
3 # kernel parameter -d
1 # kernel parameter -g
1 # kernel parameter -s
1 # kernel parameter -r
empty# kernel parameter -u
82 # highest feature index
59 # number of training documents
43 # number of support vectors plus 1
0.51192179 # threshold b, each following line is a SV (starting with alpha*y)
−0.0096518688161708 28 1:−1.3949257 2:−7.1064153 3:−7.6357293 4:−3.9997296 5:−4.3126149 6:−1.0455632 7:−1.7593037 8:−1.0766277 9:0.36871698 10:−1.4037681 11:0.43731076 12:1.5785676 13:−2.2389538 14:−1.66617 15:0.58093596 16:−1.9867874 17:1.2219658 18:−0.41062918 19:−0.68057811 20:0.72604179 21:−0.24368794 22:0.21090972 23:0.19525637 24:0.04606054 25:−0.1518749 26:−0.050912332 27:0.15238227 28:−0.017613446 29:−0.27513498 30:−0.029538082 31:−0.23303917 32:−0.11126661 33:−0.077786759 34:0.33194929 35:−0.011755408 36:−0.07646478 37:−0.16744053 38:0.23671371 39:−0.23311555 40:0.019464068 41:0.00095630309 42:−0.049225777 43:−0.022975719 44:−0.10502601 45:−0.10515327 46:0.084919095 47:−0.072050132 48:−0.044558402 49:−0.063181207 50:−0.040598646 51:−0.02891284 52:0.042690523 53:−0.028859708 54:0.024923081 55:0.016705168 56:0.042295106 57:0.0012129262 58:−0.010007722 59:0.0078843376 60:0.029451927 61:−0.14868067 62: 0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 #
−0.0058545298550235049 1:−5.3869047 2:−1.5746411 3:0.74159777 4:−0.78606075 5:0.50478119 6:3.1882224 7:0.3584249 8:−1.4646664 9:0.58070636 10:0.71917087 11:−0.33742091 12:−0.66715032 13:1.1570868 14:−0.58885461 15:0.34032476 16:−0.52852839 17:−0.38242599 18:0.32871774 19:0.82726818 20:−0.21355985 21:−0.44889992 22:0.12188943 23:0.318973 24:0.65250695 25:−0.13354878 26:−0.54600775 27:0.534747 28:0.46380267 29:0.15977333 30:0.34504783 31:−0.58266139 32:−0.0089071169 33:0.57255757 34:0.39571548 35:0.49374899 36:−0.047910046 37:−0.12103498 38:−0.088492699 39:0.13222153 40:0.36167121 41:−0.23554173 42:−0.015975783 43:0.1044606 44:−0.025533743 45:−0.17961036 46:−0.087940715 47:0.10057306 48:0.23271543 49:0.013834573 50:0.023569856 51:−0.18782079 52:0.014782355 53:0.048862826 54:−0.061514128 55:−0.052248385 56:0.036085092 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 #
−0.007302651214809581 1:2.2345536 2:−8.2382746 3:−4.5594249 4:−3.219995 5:−1.4316326 6:−1.8457229 7:1.200842 8:−0.32464877 9:−2.5554824 10:−1.8576775 11:−0.92507511 12:−2.8148921 13:1.2713544 14:0.89249134 15:−0.51592141 16:0.38930354 17:−1.9124364 18:0.36014941 19:−1.2590576 20:0.48945433 21:0.29205838 22:0.18135412 23:0.27294412 24:−0.48372957 25:−0.60903805 26:−0.48058021 27:−0.016271256 28:−0.40135047 29:−0.1528151 30:−0.062056556 31:0.021798939 32:0.30998087 33:−0.12745659 34:0.20686452 35:0.10841317 36:−0.077211976 37:0.12925135 38:0.074331902 39:−0.055461079 40:0.24180417 41:0.033905365 42:−0.022314826 43:−0.027976006 44:0.15169364 45:−0.0016659197 46:0.060984615 47:−0.00077797414 48:0.090841293 49:−0.0054340898 50:−0.028856028 51:0.04912499 52:−0.10594569 53:0.025540976 54:0.040360298 55:−0.019841935 56:−7.4499141e-005 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 #
−0.014129676532172022 1:−2.0180302 2:0.12606727 3:−0.94246083 4:−0.20122282 5:−0.56047148 6:0.56113786 7:0.70434558 8:−0.7257539 9:0.23040083 10:1.4748676 11:−0.61987633 12:−0.91619062 13:−0.62846196 14:−1.2038949 15:−1.0044348 16:0.66051829 17:−0.19564649 18:0.043287247 19:0.37605706 20:0.73170161 21:−0.7671746 22:−0.37668017 23:0.017403821 24:−0.57425302 25:0.053492785 26:0.54330796 27:0.55115807 28:−0.69889963 29:0.072593451 30:0.13369447 31:−0.20441362 32:0.31789717 33:−0.040228985 34:−0.13832618 35:−0.20594792 36:0.18423782 37:−0.24442211 38:−0.1886507 39:0.14019041 40:0.052651592 41:−0.020638961 42:0.026714545 43:−0.11363702 44:−0.070138492 45:−0.12207137 46:−0.35650167 47:0.13796353 48:−0.024700398 49:0.10319643 50:0.095969059 51:0.25174907 52:0.016045703 53:−0.070368044 54:0.049327463 55:0.055020425 56:0.12510186 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 #
−0.014129676532172022 1:−5.2945595 2:−0.057851907 3:−0.72329062 4:2.9341695 5:−2.3624232 6:1.5425693 7:−0.86508709 8:1.179958 9:−0.78581941 10:2.1316049 11:0.69332349 12:−0.7486366 13:−0.7369296 14:−0.92366105 15:−0.097363003 16:0.88752544 17:0.084749475 18:0.20195891 19:−1.8480136 20:0.22161572 21:−0.48020625 22:−0.87218893 23:0.42618835 24:0.66096395 25:0.67604554 26:0.20184891 27:−0.042575251 28:0.24330737 29:−0.14860111 30:−0.4163062 31:0.31232399 32:0.52656972 33:0.45946804 34:0.021183133 35:0.13488212 36:−0.075224601

APPENDIX C12-continued

| SVM Model Weights (82; Early/Late) |
|---|
| 37:−0.0096986843 38:−0.090070963 39:0.29243538 40:−0.20076615 41:0.10365705 42:−0.25348422 43:0.11849995 44:0.25726202 45:−0.063790902 46:0.13409184 47:−0.064501278 48:0.031401385 49:−0.092313476 50:−0.12146627 51:0.028605651 52:0.063654229 53:0.033912227 54:−0.0093408572 55:0.015822398 56:−0.017468618 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.0076853501584470641 1:7.7708535 2:4.6584039 3:−0.33929133 4:4.6656609 5:−0.84039205 6:1.5564984 7:−0.97663349 8:2.6357307 9:−1.8116711 10:−1.0474526 11:−0.85821491 12:1.0413269 13:0.69916433 14:0.55527854 15:1.1760082 16:−0.54476649 17:0.20673905 18:−0.36175492 19:0.48638582 20:0.85343492 21:−1.2359009 22:−0.26548666 23:−0.142498 24:−0.75145184 25:−0.72961819 26:−0.09415675 27:0.074696273 28:0.69541246 29:0.085497767 30:−0.18266958 31:−0.065048501 32:0.18729812 33:0.25056919 34:−0.039664168 35:−0.31293061 36:0.32177299 37:0.039813861 38:0.34916002 39:−0.018389061 40:−0.023314977 41:0.25365567 42:−0.11722416 43:0.011280437 44:0.1343195 45:−0.042727049 46:−0.1094249 47:−0.034260664 48:0.052126046 49:0.039455328 50:−0.038983751 51:−0.012039492 52:−0.16209652 53:0.05140771 54:−0.067295283 55:−0.0067475615 56:0.037642609 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.0086119130151467525 1:−7.4856787 2:1.3673226 3:−4.1349678 4:0.48727509 5:8.1332922 6:0.071281239 7:−1.7165602 8:−0.38248488 9:−1.3826156 10:−0.49927935 11:1.3427233 12:−0.37614337 13:0.65169251 14:−0.74176133 15:0.04573502 16:0.61725277 17:0.012873571 18:−0.47106525 19:−0.2478563 20:−0.051957335 21:0.15890132 22:0.045166306 23:0.077651739 24:0.06408494 25:−0.30056962 26:0.89640504 27:0.67233145 28:−0.12362359 29:0.1236674 30:0.36810777 31:−0.088824689 32:−0.19637337 33:−0.18794051 34:0.020827595 35:−0.35073787 36:0.43417227 37:−0.13088584 38:−0.12785326 39:−0.20853834 40:0.040067613 41:0.038274482 42:0.055357214 43:−0.051750574 44:0.020653274 45:−0.28747228 46:0.18108542 47:−0.10161147 48:−0.05633691 49:0.04294014 50:−0.12335854 51:−0.045288086 52:−0.0089042224 53:0.11948354 54:−0.0078766504 55:0.0034206351 56:−0.059247781 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.014129676532172022 1:1.9467391 2:−4.5085011 3:2.5395069 4:0.57270998 5:0.39287665 6:0.47288308 7:0.73798466 8:−0.18831065 9:−0.68563426 10:−0.78382367 11:−0.94249988 12:−1.4639335 13:0.82455671 14:0.65856737 15:−0.77900302 16:−0.29027078 17:0.56190169 18:−1.0196158 19:0.29380518 20:−0.050871745 21:−0.6400767 22:−0.060887337 23:0.30843309 24:0.38911167 25:0.19030938 26:0.030152237 27:−0.94034457 28:0.24949764 29:0.080111846 30:−0.22673801 31:−0.37830585 32:−0.42703098 33:−0.14493841 34:−0.49106577 35:0.016350741 36:0.28276637 37:0.072390057 38:−0.2047824 39:0.10201492 40:0.024704665 41:0.033523243 42:0.057213154 43:0.12479683 44:−0.2980141 45:−0.23055989 46:0.17928676 47:−0.097297996 48:−0.00038864795 49:−0.35897928 50:−0.058940507 51:0.086685307 52:0.017482469 53:−0.053739388 54:0.0030982296 55:0.026585994 56:0.05599812 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:0.81666607 2:0.95334482 3:−3.1056733 4:−0.057690628 5:3.8275411 6:−2.4385149 7:3.4440734 8:0.74619728 9:0.55505568 10:2.6437523 11:0.14633095 12:0.92240644 13:−0.044869356 14:0.16711205 15:0.68866873 16:−0.52052331 17:0.73232573 18:0.954364 19:−1.6296023 20:−0.69091505 21:−0.62250429 22:0.058407951 23:0.41830444 24:−0.56110144 25:0.24393879 26:−0.63272899 27:−0.37553221 28:−0.050377652 29:0.51595396 30:0.11408119 31:−0.37183687 32:0.25219274 33:−0.15020634 34:−0.089559294 35:−0.13841675 36:0.10217641 37:−0.032159291 38:0.16244814 39:0.0017291079 40:0.19467157 41:−0.020120135 42:0.17245825 43:0.13782045 44:−0.060398389 45:−0.032315724 46:−0.21202798 47:0.086270921 48:−0.17019871 49:−0.1186596 50:0.049102943 51:−0.058264028 52:−0.046889838 53:−0.01580845 54:0.041816335 55:−0.055017203 56:−0.048584573 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.014129676532172022 1:7.5134001 2:5.4316926 3:−3.8632429 4:−2.1880558 5:−0.58260357 6:1.5061033 7:2.1168497 8:−0.51475084 9:1.5293455 10:−0.59999311 11:−0.61974782 12:1.2249726 13:2.10937 14:−0.79162323 15:1.496636 16:0.13937807 17:−0.4341968 18:−0.54903346 19:−0.23939233 20:0.35801935 21:0.34853914 22:−0.89570695 23:−0.48460275 24:0.039763473 25:0.83908743 26:0.36757347 27:−0.35938147 28:0.43846372 29:0.016947255 30:−0.17417148 31:−0.19217905 32:0.11167561 33:−0.5484218 34:−0.021938972 35:0.32561988 36:0.10505087 37:0.056143723 38:−0.16184393 39:−0.11682066 40:0.28780565 41:−0.29961941 42:0.087420411 43:−0.097985625 44:0.1988422 45:0.088030674 46:0.090706497 47:−0.049987424 |

APPENDIX C12-continued

| SVM Model Weights (82; Early/Late) |
| --- |
| 48:−0.022122039 49:0.099453598 50:−0.092255555 51:0.098275162 52:0.062751897 53:0.052539878 54:0.063429095 55:−0.0036416091 56:0.044354413 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.014129676532172022 1:5.301949 2:5.0954819 3:−3.1937132 4:3.0521488 5:−1.137532 6:−1.7408873 7:2.3184443 8:2.3045175 9:−0.031264808 10:−1.1093857 11:−0.053723715 12:−0.67469305 13:−1.1992729 14:−0.22581126 15:−0.867302 16:0.59399915 17:0.90500087 18:−0.12635083 19:0.33835375 20:−0.16993706 21:−0.21663953 22:−0.24661557 23:0.65601867 24:0.33774567 25:0.19017707 26:0.076259002 27:0.37185988 28:−0.26058701 29:−0.23559505 30:−0.24838665 31:0.019096648 32:−0.17409827 33:0.049831416 34:−0.48241001 35:0.30529061 36:−0.44616678 37:0.19514658 38:−0.030325184 39:−0.45137173 40:0.31222218 41:0.076720499 42:0.17102975 43:−0.30972826 44:0.15503697 45:−0.19257012 46:−0.012695519 47:0.069403887 48:0.057886977 49:−0.024995249 50:0.13307475 51:−0.089103825 52:0.042466044 53:0.015556405 54:−0.13057841 55:0.0036390405 56:−0.023372764 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.014129676532172022 1:11.41343 2:2.1029294 3:3.2751324 4:−1.3926133 5:0.40458456 6:−5.8122339 7:−0.61423439 8:−0.17130254 9:1.0096658 10:0.24250206 11:0.045050688 12:−0.55232471 13:−0.23383944 14:1.2332162 15:−0.13347381 16:0.70798326 17:0.64344895 18:0.57295275 19:−0.38390231 20:0.54711437 21:1.0101299 22:−1.1528212 23:−0.34629637 24:0.49580625 25:−0.13806443 26:0.013054552 27:0.75510573 28:0.35193238 29:−0.20124331 30:0.1794066 31:−0.50493973 32:0.043360956 33:0.036958244 34:0.10293178 35:0.078232713 36:0.35212636 37:−0.2260811 38:0.14062934 39:−0.045567911 40:−0.16717893 41:0.084338225 42:−0.12587765 43:0.05728396 44:−0.16789278 45:0.086649664 46:−0.034939352 47:0.11746556 48:0.1111025 49:−0.092833303 50:−0.049556103 51:−0.069632351 52:0.070035905 53:0.040367518 54:0.0015955516 55:0.038746469 56:0.03146439 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.014129676532172022 1:4.4189072 2:4.3692369 3:2.2860656 4:−1.8054105 5:1.382118 6:1.7278793 7:1.1213614 8:−0.67850894 9:0.31127268 10:−0.11542724 11:−0.77878791 12:0.84395933 13:−0.7668938 14:0.32532206 15:0.27445242 16:−0.82527232 17:−0.18264107 18:−0.12096556 19:−0.62431741 20:−0.67406434 21:0.51314914 22:0.16330266 23:0.25057429 24:0.96891803 25:−0.16148108 26:0.067252308 27:0.38987663 28:0.082579486 29:0.22413567 30:−0.16642216 31:0.11901976 32:0.061192509 33:−0.10184798 34:0.2955049 35:−0.14847258 36:−0.20075336 37:0.12751804 38:−0.34627607 39:0.013910817 40:−0.0016297655 41:0.026948731 42:−0.27806681 43:−0.3052876 44:−0.030937172 45:−0.088279307 46:−0.2042761 47:−0.19258258 48:0.098071344 49:−0.17015432 50:0.10327859 51:0.082079649 52:−0.28161612 53:0.018282169 54:0.088138662 55:0.10309676 56:−0.01048686 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.014129676532172022 1:−0.39901826 2:5.0525975 3:−1.3354712 4:5.0663414 5:−1.3063396 6:−0.0088579413 7:−0.79358882 8:1.5731375 9:0.56429166 10:−1.2890133 11:−0.28271779 12:−0.44410205 13:0.72625852 14:−0.37074879 15:0.40125906 16:−0.091416262 17:−0.76463097 18:0.63509148 19:−0.78069311 20:−0.69554651 21:0.31989351 22:0.73853117 23:0.41937104 24:0.24717979 25:−0.75747973 26:0.66650116 27:−0.11373509 28:0.049650751 29:0.18096304 30:−0.70285708 31:0.17336127 32:−0.35325781 33:−0.42118025 34:0.42867085 35:−0.3496792 36:−0.20464914 37:−0.25991926 38:−0.20344743 39:0.029335737 40:−0.092420079 41:−0.06689325 42:0.10023139 43:0.13220313 44:−0.058845691 45:0.092431419 46:−0.19269715 47:0.11161025 48:0.050893798 49:−0.093638107 50:−0.014157431 51:−0.090872757 52:0.18778062 53:−0.016852411 54:−0.016636509 55:−0.039292227 56:0.079550028 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:−4.7765684 2:−0.02359442 3:1.3634911 4:1.8097149 5:−0.52088869 6:1.5549836 7:−0.63070428 8:−1.2487162 9:0.8608669 10:0.15630686 11:−1.7836016 12:0.43759513 13:−1.03545 14:0.46164683 15:−1.0568473 16:0.82734019 17:−0.57975221 18:0.098634101 19:−0.39469379 20:0.078363776 21:−0.4918679 22:0.79418427 23:−0.41378394 24:0.25666785 25:−0.21629062 26:−0.23102112 27:0.52474397 28:0.66049105 29:−0.074629761 30:−0.14192811 31:−0.18053465 32:−0.24776138 33:−0.39292866 34:0.13314253 35:0.32240921 36:0.12681988 37:0.46265233 38:0.46486846 39:0.040000834 40:−0.15794143 41:−0.094866075 42:0.3561427 43:0.044040941 44:0.1246921 45:0.010219221 46:−0.0067574698 47:0.090506971 48:−0.18555306 49:−0.020097038 50:0.033764832 51:0.064414568 52:0.04275541 53:0.089849338 54:0.034210842 55:0.14448649 56:−0.0275291 57:0.0012129262 58:−0.010007722 |

APPENDIX C12-continued

| SVM Model Weights (82; Early/Late) |
|---|
| 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:−0.089767262 80:0.030020168 81:−0.074020557 82:−0.0095585929 # |
| 0.014129676532172022 1:−1.8826247 2:−4.7402377 3:−1.7637211 4:−1.0194999 5:0.88828844 6:2.1374843 7:1.8765314 8:1.5348316 9:0.11943176 10:−1.0289681 11:−0.99235135 12:−0.24765262 13:1.0784228 14:−0.40701064 15:0.79985648 16:0.65468949 17:0.33210367 18:−0.30800489 19:−0.037534084 20:0.53839535 21:0.72973132 22:−0.17190544 23:−0.21747899 24:1.0185667 25:−0.25241295 26:−0.64798838 27:−0.17193776 28:0.33239704 29:0.035444859 30:0.77708089 31:0.72030288 32:0.097988248 33:0.20734031 34:−0.37703136 35:−0.25711492 36:−0.25376144 37:−0.050847862 38:0.18948923 39:−0.15565959 40:−0.45626885 41:−0.062553637 42:0.073139101 43:−0.082572959 44:−0.072524861 45:−0.13704994 46:−0.22155121 47:0.085569993 48:−0.11201678 49:0.04195901 50:−0.003182133 51:−0.014744091 52:0.062740803 53:−0.063215151 54:0.061876982 55:−0.03162447 56:0.012593637 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:2.8063436 2:0.011756125 3:2.7406862 4:4.4265747 5:−1.4988638 6:0.53141081 7:−1.6555473 8:−0.71232891 9:1.4945315 10:−0.77361411 11:0.35191569 12:0.71640235 13:0.016210798 14:0.47991243 15:−0.23310818 16:0.8372876 17:0.69420588 18:0.026475132 19:−0.54502255 20:1.0788943 21:0.18227693 22:0.086983949 23:0.049643338 24:0.15736559 25:−0.2831963 26:−0.56604004 27:−0.26937523 28:−0.016329646 29:−0.10222481 30:0.034749009 31:0.15993041 32:−0.70282078 33:0.28262997 34:0.054679193 35:−0.089058317 36:−0.0026721177 37:−0.61190671 38:−0.36966628 39:0.096443944 40:0.53702098 41:0.13636902 42:0.049852822 43:0.10839016 44:0.12515429 45:−0.04724028 46:0.074525915 47:0.082357585 48:−0.11921032 49:0.11789022 50:0.087786198 51:0.064588681 52:−0.059400879 53:−0.027888373 54:0.14531724 55:0.014312153 56:−0.062468328 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:1.6513064 2:2.5032537 3:0.3320598 4:0.32509437 5:−1.1070019 6:1.6343502 7:0.1419135 8:−2.8804705 9:0.1753165 10:2.648814 11:−0.089585334 12:−0.025250038 13:0.70303231 14:−0.6992172 15:0.32966924 16:0.13890818 17:−0.32249165 18:−1.3020269 19:0.47496384 20:0.32455748 21:0.93887597 22:−0.42975622 23:0.53070855 24:−0.52730739 25:0.28299841 26:−0.82076824 27:0.30226374 28:−0.24031168 29:−0.10204262 30:−0.59490901 31:0.41693404 32:−0.18604806 33:−0.22006041 34:0.29563105 35:−0.34589127 36:−0.032988764 37:−0.085533254 38:0.30426741 39:0.016492482 40:0.0050029298 41:0.25253877 42:0.24945883 43:−0.09458641 44:−0.14441213 45:−0.061058108 46:0.0026660075 47:0.094373122 48:0.15027556 49:−0.12115324 50:−0.10414898 51:0.059379701 52:−0.011304339 53:−0.028787376 54:−0.11322098 55:−0.020172762 56:−0.056384802 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.014129676532172022 1:−0.96571976 2:−2.5993257 3:−0.23476064 4:1.2248125 5:0.40335938 6:0.79708117 7:2.4676306 8:0.265775 9:1.6604223 10:1.5925993 11:−0.52952594 12:0.90458876 13:−1.3420354 14:0.27521384 15:0.37950227 16:1.1187553 17:0.16742539 18:0.61226386 19:0.63651687 20:1.1462045 21:0.50042725 22:0.080851369 23:0.63272691 24:−0.63415235 25:−0.45015541 26:0.36010066 27:−0.016628845 28:−0.14768106 29:0.38010812 30:0.3380022 31:0.045922197 32:−0.24409039 33:0.12909323 34:−0.010709869 35:−0.33740169 36:−0.45418474 37:0.66546065 38:−0.11739187 39:−0.045930211 40:0.16767259 41:−0.088031016 42:−0.17465183 43:0.16101733 44:−0.095079459 45:0.14964834 46:0.23446599 47:−0.049975783 48:0.067850389 49:−0.056486741 50:−0.13023996 51:−0.042666022 52:−0.0045993952 53:0.089822039 54:0.032871149 55:0.01176313 56:0.057380941 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:1.4929143 2:0.46152285 3:0.47216102 4:3.9558408 5:−1.1253986 6:−2.1237767 7:−0.40018395 8:−1.0884254 9:1.8166182 10:1.9606417 11:−1.0647051 12:−0.29838344 13:2.526264 14:0.58221716 15:0.074836835 16:−1.5224754 17:0.27703628 18:0.38223961 19:0.13696153 20:−0.1647654 21:0.0081644701 22:0.78893894 23:1.0695724 24:−0.41440871 25:−0.057489116 26:−0.39767295 27:0.33251187 28:−0.095487505 29:−0.32689717 30:0.32801783 31:0.41519487 32:0.1317492 33:−0.079707749 34:−0.083239987 35:0.23446526 36:0.17079853 37:−0.011479509 38:−0.1906725 39:−0.21815495 40:−0.16963418 41:0.066968992 42:−0.28013784 43:−0.048697036 44:0.057550751 45:−0.071486525 46:0.1029341 47:−0.24083661 48:−0.15175056 49:0.11427744 50:0.063046701 51:0.048548061 52:0.13254188 53:0.025507867 54:−0.040160395 55:0.064384498 56:0.025981931 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 |

APPENDIX C12-continued

| SVM Model Weights (82; Early/Late) |
| --- |
| 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:5.1715746 2:6.2560086 3:−0.63095975 4:0.17658593 5:−0.63095951 6:−0.67149538 7:2.3096206 8:0.37529075 9:0.96911699 10:−1.4502602 11:1.1469702 12:−0.28419325 13:0.85862017 14:0.51408398 15:−0.70921493 16:−0.75590521 17:0.47500339 18:−0.55762553 19:−0.16216692 20:0.15334633 21:−0.99697995 22:0.85025036 23:−0.091772884 24:0.25743744 25:0.79889548 26:0.28512514 27:0.36792576 28:−0.41102186 29:−0.46765786 30:0.38389289 31:0.42982021 32:0.22861513 33:0.39347962 34:0.45254853 35:−0.21063814 36:0.14366493 37:0.36628088 38:−0.1245158 39:0.023792306 40:−0.082779527 41:−0.028957387 42:0.26348174 43:0.18806636 44:−0.11398651 45:0.10434262 46:0.07168334 47:0.1228003 48:0.16197115 49:0.041223623 50:−0.14257708 51:−0.022670072 52:−0.044349186 53:−0.093034506 54:0.092249766 55:0.020147456 56:−0.025068847 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:7.3758655 2:3.2821889 3:−1.7203606 4:−4.3931379 5:−1.3108693 6:0.6080268 7:−3.3651302 8:1.0229824 9:−1.4112043 10:1.1802624 11:−0.26217422 12:0.093822263 13:0.70400214 14:−0.59755927 15:−0.75357497 16:−0.21350908 17:−0.54083067 18:0.62936169 19:−0.2804606 20:−0.31224173 21:−0.5117557 22:0.00050139532 23:−0.91249287 24:−0.01288317 25:−0.1213931 26:0.19709538 27:0.20050012 28:0.36305046 29:0.25924173 30:0.20948119 31:0.606278 32:−0.14346258 33:−0.018017646 34:−0.10519599 35:−0.0046970183 36:−0.14397502 37:0.3151249 38:0.030408848 39:0.19272599 40:0.43891269 41:0.10037084 42:−0.25646606 43:−0.16512167 44:−0.42187971 45:0.016143385 46:0.097658187 47:0.096621267 48:−0.10621667 49:0.0098900916 50:0.058874324 51:0.021430437 52:0.12747428 53:−0.031993873 54:−0.018980416 55:−0.020970698 56:−0.050161723 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:4.2570329 2:1.2707268 3:0.060809024 4:−0.34580216 5:−1.1684704 6:0.24985191 7:0.66774571 8:−0.98204416 9:0.39584687 10:−0.058977798 11:3.1290677 12:−0.16429007 13:−0.29575548 14:−0.79796767 15:−0.92869937 16:0.27761441 17:0.2174428 18:−1.1456994 19:0.034965035 20:−0.47711003 21:0.70377195 22:0.99227738 23:−0.098170169 24:−0.73055613 25:0.00080335321 26:0.32252979 27:−0.38844991 28:0.38073343 29:0.34492823 30:0.33707693 31:0.3116172 32:0.10197504 33:−0.0022537853 34:−0.136519 35:0.51741779 36:0.066560075 37:−0.058931071 38:0.17123541 39:0.033269901 40:−0.10582984 41:0.35384852 42:−0.10329926 43:0.083587185 44:0.089275718 45:−0.018744053 46:−0.096741848 47:0.08435224 48:0.10009018 49:−0.08898893 50:0.14042641 51:0.008147344 52:−0.021189362 53:0.18784206 54:0.09644901 55:−0.059945509 56:0.050251234 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.014129676532172022 1:5.6213579 2:−1.5978519 3:−2.3738859 4:−0.21276632 5:−2.0704916 6:1.2145759 7:−1.7947991 8:−0.38934833 9:0.68648249 10:0.07756786 11:0.96927595 12:0.85225278 13:0.82713306 14:−0.6317817 15:0.060119409 16:0.53315473 17:−0.63786036 18:−0.18419184 19:−0.17222922 20:0.23700073 21:0.41288087 22:−0.21832624 23:0.77097481 24:−0.32132939 25:−0.61861718 26:0.71403581 27:−0.74053341 28:−0.25754192 29:−0.27160236 30:0.24262851 31:−0.50720996 32:0.047787912 33:0.40053281 34:−0.001376385 35:0.31981432 36:0.18490861 37:0.20488285 38:−0.2758584 39:0.098100275 40:−0.30382162 41:−0.18340316 42:0.11217732 43:−0.095232248 44:−0.11273006 45:0.14231548 46:−0.15106419 47:0.077777244 48:−0.14272653 49:−0.021783257 50:0.057871729 51:−0.084990285 52:−0.10602037 53:−0.07485912 54:−0.1357196 55:0.061490621 56:−0.089742765 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.0081438017002357452 1:3.8165958 2:4.1213121 3:2.3161864 4:−3.0596099 5:−0.30332923 6:0.63586134 7:−2.075444 8:0.53723407 9:−0.78317535 10:1.2130451 11:−1.1261178 12:0.13925673 13:−0.00080731465 14:−0.36727998 15:−1.1007872 16:0.12220399 17:−0.16517247 18:−0.13920781 19:0.82435578 20:0.16591161 21:−0.23242782 22:−0.76459122 23:−0.14402191 24:−0.093796931 25:−0.35366574 26:0.1259172 27:0.35636061 28:−0.1561453 29:−0.30946004 30:−0.0079295421 31:0.14403719 32:0.3113471 33:−0.23919508 34:0.20372233 35:0.1873154 36:−0.35008284 37:−0.10114411 38:−0.18175358 39:−0.34891984 40:−0.12460336 41:−0.064354032 42:0.22279459 43:0.46199134 44:0.074363582 45:−0.022215648 46:−0.0055433461 47:−0.26017717 48:−0.17673591 49:−0.15347026 50:0.10561302 51:−0.070043743 52:−0.081612282 53:−0.026877183 54:0.084884487 55:−0.12513606 56:−0.0061736251 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 |

APPENDIX C12-continued

| SVM Model Weights (82; Early/Late) |
|---|
| 80:0.030020168 81:−0.074020557 82:−0.0095585929 # |
| 0.014129676532172022 1:3.8556261 2:−6.2038488 3:−5.2995944 4:1.0454292 5:−1.2555572 6:−1.9084506 7:1.4090331 8:1.3098029 9:−0.073445693 10:0.91280049 11:−0.28974295 12:−0.89815402 13:0.50741732 14:−1.1234094 15:0.40550721 16:0.05630216 17:0.3938835 18:−0.8033154 19:0.61603719 20:−1.0519572 21:0.58608907 22:0.63743144 23:−0.96908242 24:0.39583963 25:0.026809203 26:−0.079193212 27:0.61877978 28:0.26019719 29:0.20661345 30:−0.28715003 31:−0.32341436 32:0.090089537 33:0.23544869 34:−0.16739562 35:−0.16947836 36:−0.29379353 37:−0.15087201 38:−0.25694877 39:0.1403594 40:0.082345903 41:0.19221695 42:0.07712917 43:0.32862172 44:0.0046440288 45:0.19785684 46:0.061554134 47:−0.039243676 48:−0.16624986 49:0.1103835 50:−0.052750777 51:0.091612965 52:−0.13333435 53:0.011145942 54:−0.10626094 55:0.078714631 56:0.0066998564 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:−3.1721535 2:2.3815951 3:−1.3541294 4:4.4028063 5:0.37577188 6:2.038588 7:−1.1078327 8:0.077220947 9:0.1048202 10:−0.32131019 11:0.0095497658 12:−0.26672974 13:−0.97509146 14:0.22310984 15:0.5243153 16:−0.23435943 17:0.32307035 18:0.36085799 19:−0.45644122 20:0.15602706 21:0.27153984 22:0.13524668 23:−0.91608816 24:0.2268054 25:−0.066785917 26:−0.52979523 27:0.061836421 28:−0.6176818 29:−0.55444902 30:0.72187847 31:0.15699852 32:0.25975814 33:−0.1481832 34:−0.11781922 35:0.12439211 36:0.23313096 37:−0.049239758 38:−0.15831193 39:0.26736262 40:0.24202378 41:0.092940688 42:0.26663241 43:−0.20967039 44:−0.044914387 45:0.33803746 46:−0.021778662 47:−0.20199065 48:−0.03253793 49:−0.24459621 50:−0.023832891 51:0.0017655258 52:−0.015444397 53:0.098579772 54:−0.11592954 55:−0.053960361 56:0.066875026 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.0030513388082771022 1:−0.8645739 2:−11.62128 3:−3.2131777 4:−1.164062 5:−1.0675756 6:2.7200625 7:2.7925713 8:1.922492 9:0.69017261 10:0.34624994 11:0.5217886 12:1.835223 13:0.62298334 14:2.1163771 15:−0.76544005 16:0.42908949 17:0.43685991 18:0.70799941 19:0.40569007 20:−0.56678325 21:−0.36770386 22:−0.80202943 23:−0.57324862 24:−0.092164792 25:0.18516839 26:0.41106212 27:−0.034337059 28:−0.32259288 29:0.081896782 30:−0.094834358 31:0.52947354 32:−0.20463991 33:−0.20629437 34:0.59112048 35:0.15035672 36:0.22312392 37:−0.31852132 38:−0.0541518 39:−0.10897958 40:−0.05797803 41:0.15552168 42:0.017587796 43:0.013944846 44:−0.03423788 45:−0.059882317 46:0.013354502 47:−0.014535863 48:0.070811585 49:−0.01017198 50:0.097690657 51:0.0015603151 52:0.0085967192 53:0.063217014 54:−0.094367333 55:0.042437546 56:−0.00090677122 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.013353236515559627 1:−3.7090807 2:2.7140775 3:−0.075759523 4:0.041639648 5:−0.29720068 6:−0.25560203 7:0.27214682 8:1.4826385 9:−0.005190081 10:0.8440789 11:−0.95171481 12:−1.2690303 13:0.6956377 14:−1.0611616 15:−0.09884382 16:0.28663257 17:0.1654385 18:−0.023814723 19:0.26264462 20:0.559008 21:−0.47534558 22:0.11464202 23:0.10394695 24:0.43159199 25:0.13391288 26:0.26467714 27:−0.50619888 28:−0.47367036 29:0.39968583 30:0.15560305 31:−0.21721113 32:−0.23065186 33:−0.30403018 34:−0.026239848 35:0.20863502 36:−0.12888727 37:−0.4005174 38:0.51703691 39:0.015326412 40:0.0035461469 41:0.19461451 42:−0.0037955304 43:−0.033356275 44:−0.14382221 45:0.31450939 46:−0.045536093 47:−0.32493994 48:0.24123472 49:0.13549998 50:0.033126615 51:−0.13722432 52:−0.017305013 53:−0.01344727 54:0.077936843 55:0.098757863 56:−0.054080054 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.00079624676868178274 1:−2.7498724 2:−1.6573796 3:4.1532178 4:2.7497079 5:−1.4087201 6:−2.4817951 7:1.8039784 8:−1.7016865 9:−4.2841592 10:−0.42910659 11:0.02060272 12:2.3381867 13:0.48540479 14:−0.84081912 15:−0.24360225 16:0.17448187 17:−0.23134544 18:0.23256347 19:0.14132813 20:0.058838952 21:−0.039073493 22:0.025086315 23:−0.036944158 24:0.2416046 25:0.17516252 26:−0.070632339 27:0.069438867 28:−0.045433383 29:0.13883717 30:0.098388717 31:0.0079460498 32:−0.0064950241 33:−0.076680005 34:−0.005659095 35:0.02432858 36:0.016251441 37:0.026527343 38:−0.15264067 39:−0.028717915 40:−0.024141029 41:0.021502094 42:0.0095573906 43:−0.030435495 44:−0.00065544696 45:0.085420042 46:0.010500111 47:0.0072400868 48:0.017052265 49:0.0074494672 50:0.010825909 51:−0.025269559 52:0.018150901 53:−0.015518044 54:−0.0067413542 55:−0.0047379411 56:0.0081884637 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:2.0169151 2:2.7118552 3:−0.97072595 4:−1.440972 5:−0.023310574 |

APPENDIX C12-continued

SVM Model Weights
(82; Early/Late)

6:0.088995807 7:1.1742412 8:−0.26628274 9:1.0636332 10:−0.35247809 11:−0.95979816
12:0.41680926 13:−0.68784618 14:0.27777776 15:−0.62106568 16:0.1858798 17:−0.72351062
18:−0.10146288 19:0.55405843 20:0.98760915 21:−0.1066047 22:1.1175046 23:−0.10998057
24:0.76056963 25:0.62958026 26:0.093510211 27:−0.20644426 28:−0.3260636 29:−0.17479752
30:0.15545377 31:−0.2081164 32:0.13701558 33:−0.61091846 34:−0.059010141 35:−0.31059647
36:0.091375306 37:−0.26461568 38:0.14244466 39:0.17475669 40:−0.050807822 41:−0.12458584
42:−0.50552976 43:0.16471079 44:0.16536626 45:−0.043086305 46:0.043663982 47:0.15220931
48:−0.07144244 49:−0.048500348 50:0.075483367 51:−0.016357273 52:−0.053354781
53:0.0081567327 54:−0.16838992 55:−0.086322755 56:−0.046804983 57:0.0012129262
58:−0.010007722 59:0.0078843376 60:0.029451927 61:−0.14868067 62:0.016841359 63:−0.03576494
64:−0.071018636 65:−0.025739608 66:0.019898374 67:−0.06432239 68:0.041407861
69:−0.05748732 70:−0.036829431 71:−0.0151224 72:0.041355006 73:−0.065142207 74:−0.020542866
75:0.056401286 76:0.020827135 77:0.015769269 78:−0.03525912 79:0.089767262
80:0.030020168 81:−0.074020557 82:−0.0095585929 #
−0.014129676532172022 1:3.4939618 2:−2.0430965 3:−0.26417074 4:−0.24291684 5:0.55354798
6:1.9550351 7:0.2522594 8:−0.046835717 9:−0.084059164 10:−1.1158637 11:−1.5626776
12:0.14917295 13:−0.17417586 14:0.75046748 15:0.074603587 16:−0.42967603 17:0.85016102
18:0.045669194 19:0.12139843 20:−0.10238918 21:0.41630107 22:0.11402427 23:−0.19227561
24:−0.66205388 25:0.12727371 26:0.25006539 27:0.4981001 28:−0.062730476 29:0.32888475
30:0.23479638 31:−0.71796352 32:−0.026605653 33:−0.10604087 34:0.09455321 35:0.065880358
36:−0.25172642 37:0.15260281 38:−0.19098833 39:0.50333178 40:−0.22157633 41:0.4480198
42:0.040230963 43:−0.15456372 44:0.26783621 45:−0.062987752 46:0.0091908248
47:−0.10023692 48:0.062804766 49:0.00042508432 50:−0.01581303 51:0.0089618964 52:0.18848881
53:−0.16312739 54:0.052358866 55:−0.083838269 56:−0.064836018 57:0.0012129262
58:−0.010007722 59:0.0078843376 60:0.029451927 61:−0.14868067 62:0.016841359 63:−0.03576494
64:−0.071018636 65:−0.025739608 66:0.019898374 67:−0.06432239 68:0.041407861
69:−0.05748732 70:−0.036829431 71:−0.0151224 72:0.041355006 73:−0.065142207 74:−0.020542866
75:0.056401286 76:0.020827135 77:0.015769269 78:−0.03525912 79:0.089767262
80:0.030020168 81:−0.074020557 82:−0.0095585929 #
0.014129676532172022 1:−5.282063 2:−5.2253718 3:−1.6592358 4:3.7173386 5:1.5430499
6:1.4682902 7:0.43495443 8:−2.1969545 9:−0.33621359 10:0.96680242 11:0.50450617
12:−0.87444186 13:0.58921939 14:0.44602743 15:−0.14129899 16:−0.85770762 17:1.0834217
18:0.3474828 19:0.76027685 20:0.098456927 21:−0.039001197 22:−0.044088166 23:−0.85439754
24:−0.044291325 25:−0.26717257 26:0.39874998 27:−0.10484358 28:0.14233601 29:−0.88646519
30:−0.67754126 31:−0.11577591 32:0.2049365 33:−0.1397716 34:−0.30874228 35:−0.027378339
36:−0.094993576 37:0.14092611 38:−0.046402853 39:−0.27196869 40:0.11477086
41:−0.026609588 42:−0.28920403 43:−0.063654795 44:0.0042175548 45:0.20971207 46:−0.26637724
47:0.14536659 48:0.041953377 49:−0.057218485 50:−0.082538471 51:−0.056286912
52:0.017587349 53:0.011914864 54:0.12971668 55:−0.020537527 56:−0.071250014
57:0.0012129262 58:−0.010007722 59:0.0078843376 60:0.029451927 61:−0.14868067
62:0.016841359 63:−0.03576494 64:−0.071018636 65:−0.025739608 66:0.019898374
67:−0.06432239 68:0.041407861 69:−0.05748732 70:−0.036829431 71:−0.0151224 72:0.041355006
73:−0.065142207 74:−0.020542866 75:0.056401286 76:0.020827135 77:0.015769269 78:−0.03525912
79:0.089767262 80:0.030020168 81:−0.074020557 82:−0.0095585929 #
0.014129676532172022 1:2.4364457 2:−2.4952033 3:0.57494962 4:2.0859833 5:−0.11883686
6:1.6288694 7:−2.3889301 8:2.0599835 9:−0.67758435 10:0.95458645 11:−0.15813118
12:0.43315053 13:−1.697163 14:0.87463087 15:0.65608376 16:0.19616696 17:−1.4759452
18:−1.1763201 19:0.42796028 20:−0.79382294 21:0.20557302 22:0.22632639 23:0.12205228
24:0.23985142 25:0.30193824 26:−0.48972481 27:−0.36619008 28:−0.20349167 29:0.029681269
30:0.12196921 31:−0.53637582 32:0.71608567 33:0.11353444 34:0.13275488 35:−0.35313451
36:0.23008479 37:−0.0042580003 38:−0.13428803 39:−0.47737715 40:0.097381763
41:0.054409534 42:−0.0055299043 43:−0.040443998 44:−0.054542165 45:0.084923171
46:0.14314087 47:0.077368617 48:0.091301709 49:0.054922722 50:0.13933112 51:0.012715936
52:0.17065214 53:0.0039909282 54:0.096100546 55:0.032845948 56:−0.0094081471
57:0.0012129262 58:−0.010007722 59:0.0078843376 60:0.029451927 61:−0.14868067
62:0.016841359 63:−0.03576494 64:−0.071018636 65:−0.025739608 66:0.019898374
67:−0.06432239 68:0.041407861 69:−0.05748732 70:−0.036829431 71:−0.0151224 72:0.041355006
73:−0.065142207 74:−0.020542866 75:0.056401286 76:0.020827135 77:0.015769269 78:−0.03525912
79:0.089767262 80:0.030020168 81:−0.074020557 82:−0.0095585929 #
0.014129676532172022 1:2.4364948 2:0.83957785 3:0.86351651 4:5.1018496 5:−1.6327702
6:−0.31986213 7:−2.3673089 8:0.93218809 9:−0.87255412 10:0.040801834 11:0.94762993
12:−0.41336954 13:0.81564486 14:0.0982242 15:0.44914883 16:−0.17941685 17:0.65484828
18:0.80967671 19:0.58174157 20:−0.17481853 21:1.0364466 22:0.19076701 23:−0.90700734
24:0.061875243 25:0.47255123 26:0.060815111 27:−0.16194625 28:−1.0476344 29:0.48059022
30:−0.20063174 31:−0.14960603 32:−0.086357921 33:0.31174216 34:0.27688587 35:0.12793587
36:0.016264064 37:0.26090971 38:0.52480477 39:2.3840179e−005 40:0.044315793
41:−0.40265658 42:−0.070961982 43:0.01243855 44:0.077756085 45:−0.30987245 46:−0.0076297782
47:−0.058119465 48:−0.088347614 49:−0.072945476 50:−0.013072691 51:0.07988438
52:−0.048195962 53:−0.042191297 54:0.042053051 55:0.0049300063 56:0.016293736
57:0.0012129262 58:−0.010007722 59:0.0078843376 60:0.029451927 61:−0.14868067
62:0.016841359 63:−0.03576494 64:−0.071018636 65:−0.025739608 66:0.019898374
67:−0.06432239 68:0.041407861 69:−0.05748732 70:−0.036829431 71:−0.0151224 72:0.041355006
73:−0.065142207 74:−0.020542866 75:0.056401286 76:0.020827135 77:0.015769269 78:−0.03525912
79:0.089767262 80:0.030020168 81:−0.074020557 82:−0.0095585929 #
−0.014129676532172022 1:−1.1086093 2:−0.24525243 3:−0.012263828 4:4.4603519 5:−1.3567572
6:0.55176359 7:1.4479891 8:1.4906476 9:−1.1852733 10:1.3972335 11:−1.3007834 12:−0.79054368
13:−1.759953 14:0.22520538 15:−0.50055957 16:−0.78732228 17:−0.32063743 18:−1.0868118

APPENDIX C12-continued

| SVM Model Weights (82; Early/Late) |
| --- |
| 19:−0.5358454 20:−1.1556014 21:0.46605784 22:−0.61499947 23:0.14458433 24:−0.54821521 25:0.034202885 26:0.26226014 27:0.23044385 28:0.30017558 29:−0.37415487 30:0.56640071 31:0.15296586 32:−0.73695165 33:−0.2482585 34:0.010389246 35:0.18810391 36:0.20500675 37:−0.14611165 38:0.13306889 39:0.079104073 40:−0.016697284 41:−0.36889744 42:−0.16244601 43:−0.034388766 44:−0.0014241217 45:0.068406373 46:0.094277658 47:0.071897976 48:0.018016206 49:0.1492022 50:−0.069316797 51:−0.042334866 52:−0.13608441 53:−0.12525721 54:0.032958243 55:−0.062400296 56:0.018584643 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.007820634044951022 1:1.0641018 2:−1.4297172 3:4.8951802 4:−0.137775 5:0.56927812 6:−1.7847967 7:−1.9565332 8:−0.17318074 9:0.51622891 10:−0.90676576 11:1.1478916 12:−0.57857686 13:−0.92158562 14:0.36124113 15:0.61635685 16:0.8736679 17:−0.3136245 18:−0.17211984 19:0.20826191 20:−0.52801782 21:−0.71033978 22:−0.12994139 23:−0.27661556 24:−0.52243572 25:0.61371219 26:−0.52216852 27:−0.55109787 28:0.02589271 29:−0.36881804 30:0.18825398 31:−0.094376177 32:−0.05725259 33:−0.44439518 34:0.31346551 35:0.040207669 36:−0.58096075 37:0.057326291 38:−0.21623228 39:0.067602977 40:−0.057501908 41:0.09286765 42:−0.081763573 43:−0.059099127 44:−0.11942741 45:−0.22494462 46:−0.26313019 47:−0.078880414 48:−0.10077233 49:0.19876048 50:−0.25514632 51:−0.088120617 52:−0.031340431 53:0.078340799 54:−0.049516156 55:0.030113976 56:0.019137761 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.014129676532172022 1:0.38880625 2:−1.5202221 3:1.8515191 4:−0.057053305 5:−0.36625457 6:1.673123 7:−1.2837189 8:−1.2870549 9:0.50352156 10:−1.2465639 11:1.1318673 12:0.051396698 13:0.66061544 14:0.50571138 15:−1.2800717 16:0.29014322 17:0.69463599 18:0.027451562 19:−0.12588866 20:−0.53889167 21:0.012748598 22:−0.19130741 23:0.53985041 24:−0.1611672 25:0.14636391 26:0.03224428 27:0.2165996 28:0.30223122 29:0.33679906 30:0.14412227 31:−0.013372811 32:0.43927842 33:−0.10265231 34:−0.1041251 35:−0.3130199 36:−0.18684889 37:−0.1900457 38:0.24285334 39:−0.066695973 40:0.17855525 41:−0.16985112 42:−0.013048503 43:−0.063885801 44:0.088452458 45:0.18575054 46:0.040893011 47:−0.043057173 48:−0.055444524 49:−0.030102972 50:−0.050405726 51:−0.031667873 52:−0.023971891 53:−0.08683119 54:−0.042502359 55:0.028166918 56:0.028085964 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:9.1376534 2:2.54915 3:−1.474272 4:−3.2015469 5:0.42019662 6:3.2201624 7:0.59989285 8:−2.7158744 9:−3.5350218 10:0.74424917 11:1.6188122 12:−1.8388782 13:−1.7614143 14:1.5132744 15:1.8010006 16:−0.51104623 17:−0.27670467 18:1.2498407 19:0.29338449 20:0.33543548 21:−0.054673675 22:0.35196343 23:0.3611652 24:0.11363474 25:0.55755246 26:0.28965598 27:0.085346349 28:0.14621016 29:0.11303017 30:−0.036370452 31:0.21605951 32:−0.46999449 33:0.11828584 34:−0.22733067 35:0.025899749 36:0.010238539 37:−0.22034112 38:−0.027019881 39:−0.13248673 40:−0.098608032 41:−0.00081450719 42:0.139504 43:0.13038938 44:0.076654181 45:0.098132893 46:−0.028332448 47:−0.044595689 48:−0.092575513 49:0.05960054 50:0.037807971 51:−0.014507919 52:0.038878012 53:−0.034509894 54:−0.032353539 55:0.051676732 56:0.023085095 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| 0.014129676532172022 1:5.9279609 2:−4.8870487 3:−2.3137126 4:−1.7642508 5:−1.7306607 6:−3.1328332 7:−1.6333387 8:−1.1901853 9:1.2670099 10:2.7033648 11:0.80952233 12:0.31965619 13:−0.15020287 14:0.3354522 15:0.081965514 16:1.41405 17:0.032736059 18:−0.14532112 19:0.15633012 20:−0.20536461 21:−0.88627076 22:0.84299314 23:−0.593009 24:0.38754123 25:−0.40949273 26:−0.10202188 27:−0.052269038 28:0.23512483 29:0.14161985 30:−0.20515643 31:0.19169326 32:−0.26048449 33:0.035312776 34:−0.1700933 35:−0.26253361 36:0.24203417 37:0.03904609 38:−0.13614458 39:0.017573882 40:−0.12001912 41:−0.3054083 42:0.15119965 43:−0.30649367 44:0.2569271 45:−0.012436618 46:−0.0053096917 47:−0.21330121 48:0.22020388 49:0.0047446396 50:−0.021045126 51:−0.055777438 52:−0.027595868 53:−0.085848168 54:0.014862306 55:−0.094873302 56:0.020950042 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 # |
| −0.014129676532172022 1:0.38880625 2:−1.5202221 3:1.8515191 4:−0.057053305 5:−0.36625457 6:1.673123 7:−1.2837189 8:−1.2870549 9:0.50352156 10:−1.2465639 11:1.1318673 12:0.051396698 13:0.66061544 14:0.50571138 15:−1.2800717 16:0.29014322 17:0.69463599 18:0.027451562 19:−0.12588866 20:−0.53889167 21:0.012748598 22:−0.19130741 23:0.53985041 24:−0.1611672 25:0.14636391 26:0.03224428 27:0.2165996 28:0.30223122 29:0.33679906 30:0.14412227 |

APPENDIX C12-continued

SVM Model Weights
(82; Early/Late)

31:−0.013372811 32:0.43927842 33:−0.10265231 34:−0.1041251 35:−0.3130199 36:−0.18684889 37:−0.1900457 38:0.24285334 39:−0.066695973 40:0.17855525 41:−0.16985112 42:−0.013048503 43:−0.063885801 44:0.088452458 45:0.18575054 46:0.040893011 47:−0.043057173 48:−0.055444524 49:−0.030102972 50:−0.050405726 51:−0.031667873 52:−0.023971891 53:−0.08683119 54:−0.042502359 55:0.028166918 56:0.028085964 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 #
−0.0027119850464008073 1:−0.1235674 2:9.1242638 3:−3.2694976 4:−1.9610975 5:−1.0927585 6:1.739417 7:3.5246229 8:−1.5048804 9:0.71317029 10:−1.8953476 11:0.15650336 12:−0.047453586 13:−0.77944964 14:−1.0163347 15:−0.49707088 16:1.2771677 17:−0.098247908 18:0.86071211 19:0.62828761 20:−1.2553892 21:−0.27884349 22:−0.2579141 23:−0.32627985 24:−0.38073459 25:−0.66062993 26:−0.99281323 27:−0.072515115 28:−0.3559759 29:−0.1339059 30:−0.38346794 31:−0.138189 32:−0.087566212 33:0.32585442 34:−0.018183192 35:−0.03254519 36:0.37185615 37:−0.14023654 38:0.00083181128 39:−0.024392337 40:−0.21453759 41:0.0087169167 42:−0.27040747 43:−0.030262673 44:−0.067775473 45:0.029083207 46:0.18102282 47:−0.10595187 48:−0.10025868 49:0.0093888957 50:−0.080102541 51:−0.027170023 52:0.047395799 53:−0.025068192 54:0.051999666 55:0.0053025428 56:−0.0024844036 57:0.0012129262 58:−0.010007722 59:0.0078843376 60:0.029451927 61:−0.14868067 62:0.016841359 63:−0.03576494 64:−0.071018636 65:−0.025739608 66:0.019898374 67:−0.06432239 68:0.041407861 69:−0.05748732 70:−0.036829431 71:−0.0151224 72:0.041355006 73:−0.065142207 74:−0.020542866 75:0.056401286 76:0.020827135 77:0.015769269 78:−0.03525912 79:0.089767262 80:0.030020168 81:−0.074020557 82:−0.0095585929 #

APPENDIX C13

SVM Model Weights
(77; Normal/Diseased)

SVM-light Version V6.01
0 # kernel type
3 # kernel parameter -d
1 # kernel parameter -g
1 # kernel parameter -s
1 # kernel parameter -r
empty# kernel parameter -u
77 # highest feature index
138 # number of training documents
70 # number of support vectors plus 1
0.84091056 # threshold b, each following line is a SV (starting with alpha*y)
−0.0080722787272721822 1:4.4964366 2:−1.9232402 3:0.79626346 4:−1.9897418 5:0.80510318 6:2.1251585 7:−1.5002989 8:0.27981764 9:0.13564111 10:−0.74375212 11:−2.1897702 12:0.64559364 13:0.18348907 14:−0.80920774 15:0.52811146 16:0.68309391 17:−0.48481965 18:0.48805124 19:−0.56828117 20:−0.21268305 21:0.26711833 22:0.24619445 23:0.76305592 24:−0.037935089 25:−0.0027787928 26:0.16949297 27:−0.33707494 28:0.18837656 29:0.19275174 30:0.290317 31:0.087804936 32:−0.13446166 33:0.10305968 34:−0.09852086 35:−0.064386643 36:−0.046250403 37:0.1535148 38:−0.18191323 39:0.15117276 40:−0.073515728 41:−0.045017619 42:−0.11366132 43:−0.11412581 44:−0.21053967 45:0.095722117 46:0.023894051 47:0.11108802 48:0.1572502 49:0.027251426 50:−0.12324705 51:0.072330914 52:0.12066535 53:−0.020608915 54:0.041558318 55:0.13878544 56:0.07036978 57:−0.13811713 58:0.040571205 59:−0.026220437 60:0.040255491 61:−0.043604821 62:0.14185396 63:0.032436881 64:−0.030241679 65:0.0048340759 66:0.023171702 67:−0.034863781 68:−0.048638832 69:−0.069616713 70:0.051264167 71:0.0057058115 72:−0.023346355 73:−0.078577273 74:−0.018861227 75:0.0075417799 76:−0.01085316 77:0.19096926 #
0.014353309248426729 1:1.0541974 2:2.3965838 3:2.0010946 4:0.75458729 5:0.77514344 6:1.4750326 7:1.0153245 8:0.28703469 9:1.4778411 10:−0.11666621 11:0.41137302 12:0.085668772 13:−0.50968975 14:−1.9783171 15:0.83110416 16:0.12056253 17:0.09914846 18:−1.0437711 19:0.71249098 20:−0.082739554 21:0.04920321 22:−0.65606099 23:0.49226239 24:0.043491449 25:0.14755701 26:−0.29607397 27:−0.023315037 28:0.75468624 29:−0.32364133 30:0.12194663 31:0.23194517 32:−0.1660957 33:0.011016251 34:0.20845319 35:0.016992919 36:0.059358116 37:−0.22370563 38:−0.4956035 39:0.041449692 40:−0.10502515 41:−0.029065089 42:−0.14989041 43:−0.052000806 44:0.18101674 45:0.11844644 46:0.072443083 47:−0.31213465 48:0.086628787 49:−0.073447861 50:0.054050442 51:−0.015139502 52:0.012923755 53:0.067412421 54:0.16672988 55:0.042141914 56:−0.019829269 57:0.0034714264 58:−0.037610121 59:0.017614296 60:−0.086382836 61:−0.0428246 62:−0.034966465 63:−0.083110392 64:−0.024455875 65:0.11667071 66:−0.080493905 67:0.011723236 68:0.023163309 69:−0.018305045 70:−0.006845803 71:0.018221125 72:0.04826453 73:0.011845684 74:0.048712477 75:0.0014680276 76:−0.0040727593 77:0.19096926 #
−0.014353309248426729 1:0.46314588 2:3.9128089 3:−0.86363637 4:0.04046309 5:−0.51157683 6:−1.4265751 7:−0.080523364 8:−2.1386857 9:−1.3693994 10:1.1548964 11:0.52218449 12:−0.46195436 13:−0.17862622 14:0.35755825 15:−0.82406104 16:−0.53325355 17:0.39610642 18:0.051614285 19:0.10268705 20:−0.40703654 21:−0.1886259 22:−0.11897216 23:0.10170638

APPENDIX C13-continued

SVM Model Weights
(77; Normal/Diseased)

24:−0.66070902 25:−0.53536105 26:0.49288163 27:−0.70293969 28:−0.1222033 29:−0.048891608
30:0.37241495 31:0.080400266 32:−0.39068863 33:0.30465183 34:−0.13347328 35:0.28836092
36:−0.023716437 37:0.14553422 38:0.15835193 39:−0.23397873 40:0.12629595 41:0.23413505
42:0.070166387 43:−0.083833747 44:−0.016950658 45:−0.017871771 46:0.087831773
47:−0.00015709829 48:0.1673881 49:0.18956207 50:0.1952533 51:0.013547563 52:0.37886518
53:−0.050230384 54:0.13186033 55:−0.020242533 56:0.033409476 57:−0.054047745 58:0.011667713
59:−0.081895404 60:0.084315971 61:−0.17004821 62:−0.093653142 63:0.067260243
64:−0.0018483252 65:0.11754032 66:−0.063270047 67:0.095731378 68:−0.017015938 69:0.08558809
70:−0.045744702 71:0.0083405562 72:−0.060346164 73:−0.051456854 74:0.018569108
75:0.016022179 76:0.0058376403 77:0.19096926 #
−0.014353309248426729 1:−1.5467228 2:−1.5183928 3:1.1758648 4:0.6948514 5:−2.6607132
6:−2.3410974 7:−0.080892712 8:0.21044551 9:−0.036575131 10:−0.2435967 11:0.25000006
12:1.6211165 13:−0.182383 14:0.76657295 15:−0.052334391 16:0.19181778 17:−0.60221505
18:0.096046209 19:−0.51166803 20:−0.16289751 21:0.035897125 22:0.43033758 23:0.43565136
24:−0.53536803 25:0.21341068 26:−0.19518352 27:−0.46430638 28:0.38137683 29:0.45672259
30:−0.03918248 31:0.14056641 32:0.19300364 33:−0.25511897 34:0.47353798 35:−0.15196748
36:−0.083250403 37:−0.10796153 38:0.1312249 39:−0.26231718 40:0.20249712 41:0.16176087
42:−0.14357451 43:−0.34923258 44:0.33870053 45:0.02669606 46:0.005334042 47:0.17169333
48:0.071357645 49:−0.13616332 50:0.017426876 51:0.14566396 52:−0.021135578 53:−0.13017142
54:−0.048229631 55:−0.053085733 56:0.20227978 57:0.033354193 58:−0.05113541
59:−0.068235263 60:0.00012513905 61:0.012047799 62:−0.060866039 63:0.030329872
64:0.060451269 65:0.078133844 66:0.19231768 67:0.069377609 68:−0.011707771
69:−0.097945809 70:0.0088583073 71:0.053208005 72:−0.011949218 73:−0.045471206
74:−0.0034239914 75:0.012749125 76:−0.010776159 77:0.19096926 #
−0.011419236121856483 1:−0.74429584 2:2.1880109 3:−2.3696415 4:−1.9438547 5:−9.2926893
6:0.99640316 7:−0.6767 8:1.6258518 9:−0.11437076 10:−1.4794613 11:0.81431127 12:−0.21384634
13:0.53743309 14:0.077872261 15:1.3259499 16:−0.71300405 17:0.0049439492 18:1.3197745
19:−0.111271 20:0.69736075 21:0.22185689 22:−0.56547165 23:0.12162654 24:0.35936192
25:−0.49727443 26:0.093655713 27:0.21406183 28:0.067851081 29:−0.33224609 30:−0.018647455
31:−0.039257858 32:0.21896116 33:−0.22458608 34:0.35473901 35:−0.053331349 36:0.30089357
37:−0.22295676 38:−0.095555477 39:0.23255841 40:0.36355895 41:0.17061484 42:0.26699126
43:−0.077034004 44:0.20102701 45:−0.012858211 46:−0.25222632 47:−0.10690235 48:0.11655796
49:0.032803442 50:0.1501172 51:−0.069798179 52:−0.13112213 53:0.13219874 54:0.043789726
55:−0.078813396 56:−0.20198624 57:−0.10686306 58:−0.035710312 59:0.027775692 60:0.1577934
61:0.0020142384 62:−0.10952839 63:0.032901403 64:−0.11604125 65:0.030962365
66:0.015522253 67:−0.00032681588 68:0.075245097 69:0.041201141 70:−0.01021499
71:−0.0002418708 72:0.03941628 73:−0.01827208 74:0.0044438085 75:0.018536061 76:−0.021680554
77:0.19096926 #
0.01055303618580938 1:0.63907987 2:0.24358398 3:3.2116609 4:1.7944192 5:0.20658349
6:3.2340112 7:1.5370831 8:−0.92006946 9:−0.56229812 10:−0.917669 11:1.1035053 12:−1.2516662
13:−2.5576138 14:1.482617 15:0.26023376 16:0.36993003 17:−0.32038087 18:−0.4832359
19:−1.0070493 20:−0.12898561 21:1.7116643 22:−0.049816001 23:0.19220746 24:0.40307271
25:0.1162524 26:0.016468888 27:0.018475451 28:−0.60244405 29:−0.052848581 30:−0.27111408
31:0.053797923 32:0.022011327 33:−0.23369427 34:0.17803811 35:−0.12628126 36:−0.3044194
37:−0.15073486 38:−0.23449378 39:0.17781459 40:0.33798808 41:−0.098511301 42:0.11782595
43:−0.23086511 44:0.0064016082 45:−0.17139821 46:−0.031457938 47:0.34474593
48:0.056878451 49:−0.080897167 50:−0.084760666 51:−0.011466268 52:0.0065853707
53:−0.028540993 54:0.060591973 55:0.07364542 56:−0.16182698 57:0.17885795 58:0.0071241134
59:−0.11486004 60:−0.0799376 61:−0.056142498 62:−0.044058383 63:−0.10933063 64:0.15502229
65:−0.14944047 66:−0.038380347 67:−0.06491939 68:−0.0045360639 69:0.11342485
70:−0.070126586 71:−0.0040296656 72:−0.011202 73:−0.082268685 74:0.052195996 75:−0.018841717
76:0.0053762593 77:0.19096926 #
0.014353309248426729 1:−0.44587362 2:−0.57146621 3:3.9785798 4:0.90431428 5:−0.93180883
6:−2.8584714 7:1.3682934 8:1.7635593 9:−0.64695787 10:−2.8194914 11:1.680328 12:−0.97989517
13:0.2084263 14:0.50162458 15:−0.68706387 16:−0.46809956 17:0.27005327 18:0.21921048
19:0.18712009 20:−0.3836036 21:0.59743798 22:0.016304431 23:0.23604654 24:0.056548294
25:0.56529737 26:0.45598608 27:−0.057835795 28:−0.18187784 29:0.95360893 30:−0.038308233
31:0.44872221 32:0.0062184148 33:−0.36823624 34:−0.015161993 35:0.18701878 36:0.28209782
37:0.22293513 38:0.71296561 39:0.19223149 40:−0.23543128 41:−0.43254086 42:0.22386651
43:0.25073311 44:−0.026097337 45:0.15424277 46:−0.17125346 47:−0.1071639 48:0.18486938
49:−0.044301238 50:−0.0064678248 51:0.046931431 52:−0.073714353 53:−0.045696627
54:−0.021205923 55:−0.13606429 56:−0.073592998 57:0.065833367 58:0.11732139 59:−0.043805864
60:0.11605238 61:0.072203234 62:0.069763772 63:−0.024779342 64:−0.048361409 65:0.12743172
66:−0.01593416 67:−0.09024749 68:−0.0028283934 69:−0.065591566 70:0.078308754
71:0.047920544 72:−0.098944493 73:0.028319601 74:0.06064973 75:−0.017613616
76:−0.01823408 77:0.19096926 #
0.014353309248426729 1:−0.76116866 2:2.1070783 3:2.8434978 4:−3.3621957 5:−4.8477507
6:0.27703968 7:−0.40033141 8:0.59389663 9:−0.91651338 10:−2.2844291 11:−0.35302642
12:0.77133405 13:0.20549387 14:−0.44337323 15:0.26893091 16:0.36496478 17:0.48438486
18:0.92744738 19:−0.28376448 20:0.36373788 21:−0.18942082 22:−0.91629821 23:0.69637895
24:0.321549 25:0.43027249 26:0.56917667 27:−0.43815917 28:0.18907948 29:−0.33716297
30:−0.50700164 31:−0.23392172 32:−0.18396404 33:−0.47307968 34:0.43280628 35:−0.31686023
36:−0.027117359 37:−0.087249637 38:0.22449394 39:0.080588408 40:0.099335499 41:0.36332706
42:0.48767376 43:0.17989831 44:−0.2032342 45:−0.35130808 46:0.26717523 47:0.032289274
48:0.029517708 49:0.026310066 50:0.10121942 51:0.13020502 52:0.0062728929 53:0.16951694
54:0.1587085 55:0.15667053 56:0.0048121801 57:0.078118421 58:0.034498923 59:0.071819201
60:−0.065712735 61:0.00072833541 62:−0.026640892 63:0.067254961 64:0.10896165

APPENDIX C13-continued

SVM Model Weights
(77; Normal/Diseased)

65:0.091121376 66:0.041503921 67:−0.063253254 68:−0.058849603 69:−0.051496848
70:−0.041686796 71:0.023902418 72:−0.053651284 73:−0.014551555 74:−0.016947519
75:0.031618398 76:0.014569249 77:0.19096926 #
0.014353309248426729 1:−2.2298379 2:−4.4939141 3:4.5170412 4:1.3069468 5:2.3184917
6:0.24040304 7:−1.1550515 8:−1.5276875 9:0.80979383 10:0.45089707 11:0.84770244
12:0.64705956 13:−0.81330371 14:−0.3727951 15:−0.50112724 16:0.07223513 17:0.49537027
18:0.23592409 19:0.65843207 20:−0.077337176 21:0.2946696 22:−0.87977707 23:0.72163343
24:−0.003137961 25:0.26308727 26:0.043631624 27:−0.1515217 28:−0.3970727 29:0.041153982
30:−0.17486508 31:0.28032899 32:0.77467448 33:0.28497049 34:−0.27473375 35:0.39354101
36:0.1225123 37:0.16890125 38:−0.046522558 39:−0.14602707 40:−0.54183668 41:0.35876992
42:0.20727497 43:−0.07947807 44:0.27067989 45:−0.10931937 46:0.23082791 47:0.012216367
48:−0.16517885 49:−0.19009252 50:−0.067400761 51:−0.20689847 52:−0.062615551
53:−0.074973367 54:−0.15313455 55:−0.18991308 56:0.078412674 57:−0.014701044 58:−0.096595041
59:0.13159084 60:−0.11259133 61:0.032858286 62:−0.023201961 63:0.058368828 64:0.021501774
65:0.011077539 66:0.010597196 67:−0.0062902714 68:0.11205824 69:0.0065186406
70:0.053680804 71:0.055571102 72:0.033880748 73:−0.059979748 74:0.042440943
75:0.03030598 76:−0.0013416014 77:0.19096926 #
−0.014353309248426729 1:4.9410763 2:0.028376307 3:4.5598865 4:2.3924432 5:1.5779027
6:0.62230515 7:0.2012326 8:0.066585623 9:−1.2832874 10:−0.52035141 11:−1.2999072
12:0.65249121 13:1.5901349 14:0.41056466 15:0.88952464 16:1.0365381 17:1.1367617
18:1.000276 19:−0.5945102 20:−0.29482403 21:0.0075644036 22:−0.32880011 23:0.13806112
24:−0.31514499 25:0.098527983 26:−0.52334559 27:−0.073513843 28:0.30959809 29:−0.32110712
30:0.069601253 31:0.15723357 32:0.34551907 33:−0.089200102 34:0.15063688 35:−0.05898869
36:−0.57846928 37:−0.24106173 38:−0.28090253 39:0.10218818 40:0.0081301965 41:0.088019088
42:−0.014718652 43:0.055682864 44:0.18077977 45:−0.071272232 46:−0.19371572
47:−0.058893975 48:0.043162957 49:0.12905866 50:0.013424966 51:−0.041339759 52:0.089209259
53:−0.19151065 54:−0.19561097 55:0.0097125499 56:−0.077880435 57:−0.15064913
58:0.065724686 59:0.049564261 60:−0.095252328 61:0.054486036 62:−0.15566817
63:0.052545484 64:−0.12691513 65:0.046844095 66:0.023572905 67:−0.01758248 68:−0.0705797
69:0.093087055 70:0.046730079 71:−0.050051574 72:0.027777361 73:0.051185053
74:0.045371909 75:−0.018393328 76:0.029237276 77:0.19096926 #
−0.014353309248426729 1:4.4813638 2:−3.8440425 3:2.6549728 4:0.42552999 5:1.9560305
6:1.9099692 7:−0.70432049 8:0.28573781 9:1.281601 10:−0.20222963 11:−0.1215191
12:−1.0216136 13:−0.10441654 14:0.34899732 15:0.33193082 16:0.11575672 17:0.79601592
18:0.70577514 19:−0.75297785 20:−0.59386533 21:0.68368691 22:−0.24473876 23:−0.30474597
24:0.078599066 25:−0.67700851 26:−0.38023299 27:−0.40585434 28:−0.35101449 29:0.026945578
30:0.21643445 31:0.054349605 32:−0.10296464 33:0.25484857 34:−0.34924799 35:−0.40363479
36:−0.03266982 37:−0.090318248 38:0.10858562 39:0.23202638 40:−0.36166242 41:−0.02221092
42:−0.010762253 43:0.078397498 44:0.33982852 45:−0.00010069329 46:0.0052480674
47:−0.022083223 48:0.088137917 49:−0.010911894 50:−0.10745347 51:0.40995899 52:−0.071833134
53:0.13706979 54:0.13719527 55:−0.053848915 56:−0.08415883 57:−0.06813886 58:−0.1217611
59:−0.078865238 60:0.098876238 61:0.13171288 62:0.14629424 63:0.10457779 64:0.066938937
65:0.034765232 66:0.046820175 67:−0.029366124 68:−0.064977989 69:−0.013324194
70:0.025150163 71:−0.051605452 72:0.089329451 73:−0.0059083709 74:0.010806509
75:0.047982223 76:0.020032533 77:0.19096926 #
−0.014353309248426729 1:4.6218314 2:1.3604276 3:2.1358893 4:2.4516642 5:−0.77263111
6:1.4849045 7:0.020313663 8:−0.030556334 9:−1.998217 10:0.49116245 11:−0.85092783
12:−1.6515005 13:1.0444244 14:0.32572666 15:−0.048132528 16:−0.15972862 17:0.5767113
18:0.077659532 19:−0.29966244 20:−0.32004043 21:1.3344682 22:−0.70726383 23:−0.24180868
24:−0.32398933 25:0.23877986 26:0.16512501 27:−0.26871952 28:0.22163665 29:−0.49659771
30:0.034014925 31:0.090689249 32:−0.26650566 33:0.53866142 34:0.050626416 35:0.4012025
36:−0.073141925 37:−0.22068082 38:0.11073288 39:0.084362492 40:−0.12717631
41:−0.019866092 42:0.17179181 43:0.046213623 44:0.076445878 45:−0.091714337 46:0.017844126
47:0.11934163 48:0.15475342 49:0.10962146 50:0.01710429 51:0.076961666 52:0.153263
53:0.092687629 54:0.086195409 55:0.043428253 56:−0.049691103 57:0.08109501
58:−0.055613156 59:0.086764283 60:−0.11155787 61:0.1260038 62:−0.05119805 63:0.068623051
64:0.04535342 65:0.015173049 66:−0.01432985 67:−0.0083273761 68:0.066106416
69:−0.026755806 70:−0.052116465 71:0.0016122557 72:0.0098566618 73:0.065759338
74:−0.063594155 75:−0.0051325927 76:−0.024437901 77:0.19096926 #
−0.014353309248426729 1:7.4282398 2:−2.6248059 3:2.2744725 4:−1.4918871 5:1.3065705
6:−1.8817738 7:0.10123298 8:3.409272 9:−1.1257675 10:0.57093334 11:0.5125913 12:0.94756818
13:1.185836 14:1.6217183 15:0.098220505 16:0.33942458 17:−0.39164966 18:0.40921777
19:0.096525602 20:−0.47163692 21:−0.11492935 22:−0.27848256 23:−0.36137047 24:0.27162412
25:0.084303863 26:0.00047727249 27:−0.1624341 28:−0.0048333239 29:0.18919766
30:0.34176683 31:−0.12511563 32:−0.090722539 33:−0.13180412 34:0.23847516 35:0.042087033
36:−0.10052584 37:0.21115631 38:−0.066321194 39:0.10622354 40:0.159347 41:−0.099656604
42:0.00066753308 43:0.27660519 44:−0.20579761 45:0.034548622 46:−0.13626097
47:−0.0056114327 48:−0.035190638 49:−0.0033395339 50:−0.31059486 51:0.24721248 52:−0.15059415
53:−0.10924981 54:−0.061886605 55:0.21522547 56:0.041954089 57:0.049445726
58:−0.022822073 59:−0.15357602 60:−0.030031014 61:−0.04927228 62:−0.028705256 63:0.019317316
64:−0.00065417134 65:−0.015369516 66:0.022862462 67:0.037885979 68:0.016884357
69:0.015641861 70:−0.04899127 71:−0.041006796 72:0.068672843 73:0.0052308701
74:0.029559942 75:0.022282522 76:−0.034433428 77:0.19096926 #
−0.014353309248426729 1:4.8514752 2:−3.3980389 3:1.9618441 4:1.8562799 5:1.4686601
6:1.2358379 7:−0.54984504 8:−2.1043239 9:−0.77199781 10:0.28452376 11:−0.67378968
12:0.55217421 13:0.21284609 14:1.3635359 15:−0.15604992 16:0.22762947 17:0.071564324
18:−0.30310518 19:0.29381508 20:−0.66121006 21:0.21619134 22:0.45768857 23:0.25420132

APPENDIX C13-continued

| SVM Model Weights (77; Normal/Diseased) |
|---|
| 24:−0.38284421 25:0.072350442 26:−0.19524246 27:0.20096147 28:0.30810738 29:0.37903893 30:0.20721129 31:0.10489657 32:0.18264684 33:0.051573016 34:0.32168031 35:−0.0067289793 36:−0.049905371 37:−0.40784949 38:−0.62884259 39:0.28728673 40:0.15926403 41:−0.35284591 42:0.096441403 43:0.13453647 44:−0.11386138 45:−0.12181965 46:−0.12006382 47:−0.026937842 48:−0.13339894 49:0.16766343 50:−0.064012498 51:−0.17242569 52:−0.023951642 53:−0.10463927 54:0.13697778 55:−0.164499 56:−0.038791992 57:−0.039364967 58:−0.079756208 59:0.11294831 60:−0.037242748 61:−0.16044682 62:0.037739322 63:−0.031789865 64:0.10388539 65:0.12605348 66:0.037847877 67:−0.017321274 68:0.062975049 69:−0.030331185 70:−0.0080079297 71:−0.028001588 72:−0.07913015 73:0.0025401404 74:−0.045967285 75:0.022405686 76:0.018250167 77:0.19096926 # |
| 0.014353309248426729 1:−2.2572463 2:4.9335952 3:−0.56694895 4:1.0843779 5:−1.0996099 6:0.28483284 7:0.30359831 8:0.38171506 9:−0.25031024 10:0.99423325 11:0.80513161 12:0.93581688 13:−0.78284568 14:−0.28124028 15:0.45910963 16:0.45467502 17:1.7598574 18:−1.0129399 19:0.56820077 20:−0.19834319 21:−0.56580645 22:0.091331877 23:0.13443819 24:0.49826229 25:−0.097675979 26:−0.011314509 27:−0.22073109 28:0.23857851 29:−0.30153507 30:0.36173341 31:−0.17280245 32:0.057907581 33:0.15661848 34:−0.049501967 35:0.13675492 36:−0.025015023 37:0.21550058 38:−0.11524401 39:−0.070336312 40:−0.21460935 41:0.22718662 42:0.038921311 43:0.21651243 44:0.070852868 45:0.13680829 46:−0.21293902 47:−0.27537969 48:−0.014059026 49:0.12293613 50:−0.16044581 51:0.11894881 52:0.0022732774 53:−0.18749376 54:−0.15548299 55:−0.15311524 56:0.028143495 57:0.18196791 58:0.0022061404 59:−0.16124046 60:−0.013474897 61:−0.13689369 62:−0.024250872 63:0.124664 64:0.00063318567 65:−0.059331387 66:−0.010227511 67:0.092083864 68:−0.052342013 69:−0.047479596 70:−0.023824127 71:−0.011007925 72:−0.011507803 73:−0.015072041 74:0.005337317 75:0.02124987 76:0.0091837374 77:0.19096926 # |
| 0.014353309248426729 1:6.9592819 2:1.3774884 3:−3.0194819 4:0.12627706 5:−4.3371043 6:−3.1942868 7:1.5445083 8:0.8463695 9:0.51638108 10:1.4627318 11:2.4068072 12:−0.71283168 13:−0.43340632 14:0.1226351 15:0.20135117 16:−1.1858557 17:−0.23712626 18:−0.4499073 19:−0.14921801 20:0.17478763 21:0.60432476 22:−0.18867689 23:−0.24104717 24:0.74909377 25:−0.23596959 26:0.081719808 27:0.97526348 28:−0.48619637 29:−0.083923645 30:−0.51248038 31:−0.36379632 32:0.059764009 33:0.41636121 34:0.40770543 35:0.76083362 36:0.10140081 37:−0.3850067 38:−0.19243301 39:−0.028096445 40:−0.32614347 41:−0.19013552 42:0.0025015892 43:0.24576518 44:0.021531424 45:−0.093732581 46:0.12567116 47:0.20852761 48:0.14920041 49:−0.0075935456 50:0.010838507 51:−0.19169539 52:−0.044634577 53:−0.09095493 54:0.092887774 55:0.16684018 56:0.19925949 57:−0.13830015 58:−0.034867279 59:−0.13484813 60:0.11526398 61:0.079313755 62:0.048059601 63:0.15227152 64:−0.080761135 65:−0.031256091 66:0.010464945 67:0.066518672 68:−0.096629724 69:−0.0069553605 70:−0.023800366 71:0.032107353 72:−0.0015977139 73:0.016349833 74:−0.026028097 75:−0.026408292 76:0.0011199565 77:0.19096926 # |
| 0.014353309248426729 1:1.9467795 2:−0.65525383 3:−1.3458456 4:−3.1507697 5:−0.43218493 6:−2.4291291 7:0.96837443 8:0.18129982 9:0.47220087 10:−0.26647145 11:1.4806275 12:1.7461603 13:0.16688313 14:0.055250708 15:−0.80464393 16:0.26715639 17:−0.018202255 18:−0.34654555 19:0.18668748 20:−0.047953743 21:0.38636303 22:0.20377585 23:−0.19682075 24:−0.49527174 25:0.58606529 26:0.17793958 27:0.30355105 28:−0.25968778 29:−0.26261386 30:0.15440075 31:0.08969979 32:−0.10782174 33:−0.083654247 34:−0.32423192 35:−0.061030727 36:−0.60245836 37:0.047169741 38:0.10981783 39:0.22536203 40:0.36564034 41:0.20523848 42:0.15281519 43:−0.029824343 44:0.022048436 45:0.17621699 46:0.047230139 47:−0.032325555 48:0.11591725 49:−0.13120645 50:0.26160732 51:−0.019291906 52:0.20324504 53:−0.048651069 54:−0.045387633 55:−0.10453488 56:0.087177254 57:0.15782985 58:−0.051606718 59:−0.14556204 60:0.049657598 61:0.029512854 62:0.0038672241 63:−0.070933901 64:−0.051134162 65:0.070322014 66:0.020157678 67:0.010223137 68:0.056511804 69:0.081115589 70:0.040858567 71:−0.028441098 72:0.011788564 73:0.079359949 74:0.028478568 75:0.040636417 76:0.020964822 77:0.19096926 # |
| 0.014353309248426729 1:−0.15557319 2:4.3723865 3:−0.23605698 4:−2.9165714 5:−1.7426833 6:−0.63806218 7:−0.15775178 8:0.10422198 9:−1.8065854 10:0.24452505 11:−0.88657248 12:0.51000756 13:−1.8220752 14:−1.8767999 15:−0.052631695 16:−0.067146227 17:0.26439473 18:−0.18187712 19:0.78497028 20:0.72714728 21:0.55480063 22:−0.16318278 23:−0.19349746 24:−0.30053291 25:0.02575795 26:−0.11287499 27:−0.47420934 28:0.24046519 29:−0.21755555 30:−0.047029756 31:−0.22155724 32:−0.48609415 33:0.23585814 34:0.16938294 35:0.055679932 36:−0.39406148 37:0.13766672 38:0.099502437 39:0.017431935 40:0.0085642766 41:−0.037441637 42:0.19358334 43:0.12711357 44:0.17284454 45:0.0160072 46:−0.073837049 47:0.15224297 48:−0.2927115 49:−0.24626425 50:−0.16793211 51:−3.3523262e−005 52:−0.2114538 53:0.19861957 54:0.066733785 55:0.032950882 56:0.075327009 57:0.061877899 58:−0.11046685 59:−0.051397149 60:0.084722519 61:−0.020086968 62:−0.07758563 63:−0.068800606 64:0.028826082 65:−0.019862974 66:−0.082195751 67:−0.086992621 68:0.04037692 69:−0.0024737313 70:0.049855556 71:−0.10164 72:0.067814425 73:0.0081369504 74:−0.048196226 75:−0.015849108 76:−0.0062728073 77:0.19096926 # |
| 0.014353309248426729 1:−0.63522774 2:−1.8122028 3:0.46028304 4:0.041747943 5:−0.46811014 6:2.2675428 7:−0.21060076 8:1.4816533 9:−0.79302752 10:0.1739559 11:0.10976346 12:1.0899497 13:0.58113301 14:−0.65520346 15:−0.65256876 16:0.46754467 17:0.4423531 18:−0.44301495 19:−0.38169837 20:−0.56737471 21:0.39002049 22:−0.10822007 23:−0.61505824 24:−0.052359253 25:−0.160331 26:−0.46005762 27:0.47491974 28:0.27224934 29:0.23317359 30:−0.1217893 31−0.09044227 32:−0.14938219 33:0.50404501 34:0.25393423 35:0.01402833 36:0.32926172 37:0.36614433 38:−0.034436759 39:−0.38732022 40:0.36197925 41:−0.45878625 42:0.078224517 43:−0.16175719 44:−0.063902654 45:−0.058477178 46:0.057375565 47:0.12465123 48:0.1883807 49:0.15465756 50:0.17257911 51:−0.046278603 52:−0.16610728 53:0.062939979 54:−0.034222644 55:−0.27900857 56:0.016767981 57:−0.12676512 58:0.069833919 59:−0.015449548 60:−0.10493284 61:−0.11312296 62:−0.066784084 |

APPENDIX C13-continued

SVM Model Weights
(77; Normal/Diseased)

63:−0.009473376 64:0.034513686 65:0.11084645 66:−0.029376486 67:−0.06818679 68:−0.037577353 69:0.035966318 70:0.057747371 71:−0.032710411 72:0.021206157 73:−0.0062609352 74:−0.027881922 75:0.020901417 76:0.012451812 77:0.19096926 #
−0.010319975218643838 1:9.3993587 2:−1.19804 3:−4.7709165 4:−9.7187901 5:−0.46203515 6:−2.8200638 7:0.15260653 8:1.2916825 9:−0.75806254 10:−0.24209824 11:−0.55342066 12:1.3640094 13:−0.1630082 14:0.36108041 15:−0.43054807 16:−0.3536391 17:−0.60939878 18:−0.053753655 19:0.85556787 20:−0.93897331 21:0.56041497 22:0.3845863 23:0.67087048 24:0.12777601 25:0.27058715 26:0.22266127 27:−0.2092474 28:−0.26249549 29:−0.060754266 30:0.34741411 31:0.56113648 32:−0.14405504 33:0.25072095 34:0.11641443 35:0.21883674 36:−0.13888034 37:0.25070122 38:−0.1706825 39:0.05704353 40:−0.18688327 41:0.21651208 42:−0.446354 43:−0.018393507 44:0.18123221 45:0.09627863 46:−0.0086695794 47:0.012850617 48:−0.35473636 49:0.4286862 50:−0.01126251 51:0.034148861 52:0.027141018 53:0.25404912 54:−0.18210515 55:−0.088605396 56:−0.1054966 57:0.00052805536 58:−0.023626633 59:0.073317818 60:0.018437078 61:0.046114694 62:−0.056008123 63:−0.094066538 64:0.081167012 65:0.0050681685 66:0.031297997 67:0.0094710384 68:−0.061052751 69:−0.043621447 70:−0.056554295 71:0.038398534 72:0.029149842 73:0.0380724 74:0.0095785027 75:−0.059383072 76:0.018968474 77:0.19096926 #
−0.014353309248426729 1:0.55783176 2:4.1852026 3:−1.7936513 4:−2.1225643 5:−1.77618 6:−4.5577497 7:0.96169293 8:−1.1632956 9:0.62120473 10:0.5683198 11:0.99829346 12:0.55970162 13:0.41957814 14:−0.38833311 15:−0.13037378 16:0.30502588 17:−0.30768213 18:−0.1185056 19:−0.95438772 20:−0.6190002 21:0.31126055 22:0.58554107 23:0.064177908 24:0.14021122 25:−0.61616719 26:0.044506099 27:0.4478626 28:−0.20571189 29:0.87007827 30:0.7313351 31:0.086134188 32:−0.25757921 33:−0.53217393 34:0.36110353 35:−0.106413136:−0.50949872 37:−0.21266848 38:−0.1956345 39:0.19586581 40:−0.0053610634 41:0.033374704 42:0.047077887 43:−0.31137973 44:0.15809941 45:−0.27893427 46:0.25658858 47:−0.25968337 48:−0.13191912 49:0.063628182 50:−0.030129215 51:−0.19259889 52:−0.0065336903 53:0.19324036 54:−0.090310924 55:0.01654546 56:0.038154244 57:0.020546898 58:−0.043131586 59:0.046531592 60:−0.020224821 61:0.053396571 62:0.13397443 63:0.02939585 64:−0.10053076 65:−0.029972546 66:−0.08305984 67:0.026157988 68:0.08114782 69:−0.0076091839 70:0.047220051 71:−0.012726695 72:0.050144698 73:−0.068450153 74:0.0011088713 75:−0.005088157 76:0.0067782323 77:0.19096926 #
−0.013259971674367561 1:4.9170909 2:0.24498171 3:1.4921492 4:2.8226445 5:−1.9824139 6:−1.6338645 7:−1.7355236 8:0.90928531 9:0.55450684 10:−0.00079076679 11:0.54183584 12:−0.81717128 13:0.010111375 14:1.0843759 15:0.2620492 16:0.050128512 17:−0.28733078 18:0.6604327 19:−0.0048801186 20:0.16399975 21:−0.094933495 22:−0.29764932 23:−0.53233314 24:−0.55111527 25:−0.18164574 26:−0.021518005 27:−0.40798622 28:0.36103302 29:−0.58994234 30:0.22859351 31:−0.076492533 32:−0.17652856 33:−0.033358093 34:0.10846927 35:0.41113421 36:−0.48406672 37:0.23617058 38:0.19152007 39:−0.17122111 40:−0.10988266 41:0.15846995 42:−0.25915647 43:−0.081959926 44:−0.22234547 45:−0.042677384 46:0.25828609 47:0.052843571 48:0.15753846 49:−0.089786358 50:−0.087969191 51:−0.27383611 52:−0.02823001 53:0.015598758 54:−0.063495643 55:0.0074624638 56:−0.021769151 57:−0.049487364 58:−0.0016493469 59:−0.076925077 60:−0.14056399 61:−0.12364015 62:0.011578115 63:0.010628217 64:0.034212682 65:−0.049569659 66:−0.046433996 67:−0.037091695 68:−0.034406889 69:−0.033581007 70:−0.0054059015 71:−0.030539395 72:−0.078113854 73:0.016373781 74:−0.024029246 75:−0.015545838 76:0.0080719898 77:0.19096926 #
0.014353309248426729 1:5.9556971 2:−3.9141884 3:0.74362642 4:−0.83546388 5:2.2707839 6:2.6133182 7:0.69750202 8:0.34435734 9:−0.70712698 10:−1.5439632 11:−0.19805567 12:−0.39133734 13:0.98172504 14:−0.11901451 15:0.87558734 16:−1.0163729 17:−0.10674594 18:−0.75045395 19:0.13285002 20:1.0079689 21:0.037951764 22:−0.21780124 23:−0.090273701 24:0.29967195 25:−0.16260861 26:−0.045908831 27:0.17316794 28:0.15852824 29:0.53897524 30:0.33016431 31:0.067541555 32:0.067686185 33:−0.54376841 34:−0.29346713 35:0.084065534 36:−0.09260004 37:−0.12885442 38:0.12681502 39:−0.30663911 40:0.25368449 41:0.22037503 42:0.015084521 43:−0.077325933 44:0.22869365 45:0.12778468 46:−0.014559323 47:0.094691604 48:0.083088003 49:−0.06429027 50:−0.3800984 51:−0.028664147 52:0.192298 53:0.27696985 54:0.048203852 55:0.033951834 56:−0.083681874 57:−0.0014338634 58:−0.10042396 59:−0.27372143 60:−0.086212873 61:0.041977238 62:−0.035775848 63:0.042932626 64:−0.05388109 65:0.040165126 66:0.080133237 67:0.082697213 68:0.10461962 69:0.090810165 70:0.0015228875 71:−0.0024229137 72:−0.05122539 73:0.048772104 74:−0.038265396 75:−0.030125355 76:0.014639161 77:0.19096926 #
0.014353309248426729 1:3.9972777 2:−4.8784895 3:2.0307999 4:0.6114037 5:−1.863481 6:1.1202273 7:0.58167011 8:−0.58695805 9:0.53085732 10:1.2303116 11:−0.25934854 12:−0.35827774 13:−0.13902797 14:−0.27432188 15:0.16462867 16:−0.32321993 17:−0.31504294 18:−0.24832314 19:0.26840174 20:−0.32129249 21:−0.77787262 22:0.36887968 23:−0.28857508 24:0.26738095 25:−0.38637212 26:−0.37484664 27:−0.10660054 28:−0.28513494 29:−0.23566799 30:−0.70198399 31:−0.3417736 32:−0.02378506 33:−0.25416315 34:0.40531573 35:0.13978416 36:0.30868 37:−0.25277588 38:−0.30961639 39:0.081101164 40:−0.08358261 41:−0.041034237 42:−0.14691368 43:0.29719633 44:−0.074558169 45:0.36800078 46:0.1058566 47:0.18667345 48:0.24515209 49:−0.034719497 50:0.044236347 51:0.039808929 52:−0.09635783 53:0.085162275 54:0.055112023 55:0.10942905 56:0.096976653 57:−0.074628584 58:−0.03296306 59:−0.036982916 60:0.046869516 61:−0.13793884 62:0.047014769 63:−0.021881195 64:0.074361451 65:0.033877105 66:0.032080255 67:0.035054222 68:0.0093465112 69:0.023212995 70:0.16814013 71:0.082159832 72:0.016997227 73:0.037973482 74:0.042132806 75:−0.0050213025 76:−0.011269757 77:0.19096926 #
0.014353309248426729 1:2.4744589 2:−5.4028807 3:1.2627662 4:0.044713747 5:0.16699603 6:−0.67353725 7:0.94016552 8:1.2057127 9:0.95045656 10:−0.3182947 11:0.68477654 12:0.48962635 13:0.44830358 14:−0.0057733902 15:1.1272933 16:0.038393974 17:−0.27598074 18:−0.24064331 19:−0.27064306 20:−0.15513277 21:−1.2655782 22:0.69975078 23:−0.067884408

APPENDIX C13-continued

| SVM Model Weights (77; Normal/Diseased) |
|---|
| 24:0.43130171 25:0.096297719 26:0.37309849 27:−0.34194618 28:0.18837163 29:−0.39284086 |
| 30:0.14948799 31:0.070518807 32:−0.403364 33:0.15725875 34:−0.010741657 35:−0.070608504 |
| 36:−0.079830892 37:0.1424198 38:−0.11449236 39:0.019168518 40:−0.075147174 41:0.085544914 |
| 42:−0.00081659848 43:−0.01507942 44:0.15558228 45:−0.059686802 46:0.040933326 |
| 47:0.13798119 48:0.18525146 49:−0.0072453856 50:−0.076657243 51:0.0027342332 |
| 52:0.012802244 53:−0.0029421558 54:0.033918325 55:−0.00071074383 56:−0.028227104 |
| 57:0.065211311 58:0.050295778 59:0.037094761 60:0.13525249 61:−0.032472637 |
| 62:−0.0090333754 63:−0.037603613 64:−0.06100712 65:0.0049549881 66:0.012151481 |
| 67:−0.13747771 68:−0.0628177 69:−0.065721788 70:0.004662164 71:−0.11007418 72:0.018610314 |
| 73:−0.10742028 74:−0.01603958 75:−0.0051265075 76:0.032731224 77:0.19096926 # |
| −0.0038323623165111278 1:4.2893538 2:−5.2345309 3:−1.2000556 4:−0.93739718 5:−3.0942731 |
| 6:0.99917591 7:1.0002351 8:−0.9112013 9:0.96190113 10:0.79657519 11:0.25024614 |
| 12:0.61497545 13:2.3182609 14:−0.4486129 15:−0.75491154 16:0.017280445 17:0.48615381 |
| 18:−0.96390826 19:0.20012768 20:−0.75417548 21:−0.23974042 22:−0.66195297 23:−0.80147773 |
| 24:−0.19814359 25:−0.54243588 26:0.10220911 27:0.2538895 28:0.30050173 29:0.46053413 |
| 30:−0.65405566 31:−0.11487853 32:0.10232334 33:−0.16707741 34:−0.27787521 35:−0.25273025 |
| 36:−0.17336521 37:−0.40852961 38:0.39471078 39:−0.14809722 40:−0.21019436 41:−0.13097575 |
| 42:−0.028161552 43:0.1471158 44:−0.076230474 45:−0.075148255 46:0.34740126 47:−0.30463791 |
| 48:−0.14139266 49:0.25022587 50:0.056683 51:0.28616363 52:−0.053105246 53:−0.086513609 |
| 54:0.053961672 55:0.15732297 56:−0.12059868 57:0.088480346 58:0.036826268 59:0.092309855 |
| 60:−0.0042303326 61:−0.018553153 62:0.00018127541 63:−0.17700627 64:0.050290953 |
| 65:−0.13287471 66:−0.022995656 67:0.036085851 68:0.070155948 69:−0.012894882 70:−0.001624166 |
| 71:−0.082139239 72:−0.039654747 73:−0.014241439 74:0.016516613 75:0.0075132675 |
| 76:0.023724973 77:0.19096926 # |
| −0.014353309248426729 1:5.7117987 2:−3.5476892 3:−1.9275512 4:−4.6104388 5:3.8808806 |
| 6:−0.050307896 7:2.5059583 8:0.62158495 9:−0.62527925 10:−0.46950975 11:0.38747376 |
| 12:−0.083297186 13:−0.88761806 14:0.75545627 15:−1.9015464 16:−1.0466732 17:0.78937095 |
| 18:0.4392699 19:−0.29955837 20:2.7437365 21:0.39261153 22:0.17623644 23:−0.51865458 |
| 24:0.10821868 25:−0.53393173 26:−0.82497048 27:−1.1169041 28:0.2371632 29:−0.20336817 |
| 30:0.046445303 31:0.11912714 32:−0.18746027 33:0.12606077 34:0.55417848 35:−0.6567288 |
| 36:0.27108726 37:−0.49200851 38:−0.23088348 39:−0.050104309 40:−0.14605463 41:−0.058776151 |
| 42:−0.030237556 43:−0.0029275035 44:−0.39270642 45:0.19888729 46:0.098669767 |
| 47:−0.085759103 48:0.023587802 49:−0.25945893 50:0.1586591 51:0.023863504 52:0.27987778 |
| 53:−0.015695041 54:−0.16439915 55:−0.2554948 56:−0.070765734 57:0.21345666 58:−0.095435366 |
| 59:0.16742267 60:0.017690454 61:−0.035758782 62:0.011158342 63:0.077918343 |
| 64:−0.098814957 65:0.021842305 66:0.0025222716 67:−0.032652933 68:−0.048068583 |
| 69:−0.010246019 70:−0.010302986 71:0.0084776562 72:0.010113241 73:0.001541813 |
| 74:−0.0070297513 75:−0.030572709 76:0.0065082805 77:0.19096926 # |
| −0.014353309248426729 1:3.9253345 2:−4.2669892 3:2.1907012 4:−1.0499724 5:−3.688081 |
| 6:1.1189013 7:−0.081566498 8:0.87137401 9:−0.015362982 10:1.6003631 11:0.30550104 |
| 12:1.5651579 13:1.1978846 14:0.8962028 15:−0.42782384 16:0.85182959 17:−0.37655097 |
| 18:−0.54154819 19:0.37134936 20:−0.34930256 21:−0.32465181 22:0.4815377 23:0.035673629 |
| 24:0.43283093 25:−0.17426214 26:0.25506917 27:0.093261503 28:0.3065626 29:0.31031379 |
| 30:0.049134124 31:−0.49726912 32:−0.28463152 33:0.34852663 34:−0.14099483 35:−0.34122592 |
| 36:0.30178943 37:−0.38929746 38:0.077965386 39:−0.11248251 40:−0.22577305 41:0.38777775 |
| 42:0.20318374 43:−0.10661437 44:0.18389307 45:0.41715941 46:−0.34485713 47:0.20974697 |
| 48:−0.075392939 49:0.024809383 50:0.12316398 51:0.11191528 52:0.051685944 53:−0.018093724 |
| 54:0.20039506 55:−0.0053530764 56:−0.00036596131 57:0.1091022 58:−0.025140146 |
| 59:0.016901722 60:−0.071862102 61:−0.02090106 62:0.15067241 63:−0.012306364 |
| 64:−0.10836221 65:−0.0076215765 66:−0.091254219 67:−0.10657305 68:0.013235348 69:0.038714714 |
| 70:−0.055360213 71:0.082291611 72:−0.039260566 73:0.00071480253 74:0.03970826 |
| 75:0.03448401 76:−0.034296799 77:0.19096926 # |
| 0.014353309248426729 1:−0.81432414 2:2.9625859 3:1.7483604 4:−3.0337141 5:0.97058022 |
| 6:−0.44561109 7:−1.3660054 8:−1.4018486 9:−0.19439347 10:−0.26922977 11:0.49191207 |
| 12:1.7290794 13:−0.44806811 14:1.655548 15:−0.48900166 16:−0.1046706 17:−0.092815086 |
| 18:−0.13355622 19:−0.22920068 20:0.15706243 21:−0.7783702 22:0.44720861 23:−0.78833252 |
| 24:0.66153544 25:0.32056373 26:−0.076845407 27:0.11414085 28:−0.18511112 29:−0.32979673 |
| 30:−0.36256209 31:−0.11508591 32:0.029555868 33:0.363379 34:0.19966549 35:0.16595547 |
| 36:−0.020053659 37:−0.034214944 38:0.24265467 39:−0.049128458 40:0.11732477 41:0.18154845 |
| 42:0.45228785 43:−0.13252868 44:−0.030638337 45:−0.34319016 46:0.086083926 47:−0.12227067 |
| 48:0.12250787 49:0.1431071 50:−0.1375915 51:0.19549033 52:−0.057022642 53:−0.05635323 |
| 54:−0.036347188 55:−0.025616266 56:0.17378554 57:−0.00672246 58:−0.094642192 59:0.030869938 |
| 60:−0.096479021 61:−0.027775951 62:−0.056568723 63:0.020785101 64:−0.061660096 |
| 65:−0.087504745 66:−0.06723053 67:−0.089936435 68:−0.0028781898 69:−0.08156646 70:0.027107075 |
| 71:0.066165619 72:0.055132478 73:0.016442494 74:−0.026586743 75:−0.0087840818 |
| 76:0.0026594417 77:0.19096926 # |
| −0.012727246964834548 1:−5.7681317 2:3.3800209 3:0.70475888 4:0.37414134 5:−4.0587316 |
| 6:0.53702301 7:−0.81787837 8:1.9542824 9:−0.69009209 10:0.28357568 11:−0.034164213 |
| 12:1.1068258 13:−1.4185724 14:−0.22418651 15:−0.75826502 16:−0.19433145 17:0.091967136 |
| 18:0.32567826 19:−0.26227486 20:−0.22510986 21:0.59652096 22:0.78451866 23:0.24676342 |
| 24:0.54458296 25:−0.033774476 26:−0.33373573 27:0.083485432 28:0.21458457 29:−0.52964228 |
| 30:−0.12906076 31:−0.35559258 32:−0.019371232 33:0.46668157 34:0.13806987 35:−0.10158478 |
| 36:−0.50101495 37:−0.049106907 38:0.2777096 39:0.096872687 40:−0.049518894 41:−0.20658958 |
| 42:−0.3201094 43:0.021335321 44:0.025062397 45:0.108256 46:0.021068657 47:−0.22012912 |
| 48:0.026493778 49:0.074017063 50:0.060526427 51:0.0033229047 52:0.030799717 |
| 53:−0.11855436 54:0.055574674 55:−0.19472452 56:−0.025524352 57:−0.0066594286 58:0.093248457 |
| 59:−0.10573544 60:−0.077440843 61:0.11338475 62:0.010284424 63:0.0099851526 |

APPENDIX C13-continued

SVM Model Weights
(77; Normal/Diseased)

64:0.066353261 65:0.02964782 66:0.020166192 67:−0.049718421 68:0.16579597 69:−0.064580455 70:−0.11981627 71:0.049149394 72:0.017069802 73:0.03058449 74:−0.0031467082 75:−0.00036968247 76:−0.019326014 77:0.19096926 #
−0.014353309248426729 1:0.082758948 2:1.0872548 3:2.8803341 4:−1.5396197 5:−2.5253313 6:−3.6075366 7:−1.6993489 8:1.1739776 9:3.6692131 10:−3.733027 11:0.33751383 12:0.010012857 13:0.60219866 14:−1.1733193 15:−0.37753054 16:−0.22642003 17:−0.34515664 18:−0.081465483 19:0.22794649 20:0.33426246 21:0.078032874 22:−0.56855321 23:−0.29651409 24:−0.9210586 25:−0.29813138 26:1.1078171 27:−0.36025259 28:0.0054071182 29:−0.12607428 30:−0.72077239 31:−0.2994 32:0.44088459 33:−0.12537844 34:0.16938999 35:0.02498908 36:0.20270418 37:−0.24733174 38:0.015018982 39:0.43954402 40:−0.062331337 41:0.050377581 42:−0.27534309 43:−0.065629624 44:−0.036910322 45:0.1218696 46:−0.35570991 47:−0.092473418 48:−0.095120929 49:0.051577609 50:−0.15100175 51:−0.15788227 52:0.077512011 53:−0.069173761 54:−0.10127854 55:−0.082375675 56:−0.16202414 57:−0.20374335 58:−0.0020916574 59:0.038819369 60:−0.11578211 61:−0.15603676 62:0.050284915 63:−0.016810518 64:0.063662447 65:−0.095844448 66:−0.095845424 67:0.013168102 68:−0.05825362 69:0.019698553 70:0.012952586 71:−0.0051970207 72:0.043707851 73:0.055682864 74:−0.0092193978 75:0.014001511 76:0.027772471 77:0.19096926 #
−0.014353309248426729 1:−4.0776148 2:1.5589889 3:2.9645562 4:0.71601045 5:1.213555 6:−0.49636409 7:−0.72156262 8:−0.52381468 9:0.43996242 10:0.93027204 11:0.87154049 12:1.969772 13:−0.5292787 14:0.014590077 15:0.52649361 16:−0.43340084 17:−0.67611063 18:−0.015292229 19:−0.52732515 20:−0.53303039 21:−0.46886608 22:0.13809073 23:−0.17828549 24:0.64610887 25:−0.95268834 26:0.06258285 27:0.63129693 28:0.59902829 29:−0.033746153 30:0.49899831 31:−0.27329406 32:0.18182819 33:−0.10255193 34:−0.21808268 35:−0.059965365 36:0.18355176 37:0.057001028 38:0.079007231 39:0.26791966 40:0.072083674 41:−0.081331238 42:−0.048946366 43:0.034092177 44:−0.17764695 45:−0.30076477 46:0.044828691 47:−0.042201597 48:0.022877971 49:−0.11680973 50:−0.14031042 51:−0.080965742 52:0.10697637 53:0.25408578 54:0.007026956 55:0.041460473 56:0.084552802 57:0.013163003 58:−0.10577556 59:0.19998506 60:0.19360611 61:−0.045427285 62:−0.18950908 63:−0.089682907 64:0.04733032 65:0.020535992 66:0.008784866 67:−0.060156077 68:−0.024672214 69:0.027011821 70:0.01525234 71:0.049400467 72:0.0060332832 73:0.036493219 74:−0.018665573 75:0.011054345 76:−0.01024831 77:0.19096926 #
0.014353309248426729 1:2.1380572 2:−2.7228491 3:1.2488432 4:0.4102937 5:−2.9014008 6:1.1901984 7:2.0268364 8:−0.078586377 9:−1.9476318 10:−0.67066097 11:−0.69973791 12:0.16662373 13:−0.11709127 14:0.33979279 15:−0.073219918 16:0.12294708 17:0.34147784 18:−0.76447976 19:−0.41885012 20:−0.45524213 21:−0.76993948 22:−0.01575391 23:0.221663 24:−0.23476636 25:0.22703917 26:−0.018201644 27:−0.22997233 28:0.36940411 29:0.11103288 30:0.01123321 31:0.027791834 32:0.094050832 33:−0.1215522 34:0.23883559 35:0.065992586 36:0.19062608 37:0.18068065 38:−0.1867848 39:0.061832182 40:0.10152243 41:0.15965089 42:0.58526248 43:0.10788931 44:−0.099007346 45:−0.14438507 46:−0.18448305 47:0.22651905 48:−0.088431731 49:0.048532378 50:−0.090074643 51:−0.026276754 52:0.13198911 53:0.071582593 54:−0.069793433 55:−0.061632629 56:−0.21420051 57:−0.16186282 58:−0.068689398 59:0.017617565 60:0.069247358 61:0.036123745 62:0.075025037 63:−0.029326707 64:−0.014987405 65:0.037071742 66:0.074724384 67:0.1470315 68:0.046811014 69:−0.064457484 70:0.029264685 71:0.017058592 72:0.022094186 73:0.011287562 74:0.050007377 75:−0.062666759 76:−0.0012450811 77:0.19096926 #
0.014353309248426729 1:−0.64856058 2:−6.3686175 3:3.385586 4:1.4785185 5:0.17008346 6:0.76989472 7:−0.25071886 8:−1.1828032 9:−1.0129256 10:−1.2772108 11:−0.35251454 12:0.56226933 13:−0.33724108 14:−0.21011251 15:0.9427743 16:−0.78182048 17:0.24627689 18:−0.71021044 19:−0.031844568 20:1.0301566 21:−0.17616488 22:0.55726373 23:−0.29998335 24:0.35410663 25:0.15372202 26:0.081583038 27:0.16215688 28:0.28623444 29:0.42353603 30:0.10801162 31:−0.16211954 32:−0.26956493 33:−0.1242821 34:0.35228136 35:0.17744695 36:0.14529315 37:0.014221409 38:0.16702312 39:0.070314638 40:−0.16397119 41:−0.26231906 42:0.035999145 43:−0.026150649 44:−0.16076523 45:0.16333939 46:−0.073249519 47:0.10942225 48:−0.35341778 49:0.083827898 50:−0.10657682 51:−0.19550951 52:0.25171685 53:−0.085471213 54:−0.22685494 55:0.023703946 56:0.13281411 57:−0.0074602254 58:0.060045518 59:−0.14166687 60:0.054085702 61:0.18912317 62:−0.069246575 63:0.017817793 64:−0.029411279 65:−0.091163196 66:0.0055854581 67:−0.068422824 68:−0.010447497 69:−0.091840915 70:−0.062866986 71:−0.062565513 72:−0.031148555 73:0.071449175 74:−0.018378057 75:0.076994047 76:0.01484601 77:0.19096926 #
0.014353309248426729 1:3.2940178 2:3.4852583 3:−0.068326652 4:2.2685461 5:−1.3683041 6:−0.5900774 7:1.6161363 8:−0.97544795 9:1.2447773 10:−0.26147082 11:−0.21289742 12:−0.58894807 13:−0.56581414 14:−1.1017224 15:1.0360084 16:0.39687103 17:0.187462 18:−0.84980369 19:0.19174182 20:0.17375821 21:−0.21087837 22:0.61974561 23:0.35311535 24:0.36437052 25:−0.10605622 26:−0.12673147 27:−0.34484401 28:0.40545368 29:0.23593782 30:0.34041846 31:0.10304689 32:0.18522094 33:0.14664431 34:0.054209836 35:0.33021811 36:0.36457884 37:0.070981435 38:−0.081268795 39:−0.11962464 40:−0.12024318 41:0.019062767 42:0.026453383 43:0.27713117 44:0.12317705 45:−0.018520508 46:0.033485681 47:−0.24418949 48:0.12452681 49:−0.060925346 50:−0.032987438 51:0.1391587 52:−0.048510402 53:−0.047748599 54:−0.058749538 55:0.022114977 56:−0.04048197 57:0.15567501 58:−0.086711019 59:0.051557973 60:−0.02005754 61:−0.1500306 62:0.023549406 63:0.0037479368 64:0.0024145106 65:−0.056376006 66:0.041432314 67:−0.030827077 68:0.050380014 69:0.016478913 70:0.03128827 71:−0.0021580884 72:−0.007698758 73:0.030375704 74:0.046912625 75:−0.0084215887 76:−0.035981584 77:0.19096926 #
−0.011447649186984984 1:4.3545189 2:−1.4769275 3:−2.6458828 4:−0.57968295 5:0.87673432 6:3.0129831 7:2.2782133 8:−2.2911229 9:−1.2831959 10:0.9590295 11:0.26767975 12:0.32180819 13:0.48155975 14:0.1966414 15:−1.3455921 16:−0.44320408 17:0.6583581 18:−0.79036593 19:−0.13167568 20:0.55932045 21:−0.87350529 22:1.0280255 23:1.1902955 24:−1.199928

APPENDIX C13-continued

| SVM Model Weights (77; Normal/Diseased) |
|---|
| 25:−1.468623 26:−0.42590466 27:−0.049586751 28:−0.2056893 29:−0.370648 30:−0.36656046 31:0.15245692 32:−0.1797298 33:0.47243661 34:0.3869898 35:0.28878298 36:−0.21835411 37:0.12263542 38:0.67257541 39:0.32014152 40:−0.059508383 41:−0.0052744737 42:−0.10404334 43:−0.23571524 44:0.31105131 45:0.057454094 46:0.1498322 47:0.32885611 48:0.047828276 49:−0.090642288 50:−0.14175545 51:−0.10974757 52:−0.30231673 53:−0.27513027 54:0.036292296 55:0.014866372 56:−0.14898349 57:−0.067851543 58:−0.14331603 59:0.025837462 60:−0.024958115 61:−0.030946646 62:0.019508969 63:−0.048755515 64:−0.036462758 65:0.032469302 66:−0.036901686 67:0.055405159 68:−0.030194798 69:−0.045148633 70:−0.054001097 71:−0.003147841 72:0.014633867 73:0.012649227 74:0.0041115549 75:0.040350892 76:0.0011266243 77:0.19096926 # |
| 0.014353309248426729 1:0.11540952 2:0.92830622 3:3.1418462 4:−0.41937986 5:2.0858693 6:0.50137603 7:1.3615035 8:0.92547667 9:0.55925763 10:−0.47193566 11:−0.5899505 12:1.7080383 13:0.95291448 14:−0.27768236 15:−1.6006554 16:0.39250687 17:−0.25121239 18:0.47731888 19:0.25471079 20:0.21262316 21:0.0056257481 22:−0.022298859 23:−0.58346117 24:−0.57041728 25:−0.040520214 26:0.087735362 27:0.75756675 28:−0.2631653 29:−0.022054942 30:0.69768965 31:−0.80494565 32:−0.026162012 33:−0.072255358 34:−0.0054053729 35:0.077567488 36:−0.19486891 37:0.33262455 38:−0.16944002 39:−0.0042993664 40:−0.078120872 41:0.018849202 42:−0.18277751 43:−0.050406951 44:−0.011862921 45:0.081747398 46:0.13225056 47:0.0071237027 48:0.16544269 49:0.010621698 50:0.041144613 51:−0.10130383 52:−0.14631146 53:0.22944328 54:0.10978479 55:0.020815115 56:−0.052316677 57:0.12853679 58:0.065861441 59:0.0061021303 60:−0.026331592 61:0.12338864 62:−0.060127947 63:0.16905735 64:−0.030747816 65:0.052571233 66:0.03778322 67:0.0067461156 68:−0.11597879 69:−0.086529948 70:0.029151805 71:0.042045731 72:−0.0066400883 73:0.022428755 74:0.063714884 75:0.010718993 76:0.0061087315 77:0.19096926 # |
| 0.014353309248426729 1:7.3016887 2:4.6196833 3:0.56539106 4:0.8258546 5:2.1178594 6:−2.4605103 7:1.0470536 8:0.99086946 9:2.3383286 10:−0.38931999 11:1.1940433 12:0.50192273 13:0.82606328 14:0.92078054 15:1.7312194 16:1.3126773 17:0.49116307 18:0.16430971 19:0.96897626 20:0.96705741 21:0.016897254 22:−0.62750036 23:0.33334187 24:−0.018038986 25:−0.22280914 26:−0.085072614 27:−0.31288022 28:0.10823265 29:−0.21143506 30:0.58848566 31:−0.49877399 32:0.29897302 33:−0.071670614 34:−0.23520376 35:0.061247725 36:0.50099373 37:−0.0091341427 38:−0.072287723 39:−0.060008947 40:0.37008503 41:−0.09687981 42:−0.10114875 43:−4.5531283e−006 44:−0.26902145 45:0.14090419 46:0.16193986 47:0.34543023 48:−0.22811948 49:0.088336676 50:0.24418978 51:0.16058241 52:−0.14929508 53:−0.0089816526 54:−0.036122527 55:0.1035931 56:0.065650843 57:0.0028851186 58:−0.014268463 59:−0.035596605 60:0.032398522 61:−0.0085472539 62:0.098853037 63:−0.0048894407 64:0.054890506 65:0.026125254 66:−0.033926487 67:0.081910454 68:0.055059437 69:−0.07122089 70:−0.10112511 71:0.016131356 72:−0.003313852 73:−0.035084009 74:−0.011168667 75:−0.014436918 76:0.017278275 77:0.19096926 # |
| 0.014353309248426729 1:1.9750346 2:1.4936029 3:3.0633757 4:−1.8149981 5:2.0123887 6:−1.8370656 7:−1.6261933 8:−2.0175233 9:1.7223656 10:0.42213404 11:−1.1639889 12:−1.2468109 13:−0.50911361 14:1.0634505 15:0.11733207 16:−0.44616178 17:−0.68079621 18:−0.28848916 19:−0.49659124 20:0.42111152 21:−0.63590282 22:−0.082414515 23:−0.091340348 24:0.47246131 25:0.65451294 26:−0.33642098 27:0.68843603 28:0.53537869 29:−0.12977821 30:0.12734289 31:0.18795992 32:−0.20524587 33:−0.30572647 34:−0.13704926 35:−0.0305223 36:0.10478308 37:−0.50440288 38:0.39737979 39:−0.20437509 40:−0.3044723 41:0.075915121 42:−0.06875971 43:−0.11113539 44:−0.18415625 45:−0.054783233 46:−0.16862006 47:0.069796138 48:0.18669078 49:0.16507873 50:0.29271457 51:0.019540481 52:−0.29992396 53:−0.040255588 54:−0.048557773 55:−0.059663508 56:0.16851372 57:0.19011344 58:0.019624595 59:−0.042866912 60:−0.06845583 61:0.021140501 62:−0.063171804 63:−0.046577986 64:0.055850849 65:0.09724687 66:−0.027981082 67:0.12547259 68:0.020863682 69:0.031356435 70:0.0098448852 71:−0.081411898 72:0.079502635 73:0.0043864385 74:0.009323257 75:−0.022551484 76:−0.014077507 77:0.19096926 # |
| −0.0053646802018l8876 1:−4.4617 2:1.145705 3:0.54379702 4:2.6725006 5:−2.8944924 6:−1.4770155 7:1.2401086 8:−2.552834 9:−0.90042263 10:1.0540242 11:−1.5331142 12:0.11476815 13:0.44175801 14:−1.6841725 15:−0.64654225 16:−0.41620046 17:−0.32703519 18:0.86249554 19:0.64354229 20:0.63051224 21:0.97298634 22:0.25801665 23:−0.2857365 24:−0.35735887 25:−0.1900802 26:−0.15987608 27:0.4095549 28:0.23679461 29:−0.085736819 30:−0.29999727 31:0.56111211 32:0.3700524 33:0.055656578 34:0.010210637 35:−0.10547514 36:0.099844486 37:0.50572318 38:−0.13202588 39:0.023092929 40:0.0090216557 41:−0.16283445 42:−0.08010149 43:−0.1455038 44:−0.10193739 45:−0.096289724 46:−0.12532833 47:0.13968058 48:0.14324327 49:0.30586708 50:−0.14487669 51:0.19495261 52:0.070381604 53:0.080243774 54:0.20840856 55:−0.23896407 56:0.047488917 57:0.16556399 58:−0.08133883 59:−0.14387378 60:0.093251176 61:−0.11560033 62:0.10031309 63:0.022656322 64:−0.067139342 65:−0.11142465 66:−0.0056155534 67:0.00027069845 68:0.082064211 69:−0.04709189 70:−0.031160077 71:−0.0070726527 72:0.064262822 73:0.074268013 74:0.019216521 75:0.018348213 76:−0.0028032842 77:0.19096926 # |
| 0.014353309248426729 1:5.1681089 2:3.8905778 3:0.85649347 4:−3.0659745 5:−0.83048755 6:−0.71583718 7:1.811404 8:0.082849361 9:−0.10179623 10:1.1650997 11:0.63991463 12:−1.0426204 13:0.25884163 14:0.25757828 15:−2.1625547 16:1.4825215 17:0.58751225 18:−0.15917249 19:−1.4248345 20:0.8722862 21:−0.77316338 22:−0.15848532 23:0.070165589 24:0.97704637 25:0.44036943 26:−0.50653887 27:0.40390182 28:−0.11976799 29:−1.1104206 30:0.42052743 31:0.74351907 32:0.71136212 33:0.10169396 34:−0.013988553 35:−0.47268263 36:−0.102114 37:0.22977158 38:0.13137649 39:−0.28708932 40:0.059453804 41:−0.24888469 42:−0.072814882 43:0.038961537 44:0.19637577 45:0.21431477 46:−0.36375126 47:0.040507644 48:0.099144287 49:−0.017500784 50:−0.11812078 51:−0.14730179 52:0.1172575 53:0.15977181 54:−0.060262296 55:0.27235633 56:0.02939852 57:−0.28242639 58:0.1034939 59:0.11023033 60:0.14302854 61:−0.018836154 62:−0.0096775806 63:−0.090465248 64:0.053898472 65:−0.04045774 |

APPENDIX C13-continued

| SVM Model Weights (77; Normal/Diseased) |
|---|
| 66:−0.066519342 67:0.03471037 68:0.084444471 69:−0.083876237 70:−0.0091625135 71:−0.008706497 72:−0.04454371 73:−0.0052902657 74:−0.0093584629 75:0.036757134 76:−0.016912004 77:0.19096926 # |
| −0.014353309248426729 1:−2.2580619 2:−0.74999952 3:2.3983226 4:2.0305898 5:1.2371706 6:−1.0403913 7:0.66985673 8:−0.82480383 9:0.22577012 10:0.13698357 11:−1.6175935 12:1.2104175 13:−1.5889822 14:−0.71495587 15:0.24800533 16:−0.19111194 17:0.22497587 18:0.65446669 19:0.20636401 20:0.32729766 21:−0.77617592 22:−0.13585827 23:−0.33194745 24:−0.33368513 25:−0.059929766 26:−0.3069537 27:−0.0060318667 28:−0.70042473 29:−0.36326668 30:−0.21156965 31:−0.46263149 32:−0.35798684 33:−0.36553708 34:−0.49797902 35:−0.12607525 36:−0.19550359 37:−0.19481474 38:−0.28217828 39:−0.040020689 40:0.18242802 41:−0.086721882 42:−0.0082778567 43:0.15209278 44:0.054649778 45:0.095505148 46:−0.24898052 47:−0.0015707378 48:0.22134092 49:0.047570832 50:−0.1407567 51:−0.053357828 52:0.14059158 53:−0.017781129 54:−0.065120131 55:−0.032132771 56:0.22751983 57:−0.066347808 58:−0.05613932 59:0.016103817 60:0.0047480594 61:0.096812636 62:−0.077151008 63:0.010616249 64:0.088030584 65:−0.026541909 66:−0.01785568 67:0.10437169 68:−0.010325374 69:0.0415623 70:−0.0062666456 71:0.097325347 72:−0.050489869 73:−0.011737085 74:0.029957859 75:0.033704117 76:0.0079934914 77:0.19096926 # |
| 0.014353309248426729 1:3.0884993 2:1.981297 3:−1.1398543 4:−0.86785215 5:−2.389698 6:−0.4314957 7:0.77931303 8:−1.7048252 9:−0.024473883 10:0.28686044 11:−0.21931249 12:−0.98656917 13:−1.0983287 14:−0.3964476 15:1.1422379 16:0.24920951 17:0.27365485 18:0.12387553 19:−0.013152611 20:0.64328384 21:−0.29322994 22:0.057789367 23:−0.0050247526 24:0.076057069 25:0.013873781 26:0.41973639 27:0.47516504 28:−0.079813994 29:0.59356195 30:0.096937321 31:−0.046115041 32:−0.18875733 33:0.12799051 34:−0.094243601 35:0.3615579 36:0.33870414 37:−0.080631718 38:0.34249336 39:−0.0743839 40:0.21877173 41:0.14390239 42:0.20584278 43:−0.10695766 44:0.36261213 45:0.17564404 46:−0.11729231 47:0.081221953 48:0.0039519034 49:−0.027216218 50:−0.20990603 51:0.20665738 52:0.065957151 53:0.023934865 54:−0.00071565673 55:−0.024389056 56:0.043164574 57:−0.018193571 58:0.10508076 59:0.08740899 60:−0.081348434 61:0.080898941 62:−0.032613952 63:−0.028890057 64:0.15237014 65:0.17825273 66:−0.066460587 67:−0.038571354 68:−0.0045656986 69:−0.011244085 70:−0.062525511 71:−0.025582209 72:0.044963371 73:0.060001839 74:0.0069923787 75:−0.02118546 76:0.043074656 77:0.19096926 # |
| −0.014353309248426729 1:3.7709956 2:2.2916985 3:0.4144823 4:−1.6342236 5:−2.3892395 6:2.3428173 7:0.50903636 8:1.0201547 9:−0.52362841 10:−1.0182973 11:−1.0781908 12:−0.67987287 13:−0.31588501 14:−0.23168643 15:−1.2040113 16:0.84014314 17:0.43450698 18:0.25559014 19:−0.093732864 20:−0.24034321 21:0.54143316 22:0.76838344 23:−0.42845201 24:−0.18444878 25:−0.092808314 26:0.42309007 27:0.28234941 28:−0.25367036 29:0.31450471 30:0.28000441 31:−0.044647429 32:0.099567488 33:0.50172883 34:−0.27860257 35:−0.050875265 36:0.36908171 37:−0.15513867 38:0.059471838 39:0.064677007 40:0.33479691 41:0.2148615 42:0.073171228 43:−0.19603352 44:0.0086111762 45:−0.14117905 46:−0.16671801 47:−0.12582065 48:0.19409426 49:−0.1235932 50:−0.015336821 51:−0.0063993628 52:−0.035813667 53:0.0016715379 54:0.0231033 55:−0.10865419 56:0.31677461 57:0.00092012098 58:−0.0026956892 59:0.017953565 60:−0.20251472 61:−0.0074505298 62:0.010121305 63:−0.07897833 64:−0.10131301 65:−0.099549957 66:0.073265962 67:0.16470225 68:−0.009941211 69:−0.048903506 70:0.024756877 71:−0.048738398 72:−0.043162055 73:0.0044149449 74:−0.026241237 75:−0.030572822 76:−0.016924169 77:0.19096926 # |
| −0.013218935702693608 1:4.6123266 2:1.1898087 3:−0.86055368 4:−4.781992 5:−2.6512074 6:0.15617809 7:−2.1553478 8:0.20750692 9:−0.98206055 10:0.16555689 11:−2.1197071 12:0.94350427 13:−1.2438704 14:0.64875948 15:0.72078729 16:0.56791544 17:0.6103003 18:−0.30873898 19:0.63079429 20:−0.81351376 21:−0.022179842 22:−0.25283757 23:0.1574938 24:−0.24758111 25:−0.48749888 26:0.086072139 27:0.0736183 28:−0.17239293 29:0.15864182 30:0.080037251 31:0.15530773 32:−0.04076723 33:−0.063717976 34:0.10939045 35:−0.28630999 36:0.063341595 37:0.20379035 38:−0.0069661811 39:−0.21175367 40:−0.26929149 41:0.084174246 42:−0.14040722 43:0.23883584 44:0.2303872 45:−0.016048746 46:−0.057956662 47:0.0083864043 48:−0.011604009 49:−0.27359185 50:0.14214309 51:0.079140879 52:0.064751901 53:−0.045787938 54:−0.0033185792 55:−0.048183061 56:0.13623013 57:−0.060155727 58:0.090436898 59:0.022668028 60:0.17977595 61:0.018916829 62:−0.034367938 63:0.098239131 64:0.15149163 65:−0.0019625442 66:−0.05446142 67:−0.010080522 68:0.044043247 69:0.080465585 70:0.0059510749 71:0.019067947 72:0.02952336 73:0.018498404 74:0.013815727 75:−0.0012186097 76:0.022607701 77:0.19096926 # |
| 0.014353309248426729 1:−2.299067 2:0.93961471 3:3.0590062 4:3.214849 5:1.7562711 6:−1.9733551 7:−0.69230604 8:1.3756981 9:0.55064595 10:−0.88400036 11:1.2631551 12:0.096429974 13:−0.72009873 14:−0.8262729 15:−0.97890794 16:−0.36979985 17:0.66865098 18:−0.32430735 19:0.029358095 20:−0.49905798 21:−0.71508193 22:0.087118521 23:0.37459421 24:0.63442385 25:0.073748291 26:0.052770976 27:−0.071886539 28:−0.17380317 29:0.24251877 30:−0.13817701 31:−0.31174943 32:−0.56453556 33:0.25290546 34:−0.0058749635 35:−0.080181375 36:−0.034769159 37:0.10965679 38:−0.067198373 39:−0.0033875527 40:−0.058819588 41:−0.45923081 42:0.2305823 43:0.02583701944:0.10749532 45:−0.10733007 46:0.0089325653 47:−0.12102848 48:0.052897304 49:0.13717727 50:−0.12740478 51:0.13920574 52:−0.14827305 53:0.081732765 54:−0.13699077 55:−0.17185788 56:−0.089363687 57:−0.09944731 58:−0.18760204 59:0.058271162 60:−0.15870465 61:0.01208572 62:−0.10521156 63:−0.052172862 64:−0.047279935 65:0.063615672 66:−0.0090857064 67:0.036694236 68:−0.062897645 69:0.050684139 70:−0.058573592 71:0.0260201 72:−0.02638079 73:−0.017822968 74:−0.032201476 75:0.0076357853 76:0.0066252379 77:0.19096926 # |
| 0.014353309248426729 1:−2.0324311 2:−2.488168 3:2.0844831 4:0.2153381 5:−0.11928455 6:−0.024705008 7:−0.9340744 8:−0.66184205 9:−1.3984357 10:−0.9375807 11:1.2038282 12:1.1074619 13:−0.38059589 14:−1.6809449 15:1.0409421 16:−0.93187737 17:0.51309389 18:−0.19747999 19:−0.07241419 20:0.96415919 21:0.29613644 22:0.63080376 23:−0.27762979 |

APPENDIX C13-continued

| SVM Model Weights (77; Normal/Diseased) |
|---|
| 24:−0.1633727 25:0.11709277 26:0.22846806 27:0.29593119 28:0.91590369 29:0.10631433 30:0.18507333 31:−0.051598608 32:0.17270328 33:0.32453877 34:−0.021790603 35:0.23034143 36:−0.2393534 37:0.23494981 38:−0.11898818 39:0.2231466 40:0.10605485 41:−0.15794705 42:−0.10113093 43:0.0075386483 44:0.097674601 45:−0.012482278 46:0.10085529 47:0.29961026 48:0.06046313 49:0.06194406 50:0.37128592 51:0.27614561 52:0.15980665 53:−0.14313523 54:−0.078337677 55:0.126285 56:−0.042744633 57:−0.01854917 58:0.12996019 59:0.15768033 60:−0.044097099 61:0.18322614 62:0.053536184 63:−0.0057485686 64:0.0011683437 65:−0.061592255 66:−0.16034721 67:0.074150391 68:−0.03352192 69:0.060714763 70:−0.028380878 71:0.067591198 72:−0.032942295 73:−0.061004445 74:−0.023236981 75:−0.012204394 76:−0.00060660328 77:0.19096926 # |
| −0.014353309248426729 1:1.6868047 2:−5.0399818 3:2.7494919 4:−1.0758579 5:1.7470853 6:−0.042877078 7:−1.7491661 8:1.0485967 9:−0.76182526 10:−0.1358062 11:0.71993494 12:−1.0402987 13:−0.89969218 14:−0.46112117 15:0.51963258 16:−0.67106164 17:0.48678735 18:0.46047938 19:−0.0088163493 20:1.0423295 21:0.035865746 22:0.091000602 23:−0.089389339 24:−0.26636085 25:−0.082333557 26:−0.074543126 27:−0.37541911 28:0.33784151 29:0.95409024 30:0.41820842 31:−0.1562757 32:0.22448888 33:0.18840541 34:0.050042652 35:−0.23984317 36:−0.51773107 37:0.30021137 38:0.39767882 39:−0.29342529 40:0.22594847 41:0.012318637 42:−0.023129398 43:0.41812721 44:0.27129957 45:0.046497185 46:−0.32160851 47:0.0043619736 48:0.07350716 49:0.44336396 50:0.16157311 51:−0.33527333 52:−0.22676843 53:−0.073236488 54:0.23217805 55:0.15558802 56:0.09916874 57:0.077860773 58:−0.11773089 59:0.27334043 60:−0.017090674 61:−0.081757382 62:0.036702182 63:0.051659022 64:0.037854802 65:−0.12213313 66:0.078797564 67:0.0034318008 68:0.06999401 69:0.015439983 70:0.0052553406 71:0.066842534 72:0.00054181408 73:−0.015431649 74:0.0016627485 75:−0.010059119 76:0.031069618 77:0.19096926 # |
| −0.0096317992040337273 1:0.10029095 2:−5.5801401 3:2.2309003 4:−3.9803932 5:1.4787121 6:1.1376091 7:−4.2517719 8:−0.23247558 9:−2.1070492 10:1.6322012 11:5.1617475 12:0.32398614 13:1.7850295 14:−1.5233221 15:1.2233368 16:−0.013077746 17:−0.26414534 18:−0.46263587 19:−0.44582829 20:0.83916605 21:0.25784159 22:1.066766 23:1.4080256 24:−1.8076414 25:−0.30431655 26:−0.44437531 27:0.4264268 28:−1.0971532 29:−0.68410563 30:0.21219914 31:0.081946336 32:−0.16293667 33:−0.20622103 34:0.054752477 35:−0.0021561226 36:0.1752888 37:−0.29194841 38:0.021513736 39:−0.30983782 40:−0.10149197 41:−0.065066338 42:−0.014225383 43:0.26937571 44:−0.24232407 45:−0.43637878 46:−0.29823619 47:−0.2565203 48:0.0055451384 49:−0.044913791 50:0.024420453 51:0.22848457 52:−0.034373887 53:0.16623029 54:−0.055976003 55:0.030507745 56:0.0464922 57:0.039106671 58:0.089228913 59:−0.046827704 60:−0.064312391 61:−2.6088217e−005 62:−0.014219298 63:−0.0096267657 64:0.0049637514 65:0.0036958882 66:0.0023666776 67:−0.028096782 68:0.01052382 69:−0.0064321533 70:0.025961123 71:0.0087845987 72:−0.020248221 73:0.018267 74:0.0036964735 75:−0.017049873 76:−0.00085554295 77:0.19096926 # |
| −0.011582604918985615 1:−7.5790119 2:6.5505819 3:3.0748138 4:3.8777366 5:0.22004712 6:−1.9566555 7:−1.1376507 8:0.040725145 9:0.7170465 10:−0.8904922 11:0.4500643 12:−0.35941792 13:0.90739906 14:0.97919571 15:−0.47728714 16:−1.033375 17:0.91873997 18:−0.14776833 19:0.090298899 20:−0.61440623 21:−0.3768461 22:−0.2607443 23:0.76819563 24:−0.086841576 25:−0.1902944 26:−0.26672038 27:−0.36516112 28:0.32622656 29:0.10635825 30:−0.086041629 31:0.17886183 32:0.253389 33:−0.17789988 34:0.59617275 35:−0.20439127 36:−0.15065116 37:−0.021093894 38:−0.17446886 39:−0.18610066 40:0.20435792 41:−0.087490752 42:−0.13862734 43:−0.15207936 44:0.12994783 45:−0.05528757 46:−0.23665915 47:0.063674219 48:0.001943095 49:−0.13950399 50:−0.038966343 51:−0.0077552036 52:−0.10451812 53:0.066562809 54:−0.013185959 55:0.073392585 56:0.1814561 57:0.13015871 58:0.13643754 59:0.097850546 60:−0.01157839 61:0.071709059 62:0.21658824 63:−0.0030440351 64:0.013483539 65:−0.039123967 66:0.030702319 67:−0.024155745 68:−0.06262058 69:0.043377943 70:0.025644775 71:−0.013373398 72:−0.020322314 73:0.10452135 74:−0.019650195 75:−0.048054658 76:−0.0039502117 77:0.19096926 # |
| −0.012726225131857024 1:−0.59048438 2:−0.54890853 3:2.2920735 4:−0.10596693 5:3.1261718 6:0.088931702 7:−0.20144737 8:2.8812337 9:1.5193526 10:0.74850088 11:−0.67944229 12:−0.795968 13:−0.47369191 14:−0.65851074 15:−0.82592529 .16:−0.59259254 17:1.8017545 18:0.15533726 19:−0.77393395 20:0.15187424 21:0.26339552 22:−0.65441227 23:0.62924105 24:0.39691222 25:0.19459301 26:−0.017084781 27:0.53001392 28:−0.17292607 29:0.13115412 30:−0.035700768 31:0.77568269 32:−0.24740957 33:0.050896686 34:0.14415972 35:0.20591693 36:0.13207215 37:−0.20491186 38:−0.056039315 39:−0.12411451 40:0.085958987 41:−0.26387721 42:−0.087921932 43:−0.18074885 44:0.14550807 45:0.075843625 46:−0.00022254155 47:0.05060336 48:−0.14356618 49:0.22488548 50:0.12159404 51:0.16349792 52:0.090687908 53:−0.13064197 54:−0.10039066 55:0.13332009 56:0.031933166 57:0.053071015 58:−0.01242383 59:−0.11970847 60:−0.023966052 61:0.01735569 62:−0.099293403 63:−0.050414108 64:0.004519383 65:−0.016227044 66:0.013353062 67:−0.080079474 68:−0.038297076 69:0.036086313 70:0.056870129 71:0.012044545 72:0.027515942 73:0.027147811 74:0.024683228 75:−0.0097237611 76:−0.026057104 77:0.19096926 # |
| 0.014353309248426729 1:3.666008 2:2.9822176 3:−1.0896645 4:−2.3018303 5:−4.1104403 6:0.95635748 7:0.92233759 8:1.0008152 9:−0.47478738 10:−2.2138927 11:−0.9277612 12:−0.56900299 13:−2.1111259 14:0.75395566 15:−0.55192143 16:0.5055694 17:−0.15977848 18:−0.8307808 19:−0.10270375 20:0.44134381 21:0.68861991 22:0.52889454 23:−0.26066214 24:−0.60984051 25:0.85272634 26:−0.81061721 27:0.2342604 28:−0.38998395 29:0.36272934 30:−0.15877284 31:0.11416122 32:0.3548007 33:0.17147113 34:−0.26881793 35:−0.17671369 36:0.10715578 37:0.26979601 38:−0.1822515 39:0.041785672 40:−0.22157945 41:0.32829657 42:−0.06660372 43:−0.057417843 44:−0.1136876 45:−0.36893442 46:0.042875413 47:−0.03435852 48:0.141233 49:0.064115472 50:−0.038826384 51:−0.090790756 52:−0.14747368 53:−0.044202968 54:−0.096438169 55:0.21333908 56:−0.13472764 57:0.11538406 58:0.058997069 59:−0.043629795 60:0.0064461203 61:−0.021167882 62:0.077559821 63:0.094815478 64:−0.061597288 |

APPENDIX C13-continued

| SVM Model Weights (77; Normal/Diseased) |
|---|
| 65:0.03340482 66:−0.023303961 67:−0.011876567 68:−0.034856208 69:0.050844733 70:0.0034620315 71:0.04071559 72:−0.013689127 73:0.0095036188 74:−0.020375375 75:0.048812557 76:0.016354514 77:0.19096926 # |
| −0.0030715698103376717 1:−0.070714802 2:3.177454 3:−1.5759526 4:1.8860668 5:2.4001379 6:0.35558453 7:0.87289882 8:0.48343268 9:0.63605112 10:1.5815552 11:1.2621956 12:−0.97554106 13:−0.064992502 14:−0.23652077 15:0.20339635 16:−0.83336037 17:−0.48293522 18:−1.13623 19:0.40942436 20:−0.63267088 21:−0.060268722 22:0.29991403 23:0.26954034 24:−0.079866163 25:0.24177447 26:0.20452619 27:0.24936593 28:−0.033255734 29:0.099945918 30:0.037394971 31:0.35949516 32:−0.015677121 33:−0.25428253 34:−0.26878181 35:−0.4181267 36:−0.14777821 37:−0.045981683 38:−0.14642745 39:0.2894955 40:0.29183376 41:0.013813442 42:0.23503675 43:0.046419032 44:−0.09843111 45:−0.1608914 46:−0.078837797 47:0.28541952 48:−0.045045454 49:0.1705164 50:0.087945655 51:−0.015320992 52:0.032217227 53:−0.051897243 54:0.089708626 55:−0.11953514 56:−0.047337815 57:−0.16238128 58:0.1135859 59:−0.0093975281 60:0.025787955 61:−0.051308759 62:−0.019185089 63:0.19937991 64:0.035768311 65:−0.060693312 66:0.080324218 67:0.021668576 68:−0.023114704 69:−0.074131712 70:−0.085760541 71:−0.034285225 72:0.050227713 73:0.012561836 74:−0.022650542 75:−0.0068410994 76:−0.027436165 77:0.19096926 # |
| 0.014353309248426729 1:3.680866 2:0.26752141 3:1.253394 4:−4.1543145 5:1.6269178 6:2.1013806 7:−1.8205193 8:1.1527944 9:2.1712518 10:−2.1177444 11:0.95561951 12:1.9021856 13:−0.49947378 14:−0.741 39744 15:−0.43119213 16:1.2520725 17:−0.46075192 18:−1.1319407 19:0.086981885 20:−1.2889035 21:0.010601914 22:0.46948248 23:−0.47151577 24:−0.20375997 25:0.41848356 26:0.09976387 27:0.046356589 28:0.28266919 29:0.11588895 30:−0.99098873 31:0.10705765 32:−0.17921776 33:0.74361402 34:0.23332672 35:−0.19694299 36:0.11068617 37:−0.28409329 38:0.20447247 39:−0.250707 40:0.25581515 41:−0.2573278 42:−0.20802025 43:−0.0025013622 44:−0.047578361 45:−0.17257808 46:0.049059428 47:0.040889662 48:−0.05243076 49:−0.15674277 50:−0.067784511 51:−0.1623404 52:0.12797529 53:0.042302504 54:0.05736623 55:0.058036018 56:−0.064032778 57:−0.014793606 58:−0.038588338 59:0.025465781 60:0.084468596 61:0.0051239897 62:−0.039333977 63:0.044317834 64:−0.17139249 65:−0.006772283 66:0.086761668 67:0.07085605 68:0.11045215 69:0.03255628 70:−0.039234031 71:0.013549622 72:0.030149061 73:−0.0050597894 74:0.032013875 75:−0.0091848504 76:0.017574856 77:0.19096926 # |
| 0.014353309248426729 1:1.2427433 2:1.3706518 3:0.5368107 4:−0.44672567 5:0.39274105 6:−1.1520034 7:1.1453632 8:−0.61284262 9:1.3852679 10:−0.65746588 11:−1.8517658 12:−0.54778975 13:−0.36325625 14:−0.40358409 15:0.81603175 16:0.63267708 17:−0.24813806 18:−0.74993491 19:0.002058795 20:0.090415418 21:−0.62965578 22:0.93171006 23:−0.46696359 24:−0.31457534 25:0.028555501 26:0.2619057 27:−0.30925912 28:0.063059568 29:−0.20017241 30:0.26405728 31:0.15413347 32:0.28109288 33:−0.039529782 34:−0.083672456 35:0.26354465 36:0.10780171 37:−0.39854637 38:−0.099143341 39:−0.33304298 40:−0.06105949 41:0.065880105 42:0.33939272 43:0.15653868 44:−0.007003922 45:0.2188043 46:0.010645676 47:0.021517588 48:0.023331294 49:−0.012280959 50:0.052791897 51:0.099905394 52:−0.10417577 53:0.058795914 54:−0.095497519 55:−0.0085586645 56:−0.00038607544 57:0.010311273 58:0.10865234 59:−0.043781355 60:−0.1004196 61:−0.049999874 62:0.01789319 63:−0.053442601 64:−0.11123443 65:−0.08154273 66:0.027982472 67:−0.036305059 68:0.00088943593 69:−0.030517759 70:0.029887594 71:−0.024696531 72:−0.03877781 73:−0.0050225235 74:−0.060135942 75:0.0003863929 76:0.030526938 77:0.19096926 # |
| 0.014353309248426729 1:5.9057474 2:−4.767211 3:0.20555025 4:−2.3459365 5:1.671129 6:2.4856012 7:−0.14730737 8:−0.081640609 9:−0.42414698 10:−1.1787274 11:0.13732548 12:−0.44804674 13:1.5137678 14:−1.0661492 15:0.41292301 16:−1.4042665 17:0.011605706 18:−1.0287486 19:0.37523484 20:0.94304389 21:0.19226067 22:−0.1034089 23:−0.5190047 24:0.93933851 25:−0.14667861 26:−0.086714692 27:−0.12359893 28:−0.55011278 29:0.93173629 30:−0.20260881 31:−0.11777192 32:0.16852878 33:−0.12114369 34:−0.021193665 35:0.087746091 36:−0.22649559 37:0.33329174 38:−0.17637658 39:−0.42427227 40:0.44090813 41:0.25949731 42:−0.063188441 43:0.11541276 44:−0.16818027 45:−0.023929324 46:0.11389446 47:−0.4498131 48:0.18968727 49:0.044943832 50:−0.11869915 51:−0.17343287 52:0.061005928 53:−0.18013616 54:−0.10227749 55:−0.016989719 56:0.14386877 57:−0.10758385 58:0.015178842 59:0.021012606 60:0.10673301 61:0.031626016 62:0.038804144 63:−0.020766558 64:0.061640773 65:0.09034545 66:−0.046736568 67:−0.08305303 68:−0.012462557 69:−0.010515817 70:−0.060973551 71:0.007205213 72:0.051835474 73:−0.014414936 74:0.0057421033 75:0.012660991 76:−0.023579404 77:0.19096926 # |
| −0.014353309248426729 1:3.7441537 2:2.3162103 3:−1.2916063 4:2.0460212 5:1.3372414 6:1.0969115 7:0.24194705 8:−0.73323852 9:1.8554794 10:−0.25716838 11:−0.050922219 12:−0.40737891 13:−0.81729203 14:0.66206473 15:−0.1407212 16:1.2580738 17:1.1031867 18:−0.39045498 19:0.019753031 20:0.95148295 21:−0.28635272 22:0.63159025 23:0.15395395 24:−0.11255904 25:0.35239211 26:0.88030475 27:−0.25441325 28:−0.25619617 29:0.18188801 30:−0.15599005 31:−0.063941501 32:0.19795723 33:0.20076479 34:0.26202548 35:−0.046927571 36:−0.16496442 37:−0.016379377 38:0.087522313 39:0.13974649 40:0.063309439 41:−0.35355663 42:−0.17428662 43:0.23461229 44:0.076639734 45:−0.21675932 46:0.074965037 47:−0.12663379 48:−0.14785738 49:−0.019965729 50:0.10994761 51:−0.027340584 52:0.066972807 53:0.18050499 54:0.085008144 55:0.072001047 56:−0.036253553 57:−0.054752782 58:0.17720872 59:−0.1446714 60:−0.17295277 61:−0.054635704 62:−0.056451418 63:−0.014661192 64:0.0002833555 65:0.097482339 66:0.051477056 67:0.0076912516 68:−0.065960668 69:0.00043097616 70:−0.038085613 71:0.055286296 72:0.0036364133 73:−0.005965854 74:0.054932803 75:0.019141017 76:−0.010598514 77:0.19096926 # |
| −0.009640429852174821 1:2.2595334 2:5.4341373 3:−3.1003435 4:−3.0994995 5:−1.0248858 6:−1.8907695 7:−0.25694948 8:1.1080626 9:0.6625756 10:−1.2063892 11:−2.0393317 12:0.10253934 13:−1.3936769 14:−0.24712338 15:1.2500482 16:−0.54052746 17:1.2039022 18:−0.39000741 19:0.07487528 20:−0.0072274394 21:−0.18584816 22:−0.10029473 23:−0.25899917 24:−0.57858628 |

APPENDIX C13-continued

SVM Model Weights
(77; Normal/Diseased)

25:−0.85585499 26:−0.089402765 27:0.46923304 28:−0.96165836 29:0.17084518 30:−0.35636881 31:0.38115731 32:0.095866077 33:0.34083527 34:0.28986356 35:−0.13804261 36:−0.038802952 37:0.13236205 38:−0.3910377 39:−0.16336218 40:−0.29616532 41:−0.11825216 42:0.19137074 43:−0.19761637 44:−0.4307172 45:0.043072641 46:0.055928465 47:0.11477138 48:−0.043380715 49:0.073635429 50:−0.039514869 51:0.085157409 52:−0.26701492 53:0.086366408 54:−0.026240626 55:−0.088102512 56:0.022103522 57:−0.02560572 58:−0.031263635 59:0.02162783 60:−0.0073080887 61:0.18205269 62:−0.070958197 63:0.0046705217 64:0.056871273 65:0.016824864 66:−0.039006148 67:0.064347945 68:0.095751688 69:−0.019738398 70:−0.0066545028 71:−0.04158359 72:−0.13721204 73:−0.039938416 74:0.020000828 75:0.01773056 76:−0.015207112 77:0.19096926 #
0.014353309248426729 1:−2.6878188 2:1.121264 3:3.4456193 4:−1.4385917 5:−3.2312369 6:1.922717 7:−0.269324 8:−1.6225955 9:−2.1278424 10:−0.23798926 11:2.7177882 12:0.91447258 13:−0.45146745 14:0.0012731516 15:−0.5083729 16:0.26266849 17:0.45034793 18:1.5414371 19:−0.83026153 20:1.2654854 21:−0.028155914 22:−0.50004154 23:−0.32945594 24:0.11461711 25:0.23110789 26:0.21561594 27:−0.49940953 28:0.27542549 29:0.39217144 30:−0.32054046 31:−0.32642707 32:−0.21520968 33:0.25350896 34:−0.70325518 35:0.0072600511 36:−0.15557545 37:−0.22934532 38:−0.41946104 39:0.01163194 40:−0.3151722 41:0.13227686 42:−0.30065033 43:0.1370268 44:−0.074821562 45:−0.12047619 46:0.15199155 47:0.089143865 48:−0.025894878 49:0.11117977 50:−0.017316449 51:−0.052068342 52:−0.2447293 53:−0.11811594 54:−0.17160854 55:0.0083444053 56:−0.044362999 57:−0.16346233 58:0.138899 59:−0.092605613 60:0.10448389 61:0.038156223 62:0.1396447 63:−0.1837725 64:−0.039237559 65:0.090511814 66:0.11475332 67:0.025900282 68:0.080345422 69:0.0036978689 70:−0.011915413 71:−0.040313173 72:0.030062035 73:0.0033524763 74:−0.02960901 75:−0.012412534 76:−0.037850738 77:0.19096926 #
0.014353309248426729 1:0.38636443 2:0.856022 3:3.8331192 4:0.90847105 5:2.3917947 6:0.041978683 7:0.43087831 8:−0.93552274 9:1.1171921 10:0.24187095 11:−0.29452369 12:0.35834107 13:−0.92156577 14:−0.2207619 15:−0.42295644 16:0.37727049 17:0.34071356 18:0.54638869 19:0.54431421 20:0.5606817 21:0.00073621399 22:−0.58369654 23:0.51575679 24:−0.28523123 25:0.12013033 26:−0.11653052 27:−0.08614184 28:−0.022422912 29:−0.17559333 30:−0.1012346 31:0.084177695 32:−0.14712697 33:0.0009101773 34:−0.059826806 35:0.18328349 36:0.12952863 37:0.26789933 38:−0.022896804 39:0.1307006 40:0.14332886 41:−0.11044554 42:0.017367586 43:0.01041106 44:0.14261428 45:0.15194528 46:0.1476045 47:−0.066166066 48:0.1060352 49:0.010259186 50:−0.055985067 51:0.027592177 52:−0.1046881 53:0.0033757121 54:0.079849124 55:−0.16161227 56:0.0042339098 57:0.010133335 58:0.26547223 59:0.02316601 60:0.036207814 61:0.091286816 62:0.01541307 63:−0.12320108 64:0.017603537 65:−0.087876379 66:0.10118353 67:0.078634337 68:−0.04357231 69:0.059931714 70:0.065981746 71:0.038514733 72:0.058741774 73:−0.037877336 74:−0.084362388 75:0.005781529 76:0.0098638693 77:0.19096926 #
−0.014353309248426729 1:−0.6108247 2:−4.890883 3:3.6717718 4:0.54653811 5:1.0905101 6:1.6013606 7:−0.22307479 8:0.51864815 9:1.1002388 10:0.36329517 11:−0.76388901 12:0.5705992 13:0.54914296 14:−0.28607956 15:0.62665856 16:1.0845172 17:0.32712334 18:0.84988719 19:−0.61673403 20:−0.114315 21:−0.2689209 22:0.44969723 23:−0.10776665 24:−0.11753003 25:0.14449164 26:−0.40692765 27:0.023192151 28:−0.051012207 29:0.21874079 30:−0.37050259 31:0.17088012 32:−0.18013103 33:−0.058499943 34:−0.075687408 35:−0.24064673 36:0.45852095 37:0.038936045 38:0.047233377 39:0.023317542 40:−0.070746042 41:−0.050584536 42:0.0090691727 43:−0.10506802 44:0.07295581 45:−0.023731226 46:0.06961599 47:0.1121373 48:−0.061126716 49:0.00092205487 50:−0.16529496 51:−0.17807417 52:0.038804755 53:0.058140315 54:0.036813408 55:−0.093579099 56:0.13720341 57:0.040333912 58:0.016267089 59:−0.0028158459 60:0.096053921 61:−0.00048676081 62:−0.0079060597 63:−0.03561952 64:0.031539623 65:0.063989349 66:−0.055836353 67:−0.020441296 68:−0.032015163 69:0.0037031942 70:−0.12484382 71:−0.00092913298 72:−0.037305456 73:−0.050279081 74:0.043906949 75:−0.023611976 76:−0.022180807 77:0.19096926 #
−0.0065051112693648664 1:−4.7244506 2:−1.4788072 3:3.246006 4:3.4135661 5:1.3206518 6:1.1450083 7:0.32004747 8:1.0902506 9:−0.37339944 10:0.95450217 11:−0.29265964 12:0.050331764 13:−0.62245697 14:−0.40205711 15:−0.553038 16:−0.66831827 17:0.14163695 18:0.12401362 19:0.40718654 20:0.068238847 21:0.15499578 22:−0.51273233 23:0.88876188 24:0.45370814 25:−0.40780139 26:0.66089803 27:0.39906201 28:0.3952041 29:0.29094338 30:0.19685249 31:0.15844512 32:−0.041176066 33:0.20380041 34:0.30236804 35:−0.37890589 36:0.030715622 37:−0.056030415 38:0.037363097 39:−0.24172373 40:−0.25368899 41:0.31342876 42:−0.14536017 43:−0.32302657 44:−0.054644428 45:−0.03259445 46:0.034624986 47:−0.057994857 48:−0.072206028 49:0.097645193 50:0.026250103 51:0.032223776 52:−0.1892809 53:0.067073174 54:0.021010505 55:0.14280562 56:−0.04583152 57:0.071236596 58:−0.00060872111 59:−0.051703405 60:0.15946393 61:0.020198047 62:−0.10635974 63:−0.012007209 64:−0.12970571 65:−0.020762229 66:0.07996016 67:0.063909605 68:−0.077475615 69:0.0014308698 70:−0.023120901 71:0.01233064 72:−0.041852873 73:−0.025190048 74:0.0022477636 75:0.005615552 76:0.025542015 77:0.19096926 #
0.014353309248426729 1:3.4301562 2:3.0567949 3:4.5394192 4:−0.64337593 5:0.32167339 6:−0.67738569 7:−0.46988666 8:0.76128191 9:0.2474937 10:2.1036863 11:−0.83278859 12:0.48940146 13:−0.56490093 14:1.0443639 15:−0.22071312 16:0.16780683 17:−0.84399223 18:−0.14652058 19:0.65322387 20:0.41846925 21:−0.21693572 22:0.0043834453 23:−0.36042258 24:0.32709274 25:−0.53348172 26:0.46895123 27:−0.11657567 28:−0.074903637 29:0.19913344 30:0.30242568 31:−0.29666871 32:0.070150174 33:−0.020599082 34:−0.23900202 35:0.1199378 36:−0.10555006 37:−0.042823821 38:−0.34415114 39:−0.66889066 40:0.13248236 41:−0.024332533 42:0.052654237 43:−0.39057323 44:0.18161866 45:−0.51104987 46:−0.146771 47:0.062001262 48:−0.12934579 49:−0.25367245 50:0.2305323 51:0.097649507 52:0.0063738474 53:−0.29790211 54:−0.070388086 55:0.034063041 56:−0.27592105 57:−0.10702874 58:−0.12448594 59:−0.10022611

APPENDIX C13-continued

SVM Model Weights
(77; Normal/Diseased)

60:0.0080387508 61:−0.029957 62:0.012474229 63:−0.025993787 64:0.087472886
65:−0.060948823 66:0.021507204 67:−0.10869572 68:−0.030771866 69:−0.065270551 70:0.041160062
71:0.05400753 72:−0.014272934 73:0.068761297 74:−0.0012783889 75:−0.017372999
76:−0.0048428415 77:0.19096926 #
−0.014353309248426729 1:1.8845117 2:1.4235612 3:2.6579957 4:2.302196 5:−4.9185662
6:0.93702608 7:0.076878563 8:1.5084431 9:0.70339113 10:0.63013738 11:−0.24567349
12:0.1548862 13:0.23722629 14:−0.077427976 15:0.4197194 16:−0.66850233 17:−0.58223236
18:0.36675385 19:0.6199953 20:−0.24822915 21:0.28823802 22:0.1234897 23:−0.25462291
24:0.4546088 25:−0.37986326 26:−0.037897374 27:0.428518 28:−0.21972159 29:−0.52197134
30:−0.16623034 31:0.079080962 32:−0.18901961 33:0.10124938 34:0.045618232 35:0.15830931
36:−0.14288348 37:0.022093689 38:0.44562227 39:−0.11351277 40:0.075232975 41:−0.04051353
42:−0.09169592 43:0.04294543 44:−0.12951878 45:0.22500512 46:−0.12376408 47:−0.0047245692
48:0.177128 49:−0.080799922 50:0.12448369 51:−0.18917572 52:0.044513956 53:−0.10171537
54:−0.26064205 55:−0.09645211 56:−0.26438028 57:0.15707047 58:−0.097599693 59:0.066265114
60:−0.089334674 61:0.088196963 62:0.082027532 63:−0.018383436 64:0.087617084
65:−0.020650566 66:0.086799435 67:−0.0081074713 68:−0.007734458 69:0.013810502
70:0.0092310356 71:−0.0045974674 72:0.00883382 73:−0.080492005 74:0.0061278581
75:−0.00098019978 76:−0.014886374 77:0.19096926 #
−0.014353309248426729 1:−1.2919966 2:2.7169838 3:−0.77120078 4:−0.66583997 5:3.1153352
6:1.7179966 7:−0.86386865 8:−1.5422454 9:1.9817361 10:−0.15787558 11:−0.15769723
12:1.5309719 13:−2.1216869 14:−0.6070832 15:0.37934649 16:−0.2563858 17:−0.36394313
18:0.36558348 19:−0.075308233 20:0.24932837 21:−0.23962937 22:−0.75924057 23:0.48914057
24:−0.34236795 25:−0.020607596 26:−0.36175486 27:0.26637235 28:0.22738285 29:0.17209676
30:0.77106673 31:0.30831203 32:−0.12948543 33:0.4417173 34:0.10498308 35:−0.13943487
36:0.3818118 37:−0.2477821 38:0.28109893 39:0.6529476 40:−0.143105 41:0.11457469
42:0.21372136 43:0.19516136 44:−0.0053481082 45:−0.022631884 46:−0.028156653
47:−0.090385295 48:0.020062944 49:−0.12891635 50:0.092483282 51:−0.19211714 52:−0.014977222
53:−0.082764894 54:0.057773668 55:0.22149867 56:−0.070850477 57:0.0013878845
58:−0.023742817 59:−0.11230375 60:0.0097405193 61:−0.057172786 62:−0.0029098878
63:0.061118167 64:−0.027507761 65:−0.067873023 66:−0.07663054 67:−0.042784791
68:0.039686289 69:0.026780808 70:−0.030227304 71:0.0088007934 72:−0.035958048
73:0.03026359 74:−0.02229994 75:−0.0041533755 76:−0.012880161 77:0.19096926 #
−0.0063420954998275256 1:4.4839692 2:−1.933655 3:1.1295911 4:1.4495777 5:2.8864784
6:1.2935989 7:1.5865479 8:1.5299776 9:−0.70109135 10:−0.62551588 11:−1.2234299
12:−0.63515997 13:0.093730517 14:0.51283437 15:−0.61223984 16:0.17688283 17:−0.068988584
18:0.85729182 19:0.67246163 20:−0.9128961 21:0.10238393 22:0.16262417 23:−0.64654738
24:−0.33566698 25:−0.80597997 26:0.046587884 27:−0.68548918 28:−0.041130461 29:−0.039104927
30:0.554407 31:0.042255864 32:−0.053207375 33:0.025002979 34:0.081931762 35:0.32363972
36:0.27287799 37:−0.028950164 38:0.2770716 39:0.24107274 40:0.088308841 41:−0.084622517
42:−0.11231405 43:−0.026139956 44:−0.05976316 45:−0.29168698 46:−0.017887231
47:−0.36514169 48:−0.0082140518 49:−0.1327616 50:0.16306664 51:0.032149222 52:−0.091845021
53:−0.011160312 54:0.15388553 55:0.088901915 56:−0.0056396397 57:−0.14397588
58:0.018055394 59:−0.01560638 60:−0.0073435376 61:0.21125388 62:0.029312413
63:−0.027647167 64:−0.035182219 65:−0.075396672 66:0.021237938 67:0.02172924 68:0.050924309
69:0.051063191 70:−0.022577545 71:0.021975197 72:0.0033299832 73:0.019809062
74:0.031688891 75:0.024536483 76:−0.0059031551 77:0.19096926 #
−0.014353309248426729 1:−1.881453 2:4.9784918 3:−1.1905483 4:−0.41080135 5:3.0293372
6:−0.47009152 7:0.61650336 8:−0.81715041 9:1.8814139 10:0.23291425 11:0.60829055
12:−0.73279208 13:1.9074999 14:−0.60800958 15:−0.63946831 16:−0.19067039 17:−0.17029928
18:−0.78147513 19:0.043982692 20:−0.42763561 21:−0.14317738 22:0.34371379 23:−0.2587519
24:−0.069870733 25:−0.25558653 26:0.027285958 27:−0.33204433 28:−0.19557889 29:−0.15517071
30:0.36253241 31:−0.20356955 32:0.17678441 33:0.096355848 34:0.17948054 35:−0.11400372
36:−0.14646167 37:0.098548152 38:−0.33849609 39:0.26957989 40:0.071458109 41:0.25034261
42:0.31505913 43:−0.03650406 44:0.042990174 45:0.38976523 46:0.26280281 47:−0.15457815
48:0.22927296 49:0.0081744445 50:0.057624612 51:0.02428381 52:−0.15099542 53:0.14522097
54:−0.19375867 55:0.020309703 56:−0.071978018 57:0.0018869517 58:0.13639456
59:−0.072807901 60:0.049186822 61:0.0086803883 62:0.025715018 63:−0.036092147 64:0.07512112
65:−0.01522551 66:0.14732513 67:−0.10219277 68:0.051068358 69:0.11970014 70:−0.10039245
71:0.0093176626 72:−0.017781842 73:0.0021679816 74:−0.032490034 75:0.0056225099
76:−0.013356958 77:0.19096926 #
−0.003922793117878012 1:−7.3553796 2:−0.54099905 3:1.6266738 4:1.6591816 5:0.94760334
6:1.3581005 7:0.50002092 8:−0.9871431 9:−0.2893177 10:−1.7645237 11:−0.98026687
12:0.55174059 13:−1.0608153 14:1.5944568 15:0.43099496 16:0.1709785 17:0.13575226
18:0.14611977 19:−0.37696576 20:−0.39691252 21:0.53413999 22:0.19626211 23:0.28411552
24:−0.15100865 25:−0.52044135 26:−0.370794 27:0.46423438 28:−0.12109499 29:−0.10487907
30:−0.072151653 31:0.091203772 32:0.65151244 33:−0.30114272 34:−0.23560874 35:0.061270207
36:0.27106494 37:−0.095334582 38:−0.039770931 39:−0.32339928 40:0.19195817 41:0.071601868
42:0.056757957 43:0.4458411 44:0.0027926425 45:0.17143616 46:0.041628577 47:−0.063391715
48:−0.058588814 49:0.088949583 50:0.080522247 51:0.086201802 52:0.012541187
53:0.12577793 54:−0.011393614 55:−0.13095403 56:−0.034724887 57:−0.050221168
58:−0.082788557 59:−0.058772184 60:−0.051262639 61:−0.010216376 62:0.064576492
63:−0.031102885 64:−0.11214566 65:0.0024115797 66:−0.060669962 67:−0.076325484
68:0.025766443 69:−0.092353605 70:−0.023698386 71:0.065890878 72:0.083153978
73:−0.052081227 74:−0.035080932 75:−0.024408061 76:−0.00035654989 77:0.19096926 #
−0.0010011637506343123 1:−4.9384565 2:−0.76484162 3:−0.069563486 4:−0.62838149
5:1.1633202 6:−2.6455259 7:1.3576648 8:−0.77359349 9:−0.090579651 10:−1.2795808
11:−1.8614473 12:0.4444347 13:−0.18661463 14:0.66116089 15:0.0075775385 16:0.04558349

APPENDIX C13-continued

SVM Model Weights
(77; Normal/Diseased)

17:0.8491109 18:0.18629982 19:0.26734376 20:0.58067429 21:−0.74520946 22:0.33410308
23:0.43664697 24:−0.26300433 25:0.31377012 26:0.48682761 27:0.73869753 28:0.10963978
29:−0.016050184 30:−0.040780846 31:0.1344104 32:−0.3974846 33:0.093816325 34:−0.0021213908
35:0.061785888 36:−0.12574083 37:−0.18855666 38:−0.23322903 39:−0.4032129 40:0.08239767
41:−0.094555147 42:−0.076770797 43:0.013453666 44:−0.17288475 45:0.033710249
46:0.018201178 47:−0.014319062 48:−0.020584477 49:−0.095838733 50:−0.21356799
51:0.034327004 52:0.066154622 53:−0.11227368 54:0.19120167 55:0.18031305 56:−0.067326158
57:−0.035157543 58:0.031403728 59:0.031293955 60:−0.13699488 61:0.057333644 62:0.10242721
63:0.16524465 64:0.0065345503 65:0.045032009 66:0.049806785 67:−0.088267811
68:0.11953975 69:0.02820095 70:0.021735335 71:−0.06577602 72:0.047155134 73:−0.041190378
74:0.030613571 75:0.012481729 76:0.0192082 77:0.19096926 #

APPENDIX C14

SVM Model Weights
(77; Benign/Malignant)

SVM-light Version V6.01
0 # kernel type
3 # kernel parameter -d
1 # kernel parameter -g
1 # kernel parameter -s
1 # kernel parameter -r
empty# kernel parameter -u
77 # highest feature index
99 # number of training documents
68 # number of support vectors plus 1
0.36970887 # threshold b, each following line is a SV (starting with alpha*y)
−0.0047670039839831906 1:−1.6563329 2:−0.90792972 3:−0.37833497 4:−0.45280576
5:−0.16524178 6:2.9555321 7:−0.53842413 8:0.049447022 9:−0.84816146 10:0.71901792
11:−0.43790579 12:1.5116452 13:0.0036680971 14:−0.05087918 15:−0.9251247 16:−1.077577
17:0.27072039 18:−0.43112814 19:−0.59338516 20:0.34799501 21:−0.19836682 22:−0.077212512
23:0.71580291 24:0.065768823 25:0.0037815007 26:0.18621582 27:0.19125608
28:−0.0094244927 29:0.38229746 30:−0.074086182 31:0.1804693 32:0.47207373 33:−0.12141074
34:−0.15474916 35:0.10368505 36:−0.53067732 37:−0.13583614 38:0.003764563 39:0.07594268
40:−0.18249719 41:−0.11871375 42:−0.04505771 43:−0.16373485 44:−0.13975798 45:−0.074616067
46:0.013647559 47:−0.17342639 48:−0.0044888281 49:0.16663559 50:−0.032624207
51:−0.098048463 52:0.19391116 53:−0.16127816 54:0.025578693 55:0.029530497 56:0.0017475057
57:−0.080620982 58:−0.024671258 59:−0.12814216 60:−0.022246754 61:−0.10052213
62:0.0079960413 63:−0.049692061 64:−0.056385107 65:0.053242926 66:0.019412849
67:−0.0077222674 68:0.01097662 69:−0.031006116 70:−0.0086338893 71:−0.044817686
72:0.022493135 73:0.020267243 74:−0.028045543 75:−0.016310401 76:−0.0047811051
77:−0.1903552 #
−0.014366641566473147 1:−1.740266 2:1.7701211 3:0.75712073 4:−1.3327184 5:−2.1988668
6:0.31657082 7:0.30018181 8:−0.53436369 9:0.63195992 10:0.01381045 11:−0.27814031
12:0.69668186 13:0.27812037 14:−0.28406402 15:−0.28408644 16:0.31294641 17:0.59632713
18:−0.53039461 19:−0.48443183 20:−0.21528342 21:−0.057703391 22:0.26167902 23:−0.22273448
24:−0.057514388 25:0.22962983 26:−0.80169278 27:−0.37695998 28:0.24314758 29:−0.044114754
30:−0.12885384 31:−0.15732408 32:−0.36818165 33:−0.15900737 34:−0.036611117 35:−0.0049514878
36:−0.037186757 37:−0.015612408 38:−0.13223131 39:−0.010841679 40:−0.007778571
41:0.2574296 42:0.06828472 43:−0.076661251 44:−0.029198203 45:−0.041767091 46:0.19603127
47:−0.092642121 48:−0.015036577 49:−0.083312638 50:0.0015720427 51:0.056218129
52:0.24843177 53:−0.1170302 54:−0.063429236 55:0.037836757 56:0.0042755185
57:−0.029166264 58:−0.14437488 59:0.17036563 60:0.01760035 61:0.056030154 62:0.0017342395
63:−0.08895649 64:−0.058739871 65:−0.077908963 66:0.01418563 67:0.008022422
68:−0.047361556 69:0.033875536 70:0.050317977 71:−0.032308135 72:−0.028249644
73:0.0028905426 74:0.015985508 75:0.011454048 76:−0.017256115 77:−0.1903552 #
−0.014366641566473147 1:0.036439683 2:2.2658525 3:0.73857945 4:0.38687027 5:−1.7616599
6:−0.57902735 7:0.46820387 8:1.8856909 9:0.30010214 10:−0.47674653 11:−0.1517078
12:0.97765487 13:−0.73615444 14:−0.7107752 15:0.024345774 16:−0.069364123 17:−0.41455051
18:0.0079819048 19:−0.3950192 20:−0.82191217 21:0.18839969 22:−0.37523684 23:0.0013825041
24:−0.1781043 25:0.20413665 26:−0.077287562 27:0.12997273 28:0.55342335 29:0.50195873
30:−0.21374071 31:−0.18767828 32:0.16712669 33:−0.37386873 34:−0.20173211 35:−0.12790792
36:0.058619998 37:−0.22323719 38:−0.051452994 39:0.062528022 40:−0.1407471
41:0.0014115029 42:−0.10589418 43:−0.14039214 44:−0.17996028 45:0.15281458 46:0.11357176
47:−0.0091396999 48:0.010193266 49:−0.031747587 50:−0.22025725 51:−0.094614752
52:0.19704044 53:0.057131689 54:−0.079771794 55:−0.014422041 56:−0.028879851
57:0.067725852 58:−0.035659231 59:0.014082163 60:−0.05882173 61:0.034163363
62:−0.055773836 63:0.030350424 64:0.047407053 65:−0.03811083 66:0.0631532 67:−0.030351395
68:0.042218506 69:0.029870642 70:−0.024999747 71:0.041277084 72:0.0016736694
73:0.044923738 74:−0.029579919 75:−0.0047790366 76:0.035559103 77:−0.1903552 #
−0.014366641566473147 1:−0.98347896 2:1.2344706 3:−2.4781878 4:0.16657798 5:−2.129698
6:−2.2319753 7:0.55410063 8:−0.082560048 9:0.54423958 10:−0.47168082 11:−1.0636626
12:1.1748661 13:−0.56587589 14:0.42294616 15:−0.45502305 16:0.17786846 17:0.42689112

APPENDIX C14-continued

SVM Model Weights
(77; Benign/Malignant)

18:−0.37414092 19:−0.33980843 20:0.35829788 21:−0.6875391 22:−0.011590741 23:−0.21064524
24:−0.20099843 25:0.3458541 26:−0.29397207 27:−0.28811103 28:0.4587729 29:0.63381308
30:0.12795596 31:−0.25839421 32:0.043103501 33:0.2085261 34:−0.18622315 35:−0.21511634
36:−0.055485003 37:−0.18207328 38:0.17217164 39:0.091379173 40:0.046381034 41:0.22564502
42:−0.084753767 43:0.13774417 44:0.30820319 45:−0.19548804 46:0.079910964 47:−0.10296195
48:−0.038655866 49:−0.13427037 50:0.1875878 51:−0.16912539 52:−0.14845389 53:0.016987817
54:0.11804666 55:0.031396478 56:−0.022416109 57:0.047793683 58:−0.071392708 59:−0.0653954
60:0.01170331 61:−0.0020478745 62:−0.12251184 63:0.11395038 64:−0.099236965
65:0.0092254281 66:0.036124621 67:0.016300166 68:0.00010936009 69:−0.038672566
70:−0.0085039753 71:−0.0021237442 72:0.00061733427 73:−0.027944284 74:−0.0017543636
75:−0.0063691256 76:0.0038067314 77:−0.1903552 #
−0.0049190335610201745 1:−0.60882109 2:−2.8584712 3:0.57496732 4:−0.75130928 5:−9.5190458
6:0.27075091 7:0.57434607 8:−1.5538838 9:−0.20724995 10:−1.556451 11:−1.2640554
12:0.044540305 13:0.11245795 14:0.303188 15:1.3598011 16:−1.0399643 17:0.48026758
18:−0.70264804 19:0.59989923 20:0.52637458 21:0.58473629 22:−0.37666848 23:0.63706511
24:0.42897493 25:−0.36016449 26:−0.35452563 27:0.36947218 28:0.12619777 29:−0.19706982
30:0.27143911 31:−0.18326542 32:0.43465507 33:0.2273991 34:0.14241935 35:−0.60275239
36:0.23448399 37:0.2072964 38:0.072006881 39:−0.19795091 40:0.027838431 41:0.090146542
42:0.2195451 43:0.12294669 44:−0.084661804 45:−0.086269923 46:−0.062847942 47:0.084243342
48:0.10349163 49:0.031484053 50:−0.021646999 51:−0.03966447 52:−0.13390701 53:−0.22305492
54:−0.0012467239 55:0.059622936 56:−0.078484729 57:−0.067025773 58:−0.0025615105
59:0.054985862 60:−0.020052645 61:0.054060727 62:0.16339394 63:0.027179757
64:−0.033274587 65:−0.025827769 66:0.0054477784 67:−0.052448481 68:0.023569744
69:−0.0051931813 70:0.0090232827 71:0.014594394 72:−0.011770564 73:−0.0084232539
74:−0.014338799 75:−0.0038581877 76:0.0095458394 77:−0.1903552 #
0.014366641566473147 1:0.78437287 2:−4.4449344 3:0.6254968 4:−2.0615332 5:−1.9852951
6:−4.8382282 7:1.0929725 8:1.0148236 9:1.3835551 10:0.70291072 11:−1.216483 12:0.078542039
13:0.078252055 14:−0.36488366 15:0.23275189 16:0.57569152 17:0.44548485 18:−0.5930829
19:−0.94976312 20:−0.050314881 21:−0.030713934 22:−0.2388991 23:−0.58104396 24:−0.21935721
25:−0.43915537 26:−0.062811196 27:0.84503525 28:−0.56491047 29:0.46598771 30:0.36691466
31:−0.37117133 32:0.31719577 33:−0.27784258 34:−0.27265221 35:−0.11683431 36:0.18239057
37:0.012902016 38:0.24787053 39:−0.13218795 40:0.2092301 41:0.16607523 42:−0.26040837
43:−0.15192561 44:0.035929929 45:−0.11957083 46:−0.18263596 47:0.16724525 48:−0.23860328
49:0.083470352 50:0.020203048 51:0.15298387 52:−0.0108961 53:0.0050347256 54:0.055171788
55:−0.10775026 56:0.020015867 57:−0.062860578 58:0.059769709 59:−0.038123596
60:−0.073607378 61:−0.12216988 62:−0.033311035 63:−0.065274194 64:−0.030330187
65:−0.033865973 66:−0.050213091 67:−0.032892387 68:−0.00053698366 69:0.030818151
70:−0.036099114 71:0.011684739 72:−0.018427907 73:0.0028045655 74:−0.01136047
75:−0.010067336 76:−0.0058962107 77:−0.1903552 #
0.014366641566473147 1:3.7983954 2:−2.8186769 3:−1.4519434 4:−2.195426 5:−2.6533656
6:2.0825586 7:1.5454221 8:−0.20361285 9:−0.39983982 10:−1.7713724 11:0.20630343
12:−0.25136039 13:1.5657282 14:−0.93359959 15:0.28368771 16:1.0881795 17:0.37374488
18:−0.1271902 19:−0.57226348 20:−0.077341817 21:0.010985118 22:0.65819842 23:−0.14638901
24:0.024643144 25:0.093744792 26:−0.49434015 27:0.61152005 28:−0.20780563 29:0.1142092
30:−0.025295313 31:0.57843339 32:−0.28088698 33:0.25877917 34:0.28424802 35:−0.32296672
36:−0.13088454 37:0.05007704 38:−0.23703715 39:0.033998683 40:0.0054198606 41:0.079995416
42:−0.082541317 43:−0.02085815 44:0.28339902 45:−0.17407373 46:0.078345314 47:−0.17933286
48:−0.11564343 49:−0.10282493 50:0.21165572 51:0.12612395 52:0.05944553 53:−0.0808184
54:0.010386753 55:−0.035753734 56:0.07422632 57:0.10286044 58:0.029566573 59:−0.18029727
60:−0.023623358 61:0.077112935 62:−0.028325386 63:0.033707879 64:0.072590403
65:−0.040783737 66:−0.085665017 67:0.01513286 68:0.0065052523 69:0.0071727638 70:0.02547146
71:−0.051363762 72:0.002343236 73:0.019884933 74:−0.0058005424 75:0.024081431
76:0.013700188 77:−0.1903552 #
0.014366641566473147 1:2.0552936 2:−1.7792631 3:−5.0197306 4:0.85972375 5:−4.1316504
6:1.1099342 7:1.3047936 8:−0.91936928 9:0.21325256 10:0.44631198 11:−0.1789488
12:0.19074443 13:0.079187766 14:0.034948409 15:0.26068997 16:−0.88272768 17:0.48480159
18:0.32885218 19:−0.030736985 20:−0.58240139 21:0.43174028 22:0.29241329 23:0.33477703
24:0.14355983 25:−0.40937904 26:0.34898606 27:0.24922082 28:−0.21375892 29:−0.60470426
30:−0.20875707 31:0.097439334 32:0.51440519 33:0.25331017 34:−0.47551861 35:0.47468472
36:−0.21166766 37:−0.15964946 38:0.22546616 39:−0.10270288 40:−0.04926113 41:−0.05310287
42:0.27635214 43:−0.10100465 44:−0.018065732 45:0.054791205 46:0.34774545 47:−0.10473054
48:−0.14222775 49:−0.15195538 50:−0.027326245 51:0.069008194 52:−0.10841913 53:0.1092414
54:0.026860779 55:−0.0046055624 56:−0.12693685 57:0.0066170222 58:0.033388477
59:−0.020089246 60:0.011564793 61:−0.05735286 62:−0.081068389 63:0.017309515 64:−0.042013556
65:−0.01251443 66:0.023191659 67:0.024881894 68:0.070939779 69:0.025280092 70:−0.01746075
71:−0.0043585049 72:−0.036692664 73:−0.023504173 74:−0.0064078518 75:0.0046826131
76:−0.0023803851 77:−0.1903552 #
0.014366641566473147 1:−5.1383052 2:6.061408 3:4.37361 4:0.8579585 5:−1.4396833
6:−0.17067717 7:2.0178928 8:1.6520646 9:0.58065701 10:−2.8124666 11:−1.0320003 12:−0.42306098
13:−0.9122436 14:1.1388561 15:1.1089607 16:−1.1878232 17:−0.22829628 18:1.3432964
19:0.81998467 20:0.0017796567 21:−0.25963628 22:−0.26285177 23:−0.25107911 24:0.37141725
25:−0.092447728 26:0.35538772 27:0.15223113 28:0.40563262 29:0.12615278 30:−0.8609494
31:−0.053110305 32:0.040975731 33:−0.10548332 34:−0.5244019 35:0.047989517 36:−0.22594333
37:0.038242642 38:0.0072453259 39:−0.0083433632 40:−0.0034628699 41:0.019481126
42:−0.21611534 43:−0.052488517 44:−0.19659926 45:−0.20181473 46:−0.15464987 47:−0.20240843
48:0.13056521 49:0.040337201 50:0.10180105 51:0.16388451 52:0.0097404206 53:−0.15570106
54:−0.058221113 55:−0.012967933 56:0.036270004 57:−0.085033566 58:−0.051869143

APPENDIX C14-continued

SVM Model Weights
(77; Benign/Malignant)

59:−0.047491744 60:0.029157782 61:−0.030391367 62:0.013853529 63:−0.000405559 64:0.046205331
65:0.047257461 66:−0.035204515 67:−0.03280003 68:−0.011152271 69:0.020370046
70:0.0023210738 71:0.013541492 72:0.030806014 73:−0.0081412867 74:0.0070908093
75:0.021964071 76:−0.0011577503 77:−0.1903552 #
0.014366641566473147 1:−4.6132512 2:−2.2132998 3:−0.39358267 4:−6.1761389 5:2.8478413
6:−1.5153794 7:−3.6003675 8:−1.8517948 9:−0.5924933 10:0.4978095 11:0.58391923 12:−1.087587
13:0.76773041 14:0.69186771 15:−0.025593329 16:0.94396567 17:−0.4763191 18:0.19832441
19:−0.068412051 20:−0.55674487 21:0.43106011 22:1.2399471 23:1.2945429 24:−0.65441757
25:−0.22116522 26:0.42066035 27:−0.35088488 28:1.217671 29:0.028101539 30:0.20146677
31:−0.4495666 32:0.078601733 33:−0.23212147 34:−0.23553114 35:−0.024298372 36:0.15423954
37:−0.044084065 38:−0.10930698 39:−0.132782 40:0.18320324 41:0.19694602 42:−0.059566565
43:0.13453384 44:−0.11347386 45:0.029730432 46:−0.12308405 47:−0.01134504 48:−0.073274188
49:−0.011473239 50:0.14905195 51:−0.0022123195 52:−0.044021815 53:−0.13075589
54:0.19750538 55:0.032747515 56:0.013848832 57:−0.088469855 58:−0.07077118 59:−0.11277883
60:0.013603866 61:0.034485362 62:0.020442314 63:−0.060650151 64:0.014376692
65:0.011825018 66:−0.0070879878 67:−0.044207789 68:0.0032278013 69:−0.014507785
70:0.017139899 71:−0.015519584 72:−0.0012315668 73:0.01636211 74:−0.01597788
75:−0.0155767 76:0.0076164692 77:−0.1903552 #
−0.014366641566473147 1:9.7030468 2:0.66819739 3:5.8191843 4:−8.2204208 5:−1.8977799
6:−2.9315877 7:0.87953585 8:−1.3938494 9:−0.024288971 10:−0.8182686 11:−0.015446785
12:0.94455129 13:−0.79420239 14:−0.0089547783 15:−0.75263548 16:−0.33840969 17:−0.10583192
18:0.6119588 19:−0.7310642 20:−0.58650702 21:−0.64873862 22:0.29020604 23:0.14432767
24:0.17837094 25:0.16666169 26:−0.20689079 27:−0.24292582 28:−0.56125236 29:0.42615271
30:−0.3673048 31:−0.075796448 32:0.027214296 33:0.17140311 34:0.053626042 35:0.51906371
36:−0.21479538 37:0.063844308 38:0.10691347 39:0.18956216 40:−0.0045344578 41:−0.28905043
42:0.022930734 43:0.26438949 44:−0.14260268 45:−0.114551 46:−0.16839971 47:0.28382975
48:−0.20098625 49:0.1020694 50:−0.051623307 51:−0.0006920126 52:−0.092247441 53:0.050449878
54:−0.084579296 55:−0.0065942165 56:0.01643013 57:−0.0026051207 58:0.011165542
59:−0.0036284628 60:−0.10129789 61:0.11005198 62:0.03784043 63:0.017010944 64:−0.03915301
65:0.058657911 66:0.0031343189 67:−0.034388058 68:−0.02680089 69:−0.040217441
70:0.045295361 71:−0.015213866 72:0.004587749 73:0.0070424438 74:0.010509614
75:0.013796221 76:−0.013843808 77:−0.1903552 #
−0.014366641566473147 1:1.5185393 2:−8.8129206 3:1.496369 4:0.5763014 5:0.86818117
6:−1.2795037 7:−4.2156601 8:−0.56625408 9:0.58281475 10:−2.7087336 11:0.29037493
12:−2.2380741 13:−0.57472032 14:−0.57366049 15:−0.48921564 16:0.43995237 17:1.343686
18:0.90233129 19:0.70737684 20:0.03266637 21:−0.11933309 22:−0.88906592 23:−0.4235453
24:1.3271683 25:0.17175321 26:0.50722539 27:0.11574228 28:0.10196363 29:0.1490806
30:−0.18218765 31:0.53827214 32:−0.072305381 33:−0.15888329 34:−0.072632737 35:−0.15716079
36:−0.0250232 37:−0.19818978 38:−0.013534332 39:0.22498085 40:−0.017135991 41:0.050810773
42:−0.2042236 43:0.083479211 44:−0.045949049 45:−0.074102931 46:0.34702897 47:0.063935719
48:−0.083820328 49:−0.090107135 50:−0.11429744 51:−0.056466892 52:−0.1304597
53:−0.084198974 54:0.07538636 55:0.10256518 56:−0.050459389 57:−0.030328479 58:0.0098272143
59:−0.04790828 60:−0.023848668 61:0.056313559 62:−0.017050583 63:−0.090634122
64:−0.01597555 65:0.032743119 66:0.020564901 67:0.052749496 68:−0.061005428 69:0.037992712
70:−0.040777232 71:−0.01538918 72:0.0012490978 73:0.0069816988 74:0.016181387
75:−0.013619523 76:−0.00079112913 77:−0.1903552 #
−0.014366641566473147 1:2.5325806 2:−5.7316437 3:1.9835377 4:−2.9006255 5:−1.641809
6:−2.1068437 7:0.94967872 8:−0.91173142 9:−1.898164 10:−0.21437536 11:1.1519116 12:1.363669
13:0.37059438 14:0.58910161 15:1.3365549 16:0.32368144 17:−0.76552474 18:−0.40306494
19:0.82421821 20:−0.91125214 21:0.29182324 22:−0.12819739 23:−0.50142556 24:−0.25190374
25:−0.47531646 26:0.0027011398 27:−0.27696317 28:−0.50467086 29:0.52437359 30:0.30676487
31:0.31739634 32:0.048272043 33:0.33318385 34:−0.0073576286 35:0.25499216 36:0.16853769
37:0.01358237 38:−0.6349442 39:−0.12822518 40:0.015420563 41:0.017511852 42:−0.25538132
43:−0.015297978 44:0.021501888 45:0.15732731 46:0.16182385 47:−0.045688435 48:0.056720022
49:0.096763268 50:−0.17998141 51:0.094832532 52:−0.10265369 53:−0.04245732 54:0.15721294
55:0.20252867 56:−0.0011371468 57:0.071429849 58:−0.060460798 59:−0.029777113
60:0.014109003 61:−0.045574602 62:−0.029356506 63:−0.033456255 64:0.025514947
65:0.000477769 66:−0.027848693 67:−0.020461816 68:0.059311792 69:−0.042553261
70:−0.014718324 71:0.038734417 72:0.031679016 73:−0.015979243 74:0.013927356
75:−0.0049249493 76:−0.012690028 77:−0.1903552 #
−0.014366641566473147 1:0.15223588 2:5.5671854 3:4.5577908 4:0.3532874 5:1.5121263
6:−0.70956093 7:0.65128499 8:2.3218479 9:−1.4130809 10:−0.77336323 11:−0.79187053
12:0.29612634 13:−0.088514924 14:1.5564902 15:−0.23377517 16:−0.35008034 17:−0.12668104
18:−0.12717567 19:−0.52395982 20:−0.44497445 21:0.15494809 22:0.012923027 23:0.2476735
24:0.56126922 25:−0.24282584 26:0.15572092 27:−0.1244813 28:−0.37741104 29:−0.50919902
30:−0.29728022 31:−0.11964782 32:−0.19552755 33:0.075060204 34:−0.23814188 35:0.021833397
36:0.12039956 37:0.049644377 38:−0.13310903 39:−0.12495502 40:0.063030139 41:0.058026373
42:0.13628843 43:−0.053476285 44:0.27329621 45:0.10415912 46:−0.091743276 47:0.32521066
48:0.018635657 49:−0.074375622 50:0.15896845 51:−0.041640788 52:−0.069370024
53:−0.20971195 54:−0.15083238 55:0.096986167 56:−0.03871315 57:0.050148182 58:−0.031781845
59:0.00075278134 60:−0.033407014 61:−0.010646067 62:0.0072477185 63:−0.10646476
64:−0.040424731 65:−0.033647995 66:0.023068013 67:0.17061853 68:0.089212343 69:−0.028945016
70:0.014698581 71:−0.023675412 72:0.01399309 73:0.021303641 74:−0.018445684
75:−0.027594646 76:3.9542978e−005 77:−0.1903552 #
−0.014366641566473147 1:−2.0519834 2:−5.7539949 3:−0.15902525 4:1.2549058 5:0.78926295
6:1.3120089 7:−0.85973322 8:−1.8853428 9:1.9143454 10:0.53527015 11:0.41111729
12:1.0525408 13:0.81856006 14:0.22798713 15:−0.87402928 16:0.69461113 17:−0.06944979

APPENDIX C14-continued

| SVM Model Weights (77; Benign/Malignant) |
|---|
| 18:−0.71555519 19:0.12973261 20:−0.24039331 21:0.22760484 22:−0.06748949 23:−0.015550113 |
| 24:0.64965105 25:−0.55412126 26:−0.21594368 27:0.042265952 28:0.16809906 29:−0.30688173 |
| 30:0.13210297 31:0.40962413 32:−0.081069484 33:−0.49266335 34:−0.051215768 |
| 35:−0.0041669966 36:−0.16977634 37:−3.3223187e−005 38:0.004468149 39:−0.12733118 |
| 40:−0.25241435 41:0.1975453 42:−0.13768791 43:0.0025036742 44:0.081259325 45:−0.36913687 |
| 46:−0.21001345 47:−0.11908895 48:0.060489751 49:0.20157738 50:−0.028984925 51:−0.084013306 |
| 52:0.083287798 53:0.052802961 54:−0.12861001 55:0.11201138 56:−0.034325536 57:0.14037314 |
| 58:0.10583247 59:0.033109251 60:0.013871646 61:−0.01240919 62:0.023258669 63:−0.03954345 |
| 64:−0.059564836 65:0.070383109 66:−0.11011821 67:0.0084378533 68:0.03723802 |
| 69:−0.002443027 70:0.033857666 71:0.034865566 72:−0.0076245638 73:−0.014922755 |
| 74:0.011829634 75:−0.010670765 76:0.0062378836 77:−0.1903552 # |
| 0.014366641566473147 1:1.9457068 2:−0.10332045 3:0.87312281 4:4.3516202 5:−1.4211158 |
| 6:0.29477999 7:0.53621769 8:−2.8630183 9:−0.12066819 10:0.23083545 11:−0.46195114 |
| 12:−0.15937693 13:0.004128512 14:0.49301022 15:0.7722218 16:−1.1048081 17:−1.5004699 |
| 18:−0.13327286 19:−0.24647602 20:0.23584692 21:−0.96799189 22:0.53398591 23:−0.13294886 |
| 24:0.3294639 25:0.40727386 26:−0.31752932 27:0.26107958 28:−0.35459644 29:0.14212877 |
| 30:−0.29970625 31:0.099324979 32:0.13569631 33:−0.56411219 34:0.042210519 35:−0.068127505 |
| 36:−0.076867878 37:0.17296487 38:−0.0348805 39:0.054626036 40:0.17410359 41:0.15095782 |
| 42:−0.073755011 43:−0.11418944 44:−0.20694269 45:0.079271659 46:0.026105534 |
| 47:−0.33096805 48:−0.015800489 49:−0.22871546 50:−0.054274414 51:0.03232976 52:−0.09608499 |
| 53:0.095759936 54:0.076078683 55:−0.1410865 56:0.112131 57:−0.09008953 58:0.07438802 |
| 59:−0.0097225606 60:0.072573923 61:0.15597592 62:−0.013761474 63:−0.045404479 64:0.019552063 |
| 65:0.013185767 66:−0.02900492 67:0.017416527 68:0.037269637 69:−0.061688438 |
| 70:0.021983478 71:−0.010946775 72:−0.017950388 73:0.017296027 74:0.013625336 |
| 75:−0.044751812 76:−0.0025324558 77:−0.1903552 # |
| 0.014366641566473147 1:−3.9141951 2:−1.4193999 3:−2.5200441 4:2.0627365 5:−2.1883812 |
| 6:−1.718942 7:1.0744553 8:2.3557556 9:1.79149 10:−0.26809931 11:1.8130393 12:−0.016630568 |
| 13:0.34241861 14:−1.7308311 15:0.57069314 16:−0.7711826 17:0.41015607 18:−0.098526984 |
| 19:0.66631621 20:−0.12577392 21:0.32922119 22:0.60433245 23:0.97283071 24:−0.32304925 |
| 25:−0.20729925 26:−0.27250272 27:−0.086151153 28:0.1417837 29:0.48576379 30:−0.18109652 |
| 31:0.064179935 32:0.2012735 33:−0.18721823 34:−0.030852422 35:0.25314745 36:−0.20889358 |
| 37:0.1744158 38:−0.2162829 39:0.30997968 40:0.023342438 41:−0.052237552 42:−0.22249833 |
| 43:0.10204149 44:0.16170301 45:0.22650814 46:−0.013372432 47:0.22143222 48:0.11201949 |
| 49:−0.19142395 50:−0.13487062 51:−0.048036106 52:−0.0834691 53:−0.0047875619 54:−0.10635032 |
| 55:−0.14468561 56:−0.028345361 57:0.14728914 58:−0.058128905 59:0.038009007 |
| 60:0.058083087 61:0.011155581 62:0.0022722324 63:−0.06769377 64:0.030425945 |
| 65:−0.00036476023 66:−0.063926339 67:0.00058330392 68:−0.053872492 69:0.031821329 |
| 70:0.021149822 71:−0.033700339 72:0.010184064 73:−0.015983908 74:−0.04749297 |
| 75:−0.017135194 76:−0.014325701 77:−0.1903552 # |
| 0.014366641566473147 1:2.310734 2:−1.1059308 3:0.22017837 4:3.896436 5:−2.1173472 |
| 6:3.1687901 7:−1.883824 8:1.5314238 9:−3.4586222 10:1.6937501 11:1.3740205 12:−1.9752978 |
| 13:1.4086146 14:−0.81362706 15:0.4446381 16:−1.1310391 17:−0.38824621 18:−0.21221177 |
| 19:0.10883191 20:−0.21770738 21:−0.55974531 22:0.50175703 23:−0.71784461 24:−0.65432233 |
| 25:0.48026872 26:−0.15015155 27:0.50466239 28:−0.13518056 29:−0.061337456 30:0.226494 |
| 31:−0.26634458 32:−0.0049446644 33:0.48054093 34:−0.21846922 35:0.0099513186 36:0.21148196 |
| 37:−0.24660596 38:−0.075030006 39:0.19936273 40:−0.32904357 41:−0.0069841105 |
| 42:−0.13948932 43:−0.1366369 44:0.056176495 45:−0.21309447 46:−0.17469674 47:0.20021287 |
| 48:0.17017165 49:−0.089513376 50:0.11125381 51:−0.0046472549 52:−0.094008416 |
| 53:0.041407879 54:0.0033353975 55:0.062060002 56:−0.037098181 57:−0.10780364 |
| 58:0.041023109 59:−0.019434407 60:0.009155808 61:0.011127234 62:−0.028933367 |
| 63:−0.041442763 64:−0.014213523 65:0.049882438 66:0.024546318 67:−0.008226892 68:−0.04100458 |
| 69:−0.027226012 70:0.018743841 71:−0.0089705363 72:0.017702904 73:0.013409971 |
| 74:−0.0089387186 75:0.011439535 76:0.0021474792 77:−0.1903552 # |
| −0.014366641566473147 1:0.0086950473 2:7.4287958 3:−1.2594923 4:4.5742617 5:−3.5837188 |
| 6:−0.54576951 7:−0.42338333 8:−0.41678026 9:2.6206603 10:1.2880759 11:1.4479926 12:−1.8797246 |
| 13:−1.7226071 14:0.46196926 15:−0.59177333 16:−0.26631755 17:0.22360399 18:−0.90718448 |
| 19:0.83566612 20:0.43406442 21:−0.062331442 22:0.57169986 23:−0.22707027 24:−0.062218994 |
| 25:−0.016465422 26:−0.028595651 27:0.13626909 28:0.27231267 29:0.47153589 30:−0.34474158 |
| 31:−0.093787417 32:−0.0085730581 33:0.066647887 34:0.24470942 35:0.2533564 36:0.351188 |
| 37:0.21540637 38:−0.36241797 39:−0.022588084 40:0.29897743 41:0.082304008 42:0.29527587 |
| 43:−0.18651633 44:0.14638354 45:−0.10031547 46:−0.30776605 47:−0.055860866 48:−0.19704452 |
| 49:0.011295505 50:−0.20617086 51:−0.018827379 52:0.12299653 53:−0.036343422 |
| 54:0.080829255 55:0.071492098 56:−0.10682715 57:0.014258738 58:−0.065813407 |
| 59:−0.051579762 60:−0.11290349 61:−0.04513289 62:−0.0017980429 63:−0.012239976 64:0.020976108 |
| 65:0.062578693 66:0.049340863 67:0.041311506 68:−0.046389718 69:−0.018551484 |
| 70:−0.031707872 71:0.0027264338 72:−0.015166119 73:−0.016344562 74:0.025136979 |
| 75:−0.0047537675 76:−0.0022677009 77:−0.1903552 # |
| −0.014366641566473147 1:6.412724 2:3.3431029 3:0.31715581 4:2.6263151 5:−3.1070433 |
| 6:−0.64810574 7:3.0432169 8:−0.16104603 9:−0.70943946 10:0.64363986 11:0.68613762 |
| 12:−0.48589048 13:1.0245137 14:−0.3469356 15:−0.98740584 16:−0.1597576 17:−0.13679953 |
| 18:−1.1578943 19:0.081538312 20:0.35532051 21:−0.51552761 22:−0.45972785 23:−0.41673362 |
| 24:−0.45582294 25:−0.068960272 26:0.52082157 27:0.29424605 28:0.52312738 29:−0.36373743 |
| 30:−0.44826981 31:−0.069172502 32:−0.16101946 33:−0.23738526 34:0.38937423 35:−0.44238356 |
| 36:−0.16834627 37:0.084654093 38:−0.25375864 39:0.014067991 40:−0.041377466 41:−0.11094289 |
| 42:−0.044660144 43:0.26178631 44:−0.21696672 45:0.0048013031 46:0.15499312 47:0.20758098 |
| 48:−0.14034241 49:0.35604203 50:0.10976823 51:0.056843802 52:−0.090501465 53:−0.017173339 |
| 54:0.12849262 55:0.0010867481 56:0.070300519 57:0.10791802 58:0.0059871618 |

APPENDIX C14-continued

| SVM Model Weights (77; Benign/Malignant) |
|---|
| 59:0.031652883 60:−0.078071631 61:−0.015916096 62:−0.085686475 63:0.019301716 64:0.017782219 65:0.03570522 66:0.02060356 67:0.034593295 68:−0.0036056128 69:0.027084982 70:−0.0041193883 71:−0.0092219105 72:0.018324343 73:0.018377872 74:−0.013282364 75:−0.018555829 76:−0.0018179378 77:−0.1903552 # |
| −0.014366641566473147 1:−1.0241342 2:1.5231498 3:−1.076713 4:2.3327794 5:−1.3972167 6:−4.8702788 7:0.0310582 8:2.0429132 9:−2.6679163 10:1.0570183 11:−0.67595375 12:0.98076826 13:0.10744476 14:−0.77943295 15:−0.65874767 16:−0.22273232 17:0.59641743 18:−0.24587433 19:0.63810837 20:0.34959298 21:−0.23775244 22:0.37742439 23:0.21195965 24:−0.24901225 25:0.15619588 26:0.42186996 27:−0.1109751 28:−0.28490567 29:−0.47463045 30:0.14734553 31:0.045594156 32:−0.14481628 33:−0.64207554 34:−0.0048152688 35:−0.076468244 36:−0.0105918 37:−0.067119375 38:−0.022876361 39:−0.10502829 40:0.21603355 41:−0.22153759 42:−0.058958158 43:0.24596947 44:0.15167919 45:−0.12298354 46:−0.030580647 47:−0.12051544 48:−0.0095293308 49:−0.075859286 50:−0.25174901 51:−0.065942712 52:−0.078680284 53:−0.03709437 54:0.08098992 55:0.076991722 56:−0.067474872 57:0.012523067 58:0.017894564 59:0.023835968 60:0.14713436 61:0.052928206 62:0.0086156102 63:−0.062305477 64:−0.080605924 65:−0.036815394 66:0.0070435354 67:−0.062185895 68:0.0010427483 69:−0.0075971601 70:−0.0049896692 71:0.0070117707 72:−0.00080876832 73:0.04378644 74:0.020347394 75:0.03057475 76:−0.011528331 77:−0.1903552 # |
| −0.014366641566473147 1:5.0260968 2:3.33251 3:−3.0645964 4:−1.1266552 5:2.0511241 6:2.4722266 7:−0.31921747 8:0.42432824 9:−1.4342953 10:0.5985325 11:−0.58325708 12:−0.64486521 13:0.97768992 14:0.47465622 15:0.93895423 16:0.15637298 17:0.18814051 18:−0.36229941 19:−0.72116882 20:0.30202496 21:0.78613603 22:−0.12307633 23:−0.019779095 24:−0.0066971006 25:0.10877067 26:0.53886485 27:−0.19849426 28:−0.36407992 29:0.0096966689 30:0.061732315 31:0.46578792 32:−0.18557502 33:−0.042359971 34:−0.057707205 35:−0.048777331 36:0.05239854 37:0.10762736 38:0.16391441 39:0.39816695 40:0.10601038 41:0.051557846 42:−0.18948668 43:0.23557569 44:−0.060350876 45:0.091157578 46:−0.34549037 47:−0.13098626 48:0.18952692 49:0.013362135 50:−0.2112889 51:−0.037789736 52:−0.20624651 53:−0.10787465 54:−0.0088883797 55:−0.084701195 56:−0.013686365 57:−0.033450615 58:0.049604855 59:0.041098922 60:−0.033449337 61:−0.068733379 62:−0.018974565 63:0.10018054 64:−0.046381734 65:−0.034564085 66:0.05193001 67:0.007716923 68:−0.016621033 69:0.050281886 70:0.0318905 71:−0.011143728 72:−0.037554923 73:−0.0065807905 74:0.020281313 75:−0.018346354 76:−0.0055265604 77:−0.1903552 # |
| −0.014366641566473147 1:0.24181463 2:4.7720656 3:−3.8317716 4:−0.97415411 5:1.6347659 6:2.2904735 7:0.26133674 8:0.21623282 9:−0.8961876 10:0.76824886 11:−0.0099194981 12:−0.22780475 13:−1.0504795 14:−0.13816266 15:1.0356774 16:0.5986892 17:0.69159287 18:0.027103486 19:0.015305936 20:0.47779447 21:−0.50045276 22:−0.058900885 23:−0.42779335 24:−0.20147148 25:0.052400883 26:0.57754159 27:−0.095236808 28:0.29366001 29:0.011148577 30:−0.37274989 31:0.3565529 32:0.0026140241 33:0.23899651 34:−0.10363425 35:−0.25149646 36:−0.18619215 37:−0.026069565 38:−0.23767348 39:0.12850079 40:0.10601889 41:0.16910984 42:−0.10931839 43:0.16842408 44:0.071588859 45:0.17509368 46:0.064857543 47:0.052578803 48:−0.13203762 49:0.027148409 50:−0.030585466 51:0.11690807 52:0.10918447 53:−0.019145181 54:−0.18143736 55:0.037928492 56:0.047996536 57:−0.067557797 58:−0.099280432 59:0.048407283 60:−0.022102268 61:0.024244418 62:0.054017238 63:−0.0082150521 64:−0.092946753 65:0.020567844 66:−0.035734423 67:−0.11871189 68:0.043275796 69:−0.010846983 70:0.017459711 71:0.059922472 72:0.00011216601 73:0.024662396 74:0.01052844 75:−0.0055840667 76:0.00072066969 77:−0.1903552 # |
| 0.014366641566473147 1:4.8399949 2:−1.577003 3:0.4098469 4:−4.8267884 5:−3.2122846 6:0.13074312 7:−1.0679454 8:−0.46808416 9:−0.23805074 10:−1.0340061 11:1.597669 12:1.8713994 13:−0.21021381 14:0.80143857 15:0.46408594 16:0.85194242 17:−0.15311828 18:0.43129027 19:−0.12552181 20:−0.62373829 21:0.20995806 22:−0.12450007 23:−0.22205693 24:−0.19233423 25:−0.032815449 26:−0.046016943 27:−0.29073951 28:−0.035083421 29:0.31549242 30:0.082584769 31:−0.18598664 32:−0.21957016 33:0.16073878 34:−0.19274434 35:−0.27884278 36:0.006478738 37:0.0029400971 38:−0.087196238 39:0.25714919 40:0.033714667 41:−0.18430446 42:0.068434864 43:0.0026282242 44:−0.047473546 45:0.038166113 46:−0.053374574 47:−0.33356264 48:−0.0082953405 49:0.030260883 50:0.019255396 51:−0.096664444 52:−0.038342629 53:0.11823314 54:−0.13005069 55:0.083160579 56:0.037239932 57:−0.043172631 58:−0.038880426 59:0.12548071 60:0.015871141 61:−0.16188362 62:0.059044212 63:−0.0062481733 64:0.004705146 65:0.058123488 66:0.034601629 67:0.044889063 68:−0.06364727 69:−0.003280954 70:−0.021109624 71:−0.046139259 72:−0.019625781 73:−0.008342931 74:−0.014831739 75:0.0032667767 76:0.0044024824 77:−0.1903552 # |
| 0.014366641566473147 1:0.64063972 2:−4.3281217 3:−0.50341749 4:−0.40697601 5:−0.68223512 6:−1.6602443 7:−0.40938717 8:1.6942961 9:2.4347324 10:−0.60462981 11:−0.097168326 12:0.0050968276 13:1.7853876 14:0.048699632 15:−0.25621322 16:−0.12986372 17:−0.2782934 18:−0.015592704 19:−0.15302683 20:0.0092439903 21:0.48958755 22:−0.20649716 23:−0.51439488 24:0.26855186 25:0.083497152 26:−0.71435803 27:−0.47511208 28:−0.32857516 29:−0.11170151 30:−0.1165484 31:−0.35029963 32:−0.62084532 33:−0.16450997 34:0.18622608 35:−0.021761831 36:−0.10378104 37:−0.25945729 38:−0.076803081 39:−0.13550758 40:0.018108981 41:0.0017327369 42:−0.053017002 43:0.063620336 44:−0.1221275 45:−0.016810352 46:−0.10541792 47:0.084506139 48:0.0031306995 49:−0.24674615 50:0.12521923 51:−0.25683743 52:0.048571963 53:0.064598888 54:−0.1242438 55:0.021750417 56:−0.015171538 57:−0.09752132 58:−0.077803984 59:−0.032717209 60:0.053175498 61:−0.048075061 62:−0.01608794 63:0.039334778 64:0.033343799 65:0.055488307 66:0.021028349 67:−0.060814992 68:0.072204947 69:−0.010620631 70:−0.024483757 71:0.014456267 72:−0.026644867 73:0.011894991 74:0.0058649732 75:−0.0080829319 76:−0.0052256379 77:−0.1903552 # |
| 0.014366641566473147 1:−3.2744193 2:2.0898314 3:1.8613226 4:−1.7946569 5:0.07536304 6:−0.12928621 7:−1.515174 8:0.3986617 9:0.134441 10:−0.78612506 11:−0.27925241 12:0.72043931 |

APPENDIX C14-continued

| SVM Model Weights (77; Benign/Malignant) |
|---|
| 13:0.43654722 14:−0.71114331 15:0.84624708 16:−0.82258749 17:−1.3289777 18:−0.026538538 19:0.20243154 20:−0.21683165 21:−0.24498834 22:0.69101232 23:0.1044576 24:0.16307323 25:−0.017817134 26:0.29545265 27:0.3912445 28:0.3396759 29:0.018561298 30:0.25077307 31:−0.44278297 32:−0.41400778 33:0.048348423 34:0.11789599 35:0.2160524 36:−0.32623446 37:0.30840415 38:−0.15214995 39:−0.042667065 40:−0.20633234 41:−0.12931056 42:0.025408518 43:0.12419267 44:−0.18750958 45:0.1706515 46:0.02180228 47:−0.092567503 48:0.015976628 49:0.041983377 50:−0.025374098 51:−0.29746276 52:−0.030740129 53:−0.035610572 54:0.078764416 55:0.038662545 56:−0.0089781983 57:0.0099382252 58:0.046476327 59:−0.064236484 60:−0.074750856 61:0.029678604 62:−0.073459484 63:0.082319096 64:−0.011617878 65:−0.088632539 66:−0.068089172 67:0.098639116 68:−0.027461262 69:0.060167465 70:0.012938203 71:0.066889241 72:−0.023686005 73:−0.021886256 74:0.025301566 75:0.0092670666 76:0.0043329867 77:−0.1903552 # |
| −0.014366641566473147 1:1.2656516 2:−7.4226255 3:−1.2094113 4:−1.4164938 5:−2.0883899 6:−0.24654385 7:−0.40879437 8:−1.2234688 9:−0.86531705 10:1.0696479 11:0.46162176 12:−0.30605674 13:−0.15128484 14:0.23330732 15:0.27477789 16:−0.71871454 17:1.165464 18:−0.27110574 19:0.6585626 20:−0.81460595 21:0.15341932 22:−0.57634073 23:0.31279573 24:0.12532996 25:0.15610991 26:0.74201733 27:−0.23424162 28:−0.22608343 29:0.13688779 30:−0.76177925 31:−0.32971966 32:0.064240798 33:−0.043720007 34:0.092048764 35:−0.17983389 36:0.0028795414 37:−0.4229708 38:−0.18205008 39:−0.063806318 40:0.0088489326 41:−0.097641468 42:0.024118705 43:0.08669696 44:0.067386396 45:0.099886373 46:−0.11298157 47:0.11224101 48:0.056317788 49:−0.1822836 50:0.14070061 51:0.17807679 52:0.27154601 53:−0.020348374 54:0.10119686 55:0.059923604 56:0.056035247 57:0.053977996 58:0.050456658 59:0.050638363 60:0.048418 61:0.033397816 62:−0.069370568 63:0.11859584 64:−0.038821179 65:−0.027432451 66:−0.010823026 67:−0.028766898 68:−0.035266783 69:0.019661924 70:0.054376125 71:−0.0082688471 72:−0.014769667 73:−0.046848733 74:−0.0056360275 75:−0.028798208 76:−0.0026239792 77:−0.1903552 # |
| −0.0080999421653903 01 1:0.4305459 2:−1.0244814 3:−3.9335921 4:−2.7328825 5:−2.3352003 6:−3.5151963 7:0.097749971 8:−0.16376342 9:−4.7180619 10:0.5390588 11:−2.5279562 12:−0.58943939 13:−0.34163991 14:−1.0314358 15:−0.11350648 16:−0.079270646 17:0.27886191 18:0.23193325 19:0.70044869 20:−0.85416383 21:0.034811489 22:0.12679483 23:−0.047767606 24:0.62623054 25:−0.29348424 26:−0.68791932 27:−0.44419166 28:0.78568357 29:−0.15935487 30:0.20843664 31:0.20469341 32:0.086521991 33:0.35393345 34:0.31250209 35:−0.14902753 36:−0.094059557 37:0.12680252 38:0.31439894 39:−0.26907125 40:−0.16706237 41:0.096372217 42:−0.12450676 43:−0.058414344 44:−0.0067182183 45:0.2218852 46:−0.087029718 47:0.0088688498 48:−0.03858912 49:0.062550828 50:−0.18552804 51:0.018688088 52:0.16671972 53:0.098336212 54:−0.11930388 55:−0.059249781 56:−0.037765212 57:−0.06040927 58:0.089001983 59:−0.036773607 60:−0.077399097 61:0.0092704566 62:−0.045860283 63:0.013600147 64:0.057258479 65:0.065354072 66:0.016045194 67:0.038016565 68:−0.017977312 69:0.001355283 70:0.0022360161 71:−0.0099780988 72:0.0055729579 73:0.012173092 74:−0.0043740384 75:−0.013999875 76:−0.0061833486 77:−0.1903552 # |
| 0.014366641566473147 1:0.65849918 2:7.3459477 3:−2.4427726 4:2.3193429 5:−1.218644 6:1.4283658 7:−3.3438566 8:0.25067937 9:−1.3770546 10:0.41048476 11:−0.71343094 12:0.86435151 13:−0.3603079 14:0.79979289 15:0.012530287 16:0.27095726 17:0.41266367 18:−0.27426738 19:0.21218434 20:0.20119031 21:−0.13077945 22:0.40582347 23:0.044716451 24:0.41075251 25:−0.23923875 26:0.067785241 27:−0.027200775 28:−0.19376729 29:0.23991907 30:−0.17788449 31:0.044720948 32:−0.21754451 33:−0.11010751 34:−0.20842354 35:0.17920643 36:−0.018441172 37:0.24872117 38:0.053262081 39:0.071563356 40:0.30316991 41:0.62006897 42:−0.22569205 43:−0.016453605 44:−0.084960885 45:0.13689542 46:0.091712102 47:0.046738304 48:−0.21731758 49:0.10456941 50:0.10247301 51:−0.021672357 52:−0.10332356 53:0.049403485 54:−0.12049867 55:−0.0017020596 56:0.040911231 57:0.10190183 58:0.11759457 59:0.016688168 60:0.024345895 61:−0.044099554 62:−0.045886628 63:0.064227335 64:0.012302308 65:0.025947077 66:0.034070235 67:−0.036609977 68:−0.016636601 69:−0.0090474635 70:0.010177488 71:−0.02284261 72:0.0013829191 73:−0.023361189 74:−0.019384004 75:0.013908882 76:0.0065665166 77:−0.1903552 # |
| 0.014366641566473147 1:2.7474566 2:1.2460642 3:−4.0204258 4:0.83400828 5:−2.8434477 6:−1.7167914 7:−0.48103359 8:0.94106251 9:1.0425173 10:0.69047868 11:1.9439002 12:0.39881346 13:−0.43297642 14:−1.1368617 15:−1.1669015 16:0.42963937 17:−1.4883448 18:0.72490615 19:0.010568178 20:−0.33923134 21:0.23771055 22:−1.2625923 23:0.80907977 24:−0.10852986 25:0.91694248 26:−0.015900878 27:−0.46191558 28:−0.49960035 29:−0.39918709 30:0.067619972 31:0.20562081 32:−0.2038316 33:0.23505221 34:−0.59091848 35:−0.44472936 36:−0.071605511 37:0.51733172 38:−0.15707144 39:0.12074494 40:0.058549076 41:0.19994643 42:0.23099627 43:−0.18055835 44:−0.17749609 45:0.089562424 46:0.002244127 47:0.0265535 48:−0.13346855 49:0.018193174 50:0.066837363 51:0.035271257 52:0.077667221 53:−0.010307689 54:0.099288367 55:0.085801058 56:0.08327198 57:−0.078925878 58:0.1320504 59:−0.035583336 60:0.018722687 61:0.036735281 62:0.050763991 63:0.011279641 64:−0.048823617 65:−0.061285485 66:−0.036163729 67:0.0083088046 68:−0.029117899 69:−0.0035960898 70:−0.023177495 71:0.012723417 72:0.0082321661 73:0.0087283077 74:−0.01914395 75:0.0074520698 76:−0.010503807 77:−0.1903552 # |
| 0.014366641566473147 1:5.0305886 2:1.4601214 3:−1.1594079 4:−2.8912799 5:0.53912604 6:2.2991443 7:−0.5243212 8:0.19341926 9:−1.7080882 10:−0.51476121 11:1.0882531 12:0.40837818 13:−1.18138 14:−0.7188617 15:0.43729103 16:0.13707112 17:0.84905803 18:−0.57230026 19:−0.44414842 20:−0.23731495 21:−0.59159088 22:−0.40707302 23:0.023270441 24:0.24321832 25:0.12222683 26:0.15580381 27:−0.076688752 28:0.11795026 29:0.29755804 30:−0.14055456 31:−0.32282025 32:−0.28704578 33:−0.13727713 34:0.19655944 35:0.14657718 36:0.043132551 37:0.11802579 38:−0.17969567 39:0.14542013 40:−0.20095536 41:0.14669056 42:−0.14271137 43:−0.048345882 44:0.019812914 45:−0.076500297 46:0.10122601 47:0.082341999 48:0.11945991 49:−0.06983503 50:0.052922711 51:−0.11699574 52:0.03804262 |

APPENDIX C14-continued

SVM Model Weights
(77; Benign/Malignant)

53:0.015200823 54:0.04301719 55:−0.16011466 56:−0.079104267 57:−0.079046525
58:0.066463508 59:0.05129284 60:−0.016134573 61:0.016770855 62:0.060160391
63:−0.038315374 64:−0.037535146 65:−0.1285799 66:0.015116243 67:−0.012346329 68:0.025544504
69:−0.06931252 70:−0.072930224 71:0.017304057 72:0.061071869 73:−0.031499021
74:0.007641295 75:−0.0086963726 76:0.010684379 77:−0.1903552 #
−0.014366641566473147 1:4.9205275 2:4.4811344 3:0.46670663 4:−0.6917854 5:−3.1135769
6:0.83850479 7:1.0693635 8:1.4324343 9:0.52255154 10:0.69640666 11:−0.51174265
12:−1.6448867 13:−1.3560991 14:−0.55430722 15:−0.33024573 16:0.51909614 17:−1.0790735
18:0.45473811 19:−0.1579944 20:−0.48828742 21:0.91906571 22:−0.088839911 23:−0.5209924
24:−0.24924682 25:−0.51088971 26:0.18952447 27:−0.037802793 28:0.74764478 29:0.10259452
30:0.27593285 31:0.51057237 32:−0.20379345 33:0.025223717 34:−0.27037227 35:0.043877788
36:−0.14401068 37:−0.36862826 38:0.17961891 39:−0.22619173 40:0.21679848 41:−0.1764939
42:−0.146 43:−0.41315567 44:−0.29108635 45:0.023591593 46:−0.12427425 47:0.16880755
48:0.21522479 49:0.015556294 50:0.092425913 51:0.054461986 52:−0.048486341
53:0.056634054 54:0.045462266 55:0.041813437 56:0.067413501 57:0.15094164 58:0.045531269
59:0.012418463 60:0.072265632 61:0.056006514 62:0.008381064 63:−0.045618545
64:−0.015256104 65:−0.058804318 66:0.019775337 67:−0.016664984 68:−0.016195348 69:−0.03486564
70:0.018898722 71:−0.022043562 72:−0.020112196 73:−0.015305521 74:0.023465414
75:−0.0031566801 76:−0.0064918702 77:−0.1903552 #
−0.014366641566473147 1:7.2357998 2:−2.5760925 3:3.3008342 4:6.1357307 5:−1.7416829
6:−3.3115962 7:−4.1383033 8:0.44118306 9:0.85719305 10:1.2227336 11:−1.1392747 12:−0.2572121
13:1.7088685 14:1.156287 15:1.4961365 16:0.38963583 17:0.21130928 18:1.253765
19:−1.2841004 20:1.4980761 21:−0.35090634 22:0.41543338 23:0.17004517 24:−0.88354498
25:−0.50515103 26:0.20572981 27:−0.1414486 28:−0.47590399 29:0.29006901 30:−0.18332048
31:0.073717453 32:−0.1450136 33:0.21362667 34:−0.22664665 35:−0.18421994 36:−0.045662146
37:−0.16085526 38:−0.026386814 39:0.012144359 40:−0.32803783 41:−0.026165731
42:0.22778717 43:0.0042086141 44:−0.032528322 45:0.095946208 46:0.10850158
47:0.099361554 48:0.055781346 49:0.11912555 50:−0.13750966 51:−0.010643505 52:0.10181255
53:0.017897749 54:−0.017433861 55:0.056918561 56:0.030062556 57:0.035453454
58:−0.022044426 59:0.016548721 60:−0.046895131 61:0.085475959 62:0.010572768 63:0.016852925
64:0.061007608 65:−0.0033978429 66:−0.0075596976 67:−0.025634525 68:0.020283028
69:0.01139829 70:−0.027251402 71:−0.0076017044 72:−0.0086836452 73:−0.0026181575
74:−0.0067067994 75:−0.0094899526 76:0.00034936468 77:−0.1903552 #
−0.014366641566473147 1:4.3359571 2:3.8234689 3:−2.8907855 4:−1.8176922 5:−3.2642934
6:1.499356 7:0.61374962 8:−0.4559674 9:1.4580479 10:0.14982417 11:−0.69858479
12:−0.12897876 13:−1.3299537 14:0.34806621 15:−0.92856109 16:0.88607275 17:0.19600573
18:0.65819579 19:−0.37459031 20:−0.14938022 21:−0.25678331 22:0.32082316 23:−0.14041877
24:0.24039213 25:−0.2520546 26:0.61798555 27:0.48199934 28:0.20119956 29:−0.20227547
30:−0.03617036 31:0.15134418 32:−0.59117514 33:0.58974189 34:−0.16551967 35:−0.25091422
36:0.22029769 37:−0.26992726 38:−0.087550826 39:−0.24539717 40:−0.11780227 41:0.024084894
42:0.21429883 43:0.44184637 44:0.069465645 45:0.092701435 46:−0.16362673 47:−0.053413719
48:0.057747584 49:−0.11397427 50:−0.091904782 51:−0.1610052 52:0.013875943
53:−0.014354171 54:0.055742405 55:−0.17919423 56:0.051374819 57:−0.013525409 58:0.047084335
59:0.00061351567 60:0.15369767 61:−0.030611804 62:−0.082030259 63:−0.10312333
64:0.031090863 65:0.077728905 66:−0.041896563 67:0.005092477 68:−0.0019992492
69:−0.0033848579 70:−0.014885747 71:0.04874099 72:0.022693895 73:0.0031728249
74:−0.030280821 75:−0.0054558106 76:−0.011695818 77:−0.1903552 #
0.014366641566473147 1:9.299901 2:−6.3458824 3:2.7524576 4:9.9616251 5:2.8761771
6:−0.850842 7:3.0535984 8:−2.7053313 9:−1.398501 10:−2.4400167 11:−1.6164707 12:0.0070890831
13:−3.0262942 14:0.046286501 15:0.29393116 16:1.5132728 17:0.54635787 18:−1.1216282
19:0.41560301 20:−0.27752313 21:−0.20198008 22:−0.25580475 23:1.1561829 24:−0.85119969
25:−0.19575082 26:−0.15948655 27:−0.098125055 28:−0.05885601 29:−0.016427953 30:0.12314785
31:0.042117026 32:−0.40615293 33:−0.15727793 34:−0.029718058 35:0.3530089
36:−0.0079385908 37:−0.16118599 38:−0.020404682 39:−0.046971925 40:0.006325311
41:0.057021178 42:0.069116771 43:0.013899461 44:−0.12081962 45:0.02917996 46:−0.16111016
47:0.052578334 48:0.048796926 49:−0.10206705 50:0.016949844 51:−0.053259648
52:−0.035713613 53:0.05253211 54:−0.046368383 55:0.059575915 56:0.094203331 57:−0.04323082
58:0.031710036 59:−0.030030232 60:0.02446078 61:−0.01040124 62:0.046681132 63:0.05489951
64:0.0033939651 65:0.012671889 66:−0.0090807769 67:0.01221575 68:−0.0098859668
69:0.01306745 70:−0.0064815334 71:−0.0013609082 72:0.01892061 73:−0.0072198794
74:−0.017726589 75:0.0079964185 76:0.0078473007 77:−0.1903552 #
0.014366641566473147 1:−4.1357908 2:0.78054887 3:−0.20699237 4:−0.83030242 5:1.3259537
6:−2.5219975 7:1.5075016 8:1.0979512 9:−0.82589865 10:−1.2119597 11:1.0019481 12:0.43480569
13:−0.015390897 14:0.6580568 15:0.26209942 16:0.36332402 17:−0.41831663 18:0.41011378
19:0.92145783 20:0.1468721 21:−1.0389067 22:−0.26410657 23:−0.24352691 24:−0.05647945
25:−0.37149188 26:−0.36694792 27:0.36167088 28:−0.013813307 29:−0.068751395 30:−0.33328044
31:−0.14971182 32:−0.24304226 33:−0.0587334 34:−0.15603513 35:0.078162491 36:0.15516308
37:−0.19923182 38:−0.15853003 39:−0.19104345 40:−0.024287622 41:−0.1232719 42:−0.023038765
43:−0.13077544 44:0.11733308 45:−0.074740797 46:0.10486637 47:−0.07965558 48:0.29323244
49:0.099165991 50:0.049726095 51:−0.075978816 52:0.048318576 53:0.03596171 54:0.16445431
55:−0.17491266 56:−0.0005393498 57:−0.051121168 58:0.08598315 59:0.052065942
60:−0.067120552 61:−0.12598296 62:−0.0077895727 63:0.045560423 64:−0.090424232 65:−0.02112402
66:−0.041049857 67:−0.01479549 68:−0.022920636 69:0.011498102 70:−0.0047625033
71:−0.029396916 72:−0.038303874 73:0.032011807 74:−0.012711794 75:−0.01700782 76:−0.013560317
77:−0.1903552 #
0.014366641566473147 1:−0.19740181 2:−1.6914537 3:−1.212109 4:1.5638839 5:3.6735976
6:−0.86641341 7:−0.11548568 8:1.00301 9:1.7542377 10:0.78187764 11:−0.10535101 12:0.59311414

APPENDIX C14-continued

SVM Model Weights
(77; Benign/Malignant)

13:−0.6173144 14:−0.033974938 15:0.46210256 16:−0.023176683 17:0.31983504 18:0.85149676
19:0.61975396 20:1.0456136 21:−0.093077436 22:−0.048776831 23:−0.31832126 24:0.24004199
25:−0.79643059 26:0.11079787 27:−0.12254273 28:−0.31635928 29:0.019774711 30:0.52289999
31:0.14084098 32:0.32519194 33:0.31984305 34:0.34300777 35:−0.11191703 36:−0.11260098
37:−0.061156079 38:0.038387079 39:−0.23079048 40:0.24007747 41:0.10833801 42:0.0047330125
43:0.12625121 44:−0.44397509 45:0.039044093 46:0.060190111 47:0.11975911 48:0.03 5958875
49:−0.25546739 50:0.080933049 51:−0.091758505 52:0.13760297 53:−0.10658669 54:0.095461726
55:−0.0048113344 56:0.0047174729 57:0.019343717 58:0.029712265 59:0.082569741
60:−0.15629439 61:−0.069718085 62:−0.066863708 63:0.0293837 64:−0.025656275 65:−0.028321033
66:−0.021637948 67:0.024996879 68:−0.049397893 69:−0.095381103 70:0.059422418
71:−0.011811043 72:0.02806039 73:0.019222561 74:3.8411741e−005 75:0.0076575158
76:0.0077811494 77:−0.1903552 #
0.014366641566473147 1:−2.0754793 2:2.2441027 3:1.32143 4:0.092494741 5:1.6861345
6:−1.6531069 7:−0.069175199 8:0.78724957 9:0.32604992 10:0.7906251 11:−0.43592307
12:2.1313064 13:−0.41815779 14:0.18323618 15:0.58846027 16:−0.34405264 17:−0.27695465
18:0.65253121 19:0.60672343 20:0.33861098 21:0.091746293 22:0.64691567 23:0.077789068
24:−0.15233387 25:−0.070428878 26:−0.12492476 27:0.16136771 28:−0.17302732 29:−0.08467266
30:−0.017847504 31:0.15922767 32:0.065510042 33:0.1898015 34:0.065002568 35:0.083348624
36:0.10817026 37:−0.1359401 38:−0.089988567 39:−0.15030469 40:0.24749298 41:−0.02066797
42:−0.18567494 43:0.13611023 44:0.12971592 45:−0.021920126 46:−0.071041003 47:−0.13607235
48:−0.0084847948 49:−0.026072254 50:0.24444313 51:0.047727257 52:−0.020066252
53:−0.065263309 54:−0.042459652 55:0.085642733 56:−0.045929052 57:−0.0024343606
58:0.20189492 59:0.047381341 60:0.011218852 61:0.052064147 62:0.069976345 63:0.027672198
64:0.0089998841 65:0.007176517 66:0.023605336 67:−0.0078713363 68:−0.079281718
69:0.079008833 70:−0.049468607 71:0.00076955848 72:0.031440981 73:0.027338186
74:−0.022272533 75:−0.0083262511 76:0.0044506392 77:−0.1903552 #
0.014366641566473147 1:2.7063229 2:−4.3506494 3:2.6747077 4:3.3543165 5:−0.98122817
6:−0.00027557678 7:−0.069988109 8:1.2299205 9:1.6373876 10:2.5434656 11:0.68320239
12:0.45858404 13:0.92326808 14:1.5889225 15:0.98421562 16:1.4423897 17:−0.09079019
18:−0.48134744 19:0.60337049 20:−0.25679982 21:−1.0024251 22:0.15910217 23:0.4462733
24:0.93797791 25:0.44708562 26:0.11342644 27:−0.07141047 28:0.57891405 29:−0.50515521
30:0.018945307 31:−0.027702048 32:0.089621477 33:0.30205262 34:0.16768485 35:0.016360011
36:−0.47691005 37:0.13756876 38:0.062321611 39:0.053790733 40:−0.179041 41:0.0024524843
42:−0.19810379 43:−0.1487518 44:−0.035024077 45:−0.10505086 46:−0.24980108 47:0.14106636
48:0.010748983 49:−0.046355259 50:−0.039261274 51:0.12838833 52:−0.063203551
53:0.12648927 54:0.01760811 55:−0.02089154 56:−0.06092719 57:−0.038267009 58:−0.14950337
59:0.070703968 60:−0.0028991671 61:0.0090489089 62:−0.030062821 63:0.0050712796
64:−0.042555124 65:−0.029548682 66:−0.010439664 67:0.016487939 68:−0.014357359
69:0.0021431765 70:0.011924515 71:0.020823456 72:8.720358e−006 73:0.0136911
74:−0.023090824 75:0.026174394 76:−0.0010838493 77:−0.1903552 #
−0.010781108488504399 1:−6.5821438 2:0.44207531 3:−2.1462626 4:1.0547798 5:1.180431
6:1.4029725 7:0.52988899 8:1.5654591 9:−0.61592495 10:−1.9644237 11:−0.093937315
12:1.537237 13:0.74631333 14:1.2931719 15:0.25701022 16:0.30984056 17:0.34933949
18:−0.45785087 19:−0.56797022 20:−0.070442177 21:0.082712539 22:0.045857918 23:0.35205173
24:−0.63843143 25:−0.08995147 26:−0.1490113 27:−0.051159672 28:0.0095642768 29:−0.01881096
30:0.19264689 31:0.58955145 32:0.47912094 33:−0.21832766 34:−0.012995602 35:−0.38962105
36:−0.007694094 37:−0.1083969 38:−0.16571237 39:0.048781171 40:−0.11960279 41:−0.23186709
42:0.26093084 43:0.012867577 44:−0.1993043 45:−0.033703614 46:−0.0021964903 47:0.12650512
48:0.010651867 49:0.005325634 50:−0.15083952 51:−0.058811851 52:0.039342422
53:−0.024097105 54:0.02218624 55:−0.15439974 56:0.0072974195 57:0.020097731 58:−0.019011898
59:−0.15936328 60:0.029539948 61:−0.033148304 62:−0.038484979 63:−0.03436812
64:−0.070527196 65:0.029988054 66:0.011484656 67:0.013905508 68:−0.067535557 69:−0.013315265
70:−0.0010643245 71:−0.004712713 72:0.021191183 73:−0.034550902 74:0.015054468
75:0.025855923 76:−0.00085103378 77:−0.1903552 #
−0.0064500719185770 46 1:−7.1396933 2:1.8141366 3:−1.0988959 4:0.63428104 5:3.6015623
6:0.33900902 7:1.3103291 8:−0.99911022 9:1.7718525 10:−0.37654495 11:0.11989798
12:−1.2986586 13:1.1222512 14:−0.25063059 15:−0.35035196 16:−0.47471485 17:0.64198667
18:0.68408209 19:−0.012710893 20:−0.56399459 21:−0.472859 22:0.44669166 23:0.45747444
24:0.019836549 25:−0.7264502 26:−0.41062954 27:0.28519782 28:0.053799629 29:0.14973909
30:−0.36965817 31:0.46874166 32:−0.24719186 33:0.2803975 34:0.54491574 35:0.057749301
36:0.087263197 37:0.074403256 38:0.017147209 39:0.045216445 40:−0.24199891
41:0.041747771 42:−0.0033461344 43:0.114115 44:−0.05504645 45:0.14623666 46:−0.029156497
47:−0.11827833 48:−0.13301417 49:−0.058891214 50:−0.022062015 51:0.17685284
52:−0.083218463 53:0.15605856 54:0.031951416 55:0.13010892 56:−0.0074879327 57:−0.069543846
58:0.072201841 59:−0.034440085 60:−0.02125741 61:−0.14007521 62:0.063922107
63:−0.04944789 64:−0.027407987 65:−0.12551722 66:0.087008514 67:−0.042747524 68:0.02310768
69:−0.020594098 70:−0.0098113865 71:0.014459817 72:−0.0070923036 73:0.011204379
74:−0.022599053 75:0.0082032057 76:−0.0076469402 77:−0.1903552 #
0.014366641566473147 1:6.2908497 2:4.1322966 3:−2.1402988 4:1.0732908 5:−1.6359258
6:−2.2712736 7:−0.3658264 8:−3.2014685 9:−0.58703798 10:1.7586275 11:−0.016180981
12:−0.80543429 13:−0.24390385 14:0.19850019 15:−0.19716205 16:−0.31815699 17:−1.3209879
18:0.44471249 19:−0.19569649 20:0.39207447 21:0.19244437 22:−0.94942123 23:0.089598015
24:−0.028675204 25:−0.29304734 26:0.33596849 27:−0.088229902 28:0.23498572 29:0.27771956
30:0.46085128 31:0.089999184 32:−0.0040498865 33:−0.27216434 34:0.59970939 35:0.10022689
36:0.38677922 37:−0.016159385 38:0.070385285 39:0.34328794 40:−0.2404328 41:−0.059572238
42:−0.028003925 43:−0.093024634 44:0.06378606 45:−0.10930857 46:0.10696904 47:−0.18512419
48:0.12929681 49:−0.090664178 50:0.079130955 51:0.035923753 52:−0.027161768

APPENDIX C14-continued

| SVM Model Weights (77; Benign/Malignant) |
| --- |
| 53:−0.14822625 54:−0.17606069 55:0.019366128 56:0.08984305 57:−0.022130184 58:−0.10925072 |
| 59:−0.03260535 60:−0.0028966442 61:−0.14856462 62:−0.0053980113 63:−0.0084619354 |
| 64:−0.021957841 65:−0.021800039 66:−0.051191904 67:0.013776741 68:−0.018673051 |
| 69:0.0092330445 70:0.028545 71:0.020084409 72:0.0032020379 73:0.010153247 |
| 74:−0.032292794 75:−0.0086782156 76:−0.015076448 77:−0.1903552 # |
| 0.014366641566473147 1:0.74277186 2:5.3094201 3:−0.90266544 4:−4.392879 5:0.94385374 |
| 6:1.6491483 7:−5.1454759 8:−0.8783679 9:3.2627785 10:−0.17592922 11:−4.3571892 |
| 12:−1.2680314 13:−0.61281353 14:−1.1575962 15:0.92702913 16:−0.42703044 17:0.30480808 |
| 18:−1.3387237 19:1.1718658 20:−1.1734556 21:−1.1047672 22:−0.36465985 23:−0.052361097 |
| 24:−0.82047623 25:−0.081629209 26:−0.19660313 27:−0.32336375 28:−0.82187015 29:−0.37636089 |
| 30:0.052406181 31:0.1556482 32:0.072203808 33:−0.0078984434 34:−0.055886924 |
| 35:−0.20265242 36:0.055475876 37:0.046977337 38:−0.14823741 39:0.043192375 40:−0.0048444876 |
| 41:−0.43768018 42:−0.1286799 43:−0.19737934 44:−0.0035095997 45:0.011283528 46:−0.12269776 |
| 47:−0.095706932 48:−0.051259506 49:0.027083512 50:0.070143729 51:−0.0075751259 |
| 52:0.016429249 53:−0.028202564 54:0.057755399 55:−0.017524499 56:0.0039796107 |
| 57:0.054539118 58:−0.015569714 59:0.032039795 60:0.035917353 61:−0.01511176 |
| 62:−0.033686675 63:−0.0043217978 64:−0.0067565888 65:0.013805195 66:0.0073528215 |
| 67:0.016857086 68:0.02495408669:0.0051584602 70:0.0057484829 71:7.6616372e−005 |
| 72:0.016576555 73:0.0059921751 74:−0.020486955 75:0.0034857427 76:0.001467905 |
| 77:−0.1903552 # |
| −0.014366641566473147 1:4.704782 2:4.4708028 3:5.4821424 4:1.0864891 5:3.0092592 |
| 6:1.2394371 7:0.44467324 8:−0.16809298 9:−0.87816429 10:0.37826821 11:0.36679301 |
| 12:0.64987499 13:0.50997394 14:0.71106732 15:1.148718 16:−1.1566015 17:−0.60356873 |
| 18:−0.46741417 19:−0.66900063 20:−0.40817413 21:0.74780172 22:−0.32083434 23:−0.2291787 |
| 24:0.27775082 25:−0.87772751 26:−0.14774583 27:−0.46033978 28:0.24237972 29:−0.16778204 |
| 30:0.21320681 31:0.22490795 32:−0.50541466 33:0.012952773 34:−0.1328837 35:−0.20605251 |
| 36:0.18054937 37:0.01632726 38:0.26016462 39:0.30838779 40:0.2203185 41:−0.060193397 |
| 42:−0.1302716 43:−0.032657284 44:0.17477033 45:−0.19020715 46:0.030978646 47:0.15805686 |
| 48:−0.3008028 49:−0.11746826 50:−0.13984141 51:0.052750394 52:0.24813499 53:0.056923479 |
| 54:0.24947564 55:−0.075712152 56:−0.14015931 57:−0.041828025 58:−0.010120283 |
| 59:−0.017796254 60:0.076675974 61:0.00077147823 62:0.037313685 63:0.060305409 |
| 64:−0.016602395 65:0.017393747 66:−0.039628614 67:0.015170461 68:−0.025982708 69:0.02636929 |
| 70:−0.0081104748 71:0.0080847898 72:0.01865482 73:0.01061134 74:−0.014607263 |
| 75:−0.0060701752 76:0.0040028333 77:−0.1903552 # |
| −0.014366641566473147 1:4.190671 2:−2.8388617 3:−0.28293976 4:1.3450902 5:1.1610913 |
| 6:1.0457389 7:0.47015584 8:1.1996001 9:−1.1634763 10:0.95336372 11:−0.28979188 |
| 12:−0.056791935 13:1.0745566 14:0.72575712 15:0.047849305 16:1.7926745 17:0.22153218 |
| 18:0.088076927 19:0.80461758 20:−0.16434641 21:−0.90199572 22:0.34939864 23:−0.13511452 |
| 24:0.87443417 25:0.11895354 26:−0.057595495 27:0.16445172 28:0.053267665 29:0.049155794 |
| 30:0.17140107 31:0.090934522 32:0.11897995 33:0.10967227 34:0.12870722 35:0.13593522 |
| 36:−0.096683681 37:0.23736641 38:0.10764614 39:0.057837449 40:0.3695145 41:−0.36495939 |
| 42:0.028184606 43:−0.17032921 44:−0.073785976 45:0.025170946 46:0.11631646 |
| 47:−0.027700469 48:−0.0022308982 49:0.16123548 50:0.11438356 51:−0.16997306 52:0.10984468 |
| 53:−0.16759507 54:0.043375127 55:−0.086561397 56:0.031825058 57:−0.011586461 |
| 58:−0.070100956 59:−0.053697549 60:0.095749013 61:0.07513465 62:0.047453556 63:0.055098392 |
| 64:0.02032843 65:−0.0051878062 66:0.069425777 67:−0.040867504 68:0.016755449 |
| 69:−0.0055938843 70:−0.041808724 71:0.015884569 72:−0.026688019 73:−0.033210773 |
| 74:−0.041081987 75:−0.017149899 76:−0.027208256 77:−0.1903552 # |
| 0.014366641566473147 1:−1.5609734 2:0.64596158 3:−3.4728441 4:0.68456268 5:1.8903604 |
| 6:−0.57183087 7:0.95458591 8:1.1046548 9:−0.22736609 10:0.21243851 11:0.91969186 |
| 12:2.0903215 13:0.2708396 14:−0.56020921 15:0.74677414 16:−0.10647064 17:0.122265 |
| 18:0.24787137 19:1.0061011 20:−0.089977294 21:0.14996117 22:−0.00096745102 23:−0.55471444 |
| 24:−0.096021891 25:0.32503113 26:0.2211071 27:−0.096573055 28:−0.060516793 29:−0.83088976 |
| 30:−0.027305275 31:0.21841365 32:−0.12503985 33:−0.33685756 34:−0.40352473 35:−0.10934868 |
| 36:0.28092706 37:0.28567731 38:0.063681163 39:−0.17342974 40:−0.27239904 41:−0.019435594 |
| 42:−0.075720094 43:0.19086912 44:0.026125593 45:−0.086110532 46:−0.035773154 |
| 47:−0.031632774 48:0.011152843 49:−0.080407046 50:0.073940225 51:0.056417033 52:0.0087056588 |
| 53:0.096971616 54:0.042046681 55:0.083215289 56:0.069479674 57:0.10197006 58:−0.16676334 |
| 59:−0.092506878 60:−0.09343569 61:−0.055613063 62:0.088996112 63:0.044973046 |
| 64:0.096125394 65:0.035325672 66:0.074702755 67:−0.019026468 68:−0.0058201528 |
| 69:−0.041309129 70:−0.0025738482 71:−0.024511622 72:−0.0093103638 73:−0.016113136 |
| 74:0.0073633967 75:−0.022022411 76:0.0036745172 77:−0.1903552 # |
| −0.0040525145575141747 1:−6.6449065 2:−2.282712 3:−2.4150953 4:−2.2591906 5:1.6859276 |
| 6:−2.8092539 7:0.48285982 8:−0.41333944 9:−0.063334018 10:−1.3032 11:1.4590263 12:−1.5313138 |
| 13:−1.1233301 14:0.10162237 15:1.1043637 16:−0.49997714 17:−1.0986657 18:−0.90157825 |
| 19:−0.45812964 20:−0.034549352 21:−0.38758159 22:0.40236655 23:0.045684054 24:0.014210263 |
| 25:0.19888656 26:0.77423567 27:0.19520822 28:−0.26405293 29:−0.36467215 30:0.10524028 |
| 31:0.18252735 32:−0.15923986 33:0.028614478 34:0.09576948 35:−0.030707061 36:−0.2123587 |
| 37:−0.22377011 38:0.19889897 39:−0.061241325 40:−0.052854016 41:0.097108379 42:0.12156319 |
| 43:−0.10981023 44:0.14499992 45:0.069309965 46:0.014019279 47:0.0062036607 |
| 48:−0.091968417 49:0.11810234 50:−0.012317932 51:−0.061848454 52:0.072987631 53:−0.021864718 |
| 54:−0.075722598 55:0.01354252 56:0.0064444882 57:−0.0041144481 58:−0.01219611 |
| 59:0.050113317 60:0.01462376 61:0.0071906112 62:0.0028241191 63:0.025575195 |
| 64:0.0044842055 65:0.0046464358 66:−0.0030049735 67:−0.020367665 68:−0.022384886 |
| 69:−0.027067447 70:−0.016237898 71:−0.022593698 72:−0.0049617314 73:−0.0037826684 |
| 74:−0.0030824076 75:0.0016511997 76:0.00040245449 77:−0.1903552 # |
| −0.014366641566473147 1:−3.4971631 2:−1.4373981 3:−3.5486972 4:−0.62194473 5:1.6161236 |

APPENDIX C14-continued

| SVM Model Weights (77; Benign/Malignant) |
|---|
| 6:−0.027178669 7:−0.51629931 8:0.68608427 9:1.0587066 10:0.80552948 11:−1.4352655 12:1.8818492 13:−0.67903304 14:0.056124352 15:−0.10070574 16:−0.28270194 17:0.21830598 18:0.05567994 19:−0.49747363 20:−0.028172005 21:0.46443018 22:−0.032104645 23:−0.12417424 24:−0.076691642 25:−0.95175922 26:0.52167696 27:0.90511435 28:0.21411046 29:−0.4259755 30:0.021326618 31:−0.36969963 32:0.053920999 33:−0.13018064 34:0.32716259 35:−0.19991131 36:0.0059881387 37:−0.011217886 38:−0.11187682 39:0.14284708 40:0.027452974 41:−0.095972419 42:−0.21434394 43:−0.11379464 44:−0.0076430975 45:0.035183791 46:0.11524788 47:0.081869468 48:−0.072243534 49:0.021867821 50:0.028762316 51:−0.0050135003 52:−0.12027145 53:0.24901767 54:0.00436662 55:0.078267798 56:0.19288915 57:−0.16253689 58:−0.11596265 59:0.072048761 60:0.0051511494 61:0.1264853 62:0.076125003 63:−0.035499763 64:−0.024914192 65:0.021589829 66:0.00051613164 67:0.063145027 68:−0.036208335 69:0.0107712 70:−0.0072495732 71:−0.014571626 72:0.02507004 73:−0.033998802 74:−0.0057655582 75:−0.0095078759 76:−0.0061238692 77:−0.1903552 # |
| 0.014366641566473147 1:6.173727 2:2.8282158 3:3.1301613 4:−4.0596757 5:2.99299 6:0.13083841 7:2.3328772 8:0.0061792424 9:0.36844265 10:−1.2899348 11:−1.1942856 12:0.061436858 13:2.371933 14:−0.47183529 15:−1.1300091 16:0.18724763 17:−0.71200377 18:−1.2737573 19:1.7493371 20:1.7934096 21:0.54696488 22:0.75545412 23:0.77483267 24:0.39566296 25:0.41082302 26:0.75770903 27:−0.3092311 28:−0.093455166 29:0.37355992 30:−0.22538431 31:0.025226178 32:0.08254756 33:0.30007976 34:−0.36880159 35:−0.17150639 36:0.65700364 37:−0.20715316 38:0.04311103 39:−0.10247992 40:−0.33671159 41:−0.010657326 42:−0.096017316 43:−0.30633947 44:−0.12170424 45:−0.030783908 46:0.13194595 47:−0.020452913 48:−0.20795457 49:−0.068616644 50:−0.024035035 51:−0.032993939 52:−0.019023433 53:0.11777727 54:−0.090230547 55:−0.042964306 56:−0.0040088962 57:−0.015205975 58:0.013739965 59:0.058742892 60:−0.0099468315 61:0.020557445 62:−0.013901725 63:0.0076641082 64:−0.026310869 65:−0.0049181166 66:−0.028497333 67:−0.012413738 68:−0.016496982 69:−0.0010147967 70:0.005184711 71:0.0094149588 72:0.020391453 73:−0.012110969 74:−0.0027293467 75:−0.007334129 76:−0.008692502 77:−0.1903552 # |
| 0.010334289452217206 1:5.0015554 2:1.4378881 3:−2.1015527 4:0.11126679 5:3.1057103 6:1.780497 7:2.1279781 8:−0.52761024 9:−0.60034174 10:−1.2132503 11:0.42720383 12:−0.52037889 13:0.98613077 14:−0.024523219 15:0.048410475 16:−0.17936736 17:0.70332491 18:0.87213129 19:−0.66963494 20:−0.01999916 21:0.77973658 22:0.54601568 23:−0.5543291 24:−0.11018224 25:0.065008178 26:0.3398484 27:−0.55713105 28:−0.34951824 29:0.075059287 30:−0.088575356 31:−0.34586453 32:0.036542013 33:−0.11975849 34:0.38404369 35:−0.20971586 36:−0.46208331 37:0.04991401 38:0.043191649 39:−0.2400565 40:0.049733426 41:−0.031727493 42:−0.043869901 43:−0.38088956 44:0.057745401 45:−0.032377336 46:−0.26443592 47:−0.21664576 48:0.029425468 49:−0.085342377 50:−0.1146763 51:−0.00043289945 52:−0.02180106 53:−0.12649117 54:0.078819036 55:0.13521388 56:−0.028971896 57:0.086728446 58:0.040297467 59:0.091649741 60:−0.092029765 61:0.086670779 62:−0.0082465 63:−0.032009091 64:−0.020086894 65:0.033947758 66:−0.042826124 67:−0.0089442572 68:−0.020844089 69:−0.0022399174 70:−0.069170848 71:0.02450109672:0.015599416 73:−0.031837486 74:−0.043966569 75:−0.00057484652 76:−0.0072581773 77:−0.1903552 # |
| −0.014366641566473147 1:2.6174085 2:−1.1758471 3:1.2261158 4:0.90534174 5:−1.3822204 6:0.12877807 7:0.79553342 8:0.51132911 9:0.49562335 10:2.9371469 11:1.2750064 12:−1.1840981 13:−0.50379628 14:−0.60888821 15:1.1613102 16:1.7489086 17:−0.99070257 18:0.17344543 19:0.48421562 20:−0.20357025 21:0.36488065 22:0.76133275 23:0.066091493 24:0.12526777 25:−0.86309922 26:−0.26685229 27:−0.28185117 28:−0.10026424 29:0.14193116 30:−0.25900292 31:−0.14720368 32:0.15766439 33:−0.34314263 34:−0.25792575 35:−0.25448796 36:−0.16320895 37:0.17169294 38:0.015233384 39:0.020087821 40:−0.11782686 41:−0.19679108 42:0.09148369 43:0.1280089 44:0.052688394 45:0.055261444 46:0.16015707 47:−0.10274079 48:−0.015109488 49:0.023824852 50:0.13495883 51:0.01388215 52:−0.00011287264 53:−0.013989956 54:−0.036015671 55:−0.030595511 56:−0.089777477 57:−0.13217676 58:0.1342617 59:0.086803697 60:0.00020764529 61:−0.047097225 62:−0.069971941 63:−0.04822896 64:−0.071194507 65:0.055692255 66:0.013767231 67:−0.010111273 68:0.042377993 69:0.021602603 70:−2.2289745e−005 71:−0.036257643 72:0.062782981 73:−0.03542972 74:0.027682187 75:−0.0017249915 76:0.01139148 77:−0.1903552 # |
| 0.014366641566473147 1:2.3984501 2:−0.44903323 3:−2.2328677 4:−1.5060461 5:−1.2447883 6:1.7488556 7:0.37805492 8:−0.15971586 9:0.55945146 10:1.1581664 11:1.1790388 12:0.2640793 13:−0.99651766 14:−0.82696617 15:0.77283102 16:−0.72430122 17:1.1999093 18:0.59068072 19:0.4818995 20:0.16642293 21:0.7060253 22:0.14077412 23:0.26698935 24:−0.078195229 25:−0.47092012 26:0.15841962 27:−0.44912586 28:−0.1408339 29:−0.047184713 30:−0.20999011 31:−0.048968811 32:−0.051082835 33:−0.12124491 34:−0.05891246 35:−0.0099080261 36:−0.14606763 37:0.0761953 38:0.12003058 39:−7.3863463e−005 40:−0.16116092 41:0.040677059 42:0.017646452 43:−0.12339024 44:0.14436807 45:−0.30605146 46:−0.11680969 47:0.12615523 48:−0.10290959 49:−0.0038098129 50:−0.012469363 51:−0.31059882 52:−0.019162597 53:0.046570752 54:0.12158407 55:−0.13724327 56:0.22004001 57:−0.0048338803 58:0.056504957 59:−0.081610076 60:−0.069799468 61:0.0019261728 62:0.070191063 63:−0.0034936757 64:0.048619747 65:−0.011769674 66:0.026080331 67:−0.020790674 68:0.040379651 69:0.0027824764 70:0.023209935 71:0.011630218 72:0.014290011 73:0.020225827 74:0.0097006401 75:−0.0027107371 76:−0.019847143 77:−0.1903552 # |
| −0.014366641566473147 1:0.57590514 2:−0.89824545 3:−3.4850028 4:−1.9767474 5:2.4076173 6:0.92979175 7:2.2481761 8:0.40167555 9:−0.43368873 10:−0.43588397 11:−0.90713543 12:0.091067724 13:−0.87585449 14:−1.1971608 15:−0.75773376 16:0.51441824 17:0.20861198 18:1.0622408 19:0.37159473 20:0.23171926 21:0.14308375 22:0.60210252 23:0.068566076 24:−0.57222784 25:0.10942147 26:−0.27854782 27:0.51991493 28:−0.51433986 29:−0.40739107 30:0.46257877 31:−0.2238463 32:−0.15679547 33:−0.18137002 34:−0.25734714 35:0.087398142 36:−0.14347418 37:0.12627082 38:−0.22879775 39:0.24043474 40:−0.065976843 41:0.18374315 |

APPENDIX C14-continued

SVM Model Weights
(77; Benign/Malignant)

42:−0.07172206 43:0.016544567 44:−0.11553089 45:−0.22782978 46:0.0052420548 47:0.046977527 48:−0.064951755 49:0.037472285 50:−0.15507902 51:0.084931999 52:0.059432618 53:−0.19153737 54:−0.0096981786 55:0.098025978 56:−0.052280534 57:−0.12945275 58:−0.045181222 59:0.11881341 60:0.00088707323 61:0.016644375 62:−0.19433387 63:0.042121809 64:0.026499785 65:0.032822751 66:0.031225491 67:0.0085996008 68:0.017893994 69:−0.0079808198 70:0.030371858 71:0.016125945 72:−0.00044567406 73:−0.0092807086 74:−0.02004109 75:−0.021153513 76:−0.0032343536 77:−0.1903552 #
−0.014366641566473147 1:0.13555877 2:0.55830449 3:−2.610661 4:−1.6380574 5:3.3411903 6:0.88106918 7:0.76980174 8:−2.057369 9:−1.4988334 10:1.6516935 11:0.082896344 12:−0.45898053 13:0.78678232 14:−0.5470944 15:0.50073922 16:0.49596649 17:−1.5445535 18:0.12557681 19:−0.015690012 20:0.57274175 21:−0.2497953 22:−0.9991526 23:0.66384476 24:0.12585655 25:−0.12649132 26:−0.10282576 27:0.025560282 28:−0.45165968 29:0.31423828 30:−0.60636693 31:0.36806685 32:0.34885982 33:0.056382053 34:−0.12114022 35:0.22517946 36:−0.15177351 37:−0.092980735 38:0.053548697 39:−0.13785522 40:0.39630705 41:−0.072158225 42:0.023994902 43:0.20961669 44:0.084390119 45:−0.13791123 46:−0.0079733981 47:0.058619652 48:0.041597225 49:−0.044118322 50:0.049180005 51:−0.15409614 52:0.098383345 53:0.09384343 54:0.054348782 55:0.081855975 56:−0.03403936 57:0.039721496 58:−0.085251398 59:−0.031053063 60:−0.03909136 61:0.010246024 62:−0.019688906 63:−0.085387491 64:0.025501035 65:0.0087688183 66:0.042845976 67:0.039047725 68:0.0061260075 69:0.049655307 70:0.02186887 71:0.018811064 72:−0.0021942996 73:0.008674412 74:−0.010040212 75:0.0043162475 76:0.0095322626 77:−0.1903552 #
−0.0047494015149194199 1:−0.53360242 2:−2.8293376 3:0.62517828 4:−0.95634866 5:2.6118832 6:1.7751272 7:−0.76521504 8:1.8239453 9:−1.3617073 10:1.5693054 11:−0.54957205 12:2.6936245 13:−0.022518035 14:−0.40931934 15:0.094725579 16:−0.11576901 17:0.36070788 18:0.16496089 19:0.62985134 20:−0.19237439 21:0.23763283 22:−0.60449702 23:0.41005611 24:−0.26639584 25:0.41577983 26:0.18899578 27:0.47817385 28:−0.23111837 29:0.32463366 30:−0.57739949 31:−0.37472859 32:−0.23222451 33:0.24915138 34:0.74287444 35:−0.087792248 36:0.18126452 37:−0.017167022 38:0.31340608 39:0.048930164 40:0.14670014 41:0.16922502 42:0.34691551 43:−0.14075164 44:−0.10883947 45:0.1579659 46:−0.043409564 47:−0.10145523 48:0.010271741 49:0.10023642 50:0.0090193124 51:0.06978628 52:−0.031710476 53:−0.012243288 54:0.088390104 55:−0.070615724 56:−0.061080862 57:0.052077502 58:−0.030478643 59:0.068650708 60:0.098783039 61:−0.031513438 62:−0.014352945 63:−0.083888106 64:0.064698294 65:0.056545585 66:−0.086273871 67:0.0045954711 68:0.024398826 69:−0.0058428962 70:−0.0011099296 71:−0.025138635 72:−0.0098068761 73:0.0084512476 74:0.032842584 75:0.0070314491 76:0.0040651411 77:−0.1903552 #
0.014366641566473147 1:4.7836905 2:0.53860062 3:2.2162826 4:−0.2242374 5:0.31231904 6:2.610328 7:1.5593128 8:2.6654396 9:2.5287607 10:−1.2671609 11:−0.2747694 12:−0.33919075 13:1.2278448 14:−0.54101437 15:−0.79639071 16:0.48781019 17:−0.78502607 18:−0.93683034 19:0.78730911 20:−0.49823233 21:−0.57607204 22:−0.63949859 23:−0.71632129 24:−0.76481539 25:−0.76181108 26:0.47018164 27:−1.0224445 28:−0.068693258 29:−0.097097516 30:0.18545233 31:−0.48076329 32:0.39030236 33:0.11354843 34:0.078346007 35:0.19623169 36:−0.36561352 37:−0.063672714 38:0.45194075 39:0.093162343 40:0.030317577 41:0.44747904 42:0.15167207 43:0.28323579 44:0.20441671 45:0.10920403 46:0.16778319 47:−0.097991414 48:0.14895678 49:0.063386969 50:−0.094128117 51:0.088314369 52:−0.079518691 53:−0.05047331 54:0.013864363 55:0.0045257467 56:−0.0046711829 57:−0.084853277 58:0.012695179 59:−0.10226353 60:0.001139711 61:0.05730648 62:0.039836206 63:−0.035719357 64:0.040135358 65:−0.011941163 66:−0.0091619622 67:−0.012510167 68:−0.040514864 69:−0.0068833171 70:0.0050382377 71:−0.0041605029 72:−0.004189447 73:0.0061618178 74:−0.0047842679 75:−0.012781778 76:0.00043357749 77:−0.1903552 #
0.014366641566473147 1:2.4541152 2:3.0188744 3:−2.4686136 4:0.12672122 5:1.2894068 6:−0.1383266 7:−0.14189628 8:−1.0985004 9:−1.1786238 10:0.61799318 11:0.51109171 12:−0.82191783 13:1.1967033 14:−0.23443411 15:−0.71093911 16:0.50270534 17:−0.046466865 18:0.5528518 19:0.028645031 20:0.30039492 21:−0.42048141 22:−0.59308046 23:−0.36331093 24:0.056975607 25:0.54382831 26:−0.19551364 27:0.024727566 28:−0.10548808 29:−0.45257607 30:−0.21402431 31:−0.71637297 32:0.06268172 33:−0.14598565 34:−0.031840559 35:0.033299975 36:0.20132858 37:−0.26569906 38:−0.22638841 39:−0.24739943 40:0.10289112 41:−0.25182194 42:−0.12410047 43:−0.019026255 44:−0.0062140697 45:0.16524655 46:−0.083975442 47:0.073976398 48:−0.19903968 49:−0.091726005 50:−0.14070809 51:−0.019170346 52:−0.11724126 53:−0.035906505 54:−0.041020863 55:−0.049835451 56:0.0010572489 57:−0.0079945829 58:0.084231794 59:−0.09318424 60:−0.047597118 61:−0.094427727 62:0.13250042 63:−0.049581781 64:−0.027874829 65:0.014409894 66:−0.056331724 67:−0.02455225 68:−0.02946233 69:−0.0039281845 70:0.034948368 71:0.010329608 72:−0.026678858 73:−0.043035869 74:−0.016784739 75:0.0018846078 76:0.033334162 77:−0.1903552 #
0.0067151842453505089 1:3.9931593 2:0.46144915 3:3.9752553 4:2.8675051 5:2.9174421 6:1.5517694 7:−1.9018573 8:−1.4857066 9:−0.21696214 10:−2.3373742 11:1.5848693 12:0.066106856 13:−0.28632095 14:−0.66123843 15:−0.45971406 16:−0.89151531 17:−0.50640154 18:0.52405953 19:−0.077538945 20:0.58767849 21:0.43830243 22:−0.25048077 23:−0.25107831 24:0.11401466 25:−0.53833222 26:−0.26557004 27:0.33480951 28:0.27088299 29:−0.38705727 30:0.46037909 31:−0.35785043 32:0.45249826 33:0.62863505 34:−0.13367048 35:−0.0027479457 36:−0.28388605 37:−0.026834449 38:−0.55147713 39:−0.10118289 40:0.28836411 41:−0.051403724 42:−0.12996191 43:0.1805982 44:0.052310698 45:−0.021809705 46:0.029886335 47:−0.0027280715 48:−0.094091311 49:0.058240123 50:−0.056637499 51:−0.023006644 52:0.13021982 53:0.039354887 54:−0.095587134 55:−0.13634726 56:0.051813148 57:−0.028963935 58:0.031550758 59:0.062448408 60:0.076320656 61:−0.045200523 62:0.016033096 63:−0.00029995857 64:0.036202535 65:−0.016826143 66:0.022840107 67:−0.039392177 68:0.039916258 69:0.022730704 70:0.011044311 71:−0.02430043 72:−0.015622986 73:−0.01333648 74:0.0082701445 75:−0.0023897928 76:−0.015289659 77:−0.1903552 #

APPENDIX C14-continued

SVM Model Weights
(77; Benign/Malignant)

−0.014366641566473147 1:2.4252474 2:1.9030641 3:3.2429667 4:1.6645446 5:0.43997434 6:−0.33349714 7:1.5251236 8:0.37469909 9:1.4284444 10:2.3501792 11:−0.52360725 12:1.0356889 13:−0.59030461 14:−0.31990895 15:0.58108443 16:−0.57536131 17:0.12993556 18:−0.83240747 19:0.98485017 20:−0.51849413 21:0.4714503 22:−0.40052831 23:−0.28888464 24:0.13416073 25:0.65866053 26:0.57009751 27:0.10435195 28:0.6225006 29:−0.033819869 30:0.050417345 31:0.091712862 32:−0.20895889 33:0.17857563 34:−0.016849313 35:0.17562374 36:0.07460954 37:−0.11835361 38:−0.069101758 39:−0.17434591 40:0.065963186 41:−0.28625095 42:−0.1074879 43:0.14319403 44:−0.095079742 45:−0.084315024 46:0.26298091 47:−0.26860633 48:−0.16365243 49:−0.12212769 50:−0.069737017 51:−0.064663894 52:−0.098272793 53:−0.07575421 54:0.05025252 55:0.12865266 56:−0.068790443 57:−0.086706929 58:0.062708013 59:−0.0082359901 60:−0.035684764 61:0.027868286 62:−0.023953471 63:0.0025614628 64:0.030669542 65:0.02365681 66:−0.01461804 67:−0.041607089 68:0.015285047 69:−0.031584051 70:0.035983093 71:−0.040891472 72:−0.002052912 73:−0.012480216 74:−0.04171665 75:0.014764391 76:−0.0053715934 77:−0.1903552 #
−0.014366641566473147 1:−3.9835913 2:1.3548148 3:−4.329277 4:1.8808941 5:2.0825419 6:1.6971016 7:0.61094958 8:−0.63612068 9:0.70078087 10:0.15561295 11:0.14352176 12:0.57568318 13:0.83379358 14:−0.51117545 15:−0.21846972 16:−0.36947227 17:−0.31219101 18:0.51928991 19:−0.051736549 20:−0.39027506 21:0.047608733 22:−0.77814519 23:0.9207924 24:0.55152345 25:−0.51964509 26:−0.065692119 27:0.31813446 28:−0.036801234 29:0.47113785 30:−0.0086826757 31:−0.37791315 32:−0.13320056 33:0.23423246 34:−0.22559656 35:−0.019902119 36:0.012800518 37:−0.34432593 38:−0.05693344 39:0.064957418 40:0.015289573 41:0.047282267 42:−0.0541691 43:0.024579821 44:−0.015012024 45:−0.13309118 46:−0.2940506 47:0.10642475 48:−0.019096067 49:0.22427674 50:−0.0027196105 51:0.076190121 52:−0.1010415 53:0.00039427413 54:−0.004574954 55:0.13244243 56:−0.020592721 57:−0.017341565 58:−0.050946232 59:−0.045786608 60:0.083390094 61:0.064037472 62:−0.11142747 63:0.056944087 64:0.0051629012 65:−0.059854571 66:0.0015431886 67:−0.023980785 68:0.0032361019 69:−0.017300943 70:−0.036379702 71:−0.011547666 72:−0.0093765715 73:0.0033619339 74:0.015212401 75:−0.0026341195 76:−0.0048608324 77:−0.1903552 #
−0.014366641566473147 1:0.41805762 2:−3.5518277 3:0.24840108 4:1.3739471 5:2.2037084 6:0.45562485 7:0.54562068 8:−0.4009451 9:1.2182832 10:1.5885149 11:−0.7462216 12:−0.51569736 13:1.0943168 14:0.18373221 15:−0.42269874 16:−0.55351746 17:−0.21862908 18:−0.048397906 19:−0.41374448 20:−1.6143082 21:0.025760373 22:−0.036253519 23:−0.29692352 24:0.088554904 25:0.03568035 26:0.05083409 27:0.65855187 28:0.15273346 29:0.13874793 30:−0.41406131 31:0.24065006 32:0.35790256 33:−0.27541783 34:−0.20093936 35:0.02086203 36:0.14396261 37:0.21508957 38:0.017639745 39:0.0064149085 40:−0.029681921 41:0.038338833 42:0.15857887 43:0.038537402 44:0.16873474 45:0.13563363 46:0.096420988 47:0.18927839 48:−0.0064920411 49:−0.007665344 50:0.078633651 51:−0.27227512 52:−0.0081789736 53:−0.11949086 54:−0.077733912 55:0.087404408 56:−0.041289832 57:−0.018062003 58:0.069049284 59:0.067457393 60:−0.028683575 61:0.050164901 62:0.02749867 63:0.11888853 64:0.041901831 65:0.018593272 66:−0.061130099 67:−0.069895893 68:−0.068691619 69:−0.031564839 70:0.013365241 71:0.028935777 72:0.048464864 73:0.010140033 74:0.0049944059 75:−0.0035579295 76:−0.01441179 77:−0.1903552 #
0.014366641566473147 1:0.071836069 2:4.8487563 3:−2.215672 4:1.4680905 5:1.5881099 6:−1.1515033 7:−1.7309197 8:−0.62474078 9:0.67348754 10:1.2315838 11:2.4845803 12:0.73117983 13:−0.55354267 14:0.41624168 15:0.14967701 16:−0.93002748 17:1.2698739 18:0.25164443 19:0.87641495 20:−0.25837412 21:0.60393202 22:−0.094112687 23:−0.28065911 24:0.2526139 25:7.3020806e−006 26:−0.27355745 27:−0.62648284 28:−0.11828057 29:−0.093055211 30:0.39523685 31:0.2095781 32:−0.066349164 33:−0.084736906 34:0.048540287 35:0.25495401 36:0.30617094 37:−0.25350019 38:−0.056645337 39:−0.10364208 40:0.1500697 41:−0.12952897 42:0.15536623 43:−0.11613148 44:0.056030773 45:0.058140077 46:0.14535441 47:−0.0041257469 48:0.060678639 49:0.26222914 50:0.075693384 51:0.05206478 52:−0.14737394 53:−0.015263834 54:−0.17092083 55:−0.15869008 56:0.056698009 57:−0.078332327 58:−0.046087775 59:−0.082426272 60:−0.056085609 61:0.14310309 62:−0.11129104 63:0.033211831 64:−0.046493102 65:−0.0012389799 66:−0.090330295 67:−0.011751816 68:0.021484068 69:−0.0039089969 70:−0.0062384787 71:0.0081152841 72:0.0028122338 73:0.01189865 74:−0.023922989 75:0.0080133462 76:0.012590602 77:−0.1903552 #
−0.00097098878199254439 1:−7.8629179 2:0.35588935 3:−3.2571945 4:1.4298542 5:2.5883901 6:−1.2109181 7:1.1168878 8:−1.2686182 9:0.59448105 10:−0.23492582 11:0.47689033 12:1.0362921 13:−0.68728089 14:−0.84360474 15:1.0259857 16:−0.36539716 17:−0.52589875 18:−0.14472322 19:−0.83854824 20:0.17695154 21:−0.37875199 22:−0.37855518 23:−0.29236832 24:−0.080803216 25:0.25815299 26:−0.15769969 27:−0.69742638 28:0.014243821 29:0.29491684 30:0.25353625 31:0.0049112188 32:−0.045539696 33:0.1457891 34:0.23044844 35:−0.059852794 36:−0.041422591 37:0.058332112 38:−0.13023466 39:−0.091972396 40:−0.34557739 41:0.1486261 42:−0.059480567 43:−0.11081138 44:−0.25153852 45:0.095214345 46:0.034388915 47:0.23379555 48:−0.10584597 49:−0.096342869 50:0.2461904 51:0.13306455 52:−0.11081149 53:−0.11220704 54:0.054605138 55:−0.097779348 56:−0.14208321 57:0.034027342 58:0.037161097 59:−0.047887284 60:0.09498816 61:0.022926973 62:0.03572632 63:−0.02616589 64:−0.038750727 65:0.15836343 66:0.053472027 67:0.0013989802 68:0.011960867 69:0.061465014 70:0.0043248981 71:0.03346765 72:−0.013613372 73:−0.010018121 74:0.00352078 75:−0.0049258871 76:−0.017203672 77:−0.1903552 #
0.013221273585262466 1:5.1669812 2:−0.7826243 3:−3.9605892 4:1.3253595 5:−1.4790711 6:−1.2909288 7:−0.80044234 8:−0.96268177 9:−0.56133425 10:0.37993473 11:−0.8294301 12:−0.47396028 13:0.7195524 14:1.0150961 15:−0.1296147 16:−0.27335057 17:0.77942562 18:0.17952375 19:0.25965193 20:0.51637608 21:0.42478666 22:0.19525507 23:−0.26183128 24:−0.14224361 25:0.034262311 26:−0.29506069 27:−0.25205207 28:0.076541848 29:−0.48109576 30:−0.07727392 31:−0.57877499 32:0.072774194 33:−0.13109906 34:−0.077112459 35:0.54374266 36:−0.15675351 37:−0.25240073 38:−0.0051886998 39:0.15258907 40:−0.18908195 41:0.075096577

APPENDIX C14-continued

| SVM Model Weights (77; Benign/Malignant) |
|---|
| 42:−0.063482925 43:−0.058876783 44:−0.10819144 45:0.046947256 46:0.12395314 47:−0.047263294 48:−0.16129072 49:0.092977412 50:0.05710132 51:0.081340611 52:0.13110073 53:−0.075839058 54:0.043540191 55:0.046798505 56:−0.0059874132 57:−0.00095261278 58:0.053829972 59:−0.061308756 60:0.16962966 61:−0.089675106 62:0.064386658 63:0.037622489 64:0.04988924 65:−0.030233009 66:−0.024447449 67:0.068706729 68:−0.040976305 69:−0.017146224 70:−0.0034401352 71:0.015710151 72:0.039232101 73:0.018124171 74:0.020137252 75:0.01042124 76:−0.013101671 77:−0.1903552 # |
| 0.0010318873004164673 1:7.6777558 2:3.9783156 3:1.2148871 4:−1.1086204 5:−0.42434567 6:−2.811646 7:1.2507639 8:−1.8880099 9:0.2223786 10:0.2293808 11:0.082702875 12:0.043921839 13:1.0178206 14:0.67548406 15:−0.95690268 16:−1.5309349 17:0.069053039 18:0.13267767 19:−0.028182082 20:−0.35243601 21:0.11062042 22:0.80002683 23:0.19894904 24:−0.25822869 25:0.074867718 26:0.13480377 27:−0.44678697 28:−0.13302588 29:−0.31133997 30:−0.13965768 31:0.21612936 32:0.35271937 33:−0.12428162 34:0.50838381 35:−0.34227529 36:−0.094497852 37:0.096506245 38:−0.025987651 39:0.1206077 40:0.24829392 41:−0.017972006 42:−0.070537083 43:0.1274723 44:−0.037044499 45:−0.14688157 46:0.073735379 47:0.10197404 48:0.25070587 49:0.015648309 50:0.21576762 51:−0.019399447 52:0.12844208 53:0.10818917 54:−0.074071079 55:0.049050502 56:0.048534248 57:−0.062254943 58:0.034388553 59:−0.026305115 60:0.080062807 61:−0.026788618 62:−0.10811416 63:−0.060700551 64:−0.00517138 65:−0.01044256 66:0.059435513 67:−0.016494369 68:−0.016494785 69:0.004501286 70:−0.051369827 71:0.035912901 72:−0.0080498029 73:−0.027640805 74:0.0088653658 75:0.0094163492 76:0.012057649 77:−0.1903552 # |
| −0.00078516570934819606 1:−5.4016891 2:1.1443474 3:−0.63899267 4:0.77141619 5:−1.6508524 6:1.4980924 7:−0.5484854 8:1.0756733 9:0.1008146 10:−1.2078699 11:−0.45371488 12:0.04054277 13:1.612469 14:0.1403503 15:−0.53547144 16:0.19745356 17:−0.16481647 18:−0.45225912 19:−0.45747712 20:0.32239226 21:0.17449461 22:−0.7646004 23:0.031708159 24:0.49062085 25:0.048556942 26:−0.07016506 27:−0.075387172 28:−0.014282436 29:−0.26092839 30:0.20126009 31:0.35563305 32:0.033744678 33:−0.29097325 34:0.0033193079 35:0.085221402 36:0.11794299 37:−0.010074852 38:−0.22979026 39:0.16008139 40:0.10774241 41:−0.11058783 42:0.044718754 43:0.14429314 44:−0.14242066 45:0.21483551 46:−0.33903289 47:−0.033823095 48:0.011824172 49:−0.020344649 50:0.047974385 51:0.057895344 52:0.030219637 53:0.099586785 54:−0.041239824 55:−0.026610935 56:−0.16724038 57:−0.10697813 58:0.034623049 59:0.0018242775 60:0.0066079842 61:0.026075404 62:−0.075886987 63:0.0096151531 64:0.076930769 65:−0.013767097 66:−0.037970088 67:−0.031908233 68:−0.01621083 69:−0.059769168 70:−0.019708155 71:−0.031927954 72:0.03587161 73:−0.024617024 74:−0.0079870261 75:−0.015681438 76:−0.0036317117 77:−0.1903552 # |
| −9.4045468470319027e−005 1:−6.6449065 2:−2.282712 3:−2.4150953 4:−2.2591906 5:1.6859276 6:−2.8092539 7:0.48285982 8:−0.41333944 9:−0.063334018 10:−1.3032 11:1.4590263 12:−1.5313138 13:−1.1233301 14:0.10162237 15:1.1043637 16:−0.49997714 17:−1.0986657 18:−0.90157825 19:−0.45812964 20:−0.034549352 21:−0.38758159 22:0.40236655 23:0.045684054 24:0.014210263 25:0.19888656 26:0.77423567 27:0.19520822 28:−0.26405293 29:−0.36467215 30:0.10524028 31:0.18252735 32:−0.15923986 33:0.028614478 34:0.09576948 35:−0.030707061 36:−0.2123587 37:−0.22377011 38:0.19889897 39:−0.061241325 40:−0.052854016 41:0.097108379 42:0.12156319 43:−0.10981023 44:0.14499992 45:0.069309965 46:0.014019279 47:0.0062036607 48:−0.091968417 49:0.11810234 50:−0.012317932 51:−0.061848454 52:0.072987631 53:−0.021864718 54:−0.075722598 55:0.01354252 56:0.0064444882 57:−0.0041144481 58:−0.01219611 59:0.050113317 60:0.01462376 61:0.0071906112 62:0.0028241191 63:0.025575195 64:0.0044842055 65:0.0046464358 66:−0.0030049735 67:−0.020367665 68:−0.022384886 69:−0.027067447 70:−0.016237898 71:−0.022593698 72:−0.0049617314 73:−0.0037826684 74:−0.0030824076 75:0.0016511997 76:0.00040245449 77:−0.1903552 # |

APPENDIX C15

| SVM Model Weights (77; Early/Late) |
|---|
| SVM-light Version V6.01 |
| 0 # kernel type |
| 3 # kernel parameter -d |
| 1 # kernel parameter -g |
| 1 # kernel parameter -s |
| 1 # kernel parameter -r |
| empty# kernel parameter -u |
| 77 # highest feature index |
| 59 # number of training documents |
| 46 # number of support vectors plus 1 |
| 0.38319729 # threshold b, each following line is a SV (starting with alpha*y) |
| −0.014768605856240387 1:−0.65310836 2:−5.348166 3:0.42853957 4:−1.999427 5:1.1351154 6:1.1151963 7:2.4849966 8:−0.59107262 9:−0.13457212 10:−0.96609777 11:0.025228789 12:−0.68566889 13:0.051409036 14:0.48685876 15:−0.0077693337 16:0.92148668 17:0.43014637 18:−1.0630491 19:0.089162685 20:−0.0070259096 21:−1.0024557 22:−0.15302616 23:−0.082511447 24:0.20078184 25:−0.127763 26:−0.37109262 27:−0.050487068 28:−0.43910831 29:0.13851134 30:0.3189086 31:0.033191819 32:0.029357022 33:0.33727446 34:−0.050259639 35:0.033500247 36:−0.15786904 37:0.25053495 38:0.12619995 39:−0.10271732 40:0.09438996 41:−0.15584245 42:0.011130134 43:0.042157743 44:0.10351449 45:−0.085660882 46:0.14994901 47:−0.16156676 48:0.084025525 49:−0.046599038 50:0.031094465 51:0.063021466 52:0.037129652 |

APPENDIX C15-continued

SVM Model Weights (77; Early/Late)

53:−0.086593822 54:−0.057121594 55:0.006405904 56:−0.0052837064 57:−0.014566134
58:0.03016793 59:−0.040633935 60:−0.0014767371 61:−0.073092438 62:−0.035074297
63:−0.050672945 64:−0.078871444 65:−0.027396075 66:−0.087323487 67:−0.039443281
68:0.0038563253 69:−0.033224653 70:0.01565117 71:0.004062959 72:0.00027864502
73:−0.064250752 74:−0.042209428 75:0.012480129 76:−0.024839332 77:−0.013282768 #
−0.01006585055889448 1:4.4806499 2:−2.2208855 3:0.44491947 4:−3.0921922 5:0.5878458
6:−1.1640482 7:−3.2640889 8:0.27608919 9:0.6426394 10:0.88536572 11:0.4722378 12:−0.011809029
13:−0.25834092 14:0.83084697 15:−0.22664343 16:−1.6788833 17:0.14575836 18:−0.44980958
19:−0.82005578 20:−0.72094989 21:0.085186571 22:0.26806298 23:0.10388365 24:−0.42588544
25:0.27968955 26:−0.029531002 27:−0.3223868 28:0.26774424 29:0.31059614 30:0.23642597
31:0.16814935 32:0.16386989 33:−0.32911339 34:−0.015648676 35:0.18989152 36:−0.23292686
37:0.17438453 38:0.011391879 39:0.12438626 40:0.22883828 41:−0.11513934 42:0.10112371
43:0.1651936 44:0.0035736097 45:−0.01895446 46:0.14545658 47:0.089143977 48:−0.032650169
49:0.026369104 50:−0.097380094 51:−0.066749953 52:−0.014551019 53:−0.021144031
54:−0.041757647 55:−0.0019819764 56:−0.023537653 57:−0.014566134 58:0.03016793
59:−0.040633935 60:−0.0014767371 61:−0.073092438 62:−0.035074297 63:−0.050672945
64:−0.078871444 65:−0.027396075 66:−0.087323487 67:−0.039443281 68:0.0038563253
69:−0.033224653 70:0.01565117 71:0.004062959 72:0.00027864502 73:−0.064250752
74:−0.042209428 75:0.012480129 76:−0.024839332 77:−0.013282768 #
−0.014768605856240387 1:3.8449099 2:0.82015777 3:0.75213051 4:−0.89598626 5:−1.8081006
6:−1.714511 7:−0.86031747 8:−0.61509097 9:−0.081667982 10:−0.42955077 11:−1.136175
12:−0.42996916 13:1.2497891 14:0.4903751 15:0.27370095 16:0.26355076 17:0.74736363
18:−0.9190014 19:0.37923402 20:0.67191285 21:−0.13239835 22:−0.099515937 23:0.18386172
24:−0.10939878 25:0.14511964 26:0.12438848 27:0.044939578 28:−0.20866533 29:0.073249988
30:0.18016982 31:−0.24617118 32:0.17146967 33:0.045617599 34:0.1377947 35:−0.11894359
36:0.24561043 37:−0.13582173 38:−0.26891324 39:0.24234943 40:0.20000932 41:−0.19306789
42:0.0097727915 43:0.11814802 44:0.040733956 45:0.10349105 46:0.0024360355
47:0.086095296 48:−0.083288044 49:−0.083508104 50:0.094656795 51:−0.0064537991
52:−0.053828355 53:−0.075549617 54:0.092725262 55:−0.033820517 56:0.041074768
57:−0.014566134 58:0.03016793 59:−0.040633935 60:−0.0014767371 61:0.073092438
62:−0.035074297 63:−0.050672945 64:−0.078871444 65:−0.027396075 66:−0.087323487
67:−0.039443281 68:0.0038563253 69:−0.033224653 70:0.01565117 71:0.004062959
72:0.00027864502 73:−0.064250752 74:−0.042209428 75:0.012480129 76:−0.024839332
77:−0.013282768 #
−0.014768605856240387 1:5.3685942 2:−0.47820881 3:2.2096288 4:0.086805686 5:0.92509365
6:0.96576178 7:−1.6370726 8:−0.94032067 9:−0.92654872 10:−0.18881731 11:−2.2293677
12:−1.5757071 13:0.5233506 14:−0.42122918 15:0.010686772 16:0.38972896 17:−0.29049721
18:0.43376783 19:−0.44097713 20:−0.08160463 21:−0.37677664 22:0.32313052 23:−0.02829371
24:−0.15222861 25:0.20831427 26:−0.69393647 27:0.20404333 28:−0.30228293 29:−0.1955826
30:−0.028640801 31:0.25373727 32:−0.0030094788 33:−0.11732018 34:0.31931257 35:−0.24295999
36:0.10356075 37:−0.11915804 38:−0.019241996 39:−0.1277068 40:−0.0089006135
41:0.072798401 42:−0.14244753 43:0.18110909 44:0.12226792 45:−0.074952662 46:0.065850265
47:−0.033298701 48:−0.062168464 49:0.02362605 50:−0.072865129 51:−0.048128903
52:0.057814281 53:0.040432878 54:0.071615376 55:0.067603081 56:−0.054730605
57:−0.014566134 58:0.03016793 59:−0.040633935 60:−0.0014767371 61:−0.073092438
62:−0.035074297 63:−0.050672945 64:−0.078871444 65:−0.027396075 66:−0.087323487
67:−0.039443281 68:0.0038563253 69:−0.033224653 70:0.01565117 71:0.004062959
72:0.00027864502 73:−0.064250752 74:−0.042209428 75:0.012480129 76:−0.024839332
77:−0.013282768 #
0.014768605856240387 1:−0.077000916 2:−0.65690511 3:0.70682311 4:0.44899642 5:0.20025556
6:2.9533093 7:−0.76095641 8:−1.0914356 9:−0.88833517 10:−0.99500358 11:0.31500134
12:−0.72128218 13:−0.25439337 14:0.71312284 15:−0.22867978 16:−1.2032365 17:−0.23490956
18:−0.26707596 19:0.077352114 20:−0.1218089 21:0.30948564 22:−0.15193141 23:0.264375
24:−0.44324213 25:0.065101504 26:−0.23970984 27:0.58251137 28:−0.48237452 29:0.14199354
30:−0.31247333 31:0.27545878 32:−0.19605246 33:0.052668806 34:−0.28584185 35:0.15711239
36:−0.054657675 37:0.23349582 38:−0.10633268 39:0.054383971 40:−0.10407715 41:0.1215646
42:−0.15907861 43:0.023742959 44:−0.18357439 45:0.001640099 46:−0.11134329 47:0.039885283
48:−0.035845477 49:0.12604162 50:−0.014738408 51:0.032484677 52:0.10157229
53:−0.090171278 54:0.030474268 55:−0.039162897 56:0.018851226 57:−0.014566134 58:0.03016793
59:−0.040633935 60:−0.0014767371 61:−0.073092438 62:−0.035074297 63:−0.050672945
64:−0.078871444 65:−0.027396075 66:−0.087323487 67:−0.039443281 68:0.0038563253
69:−0.033224653 70:0.01565117 71:0.004062959 72:0.00027864502 73:−0.064250752
74:−0.042209428 75:0.012480129 76:−0.024839332 77:−0.013282768 #
0.014768605856240387 1:0.24787314 2:2.2118115 3:−0.60001552 4:0.80338144 5:−2.1854589
6:0.70638222 7:0.62249357 8:0.046913408 9:−0.25682223 10:−0.94438338 11:−0.37677273
12:−0.0033340275 13:0.29645291 14:0.50993258 15:−0.10506885 16:0.066127978 17:0.1065586
18:−0.29684845 19:−0.40497857 20:−0.1931008 21:−0.49557588 22:0.62404782 23:−0.019153673
24:−0.41019642 25:0.037920829 26:−0.29895034 27:−0.48646456 28:0.2969861 29:0.056378111
30:0.3302218 31:−0.37453479 32:0.090079531 33:0.23340593 34:−0.21937533 35:0.2326137
36:0.040398028 37:0.091263928 38:−0.003441019 39:−0.15769213 40:−0.121658 41:0.11463366
42:−0.012705397 43:0.099653266 44:−0.086445719 45:−0.1154434 46:−0.10698802 47:0.13379198
48:0.087051667 49:−0.01610915 50:0.16507076 51:−0.054969598 52:0.07258828 53:0.09386944
54:0.012896588 55:0.074432895 56:0.0131929 57:−0.014566134 58:0.03016793 59:−0.040633935
60:−0.0014767371 61:−0.073092438 62:−0.035074297 63:−0.050672945 64:−0.078871444
65:−0.027396075 66:−0.087323487 67:−0.039443281 68:0.0038563253 69:−0.033224653
70:0.01565117 71:0.004062959 72:0.00027864502 73:−0.064250752 74:−0.042209428
75:0.012480129 76:−0.024839332 77:−0.013282768 #
0.014768605856240387 1:5.6168327 2:1.5669624 3:−0.45197037 4:−2.1921811 5:−0.49589536

APPENDIX C15-continued

| SVM Model Weights (77; Early/Late) |
|---|
| 6:1.770943 7:0.39032048 8:−0.10080884 9:−0.66250283 10:0.65875274 11:−0.5540759 12:−0.62766379 13:0.43830335 14:0.44477317 15:−0.60418779 16:−0.1376701 17:0.28505209 18:0.35297057 19:0.009352969 20:−0.39229769 21:0.037468206 22:0.15835048 23:0.19286945 24:0.44310844 25:0.051515713 26:0.16488637 27:−0.12030152 28:0.071811818 29:0.065082066 30:0.21652003 31:0.076822758 32:0.30602899 33:0.28588521 34:−0.047113352 35:0.10323452 36:−0.083651416 37:−0.21129975 38:0.28325024 39:0.11960998 40:−0.093778767 41:0.15820789 42:−0.098587736 43:−0.1435982 44:−0.13214545 45:−0.033870924 46:0.215973 47:−0.11163162 48:−0.041745149 49:0.13097799 50:0.063140586 51:−0.012002639 52:−0.096750885 53:0.050696284 54:0.063137583 55:−0.06494236 56:−0.011568422 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| 0.014768605856240387 1:−0.26241082 2:1.6579612 3:3.0770557 4:0.15776765 5:−2.6405878 6:−1.5567635 7:0.42636272 8:0.58513981 9:−0.43532541 10:−1.4088844 11:−0.8698529 12:−0.038783818 13:−0.49919263 14:0.46379161 15:0.18918391 16:−0.19357842 17:−0.088471793 18:0.84820151 19:−0.2832433 20:0.086896248 21:−0.39720422 22:0.46660823 23:0.80052716 24:0.15751621 25:0.17219071 26:−0.020064544 27:0.090940356 28:0.29443124 29:−0.1133699 30:−0.055924039 31:−0.3201988 32:−0.061599717 33:0.080030225 34:−0.19917509 35:0.05751995 36:−0.5080781 37:−0.087533191 38:0.1574114 39:−0.226944 40:−0.082856387 41:−0.21778023 42:0.12484308 43:−0.044349365 44:0.077502236 45:−0.033442836 46:−0.11322291 47:−0.015083158 48:−0.13500367 49:−0.04017622 50:−0.10604704 51:0.022087807 52:0.0025664188 53:−0.019831514 54:0.066276833 55:−0.0026906775 56:0.039046198 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| 0.014768605856240387 1:−2.0447237 2:−1.4790374 3:−0.79834837 4:−1.9158376 5:−9.1156664 6:1.3769517 7:0.054819442 8:0.57525992 9:−1.2291856 10:0.68747211 11:−0.674815 12:0.24172276 13:0.6525085 14:−0.77808219 15:1.1988282 16:−1.0391495 17:−1.2082939 18:−0.44854626 19:0.65817082 20:−0.20480077 21:−1.007273 22:−0.59606308 23:0.060501587 24:−0.3072401 25:0.11727886 26:−0.2292316 27:0.16723646 28:0.27321938 29:−0.14932795 30:−0.11524441 31:0.18975708 32:−0.068351701 33:−0.081924707 34:0.31203604 35:−0.067111649 36:−0.012156331 37:0.061977576 38:0.15036818 39:−0.13570356 40:0.013062531 41:−0.0069843256 42:−0.01920213 43:−0.033114739 44:−0.17208321 45:−0.01038884 46:−0.00097992341 47:0.090542704 48:−0.0036640796 49:−0.035040211 50:0.03688848 51:0.04290938 52:−0.050542936 53:0.00089523644 54:−0.040883645 55:−0.0076022535 56:−0.019678598 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| −0.014768605856240387 1:−12.115985 2:3.3574667 3:−5.6082969 4:6.0348845 5:−2.5846026 6:−2.4231429 7:2.1448035 8:−1.0462431 9:−0.81006032 10:−0.6556766 11:−1.6614252 12:0.54951715 13:−1.2928978 14:0.624044 15:−0.093003377 16:0.0072963848 17:0.8406083 18:0.41484243 19:−0.27667773 20:−0.64142996 21:0.542301 22:−0.11467434 23:0.52267039 24:−0.64060003 25:0.14220157 26:0.15376514 27:−0.1120628 28:−0.12092109 29:−0.10390776 30:−0.32856432 31:0.053600498 32:−0.15062174 33:0.25416866 34:0.16487227 35:0.060682215 36:−0.029651245 37:−0.054016195 38:0.007319483 39:0.15546499 40:0.14826922 41:−0.095469102 42:−0.0632594 43:0.034099281 44:0.0010096667 45:0.049222551 46:0.14035067 47:0.017545674 48:0.037845816 49:0.0020255249 50:−0.014533123 51:0.015558103 52:−0.018336657 53:−0.00014549297 54:0.0038463818 55:0.018493677 56:−0.051807117 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| −0.014768605856240387 1:−4.7362638 2:5.0725832 3:3.8563914 4:1.7693417 5:−3.1978979 6:2.5992148 7:1.3521872 8:−0.3148208 9:1.5364193 10:−0.57626176 11:−0.76996946 12:0.66269588 13:−0.20945904 14:0.92768914 15:0.56862831 16:0.55525851 17:−0.34076726 18:0.47776577 19:−0.68509734 20:−0.39835602 21:0.36825699 22:−0.35243806 23:−0.0093009686 24:0.51333588 25:−0.19464508 26:0.31672636 27:0.17896943 28:−0.039418597 29:−0.19961922 30:0.26930153 31:−0.054182131 32:0.66182059 33:−0.2252274 34:0.20341577 35:−0.26861903 36:−0.14772312 37:0.15691525 38:−0.234787 39:−0.085837945 40:−0.15817627 41:−0.048807118 42:−0.056145661 43:0.10615161 44:0.020147625 45:0.074007459 46:−0.018481417 47:0.0028096521 48:−0.041066851 49:0.085682787 50:0.074298188 51:−0.07754498 52:0.034548849 53:−0.013288009 54:−0.053365279 55:−0.020237841 56:−0.01113834 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| −0.014768605856240387 1:−7.2030549 2:6.0908909 3:2.4940746 4:−2.6077504 5:−1.5450319 6:0.22979221 7:0.43343803 8:2.418071 9:−1.1402307 10:1.8903451 11:−0.44488525 12:−1.4681929 13:0.11235765 14:1.0160409 15:−0.35620418 16:−0.27526397 17:0.82892871 18:−0.053499669 19:0.19949929 20:1.281533 21:0.38954988 22:−0.43430865 23:−0.18369262 24:0.23353325 25:−0.27844331 26:−0.69236708 27:−0.40184727 28:0.32645166 29:−0.48730356 30:−0.19990201 31:0.35469085 32:0.22125578 33:0.10880098 34:−0.11808318 35:−0.0069064978 36:−0.041870411 37:0.19816157 38:−0.087555312 39:0.061960772 40:0.050315596 41:0.047538649 |

APPENDIX C15-continued

| SVM Model Weights (77; Early/Late) |
|---|
| 42:0.078483492 43:−0.071965918 44:0.12214092 45:0.082257569 46:−0.0043235407 47:0.041519072 48:0.040746868 49:0.036170565 50:−0.037725855 51:−0.031658966 52:0.019285435 53:0.0081537031 54:0.0092561124 55:−0.00068444834 56:−0.0079112137 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| −0.014768605856240387 1:0.096540637 2:8.3863745 3:3.4156289 4:−4.394486 5:−2.2868042 6:0.14741422 7:2.0593071 8:0.95586795 9:3.4924667 10:0.31637564 11:0.98822778 12:−1.0589476 13:−0.84030807 14:0.58004338 15:0.42723122 16:−0.49750289 17:−0.50504965 18:0.28812459 19:0.56755722 20:−0.010826425 21:−0.049219489 22:0.34049734 23:0.19028533 24:−0.72044212 25:−0.44606692 26:0.49522087 27:−0.18126942 28:−0.17162082 29:−0.0084725134 30:0.33620325 31:0.074615106 32:−0.63540918 33:0.1049494 34:−0.072359547 35:−0.15771309 36:0.14471222 37:−0.21167223 38:0.0009002497 39:−0.092798717 40:0.05478812 41:0.11047038 42:0.031474218 43:0.087471657 44:0.01696022 45:0.073114388 46:0.060918879 47:−0.042883351 48:−0.012764937 49:0.027424823 50:−0.01049536 51:−0.050252244 52:0.035564091 53:−0.02164414 54:0.0052753827 55:0.0094552161 56:−0.0065831486 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| −0.014768605856240387 1:−0.29406649 2:4.6958194 3:4.680542 4:2.8435655 5:1.3466616 6:2.4442639 7:−0.061615195 8:−1.2630672 9:0.64168459 10:0.42719305 11:0.69347537 12:0.06210788 13:0.45352629 14:−0.43332359 15:−0.45897284 16:−0.51332062 17:−1.1134859 18:0.8550548 19:−0.64172703 20:0.3340809 21:−0.071920484 22:0.41569284 23:−0.036513343 24:0.38474903 25:−0.36248863 26:0.22788762 27:−0.039216995 28:−0.056603868 29:−0.46988761 30:0.0073228194 31:−0.093437456 32:−0.058081545 33:−0.21862596 34:−0.028792746 35:0.23376 36:−0.020080958 37:0.15610203 38:−0.14672607 39:0.05056297 40:0.18414851 41:0.0061245542 42:0.0098645352 43:0.089854404 44:−0.020155432 45:−0.0012896397 46:0.076192543 47:0.031124093 48:0.042372771 49:−0.021339297 50:0.058650997 51:0.23714806 52:−0.051580954 53:−0.0011094855 54:0.03099867 55:0.014901944 56:−0.023376955 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| 0.014768605856240387 1:6.5694928 2:−0.9918015 3:3.0245953 4:0.64382195 5:1.6382658 6:−1.2099645 7:1.6713234 8:0.92417234 9:−0.59607708 10:−0.45029995 11:−0.51093268 12:0.14917231 13:−0.55258936 14:−1.5116889 15:−0.83285594 16:−0.96993989 17:0.15678959 18:0.32795009 19:0.028230233 20:0.053290673 21:−0.1397406 22:0.52616757 23:0.35810533 24:0.34629941 25:0.35620835 26:0.1471872 27:−0.16251567 28:0.11963402 29:−0.31834462 30:0.2477843 31:0.25255367 32:0.16635247 33:0.28993076 34:0.08024355 35:0.069850117 36:0.41768873 37:−0.060612235 38:0.084460989 39:0.048846893 40:0.0041252817 41:−0.2789861 42:−0.11791462 43:0.011570881 44:−0.046245933 45:0.1165259 46:−0.15123972 47:0.019106131 48:−0.0093186004 49:0.11935298 50:−0.044293307 51:0.00059594237 52:0.015253385 53:−0.029178897 54:−0.087228395 55:0.012629295 56:−0.011310181 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| 0.014768605856240387 1:−4.535821 2:−6.2433324 3:1.0493795 4:0.26412264 5:−2.1470416 6:−0.062359922 7:0.81726098 8:−0.064266913 9:−0.54053438 10:0.67009544 11:1.3543564 12:−0.63338661 13:0.12414087 14:0.33524087 15:0.050753459 16:−0.48658836 17:−1.5697033 18:−0.62426043 19:−0.14954308 20:−0.39699316 21:0.837672 22:−0.10908876 23:0.22141476 24:−0.02783216 25:0.086731285 26:−0.057393599 27:−0.4050988 28:−0.26424235 29:−0.44483185 30:−0.066056818 31:−0.46193358 32:0.085995346 33:−0.13867034 34:−0.090585083 35:−0.028534878 36:0.26227674 37:0.041619673 38:0.21850741 39:0.27431187 40:−0.20669624 41:−0.024783127 42:−0.13044158 43:0.029847413 44:0.2042821 45:−0.13040836 46:−0.012395084 47:−0.028467173 48:−0.064102955 49:−0.060277648 50:−0.033647578 51:−0.043939281 52:−0.012290573 53:−0.05316757 54:0.0097566871 55:−0.024945162 56:−0.0099840248 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| 0.014768605856240387 1:3.2546492 2:0.7044822 3:4.8429718 4:−0.086358212 5:2.0222189 6:1.7212237 7:1.1669612 8:−0.16773781 9:−0.47545147 10:0.012496617 11:−0.66409051 12:0.036561217 13:0.60627586 14:0.11498853 15:−0.12351964 16:−0.15679719 17:−0.093521841 18:−0.57795966 19:1.2486501 20:−0.56176507 21:0.50748724 22:−0.26209134 23:0.4902505 24:−0.010827732 25:0.4338606 26:0.17241924 27:0.12431052 28:−0.097320065 29:0.3177141 30:0.050298363 31:−0.17094809 32:0.03880363 33:−0.080632523 34:−0.18678777 35:−0.072257422 36:−0.029369868 37:0.2831431 38:0.074070945 39:0.086522527 40:0.1195867 41:0.038305368 42:0.010444178 43:−0.18119197 44:0.035364725 45:0.22725376 46:0.00163284 47:−0.006487187 48:−0.11214574 49:−0.12168349 50:−0.012479606 51:0.032947872 52:0.046790071 53:0.11123197 54:−0.0029186639 55:0.046970371 56:−0.051210601 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 |

APPENDIX C15-continued

SVM Model Weights (77; Early/Late)

72:0.00027864502 73:−0.064250752 74:−0.042209428 75:0.012480129 76:−0.024839332
77:−0.013282768 #
−0.014768605856240387 1:2.9727399 2:−3.6812067 3:1.6084788 4:−0.70432025 5:−4.1466174
6:1.214857 7:1.503695 8:0.45501497 9:−1.48816 10:−1.2299246 11:−0.67039973 12:−0.0013176852
13:0.5072068 14:−0.26718497 15:−0.49739206 16:0.12478317 17:0.73601609 18:0.22479108
19:−0.077745788 20:0.11766382 21:−0.050217405 22:−0.3962242 23:−0.24287438 24:0.20062862
25:−0.33630544 26:0.51604027 27:−0.20637876 28:0.33258221 29:0.68672246 30:−0.17163275
31:0.066262692 32:−0.45868894 33:−0.43544823 34:−0.040764436 35:0.0778502 36:0.29099873
37:0.089215674 38:−0.18534599 39:0.097193591 40:−0.10535464 41:−0.15558843 42:0.052791938
43:−0.022380995 44:0.095813848 45:−0.14693359 46:0.010108676 47:−0.067653626
48:0.06319426 49:0.069736734 50:−0.077035122 51:0.017272346 52:0.0026871073
53:0.048154164 54:0.033091038 55:−0.010559261 56:−0.015412796 57:−0.014566134
58:0.03016793 59:−0.040633935 60:−0.0014767371 61:−0.073092438 62:−0.035074297
63:−0.050672945 64:−0.078871444 65:−0.027396075 66:−0.087323487 67:−0.039443281
68:0.0038563253 69:−0.033224653 70:0.01565117 71:0.004062959 72:0.00027864502
73:−0.064250752 74:−0.042209428 75:0.012480129 76:−0.024839332 77:−0.013282768 #
−0.0025671653763623195 1:0.58741909 2:0.21974246 3:−0.6829626 4:3.4215374 5:1.1128082
6:−1.0766947 7:−0.51366031 8:−1.2978395 9:0.076142274 10:−1.7031164 11:1.4764253
12:−1.4646332 13:−0.45863831 14:1.802916 15:1.436672 16:−0.17571683 17:0.88386679
18:−0.28668973 19:−0.33140075 20:−0.19797878 21:−0.51897645 22:0.11357965 23:0.10134315
24:0.67155087 25:0.020734437 26:−0.20282786 27:−0.11464946 28:−0.26476386 29:−0.3228538
30:0.16799039 31:0.29011804 32:−0.25893149 33:−0.27815971 34:−0.19903478 35:−0.046062496
36:0.21216051 37:−0.018611833 38:−0.040653367 39:−0.14418592 40:−0.21231849
41:−0.059553914 42:0.014177838 43:−0.1162122 44:−0.072207756 45:0.056487262 46:0.04570882
47:0.14483447 48:−0.022110581 49:−0.07172855 50:−0.015396543 51:−0.030337607
52:−0.088083982 53:0.050440993 54:−0.025054006 55:−0.0079029994 56:−0.029021565
57:−0.014566134 58:0.03016793 59:−0.040633935 60:−0.0014767371 61:−0.073092438
62:−0.035074297 63:−0.050672945 64:−0.078871444 65:−0.027396075 66:−0.087323487
67:−0.039443281 68:0.0038563253 69:−0.033224653 70:0.01565117 71:0.004062959
72:0.00027864502 73:−0.064250752 74:−0.042209428 75:0.012480129 76:−0.024839332
77:−0.013282768 #
−0.0079775811569909767 1:4.5022511 2:−3.3845196 3:1.2118824 4:3.4120405 5:−0.094564781
6:−3.0915475 7:1.1569571 8:0.29987872 9:1.4580578 10:1.3611175 11:−0.56343496 12:−0.48917189
13:−0.39502534 14:−1.6226932 15:0.14347057 16:−0.64657885 17:0.13600728 18:−0.056554936
19:−0.55161893 20:0.12115271 21:0.11907019 22:−0.46877593 23:−0.085623056 24:−0.10240813
25:−0.63174194 26:−0.17959622 27:0.18745661 28:−0.12787168 29:0.21938048 30:−0.060862392
31:−0.032182917 32:0.1045638 33:0.10238792 34:−0.1977746 35:−0.021306232 36:−0.012299137
37:0.051979739 38:0.0089666191 39:−0.057752561 40:−0.055637997 41:0.01841332
42:0.0065761753 43:−0.023473274 44:−0.021785023 45:−0.014187905 46:0.056018978
47:0.059127633 48:−0.030585418 49:−0.042008013 50:0.017881911 51:−0.027380561
52:−0.010880641 53:0.0063928105 54:0.0094562173 55:0.0059765009 56:−0.00032366585
57:−0.014566134 58:0.03016793 59:−0.040633935 60:−0.0014767371 61:−0.073092438
62:−0.035074297 63:−0.050672945 64:−0.078871444 65:−0.027396075 66:−0.087323487
67:−0.039443281 68:0.0038563253 69:−0.033224653 70:0.01565117 71:0.004062959
72:0.00027864502 73:−0.064250752 74:−0.042209428 75:0.012480129 76:−0.024839332
77:−0.013282768 #
0.014768605856240387 1:−5.6188436 2:6.4116511 3:1.1475894 4:0.30436778 5:−2.0987704
6:1.5397984 7:−0.66749644 8:0.82414472 9:2.2661541 10:0.65989417 11:−0.3601563
12:0.97567695 13:−0.40448508 14:−0.39460355 15:0.41299406 16:0.61194468 17:0.43778253
18:−0.58751857 19:0.17369807 20:0.30362067 21:0.57112336 22:0.68445641 23:−0.56161636
24:0.63229144 25:0.53442299 26:−0.10506993 27:0.20146386 28:−0.2933456 29:0.49201888
30:−0.11767609 31:0.18337381 32:0.035612956 33:−0.17835179 34:−0.16667995 35:−0.016307712
36:0.10074685 37:−0.084197767 38:0.45726457 39:−0.042835277 40:0.1335838 41:−0.077233575
42:−0.071578376 43:−0.037783708 44:0.02196789 45:−0.12824205 46:−0.034900561
47:0.15386349 48:0.038040843 49:0.018542018 50:0.0043145288 51:0.015334957
52:−0.017541217 53:−0.045332495 54:0.029964233 55:0.033415813 56:−0.012655052
57:−0.014566134 58:0.03016793 59:−0.040633935 60:−0.0014767371 61:−0.073092438
62:−0.035074297 63:−0.050672945 64:−0.078871444 65:−0.027396075 66:−0.087323487
67:−0.039443281 68:0.0038563253 69:−0.033224653 70:0.01565117 71:0.004062959
72:0.00027864502 73:−0.064250752 74:−0.042209428 75:0.012480129 76:−0.024839332
77:−0.013282768 #
0.013477354074154678 1:−5.2925487 2:4.2979608 3:4.5720906 4:2.1898043 5:2.3349657
6:2.2912428 7:−0.58504182 8:−2.3732283 9:−0.2128852 10:0.85969615 11:0.15550362
12:−0.09981852 13:1.3295355 14:−0.37502661 15:0.72359103 16:−0.55721235 17:−0.40275583
18:−0.34295154 19:−0.84398103 20:0.66835731 21:−0.12873596 22:−0.2934854 23:−0.4840734
24:−0.49341753 25:0.76310962 26:0.31817666 27:−0.21882786 28:−0.10855637 29:0.11039914
30:−0.033242755 31:−0.23728813 32:−0.039123524 33:0.29011539 34:0.078500129 35:0.047723014
36:−0.0057103303 37:−0.21661714 38:−0.18419161 39:−0.10812484 40:0.0351284 41:−0.07000263
42:−0.015714483 43:−0.2640931 44:−0.026062164 45:−0.078878753 46:0.063261077
47:−0.0027664467 48:0.035810512 49:−0.0005976361 50:−0.10158946 51:−0.065962806
52:0.033374764 53:0.026964182 54:−0.038348094 55:−0.0096357539 56:0.024983775
57:−0.014566134 58:0.03016793 59:−0.040633935 60:−0.0014767371 61:−0.073092438
62:−0.035074297 63:−0.050672945 64:−0.078871444 65:−0.027396075 66:−0.087323487
67:−0.039443281 68:0.0038563253 69:−0.033224653 70:0.01565117 71:0.004062959
72:0.00027864502 73:−0.064250752 74:−0.042209428 75:0.012480129 76:−0.024839332
77:−0.013282768 #
0.014641439768243702 1:−9.6365938 2:0.27457154 3:0.24511299 4:−8.806778 5:0.6232543
6:−4.0140376 7:0.35930777 8:−2.5010431 9:0.36475748 10:−1.5022405 11:0.80284512 12:0.32545814

APPENDIX C15-continued

| SVM Model Weights (77; Early/Late) |
|---|
| 13:1.8913225 14:−0.93951827 15:0.38224173 16:−0.65709311 17:0.79791272 18:1.4994164 19:−0.26922241 20:−0.61654657 21:0.27758244 22:−0.08719743 23:−0.45593926 24:−0.1579437 25:0.19465989 26:−0.1421714 27:0.3423577 28:0.1200323 29:−0.0461821 30:−0.041267462 31:0.16024265 32:0.18277849 33:0.0064786077 34:−0.17402908 35:−0.066605046 36:0.13273093 37:0.064577535 38:0.031130802 39:0.024264136 40:−0.046962377 41:0.04452312 42:−5.3410531e−005 43:0.0017418667 44:0.033173565 45:0.011735925 46:−0.013195354 47:−0.046941463 48:−0.0029782543 49:−0.054463185 50:0.040772278 51:0.014879184 52:−0.032027137 53:−0.010012796 54:−0.0055688596 55:0.027304681 56:0.0097074239 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| 0.014768605856240387 1:−1.3473827 2:3.1749876 3:0.33612096 4:−0.48257682 5:−1.2504317 6:−0.3746272 7:−0.97711682 8:0.36629584 9:0.42225072 10:−0.87012446 11:−1.3887079 12:−0.17443076 13:−0.63309127 14:−0.56010276 15:−0.97693753 16:0.2054854 17:−0.034835823 18:−0.60930669 19:0.55255508 20:−0.051984124 21:0.78292656 22:0.78915751 23:0.21095176 24:0.055755083 25:0.08986932 26:−0.58408558 27:0.26925716 28:0.17020075 29:0.024584724 30:−0.043956187 31:−0.17800522 32:−0.071832761 33:−0.049348541 34:−0.10818942 35:0.16174453 36:0.079413682 37:−0.068239592 38:−0.29155758 39:−0.24701957 40:0.070737563 41:0.12238424 42:−0.13047846 43:0.10185836 44:0.01063423 45:−0.085103258 46:0.0078688981 47:−0.093020134 48:0.019335762 49:−0.12000392 50:−0.014228066 51:−0.014401478 52:−0.069268577 53:0.058600646 54:−0.087185673 55:−0.077739663 56:0.01341001 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| −0.014768605856240387 1:−3.9257259 2:3.698391 3:−1.2225096 4:−1.8593814 5:1.8608211 6:0.024244072 7:0.53273588 8:2.3171523 9:−0.10357498 10:−1.7701248 11:−0.09135022 12:−0.21410269 13:−0.56344688 14:−0.66677988 15:−0.074229777 16:−0.7781347 17:−0.58641875 18:−0.85176563 19:−0.5967322 20:0.53452975 21:0.19298361 22:0.13876431 23:0.20945406 24:0.47848332 25:−0.07573083 26:0.050581589 27:−0.078272372 28:0.037856128 29:0.2291767 30:0.0060161958 31:0.21042997 32:−0.010838528 33:−0.14502713 34:0.23592713 35:0.037833735 36:−0.18864188 37:−0.089426085 38:−0.13909236 39:0.25986913 40:−0.17642805 41:0.071576953 42:−0.07276547 43:−0.073846363 44:−0.2119693 45:0.022859307 46:0.016941356 47:−0.14853767 48:−0.0012183208 49:−0.14155316 50:−0.039153576 51:−0.040122896 52:−0.03687349 53:−0.069212034 54:0.016068714 55:0.086911023 56:−0.01319702 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| −0.014768605856240387 1:−6.0980892 2:−1.0850385 3:2.0846567 4:−1.4054723 5:2.2404287 6:0.75962156 7:−1.1134288 8:−0.08726088 9:−0.66311955 10:0.92700869 11:0.3143186 12:−0.49236116 13:0.90752244 14:0.40693727 15:−0.52368402 16:1.87501 17:−0.13043843 18:0.45364773 19:−0.50842732 20:0.16376778 21:−0.84742779 22:−0.065857552 23:0.88092017 24:0.0047743851 25:−0.7591399 26:0.38342622 27:0.046178523 28:0.17391978 29:0.36568406 30:−0.27302399 31:0.14382108 32:−0.11714852 33:0.12493263 34:−0.029038981 35:0.12052096 36:0.025696972 37:−0.043619167 38:0.096240617 39:0.11489102 40:0.12612812 41:0.10013232 42:−0.22702998 43:0.015141307 44:0.027380209 45:−0.01563058 46:−0.080043927 47:0.13000801 48:−0.12468407 49:−0.052289303 50:−0.016171705 51:−0.057180777 52:−0.048039556 53:−0.021364527 54:−0.06559214 55:0.0042922604 56:−0.016975969 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| −0.013739571789945696 1:−1.020308 2:6.5098257 3:−2.8737273 4:−0.1482313 5:2.3769107 6:−1.3385624 7:−2.4423466 8:−0.75408256 9:−0.47787622 10:0.2469745 11:−1.6656125 12:−0.62086529 13:−0.87640029 14:0.026346527 15:0.69555312 16:−0.0046009663 17:0.17967734 18:0.0062626856 19:−0.19102003 20:−0.44714066 21:−0.08058735 22:−0.56100452 23:0.24382098 24:0.18025596 25:−0.54790342 26:0.25716394 27:−0.16357571 28:−0.068810306 29:−0.2107641 30:0.15291901 31:−0.3577539 32:0.066856675 33:−0.30352947 34:0.16728601 35:0.1388651 36:0.29691589 37:0.24600162 38:0.25199899 39:−0.16875139 40:0.2384049 41:0.085038282 42:0.069243245 43:−0.12284064 44:−0.10078648 45:−0.037202626 46:−0.13449219 47:−0.15341036 48:0.046415254 49:0.010412896 50:−0.0069145584 51:−0.055796135 52:0.034799594 53:−0.025895426 54:0.022249367 55:7.5035037e−005 56:0.019897034 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| 0.014768605856240387 1:2.3002515 2:−5.0593381 3:0.54767525 4:−2.9095581 5:0.98575395 6:1.9630213 7:2.0666449 8:1.2305194 9:−1.2333636 10:1.1164197 11:0.31560028 12:−0.47594446 13:−1.5713885 14:0.94593561 15:−1.8614486 16:−0.26043862 17:0.58758771 18:−0.30997801 19:−0.90507549 20:−0.49837983 21:−0.29337564 22:−0.019367304 23:−0.33875957 24:−0.25235397 25:0.41066533 26:0.46689358 27:0.37681949 28:−0.094368756 29:−0.11137647 30:−0.30413687 31:−0.20462647 32:0.1027085 33:−0.17236865 34:0.18909617 35:−0.17418689 36:0.044706777 37:−0.096377693 38:0.038265664 39:−0.19311012 40:−0.008894789 41:0.13968413 42:0.0023501345 43:−0.011663033 44:0.056738887 45:0.10731428 46:−0.029556768 47:0.095513813 48:0.10409889 49:−0.062358104 50:0.020479832 51:0.014795416 |

APPENDIX C15-continued

| SVM Model Weights (77; Early/Late) |
| --- |

52:−0.056928173 53:−0.0021657464 54:0.011391768 55:0.026436429 56:0.05041568 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 #
−0.01224875347912743 1:0.30034208 2:−13.185742 3:0.081876874 4:−3.7991996 5:−1.8780092 6:3.5160737 7:−0.94013929 8:−0.94617838 9:−0.27504939 10:−0.1651682 11:−0.71633869 12:−0.24563058 13:−1.9614851 14:−0.40932882 15:1.8745868 16:1.0892484 17:0.29633203 18:0.65594947 19:0.0063731247 20:0.71223193 21:0.62679762 22:0.29002333 23:−0.6032474 24:−0.29016757 25:−0.19256842 26:0.1658884 27:−0.38402793 28:−0.29119509 29:−0.11247938 30:−0.033956025 31:−0.16849281 32:0.12737986 33:0.085531183 34:−0.13917033 35:0.036728151 36:−0.085652046 37:0.0034151315 38:−0.0064458023 39:0.07616502 40:0.057866748 41:−0.014705238 42:−0.004217694 43:0.082839757 44:−0.15087615 45:0.097751535 46:−0.044490345 47:−0.029348498 48:−0.033241108 49:0.0076492429 50:−0.077628687 51:0.011266585 52:−0.056414507 53:0.041344281 54:−0.018628659 55:0.023536228 56:−0.0067367326 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 #
0.014768605856240387 1:−5.6853518 2:6.2901158 3:−3.0175521 4:−1.1817129 5:4.6835108 6:0.50484461 7:0.14681561 8:−1.3797671 9:−1.3517046 10:0.87066114 11:−0.88172358 12:−0.82099658 13:−0.76520211 14:−1.3353437 15:0.45342293 16:−1.1483836 17:0.33313045 18:−0.7127254 19:0.37462318 20:−0.1366715 21:−0.55971849 22:0.32470939 23:−0.70213532 24:0.4246127 25:0.048656423 26:0.26856175 27:−0.38836086 28:0.037722096 29:0.26388341 30:−0.20854987 31:−0.29223597 32:−0.26820263 33:0.15424132 34:0.092860669 35:−0.14960667 36:−0.16632728 37:0.10264548 38:−0.0045762295 39:0.023715394 40:−0.18364209 41:0.056556012 42:0.082629576 43:0.20693606 44:0.098953694 45:0.038900699 46:−0.082065903 47:0.049894445 48:−0.10811994 49:0.046247464 50:0.049693342 51:0.012209838 52:−0.040875122 53:−0.0063443375 54:−0.0037968659 55:−0.038403396 56:−0.043268446 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 #
0.014768605856240387 1:−4.6791801 2:0.78113121 3:0.13722843 4:−1.4573936 5:−0.044365235 6:0.63921291 7:0.32270318 8:2.1303132 9:1.638996 10:0.56357241 11:2.208235 12:−0.234688 13:0.84915978 14:−1.5852739 15:−0.64974546 16:1.6790665 17:0.35662487 18:−0.1828884 19:0.08293552 20:−0.94816458 21:−0.31924927 22:0.1488418 23:−0.050127678 24:0.078796797 25:0.1085161 26:−0.19090131 27:−0.062958963 28:−0.23495914 29:−0.25450927 30:−0.26171795 31:−0.27125272 32:0.02822292 33:0.03517982 34:0.16578729 35:0.23242944 36:−0.0078806393 37:0.15218525 38:−0.13090901 39:−0.078388035 40:−0.066740684 41:−0.16554637 42:0.065331116 43:0.046006314 44:−0.19082423 45:0.082093947 46:0.021275984 47:0.036134418 48:0.019454703 49:0.0090725953 50:−0.091675192 51:−0.078451097 52:0.029702039 53:0.019248934 54:0.070125498 55:−0.031442273 56:−0.043421477 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 #
−0.014768605856240387 1:−2.6635654 2:−2.5594325 3:0.79235649 4:−1.4335438 5:2.9728413 6:0.2401166 7:1.0045772 8:1.1049131 9:−0.19391535 10:−0.23061828 11:−0.16879354 12:0.43403283 13:0.32028562 14:0.56603378 15:1.0433983 16:0.35972649 17:−0.056434259 18:−1.229013 19:−0.2553665 20:−0.10149775 21:0.57615173 22:0.43380129 23:−0.11034885 24:−0.50578207 25:−0.48187286 26:−0.29516444 27:0.54367858 28:0.19389133 29:−0.10500043 30:−0.099321276 31:−0.076419376 32:−0.055130955 33:−0.08522179 34:0.27519456 35:0.38544014 36:0.1334053 37:−0.13509947 38:−0.035015505 39:−0.094240837 40:−0.066309981 41:−0.071935475 42:0.17902936 43:−0.11800994 44:0.078383185 45:0.00014991207 46:0.041125625 47:0.0019472472 48:−0.17139809 49:0.16191401 50:0.10203282 51:0.03084469 52:−0.02912846 53:0.001344858 54:−0.017806103 55:0.043754775 56:−0.0068575386 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 #
0.014768605856240387 1:−1.7091048 2:−2.3088918 3:−0.060525764 4:1.1886284 5:2.9403498 6:1.381649 7:−1.9297744 8:−0.96428585 9:−1.315801 10:−2.1206195 11:0.67145276 12:−0.87646168 13:−0.12796399 14:−0.20867974 15:−1.1594797 16:0.24745041 17:−1.0376993 18:0.06815052 19:0.93588173 20:0.02648079 21:0.81365234 22:−0.091791868 23:0.07513044 24:−0.31452876 25:−0.39676839 26:0.20552292 27:−0.47124872 28:0.42987451 29:0.18325602 30:−0.17282228 31:0.1850965 32:0.27005395 33:0.13367508 34:−0.083268814 35:−0.22522841 36:0.075817481 37:−0.059406348 38:0.064165525 39:−0.35860172 40:−0.049105324 41:−0.13144413 42:0.12214988 43:0.013718169 44:−0.081037447 45:−0.02066524 46:0.099034026 47:0.10799399 48:0.04014821 49:−0.017932789 50:0.068594635 51:−0.028148869 52:0.0034427256 53:−0.062456384 54:0.026820326 55:0.020401014 56:−0.017075414 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332

APPENDIX C15-continued

| SVM Model Weights (77; Early/Late) |
|---|
| 77:−0.013282768 # |
| 0.014768605856240387 1:−1.7641799 2:−0.72998393 3:3.7503579 4:3.6581409 5:1.5805999 |
| 6:1.2611278 7:−0.1659939 8:0.86638123 9:−0.087680019 10:0.38896546 11:−1.2237482 |
| 12:1.3268176 13:−0.53214759 14:0.49957219 15:−0.98321253 16:0.66870946 17:−0.18509261 |
| 18:1.2336695 19:0.26198012 20:0.094865032 21:−0.17118673 22:−0.75227773 23:−0.79626405 |
| 24:−0.3319149 25:0.63394278 26:−0.40572572 27:0.050915536 28:0.12359164 29:0.035770986 |
| 30:0.51408178 31:0.010153062 32:−0.36177 33:0.011026179 34:−0.032930013 35:0.23617467 |
| 36:0.13869071 37:0.14955208 38:0.047729734 39:0.020341545 40:−0.13939571 41:0.096790649 |
| 42:0.12033851 43:0.048224244 44:−0.041510247 45:0.028498573 46:0.0083965296 |
| 47:−0.011716274 48:−0.094036303 49:−0.054714281 50:0.0099876439 51:−0.069893815 |
| 52:−0.090383455 53:−0.095715314 54:0.0068338872 55:0.0023848051 56:−0.020483032 |
| 57:−0.014566134 58:0.03016793 59:−0.040633935 60:−0.0014767371 61:−0.073092438 |
| 62:−0.035074297 63:−0.050672945 64:−0.078871444 65:−0.027396075 66:−0.087323487 |
| 67:−0.039443281 68:0.0038563253 69:−0.033224653 70:0.01565117 71:0.004062959 |
| 72:0.00027864502 73:−0.064250752 74:−0.042209428 75:0.012480129 76:−0.024839332 |
| 77:−0.013282768 # |
| 0.014768605856240387 1:−0.48986632 2:2.3641047 3:2.6310048 4:−1.5145593 5:−1.2962941 |
| 6:−4.5887156 7:−2.5533996 8:1.1677703 9:−1.4933351 10:−0.60078549 11:1.321355 12:−0.57562864 |
| 13:−0.43234751 14:0.61008942 15:−1.3298372 16:−0.13002224 17:0.050613306 18:0.43624872 |
| 19:0.46657923 20:0.171919 21:0.38072646 22:−0.61176062 23:−0.58417058 24:−0.048312832 |
| 25:−0.34663108 26:−0.13875028 27:0.059226148 28:−0.70871294 29:0.17817952 30:0.36236092 |
| 31:−0.34025535 32:−0.12339502 33:0.047481224 34:0.32950503 35:−0.019215636 36:−0.26156458 |
| 37:−0.14126162 38:0.013912342 39:0.04458563 40:−0.016974293 41:−0.11169823 42:−0.09321177 |
| 43:−0.07442686 44:−0.029472621 45:−0.078103438 46:−0.083885163 47:0.067819782 |
| 48:−0.0034453126 49:0.051646981 50:0.027854234 51:0.060220748 52:−0.0081677726 |
| 53:0.054335382 54:−0.035867997 55:0.014197615 56:−0.035021003 57:−0.014566134 |
| 58:0.03016793 59:−0.040633935 60:−0.0014767371 61:−0.073092438 62:−0.035074297 |
| 63:−0.050672945 64:−0.078871444 65:−0.027396075 66:−0.087323487 67:−0.039443281 |
| 68:0.0038563253 69:−0.033224653 70:0.01565117 71:0.004062959 72:0.00027864502 |
| 73:−0.064250752 74:−0.042209428 75:0.012480129 76:−0.024839332 77:−0.013282768 # |
| 0.014768605856240387 1:−5.9010167 2:−4.0328221 3:−1.9765494 4:1.6331258 5:−1.8146535 |
| 6:−1.9523394 7:0.46904564 8:0.14834239 9:−2.3186646 10:0.9756611 11:0.089916095 12:−1.5264442 |
| 13:−0.4749679 14:−1.7847501 15:−0.20434441 16:1.1652477 17:−0.14515577 18:−0.14447336 |
| 19:0.089038402 20:−0.30710894 21:−0.046030652 22:0.47091958 23:−0.15945408 |
| 24:−0.00044971227 25:0.39449137 26:0.44432575 27:0.021201421 28:−0.030532368 29:−0.2454444 |
| 30:0.54841805 31:0.37730277 32:−0.052458186 33:−0.43268293 34:−0.25524092 35:−0.014369486 |
| 36:−0.2128163 37:−0.14128286 38:−0.19040547 39:0.059252851 40:0.1310322 41:0.10185894 |
| 42:0.055527836 43:−0.14394827 44:0.025102727 45:−0.02773682 46:0.0029754874 |
| 47:0.024302408 48:−0.063831091 49:0.026865091 50:0.088617988 51:−0.019352101 |
| 52:0.077239297 53:−0.038459681 54:−0.0031290117 55:−0.0092261191 56:−0.00028370993 |
| 57:−0.014566134 58:0.03016793 59:−0.040633935 60:−0.0014767371 61:−0.073092438 |
| 62:−0.035074297 63:−0.050672945 64:−0.078871444 65:−0.027396075 66:−0.087323487 |
| 67:−0.039443281 68:0.0038563253 69:−0.033224653 70:0.01565117 71:0.004062959 |
| 72:0.00027864502 73:−0.064250752 74:−0.042209428 75:0.012480129 76:−0.024839332 |
| 77:−0.013282768 # |
| −0.014768605856240387 1:1.9049605 2:−1.8820572 3:3.52895 4:1.623381 5:0.8641119 |
| 6:0.19026566 7:−0.0011935582 8:−0.13901827 9:0.20222652 10:−2.8518419 11:−0.3479923 |
| 12:0.088709339 13:−0.08555308 14:−0.14782868 15:0.29343146 16:−0.055620886 17:−0.66070914 |
| 18:−0.30883488 19:0.32413155 20:−0.52922559 21:0.021073598 22:−0.50548029 23:−0.95641261 |
| 24:0.75348854 25:−0.33087933 26:0.11948154 27:0.42951742 28:0.24323775 29:−0.40914583 |
| 30:−0.22168945 31:0.10208555 32:−0.24475613 33:0.15350848 34:0.062723987 35:0.11185728 |
| 36:−0.17226228 37:−0.17001186 38:0.14773808 39:0.29176939 40:0.21205032 41:0.064550541 |
| 42:0.047816344 43:0.092291519 44:0.055294711 45:0.053621441 46:0.047355648 |
| 47:0.081085436 48:0.044272099 49:−0.0029146529 50:−0.025055079 51:−0.11126631 |
| 52:0.048958123 53:0.031906977 54:−0.007000512 55:−0.017101878 56:0.036050268 |
| 57:−0.014566134 58:0.03016793 59:−0.040633935 60:−0.0014767371 61:−0.073092438 |
| 62:−0.035074297 63:−0.050672945 64:−0.078871444 65:−0.027396075 66:−0.087323487 |
| 67:−0.039443281 68:0.0038563253 69:−0.033224653 70:0.01565117 71:0.004062959 |
| 72:0.00027864502 73:−0.064250752 74:−0.042209428 75:0.012480129 76:−0.024839332 |
| 77:−0.013282768 # |
| 0.014768605856240387 1:−1.3157859 2:0.70299256 3:3.0006199 4:3.2491477 5:2.8304772 |
| 6:0.98038137 7:1.3980098 8:−0.58263808 9:−1.2958558 10:1.0405852 11:1.7852861 12:0.5182727 |
| 13:0.81460285 14:−0.76353443 15:0.49746525 16:−0.080426998 17:0.99329841 18:0.033001561 |
| 19:0.64020813 20:0.56085485 21:0.32682621 22:−0.51742673 23:0.92242414 24:−0.20153917 |
| 25:0.16728246 26:−0.15194198 27:−0.059559919 28:−0.1619108 29:−0.06057547 30:−0.0015514743 |
| 31:0.10874921 32:−0.085824482 33:−0.43436861 34:0.097211942 35:0.0087928288 |
| 36:−0.19497071 37:−0.1644199 38:0.22987467 39:0.00072805351 40:−0.036387928 41:−0.024793714 |
| 42:0.046035178 43:0.30053556 44:−0.064070314 45:−0.025725504 46:−0.0066927713 |
| 47:−0.087981746 48:0.046682835 49:0.030051094 50:0.05447289 51:−0.056455433 52:−0.033297841 |
| 53:0.050011542 54:−0.022543613 55:0.017001271 56:0.045515299 57:−0.014566134 |
| 58:0.03016793 59:−0.040633935 60:−0.0014767371 61:−0.073092438 62:−0.035074297 |
| 63:−0.050672945 64:−0.078871444 65:−0.027396075 66:−0.087323487 67:−0.039443281 |
| 68:0.0038563253 69:−0.033224653 70:0.01565117 71:0.004062959 72:0.00027864502 |
| 73:−0.664250752 74:−0.042209428 75:0.012480129 76:−0.024839332 77:−0.013282768 # |
| −0.014768605856240387 1:−1.0982398 2:−2.4368637 3:0.79138798 4:−0.19059795 5:2.4956129 |
| 6:0.59419161 7:−1.0538421 8:1.1098379 9:1.510326 10:0.025463993 11:0.47247869 |
| 12:0.54310888 13:−1.4702748 14:−0.032527249 15:0.55360329 16:−0.18030564 17:0.28367868 |
| 18:0.55749577 19:0.49138963 20:−0.29553726 21:−0.5870961 22:−0.37311175 23:0.18747084 |

APPENDIX C15-continued

SVM Model Weights (77; Early/Late)

24:0.041127604 25:0.21029881 26:−0.40718269 27:−0.25035253 28:0.22009574 29:0.055686142 30:−0.24643996 31:−0.12602903 32:0.085209414 33:−0.12572211 34:0.0016459211 35:−0.095045388 36:0.048676528 37:−0.17387794 38:−0.1420448 39:0.11469521 40:0.031258076 41:−0.011970902 42:−0.082991265 43:−0.083747424 44:0.026539017 45:−0.056411669 46:0.040468153 47:−0.01395872 48:−0.028325625 49:0.010746783 50:0.065619737 51:0.043784723 52:0.047854524 53:−0.0096203899 54:0.0006713288 55:−0.0027980302 56:0.0017356656 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 #
−0.014768605856240387 1:5.2102227 2:3.9976118 3:0.080293134 4:−0.029725684 5:−0.95058012 6:0.11048691 7:−0.31062421 8:−0.22639115 9:−1.1626472 10:1.0553827 11:−0.090369746 12:1.0416471 13:0.55352253 14:0.64242268 15:−0.56834584 16:0.50699592 17:0.78428459 18:−0.19394138 19:−0.27866656 20:0.051096424 21:0.07269422 22:0.22581221 23:−0.1890261 24:0.10925961 25:−0.21392211 26:0.014856681 27:0.38521728 28:0.2155547 29:−0.379787 30:−0.2093354 31:−0.41027316 32:−0.074927203 33:−0.027296368 34:−0.27130839 35:−0.4485175 36:0.075121909 37:−0.15112031 38:0.046910606 39:0.16460049 40:−0.035657734 41:0.015574251 42:0.20202383 43:0.044082638 44:−0.22763637 45:−0.12267534 46:0.065599203 47:−0.037435614 48:−0.06740804 49:−0.022633193 50:−0.048605286 51:0.022895308 52:0.071274288 53:−0.049215917 54:−0.07501512 55:0.015261421 56:−0.051739872 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:0.013282768 #
0.014768605856240387 1:4.6002431 2:−7.2568059 3:4.7291026 4:−1.0225035 5:0.021546366 6:−2.0779712 7:−0.83757126 8:0.54197347 9:−0.20948814 10:0.1048112 11:−0.18034166 12:0.48489195 13:0.5373714 14:−0.13309625 15:1.3713417 16:−0.10321748 17:0.57164544 18:0.21653122 19:0.21072166 20:0.18643847 21:0.54172122 22:0.22825341 23:0.86882776 24:0.48877597 25:0.37703291 26:0.30987799 27:0.1168979 28:0.10090527 29:−0.10443282 30:−0.021420695 31:−0.31994495 32:−0.27734739 33:0.20602185 34:0.18579592 35:0.015469311 36:−0.13661198 37:0.12489217 38:−0.14398924 39:−0.089855082 40:−0.009190348 41:0.2373122 42:0.010101872 43:−0.056154639 44:0.06147819 45:−0.050348628 46:0.0048662391 47:0.086996771 48:0.16601563 49:0.047019847 50:0.055492263 51:−0.060654737 52:−0.02383565 53:−0.091649413 54:0.0068636341 55:0.0093666511 56:−0.072218902 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 #
−0.011206351909628189 1:−5.0756226 2:−8.2595215 3:−1.2156655 4:−2.7136712 5:0.74469912 6:−3.1111739 7:1.6049062 8:−4.8416181 9:2.3290875 10:1.5436403 11:−1.0302157 12:1.4037627 13:−0.52081388 14:1.0506417 15:−1.63344 16:−0.074092619 17:−0.8303957 18:−0.50330883 19:0.59144461 20:0.70327216 21:−0.29993597 22:0.15809666 23:0.22535191 24:0.47231099 25:−0.077164747 26:−0.21365905 27:−0.0089044822 28:0.069617361 29:−0.051537748 30:0.03524068 31:0.043939263 32:−0.10006648 33:−0.21139733 34:0.11636741 35:0.03831777 36:−0.061771911 37:−0.034540422 38:−0.045814056 39:0.010636433 40:−0.05437135 41:−0.014837124 42:0.02811862 43:−0.043905228 44:−0.10224012 45:0.017084097 46:−0.033059448 47:0.032695659 48:0.016907997 49:0.057397209 50:−0.032474376 51:−0.047577988 52:0.030859992 53:0.028889535 54:0.026548047 55:0.007073361 56:−0.015304038 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 #
−0.0092794577069623685 1:−1.4173634 2:−4.4854941 3:−0.39041179 4:1.0856786 5:2.5890806 6:−1.0967088 7:−1.2430353 8:1.4520231 9:1.0858341 10:0.51167381 11:0.5245589 12:1.1335742 13:0.17423496 14:0.52161896 15:0.22516307 16:0.31588632 17:0.21587253 18:−0.74981898 19:−0.67118168 20:0.14636877 21:0.44879469 22:−0.0049315616 23:−0.35790056 24:−0.28237695 25:0.11011039 26:0.38698107 27:0.074564859 28:0.55507314 29:−0.31626001 30:0.2187548 31:0.35623509 32:−0.38971603 33:0.2021132 34:0.096233301 35:−0.36095038 36:−0.099982403 37:0.30664298 38:0.066776812 39:−0.067210272 40:0.01807688 41:−0.13533093 42:−0.23607574 43:0.025971882 44:−0.053209517 45:−0.068547353 46:−0.072996713 47:−0.089486741 48:−0.044004746 49:−0.030522281 50:0.065588713 51:0.028177662 52:0.007529432 53:0.067739211 54:0.049285736 55:−0.028608471 56:−0.0039775814 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 #
−0.014768605856240387 1:−1.0982398 2:−2.4368637 3:0.79138798 4:−0.19059795 5:2.4956129 6:0.59419161 7:−1.0538421 8:1.1098379 9:1.510326 10:0.025463993 11:0.47247869 12:0.54310888 13:−1.4702748 14:−0.032527249 15:0.55360329 16:−0.18030564 17:0.28367868 18:0.55749577 19:0.49138963 20:−0.29553726 21:−0.5870961 22:−0.37311175 23:0.18747084 24:0.041127604 25:0.21029881 26:−0.40718269 27:−0.25035253 28:0.22009574 29:0.055686142 30:−0.24643996 31:−0.12602903 32:0.085209414 33:−0.12572211 34:0.0016459211 35:−0.095045388 36:0.048676528 37:−0.17387794 38:−0.1420448 39:0.11469521 40:0.031258076 41:−0.011970902 42:−0.082991265 43:−0.083747424 44:0.026539017 45:−0.056411669 46:0.040468153 47:−0.01395872 48:−0.028325625 49:0.010746783 50:0.065619737 51:0.043784723 52:0.047854524 53:−0.0096203899 54:0.0006713288 55:−0.0027980302

APPENDIX C15-continued

| SVM Model Weights (77; Early/Late) |
| --- |
| 56:0.0017356656 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |
| −0.0053398794332080689 1:2.4800396 2:1.0886033 3:−4.1771445 4:1.1192465 5:0.56247091 6:1.2176269 7:2.7507098 8:−0.42160803 9:−1.1654049 10:−1.856112 11:2.0763941 12:2.1084695 13:0.059086759 14:−0.48607701 15:0.1853876 16:−0.46677867 17:0.65311015 18:−0.15493564 19:0.064726971 20:0.64843899 21:−0.17178282 22:0.13598746 23:−0.30330279 24:−0.3721984 25:−0.45937416 26:−0.28618789 27:−0.061018307 28:0.25755653 29:0.01015126 30:0.43489286 31:−0.23160291 32:0.26822332 33:−0.18198679 34:0.11317819 35:−0.018076936 36:−0.023457909 37:−0.055039685 38:0.051811643 39:−0.11251057 40:0.15998535 41:0.21557918 42:−0.16684479 43:−0.046091679 44:0.070016332 45:0.031692948 46:−0.013790468 47:0.089666605 48:−0.04926759 49:−0.010420648 50:−0.12629215 51:−0.010580245 52:0.019162683 53:−0.032959752 54:0.038634114 55:−0.031798515 56:−0.0471939 57:−0.014566134 58:0.03016793 59:−0.040633935 60:−0.0014767371 61:−0.073092438 62:−0.035074297 63:−0.050672945 64:−0.078871444 65:−0.027396075 66:−0.087323487 67:−0.039443281 68:0.0038563253 69:−0.033224653 70:0.01565117 71:0.004062959 72:0.00027864502 73:−0.064250752 74:−0.042209428 75:0.012480129 76:−0.024839332 77:−0.013282768 # |

APPENDIX D

Ovarian Cancer
Training Dataset

| | A | B | C | D | E | F | G | H | I | J | K |
|---|---|---|---|---|---|---|---|---|---|---|---|
| 1 | Label | CA270 | CA260 | 14053 | 14522 | 13899 | 13878 | 13830 | 13819 | 13783 | 13666 |
| 2 | Sample Type | Control | Control | Early Malignant | Early Malignant | Early Malignant | Early Malignant | Early Malignant | Early Malignant | Early Malignant | Early Malignant |
| 3 | | 0 | 0 | 2 | 2 | 2 | 2 | 2 | 2 | 2 | 2 |
| 4 | | 1 | 1 | −1 | −1 | −1 | −1 | −1 | −1 | −1 | −1 |
| 5 | 409.4/255.3>GPA:Lyso 16:0 | 8.674E−01 | 1.245E+00 | 2.306E+00 | 2.177E+00 | 2.530E+00 | 2.186E+00 | 2.248E+00 | 2.212E+00 | 2.176E+00 | 2.169E+00 |
| 6 | 433.4/279.3>GPA:Lyso 18:2 | 4.753E−01 | 7.372E−01 | 5.912E−01 | 7.607E−01 | 7.672E−01 | 7.711E−01 | 5.883E−01 | 5.086E−01 | 1.008E+00 | 5.451E−01 |
| 7 | 435.4/281.3>GPA:Lyso 18:1 | 1.663E−01 | 2.039E−01 | 2.307E−01 | 3.026E−01 | 3.519E−01 | 2.929E−01 | 3.541E−01 | 2.339E−01 | 3.273E−01 | 1.878E−01 |
| 8 | 437.4/283.3>GPA:Lyso 18:0 | 8.314E−01 | 9.467E−01 | 2.947E+00 | 1.229E+00 | 1.146E+00 | 9.845E−01 | 1.152E+00 | 1.456E+00 | 9.492E−01 | 2.945E+00 |
| 9 | 451.4/283.3>GPA:Lyso 18:0 | 2.403E−02 | 1.438E−02 | 1.631E−02 | 2.865E−02 | 3.723E−02 | 2.597E−02 | 2.060E−02 | 1.856E−02 | 1.373E−02 | 2.328E−02 |
| 10 | 459.6/305.5>GPA:Lyso 20:3 | 1.298E−02 | 1.309E−02 | 9.785E−03 | 2.253E−02 | 1.073E−02 | 2.403E−02 | 1.964E−02 | 1.005E−02 | 1.073E−02 | 7.489E−03 |
| 11 | 461.6/307.5>GPA:Lyso 20:2 | 6.470E−03 | 1.642E−02 | 9.785E−03 | 1.953E−02 | 1.577E−02 | 2.071E−02 | 2.060E−02 | 1.084E−02 | 1.320E−02 | 1.127E−02 |
| 12 | 463.7/309.5>GPA:Lyso 20:1 | 1.016E−02 | 1.116E−02 | 6.524E−03 | 1.212E−02 | 1.427E−02 | 9.077E−03 | 8.552E−03 | 1.005E−02 | 1.320E−02 | 1.727E−02 |
| 13 | 465.7/311.5>GPA:Lyso 20:0 | 1.016E−02 | 1.373E−02 | 2.736E−02 | 1.406E−02 | 1.148E−02 | 9.077E−03 | 1.513E−02 | 1.320E−02 | 1.137E−02 | 3.820E−02 |
| 14 | 481.4/327.3>GPA:Lyso 22:6 | 3.691E−02 | 3.079E−02 | 4.174E−02 | 5.719E−02 | 5.944E−02 | 6.878E−02 | 4.936E−02 | 4.174E−02 | 6.395E−02 | 3.820E−02 |
| 15 | 483.4/329.3>GPA:Lyso 22:5 | 9.238E−03 | 5.891E−03 | 3.916E−03 | 6.084E−03 | 9.303E−03 | 9.077E−03 | 9.560E−03 | 9.281E−03 | 6.577E−03 | 5.998E−03 |
| 16 | 641.8/251.3>GPA:16:1/16:2 | 1.845E−03 | 1.309E−03 | 0.000E+00 | 1.824E−03 | 2.146E−03 | 0.000E+00 | 5.032E−04 | 0.000E+00 | 1.792E−03 | 2.994E−03 |
| 17 | 643.8/253.3>GPA:16:1/16:1 | 3.230E−02 | 2.361E−02 | 1.502E−02 | 1.459E−02 | 1.288E−02 | 1.298E−02 | 9.056E−03 | 1.781E−02 | 1.017E−02 | 5.998E−03 |
| 18 | 645.8/255.3>GPA:16:1/16:0 | 1.234E−01 | 7.006E−02 | 5.869E−02 | 4.989E−02 | 5.011E−02 | 7.006E−02 | 4.281E−02 | 5.569E−02 | 5.021E−02 | 6.073E−02 |
| 19 | 647.8/255.3>GPA:16:0/16:0 | 8.184E−01 | 4.260E−01 | 2.833E−01 | 2.629E−01 | 3.036E−01 | 2.650E−01 | 2.361E−01 | 1.685E−01 | 1.738E−01 | 1.064E−01 |
| 20 | 667.8/279.3>GPA:34:4 | 1.845E−03 | 1.309E−03 | 0.000E+00 | 6.084E−04 | 7.157E−04 | 1.942E−03 | 5.032E−04 | 0.000E+00 | 5.976E−04 | 1.502E−03 |
| 21 | 669.8/279.3>GPA:34:3 | 1.384E−02 | 1.706E−02 | 1.502E−02 | 1.642E−02 | 2.146E−02 | 1.685E−02 | 1.406E−02 | 2.318E−02 | 1.491E−02 | 1.953E−02 |
| 22 | 669.8/281.3>GPA:34:4 | 0.000E+00 | 1.309E−03 | 3.916E−03 | 6.084E−04 | 3.584E−03 | 2.597E−03 | 1.513E−03 | 1.545E−03 | 3.584E−03 | 1.502E−03 |
| 23 | 671.8/279.3>GPA:18:2/16:0 | 7.479E−02 | 6.223E−02 | 5.150E−02 | 4.936E−02 | 4.582E−02 | 4.796E−02 | 3.069E−02 | 5.032E−02 | 4.968E−02 | 3.970E−02 |
| 24 | 673.8/281.3>GPA:18:1/16:0 | 2.688E+00 | 1.261E+00 | 5.032E−01 | 5.622E−01 | 5.762E−01 | 4.453E−01 | 2.854E−01 | 2.758E−01 | 2.328E−01 | 1.245E−01 |
| 25 | 695.8/279.3>GPA:36:4 | 3.230E−02 | 2.425E−02 | 1.438E−02 | 2.189E−02 | 2.221E−02 | 1.685E−02 | 1.513E−02 | 2.704E−02 | 3.412E−02 | 1.277E−02 |
| 26 | 695.8/303.3>GPA:36:4 | 8.133E−02 | 4.388E−02 | 2.414E−02 | 3.648E−02 | 3.155E−02 | 2.210E−02 | 2.114E−02 | 1.706E−02 | 2.210E−02 | 1.049E−02 |
| 27 | 697.8/281.3>GPA:20:3/16:0 | 2.489E−02 | 1.373E−02 | 3.916E−03 | 9.742E−03 | 7.876E−03 | 1.363E−02 | 8.047E−03 | 4.646E−03 | 8.970E−03 | 2.253E−03 |
| 28 | 697.8/305.3>GPA:18:1/18:2 | 8.680E−02 | 5.826E−02 | 3.391E−02 | 4.206E−02 | 3.863E−02 | 4.152E−02 | 2.822E−02 | 4.099E−02 | 5.139E−02 | 2.618E−02 |
| 29 | 699.8/279.3>GPA:36:2 | 1.223E−01 | 1.002E−01 | 5.354E−02 | 5.966E−02 | 4.013E−02 | 5.515E−02 | 4.882E−02 | 4.796E−02 | 6.277E−02 | 3.895E−02 |
| 30 | 699.8/281.3>GPA:36:2 | 1.982E+00 | 9.782E−01 | 4.109E−01 | 4.142E−01 | 4.464E−01 | 3.423E−01 | 2.736E−02 | 2.264E−01 | 1.781E−01 | 9.442E−02 |
| 31 | 701.8/283.3>GPA:36:1 | 6.106E+00 | 2.466E+00 | 9.042E−01 | 7.843E−01 | 9.671E−01 | 6.513E−01 | 3.573E−01 | 3.712E−01 | 2.800E−01 | 1.266E−01 |
| 32 | 703.8/283.3>GPA:36:0 | 5.279E−01 | 2.843E−01 | 1.706E−01 | 1.234E−01 | 1.577E−01 | 9.206E−02 | 8.702E−02 | 9.742E−02 | 6.105E−02 | 8.541E−02 |
| 33 | 721.8/255.3>GPA:18:1/20:4 | 7.758E−02 | 3.863E−02 | 2.800E−02 | 1.406E−02 | 2.511E−02 | 2.071E−02 | 1.363E−02 | 1.234E−02 | 1.255E−02 | 5.998E−03 |
| 34 | 721.8/281.3>GPA:16:0/22:5 | 3.487E−01 | 3.852E−01 | 7.914E−01 | 5.032E−01 | 6.642E−01 | 6.545E−01 | 6.376E−01 | 8.879E−01 | 5.708E−01 | 1.035E+00 |
| 35 | 723.8/283.3>GPA:18:0/20:4 | 9.053E−01 | 4.227E−01 | 2.124E−01 | 2.017E−01 | 2.929E−01 | 1.738E−01 | 1.277E−01 | 1.044E−01 | 9.335E−02 | 8.315E−02 |
| 36 | 725.8/305.3>GPA:20:3/18:0 | 4.893E−02 | 3.015E−02 | 1.170E−02 | 1.524E−02 | 1.212E−02 | 1.298E−02 | 1.212E−02 | 6.191E−03 | 7.178E−03 | 5.247E−03 |
| 37 | 729.8/281.3>GPA:38:1 | 1.931E−01 | 8.712E−02 | 4.828E−02 | 3.165E−02 | 3.648E−02 | 4.024E−02 | 3.069E−02 | 2.865E−02 | 2.811E−02 | 1.502E−02 |
| 38 | 731.8/283.3>GPA:38:0 | 1.491E−01 | 8.777E−02 | 6.524E−02 | 4.442E−02 | 4.936E−02 | 3.959E−02 | 3.423E−02 | 3.948E−02 | 2.747E−02 | 4.195E−02 |
| 39 | 751.8/303.3>GPA:40:4 | 8.401E−02 | 1.760E−01 | 6.921E−02 | 6.695E−02 | 7.296E−02 | 1.057E−01 | 8.251E−02 | 4.560E−02 | 1.524E−01 | 4.721E−02 |
| 40 | 757.8/281.3>GPA:40:1 | 7.167E−01 | 4.474E−01 | 1.921E−01 | 2.221E−01 | 2.747E−01 | 2.275E−01 | 1.545E−01 | 2.833E−01 | 2.350E−01 | 1.255E−01 |
| 41 | 759.8/283.3>GPA:40:0 | 3.552E−01 | 1.953E−01 | 8.809E−02 | 8.337E−02 | 1.266E−01 | 9.861E−02 | 6.588E−02 | 8.047E−02 | 5.086E−02 | 3.970E−02 |
| 42 | 777.8/329.3>GPA:42:5 | 2.768E−03 | 6.545E−04 | 6.524E−04 | 2.436E−03 | 2.146E−03 | 1.298E−03 | 1.513E−03 | 3.090E−03 | 3.584E−03 | 8.991E−03 |
| 43 | 481.4/253.3>GPGro:Lyso 16:1 | 5.761E−03 | 6.584E−03 | 1.250E−02 | 1.371E−02 | 1.322E−02 | 1.150E−02 | 1.507E−02 | 1.000E−02 | 8.462E−03 | 1.921E−02 |
| 44 | 483.4/255.3>GPGro:Lyso 16:0 | 1.842E−01 | 2.492E−01 | 7.198E−01 | 3.548E−01 | 4.242E−01 | 3.824E−01 | 3.545E−01 | 5.564E−01 | 3.414E−01 | 7.768E−01 |
| 45 | 507.4/279.3>GPGro:Lyso 18:2 | 1.242E−01 | 1.445E−01 | 2.144E−01 | 1.332E−01 | 1.553E−01 | 1.330E−01 | 1.186E−01 | 1.669E−01 | 1.746E−01 | 2.573E−01 |

APPENDIX D-continued

| | | | | | Ovarian Cancer Training Dataset | | | | | | |
|---|---|---|---|---|---|---|---|---|---|---|---|
| 46 | 509.4/281.3>GPGro:Lyso 18:1 | 8.179E−02 | 9.979E−02 | 1.995E−01 | 1.433E−01 | 1.466E−01 | 1.263E−01 | 1.367E−01 | 1.669E−01 | 1.129E−01 | 2.465E−01 |
| 47 | 511.4/283.3>GPGro:Lyso 18:0 | 1.520E−01 | 1.674E−01 | 4.824E−01 | 2.281E−01 | 2.812E−01 | 2.489E−01 | 2.560E−01 | 3.882E−01 | 2.421E−01 | 5.767E−01 |
| 48 | 531.4/303.3>GPGro:Lyso 20:4 | 1.551E−02 | 2.464E−02 | 4.964E−02 | 3.446E−02 | 3.626E−02 | 3.266E−02 | 4.295E−02 | 2.392E−02 | 2.906E−02 | 4.604E−02 |
| 49 | 555.4/327.3>GPGro:Lyso 22:6 | 5.761E−03 | 1.021E−02 | 1.813E−02 | 1.561E−02 | 1.337E−02 | 1.633E−02 | 1.049E−02 | 1.206E−02 | 1.577E−02 | 1.438E−02 |
| 50 | 557.4/329.3>GPGro:Lyso 22:5 | 1.551E−03 | 5.015E−03 | 6.404E−03 | 3.215E−03 | 2.752E−03 | 3.575E−03 | 4.089E−03 | 2.225E−03 | 5.015E−03 | 5.221E−03 |
| 51 | 717.8/253.3>GPGro:16:1/16:1 | 6.301E−02 | 1.281E−01 | 1.499E−01 | 1.919E−01 | 2.524E−01 | 1.946E−01 | 3.746E−01 | 1.484E−01 | 1.469E−01 | 1.314E−01 |
| 52 | 719.8/253.3>GPGro:16:1/16:0 | 1.993E−03 | 1.098E−03 | 3.292E−03 | 3.935E−03 | 4.115E−03 | 5.761E−03 | 6.276E−03 | 1.854E−03 | 1.721E−03 | 7.896E−03 |
| 53 | 721.8/255.3>GPGro:16:0/16:0 | 5.478E−02 | 6.584E−02 | 1.142E−01 | 6.970E−02 | 9.388E−02 | 8.513E−02 | 8.076E−02 | 1.209E−01 | 7.587E−02 | 1.417E−01 |
| 54 | 743.8/279.3>GPGro:18:2/16:1 | 4.678E+00 | 5.371E+00 | 4.324E+00 | 4.822E+00 | 4.561E+00 | 4.698E+00 | 3.259E+00 | 4.541E+00 | 5.772E+00 | 3.197E+00 |
| 55 | 743.8/281.3>GPGro:18:1/16:2 | 4.384E−01 | 5.447E−01 | 5.997E−01 | 6.149E−01 | 6.723E−01 | 6.051E−01 | 8.006E−01 | 5.525E−01 | 5.747E−01 | 4.687E−01 |
| 56 | 745.8/279.3>GPGro:18:2/16:0 | 1.481E−01 | 1.759E−01 | 1.578E−01 | 1.579E−01 | 1.451E−01 | 1.533E−01 | 1.091E−01 | 1.577E−01 | 1.880E−01 | 1.420E−01 |
| 57 | 745.8/281.3>GPGro:18:1/16:1 | 2.533E+00 | 3.438E+00 | 3.912E+00 | 4.283E+00 | 4.623E+00 | 3.757E+00 | 5.070E+00 | 3.369E+00 | 3.590E+00 | 3.117E+00 |
| 58 | 747.8/255.2>GPGro:16:0/18:1 | 3.112E−02 | 3.832E−02 | 6.121E−02 | 5.555E−02 | 4.578E−02 | 4.141E−02 | 4.861E−02 | 5.324E−02 | 4.115E−02 | 1.011E−01 |
| 59 | 747.8/281.1>GPGro:16:0/18:1 | 1.700E−01 | 1.219E−01 | 8.462E−02 | 9.259E−02 | 9.876E−02 | 7.922E−02 | 9.208E−02 | 7.664E−02 | 7.227E−02 | 5.041E−02 |
| 60 | 749.8/283.3>GPGro:18:0/16:0 | 3.575E−02 | 2.752E−02 | 5.170E−02 | 3.395E−02 | 4.347E−02 | 3.729E−02 | 3.961E−02 | 5.453E−02 | 3.344E−02 | 6.430E−02 |
| 61 | 767.8/303.3>GPGro:20:4/16:1 | 5.538E−01 | 1.110E+00 | 9.136E−01 | 1.343E+00 | 1.158E+00 | 1.538E+00 | 1.549E+00 | 6.916E−01 | 1.163E+00 | 7.112E−01 |
| 62 | 769.8/279.3>GPGro:18:2/18:2 | 5.476E−01 | 6.074E−01 | 3.214E−01 | 3.420E−01 | 2.948E−01 | 3.865E−01 | 2.684E−01 | 4.798E−01 | 4.566E−01 | 4.073E−01 |
| 63 | 769.8/303.3>GPGro:20:4/16:0 | 7.536E−03 | 1.083E−02 | 1.188E−02 | 1.371E−02 | 1.235E−02 | 1.415E−02 | 1.618E−02 | 1.093E−02 | 8.745E−03 | 1.957E−02 |
| 64 | 771.8/279.3>GPGro:18:2/18:1 | 2.274E+00 | 2.583E+00 | 2.170E+00 | 2.503E+00 | 2.176E+00 | 2.542E+00 | 2.124E+00 | 3.098E+00 | 3.138E+00 | 2.026E+00 |
| 65 | 773.8/279.3>GPGro:18:2/18:0 | 1.008E−01 | 1.116E−01 | 1.381E−01 | 1.165E−01 | 1.127E−01 | 1.111E−01 | 9.310E−02 | 1.361E−01 | 1.232E−01 | 1.934E−01 |
| 66 | 773.8/281.3>GPGro:18:1/18:1 | 5.095E−01 | 5.736E−01 | 5.231E−01 | 6.346E−01 | 6.294E−01 | 6.019E−01 | 1.213E+00 | 6.899E−01 | 5.682E−01 | 6.789E−01 |
| 67 | 775.8/281.3>GPGro:18:1/18:0 | 4.038E−02 | 5.298E−02 | 8.873E−02 | 6.250E−02 | 7.047E−02 | 6.353E−02 | 8.050E−02 | 8.719E−02 | 5.195E−02 | 1.489E−01 |
| 68 | 777.8/283.3>GPGro:18:0/18:0 | 1.000E−01 | 1.163E−01 | 1.983E−01 | 1.355E−01 | 1.661E−01 | 1.602E−01 | 1.764E−01 | 2.981E−01 | 1.497E−01 | 3.455E−01 |
| 69 | 795.8/303.3>GPGro:20:4/18:1 | 2.336E−01 | 4.285E−01 | 4.057E−01 | 6.525E−01 | 5.259E−01 | 6.836E−01 | 8.377E−01 | 4.147E−01 | 5.125E−01 | 3.776E−01 |
| 70 | 797.8/303.3>GPGro:20:4/18:0 | 1.350E−02 | 2.752E−02 | 3.935E−02 | 2.958E−02 | 3.061E−02 | 3.446E−02 | 3.446E−02 | 3.858E−02 | 2.855E−02 | 5.170E−02 |
| 71 | 821.8/327.3>GPGro:22:6/18:0 | 4.655E−03 | 7.073E−03 | 9.079E−03 | 7.587E−03 | 9.259E−03 | 8.230E−03 | 6.507E−03 | 4.810E−03 | 8.462E−03 | 9.156E−03 |
| 72 | 823.8/329.3>GPGro:22:5/18:0 | 8.848E−04 | 2.196E−03 | 2.803E−03 | 3.935E−03 | 2.402E−03 | 1.553E−03 | 4.578E−03 | 2.040E−03 | 3.009E−03 | 1.618E−03 |
| 73 | 494.4/407.4>Lyso GPSer:16:1 | 1.069E−02 | 2.754E−03 | 1.377E−03 | 3.205E−03 | 3.770E−03 | 2.043E−03 | 1.591E−03 | 8.138E−04 | 6.287E−04 | 3.149E−03 |
| 74 | 496.4/409.4>Lyso GPSer:16:0 | 1.456E−02 | 7.573E−03 | 9.605E−03 | 6.400E−03 | 3.770E−03 | 4.097E−03 | 7.415E−03 | 6.512E−03 | 5.034E−03 | 5.519E−03 |
| 75 | 522.4/435.4>Lyso GPSer:18:1 | 5.203E−01 | 3.634E−01 | 1.411E−01 | 1.580E−01 | 3.160E−01 | 1.174E−01 | 7.619E−02 | 7.562E−02 | 1.000E−01 | 6.072E−02 |
| 76 | 524.4/437.4>Lyso GPSer:18:0 | 4.018E−01 | 2.427E−01 | 1.524E−01 | 1.354E−01 | 3.093E−01 | 8.804E−02 | 5.135E−02 | 9.842E−02 | 1.070E−01 | 1.104E−01 |
| 77 | 544.4/457.4>Lyso GPSer:20:4 | 1.456E−02 | 6.196E−03 | 2.743E−03 | 8.330E−03 | 2.032E−02 | 6.140E−03 | 8.995E−03 | 1.625E−03 | 6.919E−03 | 5.519E−03 |
| 78 | 570.4/483.4>Lyso GPSer:22:5 | 0.000E+00 | 0.000E+00 | 0.000E+00 | 6.400E−04 | 7.528E−04 | 0.000E+00 | 5.293E−04 | 2.438E−03 | 6.287E−04 | 0.000E+00 |
| 79 | 732.6/645.6>GPSer:32:1 | 1.941E−02 | 6.196E−03 | 6.174E−03 | 3.205E−03 | 3.014E−03 | 1.366E−03 | 5.824E−03 | 5.700E−03 | 3.149E−03 | 7.878E−04 |
| 80 | 734.6/647.6>GPSer:32:0 | 7.777E−03 | 3.442E−03 | 0.000E+00 | 1.919E−03 | 3.014E−03 | 0.000E+00 | 2.122E−03 | 3.251E−03 | 6.287E−04 | 0.000E+00 |
| 81 | 758.6/671.6>GPSer:34:2 | 2.912E−02 | 1.242E−02 | 1.230E−02 | 7.043E−03 | 1.433E−02 | 1.366E−02 | 1.059E−02 | 1.058E−02 | 1.196E−02 | 1.104E−02 |
| 82 | 760.8/673.8>GPSer:34:1 | 1.377E−01 | 6.546E−02 | 2.607E−02 | 3.330E−02 | 2.257E−02 | 2.325E−02 | 8.465E−03 | 8.138E−03 | 1.129E−02 | 1.580E−03 |
| 83 | 762.8/675.7>GPSer:34:0 | 5.926E−02 | 2.754E−02 | 8.239E−03 | 6.400E−03 | 6.772E−03 | 3.409E−03 | 3.702E−03 | 7.325E−03 | 1.885E−03 | 4.729E−03 |
| 84 | 782.6/695.7>GPSer:36:4 | 1.749E−02 | 1.102E−02 | 1.648E−02 | 5.767E−03 | 7.528E−03 | 1.433E−02 | 1.059E−02 | 1.140E−02 | 8.804E−03 | 1.264E−02 |
| 85 | 784.8/697.8>GPSer:36:3 | 6.806E−03 | 2.065E−03 | 4.120E−03 | 3.205E−03 | 3.014E−03 | 2.731E−03 | 4.233E−03 | 4.887E−03 | 3.149E−03 | 7.878E−04 |
| 86 | 786.8/699.8>GPSer:36:2 | 5.068E−01 | 2.291E−01 | 8.510E−02 | 6.084E−02 | 6.479E−02 | 4.707E−02 | 2.381E−02 | 3.341E−02 | 1.885E−02 | 8.668E−03 |
| 87 | 788.8/701.8>GPSer:36:1 | 3.630E+00 | 1.537E+00 | 5.293E−01 | 4.052E−01 | 4.842E−01 | 2.698E−01 | 1.479E−01 | 1.535E−01 | 1.151E−01 | 5.361E−02 |
| 88 | 790.8/703.8>GPSer:36:0 | 5.440E−01 | 2.144E−01 | 6.862E−02 | 5.576E−02 | 7.449E−02 | 4.300E−02 | 2.483E−02 | 1.874E−02 | 1.704E−02 | 1.738E−02 |
| 89 | 808.6/721.6>GPSer:38:6 | 9.041E−02 | 4.819E−02 | 2.540E−02 | 1.219E−02 | 3.318E−02 | 6.140E−03 | 6.354E−03 | 1.298E−02 | 8.183E−03 | 2.212E−02 |
| 90 | 810.8/723.8>GPSer:38:5 | 3.544E−01 | 1.321E−01 | 7.201E−02 | 6.275E−02 | 1.490E−01 | 4.233E−02 | 1.321E−02 | 3.014E−02 | 3.330E−02 | 3.860E−02 |
| 91 | 812.8/725.8>GPSer:38:4 | 1.050E−01 | 4.481E−02 | 2.472E−02 | 2.246E−02 | 3.770E−02 | 1.366E−02 | 1.163E−02 | 6.512E−03 | 1.007E−02 | 5.519E−03 |
| 92 | 814.6/727.6>GPSer:38:3 | 9.814E−01 | 4.007E−01 | 1.309E−01 | 9.989E−02 | 1.264E−01 | 9.752E−02 | 3.544E−02 | 4.153E−02 | 3.397E−02 | 1.185E−02 |
| 93 | 816.8/729.8>GPSer:38:2 | 2.465E+00 | 1.092E+00 | 3.262E−01 | 2.946E−01 | 3.228E−01 | 1.851E−01 | 1.037E−01 | 8.217E−02 | 7.235E−02 | 2.528E−02 |
| 94 | 818.8/731.8>GPSer:38:1 | 3.352E−01 | 1.400E−01 | 4.391E−02 | 4.289E−02 | 5.045E−02 | 2.111E−02 | 1.479E−02 | 1.219E−02 | 6.287E−03 | 7.099E−03 |
| 95 | 834.8/747.8>GPSer:40:6 | 5.734E−01 | 2.427E−01 | 7.686E−02 | 6.591E−02 | 6.998E−02 | 5.248E−02 | 3.126E−02 | 3.172E−02 | 2.077E−02 | 2.054E−02 |

APPENDIX D-continued

| | | Ovarian Cancer Training Dataset | | | | | | | | | |
|---|---|---|---|---|---|---|---|---|---|---|---|
| 96 | 836.8/749.8>GPSer:40:5 | 1.242E−01 | 4.334E−02 | 1.648E−02 | 1.862E−02 | 1.580E−02 | 1.298E−02 | 8.465E−03 | 4.887E−03 | 1.007E−02 | 4.729E−03 |
| 97 | 838.8/751.8>GPSer:40:4 | 1.907E−01 | 9.707E−02 | 3.296E−02 | 2.370E−02 | 3.318E−02 | 1.772E−02 | 1.059E−02 | 8.950E−03 | 8.183E−03 | 3.939E−03 |
| 98 | 840.6/753.7>GPSer:40:3 | 1.716E−01 | 9.233E−02 | 2.743E−02 | 2.630E−02 | 3.014E−02 | 2.460E−02 | 1.219E−02 | 2.280E−02 | 9.436E−03 | 7.878E−03 |
| 99 | 778.9/97>Sulfatide:16:0 | 5.494E−02 | 9.430E−02 | 1.051E−01 | 9.528E−02 | 9.001E−02 | 5.861E−02 | 6.965E−02 | 6.891E−02 | 8.952E−02 | 1.053E−01 |
| 100 | 806.9/97>Sulfatide:18:0 | 3.801E−02 | 3.139E−02 | 3.127E−02 | 1.950E−02 | 3.850E−02 | 3.188E−02 | 2.305E−02 | 4.414E−02 | 2.943E−02 | 5.481E−02 |
| 101 | 822.9/97>Sulfatide:18:0 (OH) | 1.150E−01 | 1.692E−01 | 1.521E−01 | 1.557E−01 | 1.803E−01 | 1.680E−01 | 1.373E−01 | 2.318E−01 | 1.803E−01 | 1.079E−01 |
| 102 | 834.9/97>Sulfatide:20:0 | 3.703E−01 | 3.544E−01 | 5.408E−01 | 3.568E−01 | 3.998E−01 | 4.255E−01 | 3.397E−01 | 6.671E−01 | 3.863E−01 | 8.105E−01 |
| 103 | 850.9/97>Sulfatide:20:0 (OH) | 1.557E−01 | 1.913E−01 | 1.987E−01 | 2.085E−01 | 2.918E−01 | 2.318E−01 | 1.594E−01 | 2.882E−01 | 2.465E−01 | 1.208E−01 |
| 104 | 862.9/97>Sulfatide:22:1 | 1.225E−01 | 1.692E−01 | 2.109E−01 | 1.471E−01 | 1.643E−01 | 1.692E−01 | 1.680E−01 | 3.115E−01 | 2.011E−01 | 3.593E−01 |
| 105 | 878.9/97>Sulfatide:22:1 (OH) | 4.488E−01 | 5.543E−01 | 6.818E−01 | 5.383E−01 | 6.818E−01 | 6.683E−01 | 6.062E−01 | 1.027E+00 | 6.806E−01 | 9.540E−01 |
| 106 | 888.9/97>Sulfatide:24:1 | 1.003E−01 | 1.115E−01 | 1.803E−01 | 1.197E−01 | 1.410E−01 | 1.300E−01 | 1.324E−01 | 1.288E−01 | 1.239E−01 | 1.643E−01 |
| 107 | 890.9/97>Sulfatide:24:0 | 1.182E−01 | 1.275E−01 | 1.447E−01 | 9.601E−02 | 9.577E−02 | 9.712E−02 | 8.633E−02 | 9.724E−02 | 1.128E−01 | 1.053E−01 |
| 108 | 906.7/97>Sulfatide:24:0 (OH) | 1.172E−01 | 1.300E−01 | 1.606E−01 | 1.570E−01 | 1.680E−01 | 1.888E−01 | 1.754E−01 | 1.435E−01 | 1.533E−01 | 1.704E−01 |
| 109 | 1147/281.3>CardioliGPInsn:52:3 | 6.340E−03 | 1.197E−02 | 6.708E−03 | 4.169E−03 | 1.145E−02 | 8.155E−03 | 1.035E−02 | 6.193E−03 | 1.094E−02 | 5.996E−03 |
| 110 | 1376/281.3>CardioliGPInsn:66:2 | 3.593E−02 | 3.887E−02 | 2.980E−02 | 2.293E−02 | 2.698E−02 | 3.850E−02 | 4.083E−02 | 4.071E−02 | 3.421E−02 | 1.631E−02 |
| 111 | 1400/281.3>CardioliGPInsn:68:4 | 2.109E−02 | 2.771E−02 | 1.643E−02 | 2.367E−02 | 2.869E−02 | 2.526E−02 | 2.882E−02 | 3.360E−02 | 2.465E−02 | 1.974E−02 |
| 112 | 1402/281.3>CardioliGPInsn:68:3 | 1.484E−02 | 1.422E−02 | 9.687E−03 | 1.251E−02 | 1.557E−02 | 2.146E−02 | 2.882E−02 | 2.036E−02 | 1.778E−02 | 6.855E−03 |
| 113 | 1404/281.3>CardioliGPInsn:68:2 | 6.340E−03 | 2.244E−03 | 8.204E−03 | 7.652E−03 | 6.548E−03 | 5.935E−03 | 1.035E−02 | 4.414E−03 | 4.782E−03 | 4.280E−03 |
| 114 | 1406/281.3>CardioliGPInsn:68:1 | 6.340E−03 | 5.984E−03 | 8.952E−03 | 4.169E−03 | 4.096E−03 | 5.935E−03 | 2.882E−03 | 7.075E−03 | 7.517E−03 | 1.113E−02 |
| 115 | 1426/281.3>CardioliGPInsn:70:5 | 6.340E−03 | 1.122E−02 | 9.687E−03 | 1.251E−02 | 1.386E−02 | 1.337E−02 | 2.526E−02 | 2.563E−02 | 1.162E−02 | 1.459E−02 |
| 116 | 1428/281.3>CardioliGPInsn:70:4 | 2.109E−03 | 8.976E−03 | 2.232E−03 | 3.483E−03 | 1.063E−02 | 6.671E−03 | 5.751E−03 | 3.532E−03 | 6.830E−03 | 4.280E−03 |
| 117 | 1430/281.3>CardioliGPInsn:70:3 | 1.056E−02 | 1.876E−02 | 8.952E−03 | 1.950E−02 | 1.226E−02 | 1.337E−02 | 2.354E−02 | 1.594E−02 | 1.025E−02 | 1.028E−02 |
| 118 | 1432/281.3>CardioliGPInsn:70:2 | 8.449E−03 | 8.228E−03 | 1.118E−02 | 1.251E−02 | 1.145E−02 | 9.638E−03 | 1.150E−02 | 5.310E−03 | 5.469E−03 | 1.028E−02 |
| 119 | 1434/281.3>CardioliGPInsn:70:1 | 2.845E−02 | 6.732E−03 | 1.193E−02 | 9.736E−03 | 1.717E−02 | 1.037E−02 | 1.093E−02 | 1.508E−02 | 8.890E−03 | 1.113E−02 |
| 120 | 1436/281.3>CardioliGPInsn:70:0 | 1.484E−02 | 7.480E−03 | 1.118E−02 | 9.736E−03 | 1.386E−02 | 5.935E−03 | 1.839E−02 | 1.239E−02 | 1.508E−02 | 6.855E−03 |
| 121 | 436.6/196.1>Lyso GPEtn:Lyso 16:1e/16:0p | 1.585E−01 | 4.212E−02 | 4.203E−02 | 4.354E−03 | 6.144E−02 | 3.713E−02 | 1.799E−02 | 6.643E−02 | 3.847E−02 | 8.041E−02 |
| 122 | 450.4/196.1>Lyso GPEtn:Lyso 16:1 | 1.656E−01 | 6.554E−02 | 1.077E−01 | 1.434E−01 | 1.745E−01 | 1.069E−01 | 2.992E−01 | 1.380E−01 | 1.024E−01 | 2.253E−01 |
| 123 | 452.4/196.1>Lyso GPEtn:Lyso 16:0 | 2.520E+00 | 2.458E+00 | 1.585E+00 | 3.749E+00 | 5.191E+00 | 3.980E+00 | 3.482E+00 | 4.426E+00 | 2.369E+00 | 4.212E+00 |
| 124 | 462.4/196.1>Lyso GPEtn:Lyso 18:2e/18:1p | 9.261E−02 | 2.814E−02 | 3.268E−02 | 3.045E−02 | 3.589E−02 | 2.787E−02 | 3.598E−02 | 6.643E−02 | 3.847E−02 | 6.972E−02 |
| 125 | 464.5/196.1>Lyso GPEtn:Lyso 18:1e/18:0p | 8.593E−02 | 4.684E−02 | 8.869E−02 | 2.618E−02 | 3.072E−02 | 4.176E−02 | 3.598E−02 | 8.851E−02 | 3.847E−02 | 6.972E−02 |
| 126 | 476.6/196.1>Lyso GPEtn:Lyso 18:2a | 1.184E+00 | 1.069E+00 | 4.853E−01 | 6.189E−01 | 5.637E−01 | 6.447E−01 | 7.631E−01 | 6.198E−01 | 8.602E−01 | 1.042E+00 |
| 127 | 478.4/196.1>Lyso GPEtn:Lyso 18:1 | 3.286E+00 | 2.226E+00 | 1.211E+00 | 1.808E+00 | 1.665E+00 | 1.719E+00 | 2.128E+00 | 2.066E+00 | 1.888E+00 | 2.591E+00 |
| 128 | 480.4/196.1>Lyso GPEtn:Lyso 18:0 | 2.146E+00 | 1.647E+00 | 1.309E+00 | 3.491E+00 | 3.989E+00 | 3.624E+00 | 3.651E+00 | 3.482E+00 | 2.289E+00 | 3.108E+00 |
| 129 | 492.5/196.1>Lyso GPEtn:Lyso 20:1e/20:0p | 2.048E−01 | 3.277E−02 | 5.138E−02 | 6.972E−02 | 8.192E−02 | 6.963E−02 | 3.241E−02 | 6.091E−02 | 8.130E−02 | 5.361E−02 |
| 130 | 500.4/196.1>Lyso GPEtn:Lyso 20:4 | 8.149E+00 | 8.113E+00 | 6.264E+00 | 8.917E+00 | 5.939E+00 | 8.579E+00 | 1.019E+01 | 3.785E+00 | 8.323E+00 | 8.783E+00 |
| 131 | 524.4/196.1>Lyso GPEtn:Lyso 22:6 | 4.844E+00 | 6.886E+00 | 3.366E+00 | 7.911E+00 | 6.082E+00 | 7.447E+00 | 5.739E+00 | 2.582E+00 | 6.662E+00 | 5.272E+00 |
| 132 | 688.6/196.1>GPEtn:16:0/16:1 | 3.963E−02 | 2.342E−02 | 9.350E−02 | 4.354E−02 | 3.589E−02 | 2.787E−02 | 4.684E−02 | 6.643E−02 | 5.993E−02 | 1.122E−01 |
| 133 | 690.7/196.1>GPEtn 16:0/16:0 | 3.963E−02 | 1.407E−02 | 2.333E−02 | 8.709E−03 | 5.637E−02 | 2.324E−02 | 1.077E−02 | 2.217E−02 | 1.282E−02 | 1.069E−02 |
| 134 | 698.6/196.1>GPEtn:34:2p, 34:3e | 0.000E+00 | 1.407E−02 | 2.805E−02 | 1.309E−02 | 1.541E−02 | 0.000E+00 | 1.077E−02 | 5.530E−03 | 0.000E+00 | 1.069E−02 |
| 135 | 700.6/196.1>GPEtn:34:1p, 34:2e | 3.963E−02 | 1.407E−02 | 1.398E−02 | 4.354E−03 | 5.120E−03 | 4.639E−03 | 7.204E−03 | 2.217E−02 | 1.282E−02 | 5.361E−03 |
| 136 | 702.6/196.1>GPEtn:34:0p, 34:1e | 6.607E−03 | 1.870E−02 | 1.870E−02 | 1.309E−02 | 2.048E−02 | 1.852E−02 | 1.443E−02 | 2.769E−02 | 8.557E−03 | 3.215E−02 |
| 137 | 710.8/196.1>GPEtn:18:1/16:1 | 1.318E−01 | 9.350E−02 | 7.934E−02 | 5.663E−02 | 5.120E−02 | 5.565E−02 | 2.164E−02 | 9.973E−02 | 2.137E−02 | 6.972E−02 |
| 138 | 712.8/196.1>GPEtn:18:2/16:1 | 1.318E−01 | 2.814E−02 | 3.731E−02 | 4.791E−02 | 3.589E−02 | 1.389E−02 | 3.598E−02 | 3.321E−02 | 1.282E−02 | 4.292E−02 |
| 139 | 714.7/196.1>GPEtn:18:1/16:1 | 6.411E−01 | 4.452E−01 | 9.795E−02 | 3.134E−01 | 3.072E−01 | 3.669E−01 | 2.199E−01 | 2.654E−01 | 2.351E−01 | 2.199E−01 |
| 140 | 716.7/196.1>GPEtn:18:1/16:0 | 2.378E−01 | 1.594E−01 | 6.999E−02 | 1.915E−01 | 1.745E−01 | 1.113E−01 | 1.514E−01 | 1.496E−01 | 7.275E−02 | 1.451E−01 |
| 141 | 718.6/196.1>GPEtn:18:0/16:0 | 9.884E−02 | 7.961E−02 | 5.138E−02 | 6.972E−02 | 8.709E−02 | 1.389E−02 | 6.483E−02 | 3.874E−02 | 3.847E−02 | 3.215E−02 |
| 142 | 722.6/196.1>GPEtn:36:4p | 4.630E−02 | 1.407E−02 | 9.350E−03 | 2.182E−02 | 5.120E−03 | 4.639E−03 | 1.799E−02 | 2.217E−02 | 2.137E−02 | 2.680E−02 |
| 143 | 724.6/196.1>GPEtn:36:3p, 36:4e | 0.000E+00 | 1.407E−02 | 1.398E−02 | 0.000E+00 | 2.048E−02 | 2.787E−02 | 2.164E−02 | 5.530E−03 | 8.557E−03 | 1.612E−02 |
| 144 | 726.6/196.1>GPEtn:36:2p, 36:3e | 2.645E−02 | 5.619E−02 | 5.601E−02 | 2.182E−02 | 4.613E−02 | 3.250E−02 | 1.799E−02 | 2.217E−02 | 2.565E−02 | 2.680E−02 |
| 145 | 728.6/196.1>GPEtn:36:1p, 36:2e | 3.304E−02 | 4.212E−02 | 3.731E−02 | 2.182E−02 | 3.589E−02 | 3.250E−02 | 2.164E−02 | 2.769E−02 | 7.275E−02 | 2.680E−02 |

APPENDIX D-continued

| | | Ovarian Cancer Training Dataset | | | | | | | | | |
|---|---|---|---|---|---|---|---|---|---|---|---|
| 146 | 738.8/196.1>GPEtn:20:4/16:0 | 2.110E−01 | 1.736E−01 | 7.471E−02 | 2.306E−01 | 2.814E−01 | 2.413E−01 | 2.805E−01 | 9.439E−02 | 1.710E−01 | 1.665E−01 |
| 147 | 740.8/196.1>GPEtn:18:2/18:1 | 4.292E−01 | 2.297E−01 | 4.666E−02 | 1.086E−01 | 7.685E−02 | 2.039E−01 | 1.443E−01 | 1.656E−01 | 1.630E−01 | 1.451E−01 |
| 148 | 742.8/196.1>GPEtn:18:1/18:1 | 8.130E−01 | 5.993E−01 | 1.630E−01 | 4.969E−01 | 4.862E−01 | 5.476E−01 | 5.004E−01 | 5.370E−01 | 4.194E−01 | 5.307E−01 |
| 149 | 744.6/196.1>GPEtn:18:0/18:1 | 1.656E−01 | 9.350E−02 | 5.601E−02 | 1.656E−01 | 7.168E−02 | 1.113E−01 | 1.336E−01 | 1.220E−01 | 4.711E−02 | 1.069E−01 |
| 150 | 746.8/196.1>GPEtn:18:0/18:0 | 4.363E−01 | 1.077E−01 | 2.333E−02 | 2.182E−02 | 3.072E−02 | 3.250E−02 | 4.319E−02 | 4.426E−02 | 1.710E−02 | 3.749E−02 |
| 151 | 748.6/196.1>GPEtn:38:5p, 38:6e | 7.266E−02 | 1.407E−02 | 2.805E−02 | 3.045E−02 | 2.565E−02 | 2.324E−02 | 2.164E−02 | 1.104E−02 | 8.557E−03 | 1.612E−02 |
| 152 | 750.6/196.1>GPEtn:38:4p, 38:5e | 3.304E−02 | 1.407E−02 | 4.666E−02 | 2.618E−02 | 5.637E−02 | 1.389E−02 | 3.598E−02 | 1.656E−02 | 2.992E−02 | 4.292E−02 |
| 153 | 752.6/196.1>GPEtn:38:3p, 38:4e | 2.645E−02 | 1.407E−02 | 2.333E−02 | 1.309E−02 | 2.565E−02 | 2.324E−02 | 2.876E−02 | 2.769E−02 | 2.137E−02 | 1.069E−02 |
| 154 | 754.6/196.1>GPEtn:38:2p, 38:3e | 5.948E−02 | 9.350E−03 | 4.666E−03 | 2.618E−02 | 1.024E−02 | 1.389E−02 | 2.164E−02 | 5.530E−03 | 1.710E−02 | 1.612E−02 |
| 155 | 756.6/196.1>GPEtn:38:1p, 38:2e | 5.289E−02 | 4.684E−03 | 3.268E−02 | 8.709E−03 | 3.589E−02 | 4.176E−02 | 7.204E−03 | 5.530E−03 | 1.282E−02 | 2.146E−02 |
| 156 | 762.8/196.1>GPEtn:20:4/18:2 | 1.193E−01 | 2.297E−01 | 1.585E−01 | 5.619E−01 | 5.735E−01 | 5.752E−01 | 4.034E−01 | 1.443E−01 | 3.767E−01 | 2.573E−01 |
| 157 | 764.8/196.1>GPEtn:20:4/18:1 | 1.256E−01 | 1.549E−01 | 6.536E−02 | 1.434E−01 | 1.843E−01 | 1.852E−01 | 2.199E−01 | 5.530E−02 | 1.665E−01 | 2.039E−01 |
| 158 | 766.8/196.1>GPEtn:20:4/18:0 | 2.048E−01 | 3.045E−01 | 2.289E−01 | 5.574E−01 | 4.452E−01 | 4.782E−01 | 5.183E−01 | 2.102E−01 | 3.081E−01 | 3.375E−01 |
| 159 | 768.8/196.1>GPEtn:20:3/18:0 | 2.244E−01 | 1.077E−01 | 6.999E−02 | 1.745E−01 | 1.175E−01 | 1.763E−01 | 1.941E−01 | 1.167E−01 | 8.130E−02 | 1.772E−01 |
| 160 | 770.6/196.1>GPEtn:20:2/18:0 | 4.630E−02 | 4.212E−02 | 2.333E−02 | 3.045E−02 | 1.541E−02 | 3.250E−02 | 2.876E−02 | 7.195E−02 | 3.419E−02 | 3.749E−02 |
| 161 | 772.6/196.1>GPEtn:20:1/18:0 | 5.289E−02 | 5.156E−02 | 3.731E−02 | 3.045E−02 | 3.589E−02 | 5.102E−02 | 2.520E−02 | 7.747E−02 | 3.847E−02 | 1.122E−01 |
| 162 | 776.6/196.1>GPEtn:40:5p, 40:6e | 5.289E−02 | 4.212E−02 | 1.398E−02 | 3.045E−02 | 1.024E−02 | 4.176E−02 | 3.598E−02 | 6.643E−02 | 3.419E−02 | 3.749E−02 |
| 163 | 778.6/196.1>GPEtn:40:4p, 40:5e | 6.607E−03 | 2.342E−02 | 2.333E−02 | 3.482E−02 | 2.048E−02 | 2.787E−02 | 2.164E−02 | 1.656E−02 | 2.992E−02 | 1.069E−02 |
| 164 | 780.6/196.1>GPEtn:40:3p, 40:4e | 1.318E−02 | 9.350E−03 | 2.333E−02 | 1.745E−02 | 2.565E−02 | 1.852E−02 | 2.520E−02 | 1.656E−02 | 1.710E−02 | 2.680E−02 |
| 165 | 784.6/196.1>GPEtn:40:1p, 40:2e | 3.963E−02 | 9.350E−03 | 3.268E−02 | 3.482E−02 | 5.637E−02 | 1.389E−02 | 3.598E−02 | 3.321E−02 | 3.419E−02 | 4.826E−02 |
| 166 | 788.8/196.1>GPEtn:22:4/18:3 | 1.585E−01 | 6.554E−02 | 2.805E−02 | 6.100E−02 | 8.192E−02 | 6.963E−02 | 7.925E−02 | 4.978E−02 | 6.420E−02 | 2.680E−02 |
| 167 | 790.8/196.1>GPEtn:22:4/18:2 | 1.122E−01 | 1.594E−01 | 6.999E−02 | 4.141E−01 | 4.559E−01 | 3.571E−01 | 3.099E−01 | 9.973E−02 | 1.754E−01 | 1.505E−01 |
| 168 | 792.6/196.1>GPEtn:40:5a | 7.934E−02 | 7.498E−02 | 7.471E−02 | 1.523E−01 | 1.487E−01 | 2.271E−01 | 1.585E−01 | 4.426E−02 | 7.703E−02 | 6.438E−02 |
| 169 | 794.6/196.1>GPEtn:40:4a | 1.986E−02 | 7.026E−02 | 2.805E−02 | 1.745E−02 | 5.120E−02 | 5.102E−02 | 7.560E−02 | 4.978E−02 | 2.565E−02 | 5.895E−02 |
| 170 | 796.8/196.1>GPEtn:40:3a | 1.986E−02 | 2.814E−02 | 2.805E−02 | 3.482E−02 | 4.613E−02 | 8.353E−02 | 6.118E−02 | 5.530E−02 | 4.283E−02 | 6.438E−02 |
| 171 | 798.6/196.1>GPEtn:40:2a | 5.289E−02 | 4.684E−02 | 1.870E−02 | 6.100E−02 | 3.589E−02 | 4.639E−02 | 5.761E−02 | 7.195E−02 | 1.710E−02 | 4.292E−02 |
| 172 | 569.4/241.1>GPIns:Lyso 16:1 | 6.009E−02 | 8.841E−02 | 8.547E−02 | 8.817E−02 | 1.030E−01 | 8.694E−02 | 1.692E−01 | 8.608E−02 | 7.247E−02 | 1.312E−01 |
| 173 | 571.3/241.1>GPIns:Lyso 16:0 | 2.063E+00 | 1.874E+00 | 2.765E+00 | 2.071E+00 | 2.454E+00 | 2.371E+00 | 2.407E+00 | 2.919E+00 | 2.198E+00 | 3.149E+00 |
| 174 | 595.4/241.1>GPIns:Lyso 18:2 | 2.773E+00 | 2.914E+00 | 4.544E+00 | 3.267E+00 | 3.831E+00 | 3.574E+00 | 2.938E+00 | 4.704E+00 | 3.905E+00 | 4.238E+00 |
| 175 | 597.4/241.1>GPIns:Lyso 18:1 | 1.208E+00 | 1.068E+00 | 1.078E+00 | 8.338E−01 | 8.706E−01 | 9.725E−01 | 1.093E+00 | 1.164E+00 | 1.039E+00 | 1.167E+00 |
| 176 | 599.4/241.1>GPIns:Lyso 18:0 | 2.202E+00 | 1.811E+00 | 3.039E+00 | 2.755E+00 | 2.784E+00 | 3.136E+00 | 3.399E+00 | 3.315E+00 | 2.522E+00 | 3.625E+00 |
| 177 | 619.5/241.1>GPIns:Lyso 20:4 | 5.690E−01 | 6.646E−01 | 1.177E+00 | 1.311E+00 | 1.095E+00 | 1.298E+00 | 1.568E+00 | 4.598E−01 | 9.422E−01 | 1.062E+00 |
| 178 | 621.5/241.1>GPIns:Lyso 20:3 | 1.606E−01 | 1.790E−01 | 2.624E−01 | 3.483E−01 | 1.484E−01 | 3.090E−01 | 3.532E−01 | 8.302E−02 | 1.496E−01 | 1.999E−01 |
| 179 | 623.5/241.1>GPIns:Lyso 20:2 | 2.906E−02 | 2.771E−02 | 3.090E−02 | 4.022E−02 | 1.766E−02 | 3.262E−02 | 3.814E−02 | 1.827E−02 | 3.004E−02 | 3.029E−02 |
| 180 | 625.5/241.1>GPIns:Lyso 20:1 | 2.636E−02 | 1.803E−02 | 2.440E−02 | 1.864E−02 | 1.839E−02 | 1.275E−02 | 2.036E−02 | 5.641E−02 | 2.416E−02 | 2.661E−02 |
| 181 | 627.5/241.1>GPIns:Lyso 20:0 | 2.820E−02 | 8.387E−03 | 1.741E−02 | 1.557E−02 | 1.058E−02 | 1.471E−02 | 1.337E−02 | 1.606E−02 | 1.061E−02 | 1.999E−02 |
| 182 | 679.5/241.1>GPIns:Lyso 24:2 | 3.728E−02 | 4.966E−02 | 8.093E−02 | 5.874E−02 | 5.788E−02 | 7.161E−02 | 5.898E−02 | 8.841E−02 | 5.297E−02 | 1.619E−01 |
| 183 | 835.7/241.1>GPIns:34:1 | 1.187E+00 | 1.229E+00 | 1.302E+00 | 1.007E+00 | 8.964E−01 | 1.183E+00 | 1.182E+00 | 1.582E+00 | 9.923E−01 | 2.690E+00 |
| 184 | 857.7/241.1>GPIns:36:4 | 9.392E−01 | 9.179E−01 | 1.495E+00 | 1.028E+00 | 1.081E+00 | 1.213E+00 | 1.287E+00 | 1.590E+00 | 9.799E−01 | 2.991E+00 |
| 185 | 859.8/241.1>GPIns:36:3 | 8.204E−01 | 7.909E−01 | 1.076E+00 | 7.296E−01 | 7.210E−01 | 8.907E−01 | 7.983E−01 | 1.278E+00 | 7.541E−01 | 2.051E+00 |
| 186 | 861.8/241.1>GPIns:36:2 | 1.557E+00 | 1.822E+00 | 2.038E+00 | 1.482E+00 | 1.422E+00 | 1.623E+00 | 1.458E+00 | 2.770E+00 | 1.782E+00 | 3.805E+00 |
| 187 | 863.7/241.1>GPIns:36:1 | 6.254E−01 | 6.131E−01 | 4.758E−01 | 4.255E−01 | 3.164E−01 | 4.598E−01 | 5.285E−01 | 6.928E−01 | 5.506E−01 | 9.209E−01 |
| 188 | 865.8/241.1>GPIns:36:0 | 6.376E−02 | 5.874E−02 | 5.334E−02 | 4.378E−02 | 3.029E−02 | 4.856E−02 | 5.555E−02 | 7.321E−02 | 4.709E−02 | 8.645E−02 |
| 189 | 873.8/241.1>GPIns:37:3 | 1.815E−02 | 1.349E−02 | 7.713E−03 | 7.799E−03 | 4.942E−03 | 9.589E−03 | 2.379E−02 | 1.300E−02 | 1.471E−02 | 3.691E−02 |
| 190 | 883.8/241.1>GPIns:38:5 | 1.643E−01 | 1.373E−01 | 2.636E−01 | 1.668E−01 | 1.422E−01 | 1.962E−01 | 2.882E−01 | 1.484E−01 | 1.582E−01 | 3.912E−01 |
| 191 | 885.8/241.1>GPIns:38:4 | 9.692E−01 | 1.189E+00 | 1.991E+00 | 2.253E+00 | 1.613E+00 | 2.380E+00 | 2.323E+00 | 9.183E−01 | 1.519E+00 | 3.005E+00 |
| 192 | 887.8/241.1>GPIns:38:3 | 3.519E−01 | 4.047E−01 | 6.217E−01 | 7.259E−01 | 3.605E−01 | 7.811E−01 | 7.388E−01 | 3.421E−01 | 3.679E−01 | 7.701E−01 |
| 193 | 889.8/241.1>GPIns:38:2 | 7.186E−02 | 7.223E−02 | 9.712E−02 | 8.633E−02 | 4.022E−02 | 8.375E−02 | 7.787E−02 | 8.081E−02 | 6.720E−02 | 1.263E−01 |
| 194 | 891.8/241.1>GPIns:38:1 | 6.916E−02 | 5.481E−02 | 8.608E−02 | 6.536E−02 | 5.641E−02 | 8.559E−02 | 7.382E−02 | 1.864E−01 | 9.135E−02 | 1.349E−01 |
| 195 | 893.8/241.1>GPIns:38:0 | 2.452E−02 | 2.710E−02 | 5.273E−02 | 2.403E−02 | 3.875E−02 | 3.961E−02 | 3.127E−02 | 6.634E−02 | 3.127E−02 | 6.499E−02 |

APPENDIX D-continued

Ovarian Cancer
Training Dataset

| | | | | | | | | | | | |
|---|---|---|---|---|---|---|---|---|---|---|---|
| 196 | 909.8/241.1>GPIns:40:6 | 8.645E−02 | 1.803E−01 | 1.150E−01 | 1.643E−01 | 1.015E−01 | 2.293E−01 | 1.496E−01 | 8.228E−02 | 1.680E−01 | 1.754E−01 |
| 197 | 911.8/241.1>GPIns:40:5 | 7.639E−02 | 9.614E−02 | 8.289E−02 | 1.188E−01 | 5.996E−02 | 1.275E−01 | 1.135E−01 | 5.947E−02 | 1.037E−01 | 1.337E−01 |
| 198 | 913.8/241.1>GPIns:40:4 | 4.181E−02 | 4.390E−02 | 5.273E−02 | 6.180E−02 | 4.513E−02 | 7.603E−02 | 8.081E−02 | 6.634E−02 | 5.003E−02 | 1.085E−01 |
| 199 | 915.8/241.1>GPIns:40:3 | 8.559E−02 | 5.616E−02 | 9.957E−02 | 1.062E−01 | 7.406E−02 | 1.035E−01 | 1.435E−01 | 1.631E−01 | 7.014E−02 | 2.600E−01 |
| 200 | 917.8/241.1>GPIns:40:2 | 7.002E−02 | 4.059E−02 | 6.426E−02 | 4.316E−02 | 3.666E−02 | 6.585E−02 | 5.898E−02 | 1.029E−01 | 3.948E−02 | 1.496E−01 |
| 201 | 919.8/241.1>GPIns:40:1 | 2.452E−02 | 3.090E−02 | 5.910E−02 | 3.899E−02 | 3.250E−02 | 4.341E−02 | 2.882E−02 | 8.841E−02 | 4.476E−02 | 8.486E−02 |
| 202 | 963.9/241.1>GPInsP:38:5 | 1.361E−02 | 6.450E−03 | 9.638E−03 | 1.080E−02 | 1.059E−02 | 5.751E−03 | 1.987E−02 | 1.680E−02 | 1.594E−02 | 1.471E−02 |
| 203 | 963.9/321.1>GPInsP:38:5 | 1.815E−03 | 1.288E−03 | 1.288E−03 | 5.996E−04 | 1.410E−03 | 0.000E+00 | 0.000E+00 | 7.615E−04 | 0.000E+00 | 0.000E+00 |
| 204 | 965.9/241.1>GPInsP:38:4 | 2.551E−02 | 2.134E−02 | 1.410E−02 | 1.386E−02 | 1.766E−02 | 1.852E−02 | 1.288E−02 | 1.067E−02 | 1.361E−02 | 1.692E−02 |
| 205 | 965.9/321.1>GPInsP:38:4 | 6.376E−03 | 5.800E−03 | 1.288E−03 | 2.403E−03 | 6.352E−03 | 2.551E−03 | 4.954E−03 | 3.053E−03 | 2.943E−03 | 1.471E−03 |
| 206 | 967.9/241.1>GPInsP:38:3 | 1.275E−02 | 1.161E−02 | 1.606E−02 | 1.386E−02 | 1.839E−02 | 2.367E−02 | 2.477E−02 | 2.440E−02 | 1.533E−02 | 2.882E−02 |
| 207 | 967.9/321.1>GPInsP:38:3 | 9.099E−03 | 4.513E−03 | 9.001E−03 | 3.605E−03 | 8.461E−03 | 2.551E−03 | 4.954E−03 | 9.908E−03 | 4.120E−03 | 1.034E−02 |
| 208 | 1045.9/241.1>GPInsP2:38:4 | 2.735E−03 | 3.225E−03 | 1.925E−03 | 1.803E−03 | 5.641E−03 | 5.113E−03 | 5.947E−03 | 6.855E−03 | 4.709E−03 | 3.691E−03 |
| 209 | 1045.9/321.1>GPInsP2:38:4 | 9.099E−04 | 6.450E−04 | 6.426E−04 | 5.996E−04 | 7.051E−04 | 1.275E−03 | 0.000E+00 | 0.000E+00 | 5.898E−04 | 1.471E−03 |
| 210 | 1045.9/401.1>GPInsP2:38:4 | 0.000E+00 | 6.450E−04 | 0.000E+00 | 5.996E−04 | 7.051E−04 | 1.275E−03 | 9.920E−04 | 1.521E−03 | 0.000E+00 | 0.000E+00 |
| 211 | 1047.9/321.1>GPInsP2:38:3 | 0.000E+00 | 6.450E−04 | 0.000E+00 | 0.000E+00 | 7.051E−04 | 6.389E−04 | 0.000E+00 | 0.000E+00 | 5.898E−04 | 7.382E−04 |
| 212 | 1047.9/401.1>GPInsP2:38:3 | 4.549E−03 | 1.288E−03 | 3.863E−03 | 2.403E−03 | 2.820E−03 | 2.551E−03 | 4.954E−04 | 2.281E−03 | 2.354E−03 | 2.955E−03 |
| 213 | 1047.9/241.1>GPInsP2:38:3 | 5.457E−03 | 2.575E−03 | 3.213E−03 | 3.004E−03 | 1.410E−03 | 3.838E−03 | 9.920E−04 | 6.094E−03 | 2.354E−03 | 7.382E−03 |
| 214 | 1125.9/241.1>GPInsP3:38:4 | 3.642E−03 | 6.450E−04 | 3.863E−03 | 3.605E−03 | 1.410E−03 | 1.275E−03 | 3.470E−03 | 3.053E−03 | 1.766E−03 | 5.162E−03 |
| 215 | 1125.9/321.1>GPInsP3: 38:4 | 9.099E−04 | 6.450E−04 | 6.426E−04 | 0.000E+00 | 0.060E+00 | 1.275E−03 | 4.954E−04 | 7.615E−04 | 1.178E−03 | 7.382E−04 |
| 216 | 1125.9/401.1>GPInsP3:38:4 | 0.000E+00 | 6.450E−04 | 6.426E−04 | 5.996E−04 | 7.051E−04 | 6.389E−04 | 4.954E−04 | 0.000E+00 | 1.178E−03 | 7.382E−04 |
| 217 | 1125.9/481.1>GPInsP3:38:4 | 9.099E−04 | 4.513E−03 | 0.000E+00 | 1.199E−03 | 7.051E−04 | 1.275E−03 | 9.920E−04 | 1.521E−03 | 0.000E+00 | 1.471E−03 |
| 218 | 835.7/281.1>GPIns:34:1 | 1.610E+00 | 1.473E+00 | 1.600E+00 | 1.145E+00 | 1.094E+00 | 1.352E+00 | 1.365E+00 | 1.672E+00 | 1.177E+00 | 3.013E+00 |
| 219 | 821.8/241.1>GPIns:34:1 | 1.459E−02 | 1.619E−02 | 1.668E−02 | 1.199E−02 | 1.410E−02 | 2.048E−02 | 1.435E−02 | 1.754E−02 | 1.594E−02 | 4.059E−02 |
| 220 | 494.4/184.1>GPCho:Lyso 16:1 | 1.637E+00 | 1.703E+00 | 2.145E+00 | 2.183E+00 | 2.328E+00 | 2.365E+00 | 4.231E+00 | 2.112E+00 | 1.596E+00 | 2.393E+00 |
| 221 | 496.4/184.1>GPCho:Lyso 16:0 | 6.935E+01 | 6.117E+01 | 7.010E+01 | 7.159E+01 | 7.049E+01 | 7.535E+01 | 8.480E+01 | 7.827E+01 | 6.294E+01 | 7.397E+01 |
| 222 | 520.4/184.1>GPCho:Lyso 18:2 | 7.089E+01 | 6.294E+01 | 5.083E+01 | 5.043E+01 | 4.397E+01 | 4.836E+01 | 4.504E+01 | 4.463E+01 | 5.649E+01 | 4.580E+01 |
| 223 | 522.4/184.1>GPCho:Lyso 18:1 | 3.542E+01 | 3.455E+01 | 3.527E+01 | 3.503E+01 | 3.609E+01 | 3.196E+01 | 5.131E+01 | 3.062E+01 | 3.034E+01 | 3.141E+01 |
| 224 | 524.4/184.1>GPCho:Lyso 18:0 | 2.636E+01 | 2.047E+01 | 2.317E+01 | 2.611E+01 | 2.384E+01 | 2.860E+01 | 3.749E+01 | 3.486E+01 | 2.336E+01 | 2.926E+01 |
| 225 | 544.4/184.1>GPCho:Lyso 20:4 | 1.171E+01 | 1.649E+01 | 1.425E+01 | 1.889E+01 | 1.462E+01 | 2.060E+01 | 2.700E+01 | 1.011E+01 | 1.555E+01 | 1.274E+01 |
| 226 | 568.4/184.1>GPCho:Lyso 22:6 | 3.985E+00 | 6.327E+00 | 5.101E+00 | 9.473E+00 | 7.452E+00 | 1.110E+01 | 7.758E+00 | 2.750E+00 | 8.839E+00 | 4.028E+00 |
| 227 | 570.4/184.1>GPCho:Lyso 22:5 | 1.755E+00 | 2.371E+00 | 1.968E+00 | 2.870E+00 | 2.297E+00 | 3.604E+00 | 3.824E+00 | 1.216E+00 | 2.934E+00 | 1.494E+00 |
| 228 | 678.5/184.1>GPCho:28:0 | 6.446E−01 | 8.502E−01 | 3.663E−01 | 4.349E−01 | 4.204E−01 | 4.888E−01 | 6.332E−01 | 6.506E−01 | 4.285E−01 | 4.404E−01 |
| 229 | 678.5/184.1>GPCho:28:0a | 7.251E−01 | 8.916E−01 | 4.083E−01 | 4.966E−01 | 4.630E−01 | 5.025E−01 | 7.231E−01 | 6.833E−01 | 4.540E−01 | 4.488E−01 |
| 230 | 704.6/184.1>GPCho:30:1a | 3.547E+01 | 3.408E+01 | 3.749E+01 | 3.611E+01 | 4.684E+01 | 3.301E+01 | 2.863E+01 | 4.121E+01 | 4.797E+01 | 2.579E+01 |
| 231 | 706.6/184.1>GPCho:30:0a | 5.060E+00 | 6.037E+00 | 3.969E+00 | 4.691E+00 | 5.592E+00 | 4.431E+00 | 4.770E+00 | 5.045E+00 | 4.980E+00 | 3.182E+00 |
| 232 | 718.6/184.1>GPCho:32:0p, 32:1e | 2.057E+00 | 2.093E+00 | 2.080E+00 | 1.690E+00 | 2.234E+00 | 1.871E+00 | 1.647E+00 | 2.312E+00 | 2.399E+00 | 1.732E+00 |
| 233 | 730.8/184.1>GPCho:32:2 | 4.775E+00 | 5.860E+00 | 5.187E+00 | 6.401E+00 | 7.162E+00 | 5.800E+00 | 5.423E+00 | 5.541E+00 | 6.432E+00 | 5.414E+00 |
| 234 | 732.6/184.1>GPCho:32:1a | 1.224E+01 | 1.564E+01 | 1.797E+01 | 2.066E+01 | 2.492E+01 | 1.841E+01 | 2.727E+01 | 1.690E+01 | 1.631E+01 | 1.999E+01 |
| 235 | 732.6/184.1>GPCho:32:0a | 1.032E+01 | 9.732E+00 | 1.222E+01 | 1.017E+01 | 1.321E+01 | 9.464E+00 | 1.216E+01 | 1.263E+01 | 9.965E+00 | 9.824E+00 |
| 236 | 742.6/184.1>GPCho:34:2p, 34:3e | 1.655E+00 | 1.300E+00 | 1.105E+00 | 6.719E−01 | 8.549E−01 | 7.639E−01 | 8.339E−01 | 1.204E+00 | 1.259E+00 | 1.138E+00 |
| 237 | 744.6/184.1>GPCho:34:1p, 34:2e | 7.633E+00 | 6.496E+00 | 4.729E+00 | 3.120E+00 | 3.330E+00 | 3.174E+00 | 3.393E+00 | 3.727E+00 | 5.149E+00 | 5.068E+00 |
| 238 | 746.6/184.1>GPCho:34:0p, 34:1e | 7.695E+00 | 7.676E+00 | 7.245E+00 | 6.091E+00 | 7.027E+00 | 5.433E+00 | 6.192E+00 | 7.384E+00 | 7.126E+00 | 6.615E+00 |
| 239 | 748.6/184.1>GPCho:34:0e | 1.537E+00 | 1.471E+00 | 1.508E+00 | 1.242E+00 | 1.511E+00 | 1.235E+00 | 1.352E+00 | 1.765E+00 | 1.430E+00 | 1.367E+00 |
| 240 | 756.6/184.1>GPCho:34:3a | 2.324E+01 | 1.234E+01 | 2.043E+01 | 1.178E+01 | 1.368E+01 | 1.259E+01 | 1.558E+01 | 3.099E+01 | 1.617E+01 | 2.611E+01 |
| 241 | 758.7/184.1>GPCho:34:2a | 2.747E+02 | 2.517E+02 | 2.336E+02 | 2.089E+02 | 1.871E+02 | 1.997E+02 | 1.717E+02 | 2.030E+02 | 2.190E+02 | 2.207E+02 |
| 242 | 760.6/184.1>GPCho:34:1a | 1.482E+02 | 1.530E+02 | 1.847E+02 | 1.670E+02 | 1.625E+02 | 1.437E+02 | 2.027E+02 | 1.296E+02 | 1.298E+02 | 1.822E+02 |
| 243 | 762.6/184.1>GPCho:34:0a | 1.278E+01 | 1.331E+01 | 1.734E+01 | 1.603E+01 | 1.550E+01 | 1.317E+01 | 2.024E+01 | 1.232E+01 | 1.160E+01 | 1.880E+01 |
| 244 | 768.6/184.1>GPCho:36:3p, 36:4e | 9.594E+00 | 1.161E+01 | 1.016E+01 | 7.892E+00 | 9.177E+00 | 9.712E+00 | 9.516E+00 | 6.486E+00 | 1.021E+01 | 8.446E+00 |
| 245 | 770.6/184.1>GPCho:36:2p, 36:3e | 6.159E+00 | 7.123E+00 | 5.546E+00 | 4.249E+00 | 4.292E+00 | 4.979E+00 | 4.544E+00 | 5.074E+00 | 5.674E+00 | 5.444E+00 |

APPENDIX D-continued

| | | Ovarian Cancer Training Dataset | | | | | | | | | |
|---|---|---|---|---|---|---|---|---|---|---|---|
| 246 | 772.6/184.1>GPCho:36:1p, 36:2e | 9.246E+00 | 7.952E+00 | 6.750E+00 | 5.097E+00 | 5.969E+00 | 6.174E+00 | 5.798E+00 | 1.022E+01 | 7.571E+00 | 8.629E+00 |
| 247 | 774.6/184.1>GPCho:36:0p, 36:1e | 5.187E+00 | 4.651E+00 | 4.510E+00 | 4.152E+00 | 4.721E+00 | 4.952E+00 | 5.806E+00 | 5.890E+00 | 5.320E+00 | 5.820E+00 |
| 248 | 782.6/184.1>GPCho:36:4a | 5.884E+01 | 7.095E+01 | 6.151E+01 | 7.398E+01 | 5.602E+01 | 7.916E+01 | 9.253E+01 | 4.185E+01 | 5.689E+01 | 7.310E+01 |
| 249 | 784.6/184.1>GPCho:36:3a | 6.954E+01 | 7.521E+01 | 5.857E+01 | 6.318E+01 | 4.065E+01 | 7.808E+01 | 7.025E+01 | 5.403E+01 | 4.701E+01 | 7.260E+01 |
| 250 | 786.6/184.1>GPCho:36:2a | 1.364E+02 | 1.218E+02 | 1.104E+02 | 1.082E+02 | 8.781E+01 | 1.068E+02 | 1.038E+02 | 1.192E+02 | 1.071E+02 | 1.405E+02 |
| 251 | 788.6/184.1>GPCho:36:1a | 5.339E+01 | 4.459E+01 | 4.651E+01 | 4.502E+01 | 4.290E+01 | 4.459E+01 | 6.435E+01 | 6.164E+01 | 4.293E+01 | 6.750E+01 |
| 252 | 790.8/184.1>GPCho:36:0 | 3.832E+00 | 3.217E+00 | 3.449E+00 | 3.275E+00 | 3.267E+00 | 3.332E+00 | 5.077E+00 | 4.690E+00 | 3.304E+00 | 5.287E+00 |
| 253 | 792.6/184.1>GPCho:38:5p, 38:6e | 4.150E+00 | 4.758E+00 | 4.219E+00 | 3.532E+00 | 4.157E+00 | 4.200E+00 | 3.517E+00 | 3.772E+00 | 4.551E+00 | 3.448E+00 |
| 254 | 794.6/184.1>GPCho:38:4p, 38:5e | 7.640E+00 | 1.122E+01 | 8.661E+00 | 7.789E+00 | 8.656E+00 | 8.151E+00 | 7.386E+00 | 6.686E+00 | 1.014E+01 | 7.485E+00 |
| 255 | 796.6/184.1>GPCho:38:3p, 38:4e | 7.413E+00 | 1.032E+01 | 8.187E+00 | 7.319E+00 | 8.275E+00 | 8.166E+00 | 8.555E+00 | 6.940E+00 | 8.665E+00 | 7.438E+00 |
| 256 | 798.6/184.1>GPCho:38:2p, 38:3e | 3.456E+00 | 3.491E+00 | 2.957E+00 | 2.663E+00 | 2.976E+00 | 3.384E+00 | 3.159E+00 | 4.137E+00 | 3.135E+00 | 4.052E+00 |
| 257 | 800.6/184.1>GPCho:38:1p, 38:2e | 6.239E+00 | 4.742E+00 | 5.068E+00 | 4.613E+00 | 5.796E+00 | 5.802E+00 | 4.339E+00 | 7.478E+00 | 6.901E+00 | 5.524E+00 |
| 258 | 808.6/184.1>GPCho:38:5a | 1.496E+01 | 2.189E+01 | 1.862E+01 | 2.443E+01 | 1.739E+01 | 2.892E+01 | 3.065E+01 | 1.245E+01 | 2.016E+01 | 2.186E+01 |
| 259 | 810.6/184.1>GPCho:38:4a | 2.505E+01 | 3.364E+01 | 3.273E+01 | 4.190E+01 | 3.021E+01 | 4.506E+01 | 5.825E+01 | 2.588E+01 | 2.997E+01 | 4.260E+01 |
| 260 | 812.6/184.1>GPCho:38:3a | 3.101E+01 | 3.007E+01 | 3.216E+01 | 3.867E+01 | 3.253E+01 | 4.379E+01 | 4.277E+01 | 3.391E+01 | 2.815E+01 | 3.806E+01 |
| 261 | 814.6/184.1>GPCho:38:2a | 3.170E+01 | 3.196E+01 | 3.578E+01 | 3.750E+01 | 4.551E+01 | 3.630E+01 | 2.921E+01 | 4.359E+01 | 3.790E+01 | 3.067E+01 |
| 262 | 816.6/184.1>GPCho:38:1a | 1.221E+01 | 1.089E+01 | 1.191E+01 | 1.102E+01 | 1.190E+01 | 1.371E+01 | 1.034E+01 | 1.871E+01 | 1.262E+01 | 1.249E+01 |
| 263 | 820.6/184.1>GPCho:40:5p, 40:6e | 2.431E+00 | 3.493E+00 | 2.293E+00 | 2.542E+00 | 2.739E+00 | 3.170E+00 | 2.405E+00 | 2.261E+00 | 3.217E+00 | 2.388E+00 |
| 264 | 822.6/184.1>GPCho:40:4p, 40:5e | 2.872E+00 | 3.438E+00 | 2.321E+00 | 2.428E+00 | 2.729E+00 | 2.619E+00 | 2.491E+00 | 3.313E+00 | 2.993E+00 | 3.057E+00 |
| 265 | 824.6/184.1>GPCho:40:3p, 40:4e | 2.145E+00 | 2.647E+00 | 2.023E+00 | 1.866E+00 | 2.147E+00 | 1.901E+00 | 2.112E+00 | 2.795E+00 | 1.954E+00 | 2.778E+00 |
| 266 | 826.6/184.1>GPCho:40:2p, 40:3e | 2.850E+00 | 2.007E+00 | 2.104E+00 | 1.730E+00 | 2.171E+00 | 1.870E+00 | 1.985E+00 | 4.350E+00 | 2.121E+00 | 3.872E+00 |
| 267 | 828.6/184.1>GPCho:40:1p, 40:2e | 2.924E+00 | 2.002E+00 | 2.341E+00 | 1.809E+00 | 2.747E+00 | 2.291E+00 | 2.117E+00 | 4.361E+00 | 2.407E+00 | 3.482E+00 |
| 268 | 834.6/184.1>GPCho:40:6a | 5.741E+00 | 7.895E+00 | 7.872E+00 | 1.462E+01 | 9.955E+00 | 1.582E+01 | 1.352E+01 | 5.805E+00 | 1.068E+01 | 1.094E+01 |
| 269 | 836.6/184.1>GPCho:40:5a | 5.808E+00 | 5.656E+00 | 5.348E+00 | 8.493E+00 | 6.007E+00 | 9.381E+00 | 9.903E+00 | 6.939E+00 | 6.353E+00 | 9.373E+00 |
| 270 | 838.6/184.1>GPCho:40:4a | 3.021E+00 | 2.671E+00 | 2.685E+00 | 3.091E+00 | 2.426E+00 | 3.774E+00 | 5.285E+00 | 4.160E+00 | 2.564E+00 | 5.001E+00 |
| 271 | 701.5/184.1>SM:18/16:1 | 1.225E+01 | 1.086E+01 | 1.285E+01 | 1.445E+01 | 1.751E+01 | 1.298E+01 | 1.079E+01 | 1.445E+01 | 1.730E+01 | 9.218E+00 |
| 272 | 703.5/184.1>SM:18/16:0 | 8.425E+01 | 8.268E+01 | 9.324E+01 | 8.878E+01 | 1.158E+02 | 8.535E+01 | 7.009E+01 | 1.009E+02 | 1.152E+02 | 6.302E+01 |
| 273 | 703.8/184.4>SM:d18:1/16:0 | 9.254E+01 | 9.360E+01 | 1.013E+02 | 9.756E+01 | 1.271E+02 | 9.568E+01 | 7.888E+01 | 1.134E+02 | 1.285E+02 | 6.513E+01 |
| 274 | 705.8/184.4>SM:d18:0/16:0 | 1.376E+01 | 1.477E+01 | 1.406E+01 | 1.481E+01 | 2.039E+01 | 1.363E+01 | 1.150E+01 | 1.759E+01 | 1.913E+01 | 9.047E+00 |
| 275 | 727.6/184.1>SM:18/18:2 | 7.082E−01 | 6.879E−01 | 7.392E−01 | 5.549E−01 | 8.334E−01 | 6.214E−01 | 5.383E−01 | 1.165E+00 | 1.082E+00 | 6.601E−01 |
| 276 | 729.6/184.1>SM:18/18:1 | 6.941E+00 | 7.124E+00 | 9.445E+00 | 1.164E+01 | 1.376E+01 | 9.681E+00 | 8.876E+00 | 1.034E+01 | 1.237E+01 | 8.922E+00 |
| 277 | 731.6/184.1>SM:18/18:0 | 1.618E+01 | 1.952E+01 | 2.428E+01 | 2.846E+01 | 3.778E+01 | 2.526E+01 | 2.323E+01 | 2.679E+01 | 2.788E+01 | 2.195E+01 |
| 278 | 731.8/184.4>SM:d18:1/18:0 | 1.595E+01 | 1.936E+01 | 2.387E+01 | 2.833E+01 | 3.828E+01 | 2.548E+01 | 2.376E+01 | 2.734E+01 | 2.765E+01 | 2.079E+01 |
| 279 | 733.8/184.4>SM:d18:0/18:0 | 4.217E+00 | 5.656E+00 | 6.553E+00 | 7.967E+00 | 1.086E+01 | 6.744E+00 | 1.046E+01 | 7.289E+00 | 6.322E+00 | 7.256E+00 |
| 280 | 757.6/184.1>SM:18/20:1 | 7.651E+00 | 5.437E+00 | 7.778E+00 | 6.355E+00 | 6.890E+00 | 6.131E+00 | 5.948E+00 | 1.019E+01 | 7.082E+00 | 8.403E+00 |
| 281 | 759.6/184.1>SM:18/20:0 | 1.243E+02 | 1.247E+02 | 1.123E+02 | 1.096E+02 | 9.381E+01 | 1.037E+02 | 8.415E+01 | 1.010E+02 | 1.102E+02 | 1.173E+02 |
| 282 | 759.8/184.4>SM:d18:1/20:0 | 1.087E+02 | 1.107E+02 | 9.720E+01 | 9.749E+01 | 8.677E+01 | 9.201E+01 | 7.638E+01 | 8.955E+01 | 9.949E+01 | 1.029E+02 |
| 283 | 761.8/184.4>SM:d18:0/20:0 | 4.142E+01 | 4.657E+01 | 5.688E+01 | 5.403E+01 | 5.074E+01 | 4.477E+01 | 6.800E+01 | 3.895E+01 | 3.974E+01 | 6.283E+01 |
| 284 | 773.6/184.1>SM:18/21:0 | 6.759E+00 | 5.632E+00 | 5.200E+00 | 5.060E+00 | 5.647E+00 | 6.797E+00 | 5.645E+00 | 7.592E+00 | 7.217E+00 | 5.561E+00 |
| 285 | 787.6/184.1>SM:18/22:0 | 7.878E+01 | 7.458E+01 | 6.946E+01 | 6.958E+01 | 6.394E+01 | 7.559E+01 | 6.905E+01 | 8.244E+01 | 7.458E+01 | 8.280E+01 |
| 286 | 787.9/184.4>SM:d1:1/22:0 | 5.711E+01 | 6.028E+01 | 5.548E+01 | 5.569E+01 | 5.267E+01 | 6.203E+01 | 5.464E+01 | 6.662E+01 | 6.003E+01 | 6.141E+01 |
| 287 | 789.9/184.4>SM:d18:0/22:0 | 9.387E+00 | 8.420E+00 | 8.592E+00 | 8.674E+00 | 8.277E+00 | 8.869E+00 | 1.371E+01 | 1.152E+01 | 8.311E+00 | 1.353E+01 |
| 288 | 813.6/184.1>SM:18/24:1 | 5.878E+01 | 6.382E+01 | 6.974E+01 | 7.419E+01 | 9.018E+01 | 7.462E+01 | 5.848E+01 | 7.872E+01 | 7.536E+01 | 5.301E+01 |
| 289 | 813.9/184.4>SM:d18:1/24:1 | 4.760E+01 | 5.234E+01 | 5.969E+01 | 6.186E+01 | 7.977E+01 | 6.062E+01 | 4.485E+01 | 6.446E+01 | 6.409E+01 | 4.141E+01 |
| 290 | 815.6/184.1>SM:18/24:0 | 1.824E+01 | 2.169E+01 | 2.128E+01 | 2.177E+01 | 2.471E+01 | 2.730E+01 | 1.842E+01 | 2.787E+01 | 2.363E+01 | 1.608E+01 |
| 291 | 815.9/184.4>SM:d18:0/24:1 | 1.452E+01 | 1.837E+01 | 1.764E+01 | 1.757E+01 | 2.079E+01 | 2.240E+01 | 1.503E+01 | 2.335E+01 | 2.032E+01 | 1.286E+01 |
| 292 | 817.9/184.4>SM:d18:0/24:0 | 2.223E+00 | 2.054E+00 | 2.247E+00 | 2.024E+00 | 2.084E+00 | 2.449E+00 | 1.976E+00 | 3.560E+00 | 2.383E+00 | 2.787E+00 |
| 293 | 841.9/184.4>SM:d18:1/26:1 | 1.974E+00 | 1.274E+00 | 1.569E+00 | 1.439E+00 | 1.796E+00 | 1.587E+00 | 1.730E+00 | 3.555E+00 | 1.657E+00 | 2.446E+00 |
| 294 | 843.9/184.4>SM:d18:0/26:1 | 1.828E+00 | 1.607E+00 | 1.846E+00 | 1.480E+00 | 1.358E+00 | 1.599E+00 | 1.422E+00 | 2.427E+00 | 1.663E+00 | 3.148E+00 |
| 295 | 843.9/184.4>SM:d18:1/26:0 | 1.759E+00 | 1.638E+00 | 1.847E+00 | 1.456E+00 | 1.351E+00 | 1.619E+00 | 1.444E+00 | 2.364E+00 | 1.665E+00 | 3.157E+00 |

APPENDIX D-continued

| | Ovarian Cancer Training Dataset | | | | | | | | | | |
|---|---|---|---|---|---|---|---|---|---|---|---|
| 296 | 845.9/184.4>SM:d18:0/26:0 | 9.804E−01 | 9.868E−01 | 1.470E+00 | 1.082E+00 | 1.056E+00 | 1.056E+00 | 1.265E+00 | 1.332E+00 | 1.067E+00 | 2.489E+00 |
| 297 | 538.7/264.4>Cer:d18:1/16:0 | 4.073E−01 | 3.718E−01 | 5.463E−01 | 2.975E−01 | 4.902E−01 | 3.030E−01 | 2.753E−01 | 4.580E−01 | 4.999E−01 | 3.840E−01 |
| 298 | 540.7/266.4>Cer:d18:0/16:0 | 2.617E−02 | 2.231E−02 | 2.117E−02 | 1.776E−02 | 2.617E−02 | 1.630E−02 | 1.223E−02 | 1.929E−02 | 2.467E−02 | 7.830E−03 |
| 299 | 566.7/264.4>Cer:d18:1/18:0 | 8.731E−02 | 8.323E−02 | 1.418E−01 | 1.450E−01 | 2.395E−01 | 1.203E−01 | 1.304E−01 | 1.562E−01 | 1.405E−01 | 1.392E−01 |
| 300 | 568.7/266.4>Cer:d18:0/18:0 | 7.594E−03 | 5.299E−03 | 5.942E−03 | 7.337E−03 | 1.667E−02 | 3.690E−03 | 9.224E−03 | 1.178E−02 | 9.396E−03 | 3.926E−03 |
| 301 | 594.7/264.4>Cer:d18:1/20:0 | 7.830E−02 | 8.924E−02 | 9.589E−02 | 9.847E−02 | 1.409E−01 | 9.203E−02 | 8.752E−02 | 1.274E−01 | 9.825E−02 | 7.658E−02 |
| 302 | 596.7/266.4>Cer:d18:0/20:0 | 2.130E−02 | 1.611E−02 | 2.617E−02 | 1.450E−02 | 1.667E−02 | 2.446E−02 | 3.432E−02 | 2.617E−02 | 3.990E−02 | 7.122E−03 |
| 303 | 622.8/264.4>Cer:d18:1/22:0 | 3.087E−01 | 3.659E−01 | 3.494E−01 | 3.073E−01 | 3.771E−01 | 3.440E−01 | 3.715E−01 | 3.418E−01 | 4.144E−01 | 2.019E−01 |
| 304 | 624.8/266.4>Cer:d18:0/22:0 | 5.256E−03 | 3.604E−03 | 9.031E−03 | 4.097E−03 | 5.277E−03 | 5.878E−03 | 6.929E−03 | 4.290E−03 | 4.076E−03 | 5.706E−03 |
| 305 | 648.9/264.4>Cer:d18:1/24:1 | 5.051E−01 | 6.391E−01 | 6.048E−01 | 6.406E−01 | 8.047E−01 | 4.831E−01 | 5.284E−01 | 5.756E−01 | 7.624E−01 | 3.470E−01 |
| 306 | 650.9/266.4>Cer:d18:0/24:1 | 3.883E−02 | 4.248E−02 | 3.861E−02 | 4.870E−02 | 6.114E−02 | 4.076E−02 | 4.226E−02 | 3.797E−02 | 4.355E−02 | 1.549E−02 |
| 307 | 650.9/264.4>Cer:d18:1/24:0 | 2.401E+00 | 3.066E+00 | 1.838E+00 | 2.323E+00 | 1.964E+00 | 2.717E+00 | 2.316E+00 | 1.752E+00 | 2.928E+00 | 6.131E−01 |
| 308 | 652.9/266.4>Cer:d18:0/24:0 | 3.583E−02 | 4.805E−02 | 3.025E−02 | 3.883E−02 | 3.883E−02 | 4.934E−02 | 4.183E−02 | 2.767E−02 | 4.827E−02 | 1.068E−02 |
| 309 | 676.9/264.4>Cer:d18:1/26:1 | 5.835E−03 | 6.157E−03 | 7.380E−03 | 6.479E−03 | 9.546E−03 | 4.998E−03 | 7.380E−03 | 9.117E−03 | 6.328E−03 | 4.441E−03 |
| 310 | 678.9/266.4>Cer:d18:0/26:1 | 6.715E−03 | 3.604E−03 | 2.853E−03 | 3.583E−03 | 3.647E−03 | 2.617E−03 | 3.926E−03 | 3.754E−03 | 2.660E−03 | 2.488E−03 |
| 311 | 678.9/264.4>Cer:d18:1/26:0 | 2.042E−03 | 1.907E−03 | 1.903E−03 | 5.127E−04 | 8.130E−04 | 3.046E−03 | 1.154E−03 | 2.143E−03 | 2.042E−03 | 7.122E−04 |
| 312 | 680.9/266.4>Cer:d18:0/26:0 | 1.459E−03 | 8.474E−04 | 1.665E−03 | 1.708E−04 | 8.130E−04 | 2.167E−04 | 4.612E−04 | 1.070E−03 | 2.042E−04 | 3.561E−04 |
| 313 | 700.7/264.4>MonoHexCer:d18:1/16:0 | 2.466E−01 | 2.260E−01 | 1.926E−01 | 1.512E−01 | 3.350E−01 | 1.609E−01 | 1.336E−01 | 2.400E−01 | 2.578E−01 | 4.483E−02 |
| 314 | 702.7/266.4>MonoHexCer:d18:0/16:0 | 1.781E−02 | 8.259E−03 | 7.144E−03 | 5.299E−03 | 1.321E−02 | 7.616E−03 | 7.616E−03 | 1.206E−02 | 1.184E−02 | 3.561E−03 |
| 315 | 728.7/264.4>MonoHexCer:d18:1/18:0 | 4.762E−02 | 5.792E−02 | 2.917E−02 | 3.690E−02 | 5.942E−02 | 4.076E−02 | 3.583E−02 | 4.762E−02 | 5.427E−02 | 1.246E−02 |
| 316 | 730.7/266.4>MonoHexCer:d18:0/18:0 | 4.076E−03 | 1.697E−03 | 1.188E−03 | 1.367E−03 | 2.231E−03 | 2.381E−03 | 2.317E−03 | 2.682E−03 | 2.252E−03 | 8.903E−04 |
| 317 | 756.7/264.4>MonoHexCer:d18:1/20:0 | 4.955E−02 | 4.998E−02 | 2.338E−02 | 4.054E−02 | 5.384E−02 | 3.583E−02 | 2.939E−02 | 4.097E−02 | 4.119E−02 | 1.139E−02 |
| 318 | 758.7/266.4>MonoHexCer:d18:0/20:0 | 1.459E−03 | 1.697E−03 | 3.089E−03 | 1.708E−03 | 2.853E−03 | 4.569E−03 | 2.317E−03 | 3.475E−03 | 3.883E−03 | 1.602E−03 |
| 319 | 784.8/264.4>MonoHexCer:d18:1/22:0 | 3.011E−01 | 3.052E−01 | 1.944E−01 | 1.635E−01 | 3.145E−01 | 2.515E−01 | 1.851E−01 | 3.511E−01 | 3.564E−01 | 7.251E−02 |
| 320 | 786.8/266.4>MonoHexCer:d18:0/22:0 | 8.752E−04 | 2.119E−04 | 7.144E−04 | 1.195E−03 | 1.017E−03 | 4.355E−04 | 9.224E−04 | 1.339E−03 | 1.429E−03 | 1.781E−04 |
| 321 | 810.9/264.4>MonoHexCer:d18:1/24:1 | 3.286E−01 | 3.926E−01 | 2.059E−01 | 2.178E−01 | 4.791E−01 | 2.260E−01 | 1.429E−01 | 3.372E−01 | 4.158E−01 | 6.993E−02 |
| 322 | 812.9/266.4>MonoHexCer:d18:0/24:1 | 8.752E−03 | 1.356E−02 | 8.323E−03 | 5.814E−03 | 1.300E−02 | 9.353E−03 | 5.084E−03 | 1.098E−02 | 1.714E−02 | 2.853E−03 |
| 323 | 812.9/264.4>MonoHexCer:d18:1/24:0 | 3.478E−01 | 4.218E−01 | 2.205E−01 | 1.847E−01 | 3.190E−01 | 2.873E−01 | 2.102E−01 | 3.653E−01 | 4.193E−01 | 6.757E−02 |
| 324 | 814.9/266.4>MonoHexCer:d18:0/24:0 | 1.489E−02 | 1.463E−02 | 7.380E−03 | 8.195E−03 | 8.731E−03 | 7.165E−03 | 6.929E−03 | 9.117E−03 | 9.804E−03 | 3.389E−03 |
| 325 | 838.9/264.4>MonoHexCer:d18:1/26:1 | 2.252E−02 | 1.802E−02 | 1.474E−02 | 1.502E−02 | 1.686E−02 | 1.716E−02 | 7.851E−03 | 1.500E−02 | 1.695E−02 | 6.050E−03 |
| 326 | 840.9/266.4>MonoHexCer:d18:0/26:1 | 1.459E−03 | 1.697E−03 | 1.903E−03 | 1.367E−03 | 1.422E−03 | 1.304E−03 | 2.531E−03 | 2.143E−03 | 1.429E−03 | 7.122E−04 |
| 327 | 840.9/264.4>MonoHexCer:d18:1/26:0 | 2.446E−02 | 2.231E−02 | 1.427E−02 | 1.980E−02 | 2.531E−02 | 2.381E−02 | 2.077E−02 | 1.849E−02 | 2.317E−02 | 7.658E−03 |
| 328 | 842.9/266.4>MonoHexCer:d18:0/26:0 | 1.167E−03 | 2.746E−03 | 2.381E−03 | 1.367E−03 | 2.446E−03 | 1.304E−03 | 2.767E−03 | 2.682E−03 | 1.836E−03 | 7.122E−04 |
| 329 | 862.7/264.4>DiHexCer:d18:1/16:0 | 4.488E−01 | 5.798E−01 | 4.963E−01 | 4.959E−01 | 8.273E−01 | 3.323E−01 | 3.357E−01 | 6.851E−01 | 6.499E−01 | 1.377E−01 |
| 330 | 864.7/266.4>DiHexCer:d18:0/16:0 | 5.535E−03 | 7.422E−03 | 4.526E−03 | 4.441E−03 | 9.546E−03 | 6.307E−03 | 5.771E−03 | 8.045E−03 | 7.144E−03 | 2.488E−03 |
| 331 | 890.7/264.4>DiHexCer:d18:1/18:0 | 3.540E−02 | 4.548E−02 | 3.561E−02 | 4.248E−02 | 6.715E−02 | 4.505E−02 | 4.677E−02 | 4.505E−02 | 5.535E−02 | 1.264E−02 |
| 332 | 892.7/266.4>DiHexCer:d18:0/18:0 | 5.835E−04 | 1.272E−03 | 1.903E−03 | 5.127E−04 | 1.626E−03 | 8.688E−04 | 1.384E−03 | 2.682E−03 | 6.114E−04 | 3.561E−04 |
| 333 | 918.7/264.4>DiHexCer:d18:1/20:0 | 3.025E−02 | 3.175E−02 | 2.360E−02 | 3.046E−02 | 4.870E−02 | 3.282E−02 | 3.604E−02 | 2.982E−02 | 3.518E−02 | 1.122E−02 |
| 334 | 920.7/266.4>DiHexCer:d18:0/20:0 | 1.459E−03 | 8.474E−04 | 4.762E−04 | 8.538E−04 | 4.054E−04 | 2.167E−04 | 6.929E−04 | 2.682E−04 | 2.042E−04 | 3.561E−04 |
| 335 | 946.8/264.4>DiHexCer:d18:1/22:0 | 5.942E−02 | 6.564E−02 | 4.891E−02 | 4.333E−02 | 7.380E−02 | 7.101E−02 | 5.792E−02 | 8.216E−02 | 8.881E−02 | 1.798E−02 |
| 336 | 948.8/266.4>D1HexCer:d18:0/22:0 | 7.294E−03 | 3.604E−03 | 4.290E−03 | 3.754E−03 | 2.032E−03 | 4.119E−03 | 4.848E−03 | 4.548E−03 | 3.068E−03 | 1.602E−03 |
| 337 | 972.9/264.4>DiHexCer:d18:1/24:1 | 1.030E−01 | 1.356E−01 | 1.167E−01 | 9.782E−02 | 1.920E−01 | 9.718E−02 | 7.465E−02 | 1.690E−01 | 1.750E−01 | 2.553E−02 |
| 338 | 974.9/266.4>DiHexCer:d18:0/24:1 | 2.617E−03 | 2.338E−03 | 1.188E−03 | 1.536E−03 | 3.861E−03 | 8.688E−04 | 1.384E−03 | 2.403E−03 | 1.429E−03 | 8.903E−04 |
| 339 | 974.9/264.4>DiHexCer:d18:1/24:0 | 5.277E−02 | 7.658E−02 | 5.191E−02 | 5.191E−02 | 7.916E−02 | 7.058E−02 | 5.234E−02 | 6.607E−02 | 9.310E−02 | 1.461E−02 |
| 340 | 976.9/266.4>DiHexCer:d18:0/24:0 | 6.715E−03 | 2.960E−03 | 3.325E−03 | 2.724E−03 | 3.861E−03 | 3.046E−03 | 3.926E−03 | 3.218E−03 | 4.891E−03 | 5.342E−04 |
| 341 | 1000.9/264.4>DiHexCer:d18:1/26:1 | 1.489E−02 | 1.146E−02 | 8.323E−03 | 7.680E−03 | 1.077E−02 | 6.950E−03 | 8.774E−03 | 1.206E−02 | 1.062E−02 | 5.342E−03 |
| 342 | 1002.9/266.4>DiHexCer:d18:0/26:1 | 1.750E−03 | 8.474E−04 | 1.427E−03 | 8.538E−04 | 8.130E−04 | 8.688E−04 | 2.317E−03 | 1.070E−03 | 1.021E−03 | 1.068E−03 |
| 343 | 1002.9/264.4>DiHexCer:d18:1/26:0 | 8.452E−03 | 8.903E−03 | 9.267E−03 | 9.396E−03 | 1.158E−02 | 1.238E−02 | 8.066E−03 | 1.420E−02 | 9.997E−03 | 8.731E−03 |
| 344 | 1004.9/266.4>DiHexCer:d18:0/26:0 | 2.917E−04 | 4.248E−04 | 4.762E−04 | 0.000E+00 | 8.130E−04 | 2.167E−04 | 1.154E−03 | 2.682E−04 | 0.000E+00 | 7.122E−04 |

APPENDIX D-continued

Ovarian Cancer
Training Dataset

| | L | M | N | O | P | Q | R | S | T | U | V | W | X |
|---|---|---|---|---|---|---|---|---|---|---|---|---|---|
| 1 | CA259 | CA269 | 13615 | 14660 | 13551 | 14649 | 14534 | 14432 | CA057 | CA274 | 13835 | 13848 | 13805 |
| 2 | Control | Control | Late Malignant | Early Malignant | Late Malignant | Early Malignant | Early Malignant | Early Malignant | Control | Control | Late Malignant | Late Malignant | Late Malignant |
| 3 | 0 | 0 | 3 | 2 | 3 | 2 | 2 | 2 | 0 | 0 | 3 | 3 | 3 |
| 4 | 1 | 1 | −1 | −1 | −1 | −1 | −1 | −1 | 1 | 1 | −1 | −1 | −1 |
| 5 | 2.376E+00 | 2.438E+00 | 2.729E+00 | 2.085E+00 | 2.025E+00 | 1.523E+00 | 2.427E+00 | 2.572E+00 | 2.973E+00 | 1.897E+00 | 2.961E+00 | 2.393E+00 | 2.684E+00 |
| 6 | 1.470E+00 | 1.212E+00 | 7.377E−01 | 4.163E−01 | 3.766E−01 | 7.271E−01 | 7.200E−01 | 8.278E−01 | 1.726E+00 | 6.088E−01 | 5.194E−01 | 7.252E−01 | 8.026E−01 |
| 7 | 3.047E−01 | 4.775E−01 | 3.058E−01 | 1.717E−01 | 2.178E−01 | 2.886E−01 | 2.639E−01 | 2.800E−01 | 3.605E−01 | 1.974E−01 | 2.028E−01 | 3.047E−01 | 3.519E−01 |
| 8 | 1.881E+00 | 1.373E+00 | 2.671E+00 | 2.868E+00 | 1.100E+00 | 1.111E+00 | 1.572E+00 | 1.193E+00 | 1.374E+00 | 2.216E+00 | 4.474E+00 | 1.507E+00 | 1.663E+00 |
| 9 | 3.283E−02 | 2.350E−02 | 2.457E−02 | 2.361E−02 | 1.588E−02 | 1.395E−02 | 2.124E−02 | 1.534E−02 | 4.442E−02 | 2.886E−02 | 4.099E−02 | 3.433E−02 | 2.725E−02 |
| 10 | 3.283E−02 | 3.444E−02 | 8.187E−03 | 3.380E−03 | 9.067E−03 | 3.262E−02 | 2.178E−02 | 1.127E−02 | 1.545E−02 | 1.813E−02 | 1.363E−02 | 1.459E−02 | 9.356E−03 |
| 11 | 2.371E−02 | 2.350E−02 | 1.738E−02 | 3.380E−03 | 1.058E−02 | 1.545E−02 | 1.534E−02 | 1.534E−02 | 2.039E−02 | 1.524E−02 | 6.835E−03 | 1.277E−02 | 1.105E−02 |
| 12 | 1.288E−02 | 1.127E−02 | 9.206E−03 | 1.148E−02 | 7.554E−03 | 8.552E−03 | 1.137E−02 | 9.442E−03 | 1.234E−02 | 7.833E−03 | 1.459E−02 | 9.549E−03 | 1.448E−02 |
| 13 | 1.781E−02 | 7.833E−03 | 3.176E−02 | 3.509E−02 | 1.438E−02 | 7.489E−03 | 1.234E−02 | 1.298E−02 | 1.792E−02 | 2.843E−02 | 5.268E−02 | 1.910E−02 | 1.867E−02 |
| 14 | 6.620E−02 | 6.094E−02 | 4.710E−02 | 4.056E−02 | 4.764E−02 | 3.906E−02 | 4.345E−02 | 6.084E−02 | 1.084E−01 | 3.627E−02 | 3.412E−02 | 5.665E−02 | 4.249E−02 |
| 15 | 9.152E−03 | 8.273E−03 | 6.137E−03 | 2.704E−03 | 5.290E−03 | 4.807E−03 | 4.936E−03 | 2.951E−03 | 1.352E−02 | 8.240E−03 | 1.567E−02 | 6.363E−03 | 6.803E−03 |
| 16 | 1.609E−03 | 4.356E−04 | 4.088E−03 | 0.000E+00 | 0.000E+00 | 1.070E−03 | 0.000E+00 | 3.541E−03 | 6.170E−04 | 0.000E+00 | 0.000E+00 | 0.000E+00 | 0.000E+00 |
| 17 | 1.023E−02 | 6.094E−03 | 1.438E−02 | 6.749E−03 | 3.777E−03 | 8.015E−03 | 5.440E−03 | 8.852E−03 | 5.547E−03 | 7.833E−03 | 4.882E−03 | 7.006E−03 | 1.021E−02 |
| 18 | 2.747E−02 | 3.745E−02 | 7.779E−02 | 4.657E−02 | 4.303E−02 | 5.397E−02 | 2.124E−02 | 4.485E−02 | 3.766E−02 | 3.004E−02 | 4.099E−02 | 5.279E−02 | 3.830E−02 |
| 19 | 1.599E−01 | 1.813E−01 | 1.341E−01 | 1.116E−01 | 1.406E−01 | 1.005E−01 | 1.320E−01 | 1.663E−01 | 1.974E−01 | 9.356E−02 | 1.202E−01 | 1.427E−01 | 1.899E−01 |
| 20 | 5.386E−04 | 1.738E−03 | 2.049E−03 | 1.352E−03 | 3.026E−03 | 5.343E−04 | 2.961E−03 | 5.901E−04 | 1.234E−03 | 8.240E−04 | 5.858E−03 | 1.277E−03 | 8.509E−04 |
| 21 | 2.747E−02 | 2.350E−02 | 2.350E−02 | 1.212E−02 | 1.212E−02 | 3.101E−02 | 9.388E−03 | 1.298E−02 | 2.092E−02 | 1.685E−02 | 1.459E−02 | 1.341E−02 | 2.382E−02 |
| 22 | 3.766E−03 | 2.178E−03 | 7.167E−03 | 2.704E−03 | 7.554E−03 | 2.672E−03 | 2.961E−03 | 1.770E−03 | 3.702E−03 | 2.060E−03 | 6.835E−03 | 4.453E−03 | 4.249E−03 |
| 23 | 5.494E−02 | 5.708E−02 | 6.856E−02 | 3.509E−02 | 4.002E−02 | 4.807E−02 | 4.249E−02 | 3.895E−02 | 8.391E−02 | 2.350E−02 | 7.908E−02 | 4.388E−02 | 6.556E−02 |
| 24 | 1.255E−01 | 1.481E−01 | 1.191E−01 | 1.159E−01 | 1.341E−01 | 1.116E−01 | 8.101E−02 | 1.212E−01 | 9.367E−02 | 7.092E−02 | 1.015E−01 | 8.788E−02 | 9.871E−02 |
| 25 | 3.927E−02 | 4.657E−02 | 1.738E−02 | 1.888E−02 | 9.067E−03 | 3.155E−02 | 1.137E−02 | 3.015E−02 | 5.365E−02 | 1.899E−02 | 1.953E−02 | 1.406E−02 | 2.382E−02 |
| 26 | 2.961E−02 | 1.738E−02 | 2.661E−02 | 1.888E−02 | 1.588E−02 | 1.395E−02 | 2.028E−02 | 1.534E−02 | 2.039E−02 | 9.067E−03 | 2.639E−02 | 2.039E−02 | 1.620E−02 |
| 27 | 4.839E−03 | 1.045E−02 | 2.049E−03 | 4.732E−03 | 3.777E−03 | 6.953E−03 | 6.921E−03 | 7.672E−03 | 3.702E−03 | 5.773E−03 | 5.858E−03 | 1.910E−03 | 5.107E−03 |
| 28 | 4.571E−02 | 5.923E−02 | 3.584E−02 | 3.648E−02 | 1.964E−02 | 3.262E−02 | 2.521E−02 | 2.715E−02 | 4.313E−02 | 2.725E−02 | 3.616E−02 | 2.994E−02 | 2.468E−02 |
| 29 | 7.371E−02 | 6.309E−02 | 4.710E−02 | 3.036E−02 | 3.176E−02 | 4.388E−02 | 2.715E−02 | 3.895E−02 | 7.210E−02 | 2.843E−02 | 4.689E−02 | 4.324E−02 | 3.401E−02 |
| 30 | 9.152E−02 | 1.459E−01 | 8.498E−02 | 1.116E−01 | 1.406E−01 | 1.000E−01 | 8.197E−02 | 1.057E−01 | 9.120E−02 | 8.863E−02 | 8.004E−02 | 8.916E−02 | 6.384E−02 |
| 31 | 1.180E−01 | 2.167E−01 | 1.073E−01 | 1.363E−01 | 1.695E−01 | 1.016E−01 | 8.798E−02 | 1.341E−01 | 9.067E−02 | 7.747E−02 | 9.378E−02 | 8.852E−02 | 3.745E−02 |
| 32 | 1.202E−01 | 8.015E−02 | 9.614E−02 | 9.721E−02 | 6.577E−02 | 3.530E−02 | 5.536E−02 | 7.672E−02 | 7.092E−02 | 9.485E−02 | 1.513E−01 | 7.639E−02 | 6.717E−02 |
| 33 | 2.318E−02 | 1.781E−02 | 1.642E−02 | 9.453E−03 | 6.803E−03 | 9.624E−03 | 9.882E−03 | 1.245E−02 | 6.781E−03 | 1.159E−02 | 1.266E−02 | 1.459E−02 | 4.249E−03 |
| 34 | 5.708E−01 | 5.333E−01 | 9.199E−01 | 8.625E−01 | 7.708E−01 | 4.742E−01 | 5.526E−01 | 7.361E−01 | 6.599E−01 | 6.343E−01 | 8.690E−01 | 8.111E−01 | 5.687E−01 |
| 35 | 1.148E−01 | 1.395E−01 | 7.468E−02 | 1.105E−01 | 8.541E−02 | 8.069E−02 | 9.045E−02 | 8.208E−02 | 8.262E−02 | 7.296E−02 | 1.223E−01 | 9.227E−02 | 4.506E−02 |
| 36 | 7.532E−03 | 1.395E−02 | 7.167E−03 | 4.732E−03 | 1.363E−02 | 1.070E−02 | 8.895E−03 | 5.901E−03 | 4.313E−03 | 1.072E−02 | 9.764E−03 | 5.097E−03 | 2.554E−03 |
| 37 | 1.781E−02 | 1.695E−02 | 1.738E−02 | 1.148E−02 | 1.438E−02 | 1.599E−02 | 1.384E−02 | 2.071E−02 | 1.727E−02 | 1.320E−02 | 1.953E−02 | 1.341E−02 | 2.124E−02 |
| 38 | 4.785E−02 | 3.219E−02 | 7.575E−02 | 3.852E−02 | 2.564E−02 | 2.189E−02 | 2.371E−02 | 2.425E−02 | 2.961E−02 | 2.800E−02 | 3.809E−02 | 2.414E−02 | 2.725E−02 |
| 39 | 1.127E−01 | 6.577E−02 | 2.972E−02 | 5.805E−02 | 6.041E−02 | 5.558E−02 | 9.388E−02 | 6.202E−02 | 1.042E−01 | 7.414E−02 | 2.436E−02 | 7.704E−02 | 7.060E−02 |
| 40 | 1.341E−01 | 1.341E−01 | 1.212E−01 | 2.114E−01 | 2.189E−01 | 1.427E−01 | 1.524E−01 | 1.738E−01 | 1.717E−01 | 1.234E−01 | 8.101E−02 | 1.427E−01 | 1.481E−01 |
| 41 | 4.410E−02 | 3.959E−02 | 3.584E−02 | 3.648E−02 | 4.227E−02 | 3.798E−02 | 3.015E−02 | 3.015E−02 | 3.820E−02 | 1.899E−02 | 4.195E−02 | 3.948E−02 | 2.039E−02 |
| 42 | 5.386E−04 | 8.712E−04 | 2.049E−03 | 1.352E−03 | 0.000E+00 | 1.070E−03 | 1.974E−03 | 1.770E−03 | 6.170E−04 | 8.240E−04 | 1.953E−03 | 2.543E−03 | 5.955E−03 |
| 43 | 7.613E−03 | 1.211E−02 | 2.752E−02 | 1.343E−02 | 4.887E−03 | 6.147E−03 | 8.642E−03 | 5.375E−03 | 6.790E−03 | 1.245E−02 | 2.083E−02 | 1.237E−02 | 1.204E−02 |
| 44 | 3.738E−01 | 3.128E−01 | 1.600E+00 | 4.246E−01 | 3.828E−01 | 2.264E−01 | 3.442E−01 | 3.340E−01 | 4.308E−01 | 3.719E−01 | 6.303E−01 | 4.616E−01 | 5.225E−01 |
| 45 | 2.109E−01 | 1.637E−01 | 5.960E−01 | 1.116E−01 | 9.542E−02 | 1.340E−01 | 1.283E−01 | 1.353E−01 | 2.586E−01 | 1.467E−01 | 2.493E−01 | 1.682E−01 | 2.290E−01 |
| 46 | 1.199E−01 | 1.416E−01 | 4.702E−01 | 1.453E−01 | 1.142E−01 | 9.876E−02 | 1.463E−01 | 9.953E−02 | 1.103E−01 | 1.304E−01 | 3.908E−01 | 1.595E−01 | 1.502E−01 |
| 47 | 2.955E−01 | 2.235E−01 | 1.216E+00 | 3.299E−01 | 2.848E−01 | 2.009E−01 | 2.422E−01 | 2.310E−01 | 3.127E−01 | 2.508E−01 | 5.067E−01 | 3.411E−01 | 3.565E−01 |

APPENDIX D-continued

Ovarian Cancer
Training Dataset

| | | | | | | | | | | | | | |
|---|---|---|---|---|---|---|---|---|---|---|---|---|---|
| 48 | 4.064E−02 | 3.369E−02 | 9.748E−02 | 2.299E−02 | 1.847E−02 | 2.320E−02 | 3.241E−02 | 2.009E−02 | 3.961E−02 | 2.855E−02 | 3.909E−02 | 3.626E−02 | 3.266E−02 |
| 49 | 1.006E−02 | 1.181E−02 | 6.070E−02 | 1.116E−02 | 7.613E−03 | 6.661E−03 | 1.456E−02 | 1.217E−02 | 2.217E−02 | 7.896E−03 | 2.176E−02 | 1.739E−02 | 1.713E−02 |
| 50 | 2.451E−03 | 4.269E−03 | 1.006E−02 | 3.241E−03 | 1.993E−03 | 4.861E−03 | 6.404E−03 | 2.407E−03 | 7.536E−03 | 3.163E−03 | 6.790E−03 | 3.961E−03 | 5.915E−03 |
| 51 | 1.098E−01 | 2.779E−01 | 1.209E−01 | 2.281E−01 | 9.542E−02 | 1.557E−01 | 1.795E−01 | 1.106E−01 | 5.375E−02 | 2.966E−01 | 1.257E−01 | 1.664E−01 | 1.834E−01 |
| 52 | 2.572E−03 | 5.015E−03 | 6.121E−03 | 4.707E−03 | 1.088E−03 | 3.086E−03 | 4.038E−03 | 1.556E−03 | 1.183E−03 | 6.121E−03 | 4.912E−03 | 3.806E−03 | 4.475E−03 |
| 53 | 6.919E−02 | 7.227E−02 | 1.253E−01 | 1.245E−01 | 1.219E−01 | 7.664E−02 | 7.150E−02 | 1.106E−01 | 9.542E−02 | 7.793E−02 | 1.175E−01 | 1.121E−01 | 1.049E−01 |
| 54 | 4.394E+00 | 4.505E+00 | 2.714E+00 | 3.958E+00 | 4.395E+00 | 4.231E+00 | 4.844E+00 | 5.746E+00 | 5.833E+00 | 4.226E+00 | 2.962E+00 | 4.359E+00 | 4.479E+00 |
| 55 | 4.176E−01 | 6.597E−01 | 3.542E−01 | 5.977E−01 | 5.983E−01 | 4.779E−01 | 6.216E−01 | 5.620E−01 | 4.202E−01 | 6.270E−01 | 4.093E−01 | 5.683E−01 | 5.366E−01 |
| 56 | 1.865E−01 | 1.516E−01 | 1.155E−01 | 1.422E−01 | 1.353E−01 | 1.503E−01 | 1.618E−01 | 1.887E−01 | 2.184E−01 | 1.591E−01 | 1.151E−01 | 1.417E−01 | 1.767E−01 |
| 57 | 2.369E+00 | 4.050E+00 | 2.451E+00 | 3.954E+00 | 4.349E+00 | 3.237E+00 | 4.160E+00 | 4.025E+00 | 2.911E+00 | 3.846E+00 | 2.456E+00 | 3.734E+00 | 3.780E+00 |
| 58 | 2.803E−02 | 5.710E−02 | 8.076E−02 | 6.481E−02 | 3.961E−02 | 3.626E−02 | 5.787E−02 | 2.932E−02 | 3.266E−02 | 4.707E−02 | 8.770E−02 | 5.350E−02 | 4.681E−02 |
| 59 | 6.018E−02 | 8.513E−02 | 3.729E−02 | 7.587E−02 | 7.433E−02 | 5.710E−02 | 7.973E−02 | 7.819E−02 | 6.764E−02 | 6.816E−02 | 4.990E−02 | 7.047E−02 | 7.279E−02 |
| 60 | 3.549E−02 | 3.163E−02 | 5.941E−02 | 5.710E−02 | 5.427E−02 | 3.729E−02 | 3.704E−02 | 4.141E−02 | 4.192E−02 | 3.935E−02 | 4.732E−02 | 5.504E−02 | 5.633E−02 |
| 61 | 1.565E+00 | 1.026E+00 | 4.800E−01 | 8.062E−01 | 1.086E+00 | 1.229E+00 | 1.508E+00 | 1.126E+00 | 1.157E+00 | 1.110E+00 | 5.268E−01 | 1.124E+00 | 9.090E−01 |
| 62 | 5.067E−01 | 4.282E−01 | 2.426E−01 | 2.846E−01 | 2.748E−01 | 4.911E−01 | 2.795E−01 | 2.883E−01 | 4.896E−01 | 3.279E−01 | 2.577E−01 | 3.009E−01 | 3.616E−01 |
| 63 | 1.613E−02 | 1.034E−02 | 1.399E−02 | 1.036E−02 | 1.088E−02 | 1.255E−02 | 1.078E−02 | 9.208E−03 | 1.271E−02 | 9.979E−03 | 1.170E−02 | 1.114E−02 | 1.101E−02 |
| 64 | 3.851E+00 | 3.109E+00 | 1.283E+00 | 2.340E+00 | 2.621E+00 | 3.703E+00 | 2.301E+00 | 2.660E+00 | 2.984E+00 | 2.759E+00 | 1.767E+00 | 2.526E+00 | 2.331E+00 |
| 65 | 1.487E−01 | 1.485E−01 | 1.673E−01 | 1.103E−01 | 1.178E−01 | 1.363E−01 | 1.085E−01 | 1.078E−01 | 1.499E−01 | 1.431E−01 | 1.526E−01 | 1.240E−01 | 1.294E−01 |
| 66 | 6.036E−01 | 1.161E+00 | 3.370E−01 | 6.544E−01 | 6.974E−01 | 1.102E+00 | 5.720E−01 | 5.124E−01 | 4.295E−01 | 7.403E−01 | 4.819E−01 | 6.286E−01 | 4.958E−01 |
| 67 | 5.633E−02 | 9.362E−02 | 1.405E−01 | 9.362E−02 | 7.021E−02 | 6.430E−02 | 6.919E−02 | 4.835E−02 | 5.118E−02 | 7.793E−02 | 1.432E−01 | 8.976E−02 | 7.870E−02 |
| 68 | 2.345E−01 | 1.806E−01 | 3.355E−01 | 2.757E−01 | 2.886E−01 | 2.394E−01 | 1.317E−01 | 1.703E−01 | 2.082E−01 | 1.853E−01 | 3.225E−01 | 2.547E−01 | 2.086E−01 |
| 69 | 1.091E+00 | 5.640E−01 | 2.176E−01 | 4.151E−01 | 6.076E−01 | 9.569E−01 | 6.623E−01 | 5.269E−01 | 5.452E−01 | 5.271E−01 | 2.701E−01 | 5.795E−01 | 3.722E−01 |
| 70 | 4.192E−02 | 3.086E−02 | 4.424E−02 | 3.035E−02 | 3.781E−02 | 4.295E−02 | 3.755E−02 | 2.803E−02 | 2.906E−02 | 3.626E−02 | 4.038E−02 | 3.575E−02 | 3.395E−02 |
| 71 | 5.941E−03 | 6.250E−03 | 1.471E−02 | 9.053E−03 | 7.073E−03 | 4.604E−03 | 9.130E−03 | 8.359E−03 | 1.211E−02 | 4.938E−03 | 7.253E−03 | 1.160E−02 | 8.359E−03 |
| 72 | 2.194E−03 | 2.598E−03 | 4.424E−03 | 1.618E−03 | 2.173E−03 | 3.344E−03 | 3.678E−03 | 2.407E−03 | 4.887E−03 | 3.163E−03 | 3.498E−03 | 2.906E−03 | 5.092E−03 |
| 73 | 1.693E−03 | 9.165E−04 | 0.000E+00 | 1.422E−03 | 3.183E−03 | 1.682E−03 | 1.040E−03 | 3.104E−03 | 1.298E−03 | 0.000E+00 | 0.000E+00 | 0.000E+00 | 3.578E−03 |
| 74 | 5.666E−03 | 8.239E−03 | 4.300E−03 | 1.275E−02 | 4.774E−03 | 3.375E−03 | 4.673E−03 | 7.449E−03 | 7.133E−03 | 3.036E−03 | 3.081E−03 | 2.675E−03 | 6.264E−03 |
| 75 | 7.133E−02 | 1.648E−01 | 6.456E−02 | 9.312E−02 | 7.314E−02 | 6.016E−02 | 6.185E−02 | 9.255E−02 | 5.971E−02 | 3.386E−02 | 1.196E−01 | 6.230E−02 | 2.506E−02 |
| 76 | 9.289E−02 | 2.551E−01 | 6.783E−02 | 2.404E−01 | 1.230E−01 | 9.447E−02 | 1.029E−01 | 1.591E−01 | 9.797E−02 | 5.113E−02 | 2.438E−01 | 9.176E−02 | 4.210E−02 |
| 77 | 7.923E−03 | 2.246E−02 | 2.156E−03 | 5.688E−03 | 3.183E−03 | 7.314E−03 | 1.874E−02 | 1.366E−02 | 1.230E−02 | 7.799E−03 | 1.749E−02 | 4.018E−03 | 3.578E−03 |
| 78 | 0.000E+00 | 4.582E−04 | 0.000E+00 | 7.099E−04 | 0.000E+00 | 0.000E+00 | 5.192E−04 | 0.000E+00 | 6.490E−04 | 8.668E−04 | 4.108E−03 | 1.343E−03 | 0.000E+00 |
| 79 | 4.526E−03 | 2.291E−03 | 3.228E−03 | 2.844E−03 | 3.973E−03 | 2.810E−03 | 1.040E−03 | 5.587E−03 | 0.000E+00 | 1.738E−03 | 1.027E−03 | 2.675E−03 | 2.686E−03 |
| 80 | 1.693E−03 | 1.828E−03 | 3.228E−03 | 2.133E−03 | 3.183E−03 | 5.621E−04 | 0.000E+00 | 1.862E−03 | 6.490E−04 | 0.000E+00 | 3.081E−03 | 6.693E−04 | 0.000E+00 |
| 81 | 6.795E−03 | 1.008E−02 | 2.370E−02 | 4.977E−03 | 1.113E−02 | 6.185E−03 | 5.722E−03 | 8.070E−03 | 7.788E−03 | 6.501E−03 | 1.851E−02 | 1.071E−02 | 8.059E−03 |
| 82 | 4.526E−03 | 7.325E−03 | 7.540E−03 | 2.844E−03 | 5.564E−03 | 2.246E−03 | 9.357E−03 | 1.119E−02 | 3.239E−03 | 3.905E−03 | 4.108E−03 | 2.675E−03 | 2.686E−03 |
| 83 | 1.129E−03 | 4.582E−03 | 1.077E−03 | 4.977E−03 | 5.564E−03 | 1.125E−03 | 4.153E−03 | 3.104E−03 | 3.239E−03 | 1.298E−03 | 4.108E−03 | 0.000E+00 | 8.950E−04 |
| 84 | 5.090E−03 | 8.239E−03 | 1.077E−02 | 1.490E−02 | 1.433E−02 | 6.749E−03 | 4.673E−03 | 4.345E−03 | 7.788E−03 | 6.501E−03 | 1.749E−02 | 6.693E−03 | 8.950E−03 |
| 85 | 1.129E−03 | 1.828E−03 | 2.156E−03 | 3.555E−03 | 3.183E−03 | 5.621E−04 | 1.558E−03 | 4.966E−03 | 2.596E−03 | 4.334E−04 | 4.108E−03 | 3.352E−03 | 8.950E−04 |
| 86 | 7.359E−03 | 2.427E−02 | 1.077E−02 | 2.065E−02 | 1.670E−02 | 1.298E−02 | 6.242E−03 | 2.111E−02 | 7.788E−03 | 5.632E−03 | 1.129E−02 | 8.702E−03 | 1.795E−03 |
| 87 | 4.526E−02 | 1.174E−01 | 4.086E−02 | 6.817E−02 | 8.431E−02 | 4.786E−02 | 4.368E−02 | 7.020E−02 | 4.605E−02 | 3.465E−02 | 4.312E−02 | 2.540E−02 | 1.253E−02 |
| 88 | 9.628E−03 | 1.603E−02 | 9.684E−03 | 1.851E−02 | 8.747E−03 | 7.878E−03 | 7.280E−03 | 4.345E−03 | 4.537E−03 | 7.370E−03 | 1.027E−02 | 6.693E−03 | 4.470E−03 |
| 89 | 1.580E−02 | 2.652E−02 | 4.300E−03 | 2.415E−02 | 2.223E−02 | 7.314E−03 | 1.140E−02 | 2.302E−02 | 1.885E−02 | 8.668E−03 | 1.535E−02 | 9.379E−03 | 6.264E−03 |
| 90 | 2.551E−02 | 9.436E−02 | 1.828E−02 | 4.977E−02 | 4.210E−02 | 2.472E−02 | 3.950E−02 | 4.537E−02 | 2.980E−02 | 3.160E−02 | 4.413E−02 | 1.535E−02 | 1.074E−02 |
| 91 | 9.628E−03 | 2.156E−02 | 4.300E−03 | 1.065E−02 | 6.354E−03 | 2.246E−03 | 9.876E−03 | 5.587E−03 | 3.239E−03 | 3.036E−03 | 6.163E−03 | 2.675E−03 | 0.000E+00 |
| 92 | 1.298E−02 | 3.115E−02 | 1.400E−02 | 1.986E−02 | 2.540E−02 | 1.242E−02 | 1.817E−02 | 2.359E−02 | 1.366E−02 | 5.632E−03 | 2.562E−02 | 1.411E−02 | 7.156E−03 |
| 93 | 1.874E−02 | 3.341E−02 | 2.370E−02 | 1.558E−02 | 3.025E−02 | 2.472E−02 | 1.298E−02 | 2.427E−02 | 2.404E−02 | 8.239E−03 | 1.433E−02 | 9.379E−03 | 1.433E−02 |
| 94 | 4.526E−03 | 5.497E−03 | 2.156E−03 | 4.977E−03 | 7.156E−03 | 4.503E−03 | 2.077E−03 | 1.242E−03 | 1.298E−03 | 1.738E−03 | 3.081E−03 | 3.352E−03 | 3.578E−03 |
| 95 | 1.354E−02 | 2.607E−02 | 1.287E−02 | 3.691E−02 | 2.144E−02 | 1.411E−02 | 8.837E−03 | 1.433E−02 | 1.558E−02 | 6.501E−03 | 1.749E−02 | 1.806E−02 | 1.433E−02 |
| 96 | 1.693E−03 | 1.287E−02 | 2.156E−03 | 1.704E−02 | 7.946E−03 | 1.682E−03 | 6.242E−03 | 9.932E−03 | 6.490E−03 | 4.774E−03 | 1.027E−02 | 5.361E−03 | 1.795E−03 |
| 97 | 5.090E−03 | 9.165E−03 | 3.228E−03 | 1.140E−02 | 1.113E−02 | 4.503E−03 | 5.192E−03 | 4.966E−03 | 6.490E−03 | 2.167E−03 | 1.230E−02 | 3.352E−03 | 8.950E−04 |

APPENDIX D-continued

Ovarian Cancer
Training Dataset

| | | | | | | | | | | | | | |
|---|---|---|---|---|---|---|---|---|---|---|---|---|---|
| 98 | 5.666E−03 | 1.558E−02 | 7.540E−03 | 1.772E−02 | 1.749E−02 | 7.878E−03 | 8.837E−03 | 1.614E−02 | 7.133E−03 | 5.203E−03 | 1.535E−02 | 7.370E−03 | 8.059E−03 |
| 99 | 1.120E−01 | 5.518E−02 | 9.123E−02 | 8.719E−02 | 5.874E−02 | 5.677E−02 | 1.251E−01 | 1.006E−01 | 1.162E−01 | 9.332E−02 | 8.363E−02 | 8.007E−02 | 9.332E−02 |
| 100 | 2.771E−02 | 2.244E−02 | 4.672E−02 | 4.709E−02 | 2.673E−02 | 2.379E−02 | 4.010E−02 | 3.311E−02 | 2.894E−02 | 3.066E−02 | 4.684E−02 | 4.660E−02 | 3.495E−02 |
| 101 | 2.011E−01 | 1.717E−01 | 1.251E−01 | 1.521E−01 | 2.085E−01 | 1.557E−01 | 1.754E−01 | 2.207E−01 | 2.085E−01 | 1.386E−01 | 1.026E−01 | 1.729E−01 | 1.803E−01 |
| 102 | 3.532E−01 | 3.250E−01 | 1.091E+00 | 8.676E−01 | 7.039E−01 | 3.985E−01 | 5.113E−01 | 5.212E−01 | 4.329E−01 | 5.359E−01 | 1.146E+00 | 5.898E−01 | 3.360E−01 |
| 103 | 1.999E−01 | 1.655E−01 | 1.099E−01 | 2.060E−01 | 3.053E−01 | 1.815E−01 | 2.305E−01 | 3.127E−01 | 2.698E−01 | 1.386E−01 | 1.361E−01 | 2.661E−01 | 2.796E−01 |
| 104 | 1.790E−01 | 1.557E−01 | 3.286E−01 | 3.151E−01 | 2.465E−01 | 2.109E−01 | 2.514E−01 | 2.428E−01 | 2.256E−01 | 2.771E−01 | 4.932E−01 | 2.403E−01 | 1.974E−01 |
| 105 | 6.107E−01 | 4.684E−01 | 1.347E+00 | 1.098E+00 | 1.029E+00 | 6.892E−01 | 7.124E−01 | 7.456E−01 | 6.928E−01 | 6.873E−01 | 1.625E+00 | 8.819E−01 | 6.070E−01 |
| 106 | 1.557E−01 | 1.422E−01 | 1.545E−01 | 1.422E−01 | 1.140E−01 | 1.063E−01 | 2.121E−01 | 1.521E−01 | 1.373E−01 | 2.281E−01 | 1.361E−01 | 1.496E−01 | 1.606E−01 |
| 107 | 1.212E−01 | 1.010E−01 | 1.680E−01 | 1.226E−01 | 1.312E−01 | 1.131E−01 | 1.447E−01 | 1.127E−01 | 1.521E−01 | 1.288E−01 | 1.183E−01 | 1.012E−01 | 1.570E−01 |
| 108 | 2.134E−01 | 1.557E−01 | 1.435E−01 | 1.422E−01 | 1.790E−01 | 2.121E−01 | 2.109E−01 | 1.533E−01 | 1.913E−01 | 1.582E−01 | 1.545E−01 | 1.754E−01 | 1.619E−01 |
| 109 | 7.995E−03 | 5.469E−03 | 1.987E−02 | 6.180E−03 | 9.503E−03 | 1.223E−02 | 5.077E−03 | 6.070E−03 | 4.929E−03 | 6.597E−03 | 1.790E−02 | 9.454E−03 | 1.069E−02 |
| 110 | 3.017E−02 | 4.476E−02 | 1.643E−02 | 3.470E−02 | 3.887E−02 | 3.666E−02 | 2.931E−02 | 3.446E−02 | 3.593E−02 | 3.863E−02 | 7.811E−03 | 3.127E−02 | 3.213E−02 |
| 111 | 2.465E−02 | 3.237E−02 | 4.672E−03 | 2.158E−02 | 2.587E−02 | 2.256E−02 | 2.146E−02 | 2.833E−02 | 2.109E−02 | 2.256E−02 | 1.668E−02 | 1.962E−02 | 2.048E−02 |
| 112 | 8.608E−03 | 1.937E−02 | 1.398E−02 | 1.239E−02 | 1.643E−02 | 1.533E−02 | 1.129E−02 | 1.079E−02 | 1.127E−02 | 1.084E−02 | 1.557E−02 | 1.741E−02 | 1.263E−02 |
| 113 | 4.917E−03 | 3.483E−03 | 1.170E−03 | 5.408E−03 | 9.503E−03 | 6.107E−03 | 4.513E−03 | 6.070E−03 | 4.929E−03 | 3.299E−03 | 3.348E−03 | 8.007E−03 | 1.263E−02 |
| 114 | 4.304E−03 | 3.985E−03 | 4.672E−03 | 1.386E−02 | 9.503E−03 | 6.107E−03 | 7.345E−03 | 5.395E−03 | 6.340E−03 | 4.709E−03 | 6.695E−03 | 8.731E−03 | 5.837E−03 |
| 115 | 1.471E−02 | 1.288E−02 | 1.398E−02 | 8.486E−03 | 6.904E−03 | 1.410E−02 | 1.300E−02 | 8.768E−03 | 1.057E−02 | 8.952E−03 | 1.557E−02 | 1.962E−02 | 1.069E−02 |
| 116 | 6.769E−03 | 8.461E−03 | 8.191E−03 | 6.180E−03 | 9.503E−03 | 4.893E−03 | 7.909E−03 | 2.023E−03 | 9.160E−03 | 2.820E−03 | 3.348E−03 | 7.272E−03 | 6.806E−03 |
| 117 | 9.221E−03 | 1.545E−02 | 4.672E−03 | 1.471E−02 | 1.643E−02 | 1.223E−02 | 1.073E−02 | 1.692E−02 | 1.263E−02 | 1.459E−02 | 3.348E−03 | 1.606E−02 | 1.754E−02 |
| 118 | 6.156E−03 | 1.144E−02 | 1.876E−02 | 8.486E−03 | 1.036E−02 | 5.494E−03 | 3.384E−03 | 9.442E−03 | 7.750E−03 | 8.007E−03 | 1.226E−02 | 8.007E−03 | 1.069E−02 |
| 119 | 8.608E−03 | 1.144E−02 | 1.398E−02 | 1.852E−02 | 1.471E−02 | 1.410E−02 | 9.601E−03 | 8.768E−03 | 7.051E−03 | 9.418E−03 | 1.901E−02 | 1.668E−02 | 1.557E−02 |
| 120 | 9.221E−03 | 1.349E−02 | 9.356E−03 | 1.003E−02 | 1.557E−02 | 1.223E−02 | 1.300E−02 | 8.768E−03 | 8.461E−03 | 8.473E−03 | 1.790E−02 | 1.091E−02 | 1.069E−02 |
| 121 | 5.387E−02 | 9.350E−03 | 1.095E−01 | 4.835E−02 | 3.241E−02 | 1.149E−02 | 2.476E−02 | 1.692E−02 | 1.327E−02 | 3.535E−02 | 2.796E−02 | 4.559E−02 | 3.651E−02 |
| 122 | 9.973E−02 | 2.743E−01 | 5.859E−02 | 2.467E−01 | 9.706E−02 | 9.172E−02 | 6.714E−02 | 4.648E−02 | 5.289E−02 | 1.799E−01 | 1.122E−01 | 1.095E−01 | 1.336E−01 |
| 123 | 1.790E+00 | 3.936E+00 | 1.808E+00 | 5.370E+00 | 3.224E+00 | 2.066E+00 | 2.182E+00 | 1.897E+00 | 2.110E+00 | 2.306E+00 | 5.162E+00 | 3.375E+00 | 5.565E+00 |
| 124 | 1.158E−02 | 2.805E−02 | 8.050E−02 | 5.316E−02 | 1.077E−02 | 2.680E−02 | 1.763E−02 | 2.956E−02 | 2.208E−02 | 1.772E−02 | 8.379E−02 | 2.7 34E−02 | 9.172E−02 |
| 125 | 4.239E−02 | 3.117E−02 | 5.120E−02 | 6.278E−02 | 7.569E−02 | 4.586E−02 | 1.416E−02 | 3.802E−02 | 4.408E−02 | 3.535E−02 | 7.685E−02 | 3.642E−02 | 1.158E−01 |
| 126 | 1.113E+00 | 1.817E+00 | 3.295E−01 | 4.835E−01 | 2.324E−01 | 7.614E−01 | 5.165E−01 | 4.354E−01 | 6.972E−01 | 1.024E+00 | 3.633E−01 | 5.102E−01 | 8.032E−01 |
| 127 | 2.342E+00 | 4.363E+00 | 7.979E−01 | 1.612E+00 | 1.042E+00 | 1.817E+00 | 8.629E−01 | 9.083E−01 | 1.122E+00 | 1.665E+00 | 2.021E+00 | 1.362E+00 | 2.012E+00 |
| 128 | 1.959E+00 | 3.660E+00 | 1.603E+00 | 3.108E+00 | 2.573E+00 | 2.538E+00 | 1.834E+00 | 1.434E+00 | 1.656E+00 | 1.995E+00 | 3.464E+00 | 2.654E+00 | 3.428E+00 |
| 129 | 3.847E−02 | 4.052E−02 | 7.320E−02 | 8.210E−02 | 9.706E−02 | 4.203E−02 | 3.179E−02 | 4.648E−02 | 6.616E−02 | 4.132E−02 | 5.592E−02 | 7.747E−02 | 6.091E−02 |
| 130 | 1.252E+01 | 1.124E+01 | 2.422E+00 | 4.889E+00 | 2.974E+00 | 5.718E+00 | 5.833E+00 | 5.325E+00 | 6.762E+00 | 6.650E+00 | 3.954E+00 | 5.325E+00 | 6.616E+00 |
| 131 | 5.138E+00 | 6.644E+00 | 2.306E+00 | 5.129E+00 | 2.832E+00 | 1.995E+00 | 6.882E+00 | 4.007E+00 | 6.881E+00 | 5.762E+00 | 3.688E+00 | 5.405E+00 | 4.452E+00 |
| 132 | 5.779E−02 | 3.428E−02 | 6.589E−02 | 1.692E−01 | 5.405E−02 | 4.586E−02 | 7.427E−02 | 2.110E−02 | 3.090E−02 | 8.842E−02 | 1.674E−01 | 7.747E−02 | 5.476E−02 |
| 133 | 2.306E−02 | 1.870E−02 | 7.320E−03 | 1.932E−02 | 2.707E−02 | 1.149E−02 | 1.060E−02 | 8.451E−03 | 1.327E−02 | 1.478E−02 | 2.796E−02 | 5.013E−02 | 3.651E−02 |
| 134 | 7.703E−03 | 3.117E−03 | 1.460E−02 | 2.903E−02 | 2.707E−02 | 3.446E−02 | 3.179E−02 | 8.451E−03 | 3.972E−02 | 2.654E−02 | 2.093E−02 | 2.280E−02 | 4.871E−02 |
| 135 | 2.698E−02 | 1.870E−02 | 2.930E−02 | 1.932E−02 | 3.241E−02 | 1.915E−02 | 2.476E−02 | 8.451E−03 | 1.763E−02 | 4.132E−02 | 1.398E−02 | 1.362E−02 | 3.651E−02 |
| 136 | 1.541E−02 | 1.870E−02 | 7.320E−03 | 2.903E−02 | 2.164E−02 | 3.829E−02 | 1.416E−02 | 1.264E−02 | 3.090E−02 | 5.895E−03 | 2.796E−02 | 4.559E−03 | 1.825E−02 |
| 137 | 3.081E−02 | 4.987E−02 | 5.859E−02 | 9.706E−02 | 9.706E−02 | 5.352E−02 | 6.714E−02 | 5.494E−02 | 3.090E−02 | 4.720E−02 | 4.889E−02 | 6.376E−02 | 6.091E−02 |
| 138 | 1.541E−02 | 1.870E−02 | 3.660E−02 | 2.903E−02 | 3.785E−02 | 1.532E−02 | 2.832E−02 | 1.264E−02 | 1.327E−02 | 2.360E−02 | 4.194E−02 | 2.734E−02 | 3.651E−02 |
| 139 | 2.235E−01 | 3.428E−01 | 1.460E−01 | 1.451E−01 | 1.674E−01 | 2.680E−01 | 1.523E−01 | 1.309E−01 | 2.511E−01 | 2.093E−01 | 1.603E−01 | 2.137E−01 | 3.108E−01 |
| 140 | 9.973E−02 | 2.805E−01 | 8.050E−02 | 2.030E−01 | 7.569E−02 | 1.336E−01 | 9.172E−02 | 7.177E−02 | 1.104E−01 | 1.594E−01 | 1.541E−01 | 1.416E−01 | 1.701E−01 |
| 141 | 5.779E−02 | 6.545E−02 | 7.320E−03 | 1.113E−01 | 5.948E−02 | 2.680E−02 | 4.595E−02 | 1.692E−02 | 6.180E−02 | 6.189E−02 | 1.184E−01 | 3.642E−02 | 4.871E−02 |
| 142 | 1.158E−02 | 6.233E−03 | 7.320E−03 | 1.932E−02 | 1.621E−02 | 1.149E−02 | 1.416E−02 | 4.221E−03 | 1.327E−02 | 1.772E−02 | 3.491E−02 | 9.083E−03 | 2.431E−02 |
| 143 | 1.923E−02 | 2.182E−02 | 2.199E−02 | 1.932E−02 | 0.000E+00 | 1.532E−02 | 7.070E−03 | 2.538E−02 | 1.327E−02 | 1.175E−02 | 4.194E−02 | 1.825E−02 | 3.651E−02 |
| 144 | 2.698E−02 | 3.117E−02 | 4.390E−02 | 2.903E−02 | 4.328E−02 | 3.829E−02 | 3.535E−02 | 8.451E−03 | 1.327E−02 | 3.829E−02 | 1.398E−02 | 2.734E−02 | 2.431E−02 |
| 145 | 2.698E−02 | 4.052E−02 | 3.660E−02 | 3.384E−02 | 1.621E−02 | 1.149E−02 | 2.832E−02 | 3.802E−02 | 1.327E−02 | 2.360E−02 | 2.796E−02 | 1.362E−02 | 5.476E−02 |
| 146 | 1.389E−01 | 2.208E−01 | 1.095E−01 | 1.309E−01 | 1.567E−01 | 1.184E−01 | 2.048E−01 | 1.060E−01 | 1.371E−01 | 1.532E−01 | 6.287E−02 | 1.772E−01 | 2.796E−01 |
| 147 | 1.621E−01 | 2.556E−01 | 4.390E−02 | 8.700E−02 | 8.646E−02 | 1.532E−01 | 1.060E−01 | 4.221E−02 | 9.261E−02 | 1.532E−01 | 7.685E−02 | 1.140E−01 | 1.647E−01 |

APPENDIX D-continued

Ovarian Cancer
Training Dataset

| | | | | | | | | | | | | | |
|---|---|---|---|---|---|---|---|---|---|---|---|---|---|
| 148 | 4.239E−01 | 8.994E−01 | 1.834E−01 | 3.580E−01 | 2.271E−01 | 4.363E−01 | 2.760E−01 | 1.229E−01 | 2.208E−01 | 5.307E−01 | 3.980E−01 | 4.141E−01 | 7.124E−01 |
| 149 | 1.077E−01 | 2.992E−01 | 5.120E−02 | 1.015E−01 | 5.948E−02 | 9.528E−02 | 3.891E−02 | 5.494E−02 | 8.825E−02 | 6.492E−02 | 4.889E−02 | 1.140E−01 | 1.220E−01 |
| 150 | 3.081E−02 | 3.117E−02 | 2.199E−02 | 2.413E−02 | 3.785E−02 | 1.915E−02 | 1.416E−02 | 2.110E−02 | 2.208E−02 | 1.175E−02 | 1.398E−02 | 1.825E−02 | 5.476E−02 |
| 151 | 2.306E−02 | 9.350E−03 | 2.199E−02 | 4.835E−03 | 1.621E−02 | 7.649E−03 | 1.060E−02 | 2.110E−02 | 1.763E−02 | 5.895E−03 | 1.398E−02 | 4.559E−03 | 2.431E−02 |
| 152 | 5.004E−02 | 1.558E−02 | 4.390E−02 | 2.413E−02 | 5.405E−03 | 1.532E−02 | 5.298E−02 | 4.221E−03 | 2.208E−02 | 6.189E−02 | 2.796E−02 | 2.280E−02 | 3.045E−02 |
| 153 | 3.464E−02 | 3.740E−02 | 7.320E−03 | 3.384E−02 | 5.405E−03 | 2.680E−02 | 2.832E−02 | 8.451E−03 | 1.763E−02 | 1.772E−02 | 3.491E−02 | 1.362E−02 | 3.651E−02 |
| 154 | 7.703E−03 | 9.350E−03 | 2.199E−02 | 1.451E−02 | 3.241E−02 | 7.649E−03 | 1.060E−02 | 4.221E−03 | 0.000E+00 | 1.478E−02 | 3.491E−02 | 2.280E−02 | 1.220E−02 |
| 155 | 3.081E−02 | 2.493E−02 | 7.320E−03 | 2.903E−02 | 2.707E−02 | 1.532E−02 | 2.476E−02 | 4.221E−02 | 4.408E−03 | 1.175E−02 | 6.981E−02 | 2.280E−02 | 0.000E+00 |
| 156 | 1.158E−01 | 2.769E−01 | 1.460E−01 | 3.526E−01 | 2.217E−01 | 2.030E−01 | 3.998E−01 | 1.398E−01 | 2.689E−01 | 3.277E−01 | 2.093E−01 | 4.052E−01 | 5.476E−01 |
| 157 | 8.468E−02 | 1.585E−01 | 5.120E−02 | 1.594E−01 | 8.112E−02 | 1.870E−01 | 1.202E−01 | 9.706E−02 | 1.541E−01 | 1.389E−01 | 8.379E−02 | 1.318E−01 | 2.556E−01 |
| 158 | 2.930E−01 | 3.704E−01 | 2.048E−01 | 2.903E−01 | 2.591E−01 | 4.630E−01 | 4.417E−01 | 1.861E−01 | 2.467E−01 | 3.660E−01 | 2.306E−01 | 3.731E−01 | 4.871E−01 |
| 159 | 1.077E−01 | 1.683E−01 | 4.390E−02 | 1.211E−01 | 7.569E−02 | 1.950E−01 | 7.774E−02 | 1.264E−02 | 5.735E−02 | 1.683E−01 | 8.379E−02 | 1.229E−01 | 1.888E−01 |
| 160 | 3.847E−02 | 4.675E−02 | 2.199E−02 | 4.835E−02 | 2.707E−02 | 1.532E−02 | 2.832E−02 | 2.538E−02 | 1.327E−02 | 6.189E−02 | 5.592E−02 | 3.642E−02 | 4.871E−02 |
| 161 | 1.541E−02 | 4.987E−02 | 4.390E−02 | 7.729E−02 | 5.405E−02 | 3.829E−02 | 1.416E−02 | 2.538E−02 | 4.408E−02 | 2.654E−02 | 6.287E−02 | 5.467E−02 | 4.265E−02 |
| 162 | 2.306E−02 | 1.558E−02 | 2.199E−02 | 2.903E−02 | 3.241E−02 | 3.446E−02 | 2.476E−02 | 1.692E−02 | 2.645E−02 | 1.175E−02 | 5.592E−02 | 2.734E−02 | 4.871E−02 |
| 163 | 1.923E−02 | 1.870E−02 | 2.930E−02 | 2.903E−02 | 1.621E−02 | 1.915E−02 | 3.535E−03 | 1.264E−02 | 8.825E−03 | 1.772E−02 | 6.287E−02 | 4.559E−02 | 3.045E−02 |
| 164 | 1.541E−02 | 1.247E−02 | 2.199E−02 | 4.346E−02 | 2.164E−02 | 1.149E−02 | 1.060E−02 | 1.264E−02 | 2.645E−02 | 2.947E−03 | 2.796E−02 | 2.280E−02 | 1.825E−02 |
| 165 | 3.464E−02 | 1.870E−02 | 2.930E−02 | 2.903E−02 | 1.621E−02 | 4.203E−02 | 4.595E−02 | 1.264E−02 | 6.180E−02 | 1.175E−02 | 9.083E−02 | 1.362E−02 | 6.696E−02 |
| 166 | 3.081E−02 | 3.740E−02 | 2.930E−02 | 5.797E−02 | 2.164E−02 | 2.680E−02 | 2.832E−02 | 2.538E−02 | 3.972E−02 | 5.013E−02 | 6.287E−02 | 3.642E−02 | 6.696E−02 |
| 167 | 1.042E−01 | 2.208E−01 | 8.050E−02 | 1.977E−01 | 1.354E−01 | 6.118E−02 | 3.179E−01 | 6.759E−02 | 1.541E−01 | 1.772E−01 | 9.795E−02 | 1.772E−01 | 2.066E−01 |
| 168 | 8.468E−02 | 1.060E−01 | 3.660E−02 | 1.496E−01 | 1.140E−01 | 8.032E−02 | 1.060E−01 | 8.451E−02 | 7.943E−02 | 1.033E−01 | 1.122E−01 | 1.273E−01 | 1.158E−01 |
| 169 | 6.162E−02 | 5.922E−02 | 3.660E−02 | 6.768E−02 | 7.569E−02 | 8.032E−02 | 3.535E−02 | 8.451E−03 | 5.735E−02 | 5.307E−02 | 4.194E−02 | 6.830E−02 | 7.916E−02 |
| 170 | 5.004E−02 | 2.805E−02 | 5.120E−02 | 4.346E−02 | 5.948E−02 | 6.118E−02 | 2.832E−02 | 2.110E−02 | 2.645E−02 | 1.478E−02 | 6.287E−02 | 5.467E−02 | 4.265E−02 |
| 171 | 3.847E−02 | 5.922E−02 | 3.660E−02 | 8.210E−02 | 4.862E−02 | 4.969E−02 | 7.070E−03 | 2.110E−02 | 3.090E−02 | 5.307E−02 | 6.287E−02 | 5.467E−02 | 9.172E−02 |
| 172 | 8.853E−02 | 1.188E−01 | 1.349E−01 | 1.275E−01 | 7.370E−02 | 8.694E−02 | 1.484E−01 | 9.773E−02 | 5.592E−02 | 1.570E−01 | 1.803E−01 | 1.059E−01 | 1.337E−01 |
| 173 | 2.402E+00 | 2.293E+00 | 4.723E+00 | 2.888E+00 | 3.062E+00 | 2.607E+00 | 2.159E+00 | 2.304E+00 | 2.526E+00 | 2.282E+00 | 3.649E+00 | 3.033E+00 | 3.360E+00 |
| 174 | 3.466E+00 | 3.054E+00 | 7.832E+00 | 4.687E+00 | 4.754E+00 | 4.159E+00 | 3.352E+00 | 4.172E+00 | 4.409E+00 | 3.351E+00 | 5.213E+00 | 4.714E+00 | 5.293E+00 |
| 175 | 1.161E+00 | 1.198E+00 | 1.649E+00 | 9.748E−01 | 9.687E−01 | 1.083E+00 | 8.228E−01 | 8.860E−01 | 1.080E+00 | 9.912E−01 | 1.594E+00 | 1.027E+00 | 1.377E+00 |
| 176 | 3.420E+00 | 2.409E+00 | 4.752E+00 | 3.815E+00 | 3.540E+00 | 3.390E+00 | 2.820E+00 | 3.703E+00 | 2.804E+00 | 3.091E+00 | 5.316E+00 | 3.931E+00 | 4.166E+00 |
| 177 | 1.736E+00 | 1.280E+00 | 1.327E+00 | 7.971E−01 | 6.438E−01 | 1.546E+00 | 1.575E+00 | 1.064E+00 | 1.605E+00 | 1.424E+00 | 1.606E+00 | 1.523E+00 | 1.407E+00 |
| 178 | 3.495E−01 | 4.010E−01 | 2.269E−01 | 1.373E−01 | 7.971E−02 | 4.071E−01 | 3.605E−01 | 2.085E−01 | 2.354E−01 | 4.513E−01 | 2.636E−01 | 2.072E−01 | 2.538E−01 |
| 179 | 3.556E−02 | 3.127E−02 | 3.433E−02 | 2.992E−02 | 2.305E−02 | 4.525E−02 | 3.654E−02 | 2.906E−02 | 3.519E−02 | 5.236E−02 | 2.698E−02 | 2.698E−02 | 4.108E−02 |
| 180 | 3.078E−02 | 1.717E−02 | 2.820E−02 | 3.066E−02 | 2.379E−02 | 2.685E−02 | 1.901E−02 | 2.563E−02 | 1.154E−02 | 2.440E−02 | 4.525E−02 | 2.379E−02 | 3.274E−02 |
| 181 | 1.533E−02 | 1.030E−02 | 3.826E−02 | 2.060E−02 | 1.263E−02 | 2.269E−02 | 1.950E−02 | 1.864E−02 | 1.582E−02 | 2.440E−02 | 4.034E−02 | 1.754E−02 | 2.600E−02 |
| 182 | 6.781E−02 | 4.672E−02 | 1.901E−01 | 1.288E−01 | 8.044E−02 | 7.272E−02 | 9.099E−02 | 6.806E−02 | 6.254E−02 | 9.467E−02 | 2.771E−01 | 8.841E−02 | 7.885E−02 |
| 183 | 1.074E+00 | 1.023E+00 | 2.595E+00 | 2.030E+00 | 1.581E+00 | 1.225E+00 | 1.353E+00 | 1.033E+00 | 9.768E−01 | 1.844E+00 | 3.148E+00 | 1.457E+00 | 1.397E+00 |
| 184 | 1.113E+00 | 1.099E+00 | 2.934E+00 | 2.174E+00 | 1.537E+00 | 1.640E+00 | 1.502E+00 | 1.108E+00 | 1.087E+00 | 1.809E+00 | 3.240E+00 | 1.623E+00 | 1.479E+00 |
| 185 | 8.398E−01 | 7.536E−01 | 2.069E+00 | 1.691E+00 | 1.202E+00 | 1.190E+00 | 9.463E−01 | 8.682E−01 | 7.915E−01 | 1.303E+00 | 2.432E+00 | 1.085E+00 | 9.651E−01 |
| 186 | 1.697E+00 | 1.335E+00 | 3.618E+00 | 3.201E+00 | 2.438E+00 | 2.466E+00 | 2.529E+00 | 2.193E+00 | 1.721E+00 | 2.942E+00 | 4.803E+00 | 2.247E+00 | 2.138E+00 |
| 187 | 5.248E−01 | 4.280E−01 | 7.006E−01 | 7.039E−01 | 6.021E−01 | 5.420E−01 | 5.641E−01 | 4.684E−01 | 4.329E−01 | 7.780E−01 | 1.171E+00 | 5.628E−01 | 5.101E−01 |
| 188 | 5.359E−02 | 4.157E−02 | 6.352E−02 | 5.788E−02 | 4.611E−02 | 5.690E−02 | 5.113E−02 | 3.728E−02 | 4.378E−02 | 6.818E−02 | 1.275E−01 | 5.138E−02 | 4.611E−02 |
| 189 | 1.803E−02 | 1.288E−02 | 1.210E−02 | 1.925E−02 | 1.410E−02 | 2.477E−02 | 2.097E−02 | 6.401E−03 | 7.897E−03 | 1.950E−02 | 3.078E−02 | 1.631E−02 | 1.337E−02 |
| 190 | 2.428E−01 | 1.962E−01 | 2.538E−01 | 2.538E−01 | 1.778E−01 | 3.532E−01 | 2.293E−01 | 2.256E−01 | 1.778E−01 | 3.397E−01 | 2.587E−01 | 2.109E−01 | 3.164E−01 |
| 191 | 2.670E+00 | 1.618E+00 | 2.386E+00 | 1.809E+00 | 1.308E+00 | 2.547E+00 | 3.566E+00 | 1.972E+00 | 2.256E+00 | 3.413E+00 | 2.827E+00 | 2.751E+00 | 2.146E+00 |
| 192 | 7.443E−01 | 6.490E−01 | 5.861E−01 | 5.101E−01 | 2.955E−01 | 9.328E−01 | 1.046E+00 | 5.567E−01 | 5.555E−01 | 1.527E+00 | 7.407E−01 | 6.070E−01 | 6.475E−01 |
| 193 | 7.958E−02 | 7.934E−02 | 1.361E−01 | 8.522E−02 | 5.739E−02 | 1.138E−01 | 1.129E−01 | 7.676E−02 | 6.070E−02 | 1.815E−01 | 1.324E−01 | 7.026E−02 | 8.719E−02 |
| 194 | 6.156E−02 | 5.015E−02 | 1.220E−01 | 1.496E−01 | 1.606E−01 | 1.300E−01 | 6.376E−02 | 9.712E−02 | 7.051E−02 | 9.945E−02 | 2.072E−01 | 8.473E−02 | 1.123E−01 |
| 195 | 2.600E−02 | 1.839E−02 | 7.259E−02 | 5.727E−02 | 5.739E−02 | 5.162E−02 | 3.703E−02 | 2.906E−02 | 4.194E−02 | 4.267E−02 | 7.308E−02 | 4.451E−02 | 5.371E−02 |
| 196 | 1.124E−01 | 9.050E−02 | 1.312E−01 | 1.422E−01 | 1.337E−01 | 4.525E−02 | 3.348E−01 | 1.251E−01 | 1.496E−01 | 2.624E−01 | 2.158E−01 | 1.643E−01 | 1.361E−01 |
| 197 | 8.694E−02 | 8.020E−02 | 9.479E−02 | 8.584E−02 | 4.697E−02 | 9.430E−02 | 1.937E−01 | 1.001E−01 | 8.510E−02 | 1.901E−01 | 1.312E−01 | 1.023E−01 | 1.048E−01 |

APPENDIX D-continued

Ovarian Cancer
Training Dataset

| | | | | | | | | | | | | | |
|---|---|---|---|---|---|---|---|---|---|---|---|---|---|
| 198 | 7.419E−02 | 5.359E−02 | 8.069E−02 | 5.518E−02 | 7.149E−02 | 7.529E−02 | 7.885E−02 | 5.874E−02 | 5.101E−02 | 1.300E−01 | 9.332E−02 | 7.909E−02 | 7.382E−02 |
| 199 | 1.161E−01 | 6.732E−02 | 1.864E−01 | 1.631E−01 | 1.643E−01 | 1.582E−01 | 9.834E−02 | 1.105E−01 | 5.714E−02 | 1.226E−01 | 2.465E−01 | 1.606E−01 | 1.251E−01 |
| 200 | 3.875E−02 | 4.758E−02 | 1.312E−01 | 1.064E−01 | 9.908E−02 | 1.012E−01 | 7.161E−02 | 6.695E−02 | 4.733E−02 | 8.118E−02 | 1.643E−01 | 7.971E−02 | 8.547E−02 |
| 201 | 3.495E−02 | 2.661E−02 | 7.357E−02 | 8.314E−02 | 7.517E−02 | 7.272E−02 | 5.015E−02 | 5.064E−02 | 4.672E−02 | 5.690E−02 | 8.081E−02 | 5.641E−02 | 6.879E−02 |
| 202 | 1.113E−02 | 3.863E−03 | 1.619E−02 | 1.398E−02 | 1.643E−02 | 1.471E−02 | 6.327E−03 | 1.631E−02 | 4.856E−03 | 6.904E−03 | 1.545E−02 | 1.876E−02 | 1.594E−02 |
| 203 | 0.000E+00 | 1.717E−03 | 2.011E−03 | 6.658E−04 | 0.000E+00 | 0.000E+00 | 4.868E−04 | 1.164E−03 | 1.215E−03 | 1.218E−03 | 2.882E−03 | 6.278E−04 | 2.514E−03 |
| 204 | 1.643E−02 | 1.631E−02 | 1.815E−02 | 2.330E−02 | 2.085E−02 | 1.373E−02 | 4.868E−03 | 2.502E−02 | 1.154E−02 | 4.868E−03 | 2.502E−02 | 2.134E−02 | 1.766E−02 |
| 205 | 2.649E−03 | 1.288E−03 | 1.008E−03 | 0.000E+00 | 1.484E−03 | 1.582E−03 | 2.428E−03 | 1.164E−03 | 6.070E−04 | 1.619E−03 | 2.882E−03 | 1.876E−03 | 3.348E−03 |
| 206 | 1.754E−02 | 8.584E−03 | 3.826E−02 | 2.526E−02 | 2.833E−02 | 1.950E−02 | 1.169E−02 | 3.728E−02 | 1.154E−02 | 1.137E−02 | 2.784E−02 | 4.390E−02 | 3.102E−02 |
| 207 | 7.419E−03 | 4.721E−03 | 2.219E−02 | 1.198E−02 | 1.042E−02 | 7.370E−03 | 4.378E−03 | 6.977E−03 | 1.275E−02 | 6.094E−03 | 2.023E−02 | 8.780E−03 | 5.028E−03 |
| 208 | 5.297E−03 | 2.146E−03 | 5.040E−03 | 5.984E−03 | 5.960E−03 | 6.315E−03 | 3.899E−03 | 5.812E−03 | 6.070E−04 | 4.868E−03 | 1.058E−02 | 8.780E−03 | 6.708E−03 |
| 209 | 0.000E+00 | 0.000E+00 | 0.000E+00 | 6.658E−04 | 7.443E−04 | 0.000E+00 | 0.000E+00 | 0.000E+00 | 1.215E−03 | 1.619E−03 | 0.000E+00 | 6.278E−04 | 0.000E+00 |
| 210 | 5.297E−04 | 4.292E−04 | 2.011E−03 | 0.000E+00 | 2.980E−03 | 1.053E−03 | 9.736E−04 | 5.812E−04 | 1.827E−03 | 4.059E−04 | 0.000E+00 | 6.278E−04 | 1.680E−03 |
| 211 | 0.000E+00 | 4.292E−04 | 0.000E+00 | 5.322E−03 | 1.484E−03 | 0.000E+00 | 9.736E−04 | 5.812E−04 | 0.000E+00 | 4.059E−04 | 1.925E−03 | 0.000E+00 | 1.680E−03 |
| 212 | 4.243E−03 | 4.292E−04 | 3.029E−03 | 4.660E−03 | 6.695E−03 | 2.636E−03 | 1.950E−03 | 1.741E−03 | 1.827E−03 | 2.440E−03 | 0.000E+00 | 6.278E−03 | 5.028E−03 |
| 213 | 2.121E−03 | 4.292E−03 | 3.029E−03 | 1.999E−03 | 4.464E−03 | 3.691E−03 | 4.378E−03 | 4.071E−03 | 2.428E−03 | 3.250E−03 | 9.614E−03 | 3.765E−03 | 2.514E−03 |
| 214 | 3.176E−03 | 2.146E−03 | 1.008E−03 | 1.337E−03 | 0.000E+00 | 4.746E−03 | 2.428E−03 | 1.164E−03 | 3.041E−03 | 2.036E−03 | 5.776E−03 | 3.139E−03 | 8.387E−04 |
| 215 | 1.061E−03 | 0.000E+00 | 1.008E−03 | 1.337E−03 | 7.443E−04 | 0.000E+00 | 9.736E−04 | 5.812E−04 | 1.215E−03 | 4.059E−04 | 2.882E−03 | 1.876E−03 | 8.387E−04 |
| 216 | 5.297E−04 | 0.000E+00 | 1.008E−03 | 1.999E−03 | 1.484E−03 | 5.273E−04 | 9.736E−04 | 5.812E−04 | 6.070E−04 | 8.118E−04 | 0.000E+00 | 6.278E−04 | 0.000E+00 |
| 217 | 5.297E−04 | 4.292E−04 | 1.008E−03 | 6.658E−04 | 0.000E+00 | 1.053E−03 | 4.868E−04 | 0.000E+00 | 6.070E−04 | 8.118E−04 | 9.614E−04 | 0.000E+00 | 8.387E−04 |
| 218 | 1.140E+00 | 1.261E+00 | 2.930E+00 | 2.259E+00 | 1.774E+00 | 1.265E+00 | 1.593E+00 | 1.170E+00 | 1.153E+00 | 2.090E+00 | 3.584E+00 | 1.774E+00 | 1.449E+00 |
| 219 | 1.275E−02 | 1.582E−02 | 1.913E−02 | 2.796E−02 | 2.232E−02 | 1.950E−02 | 1.901E−02 | 1.337E−02 | 9.724E−03 | 2.845E−02 | 3.372E−02 | 2.318E−02 | 1.766E−02 |
| 220 | 1.781E+00 | 3.459E+00 | 2.207E+00 | 2.200E+00 | 8.514E−01 | 2.218E+00 | 1.952E+00 | 1.308E+00 | 1.147E+00 | 2.839E+00 | 1.996E+00 | 2.025E+00 | 2.146E+00 |
| 221 | 6.086E+01 | 7.098E+01 | 6.548E+01 | 6.098E+01 | 7.316E+01 | 6.065E+01 | 5.922E+01 | 7.024E+01 | 7.060E+01 | 6.094E+01 | 7.598E+01 | 7.419E+01 | 6.549E+01 |
| 222 | 6.199E+01 | 6.488E+01 | 4.571E+01 | 3.536E+01 | 3.649E+01 | 5.956E+01 | 4.531E+01 | 5.007E+01 | 7.296E+01 | 5.099E+01 | 3.703E+01 | 4.842E+01 | 5.418E+01 |
| 223 | 2.727E+01 | 4.708E+01 | 3.074E+01 | 2.680E+01 | 2.867E+01 | 3.387E+01 | 2.999E+01 | 2.812E+01 | 3.045E+01 | 3.128E+01 | 2.609E+01 | 3.177E+01 | 3.268E+01 |
| 224 | 3.386E+01 | 3.405E+01 | 2.172E+01 | 2.291E+01 | 3.066E+01 | 3.932E+01 | 2.011E+01 | 2.373E+01 | 2.392E+01 | 2.229E+01 | 2.954E+01 | 2.913E+01 | 2.069E+01 |
| 225 | 2.430E+01 | 1.814E+01 | 1.053E+01 | 9.931E+00 | 1.292E+01 | 2.240E+01 | 1.937E+01 | 1.402E+01 | 1.760E+01 | 1.559E+01 | 1.028E+01 | 1.743E+01 | 1.284E+01 |
| 226 | 6.010E+00 | 6.649E+00 | 4.615E+00 | 3.482E+00 | 3.857E+00 | 2.592E+00 | 1.132E+01 | 6.183E+00 | 1.150E+01 | 6.246E+00 | 3.125E+00 | 7.941E+00 | 4.662E+00 |
| 227 | 2.879E+00 | 3.142E+00 | 1.643E+00 | 1.299E+00 | 1.361E+00 | 3.031E+00 | 3.671E+00 | 2.063E+00 | 3.352E+00 | 2.619E+00 | 1.124E+00 | 2.496E+00 | 1.899E+00 |
| 228 | 6.439E−01 | 7.131E−01 | 5.492E−01 | 4.742E−01 | 4.338E−01 | 3.462E−01 | 4.026E−01 | 4.628E−01 | 2.701E−01 | 7.319E−01 | 5.152E−01 | 5.952E−01 | 5.580E−01 |
| 229 | 7.002E−01 | 7.487E−01 | 6.245E−01 | 5.087E−01 | 4.844E−01 | 3.686E−01 | 4.113E−01 | 4.766E−01 | 3.078E−01 | 7.861E−01 | 5.103E−01 | 6.410E−01 | 5.972E−01 |
| 230 | 3.424E+01 | 3.028E+01 | 3.022E+01 | 3.701E+01 | 4.368E+01 | 3.157E+01 | 4.051E+01 | 4.693E+01 | 4.748E+01 | 2.487E+01 | 2.533E+01 | 4.414E+01 | 4.667E+01 |
| 231 | 6.210E+00 | 5.189E+00 | 3.891E+00 | 3.717E+00 | 5.020E+00 | 3.691E+00 | 4.875E+00 | 4.758E+00 | 4.941E+00 | 5.033E+00 | 3.521E+00 | 5.604E+00 | 5.996E+00 |
| 232 | 1.909E+00 | 1.456E+00 | 2.185E+00 | 2.877E+00 | 2.330E+00 | 1.314E+00 | 1.726E+00 | 2.448E+00 | 1.763E+00 | 1.598E+00 | 1.604E+00 | 1.858E+00 | 2.170E+00 |
| 233 | 6.060E+00 | 5.180E+00 | 6.619E+00 | 7.404E+00 | 4.851E+00 | 4.839E+00 | 4.747E+00 | 7.551E+00 | 5.365E+00 | 6.173E+00 | 4.202E+00 | 5.835E+00 | 5.969E+00 |
| 234 | 1.513E+01 | 2.177E+01 | 2.032E+01 | 2.579E+01 | 1.796E+01 | 1.422E+01 | 1.874E+01 | 1.775E+01 | 1.071E+01 | 2.606E+01 | 1.999E+01 | 2.083E+01 | 2.103E+01 |
| 235 | 9.446E+00 | 9.911E+00 | 1.056E+01 | 1.354E+01 | 1.427E+01 | 7.896E+00 | 1.217E+01 | 1.060E+01 | 9.089E+00 | 1.015E+01 | 1.326E+01 | 1.162E+01 | 1.122E+01 |
| 236 | 8.899E−01 | 8.707E−01 | 1.206E+00 | 1.372E+00 | 9.129E−01 | 7.284E−01 | 6.410E−01 | 9.200E−01 | 9.947E−01 | 8.192E−01 | 8.570E−01 | 8.543E−01 | 9.684E−01 |
| 237 | 4.451E+00 | 4.543E+00 | 3.936E+00 | 4.343E+00 | 2.784E+00 | 4.355E+00 | 3.361E+00 | 3.760E+00 | 5.407E+00 | 5.075E+00 | 2.816E+00 | 2.865E+00 | 5.095E+00 |
| 238 | 5.322E+00 | 5.790E+00 | 7.224E+00 | 8.893E+00 | 8.370E+00 | 6.183E+00 | 6.138E+00 | 6.587E+00 | 5.466E+00 | 6.757E+00 | 6.508E+00 | 5.587E+00 | 7.124E+00 |
| 239 | 1.420E+00 | 1.145E+00 | 1.482E+00 | 1.812E+00 | 1.934E+00 | 1.193E+00 | 1.223E+00 | 1.606E+00 | 1.292E+00 | 1.309E+00 | 1.391E+00 | 1.294E+00 | 1.643E+00 |
| 240 | 1.264E+01 | 1.411E+01 | 2.798E+01 | 2.224E+01 | 1.821E+01 | 1.754E+01 | 9.108E+00 | 1.510E+01 | 8.998E+00 | 1.817E+01 | 2.199E+01 | 1.493E+01 | 1.770E+01 |
| 241 | 2.069E+02 | 2.092E+02 | 2.605E+02 | 2.187E+02 | 1.860E+02 | 1.943E+02 | 1.977E+02 | 2.010E+02 | 2.396E+02 | 2.310E+02 | 2.690E+02 | 1.946E+02 | 2.160E+02 |
| 242 | 1.118E+02 | 1.663E+02 | 1.929E+02 | 1.851E+02 | 1.590E+02 | 1.303E+02 | 1.631E+02 | 1.324E+02 | 1.172E+02 | 1.926E+02 | 1.938E+02 | 1.496E+02 | 1.456E+02 |
| 743 | 1.064E+01 | 1.595E+01 | 1.679E+01 | 1.768E+01 | 1.501E+01 | 1.212E+01 | 1.704E+01 | 1.232E+01 | 1.036E+01 | 1.901E+01 | 1.653E+01 | 1.401E+01 | 1.318E+01 |
| 244 | 1.123E+01 | 6.988E+00 | 7.252E+00 | 7.123E+00 | 8.538E+00 | 9.172E+00 | 9.716E+00 | 6.392E+00 | 1.000E+01 | 1.010E+01 | 6.663E+00 | 8.845E+00 | 8.698E+00 |
| 245 | 5.539E+00 | 4.977E+00 | 4.698E+00 | 4.967E+00 | 4.236E+00 | 5.659E+00 | 4.528E+00 | 4.156E+00 | 5.917E+00 | 6.711E+00 | 4.192E+00 | 4.149E+00 | 5.296E+00 |
| 246 | 7.028E+00 | 6.188E+00 | 8.506E+00 | 9.031E+00 | 6.994E+00 | 7.213E+00 | 5.289E+00 | 7.379E+00 | 6.829E+00 | 6.676E+00 | 9.275E+00 | 5.443E+00 | 7.197E+00 |
| 247 | 4.947E+00 | 5.360E+00 | 5.756E+00 | 5.807E+00 | 4.749E+00 | 4.542E+00 | 4.317E+00 | 5.664E+00 | 3.787E+00 | 4.635E+00 | 6.400E+00 | 4.089E+00 | 4.789E+00 |

APPENDIX D-continued

Ovarian Cancer
Training Dataset

| | | | | | | | | | | | | | |
|---|---|---|---|---|---|---|---|---|---|---|---|---|---|
| 248 | 8.845E+01 | 6.655E+01 | 5.555E+01 | 5.250E+01 | 5.391E+01 | 7.455E+01 | 8.070E+01 | 5.111E+01 | 6.374E+01 | 8.473E+01 | 5.652E+01 | 6.226E+01 | 4.773E+01 |
| 249 | 7.532E+01 | 7.391E+01 | 5.243E+01 | 4.849E+01 | 4.121E+01 | 7.701E+01 | 6.285E+01 | 4.125E+01 | 5.031E+01 | 1.001E+02 | 5.693E+01 | 4.810E+01 | 4.532E+01 |
| 250 | 1.383E+02 | 1.331E+02 | 1.167E+02 | 1.140E+02 | 9.850E+01 | 1.438E+02 | 1.041E+02 | 9.263E+01 | 1.101E+02 | 1.395E+02 | 1.478E+02 | 1.046E+02 | 9.496E+01 |
| 251 | 4.909E+01 | 6.582E+01 | 5.206E+01 | 5.348E+01 | 5.263E+01 | 6.235E+01 | 4.328E+01 | 4.549E+01 | 3.923E+01 | 6.201E+01 | 6.549E+01 | 4.913E+01 | 4.350E+01 |
| 252 | 3.380E+00 | 4.252E+00 | 3.926E+00 | 4.062E+00 | 4.192E+00 | 4.453E+00 | 3.081E+00 | 3.197E+00 | 2.633E+00 | 4.260E+00 | 4.480E+00 | 3.752E+00 | 3.292E+00 |
| 253 | 3.371E+00 | 2.681E+00 | 3.834E+00 | 3.725E+00 | 4.015E+00 | 2.439E+00 | 4.159E+00 | 2.985E+00 | 4.455E+00 | 3.751E+00 | 3.637E+00 | 3.978E+00 | 3.553E+00 |
| 254 | 8.476E+00 | 6.384E+00 | 7.724E+00 | 7.298E+00 | 7.539E+00 | 8.534E+00 | 8.924E+00 | 6.167E+00 | 9.350E+00 | 8.854E+00 | 7.192E+00 | 8.288E+00 | 7.580E+00 |
| 255 | 9.549E+00 | 6.668E+00 | 7.503E+00 | 7.210E+00 | 8.762E+00 | 8.507E+00 | 8.171E+00 | 6.765E+00 | 8.758E+00 | 8.711E+00 | 7.107E+00 | 8.174E+00 | 8.614E+00 |
| 256 | 3.610E+00 | 2.914E+00 | 3.965E+00 | 3.638E+00 | 3.361E+00 | 3.271E+00 | 2.840E+00 | 2.926E+00 | 2.914E+00 | 3.496E+00 | 4.558E+00 | 2.850E+00 | 3.186E+00 |
| 257 | 5.714E+00 | 5.300E+00 | 6.568E+00 | 7.279E+00 | 5.988E+00 | 4.994E+00 | 4.675E+00 | 6.736E+00 | 5.673E+00 | 3.901E+00 | 6.404E+00 | 5.224E+00 | 5.402E+00 |
| 258 | 2.547E+01 | 2.111E+01 | 1.852E+01 | 1.671E+01 | 1.477E+01 | 2.739E+01 | 3.112E+01 | 1.628E+01 | 2.194E+01 | 2.919E+01 | 1.589E+01 | 2.002E+01 | 1.439E+01 |
| 259 | 6.223E+01 | 4.000E+01 | 2.989E+01 | 3.239E+01 | 3.456E+01 | 6.222E+01 | 4.709E+01 | 2.818E+01 | 3.220E+01 | 5.035E+01 | 3.734E+01 | 3.758E+01 | 2.480E+01 |
| 260 | 4.667E+01 | 3.950E+01 | 3.228E+01 | 3.728E+01 | 3.353E+01 | 5.537E+01 | 3.984E+01 | 3.335E+01 | 2.824E+01 | 5.005E+01 | 3.470E+01 | 3.538E+01 | 2.834E+01 |
| 261 | 3.140E+01 | 3.018E+01 | 3.620E+01 | 4.354E+01 | 5.001E+01 | 3.520E+01 | 3.710E+01 | 4.307E+01 | 3.675E+01 | 2.768E+01 | 3.357E+01 | 4.538E+01 | 4.390E+01 |
| 262 | 1.271E+01 | 1.235E+01 | 1.254E+01 | 1.248E+01 | 1.556E+01 | 1.377E+01 | 1.213E+01 | 1.637E+01 | 1.357E+01 | 1.148E+01 | 1.290E+01 | 1.506E+01 | 1.610E+01 |
| 263 | 2.308E+00 | 2.014E+00 | 2.707E+00 | 2.540E+00 | 2.283E+00 | 1.671E+00 | 3.153E+00 | 2.359E+00 | 3.463E+00 | 2.676E+00 | 2.447E+00 | 2.568E+00 | 2.328E+00 |
| 264 | 2.328E+00 | 2.039E+00 | 3.985E+00 | 3.243E+00 | 3.208E+00 | 2.269E+00 | 2.599E+00 | 2.561E+00 | 2.923E+00 | 2.544E+00 | 3.983E+00 | 2.777E+00 | 2.432E+00 |
| 265 | 2.050E+00 | 1.569E+00 | 2.812E+00 | 2.769E+00 | 2.785E+00 | 2.038E+00 | 2.082E+00 | 2.023E+00 | 2.004E+00 | 2.139E+00 | 3.481E+00 | 2.131E+00 | 2.102E+00 |
| 266 | 1.735E+00 | 1.411E+00 | 4.149E+00 | 4.032E+00 | 3.494E+00 | 1.869E+00 | 1.471E+00 | 2.718E+00 | 1.382E+00 | 1.681E+00 | 4.896E+00 | 2.606E+00 | 2.247E+00 |
| 267 | 2.134E+00 | 1.538E+00 | 3.937E+00 | 3.826E+00 | 3.585E+00 | 1.812E+00 | 1.528E+00 | 3.032E+00 | 1.621E+00 | 1.606E+00 | 4.049E+00 | 2.626E+00 | 2.610E+00 |
| 268 | 1.051E+01 | 1.155E+01 | 8.390E+00 | 8.498E+00 | 7.710E+00 | 6.336E+00 | 1.809E+01 | 8.040E+00 | 1.067E+01 | 1.345E+01 | 8.757E+00 | 1.216E+01 | 5.804E+00 |
| 269 | 7.591E+00 | 7.273E+00 | 8.706E+00 | 6.759E+00 | 6.896E+00 | 7.648E+00 | 1.117E+01 | 6.654E+00 | 5.580E+00 | 9.512E+00 | 9.087E+00 | 8.161E+00 | 4.624E+00 |
| 270 | 3.885E+00 | 3.421E+00 | 3.901E+00 | 3.552E+00 | 3.554E+00 | 4.805E+00 | 4.033E+00 | 2.871E+00 | 2.296E+00 | 4.481E+00 | 4.973E+00 | 3.390E+00 | 2.368E+00 |
| 271 | 1.249E+01 | 1.280E+01 | 1.424E+01 | 1.529E+01 | 1.220E+01 | 1.368E+01 | 1.314E+01 | 1.943E+01 | 1.716E+01 | 9.624E+00 | 9.074E+00 | 1.533E+01 | 1.439E+01 |
| 272 | 8.608E+01 | 7.367E+01 | 7.943E+01 | 8.880E+01 | 1.068E+02 | 8.027E+01 | 9.790E+01 | 1.128E+02 | 1.176E+02 | 5.657E+01 | 6.823E+01 | 1.060E+02 | 1.135E+02 |
| 273 | 9.510E+01 | 8.170E+01 | 8.837E+01 | 9.613E+01 | 1.228E+02 | 9.054E+01 | 1.012E+02 | 1.234E+02 | 1.285E+02 | 6.067E+01 | 7.104E+01 | 1.174E+02 | 1.227E+02 |
| 274 | 1.495E+01 | 1.188E+01 | 1.215E+01 | 1.281E+01 | 1.964E+01 | 1.325E+01 | 1.623E+01 | 1.836E+01 | 1.840E+01 | 8.447E+00 | 1.040E+01 | 1.867E+01 | 1.967E+01 |
| 275 | 9.392E−01 | 6.611E−01 | 8.727E−01 | 8.739E−01 | 6.546E−01 | 5.514E−01 | 5.165E−01 | 1.249E+00 | 7.827E−01 | 4.320E−01 | 5.695E−01 | 8.633E−01 | 8.181E−01 |
| 276 | 8.843E+00 | 7.886E+00 | 1.174E+01 | 1.481E+01 | 9.851E+00 | 7.149E+00 | 8.665E+00 | 1.558E+01 | 8.614E+00 | 6.717E+00 | 6.863E+00 | 1.053E+01 | 1.098E+01 |
| 277 | 2.337E+01 | 1.799E+01 | 2.426E+01 | 3.141E+01 | 3.477E+01 | 1.717E+01 | 2.434E+01 | 3.448E+01 | 2.021E+01 | 1.660E+01 | 2.530E+01 | 3.094E+01 | 3.238E+01 |
| 278 | 2.365E+01 | 1.832E+01 | 2.443E+01 | 3.149E+01 | 3.590E+01 | 1.695E+01 | 2.415E+01 | 3.480E+01 | 2.050E+01 | 1.673E+01 | 2.432E+01 | 3.037E+01 | 3.244E+01 |
| 279 | 5.707E+00 | 7.557E+00 | 7.470E+00 | 8.543E+00 | 9.092E+00 | 5.140E+00 | 7.067E+00 | 7.436E+00 | 3.582E+00 | 8.490E+00 | 8.634E+00 | 9.004E+00 | 9.345E+00 |
| 280 | 6.070E+00 | 5.652E+00 | 9.401E+00 | 8.758E+00 | 6.562E+00 | 7.039E+00 | 5.158E+00 | 7.848E+00 | 5.546E+00 | 5.931E+00 | 6.522E+00 | 6.075E+00 | 7.336E+00 |
| 281 | 1.061E+02 | 1.043E+02 | 1.185E+02 | 1.041E+02 | 9.140E+01 | 9.681E+01 | 1.119E+02 | 1.047E+02 | 1.153E+02 | 1.104E+02 | 1.186E+02 | 9.348E+01 | 1.075E+02 |
| 282 | 9.687E+01 | 9.356E+01 | 1.022E+02 | 9.373E+01 | 8.254E+01 | 8.502E+01 | 9.693E+01 | 9.480E+01 | 1.022E+02 | 9.922E+01 | 9.849E+01 | 8.238E+01 | 9.509E+01 |
| 283 | 3.059E+01 | 5.306E+01 | 5.605E+01 | 5.722E+01 | 4.944E+01 | 3.959E+01 | 5.409E+01 | 4.128E+01 | 3.282E+01 | 5.760E+01 | 5.138E+01 | 4.263E+01 | 4.381E+01 |
| 284 | 7.477E+00 | 7.016E+00 | 5.429E+00 | 6.612E+00 | 5.271E+00 | 5.508E+00 | 5.398E+00 | 7.759E+00 | 5.459E+00 | 4.636E+00 | 4.876E+00 | 4.866E+00 | 6.173E+00 |
| 285 | 8.587E+01 | 8.331E+01 | 6.831E+01 | 7.017E+01 | 7.046E+01 | 8.954E+01 | 7.184E+01 | 7.476E+01 | 7.918E+01 | 7.611E+01 | 7.871E+01 | 7.196E+01 | 7.137E+01 |
| 286 | 7.030E+01 | 6.819E+01 | 5.169E+01 | 5.277E+01 | 5.748E+01 | 7.116E+01 | 5.686E+01 | 6.425E+01 | 6.317E+01 | 5.965E+01 | 5.618E+01 | 5.761E+01 | 5.820E+01 |
| 287 | 8.796E+00 | 1.327E+01 | 9.263E+00 | 9.748E+00 | 1.045E+01 | 1.243E+01 | 8.539E+00 | 9.163E+00 | 6.940E+00 | 1.092E+01 | 1.083E+01 | 8.778E+00 | 8.538E+00 |
| 288 | 6.082E+01 | 5.783E+01 | 6.735E+01 | 8.301E+01 | 9.739E+01 | 6.927E+01 | 7.363E+01 | 8.822E+01 | 7.083E+01 | 4.597E+01 | 5.557E+01 | 8.699E+01 | 8.898E+01 |
| 289 | 5.153E+01 | 4.830E+01 | 5.447E+01 | 6.761E+01 | 8.276E+01 | 5.551E+01 | 6.122E+01 | 7.412E+01 | 5.959E+01 | 3.516E+01 | 4.429E+01 | 7.261E+01 | 7.278E+01 |
| 290 | 2.310E+01 | 2.276E+01 | 1.847E+01 | 2.088E+01 | 2.667E+01 | 2.452E+01 | 2.491E+01 | 3.179E+01 | 2.756E+01 | 1.784E+01 | 1.487E+01 | 2.800E+01 | 3.150E+01 |
| 291 | 1.940E+01 | 1.851E+01 | 1.418E+01 | 1.611E+01 | 2.189E+01 | 1.974E+01 | 1.997E+01 | 2.678E+01 | 2.227E+01 | 1.386E+01 | 1.032E+01 | 2.216E+01 | 2.585E+01 |
| 292 | 2.384E+00 | 2.314E+00 | 2.596E+00 | 2.545E+00 | 2.820E+00 | 2.615E+00 | 2.423E+00 | 2.927E+00 | 2.393E+00 | 2.089E+00 | 2.992E+00 | 2.553E+00 | 2.810E+00 |
| 293 | 1.645E+00 | 1.231E+00 | 2.770E+00 | 2.436E+00 | 2.911E+00 | 1.894E+00 | 1.311E+00 | 2.336E+00 | 9.761E−01 | 1.190E+00 | 2.894E+00 | 2.190E+00 | 1.867E+00 |
| 294 | 2.296E+00 | 1.997E+00 | 3.474E+00 | 2.703E+00 | 2.142E+00 | 1.897E+00 | 2.079E+00 | 1.894E+00 | 1.593E+00 | 2.639E+00 | 7.779E+00 | 1.870E+00 | 1.680E+00 |
| 295 | 2.298E+00 | 1.959E+00 | 3.385E+00 | 2.690E+00 | 2.104E+00 | 1.906E+00 | 2.141E+00 | 1.965E+00 | 1.597E+00 | 2.772E+00 | 7.802E+00 | 1.897E+00 | 1.623E+00 |
| 296 | 1.316E+00 | 1.575E+00 | 2.508E+00 | 2.275E+00 | 1.449E+00 | 1.133E+00 | 1.690E+00 | 1.226E+00 | 9.178E−01 | 2.190E+00 | 5.941E+00 | 1.340E+00 | 1.059E+00 |
| 297 | 2.800E−01 | 3.151E−01 | 8.211E−01 | 7.311E−01 | 5.428E−01 | 3.419E−01 | 6.526E−01 | 4.859E−01 | 5.126E−01 | 4.046E−01 | 6.766E−01 | 4.084E−01 | 5.294E−01 |

APPENDIX D-continued

Ovarian Cancer
Training Dataset

| | | | | | | | | | | | | | |
|---|---|---|---|---|---|---|---|---|---|---|---|---|---|
| 298 | 1.452E−02 | 2.081E−02 | 2.124E−02 | 1.231E−02 | 2.553E−02 | 1.530E−02 | 1.907E−02 | 2.660E−02 | 1.864E−02 | 1.180E−02 | 1.414E−02 | 1.899E−02 | 2.467E−02 |
| 299 | 8.624E−02 | 9.375E−02 | 2.294E−01 | 2.840E−01 | 2.740E−01 | 9.911E−02 | 1.502E−01 | 1.832E−01 | 7.851E−02 | 1.253E−01 | 2.462E−01 | 1.294E−01 | 1.731E−01 |
| 300 | 5.599E−03 | 7.315E−03 | 7.487E−03 | 8.431E−03 | 2.143E−02 | 6.886E−03 | 6.457E−03 | 1.158E−02 | 4.762E−03 | 4.505E−03 | 9.782E−03 | 7.380E−03 | 1.188E−02 |
| 301 | 6.328E−02 | 7.530E−02 | 1.133E−01 | 1.626E−01 | 1.467E−01 | 1.025E−01 | 1.025E−01 | 1.113E−01 | 7.701E−02 | 7.701E−02 | 1.088E−01 | 8.216E−02 | 9.010E−02 |
| 302 | 1.188E−02 | 3.132E−02 | 4.248E−02 | 1.802E−02 | 5.449E−02 | 4.097E−02 | 1.246E−02 | 2.917E−02 | 2.231E−02 | 1.753E−02 | 4.955E−02 | 2.188E−02 | 4.033E−02 |
| 303 | 2.611E−01 | 3.583E−01 | 3.756E−01 | 3.314E−01 | 4.279E−01 | 3.869E−01 | 3.765E−01 | 3.811E−01 | 4.036E−01 | 4.087E−01 | 2.647E−01 | 2.850E−01 | 3.083E−01 |
| 304 | 5.256E−03 | 4.805E−03 | 8.752E−03 | 1.049E−02 | 9.289E−03 | 5.384E−03 | 3.733E−03 | 6.800E−03 | 5.213E−03 | 6.071E−03 | 1.630E−02 | 3.583E−03 | 8.388E−03 |
| 305 | 3.489E−01 | 4.039E−01 | 8.889E−01 | 8.399E−01 | 1.053E+00 | 4.957E−01 | 5.914E−01 | 6.624E−01 | 5.337E−01 | 3.466E−01 | 5.918E−01 | 5.735E−01 | 5.851E−01 |
| 306 | 3.175E−02 | 2.703E−02 | 3.175E−02 | 3.389E−02 | 6.886E−02 | 3.111E−02 | 3.625E−02 | 4.526E−02 | 3.089E−02 | 2.012E−02 | 2.982E−02 | 4.827E−02 | 4.376E−02 |
| 307 | 1.650E+00 | 2.502E+00 | 1.225E+00 | 1.189E+00 | 2.179E+00 | 2.365E+00 | 1.865E+00 | 3.081E+00 | 2.747E+00 | 1.816E+00 | 3.233E−01 | 1.564E+00 | 1.902E+00 |
| 308 | 2.832E−02 | 3.904E−02 | 1.791E−02 | 1.710E−02 | 4.226E−02 | 4.012E−02 | 3.733E−02 | 4.419E−02 | 4.591E−02 | 2.252E−02 | 7.616E−03 | 2.617E−02 | 3.711E−02 |
| 309 | 4.376E−03 | 3.282E−03 | 5.406E−03 | 1.461E−02 | 1.188E−02 | 3.239E−03 | 7.594E−03 | 1.103E−02 | 6.071E−03 | 4.848E−03 | 5.427E−03 | 8.216E−03 | 7.229E−03 |
| 310 | 1.575E−03 | 2.119E−03 | 4.569E−03 | 2.746E−03 | 3.883E−03 | 2.574E−03 | 1.862E−03 | 3.668E−03 | 4.119E−03 | 3.990E−03 | 9.246E−03 | 2.746E−03 | 3.733E−03 |
| 311 | 1.049E−03 | 5.771E−04 | 3.325E−03 | 1.596E−03 | 1.549E−03 | 1.077E−03 | 5.728E−04 | 2.210E−03 | 1.950E−03 | 8.667E−04 | 3.261E−03 | 6.328E−04 | 3.497E−03 |
| 312 | 5.256E−04 | 5.771E−04 | 5.406E−03 | 1.141E−03 | 7.744E−04 | 4.312E−04 | 2.875E−04 | 5.513E−04 | 4.333E−04 | 6.929E−04 | 1.630E−03 | 0.000E+00 | 1.399E−03 |
| 313 | 1.678E−01 | 1.313E−01 | 1.107E−01 | 1.216E−01 | 2.577E−01 | 1.551E−01 | 1.094E−01 | 2.473E−01 | 2.348E−01 | 1.047E−01 | 3.583E−02 | 2.289E−01 | 2.982E−01 |
| 314 | 6.650E−03 | 6.157E−03 | 4.569E−03 | 4.784E−03 | 1.549E−02 | 5.814E−03 | 3.304E−03 | 1.343E−02 | 8.238E−03 | 4.677E−03 | 5.985E−03 | 1.139E−02 | 1.281E−02 |
| 315 | 2.832E−02 | 3.025E−02 | 3.046E−02 | 2.875E−02 | 4.441E−02 | 3.111E−02 | 2.079E−02 | 4.290E−02 | 4.955E−02 | 2.117E−02 | 2.274E−02 | 3.840E−02 | 6.586E−02 |
| 316 | 2.274E−03 | 1.349E−03 | 2.081E−03 | 2.053E−03 | 1.549E−03 | 1.937E−03 | 1.577E−03 | 1.838E−03 | 1.517E−03 | 1.040E−03 | 1.630E−03 | 1.688E−03 | 2.098E−03 |
| 317 | 2.682E−02 | 2.317E−02 | 2.167E−02 | 2.746E−02 | 4.140E−02 | 3.389E−02 | 2.446E−02 | 3.583E−02 | 3.947E−02 | 2.488E−02 | 9.782E−03 | 3.990E−02 | 4.419E−02 |
| 318 | 1.575E−03 | 1.733E−03 | 1.665E−03 | 2.274E−03 | 2.832E−03 | 2.574E−03 | 1.004E−03 | 2.574E−03 | 1.733E−03 | 1.388E−03 | 5.427E−04 | 3.368E−03 | 2.098E−03 |
| 319 | 2.485E−01 | 2.194E−01 | 1.429E−01 | 1.534E−01 | 2.652E−01 | 2.698E−01 | 1.879E−01 | 3.183E−01 | 3.917E−01 | 2.128E−01 | 5.213E−02 | 2.550E−01 | 3.770E−01 |
| 320 | 0.000E+00 | 5.771E−04 | 1.665E−03 | 1.596E−03 | 1.808E−03 | 6.457E−04 | 0.000E+00 | 9.203E−04 | 1.517E−03 | 5.213E−04 | 1.088E−03 | 8.431E−04 | 6.993E−04 |
| 321 | 1.896E−01 | 1.879E−01 | 1.811E−01 | 1.899E−01 | 3.977E−01 | 2.459E−01 | 1.583E−01 | 3.449E−01 | 2.950E−01 | 1.328E−01 | 4.719E−02 | 3.172E−01 | 4.220E−01 |
| 322 | 5.771E−03 | 5.384E−03 | 5.835E−03 | 5.256E−03 | 9.804E−03 | 7.530E−03 | 4.591E−03 | 9.375E−03 | 8.023E−03 | 6.071E−03 | 2.167E−03 | 8.023E−03 | 1.630E−02 |
| 323 | 2.779E−01 | 2.737E−01 | 1.553E−01 | 1.538E−01 | 3.342E−01 | 3.215E−01 | 2.089E−01 | 3.655E−01 | 4.090E−01 | 2.215E−01 | 5.642E−02 | 3.185E−01 | 5.051E−01 |
| 324 | 8.388E−03 | 1.040E−02 | 3.754E−03 | 5.706E−03 | 1.137E−02 | 9.696E−03 | 7.594E−03 | 8.281E−03 | 1.040E−02 | 6.414E−03 | 5.985E−03 | 9.074E−03 | 1.678E−02 |
| 325 | 1.066E−02 | 8.860E−03 | 1.373E−02 | 1.025E−02 | 1.420E−02 | 1.594E−02 | 9.182E−03 | 1.489E−02 | 1.733E−02 | 9.546E−03 | 1.467E−02 | 1.139E−02 | 1.725E−02 |
| 326 | 1.399E−03 | 1.156E−03 | 3.325E−03 | 1.141E−03 | 2.317E−03 | 8.602E−04 | 4.290E−04 | 1.472E−03 | 1.300E−03 | 5.213E−04 | 0.000E+00 | 1.055E−03 | 1.864E−03 |
| 327 | 1.452E−02 | 1.753E−02 | 1.832E−02 | 1.710E−02 | 1.963E−02 | 1.637E−02 | 9.460E−03 | 1.489E−02 | 2.274E−02 | 1.214E−02 | 1.847E−02 | 1.961E−02 | 2.724E−02 |
| 328 | 1.399E−03 | 2.317E−03 | 1.665E−03 | 2.053E−03 | 4.140E−03 | 1.723E−03 | 2.006E−03 | 1.654E−03 | 2.381E−03 | 2.596E−03 | 1.630E−03 | 2.109E−03 | 1.399E−03 |
| 329 | 3.970E−01 | 3.614E−01 | 2.469E−01 | 3.100E−01 | 7.435E−01 | 5.383E−01 | 3.189E−01 | 7.652E−01 | 7.034E−01 | 2.828E−01 | 6.414E−02 | 5.244E−01 | 7.316E−01 |
| 330 | 4.012E−03 | 6.736E−03 | 3.754E−03 | 3.196E−03 | 5.170E−03 | 4.097E−03 | 3.153E−03 | 7.916E−03 | 7.144E−03 | 3.647E−03 | 3.797E−03 | 7.809E−03 | 7.465E−03 |
| 331 | 3.797E−02 | 3.583E−02 | 2.531E−02 | 3.818E−02 | 6.285E−02 | 3.776E−02 | 2.467E−02 | 5.642E−02 | 5.642E−02 | 3.132E−02 | 2.066E−02 | 4.741E−02 | 7.851E−02 |
| 332 | 1.225E−03 | 1.349E−03 | 2.081E−03 | 1.369E−03 | 3.347E−03 | 1.077E−03 | 1.004E−03 | 1.654E−03 | 8.667E−04 | 6.929E−04 | 2.167E−03 | 1.899E−03 | 1.630E−03 |
| 333 | 2.875E−02 | 2.596E−02 | 1.832E−02 | 1.894E−02 | 3.175E−02 | 2.660E−02 | 1.491E−02 | 2.982E−02 | 3.196E−02 | 1.838E−02 | 1.521E−02 | 3.518E−02 | 3.818E−02 |
| 334 | 0.000E+00 | 0.000E+00 | 0.000E+00 | 0.000E+00 | 2.574E−04 | 4.312E−04 | 0.000E+00 | 1.838E−04 | 2.167E−04 | 1.735E−04 | 5.427E−04 | 4.226E−04 | 6.993E−04 |
| 335 | 5.921E−02 | 6.328E−02 | 3.583E−02 | 3.454E−02 | 5.663E−02 | 6.114E−02 | 3.818E−02 | 8.431E−02 | 9.525E−02 | 3.776E−02 | 1.956E−02 | 5.728E−02 | 9.460E−02 |
| 336 | 2.789E−03 | 2.703E−03 | 1.665E−03 | 2.510E−03 | 3.625E−03 | 3.454E−03 | 1.146E−03 | 3.132E−03 | 2.596E−03 | 2.081E−03 | 4.355E−03 | 1.899E−03 | 3.733E−03 |
| 337 | 7.508E−02 | 7.916E−02 | 7.165E−02 | 7.229E−02 | 1.519E−01 | 1.167E−01 | 6.328E−02 | 1.362E−01 | 1.429E−01 | 4.398E−02 | 2.119E−02 | 1.274E−01 | 2.122E−01 |
| 338 | 1.049E−03 | 1.349E−03 | 4.162E−04 | 9.117E−04 | 2.832E−03 | 3.025E−03 | 1.004E−03 | 3.497E−03 | 3.025E−03 | 2.252E−03 | 5.427E−04 | 3.583E−03 | 3.497E−03 |
| 339 | 4.955E−02 | 6.050E−02 | 3.497E−02 | 3.818E−02 | 7.573E−02 | 6.908E−02 | 3.776E−02 | 8.388E−02 | 9.997E−02 | 3.132E−02 | 1.630E−02 | 6.607E−02 | 1.103E−01 |
| 340 | 2.274E−03 | 4.054E−03 | 3.325E−03 | 2.274E−03 | 2.832E−03 | 4.312E−03 | 2.145E−03 | 4.054E−03 | 3.475E−03 | 2.252E−03 | 1.630E−03 | 3.368E−03 | 4.655E−03 |
| 341 | 8.045E−03 | 4.998E−03 | 1.583E−02 | 9.589E−03 | 1.446E−02 | 8.602E−03 | 5.878E−03 | 1.049E−02 | 6.929E−03 | 4.162E−03 | 1.630E−02 | 7.809E−03 | 9.782E−03 |
| 342 | 6.993E−04 | 7.701E−04 | 8.323E−04 | 4.569E−04 | 2.317E−03 | 4.312E−04 | 5.728E−04 | 3.668E−04 | 1.300E−03 | 3.475E−04 | 5.427E−04 | 1.266E−03 | 2.098E−03 |
| 343 | 7.337E−03 | 1.233E−02 | 1.583E−02 | 1.276E−02 | 1.137E−02 | 6.886E−03 | 6.028E−03 | 9.375E−03 | 9.310E−03 | 8.495E−03 | 1.577E−02 | 1.182E−02 | 1.841E−02 |
| 344 | 1.748E−04 | 7.701E−04 | 0.000E+00 | 6.843E−04 | 2.574E−04 | 2.145E−04 | 5.728E−04 | 1.838E−04 | 6.500E−04 | 1.735E−04 | 1.630E−03 | 0.000E+00 | 0.000E+00 |

APPENDIX D-continued

Ovarian Cancer
Training Dataset

| | Y | Z | AA | AB | AC | AD | AE | AF | AG | AH | AI | AJ | AK |
|---|---|---|---|---|---|---|---|---|---|---|---|---|---|
| 1 | 13828 | 13867 | 13717 | 13693 | CA265 | CA254 | 14586 | 14523 | 14537 | 14671 | 14658 | 14651 | 14648 |
| 2 | Late Malignant | Late Malignant | Late Malignant | Late Malignant | Control | Control | Late Malignant | Late Malignant | Late Malignant | Late Malignant | Late Malignant | Late Malignant | Late Malignant |
| 3 | 3 | 3 | 3 | 3 | 0 | 0 | 3 | 3 | 3 | 3 | 3 | 3 | 3 |
| 4 | −1 | −1 | −1 | −1 | 1 | 1 | −1 | −1 | −1 | −1 | −1 | −1 | −1 |
| 5 | 2.087E+00 | 2.599E+00 | 1.610E+00 | 2.609E+00 | 2.205E+00 | 3.422E+00 | 2.683E+00 | 1.466E+00 | 1.271E+00 | 2.460E+00 | 2.367E+00 | 1.912E+00 | 2.197E+00 |
| 6 | 7.024E−01 | 7.131E−01 | 5.086E−01 | 1.191E+00 | 1.140E+00 | 1.267E+00 | 1.058E+00 | 4.710E−01 | 3.112E−01 | 1.323E+00 | 5.354E−01 | 5.279E−01 | 1.418E+00 |
| 7 | 2.135E−01 | 2.983E−01 | 1.427E−01 | 3.509E−01 | 2.693E−01 | 5.783E−01 | 4.356E−01 | 2.854E−01 | 1.202E−01 | 3.498E−01 | 3.101E−01 | 2.661E−01 | 3.691E−01 |
| 8 | 1.096E+00 | 1.570E+00 | 1.529E+00 | 1.127E+00 | 1.965E+00 | 1.565E+00 | 1.472E+00 | 6.186E−01 | 5.785E−01 | 1.557E+00 | 1.032E+00 | 7.211E−01 | 1.015E+00 |
| 9 | 1.642E−02 | 2.232E−02 | 2.725E−02 | 4.925E−02 | 3.627E−02 | 3.605E−02 | 1.953E−02 | 2.983E−02 | 1.223E−02 | 2.071E−02 | 1.931E−02 | 2.350E−02 | 2.178E−02 |
| 10 | 1.878E−02 | 2.167E−02 | 8.112E−03 | 1.427E−02 | 6.406E−03 | 1.856E−02 | 2.554E−02 | 2.811E−03 | 9.142E−03 | 2.350E−02 | 1.577E−02 | 1.056E−02 | 1.288E−02 |
| 11 | 1.170E−02 | 1.384E−02 | 6.373E−03 | 1.867E−02 | 1.212E−02 | 2.157E−02 | 2.350E−02 | 5.622E−03 | 7.618E−03 | 2.532E−02 | 1.577E−02 | 6.459E−03 | 1.781E−02 |
| 12 | 4.700E−03 | 9.871E−03 | 7.532E−03 | 1.867E−02 | 1.137E−02 | 1.341E−02 | 7.403E−03 | 5.622E−03 | 1.524E−02 | 9.667E−03 | 7.597E−03 | 8.219E−03 | 1.116E−02 |
| 13 | 2.039E−02 | 1.513E−02 | 2.318E−02 | 1.202E−02 | 1.921E−02 | 2.060E−02 | 1.481E−02 | 9.002E−03 | 1.910E−02 | 1.288E−02 | 8.766E−03 | 9.979E−03 | 1.004E−02 |
| 14 | 6.266E−02 | 6.180E−02 | 4.292E−02 | 5.912E−02 | 5.697E−02 | 9.163E−02 | 8.337E−02 | 3.884E−02 | 6.856E−02 | 1.054E−01 | 4.034E−02 | 4.227E−02 | 8.262E−02 |
| 15 | 3.916E−03 | 1.974E−03 | 1.043E−02 | 6.567E−03 | 4.989E−03 | 5.150E−03 | 8.745E−03 | 1.069E−02 | 4.571E−03 | 1.288E−02 | 5.837E−03 | 1.760E−03 | 6.695E−03 |
| 16 | 7.833E−04 | 1.974E−03 | 1.159E−03 | 4.378E−03 | 0.000E+00 | 0.000E+00 | 1.341E−03 | 0.000E+00 | 7.618E−04 | 0.000E+00 | 2.339E−03 | 5.869E−04 | 1.116E−03 |
| 17 | 1.018E−02 | 7.897E−03 | 4.056E−03 | 4.378E−03 | 1.427E−03 | 6.170E−03 | 5.386E−03 | 5.622E−04 | 3.047E−03 | 2.758E−03 | 4.678E−03 | 3.519E−03 | 1.674E−03 |
| 18 | 3.133E−02 | 4.936E−02 | 3.015E−02 | 3.616E−02 | 2.210E−02 | 2.264E−02 | 3.090E−02 | 2.307E−02 | 1.524E−02 | 3.498E−02 | 4.442E−02 | 2.521E−02 | 2.790E−02 |
| 19 | 1.706E−01 | 1.438E−01 | 1.026E−01 | 1.373E−01 | 1.266E−01 | 2.468E−01 | 2.082E−01 | 1.073E−01 | 7.854E−02 | 1.674E−01 | 1.792E−01 | 1.363E−01 | 1.599E−01 |
| 20 | 7.833E−04 | 1.974E−03 | 2.897E−03 | 3.283E−03 | 2.843E−03 | 3.090E−03 | 6.727E−04 | 1.127E−03 | 1.524E−03 | 2.758E−03 | 0.000E+00 | 0.000E+00 | 5.579E−04 |
| 21 | 1.491E−02 | 2.103E−02 | 1.159E−02 | 1.749E−02 | 2.704E−02 | 2.886E−02 | 2.489E−02 | 1.127E−02 | 6.094E−03 | 2.393E−02 | 1.288E−02 | 1.170E−02 | 2.682E−02 |
| 22 | 1.567E−03 | 1.974E−03 | 2.318E−03 | 5.472E−03 | 2.135E−03 | 2.060E−03 | 1.341E−03 | 2.253E−03 | 2.285E−03 | 1.845E−03 | 2.339E−03 | 2.929E−03 | 3.348E−03 |
| 23 | 4.775E−02 | 5.526E−02 | 4.582E−02 | 5.043E−02 | 6.620E−02 | 8.433E−02 | 4.646E−02 | 2.532E−02 | 1.373E−02 | 6.631E−02 | 3.562E−02 | 3.519E−02 | 5.021E−02 |
| 24 | 1.042E−01 | 1.180E−01 | 7.479E−02 | 6.899E−02 | 7.833E−02 | 8.230E−02 | 9.485E−02 | 6.974E−02 | 7.242E−02 | 6.631E−02 | 1.023E−01 | 7.039E−02 | 6.921E−02 |
| 25 | 2.275E−02 | 3.294E−02 | 1.685E−02 | 3.616E−02 | 3.916E−02 | 4.013E−02 | 3.294E−02 | 7.876E−03 | 1.223E−02 | 4.646E−02 | 1.867E−02 | 1.524E−02 | 5.858E−02 |
| 26 | 2.972E−02 | 2.232E−02 | 2.371E−02 | 1.202E−02 | 1.856E−02 | 2.264E−02 | 2.554E−02 | 1.180E−02 | 1.148E−02 | 2.436E−02 | 1.631E−02 | 9.979E−03 | 1.395E−02 |
| 27 | 3.916E−03 | 9.206E−03 | 6.373E−03 | 5.472E−03 | 3.562E−03 | 7.200E−03 | 8.069E−03 | 2.253E−03 | 7.618E−04 | 5.064E−03 | 8.766E−03 | 1.760E−03 | 3.906E−03 |
| 28 | 2.511E−02 | 2.961E−02 | 2.371E−02 | 3.176E−02 | 3.991E−02 | 4.217E−02 | 4.174E−02 | 3.262E−02 | 1.524E−02 | 4.281E−02 | 3.391E−02 | 3.165E−02 | 5.633E−02 |
| 29 | 4.775E−02 | 5.064E−02 | 3.884E−02 | 4.496E−02 | 5.622E−02 | 6.899E−02 | 5.247E−02 | 2.811E−02 | 2.210E−02 | 6.395E−02 | 4.088E−02 | 3.637E−02 | 6.084E−02 |
| 30 | 9.163E−02 | 9.142E−02 | 6.609E−02 | 6.459E−02 | 7.124E−02 | 8.433E−02 | 7.264E−02 | 1.223E−01 | 6.094E−02 | 5.933E−02 | 9.517E−02 | 8.509E−02 | 8.873E−02 |
| 31 | 9.399E−02 | 8.090E−02 | 9.099E−02 | 4.270E−02 | 5.773E−02 | 7.618E−02 | 7.800E−02 | 8.380E−02 | 7.618E−02 | 4.603E−02 | 6.781E−02 | 5.633E−02 | 8.262E−02 |
| 32 | 7.672E−02 | 1.019E−01 | 4.925E−02 | 4.710E−02 | 8.401E−02 | 7.414E−02 | 8.745E−02 | 2.811E−02 | 2.747E−02 | 6.813E−02 | 4.732E−02 | 3.927E−02 | 6.030E−02 |
| 33 | 1.255E−02 | 1.245E−02 | 8.691E−03 | 1.309E−02 | 8.541E−03 | 1.234E−02 | 1.481E−02 | 8.433E−03 | 3.809E−03 | 9.667E−03 | 7.006E−03 | 9.388E−03 | 1.341E−02 |
| 34 | 6.860E−01 | 8.045E−01 | 5.987E−01 | 5.644E−01 | 4.657E−01 | 5.876E−01 | 6.041E−01 | 7.064E−01 | 8.353E−01 | 4.442E−01 | 8.827E−01 | 6.298E−01 | 4.560E−01 |
| 35 | 9.163E−02 | 6.642E−02 | 1.223E−01 | 6.899E−02 | 5.976E−02 | 6.481E−02 | 9.013E−02 | 4.163E−02 | 6.094E−02 | 7.092E−02 | 8.530E−02 | 5.805E−02 | 1.341E−01 |
| 36 | 5.483E−03 | 7.232E−03 | 9.850E−03 | 5.472E−03 | 4.989E−03 | 8.230E−03 | 6.727E−03 | 5.064E−03 | 6.856E−03 | 6.899E−03 | 5.258E−03 | 6.459E−03 | 6.137E−03 |
| 37 | 1.330E−02 | 1.781E−02 | 1.738E−02 | 2.082E−02 | 2.564E−02 | 1.234E−02 | 1.009E−02 | 1.012E−02 | 1.599E−02 | 1.845E−02 | 2.800E−02 | 1.234E−02 | 2.897E−02 |
| 38 | 3.916E−02 | 3.680E−02 | 2.607E−02 | 1.202E−02 | 3.208E−02 | 2.983E−02 | 2.489E−02 | 2.758E−02 | 2.060E−02 | 2.167E−02 | 2.157E−02 | 1.760E−02 | 1.953E−02 |
| 39 | 8.380E−02 | 5.193E−02 | 7.940E−02 | 9.195E−02 | 8.262E−02 | 9.678E−02 | 9.485E−02 | 4.442E−02 | 5.408E−02 | 1.223E−01 | 1.004E−01 | 3.755E−02 | 1.277E−01 |
| 40 | 1.813E−01 | 1.588E−01 | 1.470E−01 | 1.534E−01 | 1.191E−01 | 1.459E−01 | 1.899E−01 | 2.747E−01 | 1.685E−01 | 1.105E−01 | 1.974E−01 | 1.588E−01 | 1.727E−01 |
| 41 | 3.133E−02 | 3.745E−02 | 3.594E−02 | 1.534E−02 | 1.996E−02 | 2.983E−02 | 3.165E−02 | 2.361E−02 | 2.972E−02 | 1.567E−02 | 2.457E−02 | 3.047E−02 | 2.736E−02 |
| 42 | 1.567E−03 | 1.974E−03 | 5.794E−04 | 5.472E−03 | 3.562E−03 | 0.000E+00 | 3.358E−03 | 1.127E−03 | 3.047E−03 | 4.603E−04 | 2.339E−03 | 2.929E−03 | 5.579E−04 |
| 43 | 4.141E−03 | 8.205E−03 | 7.356E−03 | 7.870E−03 | 7.510E−03 | 1.160E−02 | 1.080E−02 | 7.562E−03 | 4.938E−03 | 1.181E−02 | 1.399E−02 | 6.327E−03 | 7.484E−03 |
| 44 | 4.548E−01 | 7.996E−01 | 3.096E−01 | 3.072E−01 | 2.647E−01 | 3.461E−01 | 3.536E−01 | 2.359E−01 | 3.018E−01 | 3.432E−01 | 3.429E−01 | 2.560E−01 | 3.068E−01 |
| 45 | 1.751E−01 | 3.113E−01 | 1.175E−01 | 1.445E−01 | 1.834E−01 | 1.734E−01 | 1.582E−01 | 8.230E−02 | 7.510E−02 | 2.076E−01 | 9.851E−02 | 9.388E−02 | 1.727E−01 |
| 46 | 1.276E−01 | 2.133E−01 | 1.309E−01 | 1.132E−01 | 9.722E−02 | 1.320E−01 | 1.307E−01 | 1.186E−01 | 7.227E−02 | 1.489E−01 | 1.250E−01 | 9.439E−02 | 1.006E−01 |
| 47 | 3.090E−01 | 5.499E−01 | 2.249E−01 | 2.194E−01 | 2.304E−01 | 2.444E−01 | 2.456E−01 | 1.519E−01 | 1.350E−01 | 2.273E−01 | 2.133E−01 | 1.564E−01 | 1.959E−01 |

APPENDIX D-continued

Ovarian Cancer
Training Dataset

| | | | | | | | | | | | | | |
|---|---|---|---|---|---|---|---|---|---|---|---|---|---|
| 48 | 2.778E−02 | 5.092E−02 | 2.726E−02 | 2.204E−02 | 2.150E−02 | 2.492E−02 | 3.652E−02 | 1.024E−02 | 1.314E−02 | 4.192E−02 | 1.903E−02 | 1.253E−02 | 2.958E−02 |
| 49 | 1.031E−02 | 2.428E−02 | 1.389E−02 | 1.024E−02 | 9.208E−03 | 1.381E−02 | 1.646E−02 | 8.359E−03 | 8.950E−03 | 2.073E−02 | 1.078E−02 | 5.195E−03 | 1.299E−02 |
| 50 | 4.141E−03 | 5.041E−03 | 3.755E−03 | 1.049E−03 | 3.241E−03 | 4.681E−03 | 5.324E−03 | 3.241E−03 | 1.826E−03 | 8.822E−03 | 2.382E−03 | 1.829E−03 | 4.938E−03 |
| 51 | 6.404E−02 | 1.085E−01 | 9.516E−02 | 1.103E−01 | 6.173E−02 | 2.136E−01 | 2.085E−01 | 3.242E−01 | 1.505E−01 | 2.158E−01 | 2.980E−01 | 2.326E−01 | 1.075E−01 |
| 52 | 5.633E−04 | 1.733E−03 | 2.778E−03 | 3.138E−03 | 3.935E−03 | 4.681E−03 | 4.038E−03 | 2.829E−03 | 1.096E−03 | 4.295E−03 | 3.215E−03 | 3.241E−03 | 1.739E−03 |
| 53 | 1.039E−01 | 1.103E−01 | 8.230E−02 | 8.050E−02 | 7.021E−02 | 7.639E−02 | 8.822E−02 | 9.979E−02 | 1.052E−01 | 6.816E−02 | 1.124E−01 | 8.976E−02 | 5.838E−02 |
| 54 | 6.101E+00 | 5.184E+00 | 5.352E+00 | 4.568E+00 | 5.934E+00 | 5.616E+00 | 4.381E+00 | 4.362E+00 | 4.736E+00 | 5.123E+00 | 4.408E+00 | 5.743E+00 | 5.238E+00 |
| 55 | 4.860E−01 | 5.369E−01 | 5.167E−01 | 4.555E−01 | 4.119E−01 | 7.180E−01 | 6.096E−01 | 1.002E+00 | 7.112E−01 | 5.586E−01 | 8.695E−01 | 8.446E−01 | 6.060E−01 |
| 56 | 1.911E−01 | 1.769E−01 | 1.865E−01 | 1.515E−01 | 2.134E−01 | 1.729E−01 | 1.407E−01 | 1.362E−01 | 1.697E−01 | 1.817E−01 | 1.471E−01 | 1.796E−01 | 1.892E−01 |
| 57 | 3.219E+00 | 3.439E+00 | 3.261E+00 | 3.070E+00 | 2.334E+00 | 4.577E+00 | 3.582E+00 | 5.711E+00 | 4.357E+00 | 3.058E+00 | 4.774E+00 | 5.259E+00 | 3.220E+00 |
| 58 | 3.344E−02 | 5.118E−02 | 4.475E−02 | 3.421E−02 | 4.347E−02 | 4.810E−02 | 4.372E−02 | 4.707E−02 | 2.906E−02 | 3.781E−02 | 4.089E−02 | 4.449E−02 | 2.906E−02 |
| 59 | 6.764E−02 | 6.713E−02 | 5.838E−02 | 5.453E−02 | 5.170E−02 | 8.050E−02 | 7.536E−01 | 8.950E−02 | 8.539E−02 | 6.224E−02 | 8.436E−02 | 8.693E−02 | 6.764E−02 |
| 60 | 4.990E−02 | 5.787E−02 | 3.935E−02 | 3.729E−02 | 2.983E−02 | 3.909E−02 | 3.729E−02 | 3.729E−02 | 3.806E−02 | 2.701E−02 | 4.887E−02 | 4.630E−02 | 3.112E−02 |
| 61 | 1.299E+00 | 1.103E+00 | 1.288E+00 | 9.738E−01 | 9.842E−01 | 9.615E−01 | 1.365E+00 | 5.955E−01 | 1.217E+00 | 1.441E+00 | 8.712E−01 | 7.610E−01 | 1.299E+00 |
| 62 | 3.352E−01 | 3.337E−01 | 3.185E−01 | 3.308E−01 | 5.298E−01 | 4.324E−01 | 3.299E−01 | 3.381E−01 | 3.152E−01 | 4.123E−01 | 3.260E−01 | 3.063E−01 | 4.776E−01 |
| 63 | 1.031E−02 | 1.546E−02 | 1.402E−02 | 1.024E−02 | 1.145E−02 | 1.011E−02 | 1.355E−02 | 6.739E−03 | 6.584E−03 | 1.808E−02 | 7.279E−03 | 7.742E−03 | 8.976E−03 |
| 64 | 3.018E+00 | 2.634E+00 | 2.691E+00 | 2.474E+00 | 3.614E+00 | 3.317E+00 | 2.667E+00 | 2.433E+00 | 2.731E+00 | 3.017E+00 | 2.400E+00 | 2.649E+00 | 3.415E+00 |
| 65 | 1.211E−01 | 1.547E−01 | 1.211E−01 | 1.024E−01 | 1.625E−01 | 1.246E−01 | 1.160E−01 | 8.565E−02 | 8.410E−02 | 1.242E−01 | 9.722E−02 | 9.748E−02 | 1.301E−01 |
| 66 | 4.527E−01 | 5.139E−01 | 4.905E−01 | 4.345E−01 | 5.273E−01 | 8.463E−01 | 6.412E−01 | 9.201E−01 | 6.325E−01 | 5.833E−01 | 8.291E−01 | 7.281E−01 | 5.406E−01 |
| 67 | 4.835E−02 | 9.516E−02 | 6.301E−02 | 5.272E−02 | 5.890E−02 | 6.584E−02 | 6.044E−02 | 6.327E−02 | 3.626E−02 | 6.378E−02 | 5.915E−02 | 5.581E−02 | 4.244E−02 |
| 68 | 2.183E−01 | 2.491E−01 | 1.633E−01 | 1.749E−01 | 1.517E−01 | 1.865E−01 | 1.948E−01 | 1.898E−01 | 2.335E−01 | 1.371E−01 | 2.694E−01 | 1.723E−01 | 1.743E−01 |
| 69 | 6.335E−01 | 4.715E−01 | 5.246E−01 | 4.783E−01 | 4.781E−01 | 4.435E−01 | 7.308E−01 | 2.931E−01 | 5.961E−01 | 6.436E−01 | 4.009E−01 | 3.063E−01 | 6.637E−01 |
| 70 | 3.498E−02 | 4.167E−02 | 3.755E−02 | 2.546E−02 | 2.983E−02 | 2.623E−02 | 3.395E−02 | 1.551E−02 | 2.881E−02 | 2.752E−02 | 2.726E−02 | 2.052E−02 | 3.035E−02 |
| 71 | 1.088E−02 | 1.355E−02 | 5.967E−03 | 8.410E−03 | 8.359E−03 | 5.684E−03 | 5.813E−03 | 5.941E−03 | 5.658E−03 | 8.822E−03 | 7.150E−03 | 2.392E−03 | 7.099E−03 |
| 72 | 2.065E−03 | 3.318E−03 | 2.778E−03 | 1.839E−03 | 3.935E−03 | 2.467E−03 | 2.418E−03 | 1.751E−03 | 1.826E−03 | 3.961E−03 | 2.521E−03 | 2.109E−03 | 2.407E−03 |
| 73 | 1.648E−03 | 6.919E−04 | 6.095E−04 | 0.000E+00 | 3.747E−03 | 0.000E+00 | 7.077E−04 | 0.000E+00 | 8.014E−04 | 0.000E+00 | 2.460E−03 | 6.174E−04 | 0.000E+00 |
| 74 | 8.239E−03 | 7.607E−03 | 4.876E−03 | 1.151E−02 | 4.492E−03 | 4.334E−03 | 9.199E−03 | 2.370E−03 | 4.808E−03 | 2.415E−03 | 6.761E−03 | 3.081E−03 | 6.456E−03 |
| 75 | 4.774E−02 | 2.980E−02 | 7.065E−02 | 6.332E−02 | 3.815E−02 | 9.413E−02 | 8.352E−02 | 4.616E−02 | 5.858E−02 | 5.135E−02 | 7.190E−02 | 5.858E−02 | 1.332E−01 |
| 76 | 6.749E−02 | 4.910E−02 | 1.079E−01 | 8.521E−02 | 3.600E−02 | 1.354E−01 | 1.343E−01 | 5.971E−02 | 5.688E−02 | 5.282E−02 | 1.112E−01 | 8.081E−02 | 1.716E−01 |
| 77 | 2.472E−03 | 6.919E−04 | 6.095E−03 | 1.037E−02 | 7.494E−04 | 1.298E−02 | 9.910E−03 | 2.957E−03 | 8.014E−03 | 6.783E−03 | 7.991E−03 | 4.323E−03 | 2.054E−02 |
| 78 | 8.239E−04 | 1.388E−03 | 2.438E−03 | 1.151E−03 | 0.000E+00 | 0.000E+00 | 1.411E−03 | 0.000E+00 | 0.000E+00 | 4.842E−04 | 6.140E−04 | 1.230E−03 | 1.174E−03 |
| 79 | 1.648E−03 | 0.000E+00 | 3.047E−03 | 2.302E−03 | 7.494E−04 | 1.082E−03 | 1.411E−03 | 2.957E−03 | 0.000E+00 | 1.456E−03 | 3.691E−03 | 1.230E−03 | 0.000E+00 |
| 80 | 2.472E−03 | 2.077E−03 | 6.095E−04 | 4.605E−03 | 0.000E+00 | 1.082E−03 | 2.122E−03 | 2.957E−03 | 1.603E−03 | 4.842E−04 | 2.460E−03 | 2.472E−03 | 0.000E+00 |
| 81 | 9.887E−03 | 6.230E−03 | 7.314E−03 | 1.037E−02 | 7.494E−03 | 7.573E−03 | 7.077E−03 | 5.914E−03 | 5.609E−03 | 6.298E−03 | 3.070E−03 | 4.323E−03 | 5.869E−03 |
| 82 | 1.648E−03 | 2.077E−03 | 7.923E−03 | 5.756E−03 | 7.494E−04 | 7.573E−03 | 1.411E−03 | 1.185E−03 | 2.404E−03 | 3.386E−03 | 3.691E−03 | 3.081E−03 | 3.521E−03 |
| 83 | 5.767E−03 | 1.388E−03 | 4.266E−03 | 3.454E−03 | 2.246E−03 | 1.082E−03 | 7.077E−04 | 3.544E−03 | 5.609E−03 | 9.684E−04 | 1.840E−03 | 4.323E−03 | 1.761E−03 |
| 84 | 8.239E−03 | 1.107E−02 | 1.467E−02 | 6.907E−03 | 1.124E−02 | 4.334E−03 | 9.199E−03 | 1.185E−02 | 1.208E−02 | 5.327E−03 | 1.106E−02 | 6.174E−03 | 1.580E−02 |
| 85 | 2.472E−03 | 2.765E−03 | 0.000E+00 | 1.151E−03 | 1.501E−03 | 1.082E−03 | 2.833E−03 | 1.772E−03 | 4.808E−03 | 1.456E−03 | 1.840E−03 | 4.323E−03 | 0.000E+00 |
| 86 | 9.063E−03 | 9.684E−03 | 9.142E−03 | 5.756E−03 | 1.124E−02 | 1.082E−02 | 4.955E−03 | 5.327E−03 | 7.212E−03 | 4.357E−03 | 8.600E−03 | 7.404E−03 | 1.411E−02 |
| 87 | 2.472E−02 | 1.727E−02 | 3.905E−02 | 2.991E−02 | 1.569E−02 | 2.494E−02 | 5.023E−02 | 2.190E−02 | 2.325E−02 | 1.738E−02 | 3.138E−02 | 2.596E−02 | 5.045E−02 |
| 88 | 5.767E−03 | 2.765E−03 | 3.657E−03 | 9.221E−03 | 2.246E−03 | 5.418E−03 | 3.533E−03 | 2.370E−03 | 6.411E−03 | 2.415E−03 | 5.530E−03 | 4.932E−03 | 7.043E−03 |
| 89 | 1.321E−02 | 6.230E−03 | 1.704E−02 | 1.151E−02 | 5.993E−03 | 9.740E−03 | 7.077E−03 | 5.914E−03 | 1.603E−02 | 5.327E−03 | 1.411E−02 | 1.050E−02 | 1.580E−02 |
| 90 | 1.151E−02 | 8.307E−03 | 4.142E−02 | 1.964E−02 | 6.738E−03 | 3.679E−02 | 2.619E−02 | 1.006E−02 | 2.562E−02 | 2.133E−02 | 2.822E−02 | 1.603E−02 | 6.749E−02 |
| 91 | 2.472E−03 | 6.230E−03 | 7.314E−03 | 4.605E−03 | 2.246E−03 | 5.418E−03 | 6.366E−03 | 3.544E−03 | 3.205E−03 | 5.327E−03 | 8.600E−03 | 3.081E−03 | 1.998E−02 |
| 92 | 4.120E−03 | 1.107E−02 | 1.036E−02 | 1.151E−02 | 1.648E−02 | 1.298E−02 | 9.910E−03 | 1.006E−02 | 1.524E−02 | 5.327E−03 | 8.600E−03 | 8.025E−03 | 1.704E−02 |
| 93 | 1.896E−02 | 1.107E−02 | 9.752E−03 | 8.070E−03 | 5.248E−03 | 9.740E−03 | 5.666E−03 | 7.099E−03 | 1.287E−02 | 1.065E−02 | 1.354E−02 | 1.050E−02 | 1.115E−02 |
| 94 | 5.767E−03 | 4.153E−03 | 3.047E−03 | 1.151E−03 | 7.494E−04 | 0.000E+00 | 4.244E−03 | 1.772E−03 | 0.000E+00 | 4.842E−04 | 6.140E−04 | 3.702E−03 | 5.282E−03 |
| 95 | 1.569E−02 | 8.995E−03 | 1.467E−02 | 9.221E−03 | 3.747E−03 | 9.740E−03 | 8.488E−03 | 9.470E−03 | 7.212E−03 | 1.264E−02 | 1.230E−02 | 5.553E−03 | 1.524E−02 |
| 96 | 8.239E−03 | 4.153E−03 | 4.266E−03 | 6.907E−03 | 7.494E−04 | 6.490E−03 | 6.366E−03 | 3.544E−03 | 5.609E−03 | 3.871E−03 | 3.691E−03 | 4.323E−03 | 5.869E−03 |
| 97 | 9.887E−03 | 2.765E−03 | 6.704E−03 | 3.454E−03 | 7.494E−04 | 2.167E−03 | 2.833E−03 | 3.544E−03 | 4.007E−03 | 1.941E−03 | 3.070E−03 | 4.932E−03 | 5.282E−03 |

APPENDIX D-continued

Ovarian Cancer
Training Dataset

| | | | | | | | | | | | | | |
|---|---|---|---|---|---|---|---|---|---|---|---|---|---|
| 98 | 1.230E−02 | 8.307E−03 | 1.467E−02 | 1.037E−02 | 8.984E−03 | 2.167E−03 | 8.488E−03 | 4.729E−03 | 1.122E−02 | 5.813E−03 | 6.761E−03 | 4.932E−03 | 8.804E−03 |
| 99 | 5.371E−02 | 5.861E−02 | 1.093E−01 | 1.002E−01 | 1.435E−01 | 7.762E−02 | 6.070E−02 | 3.605E−02 | 6.364E−02 | 8.155E−02 | 7.615E−02 | 6.107E−02 | 6.757E−02 |
| 100 | 3.850E−02 | 4.439E−02 | 4.500E−02 | 4.010E−02 | 3.176E−02 | 2.710E−02 | 4.378E−02 | 2.759E−02 | 3.139E−02 | 2.526E−02 | 3.544E−02 | 3.017E−02 | 2.992E−02 |
| 101 | 2.158E−01 | 1.717E−01 | 1.337E−01 | 1.717E−01 | 1.361E−01 | 1.778E−01 | 2.207E−01 | 1.106E−01 | 2.036E−01 | 1.178E−01 | 1.839E−01 | 1.704E−01 | 1.925E−01 |
| 102 | 4.966E−01 | 5.138E−01 | 7.811E−01 | 4.194E−01 | 4.979E−01 | 4.071E−01 | 4.746E−01 | 4.427E−01 | 7.117E−01 | 3.691E−01 | 4.942E−01 | 4.231E−01 | 3.850E−01 |
| 103 | 2.722E−01 | 2.575E−01 | 1.803E−01 | 2.354E−01 | 1.557E−01 | 2.526E−01 | 2.931E−01 | 1.876E−01 | 2.771E−01 | 1.410E−01 | 2.158E−01 | 2.195E−01 | 2.379E−01 |
| 104 | 2.158E−01 | 2.722E−01 | 3.029E−01 | 1.999E−01 | 2.685E−01 | 1.668E−01 | 2.219E−01 | 2.367E−01 | 2.452E−01 | 1.999E−01 | 1.852E−01 | 1.582E−01 | 1.876E−01 |
| 105 | 9.585E−01 | 8.886E−01 | 1.015E+00 | 6.094E−01 | 6.720E−01 | 5.892E−01 | 7.002E−01 | 7.925E−01 | 1.429E+00 | 4.697E−01 | 7.805E−01 | 7.419E−01 | 6.941E−01 |
| 106 | 1.373E−01 | 1.337E−01 | 1.631E−01 | 1.594E−01 | 1.582E−01 | 1.140E−01 | 1.176E−01 | 9.258E−02 | 1.210E−01 | 1.386E−01 | 1.435E−01 | 1.275E−01 | 1.570E−01 |
| 107 | 1.337E−01 | 1.373E−01 | 1.398E−01 | 1.582E−01 | 1.545E−01 | 1.129E−01 | 9.761E−02 | 9.319E−02 | 1.337E−01 | 9.258E−02 | 1.095E−01 | 1.006E−01 | 1.180E−01 |
| 108 | 1.704E−01 | 2.121E−01 | 1.803E−01 | 1.827E−01 | 2.109E−01 | 1.655E−01 | 1.741E−01 | 1.093E−01 | 1.974E−01 | 1.251E−01 | 1.754E−01 | 1.263E−01 | 1.704E−01 |
| 109 | 7.161E−03 | 7.517E−03 | 1.126E−02 | 1.251E−02 | 1.058E−02 | 4.709E−03 | 1.077E−02 | 9.638E−03 | 1.045E−02 | 6.315E−03 | 6.671E−03 | 3.348E−03 | 9.565E−03 |
| 110 | 3.495E−02 | 3.004E−02 | 1.852E−02 | 4.635E−02 | 2.526E−02 | 6.352E−02 | 2.685E−02 | 6.168E−02 | 3.924E−02 | 2.845E−02 | 5.273E−02 | 6.634E−02 | 3.948E−02 |
| 111 | 1.251E−02 | 2.330E−02 | 9.933E−03 | 2.134E−02 | 2.440E−02 | 3.409E−02 | 2.465E−02 | 3.850E−02 | 2.784E−02 | 2.367E−02 | 2.943E−02 | 3.556E−02 | 2.747E−02 |
| 112 | 1.606E−02 | 2.256E−02 | 1.594E−02 | 2.134E−02 | 2.281E−02 | 2.710E−02 | 1.312E−02 | 2.183E−02 | 8.706E−03 | 1.312E−02 | 3.066E−02 | 1.950E−02 | 1.212E−02 |
| 113 | 4.476E−03 | 6.009E−03 | 5.297E−03 | 2.502E−03 | 4.071E−03 | 8.228E−03 | 5.383E−03 | 9.001E−03 | 6.094E−03 | 1.582E−03 | 4.672E−03 | 7.382E−03 | 4.464E−03 |
| 114 | 7.161E−03 | 6.009E−03 | 7.946E−03 | 2.502E−03 | 1.221E−02 | 1.288E−02 | 6.916E−03 | 1.221E−02 | 9.577E−03 | 3.151E−03 | 1.002E−02 | 7.382E−03 | 7.014E−03 |
| 115 | 1.704E−02 | 1.803E−02 | 6.622E−03 | 8.768E−03 | 5.702E−03 | 2.121E−02 | 9.994E−03 | 1.410E−02 | 1.045E−02 | 5.788E−03 | 2.465E−02 | 1.471E−02 | 1.084E−02 |
| 116 | 8.952E−03 | 7.517E−03 | 4.635E−03 | 1.002E−02 | 8.142E−03 | 5.886E−03 | 8.461E−03 | 1.093E−02 | 1.741E−03 | 3.679E−03 | 7.345E−03 | 7.382E−03 | 2.551E−03 |
| 117 | 1.876E−02 | 1.729E−02 | 1.192E−02 | 2.134E−02 | 1.790E−02 | 2.710E−02 | 1.459E−02 | 1.221E−02 | 1.312E−02 | 8.939E−03 | 1.937E−02 | 2.477E−02 | 1.212E−02 |
| 118 | 5.371E−03 | 1.508E−02 | 1.459E−02 | 1.876E−02 | 2.440E−03 | 9.405E−03 | 1.533E−02 | 1.288E−02 | 8.706E−03 | 4.206E−03 | 9.344E−03 | 1.471E−02 | 7.652E−03 |
| 119 | 1.074E−02 | 1.275E−02 | 9.933E−03 | 1.999E−02 | 9.761E−03 | 1.876E−02 | 1.077E−02 | 1.484E−02 | 9.577E−03 | 8.939E−03 | 1.606E−02 | 7.382E−03 | 7.014E−03 |
| 120 | 9.847E−03 | 6.769E−03 | 4.635E−03 | 6.254E−03 | 8.142E−03 | 1.176E−02 | 1.153E−02 | 1.668E−02 | 7.836E−03 | 3.679E−03 | 1.068E−02 | 1.337E−02 | 1.275E−02 |
| 121 | 6.162E−02 | 2.823E−02 | 6.215E−02 | 1.015E−01 | 4.586E−02 | 5.156E−02 | 4.817E−02 | 3.215E−02 | 2.725E−02 | 3.295E−02 | 1.674E−02 | 3.357E−02 | 1.995E−02 |
| 122 | 6.162E−02 | 6.118E−02 | 1.122E−01 | 2.039E−01 | 1.630E−01 | 1.549E−01 | 1.638E−01 | 1.968E−01 | 7.631E−02 | 1.710E−01 | 1.505E−01 | 4.622E−02 | 1.354E−01 |
| 123 | 3.419E+00 | 2.636E+00 | 2.511E+00 | 4.559E+00 | 3.384E+00 | 1.808E+00 | 3.642E+00 | 4.639E+00 | 1.763E+00 | 3.232E+00 | 3.170E+00 | 2.680E+00 | 2.832E+00 |
| 124 | 6.162E−02 | 9.439E−03 | 3.731E−02 | 9.439E−02 | 5.601E−02 | 3.678E−02 | 2.885E−02 | 3.215E−02 | 3.268E−02 | 2.636E−02 | 2.930E−02 | 4.622E−02 | 2.796E−02 |
| 125 | 2.805E−02 | 0.000E+00 | 7.881E−02 | 7.053E−02 | 6.625E−02 | 8.094E−02 | 4.328E−02 | 2.814E−02 | 3.268E−02 | 2.306E−02 | 1.674E−02 | 1.683E−02 | 2.395E−02 |
| 126 | 3.918E−01 | 3.482E−01 | 4.853E−01 | 1.220E+00 | 2.004E+00 | 6.776E−01 | 7.845E−01 | 5.637E−01 | 3.330E−01 | 1.247E+00 | 5.557E−01 | 4.283E−01 | 9.973E−01 |
| 127 | 8.682E−01 | 8.994E−01 | 1.291E+00 | 2.431E+00 | 3.660E+00 | 1.763E+00 | 1.469E+00 | 2.360E+00 | 9.083E−01 | 2.547E+00 | 1.327E+00 | 9.617E−01 | 2.048E+00 |
| 128 | 2.858E+00 | 2.867E+00 | 1.523E+00 | 3.428E+00 | 3.134E+00 | 1.719E+00 | 3.455E+00 | 3.580E+00 | 1.567E+00 | 3.170E+00 | 2.191E+00 | 2.297E+00 | 2.609E+00 |
| 129 | 6.162E−02 | 4.239E−02 | 6.215E−02 | 7.053E−02 | 4.078E−02 | 1.327E−01 | 3.847E−02 | 2.012E−02 | 4.907E−02 | 3.624E−02 | 5.013E−02 | 3.357E−02 | 3.989E−02 |
| 130 | 3.188E+00 | 2.867E+00 | 7.458E+00 | 1.131E+01 | 1.136E+01 | 6.508E+00 | 7.191E+00 | 3.304E+00 | 3.669E+00 | 1.333E+01 | 4.150E+00 | 2.956E+00 | 1.067E+01 |
| 131 | 2.698E+00 | 2.992E+00 | 4.746E+00 | 6.874E+00 | 7.352E+00 | 4.425E+00 | 6.162E+00 | 3.856E+00 | 3.562E+00 | 1.243E+01 | 3.945E+00 | 2.093E+00 | 8.657E+00 |
| 132 | 4.479E−02 | 5.174E−02 | 1.371E−01 | 7.053E−02 | 1.327E−01 | 2.208E−02 | 9.617E−02 | 7.649E−02 | 2.182E−02 | 5.272E−02 | 7.943E−02 | 2.520E−02 | 4.791E−02 |
| 133 | 7.284E−02 | 1.416E−02 | 2.484E−02 | 3.918E−02 | 2.039E−02 | 1.469E−02 | 3.847E−02 | 3.215E−02 | 1.086E−02 | 1.318E−02 | 4.595E−02 | 1.256E−02 | 2.395E−02 |
| 134 | 1.683E−02 | 1.416E−02 | 2.075E−02 | 5.485E−02 | 3.054E−02 | 7.364E−03 | 1.923E−02 | 1.612E−02 | 1.086E−02 | 1.647E−02 | 2.093E−02 | 0.000E+00 | 3.989E−03 |
| 135 | 3.918E−02 | 3.295E−02 | 2.484E−02 | 3.134E−02 | 2.039E−02 | 2.208E−02 | 1.923E−02 | 8.050E−03 | 3.268E−02 | 3.295E−02 | 1.674E−02 | 8.397E−03 | 3.598E−02 |
| 136 | 1.683E−02 | 2.823E−02 | 2.075E−02 | 1.567E−02 | 3.054E−02 | 0.000E+00 | 1.923E−02 | 1.612E−02 | 1.638E−02 | 1.318E−02 | 5.850E−02 | 4.194E−03 | 1.594E−02 |
| 137 | 3.357E−02 | 5.174E−02 | 9.528E−02 | 5.485E−02 | 6.625E−02 | 2.208E−02 | 3.847E−02 | 8.050E−02 | 9.261E−02 | 2.306E−02 | 3.758E−02 | 3.776E−02 | 3.989E−02 |
| 138 | 6.162E−02 | 1.879E−02 | 2.075E−02 | 1.567E−02 | 4.586E−02 | 5.886E−02 | 1.443E−02 | 2.012E−02 | 2.725E−02 | 1.977E−02 | 2.093E−02 | 8.397E−03 | 1.995E−02 |
| 139 | 2.182E−01 | 1.834E−01 | 1.745E−01 | 3.215E−01 | 2.698E−01 | 2.208E−01 | 2.404E−01 | 3.500E−01 | 1.202E−01 | 2.565E−01 | 1.131E−01 | 1.808E−01 | 3.152E−01 |
| 140 | 1.175E−01 | 1.416E−01 | 8.290E−02 | 1.959E−01 | 1.986E−01 | 1.033E−01 | 1.496E−01 | 2.493E−01 | 9.795E−02 | 1.710E−01 | 1.211E−01 | 8.397E−02 | 2.591E−01 |
| 141 | 6.723E−02 | 1.416E−02 | 8.709E−02 | 8.620E−02 | 9.172E−02 | 8.094E−02 | 5.779E−02 | 4.025E−02 | 1.638E−02 | 7.248E−02 | 6.687E−02 | 5.459E−02 | 6.785E−02 |
| 142 | 1.683E−02 | 2.351E−02 | 1.247E−02 | 3.918E−02 | 2.039E−02 | 7.364E−03 | 2.404E−02 | 1.211E−02 | 2.182E−02 | 1.647E−02 | 2.930E−02 | 2.520E−02 | 7.988E−03 |
| 143 | 3.357E−02 | 1.416E−02 | 2.484E−02 | 1.567E−02 | 2.547E−02 | 2.208E−02 | 1.443E−02 | 4.025E−03 | 1.086E−02 | 1.318E−02 | 1.256E−02 | 2.102E−02 | 2.395E−02 |
| 144 | 2.805E−02 | 2.351E−02 | 3.313E−02 | 2.351E−02 | 9.706E−02 | 1.469E−02 | 2.404E−02 | 2.814E−02 | 1.638E−02 | 3.624E−02 | 4.595E−02 | 2.102E−02 | 3.598E−02 |
| 145 | 1.122E−02 | 2.351E−02 | 2.484E−02 | 2.351E−02 | 9.172E−02 | 1.469E−02 | 3.366E−02 | 4.426E−02 | 3.268E−02 | 2.965E−02 | 2.930E−02 | 1.683E−02 | 7.988E−03 |
| 146 | 2.573E−01 | 2.021E−01 | 2.030E−01 | 1.959E−01 | 2.547E−01 | 5.886E−02 | 3.419E−01 | 2.734E−01 | 1.416E−01 | 3.099E−01 | 1.300E−01 | 1.932E−01 | 2.119E−01 |
| 147 | 1.006E−01 | 1.131E−01 | 9.528E−02 | 1.336E−01 | 2.805E−01 | 1.621E−01 | 1.683E−01 | 1.852E−01 | 1.086E−01 | 2.440E−01 | 7.943E−02 | 8.397E−02 | 1.434E−01 |

APPENDIX D-continued

Ovarian Cancer
Training Dataset

| | | | | | | | | | | | | | |
|---|---|---|---|---|---|---|---|---|---|---|---|---|---|
| 148 | 3.695E−01 | 3.998E−01 | 2.360E−01 | 4.470E−01 | 8.201E−01 | 2.573E−01 | 4.960E−01 | 7.845E−01 | 1.256E−01 | 7.044E−01 | 3.179E−01 | 4.034E−01 | 5.948E−01 |
| 149 | 1.345E−01 | 8.468E−02 | 6.634E−02 | 1.015E−01 | 1.834E−01 | 1.256E−01 | 1.879E−01 | 2.012E−01 | 8.727E−02 | 1.612E−01 | 8.362E−02 | 5.877E−02 | 2.155E−01 |
| 150 | 4.479E−02 | 2.351E−02 | 4.150E−03 | 2.351E−02 | 3.054E−02 | 2.947E−02 | 9.617E−03 | 2.012E−02 | 5.450E−03 | 1.318E−02 | 3.339E−02 | 2.939E−02 | 3.197E−02 |
| 151 | 3.357E−02 | 1.879E−02 | 1.656E−02 | 4.702E−02 | 2.039E−02 | 6.625E−02 | 9.617E−03 | 8.050E−03 | 2.182E−02 | 1.977E−02 | 2.093E−02 | 2.102E−02 | 7.988E−03 |
| 152 | 2.805E−02 | 2.823E−02 | 4.978E−02 | 7.053E−02 | 1.273E−01 | 4.417E−02 | 2.404E−02 | 1.612E−02 | 1.086E−02 | 3.954E−02 | 1.674E−02 | 3.776E−02 | 5.592E−02 |
| 153 | 5.601E−03 | 1.879E−02 | 3.313E−02 | 3.918E−02 | 4.078E−02 | 0.000E+00 | 4.817E−02 | 2.413E−02 | 4.907E−02 | 2.965E−02 | 2.093E−02 | 8.397E−03 | 3.989E−02 |
| 154 | 3.357E−02 | 9.439E−03 | 0.000E+00 | 3.918E−02 | 2.039E−02 | 1.469E−02 | 1.443E−02 | 1.211E−02 | 0.000E+00 | 9.884E−03 | 4.176E−03 | 1.256E−02 | 1.594E−02 |
| 155 | 5.601E−03 | 9.439E−03 | 1.656E−02 | 5.485E−02 | 5.093E−02 | 2.208E−02 | 1.923E−02 | 3.624E−02 | 2.725E−02 | 1.318E−02 | 2.093E−02 | 2.102E−02 | 3.197E−02 |
| 156 | 4.203E−01 | 3.482E−01 | 3.072E−01 | 3.295E−01 | 3.259E−01 | 1.104E−01 | 5.245E−01 | 4.630E−01 | 1.745E−01 | 8.005E−01 | 1.879E−01 | 1.131E−01 | 4.951E−01 |
| 157 | 1.460E−01 | 1.273E−01 | 1.077E−01 | 1.015E−01 | 2.191E−01 | 5.886E−02 | 1.825E−01 | 1.772E−01 | 7.631E−02 | 2.440E−01 | 8.362E−02 | 7.133E−02 | 2.075E−01 |
| 158 | 5.156E−01 | 4.657E−01 | 2.734E−01 | 3.606E−01 | 4.078E−01 | 1.621E−01 | 4.524E−01 | 3.384E−01 | 2.618E−01 | 5.797E−01 | 2.093E−01 | 1.808E−01 | 6.073E−01 |
| 159 | 1.122E−01 | 1.416E−01 | 8.290E−02 | 1.407E−01 | 1.630E−01 | 5.156E−02 | 1.300E−01 | 1.042E−01 | 7.631E−02 | 1.745E−01 | 1.425E−01 | 5.040E−02 | 1.879E−01 |
| 160 | 3.357E−02 | 5.174E−02 | 3.731E−02 | 3.134E−02 | 4.586E−02 | 5.156E−02 | 1.443E−02 | 2.012E−02 | 3.268E−02 | 3.295E−02 | 1.674E−02 | 8.397E−03 | 2.395E−02 |
| 161 | 4.479E−02 | 4.239E−02 | 1.247E−02 | 7.053E−02 | 8.664E−02 | 2.208E−02 | 3.366E−02 | 6.037E−02 | 4.907E−02 | 9.884E−03 | 4.176E−02 | 7.133E−02 | 3.989E−03 |
| 162 | 1.683E−02 | 3.295E−02 | 4.559E−02 | 5.485E−02 | 4.078E−02 | 4.417E−02: | 9.617E−03 | 3.215E−02 | 2.725E−02 | 2.306E−02 | 4.595E−02 | 8.397E−03 | 2.395E−02 |
| 163 | 7.284E−02 | 2.351E−02 | 2.903E−02 | 3.134E−02 | 4.078E−02 | 4.417E−02 | 6.260E−02 | 5.227E−02 | 1.638E−02 | 1.647E−02 | 1.256E−02 | 2.102E−02 | 2.796E−02 |
| 164 | 3.357E−02 | 1.416E−02 | 2.903E−02 | 3.134E−02 | 0.000E+00 | 2.208E−02 | 2.885E−02 | 2.413E−02 | 2.725E−02 | 1.977E−02 | 4.176E−03 | 1.683E−02 | 1.202E−02 |
| 165 | 4.479E−02 | 3.295E−02 | 4.559E−02 | 3.918E−02 | 3.562E−02 | 2.947E−02 | 3.847E−02 | 2.814E−02 | 1.638E−02 | 2.306E−02 | 3.758E−02 | 4.194E−02 | 2.796E−02 |
| 166 | 6.162E−02 | 3.295E−02 | 1.656E−02 | 7.053E−02 | 6.625E−02 | 8.833E−02 | 6.741E−02 | 7.649E−02 | 1.086E−02 | 6.919E−02 | 5.850E−02 | 5.040E−02 | 7.186E−02 |
| 167 | 3.028E−01 | 2.591E−01 | 1.656E−01 | 2.271E−01 | 1.425E−01 | 6.625E−02 | 3.900E−01 | 2.048E−01 | 1.256E−01 | 5.004E−01 | 1.380E−01 | 1.175E−01 | 1.754E−01 |
| 168 | 8.994E−02 | 2.075E−01 | 1.033E−01 | 1.959E−01 | 1.220E−01 | 1.033E−01 | 1.443E−01 | 1.647E−01 | 1.416E−01 | 1.710E−01 | 1.006E−01 | 8.816E−02 | 1.354E−01 |
| 169 | 2.244E−02 | 6.118E−02 | 6.215E−02 | 8.620E−02 | 2.547E−02 | 4.417E−02 | 6.741E−02 | 4.025E−02 | 5.450E−02 | 4.283E−02 | 3.339E−02 | 3.776E−02 | 4.791E−02 |
| 170 | 4.479E−02 | 6.589E−02 | 7.462E−02 | 9.439E−02 | 5.093E−02 | 2.947E−02 | 4.817E−02 | 5.227E−02 | 5.450E−02 | 1.318E−02 | 4.176E−02 | 7.133E−02 | 2.395E−02 |
| 171 | 4.479E−02 | 7.533E−02 | 6.634E−02 | 3.918E−02 | 3.562E−02 | 7.364E−03 | 3.847E−02 | 3.215E−02 | 2.725E−02 | 2.636E−02 | 7.106E−02 | 3.776E−02 | 3.197E−02 |
| 172 | 3.863E−02 | 8.105E−02 | 7.247E−02 | 1.057E−01 | 7.088E−02 | 4.660E−02 | 1.545E−01 | 1.386E−01 | 7.210E−02 | 2.256E−01 | 1.361E−01 | 7.689E−02 | 8.363E−02 |
| 173 | 2.554E+00 | 2.804E+00 | 2.186E+00 | 3.153E+00 | 2.325E+00 | 1.818E+00 | 2.741E+00 | 2.856E+00 | 3.372E+00 | 2.158E+00 | 2.991E+00 | 2.678E+00 | 2.177E+00 |
| 174 | 4.472E+00 | 4.906E+00 | 3.545E+00 | 5.426E+00 | 3.838E+00 | 2.572E+00 | 4.635E+00 | 4.644E+00 | 5.144E+00 | 3.727E+00 | 4.193E+00 | 3.964E+00 | 2.177E+00 |
| 175 | 8.000E−01 | 1.008E+00 | 9.734E−01 | 1.147E+00 | 1.113E+00 | 7.381E−01 | 1.121E+00 | 1.203E+00 | 1.007E+00 | 1.195E+00 | 1.073E+00 | 7.590E−01 | 8.699E−01 |
| 176 | 3.029E+00 | 2.701E+00 | 3.396E+00 | 5.833E+00 | 2.923E+00 | 1.869E+00 | 3.417E+00 | 2.708E+00 | 2.615E+00 | 2.653E+00 | 4.070E+00 | 3.509E+00 | 2.641E+00 |
| 177 | 8.093E−01 | 7.356E−01 | 1.339E+00 | 1.860E+00 | 1.254E+00 | 7.016E−01 | 1.517E+00 | 6.699E−01 | 6.938E−01 | 1.883E+00 | 1.230E+00 | 9.550E−01 | 1.612E+00 |
| 178 | 8.878E−02 | 1.484E−01 | 2.146E−01 | 3.225E−01 | 1.962E−01 | 1.471E−01 | 2.354E−01 | 8.535E−02 | 9.234E−02 | 3.593E−01 | 3.532E−01 | 2.183E−01 | 2.685E−01 |
| 179 | 2.857E−02 | 2.269E−02 | 2.170E−02 | 8.633E−02 | 2.452E−02 | 2.636E−02 | 3.446E−02 | 1.275E−02 | 1.496E−02 | 4.169E−02 | 4.034E−02 | 3.642E−02 | 4.071E−02 |
| 180 | 1.545E−02 | 3.433E−02 | 2.403E−02 | 4.206E−02 | 2.735E−02 | 9.123E−03 | 1.790E−02 | 1.717E−02 | 2.330E−02 | 1.361E−02 | 2.477E−02 | 2.367E−02 | 3.850E−03 |
| 181 | 1.386E−02 | 2.403E−02 | 1.594E−02 | 2.587E−02 | 1.471E−02 | 6.082E−03 | 8.620E−03 | 1.606E−02 | 1.655E−02 | 9.982E−03 | 1.839E−02 | 1.680E−02 | 1.484E−02 |
| 182 | 7.787E−02 | 6.671E−02 | 1.165E−01 | 1.036E−01 | 7.223E−02 | 4.255E−02 | 6.291E−02 | 7.480E−02 | 8.032E−02 | 5.665E−02 | 7.885E−02 | 7.223E−02 | 6.438E−02 |
| 183 | 9.991E−01 | 1.329E+00 | 1.877E+00 | 1.408E+00 | 1.303E+00 | 8.293E−01 | 1.264E+00 | 1.552E+00 | 2.082E+00 | 1.274E+00 | 1.319E+00 | 1.042E+00 | 9.485E−01 |
| 184 | 1.231E+00 | 1.279E+00 | 2.152E+00 | 1.577E+00 | 1.490E+00 | 6.600E−01 | 1.328E+00 | 1.423E+00 | 2.160E+00 | 1.250E+00 | 1.397E+00 | 1.228E+00 | 1.057E+00 |
| 185 | 9.312E−01 | 1.053E+00 | 1.519E+00 | 1.069E+00 | 1.124E+00 | 4.414E−01 | 8.535E−01 | 1.042E+00 | 1.548E+00 | 7.908E−01 | 9.871E−01 | 8.677E−01 | 7.456E−01 |
| 186 | 2.126E+00 | 2.459E+00 | 3.255E+00 | 3.005E+00 | 2.538E+00 | 9.895E−01 | 2.171E+00 | 2.569E+00 | 3.109E+00 | 2.040E+00 | 1.782E+00 | 1.695E+00 | 1.956E+00 |
| 187 | 4.022E−01 | 5.248E−01 | 7.664E−01 | 5.714E−01 | 7.161E−01 | 3.409E−01 | 4.979E−01 | 6.738E−01 | 6.555E−01 | 5.592E−01 | 4.782E−01 | 3.262E−01 | 4.611E−01 |
| 188 | 4.476E−02 | 4.083E−02 | 8.277E−02 | 4.427E−02 | 6.941E−02 | 3.348E−02 | 4.844E−02 | 6.315E−02 | 4.206E−02 | 4.807E−02 | 5.702E−02 | 3.703E−02 | 2.587E−02 |
| 189 | 9.258E−03 | 8.424E−03 | 1.717E−02 | 1.508E−02 | 1.193E−02 | 6.082E−03 | 1.925E−02 | 1.109E−02 | 1.422E−02 | 1.815E−02 | 1.386E−02 | 1.386E−02 | 8.253E−03 |
| 190 | 1.803E−01 | 1.631E−01 | 2.649E−01 | 3.213E−01 | 2.551E−01 | 1.226E−01 | 1.557E−01 | 1.484E−01 | 1.704E−01 | 1.937E−01 | 2.600E−01 | 1.950E−01 | 1.149E−01 |
| 191 | 1.558E+00 | 1.285E+00 | 3.441E+00 | 3.225E+00 | 2.648E+00 | 9.560E−01 | 2.271E+00 | 1.200E+00 | 1.752E+00 | 2.659E+00 | 1.883E+00 | 1.504E+00 | 2.588E+00 |
| 192 | 3.200E−01 | 3.826E−01 | 8.044E−01 | 8.694E−01 | 6.511E−01 | 2.698E−01 | 5.494E−01 | 2.673E−01 | 3.433E−01 | 7.100E−01 | 7.430E−01 | 5.224E−01 | 6.757E−01 |
| 193 | 6.867E−02 | 7.198E−02 | 1.034E−01 | 1.508E−01 | 9.822E−02 | 4.770E−02 | 6.830E−02 | 5.212E−02 | 6.830E−02 | 7.345E−02 | 1.002E−01 | 7.345E−02 | 6.818E−02 |
| 194 | 1.373E−01 | 1.212E−01 | 1.484E−01 | 1.226E−01 | 7.578E−02 | 4.660E−02 | 6.634E−02 | 9.969E−02 | 2.085E−01 | 2.857E−02 | 9.148E−02 | 9.773E−02 | 4.562E−02 |
| 195 | 6.168E−02 | 5.579E−02 | 4.684E−02 | 3.237E−02 | 3.151E−02 | 1.827E−02 | 2.980E−02 | 4.880E−02 | 1.036E−01 | 1.729E−02 | 4.427E−02 | 3.176E−02 | 2.036E−02 |
| 196 | 8.020E−02 | 1.115E−01 | 1.803E−01 | 1.079E−01 | 1.508E−01 | 6.082E−02 | 2.121E−01 | 1.263E−01 | 1.209E−01 | 3.323E−01 | 1.300E−01 | 5.322E−02 | 2.121E−01 |
| 197 | 7.333E−02 | 7.259E−02 | 1.398E−01 | 1.036E−01 | 1.067E−01 | 6.180E−02 | 1.008E−01 | 8.032E−02 | 8.706E−02 | 2.207E−01 | 7.995E−02 | 6.364E−02 | 1.094E−01 |

APPENDIX D-continued

Ovarian Cancer
Training Dataset

| | | | | | | | | | | | | | |
|---|---|---|---|---|---|---|---|---|---|---|---|---|---|
| 198 | 3.630E−02 | 3.115E−02 | 6.168E−02 | 1.090E−01 | 6.450E−02 | 2.735E−02 | 4.635E−02 | 4.929E−02 | 7.357E−02 | 7.615E−02 | 7.713E−02 | 4.856E−02 | 3.679E−02 |
| 199 | 9.871E−02 | 8.486E−02 | 2.354E−01 | 2.526E−01 | 1.178E−01 | 6.793E−02 | 7.296E−02 | 9.086E−02 | 1.668E−01 | 1.312E−02 | 1.521E−01 | 1.398E−01 | 1.100E−02 |
| 200 | 7.480E−02 | 6.941E−02 | 1.159E−01 | 1.373E−01 | 5.543E−02 | 3.446E−02 | 5.101E−02 | 4.660E−02 | 8.559E−02 | 1.496E−02 | 8.976E−02 | 7.456E−02 | 2.195E−02 |
| 201 | 7.174E−02 | 8.302E−02 | 7.480E−02 | 7.235E−02 | 4.905E−02 | 2.134E−02 | 5.371E−02 | 5.653E−02 | 1.007E−01 | 2.673E−02 | 5.175E−02 | 3.936E−02 | 2.918E−02 |
| 202 | 1.778E−02 | 1.226E−02 | 1.594E−02 | 3.887E−02 | 2.109E−03 | 1.014E−02 | 1.398E−02 | 1.557E−02 | 1.051E−02 | 1.361E−03 | 1.839E−02 | 1.962E−02 | 1.100E−03 |
| 203 | 0.000E+00 | 1.300E−03 | 5.714E−04 | 4.316E−03 | 0.000E+00 | 1.014E−03 | 2.649E−03 | 5.543E−04 | 2.256E−03 | 9.074E−04 | 4.598E−03 | 2.894E−03 | 0.000E+00 |
| 204 | 1.003E−02 | 1.300E−02 | 2.060E−02 | 2.808E−02 | 1.193E−02 | 3.041E−03 | 1.193E−02 | 1.275E−02 | 3.752E−03 | 9.074E−04 | 2.011E−02 | 1.324E−02 | 7.149E−03 |
| 205 | 1.545E−03 | 2.587E−03 | 5.714E−04 | 0.000E+00 | 7.014E−04 | 2.023E−03 | 1.987E−03 | 1.109E−03 | 3.752E−03 | 1.361E−03 | 5.751E−04 | 5.776E−04 | 3.299E−03 |
| 206 | 2.551E−02 | 1.496E−02 | 3.139E−02 | 6.364E−02 | 1.680E−02 | 9.123E−03 | 1.925E−02 | 2.269E−02 | 1.496E−02 | 4.083E−03 | 2.992E−02 | 2.367E−02 | 3.850E−03 |
| 207 | 1.386E−02 | 8.424E−03 | 8.559E−03 | 1.187E−02 | 8.424E−03 | 7.100E−03 | 1.324E−02 | 1.053E−02 | 1.655E−02 | 4.991E−03 | 9.209E−03 | 8.670E−03 | 7.701E−03 |
| 208 | 1.080E−02 | 4.537E−03 | 3.998E−03 | 5.395E−03 | 4.905E−03 | 4.059E−03 | 6.634E−03 | 2.771E−03 | 3.004E−03 | 3.176E−03 | 4.598E−03 | 4.623E−03 | 1.100E−03 |
| 209 | 0.000E+00 | 0.000E+00 | 1.142E−03 | 1.079E−03 | 2.109E−03 | 1.014E−03 | 0.000E+00 | 0.000E+00 | 0.000E+00 | 1.815E−03 | 5.751E−04 | 0.000E+00 | 0.000E+00 |
| 210 | 2.318E−03 | 2.587E−03 | 2.281E−03 | 0.000E+00 | 1.398E−03 | 1.014E−03 | 0.000E+00 | 0.000E+00 | 7.505E−04 | 1.361E−03 | 5.751E−04 | 0.000E+00 | 5.494E−04 |
| 211 | 7.713E−04 | 2.587E−03 | 1.142E−03 | 3.237E−03 | 0.000E+00 | 0.000E+00 | 6.634E−04 | 0.000E+00 | 0.000E+00 | 4.537E−04 | 1.151E−03 | 1.729E−03 | 0.000E+00 |
| 212 | 6.941E−03 | 6.487E−03 | 3.998E−03 | 3.237E−03 | 2.109E−03 | 1.014E−03 | 1.987E−03 | 3.323E−03 | 6.009E−03 | 9.074E−04 | 2.305E−03 | 0.000E+00 | 5.494E−04 |
| 213 | 7.713E−04 | 1.300E−03 | 5.138E−03 | 1.079E−02 | 4.905E−03 | 4.059E−03 | 3.311E−03 | 3.323E−03 | 2.256E−03 | 1.361E−03 | 4.598E−03 | 1.729E−03 | 1.655E−03 |
| 214 | 3.863E−03 | 5.837E−03 | 1.717E−03 | 5.395E−03 | 5.616E−03 | 4.059E−03 | 2.649E−03 | 3.875E−03 | 5.261E−03 | 9.074E−04 | 4.034E−03 | 3.470E−03 | 4.954E−03 |
| 215 | 7.713E−04 | 1.300E−03 | 1.717E−03 | 1.079E−03 | 7.014E−04 | 1.014E−03 | 0.000E+00 | 0.000E+00 | 0.000E+00 | 4.537E−04 | 5.751E−04 | 0.000E+00 | 2.747E−03 |
| 216 | 0.000E+00 | 1.300E−03 | 1.717E−03 | 1.079E−03 | 0.000E+00 | 0.000E+00 | 6.634E−04 | 0.000E+00 | 0.000E+00 | 0.000E+00 | 0.000E+00 | 5.776E−04 | 5.494E−04 |
| 217 | 1.545E−03 | 6.487E−04 | 0.000E+00 | 0.000E+00 | 7.014E−04 | 0.000E+00 | 0.000E+00 | 5.543E−04 | 1.496E−03 | 4.537E−04 | 5.751E−04 | 5.776E−04 | 0.000E+00 |
| 218 | 1.267E+00 | 1.529E+00 | 2.212E+00 | 1.592E+00 | 1.668E+00 | 9.439E−01 | 1.280E+00 | 1.698E+00 | 1.806E+00 | 1.367E+00 | 1.407E+00 | 1.131E+00 | 9.848E−01 |
| 219 | 1.619E−02 | 1.300E−02 | 2.232E−02 | 1.619E−02 | 1.263E−02 | 2.023E−02 | 1.193E−02 | 2.219E−02 | 2.698E−02 | 2.134E−02 | 1.962E−02 | 1.099E−02 | 1.045E−02 |
| 220 | 5.878E−01 | 1.156E+00 | 9.769E−01 | 2.036E+00 | 1.171E+00 | 2.469E+00 | 2.335E+00 | 3.816E+00 | 1.174E+00 | 3.112E+00 | 3.461E+00 | 2.093E+00 | 1.553E+00 |
| 221 | 6.237E+01 | 6.445E+01 | 5.577E+01 | 7.513E+01 | 6.272E+01 | 8.769E+01 | 6.309E+01 | 7.815E+01 | 6.925E+01 | 6.973E+01 | 8.583E+01 | 7.313E+01 | 6.192E+01 |
| 222 | 5.211E+01 | 5.257E+01 | 4.199E+01 | 6.062E+01 | 7.448E+01 | 7.181E+01 | 5.209E+01 | 5.490E+01 | 4.218E+01 | 7.390E+01 | 5.012E+01 | 5.225E+01 | 7.328E+01 |
| 223 | 2.295E+01 | 2.925E+01 | 2.095E+01 | 3.212E+01 | 2.707E+01 | 4.683E+01 | 3.302E+01 | 5.386E+01 | 2.786E+01 | 3.486E+01 | 4.217E+01 | 3.946E+01 | 3.391E+01 |
| 224 | 2.348E+01 | 2.368E+01 | 1.862E+01 | 2.404E+01 | 2.638E+01 | 3.347E+01 | 2.615E+01 | 2.837E+01 | 2.381E+01 | 2.798E+01 | 3.203E+01 | 2.410E+01 | 2.374E+01 |
| 225 | 1.453E+01 | 1.421E+01 | 1.436E+01 | 1.585E+01 | 1.600E+01 | 1.610E+01 | 2.019E+01 | 1.090E+01 | 1.416E+01 | 2.585E+01 | 1.337E+01 | 1.032E+01 | 2.038E+01 |
| 226 | 5.246E+00 | 4.459E+00 | 5.143E+00 | 6.023E+00 | 6.305E+00 | 7.542E+00 | 7.943E+00 | 5.608E+00 | 5.441E+00 | 1.639E+01 | 5.624E+00 | 2.771E+00 | 1.182E+01 |
| 227 | 1.594E+00 | 1.643E+00 | 1.503E+00 | 1.934E+00 | 2.219E+00 | 3.119E+00 | 2.409E+00 | 2.007E+00 | 2.152E+00 | 5.687E+00 | 2.345E+00 | 1.259E+00 | 3.620E+00 |
| 228 | 4.355E−01 | 3.428E−01 | 4.699E−01 | 4.847E−01 | 4.920E−01 | 8.385E−01 | 3.802E−01 | 3.756E−01 | 4.073E−01 | 2.930E−01 | 6.413E−01 | 4.094E−01 | 1.667E−01 |
| 229 | 4.662E−01 | 3.388E−01 | 4.774E−01 | 4.993E−01 | 5.605E−01 | 9.920E−01 | 4.251E−01 | 4.054E−01 | 4.791E−01 | 3.264E−01 | 6.991E−01 | 4.170E−01 | 2.167E−01 |
| 230 | 4.865E+01 | 3.221E+01 | 3.334E+01 | 3.614E+01 | 3.486E+01 | 3.806E+01 | 4.857E+01 | 4.266E+01 | 4.071E+01 | 2.780E+01 | 3.485E+01 | 4.167E+01 | 3.864E+01 |
| 231 | 5.587E+00 | 3.402E+00 | 4.004E+00 | 3.995E+00 | 4.751E+00 | 6.018E+00 | 5.591E+00 | 5.461E+00 | 4.767E+00 | 4.157E+00 | 4.807E+00 | 4.617E+00 | 4.293E+00 |
| 232 | 2.608E+00 | 1.513E+00 | 2.121E+00 | 2.196E+00 | 1.617E+00 | 1.844E+00 | 2.032E+00 | 1.865E+00 | 1.666E+00 | 1.720E+00 | 2.304E+00 | 1.688E+00 | 1.800E+00 |
| 233 | 7.177E+00 | 4.864E+00 | 5.363E+00 | 5.051E+00 | 5.793E+00 | 5.237E+00 | 6.843E+00 | 4.131E+00 | 5.562E+00 | 4.930E+00 | 6.623E+00 | 7.200E+00 | 5.695E+00 |
| 234 | 1.861E+01 | 1.637E+01 | 1.566E+01 | 1.445E+01 | 1.179E+01 | 1.794E+01 | 2.283E+01 | 2.443E+01 | 1.937E+01 | 1.901E+01 | 2.447E+01 | 2.701E+01 | 1.483E+01 |
| 235 | 1.154E+01 | 8.316E+00 | 1.343E+01 | 8.861E+00 | 9.896E+00 | 1.047E+01 | 1.270E+01 | 1.616E+01 | 1.360E+01 | 8.676E+00 | 1.065E+01 | 1.267E+01 | 9.046E+00 |
| 236 | 9.325E−01 | 7.495E−01 | 1.053E+00 | 1.081E+00 | 8.513E−01 | 8.585E−01 | 6.461E−01 | 4.272E−01 | 4.619E−01 | 6.087E−01 | 1.168E+00 | 7.118E−01 | 4.940E−01 |
| 237 | 3.295E+00 | 2.614E+00 | 4.065E+00 | 4.724E+00 | 6.272E+00 | 4.527E+00 | 3.160E+00 | 2.820E+00 | 2.129E+00 | 5.113E+00 | 4.176E+00 | 3.343E+00 | 5.963E+00 |
| 238 | 5.923E+00 | 5.446E+00 | 7.165E+00 | 6.134E+00 | 5.933E+00 | 5.686E+00 | 6.548E+00 | 8.433E+00 | 5.115E+00 | 5.831E+00 | 7.043E+00 | 6.310E+00 | 6.718E+00 |
| 239 | 1.468E+00 | 1.083E+00 | 1.514E+00 | 1.297E+00 | 1.167E+00 | 1.179E+00 | 1.324E+00 | 1.604E+00 | 1.169E+00 | 1.103E+00 | 1.472E+00 | 1.419E+00 | 1.248E+00 |
| 240 | 1.663E+01 | 2.691E+01 | 2.239E+01 | 2.112E+01 | 1.703E+01 | 1.425E+01 | 8.591E+00 | 1.342E+01 | 1.348E+01 | 7.399E+00 | 2.048E+01 | 2.167E+01 | 4.926E+00 |
| 241 | 2.324E+02 | 2.481E+02 | 2.409E+02 | 2.235E+02 | 2.540E+02 | 2.435E+02 | 1.797E+02 | 2.144E+02 | 2.288E+02 | 2.166E+02 | 1.921E+02 | 2.090E+02 | 2.238E+02 |
| 242 | 1.219E+02 | 1.553E+02 | 1.614E+02 | 1.449E+02 | 1.321E+02 | 1.734E+02 | 1.339E+02 | 2.212E+02 | 1.733E+02 | 1.459E+02 | 1.789E+02 | 1.745E+02 | 1.358E+02 |
| 243 | 1.069E+01 | 1.343E+01 | 1.542E+01 | 1.338E+01 | 1.196E+01 | 1.557E+01 | 1.296E+01 | 2.219E+01 | 1.580E+01 | 1.403E+01 | 1.744E+01 | 1.730E+01 | 1.234E+01 |
| 244 | 6.558E+00 | 6.647E+00 | 9.772E+00 | 8.218E+00 | 9.117E+00 | 7.974E+00 | 9.111E+00 | 5.355E+00 | 6.142E+00 | 1.074E+01 | 7.364E+00 | 5.784E+00 | 1.149E+01 |
| 245 | 3.740E+00 | 4.231E+00 | 4.752E+00 | 5.042E+00 | 5.431E+00 | 4.531E+00 | 4.280E+00 | 3.512E+00 | 2.846E+00 | 5.502E+00 | 4.640E+00 | 3.915E+00 | 6.337E+00 |
| 246 | 7.422E+00 | 5.911E+00 | 8.690E+00 | 7.882E+00 | 7.781E+00 | 6.975E+00 | 4.726E+00 | 5.927E+00 | 4.901E+00 | 6.774E+00 | 6.800E+00 | 6.160E+00 | 6.855E+00 |
| 247 | 4.935E+00 | 3.434E+00 | 4.880E+00 | 5.262E+00 | 4.012E+00 | 5.741E+00 | 3.679E+00 | 4.199E+00 | 4.062E+00 | 4.691E+00 | 5.342E+00 | 4.005E+00 | 4.548E+00 |

APPENDIX D-continued

Ovarian Cancer
Training Dataset

| | | | | | | | | | | | | | |
|---|---|---|---|---|---|---|---|---|---|---|---|---|---|
| 248 | 5.726E+01 | 6.526E+01 | 8.491E+01 | 5.478E+01 | 8.021E+01 | 5.366E+01 | 6.470E+01 | 3.768E+01 | 6.225E+01 | 9.324E+01 | 5.116E+01 | 4.003E+01 | 6.685E+01 |
| 249 | 3.525E+01 | 6.314E+01 | 6.343E+01 | 4.568E+01 | 6.552E+01 | 4.935E+01 | 4.874E+01 | 4.162E+01 | 4.648E+01 | 7.766E+01 | 6.523E+01 | 5.145E+01 | 5.616E+01 |
| 250 | 1.018E+02 | 1.158E+02 | 1.211E+02 | 1.082E+02 | 1.625E+02 | 1.254E+02 | 1.020E+02 | 1.155E+02 | 1.039E+02 | 1.309E+02 | 1.071E+02 | 9.830E+01 | 1.228E+02 |
| 251 | 4.191E+01 | 4.652E+01 | 4.987E+01 | 5.060E+01 | 5.084E+01 | 5.322E+01 | 4.327E+01 | 5.713E+01 | 5.236E+01 | 4.303E+01 | 5.896E+01 | 5.553E+01 | 4.184E+01 |
| 252 | 3.097E+00 | 3.243E+00 | 3.605E+00 | 3.434E+00 | 3.015E+00 | 3.774E+00 | 2.942E+00 | 4.027E+00 | 3.418E+00 | 2.941E+00 | 4.540E+00 | 3.830E+00 | 2.593E+00 |
| 253 | 3.332E+00 | 3.283E+00 | 3.862E+00 | 3.351E+00 | 3.649E+00 | 3.753E+00 | 3.182E+00 | 2.736E+00 | 2.418E+00 | 5.339E+00 | 3.697E+00 | 2.502E+00 | 4.090E+00 |
| 254 | 6.648E+00 | 7.755E+00 | 8.823E+00 | 7.151E+00 | 8.340E+00 | 6.698E+00 | 9.019E+00 | 5.963E+00 | 5.673E+00 | 1.077E+01 | 6.557E+00 | 4.671E+00 | 1.088E+01 |
| 255 | 6.878E+00 | 7.489E+00 | 8.745E+00 | 6.852E+00 | 7.157E+00 | 6.675E+00 | 8.064E+00 | 4.922E+00 | 5.637E+00 | 8.128E+00 | 5.936E+00 | 5.323E+00 | 9.080E+00 |
| 256 | 2.706E+00 | 2.633E+00 | 3.855E+00 | 2.988E+00 | 2.525E+00 | 2.772E+00 | 2.638E+00 | 2.050E+00 | 2.214E+00 | 2.799E+00 | 3.121E+00 | 2.582E+00 | 2.715E+00 |
| 257 | 5.917E+00 | 4.350E+00 | 5.408E+00 | 6.176E+00 | 4.985E+00 | 6.244E+00 | 5.032E+00 | 3.679E+00 | 4.565E+00 | 4.965E+00 | 6.472E+00 | 4.622E+00 | 5.170E+00 |
| 258 | 1.627E+01 | 1.755E+01 | 2.280E+01 | 1.720E+01 | 2.283E+01 | 2.017E+01 | 1.759E+01 | 1.286E+01 | 1.767E+01 | 3.631E+01 | 1.921E+01 | 1.029E+01 | 2.285E+01 |
| 259 | 3.213E+01 | 3.383E+01 | 4.322E+01 | 3.200E+01 | 4.101E+01 | 2.911E+01 | 4.099E+01 | 2.298E+01 | 3.392E+01 | 5.026E+01 | 3.018E+01 | 1.997E+01 | 3.770E+01 |
| 260 | 2.846E+01 | 3.326E+01 | 3.565E+01 | 3.151E+01 | 2.922E+01 | 2.932E+01 | 3.895E+01 | 2.624E+01 | 3.339E+01 | 3.808E+01 | 3.979E+01 | 3.115E+01 | 2.858E+01 |
| 261 | 4.086E+01 | 4.223E+01 | 3.243E+01 | 3.986E+01 | 2.662E+01 | 3.340E+01 | 4.690E+01 | 4.128E+01 | 4.339E+01 | 2.937E+01 | 3.963E+01 | 4.218E+01 | 3.326E+01 |
| 262 | 1.276E+01 | 1.360E+01 | 1.137E+01 | 1.568E+01 | 1.025E+01 | 1.368E+01 | 1.215E+01 | 1.082E+01 | 1.561E+01 | 8.291E+00 | 1.515E+01 | 1.347E+01 | 1.141E+01 |
| 263 | 2.371E+00 | 1.986E+00 | 3.120E+00 | 2.278E+00 | 2.632E+00 | 2.416E+00 | 2.312E+00 | 1.785E+00 | 1.709E+00 | 3.955E+00 | 2.284E+00 | 1.446E+00 | 3.564E+00 |
| 264 | 2.563E+00 | 2.168E+00 | 3.680E+00 | 2.763E+00 | 2.426E+00 | 2.466E+00 | 2.372E+00 | 2.093E+00 | 2.075E+00 | 2.657E+00 | 2.746E+00 | 2.291E+00 | 2.690E+00 |
| 265 | 1.957E+00 | 1.781E+00 | 3.106E+00 | 2.096E+00 | 1.962E+00 | 1.894E+00 | 1.814E+00 | 1.708E+00 | 1.916E+00 | 1.505E+00 | 2.006E+00 | 1.712E+00 | 1.938E+00 |
| 266 | 2.638E+00 | 2.575E+00 | 3.932E+00 | 3.062E+00 | 1.667E+00 | 1.897E+00 | 1.746E+00 | 2.027E+00 | 1.840E+00 | 7.565E−01 | 2.854E+00 | 3.006E+00 | 9.351E−01 |
| 267 | 2.935E+00 | 2.687E+00 | 3.294E+00 | 2.800E+00 | 1.414E+00 | 2.365E+00 | 1.991E+00 | 2.257E+00 | 1.966E+00 | 1.171E+00 | 2.957E+00 | 2.810E+00 | 1.454E+00 |
| 268 | 7.862E+00 | 7.045E+00 | 1.208E+01 | 7.223E+00 | 1.016E+01 | 8.732E+00 | 1.112E+01 | 8.731E+00 | 7.604E+00 | 2.159E+01 | 7.903E+00 | 3.742E+00 | 1.249E+01 |
| 269 | 5.424E+00 | 5.528E+00 | 9.734E+00 | 7.817E+00 | 6.878E+00 | 6.880E+00 | 6.471E+00 | 6.802E+00 | 8.150E+00 | 1.021E+01 | 8.126E+00 | 5.255E+00 | 5.359E+00 |
| 270 | 2.320E+00 | 2.583E+00 | 4.357E+00 | 3.474E+00 | 2.830E+00 | 3.189E+00 | 2.632E+00 | 2.982E+00 | 3.692E+00 | 2.758E+00 | 3.841E+00 | 2.523E+00 | 1.752E+00 |
| 271 | 1.910E+01 | 1.216E+01 | 1.378E+01 | 1.540E+01 | 1.352E+01 | 1.508E+01 | 1.818E+01 | 1.266E+01 | 1.383E+01 | 1.267E+01 | 1.860E+01 | 1.425E+01 | 1.466E+01 |
| 272 | 1.203E+02 | 8.403E+01 | 8.507E+01 | 1.015E+02 | 8.428E+01 | 9.237E+01 | 1.260E+02 | 1.058E+02 | 1.021E+02 | 7.062E+01 | 9.127E+01 | 1.026E+02 | 9.810E+01 |
| 273 | 1.306E+02 | 9.165E+01 | 8.934E+01 | 1.059E+02 | 8.404E+01 | 9.181E+01 | 1.260E+02 | 1.085E+02 | 1.111E+02 | 7.409E+01 | 9.128E+01 | 1.086E+02 | 1.025E+02 |
| 274 | 2.114E+01 | 1.365E+01 | 1.304E+01 | 1.619E+01 | 1.270E+01 | 1.446E+01 | 2.044E+01 | 1.808E+01 | 1.615E+01 | 1.173E+01 | 1.395E+01 | 1.677E+01 | 1.620E+01 |
| 275 | 9.553E−01 | 7.914E−01 | 7.859E−01 | 8.029E−01 | 6.219E−01 | 5.238E−01 | 8.140E−01 | 5.657E−01 | 5.482E−01 | 4.907E−01 | 9.353E−01 | 8.102E−01 | 7.268E−01 |
| 276 | 1.444E+01 | 9.898E+00 | 1.084E+01 | 9.217E+00 | 7.798E+00 | 6.821E+00 | 1.346E+01 | 7.104E+00 | 1.117E+01 | 7.162E+00 | 1.187E+01 | 1.488E+01 | 1.089E+01 |
| 277 | 4.149E+01 | 2.913E+01 | 2.485E+01 | 2.331E+01 | 1.732E+01 | 1.807E+01 | 3.744E+01 | 2.099E+01 | 3.252E+01 | 1.725E+01 | 2.744E+01 | 4.722E+01 | 2.665E+01 |
| 278 | 4.136E+01 | 2.892E+01 | 2.399E+01 | 2.269E+01 | 1.650E+01 | 1.911E+01 | 3.642E+01 | 2.033E+01 | 3.209E+01 | 1.680E+01 | 2.611E+01 | 4.616E+01 | 2.626E+01 |
| 279 | 9.765E+00 | 7.581E+00 | 6.495E+00 | 5.523E+00 | 3.717E+00 | 5.990E+00 | 8.795E+00 | 9.484E+00 | 7.387E+00 | 6.816E+00 | 8.816E+00 | 1.142E+01 | 5.474E+00 |
| 280 | 7.268E+00 | 9.064E+00 | 8.004E+00 | 8.278E+00 | 7.017E+00 | 5.035E+00 | 5.903E+00 | 4.864E+00 | 5.942E+00 | 4.234E+00 | 8.318E+00 | 8.526E+00 | 5.231E+00 |
| 281 | 1.135E+02 | 1.192E+02 | 1.311E+02 | 1.244E+02 | 1.389E+02 | 1.015E+02 | 9.403E+01 | 1.013E+02 | 1.082E+02 | 1.228E+02 | 9.999E+01 | 1.110E+02 | 1.213E+02 |
| 282 | 1.005E+02 | 1.026E+02 | 1.131E+02 | 1.069E+02 | 1.179E+02 | 9.450E+01 | 7.931E+01 | 8.578E+01 | 9.203E+01 | 1.059E+02 | 8.570E+01 | 9.462E+01 | 1.037E+02 |
| 283 | 3.437E+01 | 4.482E+01 | 5.015E+01 | 4.480E+01 | 3.563E+01 | 4.954E+01 | 3.947E+01 | 6.873E+01 | 4.656E+01 | 4.401E+01 | 5.482E+01 | 5.398E+01 | 3.830E+01 |
| 284 | 6.615E+00 | 4.360E+00 | 5.564E+00 | 7.634E+00 | 5.994E+00 | 6.837E+00 | 5.224E+00 | 3.769E+00 | 4.973E+00 | 6.240E+00 | 7.136E+00 | 4.749E+00 | 6.564E+00 |
| 285 | 7.324E+01 | 7.394E+01 | 7.209E+01 | 7.399E+01 | 9.184E+01 | 7.387E+01 | 7.208E+01 | 6.696E+01 | 7.428E+01 | 7.717E+01 | 7.079E+01 | 6.844E+01 | 8.205E+01 |
| 286 | 5.555E+01 | 5.762E+01 | 5.545E+01 | 5.924E+01 | 6.609E+01 | 5.764E+01 | 5.566E+01 | 4.900E+01 | 5.717E+01 | 5.867E+01 | 5.548E+01 | 5.352E+01 | 6.352E+01 |
| 287 | 7.666E+00 | 8.235E+00 | 9.033E+00 | 8.206E+00 | 7.967E+00 | 9.002E+00 | 7.715E+00 | 1.001E+01 | 8.455E+00 | 7.688E+00 | 1.012E+01 | 1.015E+01 | 7.192E+00 |
| 288 | 8.329E+01 | 8.477E+01 | 6.399E+01 | 7.570E+01 | 4.963E+01 | 5.735E+01 | 9.413E+01 | 7.641E+01 | 8.264E+01 | 5.994E+01 | 7.287E+01 | 8.048E+01 | 6.917E+01 |
| 289 | 6.659E+01 | 6.864E+01 | 5.050E+01 | 6.139E+01 | 3.895E+01 | 4.808E+01 | 7.565E+01 | 6.219E+01 | 6.383E+01 | 4.750E+01 | 5.685E+01 | 6.375E+01 | 5.538E+01 |
| 290 | 2.404E+01 | 2.573E+01 | 1.710E+01 | 2.703E+01 | 1.598E+01 | 2.228E+01 | 2.650E+01 | 1.988E+01 | 2.828E+01 | 1.901E+01 | 2.460E+01 | 2.218E+01 | 2.624E+01 |
| 291 | 1.928E+01 | 1.959E+01 | 1.309E+01 | 2.223E+01 | 1.286E+01 | 1.909E+01 | 2.002E+01 | 1.511E+01 | 2.172E+01 | 1.451E+01 | 1.897E+01 | 1.776E+01 | 2.090E+01 |
| 292 | 2.289E+00 | 2.369E+00 | 2.447E+00 | 2.620E+00 | 1.752E+00 | 2.267E+00 | 1.876E+00 | 1.815E+00 | 2.355E+00 | 1.451E+00 | 2.558E+00 | 2.381E+00 | 1.890E+00 |
| 293 | 2.197E+00 | 2.180E+00 | 2.503E+00 | 2.547E+00 | 1.136E+00 | 1.412E+00 | 1.567E+00 | 1.653E+00 | 1.638E+00 | 4.940E−01 | 2.280E+00 | 2.465E+00 | 5.275E−01 |
| 294 | 1.642E+00 | 1.915E+00 | 2.755E+00 | 1.715E+00 | 1.619E+00 | 1.277E+00 | 1.145E+00 | 1.240E+00 | 1.157E+00 | 1.087E+00 | 1.700E+00 | 1.751E+00 | 1.088E+00 |
| 295 | 1.602E+00 | 1.900E+00 | 2.789E+00 | 1.772E+00 | 1.593E+00 | 1.282E+00 | 1.137E+00 | 1.222E+00 | 1.180E+00 | 1.100E+00 | 1.776E+00 | 1.758E+00 | 1.095E+00 |
| 296 | 9.374E−01 | 1.164E+00 | 1.819E+00 | 1.014E+00 | 8.920E−01 | 8.456E−01 | 7.862E−01 | 1.063E+00 | 7.020E−01 | 7.641E−01 | 1.187E+00 | 1.145E+00 | 6.933E−01 |
| 297 | 6.741E−01 | 4.706E−01 | 4.595E−01 | 3.810E−01 | 3.734E−01 | 5.471E−01 | 5.331E−01 | 4.970E−01 | 5.383E−01 | 2.882E−01 | 3.139E−01 | 4.803E−01 | 4.646E−01 |

APPENDIX D-continued

Ovarian Cancer
Training Dataset

| | | | | | | | | | | | | | |
|---|---|---|---|---|---|---|---|---|---|---|---|---|---|
| 298 | 3.604E−02 | 2.210E−02 | 1.442E−02 | 1.660E−02 | 1.613E−02 | 2.853E−02 | 2.403E−02 | 2.338E−02 | 2.596E−02 | 1.319E−02 | 1.560E−02 | 2.617E−02 | 2.531E−02 |
| 299 | 3.108E−01 | 2.230E−01 | 1.536E−01 | 8.838E−02 | 7.573E−02 | 1.787E−01 | 2.474E−01 | 1.495E−01 | 2.608E−01 | 8.152E−02 | 1.279E−01 | 3.487E−01 | 1.660E−01 |
| 300 | 2.381E−02 | 8.366E−03 | 5.899E−03 | 4.741E−03 | 3.046E−03 | 1.045E−02 | 1.169E−02 | 5.685E−03 | 1.963E−02 | 5.578E−03 | 9.975E−03 | 1.997E−02 | 1.148E−02 |
| 301 | 1.716E−01 | 1.216E−01 | 7.337E−02 | 6.693E−02 | 6.672E−02 | 1.083E−01 | 1.401E−01 | 1.025E−01 | 1.637E−01 | 5.020E−02 | 8.688E−02 | 1.965E−01 | 1.240E−01 |
| 302 | 4.548E−02 | 8.195E−02 | 7.809E−03 | 2.403E−02 | 8.281E−03 | 4.226E−02 | 1.828E−02 | 2.488E−02 | 5.213E−02 | 1.113E−02 | 4.741E−02 | 2.853E−02 | 3.475E−02 |
| 303 | 4.403E−01 | 4.520E−01 | 2.358E−01 | 2.908E−01 | 2.812E−01 | 5.295E−01 | 4.325E−01 | 3.334E−01 | 5.850E−01 | 2.049E−01 | 2.695E−01 | 4.206E−01 | 4.241E−01 |
| 304 | 1.036E−02 | 1.210E−02 | 4.333E−03 | 3.454E−03 | 5.020E−03 | 1.094E−02 | 7.015E−03 | 4.033E−03 | 9.804E−03 | 1.750E−03 | 6.715E−03 | 4.591E−03 | 6.285E−03 |
| 305 | 8.341E−01 | 9.356E−01 | 5.205E−01 | 4.901E−01 | 3.791E−01 | 8.057E−01 | 8.417E−01 | 8.371E−01 | 8.839E−01 | 4.097E−01 | 4.543E−01 | 7.771E−01 | 5.369E−01 |
| 306 | 6.307E−02 | 6.200E−02 | 2.424E−02 | 4.162E−02 | 2.274E−02 | 7.036E−02 | 5.921E−02 | 6.457E−02 | 5.985E−02 | 3.347E−02 | 3.625E−02 | 5.256E−02 | 4.097E−02 |
| 307 | 2.370E+00 | 2.422E+00 | 1.012E+00 | 2.569E+00 | 1.403E+00 | 4.356E+00 | 1.994E+00 | 1.422E+00 | 3.760E+00 | 1.356E+00 | 1.789E+00 | 1.860E+00 | 3.108E+00 |
| 308 | 4.290E−02 | 4.162E−02 | 1.718E−02 | 3.904E−02 | 2.488E−02 | 7.787E−02 | 3.561E−02 | 2.639E−02 | 6.071E−02 | 2.252E−02 | 3.218E−02 | 3.025E−02 | 5.234E−02 |
| 309 | 1.523E−02 | 1.118E−02 | 6.779E−03 | 5.814E−03 | 5.449E−03 | 7.122E−03 | 9.568E−03 | 8.988E−03 | 9.117E−03 | 3.025E−03 | 5.406E−03 | 7.380E−03 | 3.518E−03 |
| 310 | 5.792E−03 | 3.111E−03 | 2.424E−03 | 1.941E−03 | 2.617E−03 | 9.975E−03 | 4.033E−03 | 3.068E−03 | 5.964E−03 | 4.934E−03 | 2.596E−03 | 4.591E−03 | 2.596E−03 |
| 311 | 1.218E−03 | 3.111E−04 | 1.043E−03 | 1.079E−03 | 8.710E−04 | 2.381E−03 | 1.062E−03 | 0.000E+00 | 7.015E−04 | 2.703E−03 | 1.083E−03 | 5.985E−04 | 2.596E−03 |
| 312 | 3.046E−04 | 3.111E−04 | 0.000E+00 | 2.167E−04 | 0.000E+00 | 9.503E−04 | 2.126E−04 | 4.741E−04 | 3.497E−04 | 6.371E−04 | 8.667E−04 | 5.985E−04 | 9.246E−04 |
| 313 | 3.102E−01 | 1.830E−01 | 8.581E−02 | 2.134E−01 | 1.285E−01 | 2.795E−01 | 2.202E−01 | 3.102E−01 | 2.667E−01 | 1.163E−01 | 1.379E−01 | 2.107E−01 | 2.339E−01 |
| 314 | 1.188E−02 | 9.932E−03 | 4.505E−03 | 1.013E−02 | 6.972E−03 | 2.810E−02 | 8.495E−03 | 1.326E−02 | 1.648E−02 | 6.050E−03 | 9.310E−03 | 9.589E−03 | 9.997E−03 |
| 315 | 6.950E−02 | 3.604E−02 | 1.667E−02 | 3.432E−02 | 2.789E−02 | 4.526E−02 | 5.234E−02 | 4.483E−02 | 4.097E−02 | 1.892E−02 | 2.660E−02 | 5.256E−02 | 5.492E−02 |
| 316 | 3.347E−03 | 9.310E−04 | 5.213E−04 | 1.079E−03 | 6.543E−04 | 9.503E−04 | 1.062E−03 | 1.658E−03 | 1.753E−03 | 3.175E−04 | 1.517E−03 | 2.789E−03 | 1.480E−03 |
| 317 | 4.762E−02 | 3.454E−02 | 1.405E−02 | 2.360E−02 | 3.647E−02 | 3.947E−02 | 3.797E−02 | 4.419E−02 | 3.883E−02 | 2.188E−02 | 2.531E−02 | 3.711E−02 | 5.041E−02 |
| 318 | 4.870E−03 | 3.411E−03 | 1.043E−03 | 2.810E−03 | 1.963E−03 | 4.762E−03 | 1.701E−03 | 3.325E−03 | 2.102E−03 | 2.068E−03 | 2.596E−03 | 3.003E−03 | 3.518E−03 |
| 319 | 3.498E−01 | 2.221E−01 | 8.409E−02 | 2.589E−01 | 2.348E−01 | 2.895E−01 | 2.782E−01 | 2.801E−01 | 3.684E−01 | 1.665E−01 | 1.656E−01 | 2.441E−01 | 3.645E−01 |
| 320 | 1.523E−03 | 1.240E−03 | 8.688E−04 | 1.941E−03 | 8.710E−04 | 9.503E−04 | 4.248E−04 | 1.184E−03 | 7.015E−04 | 6.371E−04 | 1.300E−03 | 5.985E−04 | 5.556E−04 |
| 321 | 4.105E−01 | 2.714E−01 | 1.306E−01 | 2.568E−01 | 1.652E−01 | 2.709E−01 | 3.458E−01 | 4.277E−01 | 3.529E−01 | 2.006E−01 | 1.826E−01 | 3.310E−01 | 3.153E−01 |
| 322 | 1.401E−02 | 8.688E−03 | 3.304E−03 | 6.028E−03 | 7.186E−03 | 1.188E−02 | 9.568E−03 | 1.137E−02 | 1.156E−02 | 5.578E−03 | 5.856E−03 | 7.980E−03 | 1.184E−02 |
| 323 | 3.306E−01 | 2.382E−01 | 9.332E−02 | 3.130E−01 | 2.498E−01 | 4.088E−01 | 3.222E−01 | 3.175E−01 | 4.314E−01 | 2.201E−01 | 1.969E−01 | 2.769E−01 | 3.621E−01 |
| 324 | 1.218E−02 | 8.688E−03 | 2.960E−03 | 6.693E−03 | 7.637E−03 | 1.568E−02 | 9.997E−03 | 1.184E−02 | 1.191E−02 | 5.578E−03 | 1.019E−02 | 1.178E−02 | 1.036E−02 |
| 325 | 2.231E−02 | 2.047E−02 | 1.023E−02 | 9.482E−03 | 1.111E−02 | 1.806E−02 | 2.210E−02 | 1.043E−02 | 1.577E−02 | 1.384E−02 | 9.310E−03 | 1.478E−02 | 2.446E−02 |
| 326 | 2.746E−03 | 3.111E−03 | 6.950E−04 | 1.510E−03 | 1.090E−03 | 4.269E−03 | 1.701E−03 | 2.832E−03 | 1.753E−03 | 2.068E−03 | 2.810E−03 | 7.980E−04 | 1.109E−03 |
| 327 | 3.111E−02 | 3.540E−02 | 1.006E−02 | 1.487E−02 | 1.461E−02 | 2.424E−02 | 2.960E−02 | 1.965E−02 | 2.139E−02 | 1.560E−02 | 1.776E−02 | 1.796E−02 | 2.109E−02 |
| 328 | 3.046E−03 | 2.167E−03 | 1.043E−03 | 1.941E−03 | 1.744E−03 | 5.234E−03 | 1.274E−03 | 2.832E−03 | 1.753E−03 | 9.546E−04 | 2.167E−03 | 1.197E−03 | 9.246E−04 |
| 329 | 7.826E−01 | 3.887E−01 | 2.512E−01 | 6.718E−01 | 3.791E−01 | 7.121E−01 | 5.771E−01 | 7.040E−01 | 7.700E−01 | 3.110E−01 | 4.129E−01 | 6.551E−01 | 6.589E−01 |
| 330 | 9.139E−03 | 5.277E−03 | 3.132E−03 | 6.243E−03 | 3.711E−03 | 9.031E−03 | 6.371E−03 | 8.281E−03 | 6.650E−03 | 3.347E−03 | 4.333E−03 | 7.380E−03 | 7.208E−03 |
| 331 | 7.916E−02 | 6.479E−02 | 2.596E−02 | 4.205E−02 | 3.196E−02 | 4.998E−02 | 6.285E−02 | 4.805E−02 | 6.307E−02 | 2.596E−02 | 4.012E−02 | 5.020E−02 | 5.642E−02 |
| 332 | 5.170E−03 | 3.733E−03 | 1.043E−03 | 8.624E−04 | 2.188E−04 | 1.901E−03 | 1.701E−03 | 1.184E−03 | 2.446E−03 | 1.431E−03 | 2.381E−03 | 1.796E−03 | 1.109E−03 |
| 333 | 4.569E−02 | 4.505E−02 | 1.598E−02 | 2.574E−02 | 2.094E−02 | 3.668E−02 | 4.891E−02 | 3.218E−02 | 3.368E−02 | 2.115E−02 | 2.036E−02 | 3.068E−02 | 3.926E−02 |
| 334 | 9.139E−04 | 2.167E−03 | 3.475E−04 | 0.000E+00 | 4.355E−04 | 0.000E+00 | 6.371E−04 | 4.741E−04 | 1.403E−03 | 0.000E+00 | 2.167E−04 | 1.997E−04 | 1.849E−04 |
| 335 | 9.332E−02 | 6.114E−02 | 2.510E−02 | 6.693E−02 | 4.162E−02 | 9.546E−02 | 7.272E−02 | 7.680E−02 | 8.173E−02 | 3.411E−02 | 5.513E−02 | 6.200E−O2 | 8.710E−02 |
| 336 | 3.969E−03 | 4.033E−03 | 1.388E−03 | 1.725E−03 | 1.525E−03 | 6.650E−03 | 3.604E−03 | 4.269E−03 | 4.548E−03 | 1.750E−03 | 2.381E−03 | 3.797E−03 | 4.248E−03 |
| 337 | 1.658E−01 | 1.064E−01 | 5.170E−02 | 1.343E−01 | 6.393E−02 | 1.407E−01 | 1.519E−01 | 1.982E−01 | 1.549E−01 | 7.530E−02 | 1.025E−01 | 1.283E−01 | 1.298E−01 |
| 338 | 3.046E−03 | 2.488E−03 | 8.688E−04 | 3.025E−03 | 1.309E−03 | 3.325E−03 | 2.553E−03 | 2.832E−03 | 3.153E−03 | 1.272E−03 | 1.950E−03 | 2.188E−03 | 2.403E−03 |
| 339 | 8.045E−02 | 5.578E−02 | 2.231E−02 | 7.208E−02 | 4.333E−02 | 9.224E−02 | 7.380E−02 | 7.616E−02 | 7.015E−02 | 4.205E−02 | 4.870E−02 | 6.586E−02 | 7.594E−02 |
| 340 | 6.092E−03 | 4.655E−03 | 2.424E−03 | 3.025E−03 | 2.403E−03 | 6.178E−03 | 4.677E−03 | 6.157E−03 | 5.599E−03 | 3.347E−03 | 4.333E−03 | 4.998E−03 | 3.690E−03 |
| 341 | 1.036E−02 | 9.310E−03 | 5.041E−03 | 8.624E−03 | 7.422E−03 | 1.615E−02 | 9.782E−03 | 6.865E−03 | 1.261E−02 | 4.612E−03 | 6.715E−03 | 8.195E−03 | 4.805E−03 |
| 342 | 1.523E−03 | 2.167E−03 | 8.688E−04 | 6.479E−04 | 1.963E−03 | 9.503E−04 | 4.248E−04 | 9.482E−04 | 2.102E−03 | 1.113E−03 | 1.083E−03 | 1.397E−03 | 5.556E−04 |
| 343 | 1.553E−02 | 1.334E−02 | 8.688E−03 | 9.482E−03 | 7.637E−03 | 1.521E−02 | 1.233E−02 | 1.184E−02 | 9.117E−03 | 4.934E−03 | 7.144E−03 | 9.589E−03 | 7.208E−03 |
| 344 | 3.046E−04 | 3.111E−04 | 1.735E−04 | 4.312E−04 | 4.355E−04 | 9.503E−04 | 4.248E−04 | 2.360E−04 | 1.403E−03 | 4.762E−04 | 4.333E−04 | 3.990E−04 | 1.849E−04 |

APPENDIX D-continued

Ovarian Cancer
Training Dataset

| | AL | AM | AN | AO | AP | AQ | AR | AS | AT | AU | AV | AW | AX |
|---|---|---|---|---|---|---|---|---|---|---|---|---|---|
| 1 | CA419 | CA266 | 14627 | 14607 | 14603 | 14538 | 13908 | 13898 | CA375 | CA571 | CA256 | CA263 | CA272 |
| 2 | Control | Control | Late Malignant | Late Malignant | Late Malignant | Late Malignant | Late Malignant | Late Malignant | Control | Control | Control | Control | Control |
| 3 | 0 | 0 | 3 | 3 | 3 | 3 | 3 | 3 | 0 | 0 | 0 | 0 | 0 |
| 4 | 1 | 1 | −1 | −1 | −1 | −1 | −1 | −1 | 1 | 1 | 1 | 1 | 1 |
| 5 | 2.327E+00 | 3.151E+00 | 2.007E+00 | 1.394E+00 | 2.043E+00 | 2.589E+00 | 2.637E+00 | 2.892E+00 | 9.534E−01 | 8.979E−01 | 8.192E−01 | 1.157E+00 | 1.224E+00 |
| 6 | 2.075E+00 | 1.943E+00 | 8.070E−01 | 3.670E−01 | 5.665E−01 | 8.802E−01 | 4.796E−01 | 6.024E−01 | 2.350E−01 | 3.144E−01 | 3.305E−01 | 3.004E−01 | 4.067E−01 |
| 7 | 3.723E−01 | 3.562E−01 | 2.511E−01 | 1.234E−01 | 2.307E−01 | 3.648E−01 | 2.039E−01 | 3.348E−01 | 9.056E−02 | 1.105E−01 | 9.120E−02 | 1.277E−01 | 1.212E−01 |
| 8 | 2.037E+00 | 1.899E+00 | 8.741E−01 | 2.185E+00 | 1.517E+00 | 1.147E+00 | 3.763E+00 | 1.455E+00 | 8.871E−01 | 6.813E−01 | 7.063E−01 | 6.491E−01 | 1.333E+00 |
| 9 | 3.476E−02 | 5.504E−02 | 2.854E−02 | 2.489E−02 | 2.843E−02 | 3.112E−02 | 2.693E−02 | 3.519E−02 | 2.371E−02 | 1.770E−02 | 2.264E−02 | 1.813E−02 | 1.277E−02 |
| 10 | 2.554E−02 | 2.264E−02 | 1.170E−02 | 1.159E−02 | 1.384E−02 | 2.800E−02 | 1.094E−02 | 1.599E−02 | 1.159E−02 | 8.423E−03 | 6.513E−03 | 6.212E−03 | 6.384E−03 |
| 11 | 2.071E−02 | 2.446E−02 | 1.577E−02 | 1.084E−02 | 1.384E−02 | 2.736E−02 | 5.880E−03 | 1.438E−02 | 4.356E−03 | 2.532E−03 | 8.251E−03 | 1.053E−02 | 8.509E−03 |
| 12 | 9.238E−03 | 1.835E−02 | 1.288E−02 | 2.489E−03 | 1.056E−02 | 1.524E−02 | 1.180E−02 | 6.406E−03 | 8.230E−03 | 3.369E−03 | 4.775E−03 | 4.303E−03 | 1.105E−02 |
| 13 | 1.899E−02 | 2.200E−02 | 3.498E−03 | 1.824E−02 | 1.792E−02 | 2.543E−03 | 2.940E−02 | 2.006E−02 | 1.159E−02 | 7.157E−03 | 1.255E−02 | 5.258E−03 | 1.835E−02 |
| 14 | 7.715E−02 | 9.721E−02 | 9.335E−02 | 8.219E−02 | 4.464E−02 | 1.427E−01 | 2.854E−02 | 6.964E−02 | 1.942E−02 | 2.403E−02 | 2.564E−02 | 2.918E−02 | 2.983E−02 |
| 15 | 6.524E−03 | 9.174E−03 | 6.416E−03 | 2.489E−03 | 1.223E−02 | 1.084E−02 | 6.717E−03 | 7.210E−03 | 4.839E−03 | 2.103E−03 | 6.084E−03 | 5.258E−03 | 3.401E−03 |
| 16 | 2.178E−03 | 6.116E−04 | 5.837E−04 | 0.000E+00 | 0.000E+00 | 0.000E+00 | 2.521E−03 | 0.000E+00 | 0.000E+00 | 0.000E+00 | 0.000E+00 | 4.785E−04 | 1.277E−03 |
| 17 | 4.345E−03 | 1.835E−03 | 4.088E−03 | 1.663E−03 | 5.687E−03 | 2.543E−03 | 8.401E−04 | 6.406E−03 | 3.391E−03 | 4.217E−04 | 1.738E−03 | 2.865E−03 | 1.706E−03 |
| 18 | 2.339E−02 | 3.605E−02 | 2.221E−02 | 2.242E−02 | 3.412E−02 | 2.221E−02 | 6.212E−02 | 4.968E−02 | 2.854E−02 | 2.318E−02 | 2.650E−02 | 3.348E−02 | 2.339E−02 |
| 19 | 1.459E−01 | 1.867E−01 | 1.363E−01 | 6.148E−02 | 1.556E−01 | 1.749E−01 | 1.000E−01 | 2.167E−01 | 4.936E−02 | 4.045E−02 | 4.217E−02 | 5.258E−02 | 4.721E−02 |
| 20 | 2.178E−03 | 1.223E−03 | 0.000E+00 | 0.000E+00 | 1.620E−03 | 6.363E−04 | 8.401E−04 | 2.403E−03 | 2.425E−03 | 3.369E−03 | 1.738E−03 | 9.560E−04 | 1.277E−03 |
| 21 | 2.940E−02 | 3.058E−02 | 7.006E−03 | 7.468E−03 | 7.307E−03 | 7.629E−03 | 1.931E−02 | 8.809E−03 | 1.309E−02 | 1.094E−02 | 1.695E−02 | 1.191E−02 | 1.191E−02 |
| 22 | 2.178E−03 | 1.835E−03 | 2.918E−03 | 2.489E−03 | 3.251E−03 | 6.363E−04 | 2.521E−03 | 6.406E−03 | 1.942E−03 | 3.369E−03 | 1.298E−03 | 2.865E−03 | 8.509E−04 |
| 23 | 8.702E−02 | 9.109E−02 | 4.431E−02 | 2.242E−02 | 4.056E−02 | 4.828E−02 | 2.693E−02 | 4.807E−02 | 3.487E−02 | 3.283E−02 | 2.307E−02 | 2.436E−02 | 2.897E−02 |
| 24 | 6.137E−02 | 7.275E−02 | 7.060E−02 | 4.152E−02 | 8.691E−02 | 6.491E−02 | 8.144E−02 | 7.768E−02 | 4.506E−02 | 5.515E−02 | 4.260E−02 | 4.635E−02 | 4.421E−02 |
| 25 | 7.071E−02 | 7.768E−02 | 3.208E−02 | 1.491E−02 | 1.706E−02 | 2.350E−02 | 1.513E−02 | 1.685E−02 | 1.116E−02 | 1.266E−02 | 5.644E−03 | 1.004E−02 | 1.320E−02 |
| 26 | 2.715E−02 | 2.693E−02 | 2.157E−02 | 1.910E−02 | 2.758E−02 | 2.865E−02 | 1.845E−02 | 1.042E−02 | 8.230E−03 | 1.011E−02 | 7.822E−03 | 1.148E−02 | 9.785E−03 |
| 27 | 4.345E−03 | 6.727E−03 | 4.667E−03 | 8.305E−04 | 7.307E−03 | 3.820E−03 | 1.685E−03 | 7.210E−03 | 1.942E−03 | 2.951E−03 | 3.036E−03 | 1.438E−03 | 8.509E−04 |
| 28 | 5.054E−02 | 5.687E−02 | 3.273E−02 | 1.996E−02 | 2.275E−02 | 2.994E−02 | 2.350E−02 | 2.961E−02 | 2.661E−02 | 2.994E−02 | 1.910E−02 | 2.961E−02 | 2.811E−02 |
| 29 | 9.571E−02 | 1.027E−01 | 2.511E−02 | 2.661E−02 | 2.918E−02 | 3.562E−02 | 1.685E−02 | 4.571E−02 | 4.067E−02 | 4.045E−02 | 2.865E−02 | 3.305E−02 | 4.464E−02 |
| 30 | 3.970E−02 | 5.504E−02 | 7.532E−02 | 4.571E−02 | 8.530E−02 | 7.629E−02 | 7.897E−02 | 9.775E−02 | 6.781E−02 | 9.646E−02 | 6.642E−02 | 7.704E−02 | 5.740E−02 |
| 31 | 4.453E−02 | 4.281E−02 | 7.350E−02 | 4.818E−02 | 8.852E−02 | 6.298E−02 | 5.376E−02 | 7.607E−02 | 4.893E−02 | 8.594E−02 | 4.174E−02 | 5.064E−02 | 5.322E−02 |
| 32 | 8.155E−02 | 1.058E−01 | 4.785E−02 | 4.903E−02 | 4.710E−02 | 6.738E−02 | 1.025E−01 | 7.768E−02 | 4.410E−02 | 3.112E−02 | 4.088E−02 | 3.391E−02 | 6.845E−02 |
| 33 | 1.084E−02 | 7.951E−03 | 9.335E−03 | 7.468E−03 | 1.223E−02 | 1.395E−02 | 1.427E−02 | 1.363E−02 | 7.747E−03 | 1.352E−02 | 7.382E−03 | 1.717E−02 | 1.234E−02 |
| 34 | 4.485E−01 | 5.633E−01 | 6.373E−01 | 5.536E−01 | 6.695E−01 | 7.146E−01 | 1.208E+00 | 8.178E−01 | 1.545E−01 | 1.717E−01 | 1.459E−01 | 1.835E−01 | 1.717E−01 |
| 35 | 7.071E−02 | 7.157E−02 | 1.567E−01 | 9.549E−02 | 8.852E−02 | 8.208E−02 | 5.794E−02 | 9.850E−02 | 7.114E−02 | 9.979E−02 | 6.255E−02 | 5.740E−02 | 7.876E−02 |
| 36 | 4.345E−03 | 5.504E−03 | 9.914E−03 | 9.968E−03 | 7.307E−03 | 4.453E−03 | 3.358E−03 | 4.002E−03 | 1.017E−02 | 1.137E−02 | 5.215E−03 | 4.785E−03 | 3.401E−03 |
| 37 | 1.899E−02 | 1.652E−02 | 7.006E−03 | 9.131E−03 | 1.620E−02 | 1.781E−02 | 1.685E−02 | 9.614E−03 | 1.599E−02 | 1.727E−02 | 1.043E−02 | 1.288E−02 | 1.577E−02 |
| 38 | 3.809E−02 | 2.446E−02 | 1.459E−02 | 2.908E−02 | 3.004E−02 | 2.607E−02 | 3.112E−02 | 2.886E−02 | 1.545E−02 | 1.137E−02 | 1.298E−02 | 1.053E−02 | 1.448E−02 |
| 39 | 1.524E−01 | 1.191E−01 | 6.824E−02 | 1.191E−01 | 3.820E−02 | 1.738E−01 | 2.189E−02 | 4.249E−02 | 1.363E−01 | 1.070E−01 | 1.137E−01 | 6.502E−02 | 8.466E−02 |
| 40 | 1.288E−01 | 1.395E−01 | 1.567E−01 | 1.116E−01 | 1.341E−01 | 1.481E−01 | 1.974E−01 | 1.502E−01 | 1.352E−01 | 1.609E−01 | 1.395E−01 | 1.867E−01 | 1.620E−01 |
| 41 | 9.785E−03 | 3.122E−02 | 1.749E−02 | 2.328E−02 | 2.597E−02 | 2.414E−02 | 3.863E−02 | 2.479E−02 | 1.738E−02 | 2.532E−02 | 1.255E−02 | 2.060E−02 | 2.124E−02 |
| 42 | 5.440E−04 | 1.223E−03 | 2.339E−03 | 1.663E−03 | 4.871E−03 | 1.277E−03 | 5.043E−03 | 2.403E−03 | 9.689E−04 | 0.000E+00 | 1.738E−03 | 3.348E−03 | 0.000E+00 |
| 43 | 6.507E−03 | 7.176E−03 | 4.347E−03 | 7.176E−03 | 6.224E−03 | 8.230E−03 | 2.014E−02 | 7.690E−03 | 7.536E−03 | 4.938E−03 | 4.578E−03 | 5.607E−03 | 4.990E−03 |
| 44 | 5.410E−01 | 3.644E−01 | 2.869E−01 | 3.451E−01 | 4.221E−01 | 3.595E−01 | 7.799E−01 | 4.412E−01 | 9.593E−02 | 1.016E−01 | 8.796E−02 | 1.181E−01 | 1.039E−01 |
| 45 | 4.152E−01 | 2.275E−01 | 1.301E−01 | 1.106E−01 | 1.389E−01 | 1.309E−01 | 1.749E−01 | 1.222E−01 | 5.118E−02 | 4.732E−02 | 4.372E−02 | 4.990E−02 | 5.581E−02 |
| 46 | 1.790E−01 | 1.057E−01 | 1.093E−01 | 1.047E−01 | 1.741E−01 | 1.237E−01 | 2.181E−01 | 1.384E−01 | 7.587E−02 | 7.021E−02 | 6.121E−02 | 7.947E−02 | 5.530E−02 |
| 47 | 4.384E−01 | 2.587E−01 | 2.052E−01 | 2.721E−01 | 2.871E−01 | 2.735E−01 | 5.147E−01 | 2.799E−01 | 5.607E−02 | 6.121E−02 | 5.298E−02 | 6.096E−02 | 6.610E−02 |

APPENDIX D-continued

Ovarian Cancer
Training Dataset

| | | | | | | | | | | | | | |
|---|---|---|---|---|---|---|---|---|---|---|---|---|---|
| 48 | 7.356E−02 | 2.536E−02 | 3.035E−02 | 3.575E−02 | 2.855E−02 | 4.758E−02 | 2.315E−02 | 1.767E−02 | 9.645E−03 | 7.562E−03 | 8.745E−03 | 9.851E−03 | 6.636E−03 |
| 49 | 2.214E−02 | 1.114E−02 | 1.427E−02 | 2.130E−02 | 1.363E−02 | 3.009E−02 | 1.127E−02 | 1.114E−02 | 5.684E−03 | 3.421E−03 | 5.092E−03 | 5.272E−03 | 5.401E−03 |
| 50 | 8.462E−03 | 3.961E−03 | 5.324E−03 | 6.558E−03 | 3.112E−03 | 6.250E−03 | 2.623E−03 | 3.061E−03 | 2.906E−03 | 1.312E−03 | 2.701E−03 | 1.834E−03 | 2.040E−03 |
| 51 | 3.189E−02 | 1.047E−01 | 1.168E−01 | 1.582E−01 | 1.181E−01 | 1.255E−01 | 2.565E−01 | 1.801E−01 | 1.947E−01 | 1.926E−01 | 2.701E−03 | 2.949E−01 | 1.646E−01 |
| 52 | 2.726E−03 | 1.466E−03 | 1.538E−03 | 3.987E−03 | 2.726E−03 | 1.525E−03 | 7.047E−03 | 2.881E−03 | 4.295E−03 | 3.344E−03 | 1.978E−03 | 2.855E−03 | 2.243E−03 |
| 53 | 5.118E−02 | 7.021E−02 | 8.822E−02 | 6.867E−02 | 9.182E−02 | 9.182E−02 | 1.654E−01 | 1.232E−01 | 2.649E−02 | 2.649E−02 | 2.312E−02 | 2.881E−02 | 2.906E−02 |
| 54 | 4.727E+00 | 5.556E+00 | 5.203E+00 | 3.036E+00 | 4.612E+00 | 4.293E+00 | 3.105E+00 | 4.472E+00 | 5.805E+00 | 5.703E+00 | 6.093E+00 | 5.779E+00 | 6.435E+00 |
| 55 | 3.321E−01 | 4.096E−01 | 5.714E−01 | 5.790E−01 | 6.411E−01 | 6.069E−01 | 7.435E−01 | 6.524E−01 | 6.905E−01 | 6.929E−01 | 6.177E−01 | 7.799E−01 | 5.443E−01 |
| 56 | 1.695E−01 | 2.039E−01 | 1.749E−01 | 1.237E−01 | 1.533E−01 | 1.389E−01 | 1.358E−01 | 1.391E−01 | 1.795E−01 | 1.875E−01 | 1.918E−01 | 1.783E−01 | 1.908E−01 |
| 57 | 1.627E+00 | 2.089E+00 | 3.504E+00 | 2.926E+00 | 3.984E+00 | 3.763E+00 | 3.652E+00 | 3.943E+00 | 4.301E+00 | 4.231E+00 | 3.866E+00 | 4.611E+00 | 3.420E+00 |
| 58 | 4.038E−02 | 2.564E−02 | 3.292E−02 | 4.141E−02 | 5.581E−02 | 4.038E−02 | 6.404E−02 | 3.729E−02 | 4.141E−02 | 3.575E−02 | 2.932E−02 | 3.729E−02 | 3.575E−02 |
| 59 | 3.498E−02 | 4.630E−02 | 8.050E−02 | 5.735E−02 | 6.996E−02 | 8.256E−02 | 7.099E−02 | 8.230E−02 | 7.304E−02 | 7.690E−02 | 6.970E−02 | 8.565E−02 | 7.047E−02 |
| 60 | 3.138E−02 | 4.089E−02 | 4.064E−02 | 3.395E−02 | 3.704E−02 | 4.527E−02 | 6.739E−02 | 5.401E−02 | 1.348E−02 | 1.263E−02 | 1.134E−02 | 1.409E−02 | 1.682E−02 |
| 61 | 1.014E+00 | 1.054E+00 | 1.598E+00 | 1.721E+00 | 1.281E+00 | 1.809E+00 | 4.058E−01 | 1.087E+00 | 1.423E+00 | 1.008E+00 | 1.392E+00 | 1.082E+00 | 9.147E−01 |
| 62 | 6.676E−01 | 4.565E−01 | 3.284E−01 | 3.111E−01 | 2.433E−01 | 2.726E−01 | 3.137E−01 | 2.531E−01 | 4.201E−01 | 4.533E−01 | 4.257E−01 | 3.846E−01 | 5.824E−01 |
| 63 | 1.499E−02 | 8.205E−03 | 1.175E−02 | 1.453E−02 | 1.150E−02 | 1.692E−02 | 8.667E−03 | 8.642E−03 | 1.021E−02 | 9.079E−03 | 1.073E−02 | 9.413E−03 | 6.841E−03 |
| 64 | 3.658E+00 | 4.170E+00 | 2.996E+00 | 2.345E+00 | 1.839E+00 | 2.328E+00 | 1.766E+00 | 2.345E+00 | 3.562E+00 | 3.680E+00 | 4.023E+00 | 3.015E+00 | 3.917E+00 |
| 65 | 1.926E−01 | 1.561E−01 | 1.157E−01 | 1.070E−01 | 8.848E−02 | 9.105E−02 | 1.335E−01 | 1.016E−01 | 1.201E−01 | 1.255E−01 | 1.186E−01 | 1.078E−01 | 1.345E−01 |
| 66 | 4.541E−01 | 4.497E−01 | 5.771E−01 | 6.003E−01 | 4.509E−01 | 5.784E−01 | 5.554E−01 | 6.019E−01 | 8.158E−01 | 8.871E−01 | 7.672E−01 | 6.937E−01 | 7.416E−01 |
| 67 | 6.198E−02 | 4.424E−02 | 4.758E−02 | 7.176E−02 | 6.687E−02 | 5.787E−02 | 1.111E−01 | 6.070E−02 | 4.475E−02 | 5.453E−02 | 4.912E−02 | 4.630E−02 | 3.549E−02 |
| 68 | 1.929E−01 | 2.231E−01 | 1.979E−01 | 1.909E−01 | 1.510E−01 | 2.188E−01 | 3.488E−01 | 2.698E−01 | 4.115E−02 | 4.578E−02 | 4.167E−02 | 3.987E−02 | 4.887E−02 |
| 69 | 6.044E−01 | 5.846E−01 | 8.396E−01 | 1.002E+00 | 4.781E−01 | 1.002E+00 | 1.937E−01 | 5.040E−01 | 6.950E−01 | 4.697E−01 | 7.641E−01 | 4.747E−01 | 4.809E−01 |
| 70 | 4.012E−02 | 2.418E−02 | 3.935E−02 | 6.121E−02 | 3.163E−02 | 3.472E−02 | 3.138E−02 | 2.322E−02 | 2.983E−02 | 2.150E−02 | 2.829E−02 | 2.292E−02 | 1.888E−02 |
| 71 | 6.378E−03 | 8.513E−03 | 9.645E−03 | 1.751E−02 | 3.884E−03 | 1.541E−02 | 7.047E−03 | 6.713E−03 | 4.655E−03 | 5.967E−03 | 6.661E−03 | 4.707E−03 | 5.401E−03 |
| 72 | 2.477E−03 | 3.524E−03 | 1.957E−03 | 3.781E−03 | 3.112E−03 | 5.195E−03 | 3.009E−03 | 2.304E−03 | 2.675E−03 | 3.241E−03 | 3.215E−03 | 3.086E−03 | 1.836E−03 |
| 73 | 1.140E−03 | 6.433E−04 | 0.000E+00 | 8.736E−04 | 8.544E−04 | 1.343E−03 | 8.837E−04 | 8.431E−04 | 0.000E+00 | 1.772E−03 | 2.280E−03 | 5.034E−04 | 1.343E−03 |
| 74 | 5.147E−03 | 5.147E−03 | 4.910E−03 | 3.499E−03 | 5.982E−03 | 8.025E−03 | 5.305E−03 | 1.011E−02 | 2.551E−03 | 4.436E−03 | 2.280E−03 | 2.009E−03 | 2.686E−03 |
| 75 | 7.709E−01 | 4.628E−02 | 1.196E−01 | 3.228E−02 | 1.102E−01 | 6.084E−02 | 8.928E−02 | 6.907E−02 | 3.002E−02 | 6.907E−02 | 2.743E−02 | 3.172E−02 | 4.255E−02 |
| 76 | 1.098E−01 | 5.982E−02 | 2.156E−01 | 2.968E−02 | 1.230E−01 | 7.822E−02 | 1.580E−01 | 1.151E−01 | 4.481E−02 | 1.125E−01 | 2.833E−02 | 4.932E−02 | 6.400E−02 |
| 77 | 5.722E−03 | 1.094E−02 | 3.194E−02 | 3.499E−03 | 1.196E−02 | 4.018E−03 | 1.411E−02 | 7.585E−03 | 5.090E−03 | 5.316E−03 | 5.023E−03 | 4.029E−03 | 4.921E−03 |
| 78 | 5.722E−04 | 0.000E+00 | 5.519E−03 | 0.000E+00 | 8.544E−04 | 6.693E−04 | 0.000E+00 | 8.431E−04 | 5.090E−04 | 4.436E−04 | 1.366E−03 | 5.034E−04 | 0.000E+00 |
| 79 | 1.140E−03 | 1.930E−03 | 6.140E−04 | 3.499E−03 | 1.704E−03 | 6.693E−04 | 3.533E−03 | 4.210E−03 | 0.000E+00 | 8.860E−04 | 4.571E−04 | 1.006E−03 | 0.000E+00 |
| 80 | 5.722E−04 | 1.287E−03 | 1.840E−03 | 2.619E−03 | 1.704E−03 | 1.343E−03 | 8.837E−04 | 8.431E−04 | 1.019E−03 | 1.332E−03 | 1.366E−03 | 1.006E−03 | 1.343E−03 |
| 81 | 2.856E−03 | 9.650E−03 | 5.519E−03 | 1.309E−02 | 1.111E−02 | 1.208E−02 | 9.718E−03 | 6.738E−03 | 6.625E−03 | 3.984E−03 | 4.571E−03 | 6.038E−03 | 4.921E−03 |
| 82 | 5.722E−04 | 3.860E−03 | 3.070E−03 | 0.000E+00 | 2.562E−03 | 6.693E−04 | 4.413E−03 | 7.585E−03 | 1.019E−03 | 4.876E−03 | 0.000E+00 | 7.043E−03 | 4.481E−03 |
| 83 | 1.140E−03 | 1.287E−03 | 4.910E−03 | 0.000E+00 | 1.704E−03 | 0.000E+00 | 1.772E−03 | 4.210E−03 | 1.019E−03 | 3.104E−03 | 0.000E+00 | 2.517E−03 | 2.235E−03 |
| 84 | 9.153E−03 | 5.147E−03 | 4.910E−03 | 1.140E−02 | 1.704E−02 | 7.359E−03 | 1.772E−02 | 1.603E−02 | 8.149E−03 | 5.316E−03 | 7.314E−03 | 8.047E−03 | 5.813E−03 |
| 85 | 1.716E−03 | 2.573E−03 | 4.300E−03 | 8.736E−04 | 2.562E−03 | 1.343E−03 | 2.652E−03 | 3.375E−03 | 5.090E−04 | 2.212E−03 | 1.828E−03 | 4.029E−03 | 8.950E−04 |
| 86 | 7.438E−03 | 5.147E−03 | 8.589E−03 | 3.499E−03 | 1.287E−02 | 4.018E−03 | 1.061E−02 | 9.266E−03 | 7.641E−03 | 8.420E−03 | 2.280E−03 | 6.535E−03 | 8.059E−03 |
| 87 | 1.998E−02 | 1.163E−02 | 3.679E−02 | 1.659E−02 | 5.553E−02 | 2.946E−02 | 3.804E−02 | 3.284E−02 | 1.885E−02 | 5.666E−02 | 1.467E−02 | 2.619E−02 | 2.325E−02 |
| 88 | 7.438E−03 | 1.930E−03 | 7.980E−03 | 0.000E+00 | 8.544E−03 | 3.341E−03 | 6.185E−03 | 4.210E−03 | 3.059E−03 | 7.088E−03 | 9.142E−04 | 5.530E−03 | 2.235E−03 |
| 89 | 3.431E−03 | 9.650E−03 | 2.946E−02 | 1.749E−03 | 1.111E−02 | 1.343E−03 | 1.682E−02 | 1.264E−02 | 5.090E−03 | 1.727E−02 | 6.400E−03 | 1.006E−02 | 1.298E−02 |
| 90 | 2.291E−02 | 1.930E−02 | 8.228E−02 | 1.569E−02 | 3.070E−02 | 1.806E−02 | 2.122E−02 | 3.792E−02 | 1.783E−02 | 3.860E−02 | 1.140E−02 | 2.370E−02 | 2.099E−02 |
| 91 | 3.431E−03 | 5.790E−03 | 1.659E−02 | 6.986E−03 | 5.124E−03 | 5.350E−03 | 1.061E−02 | 5.903E−03 | 5.090E−03 | 8.860E−03 | 5.023E−03 | 1.512E−03 | 7.607E−03 |
| 92 | 4.007E−03 | 3.860E−03 | 1.591E−02 | 7.856E−03 | 1.287E−02 | 9.368E−03 | 2.032E−02 | 1.772E−02 | 1.121E−02 | 1.546E−02 | 6.851E−03 | 1.056E−02 | 1.388E−02 |
| 93 | 4.007E−03 | 4.503E−03 | 4.910E−03 | 5.237E−03 | 5.124E−03 | 8.025E−03 | 7.957E−03 | 6.738E−03 | 4.582E−03 | 1.019E−02 | 9.142E−04 | 7.551E−03 | 3.138E−03 |
| 94 | 5.722E−04 | 2.573E−03 | 1.230E−03 | 1.749E−03 | 3.420E−03 | 1.343E−03 | 3.533E−03 | 3.375E−03 | 1.524E−03 | 1.772E−03 | 3.194E−03 | 2.517E−03 | 0.000E+00 |
| 95 | 5.722E−03 | 4.503E−03 | 4.300E−02 | 4.368E−03 | 5.982E−03 | 1.467E−02 | 7.957E−03 | 1.185E−02 | 7.133E−03 | 9.300E−03 | 6.851E−03 | 1.512E−03 | 5.813E−03 |
| 96 | 3.431E−03 | 4.503E−03 | 2.144E−02 | 7.856E−03 | 2.562E−03 | 1.343E−03 | 5.305E−03 | 5.903E−03 | 2.551E−03 | 7.088E−03 | 6.400E−03 | 1.512E−03 | 8.059E−03 |
| 97 | 1.140E−03 | 2.573E−03 | 9.819E−03 | 4.368E−03 | 7.686E−03 | 6.693E−04 | 5.305E−03 | 5.903E−03 | 3.567E−03 | 5.316E−03 | 1.366E−03 | 1.512E−03 | 2.235E−03 |

APPENDIX D-continued

Ovarian Cancer
Training Dataset

| | | | | | | | | | | | | | |
|---|---|---|---|---|---|---|---|---|---|---|---|---|---|
| 98 | 5.147E−03 | 4.503E−03 | 9.210E−03 | 5.237E−03 | 1.196E−02 | 7.359E−03 | 6.185E−03 | 8.431E−03 | 1.019E−02 | 8.860E−03 | 6.400E−03 | 7.551E−03 | 1.208E−02 |
| 99 | 1.080E−01 | 1.013E−01 | 5.003E−02 | 9.209E−02 | 1.105E−01 | 7.848E−02 | 9.503E−02 | 8.792E−02 | 1.207E−01 | 7.554E−02 | 8.682E−02 | 8.633E−02 | 1.447E−01 |
| 100 | 2.980E−02 | 4.476E−02 | 2.538E−02 | 3.507E−02 | 4.831E−02 | 3.483E−02 | 6.438E−02 | 4.304E−02 | 2.489E−02 | 1.974E−02 | 2.685E−02 | 2.735E−02 | 2.428E−02 |
| 101 | 1.161E−01 | 2.121E−01 | 1.324E−01 | 1.324E−01 | 1.766E−01 | 1.619E−01 | 1.251E−01 | 2.305E−01 | 1.422E−01 | 1.349E−01 | 1.398E−01 | 1.459E−01 | 1.251E−01 |
| 102 | 3.519E−01 | 3.850E−01 | 4.905E−01 | 9.755E−01 | 6.597E−01 | 4.402E−01 | 1.096E+00 | 5.494E−01 | 6.070E−01 | 5.874E−01 | 5.028E−01 | 5.996E−01 | 5.015E−01 |
| 103 | 1.181E−01 | 2.170E−01 | 2.134E−01 | 1.631E−01 | 2.023E−01 | 2.244E−01 | 1.496E−01 | 3.078E−01 | 1.643E−01 | 1.435E−01 | 1.864E−01 | 1.729E−01 | 1.717E−01 |
| 104 | 2.195E−01 | 1.987E−01 | 2.036E−01 | 2.845E−01 | 2.428E−01 | 1.790E−01 | 3.384E−01 | 2.403E−01 | 2.477E−01 | 2.649E−01 | 1.876E−01 | 2.759E−01 | 2.624E−01 |
| 105 | 5.285E−01 | 6.070E−01 | 7.541E−01 | 1.301E+00 | 1.004E+00 | 8.007E−01 | 1.234E+00 | 9.704E−01 | 7.014E−01 | 6.830E−01 | 7.650E−01 | 7.590E−01 | 6.773E−01 |
| 106 | 1.741E−01 | 1.471E−01 | 8.866E−02 | 1.324E−01 | 1.606E−01 | 1.471E−01 | 2.060E−01 | 1.435E−01 | 1.631E−01 | 1.386E−01 | 1.349E−01 | 1.239E−01 | 1.864E−01 |
| 107 | 1.275E−01 | 1.288E−01 | 9.332E−02 | 1.300E−01 | 1.216E−01 | 1.053E−01 | 1.901E−01 | 1.717E−01 | 1.189E−01 | 9.675E−02 | 1.142E−01 | 9.834E−02 | 1.459E−01 |
| 108 | 1.582E−01 | 1.790E−01 | 1.852E−01 | 2.183E−01 | 1.508E−01 | 1.827E−01 | 1.398E−01 | 1.754E−01 | 1.876E−01 | 1.557E−01 | 1.778E−01 | 1.508E−01 | 1.937E−01 |
| 109 | 5.592E−03 | 8.387E−03 | 3.998E−03 | 1.044E−02 | 8.351E−03 | 3.630E−03 | 2.207E−02 | 5.494E−03 | 7.750E−03 | 6.254E−03 | 1.987E−03 | 4.917E−03 | 5.346E−03 |
| 110 | 1.987E−02 | 3.213E−02 | 3.139E−02 | 2.845E−02 | 2.502E−02 | 4.500E−02 | 2.685E−02 | 3.568E−02 | 2.820E−02 | 3.372E−02 | 3.127E−02 | 4.488E−02 | 3.887E−02 |
| 111 | 9.945E−03 | 2.440E−02 | 1.937E−02 | 1.239E−02 | 3.151E−02 | 1.594E−02 | 2.882E−02 | 2.649E−02 | 1.606E−02 | 2.403E−02 | 2.281E−02 | 2.575E−02 | 2.330E−02 |
| 112 | 4.353E−03 | 9.086E−03 | 1.133E−02 | 4.746E−03 | 2.134E−02 | 1.312E−02 | 2.587E−02 | 2.109E−02 | 1.827E−02 | 1.778E−02 | 8.939E−03 | 1.864E−02 | 1.410E−02 |
| 113 | 2.489E−03 | 6.291E−03 | 2.673E−03 | 3.801E−03 | 5.567E−03 | 5.089E−03 | 2.882E−03 | 4.574E−03 | 1.051E−02 | 9.148E−03 | 2.477E−03 | 4.917E−03 | 4.378E−03 |
| 114 | 2.489E−03 | 9.086E−03 | 6.671E−03 | 6.646E−03 | 7.431E−03 | 3.630E−03 | 5.763E−03 | 9.160E−03 | 6.082E−03 | 4.819E−03 | 1.042E−02 | 7.652E−03 | 4.868E−03 |
| 115 | 6.830E−03 | 6.990E−03 | 5.334E−03 | 1.901E−03 | 1.300E−02 | 1.162E−02 | 2.011E−02 | 1.459E−02 | 1.435E−02 | 1.729E−02 | 8.437E−03 | 9.834E−03 | 1.361E−02 |
| 116 | 3.102E−03 | 4.893E−03 | 5.996E−03 | 2.845E−03 | 7.431E−03 | 5.089E−03 | 1.153E−02 | 7.321E−03 | 3.875E−03 | 6.744E−03 | 1.987E−03 | 3.826E−03 | 5.346E−03 |
| 117 | 4.353E−03 | 1.398E−02 | 8.007E−03 | 8.535E−03 | 1.398E−02 | 9.454E−03 | 2.109E−02 | 1.373E−02 | 5.530E−03 | 1.059E−02 | 6.450E−03 | 1.422E−02 | 8.755E−03 |
| 118 | 8.694E−03 | 8.387E−03 | 7.333E−03 | 8.535E−03 | 1.113E−02 | 3.630E−03 | 1.056E−02 | 1.007E−02 | 2.771E−03 | 4.329E−03 | 3.973E−03 | 7.100E−03 | 1.021E−02 |
| 119 | 3.728E−03 | 1.263E−02 | 1.398E−02 | 6.646E−03 | 4.635E−03 | 7.272E−03 | 8.645E−03 | 1.557E−02 | 1.051E−02 | 1.398E−02 | 6.953E−03 | 9.834E−03 | 7.774E−03 |
| 120 | 3.102E−03 | 1.324E−02 | 8.670E−03 | 1.139E−02 | 8.351E−03 | 7.995E−03 | 1.349E−02 | 9.160E−03 | 1.107E−02 | 5.297E−03 | 1.042E−02 | 1.203E−02 | 6.315E−03 |
| 121 | 6.224E−02 | 2.627E−02 | 8.353E−03 | 1.184E−02 | 4.648E−02 | 1.362E−02 | 1.264E−01 | 2.867E−02 | 5.539E−02 | 6.625E−02 | 4.657E−02 | 8.896E−02 | 6.394E−02 |
| 122 | 1.086E−01 | 1.487E−01 | 3.758E−02 | 1.425E−01 | 9.884E−02 | 4.096E−02 | 2.164E−01 | 1.318E−01 | 8.994E−02 | 1.416E−01 | 1.674E−01 | 1.167E−01 | 1.585E−01 |
| 123 | 2.208E+00 | 2.627E+00 | 2.947E+00 | 1.362E+00 | 3.749E+00 | 2.867E+00 | 2.760E+00 | 4.666E+00 | 1.968E+00 | 2.084E+00 | 1.861E+00 | 2.315E+00 | 1.977E+00 |
| 124 | 4.274E−02 | 1.745E−02 | 2.084E−02 | 1.184E−02 | 4.648E−02 | 1.817E−02 | 7.809E−02 | 4.586E−02 | 5.886E−02 | 6.028E−02 | 6.527E−02 | 9.617E−02 | 2.743E−02 |
| 125 | 8.557E−02 | 3.936E−02 | 1.674E−02 | 4.159E−02 | 1.745E−02 | 5.459E−02 | 5.405E−02 | 4.016E−02 | 7.275E−02 | 1.354E−01 | 3.731E−02 | 1.193E−01 | 9.172E−02 |
| 126 | 1.852E+00 | 1.282E+00 | 2.841E−01 | 4.577E−01 | 3.491E−01 | 3.366E−01 | 5.289E−01 | 2.636E−01 | 7.551E−01 | 1.051E+00 | 1.033E+00 | 7.257E−01 | 8.584E−01 |
| 127 | 3.482E+00 | 2.048E+00 | 1.175E+00 | 8.851E−01 | 1.300E+00 | 9.706E−01 | 1.469E+00 | 1.069E+00 | 1.416E+00 | 3.295E+00 | 1.719E+00 | 1.906E+00 | 1.870E+00 |
| 128 | 2.431E+00 | 2.449E+00 | 2.235E+00 | 8.557E−01 | 2.752E+00 | 2.146E+00 | 1.505E+00 | 3.847E+00 | 1.532E+00 | 1.728E+00 | 1.496E+00 | 1.487E+00 | 1.487E+00 |
| 129 | 5.833E−02 | 5.690E−02 | 4.176E−02 | 2.378E−02 | 5.227E−02 | 2.734E−02 | 7.809E−02 | 5.735E−02 | 6.233E−02 | 3.010E−02 | 2.796E−02 | 5.476E−02 | 3.954E−02 |
| 130 | 1.585E+01 | 1.043E+01 | 4.809E+00 | 1.284E+01 | 4.693E+00 | 9.687E+00 | 3.874E+00 | 3.606E+00 | 1.008E+01 | 7.383E+00 | 1.106E+01 | 7.654E+00 | 8.127E+00 |
| 131 | 1.006E+01 | 6.964E+00 | 6.391E+00 | 1.018E+01 | 3.651E+00 | 1.318E+01 | 1.968E+00 | 3.081E+00 | 6.937E+00 | 5.637E+00 | 9.006E+00 | 6.330E+00 | 7.208E+00 |
| 132 | 2.725E−02 | 5.245E−02 | 5.423E−02 | 1.247E−01 | 1.282E−01 | 2.734E−02 | 9.617E−02 | 6.874E−02 | 8.664E−02 | 6.625E−02 | 1.086E−01 | 5.815E−02 | 8.522E−02 |
| 133 | 3.891E−03 | 8.744E−03 | 2.502E−02 | 2.974E−02 | 1.745E−02 | 1.362E−02 | 6.011E−03 | 3.437E−02 | 1.389E−02 | 6.028E−03 | 6.215E−03 | 2.057E−02 | 2.128E−02 |
| 134 | 7.774E−03 | 4.372E−03 | 2.084E−02 | 4.755E−02 | 2.324E−02 | 2.271E−02 | 1.799E−02 | 4.016E−02 | 2.422E−02 | 1.202E−02 | 9.350E−03 | 1.024E−02 | 2.128E−02 |
| 135 | 1.167E−02 | 1.745E−02 | 1.256E−02 | 3.562E−02 | 4.069E−02 | 1.362E−02 | 4.203E−02 | 3.437E−02 | 2.075E−02 | 1.505E−02 | 9.350E−03 | 2.395E−02 | 1.220E−02 |
| 136 | 3.891E−03 | 1.309E−02 | 8.353E−03 | 5.939E−03 | 5.815E−02 | 4.550E−03 | 3.606E−02 | 1.719E−02 | 1.389E−02 | 2.413E−02 | 1.861E−02 | 3.081E−02 | 4.265E−02 |
| 137 | 2.333E−02 | 3.500E−02 | 6.679E−02 | 8.317E−02 | 1.167E−01 | 3.642E−02 | 6.607E−02 | 5.735E−02 | 1.104E−01 | 6.028E−02 | 9.350E−02 | 8.210E−02 | 6.999E−02 |
| 138 | 7.774E−03 | 1.309E−02 | 3.339E−02 | 3.562E−02 | 0.000E+00 | 1.362E−02 | 4.809E−02 | 4.016E−02 | 1.042E−02 | 3.918E−02 | 2.173E−02 | 2.057E−02 | 2.743E−02 |
| 139 | 3.037E−01 | 1.621E−01 | 1.416E−01 | 1.069E−01 | 2.030E−01 | 1.594E−01 | 7.213E−02 | 1.834E−01 | 1.318E−01 | 2.324E−01 | 2.146E−01 | 1.300E−01 | 1.799E−01 |
| 140 | 5.441E−02 | 1.006E−01 | 1.042E−01 | 7.720E−02 | 1.104E−01 | 7.738E−02 | 5.405E−02 | 1.371E−01 | 8.994E−02 | 1.238E−01 | 1.211E−01 | 1.612E−01 | 8.219E−02 |
| 141 | 3.500E−02 | 5.690E−02 | 2.084E−02 | 9.528E−02 | 4.069E−02 | 5.459E−02 | 7.213E−02 | 2.867E−02 | 4.506E−02 | 4.221E−02 | 3.731E−02 | 2.395E−02 | 6.394E−02 |
| 142 | 1.558E−02 | 1.309E−02 | 2.502E−02 | 4.755E−02 | 2.903E−02 | 2.271E−02 | 2.404E−02 | 1.719E−02 | 2.422E−02 | 6.028E−03 | 6.215E−03 | 1.024E−02 | 6.091E−03 |
| 143 | 1.558E−02 | 2.191E−02 | 2.084E−02 | 5.939E−03 | 3.491E−02 | 4.096E−02 | 2.404E−02 | 3.437E−02 | 3.464E−02 | 2.716E−02 | 2.484E−02 | 2.734E−02 | 2.431E−02 |
| 144 | 2.725E−02 | 5.245E−02 | 2.921E−02 | 4.159E−02 | 2.324E−02 | 2.271E−02 | 1.202E−02 | 1.149E−02 | 2.769E−02 | 5.120E−02 | 5.280E−02 | 4.791E−02 | 3.651E−02 |
| 145 | 3.500E−02 | 3.063E−02 | 2.502E−02 | 3.562E−02 | 2.903E−02 | 2.271E−02 | 1.202E−02 | 2.289E−02 | 3.117E−02 | 4.817E−02 | 3.108E−02 | 3.081E−02 | 1.523E−02 |
| 146 | 2.182E−01 | 1.665E−01 | 2.422E−01 | 1.541E−01 | 2.030E−01 | 2.271E−01 | 6.607E−02 | 2.520E−01 | 1.799E−01 | 9.350E−02 | 1.674E−01 | 7.186E−02 | 1.282E−01 |
| 147 | 2.992E−01 | 1.264E−01 | 1.131E−01 | 1.131E−01 | 9.884E−02 | 6.821E−02 | 5.405E−02 | 5.156E−02 | 6.233E−02 | 1.024E−01 | 8.700E−02 | 1.131E−01 | 1.158E−01 |

APPENDIX D-continued

Ovarian Cancer
Training Dataset

| | | | | | | | | | | | | | |
|---|---|---|---|---|---|---|---|---|---|---|---|---|---|
| 148 | 8.869E−01 | 4.025E−01 | 3.045E−01 | 2.315E−01 | 2.262E−01 | 2.137E−01 | 1.683E−01 | 4.524E−01 | 2.805E−01 | 6.055E−01 | 4.292E−01 | 2.636E−01 | 2.858E−01 |
| 149 | 1.906E−01 | 6.999E−02 | 1.380E−01 | 5.939E−02 | 9.884E−02 | 5.913E−02 | 6.607E−02 | 9.706E−02 | 7.275E−02 | 1.443E−01 | 8.994E−02 | 6.500E−02 | 8.825E−02 |
| 150 | 0.000E+00 | 1.309E−02 | 8.353E−03 | 1.781E−02 | 4.648E−02 | 2.271E−02 | 3.001E−02 | 3.437E−02 | 3.464E−03 | 9.083E−03 | 6.215E−03 | 2.057E−02 | 9.172E−03 |
| 151 | 3.891E−03 | 1.309E−02 | 1.674E−02 | 4.755E−02 | 1.745E−02 | 2.271E−02 | 3.001E−02 | 1.149E−02 | 2.769E−02 | 1.202E−02 | 2.173E−02 | 2.057E−02 | 3.045E−02 |
| 152 | 5.441E−02 | 4.372E−02 | 1.674E−02 | 8.317E−02 | 2.903E−02 | 1.362E−02 | 2.404E−02 | 3.437E−02 | 6.581E−02 | 2.110E−02 | 3.419E−02 | 6.848E−02 | 5.779E−02 |
| 153 | 3.891E−02 | 2.191E−02 | 2.084E−02 | 1.184E−02 | 1.167E−02 | 1.817E−02 | 6.011E−03 | 1.149E−02 | 3.117E−02 | 1.808E−02 | 2.173E−02 | 1.024E−02 | 2.743E−02 |
| 154 | 1.167E−02 | 2.191E−02 | 1.674E−02 | 1.184E−02 | 1.745E−02 | 4.550E−03 | 2.404E−02 | 2.867E−02 | 6.928E−03 | 1.505E−02 | 3.108E−03 | 1.710E−02 | 2.431E−02 |
| 155 | 3.891E−02 | 3.936E−02 | 2.921E−02 | 1.184E−02 | 1.745E−02 | 1.817E−02 | 2.404E−02 | 4.016E−02 | 2.075E−02 | 2.110E−02 | 2.796E−02 | 1.710E−02 | 2.431E−02 |
| 156 | 2.841E−01 | 2.057E−01 | 6.385E−01 | 4.043E−01 | 2.903E−01 | 7.738E−01 | 5.405E−02 | 2.983E−01 | 2.324E−01 | 1.870E−01 | 2.894E−01 | 1.638E−01 | 2.707E−01 |
| 157 | 1.906E−01 | 1.184E−01 | 1.959E−01 | 1.362E−01 | 1.167E−01 | 1.915E−01 | 3.606E−02 | 1.834E−01 | 1.140E−01 | 1.024E−01 | 1.024E−01 | 6.500E−02 | 1.336E−01 |
| 158 | 3.037E−01 | 2.627E−01 | 4.720E−01 | 3.330E−01 | 3.019E−01 | 4.319E−01 | 3.606E−02 | 3.206E−01 | 2.734E−01 | 2.075E−01 | 3.606E−01 | 2.057E−01 | 2.591E−01 |
| 159 | 1.362E−01 | 6.999E−02 | 1.131E−01 | 1.247E−01 | 1.282E−01 | 1.861E−01 | 4.809E−02 | 1.202E−01 | 1.389E−01 | 9.350E−02 | 1.496E−01 | 5.815E−02 | 8.522E−02 |
| 160 | 3.500E−02 | 6.126E−02 | 2.084E−02 | 2.974E−02 | 3.491E−02 | 4.550E−02 | 4.203E−02 | 3.437E−02 | 4.159E−02 | 4.817E−02 | 3.108E−02 | 4.791E−02 | 3.651E−02 |
| 161 | 1.941E−02 | 2.191E−02 | 8.353E−03 | 0.000E+00 | 4.069E−02 | 1.362E−02 | 3.606E−02 | 4.586E−02 | 1.389E−02 | 5.120E−02 | 4.657E−02 | 6.848E−03 | 4.568E−02 |
| 162 | 3.500E−02 | 4.372E−02 | 3.339E−02 | 3.562E−02 | 1.167E−02 | 4.096E−02 | 6.011E−03 | 1.149E−02 | 1.736E−02 | 3.313E−02 | 2.484E−02 | 1.710E−02 | 3.954E−02 |
| 163 | 1.558E−02 | 2.191E−02 | 3.758E−02 | 3.562E−02 | 2.324E−02 | 3.642E−02 | 1.799E−02 | 3.437E−02 | 1.389E−02 | 2.716E−02 | 1.549E−02 | 3.081E−02 | 2.128E−02 |
| 164 | 2.725E−02 | 2.191E−02 | 2.084E−02 | 2.974E−02 | 1.167E−02 | 2.734E−02 | 6.011E−03 | 1.719E−02 | 2.422E−02 | 2.413E−02 | 1.247E−02 | 2.395E−02 | 3.651E−02 |
| 165 | 3.891E−03 | 2.191E−02 | 1.674E−02 | 5.939E−02 | 4.069E−02 | 2.271E−02 | 3.606E−02 | 1.719E−02 | 1.736E−02 | 1.505E−02 | 2.796E−02 | 2.734E−02 | 1.523E−02 |
| 166 | 2.725E−02 | 3.936E−02 | 3.758E−02 | 2.378E−02 | 5.227E−02 | 7.738E−02 | 1.799E−02 | 2.867E−02 | 2.422E−02 | 3.313E−02 | 3.419E−02 | 4.105E−02 | 1.825E−02 |
| 161 | 1.870E−01 | 1.229E−01 | 3.544E−01 | 1.781E−01 | 1.336E−01 | 4.728E−01 | 4.203E−02 | 1.603E−01 | 1.451E−01 | 1.051E−01 | 2.048E−01 | 1.229E−01 | 1.069E−01 |
| 168 | 1.086E−01 | 1.051E−01 | 1.131E−01 | 8.317E−02 | 1.042E−01 | 1.638E−01 | 8.415E−02 | 1.264E−01 | 1.175E−01 | 7.533E−02 | 1.122E−01 | 1.131E−01 | 1.158E−01 |
| 169 | 4.666E−02 | 5.245E−02 | 6.260E−02 | 8.317E−02 | 8.718E−02 | 4.550E−02 | 3.001E−02 | 4.016E−02 | 6.581E−02 | 5.120E−02 | 3.731E−02 | 3.767E−02 | 5.779E−02 |
| 170 | 1.558E−02 | 4.372E−02 | 1.674E−02 | 3.562E−02 | 6.972E−02 | 3.188E−02 | 2.404E−02 | 8.023E−02 | 4.159E−02 | 4.817E−02 | 6.527E−02 | 3.767E−02 | 2.431E−02 |
| 171 | 1.558E−02 | 2.627E−02 | 4.176E−03 | 4.159E−02 | 2.324E−02 | 2.271E−02 | 6.011E−02 | 5.735E−02 | 4.853E−02 | 2.413E−02 | 3.108E−02 | 3.419E−02 | 4.568E−02 |
| 172 | 5.408E−02 | 6.806E−02 | 9.258E−02 | 1.312E−01 | 9.283E−02 | 1.059E−01 | 1.484E−01 | 1.089E−01 | 5.101E−02 | 7.590E−02 | 4.917E−02 | 8.903E−02 | 4.868E−02 |
| 173 | 2.415E+00 | 2.357E+00 | 2.696E+00 | 3.375E+00 | 3.572E+00 | 2.710E+00 | 4.401E+00 | 3.232E+00 | 1.331E+00 | 1.627E+00 | 1.335E+00 | 1.869E+00 | 1.503E+00 |
| 174 | 4.610E+00 | 4.412E+00 | 4.861E+00 | 5.908E+00 | 6.096E+00 | 4.668E+00 | 5.479E+00 | 5.239E+00 | 2.008E+00 | 2.056E+00 | 2.339E+00 | 2.563E+00 | 2.241E+00 |
| 175 | 1.558E+00 | 1.008E+00 | 1.038E+00 | 1.274E+00 | 1.275E+00 | 9.411E−01 | 1.479E+00 | 1.098E+00 | 5.788E−01 | 8.693E−01 | 5.273E−01 | 8.411E−01 | 8.295E−01 |
| 176 | 3.062E+00 | 3.468E+00 | 2.280E+00 | 2.370E+00 | 4.425E+00 | 3.117E+00 | 4.819E+00 | 4.501E+00 | 1.756E+00 | 2.313E+00 | 1.581E+00 | 2.727E+00 | 2.648E+00 |
| 177 | 2.160E+00 | 1.389E+00 | 1.093E+00 | 1.588E+00 | 1.457E+00 | 2.035E+00 | 8.056E−01 | 1.031E+00 | 6.278E−01 | 5.763E−01 | 6.315E−01 | 6.904E−01 | 7.520E−01 |
| 178 | 3.556E−01 | 3.213E−01 | 1.386E−01 | 2.514E−01 | 2.183E−01 | 2.673E−01 | 1.692E−01 | 1.459E−01 | 1.410E−01 | 1.496E−01 | 1.435E−01 | 1.410E−01 | 1.182E−01 |
| 179 | 5.359E−02 | 4.697E−02 | 1.778E−02 | 2.207E−02 | 3.041E−02 | 3.568E−02 | 5.543E−02 | 2.367E−02 | 2.048E−02 | 1.913E−02 | 2.305E−02 | 1.508E−02 | 2.685E−02 |
| 180 | 1.606E−02 | 2.587E−02 | 1.496E−02 | 1.471E−02 | 4.721E−02 | 1.128E−02 | 6.291E−02 | 2.452E−02 | 1.815E−02 | 2.367E−02 | 9.418E−03 | 2.403E−02 | 3.274E−02 |
| 181 | 2.244E−02 | 2.232E−02 | 7.468E−03 | 1.876E−02 | 1.275E−02 | 1.570E−02 | 2.403E−02 | 3.004E−02 | 8.584E−03 | 9.540E−03 | 8.988E−03 | 1.410E−02 | 1.386E−02 |
| 182 | 6.426E−02 | 6.867E−02 | 8.105E−02 | 2.195E−01 | 1.208E−01 | 7.333E−02 | 2.072E−01 | 8.044E−02 | 1.155E−01 | 9.749E−02 | 1.048E−01 | 1.122E−01 | 8.596E−02 |
| 183 | 1.137E+00 | 8.674E−01 | 1.312E+00 | 2.851E+00 | 1.716E+00 | 1.070E+00 | 2.819E+00 | 1.626E+00 | 1.651E+00 | 1.914E+00 | 1.446E+00 | 1.819E+00 | 1.485E+00 |
| 184 | 1.262E+00 | 1.032E+00 | 1.404E+00 | 3.475E+00 | 1.888E+00 | 1.265E+00 | 2.987E+00 | 1.583E+00 | 1.691E+00 | 1.636E+00 | 1.560E+00 | 1.707E+00 | 1.301E+00 |
| 185 | 1.064E+00 | 7.701E−01 | 9.319E−01 | 2.137E+00 | 1.368E+00 | 7.738E−01 | 2.139E+00 | 1.151E+00 | 1.184E+00 | 1.185E+00 | 1.094E+00 | 1.268E+00 | 1.033E+00 |
| 186 | 2.600E+00 | 1.737E+00 | 2.384E+00 | 3.914E+00 | 2.708E+00 | 1.702E+00 | 3.595E+00 | 2.508E+00 | 2.393E+00 | 2.776E+00 | 2.335E+00 | 2.609E+00 | 2.864E+00 |
| 187 | 7.456E−01 | 3.948E−01 | 4.819E−01 | 8.516E−01 | 5.923E−01 | 3.814E−01 | 8.952E−01 | 5.763E−01 | 6.965E−01 | 9.386E−01 | 5.665E−01 | 6.744E−01 | 9.804E−01 |
| 188 | 8.032E−02 | 3.740E−02 | 2.759E−02 | 6.793E−02 | 6.315E−02 | 3.004E−02 | 8.105E−02 | 5.212E−02 | 5.628E−02 | 8.670E−02 | 5.224E−02 | 5.273E−02 | 1.111E−01 |
| 189 | 1.226E−02 | 6.622E−03 | 5.175E−03 | 1.717E−02 | 1.521E−02 | 8.142E−03 | 3.225E−02 | 1.337E−02 | 1.435E−02 | 2.121E−02 | 1.239E−02 | 2.403E−02 | 1.766E−02 |
| 190 | 2.085E−01 | 1.668E−01 | 1.023E−01 | 2.514E−01 | 2.391E−01 | 1.009E−01 | 2.219E−01 | 2.121E−01 | 1.717E−01 | 2.563E−01 | 1.349E−01 | 2.354E−01 | 2.857E−01 |
| 191 | 3.243E+00 | 1.917E+00 | 1.728E+00 | 4.177E+00 | 2.393E+00 | 3.015E+00 | 1.292E+00 | 1.712E+00 | 2.476E+00 | 2.228E+00 | 2.178E+00 | 2.147E+00 | 2.551E+00 |
| 192 | 8.498E−01 | 6.524E−01 | 3.826E−01 | 9.850E−01 | 5.996E−01 | 6.609E−01 | 4.304E−01 | 3.814E−01 | 7.259E−01 | 7.934E−01 | 6.714E−01 | 6.303E−01 | 6.536E−01 |
| 193 | 9.638E−02 | 6.511E−02 | 4.660E−02 | 9.896E−02 | 8.007E−02 | 5.763E−02 | 1.312E−01 | 7.345E−02 | 9.307E−02 | 1.170E−01 | 1.019E−01 | 9.430E−02 | 1.174E−01 |
| 194 | 3.691E−02 | 6.266E−02 | 5.812E−02 | 1.186E−01 | 1.056E−01 | 6.205E−02 | 1.582E−01 | 1.337E−01 | 8.682E−02 | 1.178E−01 | 8.044E−02 | 1.154E−01 | 1.132E−01 |
| 195 | 2.305E−02 | 3.127E−02 | 2.931E−02 | 6.303E−02 | 4.083E−02 | 3.630E−02 | 4.218E−02 | 6.229E−02 | 3.679E−02 | 4.439E−02 | 3.421E−02 | 4.525E−02 | 3.850E−02 |
| 196 | 1.864E−01 | 8.437E−02 | 1.778E−01 | 3.532E−01 | 1.208E−01 | 3.421E−01 | 6.953E−02 | 1.089E−01 | 1.717E−01 | 2.281E−01 | 1.594E−01 | 1.692E−01 | 2.158E−01 |
| 197 | 1.263E−01 | 7.529E−02 | 1.012E−01 | 2.060E−01 | 1.064E−01 | 1.876E−01 | 8.105E−02 | 7.345E−02 | 1.251E−01 | 1.729E−01 | 9.160E−02 | 1.187E−01 | 1.643E−01 |

APPENDIX D-continued

Ovarian Cancer
Training Dataset

| | | | | | | | | | | | | | |
|---|---|---|---|---|---|---|---|---|---|---|---|---|---|
| 198 | 6.107E−02 | 5.236E−02 | 3.679E−02 | 9.086E−02 | 7.357E−02 | 7.137E−02 | 1.101E−01 | 5.677E−02 | 6.303E−02 | 9.749E−02 | 7.063E−02 | 9.001E−02 | 9.430E−02 |
| 199 | 2.195E−02 | 1.133E−01 | 4.083E−02 | 3.605E−02 | 2.318E−01 | 3.262E−02 | 1.937E−01 | 1.827E−01 | 1.324E−01 | 2.097E−01 | 1.422E−01 | 2.256E−01 | 1.496E−01 |
| 200 | 2.036E−02 | 4.034E−02 | 3.740E−02 | 6.131E−02 | 7.922E−02 | 4.010E−02 | 1.398E−01 | 8.363E−02 | 6.818E−02 | 1.162E−01 | 6.585E−02 | 1.028E−01 | 8.547E−02 |
| 201 | 2.784E−02 | 3.188E−02 | 4.145E−02 | 5.727E−02 | 5.763E−02 | 4.194E−02 | 7.946E−02 | 6.315E−02 | 4.488E−02 | 6.511E−02 | 4.280E−02 | 5.518E−02 | 4.733E−02 |
| 202 | 5.359E−04 | 1.263E−02 | 2.869E−03 | 3.274E−03 | 2.722E−02 | 3.127E−03 | 2.146E−02 | 2.600E−02 | 1.239E−02 | 1.704E−02 | 1.239E−02 | 1.937E−02 | 1.337E−02 |
| 203 | 5.359E−04 | 0.000E+00 | 1.729E−03 | 8.179E−04 | 8.007E−04 | 1.251E−03 | 2.477E−03 | 7.897E−04 | 9.540E−04 | 8.302E−04 | 4.280E−04 | 0.000E+00 | 8.387E−04 |
| 204 | 3.752E−03 | 1.204E−02 | 4.022E−03 | 2.452E−03 | 2.085E−02 | 5.015E−03 | 2.477E−02 | 2.293E−02 | 1.717E−02 | 1.582E−02 | 6.413E−03 | 1.741E−02 | 1.337E−02 |
| 205 | 5.359E−04 | 2.403E−03 | 1.150E−03 | 2.452E−03 | 2.403E−03 | 6.266E−04 | 8.277E−04 | 0.000E+00 | 1.913E−03 | 2.072E−03 | 1.288E−03 | 4.709E−04 | 3.348E−03 |
| 206 | 2.146E−03 | 2.293E−02 | 1.150E−03 | 3.274E−03 | 4.083E−02 | 4.390E−03 | 3.470E−02 | 2.685E−02 | 1.386E−02 | 2.330E−02 | 1.459E−02 | 2.784E−02 | 2.477E−02 |
| 207 | 6.965E−03 | 4.819E−03 | 5.751E−03 | 1.717E−02 | 1.040E−02 | 1.570E−02 | 1.484E−02 | 1.815E−02 | 1.002E−02 | 6.634E−03 | 5.996E−03 | 8.952E−03 | 5.028E−03 |
| 208 | 4.280E−03 | 6.021E−04 | 2.305E−03 | 6.548E−03 | 3.200E−03 | 2.502E−03 | 5.788E−03 | 4.733E−03 | 3.335E−03 | 6.229E−03 | 2.563E−03 | 4.243E−03 | 4.611E−03 |
| 209 | 0.000E+00 | 1.204E−03 | 0.000E+00 | 0.000E+00 | 8.007E−04 | 1.876E−03 | 2.477E−03 | 0.000E+00 | 4.770E−04 | 8.302E−04 | 8.559E−04 | 4.709E−04 | 8.387E−04 |
| 210 | 0.000E+00 | 6.021E−04 | 5.751E−04 | 8.179E−04 | 0.000E+00 | 0.000E+00 | 8.277E−04 | 1.582E−03 | 0.000E+00 | 0.000E+00 | 8.559E−04 | 0.000E+00 | 0.000E+00 |
| 211 | 0.000E+00 | 6.021E−04 | 0.000E+00 | 1.631E−03 | 0.000E+00 | 1.251E−03 | 8.277E−04 | 1.582E−03 | 1.435E−03 | 8.302E−04 | 8.559E−04 | 4.709E−04 | 1.263E−03 |
| 212 | 1.071E−03 | 4.218E−03 | 2.305E−03 | 4.096E−03 | 5.604E−03 | 6.266E−03 | 2.477E−03 | 6.315E−03 | 9.540E−04 | 1.655E−03 | 1.288E−03 | 1.888E−03 | 2.514E−03 |
| 213 | 4.280E−03 | 0.000E+00 | 1.729E−03 | 5.727E−03 | 4.807E−03 | 3.765E−03 | 6.622E−03 | 7.897E−04 | 2.857E−03 | 2.072E−03 | 1.717E−03 | 3.299E−03 | 1.680E−03 |
| 214 | 4.280E−03 | 1.803E−03 | 2.869E−03 | 4.096E−03 | 2.403E−03 | 3.127E−03 | 7.443E−03 | 3.151E−03 | 2.391E−0 | 2.906E−03 | 1.288E−03 | 3.299E−03 | 1.680E−03 |
| 215 | 5.359E−04 | 0.000E+00 | 0.000E+00 | 8.179E−04 | 0.000E+00 | 0.000E+00 | 1.655E−03 | 7.897E−04 | 4.770E−04 | 4.145E−04 | 1.288E−03 | 9.430E−04 | 8.387E−04 |
| 216 | 0.000E+00 | 0.000E+00 | 5.751E−04 | 0.000E+00 | 1.606E−03 | 6.266E−04 | 2.477E−03 | 1.582E−03 | 0.000E+00 | 0.000E+00 | 0.000E+00 | 0.000E+00 | 8.387E−04 |
| 217 | 1.071E−03 | 0.000E+00 | 1.729E−03 | 1.631E−03 | 0.000E+00 | 0.000E+00 | 8.277E−04 | 7.897E−04 | 4.770E−04 | 1.655E−03 | 8.559E−04 | 1.410E−03 | 1.263E−03 |
| 218 | 1.178E+00 | 8.939E−01 | 1.315E+00 | 2.661E+00 | 1.910E+00 | 1.058E+00 | 2.577E+00 | 1.605E+00 | 1.867E+00 | 2.351E+00 | 1.509E+00 | 2.205E+00 | 1.815E+00 |
| 219 | 1.124E−02 | 9.638E−03 | 5.751E−03 | 3.029E−02 | 1.766E−02 | 9.393E−03 | 4.218E−02 | 1.974E−02 | 1.913E−02 | 3.446E−02 | 2.183E−02 | 2.735E−02 | 1.631E−02 |
| 220 | 1.279E+00 | 1.694E+00 | 1.321E+00 | 1.620E+00 | 1.608E+00 | 1.519E+00 | 3.818E+00 | 1.647E+00 | 1.801E+00 | 2.102E+00 | 1.794E+00 | 2.715E+00 | 1.661E+00 |
| 221 | 5.663E+01 | 7.255E+01 | 6.644E+01 | 4.402E+01 | 7.576E+01 | 7.035E+01 | 8.640E+01 | 7.627E+01 | 5.337E+01 | 6.207E+01 | 4.809E+01 | 7.064E+01 | 5.202E+01 |
| 222 | 9.174E+01 | 8.492E+01 | 6.060E+01 | 3.408E+01 | 5.147E+01 | 5.194E+01 | 4.119E+01 | 4.183E+01 | 4.096E+01 | 5.171E+01 | 4.525E+01 | 4.652E+01 | 5.004E+01 |
| 223 | 3.049E+01 | 2.738E+01 | 3.105E+01 | 2.255E+01 | 3.529E+01 | 3.460E+01 | 3.766E+01 | 3.182E+01 | 2.314E+01 | 3.042E+01 | 2.228E+01 | 3.026E+01 | 2.444E+01 |
| 224 | 3.052E+01 | 3.316E+01 | 2.564E+01 | 1.789E+01 | 2.130E+01 | 2.724E+01 | 2.739E+01 | 2.847E+01 | 1.988E+01 | 2.313E+01 | 1.862E+01 | 2.240E+01 | 2.100E+01 |
| 225 | 2.483E+01 | 1.817E+01 | 2.503E+01 | 2.203E+01 | 1.880E+01 | 3.134E+01 | 7.715E+00 | 1.376E+01 | 1.700E+01 | 1.343E+01 | 1.586E+01 | 1.428E+01 | 1.191E+01 |
| 226 | 9.843E+00 | 7.639E+00 | 1.303E+01 | 1.277E+01 | 3.584E+00 | 2.665E+01 | 1.360E+00 | 4.665E+00 | 6.399E+00 | 5.318E+00 | 5.782E+00 | 6.209E+00 | 6.434E+00 |
| 227 | 3.339E+00 | 2.807E+00 | 3.618E+00 | 3.657E+00 | 1.529E+00 | 6.669E+00 | 1.102E+00 | 1.588E+00 | 2.186E+00 | 2.041E+00 | 1.943E+00 | 1.860E+00 | 2.151E+00 |
| 228 | 1.858E−01 | 7.759E−01 | 2.461E−01 | 3.271E−01 | 3.150E−01 | 2.213E−01 | 7.204E−01 | 4.476E−01 | 5.578E−01 | 6.332E−01 | 3.849E−01 | 5.943E−01 | 9.122E−01 |
| 229 | 2.102E−01 | 8.305E−01 | 2.830E−01 | 3.556E−01 | 3.549E−01 | 2.861E−01 | 7.262E−01 | 4.627E−01 | 5.597E−01 | 6.186E−01 | 4.472E−01 | 5.998E−01 | 1.035E+00 |
| 230 | 2.664E+01 | 3.390E+01 | 3.879E+01 | 2.571E+01 | 4.170E+01 | 4.131E+01 | 3.004E+01 | 4.945E+01 | 3.001E+01 | 2.757E+01 | 3.104E+01 | 3.633E+01 | 3.174E+01 |
| 231 | 3.153E+00 | 5.510E+00 | 4.189E+00 | 4.193E+00 | 3.758E+00 | 4.418E+00 | 5.009E+00 | 5.731E+00 | 4.208E+00 | 4.269E+00 | 3.936E+00 | 4.766E+00 | 6.635E+00 |
| 232 | 1.352E+00 | 2.069E+00 | 2.168E+00 | 1.642E+00 | 1.546E+00 | 2.286E+00 | 2.150E+00 | 1.901E+00 | 2.090E+00 | 2.655E+00 | 1.814E+00 | 2.063E+00 | 2.560E+00 |
| 233 | 3.151E+00 | 6.832E+00 | 4.664E+00 | 5.333E+00 | 7.597E+00 | 6.268E+00 | 5.050E+00 | 7.382E+00 | 4.940E+00 | 4.534E+00 | 5.621E+00 | 5.868E+00 | 5.749E+00 |
| 234 | 6.410E+00 | 1.493E+01 | 1.617E+01 | 1.936E+01 | 1.926E+01 | 1.882E+01 | 2.644E+01 | 2.480E+01 | 1.763E+01 | 1.780E+01 | 1.935E+01 | 2.193E+01 | 1.664E+01 |
| 235 | 6.687E+00 | 8.014E+00 | 1.256E+01 | 1.036E+01 | 1.340E+01 | 1.057E+01 | 1.649E+01 | 1.356E+01 | 9.696E+00 | 1.030E+01 | 9.174E+00 | 1.135E+01 | 1.274E+01 |
| 236 | 8.373E−01 | 1.166E+00 | 4.018E−01 | 4.815E−01 | 4.838E−01 | 5.898E−01 | 1.316E+00 | 5.819E−01 | 8.667E−01 | 1.794E+00 | 6.659E−01 | 8.781E−01 | 1.423E+00 |
| 237 | 9.431E+00 | 8.165E+00 | 3.434E+00 | 4.678E+00 | 2.154E+00 | 2.588E+00 | 4.253E+00 | 1.906E+00 | 5.784E+00 | 6.467E+00 | 4.983E+00 | 4.430E+00 | 7.479E+00 |
| 238 | 6.206E+00 | 6.614E+00 | 7.622E+00 | 5.991E+00 | 6.109E+00 | 5.487E+00 | 9.853E+00 | 5.238E+00 | 6.555E+00 | 7.250E+00 | 6.231E+00 | 6.936E+00 | 7.160E+00 |
| 239 | 1.099E+00 | 1.269E+00 | 1.635E+00 | 1.237E+00 | 1.225E+00 | 1.248E+00 | 2.177E+00 | 1.239E+00 | 1.438E+00 | 1.579E+00 | 1.284E+00 | 1.472E+00 | 1.622E+00 |
| 240 | 6.358E+00 | 1.667E+01 | 5.240E+00 | 6.460E+00 | 1.529E+01 | 3.127E+00 | 4.653E+01 | 1.884E+01 | 1.606E+01 | 1.947E+01 | 1.591E+01 | 2.316E+01 | 2.048E+01 |
| 241 | 2.283E+02 | 2.377E+02 | 2.117E+02 | 2.027E+02 | 2.254E+02 | 1.753E+02 | 2.315E+02 | 1.833E+02 | 2.116E+02 | 2.216E+02 | 2.261E+02 | 2.240E+02 | 2.330E+02 |
| 242 | 1.148E+02 | 1.079E+02 | 1.415E+02 | 1.661E+02 | 1.816E+02 | 1.411E+02 | 2.190E+02 | 1.470E+02 | 1.657E+02 | 1.692E+02 | 1.522E+02 | 1.751E+02 | 1.508E+02 |
| 243 | 9.737E+00 | 9.198E+00 | 1.322E+01 | 1.646E+01 | 1.735E+01 | 1.354E+01 | 2.176E+01 | 1.376E+01 | 1.727E+01 | 1.732E+01 | 1.460E+01 | 1.759E+01 | 1.533E+01 |
| 244 | 1.629E+01 | 9.768E+00 | 9.717E+00 | 1.670E+01 | 6.077E+00 | 1.245E+01 | 6.175E+00 | 4.525E+00 | 1.220E+01 | 9.082E+00 | 1.062E+01 | 7.320E+00 | 7.607E+00 |
| 245 | 8.488E+00 | 6.732E+00 | 4.691E+00 | 6.342E+00 | 2.850E+00 | 3.951E+00 | 5.019E+00 | 2.529E+00 | 6.098E+00 | 5.508E+00 | 5.345E+00 | 4.457E+00 | 5.435E+00 |
| 246 | 8.930E+00 | 8.936E+00 | 7.339E+00 | 5.914E+00 | 5.345E+00 | 5.192E+00 | 1.245E+01 | 5.616E+00 | 7.832E+00 | 1.002E+01 | 7.193E+00 | 8.495E+00 | 1.067E+01 |
| 247 | 3.757E+00 | 5.688E+00 | 5.147E+00 | 4.663E+00 | 3.852E+00 | 4.942E+00 | 6.901E+00 | 4.032E+00 | 5.249E+00 | 6.627E+00 | 4.421E+00 | 5.343E+00 | 6.419E+00 |

APPENDIX D-continued

Ovarian Cancer
Training Dataset

| | | | | | | | | | | | | | |
|---|---|---|---|---|---|---|---|---|---|---|---|---|---|
| 248 | 9.345E+01 | 6.372E+01 | 8.007E+01 | 1.208E+02 | 7.657E+01 | 8.989E+01 | 4.064E+01 | 5.180E+01 | 8.291E+01 | 7.042E+01 | 7.731E+01 | 6.505E+01 | 6.611E+01 |
| 249 | 8.938E+01 | 5.696E+01 | 5.170E+01 | 8.153E+01 | 5.251E+01 | 4.903E+01 | 5.725E+01 | 4.056E+01 | 7.652E+01 | 7.571E+01 | 6.895E+01 | 6.539E+01 | 6.485E+01 |
| 250 | 1.794E+02 | 1.403E+02 | 1.128E+02 | 1.257E+02 | 9.364E+01 | 4.930E+01 | 1.211E+02 | 9.043E+01 | 1.400E+02 | 1.442E+02 | 1.422E+02 | 1.197E+02 | 1.506E+02 |
| 251 | 5.388E+01 | 4.919E+01 | 3.811E+01 | 4.709E+01 | 4.419E+01 | 3.799E+01 | 7.507E+01 | 4.872E+01 | 6.001E+01 | 6.692E+01 | 5.699E+01 | 5.771E+01 | 5.939E+01 |
| 252 | 2.977E+00 | 3.255E+00 | 2.457E+00 | 3.101E+00 | 3.001E+00 | 2.982E+00 | 5.772E+00 | 3.513E+00 | 4.171E+00 | 4.845E+00 | 3.845E+00 | 4.235E+00 | 4.363E+00 |
| 253 | 5.217E+00 | 4.000E+00 | 3.313E+00 | 6.520E+00 | 2.470E+00 | 6.723E+00 | 3.063E+00 | 2.455E+00 | 4.729E+00 | 3.742E+00 | 4.012E+00 | 3.220E+00 | 4.733E+00 |
| 254 | 1.420E+01 | 8.327E+00 | 1.122E+01 | 1.424E+01 | 5.879E+00 | 1.218E+01 | 5.893E+00 | 4.684E+00 | 9.207E+00 | 6.865E+00 | 8.726E+00 | 5.970E+00 | 7.930E+00 |
| 255 | 1.077E+01 | 7.849E+00 | 9.855E+00 | 1.182E+01 | 5.622E+00 | 1.128E+01 | 6.331E+00 | 4.507E+00 | 9.249E+00 | 7.998E+00 | 8.387E+00 | 6.487E+00 | 6.864E+00 |
| 256 | 2.927E+00 | 3.163E+00 | 3.123E+00 | 3.234E+00 | 2.596E+00 | 2.852E+00 | 4.625E+00 | 2.216E+00 | 4.482E+00 | 4.481E+00 | 3.388E+00 | 4.277E+00 | 3.537E+00 |
| 257 | 3.583E+00 | 6.234E+00 | 5.340E+00 | 4.329E+00 | 5.130E+00 | 5.008E+00 | 7.446E+00 | 5.356E+00 | 5.450E+00 | 6.360E+00 | 4.836E+00 | 6.352E+00 | 6.519E+00 |
| 258 | 2.883E+01 | 1.886E+01 | 2.613E+01 | 4.507E+01 | 1.576E+01 | 3.856E+01 | 1.117E+01 | 1.451E+01 | 3.034E+01 | 2.317E+01 | 2.397E+01 | 2.125E+01 | 3.156E+01 |
| 259 | 5.500E+01 | 3.533E+01 | 4.976E+01 | 7.946E+01 | 3.490E+01 | 5.482E+01 | 2.180E+01 | 2.939E+01 | 5.218E+01 | 3.861E+01 | 4.607E+01 | 3.330E+01 | 3.491E+01 |
| 260 | 2.939E+01 | 2.998E+01 | 3.357E+01 | 4.836E+01 | 3.732E+01 | 3.482E+01 | 2.991E+01 | 3.374E+01 | 4.123E+01 | 3.805E+01 | 4.006E+01 | 3.552E+01 | 2.741E+01 |
| 261 | 2.085E+01 | 3.032E+01 | 3.874E+01 | 2.946E+01 | 3.954E+01 | 4.026E+01 | 3.863E+01 | 4.856E+01 | 3.054E+01 | 3.095E+01 | 3.512E+01 | 3.547E+01 | 3.102E+01 |
| 262 | 9.045E+00 | 1.465E+01 | 9.847E+00 | 8.102E+00 | 1.057E+01 | 1.116E+01 | 1.709E+01 | 1.458E+01 | 1.301E+01 | 1.418E+01 | 1.402E+01 | 1.471E+01 | 1.423E+01 |
| 263 | 4.053E+00 | 2.908E+00 | 3.719E+00 | 4.951E+00 | 1.443E+00 | 6.002E+00 | 1.878E+00 | 1.623E+00 | 3.488E+00 | 2.898E+00 | 2.842E+00 | 2.643E+00 | 3.664E+00 |
| 264 | 3.266E+00 | 2.740E+00 | 3.241E+00 | 3.603E+00 | 2.258E+00 | 3.994E+00 | 3.118E+00 | 2.258E+00 | 4.441E+00 | 3.843E+00 | 3.265E+00 | 4.239E+00 | 4.208E+00 |
| 265 | 2.424E+00 | 2.140E+00 | 2.151E+00 | 2.371E+00 | 1.920E+00 | 2.467E+00 | 3.172E+00 | 1.784E+00 | 3.196E+00 | 3.047E+00 | 2.622E+00 | 2.784E+00 | 2.740E+00 |
| 266 | 8.672E−01 | 2.358E+00 | 1.366E+00 | 8.999E−01 | 2.571E+00 | 1.015E+00 | 5.883E+00 | 2.573E+00 | 2.784E+00 | 3.049E+00 | 2.135E+00 | 3.553E+00 | 2.775E+00 |
| 267 | 8.425E−01 | 2.152E+00 | 2.005E+00 | 1.144E+00 | 2.321E+00 | 1.674E+00 | 5.187E+00 | 2.840E+00 | 2.321E+00 | 2.775E+00 | 1.788E+00 | 3.120E+00 | 2.749E+00 |
| 268 | 1.274E+01 | 8.371E+00 | 1.664E+01 | 2.975E+01 | 4.813E+00 | 2.796E+01 | 3.086E+00 | 6.648E+00 | 1.495E+01 | 1.131E+01 | 1.209E+01 | 9.739E+00 | 1.299E+01 |
| 269 | 6.215E+00 | 6.502E+00 | 7.682E+00 | 1.313E+01 | 6.321E+00 | 1.111E+01 | 5.311E+00 | 6.431E+00 | 1.231E+01 | 1.103E+01 | 9.260E+00 | 1.047E+01 | 1.016E+01 |
| 270 | 2.477E+00 | 2.690E+00 | 2.305E+00 | 3.842E+00 | 3.502E+00 | 2.816E+00 | 4.117E+00 | 3.062E+00 | 5.113E+00 | 5.151E+00 | 4.118E+00 | 4.740E+00 | 4.389E+00 |
| 271 | 1.278E+01 | 1.360E+01 | 1.377E+01 | 1.157E+01 | 1.915E+01 | 1.350E+01 | 1.164E+01 | 1.892E+01 | 1.102E+01 | 1.040E+01 | 1.187E+01 | 1.557E+01 | 1.038E+01 |
| 272 | 7.061E+01 | 8.591E+01 | 1.005E+02 | 7.302E+01 | 1.044E+02 | 9.847E+01 | 7.537E+01 | 1.232E+02 | 7.240E+01 | 6.638E+01 | 7.503E+01 | 8.508E+01 | 7.273E+01 |
| 273 | 7.063E+01 | 9.013E+01 | 1.068E+02 | 7.295E+01 | 1.059E+02 | 1.051E+02 | 7.600E+01 | 1.310E+02 | 7.563E+01 | 6.928E+01 | 7.757E+01 | 8.720E+01 | 7.732E+01 |
| 274 | 1.101E+01 | 1.476E+01 | 1.545E+01 | 1.128E+01 | 1.449E+01 | 1.652E+01 | 1.029E+01 | 2.166E+01 | 1.162E+01 | 1.026E+01 | 1.205E+01 | 1.380E+01 | 1.367E+01 |
| 275 | 5.059E−01 | 8.021E−01 | 7.571E−01 | 5.506E−01 | 1.009E+00 | 5.273E−01 | 6.780E−01 | 9.294E−01 | 5.523E−01 | 5.159E−01 | 4.747E−01 | 8.841E−01 | 6.265E−01 |
| 276 | 3.900E+00 | 7.950E+00 | 9.474E+00 | 9.375E+00 | 1.714E+01 | 1.314E+01 | 7.183E+00 | 1.602E+01 | 6.743E+00 | 6.099E+00 | 9.186E+00 | 9.031E+00 | 6.184E+00 |
| 277 | 8.853E+00 | 2.419E+01 | 2.847E+01 | 2.112E+01 | 3.435E+01 | 3.618E+01 | 1.593E+01 | 4.747E+01 | 1.668E+01 | 1.721E+01 | 2.232E+01 | 1.945E+01 | 1.766E+01 |
| 278 | 8.342E+00 | 2.321E+01 | 2.743E+01 | 2.062E+01 | 3.308E+01 | 3.457E+01 | 1.510E+01 | 4.733E+01 | 1.669E+01 | 1.619E+01 | 2.151E+01 | 1.842E+01 | 1.677E+01 |
| 279 | 2.107E+00 | 5.289E+00 | 5.804E+00 | 7.445E+00 | 6.883E+00 | 8.082E+00 | 8.721E+00 | 1.290E+01 | 6.207E+00 | 5.901E+00 | 7.163E+00 | 7.610E+00 | 5.719E+00 |
| 280 | 3.666E+00 | 6.870E+00 | 4.040E+00 | 4.459E+00 | 7.546E+00 | 4.481E+00 | 1.315E+01 | 7.773E+00 | 5.853E+00 | 6.772E+00 | 6.229E+00 | 7.806E+00 | 6.740E+00 |
| 281 | 1.348E+02 | 1.295E+02 | 1.127E+02 | 1.038E+02 | 1.164E+02 | 9.199E+01 | 1.125E+02 | 9.395E+01 | 1.214E+02 | 1.256E+02 | 1.283E+02 | 1.200E+02 | 1.286E+02 |
| 282 | 1.144E+02 | 1.092E+02 | 9.697E+01 | 8.791E+01 | 9.742E+01 | 7.907E+01 | 9.460E+01 | 8.055E+01 | 1.082E+02 | 1.087E+02 | 1.088E+02 | 1.032E+02 | 1.182E+02 |
| 283 | 2.939E+01 | 2.739E+01 | 4.287E+01 | 5.177E+01 | 5.448E+01 | 4.164E+01 | 6.506E+01 | 4.302E+01 | 5.626E+01 | 5.514E+01 | 4.774E+01 | 5.542E+01 | 4.634E+01 |
| 284 | 5.887E+00 | 9.689E+00 | 6.252E+00 | 5.203E+00 | 4.611E+00 | 6.214E+00 | 6.397E+00 | 5.246E+00 | 5.951E+00 | 8.724E+00 | 5.422E+00 | 6.442E+00 | 7.927E+00 |
| 285 | 1.095E+02 | 9.296E+01 | 6.976E+01 | 7.589E+01 | 6.067E+01 | 6.680E+01 | 6.452E+01 | 6.833E+01 | 8.528E+01 | 8.727E+01 | 8.935E+01 | 7.204E+01 | 8.978E+01 |
| 286 | 8.339E+01 | 7.018E+01 | 5.481E+01 | 5.653E+01 | 4.472E+01 | 5.141E+01 | 4.913E+01 | 5.222E+01 | 6.523E+01 | 6.443E+01 | 6.620E+01 | 5.535E+01 | 6.838E+01 |
| 287 | 8.209E+00 | 7.813E+00 | 6.645E+00 | 8.538E+00 | 7.674E+00 | 6.900E+00 | 1.271E+01 | 8.995E+00 | 1.117E+01 | 1.185E+01 | 1.069E+01 | 1.057E+01 | 1.105E+01 |
| 288 | 3.878E+01 | 5.591E+01 | 7.840E+01 | 6.318E+01 | 7.631E+01 | 8.150E+01 | 5.843E+01 | 9.564E+01 | 5.592E+01 | 5.310E+01 | 6.565E+01 | 6.211E+01 | 5.647E+01 |
| 289 | 3.027E+01 | 4.417E+01 | 6.366E+01 | 4.914E+01 | 5.895E+01 | 6.341E+01 | 4.665E+01 | 7.379E+01 | 4.383E+01 | 4.058E+01 | 5.242E+01 | 5.009E+01 | 4.668E+01 |
| 290 | 1.873E+01 | 2.537E+01 | 2.205E+01 | 1.977E+01 | 1.893E+01 | 2.447E+01 | 1.828E+01 | 2.660E+01 | 1.896E+01 | 1.951E+01 | 2.236E+01 | 2.019E+01 | 2.048E+01 |
| 291 | 1.467E+01 | 1.943E+01 | 1.708E+01 | 1.501E+01 | 1.404E+01 | 1.919E+01 | 1.376E+01 | 2.054E+01 | 1.620E+01 | 1.538E+01 | 1.851E+01 | 1.663E+01 | 1.746E+01 |
| 292 | 1.499E+00 | 2.323E+00 | 1.610E+00 | 1.413E+00 | 1.801E+00 | 1.723E+00 | 3.399E+00 | 2.386E+00 | 2.419E+00 | 2.633E+00 | 2.521E+00 | 2.730E+00 | 2.844E+00 |
| 293 | 3.910E−01 | 1.607E+00 | 8.795E−01 | 4.485E−01 | 2.181E+00 | 6.989E−01 | 3.533E+00 | 2.540E+00 | 1.978E+00 | 2.128E+00 | 1.743E+00 | 2.512E+00 | 1.948E+00 |
| 294 | 2.118E+00 | 1.936E+00 | 1.244E+00 | 1.438E+00 | 1.862E+00 | 9.727E−01 | 3.505E+00 | 1.703E+00 | 2.496E+00 | 2.391E+00 | 2.327E+00 | 2.380E+00 | 2.216E+00 |
| 295 | 2.181E+00 | 1.900E+00 | 1.256E+00 | 1.495E+00 | 1.901E+00 | 9.669E−01 | 3.466E+00 | 1.718E+00 | 2.424E+00 | 2.402E+00 | 2.309E+00 | 2.378E+00 | 2.183E+00 |
| 296 | 9.948E−01 | 9.225E−01 | 8.456E−01 | 1.334E+00 | 1.252E+00 | 7.743E−01 | 2.963E+00 | 9.982E−01 | 1.513E+00 | 1.426E+00 | 1.303E+00 | 1.453E+00 | 1.237E+00 |
| 297 | 3.577E−01 | 4.547E−01 | 5.189E−01 | 7.628E−01 | 6.039E−01 | 5.300E−01 | 8.578E−01 | 8.945E−01 | 1.759E−01 | 1.733E−01 | 2.537E−01 | 2.448E−01 | 2.638E−01 |

APPENDIX D-continued

Ovarian Cancer
Training Dataset

| | | | | | | | | | | | | | |
|---|---|---|---|---|---|---|---|---|---|---|---|---|---|
| 298 | 1.446E−02 | 2.252E−02 | 2.446E−02 | 1.255E−02 | 1.914E−02 | 2.553E−02 | 1.315E−02 | 3.196E−02 | 8.045E−03 | 1.004E−02 | 9.653E−03 | 1.077E−02 | 1.128E−02 |
| 299 | 3.261E−02 | 1.116E−01 | 2.516E−01 | 1.768E−01 | 2.758E−01 | 2.474E−01 | 1.264E−01 | 4.108E−01 | 4.870E−02 | 4.398E−02 | 7.422E−02 | 6.393E−02 | 5.470E−02 |
| 300 | 1.729E−03 | 5.792E−03 | 1.300E−02 | 7.530E−03 | 7.616E−03 | 1.911E−02 | 1.845E−03 | 2.188E−02 | 2.381E−03 | 2.553E−03 | 2.724E−03 | 4.441E−03 | 3.239E−03 |
| 301 | 2.960E−02 | 9.568E−02 | 1.459E−01 | 1.015E−01 | 1.418E−01 | 1.439E−01 | 9.332E−02 | 1.982E−01 | 3.840E−02 | 4.140E−02 | 4.977E−02 | 4.741E−02 | 5.041E−02 |
| 302 | 8.173E−03 | 1.639E−02 | 3.025E−02 | 8.474E−03 | 1.384E−02 | 3.797E−02 | 5.985E−03 | 3.025E−02 | 4.483E−03 | 5.792E−03 | 7.465E−03 | 7.444E−03 | 5.642E−03 |
| 303 | 2.626E−01 | 3.829E−01 | 3.561E−01 | 3.268E−01 | 3.399E−01 | 4.494E−01 | 2.238E−01 | 5.138E−01 | 1.594E−01 | 1.995E−01 | 2.145E−01 | 2.167E−01 | 2.145E−01 |
| 304 | 1.886E−03 | 4.248E−03 | 3.583E−03 | 6.908E−03 | 4.612E−03 | 3.947E−03 | 5.985E−03 | 6.457E−03 | 1.847E−03 | 2.553E−03 | 3.647E−03 | 4.441E−03 | 2.231E−03 |
| 305 | 1.161E−01 | 4.065E−01 | 7.714E−01 | 5.229E−01 | 7.386E−01 | 8.351E−01 | 5.867E−01 | 9.949E−01 | 2.434E−01 | 2.509E−01 | 3.710E−01 | 3.812E−01 | 3.156E−01 |
| 306 | 6.135E−03 | 2.896E−02 | 4.505E−02 | 2.660E−02 | 4.097E−02 | 6.607E−02 | 1.798E−02 | 7.551E−02 | 1.793E−02 | 1.697E−02 | 3.153E−02 | 3.025E−02 | 2.017E−02 |
| 307 | 1.117E+00 | 2.181E+00 | 1.542E+00 | 9.624E−01 | 1.395E+00 | 2.735E+00 | 4.281E−01 | 2.150E+00 | 1.197E+00 | 1.460E+00 | 1.713E+00 | 1.746E+00 | 1.557E+00 |
| 308 | 2.210E−02 | 3.904E−02 | 2.034E−02 | 1.727E−02 | 2.360E−02 | 5.234E−02 | 6.457E−03 | 3.969E−02 | 1.899E−02 | 2.381E−02 | 2.767E−02 | 3.111E−02 | 2.724E−02 |
| 309 | 1.572E−03 | 4.634E−03 | 6.586E−03 | 3.776E−03 | 8.988E−03 | 5.406E−03 | 4.612E−03 | 1.324E−02 | 3.304E−03 | 4.376E−03 | 4.913E−03 | 4.269E−03 | 7.337E−03 |
| 310 | 5.191E−03 | 1.735E−03 | 2.446E−03 | 4.698E−03 | 3.926E−03 | 3.733E−03 | 5.535E−03 | 4.848E−03 | 1.319E−03 | 2.122E−03 | 3.089E−03 | 2.059E−03 | 2.403E−03 |
| 311 | 6.285E−04 | 7.723E−04 | 5.642E−04 | 3.132E−04 | 6.908E−04 | 6.243E−04 | 1.384E−03 | 1.937E−03 | 3.947E−04 | 1.133E−03 | 1.821E−04 | 2.059E−03 | 1.025E−03 |
| 312 | 1.572E−04 | 5.792E−04 | 1.883E−04 | 6.285E−04 | 4.612E−04 | 6.243E−04 | 6.908E−04 | 0.000E+00 | 1.319E−04 | 0.000E+00 | 1.821E−04 | 6.328E−04 | 1.708E−04 |
| 313 | 9.074E−02 | 1.787E−01 | 2.314E−01 | 8.216E−02 | 1.364E−01 | 2.325E−01 | 8.002E−02 | 2.851E−01 | 7.208E−02 | 7.380E−02 | 1.253E−01 | 1.165E−01 | 8.602E−02 |
| 314 | 4.719E−03 | 1.040E−02 | 7.723E−03 | 6.908E−03 | 6.457E−03 | 6.865E−03 | 4.376E−03 | 1.680E−02 | 5.792E−03 | 5.792E−03 | 4.913E−03 | 5.535E−03 | 4.612E−03 |
| 315 | 1.555E−02 | 4.140E−02 | 3.711E−02 | 1.946E−02 | 2.832E−02 | 4.634E−02 | 2.295E−02 | 5.749E−02 | 1.530E−02 | 1.909E−02 | 1.986E−02 | 2.767E−02 | 2.553E−02 |
| 316 | 1.572E−04 | 1.542E−03 | 1.883E−03 | 6.285E−04 | 1.384E−03 | 2.295E−03 | 1.152E−03 | 9.696E−04 | 6.586E−04 | 1.133E−03 | 3.647E−04 | 3.175E−04 | 1.197E−03 |
| 317 | 2.789E−02 | 3.883E−02 | 3.132E−02 | 1.665E−02 | 2.639E−02 | 3.711E−02 | 1.821E−02 | 4.076E−02 | 1.555E−02 | 1.783E−02 | 1.804E−02 | 2.124E−02 | 1.931E−02 |
| 318 | 4.719E−04 | 1.349E−03 | 1.317E−03 | 1.570E−03 | 2.767E−03 | 1.454E−03 | 1.845E−03 | 1.937E−03 | 1.186E−03 | 1.838E−03 | 1.459E−03 | 6.328E−04 | 1.197E−03 |
| 319 | 1.944E−01 | 2.836E−01 | 2.775E−01 | 9.417E−02 | 1.399E−01 | 2.493E−01 | 1.081E−01 | 2.538E−01 | 1.300E−01 | 1.409E−01 | 1.763E−01 | 1.860E−01 | 1.656E−01 |
| 320 | 7.851E−04 | 1.735E−03 | 1.883E−03 | 3.132E−04 | 6.908E−04 | 0.000E+00 | 2.295E−04 | 9.696E−04 | 2.639E−04 | 2.832E−04 | 9.117E−04 | 9.503E−04 | 5.127E−04 |
| 321 | 5.964E−02 | 1.961E−01 | 3.619E−01 | 9.847E−02 | 1.830E−01 | 3.185E−01 | 1.015E−01 | 3.643E−01 | 1.225E−01 | 1.043E−01 | 1.806E−01 | 1.783E−01 | 1.450E−01 |
| 322 | 2.682E−03 | 9.246E−03 | 1.206E−02 | 3.454E−03 | 6.908E−03 | 1.414E−02 | 3.690E−03 | 1.291E−02 | 4.097E−03 | 4.805E−03 | 8.752E−03 | 4.762E−03 | 5.814E−03 |
| 323 | 1.407E−01 | 3.049E−01 | 3.182E−01 | 1.090E−01 | 1.590E−01 | 3.228E−01 | 1.068E−01 | 3.006E−01 | 1.693E−01 | 1.793E−01 | 2.677E−01 | 2.346E−01 | 2.197E−01 |
| 324 | 3.304E−03 | 1.098E−02 | 5.277E−03 | 4.398E−03 | 4.848E−03 | 1.122E−02 | 3.218E−03 | 1.066E−02 | 5.020E−03 | 7.787E−03 | 9.117E−03 | 9.353E−03 | 6.500E−03 |
| 325 | 8.023E−03 | 1.098E−02 | 1.620E−02 | 8.152E−03 | 8.752E−03 | 1.641E−02 | 4.848E−03 | 1.712E−02 | 4.741E−03 | 5.663E−03 | 5.642E−03 | 3.475E−03 | 5.299E−03 |
| 326 | 9.439E−04 | 7.723E−04 | 7.530E−04 | 9.417E−04 | 4.612E−04 | 1.038E−03 | 1.152E−03 | 1.291E−03 | 1.319E−03 | 8.495E−04 | 9.117E−04 | 1.585E−04 | 6.843E−04 |
| 327 | 1.242E−02 | 1.427E−02 | 1.995E−02 | 9.096E−03 | 1.429E−02 | 1.828E−02 | 1.223E−02 | 1.808E−02 | 8.431E−03 | 9.053E−03 | 8.559E−03 | 8.559E−03 | 7.337E−03 |
| 328 | 7.851E−04 | 1.542E−03 | 3.776E−04 | 2.510E−03 | 1.152E−03 | 1.454E−03 | 9.224E−04 | 3.561E−03 | 9.224E−04 | 9.911E−04 | 1.276E−03 | 1.585E−03 | 1.538E−03 |
| 329 | 2.829E−01 | 5.253E−01 | 4.768E−01 | 2.145E−01 | 2.647E−01 | 6.962E−01 | 2.243E−01 | 7.585E−01 | 3.105E−01 | 3.520E−01 | 3.929E−01 | 4.989E−01 | 3.597E−01 |
| 330 | 2.832E−03 | 4.827E−03 | 4.891E−03 | 4.698E−03 | 2.295E−03 | 9.353E−03 | 2.295E−03 | 1.066E−02 | 2.639E−03 | 4.955E−03 | 4.012E−03 | 6.178E−03 | 5.470E−03 |
| 331 | 1.948E−02 | 3.990E−02 | 4.097E−02 | 1.600E−02 | 2.596E−02 | 6.200E−02 | 1.223E−02 | 7.036E−02 | 1.371E−02 | 1.783E−02 | 2.446E−02 | 2.077E−02 | 2.137E−02 |
| 332 | 4.719E−04 | 5.792E−04 | 1.506E−03 | 6.285E−04 | 1.152E−03 | 1.454E−03 | 9.224E−04 | 3.239E−04 | 5.277E−04 | 2.832E−04 | 7.294E−04 | 3.175E−04 | 1.708E−03 |
| 333 | 1.384E−02 | 2.141E−02 | 3.540E−02 | 1.349E−02 | 1.821E−02 | 4.376E−02 | 7.830E−03 | 3.389E−02 | 9.889E−03 | 1.188E−02 | 1.678E−02 | 1.427E−02 | 1.332E−02 |
| 334 | 0.000E+00 | 1.929E−04 | 0.000E+00 | 9.417E−04 | 0.000E+00 | 2.077E−04 | 0.000E+00 | 6.457E−04 | 0.000E+00 | 5.663E−04 | 3.647E−04 | 3.175E−04 | 6.843E−04 |
| 335 | 4.441E−02 | 4.677E−02 | 5.814E−02 | 2.660E−02 | 3.132E−02 | 7.079E−02 | 2.746E−02 | 7.101E−02 | 2.109E−02 | 3.668E−02 | 3.475E−02 | 4.097E−02 | 3.068E−02 |
| 336 | 1.886E−03 | 2.122E−03 | 2.639E−03 | 1.883E−03 | 1.613E−03 | 2.295E−03 | 6.908E−04 | 6.135E−03 | 1.186E−03 | 1.838E−03 | 1.823E−03 | 2.381E−03 | 2.051E−03 |
| 337 | 5.020E−02 | 8.817E−02 | 1.199E−01 | 5.149E−02 | 6.350E−02 | 1.572E−01 | 5.878E−02 | 1.648E−01 | 5.814E−02 | 6.221E−02 | 8.924E−02 | 8.559E−02 | 7.851E−02 |
| 338 | 6.285E−04 | 1.542E−03 | 1.317E−03 | 1.255E−03 | 1.845E−03 | 3.540E−03 | 1.613E−03 | 1.291E−03 | 1.186E−03 | 1.697E−03 | 2.553E−03 | 2.210E−03 | 1.367E−03 |
| 339 | 4.312E−02 | 5.384E−02 | 5.342E−02 | 2.446E−02 | 3.132E−02 | 7.208E−02 | 2.338E−02 | 8.452E−02 | 2.574E−02 | 4.162E−02 | 3.432E−02 | 4.419E−02 | 4.355E−02 |
| 340 | 1.257E−03 | 3.861E−03 | 2.072E−03 | 3.132E−03 | 2.295E−03 | 3.111E−03 | 1.845E−03 | 4.526E−03 | 1.583E−03 | 3.261E−03 | 1.641E−03 | 3.969E−03 | 2.724E−03 |
| 341 | 4.719E−03 | 6.757E−03 | 7.723E−03 | 9.739E−03 | 8.752E−03 | 8.109E−03 | 4.140E−03 | 1.034E−02 | 3.175E−03 | 3.540E−03 | 4.913E−03 | 4.591E−03 | 3.583E−03 |
| 342 | 9.439E−04 | 5.792E−04 | 7.530E−04 | 9.417E−04 | 9.224E−04 | 8.302E−04 | 9.224E−04 | 1.291E−03 | 5.277E−04 | 9.911E−04 | 9.117E−04 | 9.503E−04 | 1.708E−04 |
| 343 | 6.135E−03 | 7.723E−03 | 1.055E−02 | 7.229E−03 | 9.224E−03 | 1.019E−02 | 1.176E−02 | 9.696E−03 | 5.149E−03 | 5.513E−03 | 3.454E−03 | 6.972E−03 | 7.015E−03 |
| 344 | 1.572E−04 | 0.000E+00 | 0.000E+00 | 9.417E−04 | 4.612E−04 | 8.302E−04 | 0.000E+00 | 9.696E−04 | 1.319E−04 | 2.832E−04 | 0.000E+00 | 3.175E−04 | 6.843E−04 |

APPENDIX D-continued

Ovarian Cancer Training Dataset

| | AY | AZ | BA | BB | BC | BD | BE | BF | BG | BH | BI | BJ | BK |
|---|---|---|---|---|---|---|---|---|---|---|---|---|---|
| 1 | CA273 | 14272 | 14246 | 14081 | 14180 | 14453 | 14540 | CA268 | CA262 | CA267 | CA261 | CA264 | CA258 |
| 2 | Control | Late Malignant | Late Malignant | Late Malignant | Late Malignant | Benign | Late Malignant | Control | Control | Control | Control | Control | Control |
| 3 | 0 | 3 | 3 | 3 | 3 | 1 | 3 | 0 | 0 | 0 | 0 | 0 | 0 |
| 4 | 1 | −1 | −1 | −1 | −1 | −1 | −1 | 1 | 1 | 1 | 1 | 1 | 1 |
| 5 | 8.435E−01 | 1.082E+00 | 6.655E+00 | 1.167E+00 | 9.707E−01 | 7.651E−01 | 8.580E−01 | 1.140E+00 | 1.453E+00 | 1.071E+00 | 7.119E−01 | 1.159E+00 | 1.159E+00 |
| 6 | 3.702E−01 | 1.792E−01 | 2.059E+00 | 2.285E−01 | 1.545E−01 | 1.234E−01 | 2.242E−01 | 4.312E−01 | 7.221E−01 | 5.601E−01 | 2.210E−01 | 5.433E−01 | 4.785E−01 |
| 7 | 1.255E−01 | 8.723E−02 | 7.382E−01 | 7.940E−02 | 6.749E−02 | 4.818E−02 | 8.616E−02 | 1.159E−01 | 1.567E−01 | 1.148E−01 | 6.191E−02 | 1.320E−01 | 1.373E−01 |
| 8 | 4.410E−01 | 4.335E−01 | 1.801E+00 | 8.090E−01 | 3.948E−01 | 2.800E−01 | 3.144E−01 | 1.338E+00 | 7.135E−01 | 7.460E−01 | 4.131E−01 | 1.090E+00 | 7.715E−01 |
| 9 | 1.652E−02 | 3.047E−02 | 5.665E−02 | 1.373E−02 | 1.717E−02 | 9.464E−03 | 1.245E−02 | 2.575E−02 | 3.476E−02 | 2.468E−02 | 1.663E−02 | 1.352E−02 | 3.777E−02 |
| 10 | 8.616E−03 | 7.629E−03 | 3.165E−02 | 5.708E−03 | 3.873E−03 | 9.013E−04 | 3.219E−03 | 4.464E−03 | 6.567E−03 | 1.320E−02 | 3.240E−03 | 6.974E−03 | 8.530E−03 |
| 11 | 7.114E−03 | 4.903E−03 | 1.577E−02 | 6.288E−03 | 3.315E−03 | 4.506E−03 | 3.680E−03 | 9.421E−03 | 1.309E−02 | 8.079E−03 | 6.931E−03 | 3.927E−03 | 7.307E−03 |
| 12 | 5.987E−03 | 7.082E−03 | 7.908E−03 | 4.571E−03 | 6.084E−03 | 4.056E−03 | 3.219E−03 | 8.423E−03 | 6.567E−03 | 8.079E−03 | 4.624E−03 | 6.974E−03 | 1.341E−02 |
| 13 | 4.871E−03 | 1.202E−02 | 1.717E−02 | 1.028E−02 | 1.050E−02 | 3.605E−03 | 4.142E−03 | 1.438E−02 | 9.388E−03 | 1.320E−02 | 4.163E−03 | 1.180E−02 | 9.742E−03 |
| 14 | 2.736E−02 | 3.380E−02 | 1.277E−01 | 4.174E−02 | 3.648E−02 | 2.564E−02 | 3.133E−02 | 2.929E−02 | 3.187E−02 | 2.253E−02 | 2.446E−02 | 3.273E−02 | 2.189E−02 |
| 15 | 2.994E−03 | 5.451E−03 | 1.577E−02 | 6.288E−03 | 3.315E−03 | 2.704E−03 | 5.064E−03 | 6.438E−03 | 6.567E−03 | 2.972E−03 | 3.702E−03 | 3.487E−03 | 6.094E−03 |
| 16 | 7.489E−04 | 5.451E−04 | 1.320E−03 | 1.137E−03 | 1.105E−03 | 2.253E−03 | 3.219E−03 | 2.479E−03 | 9.388E−04 | 4.249E−04 | 9.249E−04 | 2.178E−03 | 0.000E+00 |
| 17 | 2.242E−03 | 1.094E−03 | 1.320E−03 | 1.717E−03 | 2.210E−03 | 1.352E−03 | 4.603E−03 | 2.479E−03 | 6.567E−03 | 2.554E−03 | 2.307E−03 | 1.309E−03 | 3.659E−03 |
| 18 | 2.393E−02 | 2.940E−02 | 6.459E−02 | 1.996E−02 | 2.103E−02 | 2.167E−02 | 1.663E−02 | 1.835E−02 | 2.060E−02 | 2.082E−02 | 3.144E−02 | 3.315E−02 | 9.742E−03 |
| 19 | 4.002E−02 | 6.212E−02 | 6.695E−01 | 4.742E−02 | 4.753E−02 | 4.957E−02 | 4.281E−02 | 4.614E−02 | 5.536E−02 | 4.378E−02 | 4.067E−02 | 5.054E−02 | 3.659E−02 |
| 20 | 3.745E−04 | 5.451E−04 | 2.639E−03 | 1.717E−03 | 5.526E−04 | 2.704E−03 | 2.768E−03 | 1.985E−03 | 1.878E−03 | 2.972E−03 | 4.624E−04 | 2.178E−03 | 1.223E−03 |
| 21 | 1.202E−02 | 3.809E−03 | 4.088E−02 | 7.425E−03 | 4.421E−03 | 5.858E−03 | 3.219E−03 | 1.384E−02 | 1.599E−02 | 1.534E−02 | 6.931E−03 | 1.695E−02 | 6.094E−03 |
| 22 | 1.867E−03 | 1.094E−03 | 1.320E−02 | 0.000E+00 | 0.000E+00 | 9.013E−04 | 4.603E−04 | 2.479E−03 | 2.811E−03 | 1.277E−03 | 2.307E−03 | 3.927E−03 | 3.659E−03 |
| 23 | 2.661E−02 | 2.285E−02 | 1.015E−01 | 2.167E−02 | 1.878E−02 | 2.393E−02 | 2.629E−02 | 2.532E−02 | 3.562E−02 | 2.425E−02 | 1.942E−02 | 2.704E−02 | 1.459E−02 |
| 24 | 4.828E−02 | 5.998E−02 | 1.824E−01 | 4.914E−02 | 5.966E−02 | 5.268E−02 | 4.700E−02 | 5.150E−02 | 2.350E−02 | 4.292E−02 | 4.764E−02 | 4.313E−02 | 3.777E−02 |
| 25 | 1.727E−02 | 5.451E−03 | 4.742E−02 | 9.710E−03 | 2.210E−03 | 1.395E−02 | 1.202E−02 | 1.191E−02 | 1.032E−02 | 1.620E−02 | 8.788E−03 | 1.878E−02 | 7.307E−03 |
| 26 | 8.616E−03 | 1.255E−02 | 6.202E−02 | 1.770E−02 | 9.399E−03 | 5.408E−03 | 8.294E−03 | 7.436E−03 | 1.406E−02 | 8.927E−03 | 9.249E−03 | 1.223E−02 | 1.459E−02 |
| 27 | 3.369E−03 | 2.178E−03 | 1.845E−02 | 2.285E−03 | 2.210E−03 | 2.704E−03 | 4.142E−03 | 1.491E−03 | 5.633E−03 | 2.972E−03 | 9.249E−04 | 3.047E−03 | 1.223E−03 |
| 28 | 2.736E−02 | 1.470E−02 | 7.253E−02 | 1.481E−02 | 2.264E−02 | 2.167E−02 | 9.667E−03 | 3.122E−02 | 3.283E−02 | 2.511E−02 | 1.620E−02 | 2.049E−02 | 1.588E−02 |
| 29 | 3.970E−02 | 1.524E−02 | 6.856E−02 | 2.060E−02 | 1.824E−02 | 2.393E−02 | 1.427E−02 | 2.876E−02 | 5.633E−02 | 4.936E−02 | 2.307E−02 | 3.745E−02 | 2.554E−02 |
| 30 | 6.406E−02 | 8.938E−02 | 1.159E−01 | 6.803E−02 | 8.959E−02 | 7.521E−02 | 7.135E−02 | 6.985E−02 | 4.131E−02 | 5.912E−02 | 6.888E−02 | 6.674E−02 | 5.118E−02 |
| 31 | 4.045E−02 | 5.880E−02 | 7.382E−02 | 6.116E−02 | 5.526E−02 | 8.648E−02 | 7.597E−02 | 7.189E−02 | 3.004E−02 | 3.144E−02 | 4.485E−02 | 3.659E−02 | 2.918E−02 |
| 32 | 1.910E−02 | 2.393E−02 | 1.094E−01 | 5.998E−02 | 2.264E−02 | 2.339E−02 | 1.567E−02 | 6.985E−02 | 2.157E−02 | 2.339E−02 | 2.865E−02 | 5.408E−02 | 1.706E−02 |
| 33 | 1.159E−02 | 7.629E−03 | 1.577E−02 | 9.142E−03 | 1.105E−02 | 1.266E−02 | 1.013E−02 | 1.384E−02 | 5.633E−03 | 8.079E−03 | 9.249E−03 | 6.974E−03 | 6.094E−03 |
| 34 | 1.341E−01 | 2.371E−01 | 9.321E−01 | 3.036E−01 | 2.403E−01 | 1.567E−01 | 1.878E−01 | 1.652E−01 | 1.330E−01 | 1.470E−01 | 2.006E−01 | 1.974E−01 | 1.024E−01 |
| 35 | 5.762E−02 | 8.605E−02 | 9.227E−02 | 9.024E−02 | 5.751E−02 | 1.491E−01 | 1.069E−01 | 8.079E−02 | 4.979E−02 | 4.421E−02 | 8.734E−02 | 5.279E−02 | 5.730E−02 |
| 36 | 5.987E−03 | 3.273E−03 | 1.055E−02 | 7.425E−03 | 8.294E−03 | 9.464E−03 | 8.294E−03 | 7.929E−03 | 7.511E−03 | 5.526E−03 | 8.326E−03 | 7.414E−03 | 2.436E−03 |
| 37 | 1.685E−02 | 1.035E−02 | 4.088E−02 | 1.427E−02 | 1.266E−02 | 9.464E−03 | 8.755E−03 | 7.929E−03 | 1.502E−02 | 1.191E−02 | 1.063E−02 | 1.309E−02 | 2.800E−02 |
| 38 | 9.732E−03 | 1.255E−02 | 4.742E−02 | 1.309E−02 | 1.717E−02 | 1.309E−02 | 6.910E−03 | 1.588E−02 | 1.406E−02 | 6.384E−03 | 1.341E−02 | 9.592E−03 | 9.742E−03 |
| 39 | 1.234E−01 | 3.755E−02 | 1.320E−01 | 3.487E−02 | 4.421E−02 | 5.590E−02 | 8.519E−02 | 5.944E−02 | 1.052E−01 | 6.298E−02 | 1.330E−01 | 8.766E−02 | 8.283E−02 |
| 40 | 1.931E−01 | 1.652E−01 | 2.361E−01 | 1.384E−01 | 1.685E−01 | 1.234E−01 | 1.277E−01 | 1.046E−01 | 1.191E−01 | 1.309E−01 | 1.094E−01 | 1.008E−01 | 8.895E−02 |
| 41 | 1.910E−02 | 2.886E−02 | 5.408E−02 | 2.511E−02 | 2.049E−02 | 2.843E−02 | 1.567E−02 | 2.532E−02 | 1.599E−02 | 1.910E−02 | 1.899E−02 | 2.178E−02 | 2.189E−02 |
| 42 | 0.000E+00 | 2.725E−03 | 6.588E−03 | 1.717E−03 | 1.105E−03 | 9.013E−04 | 4.603E−04 | 1.985E−03 | 9.388E−04 | 8.509E−04 | 0.000E+00 | 3.047E−03 | 0.000E+00 |
| 43 | 3.061E−03 | 5.607E−03 | 1.739E−02 | 3.138E−03 | 4.372E−03 | 3.446E−03 | 3.421E−03 | 9.388E−03 | 4.501E−03 | 3.061E−03 | 6.327E−03 | 5.118E−03 | 5.838E−03 |
| 44 | 9.233E−02 | 1.435E−01 | 1.528E+00 | 1.399E−01 | 1.668E−01 | 1.178E−01 | 1.142E−01 | 1.265E−01 | 1.517E−01 | 1.098E−01 | 4.916E−01 | 2.006E−01 | 1.114E−01 |
| 45 | 4.681E−02 | 3.241E−02 | 3.906E−01 | 3.318E−02 | 3.729E−02 | 3.781E−02 | 3.575E−02 | 6.273E−02 | 7.330E−02 | 6.507E−02 | 5.221E−02 | 8.999E−02 | 4.912E−02 |
| 46 | 5.144E−02 | 6.764E−02 | 3.154E−01 | 5.607E−02 | 5.633E−02 | 4.707E−02 | 5.967E−02 | 1.051E−01 | 5.067E−02 | 6.687E−02 | 1.078E−01 | 8.873E−02 | 8.256E−02 |
| 47 | 5.350E−02 | 6.430E−02 | 6.494E−01 | 6.250E−02 | 7.201E−02 | 4.990E−02 | 4.732E−02 | 7.164E−02 | 7.973E−02 | 6.198E−02 | 6.198E−02 | 1.265E−01 | 5.890E−02 |

APPENDIX D-continued

Ovarian Cancer
Training Dataset

| | | | | | | | | | | | | | |
|---|---|---|---|---|---|---|---|---|---|---|---|---|---|
| 48 | 9.336E−03 | 7.973E−03 | 1.227E−01 | 5.478E−03 | 6.636E−03 | 6.481E−03 | 7.947E−03 | 9.619E−03 | 1.057E−02 | 6.018E−03 | 1.186E−02 | 1.569E−02 | 1.052E−02 |
| 49 | 3.498E−03 | 3.138E−03 | 3.961E−02 | 3.292E−03 | 1.854E−03 | 3.241E−03 | 4.527E−03 | 4.398E−03 | 5.170E−03 | 4.578E−03 | 5.658E−03 | 5.864E−03 | 7.304E−03 |
| 50 | 1.795E−03 | 1.960E−03 | 1.358E−02 | 2.191E−03 | 6.636E−04 | 1.080E−03 | 9.928E−04 | 2.137E−03 | 2.024E−03 | 1.325E−03 | 2.217E−03 | 2.194E−03 | 2.045E−03 |
| 51 | 1.165E−01 | 1.597E−01 | 1.273E−01 | 1.430E−01 | 1.792E−01 | 2.233E−01 | 1.191E−01 | 1.743E−01 | 1.384E−01 | 1.049E−01 | 2.030E−01 | 1.705E−01 | 1.860E−01 |
| 52 | 2.243E−03 | 2.220E−03 | 1.896E−03 | 9.593E−04 | 2.778E−03 | 2.268E−03 | 1.546E−03 | 4.038E−03 | 1.800E−03 | 1.427E−03 | 2.778E−03 | 2.829E−03 | 3.806E−03 |
| 53 | 2.379E−02 | 3.086E−02 | 1.003E−01 | 3.472E−02 | 3.086E−02 | 2.528E−02 | 2.906E−02 | 1.687E−02 | 1.934E−02 | 2.425E−02 | 2.778E−02 | 2.467E−02 | 1.517E−02 |
| 54 | 6.509E+00 | 4.957E+00 | 3.283E+00 | 4.823E+00 | 5.040E+00 | 5.323E+00 | 5.483E+00 | 4.706E+00 | 5.886E+00 | 6.704E+00 | 4.456E+00 | 5.478E+00 | 4.109E+00 |
| 55 | 6.593E−01 | 7.976E−01 | 5.850E−01 | 7.161E−01 | 7.495E−01 | 7.341E−01 | 7.303E−01 | 5.638E−01 | 4.721E−01 | 5.739E−01 | 6.154E−01 | 6.189E−01 | 5.582E−01 |
| 56 | 2.001E−01 | 1.767E−01 | 1.240E−01 | 1.834E−01 | 1.982E−01 | 1.804E−01 | 2.031E−01 | 1.753E−01 | 1.901E−01 | 2.308E−01 | 1.572E−01 | 2.052E−01 | 1.322E−01 |
| 57 | 4.256E+00 | 5.318E+00 | 3.768E+00 | 4.497E+00 | 4.872E+00 | 4.622E+00 | 4.874E+00 | 3.152E+00 | 2.781E+00 | 3.499E+00 | 3.820E+00 | 3.674E+00 | 3.570E+00 |
| 58 | 2.958E−02 | 4.527E−02 | 3.292E−02 | 3.189E−02 | 3.601E−02 | 3.163E−02 | 3.961E−02 | 4.835E−02 | 2.726E−02 | 3.112E−02 | 6.713E−02 | 3.626E−02 | 4.604E−02 |
| 59 | 7.947E−02 | 8.719E−02 | 9.285E−02 | 8.719E−02 | 8.102E−02 | 8.667E−02 | 8.719E−02 | 6.178E−02 | 4.810E−02 | 6.533E−02 | 6.816E−02 | 6.944E−02 | 4.578E−02 |
| 60 | 1.042E−02 | 1.803E−02 | 4.424E−02 | 1.507E−02 | 1.656E−02 | 1.350E−02 | 1.237E−02 | 1.165E−02 | 1.530E−02 | 1.183E−02 | 1.661E−02 | 1.546E−02 | 9.336E−03 |
| 61 | 1.093E+00 | 2.170E+00 | 2.036E+00 | 1.813E+00 | 1.184E+00 | 1.549E+00 | 2.565E+00 | 9.870E−01 | 1.031E+00 | 9.005E−01 | 2.386E+00 | 1.120E+00 | 1.196E+00 |
| 62 | 5.712E−01 | 2.018E−01 | 2.377E−01 | 2.658E−01 | 3.616E−01 | 3.795E−01 | 2.486E−01 | 5.510E−01 | 7.110E−01 | 5.732E−01 | 3.279E−01 | 4.753E−01 | 4.476E−01 |
| 63 | 9.413E−03 | 1.227E−02 | 1.800E−02 | 1.137E−02 | 7.562E−03 | 8.976E−03 | 1.589E−02 | 9.619E−03 | 7.870E−03 | 8.462E−03 | 1.708E−02 | 1.013E−02 | 7.587E−03 |
| 64 | 3.638E+00 | 1.858E+00 | 1.322E+00 | 2.348E+00 | 3.695E+00 | 3.644E+00 | 2.366E+00 | 3.532E+00 | 3.528E+00 | 4.530E+00 | 2.955E+00 | 4.441E+00 | 2.368E+00 |
| 65 | 1.247E−01 | 6.198E−02 | 6.687E−02 | 8.745E−02 | 1.196E−01 | 1.134E−01 | 7.870E−02 | 1.338E−01 | 1.265E−01 | 1.520E−01 | 1.101E−01 | 1.538E−01 | 9.156E−02 |
| 66 | 7.377E−01 | 5.231E−01 | 3.410E−01 | 4.980E−01 | 7.863E−01 | 7.795E−01 | 4.679E−01 | 7.963E−01 | 6.768E−01 | 7.203E−01 | 7.716E−01 | 8.060E−01 | 7.159E−01 |
| 67 | 3.112E−02 | 4.167E−02 | 4.655E−02 | 4.192E−02 | 4.295E−02 | 4.141E−02 | 3.524E−02 | 7.793E−02 | 4.552E−02 | 4.707E−02 | 6.404E−02 | 5.298E−02 | 5.170E−02 |
| 68 | 2.829E−02 | 3.987E−02 | 2.215E−01 | 6.096E−02 | 5.967E−02 | 4.141E−02 | 3.704E−02 | 5.156E−02 | 5.298E−02 | 3.909E−02 | 4.732E−02 | 6.018E−02 | 3.524E−02 |
| 69 | 5.179E−01 | 7.724E−01 | 7.449E−01 | 7.332E−01 | 6.486E−01 | 8.769E−01 | 9.529E−01 | 5.761E−01 | 5.356E−01 | 4.448E−01 | 1.201E+00 | 6.079E−01 | 5.676E−01 |
| 70 | 2.307E−02 | 3.009E−02 | 4.321E−02 | 3.061E−02 | 2.855E−02 | 3.446E−02 | 3.446E−02 | 3.035E−02 | 2.317E−02 | 2.366E−02 | 3.575E−02 | 2.906E−02 | 2.881E−02 |
| 71 | 4.655E−03 | 6.147E−03 | 1.739E−02 | 6.584E−03 | 8.205E−03 | 5.735E−03 | 6.841E−03 | 8.205E−03 | 8.102E−03 | 4.990E−03 | 9.310E−03 | 5.118E−03 | 4.964E−03 |
| 72 | 2.243E−03 | 2.881E−03 | 5.993E−03 | 2.598E−03 | 1.988E−03 | 3.035E−03 | 2.983E−03 | 3.678E−03 | 6.739E−04 | 3.163E−03 | 2.649E−03 | 3.755E−03 | 1.461E−03 |
| 73 | 3.939E−04 | 1.716E−03 | 1.388E−03 | 3.002E−03 | 5.813E−04 | 4.740E−04 | 1.456E−03 | 0.000E+00 | 9.876E−04 | 8.950E−04 | 1.456E−03 | 4.582E−04 | 0.000E+00 |
| 74 | 1.580E−03 | 4.582E−03 | 6.930E−03 | 3.600E−03 | 4.650E−03 | 2.844E−03 | 1.941E−03 | 2.088E−03 | 5.926E−03 | 1.795E−03 | 9.729E−04 | 9.176E−04 | 6.411E−03 |
| 75 | 3.352E−02 | 3.330E−02 | 6.524E−02 | 4.865E−02 | 2.844E−02 | 7.675E−02 | 8.871E−02 | 5.790E−02 | 3.555E−02 | 1.919E−02 | 3.262E−02 | 2.889E−02 | 4.233E−02 |
| 76 | 5.237E−02 | 6.185E−02 | 9.289E−02 | 9.853E−02 | 5.406E−02 | 1.253E−01 | 1.377E−01 | 8.916E−02 | 2.562E−02 | 2.506E−02 | 4.233E−02 | 2.935E−02 | 5.000E−02 |
| 77 | 4.729E−03 | 3.442E−03 | 1.524E−02 | 8.409E−03 | 3.488E−03 | 6.637E−03 | 1.114E−02 | 4.695E−03 | 2.957E−03 | 2.235E−03 | 5.350E−03 | 3.205E−03 | 1.287E−03 |
| 78 | 3.939E−04 | 5.734E−04 | 0.000E+00 | 0.000E+00 | 0.000E+00 | 1.422E−03 | 4.842E−04 | 0.000E+00 | 0.000E+00 | 8.950E−04 | 0.000E+00 | 0.000E+00 | 0.000E+00 |
| 79 | 3.939E−04 | 0.000E+00 | 4.165E−03 | 1.196E−03 | 4.074E−03 | 1.896E−03 | 9.684E−04 | 3.126E−03 | 0.000E+00 | 2.235E−03 | 0.000E+00 | 9.176E−04 | 1.287E−03 |
| 80 | 3.939E−04 | 2.291E−03 | 2.777E−03 | 1.196E−03 | 2.325E−03 | 4.740E−04 | 1.456E−03 | 2.088E−03 | 2.957E−03 | 4.470E−04 | 1.456E−03 | 2.291E−03 | 2.562E−03 |
| 81 | 3.149E−03 | 5.158E−03 | 0.000E+00 | 9.018E−03 | 9.887E−03 | 5.688E−03 | 9.210E−03 | 5.214E−03 | 4.932E−03 | 5.372E−03 | 7.777E−03 | 4.582E−03 | 1.151E−02 |
| 82 | 1.580E−03 | 5.158E−03 | 0.000E+00 | 1.806E−03 | 3.488E−03 | 2.370E−03 | 5.327E−03 | 4.176E−03 | 1.975E−03 | 1.795E−03 | 2.427E−03 | 2.291E−03 | 0.000E+00 |
| 83 | 2.754E−03 | 2.291E−03 | 6.930E−03 | 1.196E−03 | 2.912E−03 | 1.422E−03 | 9.684E−04 | 1.043E−03 | 1.975E−03 | 1.343E−03 | 1.941E−03 | 1.840E−03 | 2.562E−03 |
| 84 | 8.273E−03 | 8.600E−03 | 4.165E−03 | 1.321E−02 | 8.725E−03 | 1.043E−02 | 7.269E−03 | 1.253E−02 | 6.907E−03 | 7.607E−03 | 1.119E−02 | 4.582E−03 | 1.025E−02 |
| 85 | 2.754E−03 | 4.007E−03 | 2.777E−03 | 3.600E−03 | 1.163E−03 | 6.163E−03 | 9.684E−04 | 1.569E−03 | 2.957E−03 | 2.686E−03 | 4.865E−04 | 1.377E−03 | 2.562E−03 |
| 86 | 4.729E−03 | 3.442E−03 | 5.542E−03 | 8.409E−03 | 1.456E−02 | 1.377E−02 | 9.684E−03 | 1.456E−02 | 4.932E−03 | 1.795E−03 | 4.865E−03 | 4.582E−03 | 1.025E−02 |
| 87 | 2.122E−02 | 1.840E−02 | 1.659E−02 | 3.781E−02 | 2.438E−02 | 7.968E−02 | 6.343E−02 | 5.113E−02 | 1.377E−02 | 6.716E−03 | 1.704E−02 | 8.713E−03 | 2.054E−02 |
| 88 | 5.508E−03 | 5.734E−03 | 0.000E+00 | 7.212E−03 | 7.562E−03 | 6.637E−03 | 1.017E−02 | 8.341E−03 | 9.876E−04 | 2.686E−03 | 3.409E−03 | 2.754E−03 | 3.849E−03 |
| 89 | 6.693E−03 | 1.321E−02 | 6.930E−03 | 7.810E−03 | 7.562E−03 | 2.562E−02 | 1.309E−02 | 1.411E−02 | 1.377E−02 | 6.264E−03 | 1.070E−02 | 4.582E−03 | 2.562E−03 |
| 90 | 2.088E−02 | 2.585E−02 | 1.253E−02 | 4.029E−02 | 2.968E−02 | 1.000E−01 | 7.077E−02 | 5.632E−02 | 8.883E−03 | 8.499E−03 | 2.088E−02 | 1.242E−02 | 3.465E−02 |
| 91 | 4.729E−03 | 6.874E−03 | 2.777E−03 | 6.005E−03 | 2.325E−03 | 1.043E−02 | 1.208E−02 | 6.253E−03 | 2.957E−03 | 1.343E−03 | 7.777E−03 | 3.205E−03 | 5.124E−03 |
| 92 | 7.483E−03 | 1.208E−02 | 4.165E−03 | 9.018E−03 | 1.163E−02 | 2.133E−02 | 1.648E−02 | 1.043E−02 | 3.950E−03 | 7.156E−03 | 9.244E−03 | 5.959E−03 | 1.151E−02 |
| 93 | 4.729E−03 | 6.309E−03 | 5.542E−03 | 6.614E−03 | 6.400E−03 | 1.806E−02 | 9.684E−03 | 1.196E−02 | 3.950E−03 | 2.235E−03 | 4.379E−03 | 6.422E−03 | 8.973E−03 |
| 94 | 7.878E−04 | 1.716E−03 | 0.000E+00 | 1.806E−03 | 1.749E−03 | 3.318E−03 | 4.842E−04 | 5.214E−04 | 9.876E−04 | 1.795E−03 | 4.865E−04 | 4.131E−03 | 1.287E−03 |
| 95 | 4.334E−03 | 6.874E−03 | 6.930E−03 | 1.377E−02 | 8.138E−03 | 1.422E−02 | 1.885E−02 | 1.043E−02 | 2.957E−03 | 1.343E−03 | 6.806E−03 | 6.885E−03 | 5.124E−03 |
| 96 | 3.544E−03 | 5.734E−03 | 2.777E−03 | 6.614E−03 | 4.650E−03 | 1.140E−02 | 1.546E−02 | 7.302E−03 | 5.926E−03 | 1.795E−03 | 2.427E−03 | 4.131E−03 | 3.849E−03 |
| 97 | 3.544E−03 | 3.442E−03 | 0.000E+00 | 6.614E−03 | 6.975E−03 | 1.185E−02 | 4.357E−03 | 9.910E−03 | 1.975E−03 | 4.470E−03 | 3.894E−03 | 2.754E−03 | 8.973E−03 |

APPENDIX D-continued

| Ovarian Cancer Training Dataset | | | | | | | | | | | | | |
|---|---|---|---|---|---|---|---|---|---|---|---|---|---|
| 98 | 6.298E−03 | 6.309E−03 | 0.000E+00 | 8.409E−03 | 1.163E−02 | 1.512E−02 | 1.163E−02 | 8.341E−03 | 4.932E−03 | 3.578E−03 | 4.865E−03 | 2.754E−03 | 1.287E−02 |
| 99 | 1.410E−01 | 5.604E−02 | 1.115E−01 | 1.025E−01 | 3.728E−02 | 6.695E−02 | 6.315E−02 | 9.577E−02 | 8.363E−02 | 9.479E−02 | 5.972E−02 | 8.069E−02 | 1.337E−01 |
| 100 | 2.440E−02 | 3.176E−02 | 5.874E−02 | 2.808E−02 | 2.784E−02 | 2.158E−02 | 1.901E−02 | 3.850E−02 | 2.256E−02 | 2.771E−02 | 2.060E−02 | 2.048E−02 | 2.367E−02 |
| 101 | 1.078E−01 | 1.288E−01 | 3.421E−01 | 1.533E−01 | 1.680E−01 | 1.741E−01 | 1.324E−01 | 1.122E−01 | 1.471E−01 | 1.570E−01 | 1.142E−01 | 1.300E−01 | 1.100E−01 |
| 102 | 4.034E−01 | 6.683E−01 | 1.987E−01 | 7.321E−01 | 6.090E−01 | 5.445E−01 | 5.530E−01 | 6.548E−01 | 3.630E−01 | 4.782E−01 | 5.273E−01 | 3.847E−01 | 4.132E−01 |
| 103 | 1.582E−01 | 1.999E−01 | 6.082E−01 | 2.232E−01 | 2.367E−01 | 1.631E−01 | 1.974E−01 | 1.386E−01 | 1.545E−01 | 1.521E−01 | 1.115E−01 | 1.361E−01 | 1.349E−01 |
| 104 | 2.281E−01 | 2.624E−01 | 1.570E−01 | 2.992E−01 | 2.293E−01 | 2.158E−01 | 1.937E−01 | 3.144E−01 | 1.717E−01 | 2.219E−01 | 2.195E−01 | 1.876E−01 | 1.447E−01 |
| 105 | 5.984E−01 | 8.682E−01 | 2.968E−01 | 9.501E−01 | 1.076E+00 | 8.199E−01 | 7.357E−01 | 7.273E−01 | 5.567E−01 | 5.690E−01 | 7.703E−01 | 5.167E−01 | 5.113E−01 |
| 106 | 1.582E−01 | 1.312E−01 | 2.379E−01 | 1.950E−01 | 1.004E−01 | 1.091E−01 | 1.194E−01 | 1.778E−01 | 1.263E−01 | 1.361E−01 | 1.288E−01 | 1.082E−01 | 1.030E−01 |
| 107 | 1.181E−01 | 8.216E−02 | 1.692E−01 | 1.545E−01 | 9.160E−02 | 6.953E−02 | 1.158E−01 | 1.337E−01 | 8.044E−02 | 1.151E−01 | 8.829E−02 | 1.046E−01 | 8.486E−02 |
| 108 | 1.790E−01 | 1.349E−01 | 3.041E−01 | 1.987E−01 | 1.766E−01 | 1.901E−01 | 1.533E−01 | 1.496E−01 | 1.790E−01 | 1.337E−01 | 1.704E−01 | 1.459E−01 | 1.790E−01 |
| 109 | 7.701E−03 | 1.373E−02 | 6.021E−03 | 5.874E−03 | 7.578E−03 | 3.605E−03 | 5.261E−03 | 7.357E−03 | 3.213E−03 | 5.837E−03 | 8.449E−03 | 7.480E−03 | 2.784E−03 |
| 110 | 3.507E−02 | 2.808E−02 | 5.579E−02 | 3.397E−02 | 3.544E−02 | 3.556E−02 | 3.421E−02 | 2.600E−02 | 2.894E−02 | 2.379E−02 | 3.323E−02 | 4.537E−02 | 2.367E−02 |
| 111 | 2.992E−02 | 2.121E−02 | 4.071E−02 | 1.888E−02 | 2.587E−02 | 2.673E−02 | 1.901E−02 | 2.600E−02 | 2.146E−02 | 2.428E−02 | 1.790E−02 | 2.293E−02 | 1.251E−02 |
| 112 | 1.410E−02 | 7.468E−03 | 3.164E−02 | 1.175E−02 | 1.200E−02 | 1.239E−02 | 9.479E−03 | 1.754E−02 | 1.288E−02 | 1.508E−02 | 2.011E−02 | 1.300E−02 | 1.668E−02 |
| 113 | 3.421E−03 | 3.115E−03 | 1.205E−02 | 4.574E−03 | 2.526E−03 | 7.210E−03 | 2.109E−03 | 6.229E−03 | 3.213E−03 | 3.887E−03 | 6.867E−03 | 6.475E−03 | 4.181E−03 |
| 114 | 4.709E−03 | 3.740E−03 | 6.021E−03 | 9.135E−03 | 8.841E−03 | 7.210E−03 | 1.052E−02 | 1.133E−02 | 2.146E−03 | 8.743E−03 | 1.110E−02 | 4.979E−03 | 5.567E−03 |
| 115 | 9.847E−03 | 8.719E−03 | 3.470E−02 | 8.486E−03 | 1.582E−02 | 1.133E−02 | 1.373E−02 | 1.251E−02 | 1.073E−02 | 6.315E−03 | 1.533E−02 | 1.046E−02 | 1.950E−02 |
| 116 | 8.130E−03 | 5.604E−03 | 1.508E−02 | 5.224E−03 | 2.526E−03 | 3.090E−03 | 4.206E−03 | 2.833E−03 | 8.584E−03 | 7.296E−03 | 8.449E−03 | 4.488E−03 | 4.181E−03 |
| 117 | 1.888E−02 | 7.468E−03 | 3.311E−02 | 6.524E−03 | 1.010E−02 | 5.665E−03 | 1.001E−02 | 9.062E−03 | 7.505E−03 | 7.774E−03 | 9.516E−03 | 5.984E−03 | 8.351E−03 |
| 118 | 5.138E−03 | 9.969E−03 | 7.529E−03 | 5.874E−03 | 3.789E−03 | 5.665E−03 | 3.164E−03 | 6.793E−03 | 4.292E−03 | 5.346E−03 | 5.285E−03 | 5.984E−03 | 2.784E−03 |
| 119 | 4.280E−03 | 6.855E−03 | 2.416E−02 | 8.486E−03 | 1.447E−02 | 8.755E−03 | 7.897E−03 | 1.864E−02 | 4.292E−03 | 5.346E−03 | 6.340E−03 | 1.096E−02 | 6.965E−03 |
| 120 | 1.239E−02 | 4.979E−03 | 7.529E−03 | 7.836E−03 | 6.953E−03 | 6.695E−03 | 9.479E−03 | 9.626E−03 | 3.213E−03 | 4.378E−03 | 9.516E−03 | 6.977E−03 | 4.181E−03 |
| 121 | 9.617E−02 | 2.342E−02 | 0.000E+00 | 6.946E−02 | 2.769E−02 | 1.932E−02 | 2.636E−02 | 4.613E−02 | 6.046E−02 | 5.476E−02 | 5.619E−02 | 4.052E−02 | 2.093E−01 |
| 122 | 1.202E−01 | 6.233E−02 | 7.542E−02 | 6.135E−02 | 1.069E−01 | 1.647E−01 | 3.954E−02 | 2.057E−01 | 2.280E−01 | 1.184E−01 | 9.617E−02 | 1.158E−01 | 3.918E−01 |
| 123 | 1.710E+00 | 3.446E+00 | 3.455E+00 | 2.947E+00 | 2.921E+00 | 2.698E+00 | 2.467E+00 | 2.425E+00 | 3.232E+00 | 1.888E+00 | 2.565E+00 | 1.950E+00 | 4.951E+00 |
| 124 | 5.361E−02 | 3.900E−02 | 1.888E−02 | 4.907E−02 | 1.184E−02 | 3.544E−02 | 1.977E−02 | 4.613E−02 | 4.702E−02 | 5.174E−02 | 3.972E−02 | 4.996E−02 | 1.042E−01 |
| 125 | 1.015E−01 | 3.508E−02 | 6.598E−02 | 2.858E−02 | 2.369E−02 | 2.903E−02 | 3.954E−02 | 7.444E−02 | 2.012E−02 | 5.779E−02 | 3.642E−02 | 4.052E−02 | 9.617E−02 |
| 126 | 1.095E+00 | 1.362E−01 | 3.393E−01 | 2.413E−01 | 2.689E−01 | 4.381E−01 | 3.197E−01 | 1.371E+00 | 1.336E+00 | 1.407E+00 | 6.215E−01 | 1.095E+00 | 1.603E+00 |
| 127 | 1.906E+00 | 8.736E−01 | 9.083E−01 | 8.014E−01 | 1.051E+00 | 1.158E+00 | 9.706E−01 | 2.681E+00 | 2.894E+00 | 2.075E+00 | 1.612E+00 | 2.779E+00 | 4.274E+00 |
| 128 | 1.282E+00 | 2.422E+00 | 2.841E+00 | 1.701E+00 | 2.431E+00 | 2.199E+00 | 1.638E+00 | 1.748E+00 | 2.796E+00 | 1.505E+00 | 2.271E+00 | 1.825E+00 | 3.713E+00 |
| 129 | 3.482E−02 | 4.675E−02 | 1.790E−01 | 2.858E−02 | 5.138E−02 | 4.194E−02 | 3.295E−02 | 3.188E−02 | 1.345E−01 | 4.568E−02 | 4.301E−02 | 3.117E−02 | 6.972E−02 |
| 130 | 1.181E+01 | 3.161E+00 | 5.227E+00 | 3.224E+00 | 3.856E+00 | 5.603E+00 | 7.523E+00 | 1.009E+01 | 1.241E+01 | 7.625E+00 | 1.132E+01 | 1.131E+01 | 2.949E+01 |
| 131 | 7.344E+00 | 3.882E+00 | 6.892E+00 | 3.464E+00 | 3.446E+00 | 4.414E+00 | 8.340E+00 | 7.212E+00 | 1.068E+01 | 6.067E+00 | 8.576E+00 | 5.808E+00 | 1.881E+01 |
| 132 | 4.550E−02 | 8.994E−02 | 9.439E−03 | 1.184E−01 | 6.723E−02 | 5.156E−02 | 5.272E−02 | 1.024E−01 | 9.439E−02 | 6.394E−02 | 5.289E−02 | 1.220E−01 | 1.131E−01 |
| 133 | 1.069E−02 | 3.117E−02 | 1.888E−02 | 1.229E−02 | 1.184E−02 | 2.582E−02 | 2.965E−02 | 3.188E−02 | 2.012E−02 | 3.348E−02 | 2.315E−02 | 3.117E−02 | 2.618E−02 |
| 134 | 1.069E−02 | 3.900E−03 | 9.439E−03 | 1.229E−02 | 3.954E−03 | 1.291E−02 | 9.884E−03 | 2.484E−02 | 4.025E−02 | 9.172E−03 | 0.000E+00 | 1.870E−02 | 2.618E−02 |
| 135 | 2.146E−02 | 1.950E−02 | 9.439E−03 | 4.087E−03 | 1.184E−02 | 1.291E−02 | 1.977E−02 | 1.060E−02 | 2.689E−02 | 2.431E−02 | 1.986E−02 | 2.493E−02 | 4.354E−02 |
| 136 | 5.361E−03 | 7.801E−03 | 0.000E+00 | 3.678E−02 | 1.977E−02 | 9.706E−03 | 1.977E−02 | 2.128E−02 | 1.345E−02 | 3.348E−02 | 1.656E−02 | 1.870E−02 | 4.354E−02 |
| 137 | 3.482E−02 | 7.801E−02 | 5.663E−02 | 1.149E−01 | 7.115E−02 | 4.515E−02 | 6.589E−02 | 4.613E−02 | 8.059E−02 | 5.476E−02 | 4.630E−02 | 4.363E−02 | 1.042E−01 |
| 138 | 2.146E−02 | 4.675E−02 | 1.888E−02 | 1.638E−02 | 5.931E−02 | 4.194E−02 | 1.977E−02 | 4.613E−02 | 3.357E−02 | 7.302E−02 | 1.327E−02 | 3.117E−02 | 1.131E−01 |
| 139 | 1.256E−01 | 1.594E−01 | 1.505E−01 | 1.843E−01 | 2.217E−01 | 2.645E−01 | 1.612E−01 | 2.556E−01 | 3.758E−01 | 1.977E−01 | 2.378E−01 | 2.680E−01 | 5.316E−01 |
| 140 | 7.765E−02 | 1.638E−01 | 9.439E−02 | 1.104E−01 | 1.817E−01 | 1.318E−01 | 2.173E−01 | 1.808E−01 | 1.478E−01 | 1.006E−01 | 1.621E−01 | 2.093E−01 | 3.054E−01 |
| 141 | 4.817E−02 | 7.017E−02 | 3.776E−02 | 3.678E−02 | 5.539E−02 | 2.253E−02 | 4.942E−02 | 6.741E−02 | 3.357E−02 | 6.696E−02 | 4.630E−02 | 5.931E−02 | 7.845E−02 |
| 142 | 1.069E−02 | 7.801E−03 | 4.720E−02 | 8.175E−03 | 1.184E−02 | 2.582E−02 | 1.318E−02 | 7.088E−03 | 4.025E−02 | 9.172E−03 | 9.884E−03 | 1.558E−02 | 2.618E−02 |
| 143 | 8.032E−03 | 1.167E−02 | 9.439E−03 | 1.638E−02 | 3.562E−02 | 6.447E−03 | 1.647E−02 | 2.128E−02 | 3.357E−02 | 2.128E−02 | 2.974E−02 | 1.247E−02 | 2.618E−02 |
| 144 | 4.550E−02 | 1.950E−02 | 4.720E−02 | 3.268E−02 | 4.746E−02 | 2.582E−02 | 2.965E−02 | 6.028E−02 | 6.046E−02 | 7.302E−02 | 9.884E−03 | 8.424E−02 | 1.220E−01 |
| 145 | 2.413E−02 | 1.167E−02 | 2.832E−02 | 3.268E−02 | 4.354E−02 | 2.253E−02 | 1.647E−02 | 3.544E−02 | 4.702E−02 | 3.651E−02 | 1.327E−02 | 4.675E−02 | 6.972E−02 |
| 146 | 1.309E−01 | 2.538E−01 | 2.360E−01 | 1.434E−01 | 1.621E−01 | 2.582E−01 | 3.295E−01 | 1.808E−01 | 2.351E−01 | 1.701E−01 | 3.010E−01 | 1.808E−01 | 3.660E−01 |
| 147 | 1.042E−01 | 8.994E−02 | 1.229E−01 | 5.726E−02 | 7.516E−02 | 6.126E−02 | 7.907E−02 | 2.591E−01 | 3.624E−01 | 1.888E−01 | 2.378E−01 | 1.656E−01 | 2.093E−01 |

APPENDIX D-continued

Ovarian Cancer
Training Dataset

| | | | | | | | | | | | | | |
|---|---|---|---|---|---|---|---|---|---|---|---|---|---|
| 148 | 2.894E−01 | 2.030E−01 | 1.505E−01 | 2.084E−01 | 4.550E−01 | 5.476E−01 | 3.491E−01 | 8.442E−01 | 1.006E+00 | 5.690E−01 | 5.058E−01 | 6.305E−01 | 9.172E−01 |
| 149 | 5.895E−02 | 3.900E−02 | 7.542E−02 | 7.765E−02 | 9.083E−02 | 8.994E−02 | 4.942E−02 | 1.309E−01 | 1.541E−01 | 9.172E−02 | 1.193E−01 | 1.532E−01 | 3.660E−01 |
| 150 | 1.069E−02 | 2.725E−02 | 1.888E−02 | 2.048E−02 | 2.769E−02 | 1.932E−02 | 9.884E−03 | 1.772E−02 | 6.046E−02 | 2.128E−02 | 1.327E−02 | 1.870E−02 | 4.354E−02 |
| 151 | 1.603E−02 | 1.950E−02 | 4.720E−02 | 2.449E−02 | 1.184E−02 | 1.932E−02 | 1.977E−02 | 2.841E−02 | 3.357E−02 | 1.523E−02 | 9.884E−03 | 3.428E−02 | 7.845E−02 |
| 152 | 6.963E−02 | 1.167E−02 | 2.832E−02 | 2.048E−02 | 2.769E−02 | 1.612E−02 | 2.965E−02 | 2.841E−02 | 1.077E−01 | 5.779E−02 | 3.972E−02 | 6.242E−02 | 7.845E−02 |
| 153 | 2.413E−02 | 1.950E−02 | 1.888E−02 | 4.087E−03 | 2.769E−02 | 2.903E−02 | 1.977E−02 | 2.841E−02 | 8.727E−02 | 2.431E−02 | 1.327E−02 | 2.182E−02 | 3.482E−02 |
| 154 | 8.032E−03 | 1.558E−02 | 3.776E−02 | 8.175E−03 | 7.907E−03 | 6.447E−03 | 9.884E−03 | 1.416E−02 | 2.689E−02 | 2.431E−02 | 9.884E−03 | 9.350E−03 | 2.618E−02 |
| 155 | 1.336E−02 | 2.342E−02 | 4.720E−02 | 4.497E−02 | 4.354E−02 | 9.706E−03 | 1.647E−02 | 2.484E−02 | 6.046E−02 | 3.045E−02 | 1.327E−02 | 9.350E−03 | 6.972E−02 |
| 156 | 1.719E−01 | 5.539E−01 | 4.052E−01 | 2.903E−01 | 3.241E−01 | 3.446E−01 | 9.350E−01 | 3.402E−01 | 4.025E−01 | 2.315E−01 | 5.850E−01 | 2.244E−01 | 5.574E−01 |
| 157 | 7.498E−02 | 1.362E−01 | 7.542E−02 | 8.175E−02 | 1.184E−01 | 1.389E−01 | 2.369E−01 | 1.487E−01 | 1.612E−01 | 1.158E−01 | 3.143E−01 | 1.345E−01 | 3.402E−01 |
| 158 | 2.841E−01 | 3.980E−01 | 2.173E−01 | 2.413E−01 | 3.874E−01 | 5.352E−01 | 6.652E−01 | 3.259E−01 | 4.898E−01 | 2.645E−01 | 6.055E−01 | 3.304E−01 | 6.189E−01 |
| 159 | 9.350E−02 | 1.478E−01 | 8.486E−02 | 8.175E−02 | 1.184E−01 | 1.647E−01 | 1.745E−01 | 1.558E−01 | 1.478E−01 | 1.184E−01 | 2.449E−01 | 9.973E−02 | 2.093E−01 |
| 160 | 3.749E−02 | 1.950E−02 | 1.888E−02 | 2.449E−02 | 1.585E−02 | 4.194E−02 | 2.636E−02 | 2.484E−02 | 3.357E−02 | 4.871E−02 | 3.642E−02 | 2.182E−02 | 6.972E−02 |
| 161 | 1.879E−02 | 2.725E−02 | 3.776E−02 | 5.316E−02 | 8.308E−02 | 4.194E−02 | 1.977E−02 | 3.188E−02 | 6.714E−02 | 4.871E−02 | 1.986E−02 | 4.675E−02 | 1.398E−01 |
| 162 | 2.680E−02 | 2.342E−02 | 4.720E−02 | 4.087E−02 | 3.161E−02 | 4.515E−02 | 1.318E−02 | 4.256E−02 | 4.702E−02 | 2.743E−02 | 1.656E−02 | 1.247E−02 | 1.398E−01 |
| 163 | 2.413E−02 | 4.675E−02 | 5.663E−02 | 3.678E−02 | 3.161E−02 | 1.612E−02 | 1.647E−02 | 1.772E−02 | 3.357E−02 | 2.743E−02 | 4.301E−02 | 3.117E−02 | 3.482E−02 |
| 164 | 1.603E−02 | 1.558E−02 | 1.888E−02 | 8.175E−03 | 7.907E−03 | 1.291E−02 | 1.977E−02 | 1.772E−02 | 4.702E−02 | 1.825E−02 | 2.645E−02 | 9.350E−03 | 8.718E−03 |
| 165 | 1.879E−02 | 3.117E−02 | 1.888E−02 | 2.449E−02 | 1.977E−02 | 1.612E−02 | 3.295E−02 | 1.772E−02 | 3.357E−02 | 1.825E−02 | 3.972E−02 | 1.870E−02 | 2.618E−02 |
| 166 | 3.482E−02 | 3.117E−02 | 6.598E−02 | 8.175E−03 | 3.562E−02 | 4.194E−02 | 3.954E−02 | 7.088E−02 | 9.439E−02 | 3.954E−02 | 5.619E−02 | 3.740E−02 | 1.220E−01 |
| 167 | 9.884E−02 | 3.348E−01 | 3.206E−01 | 1.674E−01 | 2.137E−01 | 2.965E−01 | 5.307E−01 | 2.413E−01 | 3.286E−01 | 1.398E−01 | 4.167E−01 | 1.808E−01 | 3.571E−01 |
| 168 | 6.429E−02 | 1.558E−01 | 1.131E−01 | 1.434E−01 | 1.977E−01 | 1.870E−01 | 1.487E−01 | 1.131E−01 | 1.211E−01 | 7.907E−02 | 2.484E−01 | 9.706E−02 | 2.698E−01 |
| 169 | 3.482E−02 | 9.706E−02 | 5.663E−02 | 5.316E−02 | 9.884E−02 | 8.994E−02 | 1.024E−01 | 7.088E−02 | 4.025E−02 | 4.871E−02 | 1.158E−01 | 7.801E−02 | 8.718E−02 |
| 170 | 2.413E−02 | 3.508E−02 | 9.439E−03 | 4.087E−02 | 5.138E−02 | 8.059E−02 | 2.636E−02 | 2.484E−02 | 2.689E−02 | 4.256E−02 | 4.301E−02 | 3.117E−02 | 7.845E−02 |
| 171 | 2.146E−02 | 1.558E−02 | 3.776E−02 | 4.497E−02 | 8.308E−02 | 8.709E−02 | 3.295E−02 | 3.544E−02 | 1.140E−01 | 4.568E−02 | 1.986E−02 | 4.052E−02 | 3.482E−02 |
| 172 | 4.427E−02 | 8.265E−02 | 1.373E−01 | 6.475E−02 | 3.924E−02 | 4.660E−02 | 3.716E−02 | 1.064E−01 | 9.246E−02 | 4.733E−02 | 7.787E−02 | 7.995E−02 | 1.300E−01 |
| 173 | 1.282E+00 | 1.693E+00 | 1.025E+00 | 1.844E+00 | 1.626E+00 | 1.291E+00 | 1.416E+00 | 1.839E+00 | 2.506E+00 | 1.402E+00 | 1.642E+00 | 1.617E+00 | 3.056E+00 |
| 174 | 1.949E+00 | 2.659E+00 | 1.096E+00 | 2.735E+00 | 2.568E+00 | 1.998E+00 | 2.466E+00 | 2.427E+00 | 3.951E+00 | 2.241E+00 | 2.595E+00 | 2.526E+00 | 4.076E+00 |
| 175 | 8.288E−01 | 6.658E−01 | 5.800E−01 | 6.278E−01 | 5.874E−01 | 4.500E−01 | 5.984E−01 | 1.132E+00 | 1.134E+00 | 8.489E−01 | 6.781E−01 | 9.708E−01 | 1.324E+00 |
| 176 | 1.957E+00 | 2.998E+00 | 4.288E+00 | 3.838E+00 | 2.370E+00 | 1.923E+00 | 1.689E+00 | 2.883E+00 | 3.107E+00 | 1.969E+00 | 2.144E+00 | 2.198E+00 | 3.487E+00 |
| 177 | 7.321E−01 | 9.625E−01 | 3.141E+00 | 9.186E−01 | 5.739E−01 | 6.544E−01 | 9.375E−01 | 1.081E+00 | 1.306E+00 | 6.094E−01 | 1.113E+00 | 1.014E+00 | 1.499E+00 |
| 178 | 1.692E−01 | 8.056E−02 | 3.519E−01 | 1.459E−01 | 8.056E−02 | 1.582E−01 | 1.410E−01 | 2.764E−01 | 2.759E−01 | 1.521E−01 | 2.207E−01 | 1.570E−01 | 3.630E−01 |
| 179 | 3.029E−02 | 1.987E−02 | 3.372E−02 | 1.631E−02 | 1.521E−02 | 1.729E−02 | 1.680E−02 | 3.617E−02 | 4.071E−02 | 2.771E−02 | 1.962E−02 | 3.519E−02 | 4.562E−02 |
| 180 | 2.514E−02 | 1.717E−02 | 1.300E−02 | 2.931E−02 | 2.452E−02 | 1.459E−02 | 1.225E−02 | 2.391E−02 | 2.685E−02 | 1.508E−02 | 1.545E−02 | 2.710E−02 | 3.004E−02 |
| 181 | 1.545E−02 | 1.127E−02 | 1.950E−02 | 2.649E−02 | 1.471E−02 | 1.199E−02 | 4.991E−03 | 1.361E−02 | 2.121E−02 | 1.132E−02 | 1.002E−02 | 1.031E−02 | 1.680E−02 |
| 182 | 6.671E−02 | 1.300E−01 | 4.672E−02 | 1.533E−01 | 1.226E−01 | 9.994E−02 | 9.528E−02 | 1.349E−01 | 1.183E−01 | 8.927E−02 | 1.107E−01 | 8.596E−02 | 1.876E−01 |
| 183 | 1.374E+00 | 1.956E+00 | 3.237E−01 | 2.107E+00 | 1.721E+00 | 1.430E+00 | 1.508E+00 | 2.479E+00 | 1.619E+00 | 1.516E+00 | 1.718E+00 | 1.446E+00 | 2.592E+00 |
| 184 | 1.195E+00 | 1.977E+00 | 3.421E−01 | 2.170E+00 | 1.921E+00 | 1.723E+00 | 1.703E+00 | 2.296E+00 | 1.787E+00 | 1.260E+00 | 1.869E+00 | 1.330E+00 | 2.497E+00 |
| 185 | 9.380E−01 | 1.341E+00 | 1.026E−01 | 1.621E+00 | 1.359E+00 | 1.251E+00 | 1.155E+00 | 1.681E+00 | 1.298E+00 | 1.030E+00 | 1.235E+00 | 9.343E−01 | 1.639E+00 |
| 186 | 2.324E+00 | 3.139E+00 | 5.334E−01 | 3.976E+00 | 2.928E+00 | 2.706E+00 | 2.612E+00 | 3.746E+00 | 3.093E+00 | 2.429E+00 | 2.520E+00 | 2.071E+00 | 3.113E+00 |
| 187 | 8.812E−01 | 7.296E−01 | 1.570E−01 | 7.836E−01 | 5.996E−01 | 5.248E−01 | 5.628E−01 | 1.175E+00 | 7.112E−01 | 7.909E−01 | 6.806E−01 | 7.552E−01 | 9.552E−01 |
| 188 | 8.486E−02 | 5.960E−02 | 3.507E−02 | 6.021E−02 | 4.145E−02 | 3.863E−02 | 4.672E−02 | 1.074E−01 | 7.124E−02 | 7.370E−02 | 5.150E−02 | 7.002E−02 | 8.755E−02 |
| 189 | 1.251E−02 | 1.239E−02 | 3.899E−03 | 2.477E−02 | 1.035E−02 | 1.199E−02 | 1.089E−02 | 3.912E−02 | 2.121E−02 | 1.839E−02 | 2.183E−02 | 1.251E−02 | 3.115E−02 |
| 190 | 2.036E−01 | 2.624E−01 | 1.386E−01 | 2.563E−01 | 2.097E−01 | 2.048E−01 | 1.741E−01 | 5.093E−01 | 3.200E−01 | 1.778E−01 | 3.311E−01 | 2.428E−01 | 2.784E−01 |
| 191 | 2.246E+00 | 3.675E+00 | 2.372E+00 | 3.915E+00 | 2.102E+00 | 2.829E+00 | 3.268E+00 | 4.516E+00 | 2.771E+00 | 1.895E+00 | 3.447E+00 | 2.448E+00 | 3.763E+00 |
| 192 | 7.370E−01 | 6.352E−01 | 4.206E−01 | 9.372E−01 | 4.684E−01 | 8.555E−01 | 7.541E−01 | 1.412E+00 | 8.400E−01 | 6.855E−01 | 9.360E−01 | 6.194E−01 | 1.110E+00 |
| 193 | 1.117E−01 | 5.849E−02 | 4.292E−02 | 9.847E−02 | 6.646E−02 | 9.675E−02 | 6.536E−02 | 1.655E−01 | 1.324E−01 | 8.547E−02 | 9.332E−02 | 8.596E−02 | 1.435E−01 |
| 194 | 8.044E−02 | 1.219E−01 | 1.815E−02 | 1.312E−01 | 2.244E−01 | 1.159E−01 | 6.438E−02 | 8.351E−02 | 1.704E−01 | 7.419E−02 | 9.479E−02 | 8.547E−02 | 1.080E−01 |
| 195 | 3.029E−02 | 5.800E−02 | 1.435E−02 | 5.800E−02 | 8.498E−02 | 5.101E−02 | 2.318E−02 | 3.568E−02 | 6.291E−02 | 4.059E−02 | 2.955E−02 | 3.397E−02 | 5.285E−02 |
| 196 | 1.373E−01 | 2.305E−01 | 1.888E−01 | 2.305E−01 | 9.969E−02 | 1.212E−01 | 2.109E−01 | 3.691E−01 | 1.913E−01 | 1.337E−01 | 2.293E−01 | 1.386E−01 | 2.342E−01 |
| 197 | 1.055E−01 | 1.655E−01 | 9.479E−02 | 1.680E−01 | 7.247E−02 | 9.945E−02 | 1.447E−01 | 2.011E−01 | 1.349E−01 | 1.082E−01 | 1.803E−01 | 1.194E−01 | 1.803E−01 |

APPENDIX D-continued

Ovarian Cancer
Training Dataset

| | | | | | | | | | | | | | |
|---|---|---|---|---|---|---|---|---|---|---|---|---|---|
| 198 | 6.781E−02 | 7.946E−02 | 4.942E−02 | 9.405E−02 | 7.738E−02 | 9.810E−02 | 5.714E−02 | 1.373E−01 | 7.762E−02 | 6.156E−02 | 8.424E−02 | 8.596E−02 | 1.263E−01 |
| 199 | 1.349E−01 | 2.563E−01 | 3.250E−02 | 2.784E−01 | 2.624E−01 | 2.894E−01 | 1.373E−01 | 2.121E−01 | 1.373E−01 | 1.288E−01 | 1.570E−01 | 1.337E−01 | 1.962E−01 |
| 200 | 7.272E−02 | 9.013E−02 | 1.692E−02 | 1.188E−01 | 1.239E−01 | 1.047E−01 | 4.623E−02 | 9.135E−02 | 8.228E−02 | 7.836E−02 | 7.333E−02 | 5.923E−02 | 9.601E−02 |
| 201 | 3.544E−02 | 6.928E−02 | 2.207E−02 | 7.652E−02 | 1.019E−01 | 6.254E−02 | 2.771E−02 | 5.616E−02 | 7.676E−02 | 2.980E−02 | 4.598E−02 | 4.598E−02 | 6.720E−02 |
| 202 | 1.288E−02 | 2.894E−02 | 5.199E−03 | 3.151E−02 | 2.293E−02 | 2.710E−02 | 9.074E−03 | 2.685E−02 | 1.852E−02 | 1.089E−02 | 1.002E−02 | 1.459E−02 | 1.557E−02 |
| 203 | 3.323E−03 | 1.074E−03 | 2.660E−03 | 0.000E+00 | 1.089E−03 | 4.439E−04 | 1.361E−03 | 4.880E−04 | 9.246E−04 | 1.263E−03 | 1.361E−03 | 8.596E−04 | 2.403E−03 |
| 204 | 1.106E−02 | 2.305E−02 | 1.039E−02 | 2.416E−02 | 1.852E−02 | 2.403E−02 | 9.528E−03 | 2.097E−02 | 1.570E−02 | 1.132E−02 | 1.275E−02 | 7.738E−03 | 1.200E−02 |
| 205 | 3.691E−04 | 1.606E−03 | 1.300E−03 | 1.126E−03 | 3.262E−03 | 2.219E−03 | 2.722E−03 | 1.950E−03 | 1.852E−03 | 1.263E−03 | 2.281E−03 | 1.288E−03 | 0.000E+00 |
| 206 | 1.913E−02 | 5.212E−02 | 6.499E−03 | 4.611E−02 | 4.083E−02 | 3.863E−02 | 1.680E−02 | 2.735E−02 | 3.323E−02 | 2.269E−02 | 1.962E−02 | 2.232E−02 | 2.158E−02 |
| 207 | 2.955E−03 | 1.020E−02 | 2.600E−03 | 9.565E−03 | 1.089E−02 | 8.437E−03 | 2.722E−03 | 3.421E−03 | 1.852E−03 | 5.445E−03 | 9.111E−03 | 2.146E−03 | 1.435E−02 |
| 208 | 3.323E−03 | 5.371E−03 | 3.899E−03 | 6.757E−03 | 4.905E−03 | 3.556E−03 | 5.898E−03 | 2.440E−03 | 5.543E−03 | 6.708E−03 | 5.469E−03 | 2.575E−03 | 0.000E+00 |
| 209 | 7.382E−04 | 0.000E+00 | 3.899E−03 | 1.126E−03 | 2.722E−03 | 4.439E−04 | 4.537E−04 | 4.880E−04 | 9.246E−04 | 4.194E−04 | 4.549E−04 | 0.000E+00 | 0.000E+00 |
| 210 | 0.000E+00 | 0.000E+00 | 1.300E−03 | 5.628E−04 | 1.089E−03 | 4.439E−04 | 9.074E−04 | 0.000E+00 | 0.000E+00 | 8.375E−04 | 9.111E−04 | 4.292E−04 | 0.000E+00 |
| 211 | 3.691E−04 | 1.074E−03 | 2.600E−03 | 5.628E−04 | 5.445E−04 | 0.000E+00 | 1.815E−03 | 4.880E−04 | 0.000E+00 | 4.194E−04 | 1.827E−03 | 8.596E−04 | 4.795E−03 |
| 212 | 1.471E−03 | 1.606E−03 | 0.000E+00 | 3.936E−03 | 3.814E−03 | 3.556E−03 | 3.176E−03 | 4.880E−04 | 2.771E−03 | 1.263E−03 | 3.188E−03 | 3.863E−03 | 1.200E−03 |
| 213 | 2.207E−03 | 3.225E−03 | 3.899E−03 | 6.193E−03 | 2.183E−03 | 2.219E−03 | 2.269E−03 | 2.931E−03 | 6.475E−03 | 4.194E−03 | 3.642E−03 | 1.717E−03 | 2.403E−03 |
| 214 | 2.207E−03 | 5.910E−03 | 3.899E−03 | 4.500E−03 | 2.183E−03 | 4.439E−03 | 3.176E−03 | 2.440E−03 | 3.703E−03 | 2.097E−03 | 3.188E−03 | 1.717E−03 | 4.795E−03 |
| 215 | 3.691E−04 | 5.371E−04 | 1.300E−03 | 0.000E+00 | 0.000E+00 | 1.778E−03 | 1.361E−03 | 0.000E+00 | 0.000E+00 | 8.375E−04 | 1.827E−03 | 0.000E+00 | 2.403E−03 |
| 216 | 7.382E−04 | 0.000E+00 | 0.000E+00 | 5.628E−04 | 5.445E−04 | 1.778E−03 | 1.361E−03 | 0.000E+00 | 0.000E+00 | 8.375E−04 | 4.549E−04 | 8.596E−04 | 1.200E−03 |
| 217 | 1.106E−03 | 1.606E−03 | 2.600E−03 | 1.692E−03 | 5.445E−04 | 4.439E−04 | 9.074E−04 | 4.880E−04 | 1.852E−03 | 8.375E−04 | 9.111E−04 | 1.288E−03 | 1.200E−03 |
| 218 | 1.784E+00 | 2.022E+00 | 3.875E−01 | 1.913E+00 | 1.618E+00 | 1.343E+00 | 1.553E+00 | 2.513E+00 | 1.647E+00 | 1.784E+00 | 1.766E+00 | 1.670E+00 | 2.827E+00 |
| 219 | 1.398E−02 | 1.827E−02 | 1.300E−02 | 2.416E−02 | 1.582E−02 | 2.219E−02 | 1.594E−02 | 3.078E−02 | 1.668E−02 | 2.600E−02 | 2.318E−02 | 1.545E−02 | 4.562E−02 |
| 220 | 1.512E+00 | 1.041E+00 | 1.777E+00 | 1.019E+00 | 1.257E+00 | 1.895E+00 | 7.677E−01 | 2.260E+00 | 2.534E+00 | 1.173E+00 | 1.939E+00 | 1.905E+00 | 2.083E+00 |
| 221 | 5.178E+01 | 6.607E+01 | 7.970E+01 | 6.573E+01 | 6.810E+01 | 7.119E+01 | 5.449E+01 | 5.682E+01 | 6.305E+01 | 5.071E+01 | 6.634E+01 | 6.063E+01 | 6.089E+01 |
| 222 | 5.528E+01 | 2.413E+01 | 6.168E+01 | 2.681E+01 | 3.116E+01 | 3.439E+01 | 3.196E+01 | 4.355E+01 | 6.416E+01 | 5.448E+01 | 3.982E+01 | 6.508E+01 | 4.490E+01 |
| 223 | 2.995E+01 | 2.123E+01 | 4.205E+01 | 1.987E+01 | 2.257E+01 | 2.272E+01 | 2.040E+01 | 2.367E+01 | 2.799E+01 | 2.281E+01 | 2.548E+01 | 3.167E+01 | 2.806E+01 |
| 224 | 1.901E+01 | 1.631E+01 | 2.007E+01 | 1.854E+01 | 2.484E+01 | 2.577E+01 | 1.445E+01 | 2.364E+01 | 2.565E+01 | 2.018E+01 | 2.436E+01 | 2.676E+01 | 2.138E+01 |
| 225 | 1.668E+01 | 1.515E+01 | 4.262E+01 | 1.303E+01 | 9.880E+00 | 1.371E+01 | 1.898E+01 | 1.145E+01 | 1.427E+01 | 1.030E+01 | 2.535E+01 | 1.660E+01 | 1.840E+01 |
| 226 | 5.709E+00 | 4.192E+00 | 2.277E+01 | 3.876E+00 | 3.056E+00 | 5.051E+00 | 8.835E+00 | 5.558E+00 | 8.234E+00 | 4.581E+00 | 8.878E+00 | 5.740E+00 | 6.894E+00 |
| 227 | 2.279E+00 | 1.314E+00 | 5.747E+00 | 1.579E+00 | 1.098E+00 | 2.013E+00 | 2.906E+00 | 1.878E+00 | 2.611E+00 | 1.684E+00 | 3.347E+00 | 2.402E+00 | 2.944E+00 |
| 228 | 4.718E−01 | 3.507E−01 | 2.524E−01 | 4.236E−01 | 5.122E−01 | 6.217E−01 | 2.947E−01 | 6.391E−01 | 4.554E−01 | 8.026E−01 | 5.702E−01 | 1.543E+00 | 5.673E−01 |
| 229 | 4.942E−01 | 3.766E−01 | 2.835E−01 | 4.528E−01 | 5.240E−01 | 6.190E−01 | 3.272E−01 | 8.820E−01 | 4.621E−01 | 8.400E−01 | 5.977E−01 | 1.462E+00 | 6.144E−01 |
| 230 | 3.900E+01 | 4.245E+01 | 6.425E+01 | 3.809E+01 | 3.289E+01 | 2.526E+01 | 3.198E+01 | 2.140E+01 | 2.507E+01 | 2.820E+01 | 1.878E+01 | 2.345E+01 | 2.592E+01 |
| 231 | 4.191E+00 | 4.561E+00 | 6.438E+00 | 4.809E+00 | 4.583E+00 | 3.480E+00 | 3.544E+00 | 3.670E+00 | 3.156E+00 | 5.437E+00 | 3.607E+00 | 4.939E+00 | 4.582E+00 |
| 232 | 1.913E+00 | 1.758E+00 | 1.982E+00 | 1.679E+00 | 1.577E+00 | 1.601E+00 | 1.770E+00 | 1.397E+00 | 1.813E+00 | 1.906E+00 | 1.575E+00 | 1.507E+00 | 1.589E+00 |
| 233 | 5.033E+00 | 6.990E+00 | 8.487E+00 | 5.205E+00 | 5.037E+00 | 4.835E+00 | 5.309E+00 | 4.796E+00 | 6.142E+00 | 6.351E+00 | 4.970E+00 | 5.484E+00 | 5.227E+00 |
| 234 | 1.368E+01 | 2.449E+01 | 2.416E+01 | 1.829E+01 | 2.306E+01 | 1.869E+01 | 1.580E+01 | 1.815E+01 | 1.497E+01 | 1.440E+01 | 1.829E+01 | 1.526E+01 | 1.987E+01 |
| 235 | 1.017E+01 | 1.527E+01 | 1.013E+01 | 1.662E+01 | 1.173E+01 | 9.986E+00 | 1.309E+01 | 9.332E+00 | 6.753E+00 | 9.229E+00 | 9.466E+00 | 7.615E+00 | 9.780E+00 |
| 236 | 9.578E−01 | 5.763E−01 | 3.871E−01 | 5.999E−01 | 5.721E−01 | 6.754E−01 | 5.615E−01 | 7.310E−01 | 1.300E+00 | 1.237E+00 | 9.044E−01 | 8.377E−01 | 7.548E−01 |
| 237 | 6.739E+00 | 2.028E+00 | 1.812E+00 | 3.055E+00 | 1.939E+00 | 2.524E+00 | 3.238E+00 | 4.439E+00 | 6.499E+00 | 7.148E+00 | 3.341E+00 | 4.990E+00 | 4.402E+00 |
| 238 | 7.229E+00 | 5.534E+00 | 5.485E+00 | 6.389E+00 | 4.684E+00 | 4.650E+00 | 5.716E+00 | 5.191E+00 | 5.680E+00 | 6.414E+00 | 4.765E+00 | 5.340E+00 | 5.406E+00 |
| 239 | 1.407E+00 | 1.187E+00 | 1.086E+00 | 1.559E+00 | 1.118E+00 | 1.155E+00 | 1.315E+00 | 1.087E+00 | 1.079E+00 | 1.396E+00 | 1.214E+00 | 1.195E+00 | 1.165E+00 |
| 240 | 1.719E+01 | 1.202E+01 | 2.433E+00 | 1.335E+01 | 1.981E+01 | 1.747E+01 | 7.706E+00 | 1.550E+01 | 2.290E+01 | 2.094E+01 | 1.477E+01 | 1.364E+01 | 1.352E+01 |
| 241 | 2.127E+02 | 2.101E+02 | 1.037E+02 | 2.233E+02 | 2.323E+02 | 2.296E+02 | 2.091E+02 | 2.753E+02 | 2.685E+02 | 2.286E+02 | 2.240E+02 | 2.255E+02 | 2.415E+02 |
| 242 | 1.554E+02 | 1.875E+02 | 9.555E+01 | 1.802E+02 | 1.821E+02 | 1.685E+02 | 1.746E+02 | 1.730E+02 | 1.417E+02 | 1.517E+02 | 1.719E+02 | 1.482E+02 | 1.814E+02 |
| 243 | 1.622E+01 | 1.938E+01 | 8.825E+00 | 1.890E+01 | 1.736E+01 | 1.636E+01 | 1.907E+01 | 1.589E+01 | 1.206E+01 | 1.476E+01 | 1.686E+01 | 1.397E+01 | 1.693E+01 |
| 244 | 9.376E+00 | 5.351E+00 | 8.884E+00 | 6.201E+00 | 4.873E+00 | 6.587E+00 | 1.109E+01 | 7.541E+00 | 9.468E+00 | 7.615E+00 | 1.107E+01 | 9.154E+00 | 1.217E+01 |
| 245 | 6.030E+00 | 2.422E+00 | 3.149E+00 | 3.321E+00 | 2.646E+00 | 3.506E+00 | 4.371E+00 | 5.015E+00 | 6.060E+00 | 5.470E+00 | 4.665E+00 | 4.476E+00 | 5.272E+00 |
| 246 | 8.592E+00 | 5.348E+00 | 2.684E+00 | 7.056E+00 | 6.028E+00 | 6.098E+00 | 5.757E+00 | 8.194E+00 | 9.381E+00 | 1.021E+01 | 5.826E+00 | 6.620E+00 | 5.642E+00 |
| 247 | 5.057E+00 | 4.190E+00 | 2.796E+00 | 4.776E+00 | 3.900E+00 | 4.852E+00 | 4.575E+00 | 4.760E+00 | 5.196E+00 | 6.091E+00 | 4.900E+00 | 4.916E+00 | 4.648E+00 |

APPENDIX D-continued

Ovarian Cancer
Training Dataset

| | | | | | | | | | | | | | |
|---|---|---|---|---|---|---|---|---|---|---|---|---|---|
| 248 | 7.295E+01 | 1.045E+02 | 5.693E+01 | 9.520E+01 | 5.884E+01 | 7.730E+01 | 1.195E+02 | 7.908E+01 | 7.228E+01 | 6.455E+01 | 1.365E+02 | 6.675E+01 | 8.426E+01 |
| 249 | 7.745E+01 | 4.570E+01 | 2.392E+01 | 6.336E+01 | 4.950E+01 | 7.693E+01 | 6.775E+01 | 9.043E+01 | 7.579E+01 | 7.649E+01 | 8.966E+01 | 5.690E+01 | 6.823E+01 |
| 250 | 1.370E+02 | 7.818E+01 | 4.348E+01 | 9.961E+01 | 1.263E+02 | 1.291E+02 | 9.639E+01 | 1.765E+02 | 1.546E+02 | 1.526E+02 | 1.248E+02 | 1.481E+02 | 1.307E+02 |
| 251 | 5.590E+01 | 4.222E+01 | 2.717E+01 | 4.761E+01 | 6.253E+01 | 5.884E+01 | 3.970E+01 | 6.708E+01 | 5.631E+01 | 6.098E+01 | 5.470E+01 | 6.702E+01 | 5.922E+01 |
| 252 | 3.823E+00 | 3.019E+00 | 2.016E+00 | 3.444E+00 | 4.261E+00 | 4.015E+00 | 2.745E+00 | 4.381E+00 | 3.956E+00 | 4.172E+00 | 4.219E+00 | 4.783E+00 | 4.303E+00 |
| 253 | 3.763E+00 | 2.523E+00 | 3.342E+00 | 2.646E+00 | 2.528E+00 | 2.874E+00 | 4.184E+00 | 3.790E+00 | 4.676E+00 | 3.558E+00 | 5.275E+00 | 3.437E+00 | 4.759E+00 |
| 254 | 8.169E+00 | 5.717E+00 | 1.067E+01 | 6.108E+00 | 5.239E+00 | 6.570E+00 | 9.509E+00 | 7.153E+00 | 8.185E+00 | 5.915E+00 | 1.044E+01 | 7.111E+00 | 9.303E+00 |
| 255 | 7.945E+00 | 5.879E+00 | 7.593E+00 | 6.819E+00 | 4.881E+00 | 6.234E+00 | 9.195E+00 | 7.115E+00 | 7.309E+00 | 6.351E+00 | 9.525E+00 | 6.540E+00 | 8.084E+00 |
| 256 | 3.765E+00 | 3.497E+00 | 1.924E+00 | 4.147E+00 | 2.390E+00 | 3.046E+00 | 3.322E+00 | 3.465E+00 | 3.159E+00 | 3.551E+00 | 3.834E+00 | 2.559E+00 | 3.634E+00 |
| 257 | 5.670E+00 | 4.583E+00 | 4.779E+00 | 4.698E+00 | 4.236E+00 | 4.916E+00 | 4.621E+00 | 4.252E+00 | 6.140E+00 | 5.801E+00 | 4.218E+00 | 4.488E+00 | 4.685E+00 |
| 258 | 2.381E+01 | 2.132E+01 | 1.675E+01 | 2.365E+01 | 1.552E+01 | 2.584E+01 | 3.620E+01 | 2.751E+01 | 2.634E+01 | 2.036E+01 | 5.625E+01 | 2.300E+01 | 2.848E+01 |
| 259 | 3.887E+01 | 4.381E+01 | 2.665E+01 | 4.563E+01 | 3.492E+01 | 5.325E+01 | 5.666E+01 | 4.505E+01 | 4.095E+01 | 3.233E+01 | 8.132E+01 | 4.505E+01 | 4.722E+01 |
| 260 | 3.473E+01 | 3.459E+01 | 3.493E+01 | 3.855E+01 | 3.400E+01 | 4.930E+01 | 3.705E+01 | 3.857E+01 | 3.355E+01 | 3.213E+01 | 5.115E+01 | 3.079E+01 | 3.760E+01 |
| 261 | 3.096E+01 | 4.121E+01 | 6.691E+01 | 4.124E+01 | 4.474E+01 | 3.479E+01 | 3.513E+01 | 2.685E+01 | 2.790E+01 | 2.659E+01 | 2.380E+01 | 2.551E+01 | 2.689E+01 |
| 262 | 1.191E+01 | 9.646E+00 | 1.539E+01 | 1.256E+01 | 1.510E+01 | 1.407E+01 | 1.053E+01 | 1.163E+01 | 1.263E+01 | 1.375E+01 | 9.429E+00 | 1.275E+01 | 1.174E+01 |
| 263 | 2.867E+00 | 2.025E+00 | 2.707E+00 | 2.330E+00 | 1.672E+00 | 2.294E+00 | 3.585E+00 | 3.093E+00 | 3.378E+00 | 2.594E+00 | 3.430E+00 | 2.156E+00 | 3.016E+00 |
| 264 | 3.556E+00 | 3.504E+00 | 2.558E+00 | 3.793E+00 | 2.482E+00 | 3.000E+00 | 3.814E+00 | 3.331E+00 | 2.926E+00 | 3.073E+00 | 4.063E+00 | 2.291E+00 | 3.721E+00 |
| 265 | 2.553E+00 | 2.282E+00 | 1.610E+00 | 2.732E+00 | 2.151E+00 | 2.590E+00 | 2.532E+00 | 2.421E+00 | 2.180E+00 | 2.168E+00 | 3.058E+00 | 1.804E+00 | 2.784E+00 |
| 266 | 2.405E+00 | 2.940E+00 | 9.359E−01 | 3.139E+00 | 3.449E+00 | 3.537E+00 | 1.994E+00 | 2.136E+00 | 2.317E+00 | 2.633E+00 | 2.432E+00 | 1.866E+00 | 2.235E+00 |
| 267 | 2.032E+00 | 2.876E+00 | 1.541E+00 | 2.896E+00 | 2.996E+00 | 3.150E+00 | 1.835E+00 | 2.105E+00 | 2.113E+00 | 2.378E+00 | 2.020E+00 | 1.788E+00 | 1.928E+00 |
| 268 | 9.015E+00 | 9.187E+00 | 7.081E+00 | 8.700E+00 | 7.746E+00 | 1.399E+01 | 1.736E+01 | 1.767E+01 | 1.382E+01 | 1.005E+01 | 2.014E+01 | 1.243E+01 | 1.416E+01 |
| 269 | 7.958E+00 | 9.173E+00 | 3.375E+00 | 9.584E+00 | 9.354E+00 | 1.399E+01 | 1.162E+01 | 1.140E+01 | 9.453E+00 | 8.618E+00 | 1.478E+01 | 8.791E+00 | 1.205E+01 |
| 270 | 3.912E+00 | 3.946E+00 | 1.216E+00 | 4.741E+00 | 4.523E+00 | 7.127E+00 | 4.304E+00 | 4.894E+00 | 3.664E+00 | 3.905E+00 | 7.106E+00 | 4.089E+00 | 5.388E+00 |
| 271 | 1.440E+01 | 1.530E+01 | 2.109E+01 | 1.286E+01 | 1.021E+01 | 8.996E+00 | 1.387E+01 | 9.733E+00 | 1.089E+01 | 1.145E+01 | 9.325E+00 | 1.160E+01 | 1.018E+01 |
| 272 | 8.862E+01 | 1.104E+02 | 1.688E+02 | 9.607E+01 | 8.531E+01 | 6.692E+01 | 8.359E+01 | 5.560E+01 | 5.987E+01 | 7.164E+01 | 4.846E+01 | 7.467E+01 | 6.816E+01 |
| 273 | 9.372E+01 | 1.146E+02 | 1.865E+02 | 1.024E+02 | 9.094E+01 | 7.173E+01 | 8.810E+01 | 5.741E+01 | 6.646E+01 | 7.655E+01 | 5.275E+01 | 7.491E+01 | 7.639E+01 |
| 274 | 1.433E+01 | 1.777E+01 | 2.853E+01 | 1.593E+01 | 1.540E+01 | 1.080E+01 | 1.275E+01 | 8.257E+00 | 9.189E+00 | 1.214E+01 | 7.599E+00 | 1.211E+01 | 1.156E+01 |
| 275 | 6.744E−01 | 8.439E−01 | 1.026E+00 | 6.024E−01 | 7.246E−01 | 6.532E−01 | 6.522E−01 | 7.605E−01 | 6.204E−01 | 5.910E−01 | 6.306E−01 | 4.849E−01 | 4.108E−01 |
| 276 | 8.478E+00 | 1.395E+01 | 1.752E+01 | 9.447E+00 | 9.357E+00 | 7.472E+00 | 1.050E+01 | 6.261E+00 | 6.109E+00 | 6.848E+00 | 6.463E+00 | 6.388E+00 | 7.292E+00 |
| 277 | 1.775E+01 | 4.598E+01 | 5.555E+01 | 2.729E+01 | 3.814E+01 | 2.230E+01 | 2.597E+01 | 1.580E+01 | 1.523E+01 | 1.913E+01 | 1.590E+01 | 2.012E+01 | 1.936E+01 |
| 278 | 1.769E+01 | 4.413E+01 | 5.569E+01 | 2.689E+01 | 3.784E+01 | 2.199E+01 | 2.543E+01 | 1.414E+01 | 1.499E+01 | 1.885E+01 | 1.573E+01 | 1.931E+01 | 1.883E+01 |
| 279 | 4.473E+00 | 1.004E+01 | 1.085E+01 | 7.284E+00 | 1.085E+01 | 7.486E+00 | 5.981E+00 | 5.928E+00 | 4.808E+00 | 5.216E+00 | 6.579E+00 | 6.749E+00 | 7.749E+00 |
| 280 | 6.846E+00 | 5.742E+00 | 5.156E+00 | 5.593E+00 | 6.605E+00 | 6.254E+00 | 4.952E+00 | 5.850E+00 | 7.394E+00 | 7.250E+00 | 5.275E+00 | 6.069E+00 | 5.599E+00 |
| 281 | 1.278E+02 | 1.120E+02 | 6.178E+01 | 1.174E+02 | 1.105E+02 | 1.193E+02 | 1.262E+02 | 1.363E+02 | 1.345E+02 | 1.479E+02 | 1.171E+02 | 1.424E+02 | 1.229E+02 |
| 282 | 1.116E+02 | 9.609E+01 | 5.580E+01 | 1.037E+02 | 9.723E+01 | 1.052E+02 | 1.120E+02 | 1.066E+02 | 1.180E+02 | 1.309E+02 | 1.006E+02 | 1.238E+02 | 1.055E+02 |
| 283 | 5.440E+01 | 6.120E+01 | 2.665E+01 | 5.525E+01 | 5.239E+01 | 5.298E+01 | 6.071E+01 | 4.430E+01 | 4.041E+01 | 4.839E+01 | 5.245E+01 | 5.473E+01 | 5.863E+01 |
| 284 | 6.413E+00 | 4.370E+00 | 4.053E+00 | 4.652E+00 | 4.407E+00 | 6.249E+00 | 4.787E+00 | 5.946E+00 | 6.606E+00 | 8.426E+00 | 5.390E+00 | 6.976E+00 | 5.098E+00 |
| 285 | 8.433E+01 | 5.322E+01 | 5.105E+01 | 6.197E+01 | 7.361E+01 | 7.968E+01 | 6.362E+01 | 9.420E+01 | 8.592E+01 | 9.747E+01 | 7.050E+01 | 1.038E+02 | 7.716E+01 |
| 286 | 6.254E+01 | 4.301E+01 | 4.610E+01 | 5.100E+01 | 5.875E+01 | 6.247E+01 | 5.159E+01 | 5.777E+01 | 6.836E+01 | 7.481E+01 | 5.503E+01 | 7.542E+01 | 6.155E+01 |
| 287 | 1.071E+01 | 7.618E+00 | 4.949E+00 | 8.047E+00 | 1.039E+01 | 1.062E+01 | 7.165E+00 | 8.644E+00 | 9.201E+00 | 1.106E+01 | 9.915E+00 | 1.118E+01 | 1.110E+01 |
| 288 | 5.725E+01 | 7.871E+01 | 1.352E+02 | 7.177E+01 | 7.925E+01 | 6.144E+01 | 6.906E+01 | 4.832E+01 | 4.890E+01 | 4.784E+01 | 4.280E+01 | 4.511E+01 | 5.110E+01 |
| 289 | 4.592E+01 | 6.653E+01 | 1.116E+02 | 6.140E+01 | 6.635E+01 | 4.907E+01 | 6.005E+01 | 2.564E+01 | 4.220E+01 | 3.943E+01 | 3.296E+01 | 3.514E+01 | 4.143E+01 |
| 290 | 1.790E+01 | 1.846E+01 | 3.647E+01 | 2.204E+01 | 2.155E+01 | 2.187E+01 | 2.132E+01 | 1.672E+01 | 1.878E+01 | 1.971E+01 | 1.417E+01 | 1.801E+01 | 1.937E+01 |
| 291 | 1.461E+01 | 1.495E+01 | 2.952E+01 | 1.797E+01 | 1.742E+01 | 1.780E+01 | 1.740E+01 | 9.853E+00 | 1.591E+01 | 1.653E+01 | 1.128E+01 | 1.431E+01 | 1.557E+01 |
| 292 | 2.323E+00 | 1.694E+00 | 2.165E+00 | 2.032E+00 | 2.630E+00 | 2.589E+00 | 1.814E+00 | 1.555E+00 | 2.387E+00 | 2.753E+00 | 1.799E+00 | 2.281E+00 | 2.292E+00 |
| 293 | 1.923E+00 | 2.495E+00 | 9.766E−01 | 2.399E+00 | 3.153E+00 | 3.159E+00 | 1.598E+00 | 1.206E+00 | 1.734E+00 | 2.049E+00 | 1.904E+00 | 1.730E+00 | 1.663E+00 |
| 294 | 2.093E+00 | 2.034E+00 | 6.709E−01 | 2.121E+00 | 2.151E+00 | 2.318E+00 | 1.778E+00 | 1.971E+00 | 2.296E+00 | 3.023E+00 | 2.176E+00 | 2.737E+00 | 2.419E+00 |
| 295 | 2.053E+00 | 1.989E+00 | 6.941E−01 | 2.170E+00 | 2.108E+00 | 2.330E+00 | 1.773E+00 | 2.371E+00 | 2.290E+00 | 3.095E+00 | 2.226E+00 | 2.793E+00 | 2.339E+00 |
| 296 | 1.260E+00 | 1.447E+00 | 4.892E−01 | 1.434E+00 | 1.256E+00 | 1.218E+00 | 1.248E+00 | 1.560E+00 | 1.259E+00 | 1.578E+00 | 1.444E+00 | 1.712E+00 | 1.758E+00 |
| 297 | 2.443E−01 | 3.102E−01 | 2.136E+00 | 2.879E−01 | 3.962E−01 | 2.520E−01 | 2.505E−01 | 1.643E−01 | 2.399E−01 | 1.500E−01 | 1.324E−01 | 2.265E−01 | 1.948E−01 |

APPENDIX D-continued

Ovarian Cancer
Training Dataset

| | | | | | | | | | | | | | |
|---|---|---|---|---|---|---|---|---|---|---|---|---|---|
| 298 | 1.040E−02 | 1.748E−02 | 7.079E−02 | 1.594E−02 | 2.424E−02 | 1.324E−02 | 1.266E−02 | 1.562E−02 | 9.482E−03 | 9.224E−03 | 1.259E−02 | 2.064E−02 | 8.988E−03 |
| 299 | 6.200E−02 | 2.581E−01 | 6.609E−01 | 1.388E−01 | 3.444E−01 | 1.330E−01 | 1.313E−01 | 6.886E−02 | 6.328E−02 | 4.441E−02 | 6.822E−02 | 8.881E−02 | 7.680E−02 |
| 300 | 4.634E−03 | 1.414E−02 | 3.389E−02 | 6.822E−03 | 2.029E−02 | 1.079E−02 | 6.050E−03 | 4.634E−03 | 4.891E−03 | 2.553E−03 | 4.483E−03 | 1.259E−02 | 6.071E−03 |
| 301 | 5.728E−02 | 1.199E−01 | 3.314E−01 | 9.031E−02 | 1.695E−01 | 9.525E−02 | 1.023E−01 | 6.307E−02 | 4.913E−02 | 4.183E−02 | 4.891E−02 | 6.822E−02 | 6.650E−02 |
| 302 | 8.538E−03 | 1.199E−02 | 1.167E−01 | 7.701E−03 | 2.252E−02 | 1.302E−02 | 6.736E−03 | 8.667E−03 | 8.323E−03 | 5.964E−03 | 8.452E−03 | 1.015E−02 | 7.766E−03 |
| 303 | 2.393E−01 | 2.588E−01 | 7.716E−01 | 2.630E−01 | 3.900E−01 | 3.182E−01 | 3.138E−01 | 1.873E−01 | 2.623E−01 | 2.122E−01 | 2.447E−01 | 2.723E−01 | 2.595E−01 |
| 304 | 2.875E−03 | 4.998E−03 | 1.178E−02 | 3.668E−03 | 8.774E−03 | 2.853E−03 | 2.424E−03 | 5.792E−03 | 8.624E−03 | 2.424E−03 | 2.338E−03 | 5.599E−03 | 3.883E−03 |
| 305 | 3.763E−01 | 6.154E−01 | 2.001E+00 | 5.183E−01 | 8.689E−01 | 5.148E−01 | 5.628E−01 | 2.556E−01 | 3.873E−01 | 2.463E−01 | 2.954E−01 | 3.762E−01 | 3.595E−01 |
| 306 | 2.360E−02 | 3.969E−02 | 1.176E−01 | 3.733E−02 | 6.972E−02 | 5.406E−02 | 3.475E−02 | 2.424E−02 | 2.982E−02 | 2.130E−02 | 2.102E−02 | 4.333E−02 | 3.003E−02 |
| 307 | 2.081E+00 | 1.174E+00 | 3.918E+00 | 1.899E+00 | 1.933E+00 | 2.057E+00 | 2.167E−01 | 1.379E+00 | 2.138E+00 | 1.836E+00 | 1.372E+00 | 2.332E+00 | 2.019E+00 |
| 308 | 3.282E−02 | 1.497E−02 | 6.393E−02 | 2.660E−02 | 3.776E−02 | 3.432E−02 | 2.767E−02 | 2.724E−02 | 2.896E−02 | 2.617E−02 | 2.639E−02 | 3.883E−02 | 2.939E−02 |
| 309 | 3.389E−03 | 9.653E−03 | 2.107E−02 | 9.096E−03 | 1.103E−02 | 5.492E−03 | 4.848E−03 | 2.896E−03 | 4.891E−03 | 2.982E−03 | 2.875E−03 | 5.942E−03 | 3.389E−03 |
| 310 | 2.132E−03 | 2.338E−03 | 7.508E−03 | 2.274E−03 | 5.771E−03 | 2.446E−03 | 1.480E−03 | 9.825E−03 | 2.012E−03 | 2.553E−03 | 1.437E−03 | 5.234E−03 | 1.699E−03 |
| 311 | 3.754E−04 | 3.325E−04 | 1.070E−03 | 8.752E−04 | 1.253E−03 | 8.152E−04 | 4.033E−04 | 1.735E−03 | 2.596E−03 | 1.137E−03 | 1.798E−04 | 1.049E−03 | 4.848E−04 |
| 312 | 1.255E−04 | 2.338E−03 | 3.561E−04 | 5.256E−04 | 7.508E−04 | 1.424E−03 | 1.345E−04 | 5.792E−04 | 2.875E−04 | 2.832E−04 | 0.000E+00 | 0.000E+00 | 4.848E−04 |
| 313 | 1.197E−01 | 1.382E−01 | 5.210E−01 | 1.448E−01 | 2.359E−01 | 1.542E−01 | 1.306E−01 | 1.081E−01 | 8.903E−02 | 7.036E−02 | 6.908E−02 | 1.242E−01 | 1.294E−01 |
| 314 | 5.020E−03 | 5.492E−03 | 1.929E−02 | 7.701E−03 | 1.051E−02 | 8.345E−03 | 5.642E−03 | 1.098E−02 | 4.312E−03 | 2.832E−03 | 7.015E−03 | 1.572E−02 | 1.360E−02 |
| 315 | 2.639E−02 | 4.719E−02 | 1.214E−01 | 2.639E−02 | 4.913E−02 | 2.574E−02 | 2.724E−02 | 2.660E−02 | 3.046E−02 | 1.903E−02 | 1.671E−02 | 2.724E−02 | 2.767E−02 |
| 316 | 3.754E−04 | 9.975E−04 | 1.785E−03 | 1.750E−03 | 1.753E−03 | 1.424E−03 | 9.417E−04 | 2.896E−03 | 2.012E−03 | 5.685E−04 | 1.437E−03 | 3.497E−03 | 1.699E−03 |
| 317 | 2.167E−02 | 2.703E−02 | 8.431E−02 | 2.510E−02 | 3.733E−02 | 2.639E−02 | 2.044E−02 | 2.896E−02 | 2.381E−02 | 1.349E−02 | 1.851E−02 | 2.381E−02 | 2.660E−02 |
| 318 | 1.630E−03 | 9.975E−04 | 3.218E−03 | 2.810E−03 | 3.003E−03 | 1.832E−03 | 1.077E−03 | 2.317E−03 | 2.596E−03 | 8.517E−04 | 1.259E−03 | 1.748E−03 | 2.917E−03 |
| 319 | 2.025E−01 | 1.287E−01 | 6.170E−01 | 1.828E−01 | 2.880E−01 | 2.540E−01 | 1.654E−01 | 1.568E−01 | 2.023E−01 | 1.242E−01 | 1.611E−01 | 1.304E−01 | 2.040E−01 |
| 320 | 1.004E−03 | 3.325E−04 | 1.785E−03 | 5.256E−04 | 1.504E−03 | 1.221E−03 | 8.066E−04 | 5.792E−04 | 5.749E−04 | 5.685E−04 | 1.798E−04 | 1.049E−03 | 4.848E−04 |
| 321 | 1.866E−01 | 1.875E−01 | 9.987E−01 | 2.276E−01 | 3.554E−01 | 2.783E−01 | 1.853E−01 | 1.064E−01 | 1.534E−01 | 8.581E−02 | 1.002E−01 | 1.100E−01 | 1.643E−01 |
| 322 | 5.771E−03 | 5.149E−03 | 2.960E−02 | 9.289E−03 | 1.351E−02 | 7.744E−03 | 6.050E−03 | 1.098E−02 | 6.886E−03 | 3.261E−03 | 5.749E−03 | 5.942E−03 | 5.342E−03 |
| 323 | 2.438E−01 | 1.281E−01 | 7.659E−01 | 2.122E−01 | 2.665E−01 | 3.198E−01 | 2.032E−01 | 1.735E−01 | 2.264E−01 | 1.461E−01 | 1.791E−01 | 1.798E−01 | 2.318E−01 |
| 324 | 6.135E−03 | 4.483E−03 | 2.424E−02 | 6.307E−03 | 1.002E−02 | 1.120E−02 | 6.586E−03 | 9.825E−03 | 7.186E−03 | 2.982E−03 | 5.578E−03 | 3.840E−03 | 8.259E−03 |
| 325 | 6.779E−03 | 1.032E−02 | 2.853E−02 | 7.530E−03 | 1.504E−02 | 1.139E−02 | 1.156E−02 | 1.214E−02 | 6.886E−03 | 6.393E−03 | 5.942E−03 | 9.096E−03 | 9.718E−03 |
| 326 | 1.504E−03 | 6.650E−04 | 1.429E−03 | 1.051E−03 | 1.753E−03 | 1.424E−03 | 8.066E−04 | 2.317E−03 | 2.875E−03 | 7.101E−04 | 1.259E−03 | 3.153E−03 | 1.699E−03 |
| 327 | 7.894E−03 | 1.347E−02 | 2.896E−02 | 9.632E−03 | 1.579E−02 | 1.384E−02 | 1.266E−02 | 1.040E−02 | 8.323E−03 | 6.243E−03 | 1.169E−02 | 9.782E−03 | 1.068E−02 |
| 328 | 1.379E−03 | 1.997E−03 | 1.429E−03 | 1.401E−03 | 3.754E−03 | 2.853E−03 | 2.295E−03 | 2.317E−03 | 8.624E−04 | 1.847E−03 | 1.259E−03 | 3.840E−03 | 1.941E−03 |
| 329 | 4.256E−01 | 3.909E−01 | 1.663E+00 | 3.809E−01 | 6.076E−01 | 4.631E−01 | 3.505E−01 | 2.672E−01 | 4.572E−01 | 2.291E−01 | 1.961E−01 | 2.021E−01 | 2.991E−01 |
| 330 | 4.891E−03 | 5.985E−03 | 1.607E−02 | 4.913E−03 | 6.264E−03 | 6.521E−03 | 3.497E−03 | 5.213E−03 | 5.170E−03 | 4.677E−03 | 3.776E−03 | 4.891E−03 | 5.106E−03 |
| 331 | 2.360E−02 | 3.625E−02 | 1.251E−01 | 2.639E−02 | 6.135E−02 | 3.089E−02 | 3.068E−02 | 2.083E−02 | 3.132E−02 | 1.974E−02 | 2.231E−02 | 2.381E−02 | 2.274E−02 |
| 332 | 5.020E−04 | 1.830E−03 | 3.218E−03 | 3.497E−04 | 2.252E−03 | 1.424E−03 | 4.033E−04 | 1.156E−03 | 1.725E−03 | 9.932E−04 | 1.079E−03 | 1.748E−03 | 4.848E−04 |
| 333 | 1.568E−02 | 2.317E−02 | 7.036E−02 | 1.892E−02 | 3.111E−02 | 2.553E−02 | 2.682E−02 | 1.735E−02 | 1.695E−02 | 1.193E−02 | 1.384E−02 | 1.678E−02 | 1.360E−02 |
| 334 | 1.255E−04 | 3.325E−04 | 0.000E+00 | 8.752E−04 | 2.510E−04 | 6.114E−04 | 4.033E−04 | 1.735E−03 | 5.749E−04 | 0.000E+00 | 3.604E−04 | 0.000E+00 | 4.848E−04 |
| 335 | 3.776E−02 | 3.454E−02 | 1.789E−01 | 3.583E−02 | 6.693E−02 | 5.771E−02 | 4.012E−02 | 2.424E−02 | 5.749E−02 | 3.475E−02 | 3.411E−02 | 2.724E−02 | 3.111E−02 |
| 336 | 1.255E−03 | 3.497E−03 | 7.144E−03 | 1.926E−03 | 4.505E−03 | 2.231E−03 | 2.553E−03 | 4.634E−03 | 3.153E−03 | 1.705E−03 | 2.167E−03 | 5.599E−03 | 4.848E−03 |
| 337 | 8.602E−02 | 8.581E−02 | 4.442E−01 | 8.924E−02 | 1.678E−01 | 1.004E−01 | 7.487E−02 | 3.411E−02 | 8.474E−02 | 4.848E−02 | 3.776E−02 | 3.604E−02 | 5.749E−02 |
| 338 | 1.630E−03 | 1.497E−03 | 8.216E−03 | 2.810E−03 | 3.003E−03 | 2.036E−03 | 1.345E−03 | 0.000E+00 | 2.295E−03 | 1.279E−03 | 1.259E−03 | 2.789E−03 | 2.917E−03 |
| 339 | 4.119E−02 | 2.875E−02 | 1.714E−01 | 3.861E−02 | 5.363E−02 | 5.771E−02 | 3.990E−02 | 3.475E−02 | 4.762E−02 | 3.368E−02 | 2.875E−02 | 2.167E−02 | 3.368E−02 |
| 340 | 1.504E−03 | 3.153E−03 | 8.559E−03 | 2.446E−03 | 5.513E−03 | 2.853E−03 | 6.736E−04 | 8.087E−03 | 3.733E−03 | 2.703E−03 | 1.978E−03 | 2.789E−03 | 3.389E−03 |
| 341 | 2.875E−03 | 4.827E−03 | 1.536E−02 | 4.719E−03 | 9.010E−03 | 5.706E−03 | 4.312E−03 | 9.825E−03 | 3.454E−03 | 3.840E−03 | 2.875E−03 | 5.234E−03 | 5.106E−03 |
| 342 | 3.754E−04 | 1.997E−03 | 1.785E−03 | 7.015E−04 | 1.504E−03 | 1.017E−03 | 2.682E−04 | 5.792E−04 | 5.749E−04 | 8.517E−04 | 1.798E−04 | 3.497E−03 | 7.272E−04 |
| 343 | 5.277E−03 | 8.495E−03 | 1.999E−02 | 7.015E−03 | 8.517E−03 | 6.114E−03 | 5.642E−03 | 6.371E−03 | 4.033E−03 | 4.548E−03 | 5.578E−03 | 9.782E−03 | 6.071E−03 |
| 344 | 7.530E−04 | 6.650E−04 | 3.561E−04 | 1.051E−03 | 5.020E−04 | 2.036E−04 | 2.682E−04 | 1.156E−03 | 0.000E+00 | 5.685E−04 | 1.798E−04 | 1.049E−03 | 4.848E−04 |

APPENDIX D-continued

Ovarian Cancer Training Dataset

| | BL | BM | BN | BO | BP | BQ | BR | BS | BT | BU | BV | BW | BX |
|---|---|---|---|---|---|---|---|---|---|---|---|---|---|
| 1 | 14670 | 13667 | CA056 | CA132 | CA069 | CA075 | CA253 | CA131 | 14725 | 14481 | 14486 | CA417 | CA074 |
| 2 | Benign | Late Malignant | Control | Control | Control | Control | Control | Control | Early Malignant | Late Malignant | Benign | Control | Control |
| 3 | 1 | 3 | 0 | 0 | 0 | 0 | 0 | 0 | 2 | 3 | 1 | 0 | 0 |
| 4 | −1 | −1 | 1 | 1 | 1 | 1 | 1 | 1 | −1 | −1 | −1 | 1 | 1 |
| 5 | 1.725E+00 | 1.014E+00 | 1.496E+00 | 1.241E+00 | 2.089E+00 | 1.512E+00 | 2.173E+00 | 1.859E+00 | 1.789E+00 | 1.753E+00 | 2.292E+00 | 1.780E+00 | 2.525E+00 |
| 6 | 7.178E−01 | 2.446E−01 | 7.460E−01 | 5.224E−01 | 1.008E+00 | 5.816E−01 | 1.032E+00 | 1.028E+00 | 1.064E+00 | 3.230E−01 | 8.926E−01 | 8.889E−01 | 1.165E+00 |
| 7 | 1.899E−01 | 9.979E−02 | 2.296E−01 | 1.427E−01 | 2.135E−01 | 1.609E−01 | 3.197E−01 | 2.468E−01 | 2.736E−01 | 1.159E−01 | 3.358E−01 | 2.017E−01 | 2.758E−01 |
| 8 | 1.373E+00 | 6.309E−01 | 7.407E−01 | 7.194E−01 | 1.090E+00 | 5.837E−01 | 1.060E+00 | 1.357E+00 | 8.640E−01 | 1.900E+00 | 1.106E+00 | 1.365E+00 | 1.674E+00 |
| 9 | 4.378E−02 | 3.723E−02 | 2.210E−02 | 2.307E−02 | 3.755E−02 | 2.371E−02 | 3.734E−02 | 4.324E−02 | 3.498E−02 | 2.779E−02 | 3.959E−02 | 2.650E−02 | 3.723E−02 |
| 10 | 7.961E−03 | 6.760E−03 | 2.006E−02 | 1.127E−02 | 1.406E−02 | 1.137E−02 | 2.049E−02 | 1.781E−02 | 1.363E−02 | 7.135E−03 | 2.006E−02 | 1.985E−02 | 2.124E−02 |
| 11 | 1.459E−02 | 1.695E−03 | 1.384E−02 | 1.084E−02 | 1.234E−02 | 6.470E−03 | 1.770E−02 | 1.867E−02 | 2.049E−02 | 8.723E−03 | 1.384E−02 | 1.513E−02 | 1.545E−02 |
| 12 | 1.191E−02 | 1.014E−02 | 8.584E−03 | 9.485E−03 | 9.528E−03 | 5.397E−03 | 1.094E−02 | 1.025E−02 | 1.000E−02 | 7.929E−03 | 5.783E−03 | 7.092E−03 | 1.170E−02 |
| 13 | 2.124E−02 | 8.455E−03 | 1.223E−02 | 8.584E−03 | 1.288E−02 | 7.554E−03 | 1.047E−02 | 1.781E−02 | 1.094E−02 | 3.326E−02 | 6.674E−03 | 9.453E−03 | 2.178E−02 |
| 14 | 2.918E−02 | 2.876E−02 | 5.429E−02 | 3.616E−02 | 6.052E−02 | 4.260E−02 | 7.468E−02 | 3.745E−02 | 7.457E−02 | 3.090E−02 | 5.429E−02 | 6.760E−02 | 4.517E−02 |
| 15 | 1.061E−02 | 8.455E−03 | 8.991E−03 | 3.616E−03 | 5.612E−03 | 2.157E−03 | 3.637E−03 | 5.794E−03 | 8.637E−03 | 6.341E−03 | 6.223E−03 | 6.148E−03 | 4.260E−03 |
| 16 | 0.000E+00 | 0.000E+00 | 8.176E−04 | 4.517E−04 | 1.127E−03 | 5.397E−04 | 1.363E−03 | 4.453E−04 | 0.000E+00 | 1.588E−03 | 1.330E−03 | 9.453E−04 | 1.599E−03 |
| 17 | 1.330E−03 | 6.760E−03 | 2.446E−03 | 2.264E−03 | 3.369E−03 | 1.620E−03 | 2.275E−03 | 6.234E−03 | 2.725E−03 | 3.959E−03 | 3.112E−03 | 3.305E−03 | 2.124E−03 |
| 18 | 2.253E−02 | 3.884E−02 | 2.285E−02 | 1.674E−02 | 3.981E−02 | 2.639E−02 | 2.135E−02 | 3.122E−02 | 1.813E−02 | 3.326E−02 | 2.532E−02 | 1.513E−02 | 3.036E−02 |
| 19 | 9.421E−02 | 6.760E−02 | 7.843E−02 | 4.657E−02 | 9.367E−02 | 7.500E−02 | 1.094E−01 | 8.283E−02 | 8.315E−02 | 6.738E−02 | 1.180E−01 | 8.745E−02 | 1.384E−01 |
| 20 | 0.000E+00 | 0.000E+00 | 2.446E−03 | 3.616E−03 | 2.800E−03 | 1.620E−03 | 1.363E−03 | 8.906E−04 | 9.088E−04 | 1.588E−03 | 4.453E−04 | 2.833E−03 | 2.661E−03 |
| 21 | 1.985E−02 | 5.075E−03 | 1.180E−02 | 7.682E−03 | 1.792E−02 | 1.245E−02 | 2.006E−02 | 2.178E−02 | 1.277E−02 | 7.929E−03 | 1.867E−02 | 1.416E−02 | 3.036E−02 |
| 22 | 1.330E−03 | 1.695E−03 | 0.000E+00 | 1.352E−03 | 5.612E−04 | 2.157E−03 | 9.109E−04 | 2.232E−03 | 1.813E−03 | 2.382E−03 | 1.781E−03 | 1.416E−03 | 3.187E−03 |
| 23 | 2.393E−02 | 3.380E−02 | 3.884E−02 | 2.940E−02 | 5.547E−02 | 3.777E−02 | 4.775E−02 | 4.678E−02 | 3.273E−02 | 3.015E−02 | 3.734E−02 | 3.165E−02 | 5.687E−02 |
| 24 | 3.455E−02 | 2.028E−02 | 4.614E−02 | 4.700E−02 | 6.223E−02 | 7.124E−02 | 7.371E−02 | 6.642E−02 | 8.090E−02 | 6.663E−02 | 6.631E−02 | 4.399E−02 | 5.633E−02 |
| 25 | 2.124E−02 | 8.455E−03 | 1.148E−02 | 1.856E−02 | 2.693E−02 | 1.025E−02 | 2.135E−02 | 1.867E−02 | 2.135E−02 | 6.341E−03 | 2.672E−02 | 1.845E−02 | 3.348E−02 |
| 26 | 2.650E−03 | 1.695E−02 | 1.180E−02 | 2.264E−03 | 2.071E−02 | 1.352E−02 | 1.770E−02 | 1.867E−02 | 2.403E−02 | 1.427E−02 | 1.330E−02 | 1.373E−02 | 9.571E−03 |
| 27 | 2.650E−03 | 8.455E−03 | 3.273E−03 | 9.034E−04 | 3.369E−03 | 4.313E−03 | 3.637E−03 | 6.685E−03 | 3.187E−03 | 4.753E−03 | 8.004E−03 | 4.260E−03 | 3.187E−03 |
| 28 | 1.856E−02 | 1.695E−02 | 2.167E−02 | 2.800E−02 | 2.918E−02 | 3.133E−02 | 3.090E−02 | 3.959E−02 | 3.358E−02 | 2.532E−02 | 3.873E−02 | 1.985E−02 | 5.161E−02 |
| 29 | 2.650E−02 | 2.028E−02 | 4.131E−02 | 4.335E−02 | 4.206E−02 | 3.026E−02 | 4.464E−02 | 2.983E−02 | 5.043E−02 | 2.779E−02 | 4.624E−02 | 3.788E−02 | 5.633E−02 |
| 30 | 5.043E−02 | 2.371E−02 | 6.127E−02 | 4.882E−02 | 5.998E−02 | 5.933E−02 | 7.918E−02 | 6.009E−02 | 6.631E−02 | 4.592E−02 | 7.028E−02 | 5.107E−02 | 6.277E−02 |
| 31 | 1.985E−02 | 3.047E−02 | 5.676E−02 | 4.206E−02 | 4.260E−02 | 4.421E−02 | 3.691E−02 | 2.543E−02 | 4.549E−02 | 4.914E−02 | 4.399E−02 | 3.122E−02 | 3.723E−02 |
| 32 | 3.187E−02 | 6.760E−03 | 2.575E−02 | 2.393E−02 | 5.612E−02 | 2.639E−02 | 4.689E−02 | 6.009E−02 | 2.865E−02 | 8.165E−02 | 3.251E−02 | 5.912E−02 | 7.554E−02 |
| 33 | 3.981E−03 | 3.380E−03 | 6.127E−03 | 7.232E−03 | 1.180E−02 | 1.084E−02 | 1.001E−02 | 7.575E−03 | 8.637E−03 | 8.723E−03 | 8.455E−03 | 1.084E−02 | 8.509E−03 |
| 34 | 2.221E−01 | 1.674E−01 | 1.792E−01 | 2.554E−01 | 2.908E−01 | 3.423E−01 | 2.210E−01 | 2.543E−01 | 2.028E−01 | 3.841E−01 | 2.189E−01 | 2.039E−01 | 3.240E−01 |
| 35 | 5.172E−02 | 4.903E−02 | 7.682E−02 | 5.418E−02 | 7.124E−02 | 5.182E−02 | 8.648E−02 | 5.258E−02 | 7.500E−02 | 6.577E−02 | 6.674E−02 | 7.135E−02 | 5.848E−02 |
| 36 | 5.311E−03 | 0.000E+00 | 8.991E−03 | 2.715E−03 | 6.727E−03 | 7.554E−03 | 6.373E−03 | 8.906E−03 | 7.275E−03 | 8.723E−03 | 4.453E−03 | 5.676E−03 | 5.322E−03 |
| 37 | 2.393E−02 | 1.695E−03 | 1.803E−02 | 1.631E−02 | 1.288E−02 | 1.781E−02 | 1.685E−02 | 1.824E−02 | 1.363E−02 | 1.030E−02 | 1.781E−02 | 1.416E−02 | 9.045E−03 |
| 38 | 1.459E−02 | 6.760E−03 | 8.176E−03 | 1.491E−02 | 2.414E−02 | 1.459E−02 | 8.197E−03 | 9.796E−03 | 1.545E−02 | 1.502E−02 | 1.202E−02 | 1.040E−02 | 1.438E−02 |
| 39 | 7.564E−02 | 1.856E−02 | 1.406E−01 | 1.524E−01 | 9.195E−02 | 5.290E−02 | 8.562E−02 | 5.118E−02 | 1.212E−01 | 3.412E−02 | 1.352E−01 | 1.049E−01 | 6.491E−02 |
| 40 | 1.524E−01 | 1.234E−01 | 1.245E−01 | 1.481E−01 | 1.856E−01 | 1.352E−01 | 2.006E−01 | 1.609E−01 | 1.191E−01 | 1.695E−01 | 1.749E−01 | 1.277E−01 | 9.356E−02 |
| 41 | 2.124E−02 | 2.876E−02 | 1.180E−02 | 1.803E−02 | 2.296E−02 | 2.157E−02 | 1.867E−02 | 2.049E−02 | 1.631E−02 | 3.326E−02 | 1.953E−02 | 1.470E−02 | 2.017E−02 |
| 42 | 1.330E−03 | 1.695E−03 | 4.088E−04 | 9.034E−04 | 3.927E−03 | 5.397E−04 | 1.363E−03 | 2.232E−03 | 9.088E−04 | 1.588E−03 | 1.781E−03 | 1.888E−03 | 1.599E−03 |
| 43 | 1.273E−42 | 2.829E−03 | 4.604E−03 | 3.678E−03 | 5.787E−43 | 6.456E−03 | 6.558E−03 | 5453E−03 | 6.198E−43 | 3.241E−03 | 7.047E−03 | 6.018E−03 | 5.993E−03 |
| 44 | 2.176E−01 | 1.893E−01 | 1.325E−01 | 1.357E−01 | 2.122E−01 | 2.165E−01 | 2.056E−01 | 1.677E−01 | 1.995E−01 | 1.916E−01 | 1.661E−01 | 1.651E−01 | 1.928E−01 |
| 45 | 8.487E−02 | 5.993E−02 | 7.716E−02 | 7.279E−02 | 1.088E−01 | 8.179E−02 | 8.513E−02 | 8.410E−02 | 1.006E−01 | 7.639E−02 | 7.279E−02 | 7.716E−02 | 1.036E−01 |
| 46 | 1.116E−01 | 4.861E−02 | 6.944E−02 | 6.739E−02 | 9.851E−02 | 6.970E−02 | 8.462E−02 | 8.436E−02 | 1.083E−01 | 1.201E−01 | 8.359E−02 | 9.002E−02 | 9.722E−02 |
| 47 | 1.384E−01 | 9.285E−02 | 9.310E−02 | 8.642E−02 | 1.283E−01 | 1.024E−01 | 9.722E−02 | 9.696E−02 | 1.327E−01 | 1.294E−01 | 1.073E−01 | 8.873E−02 | 1.319E−01 |

APPENDIX D-continued

Ovarian Cancer
Training Dataset

| | | | | | | | | | | | | | |
|---|---|---|---|---|---|---|---|---|---|---|---|---|---|
| 48 | 1.399E−02 | 9.722E−03 | 1.723E−02 | 1.116E−02 | 1.667E−02 | 8.410E−03 | 1.494E−02 | 9.490E−03 | 2.091E−02 | 1.008E−02 | 1.515E−02 | 1.780E−02 | 1.607E−02 |
| 49 | 5.401E−03 | 6.893E−03 | 8.410E−03 | 4.218E−03 | 6.867E−03 | 5.298E−03 | 6.996E−03 | 3.832E−03 | 9.799E−03 | 3.421E−03 | 4.912E−03 | 6.919E−03 | 5.221E−03 |
| 50 | 2.855E−03 | 4.064E−04 | 2.058E−03 | 2.701E−03 | 8.076E−04 | 1.551E−03 | 2.400E−03 | 3.215E−03 | 4.784E−03 | 2.091E−03 | 2.027E−03 | 3.061E−03 | 2.423E−03 |
| 51 | 2.427E−01 | 8.513E−02 | 2.459E−01 | 1.152E−01 | 9.851E−02 | 2.175E−01 | 1.733E−01 | 1.466E−01 | 1.674E−01 | 1.065E−01 | 2.094E−01 | 1.345E−01 | 1.175E−01 |
| 52 | 6.687E−03 | 0.000E+00 | 3.524E−03 | 1.517E−03 | 1.075E−03 | 2.726E−03 | 2.958E−03 | 3.421E−03 | 3.266E−03 | 2.649E−03 | 1.386E−03 | 2.598E−03 | 1.276E−03 |
| 53 | 3.524E−02 | 2.430E−02 | 3.292E−02 | 3.806E−02 | 3.832E−02 | 4.089E−02 | 2.958E−02 | 3.472E−02 | 2.906E−02 | 5.272E−02 | 3.163E−02 | 2.436E−02 | 4.475E−02 |
| 54 | 4.275E+00 | 3.327E+00 | 5.282E+00 | 6.619E+00 | 4.653E+00 | 5.538E+00 | 4.892E+00 | 5.463E+00 | 4.410E+00 | 5.019E+00 | 4.730E+00 | 4.960E+00 | 5.866E+00 |
| 55 | 5.579E−01 | 3.092E−01 | 5.981E−01 | 5.269E−01 | 4.748E−01 | 6.784E−01 | 7.498E−01 | 6.949E−01 | 6.615E−01 | 4.834E−01 | 6.968E−01 | 5.270E−01 | 4.820E−01 |
| 56 | 1.412E−01 | 1.281E−01 | 1.815E−01 | 2.230E−01 | 1.935E−01 | 2.195E−01 | 1.887E−01 | 2.195E−01 | 1.811E−01 | 1.453E−01 | 1.607E−01 | 1.926E−01 | 1.962E−01 |
| 57 | 3.533E+00 | 2.259E+00 | 3.766E+00 | 3.342E+00 | 2.799E+00 | 3.789E+00 | 3.999E+00 | 3.443E+00 | 3.505E+00 | 3.148E+00 | 3.917E+00 | 2.948E+00 | 2.682E+00 |
| 58 | 4.732E−02 | 2.513E−02 | 3.729E−02 | 3.009E−02 | 3.318E−02 | 3.061E−02 | 3.215E−02 | 3.781E−02 | 3.369E−02 | 5.658E−02 | 3.549E−02 | 2.778E−02 | 3.652E−02 |
| 59 | 5.401E−02 | 3.318E−02 | 6.867E−02 | 5.144E−02 | 5.401E−02 | 6.944E−02 | 7.639E−02 | 5.864E−02 | 6.841E−02 | 4.552E−02 | 7.819E−02 | 5.787E−02 | 4.887E−02 |
| 60 | 1.368E−02 | 1.744E−02 | 1.577E−02 | 1.906E−02 | 1.721E−02 | 1.901E−02 | 2.009E−02 | 1.623E−02 | 1.754E−02 | 2.598E−02 | 1.929E−02 | 1.201E−02 | 2.294E−02 |
| 61 | 8.645E−01 | 6.261E−01 | 1.622E+00 | 1.109E+00 | 1.357E+00 | 1.212E+00 | 1.390E+00 | 1.122E+00 | 1.646E+00 | 9.713E−01 | 1.427E+00 | 2.408E+00 | 1.120E+00 |
| 62 | 6.256E−01 | 3.874E−01 | 3.949E−01 | 5.496E−01 | 4.722E−01 | 4.548E−01 | 4.654E−01 | 5.404E−01 | 4.069E−01 | 3.424E−01 | 4.649E−01 | 4.135E−01 | 5.609E−01 |
| 63 | 6.996E−03 | 3.652E−03 | 1.253E−02 | 1.083E−02 | 1.317E−02 | 8.282E−03 | 8.076E−03 | 1.152E−02 | 1.263E−02 | 1.235E−02 | 9.593E−03 | 1.893E−02 | 1.186E−02 |
| 64 | 2.702E+00 | 1.543E+00 | 3.189E+00 | 4.189E+00 | 3.805E+00 | 3.582E+00 | 3.422E+00 | 3.723E+00 | 3.301E+00 | 2.990E+00 | 3.428E+00 | 3.418E+00 | 3.948E+00 |
| 65 | 1.147E−01 | 6.404E−02 | 1.119E−01 | 1.542E−01 | 1.451E−01 | 1.235E−01 | 1.134E−01 | 1.345E−01 | 1.178E−01 | 1.283E−01 | 1.121E−01 | 1.240E−01 | 1.471E−01 |
| 66 | 7.824E−01 | 3.874E−01 | 7.749E−01 | 6.467E−01 | 5.513E−01 | 6.391E−01 | 6.753E−01 | 6.477E−01 | 6.234E−01 | 5.852E−01 | 8.856E−01 | 5.157E−01 | 6.389E−01 |
| 67 | 5.067E−02 | 2.392E−02 | 5.195E−02 | 4.552E−02 | 4.990E−02 | 3.652E−02 | 4.449E−02 | 4.630E−02 | 5.041E−02 | 6.507E−02 | 5.607E−02 | 4.269E−02 | 4.604E−02 |
| 68 | 8.333E−02 | 7.304E−02 | 6.764E−02 | 1.067E−01 | 1.129E−01 | 1.238E−01 | 8.102E−02 | 8.333E−02 | 7.896E−02 | 1.345E−01 | 8.436E−02 | 6.276E−02 | 1.502E−01 |
| 69 | 4.650E−01 | 3.226E−01 | 8.369E−01 | 5.709E−01 | 7.785E−01 | 4.949E−01 | 6.494E−01 | 4.836E−01 | 9.741E−01 | 5.018E−01 | 7.596E−01 | 1.137E+00 | 5.889E−01 |
| 70 | 2.803E−02 | 1.499E−02 | 3.112E−02 | 2.803E−02 | 3.652E−02 | 2.932E−02 | 3.086E−02 | 2.382E−02 | 3.575E−02 | 2.855E−02 | 2.932E−02 | 3.909E−02 | 2.701E−02 |
| 71 | 9.233E−03 | 8.513E−03 | 7.150E−03 | 4.887E−03 | 6.327E−03 | 6.070E−03 | 8.950E−03 | 3.524E−03 | 1.003E−02 | 2.855E−03 | 5.221E−03 | 8.385E−03 | 3.832E−03 |
| 72 | 7.639E−03 | 1.217E−03 | 2.546E−03 | 1.842E−03 | 2.958E−03 | 1.939E−03 | 3.601E−03 | 3.215E−03 | 4.475E−03 | 3.241E−03 | 2.778E−03 | 3.292E−03 | 2.932E−03 |
| 73 | 1.400E−03 | 0.000E+00 | 1.716E−03 | 1.422E−03 | 5.903E−04 | 2.833E−03 | 0.000E+00 | 9.368E−04 | 0.000E+00 | 3.330E−03 | 4.684E−04 | 0.000E+00 | 1.119E−03 |
| 74 | 2.788E−03 | 7.111E−03 | 1.716E−03 | 1.896E−03 | 2.359E−03 | 3.973E−03 | 1.919E−03 | 3.284E−03 | 3.826E−03 | 4.165E−03 | 3.273E−03 | 3.476E−03 | 0.000E+00 |
| 75 | 3.634E−02 | 4.447E−02 | 4.639E−02 | 4.323E−02 | 5.011E−02 | 5.451E−02 | 4.977E−02 | 2.810E−02 | 5.158E−02 | 3.589E−02 | 3.093E−02 | 3.330E−02 | 2.291E−02 |
| 76 | 4.187E−02 | 5.508E−02 | 6.106E−02 | 7.325E−02 | 6.783E−02 | 9.312E−02 | 5.124E−02 | 3.138E−02 | 4.594E−02 | 6.749E−02 | 4.357E−02 | 5.576E−02 | 3.804E−02 |
| 77 | 4.187E−03 | 1.783E−03 | 8.600E−03 | 3.804E−03 | 1.772E−03 | 2.833E−03 | 1.006E−02 | 5.621E−03 | 6.693E−03 | 8.341E−04 | 7.020E−03 | 6.467E−03 | 1.682E−03 |
| 78 | 0.000E+00 | 1.783E−03 | 8.600E−04 | 9.503E−04 | 5.903E−04 | 5.677E−04 | 0.000E+00 | 0.000E+00 | 4.786E−04 | 8.341E−04 | 1.874E−03 | 0.000E+00 | 1.119E−03 |
| 79 | 2.788E−03 | 1.603E−02 | 4.300E−04 | 4.752E−04 | 1.772E−03 | 1.704E−03 | 4.786E−04 | 4.684E−04 | 0.000E+00 | 2.506E−03 | 4.684E−04 | 0.000E+00 | 3.352E−03 |
| 80 | 0.000E+00 | 1.783E−03 | 4.300E−04 | 9.503E−04 | 5.903E−04 | 1.704E−03 | 9.582E−04 | 4.684E−04 | 2.393E−03 | 1.670E−03 | 1.874E−03 | 4.977E−04 | 5.598E−04 |
| 81 | 0.000E+00 | 3.736E−02 | 3.871E−03 | 7.133E−03 | 2.946E−03 | 1.078E−02 | 6.704E−03 | 4.684E−03 | 3.352E−03 | 1.580E−02 | 5.147E−03 | 4.977E−03 | 2.799E−03 |
| 82 | 0.000E+00 | 1.422E−02 | 2.144E−03 | 1.896E−03 | 2.359E−03 | 1.704E−03 | 2.393E−03 | 1.411E−03 | 1.907E−03 | 2.506E−03 | 1.400E−03 | 1.986E−03 | 5.598E−03 |
| 83 | 2.788E−03 | 3.555E−03 | 1.287E−03 | 2.856E−03 | 4.131E−03 | 1.704E−03 | 9.582E−04 | 0.000E+00 | 2.393E−03 | 2.506E−03 | 3.273E−03 | 4.977E−04 | 3.352E−03 |
| 84 | 8.375E−03 | 5.339E−03 | 4.729E−03 | 8.555E−03 | 6.490E−03 | 1.309E−02 | 8.138E−03 | 6.558E−03 | 3.826E−03 | 1.580E−02 | 7.020E−03 | 5.474E−03 | 6.716E−03 |
| 85 | 1.400E−03 | 3.555E−03 | 8.600E−04 | 2.856E−03 | 1.185E−03 | 1.704E−03 | 1.433E−03 | 0.000E+00 | 4.300E−03 | 2.506E−03 | 1.400E−03 | 9.944E−04 | 2.799E−03 |
| 86 | 4.187E−03 | 7.111E−03 | 6.874E−03 | 7.607E−03 | 8.262E−03 | 9.650E−03 | 4.312E−03 | 4.221E−03 | 6.693E−03 | 9.176E−03 | 4.684E−03 | 5.474E−03 | 6.151E−03 |
| 87 | 8.375E−03 | 8.894E−03 | 2.359E−02 | 3.093E−02 | 2.709E−02 | 4.086E−02 | 1.433E−02 | 1.174E−02 | 2.009E−02 | 2.088E−02 | 1.309E−02 | 8.454E−03 | 8.397E−03 |
| 88 | 1.400E−03 | 1.783E−03 | 3.442E−03 | 6.659E−03 | 2.946E−03 | 5.677E−03 | 4.786E−04 | 5.621E−03 | 2.867E−03 | 7.506E−03 | 1.400E−03 | 3.476E−03 | 2.799E−03 |
| 89 | 2.788E−03 | 7.111E−03 | 1.242E−02 | 1.479E−02 | 7.664E−03 | 1.422E−02 | 1.102E−02 | 3.747E−03 | 9.086E−03 | 1.163E−02 | 1.123E−02 | 5.474E−03 | 5.034E−03 |
| 90 | 2.235E−02 | 1.242E−02 | 3.442E−02 | 2.325E−02 | 1.941E−02 | 2.494E−02 | 2.585E−02 | 1.591E−02 | 2.483E−02 | 1.163E−02 | 1.400E−02 | 1.490E−02 | 1.174E−02 |
| 91 | 1.400E−03 | 1.783E−03 | 5.158E−03 | 9.503E−03 | 4.718E−03 | 5.113E−03 | 6.704E−03 | 2.348E−03 | 6.219E−03 | 4.165E−03 | 2.336E−03 | 1.490E−03 | 2.799E−03 |
| 92 | 1.116E−02 | 5.339E−03 | 8.600E−03 | 1.524E−02 | 5.903E−03 | 1.422E−02 | 6.704E−03 | 4.221E−03 | 9.086E−03 | 1.084E−02 | 6.546E−03 | 5.474E−03 | 1.063E−02 |
| 93 | 1.400E−03 | 1.067E−02 | 7.731E−03 | 7.133E−03 | 2.946E−03 | 9.650E−03 | 1.433E−03 | 4.684E−04 | 7.167E−03 | 3.330E−03 | 2.810E−03 | 5.474E−03 | 2.235E−03 |
| 94 | 0.000E+00 | 1.783E−03 | 8.600E−04 | 1.422E−03 | 2.359E−03 | 2.833E−03 | 4.786E−04 | 0.000E+00 | 2.393E−03 | 2.506E−03 | 3.273E−03 | 1.490E−03 | 1.682E−03 |
| 95 | 2.788E−03 | 8.894E−03 | 9.029E−03 | 4.278E−03 | 7.077E−03 | 8.510E−03 | 4.786E−03 | 1.874E−03 | 9.086E−03 | 2.506E−03 | 1.219E−02 | 5.971E−03 | 5.598E−03 |
| 96 | 9.774E−03 | 3.555E−03 | 4.300E−03 | 3.804E−03 | 7.664E−03 | 7.946E−03 | 6.704E−03 | 1.411E−03 | 7.167E−03 | 7.506E−03 | 4.210E−03 | 2.483E−03 | 2.799E−03 |
| 97 | 5.587E−03 | 3.555E−03 | 1.287E−03 | 3.804E−03 | 4.131E−03 | 7.381E−03 | 1.919E−03 | 1.874E−03 | 2.867E−03 | 1.670E−03 | 1.874E−03 | 4.481E−03 | 0.000E+00 |

APPENDIX D-continued

Ovarian Cancer
Training Dataset

| | | | | | | | | | | | | | |
|---|---|---|---|---|---|---|---|---|---|---|---|---|---|
| 98 | 1.400E−03 | 7.111E−03 | 8.160E−03 | 6.174E−03 | 1.121E−02 | 1.021E−02 | 6.230E−03 | 2.810E−03 | 5.260E−03 | 2.088E−02 | 4.684E−03 | 4.977E−03 | 8.950E−03 |
| 99 | 1.324E−01 | 5.028E−02 | 1.111E−01 | 8.412E−02 | 1.471E−01 | 5.739E−02 | 1.275E−01 | 7.946E−02 | 7.370E−02 | 8.694E−02 | 9.552E−02 | 9.405E−02 | 8.081E−02 |
| 100 | 4.096E−02 | 1.937E−02 | 2.293E−02 | 2.269E−02 | 3.458E−02 | 2.649E−02 | 2.918E−02 | 2.747E−02 | 2.551E−02 | 4.353E−02 | 2.293E−02 | 2.759E−02 | 3.348E−02 |
| 101 | 1.213E−01 | 1.251E−01 | 1.324E−01 | 1.570E−01 | 1.827E−01 | 1.704E−01 | 1.545E−01 | 1.239E−01 | 1.226E−01 | 1.790E−01 | 1.435E−01 | 1.496E−01 | 1.533E−01 |
| 102 | 5.101E−01 | 3.458E−01 | 4.684E−01 | 4.427E−01 | 5.285E−01 | 5.346E−01 | 3.887E−01 | 4.145E−01 | 3.409E−01 | 8.890E−01 | 4.071E−01 | 4.059E−01 | 4.353E−01 |
| 103 | 1.213E−01 | 1.643E−01 | 1.704E−01 | 1.729E−01 | 2.293E−01 | 2.072E−01 | 2.023E−01 | 1.386E−01 | 1.680E−01 | 1.937E−01 | 1.729E−01 | 1.974E−01 | 1.680E−01 |
| 104 | 2.170E−01 | 2.011E−01 | 1.864E−01 | 1.950E−01 | 2.318E−01 | 2.109E−01 | 1.643E−01 | 2.011E−01 | 1.901E−01 | 3.433E−01 | 1.925E−01 | 1.815E−01 | 2.305E−01 |
| 105 | 4.979E−01 | 7.762E−01 | 6.180E−01 | 7.039E−01 | 7.983E−01 | 9.834E−01 | 6.426E−01 | 6.560E−01 | 5.469E−01 | 1.135E+00 | 5.739E−01 | 6.009E−01 | 6.683E−01 |
| 106 | 1.680E−01 | 7.345E−02 | 1.496E−01 | 1.095E−01 | 1.582E−01 | 1.202E−01 | 1.619E−01 | 1.521E−01 | 1.766E−01 | 1.545E−01 | 1.570E−01 | 1.337E−01 | 1.410E−01 |
| 107 | 1.153E−01 | 6.376E−02 | 1.018E−01 | 8.473E−02 | 1.410E−01 | 1.091E−01 | 1.093E−01 | 1.216E−01 | 9.920E−02 | 1.790E−01 | 1.109E−01 | 1.102E−01 | 1.131E−01 |
| 108 | 1.183E−01 | 1.121E−01 | 1.521E−01 | 1.655E−01 | 2.146E−01 | 1.790E−01 | 1.852E−01 | 1.471E−01 | 1.631E−01 | 1.521E−01 | 1.987E−01 | 1.876E−01 | 2.023E−01 |
| 109 | 4.549E−03 | 3.863E−03 | 7.002E−03 | 5.677E−03 | 1.154E−02 | 1.300E−02 | 7.799E−03 | 7.124E−03 | 6.229E−03 | 1.361E−02 | 3.556E−03 | 2.158E−03 | 1.275E−02 |
| 110 | 2.269E−02 | 7.725E−03 | 3.826E−02 | 3.102E−02 | 2.685E−02 | 4.500E−02 | 5.359E−02 | 3.924E−02 | 2.747E−02 | 2.440E−02 | 4.476E−02 | 3.617E−02 | 4.378E−02 |
| 111 | 9.099E−03 | 1.349E−02 | 1.962E−02 | 2.894E−02 | 2.440E−02 | 3.458E−02 | 3.066E−02 | 3.102E−02 | 2.023E−02 | 1.545E−02 | 3.458E−02 | 1.680E−02 | 3.532E−02 |
| 112 | 6.070E−03 | 3.863E−03 | 1.214E−02 | 2.170E−02 | 1.668E−02 | 1.852E−02 | 1.557E−02 | 1.582E−02 | 9.871E−03 | 1.086E−02 | 1.680E−02 | 1.410E−02 | 1.950E−02 |
| 113 | 1.521E−03 | 5.800E−03 | 3.274E−03 | 2.587E−03 | 5.126E−03 | 4.929E−03 | 5.199E−03 | 9.160E−03 | 3.115E−03 | 9.062E−03 | 6.094E−03 | 3.777E−03 | 6.683E−03 |
| 114 | 4.549E−03 | 1.937E−03 | 4.672E−03 | 3.617E−03 | 1.089E−02 | 6.168E−03 | 1.144E−02 | 5.089E−03 | 5.714E−03 | 9.969E−03 | 3.053E−03 | 5.408E−03 | 7.296E−03 |
| 115 | 4.549E−03 | 1.937E−03 | 9.344E−03 | 1.239E−02 | 9.614E−03 | 1.048E−02 | 1.093E−02 | 8.657E−03 | 8.314E−03 | 3.617E−03 | 1.324E−02 | 7.026E−03 | 1.704E−02 |
| 116 | 0.000E+00 | 9.663E−03 | 3.740E−03 | 3.102E−03 | 7.689E−03 | 1.171E−02 | 4.684E−03 | 4.586E−03 | 2.072E−03 | 6.340E−03 | 4.574E−03 | 5.408E−03 | 5.469E−03 |
| 117 | 1.521E−03 | 3.863E−03 | 1.263E−02 | 4.132E−03 | 1.410E−02 | 8.633E−03 | 1.093E−02 | 9.675E−03 | 7.272E−03 | 1.631E−02 | 1.067E−02 | 9.185E−03 | 1.094E−02 |
| 118 | 6.070E−03 | 0.000E+00 | 1.398E−03 | 3.102E−03 | 7.051E−03 | 4.316E−03 | 1.093E−02 | 6.107E−03 | 4.157E−03 | 4.525E−03 | 6.609E−03 | 2.698E−03 | 9.123E−03 |
| 119 | 3.029E−03 | 1.937E−03 | 1.074E−02 | 4.647E−03 | 8.976E−03 | 8.020E−03 | 1.197E−02 | 9.160E−03 | 9.344E−03 | 2.722E−03 | 1.118E−02 | 1.619E−03 | 7.897E−03 |
| 120 | 6.070E−03 | 3.863E−03 | 8.400E−03 | 7.235E−03 | 5.763E−03 | 8.020E−03 | 8.326E−03 | 9.675E−03 | 8.314E−03 | 5.432E−03 | 8.645E−03 | 5.947E−03 | 9.724E−03 |
| 121 | 1.327E−01 | 9.706E−02 | 1.460E−02 | 3.232E−02 | 2.805E−02 | 2.698E−02 | 6.509E−03 | 3.188E−03 | 2.930E−02 | 3.972E−02 | 3.179E−03 | 2.369E−02 | 1.140E−02 |
| 122 | 5.031E−01 | 1.932E−01 | 1.692E−01 | 9.083E−02 | 1.362E−01 | 1.505E−01 | 1.532E−01 | 2.199E−01 | 9.083E−02 | 1.131E−01 | 1.621E−01 | 1.184E−01 | 1.407E−01 |
| 123 | 2.850E+00 | 5.423E+00 | 2.484E+00 | 2.262E+00 | 3.544E+00 | 2.173E+00 | 2.253E+00 | 2.413E+00 | 2.093E+00 | 4.987E+00 | 2.413E+00 | 2.271E+00 | 3.090E+00 |
| 124 | 4.746E−02 | 4.835E−02 | 3.802E−02 | 2.262E−02 | 4.817E−02 | 2.315E−02 | 9.795E−03 | 4.461E−02 | 2.930E−02 | 3.972E−02 | 2.867E−02 | 2.030E−02 | 3.802E−02 |
| 125 | 4.746E−02 | 4.835E−02 | 3.508E−02 | 3.553E−02 | 4.817E−02 | 2.315E−02 | 6.509E−03 | 3.508E−02 | 1.300E−02 | 4.533E−02 | 5.093E−02 | 3.045E−02 | 3.802E−02 |
| 126 | 1.327E+00 | 7.988E−01 | 1.077E+00 | 8.887E−01 | 8.308E−01 | 7.293E−01 | 8.566E−01 | 1.051E+00 | 6.928E−01 | 4.933E−01 | 9.617E−01 | 7.507E−01 | 1.701E+00 |
| 127 | 2.484E+00 | 2.324E+00 | 1.674E+00 | 2.057E+00 | 1.959E+00 | 1.906E+00 | 1.781E+00 | 2.413E+00 | 1.861E+00 | 1.505E+00 | 1.959E+00 | 1.790E+00 | 3.874E+00 |
| 128 | 2.093E+00 | 4.479E+00 | 1.621E+00 | 2.271E+00 | 2.342E+00 | 1.968E+00 | 1.647E+00 | 2.075E+00 | 1.995E+00 | 3.473E+00 | 1.941E+00 | 2.182E+00 | 2.983E+00 |
| 129 | 1.897E−01 | 1.451E−01 | 8.771E−03 | 2.262E−02 | 4.817E−02 | 3.473E−02 | 2.609E−02 | 1.273E−02 | 3.900E−02 | 6.242E−02 | 1.273E−02 | 4.737E−02 | 6.474E−02 |
| 130 | 1.332E+01 | 5.966E+00 | 1.727E+01 | 1.190E+01 | 1.108E+01 | 5.211E+00 | 8.898E+00 | 5.307E+00 | 9.846E+00 | 4.684E+00 | 1.125E+01 | 1.485E+01 | 7.641E+00 |
| 131 | 9.018E+00 | 6.340E+00 | 1.359E+01 | 7.313E+00 | 5.913E+00 | 4.088E+00 | 7.572E+00 | 2.947E+00 | 1.026E+01 | 3.606E+00 | 8.840E+00 | 1.106E+01 | 3.927E+00 |
| 132 | 8.540E−02 | 2.778E−01 | 4.096E−02 | 5.174E−02 | 8.023E−02 | 3.473E−02 | 5.209E−02 | 3.820E−02 | 5.530E−02 | 1.754E−01 | 2.226E−02 | 2.030E−02 | 7.614E−02 |
| 133 | 4.746E−02 | 1.327E−01 | 8.771E−03 | 3.882E−02 | 1.202E−02 | 4.630E−02 | 1.950E−02 | 9.528E−03 | 1.950E−02 | 7.373E−02 | 1.594E−02 | 1.015E−02 | 1.906E−02 |
| 134 | 1.897E−02 | 4.835E−02 | 1.167E−02 | 9.706E−03 | 2.004E−02 | 7.720E−03 | 3.259E−03 | 2.547E−02 | 1.630E−02 | 4.533E−02 | 2.226E−02 | 6.768E−03 | 3.045E−02 |
| 135 | 4.746E−02 | 1.692E−01 | 5.841E−03 | 1.291E−02 | 5.218E−02 | 3.856E−02 | 1.630E−02 | 1.273E−02 | 6.500E−03 | 5.672E−02 | 1.273E−02 | 6.768E−03 | 1.140E−02 |
| 136 | 4.746E−02 | 7.257E−02 | 0.000E+00 | 3.553E−02 | 2.404E−02 | 7.720E−03 | 1.950E−02 | 1.915E−02 | 1.300E−02 | 2.832E−02 | 6.367E−03 | 2.369E−02 | 1.906E−02 |
| 137 | 7.596E−02 | 2.538E−01 | 2.342E−02 | 6.465E−02 | 5.619E−02 | 6.180E−02 | 3.909E−02 | 4.141E−02 | 3.900E−02 | 1.986E−01 | 2.867E−02 | 3.384E−02 | 6.848E−02 |
| 138 | 1.140E−01 | 1.817E−01 | 2.627E−02 | 1.291E−02 | 2.404E−02 | 2.698E−02 | 2.609E−02 | 1.915E−02 | 1.950E−02 | 2.271E−02 | 1.906E−02 | 3.045E−02 | 5.325E−02 |
| 139 | 3.704E−01 | 6.411E−01 | 2.716E−01 | 3.268E−01 | 2.529E−01 | 2.511E−01 | 1.923E−01 | 3.793E−01 | 1.852E−01 | 2.440E−01 | 1.496E−01 | 2.369E−01 | 2.930E−01 |
| 140 | 1.995E−01 | 3.749E−01 | 1.024E−01 | 1.264E−01 | 1.362E−01 | 1.354E−01 | 1.594E−01 | 2.582E−01 | 1.888E−01 | 2.208E−01 | 6.999E−02 | 1.282E−01 | 9.528E−02 |
| 141 | 1.042E−01 | 9.706E−02 | 2.342E−02 | 4.203E−02 | 2.004E−02 | 4.248E−02 | 4.559E−02 | 1.273E−02 | 4.550E−02 | 1.532E−01 | 3.500E−02 | 6.091E−02 | 4.185E−02 |
| 142 | 2.850E−02 | 7.257E−02 | 2.921E−03 | 0.000E+00 | 2.004E−02 | 3.856E−03 | 3.259E−03 | 1.594E−02 | 3.250E−03 | 4.533E−02 | 3.179E−03 | 2.707E−02 | 1.906E−02 |
| 143 | 4.746E−02 | 4.835E−02 | 5.841E−03 | 3.232E−02 | 1.202E−02 | 2.698E−02 | 6.509E−03 | 9.528E−03 | 1.950E−02 | 1.701E−02 | 9.528E−03 | 3.384E−03 | 3.802E−03 |
| 144 | 1.140E−01 | 6.046E−02 | 2.342E−02 | 3.232E−02 | 3.206E−02 | 4.248E−02 | 9.795E−03 | 2.547E−02 | 9.795E−03 | 5.102E−02 | 1.906E−02 | 3.384E−02 | 6.474E−02 |
| 145 | 7.596E−02 | 1.086E−01 | 3.508E−02 | 3.232E−02 | 2.004E−02 | 1.932E−02 | 1.300E−02 | 3.508E−02 | 2.280E−02 | 3.402E−02 | 6.367E−03 | 2.030E−02 | 2.663E−02 |
| 146 | 2.182E−01 | 4.114E−01 | 2.458E−01 | 1.585E−01 | 2.289E−01 | 1.968E−01 | 1.763E−01 | 2.547E−01 | 2.734E−01 | 2.102E−01 | 1.817E−01 | 2.467E−01 | 1.674E−01 |
| 147 | 1.995E−01 | 2.057E−01 | 1.345E−01 | 1.879E−01 | 1.808E−01 | 1.888E−01 | 1.140E−01 | 2.992E−01 | 1.532E−01 | 1.300E−01 | 8.905E−02 | 1.763E−01 | 2.280E−01 |

APPENDIX D-continued

Ovarian Cancer
Training Dataset

| | | | | | | | | | | | | | |
|---|---|---|---|---|---|---|---|---|---|---|---|---|---|
| 148 | 3.321E−01 | 1.051E+00 | 4.301E−01 | 7.827E−01 | 4.817E−01 | 6.064E−01 | 4.007E−01 | 9.261E−01 | 5.102E−01 | 4.764E−01 | 3.090E−01 | 4.737E−01 | 7.231E−01 |
| 149 | 7.596E−02 | 2.422E−01 | 1.051E−01 | 1.291E−01 | 1.086E−01 | 1.273E−01 | 5.209E−02 | 1.149E−01 | 1.264E−01 | 1.300E−01 | 7.952E−02 | 7.783E−02 | 1.638E−01 |
| 150 | 7.596E−02 | 2.057E−01 | 8.771E−03 | 2.262E−02 | 2.404E−02 | 3.090E−02 | 1.300E−02 | 9.528E−03 | 2.280E−02 | 3.402E−02 | 1.594E−02 | 3.384E−03 | 2.280E−02 |
| 151 | 8.540E−02 | 7.257E−02 | 8.771E−03 | 6.465E−03 | 8.023E−03 | 2.315E−02 | 9.795E−03 | 1.915E−02 | 2.280E−02 | 2.271E−02 | 1.594E−02 | 1.354E−02 | 1.523E−02 |
| 152 | 4.746E−02 | 7.257E−02 | 3.215E−02 | 5.815E−02 | 4.007E−02 | 2.698E−02 | 1.630E−02 | 1.594E−02 | 2.280E−02 | 5.102E−02 | 3.500E−02 | 5.414E−02 | 1.906E−02 |
| 153 | 5.699E−02 | 7.257E−02 | 2.342E−02 | 2.582E−02 | 4.007E−02 | 1.932E−02 | 1.630E−02 | 1.594E−02 | 2.930E−02 | 2.271E−02 | 2.547E−02 | 3.384E−02 | 2.280E−02 |
| 154 | 2.850E−02 | 8.468E−02 | 5.841E−03 | 1.941E−02 | 2.805E−02 | 3.856E−03 | 2.280E−02 | 1.915E−02 | 6.500E−03 | 2.271E−02 | 9.528E−03 | 3.384E−03 | 2.280E−02 |
| 155 | 2.850E−02 | 2.057E−01 | 5.841E−03 | 1.291E−02 | 8.023E−03 | 2.698E−02 | 2.280E−02 | 1.273E−02 | 2.600E−02 | 1.131E−02 | 1.594E−02 | 1.354E−02 | 3.802E−02 |
| 156 | 3.704E−01 | 1.113E+00 | 6.046E−01 | 3.366E−01 | 3.972E−01 | 2.280E−01 | 3.678E−01 | 2.769E−01 | 6.892E−01 | 3.856E−01 | 2.956E−01 | 6.126E−01 | 1.906E−01 |
| 157 | 1.140E−01 | 6.287E−01 | 1.728E−01 | 1.389E−01 | 1.167E−01 | 1.158E−01 | 1.888E−01 | 2.645E−01 | 2.832E−01 | 1.362E−01 | 1.719E−01 | 1.728E−01 | 1.140E−01 |
| 158 | 2.565E−01 | 8.468E−01 | 4.586E−01 | 4.524E−01 | 4.372E−01 | 2.974E−01 | 3.482E−01 | 4.114E−01 | 5.752E−01 | 3.740E−01 | 3.152E−01 | 6.465E−01 | 2.858E−01 |
| 159 | 1.710E−01 | 3.143E−01 | 8.477E−02 | 1.291E−01 | 1.968E−01 | 1.425E−01 | 8.798E−02 | 2.743E−01 | 2.012E−01 | 1.478E−01 | 9.884E−02 | 1.558E−01 | 1.104E−01 |
| 160 | 4.746E−02 | 1.086E−01 | 3.215E−02 | 3.553E−02 | 2.004E−02 | 1.541E−02 | 2.280E−02 | 1.594E−02 | 2.280E−02 | 5.102E−02 | 4.452E−02 | 5.414E−02 | 6.091E−02 |
| 161 | 9.528E−03 | 2.903E−01 | 2.342E−02 | 8.406E−02 | 3.206E−02 | 5.405E−02 | 3.580E−02 | 4.461E−02 | 6.500E−03 | 6.242E−02 | 4.141E−02 | 2.030E−02 | 6.091E−02 |
| 162 | 2.850E−02 | 8.468E−02 | 1.754E−02 | 3.553E−02 | 2.805E−02 | 3.856E−02 | 1.950E−02 | 2.547E−02 | 4.550E−02 | 5.102E−02 | 1.273E−02 | 2.030E−02 | 2.280E−02 |
| 163 | 3.793E−02 | 9.706E−02 | 2.342E−02 | 1.621E−02 | 5.218E−02 | 1.932E−02 | 2.280E−02 | 0.000E+00 | 1.630E−02 | 5.672E−02 | 2.867E−02 | 2.369E−02 | 2.663E−02 |
| 164 | 1.897E−02 | 3.633E−02 | 1.167E−02 | 3.553E−02 | 2.004E−02 | 1.541E−02 | 2.280E−02 | 9.528E−03 | 9.795E−03 | 6.242E−02 | 2.867E−02 | 1.354E−02 | 7.614E−03 |
| 165 | 5.699E−02 | 9.706E−02 | 2.921E−02 | 2.912E−02 | 4.007E−02 | 1.158E−02 | 1.300E−02 | 6.376E−03 | 5.530E−02 | 6.803E−02 | 1.594E−02 | 1.692E−02 | 1.906E−02 |
| 166 | 5.699E−02 | 1.327E−01 | 4.675E−02 | 4.524E−02 | 3.606E−02 | 3.090E−02 | 7.168E−02 | 1.594E−02 | 4.550E−02 | 6.803E−02 | 4.452E−02 | 3.722E−02 | 4.951E−02 |
| 167 | 1.897E−01 | 5.681E−01 | 3.446E−01 | 2.039E−01 | 1.443E−01 | 1.425E−01 | 2.021E−01 | 1.175E−01 | 3.152E−01 | 2.556E−01 | 2.351E−01 | 4.604E−01 | 1.104E−01 |
| 168 | 1.523E−01 | 3.508E−01 | 1.371E−01 | 1.167E−01 | 1.327E−01 | 1.238E−01 | 7.818E−02 | 1.434E−01 | 1.496E−01 | 2.155E−01 | 1.113E−01 | 1.621E−01 | 6.091E−02 |
| 169 | 9.528E−02 | 1.817E−01 | 5.263E−02 | 7.435E−02 | 6.821E−02 | 4.630E−02 | 5.209E−02 | 6.696E−02 | 8.130E−02 | 1.077E−01 | 6.046E−02 | 5.752E−02 | 9.172E−02 |
| 170 | 9.528E−03 | 6.046E−02 | 1.754E−02 | 6.144E−02 | 4.817E−02 | 1.158E−02 | 4.230E−02 | 2.867E−02 | 6.500E−03 | 1.416E−01 | 6.046E−02 | 1.015E−02 | 1.140E−02 |
| 171 | 2.850E−02 | 7.257E−02 | 1.460E−02 | 6.144E−02 | 4.817E−02 | 6.180E−02 | 5.209E−02 | 3.820E−02 | 1.300E−02 | 6.803E−02 | 4.452E−02 | 2.707E−02 | 7.231E−02 |
| 172 | 1.790E−01 | 1.729E−01 | 1.324E−01 | 4.942E−02 | 7.075E−02 | 1.218E−01 | 8.473E−02 | 1.106E−01 | 1.251E−01 | 8.351E−02 | 1.039E−01 | 1.251E−01 | 7.603E−02 |
| 173 | 3.330E+00 | 5.030E+00 | 1.934E+00 | 1.720E+00 | 2.759E+00 | 2.379E+00 | 2.007E+00 | 2.351E+00 | 2.123E+00 | 2.742E+00 | 2.026E+00 | 1.956E+00 | 2.404E+00 |
| 174 | 4.639E+00 | 9.291E+00 | 3.093E+00 | 2.652E+00 | 4.457E+00 | 3.774E+00 | 3.211E+00 | 3.896E+00 | 3.905E+00 | 4.592E+00 | 3.150E+00 | 3.370E+00 | 3.569E+00 |
| 175 | 1.594E+00 | 2.006E+00 | 9.157E−01 | 7.653E−01 | 1.314E+00 | 1.171E+00 | 1.036E+00 | 1.241E+00 | 9.743E−01 | 1.026E+00 | 9.855E−01 | 9.447E−01 | 1.178E+00 |
| 176 | 3.292E+00 | 5.987E+00 | 1.905E+00 | 2.239E+00 | 3.654E+00 | 2.460E+00 | 2.544E+00 | 2.457E+00 | 3.100E+00 | 3.484E+00 | 2.699E+00 | 2.334E+00 | 3.306E+00 |
| 177 | 1.769E+00 | 1.366E+00 | 1.408E+00 | 6.233E−01 | 1.162E+00 | 6.352E−01 | 1.405E+00 | 1.176E+00 | 2.316E+00 | 8.890E−01 | 1.532E+00 | 1.709E+00 | 9.181E−01 |
| 178 | 5.432E−01 | 2.428E−01 | 2.833E−01 | 1.533E−01 | 2.391E−01 | 1.717E−01 | 2.808E−01 | 4.304E−01 | 4.329E−01 | 1.263E−01 | 3.299E−01 | 2.575E−01 | 2.011E−01 |
| 179 | 8.240E−02 | 3.666E−02 | 3.544E−02 | 3.029E−02 | 3.372E−02 | 2.342E−02 | 3.765E−02 | 4.525E−02 | 6.315E−02 | 3.274E−02 | 4.255E−02 | 2.796E−02 | 2.673E−02 |
| 180 | 2.882E−02 | 5.996E−02 | 8.449E−03 | 2.452E−02 | 3.814E−02 | 2.281E−02 | 1.839E−02 | 2.195E−02 | 1.655E−02 | 3.752E−02 | 2.452E−02 | 1.118E−02 | 4.145E−02 |
| 181 | 2.354E−02 | 3.004E−02 | 9.258E−03 | 1.692E−02 | 1.987E−02 | 2.342E−02 | 2.060E−02 | 1.717E−02 | 8.510E−03 | 2.036E−02 | 1.275E−02 | 8.387E−03 | 2.146E−02 |
| 182 | 1.557E−01 | 2.587E−01 | 7.725E−02 | 6.634E−02 | 1.312E−01 | 9.884E−02 | 9.099E−02 | 9.344E−02 | 8.866E−02 | 2.195E−01 | 6.573E−02 | 7.124E−02 | 1.032E−01 |
| 183 | 2.268E+00 | 4.008E+00 | 1.336E+00 | 1.208E+00 | 1.602E+00 | 1.896E+00 | 1.263E+00 | 1.451E+00 | 1.088E+00 | 2.429E+00 | 1.113E+00 | 1.224E+00 | 1.313E+00 |
| 184 | 2.430E+00 | 4.051E+00 | 1.533E+00 | 1.186E+00 | 1.552E+00 | 1.639E+00 | 1.284E+00 | 1.489E+00 | 1.329E+00 | 2.760E+00 | 1.332E+00 | 1.313E+00 | 1.243E+00 |
| 185 | 1.586E+00 | 3.005E+00 | 9.603E−01 | 9.238E−01 | 1.241E+00 | 1.232E+00 | 9.028E−01 | 1.206E+00 | 8.785E−01 | 1.945E+00 | 8.518E−01 | 8.302E−01 | 1.058E+00 |
| 186 | 2.894E+00 | 7.089E+00 | 2.037E+00 | 2.267E+00 | 2.749E+00 | 2.600E+00 | 1.781E+00 | 2.565E+00 | 2.328E+00 | 4.108E+00 | 1.814E+00 | 2.073E+00 | 2.283E+00 |
| 187 | 8.302E−01 | 1.308E+00 | 5.481E−01 | 5.934E−01 | 6.597E−01 | 7.558E−01 | 5.383E−01 | 6.977E−01 | 5.138E−01 | 8.155E−01 | 4.942E−01 | 5.739E−01 | 6.475E−01 |
| 188 | 7.456E−02 | 1.239E−01 | 4.549E−02 | 5.346E−02 | 4.476E−02 | 5.788E−02 | 4.034E−02 | 5.530E−02 | 3.630E−02 | 7.112E−02 | 4.378E−02 | 5.310E−02 | 6.131E−02 |
| 189 | 3.004E−02 | 2.661E−02 | 1.373E−02 | 1.068E−02 | 7.186E−03 | 1.010E−02 | 1.435E−02 | 1.925E−02 | 1.570E−02 | 9.368E−03 | 1.275E−02 | 1.300E−02 | 1.205E−02 |
| 190 | 3.286E−01 | 4.316E−01 | 2.048E−01 | 2.011E−01 | 2.771E−01 | 2.060E−01 | 2.428E−01 | 2.085E−01 | 1.815E−01 | 2.502E−01 | 2.698E−01 | 1.288E−01 | 2.612E−01 |
| 191 | 3.243E+00 | 3.665E+00 | 2.654E+00 | 1.627E+00 | 2.151E+00 | 1.421E+00 | 2.771E+00 | 2.139E+00 | 4.014E+00 | 2.234E+00 | 2.663E+00 | 3.038E+00 | 1.688E+00 |
| 192 | 1.218E+00 | 8.510E−01 | 7.772E−01 | 5.383E−01 | 6.646E−01 | 4.868E−01 | 8.001E−01 | 9.430E−01 | 1.114E+00 | 5.224E−01 | 7.836E−01 | 7.860E−01 | 5.310E−01 |
| 193 | 1.668E−01 | 1.803E−01 | 8.412E−02 | 9.344E−02 | 7.186E−02 | 8.130E−02 | 6.683E−02 | 8.731E−02 | 1.047E−01 | 1.023E−01 | 9.160E−02 | 7.738E−02 | 8.326E−02 |
| 194 | 6.928E−02 | 6.242E−01 | 3.863E−02 | 1.188E−01 | 8.559E−02 | 1.447E−01 | 7.394E−02 | 5.359E−02 | 4.120E−02 | 1.839E−01 | 4.378E−02 | 4.476E−02 | 9.540E−02 |
| 195 | 4.574E−02 | 2.465E−01 | 2.502E−02 | 5.702E−02 | 3.200E−02 | 7.333E−02 | 3.053E−02 | 2.452E−02 | 1.570E−02 | 6.867E−02 | 2.011E−02 | 2.747E−02 | 4.819E−02 |
| 196 | 2.158E−01 | 2.465E−01 | 3.335E−01 | 1.937E−01 | 1.521E−01 | 1.074E−01 | 2.158E−01 | 1.053E−01 | 2.477E−01 | 1.288E−01 | 1.471E−01 | 2.183E−01 | 7.860E−02 |
| 197 | 1.410E−01 | 1.668E−01 | 1.435E−01 | 1.006E−01 | 9.663E−02 | 8.449E−02 | 1.349E−01 | 8.903E−02 | 2.330E−01 | 9.528E−02 | 1.226E−01 | 1.020E−01 | 7.026E−02 |

APPENDIX D-continued

Ovarian Cancer
Training Dataset

| | | | | | | | | | | | | | |
|---|---|---|---|---|---|---|---|---|---|---|---|---|---|
| 198 | 1.032E−01 | 1.166E−01 | 6.524E−02 | 6.058E−02 | 6.965E−02 | 5.371E−02 | 5.518E−02 | 5.886E−02 | 9.356E−02 | 7.885E−02 | 6.180E−02 | 4.893E−02 | 4.660E−02 |
| 199 | 1.312E−01 | 4.795E−01 | 2.293E−02 | 1.386E−01 | 1.839E−01 | 1.180E−01 | 1.050E−01 | 7.554E−02 | 2.869E−02 | 2.416E−01 | 1.008E−01 | 2.796E−02 | 1.337E−01 |
| 200 | 7.578E−02 | 2.379E−01 | 2.735E−02 | 8.817E−02 | 6.855E−02 | 7.124E−02 | 4.488E−02 | 4.831E−02 | 2.281E−02 | 1.117E−01 | 5.739E−02 | 2.980E−02 | 7.443E−02 |
| 201 | 4.709E−02 | 2.869E−01 | 2.538E−02 | 6.193E−02 | 4.476E−02 | 7.235E−02 | 2.869E−02 | 4.525E−02 | 2.906E−02 | 7.811E−02 | 3.458E−02 | 3.164E−02 | 5.874E−02 |
| 202 | 7.848E−03 | 3.495E−02 | 4.022E−03 | 7.124E−03 | 2.489E−02 | 7.971E−03 | 6.732E−03 | 3.948E−03 | 4.476E−04 | 2.109E−02 | 6.131E−03 | 2.796E−03 | 2.256E−02 |
| 203 | 1.312E−03 | 1.668E−03 | 8.044E−04 | 4.451E−04 | 1.105E−03 | 5.310E−04 | 8.964E−04 | 0.000E+00 | 0.000E+00 | 2.342E−03 | 1.754E−03 | 4.660E−04 | 5.236E−04 |
| 204 | 1.435E−02 | 5.996E−02 | 4.022E−03 | 8.007E−03 | 2.158E−02 | 1.275E−02 | 1.300E−02 | 7.897E−03 | 2.685E−03 | 3.200E−02 | 6.131E−03 | 3.262E−03 | 1.410E−02 |
| 205 | 5.224E−03 | 1.668E−03 | 1.606E−03 | 1.337E−03 | 1.655E−03 | 1.063E−03 | 8.964E−04 | 1.754E−03 | 4.476E−04 | 7.811E−04 | 2.195E−03 | 2.330E−03 | 2.097E−03 |
| 206 | 6.536E−03 | 6.658E−02 | 3.617E−03 | 8.007E−03 | 4.145E−02 | 2.710E−02 | 1.619E−02 | 6.143E−03 | 4.034E−03 | 3.752E−02 | 1.704E−02 | 6.524E−03 | 3.875E−02 |
| 207 | 7.848E−03 | 3.164E−02 | 4.831E−03 | 7.566E−03 | 5.518E−03 | 5.849E−03 | 4.929E−03 | 9.651E−03 | 3.139E−03 | 1.410E−02 | 4.819E−03 | 5.592E−03 | 4.194E−03 |
| 208 | 5.224E−03 | 9.994E−03 | 2.416E−03 | 5.346E−03 | 5.518E−03 | 3.716E−03 | 3.593E−03 | 3.507E−03 | 2.244E−03 | 3.127E−03 | 1.754E−03 | 4.194E−03 | 4.194E−03 |
| 209 | 0.000E+00 | 1.668E−03 | 4.022E−04 | 0.000E+00 | 1.105E−03 | 0.000E+00 | 1.349E−03 | 1.312E−03 | 0.000E+00 | 1.557E−03 | 4.378E−04 | 9.319E−04 | 1.048E−03 |
| 210 | 0.000E+00 | 1.668E−03 | 4.022E−04 | 1.337E−03 | 5.518E−04 | 5.310E−04 | 1.349E−03 | 0.000E+00 | 0.000E+00 | 7.811E−04 | 0.000E+00 | 1.398E−03 | 0.000E+00 |
| 211 | 5.224E−03 | 5.003E−03 | 4.022E−04 | 8.903E−04 | 1.105E−03 | 1.063E−03 | 1.790E−03 | 4.390E−04 | 4.476E−04 | 0.000E+00 | 4.378E−04 | 4.660E−04 | 5.236E−04 |
| 212 | 2.612E−03 | 1.668E−03 | 8.044E−04 | 1.337E−03 | 3.311E−03 | 6.376E−03 | 8.964E−04 | 5.261E−03 | 0.000E+00 | 4.684E−03 | 8.768E−04 | 2.330E−03 | 2.097E−03 |
| 213 | 7.848E−03 | 9.994E−03 | 1.606E−03 | 3.115E−03 | 4.414E−03 | 2.121E−03 | 1.790E−03 | 3.507E−03 | 3.139E−03 | 7.811E−03 | 4.378E−04 | 2.796E−03 | 5.763E−03 |
| 214 | 0.000E+00 | 9.994E−03 | 1.606E−03 | 2.232E−03 | 1.655E−03 | 2.121E−03 | 3.139E−03 | 4.390E−04 | 3.139E−03 | 7.026E−03 | 2.195E−03 | 4.660E−04 | 1.048E−03 |
| 215 | 1.312E−03 | 8.326E−03 | 0.000E+00 | 0.000E+00 | 5.518E−04 | 1.594E−03 | 2.244E−03 | 4.390E−04 | 4.476E−04 | 7.811E−04 | 1.754E−03 | 0.000E+00 | 5.236E−04 |
| 216 | 1.312E−03 | 1.668E−03 | 0.000E+00 | 0.000E+00 | 0.000E+00 | 1.594E−03 | 4.488E−04 | 2.195E−03 | 0.000E+00 | 7.811E−04 | 0.000E+00 | 9.319E−04 | 1.048E−03 |
| 217 | 1.312E−03 | 5.003E−03 | 1.208E−03 | 0.000E+00 | 0.000E+00 | 1.063E−03 | 4.488E−04 | 0.000E+00 | 8.952E−04 | 3.127E−03 | 1.754E−03 | 4.660E−04 | 2.097E−03 |
| 218 | 2.285E+00 | 3.768E+00 | 1.577E+00 | 1.420E+00 | 1.603E+00 | 1.778E+00 | 1.186E+00 | 1.447E+00 | 9.735E−01 | 2.571E+00 | 1.380E+00 | 1.462E+00 | 1.532E+00 |
| 219 | 3.532E−02 | 5.162E−02 | 2.219E−02 | 1.288E−02 | 1.827E−02 | 2.502E−02 | 1.754E−02 | 1.839E−02 | 1.386E−02 | 2.735E−02 | 1.582E−02 | 1.864E−02 | 1.839E−02 |
| 220 | 2.970E+00 | 1.434E+00 | 2.552E+00 | 1.294E+00 | 1.426E+00 | 2.442E+00 | 2.264E+00 | 2.227E+00 | 2.217E+00 | 9.506E−01 | 2.972E+00 | 1.636E+00 | 2.072E+00 |
| 221 | 6.097E+01 | 6.454E+01 | 5.386E+01 | 6.002E+01 | 6.426E+01 | 7.427E+01 | 6.414E+01 | 6.176E+01 | 5.365E+01 | 5.751E+01 | 7.189E+01 | 5.451E+01 | 7.604E+01 |
| 222 | 5.224E+01 | 4.343E+01 | 5.627E+01 | 6.137E+01 | 5.809E+01 | 5.945E+01 | 5.906E+01 | 7.252E+01 | 5.602E+01 | 3.189E+01 | 5.938E+01 | 5.837E+01 | 7.572E+01 |
| 223 | 3.264E+01 | 2.436E+01 | 3.118E+01 | 2.603E+01 | 2.634E+01 | 3.009E+01 | 3.633E+01 | 3.489E+01 | 3.262E+01 | 1.857E+01 | 4.010E+01 | 2.676E+01 | 3.159E+01 |
| 224 | 2.491E+01 | 2.669E+01 | 2.088E+01 | 2.430E+01 | 2.791E+01 | 2.446E+01 | 2.262E+01 | 2.237E+01 | 2.169E+01 | 2.245E+01 | 3.212E+01 | 2.094E+01 | 3.473E+01 |
| 225 | 1.363E+01 | 1.106E+01 | 2.305E+01 | 1.445E+01 | 1.763E+01 | 1.358E+01 | 1.800E+01 | 1.514E+01 | 2.390E+01 | 9.558E+00 | 2.328E+01 | 3.089E+01 | 1.801E+01 |
| 226 | 5.873E+00 | 4.220E+00 | 1.314E+01 | 6.339E+00 | 5.390E+00 | 4.650E+00 | 1.073E+01 | 2.852E+00 | 1.408E+01 | 2.291E+00 | 1.055E+01 | 1.182E+01 | 3.788E+00 |
| 227 | 2.611E+00 | 1.537E+00 | 4.103E+00 | 1.809E+00 | 1.944E+00 | 1.585E+00 | 3.577E+00 | 2.502E+00 | 5.990E+00 | 8.396E−01 | 4.060E+00 | 3.240E+00 | 2.038E+00 |
| 228 | 5.487E−01 | 5.256E−01 | 6.655E−01 | 3.690E−01 | 4.714E−01 | 4.967E−01 | 3.620E−01 | 2.188E−01 | 2.235E−01 | 3.898E−01 | 4.663E−01 | 2.353E−01 | 8.381E−01 |
| 229 | 6.029E−01 | 5.496E−01 | 7.061E−01 | 4.210E−01 | 4.698E−01 | 5.494E−01 | 4.231E−01 | 2.558E−01 | 2.619E−01 | 4.476E−01 | 4.801E−01 | 2.846E−01 | 8.916E−01 |
| 230 | 2.339E+01 | 3.201E+01 | 3.313E+01 | 2.886E+01 | 3.657E+01 | 2.760E+01 | 3.565E+01 | 2.633E+01 | 3.247E+01 | 3.549E+01 | 2.790E+01 | 3.268E+01 | 2.897E+01 |
| 231 | 4.819E+00 | 4.453E+00 | 5.630E+00 | 3.399E+00 | 4.609E+00 | 4.366E+00 | 4.683E+00 | 3.445E+00 | 4.537E+00 | 3.790E+00 | 4.523E+00 | 3.844E+00 | 5.289E+00 |
| 232 | 1.856E+00 | 2.127E+00 | 1.829E+00 | 1.429E+00 | 2.006E+00 | 1.687E+00 | 1.931E+00 | 1.360E+00 | 1.413E+00 | 1.881E+00 | 2.145E+00 | 1.637E+00 | 1.688E+00 |
| 233 | 5.808E+00 | 6.155E+00 | 5.805E+00 | 4.338E+00 | 5.765E+00 | 4.449E+00 | 5.767E+00 | 3.990E+00 | 4.246E+00 | 4.437E+00 | 5.863E+00 | 5.172E+00 | 5.099E+00 |
| 234 | 2.204E+01 | 2.006E+01 | 2.123E+01 | 1.382E+01 | 1.329E+01 | 1.847E+01 | 1.885E+01 | 1.391E+01 | 1.779E+01 | 1.668E+01 | 1.856E+01 | 1.546E+01 | 1.348E+01 |
| 235 | 9.951E+00 | 1.083E+01 | 1.033E+01 | 8.611E+00 | 9.608E+00 | 1.014E+01 | 1.017E+01 | 9.774E+00 | 1.265E+01 | 1.320E+01 | 9.379E+00 | 8.893E+00 | 9.635E+00 |
| 236 | 6.503E−01 | 9.087E−01 | 5.711E−01 | 9.154E−01 | 9.789E−01 | 8.250E−01 | 5.190E−01 | 4.189E−01 | 2.899E−01 | 7.310E−01 | 1.399E+00 | 4.450E−01 | 8.851E−01 |
| 237 | 5.915E+00 | 3.409E+00 | 4.713E+00 | 4.852E+00 | 5.262E+00 | 3.904E+00 | 4.824E+00 | 5.276E+00 | 3.836E+00 | 3.642E+00 | 6.200E+00 | 4.326E+00 | 4.688E+00 |
| 238 | 7.486E+00 | 5.762E+00 | 6.449E+00 | 4.874E+00 | 6.913E+00 | 5.683E+00 | 7.901E+00 | 7.619E+00 | 6.295E+00 | 7.430E+00 | 7.286E+00 | 5.717E+00 | 5.126E+00 |
| 239 | 1.441E+00 | 1.532E+00 | 1.267E+00 | 9.813E−01 | 1.412E+00 | 1.148E+00 | 1.451E+00 | 1.211E+00 | 1.209E+00 | 1.630E+00 | 1.544E+00 | 1.097E+00 | 1.193E+00 |
| 240 | 1.291E+01 | 2.453E+01 | 8.052E+00 | 2.255E+01 | 1.616E+01 | 2.343E+01 | 1.042E+01 | 1.498E+01 | 6.953E+00 | 2.411E+01 | 1.588E+01 | 5.482E+00 | 2.449E+01 |
| 241 | 2.566E+02 | 2.486E+02 | 2.056E+02 | 2.650E+02 | 2.141E+02 | 2.742E+02 | 2.184E+02 | 2.390E+02 | 2.063E+02 | 2.497E+02 | 1.931E+02 | 2.046E+02 | 2.362E+02 |
| 242 | 1.792E+02 | 1.494E+02 | 1.522E+02 | 1.382E+02 | 1.241E+02 | 1.637E+02 | 1.617E+02 | 1.633E+02 | 1.558E+02 | 1.627E+02 | 1.546E+02 | 1.325E+02 | 1.274E+02 |
| 243 | 1.669E+01 | 1.316E+01 | 1.519E+01 | 1.176E+01 | 1.131E+01 | 1.414E+01 | 1.538E+01 | 1.570E+01 | 1.623E+01 | 1.532E+01 | 1.600E+01 | 1.245E+01 | 1.202E+01 |
| 244 | 9.993E+00 | 5.313E+00 | 1.194E+01 | 1.172E+01 | 1.088E+01 | 6.553E+00 | 9.064E+00 | 8.218E+00 | 1.093E−01 | 6.145E+00 | 1.189E+01 | 1.307E+01 | 7.666E+00 |
| 245 | 6.308E+00 | 3.831E+00 | 5.454E+00 | 6.029E+00 | 5.648E+00 | 4.379E+00 | 4.951E+00 | 6.276E+00 | 4.361E+00 | 3.961E+00 | 6.223E+00 | 5.261E+00 | 4.738E+00 |
| 246 | 7.544E+00 | 8.012E+00 | 6.599E+00 | 6.668E+00 | 7.997E+00 | 7.076E+00 | 7.270E+00 | 7.003E+00 | 5.726E+00 | 8.956E+00 | 8.125E+00 | 6.076E+00 | 8.272E+00 |
| 247 | 5.040E+00 | 5.211E+00 | 4.798E+00 | 3.918E+00 | 4.942E+00 | 4.300E+00 | 5.065E+00 | 3.722E+00 | 4.054E+00 | 4.805E+00 | 5.824E+00 | 4.193E+00 | 4.808E+00 |

APPENDIX D-continued

Ovarian Cancer
Training Dataset

| | | | | | | | | | | | | | |
|---|---|---|---|---|---|---|---|---|---|---|---|---|---|
| 248 | 6.918E+01 | 5.292E+01 | 9.163E+01 | 6.443E+01 | 7.152E+01 | 6.795E+01 | 7.401E+01 | 7.636E+01 | 9.478E+01 | 6.621E+01 | 8.343E+01 | 1.144E+02 | 8.077E+01 |
| 249 | 7.943E+01 | 5.210E+01 | 7.148E+01 | 6.926E+01 | 6.513E+01 | 6.924E+01 | 6.728E+01 | 9.868E+01 | 6.857E+01 | 5.496E+01 | 7.329E+01 | 7.311E+01 | 7.643E+01 |
| 250 | 1.552E+02 | 1.283E+02 | 1.230E+02 | 1.480E+02 | 1.290E+02 | 1.291E+02 | 1.206E+02 | 1.460E+02 | 1.315E+02 | 1.414E+02 | 1.312E+02 | 1.227E+02 | 1.491E+02 |
| 251 | 5.829E+01 | 6.191E+01 | 4.787E+01 | 5.817E+01 | 5.073E+01 | 5.795E+01 | 4.635E+01 | 5.148E+01 | 4.581E+01 | 6.044E+01 | 5.566E+01 | 4.034E+01 | 5.863E+01 |
| 252 | 4.175E+00 | 4.333E+00 | 3.163E+00 | 3.987E+00 | 3.416E+00 | 3.795E+00 | 3.052E+00 | 3.062E+00 | 2.767E+00 | 3.965E+00 | 4.357E+00 | 2.522E+00 | 4.019E+00 |
| 253 | 3.918E+00 | 2.975E+00 | 5.048E+00 | 4.984E+00 | 4.038E+00 | 3.248E+00 | 3.812E+00 | 2.045E+00 | 4.518E+00 | 2.823E+00 | 5.068E+00 | 4.030E+00 | 2.825E+00 |
| 254 | 9.964E+00 | 5.905E+00 | 9.924E+00 | 1.070E+01 | 8.933E+00 | 6.435E+00 | 8.469E+00 | 8.543E+00 | 1.264E+01 | 6.063E+00 | 1.055E+01 | 1.175E+01 | 6.259E+00 |
| 255 | 8.567E+00 | 5.659E+00 | 9.352E+00 | 7.642E+00 | 8.848E+00 | 5.796E+00 | 7.825E+00 | 7.607E+00 | 9.107E+00 | 6.372E+00 | 9.149E+00 | 9.964E+00 | 6.576E+00 |
| 256 | 3.051E+00 | 2.818E+00 | 2.915E+00 | 2.969E+00 | 3.678E+00 | 2.679E+00 | 2.724E+00 | 2.928E+00 | 2.355E+00 | 3.274E+00 | 3.371E+00 | 2.892E+00 | 3.057E+00 |
| 257 | 4.490E+00 | 5.829E+00 | 4.882E+00 | 4.329E+00 | 7.227E+00 | 5.426E+00 | 5.247E+00 | 4.671E+00 | 3.918E+00 | 5.208E+00 | 5.503E+00 | 5.019E+00 | 5.556E+00 |
| 258 | 2.733E+01 | 1.663E+01 | 3.280E+01 | 1.940E+01 | 2.098E+01 | 1.761E+01 | 2.849E+01 | 2.431E+01 | 4.685E+01 | 1.628E+01 | 3.428E+01 | 3.012E+01 | 1.915E+01 |
| 259 | 4.427E+01 | 3.397E+01 | 4.930E+01 | 3.504E+01 | 4.611E+01 | 3.076E+01 | 3.971E+01 | 4.106E+01 | 6.631E+01 | 4.015E+01 | 5.142E+01 | 6.373E+01 | 4.176E+01 |
| 260 | 4.086E+01 | 3.368E+01 | 3.704E+01 | 3.324E+01 | 4.044E+01 | 3.385E+01 | 3.310E+01 | 4.313E+01 | 3.724E+01 | 3.514E+01 | 3.789E+01 | 3.801E+01 | 3.498E+01 |
| 261 | 2.614E+01 | 4.148E+01 | 2.845E+01 | 3.480E+01 | 3.752E+01 | 3.514E+01 | 3.350E+01 | 3.005E+01 | 3.160E+01 | 3.870E+01 | 2.916E+01 | 3.152E+01 | 2.679E+01 |
| 262 | 9.531E+00 | 1.777E+01 | 9.832E+00 | 1.639E+01 | 1.517E+01 | 1.634E+01 | 1.105E+01 | 9.956E+00 | 8.595E+00 | 1.396E+01 | 1.166E+01 | 1.008E+01 | 1.503E+01 |
| 263 | 3.065E+00 | 2.133E+00 | 4.226E+00 | 2.711E+00 | 2.706E+00 | 1.954E+00 | 3.120E+00 | 1.732E+00 | 4.352E+00 | 2.030E+00 | 3.709E+00 | 3.434E+00 | 1.888E+00 |
| 264 | 2.595E+00 | 2.769E+00 | 2.849E+00 | 2.794E+00 | 3.286E+00 | 2.488E+00 | 2.534E+00 | 2.159E+00 | 3.073E+00 | 3.414E+00 | 3.349E+00 | 3.014E+00 | 2.552E+00 |
| 265 | 2.074E+00 | 2.009E+00 | 1.974E+00 | 2.176E+00 | 2.623E+00 | 1.956E+00 | 1.947E+00 | 1.856E+00 | 1.856E+00 | 2.730E+00 | 2.445E+00 | 2.142E+00 | 2.037E+00 |
| 266 | 1.507E+00 | 3.464E+00 | 9.509E−01 | 2.197E+00 | 2.984E+00 | 2.790E+00 | 1.407E+00 | 1.390E+00 | 7.230E−01 | 4.109E+00 | 1.766E+00 | 1.031E+00 | 3.087E+00 |
| 267 | 1.511E+00 | 3.627E+00 | 1.128E+00 | 1.989E+00 | 2.779E+00 | 2.494E+00 | 1.694E+00 | 1.253E+00 | 1.042E+00 | 3.440E+00 | 1.965E+00 | 1.183E+00 | 2.685E+00 |
| 268 | 1.431E+01 | 8.520E+00 | 2.226E+01 | 1.028E+01 | 8.270E+00 | 6.298E+00 | 1.224E+01 | 4.186E+00 | 2.289E+01 | 7.463E+00 | 1.669E+01 | 1.650E+01 | 6.142E+00 |
| 269 | 9.941E+00 | 8.213E+00 | 8.963E+00 | 8.111E+00 | 7.534E+00 | 6.705E+00 | 8.087E+00 | 5.127E+00 | 1.282E+01 | 8.943E+00 | 1.090E+01 | 7.446E+00 | 6.834E+00 |
| 270 | 4.145E+00 | 3.825E+00 | 2.952E+00 | 3.550E+00 | 3.791E+00 | 3.169E+00 | 2.920E+00 | 3.023E+00 | 3.728E+00 | 4.335E+00 | 4.346E+00 | 2.385E+00 | 3.844E+00 |
| 271 | 1.114E+01 | 1.175E+01 | 1.311E+01 | 9.848E+00 | 1.772E+01 | 1.222E+01 | 1.429E+01 | 1.358E+01 | 1.142E+01 | 1.248E+01 | 1.254E+01 | 1.494E+01 | 1.138E+01 |
| 272 | 6.121E+01 | 8.098E+01 | 8.168E+01 | 7.193E+01 | 1.006E+02 | 7.281E+01 | 9.624E+01 | 7.157E+01 | 8.162E+01 | 8.783E+01 | 7.164E+01 | 8.470E+01 | 7.234E+01 |
| 273 | 7.215E+01 | 8.695E+01 | 8.766E+01 | 7.480E+01 | 1.036E+02 | 7.630E+01 | 1.008E+02 | 7.411E+01 | 8.186E+01 | 8.850E+01 | 7.241E+01 | 8.790E+01 | 7.631E+01 |
| 274 | 1.124E+01 | 1.480E+01 | 1.324E+01 | 1.090E+01 | 1.614E+01 | 1.171E+01 | 1.504E+01 | 1.121E+01 | 1.373E+01 | 1.323E+01 | 1.093E+01 | 1.380E+01 | 1.280E+01 |
| 275 | 5.335E−01 | 1.091E+00 | 5.854E−01 | 6.300E−01 | 1.124E+00 | 5.800E−01 | 7.831E−01 | 4.066E−01 | 3.986E−01 | 7.365E−01 | 6.713E−01 | 6.147E−01 | 5.941E−01 |
| 276 | 7.104E+00 | 1.158E+01 | 7.673E+00 | 7.155E+00 | 1.026E+01 | 6.035E+00 | 1.002E+01 | 5.809E+00 | 7.031E+00 | 8.632E+00 | 7.971E+00 | 9.305E+00 | 5.673E+00 |
| 277 | 1.624E+01 | 3.336E+01 | 1.991E+01 | 2.034E+01 | 2.190E+01 | 1.729E+01 | 2.578E+01 | 1.261E+01 | 1.951E+01 | 2.483E+01 | 1.855E+01 | 2.256E+01 | 1.615E+01 |
| 278 | 1.663E+01 | 3.261E+01 | 1.979E+01 | 1.994E+01 | 2.092E+01 | 1.651E+01 | 2.468E+01 | 1.200E+01 | 1.802E+01 | 2.458E+01 | 1.777E+01 | 2.205E+01 | 1.594E+01 |
| 279 | 7.525E+00 | 9.655E+00 | 7.497E+00 | 4.764E+00 | 4.577E+00 | 6.200E+00 | 6.231E+00 | 4.552E+00 | 6.332E+00 | 6.625E+00 | 6.790E+00 | 6.279E+00 | 5.219E+00 |
| 280 | 5.432E+00 | 8.219E+00 | 5.009E+00 | 7.465E+00 | 7.194E+00 | 7.379E+00 | 6.405E+00 | 6.427E+00 | 3.929E+00 | 7.498E+00 | 6.783E+00 | 4.458E+00 | 7.925E+00 |
| 281 | 1.213E+02 | 1.129E+02 | 1.185E+02 | 1.350E+02 | 1.126E+02 | 1.288E+02 | 1.158E+02 | 1.382E+02 | 1.160E+02 | 1.280E+02 | 1.099E+02 | 1.221E+02 | 1.312E+02 |
| 282 | 1.058E+02 | 9.645E+01 | 1.031E+02 | 1.126E+02 | 9.802E+01 | 1.090E+02 | 1.020E+02 | 1.190E+02 | 1.007E+02 | 1.081E+02 | 9.528E+01 | 1.056E+02 | 1.113E+02 |
| 283 | 5.405E+01 | 3.939E+01 | 4.901E+01 | 3.856E+01 | 3.406E+01 | 4.107E+01 | 4.720E+01 | 4.768E+01 | 4.897E+01 | 4.709E+01 | 5.109E+01 | 4.031E+01 | 3.633E+01 |
| 284 | 5.328E+00 | 6.390E+00 | 6.614E+00 | 5.363E+00 | 7.077E+00 | 6.020E+00 | 6.119E+00 | 4.604E+00 | 4.983E+00 | 5.336E+00 | 7.376E+00 | 6.425E+00 | 7.215E+00 |
| 285 | 8.157E+01 | 8.277E+01 | 7.951E+01 | 9.028E+01 | 7.812E+01 | 7.564E+01 | 6.837E+01 | 7.891E+01 | 7.551E+01 | 8.262E+01 | 8.310E+01 | 8.018E+01 | 9.346E+01 |
| 286 | 6.177E+01 | 6.399E+01 | 6.220E+01 | 6.529E+01 | 6.319E+01 | 5.913E+01 | 5.562E+01 | 6.078E+01 | 5.784E+01 | 6.097E+01 | 6.229E+01 | 6.159E+01 | 6.916E+01 |
| 287 | 1.052E+01 | 1.022E+01 | 8.920E+00 | 9.794E+00 | 8.332E+00 | 9.164E+00 | 7.480E+00 | 8.220E+00 | 7.733E+00 | 1.036E+01 | 1.080E+01 | 7.052E+00 | 1.063E+01 |
| 288 | 4.690E+01 | 7.481E+01 | 6.166E+01 | 6.197E+01 | 6.871E+01 | 6.111E+01 | 6.145E+01 | 5.470E+01 | 6.067E+01 | 6.971E+01 | 5.712E+01 | 6.478E+01 | 4.729E+01 |
| 289 | 3.649E+01 | 5.806E+01 | 5.070E+01 | 4.707E+01 | 5.796E+01 | 4.933E+01 | 5.265E+01 | 4.518E+01 | 4.926E+01 | 5.423E+01 | 4.406E+01 | 5.318E+01 | 3.683E+01 |
| 290 | 1.593E+01 | 2.670E+01 | 2.226E+01 | 2.263E+01 | 2.572E+01 | 2.565E+01 | 2.075E+01 | 1.833E+01 | 1.857E+01 | 1.944E+01 | 1.998E+01 | 2.235E+01 | 2.147E+01 |
| 291 | 1.218E+01 | 2.082E+01 | 1.828E+01 | 1.731E+01 | 1.990E+01 | 1.943E+01 | 1.626E+01 | 1.420E+01 | 1.426E+01 | 1.467E+01 | 1.606E+01 | 1.790E+01 | 1.711E+01 |
| 292 | 1.801E+00 | 3.059E+00 | 1.826E+00 | 2.803E+00 | 2.579E+00 | 2.504E+00 | 1.731E+00 | 1.659E+00 | 1.401E+00 | 2.554E+00 | 2.106E+00 | 1.756E+00 | 2.863E+00 |
| 293 | 1.127E+00 | 3.006E+00 | 5.821E−01 | 1.811E+00 | 2.459E+00 | 1.896E+00 | 1.145E+00 | 9.893E−01 | 5.441E−01 | 3.251E+00 | 1.350E+00 | 7.182E−01 | 2.543E+00 |
| 294 | 2.825E+00 | 2.284E+00 | 2.131E+00 | 2.725E+00 | 2.972E+00 | 2.885E+00 | 2.530E+00 | 3.208E+00 | 1.373E+00 | 2.635E+00 | 1.432E+00 | 1.495E+00 | 2.164E+00 |
| 295 | 2.798E+00 | 2.314E+00 | 2.136E+00 | 2.695E+00 | 2.914E+00 | 2.831E+00 | 2.459E+00 | 3.174E+00 | 1.388E+00 | 2.607E+00 | 1.406E+00 | 1.446E+00 | 2.133E+00 |
| 296 | 2.058E+00 | 1.225E+00 | 1.534E+00 | 1.315E+00 | 1.600E+00 | 1.565E+00 | 1.721E+00 | 1.853E+00 | 1.053E+00 | 1.523E+00 | 1.004E+00 | 9.160E−01 | 1.087E+00 |
| 297 | 1.926E−01 | 3.598E−01 | 2.427E−01 | 2.732E−01 | 2.795E−01 | 2.853E−01 | 3.108E−01 | 2.237E−01 | 7.722E−01 | 3.747E−01 | 2.104E−01 | 2.451E−01 | 2.602E−01 |

APPENDIX D-continued

Ovarian Cancer
Training Dataset

| | | | | | | | | | | | | | |
|---|---|---|---|---|---|---|---|---|---|---|---|---|---|
| 298 | 1.549E−02 | 2.036E−02 | 1.156E−02 | 8.946E−03 | 1.006E−02 | 1.206E−02 | 1.289E−02 | 8.388E−03 | 1.602E−02 | 1.330E−02 | 9.997E−03 | 9.525E−03 | 1.598E−02 |
| 299 | 5.642E−02 | 2.566E−01 | 6.586E−02 | 9.182E−02 | 7.058E−02 | 7.036E−02 | 7.894E−02 | 3.947E−02 | 1.521E−01 | 1.693E−01 | 6.865E−02 | 6.543E−02 | 5.921E−02 |
| 300 | 4.526E−03 | 2.424E−02 | 3.282E−03 | 5.685E−03 | 4.569E−03 | 8.130E−03 | 5.427E−03 | 2.574E−03 | 4.441E−03 | 9.074E−03 | 5.213E−03 | 5.106E−03 | 4.269E−03 |
| 301 | 4.998E−02 | 1.433E−01 | 5.792E−02 | 5.899E−02 | 4.784E−02 | 6.650E−02 | 6.393E−02 | 5.191E−02 | 8.688E−02 | 9.074E−02 | 5.620E−02 | 4.569E−02 | 4.977E−02 |
| 302 | 5.170E−03 | 3.711E−02 | 9.289E−03 | 1.375E−02 | 1.098E−02 | 3.389E−02 | 1.628E−02 | 5.642E−03 | 1.304E−02 | 6.200E−03 | 1.015E−02 | 5.535E−03 | 1.040E−02 |
| 303 | 1.617E−01 | 3.938E−01 | 2.270E−01 | 2.188E−01 | 1.864E−01 | 2.473E−01 | 1.817E−01 | 1.871E−01 | 3.022E−01 | 2.209E−01 | 2.345E−01 | 2.040E−01 | 2.641E−01 |
| 304 | 4.848E−03 | 1.073E−02 | 2.574E−03 | 5.685E−03 | 2.917E−03 | 6.028E−03 | 2.210E−03 | 3.561E−03 | 3.711E−03 | 4.870E−03 | 2.746E−03 | 9.675E−04 | 2.982E−03 |
| 305 | 2.053E−01 | 5.878E−01 | 3.164E−01 | 3.799E−01 | 3.112E−01 | 3.637E−01 | 3.162E−01 | 2.449E−01 | 5.619E−01 | 4.649E−01 | 3.606E−01 | 3.395E−01 | 2.377E−01 |
| 306 | 2.360E−02 | 5.792E−02 | 2.057E−02 | 2.210E−02 | 1.995E−02 | 3.111E−02 | 2.036E−02 | 1.517E−02 | 3.368E−02 | 3.261E−02 | 2.810E−02 | 2.896E−02 | 2.446E−02 |
| 307 | 1.156E+00 | 1.837E+00 | 1.973E+00 | 1.465E+00 | 1.421E+00 | 2.186E+00 | 1.539E+00 | 1.429E+00 | 1.484E+00 | 8.214E−01 | 1.747E+00 | 1.735E+00 | 2.066E+00 |
| 308 | 2.424E−02 | 4.012E−02 | 3.218E−02 | 2.574E−02 | 2.703E−02 | 3.904E−02 | 2.360E−02 | 2.510E−02 | 2.660E−02 | 1.306E−02 | 3.068E−02 | 3.153E−02 | 3.711E−02 |
| 309 | 3.540E−03 | 6.071E−03 | 4.290E−03 | 4.140E−03 | 3.111E−03 | 7.594E−03 | 4.741E−03 | 1.937E−03 | 6.521E−03 | 5.985E−03 | 4.505E−03 | 3.861E−03 | 4.462E−03 |
| 310 | 9.031E−03 | 3.926E−03 | 1.999E−03 | 2.617E−03 | 1.830E−03 | 2.875E−03 | 1.866E−03 | 2.574E−03 | 3.861E−03 | 3.325E−03 | 1.740E−03 | 2.210E−03 | 2.982E−03 |
| 311 | 9.675E−04 | 3.583E−04 | 7.144E−04 | 6.543E−04 | 7.315E−04 | 7.873E−04 | 1.188E−03 | 4.848E−04 | 4.441E−04 | 6.650E−04 | 7.251E−04 | 4.140E−04 | 2.789E−03 |
| 312 | 9.675E−04 | 7.144E−04 | 1.429E−04 | 2.188E−04 | 3.668E−04 | 0.000E+00 | 8.474E−04 | 1.613E−04 | 4.441E−04 | 6.650E−04 | 5.792E−04 | 0.000E+00 | 7.444E−04 |
| 313 | 9.224E−02 | 1.948E−01 | 1.223E−01 | 1.210E−01 | 1.401E−01 | 1.688E−01 | 1.950E−01 | 1.169E−01 | 1.742E−01 | 1.242E−01 | 1.079E−01 | 1.259E−01 | 1.058E−01 |
| 314 | 2.066E−02 | 1.180E−02 | 2.853E−03 | 5.899E−03 | 4.398E−03 | 9.182E−03 | 6.607E−03 | 5.642E−03 | 5.642E−03 | 9.074E−03 | 5.663E−03 | 4.698E−03 | 4.655E−03 |
| 315 | 2.130E−02 | 3.861E−02 | 2.982E−02 | 2.553E−02 | 2.274E−02 | 2.617E−02 | 3.625E−02 | 1.341E−02 | 3.347E−02 | 2.017E−02 | 2.087E−02 | 2.574E−02 | 1.952E−02 |
| 316 | 3.540E−03 | 3.218E−03 | 1.285E−03 | 8.731E−04 | 7.315E−04 | 2.360E−03 | 1.697E−03 | 1.131E−03 | 1.038E−03 | 1.772E−03 | 4.355E−04 | 1.519E−03 | 3.711E−04 |
| 317 | 1.873E−02 | 2.896E−02 | 2.746E−02 | 2.210E−02 | 1.995E−02 | 2.381E−02 | 3.068E−02 | 2.188E−02 | 2.960E−02 | 1.883E−02 | 2.617E−02 | 2.145E−02 | 1.746E−02 |
| 318 | 4.205E−03 | 2.143E−03 | 1.999E−03 | 3.068E−03 | 2.381E−03 | 2.875E−03 | 2.036E−03 | 1.937E−03 | 1.630E−03 | 1.995E−03 | 1.304E−03 | 1.658E−03 | 7.444E−04 |
| 319 | 1.043E−01 | 2.634E−01 | 1.965E−01 | 2.219E−01 | 1.371E−01 | 2.344E−01 | 2.275E−01 | 1.836E−01 | 1.963E−01 | 1.317E−01 | 2.001E−01 | 1.639E−01 | 1.609E−01 |
| 320 | 6.457E−04 | 1.429E−03 | 2.853E−04 | 4.376E−04 | 3.668E−04 | 1.311E−03 | 1.358E−03 | 4.848E−04 | 4.441E−04 | 6.650E−04 | 1.450E−04 | 2.767E−04 | 1.858E−04 |
| 321 | 1.006E−01 | 2.887E−01 | 1.974E−01 | 2.197E−01 | 1.984E−01 | 2.462E−01 | 2.451E−01 | 1.652E−01 | 3.079E−01 | 1.727E−01 | 1.841E−01 | 1.720E−01 | 1.075E−01 |
| 322 | 3.540E−03 | 9.997E−03 | 7.723E−03 | 8.302E−03 | 6.586E−03 | 8.645E−03 | 7.637E−03 | 5.170E−03 | 7.701E−03 | 6.436E−03 | 6.521E−03 | 6.500E−03 | 4.655E−03 |
| 323 | 1.051E−01 | 3.563E−01 | 2.745E−01 | 2.756E−01 | 1.978E−01 | 3.204E−01 | 2.916E−01 | 2.390E−01 | 2.462E−01 | 1.500E−01 | 2.497E−01 | 1.989E−01 | 1.963E−01 |
| 324 | 5.814E−03 | 1.321E−02 | 8.152E−03 | 1.244E−02 | 8.967E−03 | 8.130E−03 | 7.465E−03 | 7.594E−03 | 9.353E−03 | 6.436E−03 | 6.672E−03 | 5.663E−03 | 5.578E−03 |
| 325 | 5.492E−03 | 1.287E−02 | 6.564E−03 | 8.946E−03 | 7.144E−03 | 1.154E−02 | 9.847E−03 | 7.744E−03 | 6.371E−03 | 1.064E−02 | 5.084E−03 | 8.431E−03 | 8.924E−03 |
| 326 | 9.675E−04 | 2.143E−03 | 7.144E−04 | 1.746E−03 | 1.098E−03 | 2.098E−03 | 1.527E−03 | 6.457E−04 | 1.334E−03 | 1.107E−03 | 5.792E−04 | 1.519E−03 | 1.302E−03 |
| 327 | 1.131E−02 | 2.403E−02 | 1.058E−02 | 6.993E−03 | 9.889E−03 | 1.180E−02 | 1.255E−02 | 9.847E−03 | 1.008E−02 | 1.197E−02 | 1.015E−02 | 1.049E−02 | 6.693E−03 |
| 328 | 3.540E−03 | 2.853E−03 | 7.144E−04 | 2.188E−03 | 7.315E−04 | 2.617E−03 | 2.210E−03 | 6.457E−04 | 8.903E−04 | 2.210E−03 | 1.740E−03 | 1.244E−03 | 1.673E−03 |
| 329 | 2.656E−01 | 5.210E−01 | 4.517E−01 | 4.817E−01 | 5.049E−01 | 5.572E−01 | 5.992E−01 | 3.474E−01 | 2.892E−01 | 2.674E−01 | 3.441E−01 | 4.858E−01 | 4.028E−01 |
| 330 | 3.218E−03 | 8.216E−03 | 5.706E−03 | 8.302E−03 | 6.586E−03 | 8.645E−03 | 5.599E−03 | 4.526E−03 | 3.261E−03 | 2.210E−03 | 4.784E−03 | 4.140E−03 | 5.020E−03 |
| 331 | 1.808E−02 | 5.942E−02 | 2.574E−02 | 3.668E−02 | 3.196E−02 | 3.625E−02 | 3.733E−02 | 2.295E−02 | 2.231E−02 | 2.939E−02 | 2.446E−02 | 2.338E−02 | 3.218E−02 |
| 332 | 9.675E−04 | 2.143E−03 | 2.853E−04 | 6.543E−04 | 9.139E−04 | 4.977E−03 | 8.474E−04 | 4.848E−04 | 7.422E−04 | 6.650E−04 | 7.251E−04 | 1.382E−03 | 1.116E−03 |
| 333 | 1.420E−02 | 3.068E−02 | 1.699E−02 | 2.096E−02 | 1.463E−02 | 2.403E−02 | 2.360E−02 | 1.469E−02 | 1.542E−02 | 1.596E−02 | 1.929E−02 | 1.864E−02 | 1.914E−02 |
| 334 | 0.000E+00 | 3.583E−04 | 1.429E−04 | 4.376E−04 | 0.000E+00 | 2.617E−04 | 1.697E−04 | 1.613E−04 | 0.000E+00 | 2.210E−04 | 4.355E−04 | 8.281E−04 | 0.000E+00 |
| 335 | 3.196E−02 | 5.470E−02 | 4.376E−02 | 4.741E−02 | 4.419E−02 | 5.814E−02 | 5.149E−02 | 2.703E−02 | 3.432E−02 | 2.446E−02 | 3.561E−02 | 3.218E−02 | 4.462E−02 |
| 336 | 3.218E−03 | 6.071E−03 | 1.570E−03 | 3.711E−03 | 2.188E−03 | 4.205E−03 | 1.697E−03 | 1.613E−03 | 2.381E−03 | 2.446E−03 | 2.167E−03 | 2.210E−03 | 2.231E−03 |
| 337 | 4.419E−02 | 1.287E−01 | 8.045E−02 | 1.060E−01 | 7.787E−02 | 1.375E−01 | 1.221E−01 | 6.114E−02 | 6.500E−02 | 4.719E−02 | 7.851E−02 | 7.680E−02 | 7.337E−02 |
| 338 | 9.675E−04 | 3.583E−03 | 1.429E−03 | 2.403E−03 | 1.648E−03 | 3.153E−03 | 4.076E−03 | 9.675E−04 | 4.441E−04 | 6.650E−04 | 2.029E−03 | 1.105E−03 | 1.487E−03 |
| 339 | 2.510E−02 | 5.942E−02 | 5.041E−02 | 5.363E−02 | 5.127E−02 | 5.749E−02 | 5.149E−02 | 3.947E−02 | 3.883E−02 | 2.295E−02 | 4.226E−02 | 3.325E−02 | 5.170E−02 |
| 340 | 4.205E−03 | 3.218E−03 | 2.574E−03 | 2.403E−03 | 1.648E−03 | 4.977E−03 | 2.381E−03 | 1.776E−03 | 2.660E−03 | 3.111E−03 | 2.029E−03 | 2.488E−03 | 2.789E−03 |
| 341 | 5.170E−03 | 8.924E−03 | 4.569E−03 | 6.993E−03 | 4.762E−03 | 8.388E−03 | 5.599E−03 | 3.711E−03 | 4.741E−03 | 6.436E−03 | 2.167E−03 | 4.977E−03 | 3.904E−03 |
| 342 | 6.457E−04 | 1.073E−03 | 4.290E−04 | 1.311E−03 | 1.098E−03 | 2.617E−04 | 5.084E−04 | 3.218E−04 | 2.960E−04 | 8.860E−04 | 4.355E−04 | 4.140E−04 | 7.444E−04 |
| 343 | 6.457E−03 | 9.289E−03 | 6.436E−03 | 5.020E−03 | 4.205E−03 | 6.822E−03 | 5.427E−03 | 4.355E−03 | 4.591E−03 | 1.040E−02 | 5.363E−03 | 6.221E−03 | 5.020E−03 |
| 344 | 0.000E+00 | 3.583E−04 | 0.000E+00 | 2.188E−04 | 3.668E−04 | 0.000E+00 | 6.779E−04 | 4.848E−04 | 0.000E+00 | 6.650E−04 | 0.000E+00 | 0.000E+00 | 0.000E+00 |

APPENDIX D-continued

Ovarian Cancer
Training Dataset

| | BY | BZ | CA | CB | CC | CD | CE | CF | CG | CH | CI | CJ | CK |
|---|---|---|---|---|---|---|---|---|---|---|---|---|---|
| 1 | CA420 | 14657 | 13667 | CA0035 | CA110 | 13675 | CA128 | 14663 | CA206 | 13639 | 14633 | CA060 | 14676 |
| 2 | Control | Benign | Late Malignant | Control | Control | Benign | Control | Benign | Control | Early Malignant | Early Malignant | Control | Late Malignant |
| 3 | 0 | 1 | 3 | 0 | 0 | 1 | 0 | 1 | 0 | 2 | 2 | 0 | 3 |
| 4 | 1 | −1 | −1 | 1 | 1 | −1 | 1 | −1 | 1 | −1 | −1 | 1 | −1 |
| 5 | 1.785E+00 | 2.521E+00 | 1.067E+00 | 1.502E+00 | 1.949E+00 | 2.339E+00 | 1.888E+00 | 1.703E+00 | 9.049E−01 | 1.794E+00 | 1.426E+00 | 1.415E+00 | 1.333E+00 |
| 6 | 9.312E−01 | 4.539E−01 | 4.281E−01 | 1.416E+00 | 1.042E+00 | 1.180E+00 | 6.320E−01 | 6.159E−01 | 4.635E−01 | 3.906E−01 | 4.152E−01 | 4.024E−01 | 3.315E−01 |
| 7 | 2.253E−01 | 2.189E−01 | 1.084E−01 | 3.004E−01 | 3.670E−01 | 3.058E−01 | 3.079E−01 | 2.929E−01 | 1.212E−01 | 1.738E−01 | 1.867E−01 | 1.202E−01 | 1.845E−01 |
| 8 | 1.023E+00 | 2.741E+00 | 6.599E−01 | 9.152E−01 | 1.073E+00 | 1.757E+00 | 2.727E+00 | 1.024E+00 | 5.987E−01 | 2.368E+00 | 1.077E+00 | 2.412E+00 | 6.813E−01 |
| 9 | 2.918E−02 | 3.219E−02 | 1.620E−02 | 1.502E−02 | 3.863E−03 | 2.124E−02 | 3.809E−02 | 2.554E−02 | 2.521E−02 | 2.210E−02 | 1.899E−02 | 1.781E−02 | 2.328E−02 |
| 10 | 1.459E−02 | 1.352E−02 | 2.167E−02 | 2.403E−02 | 1.159E−02 | 4.249E−03 | 7.607E−03 | 8.498E−03 | 4.378E−03 | 5.515E−03 | 4.861E−03 | 5.097E−03 | 1.116E−02 |
| 11 | 9.431E−03 | 7.790E−03 | 0.000E+00 | 2.103E−02 | 2.318E−02 | 1.277E−02 | 3.809E−03 | 1.695E−02 | 8.208E−03 | 5.515E−03 | 6.320E−03 | 4.592E−03 | 9.002E−03 |
| 12 | 4.238E−03 | 4.152E−03 | 0.000E+00 | 6.009E−03 | 2.704E−02 | 2.124E−02 | 1.137E−02 | 1.277E−02 | 5.472E−03 | 5.515E−03 | 4.378E−03 | 3.573E−03 | 4.764E−03 |
| 13 | 9.903E−03 | 3.584E−02 | 2.167E−02 | 0.000E+00 | 1.545E−02 | 2.124E−02 | 3.047E−02 | 2.124E−02 | 1.148E−02 | 1.491E−02 | 1.363E−02 | 2.393E−02 | 1.481E−02 |
| 14 | 6.180E−02 | 4.206E−02 | 4.335E−02 | 5.708E−02 | 6.170E−02 | 3.391E−02 | 4.560E−02 | 4.667E−02 | 3.069E−02 | 3.144E−02 | 3.305E−02 | 3.616E−02 | 4.131E−02 |
| 15 | 8.959E−03 | 7.790E−03 | 1.084E−02 | 1.202E−02 | 1.159E−02 | 8.487E−03 | 3.809E−03 | 0.000E+00 | 4.378E−03 | 4.410E−03 | 3.895E−03 | 4.592E−03 | 5.826E−03 |
| 16 | 4.710E−04 | 5.193E−04 | 0.000E+00 | 0.000E+00 | 0.000E+00 | 0.000E+00 | 0.000E+00 | 0.000E+00 | 2.189E−03 | 1.105E−03 | 4.861E−04 | 0.000E+00 | 0.000E+00 |
| 17 | 1.416E−03 | 1.038E−03 | 0.000E+00 | 0.000E+00 | 0.000E+00 | 0.000E+00 | 0.000E+00 | 1.277E−02 | 2.446E−01 | 6.341E−02 | 4.818E−02 | 3.058E−02 | 5.300E−02 |
| 18 | 2.264E−02 | 2.178E−02 | 3.788E−02 | 1.202E−02 | 3.863E−02 | 6.363E−02 | 5.708E−02 | 2.554E−02 | 7.571E−01 | 1.513E−01 | 1.545E−01 | 9.388E−02 | 1.620E−01 |
| 19 | 7.736E−02 | 1.277E−01 | 4.335E−02 | 9.603E−02 | 1.770E−01 | 1.996E−01 | 1.298E−01 | 1.062E−01 | 3.766E−01 | 1.706E−01 | 1.556E−01 | 9.077E−02 | 1.159E−01 |
| 20 | 2.361E−03 | 1.556E−03 | 0.000E+00 | 3.004E−03 | 3.863E−03 | 8.487E−03 | 0.000E+00 | 4.249E−03 | 1.094E−03 | 5.515E−04 | 9.732E−04 | 2.039E−03 | 0.000E+00 |
| 21 | 1.792E−02 | 8.820E−03 | 2.704E−02 | 9.002E−03 | 1.545E−02 | 4.249E−03 | 2.285E−02 | 2.124E−02 | 4.324E−02 | 2.092E−02 | 1.803E−02 | 1.738E−02 | 5.826E−03 |
| 22 | 0.000E+00 | 1.556E−03 | 5.408E−03 | 0.000E+00 | 0.000E+00 | 1.695E−02 | 3.809E−03 | 1.277E−02 | 1.094E−02 | 0.000E+00 | 3.401E−03 | 2.554E−03 | 3.712E−03 |
| 23 | 3.916E−02 | 2.436E−02 | 4.871E−02 | 6.309E−02 | 4.635E−02 | 9.764E−02 | 6.470E−02 | 6.373E−02 | 6.127E−02 | 4.850E−02 | 3.938E−02 | 3.777E−02 | 2.543E−02 |
| 24 | 4.292E−02 | 5.708E−02 | 5.955E−02 | 4.807E−02 | 6.170E−02 | 5.944E−02 | 3.423E−02 | 8.069E−02 | 7.850E−01 | 1.685E−01 | 1.738E−01 | 9.131E−02 | 1.513E−01 |
| 25 | 1.695E−02 | 9.861E−03 | 1.084E−02 | 2.403E−02 | 3.090E−02 | 2.972E−02 | 1.524E−02 | 1.695E−02 | 2.082E−02 | 1.652E−02 | 1.266E−02 | 2.350E−02 | 1.223E−02 |
| 26 | 1.652E−02 | 2.028E−02 | 1.084E−02 | 3.605E−02 | 2.318E−02 | 1.695E−02 | 1.899E−02 | 2.972E−02 | 1.094E−02 | 1.652E−02 | 1.170E−02 | 1.170E−02 | 1.749E−02 |
| 27 | 2.361E−03 | 3.637E−03 | 0.000E+00 | 6.009E−03 | 7.715E−03 | 1.695E−02 | 0.000E+00 | 0.000E+00 | 1.094E−03 | 4.410E−03 | 1.942E−03 | 3.058E−03 | 9.002E−03 |
| 28 | 2.833E−02 | 2.124E−02 | 1.620E−02 | 1.202E−02 | 4.249E−02 | 3.820E−02 | 2.661E−02 | 3.401E−02 | 5.805E−02 | 2.865E−02 | 2.436E−02 | 2.961E−02 | 2.017E−02 |
| 29 | 4.710E−02 | 2.704E−02 | 3.251E−02 | 5.708E−02 | 5.021E−02 | 5.944E−02 | 3.423E−02 | 2.972E−02 | 7.779E−02 | 3.036E−02 | 3.594E−02 | 3.927E−02 | 2.543E−02 |
| 30 | 5.376E−02 | 6.953E−02 | 2.704E−02 | 3.004E−02 | 3.476E−02 | 2.972E−02 | 3.809E−02 | 2.972E−02 | 3.594E−01 | 1.003E−01 | 1.180E−01 | 5.708E−02 | 1.127E−01 |
| 31 | 3.723E−02 | 3.637E−02 | 5.408E−02 | 3.605E−02 | 4.249E−02 | 2.972E−02 | 3.809E−02 | 1.277E−02 | 1.824E−01 | 5.461E−02 | 7.296E−02 | 5.665E−02 | 5.880E−02 |
| 32 | 2.124E−02 | 8.251E−02 | 4.335E−02 | 1.803E−02 | 3.863E−02 | 4.249E−02 | 9.506E−02 | 2.554E−02 | 4.324E−02 | 5.569E−02 | 4.721E−02 | 5.097E−02 | 4.238E−02 |
| 33 | 8.487E−03 | 1.094E−02 | 5.408E−03 | 1.202E−02 | 1.931E−02 | 8.487E−03 | 0.000E+00 | 1.277E−02 | 1.148E−02 | 8.820E−03 | 9.238E−03 | 1.170E−02 | 1.170E−02 |
| 34 | 2.350E−01 | 3.155E−01 | 2.328E−01 | 1.652E−01 | 1.888E−01 | 3.433E−01 | 3.155E−01 | 4.077E−01 | 2.350E−01 | 6.416E−01 | 3.755E−01 | 3.916E−01 | 3.047E−01 |
| 35 | 7.500E−02 | 8.358E−02 | 5.955E−02 | 4.506E−02 | 4.249E−02 | 5.097E−02 | 4.185E−02 | 3.820E−02 | 6.406E−02 | 3.970E−02 | 5.644E−02 | 8.058E−02 | 1.059E−01 |
| 36 | 6.127E−03 | 3.637E−03 | 5.408E−03 | 1.202E−02 | 7.715E−03 | 4.249E−03 | 7.607E−03 | 8.498E−03 | 6.567E−03 | 2.210E−03 | 5.354E−03 | 6.631E−03 | 4.238E−03 |
| 37 | 9.431E−03 | 9.861E−03 | 2.704E−02 | 3.004E−02 | 3.863E−02 | 2.124E−02 | 1.899E−02 | 2.554E−02 | 2.521E−02 | 1.438E−02 | 1.363E−02 | 9.689E−03 | 1.534E−02 |
| 38 | 1.127E−02 | 1.191E−02 | 1.084E−02 | 1.502E−02 | 1.931E−02 | 3.820E−02 | 2.661E−02 | 1.695E−02 | 1.588E−02 | 2.532E−02 | 1.556E−02 | 1.223E−02 | 1.481E−02 |
| 39 | 1.352E−01 | 7.210E−02 | 4.871E−02 | 1.470E−01 | 1.309E−01 | 1.695E−02 | 4.946E−02 | 3.401E−02 | 1.309E−01 | 2.918E−02 | 8.895E−02 | 6.835E−02 | 5.773E−02 |
| 40 | 1.459E−01 | 1.202E−01 | 8.659E−02 | 1.202E−01 | 6.942E−02 | 9.764E−02 | 7.607E−02 | 7.650E−02 | 1.577E−01 | 9.431E−02 | 1.298E−01 | 7.339E−02 | 1.620E−01 |
| 41 | 9.903E−03 | 1.609E−02 | 6.491E−02 | 1.502E−02 | 3.476E−02 | 5.097E−02 | 4.560E−02 | 5.097E−02 | 2.843E−02 | 2.264E−02 | 1.609E−02 | 2.650E−02 | 3.015E−02 |
| 42 | 2.361E−03 | 4.152E−03 | 0.000E+00 | 3.004E−03 | 3.863E−03 | 8.487E−03 | 7.607E−03 | 4.249E−03 | 2.189E−03 | 7.167E−03 | 1.459E−03 | 2.554E−03 | 1.588E−03 |
| 43 | 4.861E−03 | 5.221E−03 | 6.481E−03 | 7.201E−03 | 4.630E−03 | 7.124E−03 | 6.378E−03 | 8.153E−03 | 4.449E−03 | 2.598E−02 | 6.636E−03 | 9.156E−03 | 5.324E−03 |
| 44 | 1.551E−01 | 1.715E−01 | 3.724E−01 | 2.302E−01 | 2.675E−01 | 3.549E−01 | 2.778E−01 | 3.472E−01 | 2.667E−01 | 6.836E−01 | 3.438E−01 | 3.970E−01 | 2.573E−01 |
| 45 | 6.893E−02 | 4.990E−02 | 1.453E−01 | 1.404E−01 | 1.222E−01 | 1.566E−01 | 1.085E−01 | 1.294E−01 | 1.448E−01 | 2.694E−01 | 1.283E−01 | 2.112E−01 | 8.436E−02 |
| 46 | 7.253E−02 | 8.487E−02 | 1.181E−01 | 1.409E−01 | 1.564E−01 | 1.181E−01 | 1.469E−01 | 1.731E−01 | 9.645E−02 | 2.678E−01 | 1.168E−01 | 1.404E−01 | 9.953E−02 |
| 47 | 8.822E−02 | 1.157E−01 | 1.998E−01 | 1.361E−01 | 1.749E−01 | 2.320E−01 | 1.551E−01 | 2.312E−01 | 2.383E−01 | 5.355E−01 | 2.448E−01 | 3.496E−01 | 1.919E−01 |

APPENDIX D-continued

Ovarian Cancer Training Dataset

| | | | | | | | | | | | | | |
|---|---|---|---|---|---|---|---|---|---|---|---|---|---|
| 48 | 1.831E−02 | 1.592E−02 | 1.816E−02 | 3.446E−02 | 3.781E−02 | 1.728E−02 | 2.554E−02 | 2.443E−02 | 2.322E−02 | 5.298E−02 | 1.934E−02 | 5.684E−02 | 3.112E−02 |
| 49 | 7.124E−03 | 7.973E−03 | 9.079E−03 | 1.008E−02 | 7.407E−03 | 2.034E−03 | 6.378E−03 | 1.834E−02 | 1.299E−02 | 1.692E−02 | 1.049E−02 | 1.785E−02 | 9.388E−03 |
| 50 | 3.832E−03 | 2.623E−03 | 6.481E−03 | 5.041E−03 | 5.555E−03 | 2.034E−03 | 7.304E−03 | 3.061E−03 | 3.292E−03 | 5.941E−03 | 4.089E−03 | 3.421E−03 | 2.675E−03 |
| 51 | 1.548E−01 | 1.890E−01 | 1.440E−01 | 1.440E−01 | 1.564E−01 | 1.057E−01 | 2.472E−01 | 2.220E−01 | 9.053E−02 | 2.321E−01 | 1.361E−01 | 1.016E−01 | 2.209E−01 |
| 52 | 1.129E−03 | 3.369E−03 | 6.481E−03 | 5.761E−03 | 5.555E−03 | 4.064E−03 | 1.733E−02 | 1.018E−02 | 4.064E−03 | 9.002E−03 | 3.858E−03 | 5.015E−03 | 3.292E−03 |
| 53 | 3.369E−02 | 4.861E−02 | 3.369E−02 | 2.014E−02 | 4.167E−02 | 5.298E−02 | 4.372E−02 | 7.844E−02 | 3.498E−02 | 1.011E−01 | 6.867E−02 | 6.198E−02 | 4.295E−02 |
| 54 | 5.430E+00 | 4.659E+00 | 5.234E+00 | 4.785E+00 | 4.427E+00 | 4.931E+00 | 4.271E+00 | 4.212E+00 | 5.934E+00 | 3.853E+00 | 5.820E+00 | 4.691E+00 | 4.764E+00 |
| 55 | 5.581E−01 | 6.504E−01 | 5.709E−01 | 5.311E−01 | 5.466E−01 | 3.876E−01 | 5.653E−01 | 5.559E−01 | 5.169E−01 | 6.078E−01 | 6.617E−01 | 3.953E−01 | 7.671E−01 |
| 56 | 1.736E−01 | 1.327E−01 | 1.842E−01 | 2.202E−01 | 1.849E−01 | 2.196E−01 | 1.888E−01 | 2.106E−01 | 1.849E−01 | 1.528E−01 | 1.827E−01 | 1.741E−01 | 1.476E−01 |
| 57 | 3.237E+00 | 4.397E+00 | 4.027E+00 | 3.447E+00 | 4.089E+00 | 2.883E+00 | 3.995E+00 | 4.170E+00 | 3.088E+00 | 3.360E+00 | 4.225E+00 | 2.237E+00 | 4.550E+00 |
| 58 | 3.189E−02 | 4.578E−02 | 6.867E−02 | 7.407E−02 | 1.157E−01 | 1.119E−01 | 1.157E−01 | 8.745E−02 | 4.424E−02 | 1.024E−01 | 5.838E−02 | 7.716E−02 | 5.993E−02 |
| 59 | 6.121E−02 | 8.102E−02 | 3.112E−02 | 3.601E−02 | 4.347E−02 | 3.266E−02 | 3.472E−02 | 4.990E−02 | 5.684E−02 | 4.578E−02 | 6.430E−02 | 4.244E−02 | 7.356E−02 |
| 60 | 1.481E−02 | 1.517E−02 | 1.039E−02 | 1.080E−02 | 9.259E−03 | 2.441E−02 | 1.824E−02 | 1.222E−02 | 2.454E−02 | 4.655E−02 | 2.855E−02 | 3.369E−02 | 2.045E−02 |
| 61 | 1.673E+00 | 2.470E+00 | 8.887E−01 | 1.398E+00 | 1.348E+00 | 4.334E−01 | 6.957E−01 | 1.192E+00 | 9.334E−01 | 1.083E+00 | 8.209E−01 | 1.351E+00 | 2.610E+00 |
| 62 | 4.417E−01 | 2.154E−01 | 8.784E−01 | 9.549E−01 | 8.204E−01 | 1.043E+00 | 7.778E−01 | 6.210E−01 | 4.668E−01 | 4.180E−01 | 3.368E−01 | 5.248E−01 | 2.203E−01 |
| 63 | 1.402E−02 | 1.903E−02 | 1.168E−02 | 1.942E−02 | 1.294E−02 | 1.119E−02 | 3.652E−03 | 1.119E−02 | 1.181E−02 | 1.824E−02 | 1.119E−02 | 2.567E−02 | 2.045E−02 |
| 64 | 3.315E+00 | 1.783E+00 | 1.370E+00 | 1.155E+00 | 1.147E+00 | 1.180E+00 | 8.744E−01 | 7.697E−01 | 2.767E+00 | 1.771E+00 | 1.892E+00 | 2.432E+00 | 1.656E+00 |
| 65 | 1.240E−01 | 8.024E−02 | 8.307E−02 | 8.050E−02 | 9.619E−02 | 9.053E−02 | 6.841E−02 | 6.713E−02 | 1.296E−01 | 1.911E−01 | 1.304E−01 | 2.033E−01 | 9.413E−02 |
| 66 | 6.037E−01 | 4.419E−01 | 5.268E−01 | 3.318E−01 | 3.729E−01 | 2.855E−01 | 5.170E−01 | 3.292E−01 | 5.124E−01 | 6.364E−01 | 4.815E−01 | 4.869E−01 | 5.362E−01 |
| 67 | 3.729E−02 | 5.607E−02 | 2.726E−02 | 4.527E−02 | 4.912E−02 | 4.269E−02 | 7.201E−02 | 5.401E−02 | 5.298E−02 | 1.697E−01 | 7.844E−02 | 1.186E−01 | 6.198E−02 |
| 68 | 7.381E−02 | 6.276E−02 | 1.065E−01 | 4.167E−02 | 7.767E−02 | 1.222E−01 | 7.304E−02 | 9.773E−02 | 8.359E−02 | 2.212E−01 | 9.233E−02 | 1.538E−01 | 6.944E−02 |
| 69 | 8.562E−01 | 1.032E+00 | 2.153E−01 | 2.906E−01 | 2.340E−01 | 1.036E−01 | 1.605E−01 | 1.903E−01 | 3.783E−01 | 4.652E−01 | 2.481E−01 | 6.217E−01 | 9.301E−01 |
| 70 | 3.086E−02 | 3.832E−02 | 1.947E−02 | 2.086E−02 | 2.958E−02 | 1.628E−02 | 2.096E−02 | 2.240E−02 | 2.623E−02 | 6.173E−02 | 3.189E−02 | 6.173E−02 | 5.401E−02 |
| 71 | 8.925E−03 | 9.079E−03 | 1.296E−03 | 4.321E−03 | 9.259E−04 | 1.018E−03 | 3.652E−03 | 4.064E−03 | 1.062E−02 | 1.561E−02 | 5.118E−03 | 1.003E−02 | 7.870E−03 |
| 72 | 1.808E−03 | 1.867E−03 | 0.000E+00 | 1.440E−03 | 1.849E−03 | 1.018E−03 | 5.478E−03 | 0.000E+00 | 2.752E−03 | 5.144E−03 | 1.983E−03 | 3.549E−03 | 3.163E−03 |
| 73 | 9.921E−04 | 0.000E+00 | 0.000E+00 | 3.160E−03 | 0.000E+00 | 0.000E+00 | 0.000E+00 | 0.000E+00 | 8.465E−02 | 1.445E−02 | 1.941E−02 | 9.661E−03 | 6.682E−03 |
| 74 | 2.980E−03 | 4.368E−03 | 0.000E+00 | 1.580E−02 | 4.063E−03 | 8.928E−03 | 0.000E+00 | 0.000E+00 | 2.269E−01 | 3.420E−02 | 4.549E−02 | 1.614E−02 | 3.115E−02 |
| 75 | 3.521E−02 | 3.770E−02 | 1.196E−01 | 1.512E−01 | 1.015E−01 | 7.585E−02 | 4.007E−02 | 1.027E−01 | 5.711E−01 | 1.129E−01 | 1.456E−01 | 5.903E−02 | 1.309E−01 |
| 76 | 4.458E−02 | 5.406E−02 | 1.140E−01 | 2.246E−01 | 1.298E−01 | 1.388E−01 | 8.002E−02 | 1.614E−01 | 7.201E−02 | 3.070E−02 | 6.603E−02 | 4.831E−02 | 6.072E−02 |
| 77 | 4.955E−03 | 3.273E−03 | 0.000E+00 | 6.953E−02 | 4.063E−03 | 4.470E−03 | 1.196E−02 | 4.470E−03 | 5.181E−03 | 1.163E−03 | 3.578E−03 | 1.614E−03 | 7.799E−03 |
| 78 | 4.955E−04 | 5.463E−04 | 5.688E−03 | 3.160E−03 | 0.000E+00 | 4.470E−03 | 0.000E+00 | 0.000E+00 | 0.000E+00 | 0.000E+00 | 5.113E−04 | 1.073E−03 | 5.576E−04 |
| 79 | 0.000E+00 | 5.463E−04 | 0.000E+00 | 3.160E−03 | 0.000E+00 | 4.470E−03 | 4.007E−03 | 0.000E+00 | 1.399E+00 | 1.919E−01 | 1.998E−01 | 7.077E−02 | 1.693E−01 |
| 80 | 0.000E+00 | 1.637E−03 | 1.140E−02 | 3.160E−03 | 0.000E+00 | 0.000E+00 | 1.196E−02 | 4.470E−03 | 1.287E−01 | 1.163E−02 | 2.348E−02 | 9.120E−03 | 1.614E−02 |
| 81 | 2.980E−03 | 6.546E−03 | 3.984E−02 | 3.160E−03 | 4.063E−03 | 4.470E−03 | 1.998E−02 | 2.235E−02 | 3.507E+00 | 4.424E−01 | 4.955E−01 | 1.986E−01 | 3.228E−01 |
| 82 | 2.483E−03 | 4.910E−03 | 0.000E+00 | 6.321E−03 | 4.063E−03 | 8.928E−03 | 4.007E−03 | 1.783E−02 | 1.760E+00 | 2.065E−01 | 2.178E−01 | 8.205E−02 | 1.693E−01 |
| 83 | 0.000E+00 | 5.463E−04 | 0.000E+00 | 0.000E+00 | 0.000E+00 | 4.470E−03 | 0.000E+00 | 0.000E+00 | 3.183E−01 | 2.607E−02 | 3.330E−02 | 1.343E−02 | 2.731E−02 |
| 84 | 6.941E−03 | 2.731E−03 | 1.140E−02 | 9.470E−03 | 4.063E−03 | 1.783E−02 | 8.002E−03 | 1.343E−02 | 1.670E−02 | 1.445E−02 | 1.535E−02 | 1.400E−02 | 1.727E−02 |
| 85 | 9.921E−04 | 3.273E−03 | 1.140E−02 | 3.160E−03 | 0.000E+00 | 4.470E−03 | 4.007E−03 | 1.343E−02 | 2.359E−02 | 6.964E−03 | 1.024E−02 | 4.831E−03 | 3.341E−03 |
| 86 | 4.458E−03 | 8.194E−03 | 3.420E−02 | 1.896E−02 | 0.000E+00 | 2.235E−02 | 8.002E−03 | 4.470E−03 | 1.208E−01 | 1.332E−02 | 3.014E−02 | 1.558E−02 | 1.558E−02 |
| 87 | 1.185E−02 | 1.851E−02 | 7.404E−02 | 7.585E−02 | 2.032E−02 | 1.343E−02 | 6.400E−02 | 3.126E−02 | 9.391E−02 | 8.126E−03 | 3.736E−02 | 2.302E−02 | 4.063E−02 |
| 88 | 2.483E−03 | 3.273E−03 | 1.140E−02 | 1.580E−02 | 4.063E−03 | 4.470E−03 | 1.603E−02 | 0.000E+00 | 1.501E−02 | 1.738E−03 | 7.167E−03 | 2.144E−03 | 7.246E−03 |
| 89 | 2.980E−03 | 6.546E−03 | 5.688E−03 | 3.160E−02 | 3.251E−02 | 1.783E−02 | 0.000E+00 | 3.126E−02 | 1.036E−02 | 6.964E−03 | 1.174E−02 | 1.343E−02 | 1.174E−02 |
| 90 | 1.840E−02 | 1.693E−02 | 6.828E−02 | 1.140E−01 | 7.302E−02 | 3.126E−02 | 2.404E−02 | 4.910E−02 | 3.341E−02 | 9.865E−03 | 3.939E−02 | 3.488E−02 | 2.788E−02 |
| 91 | 2.980E−03 | 4.910E−03 | 5.688E−03 | 0.000E+00 | 8.115E−03 | 1.343E−02 | 0.000E+00 | 2.235E−02 | 1.377E−02 | 1.738E−03 | 5.632E−03 | 2.686E−03 | 7.246E−03 |
| 92 | 2.980E−03 | 8.736E−03 | 1.140E−02 | 6.321E−03 | 4.063E−03 | 1.783E−02 | 8.002E−03 | 4.470E−03 | 2.359E−02 | 1.163E−02 | 1.591E−02 | 1.501E−02 | 1.332E−02 |
| 93 | 6.941E−03 | 6.005E−03 | 1.140E−02 | 3.160E−03 | 8.115E−03 | 2.675E−02 | 1.603E−02 | 8.939E−03 | 1.727E−02 | 3.476E−03 | 1.024E−02 | 7.506E−03 | 3.341E−03 |
| 94 | 4.955E−04 | 1.637E−03 | 0.000E+00 | 0.000E+00 | 0.000E+00 | 4.470E−03 | 8.002E−03 | 0.000E+00 | 8.634E−03 | 1.738E−03 | 1.024E−03 | 1.073E−03 | 5.576E−04 |
| 95 | 5.451E−03 | 1.309E−02 | 1.704E−02 | 9.470E−03 | 0.000E+00 | 0.000E+00 | 4.007E−03 | 8.939E−03 | 3.172E−02 | 8.126E−03 | 1.535E−02 | 1.287E−02 | 1.953E−02 |
| 96 | 2.483E−03 | 3.826E−03 | 1.140E−02 | 0.000E+00 | 1.219E−02 | 4.470E−03 | 0.000E+00 | 4.470E−03 | 3.047E−02 | 4.063E−03 | 9.210E−03 | 4.831E−03 | 1.174E−02 |
| 97 | 2.980E−03 | 2.178E−03 | 0.000E+00 | 1.896E−02 | 4.063E−03 | 4.470E−03 | 0.000E+00 | 8.939E−03 | 8.059E−03 | 6.964E−03 | 8.183E−03 | 7.506E−03 | 3.905E−03 |

APPENDIX D-continued

Ovarian Cancer
Training Dataset

| | | | | | | | | | | | | | |
|---|---|---|---|---|---|---|---|---|---|---|---|---|---|
| 98 | 2.980E−03 | 4.910E−03 | 1.704E−02 | 1.896E−02 | 0.000E+00 | 2.235E−02 | 2.799E−02 | 2.235E−02 | 1.501E−02 | 9.865E−03 | 1.275E−02 | 1.614E−02 | 1.558E−02 |
| 99 | 1.083E−01 | 5.996E−02 | 1.113E−01 | 1.717E−01 | 1.496E−01 | 1.790E−01 | 2.256E−01 | 1.312E−01 | 7.762E−02 | 9.074E−02 | 1.167E−01 | 1.101E−01 | 4.537E−02 |
| 100 | 2.636E−02 | 2.784E−02 | 1.852E−02 | 2.747E−02 | 4.856E−02 | 9.700E−03 | 6.524E−02 | 2.918E−02 | 2.624E−02 | 4.598E−02 | 3.507E−02 | 3.384E−02 | 3.814E−02 |
| 101 | 1.251E−01 | 1.557E−01 | 2.477E−01 | 1.852E−01 | 2.784E−01 | 2.575E−01 | 1.655E−01 | 2.477E−01 | 1.188E−01 | 1.373E−01 | 1.349E−01 | 1.101E−01 | 1.533E−01 |
| 102 | 3.470E−01 | 4.807E−01 | 9.773E−01 | 5.212E−01 | 6.573E−01 | 1.086E+00 | 1.156E+00 | 1.093E+00 | 4.390E−01 | 9.074E−01 | 7.737E−01 | 9.978E−01 | 7.382E−01 |
| 103 | 1.557E−01 | 2.587E−01 | 2.036E−01 | 2.612E−01 | 2.465E−01 | 3.004E−01 | 2.256E−01 | 2.330E−01 | 1.410E−01 | 1.410E−01 | 2.048E−01 | 1.166E−01 | 2.170E−01 |
| 104 | 1.729E−01 | 1.839E−01 | 4.083E−01 | 2.673E−01 | 3.004E−01 | 3.973E−01 | 3.777E−01 | 3.593E−01 | 2.085E−01 | 3.446E−01 | 3.237E−01 | 3.765E−01 | 2.416E−01 |
| 105 | 6.499E−01 | 6.364E−01 | 1.533E+00 | 6.965E−01 | 1.045E+00 | 1.300E+00 | 1.126E+00 | 1.349E+00 | 6.291E−01 | 1.300E+00 | 1.129E+00 | 1.193E+00 | 1.096E+00 |
| 106 | 1.471E−01 | 1.594E−01 | 1.688E−01 | 1.950E−01 | 1.582E−01 | 2.036E−01 | 2.256E−01 | 1.116E−01 | 1.263E−01 | 2.085E−01 | 2.085E−01 | 1.790E−01 | 8.596E−02 |
| 107 | 1.002E−01 | 8.719E−02 | 2.232E−01 | 1.508E−01 | 1.631E−01 | 1.643E−01 | 2.134E−01 | 1.754E−01 | 1.113E−01 | 1.962E−01 | 1.239E−01 | 1.300E−01 | 8.289E−02 |
| 108 | 1.741E−01 | 1.459E−01 | 3.458E−01 | 2.845E−01 | 2.735E−01 | 1.557E−01 | 1.778E−01 | 1.459E−01 | 1.145E−01 | 1.839E−01 | 1.422E−01 | 1.594E−01 | 1.373E−01 |
| 109 | 2.158E−03 | 3.556E−03 | 0.000E+00 | 3.433E−03 | 0.000E+00 | 4.856E−03 | 4.353E−03 | 9.712E−03 | 4.378E−03 | 6.303E−03 | 5.003E−03 | 5.825E−03 | 1.210E−02 |
| 110 | 2.968E−02 | 3.973E−02 | 6.180E−03 | 0.000E+00 | 8.817E−03 | 1.459E−02 | 0.000E+00 | 0.000E+00 | 1.570E−02 | 1.263E−02 | 1.950E−02 | 9.319E−03 | 2.121E−02 |
| 111 | 1.778E−02 | 1.606E−02 | 6.180E−03 | 3.433E−03 | 1.324E−02 | 9.700E−03 | 0.000E+00 | 0.000E+00 | 2.195E−02 | 1.386E−02 | 1.950E−02 | 6.990E−03 | 1.570E−02 |
| 112 | 1.186E−02 | 1.545E−02 | 0.000E+00 | 3.433E−03 | 1.766E−02 | 0.000E+00 | 4.353E−03 | 4.856E−03 | 6.254E−03 | 6.928E−03 | 1.496E−02 | 5.825E−03 | 1.508E−02 |
| 113 | 1.078E−03 | 3.556E−03 | 0.000E+00 | 3.433E−03 | 0.000E+00 | 0.000E+00 | 0.000E+00 | 4.856E−03 | 5.628E−03 | 1.888E−03 | 7.223E−03 | 3.495E−03 | 8.473E−03 |
| 114 | 6.462E−03 | 8.302E−03 | 0.000E+00 | 0.000E+00 | 0.000E+00 | 0.000E+00 | 0.000E+00 | 9.712E−03 | 7.505E−03 | 9.454E−03 | 8.890E−03 | 4.660E−03 | 8.473E−03 |
| 115 | 9.160E−03 | 1.127E−02 | 0.000E+00 | 0.000E+00 | 0.000E+00 | 0.000E+00 | 0.000E+00 | 1.459E−02 | 1.126E−02 | 2.526E−03 | 1.001E−02 | 1.754E−03 | 8.473E−03 |
| 116 | 6.462E−03 | 8.302E−03 | 0.000E+00 | 0.000E+00 | 0.000E+00 | 0.000E+00 | 0.000E+00 | 0.000E+00 | 3.127E−03 | 3.777E−03 | 5.555E−03 | 4.083E−03 | 3.630E−03 |
| 117 | 1.398E−02 | 8.302E−03 | 0.000E+00 | 0.000E+00 | 0.000E+00 | 0.000E+00 | 0.000E+00 | 4.856E−03 | 1.251E−02 | 5.040E−03 | 1.275E−02 | 6.990E−03 | 1.150E−02 |
| 118 | 3.777E−03 | 4.746E−03 | 0.000E+00 | 0.000E+00 | 0.000E+00 | 0.000E+00 | 0.000E+00 | 4.856E−03 | 1.815E−02 | 6.303E−03 | 6.671E−03 | 9.908E−03 | 3.630E−03 |
| 119 | 4.316E−03 | 7.713E−03 | 6.180E−03 | 0.000E+00 | 4.414E−03 | 0.000E+00 | 0.000E+00 | 0.000E+00 | 8.755E−03 | 8.191E−03 | 9.454E−03 | 6.413E−03 | 1.029E−02 |
| 120 | 5.383E−03 | 3.556E−03 | 0.000E+00 | 3.433E−03 | 0.000E+00 | 0.000E+00 | 0.000E+00 | 0.000E+00 | 8.755E−03 | 5.677E−03 | 1.056E−02 | 5.825E−03 | 9.687E−03 |
| 121 | 2.360E−02 | 3.713E−03 | 7.747E−02 | 2.146E−02 | 5.521E−02 | 6.073E−02 | 2.182E−01 | 3.037E−02 | 5.877E−02 | 1.184E−02 | 4.871E−02 | 5.476E−02 | 2.654E−02 |
| 122 | 1.318E−01 | 1.042E−01 | 2.324E−01 | 1.077E−01 | 2.484E−01 | 3.945E−01 | 4.354E−01 | 2.128E−01 | 8.620E−02 | 1.104E−01 | 1.318E−01 | 1.968E−01 | 9.083E−02 |
| 123 | 1.941E+00 | 3.143E+00 | 4.800E+00 | 4.443E+00 | 5.165E+00 | 5.895E+00 | 5.004E+00 | 4.167E+00 | 2.137E+00 | 1.033E+00 | 2.556E+00 | 2.021E+00 | 3.206E+00 |
| 124 | 3.037E−02 | 1.487E−02 | 1.549E−01 | 2.146E−02 | 5.521E−02 | 3.037E−02 | 2.182E−01 | 3.037E−02 | 4.310E−02 | 1.576E−02 | 3.134E−02 | 4.381E−02 | 3.411E−02 |
| 125 | 2.360E−02 | 2.226E−02 | 3.874E−02 | 6.447E−02 | 8.281E−02 | 9.083E−02 | 1.362E−01 | 1.211E−01 | 1.140E−01 | 3.945E−02 | 5.565E−02 | 9.528E−02 | 2.271E−02 |
| 126 | 1.042E+00 | 3.010E−01 | 4.648E−01 | 1.051E+00 | 1.158E+00 | 7.898E−01 | 1.256E+00 | 4.559E−01 | 7.088E−01 | 4.265E−01 | 8.005E−01 | 9.706E−01 | 2.012E−01 |
| 127 | 1.870E+00 | 1.122E+00 | 1.897E+00 | 3.544E+00 | 3.811E+00 | 3.063E+00 | 3.865E+00 | 2.004E+00 | 1.701E+00 | 9.795E−01 | 1.843E+00 | 1.674E+00 | 8.905E−01 |
| 128 | 1.523E+00 | 3.241E+00 | 3.909E+00 | 3.820E+00 | 4.800E+00 | 8.593E+00 | 4.114E+00 | 3.286E+00 | 1.790E+00 | 1.113E+00 | 1.558E+00 | 1.656E+00 | 2.725E+00 |
| 129 | 2.360E−02 | 2.600E−02 | 2.324E−01 | 8.593E−02 | 5.521E−02 | 1.211E−01 | 1.630E−01 | 1.211E−01 | 5.877E−02 | 5.129E−02 | 5.565E−02 | 7.293E−02 | 4.550E−02 |
| 130 | 1.512E+01 | 5.681E+00 | 5.378E+00 | 3.963E+01 | 2.656E+01 | 7.747E+00 | 1.407E+01 | 1.051E+01 | 6.580E+00 | 3.740E+00 | 7.996E+00 | 1.265E+01 | 3.330E+00 |
| 131 | 1.421E+01 | 7.159E+00 | 6.082E+00 | 2.799E+01 | 1.451E+01 | 2.431E+00 | 1.273E+01 | 7.533E+00 | 4.978E+00 | 2.565E+00 | 3.161E+00 | 5.530E+00 | 2.609E+00 |
| 132 | 5.396E−02 | 2.600E−02 | 3.874E−01 | 2.146E−02 | 8.281E−02 | 0.000E+00 | 8.166E−02 | 3.037E−02 | 2.743E−02 | 9.884E−02 | 9.439E−02 | 6.207E−02 | 1.095E−01 |
| 133 | 3.375E−02 | 2.226E−02 | 3.874E−02 | 4.292E−02 | 5.521E−02 | 3.037E−02 | 1.362E−01 | 6.073E−02 | 1.959E−02 | 2.369E−02 | 1.736E−02 | 1.825E−02 | 1.897E−02 |
| 134 | 1.015E−02 | 1.113E−02 | 7.747E−02 | 4.292E−02 | 2.760E−02 | 3.037E−02 | 2.725E−02 | 3.037E−02 | 1.567E−02 | 1.977E−02 | 2.440E−02 | 2.921E−02 | 4.924E−02 |
| 135 | 6.750E−03 | 1.861E−02 | 0.000E+00 | 0.000E+00 | 2.760E−02 | 3.037E−02 | 0.000E+00 | 9.083E−02 | 1.175E−02 | 7.890E−03 | 1.736E−02 | 1.460E−02 | 1.514E−02 |
| 136 | 1.015E−02 | 7.427E−03 | 1.549E−01 | 0.000E+00 | 5.521E−02 | 0.000E+00 | 2.725E−02 | 0.000E+00 | 1.959E−02 | 3.945E−03 | 1.736E−02 | 1.825E−02 | 1.514E−02 |
| 137 | 4.720E−02 | 4.452E−02 | 1.549E−01 | 8.593E−02 | 8.281E−02 | 1.825E−01 | 8.166E−02 | 9.083E−02 | 7.053E−02 | 8.281E−02 | 4.524E−02 | 4.381E−02 | 7.578E−02 |
| 138 | 1.683E−02 | 1.487E−02 | 3.874E−02 | 2.146E−02 | 1.104E−01 | 9.083E−02 | 2.725E−02 | 6.073E−02 | 5.485E−02 | 3.553E−02 | 2.440E−02 | 3.286E−02 | 2.654E−02 |
| 139 | 1.318E−01 | 2.084E−01 | 1.354E+00 | 6.011E−01 | 4.141E−01 | 6.679E−01 | 4.898E−01 | 2.734E−01 | 3.250E−01 | 1.024E−01 | 1.567E−01 | 2.119E−01 | 2.956E−01 |
| 140 | 1.042E−01 | 1.487E−01 | 3.099E−01 | 1.932E−01 | 2.208E−01 | 3.339E−01 | 2.182E−01 | 6.073E−02 | 1.371E−01 | 2.369E−02 | 1.077E−01 | 1.024E−01 | 2.235E−01 |
| 141 | 5.735E−02 | 1.113E−02 | 2.707E−01 | 1.719E−01 | 2.760E−02 | 1.211E−01 | 1.086E−01 | 6.073E−02 | 3.134E−02 | 7.890E−02 | 4.176E−02 | 4.381E−02 | 6.821E−02 |
| 142 | 6.750E−03 | 7.427E−03 | 0.000E+00 | 0.000E+00 | 0.000E+00 | 0.000E+00 | 5.441E−02 | 6.073E−02 | 7.836E−03 | 3.945E−03 | 1.042E−02 | 1.460E−02 | 1.140E−02 |
| 143 | 6.750E−03 | 0.000E+00 | 3.874E−02 | 0.000E+00 | 2.760E−02 | 0.000E+00 | 5.441E−02 | 0.000E+00 | 2.351E−02 | 1.977E−02 | 1.042E−02 | 2.556E−02 | 1.514E−02 |
| 144 | 2.360E−02 | 3.713E−02 | 7.747E−02 | 6.447E−02 | 2.760E−02 | 1.211E−01 | 0.000E+00 | 3.037E−02 | 1.567E−02 | 2.369E−02 | 4.871E−02 | 1.095E−02 | 2.654E−02 |
| 145 | 2.360E−02 | 1.487E−02 | 1.932E−01 | 2.146E−02 | 2.760E−02 | 6.073E−02 | 0.000E+00 | 6.073E−02 | 2.351E−02 | 1.184E−02 | 1.736E−02 | 3.286E−02 | 1.140E−02 |
| 146 | 1.621E−01 | 3.865E−01 | 2.324E−01 | 2.796E−01 | 4.969E−01 | 2.734E−01 | 2.725E−01 | 1.211E−01 | 1.843E−01 | 1.345E−01 | 1.354E−01 | 2.734E−01 | 4.889E−01 |
| 147 | 1.247E−01 | 1.077E−01 | 5.031E−01 | 1.932E−01 | 3.865E−01 | 5.165E−01 | 2.992E−01 | 1.825E−01 | 1.843E−01 | 8.281E−02 | 1.354E−01 | 1.603E−01 | 1.362E−01 |

APPENDIX D-continued

Ovarian Cancer
Training Dataset

| | | | | | | | | | | | | | |
|---|---|---|---|---|---|---|---|---|---|---|---|---|---|
| 148 | 3.678E−01 | 3.562E−01 | 6.198E−01 | 6.224E−01 | 6.625E−01 | 1.425E+00 | 8.166E−01 | 1.523E−01 | 4.265E−01 | 2.369E−01 | 3.028E−01 | 5.183E−01 | 2.654E−01 |
| 149 | 1.282E−01 | 5.939E−02 | 3.099E−01 | 1.932E−01 | 1.380E−01 | 2.128E−01 | 8.166E−02 | 1.211E−01 | 7.836E−02 | 5.922E−02 | 9.083E−02 | 1.318E−01 | 7.578E−02 |
| 150 | 2.360E−02 | 1.861E−02 | 2.707E−01 | 4.292E−02 | 5.521E−02 | 6.073E−02 | 8.166E−02 | 3.037E−02 | 9.439E−02 | 1.977E−02 | 2.084E−02 | 2.556E−02 | 4.550E−02 |
| 151 | 2.021E−02 | 1.861E−02 | 0.000E+00 | 0.000E+00 | 8.281E−02 | 3.037E−02 | 2.725E−02 | 0.000E+00 | 4.310E−02 | 1.576E−02 | 2.440E−02 | 2.191E−02 | 4.167E−02 |
| 152 | 4.381E−02 | 7.427E−03 | 7.747E−02 | 1.291E−01 | 1.104E−01 | 3.037E−02 | 2.725E−02 | 3.037E−02 | 1.567E−02 | 1.977E−02 | 3.829E−02 | 4.746E−02 | 1.514E−02 |
| 153 | 3.037E−02 | 7.427E−03 | 1.932E−01 | 4.292E−02 | 5.521E−02 | 6.073E−02 | 2.725E−02 | 6.073E−02 | 1.175E−02 | 1.977E−02 | 2.084E−02 | 2.921E−02 | 3.793E−03 |
| 154 | 1.683E−02 | 7.427E−03 | 1.158E−01 | 0.000E+00 | 2.760E−02 | 3.037E−02 | 5.441E−02 | 3.037E−02 | 1.175E−02 | 1.184E−02 | 3.482E−03 | 3.651E−03 | 1.897E−02 |
| 155 | 1.683E−02 | 1.487E−02 | 0.000E+00 | 6.447E−02 | 5.521E−02 | 3.037E−02 | 0.000E+00 | 3.037E−02 | 1.959E−02 | 1.184E−02 | 2.787E−02 | 1.825E−02 | 2.271E−02 |
| 156 | 3.811E−01 | 8.023E−01 | 4.256E−01 | 1.095E+00 | 6.073E−01 | 2.431E−01 | 2.449E−01 | 2.431E−01 | 3.286E−01 | 8.682E−02 | 1.701E−01 | 3.758E−01 | 4.702E−01 |
| 157 | 1.656E−01 | 2.974E−01 | 2.324E−01 | 3.224E−01 | 4.693E−01 | 2.128E−01 | 1.630E−01 | 6.073E−02 | 8.994E−02 | 9.439E−02 | 3.134E−02 | 2.084E−01 | 2.119E−01 |
| 158 | 3.206E−01 | 8.388E−01 | 4.648E−01 | 8.593E−01 | 5.521E−01 | 6.073E−01 | 4.630E−01 | 3.954E−01 | 2.627E−01 | 2.012E−01 | 2.440E−01 | 5.797E−01 | 7.961E−01 |
| 159 | 8.771E−02 | 1.897E−01 | 2.324E−01 | 1.719E−01 | 1.656E−01 | 9.083E−02 | 2.182E−01 | 9.083E−02 | 1.060E−01 | 1.024E−01 | 1.042E−01 | 1.567E−01 | 1.211E−01 |
| 160 | 4.381E−02 | 4.826E−02 | 1.158E−01 | 4.292E−02 | 5.521E−02 | 3.037E−02 | 2.725E−02 | 0.000E+00 | 4.310E−02 | 1.576E−02 | 3.482E−02 | 5.476E−02 | 2.654E−02 |
| 161 | 1.354E−02 | 2.226E−02 | 2.707E−01 | 6.447E−02 | 5.521E−02 | 1.523E−01 | 2.725E−01 | 6.073E−02 | 1.567E−02 | 3.945E−02 | 4.871E−02 | 3.651E−02 | 1.140E−02 |
| 162 | 2.360E−02 | 2.226E−02 | 1.874E−02 | 2.146E−02 | 0.000E+00 | 3.037E−02 | 8.166E−02 | 3.037E−02 | 1.175E−02 | 3.945E−03 | 2.440E−02 | 3.286E−02 | 3.793E−02 |
| 163 | 1.683E−02 | 1.487E−02 | 3.874E−02 | 2.146E−02 | 0.000E+00 | 0.000E+00 | 5.441E−02 | 0.000E+00 | 1.175E−02 | 1.977E−02 | 0.000E+00 | 5.111E−02 | 5.307E−02 |
| 164 | 6.750E−03 | 2.600E−02 | 3.874E−02 | 0.000E+00 | 2.760E−02 | 3.037E−02 | 2.725E−02 | 0.000E+00 | 1.175E−02 | 1.576E−02 | 3.482E−02 | 1.825E−02 | 2.654E−02 |
| 165 | 2.698E−02 | 1.487E−02 | 1.158E−01 | 2.146E−02 | 2.760E−02 | 0.000E+00 | 0.000E+00 | 0.000E+00 | 2.743E−02 | 2.760E−02 | 3.829E−02 | 3.651E−03 | 1.897E−02 |
| 166 | 7.756E−02 | 8.540E−02 | 1.549E−01 | 6.447E−02 | 1.104E−01 | 9.083E−02 | 8.166E−02 | 3.037E−02 | 6.269E−02 | 3.152E−02 | 2.787E−02 | 9.528E−02 | 4.167E−02 |
| 167 | 2.226E−01 | 6.723E−01 | 9.261E−01 | 6.011E−01 | 4.693E−01 | 3.037E−02 | 1.906E−01 | 1.211E−01 | 1.487E−01 | 9.083E−02 | 5.913E−02 | 2.734E−01 | 3.072E−01 |
| 168 | 9.795E−02 | 1.861E−01 | 7.747E−02 | 2.146E−01 | 1.104E−01 | 1.211E−01 | 2.725E−01 | 2.431E−01 | 1.060E−01 | 9.439E−02 | 8.005E−02 | 1.603E−01 | 1.362E−01 |
| 169 | 4.052E−02 | 7.801E−02 | 1.158E−01 | 6.447E−02 | 1.380E−01 | 6.073E−02 | 5.441E−02 | 9.083E−02 | 3.134E−02 | 3.152E−02 | 5.218E−02 | 4.746E−02 | 5.681E−02 |
| 170 | 1.683E−02 | 5.200E−02 | 0.000E+00 | 2.146E−02 | 0.000E+00 | 1.825E−01 | 2.725E−02 | 6.073E−02 | 4.310E−02 | 1.977E−02 | 3.134E−02 | 4.746E−02 | 7.961E−02 |
| 171 | 1.683E−02 | 2.600E−02 | 1.932E−01 | 0.000E+00 | 8.281E−02 | 9.083E−02 | 2.725E−02 | 0.000E+00 | 1.567E−02 | 1.977E−02 | 2.440E−02 | 5.476E−02 | 2.654E−02 |
| 172 | 8.363E−02 | 9.099E−02 | 9.601E−02 | 1.925E−01 | 1.717E−01 | 1.337E−01 | 2.955E−01 | 1.717E−01 | 7.554E−02 | 1.337E−01 | 6.229E−02 | 6.131E−02 | 6.781E−02 |
| 173 | 2.099E+00 | 2.679E+00 | 4.735E+00 | 3.996E+00 | 4.284E+00 | 6.126E+00 | 6.075E+00 | 6.201E+00 | 1.745E+00 | 2.410E+00 | 2.113E+00 | 1.858E+00 | 2.024E+00 |
| 174 | 3.580E+00 | 3.385E+00 | 6.063E+00 | 5.717E+00 | 5.729E+00 | 7.540E+00 | 5.401E+00 | 8.130E+00 | 2.654E+00 | 3.953E+00 | 3.693E+00 | 3.421E+00 | 3.307E+00 |
| 175 | 9.476E−01 | 7.394E−01 | 1.685E+00 | 2.073E+00 | 2.159E+00 | 2.425E+00 | 1.999E+00 | 1.942E+00 | 8.274E−01 | 8.952E−01 | 1.002E+00 | 8.179E−01 | 6.965E−01 |
| 176 | 2.186E+00 | 3.378E+00 | 5.162E+00 | 4.605E+00 | 6.292E+00 | 9.656E+00 | 7.023E+00 | 7.218E+00 | 1.917E+00 | 2.388E+00 | 2.564E+00 | 2.090E+00 | 1.991E+00 |
| 177 | 1.694E+00 | 1.646E+00 | 1.386E+00 | 3.286E+00 | 2.551E+00 | 2.133E+00 | 1.778E+00 | 2.214E+00 | 8.468E−01 | 1.407E+00 | 8.078E−01 | 1.093E+00 | 8.326E−01 |
| 178 | 2.980E−01 | 1.987E−01 | 2.502E−01 | 5.261E−01 | 5.972E−01 | 4.353E−01 | 3.863E−01 | 3.642E−01 | 1.582E−01 | 2.955E−01 | 2.158E−01 | 2.146E−01 | 9.086E−02 |
| 179 | 3.250E−02 | 2.097E−02 | 6.928E−02 | 7.100E−02 | 5.702E−02 | 9.197E−02 | 4.120E−02 | 4.598E−02 | 2.698E−02 | 2.661E−02 | 4.893E−02 | 2.060E−02 | 1.200E−02 |
| 180 | 1.208E−02 | 1.023E−02 | 6.928E−02 | 2.367E−02 | 7.223E−02 | 1.422E−01 | 9.001E−02 | 4.598E−02 | 1.888E−02 | 1.521E−02 | 2.440E−02 | 1.205E−02 | 1.096E−02 |
| 181 | 1.582E−02 | 1.226E−02 | 5.334E−03 | 2.661E−02 | 1.140E−02 | 1.251E−02 | 5.996E−02 | 8.363E−03 | 1.025E−02 | 1.631E−02 | 1.484E−02 | 1.557E−02 | 9.920E−03 |
| 182 | 9.099E−02 | 8.952E−02 | 1.925E−01 | 1.124E−01 | 1.521E−01 | 2.587E−01 | 2.403E−01 | 2.600E−01 | 6.634E−02 | 2.048E−01 | 1.221E−01 | 2.072E−01 | 9.651E−02 |
| 183 | 1.282E+00 | 1.189E+00 | 1.594E+00 | 9.050E−01 | 1.182E+00 | 1.324E+00 | 1.815E+00 | 1.582E+00 | 1.566E+00 | 2.366E+00 | 2.238E+00 | 2.730E+00 | 1.790E+00 |
| 184 | 1.488E+00 | 1.267E+00 | 1.496E+00 | 9.933E−01 | 9.651E−01 | 1.398E+00 | 1.557E+00 | 1.668E+00 | 1.408E+00 | 3.164E+00 | 2.265E+00 | 3.354E+00 | 2.072E+00 |
| 185 | 9.402E−01 | 7.799E−01 | 1.067E+00 | 6.536E−01 | 5.739E−01 | 1.032E+00 | 1.068E+00 | 9.454E−01 | 1.039E+00 | 2.033E+00 | 1.654E+00 | 2.339E+00 | 1.318E+00 |
| 186 | 1.976E+00 | 1.951E+00 | 2.218E+00 | 1.337E+00 | 1.324E+00 | 1.953E+00 | 1.974E+00 | 1.979E+00 | 2.310E+00 | 3.535E+00 | 3.397E+00 | 4.381E+00 | 2.484E+00 |
| 187 | 5.064E−01 | 3.998E−01 | 5.653E−01 | 4.083E−01 | 3.765E−01 | 3.850E−01 | 6.634E−01 | 4.562E−01 | 7.259E−01 | 6.585E−01 | 9.104E−01 | 1.032E+00 | 5.199E−01 |
| 188 | 4.414E−02 | 4.598E−02 | 8.535E−02 | 6.806E−02 | 8.363E−02 | 7.112E−02 | 1.161E−01 | 6.695E−02 | 6.953E−02 | 7.603E−02 | 9.871E−02 | 8.645E−02 | 4.120E−02 |
| 189 | 1.582E−02 | 8.179E−03 | 5.334E−03 | 1.484E−02 | 1.521E−02 | 1.668E−02 | 1.496E−02 | 1.251E−03 | 1.079E−02 | 2.771E−02 | 1.582E−02 | 4.868E−02 | 1.148E−02 |
| 190 | 1.508E−01 | 1.398E−01 | 7.468E−02 | 1.035E−01 | 9.503E−02 | 2.134E−01 | 1.533E−01 | 1.214E−01 | 2.146E−01 | 3.274E−01 | 2.256E−01 | 2.955E−01 | 1.754E−01 |
| 191 | 3.167E+00 | 3.851E+00 | 1.410E+00 | 1.839E+00 | 1.275E+00 | 1.239E+00 | 1.349E+00 | 1.410E+00 | 2.181E+00 | 3.531E+00 | 2.461E+00 | 4.972E+00 | 2.447E+00 |
| 192 | 7.823E−01 | 8.535E−01 | 3.090E−01 | 4.611E−01 | 2.968E−01 | 4.010E−01 | 4.267E−01 | 3.728E−01 | 5.849E−01 | 1.037E+00 | 9.041E−01 | 1.370E+00 | 4.807E−01 |
| 193 | 6.830E−02 | 7.468E−02 | 1.174E−01 | 7.983E−02 | 1.102E−01 | 1.213E−01 | 1.913E−01 | 1.337E−01 | 9.552E−02 | 1.398E−01 | 1.803E−01 | 1.729E−01 | 6.524E−02 |
| 194 | 5.346E−02 | 5.469E−02 | 2.882E−01 | 4.733E−02 | 1.178E−01 | 2.170E−01 | 1.459E−01 | 1.925E−01 | 7.174E−02 | 1.064E−01 | 1.198E−01 | 1.186E−01 | 7.051E−02 |
| 195 | 2.882E−02 | 3.985E−02 | 1.655E−01 | 8.878E−03 | 6.842E−02 | 8.780E−02 | 5.616E−02 | 7.529E−02 | 3.397E−02 | 3.483E−02 | 4.500E−02 | 4.574E−02 | 3.237E−02 |
| 196 | 2.085E−01 | 1.766E−01 | 1.120E−01 | 1.275E−01 | 1.410E−01 | 2.931E−02 | 1.422E−01 | 7.946E−02 | 1.508E−01 | 1.055E−01 | 1.300E−01 | 1.717E−01 | 1.018E−01 |
| 197 | 1.557E−01 | 1.251E−01 | 4.267E−02 | 6.217E−02 | 3.801E−02 | 3.765E−02 | 3.752E−02 | 7.112E−02 | 1.079E−01 | 1.071E−01 | 9.442E−02 | 1.251E−01 | 7.357E−02 |

APPENDIX D-continued

| | Ovarian Cancer Training Dataset | | | | | | | | | | | | |
|---|---|---|---|---|---|---|---|---|---|---|---|---|---|
| 198 | 5.346E−02 | 5.015E−02 | 5.334E−02 | 8.878E−03 | 4.942E−02 | 6.278E−02 | 3.004E−02 | 1.668E−02 | 7.603E−02 | 9.234E−02 | 8.719E−02 | 1.015E−01 | 4.807E−02 |
| 199 | 1.901E−02 | 8.486E−02 | 1.337E−01 | 5.910E−03 | 4.942E−02 | 1.088E−01 | 8.240E−02 | 7.112E−02 | 1.373E−01 | 2.514E−01 | 2.391E−01 | 2.465E−01 | 1.373E−01 |
| 200 | 2.968E−02 | 4.500E−02 | 9.062E−02 | 2.955E−03 | 7.223E−02 | 8.780E−02 | 6.376E−02 | 7.112E−02 | 6.683E−02 | 1.386E−01 | 1.312E−01 | 1.226E−01 | 5.371E−02 |
| 201 | 3.581E−02 | 4.500E−02 | 1.386E−01 | 1.484E−02 | 4.562E−02 | 6.695E−02 | 4.500E−02 | 8.363E−02 | 3.397E−02 | 6.303E−02 | 4.746E−02 | 5.028E−02 | 3.397E−02 |
| 202 | 1.864E−03 | 6.646E−03 | 1.594E−02 | 0.000E+00 | 1.521E−02 | 2.097E−02 | 1.124E−02 | 8.363E−03 | 1.133E−02 | 7.063E−03 | 1.386E−02 | 1.055E−02 | 6.266E−03 |
| 203 | 1.398E−03 | 0.000E+00 | 5.334E−03 | 8.878E−03 | 0.000E+00 | 4.181E−03 | 0.000E+00 | 0.000E+00 | 2.158E−03 | 1.086E−03 | 4.795E−04 | 0.000E+00 | 1.570E−03 |
| 204 | 1.864E−03 | 8.694E−03 | 5.334E−03 | 5.910E−03 | 1.140E−02 | 1.668E−02 | 7.492E−03 | 4.181E−03 | 9.172E−03 | 9.234E−03 | 7.186E−03 | 9.540E−03 | 8.351E−03 |
| 205 | 1.398E−03 | 5.113E−04 | 5.334E−03 | 0.000E+00 | 0.000E+00 | 4.181E−03 | 3.752E−03 | 0.000E+00 | 5.395E−04 | 0.000E+00 | 0.000E+00 | 0.000E+00 | 5.224E−04 |
| 206 | 3.716E−03 | 1.741E−02 | 5.334E−03 | 2.955E−03 | 1.901E−02 | 1.251E−02 | 1.876E−02 | 2.514E−02 | 1.937E−02 | 1.741E−02 | 1.435E−02 | 1.655E−02 | 1.361E−02 |
| 207 | 4.647E−03 | 4.096E−03 | 1.067E−02 | 5.910E−03 | 0.000E+00 | 4.181E−03 | 1.124E−02 | 4.181E−03 | 0.000E+00 | 1.086E−03 | 9.577E−04 | 0.000E+00 | 1.044E−03 |
| 208 | 1.398E−03 | 2.563E−03 | 1.067E−02 | 0.000E+00 | 0.000E+00 | 0.000E+00 | 0.000E+00 | 1.251E−02 | 1.619E−03 | 3.262E−03 | 4.316E−03 | 4.022E−03 | 3.127E−03 |
| 209 | 9.295E−04 | 1.023E−03 | 0.000E+00 | 2.955E−03 | 0.000E+00 | 0.000E+00 | 0.000E+00 | 0.000E+00 | 1.079E−03 | 5.432E−04 | 0.000E+00 | 0.000E+00 | 0.000E+00 |
| 210 | 1.398E−03 | 0.000E+00 | 0.000E+00 | 5.910E−03 | 0.000E+00 | 0.000E+00 | 3.752E−03 | 8.363E−03 | 0.000E+00 | 0.000E+00 | 0.000E+00 | 0.000E+00 | 5.224E−04 |
| 211 | 1.398E−03 | 5.113E−04 | 0.000E+00 | 0.000E+00 | 0.000E+00 | 0.000E+00 | 0.000E+00 | 8.363E−03 | 0.000E+00 | 0.000E+00 | 4.795E−04 | 1.004E−03 | 5.224E−04 |
| 212 | 1.864E−03 | 0.000E+00 | 0.000E+00 | 2.955E−03 | 0.000E+00 | 4.181E−03 | 7.492E−03 | 4.181E−03 | 1.079E−03 | 0.000E+00 | 0.000E+00 | 5.028E−04 | 0.000E+00 |
| 213 | 9.295E−04 | 0.000E+00 | 0.000E+00 | 2.955E−03 | 0.000E+00 | 8.363E−03 | 0.000E+00 | 0.000E+00 | 5.395E−03 | 2.722E−03 | 1.435E−03 | 2.011E−03 | 2.612E−03 |
| 214 | 2.784E−03 | 3.581E−03 | 5.334E−03 | 1.183E−02 | 3.801E−03 | 0.000E+00 | 0.000E+00 | 8.363E−03 | 3.237E−03 | 3.801E−03 | 2.391E−03 | 5.028E−04 | 1.570E−03 |
| 215 | 2.318E−03 | 0.000E+00 | 5.334E−03 | 2.955E−03 | 0.000E+00 | 8.363E−03 | 0.000E+00 | 8.363E−03 | 1.079E−03 | 1.086E−03 | 0.000E+00 | 5.028E−04 | 0.000E+00 |
| 216 | 9.295E−04 | 1.023E−03 | 0.000E+00 | 0.000E+00 | 0.000E+00 | 4.181E−03 | 0.000E+00 | 0.000E+00 | 0.000E+00 | 1.086E−03 | 4.795E−04 | 5.028E−04 | 5.224E−04 |
| 217 | 9.295E−04 | 1.533E−03 | 0.000E+00 | 0.000E+00 | 0.000E+00 | 0.000E+00 | 0.000E+00 | 4.181E−03 | 1.619E−03 | 2.722E−03 | 3.360E−03 | 5.028E−04 | 5.224E−04 |
| 218 | 1.463E+00 | 1.309E+00 | 2.320E+00 | 1.741E+00 | 2.452E+00 | 2.333E+00 | 3.943E+00 | 2.611E+00 | 2.202E+00 | 2.967E+00 | 2.756E+00 | 2.828E+00 | 2.082E+00 |
| 219 | 1.251E−02 | 1.023E−02 | 1.594E−02 | 1.183E−02 | 1.901E−02 | 3.348E−02 | 4.120E−02 | 2.514E−02 | 2.857E−02 | 2.882E−02 | 2.305E−02 | 2.869E−02 | 2.036E−02 |
| 220 | 1.985E+00 | 1.689E+00 | 1.456E+00 | 1.633E+00 | 1.600E+00 | 1.908E+00 | 2.260E+00 | 1.798E+00 | 1.140E+00 | 2.515E+00 | 1.349E+00 | 1.477E+00 | 1.168E+00 |
| 221 | 5.992E+01 | 5.837E+01 | 6.224E+01 | 5.344E+01 | 6.588E+01 | 7.724E+01 | 6.647E+01 | 6.941E+01 | 5.735E+01 | 5.531E+01 | 6.293E+01 | 5.066E+01 | 4.858E+01 |
| 222 | 6.100E+01 | 3.657E+01 | 5.764E+01 | 7.134E+01 | 6.301E+01 | 7.030E+01 | 4.409E+01 | 5.055E+01 | 5.200E+01 | 3.078E+01 | 3.651E+01 | 3.825E+01 | 2.367E+01 |
| 223 | 3.111E+01 | 2.842E+01 | 2.860E+01 | 3.350E+01 | 3.870E+01 | 3.381E+01 | 3.286E+01 | 3.140E+01 | 2.702E+01 | 2.479E+01 | 2.526E+01 | 1.800E+01 | 2.217E+01 |
| 224 | 2.320E+01 | 1.824E+01 | 2.681E+01 | 2.041E+01 | 2.394E+01 | 3.064E+01 | 2.470E+01 | 2.356E+01 | 2.207E+01 | 1.934E+01 | 1.594E+01 | 1.902E+01 | 1.465E+01 |
| 225 | 2.620E+01 | 2.836E+01 | 1.477E+01 | 2.807E+01 | 2.397E+01 | 9.746E+00 | 1.159E+01 | 2.008E+01 | 1.225E+01 | 1.208E+01 | 8.560E+00 | 1.640E+01 | 1.889E+01 |
| 226 | 1.415E+01 | 9.287E+00 | 5.758E+00 | 1.546E+01 | 9.178E+00 | 1.334E+00 | 5.450E+00 | 7.194E+00 | 5.896E+00 | 2.421E+00 | 2.215E+00 | 3.927E+00 | 2.671E+00 |
| 227 | 4.572E+00 | 2.724E+00 | 1.758E+00 | 4.303E+00 | 3.584E+00 | 1.359E+00 | 2.092E+00 | 2.183E+00 | 2.061E+00 | 1.755E+00 | 1.124E+00 | 1.674E+00 | 1.187E+00 |
| 228 | 3.334E−01 | 3.410E−01 | 4.528E−01 | 3.837E−01 | 5.122E−01 | 3.293E−01 | 6.231E−01 | 3.661E−01 | 3.672E−01 | 4.257E−01 | 3.119E−01 | 2.770E−01 | 2.633E−01 |
| 229 | 3.829E−01 | 3.769E−01 | 5.104E−01 | 4.322E−01 | 5.328E−01 | 3.734E−01 | 7.016E−01 | 4.134E−01 | 4.245E−01 | 4.336E−01 | 3.136E−01 | 2.779E−01 | 2.669E−01 |
| 230 | 3.265E+01 | 5.138E+01 | 3.612E+01 | 4.249E+01 | 4.163E+01 | 3.974E+01 | 3.000E+01 | 4.195E+01 | 3.740E+01 | 2.325E+01 | 3.864E+01 | 2.084E+01 | 4.820E+01 |
| 231 | 4.288E+00 | 6.845E+00 | 4.559E+00 | 5.348E+00 | 4.768E+00 | 3.566E+00 | 4.627E+00 | 4.726E+00 | 4.820E+00 | 3.525E+00 | 3.969E+00 | 3.105E+00 | 5.915E+00 |
| 232 | 1.735E+00 | 1.718E+00 | 2.278E+00 | 2.079E+00 | 2.174E+00 | 1.607E+00 | 1.785E+00 | 1.886E+00 | 1.673E+00 | 1.303E+00 | 1.610E+00 | 1.201E+00 | 1.444E+00 |
| 233 | 5.211E+00 | 5.220E+00 | 6.351E+00 | 5.293E+00 | 5.221E+00 | 6.313E+00 | 6.442E+00 | 5.473E+00 | 5.248E+00 | 5.979E+00 | 4.581E+00 | 4.385E+00 | 6.194E+00 |
| 234 | 1.570E+01 | 2.395E+01 | 2.000E+01 | 1.562E+01 | 1.572E+01 | 1.868E+01 | 2.161E+01 | 2.001E+01 | 1.275E+01 | 2.503E+01 | 1.512E+01 | 1.292E+01 | 2.587E+01 |
| 235 | 9.848E+00 | 1.752E+01 | 1.015E+01 | 8.300E+00 | 8.019E+00 | 7.561E+00 | 8.570E+00 | 1.198E+01 | 8.522E+00 | 8.909E+00 | 1.080E+01 | 8.224E+00 | 1.882E+01 |
| 236 | 7.452E−01 | 2.978E−01 | 6.628E−01 | 6.447E−01 | 6.205E−01 | 6.127E−01 | 9.900E−01 | 4.767E−01 | 1.068E+00 | 6.413E−01 | 9.140E−01 | 7.851E−01 | 4.981E−01 |
| 237 | 6.193E+00 | 1.698E+00 | 3.170E+00 | 5.000E+00 | 3.895E+00 | 3.103E+00 | 4.777E+00 | 2.806E+00 | 6.742E+00 | 3.695E+00 | 5.273E+00 | 6.476E+00 | 1.895E+00 |
| 238 | 6.486E+00 | 5.194E+00 | 5.739E+00 | 6.285E+00 | 5.943E+00 | 5.156E+00 | 5.805E+00 | 5.939E+00 | 6.289E+00 | 6.574E+00 | 6.595E+00 | 5.524E+00 | 7.075E+00 |
| 239 | 1.076E+00 | 1.216E+00 | 1.518E+00 | 1.157E+00 | 1.247E+00 | 9.341E−01 | 1.089E+00 | 1.141E+00 | 1.259E+00 | 1.158E+00 | 1.345E+00 | 1.252E+00 | 1.507E+00 |
| 240 | 5.658E+00 | 5.519E+00 | 1.749E+01 | 4.967E+00 | 1.009E+01 | 2.875E+01 | 1.684E+01 | 1.320E+01 | 1.562E+01 | 2.298E+01 | 2.102E+01 | 1.980E+01 | 8.611E+00 |
| 241 | 2.136E+02 | 1.800E+02 | 2.179E+02 | 2.163E+02 | 2.168E+02 | 2.643E+02 | 2.370E+02 | 2.246E+02 | 2.592E+02 | 2.402E+02 | 2.603E+02 | 2.608E+02 | 1.974E+02 |
| 242 | 1.446E+02 | 1.550E+02 | 1.395E+02 | 1.288E+02 | 1.494E+02 | 1.327E+02 | 1.954E+02 | 1.655E+02 | 1.444E+02 | 1.958E+02 | 1.918E+02 | 1.513E+02 | 1.754E+02 |
| 243 | 1.383E+01 | 1.622E+01 | 1.240E+01 | 1.158E+01 | 1.347E+01 | 1.148E+01 | 1.752E+01 | 1.517E+01 | 1.227E+01 | 1.846E+01 | 1.777E+01 | 1.326E+01 | 1.688E+01 |
| 244 | 1.327E+01 | 8.047E+00 | 5.038E+00 | 1.483E+01 | 1.123E+01 | 3.453E+00 | 6.479E+00 | 8.969E+00 | 9.647E+00 | 7.533E+00 | 9.638E+00 | 1.063E+01 | 9.378E+00 |
| 245 | 6.163E+00 | 2.644E+00 | 3.293E+00 | 5.606E+00 | 4.566E+00 | 3.750E+00 | 4.292E+00 | 3.425E+00 | 6.275E+00 | 4.958E+00 | 5.947E+00 | 5.886E+00 | 3.276E+00 |
| 246 | 5.937E+00 | 3.693E+00 | 7.301E+00 | 5.237E+00 | 5.824E+00 | 7.425E+00 | 6.668E+00 | 4.521E+00 | 8.240E+00 | 6.475E+00 | 7.118E+00 | 1.064E+01 | 5.302E+00 |
| 247 | 3.903E+00 | 4.273E+00 | 5.348E+00 | 4.101E+00 | 4.774E+00 | 3.174E+00 | 4.606E+00 | 3.479E+00 | 4.764E+00 | 4.597E+00 | 4.422E+00 | 6.433E+00 | 3.787E+00 |

APPENDIX D-continued

| | Ovarian Cancer Training Dataset | | | | | | | | | | | | |
|---|---|---|---|---|---|---|---|---|---|---|---|---|---|
| 248 | 9.786E+01 | 1.123E+02 | 4.973E+01 | 8.185E+01 | 7.731E+01 | 4.342E+01 | 6.519E+01 | 7.686E+01 | 6.441E+01 | 9.277E+01 | 5.738E+01 | 1.159E+02 | 1.173E+02 |
| 249 | 6.405E+01 | 5.071E+01 | 4.664E+01 | 5.525E+01 | 5.988E+01 | 6.100E+01 | 7.672E+01 | 5.058E+01 | 6.479E+01 | 8.280E+01 | 5.839E+01 | 9.113E+01 | 4.841E+01 |
| 250 | 1.289E+02 | 7.514E+01 | 1.233E+02 | 1.162E+02 | 1.141E+02 | 1.361E+02 | 1.326E+02 | 1.037E+02 | 1.393E+02 | 1.336E+02 | 1.098E+02 | 1.603E+02 | 7.804E+01 |
| 251 | 4.308E+01 | 3.563E+01 | 6.222E+01 | 3.960E+01 | 4.616E+01 | 5.926E+01 | 6.636E+01 | 4.782E+01 | 5.046E+01 | 6.617E+01 | 5.449E+01 | 5.787E+01 | 3.729E+01 |
| 252 | 2.721E+00 | 2.633E+00 | 4.219E+00 | 2.551E+00 | 2.943E+00 | 3.424E+00 | 4.265E+00 | 3.084E+00 | 3.571E+00 | 4.551E+00 | 3.771E+00 | 3.779E+00 | 2.697E+00 |
| 253 | 6.162E+00 | 2.772E+00 | 2.190E+00 | 5.164E+00 | 3.819E+00 | 1.398E+00 | 3.064E+00 | 3.123E+00 | 4.334E+00 | 2.381E+00 | 3.350E+00 | 3.304E+00 | 2.615E+00 |
| 254 | 1.240E+01 | 7.686E+00 | 4.642E+00 | 1.181E+01 | 8.143E+00 | 4.017E+00 | 5.091E+00 | 7.159E+00 | 8.231E+00 | 7.598E+00 | 7.988E+00 | 8.538E+00 | 1.011E+01 |
| 255 | 9.363E+00 | 7.401E+00 | 4.532E+00 | 9.204E+00 | 8.021E+00 | 3.725E+00 | 4.948E+00 | 6.302E+00 | 8.082E+00 | 7.837E+00 | 7.854E+00 | 9.439E+00 | 9.584E+00 |
| 256 | 2.576E+00 | 2.197E+00 | 2.465E+00 | 2.561E+00 | 2.791E+00 | 2.608E+00 | 3.014E+00 | 2.208E+00 | 3.495E+00 | 3.498E+00 | 3.454E+00 | 5.615E+00 | 3.418E+00 |
| 257 | 4.302E+00 | 4.917E+00 | 5.467E+00 | 5.063E+00 | 5.293E+00 | 4.038E+00 | 5373E+00 | 4.361E+00 | 5.943E+00 | 4.420E+00 | 5.389E+00 | 5.101E+00 | 3.900E+00 |
| 258 | 4.370E+01 | 2.466E+01 | 1.421E+01 | 2.684E+01 | 2.174E+01 | 1.038E+01 | 2.390E+01 | 1.890E+01 | 2.075E+01 | 2.995E+01 | 1.396E+01 | 3.086E+01 | 1.959E+01 |
| 259 | 5.411E+01 | 5.412E+01 | 3.008E+01 | 4.321E+01 | 4.046E+01 | 2.273E+01 | 3.516E+01 | 3.808E+01 | 3.477E+01 | 5.734E+01 | 2.524E+01 | 6.912E+01 | 5.878E+01 |
| 260 | 3.307E+01 | 3.061E+01 | 3.256E+01 | 3.084E+01 | 3.239E+01 | 2.847E+01 | 3.874E+01 | 3.211E+01 | 3.237E+01 | 4.360E+01 | 3.378E+01 | 4.350E+01 | 3.568E+01 |
| 261 | 2.795E+01 | 4.035E+01 | 4.099E+01 | 3.394E+01 | 3.292E+01 | 3.672E+01 | 3.013E+01 | 3.621E+01 | 3.279E+01 | 2.811E+01 | 3.839E+01 | 2.442E+01 | 4.065E+01 |
| 262 | 9.758E+00 | 1.299E+01 | 1.815E+01 | 1.201E+01 | 1.339E+01 | 1.505E+01 | 1.283E+01 | 1.349E+01 | 1.358E+01 | 1.362E+01 | 1.367E+01 | 1.147E+01 | 8.509E+00 |
| 263 | 4.050E+00 | 2.326E+00 | 1.723E+00 | 3.466E+00 | 2.594E+00 | 1.068E+00 | 2.037E+00 | 1.904E+00 | 3.151E+00 | 1.888E+00 | 2.041E+00 | 2.998E+00 | 1.857E+00 |
| 264 | 3.378E+00 | 2.079E+00 | 2.253E+00 | 2.778E+00 | 2.631E+00 | 2.551E+00 | 2.809E+00 | 2.300E+00 | 3.251E+00 | 2.613E+00 | 2.629E+00 | 4.297E+00 | 2.873E+00 |
| 265 | 2.217E+00 | 1.816E+00 | 1.696E+00 | 1.870E+00 | 2.100E+00 | 1.503E+00 | 2.020E+00 | 1.812E+00 | 2.385E+00 | 2.663E+00 | 2.568E+00 | 3.242E+00 | 2.458E+00 |
| 266 | 9.203E−01 | 1.117E+00 | 2.903E+00 | 8.333E−01 | 1.689E+00 | 3.330E+00 | 2.223E+00 | 1.826E+00 | 2.181E+00 | 2.918E+00 | 2.940E+00 | 3.110E+00 | 2.398E+00 |
| 267 | 1.005E+00 | 1.671E+00 | 3.296E+00 | 1.082E+00 | 1.663E+00 | 2.365E+00 | 1.881E+00 | 1.634E+00 | 2.104E+00 | 2.319E+00 | 2.530E+00 | 2.486E+00 | 2.098E+00 |
| 268 | 2.095E+01 | 1.325E+01 | 7.325E+00 | 1.257E+01 | 8.937E+00 | 1.979E+00 | 1.068E+01 | 8.744E+00 | 1.098E+01 | 7.977E+00 | 4.352E+00 | 1.244E+01 | 6.332E+00 |
| 269 | 9.321E+00 | 6.753E+00 | 7.157E+00 | 5.204E+00 | 7.293E+00 | 4.816E+00 | 1.024E+01 | 7.408E+00 | 7.475E+00 | 9.645E+00 | 6.262E+00 | 9.829E+00 | 5.163E+00 |
| 270 | 2.770E+00 | 2.454E+00 | 3.284E+00 | 1.837E+00 | 2.967E+00 | 2.945E+00 | 4.975E+00 | 2.976E+00 | 3.098E+00 | 6.359E+00 | 3.607E+00 | 5.032E+00 | 3.011E+00 |
| 271 | 1.379E+01 | 1.521E+01 | 1.399E+01 | 1.493E+01 | 1.730E+01 | 1.327E+01 | 1.399E+01 | 1.744E+01 | 1.388E+01 | 1.049E+01 | 1.390E+01 | 7.605E+00 | 1.739E+01 |
| 272 | 7.977E+01 | 1.170E+02 | 1.005E+02 | 1.125E+02 | 1.104E+02 | 9.889E+01 | 7.717E+01 | 1.132E+02 | 8.946E+01 | 5.628E+01 | 9.411E+01 | 5.079E+01 | 1.211E+02 |
| 273 | 8.314E+01 | 1.235E+02 | 9.695E+01 | 1.098E+02 | 1.154E+02 | 9.669E+01 | 7.652E+01 | 1.156E+02 | 9.848E+01 | 6.327E+01 | 1.047E+02 | 5.886E+01 | 1.342E+02 |
| 274 | 1.247E+01 | 2.378E+01 | 1.583E+01 | 1.789E+01 | 1.681E+01 | 1.425E+01 | 1.083E+01 | 1.641E+01 | 1.471E+01 | 9.051E+00 | 1.430E+01 | 8.728E+00 | 2.178E+01 |
| 275 | 4.948E−01 | 5.437E−01 | 1.190E+00 | 5.843E−01 | 5.672E−01 | 9.052E−01 | 5.730E−01 | 7.139E−01 | 7.207E−01 | 7.096E−01 | 6.175E−01 | 5.757E−01 | 6.650E−01 |
| 276 | 8.223E+00 | 1.053E+01 | 1.308E+01 | 8.807E+00 | 9.708E+00 | 1.307E+01 | 9.867E+00 | 1.097E+01 | 8.105E+00 | 8.430E+00 | 8.045E+00 | 4.419E+00 | 1.295E+01 |
| 277 | 1.877E+01 | 3.864E+01 | 3.763E+01 | 2.458E+01 | 2.281E+01 | 3.549E+01 | 1.899E+01 | 2.821E+01 | 1.826E+01 | 1.720E+01 | 1.818E+01 | 1.220E+01 | 4.254E+01 |
| 278 | 1.868E+01 | 3.858E+01 | 3.467E+01 | 2.241E+01 | 2.228E+01 | 3.367E+01 | 1.812E+01 | 2.673E+01 | 1.828E+01 | 1.741E+01 | 1.852E+01 | 1.234E+01 | 4.244E+01 |
| 279 | 5.585E+00 | 1.318E+01 | 9.798E+00 | 5.558E+00 | 5.278E+00 | 6.737E+00 | 7.012E+00 | 8.099E+00 | 4.258E+00 | 9.086E+00 | 5.007E+00 | 4.895E+00 | 1.175E+01 |
| 280 | 4.543E+00 | 3.824E+00 | 7.699E+00 | 4.534E+00 | 5.482E+00 | 9.372E+00 | 7.069E+00 | 6.036E+00 | 6.753E+00 | 7.911E+00 | 7.518E+00 | 5.948E+00 | 5.120E+00 |
| 281 | 1.227E+02 | 9.701E+01 | 1.118E+02 | 1.099E+02 | 1.084E+02 | 1.229E+02 | 1.190E+02 | 1.102E+02 | 1.279E+02 | 1.240E+02 | 1.330E+02 | 1.387E+02 | 1.008E+02 |
| 282 | 1.052E+02 | 8.395E+01 | 9.493E+01 | 9.753E+01 | 9.607E+01 | 1.042E+02 | 1.051E+02 | 9.536E+01 | 1.092E+02 | 1.076E+02 | 1.140E+02 | 1.185E+02 | 8.795E+01 |
| 283 | 4.502E+01 | 4.946E+01 | 3.694E+01 | 3.575E+01 | 4.211E+01 | 3.598E+01 | 5.848E+01 | 4.814E+01 | 3.952E+01 | 6.169E+01 | 5.711E+01 | 4.290E+01 | 5.523E+01 |
| 284 | 5.700E+00 | 5.795E+00 | 6.666E+00 | 6.768E+00 | 6.882E+00 | 4.066E+00 | 5.772E+00 | 4.615E+00 | 6.591E+00 | 4.411E+00 | 5.436E+00 | 6.581E+00 | 4.041E+00 |
| 285 | 8.366E+01 | 6.247E+01 | 8.309E+01 | 7.536E+01 | 6.983E+01 | 7.471E+01 | 7.471E+01 | 6.359E+01 | 8.517E+01 | 7.826E+01 | 6.887E+01 | 8.484E+01 | 5.402E+01 |
| 286 | 6.162E+01 | 5.088E+01 | 6.752E+01 | 6.072E+01 | 5.911E+01 | 5.924E+01 | 5.853E+01 | 5.383E+01 | 6.609E+01 | 6.132E+01 | 5.319E+01 | 6.586E+01 | 4.315E+01 |
| 287 | 7.917E+00 | 7.318E+00 | 1.093E+01 | 7.253E+00 | 8.486E+00 | 1.051E+01 | 1.203E+01 | 8.613E+00 | 8.901E+00 | 1.275E+01 | 9.820E+00 | 1.021E+01 | 7.424E+00 |
| 288 | 5.982E+01 | 8.304E+01 | 7.870E+01 | 6.915E+01 | 6.263E+01 | 6.759E+01 | 5.237E+01 | 7.015E+01 | 5.893E+01 | 4.675E+01 | 6.836E+01 | 4.296E+01 | 8.315E+01 |
| 289 | 4.567E+01 | 6.724E+01 | 6.267E+01 | 5.966E+01 | 5.125E+01 | 5.377E+01 | 4.148E+01 | 5.659E+01 | 4.823E+01 | 3.806E+01 | 5.461E+01 | 3.402E+01 | 6.830E+01 |
| 290 | 2.152E+01 | 2.727E+01 | 2.550E+01 | 2.493E+01 | 2.219E+01 | 1.784E+01 | 1.726E+01 | 2.152E+01 | 2.409E+01 | 1.987E+01 | 2.242E+01 | 1.604E+01 | 1.864E+01 |
| 291 | 1.725E+01 | 2.233E+01 | 2.514E+01 | 2.571E+01 | 2.288E+01 | 1.854E+01 | 1.787E+01 | 2.215E+01 | 1.946E+01 | 1.668E+01 | 1.861E+01 | 1.340E+01 | 1.531E+01 |
| 292 | 1.674E+00 | 2.178E+00 | 3.570E+00 | 2.385E+00 | 2.716E+00 | 3.318E+00 | 2.808E+00 | 2.775E+00 | 2.528E+00 | 2.942E+00 | 2.623E+00 | 2.473E+00 | 1.618E+00 |
| 293 | 5.043E−01 | 1.155E+00 | 3.148E+00 | 5.819E−01 | 1.562E+00 | 3.719E+00 | 2.259E+00 | 2.095E+00 | 1.439E+00 | 2.322E+00 | 1.876E+00 | 1.976E+00 | 1.806E+00 |
| 294 | 1.396E+00 | 1.203E+00 | 2.677E+00 | 2.057E+00 | 2.536E+00 | 3.677E+00 | 3.428E+00 | 2.667E+00 | 1.948E+00 | 3.502E+00 | 2.516E+00 | 2.957E+00 | 1.637E+00 |
| 295 | 1.408E+00 | 1.237E+00 | 2.696E+00 | 2.207E+00 | 2.494E+00 | 3.873E+00 | 3.351E+00 | 2.674E+00 | 1.938E+00 | 3.565E+00 | 2.543E+00 | 2.910E+00 | 1.601E+00 |
| 296 | 9.250E−01 | 8.695E−01 | 1.480E+00 | 1.215E+00 | 1.655E+00 | 1.834E+00 | 2.322E+00 | 1.818E+00 | 1.141E+00 | 2.715E+00 | 1.797E+00 | 1.642E+00 | 1.296E+00 |
| 297 | 2.347E−01 | 5.121E−01 | 4.493E−01 | 4.476E−01 | 4.599E−01 | 4.654E−01 | 3.037E−01 | 4.897E−01 | 2.502E−01 | 1.347E−01 | 2.444E−01 | 1.163E−01 | 3.897E−01 |

APPENDIX D-continued

Ovarian Cancer
Training Dataset

| | | | | | | | | | | | | | |
|---|---|---|---|---|---|---|---|---|---|---|---|---|---|
| 298 | 1.255E−02 | 3.733E−02 | 2.746E−02 | 1.828E−02 | 2.360E−02 | 2.832E−02 | 1.186E−02 | 2.188E−02 | 1.045E−02 | 4.848E−03 | 5.642E−03 | 3.754E−03 | 2.014E−02 |
| 299 | 5.771E−02 | 2.998E−01 | 2.880E−01 | 9.761E−02 | 1.109E−01 | 2.748E−01 | 1.068E−01 | 1.521E−01 | 6.264E−02 | 3.711E−02 | 5.771E−02 | 2.875E−02 | 2.589E−01 |
| 300 | 4.441E−03 | 2.488E−02 | 1.330E−02 | 5.556E−03 | 3.583E−03 | 9.868E−03 | 3.068E−03 | 6.500E−03 | 3.304E−03 | 4.376E−03 | 4.269E−03 | 1.255E−03 | 1.626E−02 |
| 301 | 5.149E−02 | 1.255E−01 | 1.418E−01 | 7.101E−02 | 6.157E−02 | 1.334E−01 | 6.972E−02 | 7.809E−02 | 4.913E−02 | 3.153E−02 | 4.870E−02 | 2.100E−02 | 1.223E−01 |
| 302 | 6.414E−03 | 9.975E−03 | 9.739E−03 | 7.144E−03 | 3.583E−03 | 7.229E−03 | 3.818E−03 | 1.182E−03 | 9.546E−03 | 2.049E−02 | 1.349E−02 | 1.725E−02 | 9.310E−03 |
| 303 | 2.181E−01 | 4.340E−01 | 3.943E−01 | 2.570E−01 | 2.130E−01 | 2.465E−01 | 2.544E−01 | 2.502E−01 | 2.544E−01 | 1.238E−01 | 2.092E−01 | 1.131E−01 | 2.503E−01 |
| 304 | 2.596E−03 | 4.441E−03 | 9.739E−03 | 8.731E−03 | 6.157E−03 | 5.921E−03 | 3.432E−03 | 5.921E−03 | 3.861E−03 | 1.251E−02 | 7.165E−03 | 1.098E−02 | 3.904E−03 |
| 305 | 2.698E−01 | 7.631E−01 | 6.655E−01 | 4.623E−01 | 3.824E−01 | 5.726E−01 | 3.542E−01 | 5.743E−01 | 3.370E−01 | 1.141E−01 | 4.023E−01 | 1.530E−01 | 6.456E−01 |
| 306 | 1.834E−02 | 7.551E−02 | 4.870E−02 | 3.025E−02 | 2.053E−02 | 2.767E−02 | 1.684E−02 | 4.205E−02 | 1.705E−02 | 6.264E−03 | 2.145E−02 | 9.718E−03 | 3.990E−02 |
| 307 | 1.665E+00 | 2.723E+00 | 1.806E+00 | 2.017E+00 | 1.690E+00 | 1.319E+00 | 1.677E+00 | 1.652E+00 | 1.732E+00 | 7.168E−01 | 1.418E+00 | 8.309E−01 | 8.402E−01 |
| 308 | 2.896E−02 | 5.964E−02 | 3.282E−02 | 3.647E−02 | 2.832E−02 | 1.841E−02 | 2.682E−02 | 3.668E−02 | 2.274E−02 | 1.111E−02 | 2.446E−02 | 1.270E−02 | 1.474E−02 |
| 309 | 3.818E−03 | 1.135E−02 | 4.441E−03 | 5.556E−03 | 3.583E−03 | 9.203E−03 | 3.432E−03 | 4.140E−03 | 4.033E−03 | 1.407E−03 | 2.381E−03 | 1.098E−03 | 7.272E−03 |
| 310 | 2.295E−03 | 2.617E−03 | 3.540E−03 | 3.969E−04 | 2.053E−03 | 6.564E−04 | 1.148E−03 | 2.360E−03 | 2.019E−03 | 9.375E−04 | 1.025E−03 | 1.098E−03 | 2.032E−03 |
| 311 | 1.223E−03 | 9.203E−04 | 8.860E−04 | 0.000E+00 | 5.127E−04 | 0.000E+00 | 3.818E−04 | 5.921E−04 | 1.100E−03 | 4.698E−04 | 0.000E+00 | 3.132E−04 | 0.000E+00 |
| 312 | 0.000E+00 | 1.534E−04 | 1.772E−03 | 0.000E+00 | 0.000E+00 | 0.000E+00 | 0.000E+00 | 0.000E+00 | 1.834E−04 | 1.564E−04 | 0.000E+00 | 3.132E−04 | 5.084E−04 |
| 313 | 1.154E−01 | 1.823E−01 | 2.137E−01 | 1.740E−01 | 1.504E−01 | 1.118E−01 | 6.586E−02 | 1.757E−01 | 1.639E−01 | 4.870E−02 | 1.261E−01 | 4.290E−02 | 1.888E−01 |
| 314 | 4.441E−03 | 6.757E−03 | 5.320E−03 | 7.551E−03 | 7.701E−03 | 7.229E−03 | 3.432E−03 | 5.921E−03 | 6.243E−03 | 2.338E−03 | 4.441E−03 | 1.255E−03 | 8.130E−03 |
| 315 | 2.682E−02 | 3.089E−02 | 3.625E−02 | 4.569E−02 | 2.574E−02 | 3.818E−02 | 1.491E−02 | 3.540E−02 | 3.540E−02 | 1.079E−02 | 2.360E−02 | 7.680E−03 | 3.776E−02 |
| 316 | 1.070E−03 | 1.075E−03 | 3.540E−03 | 1.191E−03 | 5.127E−04 | 2.639E−03 | 3.818E−04 | 1.182E−03 | 1.285E−03 | 1.564E−04 | 1.708E−04 | 6.264E−04 | 2.210E−03 |
| 317 | 2.467E−02 | 2.703E−02 | 2.832E−02 | 3.690E−02 | 2.403E−02 | 3.025E−02 | 1.875E−02 | 1.182E−03 | 2.467E−02 | 1.251E−02 | 1.828E−02 | 7.680E−03 | 2.210E−02 |
| 318 | 1.377E−03 | 1.995E−03 | 2.660E−03 | 1.590E−03 | 3.089E−03 | 2.639E−03 | 3.818E−04 | 2.360E−03 | 1.652E−03 | 2.188E−03 | 5.127E−04 | 7.830E−04 | 1.017E−03 |
| 319 | 2.266E−01 | 1.984E−01 | 2.667E−01 | 2.765E−01 | 2.134E−01 | 1.570E−01 | 1.231E−01 | 2.330E−01 | 2.596E−01 | 1.058E−01 | 1.517E−01 | 7.079E−02 | 1.540E−01 |
| 320 | 7.637E−04 | 1.382E−03 | 1.772E−03 | 3.969E−04 | 1.540E−03 | 0.000E+00 | 0.000E+00 | 5.921E−04 | 1.467E−03 | 0.000E+00 | 8.538E−04 | 1.568E−04 | 6.779E−04 |
| 321 | 1.823E−01 | 2.167E−01 | 3.039E−01 | 2.109E−01 | 1.847E−01 | 1.643E−01 | 9.975E−02 | 2.077E−01 | 1.959E−01 | 6.114E−02 | 1.560E−01 | 5.814E−02 | 2.143E−01 |
| 322 | 7.337E−03 | 8.431E−03 | 4.441E−03 | 9.139E−03 | 6.672E−03 | 7.894E−03 | 4.591E−03 | 7.101E−03 | 4.762E−03 | 1.720E−03 | 4.784E−03 | 2.038E−03 | 5.427E−03 |
| 323 | 2.673E−01 | 2.556E−01 | 3.465E−01 | 3.086E−01 | 2.946E−01 | 1.538E−01 | 1.656E−01 | 3.052E−01 | 2.718E−01 | 1.077E−01 | 1.815E−01 | 1.004E−01 | 1.431E−01 |
| 324 | 9.332E−03 | 1.075E−02 | 1.330E−02 | 1.111E−02 | 7.186E−03 | 3.282E−03 | 4.977E−03 | 1.064E−02 | 7.701E−03 | 3.282E−03 | 6.500E−03 | 3.604E−03 | 4.226E−03 |
| 325 | 9.031E−03 | 1.043E−02 | 1.772E−02 | 5.170E−03 | 3.583E−03 | 7.229E−03 | 4.205E−03 | 3.540E−03 | 1.285E−02 | 3.432E−03 | 3.583E−03 | 4.548E−03 | 1.100E−02 |
| 326 | 1.377E−03 | 1.227E−03 | 2.660E−03 | 7.937E−04 | 5.127E−04 | 1.971E−03 | 7.658E−04 | 0.000E+00 | 1.834E−03 | 3.132E−04 | 1.025E−03 | 6.264E−04 | 2.381E−03 |
| 327 | 1.133E−02 | 1.718E−02 | 9.739E−03 | 9.932E−03 | 6.157E−03 | 9.868E−03 | 4.977E−03 | 6.500E−03 | 1.467E−02 | 5.320E−03 | 7.337E−03 | 5.492E−03 | 2.381E−02 |
| 328 | 1.223E−03 | 1.688E−03 | 6.200E−03 | 0.000E+00 | 2.574E−03 | 6.564E−04 | 3.818E−04 | 5.921E−04 | 1.652E−03 | 3.132E−04 | 6.822E−04 | 7.830E−04 | 1.693E−03 |
| 329 | 4.736E−01 | 5.931E−01 | 6.141E−01 | 6.522E−01 | 6.647E−01 | 4.188E−01 | 2.276E−01 | 4.832E−01 | 4.714E−01 | 1.705E−01 | 3.816E−01 | 1.369E−01 | 5.451E−01 |
| 330 | 5.191E−03 | 8.431E−03 | 6.200E−03 | 5.556E−03 | 5.642E−03 | 2.639E−03 | 2.295E−03 | 2.960E−03 | 4.762E−03 | 2.660E−03 | 5.985E−03 | 1.881E−03 | 4.226E−03 |
| 331 | 3.068E−02 | 4.462E−02 | 5.663E−02 | 3.540E−02 | 2.510E−02 | 1.971E−02 | 9.568E−03 | 3.025E−02 | 3.990E−02 | 1.032E−02 | 1.999E−02 | 1.238E−02 | 4.376E−02 |
| 332 | 6.114E−04 | 1.841E−03 | 8.860E−04 | 0.000E+00 | 5.127E−04 | 1.315E−03 | 0.000E+00 | 0.000E+00 | 5.513E−04 | 4.698E−04 | 5.127E−04 | 7.830E−04 | 8.474E−04 |
| 333 | 1.652E−02 | 3.518E−02 | 2.746E−02 | 1.787E−02 | 1.283E−02 | 2.038E−02 | 7.272E−03 | 1.242E−02 | 2.338E−02 | 9.224E−03 | 1.349E−02 | 8.152E−03 | 2.510E−02 |
| 334 | 0.000E+00 | 3.068E−04 | 2.660E−03 | 3.969E−04 | 0.000E+00 | 1.971E−03 | 3.818E−04 | 0.000E+00 | 3.668E−04 | 0.000E+00 | 5.127E−04 | 9.396E−04 | 6.779E−04 |
| 335 | 4.870E−02 | 5.620E−02 | 7.894E−02 | 5.728E−02 | 4.205E−02 | 3.818E−02 | 1.759E−02 | 3.840E−02 | 5.213E−02 | 2.111E−02 | 3.475E−02 | 1.317E−02 | 4.419E−02 |
| 336 | 2.295E−03 | 3.990E−03 | 4.441E−03 | 2.789E−03 | 4.612E−03 | 1.971E−03 | 7.658E−04 | 3.540E−03 | 3.861E−03 | 2.188E−03 | 4.269E−03 | 3.604E−03 | 2.703E−03 |
| 337 | 8.667E−02 | 1.058E−01 | 1.392E−01 | 1.302E−01 | 1.165E−01 | 8.881E−02 | 4.162E−02 | 8.388E−02 | 8.667E−02 | 3.261E−02 | 7.337E−02 | 2.467E−02 | 1.154E−01 |
| 338 | 9.182E−04 | 2.446E−03 | 2.660E−03 | 1.986E−03 | 1.540E−03 | 1.971E−03 | 1.148E−03 | 4.741E−03 | 2.019E−03 | 1.251E−03 | 5.127E−04 | 4.698E−04 | 3.733E−03 |
| 339 | 5.213E−02 | 6.436E−02 | 6.736E−02 | 6.350E−02 | 4.312E−02 | 2.488E−02 | 1.798E−02 | 2.960E−02 | 6.135E−02 | 1.969E−02 | 3.540E−02 | 1.772E−02 | 4.290E−02 |
| 340 | 2.446E−03 | 2.917E−03 | 6.200E−03 | 4.762E−03 | 2.574E−03 | 3.947E−03 | 2.295E−03 | 1.774E−03 | 3.304E−03 | 1.251E−03 | 1.708E−03 | 7.830E−04 | 1.862E−03 |
| 341 | 3.368E−03 | 6.757E−03 | 1.418E−02 | 2.381E−03 | 6.157E−03 | 1.971E−03 | 7.658E−04 | 4.140E−03 | 5.513E−03 | 2.034E−03 | 2.553E−03 | 2.982E−03 | 5.921E−03 |
| 342 | 7.637E−04 | 4.612E−04 | 0.000E+00 | 7.937E−04 | 1.028E−03 | 0.000E+00 | 7.658E−04 | 0.000E+00 | 1.467E−03 | 3.132E−04 | 1.708E−04 | 6.264E−04 | 1.186E−03 |
| 343 | 5.964E−03 | 1.043E−02 | 3.540E−03 | 3.969E−03 | 2.574E−03 | 3.947E−03 | 3.818E−03 | 7.101E−03 | 6.243E−03 | 3.282E−03 | 5.814E−03 | 2.360E−03 | 7.272E−03 |
| 344 | 0.000E+00 | 0.000E+00 | 0.000E+00 | 3.969E−04 | 0.000E+00 | 0.000E+00 | 0.000E+00 | 0.000E+00 | 1.834E−04 | 0.000E+00 | 1.708E−04 | 1.568E−04 | 1.693E−04 |

APPENDIX D-continued

Ovarian Cancer Training Dataset

| | CL | CM | CN | CO | CP | CQ | CR | CS | CT | CU | CV | CW | CX |
|---|---|---|---|---|---|---|---|---|---|---|---|---|---|
| 1 | 14641 | 13814 | 13821 | 14630 | 14195 | 13768 | 14629 | 14627 | 13800 | 13620 | 13896 | 13698 | 14654 |
| 2 | Late Malignant | Benign | Benign | Early Malignant | Late Malignant | Benign | Late Malignant | Late Malignant | Benign | Late Malignant | Benign | Early Malignant | Early Malignant |
| 3 | 3 | 1 | 1 | 2 | 3 | 1 | 3 | 3 | 1 | 3 | 1 | 2 | 2 |
| 4 | −1 | −1 | −1 | −1 | −1 | −1 | −1 | −1 | −1 | −1 | −1 | −1 | −1 |
| 5 | 8.104E−01 | 1.367E+00 | 2.164E+00 | 1.511E+00 | 1.507E+00 | 1.664E+00 | 1.305E+00 | 1.394E+00 | 1.973E+00 | 1.283E+00 | 1.139E+00 | 1.295E+00 | 9.052E−01 |
| 6 | 2.940E−01 | 2.972E−01 | 4.270E−01 | 4.989E−01 | 5.172E−01 | 4.592E−01 | 4.324E−01 | 4.217E−01 | 3.702E−01 | 2.446E−01 | 7.961E−02 | 6.277E−01 | 4.742E−01 |
| 7 | 1.212E−01 | 1.277E−01 | 1.749E−01 | 1.727E−01 | 1.631E−01 | 1.985E−01 | 1.685E−01 | 1.642E−01 | 1.524E−01 | 1.781E−01 | 3.809E−02 | 2.382E−01 | 1.395E−01 |
| 8 | 5.247E−01 | 1.582E+00 | 2.274E+00 | 1.855E+00 | 1.951E+00 | 6.459E−01 | 9.004E−01 | 1.216E+00 | 2.098E+00 | 6.789E−01 | 2.824E+00 | 8.774E−01 | 5.075E−01 |
| 9 | 1.180E−02 | 4.367E−02 | 3.197E−02 | 1.996E−02 | 1.674E−02 | 2.382E−02 | 1.298E−02 | 1.255E−02 | 1.996E−02 | 1.921E−02 | 3.026E−02 | 1.556E−02 | 1.996E−02 |
| 10 | 5.612E−03 | 7.532E−03 | 5.225E−03 | 3.219E−03 | 6.298E−03 | 8.927E−03 | 1.148E−02 | 7.994E−03 | 7.983E−03 | 7.822E−03 | 8.648E−04 | 8.283E−03 | 8.187E−03 |
| 11 | 3.369E−03 | 6.030E−03 | 3.262E−03 | 4.506E−03 | 5.590E−03 | 7.736E−03 | 8.616E−03 | 7.994E−03 | 7.189E−03 | 6.009E−03 | 8.648E−04 | 7.253E−03 | 7.157E−03 |
| 12 | 7.296E−03 | 1.055E−02 | 9.142E−03 | 3.863E−03 | 6.298E−03 | 2.972E−03 | 6.223E−03 | 1.137E−02 | 8.788E−03 | 5.408E−03 | 5.193E−03 | 6.212E−03 | 8.691E−03 |
| 13 | 1.010E−02 | 1.427E−02 | 2.092E−02 | 1.159E−02 | 2.446E−02 | 8.337E−03 | 6.706E−03 | 1.255E−02 | 2.082E−02 | 1.749E−02 | 3.112E−02 | 1.035E−02 | 7.157E−03 |
| 14 | 3.755E−02 | 5.880E−02 | 4.700E−02 | 6.695E−02 | 7.200E−02 | 5.837E−02 | 4.313E−02 | 4.624E−02 | 6.395E−02 | 4.270E−02 | 2.253E−02 | 4.871E−02 | 4.603E−02 |
| 15 | 3.369E−03 | 7.532E−04 | 1.309E−03 | 2.575E−03 | 1.116E−02 | 4.163E−03 | 2.393E−03 | 3.423E−03 | 7.983E−03 | 4.206E−03 | 5.193E−03 | 4.142E−03 | 2.049E−03 |
| 16 | 1.685E−03 | 3.015E−03 | 1.309E−03 | 0.000E+00 | 6.996E−04 | 1.191E−03 | 1.438E−03 | 5.708E−04 | 7.983E−04 | 2.403E−03 | 0.000E+00 | 2.586E−03 | 1.534E−03 |
| 17 | 7.350E−02 | 2.489E−02 | 1.309E−02 | 1.159E−02 | 1.395E−02 | 2.146E−02 | 1.298E−02 | 1.255E−02 | 1.277E−02 | 1.023E−02 | 6.921E−03 | 8.809E−03 | 1.223E−02 |
| 18 | 2.382E−01 | 8.659E−02 | 5.161E−02 | 3.090E−02 | 3.777E−02 | 6.545E−02 | 2.393E−02 | 4.742E−02 | 5.193E−02 | 3.970E−02 | 1.556E−02 | 4.303E−02 | 3.884E−02 |
| 19 | 1.384E−01 | 9.421E−02 | 1.277E−01 | 1.029E−01 | 8.112E−02 | 1.116E−01 | 6.652E−02 | 9.871E−02 | 1.039E−01 | 7.575E−02 | 7.006E−02 | 9.474E−02 | 6.084E−02 |
| 20 | 2.242E−03 | 0.000E+00 | 3.262E−03 | 6.438E−04 | 2.103E−03 | 1.781E−03 | 0.000E+00 | 0.000E+00 | 7.983E−04 | 0.000E+00 | 1.727E−03 | 1.035E−03 | 2.049E−03 |
| 21 | 1.738E−02 | 6.781E−03 | 2.092E−02 | 3.219E−03 | 1.049E−02 | 1.781E−02 | 3.348E−03 | 1.202E−02 | 1.202E−02 | 1.023E−02 | 4.324E−03 | 1.084E−02 | 1.588E−02 |
| 22 | 5.612E−04 | 5.279E−03 | 3.262E−03 | 1.931E−03 | 2.800E−03 | 2.382E−03 | 1.438E−03 | 1.137E−03 | 1.599E−03 | 1.803E−03 | 2.597E−03 | 2.586E−03 | 5.118E−04 |
| 23 | 2.747E−02 | 3.916E−02 | 3.069E−02 | 5.150E−02 | 4.056E−02 | 4.163E−02 | 2.103E−02 | 4.335E−02 | 4.238E−02 | 2.403E−02 | 3.541E−02 | 4.249E−02 | 2.865E−02 |
| 24 | 1.964E−01 | 8.358E−02 | 6.524E−02 | 5.794E−02 | 4.335E−02 | 8.927E−02 | 5.365E−02 | 8.616E−02 | 6.234E−02 | 7.275E−02 | 4.925E−02 | 6.781E−02 | 6.341E−02 |
| 25 | 7.854E−03 | 9.796E−03 | 1.170E−02 | 1.803E−02 | 8.391E−03 | 1.545E−02 | 1.298E−02 | 1.202E−02 | 1.277E−02 | 6.009E−03 | 1.470E−02 | 3.112E−02 | 1.588E−02 |
| 26 | 8.970E−03 | 2.940E−02 | 1.373E−02 | 2.189E−02 | 1.674E−02 | 1.727E−02 | 1.341E−02 | 1.481E−02 | 2.800E−02 | 1.084E−02 | 2.511E−02 | 2.017E−02 | 7.672E−03 |
| 27 | 1.685E−03 | 8.283E−03 | 6.524E−04 | 2.575E−03 | 2.800E−03 | 3.573E−03 | 3.348E−03 | 3.423E−03 | 3.991E−03 | 2.403E−03 | 6.921E−03 | 3.627E−03 | 2.554E−03 |
| 28 | 2.242E−02 | 2.414E−02 | 1.170E−02 | 2.382E−02 | 1.534E−02 | 2.564E−02 | 2.157E−02 | 2.167E−02 | 7.189E−03 | 2.103E−02 | 2.597E−02 | 3.315E−02 | 2.049E−02 |
| 29 | 3.026E−02 | 3.391E−02 | 3.455E−02 | 2.060E−02 | 3.079E−02 | 3.036E−02 | 1.964E−02 | 3.251E−02 | 2.639E−02 | 2.403E−02 | 2.253E−02 | 4.453E−02 | 4.345E−02 |
| 30 | 1.298E−01 | 7.682E−02 | 6.395E−02 | 5.086E−02 | 5.247E−02 | 6.964E−02 | 5.408E−02 | 7.768E−02 | 4.388E−02 | 9.378E−02 | 4.839E−02 | 6.266E−02 | 6.448E−02 |
| 31 | 8.133E−02 | 6.030E−02 | 4.174E−02 | 4.120E−02 | 5.590E−02 | 5.601E−02 | 2.779E−02 | 4.850E−02 | 5.193E−02 | 5.536E−02 | 4.152E−02 | 4.614E−02 | 2.511E−02 |
| 32 | 2.865E−02 | 5.655E−02 | 6.266E−02 | 4.635E−02 | 4.968E−02 | 2.972E−02 | 2.103E−02 | 6.223E−02 | 4.796E−02 | 2.951E−02 | 6.663E−02 | 3.734E−02 | 1.792E−02 |
| 33 | 7.296E−03 | 1.427E−02 | 1.695E−02 | 1.223E−02 | 1.191E−02 | 1.012E−02 | 9.582E−03 | 1.652E−02 | 6.395E−03 | 8.423E−03 | 2.071E−02 | 1.298E−02 | 1.277E−02 |
| 34 | 2.157E−01 | 7.350E−01 | 7.704E−01 | 4.592E−01 | 5.182E−01 | 3.938E−01 | 2.865E−01 | 3.938E−01 | 8.330E−01 | 4.292E−01 | 2.693E−01 | 3.283E−01 | 2.446E−01 |
| 35 | 5.268E−02 | 7.532E−02 | 4.378E−02 | 7.339E−02 | 8.530E−02 | 5.483E−02 | 7.039E−02 | 1.033E−01 | 8.788E−02 | 7.639E−02 | 5.880E−02 | 6.996E−02 | 4.914E−02 |
| 36 | 7.296E−03 | 8.283E−03 | 4.571E−03 | 4.506E−03 | 2.800E−03 | 3.573E−03 | 3.348E−03 | 3.423E−03 | 4.796E−03 | 1.202E−03 | 5.193E−03 | 6.212E−03 | 3.069E−03 |
| 37 | 1.127E−02 | 1.427E−02 | 1.567E−02 | 1.029E−02 | 1.674E−02 | 1.609E−02 | 7.661E−03 | 1.137E−02 | 1.513E−02 | 1.084E−02 | 8.648E−03 | 1.609E−02 | 1.996E−02 |
| 78 | 1.180E−02 | 3.015E−02 | 3.197E−02 | 1.352E−02 | 2.028E−02 | 2.972E−03 | 6.223E−03 | 1.888E−02 | 2.715E−02 | 1.867E−02 | 9.517E−03 | 1.448E−02 | 1.023E−02 |
| 39 | 4.313E−02 | 5.429E−02 | 4.378E−02 | 8.423E−02 | 7.618E−02 | 8.155E−02 | 8.476E−02 | 3.820E−02 | 3.991E−02 | 3.670E−02 | 7.436E−02 | 1.105E−01 | 5.833E−02 |
| 40 | 1.277E−01 | 1.127E−01 | 1.050E−01 | 6.953E−02 | 1.094E−01 | 1.481E−01 | 1.127E−01 | 1.631E−01 | 7.586E−02 | 1.459E−01 | 1.330E−01 | 1.792E−01 | 1.567E−01 |
| 41 | 1.631E−02 | 2.114E−02 | 2.876E−02 | 1.288E−02 | 1.888E−02 | 1.910E−02 | 1.005E−02 | 3.251E−02 | 1.996E−02 | 2.049E−02 | 2.682E−02 | 2.951E−02 | 1.685E−02 |
| 42 | 5.612E−04 | 4.517E−03 | 2.607E−03 | 1.931E−03 | 0.000E+00 | 5.955E−04 | 4.785E−04 | 1.137E−03 | 3.197E−03 | 0.000E+00 | 8.648E−04 | 2.586E−03 | 1.023E−03 |
| 43 | 4.707E−03 | 1.245E−02 | 1.690E−02 | 1.157E−02 | 1.577E−02 | 3.704E−03 | 6.198E−03 | 4.115E−03 | 1.111E−02 | 7.922E−03 | 1.286E−02 | 5.581E−03 | 4.784E−03 |
| 44 | 1.928E−01 | 6.882E−01 | 6.608E−01 | 5.373E−01 | 5.892E−01 | 3.094E−01 | 2.653E−01 | 3.341E−01 | 9.404E−01 | 3.521E−01 | 1.139E−01 | 2.690E−01 | 1.899E−01 |
| 45 | 8.899E−02 | 2.058E−01 | 2.081E−01 | 2.316E−01 | 2.301E−01 | 1.070E−01 | 1.062E−01 | 1.075E−01 | 2.510E−01 | 9.028E−02 | 5.555E−02 | 1.625E−01 | 1.062E−01 |
| 46 | 7.613E−02 | 2.252E−01 | 2.101E−01 | 2.219E−01 | 1.703E−01 | 7.896E−02 | 1.127E−01 | 9.696E−02 | 1.681E−01 | 1.114E−01 | 1.319E−01 | 1.013E−01 | 6.841E−02 |
| 47 | 1.608E−01 | 5.620E−01 | 5.130E−01 | 3.817E−01 | 4.987E−01 | 1.959E−01 | 1.877E−01 | 2.986E−01 | 7.850E−01 | 2.348E−01 | 9.285E−02 | 2.205E−01 | 1.358E−01 |

APPENDIX D-continued

| Ovarian Cancer Training Dataset | | | | | | | | | | | | | |
|---|---|---|---|---|---|---|---|---|---|---|---|---|---|
| 48 | 1.587E−02 | 4.475E−02 | 4.192E−02 | 7.793E−02 | 3.601E−02 | 2.572E−02 | 2.983E−02 | 2.135E−02 | 5.941E−02 | 1.700E−02 | 1.160E−02 | 2.346E−02 | 1.361E−02 |
| 49 | 8.333E−03 | 3.498E−02 | 2.623E−02 | 2.343E−02 | 2.549E−02 | 1.070E−02 | 1.217E−02 | 1.397E−02 | 3.524E−02 | 1.152E−02 | 6.636E−03 | 1.093E−02 | 6.867E−03 |
| 50 | 3.215E−03 | 1.011E−02 | 6.404E−03 | 8.024E−03 | 8.050E−03 | 2.701E−03 | 3.549E−03 | 3.421E−03 | 7.459E−03 | 2.726E−03 | 2.281E−03 | 2.598E−03 | 1.103E−03 |
| 51 | 2.129E−01 | 1.731E−01 | 1.319E−01 | 9.490E−02 | 1.404E−01 | 1.461E−01 | 1.371E−01 | 1.415E−01 | 6.173E−02 | 2.841E−01 | 1.427E−01 | 1.029E−01 | 1.828E−01 |
| 52 | 1.883E−03 | 5.967E−03 | 4.372E−03 | 1.852E−03 | 6.533E−03 | 1.713E−03 | 2.526E−03 | 1.641E−03 | 3.061E−03 | 2.726E−03 | 4.964E−03 | 2.482E−03 | 1.595E−03 |
| 53 | 3.601E−02 | 1.119E−01 | 1.109E−01 | 6.816E−02 | 6.944E−02 | 5.864E−02 | 3.961E−02 | 6.378E−02 | 1.237E−01 | 6.070E−02 | 5.067E−02 | 4.681E−02 | 3.987E−02 |
| 54 | 6.455E+00 | 4.073E+00 | 3.989E+00 | 4.304E+00 | 3.626E+00 | 6.014E+00 | 5.482E+00 | 5.407E+00 | 3.391E+00 | 4.299E+00 | 2.916E+00 | 6.060E+00 | 6.041E+00 |
| 55 | 7.104E−01 | 5.792E−01 | 4.645E−01 | 4.645E−01 | 4.569E−01 | 6.553E−01 | 6.070E−01 | 6.029E−01 | 3.448E−01 | 9.436E−01 | 4.532E−01 | 6.039E−01 | 5.906E−01 |
| 56 | 2.002E−01 | 1.430E−01 | 1.643E−01 | 1.685E−01 | 1.466E−01 | 2.146E−01 | 1.806E−01 | 1.849E−01 | 1.314E−01 | 1.287E−01 | 9.182E−02 | 2.103E−01 | 2.130E−01 |
| 57 | 4.408E+00 | 3.463E+00 | 2.715E+00 | 3.011E+00 | 2.471E+00 | 4.150E+00 | 3.716E+00 | 3.718E+00 | 2.040E+00 | 5.392E+00 | 2.795E+00 | 3.331E+00 | 3.223E+00 |
| 58 | 5.890E−02 | 1.024E−01 | 7.639E−02 | 8.436E−02 | 5.247E−02 | 4.707E−02 | 5.272E−02 | 4.784E−02 | 6.533E−02 | 5.272E−02 | 8.076E−02 | 4.707E−02 | 4.167E−02 |
| 59 | 6.584E−02 | 5.838E−02 | 4.578E−02 | 3.832E−02 | 3.446E−02 | 6.173E−02 | 5.915E−02 | 6.456E−02 | 3.472E−02 | 7.484E−02 | 4.141E−02 | 4.887E−02 | 5.453E−02 |
| 60 | 1.896E−02 | 4.630E−02 | 4.887E−02 | 3.112E−02 | 4.347E−02 | 2.454E−02 | 2.148E−02 | 3.292E−02 | 6.739E−02 | 2.675E−02 | 1.597E−02 | 2.397E−02 | 1.950E−02 |
| 61 | 1.206E+00 | 9.873E−01 | 8.681E−01 | 1.972E+00 | 8.052E−01 | 2.039E+00 | 2.486E+00 | 1.162E+00 | 7.664E−01 | 8.883E−01 | 1.633E+00 | 1.138E+00 | 1.195E+00 |
| 62 | 4.104E−01 | 2.696E−01 | 4.241E−01 | 3.450E−01 | 4.179E−01 | 3.862E−01 | 2.890E−01 | 3.849E−01 | 2.818E−01 | 3.360E−01 | 3.184E−01 | 8.689E−01 | 6.273E−01 |
| 63 | 1.209E−02 | 1.337E−02 | 1.268E−02 | 3.061E−02 | 1.124E−02 | 1.456E−02 | 1.790E−02 | 1.314E−02 | 1.800E−02 | 1.008E−02 | 1.265E−02 | 1.427E−02 | 8.822E−03 |
| 64 | 2.733E+00 | 1.509E+00 | 2.038E+00 | 1.403E+00 | 1.925E+00 | 2.012E+00 | 1.909E+00 | 2.602E+00 | 1.309E+00 | 1.791E+00 | 9.856E−01 | 3.070E+00 | 3.626E+00 |
| 65 | 1.317E−01 | 1.232E−01 | 1.571E−01 | 1.335E−01 | 1.512E−01 | 9.362E−02 | 1.034E−01 | 1.348E−01 | 1.551E−01 | 9.362E−02 | 7.047E−02 | 1.557E−01 | 1.425E−01 |
| 66 | 5.976E−01 | 4.269E−01 | 5.011E−01 | 3.402E−01 | 4.323E−01 | 3.987E−01 | 4.024E−01 | 6.077E−01 | 2.443E−01 | 6.669E−01 | 4.306E−01 | 6.265E−01 | 6.116E−01 |
| 67 | 5.967E−02 | 1.235E−01 | 1.237E−01 | 1.039E−01 | 1.034E−01 | 5.015E−02 | 5.195E−02 | 6.301E−02 | 9.156E−02 | 6.430E−02 | 4.810E−02 | 6.636E−02 | 5.144E−02 |
| 68 | 8.256E−02 | 2.042E−01 | 2.564E−01 | 1.160E−01 | 2.234E−01 | 9.388E−02 | 7.870E−02 | 1.554E−01 | 2.843E−01 | 1.340E−01 | 7.021E−02 | 1.260E−01 | 1.206E−01 |
| 69 | 4.399E−01 | 3.644E−01 | 4.075E−01 | 6.605E−01 | 3.703E−01 | 7.113E−01 | 9.011E−01 | 5.517E−01 | 3.157E−01 | 3.766E−01 | 5.656E−01 | 5.592E−01 | 5.873E−01 |
| 70 | 3.061E−02 | 4.115E−02 | 4.527E−02 | 7.742E−02 | 5.658E−02 | 3.421E−02 | 4.192E−02 | 3.678E−02 | 5.401E−02 | 2.451E−02 | 4.321E−02 | 3.446E−02 | 2.906E−02 |
| 71 | 8.616E−03 | 1.824E−02 | 1.878E−02 | 1.620E−02 | 1.759E−02 | 9.413E−03 | 6.996E−03 | 1.217E−02 | 1.973E−02 | 6.919E−03 | 3.318E−03 | 8.076E−03 | 8.462E−03 |
| 72 | 2.701E−03 | 3.421E−03 | 4.218E−03 | 4.167E−03 | 3.678E−03 | 3.421E−03 | 4.012E−03 | 2.464E−03 | 5.555E−03 | 1.875E−03 | 2.073E−03 | 2.983E−03 | 2.829E−03 |
| 73 | 1.354E−02 | 7.923E−03 | 4.120E−03 | 2.709E−03 | 2.946E−03 | 4.379E−03 | 1.008E−03 | 2.404E−03 | 2.517E−03 | 1.264E−03 | 3.634E−03 | 1.637E−03 | 2.156E−03 |
| 74 | 2.415E−02 | 7.133E−03 | 8.239E−03 | 1.151E−02 | 1.104E−02 | 1.321E−02 | 4.029E−03 | 8.409E−03 | 1.093E−02 | 1.012E−02 | 7.280E−03 | 3.815E−03 | 5.384E−03 |
| 75 | 1.433E−01 | 7.370E−02 | 3.984E−02 | 3.792E−02 | 7.133E−02 | 6.264E−02 | 6.242E−02 | 7.506E−02 | 6.637E−02 | 6.005E−02 | 2.912E−02 | 5.779E−02 | 2.957E−02 |
| 76 | 6.309E−02 | 9.752E−02 | 4.391E−02 | 3.657E−02 | 9.492E−02 | 6.196E−02 | 5.847E−02 | 1.433E−01 | 1.230E−01 | 1.219E−01 | 2.551E−02 | 6.479E−02 | 2.901E−02 |
| 77 | 3.544E−03 | 9.515E−03 | 2.054E−03 | 4.063E−03 | 1.467E−02 | 3.126E−03 | 5.542E−03 | 1.321E−02 | 8.397E−03 | 4.424E−03 | 8.183E−03 | 4.357E−03 | 2.156E−03 |
| 78 | 0.000E+00 | 0.000E+00 | 6.862E−04 | 2.032E−03 | 0.000E+00 | 0.000E+00 | 2.020E−03 | 1.196E−03 | 8.397E−04 | 1.896E−03 | 9.097E−04 | 1.089E−03 | 1.076E−03 |
| 79 | 1.749E−01 | 4.199E−02 | 1.716E−02 | 1.015E−02 | 9.560E−03 | 4.639E−02 | 1.411E−02 | 2.336E−02 | 1.591E−02 | 2.212E−02 | 8.183E−03 | 1.738E−02 | 2.099E−02 |
| 80 | 1.591E−02 | 4.752E−03 | 2.054E−03 | 1.354E−03 | 7.359E−04 | 4.379E−03 | 2.517E−03 | 4.808E−03 | 2.517E−03 | 6.321E−03 | 2.731E−03 | 2.720E−03 | 3.770E−03 |
| 81 | 3.442E−01 | 8.397E−02 | 5.835E−02 | 3.995E−02 | 3.600E−02 | 1.008E−01 | 4.131E−02 | 4.740E−02 | 4.537E−02 | 4.876E−02 | 3.826E−02 | 2.619E−02 | 3.228E−02 |
| 82 | 1.490E−01 | 5.305E−02 | 2.675E−02 | 1.082E−02 | 1.104E−02 | 5.135E−02 | 1.108E−02 | 2.460E−02 | 1.264E−02 | 1.840E−02 | 9.097E−03 | 1.309E−02 | 1.828E−02 |
| 83 | 3.420E−02 | 4.752E−03 | 4.808E−03 | 4.740E−03 | 2.946E−03 | 1.501E−02 | 6.546E−03 | 6.005E−03 | 3.363E−03 | 2.528E−03 | 3.634E−03 | 5.451E−04 | 5.914E−03 |
| 84 | 1.003E−02 | 1.907E−02 | 1.986E−02 | 1.625E−02 | 3.307E−02 | 6.264E−03 | 9.571E−03 | 1.020E−02 | 3.273E−02 | 1.648E−02 | 2.460E−02 | 1.140E−02 | 1.828E−02 |
| 85 | 7.077E−03 | 3.172E−03 | 3.431E−03 | 4.740E−03 | 2.946E−03 | 3.126E−03 | 1.008E−03 | 6.603E−03 | 5.880E−03 | 5.056E−03 | 6.366E−03 | 6.535E−03 | 1.614E−03 |
| 86 | 2.302E−02 | 8.713E−03 | 9.616E−03 | 1.219E−02 | 1.321E−02 | 8.770E−03 | 9.571E−03 | 1.738E−02 | 1.851E−02 | 1.388E−02 | 1.185E−02 | 9.266E−03 | 3.770E−03 |
| 87 | 3.657E−02 | 5.068E−02 | 2.540E−02 | 1.558E−02 | 3.386E−02 | 3.442E−02 | 1.512E−02 | 3.059E−02 | 3.273E−02 | 3.352E−02 | 3.273E−02 | 3.488E−02 | 1.023E−02 |
| 88 | 1.772E−03 | 7.133E−03 | 2.054E−03 | 4.063E−03 | 1.467E−03 | 1.253E−03 | 5.034E−03 | 4.808E−03 | 5.045E−03 | 8.860E−03 | 2.731E−03 | 5.993E−03 | 2.686E−03 |
| 89 | 1.411E−02 | 1.738E−02 | 1.377E−02 | 1.015E−02 | 2.506E−02 | 5.632E−03 | 1.456E−02 | 2.878E−02 | 2.438E−02 | 2.212E−02 | 2.088E−02 | 1.693E−02 | 1.185E−02 |
| 30 | 3.781E−02 | 4.752E−02 | 1.445E−02 | 3.521E−02 | 8.533E−02 | 1.749E−02 | 2.777E−02 | 7.506E−02 | 5.293E−02 | 3.420E−02 | 3.454E−02 | 4.571E−02 | 1.343E−02 |
| 91 | 8.262E−03 | 7.133E−03 | 2.743E−03 | 1.082E−02 | 8.826E−03 | 5.011E−03 | 3.521E−03 | 9.605E−03 | 7.562E−03 | 6.953E−03 | 1.001E−02 | 4.357E−03 | 3.770E−03 |
| 92 | 1.828E−02 | 1.907E−02 | 8.239E−03 | 1.693E−02 | 2.427E−02 | 1.185E−02 | 9.063E−03 | 1.682E−02 | 2.020E−02 | 1.772E−02 | 2.178E−02 | 1.035E−02 | 9.142E−03 |
| 93 | 1.003E−02 | 9.515E−03 | 2.054E−03 | 6.095E−03 | 9.560E−03 | 4.379E−03 | 4.029E−03 | 2.404E−03 | 7.562E−03 | 1.140E−02 | 3.634E−03 | 5.993E−03 | 3.770E−03 |
| 94 | 4.718E−03 | 7.923E−04 | 6.862E−04 | 2.032E−03 | 7.359E−04 | 6.264E−04 | 5.034E−04 | 4.808E−03 | 2.517E−03 | 6.321E−04 | 3.634E−03 | 2.720E−03 | 2.156E−03 |
| 95 | 1.003E−02 | 1.030E−02 | 9.616E−03 | 8.792E−03 | 1.840E−02 | 7.517E−03 | 1.366E−02 | 2.765E−02 | 8.397E−03 | 1.264E−02 | 1.907E−02 | 9.808E−03 | 5.384E−03 |
| 96 | 5.903E−03 | 6.343E−03 | 2.743E−03 | 4.740E−03 | 6.625E−03 | 8.138E−03 | 6.050E−03 | 1.501E−02 | 5.045E−03 | 6.953E−03 | 6.366E−03 | 9.808E−03 | 3.770E−03 |
| 97 | 5.305E−03 | 4.752E−03 | 6.862E−03 | 4.063E−03 | 1.104E−02 | 2.506E−03 | 4.537E−03 | 9.605E−03 | 9.244E−03 | 3.792E−03 | 5.463E−03 | 1.035E−02 | 4.300E−03 |

APPENDIX D-continued

Ovarian Cancer
Training Dataset

| | | | | | | | | | | | | | |
|---|---|---|---|---|---|---|---|---|---|---|---|---|---|
| 98 | 1.354E−02 | 1.986E−02 | 7.551E−03 | 1.354E−02 | 2.133E−02 | 1.625E−02 | 8.567E−03 | 1.862E−02 | 2.020E−02 | 1.456E−02 | 2.280E−02 | 1.196E−02 | 1.185E−02 |
| 99 | 5.960E−02 | 6.720E−02 | 1.655E−01 | 1.410E−01 | 1.349E−01 | 9.393E−02 | 7.995E−02 | 6.070E−02 | 1.484E−01 | 5.567E−02 | 1.619E−01 | 9.589E−02 | 7.247E−02 |
| 100 | 2.367E−02 | 2.673E−02 | 5.812E−02 | 3.532E−02 | 5.359E−02 | 2.587E−02 | 2.735E−02 | 3.458E−02 | 5.837E−02 | 4.402E−02 | 6.622E−02 | 2.134E−02 | 3.274E−02 |
| 101 | 1.198E−01 | 1.102E−01 | 1.643E−01 | 1.312E−01 | 1.300E−01 | 1.803E−01 | 1.508E−01 | 1.582E−01 | 1.606E−01 | 1.410E−01 | 1.557E−01 | 1.619E−01 | 1.692E−01 |
| 102 | 7.153E−01 | 1.347E+00 | 1.167E+00 | 1.120E+00 | 1.474E+00 | 6.352E−01 | 6.426E−01 | 9.290E−01 | 1.692E+00 | 8.748E−01 | 2.510E+00 | 5.849E−01 | 6.033E−01 |
| 103 | 1.754E−01 | 1.594E−01 | 1.741E−01 | 1.680E−01 | 1.410E−01 | 2.575E−01 | 2.367E−01 | 2.097E−01 | 2.097E−01 | 1.913E−01 | 1.508E−01 | 1.852E−01 | 1.925E−01 |
| 104 | 2.367E−01 | 4.059E−01 | 4.365E−01 | 3.679E−01 | 4.598E−01 | 2.342E−01 | 2.403E−01 | 2.906E−01 | 4.880E−01 | 2.489E−01 | 7.885E−01 | 2.195E−01 | 2.170E−01 |
| 105 | 1.017E+00 | 1.948E+00 | 1.502E+00 | 1.654E+00 | 2.051E+00 | 1.116E+00 | 9.781E−01 | 1.397E+00 | 2.486E+00 | 1.596E+00 | 2.912E+00 | 1.091E+00 | 1.108E+00 |
| 106 | 8.265E−02 | 1.471E−01 | 1.754E−01 | 1.937E−01 | 2.170E−01 | 1.177E−01 | 1.386E−01 | 1.057E−01 | 1.594E−01 | 1.410E−01 | 4.047E−01 | 1.471E−01 | 1.312E−01 |
| 107 | 1.212E−01 | 1.137E−01 | 1.778E−01 | 1.447E−01 | 1.386E−01 | 9.724E−02 | 7.885E−02 | 9.001E−02 | 1.717E−01 | 1.386E−01 | 3.605E−01 | 1.251E−01 | 8.878E−02 |
| 108 | 1.198E−01 | 1.337E−01 | 2.207E−01 | 1.754E−01 | 1.655E−01 | 1.386E−01 | 1.606E−01 | 1.422E−01 | 1.901E−01 | 1.386E−01 | 2.367E−01 | 1.962E−01 | 1.827E−01 |
| 109 | 3.850E−03 | 8.608E−03 | 8.204E−03 | 2.207E−03 | 7.198E−03 | 4.083E−03 | 3.826E−03 | 4.562E−03 | 6.389E−03 | 4.807E−03 | 6.916E−03 | 5.322E−03 | 4.672E−03 |
| 110 | 1.925E−02 | 8.608E−03 | 1.045E−02 | 4.414E−03 | 1.039E−02 | 1.839E−02 | 1.803E−02 | 1.631E−02 | 4.562E−03 | 2.477E−02 | 0.000E+00 | 2.072E−02 | 2.219E−02 |
| 111 | 1.218E−02 | 6.033E−03 | 7.456E−03 | 1.029E−02 | 7.198E−03 | 2.183E−02 | 1.373E−02 | 1.888E−02 | 7.308E−03 | 2.747E−02 | 4.942E−03 | 1.839E−02 | 1.876E−02 |
| 112 | 9.614E−03 | 3.446E−03 | 4.476E−03 | 4.414E−03 | 2.403E−03 | 1.225E−02 | 1.533E−02 | 1.109E−02 | 2.735E−03 | 2.195E−02 | 3.948E−03 | 1.839E−02 | 1.459E−02 |
| 113 | 1.925E−03 | 5.162E−03 | 3.728E−03 | 2.207E−03 | 7.995E−04 | 2.036E−03 | 1.643E−03 | 2.612E−03 | 3.654E−03 | 6.867E−03 | 1.974E−03 | 4.145E−03 | 5.261E−03 |
| 114 | 4.488E−03 | 9.467E−03 | 6.708E−03 | 2.207E−03 | 1.118E−02 | 1.020E−02 | 1.040E−02 | 3.262E−03 | 6.389E−03 | 8.240E−03 | 5.935E−03 | 4.145E−03 | 7.014E−03 |
| 115 | 5.126E−03 | 3.446E−03 | 8.204E−03 | 4.414E−03 | 2.403E−03 | 8.841E−03 | 6.021E−03 | 5.874E−03 | 1.827E−03 | 1.447E−02 | 1.974E−03 | 7.701E−03 | 7.603E−03 |
| 116 | 2.563E−03 | 3.446E−03 | 1.496E−03 | 7.357E−04 | 1.594E−03 | 1.361E−03 | 4.378E−03 | 2.612E−03 | 1.827E−03 | 6.180E−03 | 2.968E−03 | 4.145E−03 | 1.754E−03 |
| 117 | 7.051E−03 | 6.891E−03 | 5.972E−03 | 2.207E−03 | 5.592E−03 | 1.020E−02 | 1.040E−02 | 9.785E−03 | 9.123E−03 | 9.626E−03 | 2.968E−03 | 1.300E−02 | 5.261E−03 |
| 118 | 4.488E−03 | 5.162E−03 | 8.952E−03 | 1.471E−03 | 4.795E−03 | 7.480E−03 | 8.216E−03 | 5.874E−03 | 9.123E−04 | 8.939E−03 | 1.974E−03 | 4.733E−03 | 2.918E−03 |
| 119 | 3.200E−03 | 6.033E−03 | 1.496E−03 | 5.886E−03 | 3.200E−03 | 1.225E−02 | 6.021E−03 | 7.174E−03 | 2.735E−03 | 8.939E−03 | 5.935E−03 | 1.066E−02 | 4.096E−03 |
| 120 | 1.090E−02 | 9.467E−03 | 0.000E+00 | 2.943E−03 | 3.200E−03 | 7.480E−03 | 9.847E−03 | 7.174E−03 | 8.216E−03 | 1.582E−02 | 1.974E−03 | 7.100E−03 | 5.849E−03 |
| 121 | 4.016E−02 | 1.621E−02 | 5.138E−02 | 2.760E−02 | 5.503E−02 | 2.556E−02 | 2.395E−02 | 2.449E−02 | 3.428E−02 | 2.582E−02 | 3.713E−02 | 1.852E−02 | 7.320E−03 |
| 122 | 8.424E−02 | 1.184E−01 | 1.585E−01 | 1.149E−01 | 9.528E−02 | 8.094E−02 | 7.195E−02 | 9.350E−02 | 4.568E−02 | 1.291E−01 | 9.261E−02 | 6.296E−02 | 8.050E−02 |
| 123 | 2.627E+00 | 2.182E+00 | 2.930E+00 | 1.158E+00 | 1.309E+00 | 1.701E+00 | 1.754E+00 | 2.271E+00 | 1.612E+00 | 3.384E+00 | 1.024E+00 | 1.986E+00 | 1.558E+00 |
| 124 | 4.016E−02 | 3.232E−02 | 2.805E−02 | 3.224E−02 | 3.001E−02 | 3.411E−02 | 3.081E−02 | 3.268E−02 | 2.858E−02 | 1.719E−02 | 4.951E−02 | 2.226E−02 | 2.199E−02 |
| 125 | 1.603E−02 | 5.387E−02 | 5.138E−02 | 3.687E−02 | 1.104E−01 | 2.556E−02 | 4.800E−02 | 1.630E−02 | 8.575E−02 | 8.602E−03 | 6.189E−02 | 3.339E−02 | 2.565E−02 |
| 126 | 3.535E−01 | 2.369E−01 | 3.918E−01 | 3.544E−01 | 4.354E−01 | 2.600E−01 | 3.259E−01 | 2.289E−01 | 3.713E−01 | 1.674E−01 | 2.912E−01 | 1.131E+00 | 5.966E−01 |
| 127 | 1.033E+00 | 6.794E−01 | 1.184E+00 | 1.024E+00 | 1.077E+00 | 7.792E−01 | 9.528E−01 | 9.439E−01 | 7.996E−01 | 8.994E−01 | 1.069E+00 | 2.395E+00 | 9.261E−01 |
| 128 | 2.386E+00 | 1.799E+00 | 1.585E+00 | 9.083E−01 | 9.528E−01 | 9.261E−01 | 1.389E+00 | 1.683E+00 | 9.172E−01 | 2.663E+00 | 4.452E−01 | 2.102E+00 | 1.345E+00 |
| 129 | 6.821E−02 | 5.387E−02 | 3.268E−02 | 3.687E−02 | 3.998E−02 | 2.983E−02 | 5.824E−02 | 3.678E−02 | 3.428E−02 | 2.582E−02 | 1.852E−02 | 4.078E−02 | 3.660E−02 |
| 130 | 3.099E+00 | 2.600E+00 | 4.301E+00 | 8.648E+00 | 4.470E+00 | 4.381E+00 | 6.767E+00 | 2.431E+00 | 5.554E+00 | 2.137E+00 | 6.118E+00 | 7.652E+00 | 5.067E+00 |
| 131 | 2.760E+00 | 4.292E+00 | 4.479E+00 | 6.118E+00 | 4.069E+00 | 3.829E+00 | 5.761E+00 | 2.422E+00 | 3.767E+00 | 1.656E+00 | 5.521E+00 | 4.025E+00 | 4.764E+00 |
| 132 | 3.206E−02 | 7.542E−02 | 1.167E−01 | 5.984E−02 | 8.994E−02 | 4.256E−02 | 7.195E−02 | 8.575E−02 | 1.140E−01 | 6.456E−02 | 4.951E−02 | 3.339E−02 | 3.295E−02 |
| 133 | 2.404E−02 | 0.000E+00 | 2.333E−02 | 1.380E−02 | 2.502E−02 | 2.556E−02 | 1.710E−02 | 1.630E−02 | 3.998E−02 | 8.602E−03 | 1.238E−02 | 5.557E−02 | 1.825E−02 |
| 134 | 8.023E−03 | 1.621E−02 | 5.601E−02 | 1.380E−02 | 3.500E−02 | 2.983E−02 | 1.024E−02 | 4.898E−02 | 2.858E−02 | 3.010E−02 | 1.238E−02 | 2.965E−02 | 1.460E−02 |
| 135 | 8.023E−03 | 1.621E−02 | 3.268E−02 | 9.172E−03 | 9.973E−03 | 2.128E−02 | 1.371E−02 | 8.166E−03 | 2.289E−02 | 1.719E−02 | 6.189E−03 | 7.409E−03 | 1.095E−02 |
| 136 | 1.603E−02 | 1.077E−02 | 1.398E−02 | 1.380E−02 | 3.001E−02 | 8.522E−03 | 6.857E−03 | 2.449E−02 | 2.858E−02 | 2.155E−02 | 3.090E−02 | 1.852E−02 | 1.095E−02 |
| 137 | 8.825E−02 | 7.542E−02 | 6.536E−02 | 1.015E−01 | 7.507E−02 | 2.983E−02 | 7.195E−02 | 7.355E−02 | 8.575E−02 | 5.165E−02 | 2.476E−02 | 4.817E−02 | 7.685E−02 |
| 138 | 4.016E−02 | 1.077E−02 | 1.398E−02 | 1.843E−02 | 2.502E−02 | 1.701E−02 | 1.710E−02 | 1.229E−02 | 1.719E−02 | 1.380E−01 | 1.852E−02 | 5.557E−02 | 2.565E−02 |
| 139 | 4.337E−01 | 1.131E−01 | 9.350E−02 | 7.364E−02 | 1.247E−01 | 1.487E−01 | 1.710E−01 | 1.719E−01 | 1.033E−01 | 1.932E−01 | 9.884E−02 | 2.894E−01 | 2.707E−01 |
| 140 | 2.449E−01 | 1.131E−01 | 7.008E−02 | 3.687E−02 | 7.008E−02 | 8.522E−02 | 1.264E−01 | 1.549E−01 | 8.575E−02 | 2.191E−01 | 4.951E−02 | 1.300E−01 | 6.955E−02 |
| 141 | 4.016E−02 | 9.172E−02 | 7.471E−02 | 8.281E−02 | 7.008E−02 | 4.684E−02 | 5.485E−02 | 7.355E−02 | 5.147E−02 | 6.456E−02 | 2.351E−01 | 4.817E−02 | 4.390E−02 |
| 142 | 1.202E−02 | 0.000E+00 | 9.350E−03 | 9.172E−03 | 5.004E−03 | 1.282E−02 | 1.024E−02 | 2.449E−02 | 1.719E−02 | 4.728E−02 | 2.476E−02 | 2.226E−02 | 2.199E−02 |
| 143 | 4.016E−03 | 3.232E−02 | 1.870E−02 | 9.172E−03 | 3.001E−02 | 1.701E−02 | 1.710E−02 | 2.039E−02 | 3.998E−02 | 8.602E−03 | 1.852E−02 | 1.852E−02 | 2.930E−02 |
| 144 | 2.404E−02 | 2.155E−02 | 2.333E−02 | 2.297E−02 | 3.500E−02 | 0.000E+00 | 4.800E−02 | 7.355E−02 | 1.719E−02 | 3.874E−02 | 6.189E−03 | 3.339E−02 | 2.199E−02 |
| 145 | 3.615E−02 | 0.000E+00 | 2.333E−02 | 9.172E−03 | 3.500E−02 | 1.282E−02 | 1.710E−02 | 2.039E−02 | 2.289E−02 | 3.437E−02 | 0.000E+00 | 3.704E−02 | 2.199E−02 |
| 146 | 3.491E−01 | 1.345E−01 | 1.264E−01 | 2.075E−01 | 1.104E−01 | 1.532E−01 | 2.983E−01 | 2.618E−01 | 8.575E−02 | 1.852E−01 | 2.102E−01 | 3.411E−01 | 1.647E−01 |
| 147 | 1.327E−01 | 9.172E−02 | 7.008E−02 | 5.984E−02 | 7.008E−02 | 8.094E−02 | 1.264E−01 | 1.264E−01 | 4.568E−02 | 6.456E−02 | 1.549E−01 | 4.114E−01 | 1.576E−01 |

APPENDIX D-continued

Ovarian Cancer
Training Dataset

| | | | | | | | | | | | | | |
|---|---|---|---|---|---|---|---|---|---|---|---|---|---|
| 148 | 6.661E−01 | 2.155E−01 | 2.894E−01 | 1.469E−01 | 2.048E−01 | 2.769E−01 | 2.395E−01 | 3.108E−01 | 1.603E−01 | 3.571E−01 | 1.362E−01 | 8.522E−01 | 3.553E−01 |
| 149 | 1.327E−01 | 7.008E−02 | 6.536E−02 | 4.604E−02 | 9.973E−02 | 2.128E−02 | 4.452E−02 | 7.355E−02 | 2.289E−02 | 8.175E−02 | 1.300E−01 | 1.781E−01 | 6.955E−02 |
| 150 | 8.023E−02 | 5.387E−03 | 9.350E−03 | 2.297E−02 | 2.502E−02 | 2.556E−02 | 3.767E−02 | 4.898E−02 | 5.147E−02 | 3.874E−02 | 6.189E−03 | 2.591E−02 | 2.199E−02 |
| 151 | 3.206E−02 | 0.000E+00 | 1.870E−02 | 1.380E−02 | 1.505E−02 | 2.556E−02 | 2.395E−02 | 1.630E−02 | 6.287E−02 | 2.582E−02 | 1.238E−02 | 4.078E−02 | 1.095E−02 |
| 152 | 8.023E−03 | 2.155E−02 | 3.731E−02 | 4.604E−02 | 9.973E−03 | 3.838E−02 | 2.395E−02 | 3.678E−02 | 2.858E−02 | 8.602E−03 | 2.476E−02 | 1.478E−02 | 2.199E−02 |
| 153 | 2.404E−02 | 2.155E−02 | 1.398E−02 | 1.380E−02 | 1.505E−02 | 2.128E−02 | 1.371E−02 | 8.166E−03 | 3.428E−02 | 3.010E−02 | 6.189E−03 | 2.965E−02 | 1.460E−02 |
| 154 | 1.202E−02 | 3.776E−02 | 9.350E−03 | 4.604E−03 | 9.973E−03 | 1.282E−02 | 2.743E−02 | 2.449E−02 | 1.140E−02 | 1.291E−02 | 0.000E+00 | 2.591E−02 | 3.660E−03 |
| 155 | 3.206E−02 | 1.077E−02 | 4.203E−02 | 2.297E−02 | 3.998E−02 | 2.983E−02 | 2.395E−02 | 1.229E−02 | 1.140E−02 | 6.020E−02 | 4.328E−02 | 4.443E−02 | 2.565E−02 |
| 156 | 4.372E−01 | 3.615E−01 | 2.146E−01 | 3.179E−01 | 1.549E−01 | 2.467E−01 | 5.654E−01 | 3.188E−01 | 1.487E−01 | 2.413E−01 | 3.402E−01 | 3.037E−01 | 3.108E−01 |
| 157 | 1.728E−01 | 1.184E−01 | 4.666E−02 | 1.104E−01 | 8.504E−02 | 1.149E−01 | 2.155E−01 | 1.184E−01 | 7.427E−02 | 1.291E−01 | 1.736E−01 | 1.968E−01 | 1.612E−01 |
| 158 | 6.376E−01 | 2.476E−01 | 2.102E−01 | 2.760E−01 | 1.852E−01 | 3.321E−01 | 5.102E−01 | 4.372E−01 | 1.719E−01 | 3.526E−01 | 4.390E−01 | 5.815E−01 | 3.143E−01 |
| 159 | 1.443E−01 | 8.620E−02 | 7.008E−02 | 7.827E−02 | 5.004E−02 | 7.667E−02 | 8.905E−02 | 1.140E−01 | 6.287E−02 | 5.592E−02 | 1.113E−01 | 1.220E−01 | 1.247E−01 |
| 160 | 2.404E−02 | 3.232E−02 | 3.268E−02 | 1.380E−02 | 2.502E−02 | 1.701E−02 | 2.743E−02 | 4.087E−02 | 2.858E−02 | 3.437E−02 | 2.476E−02 | 5.557E−02 | 2.565E−02 |
| 161 | 8.424E−02 | 2.698E−02 | 3.731E−02 | 0.000E+00 | 2.004E−02 | 1.701E−02 | 1.710E−02 | 6.536E−02 | 1.719E−02 | 2.155E−02 | 4.328E−02 | 2.965E−02 | 2.199E−02 |
| 162 | 1.202E−02 | 1.077E−02 | 1.398E−02 | 9.172E−03 | 9.973E−03 | 0.000E+00 | 3.081E−02 | 1.229E−02 | 2.289E−02 | 2.582E−02 | 3.713E−02 | 2.591E−02 | 5.120E−02 |
| 163 | 1.603E−02 | 4.310E−02 | 1.398E−02 | 9.172E−03 | 2.004E−02 | 4.256E−03 | 2.057E−02 | 2.039E−02 | 2.858E−02 | 2.155E−02 | 1.852E−02 | 2.226E−02 | 2.565E−02 |
| 164 | 1.202E−02 | 1.621E−02 | 2.805E−02 | 1.380E−02 | 3.001E−02 | 8.522E−03 | 3.428E−02 | 8.166E−03 | 1.719E−02 | 2.582E−02 | 1.852E−02 | 7.409E−03 | 1.825E−02 |
| 165 | 1.202E−02 | 5.87E−03 | 2.805E−02 | 0.380E−02 | 0.000E+00 | 1.701E−02 | 2.743E−02 | 2.449E−02 | 3.998E−02 | 3.874E−02 | 6.189E−03 | 4.078E−02 | 5.850E−02 |
| 166 | 8.825E−02 | 3.776E−02 | 3.731E−02 | 5.067E−02 | 2.502E−02 | 3.411E−02 | 6.171E−02 | 3.268E−02 | 3.428E−02 | 8.602E−02 | 6.803E−02 | 8.148E−02 | 4.025E−02 |
| 167 | 3.330E−01 | 2.369E−01 | 1.354E−01 | 1.612E−01 | 1.149E−01 | 9.795E−02 | 2.814E−01 | 1.719E−01 | 1.318E−01 | 1.247E−01 | 2.413E−01 | 2.110E−01 | 1.719E−01 |
| 168 | 2.164E−01 | 1.077E−01 | 6.073E−02 | 7.364E−02 | 9.528E−02 | 8.094E−02 | 1.060E−01 | 1.469E−01 | 2.289E−02 | 1.033E−01 | 1.612E−01 | 9.973E−02 | 8.780E−02 |
| 169 | 8.023E−02 | 4.853E−02 | 6.536E−02 | 8.281E−02 | 5.503E−02 | 2.983E−02 | 4.452E−02 | 3.678E−02 | 5.717E−02 | 5.165E−02 | 7.427E−02 | 5.931E−02 | 6.589E−02 |
| 170 | 8.023E−02 | 4.853E−02 | 2.805E−02 | 4.141E−02 | 5.004E−02 | 2.983E−02 | 1.710E−02 | 6.536E−02 | 1.140E−02 | 9.439E−02 | 2.476E−02 | 4.443E−02 | 3.660E−02 |
| 171 | 6.020E−02 | 4.310E−02 | 4.203E−02 | 9.172E−03 | 5.503E−02 | 1.701E−02 | 2.395E−02 | 6.536E−02 | 2.289E−02 | 2.155E−02 | 1.238E−02 | 8.522E−02 | 2.199E−02 |
| 172 | 5.690E−02 | 8.093E−02 | 1.447E−01 | 7.738E−02 | 1.300E−01 | 6.340E−02 | 7.836E−02 | 6.131E−02 | 8.657E−02 | 6.573E−02 | 8.694E−02 | 4.181E−02 | 5.849E−02 |
| 173 | 1.807E+00 | 3.410E+00 | 3.339E+00 | 2.396E+00 | 3.973E+00 | 1.894E+00 | 1.915E+00 | 2.763E+00 | 5.191E+00 | 2.990E+00 | 1.295E+00 | 1.985E+00 | 2.284E+00 |
| 174 | 3.105E+00 | 6.005E+00 | 5.345E+00 | 4.300E+00 | 6.940E+00 | 3.480E+00 | 3.279E+00 | 4.927E+00 | 9.481E+00 | 5.279E+00 | 1.621E+00 | 3.708E+00 | 4.126E+00 |
| 175 | 6.462E−01 | 1.130E+00 | 1.313E+00 | 9.197E−01 | 1.478E+00 | 6.891E−01 | 7.382E−01 | 9.938E−01 | 1.685E+00 | 9.828E−01 | 4.697E−01 | 8.675E−01 | 8.434E−01 |
| 176 | 1.695E+00 | 2.484E+00 | 3.438E+00 | 1.791E+00 | 2.803E+00 | 2.168E+00 | 2.036E+00 | 2.115E+00 | 3.611E+00 | 3.219E+00 | 1.502E+00 | 2.053E+00 | 2.310E+00 |
| 177 | 5.579E−01 | 6.891E−01 | 1.008E+00 | 1.566E+00 | 1.086E+00 | 8.893E−01 | 1.308E+00 | 4.598E−01 | 1.105E+00 | 7.227E−01 | 5.935E−01 | 8.445E−01 | 8.943E−01 |
| 178 | 8.338E−02 | 1.218E−01 | 1.631E−01 | 1.594E−01 | 2.551E−01 | 1.275E−01 | 2.048E−01 | 6.070E−02 | 1.521E−01 | 1.072E−01 | 1.410E−01 | 1.496E−01 | 2.367E−01 |
| 179 | 1.275E−02 | 3.041E−02 | 3.017E−02 | 1.717E−02 | 3.716E−02 | 1.876E−02 | 2.121E−02 | 1.124E−02 | 2.514E−02 | 1.901E−02 | 1.704E−02 | 2.097E−02 | 2.820E−02 |
| 180 | 1.435E−02 | 2.600E−02 | 3.151E−02 | 1.398E−02 | 2.685E−02 | 1.174E−02 | 6.609E−03 | 2.649E−02 | 2.600E−02 | 2.367E−02 | 1.193E−02 | 1.072E−02 | 1.815E−02 |
| 181 | 1.050E−02 | 2.526E−02 | 1.925E−02 | 1.140E−02 | 2.416E−02 | 1.521E−02 | 1.133E−02 | 1.239E−02 | 3.151E−02 | 1.950E−02 | 1.704E−02 | 9.700E−03 | 2.060E−02 |
| 182 | 6.524E−02 | 2.636E−01 | 2.048E−01 | 2.465E−01 | 2.526E−01 | 8.155E−02 | 1.034E−01 | 1.091E−01 | 2.661E−01 | 1.042E−01 | 6.156E−01 | 7.345E−02 | 9.368E−02 |
| 183 | 1.746E+00 | 3.086E+00 | 3.003E+00 | 2.709E+00 | 3.690E+00 | 1.519E+00 | 1.702E+00 | 2.175E+00 | 3.500E+00 | 2.098E+00 | 5.457E+00 | 1.327E+00 | 1.525E+00 |
| 184 | 1.884E+00 | 3.631E+00 | 3.030E+00 | 3.378E+00 | 4.024E+00 | 1.649E+00 | 2.136E+00 | 2.328E+00 | 4.196E+00 | 2.605E+00 | 6.608E+00 | 1.519E+00 | 1.751E+00 |
| 185 | 1.390E+00 | 2.686E+00 | 2.186E+00 | 2.120E+00 | 2.909E+00 | 1.194E+00 | 1.247E+00 | 1.697E+00 | 2.909E+00 | 1.879E+00 | 4.269E+00 | 1.174E+00 | 1.315E+00 |
| 186 | 2.736E+00 | 4.819E+00 | 4.111E+00 | 4.038E+00 | 5.295E+00 | 2.664E+00 | 2.937E+00 | 3.481E+00 | 5.076E+00 | 3.246E+00 | 6.914E+00 | 2.261E+00 | 2.726E+00 |
| 187 | 5.408E−01 | 8.437E−01 | 9.921E−01 | 7.627E−01 | 1.077E+00 | 5.445E−01 | 5.788E−01 | 6.769E−01 | 9.946E−01 | 5.751E−01 | 1.554E+00 | 4.942E−01 | 4.954E−01 |
| 188 | 4.365E−02 | 8.461E−02 | 1.126E−01 | 7.922E−02 | 9.234E−02 | 4.574E−02 | 4.292E−02 | 5.395E−02 | 7.946E−02 | 5.690E−02 | 1.754E−01 | 5.310E−02 | 3.826E−02 |
| 189 | 5.530E−03 | 2.379E−02 | 1.668E−02 | 1.140E−02 | 3.519E−02 | 1.056E−02 | 8.964E−03 | 1.181E−02 | 1.570E−02 | 1.300E−02 | 8.007E−02 | 1.020E−02 | 1.263E−02 |
| 190 | 1.471E−01 | 1.422E−01 | 2.833E−01 | 2.060E−01 | 2.318E−01 | 1.704E−01 | 1.337E−01 | 1.655E−01 | 2.293E−01 | 2.085E−01 | 6.033E−01 | 2.036E−01 | 1.974E−01 |
| 191 | 1.692E+00 | 2.156E+00 | 2.805E+00 | 5.504E+00 | 3.058E+00 | 2.582E+00 | 4.029E+00 | 1.147E+00 | 2.494E+00 | 1.769E+00 | 7.121E+00 | 2.007E+00 | 2.206E+00 |
| 192 | 3.936E−01 | 6.229E−01 | 6.818E−01 | 1.034E+00 | 8.990E−01 | 6.340E−01 | 9.933E−01 | 2.698E−01 | 6.119E−01 | 4.096E−01 | 2.137E+00 | 5.015E−01 | 6.830E−01 |
| 193 | 6.413E−02 | 1.196E−01 | 1.164E−01 | 1.072E−01 | 1.680E−01 | 8.387E−02 | 1.075E−01 | 6.462E−02 | 1.459E−01 | 7.578E−02 | 3.139E−01 | 8.927E−02 | 1.023E−01 |
| 194 | 1.337E−01 | 1.135E−01 | 1.459E−01 | 7.860E−02 | 1.557E−01 | 9.381E−02 | 6.413E−02 | 1.398E−01 | 1.643E−01 | 1.888E−01 | 1.631E−01 | 9.442E−02 | 9.822E−02 |
| 195 | 5.248E−02 | 3.262E−02 | 6.499E−02 | 4.942E−02 | 6.401E−02 | 3.348E−02 | 2.882E−02 | 6.242E−02 | 7.787E−02 | 9.185E−02 | 6.818E−02 | 3.679E−02 | 4.733E−02 |
| 196 | 7.738E−02 | 2.379E−01 | 2.587E−01 | 2.563E−01 | 2.244E−01 | 1.203E−01 | 2.575E−01 | 1.091E−01 | 1.410E−01 | 6.401E−02 | 4.034E−01 | 9.393E−02 | 1.058E−01 |
| 197 | 6.744E−02 | 1.203E−01 | 1.533E−01 | 1.852E−01 | 1.508E−01 | 9.565E−02 | 1.373E−01 | 5.457E−02 | 1.094E−01 | 6.217E−02 | 3.335E−01 | 6.070E−02 | 7.357E−02 |

APPENDIX D-continued

Ovarian Cancer Training Dataset

| | | | | | | | | | | | | | |
|---|---|---|---|---|---|---|---|---|---|---|---|---|---|
| 198 | 5.310E−02 | 7.492E−02 | 7.774E−02 | 7.799E−02 | 6.953E−02 | 5.395E−02 | 6.560E−02 | 3.765E−02 | 6.143E−02 | 6.340E−02 | 1.925E−01 | 4.893E−02 | 4.733E−02 |
| 199 | 2.072E−01 | 1.619E−01 | 1.754E−01 | 5.457E−02 | 1.459E−01 | 1.839E−01 | 6.082E−02 | 1.046E−01 | 1.447E−01 | 1.852E−01 | 1.606E−01 | 9.896E−02 | 1.361E−01 |
| 200 | 8.952E−02 | 1.471E−01 | 1.221E−01 | 6.720E−02 | 1.373E−01 | 9.086E−02 | 4.525E−02 | 8.044E−02 | 1.459E−01 | 1.191E−01 | 1.643E−01 | 6.536E−02 | 7.860E−02 |
| 201 | 6.744E−02 | 4.525E−02 | 7.272E−02 | 4.181E−02 | 6.757E−02 | 3.924E−02 | 4.341E−02 | 6.744E−02 | 8.179E−02 | 8.118E−02 | 6.303E−02 | 4.746E−02 | 5.641E−02 |
| 202 | 6.634E−03 | 1.113E−02 | 1.410E−02 | 1.263E−03 | 4.132E−03 | 8.804E−03 | 1.888E−03 | 4.500E−03 | 1.337E−02 | 1.126E−02 | 1.193E−02 | 4.083E−03 | 8.559E−03 |
| 203 | 1.105E−03 | 1.484E−03 | 0.000E+00 | 1.263E−03 | 0.000E+00 | 1.174E−03 | 0.000E+00 | 5.628E−04 | 2.367E−03 | 1.185E−03 | 3.409E−03 | 2.036E−03 | 5.040E−04 |
| 204 | 6.634E−03 | 8.167E−03 | 1.029E−02 | 1.263E−03 | 5.506E−03 | 1.115E−02 | 6.131E−03 | 7.308E−03 | 1.337E−02 | 1.067E−02 | 1.193E−02 | 6.634E−03 | 1.410E−02 |
| 205 | 1.105E−03 | 7.419E−04 | 0.000E+00 | 6.340E−04 | 6.891E−04 | 5.861E−04 | 1.410E−03 | 0.000E+00 | 2.367E−03 | 1.778E−03 | 8.522E−04 | 0.000E+00 | 1.508E−03 |
| 206 | 1.496E−02 | 1.631E−02 | 2.379E−02 | 1.901E−03 | 1.373E−02 | 1.349E−02 | 6.131E−03 | 3.372E−03 | 2.440E−02 | 2.305E−02 | 5.960E−03 | 1.072E−02 | 1.109E−02 |
| 207 | 5.530E−04 | 0.000E+00 | 0.000E+00 | 0.000E+00 | 0.000E+00 | 2.342E−03 | 4.721E−04 | 1.124E−03 | 1.570E−03 | 5.923E−04 | 8.522E−04 | 1.020E−03 | 0.000E+00 |
| 208 | 7.738E−03 | 6.683E−03 | 7.075E−03 | 6.340E−04 | 2.759E−03 | 4.697E−03 | 1.888E−03 | 3.936E−03 | 5.506E−03 | 4.145E−03 | 7.664E−03 | 5.101E−03 | 2.011E−03 |
| 209 | 5.530E−04 | 7.419E−04 | 1.288E−03 | 0.000E+00 | 0.000E+00 | 0.000E+00 | 0.000E+00 | 1.124E−03 | 1.570E−03 | 1.778E−03 | 0.000E+00 | 5.101E−04 | 1.008E−03 |
| 210 | 0.000E+00 | 7.419E−04 | 0.000E+00 | 0.000E+00 | 0.000E+00 | 1.174E−03 | 9.442E−04 | 0.000E+00 | 0.000E+00 | 0.000E+00 | 1.704E−03 | 1.020E−03 | 5.040E−04 |
| 211 | 5.530E−04 | 3.716E−03 | 1.288E−03 | 6.340E−04 | 6.891E−04 | 0.000E+00 | 4.721E−04 | 0.000E+00 | 2.367E−03 | 0.000E+00 | 0.000E+00 | 5.101E−04 | 0.000E+00 |
| 212 | 0.000E+00 | 7.419E−04 | 6.426E−04 | 0.000E+00 | 1.373E−03 | 0.000E+00 | 0.000E+00 | 5.628E−04 | 0.000E+00 | 5.923E−04 | 8.522E−04 | 5.101E−04 | 2.011E−03 |
| 213 | 4.414E−03 | 5.935E−03 | 3.863E−03 | 1.901E−03 | 2.072E−03 | 1.174E−03 | 1.888E−03 | 1.124E−03 | 3.151E−03 | 5.923E−03 | 3.409E−03 | 3.066E−03 | 2.514E−03 |
| 214 | 3.311E−03 | 1.484E−03 | 1.925E−03 | 1.901E−03 | 2.759E−03 | 5.861E−04 | 2.354E−03 | 1.692E−03 | 7.872E−04 | 6.511E−03 | 3.409E−03 | 1.020E−03 | 1.508E−03 |
| 215 | 0.000E+00 | 1.484E−03 | 1.288E−03 | 6.340E−04 | 0.000E+00 | 0.000E+00 | 9.442E−04 | 2.244E−03 | 2.367E−03 | 2.367E−03 | 0.000E+00 | 1.020E−03 | 0.000E+00 |
| 216 | 0.000E+00 | 0.000E+00 | 0.000E+00 | 0.000E+00 | 6.891E−04 | 5.861E−04 | 0.000E+00 | 2.244E−03 | 3.151E−03 | 0.000E+00 | 0.000E+00 | 0.000E+00 | 0.000E+00 |
| 217 | 5.530E−04 | 1.484E−03 | 0.000E+00 | 1.901E−03 | 6.891E−04 | 0.000E+00 | 0.000E+00 | 1.124E−03 | 0.000E+00 | 1.185E−03 | 1.704E−03 | 1.020E−03 | 5.040E−04 |
| 218 | 1.915E+00 | 3.498E+00 | 3.515E+00 | 3.043E+00 | 3.764E+00 | 1.637E+00 | 2.004E+00 | 2.259E+00 | 4.079E+00 | 2.242E+00 | 6.758E+00 | 1.488E+00 | 1.434E+00 |
| 219 | 1.655E−02 | 2.747E−02 | 3.863E−02 | 2.784E−02 | 4.758E−02 | 1.704E−02 | 1.180E−02 | 2.244E−02 | 3.703E−02 | 1.839E−02 | 9.123E−02 | 1.680E−02 | 2.722E−02 |
| 220 | 1.223E+00 | 1.567E+00 | 1.912E+00 | 8.505E−01 | 1.812E+00 | 1.279E+00 | 9.872E−01 | 1.119E+00 | 1.206E+00 | 2.124E+00 | 8.478E−01 | 1.334E+00 | 1.641E+00 |
| 221 | 4.627E+01 | 6.095E+01 | 7.581E+01 | 3.876E+01 | 4.881E+01 | 6.549E+01 | 4.710E+01 | 5.468E+01 | 6.449E+01 | 6.448E+01 | 2.203E+01 | 5.131E+01 | 5.032E+01 |
| 222 | 3.660E+01 | 2.946E+01 | 3.438E+01 | 2.693E+01 | 3.778E+01 | 4.025E+01 | 3.302E+01 | 4.114E+01 | 3.499E+01 | 3.335E+01 | 1.004E+01 | 5.639E+01 | 5.316E+01 |
| 223 | 2.284E+01 | 2.338E+01 | 2.258E+01 | 1.691E+01 | 2.244E+01 | 2.419E+01 | 1.979E+01 | 2.474E+01 | 1.889E+01 | 3.372E+01 | 7.574E+00 | 2.902E+01 | 2.443E+01 |
| 224 | 1.597E+01 | 1.815E+01 | 2.573E+01 | 9.762E+00 | 1.803E+01 | 1.731E+01 | 1.337E+01 | 2.112E+01 | 1.992E+01 | 2.193E+01 | 5.324E+00 | 2.061E+01 | 2.202E+01 |
| 225 | 9.622E+00 | 1.185E+01 | 1.123E+01 | 1.876E+01 | 1.129E+01 | 1.799E+01 | 2.232E+01 | 1.270E+01 | 1.143E+01 | 1.011E+01 | 1.308E+01 | 1.449E+01 | 1.260E+01 |
| 226 | 2.930E+00 | 7.026E+00 | 6.209E+00 | 5.524E+00 | 5.142E+00 | 6.596E+00 | 7.300E+00 | 5.194E+00 | 5.112E+00 | 2.056E+00 | 2.766E+00 | 4.730E+00 | 6.335E+00 |
| 227 | 1.186E+00 | 2.172E+00 | 1.865E+00 | 2.377E+00 | 1.912E+00 | 2.204E+00 | 2.033E+00 | 1.709E+00 | 2.081E+00 | 1.006E+00 | 1.437E+00 | 2.105E+00 | 1.972E+00 |
| 228 | 2.931E−01 | 4.278E−01 | 6.723E−01 | 1.497E−01 | 3.378E−01 | 2.650E−01 | 2.167E−01 | 3.321E−01 | 3.311E−01 | 2.856E−01 | 2.928E−01 | 2.312E−01 | 3.629E−01 |
| 229 | 2.862E−01 | 4.197E−01 | 6.737E−01 | 1.476E−01 | 3.667E−01 | 3.144E−01 | 2.245E−01 | 3.458E−01 | 3.701E−01 | 2.653E−01 | 3.060E−01 | 2.606E−01 | 3.780E−01 |
| 230 | 3.321E+01 | 2.790E+01 | 3.076E+01 | 3.316E+01 | 2.891E+01 | 4.116E+01 | 4.041E+01 | 3.476E+01 | 3.597E+01 | 3.230E+01 | 2.164E+01 | 3.818E+01 | 3.440E+01 |
| 231 | 3.985E+00 | 4.143E+00 | 4.861E+00 | 3.889E+00 | 4.152E+00 | 4.415E+00 | 5.403E+00 | 3.879E+00 | 3.979E+00 | 3.447E+00 | 3.464E+00 | 3.803E+00 | 4.342E+00 |
| 232 | 1.088E+00 | 1.883E+00 | 1.713E+00 | 1.292E+00 | 1.694E+00 | 1.735E+00 | 1.354E+00 | 1.906E+00 | 1.984E+00 | 1.398E+00 | 1.833E+00 | 1.683E+00 | 1.693E+00 |
| 233 | 5.075E+00 | 5.121E+00 | 5.374E+00 | 5.326E+00 | 4.680E+00 | 5.882E+00 | 4.335E+00 | 4.406E+00 | 5.235E+00 | 6.011E+00 | 4.456E+00 | 6.466E+00 | 5.422E+00 |
| 234 | 2.251E+01 | 2.007E+01 | 1.768E+01 | 1.597E+01 | 1.827E+01 | 1.723E+01 | 1.812E+01 | 1.654E+01 | 1.507E+01 | 2.907E+01 | 1.976E+01 | 1.385E+01 | 1.675E+01 |
| 235 | 1.276E+01 | 1.329E+01 | 1.072E+01 | 1.250E+01 | 1.116E+01 | 1.133E+01 | 1.282E+01 | 1.308E+01 | 1.067E+01 | 1.745E+01 | 1.018E+01 | 8.974E+00 | 9.408E+00 |
| 236 | 4.674E−01 | 7.908E−01 | 8.850E−01 | 2.928E−01 | 7.331E−01 | 6.894E−01 | 3.579E−01 | 7.464E−01 | 8.547E−01 | 5.194E−01 | 5.714E−01 | 6.733E−01 | 8.758E−01 |
| 237 | 2.318E+00 | 3.467E+00 | 3.386E+00 | 3.172E+00 | 5.148E+00 | 3.120E+00 | 2.527E+00 | 3.186E+00 | 4.263E+00 | 2.077E+00 | 4.946E+00 | 5.046E+00 | 6.176E+00 |
| 238 | 5.299E+00 | 6.697E+00 | 5.883E+00 | 6.531E+00 | 7.314E+00 | 5.273E+00 | 5.948E+00 | 7.577E+00 | 5.938E+00 | 6.423E+00 | 9.290E+00 | 6.526E+00 | 7.336E+00 |
| 239 | 1.175E+00 | 1.351E+00 | 1.342E+00 | 1.233E+00 | 1.398E+00 | 1.127E+00 | 1.126E+00 | 1.727E+00 | 1.412E+00 | 1.419E+00 | 2.278E+00 | 1.343E+00 | 1.495E+00 |
| 240 | 2.131E+01 | 1.971E+01 | 1.972E+01 | 4.473E+00 | 1.592E+01 | 1.284E+01 | 5.463E+00 | 2.265E+01 | 1.612E+01 | 2.473E+01 | 1.100E+01 | 1.651E+01 | 1.564E+01 |
| 241 | 2.803E+02 | 2.581E+02 | 2.508E+02 | 2.514E+02 | 2.707E+02 | 2.381E+02 | 2.248E+02 | 2.541E+02 | 2.760E+02 | 2.422E+02 | 2.435E+02 | 2.556E+02 | 2.592E+02 |
| 242 | 1.898E+02 | 2.053E+02 | 1.719E+02 | 1.771E+02 | 1.758E+02 | 1.561E+02 | 1.553E+02 | 1.690E+02 | 1.571E+02 | 2.413E+02 | 2.076E+02 | 1.427E+02 | 1.479E+02 |
| 243 | 1.662E+01 | 1.912E+01 | 1.532E+01 | 1.589E+01 | 1.516E+01 | 1.397E+01 | 1.381E+01 | 1.479E+01 | 1.307E+01 | 2.157E+01 | 1.779E+01 | 1.178E+01 | 1.263E+01 |
| 244 | 5.402E+00 | 1.003E+01 | 8.495E+00 | 1.434E+01 | 1.149E+01 | 8.333E+00 | 1.107E+01 | 6.631E+00 | 8.639E+00 | 5.650E+00 | 1.257E+01 | 1.040E+01 | 7.068E+00 |
| 245 | 3.270E+00 | 5.063E+00 | 3.928E+00 | 4.794E+00 | 6.355E+00 | 4.155E+00 | 3.805E+00 | 4.375E+00 | 4.512E+00 | 2.954E+00 | 6.291E+00 | 5.719E+00 | 5.495E+00 |
| 246 | 5.387E+00 | 6.089E+00 | 6.735E+00 | 4.921E+00 | 7.627E+00 | 5.080E+00 | 3.965E+00 | 9.040E+00 | 7.416E+00 | 6.299E+00 | 1.090E+01 | 7.622E+00 | 8.771E+00 |
| 247 | 3.544E+00 | 5.424E+00 | 5.074E+00 | 3.500E+00 | 4.849E+00 | 4.158E+00 | 3.148E+00 | 5.565E+00 | 5.750E+00 | 4.163E+00 | 9.138E+00 | 4.391E+00 | 5.523E+00 |

APPENDIX D-continued

Ovarian Cancer
Training Dataset

| | | | | | | | | | | | | | |
|---|---|---|---|---|---|---|---|---|---|---|---|---|---|
| 248 | 6.463E+01 | 7.888E+01 | 7.099E+01 | 1.384E+02 | 7.232E+01 | 9.417E+01 | 1.232E+02 | 6.516E+01 | 7.366E+01 | 5.918E+01 | 1.444E+02 | 6.709E+01 | 6.504E+01 |
| 249 | 5.262E+01 | 6.934E+01 | 6.088E+01 | 6.159E+01 | 7.656E+01 | 5.538E+01 | 6.268E+01 | 5.138E+01 | 4.404E+01 | 4.683E+01 | 1.051E+02 | 7.199E+01 | 6.396E+01 |
| 250 | 1.245E+02 | 1.119E+02 | 1.362E+02 | 9.982E+01 | 1.484E+02 | 9.095E+01 | 9.276E+01 | 1.239E+02 | 1.142E+02 | 1.038E+02 | 1.158E+02 | 1.395E+02 | 1.482E+02 |
| 251 | 5.714E+01 | 5.244E+01 | 5.579E+01 | 3.189E+01 | 5.318E+01 | 4.253E+01 | 3.494E+01 | 5.318E+01 | 4.541E+01 | 5.707E+01 | 4.425E+01 | 4.934E+01 | 5.189E+01 |
| 252 | 3.943E+00 | 4.116E+00 | 4.254E+00 | 2.140E+00 | 3.698E+00 | 3.193E+00 | 2.491E+00 | 3.892E+00 | 3.285E+00 | 4.280E+00 | 3.243E+00 | 3.411E+00 | 3.312E+00 |
| 253 | 2.554E+00 | 4.895E+00 | 4.323E+00 | 3.230E+00 | 4.471E+00 | 3.360E+00 | 3.308E+00 | 3.401E+00 | 4.256E+00 | 2.910E+00 | 4.130E+00 | 3.663E+00 | 3.444E+00 |
| 254 | 5.959E+00 | 1.029E+01 | 7.735E+00 | 1.480E+01 | 1.135E+01 | 7.761E+00 | 1.080E+01 | 7.995E+00 | 8.323E+00 | 5.668E+00 | 1.346E+01 | 9.661E+00 | 7.488E+00 |
| 255 | 5.779E+00 | 9.141E+00 | 7.046E+00 | 1.220E+01 | 1.039E+01 | 7.543E+00 | 9.716E+00 | 7.749E+00 | 7.872E+00 | 5.007E+00 | 1.611E+01 | 8.660E+00 | 6.735E+00 |
| 256 | 2.311E+00 | 5.183E+00 | 3.232E+00 | 2.666E+00 | 4.477E+00 | 2.803E+00 | 2.595E+00 | 3.444E+00 | 3.513E+00 | 2.385E+00 | 6.979E+00 | 2.937E+00 | 2.797E+00 |
| 257 | 3.413E+00 | 5.168E+00 | 5.636E+00 | 3.521E+00 | 5.360E+00 | 5.252E+00 | 3.526E+00 | 6.011E+00 | 6.371E+00 | 4.161E+00 | 6.871E+00 | 5.485E+00 | 5.757E+00 |
| 258 | 1.641E+01 | 2.936E+01 | 2.701E+01 | 3.736E+01 | 2.626E+01 | 2.474E+01 | 2.554E+01 | 2.170E+01 | 2.664E+01 | 1.477E+01 | 4.685E+01 | 2.245E+01 | 2.181E+01 |
| 259 | 3.356E+01 | 4.472E+01 | 4.217E+01 | 6.925E+01 | 4.751E+01 | 4.453E+01 | 6.085E+01 | 4.097E+01 | 4.117E+01 | 3.152E+01 | 8.475E+01 | 4.146E+01 | 4.237E+01 |
| 260 | 2.958E+01 | 3.758E+01 | 3.412E+01 | 3.101E+01 | 3.992E+01 | 3.664E+01 | 3.595E+01 | 3.280E+01 | 3.033E+01 | 3.053E+01 | 5.358E+01 | 3.251E+01 | 3.762E+01 |
| 261 | 3.333E+01 | 3.144E+01 | 3.286E+01 | 2.994E+01 | 3.105E+01 | 3.917E+01 | 4.272E+01 | 3.835E+01 | 3.474E+01 | 3.854E+01 | 3.118E+01 | 3.131E+01 | 3.341E+01 |
| 262 | 1.217E+01 | 1.218E+01 | 1.333E+01 | 7.652E+00 | 1.130E+01 | 1.492E+01 | 1.104E+01 | 1.355E+01 | 1.409E+01 | 1.036E+01 | 7.603E+00 | 1.132E+01 | 1.270E+01 |
| 263 | 1.672E+00 | 4.023E+00 | 3.207E+00 | 3.287E+00 | 3.713E+00 | 2.584E+00 | 2.859E+00 | 2.876E+00 | 3.399E+00 | 1.510E+00 | 5.359E+00 | 2.597E+00 | 2.596E+00 |
| 264 | 2.236E+00 | 6.262E+00 | 3.524E+00 | 3.517E+00 | 4.735E+00 | 2.784E+00 | 2.807E+00 | 3.285E+00 | 3.899E+00 | 2.089E+00 | 5.523E+00 | 2.649E+00 | 2.161E+00 |
| 265 | 1.984E+00 | 3.771E+00 | 2.721E+00 | 2.468E+00 | 3.573E+00 | 2.337E+00 | 2.059E+00 | 2.522E+00 | 3.090E+00 | 2.032E+00 | 4.173E+00 | 2.196E+00 | 1.707E+00 |
| 266 | 2.290E+00 | 3.788E+00 | 3.302E+00 | 9.161E−01 | 2.721E+00 | 2.016E+00 | 1.218E+00 | 2.867E+00 | 3.520E+00 | 3.178E+00 | 3.210E+00 | 2.034E+00 | 1.807E+00 |
| 267 | 2.059E+00 | 3.150E+00 | 3.043E+00 | 9.519E−01 | 2.440E+00 | 1.937E+00 | 1.491E+00 | 3.094E+00 | 2.962E+00 | 2.869E+00 | 3.625E+00 | 2.065E+00 | 1.927E+00 |
| 268 | 8.228E+00 | 1.808E+01 | 1.770E+01 | 1.560E+01 | 1.207E+01 | 8.909E+00 | 1.444E+01 | 1.120E+01 | 1.066E+01 | 4.470E+00 | 1.644E+01 | 7.869E+00 | 1.024E+01 |
| 269 | 7.522E+00 | 1.248E+01 | 1.242E+01 | 8.006E+00 | 8.449E+00 | 8.705E+00 | 7.027E+00 | 8.319E+00 | 9.164E+00 | 5.124E+00 | 1.239E+01 | 6.057E+00 | 7.703E+00 |
| 270 | 3.801E+00 | 5.050E+00 | 4.790E+00 | 2.910E+00 | 4.018E+00 | 3.858E+00 | 2.661E+00 | 3.696E+00 | 4.120E+00 | 3.369E+00 | 6.029E+00 | 3.168E+00 | 3.258E+00 |
| 271 | 9.909E+00 | 1.104E+01 | 1.174E+01 | 1.273E+01 | 1.116E+01 | 1.537E+01 | 1.181E+01 | 1.120E+01 | 1.368E+01 | 1.165E+01 | 7.219E+00 | 1.499E+01 | 1.367E+01 |
| 272 | 8.130E+01 | 6.646E+01 | 7.021E+01 | 8.304E+01 | 7.019E+01 | 9.739E+01 | 9.383E+01 | 8.563E+01 | 8.794E+01 | 7.850E+01 | 5.131E+01 | 9.237E+01 | 8.753E+01 |
| 273 | 9.167E+01 | 7.562E+01 | 8.467E+01 | 9.650E+01 | 8.332E+01 | 1.105E+02 | 1.075E+02 | 9.959E+01 | 1.029E+02 | 9.026E+01 | 6.011E+01 | 1.031E+02 | 9.801E+01 |
| 274 | 1.422E+01 | 1.134E+01 | 1.255E+01 | 1.515E+01 | 1.166E+01 | 1.659E+01 | 1.914E+01 | 1.354E+01 | 1.368E+01 | 1.207E+01 | 7.824E+00 | 1.445E+01 | 1.309E+01 |
| 275 | 6.334E−01 | 6.038E−01 | 5.900E−01 | 6.687E−01 | 5.490E−01 | 6.661E−01 | 5.695E−01 | 7.700E−01 | 7.766E−01 | 7.206E−01 | 6.831E−01 | 1.327E+00 | 6.823E−01 |
| 276 | 9.246E+00 | 8.338E+00 | 7.330E+00 | 1.071E+01 | 6.691E+00 | 1.077E+01 | 8.050E+00 | 8.127E+00 | 9.462E+00 | 1.165E+01 | 6.673E+00 | 1.245E+01 | 7.972E+00 |
| 277 | 3.224E+01 | 2.137E+01 | 1.775E+01 | 2.539E+01 | 1.600E+01 | 2.707E+01 | 2.897E+01 | 2.455E+01 | 2.395E+01 | 3.680E+01 | 1.775E+01 | 2.315E+01 | 1.976E+01 |
| 278 | 3.229E+01 | 2.142E+01 | 1.841E+01 | 2.610E+01 | 1.620E+01 | 2.744E+01 | 2.951E+01 | 2.521E+01 | 2.378E+01 | 3.683E+01 | 1.794E+01 | 2.296E+01 | 1.972E+01 |
| 279 | 1.007E+01 | 8.045E+00 | 6.919E+00 | 7.633E+00 | 6.245E+00 | 6.908E+00 | 9.569E+00 | 6.027E+00 | 5.853E+00 | 1.055E+01 | 6.551E+00 | 4.888E+00 | 5.396E+00 |
| 280 | 7.097E+00 | 6.492E+00 | 7.119E+00 | 4.393E+00 | 5.949E+00 | 6.072E+00 | 3.748E+00 | 7.786E+00 | 6.625E+00 | 8.561E+00 | 5.091E+00 | 7.564E+00 | 6.323E+00 |
| 281 | 1.341E+02 | 1.223E+02 | 1.240E+02 | 1.317E+02 | 1.255E+02 | 1.178E+02 | 1.163E+02 | 1.230E+02 | 1.290E+02 | 1.106E+02 | 1.129E+02 | 1.223E+02 | 1.267E+02 |
| 282 | 1.179E+02 | 1.064E+02 | 1.078E+02 | 1.158E+02 | 1.082E+02 | 1.011E+02 | 1.018E+02 | 1.037E+02 | 1.082E+02 | 9.641E+01 | 9.269E+01 | 1.042E+02 | 1.068E+02 |
| 283 | 5.631E+01 | 6.415E+01 | 4.918E+01 | 5.721E+01 | 4.887E+01 | 4.393E+01 | 4.652E+01 | 4.803E+01 | 4.086E+01 | 7.067E+01 | 5.817E+01 | 3.863E+01 | 3.690E+01 |
| 284 | 3.915E+00 | 4.242E+00 | 5.365E+00 | 3.628E+00 | 5.055E+00 | 5.717E+00 | 3.777E+00 | 6.492E+00 | 7.373E+00 | 4.115E+00 | 8.479E+00 | 5.826E+00 | 8.054E+00 |
| 285 | 7.488E+01 | 6.304E+01 | 7.528E+01 | 5.958E+01 | 7.428E+01 | 6.358E+01 | 6.142E+01 | 6.967E+01 | 7.414E+01 | 6.442E+01 | 6.248E+01 | 8.169E+01 | 8.192E+01 |
| 286 | 5.734E+01 | 5.004E+01 | 5.871E+01 | 4.649E+01 | 5.827E+01 | 5.178E+01 | 5.091E+01 | 5.485E+01 | 5.720E+01 | 4.967E+01 | 4.592E+01 | 6.095E+01 | 6.423E+01 |
| 287 | 1.026E+01 | 9.811E+00 | 1.039E+01 | 6.423E+00 | 9.046E+00 | 7.342E+00 | 6.647E+00 | 9.378E+00 | 7.747E+00 | 1.056E+01 | 8.001E+00 | 8.603E+00 | 7.781E+00 |
| 288 | 6.470E+01 | 5.741E+01 | 5.956E+01 | 6.557E+01 | 5.568E+01 | 7.322E+01 | 8.363E+01 | 7.205E+01 | 6.509E+01 | 7.074E+01 | 5.954E+01 | 6.065E+01 | 6.008E+01 |
| 289 | 5.004E+01 | 4.559E+01 | 4.989E+01 | 5.283E+01 | 4.566E+01 | 6.001E+01 | 7.172E+01 | 5.915E+01 | 5.343E+01 | 5.715E+01 | 4.470E+01 | 4.742E+01 | 4.880E+01 |
| 290 | 1.831E+01 | 1.909E+01 | 2.003E+01 | 1.928E+01 | 1.837E+01 | 2.844E+01 | 2.506E+01 | 2.092E+01 | 2.605E+01 | 1.648E+01 | 1.578E+01 | 2.013E+01 | 2.196E+01 |
| 291 | 1.485E+01 | 1.554E+01 | 1.662E+01 | 1.600E+01 | 1.491E+01 | 2.369E+01 | 2.148E+01 | 1.691E+01 | 2.092E+01 | 1.286E+01 | 1.184E+01 | 1.657E+01 | 1.756E+01 |
| 292 | 2.370E+00 | 2.546E+00 | 2.886E+00 | 1.993E+00 | 2.271E+00 | 2.602E+00 | 2.174E+00 | 2.592E+00 | 2.566E+00 | 1.945E+00 | 2.170E+00 | 2.230E+00 | 2.177E+00 |
| 293 | 2.170E+00 | 2.162E+00 | 2.351E+00 | 9.344E−01 | 1.417E+00 | 1.865E+00 | 1.204E+00 | 1.962E+00 | 1.995E+00 | 2.197E+00 | 1.916E+00 | 1.365E+00 | 1.567E+00 |
| 294 | 2.092E+00 | 2.297E+00 | 3.197E+00 | 3.437E+00 | 2.677E+00 | 1.993E+00 | 2.063E+00 | 2.192E+00 | 3.094E+00 | 1.910E+00 | 6.600E+00 | 1.929E+00 | 1.917E+00 |
| 295 | 2.110E+00 | 2.260E+00 | 3.164E+00 | 3.424E+00 | 2.688E+00 | 2.021E+00 | 2.139E+00 | 2.156E+00 | 3.041E+00 | 1.934E+00 | 6.469E+00 | 1.945E+00 | 1.912E+00 |
| 296 | 1.290E+00 | 1.622E+00 | 2.337E+00 | 2.602E+00 | 1.805E+00 | 1.273E+00 | 1.498E+00 | 1.455E+00 | 2.042E+00 | 1.649E+00 | 5.929E+00 | 1.240E+00 | 1.136E+00 |
| 297 | 3.165E−01 | 2.205E−01 | 2.561E−01 | 2.985E−01 | 3.067E−01 | 3.496E−01 | 3.404E−01 | 3.740E−01 | 4.985E−01 | 3.895E−01 | 2.012E−01 | 3.454E−01 | 2.689E−01 |

APPENDIX D-continued

Ovarian Cancer
Training Dataset

| | | | | | | | | | | | | | |
|---|---|---|---|---|---|---|---|---|---|---|---|---|---|
| 298 | 1.768E−02 | 8.302E−03 | 7.766E−03 | 7.229E−03 | 9.074E−03 | 1.345E−02 | 1.467E−02 | 1.375E−02 | 1.210E−02 | 1.862E−02 | 4.054E−03 | 1.384E−02 | 1.452E−02 |
| 299 | 1.811E−01 | 8.281E−02 | 5.427E−02 | 7.851E−02 | 5.878E−02 | 8.774E−02 | 1.139E−01 | 1.789E−01 | 9.954E−02 | 3.187E−01 | 4.483E−02 | 8.474E−02 | 6.908E−02 |
| 300 | 1.126E−02 | 4.634E−03 | 2.789E−03 | 2.853E−03 | 2.960E−03 | 5.878E−03 | 6.607E−03 | 7.208E−03 | 3.411E−03 | 1.073E−02 | 1.266E−03 | 3.668E−03 | 3.840E−03 |
| 301 | 9.825E−02 | 4.462E−02 | 4.483E−02 | 3.540E−02 | 3.711E−02 | 4.998E−02 | 5.921E−02 | 9.289E−02 | 4.870E−02 | 1.705E−01 | 2.832E−02 | 6.521E−02 | 5.084E−02 |
| 302 | 1.171E−02 | 2.068E−02 | 2.231E−02 | 2.531E−02 | 3.540E−02 | 1.534E−02 | 6.307E−03 | 1.420E−02 | 6.135E−02 | 3.153E−02 | 9.396E−02 | 1.493E−02 | 1.472E−02 |
| 303 | 2.862E−01 | 1.416E−01 | 1.251E−01 | 1.032E−01 | 1.435E−01 | 2.377E−01 | 1.667E−01 | 2.406E−01 | 1.896E−01 | 3.449E−01 | 7.251E−02 | 2.652E−01 | 2.221E−01 |
| 304 | 5.749E−03 | 1.585E−02 | 1.532E−02 | 2.231E−02 | 2.639E−02 | 6.243E−03 | 4.977E−03 | 7.444E−03 | 6.221E−02 | 2.062E−02 | 7.101E−02 | 7.573E−03 | 6.457E−03 |
| 305 | 4.965E−01 | 2.945E−01 | 2.760E−01 | 2.328E−01 | 2.990E−01 | 3.964E−01 | 4.126E−01 | 5.470E−01 | 2.815E−01 | 6.972E−01 | 1.540E−01 | 3.393E−01 | 3.386E−01 |
| 306 | 3.003E−02 | 1.547E−02 | 2.070E−02 | 1.195E−02 | 1.658E−02 | 3.282E−02 | 2.639E−02 | 2.403E−02 | 1.952E−02 | 4.376E−02 | 7.101E−03 | 2.381E−02 | 2.617E−02 |
| 307 | 1.301E+00 | 6.967E−01 | 5.710E−01 | 3.836E−01 | 8.793E−01 | 1.928E+00 | 9.667E−01 | 9.532E−01 | 7.378E−01 | 9.811E−01 | 2.373E−01 | 1.486E+00 | 1.838E+00 |
| 308 | 2.295E−02 | 1.429E−02 | 1.294E−02 | 7.401E−03 | 1.635E−02 | 3.904E−02 | 1.525E−02 | 1.171E−02 | 1.023E−02 | 1.581E−02 | 4.312E−03 | 2.403E−02 | 2.660E−02 |
| 309 | 3.904E−03 | 1.547E−03 | 3.175E−03 | 2.019E−03 | 3.861E−03 | 5.878E−03 | 6.157E−03 | 3.389E−03 | 2.167E−03 | 3.668E−03 | 3.282E−03 | 4.762E−03 | 4.441E−03 |
| 310 | 6.436E−03 | 9.653E−04 | 1.195E−03 | 6.736E−04 | 1.135E−03 | 1.705E−03 | 1.467E−03 | 2.252E−03 | 3.711E−03 | 1.128E−03 | 1.774E−03 | 2.167E−03 | 1.815E−03 |
| 311 | 4.591E−04 | 7.723E−04 | 1.991E−04 | 3.368E−04 | 6.822E−04 | 1.894E−04 | 5.856E−04 | 4.505E−04 | 6.200E−04 | 1.412E−03 | 1.266E−03 | 8.645E−04 | 6.050E−04 |
| 312 | 2.295E−04 | 7.723E−04 | 3.990E−04 | 8.409E−04 | 4.548E−04 | 3.797E−04 | 1.467E−04 | 4.505E−04 | 0.000E+00 | 0.000E+00 | 0.000E+00 | 2.167E−04 | 4.033E−04 |
| 313 | 1.585E−01 | 7.487E−02 | 7.851E−02 | 6.543E−02 | 9.911E−02 | 2.034E−01 | 1.523E−01 | 2.019E−01 | 9.053E−02 | 1.929E−01 | 2.051E−02 | 1.881E−01 | 1.671E−01 |
| 314 | 5.964E−03 | 2.896E−03 | 3.776E−03 | 2.019E−03 | 3.175E−03 | 5.299E−03 | 6.157E−03 | 7.444E−03 | 5.578E−03 | 5.921E−03 | 7.594E−04 | 4.333E−03 | 7.658E−03 |
| 315 | 3.604E−02 | 1.469E−02 | 1.472E−02 | 1.397E−02 | 2.111E−02 | 4.119E−02 | 2.596E−02 | 3.497E−02 | 1.581E−02 | 3.239E−02 | 5.063E−03 | 3.733E−02 | 2.960E−02 |
| 316 | 1.148E−03 | 3.861E−04 | 7.959E−04 | 8.409E−04 | 6.822E−04 | 1.137E−03 | 8.795E−04 | 1.126E−03 | 3.111E−04 | 1.693E−03 | 5.063E−04 | 1.946E−03 | 2.210E−03 |
| 317 | 3.304E−02 | 1.216E−02 | 1.633E−02 | 1.530E−02 | 1.227E−02 | 3.325E−02 | 2.424E−02 | 3.583E−02 | 1.519E−02 | 2.145E−02 | 6.843E−03 | 2.467E−02 | 2.789E−02 |
| 318 | 2.982E−03 | 7.723E−04 | 1.991E−03 | 6.736E−04 | 1.362E−03 | 9.460E−04 | 5.856E−04 | 2.027E−03 | 3.111E−04 | 2.832E−03 | 1.013E−03 | 1.298E−03 | 1.210E−03 |
| 319 | 2.074E−01 | 9.160E−02 | 1.227E−01 | 1.066E−01 | 1.163E−01 | 2.981E−01 | 1.639E−01 | 2.577E−01 | 1.392E−01 | 1.521E−01 | 4.012E−02 | 2.602E−01 | 2.598E−01 |
| 320 | 9.182E−04 | 1.933E−04 | 0.000E+00 | 1.682E−04 | 6.822E−04 | 5.685E−04 | 8.795E−04 | 1.351E−03 | 3.111E−04 | 5.642E−04 | 0.000E+00 | 4.333E−04 | 1.210E−03 |
| 321 | 2.167E−01 | 1.023E−01 | 1.191E−01 | 1.201E−01 | 1.598E−01 | 2.720E−01 | 2.256E−01 | 3.557E−01 | 1.242E−01 | 3.000E−01 | 3.368E−02 | 2.351E−01 | 2.014E−01 |
| 322 | 9.182E−03 | 5.020E−03 | 3.175E−03 | 2.531E−03 | 4.762E−03 | 9.289E−03 | 6.457E−03 | 1.015E−02 | 8.366E−03 | 1.100E−02 | 2.274E−03 | 8.431E−03 | 7.658E−03 |
| 323 | 1.875E−01 | 1.249E−01 | 1.579E−01 | 1.304E−01 | 1.763E−01 | 3.570E−01 | 2.070E−01 | 3.062E−01 | 1.673E−01 | 2.092E−01 | 4.054E−02 | 2.745E−01 | 3.112E−01 |
| 324 | 7.809E−03 | 4.827E−03 | 3.583E−03 | 2.019E−03 | 4.998E−03 | 7.573E−03 | 6.007E−03 | 8.795E−03 | 3.711E−03 | 5.363E−03 | 2.531E−03 | 6.479E−03 | 1.068E−02 |
| 325 | 1.216E−02 | 6.564E−03 | 2.789E−03 | 4.376E−03 | 7.723E−03 | 6.436E−03 | 8.645E−03 | 1.105E−02 | 5.277E−03 | 8.752E−03 | 4.054E−03 | 6.929E−03 | 8.259E−03 |
| 326 | 1.607E−03 | 1.547E−03 | 5.964E−04 | 5.041E−04 | 2.044E−03 | 1.515E−03 | 4.398E−04 | 9.010E−04 | 9.310E−04 | 3.111E−03 | 7.594E−04 | 8.645E−04 | 8.066E−04 |
| 327 | 1.976E−02 | 5.020E−03 | 8.366E−03 | 6.050E−03 | 5.213E−03 | 1.060E−02 | 8.795E−03 | 1.757E−02 | 4.333E−03 | 1.270E−02 | 4.054E−03 | 9.525E−03 | 1.291E−02 |
| 328 | 2.295E−03 | 3.861E−04 | 9.954E−04 | 3.368E−04 | 9.074E−04 | 1.894E−04 | 1.613E−03 | 1.126E−03 | 6.200E−04 | 1.693E−03 | 1.519E−03 | 2.167E−03 | 0.000E+00 |
| 329 | 4.998E−01 | 2.821E−01 | 2.326E−01 | 1.989E−01 | 3.129E−01 | 6.845E−01 | 4.002E−01 | 4.959E−01 | 3.122E−01 | 4.773E−01 | 1.025E−01 | 5.351E−01 | 4.542E−01 |
| 330 | 6.436E−03 | 4.441E−03 | 2.188E−03 | 2.188E−03 | 6.822E−03 | 6.436E−03 | 4.248E−03 | 6.543E−03 | 3.111E−03 | 5.642E−03 | 2.789E−03 | 7.787E−03 | 4.033E−03 |
| 331 | 3.432E−02 | 1.663E−02 | 1.392E−02 | 1.227E−02 | 1.317E−02 | 3.990E−02 | 2.295E−02 | 4.033E−02 | 1.860E−02 | 3.604E−02 | 4.805E−03 | 4.398E−02 | 3.904E−02 |
| 332 | 1.607E−03 | 9.653E−04 | 1.195E−03 | 0.000E+00 | 3.625E−03 | 7.573E−04 | 8.795E−04 | 1.126E−03 | 9.310E−04 | 1.128E−03 | 2.531E−03 | 1.081E−03 | 8.066E−04 |
| 333 | 2.381E−02 | 9.460E−03 | 6.757E−03 | 9.074E−03 | 8.409E−03 | 2.660E−02 | 1.701E−02 | 2.510E−02 | 8.688E−03 | 2.062E−02 | 4.805E−03 | 2.660E−02 | 2.167E−02 |
| 334 | 4.591E−04 | 3.861E−04 | 1.991E−04 | 3.368E−04 | 4.548E−03 | 0.000E+00 | 0.000E+00 | 4.505E−04 | 9.310E−04 | 8.474E−04 | 7.594E−04 | 2.167E−04 | 6.050E−04 |
| 335 | 5.642E−02 | 1.971E−02 | 2.089E−02 | 2.360E−02 | 2.134E−02 | 6.650E−02 | 3.389E−02 | 5.213E−02 | 2.982E−02 | 3.282E−02 | 1.291E−02 | 7.229E−02 | 6.328E−02 |
| 336 | 4.591E−03 | 2.896E−03 | 3.175E−03 | 2.360E−03 | 1.817E−02 | 3.604E−03 | 2.338E−03 | 6.307E−03 | 4.333E−03 | 7.894E−03 | 7.337E−03 | 6.050E−03 | 4.848E−03 |
| 337 | 1.206E−01 | 5.663E−02 | 5.277E−02 | 4.805E−02 | 6.243E−02 | 1.358E−01 | 8.710E−02 | 1.120E−01 | 4.312E−02 | 1.210E−01 | 1.875E−02 | 1.272E−01 | 1.150E−01 |
| 338 | 2.295E−03 | 5.792E−04 | 7.959E−04 | 1.682E−04 | 1.135E−03 | 1.894E−03 | 8.795E−04 | 6.757E−04 | 1.860E−03 | 2.252E−03 | 5.063E−04 | 4.119E−03 | 2.424E−03 |
| 339 | 5.942E−02 | 2.810E−02 | 2.338E−02 | 2.001E−02 | 2.810E−02 | 7.701E−02 | 3.926E−02 | 5.599E−02 | 2.703E−02 | 4.205E−02 | 6.328E−03 | 6.908E−02 | 7.144E−02 |
| 340 | 2.746E−03 | 1.740E−03 | 2.381E−03 | 1.008E−03 | 2.044E−03 | 3.797E−03 | 1.907E−03 | 2.488E−03 | 1.551E−03 | 3.668E−03 | 1.266E−03 | 2.810E−03 | 3.025E−03 |
| 341 | 7.573E−03 | 3.089E−03 | 3.583E−03 | 2.019E−03 | 3.861E−03 | 4.355E−03 | 3.518E−03 | 5.406E−03 | 3.711E−03 | 6.779E−03 | 2.027E−03 | 7.787E−03 | 4.441E−03 |
| 342 | 4.591E−04 | 5.792E−04 | 3.990E−04 | 3.368E−04 | 4.548E−04 | 5.685E−04 | 4.398E−04 | 2.252E−04 | 0.000E+00 | 1.128E−03 | 0.000E+00 | 8.645E−04 | 6.050E−04 |
| 343 | 5.513E−03 | 5.985E−03 | 3.990E−03 | 5.213E−03 | 7.272E−03 | 7.015E−03 | 3.368E−03 | 6.757E−03 | 6.822E−03 | 7.058E−03 | 2.531E−03 | 6.929E−03 | 3.432E−03 |
| 344 | 6.886E−04 | 3.861E−04 | 3.990E−04 | 1.682E−04 | 1.135E−03 | 3.797E−04 | 2.939E−04 | 4.505E−04 | 9.310E−04 | 5.642E−04 | 5.063E−04 | 4.333E−04 | 4.033E−04 |

APPENDIX D-continued

Ovarian Cancer
Training Dataset

| | CY | CZ | DA | DB | DC | DD | DE | DF | DG | DH | DI | DJ | DK |
|---|---|---|---|---|---|---|---|---|---|---|---|---|---|
| 1 | 13816 | 14550 | 13680 | 13818 | 14666 | 13868 | 13834 | N4 G | N5 K | 13637 | 13654 | 13681 | 13690 |
| 2 | Benign | Early Malignant | Benign | Control | Early Malignant | Benign | Benign | Control | Control | Benign | Benign | Benign | Benign |
| 3 | 1 | 2 | 1 | 0 | 2 | 1 | 1 | 0 | 0 | 1 | 1 | 1 | 1 |
| 4 | −1 | −1 | −1 | 1 | −1 | −1 | −1 | 1 | 1 | −1 | −1 | −1 | −1 |
| 5 | 1.609E+00 | 1.336E+00 | 1.418E+00 | 1.293E+00 | 9.790E−01 | 1.121E+00 | 1.594E+00 | 1.771E+00 | 1.797E+00 | 4.624E−01 | 1.966E+00 | 1.822E+00 | 1.321E+00 |
| 6 | 5.461E−01 | 2.886E−01 | 6.395E−01 | 4.227E−01 | 3.541E−01 | 4.238E−01 | 4.024E−01 | 7.843E−02 | 5.633E−02 | 1.878E−01 | 8.454E−01 | 7.486E−01 | 8.282E−01 |
| 7 | 2.564E−01 | 1.599E−01 | 2.350E−01 | 1.642E−01 | 1.556E−01 | 1.384E−01 | 2.264E−01 | 2.468E−02 | 2.479E−02 | 6.556E−02 | 2.886E−01 | 2.672E−01 | 1.781E−01 |
| 8 | 7.958E−01 | 8.995E−01 | 6.255E−01 | 7.270E−01 | 8.974E−01 | 7.883E−01 | 7.129E−01 | 5.836E+00 | 5.837E+00 | 1.524E−01 | 5.998E−01 | 7.190E−01 | 4.807E−01 |
| 9 | 2.082E−02 | 2.511E−02 | 2.339E−02 | 2.350E−02 | 2.682E−02 | 2.371E−02 | 1.781E−02 | 4.034E−02 | 3.830E−02 | 2.918E−02 | 2.006E−02 | 1.845E−02 | 2.178E−02 |
| 10 | 8.144E−03 | 1.255E−02 | 8.895E−03 | 7.693E−03 | 9.968E−03 | 1.159E−02 | 1.223E−02 | 0.000E+00 | 2.253E−03 | 4.163E−03 | 9.528E−03 | 1.105E−02 | 1.685E−02 |
| 11 | 8.594E−03 | 1.255E−02 | 1.030E−02 | 9.056E−03 | 1.059E−02 | 9.914E−03 | 1.116E−02 | 4.485E−03 | 2.253E−03 | 7.285E−03 | 1.059E−02 | 1.953E−02 | 8.895E−03 |
| 12 | 5.429E−03 | 6.921E−03 | 9.828E−03 | 4.528E−03 | 9.345E−03 | 6.052E−03 | 7.242E−03 | 4.485E−03 | 1.127E−02 | 1.041E−03 | 1.170E−02 | 4.753E−03 | 6.427E−03 |
| 13 | 1.180E−02 | 1.006E−02 | 3.745E−03 | 5.880E−03 | 1.867E−02 | 1.159E−02 | 1.059E−02 | 5.601E−02 | 5.633E−02 | 9.367E−03 | 8.466E−03 | 8.970E−03 | 3.466E−03 |
| 14 | 5.333E−02 | 5.912E−02 | 5.848E−02 | 5.751E−02 | 5.236E−02 | 4.185E−02 | 6.406E−02 | 6.727E−03 | 6.760E−03 | 1.878E−02 | 9.582E−02 | 5.225E−02 | 5.494E−02 |
| 15 | 2.264E−03 | 7.543E−03 | 5.150E−03 | 5.429E−03 | 1.867E−03 | 1.652E−03 | 4.464E−03 | 0.000E+00 | 0.000E+00 | 3.122E−03 | 1.373E−02 | 6.330E−03 | 2.961E−03 |
| 16 | 0.000E+00 | 2.511E−03 | 0.000E+00 | 0.000E+00 | 0.000E+00 | 5.504E−04 | 5.579E−04 | 2.242E−03 | 2.253E−03 | 0.000E+00 | 1.059E−03 | 1.588E−03 | 0.000E+00 |
| 17 | 3.165E−03 | 9.431E−03 | 8.423E−03 | 8.144E−03 | 1.491E−02 | 7.157E−03 | 5.579E−03 | 2.242E−03 | 2.253E−03 | 3.122E−03 | 5.290E−03 | 5.805E−03 | 3.466E−03 |
| 18 | 3.165E−02 | 3.841E−02 | 4.442E−02 | 3.573E−02 | 3.670E−02 | 2.972E−02 | 3.627E−02 | 2.693E−02 | 4.056E−02 | 3.959E−02 | 4.024E−02 | 2.425E−02 | 1.534E−02 |
| 19 | 8.637E−02 | 8.112E−02 | 8.798E−02 | 8.144E−02 | 7.725E−02 | 6.717E−02 | 1.084E−01 | 3.809E−02 | 3.155E−02 | 4.582E−02 | 1.054E−01 | 1.170E−01 | 7.017E−02 |
| 20 | 9.045E−04 | 1.888E−03 | 0.000E+00 | 9.056E−04 | 0.000E+00 | 3.305E−03 | 1.116E−03 | 8.970E−03 | 0.000E+00 | 2.082E−03 | 5.290E−04 | 2.639E−03 | 4.946E−04 |
| 21 | 1.674E−02 | 1.070E−02 | 1.212E−02 | 1.180E−02 | 2.114E−02 | 9.914E−03 | 8.358E−03 | 2.468E−02 | 1.803E−02 | 6.245E−03 | 9.002E−03 | 9.506E−03 | 1.438E−02 |
| 22 | 1.352E−03 | 5.665E−03 | 2.339E−03 | 1.813E−03 | 2.489E−03 | 1.652E−03 | 2.232E−03 | 0.000E+00 | 0.000E+00 | 0.000E+00 | 1.588E−03 | 1.588E−03 | 2.961E−03 |
| 23 | 3.433E−02 | 2.961E−02 | 3.884E−02 | 2.489E−02 | 3.112E−02 | 2.865E−02 | 2.790E−02 | 6.727E−03 | 4.056E−02 | 4.367E−02 | 6.084E−02 | 5.440E−02 | 5.343E−02 |
| 24 | 4.517E−02 | 5.783E−02 | 6.363E−02 | 4.936E−02 | 5.976E−02 | 5.504E−02 | 7.135E−02 | 1.567E−02 | 2.704E−02 | 3.852E−02 | 6.406E−02 | 6.073E−02 | 4.056E−02 |
| 25 | 1.985E−02 | 1.006E−02 | 1.685E−02 | 1.084E−02 | 1.373E−02 | 1.266E−02 | 1.059E−02 | 1.341E−02 | 4.506E−03 | 8.326E−03 | 2.650E−02 | 2.221E−02 | 1.931E−02 |
| 26 | 1.406E−02 | 1.137E−02 | 1.545E−02 | 1.491E−02 | 1.996E−02 | 1.545E−02 | 1.059E−02 | 2.242E−03 | 9.013E−03 | 8.326E−03 | 1.749E−02 | 2.371E−02 | 1.931E−02 |
| 27 | 1.352E−03 | 5.665E−03 | 3.273E−03 | 2.715E−03 | 3.734E−03 | 1.652E−03 | 2.232E−03 | 4.485E−03 | 6.760E−03 | 2.082E−03 | 2.650E−03 | 6.330E−03 | 3.959E−03 |
| 28 | 2.618E−02 | 2.071E−02 | 2.715E−02 | 2.307E−02 | 1.931E−02 | 1.652E−02 | 1.727E−02 | 1.341E−02 | 1.127E−02 | 1.770E−02 | 3.122E−02 | 4.013E−02 | 2.028E−02 |
| 29 | 3.884E−02 | 3.584E−02 | 5.290E−02 | 3.391E−02 | 2.865E−02 | 3.852E−02 | 4.796E−02 | 3.584E−02 | 9.013E−03 | 2.285E−02 | 4.710E−02 | 4.539E−02 | 3.509E−02 |
| 30 | 5.966E−02 | 6.545E−02 | 5.665E−02 | 6.470E−02 | 6.041E−02 | 5.837E−02 | 6.245E−02 | 1.567E−02 | 2.704E−02 | 6.663E−02 | 6.513E−02 | 6.127E−02 | 4.206E−02 |
| 31 | 3.981E−02 | 4.399E−02 | 3.326E−02 | 4.528E−02 | 4.925E−02 | 3.852E−02 | 3.959E−02 | 2.371E−01 | 4.056E−02 | 5.311E−02 | 5.665E−02 | 5.333E−02 | 4.453E−02 |
| 32 | 2.940E−02 | 3.015E−02 | 2.242E−02 | 1.770E−02 | 2.060E−02 | 2.307E−02 | 2.564E−02 | 1.459E−01 | 1.014E−01 | 7.285E−03 | 6.352E−03 | 1.534E−02 | 5.933E−03 |
| 33 | 1.127E−02 | 8.176E−03 | 5.612E−03 | 7.693E−03 | 1.180E−02 | 1.105E−02 | 9.474E−03 | 6.727E−03 | 9.013E−03 | 6.245E−03 | 1.266E−02 | 1.212E−02 | 1.931E−02 |
| 34 | 3.541E−01 | 3.509E−01 | 2.758E−01 | 3.069E−01 | 4.088E−01 | 2.961E−01 | 3.552E−01 | 1.588E−01 | 1.717E−01 | 9.367E−02 | 6.513E−02 | 5.279E−02 | 6.330E−02 |
| 35 | 6.288E−02 | 8.047E−02 | 4.496E−02 | 6.931E−02 | 6.792E−02 | 4.238E−02 | 3.959E−02 | 2.940E−01 | 5.633E−02 | 5.097E−02 | 6.567E−02 | 9.979E−02 | 7.371E−02 |
| 36 | 4.067E−03 | 4.399E−03 | 5.150E−03 | 1.534E−02 | 5.601E−03 | 6.609E−03 | 7.800E−03 | 1.116E−02 | 2.253E−03 | 5.204E−03 | 8.466E−03 | 6.330E−03 | 5.440E−03 |
| 37 | 1.577E−02 | 1.448E−02 | 2.575E−02 | 7.242E−03 | 9.968E−03 | 1.652E−02 | 1.781E−02 | 2.017E−02 | 2.253E−02 | 1.148E−02 | 1.588E−02 | 8.970E−03 | 1.534E−02 |
| 38 | 8.594E−03 | 1.760E−02 | 8.423E−03 | 8.605E−03 | 1.180E−02 | 1.427E−02 | 1.556E−02 | 6.727E−03 | 6.760E−03 | 9.367E−03 | 2.650E−03 | 7.393E−03 | 1.974E−03 |
| 39 | 1.004E−01 | 1.320E−01 | 1.330E−01 | 8.197E−02 | 6.223E−02 | 8.369E−02 | 9.807E−02 | 1.116E−01 | 1.642E−01 | 8.841E−02 | 2.039E−01 | 1.067E−01 | 1.054E−01 |
| 40 | 1.524E−01 | 1.416E−01 | 1.964E−01 | 1.059E−01 | 1.438E−01 | 1.255E−01 | 1.556E−01 | 9.185E−02 | 7.436E−02 | 1.888E−01 | 1.309E−01 | 1.384E−01 | 7.167E−02 |
| 41 | 1.406E−02 | 1.760E−02 | 2.060E−02 | 1.770E−02 | 1.931E−02 | 2.092E−02 | 2.672E−02 | 3.809E−02 | 2.704E−02 | 2.704E−02 | 1.588E−02 | 1.685E−02 | 1.234E−02 |
| 42 | 2.264E−03 | 2.511E−03 | 4.678E−04 | 1.813E−03 | 4.356E−03 | 5.504E−04 | 0.000E+00 | 0.000E+00 | 0.000E+00 | 6.245E−03 | 2.650E−03 | 2.114E−03 | 1.974E−03 |
| 43 | 7.381E−03 | 6.327E−03 | 5.272E−03 | 6.070E−03 | 1.240E−02 | 6.198E−03 | 6.018E−03 | 1.183E−02 | 5.401E−03 | 2.294E−02 | 4.810E−03 | 7.201E−03 | 6.996E−03 |
| 44 | 2.703E−01 | 3.240E−01 | 2.318E−01 | 2.392E−01 | 3.475E−01 | 2.568E−01 | 3.024E−01 | 1.944E−01 | 1.981E−01 | 3.677E−01 | 1.008E−01 | 1.000E−01 | 1.147E−01 |
| 45 | 1.142E−01 | 9.285E−02 | 1.127E−01 | 9.568E−02 | 1.456E−01 | 1.188E−01 | 9.516E−02 | 1.337E−01 | 1.685E−01 | 1.325E−01 | 5.993E−02 | 6.996E−02 | 9.130E−02 |
| 46 | 1.021E−01 | 1.039E−01 | 8.102E−02 | 9.105E−02 | 1.546E−01 | 9.542E−02 | 9.568E−02 | 2.369E−01 | 2.462E−01 | 3.365E−01 | 8.205E−02 | 1.070E−01 | 9.825E−02 |
| 47 | 2.089E−01 | 2.833E−01 | 1.669E−01 | 1.807E−01 | 3.183E−01 | 2.076E−01 | 2.055E−01 | 1.175E−01 | 1.116E−01 | 2.849E−01 | 2.932E−02 | 4.321E−02 | 5.298E−02 |
| 48 | 1.973E−02 | 3.549E−02 | 2.299E−02 | 2.420E−02 | 3.061E−02 | 2.428E−02 | 1.898E−02 | 1.826E−02 | 2.855E−02 | 1.672E−02 | 8.256E−03 | 1.114E−02 | 1.150E−02 |

APPENDIX D-continued

Ovarian Cancer
Training Dataset

| | | | | | | | | | | | | | |
|---|---|---|---|---|---|---|---|---|---|---|---|---|---|
| 49 | 1.409E−02 | 1.613E−02 | 9.979E−03 | 9.979E−03 | 1.896E−02 | 1.294E−02 | 1.643E−02 | 6.996E−03 | 9.182E−03 | 8.976E−03 | 4.810E−03 | 4.038E−03 | 7.587E−03 |
| 50 | 4.115E−03 | 2.564E−03 | 3.601E−03 | 3.678E−03 | 6.713E−03 | 1.054E−03 | 3.344E−03 | 6.996E−03 | 5.401E−03 | 1.996E−03 | 2.803E−03 | 2.279E−03 | 2.253E−03 |
| 51 | 1.638E−01 | 1.160E−01 | 1.515E−01 | 1.878E−01 | 1.448E−01 | 1.917E−01 | 1.789E−01 | 1.119E−01 | 1.322E−01 | 2.672E−01 | 8.050E−02 | 1.098E−01 | 1.080E−01 |
| 52 | 4.115E−03 | 2.261E−03 | 2.906E−03 | 3.138E−03 | 4.938E−03 | 3.421E−03 | 2.405E−03 | 3.215E−03 | 7.021E−03 | 5.735E−03 | 1.268E−03 | 3.806E−03 | 3.678E−03 |
| 53 | 5.838E−02 | 5.864E−02 | 4.269E−02 | 4.861E−02 | 6.224E−02 | 4.475E−02 | 4.501E−02 | 1.934E−02 | 3.241E−02 | 1.348E−02 | 1.168E−02 | 1.049E−02 | 8.770E−03 |
| 54 | 5.268E+00 | 4.131E+00 | 6.080E+00 | 5.703E+00 | 4.089E+00 | 5.764E+00 | 5.205E+00 | 4.217E+00 | 4.223E+00 | 6.484E+00 | 6.100E+00 | 4.585E+00 | 5.110E+00 |
| 55 | 8.108E−01 | 6.655E−01 | 6.436E−01 | 6.685E−01 | 6.730E−01 | 6.746E−01 | 8.646E−01 | 4.427E−01 | 4.799E−01 | 8.954E−01 | 5.884E−01 | 5.202E−01 | 4.536E−01 |
| 56 | 1.754E−01 | 1.314E−01 | 1.942E−01 | 1.702E−01 | 1.479E−01 | 1.941E−01 | 1.590E−01 | 1.757E−01 | 2.030E−01 | 1.908E−01 | 1.762E−01 | 1.476E−01 | 1.826E−01 |
| 57 | 4.259E+00 | 3.594E+00 | 3.855E+00 | 3.697E+00 | 3.542E+00 | 3.623E+00 | 4.865E+00 | 2.815E+00 | 2.817E+00 | 4.914E+00 | 3.368E+00 | 2.868E+00 | 2.172E+00 |
| 58 | 5.813E−02 | 4.655E−02 | 4.269E−02 | 4.424E−02 | 7.664E−02 | 4.604E−02 | 4.578E−02 | 9.465E−02 | 1.080E−01 | 7.870E−02 | 3.884E−02 | 4.681E−02 | 6.018E−02 |
| 59 | 6.636E−02 | 5.787E−02 | 5.967E−02 | 5.967E−02 | 4.887E−02 | 5.350E−02 | 8.050E−02 | 3.163E−02 | 2.855E−02 | 7.073E−02 | 5.504E−02 | 4.398E−01 | 3.601E−02 |
| 60 | 2.752E−02 | 3.781E−02 | 2.266E−02 | 2.675E−02 | 2.726E−02 | 2.361E−02 | 3.189E−02 | 1.075E−02 | 9.722E−03 | 6.481E−03 | 7.356E−03 | 6.327E−03 | 4.732E−03 |
| 61 | 1.266E+00 | 1.677E+00 | 1.384E+00 | 1.868E+00 | 9.895E−01 | 1.387E+00 | 1.025E+00 | 1.372E+00 | 1.423E+00 | 2.596E+00 | 1.752E+00 | 1.654E+00 | 1.983E+00 |
| 62 | 5.576E−01 | 4.464E−01 | 4.852E−01 | 4.982E−01 | 4.278E−01 | 5.004E−01 | 4.042E−01 | 8.231E−01 | 9.382E−01 | 5.855E−01 | 3.998E−01 | 5.777E−01 | 5.875E−01 |
| 63 | 1.301E−02 | 1.553E−02 | 1.145E−02 | 1.541E−02 | 1.283E−02 | 1.003E−02 | 9.619E−03 | 1.183E−02 | 1.836E−02 | 1.497E−02 | 9.773E−03 | 8.848E−03 | 1.054E−02 |
| 64 | 2.928E+00 | 2.469E+00 | 3.012E+00 | 2.590E+00 | 1.971E+00 | 2.836E+00 | 2.867E+00 | 1.093E+00 | 1.107E+00 | 2.142E+00 | 2.495E+00 | 2.742E+00 | 2.833E+00 |
| 65 | 1.481E−01 | 1.137E−01 | 1.235E−01 | 1.286E−01 | 1.345E−01 | 1.384E−01 | 1.183E−01 | 6.867E−02 | 9.619E−02 | 7.793E−02 | 8.770E−02 | 1.013E−01 | 1.260E−01 |
| 66 | 7.697E−01 | 6.845E−01 | 6.032E−01 | 5.696E−01 | 6.000E−01 | 5.788E−01 | 8.536E−01 | 3.519E−01 | 3.115E−01 | 6.145E−01 | 4.643E−01 | 6.231E−01 | 4.257E−01 |
| 67 | 7.639E−02 | 7.304E−02 | 4.758E−02 | 5.633E−02 | 8.462E−02 | 5.504E−02 | 6.353E−02 | 3.704E−02 | 4.372E−02 | 3.601E−02 | 2.196E−02 | 4.630E−02 | 4.912E−02 |
| 68 | 1.276E−01 | 1.871E−01 | 1.029E−01 | 1.098E−01 | 1.571E−01 | 1.157E−01 | 1.337E−01 | 3.112E−02 | 3.729E−02 | 1.620E−02 | 1.636E−02 | 1.543E−02 | 1.186E−02 |
| 69 | 5.478E−01 | 9.544E−01 | 5.677E−01 | 7.549E−01 | 4.620E−01 | 6.345E−01 | 5.701E−01 | 2.488E−01 | 2.645E−01 | 7.858E−01 | 7.294E−01 | 7.418E−01 | 7.921E−01 |
| 70 | 3.241E−02 | 4.578E−02 | 3.138E−02 | 3.498E−02 | 3.163E−02 | 3.498E−02 | 2.564E−02 | 1.559E−02 | 1.836E−02 | 2.420E−02 | 1.865E−02 | 2.392E−02 | 2.829E−02 |
| 71 | 1.008E−02 | 1.085E−02 | 8.307E−03 | 8.256E−03 | 1.373E−02 | 7.510E−03 | 1.016E−02 | 5.375E−03 | 5.401E−04 | 3.498E−03 | 5.581E−03 | 3.678E−03 | 5.221E−03 |
| 72 | 3.781E−03 | 3.472E−03 | 3.138E−03 | 2.387E−03 | 4.475E−03 | 3.292E−03 | 4.810E−03 | 2.150E−03 | 1.080E−03 | 1.996E−03 | 2.410E−03 | 3.292E−03 | 1.186E−03 |
| 73 | 2.856E−03 | 2.641E−03 | 1.479E−03 | 1.433E−03 | 3.928E−03 | 1.738E−03 | 2.348E−03 | 0.000E+00 | 0.000E+00 | 1.095E−03 | 1.114E−03 | 3.330E−03 | 2.077E−03 |
| 74 | 5.237E−03 | 5.293E−03 | 2.957E−03 | 5.711E−03 | 5.237E−03 | 6.366E−03 | 4.108E−03 | 7.077E−03 | 0.000E+00 | 5.474E−03 | 5.011E−03 | 8.330E−03 | 3.646E−03 |
| 75 | 4.571E−02 | 3.047E−02 | 3.296E−02 | 4.097E−02 | 3.995E−02 | 2.720E−02 | 2.517E−02 | 8.657E−01 | 1.964E−01 | 3.939E−02 | 6.072E−02 | 7.607E−02 | 6.445E−02 |
| 76 | 6.941E−02 | 7.348E−02 | 2.664E−02 | 7.381E−02 | 5.372E−02 | 3.826E−02 | 2.935E−02 | 1.099E+00 | 3.149E−01 | 6.783E−02 | 7.404E−02 | 1.129E−01 | 1.051E−01 |
| 77 | 1.614E−02 | 3.307E−03 | 2.460E−03 | 5.711E−03 | 1.309E−03 | 1.738E−03 | 1.761E−03 | 1.411E−01 | 4.977E−02 | 8.758E−03 | 1.058E−02 | 6.659E−03 | 8.837E−03 |
| 78 | 9.515E−04 | 6.614E−04 | 4.921E−04 | 4.763E−04 | 0.000E+00 | 5.790E−04 | 5.869E−04 | 0.000E+00 | 0.000E+00 | 0.000E+00 | 0.000E+00 | 2.777E−03 | 3.115E−03 |
| 79 | 7.133E−03 | 1.059E−02 | 6.896E−03 | 1.095E−02 | 1.242E−02 | 1.275E−02 | 8.205E−03 | 2.359E−03 | 0.000E+00 | 7.664E−03 | 6.682E−03 | 6.106E−03 | 3.646E−03 |
| 80 | 4.752E−04 | 5.959E−03 | 4.436E−03 | 4.763E−04 | 3.928E−03 | 2.314E−03 | 1.761E−03 | 2.359E−03 | 0.000E+00 | 2.190E−03 | 1.670E−03 | 5.000E−03 | 1.558E−03 |
| 81 | 1.332E−02 | 2.178E−02 | 3.397E−02 | 1.953E−02 | 3.205E−02 | 2.427E−02 | 2.054E−02 | 9.436E−03 | 7.111E−03 | 2.630E−02 | 1.558E−02 | 1.670E−02 | 1.512E−02 |
| 82 | 8.567E−03 | 8.600E−03 | 1.129E−02 | 1.047E−02 | 1.772E−02 | 1.100E−02 | 1.467E−02 | 5.655E−02 | 1.185E−02 | 1.208E−02 | 8.905E−03 | 4.447E−03 | 5.722E−03 |
| 83 | 4.752E−04 | 1.321E−03 | 4.921E−03 | 4.763E−03 | 4.582E−03 | 3.476E−03 | 3.521E−03 | 7.077E−03 | 0.000E+00 | 5.474E−03 | 1.670E−03 | 1.670E−03 | 3.646E−03 |
| 84 | 1.479E−02 | 1.716E−02 | 7.878E−03 | 8.093E−03 | 1.501E−02 | 1.625E−02 | 1.230E−02 | 7.077E−03 | 0.000E+00 | 1.095E−03 | 1.230E−02 | 1.219E−02 | 1.093E−02 |
| 85 | 9.515E−04 | 3.307E−03 | 1.479E−03 | 3.815E−03 | 1.964E−03 | 3.476E−03 | 1.174E−03 | 7.077E−03 | 4.740E−03 | 4.379E−03 | 1.670E−03 | 1.111E−03 | 2.077E−03 |
| 86 | 9.989E−03 | 1.524E−02 | 7.878E−03 | 1.242E−02 | 9.176E−03 | 6.366E−03 | 7.619E−03 | 1.275E−01 | 4.977E−02 | 2.404E−02 | 6.129E−03 | 1.275E−02 | 1.253E−02 |
| 87 | 1.998E−02 | 3.239E−02 | 7.381E−03 | 3.002E−02 | 2.686E−02 | 2.032E−02 | 1.411E−02 | 6.479E−01 | 1.727E−01 | 3.725E−02 | 3.567E−02 | 4.108E−02 | 3.228E−02 |
| 88 | 5.711E−03 | 2.641E−03 | 3.442E−03 | 4.763E−03 | 2.619E−03 | 1.163E−03 | 4.108E−03 | 7.314E−02 | 1.422E−02 | 6.569E−03 | 6.129E−03 | 7.223E−03 | 7.799E−03 |
| 89 | 1.094E−02 | 1.716E−02 | 5.418E−03 | 1.047E−02 | 1.569E−02 | 9.266E−03 | 5.282E−03 | 1.208E−01 | 4.740E−02 | 1.862E−02 | 1.230E−02 | 2.280E−02 | 2.596E−02 |
| 90 | 4.233E−02 | 2.844E−02 | 4.436E−03 | 2.957E−02 | 2.359E−02 | 1.388E−02 | 1.287E−02 | 9.714E−01 | 2.980E−01 | 6.896E−02 | 3.341E−02 | 5.113E−02 | 6.140E−02 |
| 91 | 8.567E−03 | 4.628E−03 | 3.442E−03 | 9.526E−03 | 4.582E−03 | 2.314E−03 | 1.174E−03 | 1.037E−01 | 2.844E−02 | 4.379E−03 | 7.235E−03 | 1.275E−02 | 1.558E−02 |
| 92 | 1.242E−02 | 2.178E−02 | 3.442E−03 | 1.242E−02 | 7.201E−03 | 7.528E−03 | 1.174E−02 | 1.321E−01 | 2.133E−02 | 7.664E−03 | 1.783E−02 | 8.330E−03 | 1.093E−02 |
| 93 | 2.381E−03 | 5.959E−03 | 4.436E−03 | 8.567E−03 | 4.582E−03 | 6.953E−03 | 2.935E−03 | 8.014E−02 | 2.844E−02 | 9.853E−03 | 6.682E−03 | 4.447E−03 | 8.837E−03 |
| 94 | 9.515E−04 | 1.321E−03 | 4.436E−03 | 2.856E−03 | 1.309E−03 | 5.790E−04 | 2.348E−03 | 3.070E−02 | 4.740E−03 | 3.284E−03 | 2.788E−03 | 1.111E−03 | 1.041E−03 |
| 95 | 1.806E−02 | 7.280E−03 | 7.381E−03 | 1.185E−02 | 7.201E−03 | 7.528E−03 | 8.792E−03 | 5.892E−02 | 4.029E−02 | 3.070E−02 | 5.011E−03 | 1.111E−02 | 1.512E−02 |
| 96 | 9.989E−03 | 1.321E−03 | 2.957E−03 | 5.711E−03 | 4.582E−03 | 1.738E−03 | 5.282E−03 | 6.366E−02 | 9.481E−03 | 3.284E−03 | 7.235E−03 | 9.436E−03 | 7.799E−03 |
| 97 | 3.330E−03 | 4.628E−03 | 9.842E−04 | 7.619E−03 | 4.582E−03 | 2.314E−03 | 3.521E−03 | 7.314E−02 | 2.607E−02 | 4.379E−03 | 5.011E−03 | 7.777E−03 | 6.242E−03 |
| 98 | 7.607E−03 | 1.059E−02 | 4.436E−03 | 1.095E−02 | 1.242E−02 | 8.691E−03 | 1.114E−02 | 2.359E−02 | 2.133E−02 | 6.569E−03 | 7.799E−03 | 1.111E−02 | 8.837E−03 |

APPENDIX D-continued

Ovarian Cancer
Training Dataset

| | | | | | | | | | | | | | |
|---|---|---|---|---|---|---|---|---|---|---|---|---|---|
| 99 | 8.731E−02 | 7.186E−02 | 1.032E−01 | 6.205E−02 | 9.319E−02 | 8.682E−02 | 8.535E−02 | 3.200E−01 | 1.447E−01 | 1.312E−01 | 1.216E−01 | 1.471E−01 | 1.135E−01 |
| 100 | 1.962E−02 | 2.440E−02 | 3.053E−02 | 2.330E−02 | 3.703E−02 | 2.955E−02 | 3.188E−02 | 2.048E−02 | 1.030E−02 | 4.525E−02 | 3.090E−02 | 5.248E−02 | 3.384E−02 |
| 101 | 1.496E−01 | 2.342E−01 | 2.097E−01 | 1.324E−01 | 1.312E−01 | 2.256E−01 | 2.232E−01 | 1.435E−01 | 1.133E−01 | 1.729E−01 | 2.121E−01 | 1.545E−01 | 1.142E−01 |
| 102 | 5.628E−01 | 8.209E−01 | 5.727E−01 | 5.739E−01 | 1.114E+00 | 8.091E−01 | 5.837E−01 | 2.514E−01 | 1.987E−01 | 1.888E−01 | 5.910E−01 | 8.115E−01 | 7.799E−01 |
| 103 | 1.582E−01 | 2.452E−01 | 2.636E−01 | 1.521E−01 | 1.508E−01 | 2.575E−01 | 2.232E−01 | 1.178E−01 | 1.570E−01 | 1.925E−01 | 2.857E−01 | 1.815E−01 | 1.198E−01 |
| 104 | 2.305E−01 | 2.735E−01 | 2.121E−01 | 2.134E−01 | 3.912E−01 | 2.673E−01 | 1.974E−01 | 2.538E−01 | 3.017E−01 | 1.803E−01 | 2.575E−01 | 3.323E−01 | 3.728E−01 |
| 105 | 8.955E−01 | 1.389E+00 | 9.649E−01 | 1.009E+00 | 1.601E+00 | 1.313E+00 | 1.076E+00 | 1.508E−01 | 1.570E−01 | 1.386E−01 | 8.670E−01 | 1.004E+00 | 9.804E−01 |
| 106 | 1.484E−01 | 1.373E−01 | 1.337E−01 | 1.545E−01 | 1.974E−01 | 1.398E−01 | 1.172E−01 | 2.465E−01 | 2.673E−01 | 1.582E−01 | 2.158E−01 | 2.256E−01 | 1.790E−01 |
| 107 | 1.239E−01 | 1.078E−01 | 9.945E−02 | 8.277E−02 | 1.386E−01 | 1.075E−01 | 1.071E−01 | 1.178E−01 | 1.239E−01 | 7.971E−02 | 1.410E−01 | 1.349E−01 | 1.029E−01 |
| 108 | 1.386E−01 | 2.060E−01 | 1.447E−01 | 1.337E−01 | 1.435E−01 | 1.324E−01 | 1.324E−01 | 1.741E−01 | 1.082E−01 | 1.471E−01 | 1.803E−01 | 1.876E−01 | 1.631E−01 |
| 109 | 6.720E−03 | 1.078E−02 | 6.953E−03 | 4.660E−03 | 1.068E−02 | 4.402E−03 | 7.002E−03 | 0.000E+00 | 2.575E−03 | 9.516E−03 | 4.231E−03 | 4.831E−03 | 2.820E−03 |
| 110 | 2.992E−02 | 1.937E−02 | 1.226E−02 | 1.447E−02 | 1.349E−02 | 1.324E−02 | 1.778E−02 | 2.563E−03 | 0.000E+00 | 8.326E−03 | 1.149E−02 | 8.449E−03 | 6.217E−03 |
| 111 | 2.330E−02 | 2.158E−02 | 1.447E−02 | 1.913E−02 | 9.258E−03 | 1.950E−02 | 1.974E−02 | 2.563E−03 | 0.000E+00 | 7.137E−03 | 1.029E−02 | 9.651E−03 | 7.909E−03 |
| 112 | 1.655E−02 | 1.078E−02 | 1.226E−02 | 1.086E−02 | 1.275E−02 | 1.263E−02 | 1.852E−02 | 5.126E−03 | 2.575E−03 | 8.326E−03 | 1.210E−02 | 1.086E−02 | 1.074E−02 |
| 113 | 5.162E−03 | 2.158E−03 | 2.134E−03 | 4.145E−03 | 8.547E−03 | 4.402E−03 | 5.739E−03 | 2.563E−03 | 0.000E+00 | 1.189E−03 | 5.445E−03 | 1.207E−03 | 3.384E−03 |
| 114 | 9.307E−03 | 9.344E−03 | 1.069E−02 | 6.720E−03 | 9.258E−03 | 6.291E−03 | 7.002E−03 | 0.000E+00 | 0.000E+00 | 2.379E−03 | 6.045E−03 | 5.432E−03 | 1.131E−03 |
| 115 | 8.265E−03 | 1.078E−02 | 8.559E−03 | 7.247E−03 | 5.690E−03 | 5.665E−03 | 7.639E−03 | 0.000E+00 | 0.000E+00 | 2.379E−03 | 4.231E−03 | 3.017E−03 | 4.525E−03 |
| 116 | 4.132E−03 | 1.435E−03 | 3.740E−03 | 2.587E−03 | 4.267E−03 | 1.888E−03 | 1.913E−03 | 0.000E+00 | 0.000E+00 | 0.000E+00 | 4.231E−03 | 4.218E−03 | 2.820E−03 |
| 117 | 1.496E−02 | 1.007E−02 | 1.288E−02 | 6.205E−03 | 7.112E−03 | 6.916E−03 | 1.337E−02 | 0.000E+00 | 2.575E−03 | 3.568E−03 | 4.231E−03 | 2.416E−03 | 4.525E−03 |
| 118 | 5.690E−03 | 4.316E−03 | 5.886E−03 | 5.175E−03 | 7.823E−03 | 3.777E−03 | 8.277E−03 | 0.000E+00 | 0.000E+00 | 3.568E−03 | 3.630E−03 | 3.017E−03 | 3.384E−03 |
| 119 | 1.085E−02 | 5.751E−03 | 7.492E−03 | 5.690E−03 | 4.979E−03 | 8.179E−03 | 6.376E−03 | 2.563E−03 | 0.000E+00 | 5.947E−03 | 1.210E−03 | 1.815E−03 | 2.256E−03 |
| 120 | 5.162E−03 | 1.223E−02 | 6.413E−03 | 8.792E−03 | 1.275E−02 | 9.442E−03 | 4.464E−03 | 0.000E+00 | 2.575E−03 | 2.379E−03 | 1.815E−03 | 3.017E−03 | 3.384E−03 |
| 121 | 3.562E−02 | 5.850E−02 | 4.684E−02 | 9.706E−03 | 2.671E−02 | 4.337E−02 | 1.995E−02 | 1.122E−01 | 4.835E−02 | 1.193E−01 | 1.514E−01 | 1.211E−01 | 9.884E−02 |
| 122 | 1.069E−01 | 8.994E−02 | 1.336E−01 | 1.291E−01 | 1.336E−01 | 7.088E−02 | 9.172E−02 | 4.328E−01 | 5.156E−01 | 1.861E−01 | 1.362E−01 | 1.469E−01 | 1.202E−01 |
| 123 | 2.289E+00 | 2.182E+00 | 2.021E+00 | 2.262E+00 | 2.476E+00 | 1.638E+00 | 2.093E+00 | 6.002E+00 | 5.378E+00 | 3.045E+00 | 2.698E+00 | 2.663E+00 | 2.912E+00 |
| 124 | 3.882E−02 | 2.698E−02 | 1.336E−02 | 1.941E−02 | 3.562E−02 | 7.881E−03 | 2.787E−02 | 3.206E−02 | 6.447E−02 | 7.444E−02 | 6.438E−02 | 3.402E−02 | 4.951E−02 |
| 125 | 4.533E−02 | 9.884E−02 | 8.032E−02 | 1.941E−02 | 6.242E−02 | 3.936E−02 | 6.776E−02 | 8.014E−02 | 4.835E−02 | 5.209E−02 | 1.060E−01 | 1.247E−01 | 8.139E−02 |
| 126 | 6.500E−01 | 2.476E−01 | 7.133E−01 | 3.882E−01 | 5.031E−01 | 4.292E−01 | 2.912E−01 | 2.164E+00 | 1.692E+00 | 4.096E−01 | 7.275E−01 | 6.153E−01 | 5.663E−01 |
| 127 | 1.683E+00 | 1.238E+00 | 1.434E+00 | 1.104E+00 | 1.567E+00 | 1.095E+00 | 8.611E−01 | 7.373E+00 | 7.686E+00 | 1.701E+00 | 1.719E+00 | 1.745E+00 | 1.229E+00 |
| 128 | 1.817E+00 | 1.906E+00 | 1.380E+00 | 1.888E+00 | 1.897E+00 | 1.701E+00 | 1.282E+00 | 4.363E+00 | 4.043E+00 | 1.852E+00 | 1.790E+00 | 1.977E+00 | 2.289E+00 |
| 129 | 3.882E−02 | 5.396E−02 | 3.348E−02 | 3.562E−02 | 4.898E−02 | 6.696E−02 | 5.183E−02 | 4.809E−02 | 8.059E−02 | 9.706E−02 | 5.681E−02 | 8.308E−02 | 2.119E−02 |
| 130 | 6.392E+00 | 7.056E+00 | 7.935E+00 | 6.572E+00 | 4.408E+00 | 4.898E+00 | 2.591E+00 | 7.391E+01 | 7.940E+01 | 1.608E+01 | 1.514E+01 | 1.117E+01 | 1.007E+01 |
| 131 | 6.939E+00 | 3.927E+00 | 7.490E+00 | 4.515E+00 | 5.387E+00 | 3.767E+00 | 4.577E+00 | 4.166E+01 | 4.447E+01 | 1.408E+01 | 1.579E+01 | 8.015E+00 | 9.176E+00 |
| 132 | 3.562E−02 | 2.253E−02 | 4.354E−02 | 3.562E−02 | 4.898E−02 | 4.728E−02 | 1.594E−02 | 1.603E−02 | 3.224E−02 | 5.957E−02 | 6.064E−02 | 1.514E−02 | 4.248E−02 |
| 133 | 1.941E−02 | 1.354E−02 | 3.348E−03 | 1.941E−02 | 1.781E−02 | 1.576E−02 | 2.395E−02 | 1.603E−02 | 0.000E+00 | 2.974E−02 | 1.140E−02 | 1.888E−02 | 1.772E−02 |
| 134 | 6.474E−03 | 8.994E−03 | 1.336E−02 | 1.291E−02 | 2.226E−02 | 7.881E−03 | 1.193E−02 | 3.206E−02 | 0.000E+00 | 2.235E−02 | 3.028E−02 | 1.514E−02 | 2.832E−02 |
| 135 | 3.882E−02 | 4.497E−02 | 2.680E−02 | 1.941E−02 | 2.226E−02 | 2.360E−02 | 1.995E−02 | 1.603E−02 | 1.612E−02 | 2.235E−02 | 2.271E−02 | 1.888E−02 | 1.060E−02 |
| 136 | 9.706E−03 | 1.354E−02 | 0.000E+00 | 2.271E−02 | 2.671E−02 | 3.152E−02 | 1.995E−02 | 0.000E+00 | 0.000E+00 | 2.235E−02 | 1.897E−02 | 7.551E−03 | 1.416E−02 |
| 137 | 2.591E−02 | 6.305E−02 | 2.680E−02 | 2.912E−02 | 1.024E−01 | 7.881E−02 | 4.390E−02 | 0.000E+00 | 3.224E−02 | 2.235E−02 | 6.438E−02 | 1.888E−02 | 3.535E−02 |
| 138 | 1.621E−02 | 2.698E−02 | 3.348E−02 | 3.241E−02 | 1.781E−02 | 2.360E−02 | 7.979E−03 | 3.206E−02 | 1.612E−02 | 1.487E−02 | 1.514E−02 | 1.888E−02 | 2.832E−02 |
| 139 | 1.719E−01 | 1.398E−01 | 2.378E−01 | 1.817E−01 | 1.870E−01 | 2.244E−01 | 1.158E−01 | 5.931E−01 | 3.865E−01 | 2.235E−01 | 1.398E−01 | 1.736E−01 | 3.045E−01 |
| 140 | 1.104E−01 | 1.033E−01 | 9.706E−02 | 1.487E−01 | 2.093E−01 | 1.104E−01 | 4.782E−02 | 1.923E−01 | 1.772E−01 | 7.444E−02 | 4.541E−02 | 9.795E−02 | 1.024E−01 |
| 141 | 4.203E−02 | 5.396E−02 | 2.680E−02 | 3.562E−02 | 9.795E−02 | 1.184E−02 | 3.188E−02 | 1.603E−02 | 1.612E−02 | 3.722E−02 | 4.924E−02 | 8.691E−02 | 1.024E−01 |
| 142 | 2.262E−02 | 8.994E−03 | 1.674E−02 | 1.621E−02 | 8.905E−03 | 1.184E−02 | 1.594E−02 | 4.809E−02 | 3.224E−02 | 7.444E−03 | 1.140E−02 | 1.514E−02 | 7.079E−03 |
| 143 | 6.474E−03 | 2.698E−02 | 4.016E−02 | 1.621E−02 | 4.452E−02 | 7.881E−03 | 2.395E−02 | 3.206E−02 | 1.612E−02 | 1.487E−02 | 7.578E−03 | 7.551E−03 | 1.772E−02 |
| 144 | 2.912E−02 | 5.850E−02 | 3.687E−02 | 2.271E−02 | 3.117E−02 | 5.120E−02 | 1.995E−02 | 3.206E−02 | 1.612E−02 | 4.470E−02 | 3.411E−02 | 2.262E−02 | 3.188E−02 |
| 145 | 1.941E−02 | 4.497E−03 | 3.348E−03 | 2.591E−02 | 2.226E−02 | 1.968E−02 | 1.995E−02 | 0.000E+00 | 1.131E−01 | 2.235E−02 | 1.897E−02 | 1.131E−02 | 2.119E−02 |
| 145 | 1.683E−01 | 2.297E−01 | 2.146E−01 | 2.529E−01 | 2.182E−01 | 2.440E−01 | 1.077E−01 | 6.411E−01 | 5.156E−01 | 5.289E−01 | 2.760E−01 | 2.609E−01 | 4.069E−01 |
| 147 | 9.706E−02 | 9.439E−02 | 6.358E−02 | 1.291E−01 | 1.469E−01 | 1.104E−01 | 7.578E−02 | 2.885E−01 | 2.582E−01 | 1.416E−01 | 8.335E−02 | 1.434E−01 | 1.915E−01 |
| 148 | 3.918E−01 | 3.108E−01 | 2.511E−01 | 4.310E−01 | 2.983E−01 | 3.268E−01 | 2.556E−01 | 5.610E−01 | 9.350E−01 | 3.500E−01 | 2.351E−01 | 4.007E−01 | 6.153E−01 |

APPENDIX D-continued

Ovarian Cancer
Training Dataset

| | | | | | | | | | | | | | |
|---|---|---|---|---|---|---|---|---|---|---|---|---|---|
| 149 | 1.104E−01 | 4.951E−02 | 6.358E−02 | 8.424E−02 | 9.795E−02 | 8.272E−02 | 7.177E−02 | 1.603E−01 | 1.131E−01 | 6.705E−02 | 6.821E−02 | 9.795E−02 | 6.367E−02 |
| 150 | 3.562E−02 | 4.497E−02 | 3.687E−02 | 3.241E−02 | 2.671E−02 | 2.760E−02 | 2.395E−02 | 8.014E−02 | 6.447E−02 | 4.470E−02 | 1.140E−02 | 1.888E−02 | 1.772E−02 |
| 151 | 9.706E−03 | 4.052E−02 | 2.680E−02 | 1.291E−02 | 8.905E−03 | 1.576E−02 | 2.395E−02 | 4.809E−02 | 3.224E−02 | 4.470E−02 | 2.271E−02 | 1.888E−02 | 2.476E−02 |
| 152 | 2.591E−02 | 2.253E−02 | 5.690E−02 | 2.591E−02 | 3.117E−02 | 3.152E−02 | 2.395E−02 | 3.206E−02 | 0.000E+00 | 1.487E−02 | 5.681E−02 | 3.019E−02 | 2.119E−02 |
| 153 | 1.941E−02 | 1.354E−02 | 3.348E−02 | 2.271E−02 | 8.905E−03 | 1.576E−02 | 7.979E−03 | 3.206E−02 | 1.612E−02 | 1.487E−02 | 2.271E−02 | 1.514E−02 | 3.535E−02 |
| 154 | 1.291E−02 | 4.497E−03 | 6.696E−03 | 9.706E−03 | 3.117E−02 | 1.184E−02 | 3.989E−03 | 1.603E−02 | 1.612E−02 | 2.235E−02 | 1.514E−02 | 3.019E−02 | 2.119E−02 |
| 155 | 9.706E−03 | 4.052E−02 | 2.680E−02 | 1.941E−02 | 8.905E−03 | 7.881E−03 | 1.193E−02 | 1.603E−02 | 0.000E+00 | 8.192E−02 | 1.514E−02 | 1.514E−02 | 2.119E−02 |
| 156 | 5.245E−01 | 3.241E−01 | 4.791E−01 | 5.316E−01 | 3.740E−01 | 2.048E−01 | 2.716E−01 | 1.238E+00 | 1.193E+00 | 9.795E−01 | 5.530E−01 | 4.951E−01 | 1.033E+00 |
| 157 | 1.683E−01 | 1.665E−01 | 1.505E−01 | 1.621E−01 | 1.647E−01 | 1.104E−01 | 8.771E−02 | 6.892E−01 | 3.865E−01 | 3.722E−01 | 1.549E−01 | 2.075E−01 | 3.010E−01 |
| 158 | 4.497E−01 | 5.396E−01 | 3.820E−01 | 5.859E−01 | 3.428E−01 | 3.188E−01 | 1.950E−01 | 1.362E+00 | 1.140E+00 | 7.747E−01 | 5.111E−01 | 5.361E−01 | 9.261E−01 |
| 159 | 1.425E−01 | 1.122E−01 | 5.361E−02 | 1.291E−01 | 1.336E−01 | 1.024E−01 | 6.385E−02 | 3.206E−01 | 3.063E−01 | 1.416E−01 | 1.211E−01 | 1.469E−01 | 1.879E−01 |
| 160 | 3.562E−02 | 3.598E−02 | 4.354E−02 | 3.882E−02 | 1.336E−02 | 3.544E−02 | 1.193E−02 | 4.809E−02 | 3.224E−02 | 3.722E−02 | 1.897E−02 | 4.907E−02 | 3.535E−02 |
| 161 | 2.591E−02 | 4.052E−02 | 4.016E−02 | 3.241E−02 | 3.562E−02 | 6.305E−02 | 2.395E−02 | 1.603E−02 | 9.706E−02 | 2.974E−02 | 2.654E−02 | 1.131E−02 | 3.535E−02 |
| 162 | 4.533E−02 | 2.698E−02 | 3.010E−02 | 2.912E−02 | 4.007E−02 | 1.184E−02 | 4.390E−02 | 1.603E−02 | 0.000E+00 | 2.235E−02 | 4.541E−02 | 1.131E−02 | 3.894E−02 |
| 163 | 1.291E−02 | 1.799E−02 | 3.010E−02 | 1.291E−02 | 4.007E−02 | 1.968E−02 | 3.989E−03 | 1.603E−02 | 0.000E+00 | 2.235E−02 | 3.028E−02 | 3.019E−02 | 1.416E−02 |
| 164 | 6.474E−03 | 4.052E−02 | 2.680E−02 | 9.706E−03, | 1.336E−02 | 1.576E−02 | 1.995E−02 | 1.603E−02 | 4.835E−02 | 7.444E−03 | 1.514E−02 | 1.514E−02 | 1.416E−02 |
| 165 | 1.621E−02 | 1.354E−02 | 3.348E−02 | 1.291E−02 | 3.117E−02 | 1.576E−02 | 1.594E−02 | 0.000E+00 | 1.612E−02 | 4.470E−02 | 3.411E−02 | 3.402E−02 | 1.416E−02 |
| 166 | 5.824E−02 | 5.396E−02 | 5.361E−02 | 9.350E−02 | 7.133E−02 | 3.936E−02 | 5.183E−02 | 9.617E−02 | 1.612E−01 | 6.705E−02 | 5.298E−02 | 9.795E−02 | 1.238E−01 |
| 167 | 2.458E−01 | 2.609E−01 | 2.306E−01 | 3.045E−01 | 1.603E−01 | 2.600E−01 | 1.113E−01 | 5.129E−01 | 5.316E−01 | 4.915E−01 | 2.992E−01 | 3.553E−01 | 6.866E−01 |
| 168 | 1.549E−01 | 1.754E−01 | 1.175E−01 | 1.558E−01 | 1.514E−01 | 1.060E−01 | 1.158E−01 | 1.763E−01 | 1.772E−01 | 2.235E−01 | 1.594E−01 | 1.167E−01 | 2.226E−01 |
| 169 | 2.912E−02 | 6.305E−02 | 3.687E−02 | 6.803E−02 | 2.226E−02 | 3.544E−02 | 5.583E−02 | 4.809E−02 | 6.447E−02 | 1.264E−01 | 8.709E−02 | 7.551E−02 | 7.427E−02 |
| 170 | 2.912E−02 | 4.951E−02 | 3.687E−02 | 3.882E−02 | 4.452E−02 | 5.120E−02 | 6.776E−02 | 6.411E−02 | 1.612E−02 | 5.209E−02 | 3.411E−02 | 6.046E−02 | 3.188E−02 |
| 171 | 3.562E−02 | 3.598E−02 | 1.006E−02 | 4.533E−02 | 5.343E−02 | 1.968E−02 | 1.193E−02 | 3.206E−02 | 0.000E+00 | 2.235E−02 | 2.654E−02 | 2.645E−02 | 1.060E−02 |
| 172 | 5.212E−02 | 5.212E−02 | 5.212E−02 | 8.964E−02 | 9.209E−02 | 9.270E−02 | 7.639E−02 | 1.435E−01 | 1.447E−01 | 1.128E−01 | 5.788E−02 | 1.170E−01 | 1.557E−01 |
| 173 | 1.973E+00 | 2.725E+00 | 1.807E+00 | 1.883E+00 | 3.102E+00 | 2.279E+00 | 2.090E+00 | 1.100E+00 | 1.309E+00 | 3.078E−01 | 2.228E+00 | 2.673E+00 | 2.995E+00 |
| 174 | 3.514E+00 | 4.744E+00 | 2.964E+00 | 2.929E+00 | 5.124E−00 | 3.649E+00 | 3.437E+00 | 1.033E+00 | 1.194E+00 | 4.635E−01 | 4.072E+00 | 4.353E+00 | 5.506E+00 |
| 175 | 7.925E−01 | 9.364E−01 | 8.147E−01 | 7.386E−01 | 1.088E+00 | 8.499E−01 | 7.639E−01 | 1.084E+00 | 1.309E+00 | 2.673E−01 | 8.228E−01 | 1.282E+00 | 1.358E+00 |
| 176 | 1.918E+00 | 3.046E+00 | 2.202E+00 | 2.103E+00 | 2.923E+00 | 1.980E+00 | 2.428E+00 | 3.913E+00 | 4.327E+00 | 9.598E−01 | 2.590E+00 | 2.997E+00 | 2.888E+00 |
| 177 | 1.072E+00 | 1.085E+00 | 9.770E−01 | 1.020E+00 | 1.336E+00 | 6.658E−01 | 6.953E−01 | 3.926E+00 | 3.843E+00 | 6.168E−01 | 1.765E+00 | 1.889E+00 | 1.890E+00 |
| 178 | 1.692E−01 | 1.987E−01 | 1.582E−01 | 3.188E−01 | 2.085E−01 | 1.704E−01 | 1.312E−01 | 4.880E−01 | 5.788E−01 | 6.462E−02 | 2.158E−01 | 3.151E−01 | 3.519E−01 |
| 179 | 3.078E−02 | 2.477E−02 | 2.207E−02 | 4.954E−02 | 3.740E−02 | 2.440E−02 | 3.078E−02 | 7.284E−02 | 7.321E−02 | 9.234E−03 | 2.551E−02 | 3.801E−02 | 4.623E−02 |
| 180 | 8.915E−03 | 1.987E−02 | 1.288E−02 | 1.251E−02 | 3.311E−02 | 1.193E−02 | 1.263E−02 | 1.104E−02 | 1.557E−02 | 9.234E−03 | 1.361E−02 | 2.551E−02 | 1.606E−02 |
| 181 | 1.113E−02 | 1.606E−02 | 1.521E−02 | 1.115E−02 | 6.744E−03 | 9.221E−03 | 1.533E−02 | 1.324E−02 | 2.440E−02 | 4.513E−02 | 1.827E−02 | 1.766E−02 | 1.263E−02 |
| 182 | 6.953E−02 | 1.066E−01 | 7.149E−02 | 8.694E−02 | 1.729E−01 | 9.651E−02 | 7.468E−02 | 3.090E−02 | 1.778E−02 | 1.533E−02 | 8.976E−02 | 1.361E−01 | 1.422E−01 |
| 183 | 1.346E+00 | 2.020E+00 | 1.436E+00 | 1.740E+00 | 2.730E+00 | 2.052E+00 | 1.553E+00 | 6.708E−01 | 9.013E−01 | 7.003E−01 | 1.351E+00 | 2.073E+00 | 2.148E+00 |
| 184 | 1.582E+00 | 2.213E+00 | 1.570E+00 | 1.929E+00 | 3.317E+00 | 2.049E+00 | 1.575E+00 | 7.247E−01 | 8.056E−01 | 2.943E−01 | 1.625E+00 | 2.596E+00 | 2.374E+00 |
| 185 | 1.061E+00 | 1.577E+00 | 1.010E+00 | 1.346E+00 | 2.280E+00 | 1.463E+00 | 1.073E+00 | 3.115E−01 | 3.127E−01 | 1.349E−01 | 1.014E+00 | 1.648E+00 | 1.562E+00 |
| 186 | 2.144E+00 | 2.941E+00 | 2.079E+00 | 2.344E+00 | 4.369E+00 | 2.866E+00 | 2.224E+00 | 1.301E+00 | 1.527E+00 | 1.037E+00 | 2.382E+00 | 3.516E+00 | 4.329E+00 |
| 187 | 5.506E−01 | 6.266E−01 | 5.359E−01 | 5.763E−01 | 8.510E−01 | 6.769E−01 | 5.138E−01 | 3.605E−01 | 4.721E−01 | 3.446E−01 | 4.464E−01 | 8.546E−01 | 9.129E−01 |
| 188 | 4.991E−02 | 5.886E−02 | 5.297E−02 | 4.733E−02 | 6.867E−02 | 7.161E−02 | 5.432E−02 | 4.856E−02 | 7.983E−02 | 3.483E−02 | 3.912E−02 | 7.026E−02 | 6.671E−02 |
| 189 | 1.025E−02 | 9.920E−03 | 1.288E−02 | 1.386E−02 | 1.655E−02 | 1.085E−02 | 8.792E−03 | 1.987E−02 | 1.999E−02 | 7.174E−03 | 7.296E−03 | 2.759E−02 | 1.754E−02 |
| 190 | 1.337E−01 | 2.195E−01 | 1.668E−01 | 1.827E−01 | 2.771E−01 | 1.557E−01 | 1.422E−01 | 2.269E−01 | 1.913E−01 | 1.169E−01 | 1.606E−01 | 4.316E−01 | 3.078E−01 |
| 191 | 2.603E+00 | 3.059E+00 | 2.525E+00 | 2.962E+00 | 4.163E+00 | 1.952E+00 | 1.735E+00 | 4.061E+00 | 3.890E+00 | 1.681E+00 | 3.594E+00 | 4.553E+00 | 4.129E+00 |
| 192 | 6.438E−01 | 8.471E−01 | 6.254E−01 | 1.208E+00 | 1.066E+00 | 6.266E−01 | 4.844E−01 | 8.056E−01 | 8.804E−01 | 3.164E−01 | 7.161E−01 | 1.114E+00 | 1.044E+00 |
| 193 | 9.172E−02 | 1.349E−01 | 9.454E−02 | 1.754E−01 | 2.048E−01 | 1.036E−01 | 9.221E−02 | 1.459E−01 | 1.643E−01 | 2.354E−02 | 6.573E−02 | 1.324E−01 | 1.155E−01 |
| 194 | 6.818E−02 | 1.471E−01 | 5.714E−02 | 8.069E−02 | 1.570E−01 | 1.161E−01 | 1.026E−01 | 1.766E−02 | 2.661E−02 | 3.899E−02 | 5.788E−02 | 9.834E−02 | 4.819E−02 |
| 195 | 3.335E−02 | 6.757E−02 | 2.538E−02 | 3.078E−02 | 5.702E−02 | 6.070E−02 | 4.341E−02 | 4.414E−03 | 8.878E−03 | 1.435E−02 | 3.176E−02 | 3.642E−02 | 2.342E−02 |
| 196 | 1.263E−01 | 1.570E−01 | 1.803E−01 | 1.619E−01 | 1.839E−01 | 1.422E−01 | 1.864E−01 | 2.587E−01 | 2.955E−01 | 2.735E−01 | 1.692E−01 | 2.882E−01 | 3.409E−01 |
| 197 | 1.118E−01 | 1.251E−01 | 1.208E−01 | 1.324E−01 | 1.545E−01 | 9.540E−02 | 1.170E−01 | 1.148E−01 | 1.263E−01 | 7.590E−02 | 1.422E−01 | 1.435E−01 | 2.232E−01 |
| 198 | 6.278E−02 | 7.308E−02 | 7.051E−02 | 8.473E−02 | 1.031E−01 | 7.161E−02 | 7.247E−02 | 4.635E−02 | 4.218E−02 | 2.465E−02 | 5.947E−02 | 9.418E−02 | 6.376E−02 |

APPENDIX D-continued

Ovarian Cancer
Training Dataset

| | | | | | | | | | | | | | |
|---|---|---|---|---|---|---|---|---|---|---|---|---|---|
| 199 | 9.577E−02 | 2.440E−01 | 1.386E−01 | 1.459E−01 | 2.600E−01 | 1.692E−01 | 1.484E−01 | 8.829E−03 | 8.878E−03 | 3.483E−02 | 6.315E−02 | 1.410E−01 | 2.538E−02 |
| 200 | 5.297E−02 | 1.183E−01 | 7.382E−02 | 9.773E−02 | 1.459E−01 | 1.128E−01 | 8.792E−02 | 6.622E−03 | 4.439E−03 | 1.533E−02 | 4.795E−02 | 7.124E−02 | 3.850E−02 |
| 201 | 4.010E−02 | 6.879E−02 | 3.139E−02 | 3.654E−02 | 6.193E−02 | 5.530E−02 | 4.672E−02 | 6.622E−03 | 2.219E−02 | 1.128E−02 | 3.544E−02 | 3.384E−02 | 3.164E−02 |
| 202 | 4.905E−03 | 1.422E−02 | 1.288E−02 | 6.695E−03 | 3.679E−03 | 9.761E−03 | 9.332E−03 | 2.207E−03 | 0.000E+00 | 2.048E−03 | 5.212E−03 | 6.757E−03 | 4.868E−04 |
| 203 | 1.778E−03 | 1.864E−03 | 1.386E−03 | 4.464E−04 | 0.000E+00 | 0.000E+00 | 2.195E−03 | 2.207E−03 | 2.219E−03 | 2.048E−03 | 5.212E−04 | 1.040E−03 | 4.868E−04 |
| 204 | 4.010E−03 | 1.545E−02 | 1.288E−02 | 1.071E−02 | 1.044E−02 | 9.221E−03 | 1.422E−02 | 4.414E−03 | 0.000E+00 | 4.096E−03 | 4.697E−03 | 3.642E−03 | 3.409E−03 |
| 205 | 4.451E−04 | 6.193E−04 | 3.225E−03 | 4.464E−04 | 2.452E−03 | 1.631E−03 | 2.747E−03 | 0.000E+00 | 2.219E−03 | 1.025E−03 | 1.044E−03 | 5.199E−04 | 4.868E−04 |
| 206 | 5.788E−03 | 1.545E−02 | 1.704E−02 | 1.557E−02 | 6.744E−03 | 1.361E−02 | 2.085E−02 | 0.000E+00 | 0.000E+00 | 1.025E−03 | 2.085E−03 | 5.199E−03 | 1.459E−03 |
| 207 | 1.337E−03 | 2.477E−03 | 4.611E−04 | 8.915E−04 | 6.131E−04 | 5.420E−04 | 1.099E−03 | 0.000E+00 | 0.000E+00 | 1.025E−03 | 5.212E−04 | 1.040E−03 | 0.000E+00 |
| 208 | 3.568E−03 | 3.102E−03 | 3.225E−03 | 4.464E−03 | 3.066E−03 | 2.170E−03 | 6.585E−03 | 0.000E+00 | 0.000E+00 | 1.025E−03 | 3.654E−03 | 1.557E−03 | 1.950E−03 |
| 209 | 4.451E−04 | 6.193E−04 | 9.221E−04 | 0.000E+00 | 1.839E−03 | 0.000E+00 | 0.000E+00 | 0.000E+00 | 0.000E+00 | 7.174E−03 | 1.044E−03 | 1.557E−03 | 1.950E−03 |
| 210 | 1.337E−03 | 0.000E+00 | 4.611E−04 | 1.337E−03 | 6.131E−04 | 1.085E−03 | 0.000E+00 | 0.000E+00 | 0.000E+00 | 2.048E−03 | 0.000E+00 | 5.199E−04 | 0.000E+00 |
| 211 | 4.451E−04 | 0.000E+00 | 9.221E−04 | 4.464E−04 | 1.226E−03 | 1.085E−03 | 5.494E−04 | 0.000E+00 | 0.000E+00 | 1.025E−03 | 0.000E+00 | 5.199E−04 | 9.749E−04 |
| 212 | 1.337E−03 | 0.000E+00 | 9.221E−04 | 4.464E−04 | 6.131E−04 | 5.420E−04 | 0.000E+00 | 0.000E+00 | 0.000E+00 | 1.025E−03 | 5.212E−04 | 5.199E−04 | 0.000E+00 |
| 213 | 2.232E−03 | 6.193E−04 | 5.996E−03 | 8.915E−04 | 2.452E−03 | 2.170E−03 | 3.299E−03 | 0.000E+00 | 2.219E−03 | 2.048E−03 | 1.570E−03 | 4.157E−03 | 2.918E−03 |
| 214 | 8.915E−04 | 2.477E−03 | 1.386E−03 | 1.778E−03 | 1.839E−03 | 1.085E−03 | 1.099E−03 | 0.000E+00 | 0.000E+00 | 0.000E+00 | 1.044E−03 | 4.157E−03 | 4.868E−04 |
| 215 | 4.451E−04 | 6.193E−04 | 1.839E−03 | 8.915E−04 | 0.000E+00 | 0.000E+00 | 2.195E−03 | 2.207E−03 | 0.000E+00 | 1.025E−03 | 1.044E−03 | 1.040E−03 | 0.000E+00 |
| 216 | 0.000E+00 | 3.716E−03 | 0.000E+00 | 0.000E+00 | 6.131E−04 | 5.420E−04 | 5.494E−04 | 4.414E−03 | 2.219E−03 | 1.025E−03 | 5.212E−04 | 1.557E−03 | 0.000E+00 |
| 217 | 1.337E−03 | 6.193E−04 | 0.000E+00 | 0.000E+00 | 1.226E−03 | 1.085E−03 | 5.494E−04 | 0.000E+00 | 0.000E+00 | 1.025E−03 | 5.212E−04 | 1.040E−03 | 4.868E−04 |
| 218 | 1.558E+00 | 2.144E+00 | 1.708E+00 | 2.018E+00 | 3.341E+00 | 2.380E+00 | 1.785E+00 | 1.559E+00 | 1.864E+00 | 9.331E−01 | 1.597E+00 | 2.609E+00 | 2.204E+00 |
| 219 | 1.203E−02 | 2.477E−02 | 1.251E−02 | 2.318E−02 | 2.698E−02 | 2.600E−02 | 1.974E−02 | 1.324E−02 | 6.658E−03 | 1.128E−02 | 1.570E−02 | 2.649E−02 | 2.489E−02 |
| 220 | 2.222E+00 | 1.244E+00 | 1.388E+00 | 1.735E+00 | 1.861E+00 | 1.562E+00 | 1.395E+00 | 1.391E+00 | 1.479E+00 | 1.349E+00 | 1.077E+00 | 2.177E+00 | 1.943E+00 |
| 221 | 6.808E+01 | 6.135E+01 | 5.426E+01 | 6.121E+01 | 5.247E+01 | 5.049E+01 | 6.726E+01 | 3.937E+01 | 3.468E+01 | 4.666E+01 | 6.906E+01 | 7.760E+01 | 6.051E+01 |
| 222 | 5.194E+01 | 3.404E+01 | 4.994E+01 | 4.369E+01 | 4.221E+01 | 4.252E+01 | 3.946E+01 | 6.328E+01 | 6.023E+01 | 2.895E+01 | 5.209E+01 | 5.007E+01 | 5.896E+01 |
| 223 | 3.537E+01 | 2.459E+01 | 2.632E+01 | 2.550E+01 | 2.911E+01 | 2.310E+01 | 3.020E+01 | 2.758E+01 | 2.473E+01 | 2.032E+01 | 2.691E+01 | 2.912E+01 | 2.254E+01 |
| 224 | 2.603E+01 | 2.811E+01 | 1.958E+01 | 2.210E+01 | 2.008E+01 | 1.860E+01 | 2.871E+01 | 1.537E+01 | 1.284E+01 | 1.236E+01 | 2.215E+01 | 3.058E+01 | 2.324E+01 |
| 225 | 1.617E+01 | 1.881E+01 | 1.614E+01 | 1.967E+01 | 1.503E+01 | 1.459E+01 | 1.197E+01 | 2.939E+01 | 2.780E+01 | 1.701E+01 | 2.287E+01 | 2.323E+01 | 2.671E+01 |
| 226 | 9.547E+00 | 7.828E+00 | 8.226E+00 | 8.025E+00 | 9.009E+00 | 5.410E+00 | 1.003E+01 | 1.276E+01 | 1.054E+01 | 7.018E+00 | 1.505E+01 | 1.047E+01 | 1.161E+01 |
| 227 | 3.638E+00 | 2.285E+00 | 2.297E+00 | 2.749E+00 | 3.492E+00 | 1.625E+00 | 3.175E+00 | 3.957E+00 | 3.366E+00 | 1.858E+00 | 4.384E+00 | 3.036E+00 | 3.599E+00 |
| 228 | 2.778E−01 | 3.122E−01 | 3.793E−01 | 3.793E−01 | 2.389E−01 | 3.848E−01 | 5.720E−01 | 2.219E−01 | 3.129E−01 | 2.579E−01 | 1.695E−01 | 3.809E−01 | 2.476E−01 |
| 229 | 2.834E−01 | 3.468E−01 | 4.175E−01 | 3.928E−01 | 2.505E−01 | 4.160E−01 | 5.780E−01 | 3.065E−01 | 3.573E−01 | 3.126E−01 | 1.903E−01 | 4.140E−01 | 2.790E−01 |
| 230 | 2.937E+01 | 3.767E+01 | 3.796E+01 | 2.919E+01 | 3.201E+01 | 4.172E+01 | 4.425E+01 | 3.369E+01 | 3.323E+01 | 3.332E+01 | 3.834E+01 | 2.579E+01 | 2.009E+01 |
| 231 | 3.660E+00 | 4.230E+00 | 4.685E+00 | 4.334E+00 | 3.823E+00 | 5.234E+00 | 5.503E+00 | 3.853E+00 | 4.292E+00 | 3.335E+00 | 3.675E+00 | 3.784E+00 | 3.239E+00 |
| 232 | 1.800E+00 | 1.603E+00 | 1.790E+00 | 1.313E+00 | 1.814E+00 | 1.710E+00 | 2.620E+00 | 1.514E+00 | 1.506E+00 | 1.689E+00 | 1.671E+00 | 1.445E+00 | 1.251E+00 |
| 233 | 5.853E+00 | 5.109E+00 | 6.443E+00 | 4.914E+00 | 5.780E+00 | 5.996E+00 | 5.919E+00 | 4.059E+00 | 4.358E+00 | 5.205E+00 | 6.964E+00 | 5.569E+00 | 5.781E+00 |
| 234 | 1.668E+01 | 1.578E+01 | 1.605E+01 | 1.740E+01 | 1.919E+01 | 2.088E+01 | 1.996E+01 | 1.447E+01 | 1.467E+01 | 2.038E+01 | 1.529E+01 | 1.451E+01 | 1.424E+01 |
| 235 | 9.400E+00 | 9.499E+00 | 9.522E+00 | 1.039E+01 | 1.145E+01 | 1.054E+01 | 1.068E+01 | 1.086E+01 | 1.009E+01 | 1.220E+01 | 7.821E+00 | 7.525E+00 | 7.134E+00 |
| 236 | 9.882E−01 | 8.464E−01 | 1.033E+00 | 5.608E−01 | 4.902E−01 | 6.132E−01 | 1.182E+00 | 4.414E−01 | 5.238E−01 | 5.074E−01 | 1.088E+00 | 9.731E−01 | 5.660E−01 |
| 237 | 6.100E+00 | 3.844E+00 | 6.047E+00 | 2.835E+00 | 3.729E+00 | 2.746E+00 | 4.129E+00 | 5.100E+00 | 5.517E+00 | 3.414E+00 | 4.177E+00 | 5.198E+00 | 5.216E+00 |
| 238 | 6.453E+00 | 5.342E+00 | 6.440E+00 | 4.866E+00 | 7.184E+00 | 5.418E+00 | 6.365E+00 | 6.659E+00 | 6.522E+00 | 7.699E+00 | 5.059E+00 | 6.313E+00 | 4.950E+00 |
| 239 | 1.238E+00 | 1.209E+00 | 1.237E+00 | 1.164E+00 | 1.307E+00 | 1.173E+00 | 1.393E+00 | 1.185E+00 | 1.291E+00 | 1.469E+00 | 1.062E+00 | 1.324E+00 | 1.012E+00 |
| 240 | 1.230E+01 | 1.084E+01 | 1.159E+01 | 1.227E+01 | 1.442E+01 | 1.573E+01 | 1.321E+01 | 5.513E+00 | 6.601E+00 | 1.026E+01 | 7.297E+00 | 1.590E+01 | 1.119E+01 |
| 241 | 2.360E+02 | 1.837E+02 | 2.333E+02 | 2.465E+02 | 2.428E+02 | 2.282E+02 | 1.988E+02 | 2.645E+02 | 2.597E+02 | 2.673E+02 | 2.208E+02 | 2.244E+02 | 2.614E+02 |
| 242 | 1.769E+02 | 1.484E+02 | 1.474E+02 | 1.634E+02 | 1.843E+02 | 1.433E+02 | 1.678E+02 | 1.572E+02 | 1.534E+02 | 1.946E+02 | 1.346E+02 | 1.442E+02 | 1.322E+02 |
| 243 | 1.632E+01 | 1.305E+01 | 1.315E+01 | 1.421E+01 | 1.689E+01 | 1.260E+01 | 1.540E+01 | 1.509E+01 | 1.380E+01 | 1.562E+01 | 1.146E+01 | 1.282E+01 | 1.086E+01 |
| 244 | 9.751E+00 | 1.208E+01 | 1.023E+01 | 7.033E+00 | 8.391E+00 | 7.512E+00 | 7.447E+00 | 1.364E+01 | 1.487E+01 | 1.269E+01 | 1.146E+01 | 1.351E+01 | 1.090E+01 |
| 245 | 5.115E+00 | 5.309E+00 | 5.790E+00 | 3.804E+00 | 4.837E+00 | 4.012E+00 | 4.220E+00 | 5.175E+00 | 5.915E+00 | 4.775E+00 | 4.954E+00 | 6.135E+00 | 5.253E+00 |
| 246 | 7.648E+00 | 5.281E+00 | 7.143E+00 | 5.846E+00 | 6.756E+00 | 5.280E+00 | 6.717E+00 | 6.113E+00 | 7.330E+00 | 6.006E+00 | 5.873E+00 | 8.059E+00 | 8.546E+00 |
| 247 | 5.274E+00 | 4.366E+00 | 4.859E+00 | 4.321E+00 | 4.682E+00 | 4.464E+00 | 5.475E+00 | 3.674E+00 | 4.488E+00 | 4.721E+00 | 4.112E+00 | 5.508E+00 | 4.855E+00 |
| 248 | 7.288E+01 | 8.507E+01 | 6.843E+01 | 9.865E+01 | 7.329E+01 | 6.744E+01 | 5.029E+01 | 1.089E+02 | 1.085E+02 | 1.154E+02 | 8.169E+01 | 9.850E+01 | 1.199E+02 |

APPENDIX D-continued

Ovarian Cancer
Training Dataset

| | | | | | | | | | | | | | |
|---|---|---|---|---|---|---|---|---|---|---|---|---|---|
| 249 | 5.835E+01 | 6.365E+01 | 5.164E+01 | 9.002E+01 | 5.971E+01 | 5.772E+01 | 4.418E+01 | 7.060E+01 | 7.367E+01 | 5.542E+01 | 4.102E+01 | 7.956E+01 | 9.014E+01 |
| 250 | 1.328E+02 | 1.147E+02 | 1.199E+02 | 1.297E+02 | 1.331E+02 | 1.152E+02 | 1.123E+02 | 1.553E+02 | 1.522E+02 | 1.030E+02 | 1.023E+02 | 1.400E+02 | 1.516E+02 |
| 251 | 5.188E+01 | 5.171E+01 | 4.760E+01 | 4.817E+01 | 5.416E+01 | 5.075E+01 | 5.663E+01 | 4.362E+01 | 4.187E+01 | 4.153E+01 | 3.967E+01 | 5.192E+01 | 4.125E+01 |
| 252 | 3.821E+00 | 3.936E+00 | 3.510E+00 | 3.178E+00 | 3.736E+00 | 3.678E+00 | 4.511E+00 | 2.395E+00 | 2.330E+00 | 2.818E+00 | 3.073E+00 | 3.612E+00 | 2.386E+00 |
| 253 | 4.201E+00 | 4.820E+00 | 4.469E+00 | 2.562E+00 | 3.767E+00 | 3.509E+00 | 4.836E+00 | 4.034E+00 | 4.308E+00 | 5.010E+00 | 5.290E+00 | 5.333E+00 | 3.900E+00 |
| 254 | 9.265E+00 | 9.756E+00 | 8.795E+00 | 6.642E+00 | 1.006E+01 | 7.291E+00 | 6.999E+00 | 1.180E+01 | 1.266E+01 | 1.314E+01 | 1.106E+01 | 1.347E+01 | 1.019E+01 |
| 255 | 8.110E+00 | 9.227E+00 | 8.121E+00 | 7.178E+00 | 8.200E+00 | 6.865E+00 | 6.720E+00 | 9.255E+00 | 1.040E+01 | 1.041E+01 | 1.017E+01 | 1.138E+01 | 9.886E+00 |
| 256 | 2.699E+00 | 3.509E+00 | 3.019E+00 | 2.919E+00 | 3.449E+00 | 2.943E+00 | 2.940E+00 | 2.208E+00 | 2.816E+00 | 3.199E+00 | 2.889E+00 | 3.955E+00 | 3.278E+00 |
| 257 | 5.139E+00 | 5.318E+00 | 6.202E+00 | 4.282E+00 | 4.678E+00 | 5.725E+00 | 5.759E+00 | 3.436E+00 | 4.018E+00 | 4.680E+00 | 5.467E+00 | 5.234E+00 | 4.716E+00 |
| 258 | 2.948E+01 | 2.856E+01 | 2.454E+01 | 2.841E+01 | 3.244E+01 | 1.181E+01 | 2.736E+01 | 3.515E+01 | 3.207E+01 | 3.110E+01 | 3.108E+01 | 3.569E+01 | 3.868E+01 |
| 259 | 4.233E+01 | 6.206E+01 | 3.735E+01 | 5.757E+01 | 4.842E+01 | 3.914E+01 | 3.545E+01 | 6.075E+01 | 5.761E+01 | 5.446E+01 | 4.657E+01 | 6.212E+01 | 7.261E+01 |
| 260 | 2.998E+01 | 5.078E+01 | 3.300E+01 | 4.779E+01 | 3.586E+01 | 3.776E+01 | 3.404E+01 | 2.864E+01 | 2.895E+01 | 3.142E+01 | 3.029E+01 | 4.163E+01 | 4.147E+01 |
| 261 | 2.794E+01 | 4.600E+01 | 3.813E+01 | 3.258E+01 | 3.223E+01 | 4.092E+01 | 3.773E+01 | 2.265E+01 | 2.274E+01 | 3.172E+01 | 3.751E+01 | 2.951E+01 | 2.184E+01 |
| 262 | 9.842E+00 | 1.686E+01 | 1.569E+01 | 1.139E+01 | 1.086E+01 | 1.604E+01 | 1.612E+01 | 6.915E+00 | 6.699E+00 | 8.670E+00 | 1.268E+01 | 1.149E+01 | 7.456E+00 |
| 263 | 3.400E+00 | 3.018E+00 | 3.068E+00 | 2.293E+00 | 3.898E+00 | 2.305E+00 | 3.693E+00 | 3.089E+00 | 3.547E+00 | 3.895E+00 | 4.634E+00 | 4.482E+00 | 3.663E+00 |
| 264 | 2.885E+00 | 2.949E+00 | 3.031E+00 | 2.383E+00 | 4.559E+00 | 2.276E+00 | 3.173E+00 | 2.504E+00 | 2.617E+00 | 3.873E+00 | 3.505E+00 | 4.050E+00 | 2.564E+00 |
| 265 | 2.104E+00 | 2.654E+00 | 2.329E+00 | 1.999E+00 | 3.305E+00 | 2.132E+00 | 2.438E+00 | 1.678E+00 | 1.764E+00 | 2.665E+00 | 2.387E+00 | 2.898E+00 | 1.721E+00 |
| 266 | 1.447E+00 | 2.109E+00 | 2.098E+00 | 1.918E+00 | 2.358E+00 | 2.049E+00 | 2.468E+00 | 5.863E−01 | 6.819E−01 | 1.510E+00 | 1.210E+00 | 1.730E+00 | 7.683E−01 |
| 267 | 1.595E+00 | 2.171E+00 | 2.036E+00 | 1.857E+00 | 2.101E+00 | 2.220E+00 | 2.368E+00 | 9.319E−01 | 1.016E+00 | 1.685E+00 | 1.390E+00 | 1.740E+00 | 1.081E+00 |
| 268 | 1.572E+01 | 1.498E+01 | 1.214E+01 | 1.434E+01 | 2.021E+01 | 9.903E+00 | 1.728E+01 | 1.333E+01 | 1.367E+01 | 1.455E+01 | 1.609E+01 | 1.814E+01 | 1.774E+01 |
| 269 | 9.992E+00 | 1.191E+01 | 8.574E+00 | 1.115E+01 | 1.450E+01 | 7.736E+00 | 1.367E+01 | 6.792E+00 | 6.045E+00 | 7.450E+00 | 8.205E+00 | 1.018E+01 | 8.247E+00 |
| 270 | 3.800E+00 | 5.254E+00 | 3.516E+00 | 4.661E+00 | 5.783E+00 | 3.506E+00 | 5.022E+00 | 2.306E+00 | 2.161E+00 | 2.662E+00 | 2.653E+00 | 4.087E+00 | 2.689E+00 |
| 271 | 1.185E+01 | 1.301E+01 | 1.711E+01 | 1.331E+01 | 1.133E+01 | 1.484E+01 | 1.362E+01 | 1.150E+01 | 1.012E+01 | 1.179E+01 | 1.471E+01 | 1.042E+01 | 9.522E+00 |
| 272 | 7.171E+01 | 9.329E+01 | 9.101E+01 | 6.900E+01 | 7.727E+01 | 9.872E+01 | 9.823E+01 | 8.466E+01 | 8.508E+01 | 8.165E+01 | 9.185E+01 | 6.189E+01 | 5.096E+01 |
| 273 | 8.454E+01 | 1.052E+02 | 1.013E+02 | 7.704E+01 | 8.497E+01 | 1.098E+02 | 1.129E+02 | 7.895E+01 | 8.416E+01 | 9.636E+01 | 1.082E+02 | 7.032E+01 | 5.894E+01 |
| 274 | 1.237E+01 | 1.548E+01 | 1.576E+01 | 1.146E+01 | 1.195E+01 | 1.785E+01 | 1.706E+01 | 1.272E+01 | 1.218E+01 | 1.232E+01 | 1.542E+01 | 9.838E+00 | 8.410E+00 |
| 275 | 5.070E−01 | 5.091E−01 | 7.159E−01 | 5.068E−01 | 6.600E−01 | 8.054E−01 | 5.995E−01 | 4.733E−01 | 4.670E−01 | 7.254E−01 | 6.258E−01 | 5.602E−01 | 7.770E−01 |
| 276 | 9.654E+00 | 9.090E+00 | 1.099E+01 | 7.747E+00 | 9.941E+00 | 1.080E+01 | 1.135E+01 | 6.241E+00 | 7.067E+00 | 9.978E+00 | 1.358E+01 | 7.022E+00 | 7.159E+00 |
| 277 | 2.109E+01 | 2.521E+01 | 2.350E+01 | 1.905E+01 | 2.176E+01 | 3.229E+01 | 3.069E+01 | 1.706E+01 | 1.789E+01 | 2.628E+01 | 3.078E+01 | 1.703E+01 | 1.624E+01 |
| 278 | 2.148E+01 | 2.554E+01 | 2.342E+01 | 1.924E+01 | 2.260E+01 | 3.217E+01 | 3.039E+01 | 1.669E+01 | 1.694E+01 | 2.640E+01 | 3.171E+01 | 1.716E+01 | 1.664E+01 |
| 279 | 6.271E+00 | 6.390E+00 | 6.036E+00 | 6.614E+00 | 6.941E+00 | 1.074E+01 | 7.957E+00 | 4.982E+00 | 5.323E+00 | 7.101E+00 | 6.396E+00 | 4.781E+00 | 5.043E+00 |
| 280 | 6.213E+00 | 5.190E+00 | 6.407E+00 | 5.427E+00 | 6.211E+00 | 6.667E+00 | 6.297E+00 | 3.712E+00 | 4.281E+00 | 5.831E+00 | 5.776E+00 | 6.471E+00 | 5.155E+00 |
| 281 | 1.234E+02 | 9.032E+01 | 1.179E+02 | 1.222E+02 | 1.175E+02 | 1.108E+02 | 9.880E+01 | 1.152E+02 | 1.292E+02 | 1.225E+02 | 1.165E+02 | 1.122E+02 | 1.367E+02 |
| 282 | 1.050E+02 | 7.697E+01 | 1.009E+02 | 1.036E+02 | 1.002E+02 | 9.431E+01 | 8.501E+01 | 1.128E+02 | 1.094E+02 | 9.839E+01 | 1.018E+02 | 9.504E+01 | 1.174E+02 |
| 283 | 5.476E+01 | 4.019E+01 | 4.259E+01 | 4.539E+01 | 5.485E+01 | 3.975E+01 | 4.925E+01 | 4.501E+01 | 4.592E+01 | 5.067E+01 | 3.879E+01 | 4.052E+01 | 3.429E+01 |
| 284 | 6.536E+00 | 5.214E+00 | 7.109E+00 | 5.697E+00 | 4.982E+00 | 6.471E+00 | 6.837E+00 | 4.435E+00 | 5.419E+00 | 5.115E+00 | 5.795E+00 | 6.594E+00 | 7.725E+00 |
| 285 | 8.039E+01 | 7.301E+01 | 7.781E+01 | 7.321E+01 | 7.232E+01 | 7.686E+01 | 7.732E+01 | 7.653E+01 | 7.824E+01 | 6.311E+01 | 7.348E+01 | 8.096E+01 | 8.178E+01 |
| 286 | 6.049E+01 | 5.940E+01 | 6.142E+01 | 5.523E+01 | 5.383E+01 | 6.145E+01 | 6.076E+01 | 6.316E+01 | 6.095E+01 | 4.592E+01 | 5.912E+01 | 6.230E+01 | 6.426E+01 |
| 287 | 9.981E+00 | 8.903E+00 | 8.844E+00 | 8.228E+00 | 9.975E+00 | 9.488E+00 | 1.064E+01 | 7.476E+00 | 7.640E+00 | 7.015E+00 | 7.500E+00 | 9.352E+00 | 6.599E+00 |
| 288 | 5.491E+01 | 8.616E+01 | 7.442E+01 | 6.002E+01 | 6.037E+01 | 7.835E+01 | 7.309E+01 | 4.588E+01 | 4.978E+01 | 6.317E+01 | 7.483E+01 | 5.501E+01 | 4.560E+01 |
| 289 | 4.352E+01 | 6.885E+01 | 5.715E+01 | 4.620E+01 | 4.777E+01 | 6.303E+01 | 5.678E+01 | 3.863E+01 | 3.885E+01 | 5.019E+01 | 6.456E+01 | 4.324E+01 | 3.628E+01 |
| 290 | 2.018E+01 | 3.122E+01 | 3.013E+01 | 2.071E+01 | 1.783E+01 | 2.896E+01 | 2.810E+01 | 1.407E+01 | 1.471E+01 | 1.756E+01 | 2.688E+01 | 1.921E+01 | 1.712E+01 |
| 291 | 1.615E+01 | 2.565E+01 | 2.496E+01 | 1.685E+01 | 1.411E+01 | 2.423E+01 | 2.328E+01 | 1.595E+01 | 1.612E+01 | 1.407E+01 | 2.302E+01 | 1.557E+01 | 1.351E+01 |
| 292 | 2.119E+00 | 2.796E+00 | 2.884E+00 | 2.099E+00 | 2.159E+00 | 2.978E+00 | 2.905E+00 | 1.553E+00 | 1.788E+00 | 2.079E+00 | 2.538E+00 | 2.429E+00 | 1.769E+00 |
| 293 | 1.143E+00 | 2.295E+00 | 1.613E+00 | 1.701E+00 | 1.553E+00 | 1.979E+00 | 1.955E+00 | 5.260E−01 | 5.441E−01 | 1.356E+00 | 1.073E+00 | 1.441E+00 | 7.295E−01 |
| 294 | 1.970E+00 | 1.833E+00 | 1.906E+00 | 2.108E+00 | 1.522E+00 | 2.048E+00 | 1.775E+00 | 3.524E+00 | 3.407E+00 | 6.702E+00 | 3.033E+00 | 2.954E+00 | 3.407E+00 |
| 295 | 1.919E+00 | 1.795E+00 | 2.043E+00 | 2.142E+00 | 1.508E+00 | 2.032E+00 | 1.804E+00 | 3.466E+00 | 3.381E+00 | 6.567E+00 | 2.971E+00 | 2.990E+00 | 3.469E+00 |
| 296 | 1.517E+00 | 1.167E+00 | 1.258E+00 | 1.290E+00 | 1.091E+00 | 1.087E+00 | 1.267E+00 | 2.325E+00 | 2.181E+00 | 5.275E+00 | 1.997E+00 | 2.073E+00 | 1.952E+00 |
| 297 | 2.759E−01 | 2.850E−01 | 2.245E−01 | 1.924E−01 | 2.712E−01 | 2.965E−01 | 3.409E−01 | 6.366E−01 | 7.204E−01 | 1.650E−01 | 3.965E−01 | 2.756E−01 | 2.254E−01 |
| 298 | 1.141E−02 | 1.461E−02 | 1.244E−02 | 8.195E−03 | 1.358E−02 | 1.463E−02 | 1.545E−02 | 1.420E−02 | 2.145E−02 | 5.084E−03 | 9.224E−03 | 4.097E−03 | 5.427E−03 |

APPENDIX D-continued

Ovarian Cancer
Training Dataset

| | | | | | | | | | | | | | |
|---|---|---|---|---|---|---|---|---|---|---|---|---|---|
| 299 | 1.141E−01 | 9.611E−02 | 5.749E−02 | 6.693E−02 | 8.045E−02 | 1.049E−01 | 1.146E−01 | 1.124E−01 | 1.705E−01 | 5.513E−02 | 1.173E−01 | 5.342E−02 | 5.492E−02 |
| 300 | 5.792E−03 | 7.937E−03 | 3.282E−03 | 4.698E−03 | 4.784E−03 | 9.696E−03 | 1.064E−02 | 8.281E−03 | 8.495E−03 | 2.122E−03 | 6.264E−03 | 2.134E−03 | 1.315E−03 |
| 301 | 7.830E−02 | 6.436E−02 | 4.998E−02 | 4.677E−02 | 5.363E−02 | 5.728E−02 | 7.401E−02 | 9.417E−02 | 1.045E−01 | 3.432E−02 | 6.414E−01 | 3.861E−02 | 3.196E−02 |
| 302 | 9.611E−03 | 1.667E−02 | 1.122E−02 | 9.932E−03 | 2.210E−02 | 1.045E−02 | 1.886E−02 | 1.006E−02 | 1.959E−02 | 4.248E−04 | 3.304E−03 | 3.025E−03 | 2.137E−03 |
| 303 | 2.314E−01 | 2.248E−01 | 1.525E−01 | 1.542E−01 | 1.448E−01 | 1.982E−01 | 2.829E−01 | 2.432E−01 | 2.809E−01 | 7.294E−02 | 2.014E−01 | 1.309E−01 | 1.197E−01 |
| 304 | 5.620E−03 | 7.680E−03 | 4.998E−03 | 2.789E−03 | 1.109E−02 | 6.457E−03 | 6.028E−03 | 1.184E−02 | 1.371E−02 | 0.000E+00 | 8.238E−04 | 1.778E−04 | 8.216E−04 |
| 305 | 3.870E−01 | 4.158E−01 | 2.483E−01 | 3.018E−01 | 2.993E−01 | 3.660E−01 | 4.524E−01 | 3.822E−01 | 4.768E−01 | 1.723E−01 | 2.925E−01 | 1.909E−01 | 1.446E−01 |
| 306 | 2.252E−02 | 3.025E−02 | 1.950E−02 | 2.510E−02 | 1.645E−02 | 2.982E−02 | 3.733E−02 | 2.012E−02 | 2.553E−02 | 8.903E−03 | 1.746E−02 | 1.173E−02 | 8.881E−03 |
| 307 | 1.680E+00 | 1.655E+00 | 1.358E+00 | 1.115E+00 | 8.268E−01 | 1.429E+00 | 2.262E+00 | 1.098E+00 | 1.052E+00 | 3.780E−01 | 1.058E+00 | 6.559E−01 | 5.032E−01 |
| 308 | 3.196E−02 | 2.617E−02 | 2.939E−02 | 2.210E−02 | 1.148E−02 | 3.754E−02 | 4.591E−02 | 1.774E−02 | 1.568E−02 | 6.371E−03 | 2.143E−02 | 7.830E−03 | 7.229E−03 |
| 309 | 3.797E−03 | 4.097E−03 | 2.596E−03 | 2.789E−03 | 3.625E−03 | 5.878E−03 | 3.218E−03 | 2.360E−03 | 2.617E−03 | 2.553E−03 | 3.797E−03 | 1.600E−03 | 1.974E−03 |
| 310 | 1.268E−03 | 1.793E−03 | 1.208E−03 | 1.394E−03 | 1.339E−03 | 1.330E−03 | 2.006E−04 | 7.701E−03 | 3.261E−03 | 8.066E−03 | 1.648E−03 | 1.246E−03 | 2.467E−03 |
| 311 | 9.053E−04 | 1.025E−03 | 3.454E−04 | 3.475E−04 | 1.914E−04 | 5.706E−04 | 4.012E−04 | 1.774E−03 | 0.000E+00 | 2.122E−03 | 4.934E−04 | 1.778E−04 | 4.934E−04 |
| 312 | 0.000E+00 | 1.281E−03 | 1.727E−04 | 1.742E−04 | 0.000E+00 | 3.797E−04 | 2.006E−04 | 0.000E+00 | 6.521E−04 | 0.000E+00 | 4.934E−04 | 3.561E−04 | 1.150E−03 |
| 313 | 1.403E−01 | 1.727E−01 | 1.705E−01 | 1.233E−01 | 1.257E−01 | 1.903E−01 | 2.203E−01 | 1.178E−01 | 1.124E−01 | 7.551E−02 | 1.118E−01 | 6.285E−02 | 5.106E−02 |
| 314 | 4.719E−03 | 8.452E−03 | 4.312E−03 | 3.840E−03 | 4.977E−03 | 7.208E−03 | 7.015E−03 | 1.774E−03 | 3.261E−03 | 5.513E−03 | 2.960E−03 | 3.025E−03 | 2.639E−03 |
| 315 | 3.046E−02 | 3.411E−02 | 3.089E−02 | 1.847E−02 | 3.411E−02 | 2.896E−02 | 3.711E−02 | 1.598E−02 | 2.360E−02 | 1.697E−02 | 2.875E−02 | 1.085E−02 | 9.868E−03 |
| 316 | 9.053E−04 | 2.553E−03 | 8.624E−04 | 8.710E−04 | 1.148E−03 | 9.503E−04 | 2.006E−03 | 5.921E−04 | 0.000E+00 | 4.248E−04 | 1.154E−03 | 8.903E−04 | 3.282E−04 |
| 317 | 2.746E−02 | 3.411E−02 | 3.025E−02 | 2.274E−02 | 2.917E−02 | 2.403E−02 | 4.162E−02 | 2.188E−02 | 1.633E−02 | 1.358E−02 | 2.274E−02 | 1.334E−02 | 6.414E−03 |
| 318 | 7.251E−04 | 7.680E−04 | 2.072E−03 | 1.394E−03 | 2.104E−03 | 1.899E−03 | 2.210E−03 | 1.774E−03 | 3.261E−03 | 8.495E−04 | 1.317E−03 | 7.122E−04 | 3.282E−04 |
| 319 | 2.089E−01 | 2.433E−01 | 2.428E−01 | 1.873E−01 | 1.978E−01 | 1.750E−01 | 3.098E−01 | 1.454E−01 | 1.392E−01 | 1.073E−01 | 1.937E−01 | 1.193E−01 | 1.051E−01 |
| 320 | 1.813E−04 | 5.127E−04 | 1.036E−03 | 8.710E−04 | 5.728E−04 | 1.330E−03 | 4.012E−04 | 0.000E+00 | 0.000E+00 | 0.000E+00 | 9.889E−04 | 5.342E−04 | 1.643E−04 |
| 321 | 2.010E−01 | 2.615E−01 | 2.188E−01 | 1.789E−01 | 2.886E−01 | 2.502E−01 | 2.518E−01 | 1.480E−01 | 1.326E−01 | 1.163E−01 | 1.744E−01 | 1.013E−01 | 6.865E−02 |
| 322 | 7.980E−03 | 5.384E−03 | 8.109E−03 | 4.526E−03 | 9.375E−03 | 7.980E−03 | 9.439E−03 | 3.540E−03 | 5.234E−03 | 5.084E−03 | 8.066E−03 | 4.634E−03 | 2.639E−03 |
| 323 | 2.741E−01 | 2.935E−01 | 3.022E−01 | 2.322E−01 | 2.394E−01 | 2.409E−01 | 3.517E−01 | 1.798E−01 | 1.738E−01 | 1.064E−01 | 2.205E−01 | 1.298E−01 | 1.049E−01 |
| 324 | 6.521E−03 | 1.051E−02 | 8.109E−03 | 7.487E−03 | 6.500E−03 | 7.594E−03 | 9.224E−03 | 1.184E−03 | 4.569E−03 | 4.677E−03 | 9.718E−03 | 3.904E−03 | 3.776E−03 |
| 325 | 8.345E−03 | 8.967E−03 | 7.079E−03 | 6.436E−03 | 4.205E−03 | 8.924E−03 | 1.103E−02 | 8.281E−03 | 6.521E−03 | 5.513E−03 | 7.573E−03 | 6.414E−03 | 5.427E−03 |
| 326 | 9.053E−04 | 1.538E−03 | 1.036E−03 | 1.916E−03 | 3.818E−04 | 1.519E−03 | 1.605E−03 | 5.921E−04 | 6.521E−04 | 4.248E−04 | 6.586E−04 | 8.903E−04 | 6.586E−04 |
| 327 | 9.975E−03 | 1.461E−02 | 1.002E−02 | 9.932E−03 | 6.500E−03 | 1.197E−02 | 1.304E−02 | 7.101E−03 | 4.569E−03 | 8.903E−03 | 8.903E−03 | 7.658E−03 | 5.921E−03 |
| 328 | 1.268E−03 | 1.281E−03 | 8.624E−04 | 1.742E−03 | 1.339E−03 | 1.139E−03 | 2.810E−03 | 1.774E−03 | 0.000E+00 | 1.697E−03 | 6.586E−04 | 1.068E−03 | 1.643E−04 |
| 329 | 5.178E−01 | 6.108E−01 | 4.715E−01 | 3.226E−01 | 5.850E−01 | 6.263E−01 | 9.959E−01 | 3.426E−01 | 3.370E−01 | 3.084E−01 | 2.806E−01 | 2.546E−01 | 1.557E−01 |
| 330 | 3.625E−03 | 1.103E−02 | 5.170E−03 | 3.647E−03 | 5.363E−03 | 5.878E−03 | 6.221E−03 | 2.360E−03 | 1.306E−03 | 2.960E−03 | 2.960E−03 | 3.389E−03 | 1.643E−03 |
| 331 | 3.754E−02 | 4.076E−02 | 3.368E−02 | 2.446E−02 | 3.089E−02 | 3.218E−02 | 4.398E−02 | 1.774E−02 | 1.306E−02 | 1.783E−02 | 3.368E−02 | 2.064E−02 | 1.446E−02 |
| 332 | 7.251E−04 | 2.317E−03 | 6.908E−04 | 6.972E−04 | 1.914E−04 | 1.139E−03 | 2.006E−04 | 5.921E−04 | 0.000E+00 | 8.495E−04 | 6.586E−04 | 1.778E−04 | 1.643E−04 |
| 333 | 2.360E−02 | 3.282E−02 | 2.360E−02 | 1.585E−02 | 1.549E−02 | 1.995E−02 | 2.917E−02 | 1.184E−02 | 5.878E−03 | 1.019E−02 | 1.879E−02 | 1.761E−02 | 9.031E−03 |
| 334 | 7.251E−04 | 7.680E−04 | 1.727E−04 | 0.000E+00 | 1.148E−03 | 1.899E−04 | 4.012E−04 | 0.000E+00 | 0.000E+00 | 1.272E−03 | 1.648E−04 | 0.000E+00 | 0.000E+00 |
| 335 | 5.642E−02 | 7.744E−02 | 6.157E−02 | 3.754E−02 | 4.076E−02 | 4.977E−02 | 8.130E−02 | 3.904E−02 | 2.145E−02 | 2.767E−02 | 4.762E−02 | 2.939E−02 | 1.924E−02 |
| 336 | 3.797E−03 | 6.672E−03 | 3.797E−03 | 2.446E−03 | 3.432E−03 | 3.604E−03 | 4.012E−03 | 1.184E−03 | 3.926E−03 | 8.495E−04 | 1.482E−03 | 2.488E−03 | 1.150E−03 |
| 337 | 1.298E−01 | 1.422E−01 | 1.058E−01 | 4.698E−02 | 9.889E−02 | 1.036E−01 | 1.791E−01 | 6.393E−02 | 4.441E−02 | 6.822E−02 | 6.736E−02 | 4.870E−02 | 3.432E−02 |
| 338 | 1.088E−03 | 2.553E−03 | 2.252E−03 | 3.475E−04 | 1.720E−03 | 2.089E−03 | 3.411E−03 | 5.921E−04 | 1.306E−03 | 8.495E−04 | 1.317E−03 | 5.342E−04 | 9.868E−04 |
| 339 | 6.929E−02 | 8.860E−02 | 5.556E−02 | 3.840E−02 | 5.127E−02 | 5.191E−02 | 8.045E−02 | 2.012E−02 | 2.360E−02 | 2.252E−02 | 4.548E−02 | 3.347E−02 | 1.628E−02 |
| 340 | 2.531E−03 | 2.553E−03 | 2.939E−03 | 2.446E−03 | 1.720E−03 | 4.183E−03 | 3.411E−03 | 5.921E−04 | 1.959E−03 | 1.697E−03 | 1.813E−03 | 1.600E−03 | 9.868E−04 |
| 341 | 3.261E−03 | 6.157E−03 | 2.939E−03 | 3.132E−03 | 2.875E−03 | 3.797E−03 | 5.020E−03 | 5.921E−03 | 4.569E−03 | 6.779E−03 | 2.810E−03 | 2.853E−03 | 2.960E−03 |
| 342 | 1.813E−04 | 0.000E+00 | 1.036E−03 | 0.000E+00 | 3.818E−04 | 1.139E−03 | 4.012E−04 | 1.774E−03 | 6.521E−04 | 4.248E−04 | 8.238E−04 | 8.903E−04 | 1.643E−04 |
| 343 | 2.896E−03 | 6.929E−03 | 3.625E−03 | 4.183E−03 | 5.363E−03 | 7.980E−03 | 7.422E−03 | 4.140E−03 | 8.495E−03 | 2.960E−03 | 4.441E−03 | 7.830E−03 | 2.639E−03 |
| 344 | 5.427E−04 | 0.000E+00 | 1.727E−04 | 0.000E+00 | 1.914E−04 | 5.706E−04 | 1.004E−03 | 5.921E−04 | 6.521E−04 | 0.000E+00 | 1.648E−04 | 1.778E−04 | 1.643E−04 |

APPENDIX D-continued

Ovarian Cancer
Training Dataset

| | DL | DM | DN | DO | DP | DQ | DR | DS | DT | DU | DV | DW | DX |
|---|---|---|---|---|---|---|---|---|---|---|---|---|---|
| 1 | 13692 | 13695 | 13713 | 13785 | 13789 | 13804 | 13810 | 13815 | 13817 | 13822 | 13825 | 13832 | 13840 |
| 2 | Benign | Benign | Benign | Early Malignant | Benign | Benign | Benign | Benign | Benign | Benign | Benign | Benign | Benign |
| 3 | 1 | 1 | 1 | 2 | 1 | 1 | 1 | 1 | 1 | 1 | 1 | 1 | 1 |
| 4 | −1 | −1 | −1 | −1 | −1 | −1 | −1 | −1 | −1 | −1 | −1 | −1 | −1 |
| 5 | 1.547E+00 | 1.603E+00 | 2.682E−01 | 9.673E−01 | 2.156E+00 | 1.786E+00 | 1.002E+00 | 2.285E+00 | 1.878E+00 | 1.726E+00 | 1.311E+00 | 1.922E+00 | 1.382E+00 |
| 6 | 5.483E−01 | 9.608E−01 | 7.779E−02 | 7.454E−01 | 9.010E−01 | 9.812E−01 | 5.011E−01 | 9.001E−01 | 9.106E−01 | 9.793E−01 | 7.055E−01 | 6.416E−01 | 9.632E−01 |
| 7 | 2.629E−01 | 2.693E−01 | 4.957E−02 | 2.285E−01 | 3.798E−01 | 2.908E−01 | 1.502E−01 | 3.670E−01 | 3.165E−01 | 3.798E−01 | 2.532E−01 | 3.144E−01 | 2.672E−01 |
| 8 | 5.805E−01 | 5.912E−01 | 9.195E−02 | 3.562E−01 | 7.804E−01 | 5.826E−01 | 3.208E−01 | 6.685E−01 | 5.461E−01 | 6.341E−01 | 5.107E−01 | 6.406E−01 | 5.268E−01 |
| 9 | 3.026E−02 | 2.650E−02 | 3.380E−02 | 3.562E−02 | 2.210E−02 | 1.695E−02 | 3.208E−02 | 2.232E−02 | 1.459E−02 | 1.288E−02 | 1.170E−02 | 1.642E−02 | 1.073E−02 |
| 10 | 7.124E−03 | 1.749E−02 | 3.144E−03 | 5.472E−03 | 2.157E−02 | 1.3.41E−02 | 1.137E−02 | 1.760E−02 | 1.363E−02 | 1.609E−02 | 1.067E−02 | 1.277E−02 | 8.691E−03 |
| 11 | 1.427E−02 | 1.330E−02 | 6.288E−03 | 8.766E−03 | 1.556E−02 | 1.588E−02 | 1.191E−02 | 1.427E−02 | 1.320E−02 | 1.985E−02 | 8.530E−03 | 1.588E−02 | 1.223E−02 |
| 12 | 1.069E−02 | 8.498E−03 | 5.504E−03 | 4.925E−03 | 5.923E−03 | 8.455E−03 | 4.410E−03 | 1.045E−02 | 1.170E−02 | 4.818E−03 | 5.333E−03 | 1.094E−02 | 6.137E−03 |
| 13 | 7.124E−03 | 9.560E−03 | 3.927E−03 | 8.219E−03 | 5.923E−03 | 5.966E−03 | 6.921E−03 | 4.281E−03 | 5.848E−03 | 2.146E−03 | 2.661E−03 | 6.695E−03 | 1.534E−03 |
| 14 | 5.343E−02 | 8.015E−02 | 1.105E−02 | 6.191E−02 | 9.367E−02 | 9.045E−02 | 5.976E−02 | 5.225E−02 | 6.384E−02 | 6.845E−02 | 4.270E−02 | 6.212E−02 | 5.773E−02 |
| 15 | 4.753E−03 | 3.187E−03 | 5.504E−03 | 8.766E−03 | 6.459E−03 | 1.044E−02 | 5.665E−03 | 3.326E−03 | 1.073E−02 | 6.427E−03 | 7.468E−03 | 4.871E−03 | 5.118E−03 |
| 16 | 1.191E−03 | 2.124E−03 | 7.865E−04 | 5.472E−04 | 5.386E−04 | 0.000E+00 | 6.288E−04 | 4.753E−04 | 1.459E−03 | 1.071E−03 | 0.000E+00 | 0.000E+00 | 0.000E+00 |
| 17 | 4.753E−03 | 4.249E−03 | 7.865E−04 | 1.202E−02 | 3.230E−03 | 1.985E−03 | 3.144E−03 | 5.225E−03 | 2.436E−03 | 6.427E−03 | 1.599E−03 | 5.483E−03 | 5.118E−03 |
| 18 | 3.627E−02 | 2.071E−02 | 1.964E−02 | 2.790E−02 | 2.961E−02 | 2.639E−02 | 2.521E−02 | 5.279E−02 | 1.953E−02 | 2.886E−02 | 2.082E−02 | 3.230E−02 | 2.758E−02 |
| 19 | 1.212E−01 | 9.710E−02 | 2.597E−02 | 7.178E−02 | 1.320E−01 | 8.895E−02 | 7.049E−02 | 1.609E−01 | 1.004E−01 | 1.044E−01 | 6.985E−02 | 1.363E−01 | 7.725E−02 |
| 20 | 1.781E−03 | 2.124E−03 | 0.000E+00 | 3.830E−03 | 5.386E−04 | 3.981E−03 | 3.144E−03 | 1.899E−03 | 3.412E−03 | 2.146E−03 | 1.599E−03 | 3.047E−03 | 2.554E−03 |
| 21 | 1.191E−02 | 6.899E−03 | 9.431E−03 | 1.974E−02 | 1.234E−02 | 1.288E−02 | 8.176E−03 | 1.663E−02 | 1.556E−02 | 1.556E−02 | 8.530E−03 | 1.094E−02 | 1.277E−02 |
| 22 | 3.562E−03 | 1.062E−03 | 2.361E−03 | 1.642E−03 | 1.073E−03 | 3.476E−03 | 1.255E−03 | 9.506E−04 | 4.882E−04 | 2.672E−03 | 1.599E−03 | 3.047E−03 | 1.023E−03 |
| 23 | 4.989E−02 | 4.721E−02 | 3.305E−02 | 5.150E−02 | 7.210E−02 | 6.159E−02 | 6.545E−02 | 6.888E−02 | 5.558E−02 | 6.212E−02 | 4.109E−02 | 5.118E−02 | 6.341E−02 |
| 24 | 7.006E−02 | 4.828E−02 | 5.107E−02 | 5.536E−02 | 7.318E−02 | 4.667E−02 | 6.352E−02 | 8.509E−02 | 5.311E−02 | 8.240E−02 | 3.412E−02 | 6.878E−02 | 5.730E−02 |
| 25 | 1.964E−02 | 2.650E−02 | 6.288E−03 | 2.790E−02 | 2.479E−02 | 2.929E−02 | 2.082E−02 | 3.090E−02 | 3.165E−02 | 4.174E−02 | 2.028E−02 | 1.824E−02 | 3.122E−02 |
| 26 | 2.318E−02 | 1.009E−02 | 1.255E−02 | 2.135E−02 | 4.356E−02 | 1.191E−02 | 2.457E−02 | 1.620E−02 | 1.760E−02 | 1.878E−02 | 2.028E−02 | 2.682E−02 | 1.277E−02 |
| 27 | 4.753E−03 | 2.124E−03 | 4.721E−03 | 3.283E−03 | 8.616E−03 | 6.964E−03 | 4.410E−03 | 7.124E−03 | 7.318E−03 | 5.354E−03 | 2.135E−03 | 3.648E−03 | 3.584E−03 |
| 28 | 2.436E−02 | 2.017E−02 | 8.648E−03 | 3.455E−02 | 3.873E−02 | 2.779E−02 | 3.337E−02 | 3.562E−02 | 1.803E−02 | 4.013E−02 | 3.305E−02 | 2.983E−02 | 4.034E−02 |
| 29 | 3.562E−02 | 3.873E−02 | 2.436E−02 | 3.948E−02 | 3.659E−02 | 3.326E−02 | 2.768E−02 | 4.131E−02 | 3.755E−02 | 5.354E−02 | 3.948E−02 | 2.800E−02 | 4.807E−02 |
| 30 | 7.843E−02 | 5.472E−02 | 8.723E−02 | 5.097E−02 | 5.333E−02 | 4.775E−02 | 7.232E−02 | 7.275E−02 | 7.167E−02 | 7.650E−02 | 5.011E−02 | 5.966E−02 | 5.418E−02 |
| 31 | 6.534E−02 | 3.348E−02 | 4.560E−02 | 4.818E−02 | 4.088E−02 | 3.380E−02 | 3.959E−02 | 4.088E−02 | 5.461E−02 | 6.105E−02 | 3.358E−02 | 5.354E−02 | 4.034E−02 |
| 32 | 1.309E−02 | 1.588E−02 | 8.648E−03 | 7.672E−03 | 1.395E−02 | 1.044E−02 | 8.809E−03 | 1.045E−02 | 1.127E−02 | 1.071E−02 | 6.931E−03 | 2.071E−02 | 6.642E−03 |
| 33 | 1.309E−02 | 1.384E−02 | 7.865E−03 | 1.148E−02 | 1.395E−02 | 1.191E−02 | 1.255E−02 | 9.506E−03 | 2.049E−02 | 1.663E−02 | 1.330E−02 | 1.524E−02 | 1.180E−02 |
| 34 | 7.071E−02 | 5.204E−02 | 9.828E−02 | 4.378E−02 | 7.318E−02 | 5.762E−02 | 5.730E−02 | 5.655E−02 | 6.094E−02 | 5.139E−02 | 5.279E−02 | 9.077E−02 | 3.830E−02 |
| 35 | 6.652E−02 | 6.052E−02 | 7.629E−02 | 6.352E−02 | 8.283E−02 | 5.021E−02 | 6.545E−02 | 7.124E−02 | 6.631E−02 | 8.616E−02 | 4.528E−02 | 7.006E−02 | 4.957E−02 |
| 36 | 8.315E−03 | 1.009E−02 | 1.180E−02 | 2.189E−03 | 1.556E−02 | 9.442E−03 | 6.921E−03 | 7.124E−03 | 7.318E−03 | 9.635E−03 | 4.270E−03 | 5.483E−03 | 6.137E−03 |
| 37 | 1.363E−02 | 1.009E−02 | 1.964E−02 | 2.908E−02 | 8.616E−03 | 1.395E−02 | 1.006E−02 | 1.234E−02 | 1.025E−02 | 9.635E−03 | 2.350E−02 | 1.770E−02 | 1.738E−02 |
| 38 | 2.972E−03 | 4.775E−03 | 7.865E−03 | 1.695E−02 | 4.839E−03 | 2.489E−03 | 4.410E−03 | 5.225E−03 | 4.388E−03 | 5.891E−03 | 3.197E−03 | 1.094E−02 | 9.206E−03 |
| 39 | 9.678E−02 | 1.202E−01 | 1.127E−01 | 1.931E−01 | 1.309E−01 | 1.159E−01 | 5.976E−02 | 6.985E−02 | 1.094E−01 | 9.206E−02 | 1.159E−01 | 8.219E−02: | 1.008E−01 |
| 40 | 1.770E−01 | 1.202E−01 | 1.631E−01 | 1.481E−01 | 1.033E−01 | 9.936E−02 | 9.185E−02 | 9.839E−02 | 1.094E−01 | 1.060E−01 | 1.438E−01 | 1.438E−01 | 1.202E−01 |
| 41 | 2.672E−02 | 1.438E−02 | 7.071E−03 | 1.373E−02 | 1.609E−02 | 1.835E−02 | 1.448E−02 | 1.706E−02 | 1.609E−02 | 1.234E−02 | 1.921E−02 | 2.189E−02 | 1.534E−02 |
| 42 | 2.371E−03 | 2.650E−03 | 7.865E−04 | 2.189E−03 | 2.693E−03 | 1.491E−03 | 2.521E−03 | 1.427E−03 | 2.929E−03 | 2.146E−03 | 3.734E−03 | 7.307E−03 | 2.049E−03 |
| 43 | 8.693E−03 | 7.639E−03 | 1.168E−02 | 3.806E−03 | 8.513E−03 | 1.109E−02 | 8.436E−03 | 1.070E−02 | 9.465E−03 | 6.661E−03 | 5.504E−03 | 7.742E−03 | 6.121E−03 |
| 44 | 1.124E−01 | 1.003E−01 | 1.656E−01 | 9.876E−02 | 1.304E−01 | 1.057E−01 | 1.605E−01 | 1.109E−01 | 1.242E−01 | 8.230E−02 | 8.667E−02 | 1.093E−01 | 7.484E−02 |
| 45 | 9.953E−02 | 9.259E−02 | 8.256E−02 | 7.716E−02 | 9.851E−02 | 9.285E−02 | 1.003E−01 | 7.201E−02 | 8.050E−02 | 5.272E−02 | 5.427E−02 | 5.993E−02 | 7.124E−02 |
| 46 | 1.830E−01 | 9.876E−02 | 2.538E−01 | 1.075E−01 | 1.667E−01 | 1.178E−01 | 1.837E−01 | 1.399E−01 | 1.577E−01 | 9.259E−02 | 9.208E−02 | 1.379E−01 | 9.233E−02 |
| 47 | 6.301E−02 | 4.244E−02 | 1.394E−01 | 6.790E−02 | 4.655E−02 | 3.704E−02 | 7.793E−02 | 4.115E−02 | 5.195E−02 | 2.855E−02 | 4.244E−02 | 4.321E−02 | 4.167E−02 |
| 48 | 9.105E−03 | 8.513E−03 | 1.433E−02 | 1.391E−02 | 1.690E−02 | 8.925E−03 | 1.147E−02 | 8.436E−03 | 8.642E−03 | 6.919E−03 | 7.021E−03 | 1.021E−02 | 7.716E−03 |

APPENDIX D-continued

Ovarian Cancer
Training Dataset

| | | | | | | | | | | | | | |
|---|---|---|---|---|---|---|---|---|---|---|---|---|---|
| 49 | 8.539E−03 | 7.510E−03 | 5.838E−03 | 7.742E−03 | 8.256E−03 | 8.333E−03 | 8.899E−03 | 6.378E−03 | 8.179E−03 | 3.344E−03 | 7.150E−03 | 6.867E−03 | 5.761E−03 |
| 50 | 3.704E−03 | 2.418E−03 | 3.009E−03 | 3.163E−03 | 1.677E−03 | 1.430E−03 | 1.057E−03 | 2.726E−03 | 1.286E−03 | 2.181E−03 | 1.533E−03 | 2.906E−03 | 3.421E−03 |
| 51 | 1.607E−01 | 1.047E−01 | 1.741E−01 | 8.616E−02 | 1.065E−01 | 1.137E−01 | 1.201E−01 | 2.831E−01 | 2.343E−01 | 1.751E−01 | 1.330E−01 | 2.001E−01 | 1.193E−01 |
| 52 | 3.704E−03 | 2.292E−03 | 2.649E−03 | 2.232E−03 | 1.806E−03 | 3.575E−03 | 4.527E−03 | 5.350E−03 | 4.552E−03 | 2.567E−03 | 3.575E−03 | 2.778E−03 | 2.701E−03 |
| 53 | 1.510E−02 | 9.285E−03 | 1.263E−02 | 9.310E−03 | 1.253E−02 | 1.013E−02 | 1.296E−02 | 9.799E−03 | 1.065E−02 | 6.018E−03 | 9.336E−03 | 1.649E−02 | 8.693E−03 |
| 54 | 4.065E+00 | 5.113E+00 | 6.223E+00 | 6.045E+00 | 4.166E+00 | 6.026E+00 | 5.791E+00 | 4.894E+00 | 5.439E+00 | 5.473E+00 | 5.063E+00 | 4.501E+00 | 5.778E+00 |
| 55 | 6.982E−01 | 5.402E−01 | 9.008E−01 | 5.728E−01 | 5.010E−01 | 4.883E−01 | 4.976E−01 | 6.937E−01 | 6.127E−01 | 6.202E−01 | 5.283E−01 | 7.007E−01 | 4.690E−01 |
| 56 | 1.355E−01 | 1.790E−01 | 1.769E−01 | 1.793E−01 | 1.368E−01 | 1.800E−01 | 1.707E−01 | 1.597E−01 | 1.590E−01 | 1.643E−01 | 1.574E−01 | 1.386E−01 | 1.749E−01 |
| 57 | 3.856E+00 | 2.669E+00 | 5.070E+00 | 3.014E+00 | 2.739E+00 | 2.753E+00 | 3.056E+00 | 3.743E+00 | 3.625E+00 | 3.772E+00 | 2.959E+00 | 4.110E+00 | 2.716E+00 |
| 58 | 5.941E−02 | 4.501E−02 | 7.304E−02 | 3.884E−02 | 4.578E−02 | 5.144E−02 | 8.873E−02 | 5.787E−02 | 6.353E−02 | 4.218E−02 | 4.321E−02 | 6.250E−02 | 3.729E−02 |
| 59 | 5.941E−02 | 4.990E−02 | 7.176E−02 | 5.067E−02 | 4.604E−02 | 4.707E−02 | 4.449E−02 | 5.607E−02 | 5.375E−02 | 5.375E−02 | 5.427E−02 | 6.558E−02 | 4.089E−02 |
| 60 | 6.276E−03 | 5.735E−03 | 6.018E−03 | 4.604E−03 | 6.070E−03 | 6.070E−03 | 5.118E−03 | 3.884E−03 | 5.504E−03 | 5.504E−03 | 5.375E−03 | 8.307E−03 | 5.761E−03 |
| 61 | 1.023E+00 | 1.368E+00 | 2.290E+00 | 1.417E+00 | 1.870E+00 | 1.257E+00 | 1.596E+00 | 1.112E+00 | 1.242E+00 | 1.131E+00 | 1.179E+00 | 2.115E+00 | 1.104E+00 |
| 62 | 3.983E−01 | 5.990E−01 | 5.291E−01 | 6.490E−01 | 4.785E−01 | 5.736E−01 | 3.465E−01 | 4.955E−01 | 4.404E−01 | 5.903E−01 | 6.120E−01 | 3.691E−01 | 7:891E−01 |
| 63 | 7.819E−03 | 6.096E−03 | 1.245E−02 | 6.970E−03 | 1.018E−02 | 9.285E−03 | 9.208E−03 | 7.510E−03 | 8.770E−03 | 8.462E−03 | 5.761E−03 | 1.371E−02 | 8.333E−03 |
| 64 | 2.311E+00 | 3.159E+00 | 2.212E+00 | 3.117E+00 | 2.278E+00 | 2.561E+00 | 1.941E+00 | 2.245E+00 | 2.141E+00 | 2.768E+00 | 2.813E+00 | 1.937E+00 | 3.047E+00 |
| 65 | 9.002E−02 | 1.062E−01 | 8.256E−02 | 1.006E−01 | 7.947E−02 | 9.671E−02 | 9.568E−02 | 7.896E−02 | 8.410E−02 | 9.542E−02 | 9.953E−02 | 7.742E−02 | 1.029E−01 |
| 66 | 8.609E−01 | 6.263E−01 | 6.644E−01 | 5.740E−01 | 5.291E−01 | 4.430E−01 | 4.056E−01 | 7.175E−01 | 5.877E−01 | 6.863E−01 | 7.356E−01 | 5.762E−01 | 6.176E−01 |
| 67 | 5.427E−02 | 3.524E−02 | 4.810E−02 | 3.215E−02 | 4.141E−02 | 3.421E−02 | 7.947E−02 | 5.067E−02 | 5.195E−02 | 2.906E−02 | 4.089E−02 | 4.527E−02 | 2.881E−02 |
| 68 | 1.510E−02 | 1.170E−02 | 1.150E−02 | 1.273E−02 | 1.134E−02 | 1.571E−02 | 1.358E−02 | 7.176E−03 | 1.250E−02 | 1.129E−02 | 1.317E−02 | 1.474E−02 | 1.335E−02 |
| 69 | 4.862E−01 | 6.815E−01 | 8.081E−01 | 6.295E−01 | 9.770E−01 | 4.915E−01 | 5.607E−01 | 3.944E−01 | 4.528E−01 | 4.501E−01 | 5.289E−01 | 9.183E−01 | 4.948E−01 |
| 70 | 1.821E−02 | 2.150E−02 | 2.204E−02 | 1.890E−02 | 2.052E−02 | 1.775E−02 | 2.248E−02 | 1.584E−02 | 1.543E−02 | 1.219E−02 | 1.343E−02 | 2.451E−02 | 1.543E−02 |
| 71 | 4.835E−03 | 3.678E−03 | 4.707E−03 | 1.708E−03 | 4.398E−03 | 4.167E−03 | 4.372E−03 | 3.421E−03 | 3.858E−03 | 3.344E−03 | 3.061E−03 | 5.993E−03 | 1.715E−03 |
| 72 | 1.849E−03 | 2.546E−03 | 3.215E−03 | 1.181E−03 | 2.194E−03 | 2.263E−03 | 1.960E−03 | 3.189E−03 | 2.803E−03 | 2.052E−03 | 3.832E−03 | 3.498E−03 | 2.207E−03 |
| 73 | 6.242E−03 | 2.235E−03 | 2.483E−03 | 5.756E−04 | 1.129E−03 | 1.569E−03 | 1.321E−03 | 1.501E−03 | 5.135E−04 | 5.632E−04 | 1.682E−03 | 0.000E+00 | 5.384E−04 |
| 74 | 6.242E−03 | 8.375E−03 | 1.659E−03 | 5.756E−03 | 8.488E−03 | 5.226E−03 | 3.307E−03 | 5.000E−03 | 2.054E−03 | 2.810E−03 | 3.363E−03 | 1.089E−02 | 4.300E−03 |
| 75 | 5.745E−02 | 4.244E−02 | 3.973E−02 | 5.824E−02 | 4.357E−02 | 3.871E−02 | 5.361E−02 | 4.898E−02 | 5.542E−02 | 7.257E−02 | 3.646E−02 | 5.056E−02 | 4.300E−02 |
| 76 | 8.251E−02 | 3.792E−02 | 5.214E−02 | 5.474E−02 | 4.018E−02 | 4.763E−02 | 6.095E−02 | 6.196E−02 | 9.233E−02 | 9.740E−02 | 3.194E−02 | 7.427E−02 | 4.413E−02 |
| 77 | 5.000E−03 | 4.470E−03 | 4.966E−03 | 6.919E−03 | 5.666E−03 | 7.325E−03 | 8.600E−03 | 8.002E−03 | 7.698E−03 | 1.126E−02 | 3.363E−03 | 5.767E−03 | 4.300E−03 |
| 78 | 1.253E−03 | 5.587E−04 | 0.000E+00 | 2.878E−03 | 5.666E−04 | 1.569E−03 | 0.000E+00 | 1.501E−03 | 0.000E+00 | 0.000E+00 | 0.000E+00 | 0.000E+00 | 1.076E−03 |
| 79 | 6.874E−03 | 6.704E−03 | 4.966E−03 | 1.670E−02 | 1.129E−03 | 5.756E−03 | 2.652E−03 | 1.501E−03 | 2.562E−03 | 6.761E−03 | 3.363E−03 | 1.919E−03 | 4.842E−03 |
| 80 | 6.242E−04 | 2.235E−03 | 1.659E−03 | 4.029E−03 | 1.129E−03 | 5.226E−04 | 1.321E−03 | 1.000E−03 | 2.054E−03 | 0.000E+00 | 1.122E−03 | 1.275E−03 | 5.384E−04 |
| 81 | 2.754E−02 | 1.569E−02 | 1.321E−02 | 2.935E−02 | 1.467E−02 | 1.098E−02 | 2.246E−02 | 8.995E−03 | 1.185E−02 | 1.242E−02 | 8.973E−03 | 1.025E−02 | 1.021E−02 |
| 82 | 2.494E−03 | 3.905E−03 | 5.790E−03 | 1.558E−02 | 2.833E−03 | 5.226E−03 | 5.959E−03 | 3.995E−03 | 6.670E−03 | 2.810E−03 | 2.799E−03 | 5.124E−03 | 1.076E−03 |
| 83 | 3.126E−03 | 2.235E−03 | 8.273E−04 | 3.454E−03 | 3.397E−03 | 2.619E−03 | 1.986E−03 | 5.000E−04 | 1.026E−03 | 2.257E−03 | 5.609E−04 | 6.400E−04 | 1.076E−03 |
| 84 | 1.806E−02 | 1.569E−02 | 8.273E−03 | 9.797E−03 | 1.298E−02 | 1.253E−02 | 2.246E−02 | 1.151E−02 | 1.287E−02 | 7.314E−03 | 9.537E−03 | 1.479E−02 | 1.287E−02 |
| 85 | 4.368E−03 | 1.117E−03 | 2.483E−03 | 1.151E−03 | 1.693E−03 | 3.138E−03 | 3.973E−03 | 1.000E−03 | 1.026E−03 | 5.632E−04 | 2.799E−03 | 2.562E−03 | 1.614E−03 |
| 86 | 1.309E−02 | 5.023E−03 | 8.273E−03 | 9.221E−03 | 6.230E−03 | 7.325E−03 | 1.716E−02 | 7.494E−03 | 1.490E−02 | 1.467E−02 | 2.799E−03 | 1.089E−02 | 4.842E−03 |
| 87 | 3.059E−02 | 1.117E−02 | 3.555E−02 | 2.302E−02 | 1.129E−02 | 2.923E−02 | 3.646E−02 | 1.795E−02 | 3.950E−02 | 3.713E−02 | 1.230E−02 | 5.192E−02 | 2.370E−02 |
| 88 | 5.000E−03 | 2.788E−03 | 7.438E−03 | 7.494E−03 | 1.693E−03 | 3.657E−03 | 4.639E−03 | 3.002E−03 | 7.178E−03 | 3.939E−03 | 1.122E−03 | 1.275E−02 | 2.686E−03 |
| 89 | 1.433E−02 | 8.375E−03 | 7.438E−03 | 1.037E−02 | 1.298E−02 | 9.932E−03 | 1.524E−02 | 1.298E−02 | 1.129E−02 | 1.014E−02 | 7.291E−03 | 1.727E−02 | 9.142E−03 |
| 90 | 2.810E−02 | 1.343E−02 | 4.966E−02 | 3.510E−02 | 1.761E−02 | 2.777E−02 | 3.375E−02 | 3.950E−02 | 5.135E−02 | 6.648E−02 | 1.010E−02 | 4.481E−02 | 2.201E−02 |
| 91 | 7.494E−03 | 5.587E−03 | 3.307E−03 | 2.302E−03 | 3.962E−03 | 7.844E−03 | 4.639E−03 | 1.151E−02 | 1.026E−02 | 9.571E−03 | 3.363E−03 | 7.686E−03 | 3.228E−03 |
| 92 | 1.501E−02 | 1.343E−02 | 1.321E−02 | 1.501E−02 | 8.488E−03 | 1.151E−02 | 1.524E−02 | 8.002E−03 | 1.693E−02 | 2.032E−02 | 2.799E−03 | 1.411E−02 | 6.456E−03 |
| 93 | 7.494E−03 | 3.352E−03 | 4.131E−03 | 7.494E−03 | 3.962E−03 | 5.226E−04 | 1.196E−02 | 3.995E−03 | 5.643E−03 | 7.314E−03 | 2.246E−03 | 8.962E−03 | 7.528E−03 |
| 94 | 1.874E−03 | 5.587E−04 | 2.483E−03 | 2.302E−03 | 1.693E−03 | 2.088E−03 | 1.321E−03 | 5.000E−04 | 4.108E−03 | 1.126E−03 | 1.682E−03 | 6.400E−04 | 1.076E−03 |
| 95 | 1.998E−02 | 1.230E−02 | 1.163E−02 | 8.070E−03 | 1.467E−02 | 9.932E−03 | 9.932E−03 | 1.196E−02 | 1.185E−02 | 6.196E−03 | 6.727E−03 | 2.246E−02 | 1.185E−02 |
| 96 | 5.621E−03 | 4.470E−03 | 1.163E−02 | 6.343E−03 | 7.359E−03 | 7.325E−03 | 9.266E−03 | 3.499E−03 | 8.205E−03 | 5.632E−03 | 6.727E−03 | 7.686E−03 | 9.142E−03 |
| 97 | 4.368E−03 | 7.257E−03 | 4.966E−03 | 4.605E−03 | 2.833E−03 | 3.657E−03 | 3.307E−03 | 7.494E−03 | 8.725E−03 | 3.939E−03 | 2.799E−03 | 4.481E−03 | 4.842E−03 |
| 98 | 1.433E−02 | 1.006E−02 | 4.131E−03 | 1.151E−02 | 9.063E−03 | 5.756E−03 | 1.388E−02 | 3.995E−03 | 8.725E−03 | 1.126E−02 | 5.609E−03 | 1.603E−02 | 6.986E−03 |

APPENDIX D-continued

Ovarian Cancer
Training Dataset

| | | | | | | | | | | | | | |
|---|---|---|---|---|---|---|---|---|---|---|---|---|---|
| 99 | 9.025E−02 | 1.422E−01 | 1.042E−01 | 1.002E−01 | 8.240E−02 | 1.312E−01 | 1.079E−01 | 7.872E−02 | 1.082E−01 | 1.071E−01 | 1.582E−01 | 9.810E−02 | 1.209E−01 |
| 100 | 3.532E−02 | 3.642E−02 | 4.132E−02 | 2.624E−02 | 3.323E−02 | 3.176E−02 | 4.819E−02 | 6.352E−02 | 3.397E−02 | 3.666E−02 | 3.899E−02 | 4.316E−02 | 3.617E−02 |
| 101 | 1.631E−01 | 1.545E−01 | 1.398E−01 | 1.151E−01 | 1.508E−01 | 1.324E−01 | 1.275E−01 | 1.337E−01 | 1.132E−01 | 1.162E−01 | 1.219E−01 | 1.422E−01 | 1.582E−01 |
| 102 | 1.074E+00 | 8.412E−01 | 1.754E−01 | 6.156E−01 | 7.235E−01 | 7.456E−01 | 1.394E+00 | 6.891E−01 | 7.100E−01 | 6.622E−01 | 6.622E−01 | 7.922E−01 | 7.676E−01 |
| 103 | 1.594E−01 | 1.925E−01 | 1.901E−01 | 1.631E−01 | 1.251E−01 | 1.839E−01 | 1.717E−01 | 1.337E−01 | 1.619E−01 | 1.288E−01 | 1.508E−01 | 1.974E−01 | 1.913E−01 |
| 104 | 3.691E−01 | 3.237E−01 | 1.766E−01 | 2.649E−01 | 3.409E−01 | 3.250E−01 | 4.525E−01 | 3.360E−01 | 3.004E−01 | 2.968E−01 | 3.213E−01 | 2.869E−01 | 3.286E−01 |
| 105 | 1.327E+00 | 1.083E+00 | 1.221E−01 | 8.338E−01 | 8.608E−01 | 8.759E−01 | 1.704E+00 | 7.357E−01 | 8.272E−01 | 8.191E−01 | 7.456E−01 | 1.009E+00 | 8.449E−01 |
| 106 | 1.398E−01 | 1.655E−01 | 2.330E−01 | 1.754E−01 | 2.281E−01 | 2.232E−01 | 1.790E−01 | 2.146E−01 | 1.704E−01 | 2.072E−01 | 2.403E−01 | 1.668E−01 | 2.354E−01 |
| 107 | 1.106E−01 | 1.251E−01 | 9.160E−02 | 1.158E−01 | 1.071E−01 | 1.312E−01 | 9.135E−02 | 1.239E−01 | 7.909E−02 | 1.181E−01 | 1.545E−01 | 9.528E−02 | 1.582E−01 |
| 108 | 1.508E−01 | 1.619E−01 | 1.557E−01 | 1.778E−01 | 1.717E−01 | 1.729E−01 | 1.471E−01 | 1.373E−01 | 1.386E−01 | 2.342E−01 | 1.643E−01 | 1.619E−01 | 1.839E−01 |
| 109 | 9.503E−03 | 7.284E−03 | 1.435E−02 | 1.189E−02 | 3.691E−03 | 6.254E−03 | 2.882E−03 | 4.341E−03 | 3.899E−03 | 2.452E−03 | 6.094E−03 | 9.050E−03 | 4.096E−03 |
| 110 | 1.361E−02 | 6.671E−03 | 6.291E−03 | 1.570E−02 | 7.382E−03 | 9.086E−03 | 2.882E−03 | 1.741E−02 | 1.059E−02 | 1.471E−02 | 1.398E−02 | 1.741E−02 | 1.459E−02 |
| 111 | 1.221E−02 | 9.099E−03 | 7.186E−03 | 1.373E−02 | 7.382E−03 | 5.677E−03 | 2.158E−03 | 1.251E−02 | 1.288E−02 | 1.101E−02 | 1.582E−02 | 1.183E−02 | 1.052E−02 |
| 112 | 1.288E−02 | 9.099E−03 | 4.488E−03 | 5.628E−03 | 9.221E−03 | 7.958E−03 | 4.316E−03 | 1.361E−02 | 1.508E−02 | 1.349E−02 | 9.749E−03 | 8.351E−03 | 9.933E−03 |
| 113 | 4.746E−03 | 2.428E−03 | 1.803E−03 | 4.378E−03 | 1.226E−03 | 3.973E−03 | 7.186E−04 | 3.262E−03 | 3.899E−03 | 4.280E−03 | 3.041E−03 | 2.085E−03 | 1.754E−03 |
| 114 | 5.432E−03 | 3.029E−03 | 5.395E−03 | 6.254E−03 | 2.465E−03 | 3.973E−03 | 3.593E−03 | 3.801E−03 | 2.784E−03 | 1.839E−03 | 3.041E−03 | 2.784E−03 | 2.342E−03 |
| 115 | 5.432E−03 | 4.856E−03 | 8.988E−03 | 5.003E−03 | 2.465E−03 | 3.973E−03 | 2.158E−03 | 3.801E−03 | 4.464E−03 | 3.053E−03 | 4.267E−03 | 6.953E−03 | 3.507E−03 |
| 116 | 4.071E−03 | 1.815E−03 | 3.593E−03 | 1.251E−03 | 2.465E−03 | 2.845E−03 | 1.435E−03 | 1.631E−03 | 0.000E+00 | 2.452E−03 | 1.219E−03 | 1.386E−03 | 2.342E−03 |
| 117 | 4.071E−03 | 5.457E−03 | 5.395E−03 | 6.254E−03 | 7.995E−03 | 6.254E−03 | 4.316E−03 | 9.234E−03 | 4.464E−03 | 4.280E−03 | 6.094E−03 | 1.044E−02 | 7.590E−03 |
| 118 | 6.107E−03 | 4.856E−03 | 7.186E−03 | 4.378E−03 | 1.839E−03 | 1.135E−03 | 3.593E−03 | 2.710E−03 | 3.899E−03 | 4.280E−03 | 6.094E−04 | 2.085E−03 | 2.342E−03 |
| 119 | 6.107E−03 | 1.214E−03 | 8.988E−04 | 9.393E−03 | 4.304E−03 | 1.135E−03 | 7.186E−04 | 1.631E−03 | 2.784E−03 | 2.452E−03 | 3.041E−03 | 4.169E−03 | 1.169E−03 |
| 120 | 4.071E−03 | 4.856E−03 | 3.593E−03 | 2.502E−03 | 4.917E−03 | 2.269E−03 | 1.435E−03 | 3.801E−03 | 5.015E−03 | 1.839E−03 | 5.481E−03 | 4.169E−03 | 1.754E−03 |
| 121 | 9.350E−02 | 1.104E−01 | 9.528E−02 | 1.763E−01 | 1.692E−01 | 8.531E−02 | 8.557E−02 | 1.086E−01 | 1.149E−01 | 1.451E−01 | 3.473E−01 | 1.220E−01 | 2.306E−01 |
| 122 | 8.905E−02 | 7.979E−02 | 8.433E−02 | 1.407E−01 | 1.736E−01 | 1.211E−01 | 9.439E−02 | 2.004E−01 | 1.817E−01 | 2.262E−01 | 2.289E−01 | 7.845E−02 | 1.282E−01 |
| 123 | 2.894E+00 | 2.012E+00 | 2.297E+00 | 1.852E+00 | 1.995E+00 | 2.155E+00 | 2.191E+00 | 2.529E+00 | 2.110E+00 | 1.336E+00 | 2.262E+00 | 2.618E+00 | 1.808E+00 |
| 124 | 6.794E−02 | 4.933E−02 | 9.528E−02 | 7.444E−02 | 6.545E−02 | 4.265E−02 | 4.951E−02 | 5.102E−02 | 7.329E−02 | 6.509E−02 | 1.870E−01 | 3.918E−02 | 9.528E−02 |
| 125 | 1.193E−01 | 9.528E−02 | 1.015E−01 | 1.728E−01 | 9.617E−02 | 6.759E−02 | 6.305E−02 | 9.884E−02 | 4.185E−02 | 1.380E−01 | 2.636E−01 | 7.409E−02 | 1.541E−01 |
| 126 | 2.378E−01 | 8.085E−01 | 4.443E−01 | 9.795E−01 | 7.159E−01 | 8.887E−01 | 2.609E−01 | 7.204E−01 | 5.548E−01 | 9.083E−01 | 1.051E+00 | 3.874E−01 | 1.238E+00 |
| 127 | 1.496E+00 | 1.398E+00 | 1.514E+00 | 2.119E+00 | 1.549E+00 | 1.683E+00 | 7.293E−01 | 1.647E+00 | 1.594E+00 | 1.772E+00 | 2.395E+00 | 1.398E+00 | 1.915E+00 |
| 128 | 2.093E+00 | 1.549E+00 | 1.211E+00 | 1.443E+00 | 1.879E+00 | 1.523E+00 | 1.451E+00 | 1.665E+00 | 1.523E+00 | 1.282E+00 | 1.710E+00 | 2.271E+00 | 1.380E+00 |
| 129 | 3.820E−02 | 5.699E−02 | 6.750E−02 | 3.526E−02 | 2.698E−02 | 2.841E−02 | 4.052E−02 | 5.441E−02 | 4.889E−02 | 3.829E−02 | 5.343E−02 | 5.227E−02 | 2.191E−02 |
| 130 | 7.201E+00 | 1.245E+01 | 1.266E+01 | 1.873E+01 | 1.664E+01 | 1.220E+01 | 4.105E+00 | 7.439E+00 | 7.139E+00 | 1.261E+01 | 1.371E+01 | 8.651E+00 | 1.026E+01 |
| 131 | 5.806E+00 | 9.191E+00 | 9.611E+00 | 1.051E+01 | 1.283E+01 | 1.188E+01 | 6.406E+00 | 6.283E+00 | 7.820E+00 | 9.656E+00 | 1.238E+01 | 6.682E+00 | 9.873E+00 |
| 132 | 7.222E−02 | 4.559E−02 | 3.375E−02 | 3.918E−02 | 4.239E−02 | 3.553E−02 | 3.152E−02 | 3.740E−02 | 4.889E−02 | 3.829E−02 | 6.109E−02 | 7.845E−02 | 3.660E−02 |
| 133 | 1.273E−02 | 7.596E−03 | 1.122E−02 | 1.567E−02 | 2.306E−02 | 1.069E−02 | 1.354E−02 | 1.701E−02 | 6.981E−03 | 7.658E−03 | 3.811E−03 | 8.709E−03 | 1.460E−02 |
| 134 | 1.273E−02 | 3.802E−03 | 1.683E−02 | 1.567E−02 | 2.698E−02 | 2.137E−02 | 3.598E−02 | 0.000E+00 | 4.185E−02 | 7.658E−03 | 7.631E−03 | 4.354E−03 | 7.320E−03 |
| 135 | 3.402E−02 | 3.037E−02 | 1.122E−02 | 3.134E−02 | 3.081E−02 | 1.781E−02 | 1.799E−02 | 6.803E−03 | 1.398E−02 | 7.658E−03 | 2.289E−02 | 8.709E−03 | 1.825E−02 |
| 136 | 2.974E−02 | 1.140E−02 | 0.000E+00 | 2.743E−02 | 3.847E−03 | 3.197E−02 | 4.506E−03 | 1.701E−02 | 0.000E+00 | 1.149E−02 | 7.631E−03 | 2.618E−02 | 1.460E−02 |
| 137 | 8.905E−02 | 3.419E−02 | 5.628E−03 | 3.918E−02 | 4.239E−02 | 3.197E−02 | 3.152E−02 | 3.063E−02 | 1.745E−02 | 4.212E−02 | 3.437E−02 | 2.618E−02 | 4.025E−02 |
| 138 | 1.273E−02 | 1.140E−02 | 1.683E−02 | 3.134E−02 | 1.158E−02 | 2.137E−02 | 1.354E−02 | 2.378E−02 | 1.745E−02 | 2.297E−02 | 4.194E−02 | 1.309E−02 | 4.025E−02 |
| 139 | 1.995E−01 | 1.897E−01 | 1.630E−01 | 1.451E−01 | 1.389E−01 | 2.493E−01 | 2.030E−01 | 2.110E−01 | 2.235E−01 | 1.451E−01 | 1.603E−01 | 2.137E−01 | 1.167E−01 |
| 140 | 1.193E−01 | 9.528E−02 | 9.528E−02 | 8.620E−02 | 3.464E−02 | 6.759E−02 | 1.077E−01 | 1.594E−01 | 9.795E−02 | 6.126E−02 | 1.069E−01 | 1.478E−01 | 4.025E−02 |
| 141 | 8.068E−02 | 6.839E−02 | 2.814E−02 | 3.134E−02 | 3.464E−02 | 5.334E−02 | 1.710E−01 | 5.779E−02 | 6.278E−02 | 6.509E−02 | 6.483E−02 | 9.617E−02 | 8.050E−02 |
| 142 | 4.248E−03 | 1.523E−02 | 1.122E−02 | 1.175E−02 | 1.158E−02 | 1.781E−02 | 0.000E+00 | 2.039E−02 | 1.051E−02 | 7.658E−03 | 1.906E−02 | 8.709E−03 | 3.660E−03 |
| 143 | 1.273E−02 | 2.280E−02 | 2.253E−02 | 1.959E−02 | 1.158E−02 | 7.115E−03 | 0.000E+00 | 1.701E−02 | 6.981E−03 | 1.915E−02 | 2.289E−02 | 1.745E−02 | 3.295E−02 |
| 144 | 5.102E−02 | 1.523E−02 | 1.683E−02 | 3.134E−02 | 1.541E−02 | 2.841E−02 | 8.994E−03 | 3.063E−02 | 3.143E−02 | 1.915E−02 | 2.289E−02 | 4.791E−02 | 5.850E−02 |
| 145 | 2.128E−02 | 2.280E−02 | 5.628E−03 | 1.175E−02 | 7.703E−03 | 3.197E−02 | 2.698E−02 | 1.024E−02 | 1.745E−02 | 1.532E−02 | 1.906E−02 | 1.309E−02 | 1.460E−02 |
| 146 | 2.208E−01 | 2.199E−01 | 2.137E−01 | 2.707E−01 | 2.351E−01 | 2.422E−01 | 2.297E−01 | 2.208E−01 | 2.128E−01 | 2.832E−01 | 2.556E−01 | 2.876E−01 | 1.906E−01 |
| 147 | 9.795E−02 | 1.175E−01 | 4.497E−02 | 9.795E−02 | 9.617E−02 | 7.827E−02 | 7.649E−02 | 1.630E−01 | 1.077E−01 | 1.416E−01 | 1.451E−01 | 1.131E−01 | 1.496E−01 |
| 148 | 2.547E−01 | 4.595E−01 | 2.306E−01 | 2.547E−01 | 2.582E−01 | 4.301E−01 | 3.019E−01 | 4.212E−01 | 4.114E−01 | 2.947E−01 | 3.508E−01 | 3.793E−01 | 3.918E−01 |

APPENDIX D-continued

Ovarian Cancer
Training Dataset

| | | | | | | | | | | | | | |
|---|---|---|---|---|---|---|---|---|---|---|---|---|---|
| 149 | 9.350E−02 | 6.073E−02 | 3.936E−02 | 6.661E−02 | 5.387E−02 | 5.334E−02 | 6.305E−02 | 1.024E−01 | 6.634E−02 | 5.361E−02 | 6.866E−02 | 7.845E−02 | 5.850E−02 |
| 150 | 1.701E−02 | 1.140E−02 | 5.628E−03 | 1.175E−02 | 1.158E−02 | 1.425E−02 | 4.506E−03 | 2.716E−02 | 2.440E−02 | 7.658E−03 | 1.906E−02 | 2.618E−02 | 2.565E−02 |
| 151 | 1.701E−02 | 1.897E−02 | 5.628E−03 | 4.310E−02 | 3.464E−02 | 2.137E−02 | 3.152E−02 | 2.039E−02 | 1.745E−02 | 2.297E−02 | 7.631E−03 | 1.309E−02 | 3.295E−02 |
| 152 | 2.974E−02 | 3.802E−02 | 5.628E−03 | 1.175E−02 | 3.081E−02 | 5.334E−02 | 2.253E−02 | 1.701E−02 | 2.440E−02 | 3.063E−02 | 2.671E−02 | 3.918E−02 | 2.930E−02 |
| 153 | 3.402E−02 | 2.663E−02 | 5.628E−03 | 1.567E−02 | 1.158E−02 | 2.841E−02 | 2.253E−02 | 3.402E−03 | 1.051E−02 | 1.149E−02 | 2.671E−02 | 4.791E−02 | 2.930E−02 |
| 154 | 2.128E−02 | 1.523E−02 | 1.122E−02 | 3.918E−03 | 2.698E−02 | 1.069E−02 | 8.994E−03 | 6.803E−03 | 3.491E−03 | 1.532E−02 | 2.289E−02 | 1.309E−02 | 1.095E−02 |
| 155 | 1.273E−02 | 1.523E−02 | 1.122E−02 | 7.836E−03 | 7.703E−03 | 1.069E−02 | 2.698E−02 | 2.716E−02 | 6.981E−03 | 1.532E−02 | 1.523E−02 | 2.182E−02 | 3.295E−02 |
| 156 | 4.292E−01 | 4.595E−01 | 5.512E−01 | 3.802E−01 | 5.619E−01 | 5.548E−01 | 8.415E−01 | 5.102E−01 | 3.072E−01 | 3.713E−01 | 4.123E−01 | 7.275E−01 | 4.390E−01 |
| 157 | 1.532E−01 | 1.523E−01 | 1.407E−01 | 1.728E−01 | 1.772E−01 | 2.102E−01 | 2.030E−01 | 2.146E−01 | 1.567E−01 | 1.149E−01 | 1.256E−01 | 2.093E−01 | 1.941E−01 |
| 158 | 3.865E−01 | 4.061E−01 | 4.221E−01 | 4.506E−01 | 5.316E−01 | 4.301E−01 | 4.230E−01 | 3.295E−01 | 3.838E−01 | 3.713E−01 | 2.974E−01 | 6.189E−01 | 2.965E−01 |
| 159 | 1.149E−01 | 1.211E−01 | 1.407E−01 | 7.444E−02 | 1.736E−01 | 1.069E−01 | 1.167E−01 | 8.157E−02 | 8.023E−02 | 1.683E−01 | 8.771E−02 | 1.825E−01 | 6.946E−02 |
| 160 | 2.974E−02 | 3.419E−02 | 2.814E−02 | 2.351E−02 | 3.464E−02 | 2.137E−02 | 1.354E−02 | 2.716E−02 | 2.093E−02 | 4.978E−02 | 3.054E−02 | 2.182E−02 | 3.660E−02 |
| 161 | 8.495E−03 | 7.596E−03 | 1.122E−02 | 3.134E−02 | 2.306E−02 | 3.553E−03 | 2.698E−02 | 3.063E−02 | 3.838E−02 | 2.297E−02 | 1.906E−02 | 5.227E−02 | 2.565E−02 |
| 162 | 4.675E−02 | 1.897E−02 | 2.253E−02 | 1.175E−02 | 3.464E−02 | 2.137E−02 | 3.598E−02 | 1.701E−02 | 1.051E−02 | 2.297E−02 | 3.811E−02 | 4.354E−02 | 3.660E−02 |
| 163 | 2.974E−02 | 1.523E−02 | 3.936E−02 | 7.836E−03 | 1.158E−02 | 2.137E−02 | 2.253E−02 | 1.362E−02 | 1.051E−02 | 1.915E−02 | 3.437E−02 | 4.354E−02 | 3.660E−03 |
| 164 | 2.128E−02 | 7.596E−03 | 7.872E−02 | 1.959E−02 | 2.306E−02 | 1.781E−02 | 8.994E−03 | 6.803E−03 | 1.051E−02 | 1.532E−02 | 3.437E−02 | 1.309E−02 | 3.295E−02 |
| 165 | 3.402E−02 | 2.280E−02 | 2.253E−02 | 1.567E−02 | 3.847E−02 | 3.553E−02 | 1.354E−02 | 2.716E−02 | 4.185E−02 | 1.915E−02 | 4.194E−02 | 3.045E−02 | 2.930E−02 |
| 166 | 5.948E−02 | 6.839E−02 | 0.000E+00 | 4.310E−02 | 5.387E−02 | 3.197E−02 | 9.439E−02 | 3.740E−02 | 9.083E−02 | 2.680E−02 | 4.960E−02 | 8.272E−02 | 3.660E−02 |
| 167 | 3.615E−01 | 2.850E−01 | 2.591E−01 | 1.799E−01 | 2.769E−01 | 2.351E−01 | 4.550E−01 | 2.787E−01 | 2.271E−01 | 2.333E−01 | 2.636E−01 | 3.224E−01 | 2.191E−01 |
| 168 | 1.701E−01 | 1.024E−01 | 1.576E−01 | 6.269E−02 | 1.505E−01 | 9.973E−02 | 1.576E−01 | 1.398E−01 | 8.370E−02 | 6.509E−02 | 1.149E−01 | 1.701E−01 | 1.131E−01 |
| 169 | 6.794E−02 | 5.316E−02 | 5.628E−02 | 3.918E−02 | 8.085E−02 | 4.978E−02 | 5.405E−02 | 4.764E−02 | 4.185E−02 | 4.595E−02 | 3.811E−02 | 1.086E−01 | 5.850E−02 |
| 170 | 3.402E−02 | 3.802E−02 | 6.189E−02 | 2.351E−02 | 3.081E−02 | 1.781E−02 | 3.598E−02 | 3.063E−02 | 2.093E−02 | 1.915E−02 | 3.437E−02 | 3.918E−02 | 2.191E−02 |
| 171 | 3.402E−02 | 4.176E−02 | 5.628E−02 | 1.959E−02 | 7.703E−03 | 3.197E−02 | 4.506E−02 | 3.740E−02 | 1.051E−02 | 1.149E−02 | 2.289E−02 | 1.745E−02 | 2.565E−02 |
| 172 | 1.193E−01 | 9.148E−02 | 4.022E−02 | 6.475E−02 | 1.803E−01 | 1.097E−01 | 9.356E−02 | 3.985E−01 | 2.649E−01 | 1.324E−01 | 1.113E−01 | 1.324E−01 | 9.516E−02 |
| 173 | 3.353E+00 | 2.910E+00 | 3.323E−01 | 2.340E+00 | 2.693E+00 | 2.529E+00 | 3.006E+00 | 3.078E+00 | 3.110E−00 | 2.591E+00 | 2.694E+00 | 2.681E+00 | 2.521E+00 |
| 174 | 5.599E+00 | 5.160E+00 | 1.950E−01 | 4.104E+00 | 4.685E+00 | 4.671E+00 | 5.143E+00 | 4.481E+00 | 4.936E+00 | 4.416E+00 | 4.267E+00 | 4.593E+00 | 4.414E+00 |
| 175 | 1.353E+00 | 1.241E+00 | 1.655E−01 | 1.254E+00 | 1.234E+00 | 1.141E+00 | 1.011E+00 | 1.608E+00 | 1.361E+00 | 1.202E+00 | 1.482E+00 | 1.032E+00 | 1.420E+00 |
| 176 | 3.201E+00 | 2.540E+00 | 1.104E+00 | 1.880E+00 | 3.365E+00 | 2.630E+00 | 2.047E+00 | 2.766E+00 | 3.039E+00 | 2.179E+00 | 3.204E+00 | 2.666E+00 | 2.626E+00 |
| 177 | 1.439E+00 | 1.598E+00 | 4.868E−01 | 1.421E+00 | 2.727E+00 | 1.790E+00 | 1.011E+00 | 1.666E+00 | 2.125E+00 | 1.597E+00 | 1.822E+00 | 1.443E+00 | 1.981E+00 |
| 178 | 2.048E−01 | 2.072E−01 | 9.908E−02 | 1.754E−01 | 6.732E−01 | 4.169E−01 | 2.072E−01 | 5.150E−01 | 3.998E−01 | 3.470E−01 | 3.274E−01 | 2.477E−01 | 3.299E−01 |
| 179 | 2.808E−02 | 2.882E−02 | 2.403E−02 | 2.747E−02 | 1.008E−01 | 5.530E−02 | 2.354E−02 | 5.898E−02 | 5.910E−02 | 5.162E−02 | 5.040E−02 | 3.654E−02 | 5.334E−02 |
| 180 | 3.164E−02 | 1.203E−02 | 1.007E−02 | 1.349E−02 | 2.281E−02 | 1.717E−02 | 1.925E−02 | 3.605E−02 | 1.631E−02 | 1.213E−02 | 3.151E−02 | 2.698E−02 | 1.962E−02 |
| 181 | 2.403E−02 | 2.305E−02 | 3.483E−02 | 1.888E−02 | 9.540E−03 | 1.126E−02 | 2.600E−02 | 1.876E−02 | 2.109E−02 | 1.471E−02 | 2.367E−02 | 2.636E−02 | 1.864E−02 |
| 182 | 1.766E−01 | 1.324E−01 | 5.420E−03 | 1.095E−01 | 1.129E−01 | 1.097E−01 | 2.673E−01 | 1.044E−01 | 1.095E−01 | 9.651E−02 | 1.140E−01 | 1.263E−01 | 8.719E−02 |
| 183 | 2.480E+00 | 2.045E+00 | 8.666E−01 | 1.755E+00 | 1.862E+00 | 1.904E+00 | 3.081E+00 | 2.847E+00 | 2.168E+00 | 1.883E+00 | 2.352E+00 | 1.813E+00 | 1.939E+00 |
| 184 | 2.663E+00 | 2.534E+00 | 9.347E−01 | 1.901E+00 | 2.152E+00 | 2.111E+00 | 3.529E+00 | 2.230E+00 | 2.238E+00 | 1.920E+00 | 2.154E+00 | 1.999E+00 | 2.018E+00 |
| 185 | 1.783E+00 | 1.750E+00 | 3.863E−01 | 1.419E+00 | 1.399E+00 | 1.454E+00 | 2.387E+00 | 1.549E+00 | 1.288E+00 | 1.355E+00 | 1.433E+00 | 1.416E+00 | 1.549E+00 |
| 186 | 3.908E+00 | 3.572E+00 | 1.537E+00 | 2.784E+00 | 3.458E+00 | 3.747E+00 | 4.448E+00 | 3.222E+00 | 3.132E+00 | 3.033E+00 | 3.198E+00 | 2.816E+00 | 3.251E+00 |
| 187 | 8.746E−01 | 7.676E−01 | 4.929E−01 | 7.676E−01 | 7.578E−01 | 7.836E−01 | 7.911E−01 | 1.113E+00 | 7.703E−01 | 6.941E−01 | 1.003E+00 | 6.045E−01 | 9.248E−01 |
| 188 | 7.664E−02 | 6.585E−02 | 7.431E−02 | 5.445E−02 | 7.738E−02 | 6.119E−02 | 7.382E−02 | 1.223E−01 | 6.683E−02 | 6.278E−02 | 9.773E−02 | 6.904E−02 | 8.719E−02 |
| 189 | 1.170E−02 | 2.673E−02 | 2.636E−02 | 1.025E−02 | 1.913E−02 | 2.011E−02 | 1.987E−02 | 1.729E−02 | 7.689E−03 | 2.060E−02 | 2.624E−02 | 1.803E−02 | 1.459E−02 |
| 190 | 2.612E−01 | 2.808E−01 | 2.269E−01 | 1.852E−01 | 3.102E−01 | 2.428E−01 | 1.766E−01 | 2.992E−01 | 2.551E−01 | 1.729E−01 | 3.789E−01 | 1.987E−01 | 3.213E−01 |
| 191 | 3.176E+00 | 3.399E+00 | 4.803E+00 | 3.300E+00 | 5.422E+00 | 4.247E+00 | 3.303E+00 | 3.196E+00 | 3.699E+00 | 3.215E+00 | 4.335E+00 | 3.180E+00 | 4.207E+00 |
| 192 | 7.210E−01 | 7.652E−01 | 1.362E+00 | 6.180E−01 | 1.714E+00 | 1.246E+00 | 8.531E−01 | 1.178E+00 | 9.577E−01 | 9.079E−01 | 9.825E−01 | 7.419E−01 | 1.036E+00 |
| 193 | 1.035E−01 | 8.314E−02 | 1.422E−01 | 9.503E−02 | 2.391E−01 | 1.937E−01 | 1.300E−01 | 1.778E−01 | 1.349E−01 | 1.275E−01 | 1.361E−01 | 9.834E−02 | 1.741E−01 |
| 194 | 1.373E−01 | 7.063E−02 | 5.040E−02 | 5.714E−02 | 6.573E−02 | 5.236E−02 | 1.147E−01 | 9.405E−02 | 7.492E−02 | 6.376E−02 | 7.934E−02 | 9.001E−02 | 6.646E−02 |
| 195 | 4.096E−02 | 3.446E−02 | 1.778E−02 | 3.507E−02 | 2.551E−02 | 2.845E−02 | 4.157E−02 | 3.985E−02 | 3.262E−02 | 3.323E−02 | 3.311E−02 | 4.145E−02 | 2.918E−02 |
| 196 | 2.183E−01 | 2.354E−01 | 3.899E−01 | 1.913E−01 | 4.034E−01 | 4.316E−01 | 3.115E−01 | 2.968E−01 | 3.593E−01 | 2.428E−01 | 4.390E−01 | 2.170E−01 | 3.078E−01 |
| 197 | 1.275E−01 | 1.312E−01 | 2.428E−01 | 1.176E−01 | 2.281E−01 | 2.281E−01 | 1.263E−01 | 1.741E−01 | 2.109E−01 | 1.251E−01 | 2.759E−01 | 1.188E−01 | 1.913E−01 |
| 198 | 8.363E−02 | 4.709E−02 | 1.216E−01 | 5.015E−02 | 9.969E−02 | 8.032E−02 | 6.327E−02 | 1.151E−01 | 7.259E−02 | 5.592E−02 | 1.093E−01 | 7.014E−02 | 8.768E−02 |

APPENDIX D-continued

Ovarian Cancer
Training Dataset

| | | | | | | | | | | | | | |
|---|---|---|---|---|---|---|---|---|---|---|---|---|---|
| 199 | 1.386E−01 | 7.063E−02 | 2.305E−01 | 1.888E−02 | 5.886E−02 | 2.600E−02 | 8.179E−02 | 7.590E−02 | 5.714E−02 | 2.477E−02 | 9.822E−02 | 9.540E−02 | 4.378E−02 |
| 200 | 8.952E−02 | 6.009E−02 | 7.284E−02 | 2.477E−02 | 5.089E−02 | 3.728E−02 | 7.566E−02 | 5.567E−02 | 4.611E−02 | 4.329E−02 | 5.359E−02 | 6.597E−02 | 4.635E−02 |
| 201 | 6.021E−02 | 3.765E−02 | 1.545E−02 | 1.729E−02 | 3.556E−02 | 4.353E−02 | 5.518E−02 | 3.507E−02 | 3.654E−02 | 3.581E−02 | 3.630E−02 | 4.917E−02 | 3.176E−02 |
| 202 | 5.849E−03 | 2.097E−03 | 6.193E−03 | 2.698E−03 | 3.176E−03 | 1.471E−03 | 1.864E−03 | 7.026E−03 | 9.614E−04 | 1.055E−03 | 3.679E−03 | 3.004E−03 | 1.008E−03 |
| 203 | 5.849E−04 | 0.000E+00 | 0.000E+00 | 1.079E−03 | 5.297E−04 | 4.893E−04 | 0.000E+00 | 0.000E+00 | 1.447E−03 | 5.273E−04 | 0.000E+00 | 5.996E−04 | 1.008E−03 |
| 204 | 1.349E−02 | 3.139E−03 | 6.193E−03 | 1.619E−03 | 1.594E−03 | 2.452E−03 | 2.477E−03 | 2.808E−03 | 1.447E−03 | 1.582E−03 | 3.679E−03 | 4.795E−03 | 2.514E−03 |
| 205 | 1.170E−03 | 1.570E−03 | 2.318E−03 | 1.079E−03 | 0.000E+00 | 1.962E−03 | 6.205E−04 | 9.368E−04 | 1.447E−03 | 1.055E−03 | 5.248E−04 | 0.000E+00 | 2.514E−03 |
| 206 | 1.226E−02 | 4.181E−03 | 8.522E−03 | 2.158E−03 | 2.649E−03 | 4.893E−03 | 3.102E−03 | 5.616E−03 | 1.925E−03 | 2.636E−03 | 6.830E−03 | 9.001E−03 | 3.017E−03 |
| 207 | 5.849E−04 | 0.000E+00 | 0.000E+00 | 5.395E−04 | 2.121E−03 | 0.000E+00 | 0.000E+00 | 0.000E+00 | 4.807E−04 | 5.273E−04 | 5.248E−04 | 1.199E−03 | 0.000E+00 |
| 208 | 5.261E−03 | 1.570E−03 | 2.318E−03 | 3.237E−03 | 2.649E−03 | 3.912E−03 | 3.716E−03 | 4.218E−03 | 1.925E−03 | 3.164E−03 | 1.582E−03 | 5.395E−03 | 2.011E−03 |
| 209 | 1.170E−03 | 5.236E−04 | 0.000E+00 | 0.000E+00 | 0.000E+00 | 4.893E−04 | 0.000E+00 | 1.876E−03 | 4.807E−04 | 5.273E−04 | 0.000E+00 | 0.000E+00 | 5.040E−04 |
| 210 | 1.170E−03 | 0.000E+00 | 7.750E−04 | 5.395E−04 | 1.061E−03 | 1.471E−03 | 0.000E+00 | 0.000E+00 | 4.807E−04 | 5.273E−04 | 0.000E+00 | 5.996E−04 | 0.000E+00 |
| 211 | 0.000E+00 | 0.000E+00 | 7.750E−04 | 1.079E−03 | 1.061E−03 | 4.893E−04 | 0.000E+00 | 4.684E−04 | 0.000E+00 | 5.273E−04 | 0.000E+00 | 5.996E−04 | 1.508E−03 |
| 212 | 1.170E−03 | 5.236E−04 | 0.000E+00 | 0.000E+00 | 0.000E+00 | 4.893E−04 | 6.205E−04 | 0.000E+00 | 4.807E−04 | 0.000E+00 | 0.000E+00 | 1.803E−03 | 0.000E+00 |
| 213 | 1.754E−03 | 1.046E−03 | 7.750E−04 | 1.619E−03 | 5.297E−04 | 1.962E−03 | 3.102E−03 | 4.684E−03 | 1.925E−03 | 1.055E−03 | 2.624E−03 | 2.403E−03 | 2.011E−03 |
| 214 | 1.170E−03 | 2.097E−03 | 7.750E−04 | 1.619E−03 | 1.594E−03 | 4.893E−04 | 6.205E−04 | 0.000E+00 | 4.807E−04 | 5.273E−04 | 3.151E−03 | 4.194E−03 | 1.008E−03 |
| 215 | 1.170E−03 | 5.236E−04 | 0.000E+00 | 1.079E−03 | 1.061E−03 | 0.000E+00 | 0.000E+00 | 0.000E+00 | 1.925E−03 | 0.000E+00 | 1.051E−03 | 1.803E−03 | 1.008E−03 |
| 216 | 0.000E+00 | 1.046E−03 | 0.000E+00 | 0.000E+00 | 0.000E+00 | 0.000E+00 | 6.205E−04 | 1.410E−03 | 0.000E+00 | 4.218E−03 | 5.248E−04 | 0.000E+00 | 5.040E−04 |
| 217 | 1.754E−03 | 5.236E−04 | 0.000E+00 | 0.000E+00 | 1.061E−03 | 1.962E−03 | 2.477E−03 | 9.368E−04 | 0.000E+00 | 5.273E−04 | 0.000E+00 | 1.803E−03 | 1.008E−03 |
| 218 | 3.089E+00 | 2.231E+00 | 1.369E+00 | 2.223E+00 | 2.316E+00 | 2.227E+00 | 3.502E+00 | 3.158E+00 | 2.592E+00 | 2.285E+00 | 3.020E+00 | 2.377E+00 | 2.331E+00 |
| 219 | 2.747E−02 | 2.305E−02 | 1.398E−02 | 2.269E−02 | 1.962E−02 | 2.256E−02 | 2.477E−02 | 2.440E−02 | 2.685E−02 | 2.109E−02 | 3.887E−02 | 2.943E−02 | 3.985E−02 |
| 220 | 1.681E+00 | 1.570E+00 | 9.502E−01 | 1.462E+00 | 2.265E+00 | 1.723E+00 | 1.002E+00 | 3.593E+00 | 2.765E+00 | 2.046E+00 | 1.759E+00 | 2.054E+00 | 1.840E+00 |
| 221 | 6.647E+01 | 5.849E+01 | 5.175E+01 | 6.029E+01 | 6.662E+01 | 5.865E+01 | 4.702E+01 | 7.128E+01 | 6.450E+01 | 5.446E+01 | 6.223E+01 | 6.281E+01 | 5.432E+01 |
| 222 | 4.045E+01 | 5.390E+01 | 1.479E+01 | 6.061E+01 | 4.881E+01 | 5.842E+01 | 3.606E+01 | 5.353E+01 | 5.744E+01 | 5.862E+01 | 5.582E+01 | 3.805E+01 | 6.251E+01 |
| 223 | 3.219E+01 | 2.598E+01 | 1.312E+01 | 2.886E+01 | 2.804E+01 | 2.531E+01 | 1.730E+01 | 3.518E+01 | 3.418E+01 | 3.296E+01 | 3.126E+01 | 3.006E+01 | 2.748E+01 |
| 224 | 2.483E+01 | 2.368E+01 | 1.316E+01 | 2.258E+01 | 2.625E+01 | 1.827E+01 | 1.285E+01 | 2.326E+01 | 1.966E+01 | 2.008E+01 | 2.484E+01 | 2.157E+01 | 2.178E+01 |
| 225 | 1.679E+01 | 2.010E+01 | 1.289E+01 | 2.096E+01 | 2.926E+01 | 1.849E+01 | 1.491E+01 | 1.626E+01 | 1.903E+01 | 1.685E+01 | 1.723E+01 | 2.636E+01 | 1.716E+01 |
| 226 | 7.730E+00 | 1.038E+01 | 4.287E+00 | 8.803E+00 | 1.564E+01 | 1.341E+01 | 7.905E+00 | 9.644E+00 | 1.246E+01 | 9.214E+00 | 1.029E+01 | 9.839E+00 | 9.997E+00 |
| 227 | 2.718E+00 | 2.427E+00 | 1.743E+00 | 3.447E+00 | 5.055E+00 | 3.825E+00 | 1.843E+00 | 3.613E+00 | 3.505E+00 | 2.980E+00 | 3.497E+00 | 2.645E+00 | 3.406E+00 |
| 228 | 2.621E−01 | 2.581E−01 | 2.630E−01 | 2.430E−01 | 1.493E−01 | 3.219E−01 | 2.145E−01 | 3.678E−01 | 2.700E−01 | 1.965E−01 | 5.893E−01 | 3.413E−01 | 3.954E−01 |
| 229 | 2.578E−01 | 2.674E−01 | 2.985E−01 | 2.618E−01 | 1.787E−01 | 3.294E−01 | 2.066E−01 | 3.932E−01 | 3.068E−01 | 2.085E−01 | 6.215E−01 | 3.450E−01 | 4.638E−01 |
| 230 | 3.727E+01 | 3.674E+01 | 2.826E+01 | 3.195E+01 | 2.754E+01 | 3.334E+01 | 2.476E+01 | 2.267E+01 | 2.754E+01 | 2.918E+01 | 2.733E+01 | 3.203E+01 | 2.935E+01 |
| 231 | 3.878E+00 | 4.008E+00 | 3.088E+00 | 4.132E+00 | 2.865E+00 | 4.619E+00 | 2.714E+00 | 3.555E+00 | 4.170E+00 | 3.270E+00 | 5.083E+00 | 4.141E+00 | 4.274E+00 |
| 232 | 1.810E+00 | 1.411E+00 | 1.467E+00 | 1.476E+00 | 1.322E+00 | 1.754E+00 | 1.488E+00 | 1.098E+00 | 1.459E+00 | 1.474E+00 | 1.933E+00 | 2.119E+00 | 1.623E+00 |
| 233 | 4.839E+00 | 6.339E+00 | 3.918E+00 | 5.148E+00 | 5.862E+00 | 4.343E+00 | 4.297E+00 | 5.531E+00 | 4.572E+00 | 4.839E+00 | 5.705E+00 | 6.428E+00 | 5.067E+00 |
| 234 | 1.858E+01 | 1.555E+01 | 1.396E+01 | 1.211E+01 | 1.367E+01 | 1.368E+01 | 1.399E+01 | 2.354E+01 | 2.087E+01 | 1.646E+01 | 1.552E+01 | 1.990E+01 | 1.359E+01 |
| 235 | 1.592E+01 | 9.315E+00 | 1.214E+01 | 8.435E+00 | 8.031E+00 | 9.546E+00 | 1.044E+01 | 8.046E+00 | 1.019E+01 | 7.566E+00 | 8.787E+00 | 1.386E+01 | 7.849E+00 |
| 236 | 7.464E−01 | 6.843E−01 | 4.756E−01 | 5.228E−01 | 5.908E−01 | 6.488E−01 | 5.099E−01 | 6.144E−01 | 7.126E−01 | 5.316E−01 | 9.024E−01 | 6.990E−01 | 6.303E−01 |
| 237 | 4.958E+00 | 5.175E+00 | 4.001E+00 | 6.896E+00 | 3.648E+00 | 5.753E+00 | 3.443E+00 | 4.613E+00 | 4.326E+00 | 5.490E+00 | 5.885E+00 | 3.231E+00 | 6.803E+00 |
| 238 | 1.014E+01 | 6.078E+00 | 7.142E+00 | 6.864E+00 | 4.900E+00 | 6.660E+00 | 5.698E+00 | 5.544E+00 | 6.276E+00 | 6.867E+00 | 7.190E+00 | 7.247E+00 | 6.742E+00 |
| 239 | 1.793E+00 | 1.195E+00 | 1.286E+00 | 1.300E+00 | 1.087E+00 | 1.234E+00 | 1.172E+00 | 9.166E−01 | 1.295E+00 | 1.171E+00 | 1.645E+00 | 1.776E+00 | 1.460E+00 |
| 240 | 1.458E+01 | 1.046E+01 | 9.295E+00 | 6.234E+00 | 8.231E+00 | 8.833E+00 | 1.024E+01 | 1.545E+01 | 1.091E+01 | 6.900E+00 | 1.311E+01 | 1.281E+01 | 9.229E+00 |
| 241 | 2.140E+02 | 2.279E+02 | 2.721E+02 | 2.513E+02 | 2.106E+02 | 2.587E+02 | 3.117E+02 | 2.465E+02 | 2.580E+02 | 2.480E+02 | 2.471E+02 | 2.120E+02 | 2.568E+02 |
| 242 | 1.868E+02 | 1.305E+02 | 2.086E+02 | 1.436E+02 | 1.358E+02 | 1.416E+02 | 1.775E+02 | 1.877E+02 | 1.786E+02 | 1.772E+02 | 1.535E+02 | 1.749E+02 | 1.365E+02 |
| 243 | 1.710E+01 | 1.143E+01 | 1.719E+01 | 1.233E+01 | 1.232E+01 | 1.196E+01 | 1.406E+01 | 1.734E+01 | 1.599E+01 | 1.588E+01 | 1.358E+01 | 1.619E+01 | 1.185E+01 |
| 244 | 1.643E+01 | 1.285E+01 | 1.456E+01 | 1.405E+01 | 1.423E+01 | 1.321E+01 | 9.337E+00 | 8.642E+00 | 1.153E+01 | 1.165E+01 | 1.115E+01 | 1.298E+01 | 1.140E+01 |
| 245 | 6.734E+00 | 5.700E+00 | 5.827E+00 | 6.967E+00 | 6.038E+00 | 6.443E+00 | 4.428E+00 | 5.632E+00 | 5.738E+00 | 6.168E+00 | 5.975E+00 | 5.219E+00 | 6.600E+00 |
| 246 | 6.297E+00 | 6.465E+00 | 6.041E+00 | 7.724E+00 | 7.115E+00 | 7.567E+00 | 6.189E+00 | 5.644E+00 | 5.904E+00 | 6.673E+00 | 8.893E+00 | 6.555E+00 | 1.023E+01 |
| 247 | 4.250E+00 | 4.140E+00 | 4.567E+00 | 3.877E+00 | 4.495E+00 | 4.296E+00 | 4.578E+00 | 3.652E+00 | 4.085E+00 | 4.339E+00 | 5.732E+00 | 5.477E+00 | 6.207E+00 |
| 248 | 6.334E+01 | 8.095E+01 | 1.110E+02 | 8.927E+01 | 1.123E+02 | 7.814E+01 | 1.003E+02 | 7.918E+01 | 8.043E+01 | 7.316E+01 | 7.840E+01 | 1.092E+02 | 7.566E+01 |

APPENDIX D-continued

Ovarian Cancer Training Dataset

| | | | | | | | | | | | | | |
|---|---|---|---|---|---|---|---|---|---|---|---|---|---|
| 249 | 5.276E+01 | 6.892E+01 | 7.643E+01 | 6.751E+01 | 8.028E+01 | 7.152E+01 | 7.050E+01 | 8.626E+01 | 7.066E+01 | 7.415E+01 | 7.080E+01 | 7.035E+01 | 7.782E+01 |
| 250 | 1.282E+02 | 1.397E+02 | 1.182E+02 | 1.450E+02 | 1.279E+02 | 1.323E+02 | 1.231E+02 | 1.342E+02 | 1.237E+02 | 1.434E+02 | 1.515E+02 | 1.067E+02 | 1.505E+02 |
| 251 | 6.023E+01 | 4.631E+01 | 4.687E+01 | 4.419E+01 | 4.406E+01 | 3.796E+01 | 4.290E+01 | 5.644E+01 | 4.400E+01 | 4.751E+01 | 5.542E+01 | 4.496E+01 | 4.862E+01 |
| 252 | 4.440E+00 | 3.013E+00 | 3.102E+00 | 2.577E+00 | 2.932E+00 | 2.508E+00 | 2.679E+00 | 3.741E+00 | 3.290E+00 | 3.042E+00 | 3.926E+00 | 3.407E+00 | 3.203E+00 |
| 253 | 6.533E+00 | 5.525E+00 | 5.200E+00 | 4.345E+00 | 5.424E+00 | 6.210E+00 | 4.089E+00 | 3.363E+00 | 5.581E+00 | 4.154E+00 | 5.596E+00 | 4.827E+00 | 4.646E+00 |
| 254 | 1.634E+01 | 1.270E+01 | 1.394E+01 | 1.420E+01 | 1.442E+01 | 1.221E+01 | 8.859E+00 | 8.277E+00 | 1.220E+01 | 1.106E+01 | 1.186E+01 | 1.184E+01 | 1.086E+01 |
| 255 | 1.227E+01 | 9.669E+00 | 1.161E+01 | 1.202E+01 | 1.206E+01 | 1.053E+01 | 8.772E+00 | 7.420E+00 | 9.755E+00 | 9.583E+00 | 1.043E+01 | 1.204E+01 | 1.114E+01 |
| 256 | 3.576E+00 | 3.156E+00 | 4.125E+00 | 2.882E+00 | 3.512E+00 | 3.062E+00 | 3.600E+00 | 2.781E+00 | 2.839E+00 | 2.761E+00 | 3.346E+00 | 4.138E+00 | 3.494E+00 |
| 257 | 4.078E+00 | 5.153E+00 | 4.678E+00 | 4.234E+00 | 4.459E+00 | 4.467E+00 | 4.539E+00 | 3.993E+00 | 3.634E+00 | 4.097E+00 | 5.029E+00 | 5.563E+00 | 5.314E+00 |
| 258 | 2.285E+01 | 2.599E+01 | 3.746E+01 | 3.007E+01 | 4.702E+01 | 3.445E+01 | 2.967E+01 | 3.147E+01 | 3.026E+01 | 2.497E+01 | 3.466E+01 | 3.162E+01 | 3.032E+01 |
| 259 | 4.403E+01 | 5.165E+01 | 6.392E+01 | 5.166E+01 | 7.967E+01 | 4.596E+01 | 5.371E+01 | 4.442E+01 | 4.335E+01 | 4.170E+01 | 4.711E+01 | 6.729E+01 | 4.404E+01 |
| 260 | 3.502E+01 | 3.923E+01 | 4.771E+01 | 2.779E+01 | 4.580E+01 | 3.249E+01 | 3.695E+01 | 3.829E+01 | 3.290E+01 | 3.469E+01 | 2.961E+01 | 4.364E+01 | 2.786E+01 |
| 261 | 3.485E+01 | 3.361E+01 | 3.371E+01 | 2.851E+01 | 2.785E+01 | 3.249E+01 | 2.793E+01 | 2.539E+01 | 2.835E+01 | 2.726E+01 | 2.601E+01 | 3.015E+01 | 2.569E+01 |
| 262 | 1.152E+01 | 9.966E+00 | 9.681E+00 | 8.741E+00 | 8.531E+00 | 1.007E+01 | 1.042E+01 | 9.974E+00 | 9.744E+00 | 8.213E+00 | 9.566E+00 | 1.047E+01 | 1.111E+01 |
| 263 | 4.399E+00 | 4.052E+00 | 4.346E+00 | 4.024E+00 | 5.004E+00 | 5.272E+00 | 3.690E+00 | 2.621E+00 | 4.249E+00 | 3.344E+00 | 4.967E+00 | 4.016E+00 | 4.882E+00 |
| 264 | 4.193E+00 | 3.343E+00 | 4.477E+00 | 3.135E+00 | 3.407E+00 | 3.228E+00 | 3.730E+00 | 2.443E+00 | 3.567E+00 | 2.383E+00 | 3.948E+00 | 3.686E+00 | 3.640E+00 |
| 265 | 3.187E+00 | 2.235E+00 | 3.672E+00 | 2.099E+00 | 2.159E+00 | 2.481E+00 | 2.409E+00 | 1.790E+00 | 2.255E+00 | 1.782E+00 | 2.537E+00 | 3.148E+00 | 2.445E+00 |
| 266 | 2.144E+00 | 1.246E+00 | 2.232E+00 | 8.611E−01 | 9.954E−01 | 1.131E+00 | 1.680E+00 | 1.249E+00 | 1.020E+00 | 7.813E−01 | 1.554E+00 | 2.274E+00 | 1.091E+00 |
| 267 | 1.872E+00 | 1.422E+00 | 1.856E+00 | 1.137E+00 | 1.046E+00 | 1.399E+00 | 1.700E+00 | 1.104E+00 | 1.104E+00 | 9.628E−01 | 1.578E+00 | 2.149E+00 | 1.597E+00 |
| 268 | 1.550E+01 | 1.812E+01 | 1.823E+01 | 1.288E+01 | 2.276E+01 | 1.949E+01 | 1.940E+01 | 1.656E+01 | 2.052E+01 | 1.543E+01 | 1.895E+01 | 1.878E+01 | 1.618E+01 |
| 269 | 9.546E+00 | 7.775E+00 | 1.477E+01 | 6.525E+00 | 1.188E+01 | 8.060E+00 | 8.760E+00 | 1.022E+01 | 9.040E+00 | 6.709E+00 | 9.672E+00 | 9.618E+00 | 7.667E+00 |
| 270 | 3.965E+00 | 2.738E+00 | 6.140E+00 | 2.356E+00 | 4.196E+00 | 2.466E+00 | 2.870E+00 | 4.277E+00 | 2.960E+00 | 2.260E+00 | 3.362E+00 | 3.847E+00 | 2.688E+00 |
| 271 | 1.286E+01 | 1.422E+01 | 1.104E+01 | 1.139E+01 | 1.409E+01 | 1.037E+01 | 9.286E+00 | 9.731E+00 | 9.455E+00 | 1.123E+01 | 9.073E+00 | 1.404E+01 | 1.066E+01 |
| 272 | 8.612E+01 | 8.677E+01 | 6.842E+01 | 8.002E+01 | 7.047E+01 | 7.796E+01 | 6.082E+01 | 5.232E+01 | 6.298E+01 | 7.045E+01 | 6.470E+01 | 7.490E+01 | 6.972E+01 |
| 273 | 9.919E+01 | 9.885E+01 | 7.442E+01 | 9.079E+01 | 7.985E+01 | 8.990E+01 | 7.011E+01 | 6.201E+01 | 7.355E+01 | 8.226E+01 | 7.863E+01 | 8.940E+01 | 8.019E+01 |
| 274 | 1.338E+01 | 1.371E+01 | 9.604E+00 | 1.242E+01 | 1.077E+01 | 1.414E+01 | 8.941E+00 | 8.863E+00 | 1.110E+01 | 1.120E+01 | 1.115E+01 | 1.268E+01 | 1.163E+01 |
| 275 | 4.442E−01 | 8.543E−01 | 3.583E−01 | 7.451E−01 | 9.734E−01 | 4.622E−01 | 5.488E−01 | 4.715E−01 | 4.183E−01 | 5.187E−01 | 7.120E−01 | 9.464E−01 | 7.187E−01 |
| 276 | 9.210E+00 | 9.820E+00 | 7.157E+00 | 7.911E+00 | 1.080E+01 | 5.574E+00 | 7.693E+00 | 6.152E+00 | 5.945E+00 | 7.574E+00 | 7.380E+00 | 1.211E+01 | 6.502E+00 |
| 277 | 2.403E+01 | 2.436E+01 | 1.529E+01 | 1.733E+01 | 1.973E+01 | 1.626E+01 | 1.811E+01 | 1.456E+01 | 1.623E+01 | 1.747E+01 | 1.745E+01 | 2.406E+01 | 1.618E+01 |
| 278 | 2.460E+01 | 2.498E+01 | 1.511E+01 | 1.755E+01 | 2.010E+01 | 1.691E+01 | 1.898E+01 | 1.492E+01 | 1.699E+01 | 1.825E+01 | 1.849E+01 | 2.433E+01 | 1.630E+01 |
| 279 | 6.558E+00 | 5.208E+00 | 4.750E+00 | 4.117E+00 | 5.047E+00 | 5.302E+00 | 5.156E+00 | 8.216E+00 | 7.793E+00 | 5.928E+00 | 5.452E+00 | 7.418E+00 | 4.499E+00 |
| 280 | 5.770E+00 | 6.100E+00 | 4.200E+00 | 4.330E+00 | 5.637E+00 | 4.494E+00 | 4.671E+00 | 6.433E+00 | 4.323E+00 | 4.385E+00 | 5.479E+00 | 6.339E+00 | 4.698E+00 |
| 281 | 1.023E+02 | 1.165E+02 | 1.202E+02 | 1.301E+02 | 1.070E+02 | 1.316E+02 | 1.457E+02 | 1.309E+02 | 1.294E+02 | 1.295E+02 | 1.265E+02 | 1.025E+02 | 1.330E+02 |
| 282 | 8.763E+01 | 9.971E+01 | 9.212E+01 | 1.131E+02 | 9.347E+01 | 1.191E+02 | 1.235E+02 | 1.145E+02 | 1.111E+02 | 1.131E+02 | 1.095E+02 | 8.956E+01 | 1.149E+02 |
| 283 | 5.527E+01 | 3.493E+01 | 5.305E+01 | 3.960E+01 | 3.973E+01 | 4.004E+01 | 4.697E+01 | 5.958E+01 | 5.623E+01 | 5.392E+01 | 4.475E+01 | 5.351E+01 | 3.803E+01 |
| 284 | 3.868E+00 | 5.575E+00 | 4.458E+00 | 5.073E+00 | 5.586E+00 | 6.217E+00 | 5.348E+00 | 4.497E+00 | 4.590E+00 | 5.387E+00 | 6.562E+00 | 5.977E+00 | 8.711E+00 |
| 285 | 7.310E+01 | 7.958E+01 | 6.396E+01 | 8.046E+01 | 7.634E+01 | 7.816E+01 | 7.172E+01 | 7.694E+01 | 7.405E+01 | 8.259E+01 | 8.180E+01 | 6.374E+01 | 9.280E+01 |
| 286 | 5.487E+01 | 6.154E+01 | 4.265E+01 | 6.211E+01 | 6.043E+01 | 6.013E+01 | 5.378E+01 | 6.061E+01 | 5.595E+01 | 6.449E+01 | 6.232E+01 | 4.945E+01 | 6.963E+01 |
| 287 | 1.101E+01 | 7.923E+00 | 7.665E+00 | 7.125E+00 | 7.819E+00 | 6.875E+00 | 7.424E+00 | 1.065E+01 | 8.784E+00 | 8.952E+00 | 1.029E+01 | 8.483E+00 | 8.737E+00 |
| 288 | 6.425E+01 | 6.622E+01 | 6.275E+01 | 5.519E+01 | 5.489E+01 | 5.733E+01 | 5.492E+01 | 4.672E+01 | 5.605E+01 | 5.496E+01 | 4.909E+01 | 5.989E+01 | 4.960E+01 |
| 289 | 4.996E+01 | 5.323E+01 | 4.406E+01 | 4.593E+01 | 4.482E+01 | 4.629E+01 | 4.254E+01 | 3.682E+01 | 4.418E+01 | 4.508E+01 | 4.030E+01 | 4.615E+01 | 3.915E+01 |
| 290 | 1.743E+01 | 2.064E+01 | 1.673E+01 | 2.042E+01 | 1.849E+01 | 2.255E+01 | 1.982E+01 | 1.790E+01 | 1.965E+01 | 1.918E+01 | 1.599E+01 | 1.847E+01 | 2.262E+01 |
| 291 | 1.386E+01 | 1.664E+01 | 1.249E+01 | 1.601E+01 | 1.478E+01 | 1.847E+01 | 1.560E+01 | 1.471E+01 | 1.592E+01 | 1.596E+01 | 1.319E+01 | 1.510E+01 | 1.851E+01 |
| 292 | 2.377E+00 | 2.039E+00 | 2.544E+00 | 2.059E+00 | 1.985E+00 | 2.368E+00 | 2.992E+00 | 2.651E+00 | 2.663E+00 | 2.152E+00 | 2.527E+00 | 2.395E+00 | 2.634E+00 |
| 293 | 1.620E+00 | 1.010E+00 | 2.039E+00 | 7.514E−01 | 1.020E+00 | 7.754E−01 | 1.292E+00 | 1.101E+00 | 9.609E−01 | 6.336E−01 | 1.114E+00 | 1.773E+00 | 7.834E−01 |
| 294 | 2.663E+00 | 2.667E+00 | 9.516E+00 | 2.028E+00 | 2.611E+00 | 3.206E+00 | 6.080E+00 | 3.522E+00 | 3.576E+00 | 3.264E+00 | 3.529E+00 | 2.775E+00 | 3.368E+00 |
| 295 | 2.665E+00 | 2.703E+00 | 9.473E+00 | 2.016E+00 | 2.650E+00 | 3.219E+00 | 6.041E+00 | 3.514E+00 | 3.673E+00 | 3.327E+00 | 3.493E+00 | 2.842E+00 | 3.397E+00 |
| 296 | 2.316E+00 | 1.715E+00 | 7.816E+00 | 1.511E+00 | 2.007E+00 | 2.033E+00 | 3.933E+00 | 2.883E+00 | 2.793E+00 | 2.668E+00 | 2.548E+00 | 2.380E+00 | 2.083E+00 |
| 297 | 3.519E−01 | 3.726E−01 | 1.596E−01 | 3.301E−01 | 3.171E−01 | 3.510E−01 | 3.196E−01 | 2.479E−01 | 3.247E−01 | 3.535E−01 | 3.608E−01 | 3.350E−01 | 3.713E−01 |
| 298 | 1.021E−02 | 8.817E−03 | 4.119E−03 | 8.602E−03 | 5.921E−03 | 8.538E−03 | 5.706E−03 | 5.492E−03 | 8.581E−03 | 6.779E−03 | 6.114E−03 | 7.873E−03 | 8.988E−03 |

APPENDIX D-continued

Ovarian Cancer
Training Dataset

| | | | | | | | | | | | | | |
|---|---|---|---|---|---|---|---|---|---|---|---|---|---|
| 299 | 1.034E−01 | 1.013E−01 | 3.389E−02 | 5.663E−02 | 7.680E−02 | 5.320E−02 | 6.564E−02 | 5.642E−02 | 6.800E−02 | 8.002E−02 | 7.058E−02 | 9.224E−02 | 5.427E−02 |
| 300 | 2.317E−03 | 2.832E−03 | 2.982E−03 | 1.579E−03 | 3.111E−03 | 2.338E−03 | 1.238E−03 | 1.828E−03 | 2.810E−03 | 2.810E−03 | 8.988E−04 | 4.033E−03 | 1.635E−03 |
| 301 | 6.564E−02 | 6.092E−02 | 1.570E−02 | 4.162E−02 | 4.312E−02 | 3.690E−02 | 3.711E−02 | 4.784E−02 | 4.162E−02 | 4.977E−02 | 4.183E−02 | 4.655E−02 | 3.604E−02 |
| 302 | 2.317E−03 | 1.163E−03 | 7.465E−04 | 2.467E−03 | 2.960E−03 | 1.673E−03 | 1.982E−03 | 1.828E−03 | 2.639E−03 | 2.639E−03 | 8.988E−04 | 2.295E−03 | 1.143E−03 |
| 303 | 1.452E−01 | 1.553E−01 | 5.685E−02 | 1.165E−01 | 1.733E−01 | 1.276E−01 | 1.182E−01 | 1.356E−01 | 1.484E−01 | 1.532E−01 | 1.304E−01 | 1.291E−01 | 1.547E−01 |
| 304 | 1.733E−03 | 1.163E−03 | 3.733E−04 | 1.053E−03 | 1.478E−03 | 8.366E−04 | 9.911E−04 | 7.616E−04 | 1.753E−04 | 1.158E−03 | 5.406E−04 | 1.536E−03 | 9.804E−04 |
| 305 | 2.686E−01 | 2.710E−01 | 1.296E−01 | 2.102E−01 | 1.984E−01 | 2.111E−01 | 1.746E−01 | 1.515E−01 | 2.332E−01 | 2.371E−01 | 1.971E−01 | 2.213E−01 | 1.534E−01 |
| 306 | 1.002E−02 | 1.246E−02 | 8.216E−03 | 1.193E−02 | 9.353E−03 | 1.388E−02 | 6.200E−03 | 7.916E−03 | 1.401E−02 | 1.240E−02 | 5.213E−03 | 1.594E−02 | 7.851E−03 |
| 307 | 3.731E−01 | 6.296E−01 | 2.642E−01 | 5.635E−01 | 5.871E−01 | 7.259E−01 | 3.942E−01 | 5.675E−01 | 5.483E−01 | 6.991E−01 | 4.275E−01 | 5.701E−01 | 7.108E−01 |
| 308 | 5.771E−03 | 8.967E−03 | 6.736E−03 | 1.036E−02 | 1.068E−02 | 1.203E−02 | 5.213E−03 | 7.315E−03 | 8.581E−03 | 1.158E−02 | 7.551E−03 | 9.804E−03 | 1.193E−02 |
| 309 | 2.119E−03 | 2.660E−03 | 1.495E−03 | 3.153E−03 | 4.934E−04 | 4.183E−03 | 7.422E−04 | 2.274E−03 | 2.274E−03 | 2.982E−03 | 1.980E−03 | 2.682E−03 | 1.143E−03 |
| 310 | 1.926E−03 | 9.975E−04 | 4.483E−03 | 7.015E−04 | 4.934E−04 | 8.366E−04 | 3.218E−03 | 1.218E−03 | 1.401E−03 | 1.158E−03 | 8.988E−04 | 9.611E−04 | 1.306E−03 |
| 311 | 1.926E−04 | 1.663E−04 | 7.465E−04 | 1.755E−04 | 1.641E−04 | 5.020E−04 | 1.238E−03 | 0.000E+00 | 7.015E−04 | 4.955E−04 | 0.000E+00 | 0.000E+00 | 3.261E−04 |
| 312 | 3.861E−04 | 1.663E−04 | 3.733E−04 | 7.015E−04 | 0.000E+00 | 1.673E−04 | 9.911E−04 | 6.092E−04 | 0.000E+00 | 1.654E−04 | 1.800E−04 | 1.920E−04 | 4.891E−04 |
| 313 | 1.633E−01 | 9.031E−02 | 3.818E−02 | 7.680E−02 | 5.964E−02 | 1.077E−01 | 3.625E−02 | 6.028E−02 | 6.371E−02 | 7.723E−02 | 6.007E−02 | 7.680E−02 | 4.612E−02 |
| 314 | 6.350E−03 | 3.153E−03 | 4.848E−03 | 2.274E−03 | 2.134E−03 | 3.668E−03 | 2.231E−03 | 1.371E−03 | 2.274E−03 | 2.639E−03 | 2.875E−03 | 2.875E−03 | 2.939E−03 |
| 315 | 1.984E−02 | 1.663E−02 | 8.967E−03 | 1.474E−02 | 1.083E−02 | 2.107E−02 | 7.422E−03 | 1.294E−02 | 1.210E−02 | 1.223E−02 | 1.296E−02 | 1.113E−02 | 1.143E−02 |
| 316 | 1.156E−03 | 6.650E−04 | 3.733E−04 | 8.774E−04 | 6.564E−04 | 8.366E−04 | 1.733E−03 | 7.616E−04 | 1.753E−04 | 0.000E+00 | 5.406E−04 | 5.771E−04 | 1.635E−04 |
| 317 | 2.042E−02 | 1.596E−02 | 7.465E−03 | 1.491E−02 | 1.150E−02 | 1.590E−02 | 6.436E−03 | 1.828E−02 | 9.804E−03 | 1.058E−02 | 1.098E−02 | 8.645E−03 | 8.817E−03 |
| 318 | 1.156E−03 | 0.000E+00 | 7.465E−04 | 1.403E−03 | 9.847E−04 | 1.506E−03 | 1.733E−03 | 6.092E−04 | 5.256E−04 | 6.607E−04 | 1.800E−04 | 7.680E−04 | 1.635E−04 |
| 319 | 1.564E−01 | 1.100E−01 | 6.586E−02 | 1.474E−01 | 1.064E−01 | 1.658E−01 | 6.393E−02 | 1.313E−01 | 1.113E−01 | 1.088E−01 | 1.360E−01 | 9.267E−02 | 1.096E−01 |
| 320 | 1.926E−04 | 3.325E−04 | 0.000E+00 | 5.256E−04 | 0.000E+00 | 1.171E−03 | 4.955E−04 | 6.092E−04 | 1.753E−04 | 3.304E−04 | 7.208E−04 | 5.771E−04 | 4.891E−04 |
| 321 | 1.830E−01 | 1.079E−01 | 8.452E−02 | 1.309E−01 | 7.337E−02 | 1.502E−01 | 5.234E−02 | 8.002E−02 | 8.946E−02 | 1.049E−01 | 1.055E−01 | 8.474E−02 | 5.106E−02 |
| 322 | 5.964E−03 | 4.162E−03 | 3.368E−03 | 1.264E−02 | 2.960E−03 | 7.358E−03 | 2.982E−03 | 3.797E−03 | 3.497E−03 | 2.145E−03 | 5.406E−03 | 3.261E−03 | 2.124E−03 |
| 323 | 1.714E−01 | 1.386E−01 | 9.417E−02 | 1.746E−01 | 8.238E−02 | 2.074E−01 | 6.135E−02 | 1.328E−01 | 1.287E−01 | 1.375E−01 | 1.358E−01 | 8.710E−02 | 1.028E−01 |
| 324 | 5.406E−03 | 3.153E−03 | 4.848E−03 | 7.723E−03 | 2.467E−03 | 3.840E−03 | 2.724E−03 | 2.596E−03 | 3.497E−03 | 4.955E−03 | 3.239E−03 | 3.261E−03 | 1.635E−03 |
| 325 | 5.020E−03 | 6.479E−03 | 6.350E−03 | 7.186E−03 | 5.256E−03 | 6.521E−03 | 5.449E−03 | 5.942E−03 | 7.015E−03 | 4.290E−03 | 4.848E−03 | 8.066E−03 | 4.419E−03 |
| 326 | 5.771E−04 | 4.977E−04 | 7.465E−04 | 1.931E−03 | 3.282E−04 | 3.347E−04 | 9.911E−04 | 4.569E−04 | 1.753E−04 | 3.304E−04 | 7.208E−04 | 5.771E−04 | 4.891E−04 |
| 327 | 1.311E−02 | 1.113E−02 | 8.216E−03 | 8.774E−03 | 9.203E−03 | 1.137E−02 | 4.955E−03 | 5.642E−03 | 6.135E−03 | 6.950E−03 | 5.578E−03 | 7.680E−03 | 7.508E−03 |
| 328 | 9.632E−04 | 1.330E−03 | 7.465E−04 | 3.518E−04 | 1.313E−03 | 1.171E−03 | 1.487E−03 | 4.569E−04 | 5.256E−04 | 3.304E−04 | 3.604E−04 | 1.536E−03 | 1.143E−03 |
| 329 | 3.559E−01 | 3.111E−01 | 1.532E−01 | 1.937E−01 | 1.699E−01 | 3.462E−01 | 1.667E−01 | 1.622E−01 | 1.963E−01 | 2.032E−01 | 1.776E−01 | 2.724E−01 | 1.532E−01 |
| 330 | 3.475E−03 | 2.167E−03 | 4.119E−03 | 1.229E−03 | 1.806E−03 | 3.175E−03 | 2.724E−03 | 1.371E−03 | 1.929E−03 | 2.488E−03 | 1.439E−03 | 3.454E−03 | 2.295E−03 |
| 331 | 2.167E−02 | 1.811E−02 | 9.718E−03 | 1.491E−02 | 1.690E−02 | 2.167E−02 | 7.422E−03 | 1.006E−02 | 8.946E−03 | 1.735E−02 | 8.087E−03 | 2.210E−02 | 1.079E−02 |
| 332 | 0.000E+00 | 4.977E−04 | 3.733E−04 | 3.518E−04 | 4.934E−04 | 5.020E−04 | 4.955E−04 | 3.046E−04 | 1.753E−04 | 1.654E−04 | 1.800E−04 | 1.152E−03 | 3.261E−04 |
| 333 | 1.427E−02 | 1.279E−02 | 4.119E−03 | 1.124E−02 | 1.264E−02 | 1.388E−02 | 8.173E−03 | 8.838E−03 | 7.894E−03 | 1.191E−02 | 8.645E−03 | 1.364E−02 | 9.310E−03 |
| 334 | 0.000E+00 | 0.000E+00 | 0.000E+00 | 1.755E−04 | 0.000E+00 | 3.347E−04 | 0.000E+00 | 0.000E+00 | 3.497E−04 | 3.304E−04 | 0.000E+00 | 1.920E−04 | 0.000E+00 |
| 335 | 3.454E−02 | 3.304E−02 | 2.381E−02 | 2.274E−02 | 2.832E−02 | 3.518E−02 | 1.536E−02 | 2.025E−02 | 2.381E−02 | 2.424E−02 | 1.800E−02 | 2.252E−02 | 2.042E−02 |
| 336 | 1.349E−03 | 2.488E−03 | 1.495E−03 | 1.755E−03 | 1.313E−03 | 1.171E−03 | 1.487E−03 | 7.616E−04 | 1.227E−03 | 8.259E−04 | 7.208E−04 | 9.611E−04 | 4.891E−04 |
| 337 | 8.559E−02 | 8.002E−02 | 3.540E−02 | 4.741E−02 | 4.870E−02 | 7.701E−02 | 2.338E−02 | 3.025E−02 | 4.097E−02 | 4.248E−02 | 4.290E−02 | 5.106E−02 | 3.046E−02 |
| 338 | 1.926E−03 | 8.302E−04 | 3.733E−04 | 2.467E−03 | 8.216E−04 | 1.004E−03 | 1.238E−03 | 1.066E−03 | 3.497E−04 | 8.259E−04 | 1.079E−03 | 3.840E−04 | 3.261E−04 |
| 339 | 3.561E−02 | 3.068E−02 | 1.643E−02 | 2.274E−02 | 2.553E−02 | 4.741E−02 | 1.214E−02 | 2.010E−02 | 2.102E−02 | 2.274E−02 | 2.210E−02 | 2.295E−02 | 2.446E−02 |
| 340 | 2.510E−03 | 1.995E−03 | 1.868E−03 | 1.053E−03 | 1.478E−03 | 1.673E−03 | 2.231E−03 | 1.218E−03 | 1.401E−03 | 1.158E−03 | 1.259E−03 | 1.536E−03 | 1.143E−03 |
| 341 | 4.054E−03 | 2.488E−03 | 4.119E−03 | 4.205E−03 | 2.295E−03 | 1.673E−03 | 2.982E−03 | 1.523E−03 | 2.446E−03 | 2.317E−03 | 3.068E−03 | 2.488E−03 | 1.635E−03 |
| 342 | 7.701E−04 | 4.977E−04 | 1.122E−03 | 5.256E−04 | 4.934E−04 | 3.347E−04 | 0.000E+00 | 0.000E+00 | 1.753E−04 | 1.654E−04 | 1.259E−03 | 9.611E−04 | 6.543E−04 |
| 343 | 5.406E−03 | 2.488E−03 | 4.483E−03 | 2.982E−03 | 1.969E−03 | 4.848E−03 | 3.475E−03 | 4.870E−03 | 3.325E−03 | 3.304E−03 | 4.312E−03 | 2.682E−03 | 2.446E−03 |
| 344 | 1.926E−04 | 0.000E+00 | 3.733E−04 | 1.755E−04 | 0.000E+00 | 0.000E+00 | 2.467E−04 | 1.523E−04 | 5.256E−04 | 1.654E−04 | 1.800E−04 | 1.920E−04 | 1.635E−04 |

APPENDIX D-continued

Ovarian Cancer
Training Dataset

| | DY | DZ | EA | EB | EC | ED | EE | EF | EG | EH | EI |
|---|---|---|---|---|---|---|---|---|---|---|---|
| 1 | 13865 | 13879 | 13892 | 13897 | 13920 | 13989 | 14027 | 14080 | 14100 | 14202 | 14245 |
| 2 | Early Malignant | Benign | Benign | Benign | Benign | Late Malignant | Benign | Benign | Benign | Benign | Benign |
| 3 | 2 | 1 | 1 | 1 | 1 | 3 | 1 | 1 | 1 | 1 | 1 |
| 4 | −1 | −1 | −1 | −1 | −1 | −1 | −1 | −1 | −1 | −1 | −1 |
| 5 | 1.927E+00 | 1.945E+00 | 1.874E+00 | 3.742E+00 | 7.352E−01 | 7.263E−01 | 8.948E−01 | 1.126E+00 | 9.734E−01 | 5.504E−02 | 8.884E−01 |
| 6 | 2.457E−01 | 7.553E−01 | 9.300E−01 | 2.116E+00 | 3.959E−01 | 2.597E−01 | 3.240E−01 | 5.420E−01 | 6.655E−01 | 4.957E−02 | 6.803E−01 |
| 7 | 1.888E−01 | 2.983E−01 | 2.843E−01 | 7.457E−01 | 9.968E−02 | 9.571E−02 | 1.030E−01 | 1.760E−01 | 1.854E−01 | 4.410E−02 | 2.564E−01 |
| 8 | 5.290E−01 | 7.633E−01 | 7.039E−01 | 1.190E+00 | 2.414E−01 | 2.135E−01 | 3.369E−01 | 3.054E−01 | 3.278E−01 | 7.715E−02 | 3.916E−01 |
| 9 | 3.766E−02 | 1.695E−02 | 9.067E−03 | 2.221E−02 | 9.882E−03 | 9.013E−03 | 1.631E−02 | 5.633E−02 | 3.311E−02 | 6.609E−02 | 4.002E−02 |
| 10 | 5.644E−03 | 1.749E−02 | 2.189E−02 | 3.391E−02 | 2.242E−03 | 8.155E−03 | 7.833E−03 | 3.122E−03 | 0.000E+00 | 0.000E+00 | 1.599E−02 |
| 11 | 1.223E−02 | 1.749E−02 | 1.599E−02 | 2.800E−02 | 4.496E−03 | 6.438E−03 | 5.418E−03 | 1.663E−02 | 2.650E−02 | 1.105E−02 | 2.800E−02 |
| 12 | 1.320E−02 | 9.549E−03 | 4.796E−03 | 1.044E−02 | 3.594E−03 | 4.721E−03 | 3.015E−03 | 9.378E−03 | 0.000E+00 | 5.504E−03 | 1.202E−02 |
| 13 | 1.320E−02 | 8.498E−03 | 5.869E−03 | 7.833E−03 | 5.386E−03 | 2.575E−03 | 6.019E−03 | 4.174E−03 | 3.315E−03 | 1.652E−02 | 1.202E−02 |
| 14 | 2.725E−02 | 8.863E−02 | 9.914E−02 | 2.178E−01 | 1.395E−02 | 1.073E−02 | 3.251E−02 | 3.444E−02 | 2.650E−02 | 2.758E−02 | 5.601E−02 |
| 15 | 1.223E−02 | 4.249E−03 | 5.333E−03 | 9.785E−03 | 4.045E−03 | 4.292E−04 | 4.818E−03 | 7.296E−03 | 0.000E+00 | 1.105E−02 | 4.002E−03 |
| 16 | 9.399E−04 | 5.311E−04 | 5.333E−04 | 0.000E+00 | 0.000E+00 | 1.288E−03 | 0.000E+00 | 3.122E−03 | 6.620E−03 | 0.000E+00 | 4.002E−03 |
| 17 | 5.644E−03 | 5.837E−03 | 3.734E−03 | 8.476E−03 | 4.045E−03 | 2.146E−03 | 4.818E−03 | 3.122E−03 | 1.652E−02 | 0.000E+00 | 4.002E−03 |
| 18 | 3.766E−02 | 4.249E−02 | 1.921E−02 | 4.303E−02 | 1.845E−02 | 1.459E−02 | 1.148E−02 | 5.311E−02 | 2.318E−02 | 4.410E−02 | 4.002E−02 |
| 19 | 9.496E−02 | 1.073E−01 | 9.549E−02 | 2.554E−01 | 3.187E−02 | 3.004E−02 | 3.498E−02 | 6.363E−02 | 8.939E−02 | 1.652E−02 | 1.245E−01 |
| 20 | 1.878E−03 | 3.712E−03 | 6.395E−03 | 2.607E−03 | 4.045E−03 | 1.717E−03 | 0.000E+00 | 2.082E−03 | 3.315E−03 | 5.504E−03 | 4.002E−03 |
| 21 | 6.588E−03 | 1.330E−02 | 8.530E−03 | 1.631E−02 | 8.530E−03 | 8.155E−03 | 6.620E−03 | 1.663E−02 | 4.966E−02 | 5.504E−03 | 2.403E−02 |
| 22 | 5.644E−03 | 3.187E−03 | 3.734E−03 | 2.607E−03 | 2.242E−03 | 4.292E−04 | 1.202E−03 | 1.042E−03 | 0.000E+00 | 5.504E−03 | 4.002E−03 |
| 23 | 6.964E−02 | 3.981E−02 | 4.217E−02 | 1.309E−01 | 2.607E−02 | 2.790E−02 | 2.833E−02 | 5.633E−02 | 8.939E−02 | 2.758E−02 | 4.796E−02 |
| 24 | 9.592E−02 | 6.427E−02 | 4.002E−02 | 1.191E−01 | 3.144E−02 | 3.519E−02 | 2.833E−02 | 9.796E−02 | 4.304E−02 | 4.957E−02 | 4.002E−02 |
| 25 | 1.127E−02 | 2.393E−02 | 1.706E−02 | 7.049E−02 | 1.073E−02 | 9.013E−03 | 1.084E−02 | 1.459E−02 | 3.973E−02 | 0.000E+00 | 1.599E−02 |
| 26 | 1.223E−02 | 1.749E−02 | 2.403E−02 | 5.086E−02 | 3.144E−03 | 7.725E−03 | 1.148E−02 | 1.148E−02 | 1.320E−02 | 1.105E−02 | 5.204E−02 |
| 27 | 4.700E−03 | 4.775E−03 | 1.170E−02 | 1.373E−02 | 8.981E−04 | 3.433E−03 | 1.803E−03 | 8.337E−03 | 9.936E−03 | 0.000E+00 | 4.002E−03 |
| 28 | 3.852E−02 | 2.704E−02 | 2.457E−02 | 5.740E−02 | 2.157E−02 | 1.760E−02 | 1.685E−02 | 3.755E−02 | 2.983E−02 | 5.504E−03 | 3.605E−02 |
| 29 | 3.391E−02 | 5.150E−02 | 4.163E−02 | 6.459E−02 | 3.594E−02 | 1.803E−02 | 2.951E−02 | 5.633E−02 | 3.642E−02 | 1.652E−02 | 1.599E−02 |
| 30 | 1.062E−01 | 6.792E−02 | 5.923E−02 | 8.412E−02 | 4.850E−02 | 4.893E−02 | 5.966E−02 | 9.796E−02 | 2.983E−02 | 2.758E−02 | 3.605E−02 |
| 31 | 4.700E−02 | 5.569E−02 | 4.270E−02 | 8.090E−02 | 4.624E−02 | 3.305E−02 | 4.582E−02 | 4.796E−02 | 3.311E−02 | 5.504E−03 | 2.800E−02 |
| 32 | 9.399E−03 | 1.223E−02 | 9.603E−03 | 2.157E−02 | 4.045E−03 | 2.575E−03 | 1.266E−02 | 1.770E−02 | 0.000E+00 | 5.504E−03 | 1.996E−02 |
| 33 | 6.588E−03 | 9.024E−03 | 8.530E−03 | 1.760E−02 | 4.936E−03 | 5.579E−03 | 1.084E−02 | 1.459E−02 | 9.936E−03 | 5.504E−03 | 1.599E−02 |
| 34 | 1.706E−01 | 7.586E−01 | 6.770E−02 | 7.307E−02 | 5.343E−02 | 5.279E−02 | 7.285E−02 | 1.545E−01 | 8.939E−02 | 3.305E−02 | 4.796E−02 |
| 35 | 5.644E−02 | 5.783E−02 | 9.174E−02 | 1.373E−01 | 8.401E−02 | 6.738E−02 | 8.433E−02 | 1.180E−01 | 1.985E−02 | 4.957E−02 | 5.601E−02 |
| 36 | 9.399E−04 | 4.775E−03 | 1.067E−02 | 9.131E−03 | 5.386E−03 | 8.155E−03 | 9.635E−03 | 4.174E−03 | 0.000E+00 | 0.000E+00 | 0.000E+00 |
| 37 | 2.446E−02 | 1.534E−02 | 1.223E−02 | 2.414E−02 | 2.017E−02 | 6.009E−03 | 1.024E−02 | 3.648E−02 | 3.311E−02 | 2.200E−02 | 1.202E−02 |
| 38 | 9.399E−03 | 6.373E−03 | 4.796E−03 | 1.044E−02 | 2.242E−03 | 5.579E−03 | 1.803E−03 | 6.255E−03 | 9.936E−03 | 5.504E−03 | 8.004E−03 |
| 39 | 9.871E−02 | 8.391E−02 | 1.018E−01 | 1.835E−01 | 1.770E−01 | 4.421E−02 | 1.459E−01 | 1.491E−01 | 6.622E−02 | 1.760E−01 | 1.599E−01 |
| 40 | 1.148E−01 | 1.685E−01 | 9.174E−02 | 1.470E−01 | 1.642E−01 | 4.378E−02 | 8.251E−02 | 1.717E−01 | 1.324E−01 | 9.914E−02 | 7.200E−02 |
| 41 | 2.071E−02 | 1.438E−02 | 8.530E−03 | 2.607E−02 | 1.212E−02 | 9.442E−03 | 1.320E−02 | 2.189E−02 | 3.311E−02 | 3.852E−02 | 6.406E−02 |
| 42 | 1.878E−03 | 2.650E−03 | 1.067E−03 | 5.869E−03 | 1.352E−03 | 8.584E−04 | 1.803E−03 | 5.215E−03 | 1.985E−02 | 5.504E−03 | 0.000E+00 |
| 43 | 1.780E−02 | 1.006E−02 | 8.950E−03 | 6.713E−03 | 4.964E−03 | 5.761E−03 | 5.041E−03 | 3.935E−02 | 9.524E−03 | 5.272E−03 | 6.713E−03 |
| 44 | 2.092E−01 | 9.182E−02 | 1.168E−01 | 1.553E−01 | 3.935E−02 | 5.915E−02 | 5.838E−02 | 2.401E−01 | 1.159E−01 | 7.124E−02 | 1.150E−01 |
| 45 | 1.155E−01 | 6.456E−02 | 7.459E−02 | 8.950E−02 | 5.015E−02 | 5.144E−02j | 5.401E−02 | 1.664E−01 | 9.921E−02 | 6.070E−02 | 8.822E−02 |
| 46 | 2.879E−01 | 9.413E−02 | 1.337E−01 | 1.150E−01 | 6.018E−02 | 8.873E−02 | 8.693E−02 | 3.510E−01 | 8.730E−02 | 9.362E−02 | 1.304E−01 |
| 47 | 9.799E−02 | 4.192E−02 | 5.838E−02 | 5.092E−02 | 1.700E−02 | 3.498E−02 | 3.858E−02 | 9.394E−02 | 3.809E−02 | 1.849E−02 | 3.832E−02 |
| 48 | 2.052E−02 | 6.353E−03 | 8.436E−03 | 1.641E−02 | 4.295E−03 | 3.806E−03 | 6.636E−03 | 1.875E−02 | 9.524E−03 | 5.272E−03 | 2.598E−02 |

APPENDIX D-continued

Ovarian Cancer
Training Dataset

| | | | | | | | | | | | |
|---|---|---|---|---|---|---|---|---|---|---|---|
| 49 | 5.195E−03 | 7.381E−03 | 1.163E−02 | 8.127E−03 | 3.344E−03 | 2.263E−03 | 3.601E−03 | 1.325E−02 | 4.758E−03 | 2.649E−03 | 4.784E−03 |
| 50 | 5.195E−03 | 4.321E−03 | 2.803E−03 | 3.446E−03 | 1.831E−03 | 1.852E−03 | 2.598E−03 | 9.002E−03 | 6.353E−03 | 2.649E−03 | 1.150E−02 |
| 51 | 1.502E−01 | 1.723E−01 | 1.811E−01 | 1.263E−01 | 1.391E−01 | 3.290E−01 | 1.703E−01 | 4.232E−01 | 1.040E−01 | 1.728E−01 | 1.044E−01 |
| 52 | 5.633E−03 | 2.932E−03 | 2.173E−03 | 2.803E−03 | 2.572E−03 | 5.658E−03 | 2.752E−03 | 3.086E−02 | 2.382E−03 | 2.649E−03 | 1.919E−03 |
| 53 | 2.855E−02 | 1.145E−02 | 1.175E−02 | 8.745E−03 | 7.433E−03 | 1.008E−02 | 1.343E−02 | 2.598E−02 | 7.150E−03 | 1.319E−02 | 4.784E−03 |
| 54 | 5.642E+00 | 4.931E+00 | 4.751E+00 | 4.227E+00 | 6.169E+00 | 5.643E+00 | 6.195E+00 | 7.107E+00 | 7.164E+00 | 5.888E+00 | 5.543E+00 |
| 55 | 7.797E−01 | 6.237E−01 | 5.623E−01 | 6.061E−01 | 6.240E−01 | 6.963E−01 | 6.119E−01 | 9.349E−01 | 6.960E−01 | 5.875E−01 | 4.095E−01 |
| 56 | 1.919E−01 | 1.553E−01 | 1.605E−01 | 1.574E−01 | 2.130E−01 | 2.182E−01 | 1.867E−01 | 2.808E−01 | 2.706E−01 | 2.324E−01 | 2.214E−01 |
| 57 | 4.680E+00 | 3.631E+00 | 3.262E+00 | 3.257E+00 | 3.110E+00 | 3.841E+00 | 3.453E+00 | 4.785E+00 | 4.126E+00 | 4.234E+00 | 3.116E+00 |
| 58 | 1.294E−01 | 4.372E−02 | 5.761E−02 | 3.832E−02 | 3.472E−02 | 7.690E−02 | 6.224E−02 | 1.919E−01 | 8.889E−02 | 9.773E−02 | 5.555E−02 |
| 59 | 7.099E−02 | 5.993E−02 | 5.504E−02 | 5.350E−02 | 5.195E−02 | 5.272E−02 | 5.684E−02 | 6.446E−02 | 3.175E−02 | 3.035E−02 | 2.983E−02 |
| 60 | 8.127E−03 | 7.896E−03 | 6.507E−03 | 7.510E−03 | 6.996E−03 | 4.527E−03 | 1.054E−02 | 9.490E−03 | 4.758E−03 | 6.610E−03 | 1.919E−03 |
| 61 | 2.416E+00 | 1.110E+00 | 1.541E+00 | 1.689E+00 | 1.948E+00 | 2.302E+00 | 3.158E+00 | 2.192E+00 | 1.667E+00 | 1.916E+00 | 1.328E+00 |
| 62 | 4.477E−01 | 5.121E−01 | 4.239E−01 | 4.291E−01 | 6.925E−01 | 4.847E−01 | 4.905E−01 | 7.430E−01 | 1.160E+00 | 1.106E+00 | 1.056E+00 |
| 63 | 1.579E−02 | 6.224E−03 | 7.793E−03 | 9.696E−03 | 8.513E−03 | 1.327E−02 | 1.602E−02 | 1.924E−02 | 1.111E−02 | 1.453E−02 | 6.713E−03 |
| 64 | 1.881E+00 | 2.811E+00 | 2.616E+00 | 2.133E+00 | 3.725E+00 | 2.748E+00 | 2.564E+00 | 2.780E+00 | 1.552E+00 | 1.480E+00 | 1.211E+00 |
| 65 | 1.057E−01 | 9.516E−02 | 1.024E−01 | 6.764E−02 | 1.124E−01 | 1.286E−01 | 1.214E−01 | 1.167E−01 | 8.016E−02 | 5.813E−02 | 6.327E−02 |
| 66 | 5.748E−01 | 8.205E−01 | 5.723E−01 | 4.558E−01 | 6.198E−01 | 6.794E−01 | 6.299E−01 | 6.596E−01 | 3.778E−01 | 3.419E−01 | 3.203E−01 |
| 67 | 9.619E−02 | 4.784E−02 | 6.764E−02 | 2.881E−02 | 3.009E−02 | 1.034E−01 | 7.253E−02 | 1.099E−01 | 2.619E−02 | 1.319E−02 | 1.919E−02 |
| 68 | 1.533E−02 | 1.577E−02 | 2.238E−02 | 1.721E−02 | 1.561E−02 | 1.070E−02 | 1.343E−02 | 1.998E−02 | 1.190E−02 | 1.319E−02 | 1.535E−02 |
| 69 | 9.294E−01 | 5.870E−01 | 7.331E−01 | 6.388E−01 | 9.259E−01 | 8.215E−01 | 1.323E+00 | 5.574E−01 | 3.333E−01 | 3.855E−01 | 2.762E−01 |
| 70 | 3.704E−02 | 1.502E−02 | 2.019E−02 | 2.065E−02 | 1.970E−02 | 2.253E−02 | 3.266E−02 | 1.373E−02 | 1.429E−02 | 1.319E−02 | 1.054E−02 |
| 71 | 5.633E−03 | 7.124E−03 | 6.764E−03 | 4.835E−03 | 4.089E−03 | 3.909E−03 | 4.038E−03 | 7.253E−03 | 1.587E−03 | 0.000E+00 | 2.881E−03 |
| 72 | 8.565E−03 | 2.544E−03 | 2.428E−03 | 2.503E−03 | 3.884E−03 | 3.292E−03 | 5.195E−03 | 3.498E−03 | 4.758E−03 | 2.649E−03 | 3.832E−03 |
| 73 | 3.962E−03 | 2.235E−03 | 0.000E+00 | 6.862E−04 | 4.729E−04 | 4.515E−04 | 2.528E−03 | 2.190E−03 | 0.000E+00 | 0.000E+00 | 4.210E−03 |
| 74 | 4.944E−03 | 3.352E−03 | 6.174E−03 | 1.230E−02 | 1.885E−03 | 3.612E−03 | 1.264E−03 | 5.485E−03 | 1.045E−02 | 1.163E−02 | 1.264E−02 |
| 75 | 1.783E−02 | 6.196E−02 | 6.117E−02 | 2.077E−01 | 4.391E−02 | 2.664E−02 | 4.368E−02 | 1.086E−01 | 8.359E−02 | 4.052E−02 | 8.420E−02 |
| 76 | 5.147E−02 | 7.540E−02 | 1.065E−01 | 3.826E−01 | 4.492E−02 | 3.521E−02 | 5.632E−02 | 1.648E−01 | 9.055E−02 | 5.790E−02 | 1.140E−01 |
| 77 | 4.944E−03 | 1.230E−02 | 1.682E−02 | 4.594E−02 | 8.036E−03 | 4.063E−03 | 5.700E−03 | 2.415E−02 | 6.964E−03 | 5.790E−03 | 1.264E−02 |
| 78 | 2.968E−03 | 5.587E−04 | 1.122E−03 | 6.862E−04 | 1.422E−03 | 4.515E−04 | 6.332E−04 | 0.000E+00 | 3.488E−03 | 0.000E+00 | 0.000E+00 |
| 79 | 2.968E−03 | 2.235E−03 | 2.246E−03 | 2.054E−03 | 4.255E−03 | 1.806E−03 | 2.528E−03 | 4.391E−03 | 0.000E+00 | 0.000E+00 | 0.000E+00 |
| 80 | 0.000E+00 | 1.116E−03 | 0.000E+00 | 2.054E−03 | 9.447E−04 | 4.515E−04 | 0.000E+00 | 0.000E+00 | 0.000E+00 | 0.000E+00 | 4.210E−03 |
| 81 | 1.388E−02 | 1.343E−02 | 1.230E−02 | 9.605E−03 | 7.088E−03 | 3.160E−03 | 7.596E−03 | 1.208E−02 | 1.388E−02 | 0.000E+00 | 0.000E+00 |
| 82 | 4.944E−03 | 4.470E−03 | 5.609E−04 | 7.551E−03 | 4.729E−03 | 3.612E−03 | 5.700E−03 | 8.770E−03 | 3.488E−03 | 5.790E−03 | 4.210E−03 |
| 83 | 1.975E−03 | 1.670E−03 | 0.000E+00 | 4.808E−03 | 3.307E−03 | 4.515E−04 | 0.000E+00 | 1.096E−03 | 3.488E−03 | 0.000E+00 | 0.000E+00 |
| 84 | 3.962E−03 | 7.822E−03 | 1.851E−02 | 1.377E−02 | 1.422E−03 | 1.354E−03 | 6.332E−04 | 1.422E−02 | 1.388E−02 | 1.163E−02 | 8.420E−03 |
| 85 | 9.887E−04 | 0.000E+00 | 3.928E−03 | 2.743E−03 | 9.447E−04 | 4.515E−04 | 1.896E−03 | 2.190E−03 | 3.488E−03 | 0.000E+00 | 4.210E−03 |
| 86 | 8.905E−03 | 6.140E−03 | 8.973E−03 | 1.512E−02 | 1.087E−02 | 2.257E−03 | 6.964E−03 | 3.070E−02 | 1.388E−02 | 0.000E+00 | 1.264E−02 |
| 87 | 1.885E−02 | 3.409E−02 | 2.912E−02 | 6.998E−02 | 3.544E−02 | 1.761E−02 | 3.612E−02 | 9.865E−02 | 2.438E−02 | 5.790E−03 | 2.099E−02 |
| 88 | 0.000E+00 | 8.939E−03 | 7.291E−03 | 1.163E−02 | 5.666E−03 | 3.160E−03 | 6.332E−03 | 1.535E−02 | 1.045E−02 | 0.000E+00 | 4.210E−03 |
| 89 | 2.968E−03 | 1.456E−02 | 1.065E−02 | 2.743E−02 | 9.921E−03 | 7.223E−03 | 8.871E−03 | 3.950E−02 | 6.964E−03 | 5.790E−03 | 2.099E−02 |
| 90 | 2.472E−02 | 4.582E−02 | 5.214E−02 | 1.761E−01 | 5.293E−02 | 4.289E−02 | 6.456E−02 | 2.039E−01 | 4.528E−02 | 3.476E−02 | 3.363E−02 |
| 91 | 1.975E−03 | 6.704E−03 | 1.456E−02 | 1.919E−02 | 6.614E−03 | 1.084E−02 | 8.871E−03 | 1.535E−02 | 3.488E−03 | 5.790E−03 | 4.210E−03 |
| 92 | 6.930E−03 | 7.822E−03 | 9.537E−03 | 1.919E−02 | 1.129E−02 | 5.869E−03 | 3.172E−03 | 3.397E−02 | 2.088E−02 | 5.790E−03 | 8.420E−03 |
| 93 | 1.975E−03 | 3.905E−03 | 5.609E−03 | 1.512E−02 | 5.666E−03 | 2.257E−03 | 6.332E−03 | 1.648E−02 | 3.488E−03 | 5.790E−03 | 4.210E−03 |
| 94 | 9.887E−04 | 1.670E−03 | 0.000E+00 | 2.054E−03 | 4.729E−04 | 9.029E−04 | 6.332E−04 | 4.391E−03 | 0.000E+00 | 5.790E−03 | 0.000E+00 |
| 95 | 1.388E−02 | 1.343E−02 | 2.528E−02 | 3.499E−02 | 6.614E−03 | 6.321E−03 | 1.014E−02 | 4.165E−02 | 1.388E−02 | 0.000E+00 | 0.000E+00 |
| 96 | 5.937E−03 | 3.905E−03 | 1.065E−02 | 2.336E−02 | 7.088E−03 | 6.772E−03 | 4.436E−03 | 1.862E−02 | 3.488E−03 | 0.000E+00 | 4.210E−03 |
| 97 | 4.944E−03 | 5.587E−03 | 7.856E−03 | 1.163E−02 | 4.729E−03 | 9.029E−03 | 6.964E−03 | 1.648E−02 | 0.000E+00 | 5.790E−03 | 4.210E−03 |
| 98 | 4.944E−03 | 7.822E−03 | 1.010E−02 | 1.445E−02 | 2.833E−03 | 1.354E−03 | 5.700E−03 | 1.975E−02 | 0.000E+00 | 0.000E+00 | 2.099E−02 |

APPENDIX D-continued

Ovarian Cancer
Training Dataset

| | | | | | | | | | | | |
|---|---|---|---|---|---|---|---|---|---|---|---|
| 99 | 9.454E−02 | 1.097E−01 | 8.535E−02 | 1.913E−01 | 2.146E−01 | 4.414E−02 | 8.056E−02 | 1.459E−01 | 8.325E−02 | 1.133E−01 | 1.692E−01 |
| 100 | 5.261E−02 | 4.795E−02 | 3.102E−02 | 4.329E−02 | 2.771E−02 | 3.483E−02 | 3.029E−02 | 5.714E−02 | 3.029E−02 | 2.514E−02 | 3.200E−02 |
| 101 | 1.471E−01 | 1.815E−01 | 1.582E−01 | 1.766E−01 | 1.435E−01 | 9.712E−02 | 1.312E−01 | 1.754E−01 | 1.854E−01 | 1.196E−01 | 1.741E−01 |
| 102 | 1.901E−01 | 5.960E−01 | 6.732E−01 | 5.101E−01 | 1.643E−01 | 2.109E−01 | 1.212E−01 | 3.240E−01 | 5.146E−01 | 1.631E−01 | 8.412E−01 |
| 103 | 1.987E−01 | 2.023E−01 | 1.913E−01 | 2.575E−01 | 1.766E−01 | 8.191E−02 | 1.496E−01 | 2.228E−01 | 2.043E−01 | 2.207E−01 | 2.244E−01 |
| 104 | 3.176E−01 | 3.213E−01 | 2.416E−01 | 2.489E−01 | 2.636E−01 | 2.575E−01 | 1.790E−01 | 3.955E−01 | 2.800E−01 | 2.330E−01 | 3.200E−01 |
| 105 | 1.925E−01 | 7.750E−01 | 8.459E−01 | 8.194E−01 | 1.803E−01 | 1.324E−01 | 1.999E−01 | 1.876E−01 | 8.173E−01 | 2.514E−01 | 9.552E−01 |
| 106 | 2.134E−01 | 1.606E−01 | 2.048E−01 | 2.428E−01 | 2.980E−01 | 2.882E−01 | 2.060E−01 | 3.776E−01 | 1.627E−01 | 2.391E−01 | 1.876E−01 |
| 107 | 1.275E−01 | 1.324E−01 | 1.042E−01 | 1.324E−01 | 1.766E−01 | 9.172E−02 | 9.565E−02 | 1.631E−01 | 1.173E−01 | 9.442E−02 | 1.925E−01 |
| 108 | 2.085E−01 | 2.023E−01 | 1.839E−01 | 1.962E−01 | 2.256E−01 | 1.508E−01 | 1.668E−01 | 1.766E−01 | 1.627E−01 | 2.072E−01 | 2.146E−01 |
| 109 | 7.529E−03 | 7.284E−03 | 1.827E−03 | 6.708E−03 | 5.138E−04 | 6.867E−03 | 7.566E−03 | 3.568E−03 | 7.566E−03 | 0.000E+00 | 4.574E−03 |
| 110 | 5.371E−03 | 2.060E−02 | 1.219E−02 | 1.717E−02 | 5.641E−03 | 1.177E−02 | 8.952E−03 | 7.149E−03 | 0.000E+00 | 0.000E+00 | 0.000E+00 |
| 111 | 8.596E−03 | 2.489E−02 | 1.521E−02 | 1.422E−02 | 1.337E−02 | 4.905E−03 | 1.239E−02 | 1.312E−02 | 0.000E+00 | 0.000E+00 | 4.574E−03 |
| 112 | 1.182E−02 | 1.876E−02 | 9.749E−03 | 1.118E−02 | 9.749E−03 | 6.376E−03 | 1.101E−02 | 2.379E−03 | 0.000E+00 | 0.000E+00 | 4.574E−03 |
| 113 | 7.529E−03 | 4.243E−03 | 3.053E−03 | 2.980E−03 | 4.108E−03 | 1.471E−03 | 0.000E+00 | 1.191E−03 | 0.000E+00 | 0.000E+00 | 0.000E+00 |
| 114 | 4.304E−03 | 7.885E−03 | 2.440E−03 | 9.687E−03 | 3.593E−03 | 2.452E−03 | 2.060E−03 | 3.568E−03 | 0.000E+00 | 0.000E+00 | 0.000E+00 |
| 115 | 3.225E−03 | 3.029E−03 | 5.481E−03 | 7.456E−03 | 2.048E−03 | 2.943E−03 | 4.132E−03 | 4.770E−03 | 0.000E+00 | 0.000E+00 | 4.574E−03 |
| 116 | 1.074E−03 | 4.243E−03 | 2.440E−03 | 2.232E−03 | 2.048E−03 | 1.471E−03 | 1.373E−03 | 4.770E−03 | 0.000E+00 | 0.000E+00 | 0.000E+00 |
| 117 | 9.675E−03 | 1.091E−02 | 4.880E−03 | 1.193E−02 | 7.186E−03 | 5.395E−03 | 4.819E−03 | 4.770E−03 | 3.789E−03 | 6.291E−03 | 0.000E+00 |
| 118 | 5.371E−03 | 3.642E−03 | 1.827E−03 | 8.952E−03 | 1.545E−03 | 3.433E−03 | 2.747E−03 | 0.000E+00 | 0.000E+00 | 0.000E+00 | 0.000E+00 |
| 119 | 6.450E−03 | 6.671E−03 | 4.880E−03 | 3.728E−03 | 3.078E−03 | 1.962E−03 | 2.747E−03 | 0.000E+00 | 0.000E+00 | 6.291E−03 | 4.574E−03 |
| 120 | 2.146E−03 | 7.885E−03 | 5.481E−03 | 4.476E−03 | 0.000E+00 | 1.962E−03 | 6.879E−04 | 2.379E−03 | 3.789E−03 | 0.000E+00 | 0.000E+00 |
| 121 | 1.549E−01 | 1.175E−01 | 1.523E−01 | 1.122E−01 | 9.617E−02 | 3.375E−02 | 1.728E−01 | 4.622E−01 | 3.553E−01 | 4.337E−01 | 4.292E−01 |
| 122 | 1.683E−01 | 1.175E−01 | 1.371E−01 | 9.795E−02 | 1.318E−01 | 1.719E−01 | 1.291E−01 | 1.941E−01 | 2.843E−01 | 4.728E−01 | 2.858E−01 |
| 123 | 5.076E+00 | 1.879E+00 | 2.858E+00 | 3.598E+00 | 1.719E+00 | 2.199E+00 | 2.280E+00 | 1.655E+00 | 5.780E+00 | 3.348E+00 | 3.606E+00 |
| 124 | 8.077E−02 | 6.073E−02 | 4.960E−02 | 6.064E−02 | 6.109E−02 | 3.072E−02 | 6.465E−02 | 4.550E−01 | 3.079E−01 | 3.152E−01 | 1.719E−01 |
| 125 | 8.077E−02 | 5.699E−02 | 9.528E−02 | 1.211E−01 | 9.350E−02 | 4.301E−02 | 1.077E−01 | 5.966E−01 | 4.264E−01 | 3.544E−01 | 2.858E−01 |
| 126 | 2.084E−01 | 6.118E−01 | 7.017E−01 | 8.264E−01 | 9.350E−01 | 5.316E−01 | 5.984E−01 | 3.954E−01 | 6.396E−01 | 1.264E+00 | 8.299E−01 |
| 127 | 1.291E+00 | 1.291E+00 | 1.122E+00 | 2.244E+00 | 1.443E+00 | 1.077E+00 | 1.487E+00 | 1.309E+00 | 1.848E+00 | 4.533E+00 | 3.375E+00 |
| 128 | 2.654E+00 | 1.478E+00 | 2.315E+00 | 2.413E+00 | 1.273E+00 | 1.986E+00 | 2.012E+00 | 1.443E+00 | 4.738E+00 | 3.704E+00 | 3.090E+00 |
| 129 | 3.366E−02 | 4.176E−02 | 4.960E−02 | 8.869E−02 | 5.138E−02 | 5.218E−02 | 5.174E−02 | 2.458E−01 | 3.553E−01 | 7.881E−01 | 1.434E−01 |
| 130 | 6.821E+00 | 6.782E+00 | 9.638E+00 | 1.483E+01 | 1.657E+01 | 8.310E+00 | 1.846E+01 | 8.688E+00 | 1.653E+01 | 6.517E+01 | 3.773E+01 |
| 131 | 9.056E+00 | 1.040E+01 | 1.280E+01 | 1.152E+01 | 1.149E+01 | 6.606E+00 | 1.193E+01 | 1.014E+01 | 1.353E+01 | 3.901E+01 | 2.599E+01 |
| 132 | 1.345E−01 | 1.897E−02 | 4.577E−02 | 4.203E−02 | 4.176E−02 | 5.218E−02 | 4.310E−02 | 5.966E−02 | 1.656E−01 | 1.576E−01 | 1.149E−01 |
| 133 | 2.021E−02 | 1.523E−02 | 2.289E−02 | 2.796E−02 | 1.603E−02 | 1.843E−02 | 8.620E−03 | 3.731E−02 | 2.369E−02 | 7.881E−02 | 5.726E−02 |
| 134 | 0.000E+00 | 7.596E−03 | 3.811E−03 | 2.796E−02 | 9.617E−03 | 0.000E+00 | 1.291E−02 | 8.905E−02 | 4.737E−02 | 1.184E−01 | 5.726E−02 |
| 135 | 1.345E−02 | 1.140E−02 | 1.906E−02 | 3.268E−02 | 6.429E−03 | 3.072E−03 | 1.728E−02 | 6.714E−02 | 2.369E−02 | 7.881E−02 | 5.726E−02 |
| 136 | 3.366E−02 | 7.596E−03 | 2.671E−02 | 4.203E−02 | 1.282E−02 | 3.072E−03 | 8.620E−03 | 5.966E−02 | 7.106E−02 | 7.881E−02 | 0.000E+00 |
| 137 | 6.055E−02 | 5.316E−02 | 4.960E−02 | 6.999E−02 | 1.282E−02 | 1.843E−02 | 3.874E−02 | 2.983E−02 | 4.027E−01 | 7.881E−02 | 2.289E−01 |
| 138 | 6.732E−03 | 3.037E−02 | 2.671E−02 | 2.333E−02 | 6.109E−02 | 2.760E−02 | 4.310E−02 | 5.218E−02 | 1.184E−01 | 1.576E−01 | 1.434E−01 |
| 139 | 1.888E−01 | 1.060E−01 | 2.173E−01 | 1.496E−01 | 1.354E−01 | 3.874E−01 | 2.716E−01 | 3.206E−01 | 1.113E+00 | 7.097E−01 | 4.577E−01 |
| 140 | 1.817E−01 | 1.024E−01 | 9.172E−02 | 1.585E−01 | 5.459E−02 | 2.395E−01 | 1.202E−01 | 2.012E−01 | 4.738E−01 | 4.728E−01 | 5.726E−02 |
| 141 | 6.055E−02 | 1.523E−02 | 3.437E−02 | 6.064E−02 | 1.282E−02 | 2.458E−02 | 3.019E−02 | 1.042E−01 | 7.106E−02 | 3.152E−01 | 3.152E−01 |
| 142 | 2.021E−02 | 2.663E−02 | 1.523E−02 | 4.666E−03 | 6.429E−03 | 9.172E−03 | 1.728E−02 | 2.235E−02 | 7.106E−02 | 3.945E−02 | 0.000E+00 |
| 143 | 2.021E−02 | 7.596E−03 | 7.631E−03 | 3.731E−02 | 1.932E−02 | 9.172E−03 | 4.310E−03 | 7.453E−03 | 1.425E−01 | 0.000E+00 | 0.000E+00 |
| 144 | 4.711E−02 | 3.037E−02 | 3.811E−02 | 3.268E−02 | 2.573E−02 | 3.072E−03 | 2.155E−02 | 7.453E−02 | 0.000E+00 | 7.881E−02 | 8.584E−02 |
| 145 | 6.732E−03 | 2.280E−02 | 7.631E−03 | 2.796E−02 | 1.603E−02 | 2.760E−02 | 3.446E−02 | 4.470E−02 | 7.106E−02 | 7.881E−02 | 5.726E−02 |
| 146 | 3.028E−01 | 1.104E−01 | 2.671E−01 | 3.918E−01 | 2.155E−01 | 4.978E−01 | 3.793E−01 | 2.760E−01 | 7.817E−01 | 6.696E−01 | 3.722E−01 |
| 147 | 7.400E−02 | 9.528E−02 | 1.300E−01 | 1.309E−01 | 9.350E−02 | 2.030E−01 | 1.380E−01 | 1.719E−01 | 4.501E−01 | 1.184E−01 | 2.004E−01 |
| 148 | 3.900E−01 | 2.048E−01 | 3.891E−01 | 4.061E−01 | 3.054E−01 | 8.014E−01 | 4.052E−01 | 4.105E−01 | 1.184E+00 | 9.439E−01 | 8.299E−01 |

APPENDIX D-continued

Ovarian Cancer
Training Dataset

| | | | | | | | | | | | |
|---|---|---|---|---|---|---|---|---|---|---|---|
| 149 | 6.055E−02 | 3.419E−02 | 9.528E−02 | 7.934E−02 | 3.856E−02 | 1.354E−01 | 1.460E−01 | 6.714E−02 | 5.448E−01 | 2.760E−01 | 2.289E−01 |
| 150 | 2.689E−02 | 2.663E−02 | 3.811E−03 | 1.398E−02 | 1.932E−02 | 2.760E−02 | 2.582E−02 | 7.453E−02 | 6.396E−01 | 3.544E−01 | 2.289E−01 |
| 151 | 2.021E−02 | 1.523E−02 | 3.054E−02 | 4.666E−03 | 2.253E−02 | 1.532E−02 | 1.291E−02 | 7.453E−02 | 2.128E−01 | 1.576E−01 | 5.726E−02 |
| 152 | 2.689E−02 | 4.933E−02 | 2.671E−02 | 5.138E−02 | 1.932E−02 | 1.229E−02 | 1.728E−02 | 5.966E−02 | 9.439E−02 | 3.945E−02 | 8.584E−02 |
| 153 | 2.689E−02 | 1.523E−02 | 1.523E−02 | 1.398E−02 | 9.617E−03 | 1.532E−02 | 3.019E−02 | 4.470E−02 | 2.369E−02 | 3.945E−02 | 5.726E−02 |
| 154 | 2.021E−02 | 2.280E−02 | 3.811E−03 | 9.350E−03 | 9.617E−03 | 1.843E−02 | 1.291E−02 | 4.470E−02 | 0.000E+00 | 7.881E−02 | 0.000E+00 |
| 155 | 2.689E−02 | 1.523E−02 | 2.671E−02 | 2.333E−02 | 3.535E−02 | 6.144E−03 | 3.019E−02 | 7.453E−02 | 0.000E+00 | 1.184E−01 | 2.858E−02 |
| 156 | 7.471E−01 | 4.256E−01 | 1.069E+00 | 6.251E−01 | 5.013E−01 | 8.602E−01 | 8.139E−01 | 9.439E−01 | 1.919E+00 | 1.380E+00 | 3.722E−01 |
| 157 | 1.950E−01 | 1.478E−01 | 2.636E−01 | 1.024E−01 | 1.318E−01 | 3.651E−01 | 2.582E−01 | 2.609E−01 | 7.343E−01 | 3.152E−01 | 1.719E−01 |
| 158 | 4.034E−01 | 2.164E−01 | 5.378E−01 | 4.337E−01 | 4.372E−01 | 1.140E+00 | 8.744E−01 | 3.651E−01 | 1.113E+00 | 1.336E+00 | 4.862E−01 |
| 159 | 1.345E−01 | 1.211E−01 | 1.683E−01 | 1.915E−01 | 8.994E−02 | 2.885E−01 | 1.941E−01 | 1.487E−01 | 4.027E−01 | 5.913E−01 | 2.289E−01 |
| 160 | 4.711E−02 | 3.037E−02 | 1.906E−02 | 3.731E−02 | 2.894E−02 | 4.301E−02 | 2.582E−02 | 5.966E−02 | 4.737E−02 | 1.576E−01 | 5.726E−02 |
| 161 | 2.689E−02 | 1.897E−02 | 2.671E−02 | 2.796E−02 | 1.932E−02 | 1.532E−02 | 1.728E−02 | 2.983E−02 | 2.369E−02 | 1.184E−01 | 0.000E+00 |
| 162 | 6.732E−03 | 3.793E−02 | 3.811E−02 | 2.333E−02 | 2.253E−02 | 9.172E−03 | 2.582E−02 | 7.453E−03 | 0.000E+00 | 1.184E−01 | 2.858E−02 |
| 163 | 3.366E−02 | 2.663E−02 | 3.811E−03 | 1.870E−02 | 2.573E−02 | 2.458E−02 | 1.728E−02 | 2.983E−02 | 0.000E+00 | 0.000E+00 | 2.858E−02 |
| 164 | 2.021E−02 | 1.897E−02 | 0.000E+00 | 3.268E−02. | 6.429E−03 | 9.172E−03 | 8.620E−03 | 2.983E−02 | 2.369E−02 | 0.000E+00 | 0.000E+00 |
| 165 | 4.034E−02 | 4.176E−02 | 4.194E−02 | 1.398E−02 | 2.894E−02 | 1.843E−02 | 2.155E−02 | 3.731E−02 | 4.737E−02 | 3.945E−02 | 2.858E−02 |
| 166 | 8.744E−02 | 1.523E−02 | 8.771E−02 | 6.536E−02 | 4.817E−02 | 7.373E−02 | 6.028E−02 | 1.122E−01 | 9.439E−02 | 3.945E−02 | 8.584E−02 |
| 167 | 4.167E−01 | 3.954E−01 | 6.144E−01 | 3.037E−01 | 1.959E−01 | 6.937E−01 | 6.981E−01 | 3.428E−01 | 4.027E−01 | 5.913E−01 | 4.292E−01 |
| 168 | 2.627E−01 | 1.140E−01 | 2.137E−01 | 1.630E−01 | 1.024E−01 | 2.796E−01 | 2.671E−01 | 1.567E−01 | 2.843E−01 | 4.728E−01 | 2.004E−01 |
| 169 | 8.077E−02 | 6.456E−02 | 6.483E−02 | 4.666E−02 | 9.350E−02 | 1.202E−01 | 1.167E−01 | 5.218E−02 | 1.184E−01 | 1.576E−01 | 8.584E−02 |
| 170 | 6.732E−02 | 3.419E−02 | 1.523E−02 | 4.203E−02 | 1.603E−02 | 2.146E−02 | 4.310E−02 | 5.218E−02 | 0.000E+00 | 3.945E−02 | 2.858E−02 |
| 171 | 5.378E−02 | 4.176E−02 | 3.054E−02 | 1.870E−02 | 6.429E−03 | 2.146E−02 | 3.019E−02 | 4.470E−02 | 4.737E−02 | 3.945E−02 | 5.726E−02 |
| 172 | 1.102E−01 | 2.256E−01 | 1.435E−01 | 1.398E−01 | 5.445E−02 | 1.790E−01 | 9.614E−02 | 1.337E−02 | 8.807E−02 | 1.194E−01 | 1.064E−01 |
| 173 | 6.205E−01 | 2.886E+00 | 2.690E+00 | 3.950E+00 | 3.433E−01 | 6.107E−01 | 3.666E−01 | 1.337E−02 | 2.469E+00 | 3.801E−01 | 4.577E+00 |
| 174 | 4.746E−01 | 4.399E+00 | 4.776E+00 | 6.432E+00 | 6.107E−01 | 7.892E−01 | 5.800E−01 | 9.246E−02 | 3.445E+00 | 3.311E−01 | 6.090E+00 |
| 175 | 3.936E−01 | 1.527E+00 | 1.101E+00 | 1.683E+00 | 4.549E−01 | 4.022E−01 | 2.808E−01 | 1.078E−01 | 1.047E+00 | 2.980E−01 | 2.003E+00 |
| 176 | 2.590E+00 | 3.276E+00 | 3.140E+00 | 3.387E+00 | 1.574E+00 | 1.876E+00 | 1.696E+00 | 4.375E−01 | 3.073E+00 | 1.243E+00 | 4.801E+00 |
| 177 | 1.196E+00 | 1.729E+00 | 2.419E+00 | 2.460E+00 | 1.424E+00 | 1.823E+00 | 1.674E+00 | 2.783E−01 | 2.075E+00 | 8.682E−01 | 2.866E+00 |
| 178 | 1.901E−01 | 3.433E−01 | 5.334E−01 | 4.255E−01 | 2.219E−01 | 4.966E−01 | 3.703E−01 | 3.691E−02 | 2.740E−01 | 2.330E−01 | 4.181E−01 |
| 179 | 2.869E−02 | 4.132E−02 | 6.781E−02 | 4.623E−02 | 2.833E−02 | 3.384E−02 | 3.262E−02 | 9.246E−03 | 3.914E−02 | 3.262E−02 | 4.733E−02 |
| 180 | 2.502E−02 | 3.188E−02 | 1.422E−02 | 1.668E−02 | 9.295E−03 | 3.801E−03 | 5.334E−03 | 2.048E−03 | 1.631E−02 | 1.085E−02 | 4.341E−02 |
| 181 | 2.134E−02 | 2.244E−02 | 2.367E−02 | 1.349E−02 | 2.256E−02 | 7.186E−03 | 1.300E−02 | 2.048E−03 | 1.962E−02 | 0.000E+00 | 1.582E−02 |
| 182 | 2.685E−02 | 7.787E−02 | 9.148E−02 | 8.351E−02 | 1.062E−02 | 1.778E−02 | 1.839E−02 | 1.026E−03 | 8.807E−02 | 1.085E−02 | 1.422E−01 |
| 183 | 7.750E−01 | 1.944E+00 | 1.596E+00 | 1.292E+00 | 9.076E−01 | 1.350E+00 | 5.236E−01 | 2.085E−01 | 6.426E−01 | 9.116E−01 | 1.596E+00 |
| 184 | 7.468E−01 | 1.692E+00 | 1.983E+00 | 1.456E+00 | 8.062E−01 | 1.495E+00 | 9.062E−01 | 2.228E−01 | 6.654E−01 | 1.031E+00 | 1.340E+00 |
| 185 | 2.575E−01 | 1.160E+00 | 1.204E+00 | 9.062E−01 | 4.525E−01 | 6.916E−01 | 3.409E−01 | 8.118E−02 | 4.567E−01 | 4.611E−01 | 8.363E−01 |
| 186 | 1.606E+00 | 2.923E+00 | 2.834E+00 | 1.681E+00 | 2.363E+00 | 2.655E+00 | 1.497E+00 | 3.758E−01 | 1.054E+00 | 1.194E+00 | 1.770E+00 |
| 187 | 4.414E−01 | 8.832E−01 | 5.947E−01 | 4.194E−01 | 8.155E−01 | 7.002E−01 | 3.311E−01 | 1.017E−01 | 2.022E−01 | 5.910E−01 | 5.322E−01 |
| 188 | 5.285E−02 | 9.307E−02 | 4.255E−02 | 4.047E−02 | 7.345E−02 | 7.787E−02 | 3.740E−02 | 1.852E−02 | 2.931E−02 | 1.085E−01 | 5.910E−02 |
| 189 | 2.502E−02 | 1.729E−02 | 1.888E−02 | 1.093E−02 | 1.288E−02 | 2.833E−02 | 2.735E−02 | 3.078E−03 | 3.262E−03 | 3.801E−02 | 2.367E−02 |
| 190 | 2.918E−01 | 3.102E−01 | 1.803E−01 | 1.086E−01 | 3.421E−01 | 2.526E−01 | 1.876E−01 | 7.701E−02 | 1.044E−01 | 1.901E−01 | 1.223E−01 |
| 191 | 4.754E+00 | 3.028E+00 | 4.765E+00 | 2.352E+00 | 6.898E+00 | 7.266E+00 | 5.709E+00 | 9.673E−01 | 1.638E+00 | 5.291E+00 | 2.184E+00 |
| 192 | 1.134E+00 | 9.131E−01 | 1.447E+00 | 5.677E−01 | 1.539E+00 | 2.452E+00 | 1.607E+00 | 2.228E−01 | 3.295E−01 | 1.248E+00 | 4.733E−01 |
| 193 | 1.121E−01 | 1.224E−01 | 1.790E−01 | 7.774E−02 | 1.435E−01 | 2.489E−01 | 1.533E−01 | 4.206E−02 | 7.829E−02 | 1.680E−01 | 9.859E−02 |
| 194 | 7.689E−02 | 8.473E−02 | 5.776E−02 | 4.623E−02 | 2.121E−02 | 1.729E−02 | 1.484E−02 | 1.643E−02 | 4.241E−02 | 3.262E−02 | 8.670E−02 |
| 195 | 2.685E−02 | 3.139E−02 | 2.256E−02 | 3.151E−02 | 8.853E−03 | 9.724E−03 | 6.524E−03 | 7.186E−03 | 3.262E−03 | 4.341E−02 | 4.341E−02 |
| 196 | 2.452E−01 | 3.863E−01 | 3.532E−01 | 1.803E−01 | 3.544E−01 | 3.225E−01 | 3.053E−01 | 1.398E−01 | 1.109E−01 | 4.231E−01 | 1.337E−01 |
| 197 | 1.987E−01 | 2.036E−01 | 2.379E−01 | 9.638E−02 | 2.109E−01 | 2.636E−01 | 2.146E−01 | 2.869E−02 | 3.914E−02 | 1.139E−01 | 5.518E−02 |
| 198 | 1.019E−01 | 8.633E−02 | 1.003E−01 | 4.047E−02 | 9.822E−02 | 1.324E−01 | 8.964E−02 | 2.256E−02 | 1.631E−02 | 3.801E−02 | 2.367E−02 |

APPENDIX D-continued

Ovarian Cancer
Training Dataset

| | | | | | | | | | | | |
|---|---|---|---|---|---|---|---|---|---|---|---|
| 199 | 1.839E−01 | 6.646E−02 | 2.465E−02 | 1.545E−02 | 1.901E−02 | 3.041E−02 | 1.361E−02 | 7.186E−03 | 1.962E−02 | 2.710E−02 | 2.759E−02 |
| 200 | 7.039E−02 | 6.646E−02 | 2.833E−02 | 2.502E−02 | 9.295E−03 | 1.015E−02 | 4.157E−03 | 7.186E−03 | 1.631E−02 | 0.000E+00 | 4.733E−02 |
| 201 | 3.433E−02 | 4.083E−02 | 2.207E−02 | 1.484E−02 | 2.207E−02 | 1.950E−02 | 1.655E−02 | 1.435E−02 | 1.300E−02 | 2.710E−02 | 5.126E−02 |
| 202 | 9.270E−03 | 4.709E−03 | 1.051E−03 | 6.426E−04 | 2.207E−03 | 8.461E−04 | 1.778E−03 | 2.048E−03 | 6.524E−03 | 1.631E−02 | 0.000E+00 |
| 203 | 3.703E−03 | 1.046E−03 | 1.051E−03 | 6.426E−04 | 1.324E−03 | 8.461E−04 | 0.000E+00 | 1.026E−03 | 0.000E+00 | 0.000E+00 | 0.000E+00 |
| 204 | 1.204E−02 | 3.666E−03 | 3.679E−03 | 1.288E−03 | 1.324E−03 | 1.692E−03 | 2.379E−03 | 1.026E−03 | 0.000E+00 | 0.000E+00 | 0.000E+00 |
| 205 | 9.270E−04 | 0.000E+00 | 1.582E−03 | 6.426E−04 | 8.853E−04 | 1.263E−03 | 0.000E+00 | 0.000E+00 | 3.262E−03 | 0.000E+00 | 0.000E+00 |
| 206 | 1.570E−02 | 5.751E−03 | 4.206E−03 | 1.288E−03 | 1.324E−03 | 2.538E−03 | 4.746E−03 | 0.000E+00 | 0.000E+00 | 0.000E+00 | 3.936E−03 |
| 207 | 1.852E−03 | 0.000E+00 | 1.051E−03 | 1.288E−03 | 0.000E+00 | 4.231E−04 | 1.187E−03 | 0.000E+00 | 0.000E+00 | 0.000E+00 | 0.000E+00 |
| 208 | 3.703E−03 | 2.097E−03 | 3.151E−03 | 3.850E−03 | 3.544E−03 | 8.461E−04 | 5.935E−04 | 0.000E+00 | 3.262E−03 | 0.000E+00 | 0.000E+00 |
| 209 | 1.852E−03 | 0.000E+00 | 0.000E+00 | 1.288E−03 | 0.000E+00 | 1.263E−03 | 0.000E+00 | 0.000E+00 | 0.000E+00 | 0.000E+00 | 0.000E+00 |
| 210 | 0.000E+00 | 1.570E−03 | 0.000E+00 | 0.000E+00 | 4.427E−04 | 0.000E+00 | 1.187E−03 | 0.000E+00 | 0.000E+00 | 0.000E+00 | 0.000E+00 |
| 211 | 0.000E+00 | 0.000E+00 | 1.051E−03 | 0.000E+00 | 8.853E−04 | 4.231E−04 | 0.000E+00 | 0.000E+00 | 0.000E+00 | 0.000E+00 | 0.000E+00 |
| 212 | 1.852E−03 | 5.224E−04 | 5.248E−04 | 6.426E−04 | 0.000E+00 | 4.231E−04 | 0.000E+00 | 0.000E+00 | 0.000E+00 | 5.432E−03 | 0.000E+00 |
| 213 | 1.852E−03 | 5.751E−03 | 2.624E−03 | 2.575E−03 | 4.427E−03 | 2.955E−03 | 0.000E+00 | 0.000E+00 | 0.000E+00 | 0.000E+00 | 0.000E+00 |
| 214 | 1.852E−03 | 4.181E−03 | 1.051E−03 | 6.426E−04 | 1.766E−03 | 4.231E−04 | 1.187E−03 | 0.000E+00 | 0.000E+00 | 1.085E−02 | 0.000E+00 |
| 215 | 0.000E+00 | 5.224E−04 | 1.051E−03 | 6.426E−04 | 0.000E+00 | 8.461E−04 | 5.935E−04 | 0.000E+00 | 0.000E+00 | 0.000E+00 | 3.936E−03 |
| 216 | 9.270E−04 | 2.612E−03 | 5.248E−04 | 6.426E−04 | 4.427E−04 | 8.461E−04 | 5.935E−04 | 1.026E−03 | 3.262E−03 | 0.000E+00 | 0.000E+00 |
| 217 | 1.852E−03 | 2.612E−03 | 5.248E−04 | 1.288E−03 | 0.000E+00 | 4.231E−04 | 1.778E−03 | 0.000E+00 | 0.000E+00 | 0.000E+00 | 0.000E+00 |
| 218 | 1.198E+00 | 2.580E+00 | 1.746E+00 | 1.544E+00 | 1.127E+00 | 1.738E+00 | 6.585E−01 | 4.816E−01 | 1.288E+00 | 2.024E+00 | 2.700E+00 |
| 219 | 9.270E−03 | 2.661E−02 | 2.048E−02 | 1.803E−02 | 1.106E−02 | 9.307E−03 | 1.300E−02 | 4.108E−03 | 3.262E−03 | 3.262E−02 | 3.936E−03 |
| 220 | 1.761E+00 | 2.131E+00 | 2.009E+00 | 2.040E+00 | 1.613E+00 | 2.233E+00 | 1.533E+00 | 1.722E+00 | 1.267E+00 | 9.582E−01 | 1.432E+00 |
| 221 | 1.030E+02 | 6.659E+01 | 6.377E+01 | 8.020E+01 | 4.832E+01 | 5.834E+01 | 5.626E+01 | 4.300E+01 | 9.256E+01 | 3.645E+01 | 6.488E+01 |
| 222 | 2.134E+01 | 5.362E+01 | 5.345E+01 | 6.824E+01 | 3.789E+01 | 3.488E+01 | 3.406E+01 | 2.840E+01 | 9.111E+01 | 2.251E+01 | 6.460E+01 |
| 223 | 1.958E+01 | 3.219E+01 | 2.769E+01 | 4.287E+01 | 1.766E+01 | 1.951E+01 | 1.711E+01 | 1.983E+01 | 4.503E+01 | 1.252E+01 | 2.977E+01 |
| 224 | 2.647E+01 | 2.766E+01 | 2.331E+01 | 2.686E+01 | 1.771E+01 | 1.802E+01 | 1.914E+01 | 1.359E+01 | 3.088E+01 | 1.201E+01 | 2.632E+01 |
| 225 | 1.655E+01 | 1.708E+01 | 2.174E+01 | 3.000E+01 | 1.698E+01 | 1.964E+01 | 2.653E+01 | 1.356E+01 | 3.015E+01 | 1.612E+01 | 2.571E+01 |
| 226 | 6.307E+00 | 1.914E+01 | 1.749E+01 | 1.784E+01 | 6.248E+00 | 6.178E+00 | 1.026E+01 | 8.423E+00 | 1.604E+01 | 5.026E+00 | 1.015E+01 |
| 227 | 2.454E+00 | 5.574E+00 | 5.398E+00 | 4.985E+00 | 2.209E+00 | 2.471E+00 | 3.351E+00 | 2.778E+00 | 3.801E+00 | 1.800E+00 | 3.596E+00 |
| 228 | 3.262E−01 | 3.711E−01 | 2.255E−01 | 1.731E−01 | 2.762E−01 | 2.053E−01 | 2.473E−01 | 4.745E−01 | 3.620E−01 | 3.469E−01 | 3.086E−01 |
| 229 | 3.480E−01 | 3.779E−01 | 2.564E−01 | 1.860E−01 | 3.081E−01 | 2.006E−01 | 2.661E−01 | 4.745E−01 | 3.982E−01 | 4.156E−01 | 3.894E−01 |
| 230 | 2.444E+01 | 3.142E+01 | 3.389E+01 | 4.121E+01 | 3.042E+01 | 1.479E+01 | 2.339E+01 | 3.160E+01 | 3.942E+01 | 3.093E+01 | 3.674E+01 |
| 231 | 3.748E+00 | 4.268E+00 | 4.732E+00 | 4.640E+00 | 4.729E+00 | 2.579E+00 | 3.539E+00 | 5.249E+00 | 3.222E+00 | 4.334E+00 | 4.012E+00 |
| 232 | 1.409E+00 | 1.511E+00 | 1.553E+00 | 1.715E+00 | 1.820E+00 | 6.410E−01 | 1.352E+00 | 1.585E+00 | 1.267E+00 | 1.242E+00 | 1.453E+00 |
| 233 | 4.164E+00 | 5.317E+00 | 4.462E+00 | 5.367E+00 | 6.430E+00 | 4.545E+00 | 5.937E+00 | 4.268E+00 | 4.452E+00 | 5.153E+00 | 5.905E+00 |
| 234 | 1.467E+01 | 1.575E+01 | 1.733E+01 | 1.509E+01 | 1.529E+01 | 2.197E+01 | 1.606E+01 | 2.000E+01 | 1.057E+01 | 1.684E+01 | 1.429E+01 |
| 235 | 1.308E+01 | 9.236E+00 | 1.104E+01 | 8.200E+00 | 1.009E+01 | 8.784E+00 | 8.484E+00 | 1.156E+01 | 7.891E+00 | 9.519E+00 | 7.213E+00 |
| 236 | 4.736E−01 | 1.097E+00 | 9.119E−01 | 7.007E−01 | 6.458E−01 | 2.145E−01 | 6.066E−01 | 4.731E−01 | 3.258E−01 | 2.062E−01 | 5.732E−01 |
| 237 | 2.844E+00 | 5.255E+00 | 3.937E+00 | 4.429E+00 | 7.235E+00 | 2.362E+00 | 4.081E+00 | 4.133E+00 | 3.366E+00 | 4.379E+00 | 4.894E+00 |
| 238 | 6.483E+00 | 6.101E+00 | 5.421E+00 | 6.696E+00 | 7.061E+00 | 3.258E+00 | 4.245E+00 | 6.987E+00 | 4.959E+00 | 4.865E+00 | 5.176E+00 |
| 239 | 1.325E+00 | 1.194E+00 | 1.158E+00 | 1.157E+00 | 1.430E+00 | 6.334E−01 | 9.630E−01 | 1.334E+00 | 1.050E+00 | 7.315E−01 | 9.996E−01 |
| 240 | 1.273E+01 | 1.108E+01 | 5.339E+00 | 3.450E+00 | 9.701E+00 | 1.039E+01 | 7.346E+00 | 8.549E+00 | 5.068E+00 | 7.187E+00 | 7.489E+00 |
| 241 | 2.485E+02 | 2.140E+02 | 2.262E+02 | 2.023E+02 | 2.552E+02 | 2.716E+02 | 2.419E+02 | 2.643E+02 | 2.333E+02 | 3.144E+02 | 2.487E+02 |
| 242 | 1.848E+02 | 1.507E+02 | 1.496E+02 | 1.404E+02 | 1.433E+02 | 1.919E+02 | 1.442E+02 | 1.939E+02 | 1.294E+02 | 1.753E+02 | 1.317E+02 |
| 243 | 1.604E+01 | 1.366E+01 | 1.330E+01 | 1.170E+01 | 1.290E+01 | 1.746E+01 | 1.269E+01 | 1.689E+01 | 1.057E+01 | 1.470E+01 | 1.131E+01 |
| 244 | 1.572E+01 | 9.512E+00 | 1.332E+01 | 1.513E+01 | 1.242E+01 | 7.729E+00 | 1.354E+01 | 1.066E+01 | 7.493E+00 | 1.048E+01 | 1.454E+01 |
| 245 | 5.480E+00 | 5.744E+00 | 5.800E+00 | 6.320E+00 | 6.301E+00 | 3.186E+00 | 5.067E+00 | 4.695E+00 | 3.149E+00 | 4.781E+00 | 5.608E+00 |
| 246 | 5.547E+00 | 6.296E+00 | 5.303E+00 | 4.879E+00 | 8.304E+00 | 3.926E+00 | 5.621E+00 | 5.975E+00 | 4.452E+00 | 5.560E+00 | 5.881E+00 |
| 247 | 4.978E+00 | 4.394E+00 | 3.891E+00 | 3.561E+00 | 4.956E+00 | 2.798E+00 | 3.583E+00 | 4.112E+00 | 3.330E+00 | 3.630E+00 | 3.630E+00 |
| 248 | 1.159E+02 | 6.310E+01 | 8.556E+01 | 8.203E+01 | 1.015E+02 | 1.349E+02 | 1.470E+02 | 9.220E+01 | 7.620E+01 | 1.324E+02 | 8.866E+01 |

APPENDIX D-continued

Ovarian Cancer
Training Dataset

| | | | | | | | | | | | |
|---|---|---|---|---|---|---|---|---|---|---|---|
| 249 | 7.605E+01 | 7.054E+01 | 7.097E+01 | 5.560E+01 | 6.872E+01 | 1.159E+02 | 8.913E+01 | 7.244E+01 | 5.687E+01 | 8.726E+01 | 6.523E+01 |
| 250 | 1.041E+02 | 1.274E+02 | 1.234E+02 | 9.756E+01 | 1.459E+02 | 1.477E+02 | 1.262E+02 | 1.288E+02 | 1.261E+02 | 1.636E+02 | 1.388E+02 |
| 251 | 4.378E+01 | 5.333E+01 | 4.060E+01 | 3.503E+01 | 4.232E+01 | 4.794E+01 | 3.991E+01 | 4.446E+01 | 3.700E+01 | 4.403E+01 | 4.150E+01 |
| 252 | 3.313E+00 | 3.927E+00 | 3.058E+00 | 2.304E+00 | 2.715E+00 | 3.009E+00 | 2.878E+00 | 2.465E+00 | 1.738E+00 | 2.102E+00 | 2.366E+00 |
| 253 | 6.235E+00 | 6.325E+00 | 7.466E+00 | 5.348E+00 | 4.336E+00 | 2.224E+00 | 4.734E+00 | 5.038E+00 | 3.294E+00 | 3.563E+00 | 4.204E+00 |
| 254 | 1.470E+01 | 1.001E+01 | 1.295E+01 | 1.454E+01 | 1.253E+01 | 6.204E+00 | 1.098E+01 | 1.144E+01 | 7.276E+00 | 9.357E+00 | 1.151E+01 |
| 255 | 1.361E+01 | 7.887E+00 | 9.848E+00 | 1.219E+01 | 1.070E+01 | 6.055E+00 | 1.030E+01 | 7.978E+00 | 8.326E+00 | 8.117E+00 | 9.636E+00 |
| 256 | 5.334E+00 | 3.042E+00 | 2.843E+00 | 2.924E+00 | 2.963E+00 | 1.879E+00 | 2.817E+00 | 2.696E+00 | 2.281E+00 | 2.383E+00 | 2.778E+00 |
| 257 | 4.499E+00 | 5.680E+00 | 3.816E+00 | 4.972E+00 | 4.897E+00 | 2.224E+00 | 3.353E+00 | 4.117E+00 | 3.656E+00 | 3.567E+00 | 4.572E+00 |
| 258 | 3.925E+01 | 4.066E+01 | 4.361E+01 | 2.656E+01 | 3.215E+01 | 3.835E+01 | 4.808E+01 | 3.883E+01 | 2.241E+01 | 3.598E+01 | 2.513E+01 |
| 259 | 6.937E+01 | 4.492E+01 | 5.598E+01 | 4.406E+01 | 6.115E+01 | 7.857E+01 | 9.200E+01 | 4.620E+01 | 3.790E+01 | 6.773E+01 | 4.736E+01 |
| 260 | 4.460E+01 | 4.124E+01 | 4.071E+01 | 3.483E+01 | 3.355E+01 | 5.336E+01 | 4.803E+01 | 2.788E+01 | 2.519E+01 | 3.520E+01 | 2.991E+01 |
| 261 | 3.036E+01 | 3.379E+01 | 2.930E+01 | 3.872E+01 | 2.834E+01 | 1.684E+01 | 2.271E+01 | 2.360E+01 | 2.519E+01 | 2.366E+01 | 2.870E+01 |
| 262 | 1.090E+01 | 1.237E+01 | 9.511E+00 | 1.119E+01 | 7.790E+00 | 5.595E+00 | 7.753E+00 | 7.540E+00 | 8.362E+00 | 7.664E+00 | 9.846E+00 |
| 263 | 4.955E+00 | 4.436E+00 | 5.030E+00 | 4.291E+00 | 4.088E+00 | 1.951E+00 | 4.009E+00 | 4.244E+00 | 2.498E+00 | 2.842E+00 | 3.201E+00 |
| 264 | 5.828E+00 | 3.222E+00 | 2.987E+00 | 3.295E+00 | 3.126E+00 | 1.528E+00 | 2.762E+00 | 3.341E+00 | 1.810E+00 | 2.100E+00 | 2.409E+00 |
| 265 | 4.590E+00 | 2.174E+00 | 1.762E+00 | 2.444E+00 | 2.195E+00 | 1.125E+00 | 1.882E+00 | 2.386E+00 | 1.701E+00 | 1.458E+00 | 1.795E+00 |
| 266 | 3.014E+00 | 1.548E+00 | 7.356E−01 | 1.028E+00 | 9.522E−01 | 4.428E−01 | 6.932E−01 | 1.889E+00 | 1.629E+00 | 8.225E−01 | 9.466E−01 |
| 267 | 2.434E+00 | 1.563E+00 | 1.036E+00 | 1.067E+00 | 1.352E+00 | 4.872E−01 | 8.862E−01 | 3.225E+00 | 3.873E+00 | 1.212E+00 | 1.114E+00 |
| 268 | 2.149E+01 | 2.999E+01 | 2.576E+01 | 1.458E+01 | 1.671E+01 | 2.022E+01 | 2.510E+01 | 2.404E+01 | 9.556E+00 | 1.273E+01 | 1.027E+01 |
| 269 | 1.698E+01 | 1.424E+01 | 1.136E+01 | 5.848E+00 | 7.493E+00 | 1.114E+01 | 1.125E+01 | 1.014E+01 | 4.887E+00 | 6.445E+00 | 5.590E+00 |
| 270 | 7.515E+00 | 4.237E+00 | 2.805E+00 | 1.871E+00 | 2.423E+00 | 4.854E+00 | 3.270E+00 | 3.018E+00 | 1.738E+00 | 2.363E+00 | 2.103E+00 |
| 271 | 7.810E+00 | 1.347E+01 | 1.166E+01 | 1.434E+01 | 1.127E+01 | 7.293E+00 | 1.037E+01 | 1.213E+01 | 1.730E+01 | 1.083E+01 | 1.516E+01 |
| 272 | 5.786E+01 | 7.680E+01 | 8.703E+01 | 1.001E+02 | 7.512E+01 | 3.602E+01 | 5.909E+01 | 9.778E+01 | 1.233E+02 | 7.727E+01 | 9.989E+01 |
| 273 | 6.648E+01 | 8.901E+01 | 1.007E+02 | 1.172E+02 | 8.670E+01 | 4.126E+01 | 6.860E+01 | 8.377E+01 | 1.113E+02 | 6.802E+01 | 1.057E+02 |
| 274 | 1.058E+01 | 1.267E+01 | 1.452E+01 | 1.762E+01 | 1.330E+01 | 5.801E+00 | 1.027E+01 | 1.240E+01 | 1.433E+01 | 1.040E+01 | 1.417E+01 |
| 275 | 5.424E−01 | 8.705E−01 | 3.933E−01 | 5.118E−01 | 6.739E−01 | 3.963E−01 | 5.262E−01 | 3.291E−01 | 3.982E−01 | 6.199E−01 | 6.940E−01 |
| 276 | 7.023E+00 | 7.871E+00 | 6.347E+00 | 9.518E+00 | 8.063E+00 | 5.466E+00 | 9.384E+00 | 6.156E+00 | 1.017E+01 | 7.676E+00 | 1.132E+01 |
| 277 | 1.828E+01 | 1.762E+01 | 1.991E+01 | 2.376E+01 | 2.015E+01 | 1.187E+01 | 2.076E+01 | 1.682E+01 | 2.281E+01 | 1.890E+01 | 2.280E+01 |
| 278 | 1.841E+01 | 1.786E+01 | 2.030E+01 | 2.471E+01 | 2.036E+01 | 1.164E+01 | 2.115E+01 | 1.396E+01 | 2.060E+01 | 1.885E+01 | 2.126E+01 |
| 279 | 6.779E+00 | 5.598E+00 | 6.992E+00 | 5.450E+00 | 5.487E+00 | 8.558E+00 | 6.757E+00 | 7.012E+00 | 4.090E+00 | 4.952E+00 | 4.340E+00 |
| 280 | 4.827E+00 | 5.435E+00 | 3.396E+00 | 4.476E+00 | 5.263E+00 | 4.024E+00 | 4.512E+00 | 4.716E+00 | 4.054E+00 | 4.118E+00 | 5.313E+00 |
| 281 | 1.124E+02 | 1.075E+02 | 1.118E+02 | 9.743E+01 | 1.338E+02 | 1.419E+02 | 1.221E+02 | 1.352E+02 | 1.306E+02 | 1.232E+02 | 1.083E+02 |
| 282 | 9.435E+01 | 9.300E+01 | 9.577E+01 | 8.699E+01 | 1.164E+02 | 1.235E+02 | 1.047E+02 | 1.087E+02 | 1.058E+02 | 1.129E+02 | 1.107E+02 |
| 283 | 5.077E+01 | 4.349E+01 | 4.130E+01 | 3.908E+01 | 3.911E+01 | 6.009E+01 | 4.104E+01 | 5.443E+01 | 3.964E+01 | 3.666E+01 | 3.565E+01 |
| 284 | 4.333E+00 | 5.898E+00 | 4.813E+00 | 4.931E+00 | 6.648E+00 | 3.280E+00 | 4.764E+00 | 5.102E+00 | 5.140E+00 | 4.230E+00 | 5.581E+00 |
| 285 | 5.885E+01 | 7.788E+01 | 7.084E+01 | 6.604E+01 | 8.167E+01 | 7.713E+01 | 7.394E+01 | 7.675E+01 | 6.947E+01 | 7.569E+01 | 7.249E+01 |
| 286 | 4.342E+01 | 6.253E+01 | 5.686E+01 | 5.387E+01 | 6.352E+01 | 5.652E+01 | 5.549E+01 | 5.121E+01 | 4.898E+01 | 4.492E+01 | 6.256E+01 |
| 287 | 7.961E+00 | 9.703E+00 | 7.031E+00 | 6.314E+00 | 7.236E+00 | 8.656E+00 | 7.358E+00 | 7.400E+00 | 6.552E+00 | 7.046E+00 | 6.911E+00 |
| 288 | 5.473E+01 | 6.364E+01 | 5.757E+01 | 7.879E+01 | 5.612E+01 | 3.710E+01 | 4.996E+01 | 5.516E+01 | 5.003E+01 | 4.568E+01 | 5.847E+01 |
| 289 | 4.122E+01 | 5.194E+01 | 4.749E+01 | 6.535E+01 | 4.677E+01 | 2.608E+01 | 3.878E+01 | 3.975E+01 | 3.685E+01 | 3.861E+01 | 4.031E+01 |
| 290 | 1.771E+01 | 2.463E+01 | 2.158E+01 | 2.629E+01 | 1.839E+01 | 1.236E+01 | 1.782E+01 | 1.620E+01 | 1.484E+01 | 1.338E+01 | 1.780E+01 |
| 291 | 1.398E+01 | 1.954E+01 | 1.777E+01 | 2.168E+01 | 1.499E+01 | 9.848E+00 | 1.446E+01 | 1.501E+01 | 1.879E+01 | 1.710E+01 | 2.022E+01 |
| 292 | 2.667E+00 | 2.505E+00 | 2.076E+00 | 2.124E+00 | 2.003E+00 | 2.019E+00 | 2.016E+00 | 1.720E+00 | 1.810E+00 | 1.649E+00 | 2.174E+00 |
| 293 | 2.570E+00 | 1.147E+00 | 6.846E−01 | 6.861E−01 | 8.254E−01 | 7.730E−01 | 8.052E−01 | 8.139E−01 | 1.014E+00 | 5.323E−01 | 8.518E−01 |
| 294 | 5.291E+00 | 2.603E+00 | 2.515E+00 | 2.019E+00 | 3.374E+00 | 4.033E+00 | 3.261E+00 | 2.518E+00 | 3.041E+00 | 2.821E+00 | 2.974E+00 |
| 295 | 5.338E+00 | 2.549E+00 | 2.521E+00 | 1.923E+00 | 3.440E+00 | 3.932E+00 | 3.238E+00 | 2.624E+00 | 2.679E+00 | 2.289E+00 | 2.959E+00 |
| 296 | 4.041E+00 | 2.018E+00 | 1.983E+00 | 1.579E+00 | 2.258E+00 | 3.102E+00 | 2.312E+00 | 1.954E+00 | 2.063E+00 | 1.776E+00 | 1.521E+00 |
| 297 | 1.420E−01 | 3.942E−01 | 4.516E−01 | 3.725E−01 | 1.317E−01 | 6.779E−02 | 1.128E−01 | 3.835E−01 | 1.014E+00 | 3.228E−01 | 5.742E−01 |
| 298 | 3.604E−03 | 1.013E−02 | 1.116E−02 | 1.300E−02 | 2.917E−03 | 1.843E−03 | 4.891E−03 | 1.615E−02 | 3.625E−02 | 1.373E−02 | 1.598E−02 |

APPENDIX D-continued

Ovarian Cancer
Training Dataset

| | | | | | | | | | | | |
|---|---|---|---|---|---|---|---|---|---|---|---|
| 299 | 4.655E−02 | 7.873E−02 | 9.889E−02 | 8.323E−02 | 3.239E−02 | 3.046E−02 | 3.990E−02 | 7.487E−02 | 1.448E−01 | 1.253E−01 | 1.607E−01 |
| 300 | 2.574E−03 | 4.012E−03 | 5.492E−03 | 4.097E−03 | 1.298E−03 | 2.295E−03 | 2.789E−03 | 1.176E−02 | 3.625E−02 | 5.149E−03 | 6.993E−03 |
| 301 | 2.488E−02 | 4.934E−02 | 5.256E−02 | 5.792E−02 | 2.188E−02 | 2.167E−02 | 2.446E−02 | 7.787E−02 | 2.167E−01 | 6.521E−02 | 1.008E−01 |
| 302 | 1.798E−03 | 4.183E−03 | 1.064E−03 | 4.569E−03 | 1.622E−03 | 7.680E−04 | 1.049E−03 | 0.000E+00 | 0.000E+00 | 1.716E−03 | 6.993E−03 |
| 303 | 7.894E−02 | 1.714E−01 | 1.993E−01 | 1.909E−01 | 7.573E−02 | 8.495E−02 | 8.045E−02 | 1.793E−01 | 7.602E−01 | 2.456E−01 | 2.377E−01 |
| 304 | 2.574E−04 | 6.993E−04 | 1.064E−03 | 1.139E−03 | 3.239E−04 | 4.612E−04 | 3.497E−04 | 0.000E+00 | 0.000E+00 | 0.000E+00 | 9.975E−04 |
| 305 | 1.300E−01 | 2.521E−01 | 2.872E−01 | 3.832E−01 | 1.276E−01 | 7.530E−02 | 8.817E−02 | 4.202E−01 | 6.878E−01 | 3.829E−01 | 4.284E−01 |
| 306 | 1.105E−02 | 1.066E−02 | 1.665E−02 | 1.847E−02 | 1.070E−02 | 7.830E−03 | 8.388E−03 | 2.360E−02 | 1.085E−01 | 2.574E−02 | 1.798E−02 |
| 307 | 3.870E−01 | 8.595E−01 | 9.292E−01 | 1.182E+00 | 4.685E−01 | 5.690E−01 | 5.333E−01 | 1.462E+00 | 3.185E+00 | 1.698E+00 | 1.235E+00 |
| 308 | 1.131E−02 | 1.118E−02 | 1.469E−02 | 1.847E−02 | 9.568E−03 | 1.197E−02 | 1.049E−02 | 2.939E−02 | 1.085E−01 | 2.403E−02 | 1.798E−02 |
| 309 | 2.832E−03 | 2.274E−03 | 4.248E−03 | 3.647E−03 | 1.948E−03 | 1.227E−03 | 1.399E−03 | 5.878E−03 | 0.000E+00 | 3.432E−03 | 0.000E+00 |
| 310 | 1.798E−03 | 5.234E−04 | 1.594E−03 | 1.139E−03 | 9.739E−04 | 0.000E+00 | 1.748E−03 | 4.398E−03 | 3.625E−02 | 8.581E−03 | 9.975E−03 |
| 311 | 0.000E+00 | 5.234E−04 | 7.079E−04 | 6.843E−04 | 3.239E−04 | 4.612E−04 | 3.497E−04 | 0.000E+00 | 0.000E+00 | 0.000E+00 | 9.975E−04 |
| 312 | 0.000E+00 | 0.000E+00 | 0.000E+00 | 0.000E+00 | 0.000E+00 | 0.000E+00 | 0.000E+00 | 0.000E+00 | 1.085E−01 | 0.000E+00 | 0.000E+00 |
| 313 | 5.771E−02 | 8.688E−02 | 1.133E−01 | 1.673E−01 | 5.728E−02 | 2.510E−02 | 5.041E−02 | 3.820E−01 | 9.412E−01 | 1.493E−01 | 1.757E−01 |
| 314 | 3.604E−03 | 4.548E−03 | 5.320E−03 | 5.020E−03 | 3.411E−03 | 1.382E−03 | 1.225E−03 | 1.469E−02 | 7.229E−02 | 3.432E−03 | 3.003E−03 |
| 315 | 8.216E−03 | 9.096E−03 | 1.718E−02 | 3.518E−02 | 1.444E−02 | 3.540E−03 | 7.873E−03 | 5.427E−02 | 3.625E−02 | 2.403E−02 | 3.690E−02 |
| 316 | 2.574E−04 | 6.993E−04 | 8.860E−04 | 9.117E−04 | 3.239E−04 | 4.612E−04 | 0.000E+00 | 2.939E−03 | 0.000E+00 | 3.432E−03 | 3.003E−03 |
| 317 | 1.002E−02 | 1.678E−02 | 1.701E−02 | 2.553E−02 | 1.542E−02 | 4.762E−03 | 1.137E−02 | 7.337E−02 | 7.229E−02 | 3.432E−02 | 3.797E−02 |
| 318 | 1.540E−03 | 1.049E−03 | 7.079E−04 | 1.596E−03 | 8.109E−04 | 1.534E−04 | 1.748E−04 | 8.817E−03 | 0.000E+00 | 6.865E−03 | 9.975E−04 |
| 319 | 1.085E−01 | 1.173E−01 | 1.530E−01 | 2.268E−01 | 1.137E−01 | 5.449E−02 | 9.353E−02 | 4.980E−01 | 7.602E−01 | 3.074E−01 | 2.536E−01 |
| 320 | 0.000E+00 | 5.234E−04 | 3.540E−04 | 4.569E−04 | 4.870E−04 | 0.000E+00 | 3.497E−04 | 2.939E−03 | 0.000E+00 | 0.000E+00 | 0.000E+00 |
| 321 | 9.889E−02 | 1.002E−01 | 1.349E−01 | 2.708E−01 | 9.954E−02 | 2.789E−02 | 5.685E−02 | 5.833E−01 | 7.602E−01 | 1.787E−01 | 2.087E−01 |
| 322 | 3.861E−03 | 4.012E−03 | 5.320E−03 | 7.980E−03 | 5.835E−03 | 1.534E−03 | 3.325E−03 | 1.763E−02 | 3.625E−02 | 1.373E−02 | 4.998E−03 |
| 323 | 1.367E−01 | 1.360E−01 | 1.834E−01 | 2.863E−01 | 1.407E−01 | 5.728E−02 | 1.118E−01 | 7.889E−01 | 1.122E+00 | 3.194E−01 | 2.726E−01 |
| 324 | 3.861E−03 | 3.668E−03 | 5.856E−03 | 7.980E−03 | 4.548E−03 | 1.534E−03 | 3.153E−03 | 1.615E−02 | 3.625E−02 | 5.149E−03 | 7.980E−03 |
| 325 | 6.672E−03 | 6.993E−03 | 8.152E−03 | 1.163E−02 | 6.007E−03 | 3.840E−03 | 5.771E−03 | 1.028E−02 | 3.625E−02 | 1.716E−02 | 1.199E−02 |
| 326 | 1.540E−03 | 5.234E−04 | 7.079E−04 | 9.117E−04 | 1.622E−04 | 1.075E−03 | 8.752E−04 | 2.939E−03 | 0.000E+00 | 0.000E+00 | 9.975E−04 |
| 327 | 5.384E−03 | 1.013E−02 | 1.135E−02 | 1.504E−02 | 3.411E−03 | 1.843E−03 | 5.063E−03 | 8.817E−03 | 0.000E+00 | 6.865E−03 | 5.985E−03 |
| 328 | 2.574E−04 | 8.731E−04 | 8.860E−04 | 2.051E−03 | 1.622E−04 | 4.612E−04 | 5.256E−04 | 1.469E−03 | 0.000E+00 | 0.000E+00 | 0.000E+00 |
| 329 | 2.019E−01 | 2.329E−01 | 2.204E−01 | 4.869E−01 | 1.630E−01 | 8.581E−02 | 1.369E−01 | 9.359E−01 | 1.376E+00 | 5.735E−01 | 6.151E−01 |
| 330 | 2.832E−03 | 2.096E−03 | 2.660E−03 | 5.234E−03 | 2.767E−03 | 1.075E−03 | 1.924E−03 | 1.176E−02 | 0.000E+00 | 1.201E−02 | 4.998E−03 |
| 331 | 8.216E−03 | 1.660E−02 | 2.019E−02 | 3.368E−02 | 1.249E−02 | 8.602E−03 | 1.225E−02 | 5.878E−02 | 1.811E−01 | 2.917E−02 | 2.098E−02 |
| 332 | 0.000E+00 | 6.993E−04 | 5.320E−04 | 2.274E−04 | 1.298E−03 | 9.203E−04 | 6.993E−04 | 0.000E+00 | 0.000E+00 | 1.716E−03 | 0.000E+00 |
| 333 | 7.701E−03 | 1.100E−02 | 1.630E−02 | 2.660E−02 | 8.281E−03 | 8.452E−03 | 8.388E−03 | 4.548E−02 | 3.625E−02 | 1.030E−02 | 1.298E−02 |
| 334 | 2.574E−04 | 1.746E−04 | 3.540E−04 | 0.000E+00 | 4.870E−04 | 3.068E−04 | 8.752E−04 | 1.469E−03 | 0.000E+00 | 1.716E−03 | 0.000E+00 |
| 335 | 1.412E−02 | 3.089E−02 | 3.668E−02 | 6.050E−02 | 1.461E−02 | 9.825E−03 | 2.167E−02 | 1.088E−01 | 1.448E−01 | 5.835E−02 | 4.998E−02 |
| 336 | 1.285E−03 | 1.746E−03 | 1.240E−03 | 1.369E−03 | 2.424E−03 | 2.617E−03 | 1.399E−03 | 8.817E−03 | 0.000E+00 | 0.000E+00 | 1.997E−03 |
| 337 | 4.784E−02 | 4.805E−02 | 6.243E−02 | 1.141E−01 | 3.239E−02 | 1.028E−02 | 2.510E−02 | 1.954E−01 | 1.811E−01 | 9.096E−02 | 9.096E−02 |
| 338 | 1.285E−03 | 8.731E−04 | 1.418E−03 | 1.369E−03 | 6.500E−04 | 3.068E−04 | 1.748E−04 | 1.469E−03 | 0.000E+00 | 0.000E+00 | 1.997E−03 |
| 339 | 2.132E−02 | 2.789E−02 | 3.111E−02 | 6.908E−02 | 1.866E−02 | 9.675E−03 | 1.592E−02 | 8.967E−02 | 2.167E−01 | 3.261E−02 | 4.483E−02 |
| 340 | 1.028E−03 | 1.572E−03 | 1.594E−03 | 2.274E−03 | 1.298E−03 | 9.203E−04 | 1.575E−03 | 1.469E−03 | 0.000E+00 | 6.865E−03 | 3.003E−03 |
| 341 | 3.347E−03 | 3.153E−03 | 3.540E−03 | 6.157E−03 | 1.298E−03 | 1.534E−03 | 1.225E−03 | 5.878E−03 | 0.000E+00 | 3.432E−03 | 0.000E+00 |
| 342 | 5.127E−04 | 1.223E−03 | 0.000E+00 | 2.274E−04 | 9.739E−04 | 7.680E−04 | 8.752E−04 | 0.000E+00 | 0.000E+00 | 0.000E+00 | 1.997E−03 |
| 343 | 3.347E−03 | 2.960E−03 | 5.149E−03 | 4.569E−03 | 2.109E−03 | 1.688E−03 | 2.274E−03 | 7.337E−03 | 0.000E+00 | 3.432E−03 | 3.990E−03 |
| 344 | 5.127E−04 | 0.000E+00 | 0.000E+00 | 2.274E−04 | 3.239E−04 | 0.000E+00 | 0.000E+00 | 0.000E+00 | 0.000E+00 | 0.000E+00 | 0.000E+00 |

APPENDIX E1

Cumulative Performance of Model versus Number of Principal Components Selected (Normal vs Diseased; 340 Lipids)

| No. | Sensitivity | Specificity | PPV | NPV | Accuracy | TN | FN | FP | TP |
|---|---|---|---|---|---|---|---|---|---|
| 1 | 100 | 0 | 71.73913 | NaN | 71.73913 | 0 | 39 | 0 | 99 |
| 2 | 100 | 0 | 71.73913 | NaN | 71.73913 | 0 | 39 | 0 | 99 |
| 3 | 100 | 2.564103 | 72.262774 | 100 | 72.463768 | 1 | 38 | 0 | 99 |
| 4 | 100 | 12.820513 | 74.43609 | 100 | 75.362319 | 5 | 34 | 0 | 99 |
| 5 | 96.969697 | 43.589744 | 81.355932 | 85 | 81.884058 | 17 | 22 | 3 | 96 |
| 6 | 96.969697 | 53.846154 | 84.210526 | 87.5 | 84.782609 | 21 | 18 | 3 | 96 |
| 7 | 95.959596 | 56.410256 | 84.821429 | 84.615385 | 84.782609 | 22 | 17 | 4 | 95 |
| 8 | 96.969697 | 53.846154 | 84.210526 | 87.5 | 84.782609 | 21 | 18 | 3 | 96 |
| 9 | 96.969697 | 51.282051 | 83.478261 | 86.956522 | 84.057971 | 20 | 19 | 3 | 96 |
| 10 | 97.979798 | 51.282051 | 83.62069 | 90.909091 | 84.782609 | 20 | 19 | 2 | 97 |
| 11 | 94.949495 | 61.538462 | 86.238532 | 82.758621 | 85.507246 | 24 | 15 | 5 | 94 |
| 12 | 95.959596 | 61.538462 | 86.363636 | 85.714286 | 86.231884 | 24 | 15 | 4 | 95 |
| 13 | 97.979798 | 58.974359 | 85.840708 | 92 | 86.956522 | 23 | 16 | 2 | 97 |
| 14 | 94.949495 | 58.974359 | 85.454545 | 82.142857 | 84.782609 | 23 | 16 | 5 | 94 |
| 15 | 94.949495 | 58.974359 | 85.454545 | 82.142857 | 84.782609 | 23 | 16 | 5 | 94 |
| 16 | 98.989899 | 61.538462 | 86.725664 | 96 | 88.405797 | 24 | 15 | 1 | 98 |
| 17 | 96.969697 | 66.666667 | 88.073394 | 89.655172 | 88.405797 | 26 | 13 | 3 | 96 |
| 18 | 97.979798 | 66.666667 | 88.181818 | 92.857143 | 89.130435 | 26 | 13 | 2 | 97 |
| 19 | 97.979798 | 66.666667 | 88.181818 | 92.857143 | 89.130435 | 26 | 13 | 2 | 97 |
| 20 | 96.969697 | 71.794872 | 89.719626 | 90.322581 | 89.855072 | 28 | 11 | 3 | 96 |
| 21 | 96.969697 | 71.794872 | 89.719626 | 90.322581 | 89.855072 | 28 | 11 | 3 | 96 |
| 22 | 96.969697 | 76.923077 | 91.428571 | 90.909091 | 91.304348 | 30 | 9 | 3 | 96 |
| 23 | 96.969697 | 76.923077 | 91.428571 | 90.909091 | 91.304348 | 30 | 9 | 3 | 96 |
| 24 | 98.989899 | 79.487179 | 92.45283 | 96.875 | 93.478261 | 31 | 8 | 1 | 98 |
| 25 | 98.989899 | 79.487179 | 92.45283 | 96.875 | 93.478261 | 31 | 8 | 1 | 98 |
| 26 | 98.989899 | 79.487179 | 92.45283 | 96.875 | 93.478261 | 31 | 8 | 1 | 98 |
| 27 | 98.989899 | 79.487179 | 92.45283 | 96.875 | 93.478261 | 31 | 8 | 1 | 98 |
| 28 | 98.989899 | 79.487179 | 92.45283 | 96.875 | 93.478261 | 31 | 8 | 1 | 98 |
| 29 | 98.989899 | 79.487179 | 92.45283 | 96.875 | 93.478261 | 31 | 8 | 1 | 98 |
| 30 | 98.989899 | 79.487179 | 92.45283 | 96.875 | 93.478261 | 31 | 8 | 1 | 98 |
| 31 | 98.989899 | 79.487179 | 92.45283 | 96.875 | 93.478261 | 31 | 8 | 1 | 98 |
| 32 | 98.989899 | 76.923077 | 91.588785 | 96.774194 | 92.753623 | 30 | 9 | 1 | 98 |
| 33 | 98.989899 | 74.358974 | 90.740741 | 96.666667 | 92.028986 | 29 | 10 | 1 | 98 |
| 34 | 98.989899 | 79.487179 | 92.45283 | 96.875 | 93.478261 | 31 | 8 | 1 | 98 |
| 35 | 98.989899 | 79.487179 | 92.45283 | 96.875 | 93.478261 | 31 | 8 | 1 | 98 |
| 36 | 98.989899 | 79.487179 | 92.45283 | 96.875 | 93.478261 | 31 | 8 | 1 | 98 |
| 37 | 98.989899 | 82.051282 | 93.333333 | 96.969697 | 94.202899 | 32 | 7 | 1 | 98 |
| 38 | 98.989899 | 79.487179 | 92.45283 | 96.875 | 93.478261 | 31 | 8 | 1 | 98 |
| 39 | 98.989899 | 82.051282 | 93.333333 | 96.969697 | 94.202899 | 32 | 7 | 1 | 98 |
| 40 | 98.989899 | 79.487179 | 92.45283 | 96.875 | 93.478261 | 31 | 8 | 1 | 98 |
| 41 | 98.989899 | 82.051282 | 93.333333 | 96.969697 | 94.202899 | 32 | 7 | 1 | 98 |
| 42 | 98.989899 | 82.051282 | 93.333333 | 96.969697 | 94.202899 | 32 | 7 | 1 | 98 |
| 43 | 98.989899 | 87.179487 | 95.145631 | 97.142857 | 95.652174 | 34 | 5 | 1 | 98 |
| 44 | 98.989899 | 87.179487 | 95.145631 | 97.142857 | 95.652174 | 34 | 5 | 1 | 98 |
| 45 | 98.989899 | 89.74359 | 96.078431 | 97.222222 | 96.376812 | 35 | 4 | 1 | 98 |
| 46 | 98.989899 | 89.74359 | 96.078431 | 97.222222 | 96.376812 | 35 | 4 | 1 | 98 |
| 47 | 98.989899 | 89.74359 | 96.078431 | 97.222222 | 96.376812 | 35 | 4 | 1 | 98 |
| 48 | 98.989899 | 84.615385 | 94.230769 | 97.058824 | 94.927536 | 33 | 6 | 1 | 98 |
| 49 | 98.989899 | 84.615385 | 94.230769 | 97.058824 | 94.927536 | 33 | 6 | 1 | 98 |
| 50 | 98.989899 | 89.74359 | 96.078431 | 97.222222 | 96.376812 | 35 | 4 | 1 | 98 |
| 51 | 98.989899 | 89.74359 | 96.078431 | 97.222222 | 96.376812 | 35 | 4 | 1 | 98 |
| 52 | 98.989899 | 89.74359 | 96.078431 | 97.222222 | 96.376812 | 35 | 4 | 1 | 98 |
| 53 | 98.989899 | 89.74359 | 96.078431 | 97.222222 | 96.376812 | 35 | 4 | 1 | 98 |
| 54 | 98.989899 | 89.74359 | 96.078431 | 97.222222 | 96.376812 | 35 | 4 | 1 | 98 |
| 55 | 98.989899 | 89.74359 | 96.078431 | 97.222222 | 96.376812 | 35 | 4 | 1 | 98 |
| 56 | 98.989899 | 89.74359 | 96.078431 | 97.222222 | 96.376812 | 35 | 4 | 1 | 98 |
| 57 | 98.989899 | 89.74359 | 96.078431 | 97.222222 | 96.376812 | 35 | 4 | 1 | 98 |
| 58 | 98.989899 | 89.74359 | 96.078431 | 97.222222 | 96.376812 | 35 | 4 | 1 | 98 |
| 59 | 98.989899 | 89.74359 | 96.078431 | 97.222222 | 96.376812 | 35 | 4 | 1 | 98 |
| 60 | 98.989899 | 89.74359 | 96.078431 | 97.222222 | 96.376812 | 35 | 4 | 1 | 98 |
| 61 | 98.989899 | 89.74359 | 96.078431 | 97.222222 | 96.376812 | 35 | 4 | 1 | 98 |
| 62 | 98.989899 | 89.74359 | 96.078431 | 97.222222 | 96.376812 | 35 | 4 | 1 | 98 |
| 63 | 98.989899 | 89.74359 | 96.078431 | 97.222222 | 96.376812 | 35 | 4 | 1 | 98 |
| 64 | 98.989899 | 89.74359 | 96.078431 | 97.222222 | 96.376812 | 35 | 4 | 1 | 98 |
| 65 | 98.989899 | 89.74359 | 96.078431 | 97.222222 | 96.376812 | 35 | 4 | 1 | 98 |
| 66 | 98.989899 | 89.74359 | 96.078431 | 97.222222 | 96.376812 | 35 | 4 | 1 | 98 |
| 67 | 98.989899 | 89.74359 | 96.078431 | 97.222222 | 96.376812 | 35 | 4 | 1 | 98 |
| 68 | 98.989899 | 89.74359 | 96.078431 | 97.222222 | 96.376812 | 35 | 4 | 1 | 98 |
| 69 | 98.989899 | 89.74359 | 96.078431 | 97.222222 | 96.376812 | 35 | 4 | 1 | 98 |
| 70 | 98.989899 | 89.74359 | 96.078431 | 97.222222 | 96.376812 | 35 | 4 | 1 | 98 |
| 71 | 98.989899 | 89.74359 | 96.078431 | 97.222222 | 96.376812 | 35 | 4 | 1 | 98 |
| 72 | 98.989899 | 89.74359 | 96.078431 | 97.222222 | 96.376812 | 35 | 4 | 1 | 98 |

APPENDIX E1-continued

Cumulative Performance of Model versus Number of Principal Components Selected (Normal vs Diseased; 340 Lipids)

| No. | Sensitivity | Specificity | PPV | NPV | Accuracy | TN | FN | FP | TP |
|---|---|---|---|---|---|---|---|---|---|
| 73 | 98.989899 | 89.74359 | 96.078431 | 97.222222 | 96.376812 | 35 | 4 | 1 | 98 |
| 74 | 98.989899 | 89.74359 | 96.078431 | 97.222222 | 96.376812 | 35 | 4 | 1 | 98 |
| 75 | 98.989899 | 92.307692 | 97.029703 | 97.297297 | 97.101449 | 36 | 3 | 1 | 98 |
| 76 | 98.989899 | 92.307692 | 97.029703 | 97.297297 | 97.101449 | 36 | 3 | 1 | 98 |
| 77 | 98.989899 | 89.74359 | 96.078431 | 97.222222 | 96.376812 | 35 | 4 | 1 | 98 |
| 78 | 98.989899 | 89.74359 | 96.078431 | 97.222222 | 96.376812 | 35 | 4 | 1 | 98 |
| 79 | 98.989899 | 89.74359 | 96.078431 | 97.222222 | 96.376812 | 35 | 4 | 1 | 98 |
| 80 | 98.989899 | 89.74359 | 96.078431 | 97.222222 | 96.376812 | 35 | 4 | 1 | 98 |
| 81 | 98.989899 | 89.74359 | 96.078431 | 97.222222 | 96.376812 | 35 | 4 | 1 | 98 |
| 82 | 98.989899 | 89.74359 | 96.078431 | 97.222222 | 96.376812 | 35 | 4 | 1 | 98 |
| 83 | 98.989899 | 89.74359 | 96.078431 | 97.222222 | 96.376812 | 35 | 4 | 1 | 98 |
| 84 | 98.989899 | 89.74359 | 96.078431 | 97.222222 | 96.376812 | 35 | 4 | 1 | 98 |
| 85 | 98.989899 | 92.307692 | 97.029703 | 97.297297 | 97.101449 | 36 | 3 | 1 | 98 |
| 86 | 98.989899 | 92.307692 | 97.029703 | 97.297297 | 97.101449 | 36 | 3 | 1 | 98 |
| 87 | 98.989899 | 92.307692 | 97.029703 | 97.297297 | 97.101449 | 36 | 3 | 1 | 98 |
| 88 | 98.989899 | 92.307692 | 97.029703 | 97.297297 | 97.101449 | 36 | 3 | 1 | 98 |
| 89 | 98.989899 | 92.307692 | 97.029703 | 97.297297 | 97.101449 | 36 | 3 | 1 | 98 |
| 90 | 98.989899 | 92.307692 | 97.029703 | 97.297297 | 97.101449 | 36 | 3 | 1 | 98 |
| 91 | 98.989899 | 92.307692 | 97.029703 | 97.297297 | 97.101449 | 36 | 3 | 1 | 98 |
| 92 | 98.989899 | 92.307692 | 97.029703 | 97.297297 | 97.101449 | 36 | 3 | 1 | 98 |
| 93 | 98.989899 | 92.307692 | 97.029703 | 97.297297 | 97.101449 | 36 | 3 | 1 | 98 |
| 94 | 98.989899 | 92.307692 | 97.029703 | 97.297297 | 97.101449 | 36 | 3 | 1 | 98 |
| 95 | 98.989899 | 92.307692 | 97.029703 | 97.297297 | 97.101449 | 36 | 3 | 1 | 98 |
| 96 | 98.989899 | 92.307692 | 97.029703 | 97.297297 | 97.101449 | 36 | 3 | 1 | 98 |
| 97 | 98.989899 | 92.307692 | 97.029703 | 97.297297 | 97.101449 | 36 | 3 | 1 | 98 |
| 98 | 98.989899 | 92.307692 | 97.029703 | 97.297297 | 97.101449 | 36 | 3 | 1 | 98 |
| 99 | 98.989899 | 92.307692 | 97.029703 | 97.297297 | 97.101449 | 36 | 3 | 1 | 98 |
| 100 | 98.989899 | 92.307692 | 97.029703 | 97.297297 | 97.101449 | 36 | 3 | 1 | 98 |

APPENDIX E2

Cumulative Performance of Model versus Number of Principal Components Selected (Benign vs Malignant; 340 Lipids)

| No | Sensitivity | Specificity | PPV | NPV | Accuracy | TN | FN | FP | TP |
|---|---|---|---|---|---|---|---|---|---|
| 1 | 79.661017 | 65 | 77.04918 | 68.421053 | 73.737374 | 26 | 14 | 12 | 47 |
| 2 | 84.745763 | 67.5 | 79.365079 | 75 | 77.777778 | 27 | 13 | 9 | 50 |
| 3 | 84.745763 | 67.5 | 79.365079 | 75 | 77.777778 | 27 | 13 | 9 | 50 |
| 4 | 88.135593 | 70 | 81.25 | 80 | 80.808081 | 28 | 12 | 7 | 52 |
| 5 | 88.135593 | 70 | 81.25 | 80 | 80.808081 | 28 | 12 | 7 | 52 |
| 6 | 86.440678 | 67.5 | 79.6875 | 77.142857 | 78.787879 | 27 | 13 | 8 | 51 |
| 7 | 88.135593 | 67.5 | 80 | 79.411765 | 79.79798 | 27 | 13 | 7 | 52 |
| 8 | 88.135593 | 67.5 | 80 | 79.411765 | 79.79798 | 27 | 13 | 7 | 52 |
| 9 | 88.135593 | 70 | 81.25 | 80 | 80.808081 | 28 | 12 | 7 | 52 |
| 10 | 89.830508 | 72.5 | 82.8125 | 82.857143 | 82.828283 | 29 | 11 | 6 | 53 |
| 11 | 91.525424 | 72.5 | 83.076923 | 85.294118 | 83.838384 | 29 | 11 | 5 | 54 |
| 12 | 94.915254 | 72.5 | 83.58209 | 90.625 | 85.858586 | 29 | 11 | 3 | 56 |
| 13 | 96.610169 | 75 | 85.074627 | 93.75 | 87.878788 | 30 | 10 | 2 | 57 |
| 14 | 96.610169 | 72.5 | 83.823529 | 93.548387 | 86.868687 | 29 | 11 | 2 | 57 |
| 15 | 94.915254 | 75 | 84.848485 | 90.909091 | 86.868687 | 30 | 10 | 3 | 56 |
| 16 | 94.915254 | 75 | 84.848485 | 90.909091 | 86.868687 | 30 | 10 | 3 | 56 |
| 17 | 94.915254 | 75 | 84.848485 | 90.909091 | 86.868687 | 30 | 10 | 3 | 56 |
| 18 | 94.915254 | 77.5 | 86.153846 | 91.176471 | 87.878788 | 31 | 9 | 3 | 56 |
| 19 | 94.915254 | 77.5 | 86.153846 | 91.176471 | 87.878788 | 31 | 9 | 3 | 56 |
| 20 | 94.915254 | 77.5 | 86.153846 | 91.176471 | 87.878788 | 31 | 9 | 3 | 56 |
| 21 | 94.915254 | 77.5 | 86.153846 | 91.176471 | 87.878788 | 31 | 9 | 3 | 56 |
| 22 | 94.915254 | 77.5 | 86.153846 | 91.176471 | 87.878788 | 31 | 9 | 3 | 56 |
| 23 | 94.915254 | 75 | 84.848485 | 90.909091 | 86.868687 | 30 | 10 | 3 | 56 |
| 24 | 94.915254 | 75 | 84.848485 | 90.909091 | 86.868687 | 30 | 10 | 3 | 56 |
| 25 | 94.915254 | 75 | 84.848485 | 90.909091 | 86.868687 | 30 | 10 | 3 | 56 |
| 26 | 94.915254 | 75 | 84.848485 | 90.909091 | 86.868687 | 30 | 10 | 3 | 56 |
| 27 | 94.915254 | 77.5 | 86.153846 | 91.176471 | 87.878788 | 31 | 9 | 3 | 56 |
| 28 | 94.915254 | 75 | 84.848485 | 90.909091 | 86.868687 | 30 | 10 | 3 | 56 |
| 29 | 94.915254 | 77.5 | 86.153846 | 91.176471 | 87.878788 | 31 | 9 | 3 | 56 |
| 30 | 94.915254 | 77.5 | 86.153846 | 91.176471 | 87.878788 | 31 | 9 | 3 | 56 |

APPENDIX E2-continued

Cumulative Performance of Model versus Number of Principal Components Selected (Benign vs Malignant; 340 Lipids)

| No | Sensitivity | Specificity | PPV | NPV | Accuracy | TN | FN | FP | TP |
|---|---|---|---|---|---|---|---|---|---|
| 31 | 94.915254 | 77.5 | 86.153846 | 91.176471 | 87.878788 | 31 | 9 | 3 | 56 |
| 32 | 94.915254 | 77.5 | 86.153846 | 91.176471 | 87.878788 | 31 | 9 | 3 | 56 |
| 33 | 94.915254 | 77.5 | 86.153846 | 91.176471 | 87.878788 | 31 | 9 | 3 | 56 |
| 34 | 94.915254 | 77.5 | 86.153846 | 91.176471 | 87.878788 | 31 | 9 | 3 | 56 |
| 35 | 94.915254 | 77.5 | 86.153846 | 91.176471 | 87.878788 | 31 | 9 | 3 | 56 |
| 36 | 94.915254 | 80 | 87.5 | 91.428571 | 88.888889 | 32 | 8 | 3 | 56 |
| 37 | 94.915254 | 77.5 | 86.153846 | 91.176471 | 87.878788 | 31 | 9 | 3 | 56 |
| 38 | 94.915254 | 77.5 | 86.153846 | 91.176471 | 87.878788 | 31 | 9 | 3 | 56 |
| 39 | 94.915254 | 80 | 87.5 | 91.428571 | 88.888889 | 32 | 8 | 3 | 56 |
| 40 | 94.915254 | 77.5 | 86.153846 | 91.176471 | 87.878788 | 31 | 9 | 3 | 56 |
| 41 | 94.915254 | 80 | 87.5 | 91.428571 | 88.888889 | 32 | 8 | 3 | 56 |
| 42 | 94.915254 | 80 | 87.5 | 91.428571 | 88.888889 | 32 | 8 | 3 | 56 |
| 43 | 94.915254 | 80 | 87.5 | 91.428571 | 88.888889 | 32 | 8 | 3 | 56 |
| 44 | 94.915254 | 80 | 87.5 | 91.428571 | 88.888889 | 32 | 8 | 3 | 56 |
| 45 | 94.915254 | 80 | 87.5 | 91.428571 | 88.888889 | 32 | 8 | 3 | 56 |
| 46 | 94.915254 | 80 | 87.5 | 91.428571 | 88.888889 | 32 | 8 | 3 | 56 |
| 47 | 94.915254 | 80 | 87.5 | 91.428571 | 88.888889 | 32 | 8 | 3 | 56 |
| 48 | 94.915254 | 80 | 87.5 | 91.428571 | 88.888889 | 32 | 8 | 3 | 56 |
| 49 | 94.915254 | 80 | 87.5 | 91.428571 | 88.888889 | 32 | 8 | 3 | 56 |
| 50 | 94.915254 | 80 | 87.5 | 91.428571 | 88.888889 | 32 | 8 | 3 | 56 |
| 51 | 94.915254 | 80 | 87.5 | 91.428571 | 88.888889 | 32 | 8 | 3 | 56 |
| 52 | 94.915254 | 80 | 87.5 | 91.428571 | 88.888889 | 32 | 8 | 3 | 56 |
| 53 | 94.915254 | 80 | 87.5 | 91.428571 | 88.888889 | 32 | 8 | 3 | 56 |
| 54 | 94.915254 | 80 | 87.5 | 91.428571 | 88.888889 | 32 | 8 | 3 | 56 |
| 55 | 94.915254 | 82.5 | 88.888889 | 91.666667 | 89.89899 | 33 | 7 | 3 | 56 |
| 56 | 94.915254 | 80 | 87.5 | 91.428571 | 88.888889 | 32 | 8 | 3 | 56 |
| 57 | 94.915254 | 82.5 | 88.888889 | 91.666667 | 89.89899 | 33 | 7 | 3 | 56 |
| 58 | 94.915254 | 82.5 | 88.888889 | 91.666667 | 89.89899 | 33 | 7 | 3 | 56 |
| 59 | 94.915254 | 82.5 | 88.888889 | 91.666667 | 89.89899 | 33 | 7 | 3 | 56 |
| 60 | 94.915254 | 82.5 | 88.888889 | 91.666667 | 89.89899 | 33 | 7 | 3 | 56 |
| 61 | 94.915254 | 82.5 | 88.888889 | 91.666667 | 89.89899 | 33 | 7 | 3 | 56 |
| 62 | 94.915254 | 82.5 | 88.888889 | 91.666667 | 89.89899 | 33 | 7 | 3 | 56 |
| 63 | 94.915254 | 82.5 | 88.888889 | 91.666667 | 89.89899 | 33 | 7 | 3 | 56 |
| 64 | 94.915254 | 82.5 | 88.888889 | 91.666667 | 89.89899 | 33 | 7 | 3 | 56 |
| 65 | 94.915254 | 82.5 | 88.888889 | 91.666667 | 89.89899 | 33 | 7 | 3 | 56 |
| 66 | 94.915254 | 82.5 | 88.888889 | 91.666667 | 89.89899 | 33 | 7 | 3 | 56 |
| 67 | 94.915254 | 82.5 | 88.888889 | 91.666667 | 89.89899 | 33 | 7 | 3 | 56 |
| 68 | 94.915254 | 82.5 | 88.888889 | 91.666667 | 89.89899 | 33 | 7 | 3 | 56 |
| 69 | 94.915254 | 82.5 | 88.888889 | 91.666667 | 89.89899 | 33 | 7 | 3 | 56 |
| 70 | 94.915254 | 82.5 | 88.888889 | 91.666667 | 89.89899 | 33 | 7 | 3 | 56 |
| 71 | 94.915254 | 82.5 | 88.888889 | 91.666667 | 89.89899 | 33 | 7 | 3 | 56 |
| 72 | 94.915254 | 82.5 | 88.888889 | 91.666667 | 89.89899 | 33 | 7 | 3 | 56 |
| 73 | 94.915254 | 82.5 | 88.888889 | 91.666667 | 89.89899 | 33 | 7 | 3 | 56 |
| 74 | 94.915254 | 82.5 | 88.888889 | 91.666667 | 89.89899 | 33 | 7 | 3 | 56 |
| 75 | 94.915254 | 82.5 | 88.888889 | 91.666667 | 89.89899 | 33 | 7 | 3 | 56 |
| 76 | 94.915254 | 82.5 | 88.888889 | 91.666667 | 89.89899 | 33 | 7 | 3 | 56 |
| 77 | 94.915254 | 82.5 | 88.888889 | 91.666667 | 89.89899 | 33 | 7 | 3 | 56 |
| 78 | 94.915254 | 82.5 | 88.888889 | 91.666667 | 89.89899 | 33 | 7 | 3 | 56 |
| 79 | 94.915254 | 82.5 | 88.888889 | 91.666667 | 89.89899 | 33 | 7 | 3 | 56 |
| 80 | 94.915254 | 82.5 | 88.888889 | 91.666667 | 89.89899 | 33 | 7 | 3 | 56 |
| 81 | 94.915254 | 82.5 | 88.888889 | 91.666667 | 89.89899 | 33 | 7 | 3 | 56 |
| 82 | 94.915254 | 80 | 87.5 | 91.428571 | 88.888889 | 32 | 8 | 3 | 56 |
| 83 | 94.915254 | 80 | 87.5 | 91.428571 | 88.888889 | 32 | 8 | 3 | 56 |
| 84 | 94.915254 | 80 | 87.5 | 91.428571 | 88.888889 | 32 | 8 | 3 | 56 |
| 85 | 94.915254 | 80 | 87.5 | 91.428571 | 88.888889 | 32 | 8 | 3 | 56 |
| 86 | 94.915254 | 80 | 87.5 | 91.428571 | 88.888889 | 32 | 8 | 3 | 56 |
| 87 | 94.915254 | 82.5 | 88.888889 | 91.666667 | 89.89899 | 33 | 7 | 3 | 56 |
| 88 | 94.915254 | 82.5 | 88.888889 | 91.666667 | 89.89899 | 33 | 7 | 3 | 56 |
| 89 | 94.915254 | 82.5 | 88.888889 | 91.666667 | 89.89899 | 33 | 7 | 3 | 56 |
| 90 | 94.915254 | 82.5 | 88.888889 | 91.666667 | 89.89899 | 33 | 7 | 3 | 56 |
| 91 | 94.915254 | 82.5 | 88.888889 | 91.666667 | 89.89899 | 33 | 7 | 3 | 56 |
| 92 | 94.915254 | 82.5 | 88.888889 | 91.666667 | 89.89899 | 33 | 7 | 3 | 56 |
| 93 | 94.915254 | 82.5 | 88.888889 | 91.666667 | 89.89899 | 33 | 7 | 3 | 56 |
| 94 | 94.915254 | 82.5 | 88.888889 | 91.666667 | 89.89899 | 33 | 7 | 3 | 56 |
| 95 | 94.915254 | 82.5 | 88.888889 | 91.666667 | 89.89899 | 33 | 7 | 3 | 56 |
| 96 | 94.915254 | 82.5 | 88.888889 | 91.666667 | 89.89899 | 33 | 7 | 3 | 56 |
| 97 | 94.915254 | 82.5 | 88.888889 | 91.666667 | 89.89899 | 33 | 7 | 3 | 56 |
| 98 | 94.915254 | 82.5 | 88.888889 | 91.666667 | 89.89899 | 33 | 7 | 3 | 56 |
| 99 | 94.915254 | 82.5 | 88.888889 | 91.666667 | 89.89899 | 33 | 7 | 3 | 56 |
| 100 | 94.915254 | 82.5 | 88.888889 | 91.666667 | 89.89899 | 33 | 7 | 3 | 56 |

APPENDIX E3

Cumulative Performance of Model versus Number of Principal Components Selected (Early vs Late; 340 Lipids)

| No | Sensitivity | Specificity | PPV | NPV | Accuracy | TN | FN | FP | TP |
|---|---|---|---|---|---|---|---|---|---|
| 1 | 100 | 0 | 62.711864 | NaN | 62.711864 | 0 | 22 | 0 | 37 |
| 2 | 100 | 0 | 62.711864 | NaN | 62.711864 | 0 | 22 | 0 | 37 |
| 3 | 100 | 0 | 62.711864 | NaN | 62.711864 | 0 | 22 | 0 | 37 |
| 4 | 86.486486 | 22.727273 | 65.306122 | 50 | 62.711864 | 5 | 17 | 5 | 32 |
| 5 | 91.891892 | 40.909091 | 72.340426 | 75 | 72.881356 | 9 | 13 | 3 | 34 |
| 6 | 91.891892 | 27.272727 | 68 | 66.666667 | 67.79661 | 6 | 16 | 3 | 34 |
| 7 | 86.486486 | 59.090909 | 78.04878 | 72.222222 | 76.271186 | 13 | 9 | 5 | 32 |
| 8 | 89.189189 | 63.636364 | 80.487805 | 77.777778 | 79.661017 | 14 | 8 | 4 | 33 |
| 9 | 91.891892 | 68.181818 | 82.926829 | 83.333333 | 83.050847 | 15 | 7 | 3 | 34 |
| 10 | 100 | 68.181818 | 84.090909 | 100 | 88.135593 | 15 | 7 | 0 | 37 |
| 11 | 100 | 68.181818 | 84.090909 | 100 | 88.135593 | 15 | 7 | 0 | 37 |
| 12 | 100 | 63.636364 | 82.222222 | 100 | 86.440678 | 14 | 8 | 0 | 37 |
| 13 | 100 | 63.636364 | 82.222222 | 100 | 86.440678 | 14 | 8 | 0 | 37 |
| 14 | 100 | 63.636364 | 82.222222 | 100 | 86.440678 | 14 | 8 | 0 | 37 |
| 15 | 100 | 63.636364 | 82.222222 | 100 | 86.440678 | 14 | 8 | 0 | 37 |
| 16 | 100 | 59.090909 | 80.434783 | 100 | 84.745763 | 13 | 9 | 0 | 37 |
| 17 | 97.297297 | 63.636364 | 81.818182 | 93.333333 | 84.745763 | 14 | 8 | 1 | 36 |
| 18 | 100 | 59.090909 | 80.434783 | 100 | 84.745763 | 13 | 9 | 0 | 37 |
| 19 | 100 | 59.090909 | 80.434783 | 100 | 84.745763 | 13 | 9 | 0 | 37 |
| 20 | 100 | 72.727273 | 86.046512 | 100 | 89.830508 | 16 | 6 | 0 | 37 |
| 21 | 100 | 72.727273 | 86.046512 | 100 | 89.830508 | 16 | 6 | 0 | 37 |
| 22 | 100 | 72.727273 | 86.046512 | 100 | 89.830508 | 16 | 6 | 0 | 37 |
| 23 | 100 | 68.181818 | 84.090909 | 100 | 88.135593 | 15 | 7 | 0 | 37 |
| 24 | 100 | 72.727273 | 86.046512 | 100 | 89.830508 | 16 | 6 | 0 | 37 |
| 25 | 100 | 72.727273 | 86.046512 | 100 | 89.830508 | 16 | 6 | 0 | 37 |
| 26 | 100 | 72.727273 | 86.046512 | 100 | 89.830508 | 16 | 6 | 0 | 37 |
| 27 | 100 | 63.636364 | 82.222222 | 100 | 86.440678 | 14 | 8 | 0 | 37 |
| 28 | 100 | 63.636364 | 82.222222 | 100 | 86.440678 | 14 | 8 | 0 | 37 |
| 29 | 100 | 63.636364 | 82.222222 | 100 | 86.440678 | 14 | 8 | 0 | 37 |
| 30 | 100 | 63.636364 | 82.222222 | 100 | 86.440678 | 14 | 8 | 0 | 37 |
| 31 | 100 | 68.181818 | 84.090909 | 100 | 88.135593 | 15 | 7 | 0 | 37 |
| 32 | 100 | 68.181818 | 84.090909 | 100 | 88.135593 | 15 | 7 | 0 | 37 |
| 33 | 100 | 68.181818 | 84.090909 | 100 | 88.135593 | 15 | 7 | 0 | 37 |
| 34 | 100 | 68.181818 | 84.090909 | 100 | 88.135593 | 15 | 7 | 0 | 37 |
| 35 | 100 | 68.181818 | 84.090909 | 100 | 88.135593 | 15 | 7 | 0 | 37 |
| 36 | 100 | 68.181818 | 84.090909 | 100 | 88.135593 | 15 | 7 | 0 | 37 |
| 37 | 100 | 63.636364 | 82.222222 | 100 | 86.440678 | 14 | 8 | 0 | 37 |
| 38 | 100 | 63.636364 | 82.222222 | 100 | 86.440678 | 14 | 8 | 0 | 37 |
| 39 | 100 | 63.636364 | 82.222222 | 100 | 86.440678 | 14 | 8 | 0 | 37 |
| 40 | 100 | 63.636364 | 82.222222 | 100 | 86.440678 | 14 | 8 | 0 | 37 |
| 41 | 100 | 63.636364 | 82.222222 | 100 | 86.440678 | 14 | 8 | 0 | 37 |
| 42 | 100 | 63.636364 | 82.222222 | 100 | 86.440678 | 14 | 8 | 0 | 37 |
| 43 | 100 | 68.181818 | 84.090909 | 100 | 88.135593 | 15 | 7 | 0 | 37 |
| 44 | 100 | 72.727273 | 86.046512 | 100 | 89.830508 | 16 | 6 | 0 | 37 |
| 45 | 100 | 72.727273 | 86.046512 | 100 | 89.830508 | 16 | 6 | 0 | 37 |
| 46 | 100 | 72.727273 | 86.046512 | 100 | 89.830508 | 16 | 6 | 0 | 37 |
| 47 | 100 | 72.727273 | 86.046512 | 100 | 89.830508 | 16 | 6 | 0 | 37 |
| 48 | 100 | 72.727273 | 86.046512 | 100 | 89.830508 | 16 | 6 | 0 | 37 |
| 49 | 100 | 72.727273 | 86.046512 | 100 | 89.830508 | 16 | 6 | 0 | 37 |
| 50 | 100 | 72.727273 | 86.046512 | 100 | 89.830508 | 16 | 6 | 0 | 37 |
| 51 | 100 | 72.727273 | 86.046512 | 100 | 89.830508 | 16 | 6 | 0 | 37 |
| 52 | 100 | 72.727273 | 86.046512 | 100 | 89.830508 | 16 | 6 | 0 | 37 |
| 53 | 100 | 72.727273 | 86.046512 | 100 | 89.830508 | 16 | 6 | 0 | 37 |
| 54 | 100 | 72.727273 | 86.046512 | 100 | 89.830508 | 16 | 6 | 0 | 37 |
| 55 | 100 | 72.727273 | 86.046512 | 100 | 89.830508 | 16 | 6 | 0 | 37 |
| 56 | 100 | 72.727273 | 86.046512 | 100 | 89.830508 | 16 | 6 | 0 | 37 |
| 57 | 100 | 72.727273 | 86.046512 | 100 | 89.830508 | 16 | 6 | 0 | 37 |
| 58 | 100 | 72.727273 | 86.046512 | 100 | 89.830508 | 16 | 6 | 0 | 37 |
| 59 | 100 | 72.727273 | 86.046512 | 100 | 89.830508 | 16 | 6 | 0 | 37 |
| 60 | 100 | 72.727273 | 86.046512 | 100 | 89.830508 | 16 | 6 | 0 | 37 |
| 61 | 100 | 72.727273 | 86.046512 | 100 | 89.830508 | 16 | 6 | 0 | 37 |
| 62 | 100 | 72.727273 | 86.046512 | 100 | 89.830508 | 16 | 6 | 0 | 37 |
| 63 | 100 | 72.727273 | 86.046512 | 100 | 89.830508 | 16 | 6 | 0 | 37 |
| 64 | 100 | 72.727273 | 86.046512 | 100 | 89.830508 | 16 | 6 | 0 | 37 |
| 65 | 100 | 72.727273 | 86.046512 | 100 | 89.830508 | 16 | 6 | 0 | 37 |
| 66 | 100 | 72.727273 | 86.046512 | 100 | 89.830508 | 16 | 6 | 0 | 37 |
| 67 | 100 | 72.727273 | 86.046512 | 100 | 89.830508 | 16 | 6 | 0 | 37 |
| 68 | 100 | 72.727273 | 86.046512 | 100 | 89.830508 | 16 | 6 | 0 | 37 |
| 69 | 100 | 72.727273 | 86.046512 | 100 | 89.830508 | 16 | 6 | 0 | 37 |
| 70 | 100 | 72.727273 | 86.046512 | 100 | 89.830508 | 16 | 6 | 0 | 37 |
| 71 | 100 | 72.727273 | 86.046512 | 100 | 89.830508 | 16 | 6 | 0 | 37 |
| 72 | 100 | 72.727273 | 86.046512 | 100 | 89.830508 | 16 | 6 | 0 | 37 |
| 73 | 100 | 72.727273 | 86.046512 | 100 | 89.830508 | 16 | 6 | 0 | 37 |

APPENDIX E3-continued

Cumulative Performance of Model versus Number of Principal Components Selected (Early vs Late; 340 Lipids)

| No | Sensitivity | Specificity | PPV | NPV | Accuracy | TN | FN | FP | TP |
|---|---|---|---|---|---|---|---|---|---|
| 74 | 100 | 72.727273 | 86.046512 | 100 | 89.830508 | 16 | 6 | 0 | 37 |
| 75 | 100 | 72.727273 | 86.046512 | 100 | 89.830508 | 16 | 6 | 0 | 37 |
| 76 | 100 | 72.727273 | 86.046512 | 100 | 89.830508 | 16 | 6 | 0 | 37 |
| 77 | 100 | 72.727273 | 86.046512 | 100 | 89.830508 | 16 | 6 | 0 | 37 |
| 78 | 100 | 72.727273 | 86.046512 | 100 | 89.830508 | 16 | 6 | 0 | 37 |
| 79 | 100 | 72.727273 | 86.046512 | 100 | 89.830508 | 16 | 6 | 0 | 37 |
| 80 | 100 | 72.727273 | 86.046512 | 100 | 89.830508 | 16 | 6 | 0 | 37 |
| 81 | 100 | 72.727273 | 86.046512 | 100 | 89.830508 | 16 | 6 | 0 | 37 |
| 82 | 100 | 72.727273 | 86.046512 | 100 | 89.830508 | 16 | 6 | 0 | 37 |
| 83 | 100 | 72.727273 | 86.046512 | 100 | 89.830508 | 16 | 6 | 0 | 37 |
| 84 | 100 | 72.727273 | 86.046512 | 100 | 89.830508 | 16 | 6 | 0 | 37 |
| 85 | 100 | 72.727273 | 86.046512 | 100 | 89.830508 | 16 | 6 | 0 | 37 |
| 86 | 100 | 72.727273 | 86.046512 | 100 | 89.830508 | 16 | 6 | 0 | 37 |
| 87 | 100 | 72.727273 | 86.046512 | 100 | 89.830508 | 16 | 6 | 0 | 37 |
| 88 | 100 | 72.727273 | 86.046512 | 100 | 89.830508 | 16 | 6 | 0 | 37 |
| 89 | 100 | 72.727273 | 86.046512 | 100 | 89.830508 | 16 | 6 | 0 | 37 |
| 90 | 100 | 72.727273 | 86.046512 | 100 | 89.830508 | 16 | 6 | 0 | 37 |
| 91 | 100 | 72.727273 | 86.046512 | 100 | 89.830508 | 16 | 6 | 0 | 37 |
| 92 | 100 | 72.727273 | 86.046512 | 100 | 89.830508 | 16 | 6 | 0 | 37 |
| 93 | 100 | 72.727273 | 86.046512 | 100 | 89.830508 | 16 | 6 | 0 | 37 |
| 94 | 100 | 72.727273 | 86.046512 | 100 | 89.830508 | 16 | 6 | 0 | 37 |
| 95 | 100 | 72.727273 | 86.046512 | 100 | 89.830508 | 16 | 6 | 0 | 37 |
| 96 | 100 | 72.727273 | 86.046512 | 100 | 89.830508 | 16 | 6 | 0 | 37 |
| 97 | 100 | 72.727273 | 86.046512 | 100 | 89.830508 | 16 | 6 | 0 | 37 |
| 98 | 100 | 72.727273 | 86.046512 | 100 | 89.830508 | 16 | 6 | 0 | 37 |
| 99 | 100 | 72.727273 | 86.046512 | 100 | 89.830508 | 16 | 6 | 0 | 37 |
| 100 | 100 | 72.727273 | 86.046512 | 100 | 89.830508 | 16 | 6 | 0 | 37 |

The invention claimed is:

1. A method for the treatment of ovarian cancer in an individual, the method comprising:

(I) providing a dataset comprising concentrations of a plurality of lipids in a sample from said individual, and (II) applying a classification model according to one of (A)-(C) as follows to generate a transformed dataset:

Classification Model A:

(i) a 340×340 transformation matrix as shown in Appendix B1 and an SVM model as shown in Appendix C1;

(ii) a 340×85 transformation matrix comprising the first 85 columns of the matrix as shown in Appendix B1 and an SVM model as shown in Appendix C4;

(iii) a 340×10 transformation matrix comprising the first 10 columns of the matrix as shown in Appendix B1 and an SVM model as shown in Appendix C7;

(iv) a 82×82 transformation matrix as shown in Appendix B4 and an SVM model as shown in Appendix C10; or (v) a 77×77 transformation matrix as shown in Appendix B7 and an SVM model as shown in Appendix C13;

Classification Model B:

(i) a 340×340 transformation matrix as shown in Appendix B2 and an SVM model as shown in Appendix C2;

(ii) a 340×87 transformation matrix comprising the first 87 columns of the matrix as shown in Appendix B2 and an SVM model as shown in Appendix C5;

(iii) a 340×29 transformation matrix comprising the first 29 columns of the matrix as shown in Appendix B2 and an SVM model as shown in Appendix C8;

(iv) a 82×82 transformation matrix as shown in Appendix B5 and an SVM model as shown in Appendix C11; or (v) a 77×77 transformation matrix as shown in Appendix B8 and an SVM model as shown in Appendix C14; or Classification Model C:

(i) a 340×340 transformation matrix as shown in Appendix B3 and an SVM model as shown in Appendix C3;

(ii) a 340×44 transformation matrix comprising the first 44 columns of the matrix as shown in Appendix B3 and an SVM model as shown in Appendix C6;

(iii) a 340×9 transformation matrix comprising the first 9 columns of the matrix as shown in Appendix B3 and an SVM model as shown in Appendix C9;

(iv) a 82×82 transformation matrix as shown in Appendix B6 and an SVM model as shown in Appendix C12; or (v) a 77×77 transformation matrix as shown in Appendix B9 and an SVM model as shown in Appendix C 15; and (III) subjecting the transformed dataset of step (II) to SVM analysis with an SVM model of the classification model, in which:

a) when a classification model according to Classification Model A is used, an output of >0 indicates a normal sample, and an output of <0 indicates an ovarian cancer sample;

b) when a classification model according to Classification Model B is used, an output of >0 indicates a benign sample, and an output of <0 indicates a malignant sample; and c) when a classification model according to Classification Model C is used, an output of >0 indicates an early stage ovarian cancer sample, and an output of <0 indicates a late stage ovarian cancer sample;

whereby a status of the sample is determined, and wherein, when said output <0 indicates an ovarian cancer sample, a malignant sample, or a late-stage ovarian cancer sample, a treatment is administered comprising administering a therapeutic agent selected from the group consisting of carboplatin, paclitaxel, topotecan, liposomal doxorubicin, gemcitabine, cisplatin, and a combination of carboplatin and paclitaxel.

2. The method of claim 1, which is a computer implemented method.

3. The method of claim 1 further comprising the step, before step (I), of measuring the concentration of a plurality of lipids in a sample from or of the individual to generate a dataset comprising concentrations of said lipids.

4. The method of claim 1, in which the plurality of lipids includes a plurality of choline lipids, and further optionally comprises phosphatidic acid (GPA), phosphatidylglycerol (GPGro), phosphatidylserine acid (GPSer), sulfatides, cardiolipin, phosphatidylethanolamine (GPEtn), phosphatidylinositol (GPIns), phosphatidylinositol phosphates (GPInsPs), ceramide (Cer), mono hexosyl ceramide (MonoHexCer) and di hexosyl ceramide (DiHexCer).

5. The method of claim 4 wherein the choline lipids include phosphatidylcholine (GPCho) or sphingomyelin (SM) or both.

6. The method of claim 1 wherein the plurality of lipids comprises the lipids set out in Table D1, Table D2, Table D3, Table E4 or Table E6.

7. The method of claim 1 in which the sample comprises a serum sample of or from an individual.

8. The method of claim 3 wherein the lipids are identified by mass spectroscopy, electrospray ionization mass spectrometry (ESI-MS), or quantified by multiple reaction monitoring (MRM), or both ESI-MS and MRM.

9. The method of claim 3 claim, in which the concentration of each lipid is normalized by obtaining $$\text{Lipid}_i = \frac{x_i}{[Std] \cdot \sum_{i=1}^{n} x_i},$$

where $x_i$ is the intensity of a $\text{lipid}_i$ and Std is the ratio of the intensity to the amount in pmoles of a lipid standard.

* * * * *